United States Patent
Mainolfi et al.

(10) Patent No.: US 11,352,350 B2
(45) Date of Patent: Jun. 7, 2022

(54) IRAK DEGRADERS AND USES THEREOF

(71) Applicant: Kymera Therapeutics, Inc., Cambridge, MA (US)

(72) Inventors: Nello Mainolfi, Belmont, MA (US); Nan Ji, Arlington, MA (US); Arthur F. Kluge, Concord, MA (US); Matthew M. Weiss, Boston, MA (US); Yi Zhang, Belmont, MA (US); Xiaozhang Zheng, Lexington, MA (US)

(73) Assignee: KYMERA THERAPEUTICS, INC., Watertown, MA (US)

( * ) Notice: Subject to any disclaimer, the term of this patent is extended or adjusted under 35 U.S.C. 154(b) by 0 days.

(21) Appl. No.: 16/701,077

(22) Filed: Dec. 2, 2019

(65) Prior Publication Data

US 2021/0323952 A1    Oct. 21, 2021

Related U.S. Application Data

(60) Provisional application No. 62/879,117, filed on Jul. 26, 2019, provisional application No. 62/875,347, filed on Jul. 17, 2019, provisional application No. 62/868,574, filed on Jun. 28, 2019, provisional application No. 62/851,427, filed on May 22, 2019, provisional application No. 62/831,007, filed on Apr. 8, 2019, provisional application No. 62/826,743, filed on Mar. 29, 2019, provisional application No. 62/793,992, filed on Jan. 18, 2019, provisional application No. 62/788,460, filed on Jan. 4, 2019, provisional application No. 62/774,051, filed on Nov. 30, 2018.

(51) Int. Cl.
*C07D 413/14* (2006.01)
*A61P 29/00* (2006.01)

(52) U.S. Cl.
CPC ............ *C07D 413/14* (2013.01); *A61P 29/00* (2018.01)

(58) Field of Classification Search
CPC ................................. C07D 413/14; A61P 29/00
See application file for complete search history.

(56) References Cited

U.S. PATENT DOCUMENTS

| | | | |
|---|---|---|---|
| 4,650,750 A | 3/1987 | Giese | |
| 4,709,016 A | 11/1987 | Giese | |
| 5,360,811 A | 11/1994 | Tegeler et al. | |
| 5,360,819 A | 11/1994 | Giese | |
| 5,516,931 A | 5/1996 | Giese et al. | |
| 5,602,273 A | 2/1997 | Giese et al. | |
| 5,604,104 A | 2/1997 | Giese et al. | |
| 5,610,020 A | 3/1997 | Giese et al. | |
| 5,650,270 A | 7/1997 | Giese et al. | |
| 5,721,246 A | 2/1998 | Yoshino et al. | |
| 6,306,663 B1 | 10/2001 | Kenten et al. | |
| 6,552,065 B2 | 4/2003 | Remiszewski et al. | |
| 6,559,280 B2 | 5/2003 | Kenten et al. | |
| 6,627,754 B2 | 9/2003 | Blumenkopf et al. | |
| 6,949,537 B2 | 9/2005 | Garlich et al. | |
| 7,041,298 B2 | 5/2006 | Deshaies et al. | |
| 7,071,189 B2 | 7/2006 | Kawashima et al. | |
| 7,074,620 B2 | 7/2006 | Kenten et al. | |
| 7,173,015 B2 | 2/2007 | Schreiber et al. | |
| 7,208,157 B2 | 4/2007 | Deshaies et al. | |
| 7,273,920 B2 | 9/2007 | Kenten et al. | |
| 7,307,077 B2 | 12/2007 | Kawashima et al. | |
| 7,390,799 B2 | 6/2008 | Bruncko et al. | |
| 7,402,325 B2 | 7/2008 | Addington | |
| 7,449,458 B2 | 11/2008 | Bhamidipati et al. | |
| 7,501,496 B1 | 3/2009 | Endl et al. | |
| 7,514,444 B2 | 4/2009 | Honigberg et al. | |
| 7,528,143 B2 | 5/2009 | Noronha et al. | |
| 7,557,210 B2 | 7/2009 | Singh et al. | |
| 7,598,257 B2 | 10/2009 | Rodgers et al. | |
| 7,622,496 B2 | 11/2009 | Larsen et al. | |
| 7,667,039 B2 | 2/2010 | Garcia-Echeverria et al. | |
| 7,713,943 B2 | 5/2010 | Klippel-Giese et al. | |
| 7,781,433 B2 | 8/2010 | Chuckowree et al. | |
| 7,932,260 B2 | 4/2011 | Fowler et al. | |
| 7,989,622 B2 | 8/2011 | Bajjalieh et al. | |
| 8,138,347 B2 | 3/2012 | Knight et al. | |
| 8,185,616 B2 | 5/2012 | Nagata et al. | |
| 8,217,035 B2 | 7/2012 | Burger et al. | |
| 8,338,439 B2 | 12/2012 | Singh et al. | |
| 8,486,941 B2 | 7/2013 | Burns et al. | |
| 8,906,682 B2 | 12/2014 | June et al. | |
| 9,500,653 B2 | 11/2016 | Crews et al. | |
| 9,632,089 B2 | 4/2017 | Crews et al. | |
| 9,694,084 B2 | 4/2017 | Bradner et al. | |
| 9,750,816 B2 | 9/2017 | Bradner et al. | |
| 9,770,512 B2 | 9/2017 | Bradner et al. | |

(Continued)

FOREIGN PATENT DOCUMENTS

| | | |
|---|---|---|
| CN | 105085620 | 5/2018 |
| WO | WO2001042246 | 6/2001 |

(Continued)

OTHER PUBLICATIONS

U.S. Appl. No. 62/832,103, filed Apr. 10, 2019, Nello Mainolfi.
U.S. Appl. No. 62/912,252, filed Oct. 8, 2019, Nello Mainolfi.
U.S. Appl. No. 62/948,936, filed Dec. 17, 2019, Nello Mainolfi.
U.S. Appl. No. 62/948,992, filed Dec. 17, 2019, Nello Mainolfi.
U.S. Appl. No. 62/949,195, filed Dec. 17, 2019, Nello Mainolfi.
U.S. Appl. No. 62/949,298, filed Dec. 17, 2019, Matthew M. Weiss.
U.S. Appl. No. 62/949,320, filed Dec. 17, 2019, Matthew M. Weiss.
U.S. Appl. No. 62/959,332, filed Jan. 10, 2020, Nello Mainolfi.
U.S. Appl. No. 62/964,955, filed Jan. 23, 2020, Nello Mainolfi.
U.S. Appl. No. 62/969,418, filed Feb. 3, 2020, Matthew M. Weiss.
Moynagh, "The Pellino Family: IRAK E3 ligases with emerging roles in innate immune signalling," Trends Immunol. 2009, 30(1): 33 42.

(Continued)

*Primary Examiner* — Timothy R Rozof
(74) *Attorney, Agent, or Firm* — Dechert LLP; Andrea L. C. Reid; Todd K. Macklin

(57) ABSTRACT

The present invention provides compounds, compositions thereof, and methods of using the same.

11 Claims, 22 Drawing Sheets

(56) References Cited

U.S. PATENT DOCUMENTS

| | | |
|---|---|---|
| 9,821,068 B2 | 11/2017 | Bradner et al. |
| 9,969,710 B2 | 5/2018 | Jorand-Lebrun et al. |
| 10,125,114 B2 | 11/2018 | Bradner et al. |
| 10,336,744 B2 | 7/2019 | Harling et al. |
| 10,874,743 B2 | 12/2020 | Mainolfi et al. |
| 2001/0053782 A1 | 12/2001 | Blumenkopf et al. |
| 2002/0042427 A1 | 4/2002 | Tang et al. |
| 2002/0068063 A1 | 6/2002 | Deshaies et al. |
| 2002/0183360 A1 | 12/2002 | Muller et al. |
| 2004/0029902 A1 | 2/2004 | Singh et al. |
| 2004/0048859 A1 | 3/2004 | Germann et al. |
| 2004/0106569 A1 | 6/2004 | Klippel-Giese et al. |
| 2004/0116421 A1 | 6/2004 | Kawashima et al. |
| 2004/0242631 A1 | 12/2004 | Garlich et al. |
| 2005/0014802 A1 | 1/2005 | Attardo et al. |
| 2005/0075306 A1 | 4/2005 | Schreiber et al. |
| 2006/0211657 A1 | 9/2006 | Singh et al. |
| 2007/0098719 A1 | 5/2007 | Smith et al. |
| 2007/0135461 A1 | 6/2007 | Rodgers et al. |
| 2007/0191405 A1 | 8/2007 | Noronha et al. |
| 2008/0076768 A1 | 3/2008 | Chuckowree et al. |
| 2008/0108636 A1 | 5/2008 | Honigberg et al. |
| 2008/0194579 A1 | 8/2008 | Garcia-Echeverria et al. |
| 2008/0275067 A1 | 11/2008 | Fowler et al. |
| 2009/0055944 A1 | 2/2009 | Korman et al. |
| 2009/0136494 A1 | 5/2009 | Ponath et al. |
| 2009/0233903 A1 | 9/2009 | Rodgers et al. |
| 2010/0087440 A1 | 4/2010 | Bajjalieh et al. |
| 2010/0150892 A1 | 6/2010 | Han |
| 2010/0197671 A1 | 8/2010 | Burns et al. |
| 2010/0197686 A1 | 8/2010 | Xing et al. |
| 2010/0203056 A1 | 8/2010 | Irving et al. |
| 2010/0233183 A1 | 9/2010 | Triebel et al. |
| 2010/0247554 A1 | 9/2010 | Lemke et al. |
| 2010/0249092 A1 | 9/2010 | Singh et al. |
| 2010/0249126 A1 | 9/2010 | Burger et al. |
| 2010/0279316 A1 | 11/2010 | Gorelik et al. |
| 2011/0008331 A1 | 1/2011 | Triebel et al. |
| 2011/0053941 A1 | 3/2011 | Mautino et al. |
| 2011/0136796 A1 | 6/2011 | Mautino et al. |
| 2011/0165156 A1 | 7/2011 | Dimoudis et al. |
| 2011/0223611 A1 | 9/2011 | Salamone et al. |
| 2011/0274683 A1 | 11/2011 | Wong et al. |
| 2012/0015962 A1 | 1/2012 | Arora et al. |
| 2012/0189639 A1 | 7/2012 | Schebye et al. |
| 2012/0277217 A1 | 11/2012 | Mautino et al. |
| 2012/0283238 A1 | 11/2012 | Romero et al. |
| 2012/0329997 A1 | 12/2012 | Fertig et al. |
| 2013/0005949 A1 | 1/2013 | Fertig et al. |
| 2013/0149236 A1 | 6/2013 | Johnson et al. |
| 2013/0190340 A1 | 7/2013 | Hedstrom et al. |
| 2013/0231328 A1 | 9/2013 | Harriman et al. |
| 2013/0274241 A1 | 10/2013 | Jorand-Lebrun et al. |
| 2014/0018343 A1 | 1/2014 | Romero et al. |
| 2014/0018357 A1 | 1/2014 | Harriman et al. |
| 2014/0018361 A1 | 1/2014 | Harriman et al. |
| 2014/0066625 A1 | 3/2014 | Mautino et al. |
| 2014/0079699 A1 | 3/2014 | Wong et al. |
| 2014/0079706 A1 | 3/2014 | Cannarile et al. |
| 2014/0093511 A1 | 4/2014 | Lonberg et al. |
| 2014/0155379 A1 | 6/2014 | Ho et al. |
| 2014/0194404 A1 | 7/2014 | Mcelroy et al. |
| 2014/0302523 A1 | 10/2014 | Crews et al. |
| 2014/0329799 A1 | 11/2014 | Seganish et al. |
| 2014/0336363 A1 | 11/2014 | Fertig et al. |
| 2014/0341917 A1 | 11/2014 | Nastri et al. |
| 2014/0356322 A1 | 12/2014 | Crews et al. |
| 2015/0011532 A1 | 1/2015 | Paidi et al. |
| 2015/0018344 A1 | 1/2015 | Paidi et al. |
| 2015/0045347 A1 | 2/2015 | Dodd et al. |
| 2015/0094305 A1 | 4/2015 | Romero et al. |
| 2015/0133451 A1 | 5/2015 | Yoshida et al. |
| 2015/0141396 A1 | 5/2015 | Crosignani et al. |
| 2015/0191464 A1 | 7/2015 | Santella et al. |
| 2015/0002254 A1 | 8/2015 | Castro et al. |
| 2015/0225449 A1 | 8/2015 | Donnell et al. |
| 2015/0274708 A1 | 10/2015 | Seganish et al. |
| 2015/0274738 A1 | 10/2015 | Gray et al. |
| 2015/0284382 A1 | 10/2015 | Bhide et al. |
| 2015/0284405 A1 | 10/2015 | Trzupek et al. |
| 2015/0291562 A1 | 10/2015 | Crew et al. |
| 2015/0299224 A1 | 10/2015 | Seganish et al. |
| 2015/0329498 A1 | 11/2015 | Romero et al. |
| 2015/0374678 A1 | 12/2015 | Chamberlain et al. |
| 2015/0376167 A1 | 12/2015 | Jorand-Lebrun et al. |
| 2015/0376206 A1 | 12/2015 | Jorand-Lebrun et al. |
| 2016/0002265 A1 | 1/2016 | Jenkins et al. |
| 2016/0022642 A1 | 1/2016 | Crews et al. |
| 2016/0045607 A1 | 2/2016 | Crews et al. |
| 2016/0058872 A1 | 3/2016 | Crew et al. |
| 2016/0145252 A1 | 5/2016 | Jorand-Lebrun et al. |
| 2016/0176916 A1 | 6/2016 | Bradner et al. |
| 2016/0214972 A1 | 7/2016 | Jin et al. |
| 2016/0235730 A1 | 8/2016 | Bradner et al. |
| 2016/0235731 A1 | 8/2016 | Bradner et al. |
| 2016/0243247 A1 | 8/2016 | Bradner et al. |
| 2016/0272596 A1 | 9/2016 | Chen et al. |
| 2016/0272639 A1 | 9/2016 | Crew et al. |
| 2016/0311833 A1 | 10/2016 | Bothe et al. |
| 2016/0311839 A1 | 10/2016 | Li et al. |
| 2016/0326151 A1 | 11/2016 | Gummadi et al. |
| 2016/0340366 A1 | 11/2016 | Gummadi et al. |
| 2017/0000088 A1 | 1/2017 | Dahmann et al. |
| 2017/0001990 A1 | 1/2017 | Chen et al. |
| 2017/0008904 A1 | 1/2017 | Crew et al. |
| 2017/0022189 A1 | 1/2017 | Zhang |
| 2017/0037004 A1 | 2/2017 | Crew et al. |
| 2017/0121321 A1 | 5/2017 | Crews et al. |
| 2017/0152263 A1 | 6/2017 | Gummadi et al. |
| 2017/0204093 A1 | 7/2017 | Chan et al. |
| 2017/0247388 A1 | 8/2017 | Altman et al. |
| 2017/0281784 A1 | 10/2017 | Wang et al. |
| 2017/0327469 A1 | 11/2017 | Crew et al. |
| 2017/0369476 A1 | 12/2017 | Chen et al. |
| 2018/0009779 A1 | 1/2018 | Bradner et al. |
| 2018/0015087 A1 | 1/2018 | Liu et al. |
| 2018/0051027 A1 | 2/2018 | Lim et al. |
| 2018/0051028 A1 | 2/2018 | Lim et al. |
| 2018/0051029 A1 | 2/2018 | Lim et al. |
| 2018/0051030 A1 | 2/2018 | Lim et al. |
| 2018/0051035 A1 | 2/2018 | Lim et al. |
| 2018/0085465 A1 | 3/2018 | Bradner et al. |
| 2018/0118733 A1 | 5/2018 | Harling et al. |
| 2018/0134684 A1 | 5/2018 | Bradner et al. |
| 2018/0147202 A1 | 5/2018 | Crew et al. |
| 2018/0186799 A1 | 7/2018 | Gardner et al. |
| 2018/0201609 A1 | 7/2018 | Gummadi et al. |
| 2018/0208605 A1 | 7/2018 | Gummadi et al. |
| 2018/0228907 A1 | 8/2018 | Crew et al. |
| 2018/0230157 A1 | 8/2018 | Bacon et al. |
| 2019/0071415 A1 | 3/2019 | Bradner et al. |
| 2019/0076539 A1 | 3/2019 | Phillips et al. |
| 2019/0076540 A1 | 3/2019 | Phillips et al. |
| 2019/0076541 A1 | 3/2019 | Phillips et al. |
| 2019/0076542 A1 | 3/2019 | Phillips et al. |
| 2019/0151457 A1 | 5/2019 | Bradner et al. |
| 2019/0192668 A1 | 6/2019 | Mainolfi et al. |
| 2019/0276474 A1 | 9/2019 | Chan et al. |
| 2020/0010468 A1 | 1/2020 | Ji et al. |
| 2020/0347045 A1 | 11/2020 | Mainolfi et al. |
| 2020/0377469 A1 | 12/2020 | Mainolfi et al. |
| 2021/0002296 A1 | 1/2021 | Mainolfi et al. |
| 2021/0228562 A1 | 7/2021 | Weiss |

FOREIGN PATENT DOCUMENTS

| | | |
|---|---|---|
| WO | WO2002020740 | 3/2002 |
| WO | WO2002088112 | 11/2002 |
| WO | WO2003063794 | 8/2003 |
| WO | WO2004019973 | 3/2004 |
| WO | WO2004089925 | 10/2004 |
| WO | WO2004106328 | 12/2004 |
| WO | WO2005007623 | 1/2005 |
| WO | WO2005113554 | 12/2005 |

(56) References Cited

FOREIGN PATENT DOCUMENTS

| | | |
|---|---|---|
| WO | WO2006029879 | 3/2006 |
| WO | WO2006078846 | 7/2006 |
| WO | WO2006105021 | 10/2006 |
| WO | WO2006122806 | 11/2006 |
| WO | WO2007005874 | 1/2007 |
| WO | WO2007016176 | 2/2007 |
| WO | WO2007044729 | 4/2007 |
| WO | WO2007053452 | 5/2007 |
| WO | WO2007070514 | 6/2007 |
| WO | WO2007084786 | 7/2007 |
| WO | WO2007129161 | 11/2007 |
| WO | WO2008039218 | 4/2008 |
| WO | WO2008109943 | 9/2008 |
| WO | WO2008118802 | 10/2008 |
| WO | WO2008132601 | 11/2008 |
| WO | WO2009009161 | 1/2009 |
| WO | WO2009044273 | 4/2009 |
| WO | WO2009073620 | 6/2009 |
| WO | WO2009114512 | 9/2009 |
| WO | WO2009132238 | 10/2009 |
| WO | WO2010019570 | 2/2010 |
| WO | WO2010077634 | 7/2010 |
| WO | WO2011028683 | 3/2011 |
| WO | WO2011043371 | 4/2011 |
| WO | WO2011056652 | 5/2011 |
| WO | WO2011070024 | 6/2011 |
| WO | WO2011090760 | 7/2011 |
| WO | WO2011107553 | 9/2011 |
| WO | WO2011109400 | 9/2011 |
| WO | WO2011131407 | 10/2011 |
| WO | WO2011140249 | 11/2011 |
| WO | WO2012003281 | 1/2012 |
| WO | WO2012007375 | 1/2012 |
| WO | WO2012032433 | 3/2012 |
| WO | WO2012145493 | 4/2012 |
| WO | WO2012068546 | 5/2012 |
| WO | WO2012078559 | 6/2012 |
| WO | WO2012084704 | 6/2012 |
| WO | WO2012097013 | 7/2012 |
| WO | WO2012129258 | 9/2012 |
| WO | WO2012142237 | 10/2012 |
| WO | WO2013042137 | 3/2013 |
| WO | WO2013066729 | 5/2013 |
| WO | WO2013079174 | 6/2013 |
| WO | WO2013087699 | 6/2013 |
| WO | WO2013106535 | 7/2013 |
| WO | WO2013106612 | 7/2013 |
| WO | WO2013106614 | 7/2013 |
| WO | WO2013106641 | 7/2013 |
| WO | WO2013106643 | 7/2013 |
| WO | WO2013106646 | 7/2013 |
| WO | WO2013119716 | 8/2013 |
| WO | WO2013132044 | 9/2013 |
| WO | WO2013169264 | 11/2013 |
| WO | WO2014008218 | 1/2014 |
| WO | WO2014008992 | 1/2014 |
| WO | WO2014011902 | 1/2014 |
| WO | WO2014011906 | 1/2014 |
| WO | WO2014011911 | 1/2014 |
| WO | WO2014036357 | 3/2014 |
| WO | WO2014044622 | 3/2014 |
| WO | WO2014058685 | 4/2014 |
| WO | WO2014058691 | 4/2014 |
| WO | WO2014063061 | 4/2014 |
| WO | WO2014074675 | 5/2014 |
| WO | WO2014108452 | 7/2014 |
| WO | WO2014121931 | 8/2014 |
| WO | WO2014121942 | 8/2014 |
| WO | WO2014143672 | 9/2014 |
| WO | WO2015048281 | 4/2015 |
| WO | WO2015068856 | 5/2015 |
| WO | WO2015071393 | 5/2015 |
| WO | WO2015091426 | 6/2015 |
| WO | WO2015103453 | 7/2015 |
| WO | WO2015104662 | 7/2015 |
| WO | WO2015104688 | 7/2015 |
| WO | WO2015150995 | 10/2015 |
| WO | WO2015160845 | 10/2015 |
| WO | WO2015164374 | 10/2015 |
| WO | WO2015193846 | 12/2015 |
| WO | WO2016011390 | 1/2016 |
| WO | WO2016053769 | 4/2016 |
| WO | WO2016053770 | 4/2016 |
| WO | WO2016053771 | 4/2016 |
| WO | WO2016053772 | 4/2016 |
| WO | WO2016081679 | 5/2016 |
| WO | WO2016105518 | 6/2016 |
| WO | WO2016118666 | 7/2016 |
| WO | WO2016144844 | 9/2016 |
| WO | WO2016144846 | 9/2016 |
| WO | WO2016144847 | 9/2016 |
| WO | WO2016144848 | 9/2016 |
| WO | WO2016144849 | 9/2016 |
| WO | WO2016149668 | 9/2016 |
| WO | WO2016169989 | 10/2016 |
| WO | WO2016172560 | 10/2016 |
| WO | WO2016174183 | 11/2016 |
| WO | WO2016197032 | 12/2016 |
| WO | WO2016197114 | 12/2016 |
| WO | WO2016210034 | 12/2016 |
| WO | WO2017004133 | 1/2017 |
| WO | WO2017004134 | 1/2017 |
| WO | WO2017007612 | 1/2017 |
| WO | WO2017009798 | 1/2017 |
| WO | WO2017009806 | 1/2017 |
| WO | WO2017011371 | 1/2017 |
| WO | WO2017011590 | 1/2017 |
| WO | WO2017030814 | 2/2017 |
| WO | WO2017033093 | 3/2017 |
| WO | WO2017049068 | 3/2017 |
| WO | WO2017059280 | 4/2017 |
| WO | WO2017079267 | 5/2017 |
| WO | WO2017108723 | 6/2017 |
| WO | WO2017117473 | 7/2017 |
| WO | WO2017117474 | 7/2017 |
| WO | WO2017127430 | 7/2017 |
| WO | WO2017161119 | 9/2017 |
| WO | WO2017176708 | 10/2017 |
| WO | WO2017176957 | 10/2017 |
| WO | WO2017176958 | 10/2017 |
| WO | WO2017197036 | 11/2017 |
| WO | WO2017197046 | 11/2017 |
| WO | WO2017197051 | 11/2017 |
| WO | WO2017197055 | 11/2017 |
| WO | WO2017197056 | 11/2017 |
| WO | WO2017201449 | 11/2017 |
| WO | WO2017205762 | 11/2017 |
| WO | WO2017205766 | 11/2017 |
| WO | WO2017207385 | 12/2017 |
| WO | WO2017211924 | 12/2017 |
| WO | WO2018052058 | 3/2018 |
| WO | WO2018098367 | 5/2018 |
| WO | WO2018144649 | 8/2018 |
| WO | WO2018209012 | 11/2018 |
| WO | WO2018237026 | 12/2018 |
| WO | WO2019043214 | 3/2019 |
| WO | WO2019060693 | 3/2019 |
| WO | WO2019060742 | 3/2019 |
| WO | WO2019084026 | 5/2019 |
| WO | WO2019084030 | 5/2019 |
| WO | WO2019099868 | 5/2019 |
| WO | WO2019099926 | 5/2019 |
| WO | WO2019133531 | 7/2019 |
| WO | WO2019140380 | 7/2019 |
| WO | WO2019140387 | 7/2019 |
| WO | WO2019/0160915 A1 * | 8/2019 |
| WO | WO2019165229 | 8/2019 |
| WO | 2019236483 | 12/2019 |
| WO | 2020018788 A1 | 1/2020 |
| WO | WO2020010177 | 1/2020 |
| WO | WO2020010210 | 1/2020 |
| WO | WO2020010227 | 1/2020 |
| WO | 2020251969 A1 | 12/2020 |
| WO | 2020251971 A1 | 12/2020 |

(56) References Cited

FOREIGN PATENT DOCUMENTS

| | | |
|---|---|---|
| WO | 2020251972 A1 | 12/2020 |
| WO | 2020251974 A1 | 12/2020 |
| WO | 2020264490 A1 | 12/2020 |
| WO | 2020264499 A1 | 12/2020 |
| WO | 2021011631 A1 | 1/2021 |
| WO | 2021011634 A1 | 1/2021 |
| WO | 2021011868 A1 | 1/2021 |
| WO | 2021011871 A1 | 1/2021 |
| WO | 2021127190 A1 | 6/2021 |
| WO | 2021127278 A1 | 6/2021 |

OTHER PUBLICATIONS

Nunes et al., "Targeting IRAK4 for Degradation with PROTACTSs", ACS Med Chem Lett. 2019, 10(7):1081-1085, entire document.
PCT International Search Report and Written Opinion for PCT/US2020/040101, dated Nov. 10, 2020.
PCT International Search Report and Written Opinion for PCT/US2020/040125, dated Nov. 13, 2020.
PCT International Search Report and Written Opinion for PCT/US2020/042530, dated Oct. 16, 2020.
PCT International Search Report and Written Opinion from PCT/US2019/064070, dated Apr. 6, 2020.
Adams, el al., "Big opportunities for small molecules in immuno-oncology," Nature Reviews: Drug Discovery, vol. 14, No. 9, 2015 (pp. 603-622).
Aruri et al., "Metal-free Cross-Dehydrogenative Coupling of HN-azoles with a-C(sp3)-H Amides via C—H Activation and Its Mechanistic and Application Studies," The Journal of Organic Chemistry, vol. 82, No. 2, 2016 (pp. 1000-1012).
Aurigene Discovery Tech. Ltd. Presentation: Novel IRAK-4 Inhibitors exhibit highly potent anti-proliferative activity in DLBCL cell lines with activation MYD88 L264P mutation, 2015 (2 pages).
Berge et al., "Pharmaceutical Salts," Journal of Pharmaceutical Sciences, vol. 66, No. 1, 1977 (pp. 1-19).
Berndsen et al., "New insights into ubiquitin E3 ligase mechanism, Nature Structural and Molecular Biology," vol. 21, No. 4, 2014 (pp. 301-307).
Boichenko et al. "A FRET-Based Assay for the Identification and Characterization of Cereblon Ligands," Journal of Medicinal Chemistry, vol. 59, No. 2, 2016 (pp. 770-774).
Buckley et al., "IRAK-4 inhibitors. Part 1: a series of amides," Bioorganic & Medicinal Chemistry Letters, vol. 18, No. 11, 2008 (pp. 3211-3214).
Buckley et al., "IRAK-4 inhibitors. Part II: a structure-based assessment of imidazo[l,2-a]pyridine binding," Bioorganic & Medicinal Chemistry Letters, vol. 18, 2008 (pp. 3291-3295).
Buckley el al., "IRAK-4 inhibitors. Part III: A series of imidazo[1,2-a]pyridines," Bioorganic & Medicinal Chemistry Letters, vol. 18, 2008 (pp. 3656-3660).
Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience, vol. 32, No. 43, 2012 (pp. 15112-15123).
Cario, E., "Therapeutic Impact of Toll-like Receptors on Inflammatory Bowel Diseases: A Multiple-edged Sword," Inflammatory Bowel Diseases, vol. 14, No. 3, 2008 (pp. 411-421).
Chang et al., "What is the functional role of the thalidomide binding protein cereblon?", International Journal of Biochemistry and Molecular Biology, vol. 2, No. 3, 2011 (pp. 287-294).
Chaudhary et al., "Recent Advances in the Discovery of Small Molecule Inhibitors of Interleukin-1 Receptor-Associated Kinase 4 (IRAK4) as a Therapeutic Target for Inflammation and Oncology Disorders," Journal of Medicinal Chemistry, vol. 58, No. 1, 2015 (pp. 96-110).
Chiang, E.Y. et al., "Immune Complex-Mediated Cell Activation from Systemic Lupus Erythematosus and Rheumatoid Arthritis Patients Elaborate Different Requirements for IRAK1/4 Kinase Activity across human Cell Types," The Journal of Immunology, vol. 186, No. 2, 2011 (pp. 1279-1288).
Cohen et al., "Targeting protein kinases for the development of anti-inflammatory drugs," Current Opinion Cell Biology, vol. 21, No. 2, 2009 (pp. 317-324).
Connolly et al., "Complexities of TGF-β Targeted Cancer Therapy," International Journal of Biological Sciences, vol. 8, 2012 (pp. 964-978).
Contino-Pepin et al., "Preliminary biological evaluations of new thalidomide analogues for multiple sclerosis application," Bioorganic & Medicinal Chemistry Letters, vol. 19, No. 2, 2009 (pp. 878-881).
Crews et al., "Targeting the Undruggable Proteome: The Small Molecules of My Dreams," Chemistry & Biology, vol. 17, No. 6, 2010 (pp. 551-555).
Cushing et al.,"IRAK4 kinase controls Toll-like receptor induced inflammation through the transcription factor IRF5 in primary human monocytes," Journal of Biological Chemistry, vol. 292, No. 45, 2017 (pp. 18689-18698).
Dalbeth et al., "Hyperuricaemia and gout: state of the art and future perspectives," Annals of Rheumatic Diseases, vol. 69, No. 10, 2010 (pp. 1738-1743).
Degorce et al., "Optimization of permeability in a series of pyrrolotriazine inhibitors of IRAK4," Bioorganic and Medicinal Chemistry, vol. 26, No. 4, 2018 (pp. 913-924).
Deshaies et al., "RING domain E3 ubiquitin ligases," Annual Review of Biochemistry, vol. 78, 2009, (pp. 399-434).
Dinarello, C. "IL-1: Discoveries, controversies and future directions," European Journal of Immunology, vol. 40, 2010 (pp. 595-653).
Dinarello, C. "Interleukin 1 and interleukin 18 as mediators of inflammation and the aging process," The American Journal of Clinical Nutrition, vol. 83, 2006 (pp. 447S-455S).
Dinarello, C., "Interleukin-18 and the Pathogenesis of Inflammatory Diseases," Seminars in Nephrology, vol. 27, No. 1, 2007 (pp. 98-114).
Dudhgaonkar et al., "Selective IRAK4 Inhibition Attenuates Disease in Murine Lupus Models and Demonstrates Steroid Sparing Activity," Journal of Immunology, vol. 198, No. 3, 2017 (pp. 1308-1319).
Dunne et al., "IRAK1 and IRAK4 Promote Phosphorylation, Ubiquitation, and Degradation of MyD88 Adaptor-like (Ma1)," The Journal of Biological Chemistry, 2010, vol. 285, No. 24, 2010 (pp. 18276-18282).
Fischer et al., "Structure of the DDB1-CRBN E3 ubiquitin ligase in complex with thalidomide," Nature, vol. 512, No. 7512, 2014 (pp. 49-53).
Flannery et al., "The interleukin-1 receptor-associated kinases: Critical regulators of innate immune signaling" Biochemical Pharmacology, vol. 80, No. 12, 2010 (pp. 1981-1991).
Gearing, A. "Targeting toll-like receptors for drug development: a summary of commercial approaches," Immunology and Cell Biology, vol. 85, No. 6, 2007 (pp. 490-494).
Geyer, M. et al., "Actual status of antiinterleukin-1 therapies in rheumatic diseases," Current Opinion in Rheumatology, vol. 22, No. 3, 2010 (pp. 246-251).
Gottipati et al., "IRAK1: A critical signaling mediator of innate immunity," Cellular Signaling, vol. 20, No. 2, 2008 (pp. 269-276).
Hagner et al., "CC-122, a pleiotropic pathway modifier, mimics an interferon response and has antitumor activity in DLBCL," Blood, vol. 126, 2015 (pp. 779-789).
Hennessy et al., "Targeting Toll-like receptors: emerging therapeutics?" Nature Reviews Drug Discovery, vol. 9, 2010 (pp. 293-307).
Hines et al., "MDM2-Recruiting PROTAC Offers Superior, Synergistic Antiproliferative Activity via Simultaneous Degradation of BRD4 and Stabilization of p53," Cancer Research, vol. 79. No. 1, 2019 (pp. 251-262).
Hoffman, H. et al., "Efficacy and Safety of Rilonacept (Interleukin-1 Trap) in Patients with Cryopyrin-Associated Periodic Syndromes," Arthritis & Rheumatism, vol. 58, No. 8, 2008 (pp. 2443-2452).
Iannello et al., "Role of Interleukin-18 in the Development and Pathogenesis of AIDS," AIDS Reviews, vol. 11, No. 3, 2009 (pp. 115-125).

(56) References Cited

OTHER PUBLICATIONS

Iconomou et al., "Systematic approaches to identify E3 ligase substrates," Biochemical Journal, vol. 473, 2016 (pp. 4083-4101).
International Search Report and Written Opinion issued by the United States Patent and Trademark Office as International Searching Authority for International Patent Application No. PCT/US2018/052181, dated Feb. 26, 2019 (14 pages).
International Search Report and Written Opinion issued by the United States Patent and Trademark Office as International Searching Authority for International Patent Application No. PCT/US2018/052242, dated Jan. 30, 2019 (8 pages).
International Search Report and Written Opinion issued by the United States Patent and Trademark Office as International Searching Authority for International Patent Application No. PCT/US2018/067304, dated Apr. 30, 2019 (13 pages).
International Search Report and Written Opinion issued by the United States Patent and Trademark Office as International Searching Authority for International Patent Application No. PCT/US2019/013481, dated Mar. 15, 2019 (9 pages).
International Search Report and Written Opinion issued by the United States Patent and Trademark Office as International Searching Authority for International Patent Application No. PCT/US2019/013491, dated Mar. 18, 2019 (9 pages).
International Search Report and Written Opinion issued by the United States Patent and Trademark Office as International Searching Authority for International Patent Application No. PCT/US2019/040462, dated Sep. 20, 2019 (14 pages).
International Search Report and Written Opinion issued by the United States Patent and Trademark Office as International Searching Authority for International Patent Application No. PCT/US2019/040520, dated Nov. 13, 2019 (11 pages).
International Search Report and Written Opinion issued by the United States Patent and Trademark Office as International Searching Authority for International Patent Application No. PCT/US2019/040545, dated Oct. 21, 2019 (8 pages).
Iriyama et al., "Clinical significance of genetic mutations of CD79B, CARD11, MYD88, and EZH2 genes in diffuse large B-cell lymphoma patients" 53rd ASH Annual Meeting, San Diego, California, Dec. 10-13, 2011 (6 pages).
Ito et al., "Identification of a primary target of thalidomide teratogenicity," Science, vol. 327, No. 5971, 2010 (pp. 1345-1350).
Kelly et al., "Selective interleukin-1 receptor-associated kinase 4 inhibitors for the treatment of autoimmune disorders and lymphoid malignancy," Journal of Experimental Medicine, vol. 212, No. 13, 2015 (pp. 2189-2201).
Kester et al., "Optimization of Benzodiazepinones as Selective Inhibitors of the X-Linked Inhibitor of Apoptosis Protein (XIAP) Second Baculovirus IAP Repeat (BIR2) Domain," Journal of Medicinal Chemistry, vol. 56, No. 20, 2013 (pp. 7788-7803).
Kim et al., "A critical role for IRAK4 kinase activity in Toll-like receptor-mediated innate immunity," Journal of Experimental Medicine, vol. 204, No. 5, 2007 (pp. 1025-1036).
Kondo et al., "Renoprotective effects of novel interleukin-1 receptor-associated kinase 4 inhibitor AS2444697 through anti-inflammatory action in 5/6 nephrectomized rats," Naunyn-Schmiedeberg's Archives of Pharmacology, vol. 387, No. 10, 2014 (pp. 909-919).
Kou et al., "Effects of RuPeng15 Powder (RPP15) on Monosodium Urate Crystal-Induced Gouty Arthritis in Rats," Evidence-Based Complementary and Alternative Medicine, vol. 2015, art. 527019, 2015 (7 pages).
Koziczak-Holbro et al., "IRAK-4 Kinase Activity Is Required for Interleukin-1 (IL-1) Receptor- and Toll-like Receptor 7-mediated Signaling and Gene Expression," Journal of Biological Chemistry, vol. 282, No. 18, 2007 (pp. 13552-13560).
Krönke et al., "Lenalidomide causes selective degradation of IKZF1 and IKZF3 in multiple myeloma cells" Science, vol. 343, No. 6168, 2014 (pp. 301-305).
Ku et al., "Selective predisposition to bacterial infections in IRAK-4-deficient children: IRAK-4-dependent TLRs are otherwise redundant in protective immunity," Journal of Experiemental Medicine, vol. 204, No. 10, 2007 (pp. 2407-2422).
Kubo-Murai et al., "IRAK-4-dependent Degradation of IRAK-1 is a Negative Feedback Signal for TLR-mediated NF-kB Activation," Journal of Biochemistry, vol. 143, 2008 (pp. 295-302).
Küppers R., IRAK inhibition to shut down TLR signaling in autoimmunity and MyD88-dependent lymphomas, Journal of Experimental Medicine, vol. 212, No. 13, 2015 (pp. 2184-2188).
Lebakken et al., "A Fluorescence Lifetime Based Binding Assay to Characterize Kinase Inhibitors," Journal of Biomedical Screening, vol. 12, No. 6, 2007 (pp. 828-841).
Lee et al., "Discovery of Clinical Candidate 1-{[2S,3S,4S)-3-ethyl-4-fluoro-5-oxopyrrolidin-2-yl]methoxy}-7-methoxyisoquinoine-6-carboxamide (PF-06650833), a Potent, Selective Inhibitor of Interleukin-1 Receptor Associated Kinase 4 9IRAK4), by Fragment-Based Drug Design," Journal of Medicinal Chemistry, vol. 60, No. 13, 2017 (pp. 5521-5542).
Li et al., "Genome-wide and functional annotation of human E3 ubiquitin ligases identifies MULAN, a mitochondrial E3 that regulates the organelle's dynamics and signaling," PLoS ONE, vol. 3, No. 1: e1487, Feb. 2008 (pp. 1-14).
Li et al., "IRAK-4: A novel member of the IRAK family with the properties of an IRAK-kinase," PNAS, vol. 99, No. 8, 2002 (pp. 5567-5572).
Li, "IRAK4 inTLR/IL-1R signaling: Possible clinical applications," European Journal of Immunology, vol. 38, 2008 (pp. 614-618).
Li, N. et al., "Targeting interleukin-1 receptor-associated kinase for human hepatocellular carcinoma," Journal of Experimental and Clinical Cancer Research, vol. 35, No. 1, 2016 (pp. 140-150).
Lim et al. "Discovery of 5-Amino-N-(1H-pyrazol-4-yl)pyrazolo[1,5-a]pyrimidine-3-carboxamide Inhibitors of IRAK4," ACS Medicinal Chemistry Letters, 2015, vol. 6., No. 6, 2015 (pp. 683-688).
Lin et al., "Helical assembly in the MyD88-IRAK4-IRAK2 complex in TLR /IL-1R signalling," Nature, vol. 465, No. 17, 2010 (pp. 885-891).
Lu et al., "Hijacking the E3 Ubiquitin Ligase Cereblon to Efficiently Target BRD4," Chemistry & Biology, vol. 22, No. 6. 2015 (pp. 755-763).
Lu et al., "The myeloma drug lenalidomide promotes the cereblon-dependent destruction of Ikaros proteins," Science, vol. 343, No. 6168 2014 (pp. 305-309).
Lust et al., "Induction of a Chronic Disease State in patients With Smoldering of Indolent Multiple Myeloma by Targeting Interleukin 1β-Induced Interleukin 6 Production and the Myeloma Proliferative Component," Mayo Clinic Proceedings, vol. 84, No. 2, 2009 (pp. 114-122).
Martinon et al., "Gout-associated uric acid crystals activate the NALP3 inflammasome," Nature, vol. 440, 2006 (pp. 237-241).
Maschera et al., "Overexpression of an enzymatically inactive interleukin-1-receptor-associated kinase activates nuclear factor-κB," Biochemical Journal, vol. 339, 1999 (pp. 227-231).
McElroy et al., "Discovery and hit-to-lead optimization of 2,6-diaminopyrimidine Inhibitors of interleukin-1 receptor-associated kinase 4," Bioorganic and Medicinal Chemistry Letters, vol. 25, No. 9, 2015 (pp. 1836-1841).
McElroy et al., "Potent and Selective Amidopyrazole Inhibitors of IRAK4 That Are Efficacious in a Rodent Model of Inflammation," ACS Medicinal Chemistry Letters, vol. 6, No. 6, 2015 (pp. 677-682).
Muller et al. "Amino-Substituted Thalidomide Analogs: Potent Inhibitors of TNF-α Production," Bioorganic & Medicinal Chemistry Letters, vol. 9, 1999 (pp. 1625-1630).
Ngo et al., "Oncogenically active MYD88 mutations in human lymphoma," Nature, vol. 470, No. 7332, 2011 (pp. 115-119).
Ohoka et al., "In Vivo Knockdown of Pathogenic Proteins via Specific and Nongenetic Inhibitor of Apoptosis Protein (IAP)-dependent Protein Erasers (SNIPERs)," Journal of Biological Chemistry, vol. 292, No. 11, Mar. 2017 (pp. 4556-4570).
Okazaki, et al., "A rheostat for immune responses: the unique properties of PD-1 and their advantages for clinical application," Nature Immunology, vol. 14,, No. 12, 2013 (pp. 1212-1218).

(56) References Cited

OTHER PUBLICATIONS

Picard et al., "Clinical features and outcome of patients with IRAK-4 and MyD88 deficiency," Medicine (Baltimore), vol. 89, No. 6, 2010 (pp. 043-25).
Picard el al., "Inherited human IRAK-4 deficiency: an update," Immunologic Research, 2007, vol. 38, No. 1-3, 2007 (pp. 347-352).
Piya et al., "BRD4 Proteolysis Targeting Chimera (PROTAC) Leads to Sustained Degradation of BRD4 with Broad Activity Against Acute Leukemias and Overcomes Stroma Mediated Resistance By Modulating Surface Expression of CXCR4," Blood, American Society of Hematology, vol. 126, No. 23, 2015, (pp. 675-676).
Powers et al., "Discovery and initial SAR of inhibitors of interleukin-1 receptor-associated kinase-4," Bioorganic & Medicinal Chemistry Letters, vol. 16, No. 11, 2006 (pp. 2842-2845).
Priyadarshini et al., "Copper catalyzed oxidative cross-coupling of aromatic amines with 2-pyrrolidinone: a facile synthesis of N-aryl-r-amino-r-lactams," Tetrahedron, vol. 70, No. 36, 2014 (pp. 6068-6074).
Pubmed Compound Summary for CID 101524675, "(2R)-3-Fluoro-2-(2-methylpropyl)-3-phenyl-1,3-azasilinan-6-one," U.S. National Library of Medicine, created Dec. 18, 2015, https://pubchem.ncbi.nlm.nih.gov/compound/101524675. Date Accessed: Sep. 5, 2019 (5 pages).
Pubmed Compound Summary for CID 102164987, "3-[(4S)-2,5-Dioxo-4-phenylimidazolidine-1-yl]-2,6-piperidinedione," U.S. National Library of Medicine, created Dec. 24, 2015, https://pubchem.ncbi.nlm.nih.gov/compound/102164987. Date Accessed: Feb. 25, 2020 (7 pages).
Pubmed Compound Summary for CID 115370667, "5-(2-Oxoimidazolidin-1-yl)piperidin-2-one." U.S. National Library of Medicine, created Jan. 29, 2016, https://pubchem.ncbi.nlm.nih.gov/compound/115370667. Date Accessed: Feb. 25, 2020 (10 pages).
Pubmed Compound Summary for CID 138728787, "3-(6-Ethylpyrido[2,3-b]indol-9-yl)piperidine-2,6-dione," U.S. National Library of Medicine, created Jul. 20, 2019, https://pubchem.ncbi.nlm.nih.gov/compound/138728787. Date Accessed: Sep. 5, 2019 (6 pages).
Pubmed Compound Summary for CID 17607528, "4-(Carbazol-9-ylmethyl)-1,3-oxazolidin-2-one," U.S. National Library of Medicine, Nov. 13, 2007, https://pubchem.ncbi.nlm.nih.gov/compound/17607528. Date Accessed: Feb. 25, 2020 (6 pages).
Pubmed Compound Summary for CID 63661260,"5-[2-(1-Chloroethyl)benzimidazol-1-yl]piperidin-2-one," U.S. National Library of Medicine, created Oct. 22, 2012, https://pubchem.ncbi.nlm.nih.gov/compound/63661260. Date Accessed: Sep. 4, 2019 (6 pages).
Pubmed Compound Summary for CID 63661460, "6-Oxo-1-(6-oxopiperidin-3-yl)piperidine-3-carboxylic acid," U.S. National Library of Medicine, created Oct. 22, 2012, https://pubchem.ncbi.nlm.nih.gov/compound/63661460. Date Accessed: Feb. 25, 2020 (7 pages).
Pubmed Compound Summary for CID 65967733, "3-(2,5-Dioxo-3-phenylpyrrolidin-1-yl)piperidine-2,6-dione," U.S. National Library of Medicine, created Dec. 24, 2015, https://pubchem.ncbi.nlm.nih.gov/compound/65967733. Date Accessed: Feb. 25, 2020 (7 pages).
Pubmed Compound Summary for CID 65968760, "1-(2,6-Dioxopiperidin-3-yl)benzimidazole-5-carboxylic acid," U.S. National Library of Medicine, created Oct. 24, 2012, https://pubchem.ncbi.nlm.nih.gov/compound/65968760. Date Accessed: Sep. 4, 2019 (6 pages).
Pubmed Compound Summary for CID 67258040, "[1-(9H-Fluoren-9-yl)-1-(6-oxopiperidin-3-yl)ethyl] hydrogen carbonate," U.S. National Library of Medicine, Nov. 30, 2012, https://pubchem.ncbi.nlm.nih.gov/compound/67258040. Date Accessed: Feb. 25, 2020 (9 pages).
Pubmed Compound Summary for CID 83543479, "5(Aminomethyl)-5-(1H-indol-3-yl)piperidin-2-one," U.S. National Library of Medicine, created Oct. 20, 2014, https://pubchem.ncbi.nlm.nih.gov/compound/83543479. Date Accessed: Feb. 25, 2020 (6 pages).
Pubmed Compound Summary for CID 84036945, '1-Piperidin-3-yl-3H-indol-2-one, U.S. Library of Medicine, created Oct. 20, 2014, https://pubchem.ncbi.nlm.nih.gov/compound/84036945. Date Accessed: Feb. 25, 2020 (7 pages).
Pubmed Compound Summary for CID 110491408, '3-(5-Amino-2-oxo-3H-benzimidazol-1-yl)piperidine-2,6-dione, U.S. Library of Medicine, created Jan. 18, 2016, https://pubchem.ncbi.nlm.nih.gov/compound/110491408. Date Accessed: Feb. 25, 2020 (7 pages).
Pubmed Compound Summary for CID 110491555, '3-(6-Amino-2-oxo-3H-benzimidazol-1-yl)piperidine-2,6-dione, U.S. Library of Medicine, created Jan. 18, 2016, https://pubchem.ncbi.nlm.nih.gov/compound/110491555. Date Accessed: Feb. 25, 2020 (7 pages).
Raina et al., "Chemical Inducers of Targeted Protein Degradation," Journal of Biological Chemistry, vol. 285, No. 15, 2010 (pp. 11057-11060).
Ramirez, et al., "Defining causative factors contributing in the activation of hedgehog signaling in diffuse large B-cell lymphoma" Leukemia Research, vol. 36, No. 10, 2012 (pp. 1267-1273).
Rokosz et al., "Kinase inhibitors as drugs for chronic inflammatory and immunological diseases: progress and challenges," Expert Opinions on Therapeutic Targets, vol. 12, No. 7, 2008 (pp. 883-903).
Ronnebaum et al., "Synthesis of 1, 2, 3-triazole 'click' analogues of thalidomide," Tetrahedron, vol. 72, No. 40, 2016 (pp. 6136-6141).
Ross et al., "Bispecific T cell engager (BiTE®) antibody constructs can mediate bystander tumor cell killing", PLoS ONE, vol. 12, No. 8, (e0183390), Aug. 24, 2017, https://doi.org/10.1371/journal.pone.0183390. Date Accessed: Feb. 12, 2020 (24 pages).
Rostovtsev et al., "A Stepwise Huisgen Cycloaddition Process: Copper(I)-Catalyzed Regioselective "Ligation" of Azides and Terminal Alkynes," Angewandte Chemie International Edition, vol. 41, No. 14, Jul. 2002, (pp. 2596-2599).
Schnnekloth el al., "Chemical approaches to controlling intracellular protein degradation," Chembiochem: a European Journal of Chemical Biology, vol. 6, No. 1, 2005 (pp. 40-46).
Scott et al., "Discovery and Optimization of Pyrrolopyrimidine Inhibitors of Interleukin-1 Receptor Associated Kinase 4 (IRAK4) for the Treatment of Mutant MYD88L265P Diffuse Large B-Cell Lymphoma," Journal of Medicinal Chemistry, 2017, vol. 60, No. 24, 2017 (pp. 10071-10091).
Seganish et al., "Discovery and Structure Enabled Synthesis of 2,6-diaminopyrimidine-4-one IRAK4 Inhibitors," ACS Medicinal Chemistry Letters, vol. 6, No. 8, 2015 (pp. 942-947).
Seganish et al., "Initial optimization and series evolution of diaminopyrimidine inhibitors of interleukin-1 receptor associated kinase 4," Bioorganic and Medicinal Chemistry Letters, vol. 25, No. 16, 2015 (pp. 3203-3207).
Sen et al., "Transcriptional signaling by double-stranded RNA: role of TLR3," Cytokine & Growth Factor Reviews, vol. 16, No. 1, 2005 (pp. 1-14).
Shanmugasundaram, K. et al., "A modular PROTAC design for target destruction using a degradation signal based on a single amino acid," Journal of Biochemical Chemistry, Sep. 11, 2019, https://www.jbc.org/content/early/2019/09/11/jbc.AC119.010790.full.pdf. Date Accessed: Feb. 11, 2020 (10 pages).
Smith et al., "Identification of quinazoline based inhibitors of IRAK4 for the treatment of inflammation," Bioorganic and Medicinal Chemistry Letters, vol. 27, No. 12, 2017 (pp. 2721-2726).
So et al., "A pilot study of IL-1 inhibition by anakinra in acute gout," Arthritis Research & Therapy, vol. 9, No. 2, 2007 (pp. 1-6).
Song et al., "The kinase activities of interleukin-e receptor associated kinase (IRAK)-1 and 4 are redundant in the control of inflammatory cytokine expression in human cells," Molecular Immunology, vol. 46, No. 7, 2009 (pp. 1458-1466).
Spradin et al., "Harnessing the Anti-Cancer Natural Product Nimbolide for Targeted Protein Degradation," bioRxiv.org (doi: https://doi.org/10.1101/436998), First Posted, Oct. 15, 2018, https://www.biorxiv.org/content/biorxiv/early/2019/04/09/436998.full.pdf. Date Accessed, Oct. 3, 2019 (41 pages).
Spratt et al., "RBR E3 ubiquitin ligases: new structures, new insights, new question," Biochemical Journal, vol. 458, Pt. 3, 2014 (pp. 421-437).
Stewart et al., "Efforts toward elucidating Thalidomide's molecular target: an expedient synthesis of the first Thalidomide biotin analogue," Organic & Biomolecular Chemistry, vol. 8, No. 18, 2010, (pp. 4059-4062).

(56) References Cited

OTHER PUBLICATIONS

Sun et al., "Carbohydrate and protein immobilization onto solid surfaces by sequential Diels-Alder and azide-alkyne cycloadditions," Bioconjugate Chemistry, vol. 17, No. 1, 2006 (pp. 52-57).
Suzuki et al., "IRAK-4 as the central HR signaling mediator in innate immunity," TRENDS in Immunology, vol. 23, No. 10, 2002 (pp. 503-506).
Suzuki et al., "Severe impairment of interleukin-1 and Toll-like receptor signalling in mice lacking IRAK-4," Nature, vol. 416, No. 6882, 2002 (pp. 750-756).
Swantek et al., "IL-1 Receptor-Associated Kinase Modulates Host Responsiveness to Endotoxin," Journal of Immunology, vol. 164, 2000 (pp. 4301-4306).
Terkeltaub et al., "The interleukin 1 inhibitor rilonacept in treatment of chronic gouty arthritis: results of a placebo-controlled, monosequence crossover, non-randomised, single-blind pilot study," Annals of Rheumatic Diseases, vol. 68, No. 10, 2009 (pp. 1613-1617).
Terkeltaub, R., "Update on gout: new therapeutic strategies and options," Nature, vol. 6, 2010 (pp. 30-38).
Toogood, P., "Small molecule immuno-oncology therapeutic agents," Bioorganic & Medicinal Chemistry Letters, vol. 28, No. 3, 2017 (pp. 319-329).
Torres el al., "Hyperalgesia, synovitis and multiple biomarkers of inflammation are suppressed by interleukin 1 inhibition in a novel animal model of gouty arthritis," Annals of Rheumatic Diseases, vol. 68, 2009 (pp. 1602-1608).
Toure et al., "Small-Molecule PROTACS: New Approaches to Protein Degradation," Angewandte Chemie International Edition, vol. 55, No. 6, 2016 (pp. 1966-1973).
Treon, et al., "Whole genome sequencing reveals a widely expressed mutation (MYD88 L265P) with oncogenic activity in Waldenström's Macroglobulinemia" 53rd ASH Annual Meeting, San Diego, California, Dec. 10-13, 2011 [abstract] (1 page).
Troseid, M. "The role of interleukin-18 in the metabolic syndrome," Cardiovascular Diabetology, vol. 9, No. 11, 2009 (pp. 1-8).
Tumey et al., "Identification and optimization of indolo[2,3-c]quinoline inhibitors of IRAK4," Bioorganic and Medicinal Chemistry Letters, vol. 24, No. 9, 2014 (pp. 2066-2072).
Uehara et al., "Selective degradation of splicing factor CAPERα by anticancer sulfonamides," Nature Chemical Biology, vol. 13, No. 6, 2017 (pp. 675-680).
Varfolomeev et al., "IAP antagonists induce autoubiquitination of c-IAPs, NF-kappaB activation, and TNFalpha-dependent apoptosis," Cell, vol. 131, No. 4, 2007 (pp. 669-681).
Vollmer, S., "The mechanism of activation of IRAK1 and IRAK4 by interleukin-1 and Toll-like receptor agonists," The Biochemical Journal, vol. 474, No. 12, 2017 (pp. 2027-2038).
Wang et al., "Crystal Structure of IRAK-4 Kinase in Complex with Inhibitors: Serine/Threonine Kinase with Tyrosine as a Gatekeeper," Structure, vol. 14, No. 12, 2006 (pp. 1835-1844).
Wang et al., "Discovery of potent, selective, and orally bioavailable inhibitors of interleukin-1 receptor-associated kinase 4," Bioorganic & Medicinal Chemistry Letters, vol. 25, No. 23, 2015 (pp. 5546-5550).
Wang et al., "IRAK-4 Inhibitors for Inflammation," Current Topics in Medicinal Chemistry, vol. 9, No. 8, 2009 (pp. 724-737).
Wang el al., "Roles of F-box proteins in cancer," Nature Reviews. Cancer, vol. 14, No. 4, 2014 (pp. 233-247).
Ward et al., "Covalent Ligand Screening Uncovers a RNF4 E3 Ligase Recruiter for Targeted Protein Degradation Applications," bioRxiv.org (doi: https://doi.org/10.1101/439125) First Posted, Oct. 16, 2018, https://www.biorxiv.org/content/biorxiv/early/2018/11/16/439125.full.pdf. Date Accessed, Oct. 3, 2019 (24 pages).
Weaver, A. "Epidemiology of gout," Cleveland Clinic Journal of Medicine, vol. 75, suppl. 5, 2008 (pp. S9-S12).
Winter et al., "Selective Target Protein Degradation via Phthalimide Conjugation,"Science, vol. 348, No. 6241, 2015 (pp. 1376-1381).
Xu, et al., "A somatic variant in MYD88 (L256P) revealed by whole genome sequencing differentiates lymphoplasmacytic lymphoma from marginal zone lymphomas" 53rd ASH Annual Meeting, San Diego, California, Dec. 10-13, 2011 (1 page).
Yang et al., "Disruption of MYD88 pathway signaling leads to loss of constitutive IRAK1, NK-κB and JAK/STAT signaling and induces apoptosis of cells expressing the MYD88 L265P mutation in Waldenström's Macroglobulinemia" 53rd ASH Annual Meeting, San Diego, California, Dec. 10-13, 2011 (1 page).
Yang et al., "Exploiting synthetic lethality for the therapy of ABC diffuse large B cell lymphoma" Cancer Cell, vol. 21, No. 6, 2012 (pp. 723-737).
Zhang et al., "Electrophilic PROTACs that degrade nuclear proteins by engaging DCAF16," bioRxiv.org (doi: https://doi.org/10.1101/443804), First Posted, Oct. 15, 2018, https://www.biorxiv.org/content/biorxiv/early/2018/10/15/443804.full.pdf. Date Accessed, Oct. 3, 2019 (38 pages).
Zhang et al., "Constitutive IRAK4 Activation Underlies Poor Prognosis and Chemoresistance in Pancreatic Ductal Adenocarcinoma," Clinical Cancer Research: an Official Journal of the American Association for Cancer Research, vol. 23, No. 7, 2017 (pp. 1748-1759).
Zhou et al., "Targets of curcumin," Current Drug Targets, vol. 12, No. 3, 2011 (pp. 332-347).
Zou et al., "PD-L1 (B7-H1) and PD-1 Pathway Blockade for Cancer Therapy: Mechanisms, Response Biomarkers and Combinations," Science Translatonal Medicine, vol. 8., No. 328, Mar. 2016 (pp. 1-34).
Charrier et al., "Desulfonylative Radical Ring Closure onto Aromatics. A Modular Route to Benzazepin-2-ones and 5-Arylpiperidin-2-ones," Org. Lett. 2012, 14(8): 2018-2021.
Devi et al. "Medicinal Attributes of Imidazo[1,2-a]pyridine Derivatives: An Update," Curr Top Med Chem, 2016, 16(26):2963-2994.
Heightman et al., "Structure-Activity and Structure-Conformation Relationships of Aryl Propionic Acid Inhibitors of the Kelch-like ECH-Associated Protein 1/Nuclear Factor Erythroid 2-Related Factor 2 (KEAP1/NRF2) Protein-Protein Interaction," J. Med. Chem., 2019, 62(9): 4683-4702.
Kargbo, "Protac Degradation of IRAK4 for the Treatment of Cancer," ACS Med. Chem. Lett., 2019, 10(10):1370-1371.
Lu et al., "Discovery of a Keap1-dependent peptide PROTAC to knockdown Tau by ubiquitination-proteasome degradation pathway," Euro. J. Med. Chem., 2018, 146:251-9.
Ohoka et al., "Development of Small Molecule Chimeras That Recruit AhR E3 Ligase to Target Proteins,"ACS Chem. Biol. 2019, 14(12):2822-2832.
PCT International Preliminary Report on Patentability from PCT/US2018/067304, dated Jun. 30, 2020.
PCT International Preliminary Report on Patentability from PCT/US2019/040462, dated Jan. 21, 2021.
PCT International Search Report and Written Opinion from PCT/US2020/026869, dated Jul. 27, 2020.
PCT International Search Report and Written Opinion from PCT/US2020/036913, dated Oct. 26, 2020.
PCT International Search Report and Written Opinion from PCT/US2020/036916, dated Oct. 26, 2020.
PCT International Search Report and Written Opinion from PCT/US2020/036918, dated Oct. 26, 2020.
PCT International Search Report and Written Opinion from PCT/US2020/036921, dated Oct. 26, 2020.
PCT International Search Report and Written Opinion from PCT/US2020/042105, dated Nov. 20, 2020.
PCT International Search Report and Written Opinion from PCT/US2020/042534, dated Oct. 26, 2020.
PCT International Search Report and Written Opinion from PCT/US2020/064061, dated Apr. 9, 2021.
PCT International Search Report and Written Opinion from PCT/US2020/065752, dated Mar. 25, 2021.
PCT International Search Report and Written Opinion from PCT/US2020/066859, dated May 4, 2021.
Rusnac et al., "Recognition of the Diglycine C-End Degron by CRL2 KLHDC2 Ubiquitin Ligase," Mol. Cell. 2018, 72(5):813-822.e4.

(56) References Cited

OTHER PUBLICATIONS

Tong et al., "Targeted Protein Degradation via a Covalent Reversible Degrader Based on Bardoxolone", ChemRxiv. First Posted Online: Apr. 2, 2020.

* cited by examiner

FIG. 5

Cellular Viability (CTG; $IC_{50}$; µM)
OCI-LY10 (MYD88 L265P): 0.19
Daudi (MYD88 WT): 0.33

Dose-dependent IRAK4 knockdown was observed in wild-type mouse skin and spleen with treatment of I-417

IRAK DEGRADERS AND USES THEREOF

CROSS-REFERENCE TO RELATED APPLICATIONS

This application claims the benefit of U.S. Provisional App. No. 62/774,051, filed on Nov. 30, 2018, U.S. Provisional App. No. 62/788,460, filed on Jan. 4, 2019, U.S. Provisional App. No. 62/793,992, filed on Jan. 18, 2019, U.S. Provisional App. No. 62/826,743, filed on Mar. 29, 2019, U.S. Provisional App. No. 62/831,007, filed on Apr. 8, 2019, U.S. Provisional App. No. 62/851,427, filed on May 22, 2019, U.S. Provisional App. No. 62/868,574, filed on Jun. 28, 2019, U.S. Provisional App. No. 62/875,347, filed on Jul. 17, 2019, and U.S. Provisional App. No. 62/879,117, filed on Jul. 26, 2019, the content of each of which is hereby incorporated by reference.

TECHNICAL FIELD OF THE INVENTION

The present invention relates to compounds and methods useful for the modulation of one or more interleukin-1 receptor-associated kinases ("IRAK") via ubiquitination and/or degradation by compounds according to the present invention. The invention also provides pharmaceutically acceptable compositions comprising compounds of the present invention and methods of using said compositions in the treatment of various disorders.

BACKGROUND OF THE INVENTION

Ubiquitin-Proteasome Pathway (UPP) is a critical pathway that regulates key regulator proteins and degrades misfolded or abnormal proteins. UPP is central to multiple cellular processes, and if defective or imbalanced, it leads to pathogenesis of a variety of diseases. The covalent attachment of ubiquitin to specific protein substrates is achieved through the action of E3 ubiquitin ligases.

There are over 600 E3 ubiquitin ligases which facilitate the ubiquitination of different proteins in vivo, which can be divided into four families: HECT-domain E3s, U-box E3s, monomeric RING E3s and multi-subunit E3s. See generally Li et al. (PLOS One, 2008, 3, 1487) titled "Genome-wide and functional annotation of human E3 ubiquitin ligases identifies MULAN, a mitochondrial E3 that regulates the organelle's dynamics and signaling."; Berndsen et al. (Nat. Struct. Mol. Biol., 2014, 21, 301-307) titled "New insights into ubiquitin E3 ligase mechanism"; Deshaies et al. (Ann. Rev. Biochem., 2009, 78, 399-434) titled "RING domain E3 ubiquitin ligases."; Spratt et al. (Biochem. 2014, 458, 421-437) titled "RBR E3 ubiquitin ligases: new structures, new insights, new questions."; and Wang et al. (Nat. Rev. Cancer., 2014, 14, 233-347) titled "Roles of F-box proteins in cancer."

UPP plays a key role in the degradation of short-lived and regulatory proteins important in a variety of basic cellular processes, including regulation of the cell cycle, modulation of cell surface receptors and ion channels, and antigen presentation. The pathway has been implicated in several forms of malignancy, in the pathogenesis of several genetic diseases (including cystic fibrosis, Angelman's syndrome, and Liddle syndrome), in immune surveillance/viral pathogenesis, and in the pathology of muscle wasting. Many diseases are associated with an abnormal UPP and negatively affect cell cycle and division, the cellular response to stress and to extracellular modulators, morphogenesis of neuronal networks, modulation of cell surface receptors, ion channels, the secretory pathway, DNA repair and biogenesis of organelles.

Aberrations in the process have recently been implicated in the pathogenesis of several diseases, both inherited and acquired. These diseases fall into two major groups: (a) those that result from loss of function with the resultant stabilization of certain proteins, and (b) those that result from gain of function, i.e. abnormal or accelerated degradation of the protein target.

The UPP is used to induce selective protein degradation, including use of fusion proteins to artificially ubiquitinate target proteins and synthetic small-molecule probes to induce proteasome-dependent degradation. Bifunctional compounds composed of a target protein-binding ligand and an E3 ubiquitin ligase ligand, induced proteasome-mediated degradation of selected proteins via their recruitment to E3 ubiquitin ligase and subsequent ubiquitination. These drug-like molecules offer the possibility of temporal control over protein expression. Such compounds are capable of inducing the inactivation of a protein of interest upon addition to cells or administration to an animal or human, and could be useful as biochemical reagents and lead to a new paradigm for the treatment of diseases by removing pathogenic or oncogenic proteins (Crews C, Chemistry & Biology, 2010, 17 (6):551-555; Schnnekloth J S Jr., Chembiochem, 2005, 6 (1):40-46).

An ongoing need exists in the art for effective treatments for disease, especially hyperplasias and cancers, such as multiple myeloma. However, non-specific effects, and the inability to target and modulate certain classes of proteins altogether, such as transcription factors, remain as obstacles to the development of effective anti-cancer agents. As such, small molecule therapeutic agents that leverage E3 ligase mediated protein degradation to target cancer-associated proteins such as interleukin-1 receptor-associated kinases ("IRAK") hold promise as therapeutic agents. Accordingly, there remains a need to find compounds that are IRAK degraders useful as therapeutic agents.

SUMMARY OF THE INVENTION

The present application relates novel bifunctional compounds, which function to recruit IRAK kinases to E3 Ubiquitin Ligase for degradation, and methods of preparation and uses thereof. In particular, the present disclosure provides bifunctional compounds, which find utility as modulators of targeted ubiquitination of IRAK kinases, which are then degraded and/or otherwise inhibited by the bifunctional compounds as described herein. Also provided are monovalent compounds, which find utility as inducers of targeted ubiquitination of IRAK kinases, which are then degraded and/or otherwise inhibited by the monovalent compounds as described herein. An advantage of the compounds provided herein is that a broad range of pharmacological activities is possible, consistent with the degradation/inhibition of IRAK kinases. In addition, the description provides methods of using an effective amount of the compounds as described herein for the treatment or amelioration of a disease condition, such as cancer, e.g., multiple myeloma.

The present application further relates to targeted degradation of IRAK kinases through the use of bifunctional molecules, including bifunctional molecules that link a cereblon-binding moiety to a ligand that binds IRAK kinases.

It has now been found that compounds of this invention, and pharmaceutically acceptable compositions thereof, are effective as degraders of IRAK kinases. Such compounds have the general formula I:

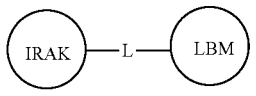

I or a pharmaceutically acceptable salt thereof, wherein each variable is as defined and described herein.

It has also now been found that compounds of this invention, and pharmaceutically acceptable compositions thereof, are effective as degraders of IRAK kinases. Such compounds have the general formula V:

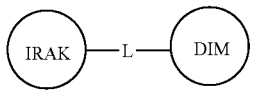

V or a pharmaceutically acceptable salt thereof, wherein each variable is as defined and described herein.

Compounds of the present invention, and pharmaceutically acceptable compositions thereof, are useful for treating a variety of diseases, disorders or conditions, associated with regulation of signaling pathways implicating IRAK kinases. Such diseases, disorders, or conditions include those described herein.

Compounds provided by this invention are also useful for the study of IRAK enzymes in biological and pathological phenomena; the study of intracellular signal transduction pathways occurring in bodily tissues; and the comparative evaluation of new IRAK inhibitors or IRAK degraders or other regulators of kinases, signaling pathways, and cytokine levels in vitro or in vivo.

BRIEF DESCRIPTION OF THE FIGURES

FIG. 5 shows the results (CTG; $IC_{50}$ in μM) of the cellular viability assay using degrader I-30 with OCI-LY10 and Daudi.

(C), and LPS (TLR4)-induced IL-1β (D) showing DMSO control (%) (y-axis) versus concentration (log μM) (x-axis) in human whole blood.

Figure 17:
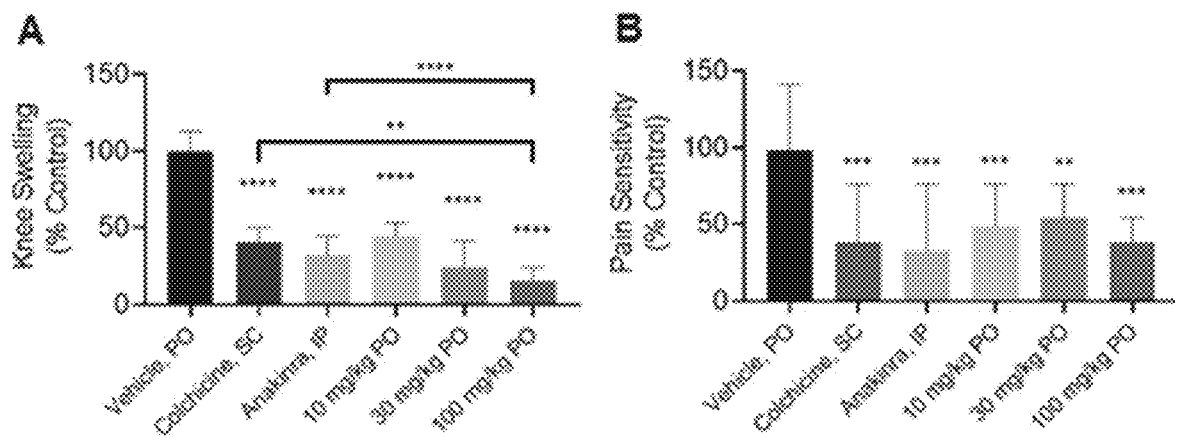

FIG. 17 includes graphical images of MSU induced gouty arthritis anti-inflammatory and analgesic results showing knee swelling (% control) (x-axis) and (Vehicle PO; colchicine SC; anakinra IP; and PO doses of degrader I-75: 10 mg/kg; 30 mg/kg; and 100 mg/kg) (x-axis) (A); and pain sensitivity (% control) (x-axis) and (Vehicle PO; colchicine SC; anakinra IP; and PO doses of degrader: 10 mg/kg; 30 mg/kg; and 100 mg/kg) (x-axis) (B).

Figure 18:
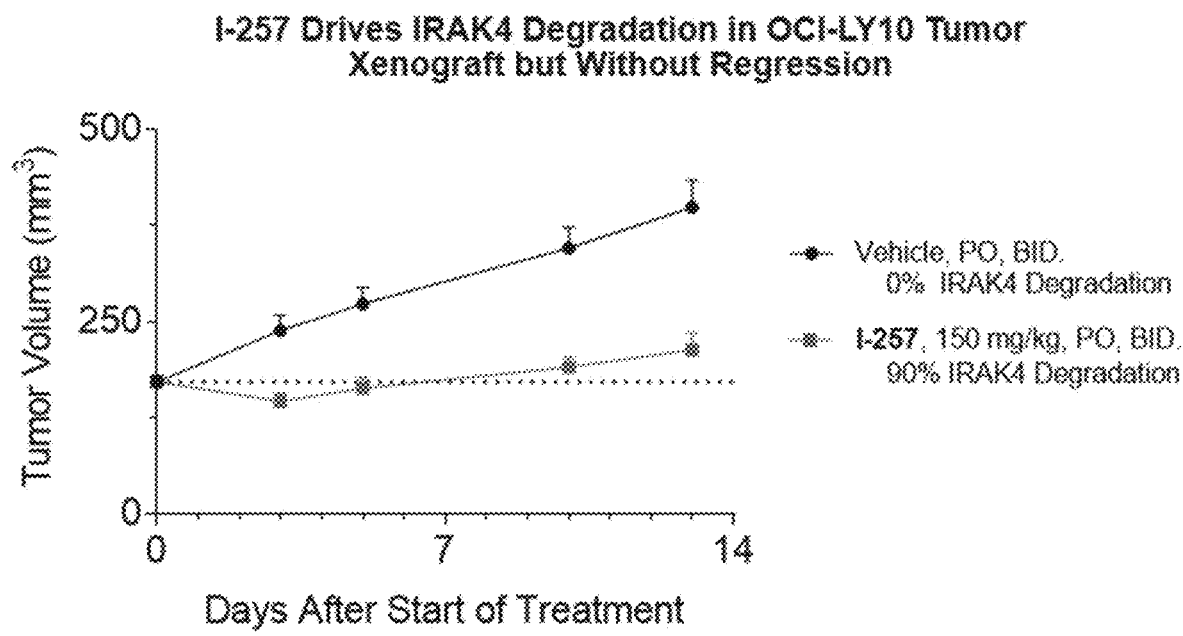

FIG. 18 is a graphical image of IRAK4 degradation in OCI-LY10 tumor xenograft without regression for vehicle (PO, BID) and degrader I-257 (PO, BID, 150 mg/kg), showing tumor volume (mm$^3$) (y-axis) versus dosing interval (days after start of treatment) (x-axis).

Figure 19:
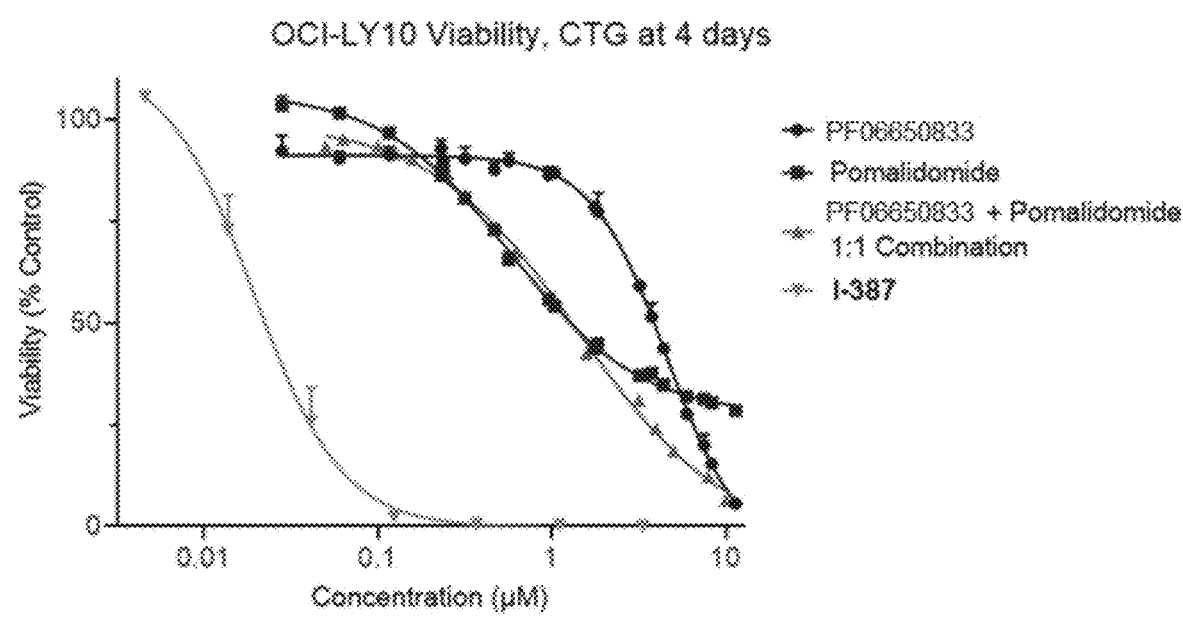

FIG. 19 is a graphical image of viability results using PF-06650833, pomalidoamide, 1:1 PF-06650833:pomalidomide, and degrader I-387 showing viability (% control) (y-axis) versus concentration (μM) (x-axis) for OCI-LY10 (MYD88 L265P, CD79 mutant) cells.

Figure 20:
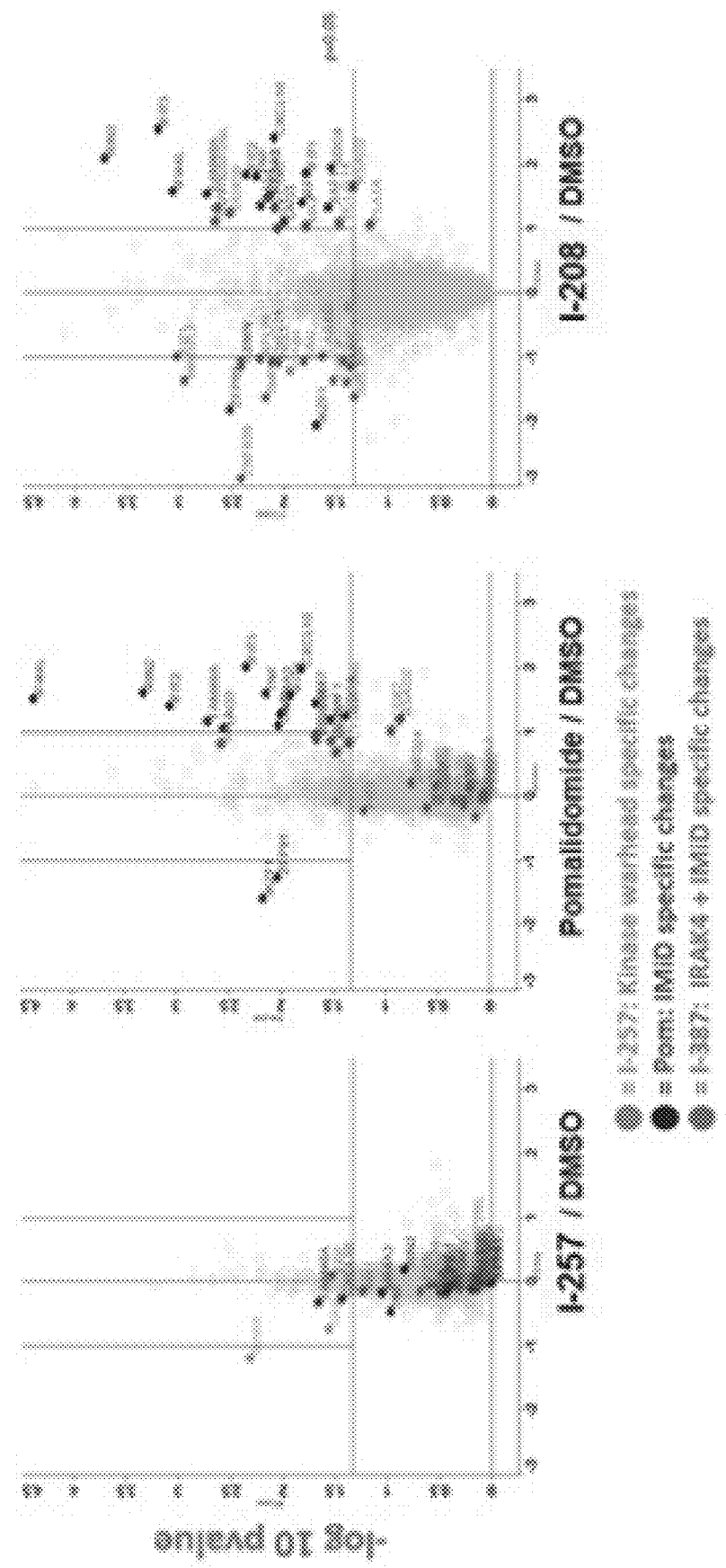

FIG. 20 includes transcriptome scatterplots of IFN signaling results showing −log 10 p-values of I-257, pomalidomide, and I-208 in DMSO (y-axis).

Figure 21:
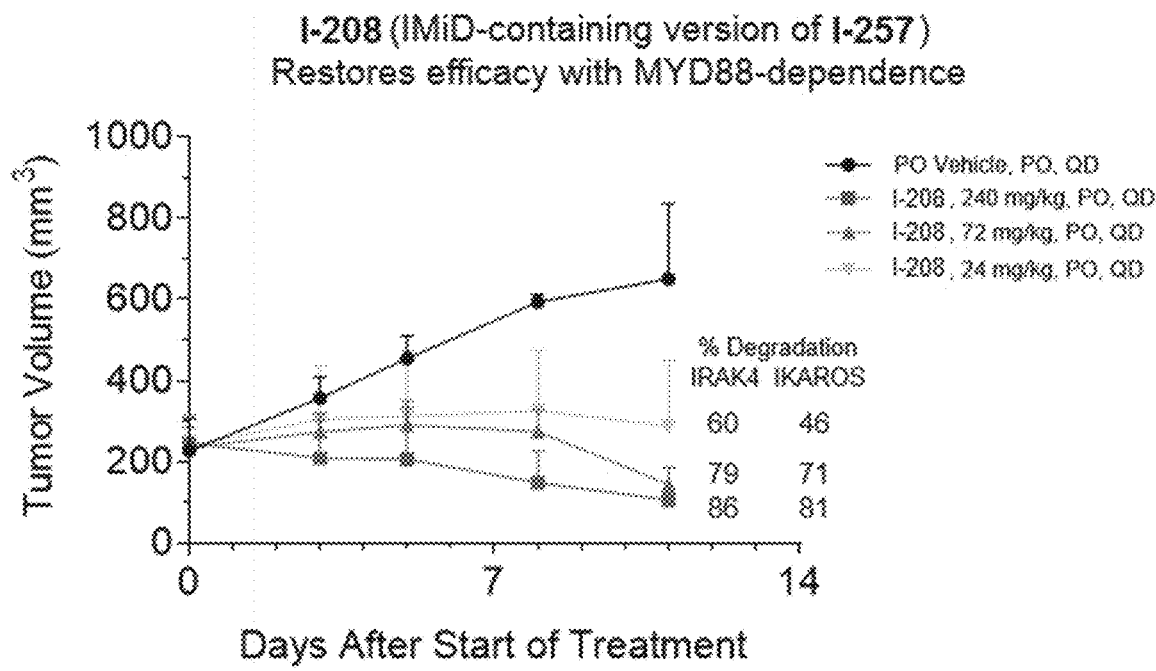

FIG. 21 is a graphical image of IRAK4 and Ikaros degradation in OCI-LY10 tumor xenograft with regression for vehicle (PO, QD) and degrader I-208 (PO, QD; 24, 72, and 240 mg/kg), showing tumor volume (mm$^3$) (y-axis) versus dosing interval (days after start of treatment) (x-axis).

Figure 22:
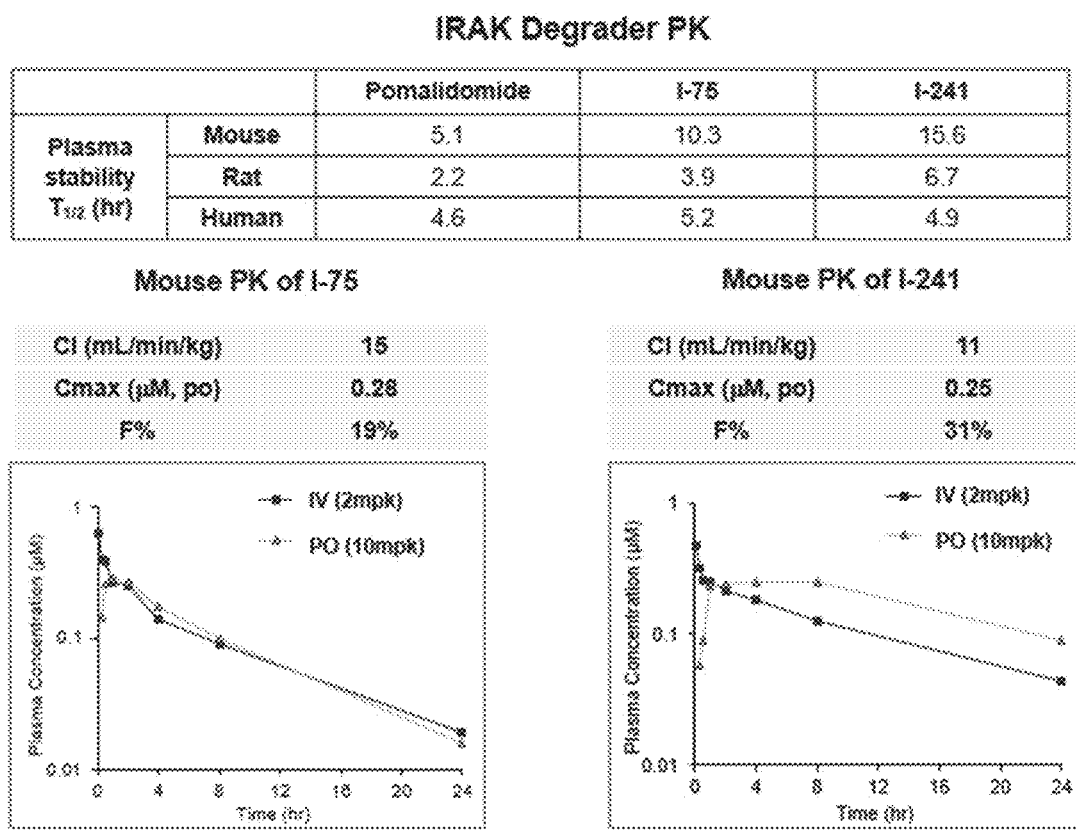

FIG. 22 shows pharmacokinetic results of I-75 and I-241.

Figure 23:
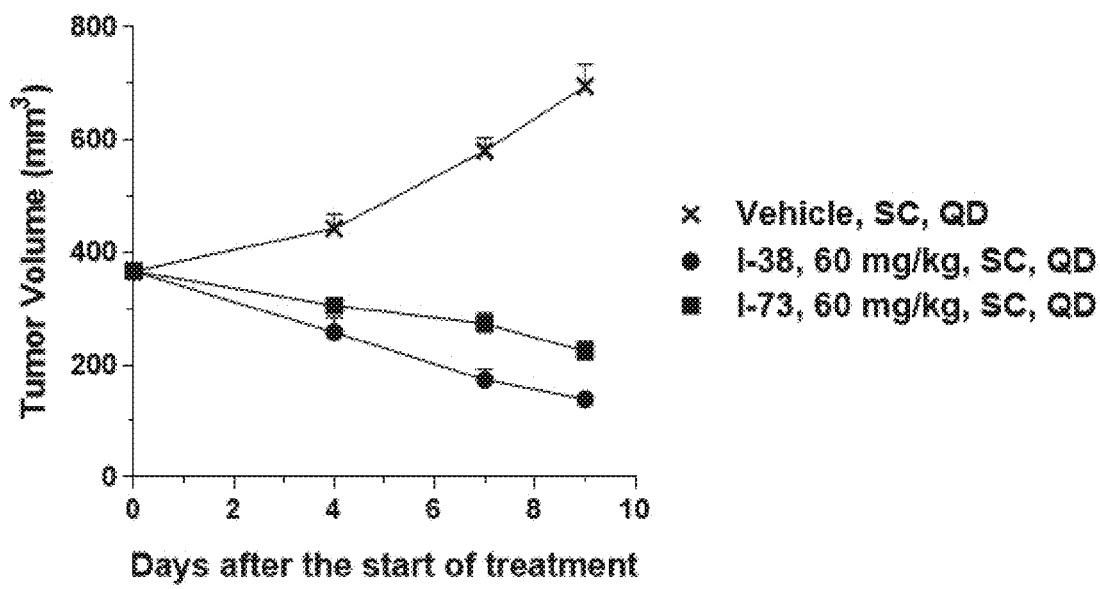

FIG. 23 is a graphical image of xenograph results for vehicle (SC, QD) and degrader I-38 and I-73 (SC, QD: 60 mg/kg) showing tumor volume (mm$^3$) (y-axis) versus dosing interval (days after start of treatment) (x-axis) for OCI-LY10 (MYD88 mutant) cells.

Figure 24:
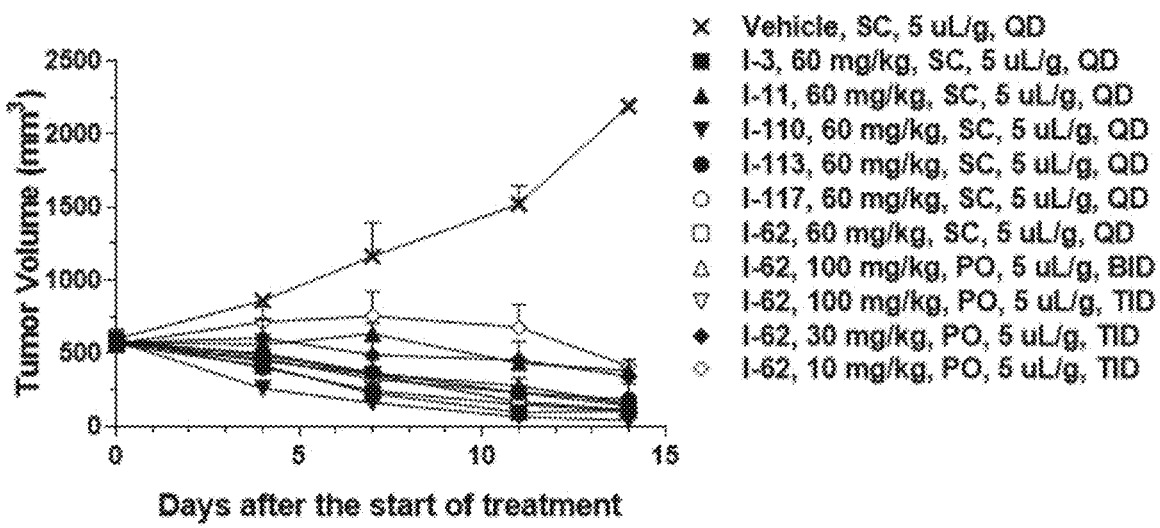

FIG. 24 is a graphical image of xenograph results for vehicle (SC, 5 μL/g, QD) and degrader I-3, I-11, I-62, I-110, I-113, and I-117 at various dosing regimens showing tumor volume (mm$^3$) (y-axis) versus dosing interval (days after start of treatment) (x-axis) for OCI-LY10 (MYD88 mutant) cells.

Figure 25:
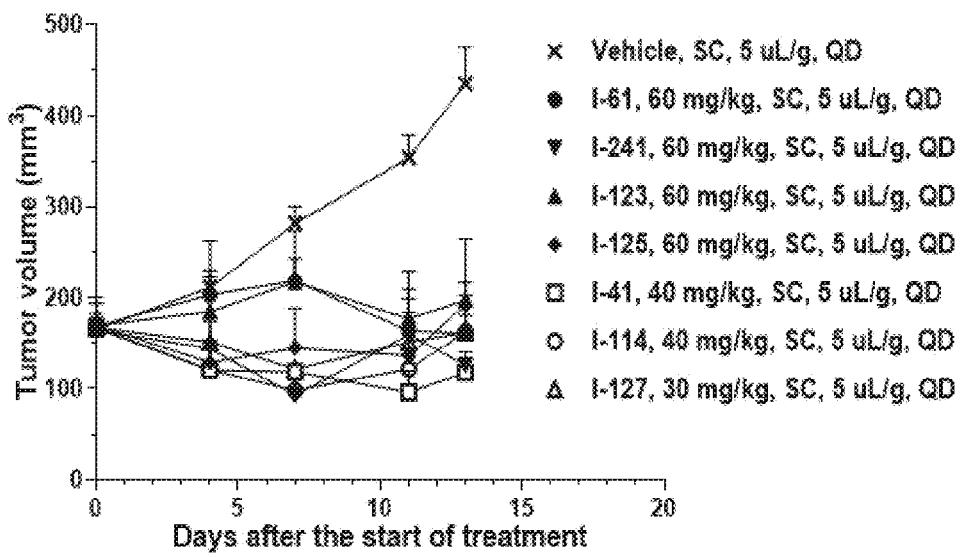

FIG. 25 is a graphical image of xenograph results for vehicle (SC, 5 μL/g, QD) and degrader I-41, I-61, I-114, I-123, I-125, I-127, and I-241 at various dosing regimens showing tumor volume (mm$^3$) (y-axis) versus dosing interval (days after start of treatment) (x-axis) for OCI-LY10 (MYD88 mutant) cells.

Figure 26:
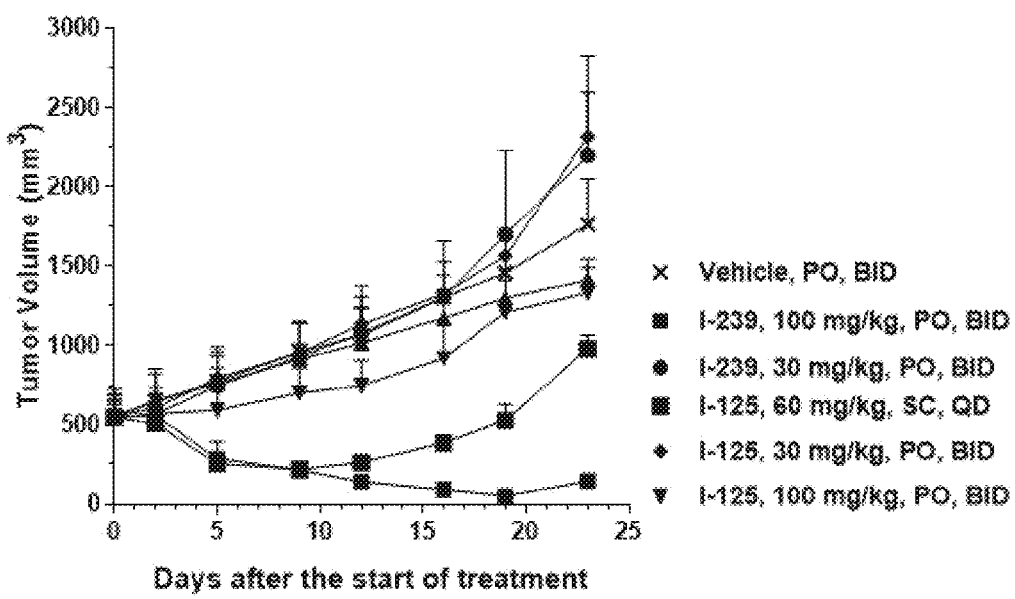

FIG. 26 is a graphical image of xenograph results for vehicle (PO, BID) and degrader I-125 and I-239 at various dosing regimens showing tumor volume (mm$^3$) (y-axis) versus dosing interval (days after start of treatment) (x-axis) for OCI-LY10 (MYD88 mutant) cells.

Figure 27:
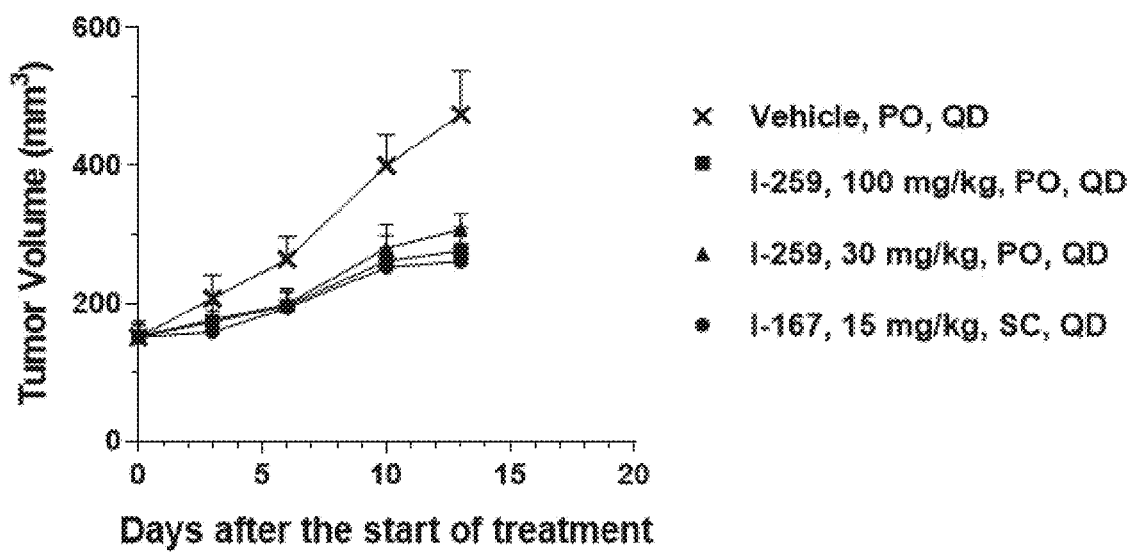

FIG. 27 is a graphical image of xenograph results for vehicle (PO, QD) and degrader I-167 and I-259 at various dosing regimens showing tumor volume (mm$^3$) (y-axis) versus dosing interval (days after start of treatment) (x-axis) for OCI-LY10 (MYD88 mutant) cells.

Figure 28:
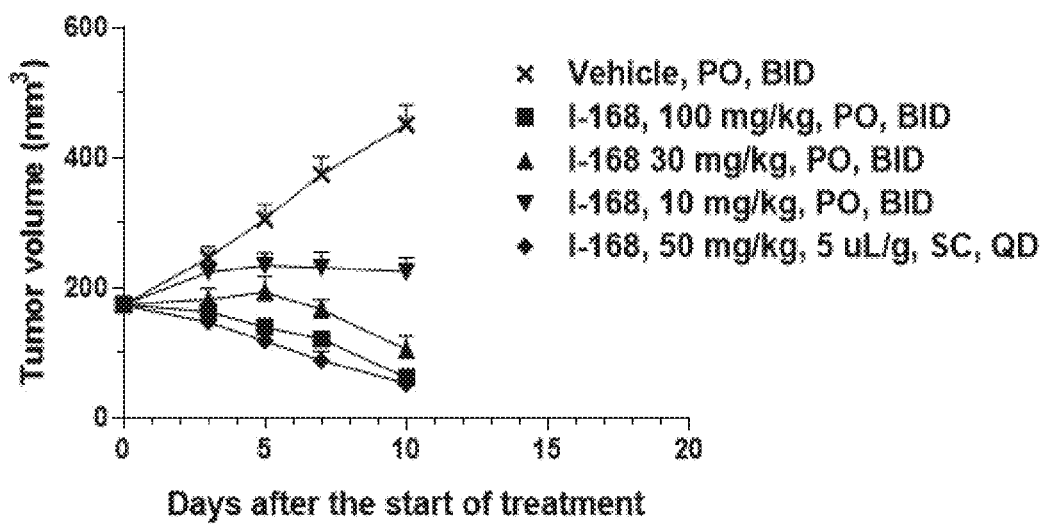

FIG. 28 is a graphical image of xenograph results for vehicle (PO, BID) and degrader I-168 at various dosing regimens showing tumor volume (mm$^3$) (y-axis) versus dosing interval (days after start of treatment) (x-axis) for OCI-LY10 (MYD88 mutant) cells.

Figure 29:
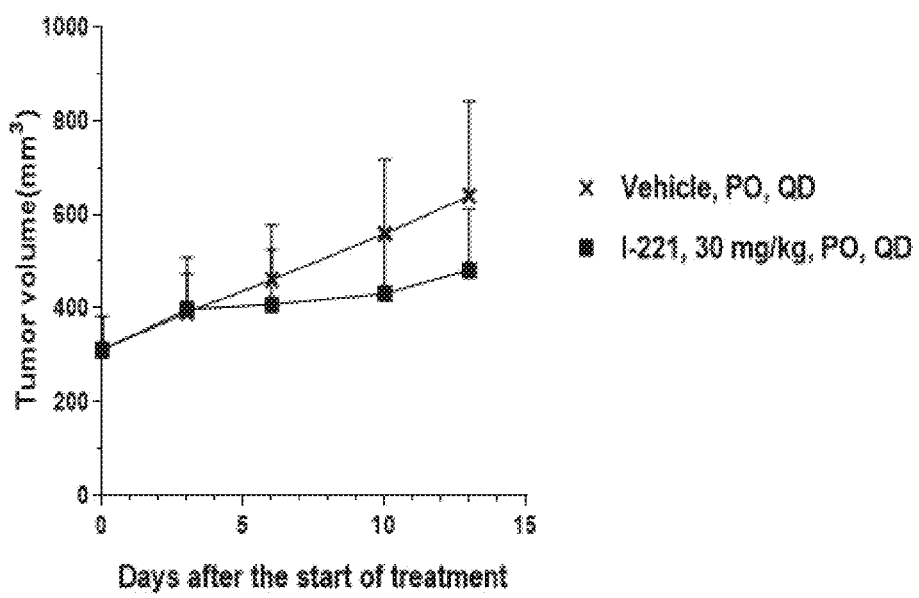

FIG. 29 is a graphical image of xenograph results for vehicle (PO, QD) and degrader I-221 (30 mg/kg, PO, QD) showing tumor volume (mm$^3$) (y-axis) versus dosing interval (days after start of treatment) (x-axis) for OCI-LY10 (MYD88 mutant) cells.

Figure 30:
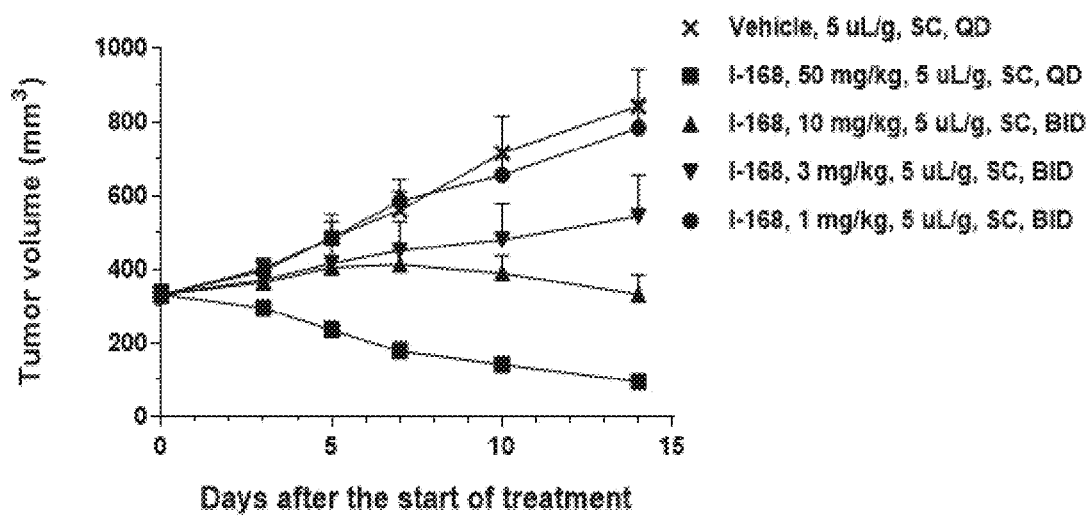

FIG. 30 is a graphical image of xenograph results for vehicle (SC, 5 μL/g, QD) and degrader I-168 at various dosing regimens showing tumor volume (mm$^3$) (y-axis) versus dosing interval (days after start of treatment) (x-axis) for OCI-LY10 (MYD88 mutant) cells.

Figure 31:
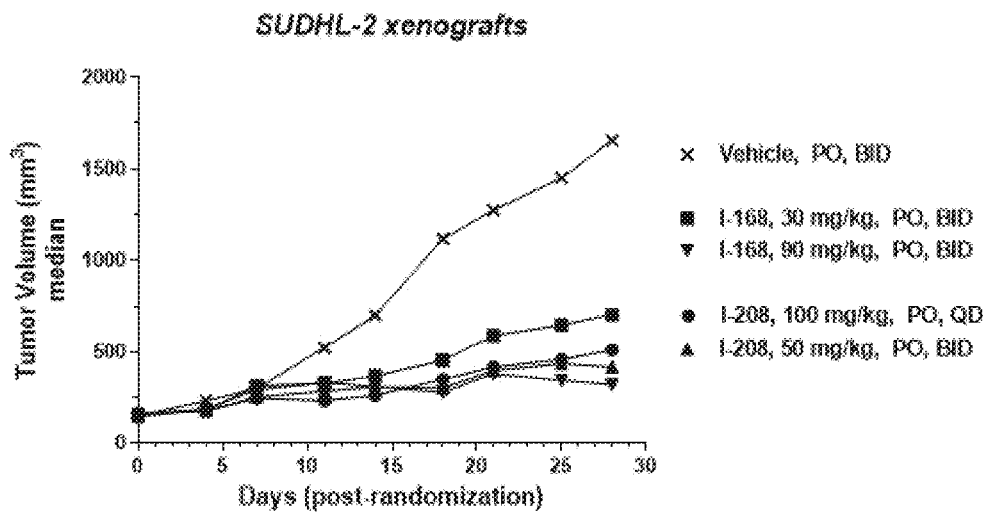

FIG. 31 is a graphical image of xenograph results for vehicle (PO, BID) and degrader I-168 and I-208 at various dosing regimens showing tumor volume (mm$^3$) (y-axis) versus dosing interval (days post-randomization) (x-axis) for SUDHL-2 cells.

Figure 32:
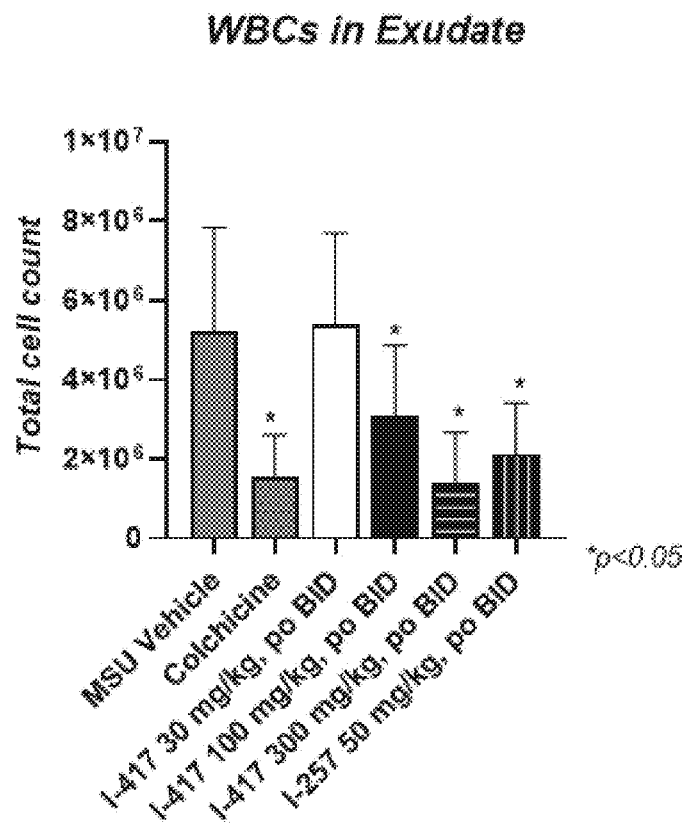

FIG. 32 is a graphical image depicting WBCs in exudate collected from air pouch in mouse following MSU crystal challenge using showing total cell count (% cells in extrudate) (y-axis) and (MSU; colchicine; 30, 100, and 300 mg/kg PO BID I-417; and 50 mg/kg PO BID I-257) (x-axis).

Figure 33:
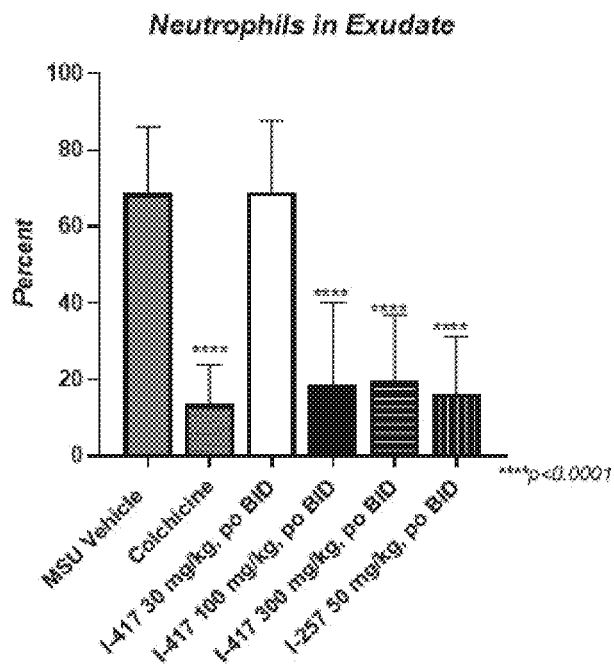

FIG. 33 is a graphical image depicting neutrophils in exudate collected from air pouch in mouse following MSU crystal challenge using showing total cell count (% cells in extrudate) (y-axis) and (MSU; colchicine; 30, 100, and 300 mg/kg PO BID I-417; and 50 mg/kg PO BID I-257) (x-axis).

Figure 34:
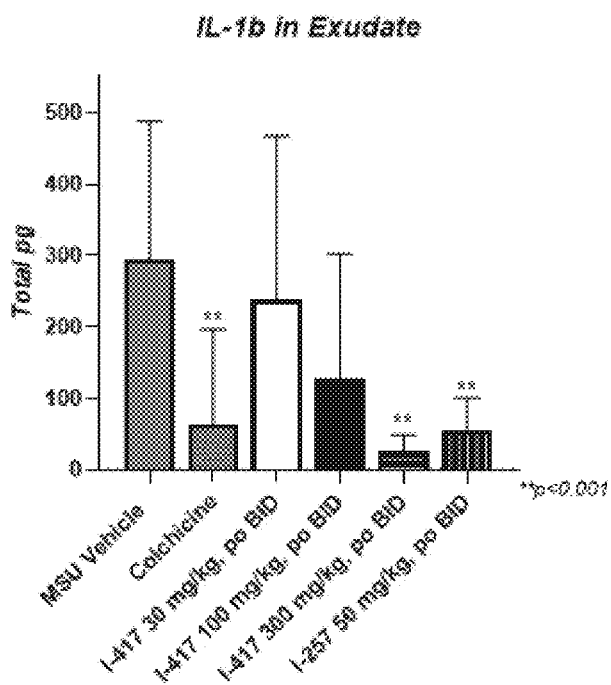

FIG. 34 is a graphical image depicting IL-1b in exudate collected from air pouch in mouse following MSU crystal challenge using showing total cell count (% cells in extrudate) (y-axis) and (MSU; colchicine; 30, 100, and 300 mg/kg PO BID I-417; and 50 mg/kg PO BID I-257) (x-axis).

Figure 35:
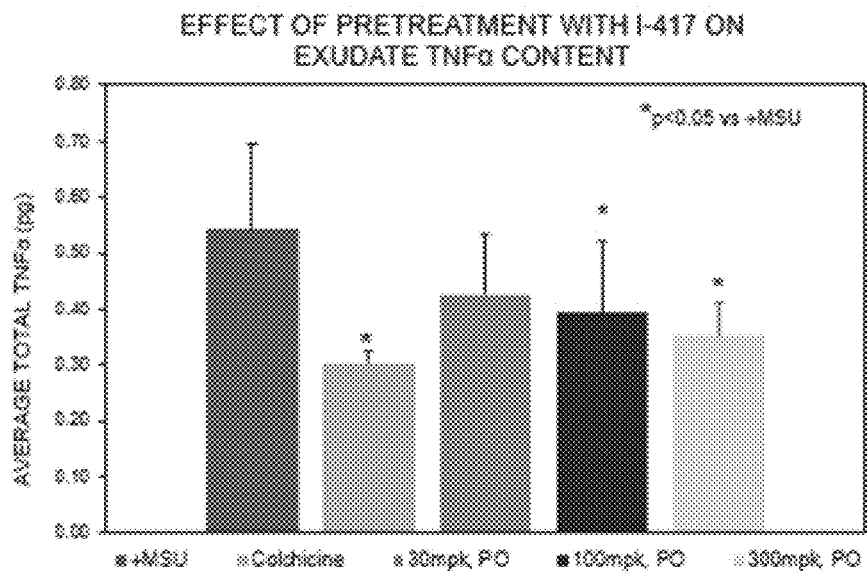

FIG. 35 includes graphical images depicting the effect of pretreatment with I-417 on exudate TNFα content showing average TNFα (pg) (y-axes) and MSU, colchicine, and 30, 100, and 300 mg/kg PO I-417 (x-axes).

Figure 36:
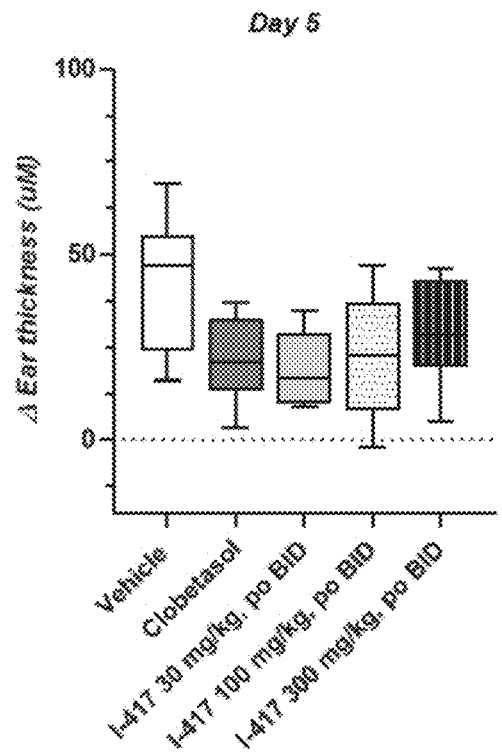

FIG. 36 is a graphical image depicting mouse imiquimod (IMQ) induced skin inflammation showing change in ear thicknesss (μm) (y-axis) and vehicle, clobetasol, and I-417 (30, 100, and 300 mg/kg, PO, BID) (x-axis).

Figure 37:
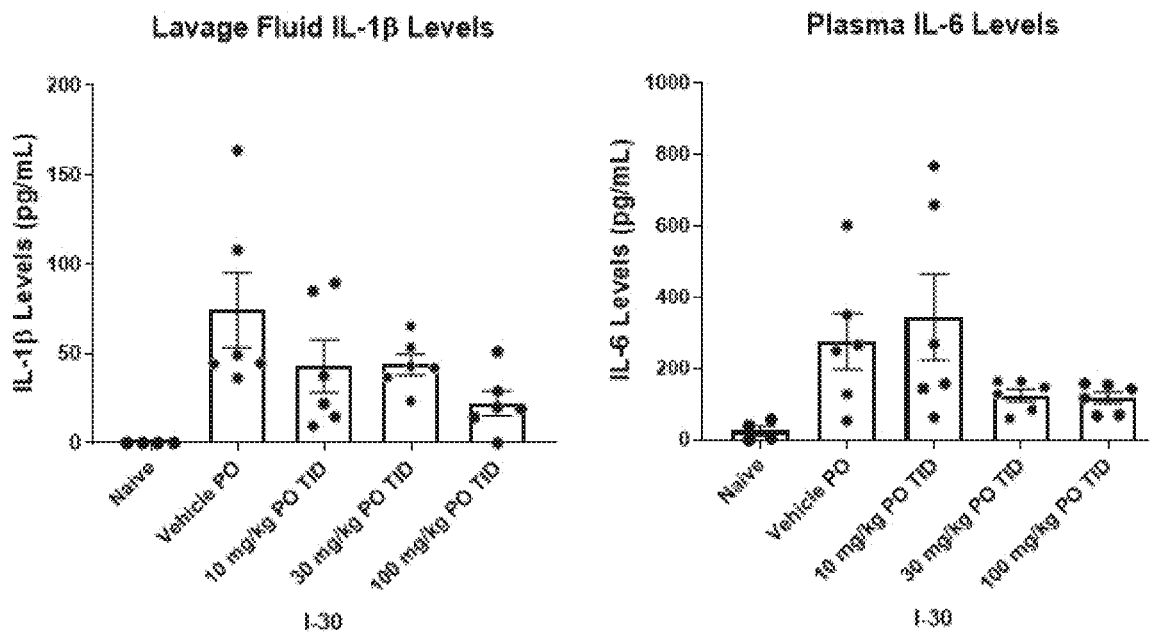

FIG. 37 includes graphical images depicting the results of the mouse intra peritoneal MSU induced peritonitis model showing lavage fluid IL-1b levels (left) and plasma IL-6 levels (right) (pg/mL) (y-axis) and naive, vehicle (PO), and 10, 30, and 100 mg/kg I-30 (PO TID) (x-axis).

Figure 38:
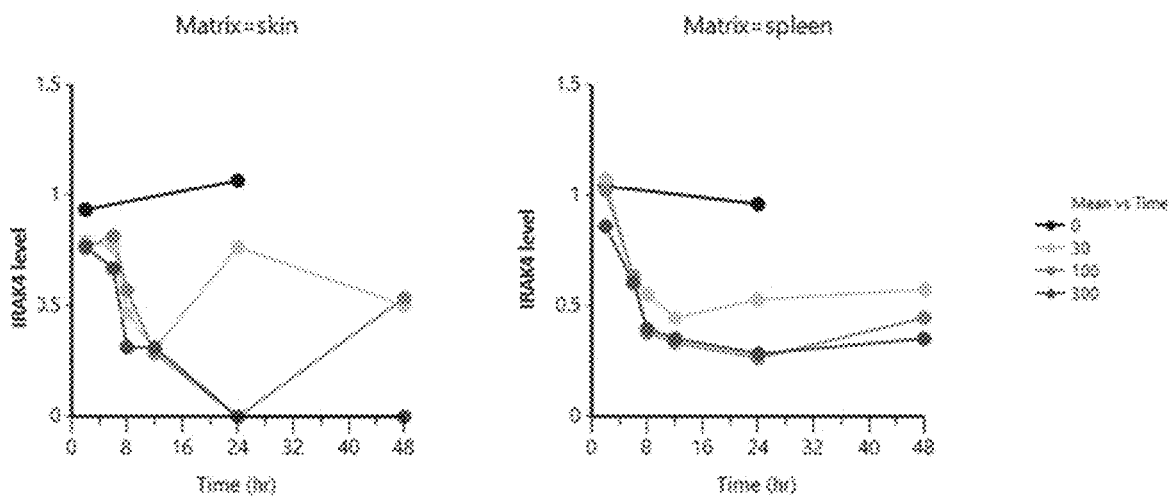

FIG. 38 includes graphical images depicting the results of a PD study using I-417 in wild-type mice showing IRAK4 level (y-axis) over time (hr) (x-axis) in skin (left) and spleen (right).

DETAILED DESCRIPTION OF CERTAIN EMBODIMENTS

1. General Description of Certain Embodiments of the Invention

Compounds of the present invention, and compositions thereof, are useful as degraders and/or inhibitors of one or more IRAK protein kinases. In some embodiments, a provided compound degrades and/or inhibits IRAK-1/2/3/4.

In certain embodiments, the present invention provides a compound of formula I:

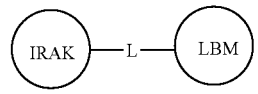

I or a pharmaceutically acceptable salt thereof, wherein:
IRAK is an IRAK binding moiety capable of binding to one or more of IRAK-1, -2, -3, or -4;
L is a bivalent moiety that connects IRAK to LBM; and
LBM is a ligase binding moiety.

In certain embodiments, the present invention provides a compound of Formula V:

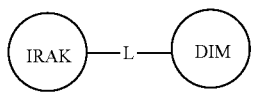

V or a pharmaceutically acceptable salt thereof, wherein:
IRAK is an IRAK binding moiety capable of binding to one or more of IRAK-1, -2, -3, or -4;
L is a bivalent moiety that connects IRAK to DIM; and
DIM is a degradation inducing moiety.

2. Compounds and Definitions

Compounds of the present invention include those described generally herein, and are further illustrated by the classes, subclasses, and species disclosed herein. As used herein, the following definitions shall apply unless otherwise indicated. For purposes of this invention, the chemical elements are identified in accordance with the Periodic Table of the Elements, CAS version, Handbook of Chemistry and Physics, 75$^{th}$ Ed. Additionally, general principles of organic chemistry are described in "Organic Chemistry", Thomas Sorrell, University Science Books, Sausalito: 1999, and "March's Advanced Organic Chemistry", 5$^{th}$ Ed., Ed.: Smith, M. B. and March, J., John Wiley & Sons, New York: 2001, the entire contents of which are hereby incorporated by reference.

The term "aliphatic" or "aliphatic group", as used herein, means a straight-chain (i.e., unbranched) or branched, substituted or unsubstituted hydrocarbon chain that is completely saturated or that contains one or more units of unsaturation, or a monocyclic hydrocarbon or bicyclic hydrocarbon that is completely saturated or that contains one or more units of unsaturation, but which is not aromatic (also referred to herein as "carbocycle," "cycloaliphatic" or "cycloalkyl"), that has a single point of attachment to the rest of the molecule. Unless otherwise specified, aliphatic groups contain 1-6 aliphatic carbon atoms. In some embodiments, aliphatic groups contain 1-5 aliphatic carbon atoms. In other embodiments, aliphatic groups contain 1-4 aliphatic carbon atoms. In still other embodiments, aliphatic groups contain 1-3 aliphatic carbon atoms, and in yet other embodiments, aliphatic groups contain 1-2 aliphatic carbon atoms. In some embodiments, "cycloaliphatic" (or "carbocycle" or "cycloalkyl") refers to a monocyclic $C_3$-$C_6$ hydrocarbon that is completely saturated or that contains one or more units of unsaturation, but which is not aromatic, that has a single point of attachment to the rest of the molecule. Suitable aliphatic groups include, but are not limited to, linear or branched, substituted or unsubstituted alkyl, alkenyl, alkynyl groups and hybrids thereof such as (cycloalkyl)alkyl, (cycloalkenyl)alkyl or (cycloalkyl)alkenyl.

As used herein, the term "bridged bicyclic" refers to any bicyclic ring system, i.e. carbocyclic or heterocyclic, saturated or partially unsaturated, having at least one bridge. As defined by IUPAC, a "bridge" is an unbranched chain of atoms or an atom or a valence bond connecting two bridgeheads, where a "bridgehead" is any skeletal atom of the ring system which is bonded to three or more skeletal atoms (excluding hydrogen). In some embodiments, a bridged bicyclic group has 7-12 ring members and 0-4 heteroatoms independently selected from nitrogen, oxygen, or sulfur. Such bridged bicyclic groups are well known in the art and include those groups set forth below where each group is attached to the rest of the molecule at any substitutable carbon or nitrogen atom. Unless otherwise specified, a bridged bicyclic group is optionally substituted with one or more substituents as set forth for aliphatic groups. Additionally or alternatively, any substitutable nitrogen of a bridged bicyclic group is optionally substituted. Exemplary bridged bicyclics include:

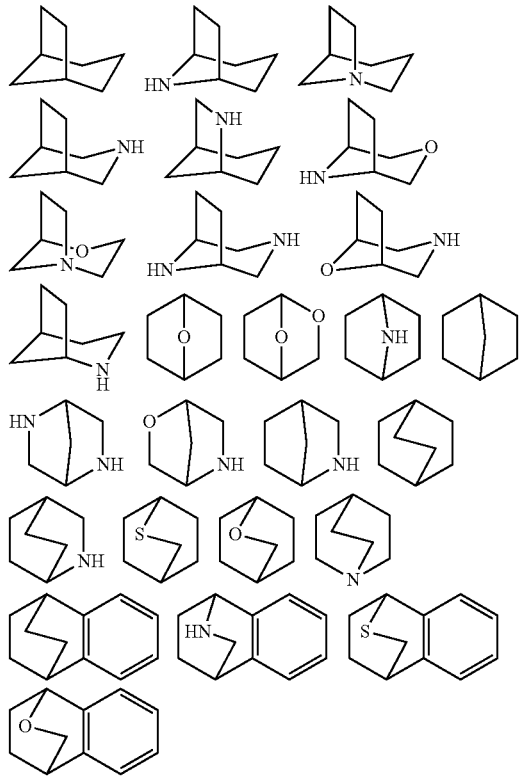

The term "lower alkyl" refers to a $C_{1-4}$ straight or branched alkyl group. Exemplary lower alkyl groups are methyl, ethyl, propyl, isopropyl, butyl, isobutyl, and tert-butyl.

The term "lower haloalkyl" refers to a $C_{1-4}$ straight or branched alkyl group that is substituted with one or more halogen atoms.

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or NR$^+$ (as in N-substituted pyrrolidinyl)).

The term "unsaturated," as used herein, means that a moiety has one or more units of unsaturation.

As used herein, the term "bivalent $C_{1-8}$ (or $C_{1-6}$) saturated or unsaturated, straight or branched, hydrocarbon chain", refers to bivalent alkylene, alkenylene, and alkynylene chains that are straight or branched as defined herein.

The term "alkylene" refers to a bivalent alkyl group. An "alkylene chain" is a polymethylene group, i.e., —(CH$_2$)$_n$—, wherein n is a positive integer, preferably from 1 to 6, from 1 to 4, from 1 to 3, from 1 to 2, or from 2 to 3. A substituted alkylene chain is a polymethylene group in which one or more methylene hydrogen atoms are replaced with a substituent. Suitable substituents include those described below for a substituted aliphatic group.

The term "alkenylene" refers to a bivalent alkenyl group. A substituted alkenylene chain is a polymethylene group containing at least one double bond in which one or more hydrogen atoms are replaced with a substituent. Suitable substituents include those described below for a substituted aliphatic group.

As used herein, the term "cyclopropylenyl" refers to a bivalent cyclopropyl group of the following structure:

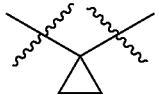

The term "halogen" means F, Cl, Br, or I.

The term "aryl" used alone or as part of a larger moiety as in "aralkyl," "aralkoxy," or "aryloxyalkyl," refers to monocyclic or bicyclic ring systems having a total of five to fourteen ring members, wherein at least one ring in the system is aromatic and wherein each ring in the system contains 3 to 7 ring members. The term "aryl" may be used interchangeably with the term "aryl ring." In certain embodiments of the present invention, "aryl" refers to an aromatic ring system which includes, but not limited to, phenyl, biphenyl, naphthyl, anthracyl and the like, which may bear one or more substituents. Also included within the scope of the term "aryl," as it is used herein, is a group in which an aromatic ring is fused to one or more non-aromatic rings, such as indanyl, phthalimidyl, naphthimidyl, phenanthridinyl, or tetrahydronaphthyl, and the like.

The terms "heteroaryl" and "heteroar-," used alone or as part of a larger moiety, e.g., "heteroaralkyl," or "heteroaralkoxy," refer to groups having 5 to 10 ring atoms, preferably 5, 6, or 9 ring atoms; having 6, 10, or 14π electrons shared in a cyclic array; and having, in addition to carbon atoms, from one to five heteroatoms. The term "heteroatom" refers to nitrogen, oxygen, or sulfur, and includes any oxidized form of nitrogen or sulfur, and any quaternized form of a basic nitrogen. Heteroaryl groups include, without limitation, thienyl, furanyl, pyrrolyl, imidazolyl, pyrazolyl, triazolyl, tetrazolyl, oxazolyl, isoxazolyl, oxadiazolyl, thiazolyl, isothiazolyl, thiadiazolyl, pyridyl, pyridazinyl, pyrimidinyl, pyrazinyl, indolizinyl, purinyl, naphthyridinyl, and pteridinyl. The terms "heteroaryl" and "heteroar-", as used herein, also include groups in which a heteroaromatic ring is fused to one or more aryl, cycloaliphatic, or heterocyclyl rings, where the radical or point of attachment is on the heteroaromatic ring. Nonlimiting examples include indolyl, isoindolyl, benzothienyl, benzofuranyl, dibenzofuranyl, indazolyl, benzimidazolyl, benzthiazolyl, quinolyl, isoquinolyl, cinnolinyl, phthalazinyl, quinazolinyl, quinoxalinyl, 4H-quinolizinyl, carbazolyl, acridinyl, phenazinyl, phenothiazinyl, phenoxazinyl, tetrahydroquinolinyl, tetrahydroisoquinolinyl, and pyrido[2,3-b]-1,4-oxazin-3 (4H)-one. A heteroaryl group may be mono- or bicyclic. The term "heteroaryl" may be used interchangeably with the terms "heteroaryl ring," "heteroaryl group," or "heteroaromatic," any of which terms include rings that are optionally substituted. The term "heteroaralkyl" refers to an alkyl group substituted by a heteroaryl, wherein the alkyl and heteroaryl portions independently are optionally substituted.

As used herein, the terms "heterocycle," "heterocyclyl," "heterocyclic radical," and "heterocyclic ring" are used interchangeably and refer to a stable 5- to 7-membered monocyclic or 7-10-membered bicyclic heterocyclic moiety that is either saturated or partially unsaturated, and having, in addition to carbon atoms, one or more, preferably one to four, heteroatoms, as defined above. When used in reference to a ring atom of a heterocycle, the term "nitrogen" includes a substituted nitrogen. As an example, in a saturated or partially unsaturated ring having 0-3 heteroatoms selected from oxygen, sulfur or nitrogen, the nitrogen may be N (as in 3,4-dihydro-2H-pyrrolyl), NH (as in pyrrolidinyl), or +NR (as in N-substituted pyrrolidinyl).

A heterocyclic ring can be attached to its pendant group at any heteroatom or carbon atom that results in a stable structure and any of the ring atoms can be optionally substituted. Examples of such saturated or partially unsaturated heterocyclic radicals include, without limitation, tetrahydrofuranyl, tetrahydrothiophenyl pyrrolidinyl, piperidinyl, pyrrolinyl, tetrahydroquinolinyl, tetrahydroisoquinolinyl, decahydroquinolinyl, oxazolidinyl, piperazinyl, dioxanyl, dioxolanyl, diazepinyl, oxazepinyl, thiazepinyl, morpholinyl, and quinuclidinyl. The terms "heterocycle," "heterocyclyl," "heterocyclyl ring," "heterocyclic group," "heterocyclic moiety," and "heterocyclic radical," are used interchangeably herein, and also include groups in which a heterocyclyl ring is fused to one or more aryl, heteroaryl, or cycloaliphatic rings, such as indolinyl, 3H-indolyl, chromanyl, phenanthridinyl, or tetrahydroquinolinyl. A heterocyclyl group may be mono- or bicyclic. The term "heterocyclylalkyl" refers to an alkyl group substituted by a heterocyclyl, wherein the alkyl and heterocyclyl portions independently are optionally substituted.

As used herein, the term "partially unsaturated" refers to a ring moiety that includes at least one double or triple bond. The term "partially unsaturated" is intended to encompass rings having multiple sites of unsaturation, but is not intended to include aryl or heteroaryl moieties, as herein defined.

As described herein, compounds of the invention may contain "optionally substituted" moieties. In general, the term "substituted," whether preceded by the term "optionally" or not, means that one or more hydrogens of the designated moiety are replaced with a suitable substituent. Unless otherwise indicated, an "optionally substituted" group may have a suitable substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds. The term "stable," as used herein, refers to compounds that are not substantially altered when subjected to conditions to allow for their production, detection, and, in certain embodiments, their recovery, purification, and use for one or more of the purposes disclosed herein.

Suitable monovalent substituents on a substitutable carbon atom of an "optionally substituted" group are independently halogen; —(CH$_2$)$_{0-4}$R°; —(CH$_2$)$_{0-4}$OR°; —O(CH$_2$)$_{0-4}$R°, —O—(CH$_2$)$_{0-4}$C(O)OR°; —(CH$_2$)$_{0-4}$CH (OR°)$_2$; —(CH$_2$)$_{0-4}$SR°; —(CH$_2$)$_{0-4}$Ph, which may be substituted with R°; —(CH$_2$)$_{0-4}$O(CH$_2$)$_{0-1}$Ph which may be substituted with R°; —CH=CHPh, which may be substituted with R°; —(CH$_2$)$_{0-4}$O(CH$_2$)$_{0-1}$-pyridyl which may be substituted with R°; —NO$_2$; —CN; —N$_3$; —(CH$_2$)$_{0-4}$N(R°)$_2$; —(CH$_2$)$_{0-4}$N(R)C(O)R°; —N(R°)C(S)R°; —(CH$_2$)$_{0-4}$N(R°)C(O)NR°$_2$; —N(R°)C(S)NR°$_2$; —(CH$_2$)$_{0-4}$N(R°)C(O)OR°; —N(R°)N(R°)C(O)R°; —N(R°)N(R°)C(O)NR°$_2$; —N(R°)N(R°)C(O)OR°; —(CH$_2$)$_{0-4}$C(O)R°; —C(S)R°; —(CH$_2$)$_{0-4}$C(O)OR°; —(CH$_2$)$_{0-4}$C(O)SR°; —(CH$_2$)$_{0-4}$C(O)OSiR°$_3$; —(CH$_2$)$_{0-4}$OC(O)R°; —OC(O)(CH$_2$)$_{0-4}$SR—, SC(S)SR°; —(CH$_2$)$_{0-4}$SC(O)R°; —(CH$_2$)$_{0-4}$C(O)NR°$_2$; —C(S)NR°$_2$; —C(S)SR°; —SC(S)SR°, —(CH$_2$)$_{0-4}$OC(O)NR°$_2$; —C(O)N(OR°)R°; —C(O)C(O)R°; —C(O)CH$_2$C(O)R°; —C(NOR°)R°; —(CH$_2$)$_{0-4}$SSR°; —(CH$_2$)$_{0-4}$S(O)$_2$R°; —(CH$_2$)$_{0-4}$S(O)$_2$OR°; —(CH$_2$)$_{0-4}$OS(O)$_2$R°; —S(O)$_2$NR$_2$; —(CH$_2$)$_{0-4}$S(O)R°; —N(R°)S(O)$_2$NR°$_2$; —N(R°)S(O)$_2$R°; —N(OR°)R°; —C(NH)NR°$_2$; —P(O)$_2$R°; —P(O)R°$_2$; —OP(O)R°$_2$; —OP(O)(OR°)$_2$; SiR°$_3$; —(C$_{1-4}$ straight or branched alkylene)O—N(R°)$_2$; or —(C$_{1-4}$ straight or branched alkylene)C(O)O—N(R°)$_2$, wherein each R° may be substituted as defined below and is independently hydrogen, C$_{1-6}$ aliphatic, —CH$_2$Ph, —O(CH$_2$)$_{0-1}$Ph, —CH$_2$-(5-6 membered heteroaryl ring), or a 5-6-membered saturated, partially unsaturated, or aryl ring having 0-4 heteroatoms independently selected from nitrogen, oxygen, or sulfur, or, notwithstanding the definition above, two independent occurrences of R°, taken together with their intervening atom(s), form a 3-12-membered saturated, partially unsaturated, or aryl mono- or bicyclic ring having 0-4 heteroatoms independently selected from nitrogen, oxygen, or sulfur, which may be substituted as defined below.

Suitable monovalent substituents on R° (or the ring formed by taking two independent occurrences of R° together with their intervening atoms), are independently halogen, —(CH$_2$)$_{0-2}$R$^•$, -(haloR$^•$), —(CH$_2$)$_{0-2}$OH, —(CH$_2$)$_{0-2}$OR$^•$, —(CH$_2$)$_{0-2}$CH(OR$^•$)$_2$; —O(haloR$^•$), —CN, —N$_3$, —(CH$_2$)$_{0-2}$C(O)R$^•$, —(CH$_2$)$_{0-2}$C(O)OH, —(CH$_2$)$_{0-2}$C(O)OR$^•$, —(CH$_2$)$_{0-2}$SR$^•$, —(CH$_2$)$_{0-2}$SH, —(CH$_2$)$_{0-2}$NH$_2$, —(CH$_2$)$_{0-2}$NHR$^•$, —(CH$_2$)$_{0-2}$NR$^•_2$, —NO$_2$, —SiR$^•_3$, —OSiR$^•_3$, —C(O)SR$^•$, —(C$_{1-4}$ straight or branched alkylene)C(O)OR$^•$, or —SSR$^•$ wherein each R$^•$ is unsubstituted or where preceded by "halo" is substituted only with one or more halogens, and is independently selected from C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur. Suitable divalent substituents on a saturated carbon atom of R° include =O and =S.

Suitable divalent substituents on a saturated carbon atom of an "optionally substituted" group include the following: =O, =S, =NNR*$_2$, =NNHC(O)R*, =NNHC(O)OR*, =NNHS(O)$_2$R*, =NR*, =NOR*, —O(C(R*$_2$))$_{2-3}$O—, or —S(C(R*$_2$))$_{2-3}$S—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur. Suitable divalent substituents that are bound to vicinal substitutable carbons of an "optionally substituted" group include: —O(CR*$_2$)$_{2-3}$O—, wherein each independent occurrence of R* is selected from hydrogen, C$_{1-6}$ aliphatic which may be substituted as defined below, or an unsubstituted 5-6-membered saturated, partially unsaturated, or aryl ring having 0-4 heteroatoms independently selected from nitrogen, oxygen, or sulfur.

Suitable substituents on the aliphatic group of R* include halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

Suitable substituents on a substitutable nitrogen of an "optionally substituted" group include —R$^†$, —NR$^†_2$, —C(O)R$^†$, —C(O)OR$^†$, —C(O)C(O)R$^†$, —C(O)CH$_2$C(O)R$^†$, —S(O)$_2$R$^†$, —S(O)$_2$NR$^†_2$, —C(S)NR$^†_2$, —C(NH)NR$^†_2$, or —N(R$^†$)S(O)$_2$R$^†$; wherein each R$^†$ is independently hydrogen, C$_{1-6}$ aliphatic which may be substituted as defined below, unsubstituted —OPh, or an unsubstituted 5-6-membered saturated, partially unsaturated, or aryl ring having 0-4 heteroatoms independently selected from nitrogen, oxygen, or sulfur, or, notwithstanding the definition above, two independent occurrences of R$^†$, taken together with their intervening atom(s) form an unsubstituted 3-12-membered saturated, partially unsaturated, or aryl mono- or bicyclic ring having 0-4 heteroatoms independently selected from nitrogen, oxygen, or sulfur.

Suitable substituents on the aliphatic group of R$^†$ are independently halogen, —R$^•$, -(haloR$^•$), —OH, —OR$^•$, —O(haloR$^•$), —CN, —C(O)OH, —C(O)OR$^•$, —NH$_2$, —NHR$^•$, —NR$^•_2$, or —NO$_2$, wherein each R$^•$ is unsubstituted or where preceded by "halo" is substituted only with one or more halogens, and is independently C$_{1-4}$ aliphatic, —CH$_2$Ph, —O(CH$_2$)$_{0-1}$Ph, or a 5-6-membered saturated, partially unsaturated, or aryl ring having 0-4 heteroatoms independently selected from nitrogen, oxygen, or sulfur.

As used herein, the term "provided compound" refers to any genus, subgenus, and/or species set forth herein.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge et al., describe pharmaceutically acceptable salts in detail in J. Pharmaceutical Sciences, 1977, 66, 1-19, incorporated herein by reference. Pharmaceutically acceptable salts of the compounds of this invention include those derived from suitable inorganic and organic acids and bases. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pivalate, propionate, stearate, succinate, sulfate, tartrate, thiocyanate, p-toluenesulfonate, undecanoate, valerate salts, and the like.

Salts derived from appropriate bases include alkali metal, alkaline earth metal, ammonium and $N^+(C_{1-4}alkyl)_4$ salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

Unless otherwise stated, structures depicted herein are also meant to include all isomeric (e.g., enantiomeric, diastereomeric, and geometric (or conformational)) forms of the structure; for example, the R and S configurations for each asymmetric center, Z and E double bond isomers, and Z and E conformational isomers. Therefore, single stereochemical isomers as well as enantiomeric, diastereomeric, and geometric (or conformational) mixtures of the present compounds are within the scope of the invention. Unless otherwise stated, all tautomeric forms of the compounds of the invention are within the scope of the invention. Additionally, unless otherwise stated, structures depicted herein are also meant to include compounds that differ only in the presence of one or more isotopically enriched atoms. For example, compounds having the present structures including the replacement of hydrogen by deuterium or tritium, or the replacement of a carbon by a $^{13}C$- or $^{14}C$-enriched carbon are within the scope of this invention. Such compounds are useful, for example, as analytical tools, as probes in biological assays, or as therapeutic agents in accordance with the present invention As used herein, the term "inhibitor" is defined as a compound that binds to and/or inhibits an IRAK kinase with measurable affinity. In certain embodiments, an inhibitor has an $IC_{50}$ and/or binding constant of less than about 50 µM, less than about 1 µM, less than about 500 nM, less than about 100 nM, less than about 10 nM, or less than about 1 nM.

As used herein, the term "degrader" is defined as a heterobifunctional compound that binds to and/or inhibits both an IRAK kinase and an E3 ligase with measurable affinity resulting in the ubiqitination and subsequent degradation of the IRAK kinase. In certain embodiments, a degrader has an $DC_{50}$ of less than about 50 µM, less than about 1 µM, less than about 500 nM, less than about 100 nM, less than about 10 nM, or less than about 1 nM. As used herein, the term "monovalent" refers to a degrader compound without an appended E3 ligase binding moiety.

A compound of the present invention may be tethered to a detectable moiety. It will be appreciated that such compounds are useful as imaging agents. One of ordinary skill in the art will recognize that a detectable moiety may be attached to a provided compound via a suitable substituent. As used herein, the term "suitable substituent" refers to a moiety that is capable of covalent attachment to a detectable moiety. Such moieties are well known to one of ordinary skill in the art and include groups containing, e.g., a carboxylate moiety, an amino moiety, a thiol moiety, or a hydroxyl moiety, to name but a few. It will be appreciated that such moieties may be directly attached to a provided compound or via a tethering group, such as a bivalent saturated or unsaturated hydrocarbon chain. In some embodiments, such moieties may be attached via click chemistry. In some embodiments, such moieties may be attached via a 1,3-cycloaddition of an azide with an alkyne, optionally in the presence of a copper catalyst. Methods of using click chemistry are known in the art and include those described by Rostovtsev et al., Angew. Chem. Int. Ed. 2002, 41, 2596-99 and Sun et al., Bioconjugate Chem., 2006, 17, 52-57.

As used herein, the term "detectable moiety" is used interchangeably with the term "label" and relates to any moiety capable of being detected, e.g., primary labels and secondary labels. Primary labels, such as radioisotopes (e.g., tritium, $^{32}P$, $^{33}P$, $^{35}S$, or $^{14}C$), mass-tags, and fluorescent labels are signal generating reporter groups which can be detected without further modifications. Detectable moieties also include luminescent and phosphorescent groups.

The term "secondary label" as used herein refers to moieties such as biotin and various protein antigens that require the presence of a second intermediate for production of a detectable signal. For biotin, the secondary intermediate may include streptavidin-enzyme conjugates. For antigen labels, secondary intermediates may include antibody-enzyme conjugates. Some fluorescent groups act as secondary labels because they transfer energy to another group in the process of nonradiative fluorescent resonance energy transfer (FRET), and the second group produces the detected signal.

The terms "fluorescent label", "fluorescent dye", and "fluorophore" as used herein refer to moieties that absorb light energy at a defined excitation wavelength and emit light energy at a different wavelength. Examples of fluorescent labels include, but are not limited to: Alexa Fluor dyes (Alexa Fluor 350, Alexa Fluor 488, Alexa Fluor 532, Alexa Fluor 546, Alexa Fluor 568, Alexa Fluor 594, Alexa Fluor 633, Alexa Fluor 660 and Alexa Fluor 680), AMCA, AMCA-S, BODIPY dyes (BODIPY FL, BODIPY R6G, BODIPY TMR, BODIPY TR, BODIPY 530/550, BODIPY 558/568, BODIPY 564/570, BODIPY 576/589, BODIPY 581/591, BODIPY 630/650, BODIPY 650/665), Carboxyrhodamine 6G, carboxy-X-rhodamine (ROX), Cascade Blue, Cascade Yellow, Coumarin 343, Cyanine dyes (Cy3, Cy5, Cy3.5, Cy5.5), Dansyl, Dapoxyl, Dialkylaminocoumarin, 4',5'-Dichloro-2',7'-dimethoxy-fluorescein, DM-NERF, Eosin, Erythrosin, Fluorescein, FAM, Hydroxycoumarin, IRDyes (IRD40, IRD 700, IRD 800), JOE, Lissamine rhodamine B, Marina Blue, Methoxycoumarin, Naphthofluorescein, Oregon Green 488, Oregon Green 500, Oregon Green 514, Pacific Blue, PyMPO, Pyrene, Rhodamine B, Rhodamine 6G, Rhodamine Green, Rhodamine Red, Rhodol Green, 2',4',5',7'-Tetra-bromosulfone-fluorescein, Tetramethyl-rhodamine (TMR), Carboxytetramethylrhodamine (TAMRA), Texas Red, Texas Red-X.

The term "mass-tag" as used herein refers to any moiety that is capable of being uniquely detected by virtue of its mass using mass spectrometry (MS) detection techniques. Examples of mass-tags include electrophore release tags such as N-[3-[4'-[(p-Methoxytetrafluorobenzyl)oxy]phenyl]-3-methylglyceronyl]isonipecotic Acid, 4'-[2,3,5,6-Tetrafluoro-4-(pentafluorophenoxyl)]methyl acetophenone, and their derivatives. The synthesis and utility of these mass-tags is described in U.S. Pat. Nos. 4,650,750, 4,709,016, 5,360, 8191, 5,516,931, 5,602,273, 5,604,104, 5,610,020, and 5,650,270. Other examples of mass-tags include, but are not limited to, nucleotides, dideoxynucleotides, oligonucleotides of varying length and base composition, oligopeptides, oligosaccharides, and other synthetic polymers of varying length and monomer composition. A large variety of organic molecules, both neutral and charged (biomolecules or synthetic compounds) of an appropriate mass range (100-2000 Daltons) may also be used as mass-tags.

The terms "measurable affinity" and "measurably inhibit," as used herein, means a measurable change in an IRAK protein kinase activity between a sample comprising a compound of the present invention, or composition thereof, and an IRAK protein kinase, and an equivalent sample comprising an IRAK protein kinase, in the absence of said compound, or composition thereof.

3. Description of Exemplary Embodiments

As described above, in certain embodiments, the present invention provides a compound of formula I:

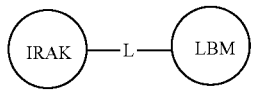

I or a pharmaceutically acceptable salt thereof, wherein:
IRAK is an IRAK binding moiety capable of binding to one or more of IRAK-1, -2, -3, or -4;
L is a bivalent moiety that connects IRAK to LBM; and
LBM is a ligase binding moiety.

In some embodiments, the present invention provides a compound of formula I:

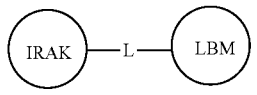

I or a pharmaceutically acceptable salt thereof, wherein:
IRAK is an IRAK-4 binding moiety;
L is a bivalent moiety that connects IRAK to LBM; and
LBM is a cereblon ligase binding moiety.

As described above, in certain embodiments, the present invention provides a compound of formula V:

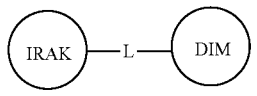

V or a pharmaceutically acceptable salt thereof, wherein:
IRAK is an IRAK binding moiety capable of binding to one or more of IRAK-1, -2, -3, or -4;
L is a bivalent moiety that connects IRAK to DIM; and
DIM is a degradation inducing moiety.

In some embodiments, the present invention provides a compound of formula V:

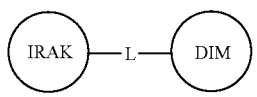

V or a pharmaceutically acceptable salt thereof, wherein:
IRAK is an IRAK-4 binding moiety;
L is a bivalent moiety that connects IRAK to DIM; and
DIM is LBM, a lysine mimetic, or a hydrogen atom.

IRAK Binding Moeity (IRAK)

In certain embodiments, the present invention provides a compound of formula I, where IRAK is a IRAK-4 binding moiety thereby forming a compound of formula II:

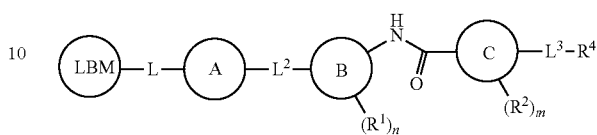

II or a pharmaceutically acceptable salt thereof, wherein L and LBM are as defined above and described in embodiments herein, and wherein:

Ring A is a 4-10 membered saturated mono- or bicyclic carbocyclic or hetereocyclic ring having 0-2 heteroatoms independently selected from nitrogen, oxygen, and sulfur;

Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur;

Ring C is phenyl or a 5-10 membered mono- or bicyclic heteroaryl ring having 1-5 heteroatoms independently selected from nitrogen, oxygen, and sulfur;

each of $L^2$ and $L^3$ is independently a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—;

each $R^1$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CFR$_2$, —CF$_2$(R), —CF$_3$, —CR$_2$(OR), —CR$_2$(NR$_2$), —C(O)R, —C(O)OR, or —C(O)NR$_2$;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each $R^2$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, N(R)C(O)OR, —N(R)C(O)R, —N(R)C(O)NR$_2$, or —N(R)S(O)$_2$R;

$R^4$ is selected from

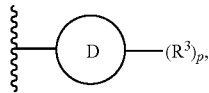

hydrogen, or an optionally substituted group selected from $C_{1-6}$ aliphatic or a 4-11 membered saturated or partially unsaturated carbocyclic or heterocyclic monocyclic, bicyclic, bridged bicyclic, or spiro ring having 1-3 heteroatoms independently selected from nitrogen, oxygen, and sulfur;

Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;

each $R^3$ is independently hydrogen, deuterium, —$R^5$, halogen, —CN, —$NO_2$, —OR, —SR, —$NR_2$, —$S(O)_2R$, —$S(O)_2NR_2$, —S(O)R, —S(O)(NR)R, —$P(O)(OR)_2$, —$P(O)(NR_2)_2$, —$CF_2(R)$, —$CF_3$, —$CR_2(OR)$, —$CR_2(NR_2)$, —C(O)R, —C(O)OR, C(O)$NR_2$, —C(O)N(R)OR, —OC(O)R, —OC(O)$NR_2$, N(R)C(O)OR, —N(R)C(O)R, —N(R)C(O)$NR_2$, or —N(R)$S(O)_2R$;

each $R^5$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, or 2;

each m is 0, 1, 2, 3 or 4; and each p is 0, 1, 2, 3 or 4;

wherein the compound of formula II is not compound I-99 or I-100 in Table 1A.

In certain embodiments, the present invention provides a compound of Formula II':

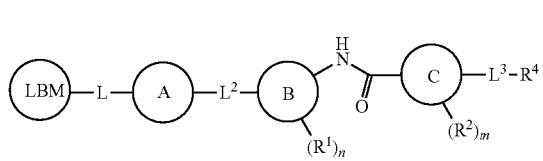

II' or a pharmaceutically acceptable salt thereof, wherein:

Ring A is an optionally substituted 4-10 membered saturated mono- or bicyclic carbocyclic or heterocyclic ring having 0-2 heteroatoms independently selected from nitrogen, oxygen, and sulfur;

Ring B is phenyl, a 4-7 membered saturated or partially unsaturated carbocyclic ring or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;

Ring C is phenyl, a 4-7 membered saturated or partially unsaturated carbocyclic ring or heterocyclic ring having 1-3 heteroatoms independently selected from nitrogen, oxygen, and sulfur, or a 5-6 membered heteroaryl ring having 1-5 heteroatoms independently selected from nitrogen, oxygen, and sulfur;

each of $L^2$ and $L^3$ is independently a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —$C(R)_2$—, —CH(R)—, —$C(F)_2$—, —N(R)—, —S—, —$S(O)_2$— or —CR=CR—;

each $R^1$ is independently hydrogen, deuterium, —$R^5$, halogen, —CN, —$NO_2$, —OR, —SR, —$NR_2$, —$S(O)_2R$, —$S(O)_2NR_2$, —S(O)R, —S(O)(NR)R, —$P(O)(OR)_2$, —$P(O)(NR_2)_2$, —$CFR_2$, —$CF_2(R)$, —$CF_3$, —$CR_2(OR)$, —$CR_2(NR_2)$, —C(O)R, —C(O)OR, or —C(O)$NR_2$, or two $R^1$ on the same carbon together form =O or =S;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each $R^2$ is independently hydrogen, deuterium, —$R^5$, halogen, —CN, —$NO_2$, —OR, —SR, —$NR_2$, —$S(O)_2R$, —$S(O)_2NR_2$, —S(O)R, —S(O)(NR)R, —$P(O)(OR)_2$, —$P(O)(NR_2)_2$, —$CF_2(R)$, —$CF_3$, —$CR_2(OR)$, —$CR_2(NR_2)$, —C(O)R, —C(O)OR, C(O)$NR_2$, —C(O)N(R)OR, —OC(O)R, —OC(O)$NR_2$, N(R)C(O)OR, —N(R)C(O)R, —N(R)C(O)$NR_2$, or —N(R)$S(O)_2R$, or two $R^2$ on the same carbon together form =O or =S;

$R^4$ is selected from hydrogen or

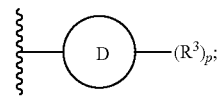

Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;

each $R^3$ is independently hydrogen, deuterium, —$R^5$, halogen, —CN, —$NO_2$, —OR, —SR, —$NR_2$, —$S(O)_2R$, —$S(O)_2NR_2$, —S(O)R, —S(O)(NR)R, —$P(O)(OR)_2$, —$P(O)(NR_2)_2$, —$CF_2(R)$, —$CF_3$, —$CR_2(OR)$, —$CR_2(NR_2)$, —C(O)R, —C(O)OR, C(O)$NR_2$, —C(O)N(R)OR, —OC(O)R, —OC(O)$NR_2$, N(R)C(O)OR, —N(R)C(O)R, —N(R)C(O)$NR_2$, or —N(R)$S(O)_2R$, or two $R^3$ on the same carbon together form =O or =S;

each $R^5$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, or 2;
each m is 0, 1, 2, 3 or 4;
each p is 0, 1, 2, 3 or 4;

In certain embodiments, the present invention provides a compound of formula V, where IRAK is a IRAK-4 binding moiety thereby forming a compound of formula V-a:

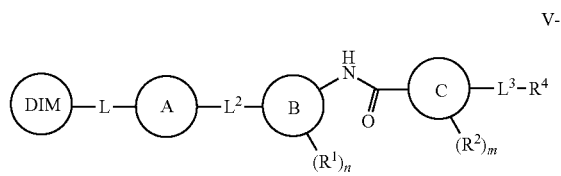

V-a or a pharmaceutically acceptable salt thereof, wherein L and DIM are as defined above and described in embodiments herein, and wherein:

Ring A is a 4-10 membered saturated mono- or bicyclic carbocyclic or hetereocyclic ring having 0-2 heteroatoms independently selected from nitrogen, oxygen, and sulfur;

Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur;

Ring C is phenyl or a 5-10 membered mono- or bicyclic heteroaryl ring having 1-5 heteroatoms independently selected from nitrogen, oxygen, and sulfur;

each of $L^2$ and $L^3$ is independently a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—;

each $R^1$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CFR$_2$, —CF$_2$(R), —CF$_3$, —CR$_2$(OR), —CR$_2$(NR$_2$), —C(O)R, —C(O)OR, or —C(O)NR$_2$;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each $R^2$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, N(R)C(O)OR, —N(R)C(O)R, —N(R)C(O)NR$_2$, or —N(R)S(O)$_2$R;

$R^4$ is selected from

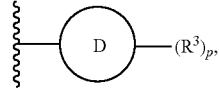

hydrogen, or an optionally substituted group selected from $C_{1-6}$ aliphatic or a 4-11 membered saturated or partially unsaturated carbocyclic or heterocyclic monocyclic, bicyclic, bridged bicyclic, or spiro ring having 1-3 heteroatoms independently selected from nitrogen, oxygen, and sulfur;

Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;

each $R^3$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, N(R)C(O)OR, —N(R)C(O)R, —N(R)C(O)NR$_2$, or —N(R)S(O)$_2$R;

each $R^5$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, or 2;
each m is 0, 1, 2, 3 or 4; and
each p is 0, 1, 2, 3 or 4;
wherein the compound of formula V-a is not compound I-99 or I-100 in Table 1A.

The below embodiments are to compounds of formula II, II' and V-a.

As defined generally above, Ring A is a 4-10 membered saturated mono- or bicyclic carbocyclic or hetereocyclic ring having 0-2 heteroatoms independently selected from nitrogen, oxygen, and sulfur.

In some embodiments, Ring A is cyclobutyl. In some embodiments, Ring A is cyclopentyl. In some embodiments, Ring A is cyclohexyl. In some embodiments, Ring A is cycloheptyl. In some embodiments, Ring A is

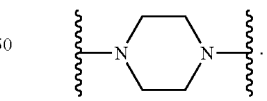

In some embodiments, Ring A is

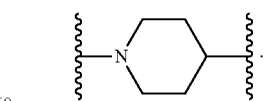

In some embodiments, Ring A is selected from those depicted in Table 1, below.

As generally defined above, Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur.

In some embodiments, Ring B is phenyl. In some embodiments, Ring B is a 4-10 membered saturated or partially unsaturated mono- or bicyclic carbocyclic or heterocyclic ring having 1-3 heteroatoms independently selected from nitrogen, oxygen, and sulfur. In some embodiments, Ring B is a 5-9 membered mono- or bicyclic heteroaryl ring having 1-4 heteroatoms independently selected from nitrogen, oxygen, and sulfur.

In some embodiments, Ring B is

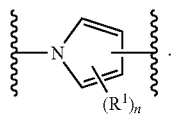

In some embodiments, Ring B is

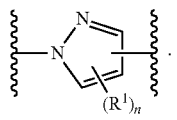

In some embodiments, Ring B is

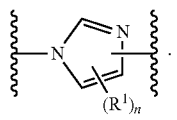

In some embodiments, Ring B is

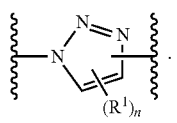

In some embodiments, Ring B is

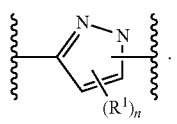

In some embodiments, Ring B is

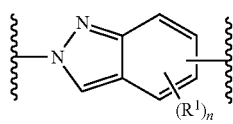

As defined generally above, Ring C is phenyl or a 5-10 membered mono- or bicyclic heteroaryl ring having 1-5 heteroatoms independently selected from nitrogen, oxygen, and sulfur.

In some embodiments, Ring C is phenyl. In some embodiments, Ring C is a 5-10 membered mono- or bicyclic heteroaryl ring having 1-5 heteroatoms independently selected from nitrogen, oxygen, and sulfur.

In some embodiments, Ring C is

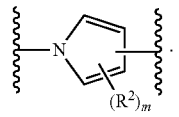

In some embodiments, Ring C is

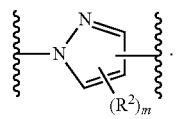

In some embodiments, Ring C is

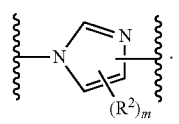

In some embodiments, Ring C is

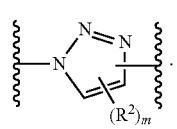

In some embodiments, Ring C is

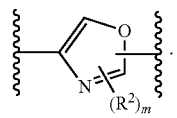

In some embodiments, Ring C is

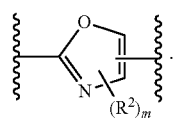

In some embodiments, Ring C is

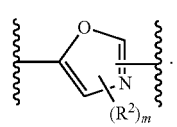

In some embodiments, Ring C is

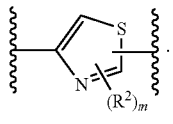

In some embodiments, Ring C is

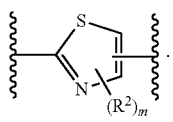

In some embodiments, Ring C is

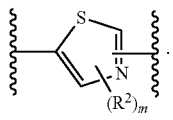

In some embodiments, Ring C is

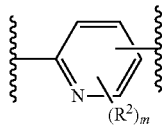

In some embodiments, Ring C is

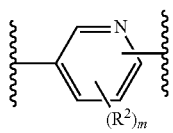

In some embodiments, Ring C is

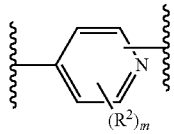

In some embodiments, Ring C is

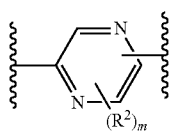

In some embodiments, Ring C is

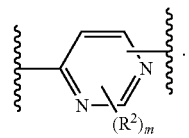

In some embodiments, Ring C is

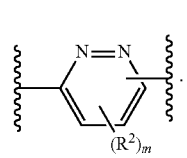

In some embodiments, Ring C is

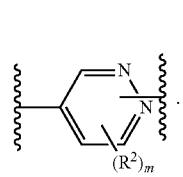

In some embodiments, Ring C is

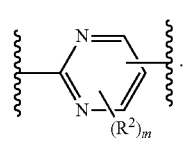

In some embodiments, Ring C is

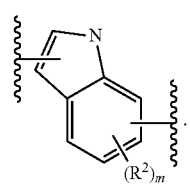

In some embodiments, Ring C is

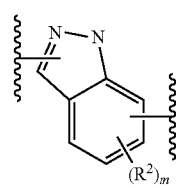

In some embodiments, Ring C is

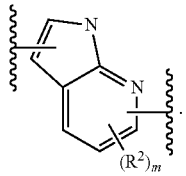

In some embodiments, Ring C is

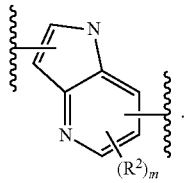

In some embodiments, Ring C is

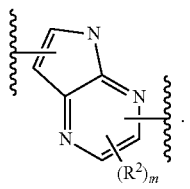

In some embodiments, Ring C is

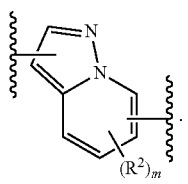

In some embodiments, Ring C is

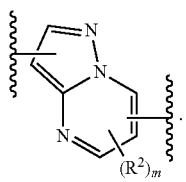

In some embodiments, Ring C is selected from those depicted in Table 1, below.

As generally defined above, $L^2$ is a bivalent moiety selected from a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—.

In some embodiments, $L^2$ a covalent bond. In some embodiments, $L^2$ is a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—. In some embodiments, $L^2$ is a $C_{1-3}$ aliphatic. In some embodiments, $L^2$ is —CH$_2$—. In some embodiments, $L^2$ is —C(D)(H)—. In some embodiments, $L^2$ is —C(D)$_2$-. In some embodiments, $L^2$ is —CH$_2$CH$_2$—. In some embodiments, $L^2$ is —NR—. In some embodiments, $L^2$ is —CH$_2$NR—. In some embodiments, $L^2$ is or —O—. In some embodiments, $L^2$ is —CH$_2$O—. In some embodiments, $L^2$ is —S—. In some embodiments, $L^2$ is —OC(O)—. In some embodiments, $L^2$ is —C(O)O—. In some embodiments, $L^2$ is —C(O)—. In some embodiments, $L^2$ is —S(O)—. In some embodiments, $L^2$ is —S(O)$_2$—. In some embodiments, $L^2$ is —NRS(O)$_2$—. In some embodiments, $L^2$ is —S(O)$_2$NR—. In some embodiments, $L^2$ is —NRC(O)—. In some embodiments, $L^2$ is —C(O)NR—. In some embodiments, $L^2$ is —OC(O)NR—. In some embodiments, $L^2$ is —NRC(O)O—.

As generally defined above, $L^3$ is a bivalent moiety selected from a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—.

In some embodiments, $L^3$ is a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—. In some embodiments, $L^3$ is a $C_{1-3}$ aliphatic. In some embodiments, $L^3$ is —CH$_2$—. In some embodiments, $L^3$ is —C(D)(H)—. In some embodiments, $L^3$ is —C(D)$_2$-. In some embodiments, $L^3$ is —CH$_2$CH$_2$—. In some embodiments, $L^3$ is —NR—. In some embodiments, $L^3$ is —CH$_2$NR—. In some embodiments, $L^3$ is or —O—. In some embodiments, $L^3$ is —CH$_2$O—. In some embodiments, $L^3$ is —S—. In some embodiments, $L^3$ is —OC(O)—. In some embodiments, $L^3$ is —C(O)O—. In some embodiments, $L^3$ is —C(O)—. In some embodiments, $L^3$ is —S(O)—. In some embodiments, $L^3$ is —S(O)$_2$—. In some embodiments, $L^3$ is —NRS(O)$_2$—. In some embodiments, $L^3$ is —S(O)$_2$NR—. In some embodiments, $L^3$ is —NRC(O)—. In some embodiments, $L^3$ is —C(O)NR—. In some embodiments, $L^3$ is —OC(O)NR—. In some embodiments, $L^3$ is —NRC(O)O—.

In some embodiments, $L^2$ and $L^3$ are selected from those depicted in Table 1, below.

As defined generally above, each $R^1$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CFR$_2$, —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$^2$, —OP(O)R$^2$, —OP(O)(OR)$_2$, —OP(O)(OR)NR$_2$, —OP(O)(NR$_2$)$_2$, —P(O)R$^2$, —SiR$_3$, —Si(OR)R$^2$, —SF$_5$, or

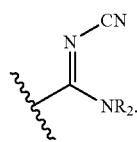

In some embodiments, each $R^1$ is independently hydrogen. In some embodiments, $R^1$ is deuterium. In some embodiments, each $R^1$ is independently —$R^5$. In some embodiments, each $R^1$ is independently halogen. In some embodiments, each $R^1$ is independently —CN. In some embodiments, each $R^1$ is independently —$NO_2$. In some embodiments, each $R^1$ is independently —OR. In some embodiments, each $R^1$ is independently —SR. In some embodiments, each $R^1$ is independently —$NR_2$. In some embodiments, each $R^1$ is independently —$S(O)_2R$. In some embodiments, each $R^1$ is independently —$S(O)_2NR_2$. In some embodiments, each $R^1$ is independently —S(O)R. In some embodiments, each $R^1$ is independently —S(O)(NR)R. In some embodiments, each $R^1$ is independently —P(O)(OR)$_2$. In some embodiments, each $R^1$ is independently —P(O)(NR$_2$)$_2$. In some embodiments, each $R^1$ is independently —$CF_2(R)$. In some embodiments, each $R^1$ is independently —$CFR_2$. In some embodiments, each $R^1$ is independently —$CF_3$. In some embodiments, each $R^1$ is independently —$CR_2(OR)$. In some embodiments, each $R^1$ is independently —$CR_2(NR_2)$. In some embodiments, each $R^1$ is independently —C(O)R. In some embodiments each $R^1$ is independently —C(O)OR. In some embodiments, each $R^1$ is independently —C(O)NR$_2$. In some embodiments, each $R^1$ is independently —C(O)N(R)OR. In some embodiments, each $R^1$ is independently —OC(O)R. In some embodiments, each $R^1$ is independently —OC(O)NR$_2$. In some embodiments, each $R^1$ is independently —N(R)C(O)OR. In some embodiments, each $R^1$ is independently —N(R)C(O)R. In some embodiments, each $R^1$ is independently —N(R)C(O)NR$_2$. In some embodiments, each $R^1$ is independently —N(R)S(O)$_2$R. In some embodiments, each $R^1$ is independently —N$^+$(O$^-$)R$_2$. In some embodiments, each $R^1$ is independently —OP(O)R$^2$. In some embodiments, each $R^1$ is independently —OP(O)(OR)$_2$. In some embodiments, each $R^1$ is independently —OP(O)(OR)NR$_2$. In some embodiments, each $R^1$ is independently —OP(O)(NR$_2$)$_2$. In some embodiments, each $R^1$ is independently —P(O)R$^2$. In some embodiments, each $R^1$ is independently —SiR$_3$. In some embodiments, each $R^1$ is independently —Si(OR)R$^2$. In some embodiments, each $R^1$ is independently —SF$_5$. In some embodiments, each $R^1$ is independently

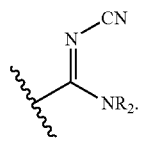

In some embodiments, $R^1$ is —CHF$_2$. In some embodiments, $R^1$ is —C(OH)(CH$_3$)$_2$. In some embodiments, $R^1$ is —C(O)NH$_2$. In some embodiments, $R^1$ is —CF$_3$. In some embodiments, $R^1$ is -iPr. In some embodiments, $R^1$ is isoprene. In some embodiments, $R^1$ is

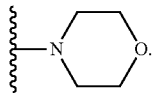

In some embodiments, $R^1$ is

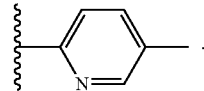

As defined generally above, each $R^2$ and $R^3$ are independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CFR$_2$, —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —N$^+$(O$^-$)R$_2$, —OP(O)R$^2$, —OP(O)(OR)$_2$, —OP(O)(OR)NR$_2$, —OP(O)(NR$_2$)$_2$, —P(O)R$^2$, —SiR$_3$, —Si(OR)R$^2$, —SF$_5$, or

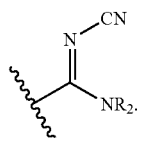

In some embodiments, each $R^2$ and $R^3$ are independently hydrogen. In some embodiments, each $R^2$ and $R^3$ are independently deuterium. In some embodiments, each $R^2$ and $R^3$ are independently —$R^5$. In some embodiments, each $R^2$ and $R^3$ are independently halogen. In some embodiments, each $R^2$ and $R^3$ are independently —CN. In some embodiments, each $R^2$ and $R^3$ are independently —NO$_2$. In some embodiments, each $R^2$ and $R^3$ are independently —OR. In some embodiments, each $R^2$ and $R^3$ are independently —SR. In some embodiments, each $R^2$ and $R^3$ are independently —NR$_2$. In some embodiments, each $R^2$ and $R^3$ are independently —S(O)$_2$R. In some embodiments, each $R^2$ and $R^3$ are independently —S(O)$_2$NR$_2$. In some embodiments, each $R^2$ and $R^3$ are independently —S(O)R. In some embodiments, each $R^2$ and $R^3$ are independently —S(O)(NR)R. In some embodiments, each $R^2$ and $R^3$ are independently —P(O)(OR)$_2$. In some embodiments, each $R^2$ and $R^3$ are independently —P(O)(NR$_2$)$_2$. In some embodiments, each $R^2$ and $R^3$ are independently —CF$_2$(R). In some embodiments, each $R^2$ and $R^3$ are independently —CFR$_2$. In some embodiments, each $R^2$ and $R^3$ are independently —CF$_3$. In some embodiments, each $R^2$ and $R^3$ are independently —CR$_2$(OR). In some embodiments, each $R^2$ and $R^3$ are independently —CR$_2$(NR$_2$). In some embodiments, each $R^2$ and $R^3$ are independently —C(O)R. In some embodiments, each $R^2$ and $R^3$ are independently —C(O)OR. In some embodiments, each $R^2$ and $R^3$ are independently —C(O)NR$_2$. In some embodiments, each $R^2$ and $R^3$ are independently —C(O)N(R)OR. In some embodiments, each $R^2$ and $R^3$ are independently —OC(O)R. In some embodiments, each $R^2$ and $R^3$ are independently —OC(O)NR$_2$. In some embodiments, each $R^2$ and $R^3$ are independently —N(R)C(O)OR. In some embodiments, each $R^2$ and $R^3$ are independently —N(R)C(O)R. In some embodiments, each $R^2$ and $R^3$ are independently —N(R)C(O)NR$_2$. In some embodiments, each $R^1$ and $R^2$ are independently —N(R)S(O)$_2$R. In some embodiments, each $R^2$ and $R^3$ are independently —N$^+$(O$^-$)R$_2$. In some embodiments, each $R^2$ and $R^3$ are independently —OP(O)R$^2$. In some embodiments, each $R^2$ and $R^3$ are independently —OP(O)(OR)$_2$. In some embodiments, each $R^2$ and $R^3$ are independently —OP(O)(OR)NR$_2$. In some embodiments, each $R^2$ and $R^3$ are independently —OP(O)

$(NR_2)_2$. In some embodiments, each $R^2$ and $R^3$ are independently —$P(O)R^2$. In some embodiments, each $R^2$ and $R^3$ are independently —$SiR_3$. In some embodiments, each $R^2$ and $R^3$ are independently —$Si(OR)R^2$. In some embodiments, each $R^2$ and $R^3$ are independently —$SF_5$. In some embodiments, each $R^2$ and $R^3$ are independently

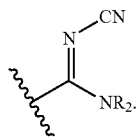

In some embodiments, $R^2$ is —$CF_3$. In some embodiments, $R^2$ is

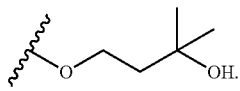 [SMILES: *OCCC(C)(C)O]

In some embodiments, $R^2$ is

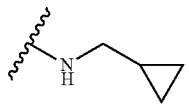

In some embodiments, $R^2$ is

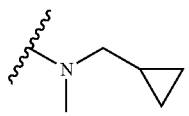

In some embodiments, $R^2$ is —$C(OH)(CH_3)_2$. In some embodiments, $R^2$ is

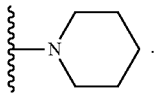

In some embodiments, $R^3$ is —$NHCH_3$. In some embodiments, $R^3$ is —$CH_3$. In some embodiments, $R^3$ is

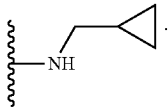

In some embodiments, $R^3$ is

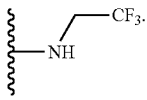

In some embodiments, $R^3$ is —$C(OH)(CH_3)_2$. In some embodiments, $R^3$ is

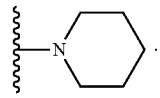

In some embodiments, each $R^1$, $R^2$, and $R^3$ are independently selected from those depicted in Table 1, below.

As generally defined above, $R^4$ is selected from

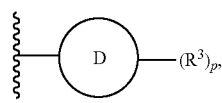

hydrogen, or an optionally substituted group selected from $C_{1-6}$ aliphatic or a 4-11 membered saturated or partially unsaturated carbocyclic or heterocyclic monocyclic, bicyclic, bridged bicyclic, or spiro ring having 1-3 heteroatoms independently selected from nitrogen, oxygen, and sulfur.

In some embodiments, $R^4$ is

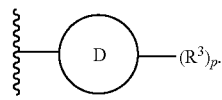

In some embodiments, $R^4$ is hydrogen. In some embodiments, $R^4$ is an optionally substituted group selected from $C_{1-6}$ aliphatic. In some embodiments, $R^4$ is an optionally substituted 4-11 membered saturated or partially unsaturated carbocyclic or heterocyclic monocyclic, bicyclic, bridged bicyclic, or spiro ring having 1-3 heteroatoms independently selected from nitrogen, oxygen, and sulfur.

In some embodiments, $R^4$ is

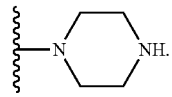

In some embodiments, $R^4$ is

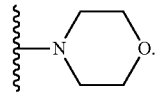

In some embodiments, $R^4$ is

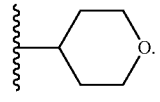

In some embodiments, R⁴ is
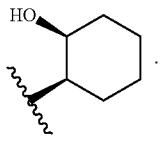
In some embodiments, R⁴ is
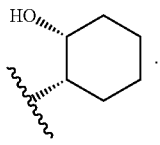
In some embodiments, R⁴ is
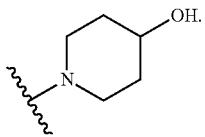 [SMILES: *N1CCC(O)CC1]
In some embodiments, R⁴ is
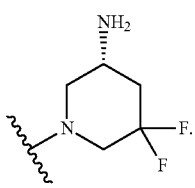
In some embodiments, R⁴ is
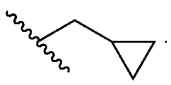
In some embodiments, R⁴ is
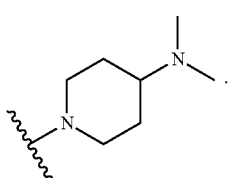 [SMILES: *N1CCC(N(C)C)CC1]
In some embodiments, R⁴ is
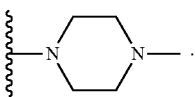
In some embodiments, R⁴ is
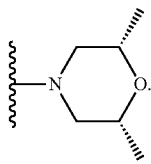 [SMILES: *N1C[C@@H](C)O[C@@H](C)C1]
In some embodiments, R⁴ is
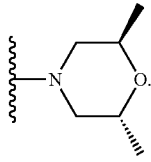
In some embodiments, R⁴ is
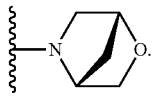
In some embodiments, R⁴ is
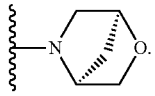
In some embodiments, R⁴ is
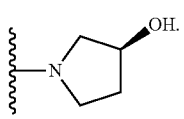
In some embodiments, R⁴ is
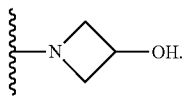 [SMILES: *N1CC(O)C1]
In some embodiments, R⁴ is
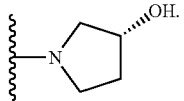 [SMILES: *N1CC[C@@H](O)C1]

In some embodiments, R⁴ is

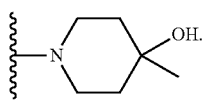

In some embodiments, R⁴ is

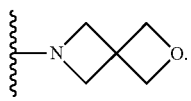

In some embodiments, R⁴ is

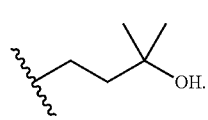 [SMILES: *CCC(C)(C)O]

In some embodiments, R⁴ is

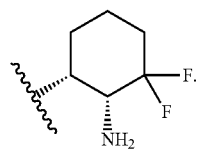

In some embodiments, R⁴ is

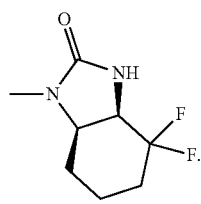

In some embodiments, R⁴ is

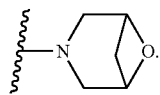

In some embodiments, R⁴ is

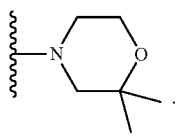 [SMILES: *N1CCOC(C)(C)C1]

In some embodiments, R⁴ is

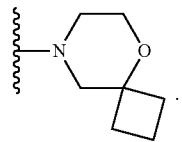 [SMILES: *N1CCOC2(CCC2)C1]

In some embodiments, R⁴ is

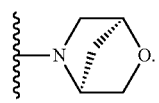

In some embodiments, R⁴ is

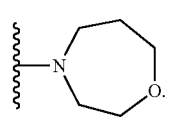

In some embodiments, R⁴ is

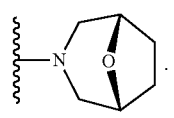

As defined generally above, Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur.

In some embodiments, Ring D is phenyl. In some embodiments, Ring D is a 4-10 membered saturated or partially unsaturated mono- or bicyclic carbocyclic or heterocyclic ring having 1-3 heteroatoms independently selected from nitrogen, oxygen, and sulfur. In some embodiments, Ring D is a 5-6 membered heteroaryl ring having 1-4 heteroatoms independently selected from nitrogen, oxygen, and sulfur.

In some embodiments, Ring D is

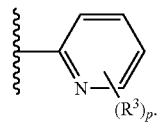

In some embodiments, Ring D is

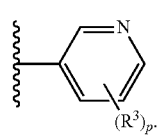

In some embodiments, Ring D is

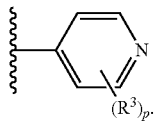

In some embodiments, Ring D is

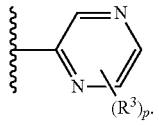

In some embodiments, Ring D is

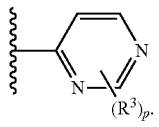

In some embodiments, Ring D is

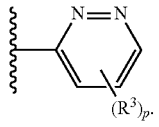

In some embodiments, Ring D is

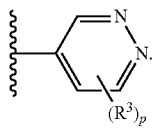

In some embodiments, Ring D is

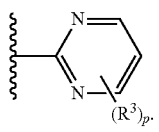

In some embodiments, Ring D is selected from those depicted in Table 1, below.

As generally defined above, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur.

In some embodiments, each R is independently hydrogen. In some embodiments, each R is an optionally substituted group selected from $C_{1-6}$ aliphatic. In some embodiments, each R is an optionally substituted phenyl. In some embodiments, each R is an optionally substituted 4-7 membered saturated or partially unsaturated heterocyclic having 1-2 heteroatoms independently selected from nitrogen, oxygen, and sulfur. In some embodiments, each R is an optionally substituted 5-6 membered heteroaryl ring having 1-4 heteroatoms independently selected from nitrogen, oxygen, and sulfur. In some embodiments, two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur.

In some embodiments, each R is selected from those depicted in Table 1, below.

As generally defined above, each $R^5$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, each $R^5$ is independently an optionally substituted group selected from $C_{1-6}$ aliphatic. In some embodiments, each $R^5$ is independently an optionally substituted phenyl. In some embodiments, each $R^5$ is independently an optionally substituted 3-7 membered saturated or partially unsaturated carbocyclic or heterocyclic ring having 1-2 heteroatoms independently selected from nitrogen, oxygen, and sulfur. In some embodiments, each $R^5$ is independently an optionally substituted 5-6 membered heteroaryl ring having 1-4 heteroatoms independently selected from nitrogen, oxygen, and sulfur.

In some embodiments, $R^5$ is

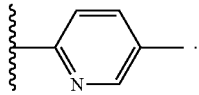

In some embodiments, $R^5$ is optionally substituted

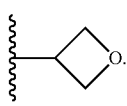

In some embodiments, each $R^5$ is selected from those depicted in Table 1, below.

As generally defined above, each n is independently 0, 1, or 2.

In some embodiments, each n is independently 0. In some embodiments, each n is independently 1. In some embodiments, each n is independently 2.

As generally defined above, each m and p are independently 0, 1, 2, 3 or 4.

In some embodiments, each m and p are independently 0. In some embodiments, each m and p are independently 1. In some embodiments, each m and p are independently 2. In some embodiments, each m and p are independently 3. In some embodiments, each m and p are independently 4.

In some embodiments, each m and p are selected from those depicted in Table 1, below.

In some embodiments, the present invention provides the compound of formula II, wherein Ring A is cyclohexyl, Ring B is pyrazolyl, and $L^3$ is a covalent bond thereby forming a compound of formula II-a:

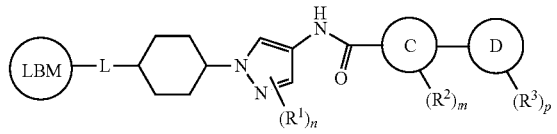

or a pharmaceutically acceptable salt thereof, wherein each of LBM, L, $R^1$, $R^2$, $R^3$, Ring C, Ring D, n, m, and p is as defined above and described in embodiments herein, both singly and in combination.

In some embodiments, the present invention provides the compound of formula II, wherein Ring A is cyclohexyl, Ring B is pyrazolyl, Ring C is oxazolyl, and $L^3$ is a covalent bond thereby forming a compound of formula II-b:

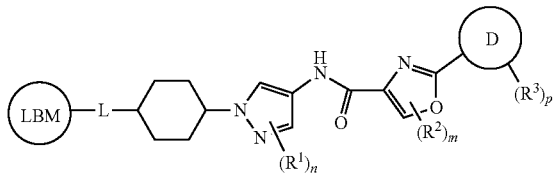

or a pharmaceutically acceptable salt thereof, wherein each of LBM, L, $R^1$, $R^2$, $R^3$, Ring D, n, m, and p is as defined above and described in embodiments herein, both singly and in combination.

In some embodiments, the present invention provides the compound of formula II, wherein Ring A is cyclohexyl, Ring B is pyrazolyl, Ring D is pyridyl, and $L^3$ is a covalent bond thereby forming a compound of formula II-c:

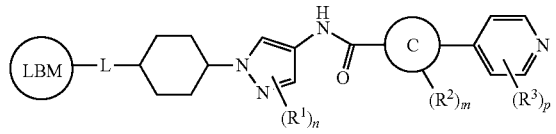

or a pharmaceutically acceptable salt thereof, wherein each of LBM, L, $R^1$, $R^2$, $R^3$, Ring C, n, m, and p is as defined above and described in embodiments herein, both singly and in combination.

In some embodiments, the present invention provides the compound of formula II, wherein Ring A is cyclohexyl, Ring B is pyrazolyl, thereby forming a compound of formula II-d:


or a pharmaceutically acceptable salt thereof, wherein each of LBM, L, $L^3$, $R^1$, $R^2$, $R^4$, Ring C, n, and m is as defined above and described in embodiments herein, both singly and in combination.

In certain embodiments, the present invention provides a compound of formula II-d:

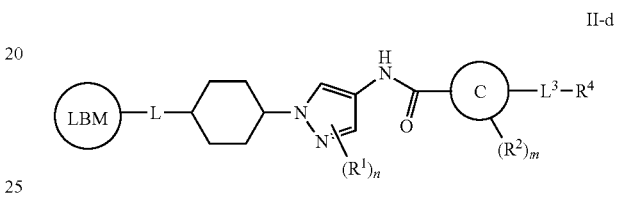

or a pharmaceutically acceptable salt thereof, wherein L and LBM are as defined above and described in embodiments herein, and wherein:

Ring C is phenyl or a 5-10 membered mono- or bicyclic heteroaryl ring having 1-5 heteroatoms independently selected from nitrogen, oxygen, and sulfur;

$L^3$ a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—;

each $R^1$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CFR$_2$, —CF$_2$(R), —CF$_3$, —CR$_2$(OR), —CR$_2$(NR$_2$), —C(O)R, —C(O)OR, or —C(O)NR$_2$;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each $R^2$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, N(R)C(O)OR, —N(R)C(O)R, —N(R)C(O)NR$_2$, or —N(R)S(O)$_2$R;

$R^4$ is selected from

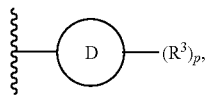

hydrogen, or an optionally substituted group selected from $C_{1-6}$ aliphatic or a 4-11 membered saturated or partially unsaturated carbocyclic or heterocyclic monocyclic, bicyclic, bridged bicyclic, or spiro ring having 1-3 heteroatoms independently selected from nitrogen, oxygen, and sulfur.

Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;

each $R^3$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, N(R)C(O)OR, —N(R)C(O)R, —N(R)C(O)NR$_2$, or —N(R)S(O)$_2$R;

each $R^5$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, or 2;

each m is 0, 1, 2, 3 or 4; and each p is 0, 1, 2, 3 or 4.

In some embodiments, the present invention provides the compound of formula II, wherein Ring A is cyclohexyl, Ring B is pyrazolyl, Ring C is pyrazolo[1,5-a]pyrimidyl, thereby forming a compound of formula II-e:

II-e

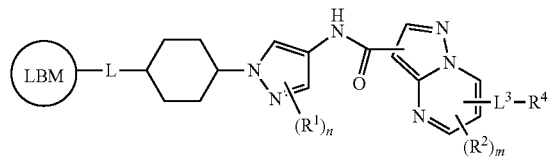

or a pharmaceutically acceptable salt thereof, wherein each of LBM, L, $L^3$, $R^1$, $R^2$, $R^4$, n, and m is as defined above and described in embodiments herein, both singly and in combination.

In certain embodiments, the present invention provides a compound of formula II-e:

II-e

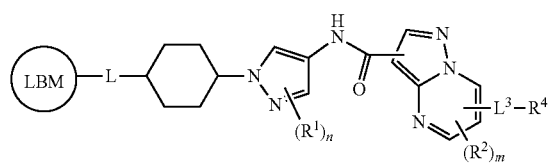

or a pharmaceutically acceptable salt thereof, wherein L and LBM are as defined above and described in embodiments herein, and wherein:

$L^3$ a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—;

each $R^1$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CFR$_2$, —CF$_2$(R), —CF$_3$, —CR$_2$(OR), —CR$_2$(NR$_2$), —C(O)R, —C(O)OR, or —C(O)NR$_2$;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each $R^2$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, N(R)C(O)OR, —N(R)C(O)R, —N(R)C(O)NR$_2$, or —N(R)S(O)$_2$R;

$R^4$ is selected from

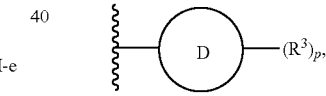

hydrogen, or an optionally substituted group selected from $C_{1-6}$ aliphatic or a 4-11 membered saturated or partially unsaturated carbocyclic or heterocyclic monocyclic, bicyclic, bridged bicyclic, or spiro ring having 1-3 heteroatoms independently selected from nitrogen, oxygen, and sulfur.

Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;

each $R^3$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR$_2$)$_2$, —CF$_2$(R), —CF$_3$, —CR$_2$(OR), —CR$_2$(NR$_2$), —C(O)R, —C(O)OR, C(O)NR$_2$, —C(O)N(R)OR, —OC(O)R, —OC(O)NR$_2$, N(R)C(O)OR, —N(R)C(O)R, —N(R)C(O)NR$_2$, or —N(R)S(O)$_2$R;

each $R^5$ is independently an optionally substituted group selected from $C_{1-6}$ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each n is 0, 1, or 2;

each m is 0, 1, 2, 3 or 4; and each p is 0, 1, 2, 3 or 4.

In some embodiments, the present invention provides the compound of formula V-a, wherein Ring A is cyclohexyl, Ring B is pyrazolyl, and L³ is a covalent bond thereby forming a compound of formula V-b:

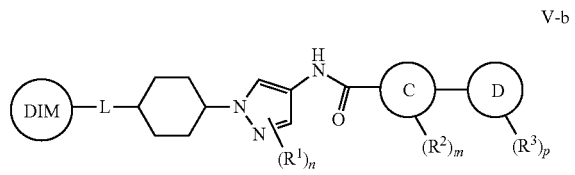

V-b or a pharmaceutically acceptable salt thereof, wherein each of DIM, L, R¹, R², R³, Ring C, Ring D, n, m, and p is as defined above and described in embodiments herein, both singly and in combination.

In some embodiments, the present invention provides the compound of formula V-a, wherein Ring A is cyclohexyl, Ring B is pyrazolyl, Ring C is oxazolyl, and L³ is a covalent bond thereby forming a compound of formula V-c:

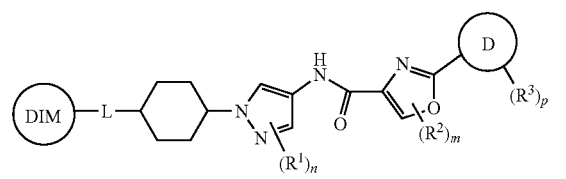

V-c or a pharmaceutically acceptable salt thereof, wherein each of DIM, L, R¹, R², R³, Ring D, n, m, and p is as defined above and described in embodiments herein, both singly and in combination.

In some embodiments, the present invention provides the compound of formula V-a, wherein Ring A is cyclohexyl, Ring B is pyrazolyl, Ring D is pyridyl, and L³ is a covalent bond thereby forming a compound of formula V-d:

V-d

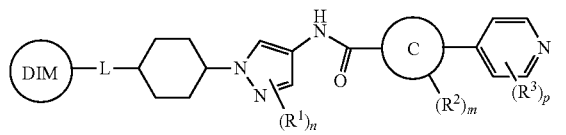

or a pharmaceutically acceptable salt thereof, wherein each of DIM, L, R¹, R², R³, Ring C, n, m, and p is as defined above and described in embodiments herein, both singly and in combination.

In some embodiments, the present invention provides the compound of formula V-a, wherein Ring A is cyclohexyl, Ring B is pyrazolyl, L³ is a covalent bond, and R⁴ is hydrogen thereby forming a compound of formula V-e:

V-e

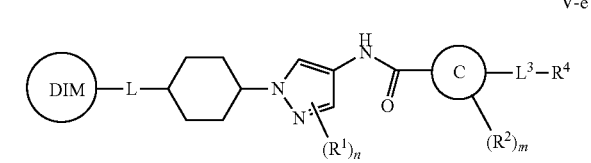

or a pharmaceutically acceptable salt thereof, wherein each of DIM, L, L³, R¹, R², R⁴, Ring C, n, and m is as defined above and described in embodiments herein, both singly and in combination.

In some embodiments, the present invention provides the compound of formula V-a, wherein Ring A is cyclohexyl, Ring B is pyrazolyl, Ring C is pyrazolo[1,5-a]pyrimidyl, L³ is a covalent bond, and R⁴ is hydrogen thereby forming a compound of formula V-f:

V-f

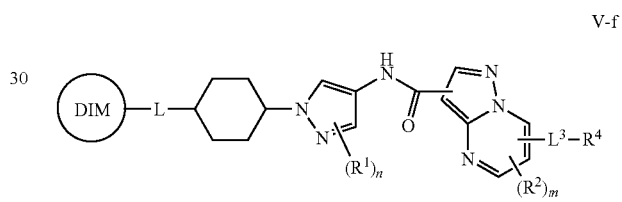

or a pharmaceutically acceptable salt thereof, wherein each of DIM, L, L³, R¹, R², R⁴, n, and m is as defined above and described in embodiments herein, both singly and in combination.

In some embodiments, IRAK is

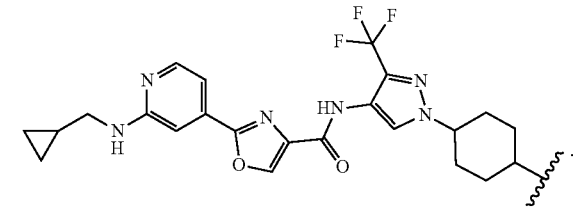

In some embodiments, IRAK is

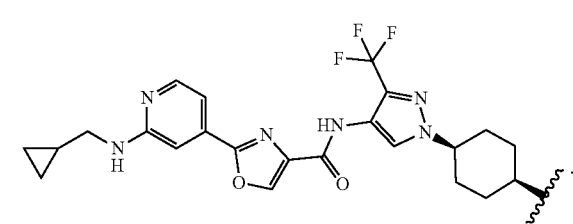

In some embodiments, IRAk is
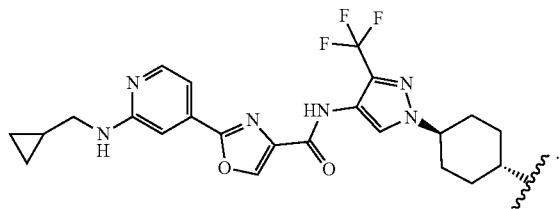
In some embodiments, IRAK is
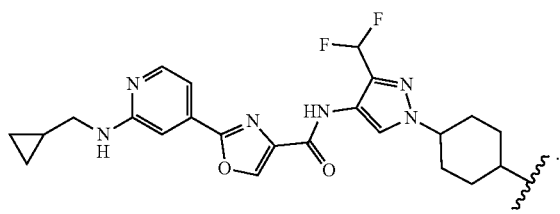
In some embodiments, IRAK is
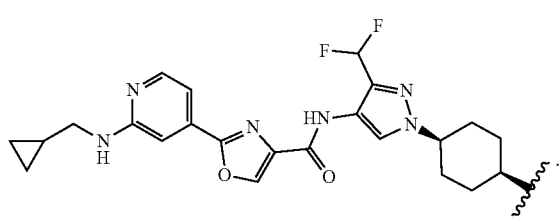
In some embodiments, IRAK is
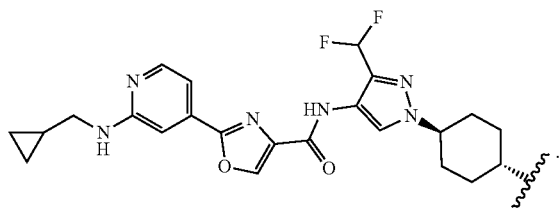
In some embodiments, IRAK is
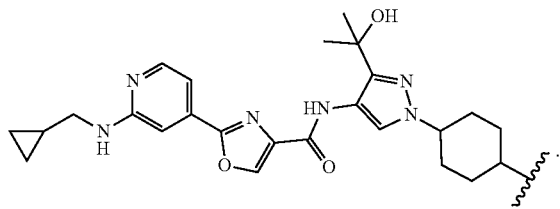
In some embodiments, IRAK is
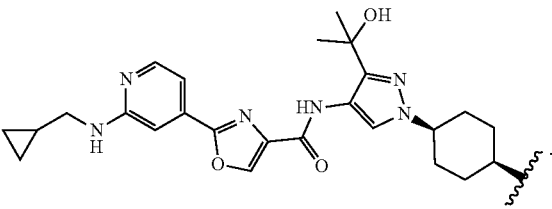
In some embodiments, IRAK is
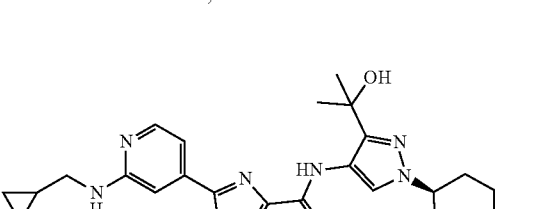
In some embodiments, IRAK is
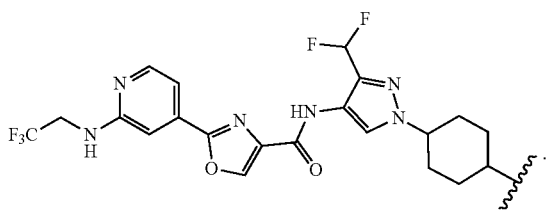
In some embodiments, IRAK is
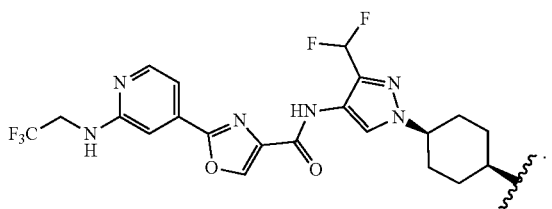
In some embodiments, IRAK is
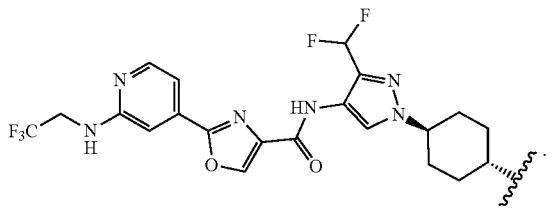

In some embodiments, IRAK is
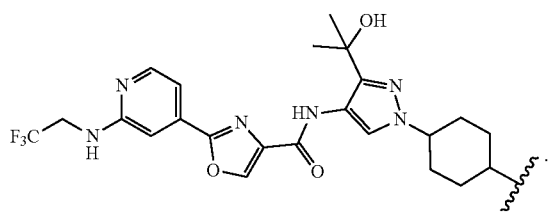
In some embodiments, IRAK is
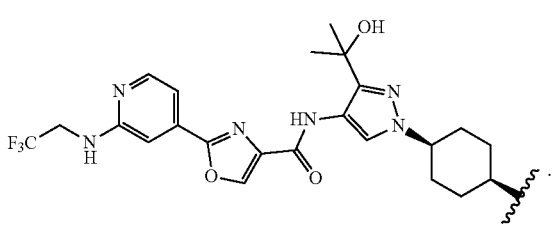
In some embodiments, IRAK is
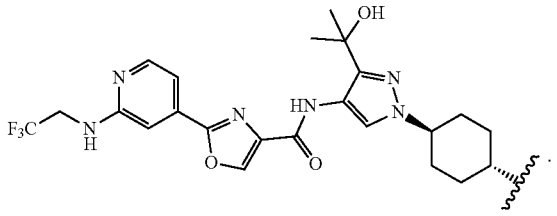
In some embodiments, IRAK is
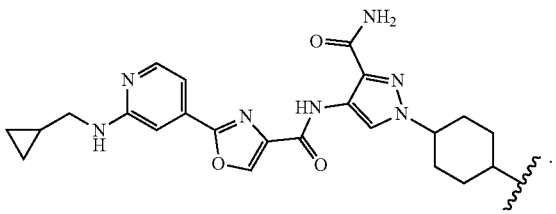
In some embodiments, IRAK is
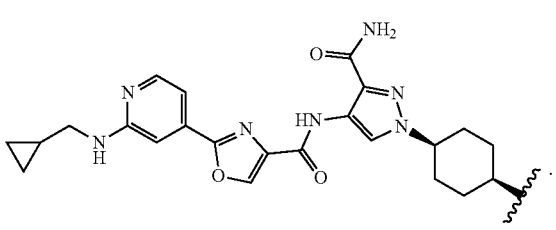
In some embodiments, IRAK is
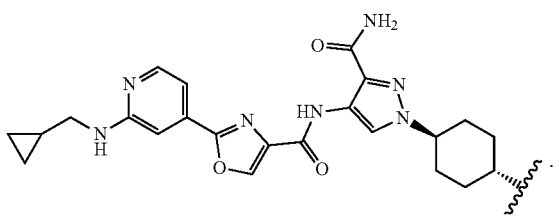
In some embodiments, IRAK is
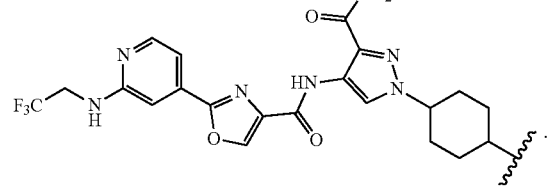
In some embodiments, IRAK is
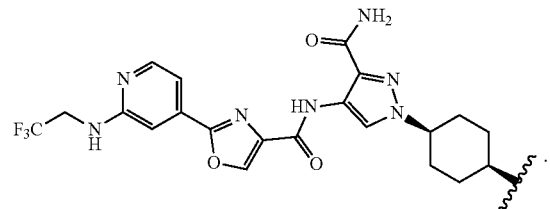
In some embodiments, IRAK is
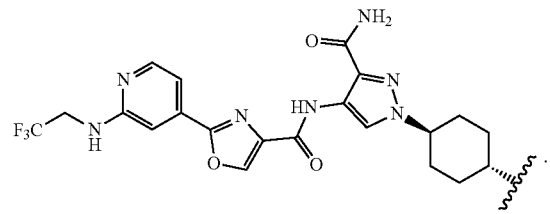
In some embodiments, IRAK is
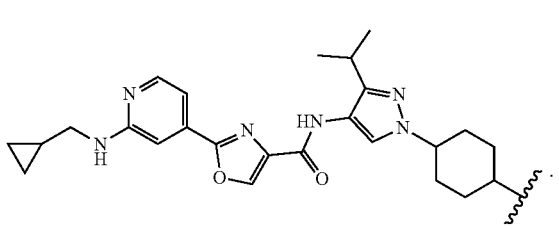

In some embodiments, IRAK is
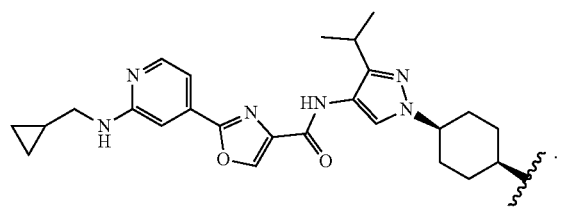
In some embodiments, IRAK is
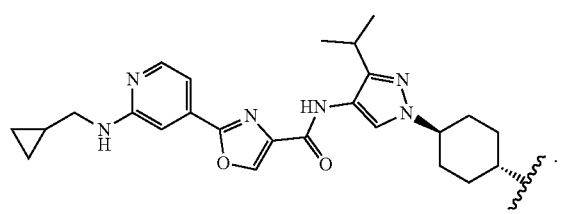
In some embodiments, IRAK is
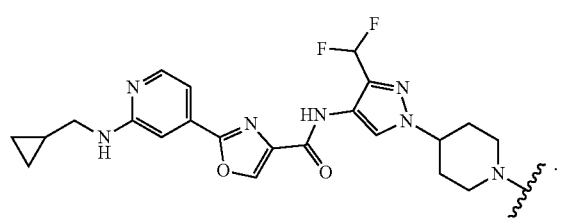
In some embodiments, IRAK is
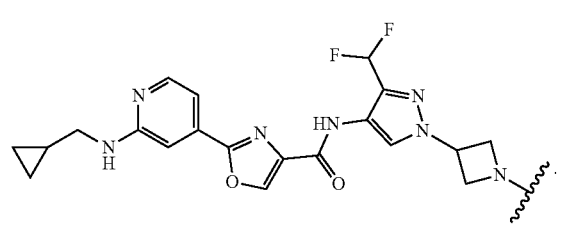
In some embodiments, IRAK is
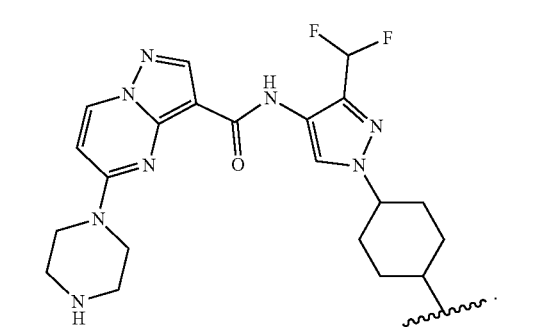
In some embodiments, IRAK is
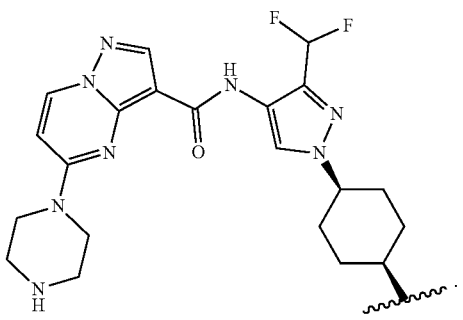
In some embodiments, IRAK is
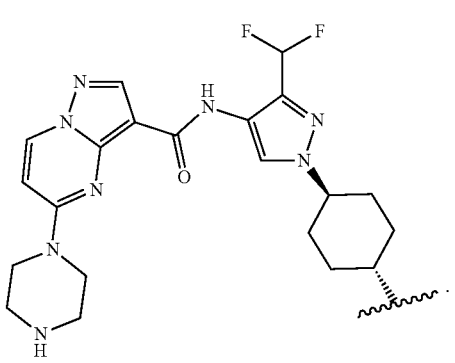
In some embodiments, IRAK is
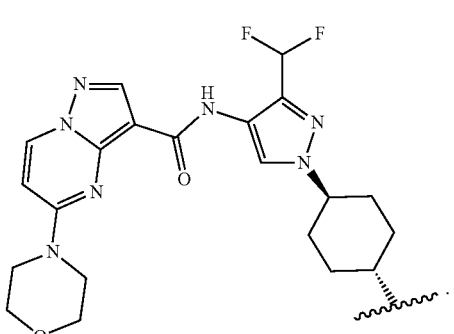
In some embodiments, IRAK is
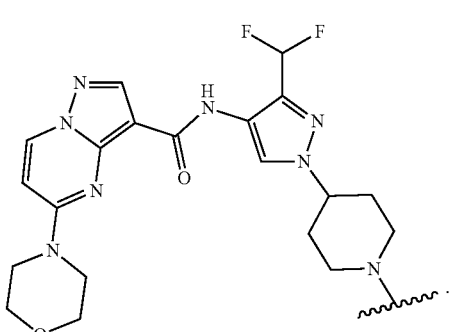

In some embodiments, IRAK is
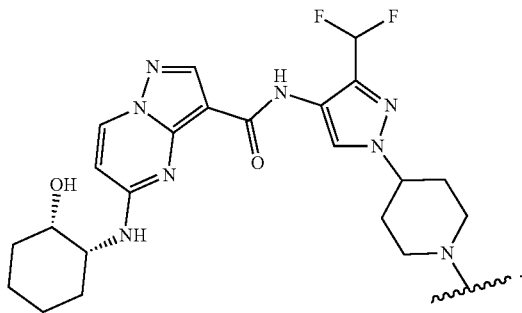
In some embodiments, IRAK is
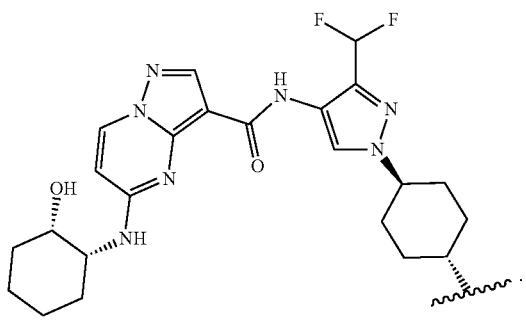
In some embodiments, IRAK is
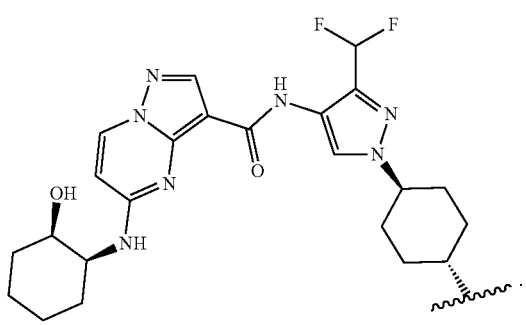
In some embodiments, IRAK is
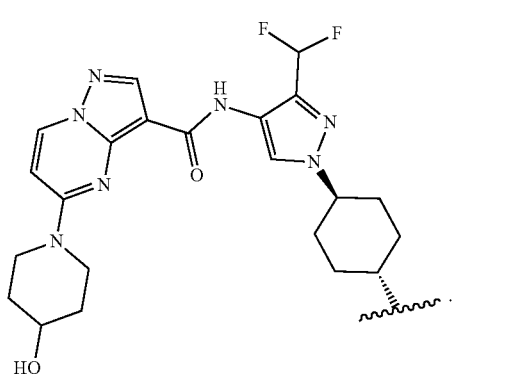
In some embodiments, IRAK is
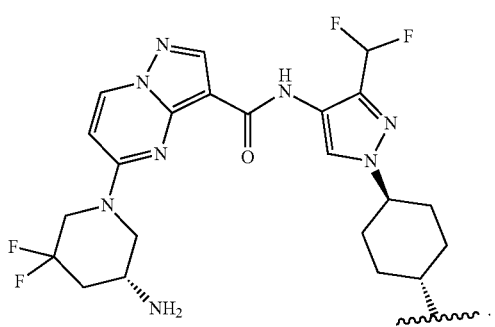
In some embodiments, IRAK is
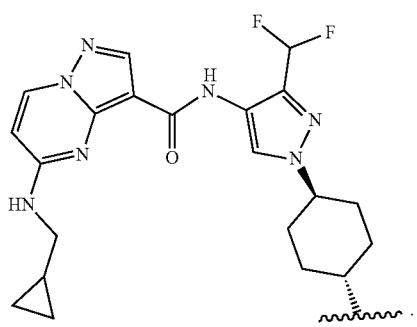
In some embodiments, IRAK is
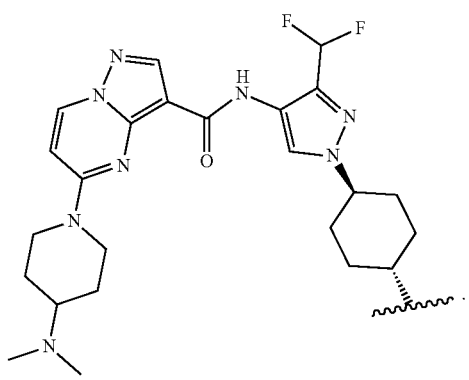

In some embodiments, IRAK is
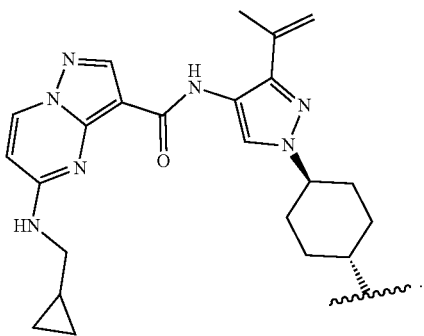
In some embodiments, IRAK is
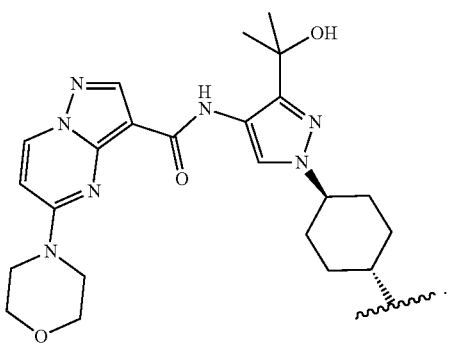
In some embodiments, IRAK is
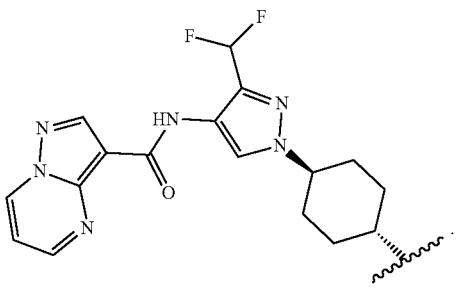 [SMILES: *[C@H]1CC[C@H](n2cc(NC(=O)c3cnn4cccnc34)c(C(F)F)n2)CC1]
In some embodiments, IRAK is
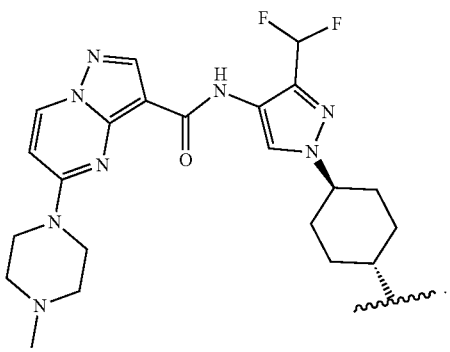
In some embodiments, IRAK is
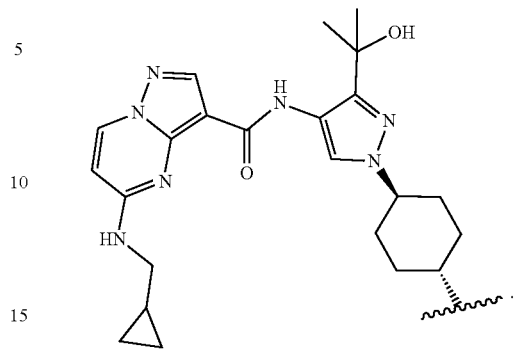
In some embodiments, IRAK is
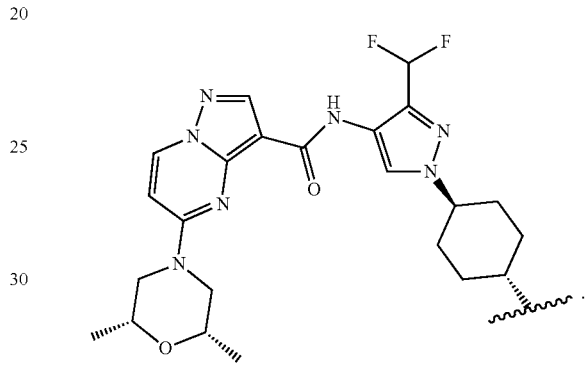
In some embodiments, IRAK is
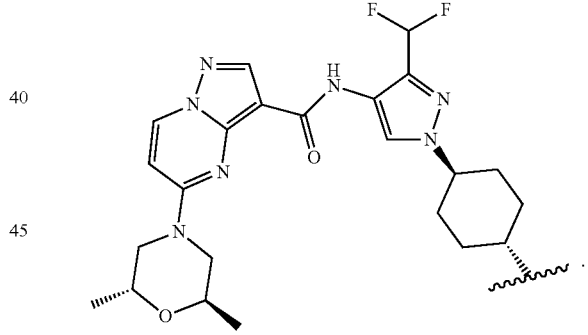
In some embodiments, IRAK is
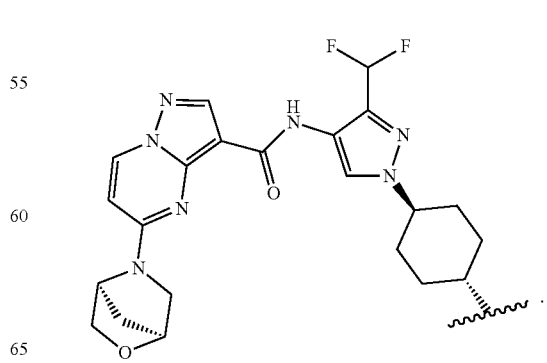

In some embodiments, IRAK is
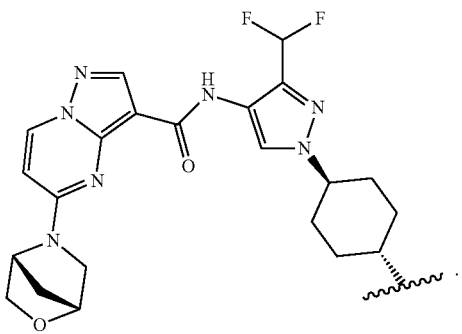
In some embodiments, IRAK is
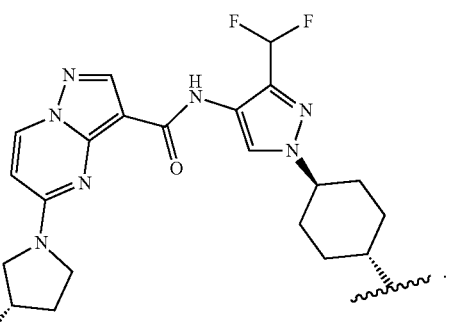
In some embodiments, IRAK is
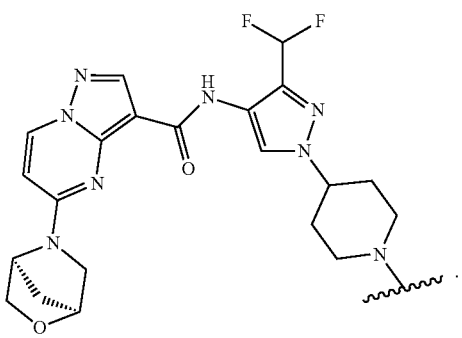
In some embodiments, IRAK is
In some embodiments, IRAK is
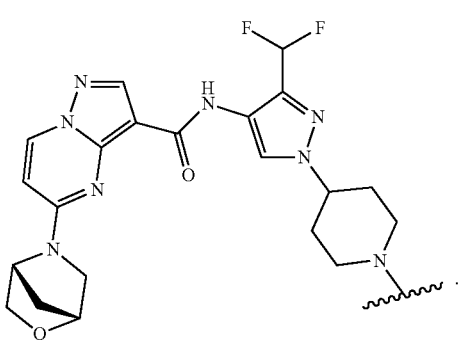
In some embodiments, IRAK is
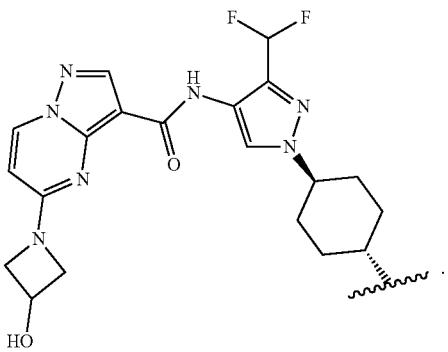

In some embodiments, IRAK is
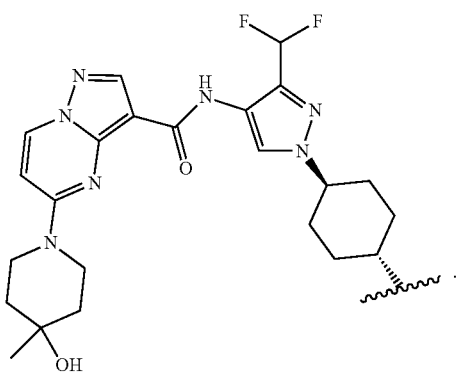
In some embodiments, IRAK is
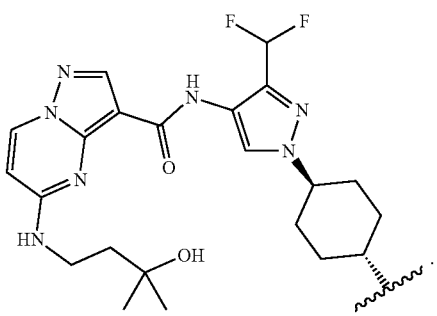
In some embodiments, IRAK is
In some embodiments, IRAK is
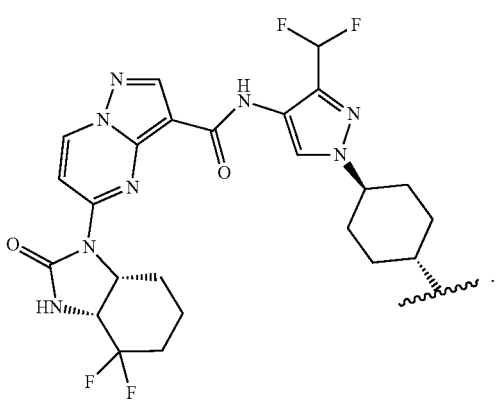
In some embodiments, IRAK is
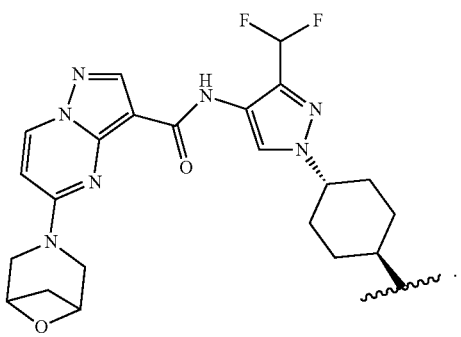
In some embodiments, IRAK is In some embodiments, IRAK is
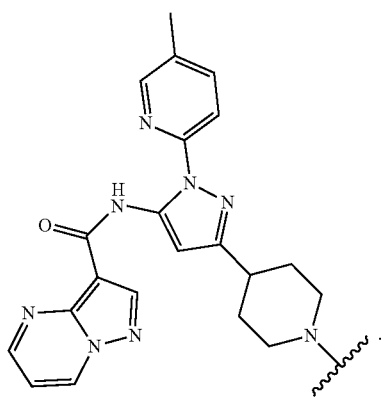
In some embodiments, IRAK is
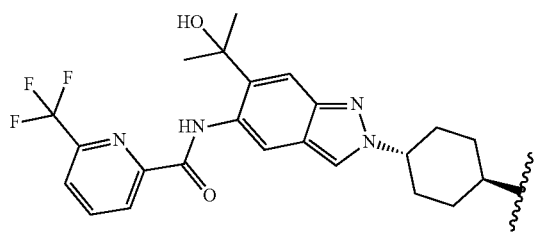
In some embodiments, IRAK is
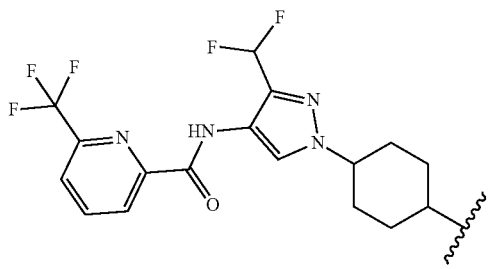
In some embodiments, IRAK is
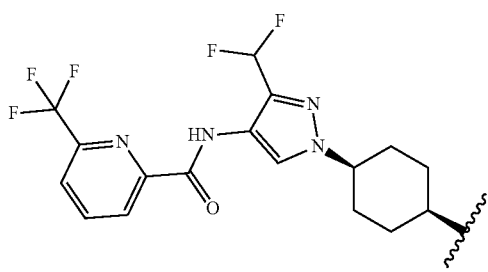
In some embodiments, IRAK is
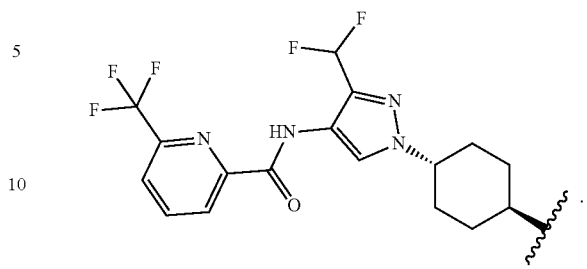
In some embodiments, IRAK is
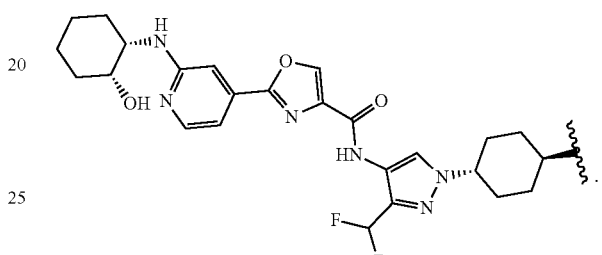
In some embodiments, IRAK is
In some embodiments, IRAK is

In some embodiments, IRAK is
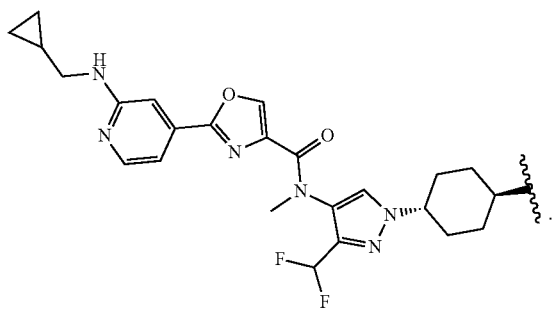
In some embodiments, IRAK is
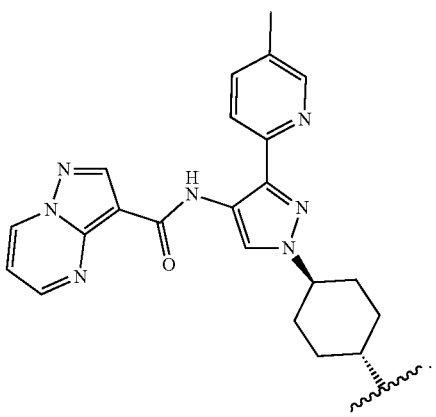
In some embodiments, IRAK is
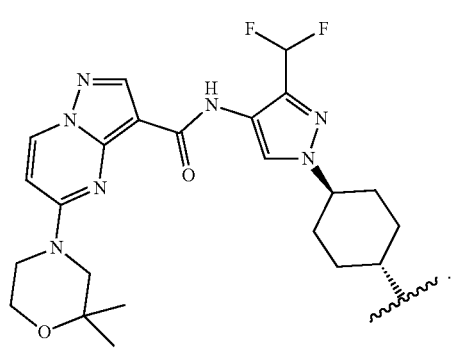
In some embodiments, IRAK is
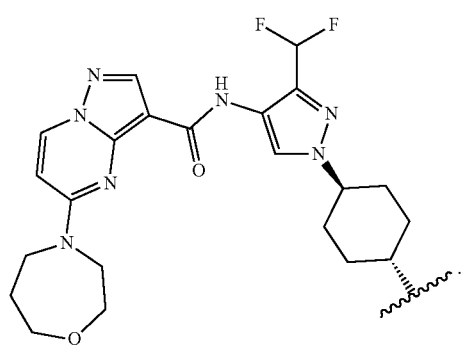
In some embodiments, IRAK is
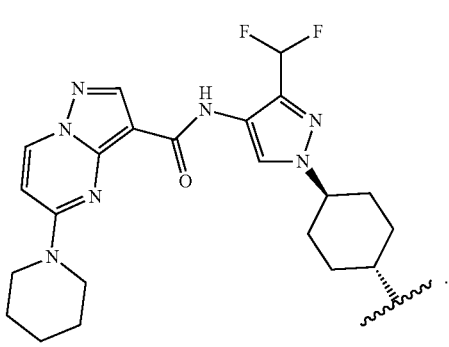
In some embodiments, IRAK is In some embodiments, IRAK is

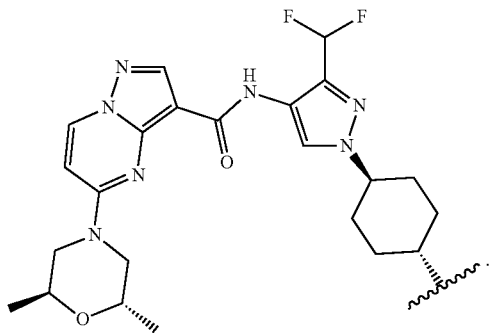

In some embodiments, IRAK is

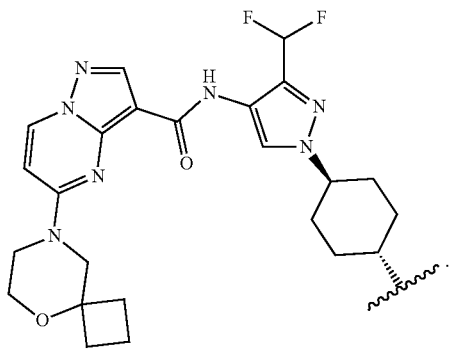

In some embodiments, IRAK is

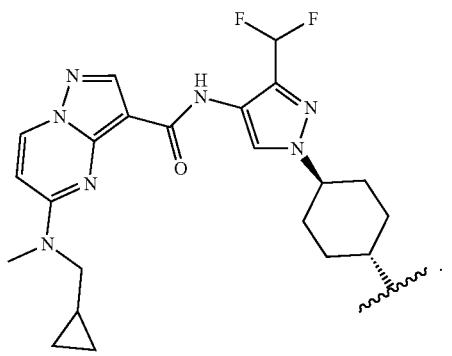

In some embodiments, IRAK is

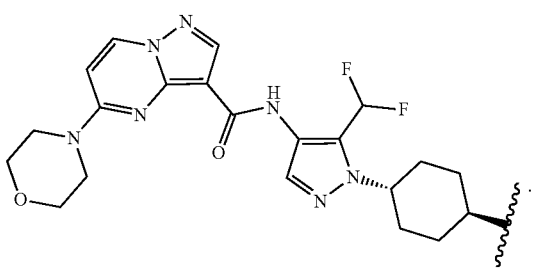

In certain embodiments, the present invention provides a compound of formula I, where IRAK is a IRAK-4 binding moiety thereby forming a compound of formula III:

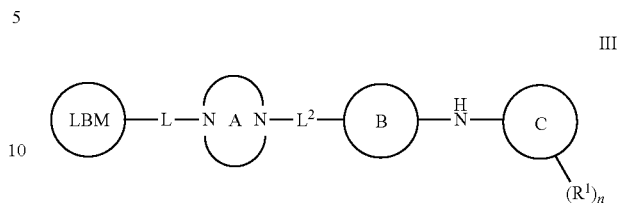

or a pharmaceutically acceptable salt thereof, wherein L and LBM are as defined above and described in embodiments herein, and wherein:

Ring A is a 4-7 membered saturated monocyclic ring having two ring nitrogen atoms;

Ring B is a 4-10 membered saturated mono- or bicyclic carbocyclic or hetereocyclic ring having 0-2 heteroatoms independently selected from nitrogen, oxygen, and sulfur;

Ring C is phenyl, a 4-10 membered saturated or partially unsaturated mono- or bicyclic carbocyclic or heterocyclic ring having 1-3 heteroatoms independently selected from nitrogen, oxygen, and sulfur, or a 5-10 membered mono- or bicyclic heteroaryl ring having 1-4 heteroatoms independently selected from nitrogen, oxygen, and sulfur;

$L^2$ is a bivalent moiety selected from a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—;

each $R^1$ is independently hydrogen, deuterium, —$R^4$, halogen, —CN, —NO$_2$, —OR, —SR, —NR$_2$, —S(O)$_2$R, —S(O)$_2$NR$_2$, —S(O)R, —CF$_2$(R), —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; and each n is 0, 1, 2, 3 or 4;

wherein the compound of formula III is not compound I-101, I-102, I-103, I-104, or I-105 in Table 1A.

In certain embodiments, the present invention provides a compound of formula V, where IRAK is a IRAK-4 binding moiety thereby forming a compound of formula V-g:

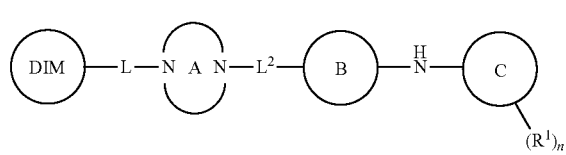

V-g or a pharmaceutically acceptable salt thereof, wherein L and DIM are as defined above and described in embodiments herein, and wherein:

Ring A is a 4-7 membered saturated monocyclic ring having two ring nitrogen atoms;

Ring B is a 4-10 membered saturated mono- or bicyclic carbocyclic or hetereocyclic ring having 0-2 heteroatoms independently selected from nitrogen, oxygen, and sulfur;

Ring C is phenyl, a 4-10 membered saturated or partially unsaturated mono- or bicyclic carbocyclic or heterocyclic ring having 1-3 heteroatoms independently selected from nitrogen, oxygen, and sulfur, or a 5-10 membered mono- or bicyclic heteroaryl ring having 1-4 heteroatoms independently selected from nitrogen, oxygen, and sulfur;

$L^2$ is a bivalent moiety selected from a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—;

each $R^1$ is independently hydrogen, deuterium, —$R^4$, halogen, —CN, —NO$_2$, —OR, —SR, —NR$_2$, —S(O)$_2$R, —S(O)$_2$NR$_2$, —S(O)R, —CF$_2$(R), —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^4$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur; and each n is 0, 1, 2, 3 or 4;

wherein the compound of formula V-g is not compound I-101, I-102, I-103, I-104, or I-105 in Table 1A.

The below embodiments are to compounds of formula III and V-g.

As defined generally above, Ring A is a 4-7 membered saturated monocyclic ring having two ring nitrogen atoms.

In some embodiments, Ring A is piperazine. In some embodiments, Ring A is 1,4-diazepane.

In some embodiments, Ring A is selected from those depicted in Table 1, below.

As defined generally above, Ring B a 4-10 membered saturated mono- or bicyclic carbocyclic or hetereocyclic ring having 0-2 heteroatoms independently selected from nitrogen, oxygen, and sulfur.

In some embodiments, Ring B is cyclobutyl. In some embodiments, Ring B is cyclopentyl. In some embodiments, Ring B is cyclohexyl. In some embodiments, Ring B is cycloheptyl.

In some embodiments, Ring B is selected from those depicted in Table 1, below.

As defined generally above, Ring C is a 9 membered bicyclic heteroaryl ring having 1-3 nitrogen atoms.

In some embodiments, Ring C is phenyl, a 4-10 membered saturated or partially unsaturated mono- or bicyclic carbocyclic or heterocyclic ring having 1-3 heteroatoms independently selected from nitrogen, oxygen, and sulfur, or a 5-10 membered mono- or bicyclic heteroaryl ring having 1-4 heteroatoms independently selected from nitrogen, oxygen, and sulfur.

In some embodiments, Ring B is phenyl. In some embodiments, Ring is a 4-10 membered saturated or partially unsaturated mono- or bicyclic carbocyclic or heterocyclic ring having 1-3 heteroatoms independently selected from nitrogen, oxygen, and sulfur. In some embodiments, Ring B is a 5-6 membered heteroaryl ring having 1-4 heteroatoms independently selected from nitrogen, oxygen, and sulfur.

In some embodiments, Ring C is

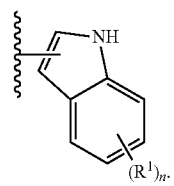

In some embodiments, Ring C is

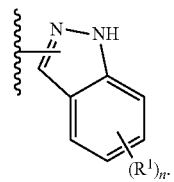

In some embodiments, Ring C is

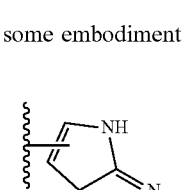

In some embodiments, Ring C is

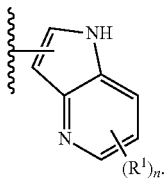

In some embodiments, Ring C is

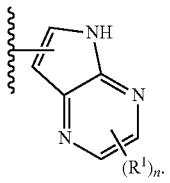

In some embodiments, Ring C is

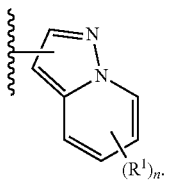

In some embodiments, Ring C is

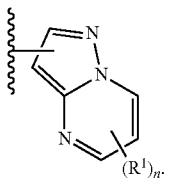

In some embodiments, Ring C is

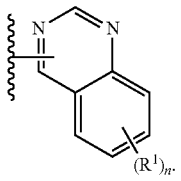

In some embodiments, Ring C is

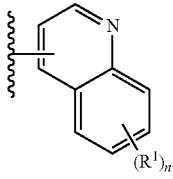

In some embodiments, Ring C is selected from those depicted in Table 1, below.

As generally defined above, $L^2$ is a bivalent moiety selected from a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR═CR—.

In some embodiments, $L^2$ a covalent bond. In some embodiments, $L^2$ is a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR═CR—. In some embodiments, $L^2$ is a $C_{1-3}$ aliphatic. In some embodiments, $L^2$ is —CH$_2$—. In some embodiments, $L^2$ is —C(D)(H)—. In some embodiments, $L^2$ is —C(D)$_2$-. In some embodiments, $L^2$ is —CH$_2$CH$_2$—. In some embodiments, $L^2$ is —NR—. In some embodiments, $L^2$ is —CH$_2$NR—. In some embodiments, $L^2$ is or —O—. In some embodiments, $L^2$ is —CH$_2$O—. In some embodiments, $L^2$ is —S—. In some embodiments, $L^2$ is —OC(O)—. In some embodiments, $L^2$ is —C(O)O—. In some embodiments, $L^2$ is —C(O)—. In some embodiments, $L^2$ is —S(O)—. In some embodiments, $L^2$ is —S(O)$_2$—. In some embodiments, $L^2$ is —NRS(O)$_2$—. In some embodiments, $L^2$ is —S(O)$_2$NR—. In some embodiments, $L^2$ is —NRC(O)—. In some embodiments, $L^2$ is —C(O)NR—. In some embodiments, $L^2$ is —OC(O)NR—. In some embodiments, $L^2$ is —NRC(O)O—.

In some embodiments, $L^2$ is selected from those depicted in Table 1, below.

As defined generally above, each $R^1$ is independently hydrogen, —$R^4$, halogen, —CN, —NO$_2$, —OR, —SR, —NR$_2$, —S(O)$_2$R, —S(O)$_2$NR$_2$, —S(O)R, —CF$_2$(R), —CR$_2$(CN), —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R.

In some embodiments, each $R^1$ is independently hydrogen. In some embodiments, each $R^1$ is independently —$R^4$. In some embodiments, each $R^1$ is independently halogen. In some embodiments, each $R^1$ is independently —CN. In some embodiments, each $R^1$ is independently —NO$_2$. In some embodiments, each $R^1$ is independently —OR. In some embodiments, each $R^1$ is independently —SR. In some embodiments, each $R^1$ is independently —NR$_2$. In some embodiments, each $R^1$ is independently —S(O)$_2$R. In some embodiments, each $R^1$ is independently —S(O)$_2$NR$_2$. In some embodiments, each $R^1$ is independently —S(O)R. In some embodiments, each $R^1$ is independently —CF$_2$(R). In some embodiments, each $R^1$ is independently —CR$_2$(CN). In some embodiments, each $R^1$ is independently —CF$_3$. In some embodiments, each $R^1$ is independently —CR$_2$(OR). In some embodiments, each $R^1$ is independently —CR$_2$(NR$_2$). In some embodiments, each $R^1$ is independently —C(O)R. In some embodiments, each $R^1$ is independently —C(O)OR. In some embodiments, each $R^1$ is independently —C(O)NR$_2$. In some embodiments, each $R^1$ is independently —C(O)NR$_2$. In some embodiments, each $R^1$ is independently —C(O)N(R)OR. In some embodiments, each $R^1$ is independently —OC(O)R. In some embodiments, each $R^1$ is independently —OC(O)NR$_2$. In some embodiments, each $R^1$ is independently —N(R)C(O)OR. In some embodiments, each $R^1$ is independently —N(R)C(O)R. In some embodiments, each R¹ is independently —N(R)C(O)NR₂. In some embodiments, each R¹ is independently —N(R)S(O)₂R.

In some embodiments, R¹ is

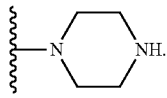

In some embodiments, R¹ is

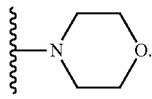

In some embodiments, R¹ is

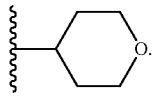

In some embodiment, R¹ is methyl. In some embodiments, R¹ is —CH₂(CN). In some embodiments, R¹ is —CN.

In some embodiments, each R¹ is independently selected from those depicted in Table 1, below.

As generally defined above, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, each R is independently hydrogen. In some embodiments, each R is an optionally substituted group selected from $C_{1-6}$ aliphatic. In some embodiments, each R is a phenyl. In some embodiments, each R is a 4-7 membered saturated or partially unsaturated heterocyclic having 1-2 heteroatoms independently selected from nitrogen, oxygen, and sulfur. In some embodiments, each R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, each R is selected from those depicted in Table 1, below.

As generally defined above, each R⁴ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, each R⁴ is independently an optionally substituted group selected from $C_{1-6}$ aliphatic. In some embodiments, each R⁴ is independently an optionally substituted phenyl. In some embodiments, each R⁴ is independently an optionally substituted 4-7 membered saturated or partially unsaturated heterocyclic ring having 1-2 heteroatoms independently selected from nitrogen, oxygen, and sulfur. In some embodiments, each R⁴ is independently an optionally substituted 5-6 membered heteroaryl ring having 1-4 heteroatoms independently selected from nitrogen, oxygen, and sulfur.

In some embodiments, each R⁴ is selected from those depicted in Table 1, below.

A As generally defined above, each n is independently 0, 1, or 2.

In some embodiments, each n is independently 0. In some embodiments, each n is independently 1. In some embodiments, each n is independently 2.

In some embodiments, each n is selected from those depicted in Table 1, below.

In some embodiments, the present invention provides the compound of formula III, wherein Ring B is cyclohexyl thereby forming a compound of formula III-a:

III-a

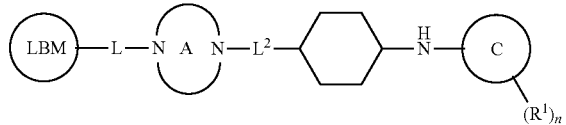

or a pharmaceutically acceptable salt thereof, wherein each of LBM, L, L², Ring A, R¹, Ring C, and n is as defined above and described in embodiments herein, both singly and in combination.

In some embodiments, the invention provides the compound of formula III, wherein L² is a covalent bond, Ring B is cyclohexyl, and Ring C is pyrrolo[2,1-f][1,2,4]triazinyl, 7H-pyrrolo[2,3-d]pyrimidinyl, or quinazolinyl thereby forming a compound of formula III-b, III-c, or III-d respectively:

III-b

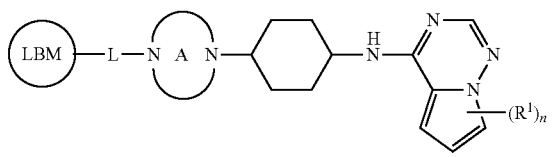

III-c

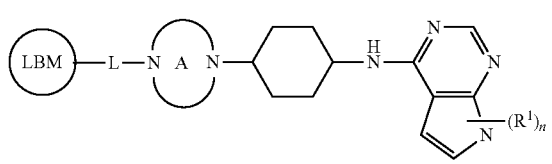

III-d

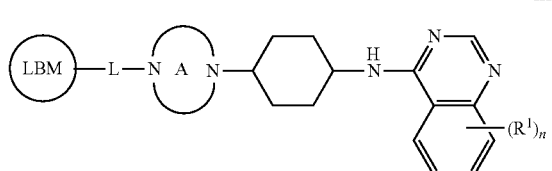

or a pharmaceutically acceptable salt thereof, wherein each of LBM, L, Ring A, $R^1$, and n is as defined above and described in embodiments herein, both singly and in combination.

In some embodiments, the present invention provides the compound of formula V-g, wherein Ring B is cyclohexyl thereby a compound of formula V-h:

V-h

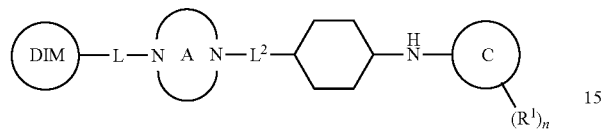

or a pharmaceutically acceptable salt thereof, wherein each of DIM, L, $L^2$, Ring A, $R^1$, Ring C, and n is as defined above and described in embodiments herein, both singly and in combination.

In some embodiments, the invention provides the compound of formula V-g, wherein $L^2$ is a covalent bond, Ring B is cyclohexyl, and Ring C is pyrrolo[2,1-f][1,2,4]triazinyl, 7H-pyrrolo[2,3-d]pyrimidinyl, or quinazolinyl thereby forming a compound of formula V-i-1, V-i-2, or V-i-3 respectively:

V-i-1

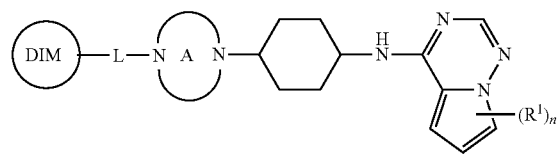

V-i-2

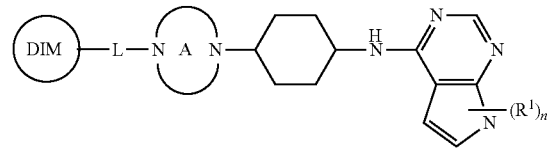

V-i-3

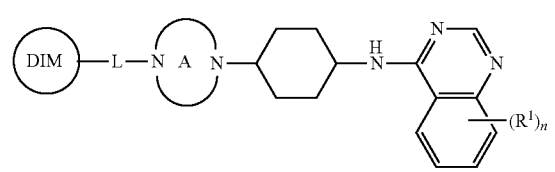

or a pharmaceutically acceptable salt thereof, wherein each of DIM, L, Ring A, $R^1$, and n is as defined above and described in embodiments herein, both singly and in combination.

In some embodiments, IRAK is

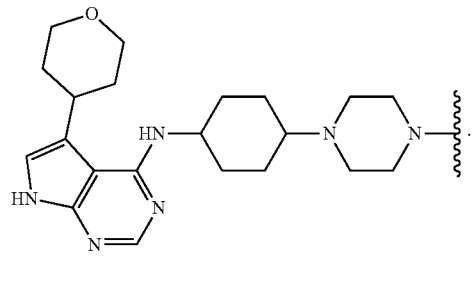 [SMILES: *N1CCN(C2CCC(Nc3ncnc4[nH]cc(C5CCOCC5)c34)CC2)CC1]

In some embodiments, IRAK is

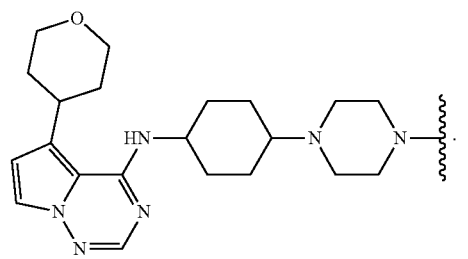 [SMILES: *N1CCN(C2CCC(Nc3ncnn4ccc(C5CCOCC5)c34)CC2)CC1]

In some embodiments, IRAK is

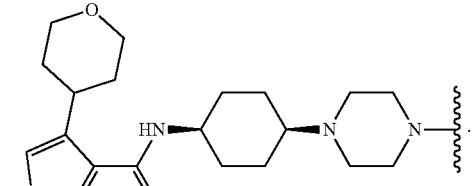

In some embodiments, IRAK is

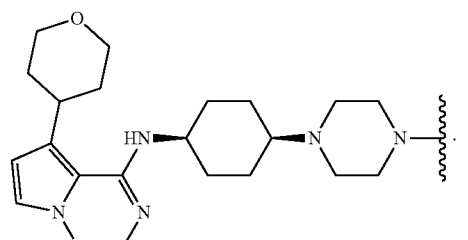

In some embodiments, IRAK is
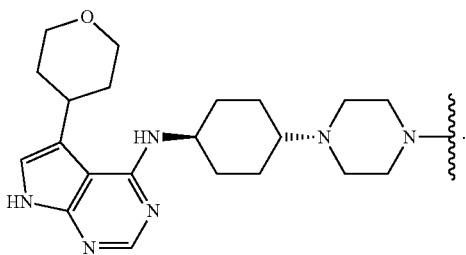
In some embodiments, IRAK is
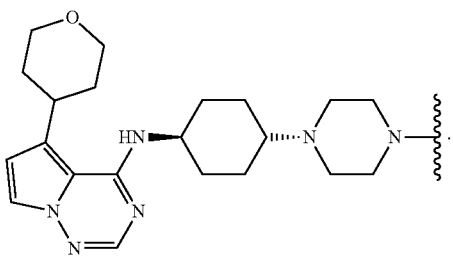
In some embodiments, IRAK is
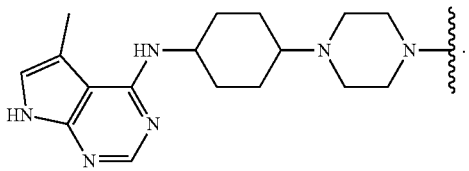 [SMILES: *N1CCN(C2CCC(Nc3ncnc4[nH]cc(C)c34)CC2)CC1]
In some embodiments, IRAK is
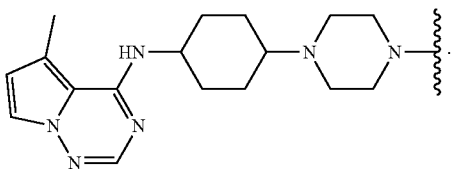 [SMILES: *N1CCN(C2CCC(Nc3ncnn4ccc(C)c34)CC2)CC1]
In some embodiments, IRAK is
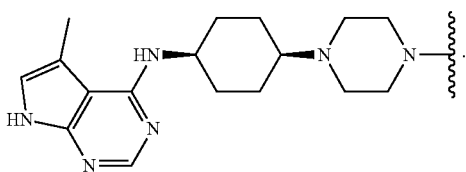 [SMILES: *N1CCN([C@H]2CC[C@@H](Nc3ncnc4[nH]cc(C)c34)CC2)CC1]
In some embodiments, IRAK is
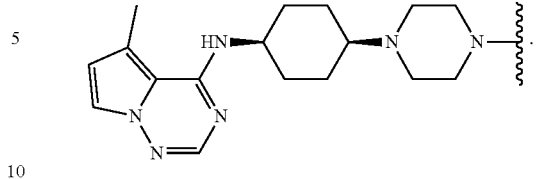
In some embodiments, IRAK is
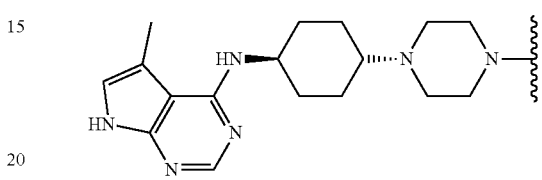
In some embodiments, IRAK is
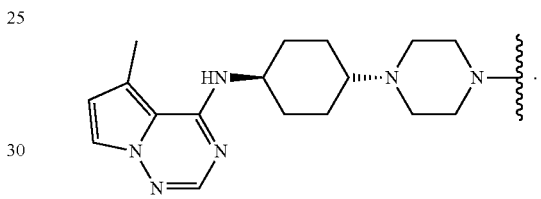
In some embodiments, IRAK is
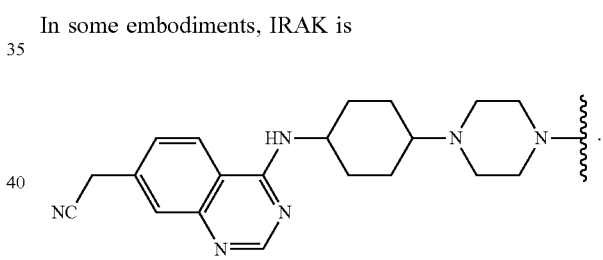
In some embodiments, IRAK is
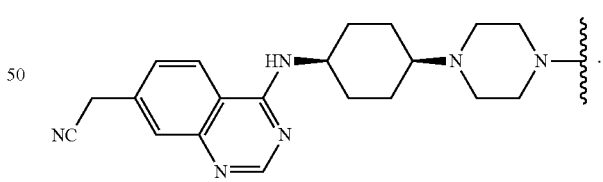
In some embodiments, IRAK is
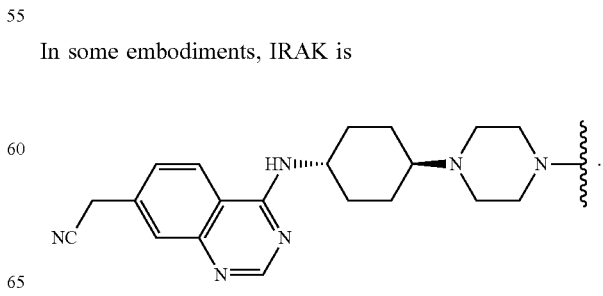

In some embodiments, IRAK is

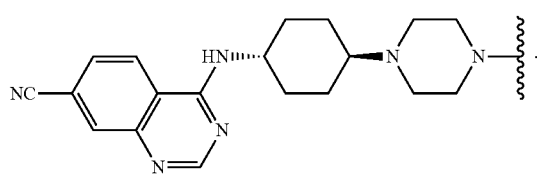 [SMILES: *N1CCN([C@H]2CC[C@H](Nc3ncnc4cc(C#N)ccc34)CC2)CC1]

In some embodiments, IRAK is selected from those in Table 1, below.

In some embodiments, the present invention provides a compound of Formula I, wherein IRAK is an IRAK-4 inhibitor

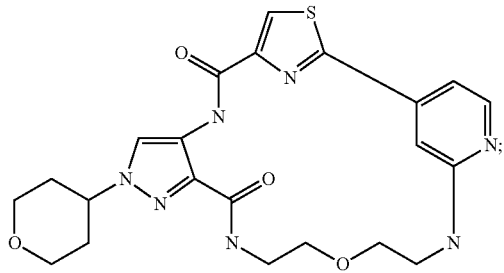 [SMILES: O=C1Nc2cn(C3CCOCC3)nc2C(=O)NCCOCCNc2cc(ccn2)-c2nc1cs2]

thereby forming a compound of formula IV:

IV

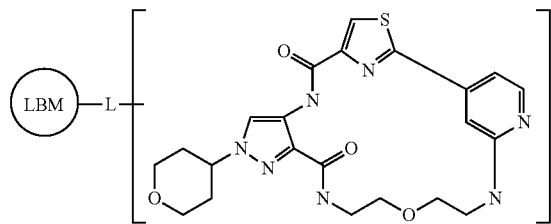

or a pharmaceutically acceptable salt thereof, wherein

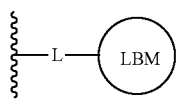

is attached to a modifiable carbon, oxygen, or nitrogen, and wherein L and LBM are as defined above and described in embodiments herein.

In some embodiments, IRAK is N

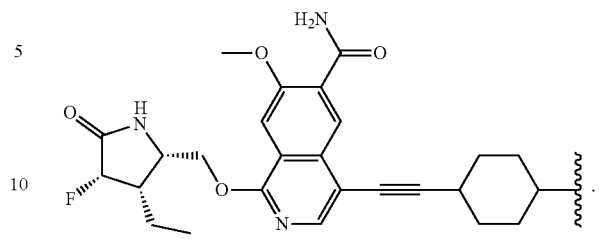

In some embodiments, IRAK is

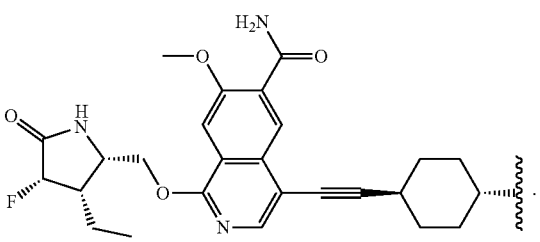

In some embodiments, IRAK is


In some embodiments, IRAK is In some embodiments, IRAK is

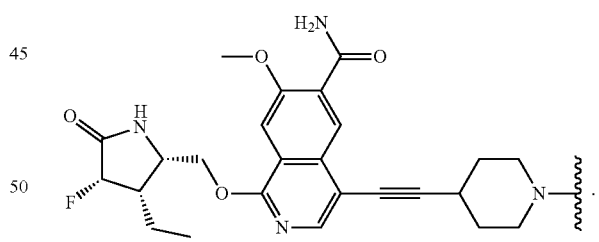

In some embodiments, IRAK is


In some embodiments, IRAK is

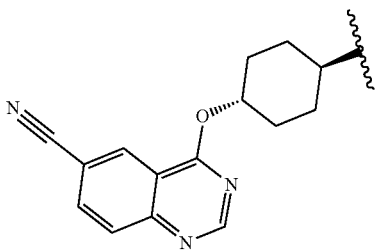

In some embodiments, IRAK is

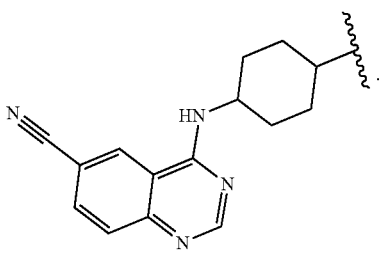 [SMILES: *C1CCC(Nc2ncnc3ccc(C#N)cc23)CC1]

In some embodiments, IRAK is

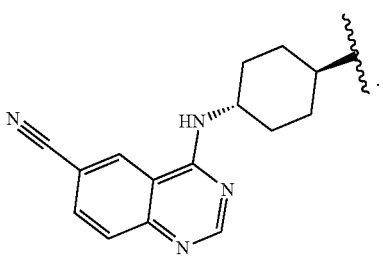 [SMILES: *[C@H]1CC[C@H](Nc2ncnc3ccc(C#N)cc23)CC1]

In some embodiments, IRAK is

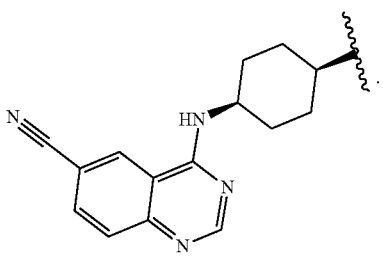 [SMILES: *[C@H]1CC[C@@H](Nc2ncnc3ccc(C#N)cc23)CC1]

In some embodiments, IRAK is

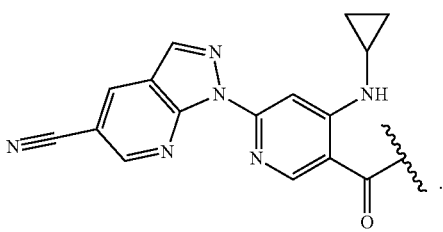 [SMILES: *C(=O)c1cnc(-n2ncc3cc(C#N)cnc32)cc1NC1CC1]

In some embodiments, IRAK is

In some embodiments, IRAK is selected from those in Table 1, below.

Ligase Binding Moiety (LBM)

In some embodiments, LBM is an E3 ligase ligand. Such E3 ligase ligands are well known to one of ordinary skill in the art and include those described in M. Toure, C. M. Crews, Angew. Chem. Int. Ed. 2016, 55, 1966, T. Uehara et al. *Nature Chemical Biology* 2017, 13, 675, WO 2017/176708, US 2017/0281784, WO 2017/161119, WO 2017/176957, WO 2017/176958, WO 2015/160845, US 2015/0291562, WO 2016/197032, WO 2016/105518, US 2018/0009779, WO 2017/007612, 2018/0134684, WO 2013/106643, US 2014/0356322, WO 2002/020740, US 2002/0068063, WO 2012/078559, US 2014/0302523, WO 2012/003281, US 2013/0190340, US 2016/0022642, WO 2014/063061, US 2015/0274738, WO 2016/118666, US 2016/0214972, WO 2016/149668, US 2016/0272639, WO 2016/169989, US 2018/0118733, WO 2016/197114, US 2018/0147202, WO 2017/011371, US 2017/0008904, WO 2017/011590, US 2017/0037004, WO 2017/079267, US 2017/0121321, WO 2017/117473, WO 2017/117474, WO 2013/106646, WO 2014/108452, WO 2017/197036, US 2019/0076540, WO 2017/197046, US 2019/0076542, WO 2017/197051, US 2019/0076539, WO 2017/197055, US 2019/0076541, and WO 2017/197056, the entirety of each of which is herein incorporated by reference.

In certain embodiments, the present invention provides a compound of formula I, wherein LBM is an E3 ubiquitin ligase (cereblon) binding moiety

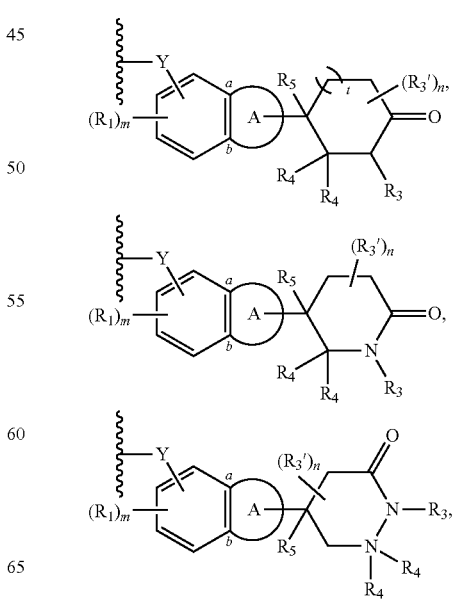

-continued
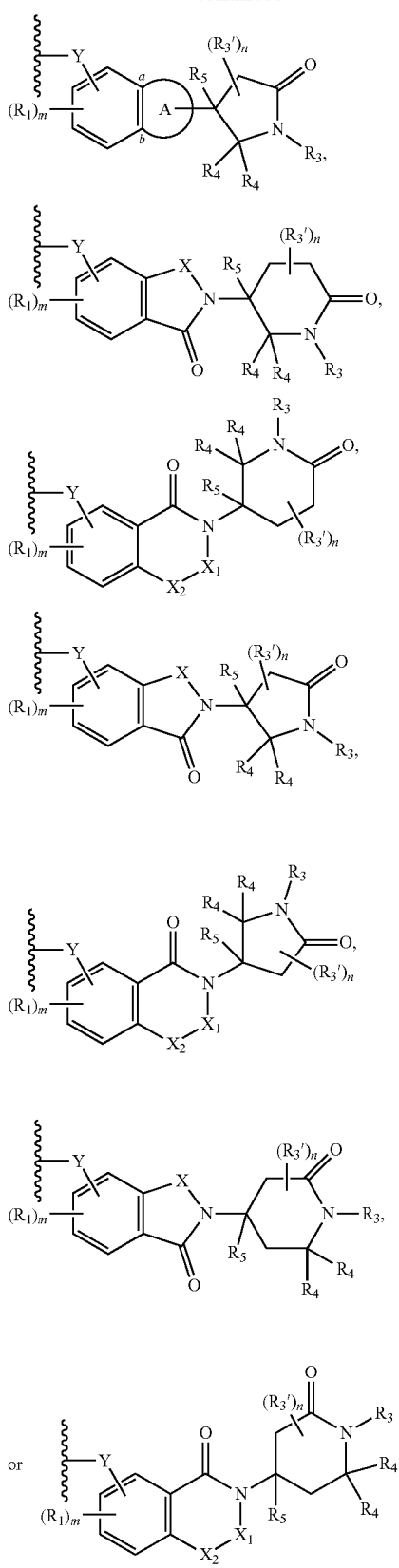
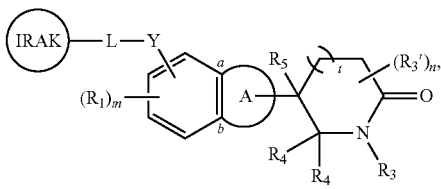
I-a-1
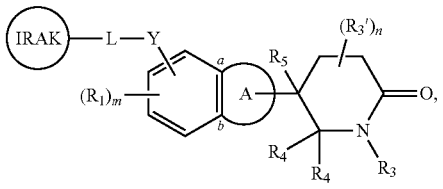
I-a-2
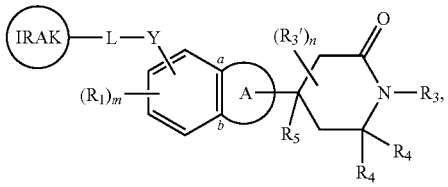
I-a-3
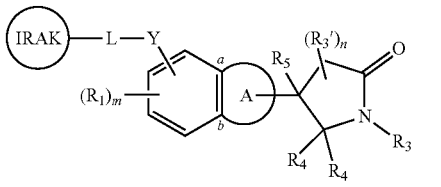
I-a-4
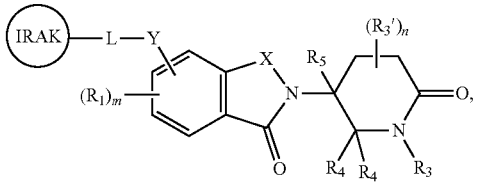
I-a-5
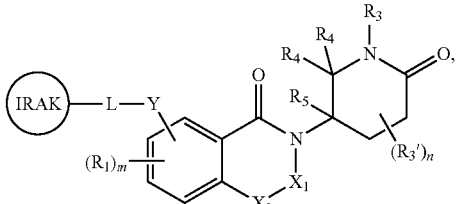
I-a-6
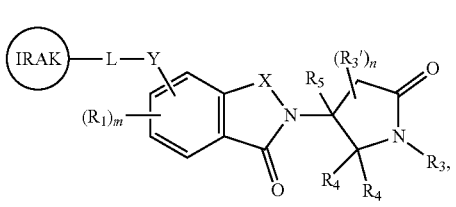
I-a-7
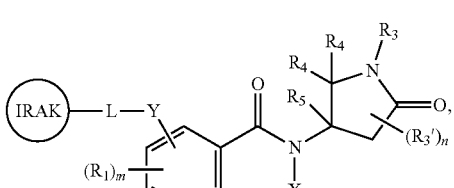
I-a-8
thereby forming a compound of formula I-a-1, I-a-2, I-a-3, I-a-4, I-a-5, I-a-6, I-a-7, I-a-8, I-a-9, or I-a-10 respectively:

-continued

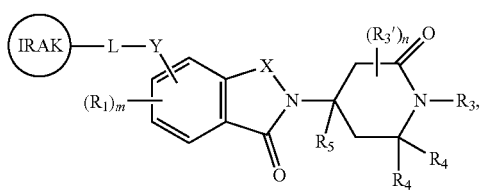

I-a-9

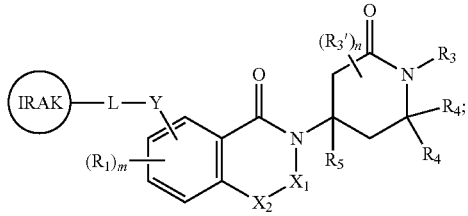

I-a-10 or a pharmaceutically acceptable salt thereof, wherein L and IRAK are as defined above and described in embodiments herein, and wherein:

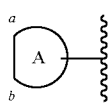

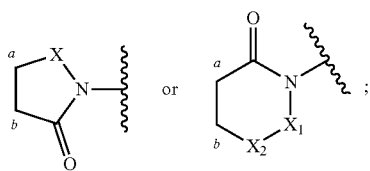

Y is a bond, $Y_1$, O, NH, $NR_2$, C(O)O, OC(O), C(O)$NR_2$', $NR_2$'C(O), $Y_1$—O, $Y_1$—NH, $Y_1$—$NR_2$, $Y_1$—C(O), $Y_1$—C(O)O, $Y_1$—OC(O), $Y_1$—C(O)$NR_2$', or $Y_1$—$NR_2$'C(O), wherein $Y_1$ is $C_{1-6}$ alkylene, $C_{2-6}$ alkenylene, or $C_2$-$C_6$ alkynylene;

X is C(O) or C($R^3$)$_2$;

$X_1$—$X_2$ is C($R^3$)=N or C($R^3$)$_2$—C($R^3$)$_2$;

each $R^1$ is independently halogen, nitro, $NH_2$, OH, C(O)OH, $C_{1-6}$ alkyl, or $C_{1-6}$ alkoxy;

$R^2$ is $C_{1-6}$ alkyl, $C_{2-6}$ alkenyl, $C_{3-8}$ cycloalkyl, 3- to 8-membered heterocycloalkyl, C(O)—$C_{1-6}$ alkyl, C(O)—$C_{2-6}$ alkenyl, C(O)—$C_{3-8}$ cycloalkyl, or C(O)-3- to 8-membered heterocycloalkyl, and $R^2$ is optionally substituted with one or more of halogen, N($R_a$)$_2$, NHC(O)$R_a$, NHC(O)O$R_a$, O$R_b$, $C_{3-8}$ cycloalkyl, 3- to 8-membered heterocycloalkyl, $C_{6-10}$ aryl, or 5- to 10-membered heteroaryl, wherein each of the $C_3$-s cycloalkyl, 3- to 8-membered heterocycloalkyl, $C_{6-10}$ aryl or 5- to 10-membered heteroaryl is optionally further substituted with one or more of halogen, $NH_2$, CN, nitro, OH, C(O)OH, $C_{1-6}$ alkyl, $C_{1-6}$ haloalkyl, $C_{1-6}$ alkoxy, or $C_{1-6}$ haloalkoxy;

R2' is H, $C_{1-6}$ alkyl, $C_{2-6}$ alkenyl, $C_{3-8}$ cycloalkyl, or 3- to 8-membered heterocycloalkyl, and R2', when not being H, is optionally substituted with one or more of halogen, N($R_a$)$_2$, NHC(O)$R_a$, NHC(O)O$R_a$, O$R_b$, $C_{3-8}$ cycloalkyl, 3- to 8-membered heterocycloalkyl, $C_{6-10}$ aryl, or 5- to 10-membered heteroaryl, wherein each of the $C_{3-8}$ cycloalkyl, 3- to 8-membered heterocycloalkyl, $C_{6-10}$ aryl or 5- to 10-membered heteroaryl is optionally further substituted with one or more of halogen, $NH_2$, CN, nitro, OH, C(O)OH, $C_{1-6}$ alkyl, $C_{1-6}$ haloalkyl, $C_{1-6}$ alkoxy, or $C_{1-6}$ haloalkoxy;

each $R^3$ is independently H or $C_{1-3}$ alkyl optionally substituted with $C_{6-10}$ aryl or 5- to 10-membered heteroaryl;

each R3' is independently $C_{1-3}$ alkyl;

each $R^4$ is independently H or $C_{1-3}$ alkyl; or two $R^4$, together with the carbon atom to which they are attached, form C(O), a $C_{3-6}$ carbocycle, or a 4-, 5-, or 6-membered heterocycle comprising 1 or 2 heteroatoms selected from N and O;

$R^5$ is H, $C_{1-3}$ alkyl, F, or Cl;

each $R_a$ independently is H or $C_{1-6}$ alkyl;

Rb is H or tosyl;

t is 0 or 1;

m is 0, 1, 2 or 3; and n is 0, 1 or 2, as defined and described in WO 2017/007612 and US 2018/0134684, the entirety of each of which is herein incorporated by reference.

In certain embodiments, the present invention provides a compound of formula I, wherein LBM is an E3 ubiquitin ligase (cereblon) binding moiety

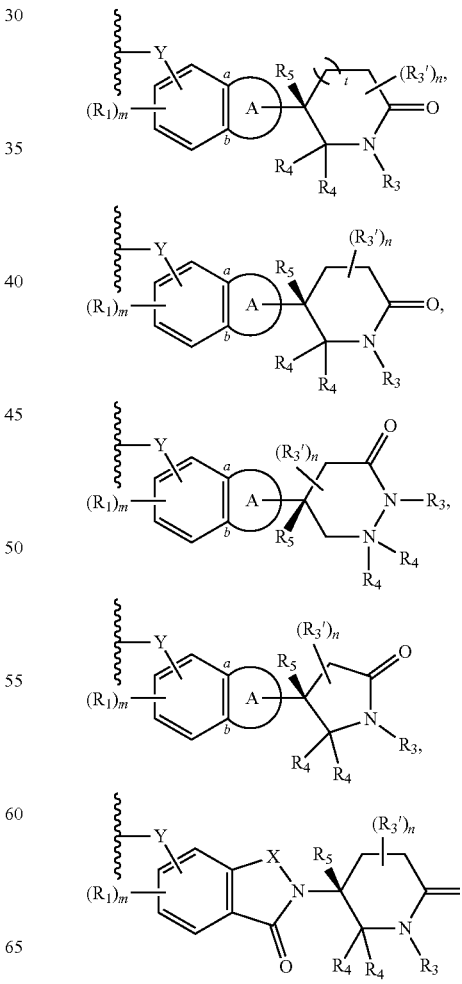

-continued
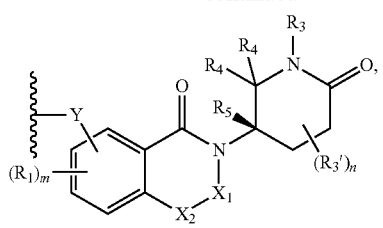
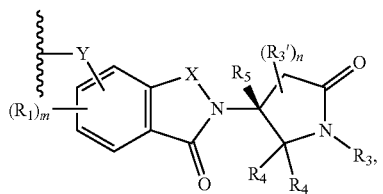
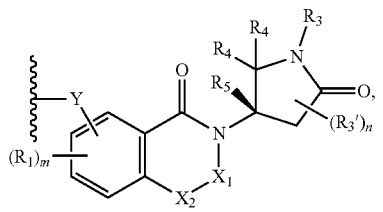
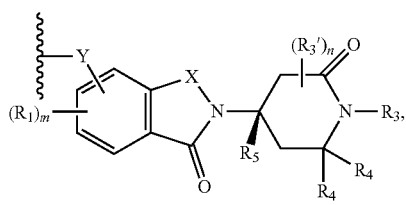
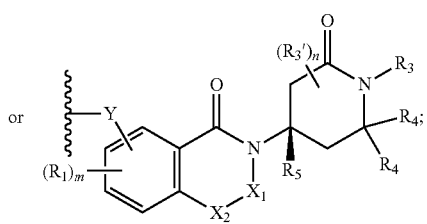
thereby forming a compound of formula I-a'-1, I-a'-2, I-a'-3, I-a'-4, I-a'-5, I-a'-6, I-a'-7, I-a'-8, I-a'-9, or I-a'-10 respectively:
I-a'-1
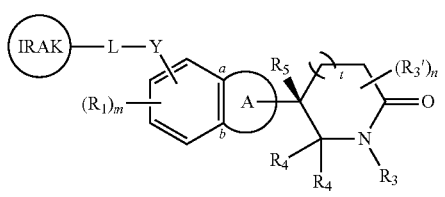
I-a'-2
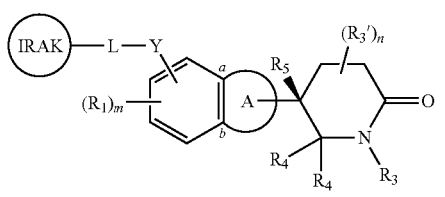
I-a'-3
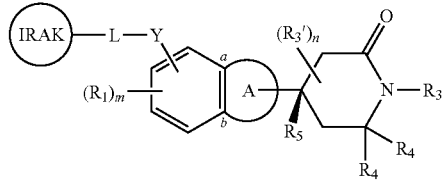
I-a'-4
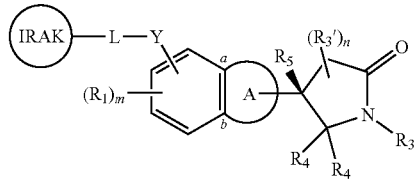
I-a'-5
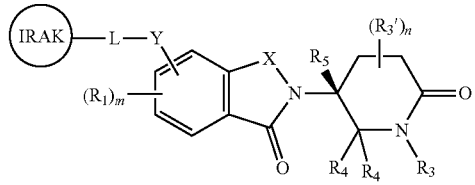
I-a'-6
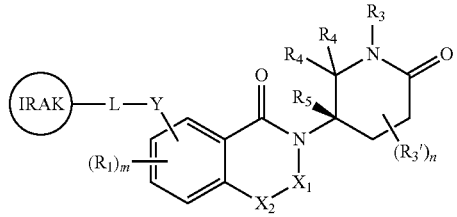
I-a'-7
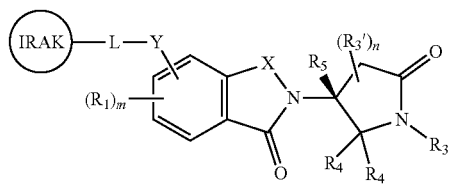
I-a'-8
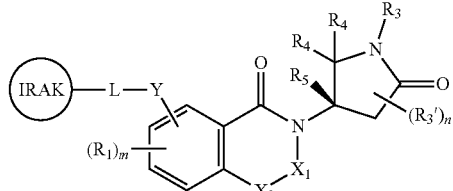
I-a'-9
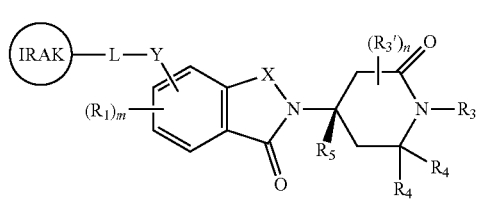

-continued

I-a'-10

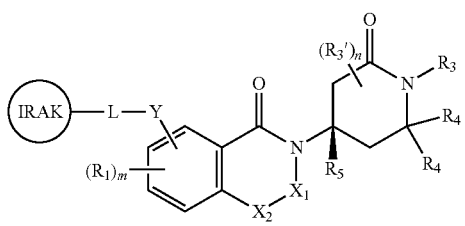

or a pharmaceutically acceptable salt thereof, wherein L and IRAK are as defined above and described in embodiments herein, and wherein each of the variables

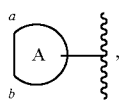

X, $X_1$, $X_2$, Y, $R_1$, $R_3$, $R_3'$, $R_4$, $R_5$, t, m and n is as defined and described in WO 2017/007612 and US 2018/0134684, the entirety of each of which is herein incorporated by reference.

In certain embodiments, the present invention provides a compound of formula I, wherein LBM is an E3 ubiquitin ligase (cereblon) binding moiety

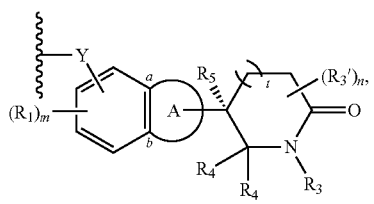

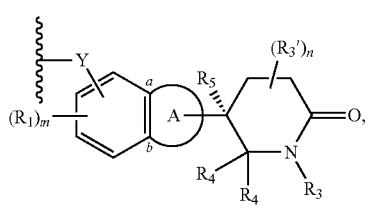

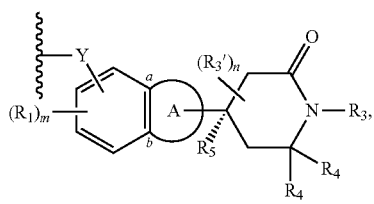

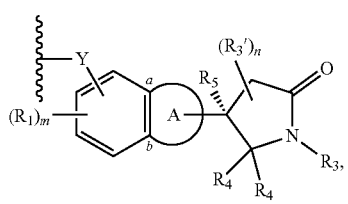

-continued

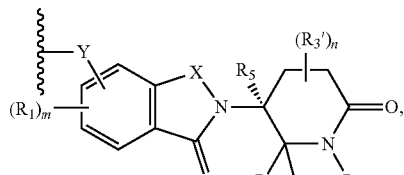

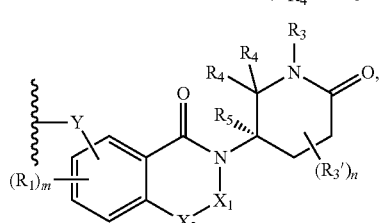

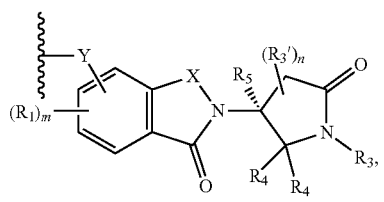

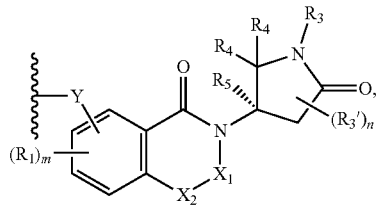

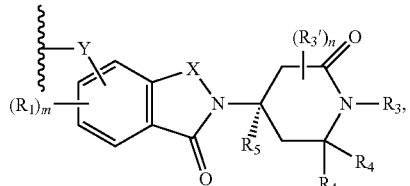

or

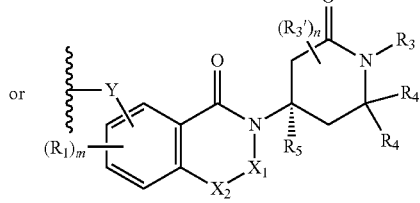

thereby forming a compound of formula I-a''-1, I-a''-2, I-a''-3, I-a''-4, I-a''-5, I-a''-6, I-a''-7, I-a''-8, I-a''-9, or I-a'-10 respectively:

I-a''-1

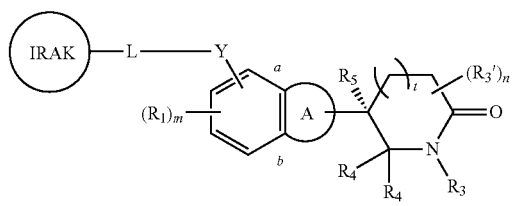


I-a″-2


I-a″-3

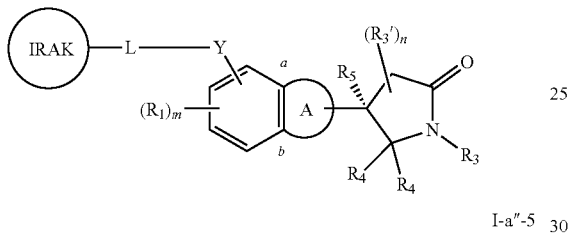

I-a″-4

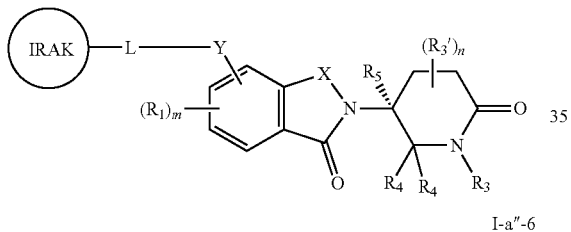

I-a″-5

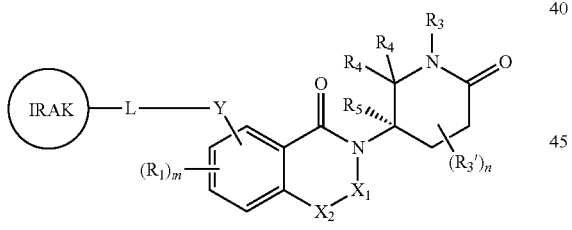

I-a″-6

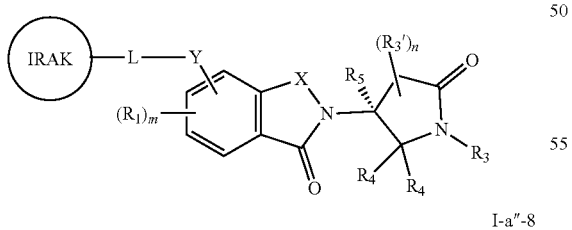

I-a″-7

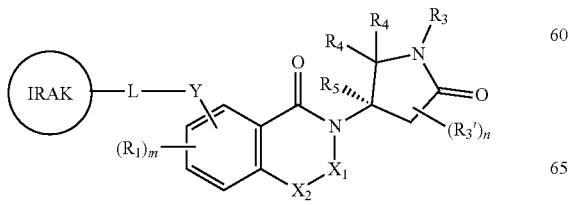

I-a″-8

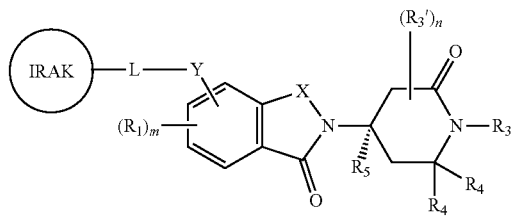

I-a″-9

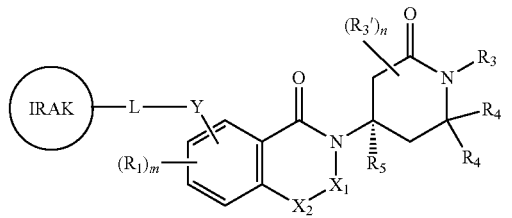

I-a″-10 or a pharmaceutically acceptable salt thereof, wherein L and IRAK are as defined above and

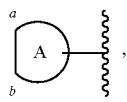

described in embodiments herein, and wherein each of the variables b, X, $X_1$, $X_2$, Y, $R^1$, $R_3$, $R_3'$, $R_4$, $R_5$, t, m and n is as defined and described in WO 2017/007612 and US 2018/0134684, the entirety of each of which is herein incorporated by reference.

In certain embodiments, the present invention provides a compound of formula I, wherein LBM is a VHL E3 ubiquitin ligase binding moiety

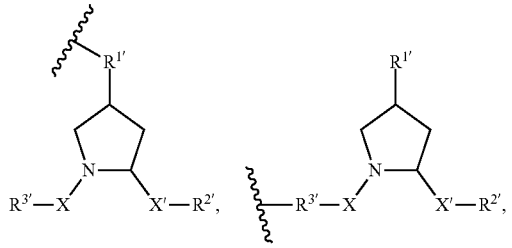

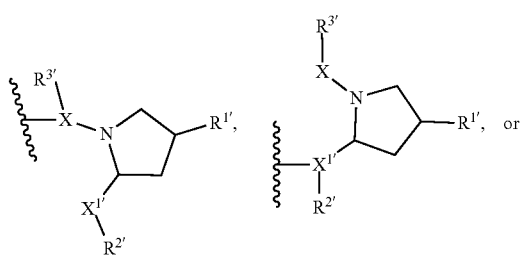

-continued

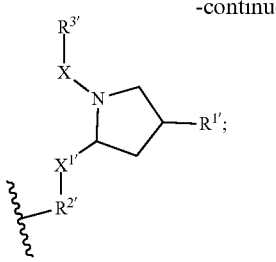

thereby forming a compound of formula I-b-1, I-b-2, I-b-3, I-b-4, or I-b-5 respectively:

I-b-1

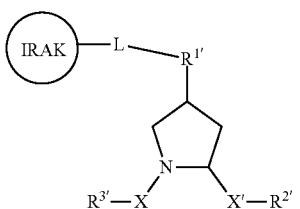

I-b-2

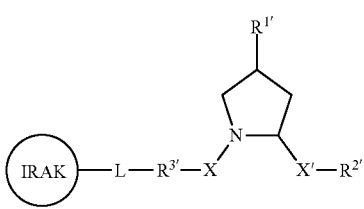

I-b-3

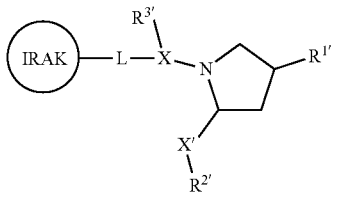

I-b-4

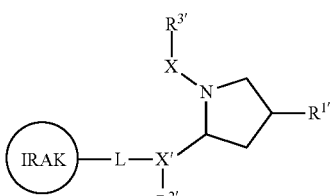

I-b-5 or a pharmaceutically acceptable salt thereof, wherein L and IRAK are as defined above and described in embodiments herein, and wherein each of the variables R$^{1'}$, R$^{2'}$, R$^{3'}$, X, and X' is as defined and described in WO 2013/106643 and US 2014/0356322, the entirety of each of which is herein incorporated by reference.

In certain embodiments, the present invention provides a compound of formula I, wherein LBM is an E3 ubiquitin ligase (cereblon) binding moiety

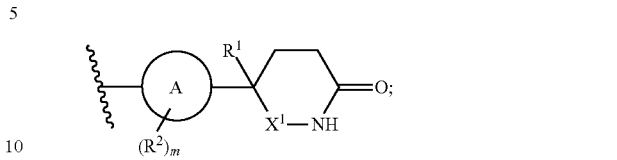

thereby forming a compound of formula I-c:

I-c

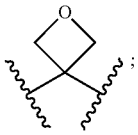 [SMILES: *C1(*)COC1]

or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

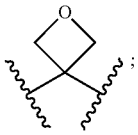 [SMILES: *C1(*)COC1]

$R^1$ is hydrogen, deuterium, halogen, —CN, —OR, —SR, —S(O)R, —S(O)$_2$R, —NR$_2$, or an optionally substituted C$_{1-4}$ aliphatic;

each $R^2$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

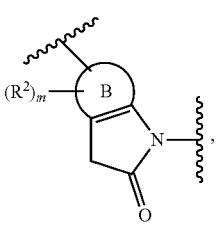 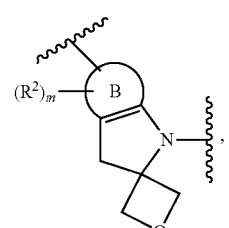

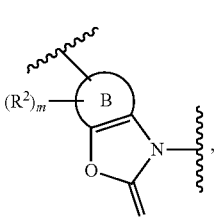 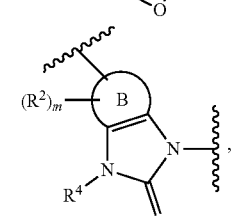

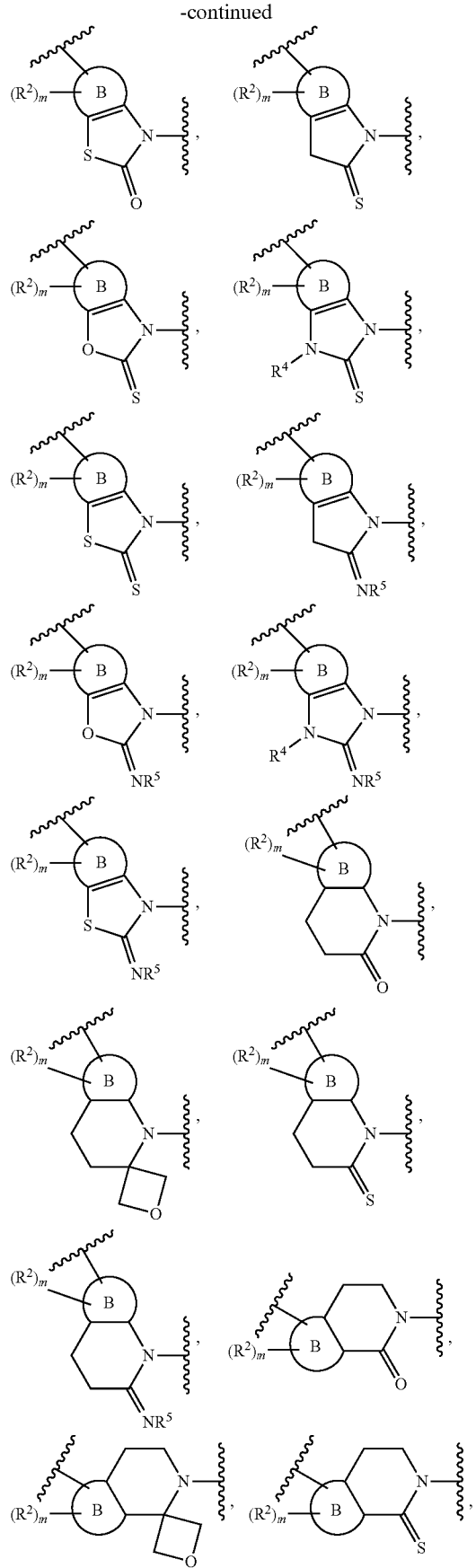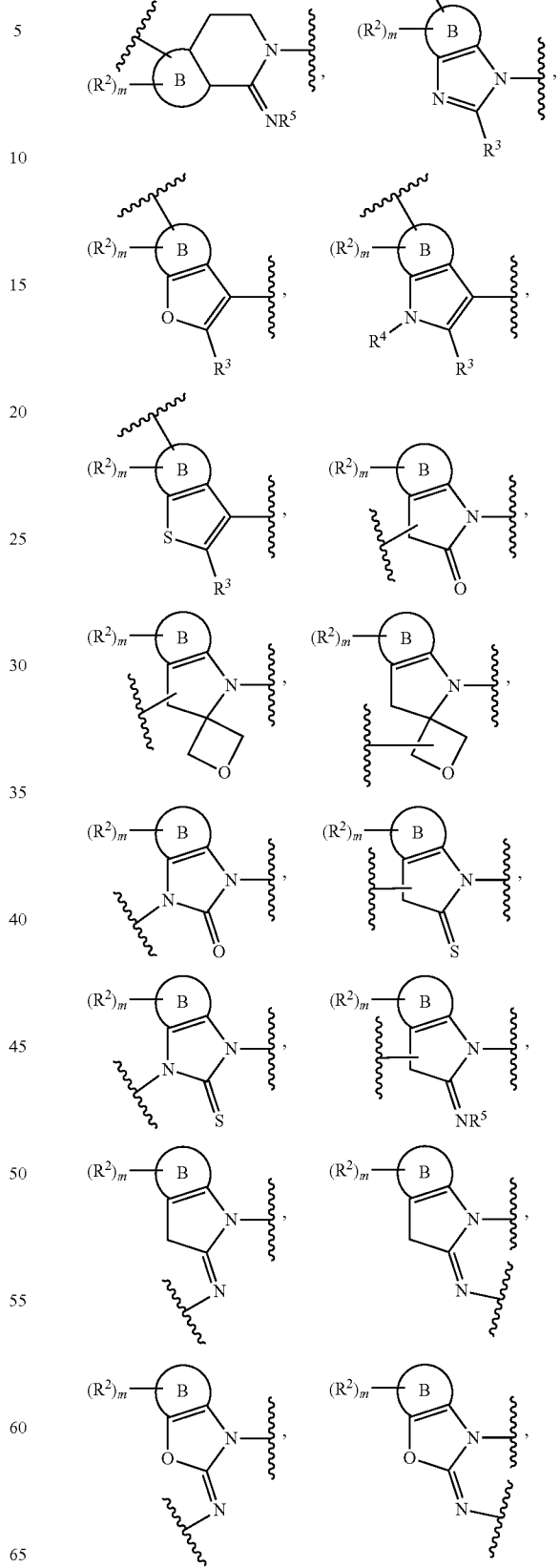

-continued

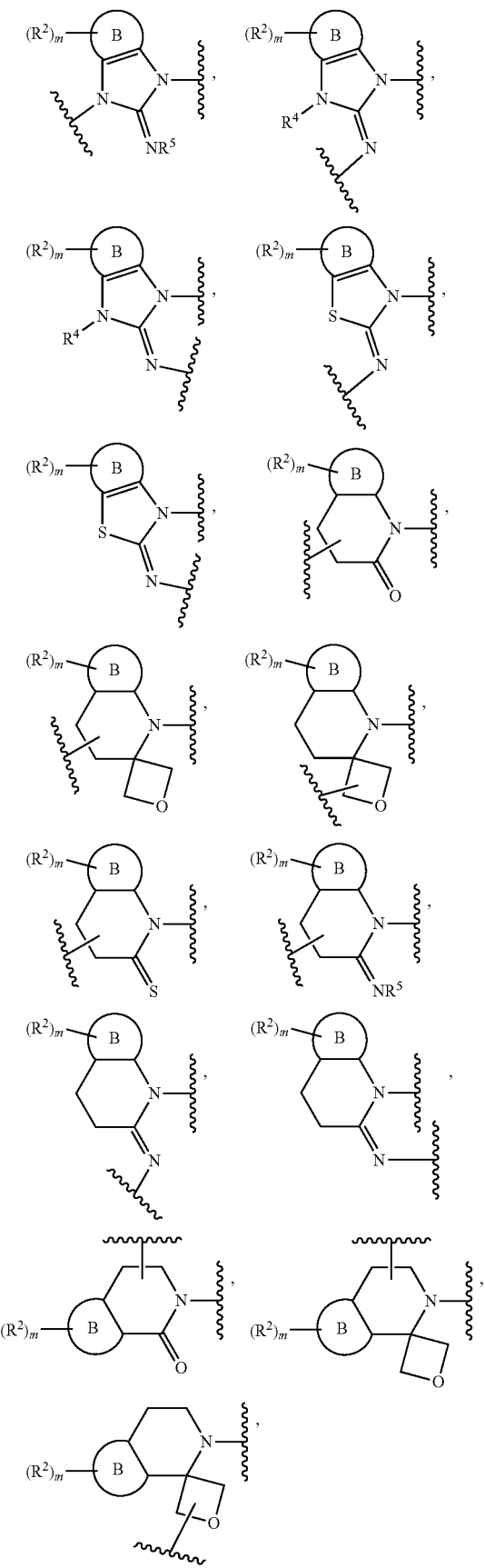
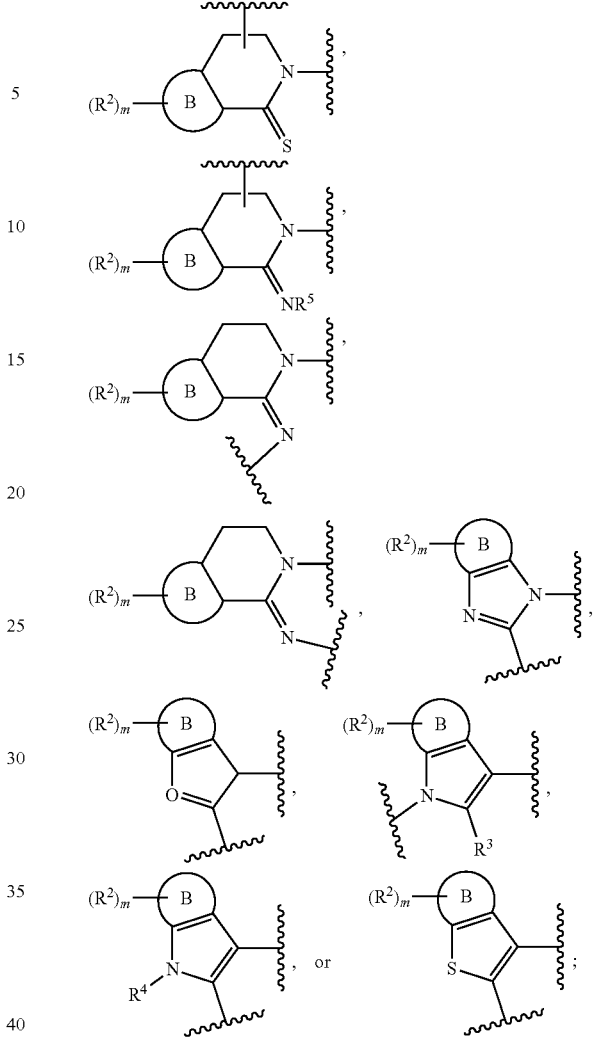

Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

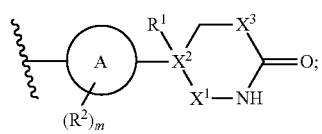

thereby forming a compound of formula I-c':

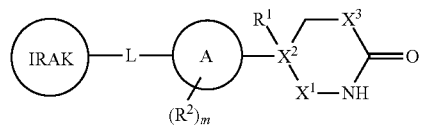

I-c' or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

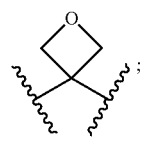 [SMILES: *C1(*)COC1]

$X^2$ is a carbon atom or silicon atom;

$X^3$ is a bivalent moiety selected from —CH$_2$— or —Si(R$^2$)—;

$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each $R^2$ is independently hydrogen, deuterium, —R$^6$, halogen, —CN, —NO$_2$, —OR, —SR, —NR$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

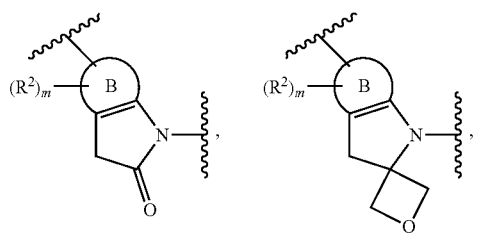

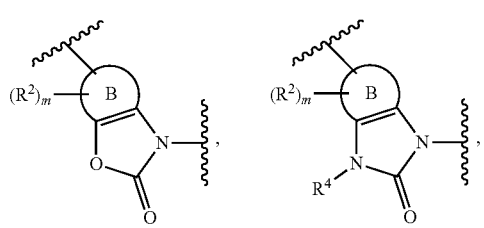

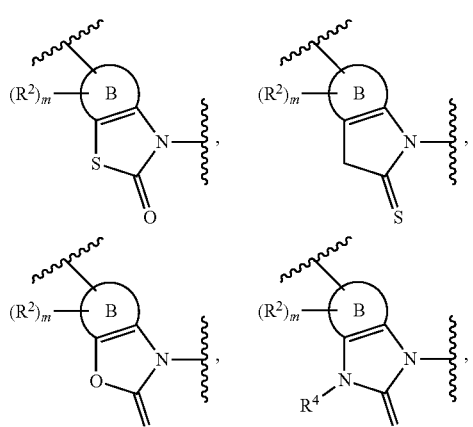

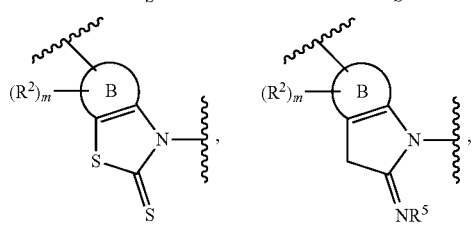

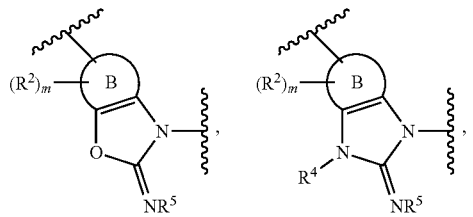

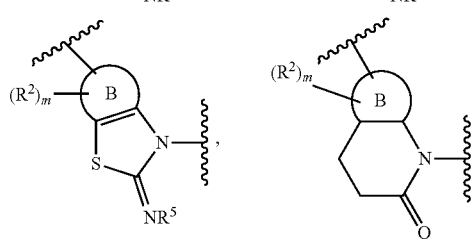

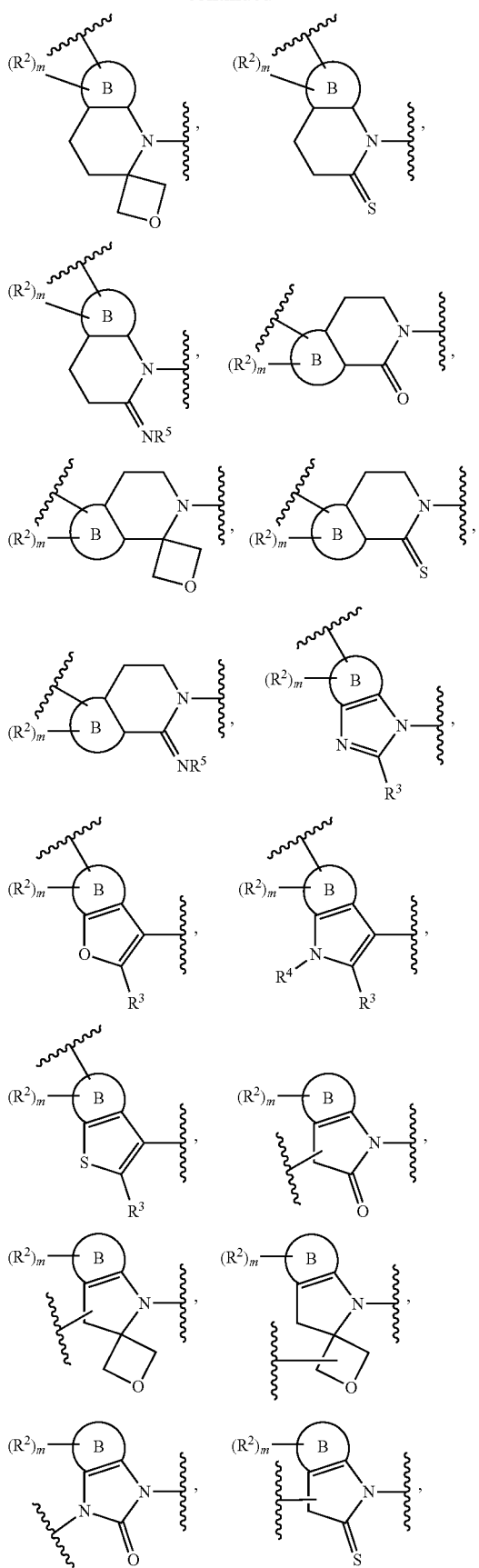
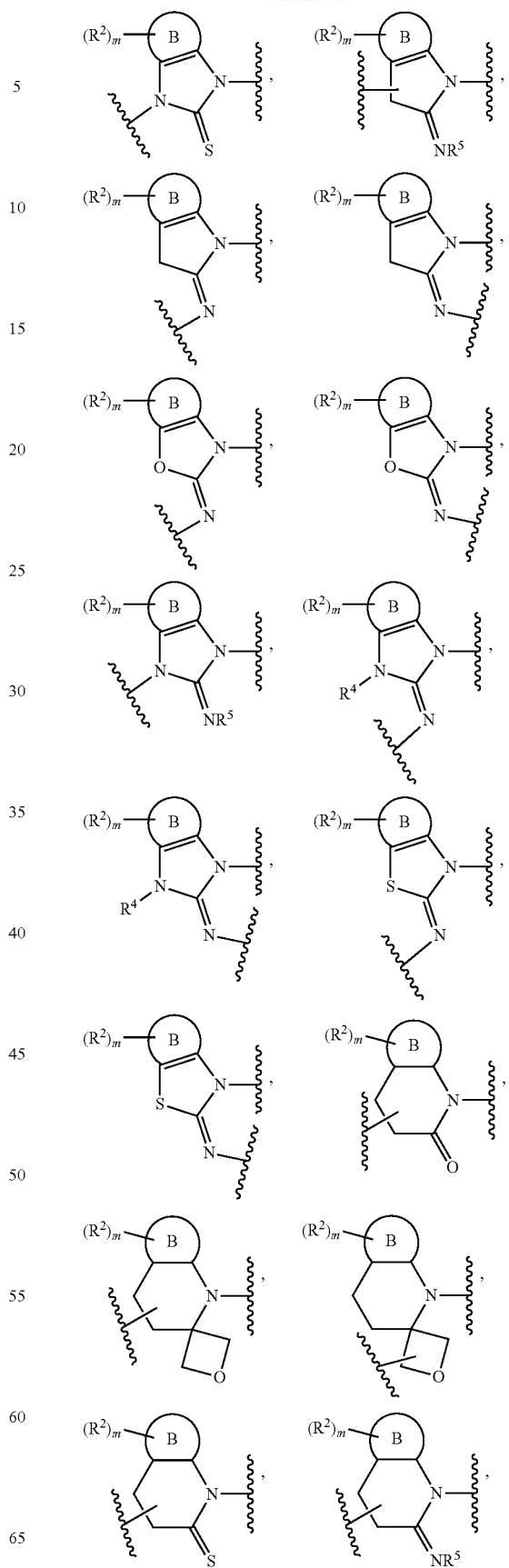

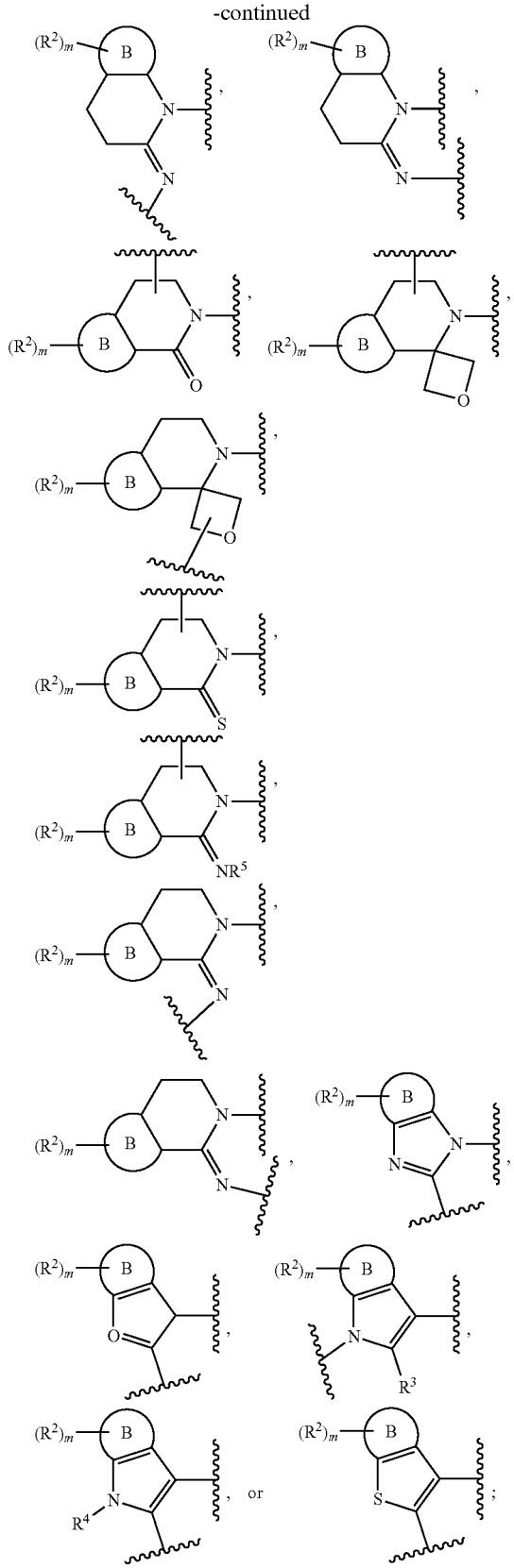

Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from boron, nitrogen, oxygen, silicon, or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-c' above is provided as a compound of formula I-c" or formula I-c'":

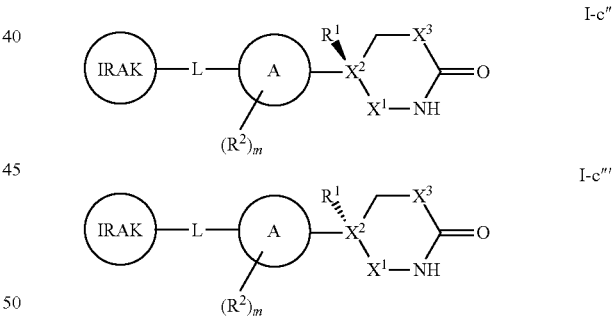

or a pharmaceutically acceptable salt thereof, wherein:
each of IRAK, Ring A, L, $R^1$, $R^2$, $X^1$, $X^2$, $X^3$, and m is as defined above.

In certain embodiments, the present invention provides a compound of formula I, wherein LBM is an E3 ubiquitin ligase (cereblon) binding moiety

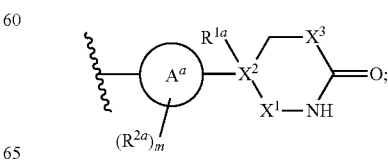

thereby forming a compound of formula I-c-1:

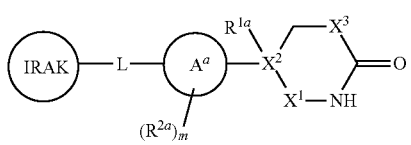

I-c-1 or a pharmaceutically acceptable salt thereof, wherein L and IRAK are as defined above and described in embodiments herein, and wherein:

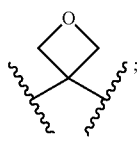 [SMILES: *C1(*)COC1]

$X^1$ is a bivalent moiety selected from a covalent bond, —CH$_2$—, —C(O)—, —C(S)—, or;

$X^2$ is a carbon atom or silicon atom;

$X^3$ is a bivalent moiety selected from —CH$_2$— or —Si(R$^2$)—;

$R^{1a}$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each $R^{2a}$ is independently hydrogen, deuterium, —R$^{6a}$, halogen, —CN, —NO$_2$, —OR, —SR, —NR$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring $A^a$ is a bi- or tricyclic ring selected from

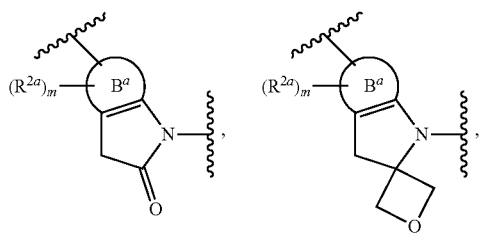

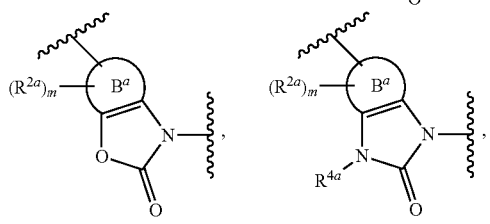

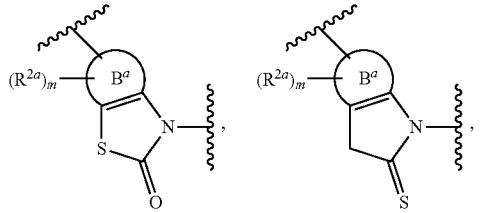

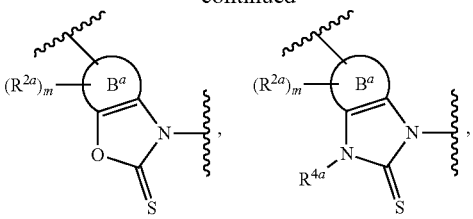

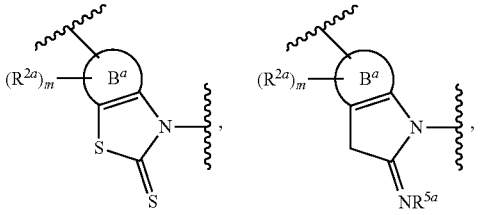

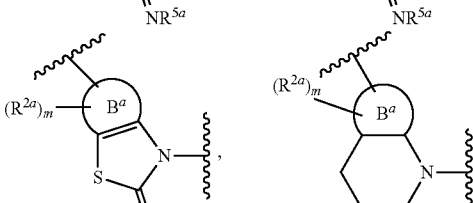

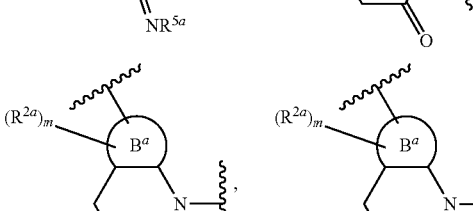

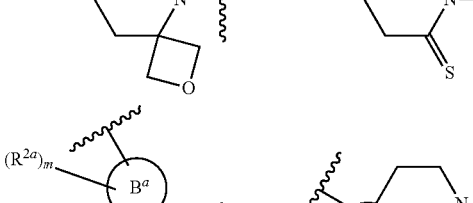

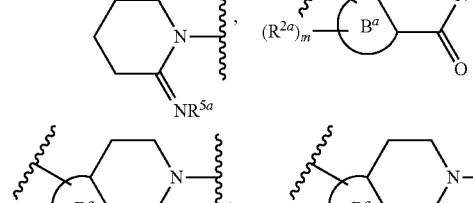

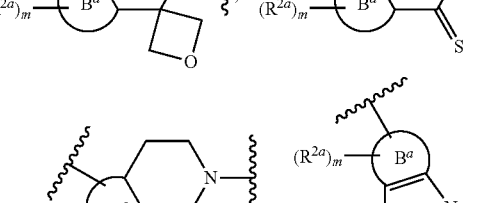

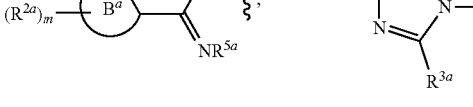

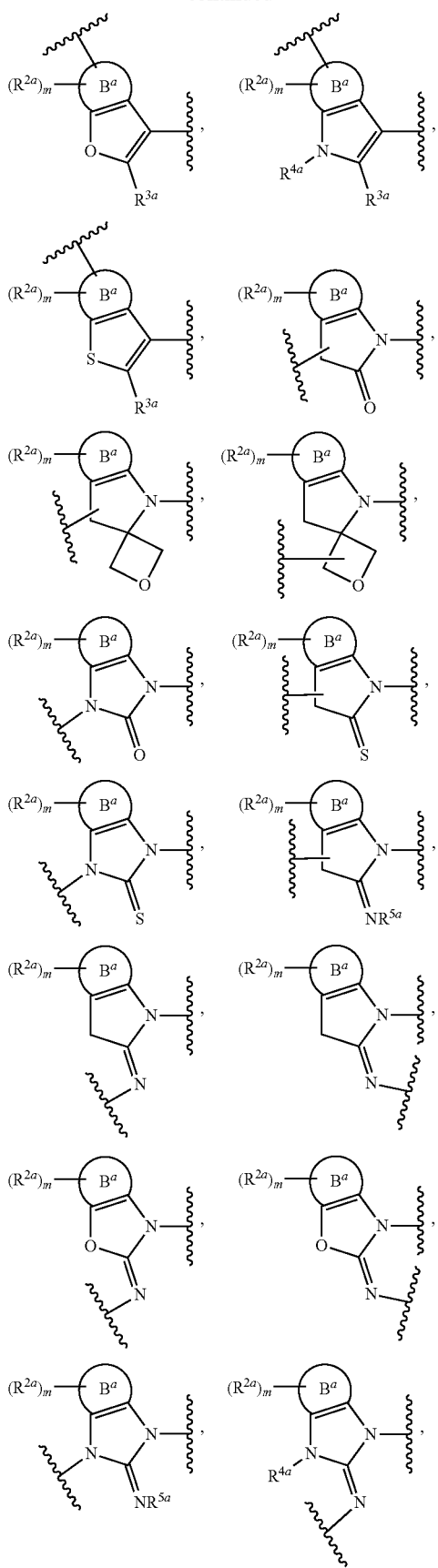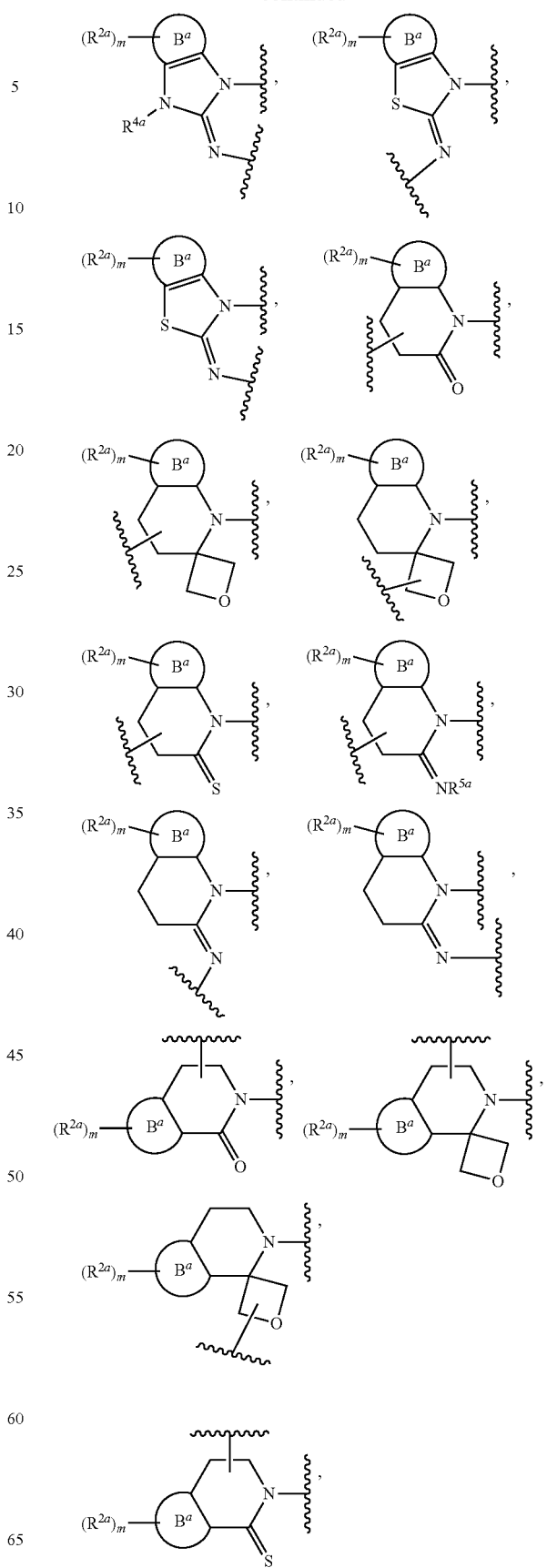

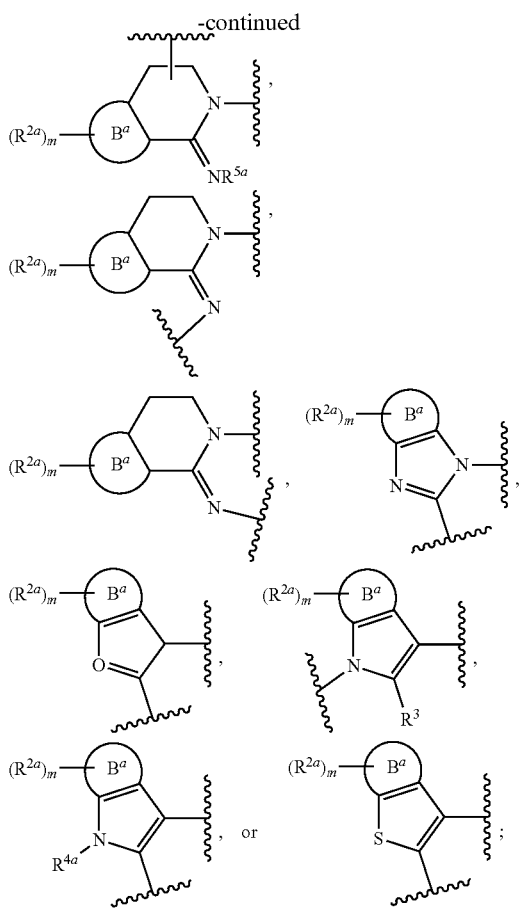

Ring $B^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from boron, nitrogen, oxygen, silicon, or sulfur, or 5-membered heteroaryl with 1-3 heteroatoms independently selected from nitrogen, oxygen or sulfur;

$R^{3a}$ is selected from hydrogen, halogen, —OR, —N(R)$_2$, or —SR;

each $R^{4a}$ is independently hydrogen, —$R^{6a}$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^{5a}$ is hydrogen, $C_{1-4}$ aliphatic, or —CN;

each $R^{6a}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-c-1 above is provided as a compound of formula I-c-1' or formula I-c-1":

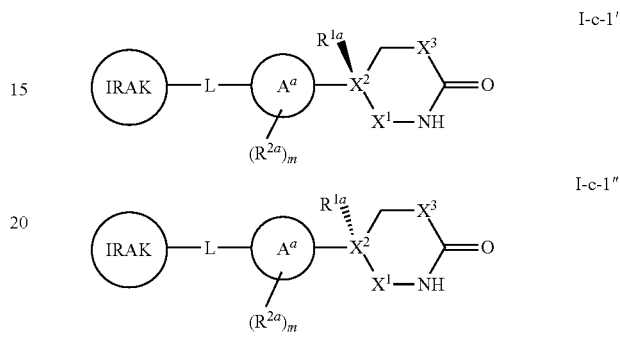

or a pharmaceutically acceptable salt thereof, wherein:
each of IRAK, Ring $A^a$, L, $R^{1a}$, $R^{2a}$, $X^1$, $X^2$, $X^3$, and m is as defined above.

In certain embodiments, the present invention provides a compound of formula I, wherein LBM is an E3 ubiquitin ligase (cereblon) binding moiety

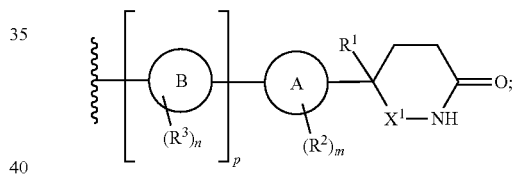

thereby forming a compound of formula I-d:

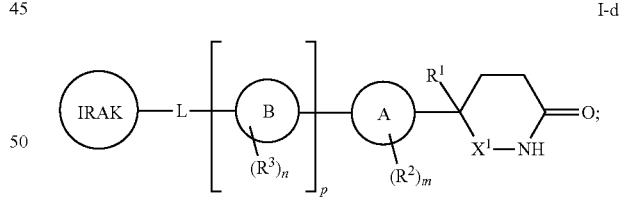

or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

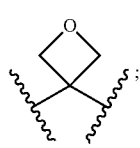

R[1] is hydrogen, deuterium, halogen, —CN, —OR, —SR, —S(O)R, —S(O)₂R, —NR₂, or an optionally substituted C₁₋₄ aliphatic;
Ring A is a mono- or bicyclic ring selected from
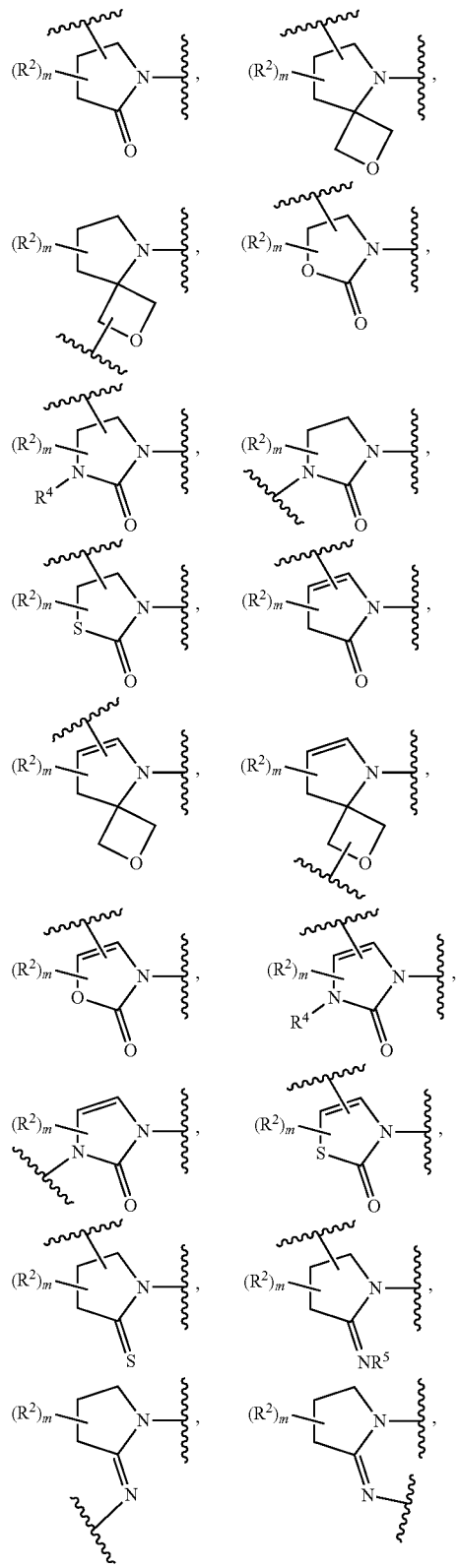
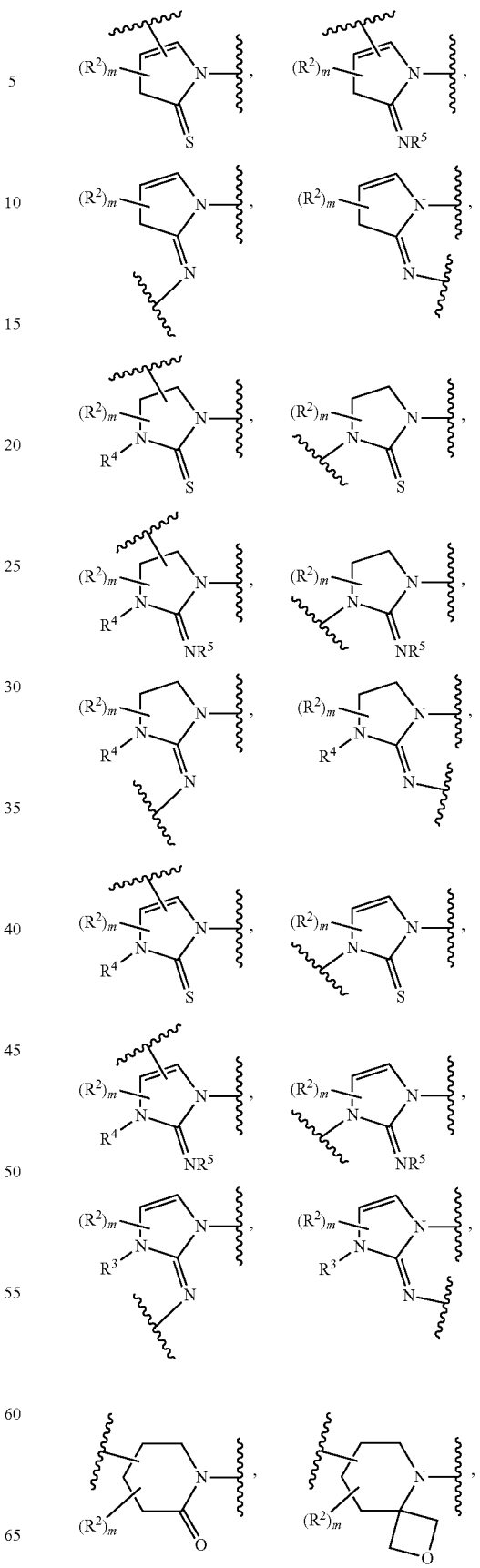

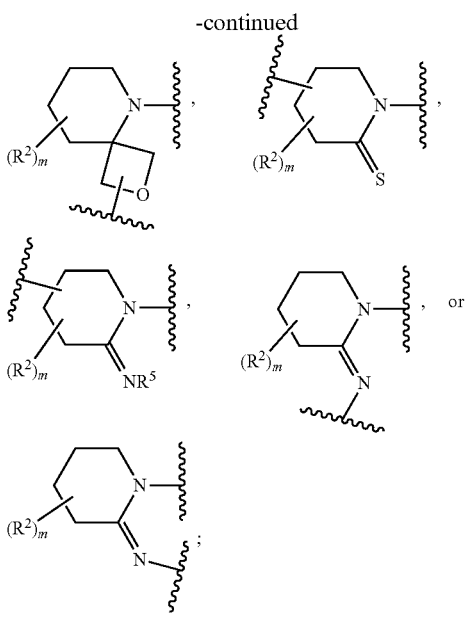

each $R^2$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring A and Ring B is connected to

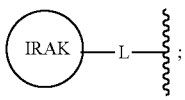

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

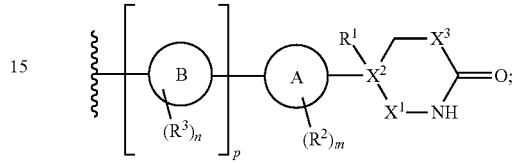

thereby forming a compound of formula I-d':

I-d'

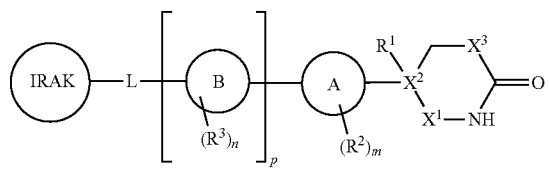

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

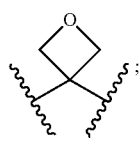 [SMILES: *C1(*)COC1]

$X^2$ is a carbon atom or silicon atom;

$X^3$ is a bivalent moiety selected from —$CH_2$— or —Si($R^2$)—;

$R^1$ is hydrogen, deuterium, halogen, —CN, —OR, —SR, —S(O)R, —$S(O)_2R$, —$N(R)_2$, —$Si(R)_3$, or an optionally substituted $C_{1-4}$ aliphatic;

Ring A is a mono- or bicyclic ring selected from

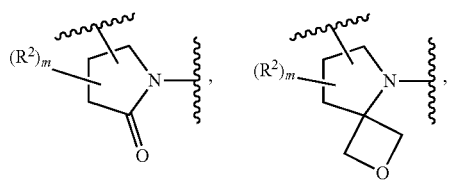

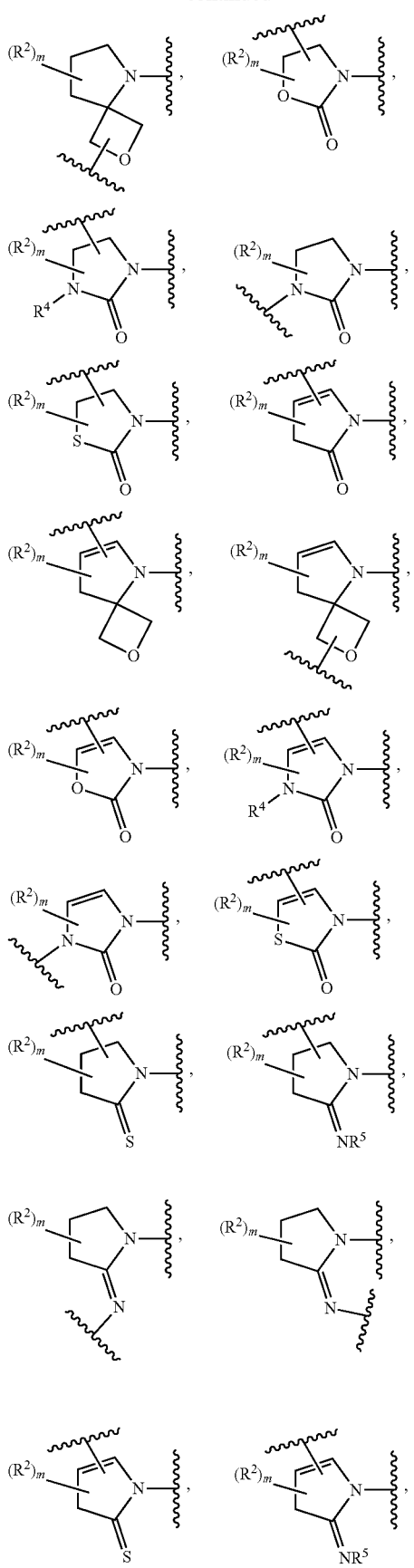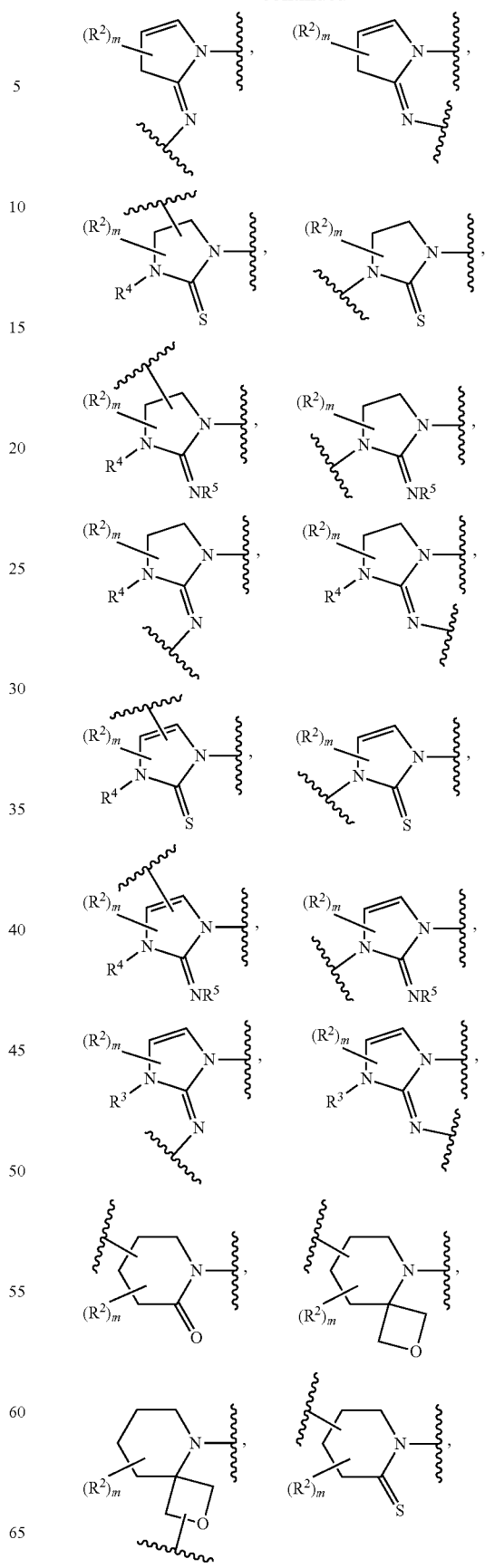

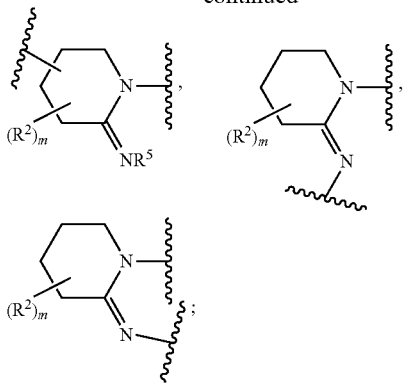

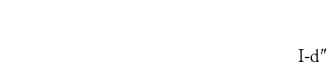

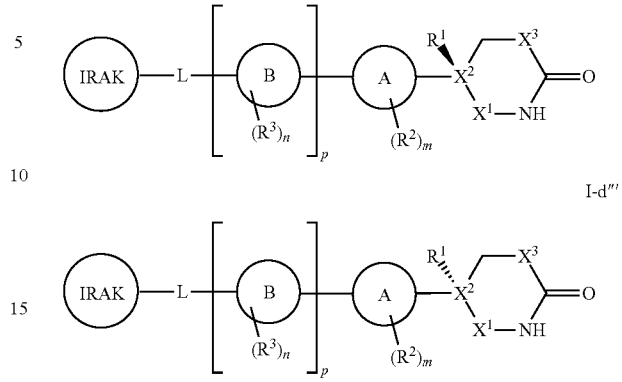

or a pharmaceutically acceptable salt thereof, wherein:

each of IRAK, Ring A, Ring B, L, $R^1$, $R^2$, $R^3$, $X^1$, $X^2$, $X^3$, m, and p is as defined above.

In certain embodiments, the present invention provides a compound of formula I, wherein LBM is an E3 ubiquitin ligase (cereblon) binding moiety

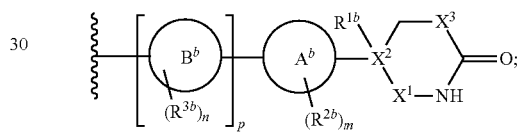

thereby forming a compound of formula I-d-1:

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

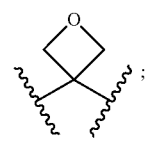 [SMILES: *C1(*)COC1]

$X^2$ is a carbon atom or silicon atom;

$X^3$ is a bivalent moiety selected from —$CH_2$— or —Si($R^2$)—;

$R^{1b}$ is hydrogen, deuterium, halogen, —CN, —OR, —SR, —S(O)R, —$S(O)_2$R, —$N(R)_2$, —$Si(R)_3$, or an optionally substituted $C_{1-4}$ aliphatic;

each $R^2$ is independently hydrogen, deuterium, —$R^6$, halogen, —CN, —$NO_2$, —OR, —SR, —$NR_2$, —$Si(R)_3$, —$S(O)_2$R, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2$R;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, —$R^6$, halogen, —CN, —$NO_2$, —OR, —SR, —$NR_2$, —$S(O)_2$R, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring A and Ring B is connected to

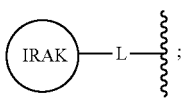

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-d' above is provided as a compound of formula I-d" or formula I-d"':

Ring $A^b$ is a mono- or bicyclic ring selected from
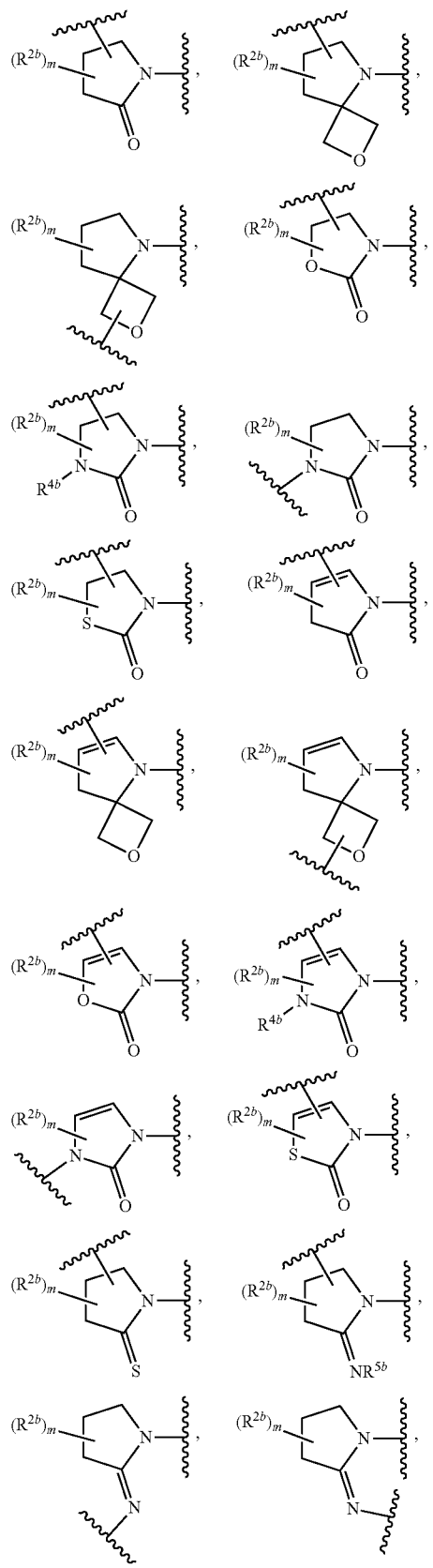
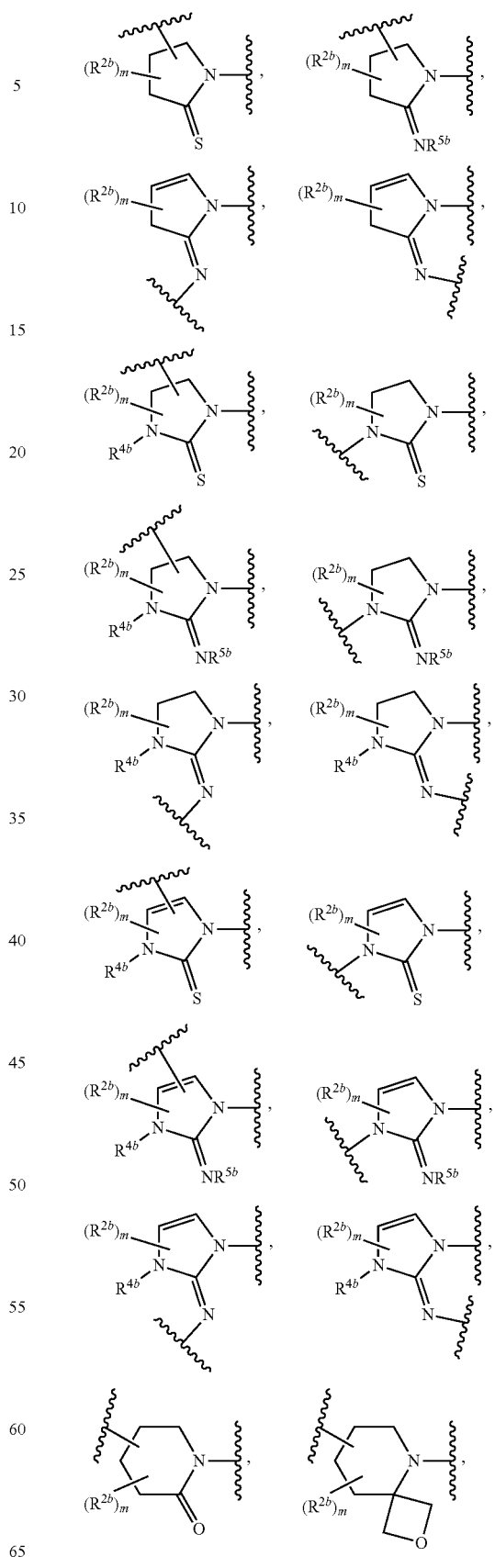

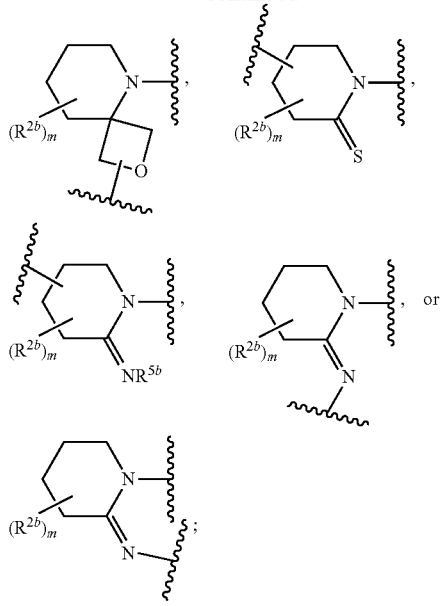

each $R^{2b}$ is independently hydrogen, deuterium, —$R^{6b}$, halogen, —CN, —$NO_2$, —OR, —SR, —$NR_2$, —$Si(R)_3$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring $B^b$ is selected from a 6-membered aryl containing 0-2 nitrogen atoms or a 5-membered heteroaryl with 1-3 heteroatoms independently selected from nitrogen, oxygen or sulfur;

each of $R^{3b}$ and $R^{4b}$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^{5b}$ is hydrogen, $C_{1-4}$ aliphatic, or —CN;

each $R^{6b}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring $A^b$ and Ring $B^b$ is connected to

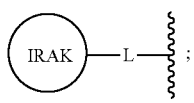

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-d-1 above is provided as a compound of formula I-d-1' or formula I-d-1":

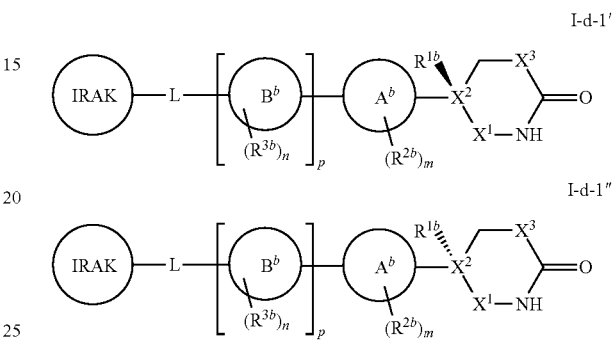

or a pharmaceutically acceptable salt thereof, wherein:

each of IRAK, Ring $A^b$, Ring $B^b$, L, R1b, $R^{2b}$, $R^{3b}$, $X^1$, $X^2$, $X^3$, m, and p is as defined above.

In certain embodiments, the present invention provides a compound of formula I, wherein LBM is an E3 ubiquitin ligase (cereblon) binding moiety

thereby forming a compound of formula I-e:

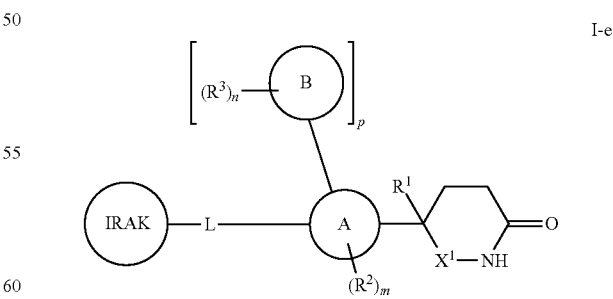

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

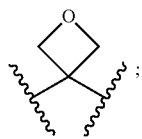 [SMILES: *C1(*)COC1]
R¹ is hydrogen, deuterium, halogen, —CN, —OR, —SR, —S(O)R, —S(O)₂R, —NR₂, or an optionally substituted $C_{1-4}$ aliphatic;
Ring A is a mono- or bicyclic ring selected from
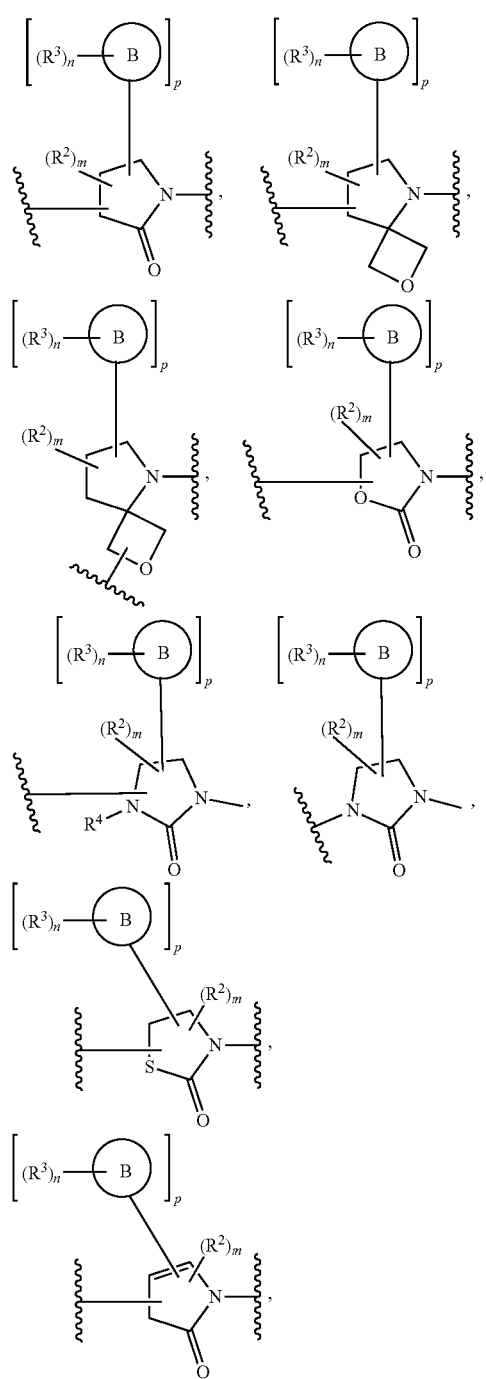
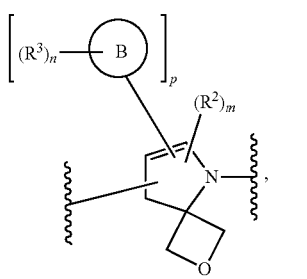
-continued
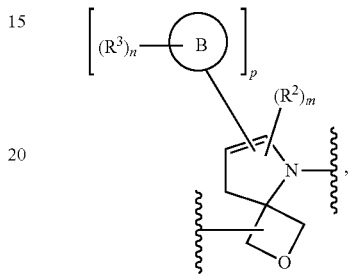
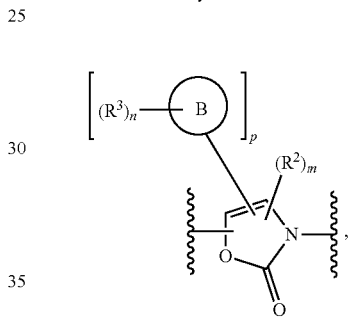
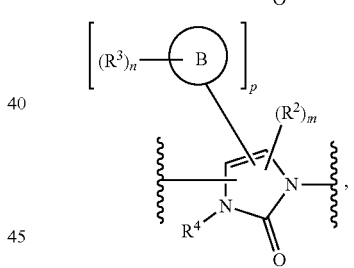
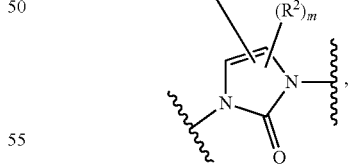
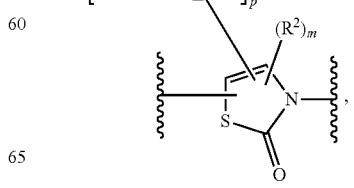
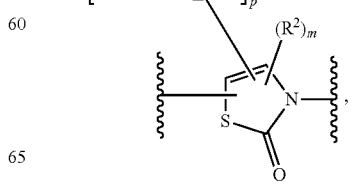

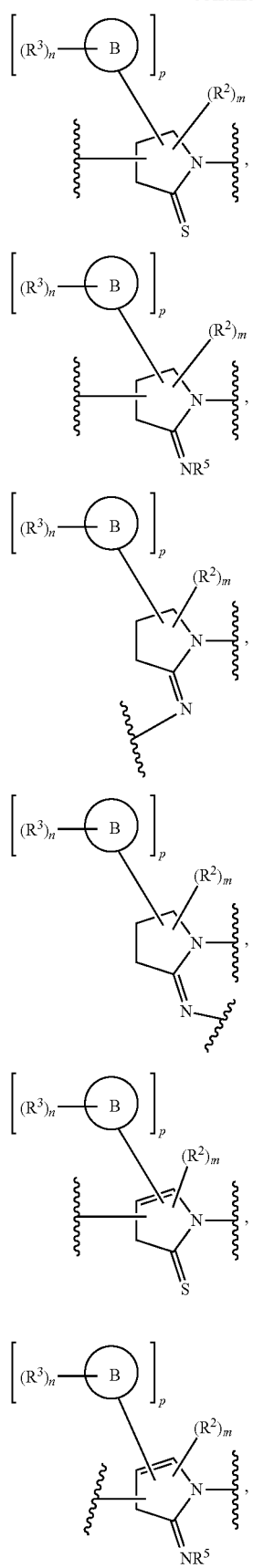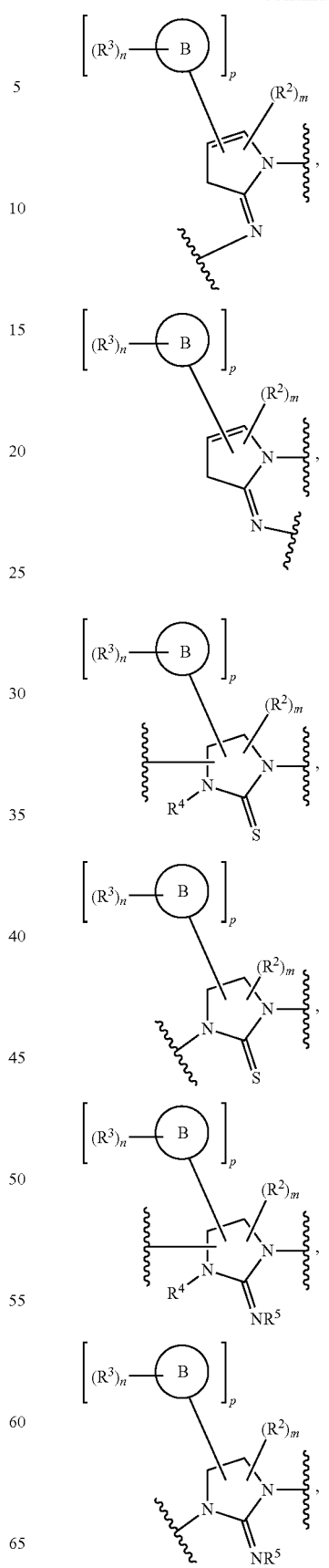

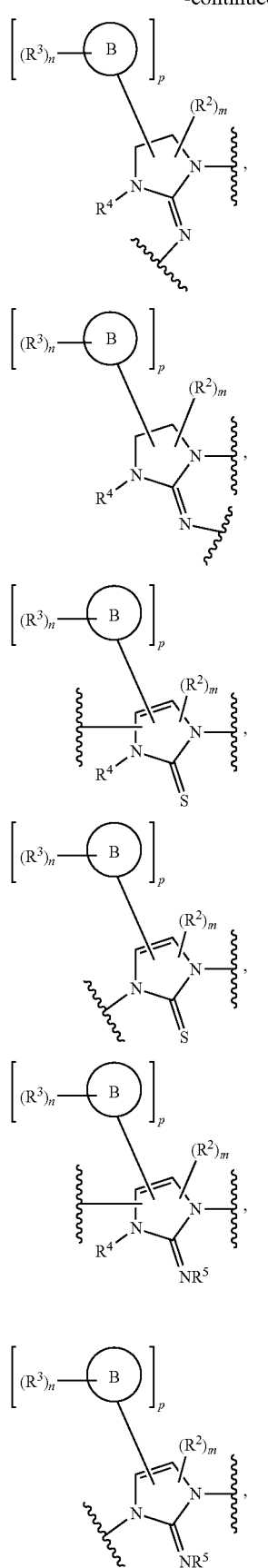
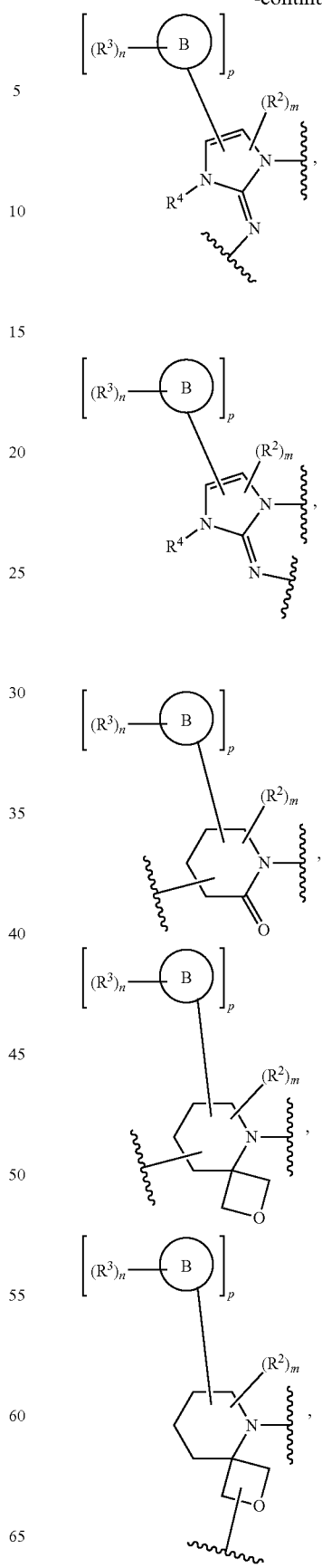

-continued

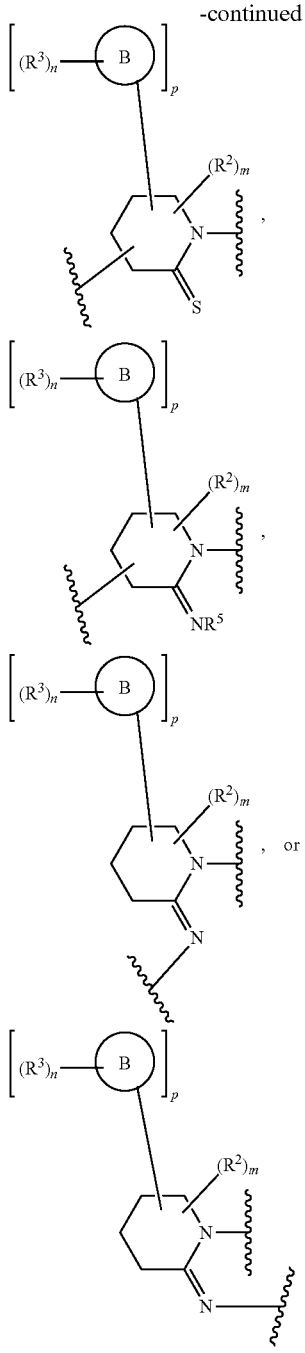

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

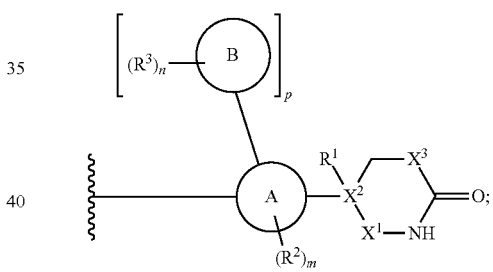

thereby forming a compound of formula I-e':

I-e'

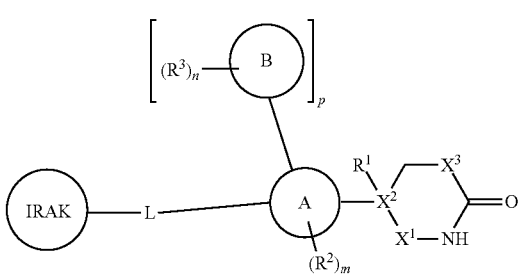

or a pharmaceutically acceptable salt thereof, wherein L and IRAK are as defined above and described in embodiments herein, and wherein:

X¹ is a bivalent moiety selected from a covalent bond, —CH₂—, —C(O)—, —C(S)—, or

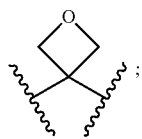
$X^2$ is a carbon atom or silicon atom;
$X^3$ is a bivalent moiety selected from —CH$_2$— or —Si(R$^2$)—;
R$^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;
Ring A is a mono- or bicyclic ring selected from
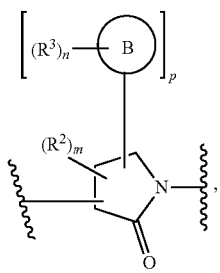 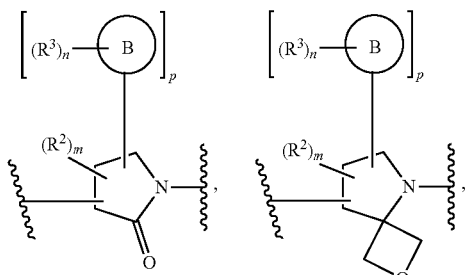
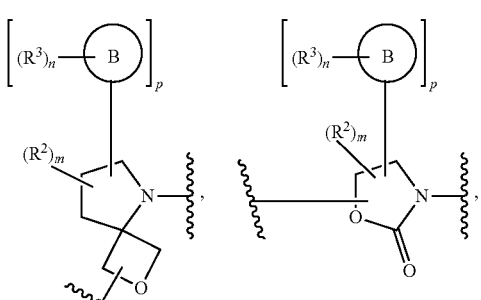
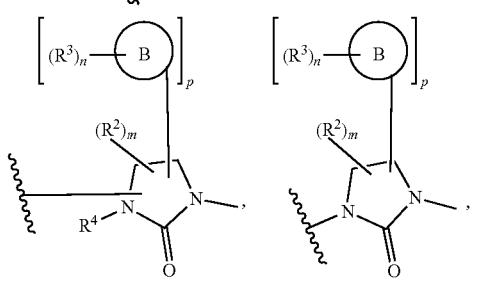
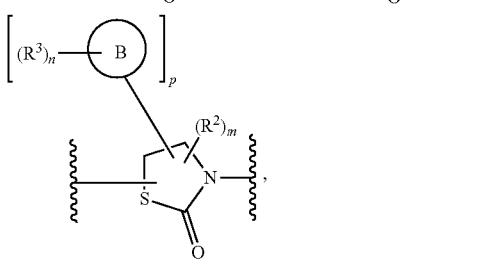
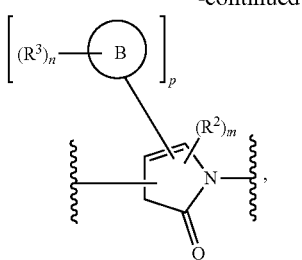
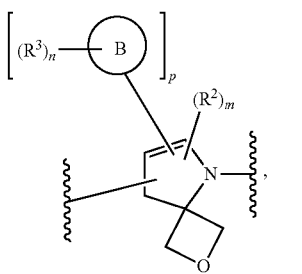
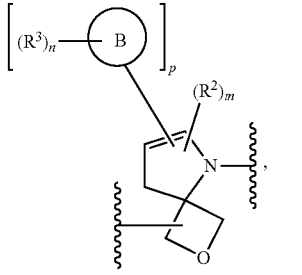
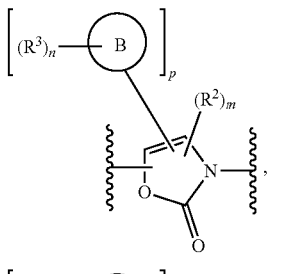
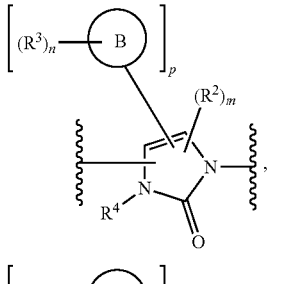
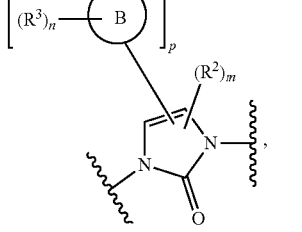

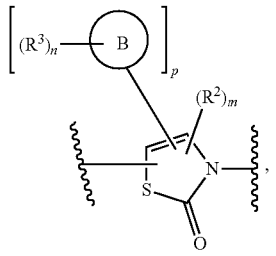,
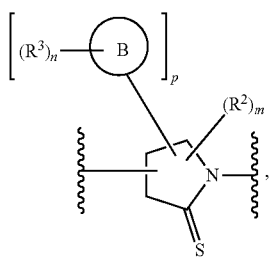,
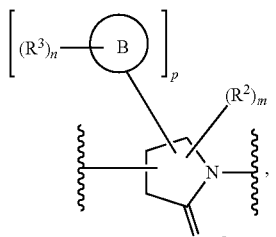,
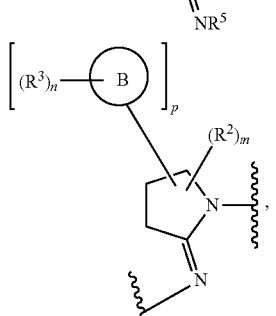,
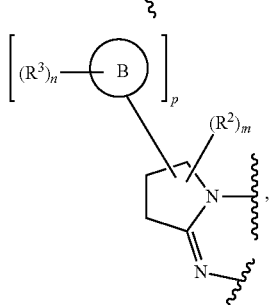,
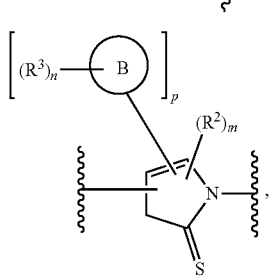,
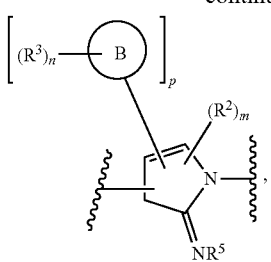,
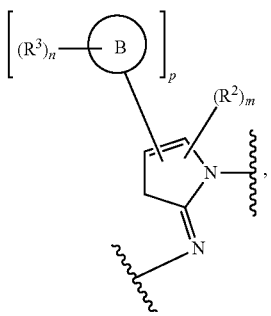,
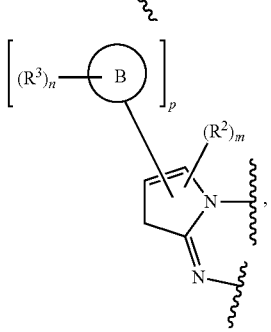,
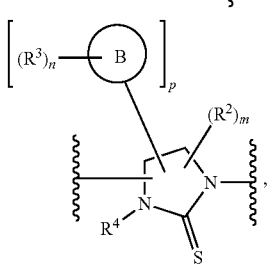,
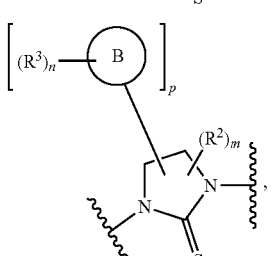,
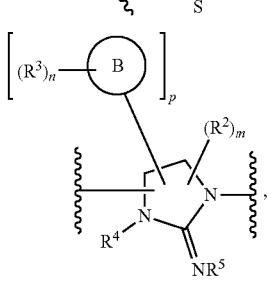,

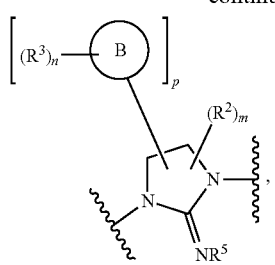
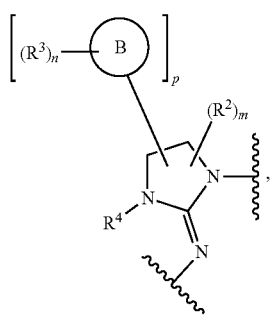
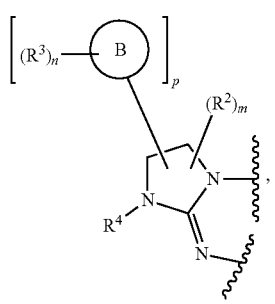
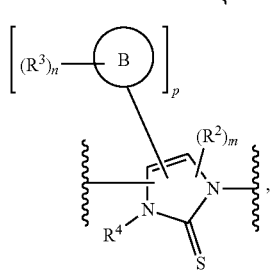
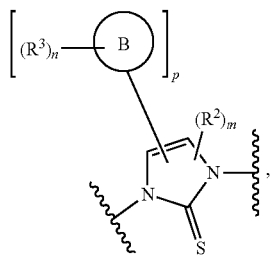
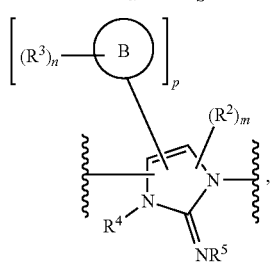
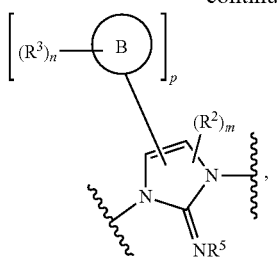
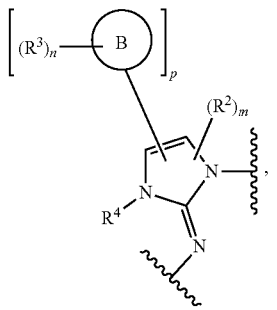
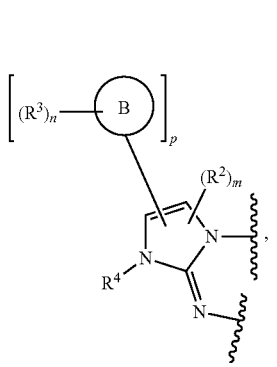
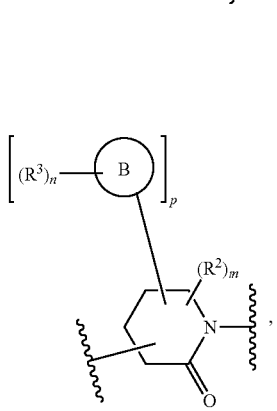
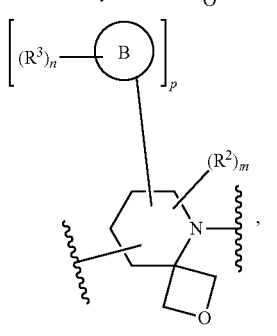

-continued

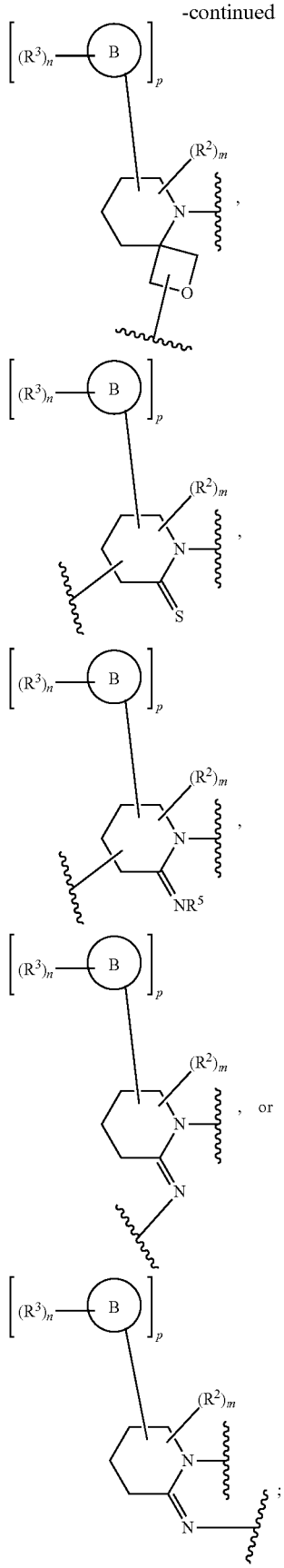

each $R^2$ is independently hydrogen, deuterium, —$R^6$, halogen, —CN, —$NO_2$, —OR, —SR, —$NR_2$, —$Si(R)_3$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-e' above is provided as a compound of formula I-e" or formula I-e''':

I-e"

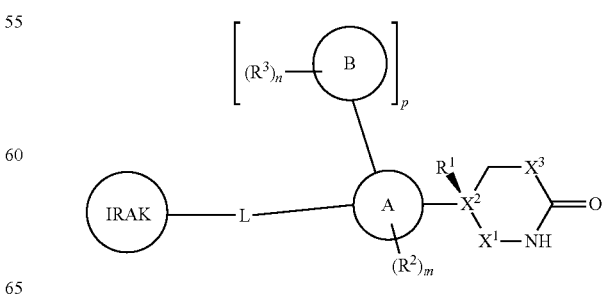

-continued

I-e'''

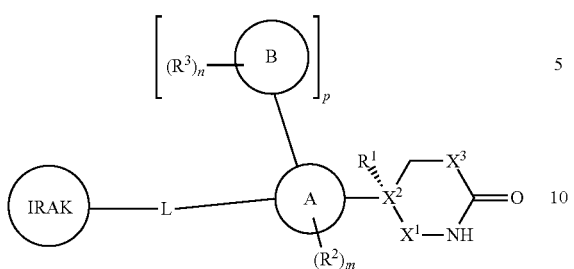

or a pharmaceutically acceptable salt thereof, wherein: each of IRAK, Ring A, Ring B, L, $R^1$, $R^2$, $R^3$, $X^1$, $X^2$, $X^3$, p, and m is as defined above.

In certain embodiments, the present invention provides a compound of formula I, wherein LBM is an E3 ubiquitin ligase (cereblon) binding moiety

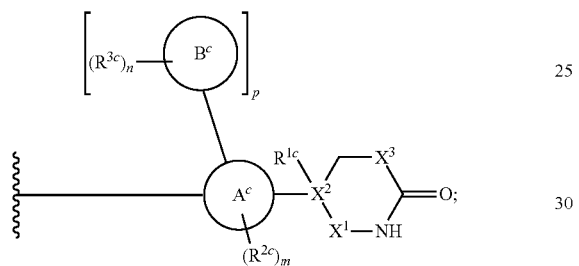

thereby forming a compound of formula I-e-1:

I-e-1

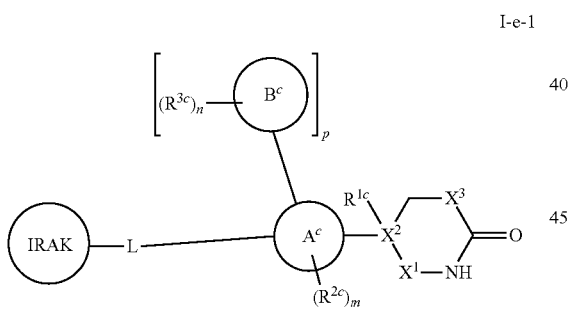

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

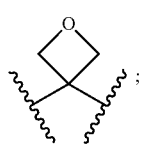 [SMILES: *C1(*)COC1];

$X^2$ is a carbon atom or silicon atom;
$X^3$ is a bivalent moiety selected from —$CH_2$— or —Si($R^2$)—;

$R^{1c}$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

Ring $A^c$ is a mono- or bicyclic ring selected from

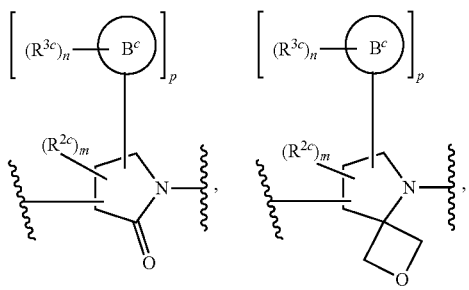

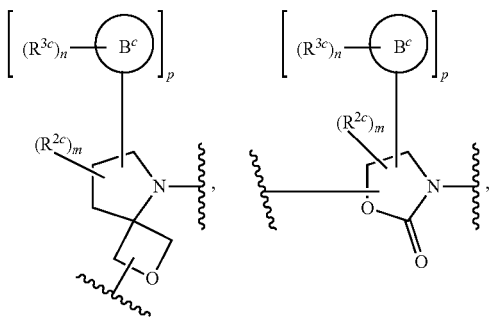

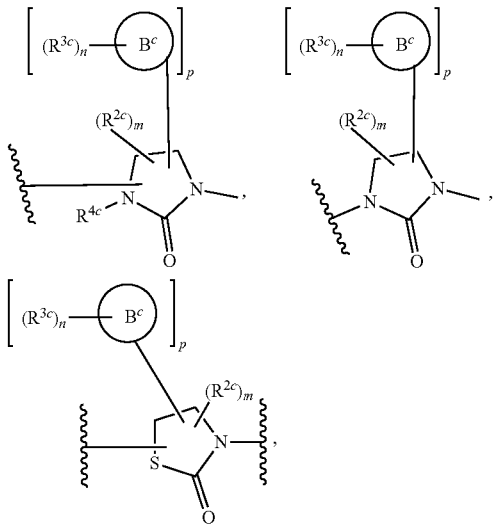

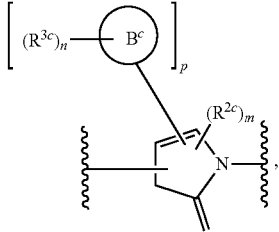

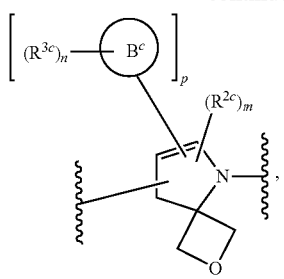
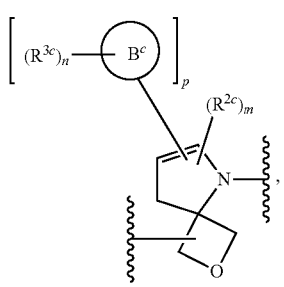
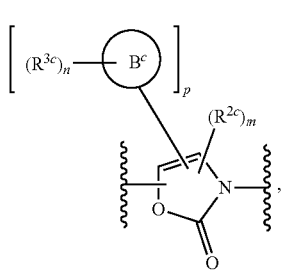
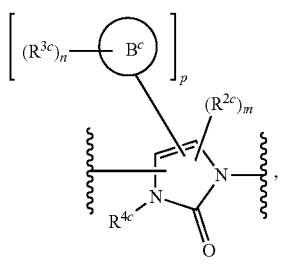
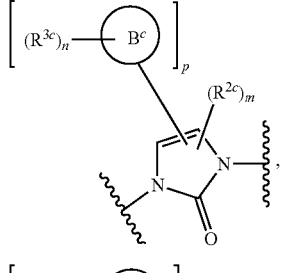
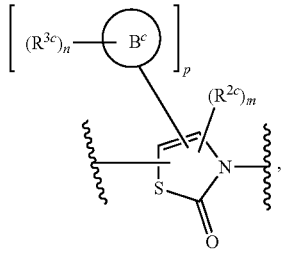
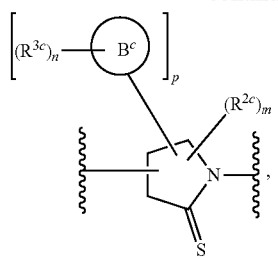
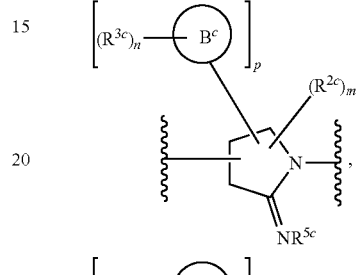
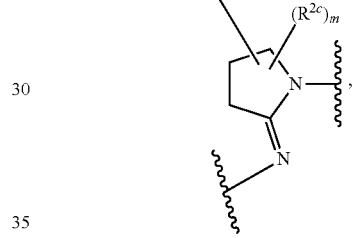
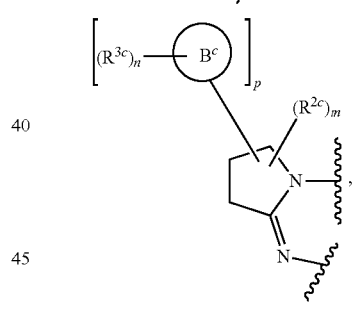
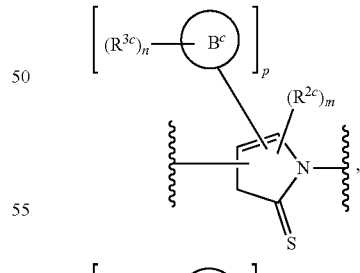
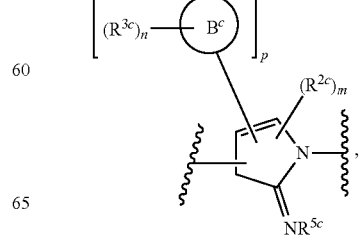

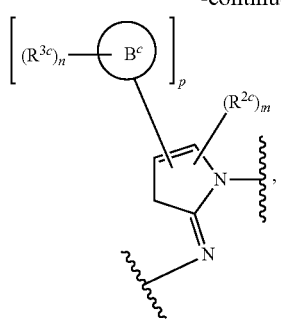
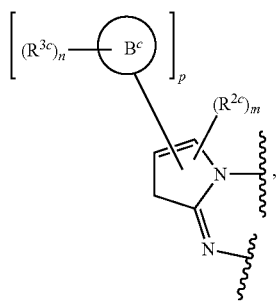
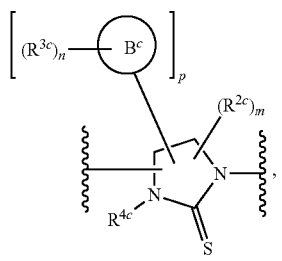
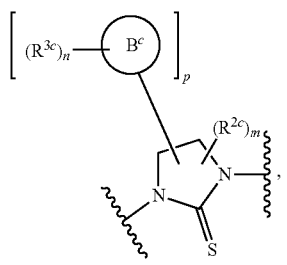
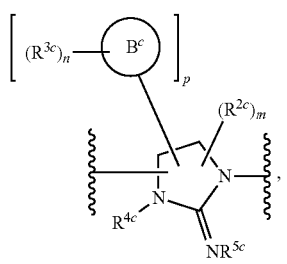
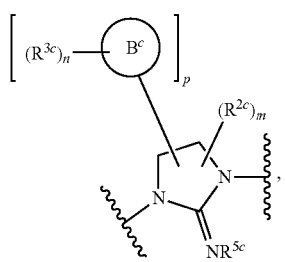
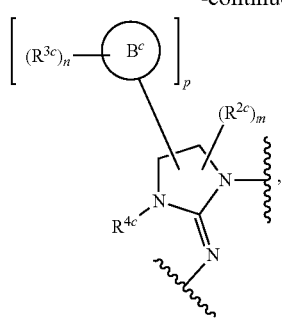
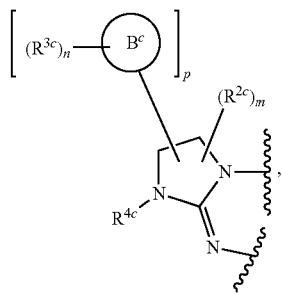
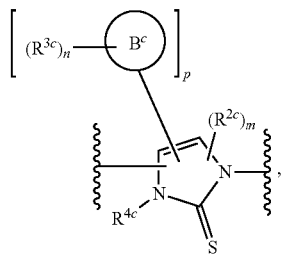
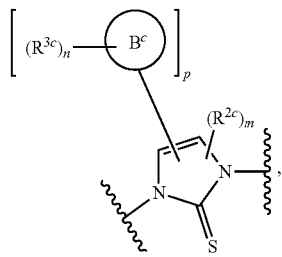
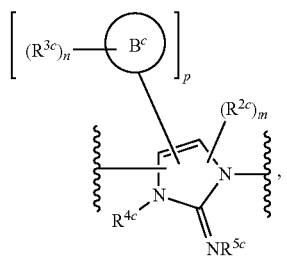
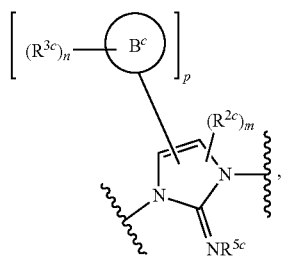

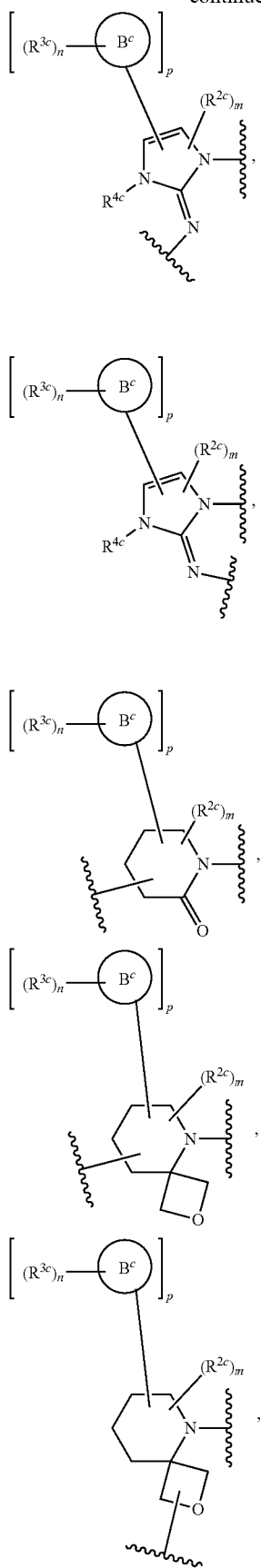

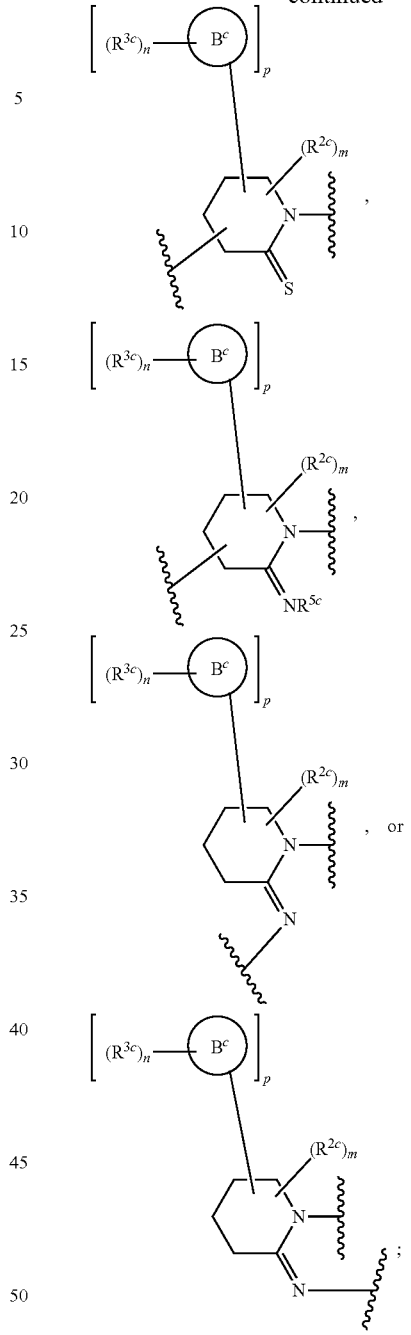

each $R^{2c}$ is independently hydrogen, deuterium, $-R^{6c}$, halogen, $-CN$, $-NO_2$, $-OR$, $-SR$, $-NR_2$, $-Si(R)_3$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each of $R^{3c}$ and $R^{4c}$ is independently hydrogen, $-R^{6c}$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)$ NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

R$^{5c}$ is hydrogen, C$_{1-4}$ aliphatic, or —CN;

each R$^{6c}$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-e-1 above is provided as a compound of formula I-e-1' or formula I-e-1":

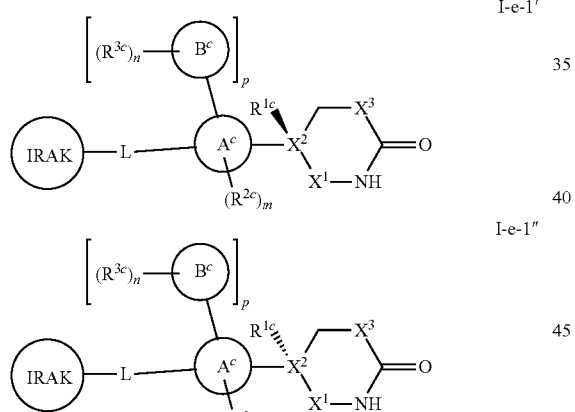

or a pharmaceutically acceptable salt thereof, wherein:
each of IRAK, Ring Ac, Ring B$^c$, L, R$^{1c}$, R$^{2c}$, R$^{3c}$, X$^1$, X$^2$, X$^3$, p, and m is as defined above.

In certain embodiments, the present invention provides a compound of formula I, wherein LBM is a VHL E3 ubiquitin ligase binding moiety

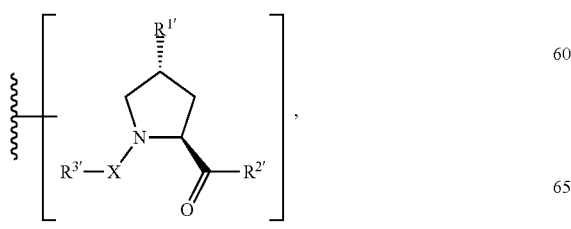

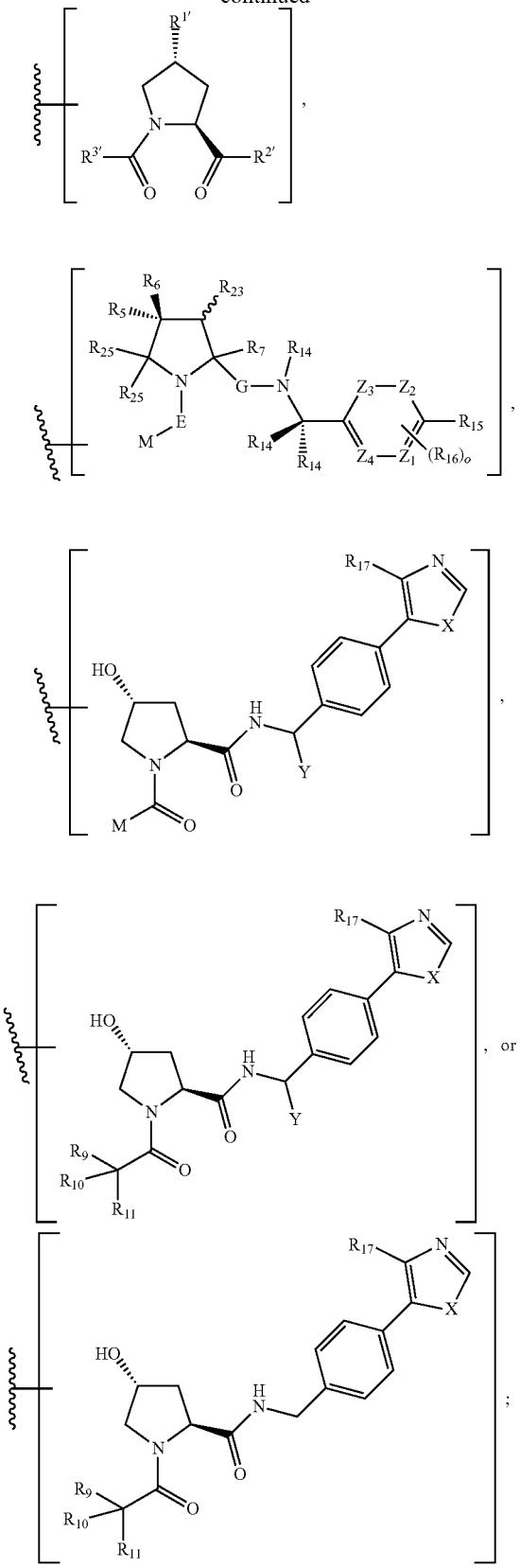

thereby forming a compound of formula I-f-1, I-f-2, I-f-3, I-f-4, I-f-5 or I-f-6 respectively:

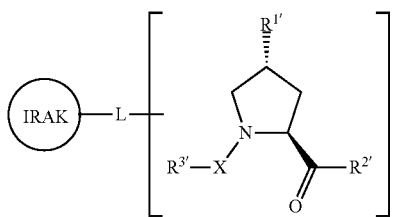

I-f-1

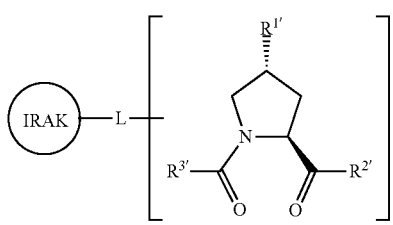

I-f-2

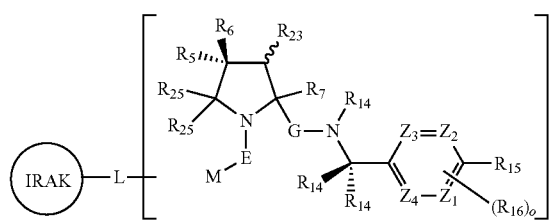

I-f-3

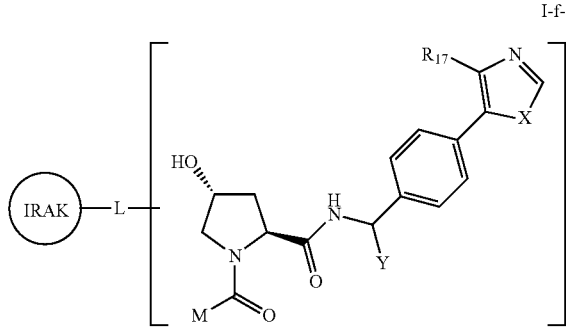

I-f-4

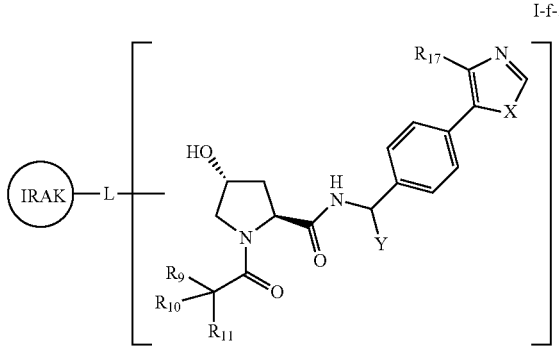

I-f-5

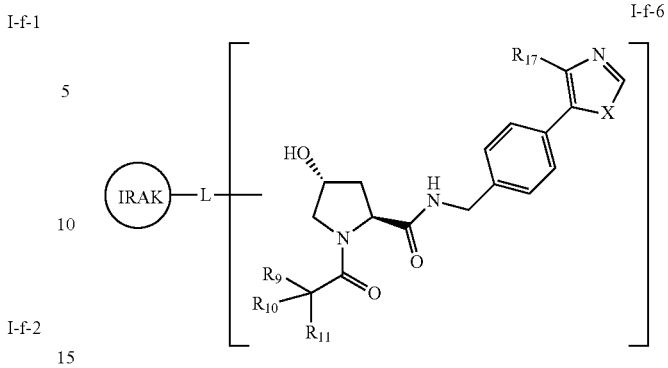

I-f-6 or a pharmaceutically acceptable salt thereof, wherein L and IRAK are as defined above and described in embodiments herein, and wherein each of the variables $R^{1'}$, $R^{2'}$, $R^{3'}$, $R_5$, $R_6$, $R_7$, $R_9$, $R_{10}$, $R_{11}$, $R_{14}$, $R_{15}$, $R_{16}$, $R_{17}$, $R_{23}$, $R_{25}$, E, G, M, X, X', Y, $Z_1$, $Z_2$, $Z_3$, $Z_4$, and o is as defined and described in WO 2016/149668 and US 2016/0272639, the entirety of each of which is herein incorporated by reference.

In certain embodiments, LBM is VHL E3 ubiquitin ligase binding moiety

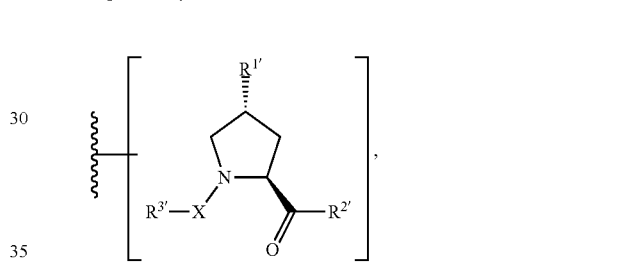

or a pharmaceutically acceptable salt thereof, wherein:

$R^{1'}$ is an optionally substituted $C_{1-6}$ alkyl group, an optionally substituted —(CH$_2$)$_n$OH, an optionally substituted —(CH$_2$)$_n$SH, an optionally substituted (CH$_2$)$_n$—O—(C$_1$-C$_6$)alkyl group, an optionally substituted (CH$_2$)$_n$—WCOCW—(C$_{0-6}$) alkyl group containing an epoxide moiety WCOCW where each W is independently H or a $C_{1-3}$ alkyl group, an optionally substituted —(CH$_2$)$_n$COOH, an optionally substituted —(CH$_2$)$_n$C(O)—(C$_{1-6}$ alkyl), an optionally substituted —(CH$_2$)$_n$NHC(O)—R$_1$, an optionally substituted —(CH$_2$)$_n$C(O)—NR$_1$R$_2$, an optionally substituted —(CH$_2$)$_n$OC(O)—NR$_1$R$_2$, —(CH$_2$O)$_n$H, an optionally substituted —(CH$_2$)$_n$OC(O)—(C$_{1-6}$ alkyl), an optionally substituted —(CH$_2$)$_n$C(O)—O—(C$_{1-6}$ alkyl), an optionally substituted —(CH$_2$O)$_n$COOH, an optionally substituted —(OCH$_2$)$_n$O—(C$_1$-C$_6$ alkyl), an optionally substituted —(CH$_2$O)$_n$C(O)—(C$_{1-6}$ alkyl), an optionally substituted —(OCH$_2$)$_n$NHC(O)—R$_1$, an optionally substituted —(CH$_2$O)$_n$C(O)—NR$_1$R$_2$, —(CH$_2$CH$_2$O)$_n$H, an optionally substituted —(CH$_2$CH$_2$O)$_n$COOH, an optionally substituted —(OCH$_2$CH$_2$)$_n$O—(C$_{1-6}$ alkyl), an optionally substituted —(CH$_2$CH$_2$O)$_n$C(O)—(C$_1$-C$_6$ alkyl), an optionally substituted —(OCH$_2$CH$_2$)$_n$NHC(O)—R$_1$, an optionally substituted —(CH$_2$CH$_2$O)$_n$C(O)—NR$_1$R$_2$, an optionally substituted —SO$_2$R$_S$, an optionally substituted S(O)R$_S$, NO$_2$, CN, or halogen;

$R_1$ and $R_2$ are each independently H or a $C_{1-6}$ alkyl group which may be optionally substituted with one or two hydroxyl groups or up to three halogen groups;

$R_S$ is a $C_{1-6}$ alkyl group, an optionally substituted aryl, heteroaryl or heterocycle group or a —$(CH_2)_m NR_1 R_2$ group;

X and X' are each independently C=O, C=S, —S(O), $S(O)_2$;

R is an optionally substituted —$(CH_2)_n$—$(C=O)_u(NR_1)_v(SO_2)_w$alkyl group, an optionally substituted —$(CH_2)_n$—$(C=O)_u(NR)_v(SO_2)_w NR_{1N} R_{2N}$ group, an optionally substituted —$(CH_2)_n$—$(C=O)_u(NR_1)_v(SO_2)_w$-Aryl, an optionally substituted —$(CH_2)_n$—$(C=O)_u(NR_1)_v(SO_2)_w$-heteroaryl, an optionally substituted —$(CH_2)_n$—$(C=O)_v NR_1(SO_2)_w$-heterocycle, an optionally substituted —$NR^1$—$(CH_2)_n$—$C(O)_u(NR_1)_v(SO_2)_w$-alkyl, an optionally substituted —$NR^1$—$(CH_2)_n$—$C(O)_u(NR_1)_v(SO_2)_w$—$NR_1 NR_2 N$, an optionally substituted —$NR^1$—$(CH_2)_n$—$C(O)_u(NR_1)_v(SO_2)_w$—$NR_1 C(O)R_{1N}$, an optionally substituted —$NR^1$—$(CH_2)_n$—$(C=O)_u(NR_1)_v(SO_2)_w$-aryl, an optionally substituted —$NR^1$—$(CH_2)_n$—$(C=O)_u(NR_1)_v(SO_2)_w$-heteroaryl or an optionally substituted —$NR$—$(CH_2)_n$—$(C=O)_v NR_1(SO_2)_w$-heterocycle, an optionally substituted —$X^{R2'}$-alkyl group; an optionally substituted —$X^{R2'}$-aryl group; an optionally substituted —$X^{R2'}$-heteroaryl group; an optionally substituted —$X^{R2'}$-heterocycle group;

$R^{3'}$ is an optionally substituted alkyl, an optionally substituted —$(CH_2)_n$—$(O)_u(NR_1)_v(SO_2)_w$-alkyl, an optionally substituted —$(CH_2)_n$—$C(O)_u(NR_1)_v(SO_2)_w$—$NR_1 NR_2 N$, an optionally substituted —$(CH_2)_n$—$C(O)_u(NR_1)_v(SO_2)_w$—$NR_1 C(O)R_{1N}$, an optionally substituted —$(CH_2)_n$—$C(O)_u(NR_1)_v(SO_2)_w$—$C(O)NR_1 R_2$, an optionally substituted —$(CH_2)_n$—$C(O)_u(NR_1)_v(SO_2)_w$-Aryl, an optionally substituted —$(CH_2)_n$—$C(O)_u(NR_1)_v(SO_2)_w$-heteroaryl, an optionally substituted —$(CH_2)_n$—$C(O)_u(NR_1)_v(SO_2)_w$-heterocycle, an optionally substituted —$NR^{1'}(CH_2)_n$—$C(O)_u(NR_1)_v(SO_2)_w$-alkyl, an optionally substituted —$NR^1$—$(CH_2)_n$—$C(O)_u(NR_1)_v(SO_2)_w$—$NR_1 NR_2 N$, an optionally substituted —$NR^1$—$(CH_2)_n$—$C(O)_u(NR_1)_v(SO_2)_w$—$NR_1 C(O)R_{1N}$, an optionally substituted —$NR^1$—$(CH_2)_n$—$C(O)_u(NR_1)_v(SO_2)_w$-Aryl, an optionally substituted —$NR^1$—$(CH_2)_n$—$C(O)_u(NR_1)_v(SO_2)_w$-heteroaryl, an optionally substituted —$NR^1$—$(CH_2)_n$—$C(O)_u(NR_1)_v(SO_2)_w$-heterocycle, an optionally substituted —$O$—$(CH_2)_n$—$(C=O)_u(NR_1)_v(SO_2)_w$-alkyl, an optionally substituted —$O$—$(CH_2)_n$—$(C=O)_u(NR_1)_v(SO_2)_w$—$NR_{1N} R_{2N}$, an optionally substituted —$O$—$(CH_2)_n$—$(C=O)_u(NR_1)_v(SO_2)_w$—$NR_1 C(O)R_{1N}$, an optionally substituted —$O$—$(CH_2)_n$—$(C=O)_u(NR_1)_v(SO_2)_w$-Aryl, an optionally substituted —$O$—$(CH_2)_n$—$(C=O)_u(NR_1)_v(SO_2)_w$-heteroaryl or an optionally substituted —$O$—$(CH_2)_n$—$(C=O)_u(NR_1)_v(SO_2)_w$-heterocycle; —$(CH_2)_n$—$(V)_{n'}$—$(CH_2)_n$—$(V)_{n'}$-alkyl group, an optionally substituted —$(CH_2)_n$—$(V)_{n'}$—$(CH_2)_n$—$(V)_{n'}$-aryl group, an optionally substituted —$(CH_2)_n$—$(V)_{n'}$—$(CH_2)_n$—$(V)_{n'}$-heteroaryl group, an optionally substituted —$(CH_2)_n$—$(V)_{n'}$—$(CH_2)_n$—$(V)_{n'}$-heterocycle group, an optionally substituted —$(CH_2)_n$—$N(R_{1'})(C=O)_{m'}$—$(V)_{n'}$-alkyl group, an optionally substituted —$(CH_2)$—$N(R_{1'})(C=O)_{m'}$—$(V)_{n'}$-aryl group, an optionally substituted —$(CH_2)_n$—$N(R_{1'})(C=O)_{m'}$—$(V)_{n'}$-heteroaryl group, an optionally substituted —$(CH_2)_n$—$N(R_{1'})(C=O)_{m'}$—$(V)_{n'}$-heterocycle group, an optionally substituted —$X^{R3'}$-alkyl group, an optionally substituted —$X^{R3'}$-aryl group, an optionally substituted —$X^{R3'}$-heteroaryl group, an optionally substituted —$X^{R3'}$-heterocycle group, wherein $R_{1N}$ and $R_{2N}$ are each independently H, $C_{1-6}$ alkyl which is optionally substituted with one or two hydroxyl groups and up to three halogen groups or an optionally substituted —$(CH_2)_n$-aryl, —$(CH_2)_n$-heteroaryl or —$(CH_2)_n$-heterocycle group;

V is O, S or $NR_1$;

$R_1$ is the same as above;

$R^1$ and $R_{1'}$ are each independently H or a $C_1$-$C_3$ alkyl group;

$X^{R2'}$ and $X^{R3'}$ are each independently an optionally substituted —$(CH_2)_n$—, —$(CH_2)_n$—$CH(X_v)$=$CH(X_v)$—, —$(CH_2)_n$—$CH\equiv CH$—, —$(CH_2 CH_2 O)_n$— or a $C_3$-$C_6$ cycloalkyl group, where $X_v$ is H, a halo or a $C_1$-$C_3$ alkyl group which is optionally substituted;

each m is independently 0, 1, 2, 3, 4, 5, 6;

each m' is independently 0 or 1;

each n is independently 0, 1, 2, 3, 4, 5, 6;

each n' is independently 0 or 1;

each u is independently 0 or 1;

each v is independently 0 or 1; and each w is independently 0 or 1.

As used herein, depiction of brackets around any LBM

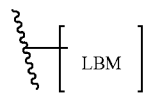

means that the

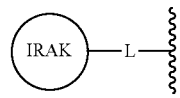

moiety is covalently attached to said LBM at any available modifiable carbon, nitrogen, oxygen, or sulfur atom. For purposes of clarity and by way of example, such available modifiable carbon, nitrogen, oxygen, or sulfur atoms in the following LBM compound structure are depicted below, wherein each wavy bond defines the point of attachment to said

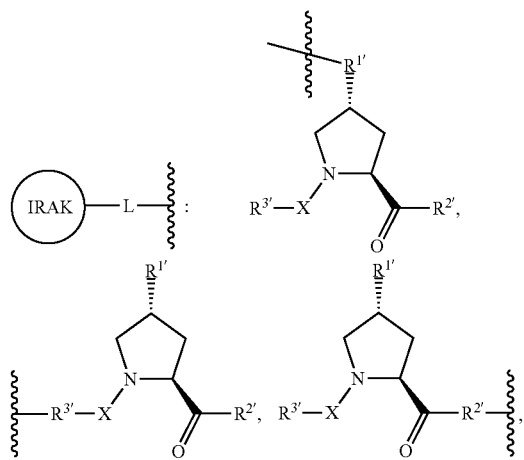

-continued

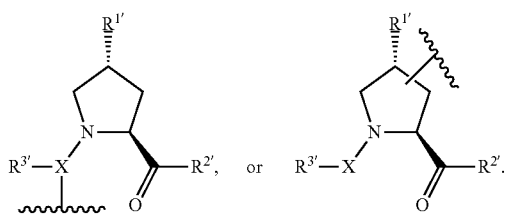

In certain embodiments, the present invention provides a compound of formula I, wherein LBM is a VHL E3 ubiquitin ligase binding moiety

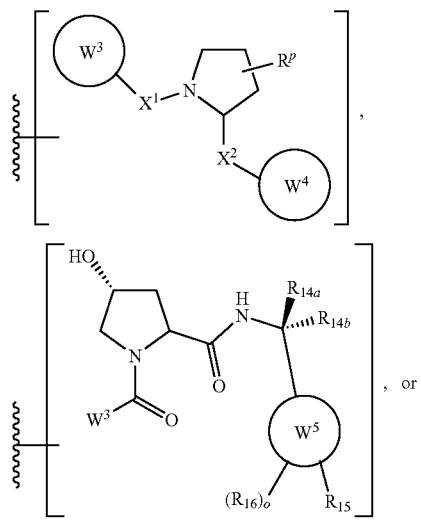

thereby forming a compound of formula I-g-1, I-g-2, or I-g-3 respectively:

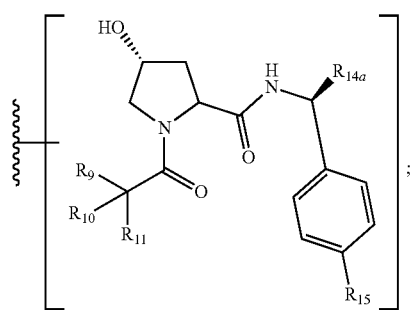

I-g-1

-continued

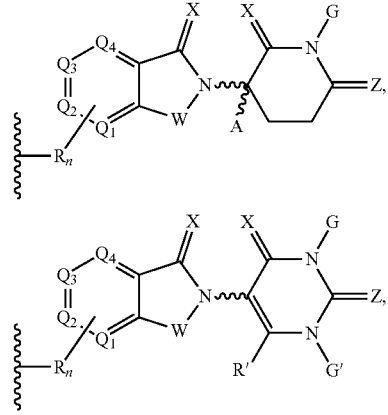

I-g-2

I-g-3 or a pharmaceutically acceptable salt thereof, wherein L and IRAK are as defined above and described in embodiments herein, and wherein each of the variables $R^P$, $R_9$, $R_{10}$, $R_{11}$, $R_{14a}$, $R_{14b}$, $R_{15}$, $R_{16}$, $W^3$, $W^4$, $W^5$, $X^1$, $X^2$, and o is as defined and described in WO 2017/030814, WO 2016/118666 and US 2016/0214972, the entirety of each of which is herein incorporated by reference.

In certain embodiments, the present invention provides a compound of formula I, wherein LBM is an E3 ubiquitin ligase (cereblon) binding moiety

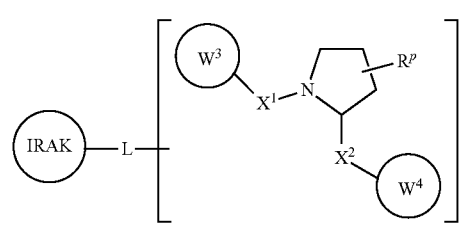

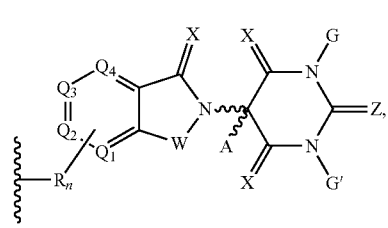

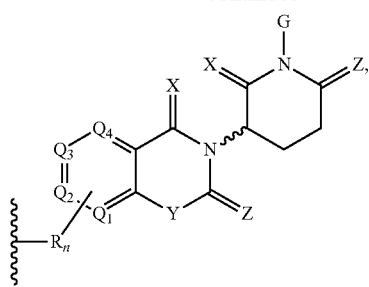

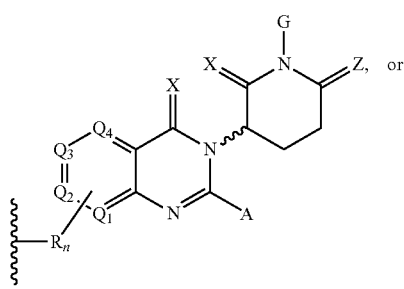

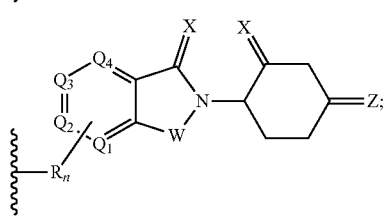

thereby forming a compound of formula I-h-1, I-h-2, I-h-3, I-h-4, I-h-5, or I-h-6 respectively:

I-h-1

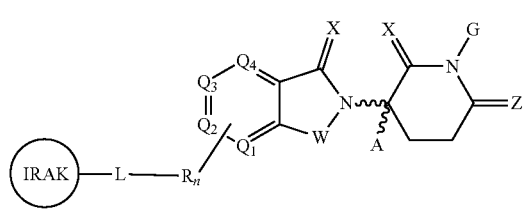

I-h-2

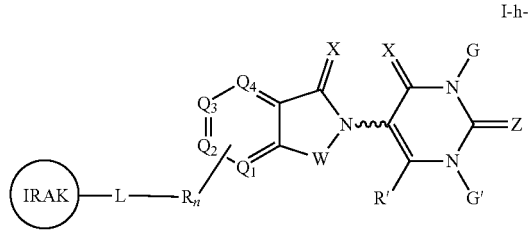

I-h-3

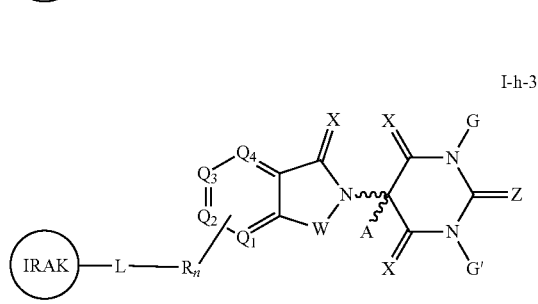

I-h-4

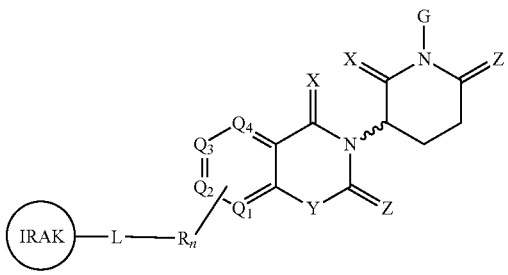

I-h-5

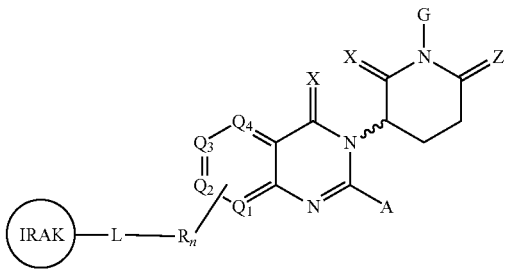

I-h-6

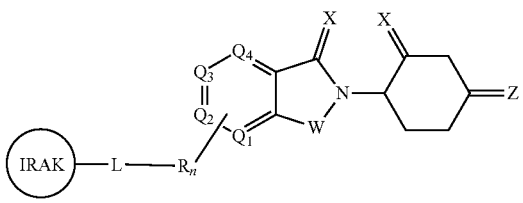

or a pharmaceutically acceptable salt thereof, wherein L and IRAK are as defined above and described in embodiments herein, and wherein each of the variables A, G, G', $Q_1$, $Q_2$, $Q_3$, $Q_4$, R, R', W, X, Z, and n is as defined and described in WO 2016/197114 and US 2018/0147202, the entirety of each of which is herein incorporated by reference.

In certain embodiments, the present invention provides a compound of formula I, wherein LBM is a MDM2 (i.e. human double minute 2 or HDM2) E3 ligase binding moiety

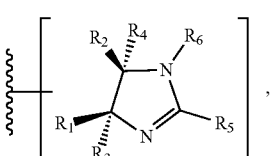

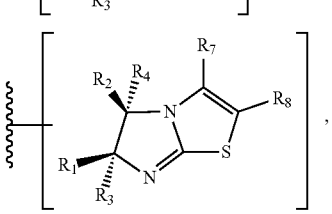

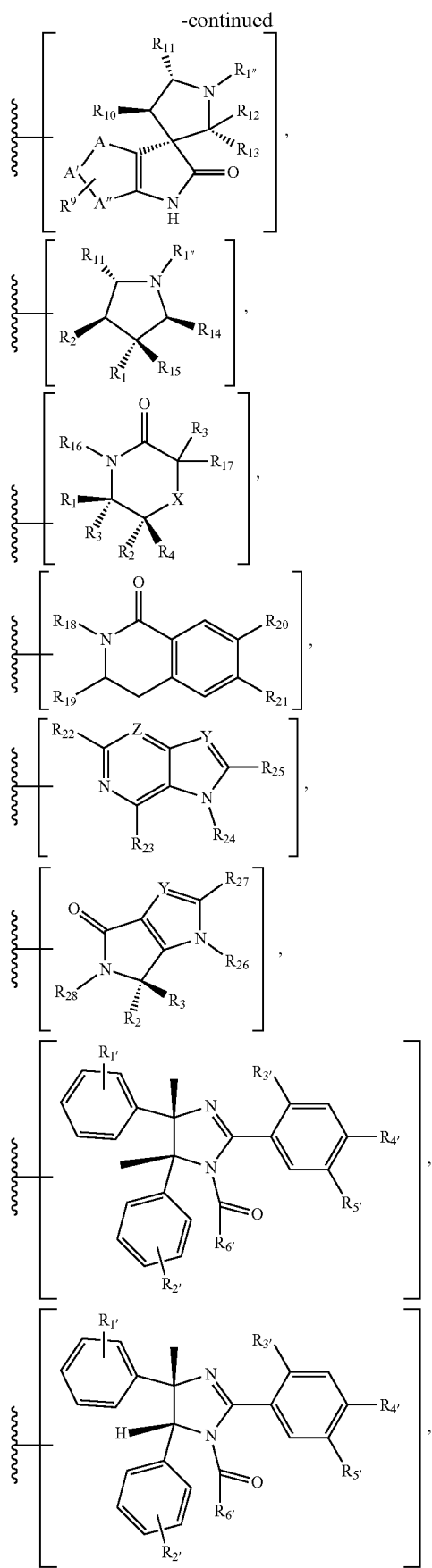
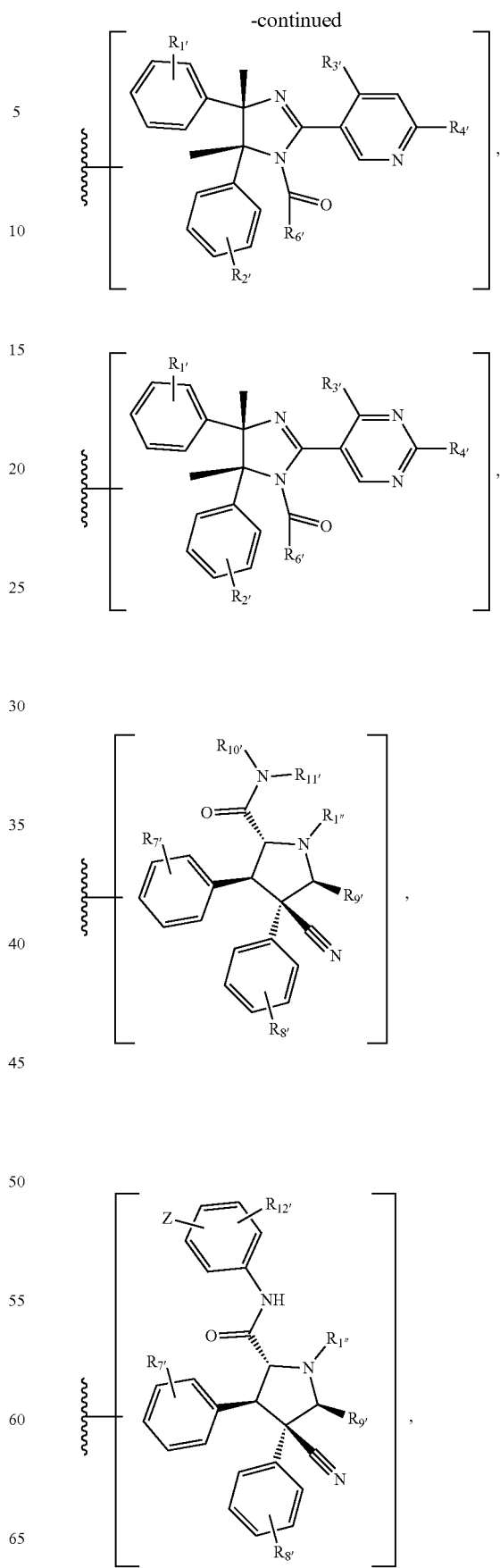

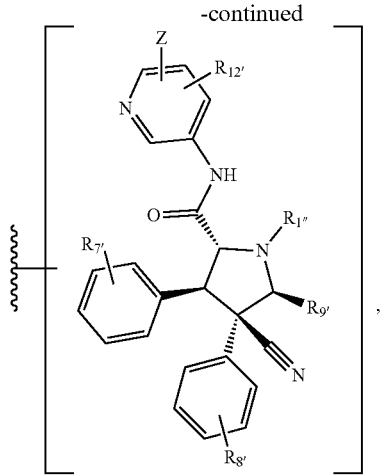
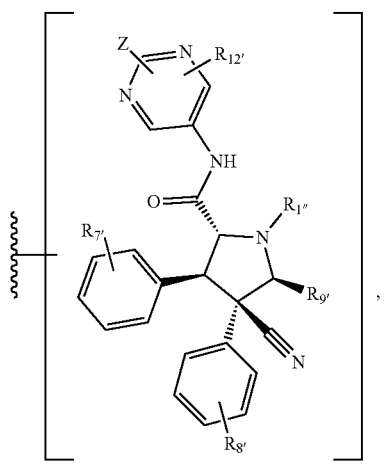
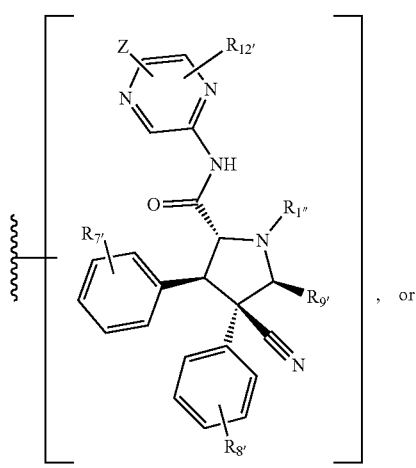
, or
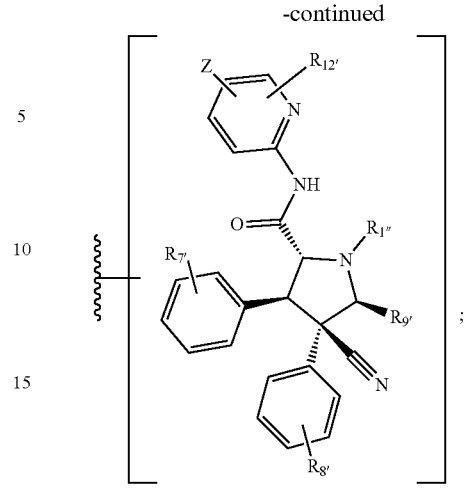
;
thereby forming a compound of formula I-i-1, I-i-2, I-i-3, I-i-4, I-i-5, I-i-6, I-i-7, I-i-8, I-i-9, I-i-10, I-i-11, I-i-12, I-i-13, I-i-14, I-i-15 I-i-16, I-i-17, or I-i-18 respectively:
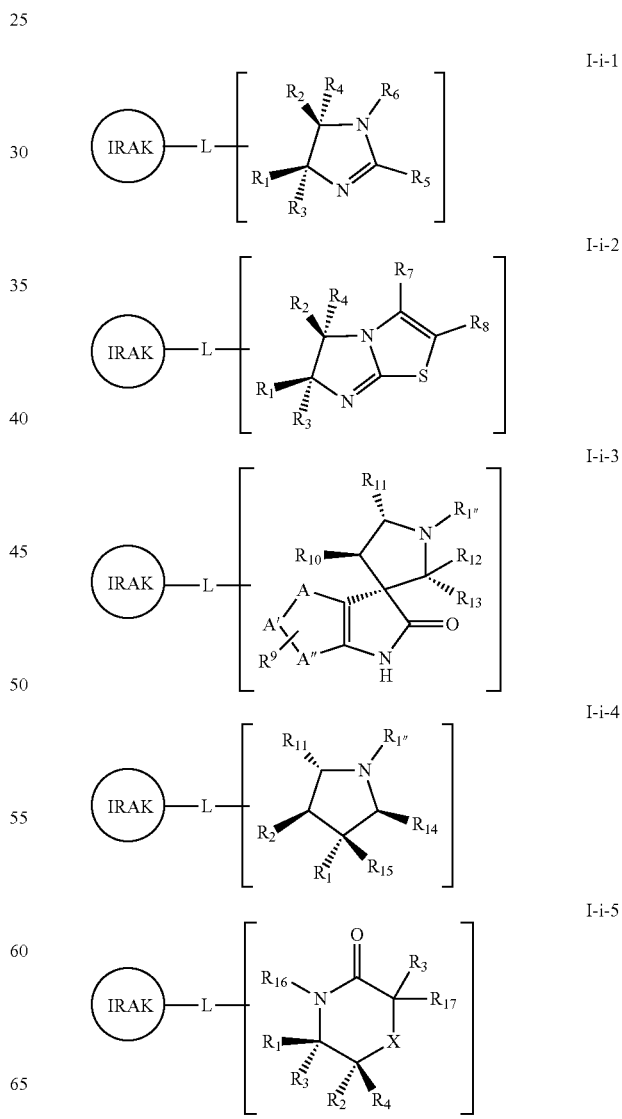

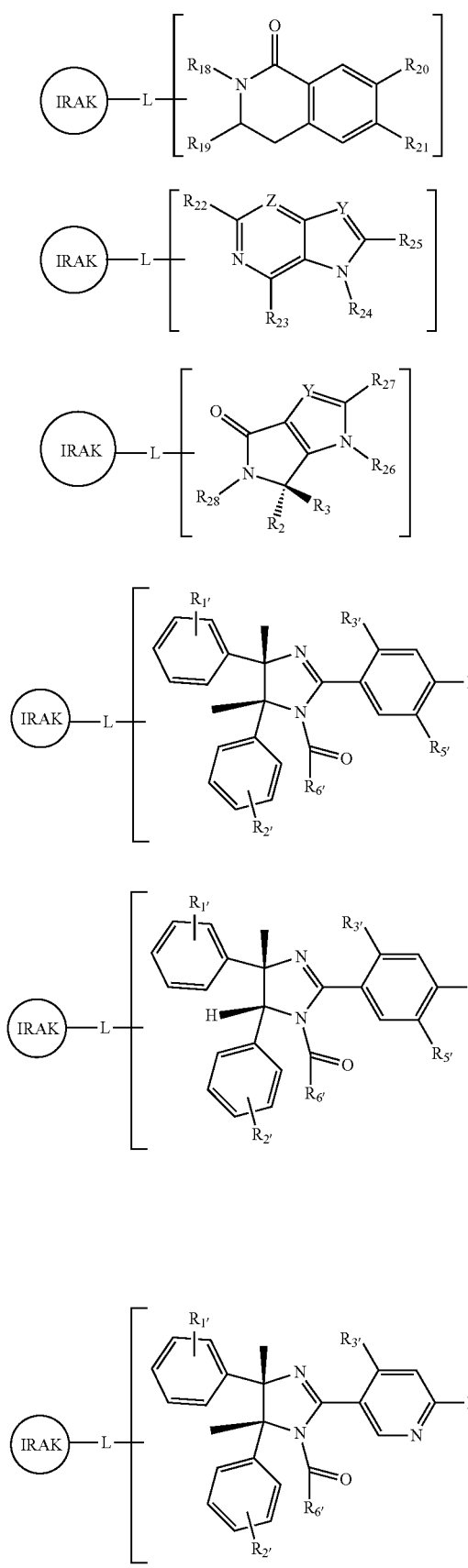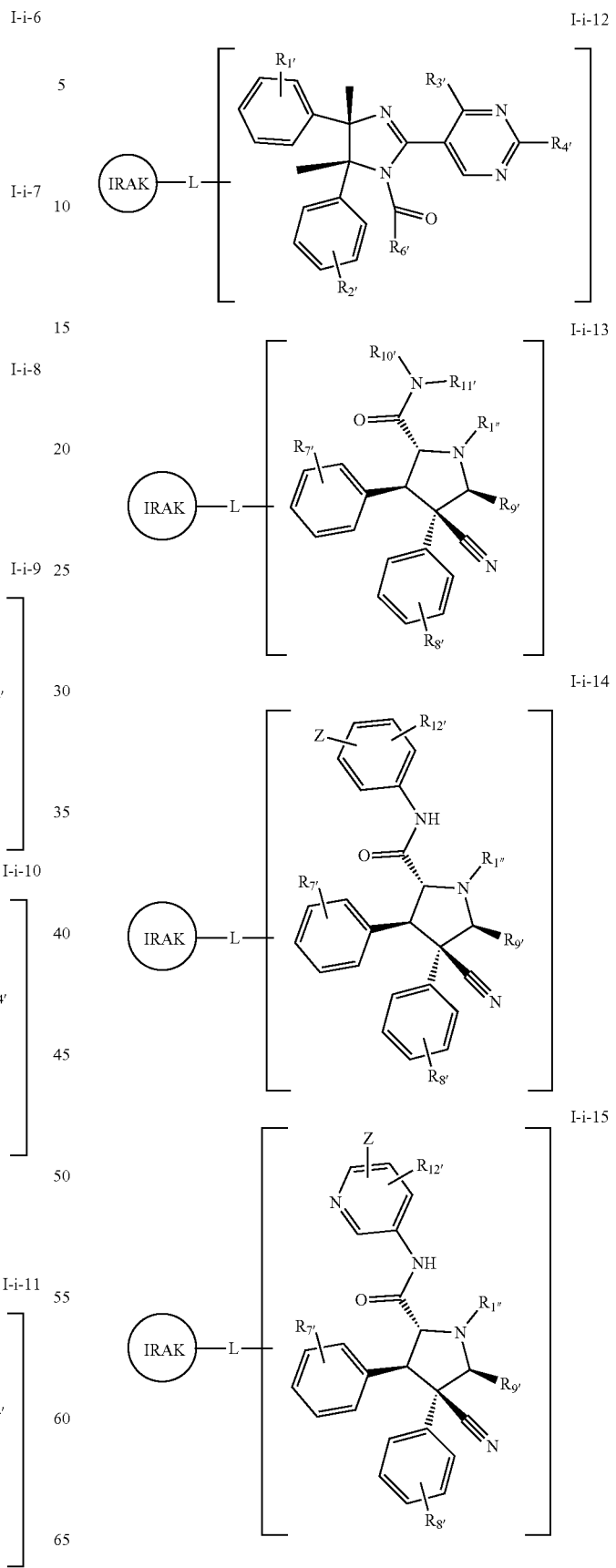

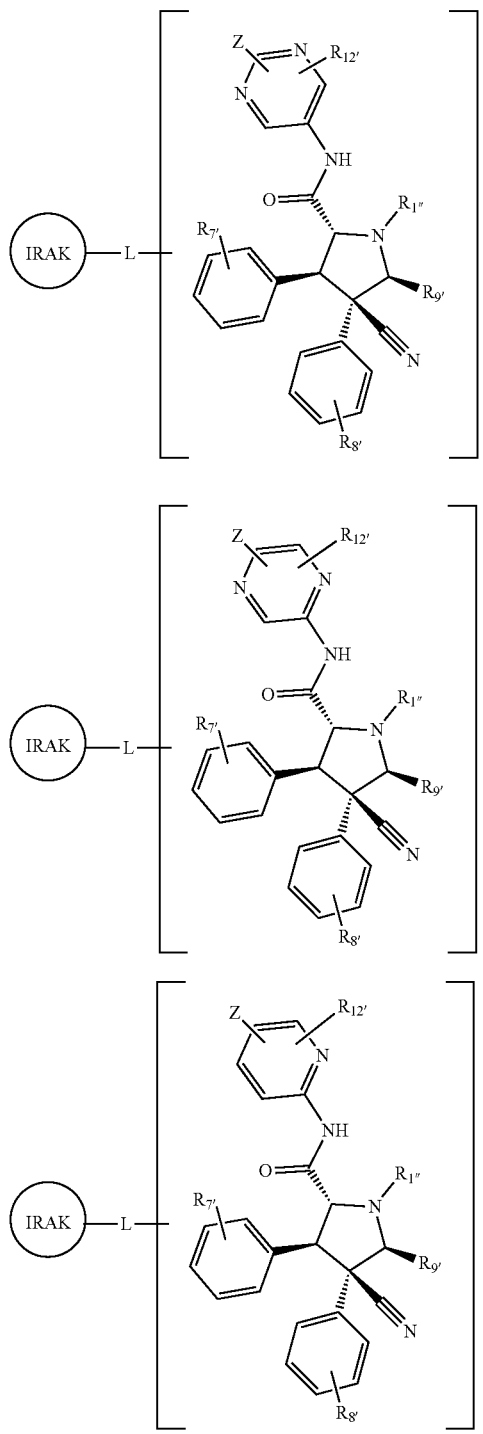

or a pharmaceutically acceptable salt thereof, wherein L and IRAK are as defined above and described in embodiments herein, and wherein each of the variables $R_1$, $R_2$, $R_3$, $R_4$, $R_5$, $R_6$, $R_7$, $R_8$, $R_9$, $R_{10}$, $R_{11}$, $R_{12}$, $R_{13}$, $R_{14}$, $R_{15}$, $R_{16}$, $R_{17}$, $R_{18}$, $R_{19}$, $R_{20}$, $R_{21}$, $R_{22}$, $R_{23}$, $R_{24}$, $R_{25}$, $R_{26}$, $R_{27}$, $R_{28}$, $R_{1'}$, $R_{2'}$, $R_{3'}$, $R_{4'}$, $R_{5'}$, $R_{6'}$, $R_{7'}$, $R_{8'}$, $R_{9'}$, $R_{10'}$, $R_{11'}$, $R_{12'}$, $R_{1''}$, A, A', A'', X, Y, and Z is as defined and described in WO 2017/011371 and US 2017/0008904, the entirety of each of which is herein incorporated by reference.

In certain embodiments, LBM is a MDM2 E3 ligase binding moiety

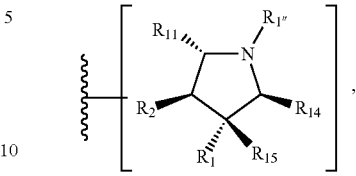

or a pharmaceutically acceptable salt thereof, wherein:

$R^1$ and $R^2$ are independently selected from the group consisting of an aryl or heteroaryl group, a heteroaryl group having one or two heteroatoms independently selected from sulfur or nitrogen, wherein the aryl or heteroaryl group can be mono-cyclic or bi-cyclic, or unsubstituted or substituted with one to three substituents independently selected from the group consisting of: halogen, —CN, $C_{1-6}$ alkyl group, $C_{3-6}$ cycloalkyl, —OH, alkoxy with 1 to 6 carbons, fluorine substituted alkoxy with 1-6 carbons, sulfoxide with 1-6 carbons, sulfone with 1-6 carbons, ketone with 2-6 carbons, amides with 2-6 carbons, and dialkyl amine with 2-6 carbons;

$R_{11}$ is —C(O)—N($R^h$)($R^i$), wherein $R^h$ and $R^i$ are selected from groups consisting of the following: H, C1 to C6 alkyl, alkoxy substituted alkyl, sulfone substituted alkyl, aryl, heterol aryl, mono-, bis- or tri-substituted aryl or hetero aryl, alkyl carboxylic acid, heteroaryl carboxylic acid, alkyl carboxylic acid, fluorine substituted alkyl carboxylic acid, aryl substituted cycloalkyl, hetero aryl substituted cycloalkyl; wherein $R^h$ and $R^i$ are independently selected from the group consisting of H, connected to form a ring, 4-hydroxycyclohehexane; mono- and di-hydroxy substituted alkyl ($C_{3-6}$); 3-hydroxycyclobutane; phenyl-4-carboxylic acid, and substituted phenyl-4-carboxylic acid;

$R^{14}$ is selected from the group consisting of alkyl, substituted alkyl, alkenyl, substituted alkenyl, aryl, substituted aryl, heteroaryl, substituted heteroaryl, heterocycle, substituted heterocycle, cycloalkyl, substituted cycloalkyl, cycloalkenyl and substituted cycloalkenyl;

$R_{15}$ is CN;

$R_{1''}$ is selected from the group consisting of alkyl, aryl substituted alkyl, alkoxy substituted alkyl, cycloalkyl, aryl-substituted cycloalkyl, and alkoxy substituted cycloalkyl, as defined and described in WO 2017/011371 and US 2017/0008904, the entirety of each of which is herein incorporated by reference.

In certain embodiments, the present invention provides a compound of formula I, wherein LBM is a CRBN or VHL E3 ubiquitin ligase binding moiety selected from the group consisting of

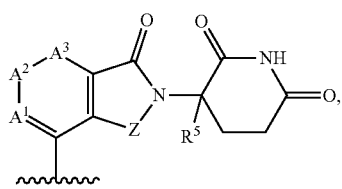

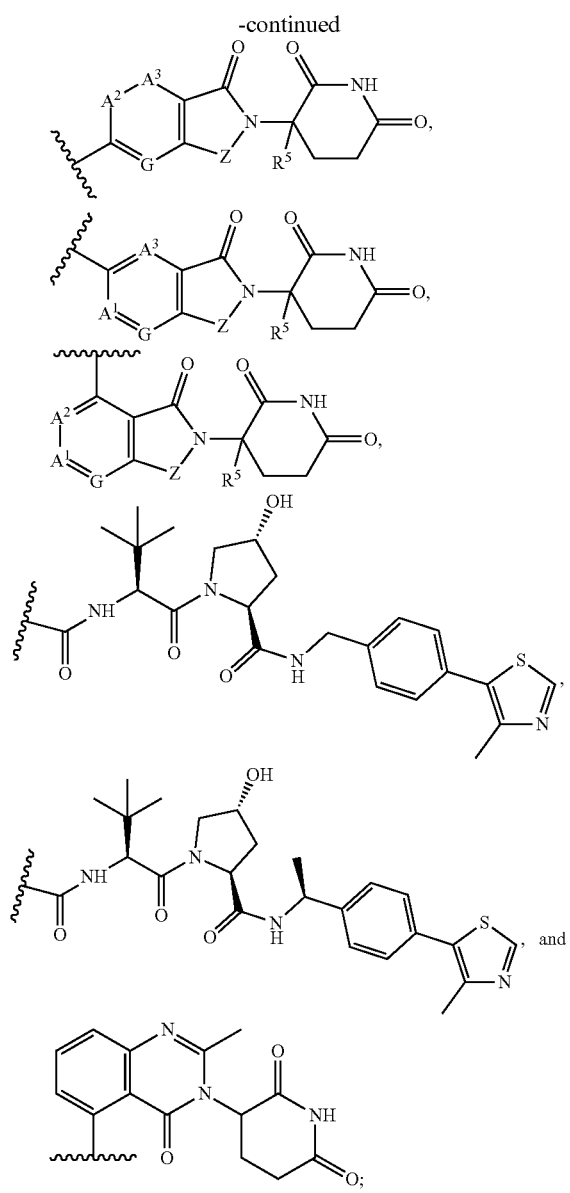
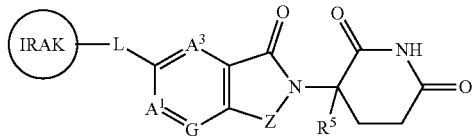
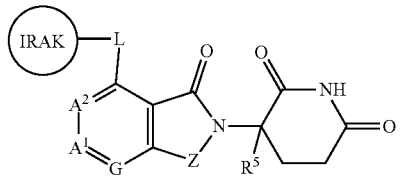
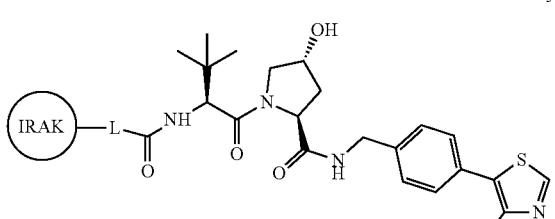
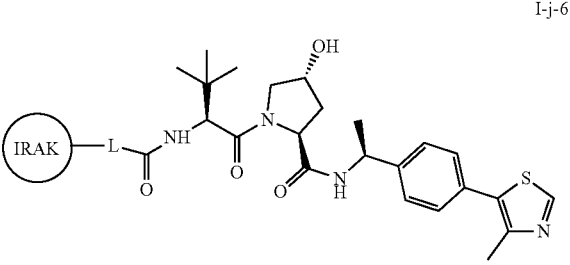
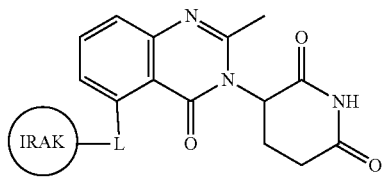

thereby forming a compound of formula I-j-1, I-j-2, I-j-3, I-j-4, I-j-5, I-j-6, or I-j-7 respectively:

I-j-1

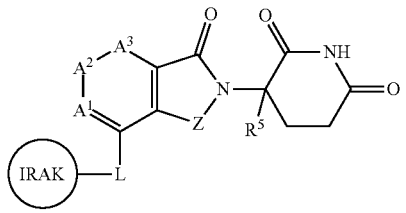

I-j-2

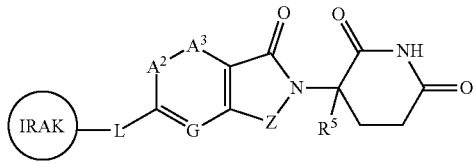

or a pharmaceutically acceptable salt thereof, wherein L and IRAK are as defined above and described in embodiments herein, and wherein each of the variables $A^1$, $A^2$, $A^3$, $R^5$, G and Z is as defined and described in WO 2017/176958 the entirety of each of which is herein incorporated by reference.

In certain embodiments, the present invention provides a compound of formula I, wherein LBM is a CRBN or VHL E3 ubiquitin ligase binding moiety selected from the group consisting of

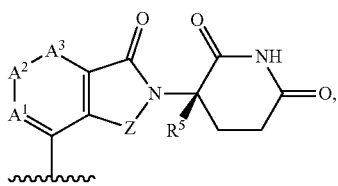

161
-continued
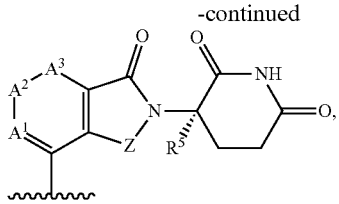
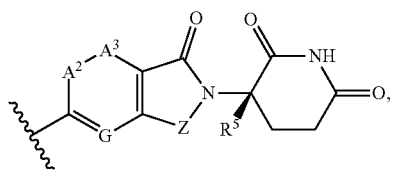
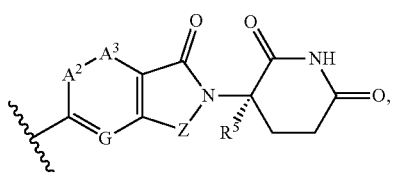
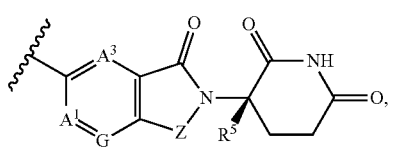
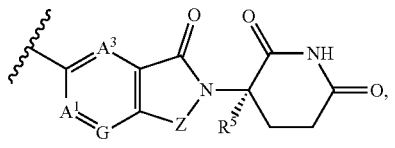
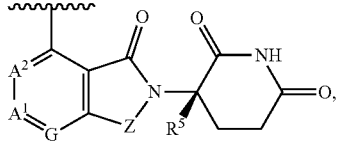
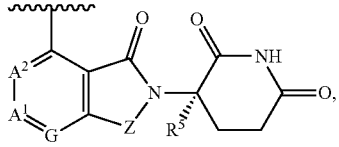
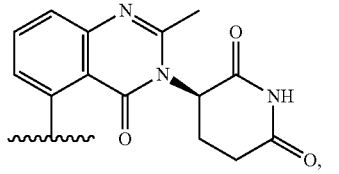
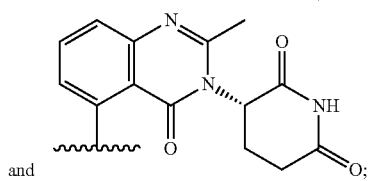
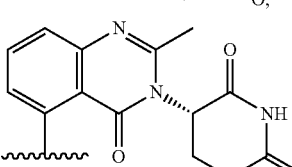
and
thereby forming a compound of formula I-j'-1, I-j"-1, I-j'-2, I-j"-2, I-j'-3, I-j"-3, I-j'-4, I-j"-4, I-j'-7 or I-j"-7 respectively:
162
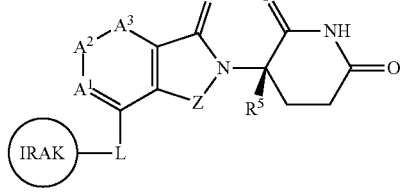 I-j'-1
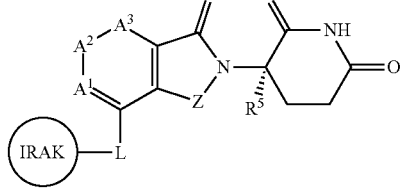 I-j"-1
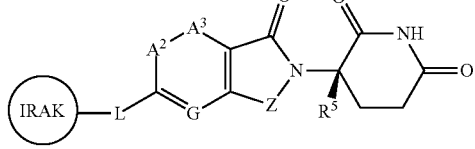 I-j'-2
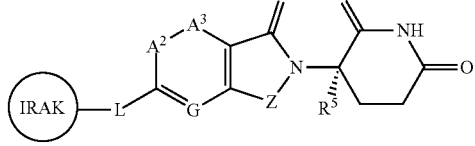 I-j"-2
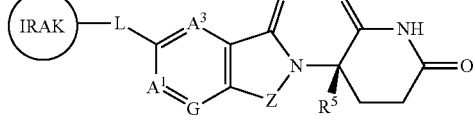 I-j'-3
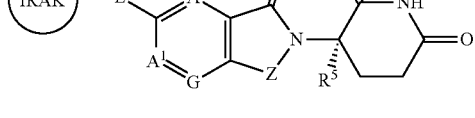 I-j"-3
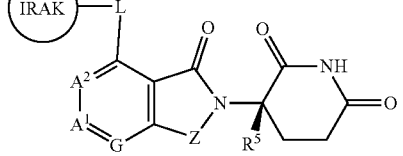 I-j'-4
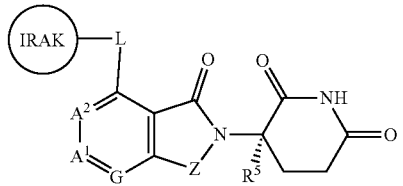 I-j"-4

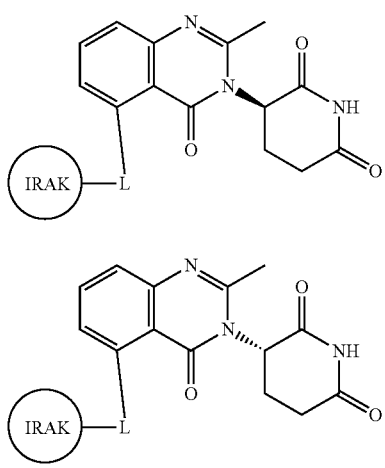

or a pharmaceutically acceptable salt thereof, wherein L and IRAK are as defined above and described in embodiments herein, and wherein each of the variables $A^1$, $A^2$, $A^3$, $R^5$, G and Z is as defined and described in WO 2017/176958, the entirety of each of which is herein incorporated by reference.

In certain embodiments, the present invention provides a compound of formula I, wherein LBM is an IAP E3 ubiquitin ligase binding moiety

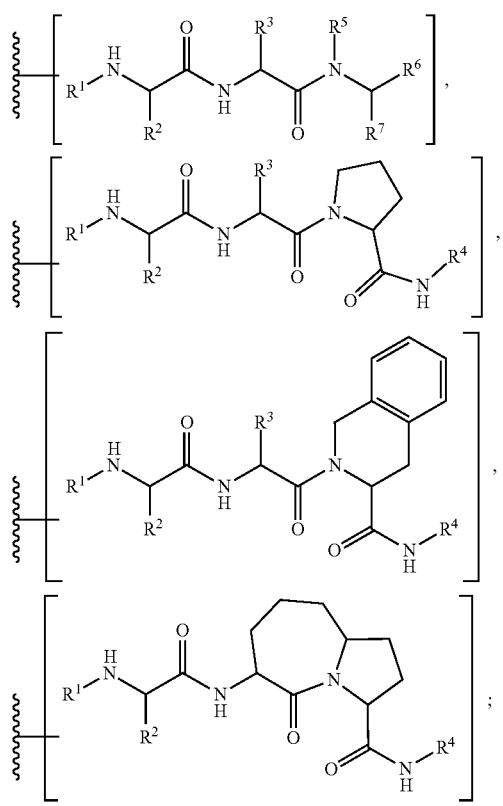

thereby forming a compound of formula I-k-1, I-k-2, I-k-3, or I-k-4 respectively:

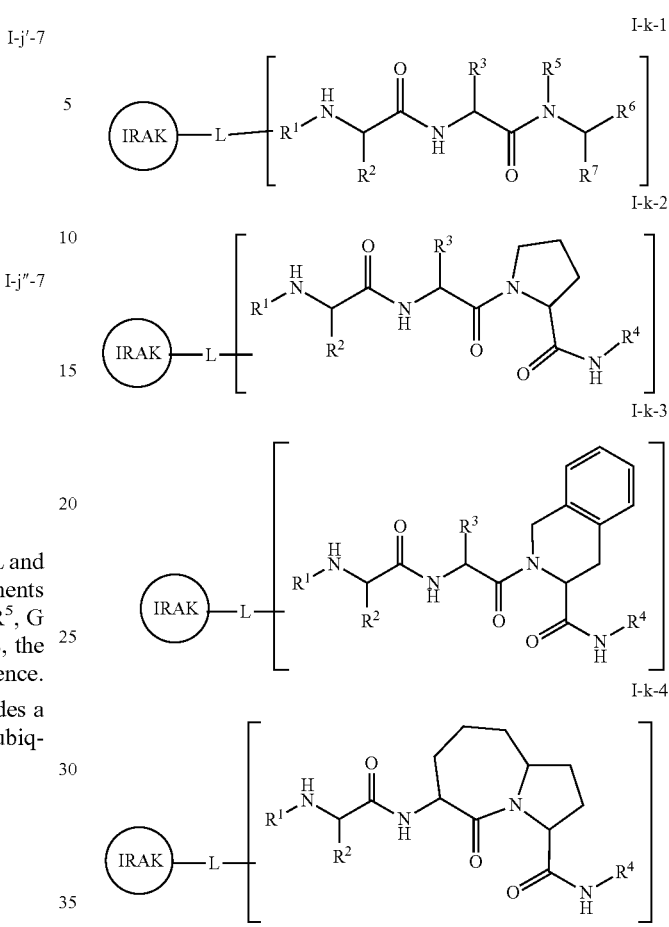

or a pharmaceutically acceptable salt thereof, wherein L and IRAK are as defined above and described in embodiments herein, and wherein:

$R^1$ is selected from hydrogen or alkyl;

$R^2$ is selected from hydrogen or alkyl;

$R^3$ is selected from hydrogen, alkyl, cycloalkyl and heterocycloalkyl;

$R^5$ and $R^6$ are independently selected from hydrogen, alkyl, cycloalkyl, heterocycloalkyl, or $R^5$ and $R^6$ are taken together to form a pyrrolidine or a piperidine ring further optionally fused to 1-2 cycloalkyl, heterocycloalkyl, aryl or heteroaryl rings, each of which can then be further fused to another cycloalkyl, heterocycloalkyl, aryl or heteroaryl ring, or $R^3$ and $R^5$ are taken together to form a 5-8-membered ring further optionally fused to 1-2 cycloalkyl, heterocycloalkyl, aryl or heteroaryl ring;

$R^7$ is selected from cycloalkyl, cycloalkylalkyl, heterocycloalkyl, heterocycloalkylalkyl, aryl, arylalkyl, heteroaryl or heteroarylalkyl, each one further optionally substituted with 1-3 substituents selected from halogen, alkyl, haloalkyl, hydroxyl, alkoxy, cyano, (hetero)cycloalkyl or (hetero)aryl, or $R^7$ is C(O)NHR$^4$; and $R^4$ is selected from alkyl, cycloalkyl, heterocycloalkyl, cycloalkylalkyl, heterocycloalkylalkyl, aryl, arylalkyl, heteroaryl, heteroarylalkyl, further optionally substituted with 1-3 substituents selected from halogen, alkyl, haloalkyl, hydroxyl, alkoxy, cyano, (hetero)cycloalkyl or (hetero)aryl, or $R^7$ is C(O)NHR$^4$, as defined and described in WO 2017/011590 and US 2017/0037004, the entirety of each of which is herein incorporated by reference.

In certain embodiments, the present invention provides a compound of formula I, wherein LBM is an IAP E3 ubiquitin ligase binding moiety

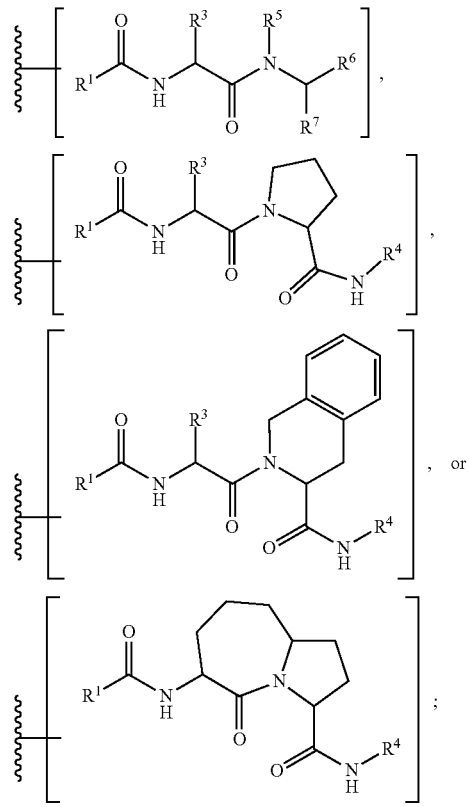

thereby forming a compound of formula I-k'-1, I-k'-2, I-k'-3, or I-k'-4 respectively:

I-k'-1

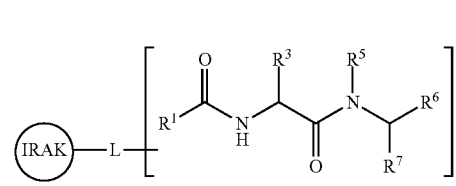

I-k'-2

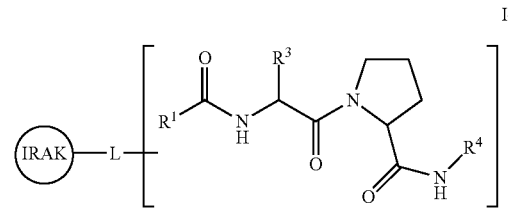

I-k'-3

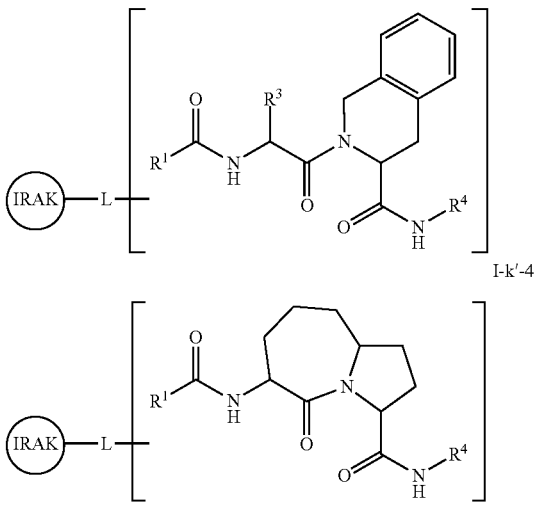

I-k'-4

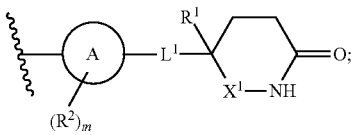

or a pharmaceutically acceptable salt thereof, wherein L and IRAK are as defined above and described in embodiments herein, and wherein each of the variables $R^1$, $R^3$, $R^4$, $R^5$, $R^6$, and $R^7$, is as defined and described in WO 2017/011590 and US 2017/0037004, the entirety of each of which is herein incorporated by reference.

In certain embodiments, the present invention provides a compound of formula I, wherein LBM is an E3 ubiquitin ligase (cereblon) binding moiety

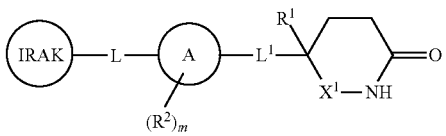

thereby forming a compound of formula I-1:

I-1

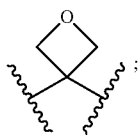 [SMILES: *C1(*)COC1]

or a pharmaceutically acceptable salt thereof, wherein L and IRAK are as defined above and described herein, and wherein:

$X^1$ is a bivalent moiety selected from a covalent bond, —$CH_2$—, —C(O)—, —C(S)—, or

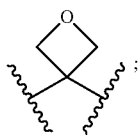 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;
Ring A is a bi- or tricyclic ring selected from
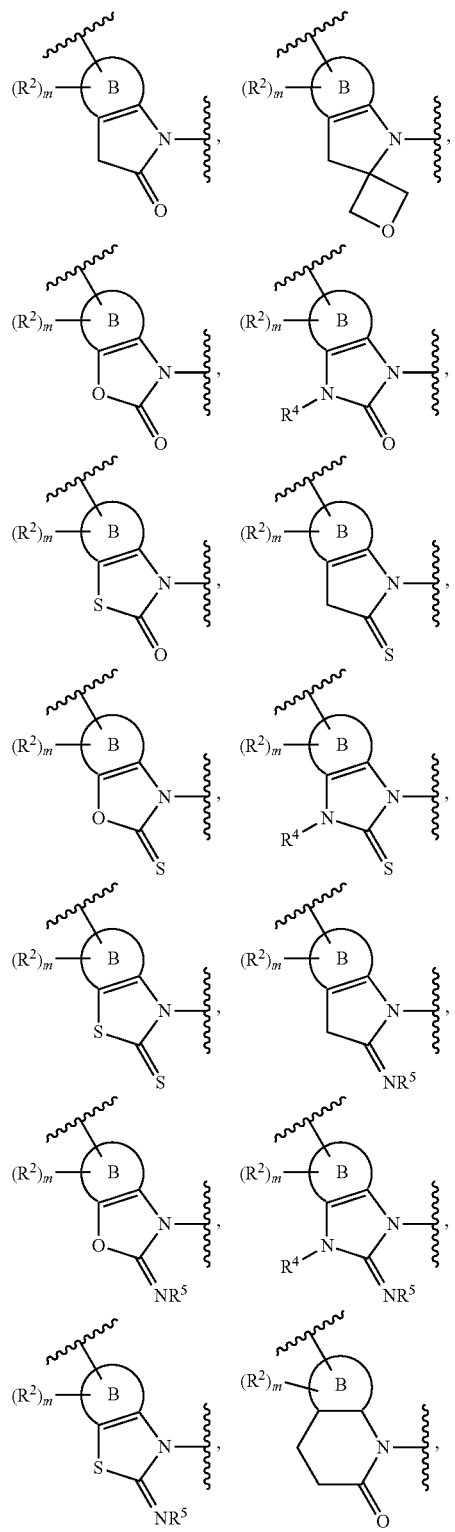
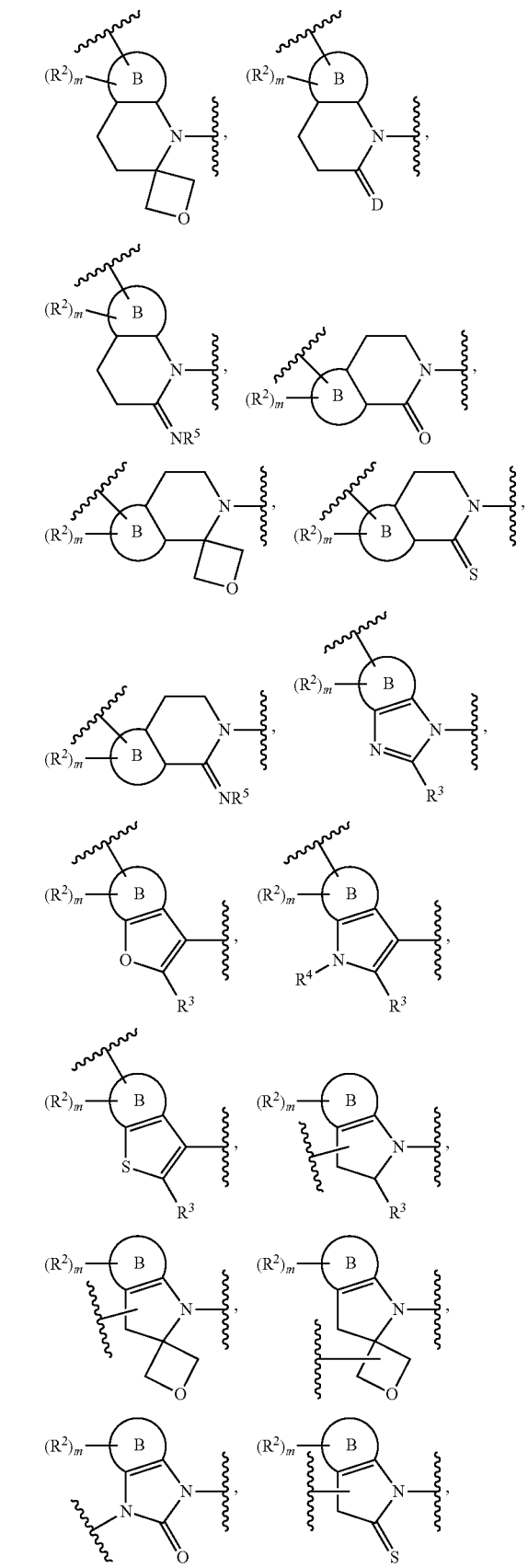

-continued

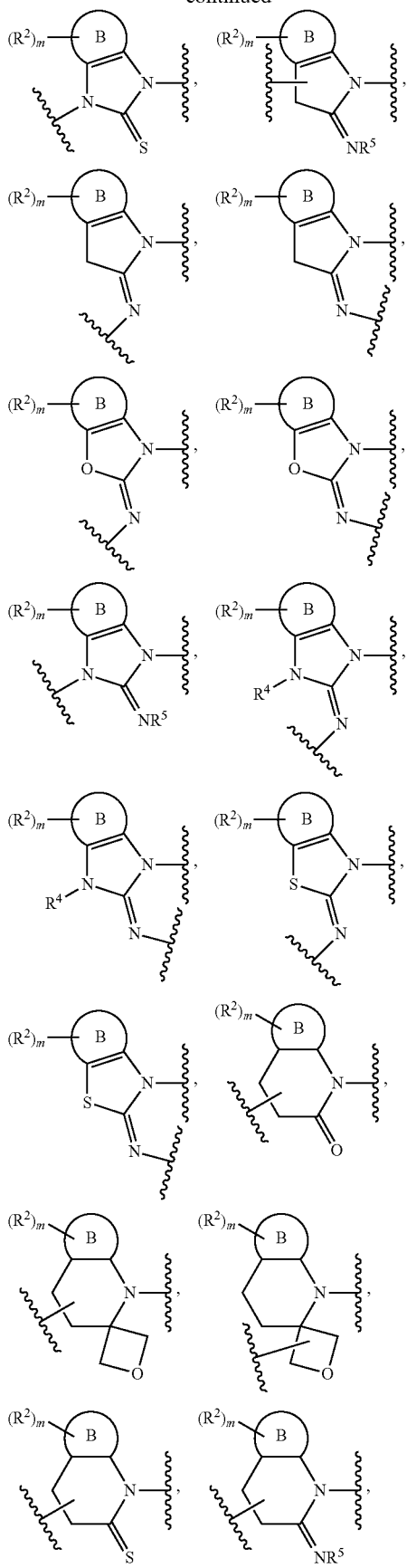

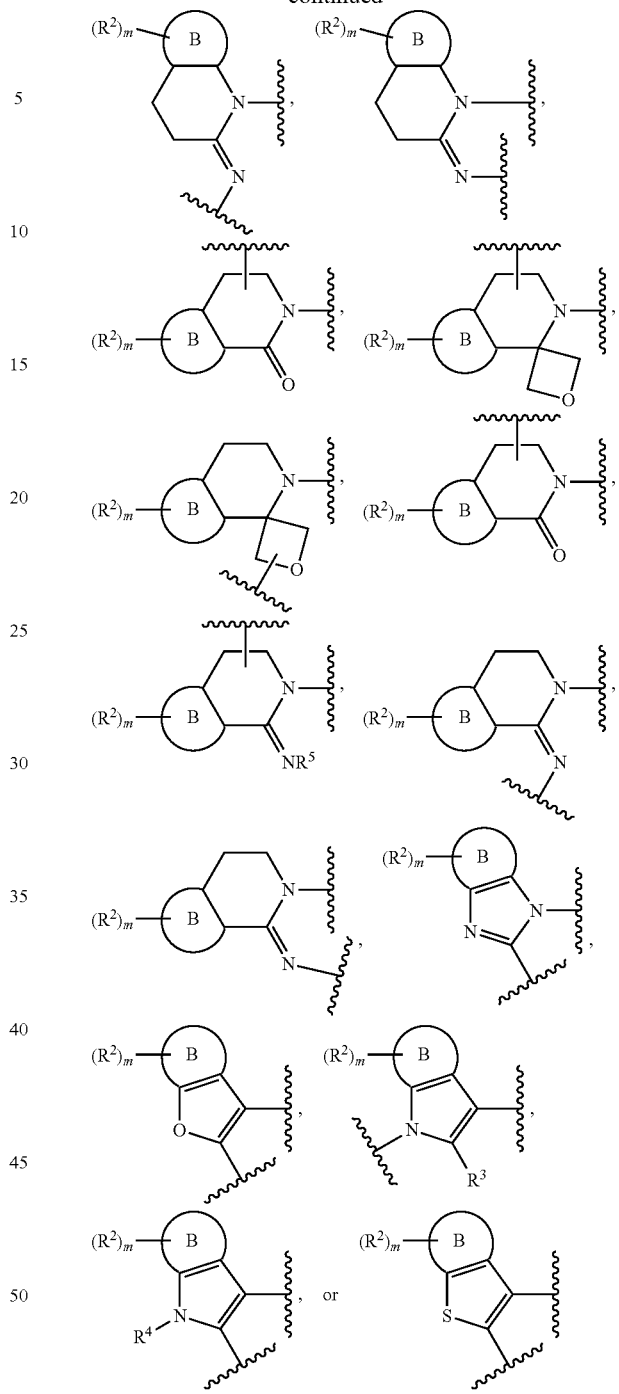

wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

R$^5$ is hydrogen, C$_{1-4}$ aliphatic, or —CN;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L$^1$ is a covalent bond or a bivalent, saturated or unsaturated, straight or branched C$_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

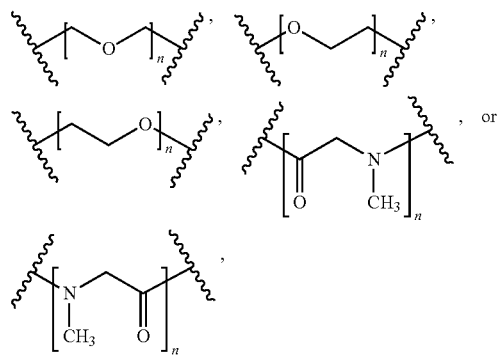

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, 2, 3 or 4;

each of n is independently 1, 2, 3, 4, 5, 6, 7, 8, 9, or 10; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur; or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_n$ is depicted on Ring B, it is intended, and one of ordinary skill in the art would appreciate, that the point of attachment of —(R$^2$)$_n$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In certain embodiments, the present invention provides a compound of formula I, wherein LBM is an E3 ubiquitin ligase (cereblon) binding moiety

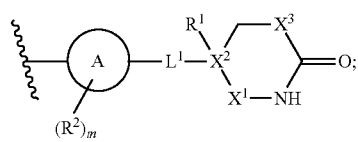

thereby forming a compound of formula I-i':

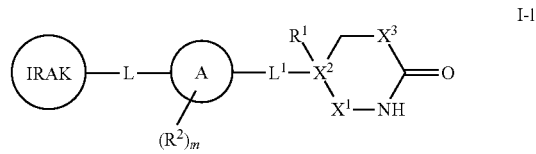

I-i' or a pharmaceutically acceptable salt thereof, wherein L and IRAK are as defined above and described herein, and wherein:

X$^1$ is a bivalent moiety selected from a covalent bond, —CH$_2$—, —C(O)—, —C(S)—, or

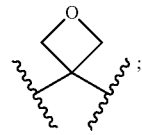 [SMILES: *C1(*)COC1]

X$^2$ is a carbon atom or silicon atom;

X$^3$ is a bivalent moiety selected from —CH$_2$— or —Si(R$_2$)—;

R$^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each R$^2$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from
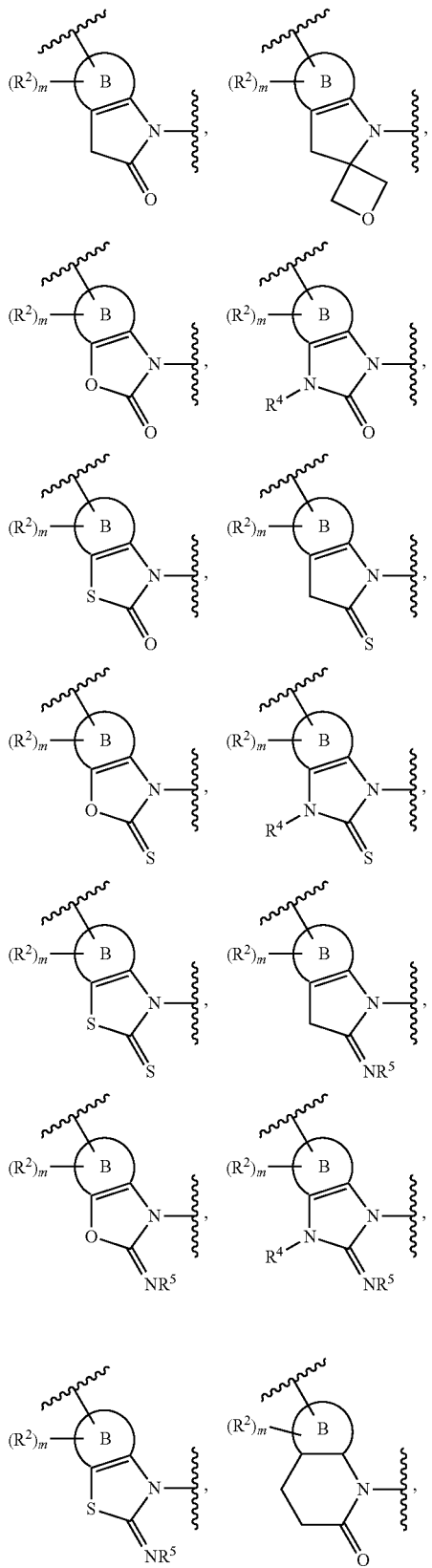
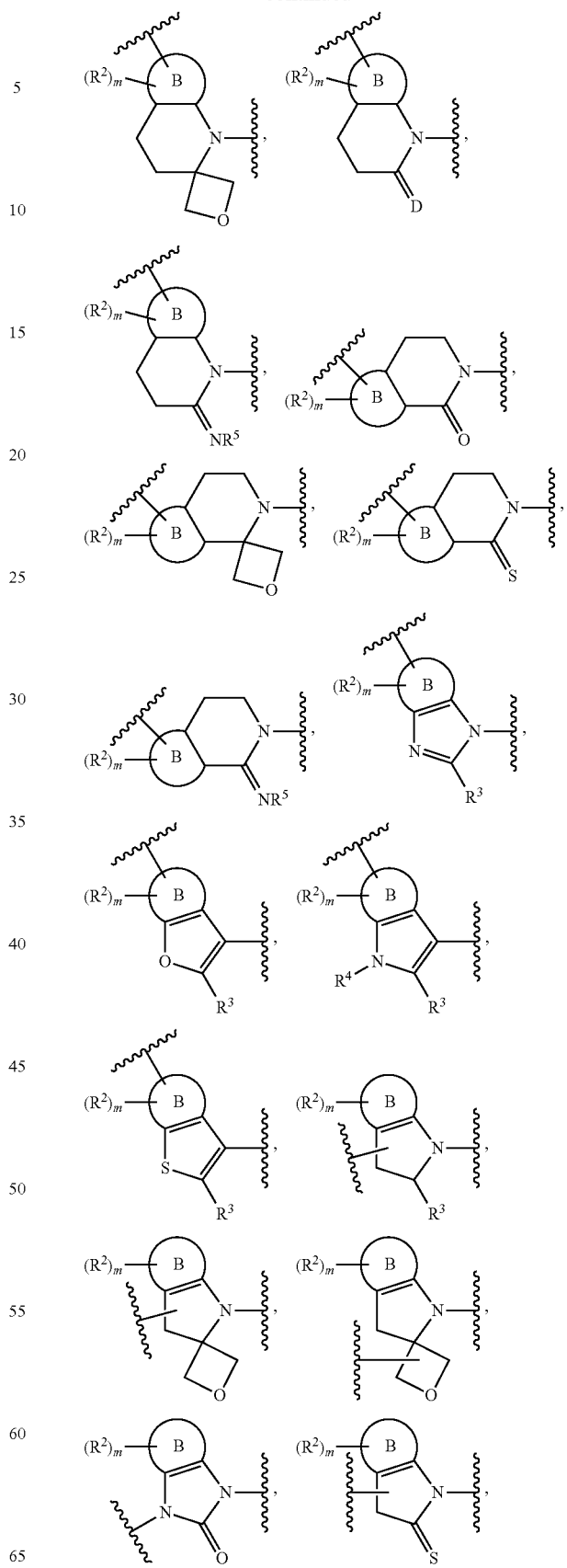
-continued

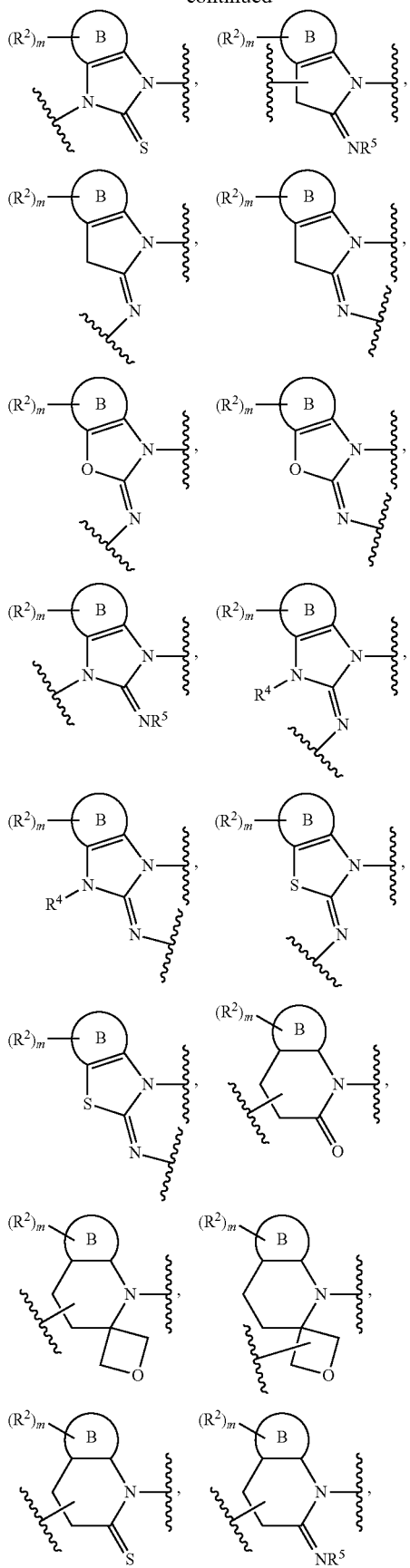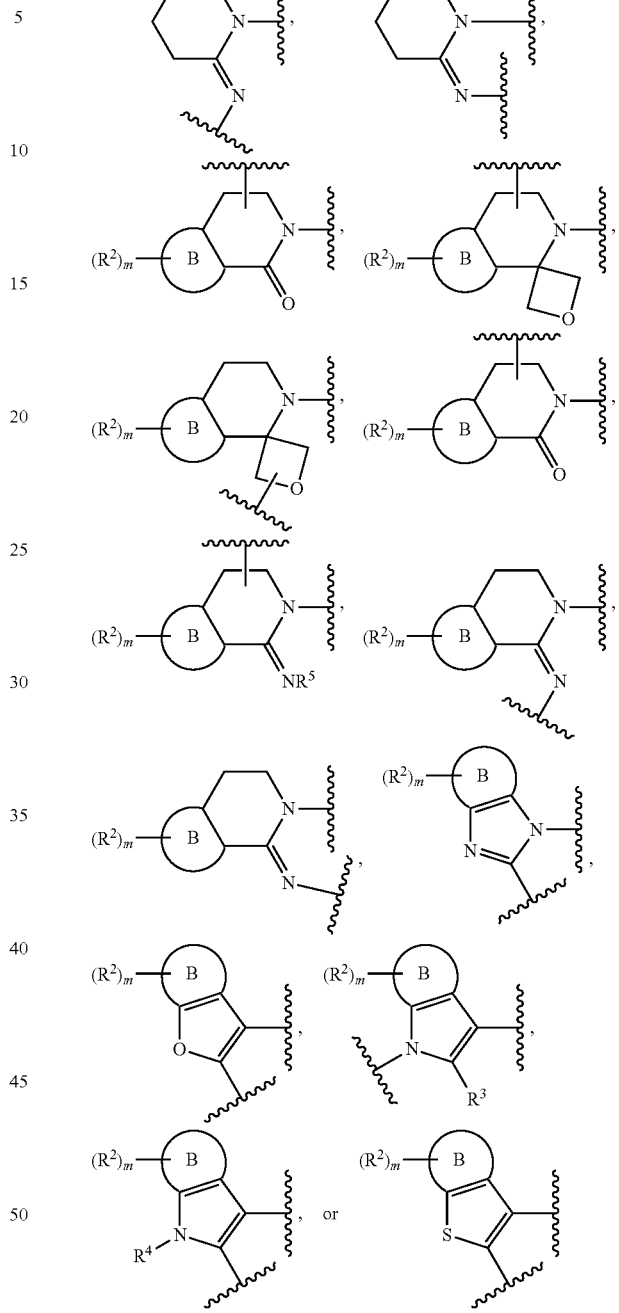

wherein
Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;
$R^3$ is selected from hydrogen, halogen, —OR, —N(R)$_2$, or —SR;
each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

R$^5$ is hydrogen, C$_{1-4}$ aliphatic, or —CN;

each R$^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L$^1$ is a covalent bond or a bivalent, saturated or unsaturated, straight or branched C$_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

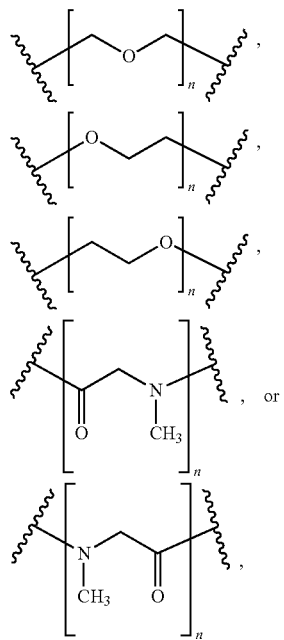

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, 2, 3 or 4;

each of n is independently 1, 2, 3, 4, 5, 6, 7, 8, 9, or 10; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^2$)$_n$ is depicted on Ring B, it is intended, and one of ordinary skill in the art would appreciate, that the point of attachment of —(R$^2$)$_n$ may be on Ring A and may also be at any available carbon or nitrogen atom on Ring A including the ring to which Ring B is fused. Where —R$^2$ is attached to a nitrogen atom bound to R$^4$ or R$^5$, R$^4$ or R$^5$ is absent and —R$^2$ takes the place of the R$^4$ or R$^5$ group. Where —R$^2$ is attached to a carbon atom bound to R$^3$, R$^3$ is absent and —R$^2$ takes the place of the R$^3$ group.

In some embodiments, a compound of formula I-i' above is provided as a compound of formula I-1" or formula I-1"':

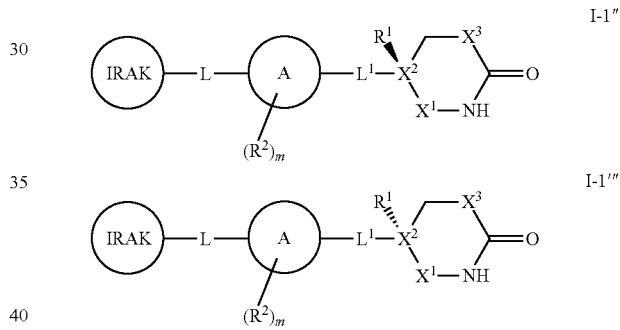

or a pharmaceutically acceptable salt thereof, wherein:
each of IRAK, Ring A, L, L$^1$, R$^1$, R$^2$, X$^1$, X$^2$, X$^3$, and m is as defined above.

In certain embodiments, the present invention provides a compound of formula I, wherein LBM is an E3 ubiquitin ligase (cereblon) binding moiety

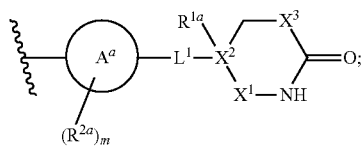

thereby forming a compound of formula I-l-1:

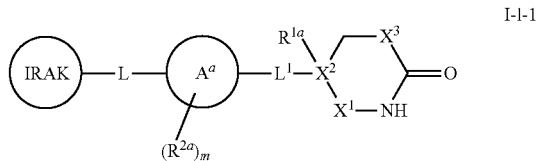

or a pharmaceutically acceptable salt thereof, wherein L and IRAK are as defined above and described herein, and wherein:

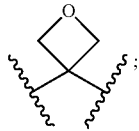 [SMILES: *C1(*)COC1]

$X^1$ is a bivalent moiety selected from a covalent bond, —CH$_2$—, —C(O)—, —C(S)—, or $X^2$ is a carbon atom or silicon atom;

$X^3$ is a bivalent moiety selected from —CH$_2$— or —Si(R$^2$)—;

$R^{1a}$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each $R^{2a}$ is independently hydrogen, —R$^{6a}$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring $A^a$ is a bi- or tricyclic ring selected from

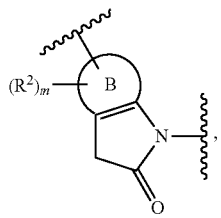 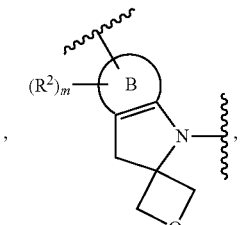

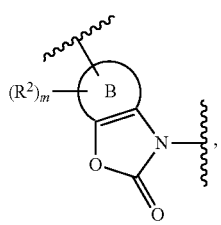 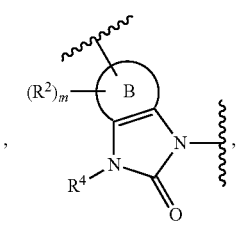

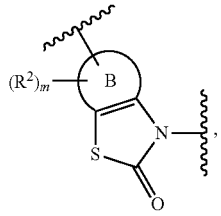 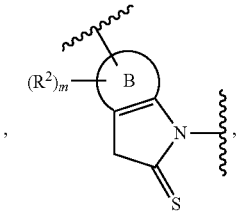

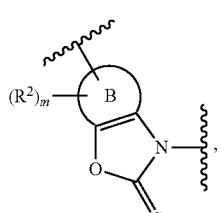 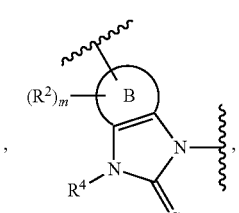

-continued

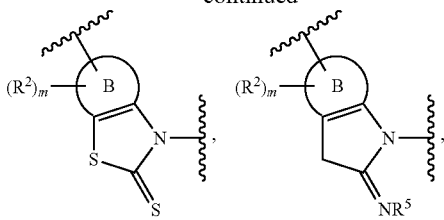

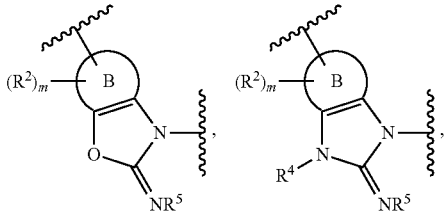

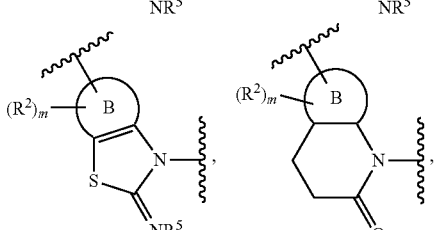

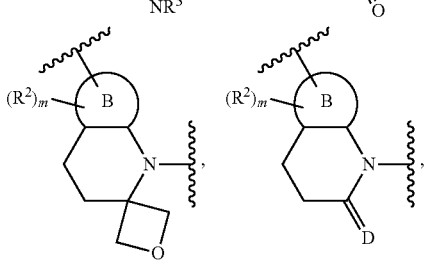

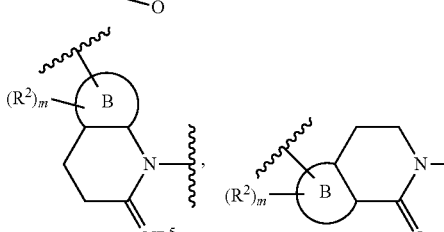

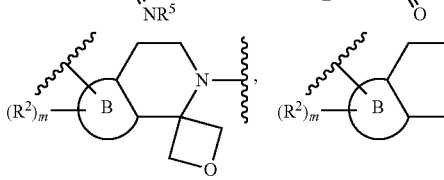

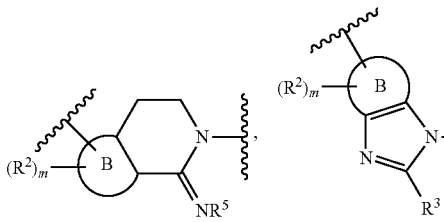

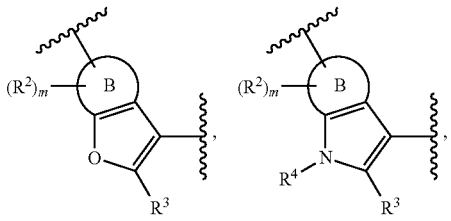

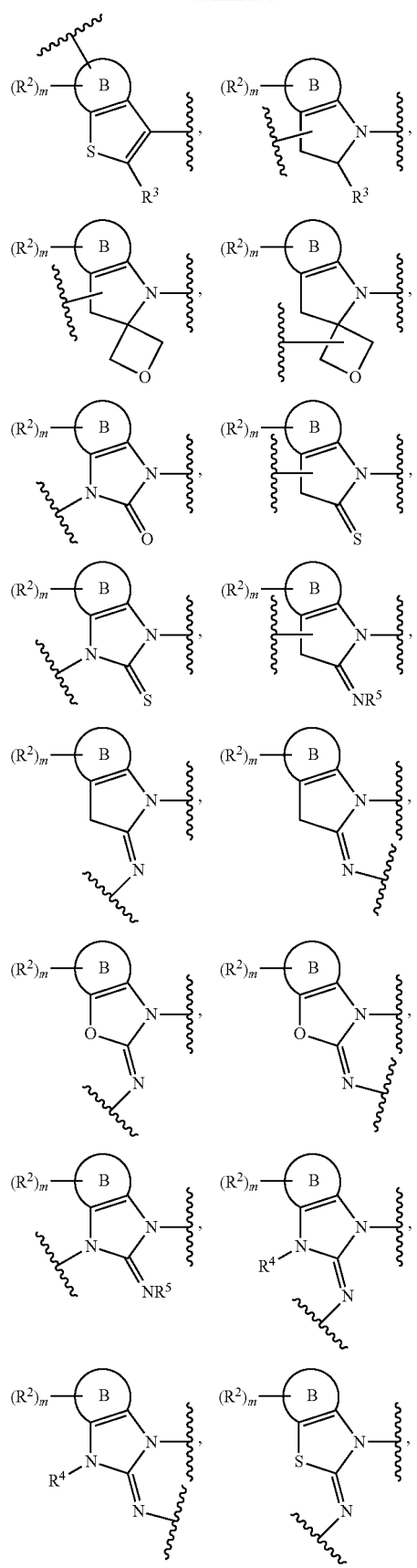
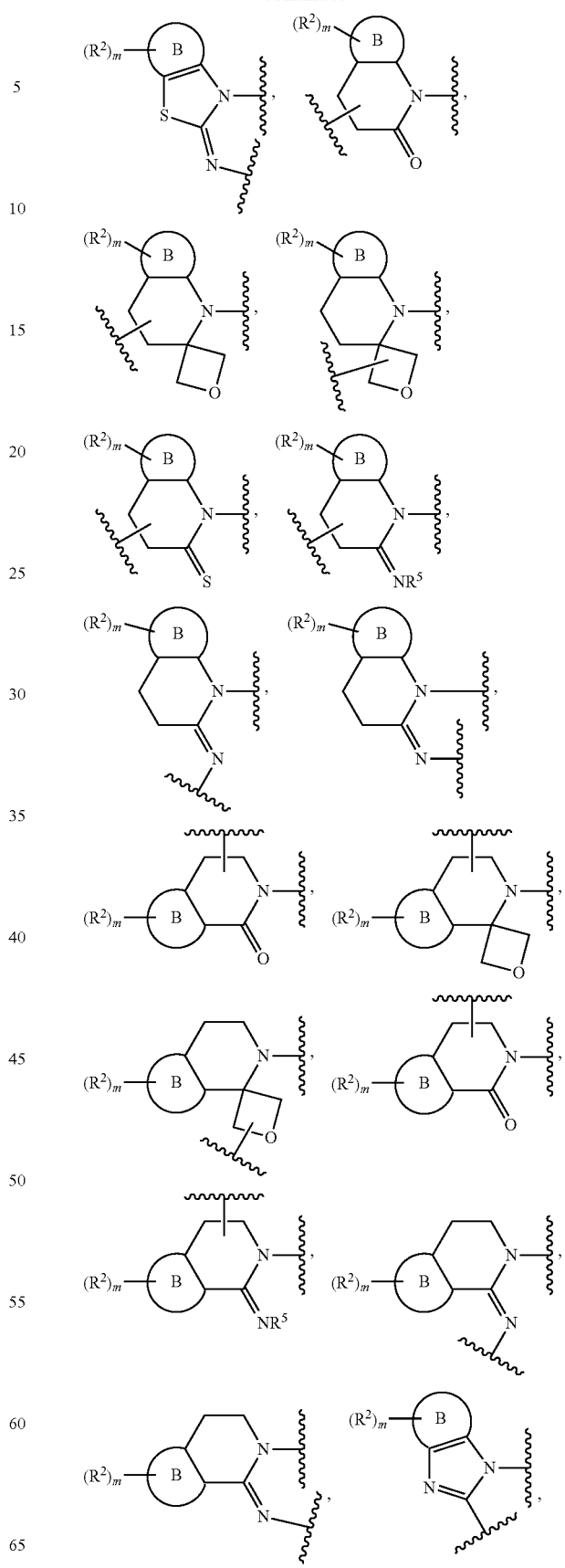

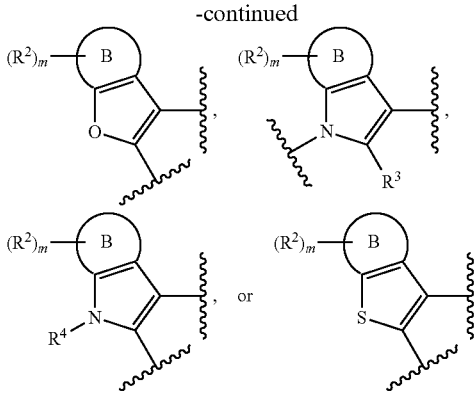

P Ring $B^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^{3a}$ is selected from hydrogen, halogen, —OR, —N(R)$_2$, or —SR;

each $R^{4a}$ is independently hydrogen, —$R^{6a}$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^{5a}$ is hydrogen, $C_{1-4}$ aliphatic, or —CN;

each $R^{6a}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

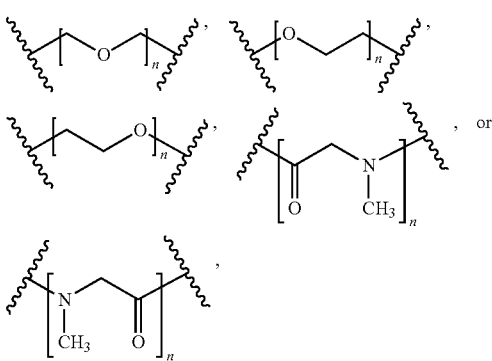

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, 2, 3 or 4;

each of n is independently 1, 2, 3, 4, 5, 6, 7, 8, 9, or 10; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

Where a point of attachment of —(R$^{2a}$)$_n$ is depicted on Ring B, it is intended, and one of ordinary skill in the art would appreciate, that the point of attachment of —(R$^{2a}$)$_n$ may be on Ring A and may also be at any available carbon or nitrogen atom on Ring A including the ring to which Ring B is fused. Where —R$^{2a}$ is attached to a nitrogen atom bound to R$^{4a}$ or R$^{5a}$, R$^{4a}$ or R$^{5a}$ is absent and —R$^{2a}$ takes the place of the R$^{4a}$ or R$^{5a}$ group. Where —R$^{2a}$ is attached to a carbon atom bound to R$^{3a}$, R$^{3a}$ is absent and —R$^{2a}$ takes the place of the R$^{3a}$ group.

In some embodiments, a compound of formula I-1-1 above is provided as a compound of formula I-1-1' or formula I-1-1":

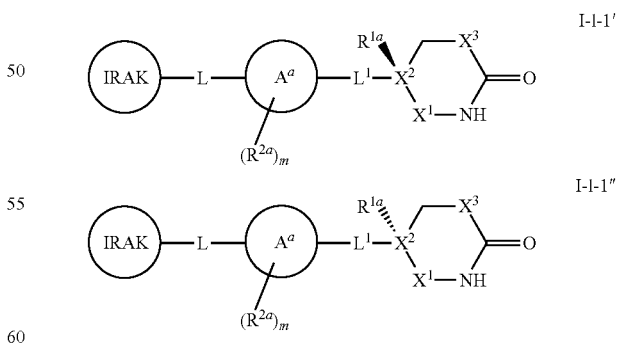

or a pharmaceutically acceptable salt thereof, wherein:
each of IRAK, Ring $A^a$, L, $L^1$, $R^{1a}$, $R^{2a}$, $X^1$, $X^2$, $X^3$, and m is as defined above.

In certain embodiments, the present invention provides a compound of formula I, wherein LBM is an E3 ubiquitin ligase (cereblon) binding moiety

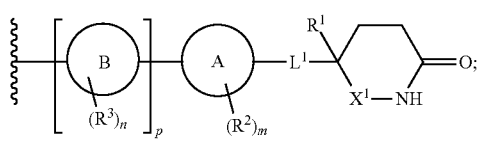

thereby forming a compound of formula I-m:

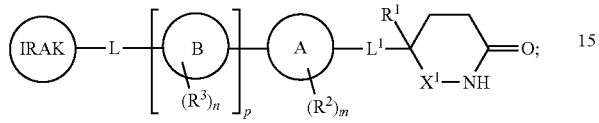

or a pharmaceutically acceptable salt thereof, wherein, L and IRAK are as defined above and described in embodiments herein, and wherein:

X¹ is a bivalent moiety selected from a covalent bond, —CH₂—, —C(O)—, —C(S)—, or

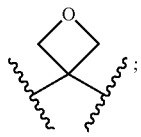 [SMILES: *C1(*)COC1]

R¹ is hydrogen, deuterium, halogen, —CN, —OR, —SR, —S(O)R, —S(O)₂R, —NR₂, or an optionally substituted C₁₋₄ aliphatic;

Ring A is a mono- or bicyclic ring selected from

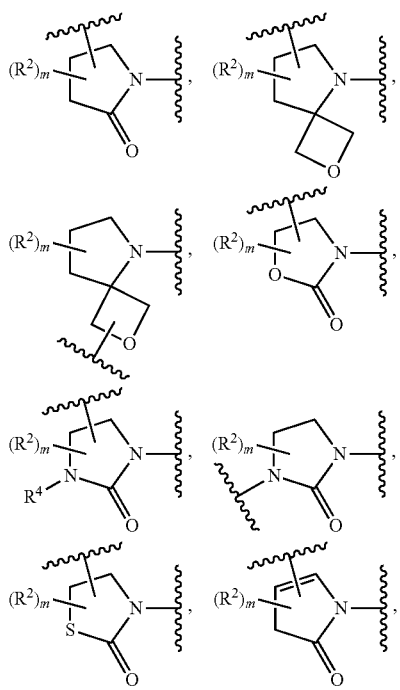

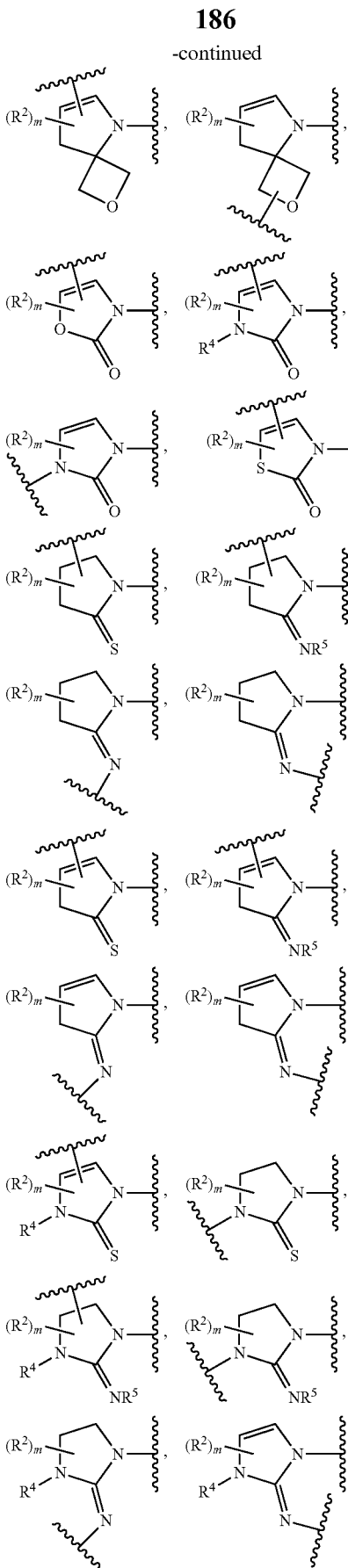

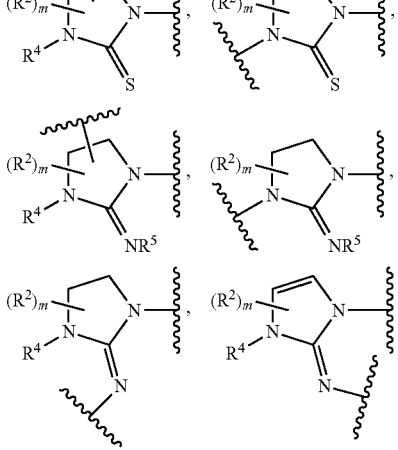

-continued

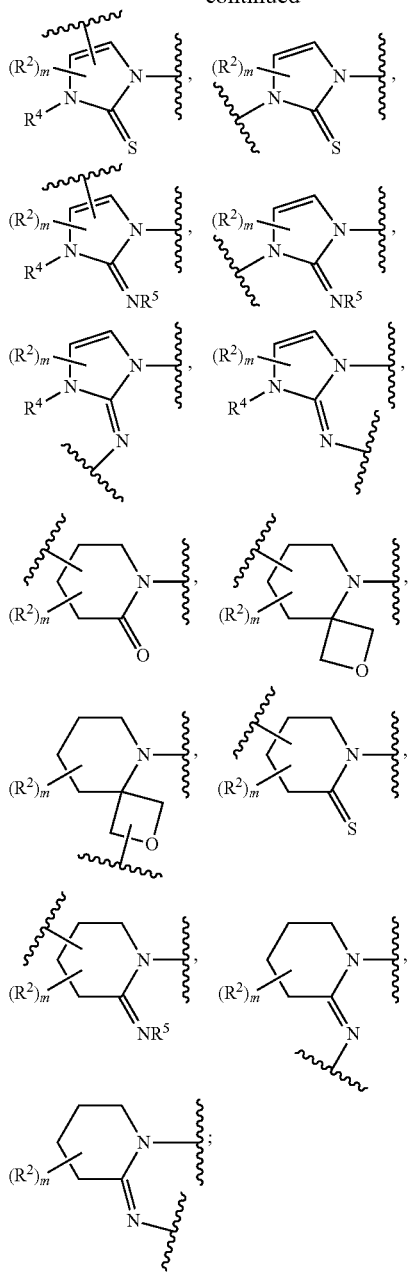

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, $C_{1-4}$ aliphatic, or —CN;

each R⁶ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

L¹ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)₂—, —NRS(O)₂—, —S(O)₂NR—, —NRC(O)—, —C(O)NR—, —OC(O)NR—, —NRC(O)O—,

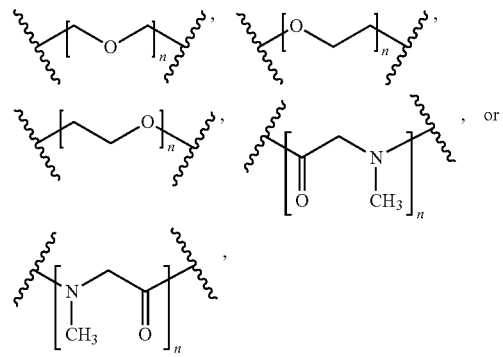

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;

n is 0, 1, 2, 3, or 4;

p is 0 or 1, wherein when p is 0, the bond connecting Ring A and Ring B is connected to

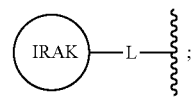

each of q is independently 1, 2, 3, 4, 5, 6, 7, 8, 9, or 10; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

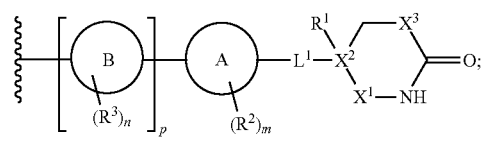

thereby forming a compound of formula I-m':

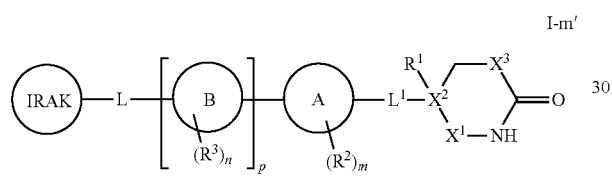

I-m' or a pharmaceutically acceptable salt thereof, wherein, L and IRAK are as defined above and described in embodiments herein, and wherein:

$X^1$ is a bivalent moiety selected from a covalent bond, —$CH_2$—, —C(O)—, —C(S)—, or

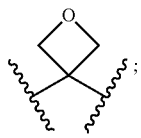 [SMILES: *C1(*)COC1]

$X^2$ is a carbon atom or silicon atom;

$X^3$ is a bivalent moiety selected from —$CH_2$— or —Si($R^2$)—;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

Ring A is a mono- or bicyclic ring selected from

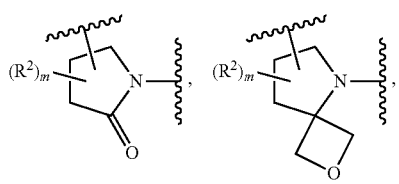

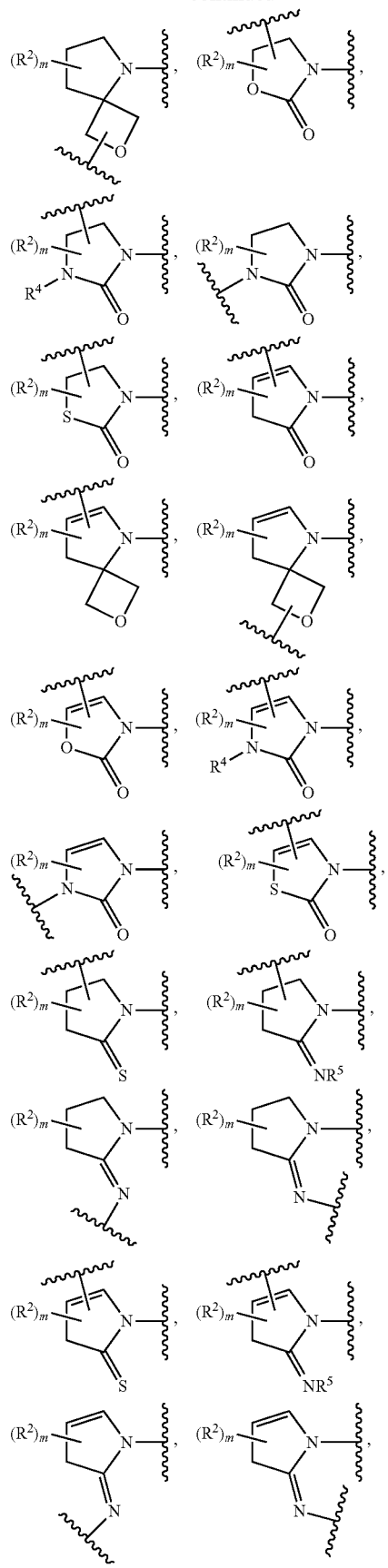

-continued

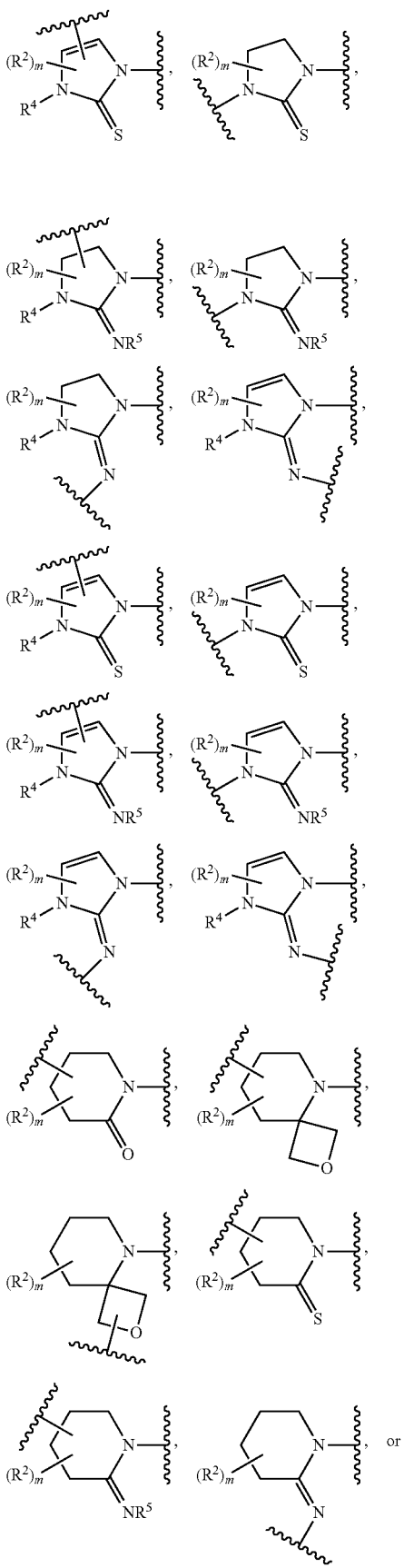

each $R^2$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

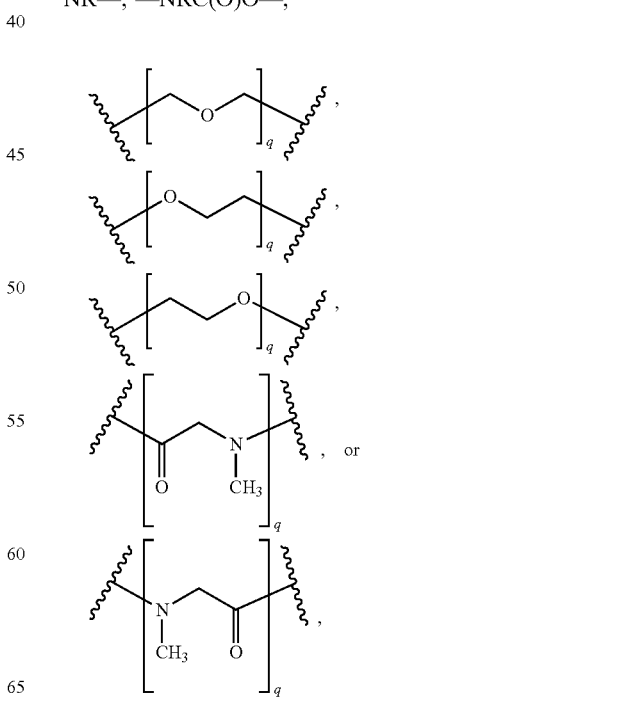

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;

n is 0, 1, 2, 3, or 4;

p is 0 or 1, wherein when p is 0, the bond connecting Ring A and Ring B is connected to

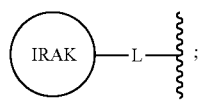

each of q is independently 1, 2, 3, 4, 5, 6, 7, 8, 9, or 10; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-m' above is provided as a compound of formula I-m" or formula I-m''':

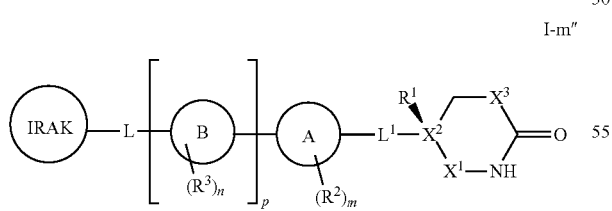

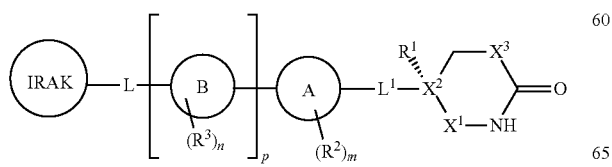

or a pharmaceutically acceptable salt thereof, wherein:

each of IRAK, Ring A, Ring B, L, $L^1$, $R^1$, $R^2$, $R^3$, $X^1$, $X^2$, $X^3$, n, p, and m is as defined above.

In certain embodiments, the present invention provides a compound of formula I, wherein LBM is an E3 ubiquitin ligase (cereblon) binding moiety

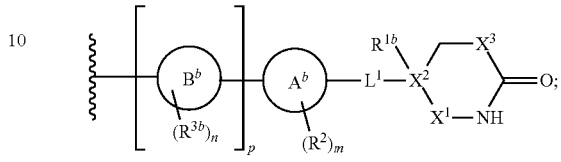

thereby forming a compound of formula I-m-1:

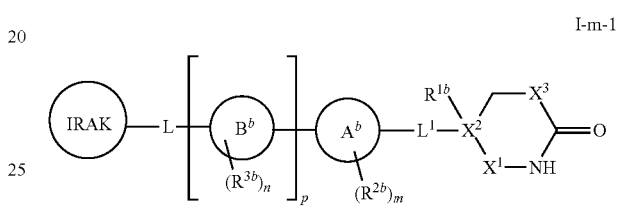

or a pharmaceutically acceptable salt thereof, wherein, L and IRAK are as defined above and described in embodiments herein, and wherein:

$X^1$ is a bivalent moiety selected from a covalent bond, —$CH_2$—, —C(O)—, —C(S)—, or

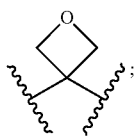

$X^2$ is a carbon atom or silicon atom;

$X^3$ is a bivalent moiety selected from —$CH_2$— or —Si($R^2$)—;

$R^{1b}$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

Ring $A^b$ is a mono- or bicyclic ring selected from

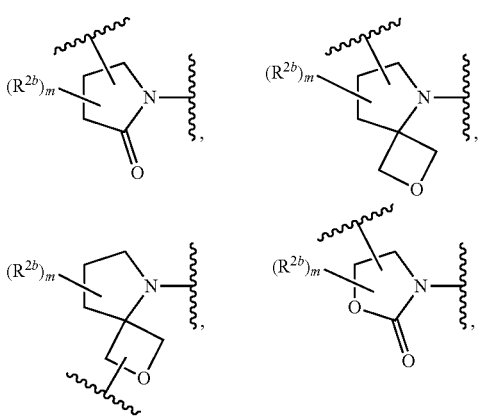

-continued
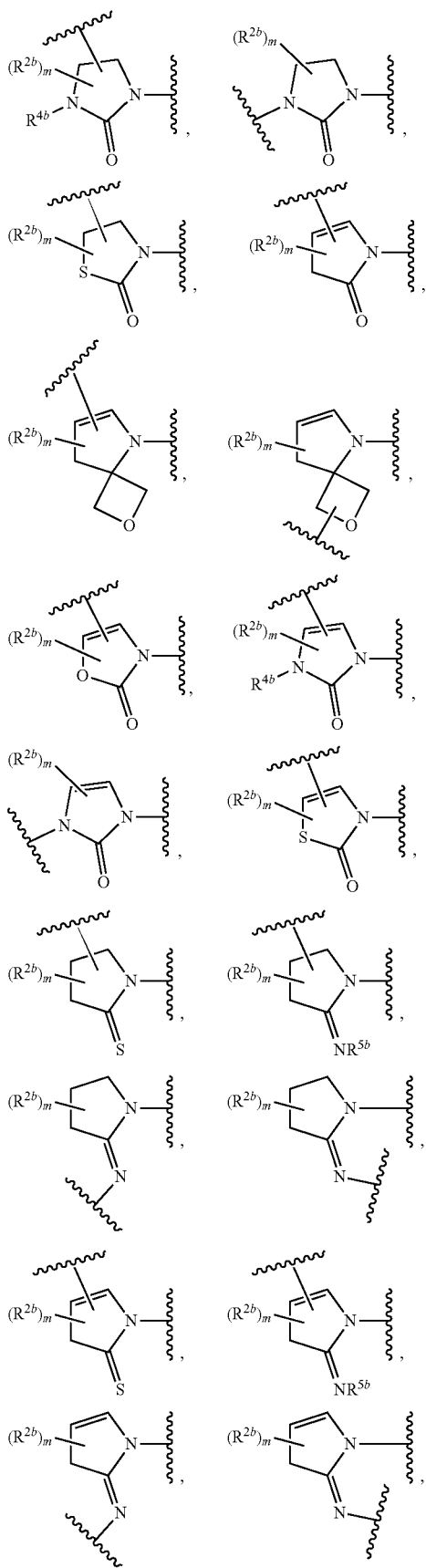
-continued
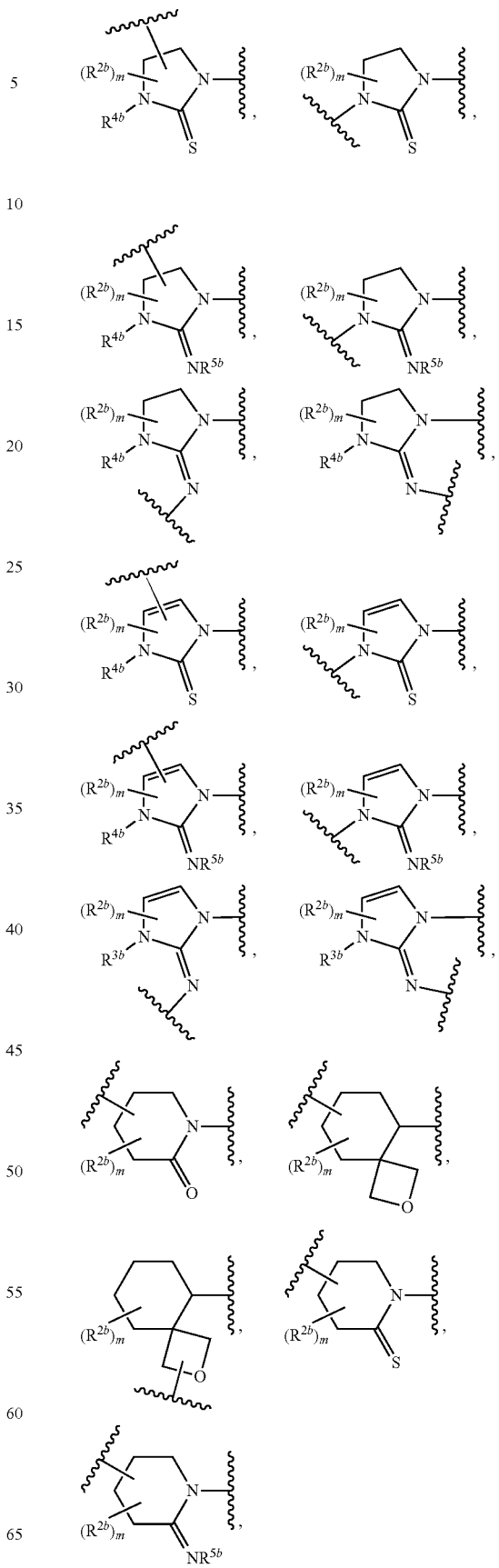

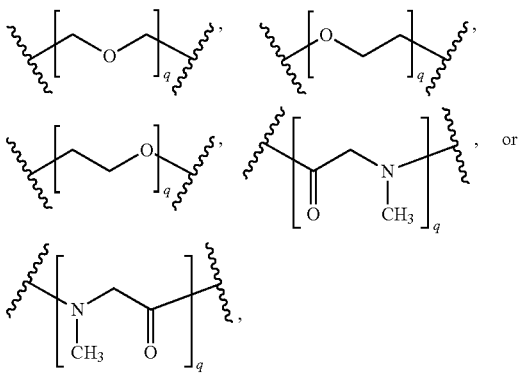

each $R^{2b}$ is independently hydrogen, —$R^{6b}$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$;

Ring $B^b$ is selected from a 6-membered aryl containing 0-2 nitrogen atoms or a 5-membered heteroaryl with 1-3 heteroatoms independently selected from nitrogen, oxygen or sulfur;

each of $R^{3b}$ and $R^{4b}$ is independently hydrogen, —$R^{6b}$, halogen, —CN, —$NO_2$, —OR, —SR, —$NR_2$, —$S(O)_2R$, —$S(O)_2NR_2$, —$S(O)R$, —$C(O)R$, —$C(O)OR$, —$C(O)NR_2$, —$C(O)N(R)OR$, —$OC(O)R$, —$OC(O)NR_2$, —$N(R)C(O)OR$, —$N(R)C(O)R$, —$N(R)C(O)NR_2$, or —$N(R)S(O)_2R$;

$R^{5b}$ is hydrogen, $C_{1-4}$ aliphatic, or —CN;

each $R^{6b}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —$S(O)_2$—, —$NRS(O)_2$—, —$S(O)_2NR$—, —NRC(O)—, —C(O)NR—, —OC(O)NR—, —NRC(O)O—,

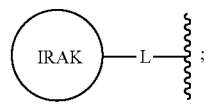

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;

n is 0, 1, 2, 3, or 4;

p is 0 or 1, wherein when p is 0, the bond connecting Ring A and Ring B is connected to

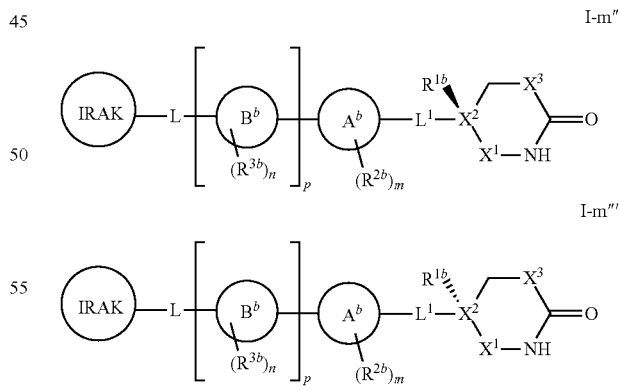

each of q is independently 1, 2, 3, 4, 5, 6, 7, 8, 9, or 10; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-m' above is provided as a compound of formula I-m'' or formula I-m''':

I-m''

I-m''' or a pharmaceutically acceptable salt thereof, wherein:

each of IRAK, Ring $A^b$, Ring $B^b$, L, $L^1$, $R^{1b}$, $R^{2b}$, $R^{3b}$, $X^1$, $X^2$, $X^3$, n, p, and m is as defined above.

In certain embodiments, the present invention provides a compound of formula I, wherein LBM is an E3 ubiquitin ligase (cereblon) binding moiety

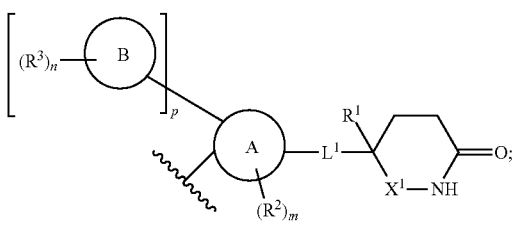

thereby forming a compound of formula I-n:

I-n

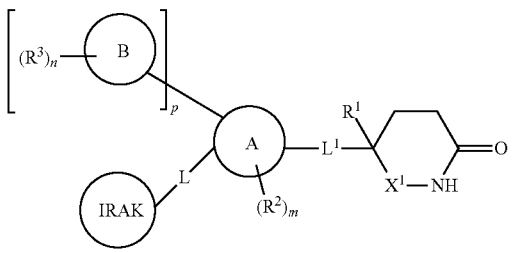

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

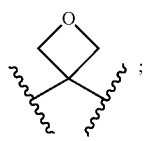;

$R^1$ is hydrogen, deuterium, halogen, —CN, —OR, —SR, —S(O)R, —S(O)$_2$R, —NR$_2$, or an optionally substituted $C_{1-4}$ aliphatic;

Ring A is a mono- or bicyclic ring selected from

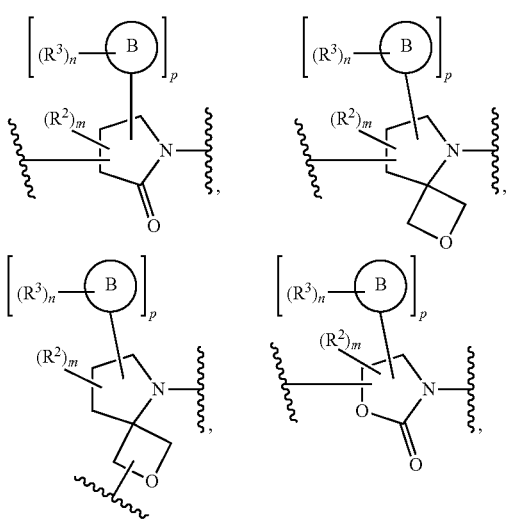

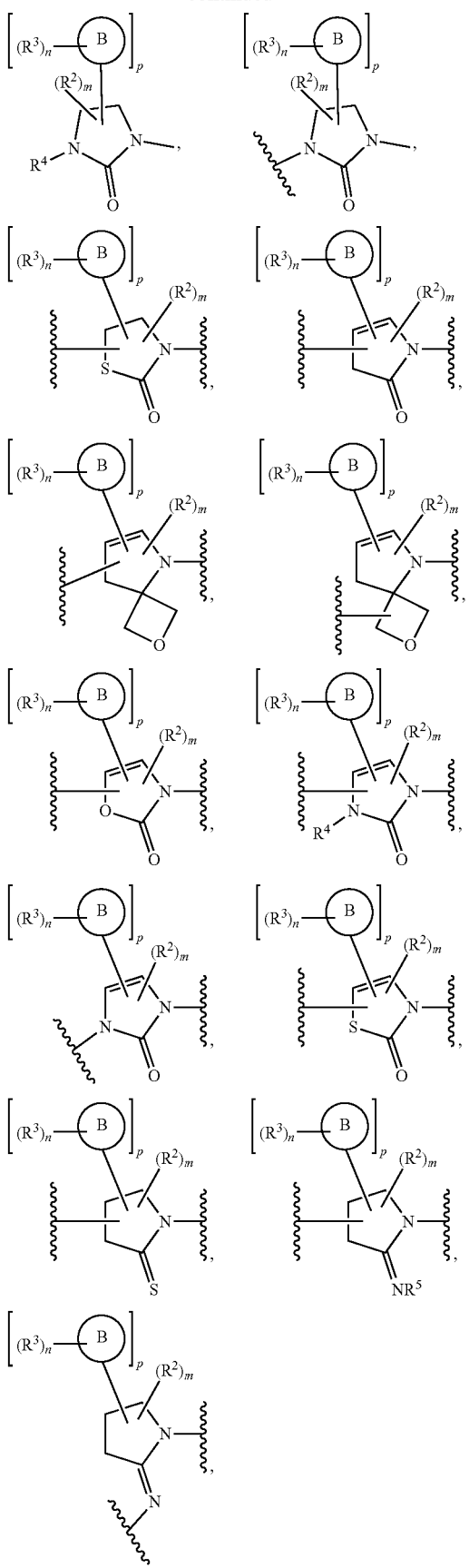

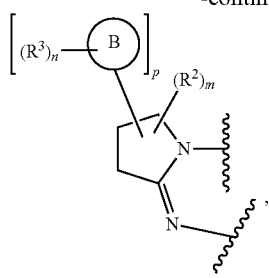,
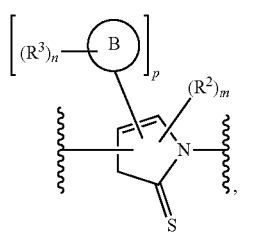 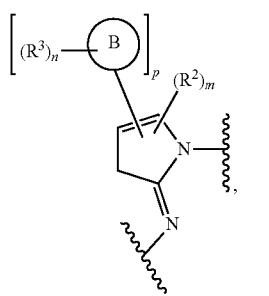,
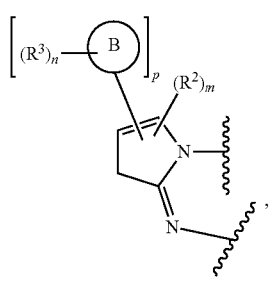,
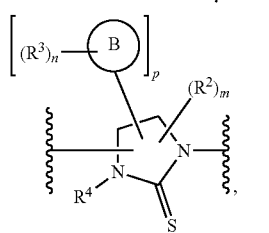,
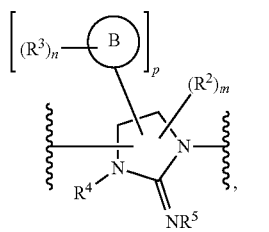 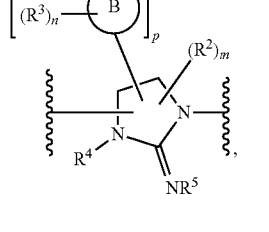,
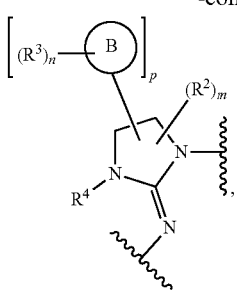,
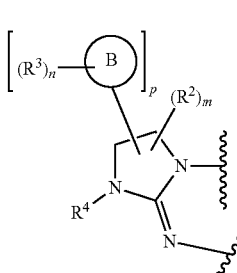,
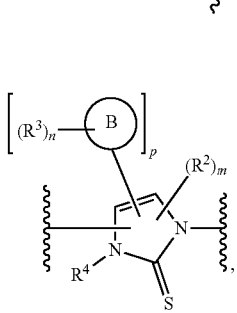,
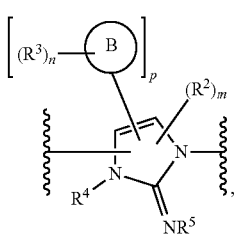 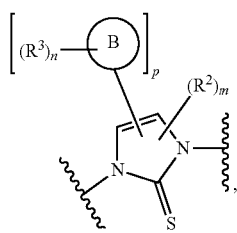,
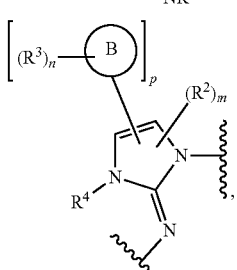 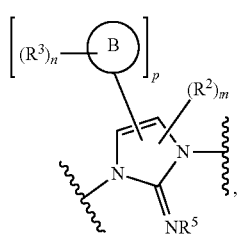,
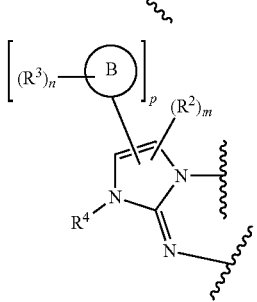,
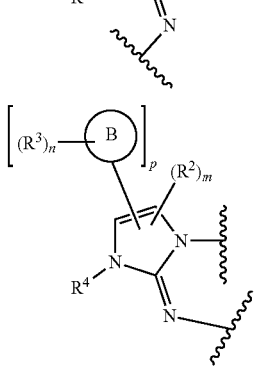 , -continued

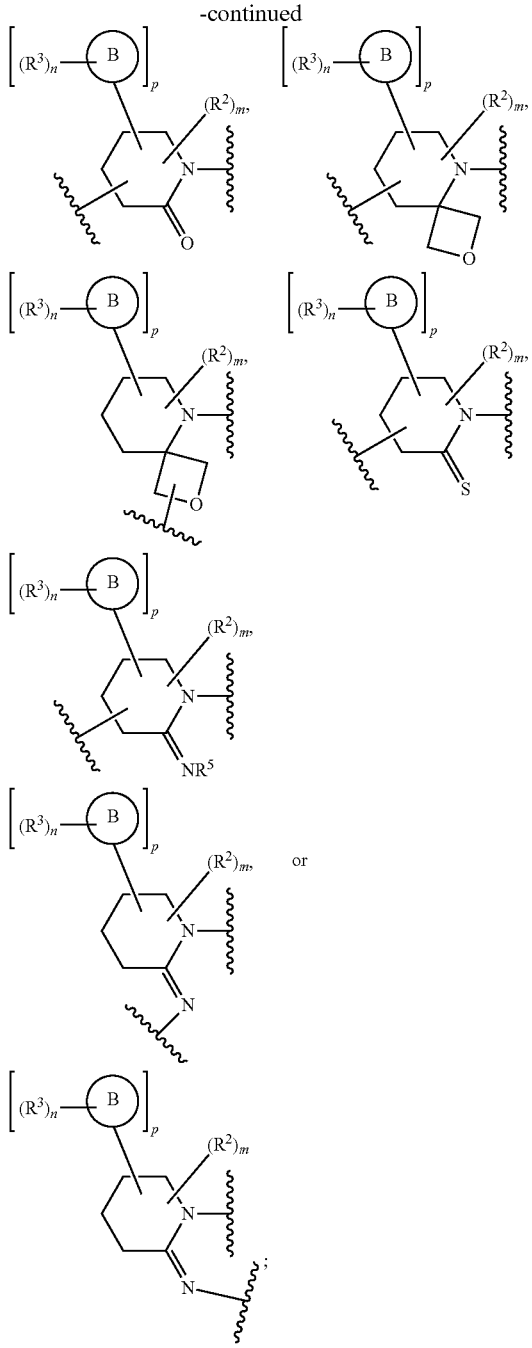

each $R^2$ is independently hydrogen, $-R^6$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, $-R^6$, halogen, $-CN$, $-NO_2$, $-OR$, $-SR$, $-NR_2$, $-S(O)_2R$, $-S(O)_2NR_2$, $-S(O)R$, $-C(O)R$, $-C(O)OR$, $-C(O)NR_2$, $-C(O)N(R)OR$, $-OC(O)R$, $-OC(O)NR_2$, $-N(R)C(O)OR$, $-N(R)C(O)R$, $-N(R)C(O)NR_2$, or $-N(R)S(O)_2R$;

Ring B is hydrogen, $C_{1-4}$ aliphatic, or $-CN$;

each $R^6$ is with 1-3 heteroatoms independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, $-O-$, $-NR-$, $-S-$, $-OC(O)-$, $-C(O)O-$, $-C(O)-$, $-S(O)-$, $-S(O)_2-$, $-NRS(O)_2-$, $-S(O)_2NR-$, $-NRC(O)-$, $-C(O)NR-$, $-OC(O)NR-$, $-NRC(O)-$,

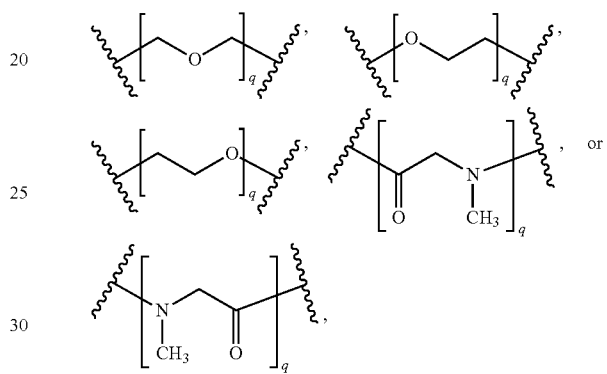

wherein:
each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;
n is 0, 1, 2, 3, or 4;
p is 0 or 1;
each of q is independently 1, 2, 3, 4, 5, 6, 7, 8, 9, or 10; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

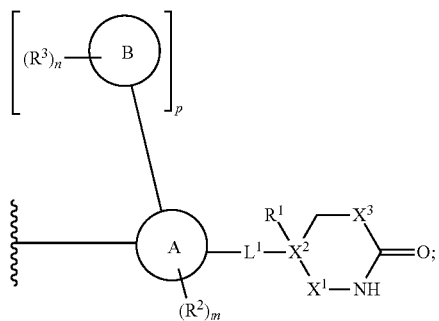

thereby forming a compound of formula I-n':

I-n'

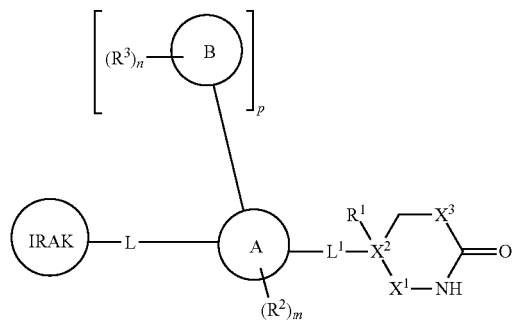

or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

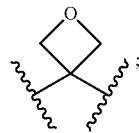 [SMILES: *C1(*)COC1]

$X^2$ is a carbon atom or silicon atom;

$X^3$ is a bivalent moiety selected from —$CH_2$— or —Si($R^2$)—;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

Ring A is a mono- or bicyclic ring selected from

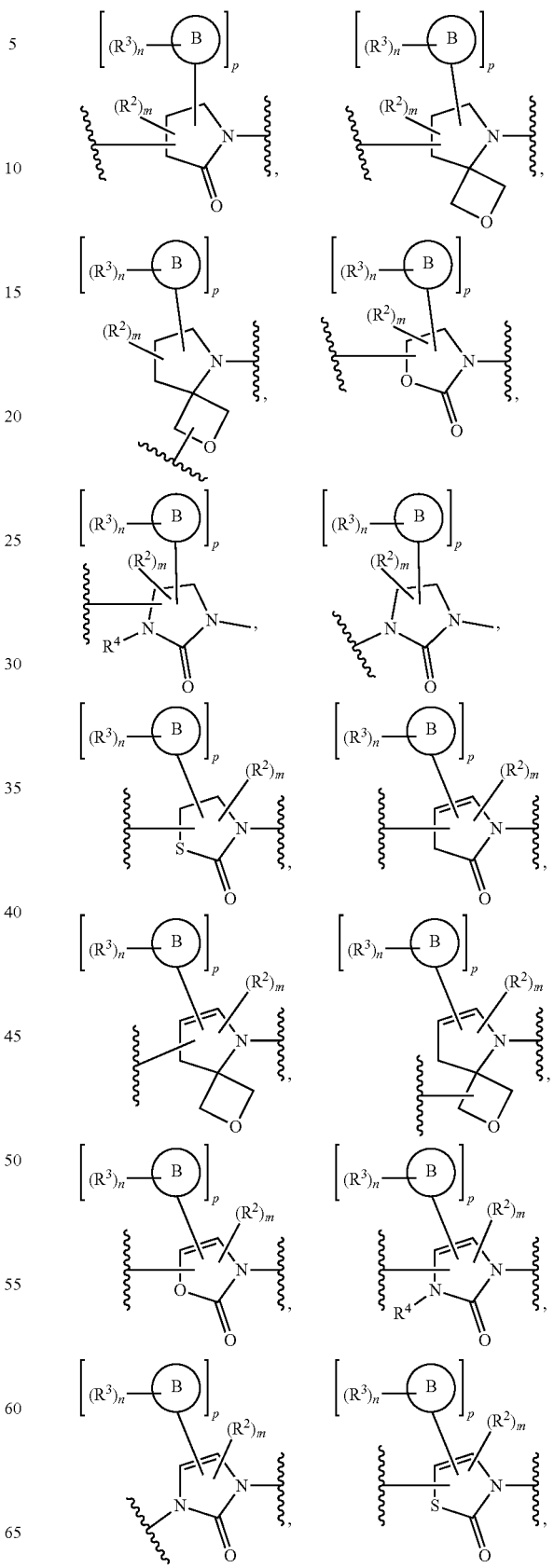

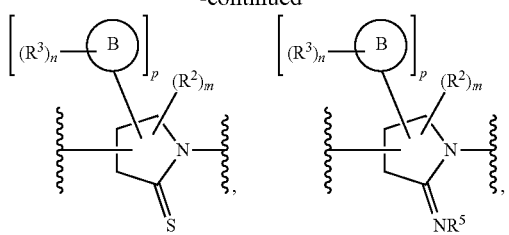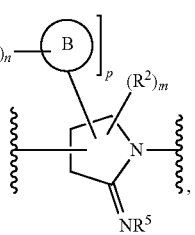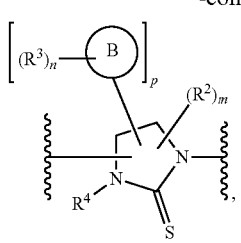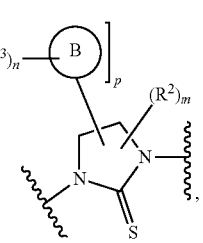
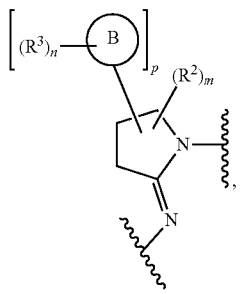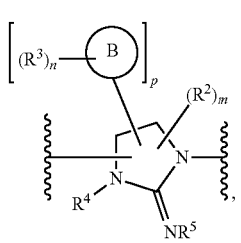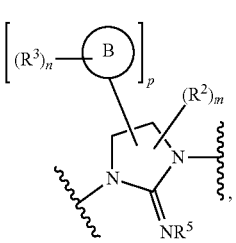
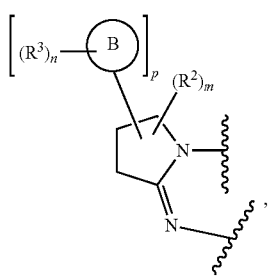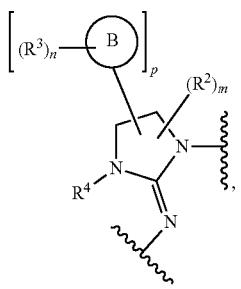
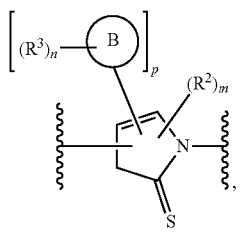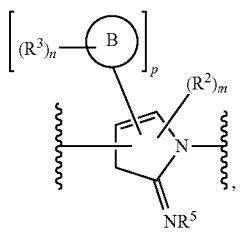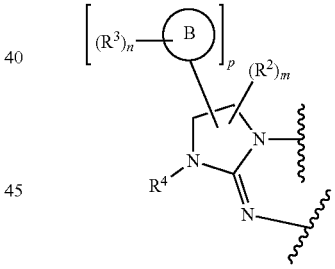
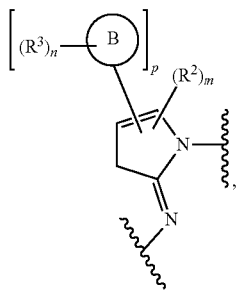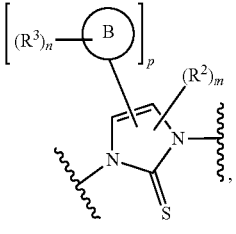
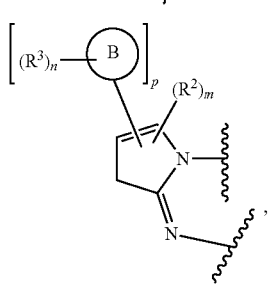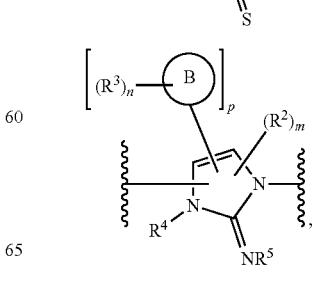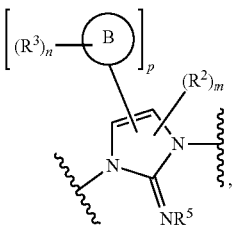

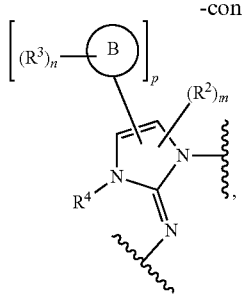

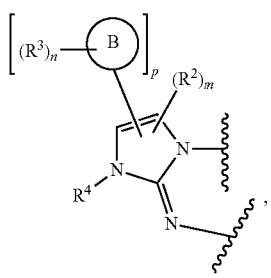

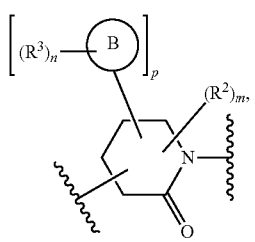

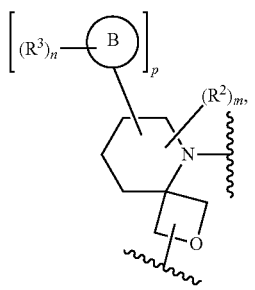

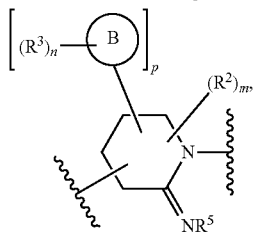

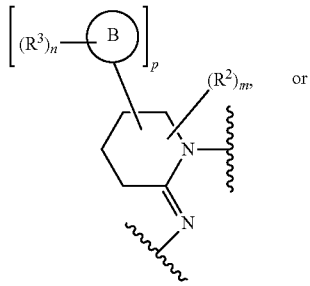

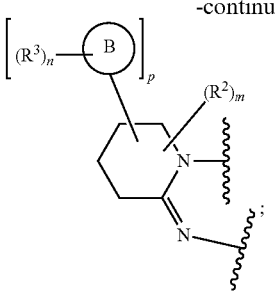

each $R^2$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, or —N(R)$S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —$S(O)_2$—, —$NRS(O)_2$—, —$S(O)_2NR$—, —NRC(O)—, —C(O)NR—, —OC(O)NR—, —NRC(O)O—,

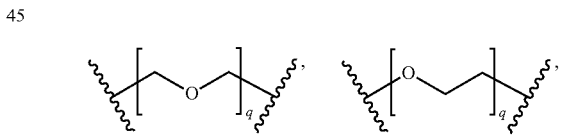

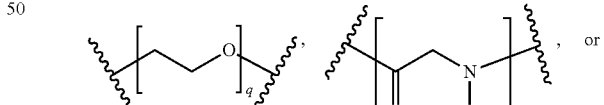

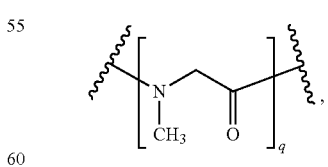

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;

n is 0, 1, 2, 3, or 4;

p is 0 or 1;

each of q is independently 1, 2, 3, 4, 5, 6, 7, 8, 9, or 10; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-n' above is provided as a compound of formula I-n'' or formula I-n''':

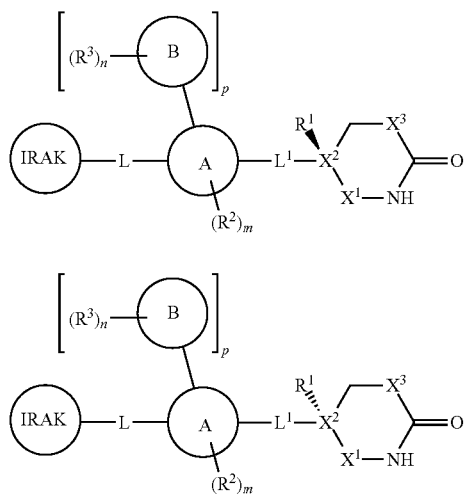

I-n''

I-n''' or a pharmaceutically acceptable salt thereof, wherein:

each of IRAK, Ring A, Ring B, L, $L^1$, $R^1$, $R^2$, $R^3$, $X^1$, $X^2$, $X^3$, n, p, and m is as defined above.

In certain embodiments, the present invention provides a compound of formula I, wherein LBM is an E3 ubiquitin ligase (cereblon) binding moiety

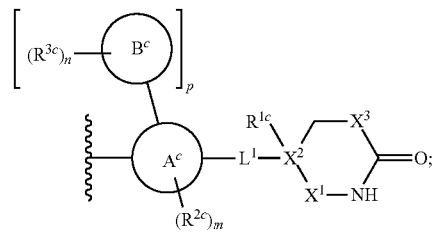

thereby forming a compound of formula I-n-1:

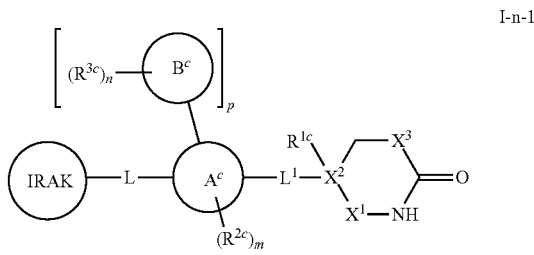

I-n-1 or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

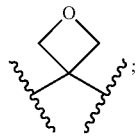 [SMILES: *C1(*)COC1]

$X^2$ is a carbon atom or silicon atom;

$X^3$ is a bivalent moiety selected from —$CH_2$— or —Si($R^2$)—;

$R^{1c}$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

Ring AC is a mono- or bicyclic ring selected from

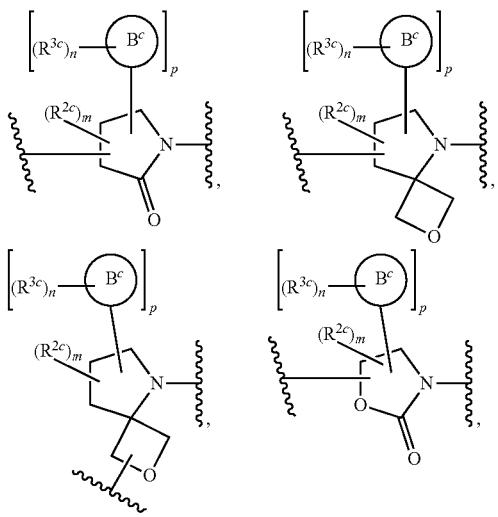

-continued
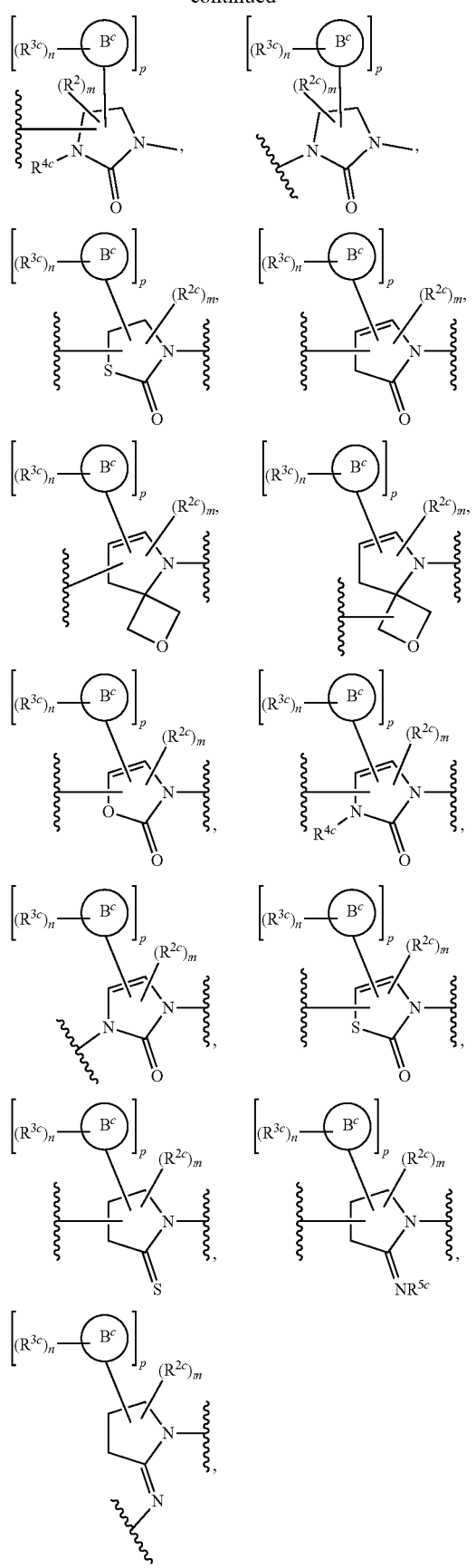
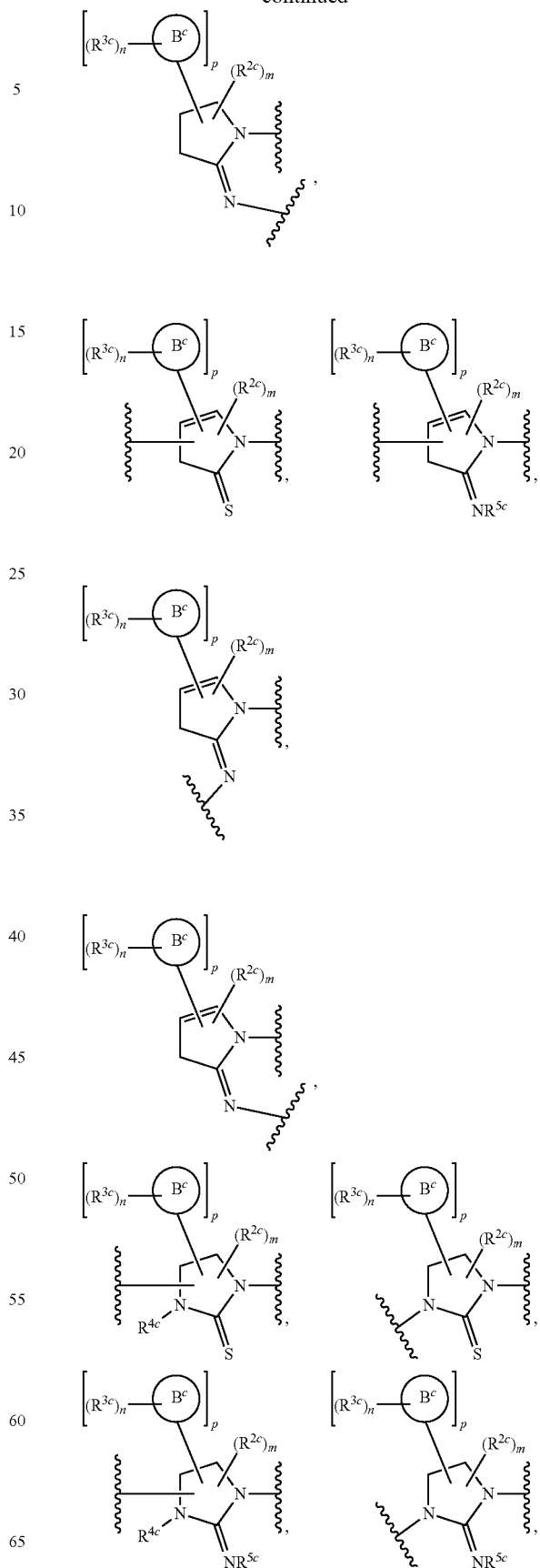

-continued

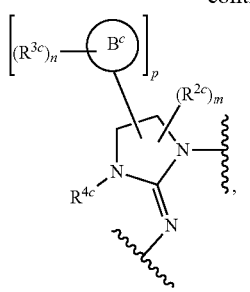

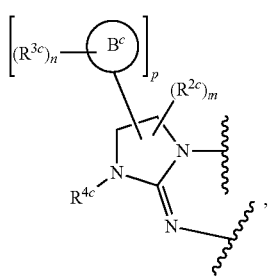

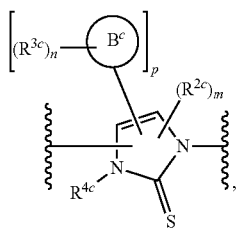 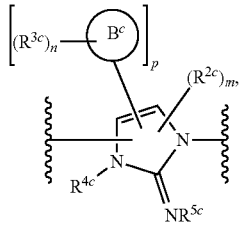

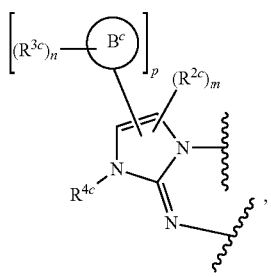

-continued

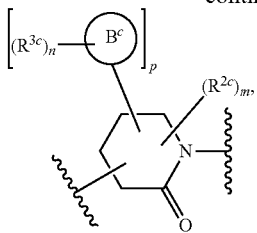 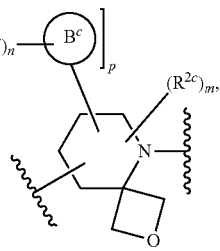

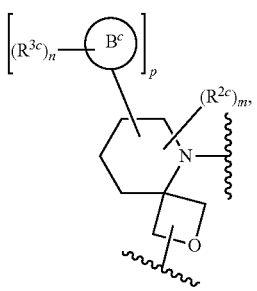 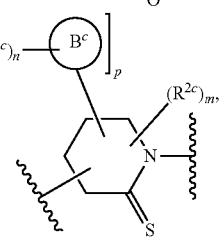

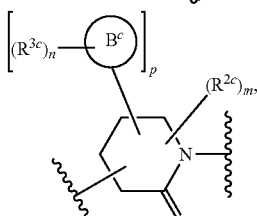

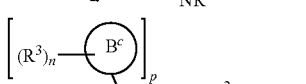 or

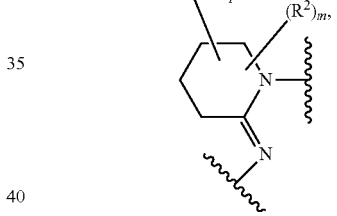

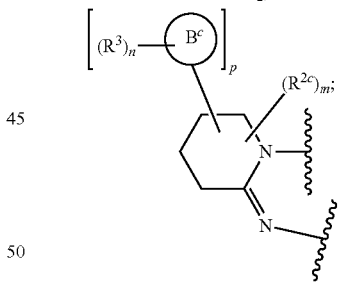

each $R^{2c}$ is independently hydrogen, —$R^{6c}$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring $B^c$ is selected from a 6-membered aryl containing 0-2 nitrogen atoms or a 5-membered heteroaryl with 1-3 heteroatoms independently selected from nitrogen, oxygen or sulfur;

each of $R^{3c}$ and $R^{4c}$ is independently hydrogen, —$R^{6c}$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^{5c}$ is hydrogen, $C_{1-4}$ aliphatic, or —CN;

each $R^{6c}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

$L^1$ is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

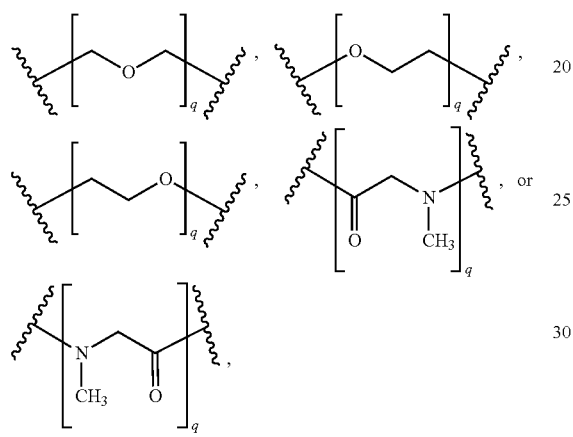

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, or 2;
n is 0, 1, 2, 3, or 4;
p is 0 or 1;
each of q is independently 1, 2, 3, 4, 5, 6, 7, 8, 9, or 10; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-n-1 above is provided as a compound of formula I-n-1' or formula I-n-1":

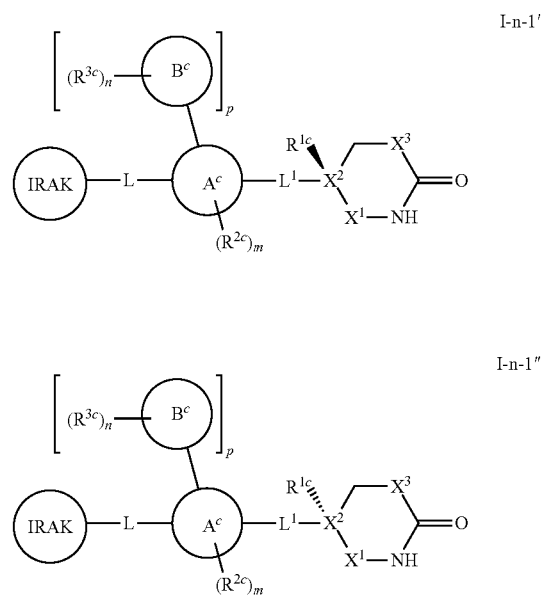

or a pharmaceutically acceptable salt thereof, wherein:

each of IRAK, Ring $A^c$, Ring $B^c$, L, $L^1$, $R^{1c}$, $R^{2c}$, $R^{3c}$, $X^1$, $X^2$, $X^3$, n, p, and m is as defined above.

In some embodiments, LBM is

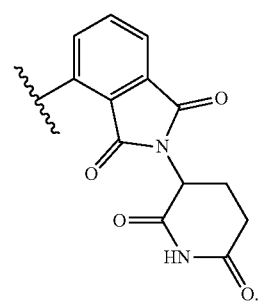 [SMILES: *c1cccc2c1C(=O)N(C1CCC(=O)NC1=O)C2=O]

In some embodiments, LBM is

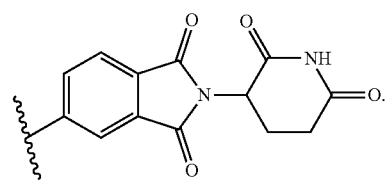 [SMILES: *c1ccc2c(c1)C(=O)N(C1CCC(=O)NC1=O)C2=O]

In some embodiments, LBM is
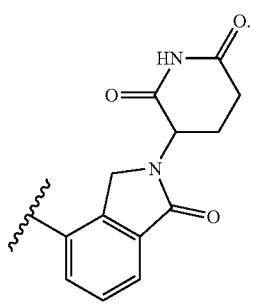 [SMILES: *c1cccc2c1CN(C1CCC(=O)NC1=O)C2=O]
In some embodiments, LBM is
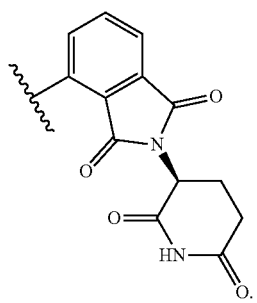 [SMILES: *c1cccc2c1C(=O)N([C@H]1CCC(=O)NC1=O)C2=O]
In some embodiments, LBM is
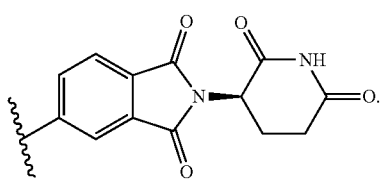 [SMILES: *c1ccc2c(c1)C(=O)N([C@@H]1CCC(=O)NC1=O)C2=O]
In some embodiments, LBM is
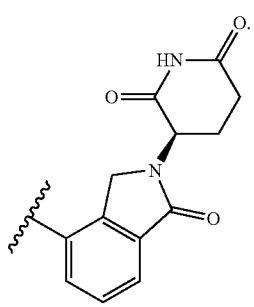 [SMILES: *c1cccc2c1CN([C@@H]1CCC(=O)NC1=O)C2=O]
In some embodiments, LBM is
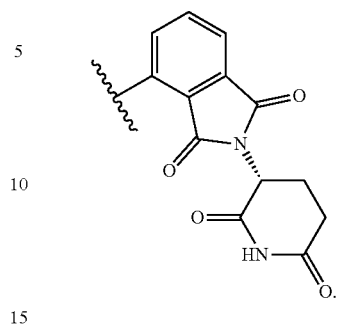
In some embodiments, LBM is
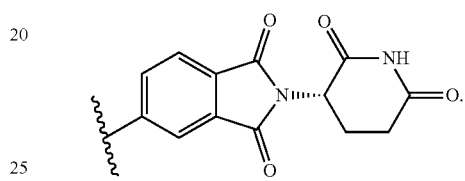
In some embodiments, LBM is
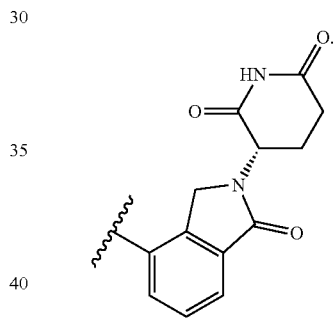
In some embodiments, LBM is
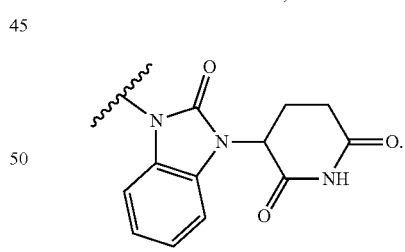
In some embodiments, LBM is
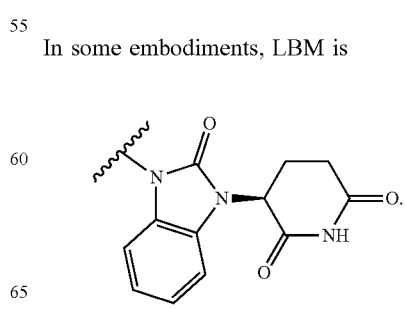

In some embodiments, LBM is
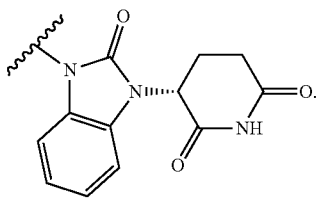 [SMILES: *n1c(=O)n([C@@H]2CCC(=O)NC2=O)c2ccccc21]
In some embodiments, LBM is
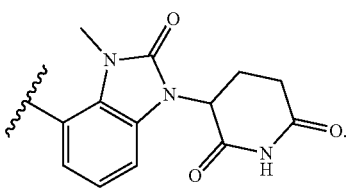
In some embodiments, LBM is
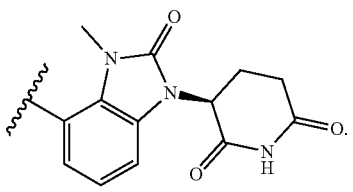
In some embodiments, LBM is
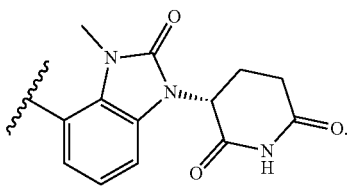
In some embodiments, LBM is
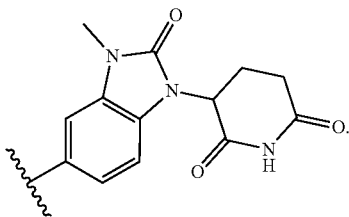
In some embodiments, LBM is
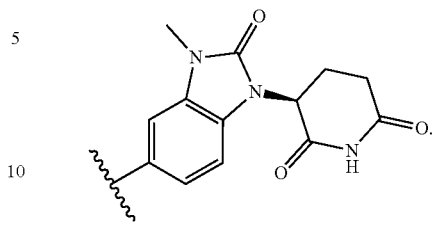
In some embodiments, LBM is
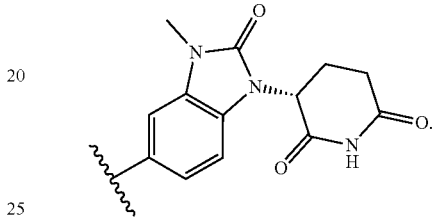
In some embodiments, LBM is
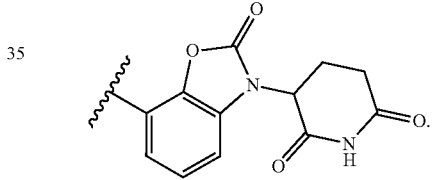
In some embodiments, LBM is
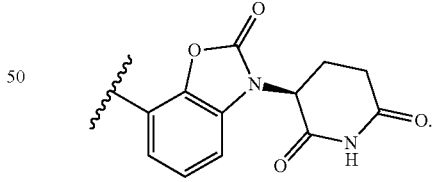
In some embodiments, LBM is
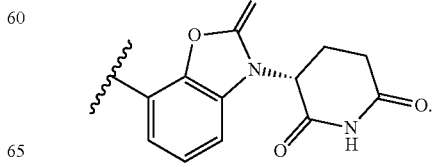

In some embodiments, LBM is

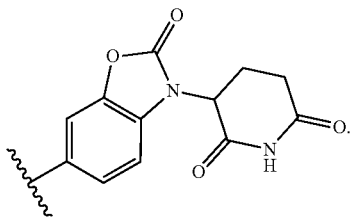

In some embodiments, LBM is

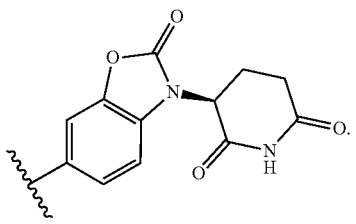

In some embodiments, LBM is

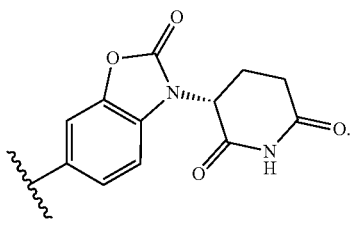

In some embodiments, LBM is

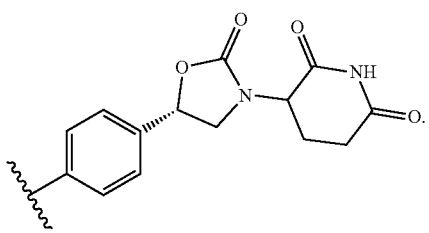 [SMILES: *c1ccc([C@H]2CN(C3CCC(=O)NC3=O)C(=O)O2)cc1]

In some embodiments, LBM is

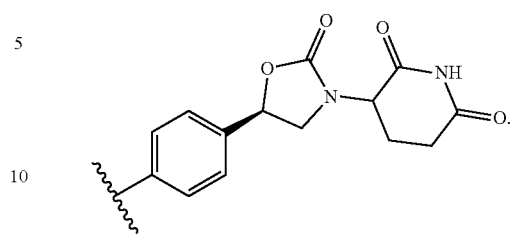

In some embodiments, LBM is

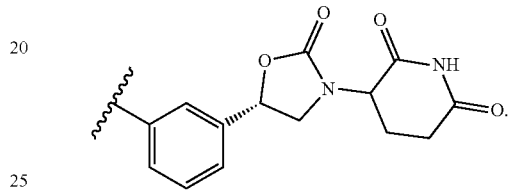

In some embodiments, LBM is

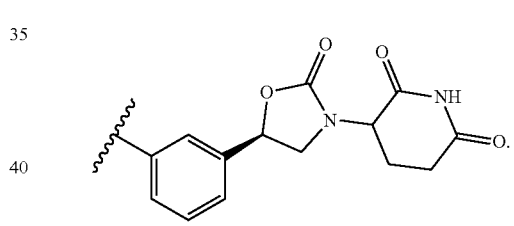

In some embodiments, LBM is selected from those depicted in Table 1, below.

In some embodiments, the present invention provides the compound of formula II as a compound of formula II-f:

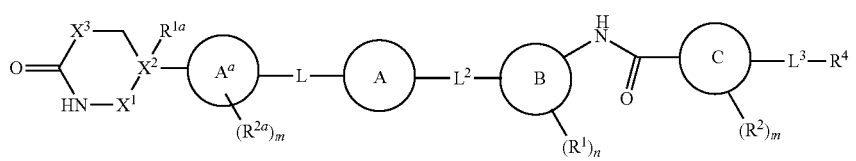

II-f or a pharmaceutically acceptable salt thereof, wherein each of $X^1$, $X^2$, $X^3$, $R^{1a}$, $R^{2a}$, Ring $A^a$, and m of the LBM moiety, L, and $L^2$, $L^3$, Ring A, Ring B, Ring C, $R^1$, $R^2$, $R^4$, n, and m of the IRAK moiety is as defined above and described in embodiments herein, both singly and in combination.

In certain embodiments, the present invention provides a compound of formula II-f:

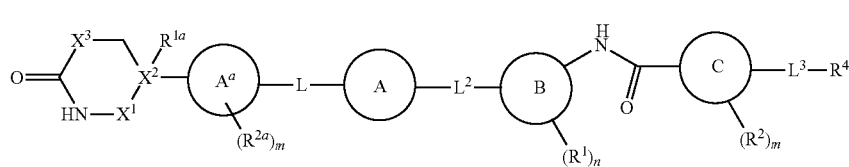

II-f or a pharmaceutically acceptable salt thereof, wherein:
L is a bivalent moiety that connects Ring $A^a$ to Ring A;
$X^1$ is a bivalent moiety selected from a covalent bond, —CH$_2$—, —C(O)—, —C(S)—, or

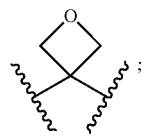;

$X^2$ is a carbon atom or silicon atom;
$X^3$ is a bivalent moiety selected from —CH$_2$— or —Si(R$^2$)—;
$R^{1a}$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;
each $R^{2a}$ is independently hydrogen, $R^{6a}$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
Ring $A^a$ is a bi- or tricyclic ring selected from

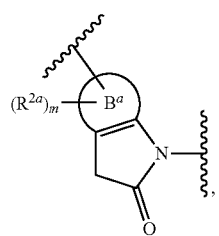

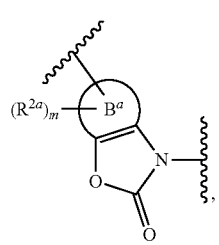

-continued

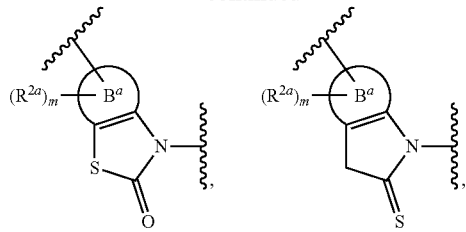

-continued

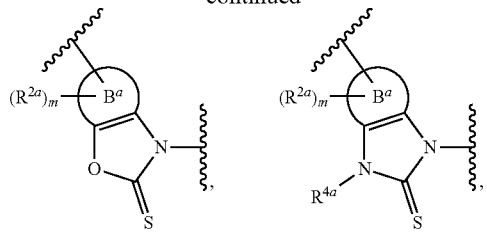

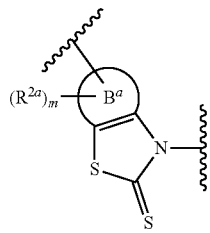
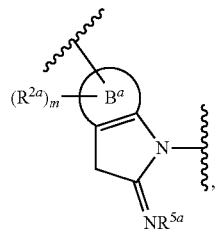

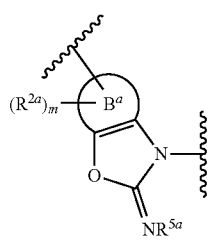
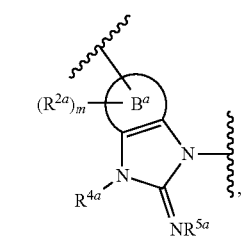

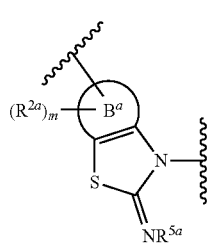
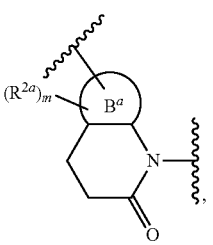

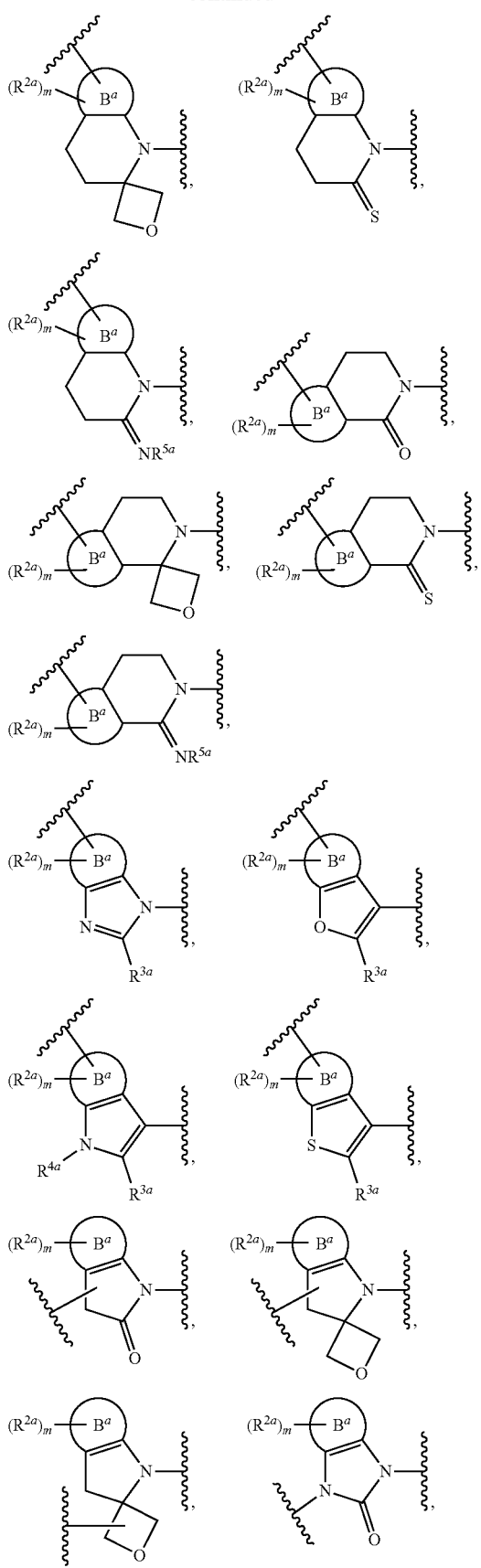
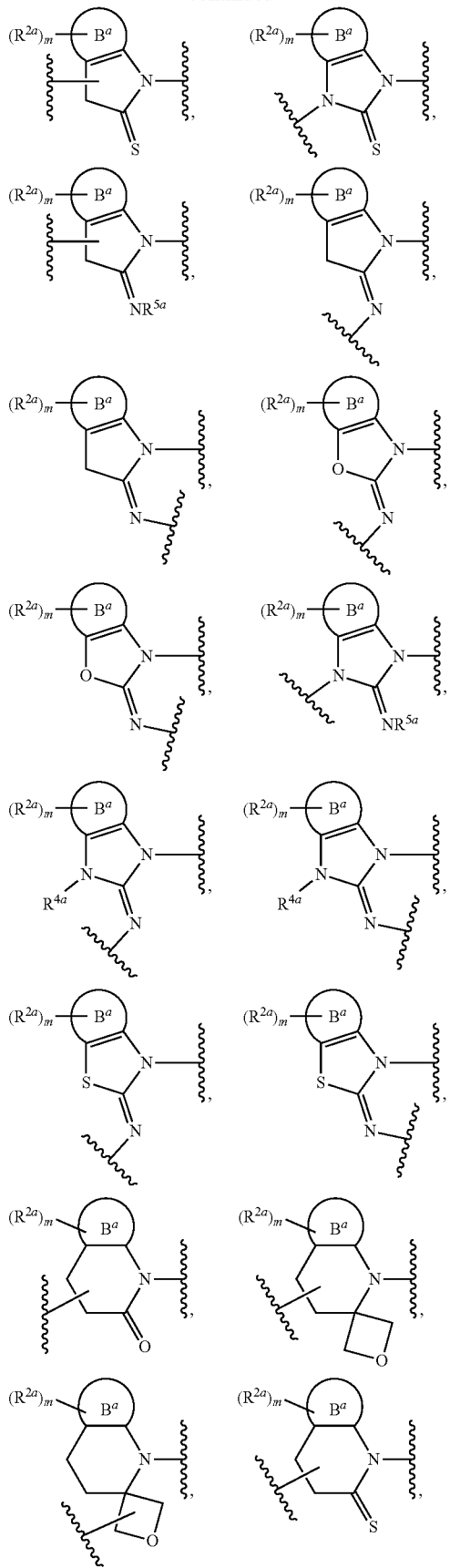

-continued

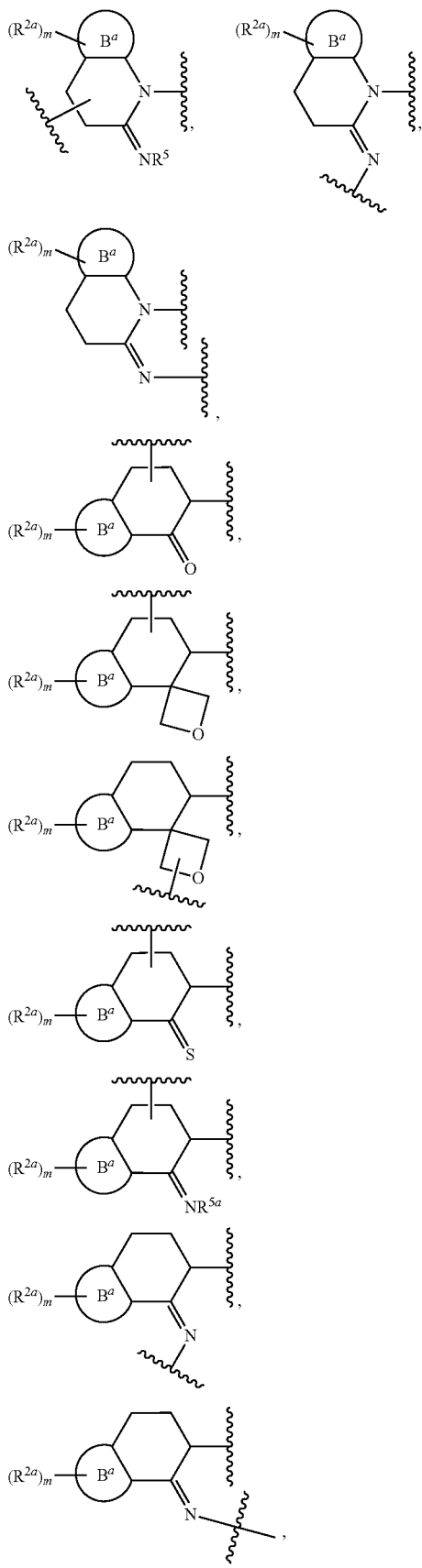

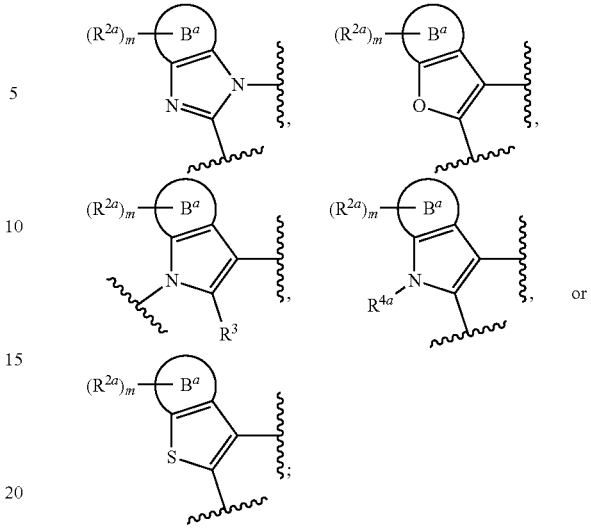

Ring $B^a$ is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^{3a}$ is selected from hydrogen, halogen, —OR, —N(R)$_2$, or —SR;

each $R^{4a}$ is independently hydrogen, $R^{6a}$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^{5a}$ is hydrogen, $C_{1-4}$ aliphatic, or —CN;

each $R^{6a}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a 4-10 membered saturated mono- or bicyclic carbocyclic or heterocyclic ring having 0-2 heteroatoms independently selected from nitrogen, oxygen, and sulfur;

Ring B is phenyl, a 4-10 membered saturated or partially unsaturated mono- or bicyclic carbocyclic or heterocyclic ring having 1-3 heteroatoms independently selected from nitrogen, oxygen, and sulfur, or a 5-9 membered mono- or bicyclic heteroaryl ring having 1-4 heteroatoms independently selected from nitrogen, oxygen, and sulfur;

Ring C is phenyl or a 5-10 membered mono- or bicyclic heteroaryl ring having 1-5 heteroatoms independently selected from nitrogen, oxygen, and sulfur;

each of $L^2$ and $L^3$ is independently a covalent bond or a $C_{1-3}$ bivalent straight or branched saturated or unsaturated hydrocarbon chain wherein 1-3 methylene units of the chain are independently and optionally replaced with —O—, —C(O)—, —C(S)—, —C(R)$_2$—, —CH(R)—, —C(F)$_2$—, —N(R)—, —S—, —S(O)$_2$— or —CR=CR—;

each $R^1$ is independently hydrogen, deuterium, $R^5$, halogen, —CN, —NO$_2$, —OR, —SR, —NR$_2$, —S(O)$_2$R, —S(O)$_2$NR$_2$, —S(O)R, —S(O)(NR)R, —P(O)(OR)$_2$, —P(O)(NR₂)₂, —CFR₂, —CF₂(R), —CF₃, —CR₂(OR), —CR₂(NR₂), —C(O)R, —C(O)OR, or —C(O)NR₂;

each R is independently hydrogen, deuterium, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same atom are optionally taken together with their intervening atom to form an optionally substituted 4-11 membered saturated or partially unsaturated carbocyclic or heterocyclic monocyclic, bicyclic, bridged bicyclic, spiro, or heteroaryl ring having 0-3 heteroatoms, in addition to the atom to which they are attached, independently selected from nitrogen, oxygen, and sulfur;

each R² is independently hydrogen, deuterium, R⁵, halogen, —CN, —NO₂, —OR, —SR, —NR₂, —S(O)₂R, —S(O)₂NR₂, —S(O)R, —S(O)(NR)R, —P(O)(OR)₂, —P(O)(NR₂)₂, —CF₂(R), —CF₃, —CR₂(OR), —CR₂(NR₂), —C(O)R, —C(O)OR, C(O)NR₂, —C(O)N(R)OR, —OC(O)R, —OC(O)NR₂, N(R)C(O)OR, —N(R)C(O)R, —N(R)C(O)NR₂, or —N(R)S(O)₂R;

R⁴ is selected from

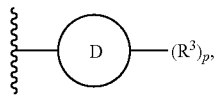

hydrogen, or an optionally substituted group selected from C₁₋₆ aliphatic or a 4-11 membered saturated or partially unsaturated carbocyclic or heterocyclic monocyclic, bicyclic, bridged bicyclic, or spiro ring having 1-3 heteroatoms independently selected from nitrogen, oxygen, and sulfur;

Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;

each R³ is independently hydrogen, deuterium, R⁵, halogen, —CN, —NO₂, —OR, —SR, —NR₂, —S(O)₂R, —S(O)₂NR₂, —S(O)R, —S(O)(NR)R, —P(O)(OR)₂, —P(O)(NR₂)₂, —CF₂(R), —CF₃, —CR₂(OR), —CR₂(NR₂), —C(O)R, —C(O)OR, C(O)NR₂, —C(O)N(R)OR, —OC(O)R, —OC(O)NR₂, N(R)C(O)OR, —N(R)C(O)R, —N(R)C(O)NR₂, or —N(R)S(O)₂R;

each R⁵ is independently an optionally substituted group selected from C₁₋₆ aliphatic, phenyl, a 3-7 membered saturated or partially unsaturated carbocyclic or heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

n is 0, 1, or 2;

each m is independently 0, 1, 2, 3 or 4; and p is 0, 1, 2, 3 or 4;

In some embodiments, the present invention provides the compound of formula II-f, wherein X² is a carbon atom, X³ is —CH₂—, and Ring B is pyrazolyl as shown, thereby providing a compound of formula II-f-1:

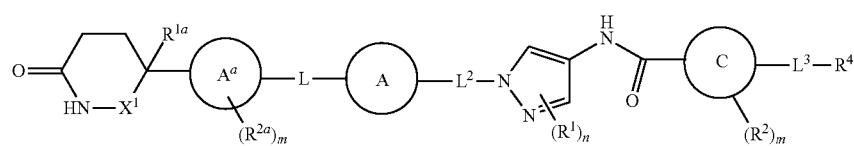

II-f-1 or a pharmaceutically acceptable salt thereof, wherein each of X¹, R¹ᵃ, R²ᵃ, Ring Aᵃ, and m of the LBM moiety, L, and L², L³, Ring A, Ring C, R¹, R², R⁴, n, and m of the IRAK moiety is as defined above and described in embodiments herein, both singly and in combination.

In some embodiments, the present invention provides the compound of formula II-f, wherein X² is a carbon atom, X³ is —CH₂—, Ring Aᵃ is

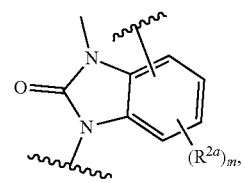

and Ring B is pyrazolyl as shown, thereby providing a compound of formula II-f-2:

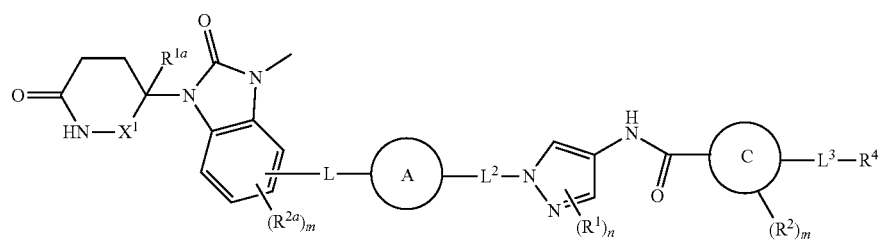

II-f-2 or a pharmaceutically acceptable salt thereof, wherein each of X¹, R¹ᵃ, R²ᵃ, and m of the LBM moiety, L, and L², L³, Ring A, Ring C, $R^1$, $R^2$, $R^4$, n, and m of the IRAK moiety is as defined above and described in embodiments herein, both singly and in combination.

In some embodiments, the present invention provides the compound of formula II-f, wherein $X^2$ is a carbon atom, $X^3$ is —$CH_2$—, Ring A is cyclohexyl, $L^2$ is a covalent bond, and Ring B is pyrazolyl as shown, thereby providing a compound of formula II-f-3:

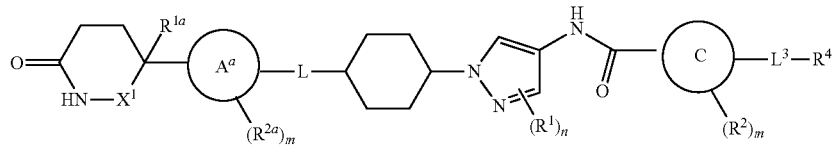

II-f-3 or a pharmaceutically acceptable salt thereof, wherein each of $X^1$, $R^{1a}$, $R^{2a}$, Ring $A^a$, and m of the LBM moiety, L, and $L^3$, Ring C, $R^1$, $R^2$, $R^4$, n, and m of the IRAK moiety is as defined above and described in embodiments herein, both singly and in combination.

In some embodiments, the present invention provides the compound of formula II-f, wherein $X^2$ is a carbon atom, $X^3$ is —$CH_2$—, Ring C is pyrazolo[1,5-a]pyrimidine, and Ring B is pyrazolyl as shown, thereby providing a compound of formula II-f-4:

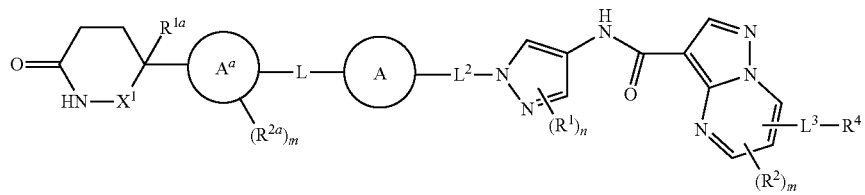

II-f-4 or a pharmaceutically acceptable salt thereof, wherein each of $X^1$, $R^{1a}$, $R^{2a}$, Ring $A^a$, and m of the LBM moiety, L, and $L^2$, $L^3$, Ring A, Ring C, $R^1$, $R^2$, $R^4$, n, and m of the IRAK moiety is as defined above and described in embodiments herein, both singly and in combination.

In some embodiments, the present invention provides the compound of formula II-f, wherein $X^2$ is a carbon atom, $X^3$ is —$CH_2$—, L is

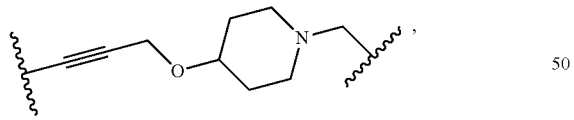

and Ring B is pyrazolyl as shown, thereby providing a compound of formula II-f-5:

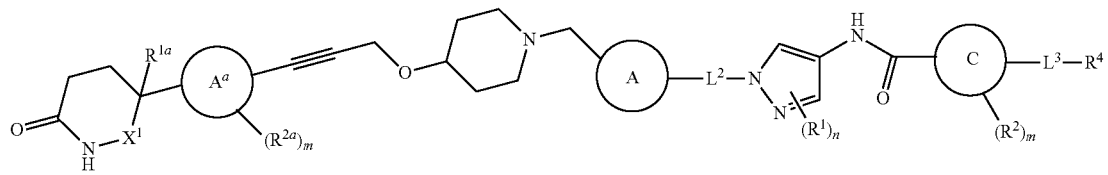

II-f-5 or a pharmaceutically acceptable salt thereof, wherein each of $X^1$, $R^{1a}$, $R^{2a}$, Ring $A^a$, and m of the LBM moiety, and $L^2$, $L^3$, Ring A, Ring C, $R^1$, $R^2$, $R^4$, n, and m of the IRAK moiety is as defined above and described in embodiments herein, both singly and in combination.

In some embodiments, the present invention provides the compound of formula II, wherein $L^2$ is a covalent bond, Ring A is cyclohexyl, Ring B is pyrazolyl, Ring C is oxazolyl, and Ring D is pyridyl thereby forming a compound of formula II-g:

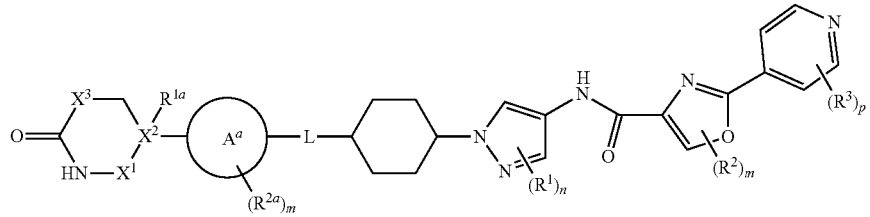

II-g or a pharmaceutically acceptable salt thereof, wherein each of $X^1$, $X^2$, $X^3$, $R^{1a}$, $R^{2a}$, Ring $A^a$, and m of the LBM moiety, L, and $R^1$, $R^2$, $R^3$, n, m, and p of the IRAK moiety is as defined above and described in embodiments herein, both singly and in combination.

In some embodiments, the present invention provides the compound of formula II, wherein LBM is

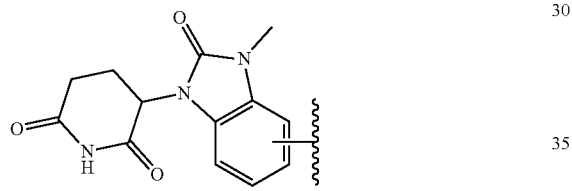

thereby forming a compound of formula II-h:

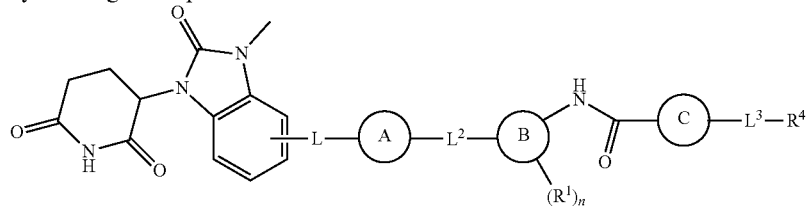

II-h or a pharmaceutically acceptable salt thereof, wherein each of L, $L^2$, $L^3$, Ring A, Ring B, Ring C, $R^1$, $R^2$, $R^4$, n, and m is as defined above and described in embodiments herein, both singly and in combination.

In some embodiments, the present invention provides the compound of formula II, wherein LBM is

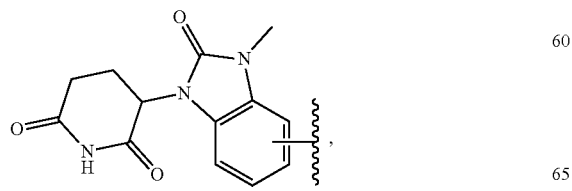

$L^2$ is a covalent bond, Ring A is cyclohexyl, Ring B is pyrazolyl, Ring C is oxazolyl, and Ring D is pyridyl thereby forming a compound of formula II-i:

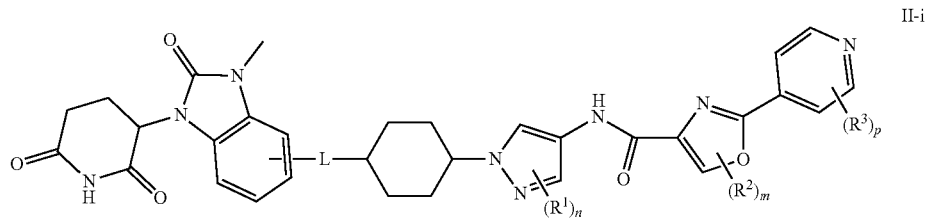

II-i or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-d, wherein LBM is

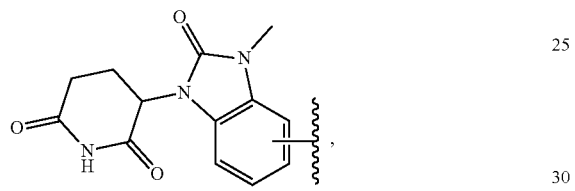

$L^2$ is a covalent bond, Ring A is cyclohexyl, and Ring B is pyrazolyl as shown, thereby forming a compound of formula II-d-1:

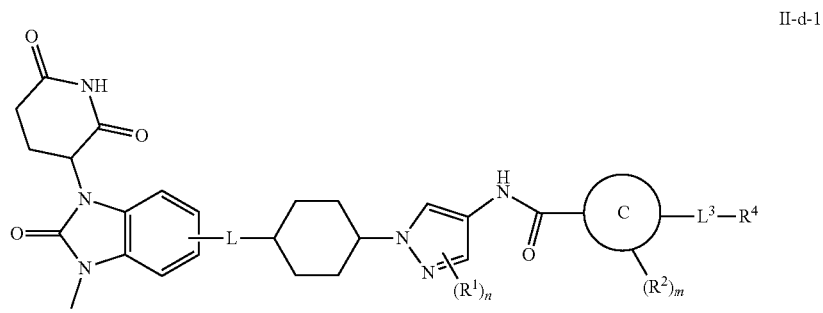

II-d-1 or a pharmaceutically acceptable salt thereof, wherein each of L, $L^3$, Ring C, $R^1$, $R^2$, $R^4$, n, and m is as defined above and described in embodiments herein, both singly and in combination.

In certain embodiments, the present invention provides the compound of formula II-e, wherein LBM is

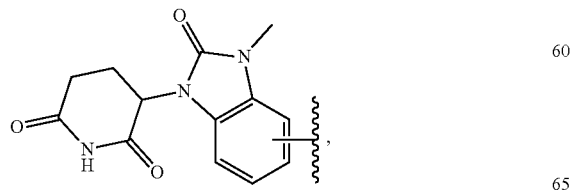

L² is a covalent bond, Ring A is cyclohexyl, Ring C is pyrazolo[1,5-a]pyrimidine, and Ring B is pyrazolyl as shown, thereby forming a compound of formula II-e-1:

II-e-1

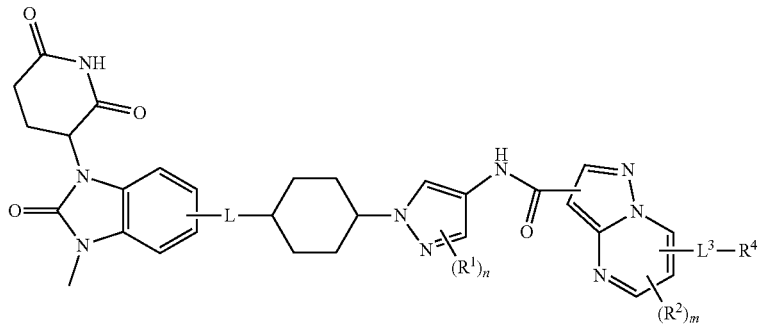

or a pharmaceutically acceptable salt thereof, wherein each of L, R¹, R², R³, n, m, and p is as defined above and described in embodiments herein, both singly and in combination.

In some embodiments, the present invention provides the compound of formula II, wherein LBM is

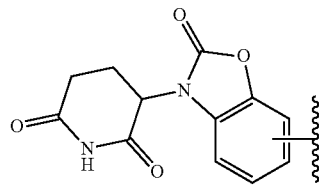

thereby forming a compound of formula II-j:

II-j

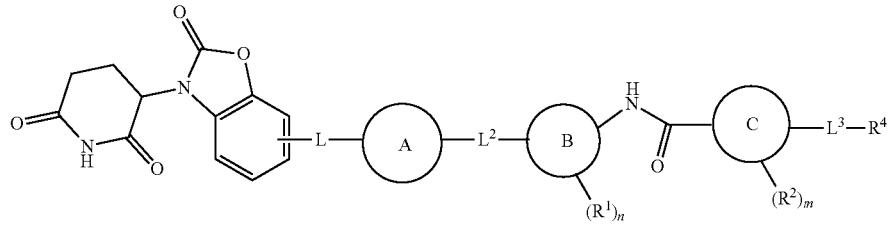

or a pharmaceutically acceptable salt thereof, wherein each of L, L², L³, Ring A, Ring B, Ring C, R¹, R², R⁴, n, and m is as defined above and described in embodiments herein, both singly and in combination.

In some embodiments, the present invention provides the compound of formula II, wherein LBM is

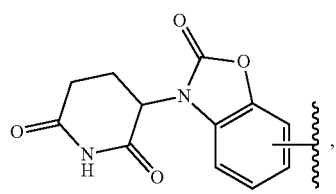

L² is a covalent bond, Ring A is cyclohexyl, Ring B is pyrazolyl, Ring C is oxazolyl, and Ring D is pyridyl thereby forming a compound of formula II-k:

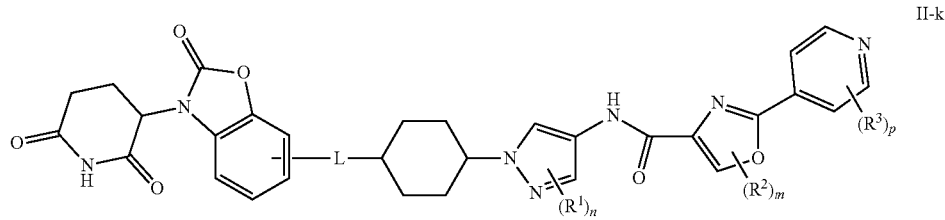

II-k or a pharmaceutically acceptable salt thereof, wherein each of L, R¹, R², R³, n, m, and p is as defined above and described in embodiments herein, both singly and in combination.

In certain embodiments, the present invention provides the compound of formula II-d, wherein LBM is

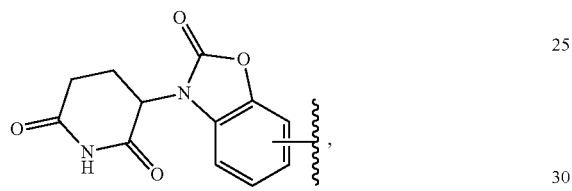

L² is a covalent bond, Ring A is cyclohexyl, and Ring B is pyrazolyl as shown, thereby forming a compound of formula II-d-2:

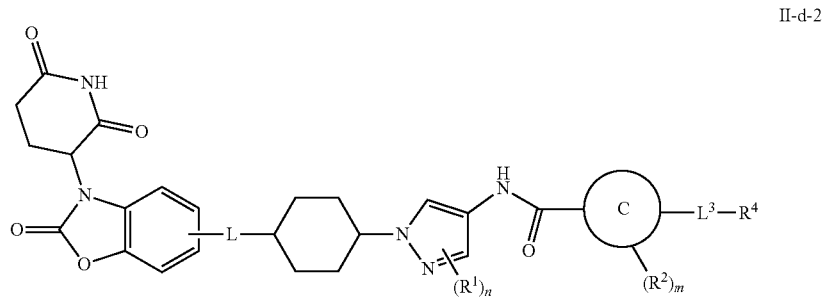

II-d-2 or a pharmaceutically acceptable salt thereof, wherein each of L, L³, Ring C, R¹, R², R⁴, n, and m is as defined above and described in embodiments herein, both singly and in combination.

In certain embodiments, the present invention provides the compound of formula II-e, wherein LBM is

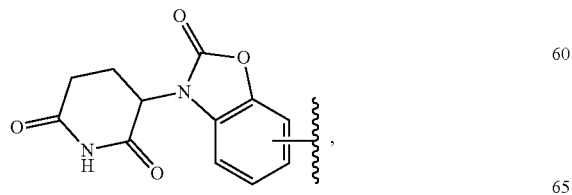

L² is a covalent bond, Ring A is cyclohexyl, Ring C is pyrazolo[1,5-a]pyrimidine, and Ring B is pyrazolyl as shown, thereby forming a compound of formula II-e-2:

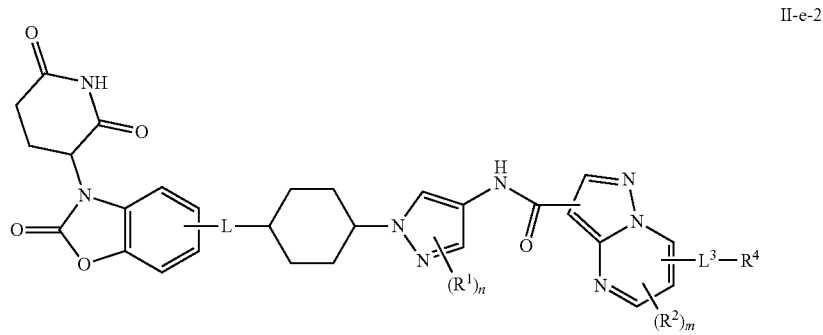

II-e-2 or a pharmaceutically acceptable salt thereof, wherein each of L, R¹, R², R³, n, m, and p is as defined above and described in embodiments herein, both singly and in combination.

In some embodiments, the present invention provides the compound of formula II, wherein LBM is

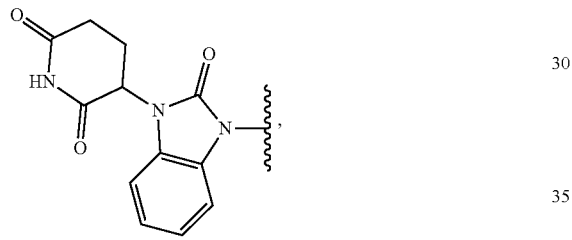

L² is a covalent bond, Ring A is cyclohexyl, Ring B is pyrazolyl, Ring C is oxazolyl, and Ring D is pyridyl thereby forming a compound of formula II-1:

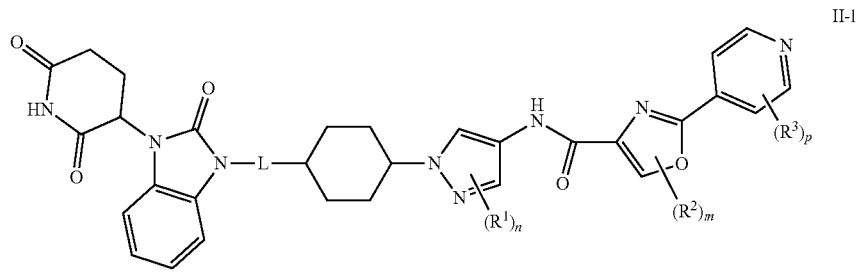

II-1 or a pharmaceutically acceptable salt thereof, wherein each of L, R¹, R², R³, n, m, and p is as defined above and described in embodiments herein, both singly and in combination.

In certain embodiments, the present invention provides the compound of formula II-d, wherein LBM is

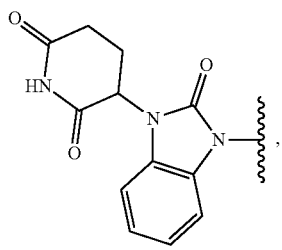 [SMILES: *n1c(=O)n(C2CCC(=O)NC2=O)c2ccccc21]

$L^2$ is a covalent bond, Ring A is cyclohexyl, and Ring B is pyrazolyl as shown, thereby forming a compound of formula II-d-3:

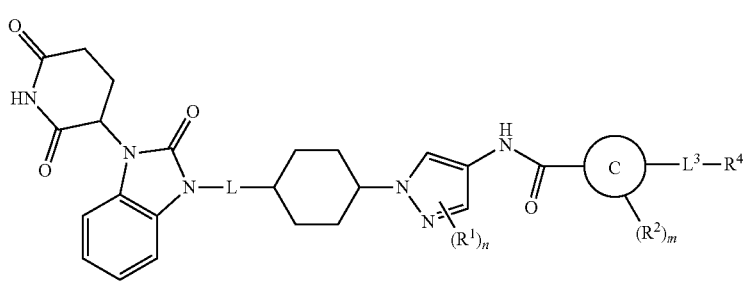

II-d-3 or a pharmaceutically acceptable salt thereof, wherein each of L, $L^3$, Ring C, $R^1$, $R^2$, $R^4$, n, and m is as defined above and described in embodiments herein, both singly and in combination.

In certain embodiments, the present invention provides the compound of formula II-e, wherein LBM is

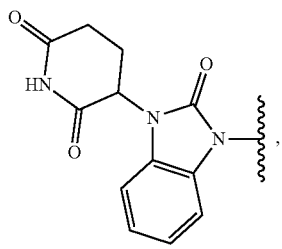 [SMILES: *n1c(=O)n(C2CCC(=O)NC2=O)c2ccccc21]

$L^2$ is a covalent bond, Ring A is cyclohexyl, Ring C is pyrazolo[1,5-a]pyrimidine, and Ring B is pyrazolyl as shown, thereby forming a compound of formula II-e-3:

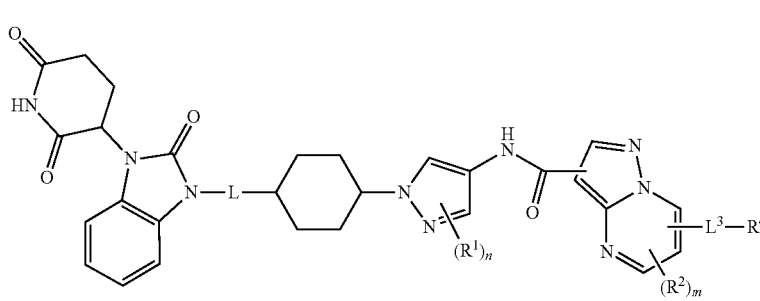

II-e-3 or a pharmaceutically acceptable salt thereof, wherein each of L, $R^1$, $R^2$, $R^3$, n, m, and p is as defined above and described in embodiments herein, both singly and in combination.

In some embodiments, the present invention provides the compound of formula II, wherein LBM is

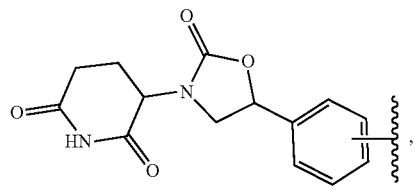

Ring A is cyclohexyl, Ring B is pyrazolyl, Ring C is oxazolyl, and Ring D is pyridyl thereby forming a compound of formula II-m:

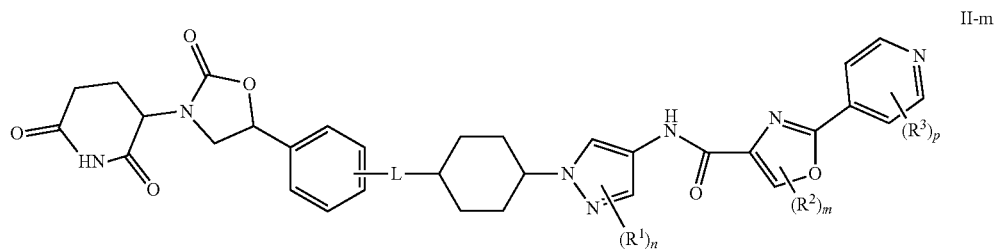

II-m or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-d, wherein LBM is

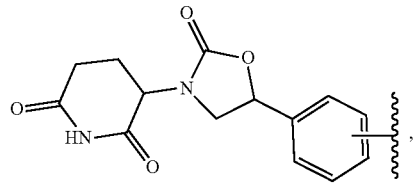

thereby forming a compound of formula II-d-4:

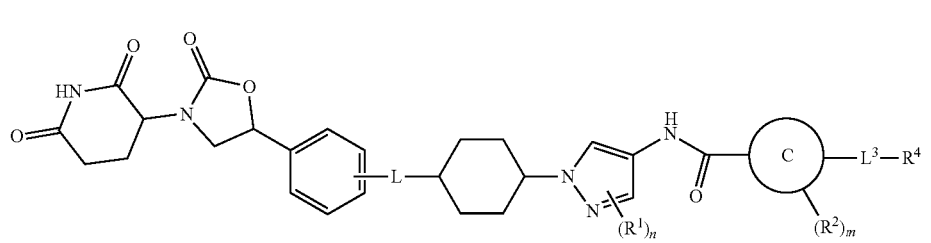

II-d-4 or a pharmaceutically acceptable salt thereof, wherein each of L, L³, Ring C, R¹, R², R⁴, n, and m is as defined above and described in embodiments herein, both singly and in combination.

In certain embodiments, the present invention provides the compound of formula II-e, wherein LBM is

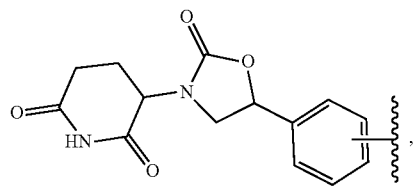

thereby forming a compound of formula II-e-4:

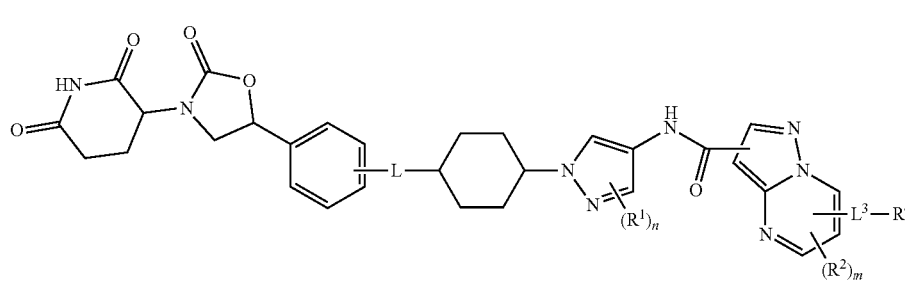

II-e-4 or a pharmaceutically acceptable salt thereof, wherein each of L, R¹, R², R³, n, m, and p is as defined above and described in embodiments herein, both singly and in combination.

In some embodiments, the present invention provides the compound of formula II, wherein LBM is

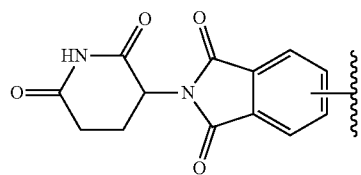

thereby forming a compound of formula II-n:

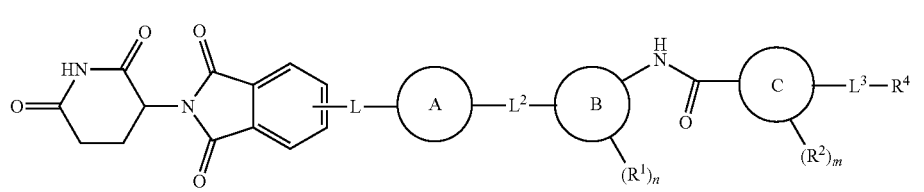

II-n or a pharmaceutically acceptable salt thereof, wherein each of L, L², L³, Ring A, Ring B, Ring C, R¹, R², R⁴, n, and m is as defined above and described in embodiments herein, both singly and in combination.

In some embodiments, the present invention provides the compound of formula II, wherein LBM is

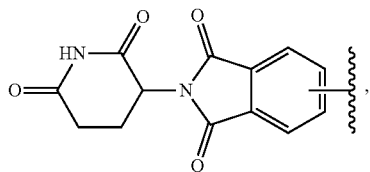

Ring A is cyclohexyl, Ring B is pyrazolyl, Ring C is oxazolyl, and Ring D is pyridyl thereby forming a compound of formula II-o:

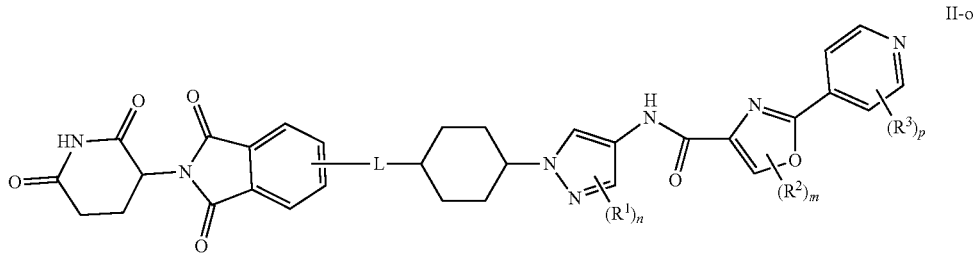

II-o or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-d, wherein LBM is

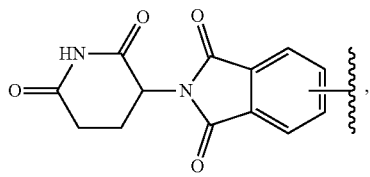

thereby forming a compound of formula II-d-5:

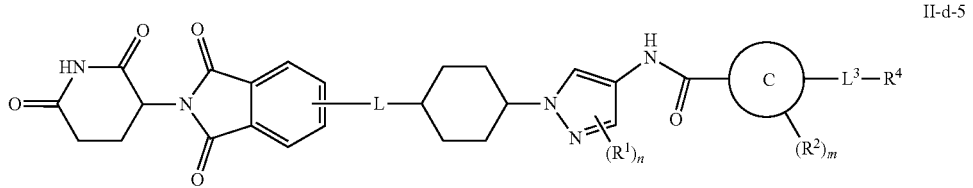

II-d-5 or a pharmaceutically acceptable salt thereof, wherein each of L, $L^3$, Ring C, $R^1$, $R^2$, $R^4$, n, and m is as defined above and described in embodiments herein, both singly and in combination.

In certain embodiments, the present invention provides the compound of formula II-e, wherein LBM is

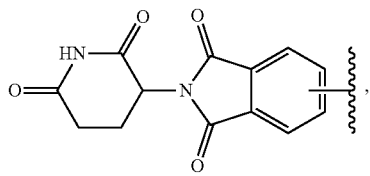

thereby forming a compound of formula II-e-5:

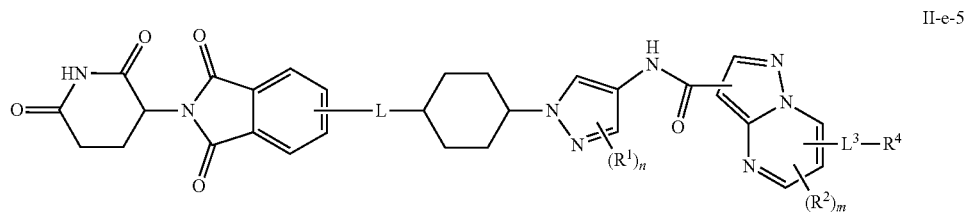

II-e-5 or a pharmaceutically acceptable salt thereof, wherein each of L, $R^1$, $R^2$, $R^3$, n, m, and p is as defined above and described in embodiments herein, both singly and in combination.

In some embodiments, the present invention provides the compound of formula II, wherein LBM is

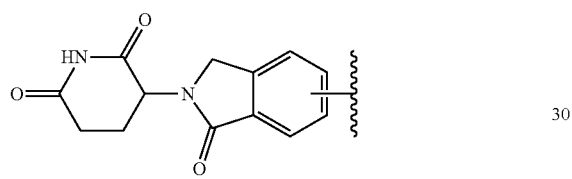

thereby forming a compound a compound of formula II-p:

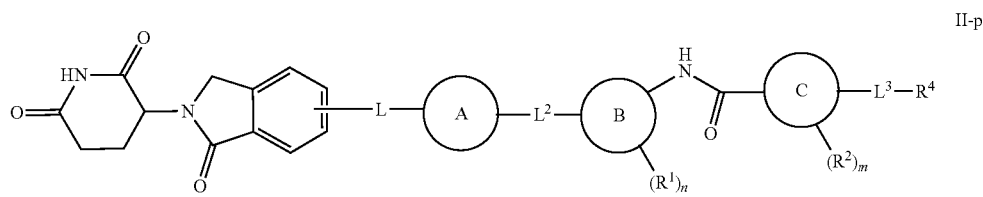

II-p or a pharmaceutically acceptable salt thereof, wherein each of L, $L^2$, $L^3$, Ring A, Ring B, Ring C, $R^1$, $R^2$, $R^4$, n, and m is as defined above and described in embodiments herein, both singly and in combination.

In some embodiments, the present invention provides the compound of formula II, wherein LBM is

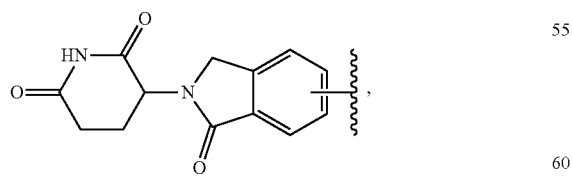

,

Ring A is cyclohexyl, Ring B is pyrazolyl, Ring C is oxazolyl, and Ring D is pyridyl thereby forming a compound of formula II-q:

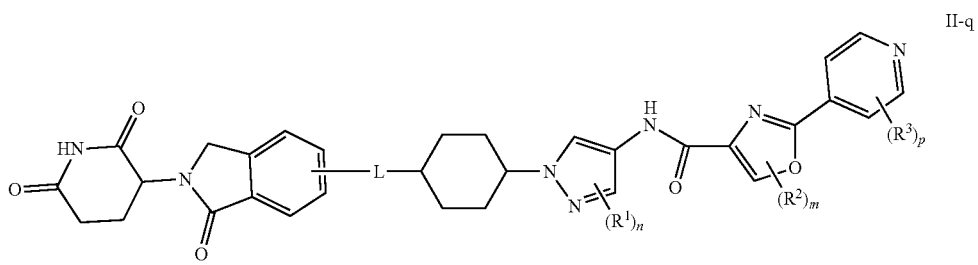

II-q or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-d, wherein LBM is

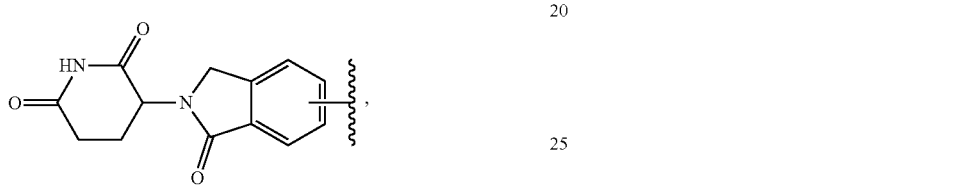

thereby forming a compound of formula II-d-6:

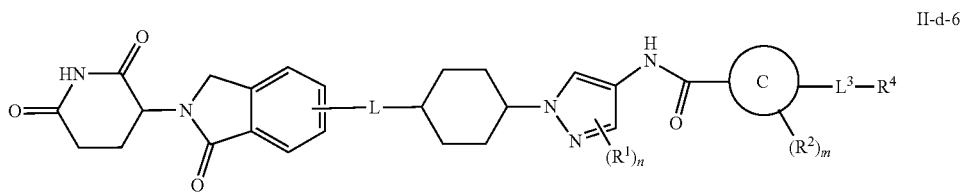

II-d-6 or a pharmaceutically acceptable salt thereof, wherein each of L, $L^3$, Ring C, $R^1$, $R^2$, $R^4$, n, and m is as defined above and described in embodiments herein, both singly and in combination.

In certain embodiments, the present invention provides the compound of formula II-e, wherein LBM is

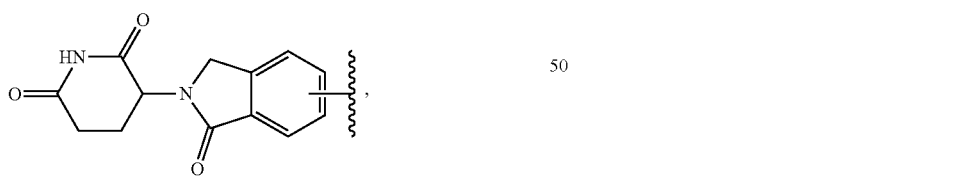

thereby forming a compound of formula II-e-6:

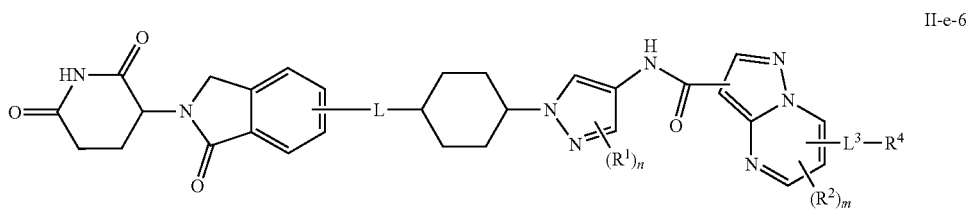

II-e-6 or a pharmaceutically acceptable salt thereof, wherein each of L, R¹, R², R³, n, m, and p is as defined above and described in embodiments herein, both singly and in combination.

In certain embodiments, the present invention provides a compound of formula I, wherein LBM is an E3 ubiquitin ligase (cereblon) binding moiety

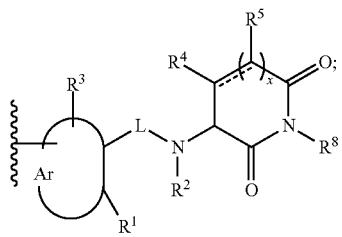

thereby forming a compound of formula I-o:

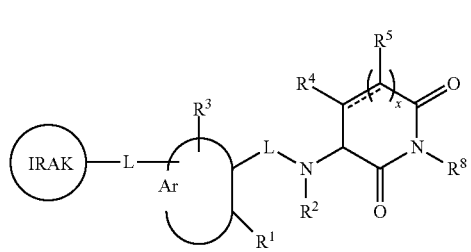

or a pharmaceutically acceptable salt thereof, wherein L and IRAK are as defined above and described in embodiments herein, and wherein each of the variables Ar, R¹, R², R³, R⁴, R⁵, R⁸, L, x, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety

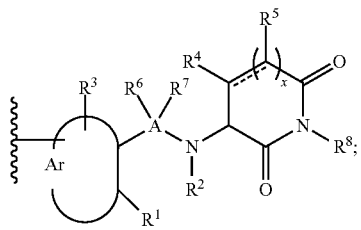

thereby forming a compound of formula I-p:

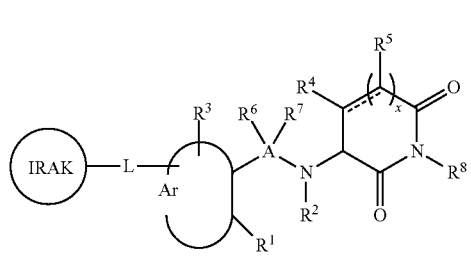

or a pharmaceutically acceptable salt thereof, wherein L and IRAK are as defined above and described in embodiments herein, and wherein each of the variables Ar, R¹, R², R³, R⁴, R⁵, R⁶, R⁷, R⁸, A, x, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety

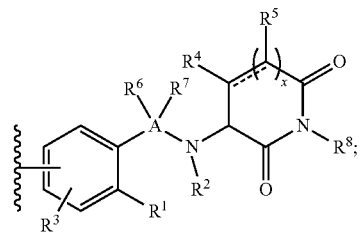

thereby forming a compound of formula I-q:

or a pharmaceutically acceptable salt thereof, wherein L and IRAK are as defined above and described in embodiments herein, and wherein each of the variables R¹, R², R³, R⁴, R⁵, R⁶, R⁷, R⁸, A, x, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety

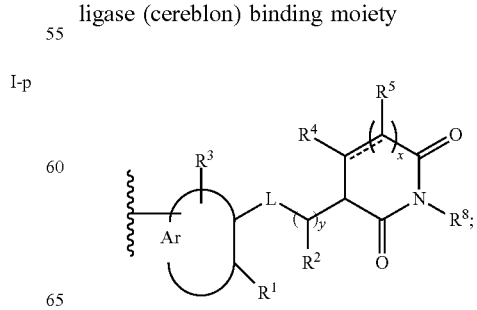

thereby forming a compound of formula I-r:

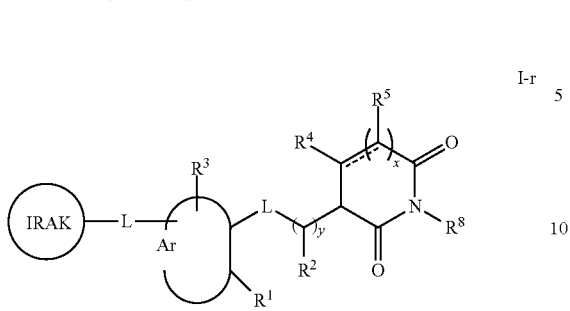

or a pharmaceutically acceptable salt thereof, wherein L and IRAK are as defined above and described in embodiments herein, and wherein each of the variables Ar, $R^1$, $R^2$, $R^3$, $R^4$, $R^5$, $R^8$, L, x, y, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety

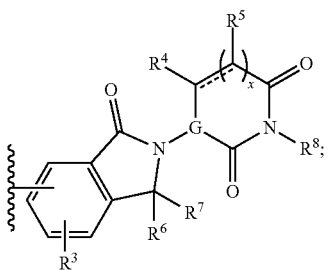

thereby forming a compound of formula I-s:

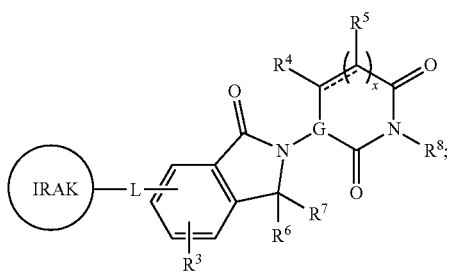

or a pharmaceutically acceptable salt thereof, wherein L and IRAK are as defined above and described in embodiments herein, and wherein each of the variables G, $R^3$, $R^4$, $R^5$, $R^6$, $R^7$, $R^8$, x, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety

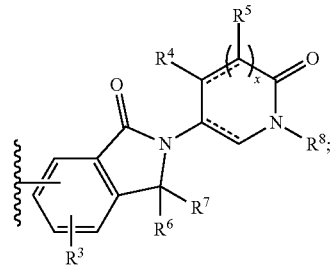

thereby forming a compound of formula I-t:

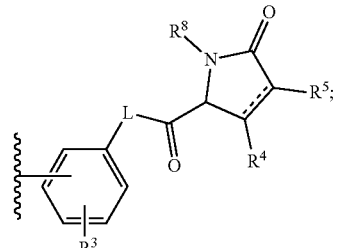

or a pharmaceutically acceptable salt thereof, wherein L and IRAK are as defined above and described in embodiments herein, and wherein each of the variables $R^3$, $R^4$, $R^5$, $R^6$, $R^7$, $R^8$, x, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety thereby forming a compound of formula I-u:

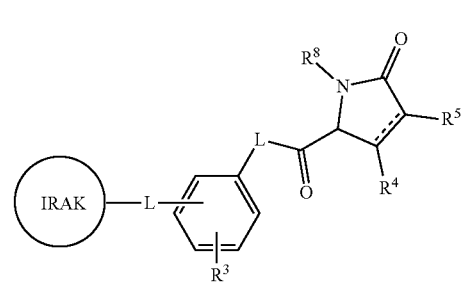

or a pharmaceutically acceptable salt thereof, wherein L and IRAK are as defined above and described in embodiments herein, and wherein each of the variables $R^3$, $R^4$, $R^5$, $R^8$, L, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety

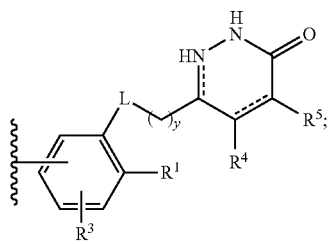

thereby forming a compound of formula I-v:

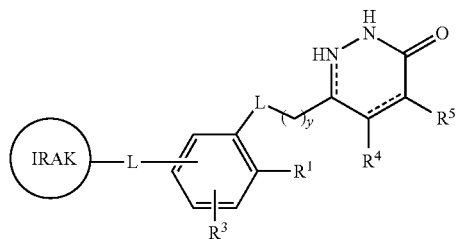

or a pharmaceutically acceptable salt thereof, wherein L and IRAK are as defined above and described in embodiments herein, and wherein each of the variables $R^1$, $R^3$, $R^4$, $R^5$, L, y, and the bond --- is as described and defined in WO 2017/161119, the entirety of each of which is herein incorporated by reference.

In certain embodiments, the present invention provides a compound of formula I, wherein LBM is an E3 ubiquitin ligase (cereblon) binding moiety

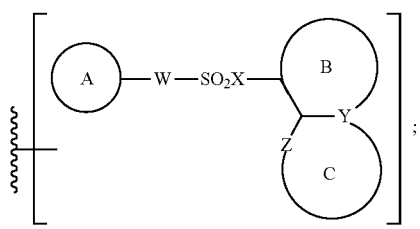

thereby forming a compound of formula I-x:

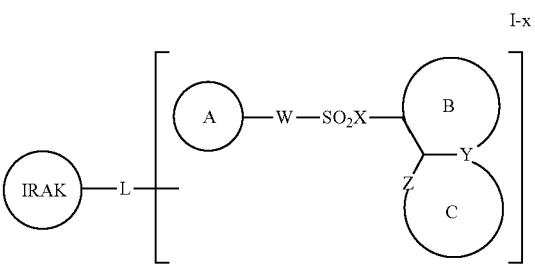

or a pharmaceutically acceptable salt thereof, wherein L and IRAK are as defined above and described in embodiments herein, and wherein each of the variables A, B, C, W, X, Y, and Z is as described and defined in U.S. Pat. No. 5,721,246, the entirety of each of which is herein incorporated by reference.

In certain embodiments, the present invention provides a compound of Formula I, wherein LBM is an E3 ubiquitin ligase (cereblon) binding moiety

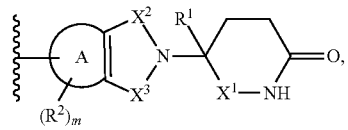

a DCAF15 E3 ubiquitin ligase binding moiety

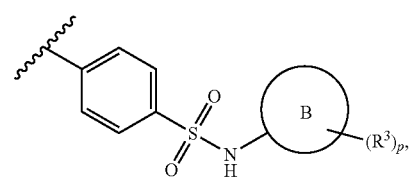

or a VHL E3 ubiquitin ligase binding moiety

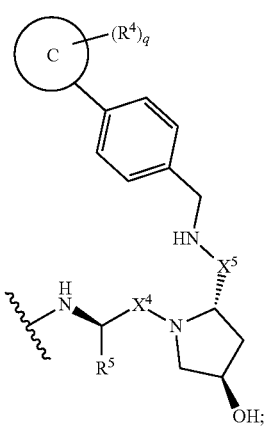

thereby forming a compound of formula I-y-1, I-y-2, or I-y-3:

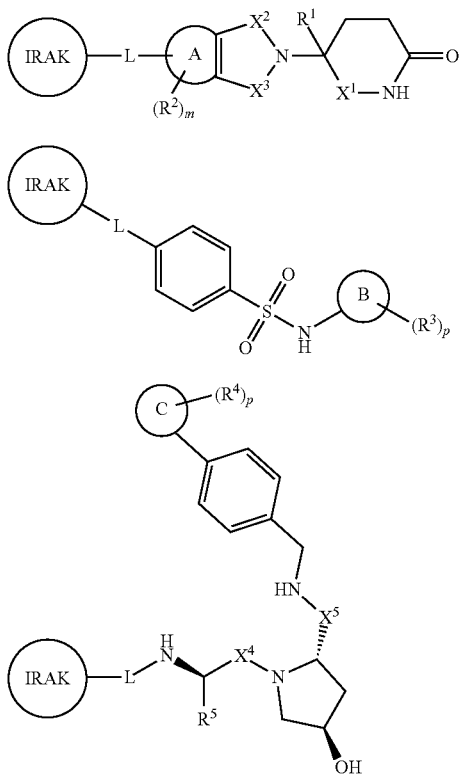

I-y-1

I-y-2

I-y-3 or a pharmaceutically acceptable salt thereof, wherein IRAK is as defined above and described in embodiments herein, and wherein:

each of $X^1$, $X^2$, and $X^3$ is independently a bivalent moiety selected from a covalent bond, —CH$_2$—, —C(O)—, —C(S)—, or

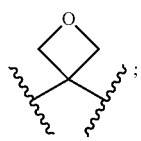 [SMILES: *C1(*)COC1];

each of $X^4$ and $X^5$ is independently a bivalent moiety selected from —CH$_2$—, —C(O)—, —C(S)—, or

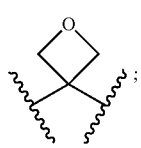 [SMILES: *C1(*)COC1];

$R^1$ is hydrogen, deuterium, halogen, —CN, —OR, —SR, —S(O)R, —S(O)$_2$R, —NR$_2$, or an optionally substituted C$_{1-4}$ aliphatic;

each of $R^2$, $R^3$, and $R^4$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen or C$_{1-6}$ aliphatic;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring B is selected from 6-membered aryl containing 0-2 nitrogen atoms or a 8-10 membered bicyclic heteroaryl having 1-5 heteroatoms independently selected from nitrogen, oxygen, or sulfur;

Ring C is a selected from 6-membered aryl containing 0-2 nitrogen atoms or a 5-membered heteroaryl with 1-3 heteroatoms independently selected from nitrogen, oxygen or sulfur;

L is a covalent bond or a bivalent, saturated or unsaturated, straight or branched C$_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

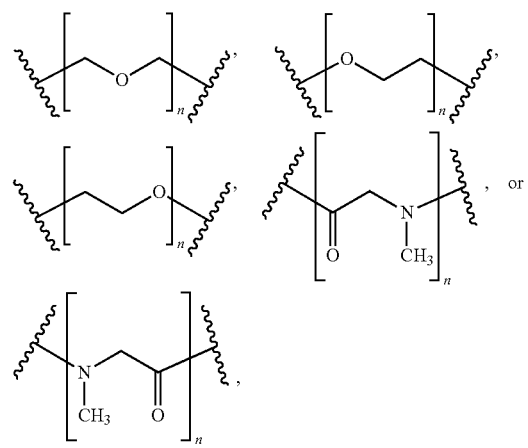

wherein:

each -Cy- is independently an optionally substituted bivalent ring selected from phenylenyl, an 8-10 membered bicyclic arylenyl, a 4-7 membered saturated or partially unsaturated carbocyclylenyl, a 4-7 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-7 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur;

m is 0, 1, 2, 3 or 4;
each of n is independently 1, 2, 3, 4, 5, 6, 7, 8, 9, or 10;
p is 0, 1, 2, 3 or 4;
q is 0, 1, 2, 3 or 4; and
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

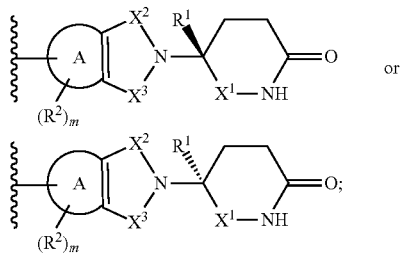

thereby forming a compound of formula I-y'-1 or I-y"-1:

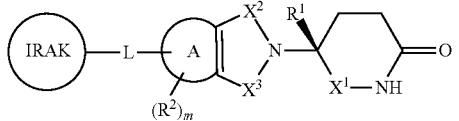

I-y'-1

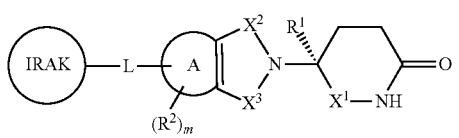

I-y"-1 wherein IRAK, L, Ring A, $X^1$, $X^2$, $X^3$, $R^1$, $R^2$ and m are as defined above.

In certain embodiments, the present invention provides a compound of formula I, wherein LBM is an E3 ubiquitin ligase (cereblon) binding moiety

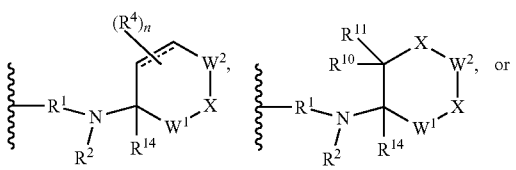

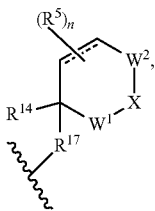

thereby forming a compound of formula I-z-1, I-z-2, or I-z-3 respectively:

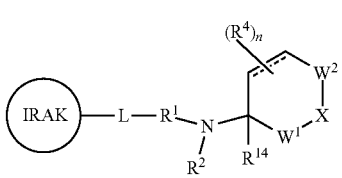

I-z-1

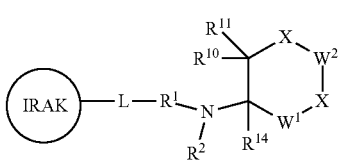

I-z-2

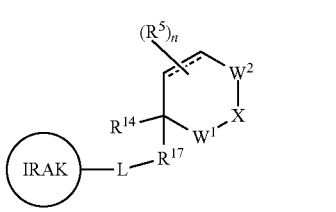

I-z-3 or a pharmaceutically acceptable salt thereof, wherein L and IRAK are as defined above and described herein, and wherein each of the variables $R^1$, $R^2$, $R^4$, $R^5$, $R^{10}$, $R^{11}$, $R^{14}$, $R^{17}$, $W^1$, $W^2$, X and n is as defined in WO 2017/197051, the entirety of each of which is herein incorporated by reference, and wherein

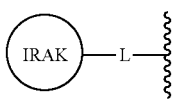

is attached to $R^1$, the ring formed by combining $R^1$ and $R^2$, or $R^{17}$ at the site of attachment of $R^{12}$ as defined in WO 2017/197051 such that

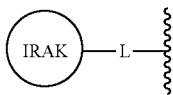

takes the place of the $R^{12}$ substituent.

In certain embodiments, the present invention provides a compound of formula I, wherein LBM is an E3 ubiquitin ligase (cereblon) binding moiety

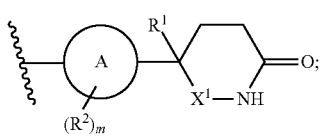

thereby forming a compound of formula I-aa:

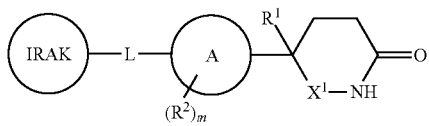

I-aa or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

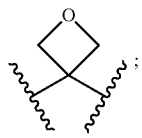 [SMILES: *C1(*)COC1]

$R^1$ is hydrogen, deuterium, halogen, —CN, —OR, —SR, —S(O)R, —S(O)$_2$R, —NR$_2$, or an optionally substituted $C_{1-4}$ aliphatic;

each $R^2$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

Ring A is a bi- or tricyclic ring selected from

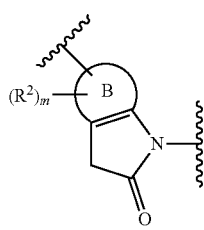

wherein Ring B is other than imidazo or benzo, wherein Ring B is other than benzo,

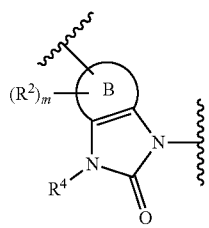

wherein Ring B is other than benzo,

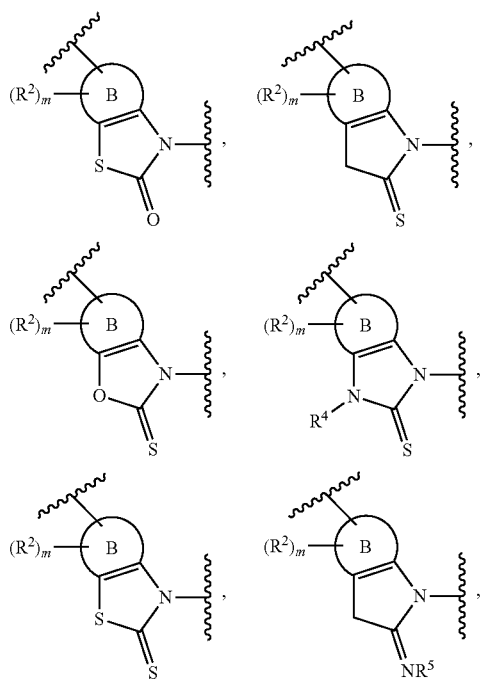

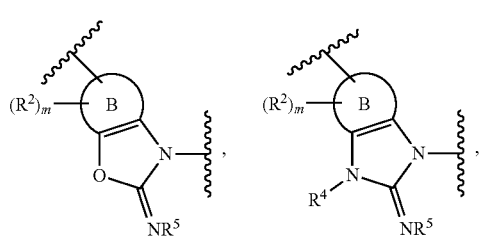

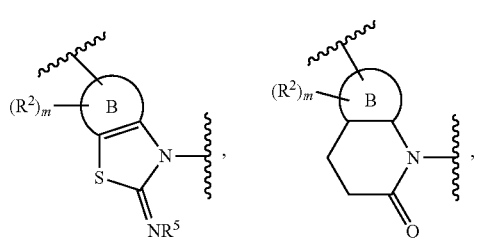

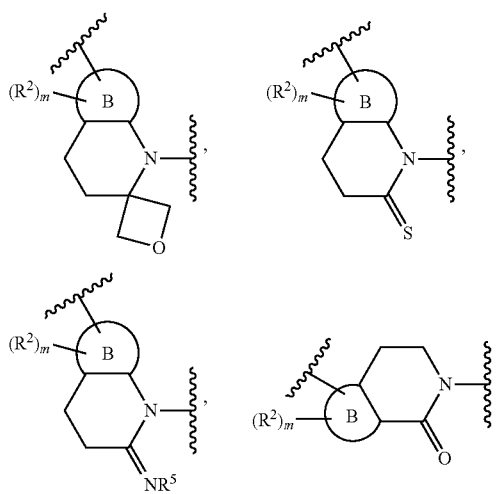
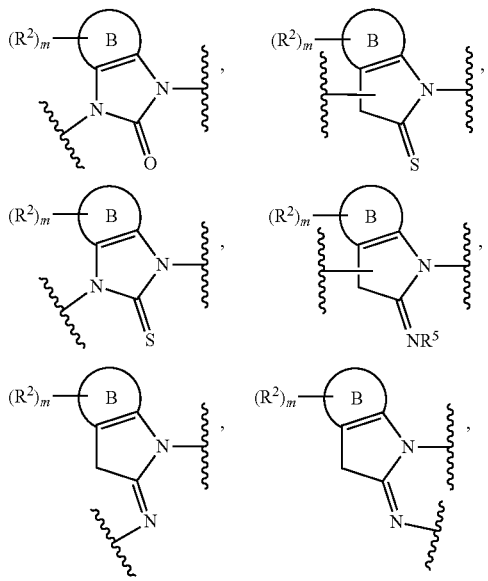
wherein Ring B is other than benzo,
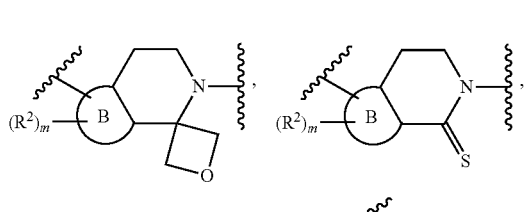
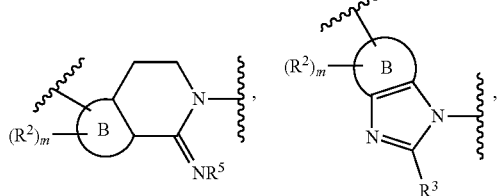
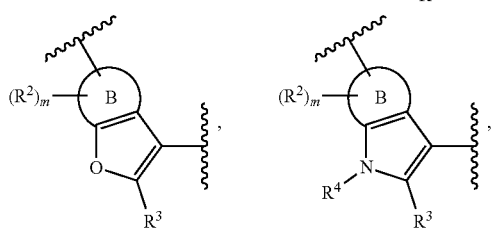
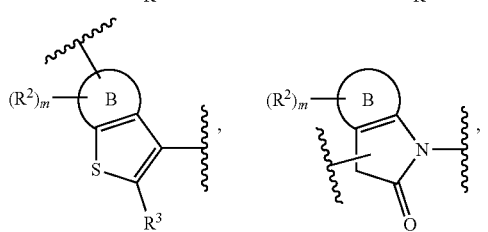
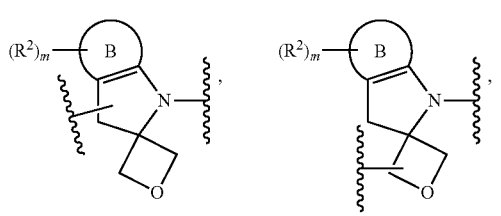
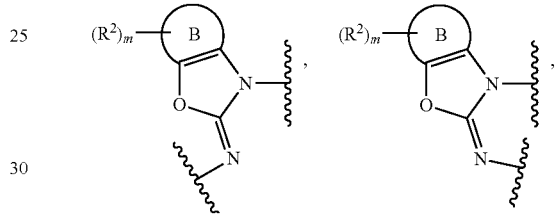
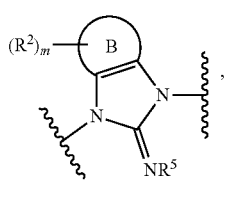 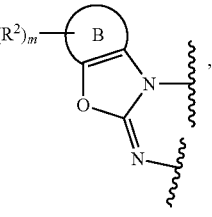
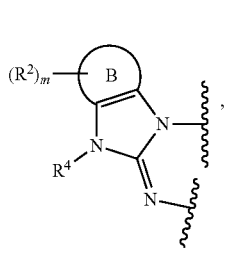 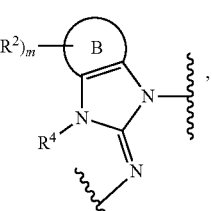
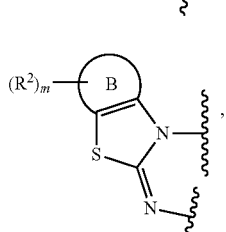 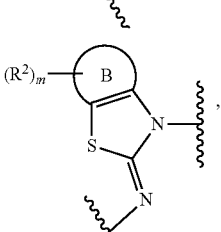
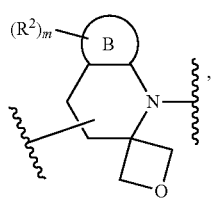 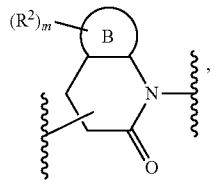
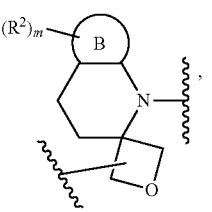

-continued

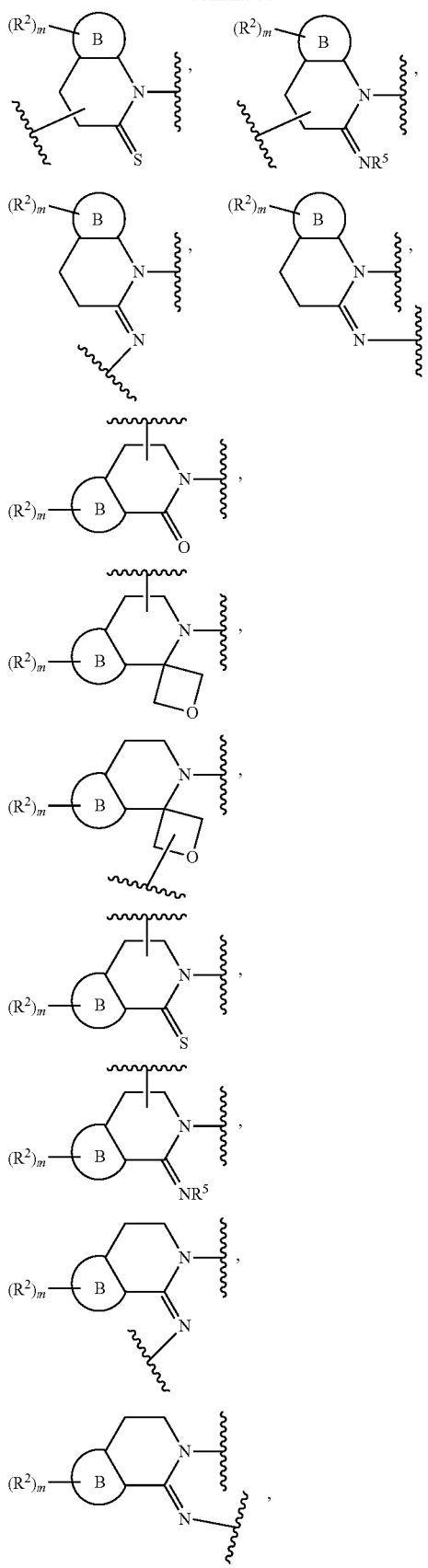

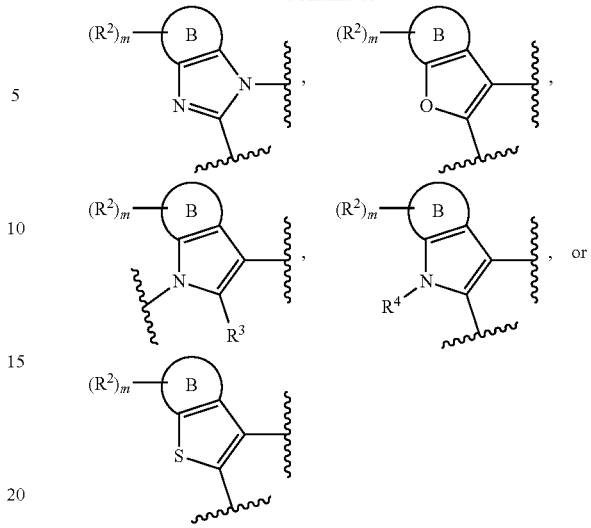

wherein

Ring B is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

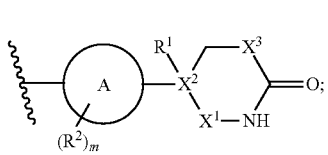

thereby forming a compound of formula I-aa':

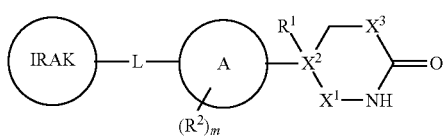

I-aa' or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

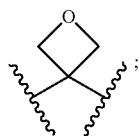 [SMILES: *C1(*)COC1]

;

$X^2$ is a carbon atom or silicon atom;
$X^3$ is a bivalent moiety selected from —CH$_2$— or —Si(R$^2$)—;
$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;
each $R^2$ is independently hydrogen, deuterium, —R$^6$, halogen, —CN, —NO$_2$, —OR, —SR, —NR$_2$, —Si(R)$_3$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;
Ring A is a bi- or tricyclic ring selected from

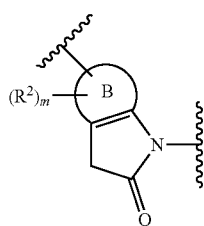

wherein Ring B is other than imidazo or benzo,

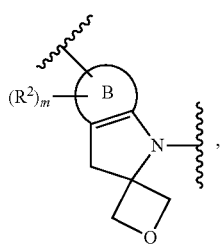 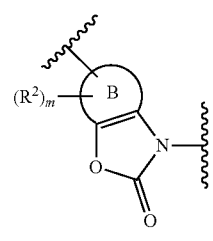

wherein Ring B is other than benzo,

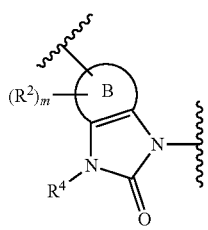

wherein Ring B is other than benzo,

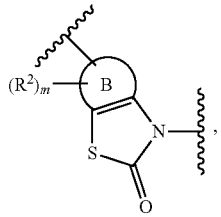 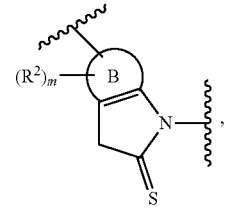

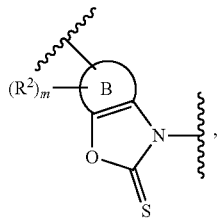

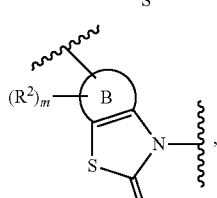

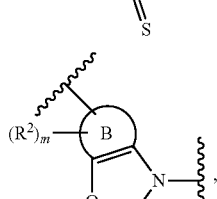

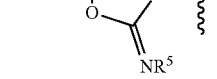

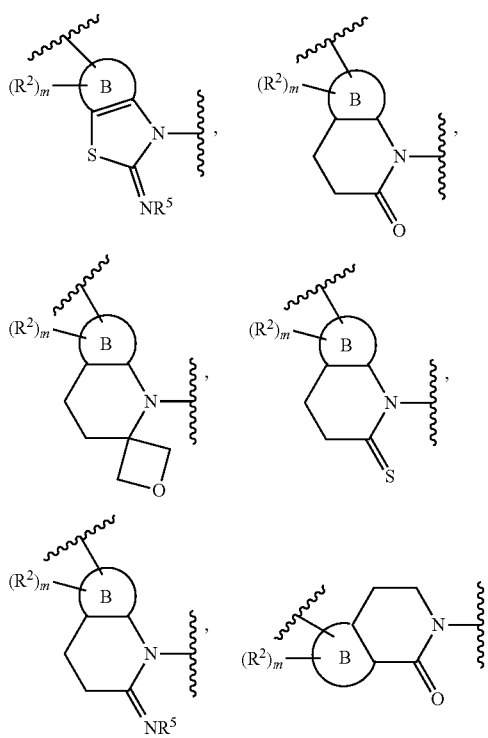
wherein Ring B is other than benzo,
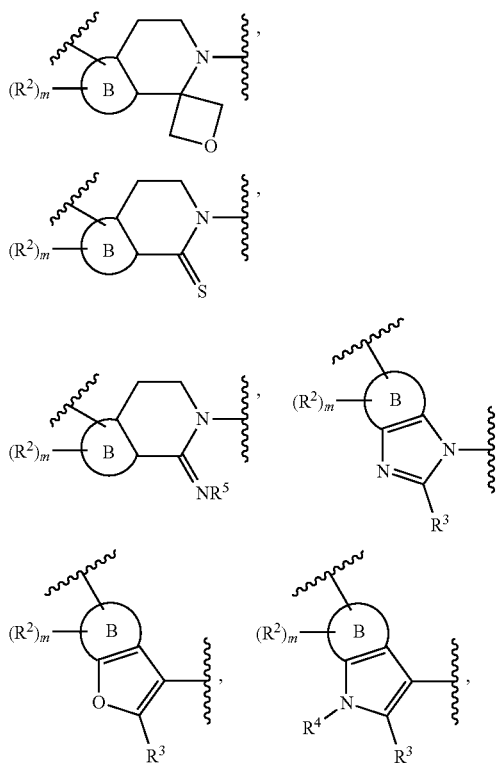
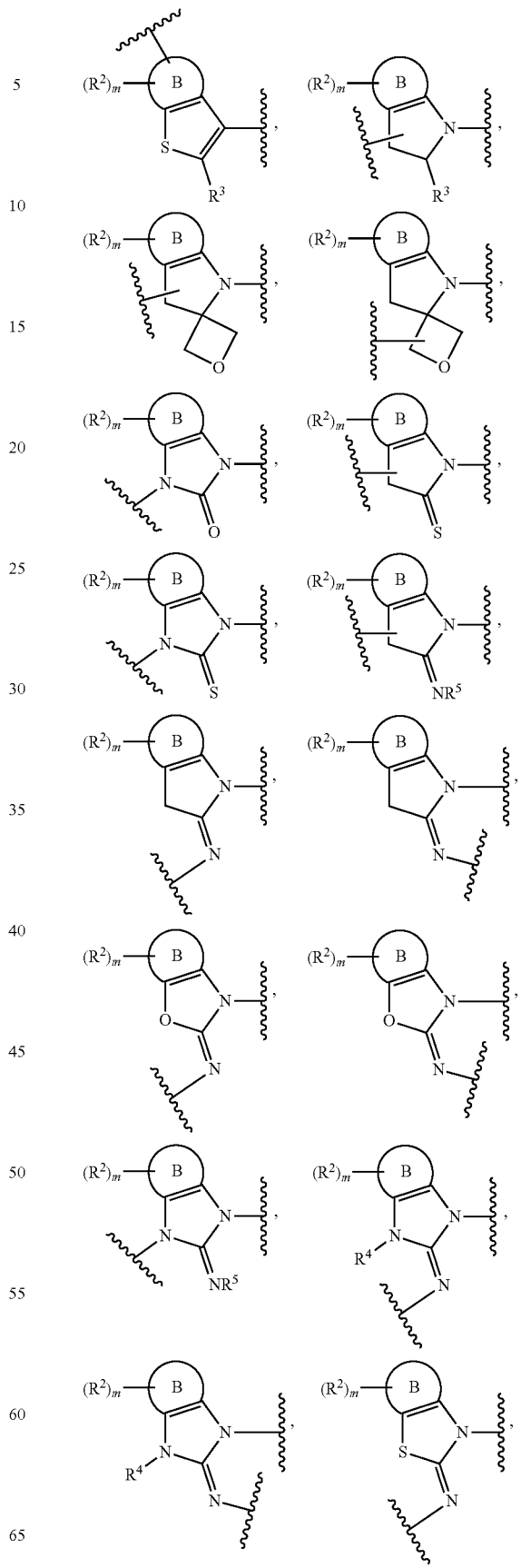

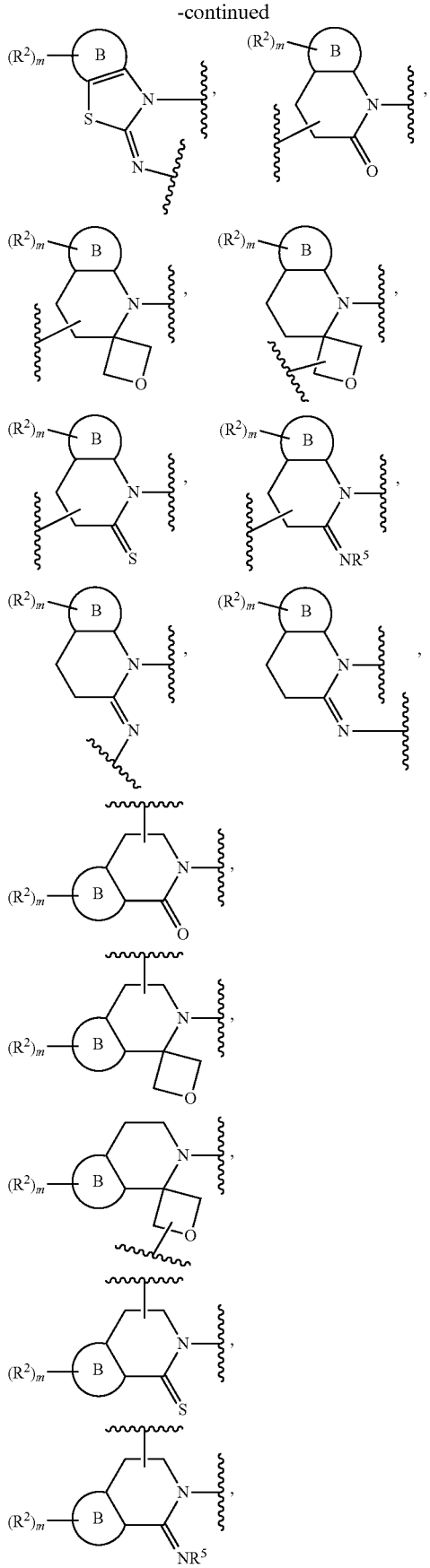

wherein
Ring B is a fused ring selected from 6-membered aryl containing 0-2 nitrogen atoms, 5 to 7-membered partially saturated carbocyclyl, 5 to 7-membered partially saturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur;

$R^3$ is selected from hydrogen, halogen, —OR, —N(R)$_2$, or —SR;

each $R^4$ is independently hydrogen, —$R^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen, C-4 aliphatic, or —CN;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, 2, 3 or 4; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-aa' above is provided as a compound of formula I-aa" or formula I-aa''':

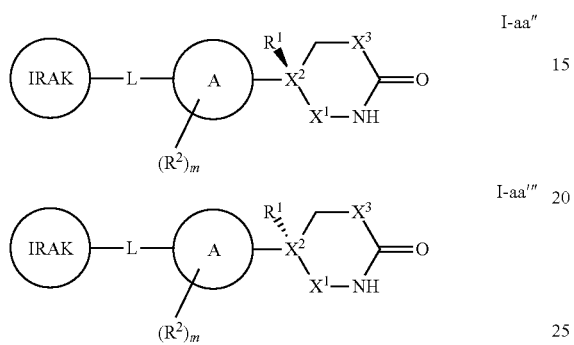

or a pharmaceutically acceptable salt thereof, wherein:
each of IRAK, Ring A, L, $R^1$, $R^2$, $X^1$, $X^2$, $X^3$, and m is as defined above.

In certain embodiments, the present invention provides a compound of formula I, wherein LBM is an E3 ubiquitin ligase (cereblon) binding moiety

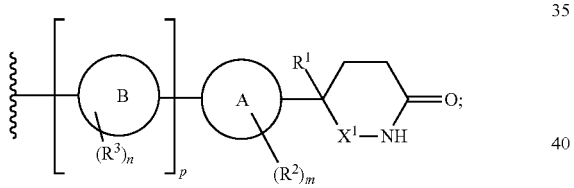

thereby forming a compound of formula I-bb:

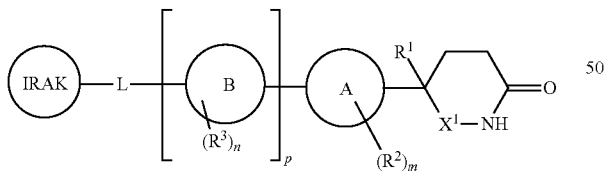

or a pharmaceutically acceptable salt thereof, wherein L and IRAK are as defined above and described in embodiments herein, and wherein:

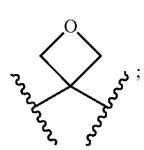

$X^1$ is a bivalent moiety selected from a covalent bond, —$CH_2$—, —C(O)—, —C(S)—, or $R^1$ is hydrogen, deuterium, halogen, —CN, —OR, —SR, —S(O)R, —S(O)$_2$R, —NR$_2$, or an optionally substituted $C_{1-4}$ aliphatic;

Ring A is a mono- or bicyclic ring selected from

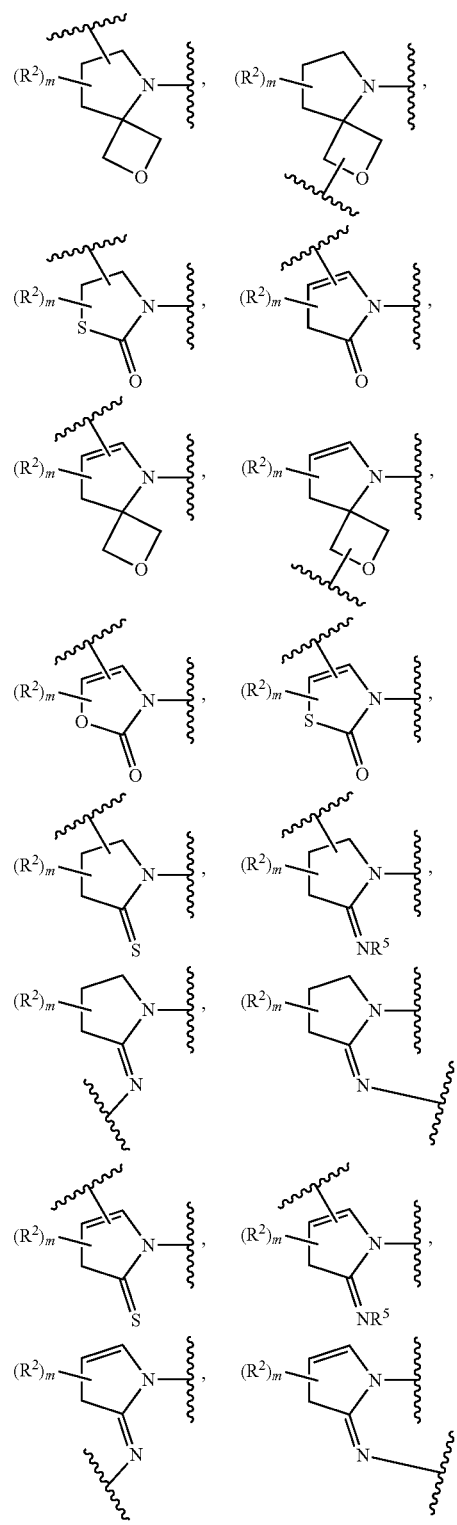

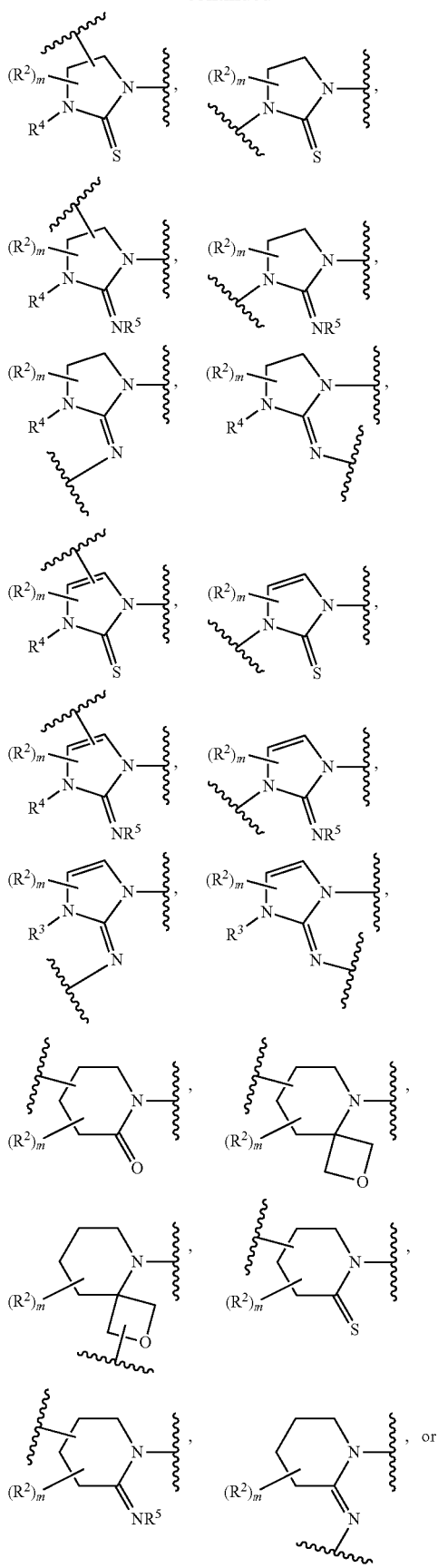

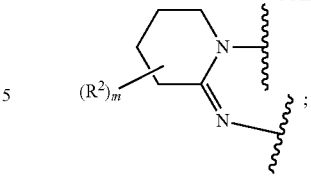

each $R^2$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

Ring B is selected from a 6-membered aryl containing 0-2 nitrogen atoms or a 5-membered heteroaryl with 1-3 heteroatoms independently selected from nitrogen, oxygen or sulfur;

each of $R^3$ and $R^4$ is independently hydrogen, —$R^6$, halogen, —CN, —$NO_2$, —OR, —SR, —$NR_2$, —$S(O)_2R$, —$S(O)_2NR_2$, —S(O)R, —C(O)R, —C(O)OR, —$C(O)NR_2$, —C(O)N(R)OR, —OC(O)R, —$OC(O)NR_2$, —N(R)C(O)OR, —N(R)C(O)R, —$N(R)C(O)NR_2$, or —$N(R)S(O)_2R$;

$R^5$ is hydrogen, $C_{1-4}$ aliphatic, or —CN;

each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1, wherein when p is 0, the bond connecting Ring A and Ring B is connected to

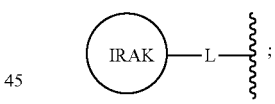

and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

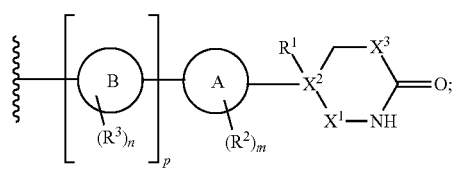

thereby forming a compound of formula I-bb':

I-bb'

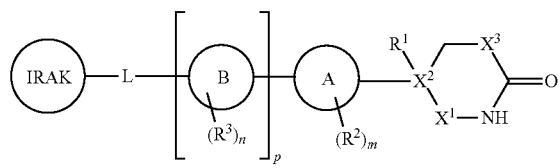

or a pharmaceutically acceptable salt thereof, wherein L and IRAK are as defined above and described in embodiments herein, and wherein:

$X^1$ is a bivalent moiety selected from a covalent bond, —CH$_2$—, —C(O)—, —C(S)—, or

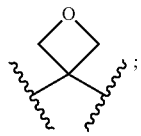 [SMILES: *C1(*)COC1]

$X^2$ is a carbon atom or silicon atom;

$X^3$ is a bivalent moiety selected from —CH$_2$— or —Si(R$^2$)—;

$R^1$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

Ring A is a mono- or bicyclic ring selected from

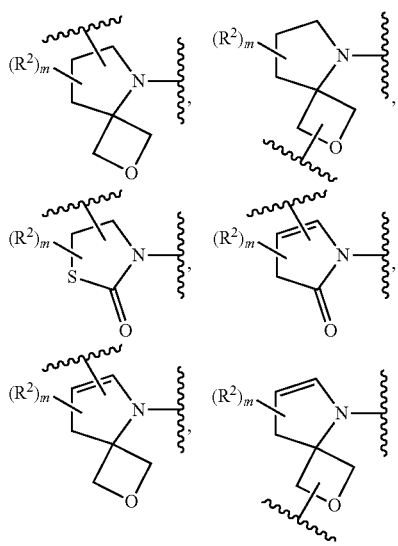

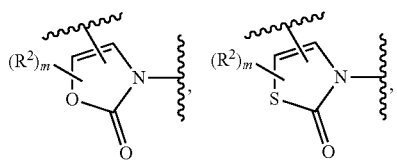

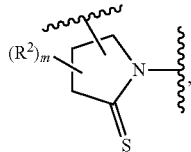

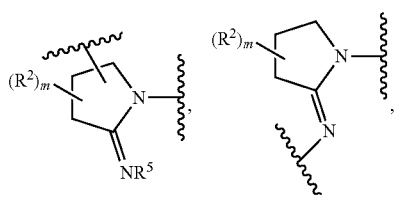

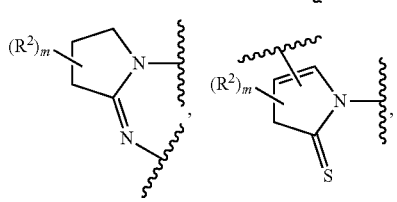

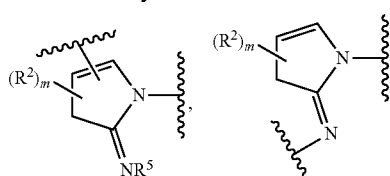

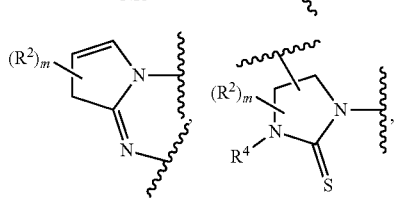

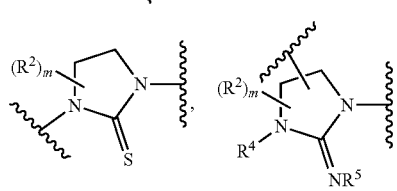

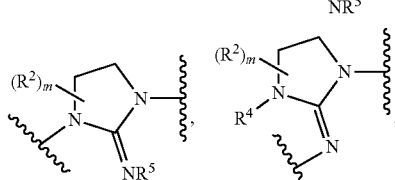

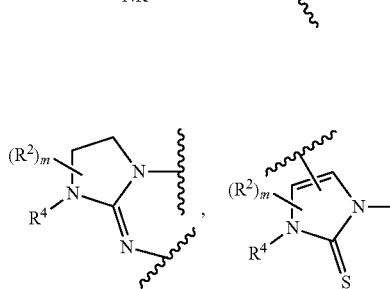

-continued

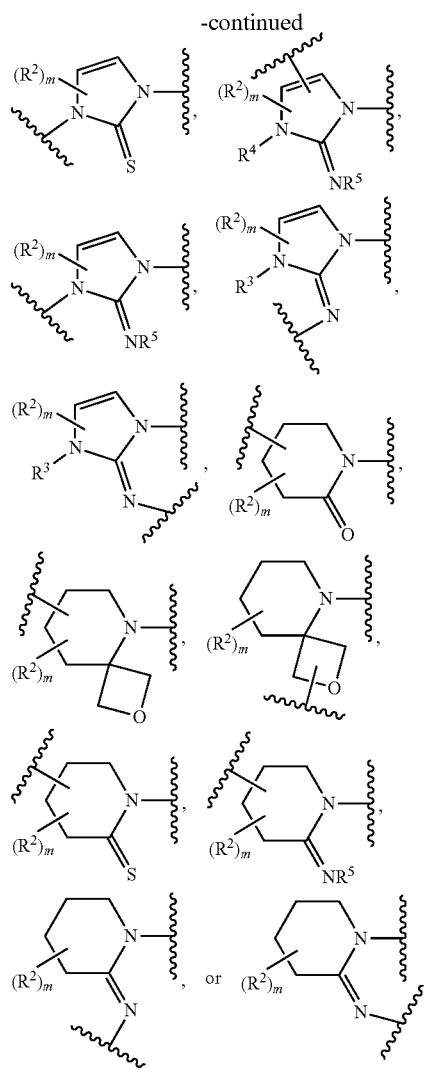

each R² is independently hydrogen, deuterium, —R⁶, halogen, —CN, —NO₂, —OR, —SR, —NR₂, —Si(R)₃, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;
n is 0, 1, 2, 3, or 4;
p is 0 or 1, wherein when p is 0, the bond connecting Ring A and Ring B is connected to

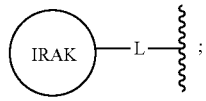

and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, the compound of formula I-bb' above is provided as a compound of formula I-bb" or formula I-bb''':

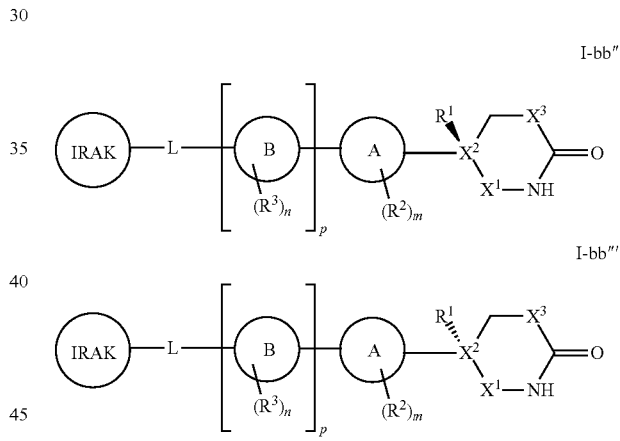

or a pharmaceutically acceptable salt thereof, wherein:
each of IRAK, Ring A, Ring B, L, R¹, R², R³, X¹, X², X³, p, and m is as defined above.

In certain embodiments, the present invention provides a compound of formula I, wherein LBM is an E3 ubiquitin ligase (cereblon) binding moiety

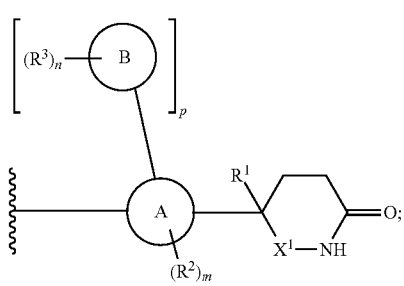

thereby forming a compound of formula I-cc:

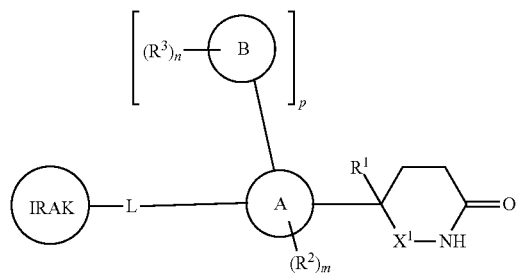

I-cc or a pharmaceutically acceptable salt thereof, wherein L and IRAK are as defined above and described in embodiments herein, and wherein:

$X^1$ is a bivalent moiety selected from a covalent bond, —$CH_2$—, —C(O)—, —C(S)—, or

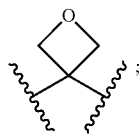 [SMILES: *C1(*)COC1];

$R^1$ is hydrogen, deuterium, halogen, —CN, —OR, —SR, —S(O)R, —S(O)$_2$R, —NR$_2$, or an optionally substituted $C_{1-4}$ aliphatic;

Ring A is a mono- or bicyclic ring selected from

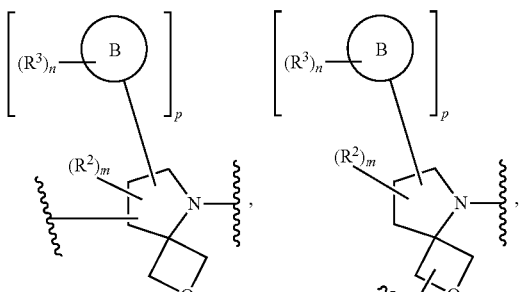

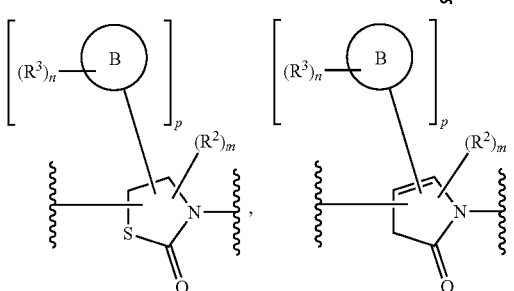

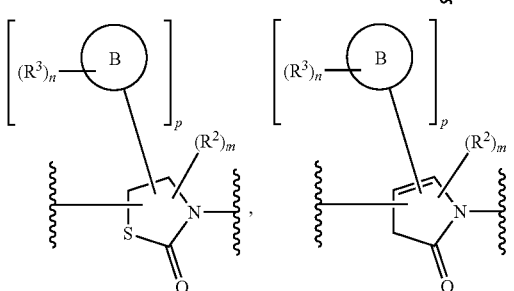

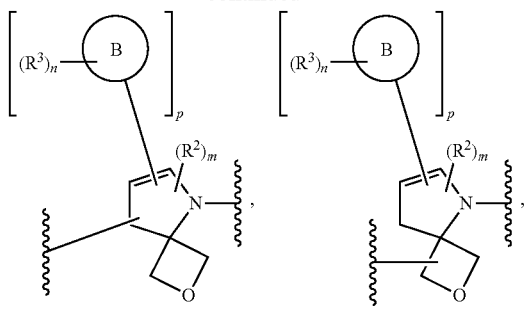

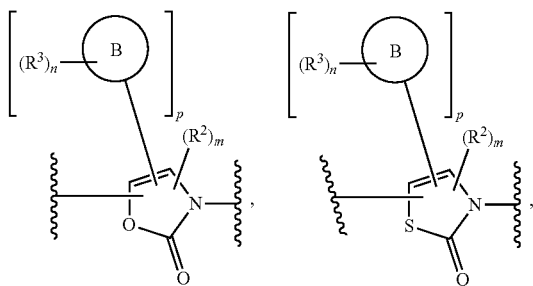

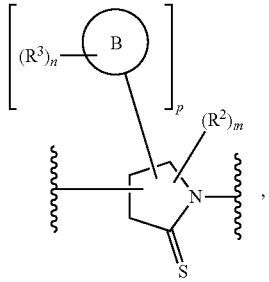

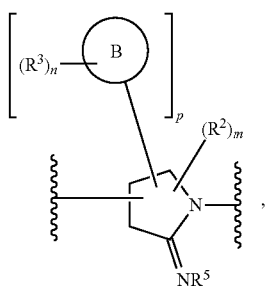

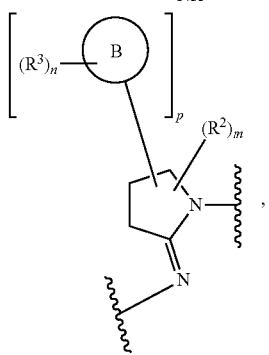

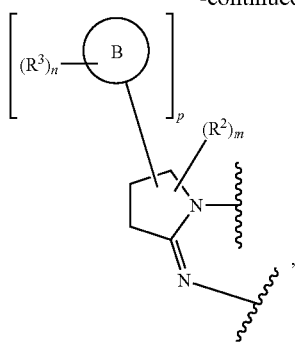,
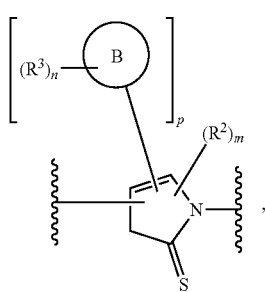,
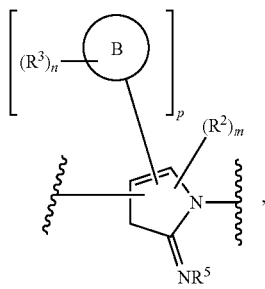,
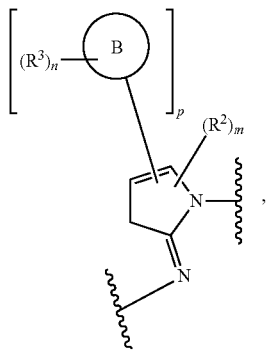,
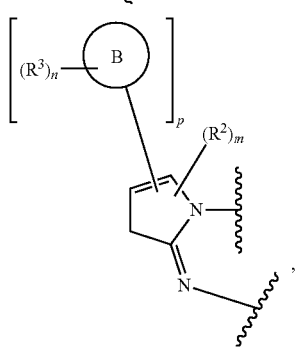,
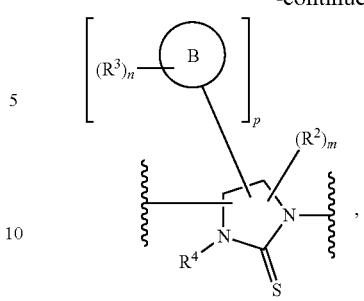,
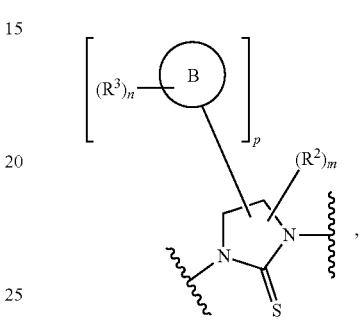,
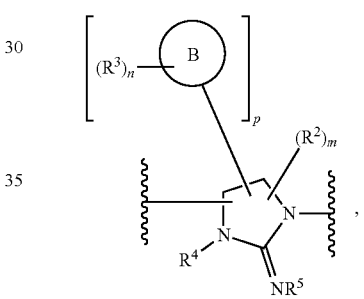,
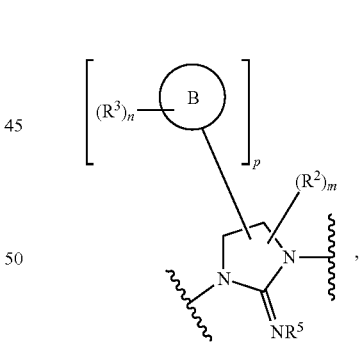,
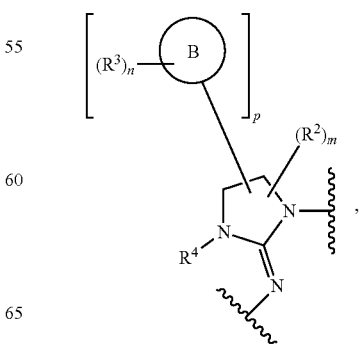,

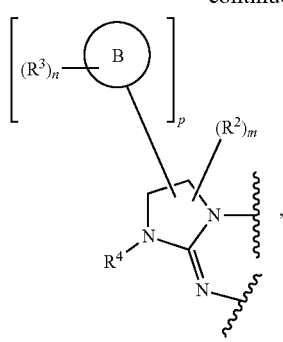,
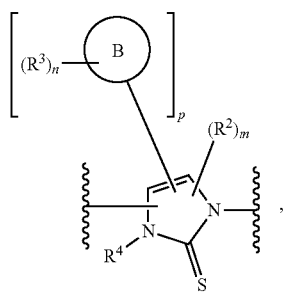,
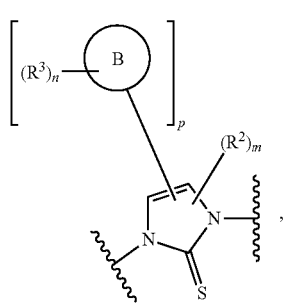,
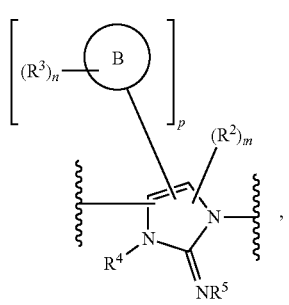,
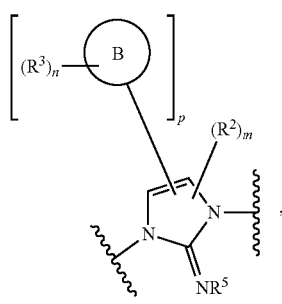,
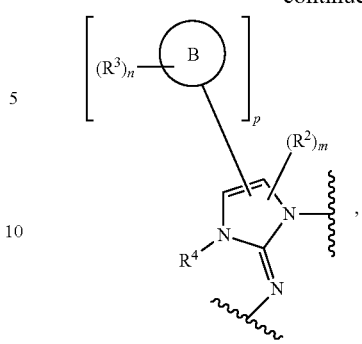,
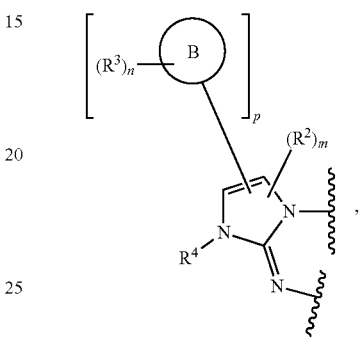,
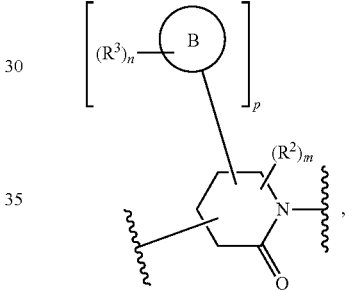,
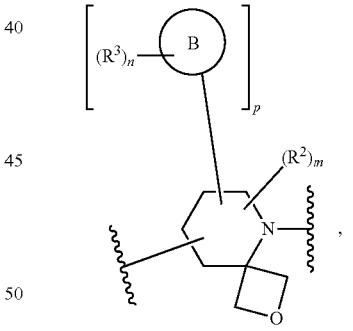,
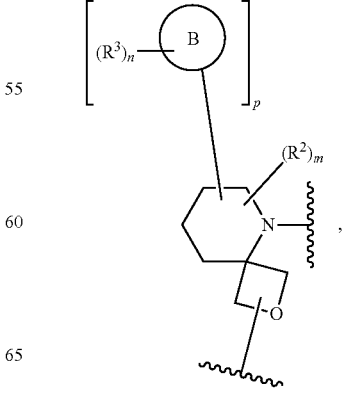,

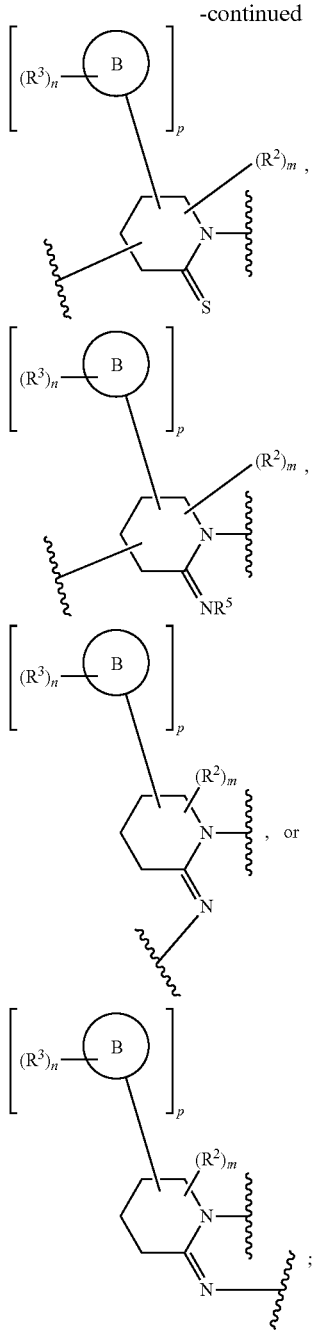

each R² is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, C₁₋₄ aliphatic, or —CN;

each R⁶ is independently an optionally substituted group selected from C₁₋₆ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from C₁₋₆ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In certain embodiments, the present invention provides a compound of formula I, wherein LBM is an E3 ubiquitin ligase (cereblon) binding moiety

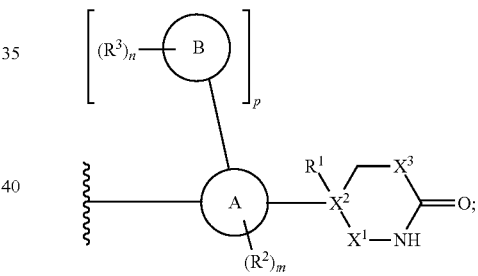

thereby forming a compound of formula I-cc':

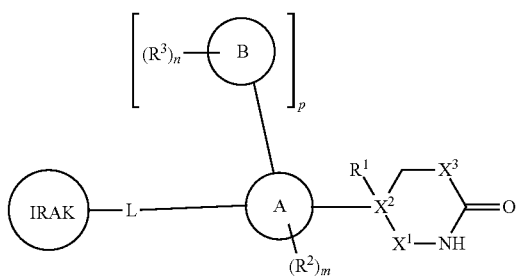

I-cc' or a pharmaceutically acceptable salt thereof, wherein L and IRAK are as defined above and described in embodiments herein, and wherein:

X¹ is a bivalent moiety selected from a covalent bond, —CH₂—, —C(O)—, —C(S)—, or

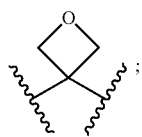
X² is a carbon atom or silicon atom;
X³ is a bivalent moiety selected from —CH₂— or —Si(R²)—;
R¹ is hydrogen, deuterium, halogen, —CN, —OR, —SR, —S(O)R, —S(O)₂R, —N(R)₂, —Si(R)₃, or an optionally substituted $C_{1-4}$ aliphatic;
Ring A is a mono- or bicyclic ring selected from
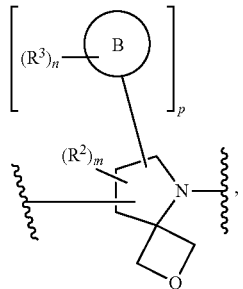 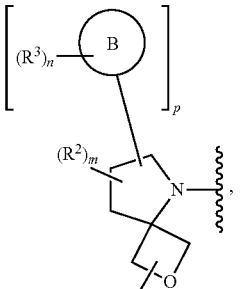
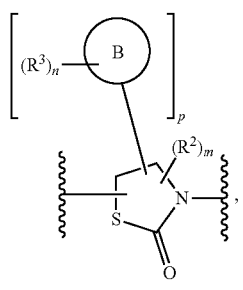 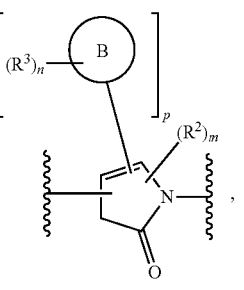
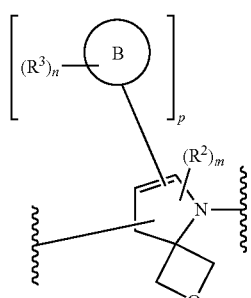 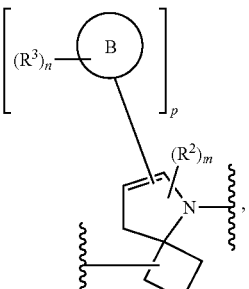
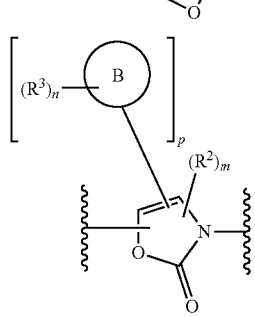 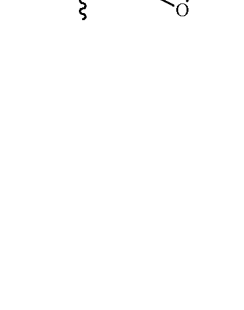
-continued
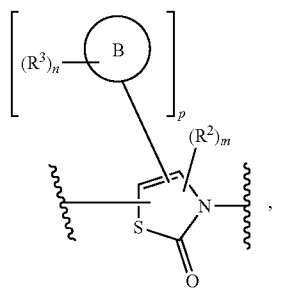
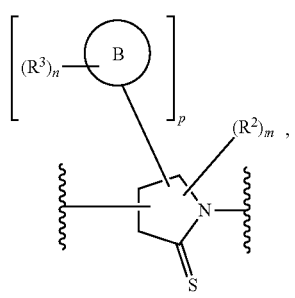
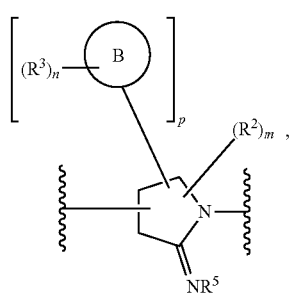
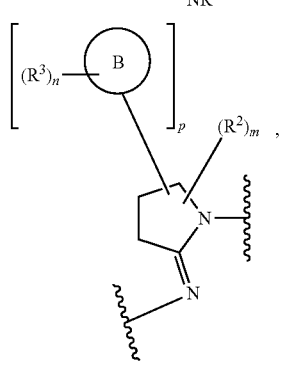
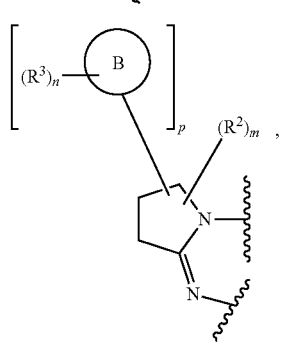

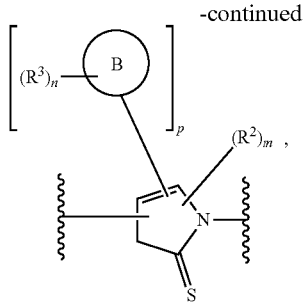
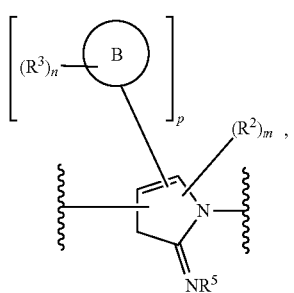
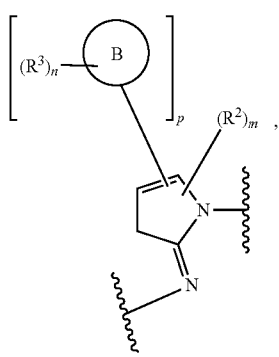
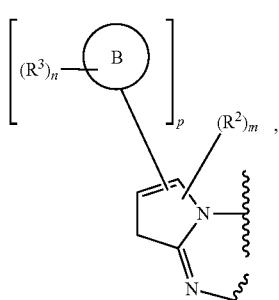
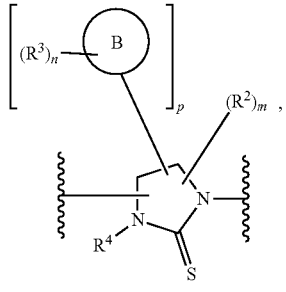
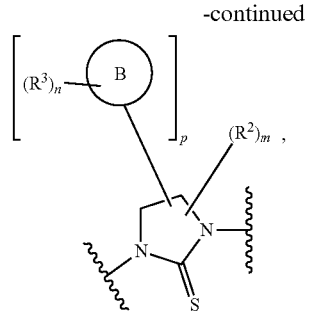
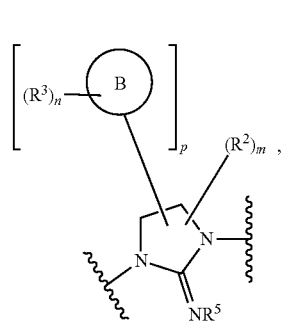
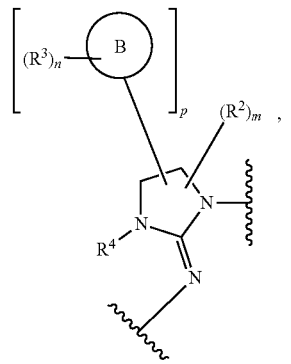
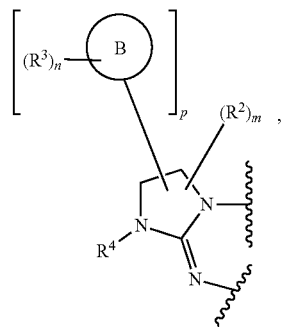

-continued
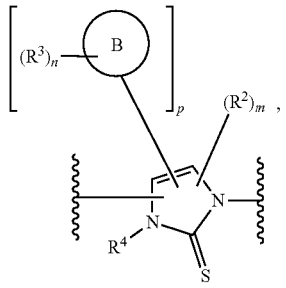
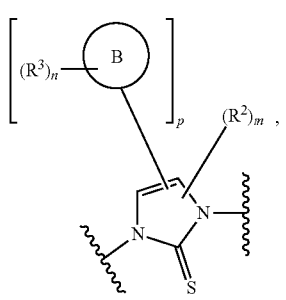
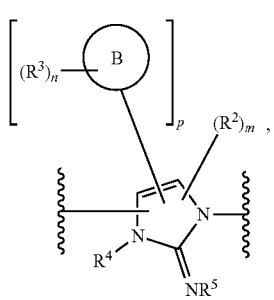
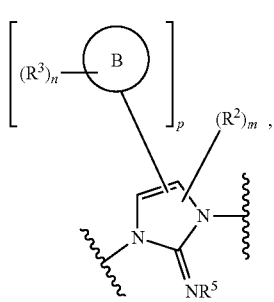
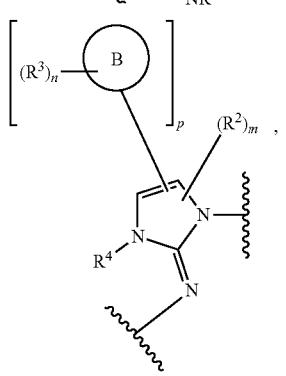
-continued
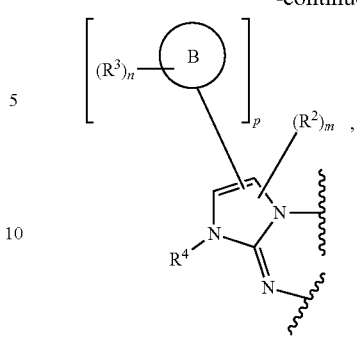
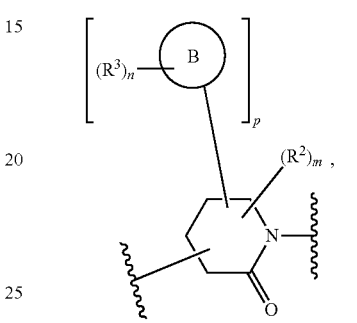
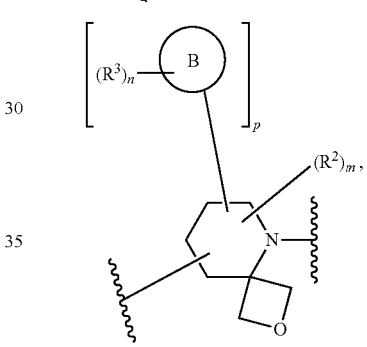
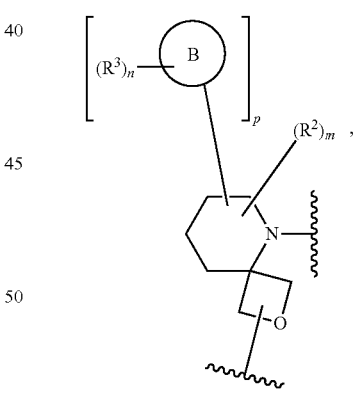
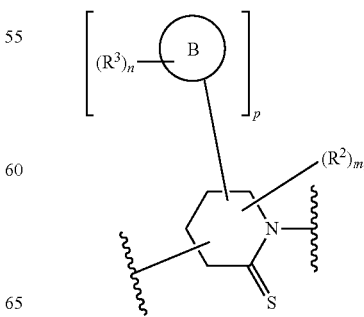

-continued

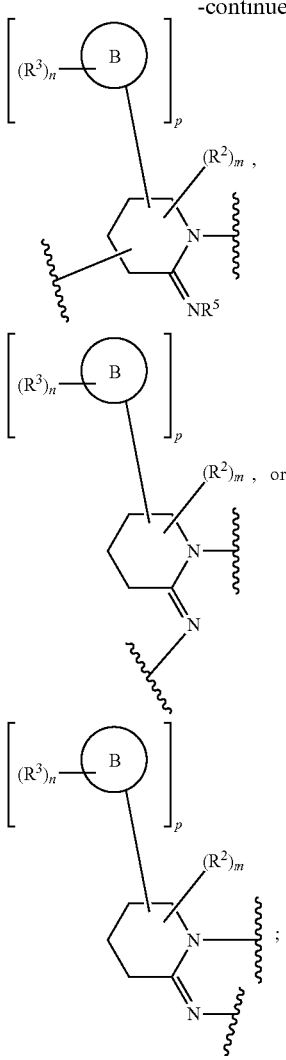

each R² is independently hydrogen, deuterium, —R⁶, halogen, —CN, —NO₂, —OR, —SR, —NR₂, —Si(R)₃, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

Ring B is selected from a 6-membered aryl containing 0-2 nitrogen atoms or a 5-membered heteroaryl with 1-3 heteroatoms independently selected from nitrogen, oxygen or sulfur;

each of R³ and R⁴ is independently hydrogen, —R⁶, halogen, —CN, —NO₂, —OR, —SR, —NR₂, —S(O)₂R, —S(O)₂NR₂, —S(O)R, —C(O)R, —C(O)OR, —C(O)NR₂, —C(O)N(R)OR, —OC(O)R, —OC(O)NR₂, —N(R)C(O)OR, —N(R)C(O)R, —N(R)C(O)NR₂, or —N(R)S(O)₂R;

R⁵ is hydrogen, $C_{1-4}$ aliphatic, or —CN;

each R⁶ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

m is 0, 1, or 2;

n is 0, 1, 2, 3, or 4;

p is 0 or 1; and each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, a compound of formula I-cc' above is provided as a compound of formula I-cc'' or formula I-cc''':

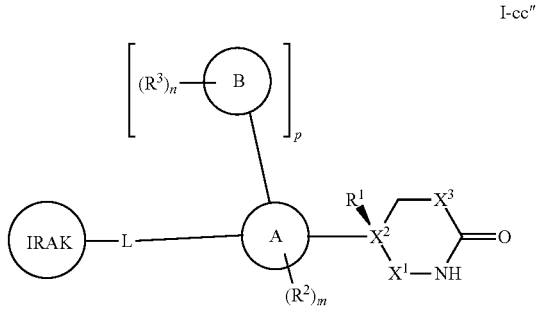

or a pharmaceutically acceptable salt thereof, wherein:

each of IRAK, Ring A, Ring B, L, R¹, R², R³, X¹, X², X³, p, n, and m is as defined above.

As defined above and described herein, LBM is a ligase binding moiety.

In some embodiments, LBM is an E3 ubiquitin ligase (cereblon) binding moiety a DCAF15 E3 ubiquitin ligase binding moiety

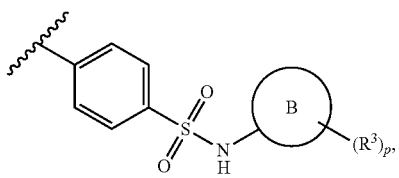

or a VHL E3 ubiquitin ligase binding moiety

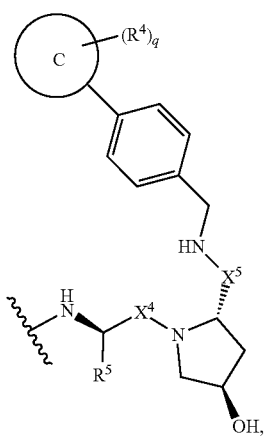

wherein each of $X^1$, $X^2$, and $X^3$ is independently a bivalent moiety selected from a covalent bond, —CH$_2$—, —C(O)—, —C(S)—, or

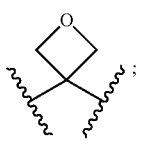 [SMILES: *C1(*)COC1]

each of $X^4$ and $X^5$ is independently a bivalent moiety selected from —CH$_2$—, —C(O)—, —C(S)—, or

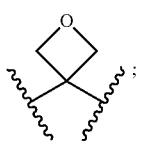 [SMILES: *C1(*)COC1]

$R^1$ is hydrogen, deuterium, halogen, —CN, —OR, —SR, —S(O)R, —S(O)$_2$R, —NR$_2$, or an optionally substituted C$_{1-4}$ aliphatic;

each of $R^2$, $R^3$, and $R^4$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, or —N(R)S(O)$_2$R;

$R^5$ is hydrogen or C$_{1-6}$ aliphatic;

each $R^6$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur;

Ring B is selected from 6-membered aryl containing 0-2 nitrogen atoms or a 8-10 membered bicyclic heteroaryl having 1-5 heteroatoms independently selected from nitrogen, oxygen, or sulfur;

Ring C is a selected from 6-membered aryl containing 0-2 nitrogen atoms or a 5-membered heteroaryl with 1-3 heteroatoms independently selected from nitrogen, oxygen or sulfur;

m is 0, 1, 2, 3 or 4;

each of n is independently 1, 2, 3, 4, 5, 6, 7, 8, 9, or 10;

p is 0, 1, 2, 3 or 4;

q is 0, 1, 2, 3 or 4; and each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, LBM is selected from those depicted in Table 1, below.

As defined above and described herein, each of $X^1$, $X^2$, and $X^3$ is independently a bivalent moiety selected from a covalent bond, —CH$_2$—, —C(O)—, —C(S)—, or

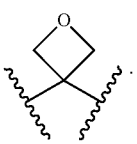 [SMILES: *C1(*)COC1]

In some embodiments, $X^1$ is a covalent bond, —CH$_2$—, —C(O)—, —C(S)—, or

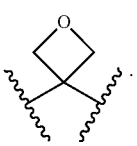 [SMILES: *C1(*)COC1]

In some embodiments, $X^1$ is selected from those depicted in Table 1, below.

In some embodiments, $X^2$ is a covalent bond, —CH$_2$—, —C(O)—, —C(S)—, or

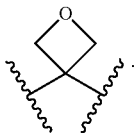 [SMILES: *C1(*)COC1]

In some embodiments, $X^2$ is selected from those depicted in Table 1, below.

In some embodiments, $X^3$ is a covalent bond, —CH$_2$—, —C(O)—, —C(S)—, or

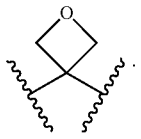 [SMILES: *C1(*)COC1]

In some embodiments, $X^3$ is selected from those depicted in Table 1, below.

As defined above and described herein, each of $X^4$ and $X^5$ is independently a bivalent moiety selected from —CH$_2$—, —C(O)—, —C(S)—, or

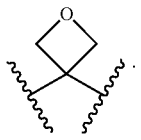 [SMILES: *C1(*)COC1]

In some embodiments, $X^4$ is —CH$_2$—, —C(O)—, —C(S)—, or

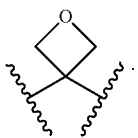

In some embodiments, $X^4$ is selected from those depicted in Table 1, below.

In some embodiments, $X^5$ is —CH$_2$—, —C(O)—, —C(S)—, or

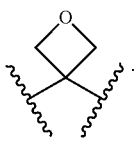

In some embodiments, $X^5$ is selected from those depicted in Table 1, below.

As defined above and described herein, $R^1$ is hydrogen, deuterium, halogen, —CN, —OR, —SR, —S(O)R, —S(O)$_2$R, —NR$_2$, or an optionally substituted $C_{1-4}$ aliphatic.

In some embodiments, $R^1$ is hydrogen, deuterium, halogen, —CN, —OR, —SR, —S(O)R, —S(O)$_2$R, —NR$_2$, or an optionally substituted $C_{1-4}$ aliphatic.

In some embodiments, $R^1$ is selected from those depicted in Table 1, below.

As defined above and described herein, each of $R^2$, $R^3$, and $R^4$ is independently hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R) OR, —OC(O)R, —OC(O)NR$_2$, —N(R)C(O)OR, —N(R)C (O)R, —N(R)C(O)NR$_2$, or —N(R)S(O)$_2$R.

In some embodiments, $R^2$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O) OR, —N(R)C(O)R, —N(R)C(O)NR$_2$, or —N(R)S(O)$_2$R.

In some embodiments, $R^2$ is selected from those depicted in Table 1, below.

In some embodiments, $R^3$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O) OR, —N(R)C(O)R, —N(R)C(O)NR$_2$, or —N(R)S(O)$_2$R.

In some embodiments, $R^3$ is methyl.

In some embodiments, $R^3$ is selected from those depicted in Table 1, below.

In some embodiments, $R^4$ is hydrogen, —R$^6$, halogen, —CN, —NO$_2$, —OR, —SR, —NR$_2$, —S(O)$_2$R, —S(O)$_2$NR$_2$, —S(O)R, —C(O)R, —C(O)OR, —C(O)NR$_2$, —C(O)N(R)OR, —OC(O)R, —OC(O)NR$_2$, —N(R)C(O) OR, —N(R)C(O)R, —N(R)C(O)NR$_2$, or —N(R)S(O)$_2$R.

In some embodiments, $R^4$ is methyl.

In some embodiments, $R^4$ is selected from those depicted in Table 1, below.

As defined above and described herein, $R^5$ is hydrogen or $C_{1-6}$ aliphatic.

In some embodiments, $R^5$ is t-butyl.

In some embodiments, $R^5$ is selected from those depicted in Table 1, below.

As defined above and described herein, each $R^6$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^6$ is an optionally substituted $C_{1-6}$ aliphatic group. In some embodiments, $R^6$ is an optionally substituted phenyl. In some embodiments, $R^6$ is an optionally substituted 4-7 membered saturated or partially unsaturated heterocyclic ring having 1-2 heteroatoms independently selected from nitrogen, oxygen, and sulfur. In some embodiments, $R^6$ is an optionally substituted 5-6 membered heteroaryl ring having 1-4 heteroatoms independently selected from nitrogen, oxygen, and sulfur.

In some embodiments, $R^6$ is selected from those depicted in Table 1, below.

As defined above and described herein, Ring A is a fused ring selected from 6-membered aryl containing 0-2 nitrogen atoms, 5 to 7-membered partially saturated carbocyclyl, 5 to 7-membered partially saturated heterocyclyl with 1-2 heteroatoms independently selected from nitrogen, oxygen or sulfur, or 5-membered heteroaryl with 1-3 heteroatoms independently selected from nitrogen, oxygen or sulfur.

In some embodiments Ring A is a fused 6-membered aryl containing 0-2 nitrogen atoms. In some embodiments Ring A is a fused 5 to 7-membered partially saturated carbocyclyl. In some embodiments Ring A is a fused 5 to 7-membered partially saturated heterocyclyl with 1-2 heteroatoms independently selected from nitrogen, oxygen or sulfur. In some embodiments Ring A is a fused 5-membered heteroaryl with 1-3 heteroatoms independently selected from nitrogen, oxygen or sulfur.

In some embodiments, Ring A is a fused phenyl.

In some embodiments, Ring A is selected from those depicted in Table 1, below.

As defined above and described herein, Ring B is selected from 6-membered aryl containing 0-2 nitrogen atoms or a 8-10 membered bicyclic heteroaryl having 1-5 heteroatoms independently selected from nitrogen, oxygen, or sulfur.

In some embodiments, Ring B is a 6-membered aryl containing 0-2 nitrogen atoms. In some embodiments, Ring B is a 8-10 membered bicyclic heteroaryl having 1-5 heteroatoms independently selected from nitrogen, oxygen, or sulfur.

In some embodiments, Ring B is

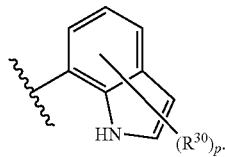

In some embodiments, Ring B is selected from those depicted in Table 1, below.

As defined above and described herein, Ring C is selected from 6-membered aryl containing 0-2 nitrogen atoms or a 5-membered heteroaryl with 1-3 heteroatoms independently selected from nitrogen, oxygen or sulfur.

In some embodiments, Ring C is a 6-membered aryl containing 0-2 nitrogen atoms. In some embodiments, Ring C is a 5-membered heteroaryl with 1-3 heteroatoms independently selected from nitrogen, oxygen or sulfur.

In some embodiments, Ring C is

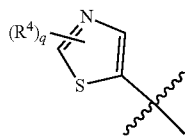

In some embodiments, Ring C is selected from those depicted in Table 1, below.

As defined above and described herein, m is 0, 1, 2, 3 or 4.

In some embodiments, m is 0. In some embodiments, m is 1. In some embodiments, m is 2. In some embodiments, m is 3. In some embodiments, m is 4.

In some embodiments, m is selected from those depicted in Table 1, below.

As defined above and described herein, each of n is independently 1, 2, 3, 4, 5, 6, 7, 8, 9, or 10.

In some embodiments, n is 0. In some embodiments, n is 1. In some embodiments, n is 2. In some embodiments, n is 3. In some embodiments, n is 4. In some embodiments, n is 5. In some embodiments, n is 6. In some embodiments, n is 7. In some embodiments, n is 8. In some embodiments, n is 9. In some embodiments, n is 10.

In some embodiments, n is selected from those depicted in Table 1, below.

As defined above and described herein, p is 0, 1, 2, 3 or 4.

In some embodiments, p is 0. In some embodiments, p is 1. In some embodiments, p is 2. In some embodiments, p is 3. In some embodiments, p is 4.

In some embodiments, p is selected from those depicted in Table 1, below.

As defined above and described herein, q is 0, 1, 2, 3 or 4.

In some embodiments, q is 0. In some embodiments, q is 1. In some embodiments, q is 2. In some embodiments, q is 3. In some embodiments, q is 4.

In some embodiments, q is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is phenyl. In some embodiments, R is a 4-7 membered saturated or partially unsaturated heterocyclic having 1-2 heteroatoms independently selected from nitrogen, oxygen, and sulfur. In some embodiments, R is a 5-6 membered heteroaryl ring having 1-4 heteroatoms independently selected from nitrogen, oxygen, and sulfur. In some embodiments, two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

In some embodiments, LBM is a E3 Ubiquitin ligase (cereblon) binding moiety recited in Varfolomeev, E. et al., *IAP Antagonists Induce Autoubiquitination of c-IAPs, NF-κB activation, and TNFα-Dependent Apoptosis*, Cell, 2007, 131 (4): 669-81, such as, for example:

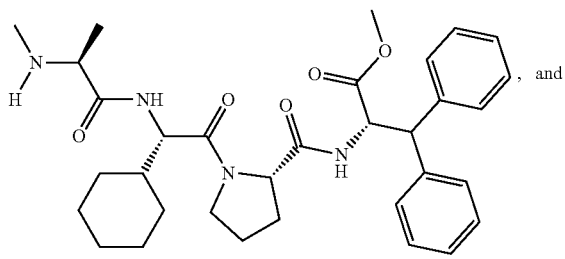, and

MV1

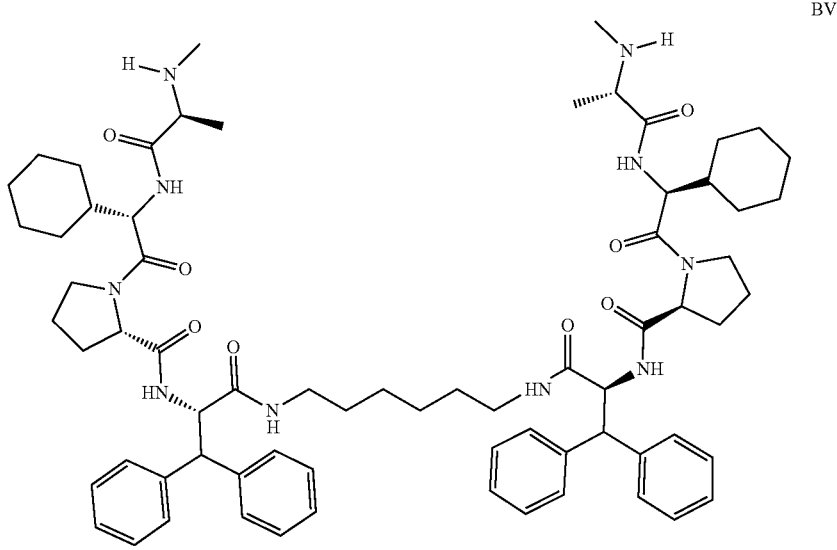

BV6 wherein

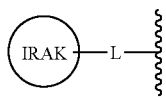

is attached to a modifiable carbon, oxygen, nitrogen or sulfur atom.

In some embodiments, R is selected from those depicted in Table 1, below.

In certain embodiments, the present invention provides a compound of formula I, wherein LBM is an E3 ubiquitin ligase (cereblon) binding moiety thereby forming a compound of formula I-dd:

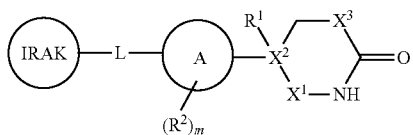

I-dd or a pharmaceutically acceptable salt thereof, wherein:

$X^1$ is a bivalent moiety selected from a covalent bond, —$CH_2$—, —C(O)—, —C(S)—, or

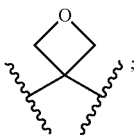;

$X^2$ is a carbon atom or silicon atom;

$X^3$ is a bivalent moiety selected from —$CH_2$— or —Si($R^2$)—;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each R³ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

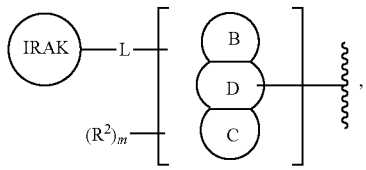

wherein each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16;

wherein L and IRAK are as described in embodiments herein.

In some embodiments, a compound of formula I-dd above is provided as a compound of formula I-dd' or formula I-dd":

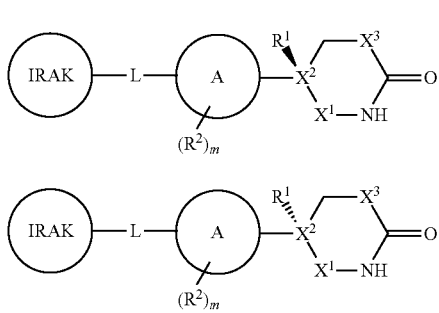

or a pharmaceutically acceptable salt thereof, wherein:

each of IRAK, Ring A, L, R¹, R², X¹, X², X³, and m is as defined above.

In certain embodiments, the present invention provides a compound of formula I, wherein LBM is an E3 ubiquitin ligase (cereblon) binding moiety

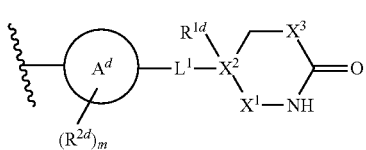

thereby forming a compound of formula I-dd-1:

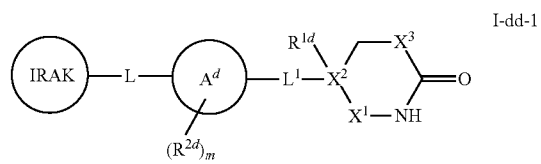

or a pharmaceutically acceptable salt thereof, wherein:

X¹ is a bivalent moiety selected from a covalent bond, —CH$_2$—, —C(O)—, —C(S)—, or

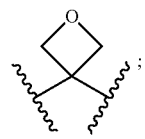 [SMILES: *C1(*)COC1]

X² is a carbon atom or silicon atom;

X³ is a bivalent moiety selected from —CH$_2$— or —Si(R²)—;

R$^{1d}$ is hydrogen, deuterium, halogen, —CN, —OR, —SR, —S(O)R, —S(O)$_2$R, —N(R)$_2$, —Si(R)$_3$, or an optionally substituted C$_{1-4}$ aliphatic;

each R is independently hydrogen, or an optionally substituted group selected from C$_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each R$^{2d}$ is independently hydrogen, —R$^{3d}$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each R$^{3d}$ is independently an optionally substituted group selected from C$_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A$^d$ is a tricyclic ring selected from

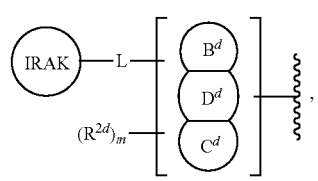

wherein
each of Ring $B^d$, Ring $C^d$, and Ring Dd is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and m is 0, 1, 2, 3, 4, 5, 6, 7, 8, 9, 10, 11, 12, 13, 14, 15, or 16;
wherein L and IRAK are as described in embodiments herein.

In some embodiments, a compound of formula I-dd-1 above is provided as a compound of formula I-dd-1' or formula I-dd-1":

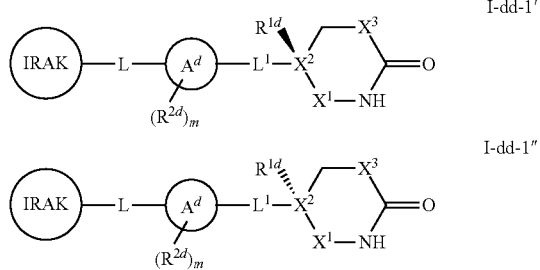

or a pharmaceutically acceptable salt thereof, wherein:
each of IRAK, Ring $A^d$, L, $R^{1d}$, $R^{2d}$, $X^1$, $X^2$, $X^3$, and m is as defined above.

In certain embodiments, the present invention provides a compound of Formula I, wherein LBM is an E3 ubiquitin ligase (cereblon) binding moiety thereby forming a compound of formula I-dd-2 or I-dd-3:

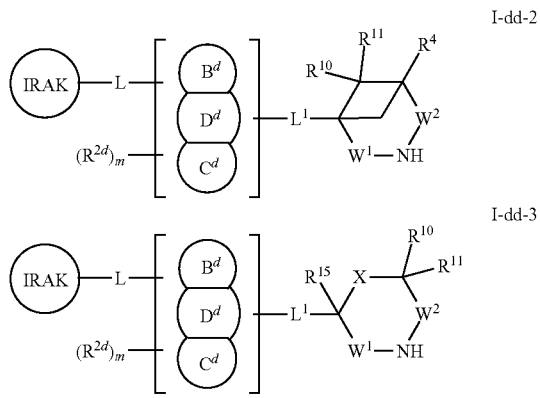

or a pharmaceutically acceptable salt thereof, wherein L and SMARCA are as defined above and described in embodiments herein, and wherein:
each $R^{2d}$ is independently hydrogen, deuterium, $-R^{3d}$, halogen, $-CN$, $-NO_2$, $-OR$, $-SR$, $-NR_2$, $-SiR_3$, $-S(O)_2R$, $-S(O)_2NR_2$, $-S(O)R$, $-C(O)R$, $-C(O)OR$, $-C(O)NR_2$, $-C(O)N(R)OR$, $-C(R)_2N(R)C(O)R$, $-C(R)_2N(R)C(O)N(R)_2$, $-OC(O)R$, $-OC(O)N(R)_2$, $-OP(O)R_2$, $-OP(O)(OR)_2$, $-OP(O)(OR)NR_2$, $-OP(O)(NR_2)_2$, $N(R)C(O)OR$, $-N(R)C(O)R$, $-N(R)C(O)NR_2$, $-N(R)S(O)_2R$, $-NP(O)R_2$, $-N(R)P(O)(OR)_2$, $-N(R)P(O)(OR)NR_2$, $-N(R)P(O)(NR_2)_2$, or $-N(R)S(O)_2R$;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^{3d}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

each of Ring $B^d$, Ring $C^d$, and Ring $D^d$ is independently a fused ring selected from 6-membered aryl, 6-membered heteroaryl containing 1-4 heteroatoms independently selected from nitrogen, oxygen, or sulfur, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-4 heteroatoms independently selected from nitrogen, oxygen or sulfur;

$L^1$ is a covalent bond or a $C_{1-3}$ bivalent straight or branched saturated or unsaturated hydrocarbon chain wherein 1-2 methylene units of the chain are independently and optionally replaced with $-O-$, $-C(O)-$, $-C(S)-$, $-C(R)_2-$, $-CH(R)-$, $-C(F)_2-$, $-N(R)-$, $-S-$, $-S(O)_2-$ or $-CR=CR-$;

m is 0, 1, 2, 3, 4, 5, 6, 7, 8, 9, 10, 11, 12, 13, 14, 15, or 16; and $R^4$, $R^{10}$, $R^{11}$, $R^{15}$, $W^1$, $W^2$, and X is as defined in WO 2019/099868, the entirety of each of which is herein incorporated by reference.

Where a point of attachment of

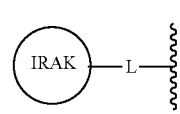

is depicted on Ring $B^d$, Ring $C_d$, or Ring $D^d$, it is intended, and one of ordinary skill in the art would appreciate, that the point of attachment of

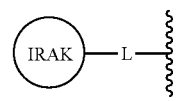

may be on any available carbon or nitrogen atom on Ring $B^d$, Ring $C^d$, or Ring $D^d$, including the ring to which Ring $B^d$ or Ring $D^d$ is fused to Ring $C^d$.

Where a point of attachment of $-(R^{2d})_m$ is depicted on Ring $B^d$, Ring $C^d$, or Ring $D^d$, it is intended, and one of ordinary skill in the art would appreciate, that the point of attachment of $-(R^2)m$ may be at any available carbon or nitrogen atom on Ring $B^d$, Ring $C^d$, or Ring $D^d$ including the carbon atom to which Ring $B^d$ or Ring $D^d$ are fused to Ring $C^d$.

Where a point of attachment of

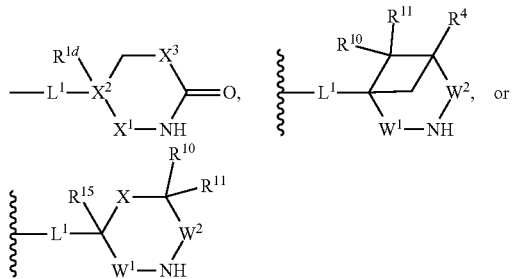

is depicted on Ring $B^d$, Ring $C^d$, or Ring $D^d$, it is intended, and one of ordinary skill in the art would appreciate, that the point of attachment of

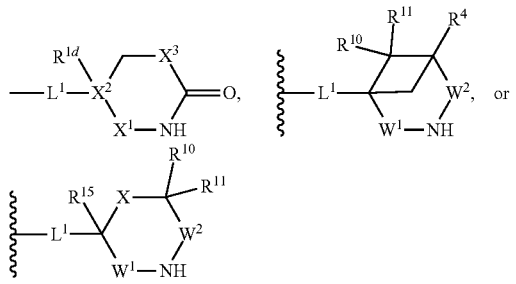

may be on any available carbon or nitrogen atom on Ring $B^d$, Ring $C^d$, or Ring $D^d$, including the carbon atom to which Ring $B^d$ or Ring $D^d$ are fused to Ring $C^d$.

In certain embodiments, the present invention provides a compound of formula I, wherein LBM is an E3 ubiquitin ligase (cereblon) binding moiety thereby forming a compound of formula I-ee:

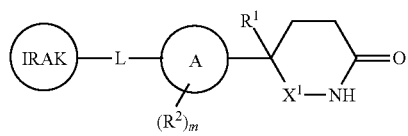

I-ee or a pharmaceutically acceptable salt thereof, wherein:
$X^1$ is a bivalent moiety selected from a covalent bond, —CH$_2$—, —C(O)—, —C(S)—, or

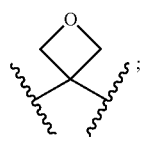 [SMILES: *C1(*)COC1]

;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each $R^2$ is independently hydrogen, —$R^3$, halogen, —CN, —NO$_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;
each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
Ring A is a tricyclic ring selected from

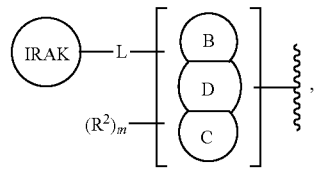

wherein
each of Ring B, Ring C, and Ring D is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur; and
m is 0, 1, 2, 3, 4, 5, 6, 7, 8, 9, 10, 11, 12, 13, 14, 15, or 16;
wherein L and IRAK are as described in embodiments herein.

In some embodiments, a compound of formula I-ee above is provided as a compound of formula I-ee' or formula I-ee":

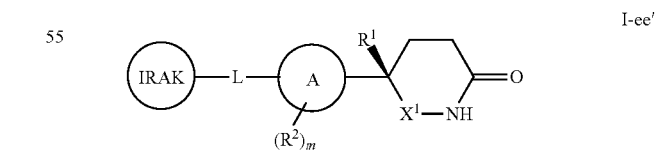

I-ee'

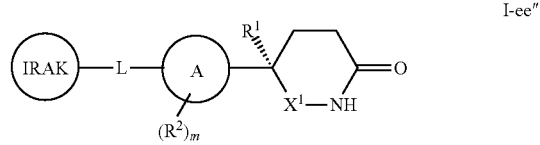

I-ee"

or a pharmaceutically acceptable salt thereof, wherein:
each of IRAK, Ring A, L, R¹, R², X¹, and m is as defined above.

In certain embodiments, the present invention provides a compound of formula I, wherein LBM is an E3 ubiquitin ligase (cereblon) binding moiety thereby forming a compound of formula I-ff:

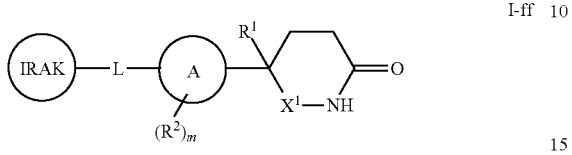

I-ff or a pharmaceutically acceptable salt thereof, wherein:
X¹ is a bivalent moiety selected from a covalent bond, —CH₂—, —C(O)—, —C(S)—, or

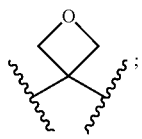 [SMILES: *C1(*)COC1]

;

R¹ is hydrogen, deuterium, halogen, —CN, —OR, —SR, —S(O)R, —S(O)₂R, —N(R)₂, —Si(R)₃, or an optionally substituted $C_{1-4}$ aliphatic;
each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each R² is independently hydrogen, —R³, halogen, —CN, —NO₂, —OR, —SR, —N(R)₂, —Si(R)₃, —S(O)₂R, —S(O)₂N(R)₂, —S(O)R, —C(O)R, —C(O)OR, —C(O)N(R)₂, —C(O)N(R)OR, —C(R)₂N(R)C(O)R, —C(R)₂N(R)C(O)N(R)₂, —OC(O)R, —OC(O)N(R)₂, —N(R)C(O)OR, —N(R)C(O)R, —N(R)C(O)N(R)₂, or —N(R)S(O)₂R;
each R³ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
Ring A is a tricyclic ring selected from

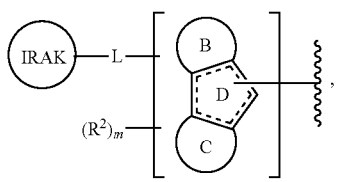

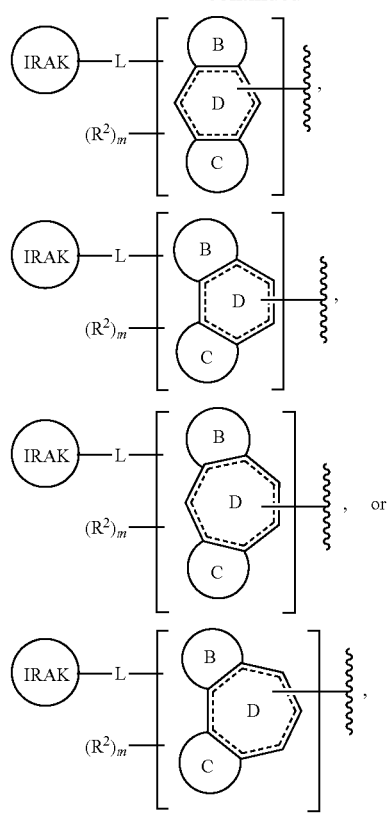

wherein
each of Ring B and Ring C is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen or sulfur, or 5-membered heteroaryl with 1-3 heteroatoms independently selected from nitrogen, oxygen or sulfur;
Ring D is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur;
=== is a single or double bond;
m is 0, 1, 2, 3, 4, 5, 6, 7, 8, 9, 10, 11, 12, 13, 14, 15, or 16;
wherein L and IRAK are as described in embodiments herein.

In some embodiments, a compound of formula I-ff above is provided as a compound of formula I-ff' or formula I-ff":

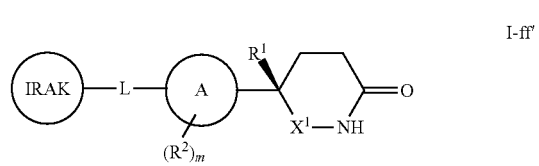

I-ff'

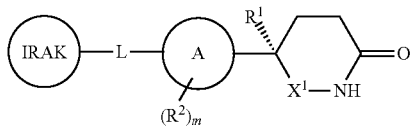

I-ff″ or a pharmaceutically acceptable salt thereof, wherein:
each of IRAK, Ring A, L, $R^1$, $R^2$, $X^1$, and m is as defined above.

In certain embodiments, the present invention provides a compound of formula I, wherein LBM is an E3 ubiquitin ligase (cereblon) binding moiety thereby forming a compound of formula I-gg:

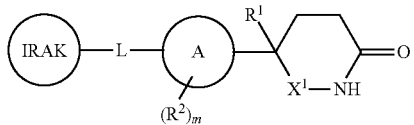

I-gg or a pharmaceutically acceptable salt thereof, wherein:
$X^1$ is a bivalent moiety selected from a covalent bond, —$CH_2$—, —C(O)—, —C(S)—, or

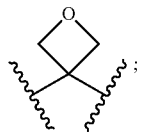 [SMILES: *C1(*)COC1]

;

$R^1$ is hydrogen, deuterium, halogen, —CN, —OR, —SR, —S(O)R, —S(O)$_2$R, —N(R)$_2$, —Si(R)$_3$, or an optionally substituted $C_{1-4}$ aliphatic;

each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur;

each $R^2$ is independently hydrogen, —$R^3$, halogen, —CN, —$NO_2$, —OR, —SR, —N(R)$_2$, —Si(R)$_3$, —S(O)$_2$R, —S(O)$_2$N(R)$_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, —N(R)C(O)OR, —N(R)C(O)R, —N(R)C(O)N(R)$_2$, or —N(R)S(O)$_2$R;

each $R^3$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

Ring A is a tricyclic ring selected from

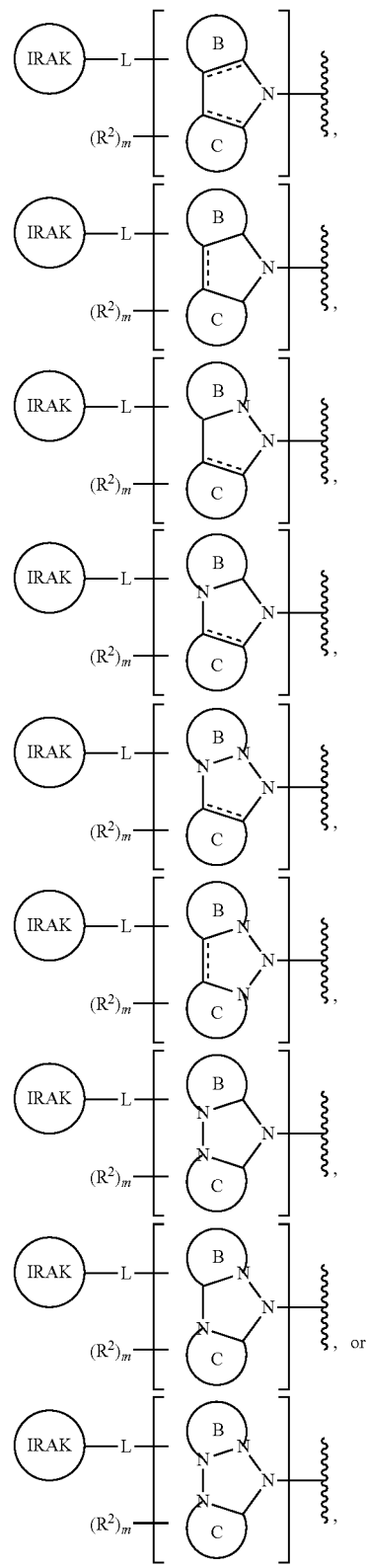

wherein
each of Ring B and Ring C is independently a fused ring selected from 6-membered aryl containing 0-2 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur;

--- is a single or double bond;

m is 0, 1, 2, 3, 4, 5, 6, 7, or 8;

wherein L and IRAK are as described in embodiments herein.

In some embodiments, a compound of formula I-gg above is provided as a compound of formula I-gg' or formula I-gg":

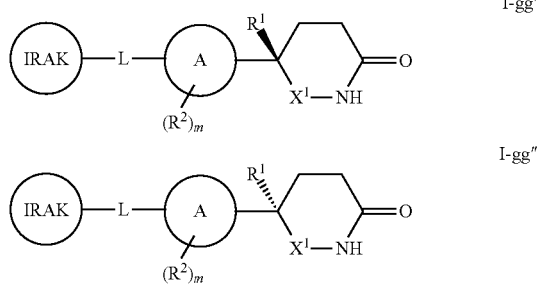

or a pharmaceutically acceptable salt thereof, wherein:
each of IRAK, Ring A, L, $R^1$, $R^2$, $X^1$, and m is as defined above.

As defined above and described herein, $X^1$ is a bivalent moiety selected from a covalent bond, —$CH_2$—, —C(O)—, —C(S)—, or

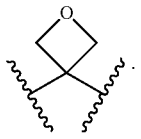 [SMILES: *C1(*)COC1]

In some embodiments, $X^1$ is a covalent bond. In some embodiments, $X^1$ is —$CH_2$—. In some embodiments, $X^1$ is —C(O)—. In some embodiments, $X^1$ is —C(S)—. In some embodiments, $X^1$ is

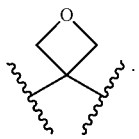 [SMILES: *C1(*)COC1]

In some embodiments, $X^1$ is selected from those depicted in Table 1, below.

As defined above and described herein, $X^2$ is a carbon atom or silicon atom.

In some embodiments, $X^2$ is a carbon atom. In some embodiments, $X^2$ is a silicon atom.

In some embodiments, $X^2$ is selected from those depicted in Table 1, below.

As defined above and described herein, $X^3$ is a bivalent moiety selected from —$CH_2$— or —Si($R^2$)—.

In some embodiments, $X^3$ is —$CH_2$—. In some embodiments, $X^2$ is —Si($R^2$)—.

In some embodiments, $X^3$ is selected from those depicted in Table 1, below.

As defined above and described herein, $R^1$ or $R^{1d}$ is hydrogen, deuterium, halogen, —CN, —OR, —SR, —S(O)R, —$S(O)_2R$, —$NR_2$, —Si($R^3$), or an optionally substituted $C_{1-4}$ aliphatic.

In some embodiments, $R^1$ or $R^{1d}$ is hydrogen. In some embodiments, $R^1$ or $R^{1d}$ is deuterium. In some embodiments, $R^1$ or $R^{1d}$ is halogen. In some embodiments, $R^1$ or $R^{1d}$ is —CN. In some embodiments, $R^1$ or $R^{1d}$ is —OR. In some embodiments, $R^1$ or $R^{1d}$ is —SR. In some embodiments, $R^1$ or $R^{1d}$ is —S(O)R. In some embodiments, $R^1$ or $R^{1d}$ is —$S(O)_2R$. In some embodiments, $R^1$ or $R^{1d}$ is —$NR_2$. In some embodiments, $R^1$ or $R^{1d}$ is —Si($R^3$). In some embodiments, $R^1$ or $R^{1d}$ is an optionally substituted $C_{1-4}$ aliphatic.

In some embodiments, $R^1$ or $R^{1d}$ is selected from those depicted in Table 1, below.

As defined above and described herein, each R is independently hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or: two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is hydrogen. In some embodiments, R is optionally substituted $C_{1-6}$ aliphatic. In some embodiments, R is optionally substituted phenyl. In some embodiments, R is optionally substituted 4-7 membered saturated or partially unsaturated heterocyclic having 1-2 heteroatoms independently selected from nitrogen, oxygen, and sulfur. In some embodiments, R is optionally substituted 5-6 membered heteroaryl ring having 1-4 heteroatoms independently selected from nitrogen, oxygen, and sulfur. In some embodiments, two R groups on the same nitrogen are taken together with their intervening atoms to form a 4-7 membered saturated, partially unsaturated, or heteroaryl ring having 0-3 heteroatoms, in addition to the nitrogen, independently selected from nitrogen, oxygen, and sulfur.

In some embodiments, R is selected from those depicted in Table 1, below.

As defined above and described herein, each $R^2$ or $R^{2d}$ is independently hydrogen, —$R^3$, —$R^{3d}$, halogen, —CN, —$NO_2$, —OR, —SR, —$N(R)_2$, Si($R_3$), —$S(O)_2R$, —$S(O)_2N(R)_2$, —S(O)R, —C(O)R, —C(O)OR, —C(O)N(R)$_2$, —C(O)N(R)OR, —C(R)$_2$N(R)C(O)R, —C(R)$_2$N(R)C(O)N(R)$_2$, —OC(O)R, —OC(O)N(R)$_2$, N(R)C(O)OR, —N(R)C(O)R, —N(R)C(O)N(R)$_2$, or —N(R)S(O)$_2$R.

In some embodiments, $R^2$ or $R^{2d}$ is hydrogen. In some embodiments, $R^2$ is —$R^3$. In some embodiments, $R^{2d}$ is —$R^{3d}$. In some embodiments, $R^2$ or $R^{2d}$ is halogen. In some embodiments, $R^2$ or $R^{2d}$ is —CN. In some embodiments, $R^2$ or $R^{2d}$ is —$NO_2$. In some embodiments, $R^2$ or $R^{2d}$ is —OR. In some embodiments, $R^2$ or $R^{2d}$ is —SR. In some embodiments, $R^2$ is —$NR_2$. In some embodiments, $R^2$ or $R^{2d}$ is —Si($R_3$). In some embodiments, $R^2$ or $R^{2d}$ is —$S(O)_2R$. In some embodiments, $R^2$ or $R^{2d}$ is —$S(O)_2NR_2$. In some embodiments, $R^2$ or $R^{2d}$ is —S(O)R. In some embodiments, $R^2$ or $R^{2d}$ is —C(O)R. In some embodiments, $R^2$ or $R^{2d}$ is —C(O)OR. In some embodiments, $R^2$ or $R^{2d}$ is —C(O)NR$_2$. In some embodiments, $R^2$ or $R^{2d}$ is —C(O)N(R)OR. In some embodiments, $R^2$ or $R^{2d}$ is —C(R)$_2$N(R)C(O)R. In some embodiments, $R^2$ or $R^{2d}$ is —C(R)$_2$N(R)C(O)N(R)$_2$. In some embodiments, $R^2$ or $R^{2d}$ is —OC(O)R. In some embodiments, $R^2$ or $R^{2d}$ is —OC(O)NR$_2$. In some embodiments, $R^2$ or $R^{2d}$ is —N(R)C(O)OR. In some embodiments, $R^2$ or $R^{2d}$ is —N(R)C(O)R. In some embodiments, $R^2$ or $R^{2d}$ is —N(R)C(O)NR$_2$. In some embodiments, $R^2$ or $R^{2d}$ is —N(R)S(O)$_2$R.

In some embodiments, $R^2$ is selected from those depicted in Table 1, below.

As defined above and described herein, each $R^3$ or $R^{3d}$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^3$ or $R^{3d}$ is an optionally substituted $C_{1-6}$ aliphatic. In some embodiments, $R^3$ or $R^{3d}$ is an optionally substituted phenyl. In some embodiments, $R^3$ or $R^{3d}$ is an optionally substituted 4-7 membered saturated or partially unsaturated heterocyclic ring having 1-2 heteroatoms independently selected from nitrogen, oxygen, and sulfur. In some embodiments, $R^3$ or $R^{3d}$ is an optionally substituted 5-6 membered heteroaryl ring having 1-4 heteroatoms independently selected from nitrogen, oxygen, and sulfur.

In some embodiments, $R^3$ or $R^{3d}$ is selected from those depicted in Table 1, below.

As defined above and described herein, Ring A is a tricyclic ring selected from

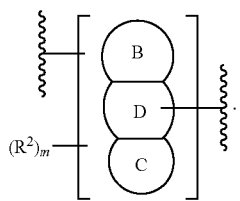

In some embodiments, Ring A is

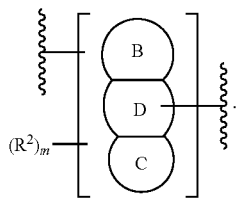

In some embodiments, Ring A is selected from those depicted in Table 1, below.

As defined above and described herein, Ring $A^d$ is a tricyclic ring selected from

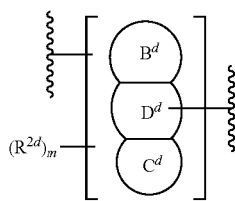

In some embodiments, Ring $A^d$ is

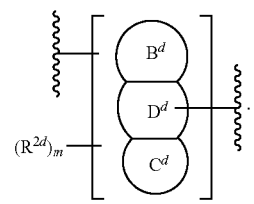

In some embodiments, Ring Ad is selected from those depicted in Table 1, below.

As defined above and described herein, each of Ring B, Ring C, and Ring D or Ring $B^d$, Ring $C^d$, and Ring $D^d$ is independently a fused ring selected from 6-membered aryl containing 0-3 nitrogens, 5 to 7-membered saturated or partially unsaturated carbocyclyl, 5 to 7-membered saturated or partially unsaturated heterocyclyl ring with 1-3 heteroatoms independently selected from boron, nitrogen, oxygen, silicon, or sulfur, or 5-membered heteroaryl with 1-3 heteroatoms independently selected from nitrogen, oxygen or sulfur.

In some embodiments, each Ring B, Ring C, and Ring D or Ring $B^d$, Ring $C^d$, and Ring $D^d$ is independently a 6-membered aryl containing 0-2 nitrogen atoms. In some embodiments, each Ring B, Ring C, and Ring D or Ring $B^d$, Ring $C^d$, and Ring $D^d$ is independently a 5 to 7-membered saturated or partially unsaturated carbocyclyl. In some embodiments, each Ring B, Ring C, and Ring D or Ring $B^d$, Ring $C^d$, and Ring $D^d$ is independently a 5 to 7-membered saturated or partially unsaturated heterocyclyl with 1-2 heteroatoms independently selected from boron, nitrogen, oxygen, silicon, or sulfur. In some embodiments, each Ring B, Ring C, and Ring D or Ring $B^d$, Ring $C^d$, and Ring $D^d$ is independently a 5-membered heteroaryl with 1-3 heteroatoms independently selected from nitrogen, oxygen or sulfur.

In some embodiments, Ring B, Ring C, and Ring D or Ring $B^d$, Ring $C^d$, and Ring Dd is selected from those depicted in Table 1, below.

As defined above and described herein, Ring A is a tricyclic ring selected from

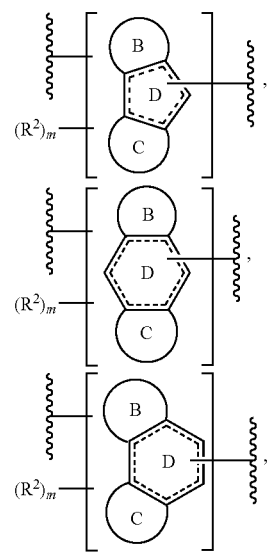

-continued

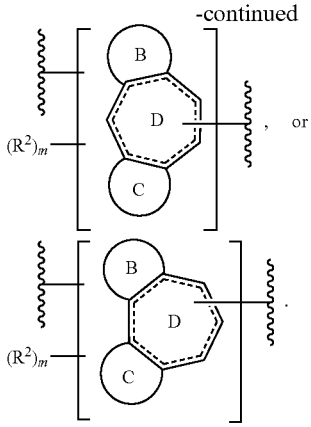

In some embodiments, Ring A is

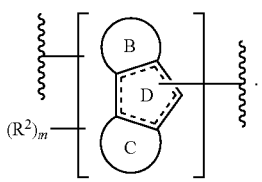

In some embodiments, Ring A is

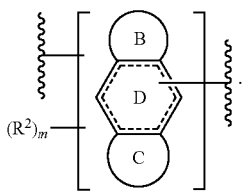

In some embodiment, Ring A is

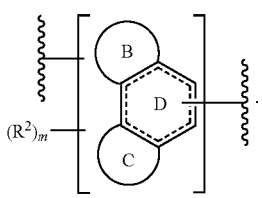

In some embodiments, Ring A is

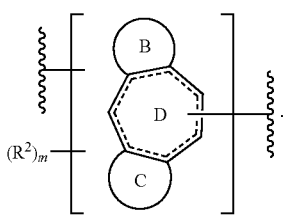

In some embodiments, Ring A is

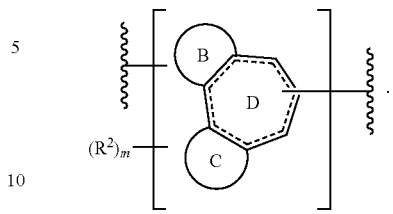

In some embodiments, Ring A is selected from those depicted in Table 1, below.

As defined above and described herein, Ring D or Ring $D^d$ is a fused ring selected from aryl containing 0-3 nitrogens, saturated or partially unsaturated carbocyclyl, saturated or partially unsaturated heterocyclyl ring with 1-2 heteroatoms independently selected from nitrogen, oxygen, silicon, or sulfur, or heteroaryl with 1-3 heteroatoms independently selected from nitrogen, oxygen or sulfur.

In some embodiments, Ring D or Ring $D^d$ is an aryl containing 0-2 nitrogen atoms. In some embodiments, Ring D or Ring $D^d$ is a saturated or partially unsaturated carbocyclyl. In some embodiments, each Ring D or Ring $D^d$ is a saturated or partially unsaturated heterocyclyl with 1-2 heteroatoms independently selected from nitrogen, oxygen, silicon, or sulfur. In some embodiments, Ring D or Ring $D^d$ is a heteroaryl with 1-3 heteroatoms independently selected from nitrogen, oxygen or sulfur.

In some embodiments, Ring D is

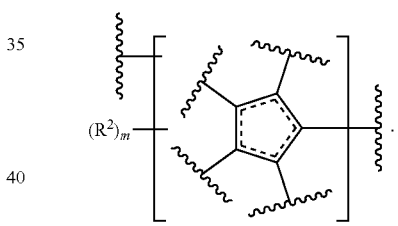

In some embodiments, Ring D is

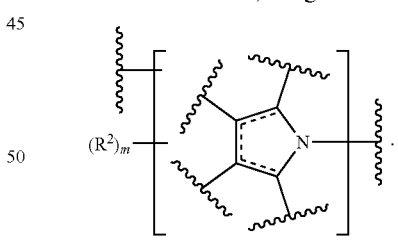

In some embodiments, Ring D is

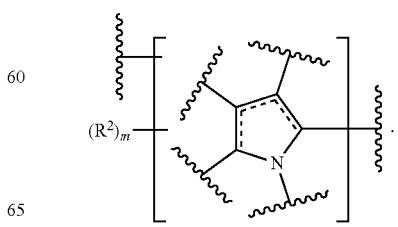

In some embodiments, Ring D is
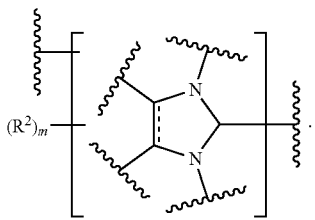
In some embodiments, Ring D is
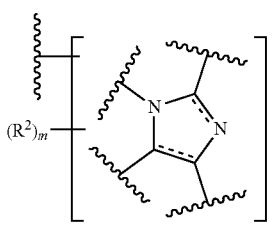
In some embodiments, Ring D is
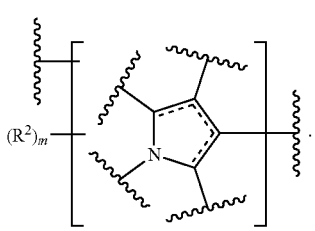
In some embodiments, Ring D is
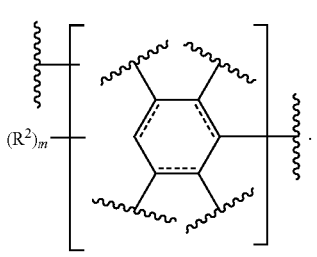
In some embodiments, Ring D is
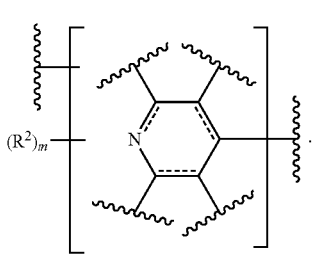
In some embodiments, Ring D is

In some embodiments, Ring D is
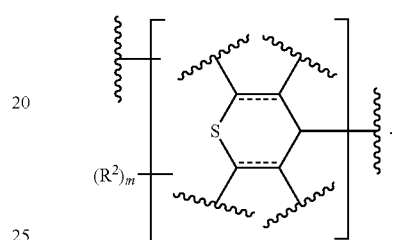
In some embodiments, Ring D is
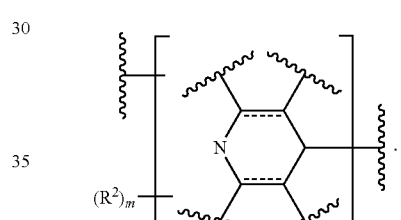
In some embodiments, Ring D is
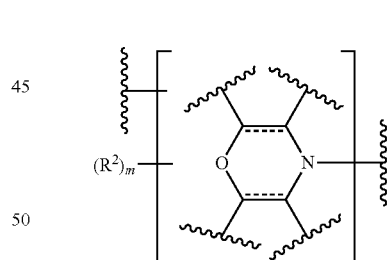
In some embodiments, Ring D is

In some embodiments, Ring D is
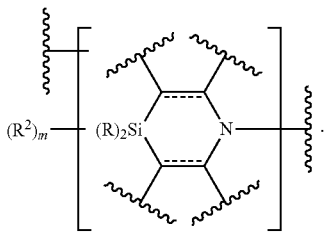
In some embodiments, Ring D is
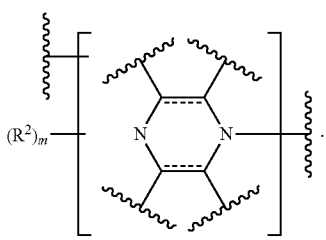
In some embodiments, Ring D is
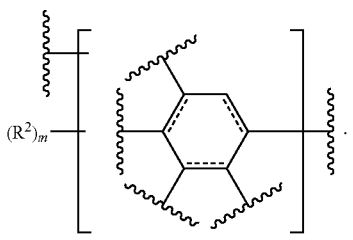
In some embodiments, Ring D is
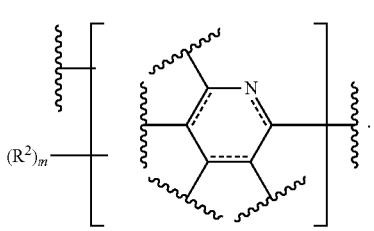
In some embodiments, Ring D is
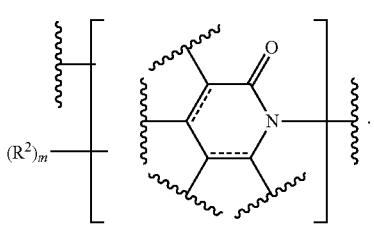
In some embodiments, Ring D is

In some embodiments, Ring D is
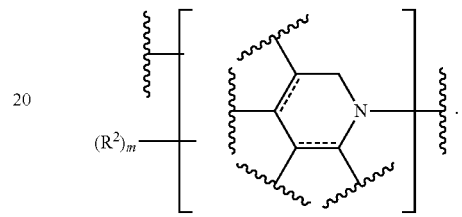
In some embodiments, Ring D is
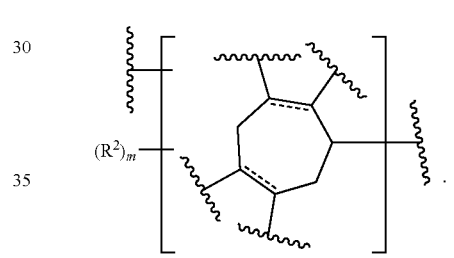
In some embodiments, Ring D is
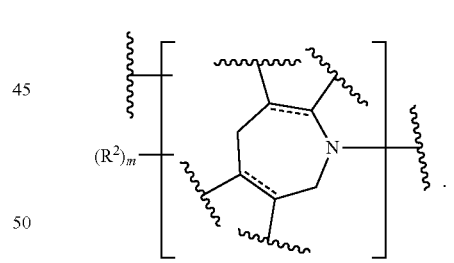
In some embodiments, Ring D is
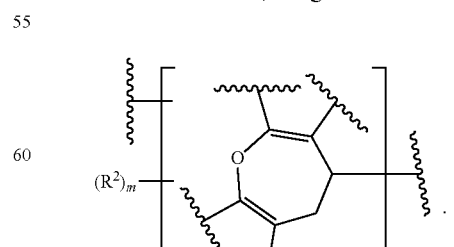

In some embodiments, Ring D is
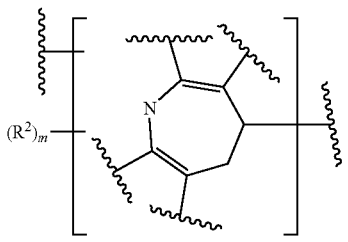
In some embodiments, Ring D is
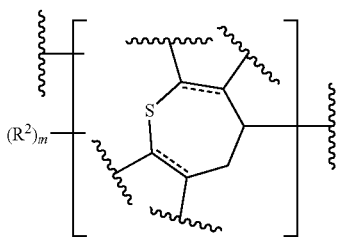
In some embodiments, Ring D is
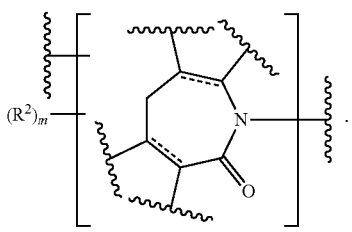
In some embodiments, Ring D is
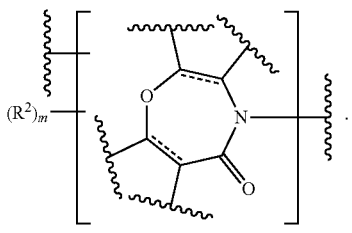
In some embodiments, Ring D is
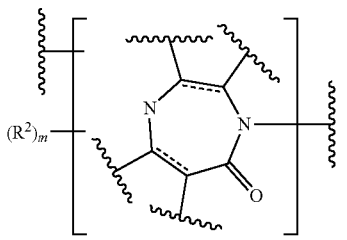
In some embodiments, Ring D is

In some embodiments, Ring D is
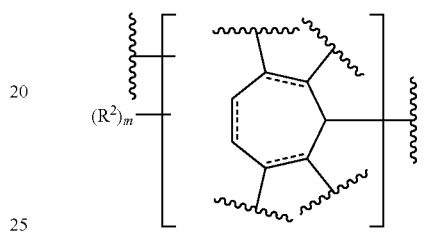
In some embodiments, Ring D is
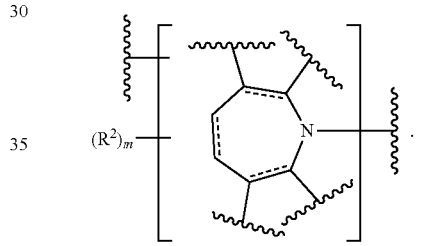
In some embodiments, Ring D is
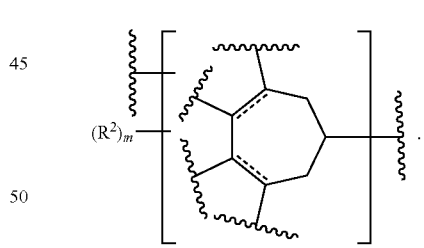
In some embodiments, Ring D is
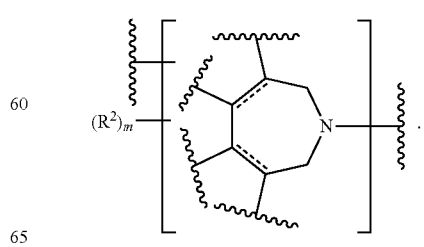

In some embodiments, Ring D is

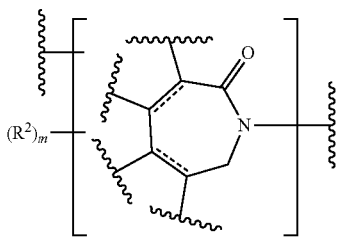

In some embodiments, Ring D is

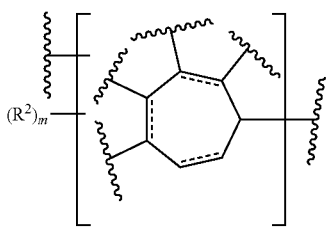

In some embodiments, Ring D is

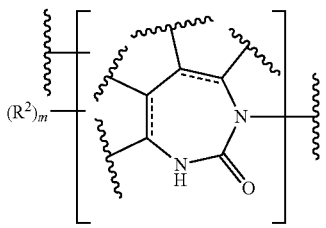

In some embodiments, Ring D is

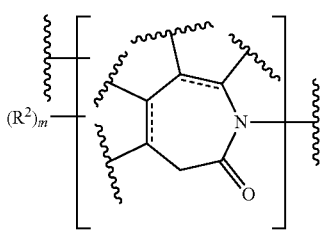

In some embodiments, Ring D is selected from those depicted in Table 1, below.

As defined above and described herein, m is 0, 1, 2, 3, 4, 5, 6, 7, 8, 9, 10, 11, 12, 13, 14, 15, or 16.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8. In some embodiments, m is 9. In some embodiments, m is 10. In some embodiments, m is 11. In some embodiments, m is 12. In some embodiments, m is 13. In some embodiments, m is 14. In some embodiments, m is 15. In some embodiments, m is 16.

In some embodiments, m is selected from those depicted in Table 1, below.

As defined above and described herein, Ring A is a tricyclic ring selected from

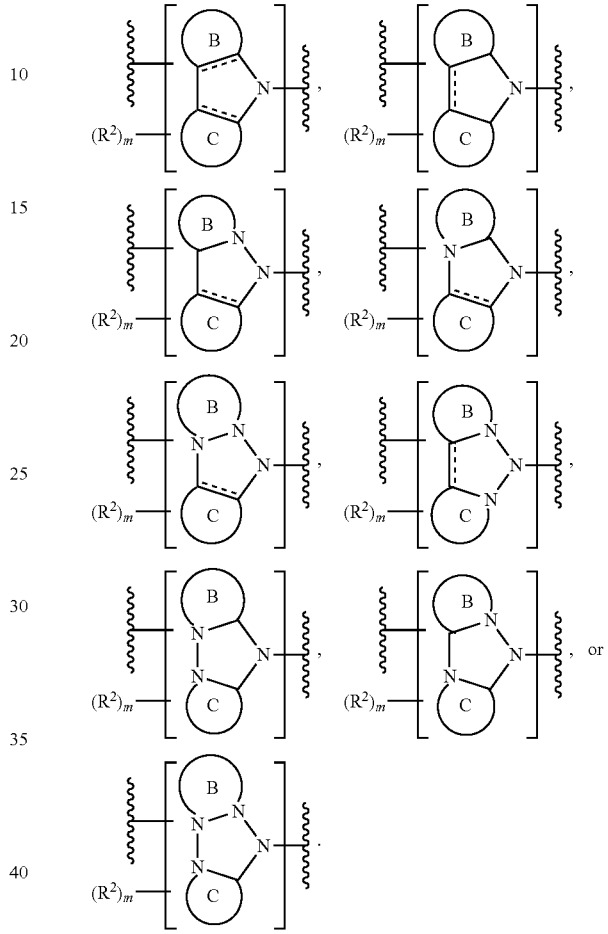

In some embodiments, Ring A is

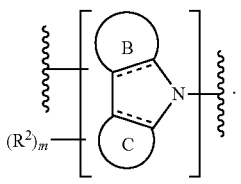

In some embodiments, Ring A is

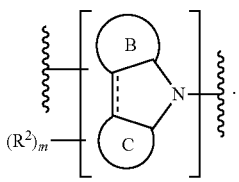

In some embodiment, Ring A is

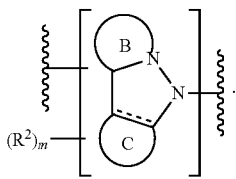

In some embodiments, Ring A is

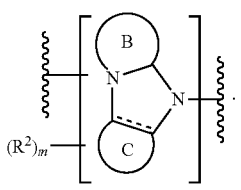

In some embodiments, Ring A is

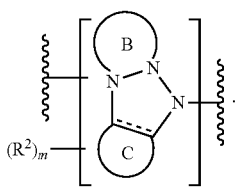

In some embodiments, Ring A is

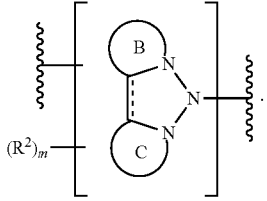

In some embodiments, Ring A is

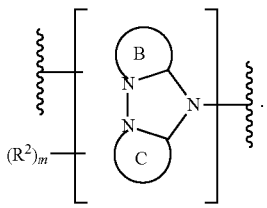

In some embodiments, Ring A is


In some embodiments, Ring A is

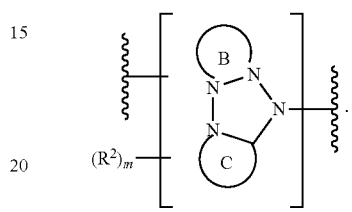

In some embodiments, Ring A is selected from those depicted in Table 1, below.

As defined above and described herein, each Ring B and Ring C or Ring $B^d$ and Ring $C^d$ is independently a fused ring selected from 6-membered aryl containing 0-2 nitrogen atoms, 5 to 7-membered saturated or partially unsaturated carbocyclyl, 5 to 7-membered saturated or partially unsaturated heterocyclyl with 1-3 heteroatoms independently selected from boron, nitrogen, oxygen, silicon, or sulfur, or 5-membered heteroaryl with 1-3 heteroatoms independently selected from nitrogen, oxygen or sulfur.

In some embodiments, each Ring B and Ring C or Ring $B^d$ and Ring $C^d$ is independently a 6-membered aryl containing 0-2 nitrogen atoms. In some embodiments, each Ring B and Ring C or Ring $B^d$ and Ring $C^d$ is independently a 5 to 7-membered saturated or partially unsaturated carbocyclyl. In some embodiments, each Ring B and Ring C or Ring $B^d$ and Ring $C^d$ is independently a 5 to 7-membered saturated or partially unsaturated heterocyclyl with 1-3 heteroatoms independently selected from boron, nitrogen, oxygen, silicon, or sulfur. In some embodiments, each Ring B and Ring C or Ring $B^d$ and Ring $C^d$ is independently a 5-membered heteroaryl with 1-3 heteroatoms independently selected from nitrogen, oxygen or sulfur.

In some embodiments, each Ring B and Ring C is independently

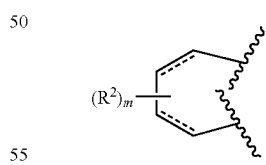

In some embodiments, each Ring B and Ring C is independently

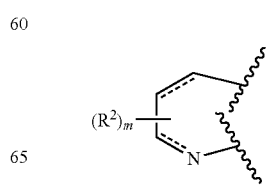

In some embodiments, each Ring B and Ring C is independently

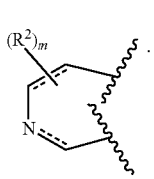

In some embodiments, each Ring B and Ring C is independently

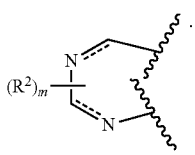

In some embodiments, Ring B and Ring C is independently

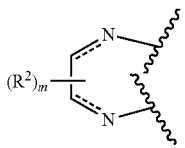

In some embodiments, Ring B and Ring C is independently is

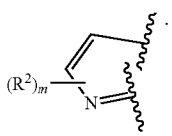

In some embodiments, Ring B and Ring C is independently

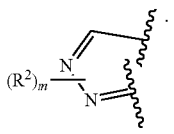

In some embodiments, Ring B and Ring C is independently

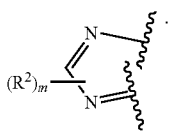

In some embodiments, Ring B and Ring C is independently

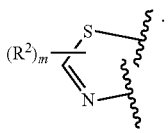

In some embodiments, Ring B and Ring C is independently

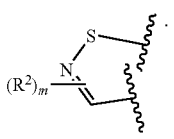

In some embodiments, Ring B and Ring C is independently

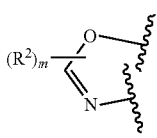

In some embodiments, Ring B and Ring C is independently

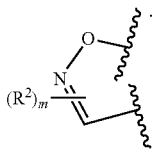

In some embodiments, Ring B and Ring C is independently

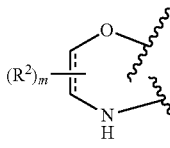

In some embodiments, Ring B and Ring C is independently

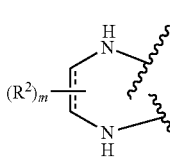

In some embodiments, B and Ring C is independently

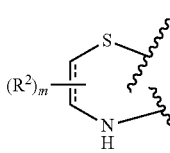

In some embodiments, Ring B and Ring C is independently

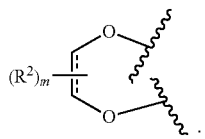

In some embodiments, Ring B and Ring C is independently

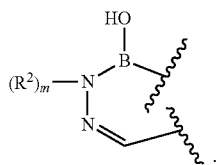

In some embodiments, Ring B and Ring C is independently selected from those depicted in Table 1, below.

As defined above and described herein, === is a single or double bond

In some embodiments, === is a single bond. In some embodiments, === is a double bond.

As defined above and described herein, m is 0, 1, 2, 3, 4, 5, 6, 7, or 8.

In some embodiments, m is 0. In some embodiments, m is 1. In some embodiments, m is 2. In some embodiments, m is 3. In some embodiments, m is 4. In some embodiments, m is 5. In some embodiments, m is 6. In some embodiments, m is 7. In some embodiments, m is 8.

In some embodiments, m is selected from those depicted in Table 1, below.

In some embodiments, In some embodiments, LBM is

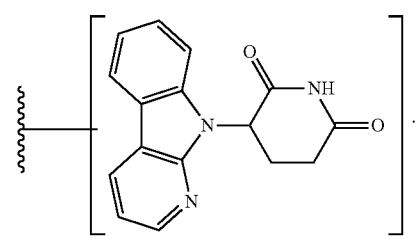

In some embodiments, LBM is

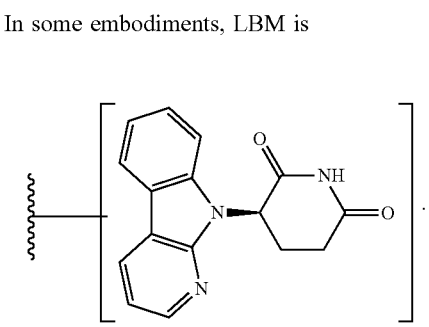

In some embodiments, LBM is

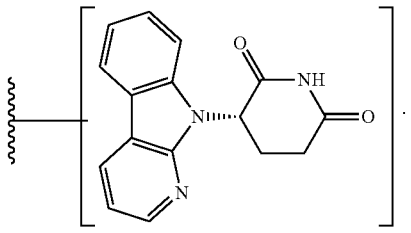

In some embodiments, In some embodiments, LBM is

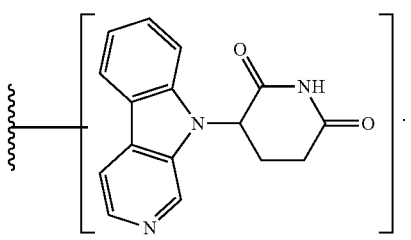

In some embodiments, LBM is

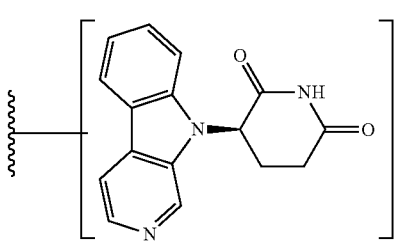

In some embodiments, LBM is

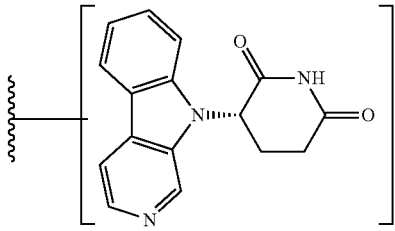

In some embodiments, LBM is

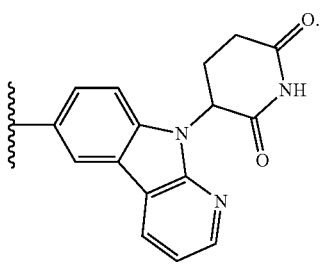 [SMILES: *c1ccc2c(c1)c1cccnc1n2C1CCC(=O)NC1=O]

In some embodiments, LBM is
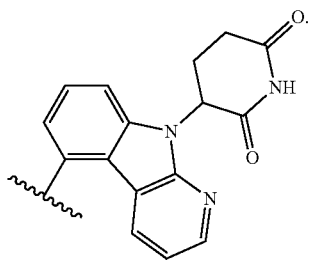 [SMILES: *c1cccc2c1c1cccnc1n2C1CCC(=O)NC1=O]
In some embodiments, LBM is
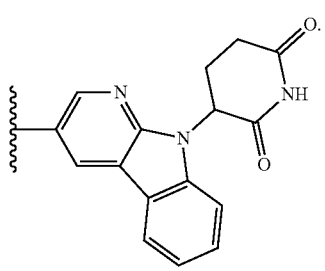
In some embodiments, LBM is
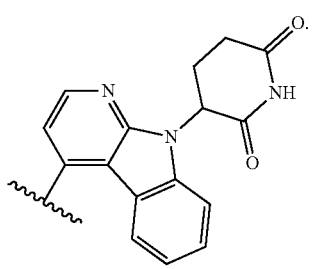 [SMILES: *c1ccnc2c1c1ccccc1n2C1CCC(=O)NC1=O]
In some embodiments, LBM is
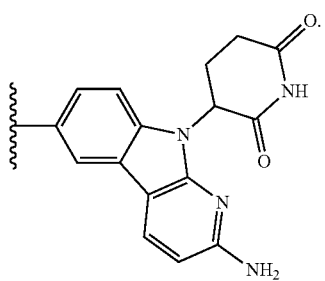 [SMILES: *c1ccc2c(c1)c1ccc(N)nc1n2C1CCC(=O)NC1=O]
In some embodiments, LBM is
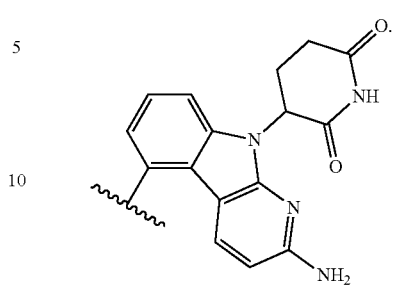
In some embodiments, LBM is
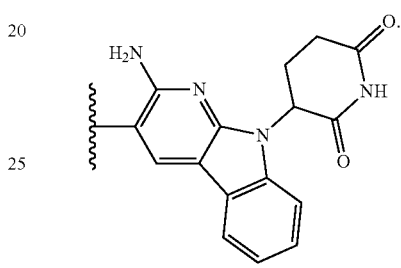
In some embodiments, LBM is
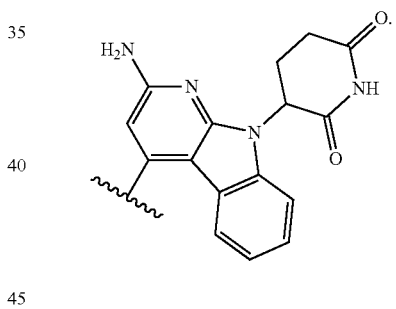
In some embodiments, LBM is selected from those in Table 1 below.
In some embodiments, the present invention provides the compound of formula II, wherein LBM is
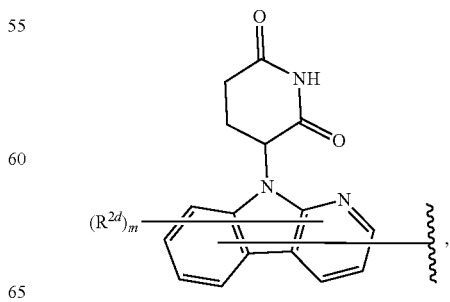

thereby forming a compound of formula II-r:

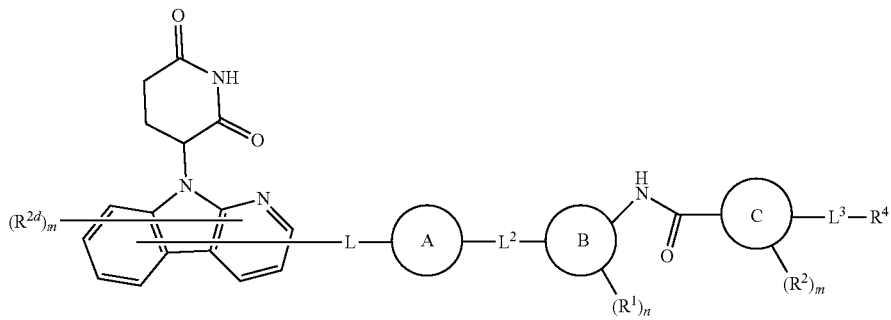

II-r or a pharmaceutically acceptable salt thereof, wherein each of L, L², L³, Ring A, Ring B, Ring C, R¹, R², R²ᵈ, R⁴, n, and each m is as defined above and described in embodiments herein, both singly and in combination.

In some embodiments, the present invention provides the compound of formula II, wherein LBM is

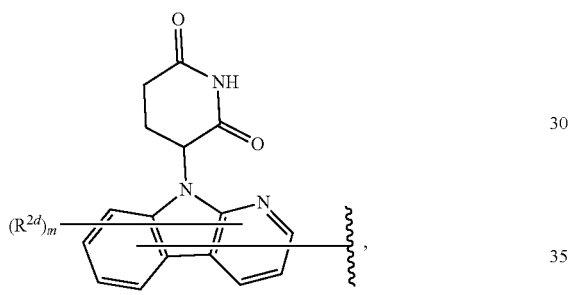

L² is a covalent bond, Ring A is cyclohexyl, Ring B is pyrazolyl, Ring C is oxazolyl, and Ring D is pyridyl thereby forming a compound of formula II-s:

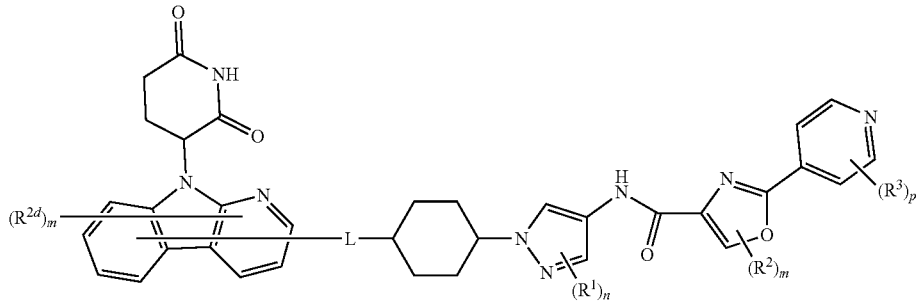

II-s or a pharmaceutically acceptable salt thereof, wherein each of L, R¹, R², R²ᵈ, R³, n, each m, and p is as defined above and described in embodiments herein, both singly and in combination.

In certain embodiments, the present invention provides the compound of formula II-d, wherein LBM is

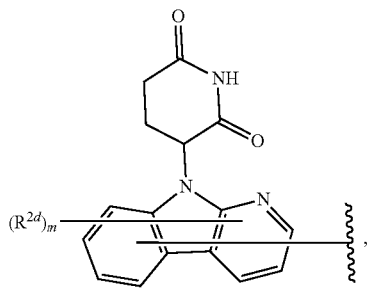

$L^2$ is a covalent bond, Ring A is cyclohexyl, and Ring B is pyrazolyl as shown, thereby forming a compound of formula II-d-7:

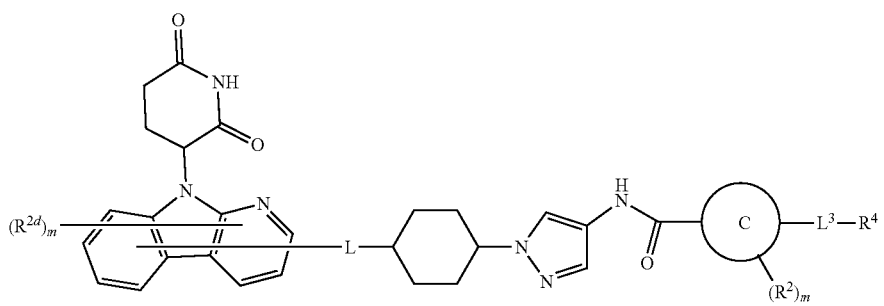

II-d-7 or a pharmaceutically acceptable salt thereof, wherein each of L, $L^3$, Ring C, $R^1$, $R^2$, $R^{2d}$, $R^4$, n, and each m is as defined above and described in embodiments herein, both singly and in combination.

In certain embodiments, the present invention provides the compound of formula II-e, wherein LBM is

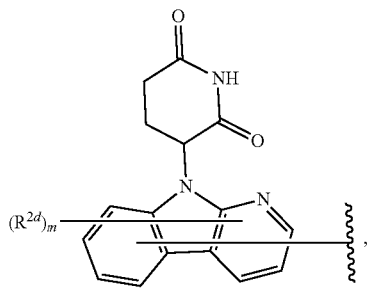

$L^2$ is a covalent bond, Ring A is cyclohexyl, Ring C is pyrazolo[1,5-a]pyrimidine, and Ring B is pyrazolyl as shown, thereby forming a compound of formula II-e-7:

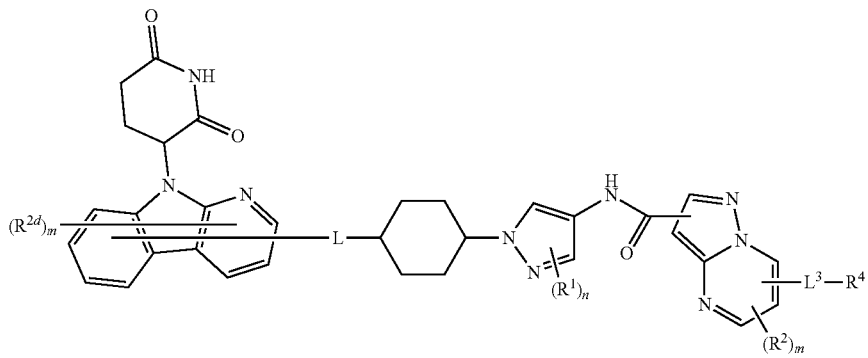

II-e-7 or a pharmaceutically acceptable salt thereof, wherein each of L, $L^3$, $R^1$, $R^2$, $R^{2d}$, $R^4$, n, and each m is as defined above and described in embodiments herein, both singly and in combination.

In certain embodiments, the present invention provides a compound of formula I, wherein LBM is VHL binding moiety

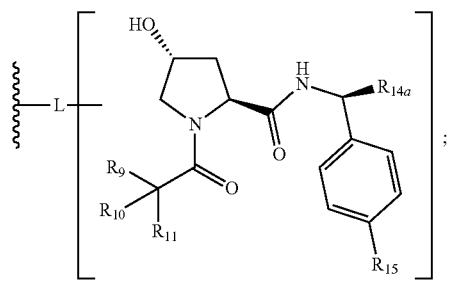

thereby forming a compound of formula I-hh:

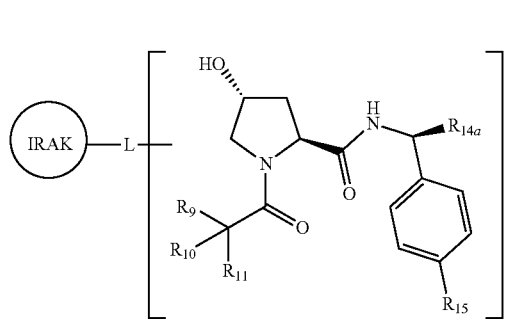

I-hh or a pharmaceutically acceptable salt thereof, wherein L and IRAK are as defined above and described in embodiments herein, and wherein each of the variables $R_9$, $R_{10}$, $R_{11}$, $R_{14a}$, and $R_{15}$ is as described and defined in WO 2017/030814, WO 2016/118666, and US 2017/0327469, the entirety of each of which is herein incorporated by reference.

In certain embodiments, the present invention provides a compound of formula I, wherein LBM is VHL binding moiety

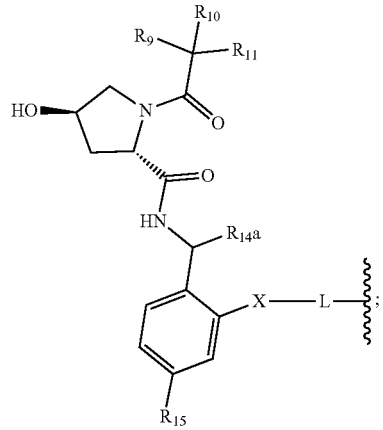

thereby forming a compound of formula I-ii:

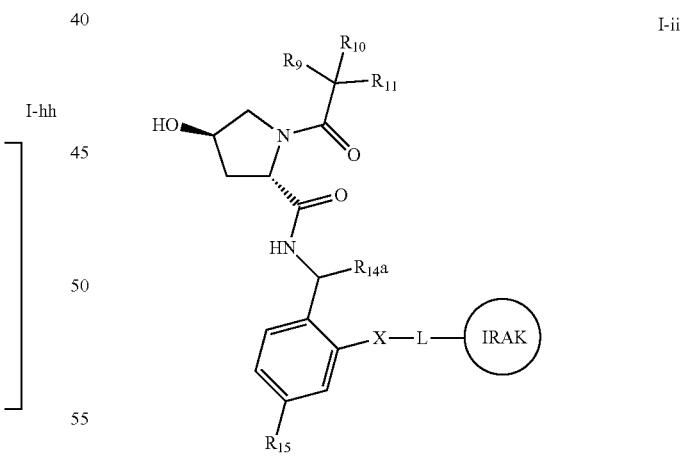

I-ii or a pharmaceutically acceptable salt thereof, wherein L and IRAK are as defined above and described in embodiments herein, and wherein each of the variables X, $R_9$, $R_{10}$, $R_{11}$, $R_{14a}$, and $R_{15}$ is as described and defined in WO 2017/030814, WO 2016/118666, and US 2017/0327469, the entirety of each of which is herein incorporated by reference.

In certain embodiments, the present invention provides a compound of formula I, wherein LBM is an IAP binding moiety

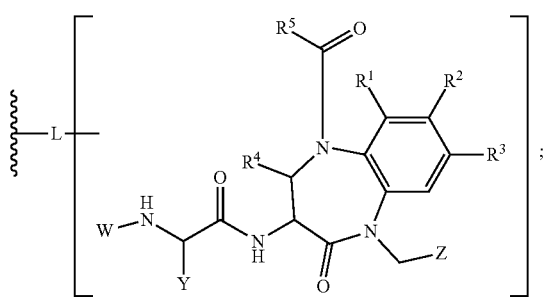

thereby forming a compound of formula I-jj:

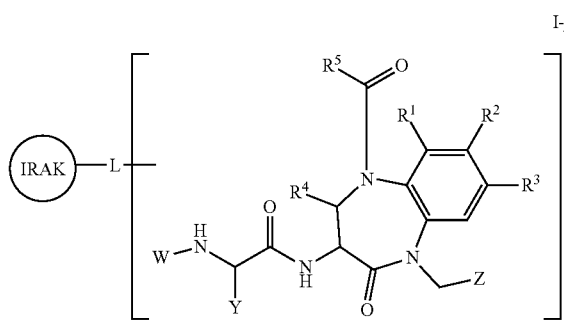

or a pharmaceutically acceptable salt thereof, wherein L and IRAK are as defined above and described in embodiments herein, and wherein each of the variables W, Y, Z, $R^1$, $R^2$, $R^3$, $R^4$, and $R^5$ is as described and defined in WO 2014/044622, US 2015/0225449, WO 2015/071393, and US 2016/0272596, the entirety of each of which is herein incorporated by reference.

In certain embodiments, the present invention provides a compound of formula I, wherein LBM is IAP binding moiety

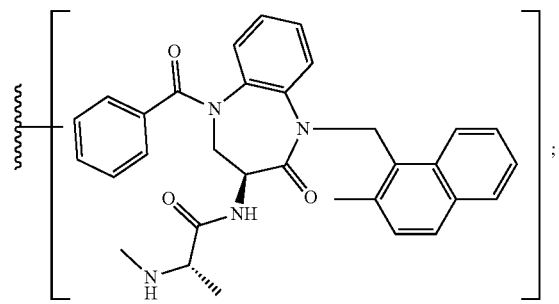

thereby forming a compound of formula I-kk:

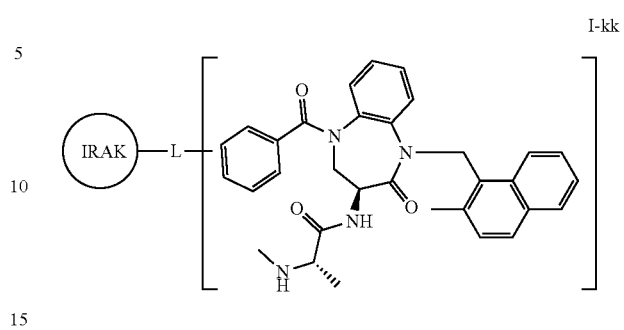

or a pharmaceutically acceptable salt thereof, wherein L and IRAK are as defined above and described in embodiments herein, as described and defined in Kester R. F., et al., *J. Med. Chem.* 2013, 56 (20), 7788-7803, the entirety of which is herein incorporated by reference.

In certain embodiments, the present invention provides a compound of formula I, wherein LBM is MDM2 binding moiety

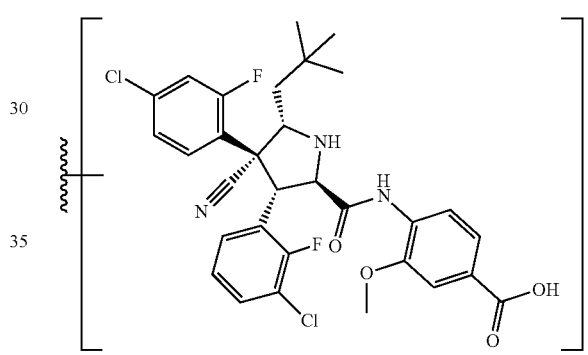

thereby forming a compound of formula I-ll:

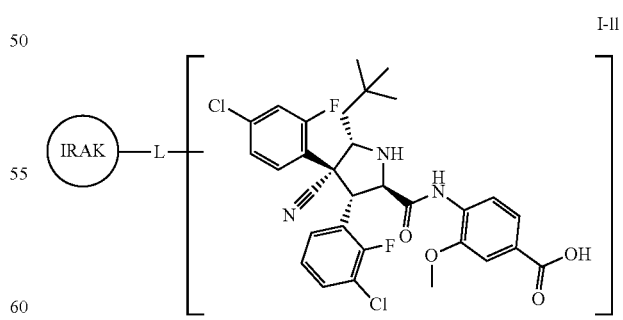

or a pharmaceutically acceptable salt thereof, wherein L and IRAK are as defined above and described in embodiments herein, as described and defined in Hines, J. et al., *Cancer Res.* (DOI: 10.1158/0008-5472.CAN-18-2918), the entirety of which is herein incorporated by reference.

In certain embodiments, the present invention provides a compound of formula I, wherein LBM is DCAF16 binding moiety

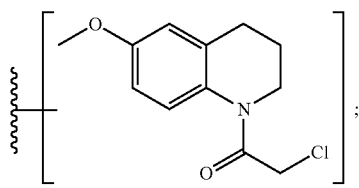

thereby forming a compound of formula I-mm:

I-mm

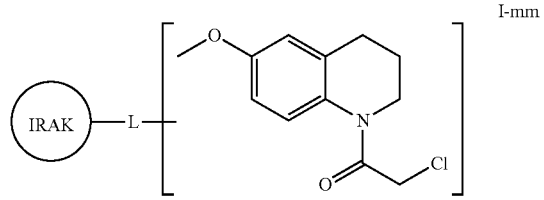

or a pharmaceutically acceptable salt thereof, wherein L and IRAK are as defined above and described in embodiments herein, as described and defined in Zhang, X. et al., *bioRxiv* (doi: https://doi.org/10.1101/443804), the entirety of which is herein incorporated by reference.

In certain embodiments, the present invention provides a compound of formula I,
wherein LBM is RNF 114 binding moiety

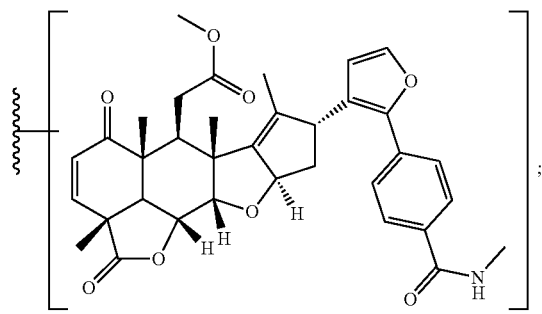

thereby forming a compound of formula I-nn:

I-nn

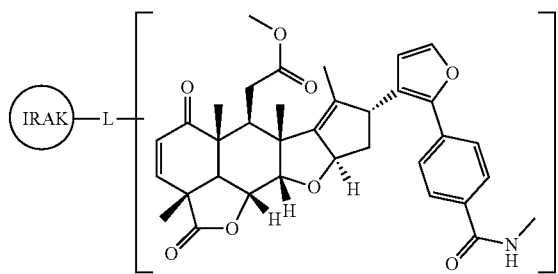

or a pharmaceutically acceptable salt thereof, wherein L and IRAK are as defined above and described in embodiments herein, as described and defined in Spradin, J. N. et al., *bioRxiv* (doi: https://doi.org/10.1101/436998), the entirety of which is herein incorporated by reference.

In certain embodiments, the present invention provides a compound of formula I, wherein LBM is a RNF4 binding moiety

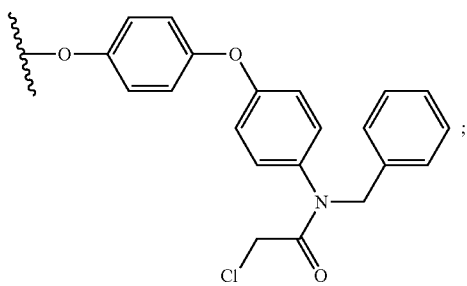 [SMILES: *Oc1ccc(Oc2ccc(N(Cc3ccccc3)C(=O)CCl)cc2)cc1]

thereby forming a compound of formula I-oo:

I-oo

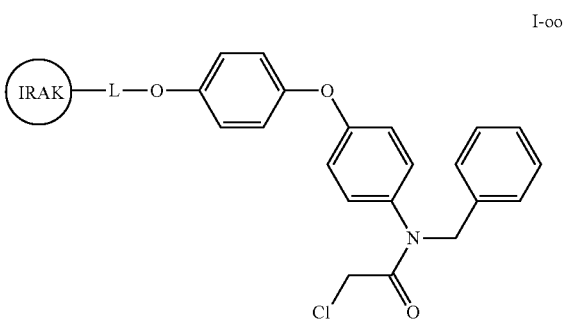

or a pharmaceutically acceptable salt thereof, wherein L and IRAK are as defined above and described in embodiments herein, as described and defined in Ward, C. C., et al., *bioRxiv* (doi: https://doi.org/10.1101/439125), the entirety of which is herein incorporated by reference.

In some embodiments, the present invention provides a compound of formula I, wherein LBM is an E3 ubiquitin ligase (cereblon) binding moiety

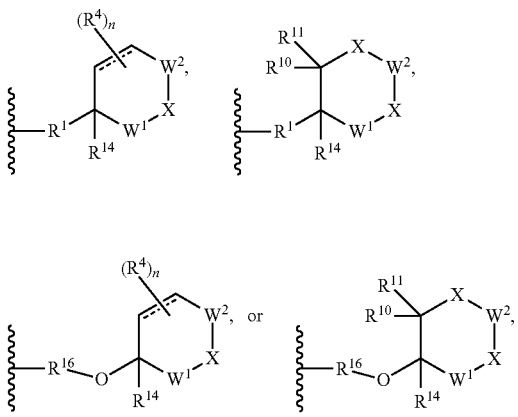

thereby forming a compound of formula I-pp-1, I-pp-2, I-pp-3, or I-pp-4, respectively:

I-pp-1

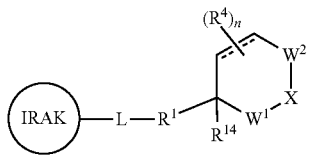

I-pp-2

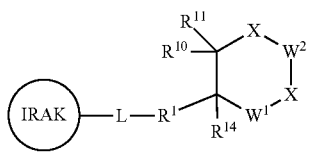

I-pp-3

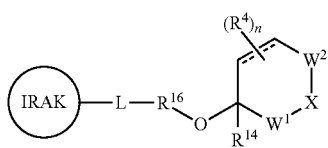

I-pp-4

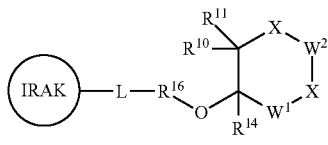

or a pharmaceutically acceptable salt thereof, wherein L and IRAK are as defined above and described herein, and wherein each of the variables $R^1$, $R^4$, $R^{10}$, R, $R^{14}$, $R^{16}$, $W^1$, $W^2$, X and n is as defined in WO 2018/237026, the entirety of each of which is herein incorporated by reference, and wherein

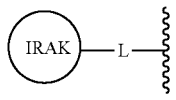

is attached to $R^1$ or $R^{16}$ at the site of attachment of $R^{12}$ as defined in WO 2018/237026, such that

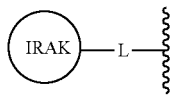

takes the place of the $R^{12}$ substituent.

In some embodiments, the present invention provides a compound of formula I, wherein LBM is an E3 ubiquitin ligase (cereblon) binding moiety

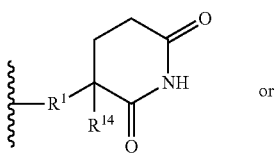

thereby forming a compound of formula I-pp'-1 or I-pp'-3, respectively:

I-pp'-1

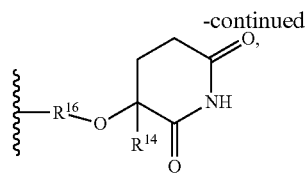

I-pp'-3

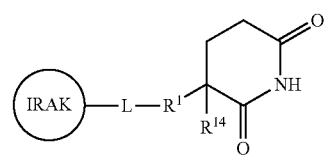

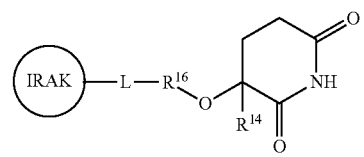

or a pharmaceutically acceptable salt thereof, wherein L and IRAK are as defined above and described herein, and wherein each of the variables $R^1$, $R^{14}$, and $R^{16}$ is as defined in WO 2018/237026, the entirety of each of which is herein incorporated by reference, and wherein

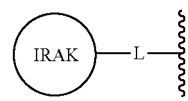

is attached to $R^1$ or $R^{16}$ at the site of attachment of $R^{12}$ as defined in WO 2018/237026, such that

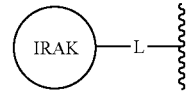

takes the place of the $R^{12}$ substituent.

In certain embodiments, the present invention provides a compound of formula I, wherein LBM is an E3 ubiquitin ligase (cereblon) binding moiety

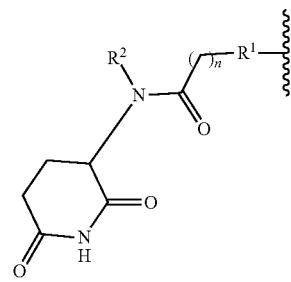

thereby forming a compound of formula I-qq:

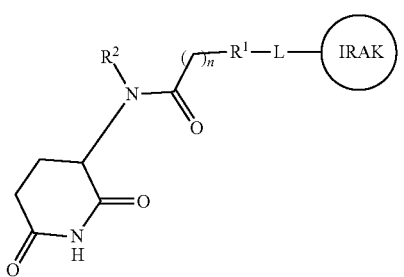

I-qq or a pharmaceutically acceptable salt thereof, wherein L and IRAK are as defined above and described in embodiments herein, and wherein each of the variables $R_1$, $R_2$, and n is as described and defined in WO 2019/043214, the entirety of each of which is herein incorporated by reference.

In certain embodiments, the present invention provides a compound of formula I, wherein LBM is a VHL binding moiety thereby forming a compound of formula I-rr-1 or I-rr-2:

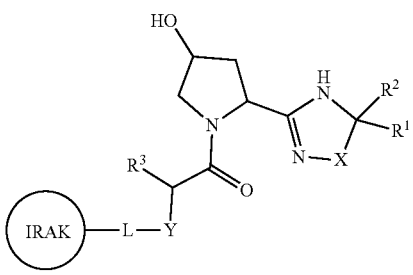

I-rr-1

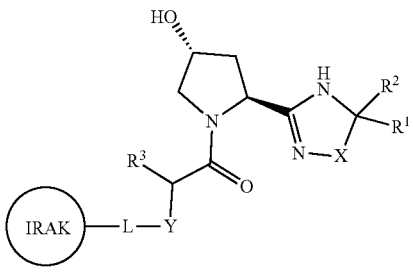

I-rr-2 or a pharmaceutically acceptable salt thereof, wherein L and IRAK are as defined above and described in embodiments herein, and wherein each of the variables $R^1$, $R^2$, $R^3$, X, and Y is as defined and described in WO 2019/084026, the entirety of each of which is herein incorporated by reference.

In certain embodiments, the present invention provides a compound of formula I, wherein LBM is a VHL binding moiety thereby forming a compound of formula I-ss-1 or I-ss-2:

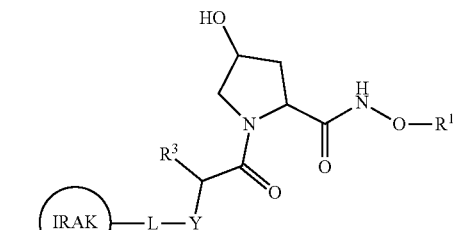

I-ss-1

I-ss-2 or a pharmaceutically acceptable salt thereof, wherein L and IRAK are as defined above and described in embodiments herein, and wherein each of the variables $R^1$, $R^3$, and Y is as defined and described in WO 2019/084030, the entirety of each of which is herein incorporated by reference.

In certain embodiments, the present invention provides a compound of formula I, wherein LBM is a E3 ubiquitin ligase (cereblon) binding moiety thereby forming a compound of formula I-tt-1, I-tt-2, I-tt-3, or I-tt-4:

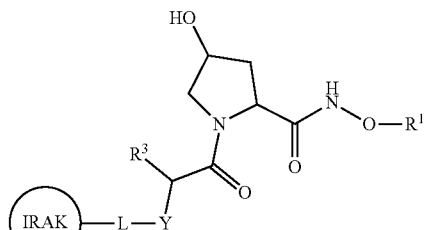

I-tt-1

I-tt-2

I-tt-3

I-tt-4 or a pharmaceutically acceptable salt thereof, wherein L and IRAK are as defined above and described herein, and wherein each of the variables $R^4$, $R^{10}$, $R^{11}$, $R^{15}$, $R^{16}$, $R^{17}$, $W^1$, $W^2$, and X is as defined in WO 2019/099868 which is herein incorporated by reference in its entirety, and wherein

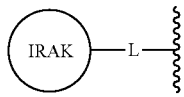

is attached to $R^{17}$ or $R^{16}$ at the site of attachment of $R^{12}$ as defined in WO 2018/237026, such that

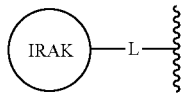

takes the place of the $R^{12}$ substituent.

In certain embodiments, the present invention provides a compound of formula I, wherein LBM is a E3 ubiquitin ligase (cereblon) binding moiety thereby forming a compound of formula I-uu:

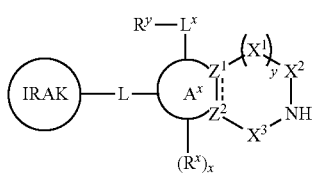

I-uu or a pharmaceutically acceptable salt thereof, wherein L and IRAK are as defined above and described in embodiments herein, wherein:

each $X^1$ is independently —$CH_2$—, —O—, —NR—, —$CF_2$—,

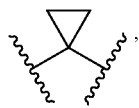

—C(O)—, —C(S)—, or

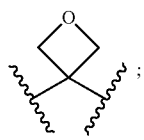 [SMILES: *C1(*)COC1]

$X^2$ and $X^3$ are independently —$CH_2$—, —C(O)—, —C(S)—, or

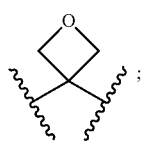 [SMILES: *C1(*)COC1]

$Z^1$ and $Z^2$ are independently a carbon atom or a nitrogen atom;

Ring $A^x$ is a fused ring selected from benzo or a 5-6 membered heteroaryl ring having 1-4 heteroatoms independently selected from nitrogen, oxygen, and sulfur;

$L^x$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —$CR_2$—, —CRF—, —$CF_2$—, —NR—, or —$S(O)_2$—;

each $R^x$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —C(S)$NR_2$, —N(R)C(O)OR, —N(R)C(O)R, —N(R)C(O)$NR_2$, —N(R)$S(O)_2R$, —$OP(O)R^2$, —OP(O)$(OR)_2$, —OP(O)(OR)$NR_2$, —OP(O)$(NR_2)_2$, —$Si(OR)R^2$, and —$SiR_3$; or two $R^x$ groups are optionally taken together to form an optionally substituted 5-8 membered partially unsaturated or aryl fused ring having 0-2 heteroatoms independently selected from nitrogen, oxygen, or sulfur;

each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:

two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur;

$R^y$ is selected from

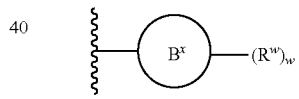

or hydrogen;

Ring $B^x$ is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring $B^x$ is further optionally substituted with 1-2 oxo groups;

each $R^w$ is independently selected from hydrogen, deuterium, $R^z$, halogen, —CN, —$NO_2$, —OR, —SR, —$NR_2$, —$S(O)_2R$, —$S(O)_2NR_2$, —S(O)R, —$CF_2R$, —$CF_3$, —$CR_2(OR)$, —$CR_2(NR_2)$, —C(O)R, —C(O)OR, —C(O)$NR_2$, —C(O)N(R)OR, —OC(O)R, —OC(O)$NR_2$, —N(R)C(O)OR, —N(R)C(O)R, —N(R)C(O)$NR_2$, —N(R)$S(O)_2R$, —$OP(O)R^2$, —OP(O)$(OR)_2$, —OP(O)(OR)$NR_2$, —OP(O)$(NR_2)_2$, and —$SiR_3$;

each $R^z$ is independently selected from an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;

is a single or double bond;
x is 0, 1, 2, 3 or 4;
y is 0, 1 or 2; and
w is 0, 1, 2, 3 or 4.

As defined above and described herein, each $X^1$ is independently —CH$_2$—, —O—, —NR—, —CF$_2$—,

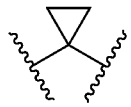 [SMILES: *C1(*)CC1]

—C(O)—, —C(S)—, or

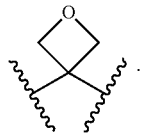 [SMILES: *C1(*)COC1]

In some embodiments, $X^1$ is a covalent bond. In some embodiments, $X^1$ is —CH$_2$—. In some embodiments, $X^1$ is —O—. In some embodiments, $X^1$ is —NR—. In some embodiments, $X^1$ is —CF$_2$—. In some embodiments, $X^1$ is

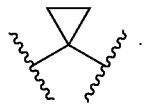

In some embodiments, $X^1$ is —C(O)—. In some embodiments, $X^1$ is —C(S)—. In some embodiments, $X^1$ is

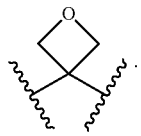 [SMILES: *C1(*)COC1]

In certain embodiments, $X^1$ is selected from those shown in the compounds of Table 1.

As defined above and described herein, $X^2$ and $X^3$ are independently —CH$_2$—, —C(O)—, —C(S)—, or

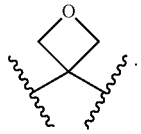 [SMILES: *C1(*)COC1]

In some embodiments, $X^2$ and $X^3$ are independently —CH$_2$—. In some embodiments, $X^2$ and $X^3$ are independently —C(O)—. In some embodiments, $X^2$ and $X^3$ are independently —C(S)—. In some embodiments, $X^2$ and $X^3$ are independently

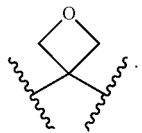

In certain embodiments, $X^2$ and $X^3$ are independently selected from those shown in the compounds of Table 1.

As define above and described herein, $Z^1$ and $Z^2$ are independently a carbon atom or a nitrogen atom.

In some embodiments, $Z^1$ and $Z^2$ are independently a carbon atom. In some embodiments, $Z^1$ and $Z^2$ are independently a carbon atom.

In certain embodiments, $Z^1$ and $Z^2$ are independently selected from those shown in the compounds of Table 1.

As defined above and described herein, Ring $A^x$ is fused ring selected from benzo or a 5-6 membered heteroaryl ring having 1-4 heteroatoms independently selected from nitrogen, oxygen, and sulfur.

In some embodiments, Ring $A^x$ is benzo. In some embodiments, Ring $A^x$ is a 5-6 membered heteroaryl ring having 1-4 heteroatoms independently selected from nitrogen, oxygen, and sulfur.

In some embodiments, Ring $A^x$ is

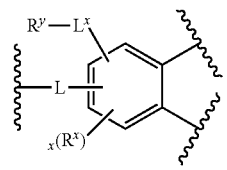

In some embodiments, Ring $A^x$ is

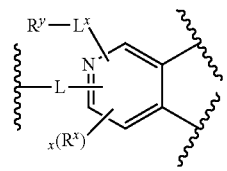

In some embodiments, Ring $A^x$ is

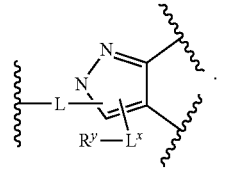

In some embodiments, Ring $A^x$ is

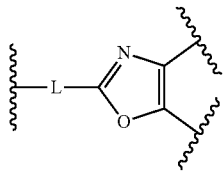

In certain embodiments, Ring $A^x$ is selected from those shown in the compounds of Table 1.

As defined above and described herein, $L^x$ is a covalent bond or a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—.

In some embodiments, $L^x$ is a covalent bond. In some embodiments, $L^x$ is a $C_{1-3}$ bivalent straight or branched saturated or unsaturated hydrocarbon chain wherein 1-2 methylene units of the chain are independently and optionally replaced with —O—, —S—, —C(O)—, —C(S)—, —CR$_2$—, —CRF—, —CF$_2$—, —NR—, or —S(O)$_2$—.

In some embodiments, $L^x$ is —C(O)—.

In certain embodiments, $L^x$ is selected from those shown in the compounds of Table 1.

As defined above and described herein, each $R^x$ is independently selected from hydrogen, deuterium, $R^z$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —C(S)NR$_2$, N(R)C(O)OR, —N(R)C(O)R, —N(R)C(O)NR$_2$, —N(R)S(O)$_2$R, —OP(O)R$^2$, —OP(O)(OR)$_2$, OP(O)(OR)NR$_2$, —OP(O)(NR$_2$)$_2$, —Si(OR)R$^2$, —SF$_5$, and —SiR$_3$, or two $R^x$ groups are optionally taken together to form an optionally substituted 5-8 membered partially unsaturated or aryl fused ring having 0-2 heteroatoms independently selected from nitrogen, oxygen, or sulfur.

In some embodiments, $R^x$ is hydrogen. In some embodiments, $R^x$ is deuterium. In some embodiments, $R^x$ is $R^z$. In some embodiments, $R^x$ is halogen. In some embodiments, $R^x$ is —CN. In some embodiments, $R^x$ is —NO$_2$. In some embodiments, $R^x$ is —OR. In some embodiments, $R^x$ is —SR. In some embodiments, $R^x$ is —NR$_2$. In some embodiments, $R^x$ is —S(O)$_2$R. In some embodiments, $R^x$ is —S(O)$_2$NR$_2$. In some embodiments, $R^x$ is —S(O)R. In some embodiments, $R^x$ is —CF$_2$R. In some embodiments, $R^x$ is —CF$_3$. In some embodiments, $R^x$ is —CR$_2$(OR). In some embodiments, $R^x$ is —CR$_2$(NR$_2$). In some embodiments, $R^x$ is —C(O)R. In some embodiments, $R^x$ is —C(O)OR. In some embodiments, $R^x$ is —C(O)NR$_2$. In some embodiments, $R^x$ is —C(O)N(R)OR. In some embodiments, $R^x$ is —OC(O)R. In some embodiments, $R^x$ is —OC(O)NR$_2$. In some embodiments, $R^x$ is —C(S)NR$_2$. In some embodiments, $R^x$ is —N(R)C(O)OR. In some embodiments, $R^x$ is —N(R)C(O)R. In some embodiments, $R^x$ is —N(R)C(O)NR$_2$. In some embodiments, $R^x$ is —N(R)S(O)$_2$R. In some embodiments, $R^x$ is —OP(O)R$^2$. In some embodiments, $R^x$ is —OP(O)(OR)$_2$. In some embodiments, $R^x$ is —OP(O)(OR)NR$_2$. In some embodiments, $R^x$ is —OP(O)(NR$_2$)$_2$. In some embodiments, $R^x$ is —Si(OR)R$^2$. In some embodiments, $R^x$ is —SF$_5$. In some embodiments, $R^x$ is —SiR$_3$. In some embodiments, two $R^x$ groups are optionally taken together to form an optionally substituted 5-8 membered partially unsaturated or aryl fused ring having 0-2 heteroatoms independently selected from nitrogen, oxygen, or sulfur.

In some embodiments, $R^x$ is fluoro. In some embodiments, $R^x$ is bromo. In some embodiments, $R^x$ is methyl. In some embodiments, $R^x$ is —OH. In some embodiments, $R^x$ is —NH$_2$. In some embodiments, $R^x$ is —NHCH$_3$. In some embodiments, $R^x$ is —N(CH$_3$)$_2$. In some embodiments, $R^x$ is —NHCH(CH$_3$)$_2$. In some embodiments, $R^x$ is —NHSO$_2$CH$_3$. In some embodiments, $R^x$ is —CH$_2$OH. In some embodiments, $R^x$ is —CH$_2$NH$_2$. In some embodiments, $R^x$ is —C(O)NH$_2$. In some embodiments, $R^x$ is —C(O)NHCH$_3$. In some embodiments, $R^x$ is

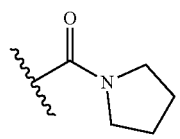 [SMILES: *C(=O)N1CCCC1]

In some embodiments, $R^x$ is

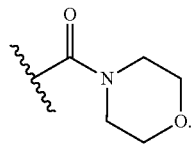 [SMILES: *C(=O)N1CCOCC1]

In some embodiments, $R^x$ is

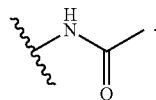

In some embodiments, $R^x$ is

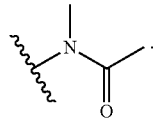

In some embodiments, $R^x$ is

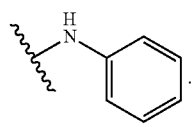

In some embodiments, $R^x$ is

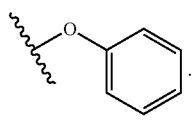 [SMILES: *Oc1ccccc1]

In some embodiments, $R^x$ is

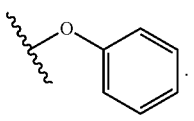 [SMILES: *Oc1ccccc1]

In some embodiments, $R^x$ is

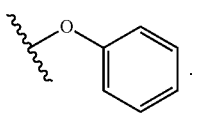 [SMILES: *Oc1ccccc1]

In some embodiments, $R^x$ is

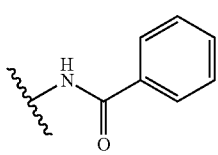

In some embodiments, $R^x$ is

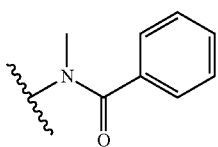

In certain embodiments, each $R^x$ is independently selected from those shown in the compounds of Table 1.

As defined above and described here, each R is independently selected from hydrogen, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

In some embodiments, R is hydrogen. In some embodiments, R is an optionally substituted $C_{1-6}$ aliphatic. In some embodiments, R is an optionally substituted phenyl. In some embodiments, R is an optionally substituted 4-7 membered saturated or partially unsaturated heterocyclic having 1-2 heteroatoms independently selected from nitrogen, oxygen, and sulfur. In some embodiments, R is an optionally substituted a 5-6 membered heteroaryl ring having 1-4 heteroatoms independently selected from nitrogen, oxygen, and sulfur. In some embodiments, two R groups on the same carbon or nitrogen are optionally taken together with their intervening atoms to form an optionally substituted 4-7 membered saturated, partially unsaturated, or heteroaryl ring having 0-3 heteroatoms, in addition to the carbon or nitrogen, independently selected from nitrogen, oxygen, and sulfur.

As defined above and described herein, $R^y$ is selected from


or hydrogen.

In some embodiment $R^y$ is


In some embodiments, $R^y$ is hydrogen.

In certain embodiments, $R^y$ is selected from those shown in the compounds of Table 1.

As defined above and described herein, Ring $B^x$ is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur, wherein Ring $B^x$ is further optionally substituted with 1-2 oxo groups.

In some embodiments, Ring $B^x$ is phenyl. In some embodiments, Ring $B^x$ is a 4-10 membered saturated or partially unsaturated mono- or bicyclic carbocyclic or heterocyclic ring having 1-3 heteroatoms independently selected from nitrogen, oxygen, and sulfur In some embodiments, Ring $B^x$ is a 5-6 membered heteroaryl ring having 1-4 heteroatoms independently selected from nitrogen, oxygen, and sulfur. In some embodiments, Ring $B^x$ is further optionally substituted with 1-2 oxo groups.

In some embodiments, Ring $B^x$ is

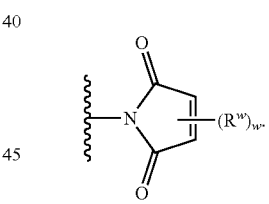

In some embodiments, Ring $B^x$ is

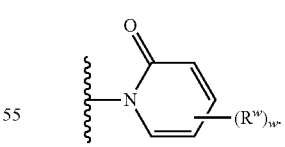

In some embodiments, Ring $B^x$ is

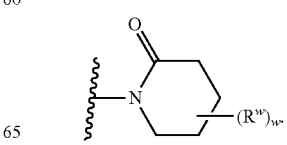

In some embodiments Ring $B^x$ is

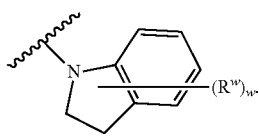

In some embodiments Ring $B^x$ is

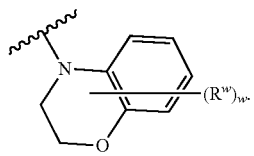

In certain embodiments, Ring $B^x$ is selected from those shown in the compounds of Table 1.

As defined above and described herein, each $R^w$ is independently selected from hydrogen, deuterium, $R^z$, halogen, —CN, —NO$_2$, —OR, —SR, —NR$_2$, —S(O)$_2$R, —S(O)$_2$NR$_2$, —S(O)R, —CF$_2$R, —CF$_3$, —CR$_2$(OR), —CR$_2$(NR$_2$), —C(O)R, —C(O)OR, —C(O)NR$_2$, —C(O)N(R)OR, —OC(O)R, —OC(O)NR$_2$, —N(R)C(O)OR, —N(R)C(O)R, —N(R)C(O)NR$_2$, —N(R)S(O)$_2$R, —OP(O)R$_2$, —OP(O)(OR)$_2$, —OP(O)(OR)NR$_2$, —OP(O)(NR$_2$)$_2$, —SF$_5$, and —SiR$_3$.

In some embodiments, $R^w$ is hydrogen. In some embodiments, $R^w$ is deuterium. In some embodiments, $R^w$ is $R^z$. In some embodiments, $R^w$ is halogen. In some embodiments, $R^w$ is —CN. In some embodiments, $R^w$ is —NO$_2$. In some embodiments, $R^w$ is —OR. In some embodiments, $R^w$ is —SR. In some embodiments, $R^w$ is —NR$_2$. In some embodiments, $R^w$ is —S(O)$_2$R. In some embodiments, $R^w$ is —S(O)$_2$NR$_2$. In some embodiments, $R^w$ is —S(O)R. In some embodiments, $R^w$ is —CF$_2$R. In some embodiments, $R^w$ is —CF$_3$. In some embodiments, $R^w$ is —CR$_2$(OR). In some embodiments, $R^w$ is —CR$_2$(NR$_2$). In some embodiments, $R^w$ is —C(O)R. In some embodiments, $R^w$ is —C(O)OR. In some embodiments, $R^w$ is —C(O)NR$_2$. In some embodiments, $R^w$ is —C(O)N(R)OR. In some embodiments, $R^w$ is —OC(O)R. In some embodiments, $R^w$ is —OC(O)NR$_2$. In some embodiments, $R^w$ is —N(R)C(O)OR. In some embodiments, $R^w$ is —N(R)C(O)R. In some embodiments, $R^w$ is —N(R)C(O)NR$_2$. In some embodiments, $R^w$ is —N(R)S(O)$_2$R. In some embodiments, $R^w$ is —OP(O)R$^2$. In some embodiments, $R^w$ is —OP(O)(OR)$_2$. In some embodiments, $R^w$ is —OP(O)(OR)NR$_2$. In some embodiments, $R^w$ is —OP(O)(NR$_2$)$_2$. In some embodiments, $R^w$ is —SF$_5$. In some embodiments, $R^w$ is —SiR$_3$.

In certain embodiments, $R^w$ is selected from those shown in the compounds of Table 1.

As defined above and described herein, each $R^z$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur.

In some embodiments, $R^z$ is an optionally substituted $C_{1-6}$ aliphatic. In some embodiments, $R^z$ is an optionally substituted phenyl. In some embodiments, $R^z$ is an optionally substituted 4-7 membered saturated or partially unsaturated heterocyclic ring having 1-2 heteroatoms independently selected from nitrogen, oxygen, and sulfur. In some embodiments, $R^z$ is an optionally substituted 5-6 membered heteroaryl ring having 1-4 heteroatoms independently selected from nitrogen, oxygen, and sulfur.

In some embodiments, $R^z$ is

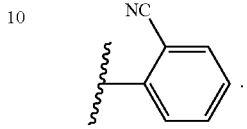

In some embodiments, $R^z$ is

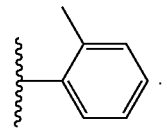 [SMILES: *c1ccccc1C]

In some embodiments, $R^z$ is

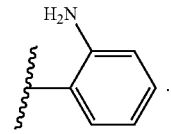

In some embodiments, $R^z$ is

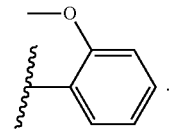 [SMILES: *c1ccccc1OC]

In some embodiments, $R^Z$ is

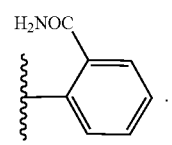

In some embodiments, $R^Z$ is

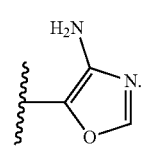 [SMILES: *c1ocnc1N]

In some embodiments, $R^z$ is

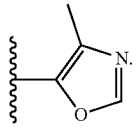

In certain embodiments, $R^z$ is selected from those shown in the compounds of Table 1.

As defined above and described herein, ≡ is a single or double bond.

In some embodiments, ≡ is a single bond. In some embodiments, ≡ is a double bond.

In certain embodiments, ≡ is selected from those shown in the compounds of Table 1.

As defined above and described herein, w is 0, 1, 2, 3 or 4.

In some embodiments, w is 0. In some embodiments, w is 1. In some embodiments, w is 2. In some embodiments, w is 3. In some embodiments, w is 4.

In certain embodiments, w is selected from those shown in the compounds of Table 1.

As defined above and described herein, x is 0, 1, 2, 3 or 4.

In some embodiments, x is 0. In some embodiments, x is 1. In some embodiments, m is 2. In some embodiments, x is 3. In some embodiments, x is 4.

In certain embodiments, x is selected from those shown in the compounds of Table 1.

As defined above and described herein, y is 0, 1 or 2.

In some embodiments, y is 0. In some embodiments, y is 1. In some embodiments, y is 2.

In certain embodiments, y is selected from those shown in the compounds of Table 1.

In some embodiments, the present invention provides a compound of formula I-uu, wherein Ring $A^x$ is benzo, y is 1, $X^1$ is —CH$_2$—, $X^2$ and $X^3$ are —C(O)—, and $Z^1$ and $Z^2$ are carbon atoms as shown, to provide a compound of formula I-uu-1:

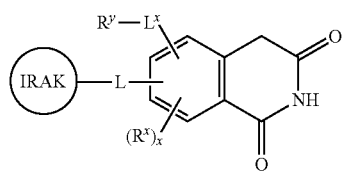

I-uu-1 or a pharmaceutically acceptable salt thereof, wherein each of IRAK, L, $L^x$, $R^x$, $R^y$, and x is as defined above and described in embodiments herein, both singly and in combination.

In some embodiments, the present invention provides a compound of formula I-uu, wherein Ring $A^x$ is imidazolyl, y is 1, $X^1$ is —CH$_2$—, $X^2$ and $X^3$ are —C(O)—, and $Z^1$ and $Z^2$ are carbon atoms as shown, to provide a compound of formula I-uu-2:

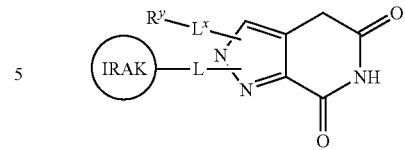

I-uu-2 or a pharmaceutically acceptable salt thereof, wherein each of IRAK, L, $L^x$, and $R^y$ is as defined above and described in embodiments herein, both singly and in combination.

In some embodiments, the present invention provides a compound of formula I-uu, wherein Ring $A^x$ is imidazolyl, y is 1, $X^1$ is —CH$_2$—, $X^2$ and $X^3$ are —C(O)—, and $Z^1$ and $Z^2$ are carbon atoms as shown, to provide a compound of formula I-uu-3:

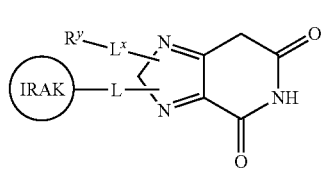

I-uu-3 or a pharmaceutically acceptable salt thereof, wherein each of IRAK, L, $L^x$, and $R^y$ is as defined above and described in embodiments herein, both singly and in combination.

In some embodiments, the present invention provides a compound of formula I-uu, wherein Ring $A^x$ is oxazolyl, y is 1, $X^1$ is —CH$_2$—, $X^2$ and $X^3$ are —C(O)—, and $Z^1$ and $Z^2$ are carbon atoms as shown, to provide a compound of formula I-uu-4:

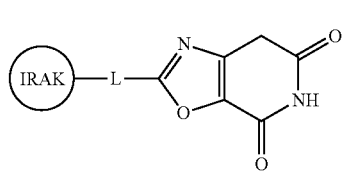

I-uu-4 or a pharmaceutically acceptable salt thereof, wherein each of IRAK and L is as defined above and described in embodiments herein, both singly and in combination.

In some embodiments, the present invention provides a compound of formula I-uu, wherein Ring $A^x$ is benzo, y is 0, $X^2$ and $X^3$ are —C(O)—, and $Z^1$ and $Z^2$ are carbon atoms as shown, to provide a compound of formula I-uu-5:

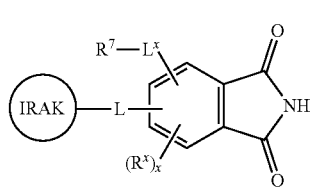

I-uu-5 or a pharmaceutically acceptable salt thereof, wherein each of IRAK, L, $L^x$, $R^x$, $R^y$, and x is as defined above and described in embodiments herein, both singly and in combination.

In some embodiments, the present invention provides a compound of formula I-uu, wherein Ring $A^x$ is benzo, y is 1, $X^1$ is —O—, $X^2$ and $X^3$ are —C(O)—, and $Z^1$ and $Z^2$ are carbon atoms as shown, to provide a compound of formula I-uu-6:

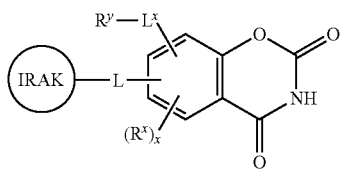

I-uu-6 or a pharmaceutically acceptable salt thereof, wherein each of IRAK, L, $L^x$, $R^x$, $R^y$, and x is as defined above and described in embodiments herein, both singly and in combination.

In some embodiments, the present invention provides a compound of formula I-uu, wherein Ring $A^x$ is benzo, y is 1, $X^1$ is —NR—, $X^2$ and $X^3$ are —C(O)—, and $Z^1$ and $Z^2$ are carbon atoms as shown, to provide a compound of formula I-uu-7:

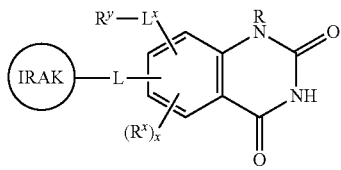

I-uu-7 or a pharmaceutically acceptable salt thereof, wherein each of IRAK, L, $L^x$, R, $R^x$, $R^y$, and x is as defined above and described in embodiments herein, both singly and in combination.

In some embodiments, the present invention provides a compound of formula I-uu, wherein Ring $A^x$ is benzo, y is 1, $X^1$ is —CF$_2$—, $X^2$ and $X^3$ are —C(O)—, and $Z^1$ and $Z^2$ are carbon atoms as shown, to provide a compound of formula I-uu-8:

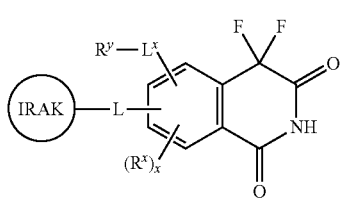

I-uu-8 or a pharmaceutically acceptable salt thereof, wherein each of IRAK, L, $L^x$, $R^x$, $R^y$, and x is as defined above and described in embodiments herein, both singly and in combination.

In some embodiments, the present invention provides a compound of formula I-uu, wherein Ring $A^x$ is benzo, y is 1, $X^1$ is

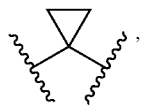 [SMILES: *C1(*)CC1]

$X^2$ and $X^3$ are —C(O)—, and $Z^1$ and $Z^2$ are carbon atoms as shown, to provide a compound of formula I-uu-9:

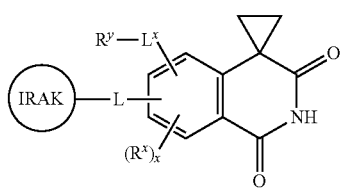

I-uu-9 or a pharmaceutically acceptable salt thereof, wherein each of IRAK, L, $L^x$, $R^x$, $R^y$, and x is as defined above and described in embodiments herein, both singly and in combination.

In some embodiments, the present invention provides a compound of formula I-uu, wherein Ring $A^x$ is pyridyl, y is 1, $X^1$ is —CH$_2$—, $X^2$ and $X^3$ are —C(O)—, and $Z^1$ and $Z^2$ are carbon atoms as shown, to provide a compound of formula I-uu-10:

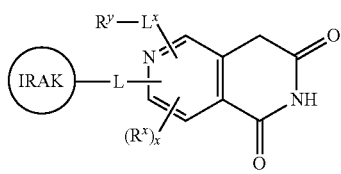

I-uu-10 or a pharmaceutically acceptable salt thereof, wherein each of IRAK, L, $L^x$, $R^x$, $R^y$, and x is as defined above and described in embodiments herein, both singly and in combination.

In some embodiments, the present invention provides a compound of formula I-uu, wherein Ring $A^x$ is pyridyl, y is 1, $X^1$ is —CH$_2$—, $X^2$ and $X^3$ are —C(O)—, and $Z^1$ and $Z^2$ are carbon atoms as shown, to provide a compound of formula I-uu-11:

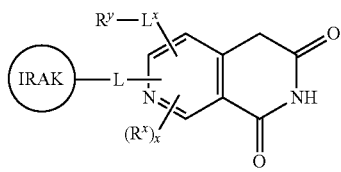

I-uu-11 or a pharmaceutically acceptable salt thereof, wherein each of IRAK, L, $L^x$, $R^x$, $R^y$, and x is as defined above and described in embodiments herein, both singly and in combination.

In some embodiments, the present invention provides a compound of formula I-uu, wherein Ring A is benzo, y is 1, $X^1$, $X^2$ and $X^3$ are —C(O)—, and $Z^1$ and $Z^2$ are carbon atoms as shown, to provide a compound of formula I-uu-12:

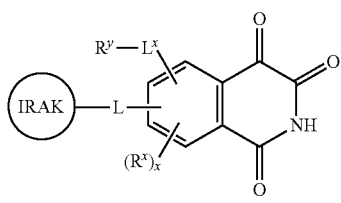

I-uu-12 or a pharmaceutically acceptable salt thereof, wherein each of IRAK, L, $L^x$, $R^x$, $R^y$, and x is as defined above and described in embodiments herein, both singly and in combination.

In some embodiments, LBM is

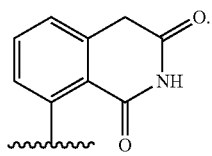

In some embodiments, LBM is

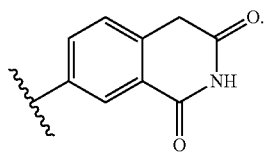 [SMILES: *c1ccc2c(c1)C(=O)NC(=O)C2]

In some embodiments, LBM is

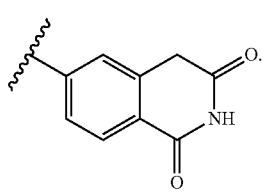 [SMILES: *c1ccc2c(c1)CC(=O)NC2=O]

In some embodiments, LBM is

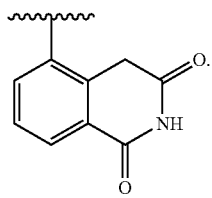 [SMILES: *c1cccc2c1CC(=O)NC2=O]

In some embodiments, LBM is

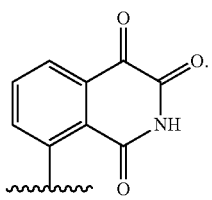 [SMILES: *c1cccc2c1C(=O)NC(=O)C2=O]

In some embodiments, LBM is

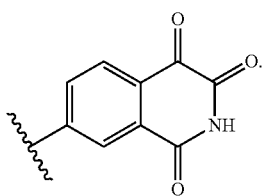 [SMILES: *c1ccc2c(c1)C(=O)NC(=O)C2=O]

In some embodiments, LBM is

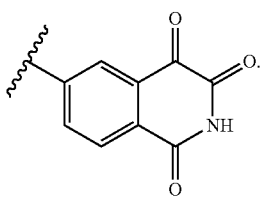 [SMILES: *c1ccc2c(c1)C(=O)C(=O)NC2=O]

In some embodiments, LBM is

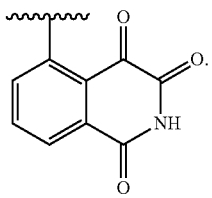 [SMILES: *c1cccc2c1C(=O)C(=O)NC2=O]

In some embodiments, LBM is

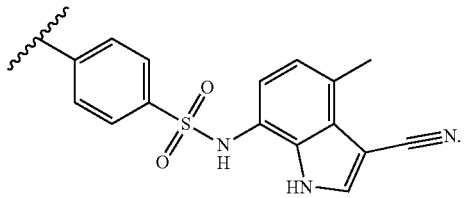

In some embodiments, LBM is
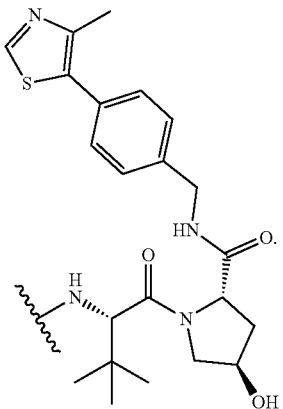
In some embodiments, LBM is
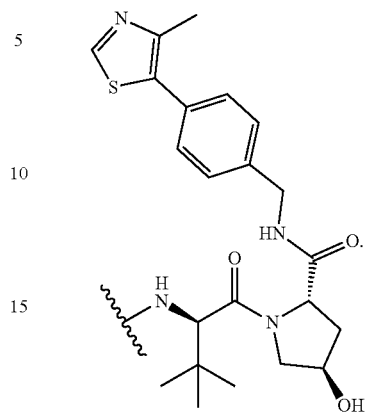
In some embodiments, LBM is
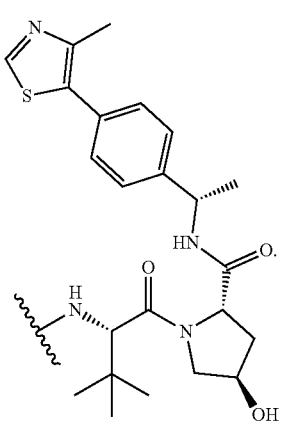
In some embodiments, LBM is
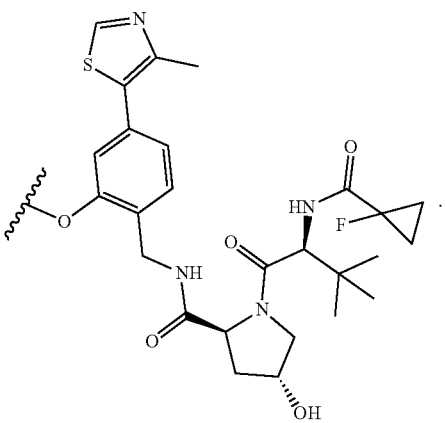
In some embodiments, LBM is
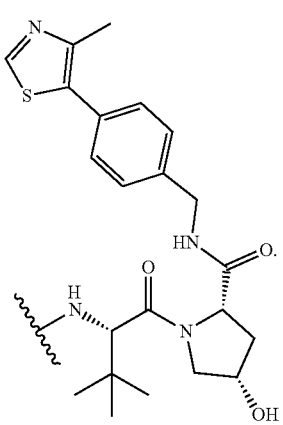
In some embodiments, LBM is
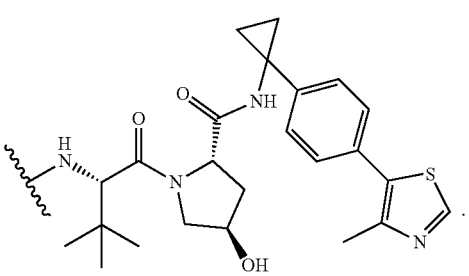

In some embodiments, LBM is
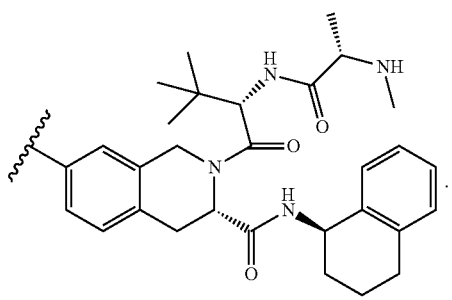
In some embodiments, LBM is
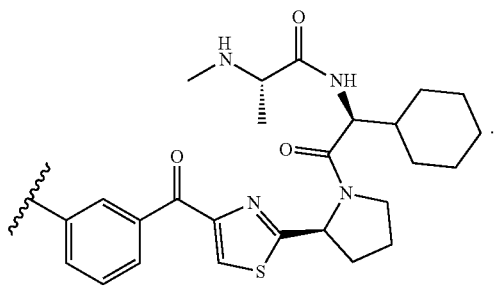
In some embodiments, LBM is
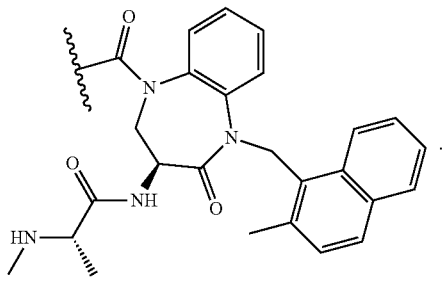 [SMILES: *C(=O)N1C[C@H](NC(=O)[C@H](C)NC)C(=O)N(Cc2c(C)ccc3ccccc23)c2ccccc21]
In some embodiments, LBM is
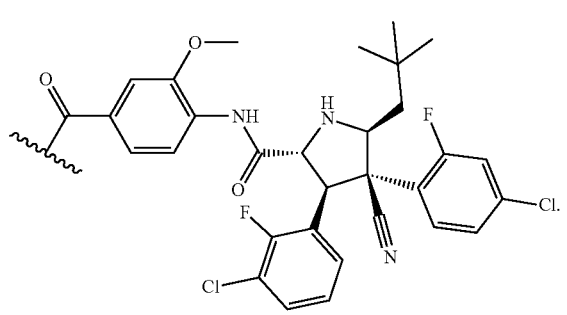
In some embodiments, LBM is
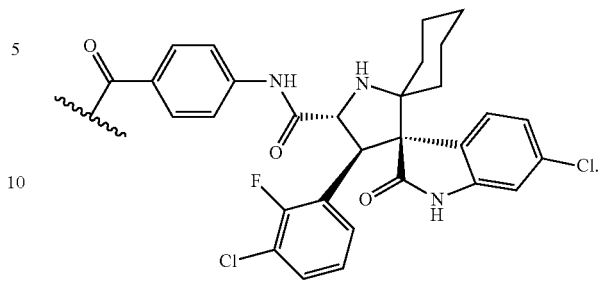
In some embodiments, LBM is
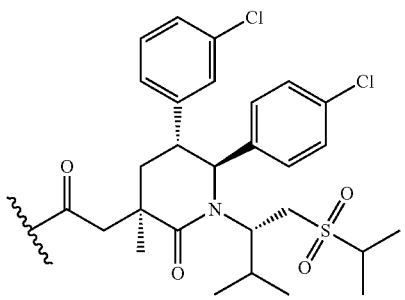
In some embodiments, LBM is
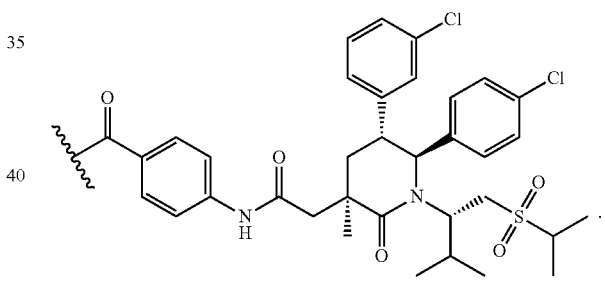
In some embodiments, LBM is
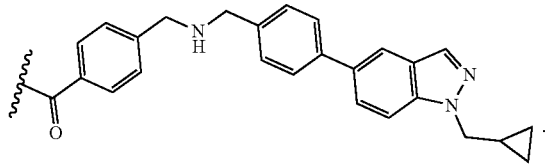
In some embodiments, LBM is
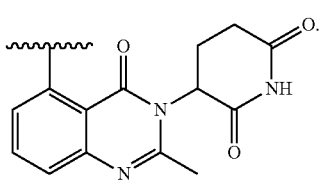 [SMILES: *c1cccc2nc(C)n(C3CCC(=O)NC3=O)c(=O)c12]

In some embodiments, LBM is selected from those in Table 1, below.

In some embodiments, the present invention provides the compound of formula II, wherein LBM is IAP binding moeity

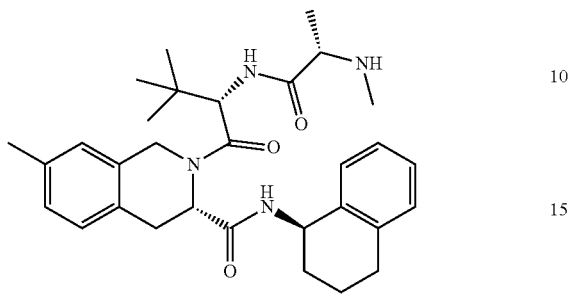

thereby forming a compound of formula II-vv:

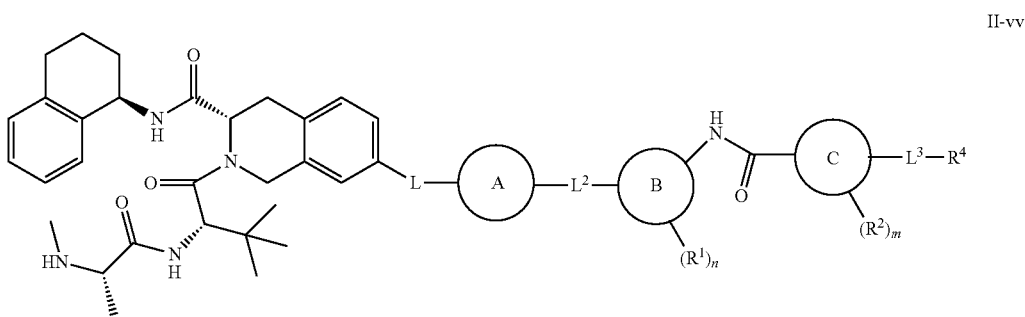

II-vv or a pharmaceutically acceptable salt thereof, wherein each of L, $L^2$, $L^3$, Ring A, Ring B, Ring C, $R^1$, $R^2$, $R^4$, n, and m is as defined above and described in embodiments herein, both singly and in combination.

In some embodiments, the present invention provides the compound of formula II, wherein LBM is IAP binding moeity

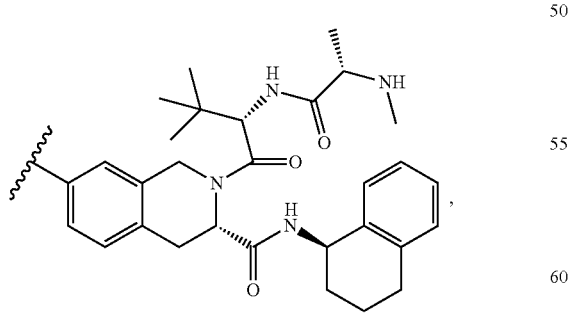

$L^2$ is a covalent bond, Ring A is cyclohexyl, Ring B is pyrazolyl, Ring C is oxazolyl, and Ring D is pyridyl thereby forming a compound of formula II-ww:

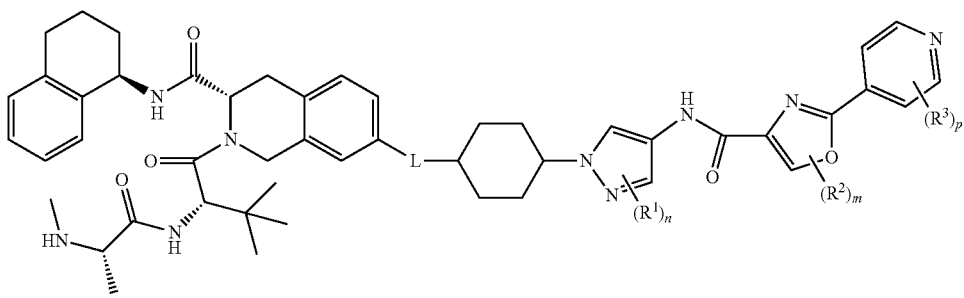

II-ww or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-d, wherein LBM is IAP binding moiety

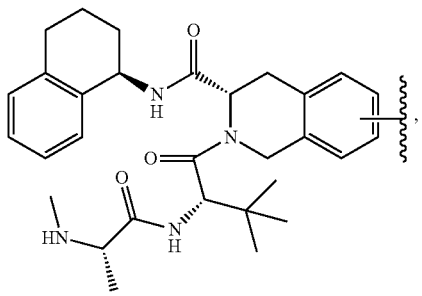

$L^2$ is a covalent bond, Ring A is cyclohexyl, and Ring B is pyrazolyl as shown, thereby forming a compound of formula II-d-8:

or a pharmaceutically acceptable salt thereof, wherein each of L, $L^3$, Ring C, $R^1$, $R^2$, $R^4$, n, and m is as defined above and described in embodiments herein, both singly and in combination.

In certain embodiments, the present invention provides the compound of formula II-e, wherein LBM is IAP binding moiety

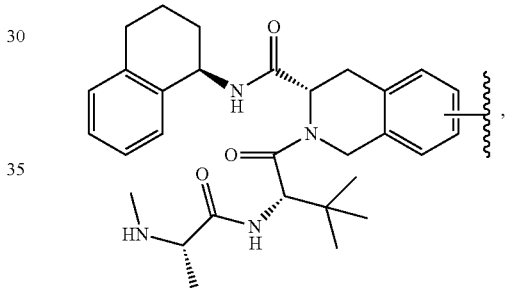

$L^2$ is a covalent bond, Ring A is cyclohexyl, Ring C is pyrazolo[1,5-a]pyrimidine, and Ring B is pyrazolyl as shown, thereby forming a compound of formula II-e-8:

II-d-8

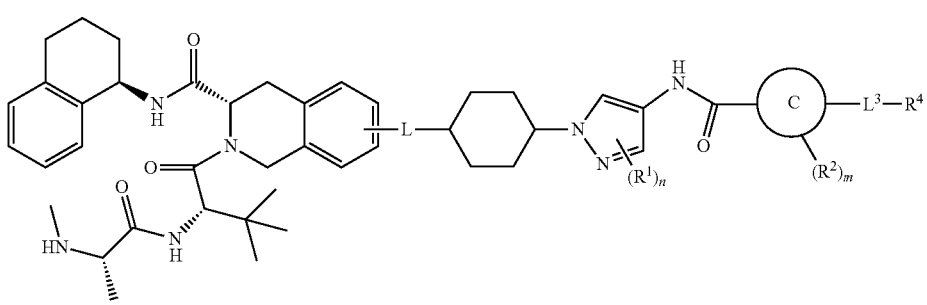

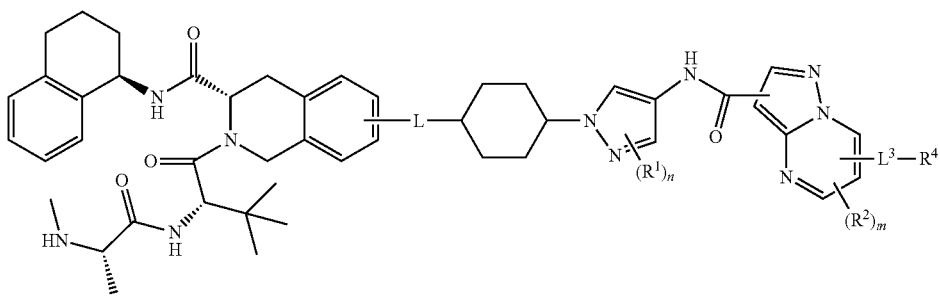

II-e-8 or a pharmaceutically acceptable salt thereof, wherein each of L, $R^1$, $R^2$, $R^3$, n, m, and p is as defined above and described in embodiments herein, both singly and in combination.

In some embodiments, the present invention provides the compound of formula II, wherein LBM is MDM2 binding moiety or a pharmaceutically acceptable salt thereof, wherein each of L, $L^2$, $L^3$, Ring A, Ring B, Ring C, $R^1$, $R^2$, $R^4$, n, and m is as defined above and described in embodiments herein, both singly and in combination.

In some embodiments, the present invention provides the compound of formula II, wherein LBM is MDM2 binding moiety

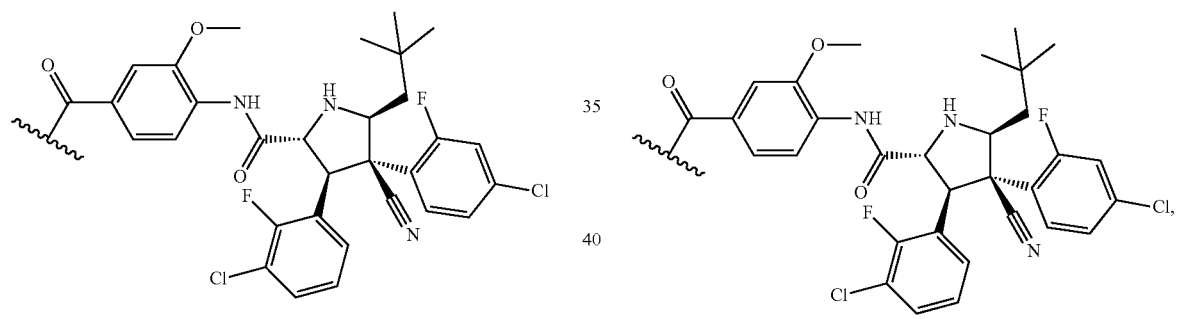

thereby forming a compound of formula II-xx:

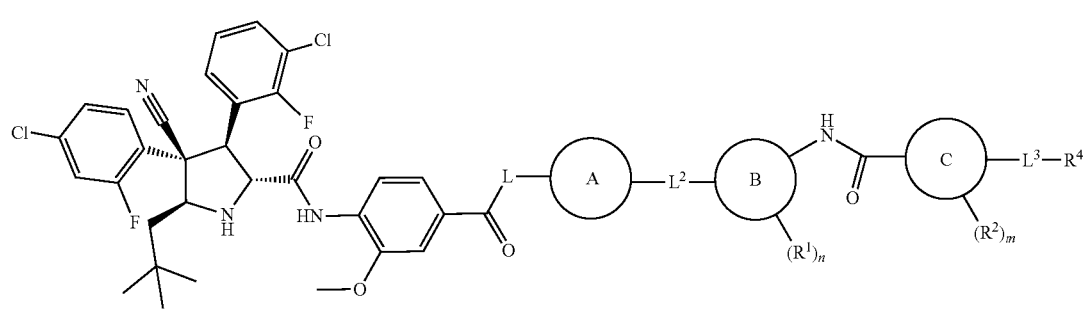

II-xx

L² is a covalent bond, Ring A is cyclohexyl, Ring B is pyrazolyl, Ring C is oxazolyl, and Ring D is pyridyl thereby forming a compound of formula II-yy:

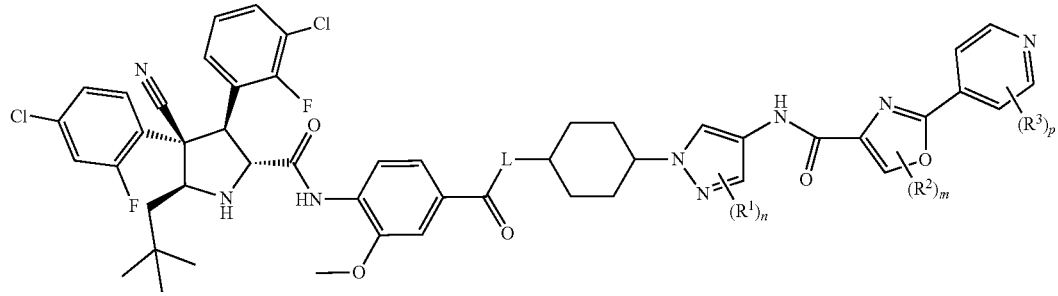

II-yy or a pharmaceutically acceptable salt thereof, wherein each of L, R¹, R², R³, n, m, and p is as defined above and described in embodiments herein, both singly and in combination.

In certain embodiments, the present invention provides the compound of formula II-d, wherein LBM is MDM2 binding moeity

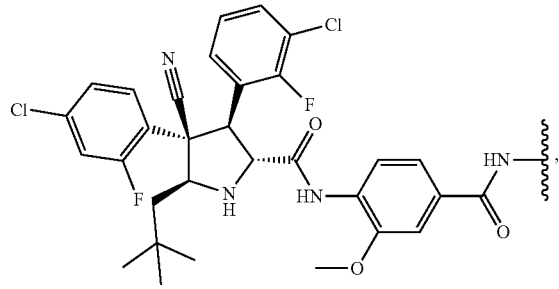

L² is a covalent bond, Ring A is cyclohexyl, and Ring B is pyrazolyl as shown, thereby forming a compound of formula II-d-9:

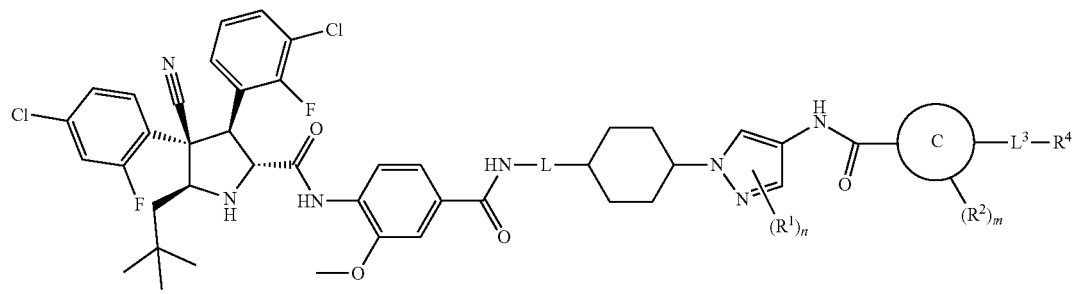

II-d-9 or a pharmaceutically acceptable salt thereof, wherein each of L, L³, Ring C, R¹, R², R⁴, n, and m is as defined above and described in embodiments herein, both singly and in combination.

In certain embodiments, the present invention provides the compound of formula II-e, wherein LBM is MDM2 binding moeity

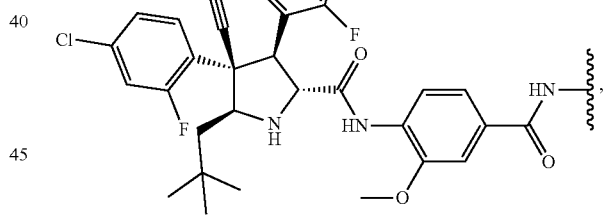

L² is a covalent bond, Ring A is cyclohexyl, Ring C is pyrazolo[1,5-a]pyrimidine, and Ring B is pyrazolyl as shown, thereby forming a compound of formula II-e-9:

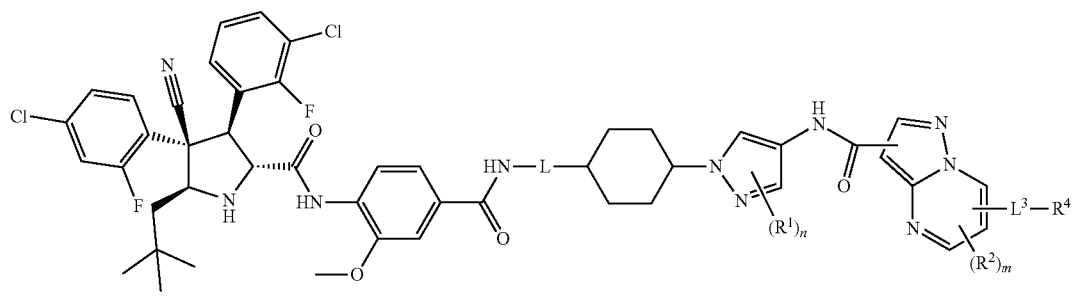

II-e-9 or a pharmaceutically acceptable salt thereof, wherein each of L, R¹, R², R³, n, m, and p is as defined above and described in embodiments herein, both singly and in combination.

In some embodiments, the present invention provides the compound of formula II, wherein LBM is IAP binding moeity

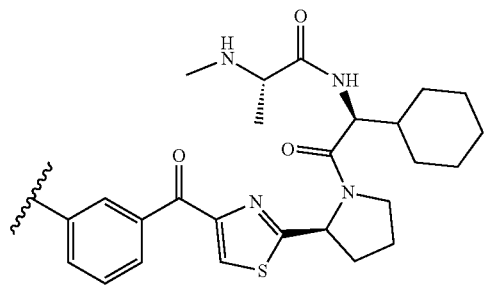

thereby forming a compound of formula II-zz:

or a pharmaceutically acceptable salt thereof, wherein each of L, L², L³, Ring A, Ring B, Ring C, R¹, R², R⁴, n, and m is as defined above and described in embodiments herein, both singly and in combination.

In some embodiments, the present invention provides the compound of formula II, wherein LBM is IAP binding moeity

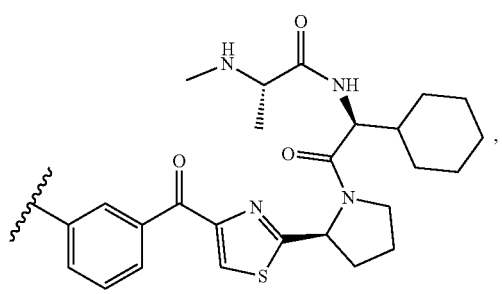

II-zz

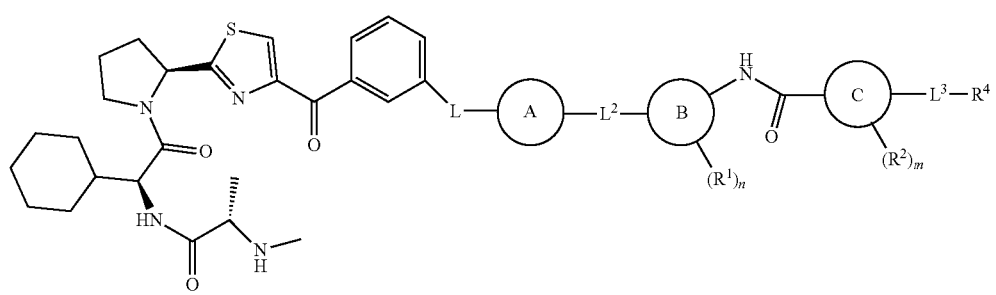

L² is a covalent bond, Ring A is cyclohexyl, Ring B is pyrazolyl, Ring C is oxazolyl, and Ring D is pyridyl thereby forming a compound of formula II-aaa:

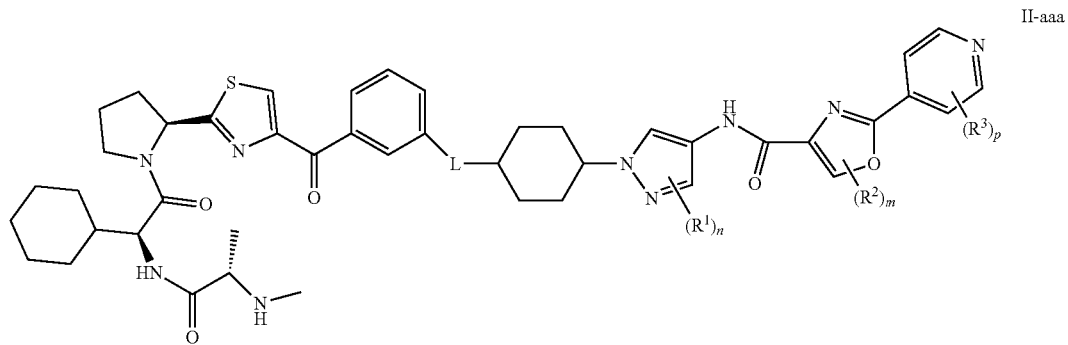

or a pharmaceutically acceptable salt thereof, wherein each of L, R¹, R², R³, n, m, and p is as defined above and described in embodiments herein, both singly and in combination.

In certain embodiments, the present invention provides the compound of formula II-d, wherein LBM is IAP binding moeity

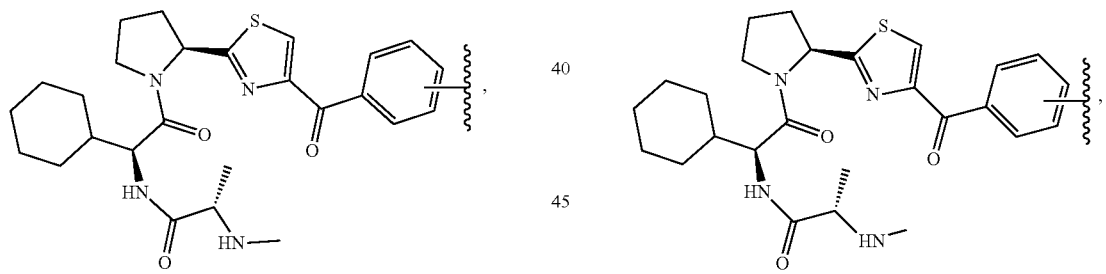

L² is a covalent bond, Ring A is cyclohexyl, and Ring B is pyrazolyl as shown, thereby forming a compound of formula II-d-10:

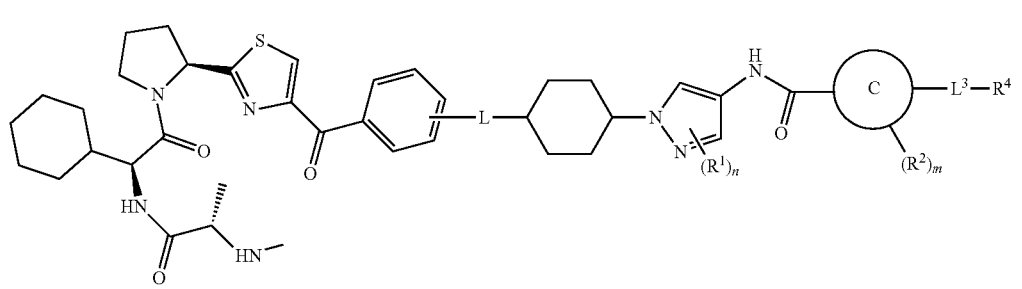

or a pharmaceutically acceptable salt thereof, wherein each of L, L³, Ring C, R¹, R², R⁴, n, and m is as defined above and described in embodiments herein, both singly and in combination.

In certain embodiments, the present invention provides the compound of formula II-e, wherein LBM is IAP binding moeity L² is a covalent bond, Ring A is cyclohexyl, Ring C is pyrazolo[1,5-a]pyrimidine, and Ring B is pyrazolyl as shown, thereby forming a compound of formula II-e-10:

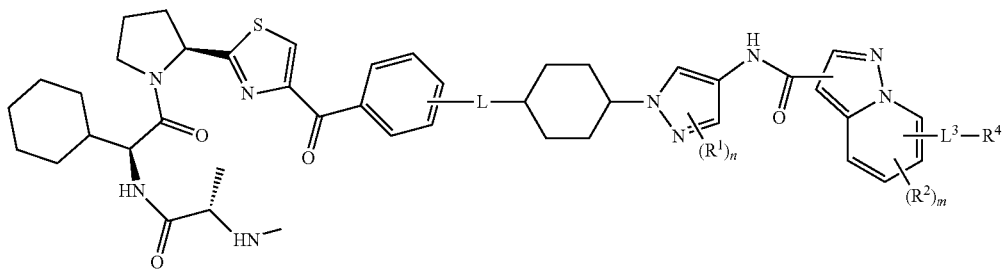

II-e-10 or a pharmaceutically acceptable salt thereof, wherein each of L, R¹, R², R³, n, m, and p is as defined above and described in embodiments herein, both singly and in combination.

In some embodiments, the present invention provides the compound of formula II, wherein LBM is VHL binding moiety

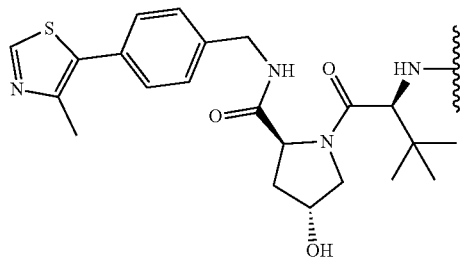 [SMILES: *N[C@H](C(=O)N1C[C@H](O)C[C@H]1C(=O)NCc1ccc(-c2scnc2C)cc1)C(C)(C)C]

thereby forming a compound of formula II-bbb:

or a pharmaceutically acceptable salt thereof, wherein each of L, L², L³, Ring A, Ring B, Ring C, R¹, R², R⁴, n, and m is as defined above and described in embodiments herein, both singly and in combination.

In some embodiments, the present invention provides the compound of formula II, wherein LBM is VHL binding moiety

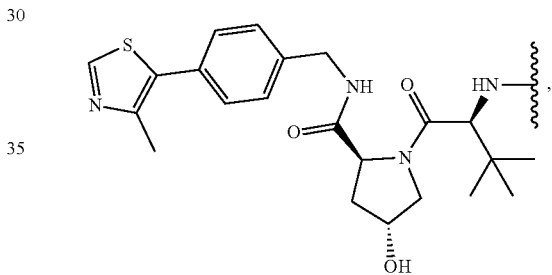

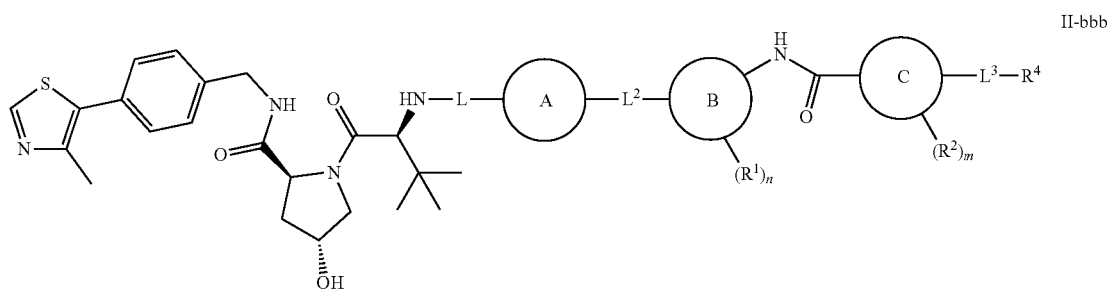

II-bbb

L² is a covalent bond, Ring A is cyclohexyl, Ring B is pyrazolyl, Ring C is oxazolyl, and Ring D is pyridyl thereby forming a compound of formula II-ccc:

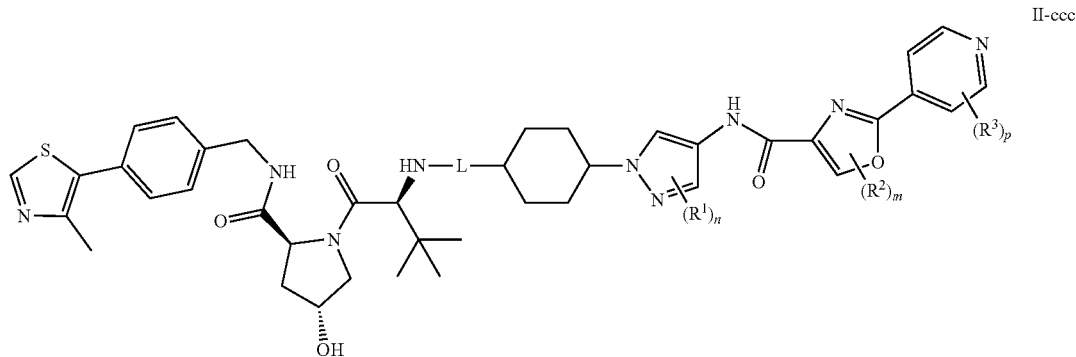

II-ccc or a pharmaceutically acceptable salt thereof, wherein each of L, R¹, R², R³, n, m, and p is as defined above and described in embodiments herein, both singly and in combination.

In certain embodiments, the present invention provides the compound of formula II-e, wherein LBM is VHL binding moeity

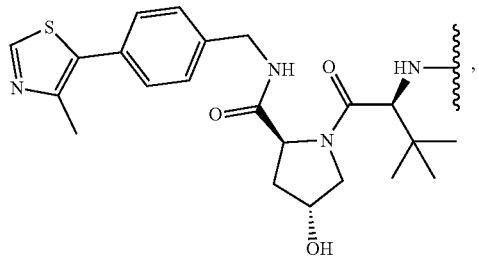 [SMILES: *N[C@H](C(=O)N1C[C@H](O)C[C@H]1C(=O)NCc1ccc(-c2scnc2C)cc1)C(C)(C)C]

L² is a covalent bond, Ring A is cyclohexyl, and Ring B is pyrazolyl as shown, thereby forming a compound of formula II-d-11:

or a pharmaceutically acceptable salt thereof, wherein each of L, L², L³, Ring A, Ring B, Ring C, R¹, R², R⁴, n, and m is as defined above and described in embodiments herein, both singly and in combination.

In certain embodiments, the present invention provides the compound of formula II-e, wherein LBM is VHL binding moeity

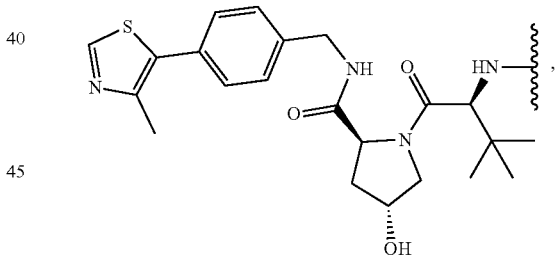

L² is a covalent bond, Ring A is cyclohexyl, Ring C is pyrazolo[1,5-a]pyrimidine, and Ring B is pyrazolyl as shown, thereby forming a compound of formula II-e-11:

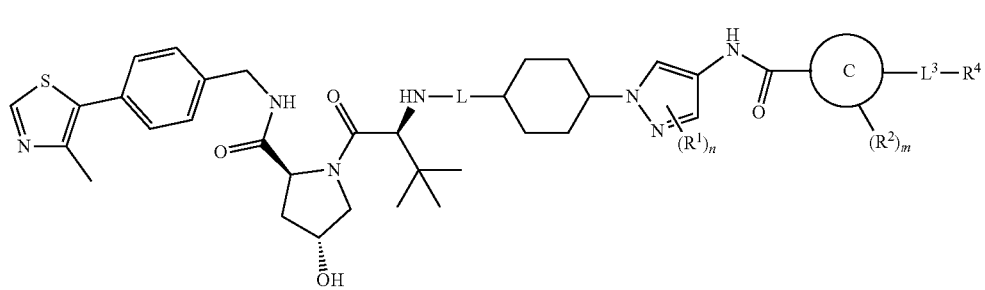

Id-d-11

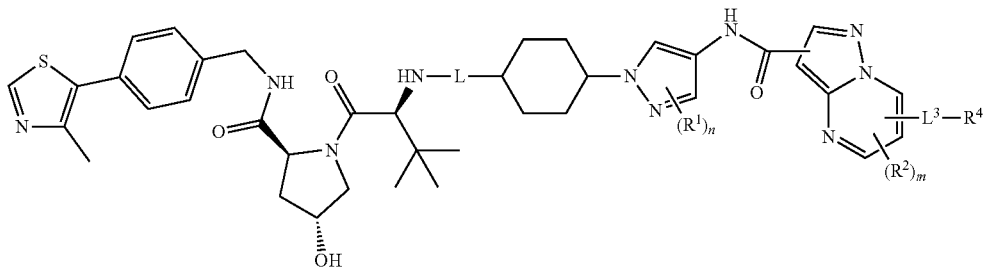

II-e-11 or a pharmaceutically acceptable salt thereof, wherein each of L, L³, R¹, R², R⁴, n, and each m is as defined above and described in embodiments herein, both singly and in combination.

In certain embodiments, the present invention provides a compound of formula II-e-12:

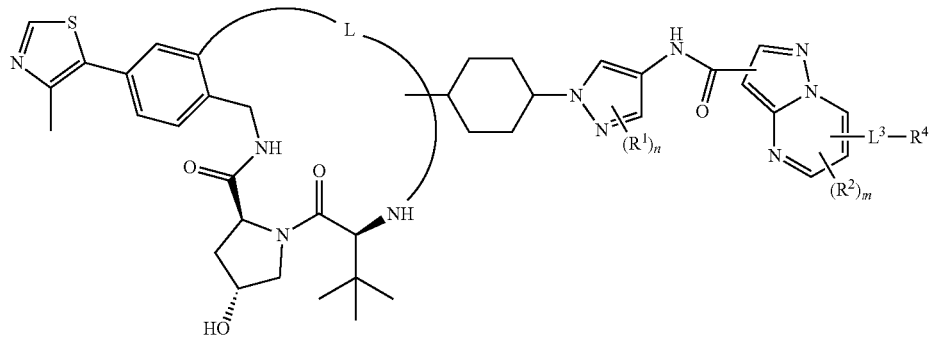

II-e-12 or a pharmaceutically acceptable salt thereof, wherein the VHL binding moeity forms a macrocycle with L as shown and the IRAK binding moeity attaches to any modifiable carbon, oxygen, or nitrogen atom of L, wherein each of L, L³, R¹, R², R⁴, n, and each m is as defined above and described in embodiments herein, both singly and in combination.

In certain embodiments, the present invention provides a compound of formula II-e-13:

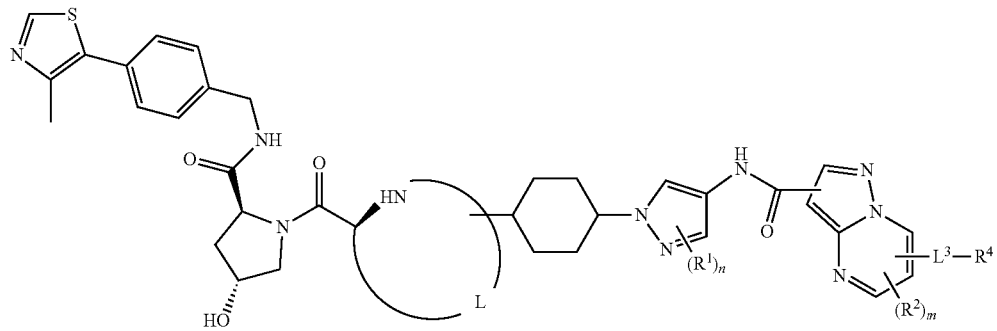

II-e-13 or a pharmaceutically acceptable salt thereof, wherein the VHL binding moeity forms a macrocycle with L as shown and the IRAK binding moeity attaches to any modifiable carbon, oxygen, or nitrogen atom of L, wherein each of L, $L^3$, $R^1$, $R^2$, $R^4$, n, and each m is as defined above and described in embodiments herein, both singly and in combination.

In certain embodiments, the present invention provides the compound of formula II-e, wherein LBM is VHL binding moeity

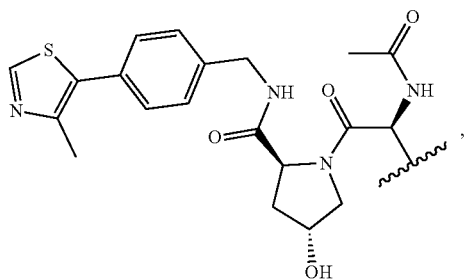 [SMILES: *[C@H](NC(C)=O)C(=O)N1C[C@H](O)C[C@H]1C(=O)NCc1ccc(-c2scnc2C)cc1]

$L^2$ is a covalent bond, Ring A is cyclohexyl, Ring C is pyrazolo[1,5-a]pyrimidine, and Ring B is pyrazolyl as shown, thereby forming a compound of formula II-e-14:

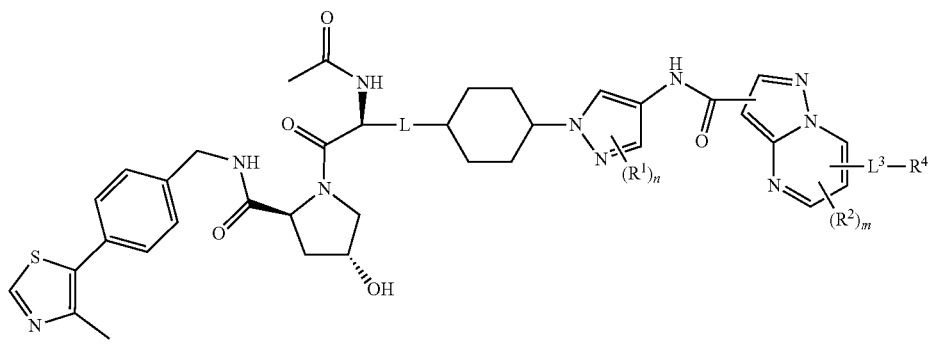

II-e-14 or a pharmaceutically acceptable salt thereof, wherein each of L, $L^3$, $R^1$, $R^2$, $R^4$, n, and each m is as defined above and described in embodiments herein, both singly and in combination.

In certain embodiments, the present invention provides the compound of formula II-e, wherein LBM is VHL binding moeity

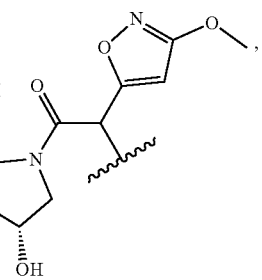

$L^2$ is a covalent bond, Ring A is cyclohexyl, Ring C is pyrazolo[1,5-a]pyrimidine, and Ring B is pyrazolyl as shown, thereby forming a compound of formula II-e-15:

II-e-15

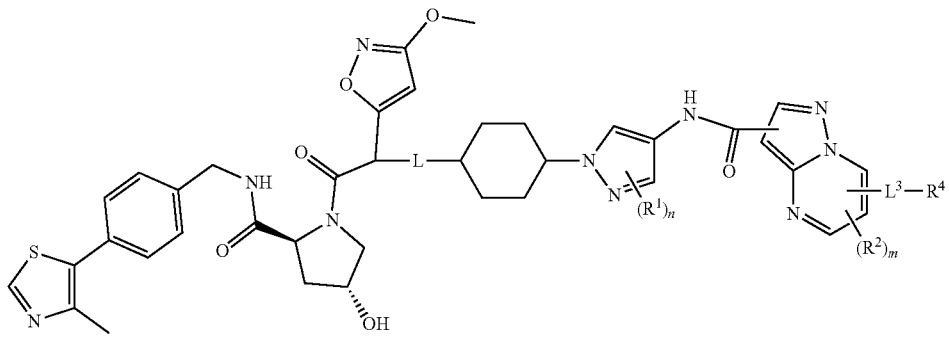

or a pharmaceutically acceptable salt thereof, wherein each of L, L³, R¹, R², R⁴, n, and each m is as defined above and described in embodiments herein, both singly and in combination.

In certain embodiments, the present invention provides the compound of formula II-e, wherein LBM is VHL binding moiety

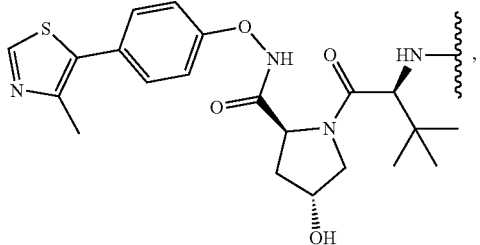 [SMILES: *N[C@H](C(=O)N1C[C@H](O)C[C@H]1C(=O)NOc1ccc(-c2scnc2C)cc1)C(C)(C)C]

L² is a covalent bond, Ring A is cyclohexyl, Ring C is pyrazolo[1,5-a]pyrimidine, and Ring B is pyrazolyl as shown, thereby forming a compound of formula II-e-16:

or a pharmaceutically acceptable salt thereof, wherein each of L, L³, R¹, R², R⁴, n, and each m is as defined above and described in embodiments herein, both singly and in combination.

In certain embodiments, the present invention provides the compound of formula II-e, wherein LBM is VHL binding moiety

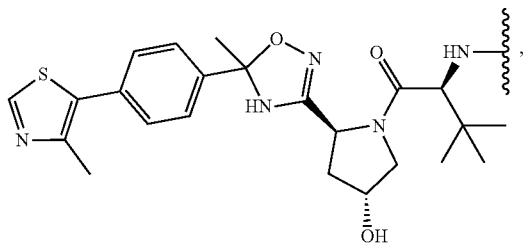 [SMILES: *N[C@H](C(=O)N1C[C@H](O)C[C@H]1C1=NOC(C)(c2ccc(-c3scnc3C)cc2)N1)C(C)(C)C]

L² is a covalent bond, Ring A is cyclohexyl, Ring C is pyrazolo[1,5-a]pyrimidine, and Ring B is pyrazolyl as shown, thereby forming a compound of formula II-e-17:

II-e-16

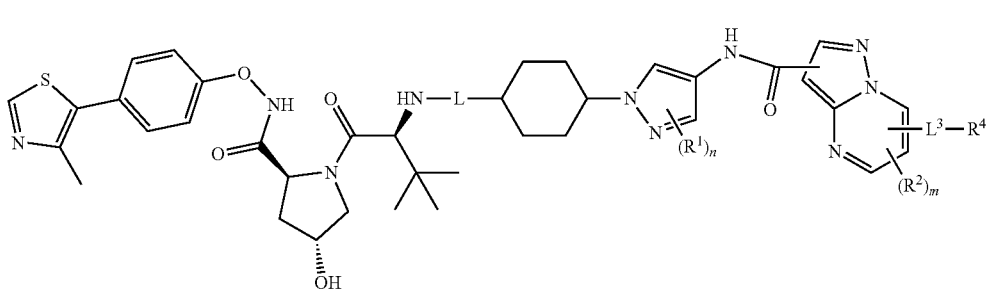

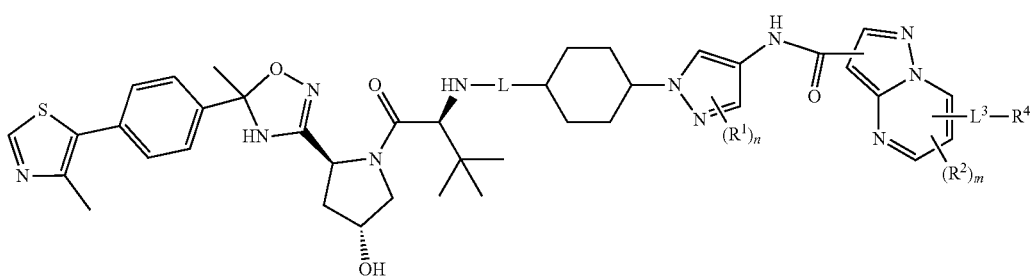

II-e-17 or a pharmaceutically acceptable salt thereof, wherein each of L, L³, R¹, R², R⁴, n, and each m is as defined above and described in embodiments herein, both singly and in combination.

In certain embodiments, the present invention provides the compound of formula II-e, wherein LBM is IAP binding moeity or a pharmaceutically acceptable salt thereof, wherein each of L, R¹, R², R³, n, m, and p is as defined above and described in embodiments herein, both singly and in combination.

In certain embodiments, the present invention provides the compound of formula II-e, wherein LBM is MDM2 binding moeity

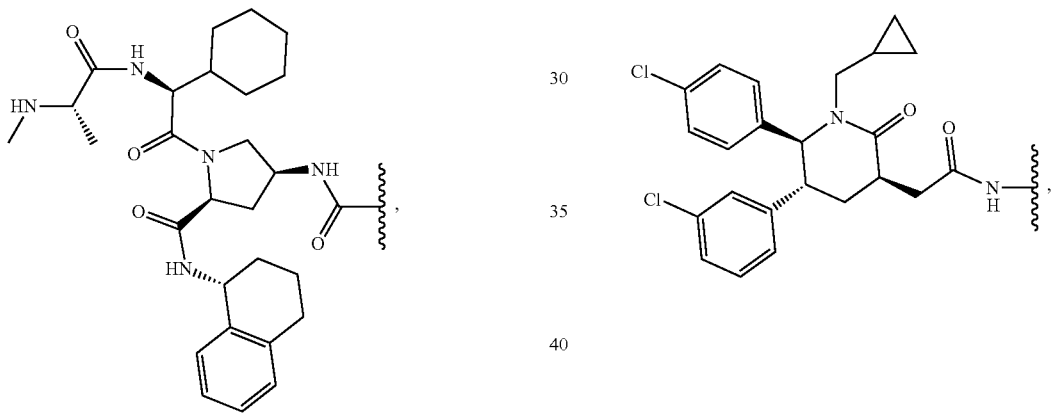

L² is a covalent bond, Ring A is cyclohexyl, Ring C is pyrazolo[1,5-a]pyrimidine, and Ring B is pyrazolyl as shown, thereby forming a compound of formula II-e-18:

L² is a covalent bond, Ring A is cyclohexyl, Ring C is pyrazolo[1,5-a]pyrimidine, and Ring B is pyrazolyl as shown, thereby forming a compound of formula II-e-19:

II-e-18

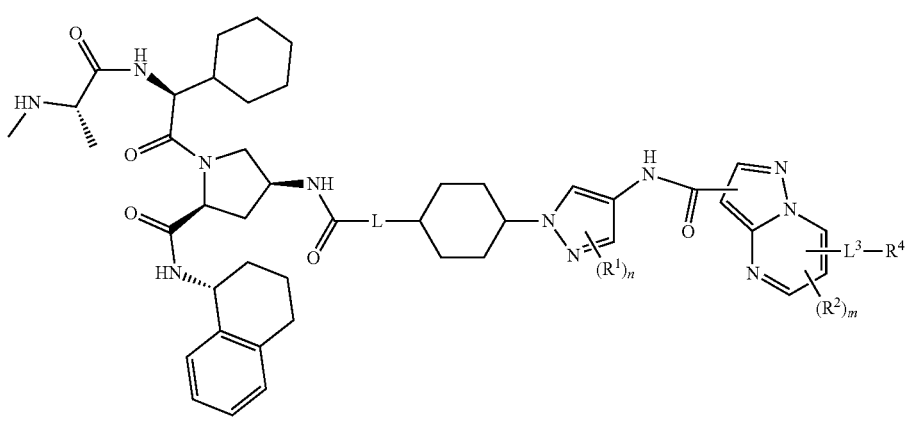

II-e-19

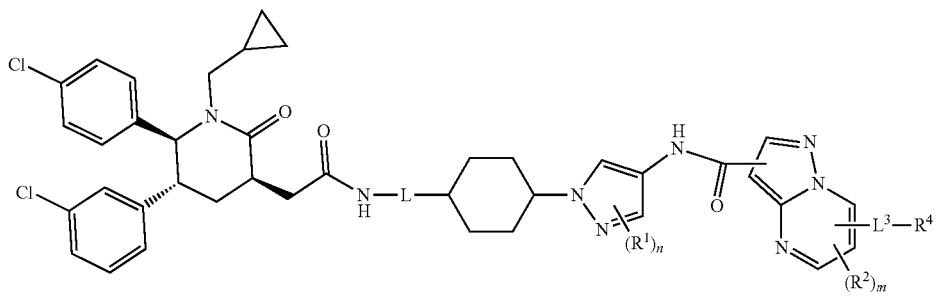

or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-e, wherein LBM is MDM2 binding moiety

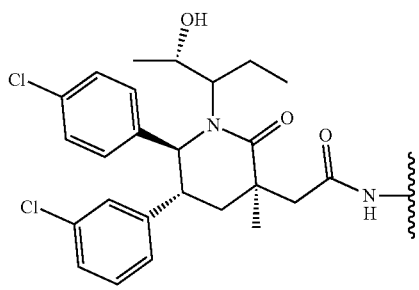

$L^2$ is a covalent bond, Ring A is cyclohexyl, Ring C is pyrazolo[1,5-a]pyrimidine, and Ring B is pyrazolyl as shown, thereby forming a compound of formula II-e-20:

or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-e, wherein LBM is MDM2 binding moiety

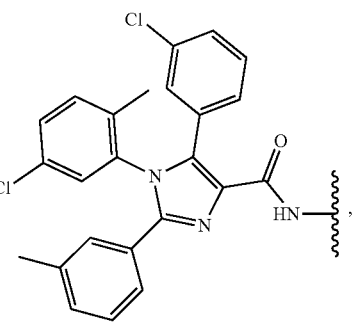

II-e-20

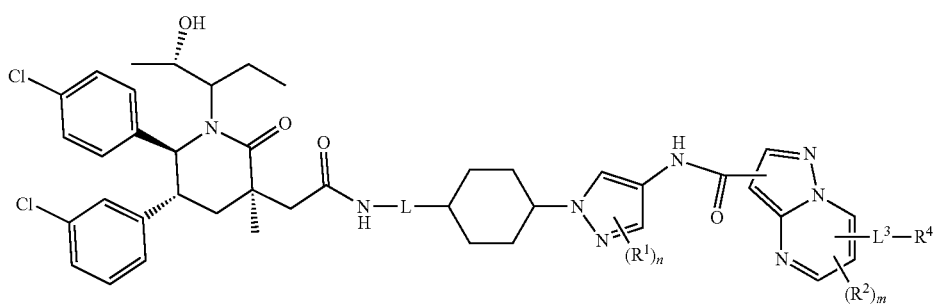

$L^2$ is a covalent bond, Ring A is cyclohexyl, Ring C is pyrazolo[1,5-a]pyrimidine, and Ring B is pyrazolyl as shown, thereby forming a compound of formula II-e-21:

II-e-21

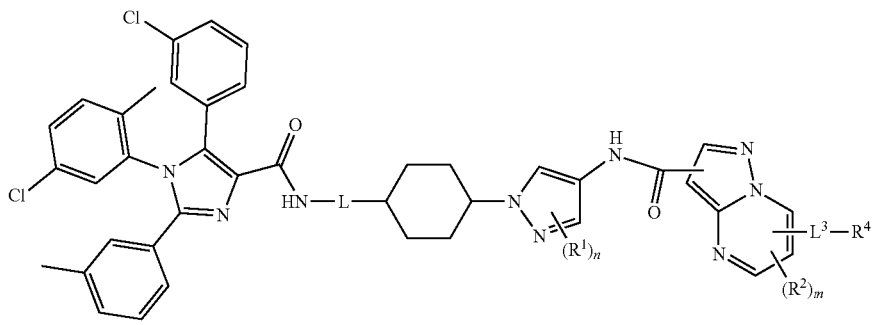

or a pharmaceutically acceptable salt thereof, wherein each of L, $R^1$, $R^2$, $R^3$, n, m, and p is as defined above and described in embodiments herein, both singly and in combination.

In certain embodiments, the present invention provides the compound of formula II-e, wherein LBM is MDM2 binding moiety

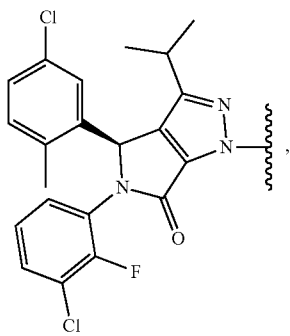 [SMILES: *n1nc(C(C)C)c2c1C(=O)N(c1cccc(Cl)c1F)[C@H]2c1cc(Cl)ccc1C]

$L^2$ is a covalent bond, Ring A is cyclohexyl, Ring C is pyrazolo[1,5-a]pyrimidine, and Ring B is pyrazolyl as shown, thereby forming a compound of formula II-e-22:

II-e-22 or a pharmaceutically acceptable salt thereof, wherein each of L, $R^1$, $R^2$, $R^3$, n, m, and p is as defined above and described in embodiments herein, both singly and in combination.

In certain embodiments, the present invention provides a compound of formula I, wherein LBM is a RPN13 binding moiety thereby forming a compound of formula I-ddd:

I-ddd

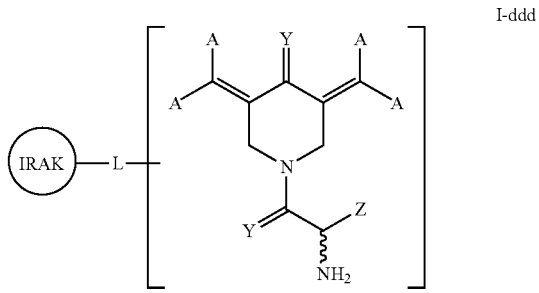

or a pharmaceutically acceptable salt thereof, wherein L and IRAK are as defined above and described in embodiments herein, and wherein each of the variables A, Y, and Z is as described and defined in WO 2019/165229, the entirety of each of which is herein incorporated by reference.

In certain embodiments, the present invention provides a compound of formula I, wherein LBM is a Ubr1 binding moiety as described in Shanmugasundaram, K. et al, J. Bio. Chem. 2019, doi: 10.1074/jbc.AC119.010790, the entirety of each of which is herein incorporated by reference, thereby forming a compound of formula I-eee-1 or I-eee-2:

I-eee-1

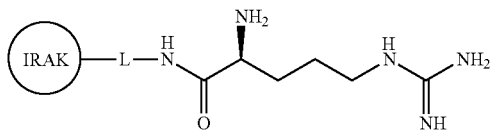

I-eee-2

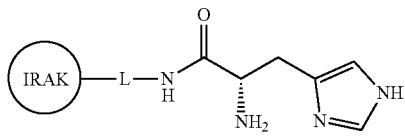

or a pharmaceutically acceptable salt thereof, wherein L and IRAK are as defined above and described in embodiments herein.

In certain embodiments, the present invention provides a compound of formula I, wherein LBM is a CRBN binding moiety thereby forming a compound of formula I-fff:

I-fff

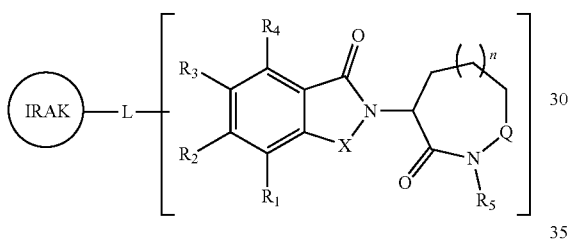

or a pharmaceutically acceptable salt thereof, wherein L and IRAK are as defined above and described in embodiments herein, and wherein each of the variables $R_1$, $R_2$, $R_3$, $R_4$, $R_5$, Q, X, and n is as described and defined in US 2019/276474, the entirety of each of which is herein incorporated by reference.

Lysine Mimetic

In some embodiments, DIM is LBM as described above and herein. In some embodiments, DIM is lysine mimetic. In some embodiments, the covalent attachment of ubiquitin to a member of the IRAK kinase family (i.e., IRAK-1, -2, -3, or -4) is achieved through the action of a lysine mimetic. In some embodiments, upon the binding of a compound of formula V to IRAK-1, the moiety that mimics a lysine undergoes ubiquitination thereby marking IRAK-1 for degradation via the Ubiquitin-Proteasome Pathway (UPP). In some embodiments, upon the binding of a compound of formula V to IRAK-2, the moiety that mimics a lysine undergoes ubiquitination thereby marking IRAK-2 for degradation via the Ubiquitin-Proteasome Pathway (UPP). In some embodiments, upon the binding of a compound of formula V to IRAK-3, the moiety that mimics a lysine undergoes ubiquitination thereby marking IRAK-3 for degradation via the Ubiquitin-Proteasome Pathway (UPP). In some embodiments, upon the binding of a compound of formula V to IRAK-4, the moiety that mimics a lysine undergoes ubiquitination thereby marking IRAK-4 for degradation via the Ubiquitin-Proteasome Pathway (UPP).

In some embodiments, DIM is

In some embodiments, DIM is

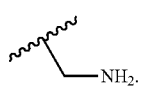

In some embodiments, DIM is

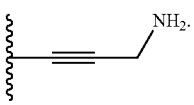

In some embodiments, DIM is selected from those depicted in Table 1, below.

In certain embodiments, the present invention provides a compound of Formula V, wherein DIM is a lysine mimetic

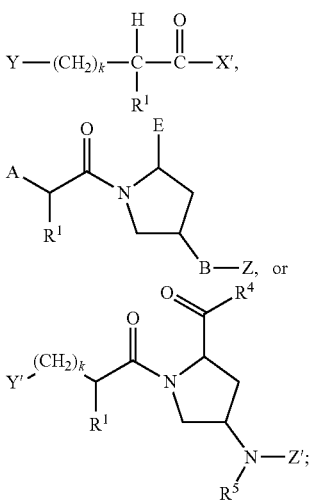

thereby forming a compound of Formulae V-j-1, V-j-2, or V-j-3, respectively:

V-j-1

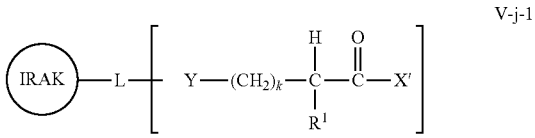

V-j-2

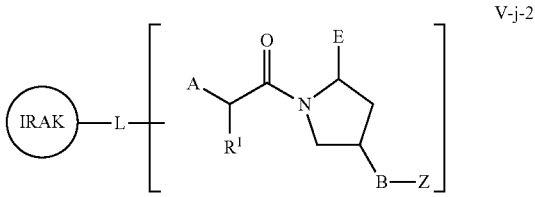

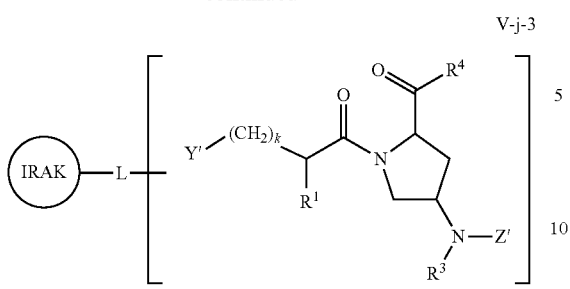

V-j-3 or a pharmaceutically acceptable salt thereof, wherein L and IRAK are as defined above and described in embodiments herein, and wherein each of the variables $R^1$, $R^4$, $R^5$, A, B, E, Y, Y', Z, Z', and k are as defined and described in U.S. Pat. No. 7,622,496, the entirety of each of which is herein incorporated by reference.

In some embodiments, the present invention provides the compound of formula V wherein DIM is

thereby forming a compound of formula V-k:

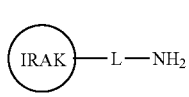

V-k or a pharmaceutically acceptable salt thereof, wherein each of IRAK and L is as defined above and described in embodiments herein, both singly and in combination.

In some embodiments, the present invention provides the compound of formula V wherein DIM is

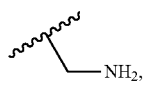

thereby forming a compound of formula V-l:

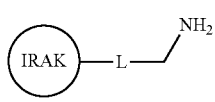

V-l or a pharmaceutically acceptable salt thereof, wherein each of IRAK and L is as defined above and described in embodiments herein, both singly and in combination.

In some embodiments, the present invention provides the compound of formula V wherein DIM is

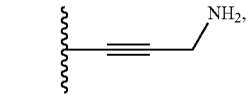 [SMILES: *C#CCN]

thereby forming a compound of formula V-m:

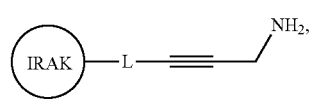

V-m or a pharmaceutically acceptable salt thereof, wherein each of IRAK and L is as defined above and described in embodiments herein, both singly and in combination.

Hydrogen Atom

In some embodiments, DIM is a hydrogen atom. In some embodiments, the covalent attachment of ubiquitin to one or more members of the IRAK kinase family (i.e., IRAK-1, -2, -3, or -4) is achieved through a provided compound wherein DIM is a hydrogen atom. In some embodiments, upon the binding of a compound of formula V to IRAK-1, the DIM moiety being hydrogen effectuates ubiquitination thereby marking IRAK-1 for degradation via the Ubiquitin-Proteasome Pathway (UPP). In some embodiments, upon the binding of a compound of formula V to IRAK-2, the DIM moiety being hydrogen effectuates ubiquitination thereby marking IRAK-2 for degradation via the Ubiquitin-Proteasome Pathway (UPP). In some embodiments, upon the binding of a compound of formula V to IRAK-3, the DIM moiety being hydrogen effectuates ubiquitination thereby marking IRAK-3 for degradation via the Ubiquitin-Proteasome Pathway (UPP). In some embodiments, upon the binding of a compound of formula V to IRAK-4, the DIM moiety being hydrogen effectuates ubiquitination thereby marking IRAK-4 for degradation via the Ubiquitin-Proteasome Pathway (UPP).

In some embodiments, DIM is selected from those depicted in Table 1, below.

In some embodiments, the present invention provides the compound of formula V wherein DIM is a hydrogen atom, thereby forming a compound of formula V-n:

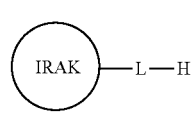

V-n or a pharmaceutically acceptable salt thereof, wherein each of IRAK and L is as defined above and described in embodiments herein, both singly and in combination.

Linker (L)

As defined above and described herein, L is a bivalent moiety that connects IRAK to LBM or IRAK to DIM.

In some embodiments, L is a bivalent moiety that connects IRAK to LBM. In some embodiments, L is a bivalent moiety that connects IRAK to DIM. In some embodiments, L is a bivalent moiety that connects IRAK to a lysine mimetic. In some embodiments, L is a bivalent moiety that connects IRAK to a hydrogen atom.

In some embodiments, L is a covalent bond or a bivalent, saturated or unsaturated, straight or branched $C_{1-50}$ hydrocarbon chain, wherein 0-6 methylene units of L are independently replaced by -Cy-, —O—, —NR—, —S—, —OC(O)—, —C(O)O—, —C(O)—, —S(O)—, —S(O)$_2$—, —NRS(O)$_2$—, —S(O)$_2$NR—, —NRC(O)—, —C(O)NR—, —OC(O)NR—, —NRC(O)O—,

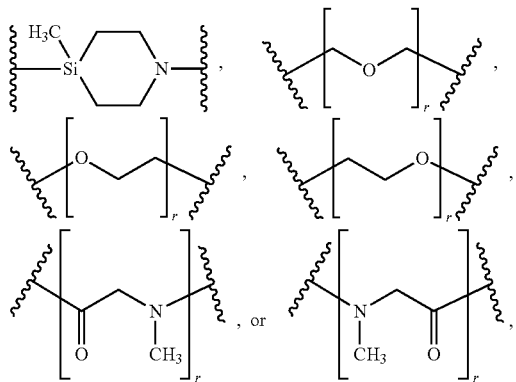

wherein: each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, or an 8-10 membered bicyclic heteroarylenyl having 1-5 heteroatoms independently selected from nitrogen, oxygen, or sulfur, and wherein r is 0, 1, 2, 3, 4, 5, 6, 7, 8, 9, or 10.

In some embodiments, each -Cy- is independently an optionally substituted bivalent phenylenyl. In some embodiments, each -Cy- is independently an optionally substituted 8-10 membered bicyclic arylenyl. In some embodiments, each -Cy- is independently an optionally substituted 4-11 membered saturated or partially unsaturated carbocyclylenyl. In some embodiments, each -Cy- is independently an optionally substituted 4-7 membered saturated or partially unsaturated spiro carbocyclylenyl. In some embodiments, each -Cy- is independently an optionally substituted 8-10 membered bicyclic saturated or partially unsaturated carbocyclylenyl. In some embodiments, each -Cy- is independently an optionally substituted 4-7 membered saturated or partially unsaturated heterocyclylenyl having 1-2 heteroatoms independently selected from nitrogen, oxygen, and sulfur. In some embodiments, each -Cy- is independently an optionally substituted 4-11 membered saturated or partially unsaturated spiro heterocyclylenyl having 1-2 heteroatoms independently selected from nitrogen, oxygen, and sulfur. In some embodiments, each -Cy- is independently an optionally substituted 8-10 membered bicyclic saturated or partially unsaturated heterocyclylenyl having 1-2 heteroatoms independently selected from nitrogen, oxygen, and sulfur. In some embodiments, each -Cy- is independently an optionally substituted 5-6 membered heteroarylenyl having 1-4 heteroatoms independently selected from nitrogen, oxygen, and sulfur. In some embodiments, each -Cy- is independently an optionally substituted 8-10 membered bicyclic heteroarylenyl having 1-5 heteroatoms independently selected from nitrogen, oxygen, or sulfur.

In some embodiments, -Cy- is

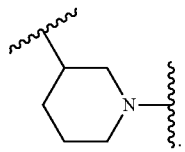 [SMILES: *C1CCCN(*)C1]

In some embodiments, -Cy- is

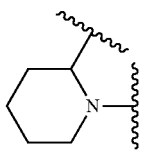 [SMILES: *C1CCCCN1*]

In some embodiments, -Cy- is

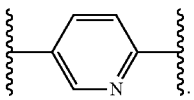 [SMILES: *c1ccc(*)nc1]

In some embodiments, -Cy- is

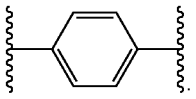

In some embodiments, -Cy- is

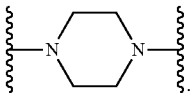

In some embodiments, -Cy- is

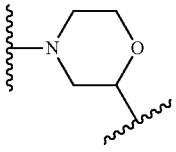

In some embodiments, -Cy- is
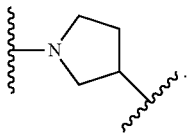
In some embodiments, -Cy- is
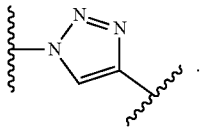
In some embodiments, -Cy- is
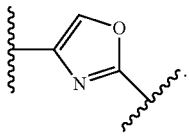
In some embodiments, -Cy- is
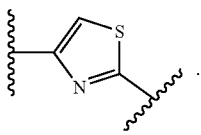 [SMILES: *c1csc(*)n1]
In some embodiments, -Cy- is
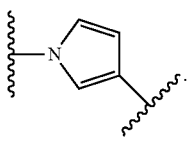
In some embodiments, -Cy- is
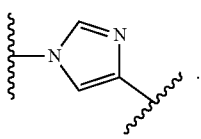 [SMILES: *c1cn(*)cn1]
In some embodiments, -Cy- is
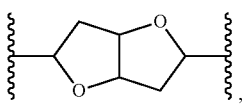
In some embodiments, -Cy- is
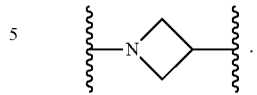
In some embodiments, -Cy- is
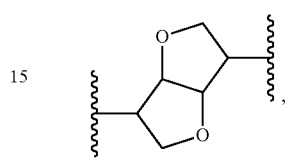
In some embodiments, -Cy- is
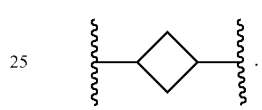
In some embodiments, -Cy- is
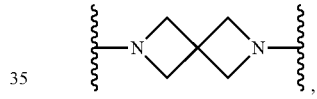
In some embodiments, -Cy- is
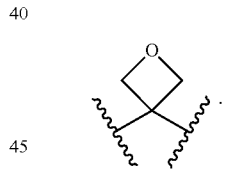
In some embodiments, -Cy- is
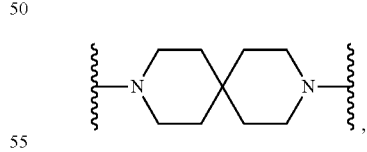
In some embodiments, -Cy- is
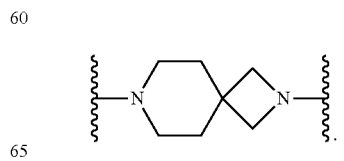

In some embodiments, -Cy- is
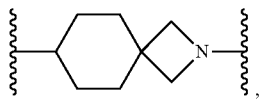 [SMILES: *C1CCC2(CC1)CN(*)C2]
In some embodiments, -Cy- is
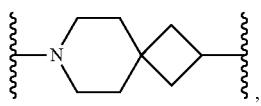
In some embodiments, -Cy- is
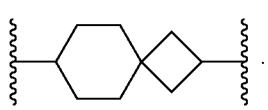
In some embodiments, -Cy- is
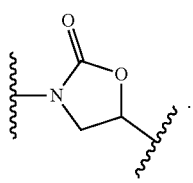 [SMILES: *C1CN(*)C(=O)O1]
In some embodiments, -Cy- is
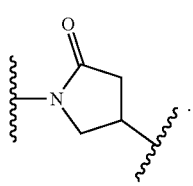 [SMILES: *C1CC(=O)N(*)C1]
In some embodiments, -Cy- is
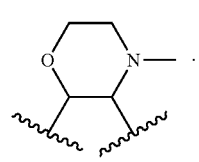 [SMILES: *C1OCCN(C)C1*]
In some embodiments, -Cy- is
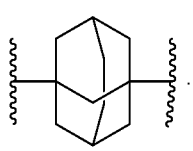
In some embodiments, -Cy- is
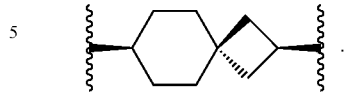
In some embodiments, -Cy- is
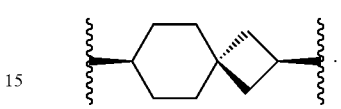
In some embodiments, -Cy- is
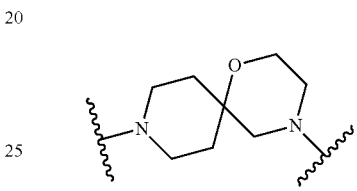
In some embodiments, -Cy- is
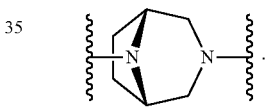
In some embodiments, -Cy- is
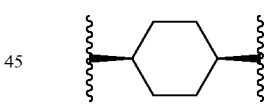
In some embodiments, -Cy- is
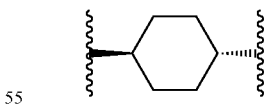
In some embodiments, -Cy- is
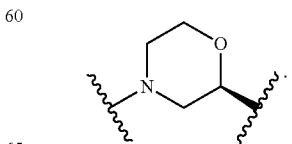

In some embodiments, -Cy- is

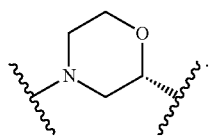 [SMILES: *[C@@H]1CN(*)CCO1]

In some embodiments, -Cy- is

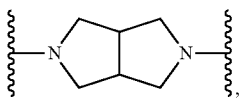 [SMILES: *N1CC2CN(*)CC2C1]

In some embodiments, -Cy- is

In some embodiments, -Cy- is

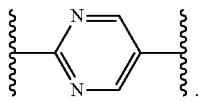 [SMILES: *c1cnc(*)nc1]

In some embodiments, -Cy- is

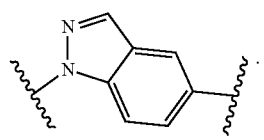 [SMILES: *c1ccc2c(cnn2*)c1]

In some embodiments, -Cy- is selected from those depicted in Table 1, below.

In some embodiments, L is selected from those depicted in Table 1, below.

In some embodiments, r is 0. In some embodiments, r is 1. In some embodiments, r is 2. In some embodiments, r is 3. In some embodiments, r is 4. In some embodiments, r is 5. In some embodiments, r is 6. In some embodiments, r is 7. In some embodiments, r is 8. In some embodiments, r is 9. In some embodiments, r is 10.

In some embodiments, r is selected from those depicted in Table 1, below.

In some embodiments, L is

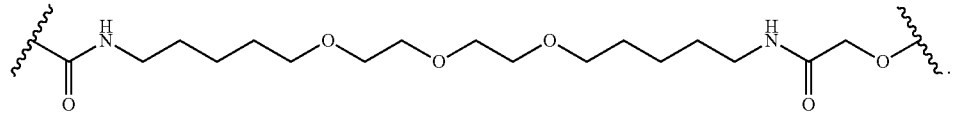 [SMILES: *OCC(=O)NCCCCCOCCOCCOCCCCCNC(*)=O]

In some embodiments, L is

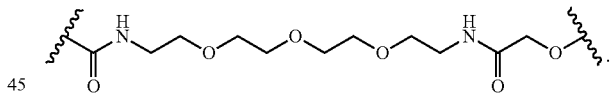

In some embodiments, L is

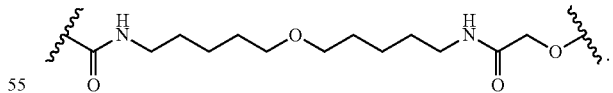

In some embodiments, L is

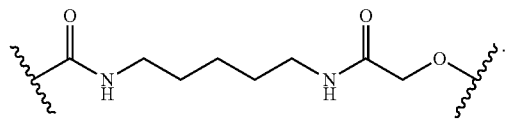 [SMILES: *OCC(=O)NCCCCCNC(*)=O]

In some embodiments, L is
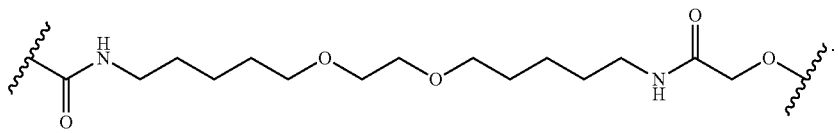 [SMILES: *OCC(=O)NCCCCCOCCOCCCCCNC(*)=O]
In some embodiments, L is
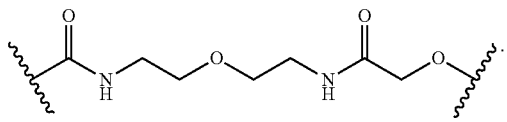 [SMILES: *OCC(=O)NCCOCCNC(*)=O]
In some embodiments, L is
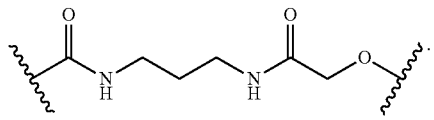 [SMILES: *OCC(=O)NCCCNC(*)=O]
In some embodiments, L is
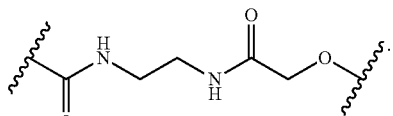
In some embodiments, L is
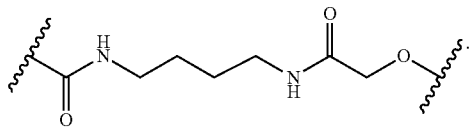 [SMILES: *OCC(=O)NCCCCNC(*)=O]
In some embodiments, L is
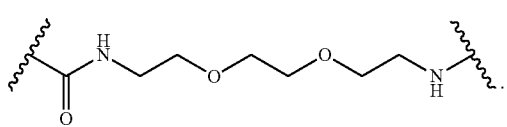 [SMILES: *NCCOCCOCCNC(*)=O]
In some embodiments, L is
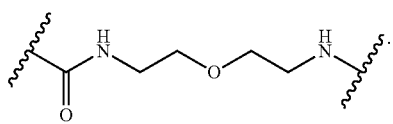 [SMILES: *NCCOCCNC(*)=O]
In some embodiments, L is
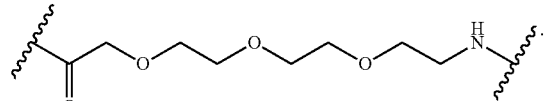
In some embodiments, L is
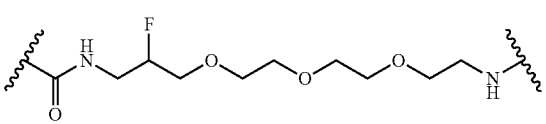

In some embodiments, L is
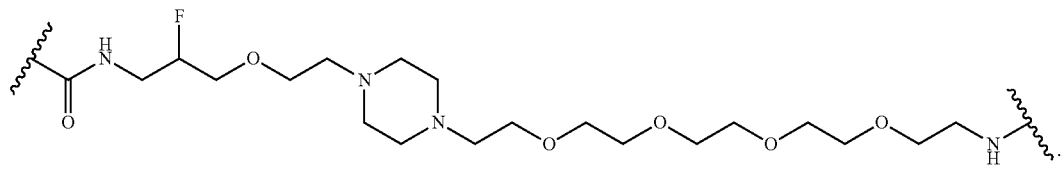 [SMILES: *NCCOCCOCCOCCOCCN1CCN(CCOCC(F)CNC(*)=O)CC1]
In some embodiments, L is
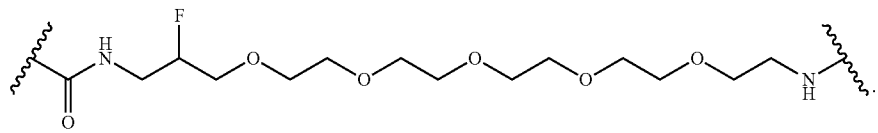 [SMILES: *NCCOCCOCCOCCOCCOCC(F)CNC(*)=O]
In some embodiments, L is
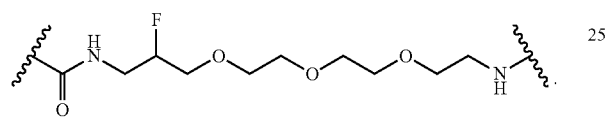
In some embodiments, L is
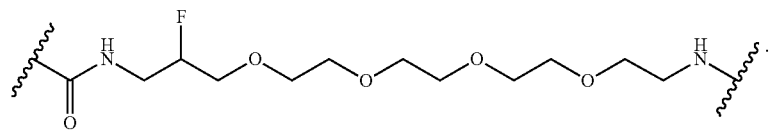 [SMILES: *NCCOCCOCCOCCOCC(F)CNC(*)=O]
In some embodiments, L is
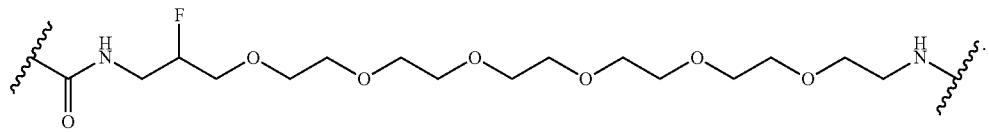 [SMILES: *NCCOCCOCCOCCOCCOCCOCC(F)CNC(*)=O]
In some embodiments, L is
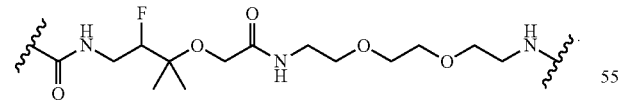
In some embodiments, L is
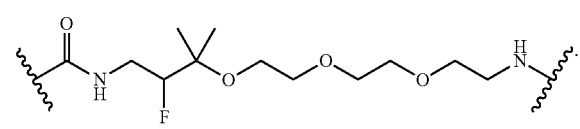 [SMILES: *NCCOCCOCCOC(C)(C)C(F)CNC(*)=O]
In some embodiments, L is
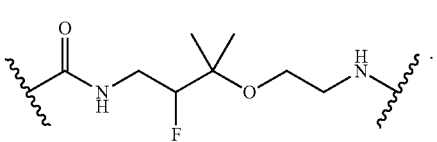 [SMILES: *NCCOC(C)(C)C(F)CNC(*)=O]

In some embodiments, L is
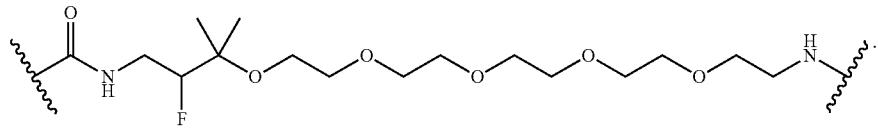 [SMILES: *NCCOCCOCCOCCOCCOC(C)(C)C(F)CNC(*)=O]
In some embodiments, L is
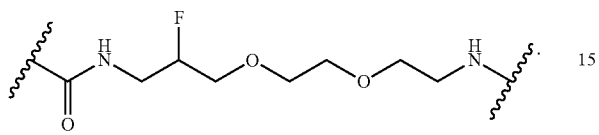
In some embodiments, L is
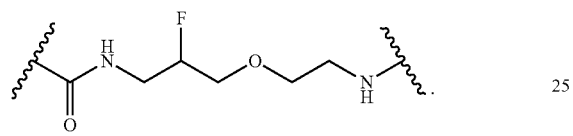
In some embodiments, L is
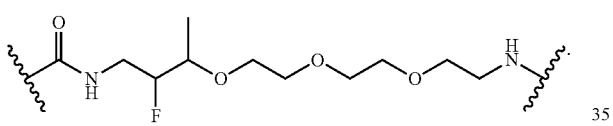
In some embodiments, L is
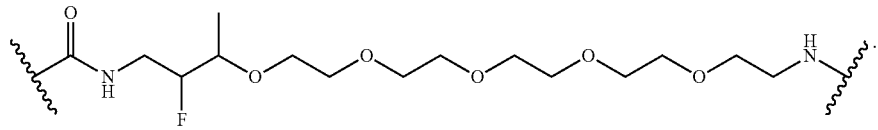 [SMILES: *NCCOCCOCCOCCOCCOC(C)C(F)CNC(*)=O]
In some embodiments, L is
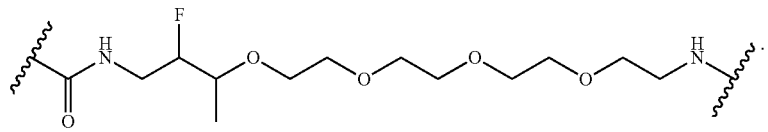 [SMILES: *NCCOCCOCCOCCOC(C)C(F)CNC(*)=O]
In some embodiments, L is
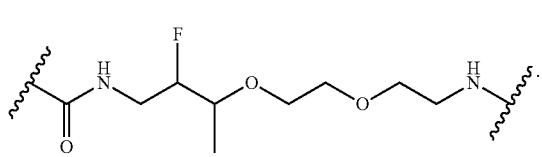 [SMILES: *NCCOCCOC(C)C(F)CNC(*)=O]
In some embodiments, L is
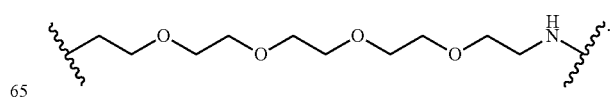

In some embodiments, L is
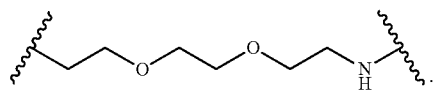 [SMILES: *CCOCCOCCN*]
In some embodiments, L is
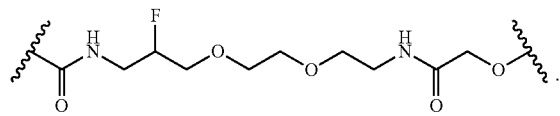 [SMILES: *OCC(=O)NCCOCCOCC(F)CNC(*)=O]
In some embodiments, L is
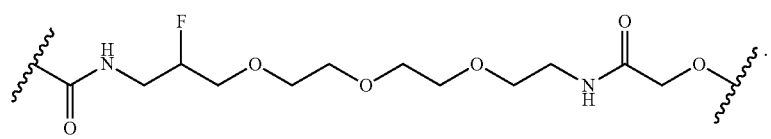 [SMILES: *OCC(=O)NCCOCCOCCOCC(F)CNC(*)=O]
In some embodiments, L is
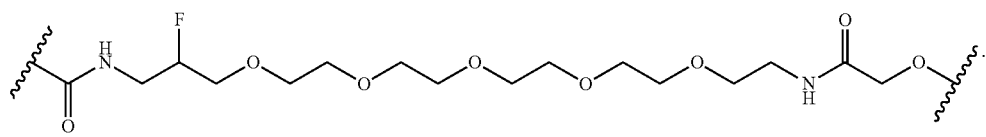 [SMILES: *OCC(=O)NCCOCCOCCOCCOCCOCC(F)CNC(*)=O]
In some embodiments, L is
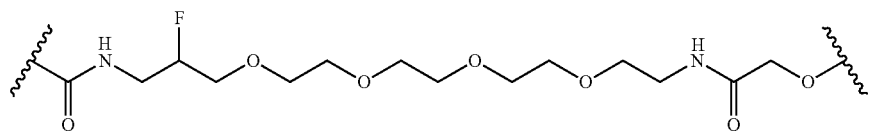
In some embodiments, L is
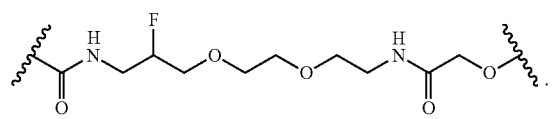
In some embodiments, L is
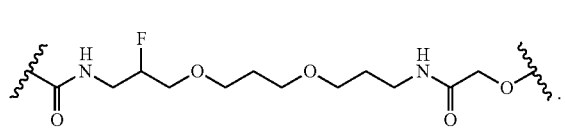
In some embodiments, L is
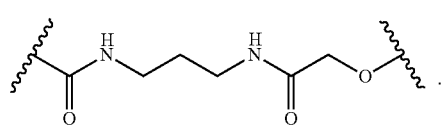

In some embodiments, L is
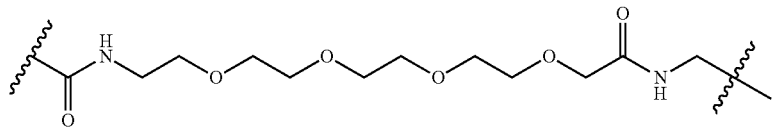
In some embodiments, L is
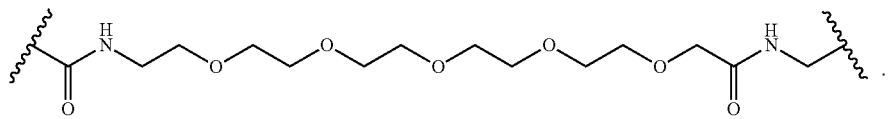
In some embodiments, L is
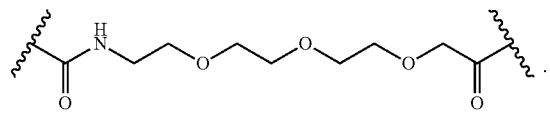
In some embodiments, L is
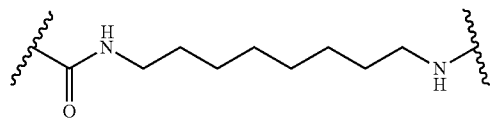
In some embodiments, L is
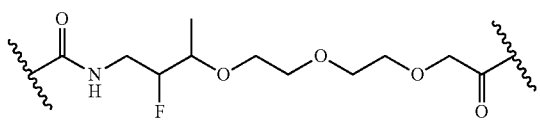
In some embodiments, L is
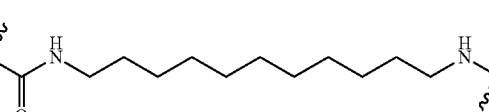
In some embodiments, L is
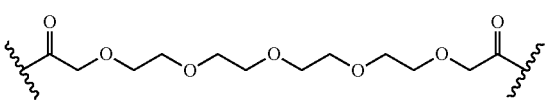
In some embodiments, L is
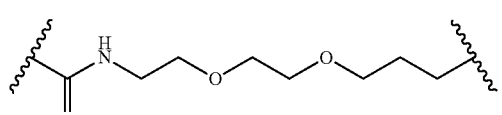
In some embodiments, L is
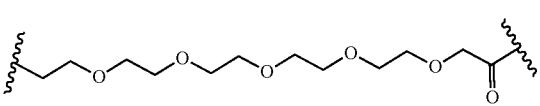
In some embodiments, L is
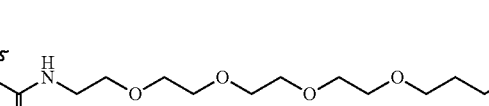
In some embodiments, L is
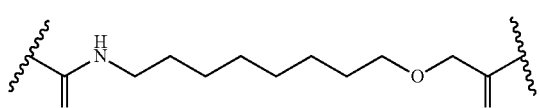
In some embodiments, L is
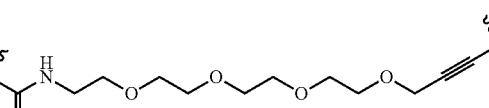

In some embodiments, L is

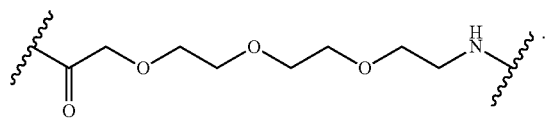 [SMILES: *NCCOCCOCCOCC(*)=O]

In some embodiments, L is

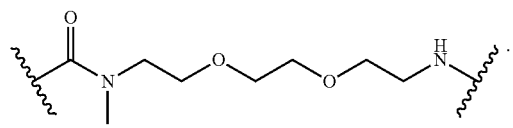 [SMILES: *NCCOCCOCCN(C)C(*)=O]

In some embodiments, L is

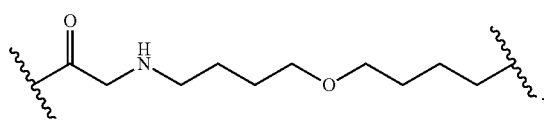 [SMILES: *CCCCOCCCCNCC(*)=O]

In some embodiments, L is

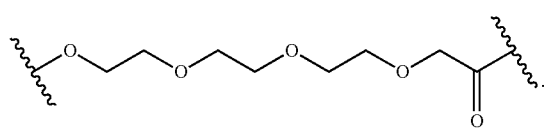 [SMILES: *OCCOCCOCCOCC(*)=O]

In some embodiments, L is

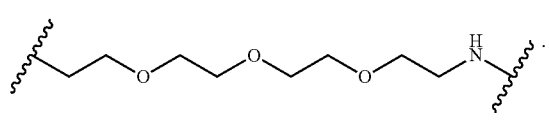 [SMILES: *CCOCCOCCOCCN*]

In some embodiments, L is

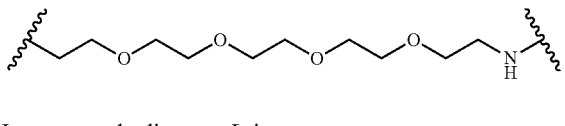

In some embodiments, L is

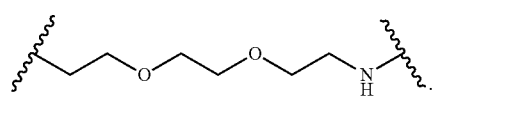 [SMILES: *CCOCCOCCN*]

In some embodiments, L is

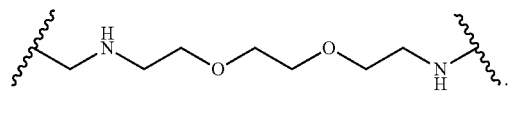 [SMILES: *CNCCOCCOCCN*]

In some embodiments, L is

In some embodiments, L is

In some embodiments, L is

In some embodiments, L is

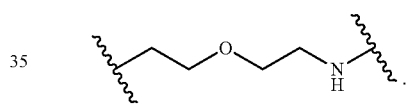

In some embodiments, L is

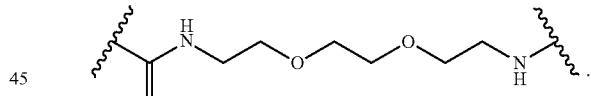

In some embodiments, L is


In some embodiments, L is

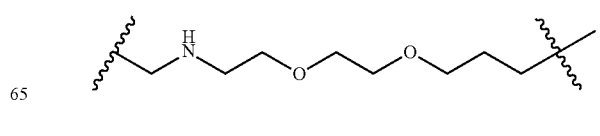

In some embodiments, L is
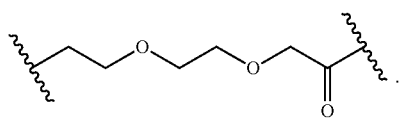 [SMILES: *CCOCCOCC(*)=O]
In some embodiments, L is
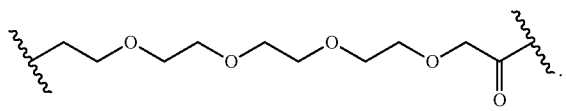 [SMILES: *CCOCCOCCOCCOCC(*)=O]
In some embodiments, L is
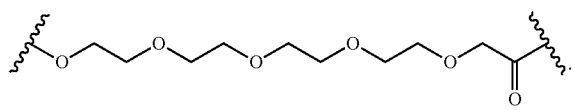 [SMILES: *OCCOCCOCCOCCOCC(*)=O]
In some embodiments, L is
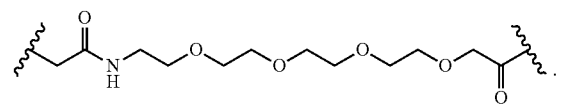 [SMILES: *CC(=O)NCCOCCOCCOCCOCC(*)=O]
In some embodiments, L is
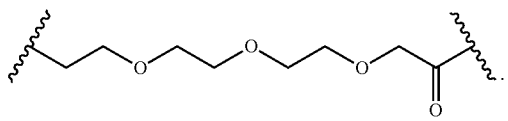 [SMILES: *CCOCCOCCOCC(*)=O]
In some embodiments, L is
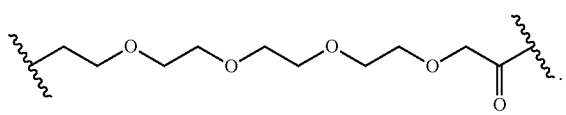 [SMILES: *CCOCCOCCOCCOCC(*)=O]
In some embodiments, L is
In some embodiments, L is
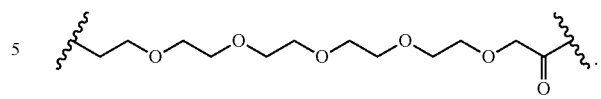
In some embodiments, L is
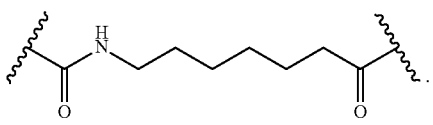 [SMILES: *C(=O)CCCCCCNC(*)=O]
In some embodiments, L is
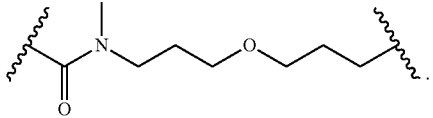 [SMILES: *CCCOCCCN(C)C(*)=O]
In some embodiments, L is
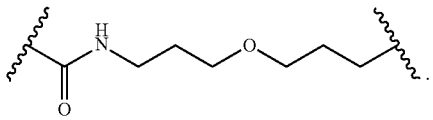 [SMILES: *CCCOCCCNC(*)=O]
In some embodiments, L is
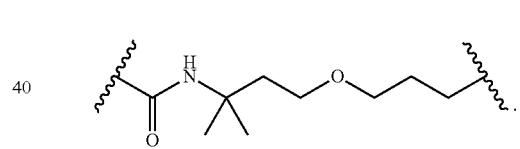
In some embodiments, L is
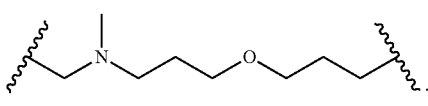 [SMILES: *CCCOCCCN(C)C*]
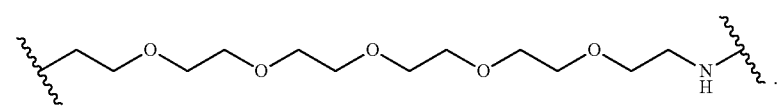

In some embodiments, L is

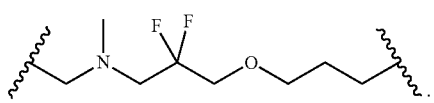 [SMILES: *CCCOCC(F)(F)CN(C)C*]

In some embodiments, L is

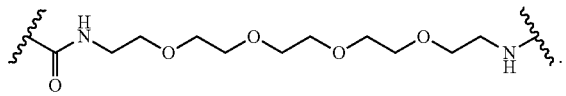 [SMILES: *NCCOCCOCCOCCOCCNC(*)=O]

In some embodiments, L is

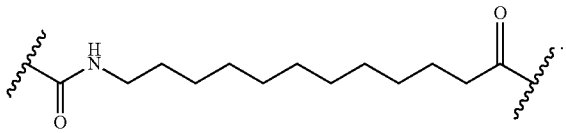 [SMILES: *C(=O)CCCCCCCCCCCNC(*)=O]

In some embodiments, L is

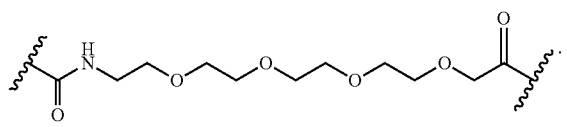 [SMILES: *C(=O)COCCOCCOCCOCCNC(*)=O]

In some embodiments, L is

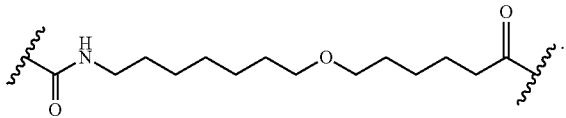 [SMILES: *C(=O)CCCCCOCCCCCCCNC(*)=O]

In some embodiments, L is

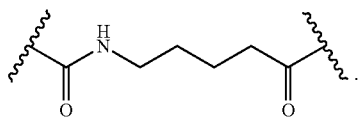 [SMILES: *C(=O)CCCCNC(*)=O]

In some embodiments, L is

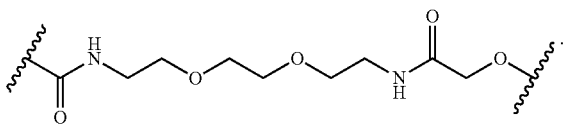 [SMILES: *OCC(=O)NCCOCCOCCNC(*)=O]

In some embodiments, L is

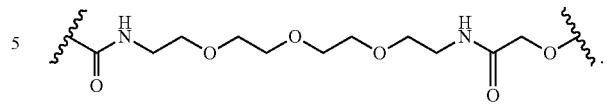

In some embodiments, L is

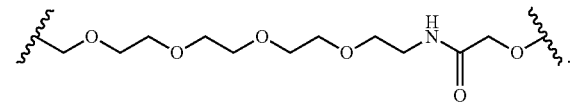 [SMILES: *COCCOCCOCCOCCNC(=O)CO*]

In some embodiments, L is

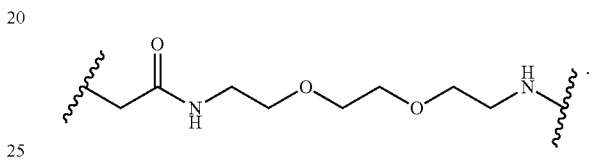

In some embodiments, L is

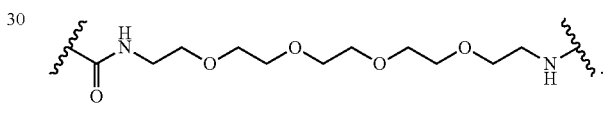

In some embodiments, L is

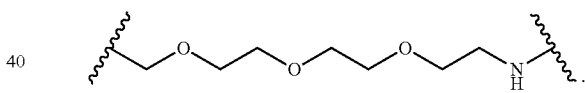

In some embodiments, L is

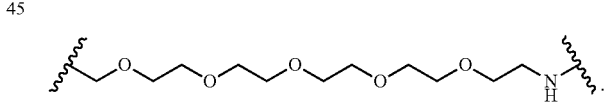

In some embodiments, L is

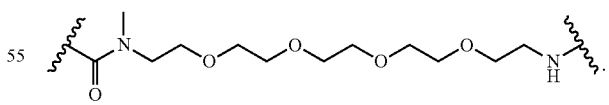

In some embodiments, L is

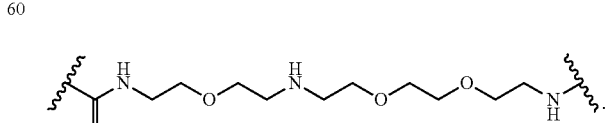

In some embodiments, L is
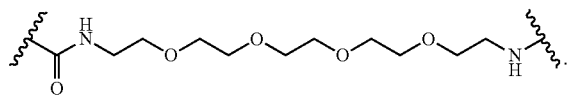 [SMILES: *NCCOCCOCCOCCOCCNC(*)=O]
In some embodiments, L is
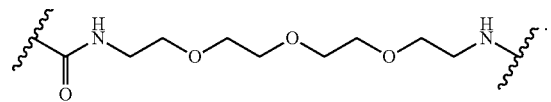 [SMILES: *NCCOCCOCCOCCNC(*)=O]
In some embodiments, L is
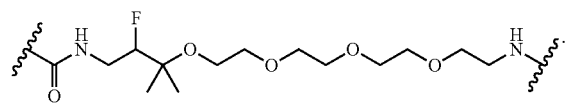 [SMILES: *NCCOCCOCCOCCOC(C)(C)C(F)CNC(*)=O]
In some embodiments, L is
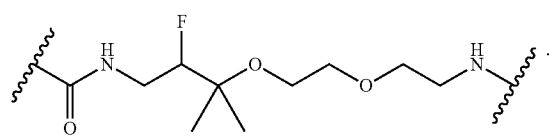 [SMILES: *NCCOCCOC(C)(C)C(F)CNC(*)=O]
In some embodiments, L is
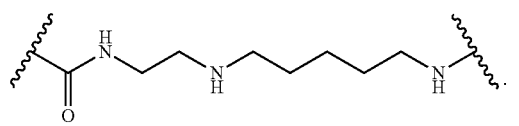 [SMILES: *NCCCCCNCCNC(*)=O]
In some embodiments, L is
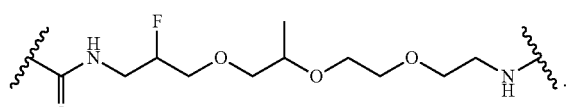
In some embodiments, L is
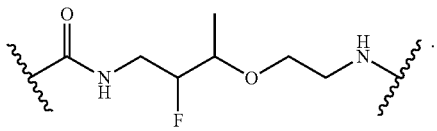 [SMILES: *NCCOC(C)C(F)CNC(*)=O]
In some embodiments, L is
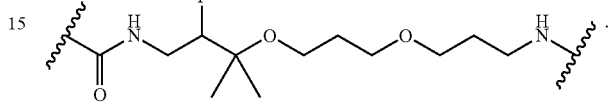
In some embodiments, L is
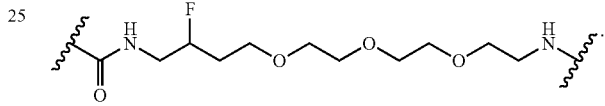
In some embodiments, L is
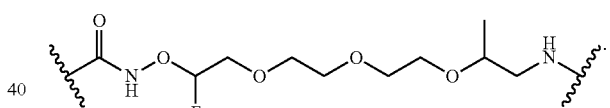
In some embodiments, L is
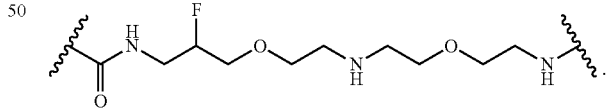
In some embodiments, L is
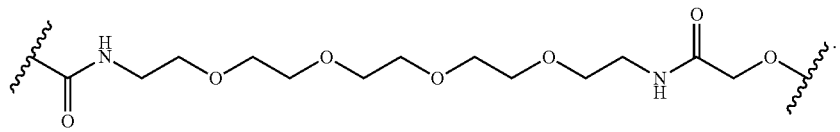

In some embodiments, L is
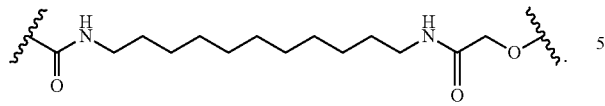
In some embodiments, L is
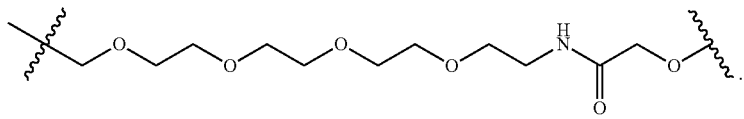 [SMILES: *COCCOCCOCCOCCNC(=O)CO*]
In some embodiments, L is
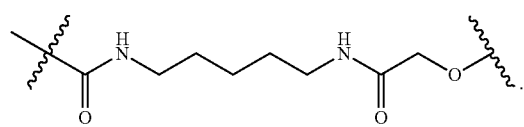 [SMILES: *OCC(=O)NCCCCCNC(*)=O]
In some embodiments, L is
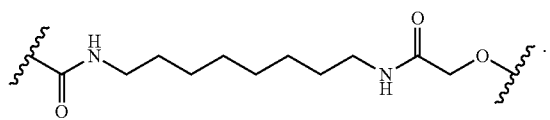
In some embodiments, L is
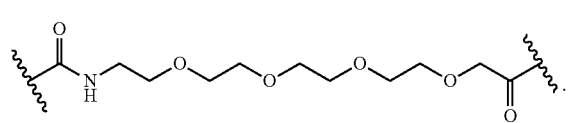 [SMILES: *C(=O)COCCOCCOCCOCCNC(*)=O]
In some embodiments, L is
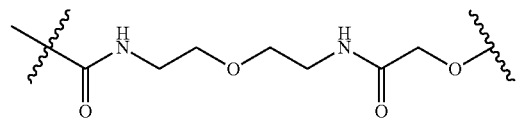
In some embodiments, L is
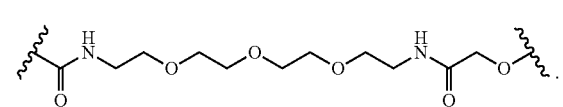 [SMILES: *OCC(=O)NCCOCCOCCOCCNC(*)=O]
In some embodiments, L is
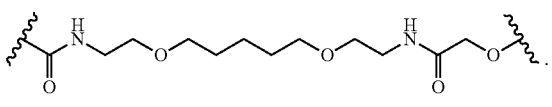 [SMILES: *OCC(=O)NCCOCCCCCOCCNC(*)=O]
In some embodiments, L is
In some embodiments, L is

In some embodiments, L is

In some embodiments, L is
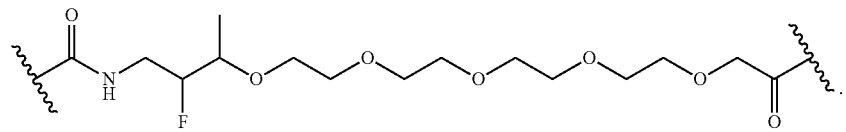 [SMILES: *C(=O)COCCOCCOCCOCCOC(C)C(F)CNC(*)=O]
In some embodiments, L is
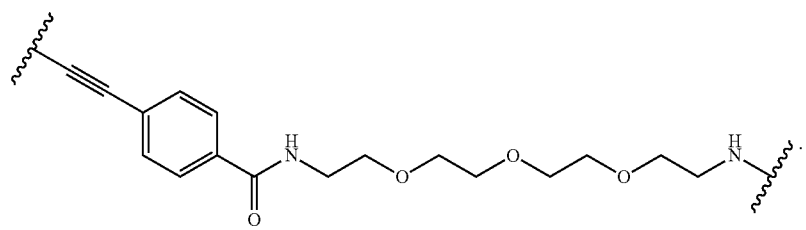 [SMILES: *C#Cc1ccc(C(=O)NCCOCCOCCOCCN*)cc1]
In some embodiments, L is
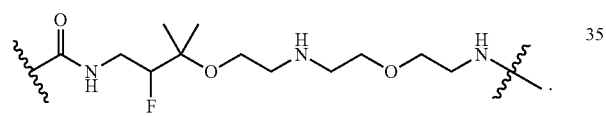
In some embodiments, L is
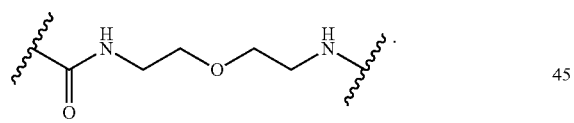
In some embodiments, L is
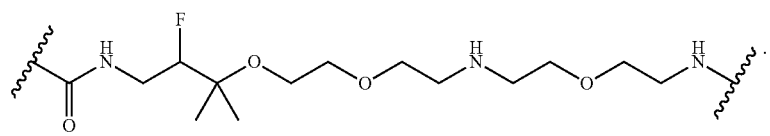 [SMILES: *NCCOCCNCCOCCOC(C)(C)C(F)CNC(*)=O]
In some embodiments, L is
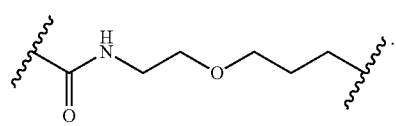 [SMILES: *CCCOCCNC(*)=O]

In some embodiments, L is
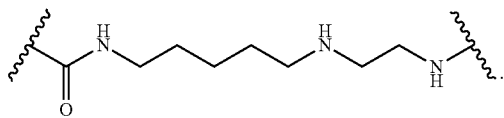 [SMILES: *NCCNCCCCCNC(*)=O]
In some embodiments, L is
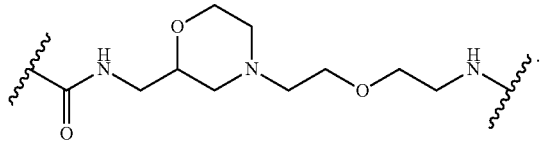 [SMILES: *NCCOCCN1CCOC(CNC(*)=O)C1]
In some embodiments, L is
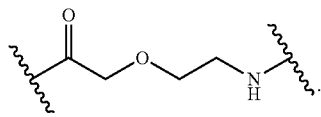 [SMILES: *NCCOCC(*)=O]
In some embodiments, L is
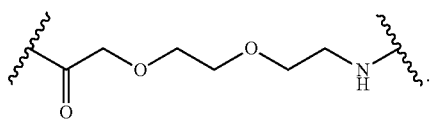 [SMILES: *NCCOCCOCC(*)=O]
In some embodiments, L is
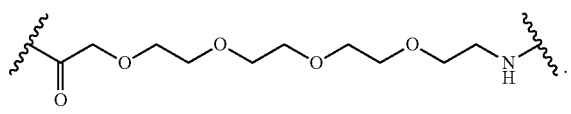 [SMILES: *NCCOCCOCCOCCOCC(*)=O]
In some embodiments, L is
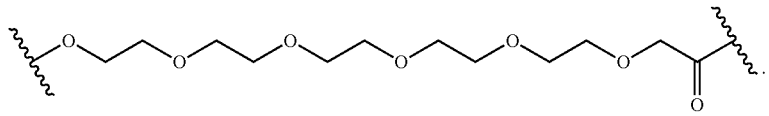 [SMILES: *OCCOCCOCCOCCOCCOCC(*)=O]
In some embodiments, L is
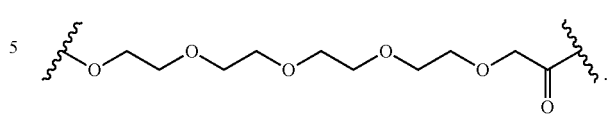
In some embodiments, L is
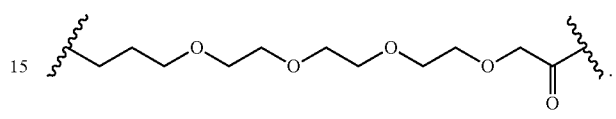
In some embodiments, L is
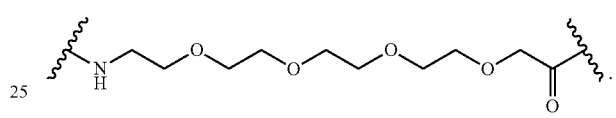
In some embodiments, L is
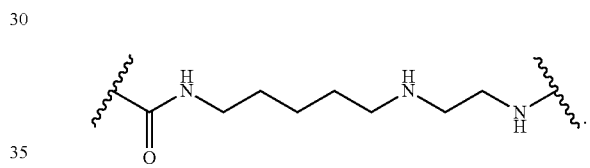
In some embodiments, L is
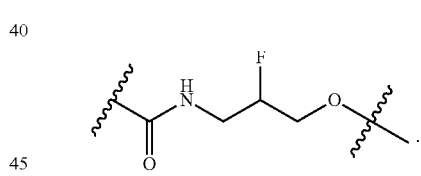
In some embodiments, L is
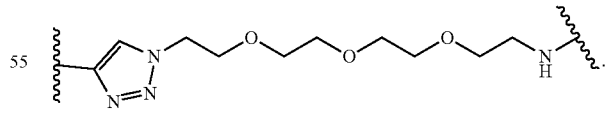

In some embodiments, L is
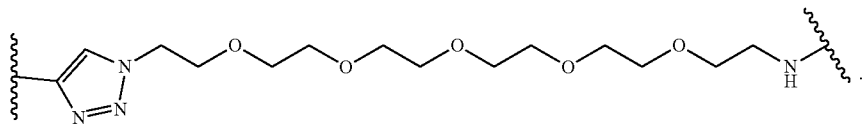 [SMILES: *NCCOCCOCCOCCOCCOCCn1cc(*)nn1]
In some embodiments, L is
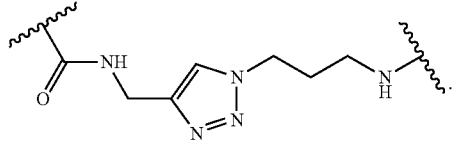 [SMILES: *NCCCn1cc(CNC(*)=O)nn1]
In some embodiments, L is
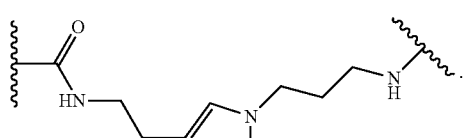
In some embodiments, L is
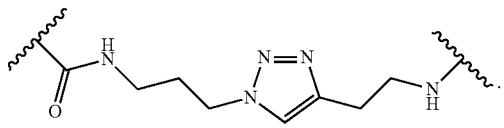 [SMILES: *NCCc1cn(CCCNC(*)=O)nn1]
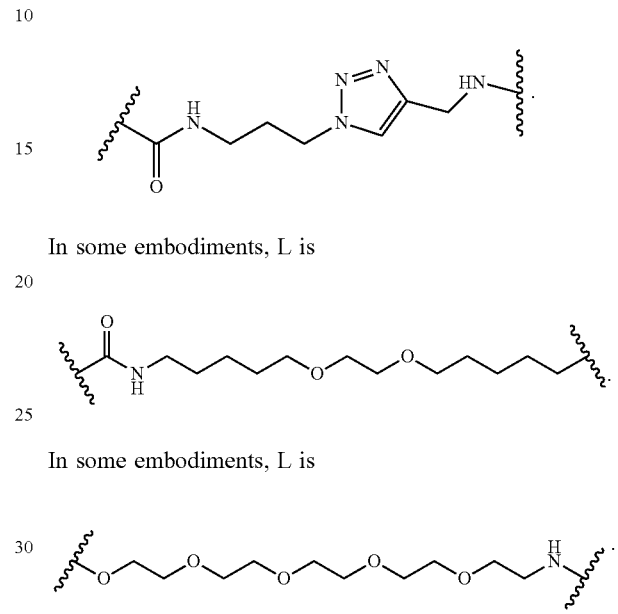
In some embodiments, L is
In some embodiments, L is
In some embodiments, L is
In some embodiments, L is
In some embodiments, L is
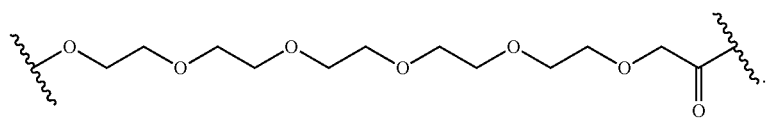 [SMILES: *OCCOCCOCCOCCOCCOCC(*)=O]
In some embodiments, L is
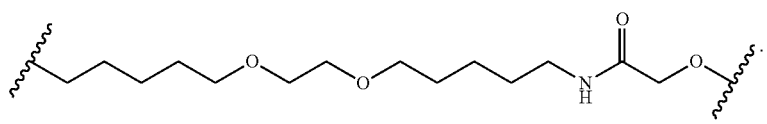 [SMILES: *CCCCCOCCOCCCCCNC(=O)CO*]

In some embodiments, L is
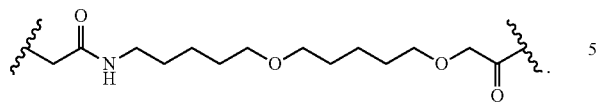
In some embodiments, L is
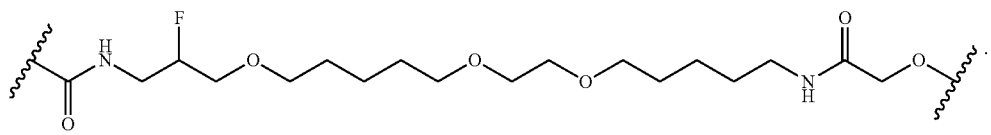 [SMILES: *OCC(=O)NCCCCCOCCOCCCCCOCC(F)CNC(*)=O]
In some embodiments, L is
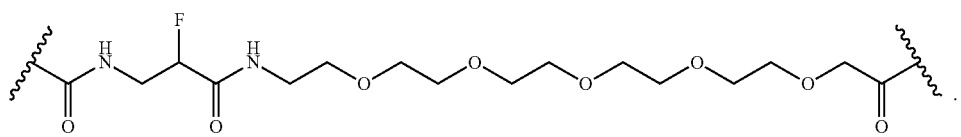 [SMILES: *C(=O)COCCOCCOCCOCCOCCNC(=O)C(F)CNC(*)=O]
In some embodiments, L is
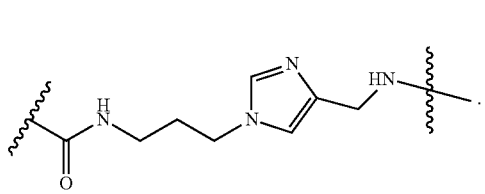 [SMILES: *NCc1cn(CCCNC(*)=O)cn1]
In some embodiments, L is
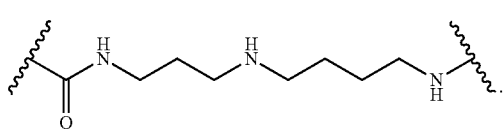 [SMILES: *NCCCCNCCCNC(*)=O]
In some embodiments, L is
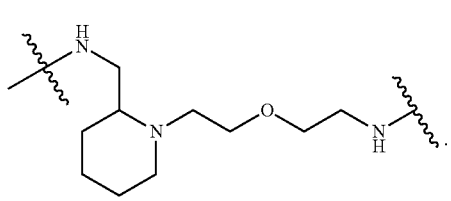 [SMILES: *NCCOCCN1CCCCC1CN*]
In some embodiments, L is
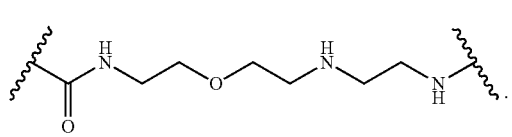 [SMILES: *NCCNCCOCCNC(*)=O]
In some embodiments, L is
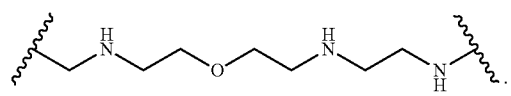 [SMILES: *CNCCOCCNCCN*]
In some embodiment, L is
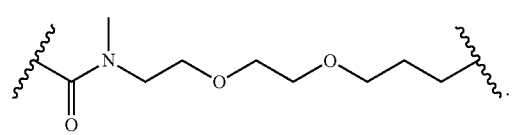 [SMILES: *CCCOCCOCCN(C)C(*)=O]
In some embodiment, L is
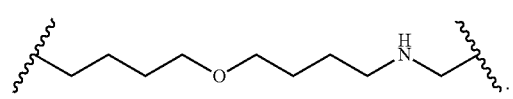 [SMILES: *CCCCOCCCCNC*]
In some embodiment, L is
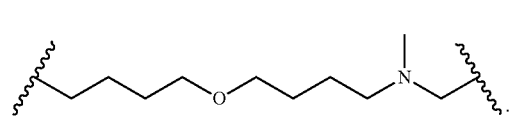 [SMILES: *CCCCOCCCCN(C)C*]

In some embodiments, L is
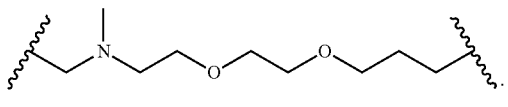 [SMILES: *CCCOCCOCCN(C)C*]
In some embodiments, L is
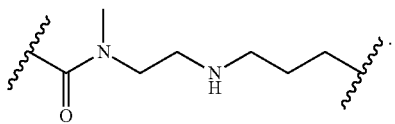 [SMILES: *CCCNCCN(C)C(*)=O]
In some embodiments, L is
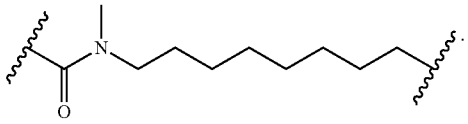 [SMILES: *CCCCCCCCN(C)C(*)=O]
In some embodiments, L is
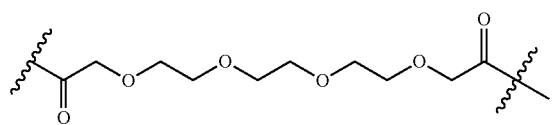
In some embodiments, L is
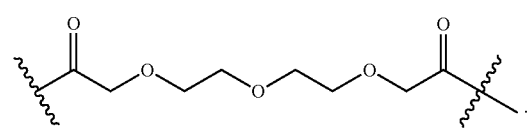 [SMILES: *C(=O)COCCOCCOCC(*)=O]
In some embodiments, L is
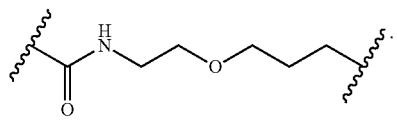 [SMILES: *CCCOCCNC(*)=O]
In some embodiments, L is
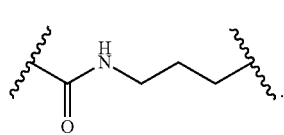 [SMILES: *CCCNC(*)=O]
In some embodiments, L is
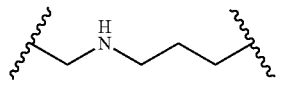
In some embodiments, L is
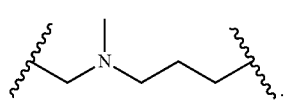 [SMILES: *CCCN(C)C*]
In some embodiments, L is
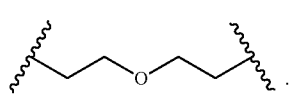 [SMILES: *CCOCC*]
In some embodiments, L is
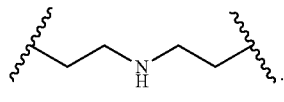 [SMILES: *CCNCC*]
In some embodiments, L is
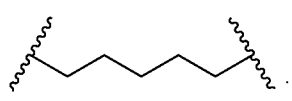 [SMILES: *CCCCC*]
In some embodiments, L is
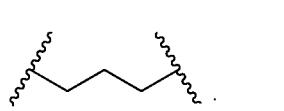 [SMILES: *CCC*]

In some embodiments, L is
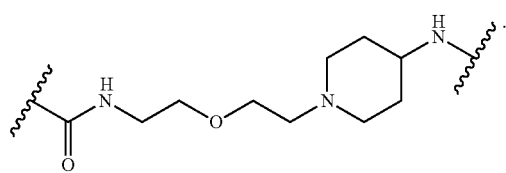
In some embodiments, L is
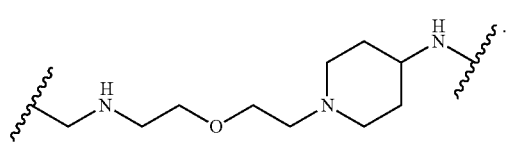
In some embodiments, L is
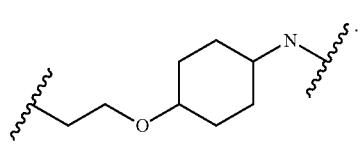 [SMILES: *CCOC1CCC(N*)CC1]
In some embodiments, L is
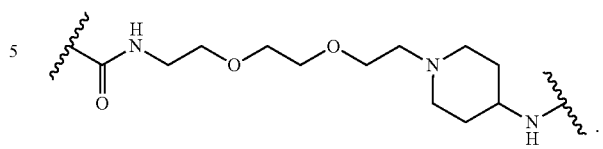
In some embodiments, L is

In some embodiments, L is
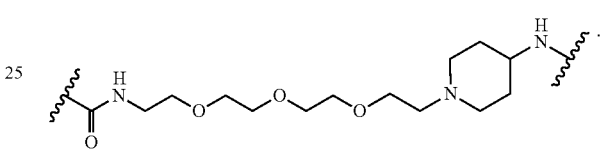
In some embodiments, L is
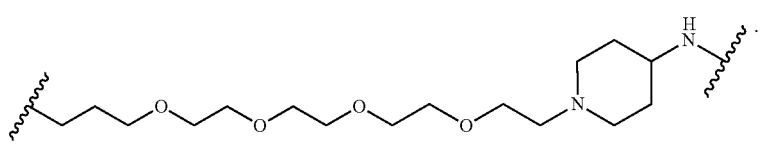
In some embodiments, L is
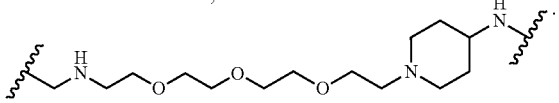
In some embodiments, L is
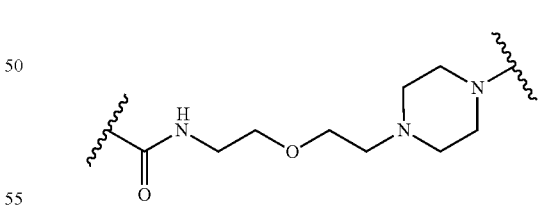
In some embodiments, L is
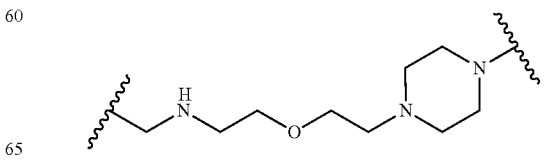

In some embodiments, L is
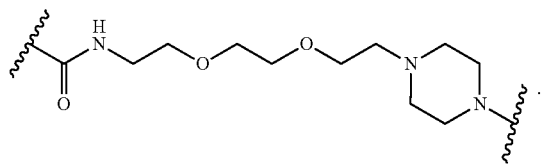
In some embodiments, L is
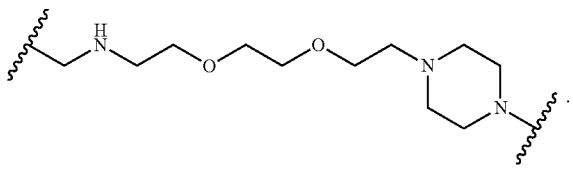 [SMILES: *CNCCOCCOCCN1CCN(*)CC1]
In some embodiments, L is
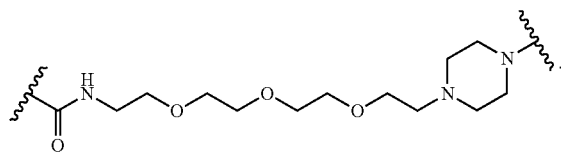 [SMILES: *C(=O)NCCOCCOCCOCCN1CCN(*)CC1]
In some embodiments, L is
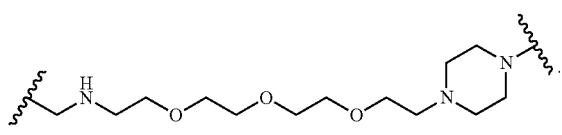 [SMILES: *CNCCOCCOCCOCCN1CCN(*)CC1]
In some embodiments, L is
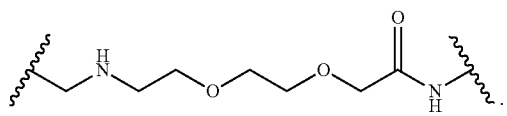 [SMILES: *CNCCOCCOCC(=O)N*]
In some embodiments, L is
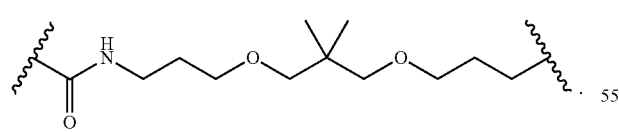
In some embodiments, L is
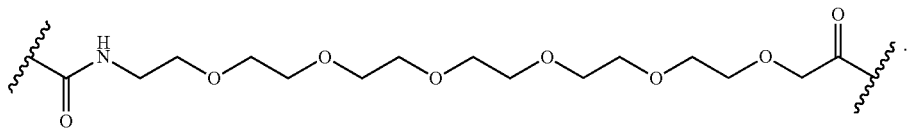 [SMILES: *C(=O)COCCOCCOCCOCCOCCOCCNC(*)=O]
In some embodiments, L is
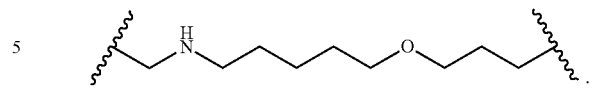
In some embodiments, L is
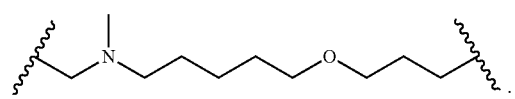 [SMILES: *CCCOCCCCCN(C)C*]
In some embodiments, L is
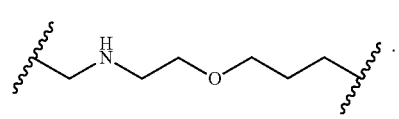 [SMILES: *CCCOCCNC*]
In some embodiments, L is
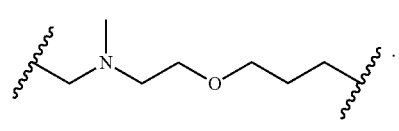 [SMILES: *CCCOCCN(C)C*]
In some embodiments, L is
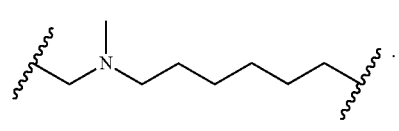 [SMILES: *CCCCCCN(C)C*]
In some embodiments, L is
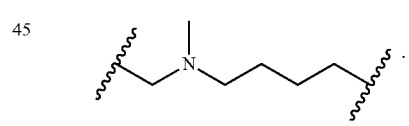
In some embodiments, L is
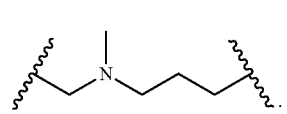 [SMILES: *CCCN(C)C*]

In some embodiments, L is
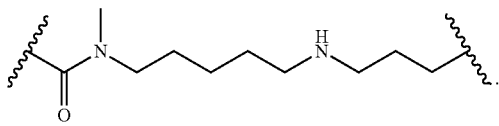 [SMILES: *CCCNCCCCCN(C)C(*)=O]
In some embodiments, L is
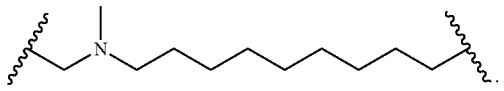 [SMILES: *CCCCCCCCCN(C)C*]
In some embodiments, L is
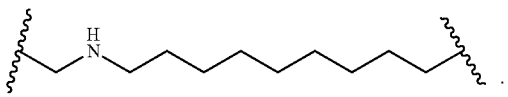
In some embodiments, L is
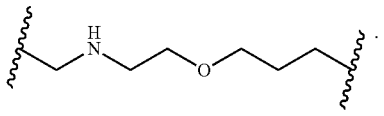
In some embodiments, L is
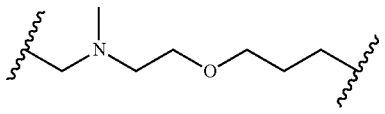
In some embodiments, L is
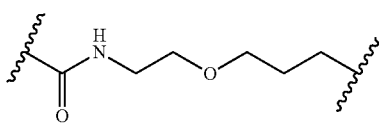
In some embodiments, L is
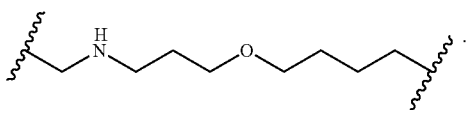
In some embodiments, L is
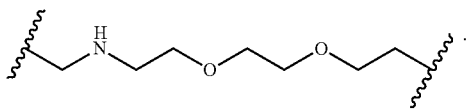
In some embodiments, L is
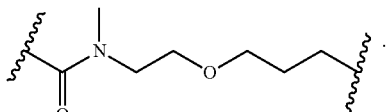
In some embodiments, L is
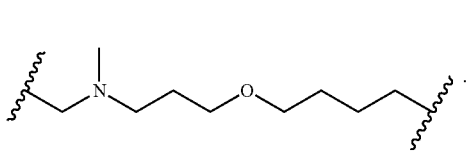 [SMILES: *CCCCOCCCN(C)C*]
In some embodiments, L is
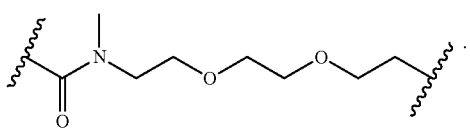 [SMILES: *CCOCCOCCN(C)C(*)=O]
In some embodiments, L is
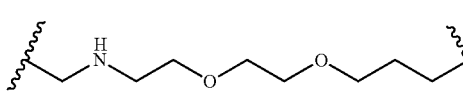
In some embodiments, L is
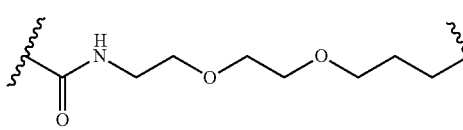
In some embodiments, L is
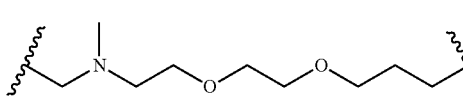

In some embodiments, L is
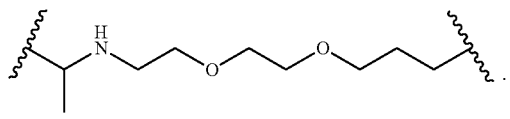
In some embodiments, L is
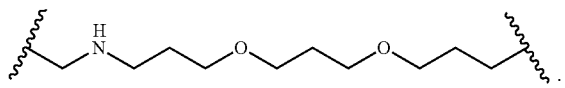
In some embodiment, L is
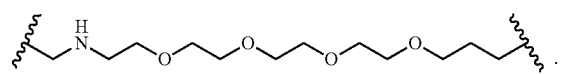
In some embodiment, L is
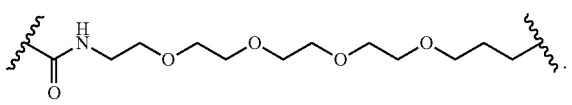 [SMILES: *CCCOCCOCCOCCOCCNC(*)=O]
In some embodiments, L is
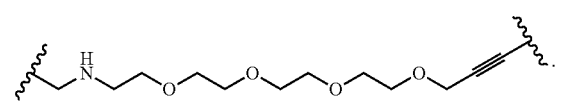 [SMILES: *C#CCOCCOCCOCCOCCNC*]
In some embodiments, L is
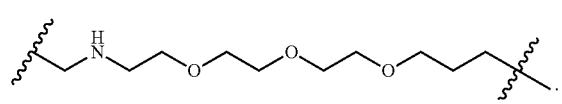 [SMILES: *CCCOCCOCCOCCNC*]
In some embodiments, L is
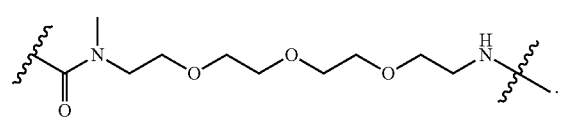 [SMILES: *NCCOCCOCCOCCN(C)C(*)=O]
In some embodiments, L is
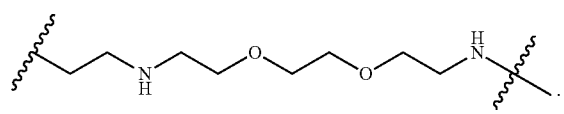 [SMILES: *CCNCCOCCOCCN*]
In some embodiments, L is
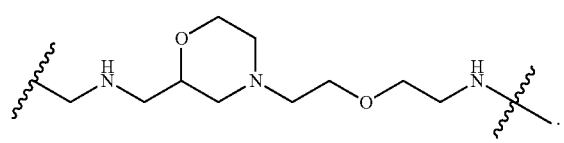 [SMILES: *CNCC1CN(CCOCCN*)CCO1]
In some embodiments, L is
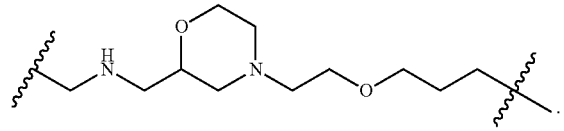 [SMILES: *CCCOCCN1CCOC(CNC*)C1]
In some embodiments, L is
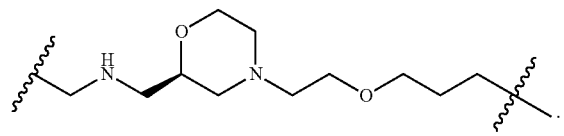 [SMILES: *CCCOCCN1CCO[C@H](CNC*)C1]
In some embodiments, L is
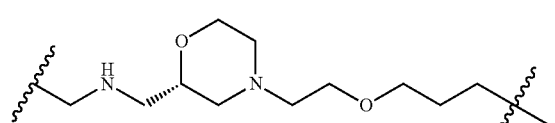
In some embodiments, L is
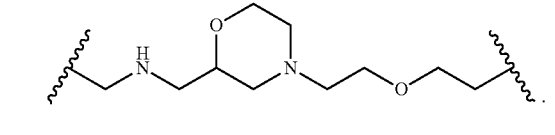 [SMILES: *CCOCCN1CCOC(CNC*)C1]
In some embodiments, L is
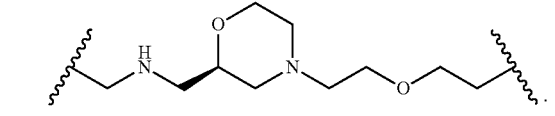 [SMILES: *CCOCCN1CCO[C@H](CNC*)C1]
In some embodiments, L is
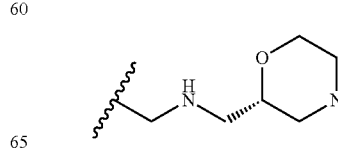

In some embodiments, L is
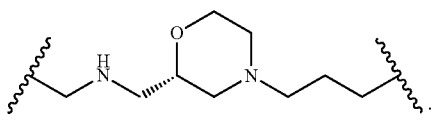 [SMILES: *CCCN1CCO[C@@H](CNC*)C1]
In some embodiments, L is
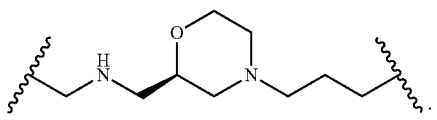 [SMILES: *CCCN1CCO[C@H](CNC*)C1]
In some embodiments, L is
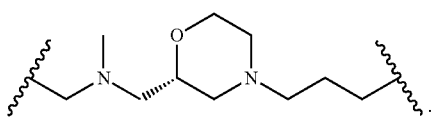 [SMILES: *CCCN1CCO[C@@H](CN(C)C*)C1]
In some embodiments, L is
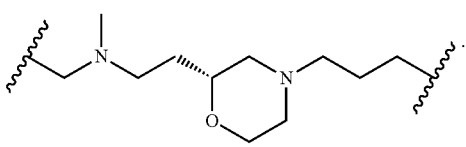 [SMILES: *CCCN1CCO[C@H](CCN(C)C*)C1]
In some embodiments, L is
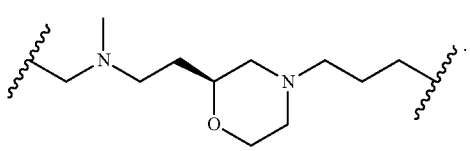 [SMILES: *CCCN1CCO[C@@H](CCN(C)C*)C1]
In some embodiments, L
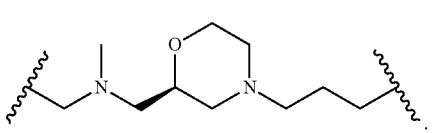 [SMILES: *CCCN1CCO[C@H](CN(C)C*)C1]
In some embodiments, L is
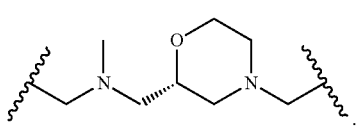 [SMILES: *CN(C)C[C@H]1CN(C*)CCO1]
In some embodiments, L is
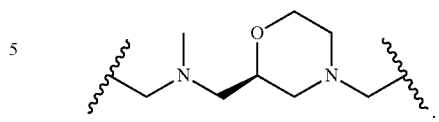
In some embodiments, L is
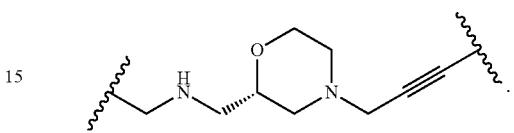
In some embodiments, L is
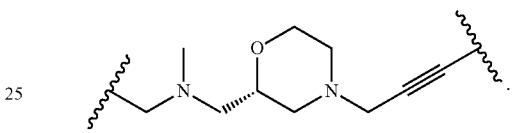
In some embodiments, L is
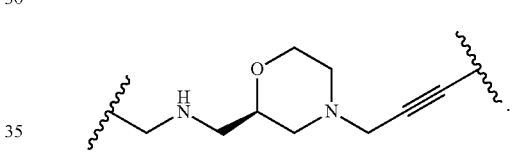
In some embodiments, L is
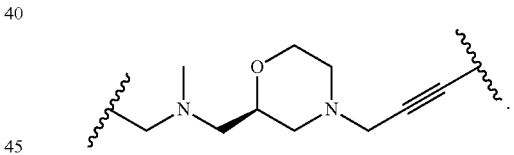
In some embodiments, L is
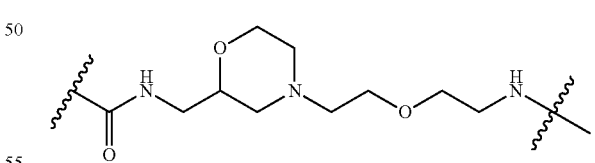
In some embodiments, L is
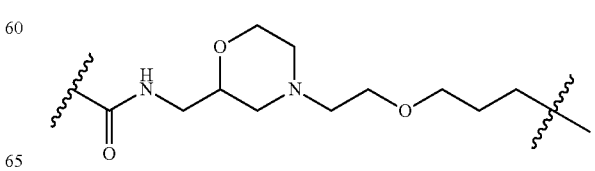

In some embodiments, L is
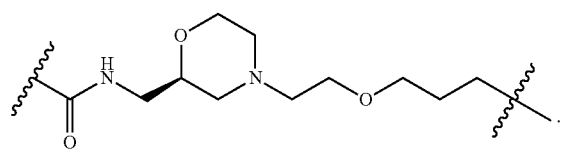 [SMILES: *CCCOCCN1CCO[C@H](CNC(*)=O)C1]
In some embodiments, L is
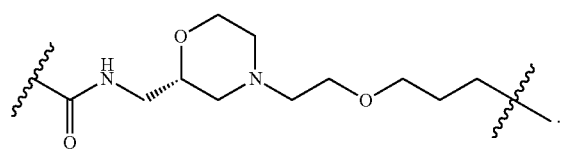 [SMILES: *CCCOCCN1CCO[C@@H](CNC(*)=O)C1]
In some embodiments, L is
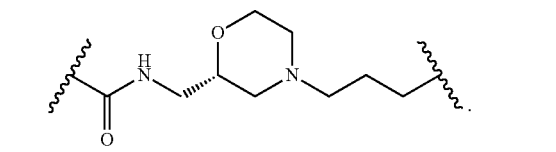 [SMILES: *CCCN1CCO[C@@H](CNC(*)=O)C1]
In some embodiments, L is
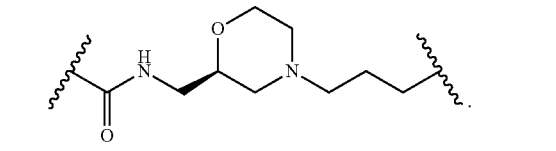 [SMILES: *CCCN1CCO[C@H](CNC(*)=O)C1]
In some embodiments, L is
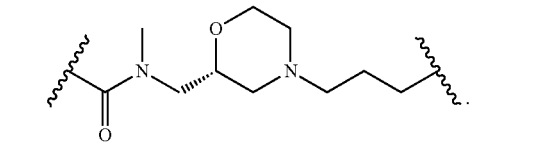 [SMILES: *CCCN1CCO[C@@H](CN(C)C(*)=O)C1]
In some embodiments, L is
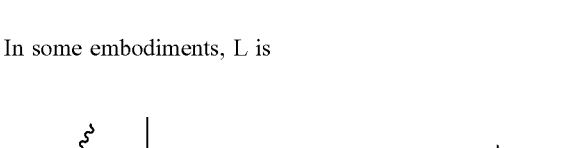
In some embodiments, L is

In some embodiments, L is
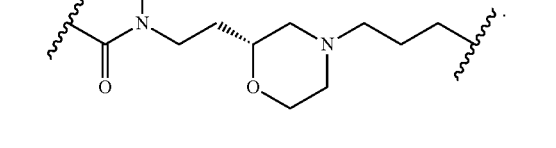
In some embodiments, L is
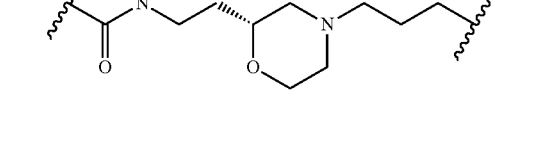
In some embodiments, L is
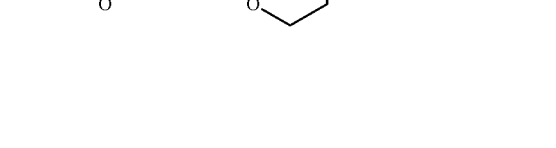
In some embodiments, L is
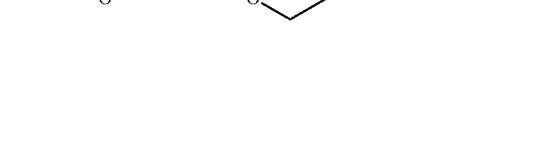
In some embodiments, L is
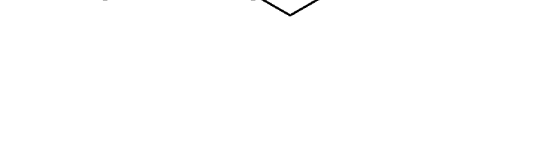

In some embodiments, L is
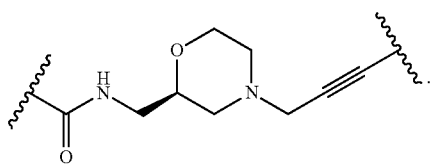 [SMILES: *C#CCN1CCO[C@H](CNC(*)=O)C1]
In some embodiments, L is
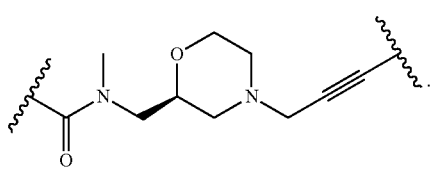 [SMILES: *C#CCN1CCO[C@H](CN(C)C(*)=O)C1]
In some embodiments, L is
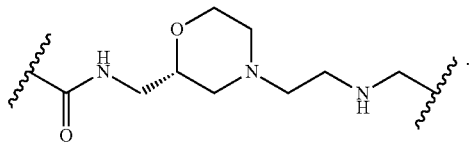 [SMILES: *CNCCN1CCO[C@@H](CNC(*)=O)C1]
In some embodiments, L is
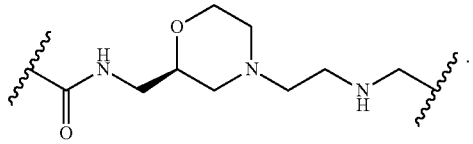 [SMILES: *CNCCN1CCO[C@H](CNC(*)=O)C1]
In some embodiments, L is
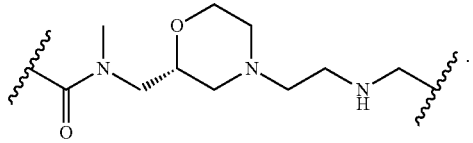 [SMILES: *CNCCN1CCO[C@@H](CN(C)C(*)=O)C1]
In some embodiments, L is
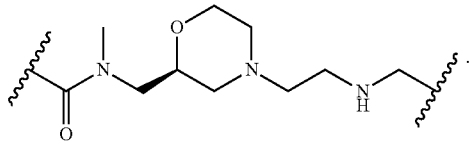 [SMILES: *CNCCN1CCO[C@H](CN(C)C(*)=O)C1]
In some embodiments, L is
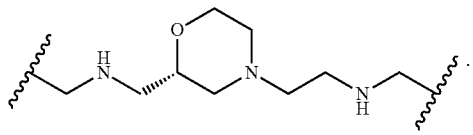 [SMILES: *CNCCN1CCO[C@@H](CNC*)C1]
In some embodiments, L is
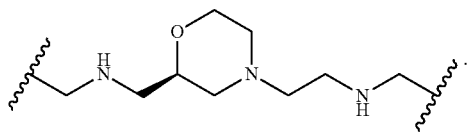 [SMILES: *CNCCN1CCO[C@H](CNC*)C1]
In some embodiments, L is
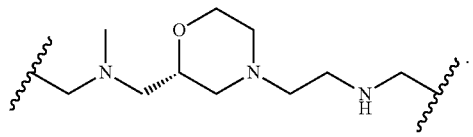 [SMILES: *CNCCN1CCO[C@@H](CN(C)C*)C1]
In some embodiments, L is
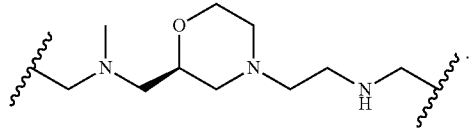 [SMILES: *CNCCN1CCO[C@H](CN(C)C*)C1]
In some embodiments, L is
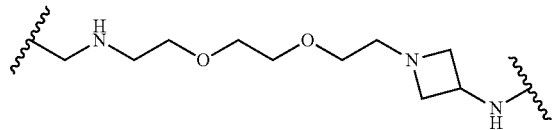
In some embodiments, L is
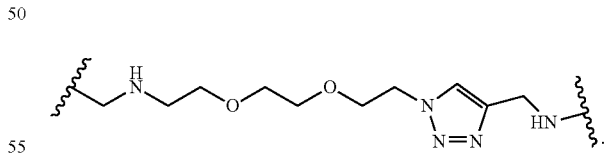
In some embodiments, L is
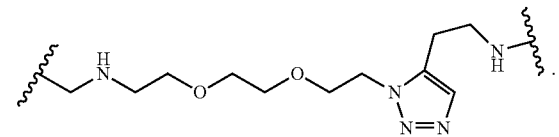 [SMILES: *CNCCOCCOCCn1nncc1CCN*]

In some embodiments, L is

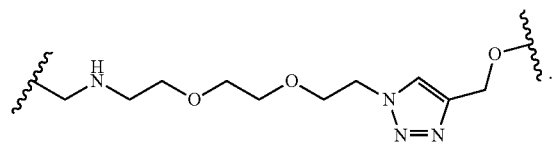 [SMILES: *CNCCOCCOCCn1cc(CO*)nn1]

In some embodiments, L is

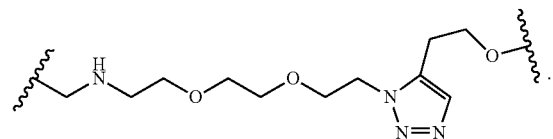 [SMILES: *CNCCOCCOCCn1nncc1CCO*]

In some embodiments, L is

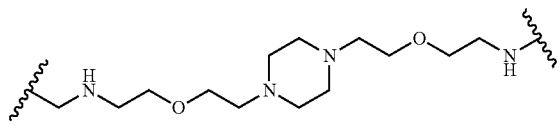

In some embodiments, L is

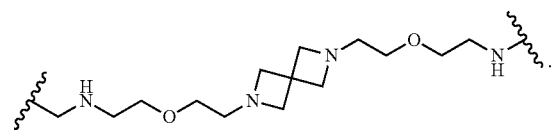 [SMILES: *CNCCOCCN1CC2(CN(CCOCCN*)C2)C1]

In some embodiments, L is

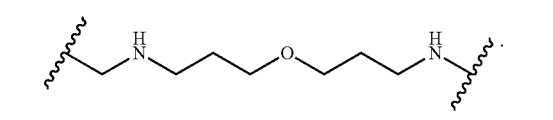 [SMILES: *CNCCCOCCCN*]

In some embodiments, L is

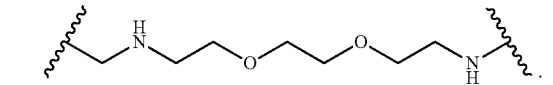 [SMILES: *CNCCOCCOCCN*]

In some embodiments, L is

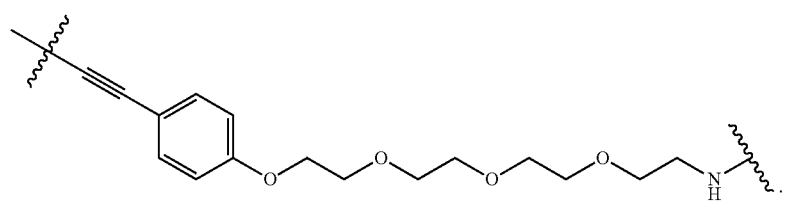 [SMILES: *C#Cc1ccc(OCCOCCOCCOCCN*)cc1]

In some embodiments, L is

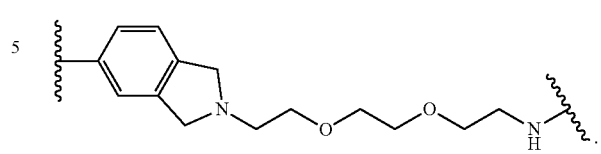

In some embodiments, L is

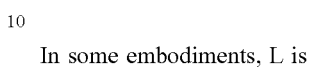

In some embodiments, L is

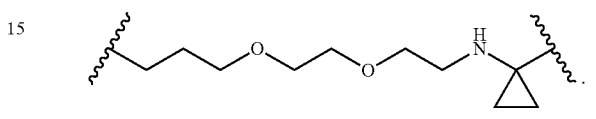

In some embodiments, L is

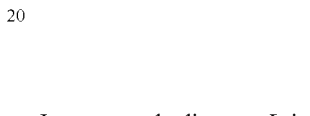

In some embodiments, L is

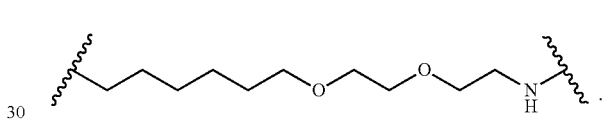

In some embodiments, L is

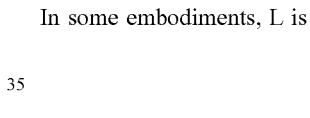

In some embodiments, L is

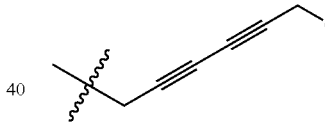

In some embodiments, L is

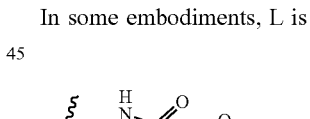

In some embodiments, L is

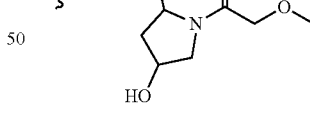

In some embodiments, L is
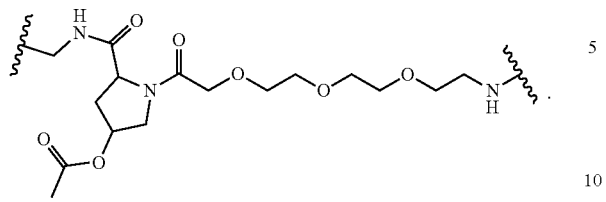
In some embodiments, L is
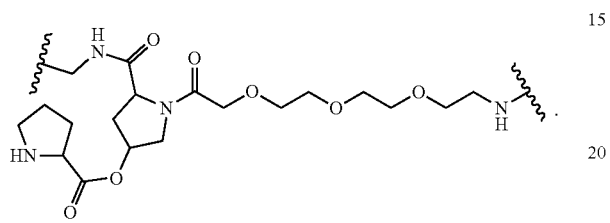
In some embodiments, L is
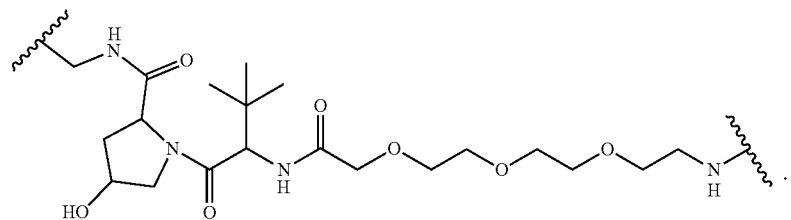
In some embodiments, L is
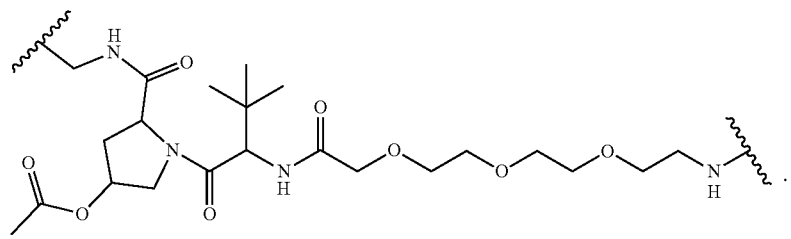
In some embodiments, L is
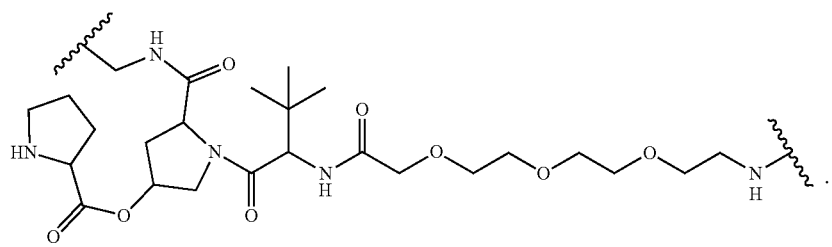

In some embodiments, L is
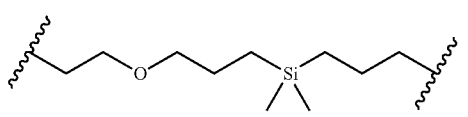
In some embodiments, L is
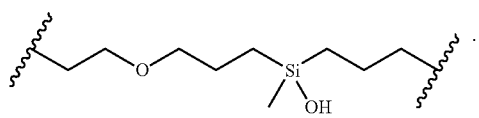 [SMILES: *CCC[Si](C)(O)CCCOCC*]
In some embodiments, L is
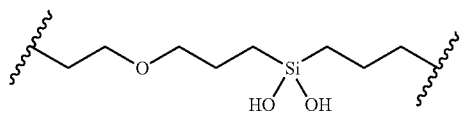
In some embodiments, L is
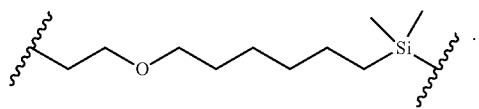 [SMILES: *CCOCCCCCC[Si](*)(C)C]
In some embodiments, L is
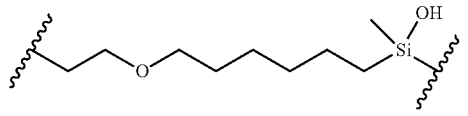
In some embodiments, L is
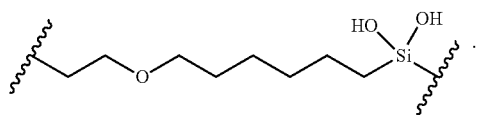 [SMILES: *CCOCCCCCC[Si](*)(O)O]
In some embodiments, L is
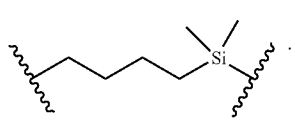 [SMILES: *CCCC[Si](*)(C)C]
In some embodiments, L is
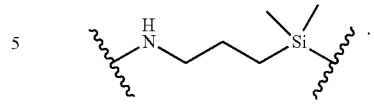
In some embodiments, L is
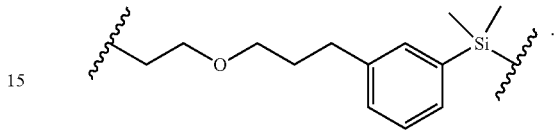
In some embodiments, L is
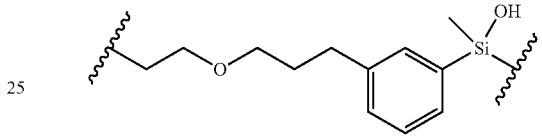
In some embodiments, L is
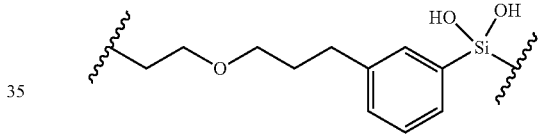
In some embodiments, L is
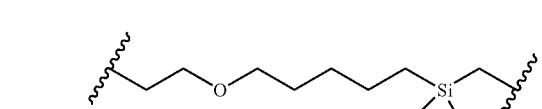
In some embodiments, L is
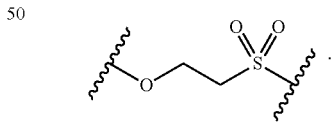
In some embodiments, L is
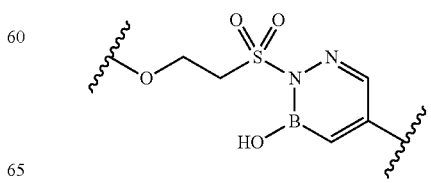

In some embodiments, L is

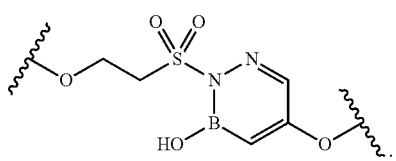 [SMILES: *OCCS(=O)(=O)N1N=CC(O*)=CB1O]

In some embodiments, L is

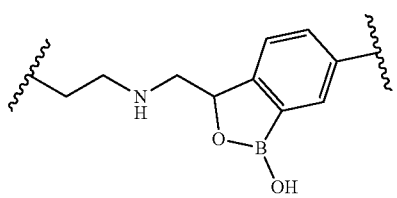

In some embodiments, L is

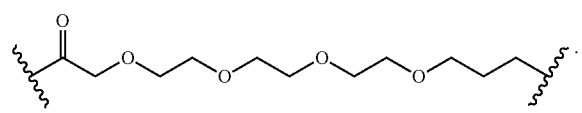 [SMILES: *CCCOCCOCCOCCOCC(*)=O]

In some embodiments, L is

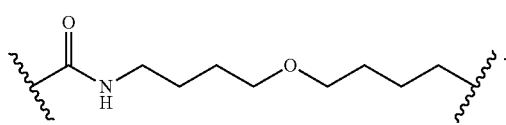 [SMILES: *CCCCOCCCCNC(*)=O]

In some embodiments, L is

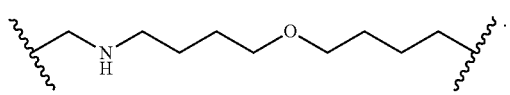 [SMILES: *CCCCOCCCCNC*]

In some embodiments, L is

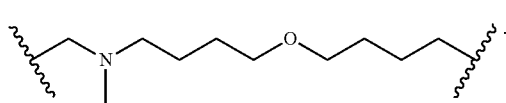 [SMILES: *CCCCOCCCCN(C)C*]

In some embodiments, L is

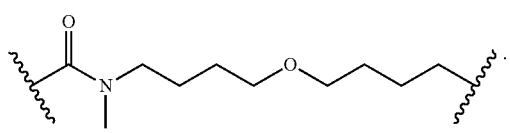 [SMILES: *CCCCOCCCCN(C)C(*)=O]

In some embodiments, L is

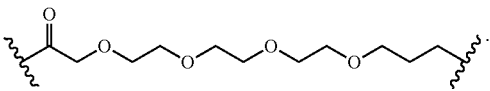 [SMILES: *CCCOCCOCCOCCOCC(*)=O]

In some embodiments, L is

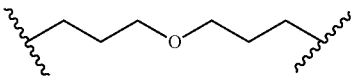

In some embodiments, L is

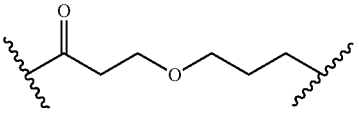

In some embodiments, L is

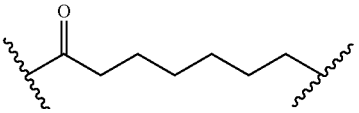

In some embodiments, L is

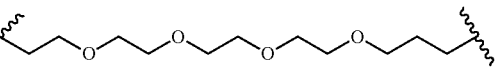

In some embodiments, L is

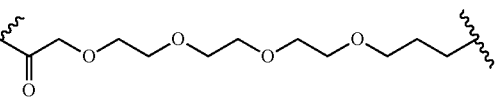

In some embodiments, L is

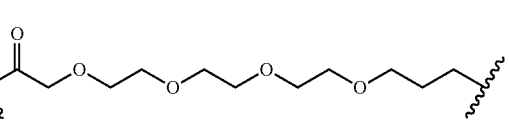

In some embodiments, L is

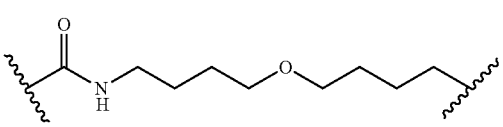

In some embodiments, L is
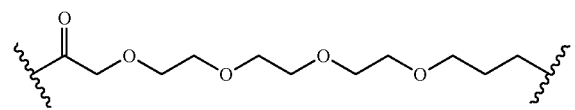
In some embodiments, L is
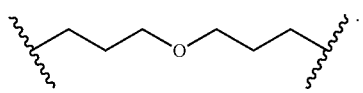 [SMILES: *CCCOCCC*]
In some embodiments, L is
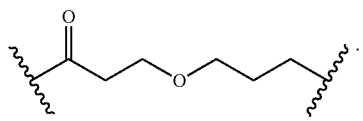 [SMILES: *CCCOCCC(*)=O]
In some embodiments, L is
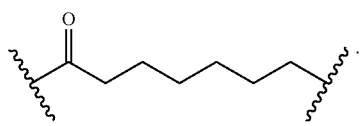 [SMILES: *CCCCCCC(*)=O]
In some embodiments, L is
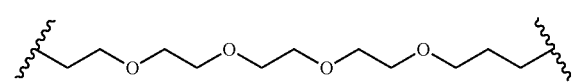
In some embodiments, L is
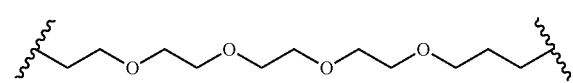
In some embodiments, L is
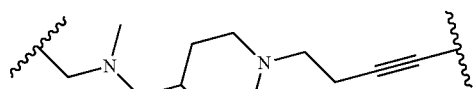
In some embodiments, L is
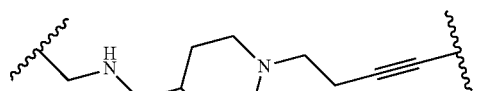
In some embodiments, L is
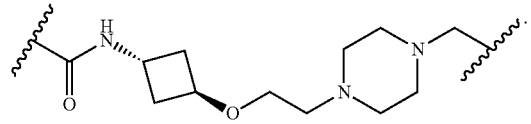 [SMILES: *CN1CCN(CCO[C@H]2C[C@H](NC(*)=O)C2)CC1]
In some embodiments, L is
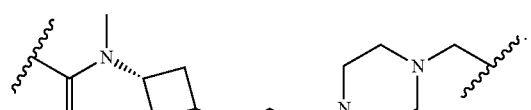
In some embodiments, L is
In some embodiments, L is
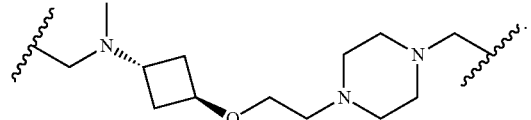
In some embodiments, L is
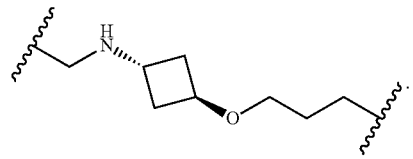 [SMILES: *CCCO[C@H]1C[C@H](NC*)C1]
In some embodiments, L is

In some embodiments, L is
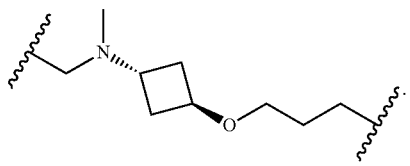 [SMILES: *CCCO[C@H]1C[C@H](N(C)C*)C1]
In some embodiments, L is
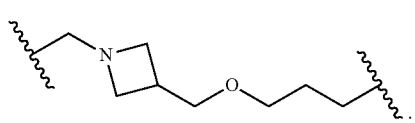 [SMILES: *CCCOCC1CN(C*)C1]
In some embodiments, L is
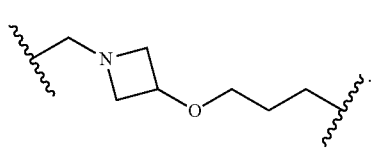 [SMILES: *CCCOC1CN(C*)C1]
In some embodiments, L is
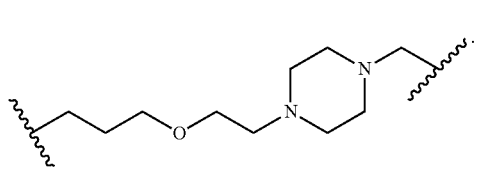 [SMILES: *CCCOCCN1CCN(C*)CC1]
In some embodiments, L is
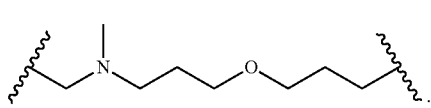 [SMILES: *CCCOCCCN(C)C*]
In some embodiments, L is
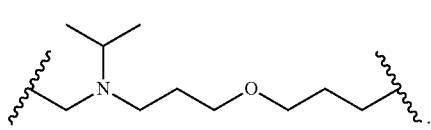 [SMILES: *CCCOCCCN(C*)C(C)C]
In some embodiments, L is
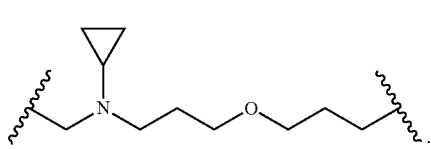 [SMILES: *CCCOCCCN(C*)C1CC1]
In some embodiments, L is
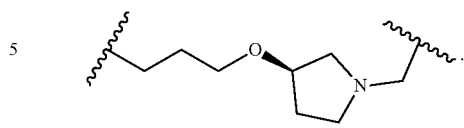
In some embodiments, L is
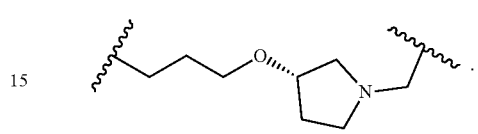
In some embodiments, L is
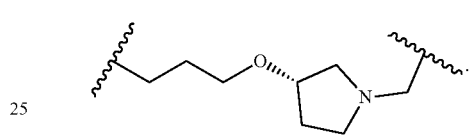
In some embodiments, L is
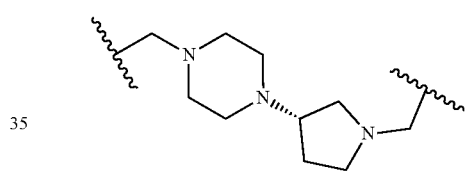
In some embodiments, L is
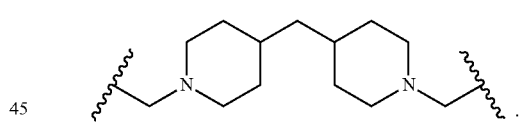
In some embodiments, L is
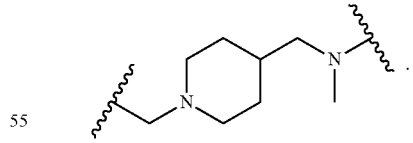
In some embodiments, L is
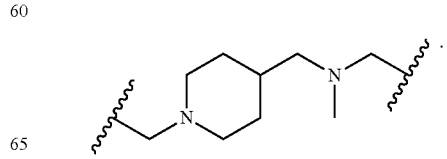

In some embodiments, L is
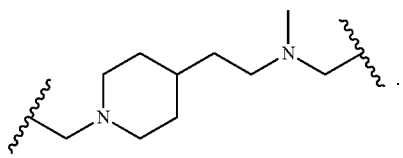 [SMILES: *CN(C)CCC1CCN(C*)CC1]
In some embodiments, L is
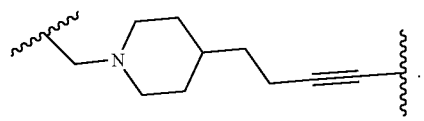 [SMILES: *C#CCCC1CCN(C*)CC1]
In some embodiments, L is
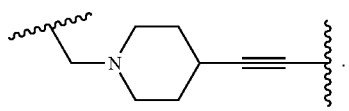
In some embodiments, L is
In some embodiments, L is
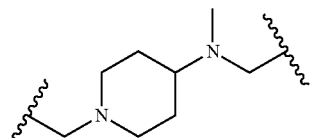
In some embodiments, L is
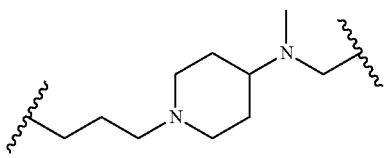
In some embodiments, L is
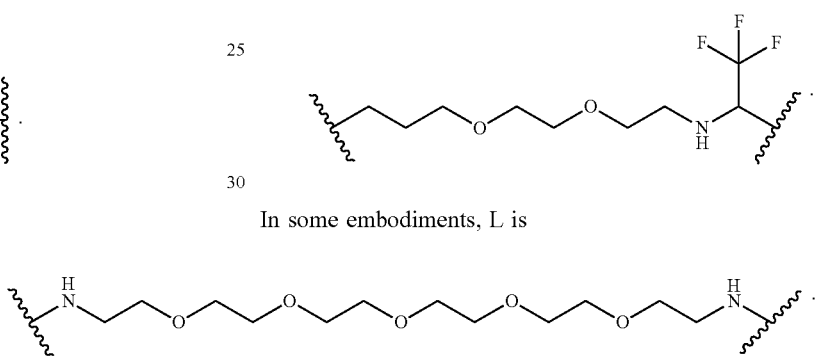
In some embodiments, L is
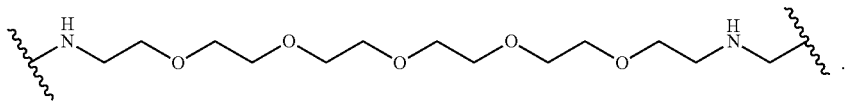
In some embodiments, L is
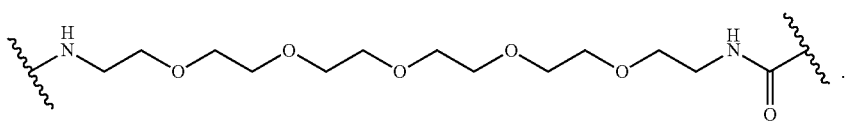

In some embodiments, L is
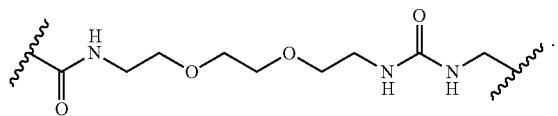
In some embodiments, L is
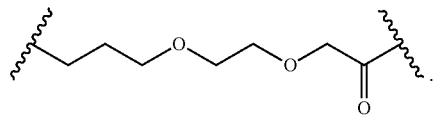 [SMILES: *CCCOCCOCC(*)=O]
In some embodiments, L is
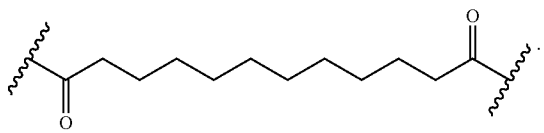 [SMILES: *C(=O)CCCCCCCCCCC(*)=O]
In some embodiments, L is
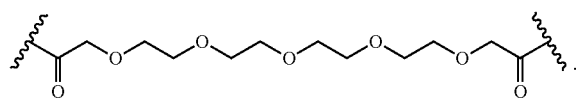 [SMILES: *C(=O)COCCOCCOCCOCCOCC(*)=O]
In some embodiments, L is
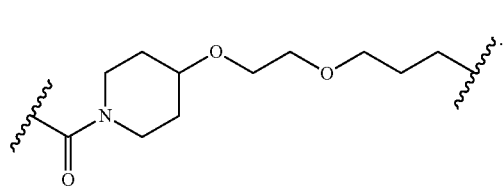 [SMILES: *CCCOCCOC1CCN(C(*)=O)CC1]
In some embodiments, L is
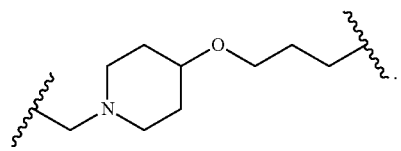 [SMILES: *CCCOC1CCN(C*)CC1]
In some embodiments, L is
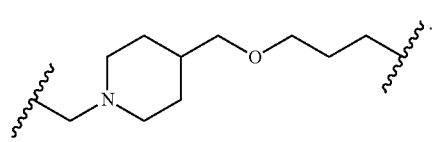 [SMILES: *CCCOCC1CCN(C*)CC1]
In some embodiments, L is
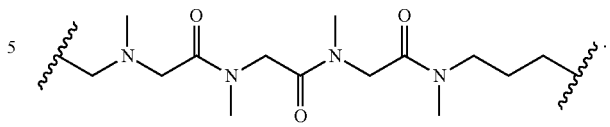
In some embodiments, L is
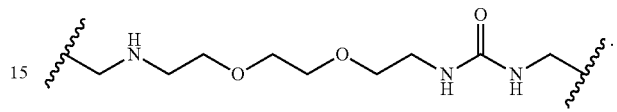
In some embodiment, L is
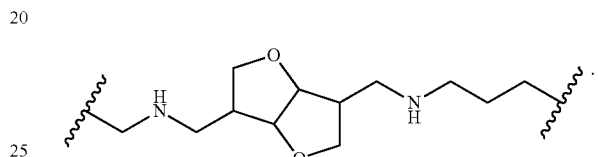
In some embodiments, L is
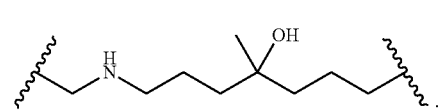 [SMILES: *CCCC(C)(O)CCCNC*]
In some embodiments, L is
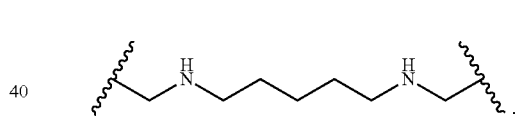
In some embodiments, L is
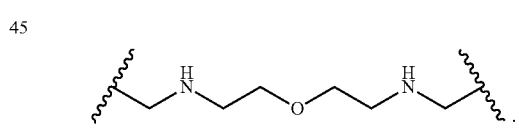
In some embodiments, L is
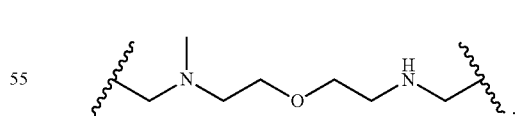
In some embodiments, L is
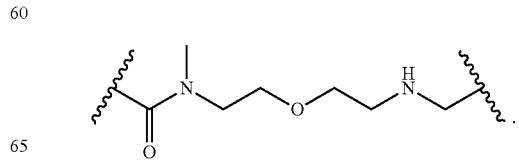

In some embodiments, L is
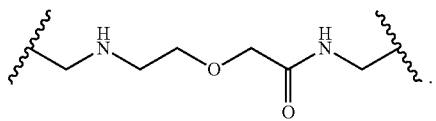 [SMILES: *CNCCOCC(=O)NC*]
In some embodiments, L is
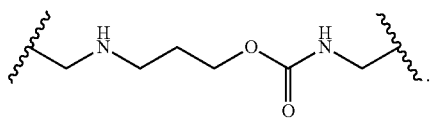
In some embodiments, L is
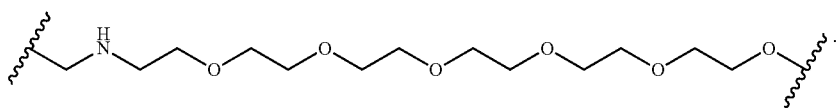 [SMILES: *CNCCOCCOCCOCCOCCOCCO*]
In some embodiments, L is
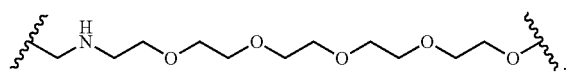 [SMILES: *CNCCOCCOCCOCCOCCO*]
In some embodiments, L is
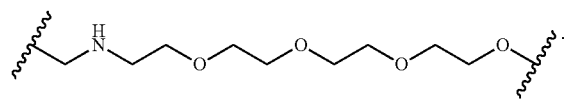 [SMILES: *CNCCOCCOCCOCCO*]
In some embodiments, L is
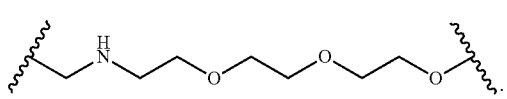 [SMILES: *CNCCOCCOCCO*]
In some embodiments, L is
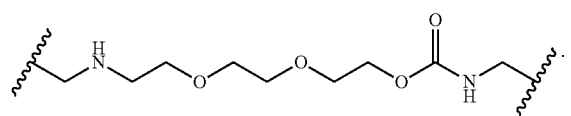 [SMILES: *CNCCOCCOCCOC(=O)NC*]
In some embodiments, L is
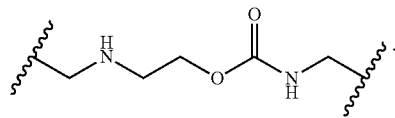 [SMILES: *CNCCOC(=O)NC*]
In some embodiments, L is
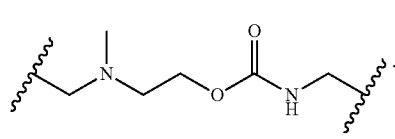 [SMILES: *CNC(=O)OCCN(C)C*]
In some embodiments, L is
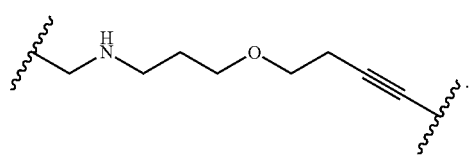 [SMILES: *C#CCCOCCCNC*]
In some embodiments, L is
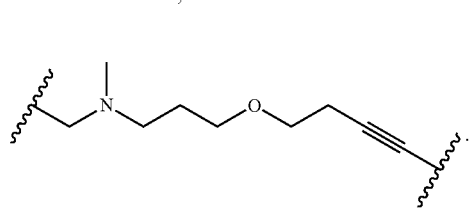
In some embodiments, L is
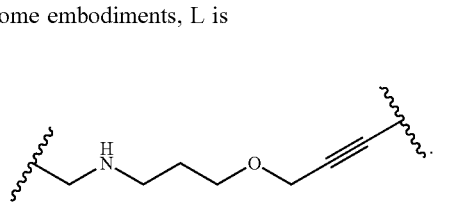
In some embodiments, L is
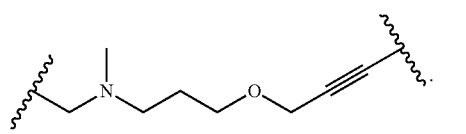 [SMILES: *C#CCOCCCN(C)C*]

In some embodiments, L is
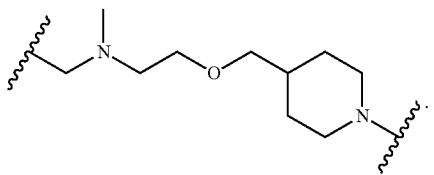 [SMILES: *CN(C)CCOCC1CCN(*)CC1]
In some embodiments, L is
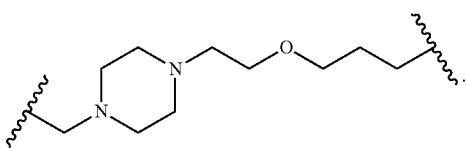 [SMILES: *CCCOCCN1CCN(C*)CC1]
In some embodiments, L is
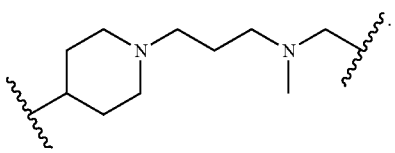 [SMILES: *CN(C)CCCN1CCC(*)CC1]
In some embodiments, L is
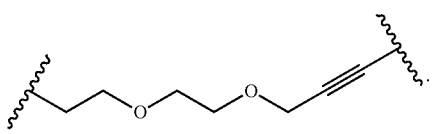 [SMILES: *C#CCOCCOCC*]
In some embodiments, L is
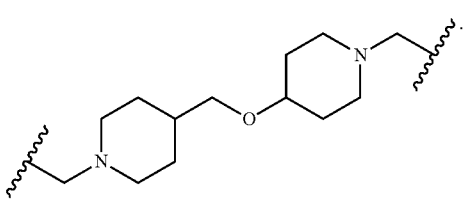 [SMILES: *CN1CCC(COC2CCN(C*)CC2)CC1]
In some embodiments, L is
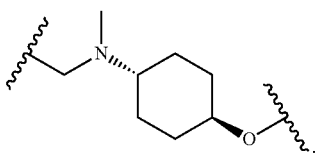 [SMILES: *CN(C)[C@H]1CC[C@H](O*)CC1]
In some embodiments, L is
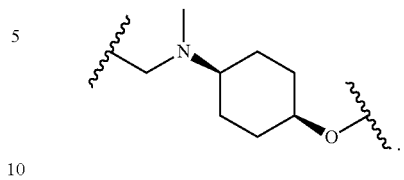
In some embodiments, L is
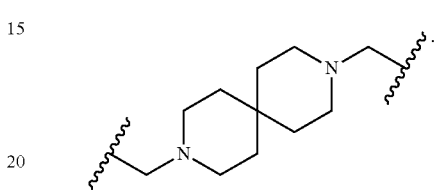
In some embodiments, is
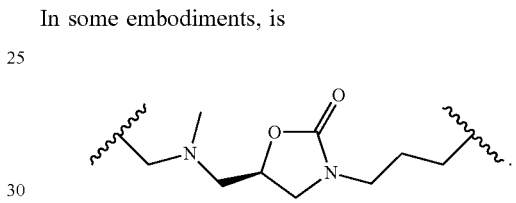
In some embodiments, L is
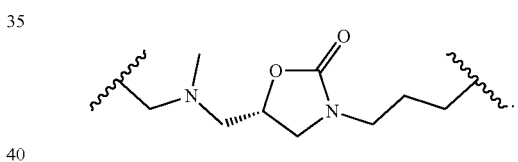
In some embodiments, L is
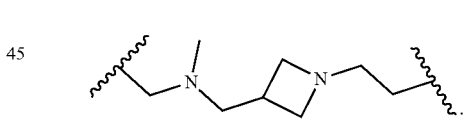
In some embodiments, L is
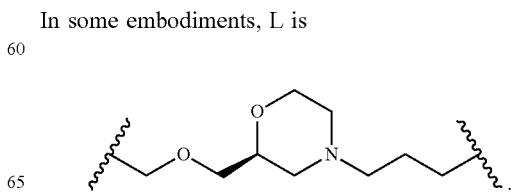

In some embodiments, L is
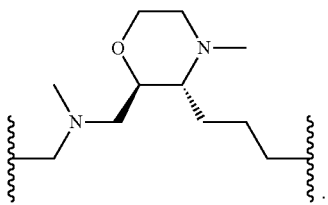 [SMILES: *CCC[C@@H]1[C@@H](CN(C)C*)OCCN1C]
In some embodiments, L is
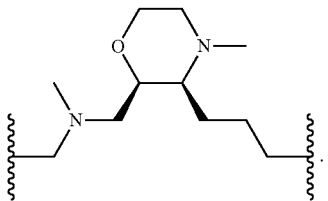 [SMILES: *CCC[C@H]1[C@@H](CN(C)C*)OCCN1C]
In some embodiments, L is
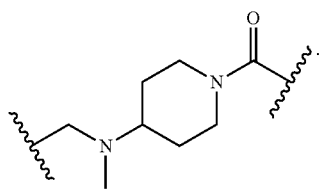 [SMILES: *CN(C)C1CCN(C(*)=O)CC1]
In some embodiments, L is
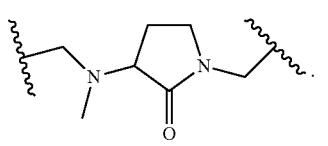 [SMILES: *CN1CCC(N(C)C*)C1=O]
In some embodiments, L is
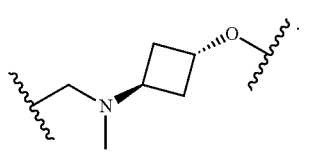 [SMILES: *CN(C)[C@H]1C[C@H](O*)C1]
In some embodiments, L is
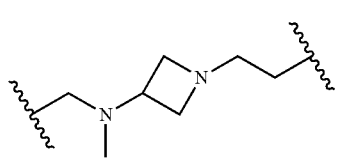
In some embodiments, L is
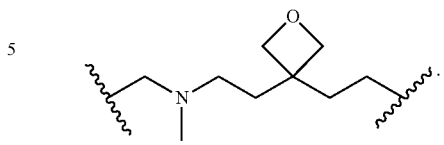
In some embodiments, L is
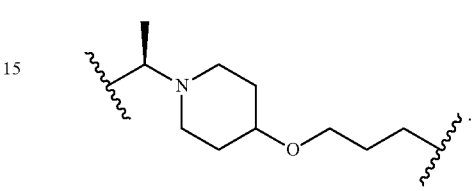
In some embodiments, L is

In some embodiments, L is
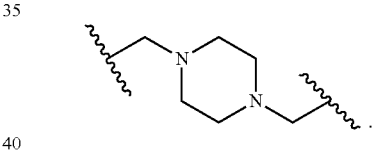
In some embodiments, L is
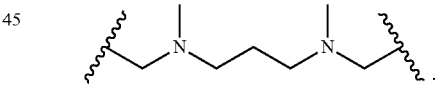
In some embodiments, L is
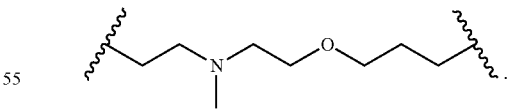
In some embodiments, L is
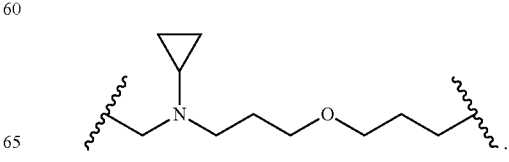

In some embodiments, L is

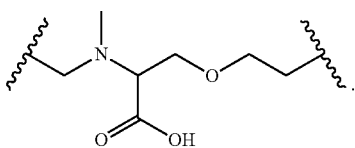 [SMILES: *CCOCC(C(=O)O)N(C)C*]

In some embodiments, L is

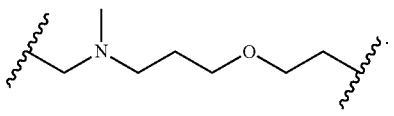 [SMILES: *CCOCCCN(C)C*]

In some embodiments, L is

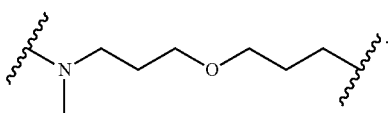 [SMILES: *CCCOCCCN(*)C]

In some embodiments, L is

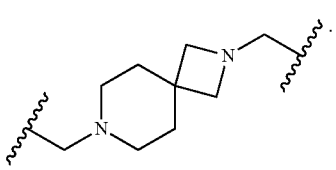 [SMILES: *CN1CCC2(CC1)CN(C*)C2]

In some embodiments, L is

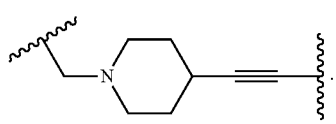 [SMILES: *C#CC1CCN(C*)CC1]

In some embodiments, L is

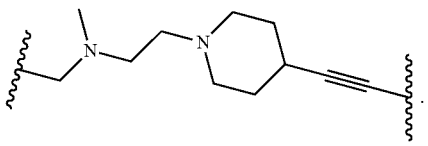 [SMILES: *C#CC1CCN(CCN(C)C*)CC1]

In some embodiments, L is

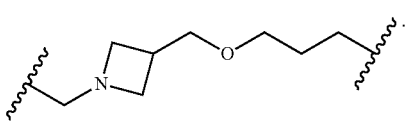 [SMILES: *CCCOCC1CN(C*)C1]

In some embodiments, L is a covalent bond. In some embodiments, L is

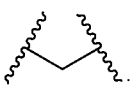

In some embodiments, L is

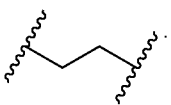 [SMILES: *CC*]

In some embodiments, L is

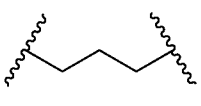

In some embodiments, L is

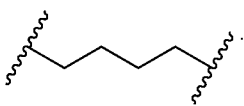 [SMILES: *CCCC*]

In some embodiments, L is

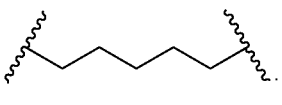 [SMILES: *CCCCC*]

In some embodiments, L is

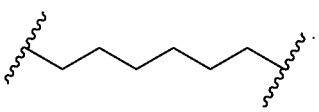 [SMILES: *CCCCCC*]

In some embodiments, L is

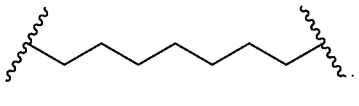 [SMILES: *CCCCCCC*]

In some embodiments, L is

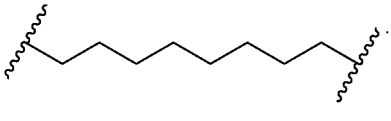 [SMILES: *CCCCCCCC*]

In some embodiments, L is

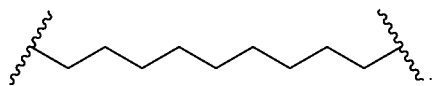 [SMILES: *CCCCCCCCC*]

In some embodiments, L is a covalent bond. In some embodiments, L is

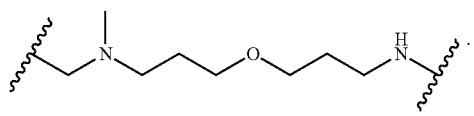 [SMILES: *CN(C)CCCOCCCN*]

In some embodiments, L is

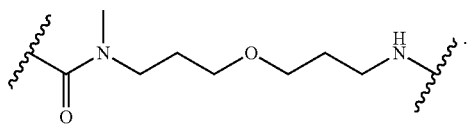 [SMILES: *NCCCOCCCN(C)C(*)=O]

In some embodiments, L is

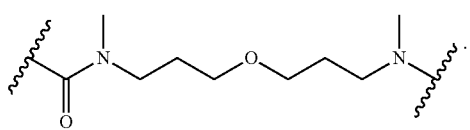 [SMILES: *C(=O)N(C)CCCOCCCN(*)C]

In some embodiments, L is

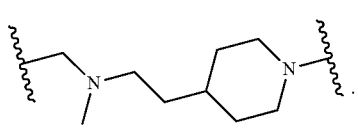

In some embodiments, L is

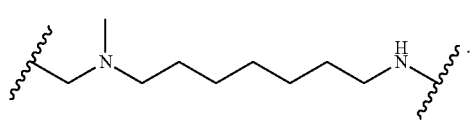 [SMILES: *CN(C)CCCCCCCN*]

In some embodiments, L is

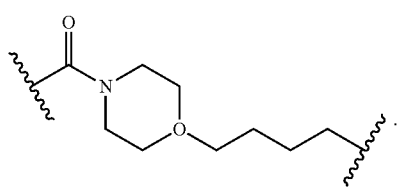

In some embodiments, L is

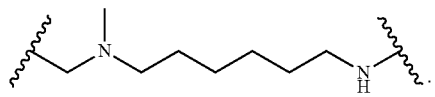 [SMILES: *CN(C)CCCCCCN*]

In some embodiments, L is

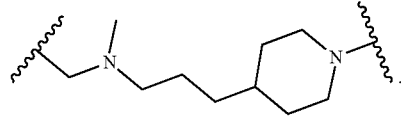 [SMILES: *CN(C)CCCC1CCN(*)CC1]

In some embodiments, L is

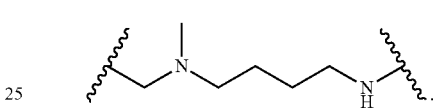

In some embodiments, L is

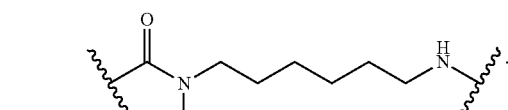

In some embodiments, L is

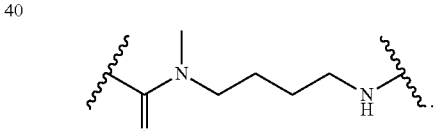

In some embodiments, L is

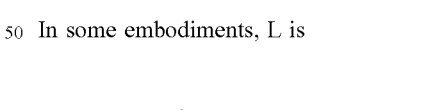

In some embodiments, L is

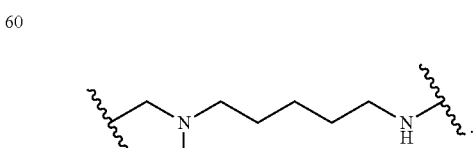

In some embodiments, L is
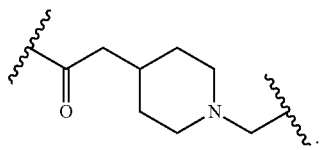 [SMILES: *CN1CCC(CC(*)=O)CC1]
In some embodiments, L is
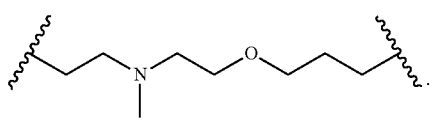 [SMILES: *CCCOCCN(C)CC*]
In some embodiments, L is
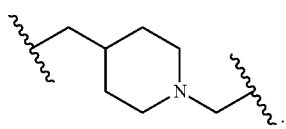
In some embodiments, L is
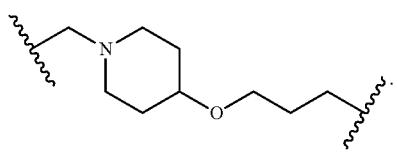 [SMILES: *CCCOC1CCN(C*)CC1]
In some embodiments, L is
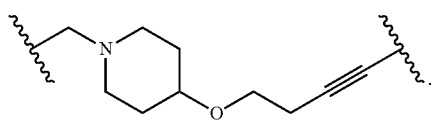 [SMILES: *C#CCCOC1CCN(C*)CC1]
In some embodiments, is
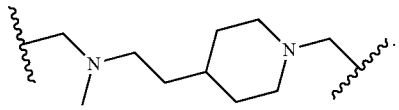 [SMILES: *CN(C)CCC1CCN(C*)CC1]
In some embodiments, L is
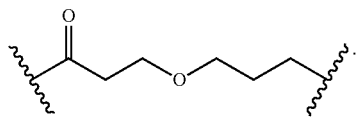 [SMILES: *CCCOCCC(*)=O]
In some embodiments, L is
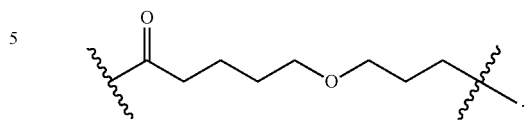
In some embodiments, L is
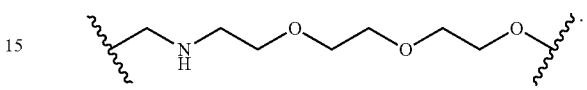
In some embodiments, L is
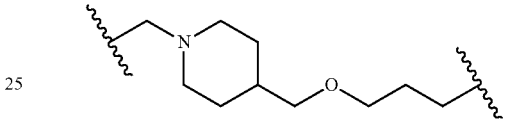
In some embodiments, L is
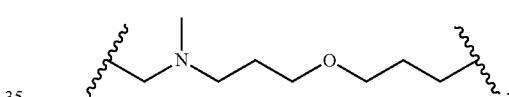
In some embodiments, L is
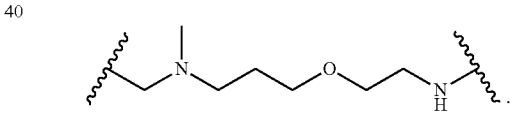
In some embodiments, L is
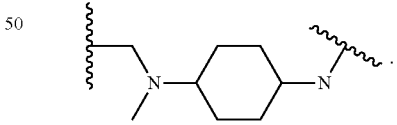
In some embodiments, L is
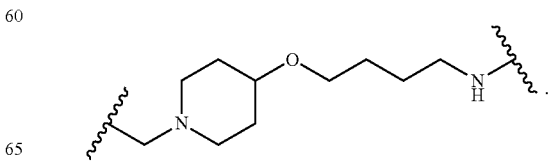

In some embodiments, L is
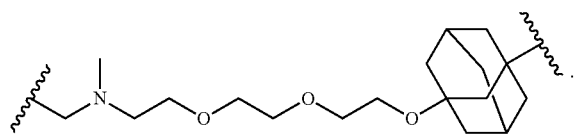 [SMILES: *CN(C)CCOCCOCCOC12CC3CC(CC(*)(C3)C1)C2]
In some embodiments, L is
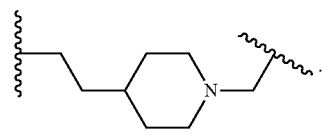 [SMILES: *CCC1CCN(C*)CC1]
In some embodiments, L is
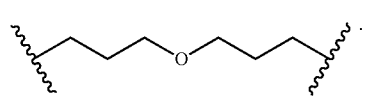 [SMILES: *CCCOCCC*]
In some embodiments, L is
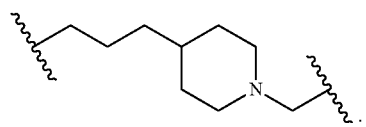 [SMILES: *CCCC1CCN(C*)CC1]
In some embodiments, L is
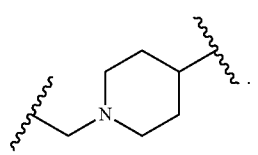 [SMILES: *CN1CCC(*)CC1]
In some embodiments, L is
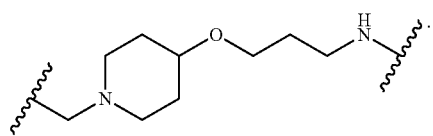 [SMILES: *CN1CCC(OCCCN*)CC1]
In some embodiments, L is
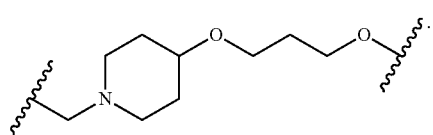 [SMILES: *CN1CCC(OCCCO*)CC1]
In some embodiments, L is
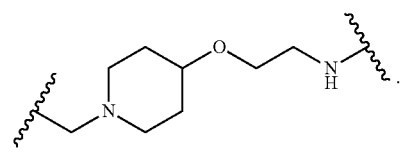 [SMILES: *CN1CCC(OCCN*)CC1]
In some embodiments, L is
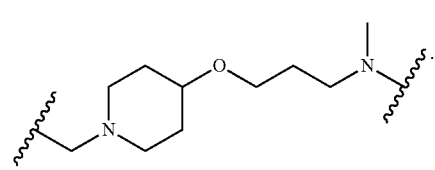 [SMILES: *CN1CCC(OCCCN(*)C)CC1]
In some embodiments, L is
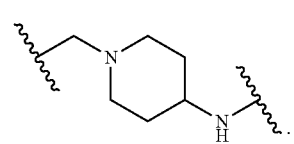 [SMILES: *CN1CCC(N*)CC1]
In some embodiments, L is
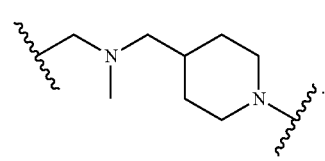 [SMILES: *CN(C)CC1CCN(*)CC1]
In some embodiments, L is
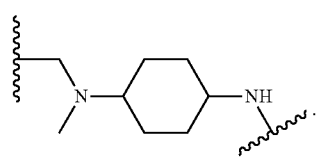 [SMILES: *CN(C)C1CCC(N*)CC1]
In some embodiments, L is
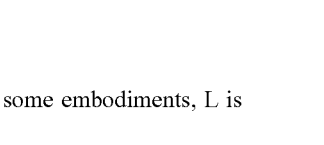
In some embodiments, L is
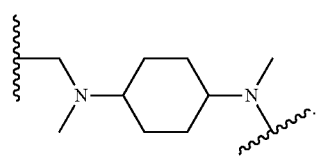 [SMILES: *CN(C)C1CCC(N(*)C)CC1]

In some embodiments, L is
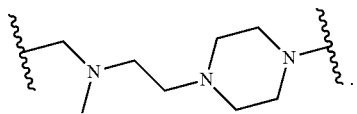
In some embodiments, L is
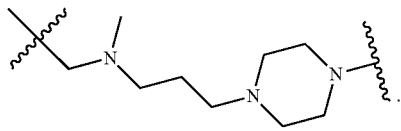 [SMILES: *CN(C)CCCN1CCN(*)CC1]
In some embodiments, L is
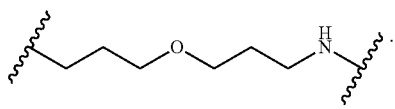
In some embodiments, L is
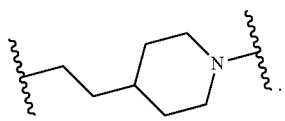 [SMILES: *CCC1CCN(*)CC1]
In some embodiments, L is
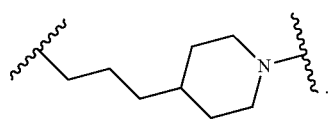 [SMILES: *CCCC1CCN(*)CC1]
In some embodiments, L is
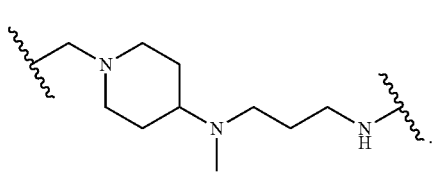 [SMILES: *CN1CCC(N(C)CCCN*)CC1]
In some embodiments, L is
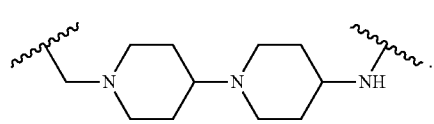 [SMILES: *CN1CCC(N2CCC(N*)CC2)CC1]
In some embodiments, L is
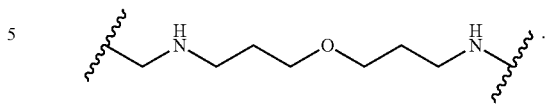
In some embodiments, L is
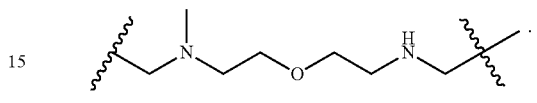
In some embodiments, L is
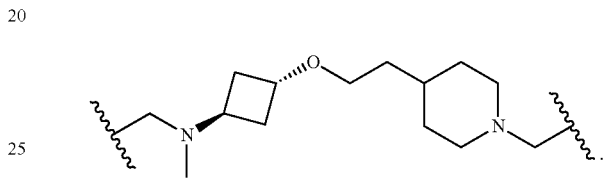
In some embodiments, L is
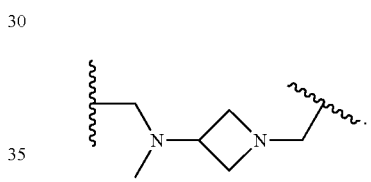
In some embodiments, L is
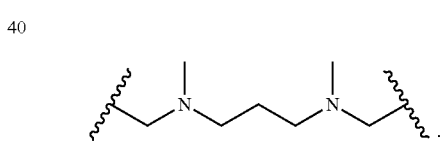
In some embodiments, L is
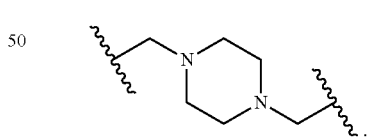
In some embodiments, L is
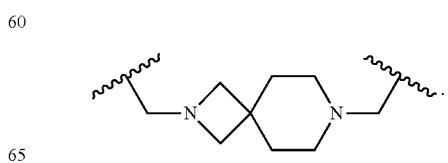

In some embodiments, L is
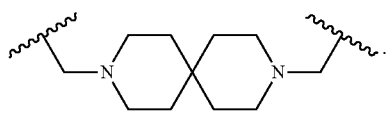 [SMILES: *CN1CCC2(CC1)CCN(C*)CC2]
In some embodiments, L is
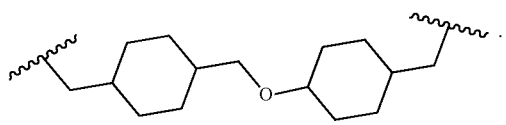 [SMILES: *CC1CCC(COC2CCC(C*)CC2)CC1]
In some embodiments, L is
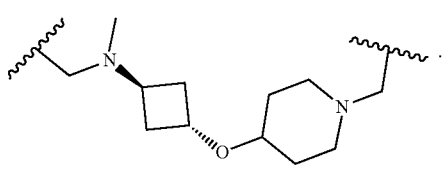 [SMILES: *CN1CCC(O[C@H]2C[C@H](N(C)C*)C2)CC1]
In some embodiments, L is
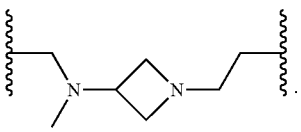 [SMILES: *CCN1CC(N(C)C*)C1]
In some embodiments, L is
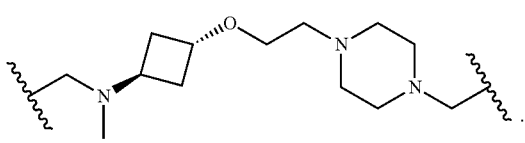 [SMILES: *CN1CCN(CCO[C@H]2C[C@H](N(C)C*)C2)CC1]
In some embodiments, L is
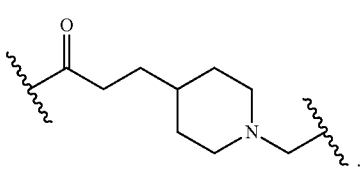 [SMILES: *CN1CCC(CCC(*)=O)CC1]
In some embodiments, L is
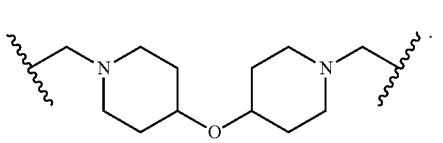 [SMILES: *CN1CCC(OC2CCN(C*)CC2)CC1]
In some embodiments, L is
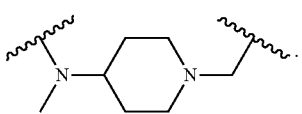 [SMILES: *CN1CCC(N(*)C)CC1]
In some embodiments, L is
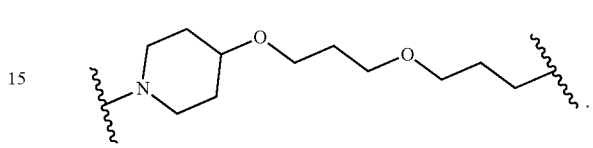
In some embodiments, L is
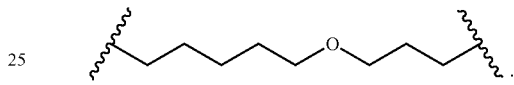
In some embodiments, L is
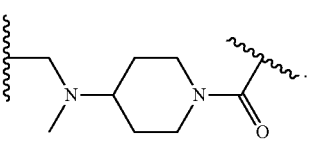 [SMILES: *CN(C)C1CCN(C(*)=O)CC1]
In some embodiments, L is
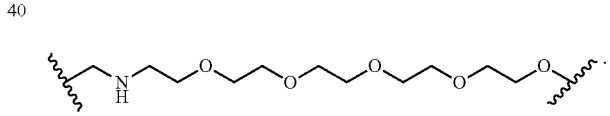
In some embodiments, L is
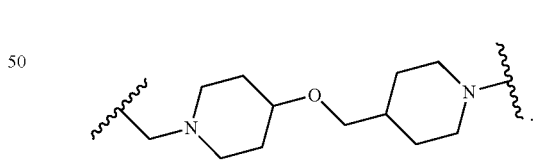
In some embodiments, L is
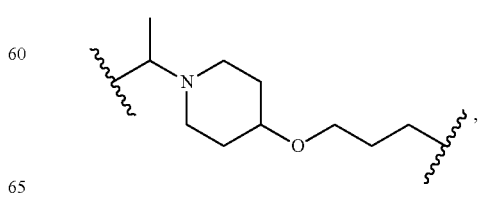

In some embodiments, L is
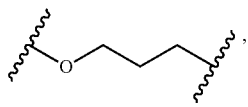
In some embodiments, L is
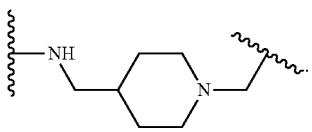 [SMILES: *CN1CCC(CN*)CC1]
In some embodiments, L is
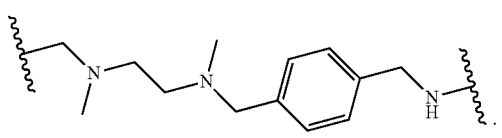 [SMILES: *CN(C)CCN(C)Cc1ccc(CN*)cc1]
In some embodiments, L is
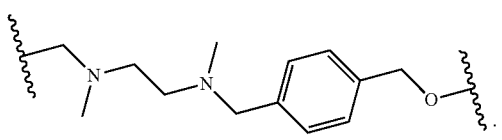 [SMILES: *CN(C)CCN(C)Cc1ccc(CO*)cc1]
In some embodiments, L is
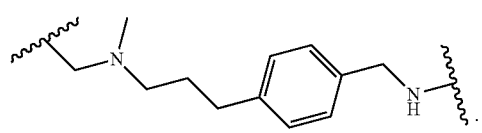 [SMILES: *CN(C)CCCc1ccc(CN*)cc1]
In some embodiments, L is
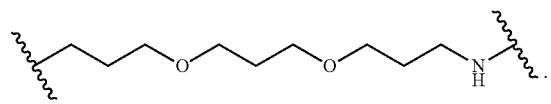 [SMILES: *CCCOCCCOCCCN*]
In some embodiments, L is
In some embodiments, L is
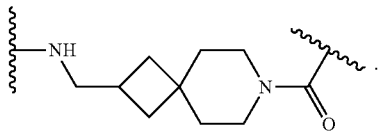 [SMILES: *NCC1CC2(CCN(C(*)=O)CC2)C1]
In some embodiments, L is
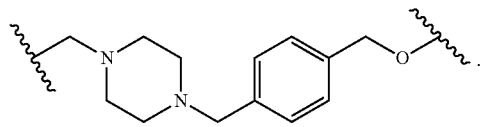 [SMILES: *CN1CCN(Cc2ccc(CO*)cc2)CC1]
In some embodiments, L is
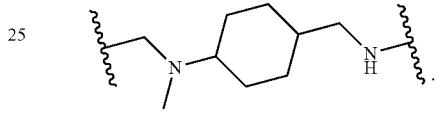
In some embodiments, L is
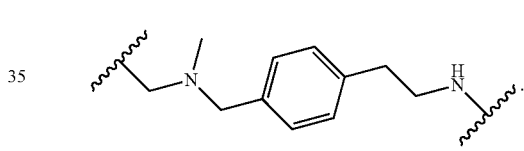
In some embodiments, L is
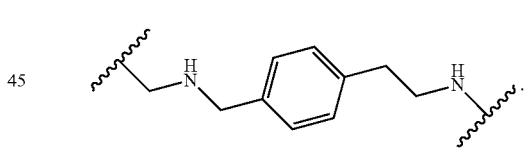
In some embodiments, L is
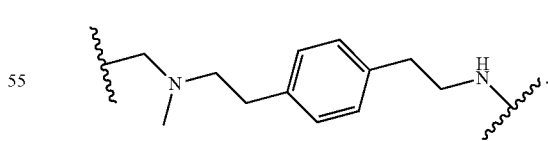
In some embodiments, L is
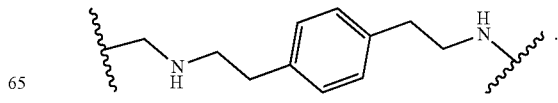

In some embodiments, L is
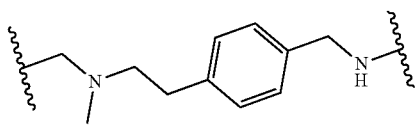
In some embodiments, L is
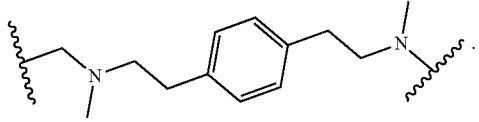 [SMILES: *CN(C)CCc1ccc(CCN(*)C)cc1]
In some embodiments, L is
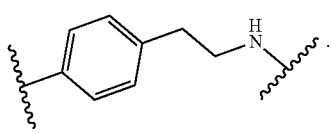
In In some embodiments, L is
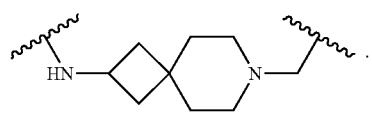
In some In In some embodiments, L is
embodiments, L is
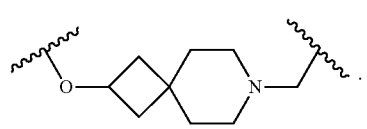 [SMILES: *CN1CCC2(CC1)CC(O*)C2]
In some embodiments, L is
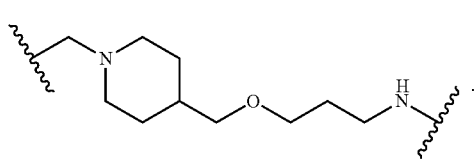
In some embodiments, L is
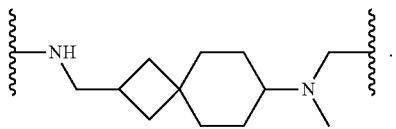 [SMILES: *CN(C)C1CCC2(CC1)CC(CN*)C2]
In some embodiments, L is
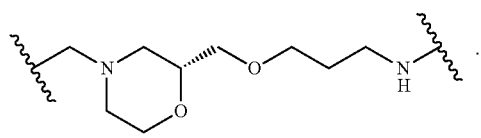
In some embodiments, L is
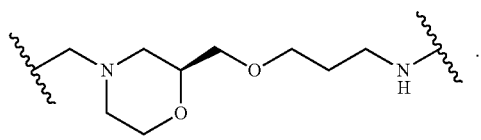
In some embodiments, L is
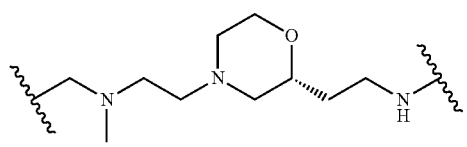
In some embodiments, L is
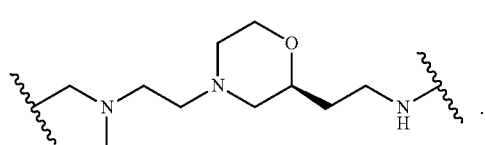
In some embodiments, L is
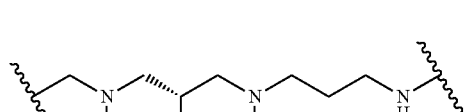
In some embodiments, L is
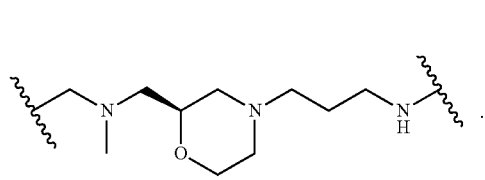

In some embodiments, L is
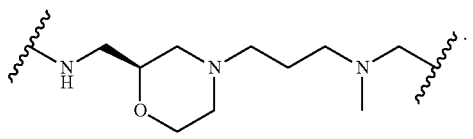 [SMILES: *CN(C)CCCN1CCO[C@@H](CN*)C1]
In some embodiments, L is
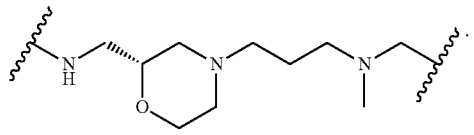 [SMILES: *CN(C)CCCN1CCO[C@H](CN*)C1]
In some embodiments, L is
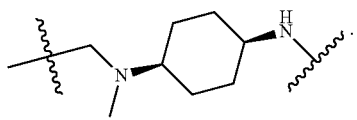 [SMILES: *CN(C)[C@H]1CC[C@@H](N*)CC1]
In some embodiments, L is
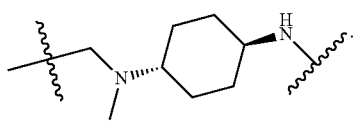 [SMILES: *CN(C)[C@H]1CC[C@H](N*)CC1]
In some embodiments, L is
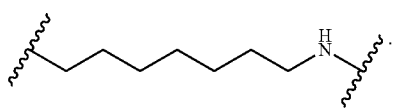 [SMILES: *CCCCCCCN*]
In some embodiments, L is
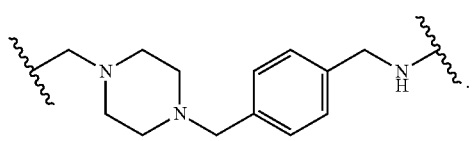 [SMILES: *CN1CCN(Cc2ccc(CN*)cc2)CC1]
some embodiments, L is
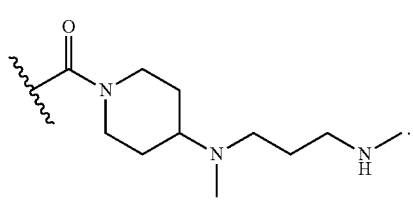 [SMILES: *C(=O)N1CCC(N(C)CCCNC)CC1]
In some embodiments, L is
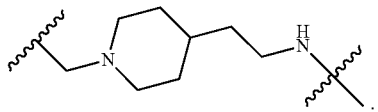 [SMILES: *CN1CCC(CCN*)CC1]
In some embodiments, L is
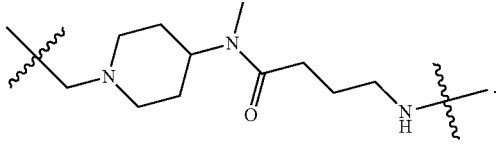 [SMILES: *CN1CCC(N(C)C(=O)CCCN*)CC1]
In some embodiments, L is
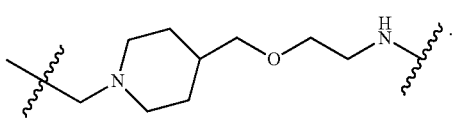 [SMILES: *CN1CCC(COCCN*)CC1]
In some embodiments, L is
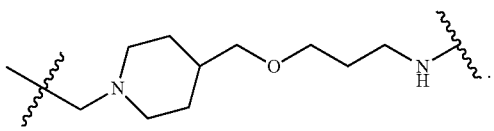 [SMILES: *CN1CCC(COCCCN*)CC1]
In some embodiments, L is
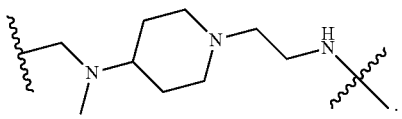
In some embodiments, L is
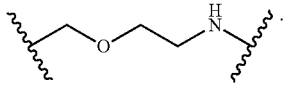
In some embodiments, L is
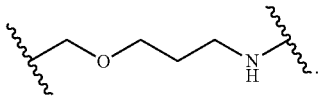 [SMILES: *COCCCN*]

In some embodiments, L is
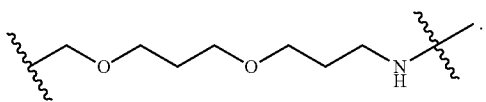 [SMILES: *COCCCOCCCN*]
In some embodiments, L is
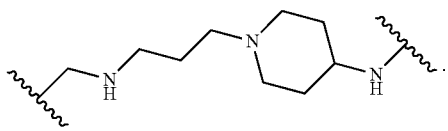 [SMILES: *CNCCCN1CCC(N*)CC1]
In some embodiments, L is
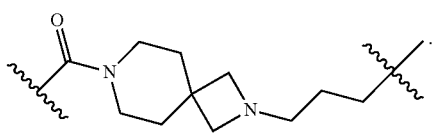 [SMILES: *CCCN1CC2(CCN(C(*)=O)CC2)C1]
In some embodiments, L is
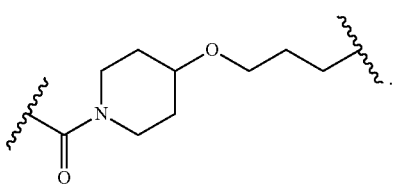 [SMILES: *CCCOC1CCN(C(*)=O)CC1]
In some embodiments, L is
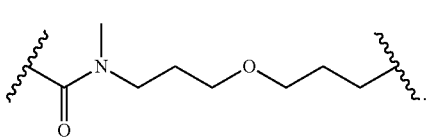 [SMILES: *CCCOCCCN(C)C(*)=O]
In some embodiments, L is
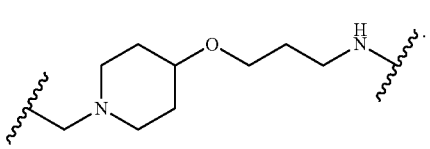 [SMILES: *CN1CCC(OCCCN*)CC1]
In some embodiments, L is
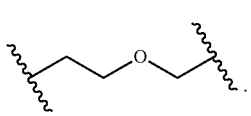 [SMILES: *CCOC*]
In some embodiments, L is
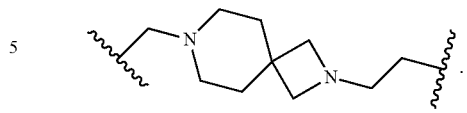
In some embodiments, L is
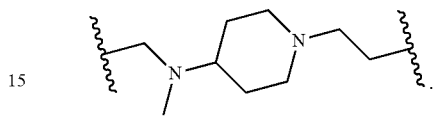
In some embodiments, L is
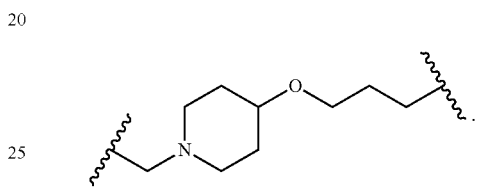
In some embodiments, L is
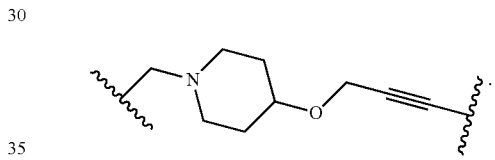
In some embodiments, L is
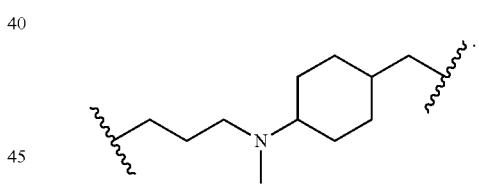
In some embodiments, L is
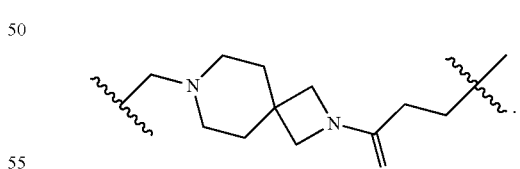
In some embodiments, L is
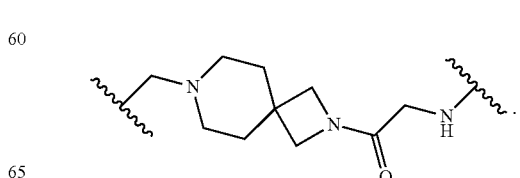

In some embodiments, L is
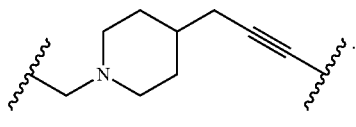 [SMILES: *C#CCC1CCN(C*)CC1]
In some embodiments, L is
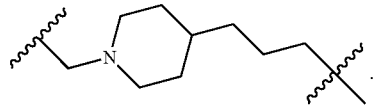 [SMILES: *CCCC1CCN(C*)CC1]
In some embodiments, L is
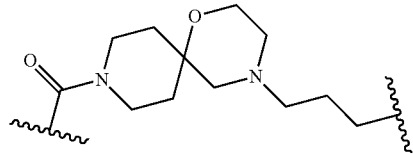
In some embodiments, L is
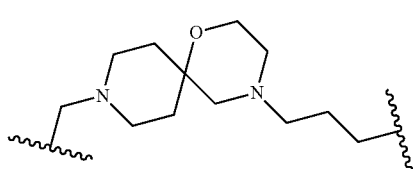
In some embodiments, L is
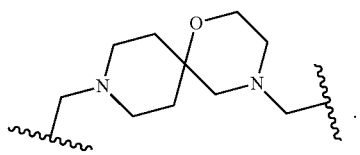 [SMILES: *CN1CCC2(CC1)CN(C*)CCO2]
In some embodiments, L is
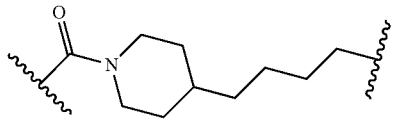
In some embodiments, L is
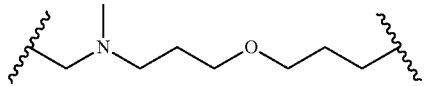
In some embodiments, L is
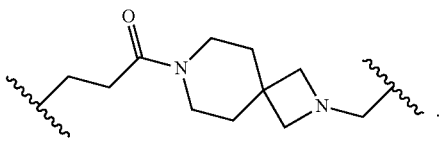 [SMILES: *CCC(=O)N1CCC2(CC1)CN(C*)C2]
In some embodiments, L is
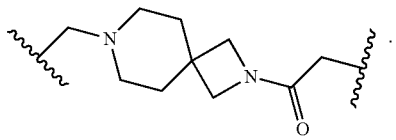 [SMILES: *CC(=O)N1CC2(CCN(C*)CC2)C1]
In some embodiments, L is
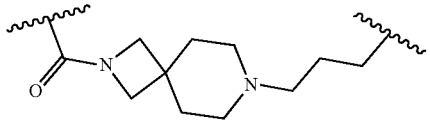
In some embodiments, L is
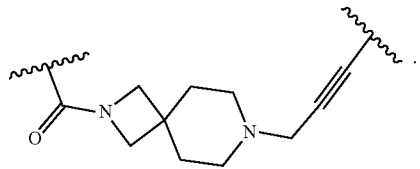 [SMILES: *C#CCN1CCC2(CC1)CN(C(*)=O)C2]
In some embodiments, L is
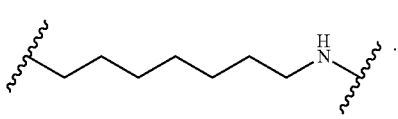
In some embodiments, L is
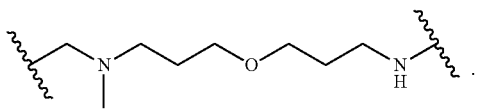
In some embodiments, L is
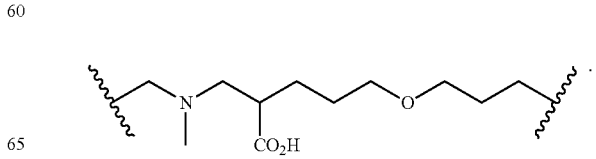

In some embodiments, L is
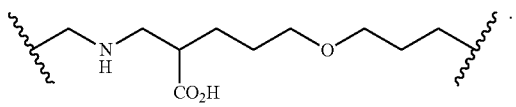
In some embodiments, L is
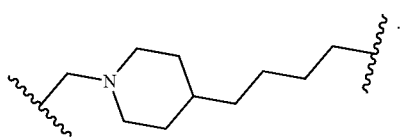 [SMILES: *CCCCC1CCN(C*)CC1]
In some embodiments, L is
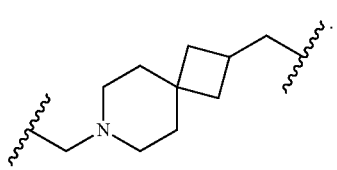 [SMILES: *CC1CC2(CCN(C*)CC2)C1]
In some embodiments, L is
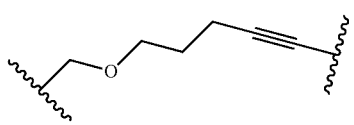
In some embodiments, L is
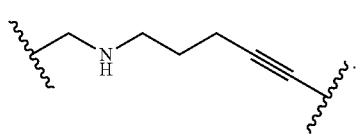 [SMILES: *C#CCCCNC*]
In some embodiments, L is
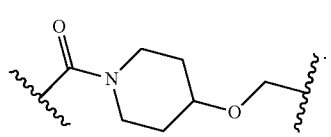 [SMILES: *COC1CCN(C(*)=O)CC1]
In some embodiments, L is
In some embodiments, L is
In some embodiments, L is
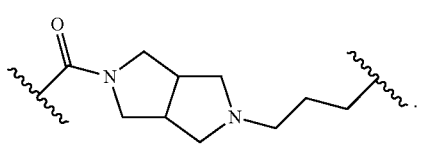 [SMILES: *CCCN1CC2CN(C(*)=O)CC2C1]
In some embodiments, L is
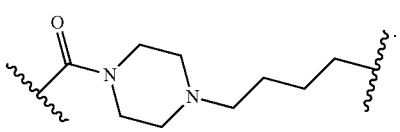
In some embodiments, L is
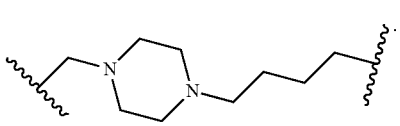 [SMILES: *CCCCN1CCN(C*)CC1]
In some embodiments, L is
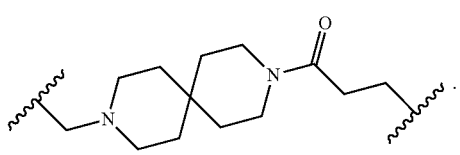 [SMILES: *CCC(=O)N1CCC2(CCN(C*)CC2)CC1]
In some embodiments, L is
In some embodiments, L is
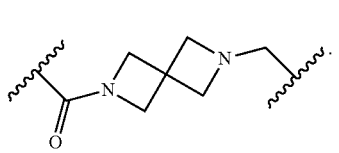 [SMILES: *CN1CC2(C1)CN(C(*)=O)C2]

In some embodiments, L is
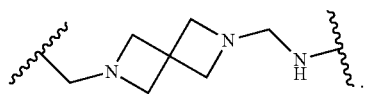 [SMILES: *CN1CC2(C1)CN(CN*)C2]
In some embodiments, L is
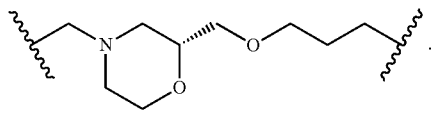 [SMILES: *CCCOC[C@H]1CN(C*)CCO1]
In some embodiments, L is
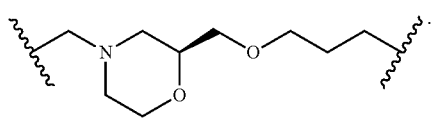 [SMILES: *CCCOC[C@@H]1CN(C*)CCO1]
In some embodiments, L is
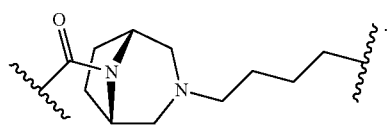 [SMILES: *CCCCN1C[C@H]2CC[C@@H](C1)N2C(*)=O]
In some embodiments, L is
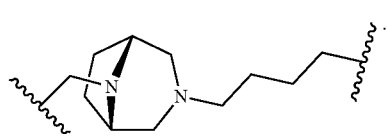 [SMILES: *CCCCN1C[C@H]2CC[C@@H](C1)N2C*]
In some embodiments, L is
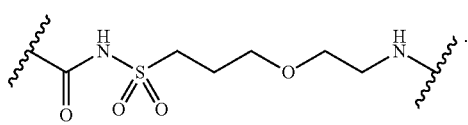 [SMILES: *NCCOCCCS(=O)(=O)NC(*)=O]
In some embodiments, L is
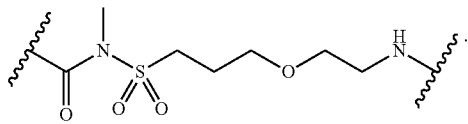 [SMILES: *NCCOCCCS(=O)(=O)N(C)C(*)=O]
In some embodiments, L is
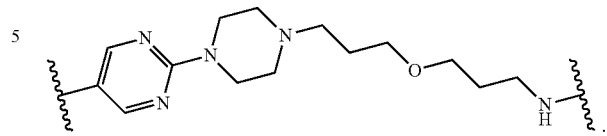
In some embodiments, L is
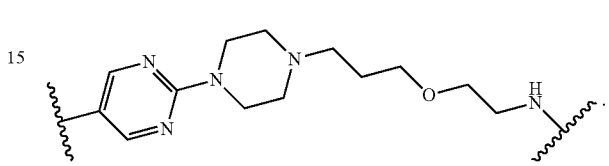
In some embodiments, L is
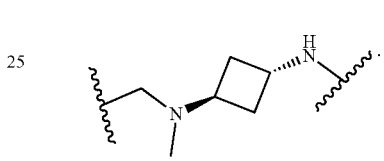
In some embodiments, L is
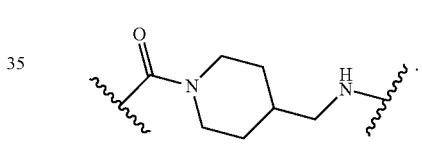
In some embodiments, L is
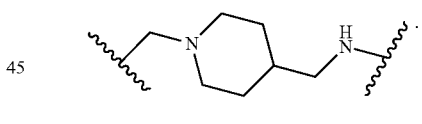
In some embodiments, L is
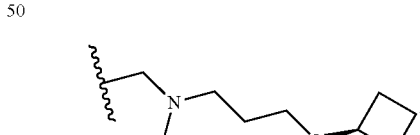
In some embodiments, L is
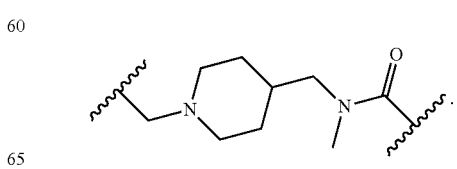

In some embodiments, L is
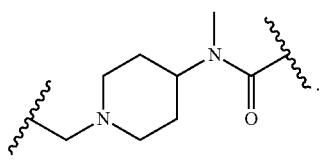 [SMILES: *CN1CCC(N(C)C(*)=O)CC1]
In some embodiments, L is
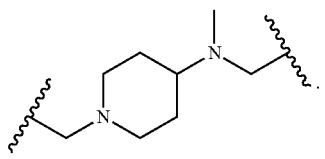 [SMILES: *CN1CCC(N(C)C*)CC1]
In some embodiments, L is
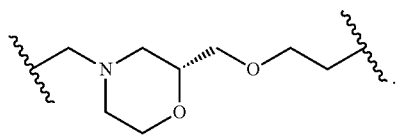 [SMILES: *CCOC[C@H]1CN(C*)CCO1]
In some embodiments, L is
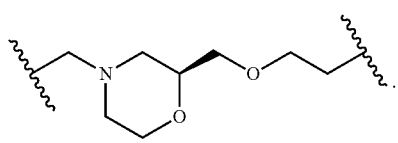 [SMILES: *CCOC[C@@H]1CN(C*)CCO1]
In some embodiments, L is
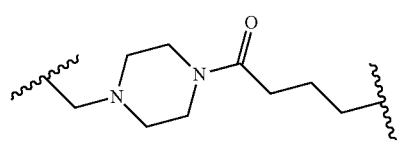
In some embodiments, L is
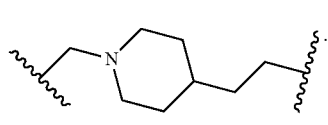 [SMILES: *CCC1CCN(C*)CC1]
In some embodiments, L is
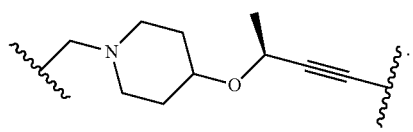 [SMILES: *C#C[C@H](C)OC1CCN(C*)CC1]
In some embodiments, L is
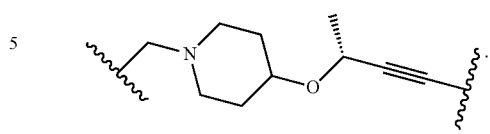
In some embodiments, L is
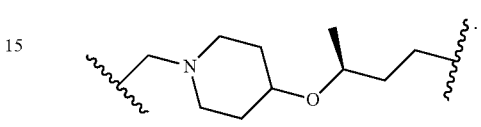
In some embodiments, L is
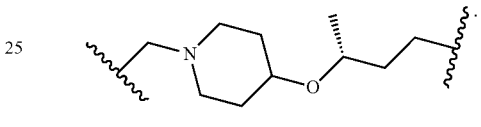
In some embodiments, L is
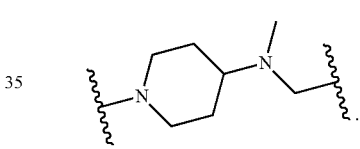
In some embodiments, L is
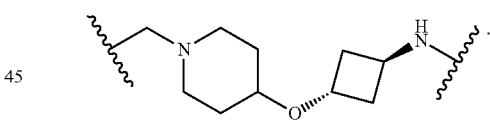
In some embodiments, L is
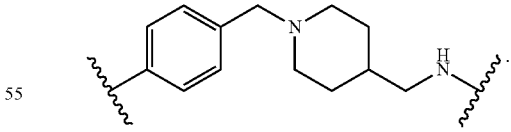
In some embodiments, L is
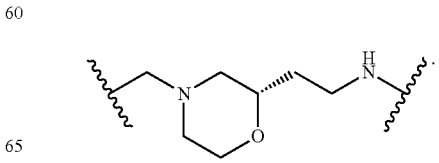

In some embodiments, L is
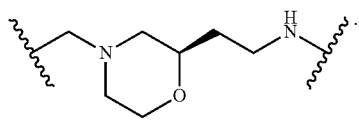 [SMILES: *CN1CCO[C@H](CCN*)C1]
In some embodiments, L is
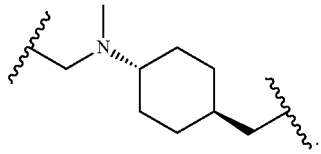 [SMILES: *CN(C)[C@H]1CC[C@H](C*)CC1]
In some embodiments, L is
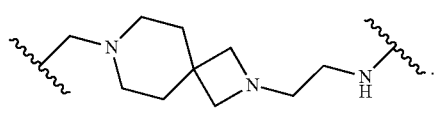 [SMILES: *CN1CCC2(CC1)CN(CCN*)C2]
In some embodiments, L is
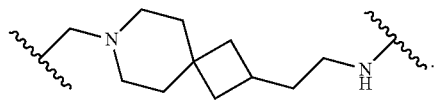 [SMILES: *CN1CCC2(CC1)CC(CCN*)C2]
In some embodiments, L is
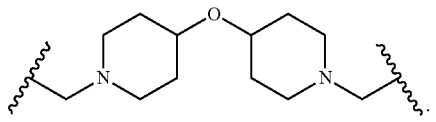 [SMILES: *CN1CCC(OC2CCN(C*)CC2)CC1]
In some embodiments, L is
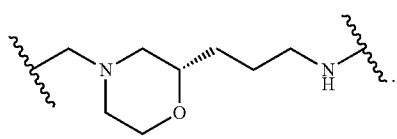 [SMILES: *CN1CCO[C@@H](CCCN*)C1]
In some embodiments, L is
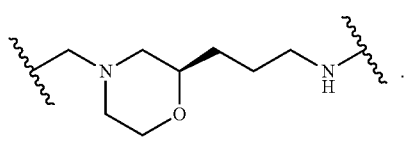
In some embodiments, L is
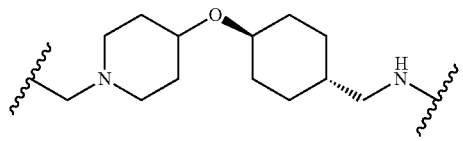
In some embodiments, L is
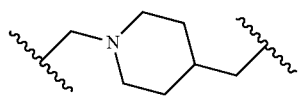
In some embodiments, L is
In some embodiments, L is
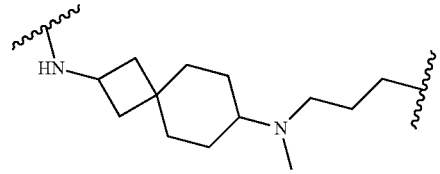
In some embodiments, L is
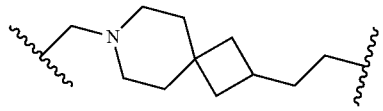
In some embodiments, L is
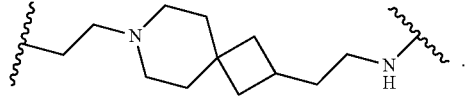
In some embodiments, L is
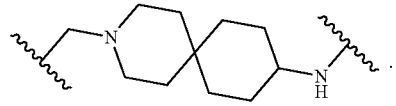

In some embodiments, L is
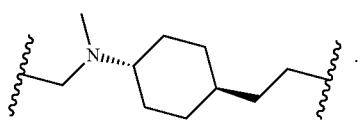 [SMILES: *CC[C@H]1CC[C@H](N(C)C*)CC1]
In some embodiments, L is
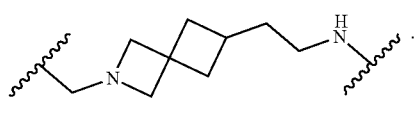
In some embodiments, L is
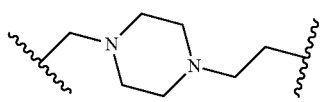
In some embodiments, L is
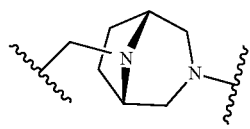
In some embodiments, L is
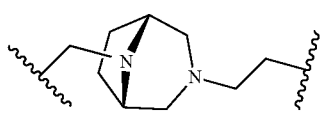
In some embodiments, L is
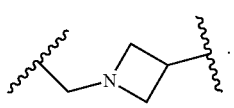 [SMILES: *CN1CC(*)C1]
In some embodiments, L is
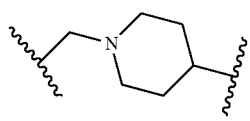
In some embodiments, L is
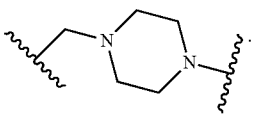 [SMILES: *CN1CCN(*)CC1]
In some embodiments, L is
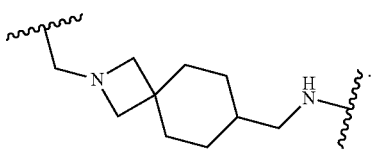 [SMILES: *CN1CC2(CCC(CN*)CC2)C1]
In some embodiments, L is
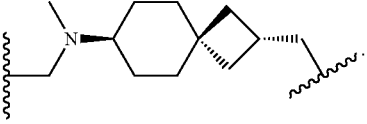
In some embodiments, L is
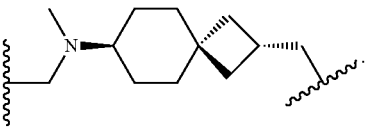
In some embodiments, L is
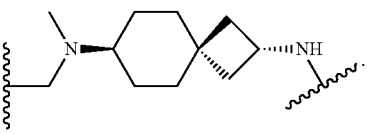
In some embodiments, L is
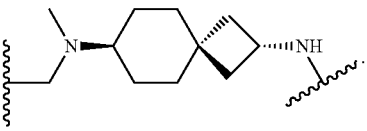
In some embodiments, L is
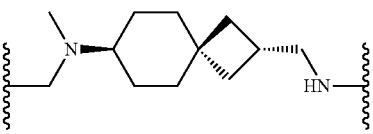

In some embodiments, L is
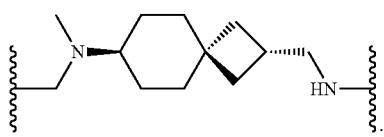
In some embodiments, L is
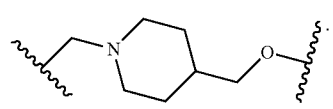 [SMILES: *CN1CCC(CO*)CC1]
In some embodiments, L is
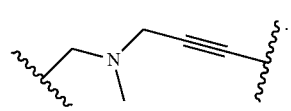
In some embodiments, L is
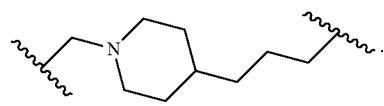 [SMILES: *CCCC1CCN(C*)CC1]
In some embodiments, L is
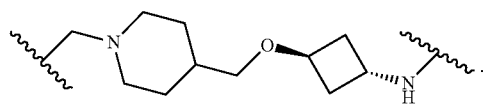 [SMILES: *CN1CCC(CO[C@H]2C[C@H](N*)C2)CC1]
In some embodiments, L is
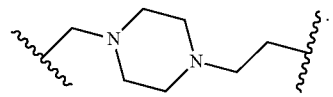 [SMILES: *CCN1CCN(C*)CC1]
In some embodiments, L is
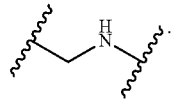 [SMILES: *CN*]
In some embodiments, L is
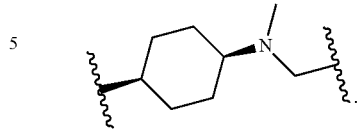
In some embodiments, L is
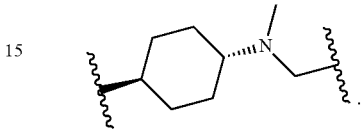
In some embodiments, L is
In some embodiments, L is
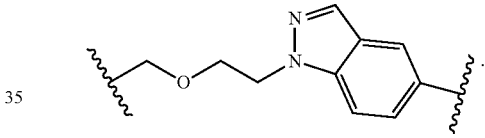
In some embodiments, L is
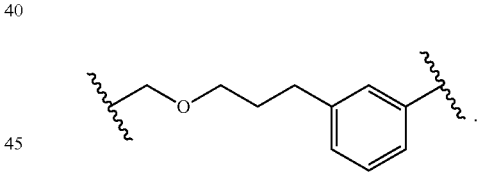
In some embodiments, L is
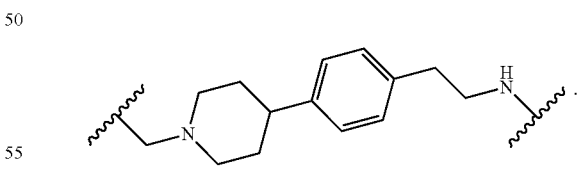
In some embodiments, L is
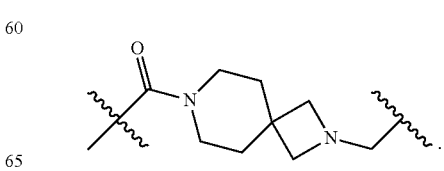

In some embodiments, L is
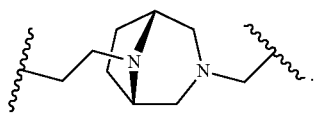 [SMILES: *CCN1[C@@H]2CC[C@H]1CN(C*)C2]
In some embodiments, L is
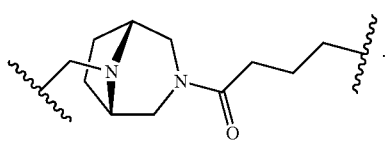 [SMILES: *CCCC(=O)N1C[C@H]2CC[C@@H](C1)N2C*]
In some embodiments, L is
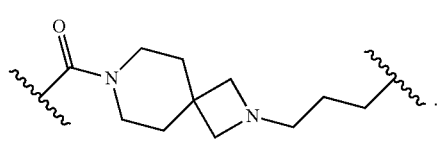 [SMILES: *CCCN1CC2(CCN(C(*)=O)CC2)C1]
In some embodiments, L is
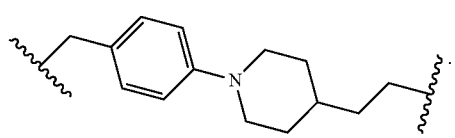 [SMILES: *CCC1CCN(c2ccc(C*)cc2)CC1]
In some embodiments, L is
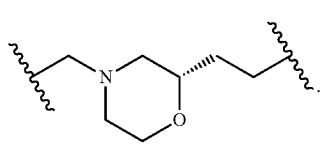 [SMILES: *CC[C@H]1CN(C*)CCO1]
In some embodiments, L is
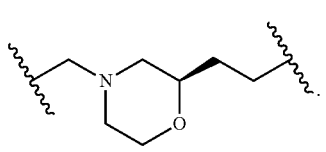 [SMILES: *CC[C@@H]1CN(C*)CCO1]
In some embodiments, L is
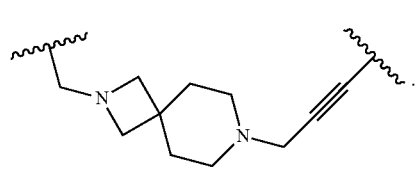 [SMILES: *C#CCN1CCC2(CC1)CN(C*)C2]
In some embodiments, L is
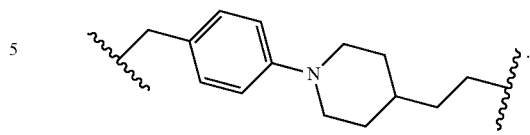
In some embodiments, L is
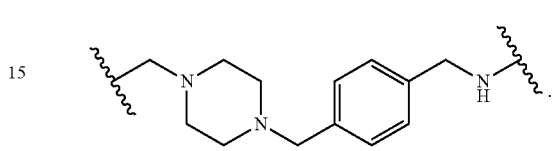
In some embodiments, L is
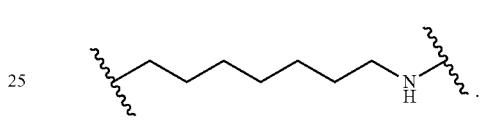
In some embodiments, L is
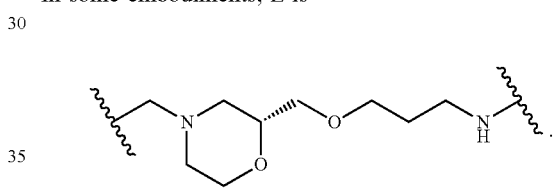
In some embodiments, L is
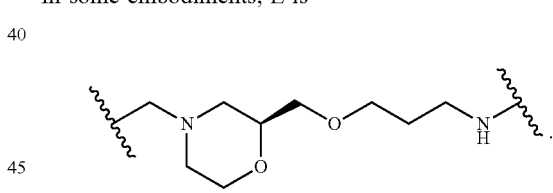
In some embodiments, L is
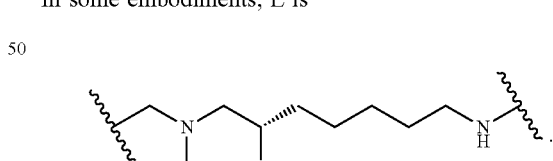
In some embodiments, L is
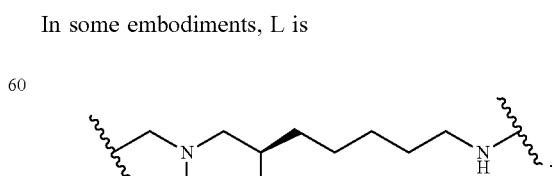

In some embodiments, L is

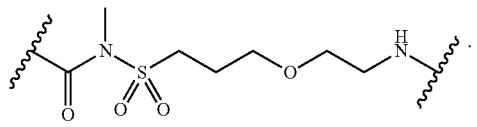 [SMILES: *NCCOCCCS(=O)(=O)N(C)C(*)=O]

In some embodiments, L is

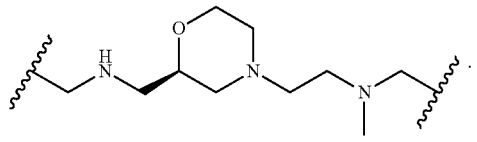 [SMILES: *CNC[C@@H]1CN(CCN(C)C*)CCO1]

In some embodiments, L is

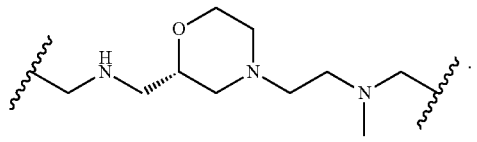 [SMILES: *CNC[C@H]1CN(CCN(C)C*)CCO1]

In some embodiments, L is

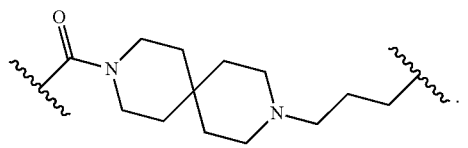 [SMILES: *CCCN1CCC2(CC1)CCN(C(*)=O)CC2]

In some embodiments, L is

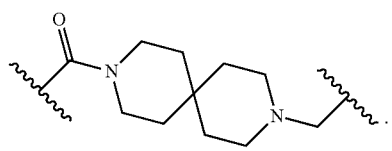 [SMILES: *CN1CCC2(CC1)CCN(C(*)=O)CC2]

In some embodiments, L is

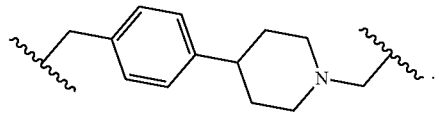 [SMILES: *Cc1ccc(C2CCN(C*)CC2)cc1]

In some embodiments, L is

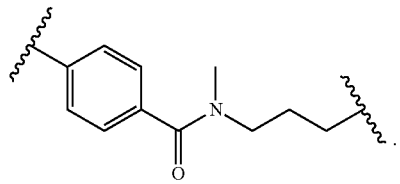 [SMILES: *CCCN(C)C(=O)c1ccc(*)cc1]

In some embodiments, L is

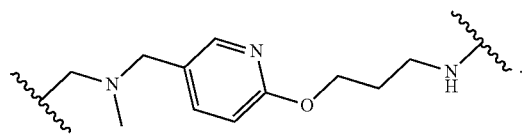 [SMILES: *CN(C)Cc1ccc(OCCCN*)nc1]

In some embodiments, L is

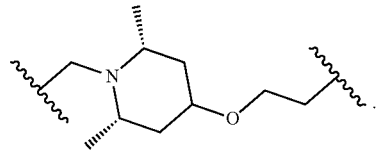 [SMILES: *CCOC1C[C@@H](C)N(C*)[C@@H](C)C1]

In some embodiments, L is

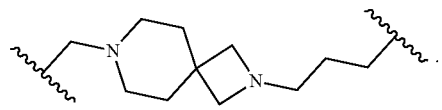 [SMILES: *CCCN1CC2(CCN(C*)CC2)C1]

In some embodiments, L is

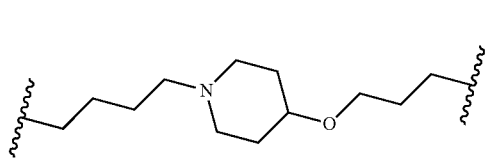

In some embodiments, L is

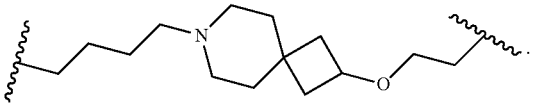 [SMILES: *CCCCN1CCC2(CC1)CC(OCC*)C2]

In some embodiments, L is selected from those depicted in Table 1, below.

In some embodiments, a provided compound or pharmaceutically acceptable salt thereof, is selected from those wherein IRAK is

521

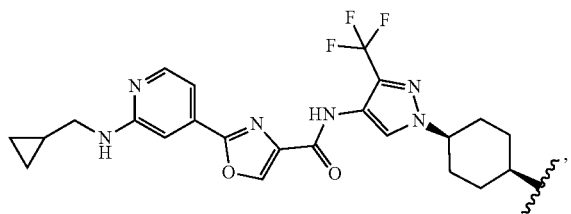 [SMILES: *[C@H]1CC[C@@H](n2cc(NC(=O)c3coc(-c4ccnc(NCC5CC5)c4)n3)c(C(F)(F)F)n2)CC1]

LBM is selected from any of those in Table A below, and L is selected from any of those in Table B below.

In some embodiments, a provided compound or pharmaceutically acceptable salt thereof, is selected from those wherein IRAK is

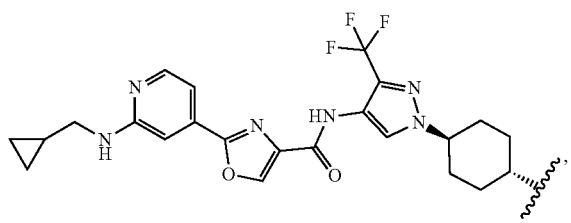 [SMILES: *[C@H]1CC[C@H](n2cc(NC(=O)c3coc(-c4ccnc(NCC5CC5)c4)n3)c(C(F)(F)F)n2)CC1]

LBM is selected from any of those in Table A below, and L is selected from any of those in Table B below.

In some embodiments, a provided compound or pharmaceutically acceptable salt thereof, is selected from those wherein IRAK is

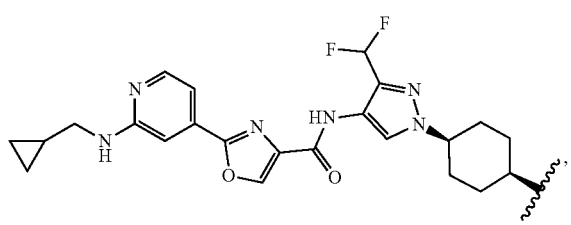 [SMILES: *[C@H]1CC[C@@H](n2cc(NC(=O)c3coc(-c4ccnc(NCC5CC5)c4)n3)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

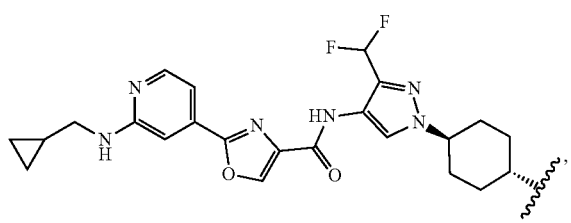 [SMILES: *[C@H]1CC[C@H](n2cc(NC(=O)c3coc(-c4ccnc(NCC5CC5)c4)n3)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

522

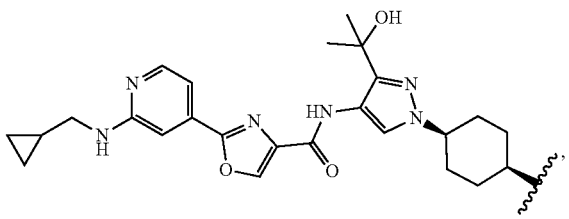 [SMILES: *[C@H]1CC[C@@H](n2cc(NC(=O)c3coc(-c4ccnc(NCC5CC5)c4)n3)c(C(C)(C)O)n2)CC1]

LBM is selected from any of those in Table A below, and L is selected from any of those in Table B below.

In some embodiments, a provided compound or pharmaceutically acceptable salt thereof, is selected from those wherein IRAK is

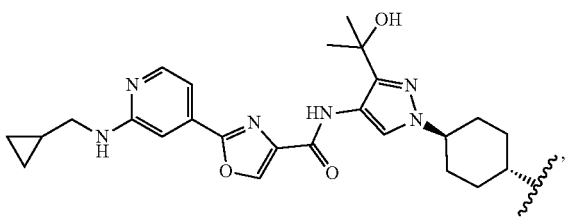 [SMILES: *[C@H]1CC[C@H](n2cc(NC(=O)c3coc(-c4ccnc(NCC5CC5)c4)n3)c(C(C)(C)O)n2)CC1]

LBM is selected from any of those in Table A below, and L is selected from any of those in Table B below.

In some embodiments, a provided compound or pharmaceutically acceptable salt thereof, is selected from those wherein IRAK is

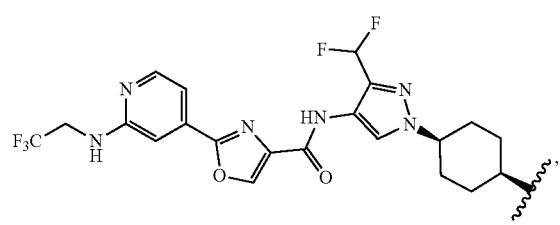 [SMILES: *[C@H]1CC[C@@H](n2cc(NC(=O)c3coc(-c4ccnc(NCC(F)(F)F)c4)n3)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

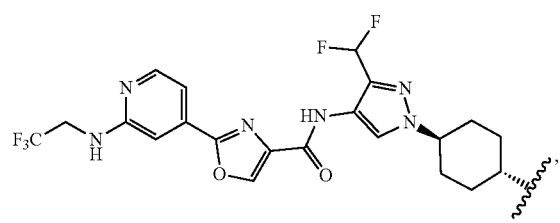 [SMILES: *[C@H]1CC[C@H](n2cc(NC(=O)c3coc(-c4ccnc(NCC(F)(F)F)c4)n3)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

523

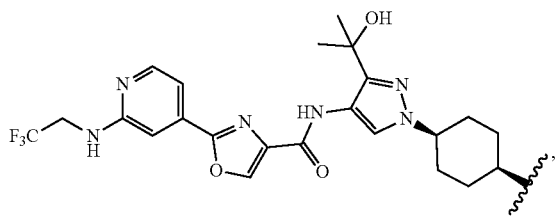 [SMILES: *[C@H]1CC[C@@H](n2cc(NC(=O)c3coc(-c4ccnc(NCC(F)(F)F)c4)n3)c(C(C)(C)O)n2)CC1]

LBM is selected from any of those in Table A below, and L is selected from any of those in Table B below.

In some embodiments, a provided compound or pharmaceutically acceptable salt thereof, is selected from those wherein IRAK is

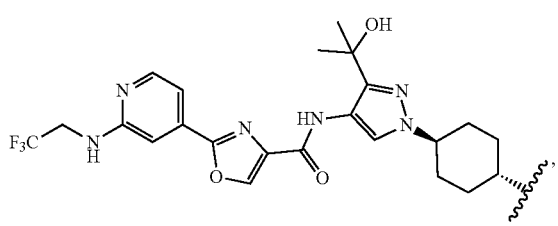 [SMILES: *[C@H]1CC[C@H](n2cc(NC(=O)c3coc(-c4ccnc(NCC(F)(F)F)c4)n3)c(C(C)(C)O)n2)CC1]

LBM is selected from any of those in Table A below, and L is selected from any of those in Table B below.

In some embodiments, a provided compound or pharmaceutically acceptable salt thereof, is selected from those wherein IRAK is

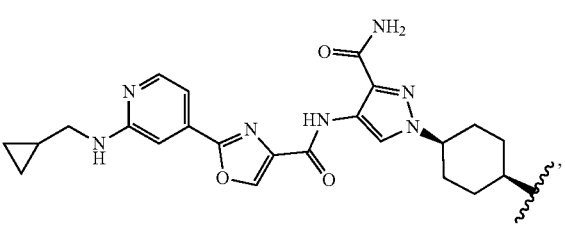 [SMILES: *[C@H]1CC[C@@H](n2cc(NC(=O)c3coc(-c4ccnc(NCC5CC5)c4)n3)c(C(N)=O)n2)CC1]

LBM is selected from any of those in Table A below, and L is selected from any of those in Table B below.

In some embodiments, a provided compound or pharmaceutically acceptable salt thereof, is selected from those wherein IRAK is

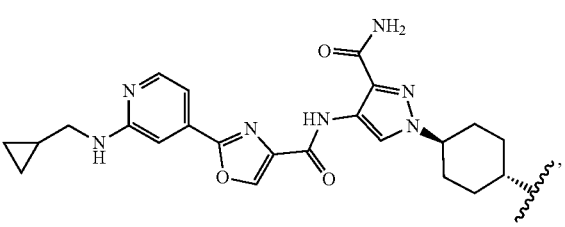 [SMILES: *[C@H]1CC[C@H](n2cc(NC(=O)c3coc(-c4ccnc(NCC5CC5)c4)n3)c(C(N)=O)n2)CC1]

LBM is selected from any of those in Table A below, and L is selected from any of those in Table B below.

In some embodiments, a provided compound or pharmaceutically acceptable salt thereof, is selected from those wherein IRAK is

524

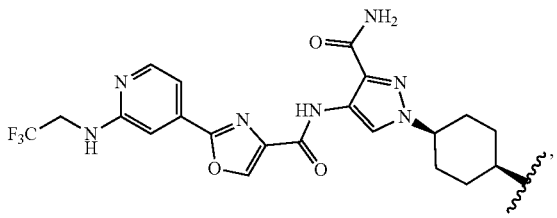 [SMILES: *[C@H]1CC[C@@H](n2cc(NC(=O)c3coc(-c4ccnc(NCC(F)(F)F)c4)n3)c(C(N)=O)n2)CC1]

LBM is selected from any of those in Table A below, and L is selected from any of those in Table B below.

In some embodiments, a provided compound or pharmaceutically acceptable salt thereof, is selected from those wherein IRAK is

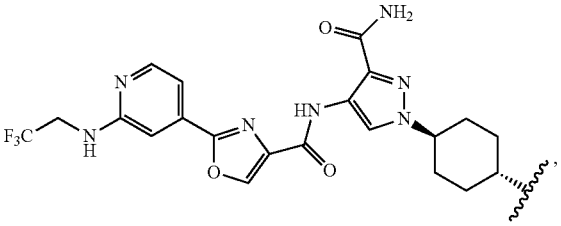 [SMILES: *[C@H]1CC[C@H](n2cc(NC(=O)c3coc(-c4ccnc(NCC(F)(F)F)c4)n3)c(C(N)=O)n2)CC1]

LBM is selected from any of those in Table A below, and L is selected from any of those in Table B below.

In some embodiments, a provided compound or pharmaceutically acceptable salt thereof, is selected from those wherein IRAK is

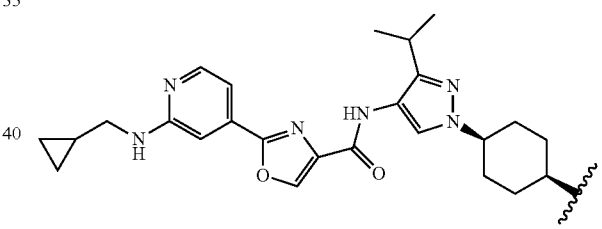

LBM is selected from any of those in Table A below, and L is selected from any of those in Table B below.

In some embodiments, a provided compound or pharmaceutically acceptable salt thereof, is selected from those wherein IRAK is

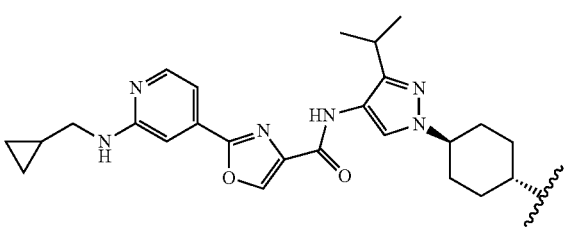

LBM is selected from any of those in Table A below, and L is selected from any of those in Table B below.

In some embodiments, a provided compound or pharmaceutically acceptable salt thereof, is selected from those wherein IRAK is

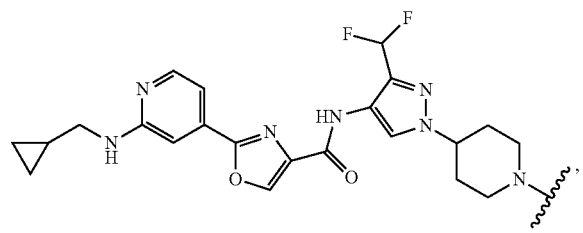 [SMILES: *N1CCC(n2cc(NC(=O)c3coc(-c4ccnc(NCC5CC5)c4)n3)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

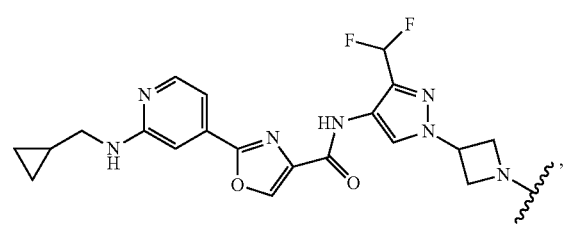 [SMILES: *N1CC(n2cc(NC(=O)c3coc(-c4ccnc(NCC5CC5)c4)n3)c(C(F)F)n2)C1]

LBM is selected from any of those in Table A below, and L is selected from any of those in Table B below.

In some embodiments, a provided compound or pharmaceutically acceptable salt thereof, is selected from those wherein IRAK is

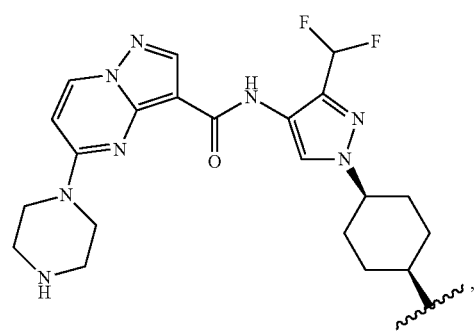 [SMILES: *[C@H]1CC[C@@H](n2cc(NC(=O)c3cnn4ccc(N5CCNCC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

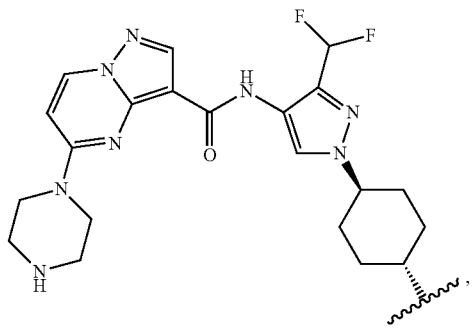 [SMILES: *[C@H]1CC[C@H](n2cc(NC(=O)c3cnn4ccc(N5CCNCC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

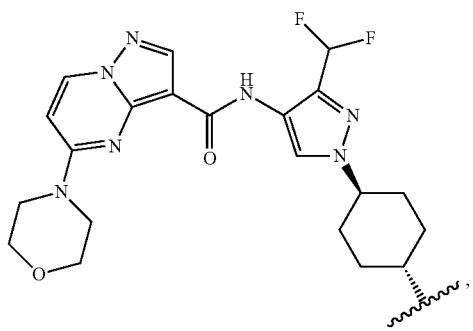 [SMILES: *[C@H]1CC[C@H](n2cc(NC(=O)c3cnn4ccc(N5CCOCC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

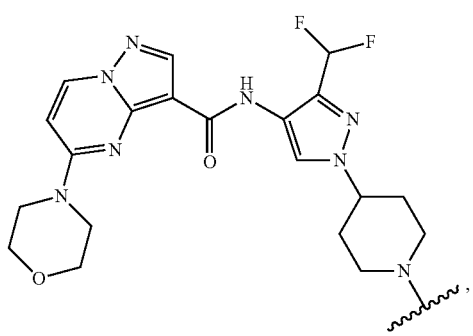 [SMILES: *N1CCC(n2cc(NC(=O)c3cnn4ccc(N5CCOCC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

527

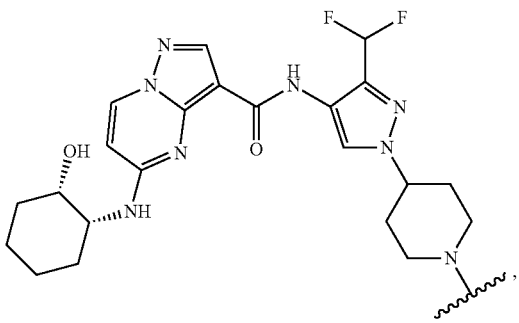 [SMILES: *N1CCC(n2cc(NC(=O)c3cnn4ccc(N[C@@H]5CCCC[C@@H]5O)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

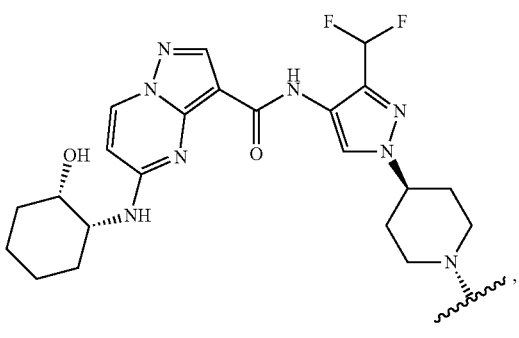

LBM is selected from any of those in Table A below, and L is selected from any of those in Table B below.

In some embodiments, a provided compound or pharmaceutically acceptable salt thereof, is selected from those wherein IRAK is

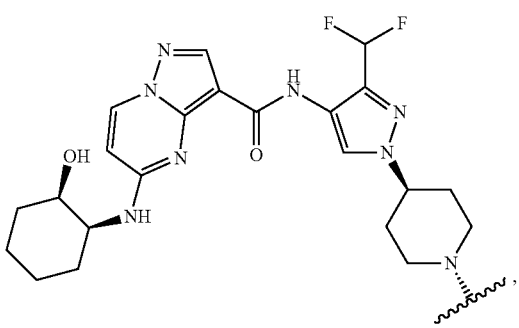

LBM is selected from any of those in Table A below, and L is selected from any of those in Table B below.

In some embodiments, a provided compound or pharmaceutically acceptable salt thereof, is selected from those wherein IRAK is

528

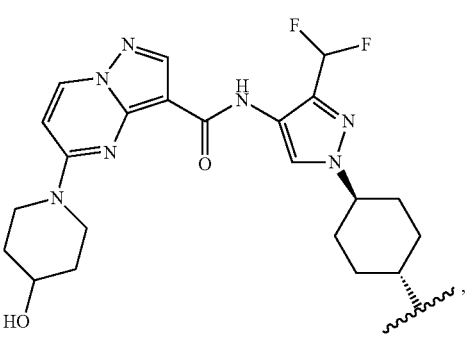 [SMILES: *[C@H]1CC[C@H](n2cc(NC(=O)c3cnn4ccc(N5CCC(O)CC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

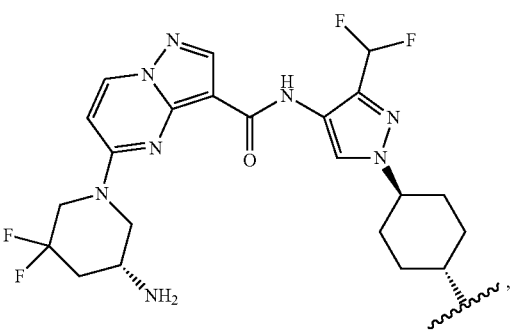 [SMILES: *[C@H]1CC[C@H](n2cc(NC(=O)c3cnn4ccc(N5C[C@H](N)CC(F)(F)C5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

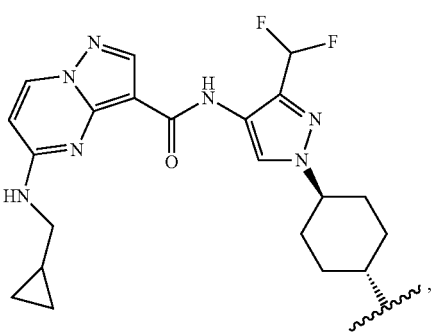 [SMILES: *[C@H]1CC[C@H](n2cc(NC(=O)c3cnn4ccc(NCC5CC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

529

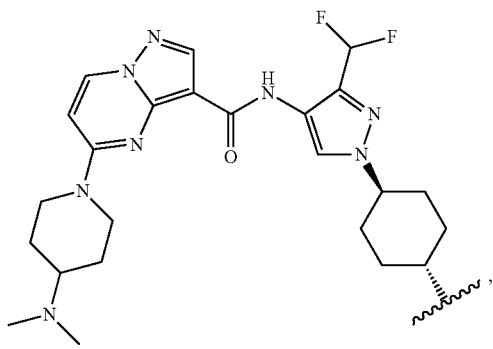 [SMILES: *[C@H]1CC[C@H](n2cc(NC(=O)c3cnn4ccc(N5CCC(N(C)C)CC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

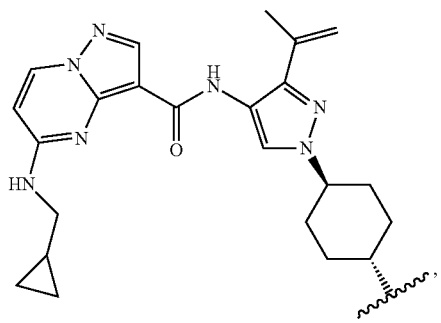 [SMILES: *[C@H]1CC[C@H](n2cc(NC(=O)c3cnn4ccc(NCC5CC5)nc34)c(C(=C)C)n2)CC1]

LBM is selected from any of those in Table A below, and L is selected from any of those in Table B below.

In some embodiments, a provided compound or pharmaceutically acceptable salt thereof, is selected from those wherein IRAK is

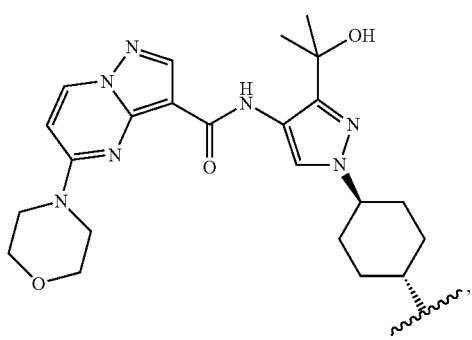 [SMILES: *[C@H]1CC[C@H](n2cc(NC(=O)c3cnn4ccc(N5CCOCC5)nc34)c(C(C)(C)O)n2)CC1]

LBM is selected from any of those in Table A below, and L is selected from any of those in Table B below.

In some embodiments, a provided compound or pharmaceutically acceptable salt thereof, is selected from those wherein IRAK is

530

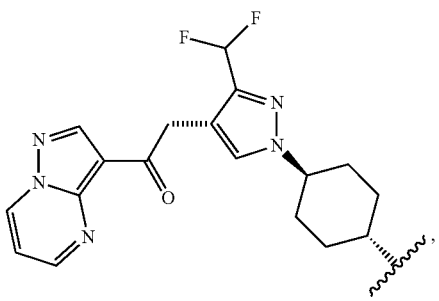

LBM is selected from any of those in Table A below, and L is selected from any of those in Table B below.

In some embodiments, a provided compound or pharmaceutically acceptable salt thereof, is selected from those wherein IRAK is

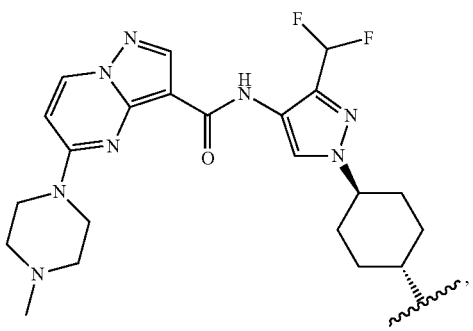 [SMILES: *[C@H]1CC[C@H](n2cc(NC(=O)c3cnn4ccc(N5CCN(C)CC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

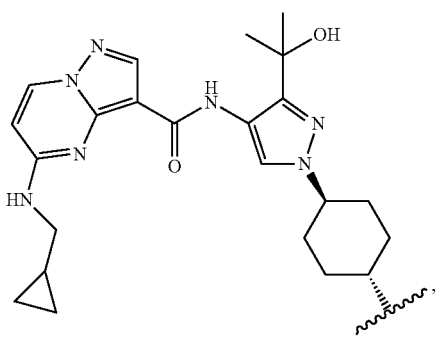 [SMILES: *[C@H]1CC[C@H](n2cc(NC(=O)c3cnn4ccc(NCC5CC5)nc34)c(C(C)(C)O)n2)CC1]

LBM is selected from any of those in Table A below, and L is selected from any of those in Table B below.

In some embodiments, a provided compound or pharmaceutically acceptable salt thereof, is selected from those wherein IRAK is

531

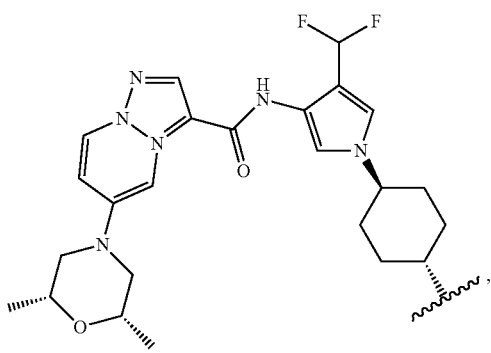

LBM is selected from any of those in Table A below, and L is selected from any of those in Table B below.

In some embodiments, a provided compound or pharmaceutically acceptable salt thereof, is selected from those wherein IRAK is

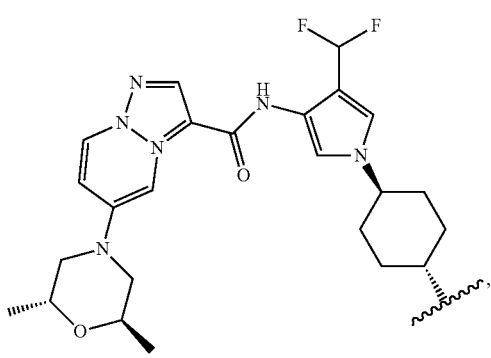

LBM is selected from any of those in Table A below, and L is selected from any of those in Table B below.

In some embodiments, a provided compound or pharmaceutically acceptable salt thereof, is selected from those wherein IRAK is

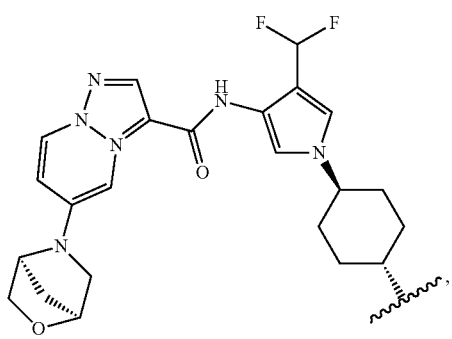

LBM is selected from any of those in Table A below, and L is selected from any of those in Table B below.

In some embodiments, a provided compound or pharmaceutically acceptable salt thereof, is selected from those wherein IRAK is

532

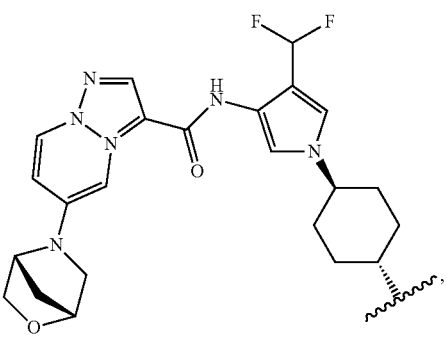

LBM is selected from any of those in Table A below, and L is selected from any of those in Table B below.

In some embodiments, a provided compound or pharmaceutically acceptable salt thereof, is selected from those wherein IRAK is

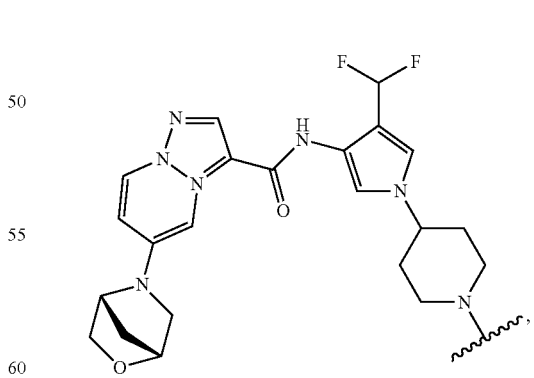

LBM is selected from any of those in Table A below, and L is selected from any of those in Table B below.

In some embodiments, a provided compound or pharmaceutically acceptable salt thereof, is selected from those wherein IRAK is LBM is selected from any of those in Table A below, and L is selected from any of those in Table B below.

In some embodiments, a provided compound or pharmaceutically acceptable salt thereof, is selected from those wherein IRAK is

533

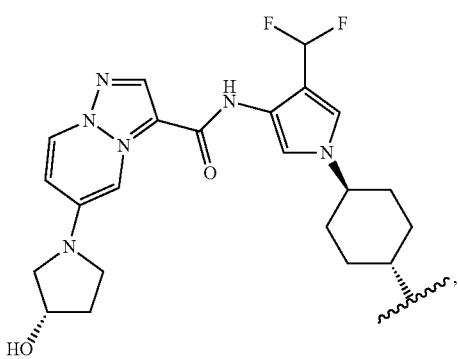

LBM is selected from any of those in Table A below, and L is selected from any of those in Table B below.

In some embodiments, a provided compound or pharmaceutically acceptable salt thereof, is selected from those wherein IRAK is

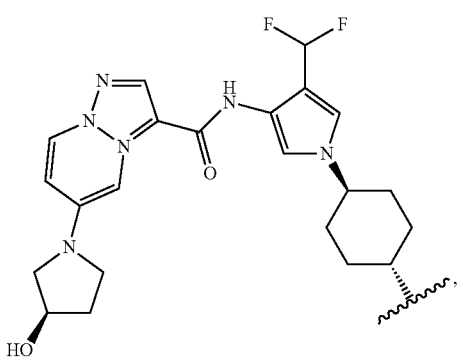

LBM is selected from any of those in Table A below, and L is selected from any of those in Table B below.

In some embodiments, a provided compound or pharmaceutically acceptable salt thereof, is selected from those wherein IRAK is

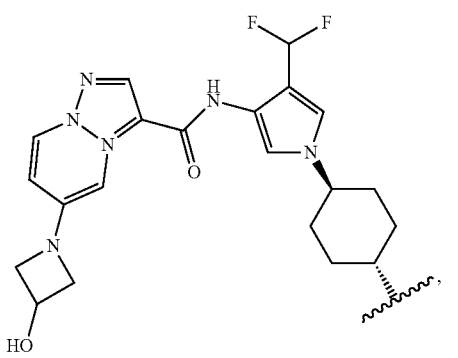

LBM is selected from any of those in Table A below, and L is selected from any of those in Table B below.

In some embodiments, a provided compound or pharmaceutically acceptable salt thereof, is selected from those wherein IRAK is

534

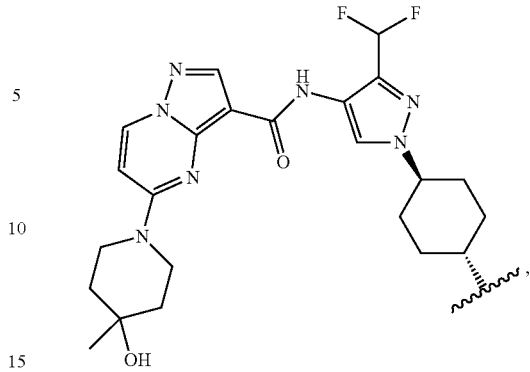

LBM is selected from any of those in Table A below, and L is selected from any of those in Table B below.

In some embodiments, a provided compound or pharmaceutically acceptable salt thereof, is selected from those wherein IRAK is

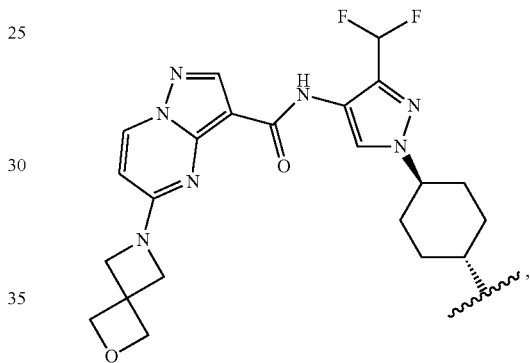

LBM is selected from any of those in Table A below, and L is selected from any of those in Table B below.

In some embodiments, a provided compound or pharmaceutically acceptable salt thereof, is selected from those wherein IRAK is

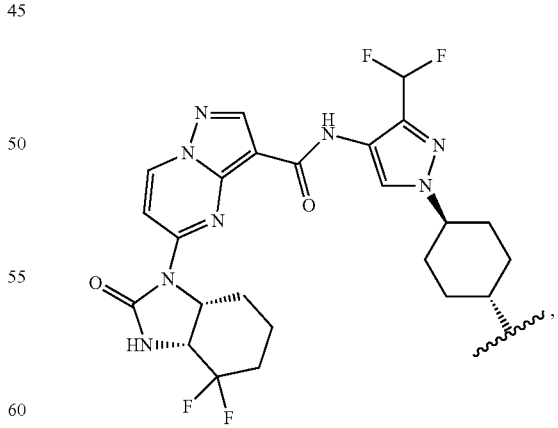

LBM is selected from any of those in Table A below, and L is selected from any of those in Table B below.

In some embodiments, a provided compound or pharmaceutically acceptable salt thereof, is selected from those wherein IRAK is

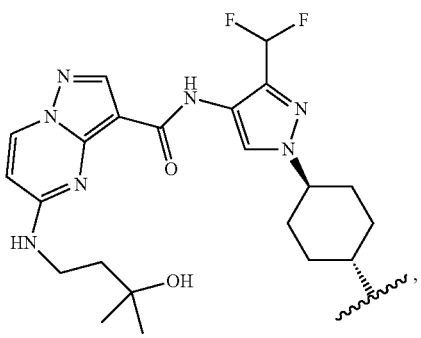 [SMILES: *[C@H]1CC[C@H](n2cc(NC(=O)c3cnn4ccc(NCCC(C)(C)O)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

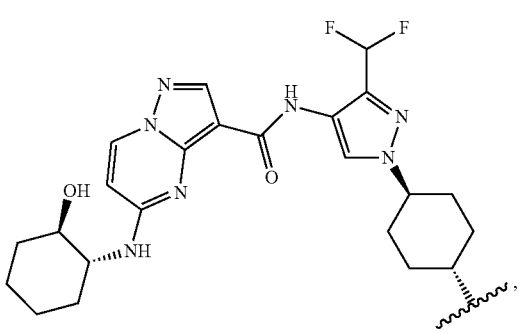 [SMILES: *[C@H]1CC[C@H](n2cc(NC(=O)c3cnn4ccc(N[C@@H]5CCCC[C@H]5O)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

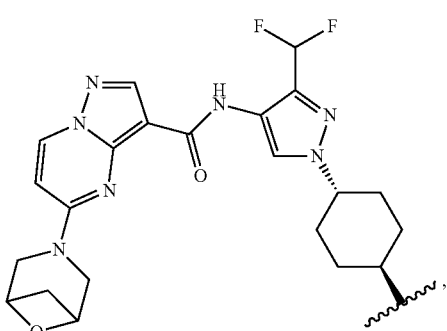

LBM is selected from any of those in Table A below, and L is selected from any of those in Table B below.

In some embodiments, a provided compound or pharmaceutically acceptable salt thereof, is selected from those wherein IRAK is

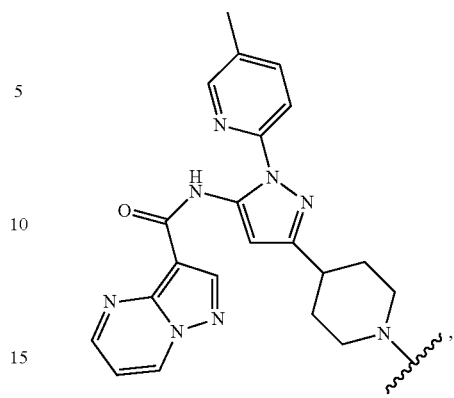

LBM is selected from any of those in Table A below, and L is selected from any of those in Table B below.

In some embodiments, a provided compound or pharmaceutically acceptable salt thereof, is selected from those wherein IRAK is

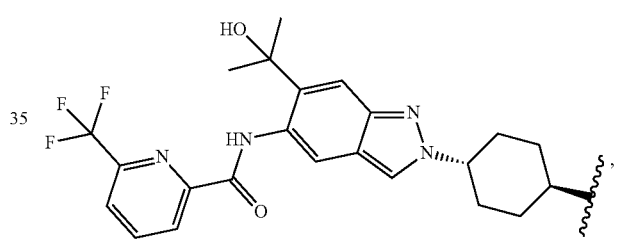

LBM is selected from any of those in Table A below, and L is selected from any of those in Table B below.

In some embodiments, a provided compound or pharmaceutically acceptable salt thereof, is selected from those wherein IRAK is

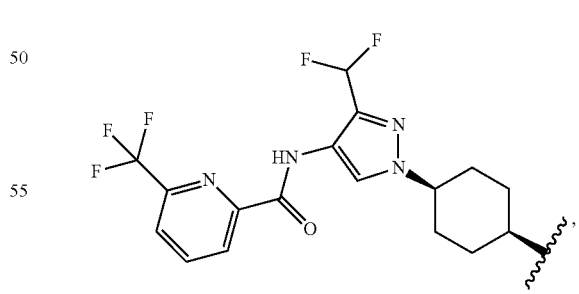

LBM is selected from any of those in Table A below, and L is selected from any of those in Table B below.

In some embodiments, a provided compound or pharmaceutically acceptable salt thereof, is selected from those wherein IRAK is

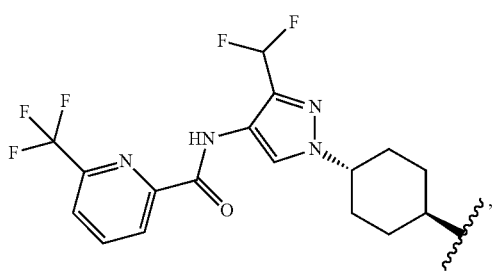 [SMILES: *[C@H]1CC[C@H](n2cc(NC(=O)c3cccc(C(F)(F)F)n3)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is


LBM is selected from any of those in Table A below, and L is selected from any of those in Table B below.

In some embodiments, a provided compound or pharmaceutically acceptable salt thereof, is selected from those wherein IRAK is


LBM is selected from any of those in Table A below, and L is selected from any of those in Table B below.

In some embodiments, a provided compound or pharmaceutically acceptable salt thereof, is selected from those wherein IRAK is

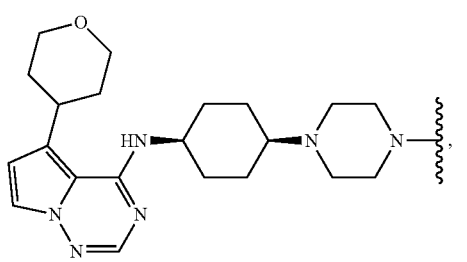 [SMILES: *N1CCN([C@H]2CC[C@@H](Nc3ncnn4ccc(C5CCOCC5)c34)CC2)CC1]

LBM is selected from any of those in Table A below, and L is selected from any of those in Table B below.

In some embodiments, a provided compound or pharmaceutically acceptable salt thereof, is selected from those wherein IRAK is

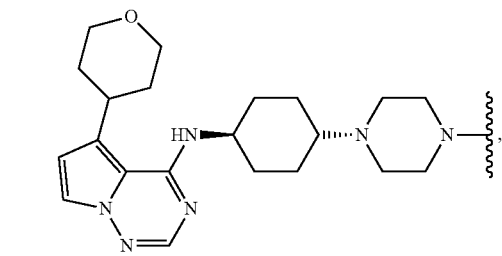

LBM is selected from any of those in Table A below, and L is selected from any of those in Table B below.

In some embodiments, a provided compound or pharmaceutically acceptable salt thereof, is selected from those wherein IRAK is

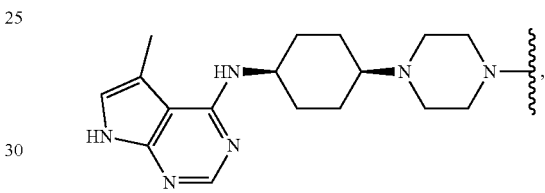

LBM is selected from any of those in Table A below, and L is selected from any of those in Table B below.

In some embodiments, a provided compound or pharmaceutically acceptable salt thereof, is selected from those wherein IRAK is

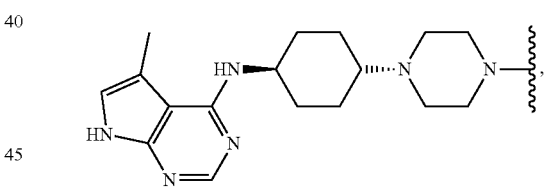

LBM is selected from any of those in Table A below, and L is selected from any of those in Table B below.

In some embodiments, a provided compound or pharmaceutically acceptable salt thereof, is selected from those wherein IRAK is

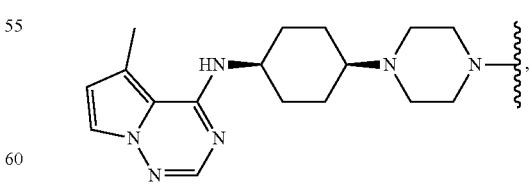

LBM is selected from any of those in Table A below, and L is selected from any of those in Table B below.

In some embodiments, a provided compound or pharmaceutically acceptable salt thereof, is selected from those wherein IRAK is

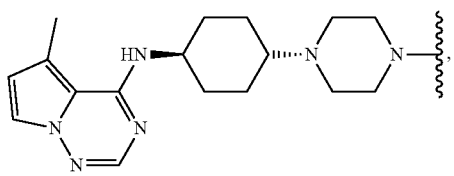

LBM is selected from any of those in Table A below, and L is selected from any of those in Table B below.

In some embodiments, a provided compound or pharmaceutically acceptable salt thereof, is selected from those wherein IRAK is

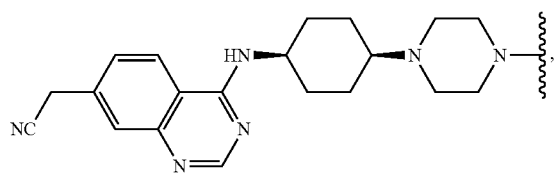 [SMILES: *N1CCN([C@H]2CC[C@@H](Nc3ncnc4cc(CC#N)ccc34)CC2)CC1]

LBM is selected from any of those in Table A below, and L is selected from any of those in Table B below.

In some embodiments, a provided compound or pharmaceutically acceptable salt thereof, is selected from those wherein IRAK is

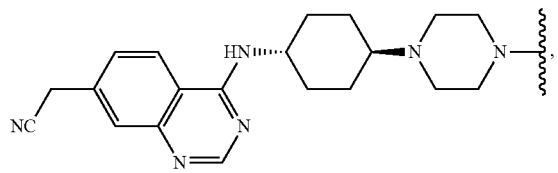 [SMILES: *N1CCN([C@H]2CC[C@H](Nc3ncnc4cc(CC#N)ccc34)CC2)CC1]

LBM is selected from any of those in Table A below, and L is selected from any of those in Table B below.

In some embodiments, a provided compound or pharmaceutically acceptable salt thereof, is selected from those wherein IRAK is

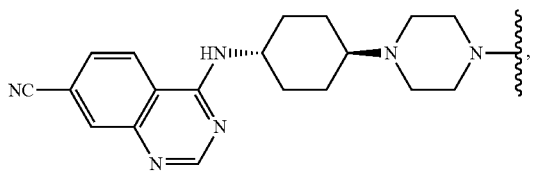 [SMILES: *N1CCN([C@H]2CC[C@H](Nc3ncnc4cc(C#N)ccc34)CC2)CC1]

LBM is selected from any of those in Table A below, and L is selected from any of those in Table B below.

In some embodiments, a provided compound or pharmaceutically acceptable salt thereof, is selected from those wherein IRAK is

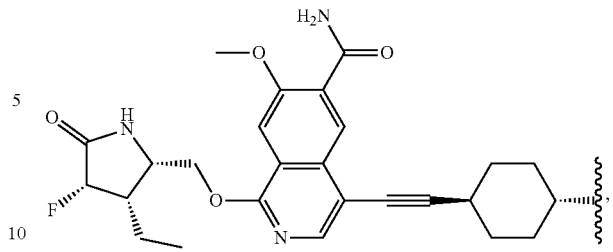

LBM is selected from any of those in Table A below, and L is selected from any of those in Table B below.

In some embodiments, a provided compound or pharmaceutically acceptable salt thereof, is selected from those wherein IRAK is

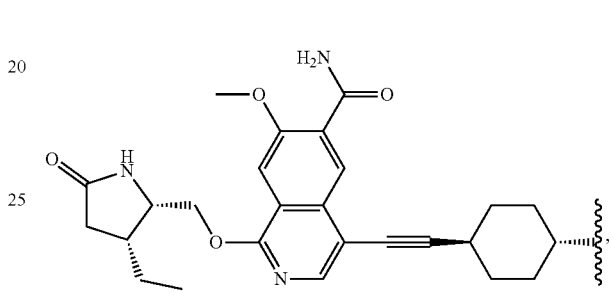

LBM is selected from any of those in Table A below, and L is selected from any of those in Table B below.

In some embodiments, a provided compound or pharmaceutically acceptable salt thereof, is selected from those wherein IRAK is

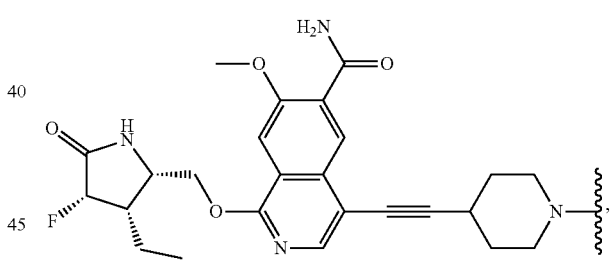

LBM is selected from any of those in Table A below, and L is selected from any of those in Table B below.

In some embodiments, a provided compound or pharmaceutically acceptable salt thereof, is selected from those wherein IRAK is

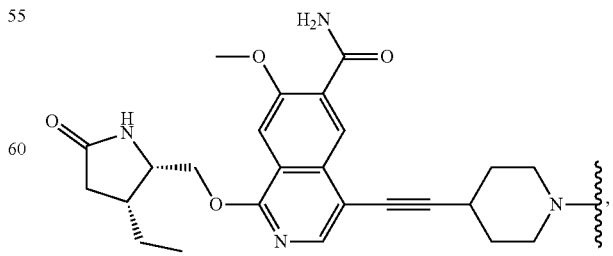

LBM is selected from any of those in Table A below, and L is selected from any of those in Table B below.

In some embodiments, a provided compound or pharmaceutically acceptable salt thereof, is selected from those wherein IRAK is

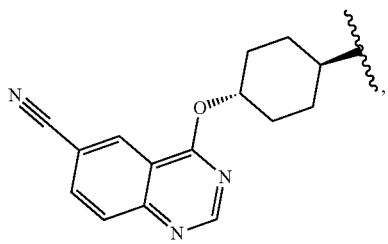 [SMILES: *[C@H]1CC[C@H](Oc2ncnc3ccc(C#N)cc23)CC1]

LBM is selected from any of those in Table A below, and L is selected from any of those in Table B below.

In some embodiments, a provided compound or pharmaceutically acceptable salt thereof, is selected from those wherein IRAK is

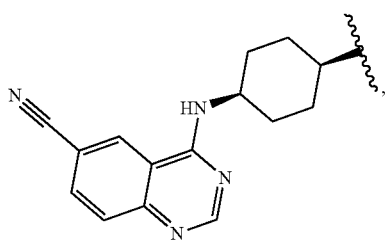 [SMILES: *[C@H]1CC[C@@H](Nc2ncnc3ccc(C#N)cc23)CC1]

LBM is selected from any of those in Table A below, and L is selected from any of those in Table B below.

In some embodiments, a provided compound or pharmaceutically acceptable salt thereof, is selected from those wherein IRAK is

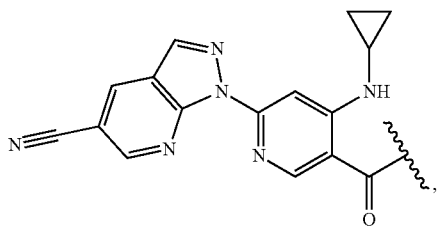 [SMILES: *C(=O)c1cnc(-n2ncc3cc(C#N)cnc32)cc1NC1CC1]

LBM is selected from any of those in Table A below, and L is selected from any of those in Table B below.

In some embodiments, a provided compound or pharmaceutically acceptable salt thereof, is selected from those wherein IRAK is

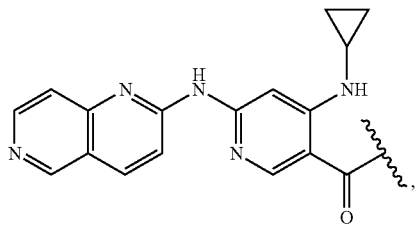 [SMILES: *C(=O)c1cnc(Nc2ccc3cnccc3n2)cc1NC1CC1]

LBM is selected from any of those in Table A below, and L is selected from any of those in Table B below.

In some embodiments, a provided compound or pharmaceutically acceptable salt thereof, is selected from those wherein IRAK is

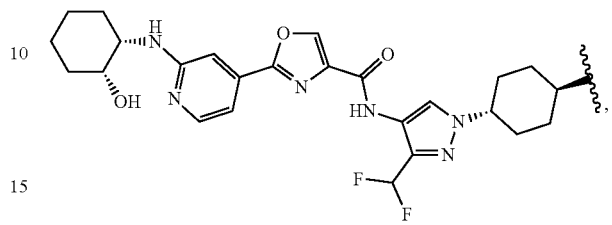

LBM is selected from any of those in Table A below, and L is selected from any of those in Table B below.

In some embodiments, a provided compound or pharmaceutically acceptable salt thereof, is selected from those wherein IRAK is

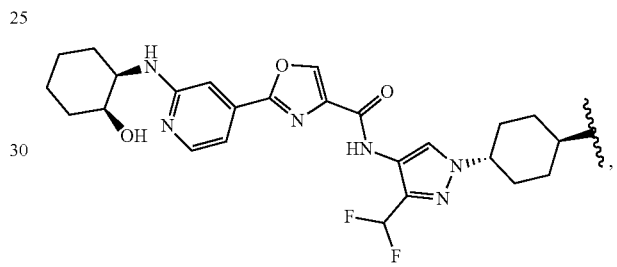

LBM is selected from any of those in Table A below, and L is selected from any of those in Table B below.

In some embodiments, a provided compound or pharmaceutically acceptable salt thereof, is selected from those wherein IRAK is

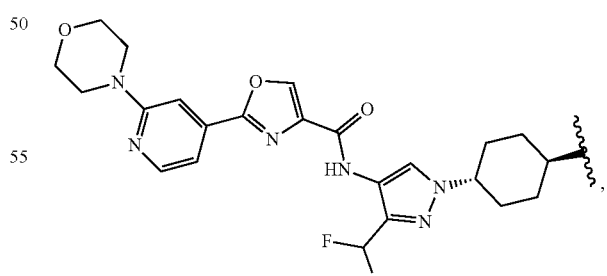

LBM is selected from any of those in Table A below, and L is selected from any of those in Table B below.

In some embodiments, a provided compound or pharmaceutically acceptable salt thereof, is selected from those wherein IRAK is

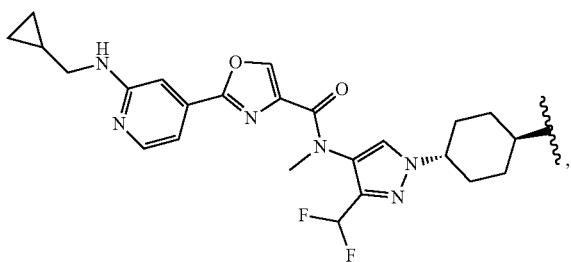 [SMILES: *[C@H]1CC[C@H](n2cc(N(C)C(=O)c3coc(-c4ccnc(NCC5CC5)c4)n3)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

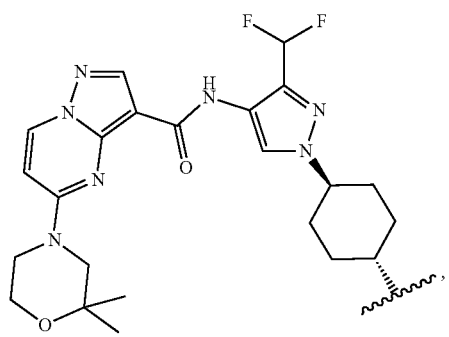 [SMILES: *[C@H]1CC[C@H](n2cc(NC(=O)c3cnn4ccc(N5CCOC(C)(C)C5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

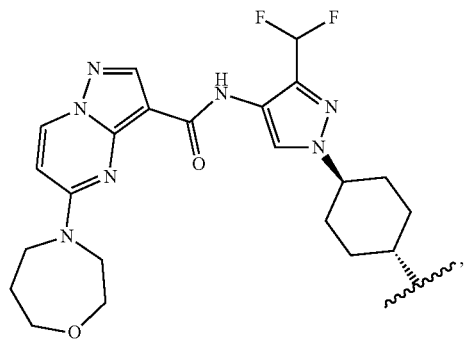 [SMILES: *[C@H]1CC[C@H](n2cc(NC(=O)c3cnn4ccc(N5CCCOCC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

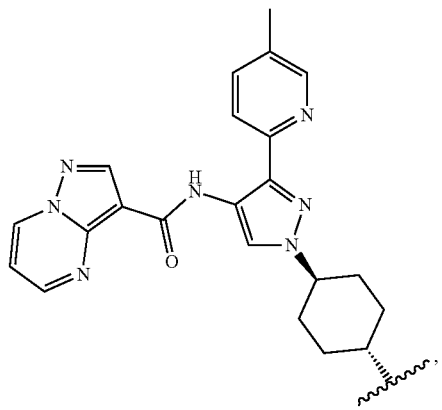 [SMILES: *[C@H]1CC[C@H](n2cc(NC(=O)c3cnn4cccnc34)c(-c3ccc(C)cn3)n2)CC1]

LBM is selected from any of those in Table A below, and L is selected from any of those in Table B below.

In some embodiments, a provided compound or pharmaceutically acceptable salt thereof, is selected from those wherein IRAK is

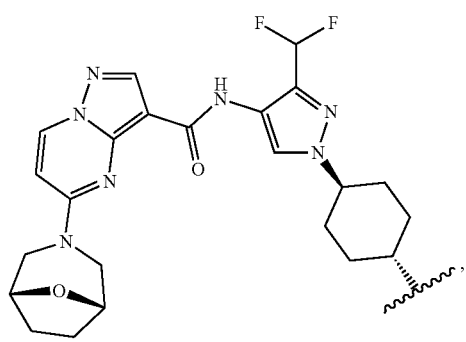 [SMILES: *[C@H]1CC[C@H](n2cc(NC(=O)c3cnn4ccc(N5C[C@H]6CC[C@@H](C5)O6)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

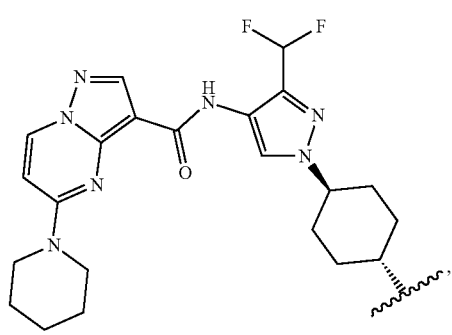 [SMILES: *[C@H]1CC[C@H](n2cc(NC(=O)c3cnn4ccc(N5CCCCC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

545

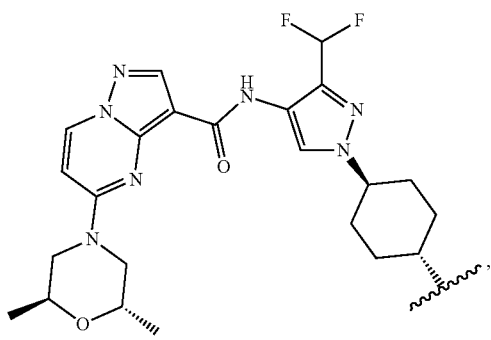 [SMILES: *[C@H]1CC[C@H](n2cc(NC(=O)c3cnn4ccc(N5C[C@H](C)O[C@@H](C)C5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

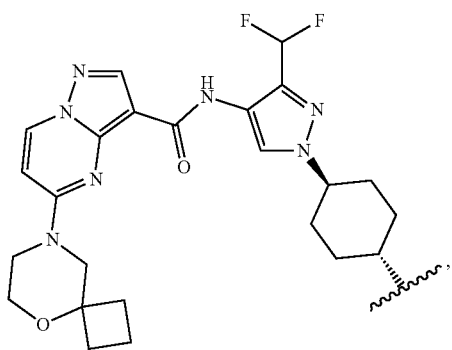 [SMILES: *[C@H]1CC[C@H](n2cc(NC(=O)c3cnn4ccc(N5CCOC6(CCC6)C5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

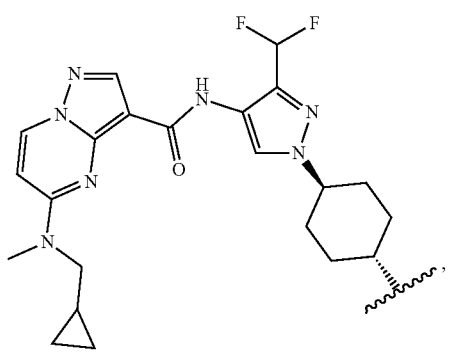 [SMILES: *[C@H]1CC[C@H](n2cc(NC(=O)c3cnn4ccc(N(C)CC5CC5)nc34)c(C(F)F)n2)CC1]

LBM is selected from any of those in Table A below, and L is selected from any of those in Table B below.

In some embodiments, a provided compound or pharmaceutically acceptable salt thereof, is selected from those wherein IRAK is

546

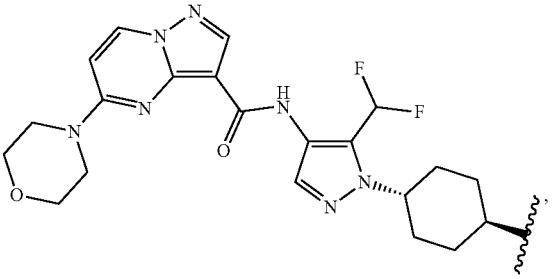 [SMILES: *[C@H]1CC[C@H](n2ncc(NC(=O)c3cnn4ccc(N5CCOCC5)nc34)c2C(F)F)CC1]

LBM is selected from any of those in Table A below, and L is selected from any of those in Table B below.

TABLE A

Exemplified E3 ligases (LBM)

(a)
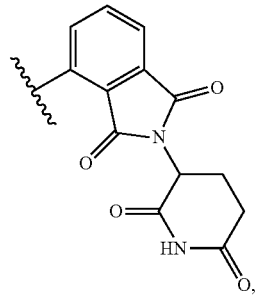 [SMILES: *c1cccc2c1C(=O)N(C1CCC(=O)NC1=O)C2=O]

(b)
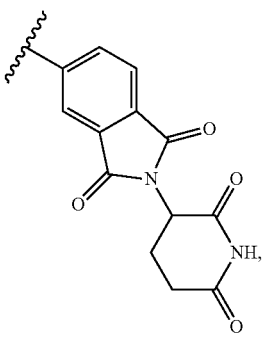 [SMILES: *c1ccc2c(c1)C(=O)N(C1CCC(=O)NC1=O)C2=O]

(c)
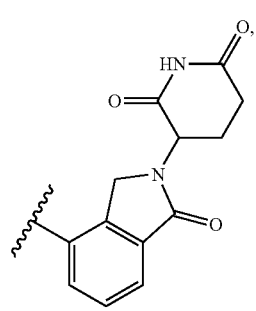

TABLE A-continued
Exemplified E3 ligases (LBM)
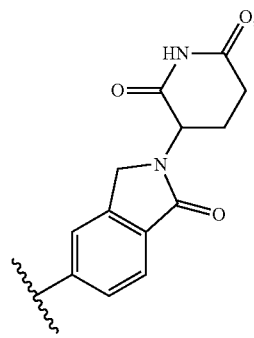 (d)
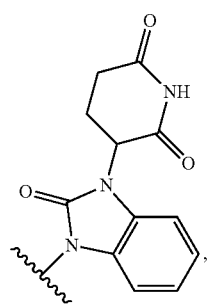 [SMILES: *n1c(=O)n(C2CCC(=O)NC2=O)c2ccccc21] (e)
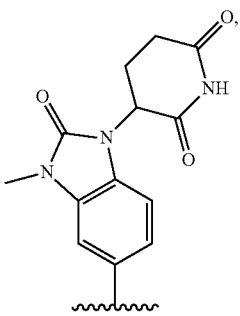 [SMILES: *c1ccc2c(c1)n(C)c(=O)n2C1CCC(=O)NC1=O] (f)
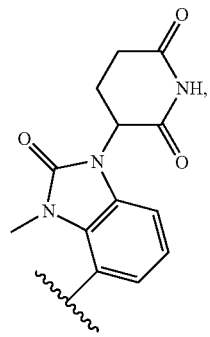 [SMILES: *c1cccc2c1n(C)c(=O)n2C1CCC(=O)NC1=O] (g)
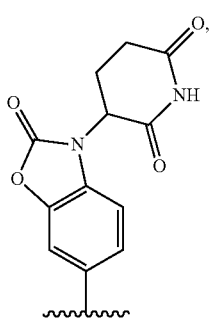 [SMILES: *c1ccc2c(c1)oc(=O)n2C1CCC(=O)NC1=O] (h)
TABLE A-continued
Exemplified E3 ligases (LBM)
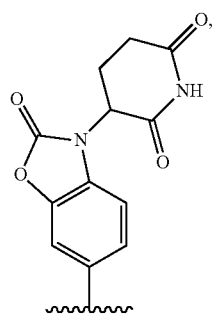 (i)
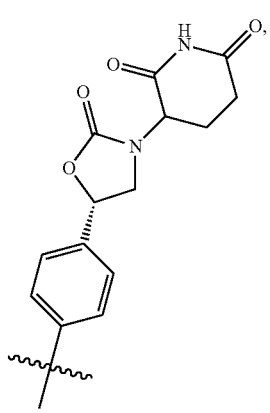 [SMILES: *c1ccc([C@H]2CN(C3CCC(=O)NC3=O)C(=O)O2)cc1] (j)
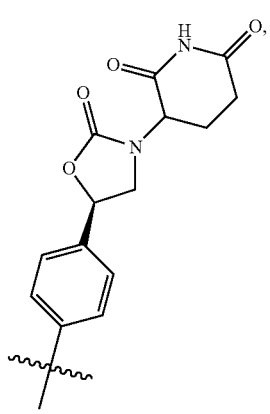 [SMILES: *c1ccc([C@@H]2CN(C3CCC(=O)NC3=O)C(=O)O2)cc1] (k)
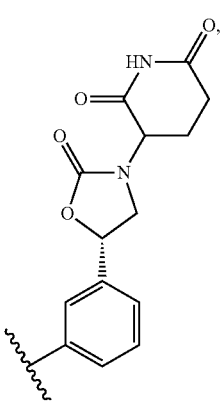 [SMILES: *c1cccc([C@H]2CN(C3CCC(=O)NC3=O)C(=O)O2)c1] (l)

TABLE A-continued
Exemplified E3 ligases (LBM)
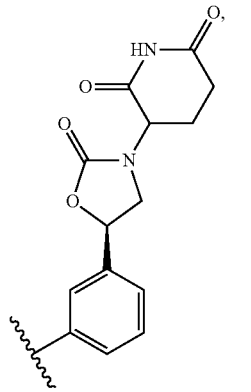 [SMILES: *c1cccc([C@@H]2CN(C3CCC(=O)NC3=O)C(=O)O2)c1]
(m)
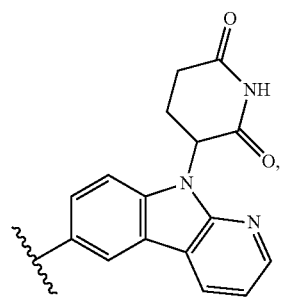 [SMILES: *c1ccc2c(c1)c1cccnc1n2C1CCC(=O)NC1=O]
(n)
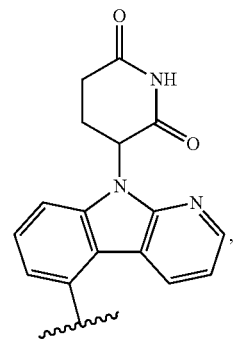 [SMILES: *c1cccc2c1c1cccnc1n2C1CCC(=O)NC1=O]
(o)
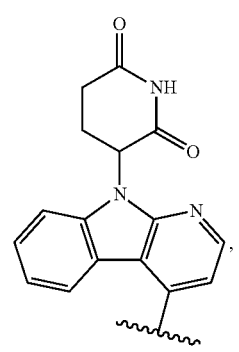 [SMILES: *c1ccnc2c1c1ccccc1n2C1CCC(=O)NC1=O]
(p)
TABLE A-continued
Exemplified E3 ligases (LBM)
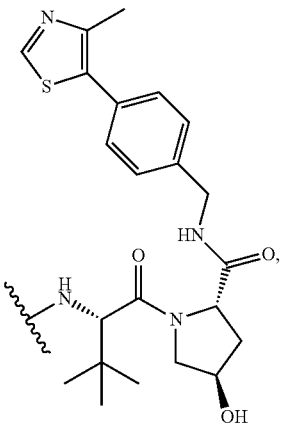 [SMILES: *N[C@H](C(=O)N1C[C@H](O)C[C@H]1C(=O)NCc1ccc(-c2scnc2C)cc1)C(C)(C)C]
(q)
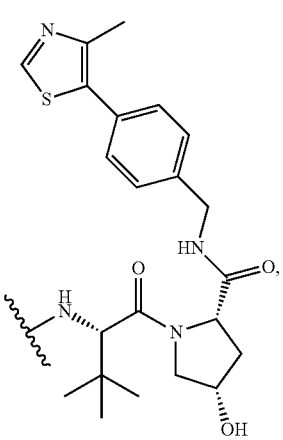 [SMILES: *N[C@H](C(=O)N1C[C@@H](O)C[C@H]1C(=O)NCc1ccc(-c2scnc2C)cc1)C(C)(C)C]
(r)
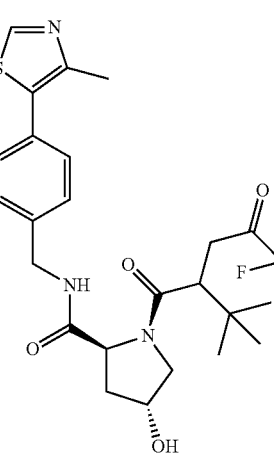
(s)

TABLE A-continued
Exemplified E3 ligases (LBM)
(t)
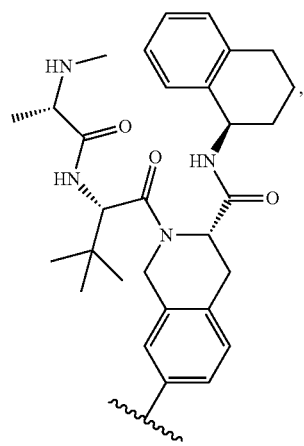 [SMILES: *c1ccc2c(c1)CN(C(=O)[C@@H](NC(=O)[C@H](C)NC)C(C)(C)C)[C@H](C(=O)N[C@@H]1CCCc3ccccc31)C2]
(u)
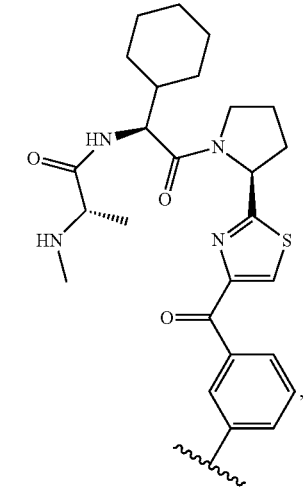 [SMILES: *c1cccc(C(=O)c2csc([C@@H]3CCCN3C(=O)[C@@H](NC(=O)[C@H](C)NC)C3CCCCC3)n2)c1]
(v)
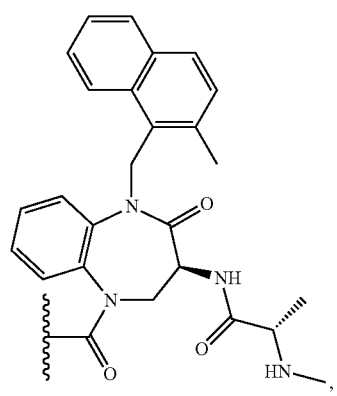 [SMILES: *C(=O)N1C[C@H](NC(=O)[C@H](C)NC)C(=O)N(Cc2c(C)ccc3ccccc23)c2ccccc21]
TABLE A-continued
Exemplified E3 ligases (LBM)
(w)
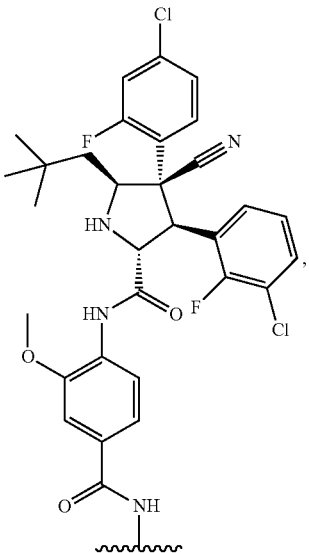 [SMILES: *NC(=O)c1ccc(NC(=O)[C@@H]2N[C@@H](CC(C)(C)C)[C@](C#N)(c3ccc(Cl)cc3F)[C@H]2c2cccc(Cl)c2F)c(OC)c1]
(x)
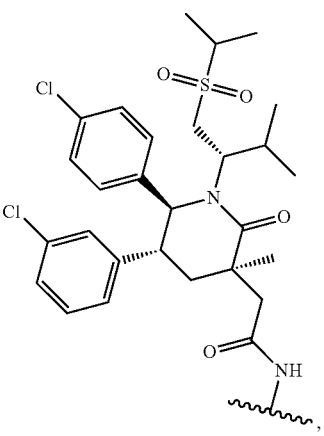 [SMILES: *NC(=O)C[C@@]1(C)C[C@H](c2cccc(Cl)c2)[C@@H](c2ccc(Cl)cc2)N([C@H](CS(=O)(=O)C(C)C)C(C)C)C1=O]
(y)
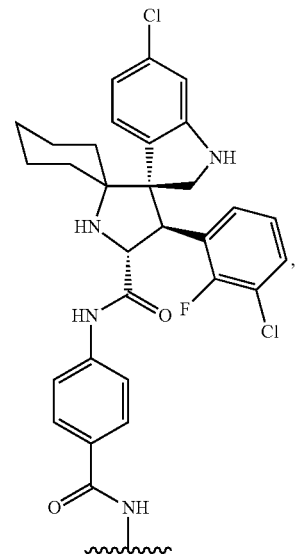 [SMILES: *NC(=O)c1ccc(NC(=O)[C@@H]2NC3(CCCCC3)[C@@]3(CNc4cc(Cl)ccc43)[C@H]2c2cccc(Cl)c2F)cc1]

TABLE A-continued
Exemplified E3 ligases (LBM)
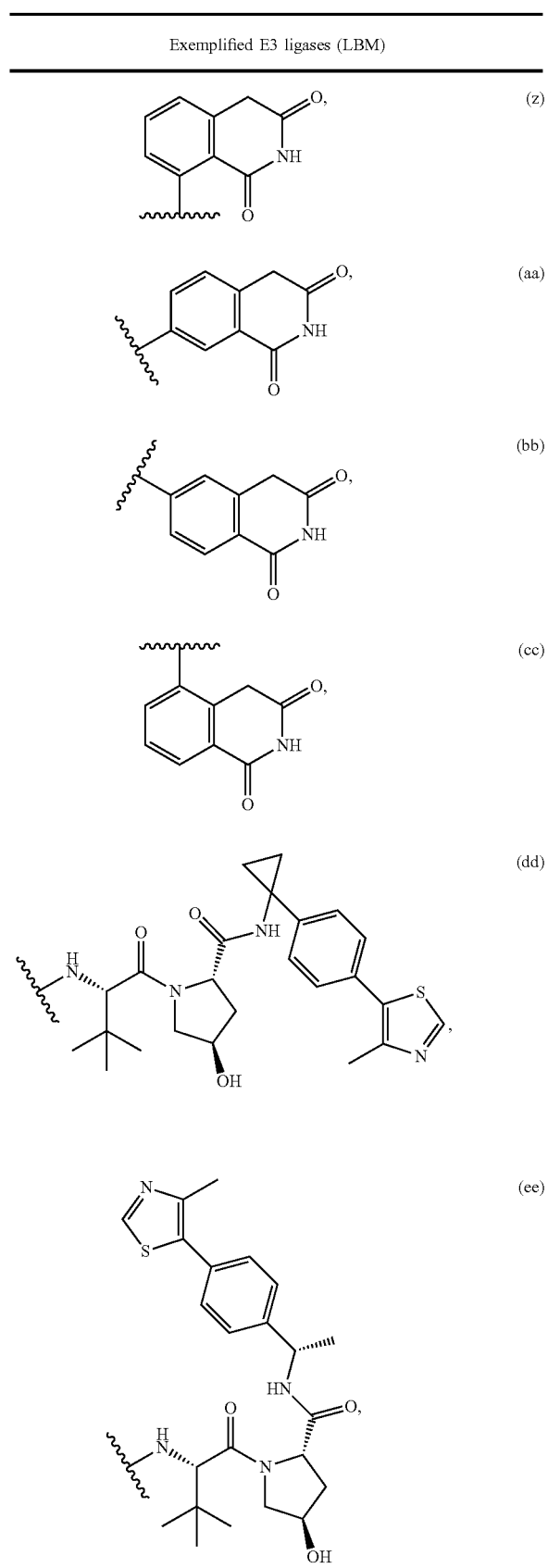
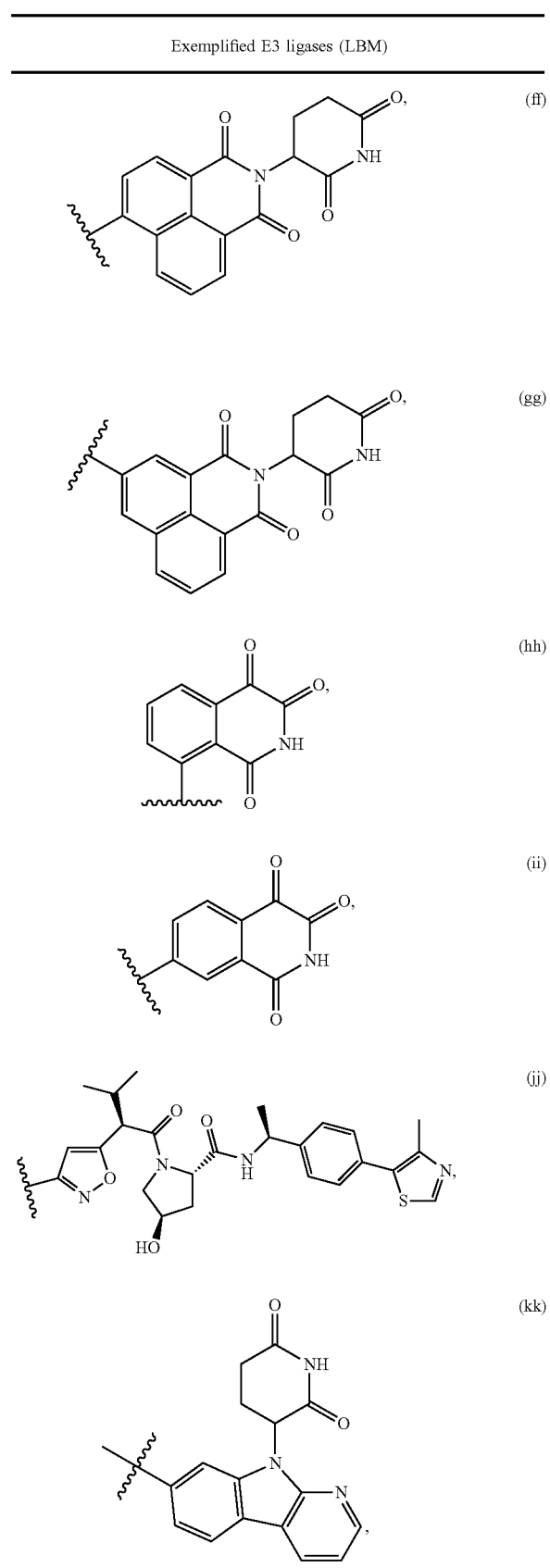

TABLE A-continued
Exemplified E3 ligases (LBM)
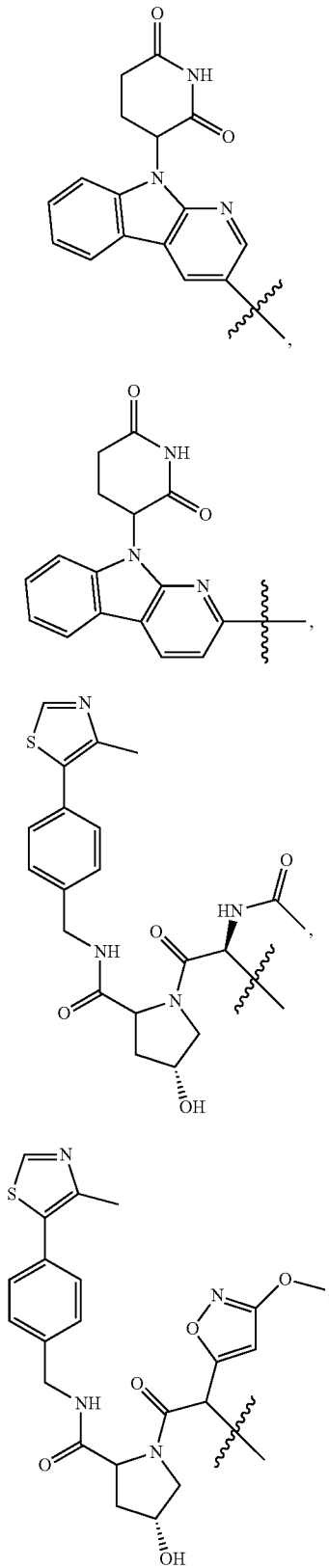
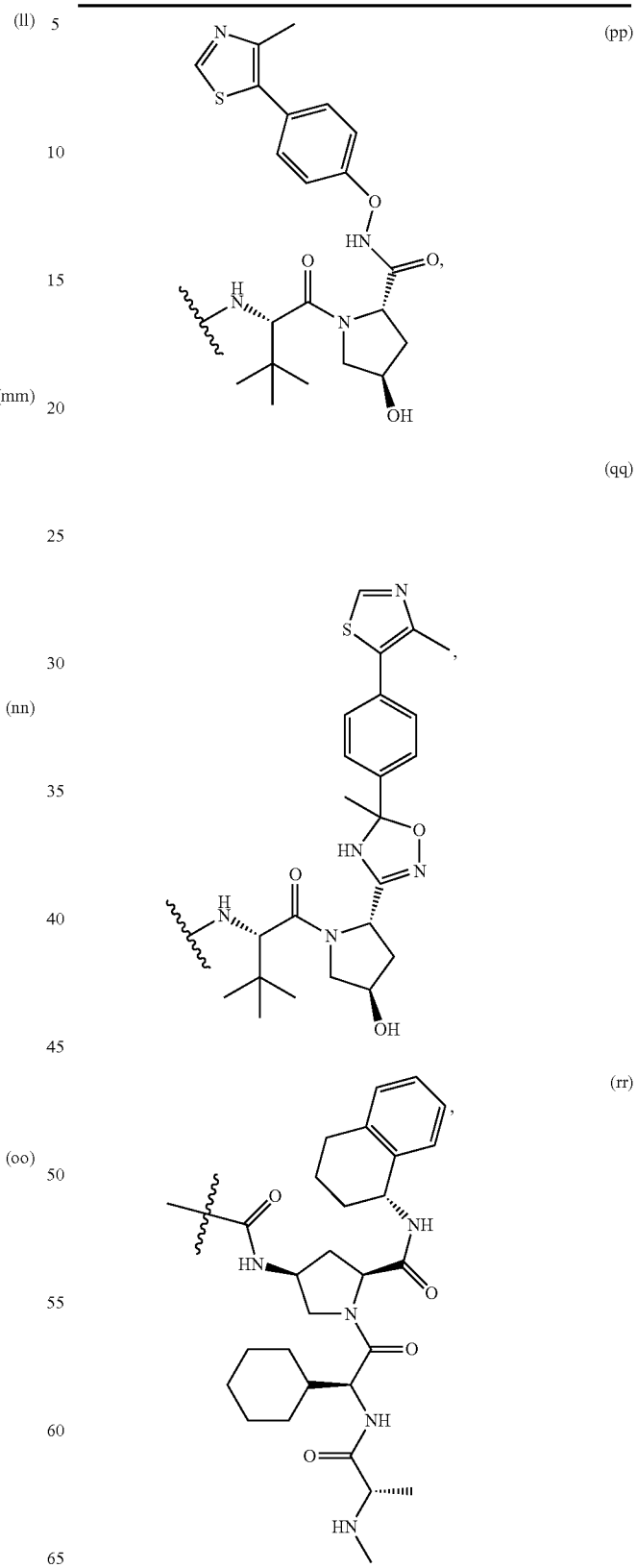

TABLE A-continued
Exemplified E3 ligases (LBM)
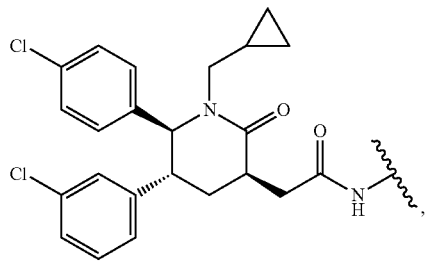 [SMILES: *NC(=O)C[C@H]1C[C@H](c2cccc(Cl)c2)[C@@H](c2ccc(Cl)cc2)N(CC2CC2)C1=O]
(ss)
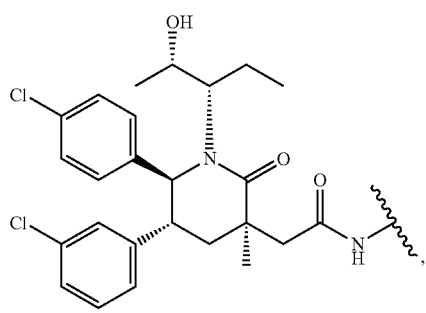 [SMILES: *NC(=O)C[C@@]1(C)C[C@H](c2cccc(Cl)c2)[C@@H](c2ccc(Cl)cc2)N([C@@H](CC)[C@H](C)O)C1=O]
(tt)
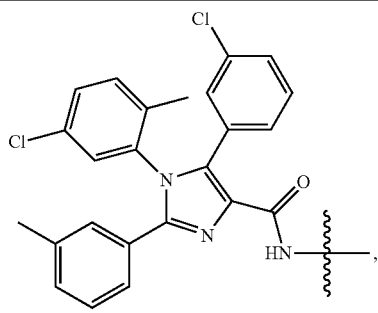
(uu)
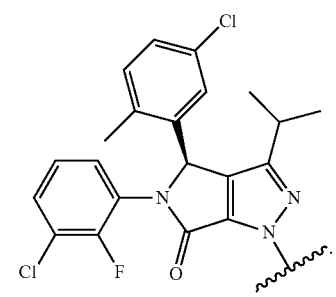 [SMILES: *n1nc(C(C)C)c2c1C(=O)N(c1cccc(Cl)c1F)[C@H]2c1cc(Cl)ccc1C]
(vv)
TABLE B
Exemplified Linkers (L)
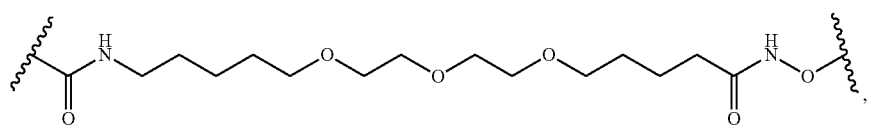 [SMILES: *ONC(=O)CCCCOCCOCCOCCCCCNC(*)=O]
(1)
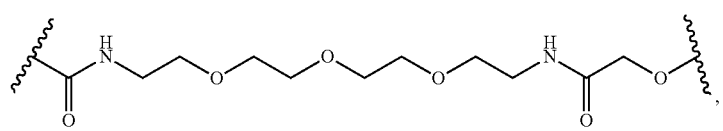 [SMILES: *OCC(=O)NCCOCCOCCOCCNC(*)=O]
(2)
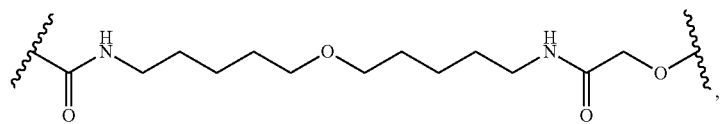 [SMILES: *OCC(=O)NCCCCCOCCCCCNC(*)=O]
(3)
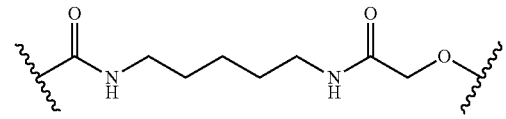
(4)
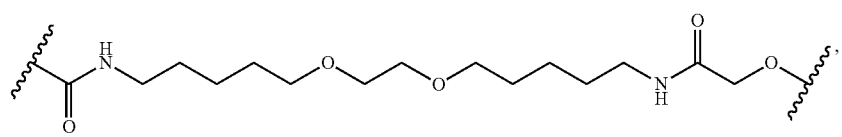 [SMILES: *OCC(=O)NCCCCCOCCOCCCCCNC(*)=O]
(5)
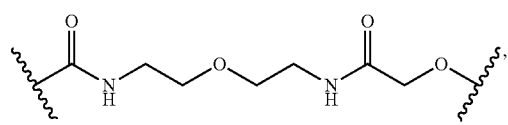 [SMILES: *OCC(=O)NCCOCCNC(*)=O]
(6)

TABLE B-continued
Exemplified Linkers (L)
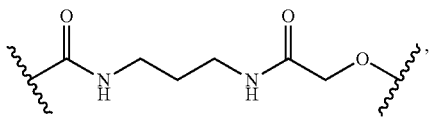 [SMILES: *OCC(=O)NCCCNC(*)=O]
(7)
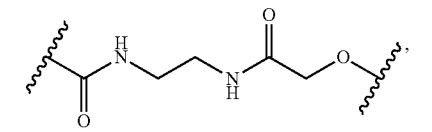 [SMILES: *OCC(=O)NCCNC(*)=O]
(8)
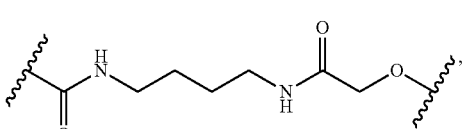
(9)
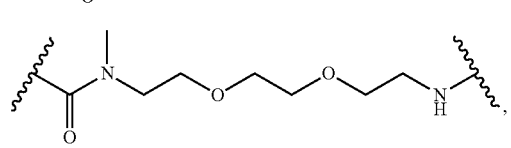
(10)
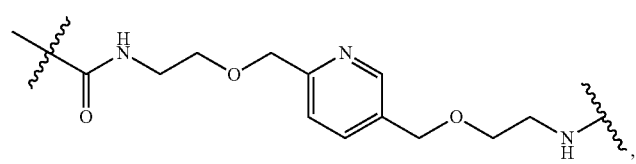 [SMILES: *NCCOCc1ccc(COCCNC(*)=O)nc1]
(11)
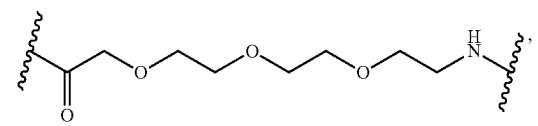 [SMILES: *NCCOCCOCCOCC(*)=O]
(12)
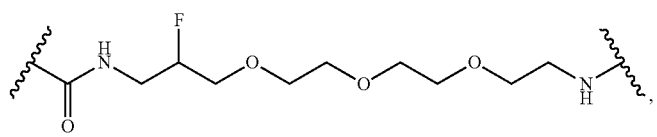 [SMILES: *NCCOCCOCCOCC(F)CNC(*)=O]
(13)
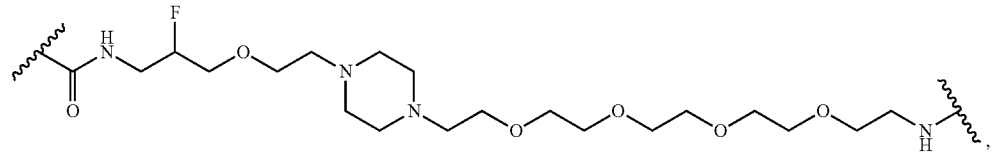 [SMILES: *NCCOCCOCCOCCOCCN1CCN(CCOCC(F)CNC(*)=O)CC1]
(14)
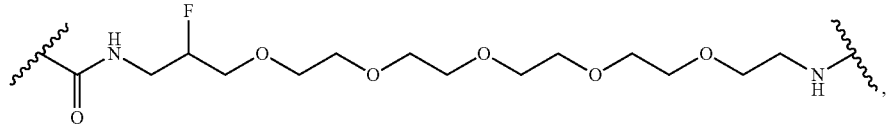 [SMILES: *NCCOCCOCCOCCOCCOCC(F)CNC(*)=O]
(15)
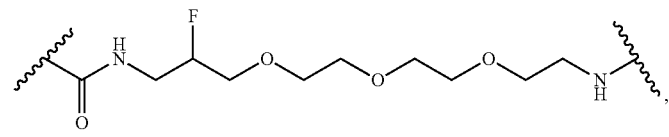 [SMILES: *NCCOCCOCCOCC(F)CNC(*)=O]
(16)
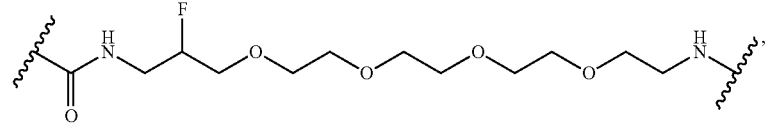 [SMILES: *NCCOCCOCCOCCOCC(F)CNC(*)=O]
(17)

TABLE B-continued

Exemplified Linkers (L)

TABLE B-continued
Exemplified Linkers (L)
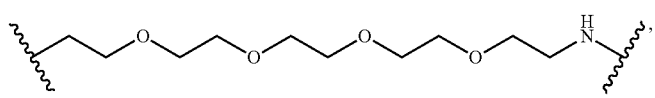 [SMILES: *CCOCCOCCOCCOCCN*] (29)
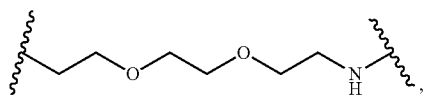 [SMILES: *CCOCCOCCN*] (30)
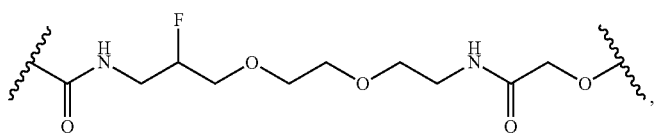 [SMILES: *OCC(=O)NCCOCCOCC(F)CNC(*)=O] (31)
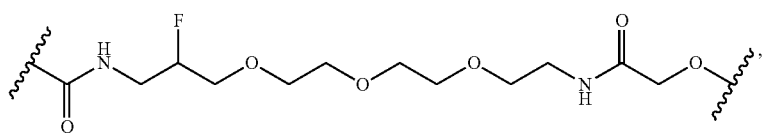 [SMILES: *OCC(=O)NCCOCCOCCOCC(F)CNC(*)=O] (32)
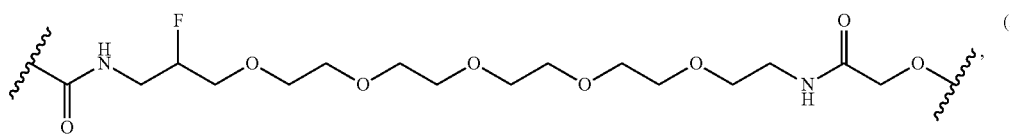 (33)
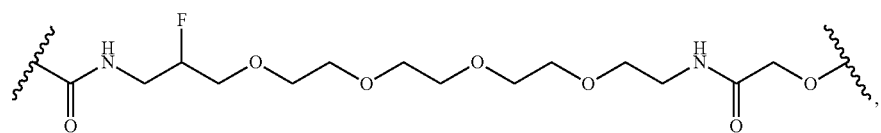 [SMILES: *OCC(=O)NCCOCCOCCOCCOCC(F)CNC(*)=O] (34)
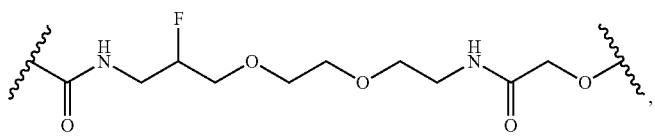 [SMILES: *OCC(=O)NCCOCCOCC(F)CNC(*)=O] (35)
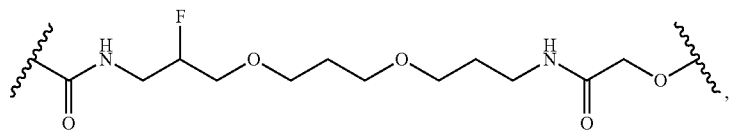 [SMILES: *OCC(=O)NCCCOCCCOCC(F)CNC(*)=O] (36)
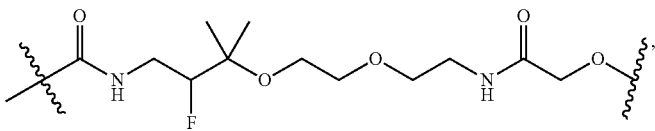 [SMILES: *OCC(=O)NCCOCCOC(C)(C)C(F)CNC(*)=O] (37)
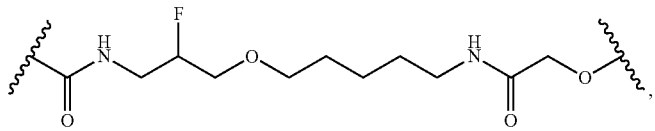 [SMILES: *OCC(=O)NCCCCCOCC(F)CNC(*)=O] (38)
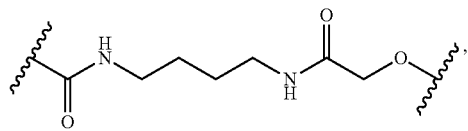 [SMILES: *OCC(=O)NCCCCNC(*)=O] (39)

TABLE B-continued
Exemplified Linkers (L)
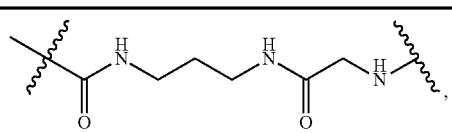 (40)
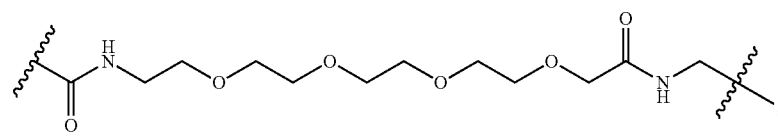 (41)
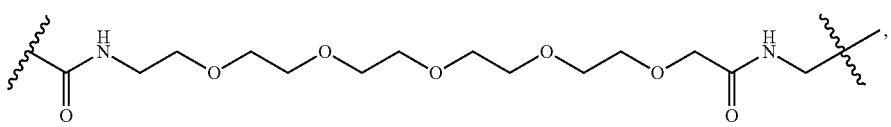 [SMILES: *CNC(=O)COCCOCCOCCOCCOCCNC(*)=O] (42)
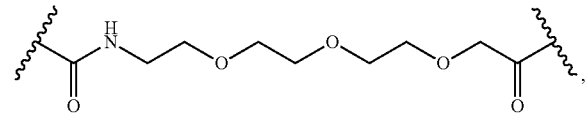 [SMILES: *C(=O)COCCCCCCCCNC(*)=O] (43)
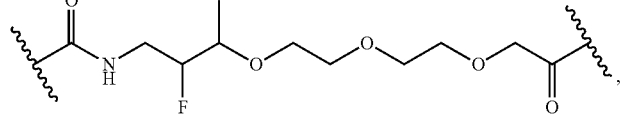 (44)
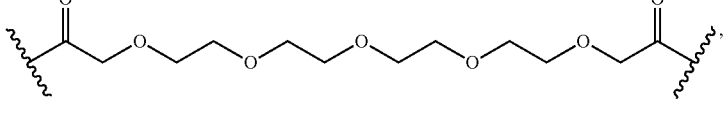 (45)
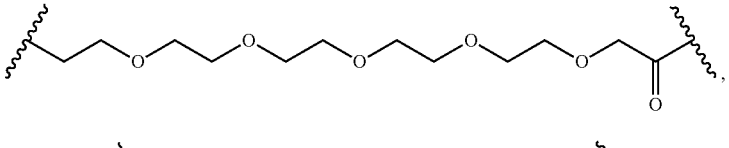 (46)
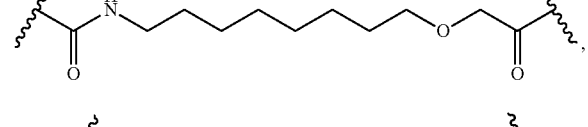 (47)
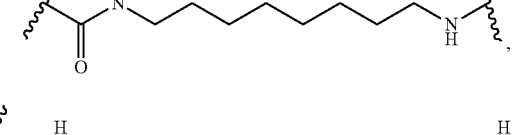 (48)
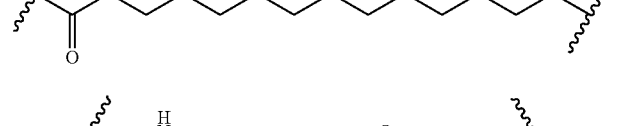 (50)
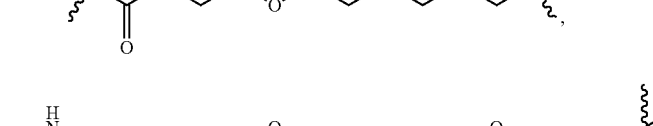 (51)
 (52)

TABLE B-continued
Exemplified Linkers (L)
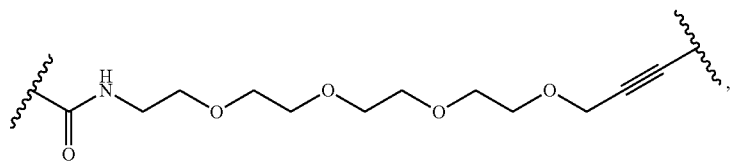 [SMILES: *C#CCOCCOCCOCCOCCNC(*)=O] (53)
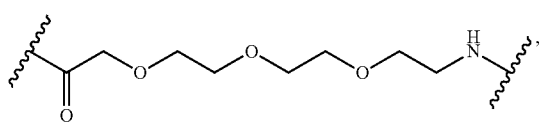 [SMILES: *NCCOCCOCCOCC(*)=O] (54)
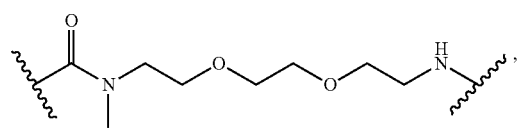 [SMILES: *NCCOCCOCCN(C)C(*)=O] (55)
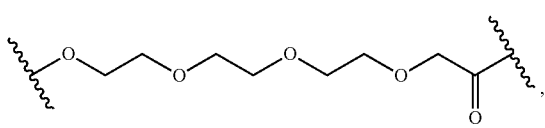 [SMILES: *OCCOCCOCCOCC(*)=O] (56)
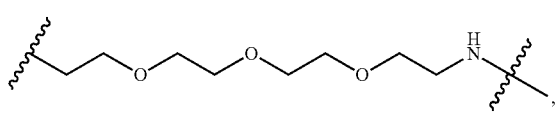 [SMILES: *CCOCCOCCOCCN*] (57)
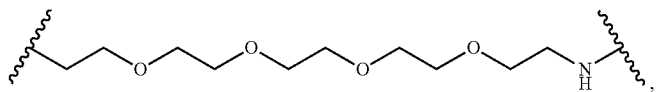 [SMILES: *CCOCCOCCOCCOCCN*] (58)
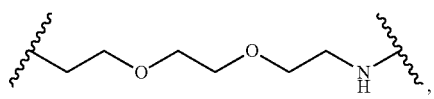 [SMILES: *CCOCCOCCN*] (59)
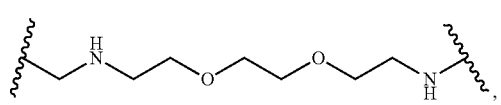 [SMILES: *CNCCOCCOCCN*] (60)
 (61)
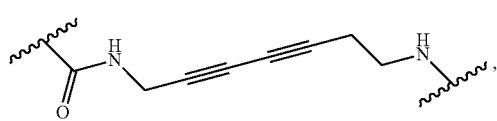 [SMILES: *NCCC#CC#CCNC(*)=O] (62)
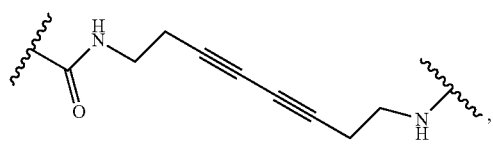 [SMILES: *NCCC#CC#CCCNC(*)=O] (63)
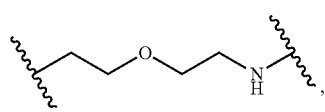 [SMILES: *CCOCCN*] (64)

TABLE B-continued

Exemplified Linkers (L)

TABLE B-continued
Exemplified Linkers (L)
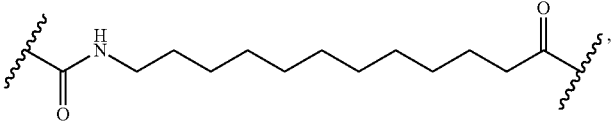 [SMILES: *C(=O)CCCCCCCCCCCNC(*)=O]
(77)
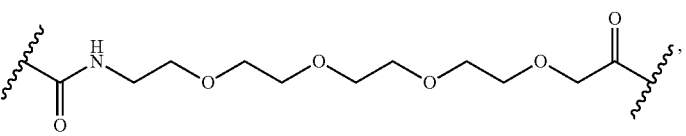 [SMILES: *C(=O)COCCOCCOCCOCCNC(*)=O]
(78)
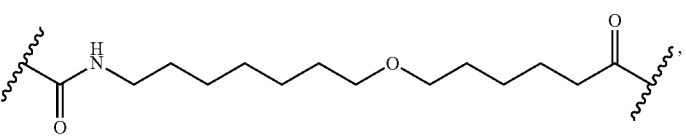 [SMILES: *C(=O)CCCCCOCCCCCCCNC(*)=O]
(79)
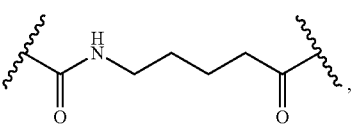 [SMILES: *C(=O)CCCCNC(*)=O]
(80)
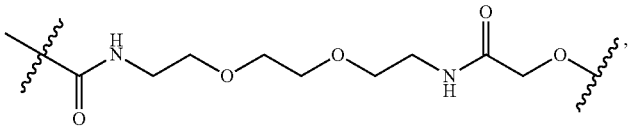 [SMILES: *OCC(=O)NCCOCCOCCNC(*)=O]
(81)
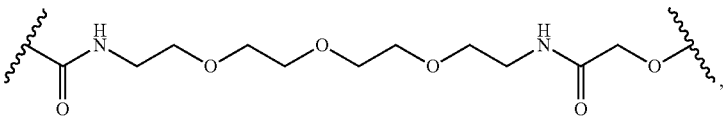 [SMILES: *OCC(=O)NCCOCCOCCOCCNC(*)=O]
(82)
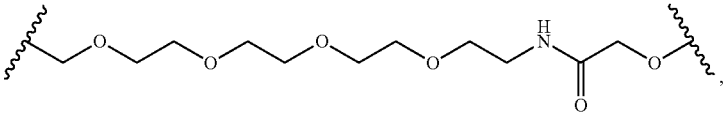 [SMILES: *COCCOCCOCCOCCNC(=O)CO*]
(83)
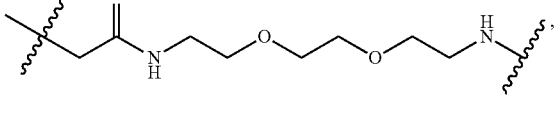
(84)
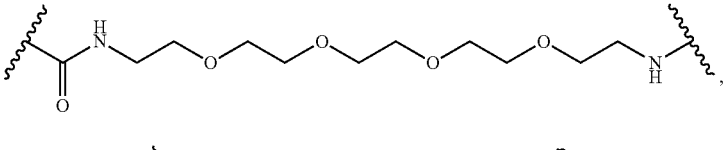
(85)
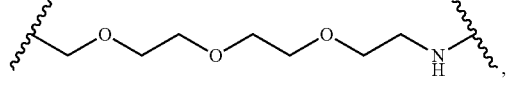
(86)
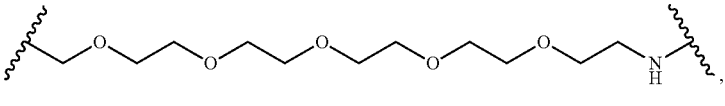 [SMILES: *COCCOCCOCCOCCOCCN*]
(87)
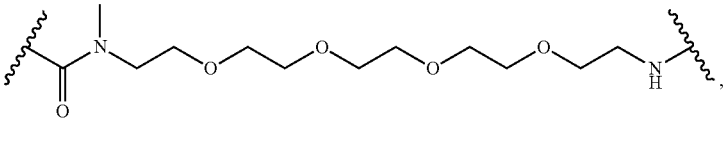 [SMILES: *NCCOCCOCCOCCOCCN(C)C(*)=O]
(88)

TABLE B-continued

Exemplified Linkers (L)

TABLE B-continued

Exemplified Linkers (L)

TABLE B-continued
Exemplified Linkers (L)
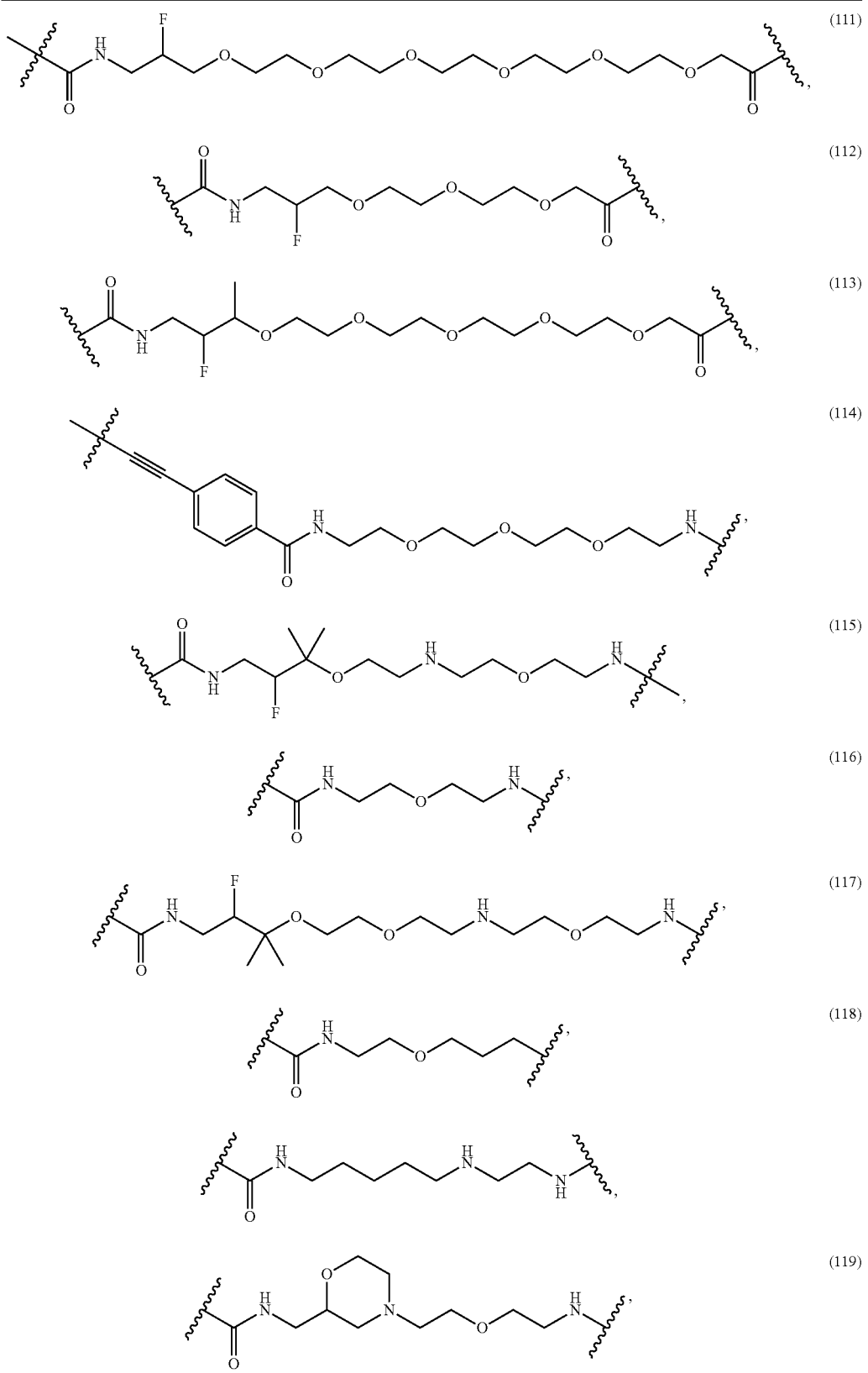

TABLE B-continued
Exemplified Linkers (L)
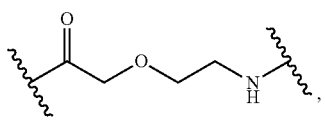 [SMILES: *NCCOCC(*)=O]
(120)
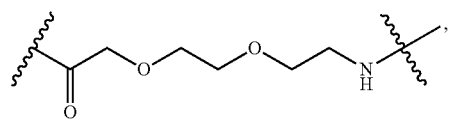 [SMILES: *NCCOCCOCC(*)=O]
(121)
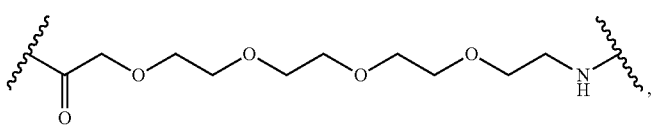 [SMILES: *NCCOCCOCCOCCOCC(*)=O]
(122)
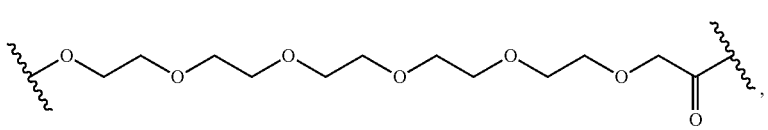 [SMILES: *OCCOCCOCCOCCOCCOCC(*)=O]
(123)
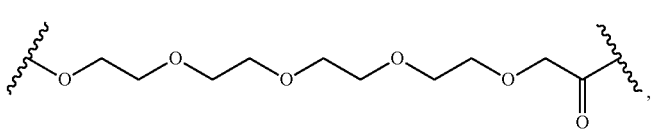 [SMILES: *OCCOCCOCCOCCOCC(*)=O]
(124)
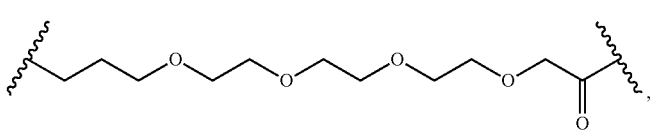 [SMILES: *CCCOCCOCCOCCOCC(*)=O]
(125)
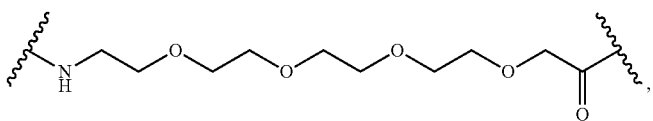 [SMILES: *NCCOCCOCCOCCOCC(*)=O]
(126)
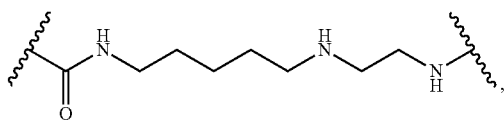 [SMILES: *NCCNCCCCCNC(*)=O]
(127)
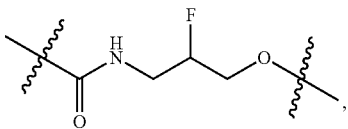 [SMILES: *OCC(F)CNC(*)=O]
(128)
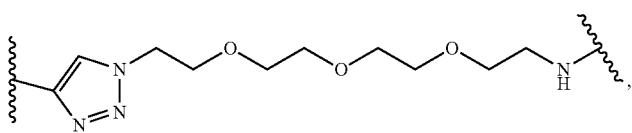 [SMILES: *NCCOCCOCCOCCn1cc(*)nn1]
(127)
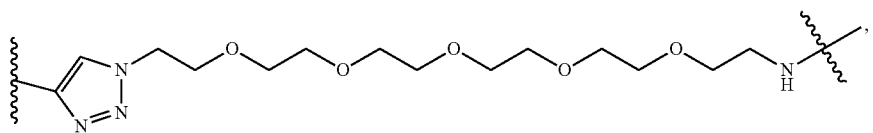 [SMILES: *NCCOCCOCCOCCOCCOCCn1cc(*)nn1]
(128)

TABLE B-continued
Exemplified Linkers (L)
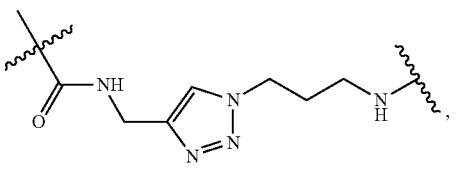 [SMILES: *NCCCn1cc(CNC(*)=O)nn1]  (129)
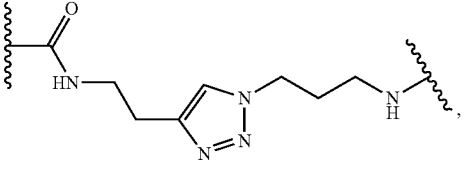 [SMILES: *NCCCn1cc(CCNC(*)=O)nn1]  (130)
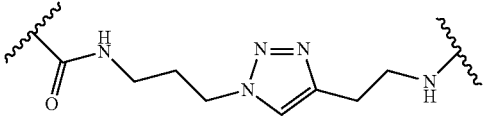  (131)
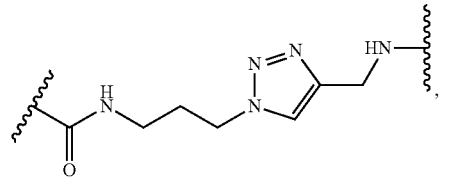 [SMILES: *NCc1cn(CCCNC(*)=O)nn1]  (132)
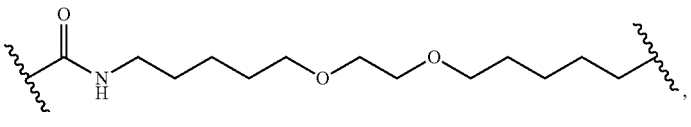 [SMILES: *CCCCCOCCOCCCCCNC(*)=O]  (133)
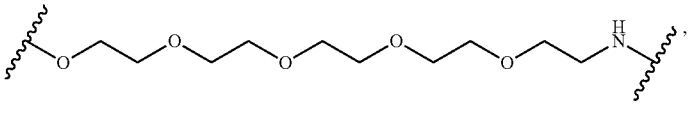 [SMILES: *NCCOCCOCCOCCOCCO*]  (134)
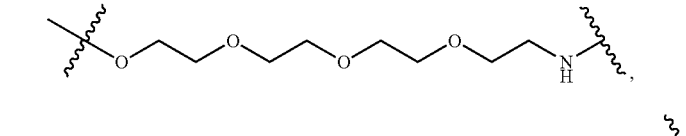  (135)
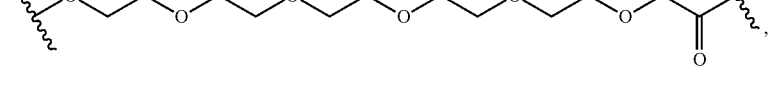  (136)
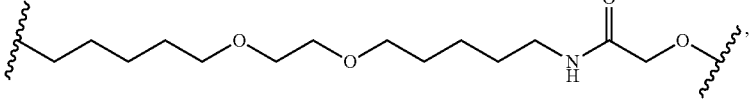  (137)
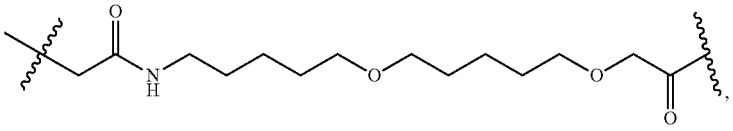 [SMILES: *CC(=O)NCCCCCOCCCCCOCC(*)=O]  (138)
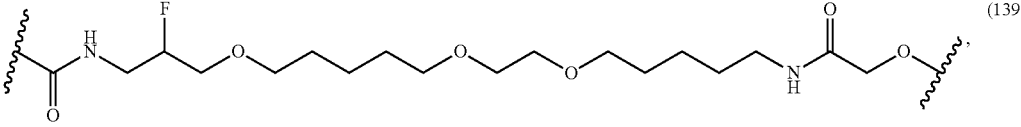  (139)

TABLE B-continued
Exemplified Linkers (L)
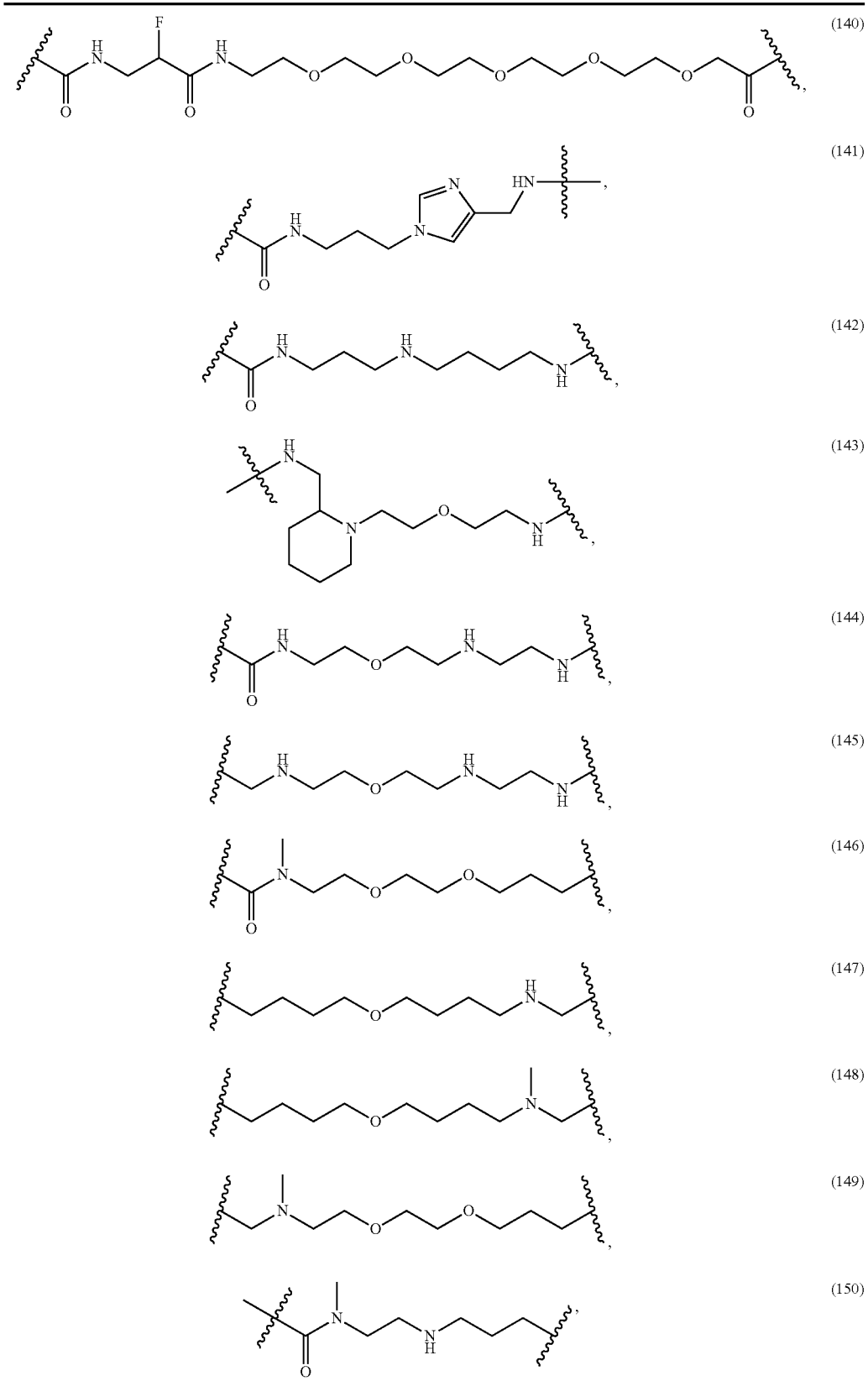

TABLE B-continued

Exemplified Linkers (L)

(151)

(152)

(153)

(154)

(155)

(156)

(157)

(158)

(159)

(160)

(161)

(162)

TABLE B-continued
Exemplified Linkers (L)
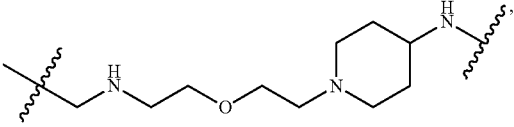 [SMILES: *CNCCOCCN1CCC(N*)CC1] (163)
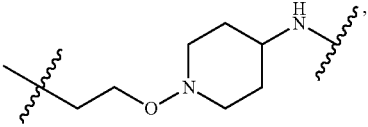 [SMILES: *CCON1CCC(N*)CC1] (164)
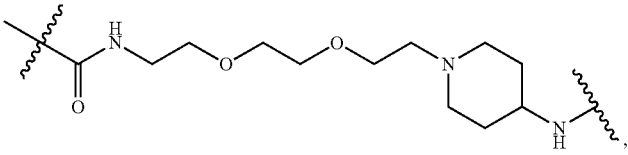 [SMILES: *NC1CCN(CCOCCOCCNC(*)=O)CC1] (165)
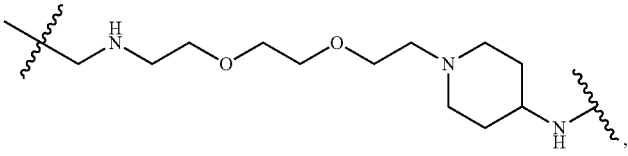 [SMILES: *CNCCOCCOCCN1CCC(N*)CC1] (166)
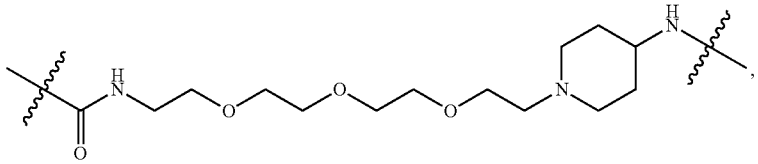 [SMILES: *NC1CCN(CCOCCOCCOCCNC(*)=O)CC1] (167)
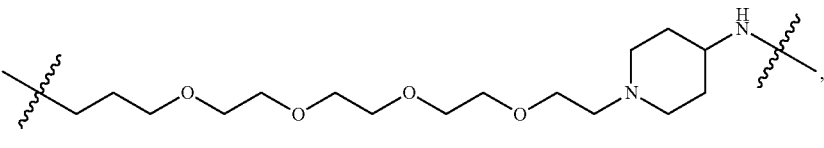 [SMILES: *CCCOCCOCCOCCOCCN1CCC(N*)CC1] (168)
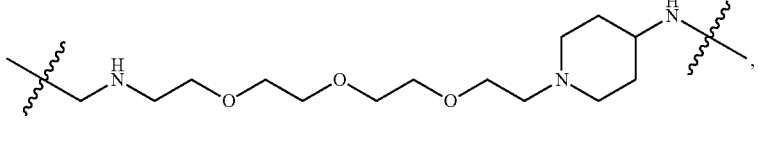 (169)
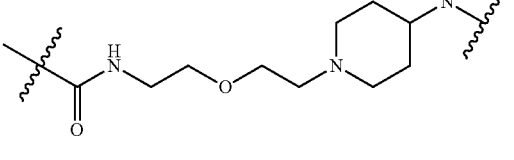 (170)
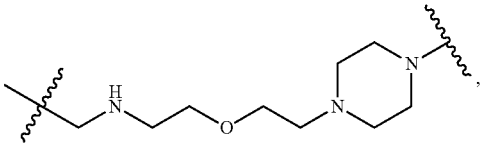 [SMILES: *CNCCOCCN1CCN(*)CC1] (171)

TABLE B-continued

Exemplified Linkers (L)

(172)

(173)

(174)

(175)

(176)

(177)

(178)

(179)

(180)

(181)

(182)

TABLE B-continued
Exemplified Linkers (L)
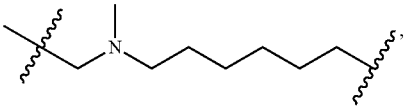 [SMILES: *CCCCCCN(C)C*]  (183)
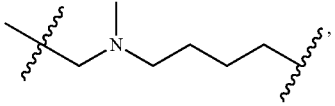 [SMILES: *CCCCN(C)C*]  (184)
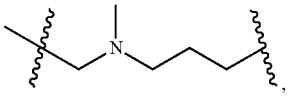  (185)
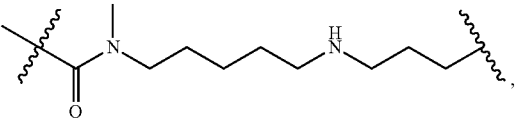 [SMILES: *CCCNCCCCCN(C)C(*)=O]  (186)
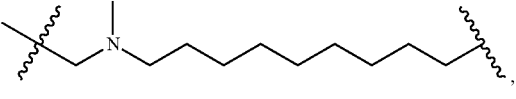 [SMILES: *CCCCCCCCCN(C)C*]  (187)
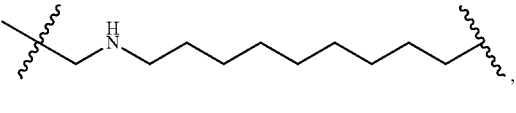 [SMILES: *CCCCCCCCCNC*]  (188)
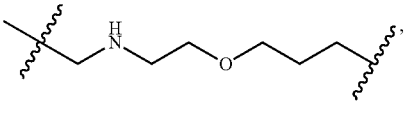 [SMILES: *CCCOCCNC*]  (189)
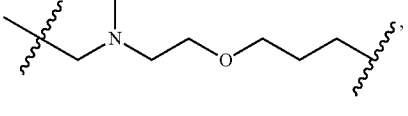  (190)
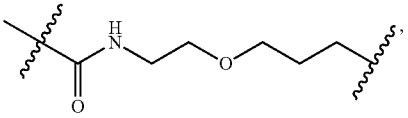 [SMILES: *CCCOCCNC(*)=O]  (191)
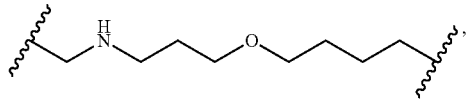 [SMILES: *CCCCOCCCNC*]  (192)
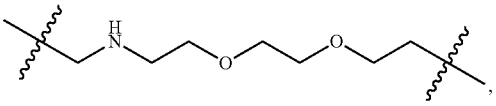 [SMILES: *CCOCCOCCNC*]  (193)
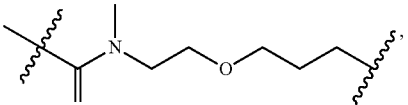  (194)
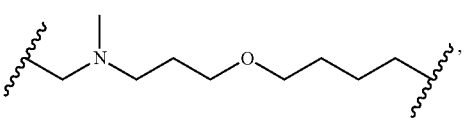 [SMILES: *CCCCOCCCN(C)C*]  (195)

TABLE B-continued
Exemplified Linkers (L)
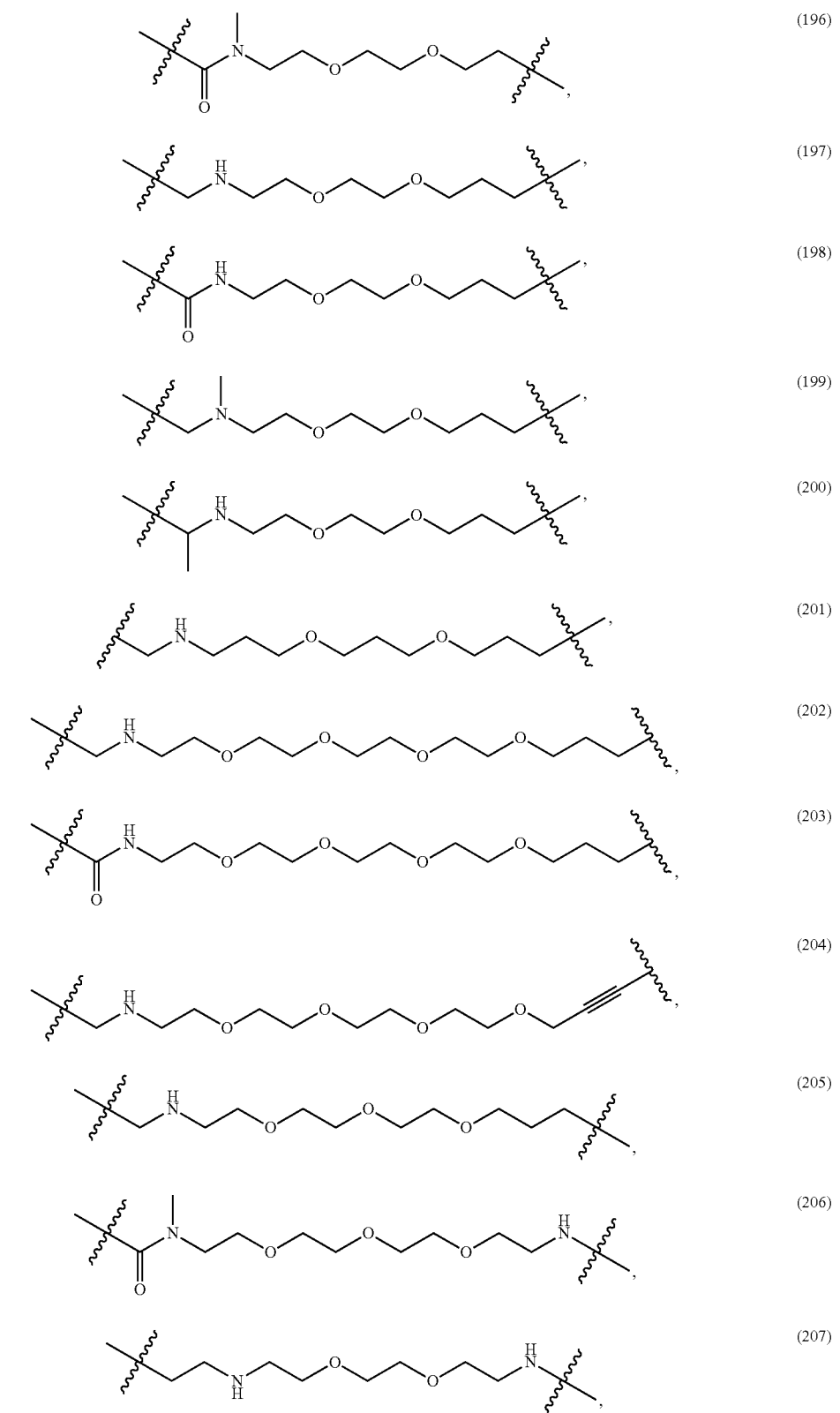

TABLE B-continued

Exemplified Linkers (L)

(208) — (218) [chemical structures of linkers containing morpholine rings with amine and ether linkages]

TABLE B-continued

Exemplified Linkers (L)

(219) [structure]

(220) [structure]

(221) [structure]

(222) [structure]

(223) [structure]

(224) [structure]

(225) [structure]

(226) [structure]

(227) [structure]

(228) [structure]

(229) [structure]

TABLE B-continued
Exemplified Linkers (L)
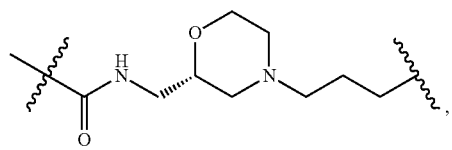 [SMILES: *CCCN1CCO[C@@H](CNC(*)=O)C1]
(230)
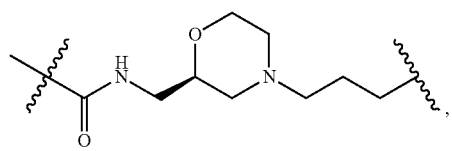 [SMILES: *CCCN1CCO[C@H](CNC(*)=O)C1]
(231)
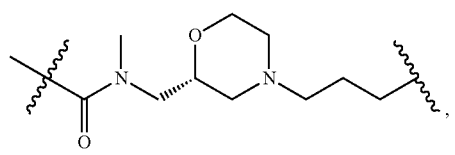 [SMILES: *CCCN1CCO[C@@H](CN(C)C(*)=O)C1]
(232)
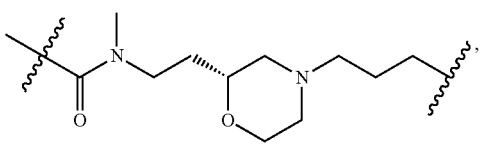 [SMILES: *CCCN1CCO[C@H](CCN(C)C(*)=O)C1]
(233)
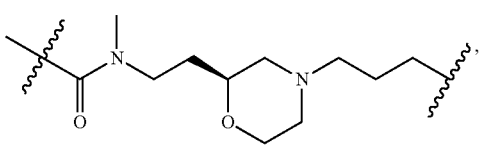 [SMILES: *CCCN1CCO[C@@H](CCN(C)C(*)=O)C1]
(234)
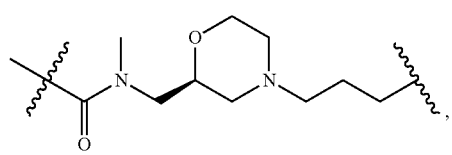 [SMILES: *CCCN1CCO[C@H](CN(C)C(*)=O)C1]
(235)
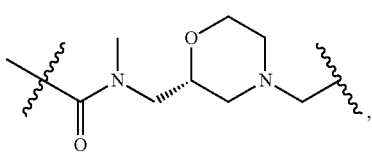 [SMILES: *CN1CCO[C@@H](CN(C)C(*)=O)C1]
(236)
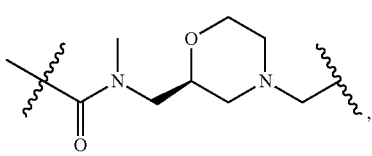 [SMILES: *CN1CCO[C@H](CN(C)C(*)=O)C1]
(237)
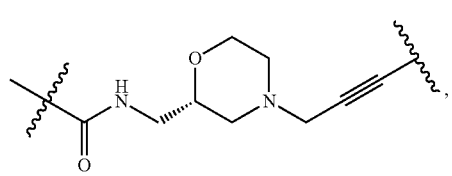 [SMILES: *C#CCN1CCO[C@@H](CNC(*)=O)C1]
(238)

TABLE B-continued
Exemplified Linkers (L)
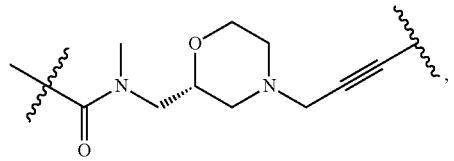 [SMILES: *C#CCN1CCO[C@@H](CN(C)C(*)=O)C1] (239)
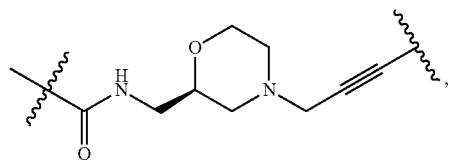 [SMILES: *C#CCN1CCO[C@H](CNC(*)=O)C1] (240)
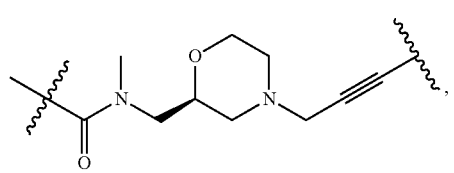 [SMILES: *C#CCN1CCO[C@H](CN(C)C(*)=O)C1] (241)
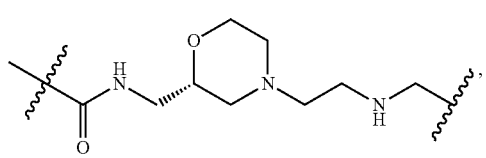 [SMILES: *CNCCN1CCO[C@@H](CNC(*)=O)C1] (242)
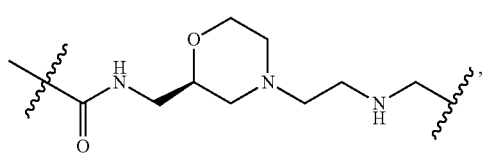 [SMILES: *CNCCN1CCO[C@H](CNC(*)=O)C1] (243)
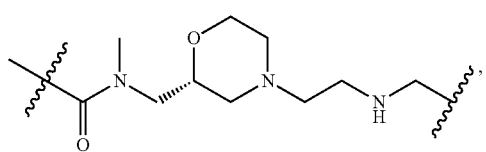 [SMILES: *CNCCN1CCO[C@@H](CN(C)C(*)=O)C1] (244)
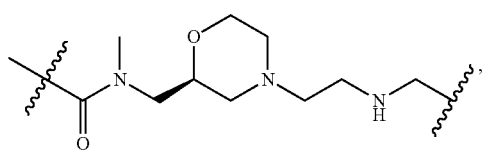 [SMILES: *CNCCN1CCO[C@H](CN(C)C(*)=O)C1] (245)
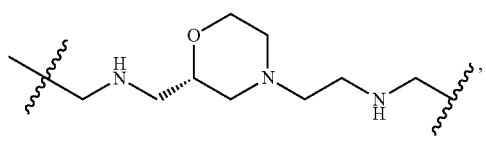 [SMILES: *CNCCN1CCO[C@@H](CNC*)C1] (246)
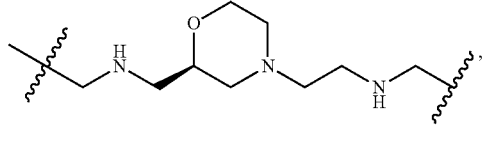 [SMILES: *CNCCN1CCO[C@H](CNC*)C1] (247)
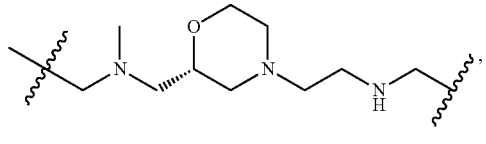 [SMILES: *CNCCN1CCO[C@@H](CN(C)C*)C1] (248)

TABLE B-continued
Exemplified Linkers (L)
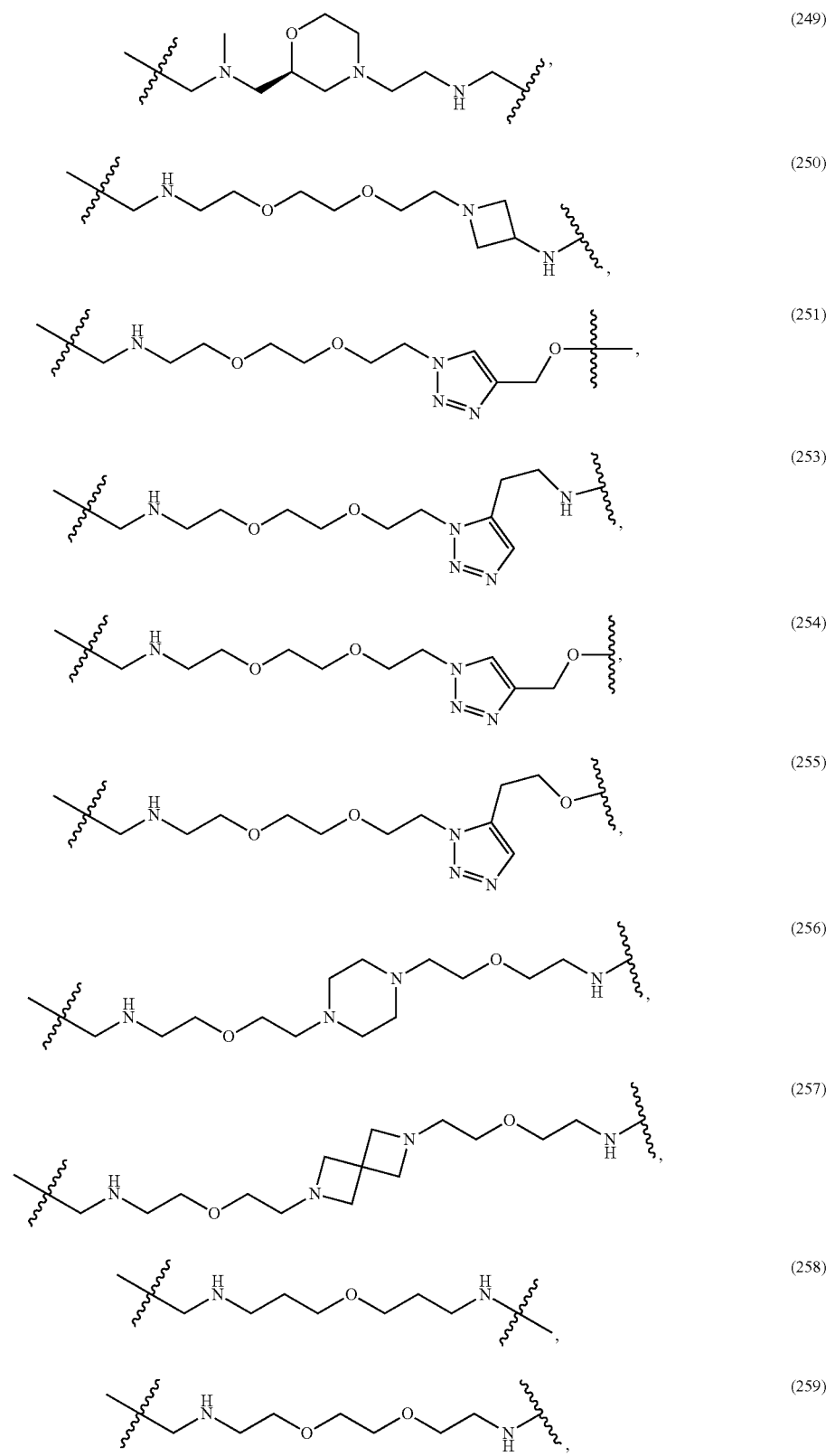

TABLE B-continued
Exemplified Linkers (L)
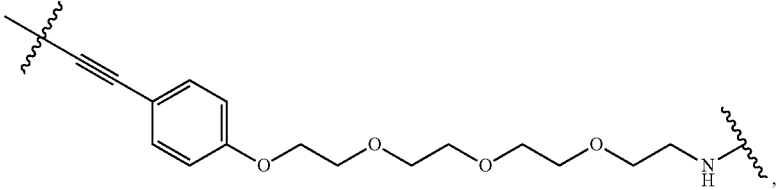 [SMILES: *C#Cc1ccc(OCCOCCOCCOCCN*)cc1] (260)
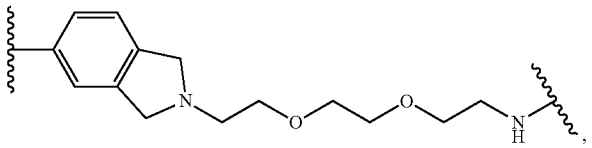 [SMILES: *NCCOCCOCCN1Cc2ccc(*)cc2C1] (261)
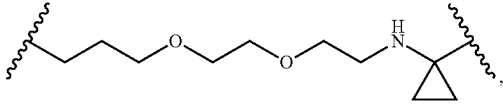 [SMILES: *CCCOCCOCCNC1(*)CC1] (262)
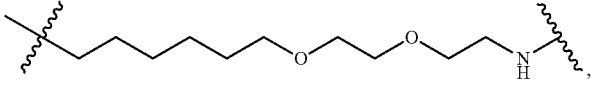 [SMILES: *CCCCCCOCCOCCN*] (263)
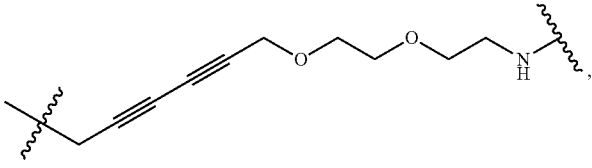 [SMILES: *CC#CC#CCOCCOCCN*] (264)
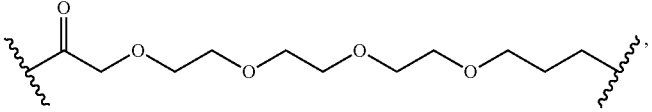 [SMILES: *CCCOCCOCCOCCOCC(*)=O] (265)
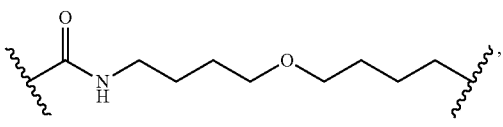 [SMILES: *CCCCOCCCCNC(*)=O] (266)
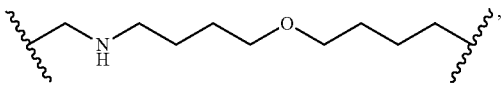 [SMILES: *CCCCOCCCCNC*] (267)
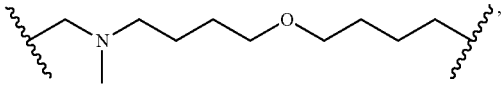 [SMILES: *CCCCOCCCCN(C)C*] (268)
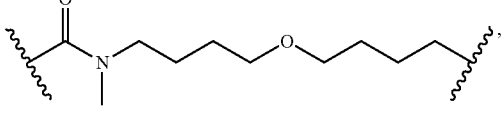 (269)
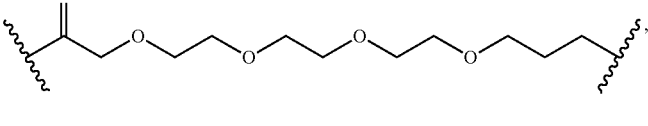 (270)

TABLE B-continued

Exemplified Linkers (L)

TABLE B-continued
Exemplified Linkers (L)
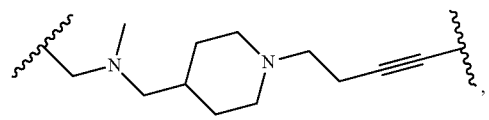 [SMILES: *C#CCCN1CCC(CN(C)C*)CC1] (284)
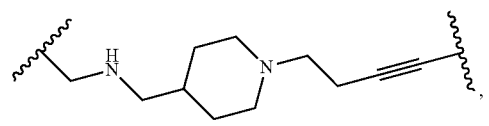 [SMILES: *C#CCCN1CCC(CNC*)CC1] (285)
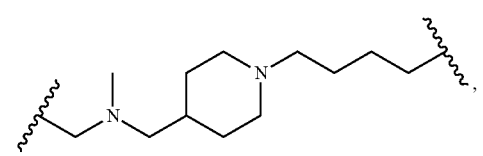 [SMILES: *CCCCN1CCC(CN(C)C*)CC1] (286)
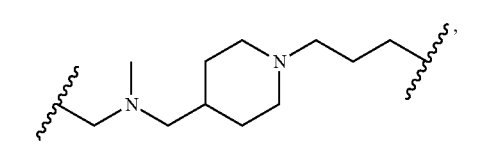 [SMILES: *CCCN1CCC(CN(C)C*)CC1] (287)
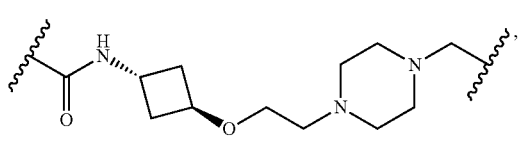 [SMILES: *CN1CCN(CCO[C@H]2C[C@H](NC(*)=O)C2)CC1] (288)
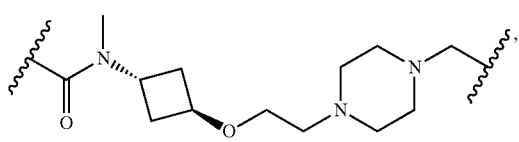 [SMILES: *CN1CCN(CCO[C@H]2C[C@H](N(C)C(*)=O)C2)CC1] (289)
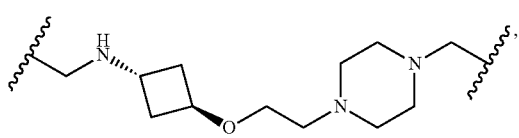 [SMILES: *CN[C@H]1C[C@H](OCCN2CCN(C*)CC2)C1] (290)
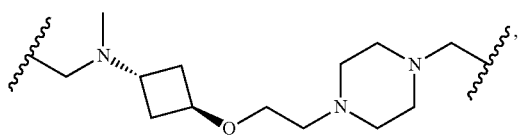 [SMILES: *CN1CCN(CCO[C@H]2C[C@H](N(C)C*)C2)CC1] (291)
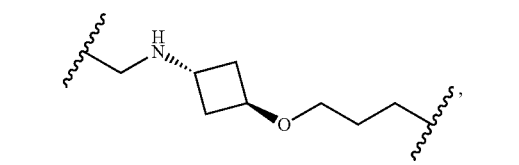 [SMILES: *CCCO[C@H]1C[C@H](NC*)C1] (292)
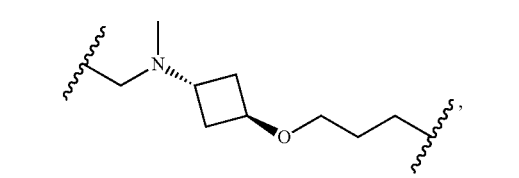 [SMILES: *CCCO[C@H]1C[C@H](N(C)C*)C1] (293)

TABLE B-continued
Exemplified Linkers (L)
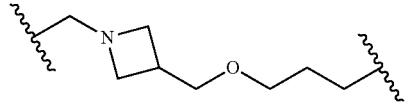 (294)
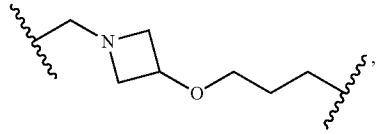 [SMILES: *CCCOC1CN(C*)C1] (295)
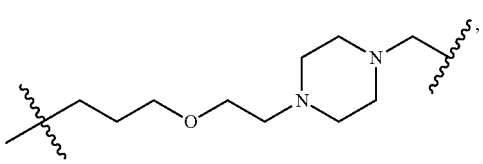 [SMILES: *CCCOCCN1CCN(C*)CC1] (296)
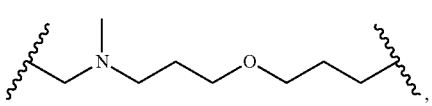 (297)
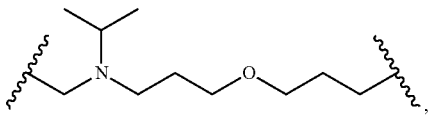 [SMILES: *CCCOCCCN(C*)C(C)C] (298)
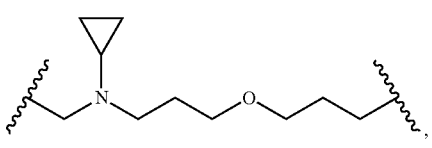 [SMILES: *CCCOCCCN(C*)C1CC1] (299)
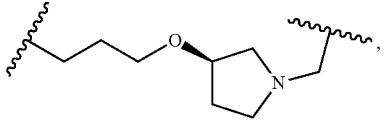 [SMILES: *CCCO[C@@H]1CCN(C*)C1] (300)
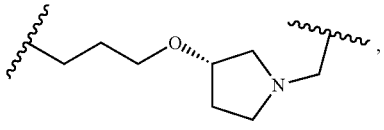 [SMILES: *CCCO[C@H]1CCN(C*)C1] (301)
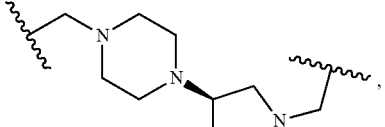 (302)
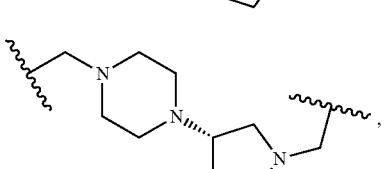 (303)
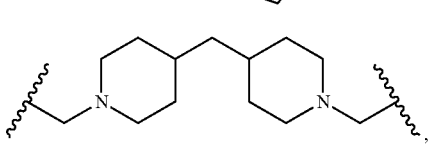 (304)

TABLE B-continued
Exemplified Linkers (L)
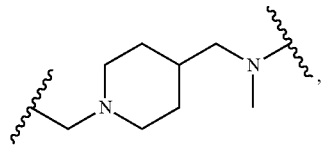 [SMILES: *CN1CCC(CN(*)C)CC1] (305)
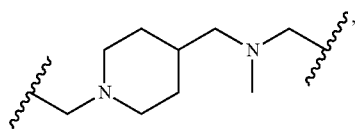 [SMILES: *CN(C)CC1CCN(C*)CC1] (306)
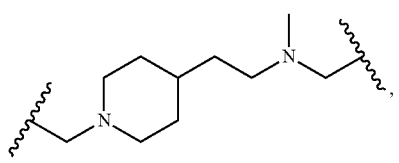 [SMILES: *CN(C)CCC1CCN(C*)CC1] (307)
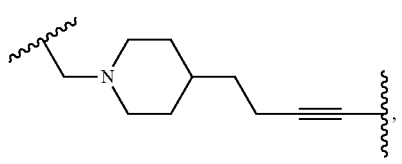 [SMILES: *C#CCCC1CCN(C*)CC1] (308)
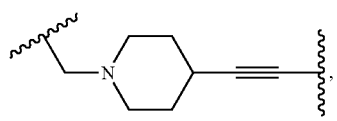 [SMILES: *C#CC1CCN(C*)CC1] (309)
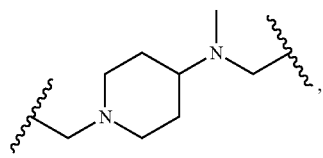 [SMILES: *CN1CCC(N(C)C*)CC1] (310)
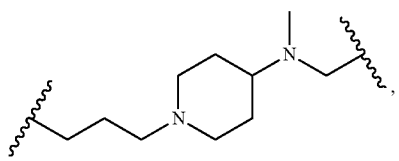 [SMILES: *CCCN1CCC(N(C)C*)CC1] (311)
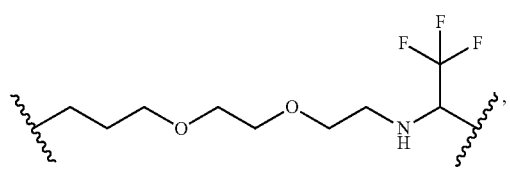 [SMILES: *CCCOCCOCCNC(*)C(F)(F)F] (312)
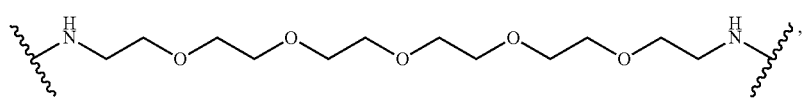 [SMILES: *NCCOCCOCCOCCOCCOCCN*] (313)
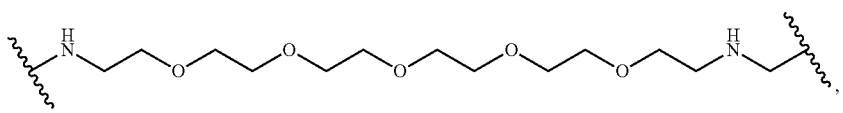 [SMILES: *CNCCOCCOCCOCCOCCOCCN*] (314)

TABLE B-continued
Exemplified Linkers (L)
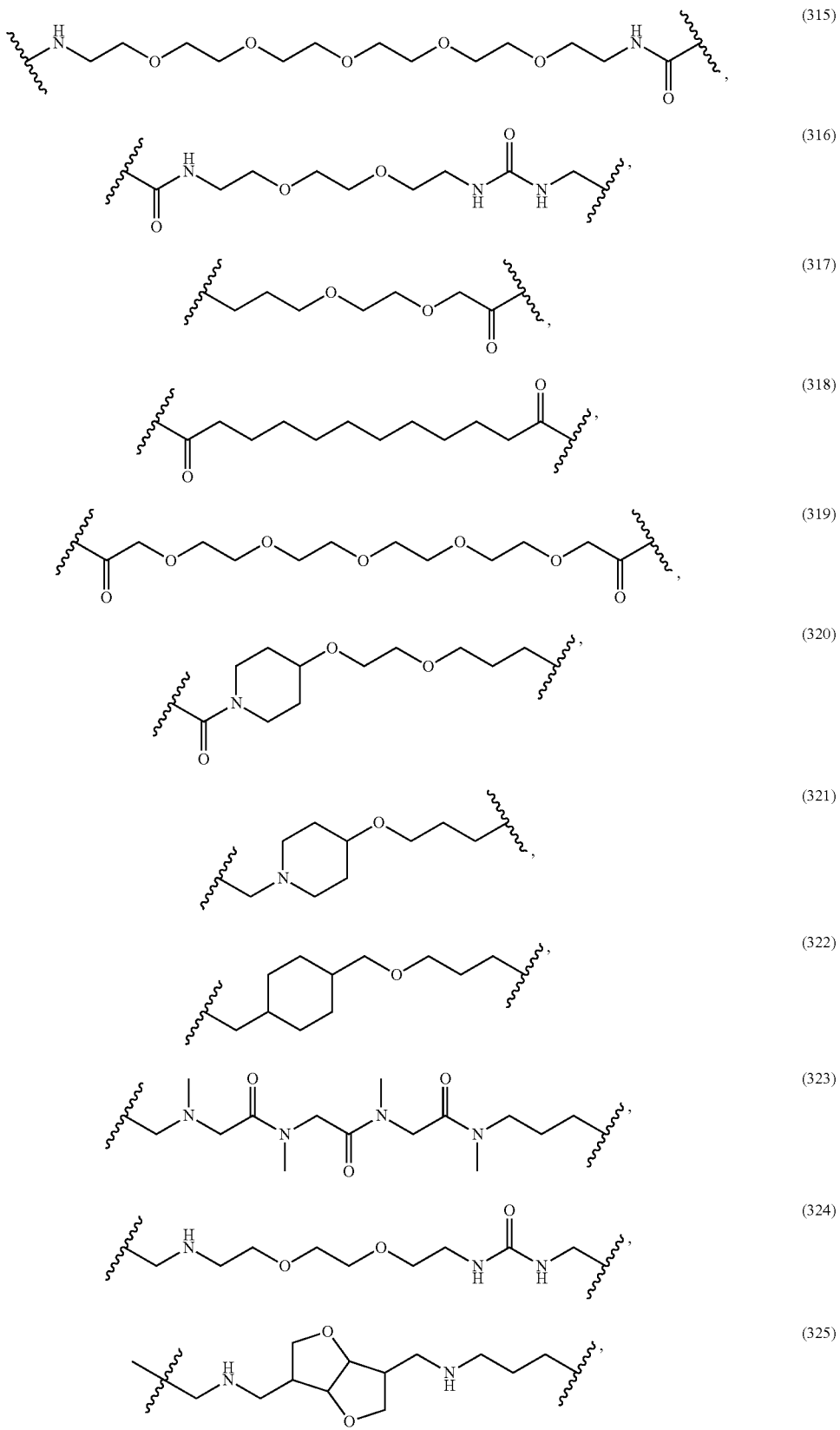

TABLE B-continued

Exemplified Linkers (L)

TABLE B-continued

Exemplified Linkers (L)

(339)

(340)

(341)

(342)

(343)

(344)

(345)

(346)

(347)

(348)

TABLE B-continued
Exemplified Linkers (L)
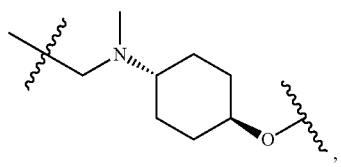 [SMILES: *CN(C)[C@H]1CC[C@H](O*)CC1] (349)
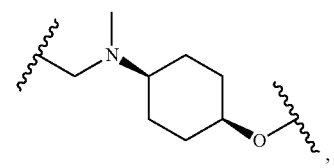 [SMILES: *CN(C)[C@H]1CC[C@@H](O*)CC1] (350)
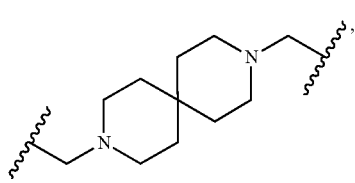 [SMILES: *CN1CCC2(CC1)CCN(C*)CC2] (351)
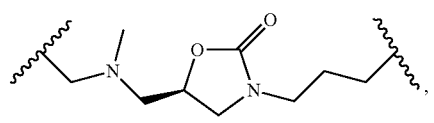 [SMILES: *CCCN1C[C@@H](CN(C)C*)OC1=O] (352)
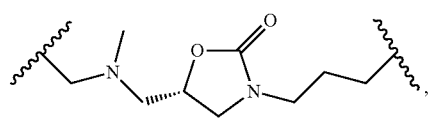 [SMILES: *CCCN1C[C@H](CN(C)C*)OC1=O] (353)
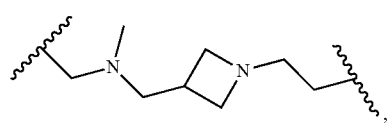 [SMILES: *CCN1CC(CN(C)C*)C1] (354)
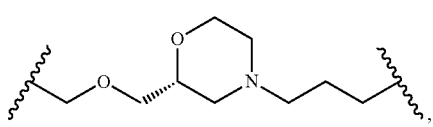 (355)
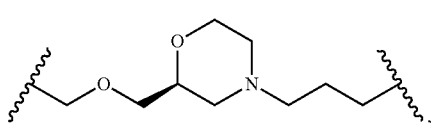 (356)
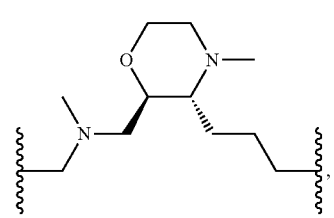 [SMILES: *CCC[C@@H]1[C@@H](CN(C)C*)OCCN1C] (357)

TABLE B-continued
Exemplified Linkers (L)
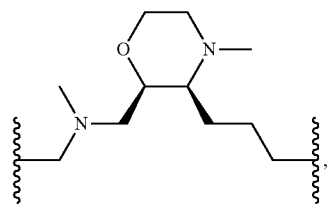 [SMILES: *CCC[C@H]1[C@@H](CN(C)C*)OCCN1C]  (358)
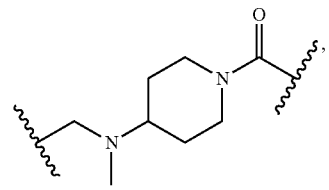 [SMILES: *CN(C)C1CCN(C(*)=O)CC1]  (359)
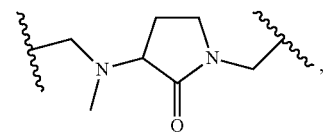 [SMILES: *CN1CCC(N(C)C*)C1=O]  (360)
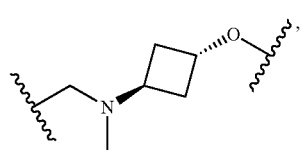 [SMILES: *CN(C)[C@H]1C[C@H](O*)C1]  (361)
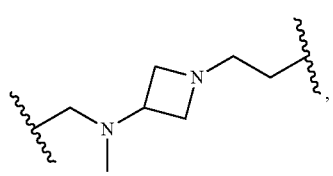 [SMILES: *CCN1CC(N(C)C*)C1]  (362)
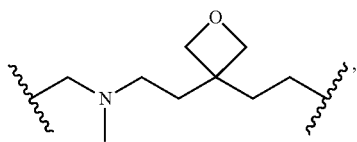 [SMILES: *CCC1(CCN(C)C*)COC1]  (363)
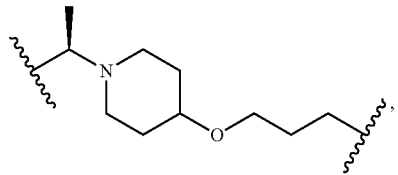 [SMILES: *CCCOC1CCN([C@@H](*)C)CC1]  (364)
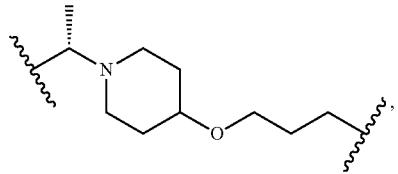 [SMILES: *CCCOC1CCN([C@H](*)C)CC1]  (365)
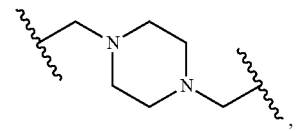 [SMILES: *CN1CCN(C*)CC1]  (366)

TABLE B-continued

Exemplified Linkers (L)

(367), (368), (369), (370), (371), (372), (373), (374), (375), (376), (377)

TABLE B-continued
Exemplified Linkers (L)
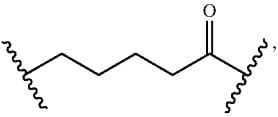 [SMILES: *CCCCC(*)=O] (378)
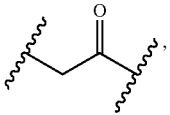 [SMILES: *CC(*)=O] (379)
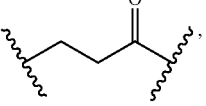 (380)
 (381)
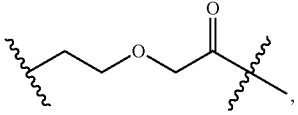 [SMILES: *CCOCC(*)=O] (382)
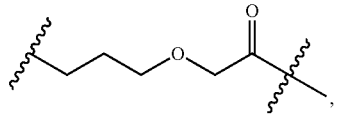 [SMILES: *CCCOCC(*)=O] (383)
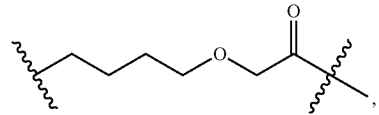 [SMILES: *CCCCOCC(*)=O] (384)
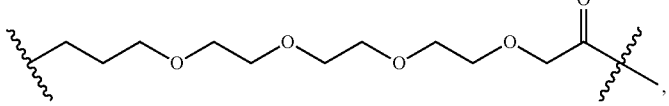 (385)
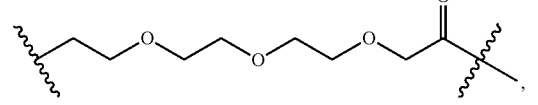 (386)
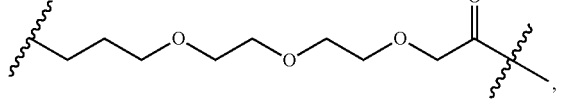 (387)
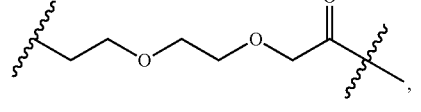 (388)
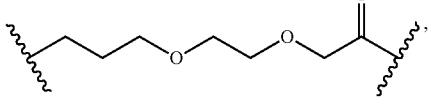 (389)

TABLE B-continued
Exemplified Linkers (L)
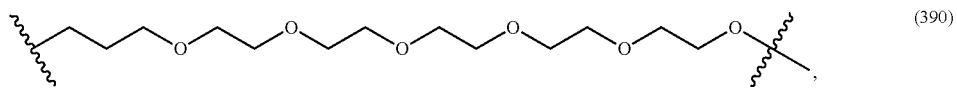 (390)
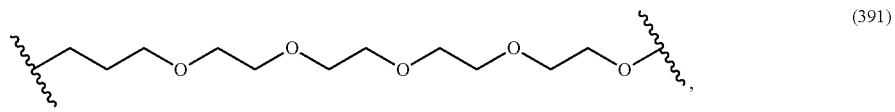 (391)
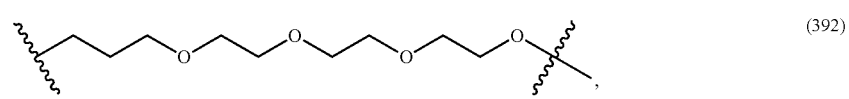 (392)
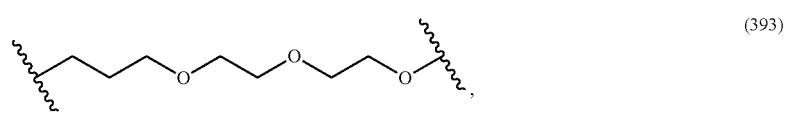 (393)
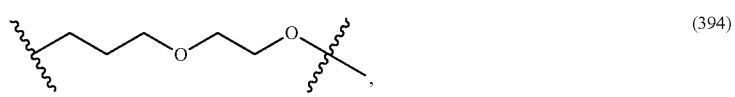 (394)
 (395)
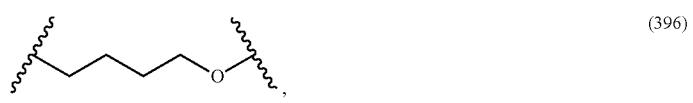 (396)
 (397)
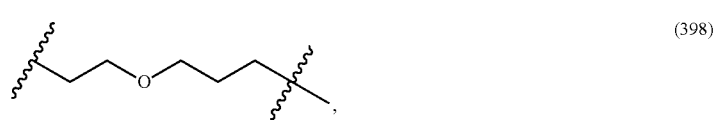 (398)
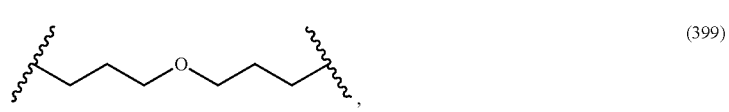 (399)
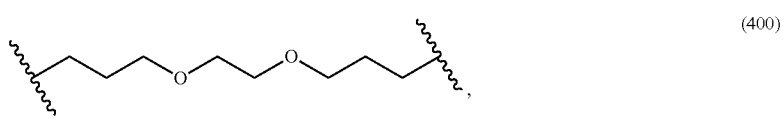 (400)
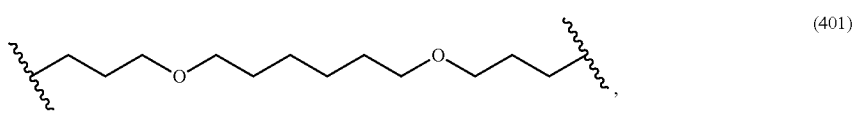 (401)
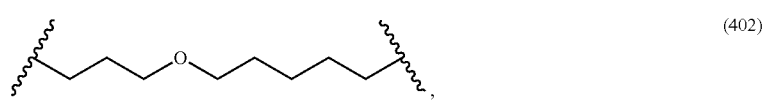 (402)
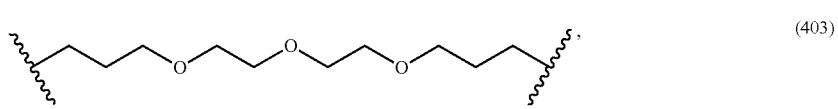 (403)

TABLE B-continued
Exemplified Linkers (L)
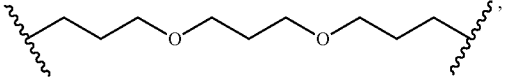 [SMILES: *CCCOCCCOCCC*] (404)
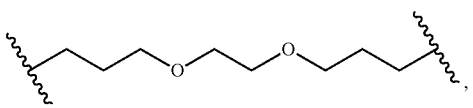 [SMILES: *CCCOCCOCCC*] (405)
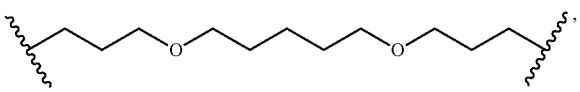 [SMILES: *CCCOCCCCCOCCC*] (406)
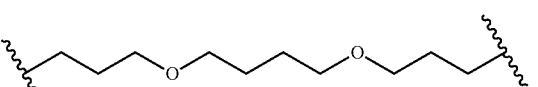 (407)
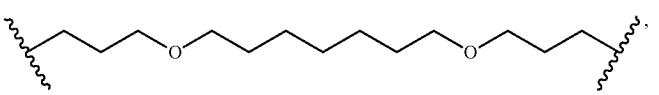 [SMILES: *CCCOCCCCCCCOCCC*] (408)
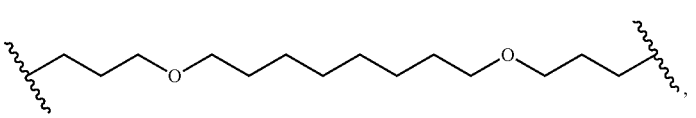 [SMILES: *CCCOCCCCCCCCOCCC*] (409)
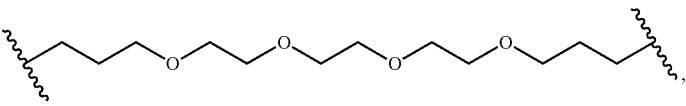 [SMILES: *CCCOCCOCCOCCOCCC*] (410)
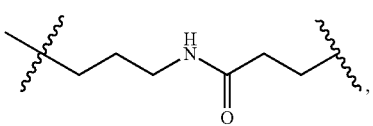 [SMILES: *CCCNC(=O)CC*] (411)
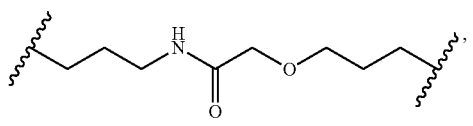 [SMILES: *CCCNC(=O)COCCC*] (412)
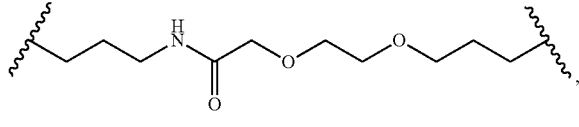 [SMILES: *CCCNC(=O)COCCOCCC*] (413)
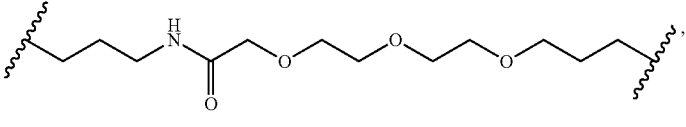 [SMILES: *CCCNC(=O)COCCOCCOCCC*] (414)
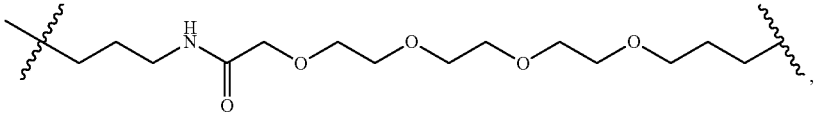 [SMILES: *CCCNC(=O)COCCOCCOCCOCCC*] (415)

TABLE B-continued
Exemplified Linkers (L)
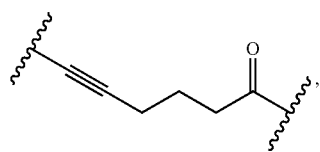 [SMILES: *C#CCCCC(*)=O]
(416)
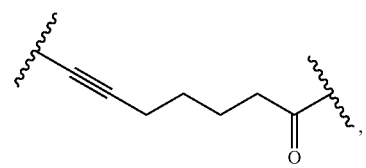 [SMILES: *C#CCCCCC(*)=O]
(417)
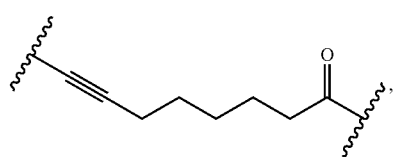 [SMILES: *C#CCCCCCC(*)=O]
(418)
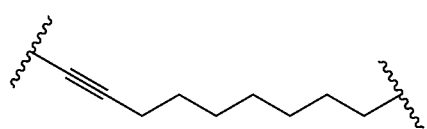 [SMILES: *C#CCCCCCCC*]
(419)
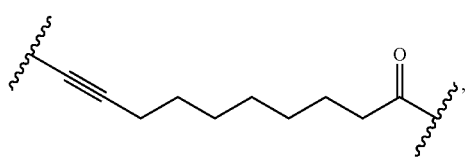 [SMILES: *C#CCCCCCCCC(*)=O]
(420)
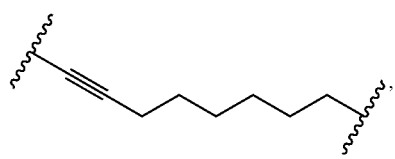 [SMILES: *C#CCCCCCC*]
(421)
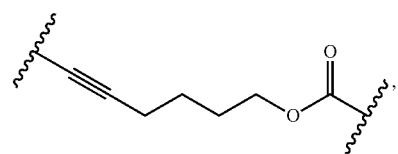 [SMILES: *C#CCCCCOC(*)=O]
(422)
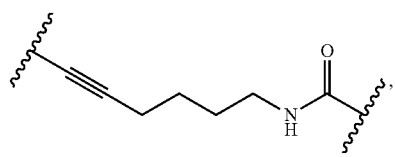 [SMILES: *C#CCCCCNC(*)=O]
(423)
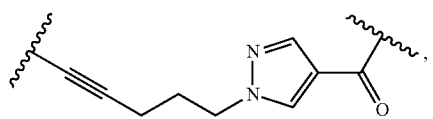 [SMILES: *C#CCCCn1cc(C(*)=O)cn1]
(424)
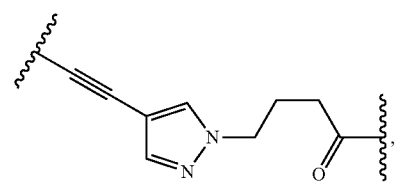 [SMILES: *C#Cc1cnn(CCCC(*)=O)c1]
(425)

TABLE B-continued
Exemplified Linkers (L)
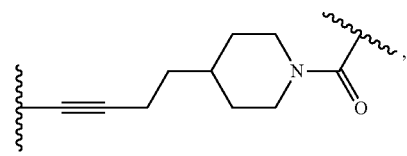 [SMILES: *C#CCCC1CCN(C(*)=O)CC1] (426)
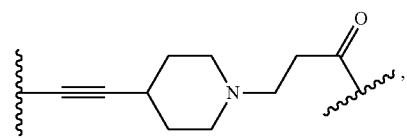 [SMILES: *C#CC1CCN(CCC(*)=O)CC1] (427)
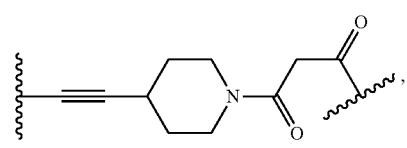 [SMILES: *C#CC1CCN(C(=O)CC(*)=O)CC1] (428)
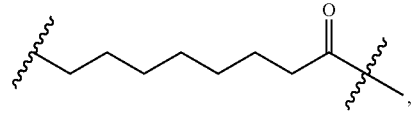 [SMILES: *CCCCCCCC(*)=O] (429)
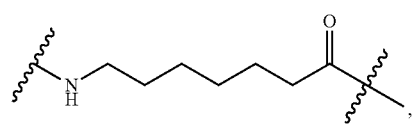 [SMILES: *NCCCCCCC(*)=O] (430)
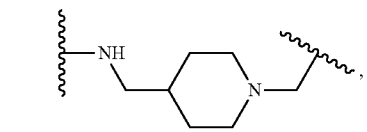 [SMILES: *CN1CCC(CN*)CC1] (431)
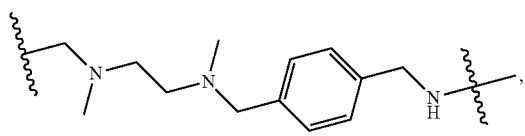 [SMILES: *CN(C)CCN(C)Cc1ccc(CN*)cc1] (432)
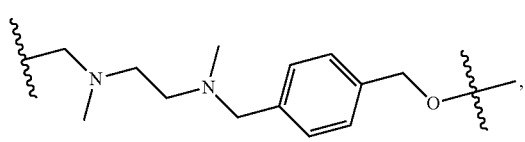 [SMILES: *CN(C)CCN(C)Cc1ccc(CO*)cc1] (433)
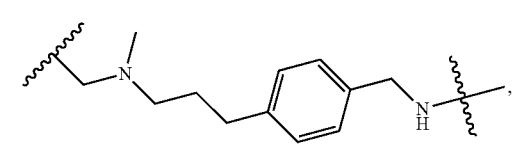 [SMILES: *CN(C)CCCc1ccc(CN*)cc1] (434)
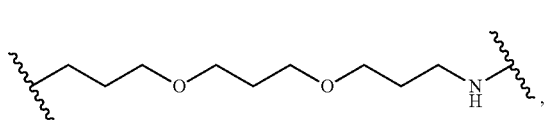 [SMILES: *CCCOCCCOCCCN*] (435)
 (436)

TABLE B-continued

Exemplified Linkers (L)

(437)

(438)

(438)

(439)

(440)

(441)

(442)

(443)

(444)

(445)

(446)

TABLE B-continued

Exemplified Linkers (L)

TABLE B-continued
Exemplified Linkers (L)
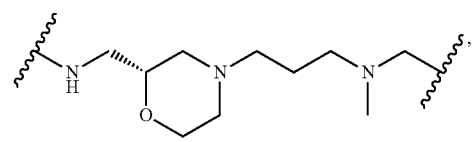 [SMILES: *CN(C)CCCN1CCO[C@H](CN*)C1] (458)
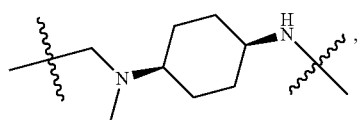 [SMILES: *CN(C)[C@H]1CC[C@@H](N*)CC1] (459)
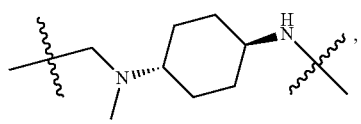 [SMILES: *CN(C)[C@H]1CC[C@H](N*)CC1] (460)
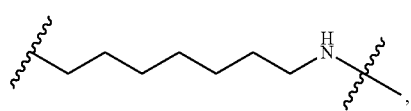 [SMILES: *CCCCCCCN*] (461)
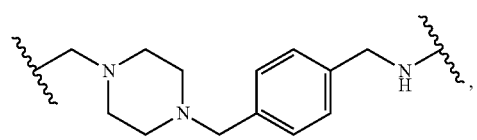 [SMILES: *CN1CCN(Cc2ccc(CN*)cc2)CC1] (462)
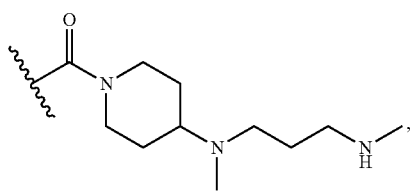 (463)
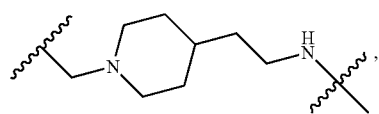 [SMILES: *CN1CCC(CCN*)CC1] (464)
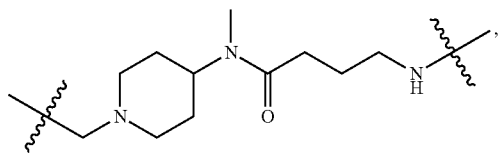 [SMILES: *CN1CCC(N(C)C(=O)CCCN*)CC1] (465)
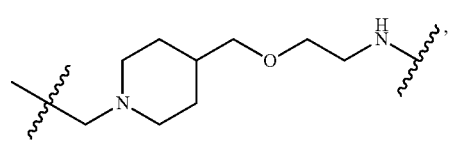 [SMILES: *CN1CCC(COCCN*)CC1] (466)
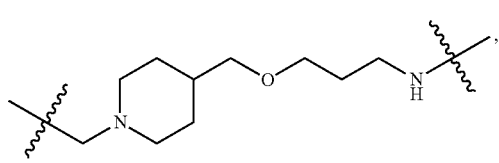 [SMILES: *CN1CCC(COCCCN*)CC1] (467)

TABLE B-continued
Exemplified Linkers (L)
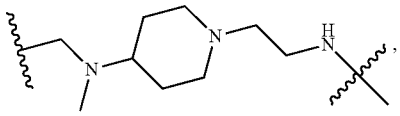 [SMILES: *CN(C)C1CCN(CCN*)CC1] (468)
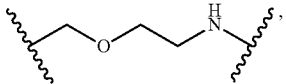 [SMILES: *COCCN*] (469)
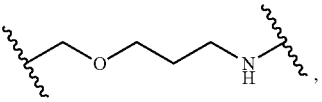 [SMILES: *COCCCN*] (470)
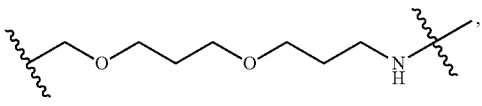 [SMILES: *COCCCOCCCN*] (471)
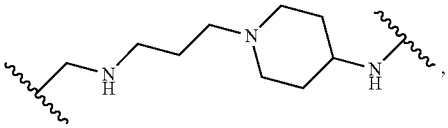 [SMILES: *CNCCCN1CCC(N*)CC1] (472)
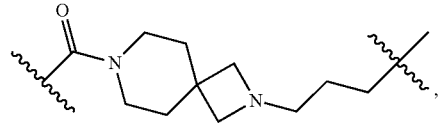 [SMILES: *CCCN1CC2(CCN(C(*)=O)CC2)C1] (473)
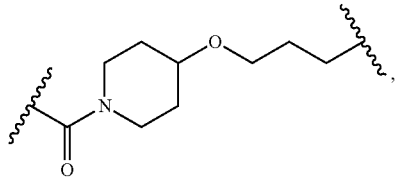 [SMILES: *CCCOC1CCN(C(*)=O)CC1] (474)
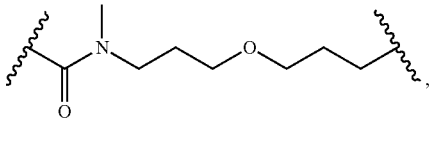 [SMILES: *CCCOCCCN(C)C(*)=O] (475)
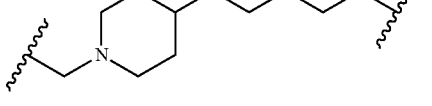 (475)
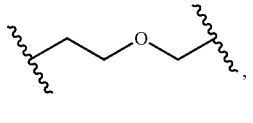 [SMILES: *CCOC*] (476)
 (477)

TABLE B-continued
Exemplified Linkers (L)
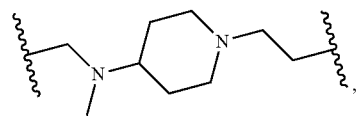 [SMILES: *CCN1CCC(N(C)C*)CC1] (478)
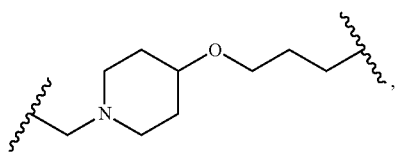 [SMILES: *CCCOC1CCN(C*)CC1] (489)
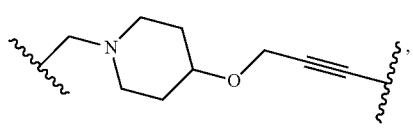 [SMILES: *C#CCOC1CCN(C*)CC1] (480)
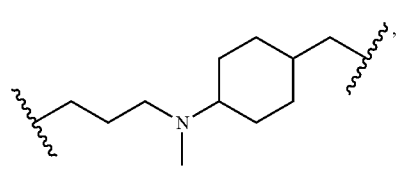 [SMILES: *CCCN(C)C1CCC(C*)CC1] (481)
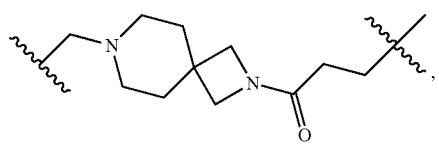 [SMILES: *CCC(=O)N1CC2(CCN(C*)CC2)C1] (482)
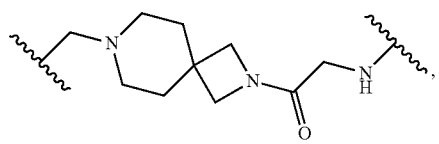 [SMILES: *CN1CCC2(CC1)CN(C(=O)CN*)C2] (483)
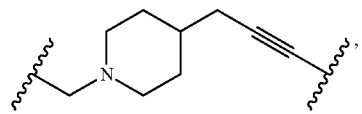 [SMILES: *C#CCC1CCN(C*)CC1] (484)
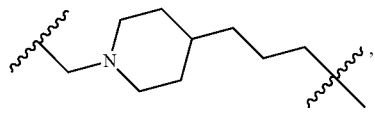 [SMILES: *CCCC1CCN(C*)CC1] (485)
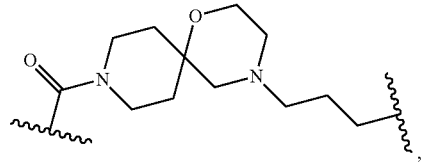 [SMILES: *CCCN1CCOC2(CCN(C(*)=O)CC2)C1] (486)
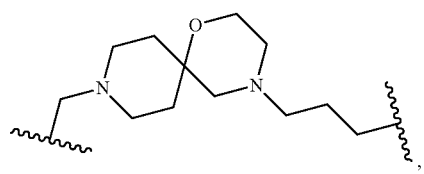 [SMILES: *CCCN1CCOC2(CCN(C*)CC2)C1] (487)

TABLE B-continued
Exemplified Linkers (L)
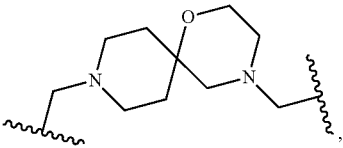 [SMILES: *CN1CCC2(CC1)CN(C*)CCO2]
(488)
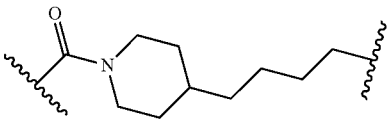
(489)
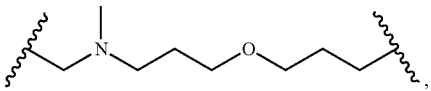
(490)
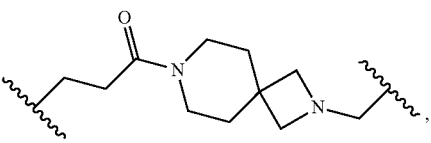 [SMILES: *CCC(=O)N1CCC2(CC1)CN(C*)C2]
(491)
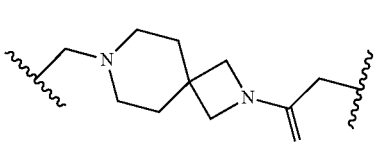
(492)
(493)
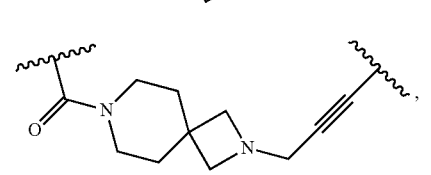
(494)
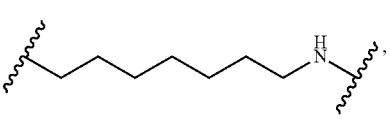
(495)
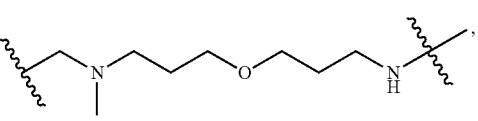 [SMILES: *CN(C)CCCOCCCN*]
(496)
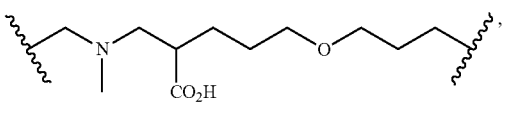
(497)
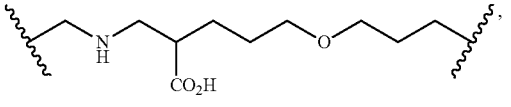 [SMILES: *CCCOCCCC(CNC*)C(=O)O]
(498)

TABLE B-continued
Exemplified Linkers (L)
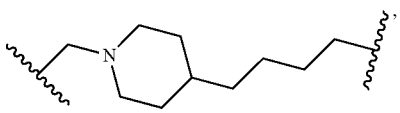 [SMILES: *CCCCC1CCN(C*)CC1] (499)
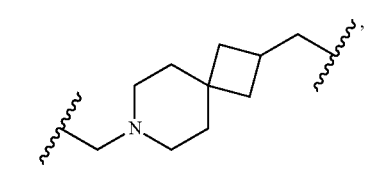 [SMILES: *CC1CC2(CCN(C*)CC2)C1] (500)
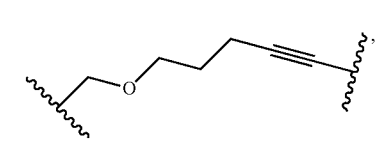 [SMILES: *C#CCCCOC*] (501)
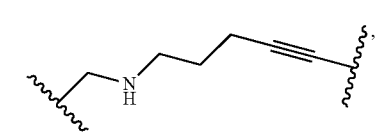 [SMILES: *C#CCCCNC*] (502)
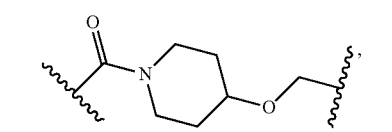 [SMILES: *COC1CCN(C(*)=O)CC1] (503)
 (504)
 (505)
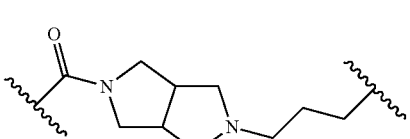 (506)
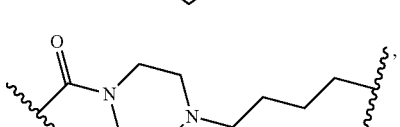 (507)
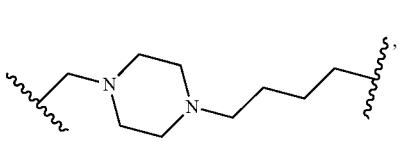 [SMILES: *CCCCN1CCN(C*)CC1] (508)
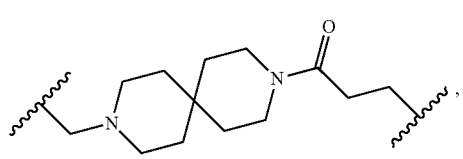 [SMILES: *CCC(=O)N1CCC2(CCN(C*)CC2)CC1] (509)

TABLE B-continued

Exemplified Linkers (L)

(510)

(511)

(512)

(513)

(514)

(515)

(516)

(517)

(518)

(519)

(520)

TABLE B-continued
Exemplified Linkers (L)
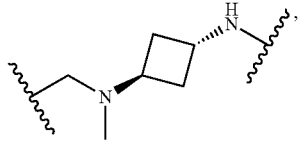 [SMILES: *CN(C)[C@H]1C[C@H](N*)C1] (521)
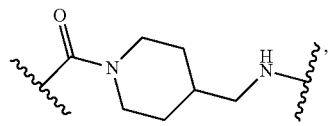 [SMILES: *NCC1CCN(C(*)=O)CC1] (522)
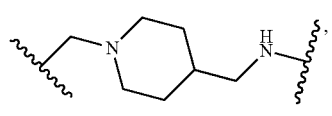 [SMILES: *CN1CCC(CN*)CC1] (523)
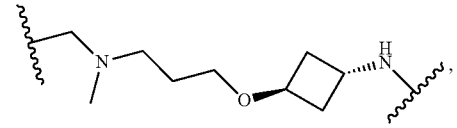 [SMILES: *CN(C)CCCO[C@H]1C[C@H](N*)C1] (524)
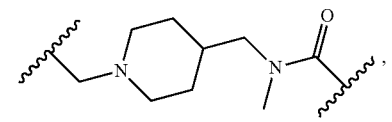 [SMILES: *CN1CCC(CN(C)C(*)=O)CC1] (525)
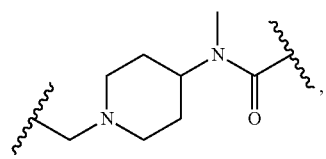 [SMILES: *CN1CCC(N(C)C(*)=O)CC1] (526)
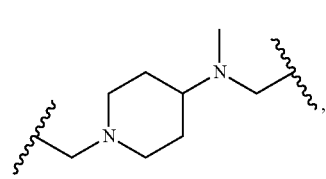 [SMILES: *CN1CCC(N(C)C*)CC1] (527)
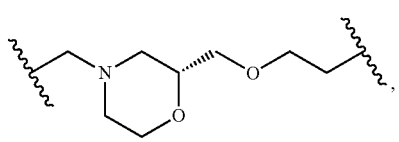 [SMILES: *CCOC[C@H]1CN(C*)CCO1] (528)
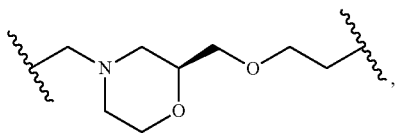 [SMILES: *CCOC[C@@H]1CN(C*)CCO1] (529)
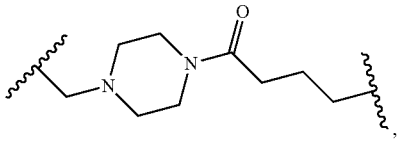 [SMILES: *CCCC(=O)N1CCN(C*)CC1] (530)
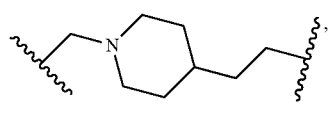 [SMILES: *CCC1CCN(C*)CC1] (531)

TABLE B-continued
Exemplified Linkers (L)
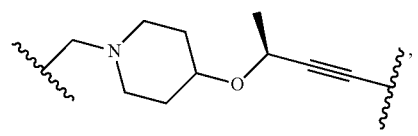 [SMILES: *C#C[C@H](C)OC1CCN(C*)CC1] (532)
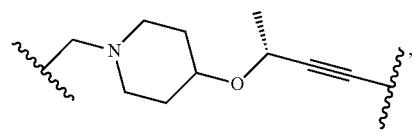 [SMILES: *C#C[C@@H](C)OC1CCN(C*)CC1] (533)
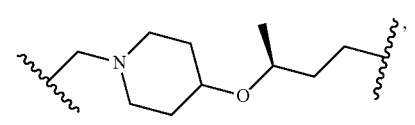 [SMILES: *CC[C@H](C)OC1CCN(C*)CC1] (534)
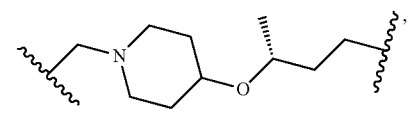 [SMILES: *CC[C@@H](C)OC1CCN(C*)CC1] (535)
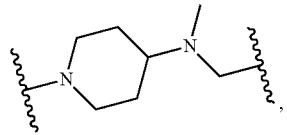 [SMILES: *CN(C)C1CCN(*)CC1] (536)
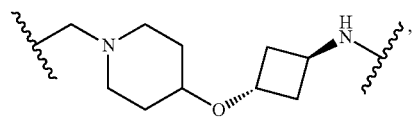 [SMILES: *CN1CCC(O[C@H]2C[C@H](N*)C2)CC1] (537)
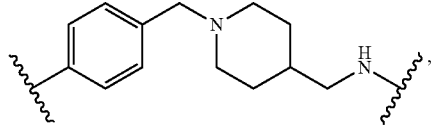 [SMILES: *NCC1CCN(Cc2ccc(*)cc2)CC1] (538)
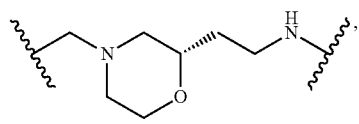 [SMILES: *CN1CCO[C@@H](CCN*)C1] (539)
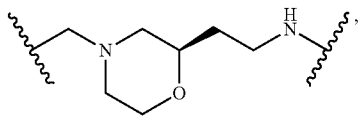 (540)
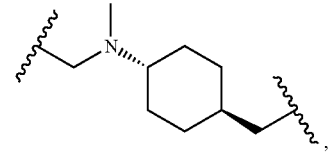 [SMILES: *CN(C)[C@H]1CC[C@H](C*)CC1] (541)
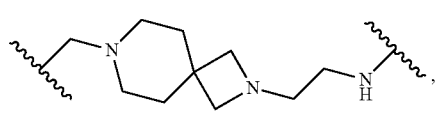 [SMILES: *CN1CCC2(CC1)CN(CCN*)C2] (542)

TABLE B-continued
Exemplified Linkers (L)
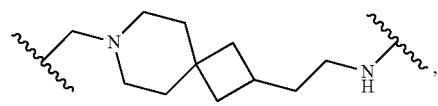 [SMILES: *CN1CCC2(CC1)CC(CCN*)C2] (543)
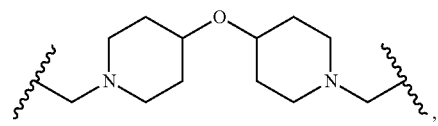 [SMILES: *CN1CCC(OC2CCN(C*)CC2)CC1] (544)
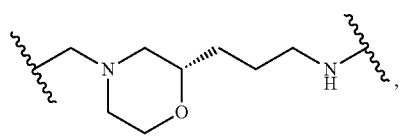 [SMILES: *CN1CCO[C@@H](CCCN*)C1] (545)
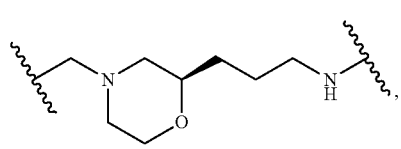 [SMILES: *CN1CCO[C@H](CCCN*)C1] (546)
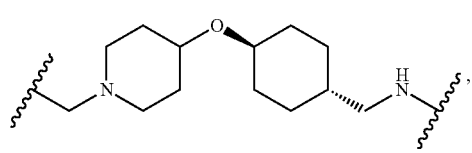 [SMILES: *CN1CCC(O[C@H]2CC[C@H](CN*)CC2)CC1] (547)
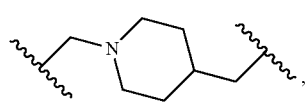 [SMILES: *CC1CCN(C*)CC1] (548)
 (549)
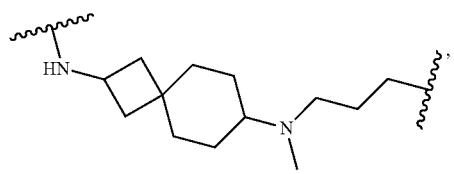 [SMILES: *CCCN(C)C1CCC2(CC1)CC(N*)C2] (550)
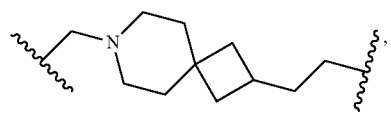 [SMILES: *CCC1CC2(CCN(C*)CC2)C1] (551)
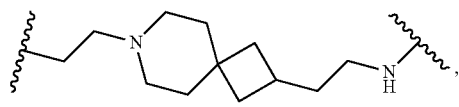 [SMILES: *CCN1CCC2(CC1)CC(CCN*)C2] (552)
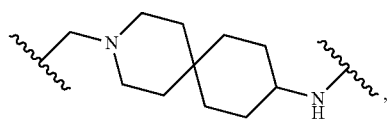 [SMILES: *CN1CCC2(CCC(N*)CC2)CC1] (553)

TABLE B-continued

Exemplified Linkers (L)

TABLE B-continued

Exemplified Linkers (L)

(566), (567), (568), (569), (570), (571), (572), (573), (574), (575), (576), (577)

TABLE B-continued
Exemplified Linkers (L)
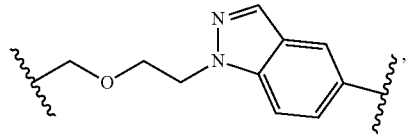 [SMILES: *COCCn1ncc2cc(*)ccc21]
(578)
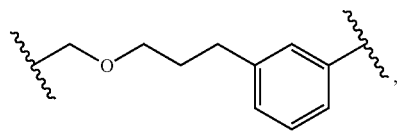 [SMILES: *COCCCc1cccc(*)c1]
(579)
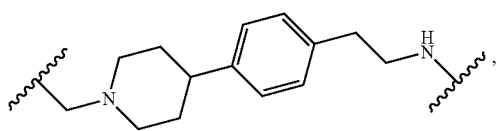 [SMILES: *CN1CCC(c2ccc(CCN*)cc2)CC1]
(580)
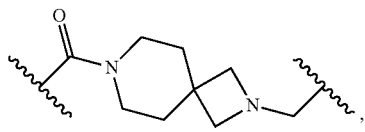 [SMILES: *CN1CC2(CCN(C(*)=O)CC2)C1]
(581)
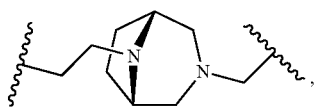 [SMILES: *CCN1[C@@H]2CC[C@H]1CN(C*)C2]
(582)
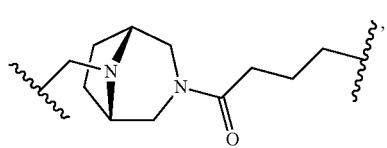 [SMILES: *CCCC(=O)N1C[C@H]2CC[C@@H](C1)N2C*]
(583)
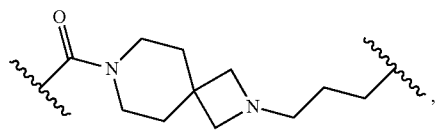 [SMILES: *CCCN1CC2(CCN(C(*)=O)CC2)C1]
(584)
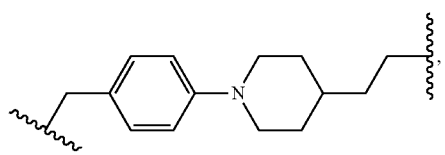 [SMILES: *CCC1CCN(c2ccc(C*)cc2)CC1]
(585)
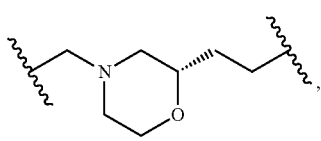 [SMILES: *CC[C@H]1CN(C*)CCO1]
(586)
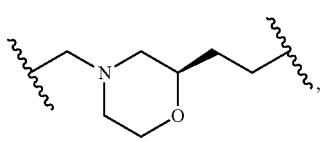 [SMILES: *CC[C@@H]1CN(C*)CCO1]
(587)

TABLE B-continued
Exemplified Linkers (L)
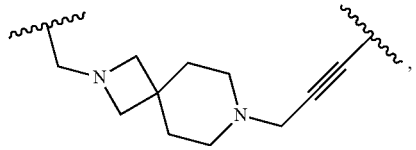 [SMILES: *C#CCN1CCC2(CC1)CN(C*)C2] (588)
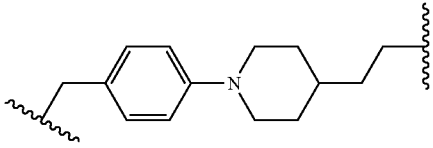 (589)
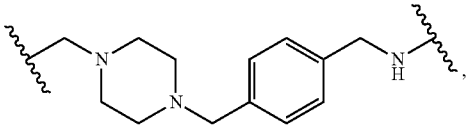 [SMILES: *CN1CCN(Cc2ccc(CN*)cc2)CC1] (590)
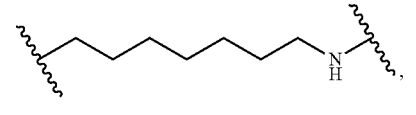 [SMILES: *CCCCCCCN*] (591)
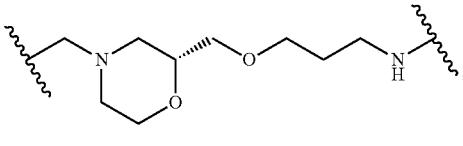 (592)
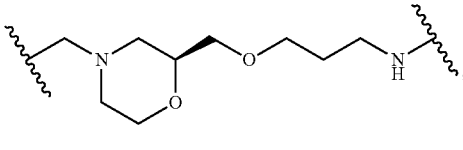 (593)
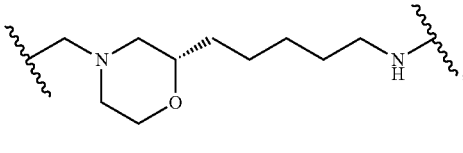 (594)
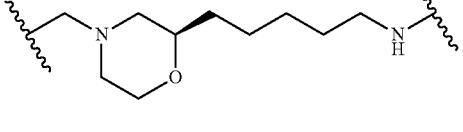 (595)
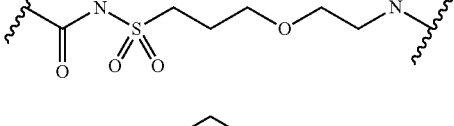 (596)
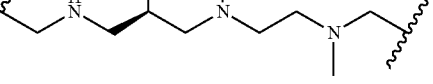 (597)

TABLE B-continued
Exemplified Linkers (L)
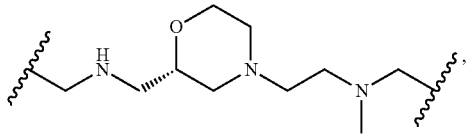 [SMILES: *CNC[C@H]1CN(CCN(C)C*)CCO1] (598)
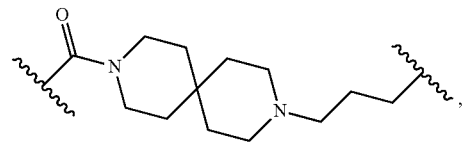 [SMILES: *CCCN1CCC2(CC1)CCN(C(*)=O)CC2] (599)
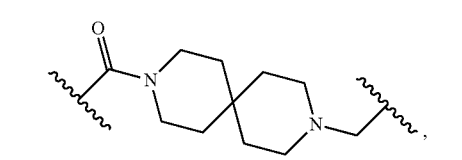 [SMILES: *CN1CCC2(CC1)CCN(C(*)=O)CC2] (600)
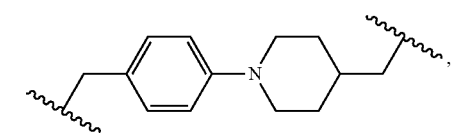 [SMILES: *Cc1ccc(N2CCC(C*)CC2)cc1] (601)
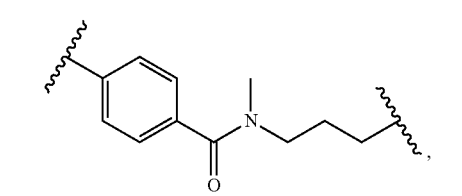 [SMILES: *CCCN(C)C(=O)c1ccc(*)cc1] (602)
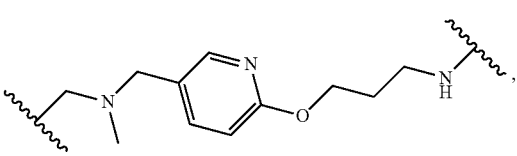 [SMILES: *CN(C)Cc1ccc(OCCCN*)nc1] (603)
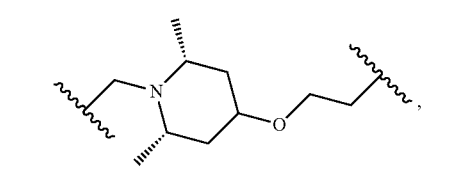 [SMILES: *CCOC1C[C@@H](C)N(C*)[C@@H](C)C1] (604)
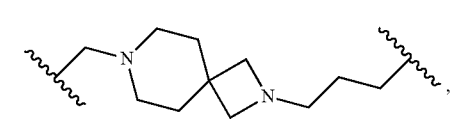 [SMILES: *CCCN1CC2(CCN(C*)CC2)C1] (605)
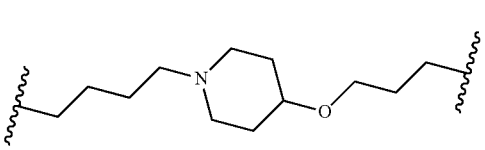 (606)
 (607)

In some embodiments, the present invention provides a compound having an IRAK binding moiety described and disclosed herein, a LBM set forth in Table A above, and a linker set forth in Table B above, or a pharmaceutically acceptable salt thereof.

Exemplary compounds of the invention are set forth in Table 1, below.

TABLE 1

Exemplary Compounds

| I # | Structure |
|---|---|
| I-1 | 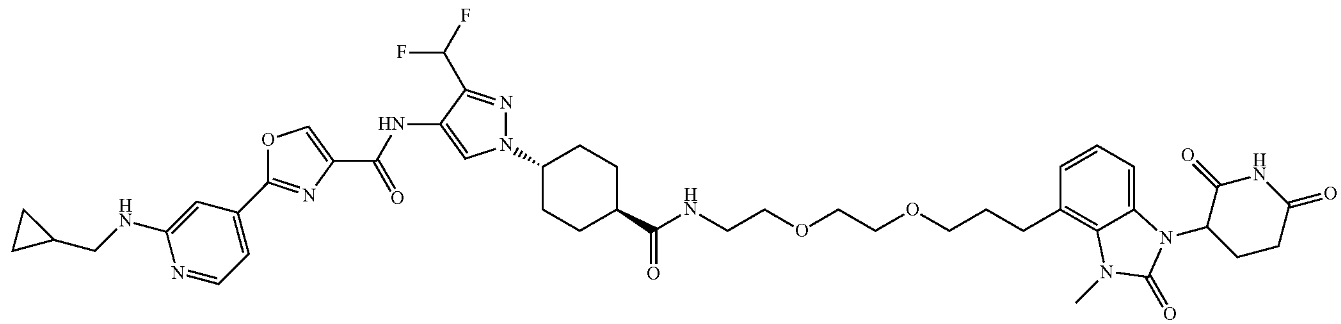 [SMILES: Cn1c(=O)n(C2CCC(=O)NC2=O)c2cccc(CCCOCCOCCNC(=O)[C@H]3CC[C@H](n4cc(NC(=O)c5coc(-c6ccnc(NCC7CC7)c6)n5)c(C(F)F)n4)CC3)c21] |
| I-2 | 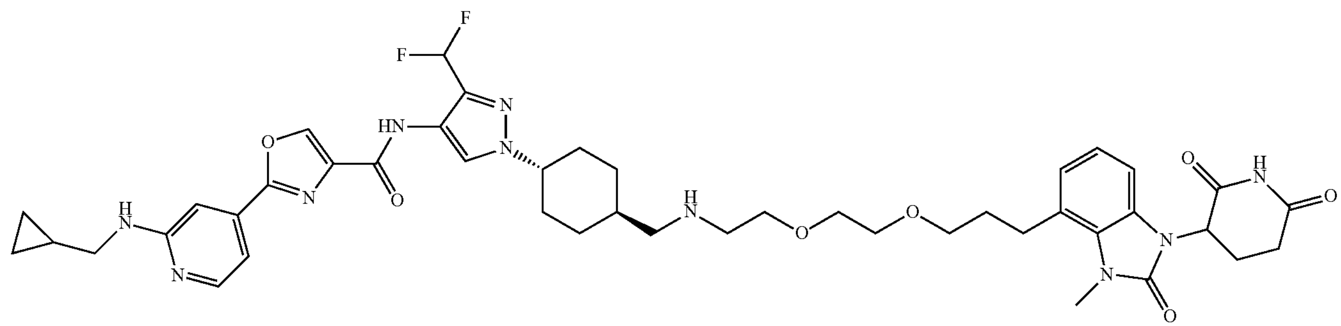 [SMILES: Cn1c(=O)n(C2CCC(=O)NC2=O)c2cccc(CCCOCCOCCNC[C@H]3CC[C@H](n4cc(NC(=O)c5coc(-c6ccnc(NCC7CC7)c6)n5)c(C(F)F)n4)CC3)c21] |
| I-3 | 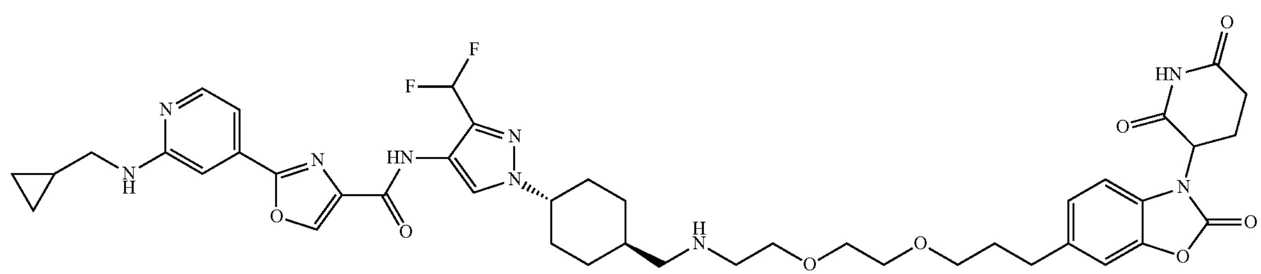 [SMILES: O=C1CCC(n2c(=O)oc3cc(CCCOCCOCCNC[C@H]4CC[C@H](n5cc(NC(=O)c6coc(-c7ccnc(NCC8CC8)c7)n6)c(C(F)F)n5)CC4)ccc32)C(=O)N1] |

TABLE 1-continued
Exemplary Compounds
| I-# | Structure |
|---|---|
| I-5 | 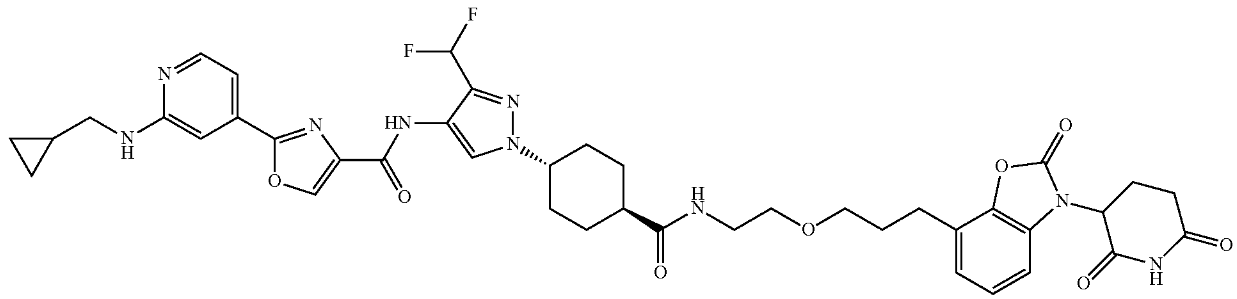 [SMILES: O=C1CCC(n2c(=O)oc3c(CCCOCCNC(=O)[C@H]4CC[C@H](n5cc(NC(=O)c6coc(-c7ccnc(NCC8CC8)c7)n6)c(C(F)F)n5)CC4)cccc32)C(=O)N1] |
| I-6 | 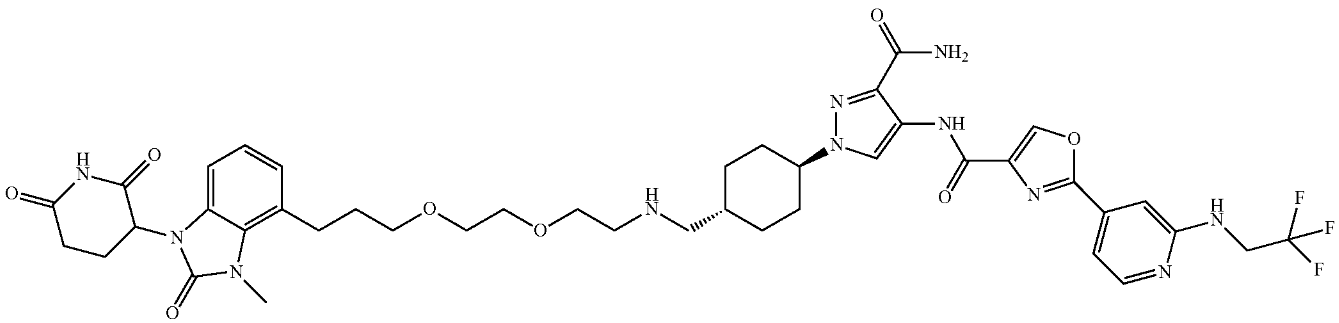 [SMILES: Cn1c(=O)n(C2CCC(=O)NC2=O)c2cccc(CCCOCCOCCNC[C@H]3CC[C@H](n4cc(NC(=O)c5coc(-c6ccnc(NCC(F)(F)F)c6)n5)c(C(N)=O)n4)CC3)c21] |
| I-7 | 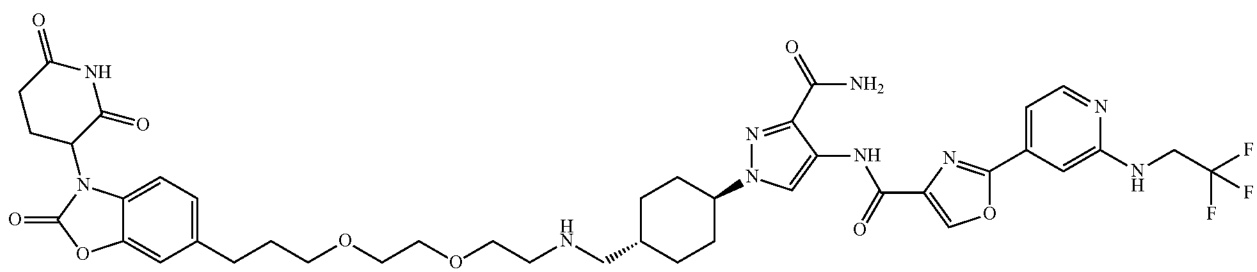 [SMILES: NC(=O)c1nn([C@H]2CC[C@H](CNCCOCCOCCCc3ccc4c(c3)oc(=O)n4C3CCC(=O)NC3=O)CC2)cc1NC(=O)c1coc(-c2ccnc(NCC(F)(F)F)c2)n1] |

TABLE 1-continued
Exemplary Compounds
| I-# | Structure |
|---|---|
| I-8 | 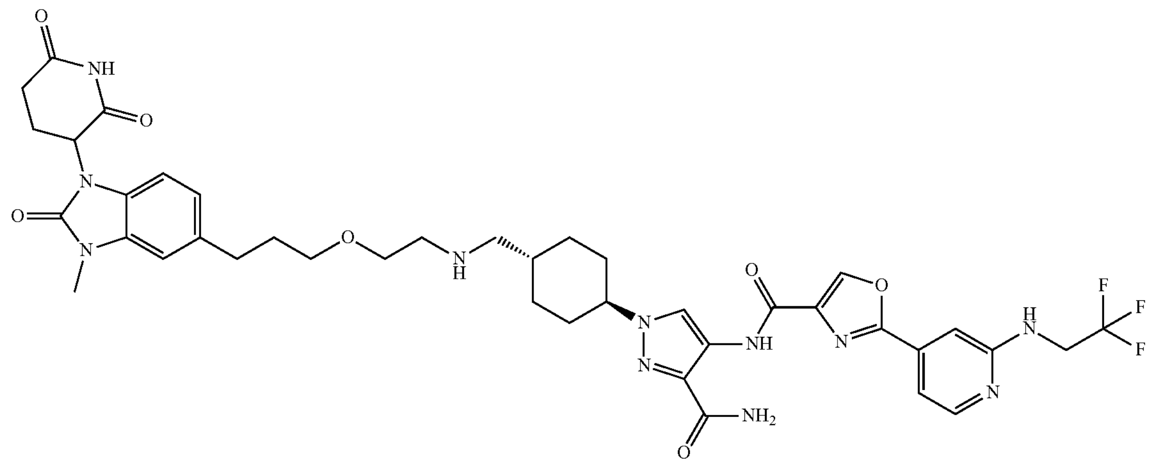 [SMILES: Cn1c(=O)n(C2CCC(=O)NC2=O)c2ccc(CCCOCCNC[C@H]3CC[C@H](n4cc(NC(=O)c5coc(-c6ccnc(NCC(F)(F)F)c6)n5)c(C(N)=O)n4)CC3)cc21] |
| I-9 | 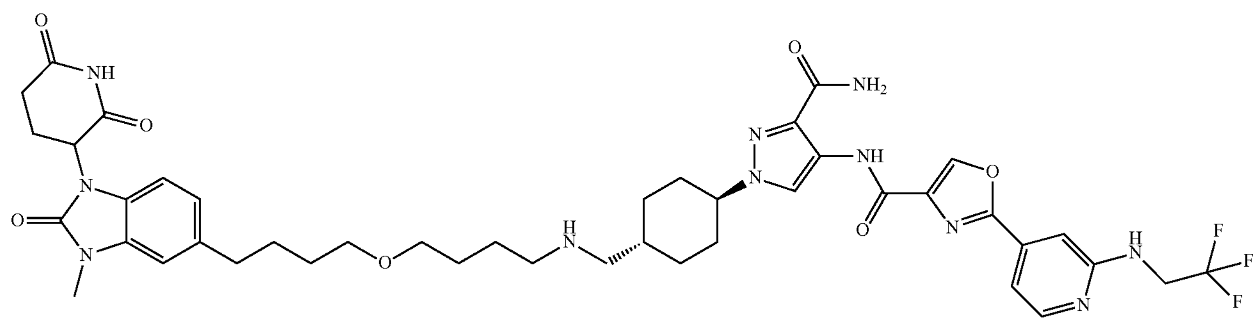 [SMILES: Cn1c(=O)n(C2CCC(=O)NC2=O)c2ccc(CCCCOCCCCNC[C@H]3CC[C@H](n4cc(NC(=O)c5coc(-c6ccnc(NCC(F)(F)F)c6)n5)c(C(N)=O)n4)CC3)cc21] |

TABLE 1-continued
Exemplary Compounds
| I-# | Structure |
|---|---|
| I-10 | 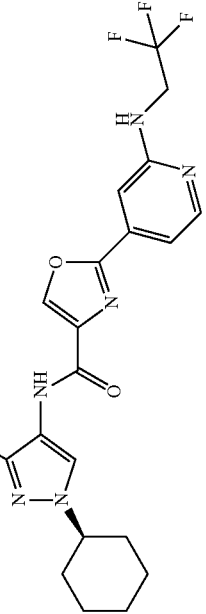 |
| I-11 | 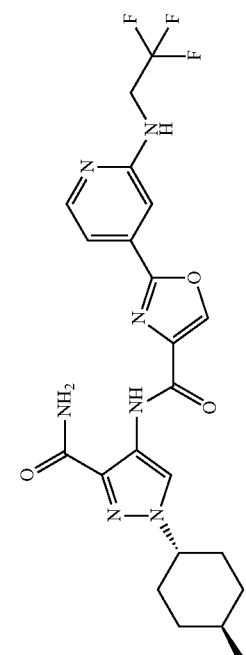 |
| I-12 | 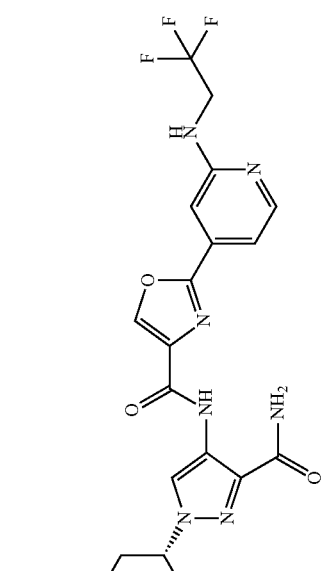 |

TABLE 1-continued
Exemplary Compounds
| I-# | Structure |
|---|---|
| I-13 | 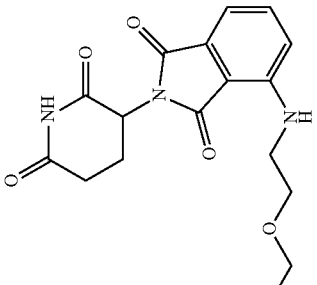 |
| I-14 | 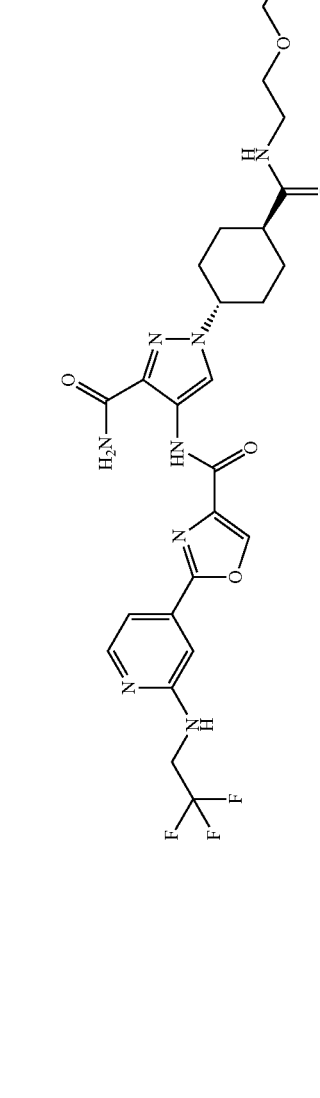 |
| I-15 | 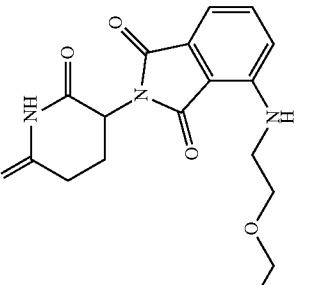 |

TABLE 1-continued
Exemplary Compounds
| I-# | Structure |
|---|---|
| I-16 | 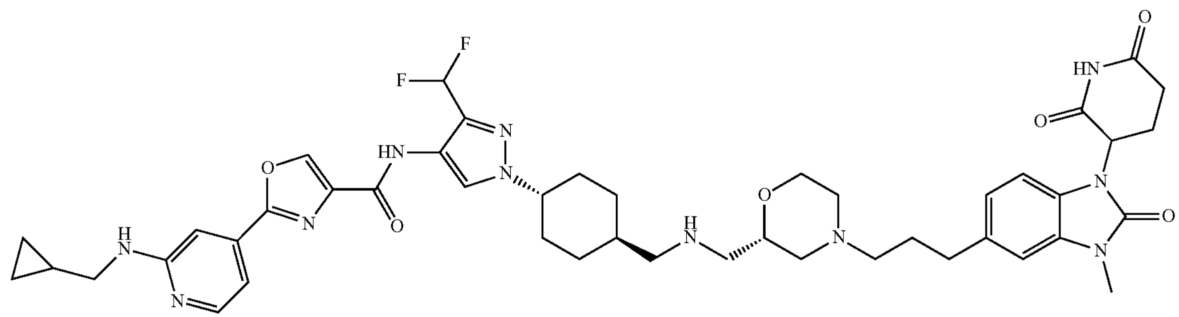 [SMILES: Cn1c(=O)n(C2CCC(=O)NC2=O)c2ccc(CCCN3CCO[C@@H](CNC[C@H]4CC[C@H](n5cc(NC(=O)c6coc(-c7ccnc(NCC8CC8)c7)n6)c(C(F)F)n5)CC4)C3)cc21] |
| I-17 | 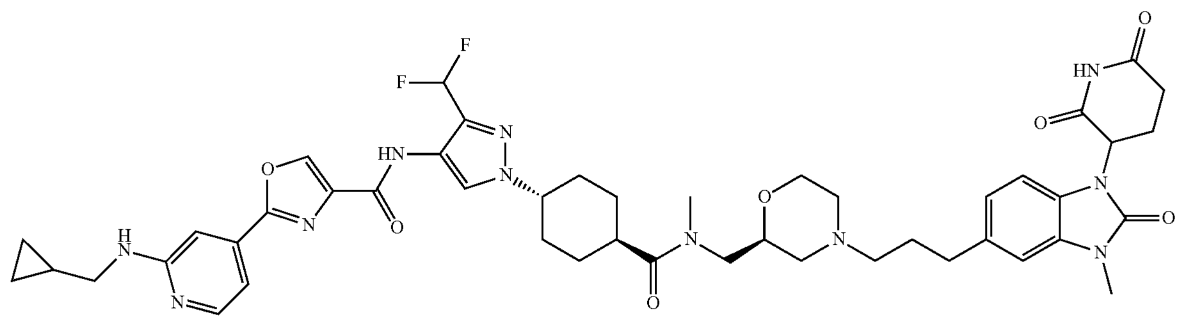 [SMILES: CN(C[C@@H]1CN(CCCc2ccc3c(c2)n(C)c(=O)n3C2CCC(=O)NC2=O)CCO1)C(=O)[C@H]1CC[C@H](n2cc(NC(=O)c3coc(-c4ccnc(NCC5CC5)c4)n3)c(C(F)F)n2)CC1] |
| I-18 | 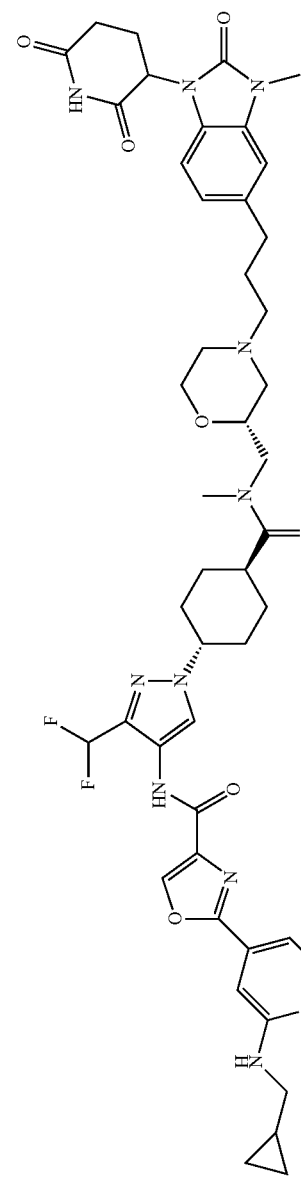 |

TABLE 1-continued
Exemplary Compounds
| I-# | Structure |
|---|---|
| I-19 | 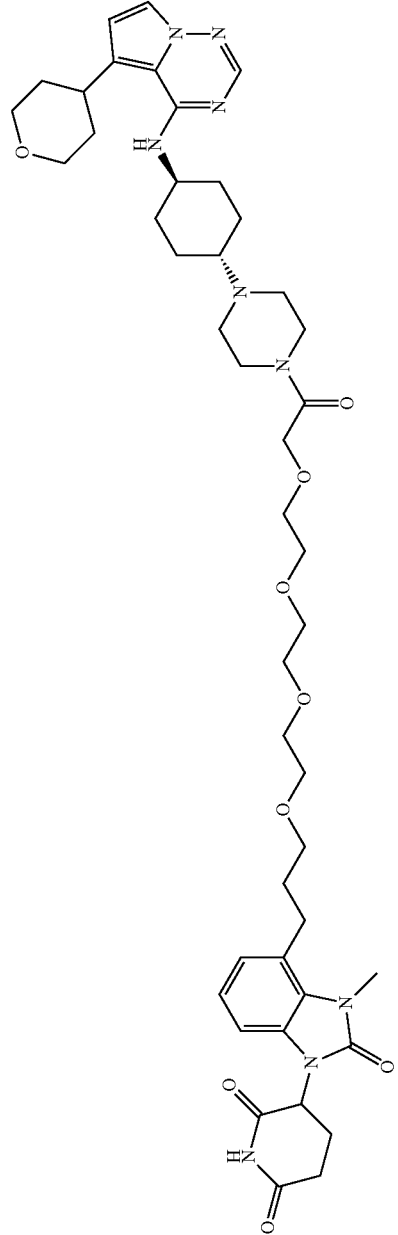 |
| I-20 | 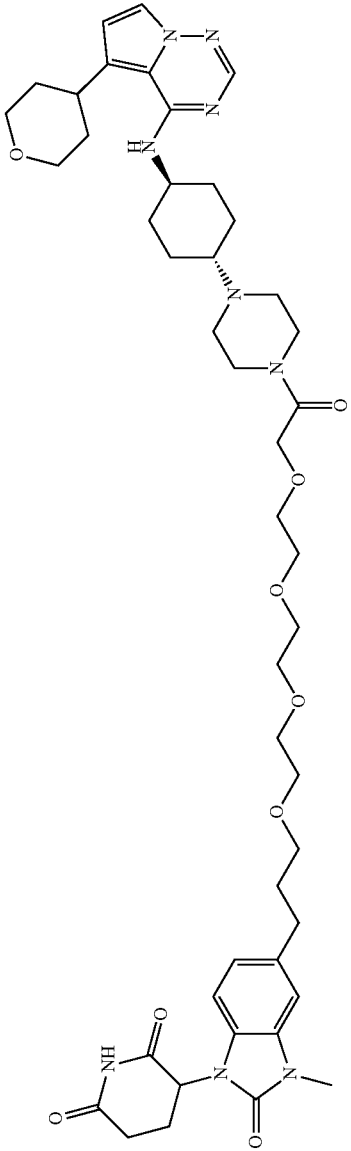 |

TABLE 1-continued
Exemplary Compounds
| I-# | Structure |
|---|---|
| I-21 | 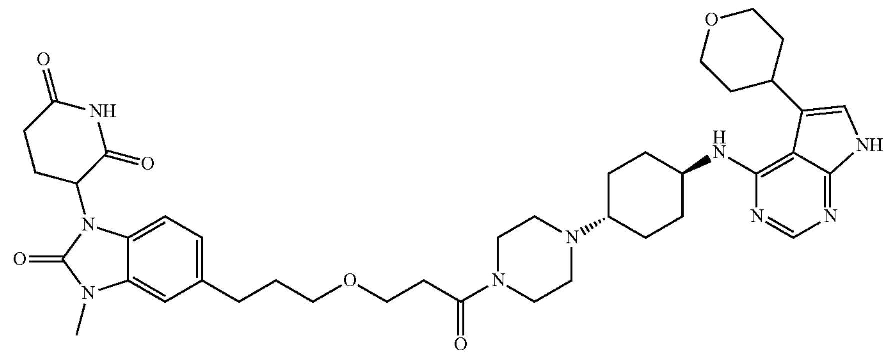 [SMILES: Cn1c(=O)n(C2CCC(=O)NC2=O)c2ccc(CCCOCCC(=O)N3CCN([C@H]4CC[C@H](Nc5ncnc6[nH]cc(C7CCOCC7)c56)CC4)CC3)cc21] |
| I-22 | 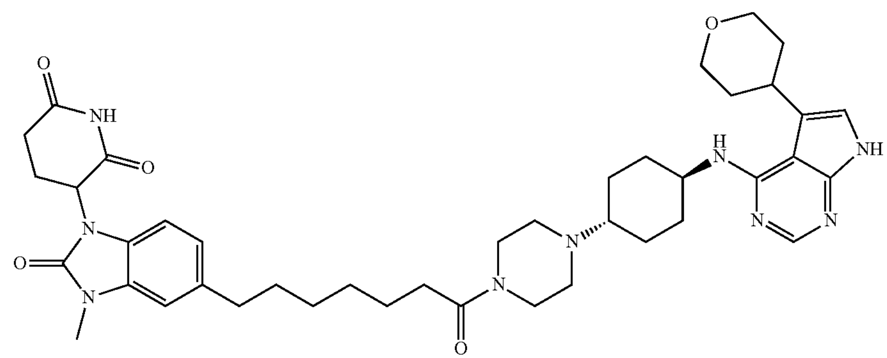 [SMILES: Cn1c(=O)n(C2CCC(=O)NC2=O)c2ccc(CCCCCCC(=O)N3CCN([C@H]4CC[C@H](Nc5ncnc6[nH]cc(C7CCOCC7)c56)CC4)CC3)cc21] |

TABLE 1-continued
Exemplary Compounds
| I-# | Structure |
|---|---|
| I-23 | 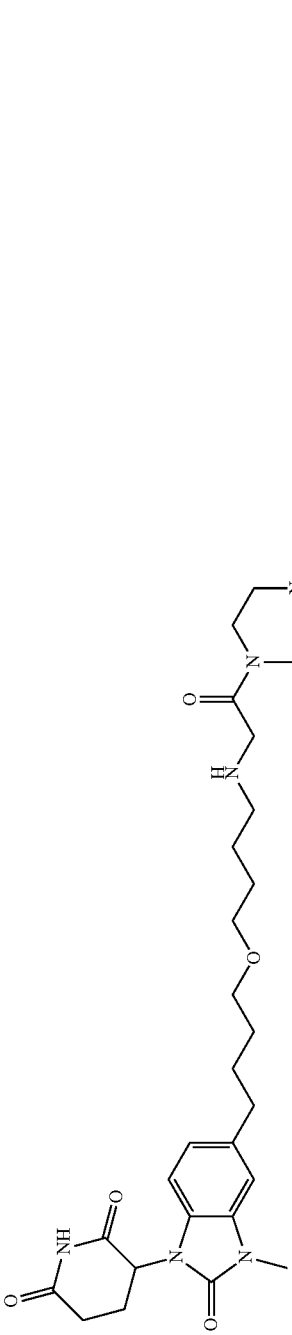 |
| I-24 | 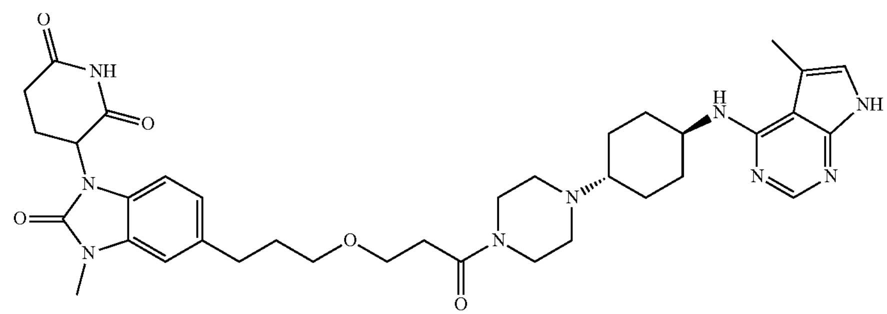 [SMILES: Cc1c[nH]c2ncnc(N[C@H]3CC[C@H](N4CCN(C(=O)CCOCCCc5ccc6c(c5)n(C)c(=O)n6C5CCC(=O)NC5=O)CC4)CC3)c12] |

TABLE 1-continued
Exemplary Compounds
| I-# | Structure |
|---|---|
| I-25 | 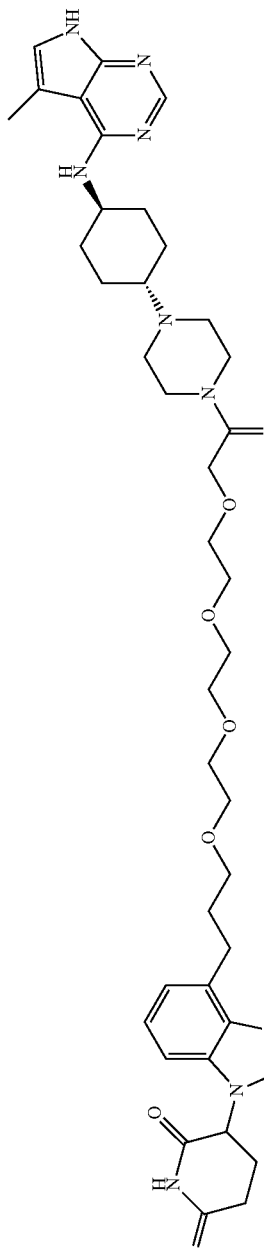 |
| I-26 | 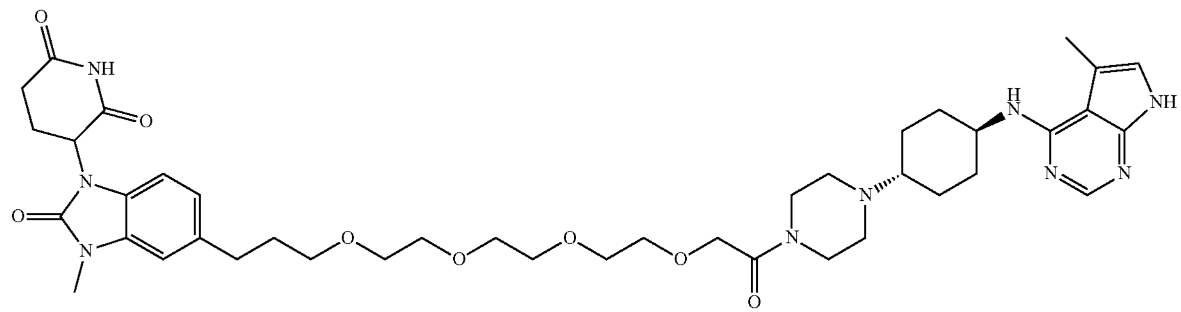 [SMILES: Cc1c[nH]c2ncnc(N[C@H]3CC[C@H](N4CCN(C(=O)COCCOCCOCCOCCCc5ccc6c(c5)n(C)c(=O)n6C5CCC(=O)NC5=O)CC4)CC3)c12] |

TABLE 1-continued
Exemplary Compounds
| I-# | Structure |
|---|---|
| I-27 | 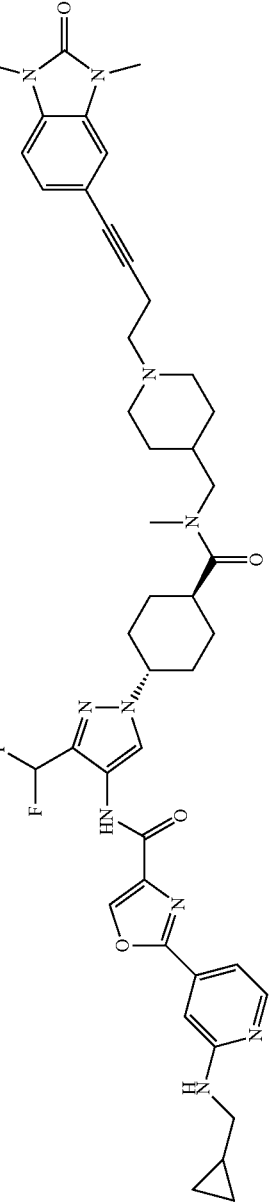 |
| I-28 | 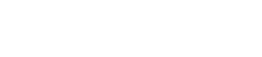 |

TABLE 1-continued
Exemplary Compounds
| I-# | Structure |
|---|---|
| I-29 | 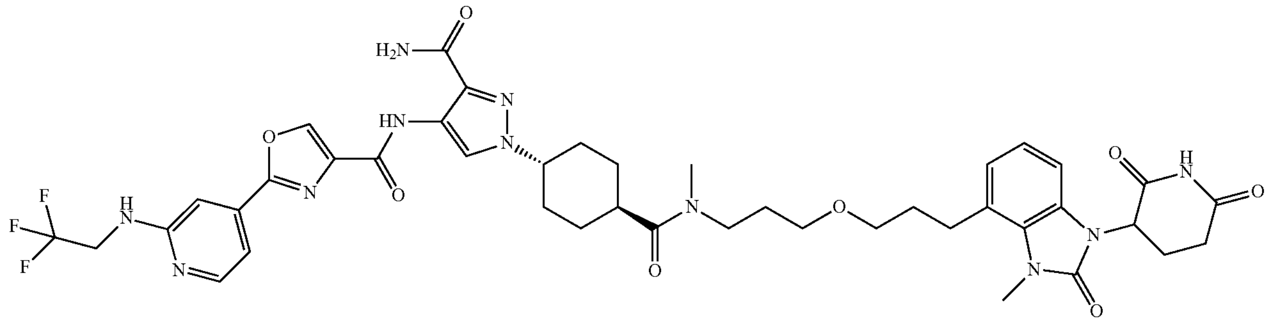 [SMILES: CN(CCCOCCCc1cccc2c1n(C)c(=O)n2C1CCC(=O)NC1=O)C(=O)[C@H]1CC[C@H](n2cc(NC(=O)c3coc(-c4ccnc(NCC(F)(F)F)c4)n3)c(C(N)=O)n2)CC1] |
| I-30 | 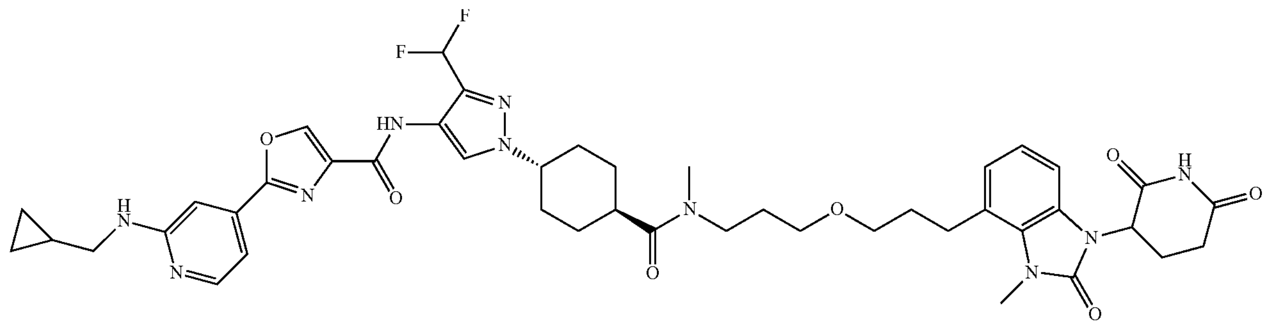 [SMILES: CN(CCCOCCCc1cccc2c1n(C)c(=O)n2C1CCC(=O)NC1=O)C(=O)[C@H]1CC[C@H](n2cc(NC(=O)c3coc(-c4ccnc(NCC5CC5)c4)n3)c(C(F)F)n2)CC1] |
| I-31 | 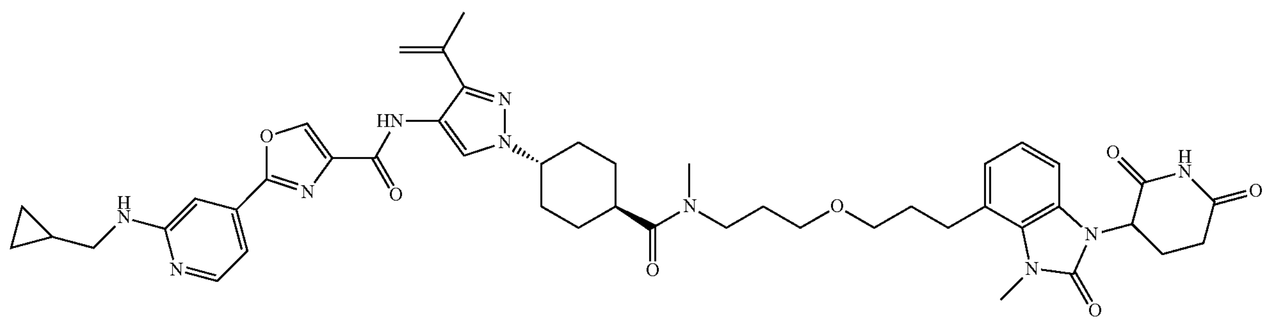 [SMILES: C=C(C)c1nn([C@H]2CC[C@H](C(=O)N(C)CCCOCCCc3cccc4c3n(C)c(=O)n4C3CCC(=O)NC3=O)CC2)cc1NC(=O)c1coc(-c2ccnc(NCC3CC3)c2)n1] |

TABLE 1-continued

Exemplary Compounds

| I-# | Structure |
|---|---|
| I-32 | 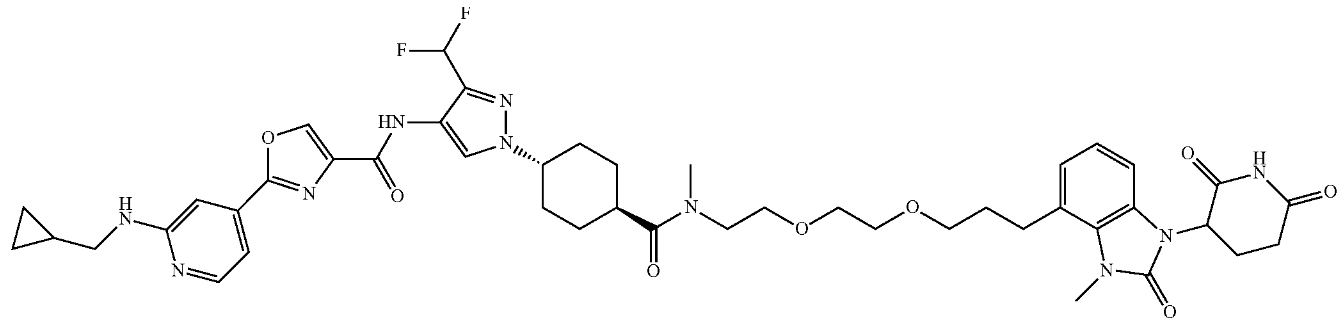 [SMILES: CN(CCOCCOCCCc1cccc2c1n(C)c(=O)n2C1CCC(=O)NC1=O)C(=O)[C@H]1CC[C@H](n2cc(NC(=O)c3coc(-c4ccnc(NCC5CC5)c4)n3)c(C(F)F)n2)CC1] |
| I-33 | 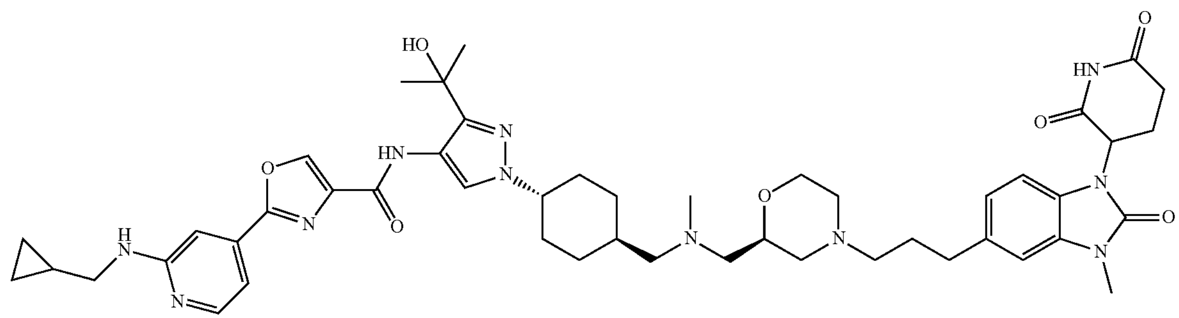 [SMILES: CN(C[C@@H]1CN(CCCc2ccc3c(c2)n(C)c(=O)n3C2CCC(=O)NC2=O)CCO1)C[C@H]1CC[C@H](n2cc(NC(=O)c3coc(-c4ccnc(NCC5CC5)c4)n3)c(C(C)(C)O)n2)CC1] |
| I-34 | 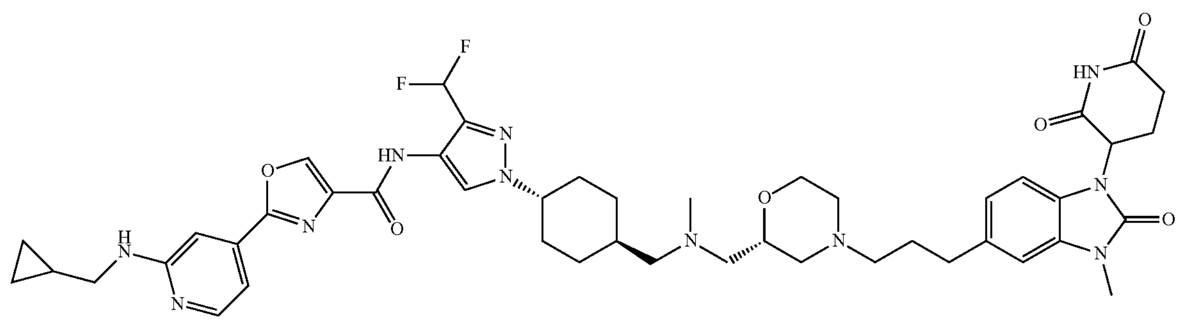 [SMILES: CN(C[C@H]1CN(CCCc2ccc3c(c2)n(C)c(=O)n3C2CCC(=O)NC2=O)CCO1)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-35 | 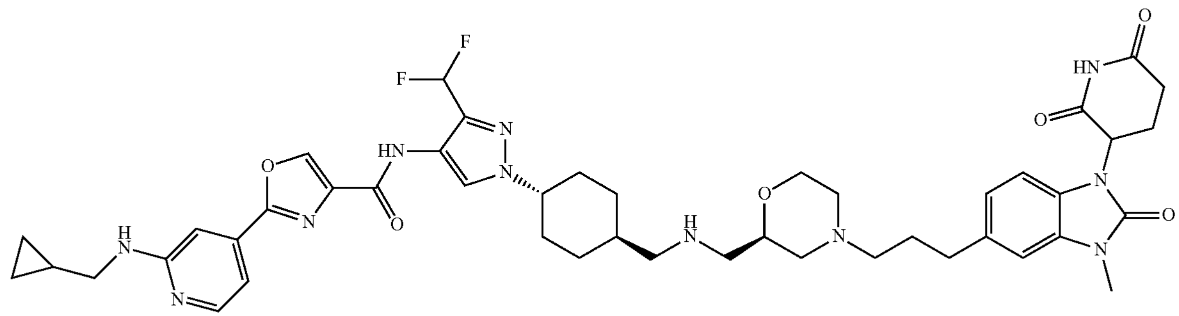 [SMILES: Cn1c(=O)n(C2CCC(=O)NC2=O)c2ccc(CCCN3CCO[C@H](CNC[C@H]4CC[C@H](n5cc(NC(=O)c6coc(-c7ccnc(NCC8CC8)c7)n6)c(C(F)F)n5)CC4)C3)cc21] |
| I-36 | 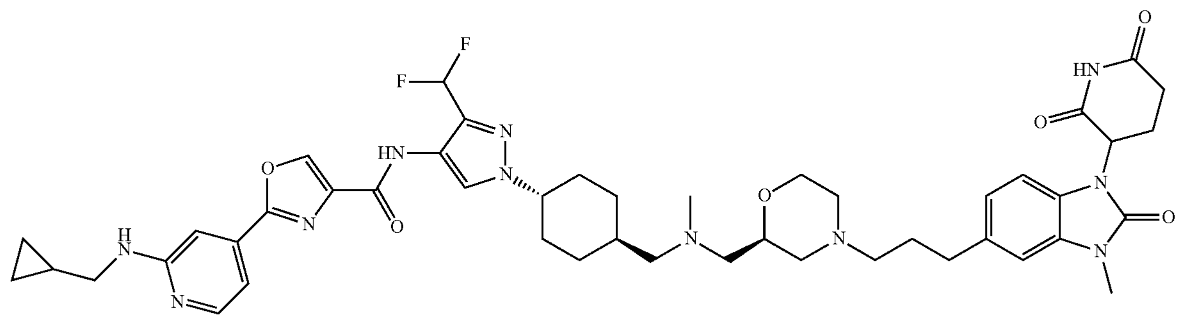 [SMILES: CN(C[C@@H]1CN(CCCc2ccc3c(c2)n(C)c(=O)n3C2CCC(=O)NC2=O)CCO1)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-37 | 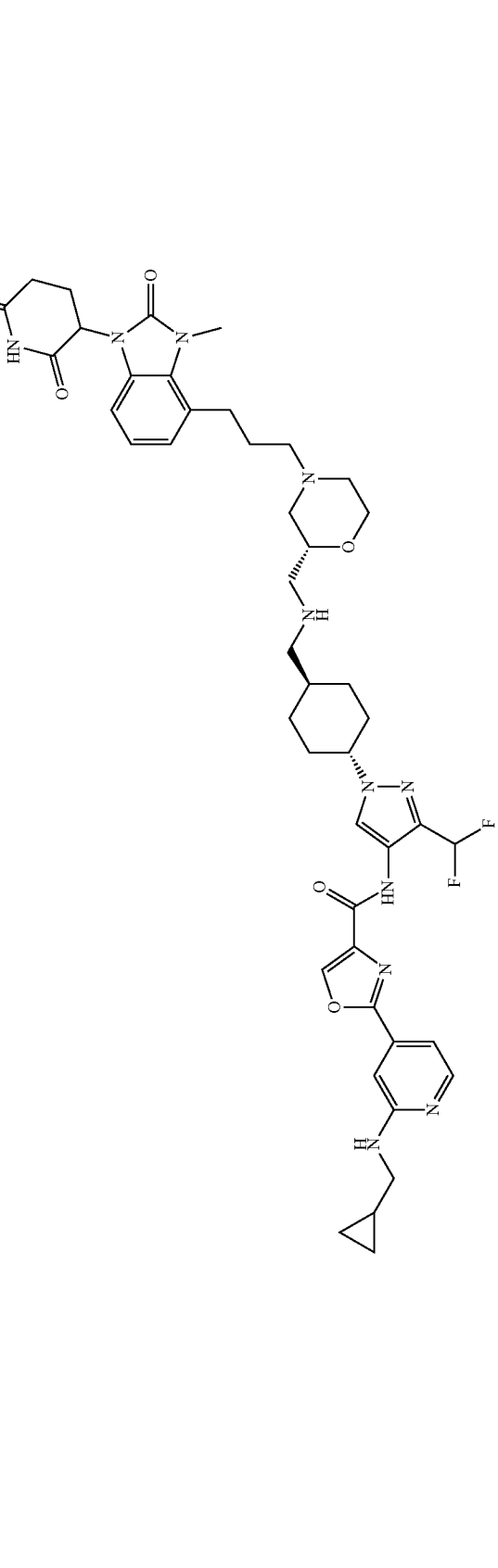 |

TABLE 1-continued
Exemplary Compounds
| I-# | Structure |
|---|---|
| I-38 | 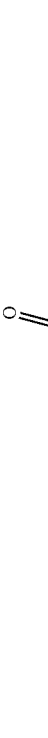 |
| I-39 | 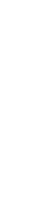 |

TABLE 1-continued
Exemplary Compounds
| I-# | Structure |
|---|---|
| I-40 | 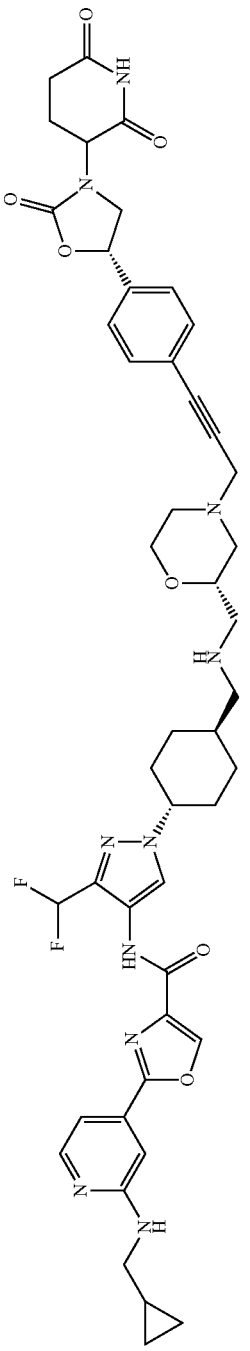 |
| I-41 | 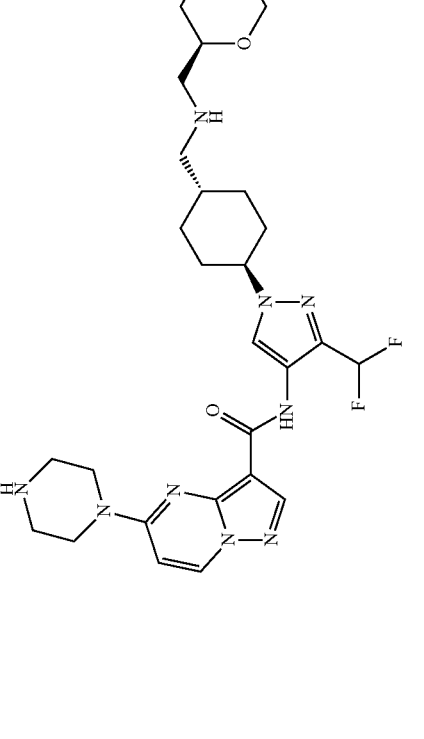 |

TABLE 1-continued
Exemplary Compounds
| I-# | Structure |
|---|---|
| I-42 | 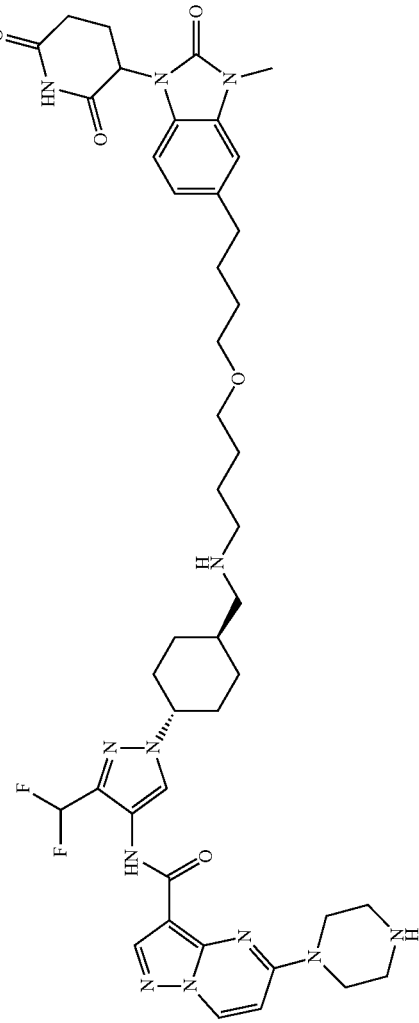 |
| I-43 | 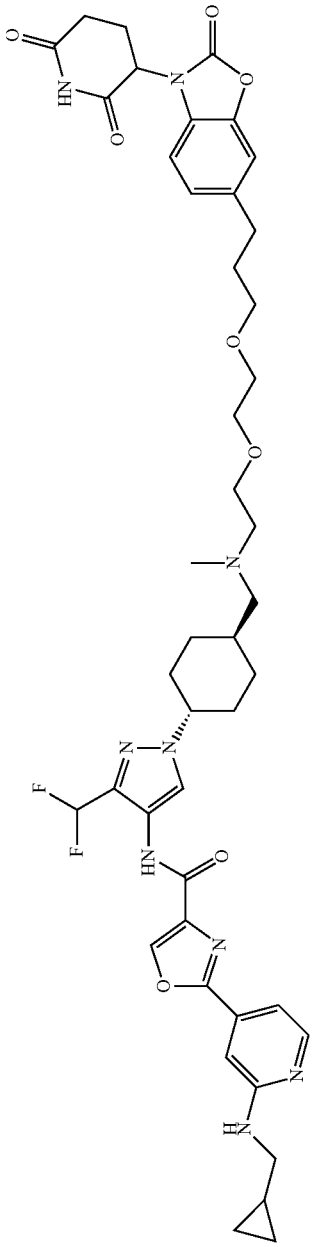 |

TABLE 1-continued
Exemplary Compounds
| I-# | Structure |
|---|---|
| I-44 | 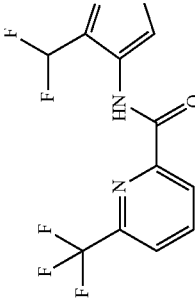 |
| I-45 | 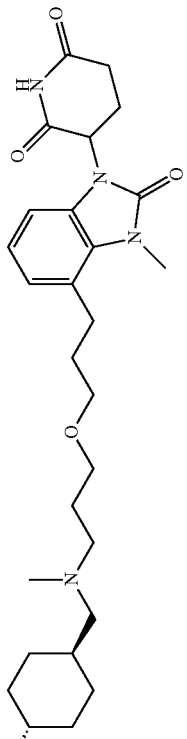 |

TABLE 1-continued
Exemplary Compounds
| I-# | Structure |
|---|---|
| I-46 | 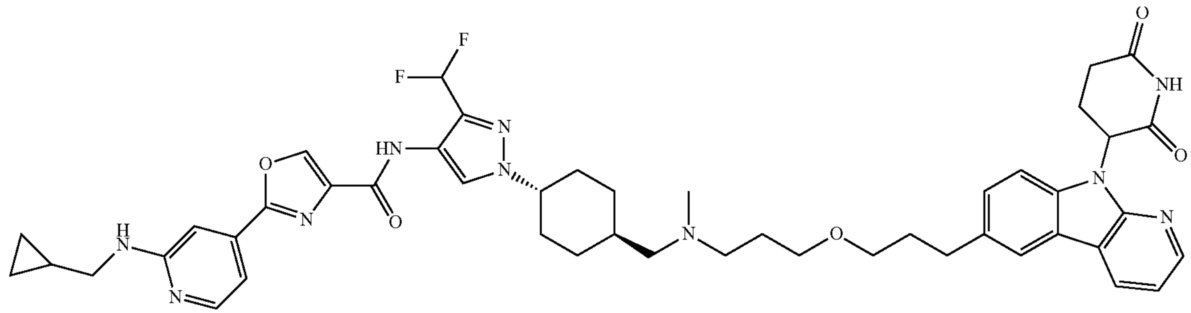 [SMILES: CN(CCCOCCCc1ccc2c(c1)c1cccnc1n2C1CCC(=O)NC1=O)C[C@H]1CC[C@H](n2cc(NC(=O)c3coc(-c4ccnc(NCC5CC5)c4)n3)c(C(F)F)n2)CC1] |
| I-47 | 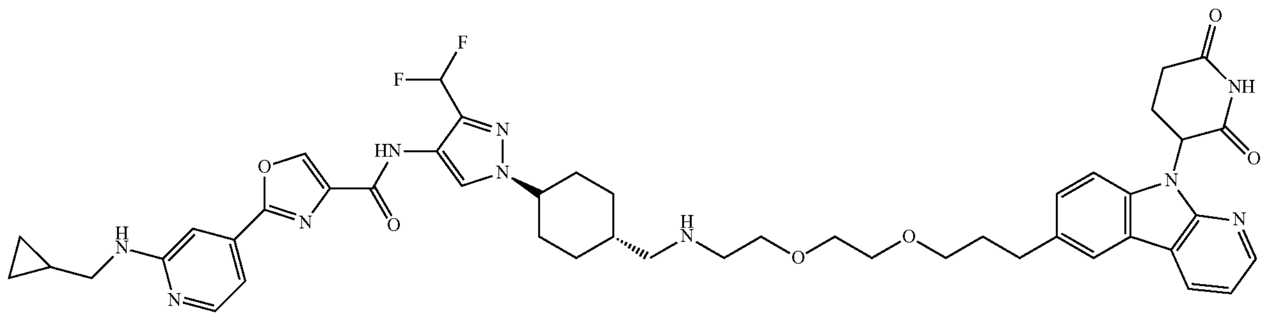 |

TABLE 1-continued
Exemplary Compounds
| I-# | Structure |
|---|---|
| I-48 |  |
| I-49 |  |

TABLE 1-continued
Exemplary Compounds
| I-# | Structure |
|---|---|
| I-50 | 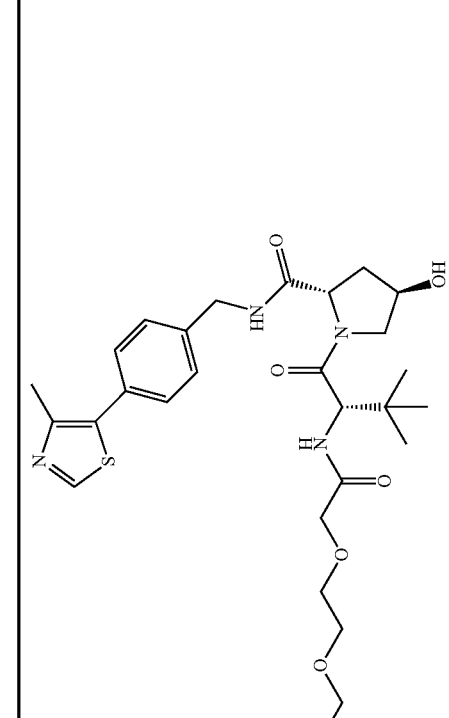 |
| I-51 | 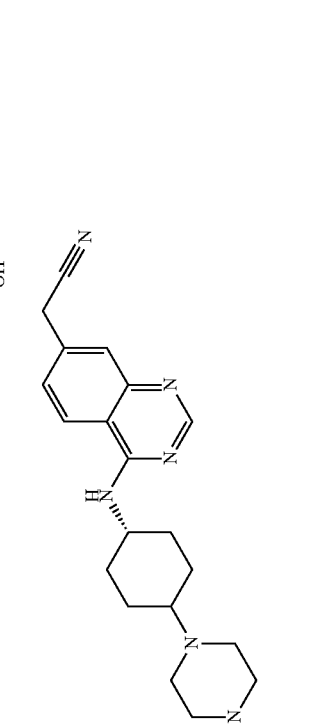 |

TABLE 1-continued
Exemplary Compounds
| I-# | Structure |
|---|---|
| I-52 | 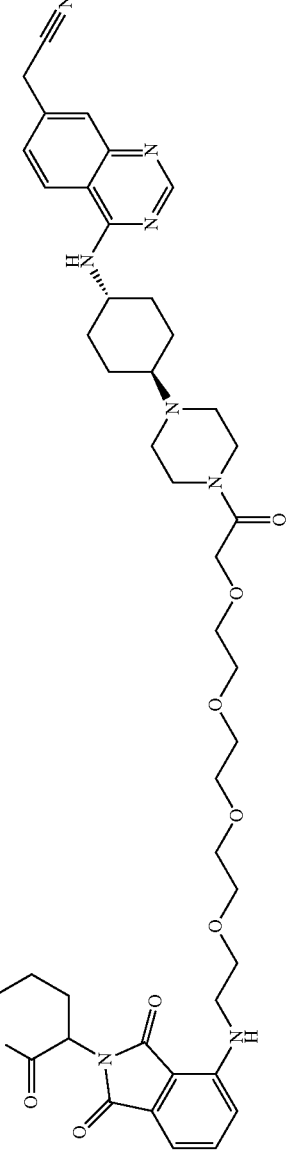 |
| I-53 | 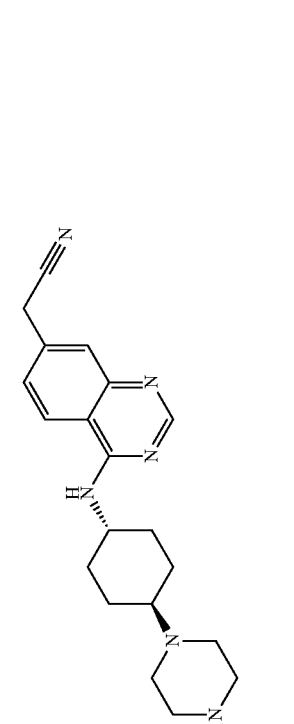 |

TABLE 1-continued

Exemplary Compounds

| I-# | Structure |
|---|---|
| I-54 | 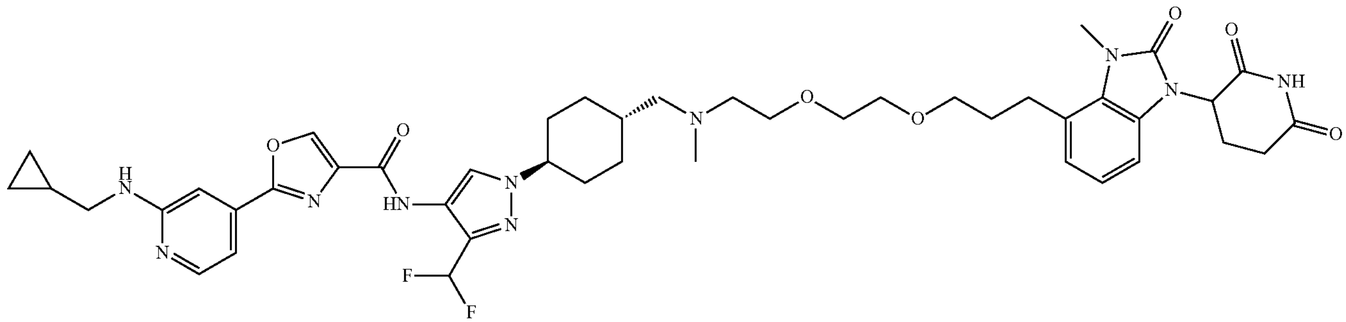 [SMILES: CN(CCOCCOCCCc1cccc2c1n(C)c(=O)n2C1CCC(=O)NC1=O)C[C@H]1CC[C@H](n2cc(NC(=O)c3coc(-c4ccnc(NCC5CC5)c4)n3)c(C(F)F)n2)CC1] |
| I-55 | 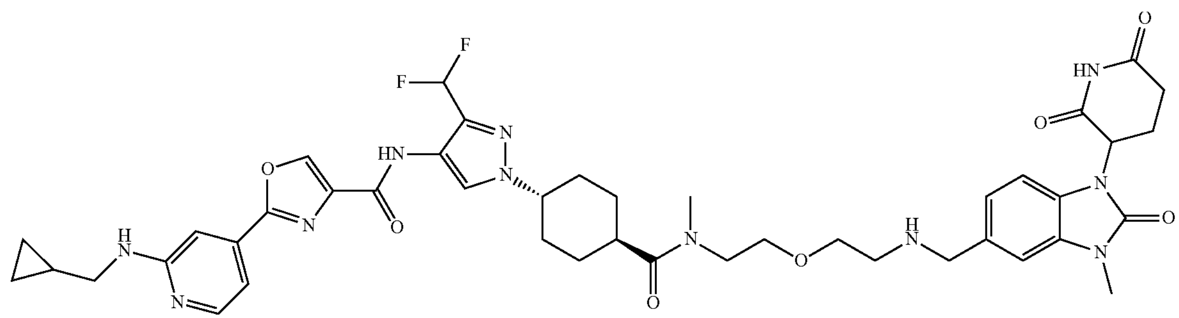 [SMILES: CN(CCOCCNCc1ccc2c(c1)n(C)c(=O)n2C1CCC(=O)NC1=O)C(=O)[C@H]1CC[C@H](n2cc(NC(=O)c3coc(-c4ccnc(NCC5CC5)c4)n3)c(C(F)F)n2)CC1] |
| I-56 | 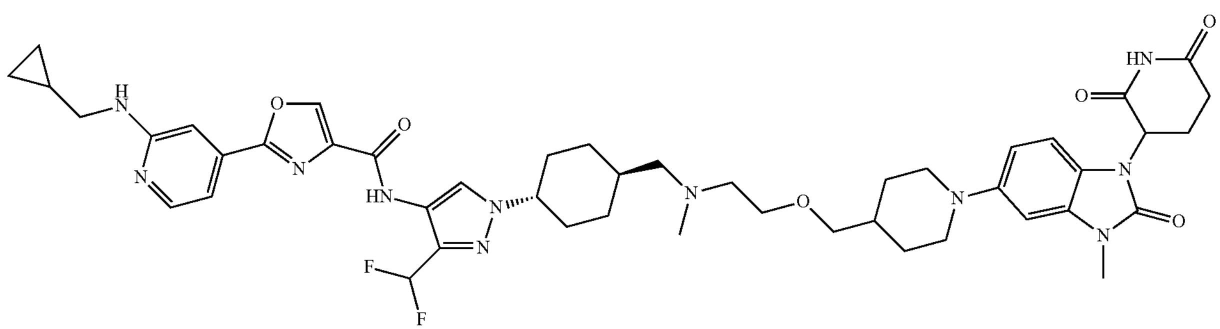 [SMILES: CN(CCOCC1CCN(c2ccc3c(c2)n(C)c(=O)n3C2CCC(=O)NC2=O)CC1)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-57 | 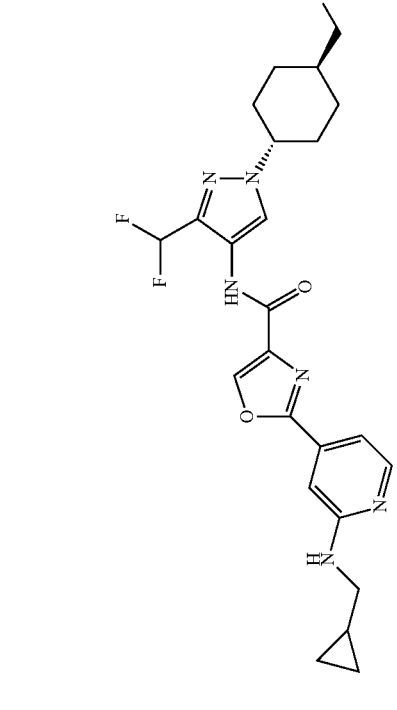 |
| I-58 | 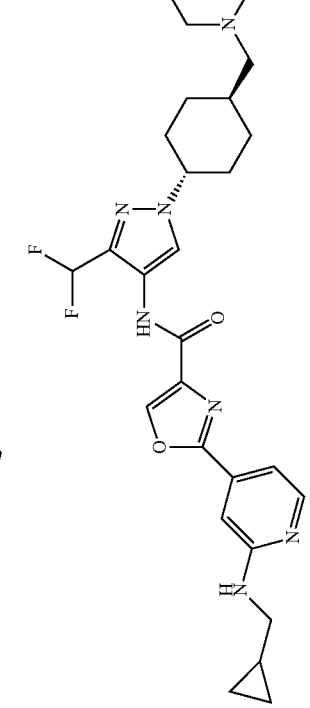 |

TABLE 1-continued
Exemplary Compounds
| I-# | Structure |
|---|---|
| I-59 | 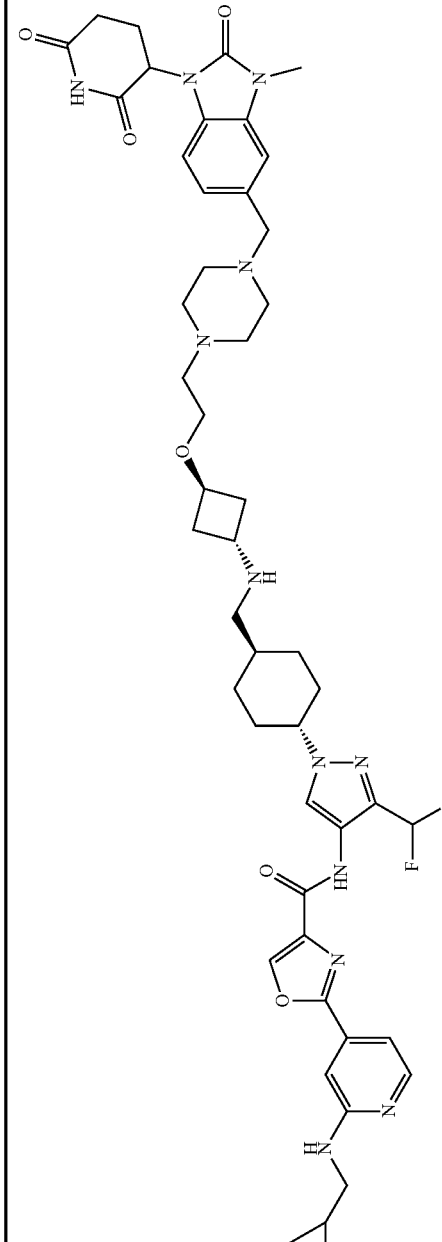 |
| I-60 | 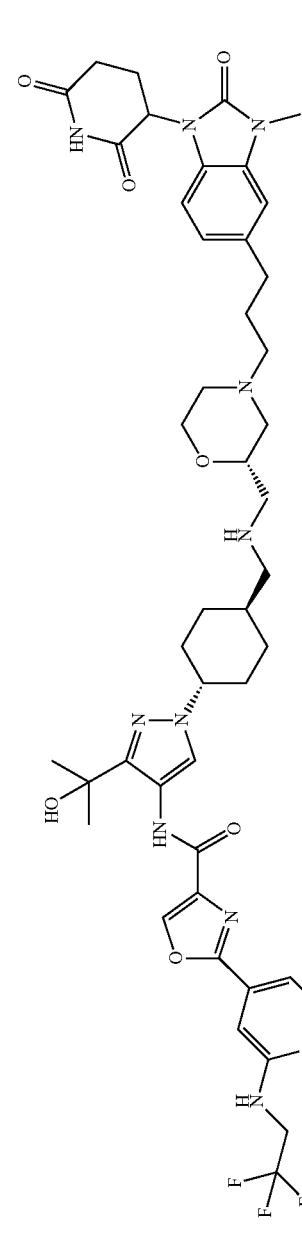 |

TABLE 1-continued
Exemplary Compounds
| I-# | Structure |
|---|---|
| I-61 | 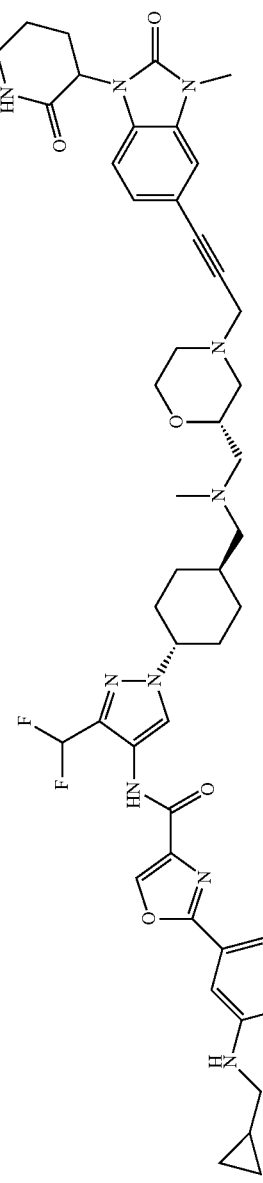 |
| I-62 | 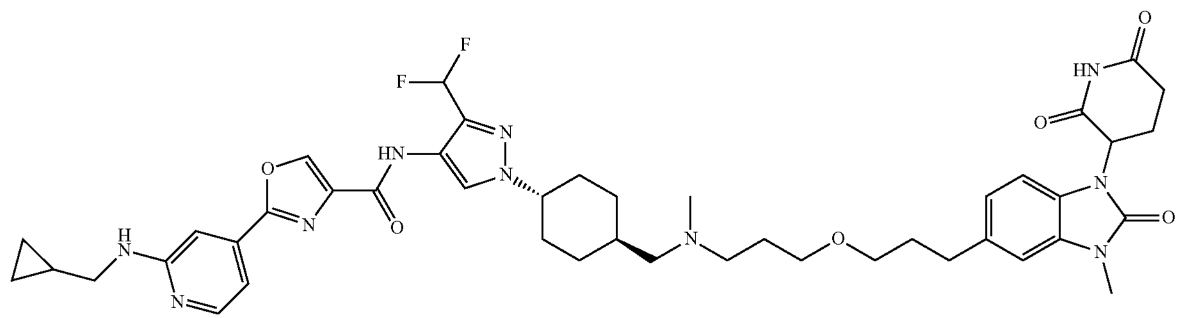 [SMILES: CN(CCCOCCCc1ccc2c(c1)n(C)c(=O)n2C1CCC(=O)NC1=O)C[C@H]1CC[C@H](n2cc(NC(=O)c3coc(-c4ccnc(NCC5CC5)c4)n3)c(C(F)F)n2)CC1] |
| I-63 | 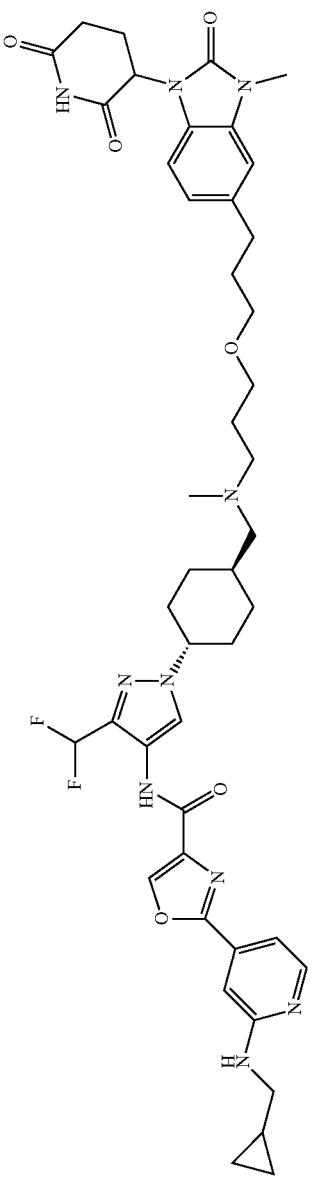 |

TABLE 1-continued
Exemplary Compounds
| I-# | Structure |
|---|---|
| I-64 | 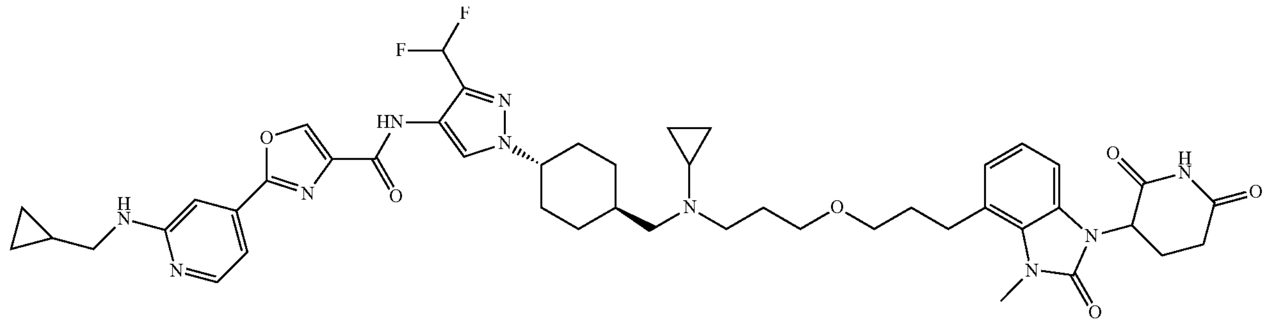 [SMILES: Cn1c(=O)n(C2CCC(=O)NC2=O)c2cccc(CCCOCCCN(C[C@H]3CC[C@H](n4cc(NC(=O)c5coc(-c6ccnc(NCC7CC7)c6)n5)c(C(F)F)n4)CC3)C3CC3)c21] |
| I-65 | 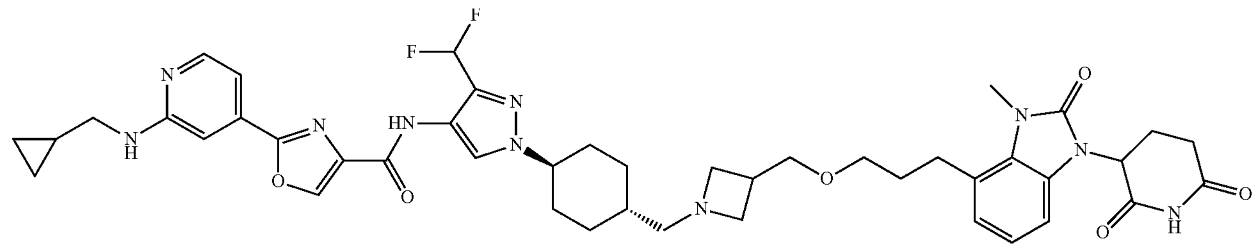 [SMILES: Cn1c(=O)n(C2CCC(=O)NC2=O)c2cccc(CCCOCC3CN(C[C@H]4CC[C@H](n5cc(NC(=O)c6coc(-c7ccnc(NCC8CC8)c7)n6)c(C(F)F)n5)CC4)C3)c21] |
| I-66 | 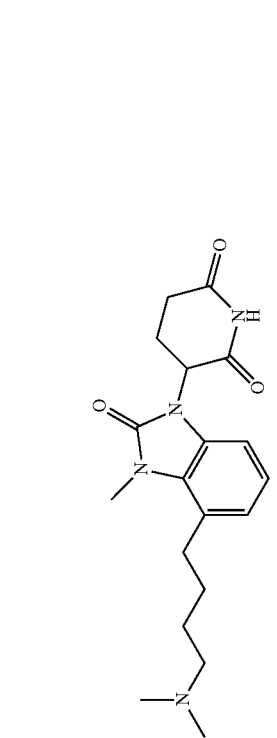 |

TABLE 1-continued
Exemplary Compounds
| I-# | Structure |
|---|---|
| I-67 | 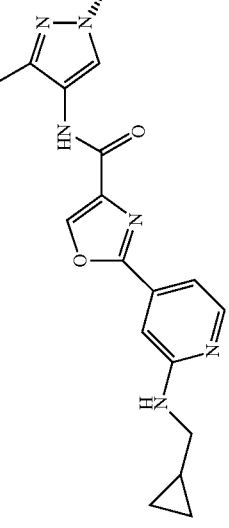 |
| I-68 | 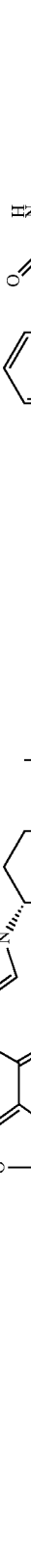 |
| I-69 | 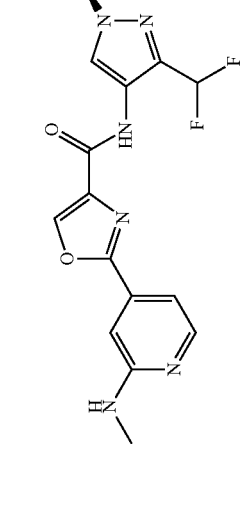 |

TABLE 1-continued
Exemplary Compounds
| I-# | Structure |
|---|---|
| I-70 | 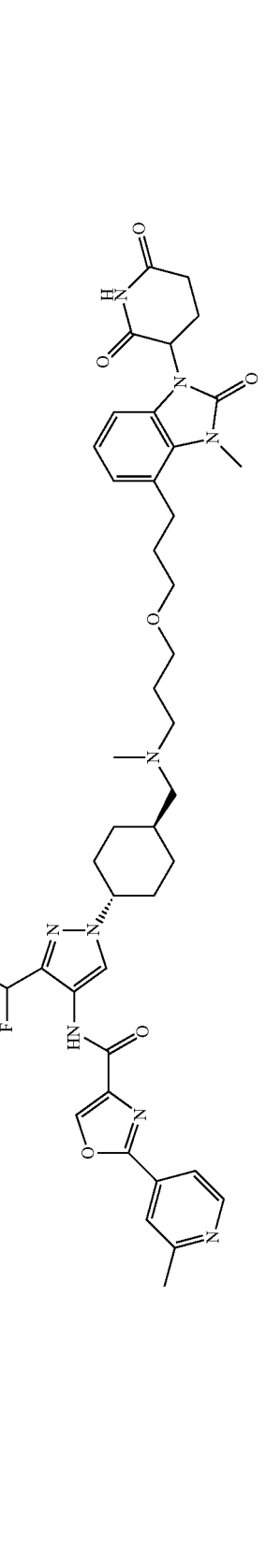 |
| I-71 | 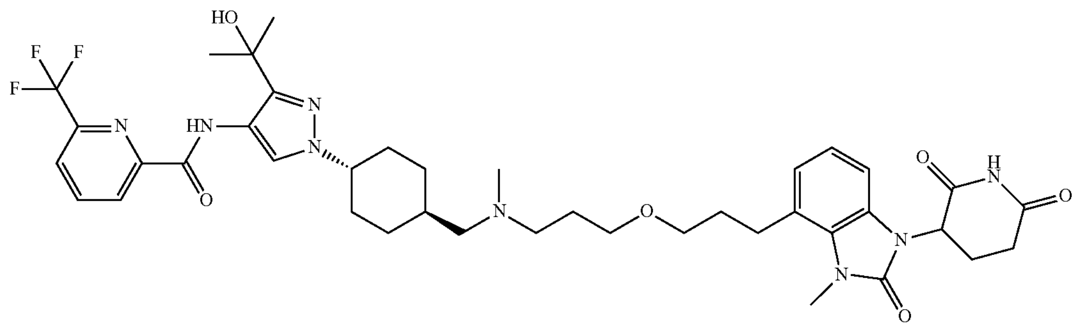 [SMILES: CN(CCCOCCCc1cccc2c1n(C)c(=O)n2C1CCC(=O)NC1=O)C[C@H]1CC[C@H](n2cc(NC(=O)c3cccc(C(F)(F)F)n3)c(C(C)(C)O)n2)CC1] |
| I-72 | 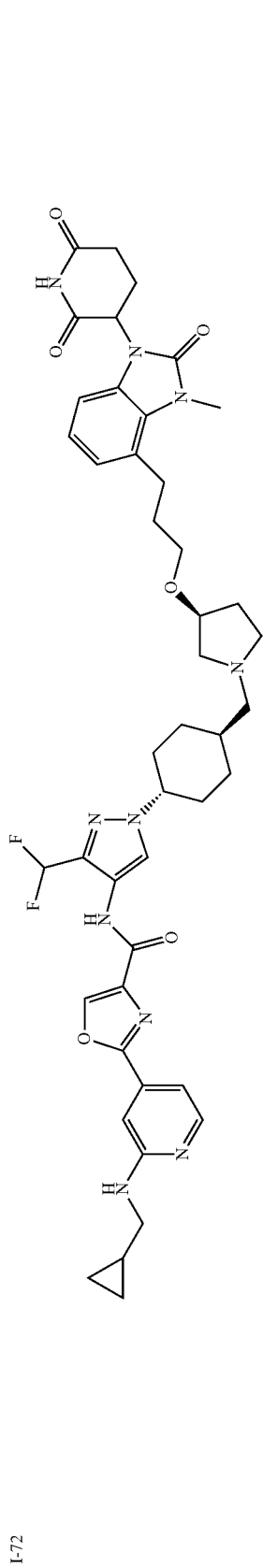 |

TABLE 1-continued
Exemplary Compounds
| I-# | Structure |
|---|---|
| I-73 | 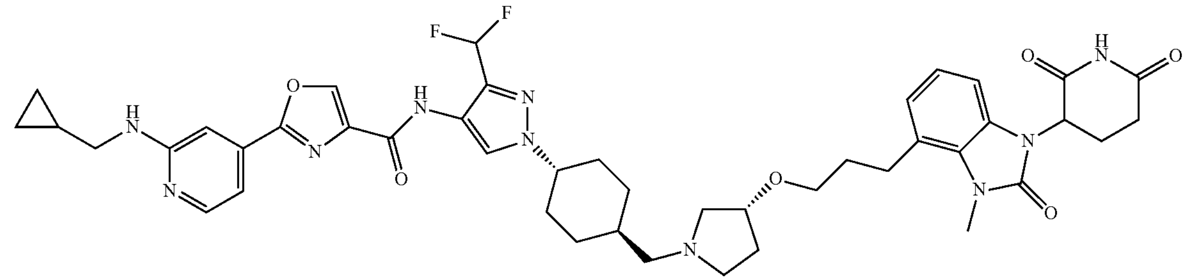 [SMILES: Cn1c(=O)n(C2CCC(=O)NC2=O)c2cccc(CCCO[C@@H]3CCN(C[C@H]4CC[C@H](n5cc(NC(=O)c6coc(-c7ccnc(NCC8CC8)c7)n6)c(C(F)F)n5)CC4)C3)c21] |
| I-74 | 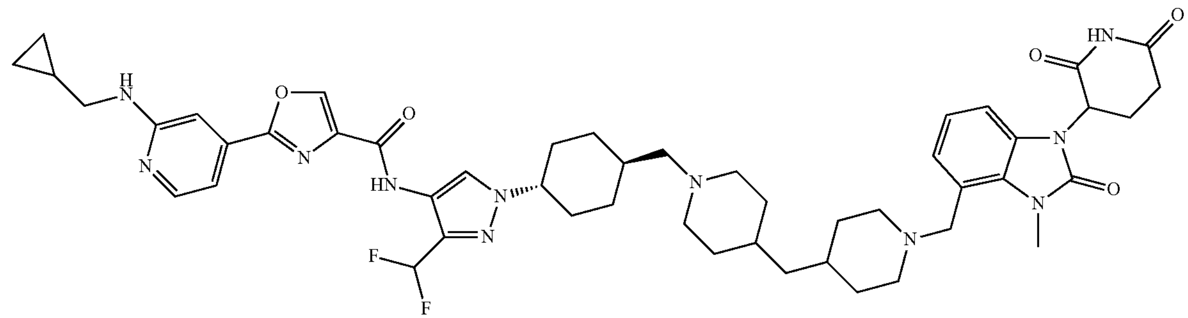 [SMILES: Cn1c(=O)n(C2CCC(=O)NC2=O)c2cccc(CN3CCC(CC4CCN(C[C@H]5CC[C@H](n6cc(NC(=O)c7coc(-c8ccnc(NCC9CC9)c8)n7)c(C(F)F)n6)CC5)CC4)CC3)c21] |
| I-75 | 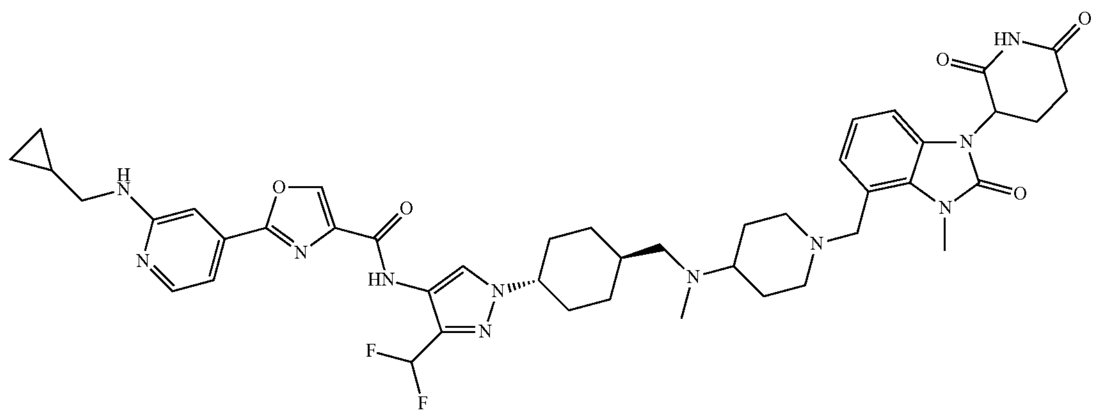 [SMILES: CN(C[C@H]1CC[C@H](n2cc(NC(=O)c3coc(-c4ccnc(NCC5CC5)c4)n3)c(C(F)F)n2)CC1)C1CCN(Cc2cccc3c2n(C)c(=O)n3C2CCC(=O)NC2=O)CC1] |

TABLE 1-continued
Exemplary Compounds
| I-# | Structure |
|---|---|
| I-76 | 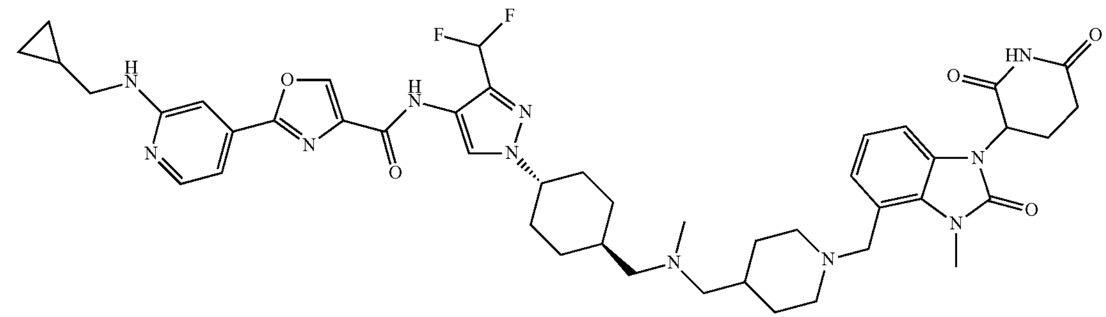 [SMILES: CN(CC1CCN(Cc2cccc3c2n(C)c(=O)n3C2CCC(=O)NC2=O)CC1)C[C@H]1CC[C@H](n2cc(NC(=O)c3coc(-c4ccnc(NCC5CC5)c4)n3)c(C(F)F)n2)CC1] |
| I-77 | 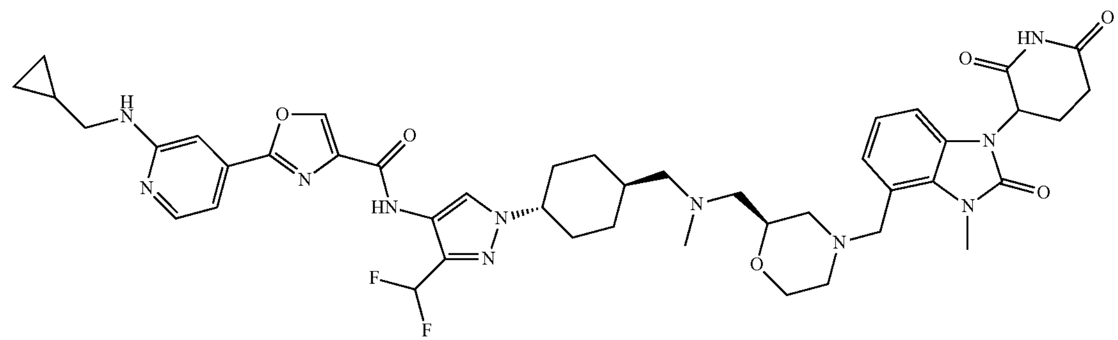 [SMILES: CN(C[C@H]1CN(Cc2cccc3c2n(C)c(=O)n3C2CCC(=O)NC2=O)CCO1)C[C@H]1CC[C@H](n2cc(NC(=O)c3coc(-c4ccnc(NCC5CC5)c4)n3)c(C(F)F)n2)CC1] |
| I-78 | 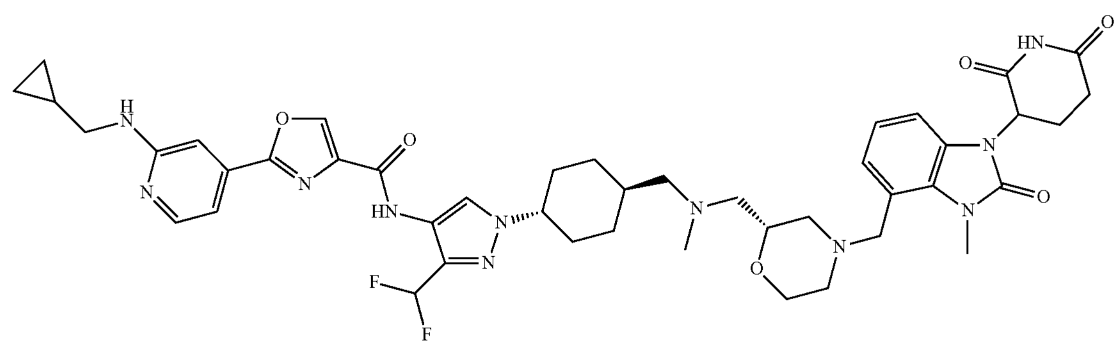 [SMILES: CN(C[C@@H]1CN(Cc2cccc3c2n(C)c(=O)n3C2CCC(=O)NC2=O)CCO1)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-79 | 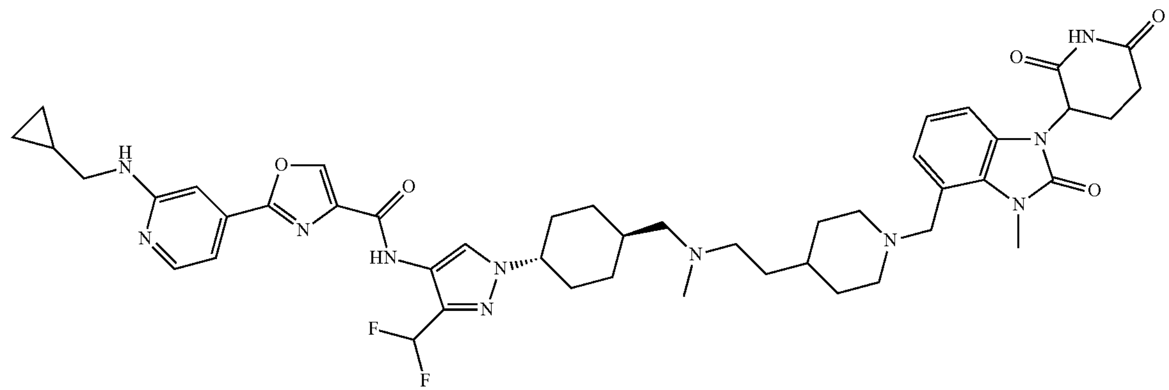 [SMILES: CN(CCC1CCN(Cc2cccc3c2n(C)c(=O)n3C2CCC(=O)NC2=O)CC1)C[C@H]1CC[C@H](n2cc(NC(=O)c3coc(-c4ccnc(NCC5CC5)c4)n3)c(C(F)F)n2)CC1] |
| I-80 | 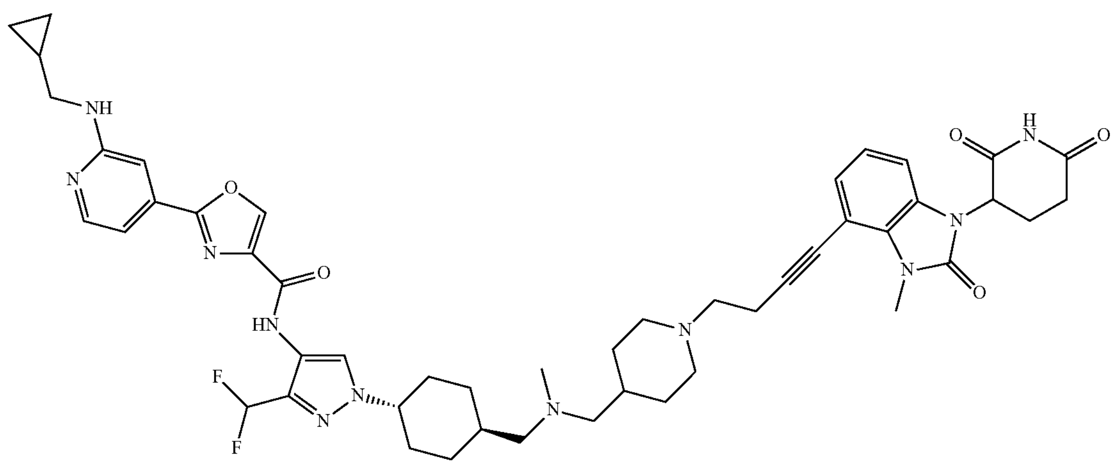 [SMILES: CN(CC1CCN(CCC#Cc2cccc3c2n(C)c(=O)n3C2CCC(=O)NC2=O)CC1)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-81 | 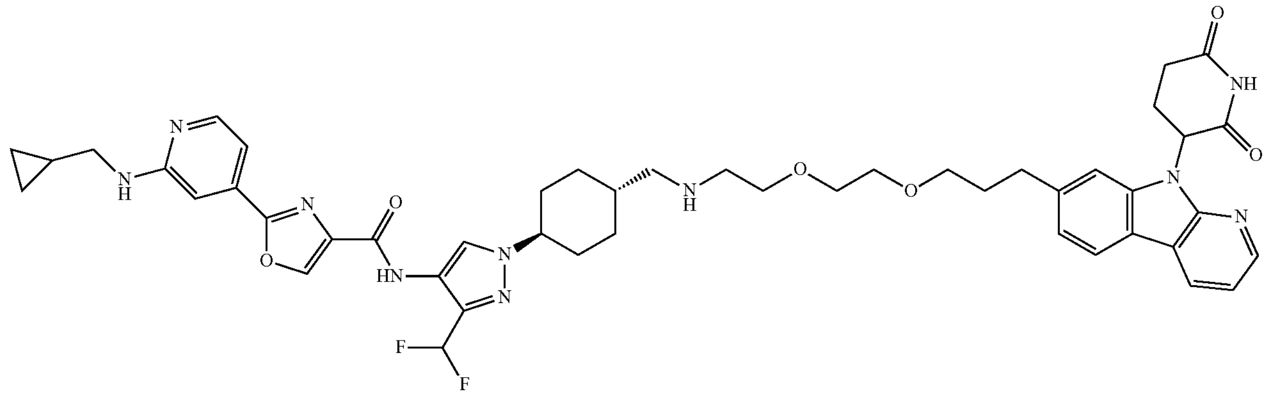 [SMILES: O=C1CCC(n2c3cc(CCCOCCOCCNC[C@H]4CC[C@H](n5cc(NC(=O)c6coc(-c7ccnc(NCC8CC8)c7)n6)c(C(F)F)n5)CC4)ccc3c3cccnc32)C(=O)N1] |
| I-82 | 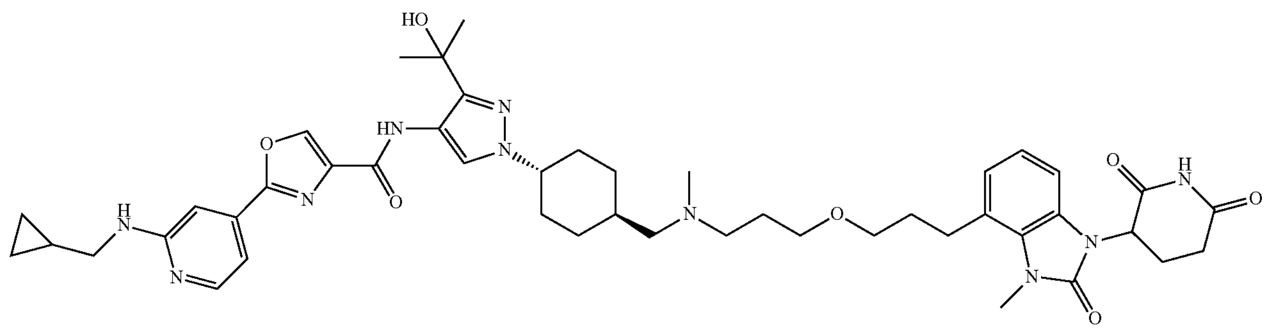 [SMILES: CN(CCCOCCCc1cccc2c1n(C)c(=O)n2C1CCC(=O)NC1=O)C[C@H]1CC[C@H](n2cc(NC(=O)c3coc(-c4ccnc(NCC5CC5)c4)n3)c(C(C)(C)O)n2)CC1] |

TABLE 1-continued
Exemplary Compounds
| I-# | Structure |
|---|---|
| I-83 | 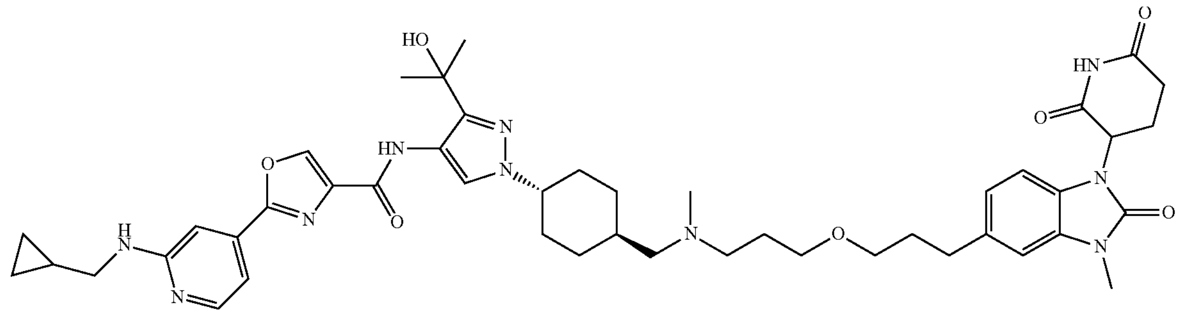 [SMILES: CN(CCCOCCCc1ccc2c(c1)n(C)c(=O)n2C1CCC(=O)NC1=O)C[C@H]1CC[C@H](n2cc(NC(=O)c3coc(-c4ccnc(NCC5CC5)c4)n3)c(C(C)(C)O)n2)CC1] |
| I-84 | 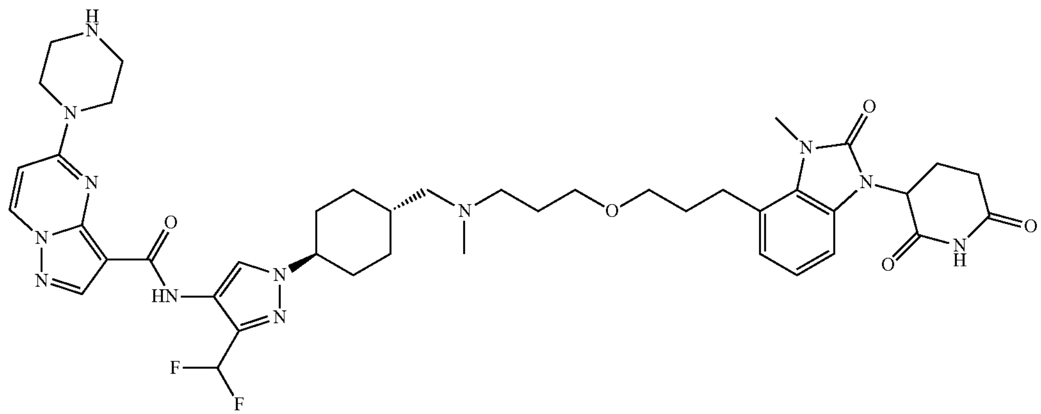 [SMILES: CN(CCCOCCCc1cccc2c1n(C)c(=O)n2C1CCC(=O)NC1=O)C[C@H]1CC[C@H](n2cc(NC(=O)c3cnn4ccc(N5CCNCC5)nc34)c(C(F)F)n2)CC1] |

TABLE 1-continued
Exemplary Compounds
| I-# | Structure |
|---|---|
| I-85 | 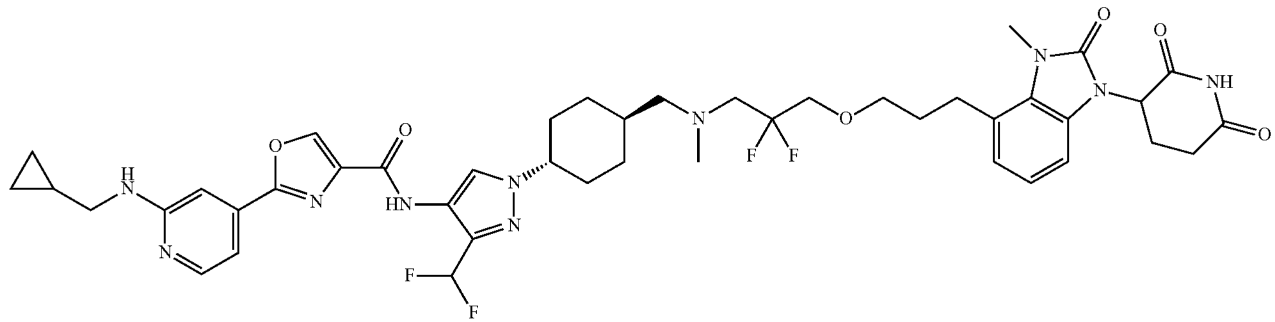 [SMILES: CN(CC(F)(F)COCCCc1cccc2c1n(C)c(=O)n2C1CCC(=O)NC1=O)C[C@H]1CC[C@H](n2cc(NC(=O)c3coc(-c4ccnc(NCC5CC5)c4)n3)c(C(F)F)n2)CC1] |
| I-86 | 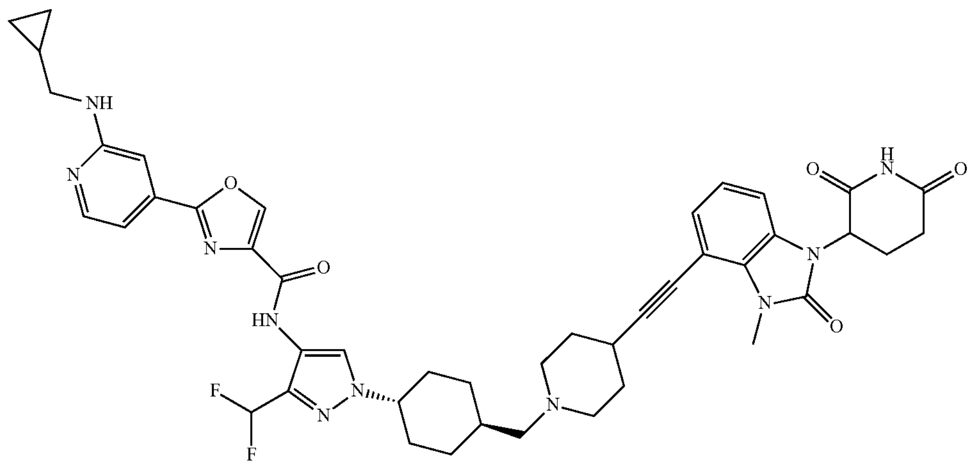 [SMILES: Cn1c(=O)n(C2CCC(=O)NC2=O)c2cccc(C#CC3CCN(C[C@H]4CC[C@H](n5cc(NC(=O)c6coc(-c7ccnc(NCC8CC8)c7)n6)c(C(F)F)n5)CC4)CC3)c21] |

TABLE 1-continued
Exemplary Compounds
| I-# | Structure |
|---|---|
| I-87 | 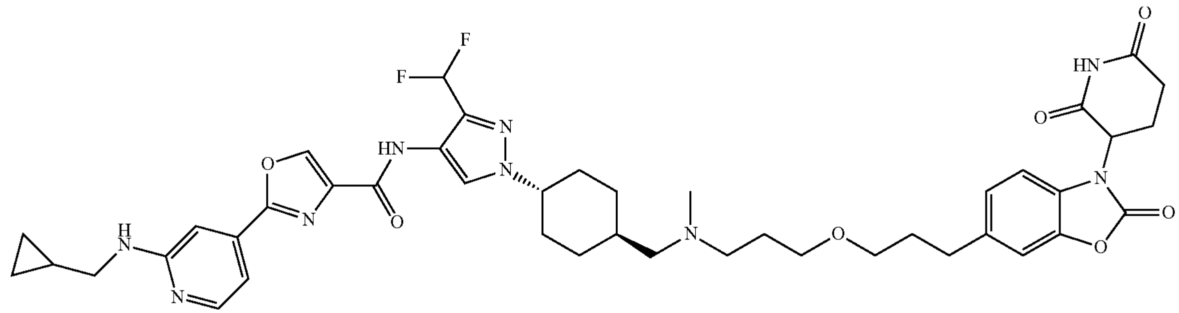 [SMILES: CN(CCCOCCCc1ccc2c(c1)oc(=O)n2C1CCC(=O)NC1=O)C[C@H]1CC[C@H](n2cc(NC(=O)c3coc(-c4ccnc(NCC5CC5)c4)n3)c(C(F)F)n2)CC1] |
| I-88 | 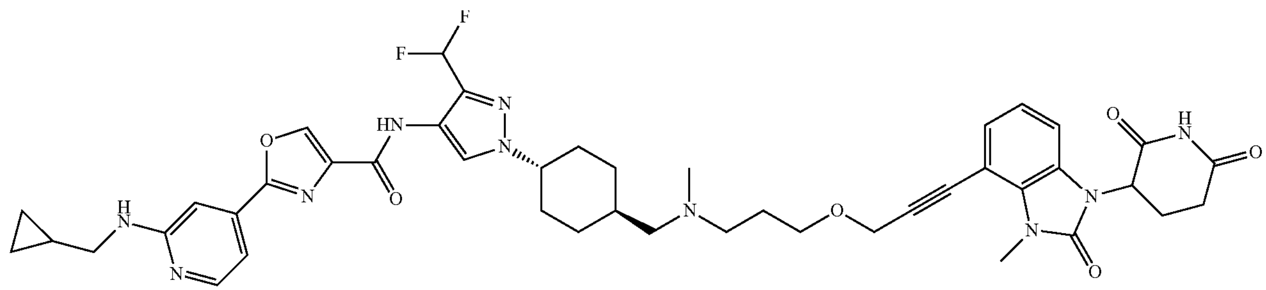 [SMILES: CN(CCCOCC#Cc1cccc2c1n(C)c(=O)n2C1CCC(=O)NC1=O)C[C@H]1CC[C@H](n2cc(NC(=O)c3coc(-c4ccnc(NCC5CC5)c4)n3)c(C(F)F)n2)CC1] |
| I-89 | 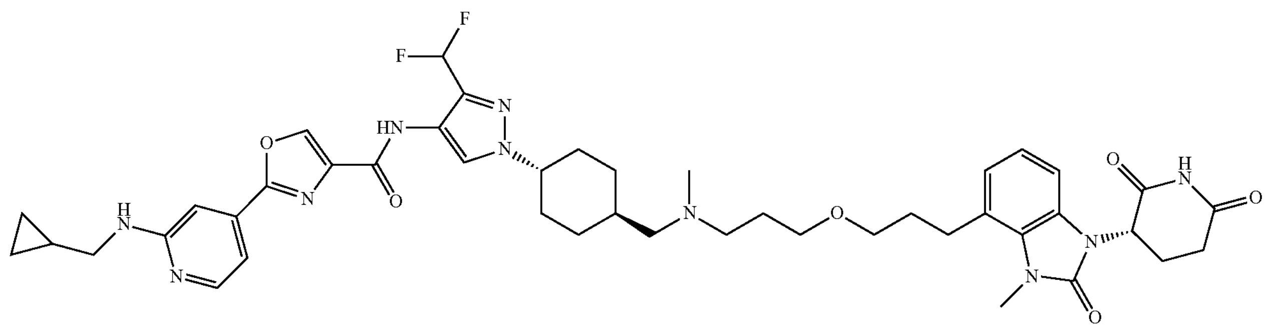 [SMILES: CN(CCCOCCCc1cccc2c1n(C)c(=O)n2[C@H]1CCC(=O)NC1=O)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-90 | 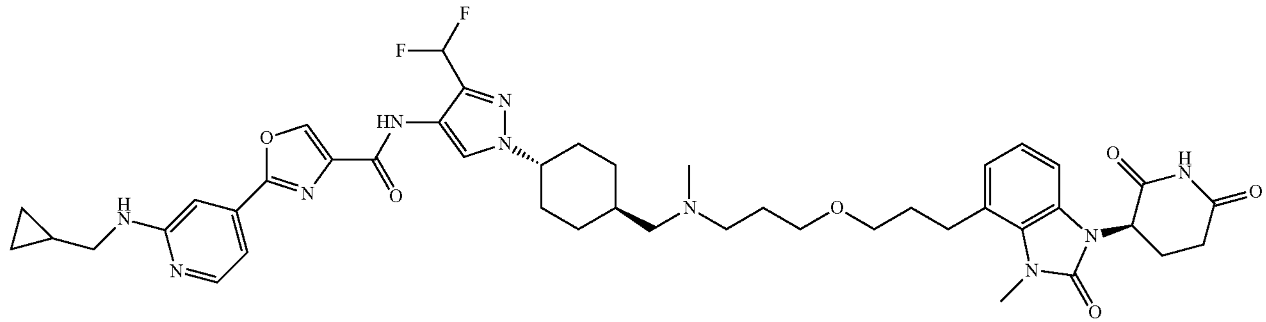 [SMILES: CN(CCCOCCCc1cccc2c1n(C)c(=O)n2[C@@H]1CCC(=O)NC1=O)C[C@H]1CC[C@H](n2cc(NC(=O)c3coc(-c4ccnc(NCC5CC5)c4)n3)c(C(F)F)n2)CC1] |
| I-91 | 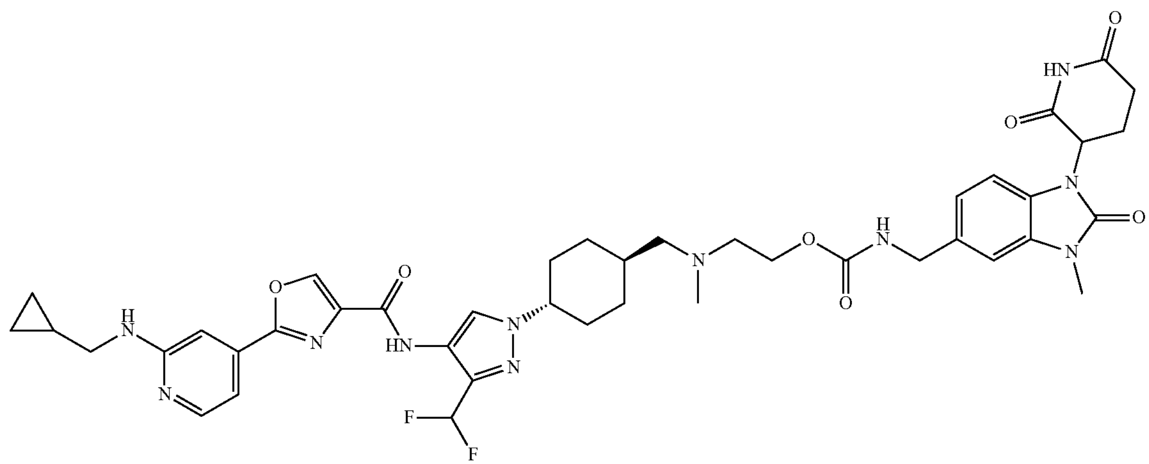 [SMILES: CN(CCOC(=O)NCc1ccc2c(c1)n(C)c(=O)n2C1CCC(=O)NC1=O)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-92 | 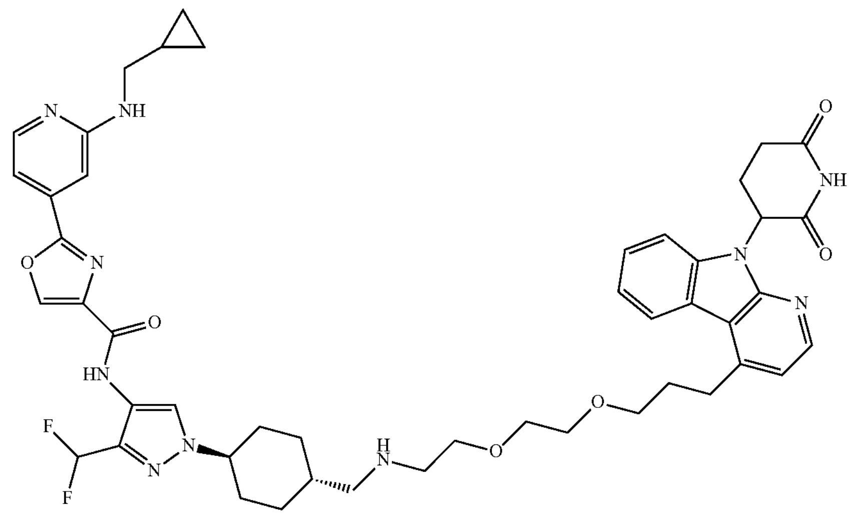 [SMILES: O=C1CCC(n2c3ccccc3c3c(CCCOCCOCCNC[C@H]4CC[C@H](n5cc(NC(=O)c6coc(-c7ccnc(NCC8CC8)c7)n6)c(C(F)F)n5)CC4)ccnc32)C(=O)N1] |
| I-93 | 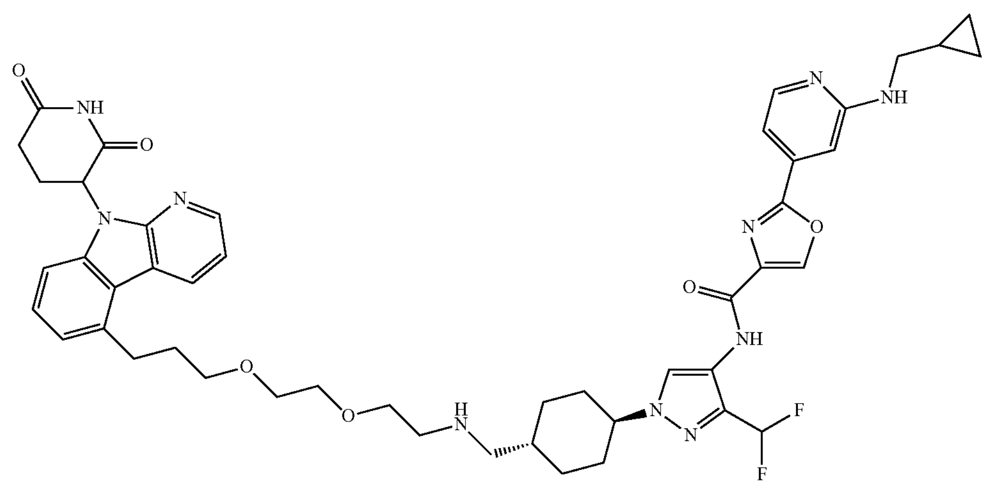 [SMILES: O=C1CCC(n2c3cccc(CCCOCCOCCNC[C@H]4CC[C@H](n5cc(NC(=O)c6coc(-c7ccnc(NCC8CC8)c7)n6)c(C(F)F)n5)CC4)c3c3cccnc32)C(=O)N1] |

TABLE 1-continued
Exemplary Compounds
| I-# | Structure |
|---|---|
| I-94 | 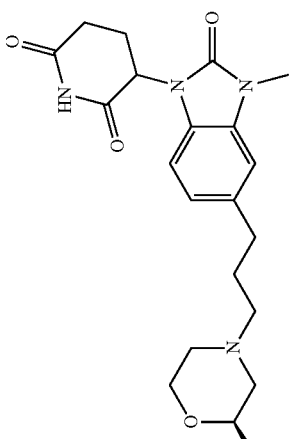 |
| I-95 | 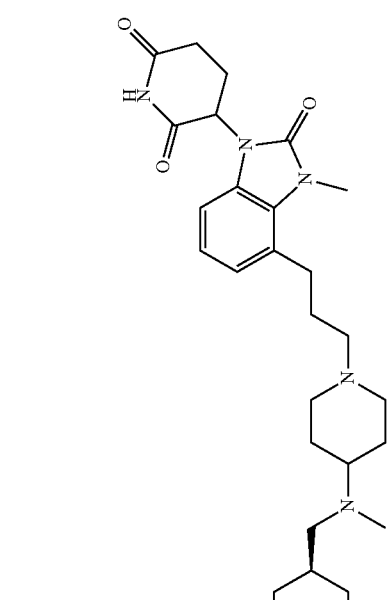 |

TABLE 1-continued
Exemplary Compounds
| I-# | Structure |
|---|---|
| I-96 | 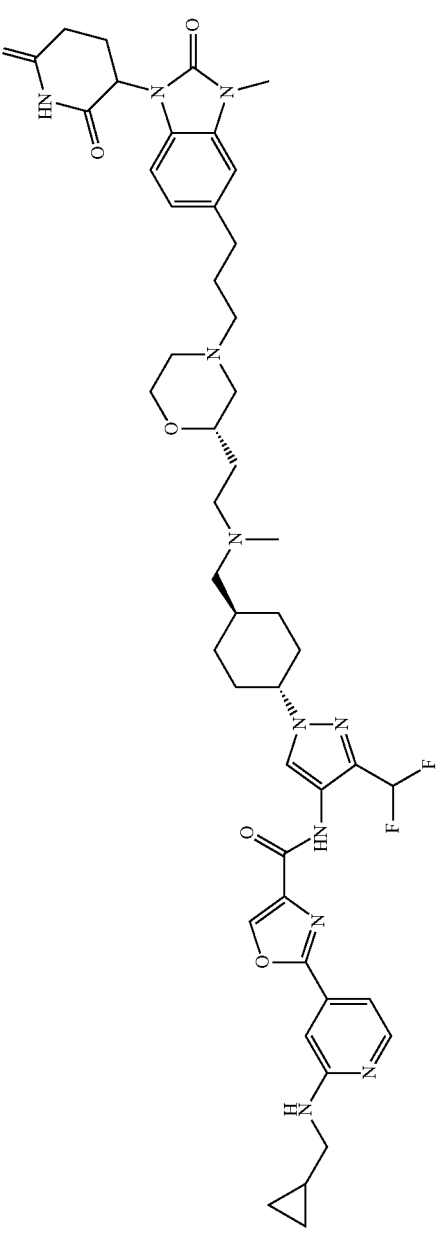 |
| I-97 | 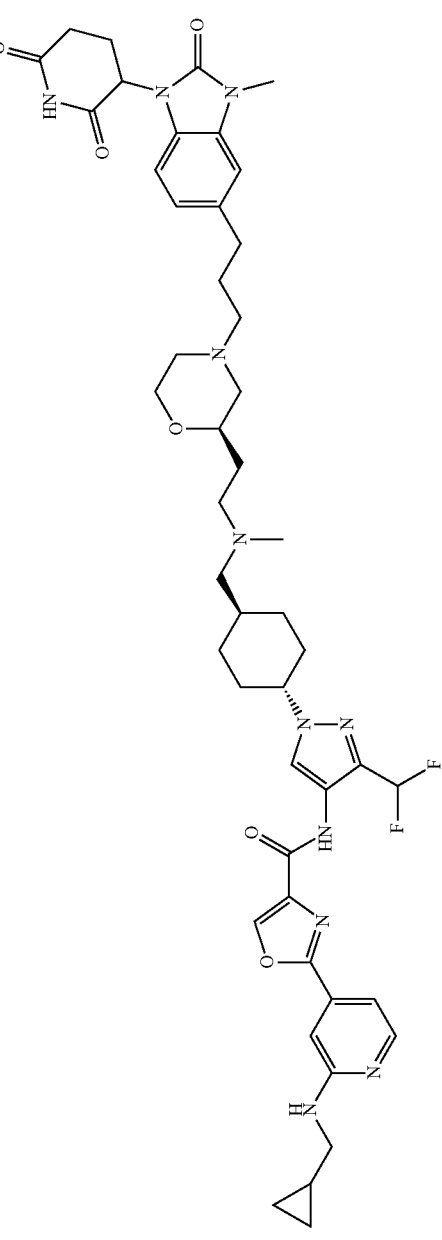 |

TABLE 1-continued
Exemplary Compounds
| I-# | Structure |
|---|---|
| I-98 | 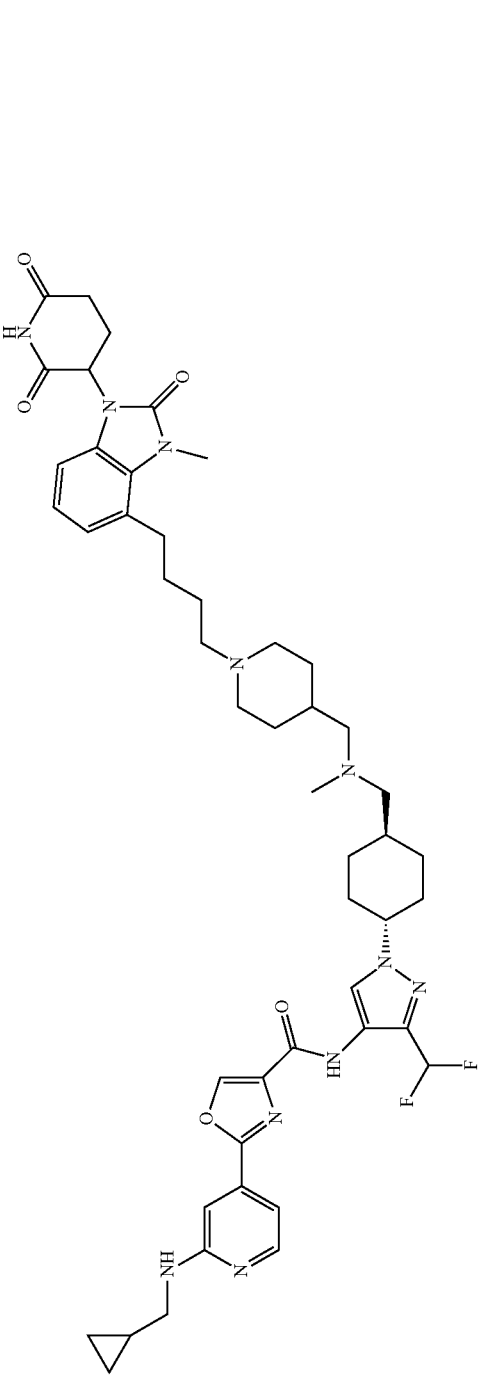 |
| I-106 | 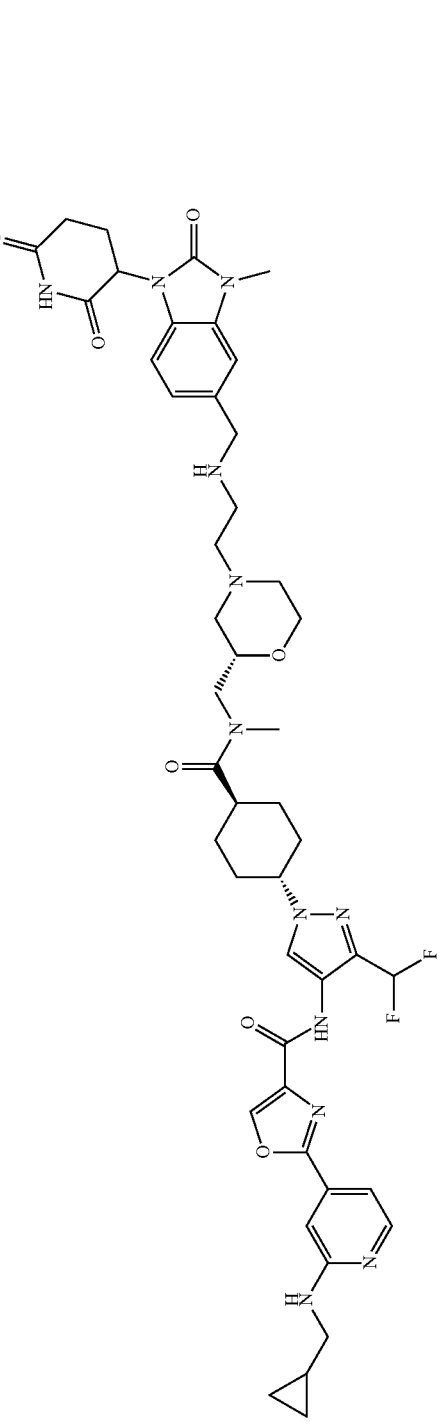 |

TABLE 1-continued
Exemplary Compounds
| I-# | Structure |
|---|---|
| I-107 | 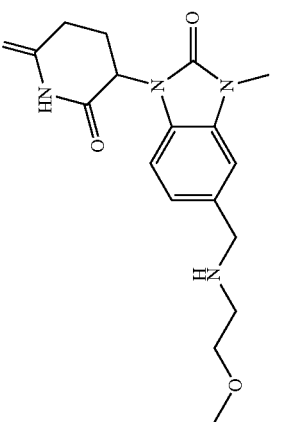 |
| I-108 | 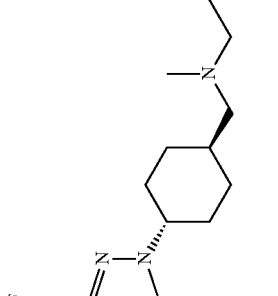 |

TABLE 1-continued
Exemplary Compounds
| I-# | Structure |
|---|---|
| I-109 | 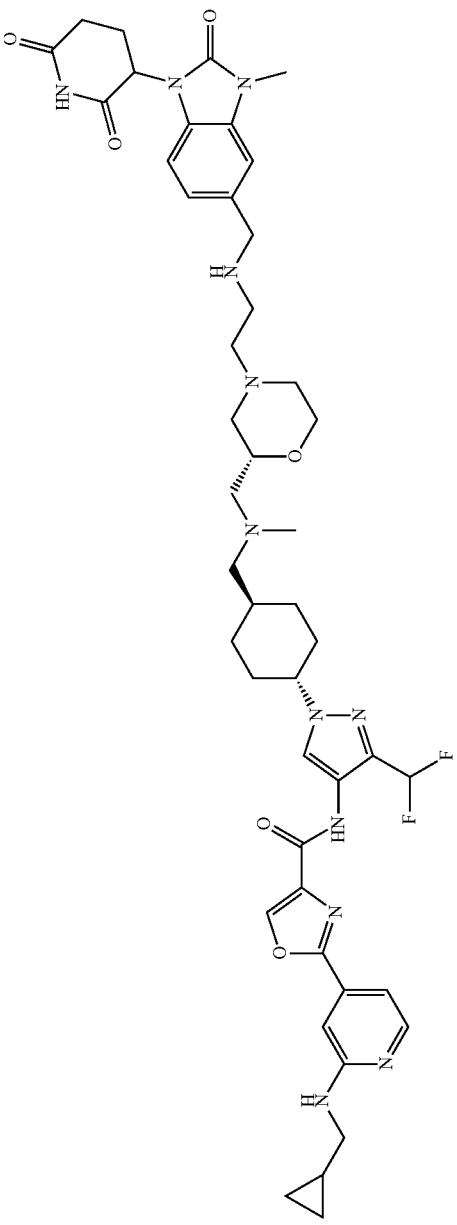 |
| I-110 | 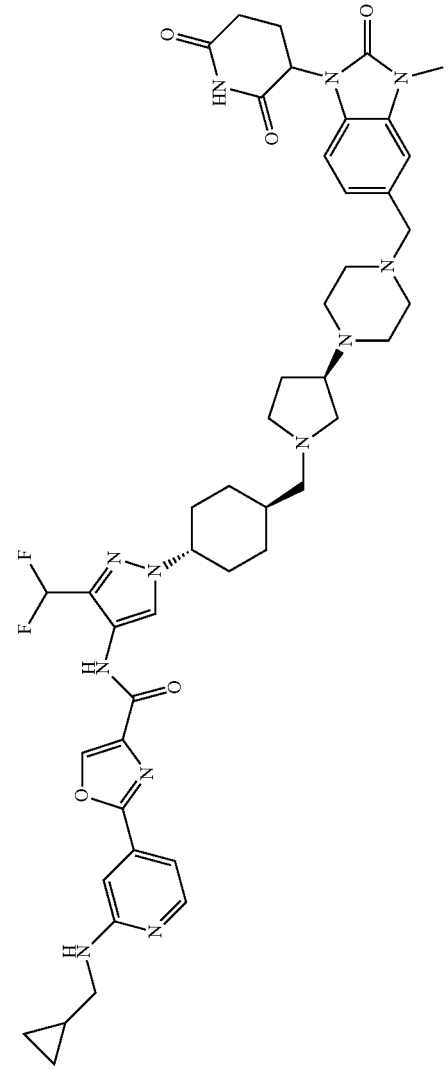 |

TABLE 1-continued
Exemplary Compounds
| I-# | Structure |
|---|---|
| I-111 | 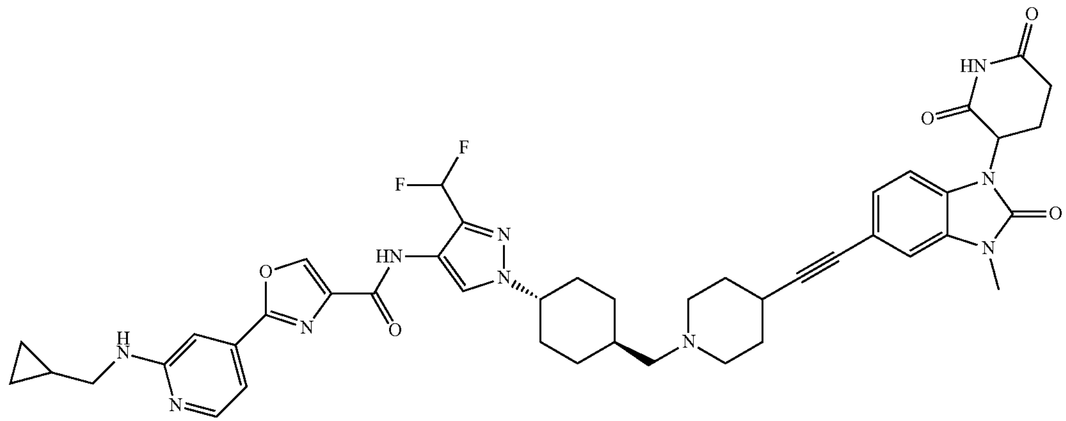 [SMILES: Cn1c(=O)n(C2CCC(=O)NC2=O)c2ccc(C#CC3CCN(C[C@H]4CC[C@H](n5cc(NC(=O)c6coc(-c7ccnc(NCC8CC8)c7)n6)c(C(F)F)n5)CC4)CC3)cc21] |
| I-112 | 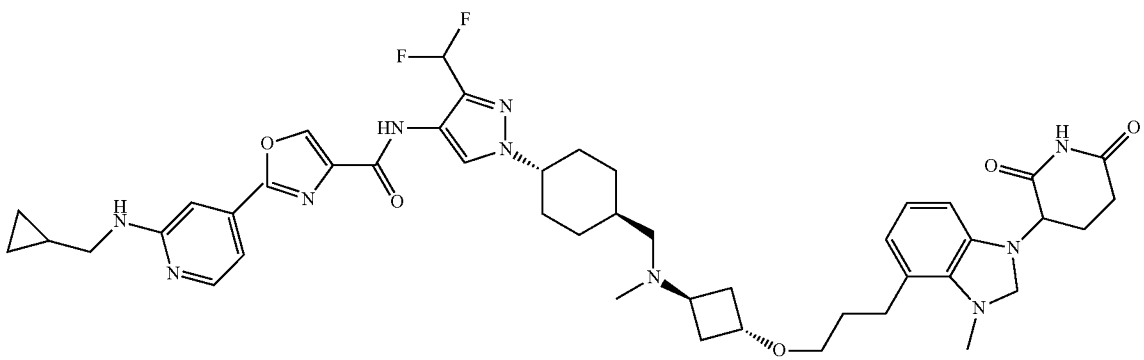 |

TABLE 1-continued
Exemplary Compounds
| I-# | Structure |
|---|---|
| I-113 | 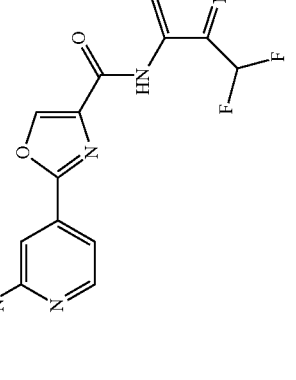 |
| I-114 | 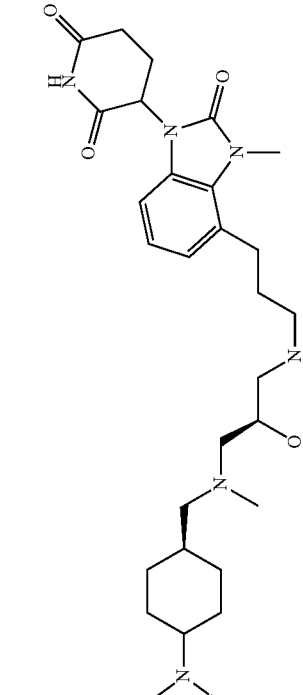 |

TABLE 1-continued
Exemplary Compounds
| I-# | Structure |
|---|---|
| I-115 | 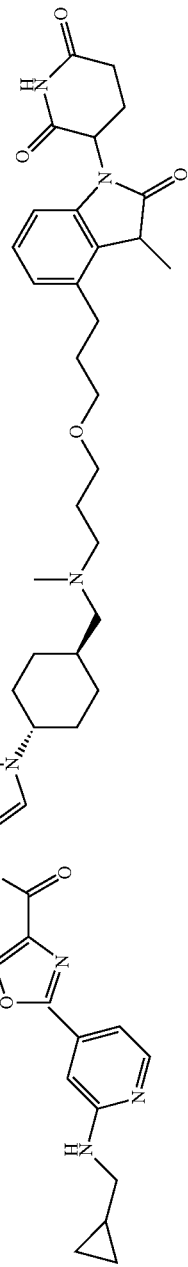 |
| I-116 | 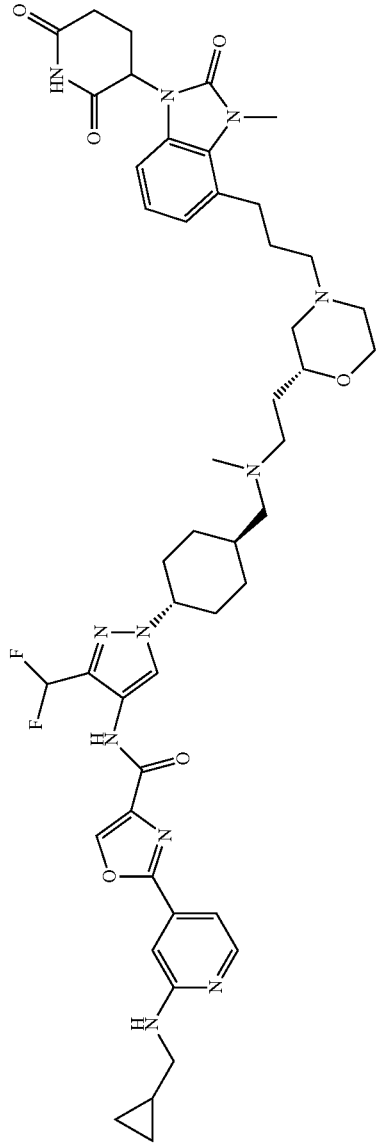 |

TABLE 1-continued
Exemplary Compounds
| I-# | Structure |
|---|---|
| I-117 | 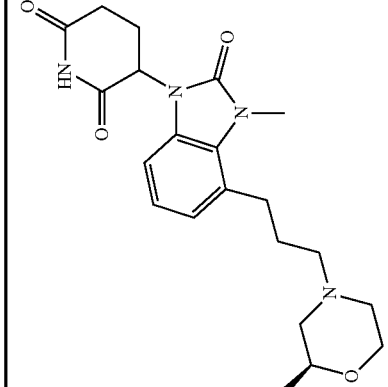 |
| I-118 | 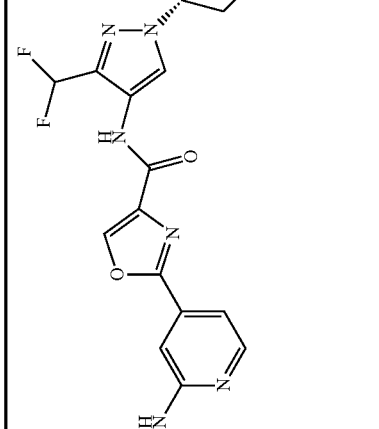 |

TABLE 1-continued

Exemplary Compounds

| I-# | Structure |
|---|---|
| I-119 | 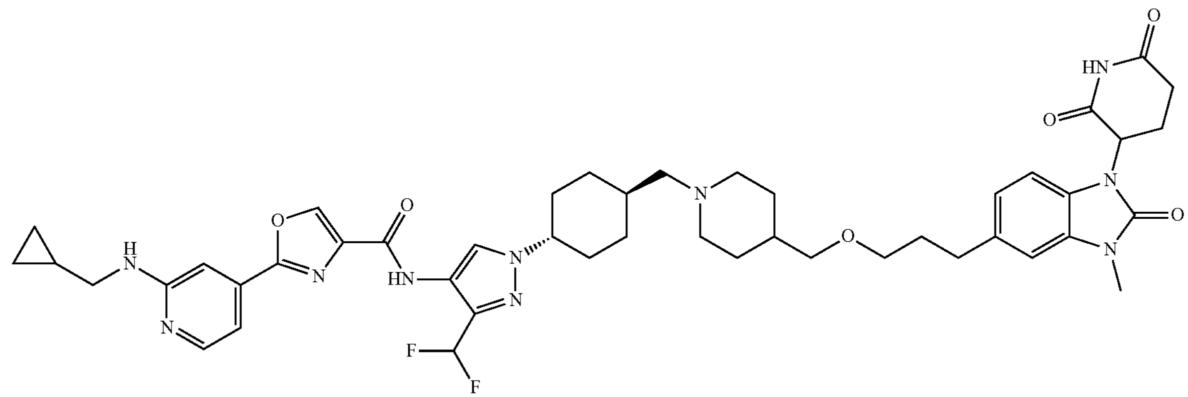 [SMILES: Cn1c(=O)n(C2CCC(=O)NC2=O)c2ccc(CCCOCC3CCN(C[C@H]4CC[C@H](n5cc(NC(=O)c6coc(-c7ccnc(NCC8CC8)c7)n6)c(C(F)F)n5)CC4)CC3)cc21] |
| I-120 | 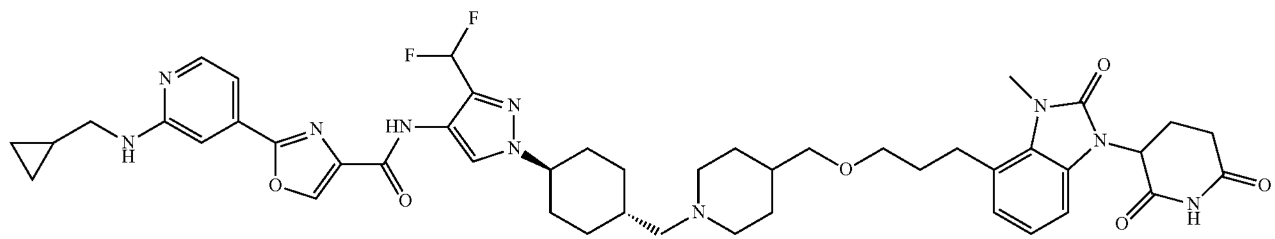 [SMILES: Cn1c(=O)n(C2CCC(=O)NC2=O)c2cccc(CCCOCC3CCN(C[C@H]4CC[C@H](n5cc(NC(=O)c6coc(-c7ccnc(NCC8CC8)c7)n6)c(C(F)F)n5)CC4)CC3)c21] |
| I-121 | 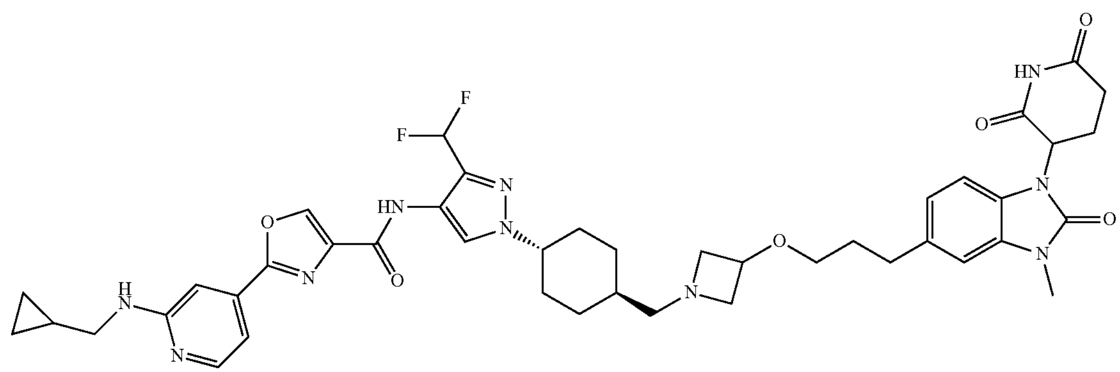 [SMILES: Cn1c(=O)n(C2CCC(=O)NC2=O)c2ccc(CCCOC3CN(C[C@H]4CC[C@H](n5cc(NC(=O)c6coc(-c7ccnc(NCC8CC8)c7)n6)c(C(F)F)n5)CC4)C3)cc21] |

TABLE 1-continued
Exemplary Compounds
| I-# | Structure |
|---|---|
| I-122 | 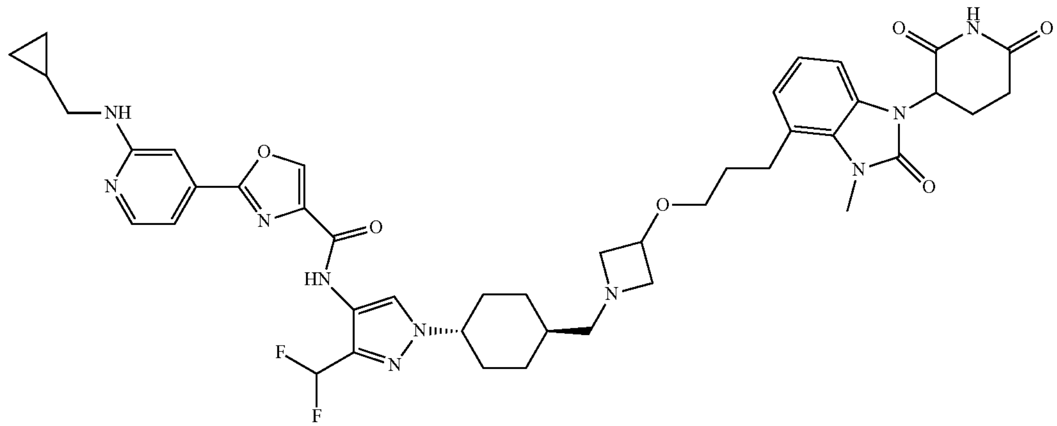 [SMILES: Cn1c(=O)n(C2CCC(=O)NC2=O)c2cccc(CCCOC3CN(C[C@H]4CC[C@H](n5cc(NC(=O)c6coc(-c7ccnc(NCC8CC8)c7)n6)c(C(F)F)n5)CC4)C3)c21] |
| I-123 | 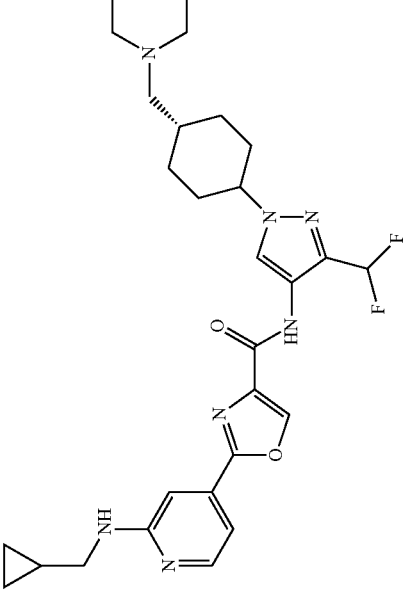 |

TABLE 1-continued
Exemplary Compounds
| I-# | Structure |
|---|---|
| I-124 | 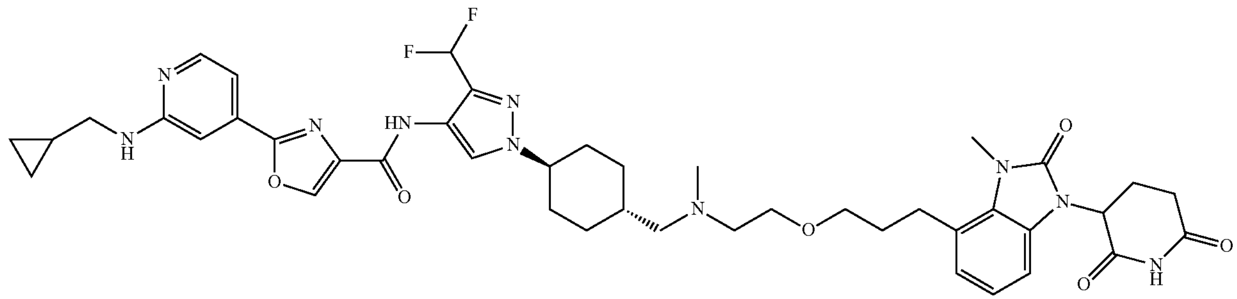 [SMILES: CN(CCOCCCc1cccc2c1n(C)c(=O)n2C1CCC(=O)NC1=O)C[C@H]1CC[C@H](n2cc(NC(=O)c3coc(-c4ccnc(NCC5CC5)c4)n3)c(C(F)F)n2)CC1] |
| I-125 | 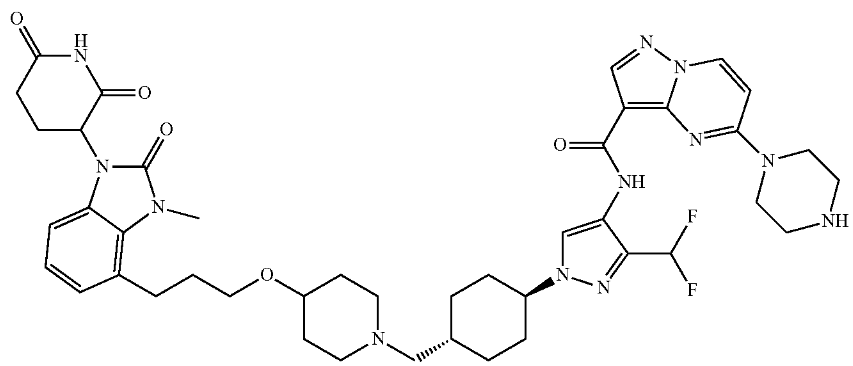 [SMILES: Cn1c(=O)n(C2CCC(=O)NC2=O)c2cccc(CCCOC3CCN(C[C@H]4CC[C@H](n5cc(NC(=O)c6cnn7ccc(N8CCNCC8)nc67)c(C(F)F)n5)CC4)CC3)c21] |
| I-126 | 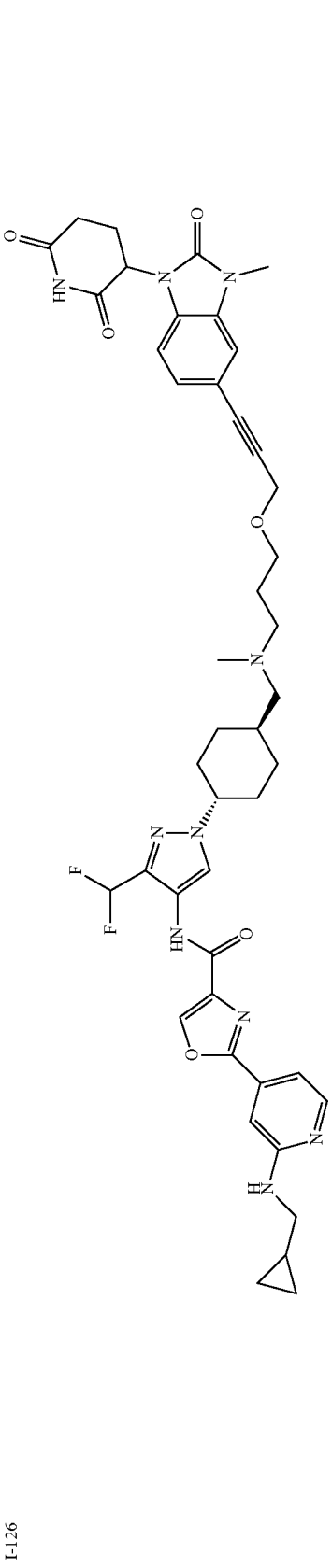 |

TABLE 1-continued
Exemplary Compounds
| I-# | Structure |
|---|---|
| I-127 | 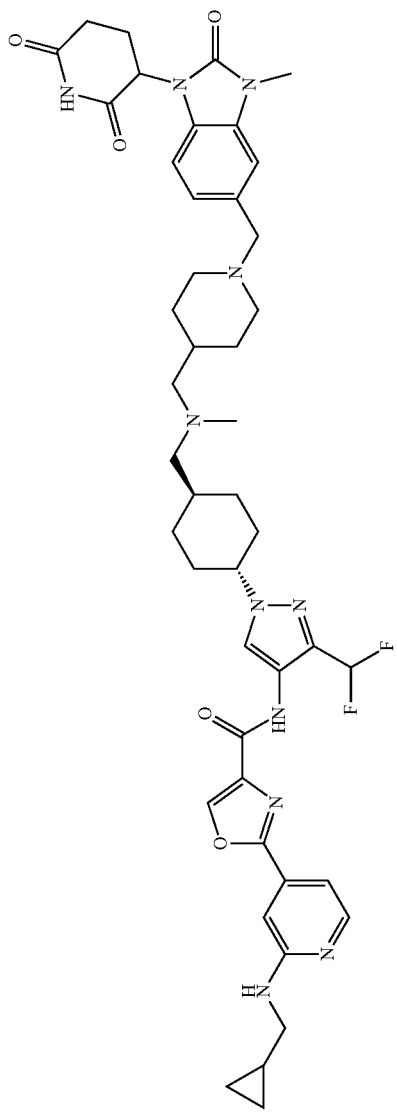 |
| I-128 | 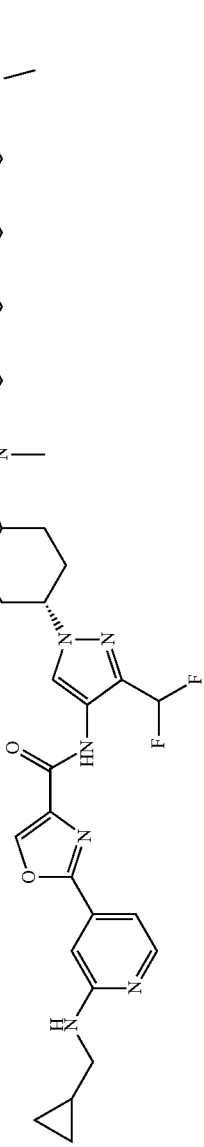 |

TABLE 1-continued
Exemplary Compounds
| I-# | Structure |
|---|---|
| I-129 | 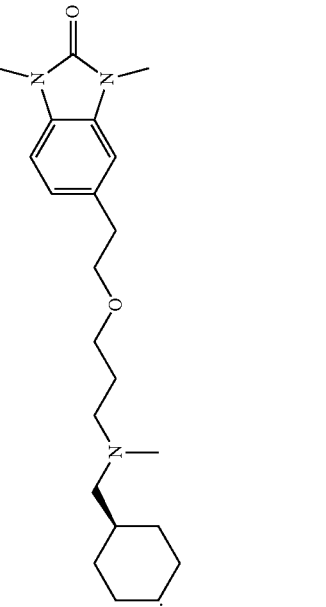 |
| I-130 | 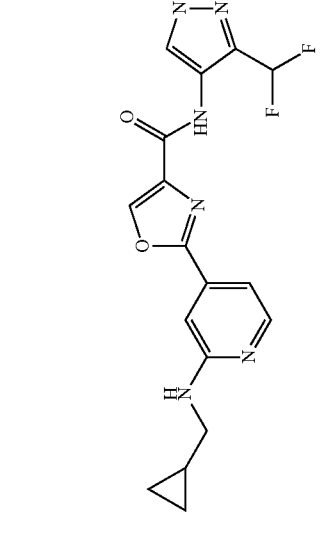 |

TABLE 1-continued
Exemplary Compounds
| I-# | Structure |
|---|---|
| I-131 | 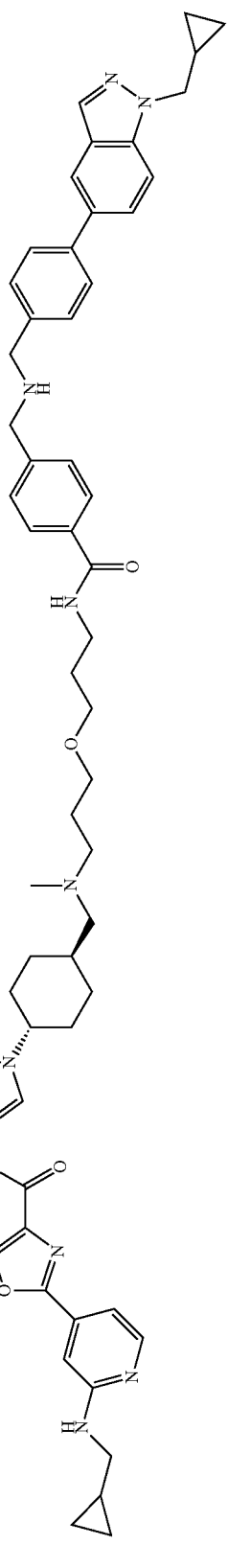 |
| I-132 | 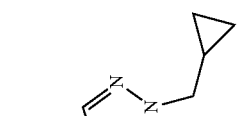 |

TABLE 1-continued
Exemplary Compounds
| I-# | Structure |
|---|---|
| I-133 | 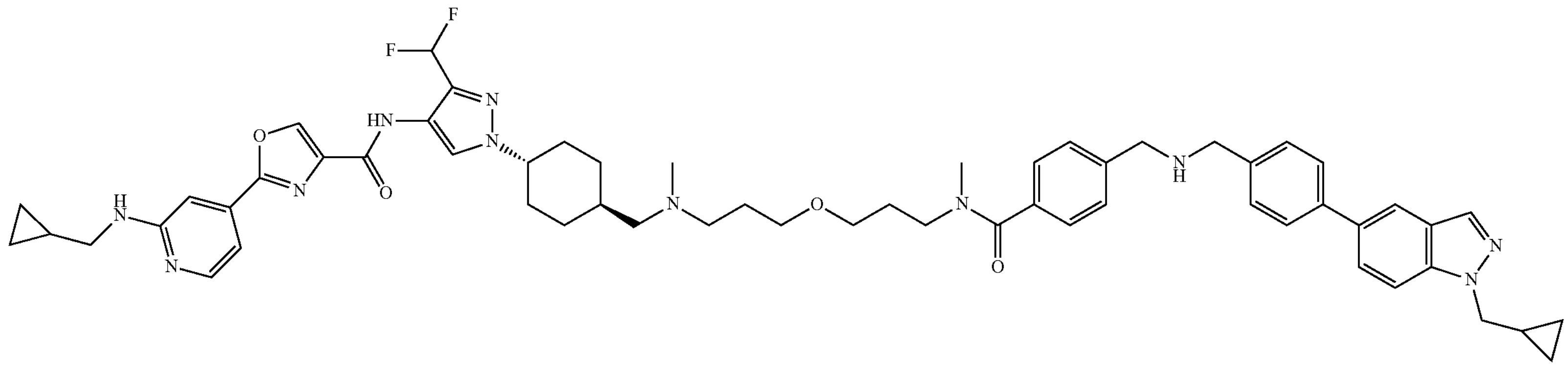 [SMILES: CN(CCCOCCCN(C)C(=O)c1ccc(CNCc2ccc(-c3ccc4c(cnn4CC4CC4)c3)cc2)cc1)C[C@H]1CC[C@H](n2cc(NC(=O)c3coc(-c4ccnc(NCC5CC5)c4)n3)c(C(F)F)n2)CC1] |
| I-134 | 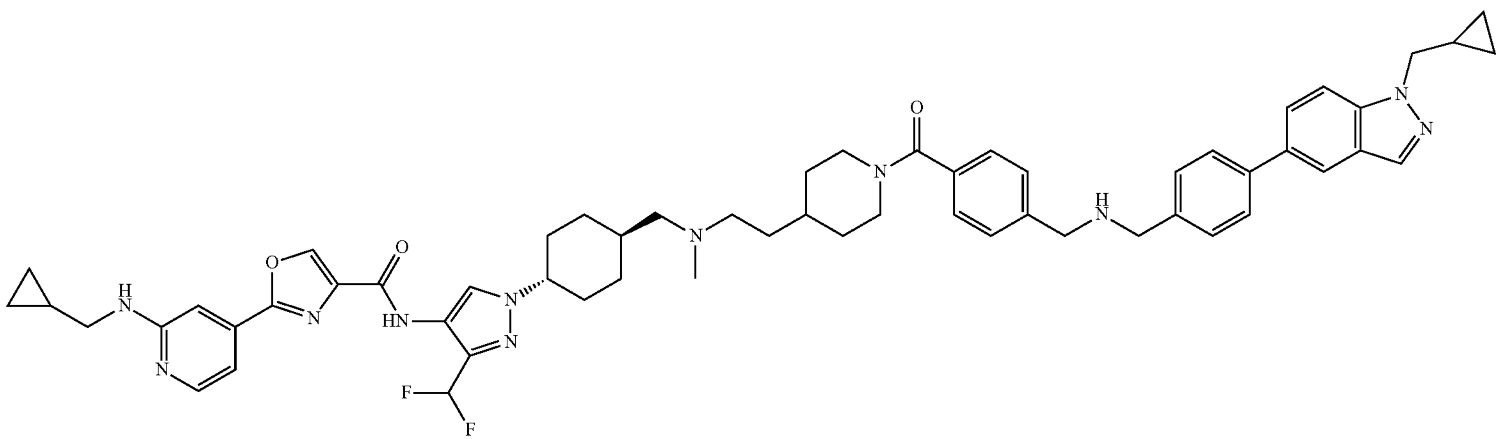 [SMILES: CN(CCC1CCN(C(=O)c2ccc(CNCc3ccc(-c4ccc5c(cnn5CC5CC5)c4)cc3)cc2)CC1)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-135 | 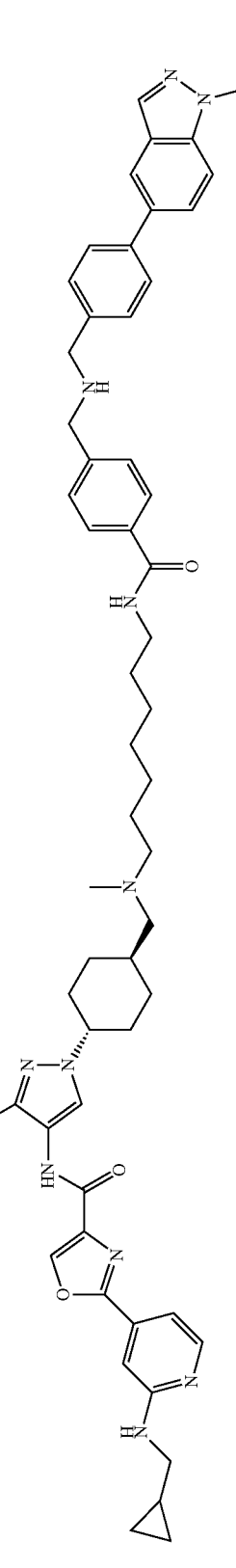 |
| I-136 | 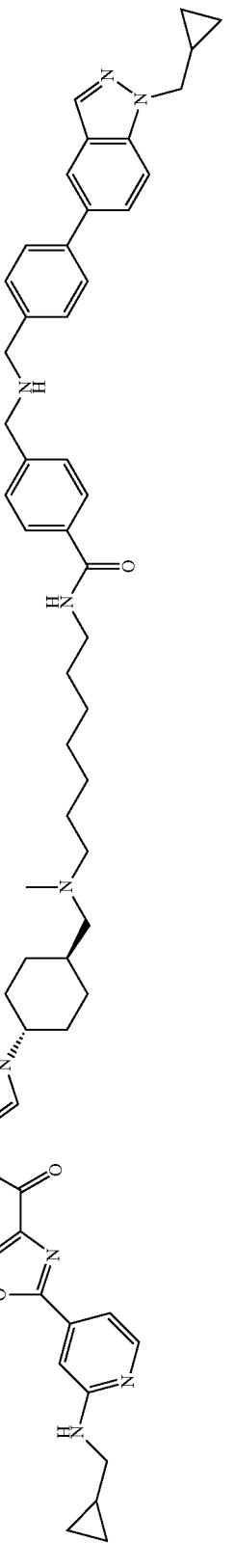 |

TABLE 1-continued
Exemplary Compounds
| I-# | Structure |
|---|---|
| I-137 | 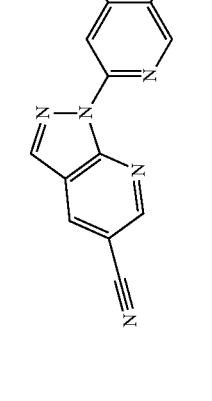 |
| I-138 | 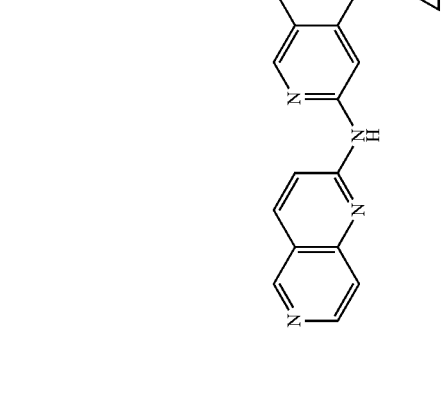 |
| I-139 | 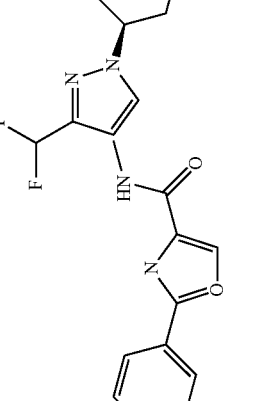 |

TABLE 1-continued
Exemplary Compounds
| I-# | Structure |
|---|---|
| I-140 | 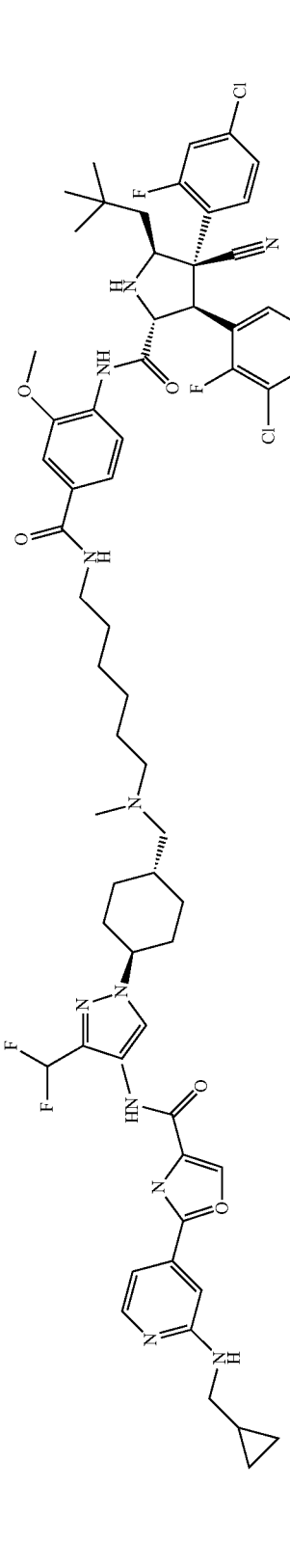 |
| I-141 | 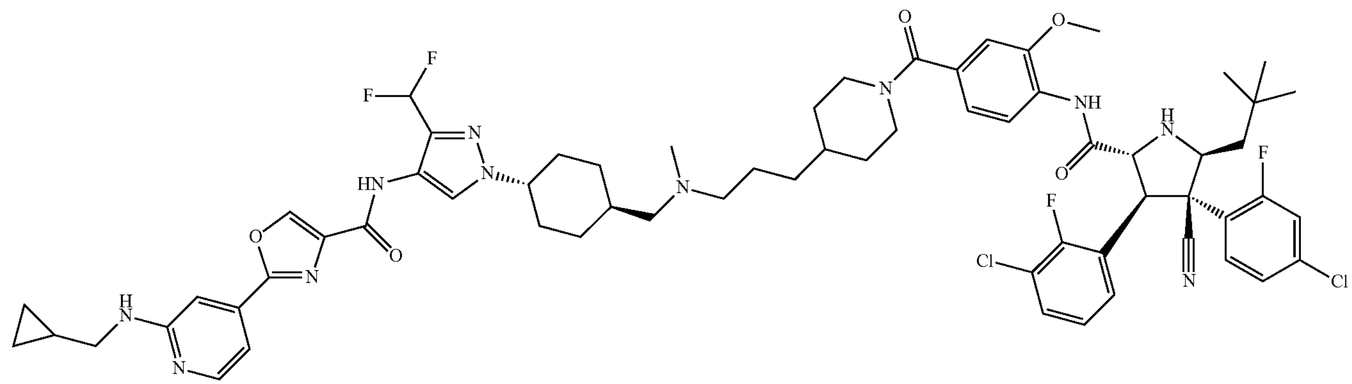 [SMILES: COc1cc(C(=O)N2CCC(CCCN(C)C[C@H]3CC[C@H](n4cc(NC(=O)c5coc(-c6ccnc(NCC7CC7)c6)n5)c(C(F)F)n4)CC3)CC2)ccc1NC(=O)[C@@H]1N[C@@H](CC(C)(C)C)[C@](C#N)(c2ccc(Cl)cc2F)[C@H]1c1cccc(Cl)c1F] |

TABLE 1-continued

Exemplary Compounds

| I-# | Structure |
|---|---|
| I-142 | 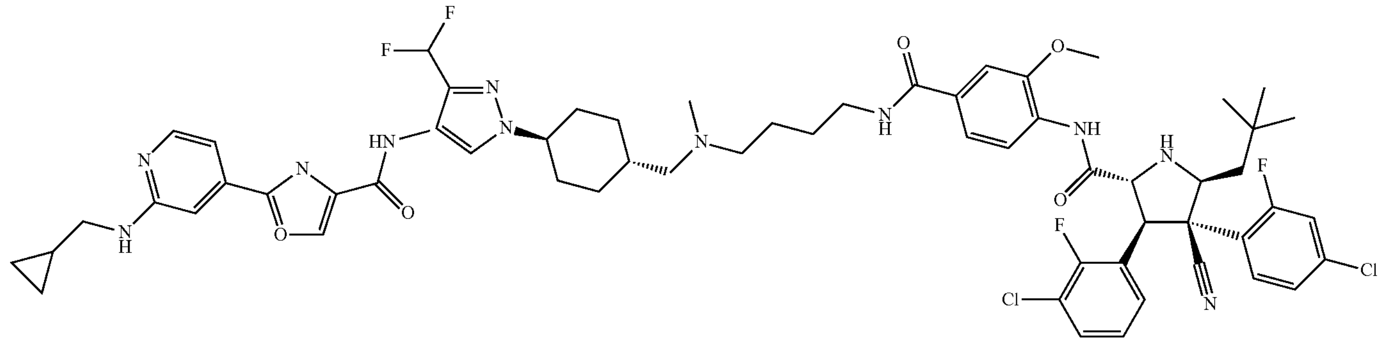 |
| I-143 | 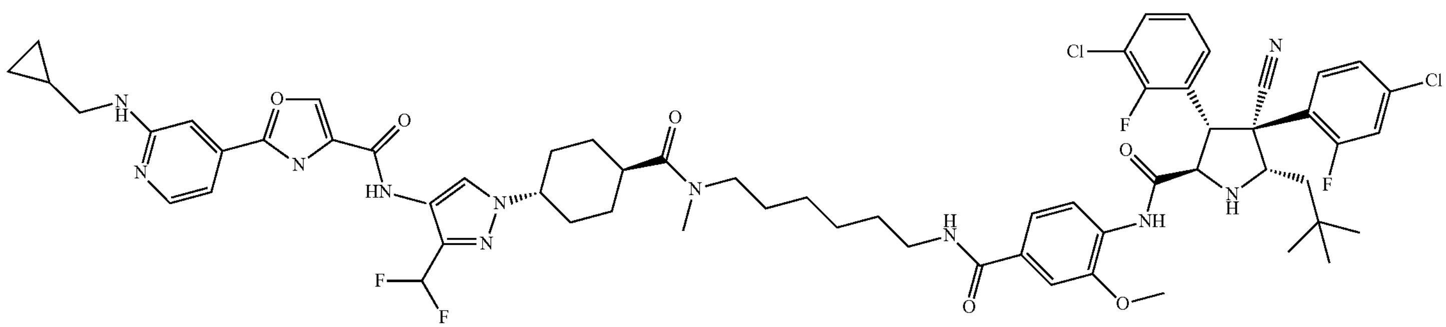 |

TABLE 1-continued

Exemplary Compounds

| I-# | Structure |
|---|---|
| I-144 | 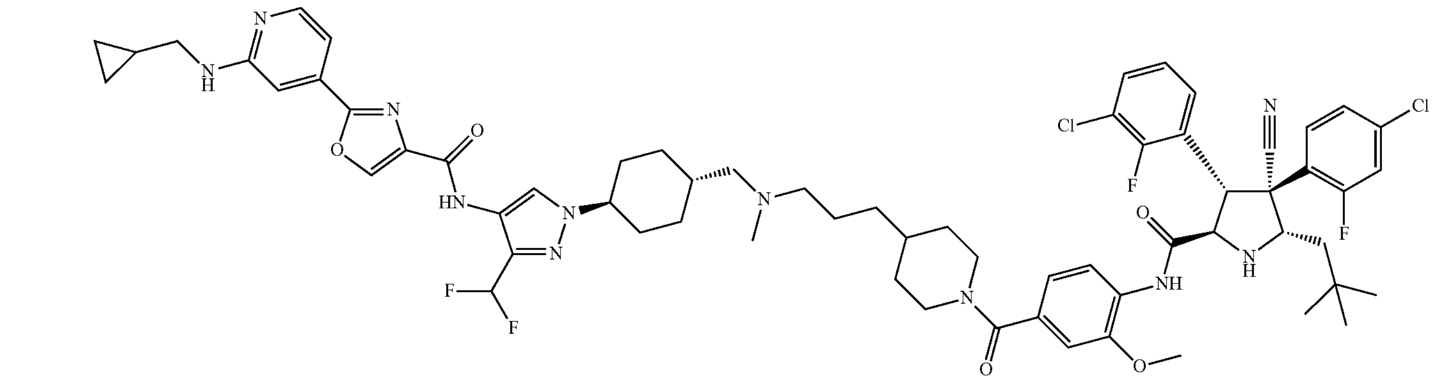 [SMILES: COc1cc(C(=O)N2CCC(CCCN(C)C[C@H]3CC[C@H](n4cc(NC(=O)c5coc(-c6ccnc(NCC7CC7)c6)n5)c(C(F)F)n4)CC3)CC2)ccc1NC(=O)[C@@H]1N[C@@H](CC(C)(C)C)[C@](C#N)(c2ccc(Cl)cc2F)[C@H]1c1cccc(Cl)c1F] |
| I-145 | 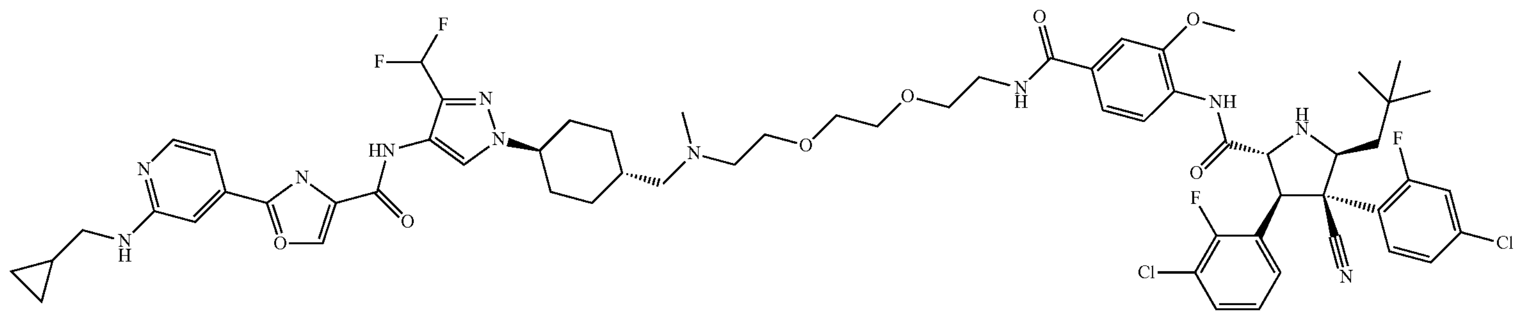 |

TABLE 1-continued
Exemplary Compounds
| I-# | Structure |
|---|---|
| I-146 | 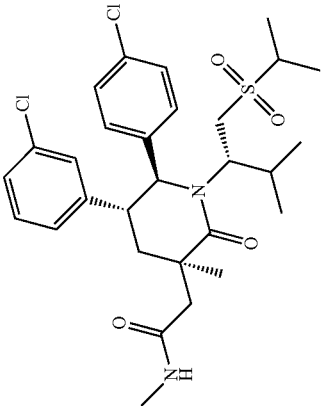 |
| I-147 | 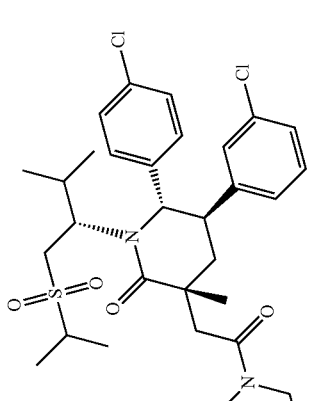 |

TABLE 1-continued
Exemplary Compounds
| I-# | Structure |
|---|---|
| I-148 | 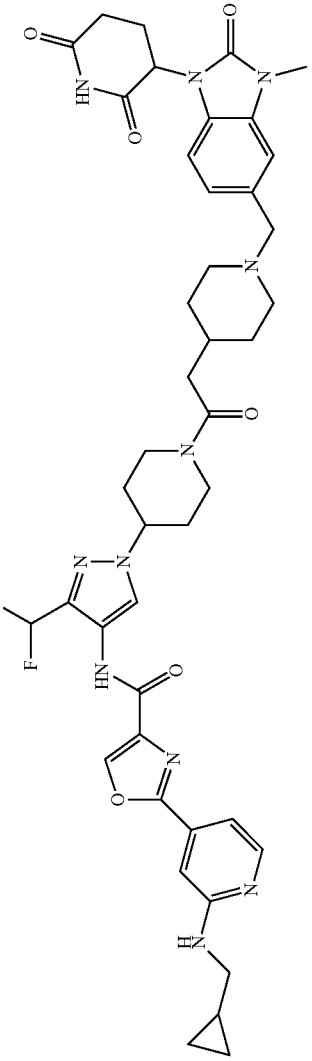 |
| I-149 | 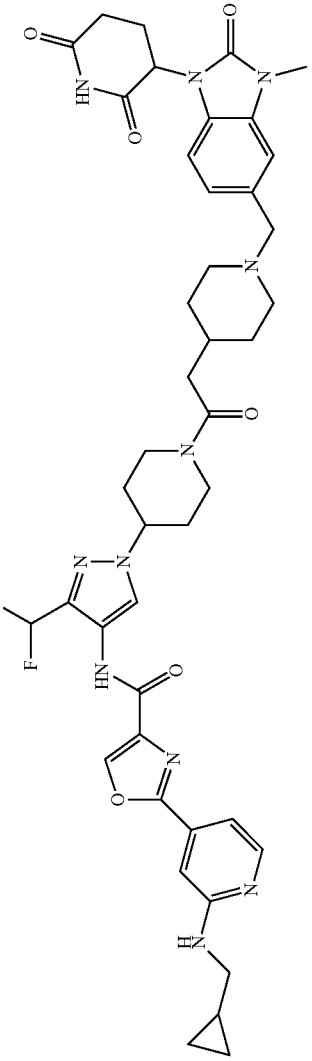 |

TABLE 1-continued
Exemplary Compounds
| I-# | Structure |
|---|---|
| I-150 | 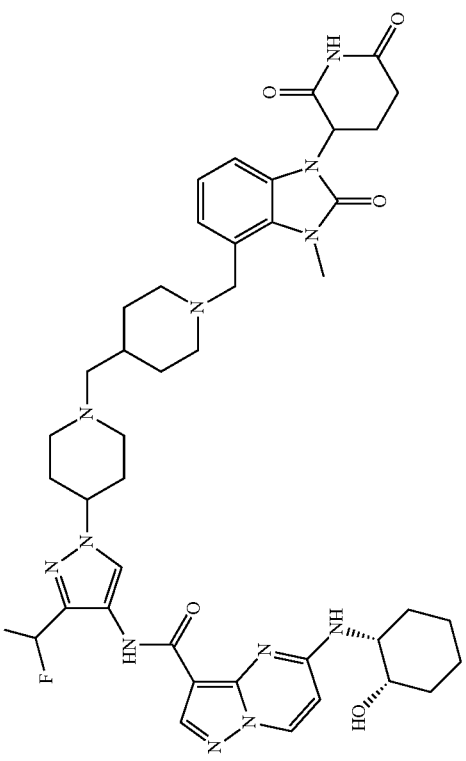 |
| I-151 | 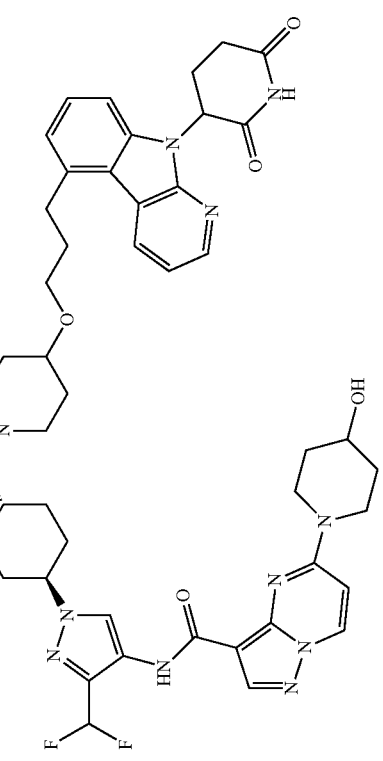 |

TABLE 1-continued
Exemplary Compounds
| I-# | Structure |
|---|---|
| I-152 | 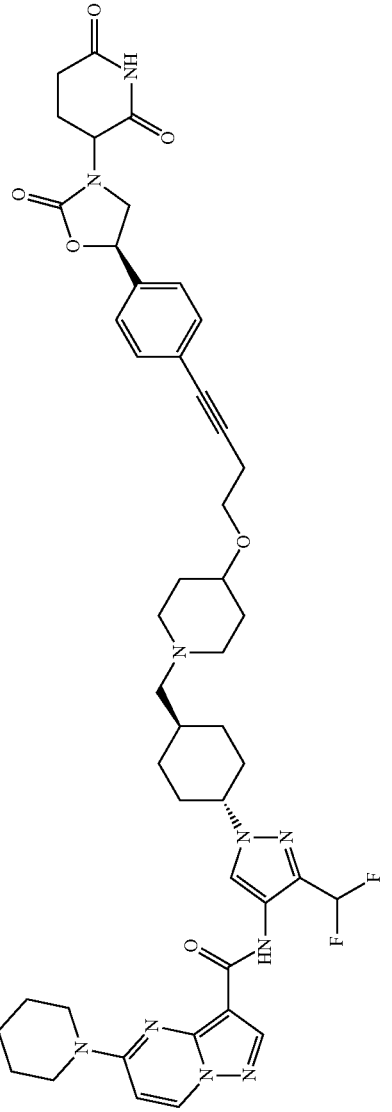 |
| I-153 | 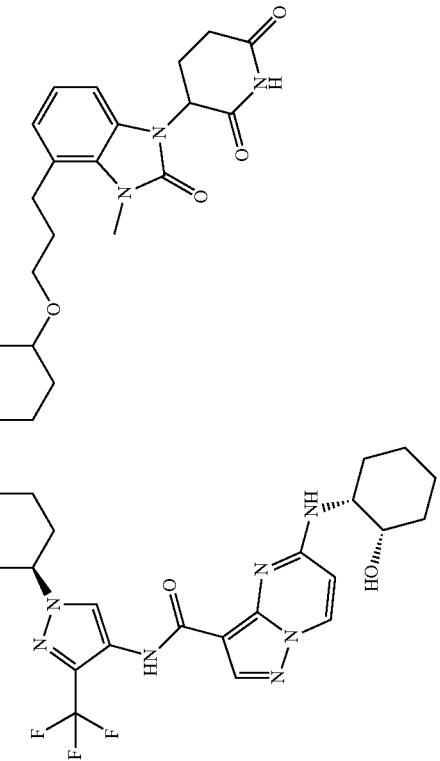 |

TABLE 1-continued
Exemplary Compounds
| I-# | Structure |
|---|---|
| I-154 | 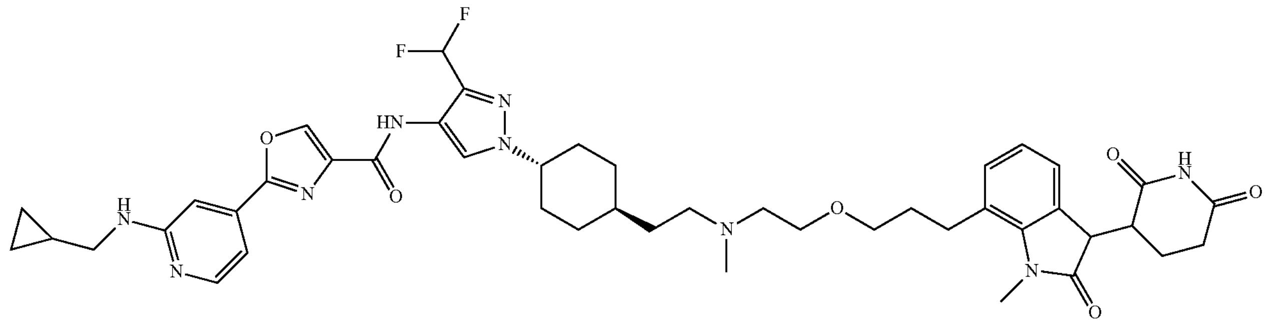 [SMILES: CN(CCOCCCc1cccc2c1N(C)C(=O)C2C1CCC(=O)NC1=O)CC[C@H]1CC[C@H](n2cc(NC(=O)c3coc(-c4ccnc(NCC5CC5)c4)n3)c(C(F)F)n2)CC1] |
| I-155 | 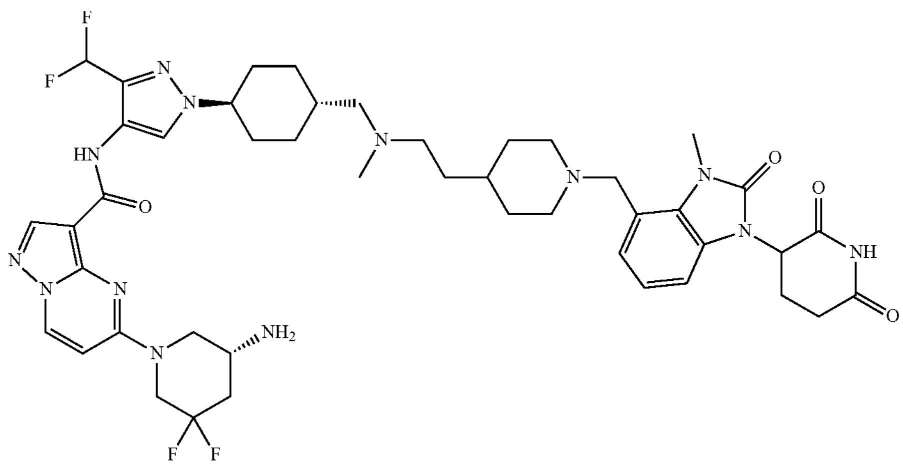 [SMILES: CN(CCC1CCN(Cc2cccc3c2n(C)c(=O)n3C2CCC(=O)NC2=O)CC1)C[C@H]1CC[C@H](n2cc(NC(=O)c3cnn4ccc(N5C[C@H](N)CC(F)(F)C5)nc34)c(C(F)F)n2)CC1] |

TABLE 1-continued
Exemplary Compounds
| I-# | Structure |
|---|---|
| I-156 | 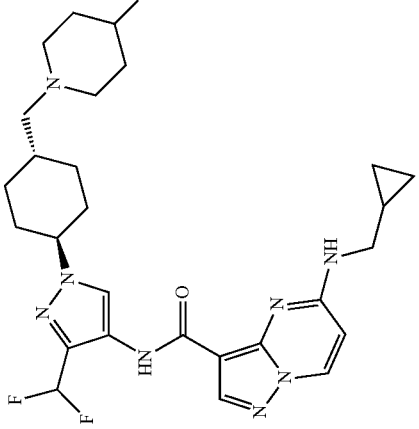 |
| I-157 | 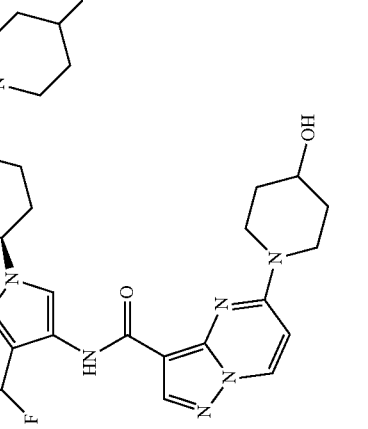 |

TABLE 1-continued
Exemplary Compounds
| I-# | Structure |
|---|---|
| I-158 | 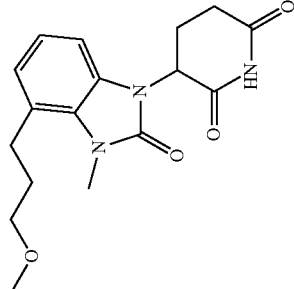 |
| I-159 | 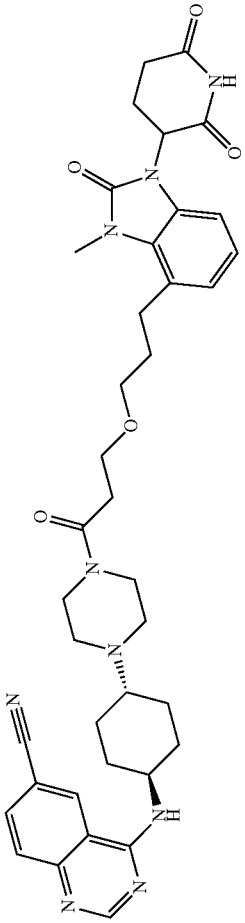 |
| I-160 | 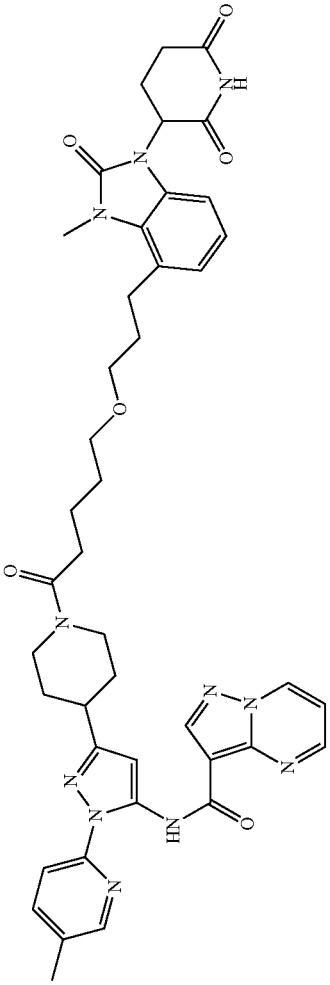 |

TABLE 1-continued
Exemplary Compounds
| I-# | Structure |
|---|---|
| I-161 | 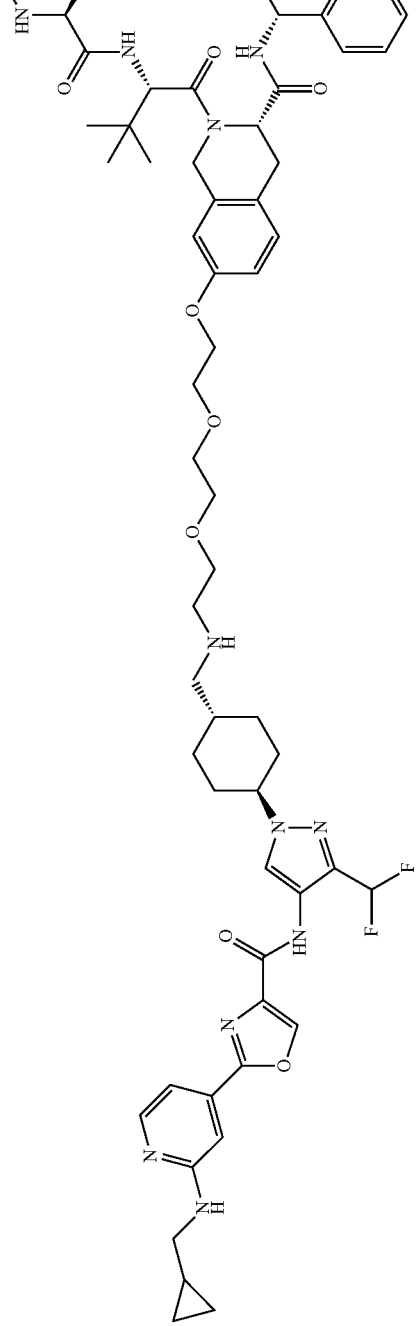 |
| I-162 | 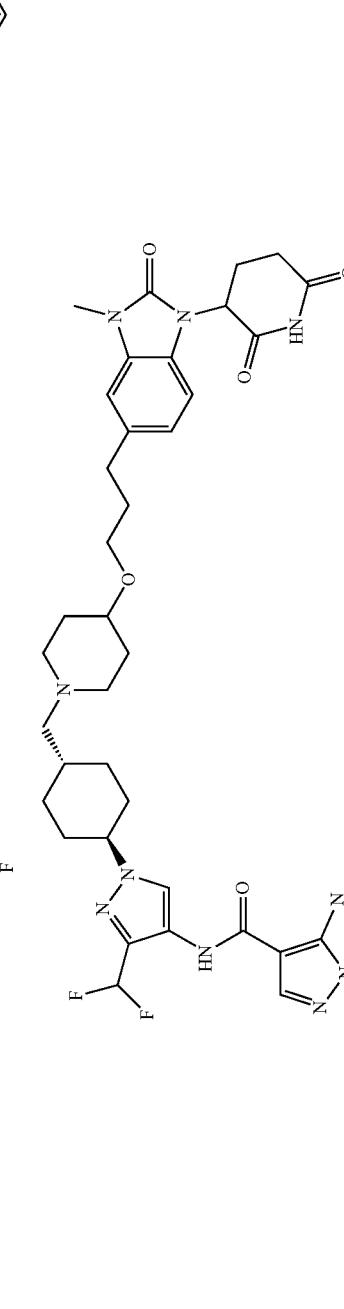 |

TABLE 1-continued
Exemplary Compounds
| I-# | Structure |
|---|---|
| I-163 | 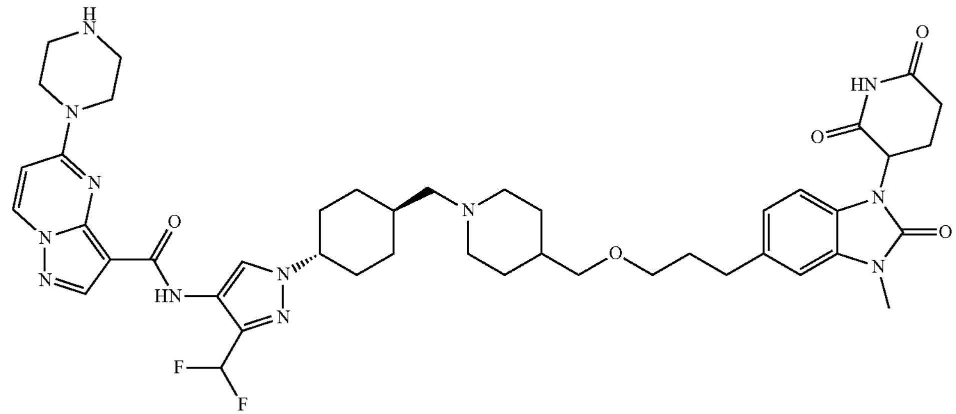 [SMILES: Cn1c(=O)n(C2CCC(=O)NC2=O)c2ccc(CCCOCC3CCN(C[C@H]4CC[C@H](n5cc(NC(=O)c6cnn7ccc(N8CCNCC8)nc67)c(C(F)F)n5)CC4)CC3)cc21] |
| I-164 | 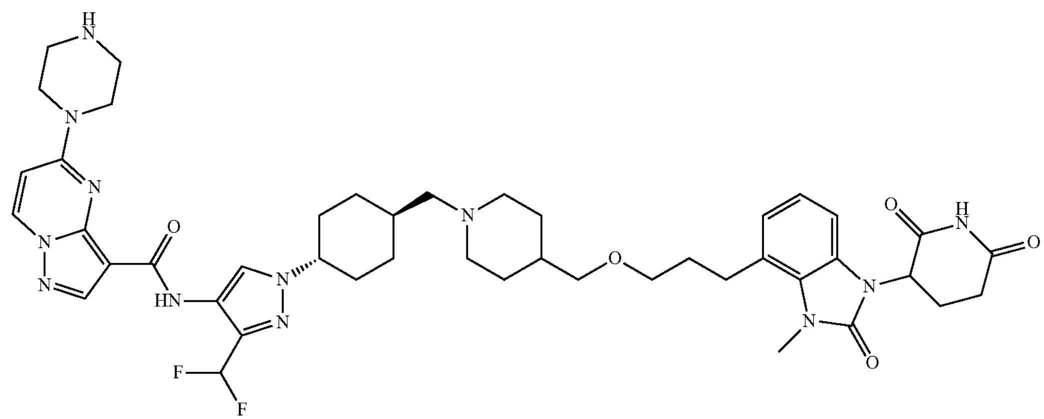 [SMILES: Cn1c(=O)n(C2CCC(=O)NC2=O)c2cccc(CCCOCC3CCN(C[C@H]4CC[C@H](n5cc(NC(=O)c6cnn7ccc(N8CCNCC8)nc67)c(C(F)F)n5)CC4)CC3)c21] |

TABLE 1-continued
Exemplary Compounds
| I-# | Structure |
|---|---|
| I-165 | 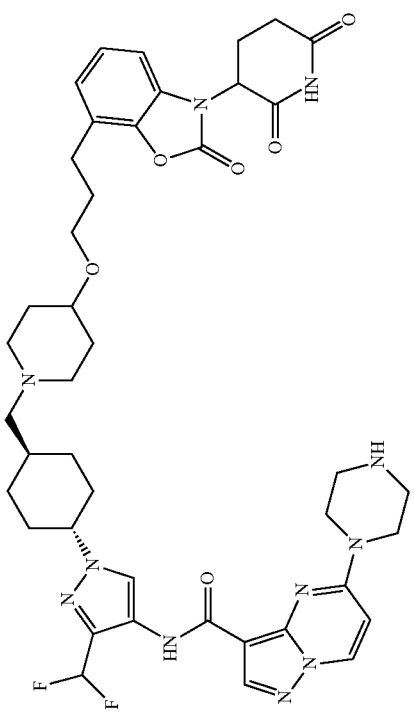 |
| I-166 | 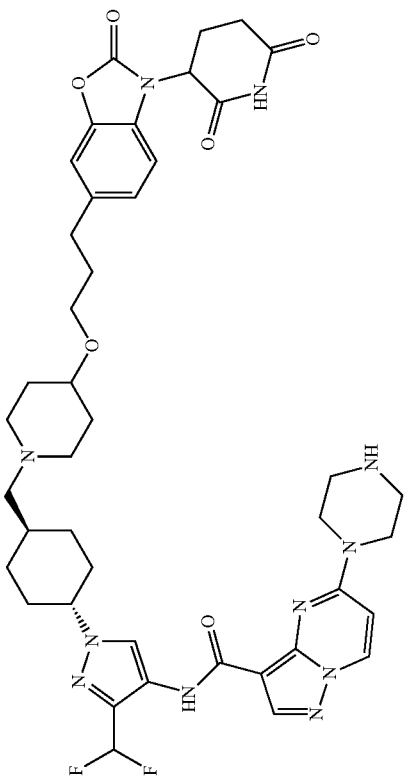 |

TABLE 1-continued

Exemplary Compounds

| I-# | Structure |
|---|---|
| I-167 | 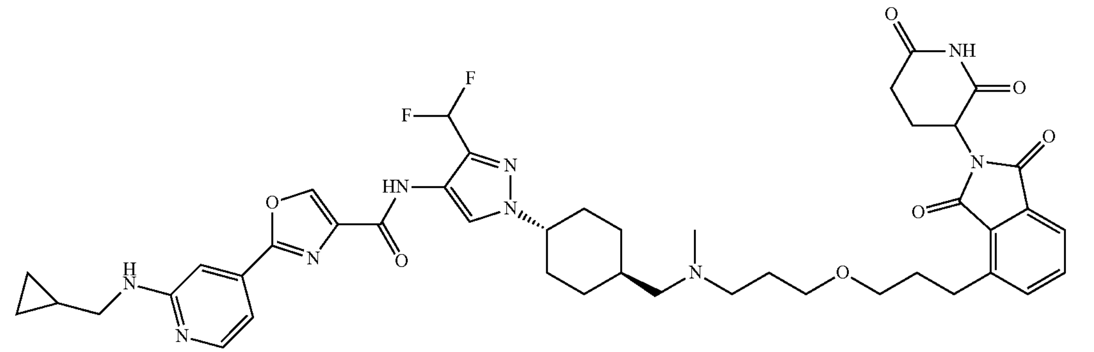 [SMILES: CN(CCCOCCCc1cccc2c1C(=O)N(C1CCC(=O)NC1=O)C2=O)C[C@H]1CC[C@H](n2cc(NC(=O)c3coc(-c4ccnc(NCC5CC5)c4)n3)c(C(F)F)n2)CC1] |
| I-168 | 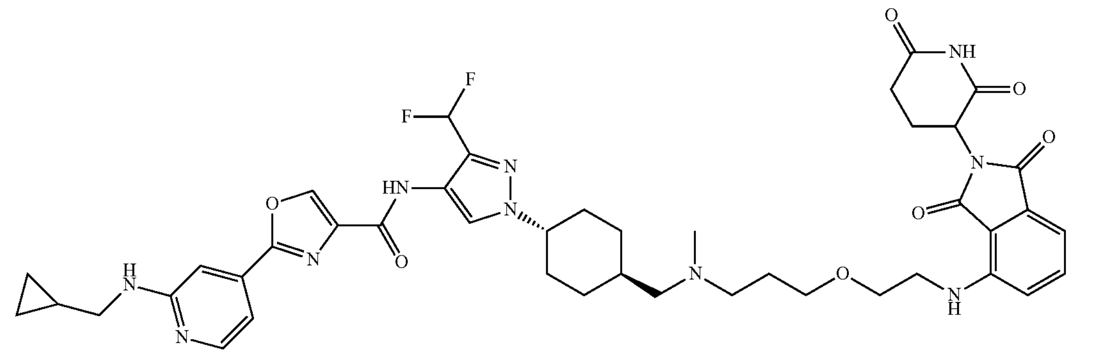 [SMILES: CN(CCCOCCNc1cccc2c1C(=O)N(C1CCC(=O)NC1=O)C2=O)C[C@H]1CC[C@H](n2cc(NC(=O)c3coc(-c4ccnc(NCC5CC5)c4)n3)c(C(F)F)n2)CC1] |
| I-169 | 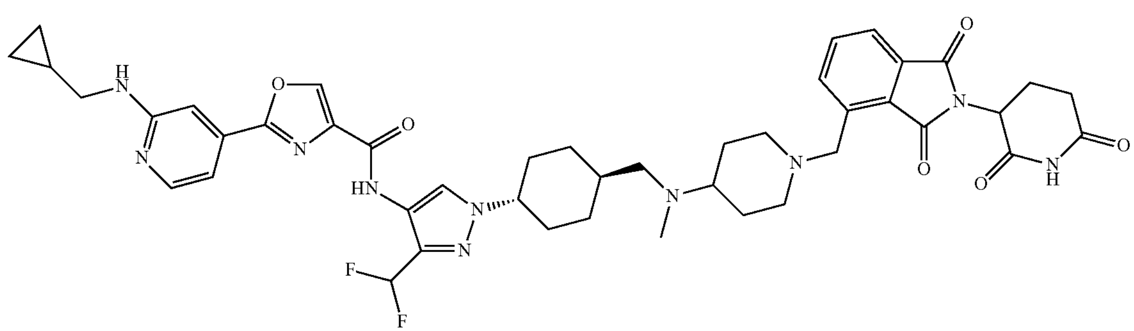 [SMILES: CN(C[C@H]1CC[C@H](n2cc(NC(=O)c3coc(-c4ccnc(NCC5CC5)c4)n3)c(C(F)F)n2)CC1)C1CCN(Cc2cccc3c2C(=O)N(C2CCC(=O)NC2=O)C3=O)CC1] |

TABLE 1-continued
Exemplary Compounds
| I-# | Structure |
|---|---|
| I-170 | 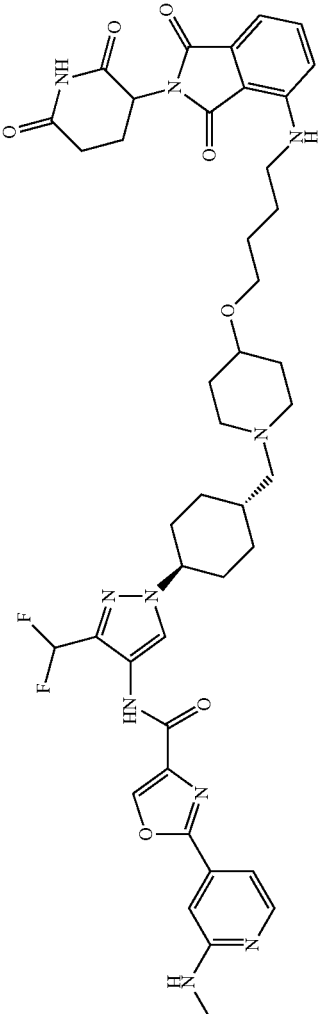 |
| I-171 | 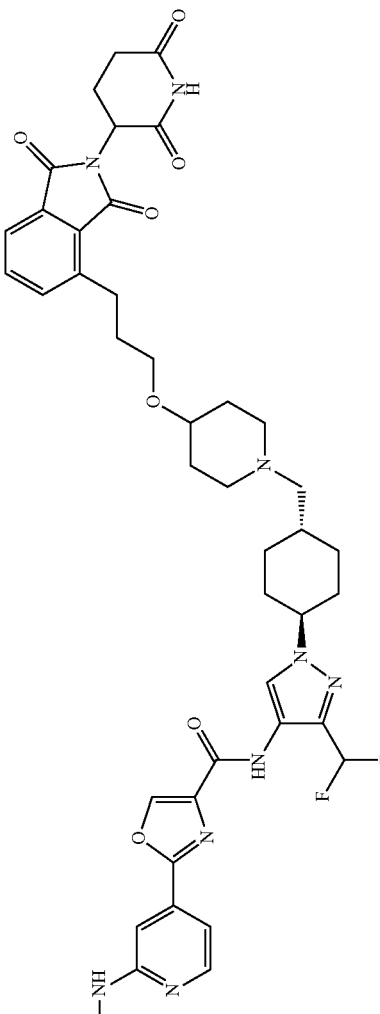 |

TABLE 1-continued
Exemplary Compounds
| I-# | Structure |
|---|---|
| I-172 | 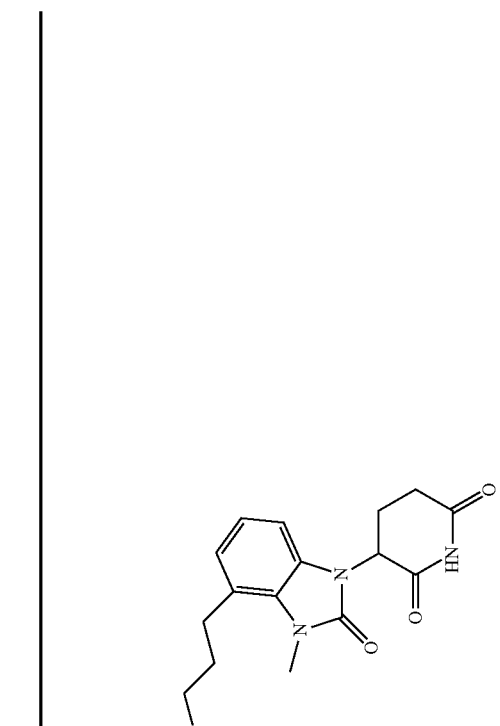 |
| I-173 | 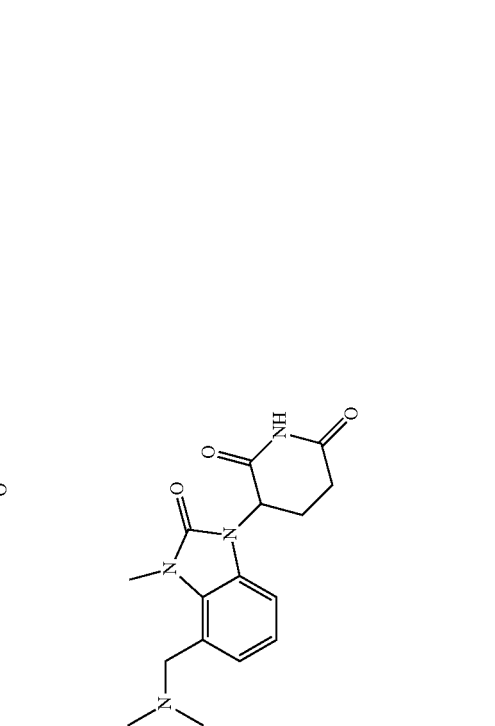 |

TABLE 1-continued
Exemplary Compounds
| I-# | Structure |
|---|---|
| I-174 | 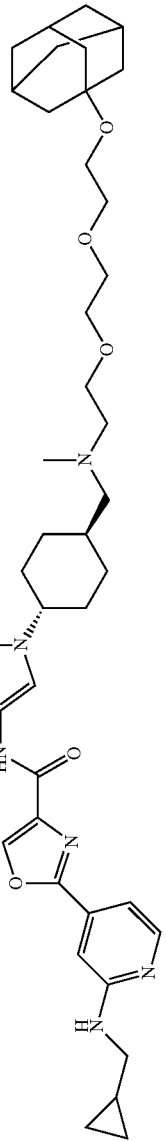 |
| I-175 | 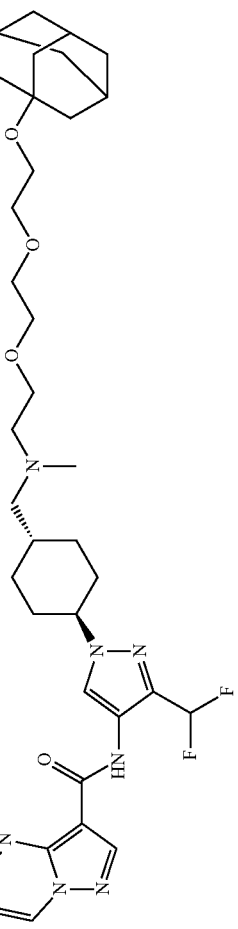 |

TABLE 1-continued

Exemplary Compounds

| I-# | Structure |
|---|---|
| I-176 | 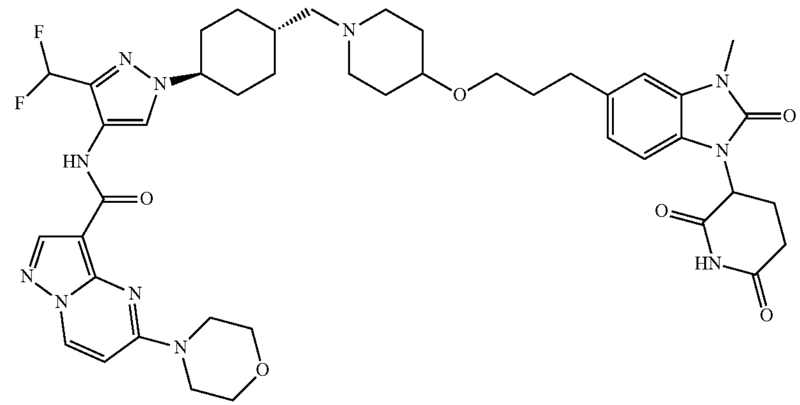 [SMILES: Cn1c(=O)n(C2CCC(=O)NC2=O)c2ccc(CCCOC3CCN(C[C@H]4CC[C@H](n5cc(NC(=O)c6cnn7ccc(N8CCOCC8)nc67)c(C(F)F)n5)CC4)CC3)cc21] |
| I-177 | 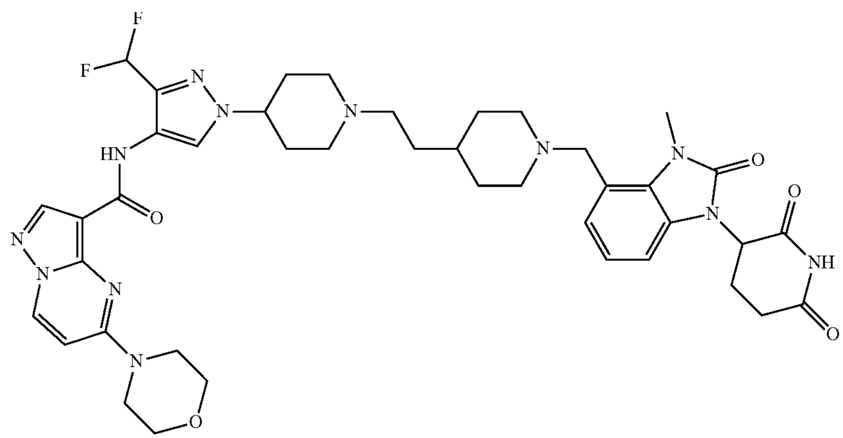 [SMILES: Cn1c(=O)n(C2CCC(=O)NC2=O)c2cccc(CN3CCC(CCN4CCC(n5cc(NC(=O)c6cnn7ccc(N8CCOCC8)nc67)c(C(F)F)n5)CC4)CC3)c21] |

TABLE 1-continued
Exemplary Compounds
| I-# | Structure |
|---|---|
| I-178 | 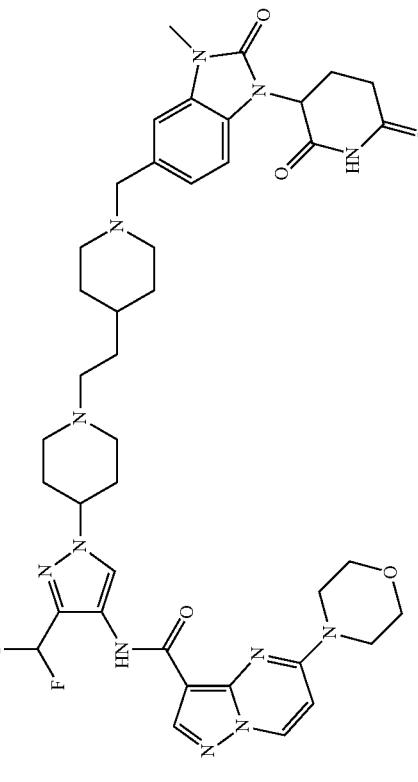 |
| I-179 | 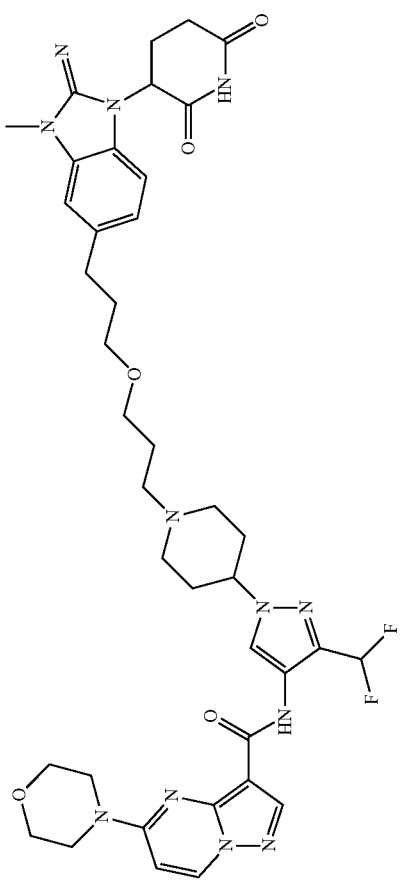 |

TABLE 1-continued
Exemplary Compounds
| I-# | Structure |
|---|---|
| I-180 | 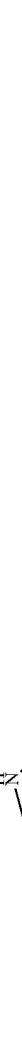 |
| I-181 | 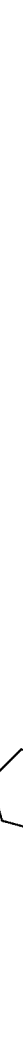 |

TABLE 1-continued
Exemplary Compounds
| I-# | Structure |
|---|---|
| I-182 | 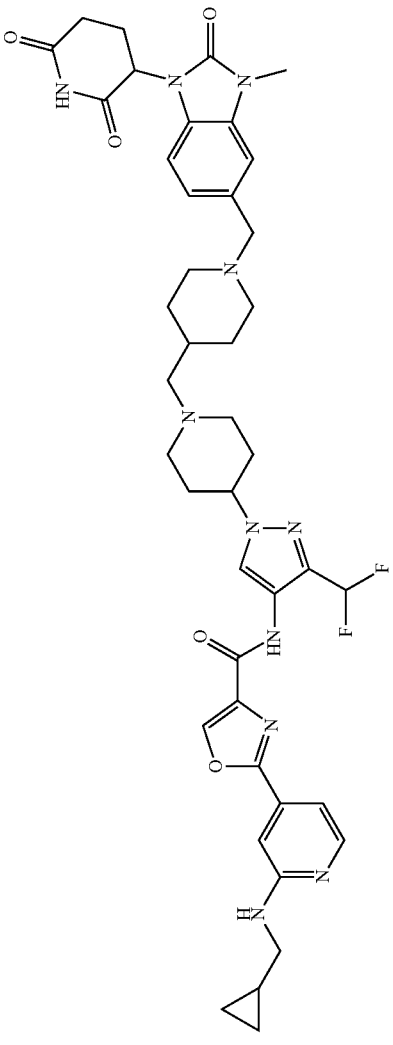 |
| I-183 | 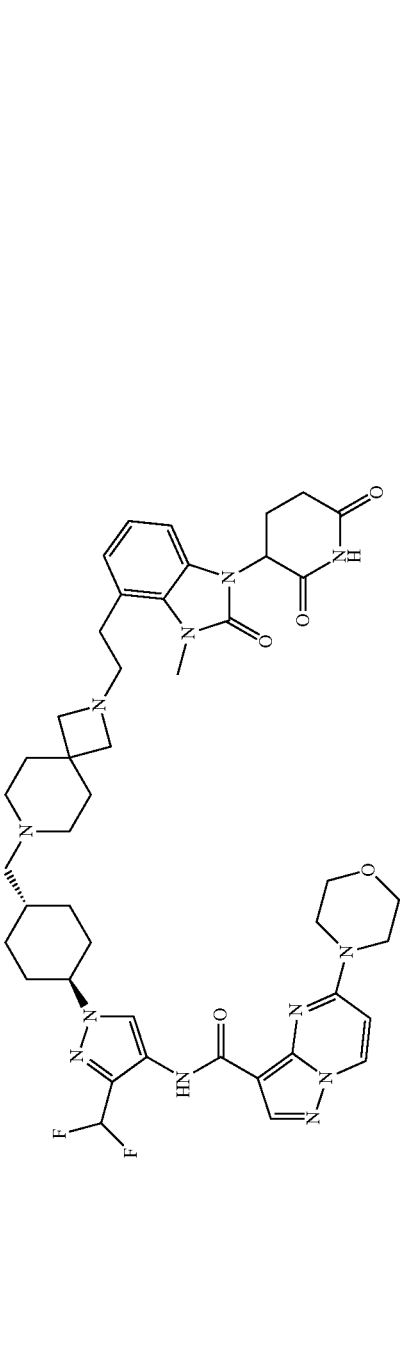 |

TABLE 1-continued
Exemplary Compounds
| I-# | Structure |
|---|---|
| I-184 | 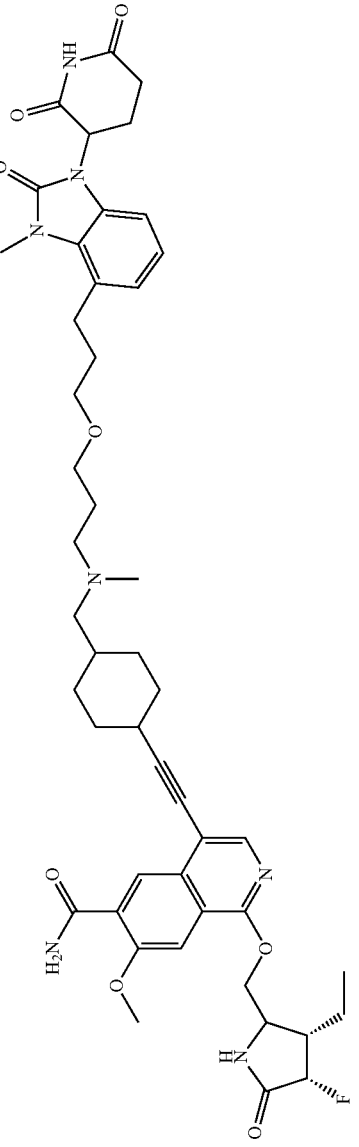 |
| I-185 | 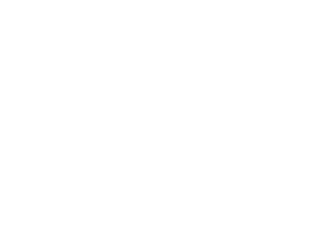 |

TABLE 1-continued
Exemplary Compounds
| I-# | Structure |
|---|---|
| I-186 | 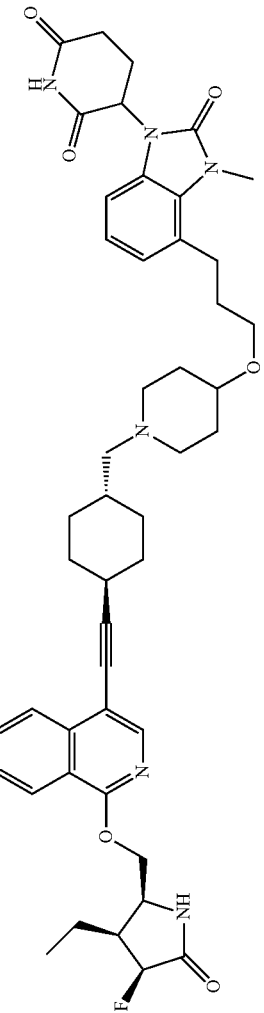 |
| I-187 | 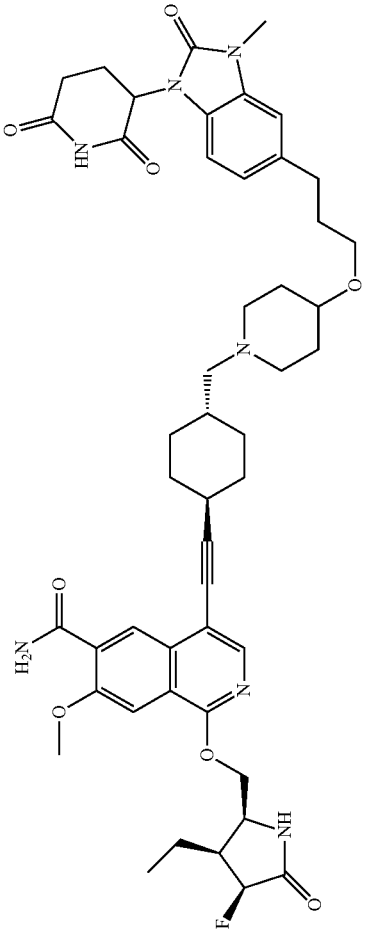 |
| I-188 | 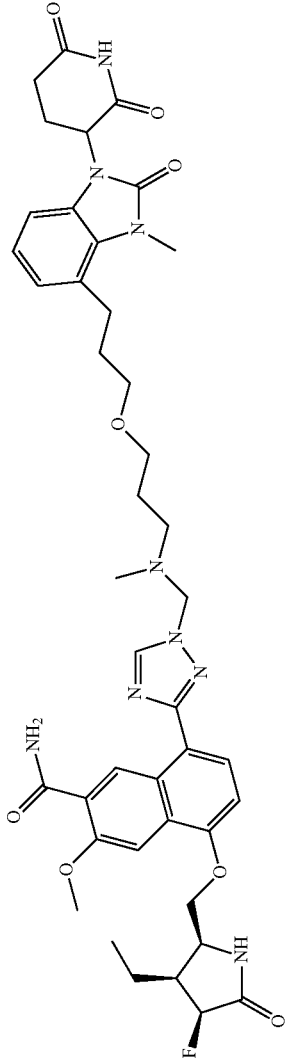 |

TABLE 1-continued
Exemplary Compounds
| I-# | Structure |
|---|---|
| I-189 | 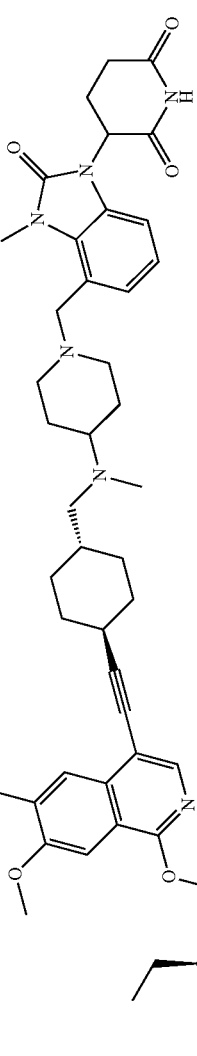 |
| I-190 | 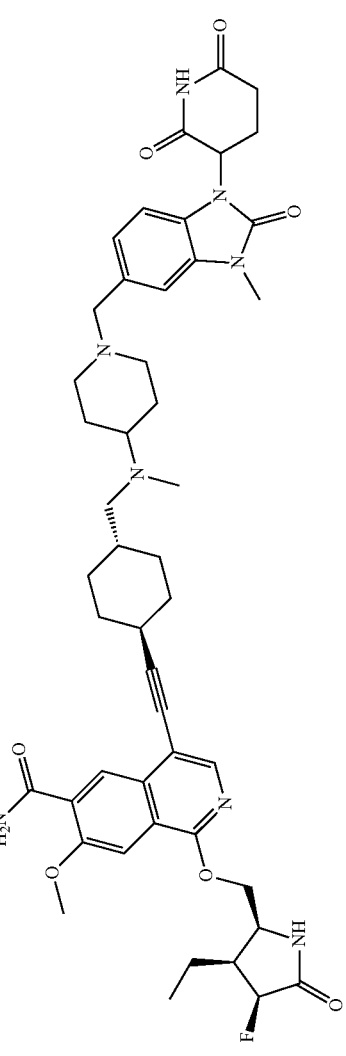 |
| I-191 | 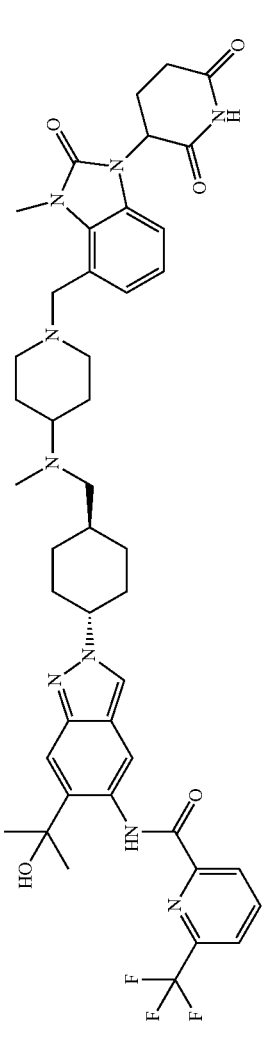 |

TABLE 1-continued
Exemplary Compounds
| I-# | Structure |
|---|---|
| I-192 | 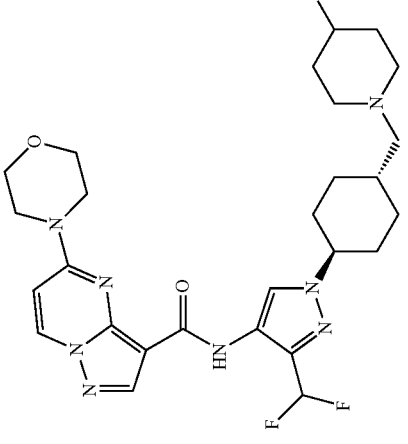 |
| I-193 |  |

TABLE 1-continued
Exemplary Compounds
| I-# | Structure |
|---|---|
| I-194 | 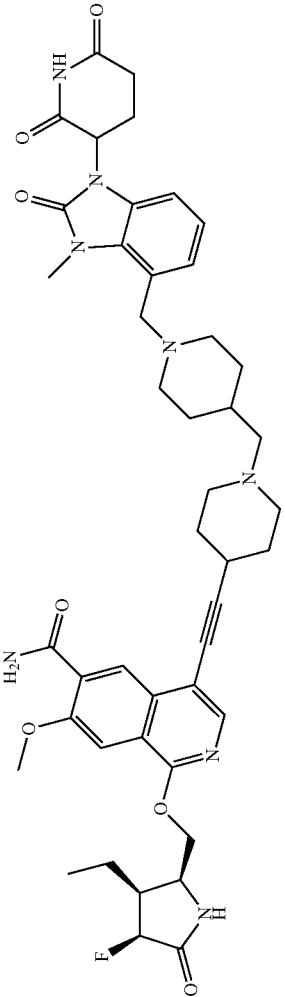 |
| I-195 | 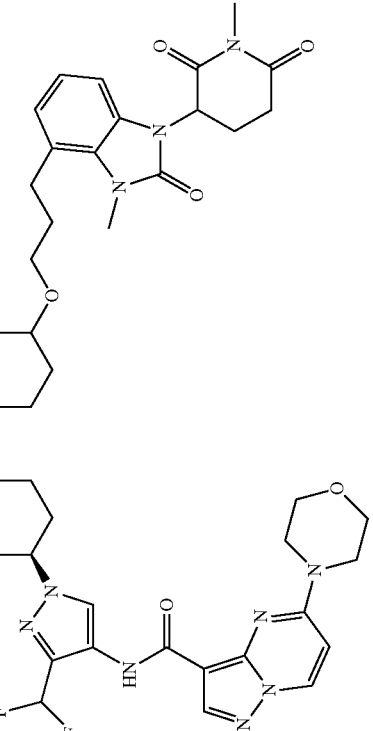 |

TABLE 1-continued
Exemplary Compounds
| I-# | Structure |
|---|---|
| I-196 | 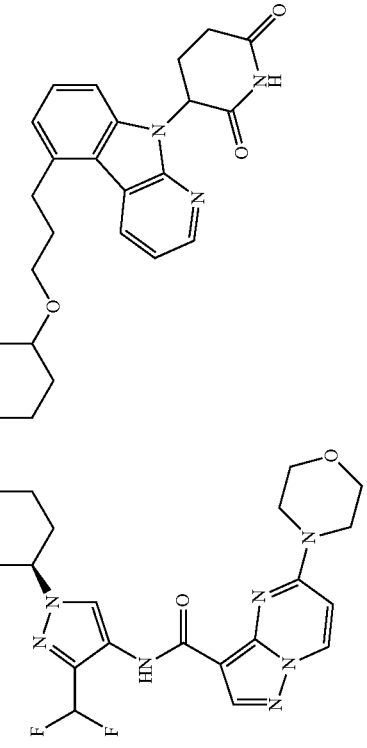 |
| I-197 | 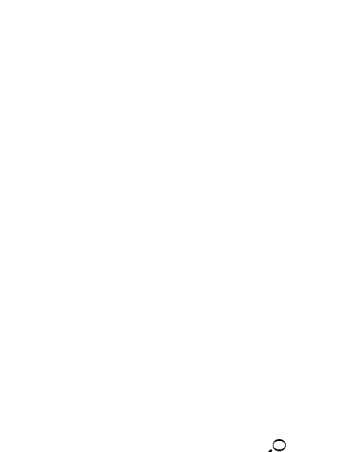 |

TABLE 1-continued
Exemplary Compounds
| I-# | Structure |
|---|---|
| I-198 | 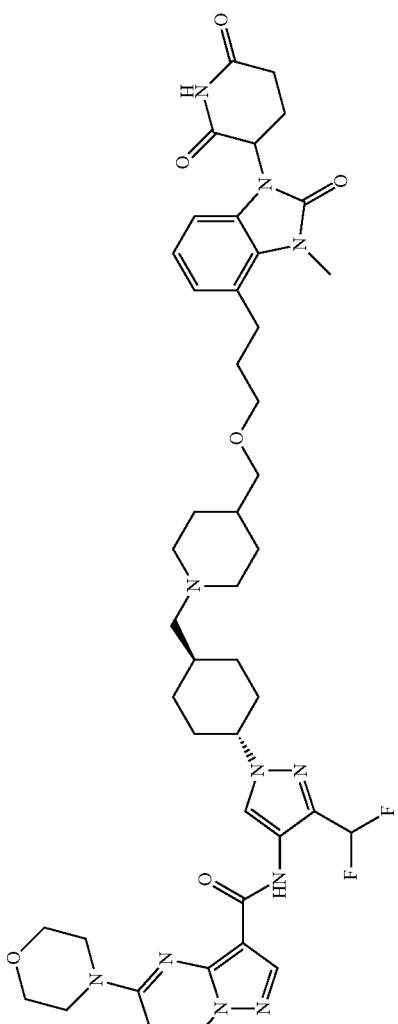 |
| I-199 | 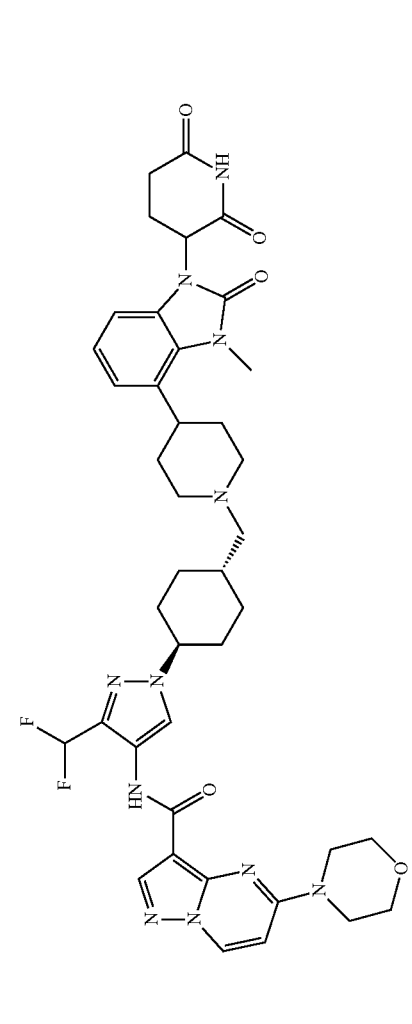 |

TABLE 1-continued
Exemplary Compounds
| I-# | Structure |
|---|---|
| I-200 | 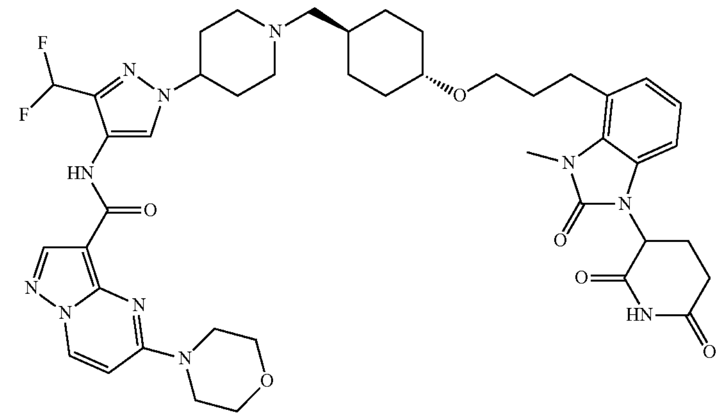 [SMILES: Cn1c(=O)n(C2CCC(=O)NC2=O)c2cccc(CCCO[C@H]3CC[C@H](CN4CCC(n5cc(NC(=O)c6cnn7ccc(N8CCOCC8)nc67)c(C(F)F)n5)CC4)CC3)c21] |
| I-201 | 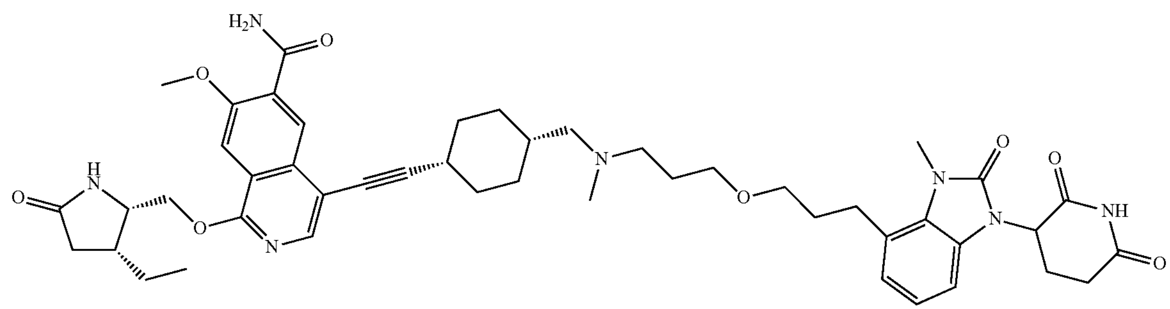 [SMILES: CC[C@@H]1CC(=O)N[C@@H]1COc1ncc(C#C[C@H]2CC[C@@H](CN(C)CCCOCCCc3cccc4c3n(C)c(=O)n4C3CCC(=O)NC3=O)CC2)c2cc(C(N)=O)c(OC)cc12] |
| I-202 | 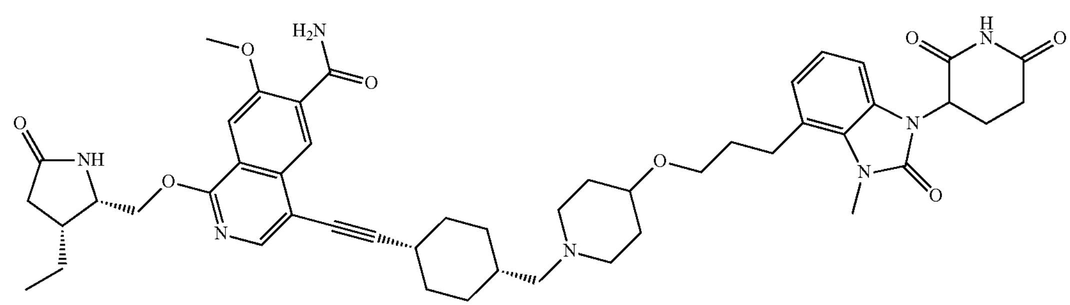 [SMILES: CC[C@@H]1CC(=O)N[C@@H]1COc1ncc(C#C[C@H]2CC[C@@H](CN3CCC(OCCCc4cccc5c4n(C)c(=O)n5C4CCC(=O)NC4=O)CC3)CC2)c2cc(C(N)=O)c(OC)cc12] |

TABLE 1-continued
Exemplary Compounds
| I-# | Structure |
|---|---|
| I-203 | 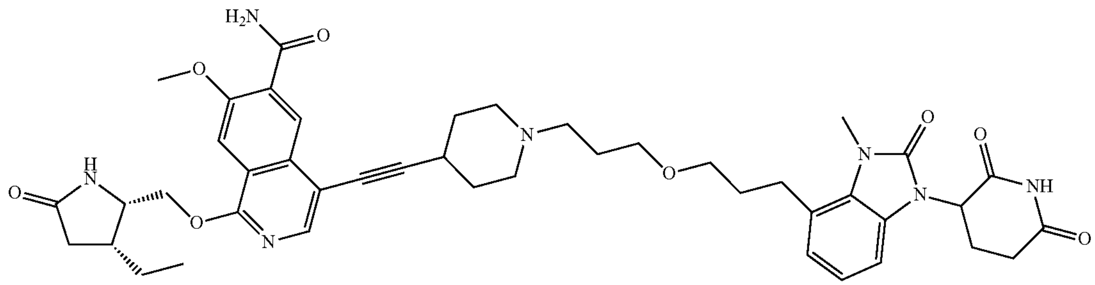 [SMILES: CC[C@@H]1CC(=O)N[C@@H]1COc1ncc(C#CC2CCN(CCCOCCCc3cccc4c3n(C)c(=O)n4C3CCC(=O)NC3=O)CC2)c2cc(C(N)=O)c(OC)cc12] |
| I-204 | 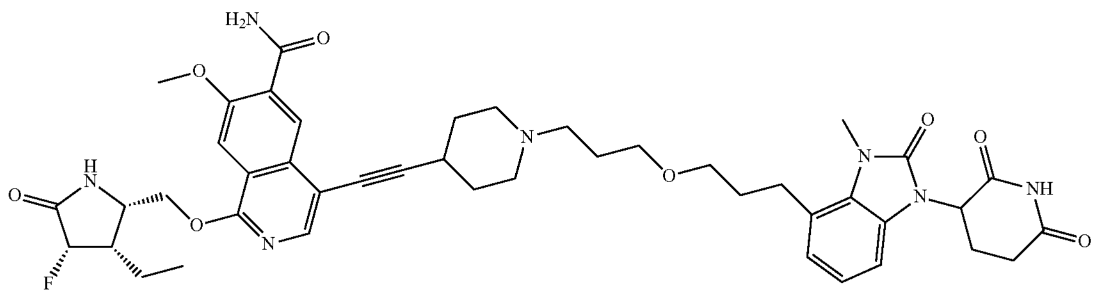 [SMILES: CC[C@@H]1[C@H](F)C(=O)N[C@@H]1COc1ncc(C#CC2CCN(CCCOCCCc3cccc4c3n(C)c(=O)n4C3CCC(=O)NC3=O)CC2)c2cc(C(N)=O)c(OC)cc12] |
| I-205 | 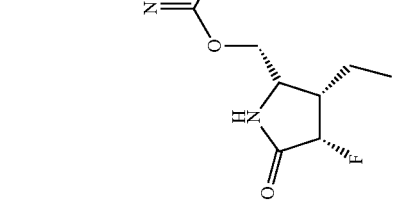 |

TABLE 1-continued
Exemplary Compounds
| I-# | Structure |
|---|---|
| I-206 | 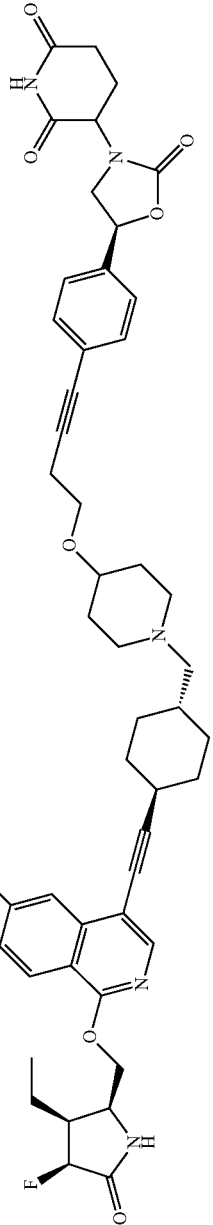 |
| I-207 | 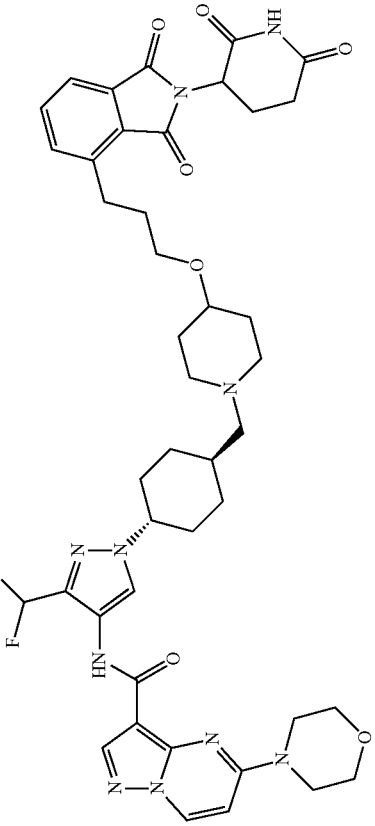 |

TABLE 1-continued
Exemplary Compounds
| I-# | Structure |
|---|---|
| I-208 | 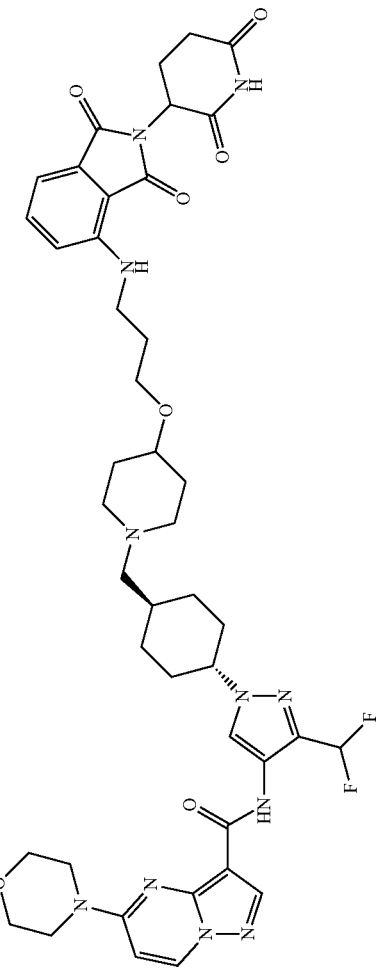 |
| I-209 |  |

TABLE 1-continued
Exemplary Compounds
| I-# | Structure |
|---|---|
| I-210 | 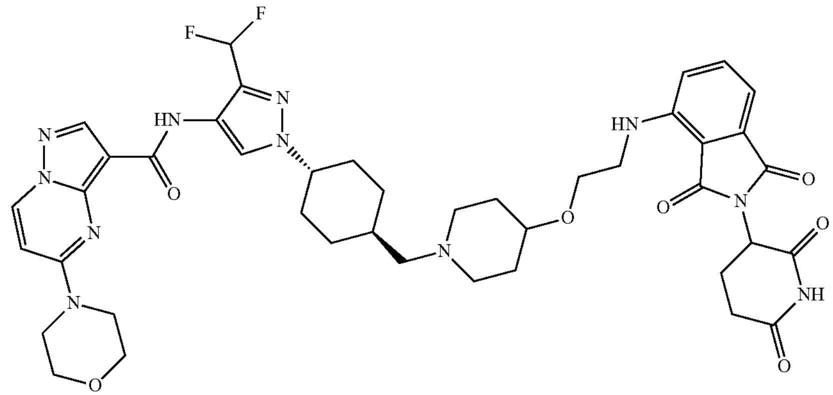 [SMILES: O=C1CCC(N2C(=O)c3cccc(NCCOC4CCN(C[C@H]5CC[C@H](n6cc(NC(=O)c7cnn8ccc(N9CCOCC9)nc78)c(C(F)F)n6)CC5)CC4)c3C2=O)C(=O)N1] |
| I-211 | 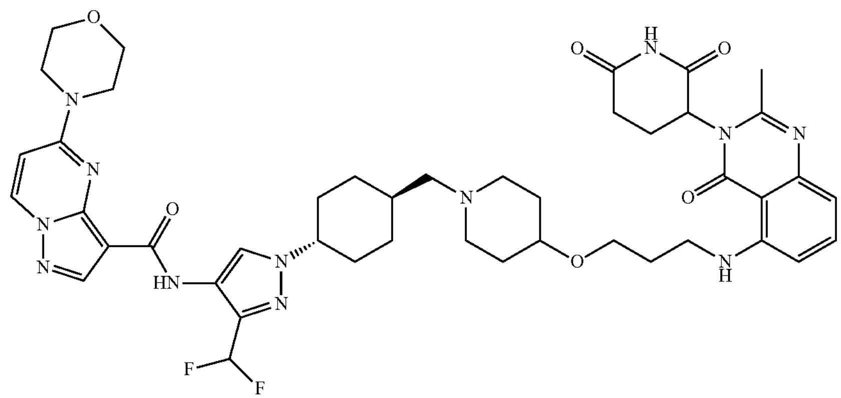 [SMILES: Cc1nc2cccc(NCCCOC3CCN(C[C@H]4CC[C@H](n5cc(NC(=O)c6cnn7ccc(N8CCOCC8)nc67)c(C(F)F)n5)CC4)CC3)c2c(=O)n1C1CCC(=O)NC1=O] |

TABLE 1-continued
Exemplary Compounds
| I-# | Structure |
|---|---|
| I-212 | 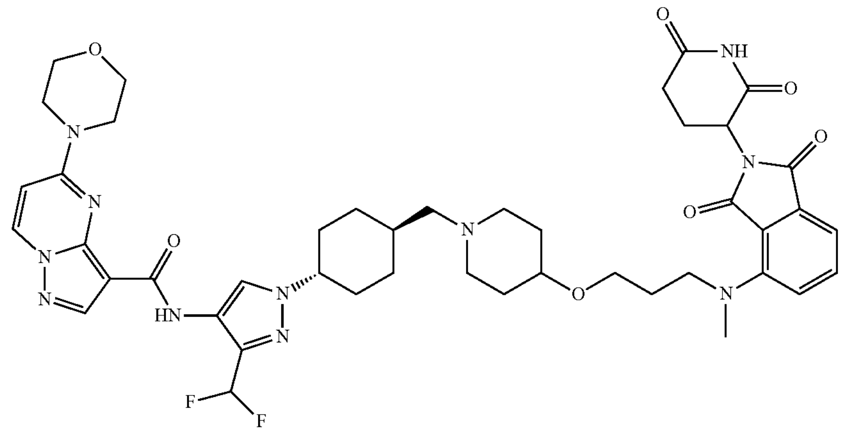 [SMILES: CN(CCCOC1CCN(C[C@H]2CC[C@H](n3cc(NC(=O)c4cnn5ccc(N6CCOCC6)nc45)c(C(F)F)n3)CC2)CC1)c1cccc2c1C(=O)N(C1CCC(=O)NC1=O)C2=O] |
| I-213 | 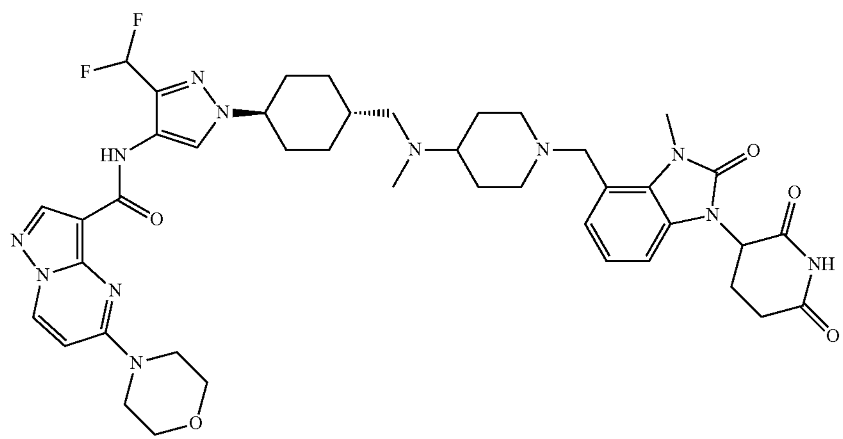 [SMILES: CN(C[C@H]1CC[C@H](n2cc(NC(=O)c3cnn4ccc(N5CCOCC5)nc34)c(C(F)F)n2)CC1)C1CCN(Cc2cccc3c2n(C)c(=O)n3C2CCC(=O)NC2=O)CC1] |

TABLE 1-continued

Exemplary Compounds

| I-# | Structure |
|---|---|
| I-214 | 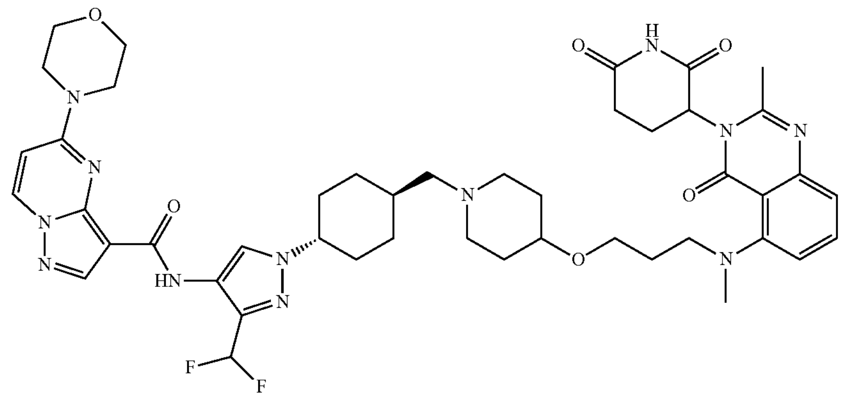 [SMILES: Cc1nc2cccc(N(C)CCCOC3CCN(C[C@H]4CC[C@H](n5cc(NC(=O)c6cnn7ccc(N8CCOCC8)nc67)c(C(F)F)n5)CC4)CC3)c2c(=O)n1C1CCC(=O)NC1=O] |
| I-215 | 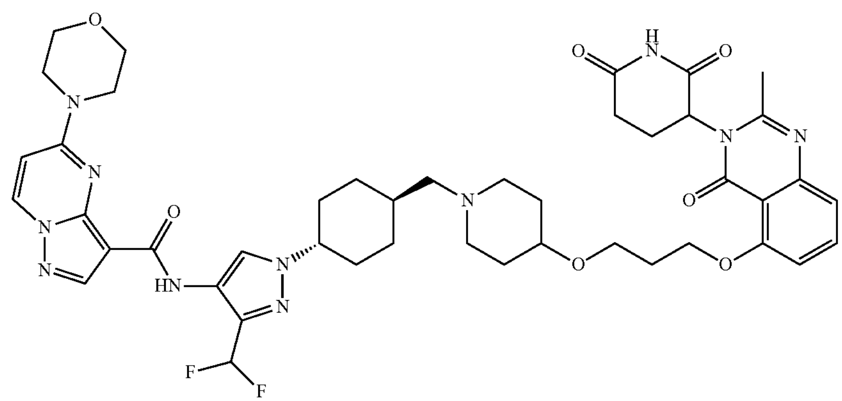 [SMILES: Cc1nc2cccc(OCCCOC3CCN(C[C@H]4CC[C@H](n5cc(NC(=O)c6cnn7ccc(N8CCOCC8)nc67)c(C(F)F)n5)CC4)CC3)c2c(=O)n1C1CCC(=O)NC1=O] |

TABLE 1-continued
Exemplary Compounds
| I-# | Structure |
|---|---|
| I-216 | 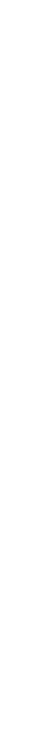 |
| I-217 | 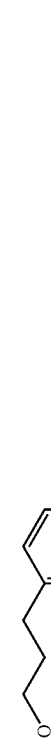 |

TABLE 1-continued
Exemplary Compounds
| I-# | Structure |
|---|---|
| I-218 | 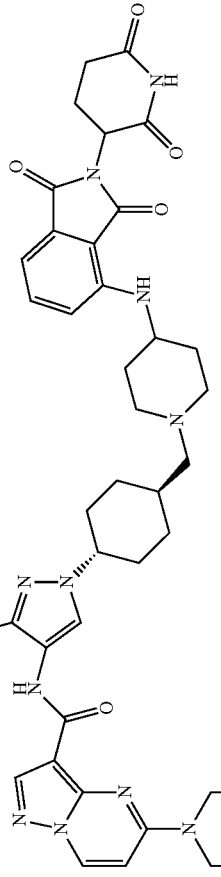 |
| I-219 | 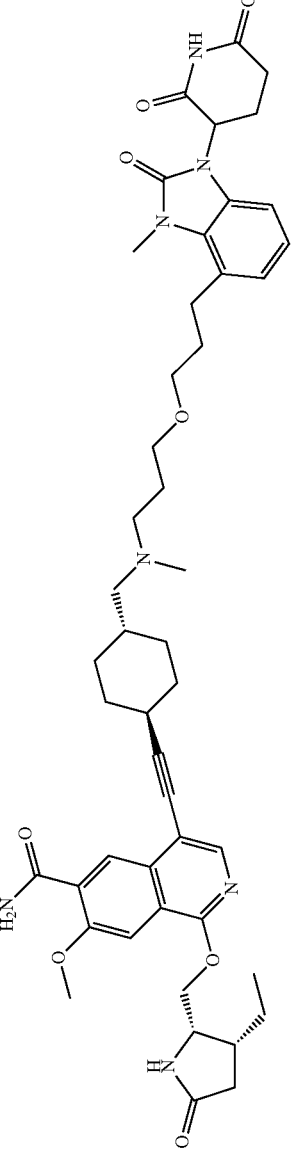 |

TABLE 1-continued
Exemplary Compounds
| I-# | Structure |
|---|---|
| I-220 | 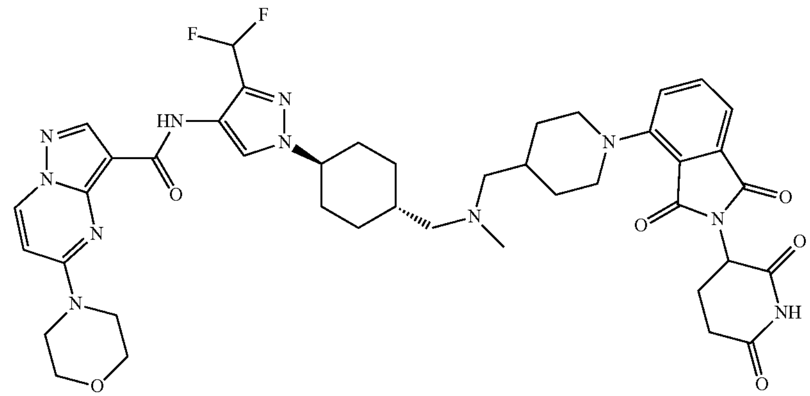 [SMILES: CN(CC1CCN(c2cccc3c2C(=O)N(C2CCC(=O)NC2=O)C3=O)CC1)C[C@H]1CC[C@H](n2cc(NC(=O)c3cnn4ccc(N5CCOCC5)nc34)c(C(F)F)n2)CC1] |
| I-221 | 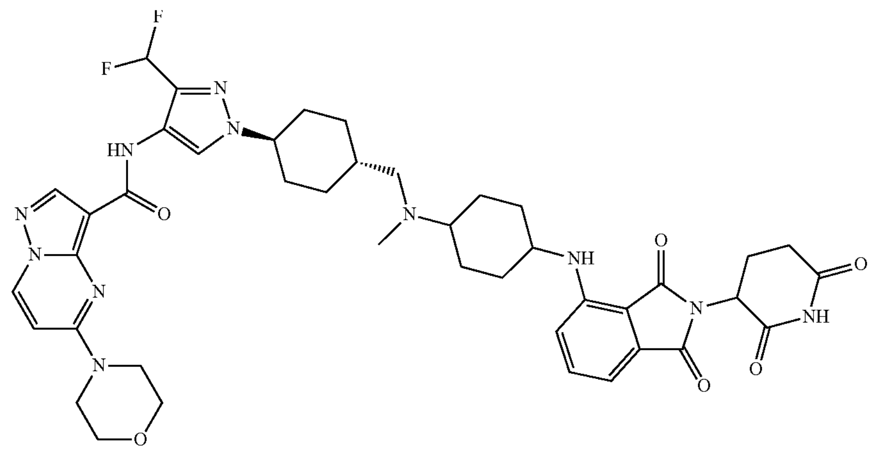 [SMILES: CN(C[C@H]1CC[C@H](n2cc(NC(=O)c3cnn4ccc(N5CCOCC5)nc34)c(C(F)F)n2)CC1)C1CCC(Nc2cccc3c2C(=O)N(C2CCC(=O)NC2=O)C3=O)CC1] |

TABLE 1-continued
Exemplary Compounds
| I-# | Structure |
|---|---|
| I-222 | 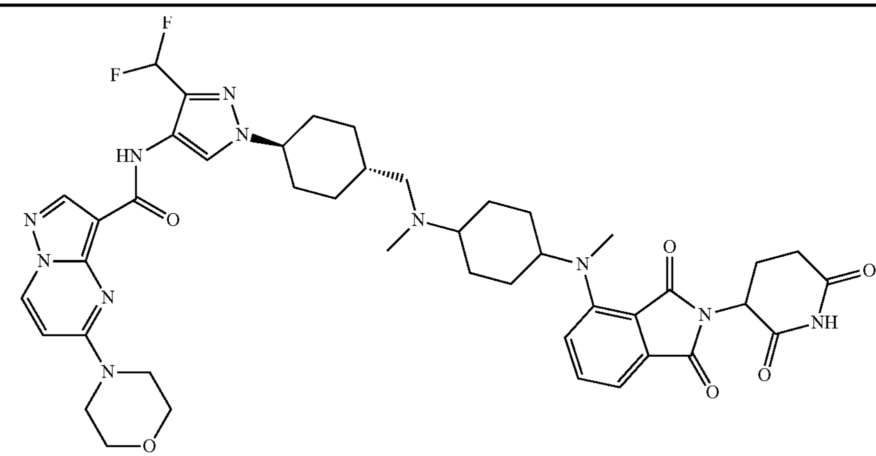 |
| I-223 | 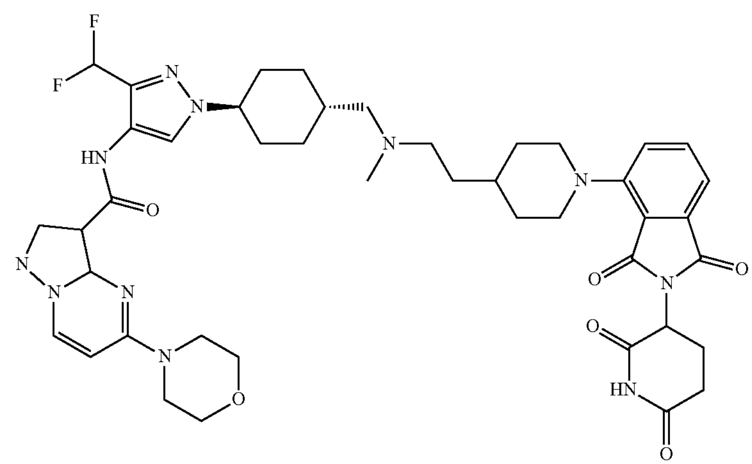 [SMILES: CN(CCC1CCN(c2cccc3c2C(=O)N(C2CCC(=O)NC2=O)C3=O)CC1)C[C@H]1CC[C@H](n2cc(NC(=O)C3CNN4C=CC(N5CCOCC5)=NC34)c(C(F)F)n2)CC1] |

TABLE 1-continued
Exemplary Compounds
| I-# | Structure |
|---|---|
| I-224 | 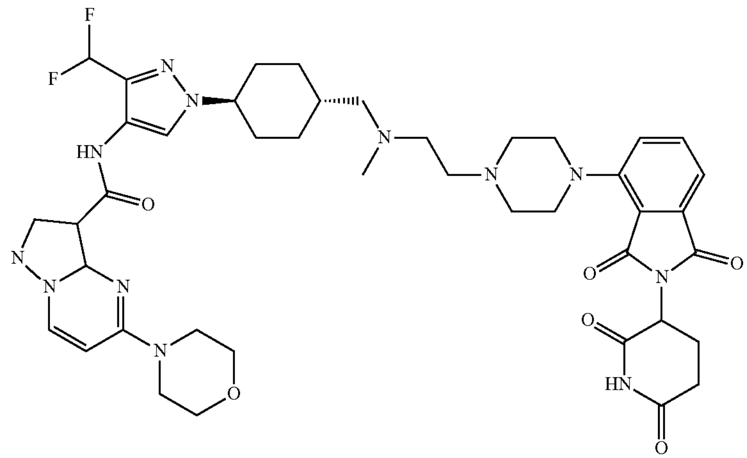 [SMILES: CN(CCN1CCN(c2cccc3c2C(=O)N(C2CCC(=O)NC2=O)C3=O)CC1)C[C@H]1CC[C@H](n2cc(NC(=O)C3CNN4C=CC(N5CCOCC5)=NC34)c(C(F)F)n2)CC1] |
| I-225 | 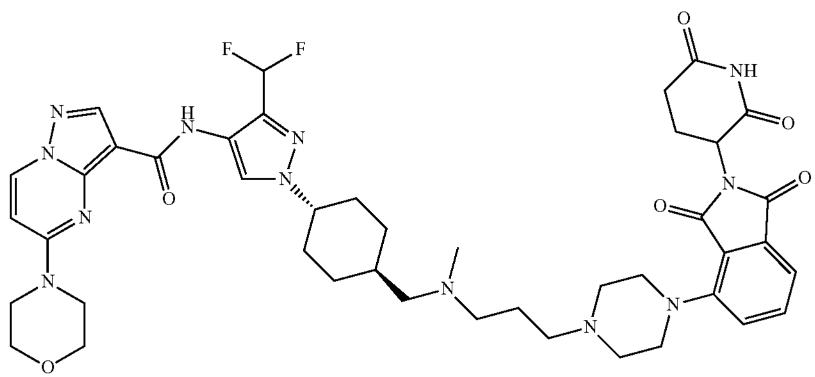 [SMILES: CN(CCCN1CCN(c2cccc3c2C(=O)N(C2CCC(=O)NC2=O)C3=O)CC1)C[C@H]1CC[C@H](n2cc(NC(=O)c3cnn4ccc(N5CCOCC5)nc34)c(C(F)F)n2)CC1] |

TABLE 1-continued
Exemplary Compounds
| I-# | Structure |
|---|---|
| I-226 | 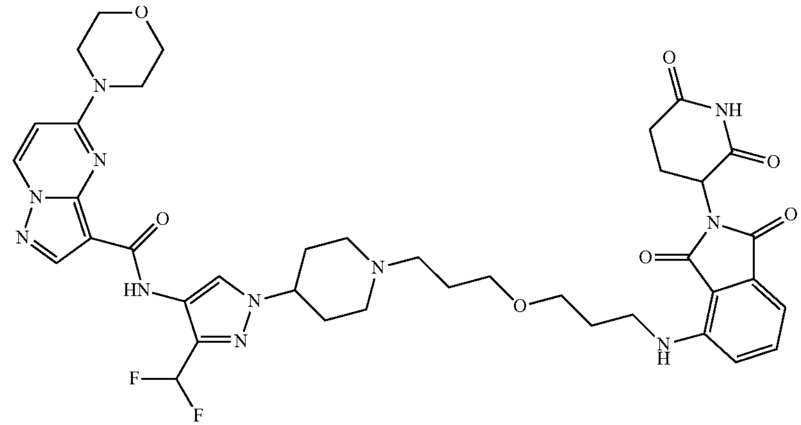 [SMILES: O=C1CCC(N2C(=O)c3cccc(NCCCOCCCN4CCC(n5cc(NC(=O)c6cnn7ccc(N8CCOCC8)nc67)c(C(F)F)n5)CC4)c3C2=O)C(=O)N1] |
| I-227 | 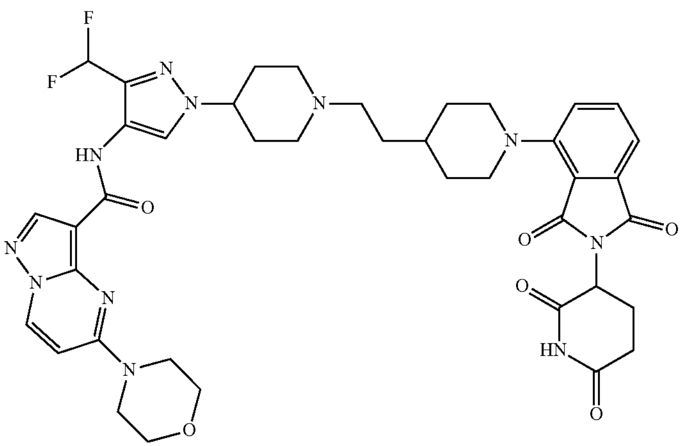 [SMILES: O=C1CCC(N2C(=O)c3cccc(N4CCC(CCN5CCC(n6cc(NC(=O)c7cnn8ccc(N9CCOCC9)nc78)c(C(F)F)n6)CC5)CC4)c3C2=O)C(=O)N1] |

TABLE 1-continued
Exemplary Compounds
| I-# | Structure |
|---|---|
| I-228 | 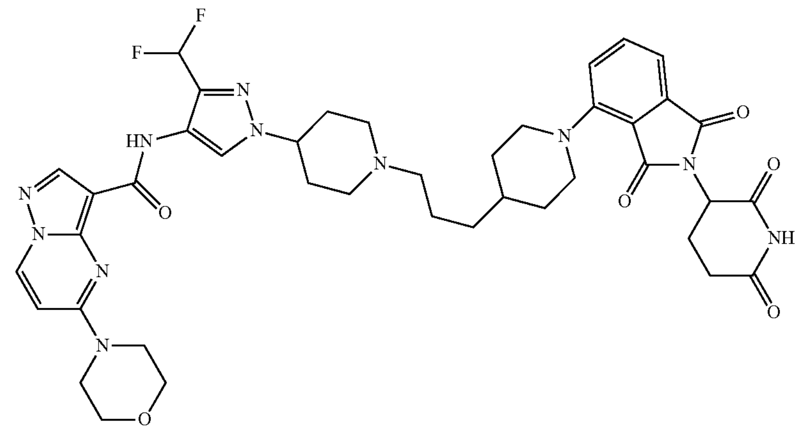 [SMILES: O=C1CCC(N2C(=O)c3cccc(N4CCC(CCCN5CCC(n6cc(NC(=O)c7cnn8ccc(N9CCOCC9)nc78)c(C(F)F)n6)CC5)CC4)c3C2=O)C(=O)N1] |
| I-229 | 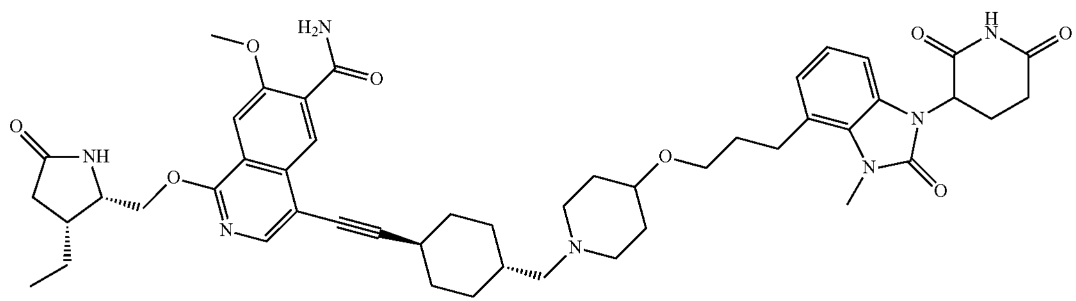 [SMILES: CC[C@@H]1CC(=O)N[C@@H]1COc1ncc(C#C[C@H]2CC[C@H](CN3CCC(OCCCc4cccc5c4n(C)c(=O)n5C4CCC(=O)NC4=O)CC3)CC2)c2cc(C(N)=O)c(OC)cc12] |

TABLE 1-continued
Exemplary Compounds
| I-# | Structure |
|---|---|
| I-230 | 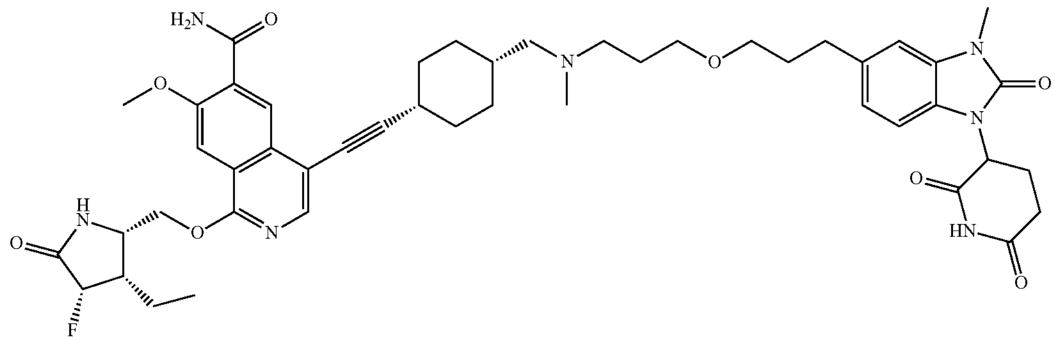 [SMILES: CC[C@@H]1[C@H](F)C(=O)N[C@@H]1COc1ncc(C#C[C@H]2CC[C@@H](CN(C)CCCOCCCc3ccc4c(c3)n(C)c(=O)n4C3CCC(=O)NC3=O)CC2)c2cc(C(N)=O)c(OC)cc12] |
| I-231 | 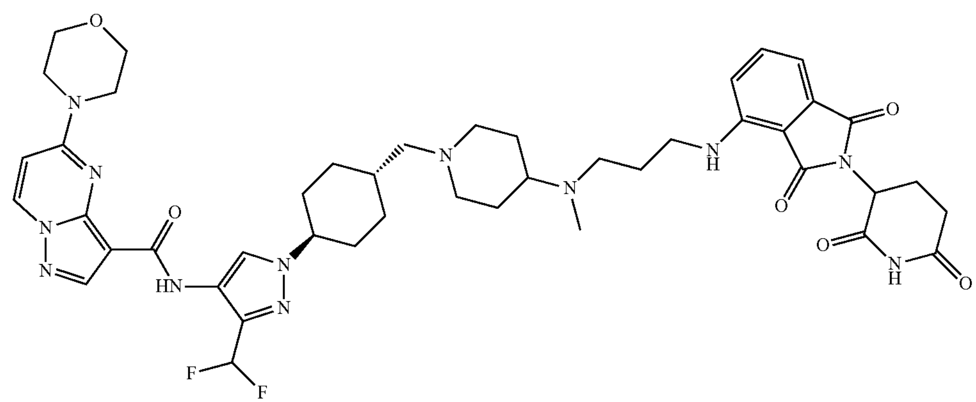 [SMILES: CN(CCCNc1cccc2c1C(=O)N(C1CCC(=O)NC1=O)C2=O)C1CCN(C[C@H]2CC[C@H](n3cc(NC(=O)c4cnn5ccc(N6CCOCC6)nc45)c(C(F)F)n3)CC2)CC1] |

TABLE 1-continued
Exemplary Compounds
| I-# | Structure |
|---|---|
| I-232 | 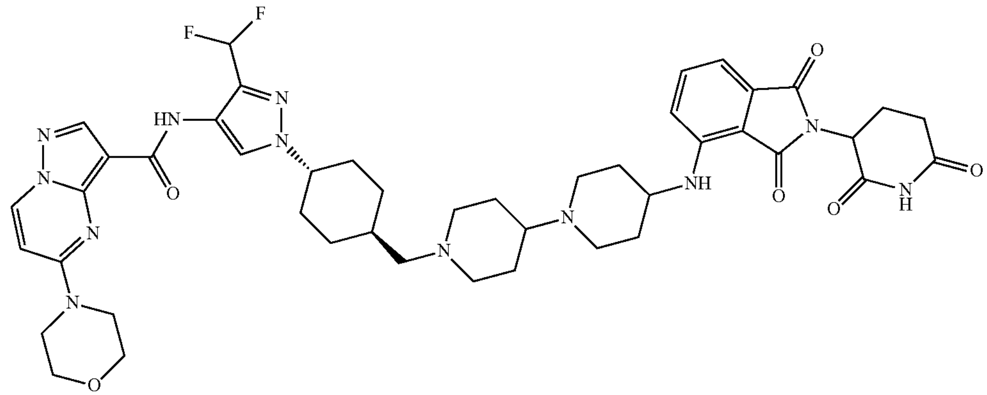 [SMILES: O=C1CCC(N2C(=O)c3cccc(NC4CCN(C5CCN(C[C@H]6CC[C@H](n7cc(NC(=O)c8cnn9ccc(N%10CCOCC%10)nc89)c(C(F)F)n7)CC6)CC5)CC4)c3C2=O)C(=O)N1] |
| I-233 | 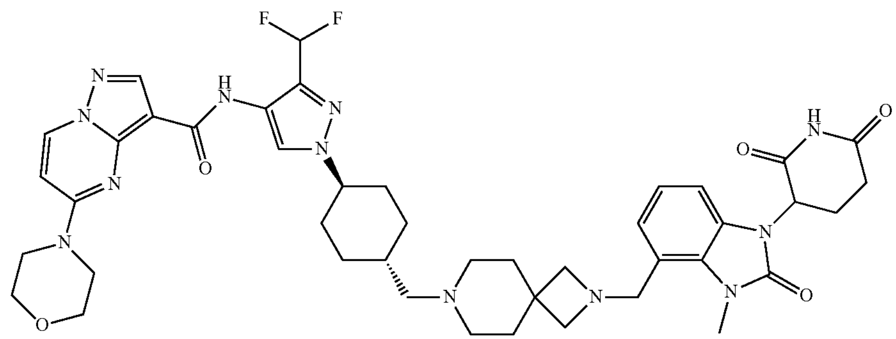 [SMILES: Cn1c(=O)n(C2CCC(=O)NC2=O)c2cccc(CN3CC4(CCN(C[C@H]5CC[C@H](n6cc(NC(=O)c7cnn8ccc(N9CCOCC9)nc78)c(C(F)F)n6)CC5)CC4)C3)c21] |

TABLE 1-continued

Exemplary Compounds

| I-# | Structure |
|---|---|
| I-234 | 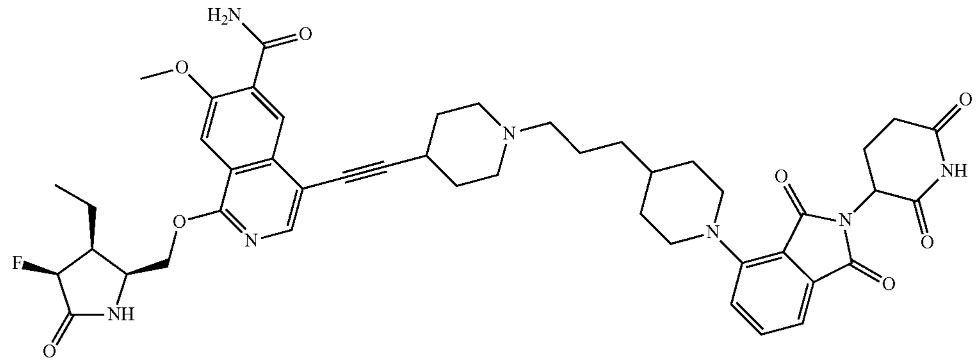 [SMILES: CC[C@@H]1[C@H](F)C(=O)N[C@@H]1COc1ncc(C#CC2CCN(CCCC3CCN(c4cccc5c4C(=O)N(C4CCC(=O)NC4=O)C5=O)CC3)CC2)c2cc(C(N)=O)c(OC)cc12] |
| I-235 | 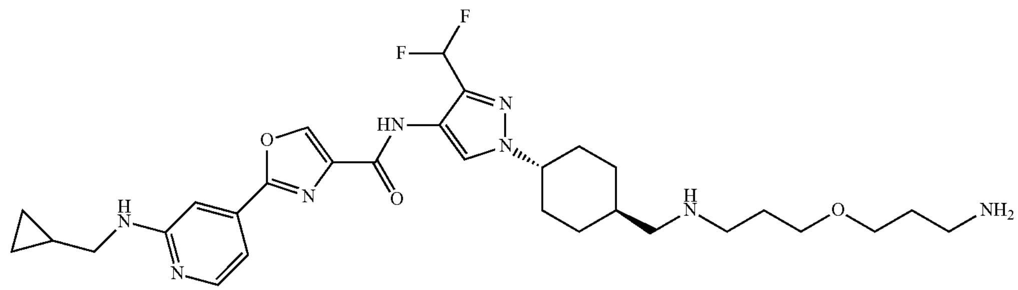 [SMILES: NCCCOCCCNC[C@H]1CC[C@H](n2cc(NC(=O)c3coc(-c4ccnc(NCC5CC5)c4)n3)c(C(F)F)n2)CC1] |
| I-236 | 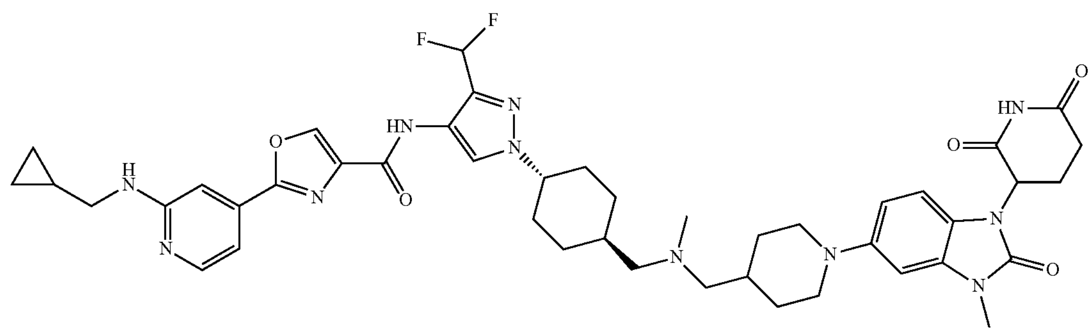 [SMILES: CN(CC1CCN(c2ccc3c(c2)n(C)c(=O)n3C2CCC(=O)NC2=O)CC1)C[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-237 | 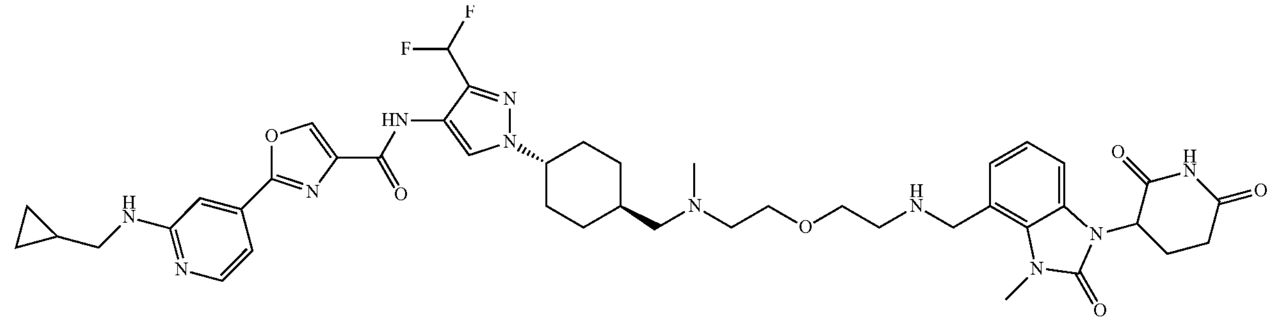 [SMILES: CN(CCOCCNCc1cccc2c1n(C)c(=O)n2C1CCC(=O)NC1=O)C[C@H]1CC[C@H](n2cc(NC(=O)c3coc(-c4ccnc(NCC5CC5)c4)n3)c(C(F)F)n2)CC1] |
| I-238 | 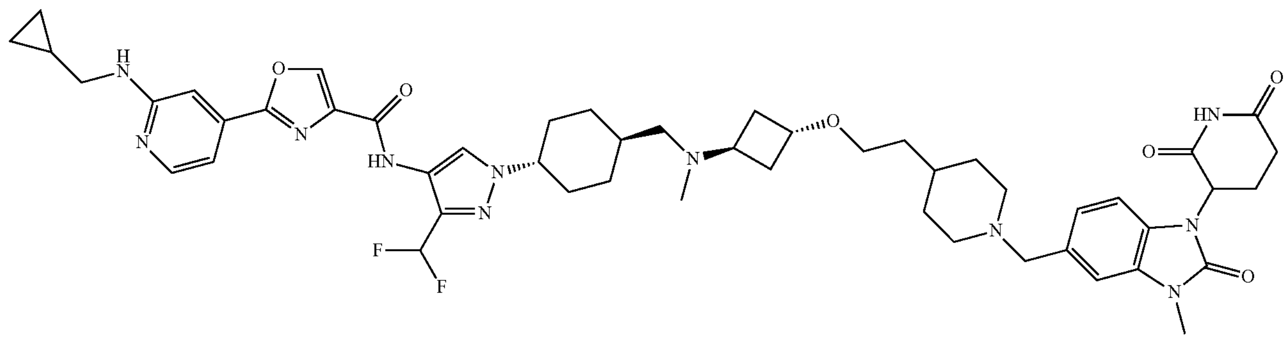 [SMILES: Cn1c(=O)n(C2CCC(=O)NC2=O)c2ccc(CN3CCC(CCO[C@H]4C[C@H](N(C)C[C@H]5CC[C@H](n6cc(NC(=O)c7coc(-c8ccnc(NCC9CC9)c8)n7)c(C(F)F)n6)CC5)C4)CC3)cc21] |
| I-239 | 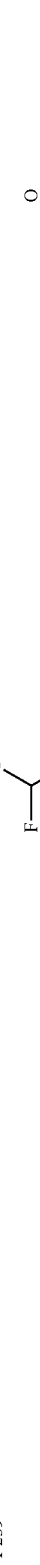 |

TABLE 1-continued
Exemplary Compounds
| I-# | Structure |
|---|---|
| I-240 | 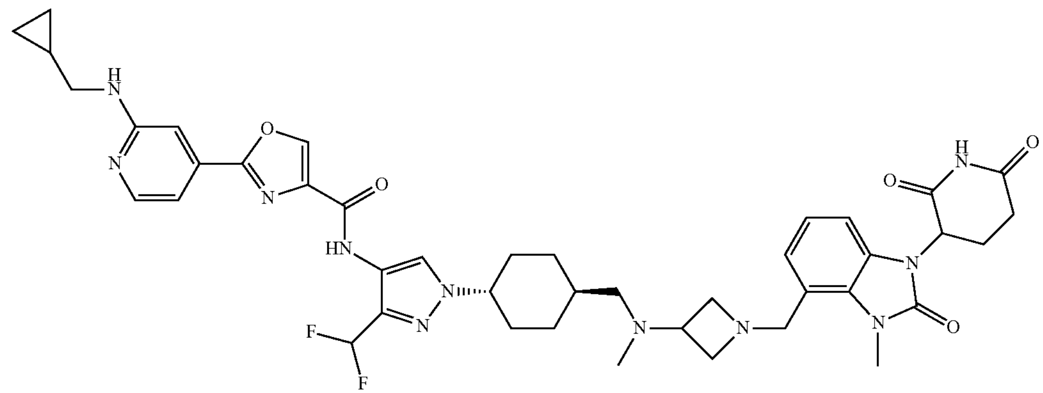 [SMILES: CN(C[C@H]1CC[C@H](n2cc(NC(=O)c3coc(-c4ccnc(NCC5CC5)c4)n3)c(C(F)F)n2)CC1)C1CN(Cc2cccc3c2n(C)c(=O)n3C2CCC(=O)NC2=O)C1] |
| I-241 | 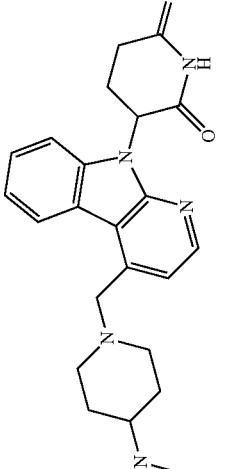 |

TABLE 1-continued
Exemplary Compounds
| I-# | Structure |
|---|---|
| I-242 | 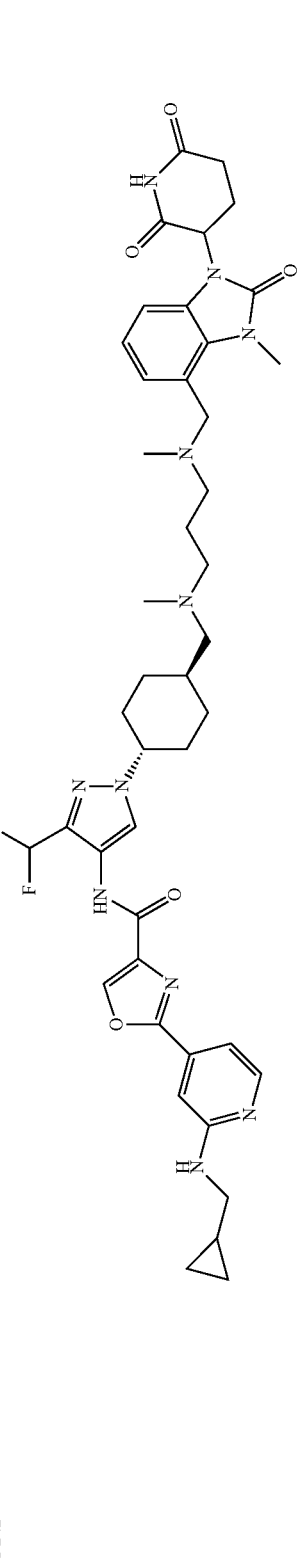 |
| I-243 | 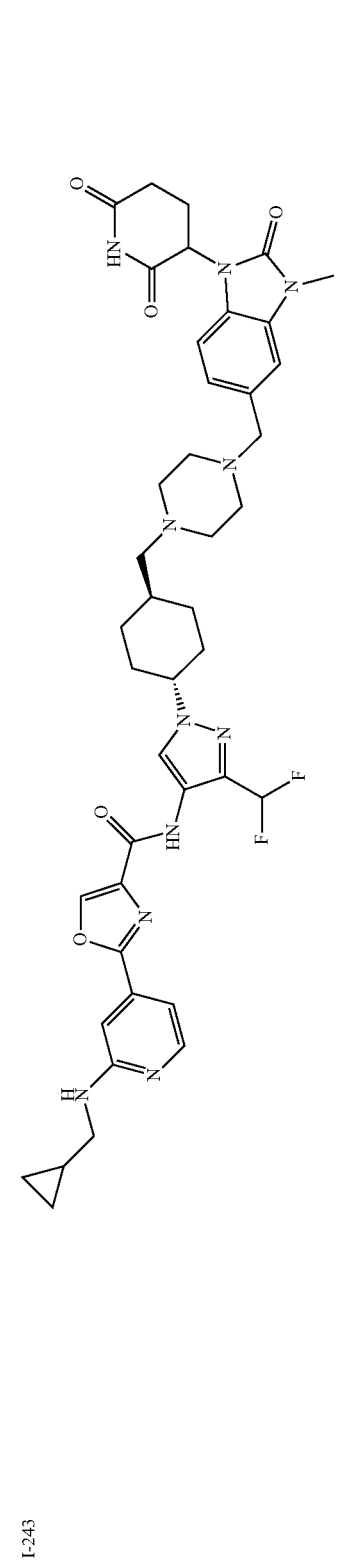 |
| I-244 | 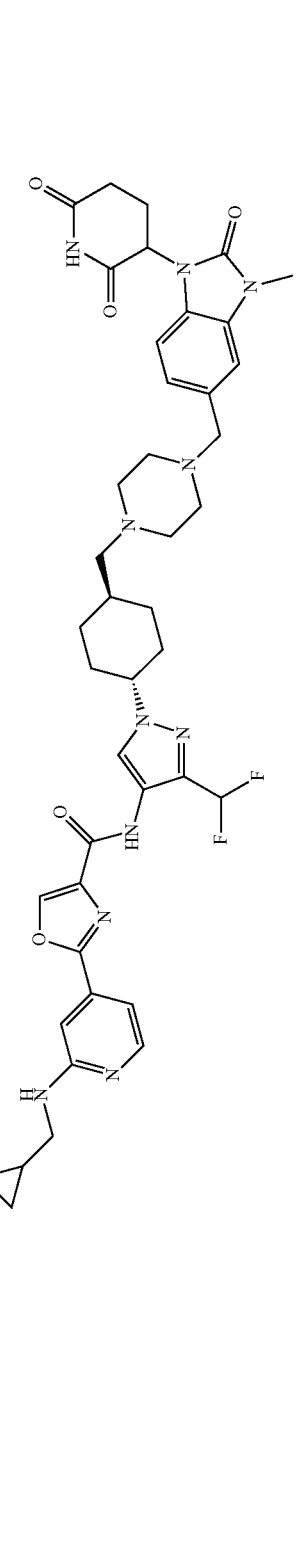 |

TABLE 1-continued
Exemplary Compounds
| I-# | Structure |
|---|---|
| I-245 | 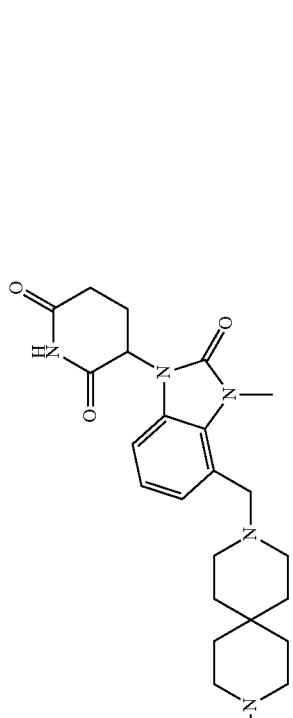 |
| I-246 | 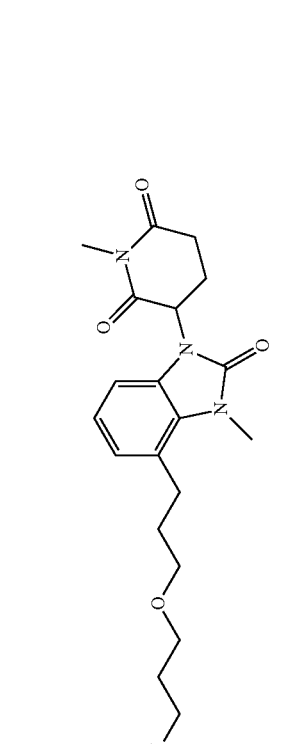 |

TABLE 1-continued
Exemplary Compounds
| I-# | Structure |
|---|---|
| I-247 | 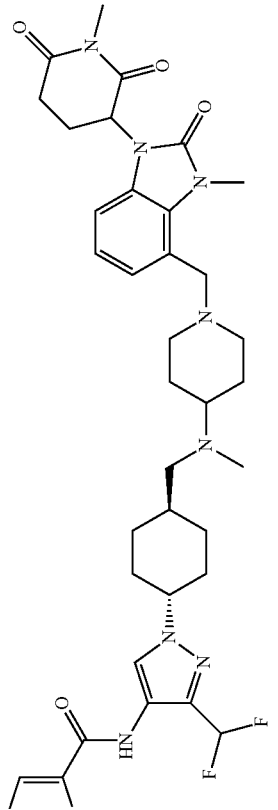 |
| I-248 | 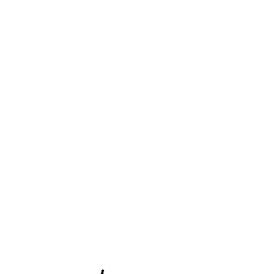 |

TABLE 1-continued
Exemplary Compounds
| I-# | Structure |
|---|---|
| I-249 | 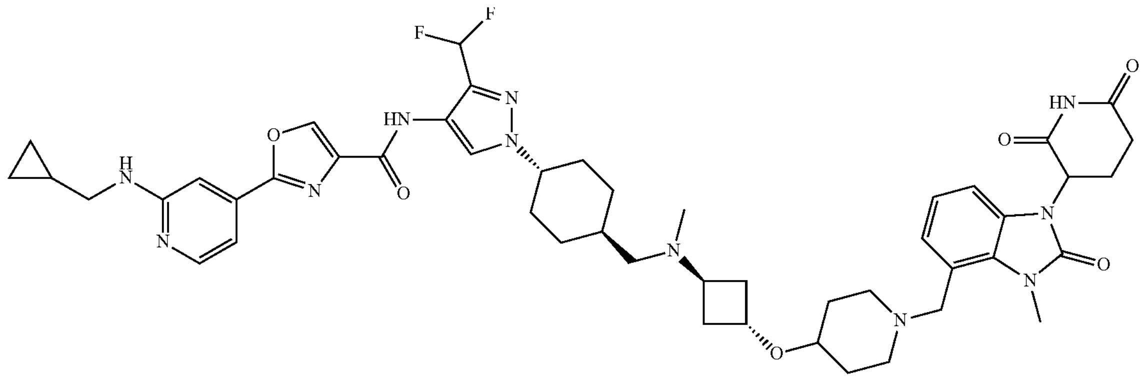 [SMILES: Cn1c(=O)n(C2CCC(=O)NC2=O)c2cccc(CN3CCC(O[C@H]4C[C@H](N(C)C[C@H]5CC[C@H](n6cc(NC(=O)c7coc(-c8ccnc(NCC9CC9)c8)n7)c(C(F)F)n6)CC5)C4)CC3)c21] |
| I-250 | 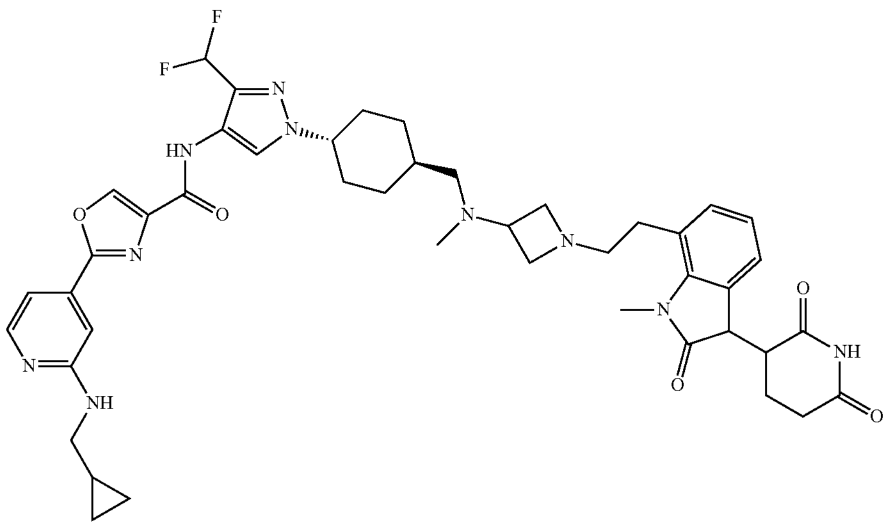 [SMILES: CN1C(=O)C(C2CCC(=O)NC2=O)c2cccc(CCN3CC(N(C)C[C@H]4CC[C@H](n5cc(NC(=O)c6coc(-c7ccnc(NCC8CC8)c7)n6)c(C(F)F)n5)CC4)C3)c21] |

TABLE 1-continued
Exemplary Compounds
| I-# | Structure |
|---|---|
| I-251 | 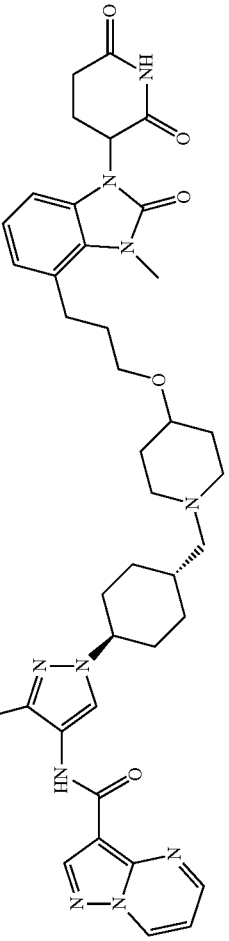 |
| I-252 | 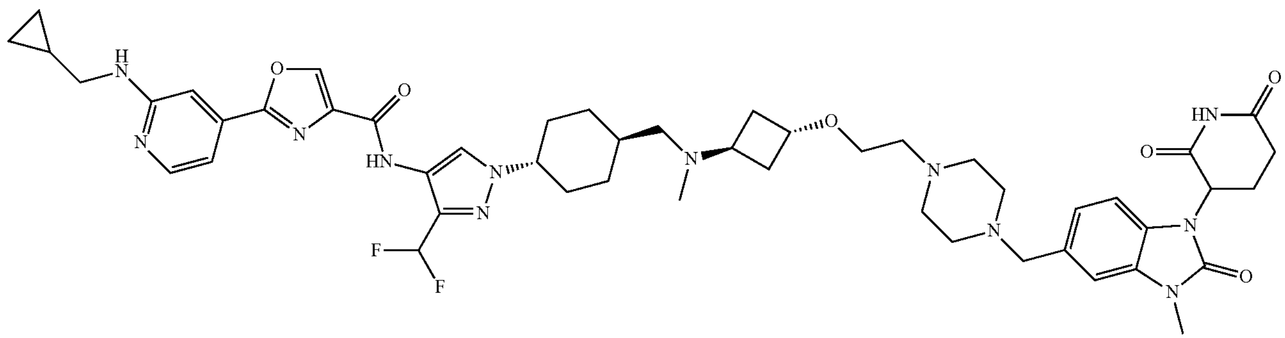 [SMILES: Cn1c(=O)n(C2CCC(=O)NC2=O)c2ccc(CN3CCN(CCO[C@H]4C[C@H](N(C)C[C@H]5CC[C@H](n6cc(NC(=O)c7coc(-c8ccnc(NCC9CC9)c8)n7)c(C(F)F)n6)CC5)C4)CC3)cc21] |
| I-253 | 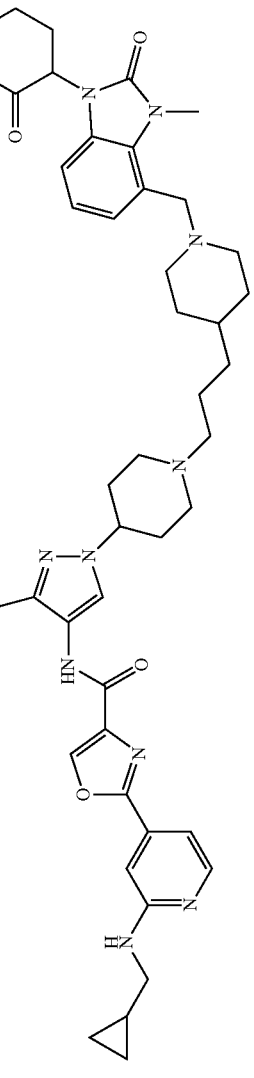 |

TABLE 1-continued
Exemplary Compounds
| I-# | Structure |
|---|---|
| I-254 | 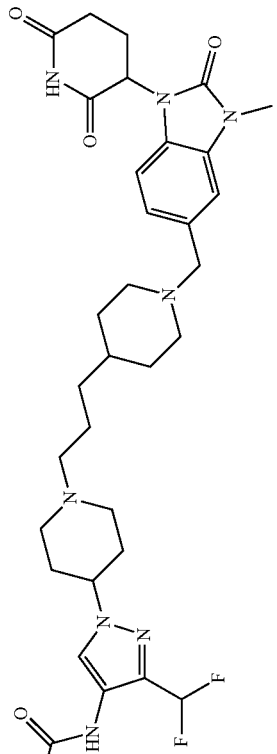 |
| I-255 | 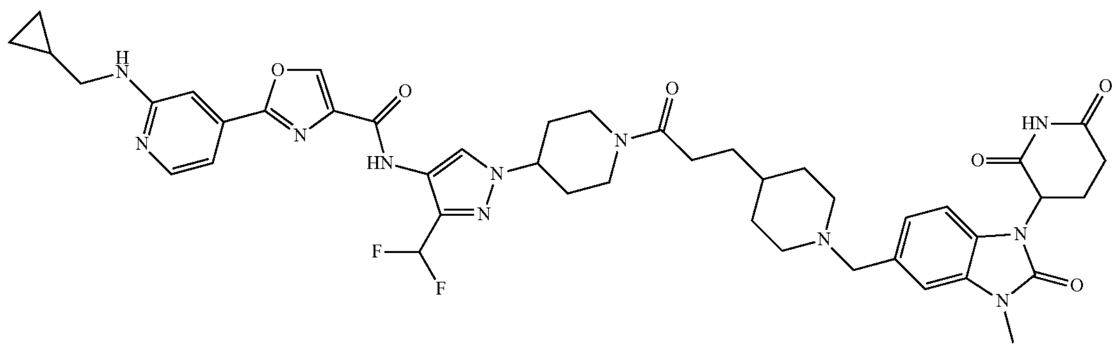 [SMILES: Cn1c(=O)n(C2CCC(=O)NC2=O)c2ccc(CN3CCC(CCC(=O)N4CCC(n5cc(NC(=O)c6coc(-c7ccnc(NCC8CC8)c7)n6)c(C(F)F)n5)CC4)CC3)cc21] |

TABLE 1-continued
Exemplary Compounds
| I-# | Structure |
|---|---|
| I-256 | 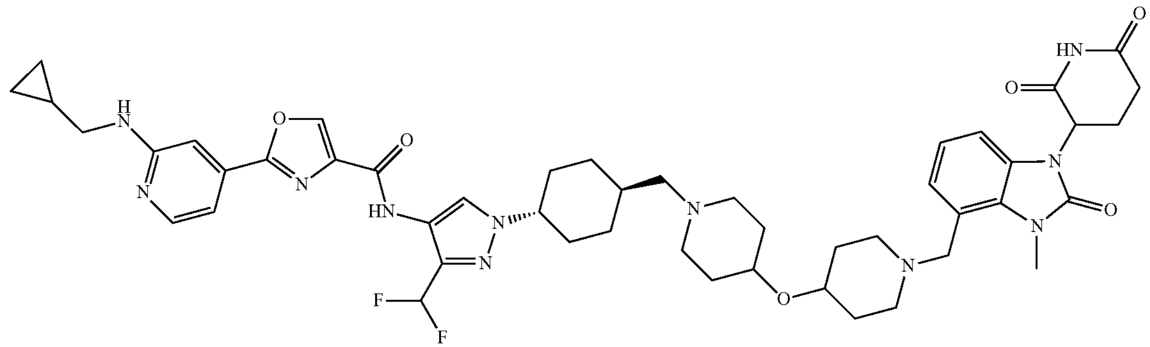 [SMILES: Cn1c(=O)n(C2CCC(=O)NC2=O)c2cccc(CN3CCC(OC4CCN(C[C@H]5CC[C@H](n6cc(NC(=O)c7coc(-c8ccnc(NCC9CC9)c8)n7)c(C(F)F)n6)CC5)CC4)CC3)c21] |
| I-257 | 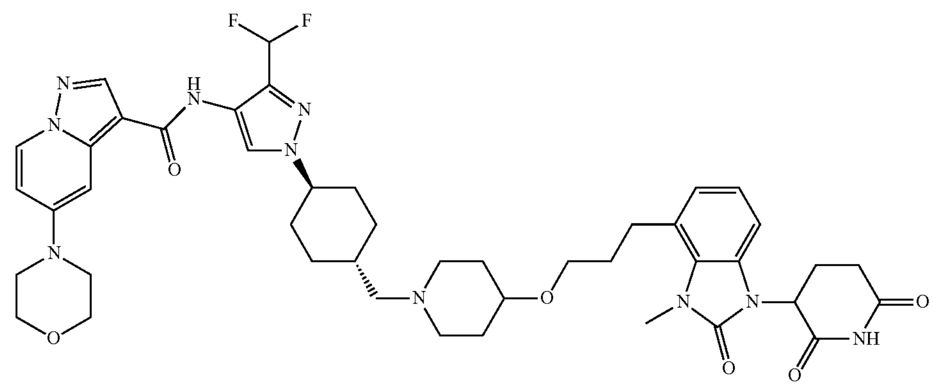 [SMILES: Cn1c(=O)n(C2CCC(=O)NC2=O)c2cccc(CCCOC3CCN(C[C@H]4CC[C@H](n5cc(NC(=O)c6cnn7ccc(N8CCOCC8)cc67)c(C(F)F)n5)CC4)CC3)c21] |

TABLE 1-continued
Exemplary Compounds
| I-# | Structure |
|---|---|
| I-258 | 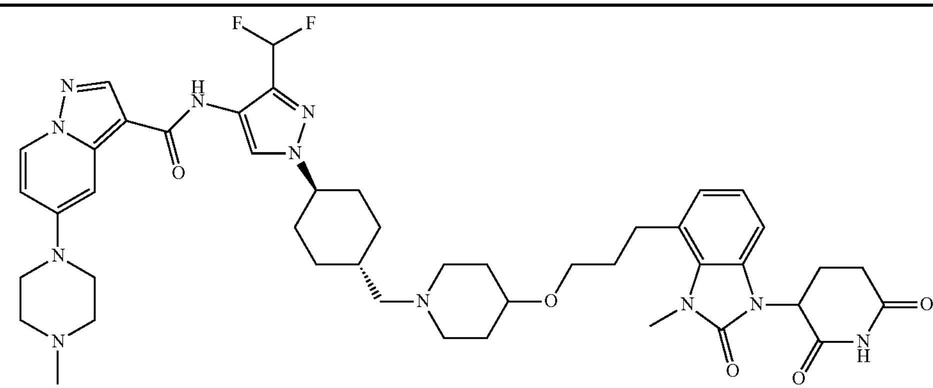 |
| I-259 | 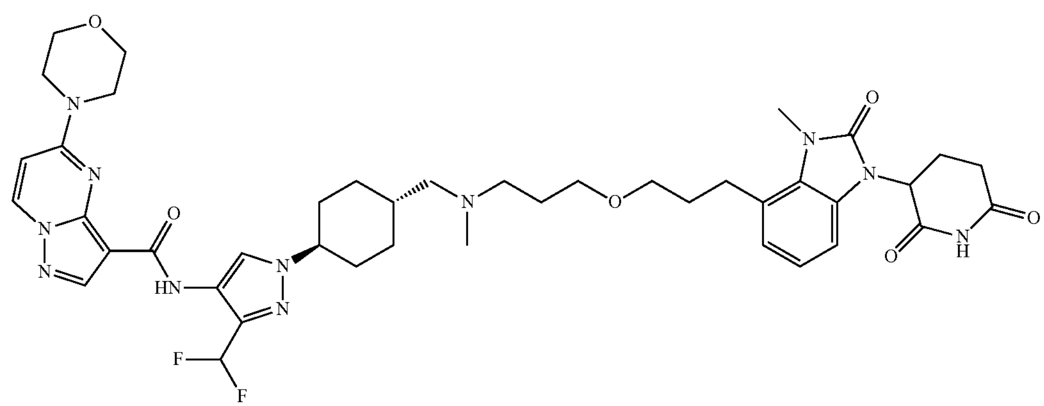 [SMILES: CN(CCCOCCCc1cccc2c1n(C)c(=O)n2C1CCC(=O)NC1=O)C[C@H]1CC[C@H](n2cc(NC(=O)c3cnn4ccc(N5CCOCC5)nc34)c(C(F)F)n2)CC1] |

TABLE 1-continued
Exemplary Compounds
| I-# | Structure |
|---|---|
| I-260 | 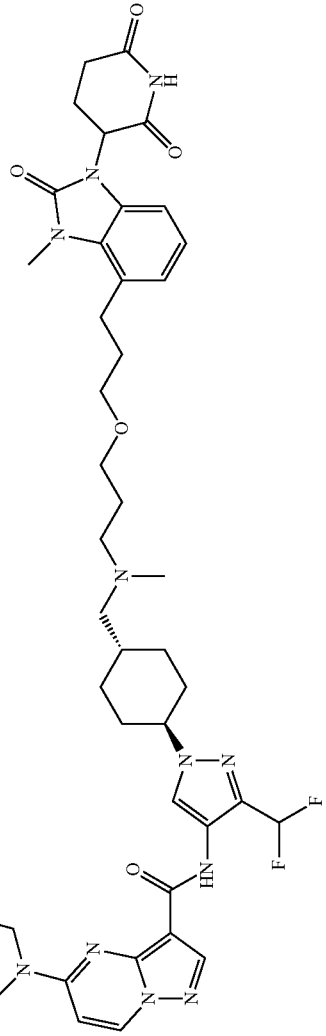 |
| I-261 | 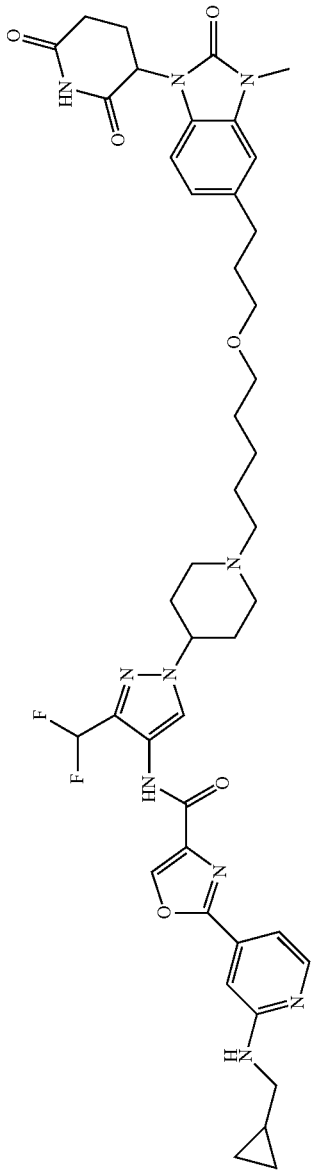 |

TABLE 1-continued
Exemplary Compounds
| I-# | Structure |
|---|---|
| I-262 | 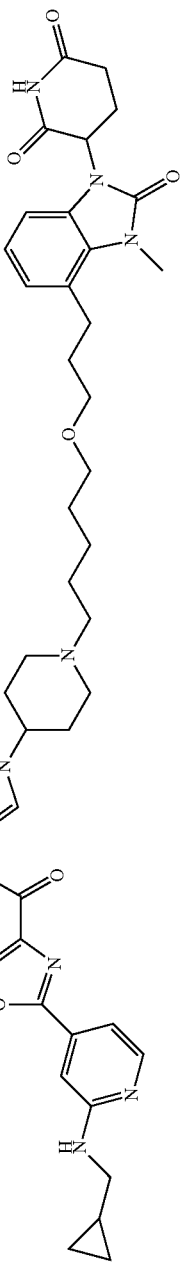 |
| I-263 | 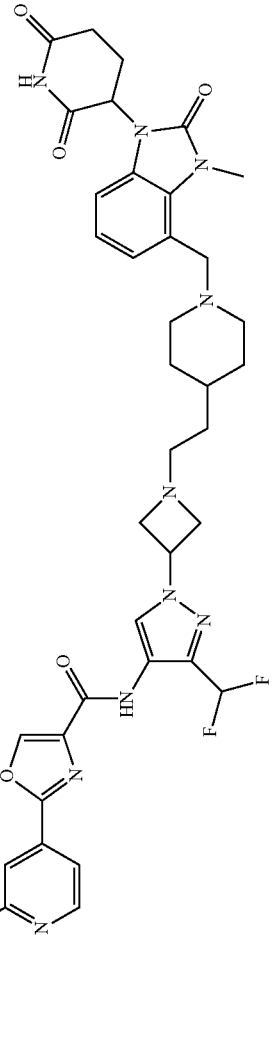 |

TABLE 1-continued
Exemplary Compounds
| I-# | Structure |
|---|---|
| I-264 | 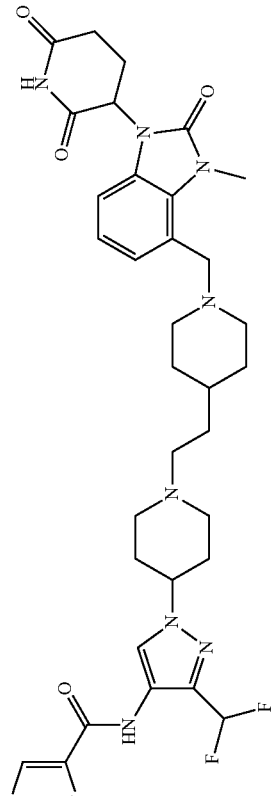 |
| I-265 | 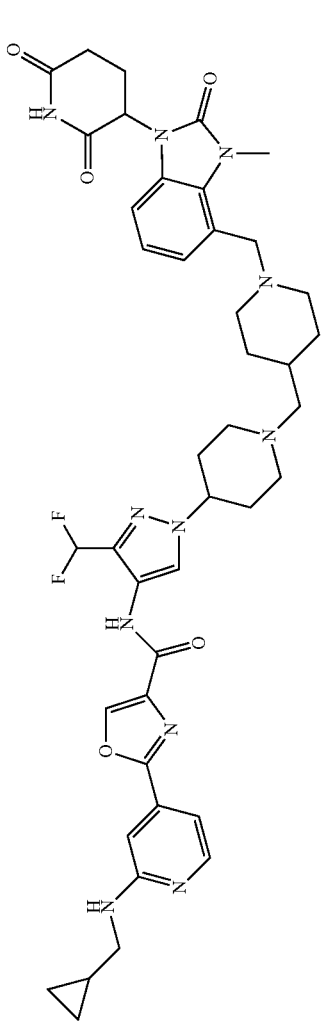 |

TABLE 1-continued
Exemplary Compounds
| I-# | Structure |
|---|---|
| I-266 | 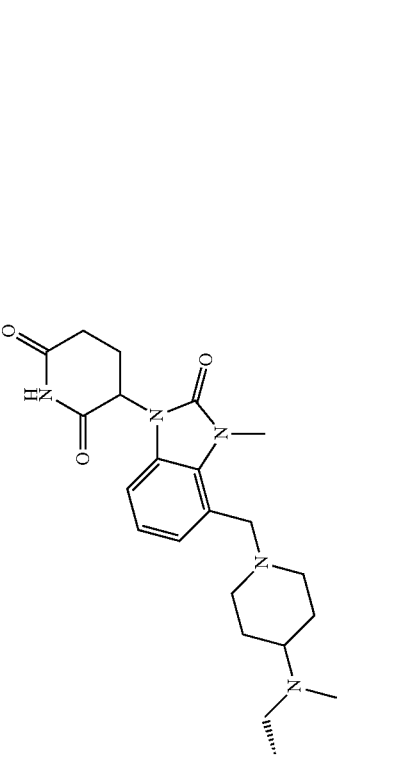 |
| I-267 | 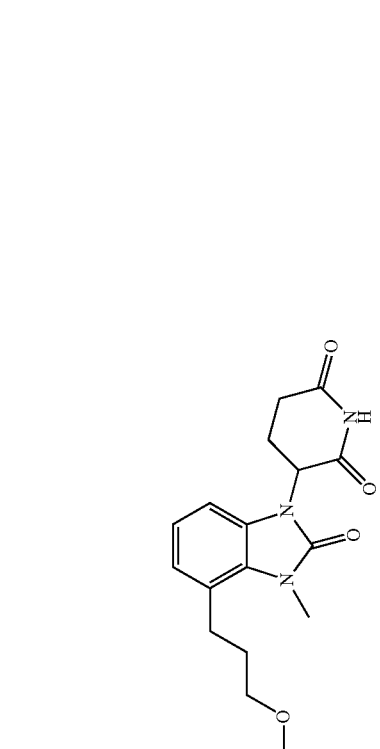 |

TABLE 1-continued

Exemplary Compounds

| I-# | Structure |
|---|---|
| I-268 | 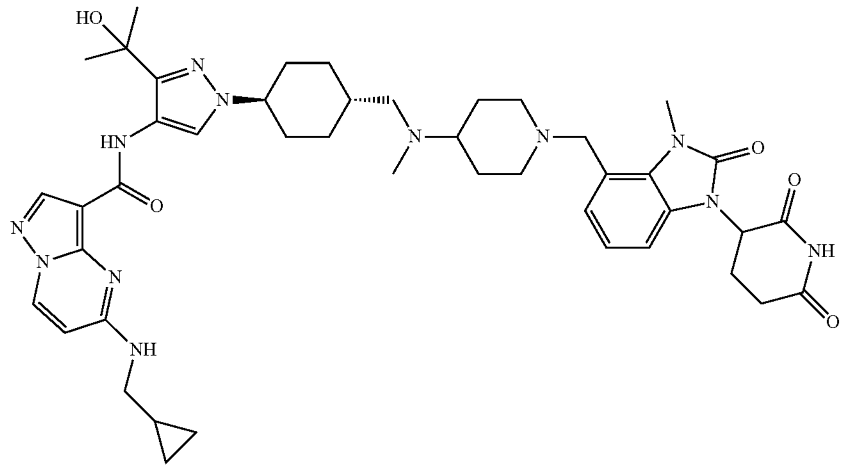 [SMILES: CN(C[C@H]1CC[C@H](n2cc(NC(=O)c3cnn4ccc(NCC5CC5)nc34)c(C(C)(C)O)n2)CC1)C1CCN(Cc2cccc3c2n(C)c(=O)n3C2CCC(=O)NC2=O)CC1] |
| I-269 | 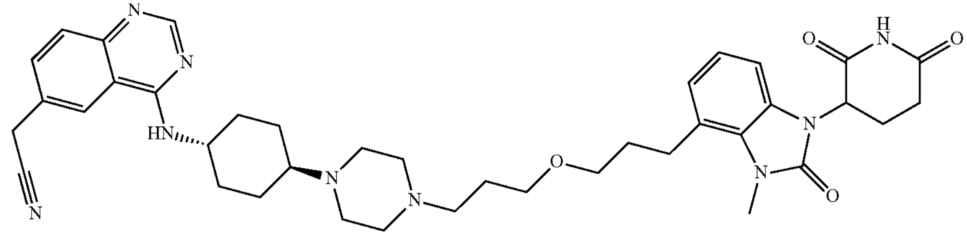 [SMILES: Cn1c(=O)n(C2CCC(=O)NC2=O)c2cccc(CCCOCCCN3CCN([C@H]4CC[C@H](Nc5ncnc6ccc(CC#N)cc56)CC4)CC3)c21] |
| I-270 | 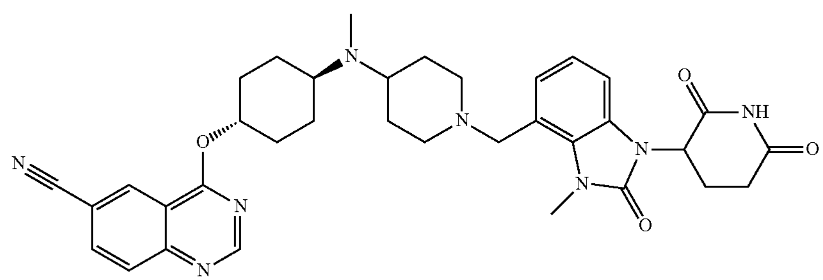 [SMILES: Cn1c(=O)n(C2CCC(=O)NC2=O)c2cccc(CN3CCC(N(C)[C@H]4CC[C@H](Oc5ncnc6ccc(C#N)cc56)CC4)CC3)c21] |

TABLE 1-continued
Exemplary Compounds
| I-# | Structure |
|---|---|
| I-271 | 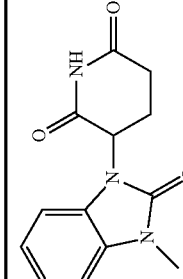 |
| I-272 | 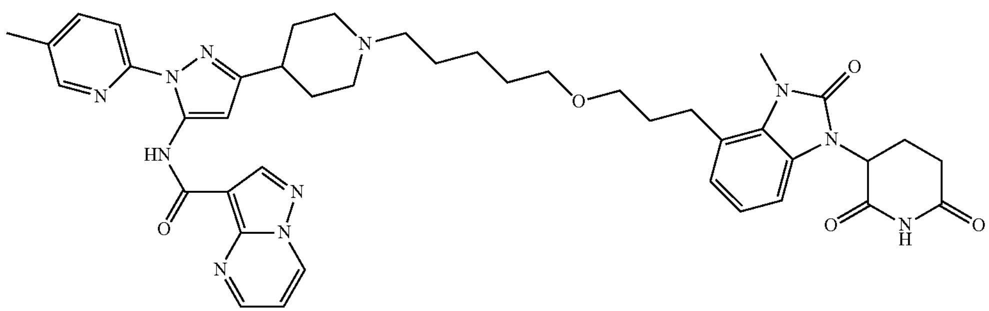 [SMILES: Cc1ccc(-n2nc(C3CCN(CCCCCOCCCc4cccc5c4n(C)c(=O)n5C4CCC(=O)NC4=O)CC3)cc2NC(=O)c2cnn3cccnc23)nc1] |
| I-273 | 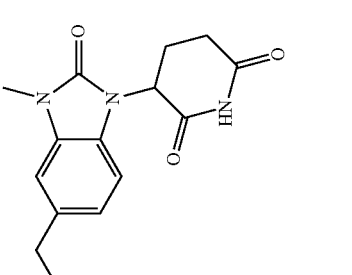 |

TABLE 1-continued
Exemplary Compounds
| I-# | Structure |
|---|---|
| I-274 | 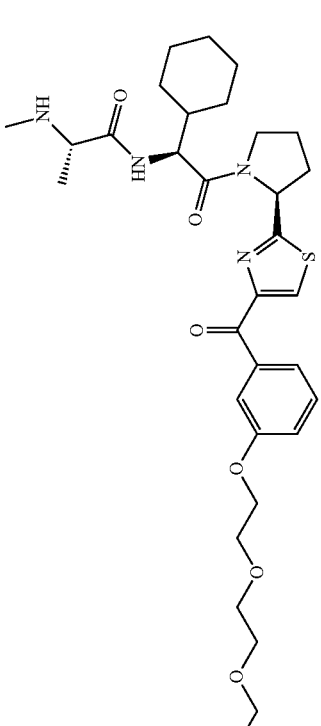 |
| I-275 | 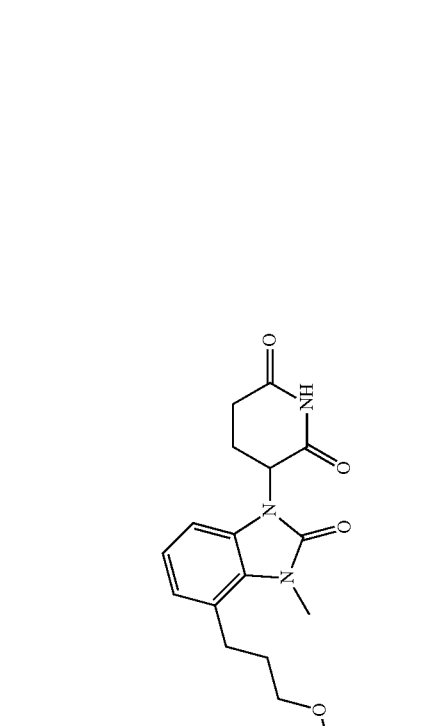 |

TABLE 1-continued
Exemplary Compounds
| I-# | Structure |
|---|---|
| I-276 | 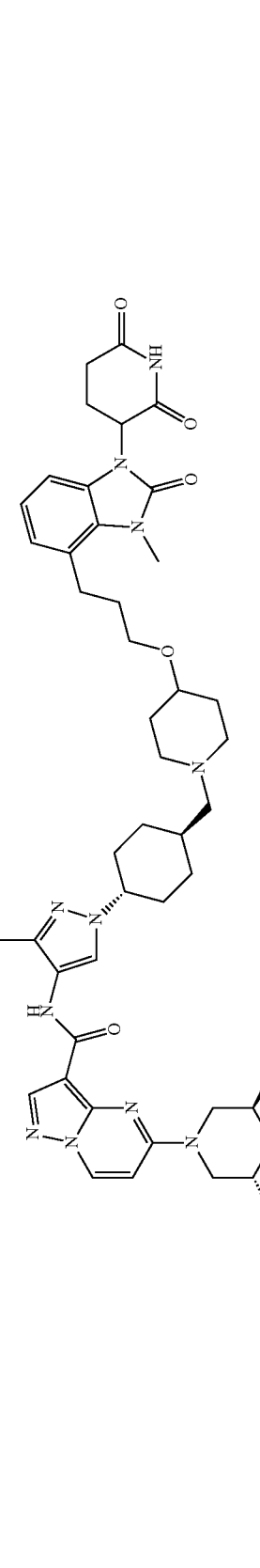 |
| I-277 | 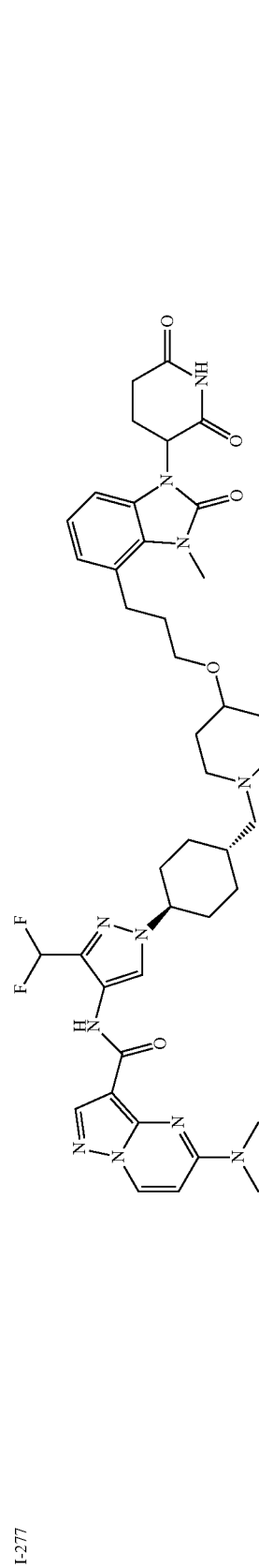 |
| I-278 | 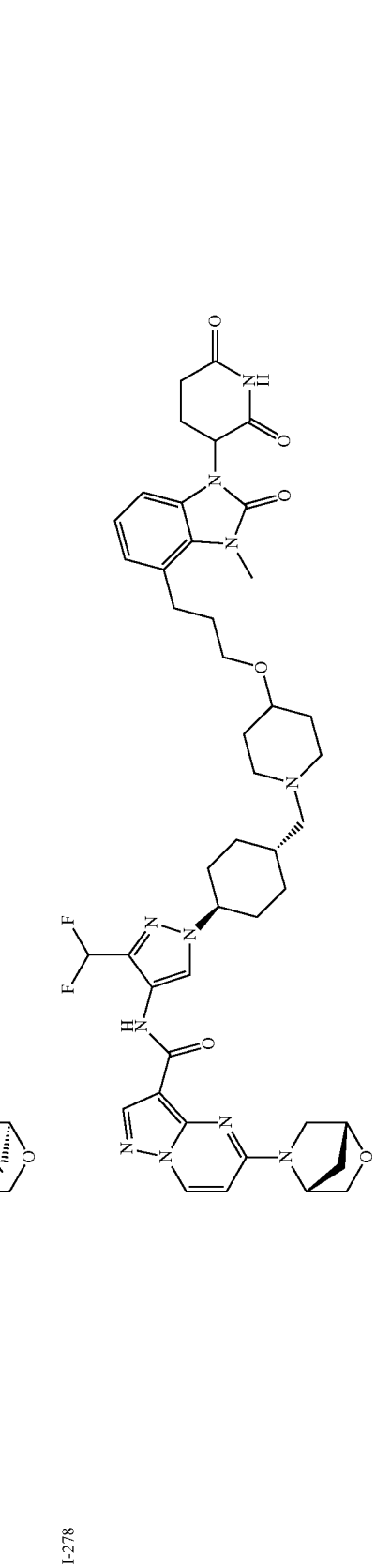 |

TABLE 1-continued
Exemplary Compounds
| I-# | Structure |
|---|---|
| I-279 | 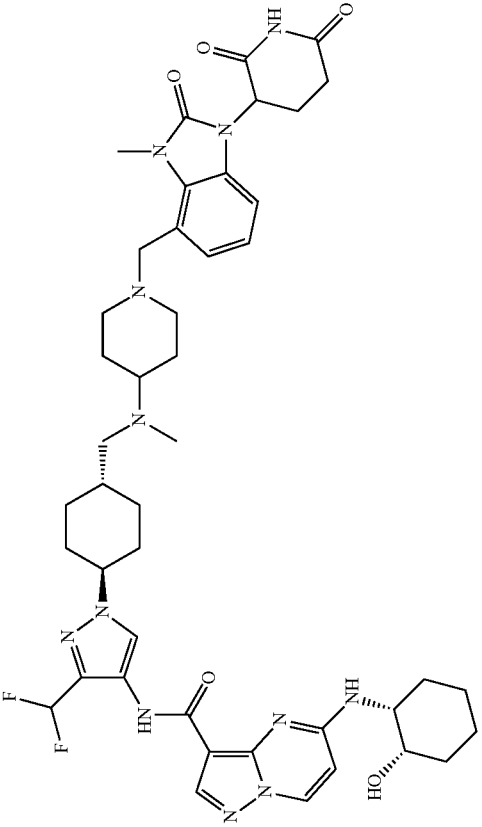 |
| I-280 | 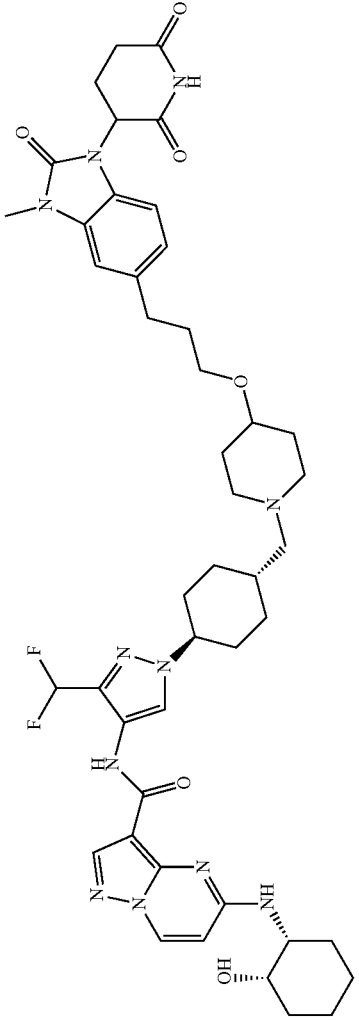 |

TABLE 1-continued
Exemplary Compounds
| I-# | Structure |
|---|---|
| I-282 | 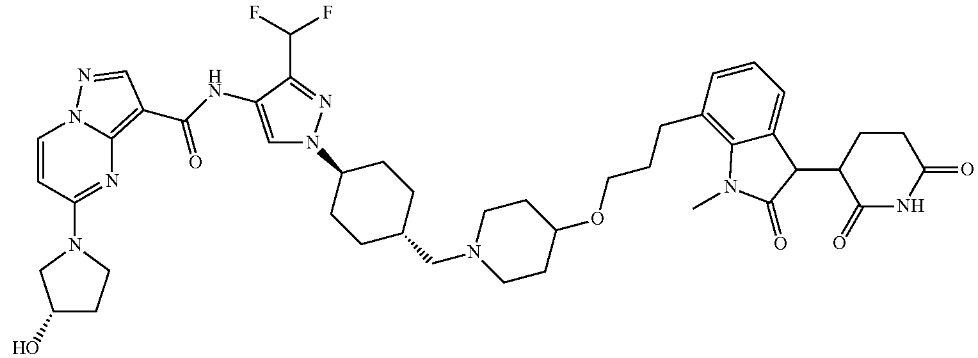 [SMILES: CN1C(=O)C(C2CCC(=O)NC2=O)c2cccc(CCCOC3CCN(C[C@H]4CC[C@H](n5cc(NC(=O)c6cnn7ccc(N8CC[C@H](O)C8)nc67)c(C(F)F)n5)CC4)CC3)c21] |
| I-283 | 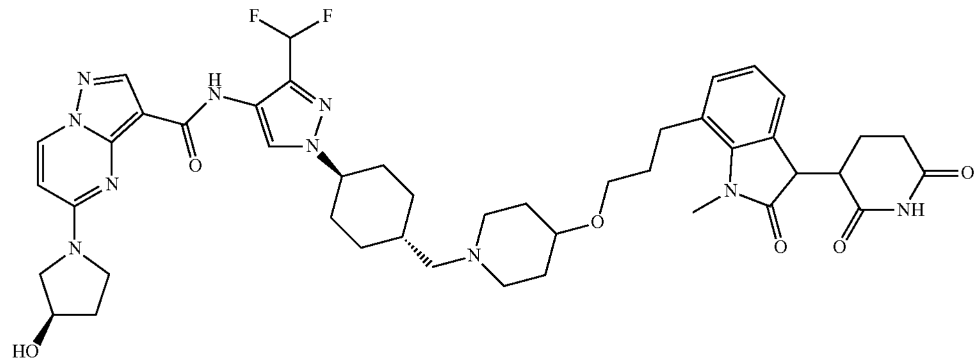 [SMILES: CN1C(=O)C(C2CCC(=O)NC2=O)c2cccc(CCCOC3CCN(C[C@H]4CC[C@H](n5cc(NC(=O)c6cnn7ccc(N8CC[C@@H](O)C8)nc67)c(C(F)F)n5)CC4)CC3)c21] |

TABLE 1-continued
Exemplary Compounds
| I-# | Structure |
|---|---|
| I-284 | 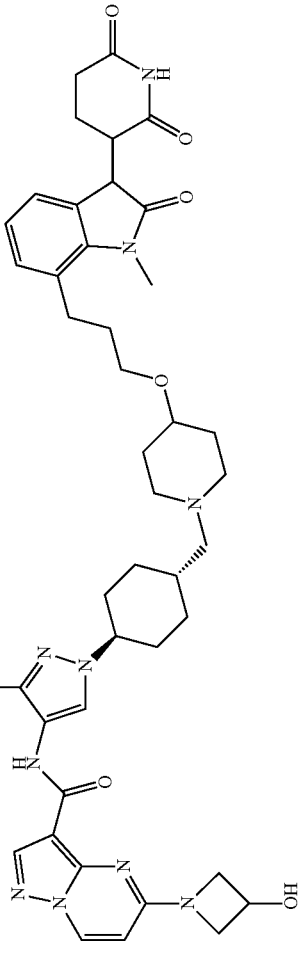 |
| I-285 | 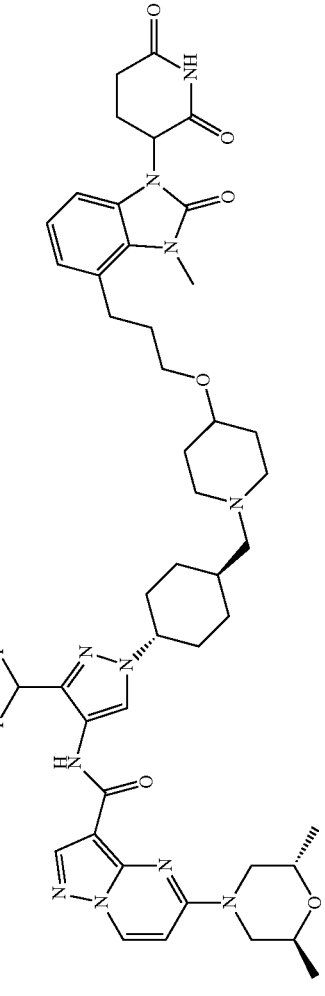 |

TABLE 1-continued
Exemplary Compounds
| I-# | Structure |
|---|---|
| I-286 | 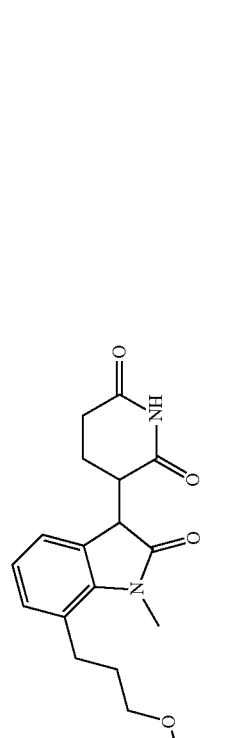 |
| I-287 | 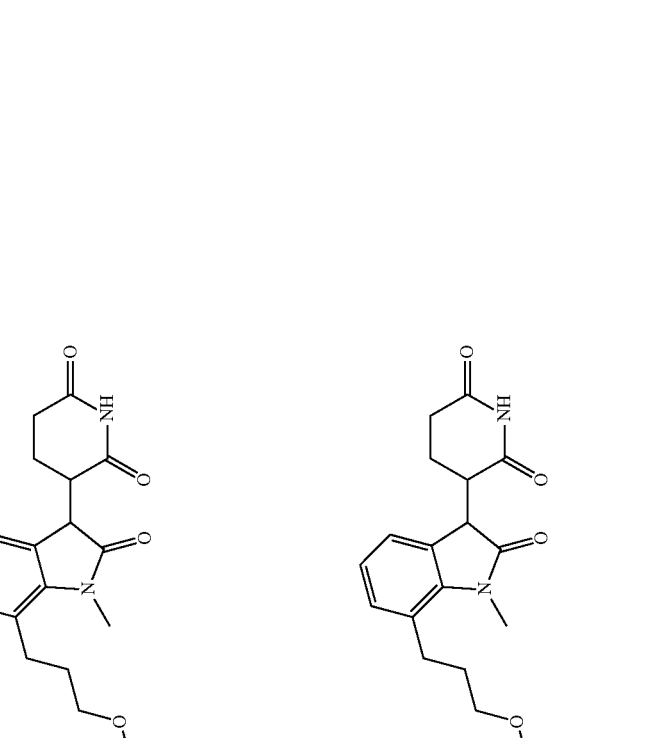 |

TABLE 1-continued
Exemplary Compounds
| I-# | Structure |
|---|---|
| I-288 | 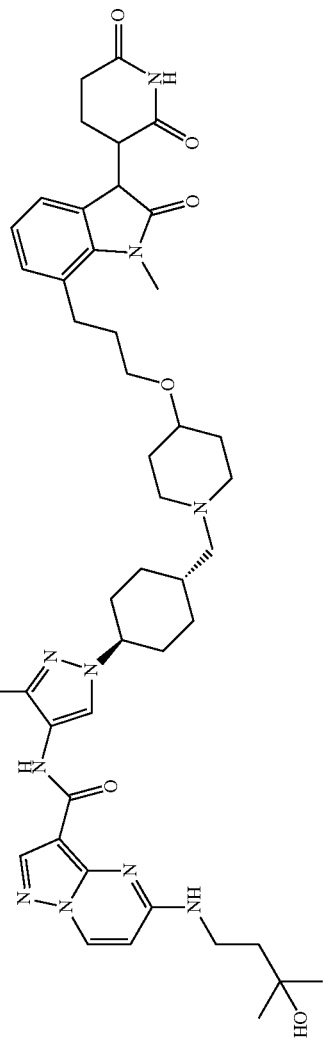 |
| I-289 | 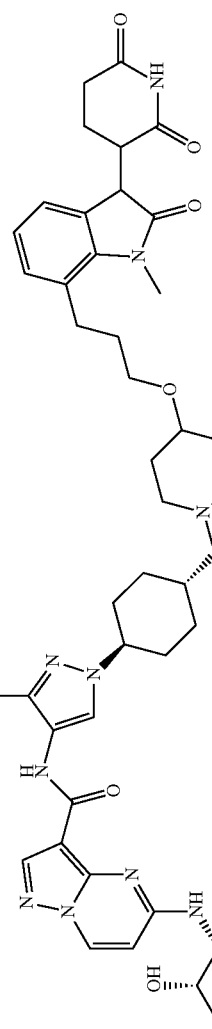 |

TABLE 1-continued
Exemplary Compounds
| I-# | Structure |
|---|---|
| I-290 | 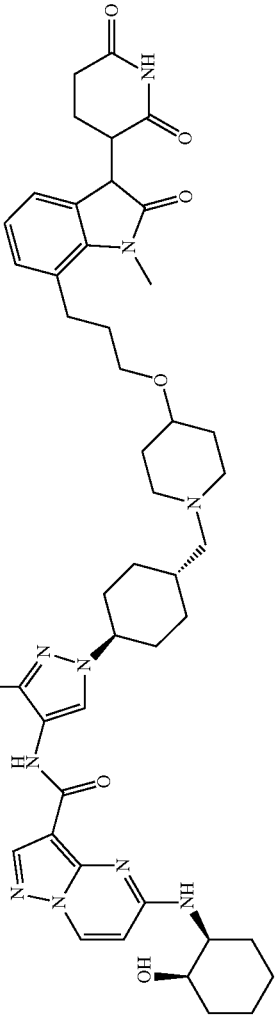 |
| I-291 | 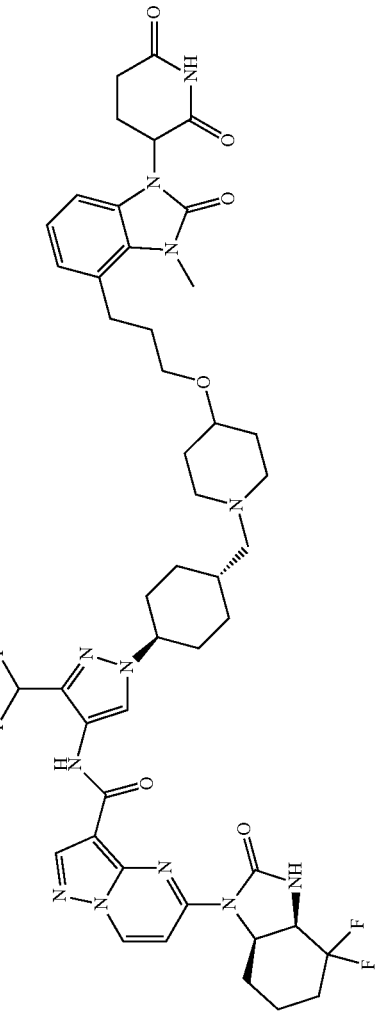 |

TABLE 1-continued

Exemplary Compounds

| I-# | Structure |
|---|---|
| I-292 | 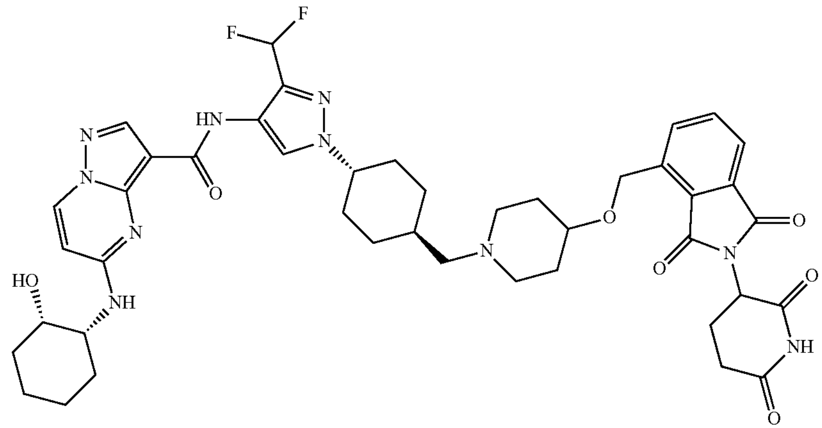 [SMILES: O=C1CCC(N2C(=O)c3cccc(COC4CCN(C[C@H]5CC[C@H](n6cc(NC(=O)c7cnn8ccc(N[C@@H]9CCCC[C@@H]9O)nc78)c(C(F)F)n6)CC5)CC4)c3C2=O)C(=O)N1] |
| I-293 | 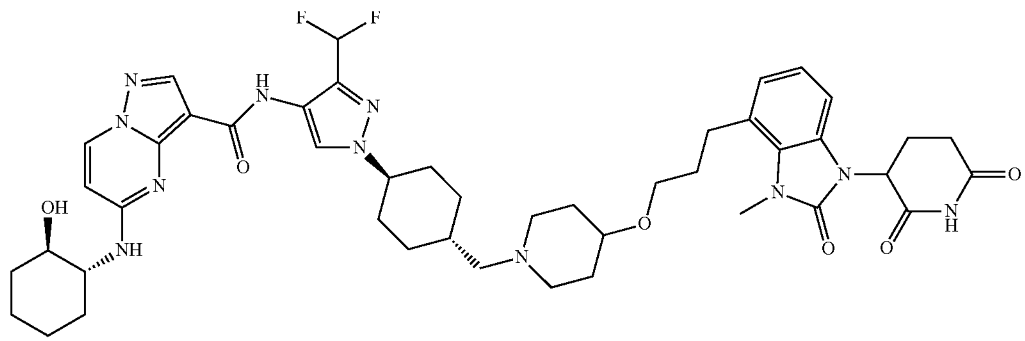 [SMILES: Cn1c(=O)n(C2CCC(=O)NC2=O)c2cccc(CCCOC3CCN(C[C@H]4CC[C@H](n5cc(NC(=O)c6cnn7ccc(N[C@@H]8CCCC[C@H]8O)nc67)c(C(F)F)n5)CC4)CC3)c21] |

TABLE 1-continued
Exemplary Compounds
| I-# | Structure |
|---|---|
| I-294 | 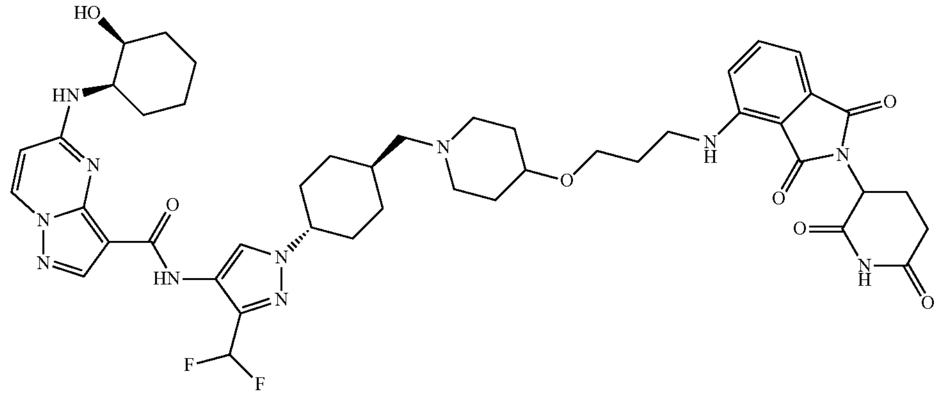 [SMILES: O=C1CCC(N2C(=O)c3cccc(NCCCOC4CCN(C[C@H]5CC[C@H](n6cc(NC(=O)c7cnn8ccc(N[C@@H]9CCCC[C@@H]9O)nc78)c(C(F)F)n6)CC5)CC4)c3C2=O)C(=O)N1] |
| I-296 | 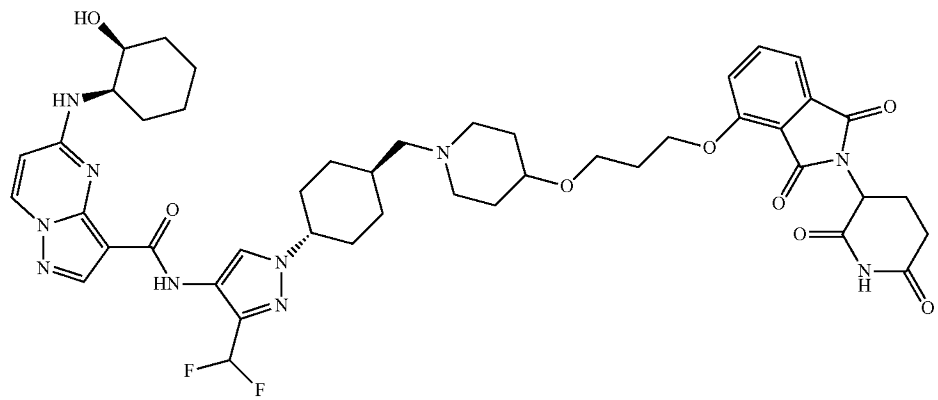 [SMILES: O=C1CCC(N2C(=O)c3cccc(OCCCOC4CCN(C[C@H]5CC[C@H](n6cc(NC(=O)c7cnn8ccc(N[C@@H]9CCCC[C@@H]9O)nc78)c(C(F)F)n6)CC5)CC4)c3C2=O)C(=O)N1] |

TABLE 1-continued
Exemplary Compounds
| I-# | Structure |
|---|---|
| I-297 | 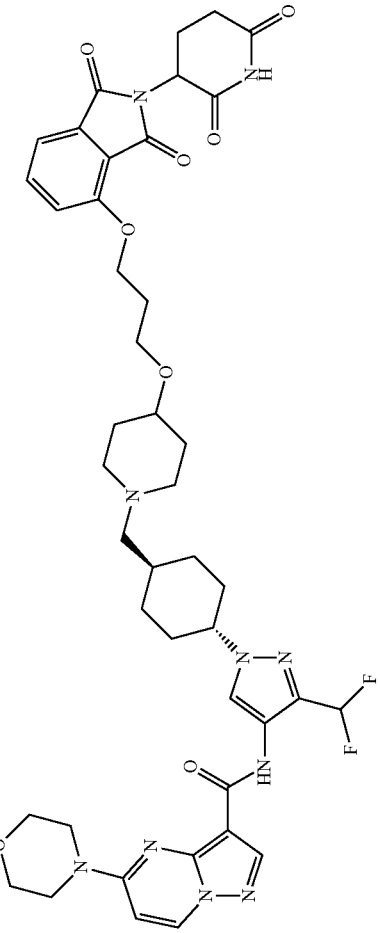 |
| I-298 | 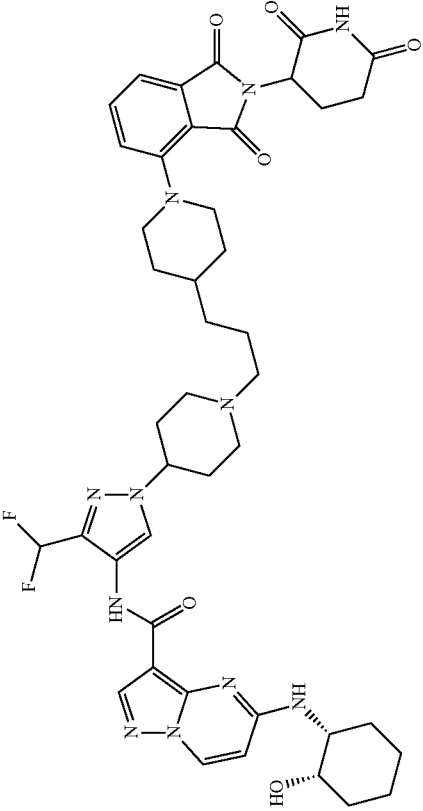 |

TABLE 1-continued
Exemplary Compounds
| I-# | Structure |
|---|---|
| I-299 | 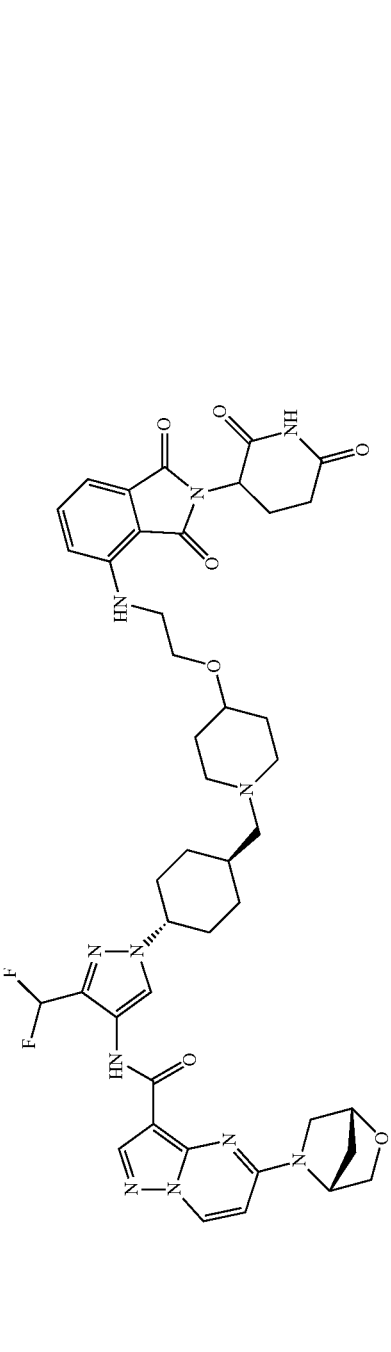 |
| I-300 | 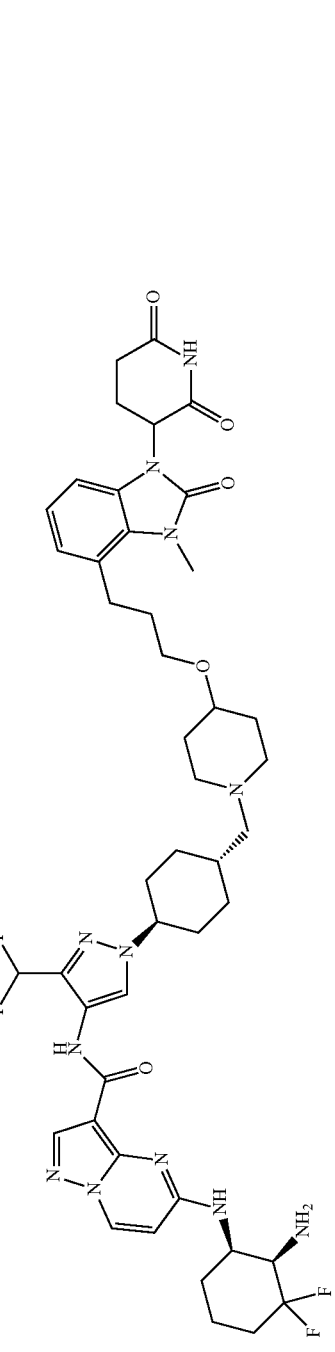 |

TABLE 1-continued
Exemplary Compounds
| I-# | Structure |
|---|---|
| I-301 | 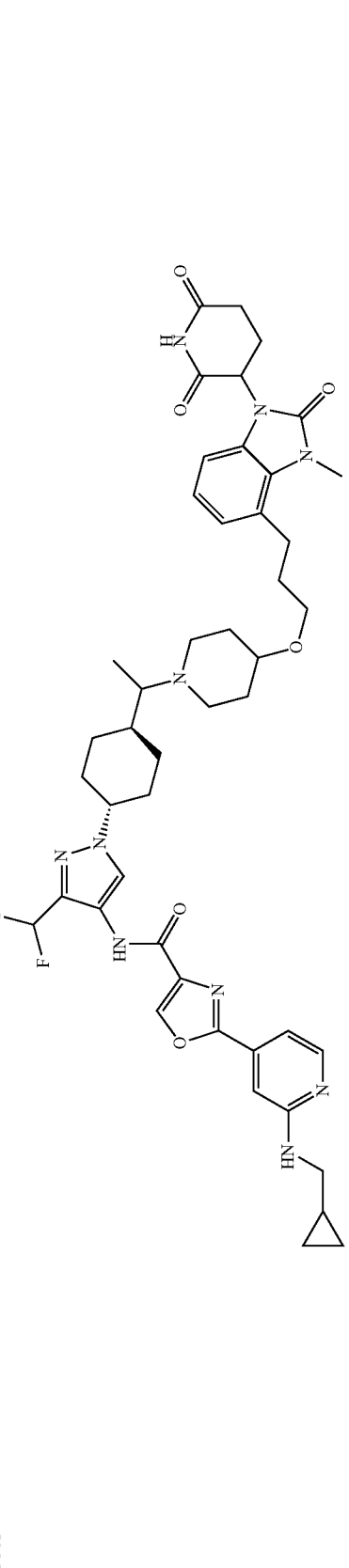 |
| I-302 | 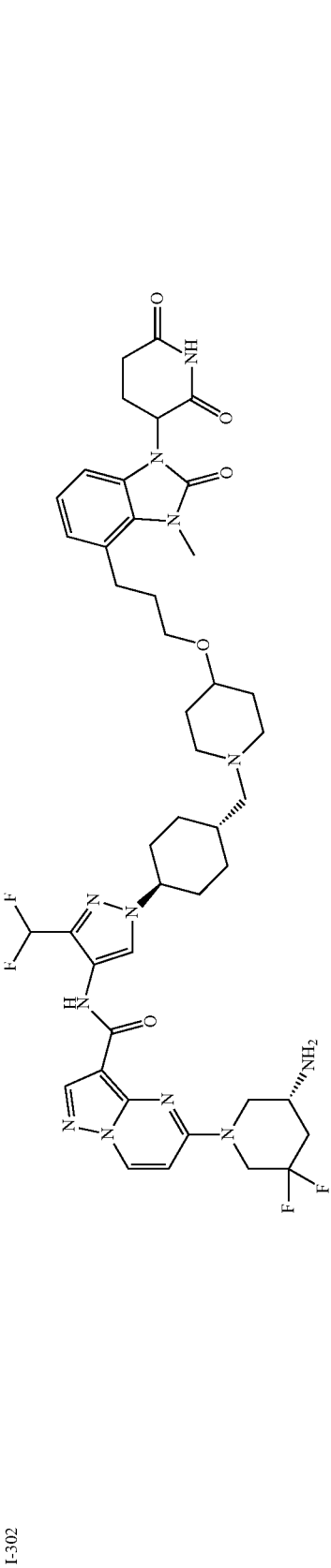 |

TABLE 1-continued

Exemplary Compounds

| I-# | Structure |
|---|---|
| I-303 | 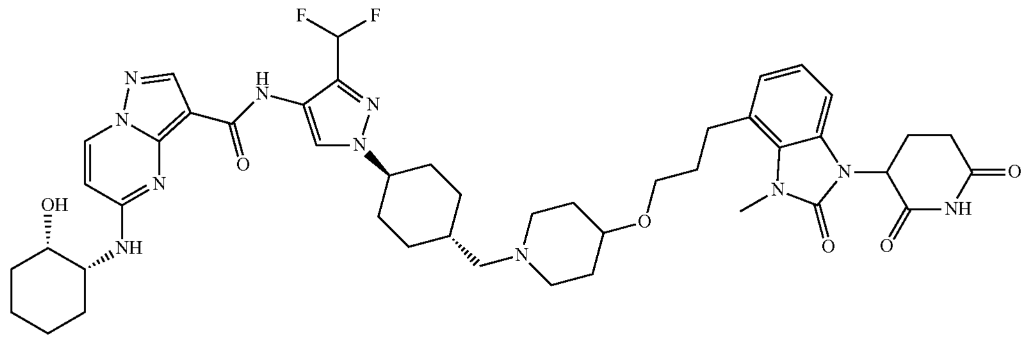 [SMILES: Cn1c(=O)n(C2CCC(=O)NC2=O)c2cccc(CCCOC3CCN(C[C@H]4CC[C@H](n5cc(NC(=O)c6cnn7ccc(N[C@@H]8CCCC[C@@H]8O)nc67)c(C(F)F)n5)CC4)CC3)c21] |
| I-304 | 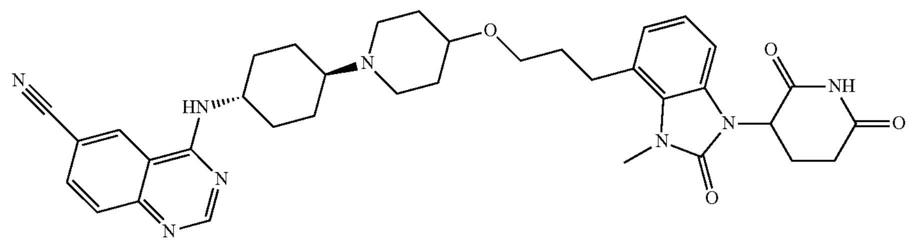 [SMILES: Cn1c(=O)n(C2CCC(=O)NC2=O)c2cccc(CCCOC3CCN([C@H]4CC[C@H](Nc5ncnc6ccc(C#N)cc56)CC4)CC3)c21] |
| I-305 | 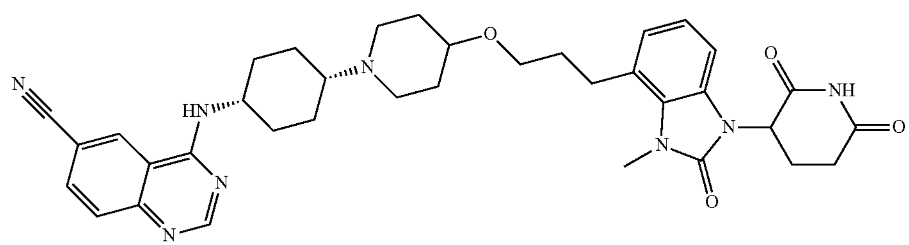 [SMILES: Cn1c(=O)n(C2CCC(=O)NC2=O)c2cccc(CCCOC3CCN([C@H]4CC[C@@H](Nc5ncnc6ccc(C#N)cc56)CC4)CC3)c21] |

TABLE 1-continued
Exemplary Compounds
| I-# | Structure |
|---|---|
| I-306 | 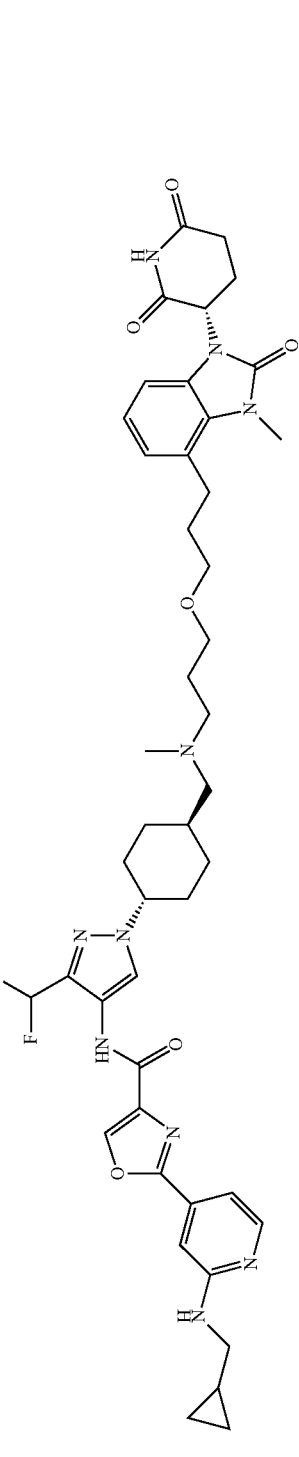 |
| I-307 | 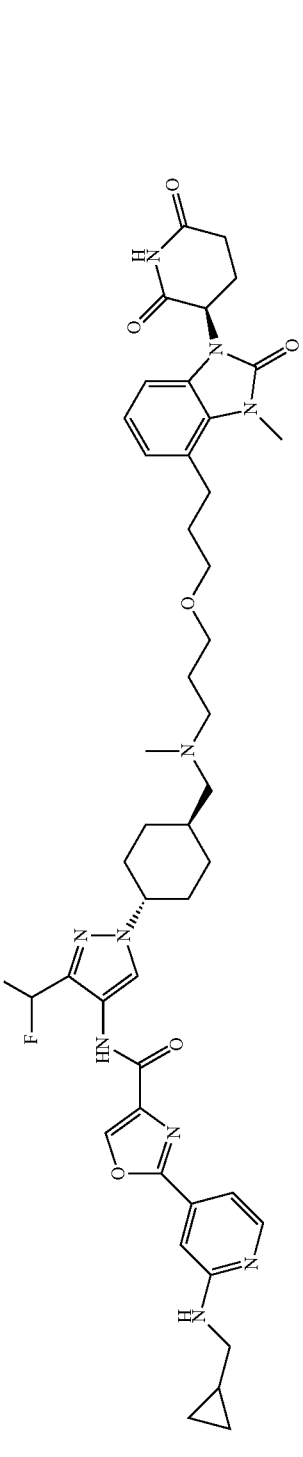 |

TABLE 1-continued
Exemplary Compounds
| I-# | Structure |
|---|---|
| I-308 | 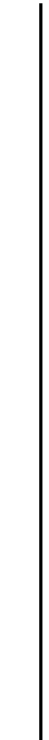 |
| I-309 | 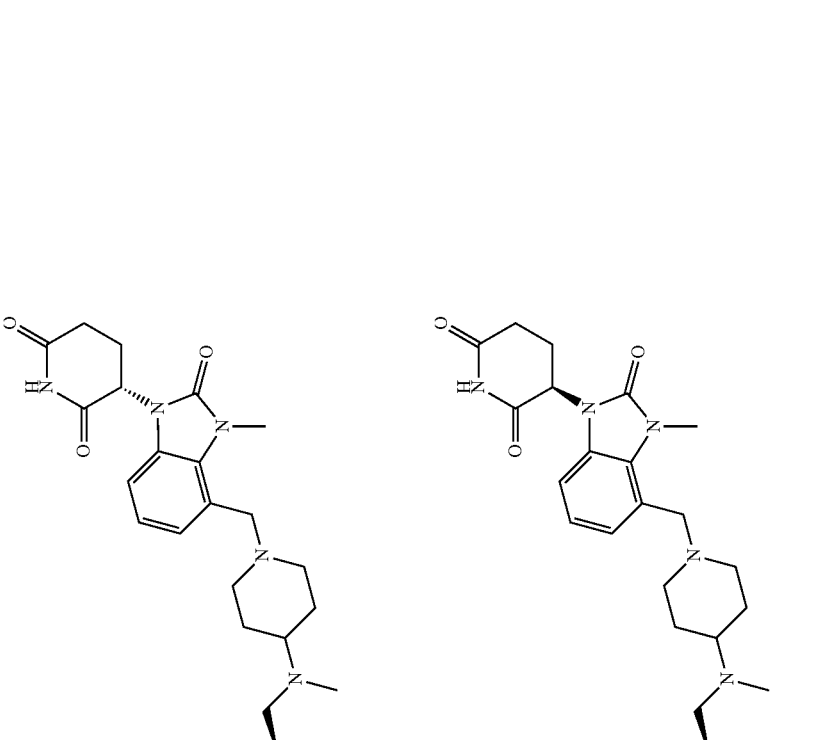 |

TABLE 1-continued

Exemplary Compounds

| I-# | Structure |
|---|---|
| I-310 | 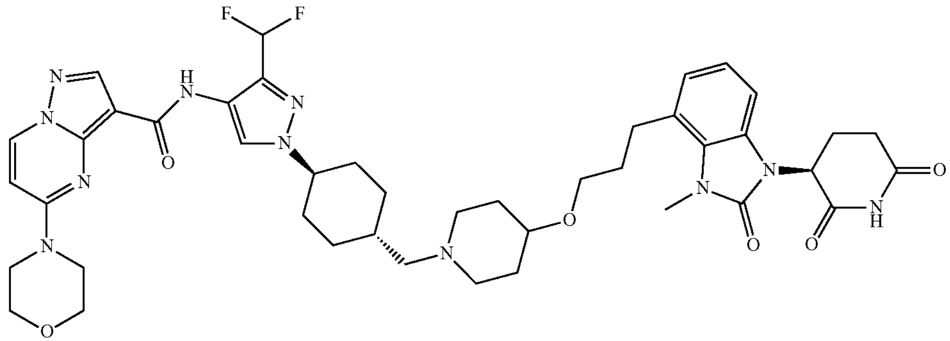 [SMILES: Cn1c(=O)n([C@H]2CCC(=O)NC2=O)c2cccc(CCCOC3CCN(C[C@H]4CC[C@H](n5cc(NC(=O)c6cnn7ccc(N8CCOCC8)nc67)c(C(F)F)n5)CC4)CC3)c21] |
| I-311 | 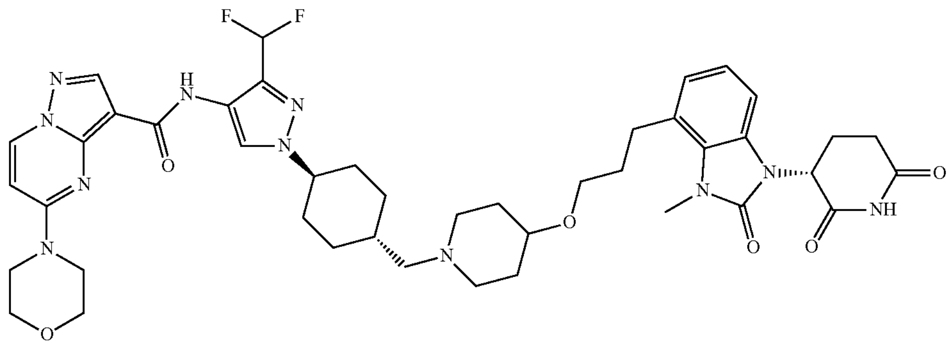 [SMILES: Cn1c(=O)n([C@@H]2CCC(=O)NC2=O)c2cccc(CCCOC3CCN(C[C@H]4CC[C@H](n5cc(NC(=O)c6cnn7ccc(N8CCOCC8)nc67)c(C(F)F)n5)CC4)CC3)c21] |
| I-312 | 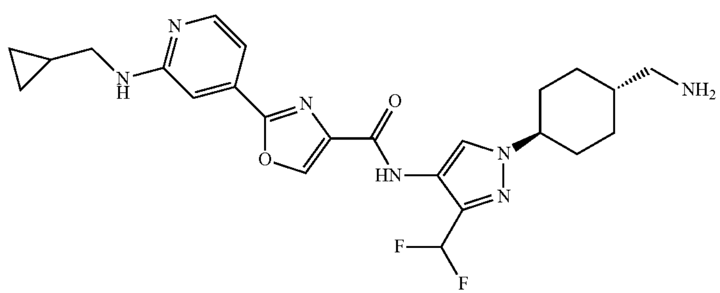 [SMILES: NC[C@H]1CC[C@H](n2cc(NC(=O)c3coc(-c4ccnc(NCC5CC5)c4)n3)c(C(F)F)n2)CC1] |

TABLE 1-continued
Exemplary Compounds
| I-# | Structure |
|---|---|
| I-313 | 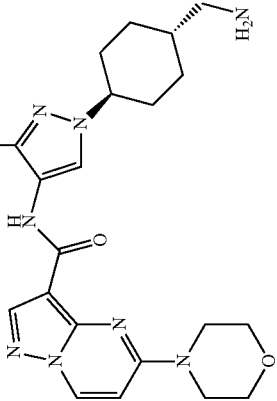 |
| I-314 | 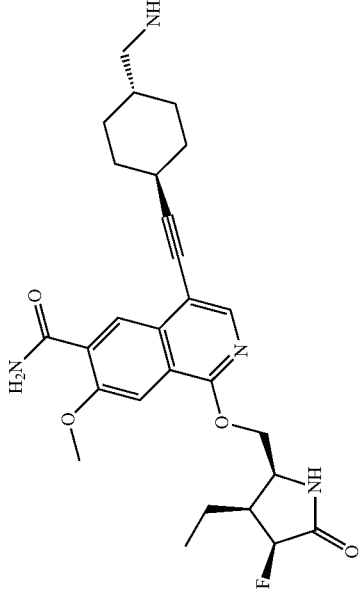 |

TABLE 1-continued
Exemplary Compounds
| I-# | Structure |
|---|---|
| I-315 | 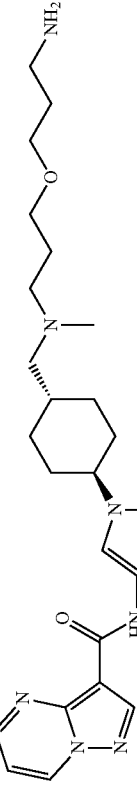 |
| I-316 | 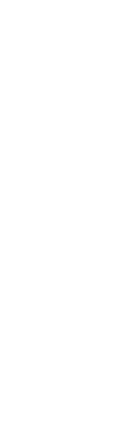 |

TABLE 1-continued
Exemplary Compounds
| I-# | Structure |
|---|---|
| I-317 | 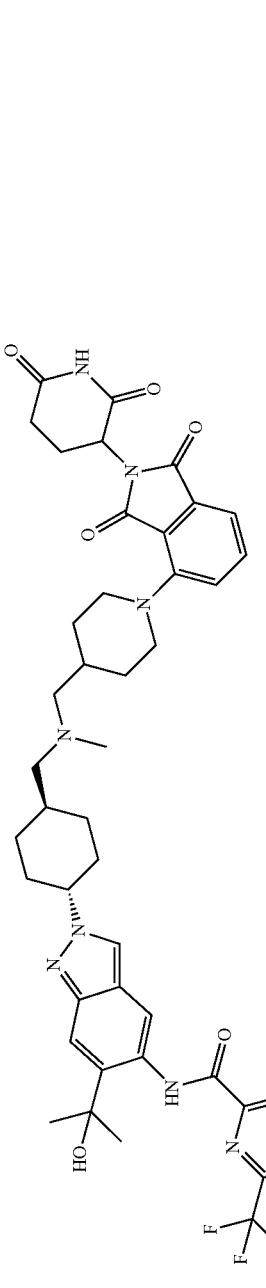 |
| I-318 | 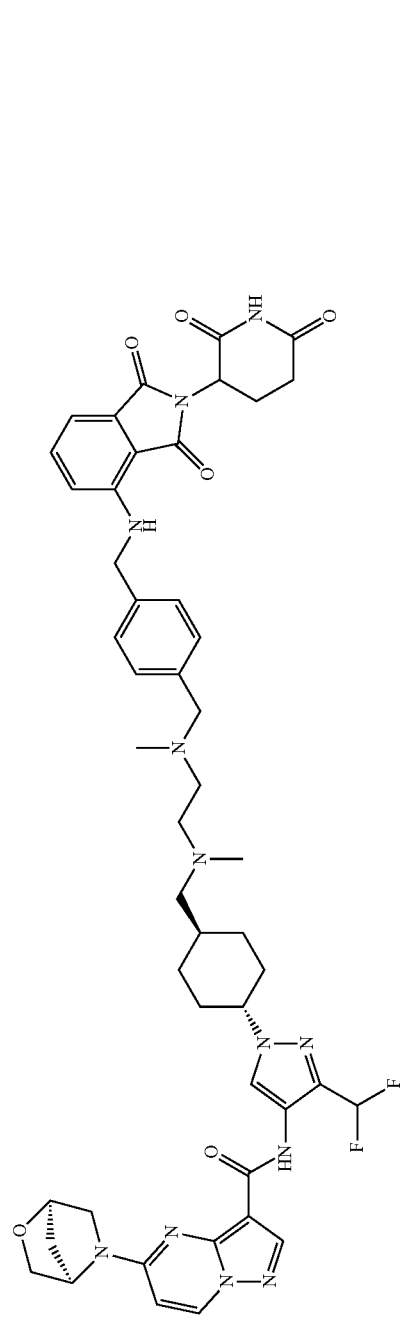 |

TABLE 1-continued
Exemplary Compounds
| I-# | Structure |
|---|---|
| I-320 | 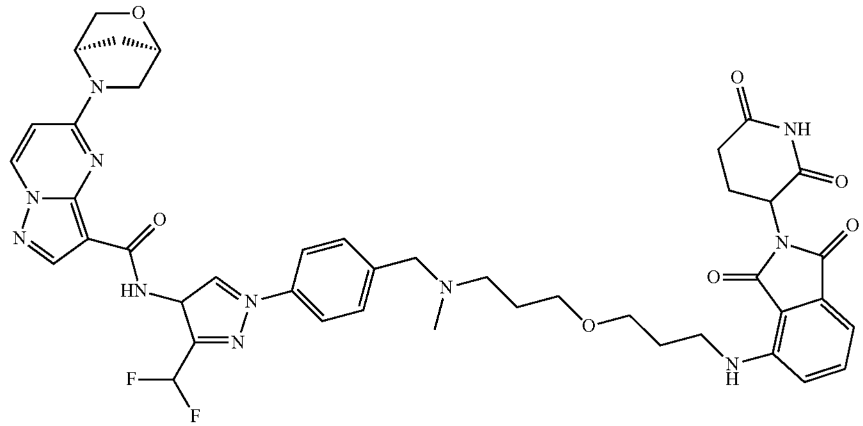 |
| I-321 | 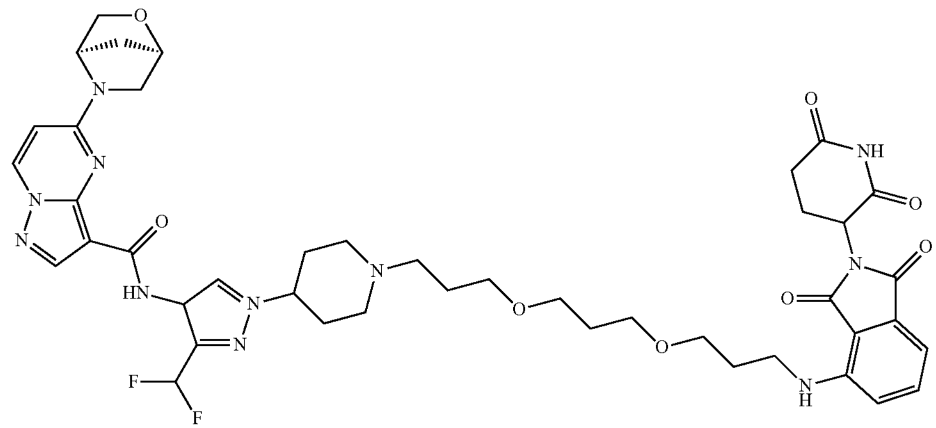 |

TABLE 1-continued
Exemplary Compounds
| I-# | Structure |
|---|---|
| I-322 | 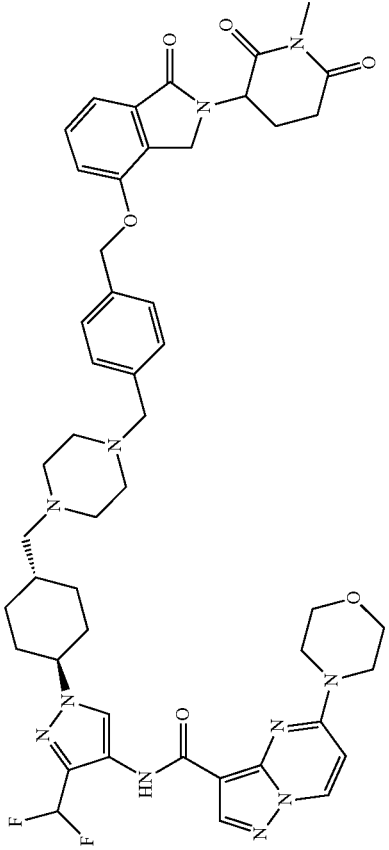 |
| I-323 | 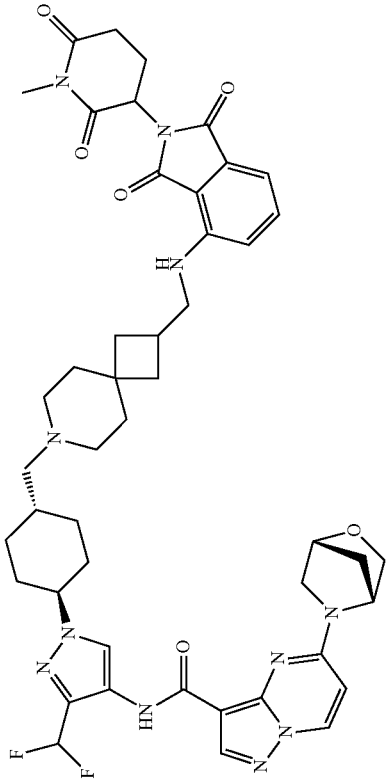 |

TABLE 1-continued
Exemplary Compounds
| I-# | Structure |
|---|---|
| I-324 | 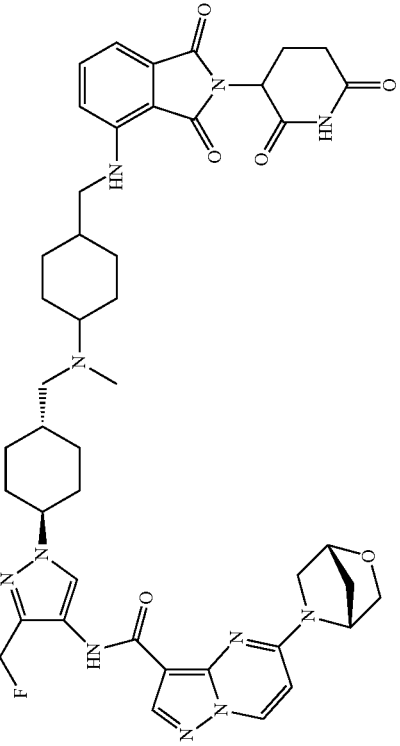 |
| I-325 | 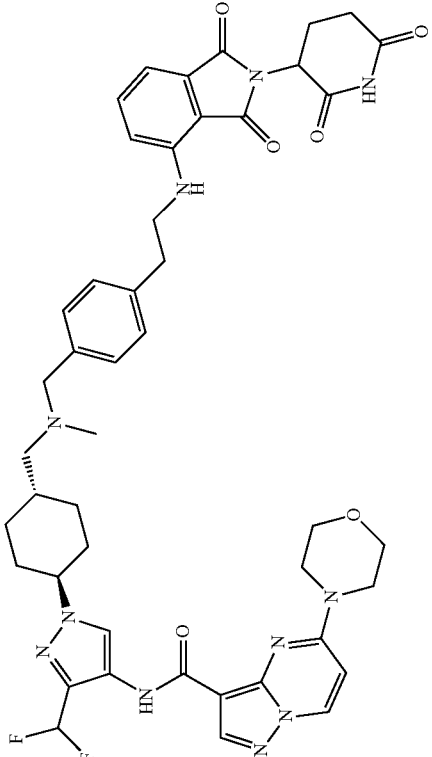 |

TABLE 1-continued
Exemplary Compounds
| I-# | Structure |
|---|---|
| I-326 | 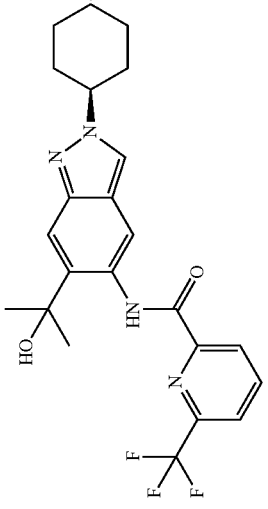 |
| I-327 | 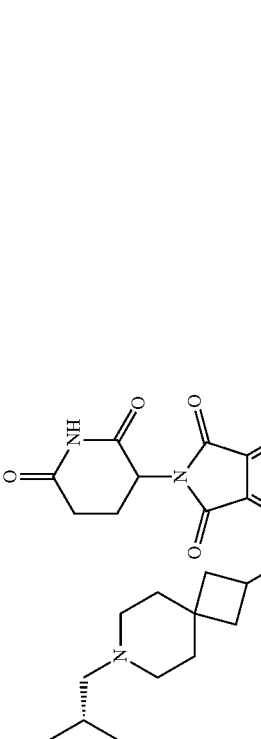 |

TABLE 1-continued
Exemplary Compounds
| I-# | Structure |
|---|---|
| I-328 | 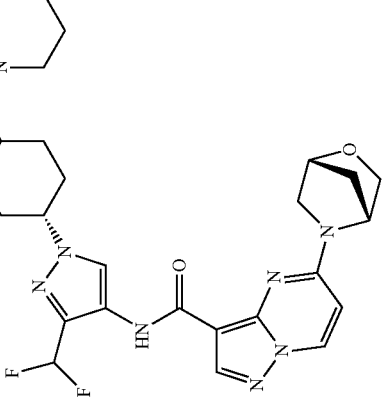 |
| I-329 | 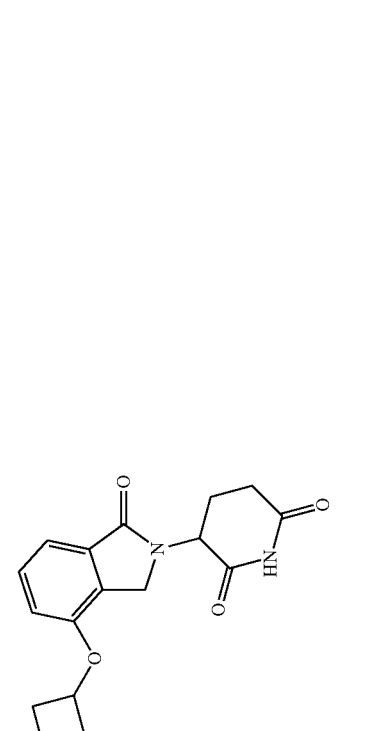 |

TABLE 1-continued
Exemplary Compounds
| I-# | Structure |
|---|---|
| I-330 | 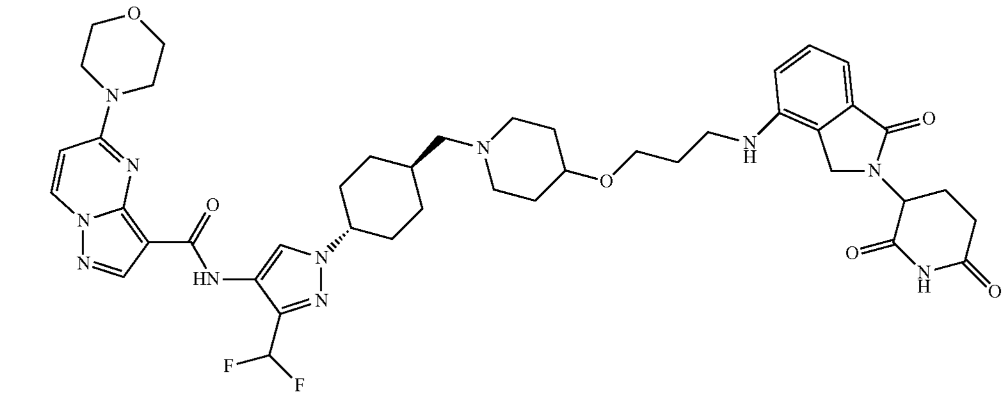 [SMILES: O=C1CCC(N2Cc3c(NCCCOC4CCN(C[C@H]5CC[C@H](n6cc(NC(=O)c7cnn8ccc(N9CCOCC9)nc78)c(C(F)F)n6)CC5)CC4)cccc3C2=O)C(=O)N1] |
| I-331 | 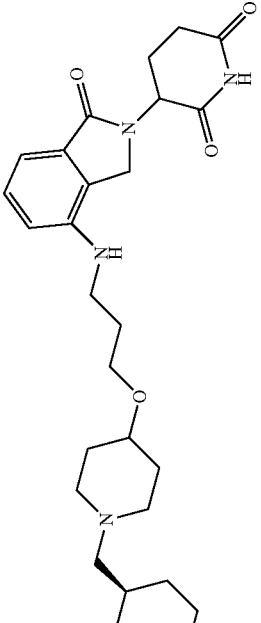 |

TABLE 1-continued
Exemplary Compounds
| I-# | Structure |
|---|---|
| I-332 | 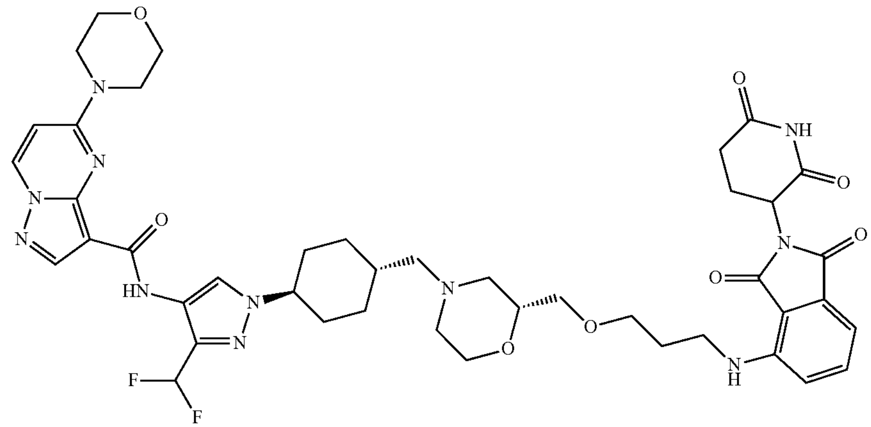 [SMILES: O=C1CCC(N2C(=O)c3cccc(NCCCOC[C@H]4CN(C[C@H]5CC[C@H](n6cc(NC(=O)c7cnn8ccc(N9CCOCC9)nc78)c(C(F)F)n6)CC5)CCO4)c3C2=O)C(=O)N1] |
| I-333 | 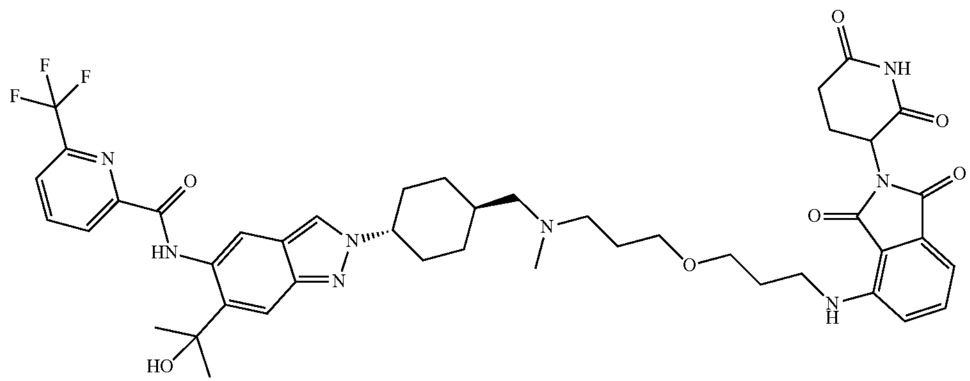 [SMILES: CN(CCCOCCCNc1cccc2c1C(=O)N(C1CCC(=O)NC1=O)C2=O)C[C@H]1CC[C@H](n2cc3cc(NC(=O)c4cccc(C(F)(F)F)n4)c(C(C)(C)O)cc3n2)CC1] |

TABLE 1-continued
Exemplary Compounds
| I-# | Structure |
|---|---|
| I-334 | 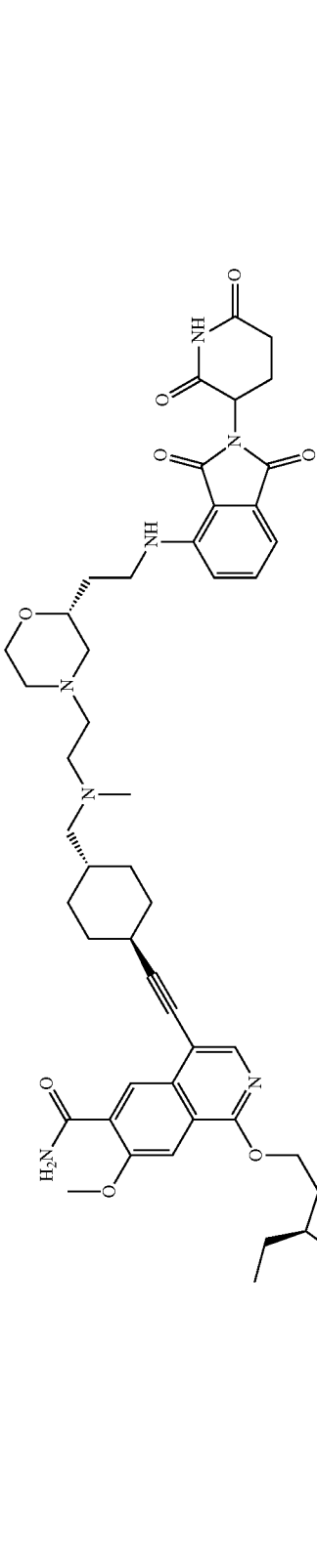 |
| I-335 | 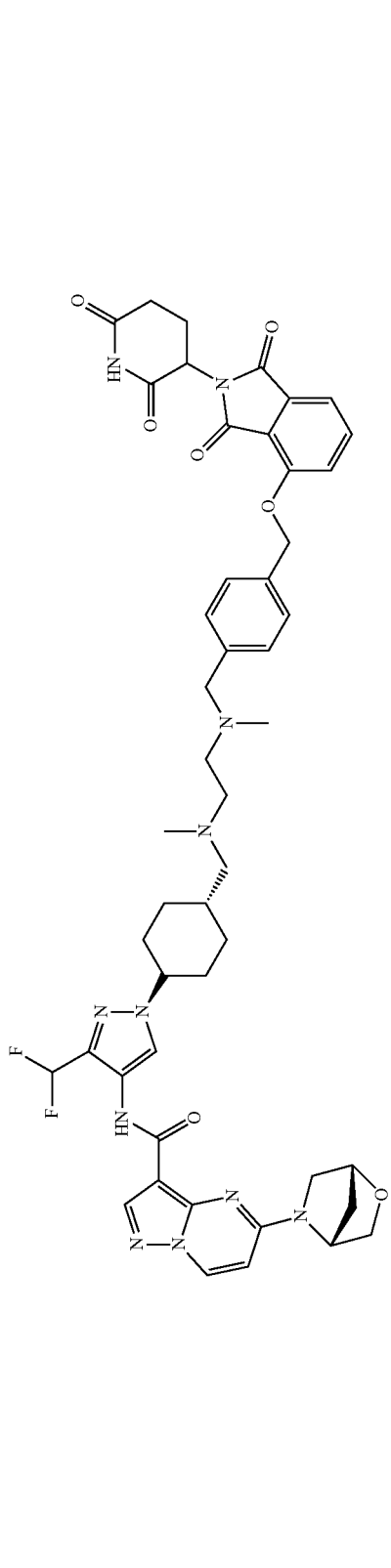 |

TABLE 1-continued
Exemplary Compounds
| I-# | Structure |
|---|---|
| I-336 | 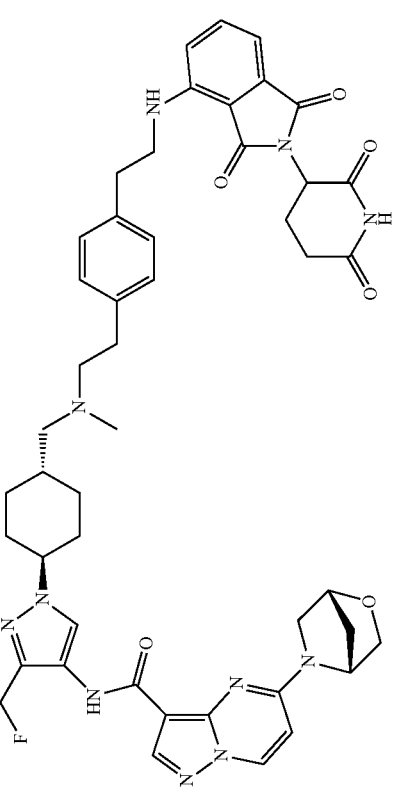 |
| I-337 | 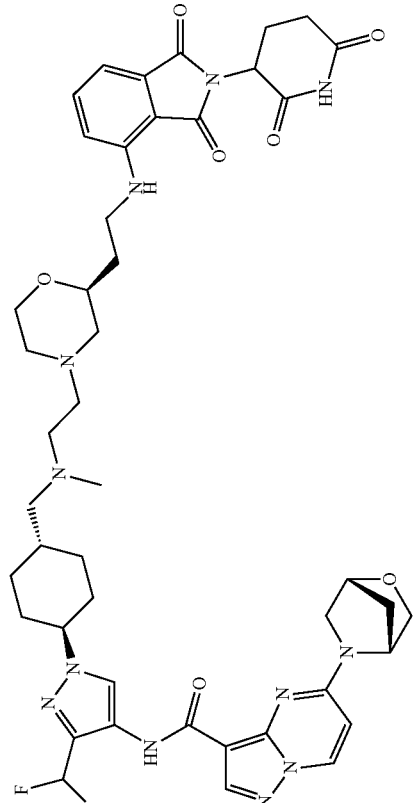 |

TABLE 1-continued
Exemplary Compounds
| I-# | Structure |
|---|---|
| I-338 | 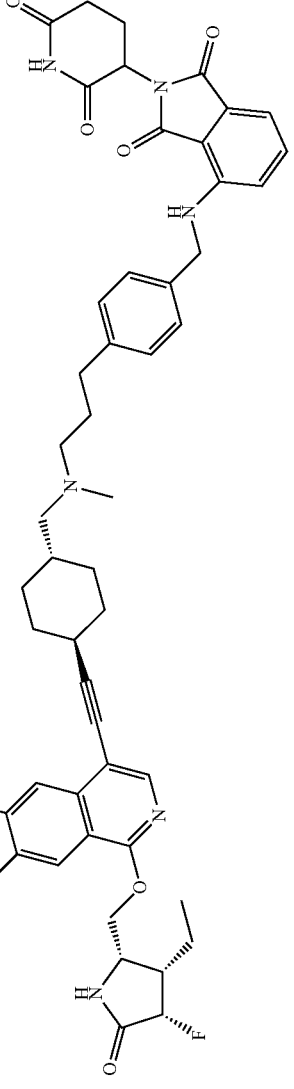 |
| I-339 | 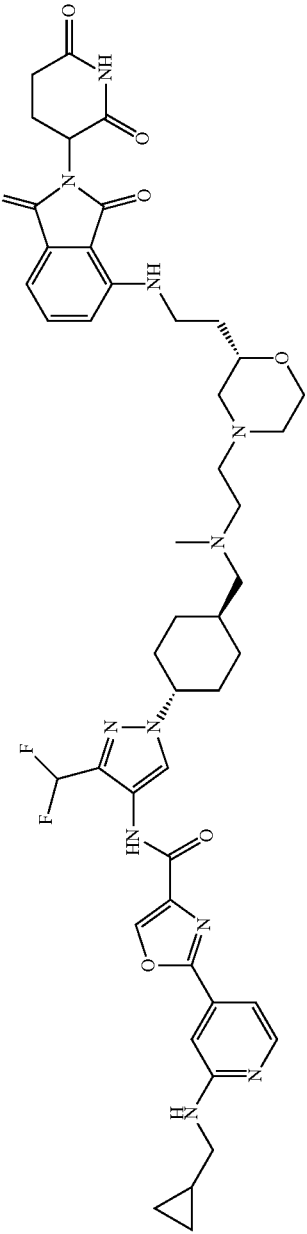 |

TABLE 1-continued
Exemplary Compounds
| I-# | Structure |
|---|---|
| I-340 | 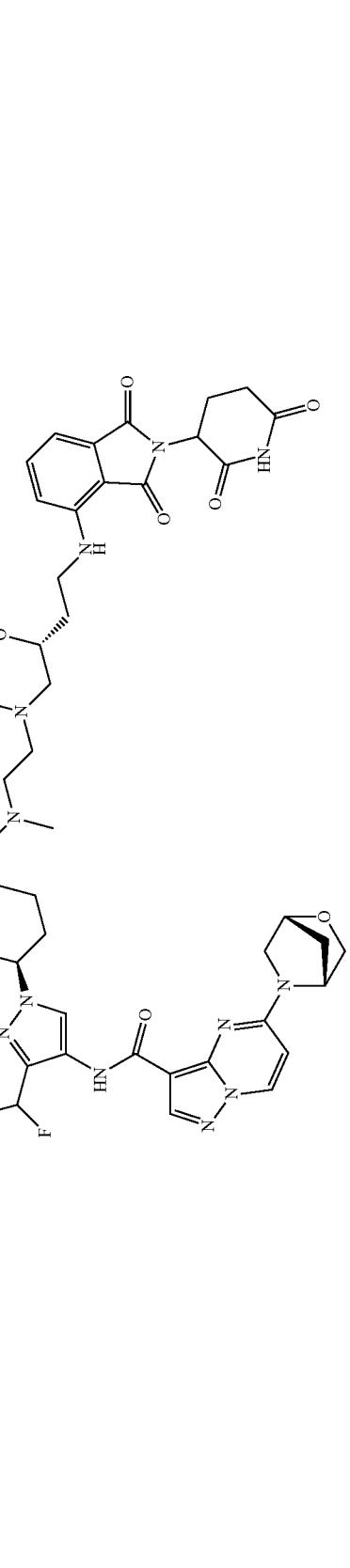 |
| I-341 | 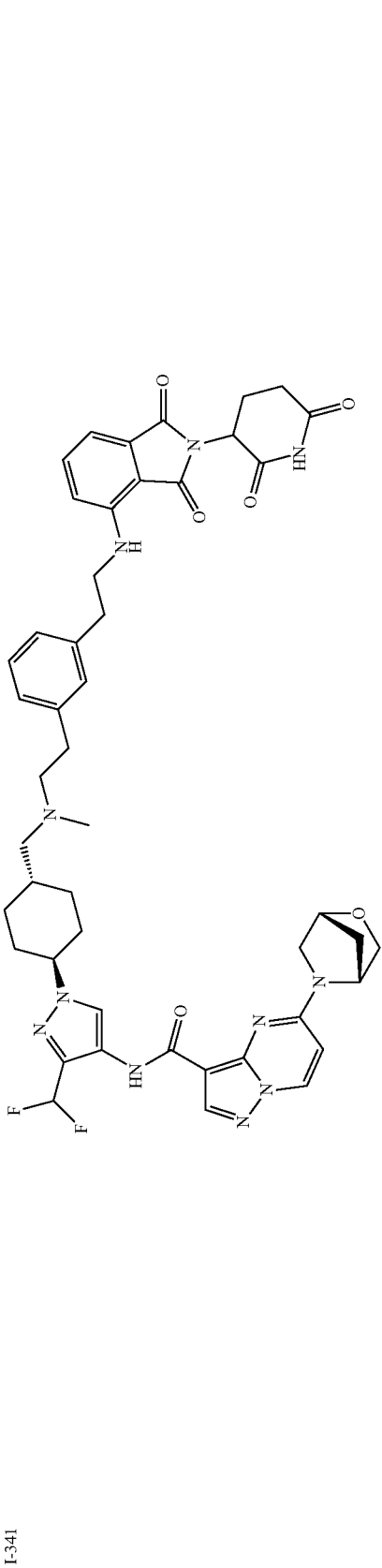 |

TABLE 1-continued

Exemplary Compounds

| I-# | Structure |
| --- | --- |
| I-342 | 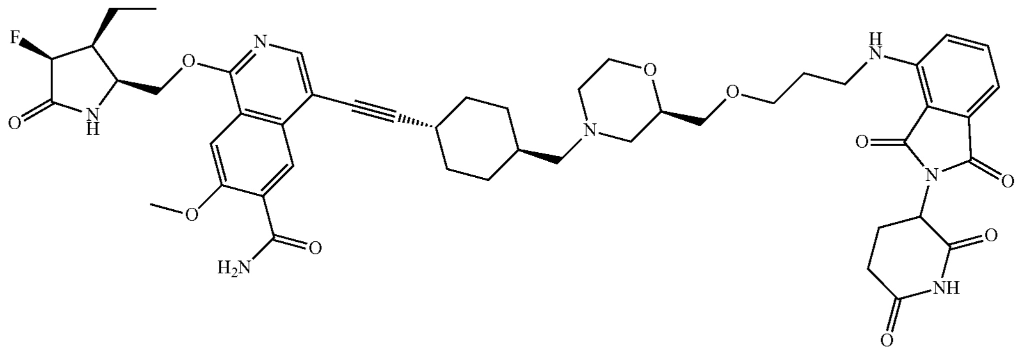 [SMILES: CC[C@@H]1[C@H](F)C(=O)N[C@@H]1COc1ncc(C#C[C@H]2CC[C@H](CN3CCO[C@@H](COCCCNc4cccc5c4C(=O)N(C4CCC(=O)NC4=O)C5=O)C3)CC2)c2cc(C(N)=O)c(OC)cc12] |
| I-343 | 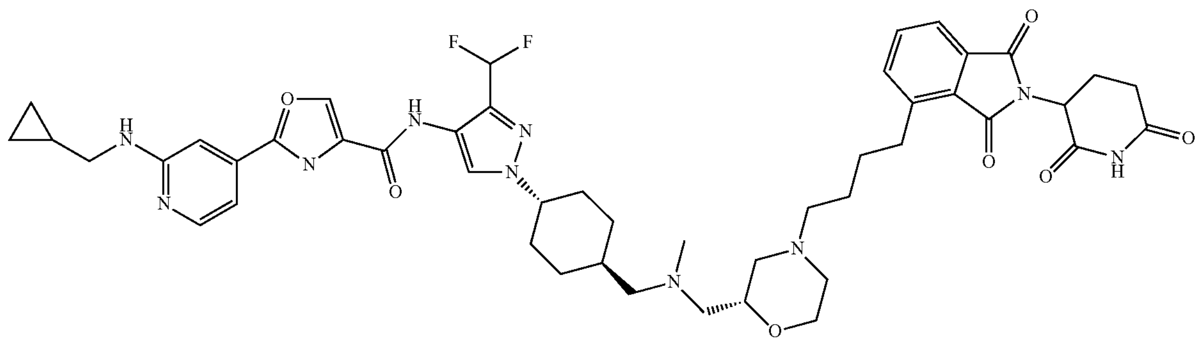 |

TABLE 1-continued
Exemplary Compounds
| I-# | Structure |
|---|---|
| I-344 | 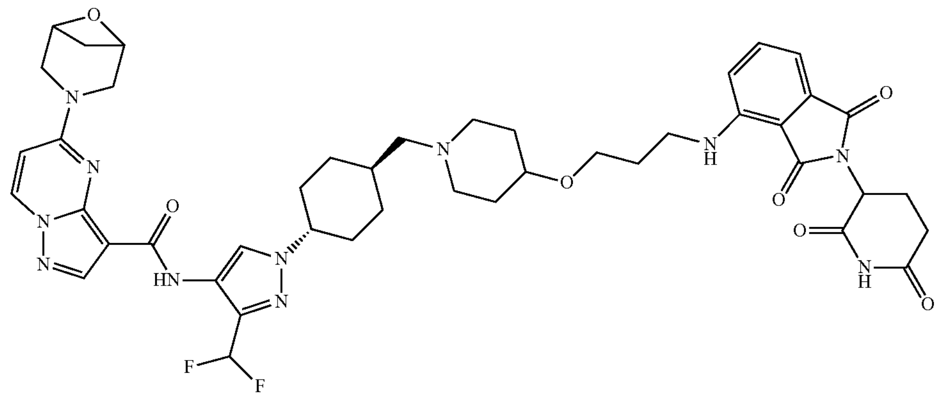 [SMILES: O=C1CCC(N2C(=O)c3cccc(NCCCOC4CCN(C[C@H]5CC[C@H](n6cc(NC(=O)c7cnn8ccc(N9CC%10CC(C9)O%10)nc78)c(C(F)F)n6)CC5)CC4)c3C2=O)C(=O)N1] |
| I-345 | 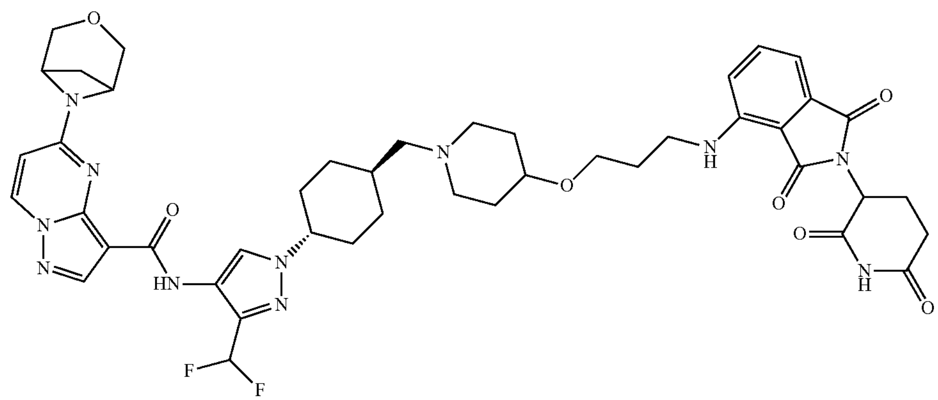 [SMILES: O=C1CCC(N2C(=O)c3cccc(NCCCOC4CCN(C[C@H]5CC[C@H](n6cc(NC(=O)c7cnn8ccc(N9C%10COCC9C%10)nc78)c(C(F)F)n6)CC5)CC4)c3C2=O)C(=O)N1] |

TABLE 1-continued
Exemplary Compounds
| I-# | Structure |
|---|---|
| I-346 | 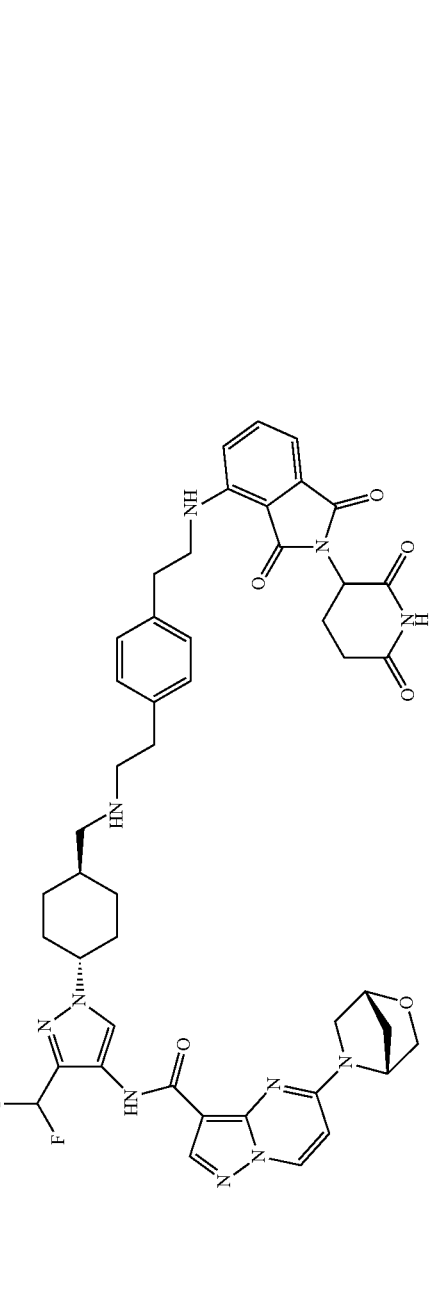 |
| I-347 | 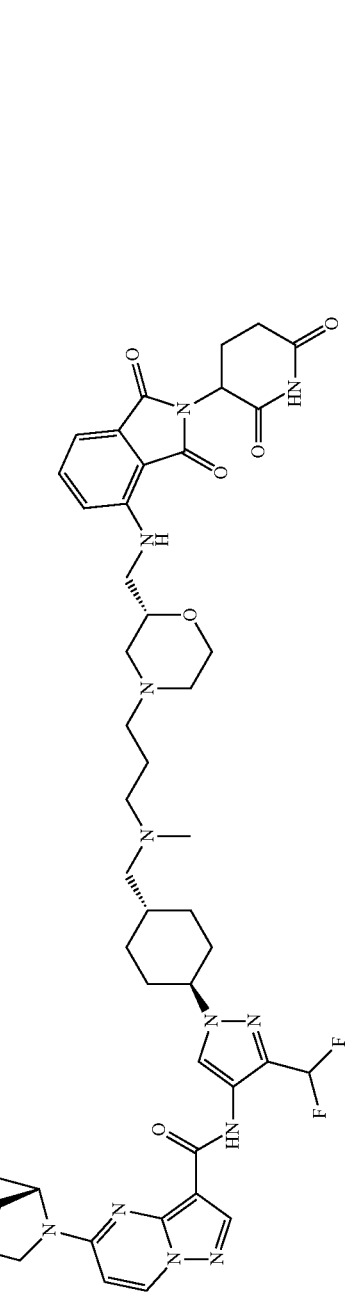 |

TABLE 1-continued
Exemplary Compounds
| I-# | Structure |
|---|---|
| I-348 | 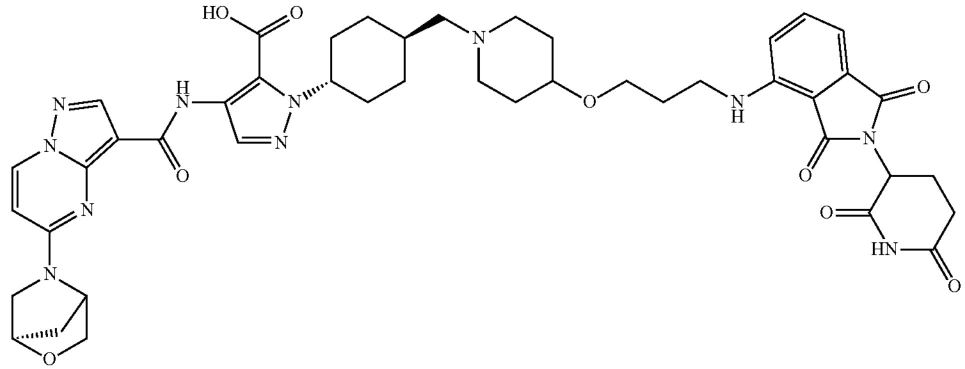 [SMILES: O=C1CCC(N2C(=O)c3cccc(NCCCOC4CCN(C[C@H]5CC[C@H](n6ncc(NC(=O)c7cnn8ccc(N9C[C@H]%10CC9CO%10)nc78)c6C(=O)O)CC5)CC4)c3C2=O)C(=O)N1] |
| I-349 | 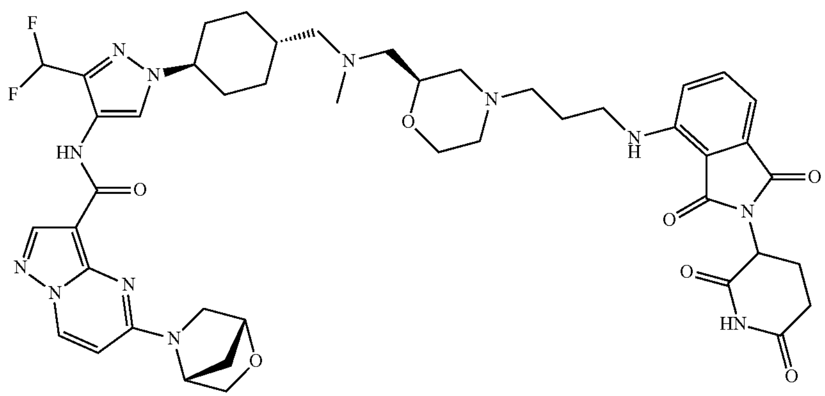 [SMILES: CN(C[C@H]1CN(CCCNc2cccc3c2C(=O)N(C2CCC(=O)NC2=O)C3=O)CCO1)C[C@H]1CC[C@H](n2cc(NC(=O)c3cnn4ccc(N5C[C@H]6C[C@@H]5CO6)nc34)c(C(F)F)n2)CC1] |

TABLE 1-continued
Exemplary Compounds
| I-# | Structure |
|---|---|
| I-350 | 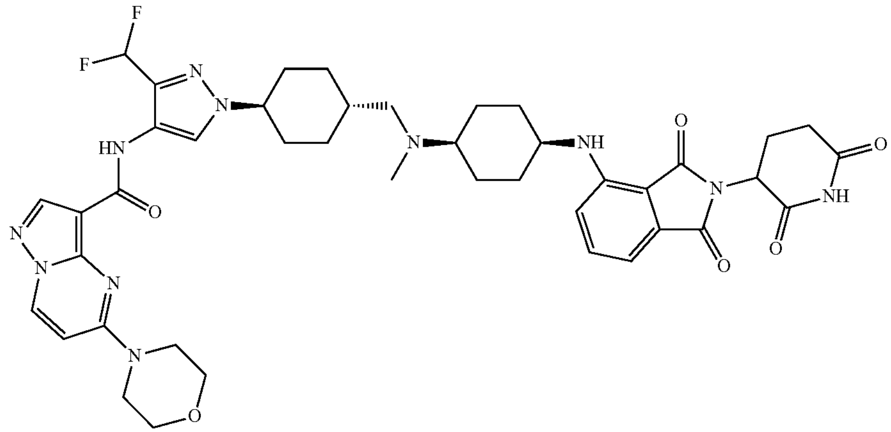 [SMILES: CN(C[C@H]1CC[C@H](n2cc(NC(=O)c3cnn4ccc(N5CCOCC5)nc34)c(C(F)F)n2)CC1)[C@H]1CC[C@@H](Nc2cccc3c2C(=O)N(C2CCC(=O)NC2=O)C3=O)CC1] |
| I-351 | 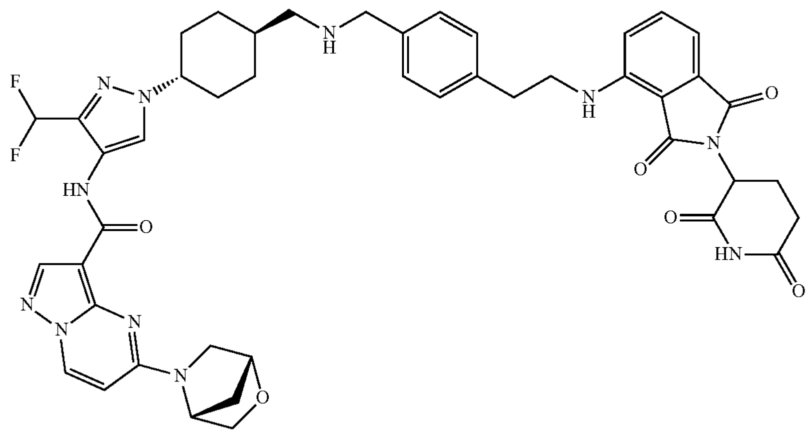 [SMILES: O=C1CCC(N2C(=O)c3cccc(NCCc4ccc(CNC[C@H]5CC[C@H](n6cc(NC(=O)c7cnn8ccc(N9C[C@H]%10C[C@@H]9CO%10)nc78)c(C(F)F)n6)CC5)cc4)c3C2=O)C(=O)N1] |

TABLE 1-continued
Exemplary Compounds
| I-# | Structure |
|---|---|
| I-352 | 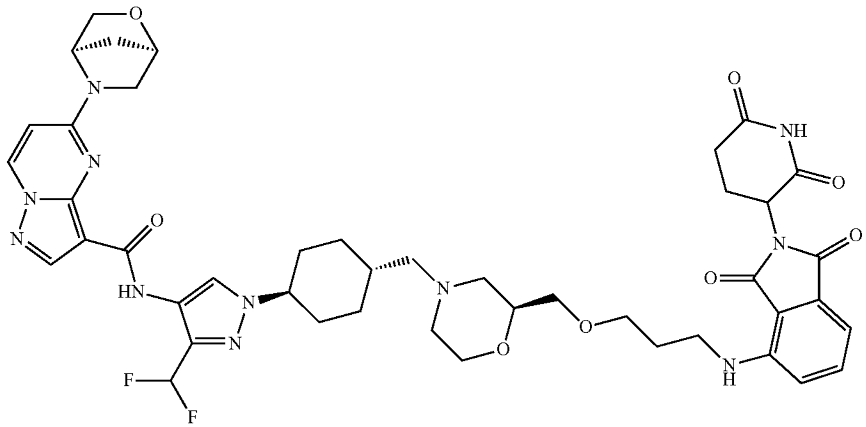 [SMILES: O=C1CCC(N2C(=O)c3cccc(NCCCOC[C@@H]4CN(C[C@H]5CC[C@H](n6cc(NC(=O)c7cnn8ccc(N9C[C@H]%10C[C@@H]9CO%10)nc78)c(C(F)F)n6)CC5)CCO4)c3C2=O)C(=O)N1] |
| I-353 | 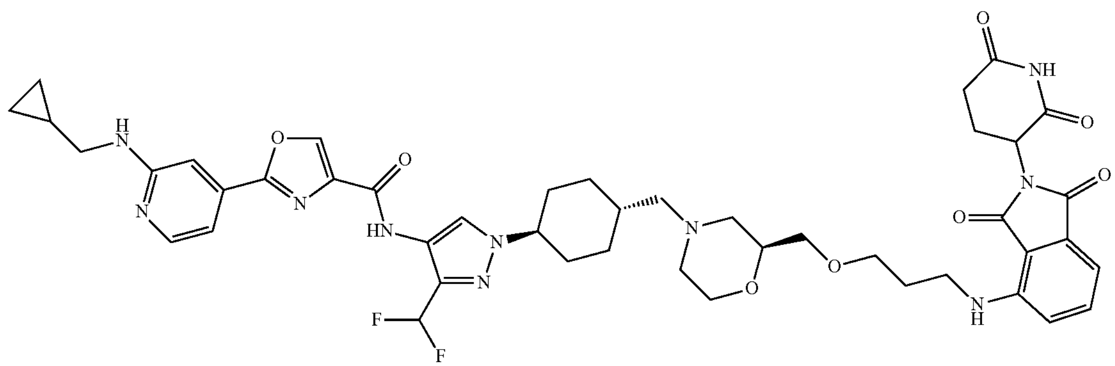 [SMILES: O=C1CCC(N2C(=O)c3cccc(NCCCOC[C@@H]4CN(C[C@H]5CC[C@H](n6cc(NC(=O)c7coc(-c8ccnc(NCC9CC9)c8)n7)c(C(F)F)n6)CC5)CCO4)c3C2=O)C(=O)N1] |
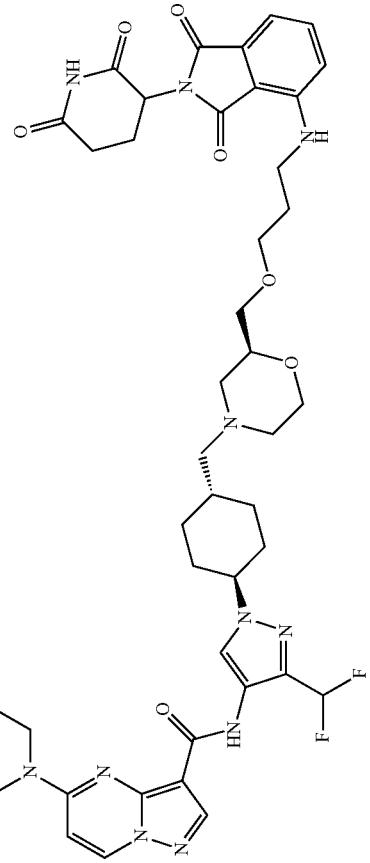

TABLE 1-continued
Exemplary Compounds
| I-# | Structure |
|---|---|
| I-354 | 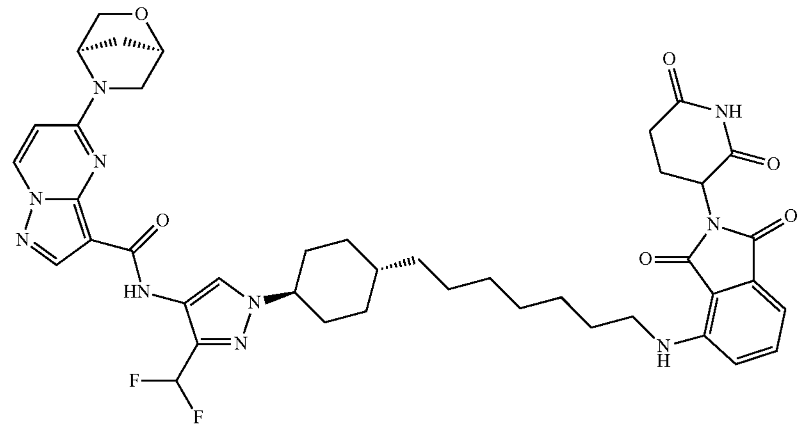 [SMILES: O=C1CCC(N2C(=O)c3cccc(NCCCCCCC[C@H]4CC[C@H](n5cc(NC(=O)c6cnn7ccc(N8C[C@H]9C[C@@H]8CO9)nc67)c(C(F)F)n5)CC4)c3C2=O)C(=O)N1] |
| I-355 | 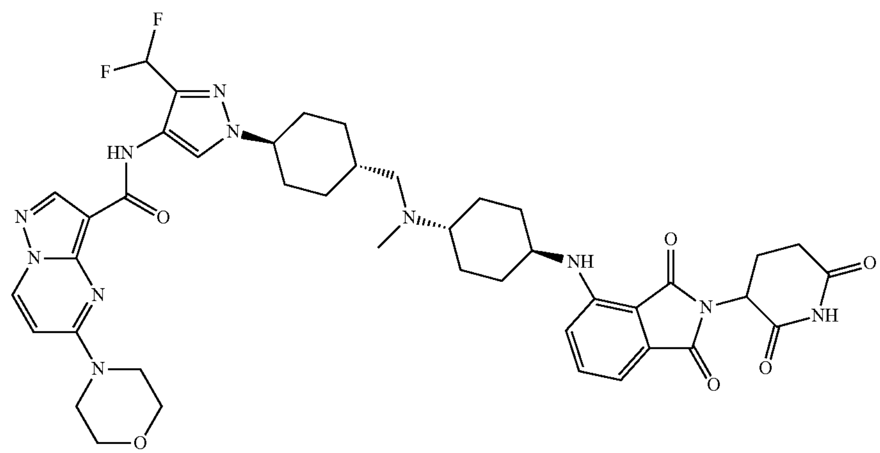 [SMILES: CN(C[C@H]1CC[C@H](n2cc(NC(=O)c3cnn4ccc(N5CCOCC5)nc34)c(C(F)F)n2)CC1)[C@H]1CC[C@H](Nc2cccc3c2C(=O)N(C2CCC(=O)NC2=O)C3=O)CC1] |

TABLE 1-continued
Exemplary Compounds
| I-# | Structure |
|---|---|
| I-356 | 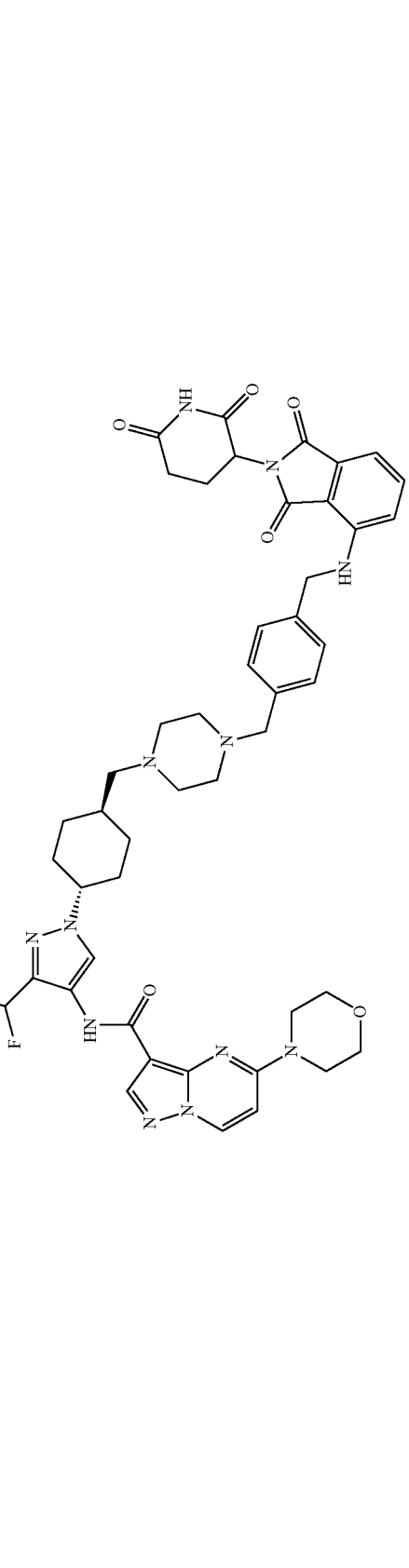 |
| I-357 | 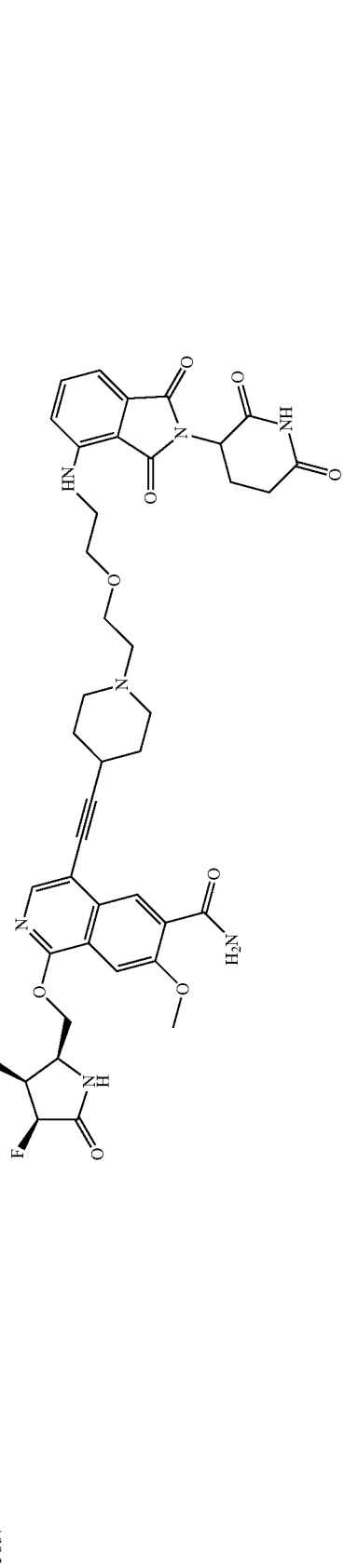 |

TABLE 1-continued
Exemplary Compounds
| I-# | Structure |
|---|---|
| I-358 | 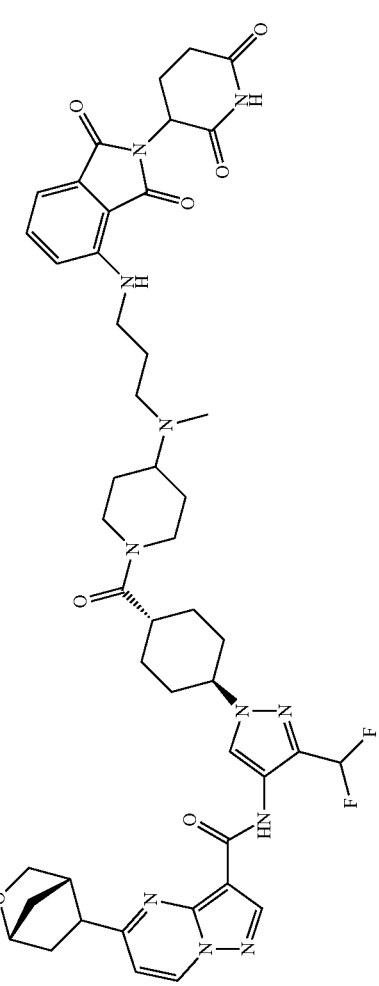 |
| I-359 | 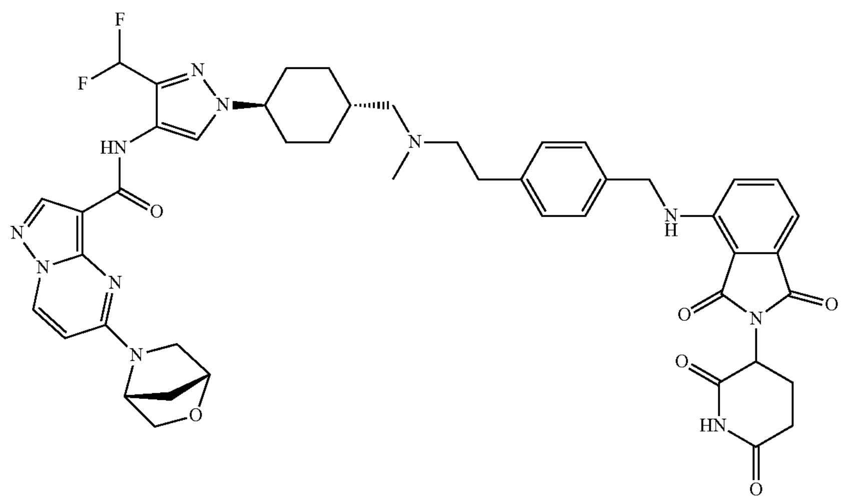 [SMILES: CN(CCc1ccc(CNc2cccc3c2C(=O)N(C2CCC(=O)NC2=O)C3=O)cc1)C[C@H]1CC[C@H](n2cc(NC(=O)c3cnn4ccc(N5C[C@H]6C[C@@H]5CO6)nc34)c(C(F)F)n2)CC1] |

TABLE 1-continued
Exemplary Compounds
| I-# | Structure |
|---|---|
| I-360 | 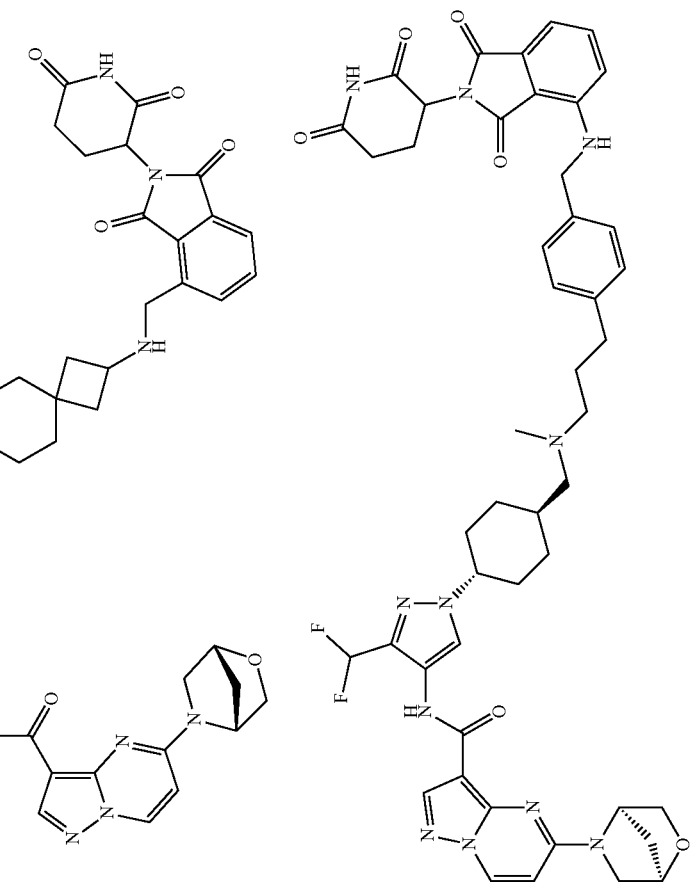 |
| I-361 | 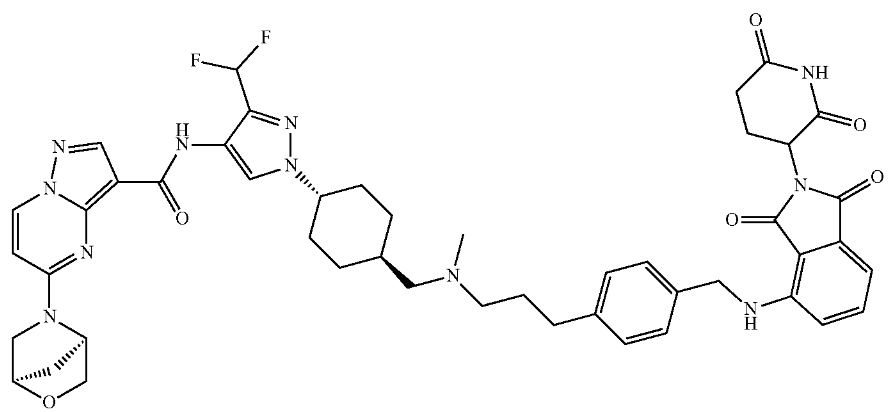 [SMILES: CN(CCCc1ccc(CNc2cccc3c2C(=O)N(C2CCC(=O)NC2=O)C3=O)cc1)C[C@H]1CC[C@H](n2cc(NC(=O)c3cnn4ccc(N5C[C@H]6C[C@@H]5CO6)nc34)c(C(F)F)n2)CC1] |

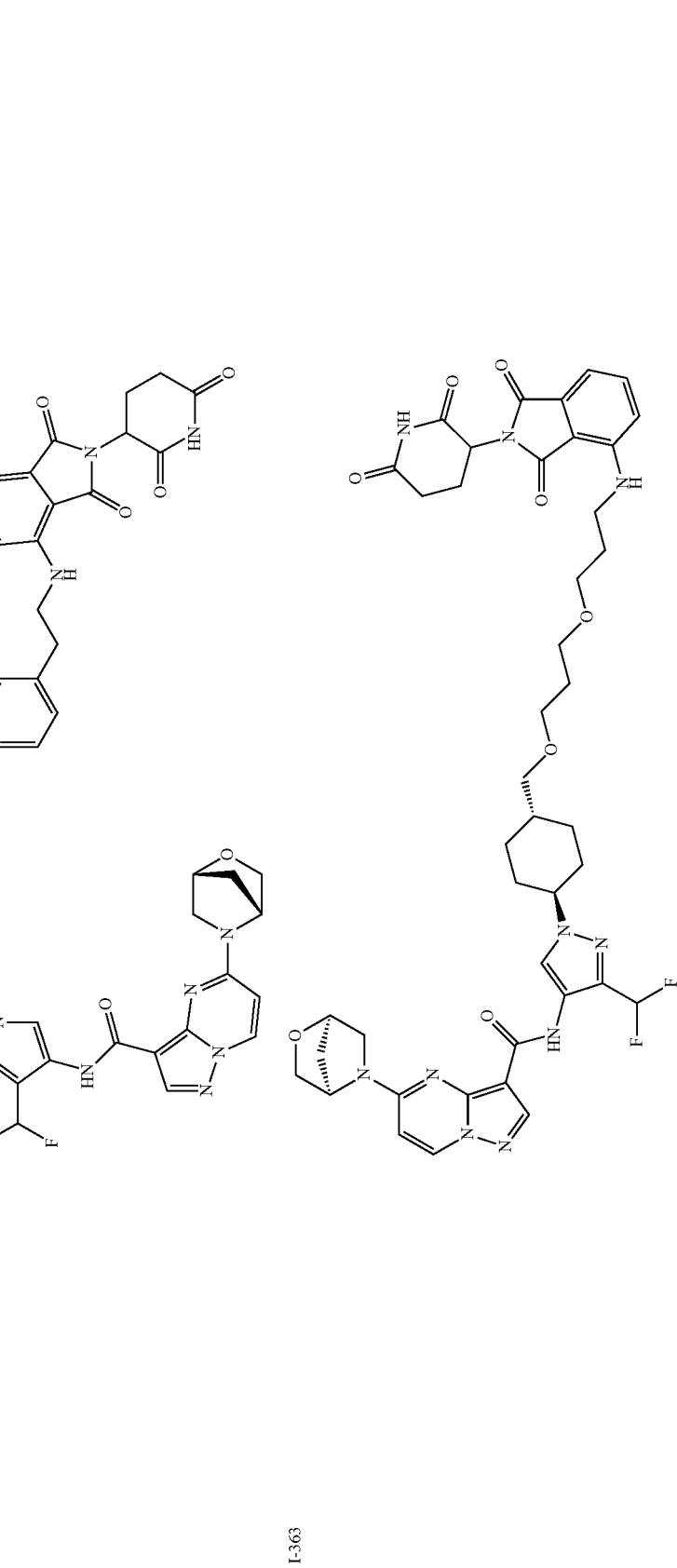

TABLE 1-continued
Exemplary Compounds
| I-# | Structure |
|---|---|
| I-364 | 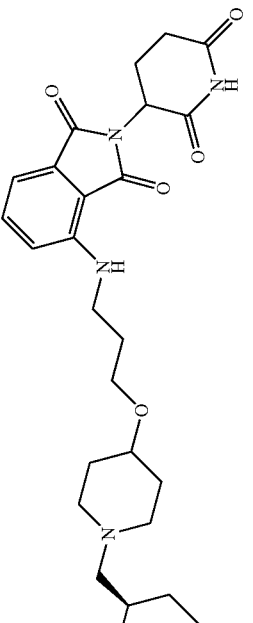 |
| I-365 | 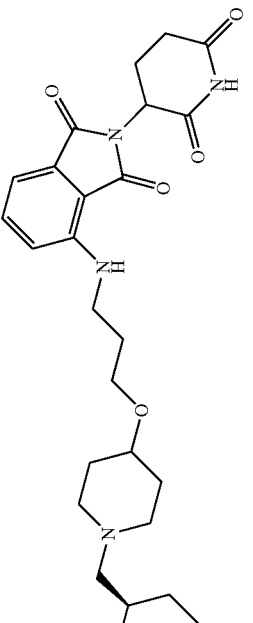 |

TABLE 1-continued

Exemplary Compounds

| I-# | Structure |
|---|---|
| I-366 | 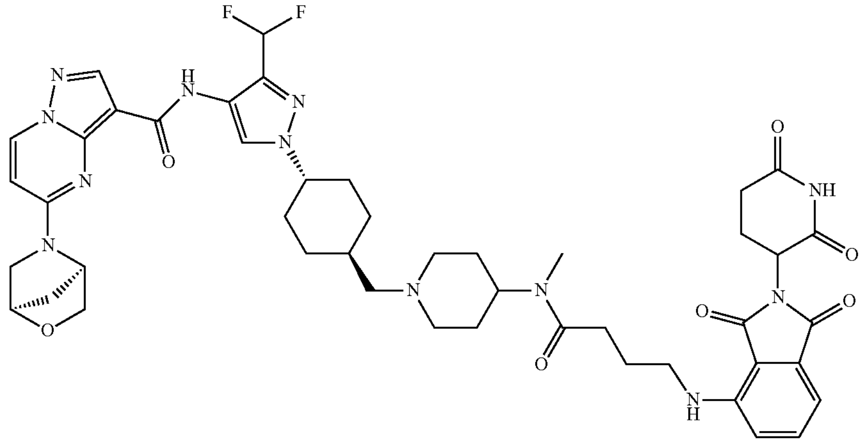 [SMILES: CN(C(=O)CCCNc1cccc2c1C(=O)N(C1CCC(=O)NC1=O)C2=O)C1CCN(C[C@H]2CC[C@H](n3cc(NC(=O)c4cnn5ccc(N6C[C@H]7C[C@@H]6CO7)nc45)c(C(F)F)n3)CC2)CC1] |
| I-367 | 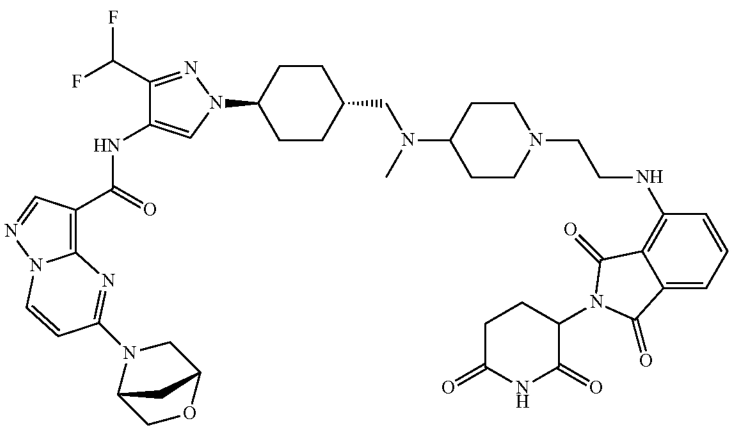 [SMILES: CN(C[C@H]1CC[C@H](n2cc(NC(=O)c3cnn4ccc(N5C[C@H]6C[C@@H]5CO6)nc34)c(C(F)F)n2)CC1)C1CCN(CCNc2cccc3c2C(=O)N(C2CCC(=O)NC2=O)C3=O)CC1] |

TABLE 1-continued
Exemplary Compounds
| I-# | Structure |
|---|---|
| I-368 | 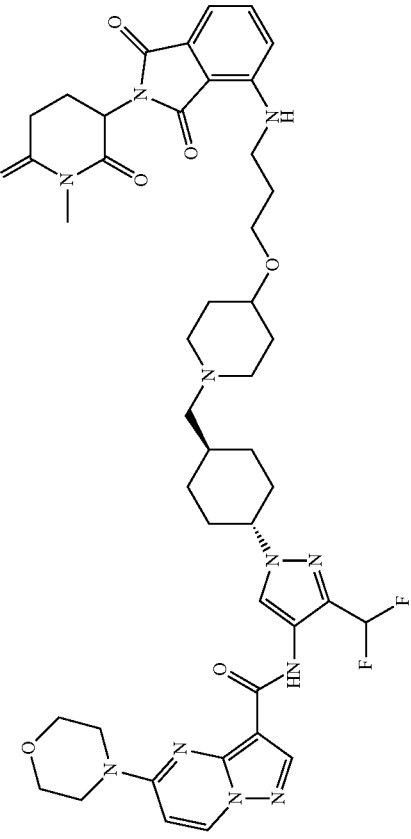 |
| I-369 | 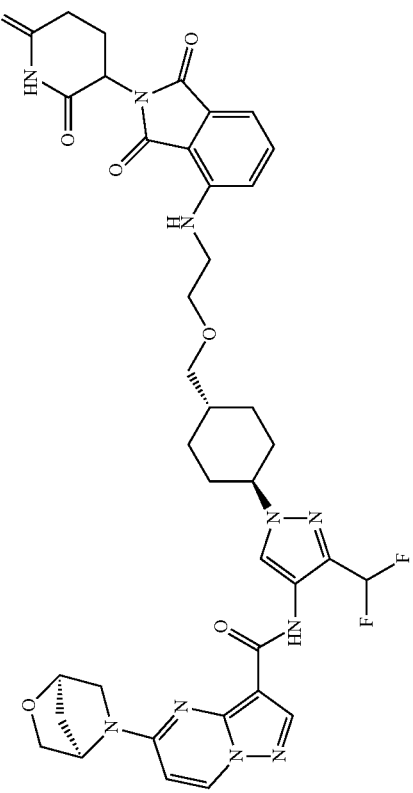 |

TABLE 1-continued
Exemplary Compounds
| I-# | Structure |
|---|---|
| I-370 | 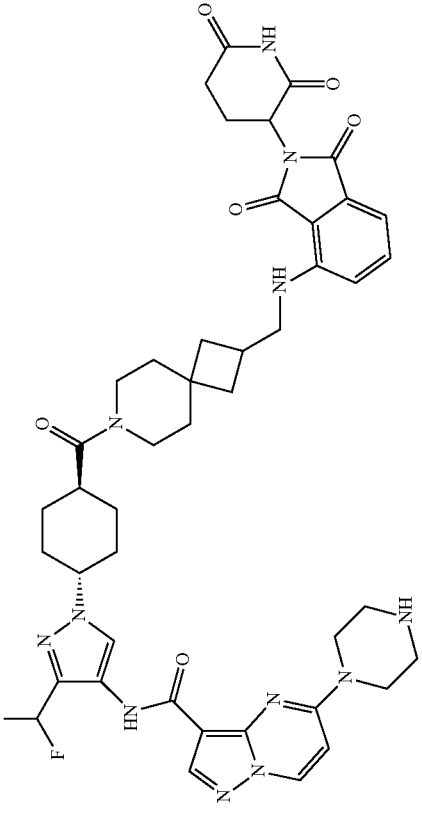 |
| I-371 | 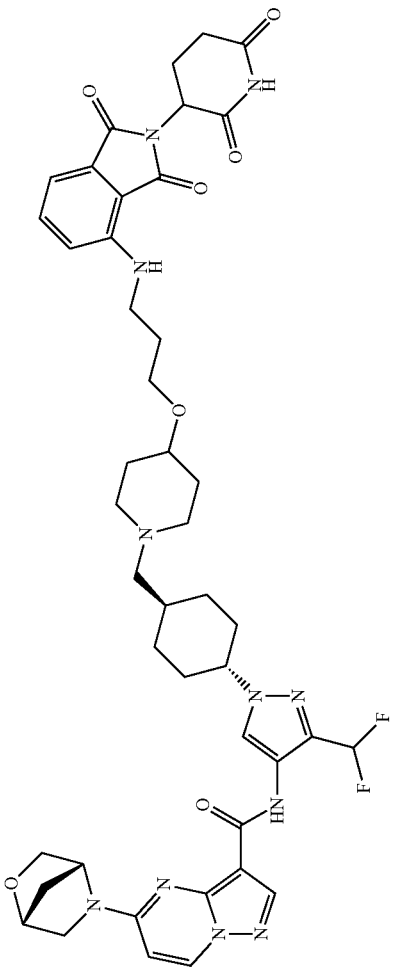 |

TABLE 1-continued
Exemplary Compounds
| I-# | Structure |
|---|---|
| I-372 | 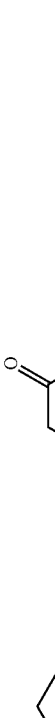 |
| I-373 | 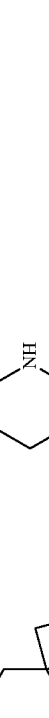 |

TABLE 1-continued
Exemplary Compounds
| I-# | Structure |
|---|---|
| I-374 | 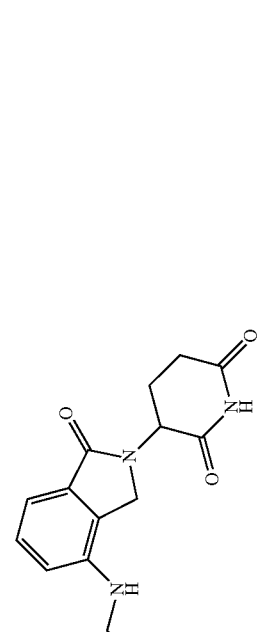 |
| I-375 | 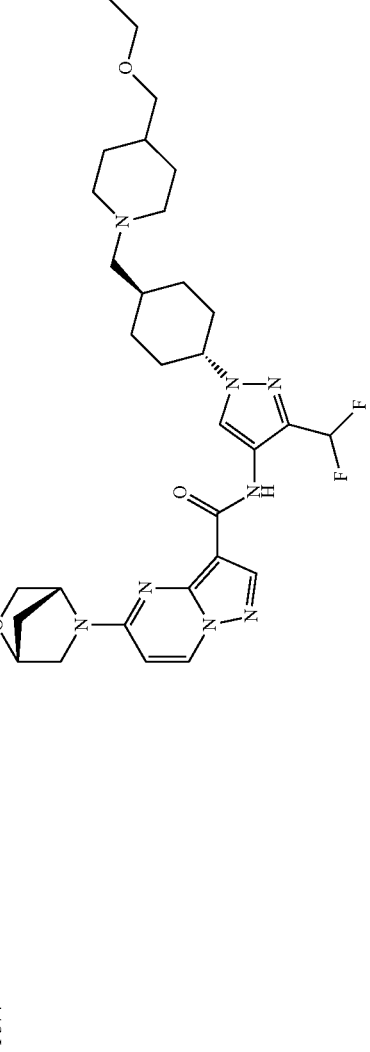 |

TABLE 1-continued
Exemplary Compounds
| I-# | Structure |
|---|---|
| I-376 | 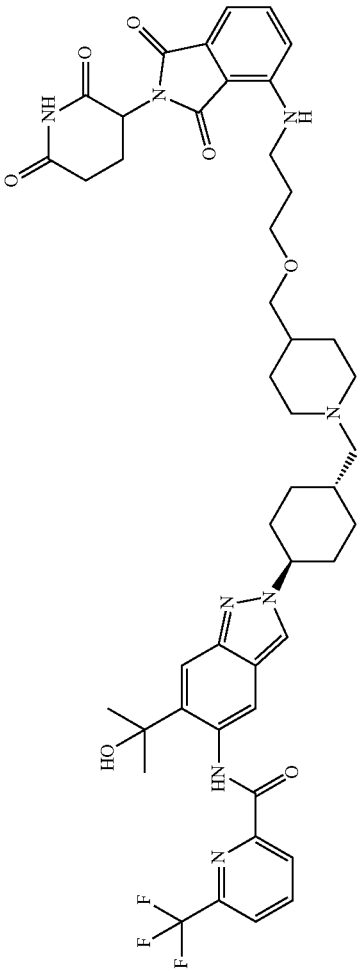 |
| I-377 | 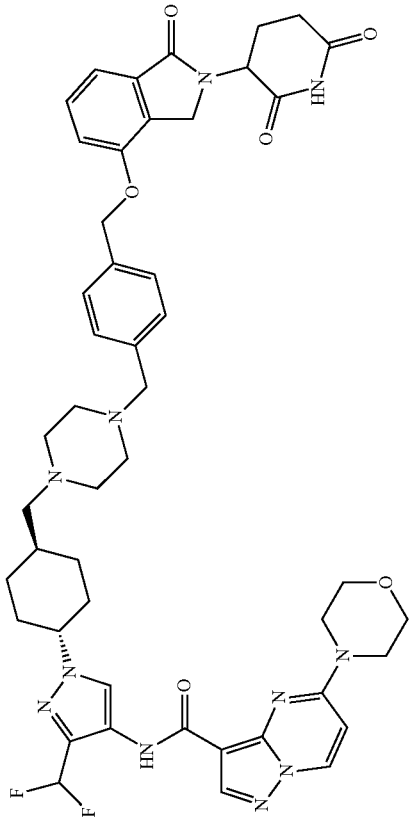 |

TABLE 1-continued
Exemplary Compounds
| I-# | Structure |
|---|---|
| I-379 | 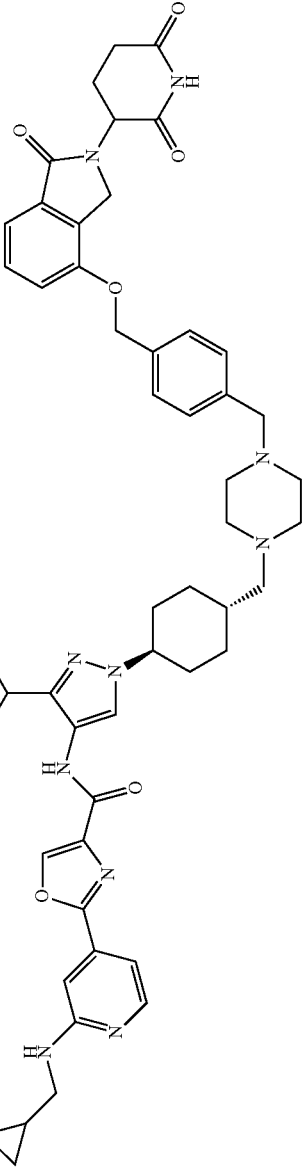 |
| I-380 | 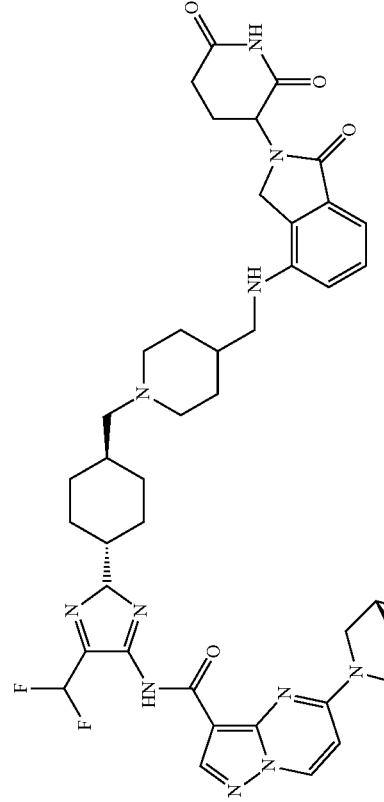 |

TABLE 1-continued
Exemplary Compounds
| I-# | Structure |
|---|---|
| I-381 | 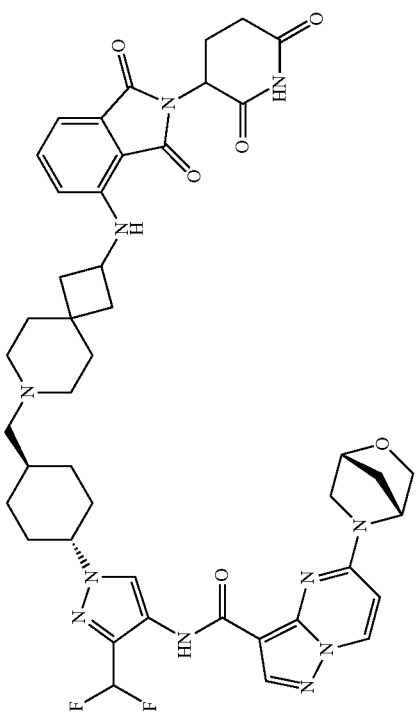 |
| I-382 | 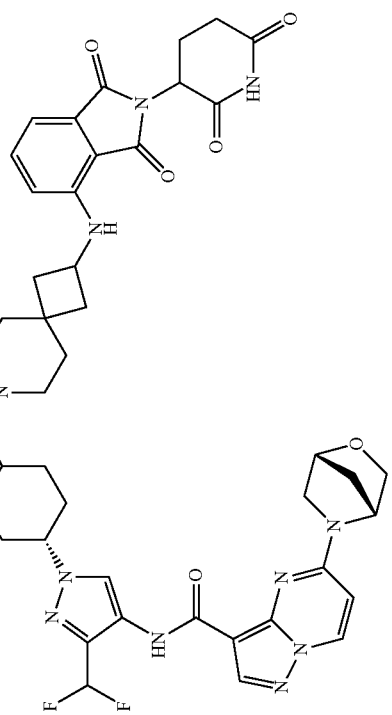 |

TABLE 1-continued

Exemplary Compounds

| I-# | Structure |
|---|---|
| I-384 | 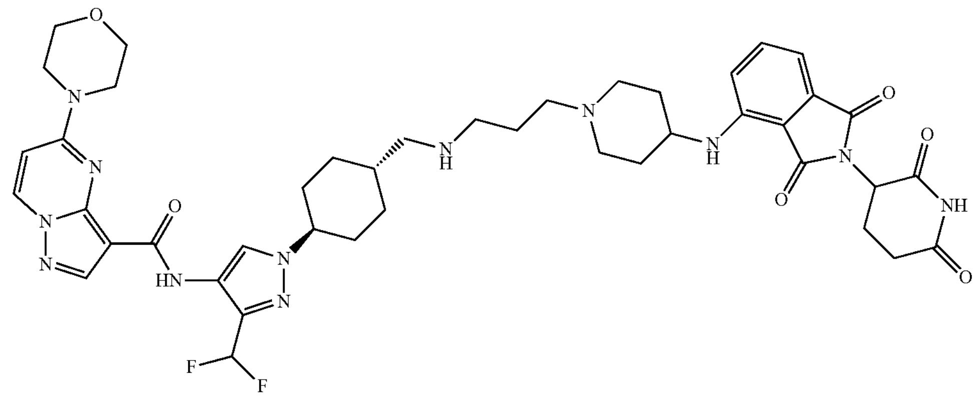 [SMILES: O=C1CCC(N2C(=O)c3cccc(NC4CCN(CCCNC[C@H]5CC[C@H](n6cc(NC(=O)c7cnn8ccc(N9CCOCC9)nc78)c(C(F)F)n6)CC5)CC4)c3C2=O)C(=O)N1] |
| I-385 | 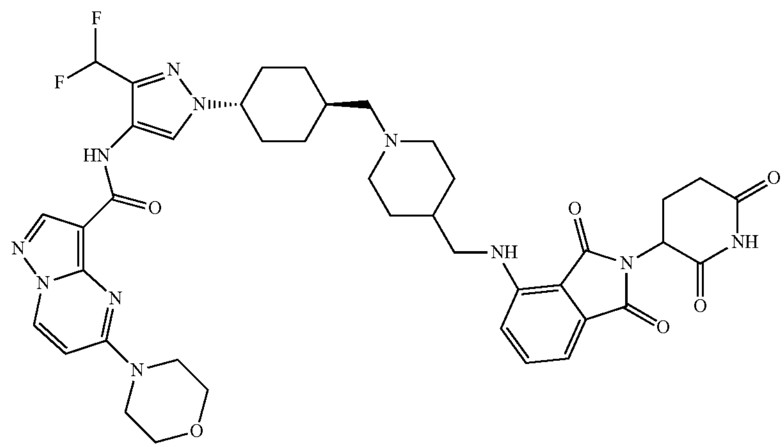 [SMILES: O=C1CCC(N2C(=O)c3cccc(NCC4CCN(C[C@H]5CC[C@H](n6cc(NC(=O)c7cnn8ccc(N9CCOCC9)nc78)c(C(F)F)n6)CC5)CC4)c3C2=O)C(=O)N1] |

TABLE 1-continued
Exemplary Compounds
| I-# | Structure |
|---|---|
| I-386 | 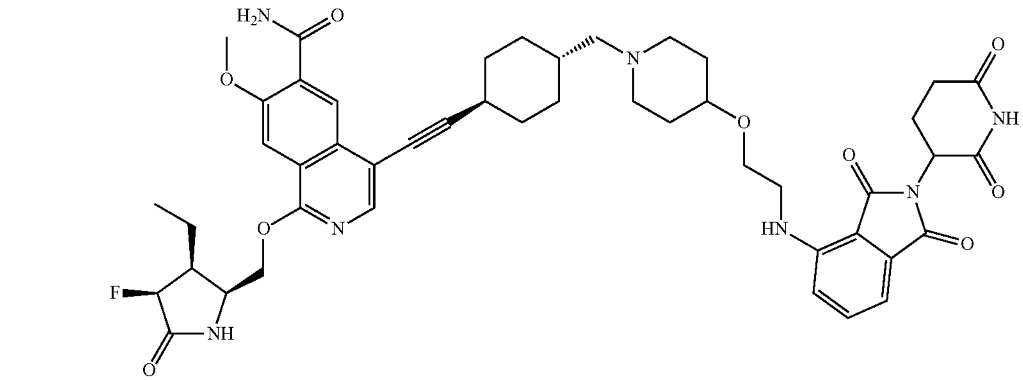 [SMILES: CC[C@@H]1[C@H](F)C(=O)N[C@@H]1COc1ncc(C#C[C@H]2CC[C@H](CN3CCC(OCCNc4cccc5c4C(=O)N(C4CCC(=O)NC4=O)C5=O)CC3)CC2)c2cc(C(N)=O)c(OC)cc12] |
| I-387 | 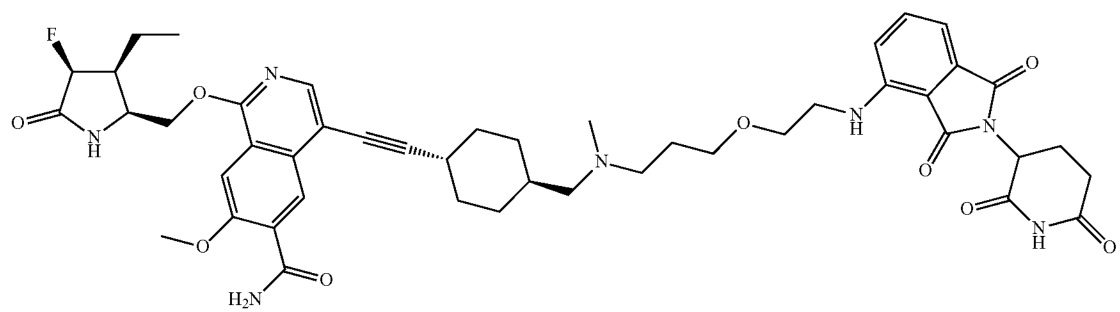 [SMILES: CC[C@@H]1[C@H](F)C(=O)N[C@@H]1COc1ncc(C#C[C@H]2CC[C@H](CN(C)CCCOCCNc3cccc4c3C(=O)N(C3CCC(=O)NC3=O)C4=O)CC2)c2cc(C(N)=O)c(OC)cc12] |

TABLE 1-continued
Exemplary Compounds
| I-# | Structure |
|---|---|
| I-388 | 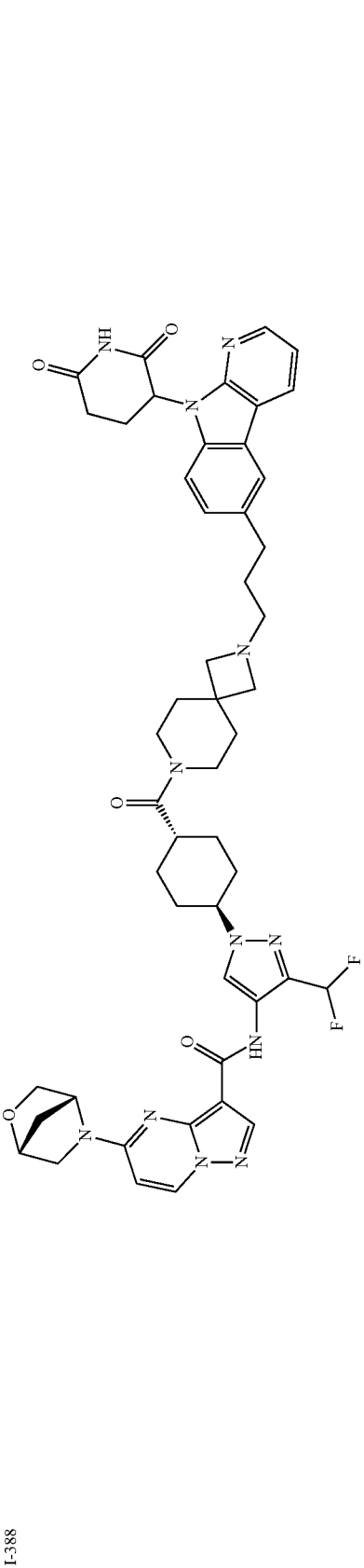 |
| I-389 | 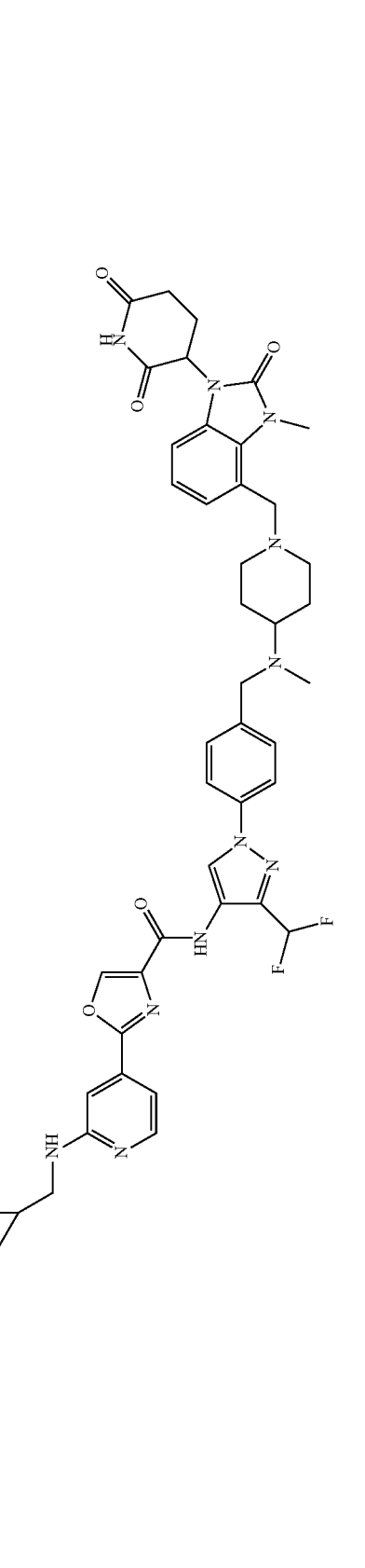 |

TABLE 1-continued
Exemplary Compounds
| I-# | Structure |
|---|---|
| I-390 | 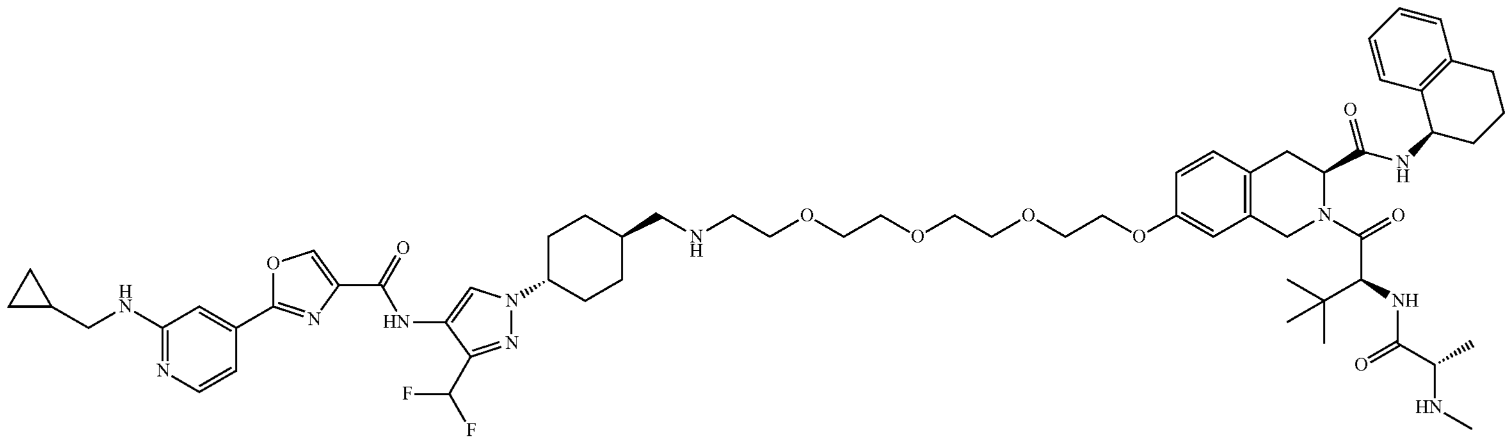 [SMILES: CN[C@@H](C)C(=O)N[C@H](C(=O)N1Cc2cc(OCCOCCOCCOCCNC[C@H]3CC[C@H](n4cc(NC(=O)c5coc(-c6ccnc(NCC7CC7)c6)n5)c(C(F)F)n4)CC3)ccc2C[C@H]1C(=O)N[C@@H]1CCCc2ccccc21)C(C)(C)C] |
| I-391 | 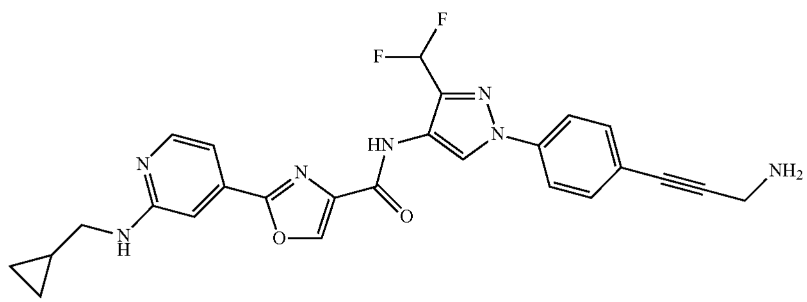 [SMILES: NCC#Cc1ccc(-n2cc(NC(=O)c3coc(-c4ccnc(NCC5CC5)c4)n3)c(C(F)F)n2)cc1] |
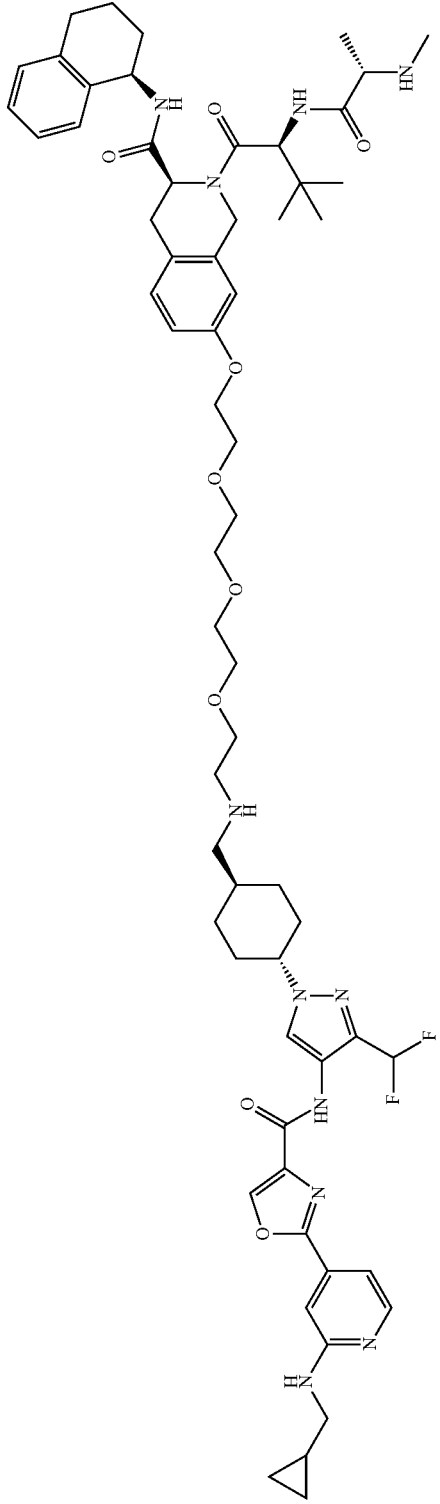

TABLE 1-continued
Exemplary Compounds
| I-# | Structure |
|---|---|
| I-392 | 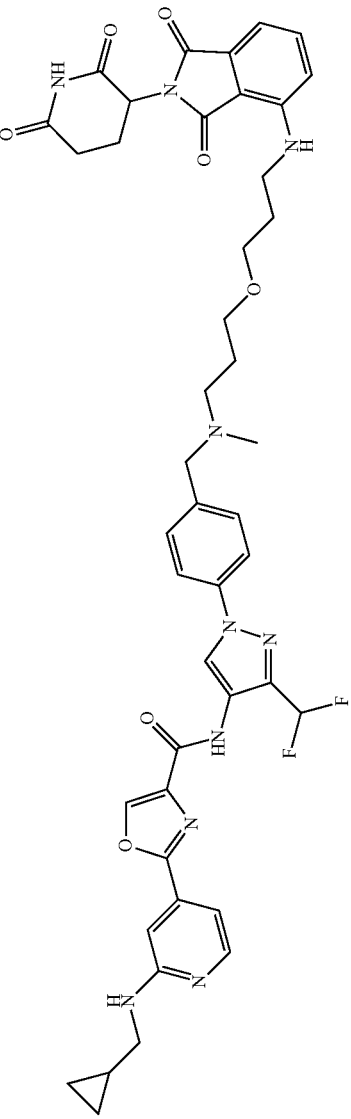 |
| I-393 | 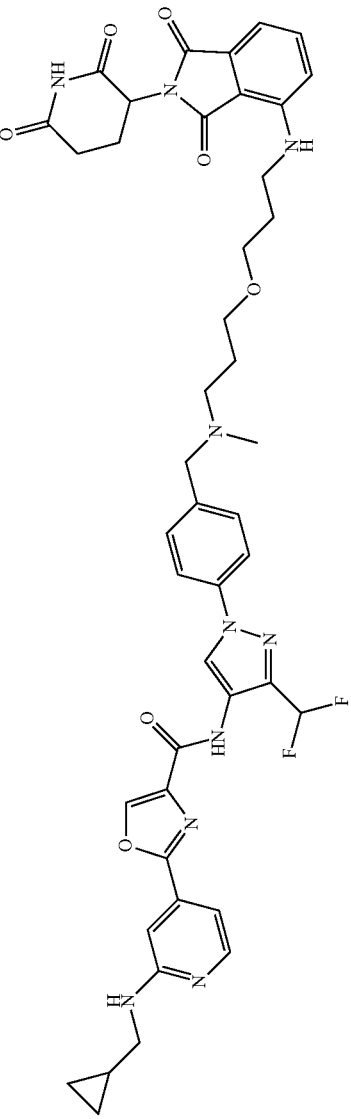 |

TABLE 1-continued
Exemplary Compounds
| I-# | Structure |
|---|---|
| I-395 | 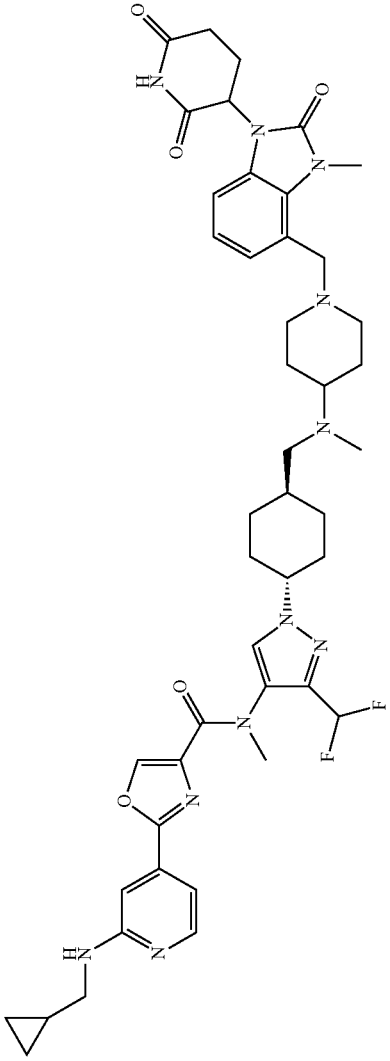 |
| I-396 | 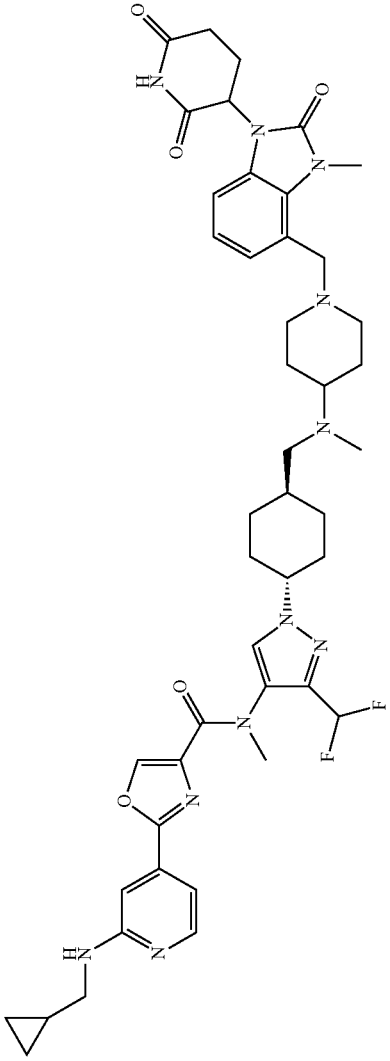 |

TABLE 1-continued
Exemplary Compounds
| I-# | Structure |
|---|---|
| I-397 | 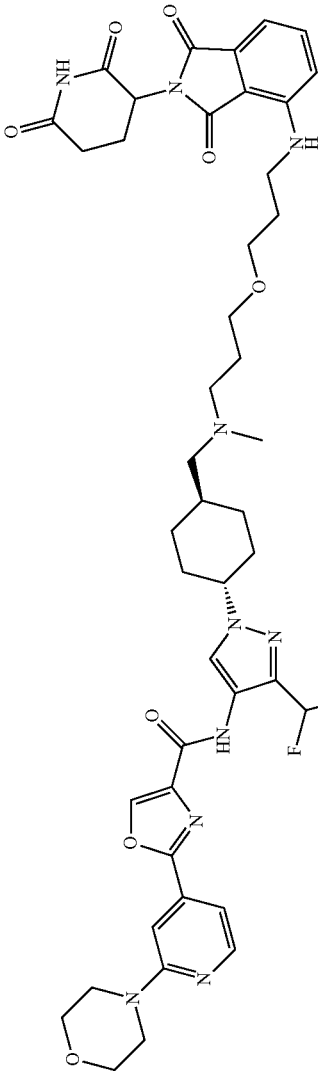 |
| I-398 | 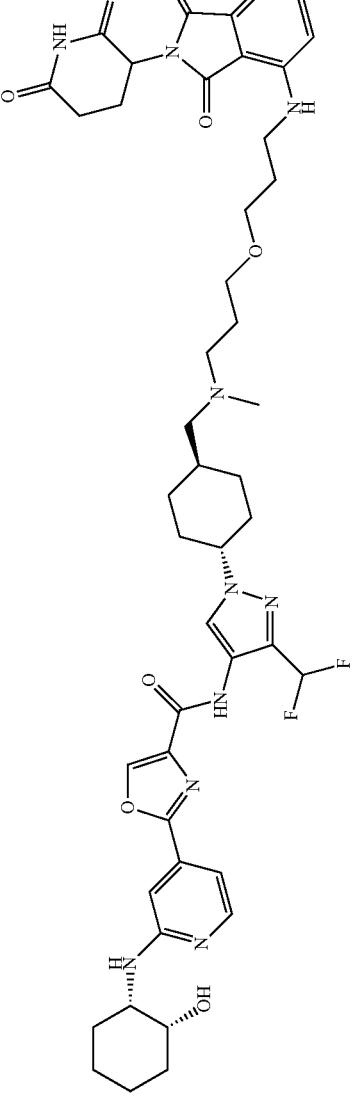 |

TABLE 1-continued
Exemplary Compounds
| I-# | Structure |
|---|---|
| I-399 | 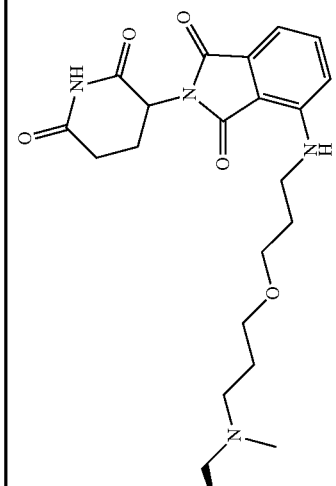 |
| I-400 | 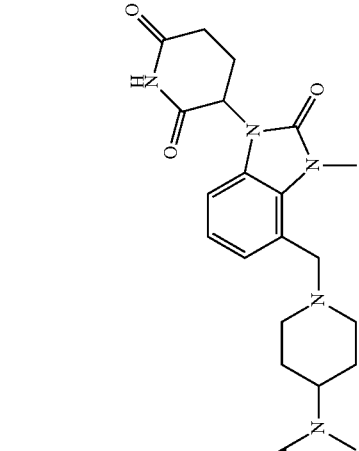 |

TABLE 1-continued
Exemplary Compounds
| I-# | Structure |
|---|---|
| I-401 | 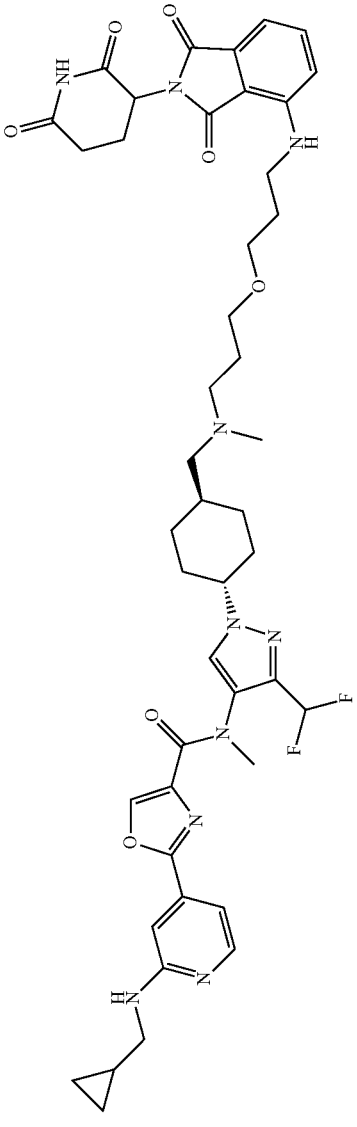 |
| I-402 | 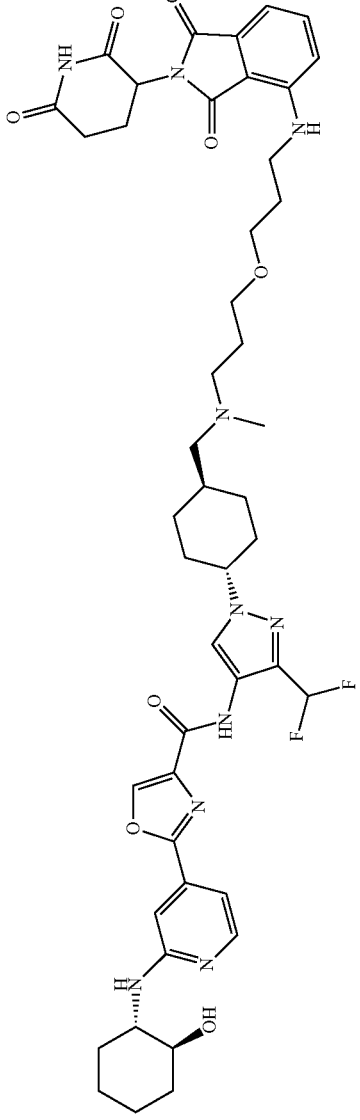 |

TABLE 1-continued
Exemplary Compounds
| I-# | Structure |
|---|---|
| I-403 | 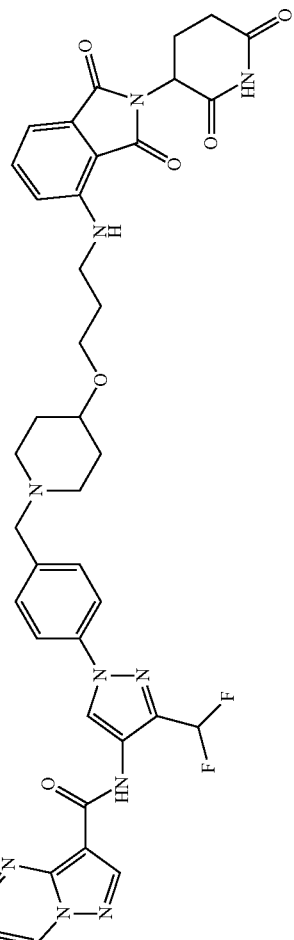 |
| I-404 | 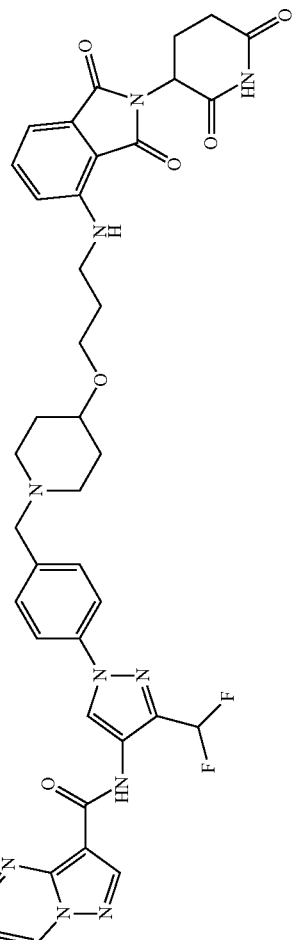 |

TABLE 1-continued
Exemplary Compounds
| I-# | Structure |
|---|---|
| I-405 | 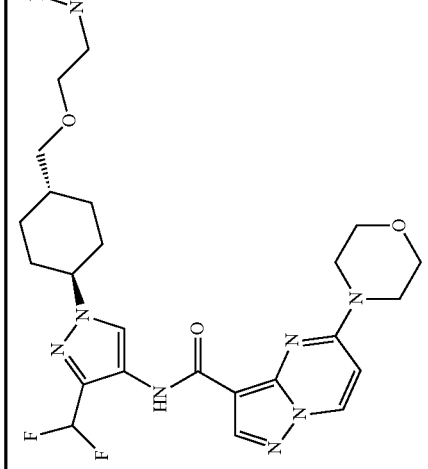 |
| I-406 | 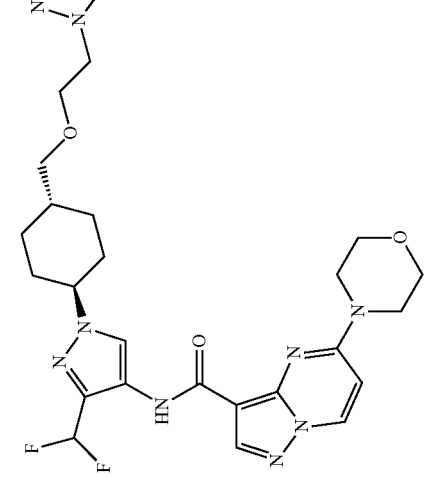 |

TABLE 1-continued
Exemplary Compounds
| I-# | Structure |
|---|---|
| I-407 | 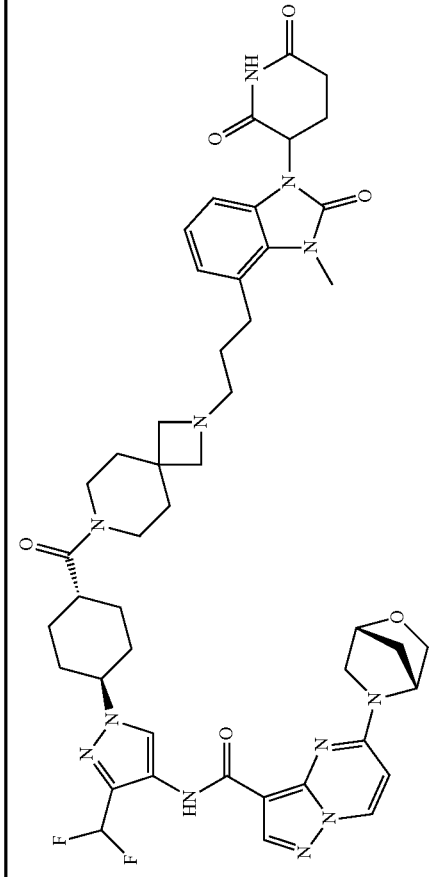 |
| I-408 | 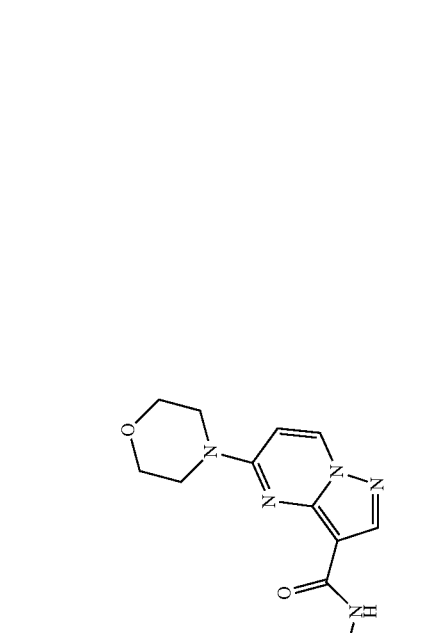 |

TABLE 1-continued
Exemplary Compounds
| I-# | Structure |
|---|---|
| I-409 | 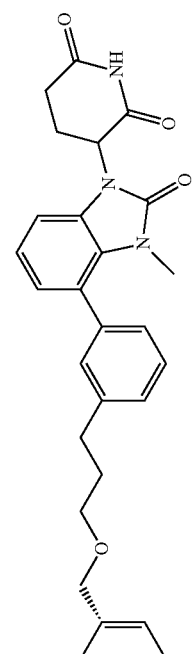 |
| I-410 | 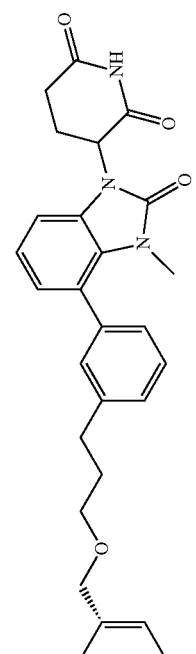 |

TABLE 1-continued
Exemplary Compounds
| I-# | Structure |
|---|---|
| I-411 | 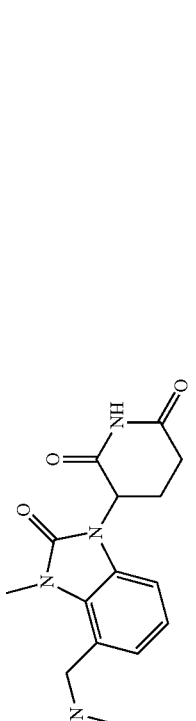 |
| I-412 | 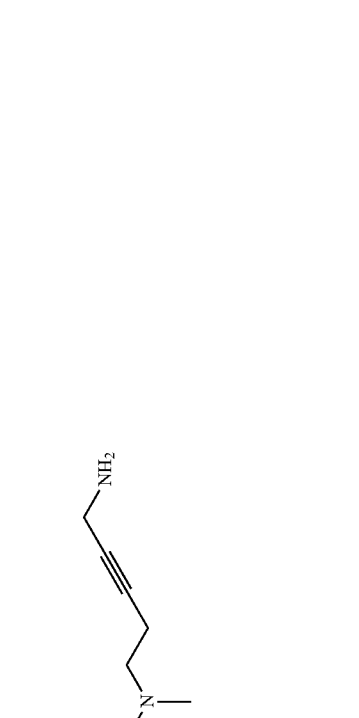 |

TABLE 1-continued
Exemplary Compounds
| I-# | Structure |
|---|---|
| I-413 | 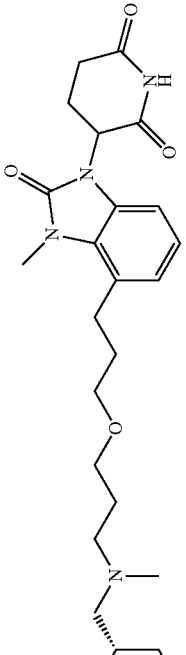 |
| I-414 | 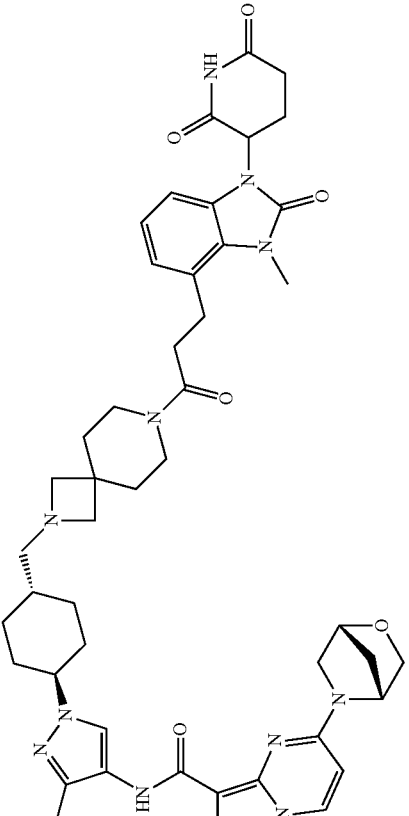 |

TABLE 1-continued
Exemplary Compounds
| I-# | Structure |
|---|---|
| I-415 | 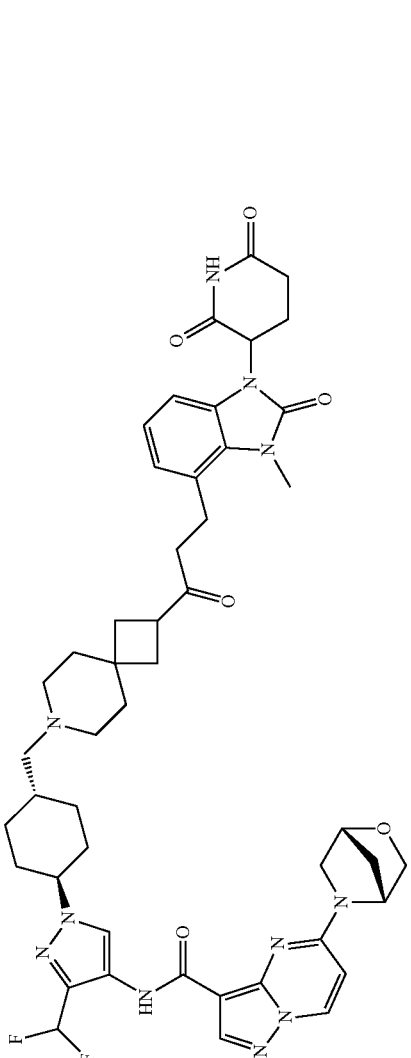 |
| I-416 | 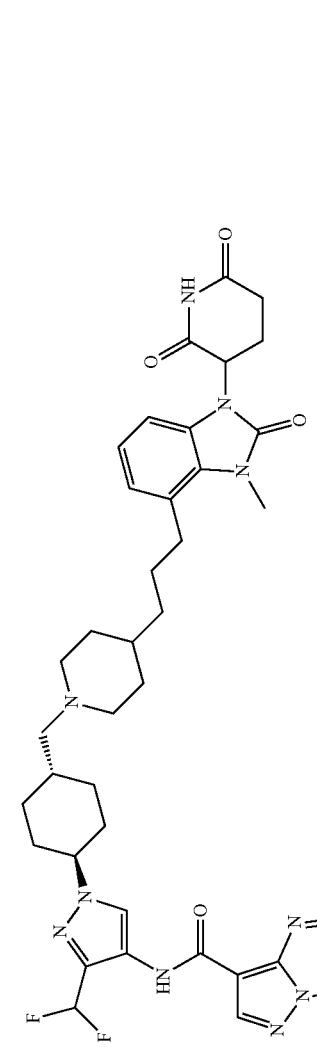 |

TABLE 1-continued
Exemplary Compounds
| I-# | Structure |
|---|---|
| I-417 | 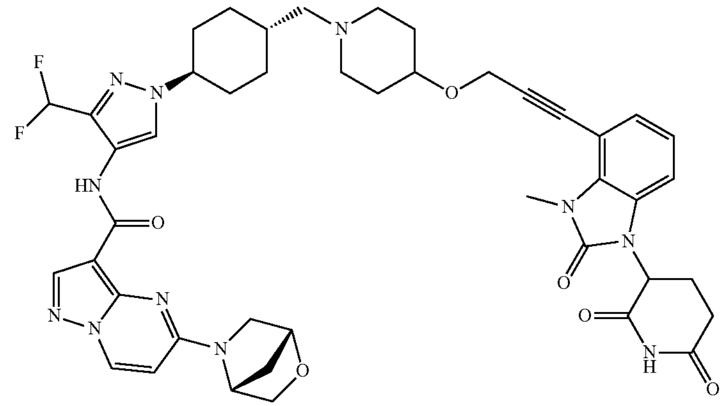 [SMILES: Cn1c(=O)n(C2CCC(=O)NC2=O)c2cccc(C#CCOC3CCN(C[C@H]4CC[C@H](n5cc(NC(=O)c6cnn7ccc(N8C[C@H]9C[C@@H]8CO9)nc67)c(C(F)F)n5)CC4)CC3)c21] |
| I-418 | 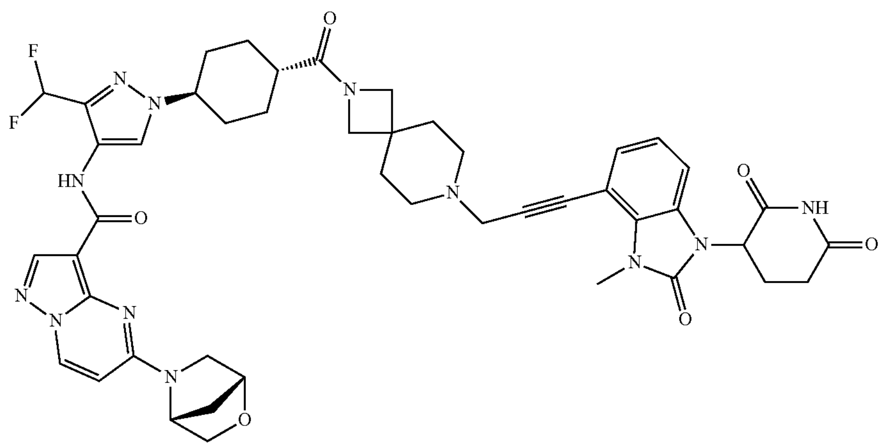 [SMILES: Cn1c(=O)n(C2CCC(=O)NC2=O)c2cccc(C#CCN3CCC4(CC3)CN(C(=O)[C@H]3CC[C@H](n5cc(NC(=O)c6cnn7ccc(N8C[C@H]9C[C@@H]8CO9)nc67)c(C(F)F)n5)CC3)C4)c21] |

TABLE 1-continued
Exemplary Compounds
| I-# | Structure |
|---|---|
| I-419 | 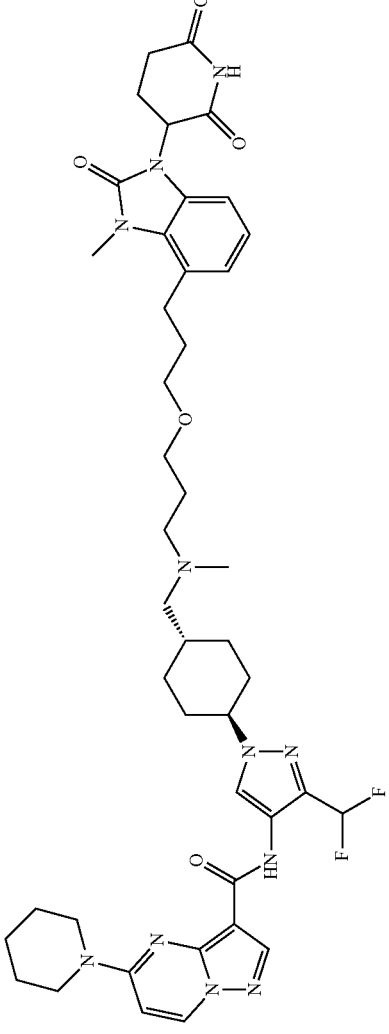 |
| I-420 | 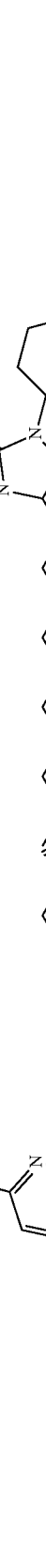 |

TABLE 1-continued
Exemplary Compounds
| I-# | Structure |
|---|---|
| I-421 | 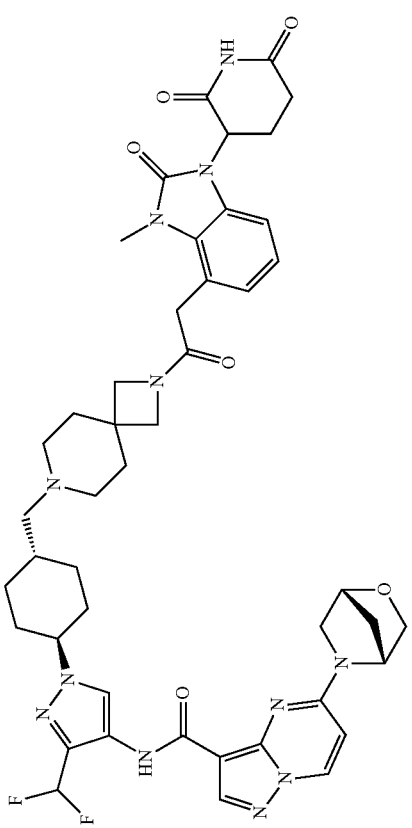 |
| I-422 | 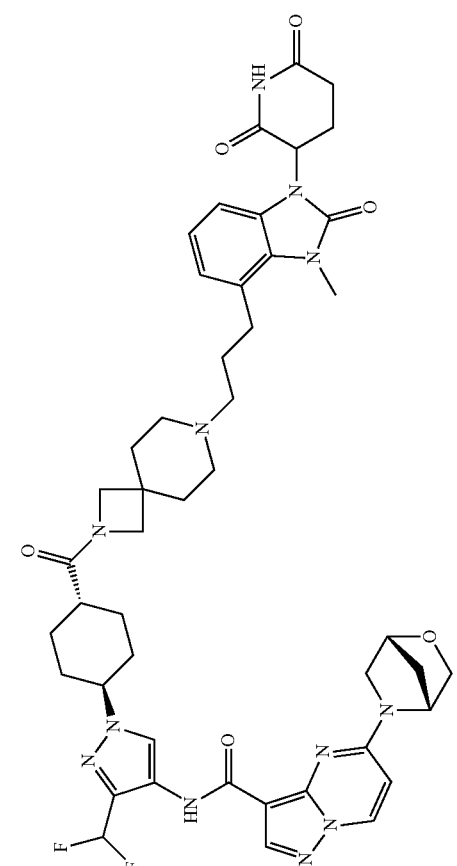 |

TABLE 1-continued
Exemplary Compounds
| I-# | Structure |
|---|---|
| I-423 | 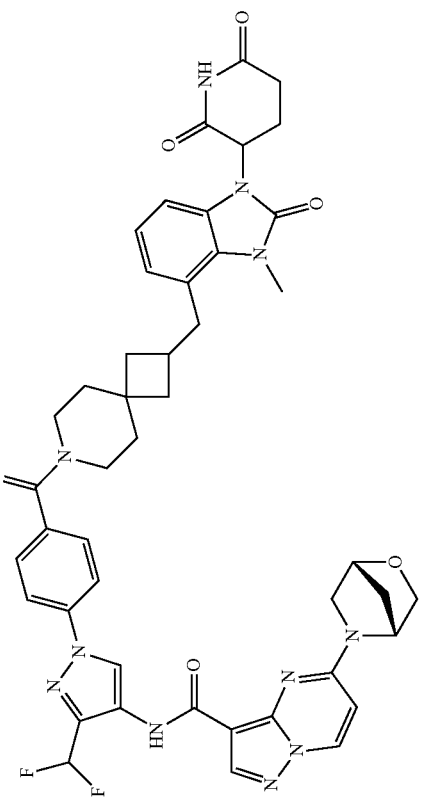 |
| I-424 | 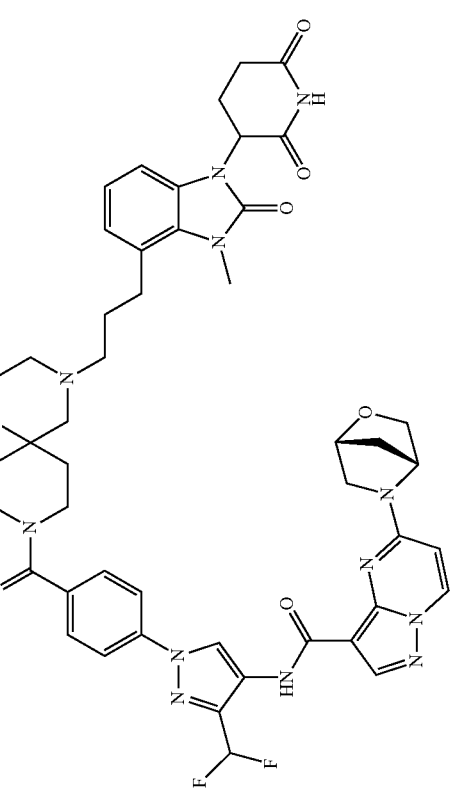 |

TABLE 1-continued
Exemplary Compounds
| I-# | Structure |
|---|---|
| I-425 | 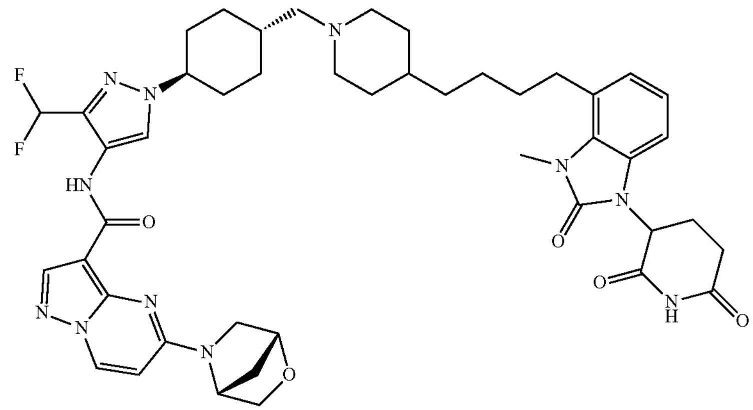 [SMILES: Cn1c(=O)n(C2CCC(=O)NC2=O)c2cccc(CCCCC3CCN(C[C@H]4CC[C@H](n5cc(NC(=O)c6cnn7ccc(N8C[C@H]9C[C@@H]8CO9)nc67)c(C(F)F)n5)CC4)CC3)c21] |
| I-426 | 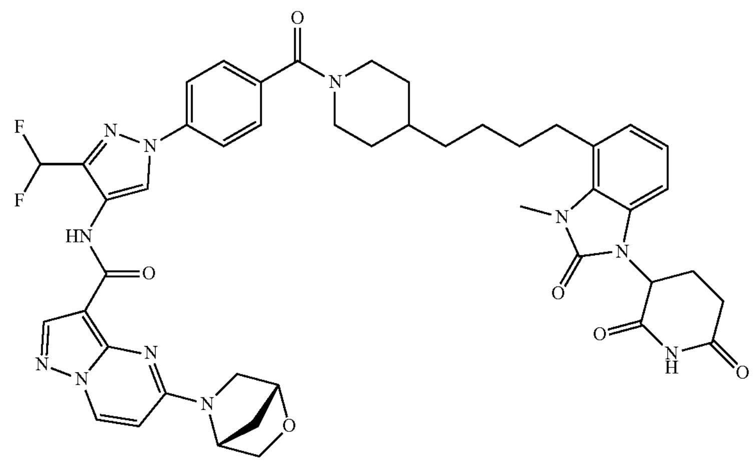 [SMILES: Cn1c(=O)n(C2CCC(=O)NC2=O)c2cccc(CCCCC3CCN(C(=O)c4ccc(-n5cc(NC(=O)c6cnn7ccc(N8C[C@H]9C[C@@H]8CO9)nc67)c(C(F)F)n5)cc4)CC3)c21] |

TABLE 1-continued
Exemplary Compounds
| I-# | Structure |
|---|---|
| I-427 | 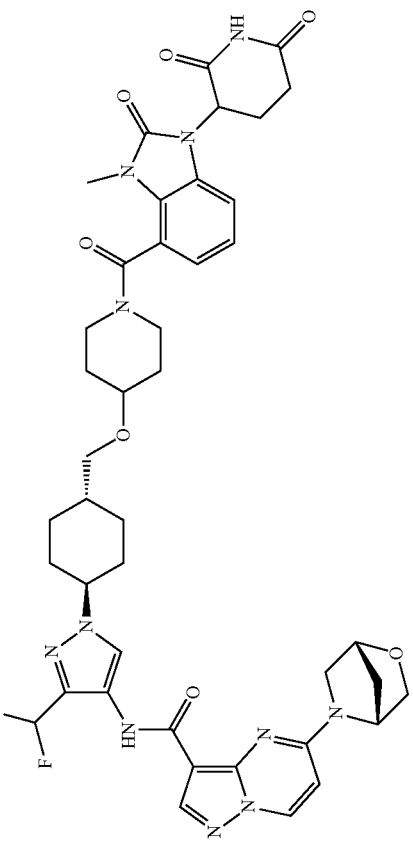 |
| I-428 | 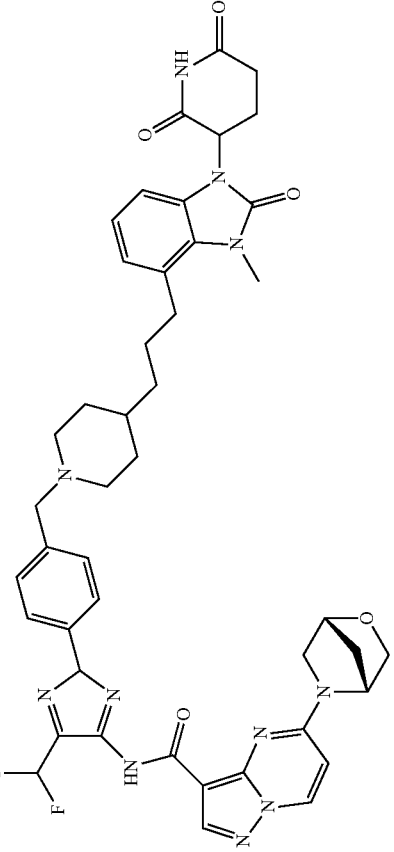 |

TABLE 1-continued
Exemplary Compounds
| I-# | Structure |
|---|---|
| I-429 | 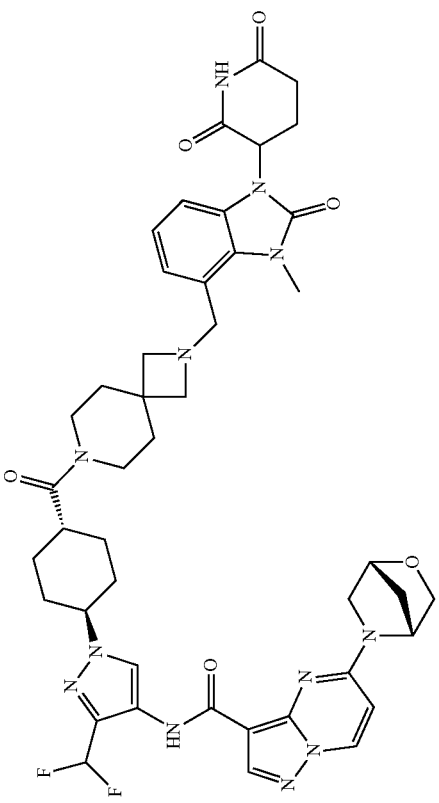 |
| I-430 | 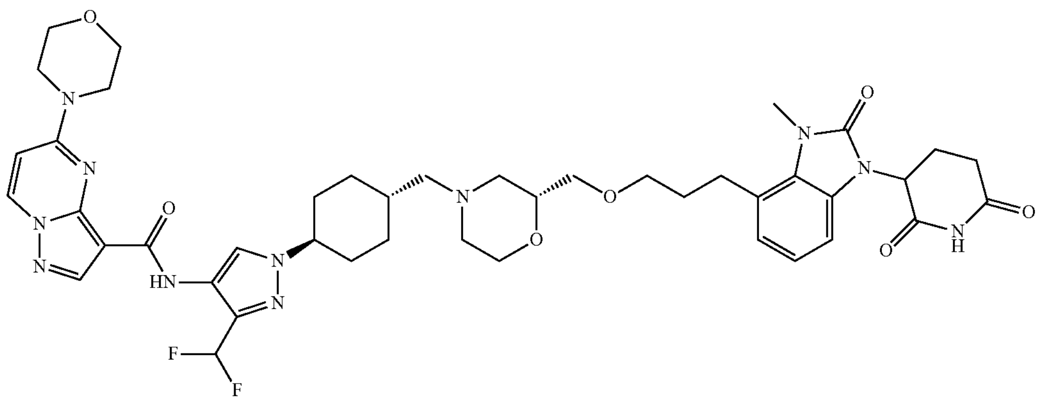 [SMILES: Cn1c(=O)n(C2CCC(=O)NC2=O)c2cccc(CCCOC[C@H]3CN(C[C@H]4CC[C@H](n5cc(NC(=O)c6cnn7ccc(N8CCOCC8)nc67)c(C(F)F)n5)CC4)CCO3)c21] |

TABLE 1-continued
Exemplary Compounds
| I-# | Structure |
|---|---|
| I-431 | 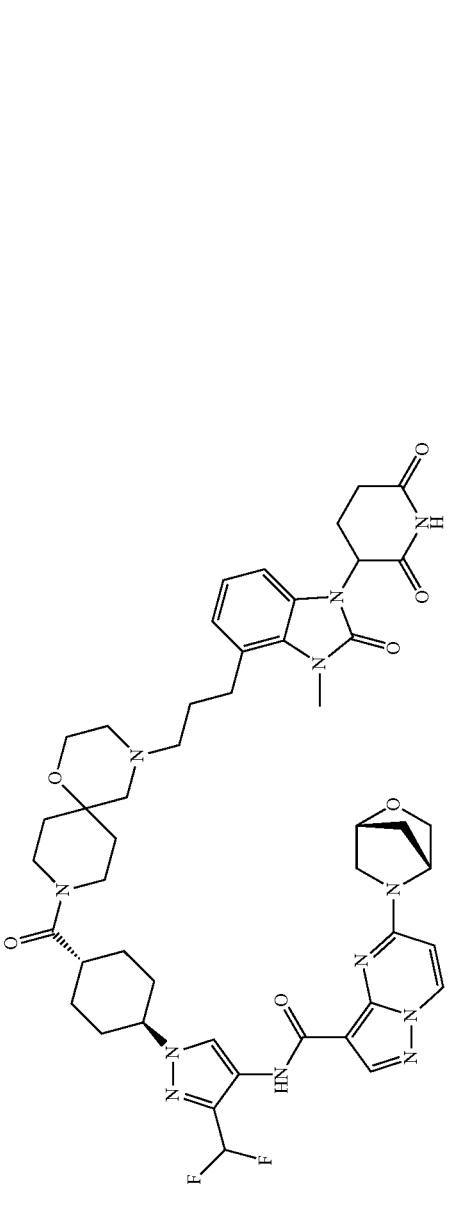 |
| I-432 | 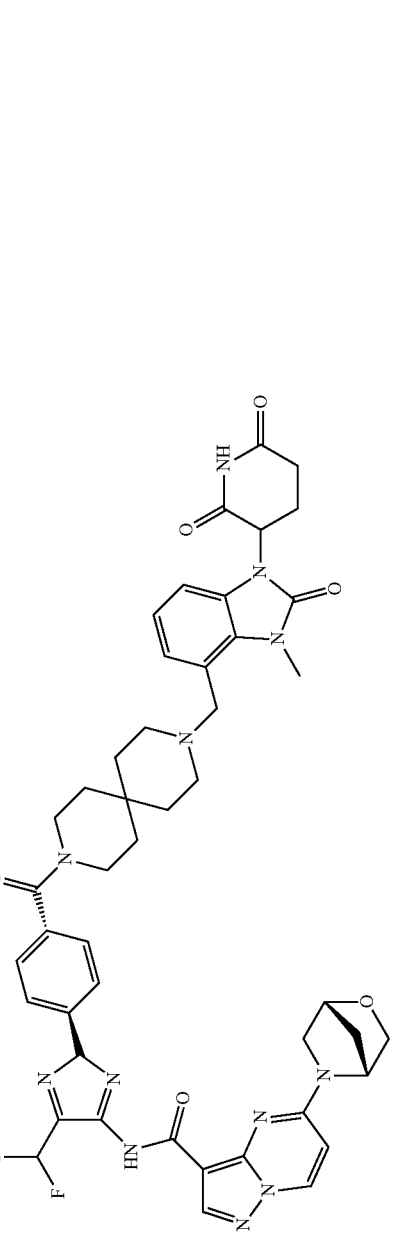 |

TABLE 1-continued
Exemplary Compounds
| I-# | Structure |
|---|---|
| I-433 | 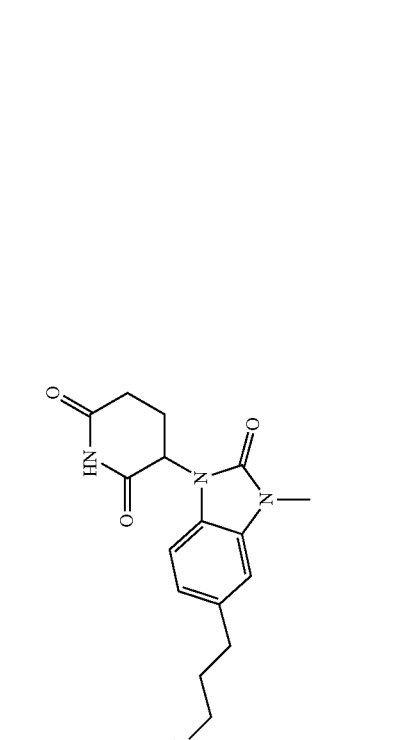 |
| I-434 | 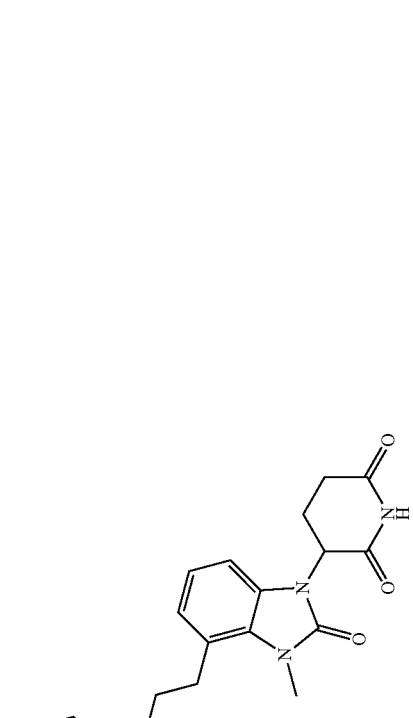 |

TABLE 1-continued
Exemplary Compounds
| I-# | Structure |
|---|---|
| I-435 | 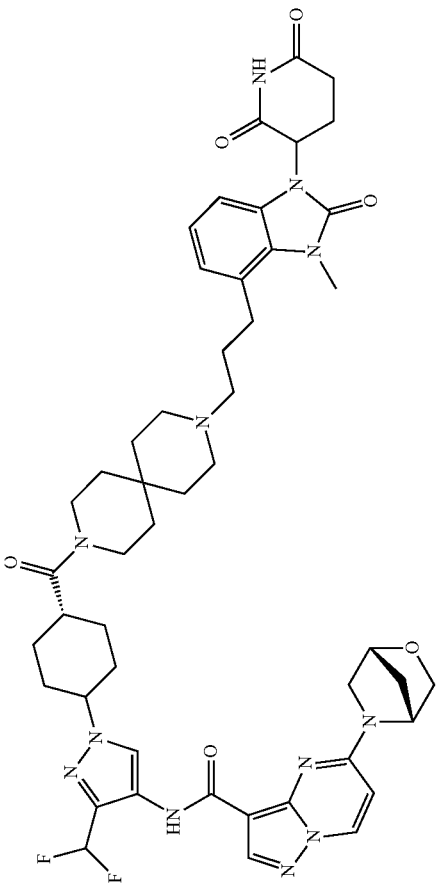 |
| I-436 | 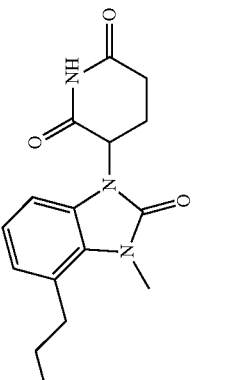 |

TABLE 1-continued
Exemplary Compounds
| I-# | Structure |
|---|---|
| I-437 | 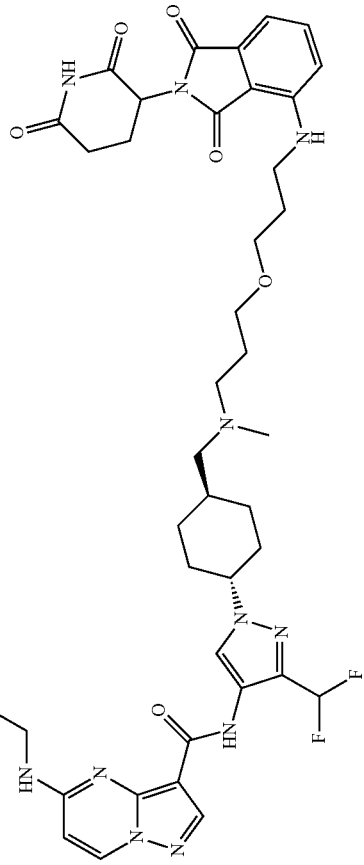 |
| I-438 | 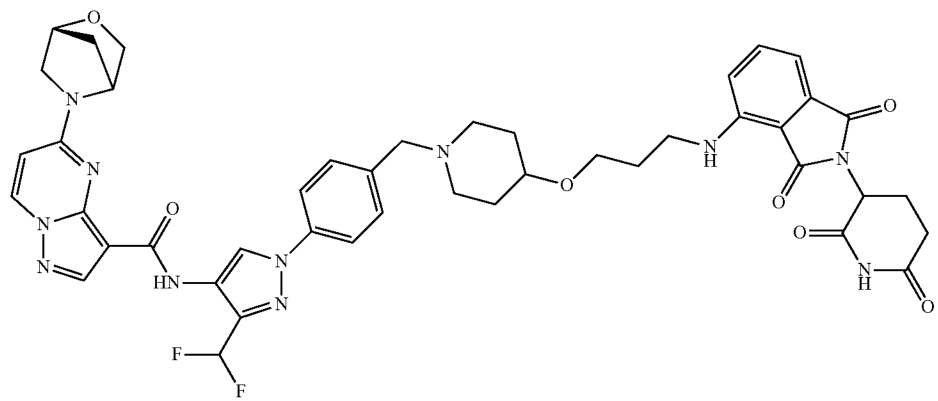 [SMILES: O=C1CCC(N2C(=O)c3cccc(NCCCOC4CCN(Cc5ccc(-n6cc(NC(=O)c7cnn8ccc(N9C[C@H]%10CC9CO%10)nc78)c(C(F)F)n6)cc5)CC4)c3C2=O)C(=O)N1] |

TABLE 1-continued
Exemplary Compounds
| I-# | Structure |
|---|---|
| I-439 | 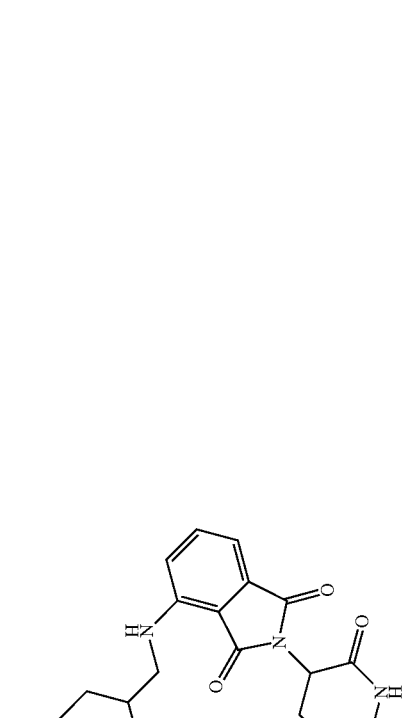 |
| I-440 | 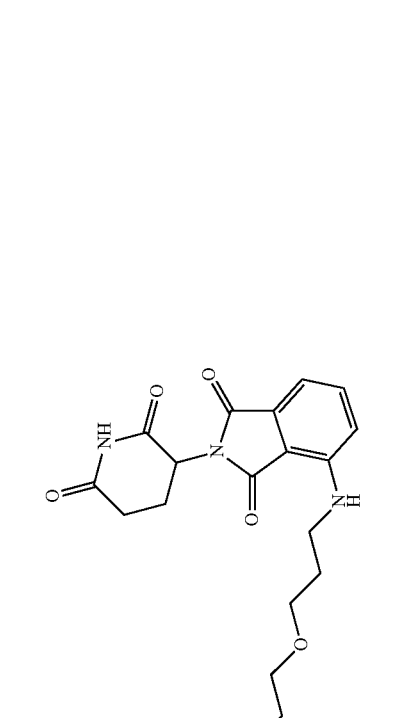 |

TABLE 1-continued
Exemplary Compounds
| I-# | Structure |
|---|---|
| I-441 | 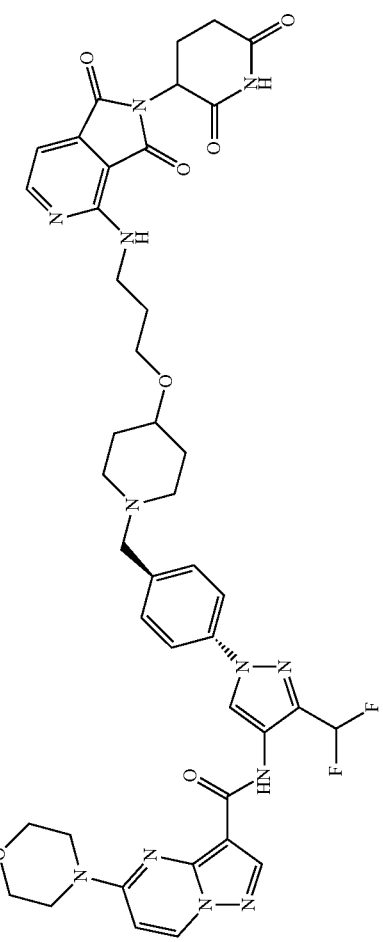 |
| I-442 | 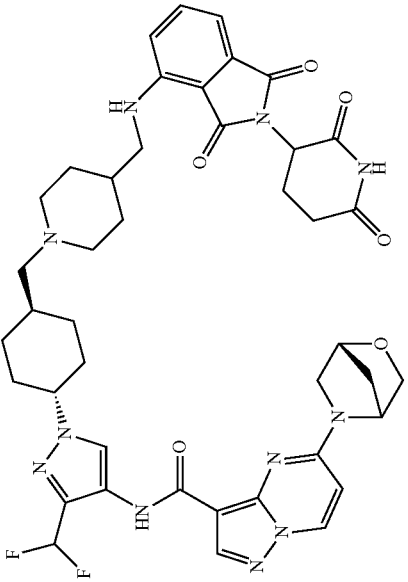 |

TABLE 1-continued
Exemplary Compounds
| I-# | Structure |
|---|---|
| I-443 | 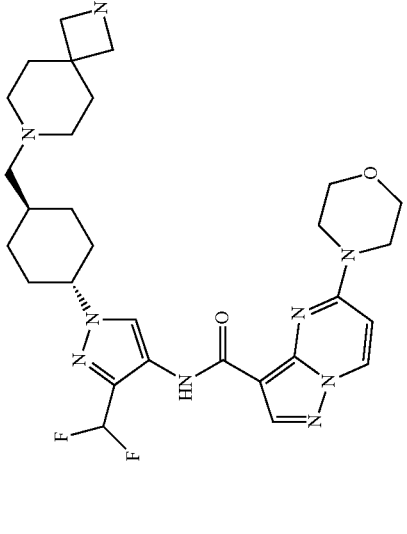 |
| I-444 | 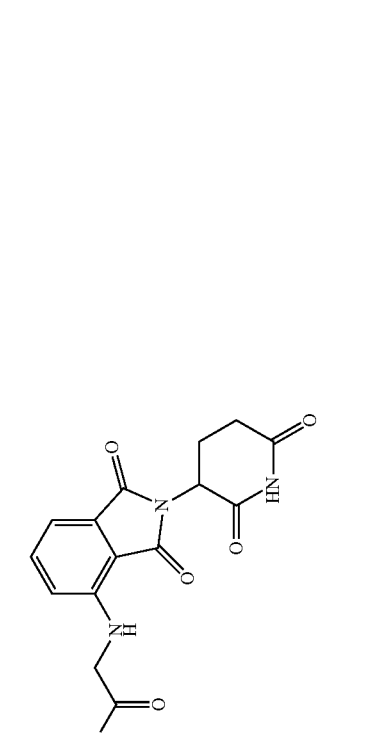 |

TABLE 1-continued
Exemplary Compounds
| I-# | Structure |
|---|---|
| I-445 | 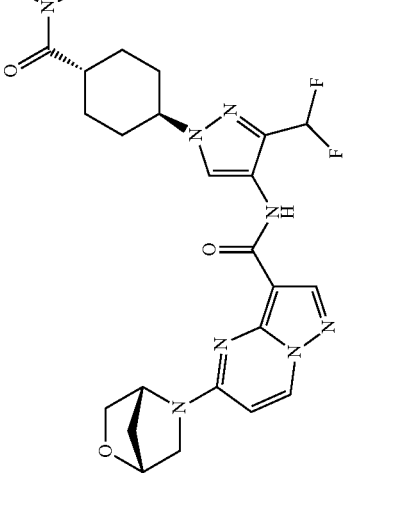 |
| I-446 | 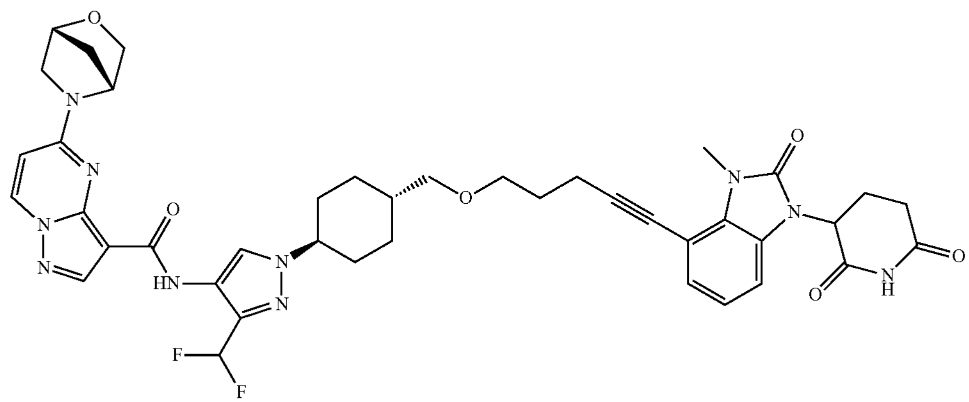 [SMILES: Cn1c(=O)n(C2CCC(=O)NC2=O)c2cccc(C#CCCCOC[C@H]3CC[C@H](n4cc(NC(=O)c5cnn6ccc(N7C[C@H]8C[C@@H]7CO8)nc56)c(C(F)F)n4)CC3)c21] |

TABLE 1-continued
Exemplary Compounds
| I-# | Structure |
|---|---|
| I-447 | 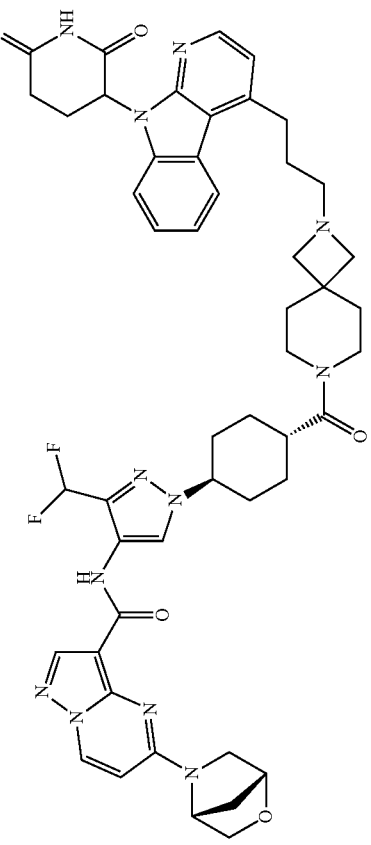 |
| I-448 | 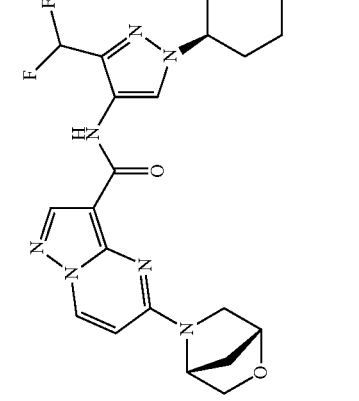 |

TABLE 1-continued
Exemplary Compounds
| I-# | Structure |
|---|---|
| I-449 | 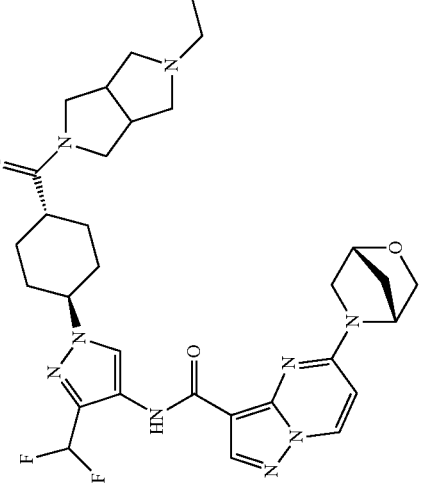 |
| I-450 | 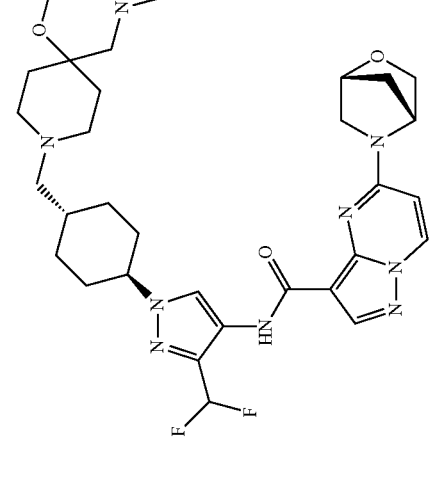 |

TABLE 1-continued
Exemplary Compounds
| I-# | Structure |
|---|---|
| I-451 | 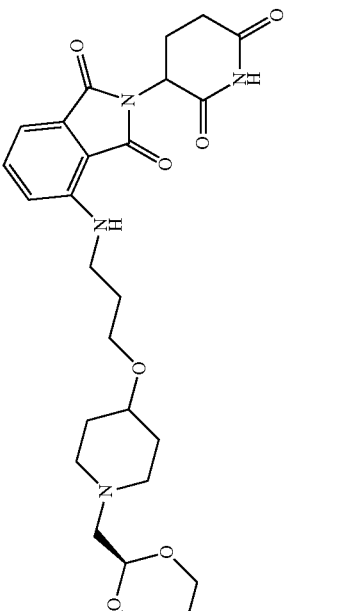 |
| I-452 | 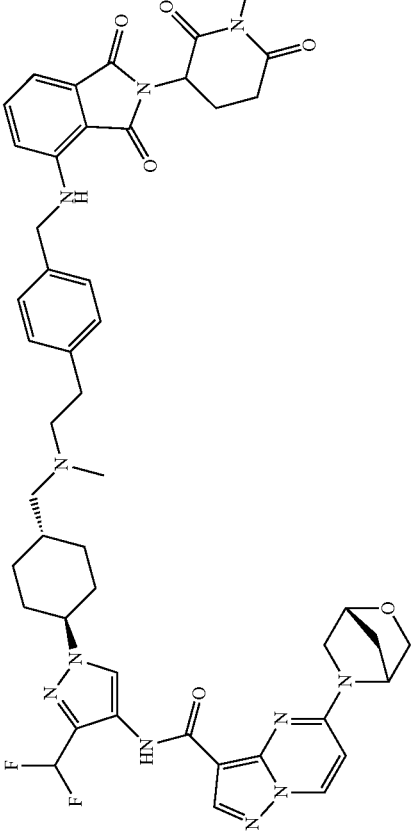 |

TABLE 1-continued
Exemplary Compounds
| I-# | Structure |
|---|---|
| I-453 | 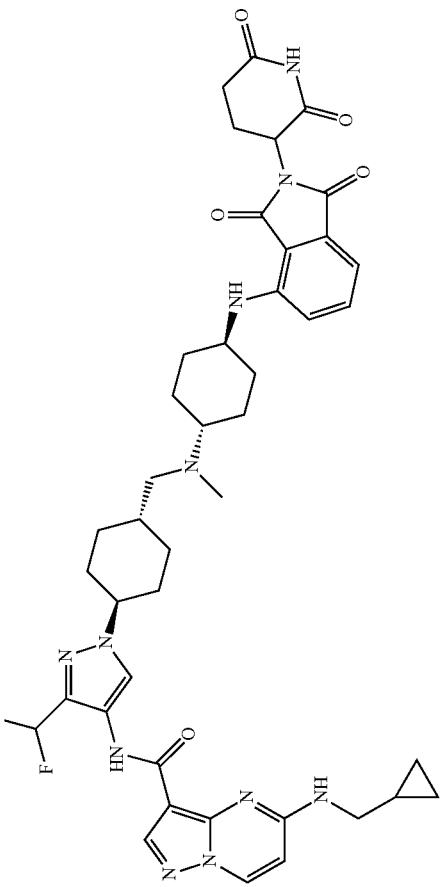 |
| I-454 | 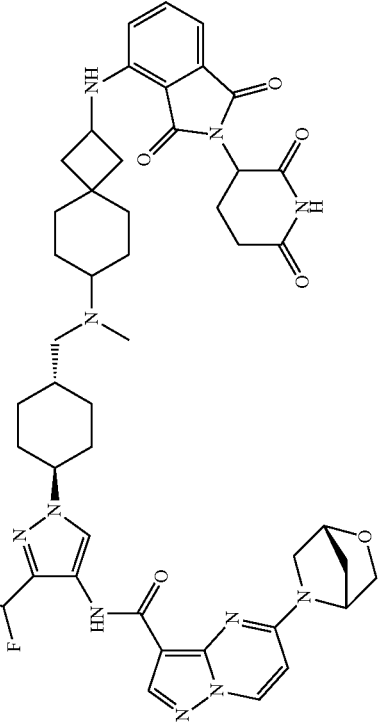 |

TABLE 1-continued
Exemplary Compounds
| I-# | Structure |
|---|---|
| I-455 | 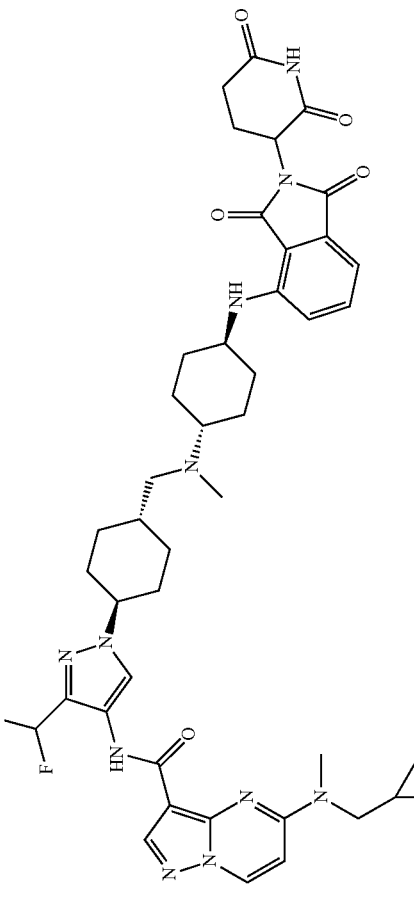 |
| I-456 | 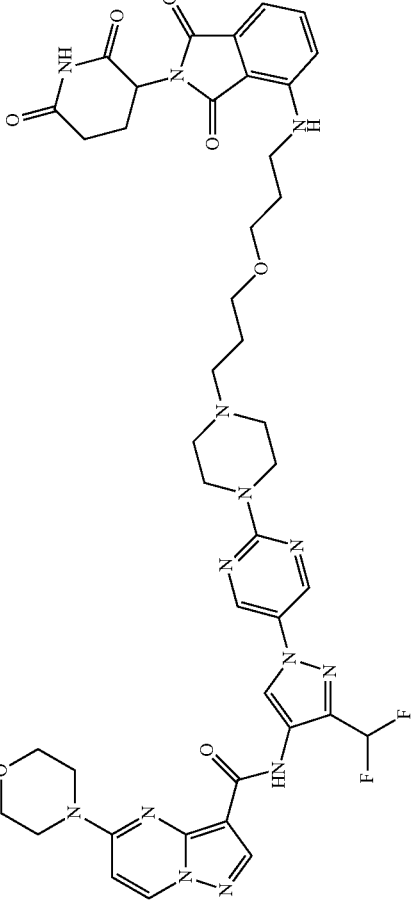 |

TABLE 1-continued

Exemplary Compounds

| I-# | Structure |
|---|---|
| I-457 | 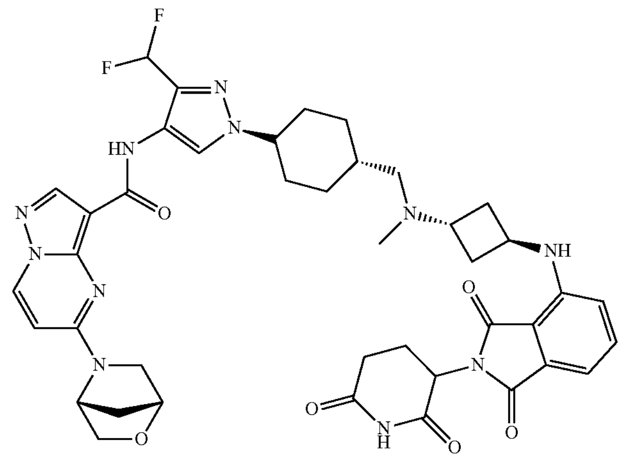 |
| I-458 | 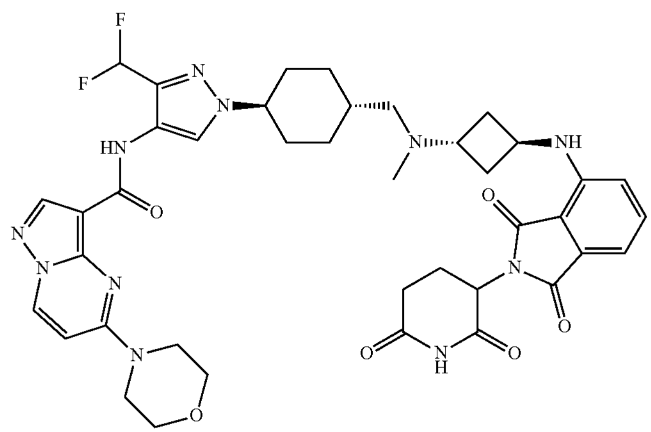 [SMILES: CN(C[C@H]1CC[C@H](n2cc(NC(=O)c3cnn4ccc(N5CCOCC5)nc34)c(C(F)F)n2)CC1)[C@H]1C[C@H](Nc2cccc3c2C(=O)N(C2CCC(=O)NC2=O)C3=O)C1] |

TABLE 1-continued
Exemplary Compounds
| I-# | Structure |
|---|---|
| I-459 | 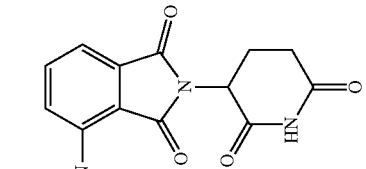 |
| I-460 | 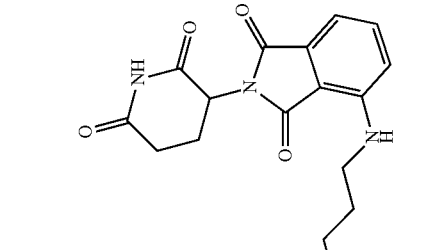 |

TABLE 1-continued
Exemplary Compounds
| I-# | Structure |
|---|---|
| I-461 | 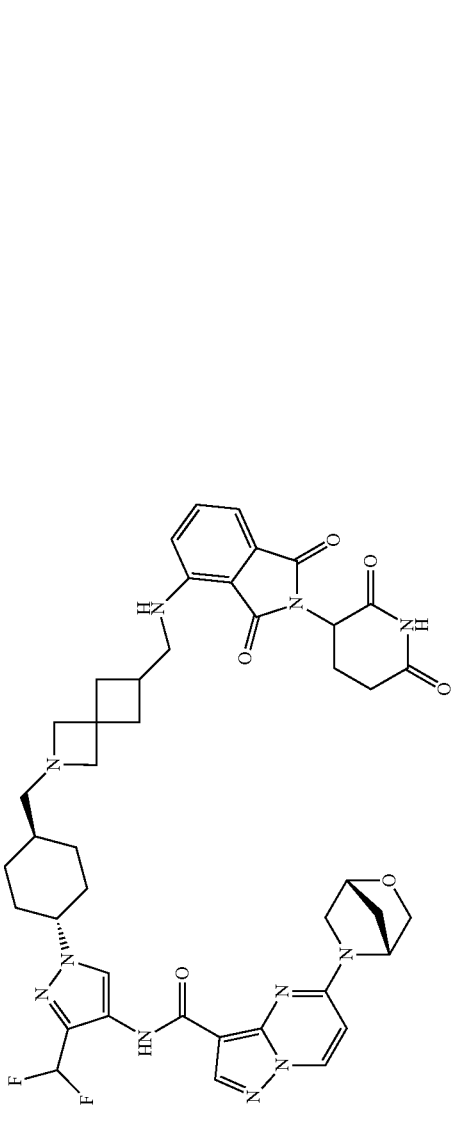 |
| I-462 | 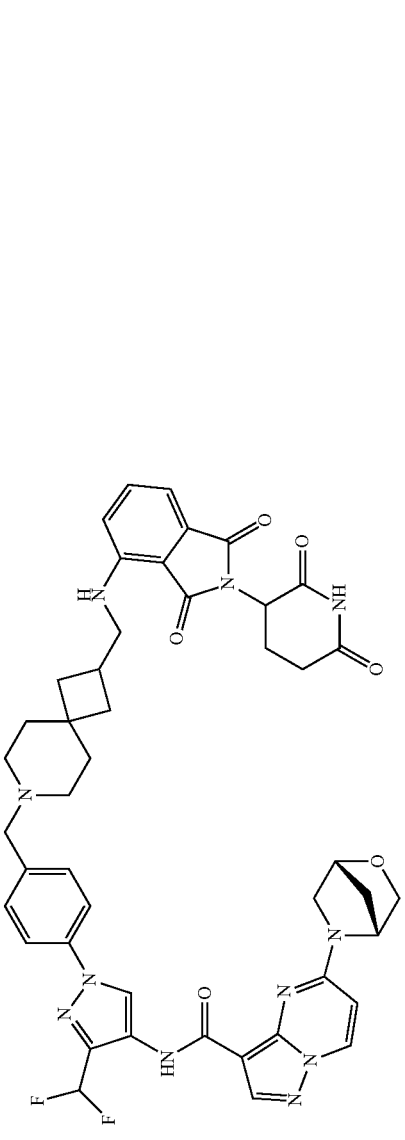 |

TABLE 1-continued
Exemplary Compounds
| I-# | Structure |
|---|---|
| I-463 | 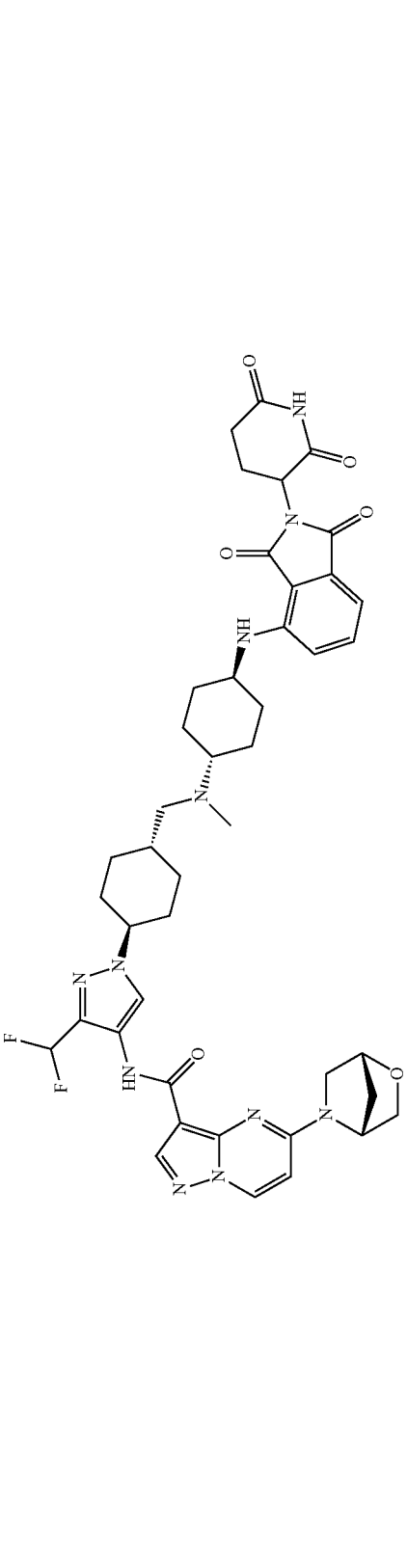 |
| I-464 | 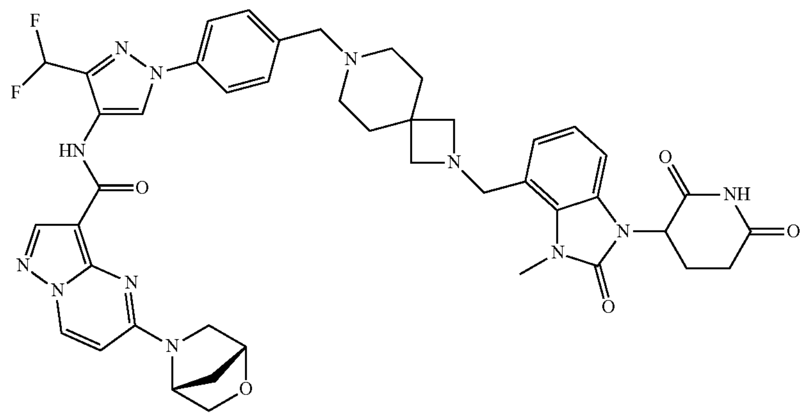 [SMILES: Cn1c(=O)n(C2CCC(=O)NC2=O)c2cccc(CN3CC4(CCN(Cc5ccc(-n6cc(NC(=O)c7cnn8ccc(N9C[C@H]%10C[C@@H]9CO%10)nc78)c(C(F)F)n6)cc5)CC4)C3)c21] |

TABLE 1-continued
Exemplary Compounds
| I-# | Structure |
|---|---|
| I-465 | 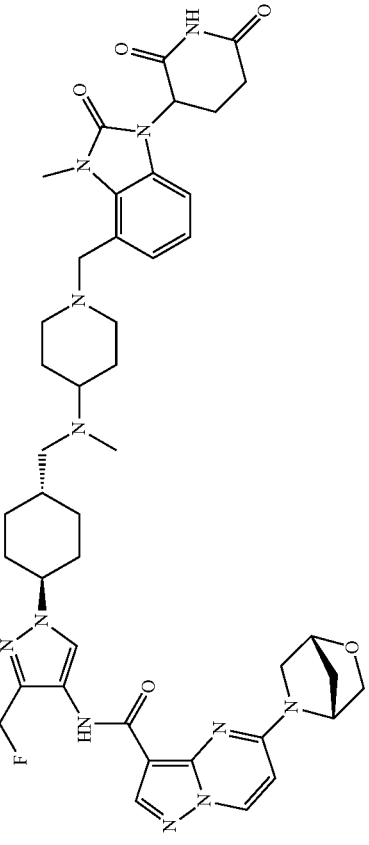 |
| I-466 | 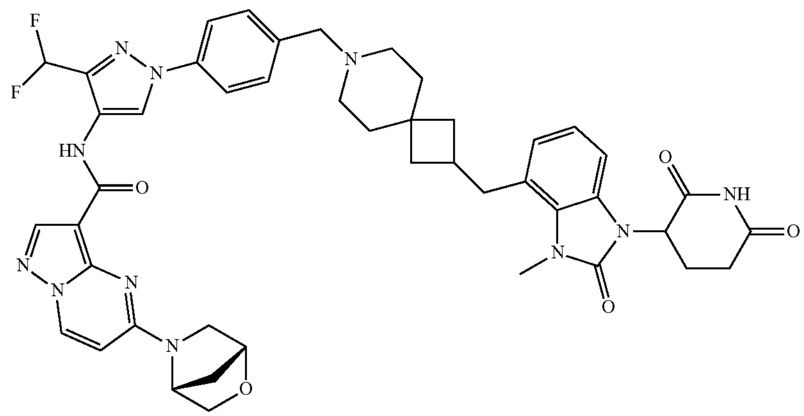 |

TABLE 1-continued
Exemplary Compounds
| I-# | Structure |
|---|---|
| I-467 | 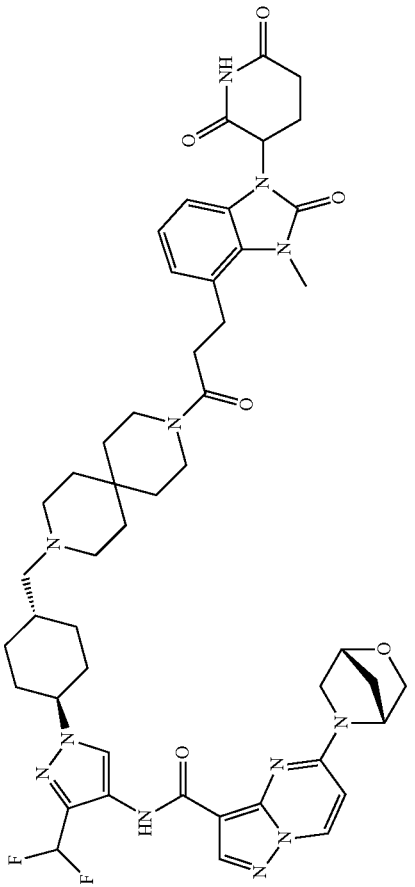 |
| I-468 | 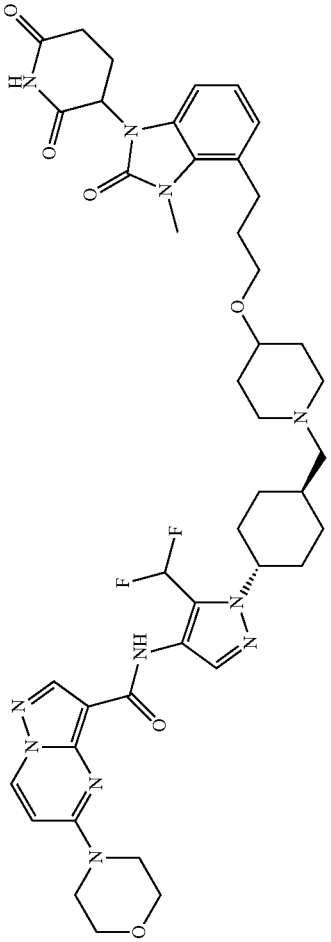 |

TABLE 1-continued
Exemplary Compounds
| I-# | Structure |
|---|---|
| I-469 | 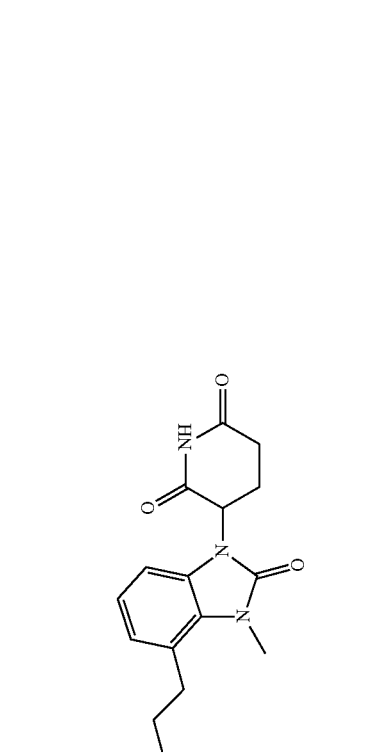 |
| I-470 | 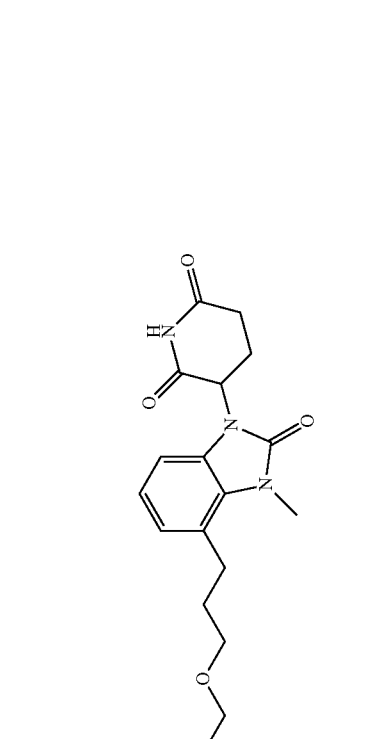 |

TABLE 1-continued
Exemplary Compounds
| I-# | Structure |
|---|---|
| I-471 | 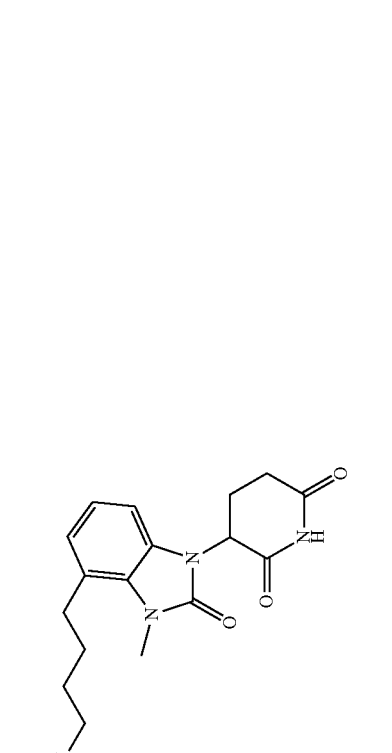 |
| I-472 | 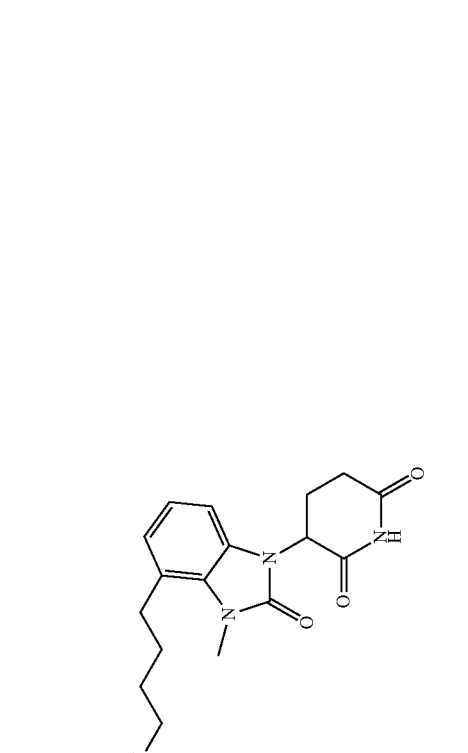 |

TABLE 1-continued
Exemplary Compounds
| I-# | Structure |
|---|---|
| I-473 | 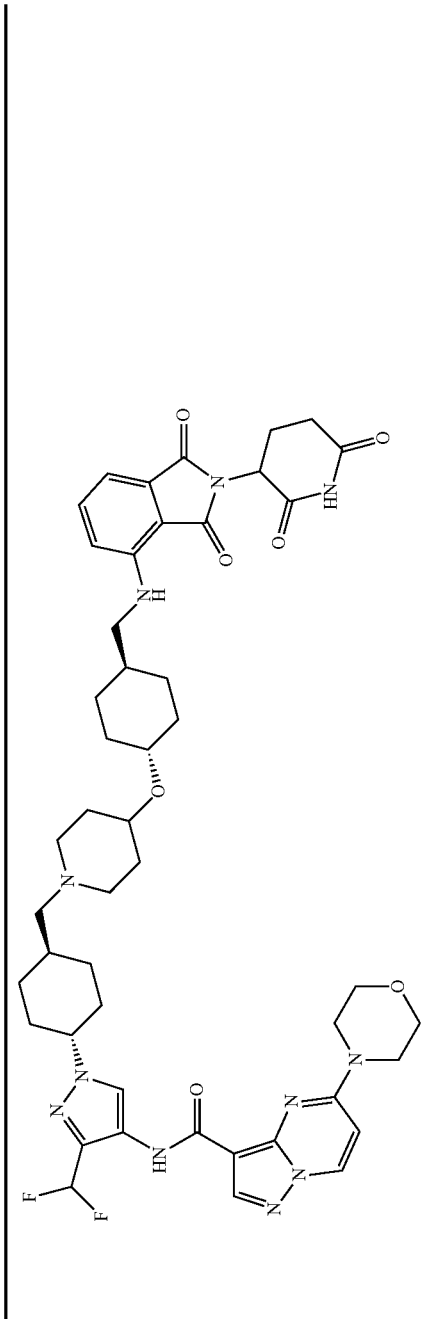 |
| I-474 | 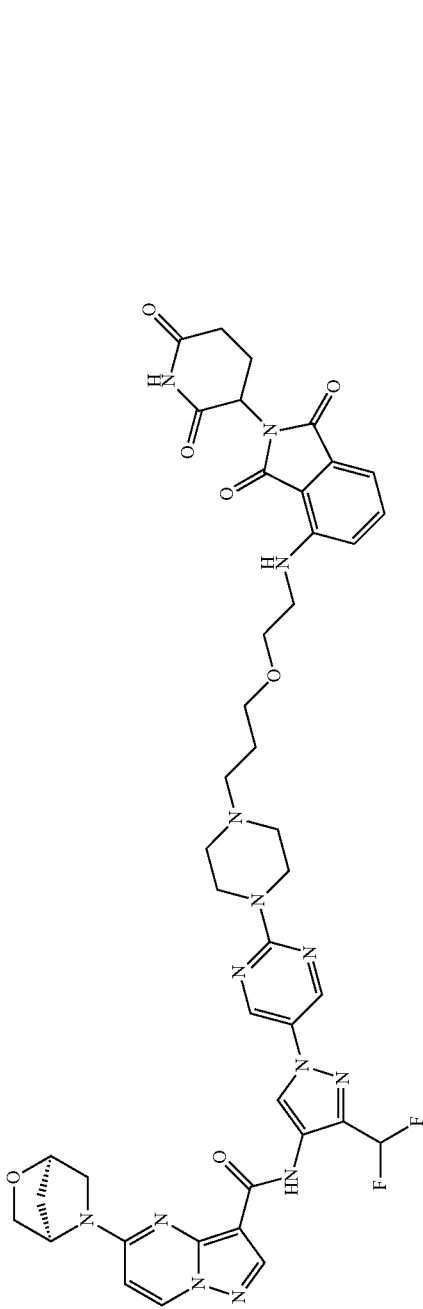 |

TABLE 1-continued
Exemplary Compounds
| I-# | Structure |
|---|---|
| I-475 | 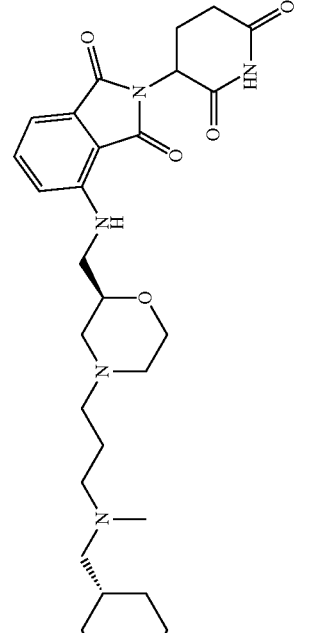 |
| I-476 | 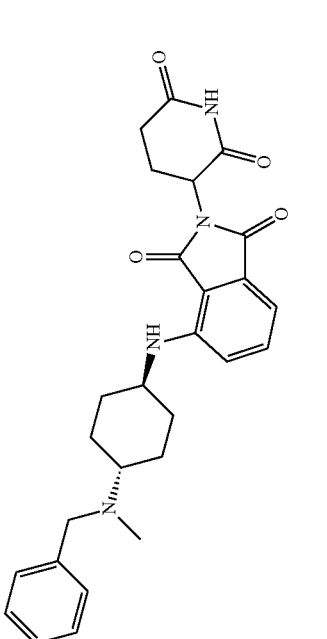 |

TABLE 1-continued
Exemplary Compounds
| I-# | Structure |
|---|---|
| I-477 | 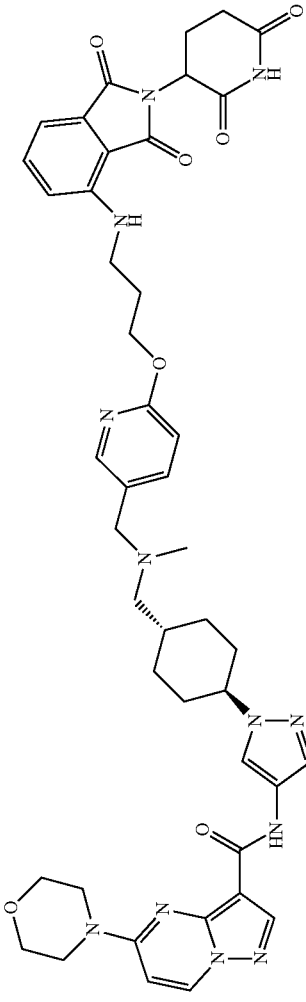 |
| I-478 | 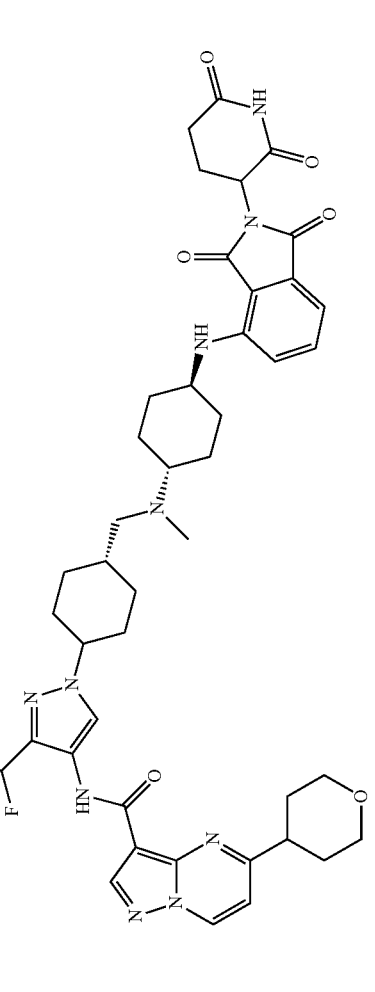 |

TABLE 1-continued
Exemplary Compounds
| I-# | Structure |
|---|---|
| I-479 | 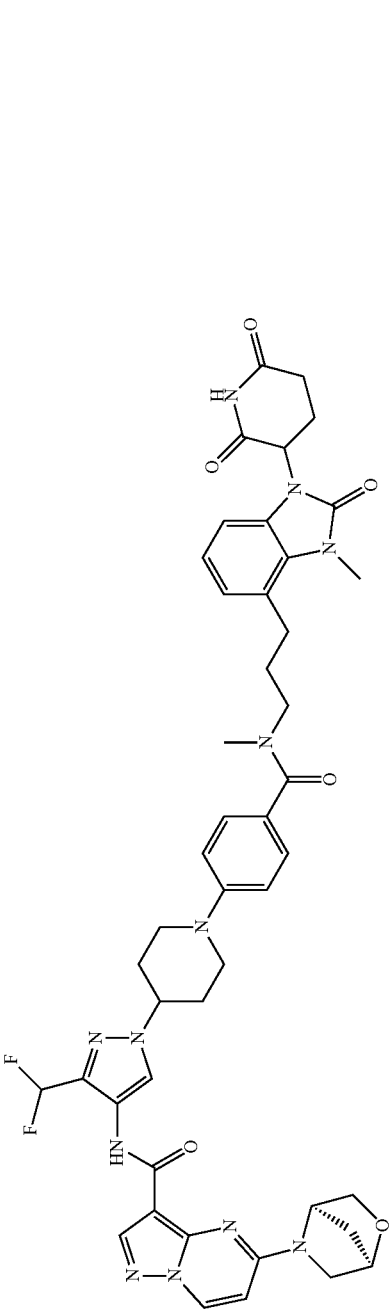 |
| I-480 | 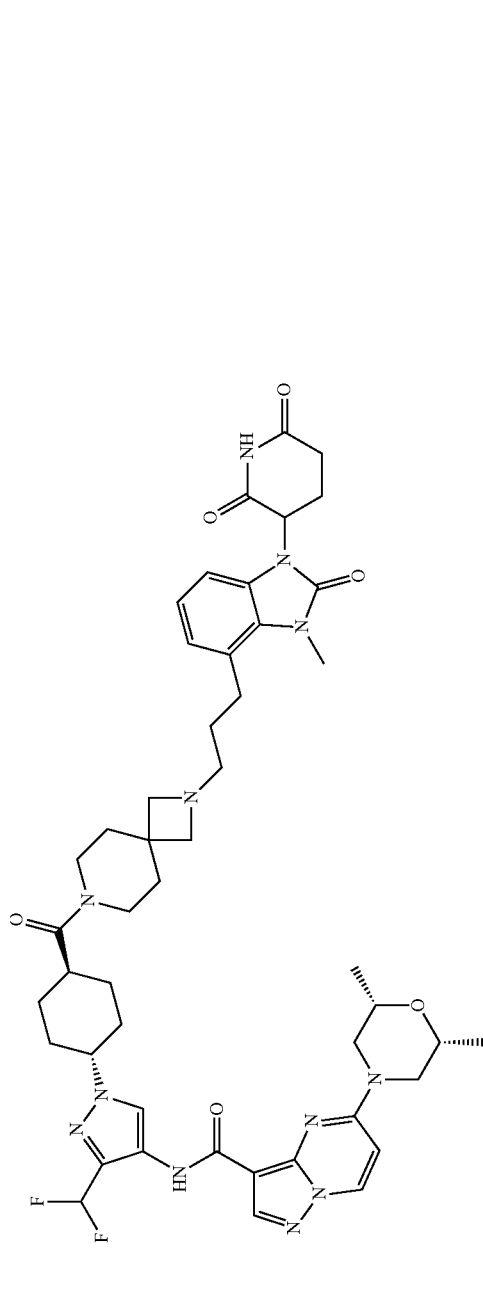 |

TABLE 1-continued
Exemplary Compounds
| I-# | Structure |
|---|---|
| I-481 | 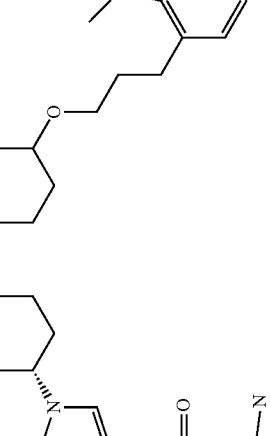 |
| I-482 | 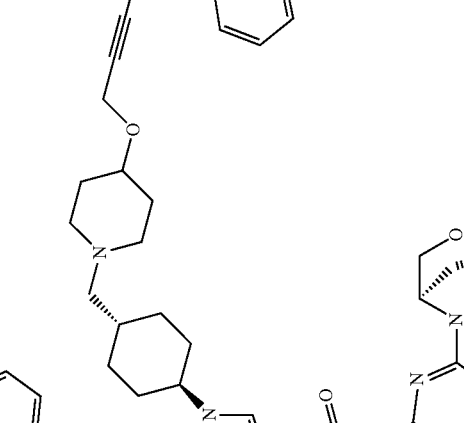 |

TABLE 1-continued
Exemplary Compounds
| I-# | Structure |
|---|---|
| I-483 | 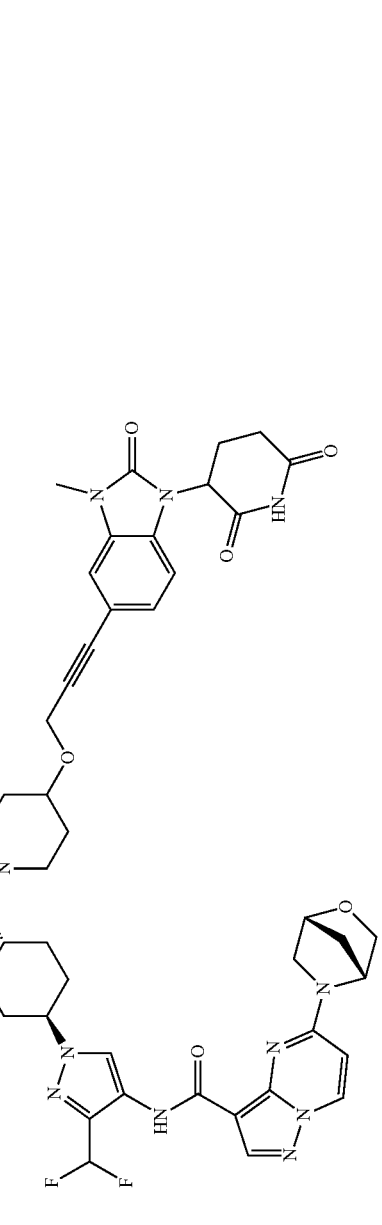 |
| I-484 | 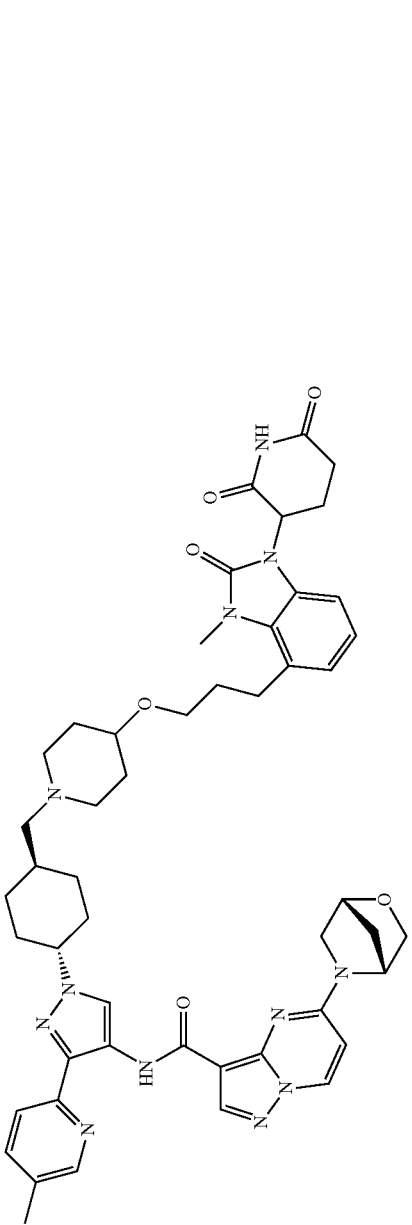 |

TABLE 1-continued

Exemplary Compounds

| I-# | Structure |
|---|---|
| I-485 | 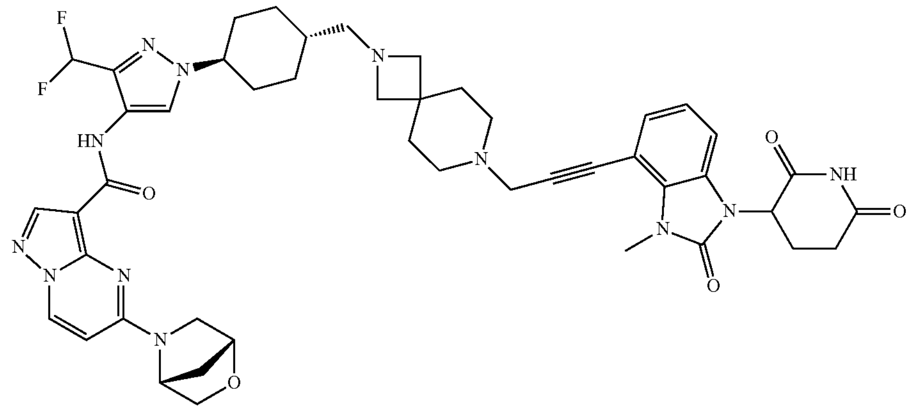 [SMILES: Cn1c(=O)n(C2CCC(=O)NC2=O)c2cccc(C#CCN3CCC4(CC3)CN(C[C@H]3CC[C@H](n5cc(NC(=O)c6cnn7ccc(N8C[C@H]9C[C@@H]8CO9)nc67)c(C(F)F)n5)CC3)C4)c21] |
| I-486 | 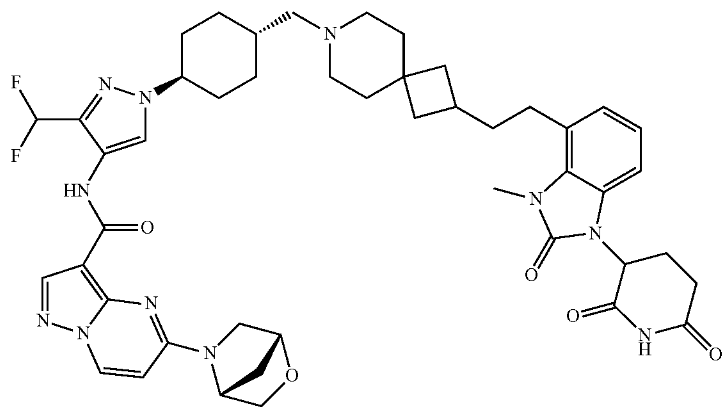 [SMILES: Cn1c(=O)n(C2CCC(=O)NC2=O)c2cccc(CCC3CC4(CCN(C[C@H]5CC[C@H](n6cc(NC(=O)c7cnn8ccc(N9C[C@H]%10C[C@@H]9CO%10)nc78)c(C(F)F)n6)CC5)CC4)C3)c21] |

TABLE 1-continued
Exemplary Compounds
| I-# | Structure |
|---|---|
| I-487 | 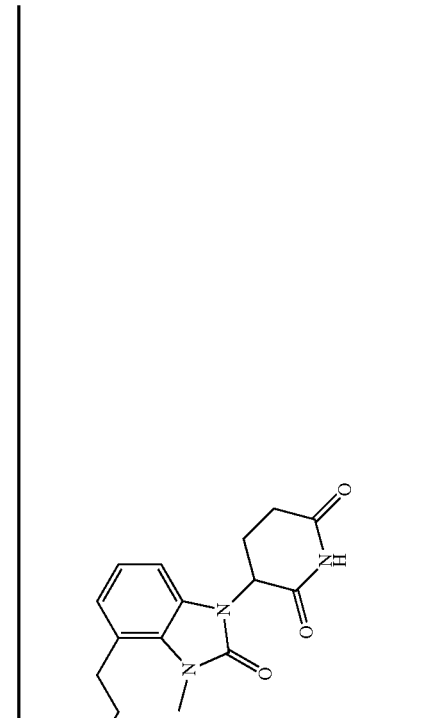 |
| I-488 | 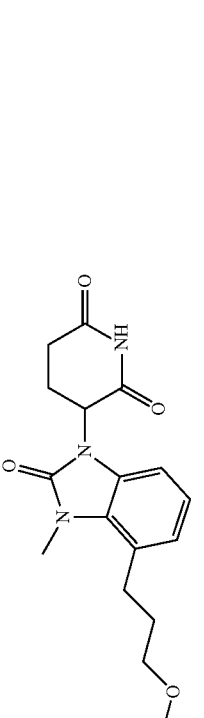 |

TABLE 1-continued
Exemplary Compounds
| I-# | Structure |
|---|---|
| I-489 | 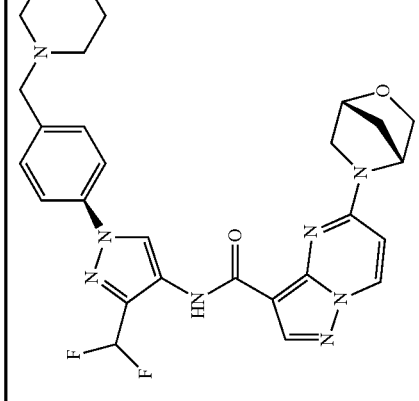 |
| I-490 | 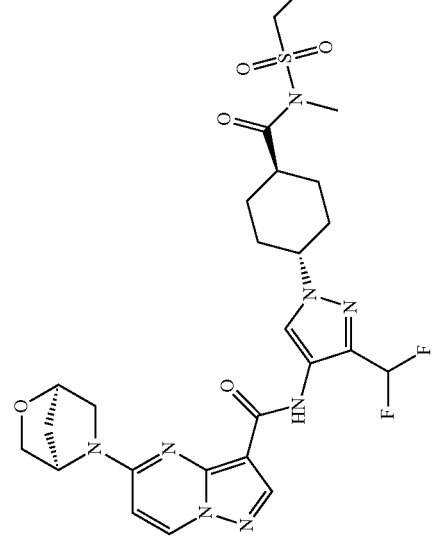 |

TABLE 1-continued
Exemplary Compounds
| I-# | Structure |
|---|---|
| I-491 | 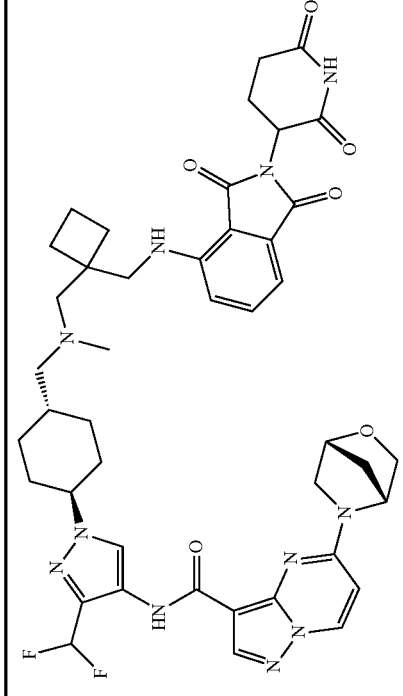 |
| I-492 | 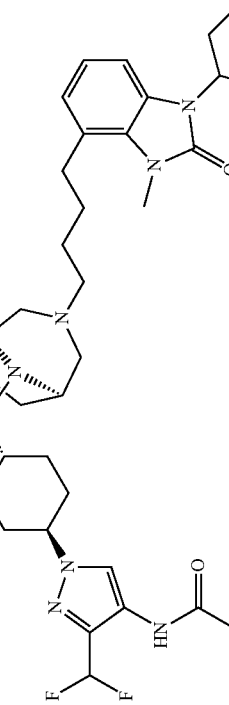 |

TABLE 1-continued
Exemplary Compounds
| I-# | Structure |
|---|---|
| I-493 | 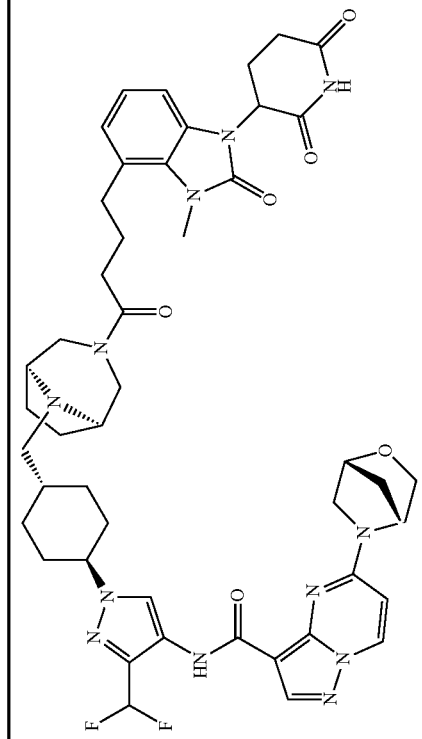 |
| I-494 | 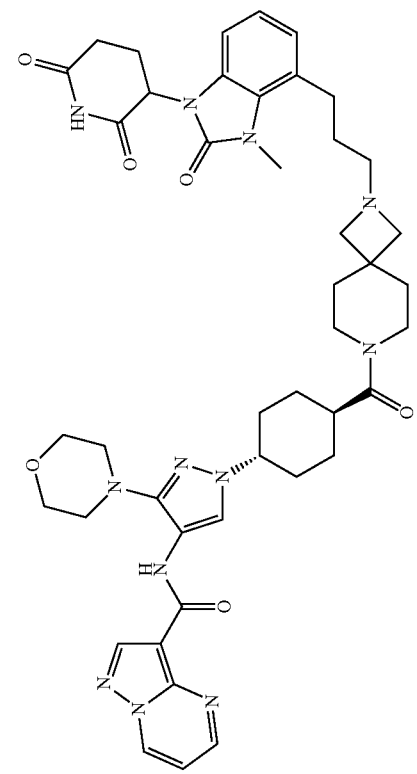 |

TABLE 1-continued
Exemplary Compounds
| I-# | Structure |
|---|---|
| I-495 | 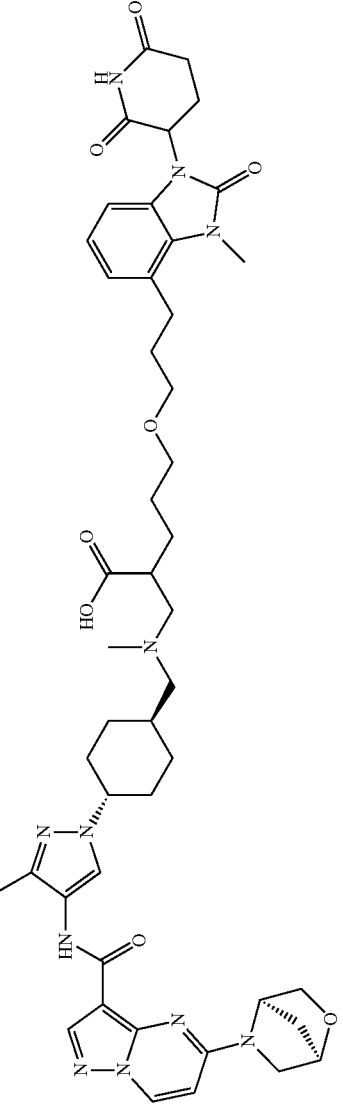 |
| I-496 | 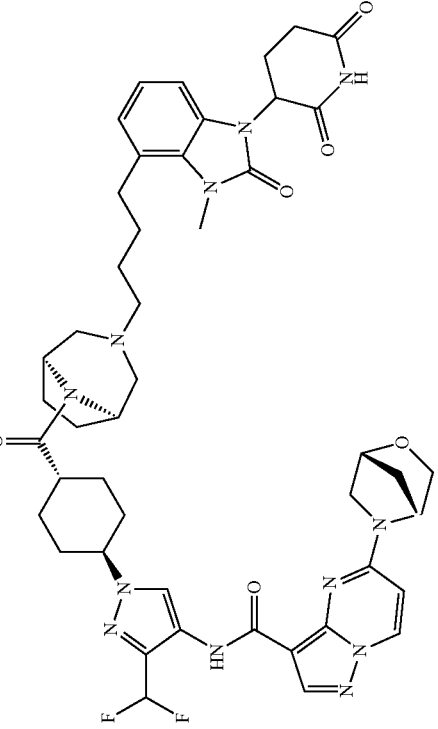 |

TABLE 1-continued
Exemplary Compounds
| I-# | Structure |
|---|---|
| I-497 | 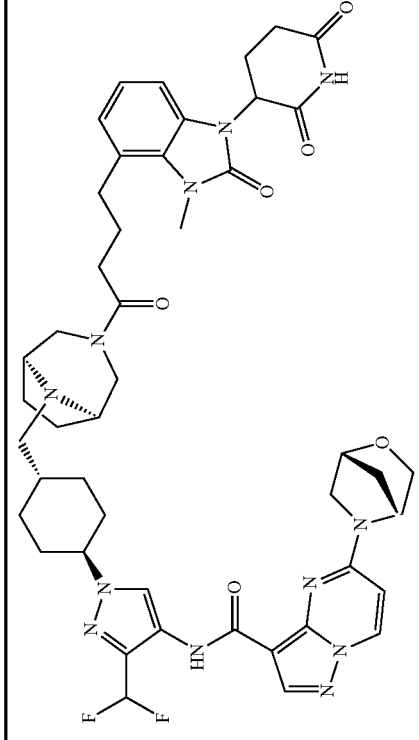 |
| I-498 | 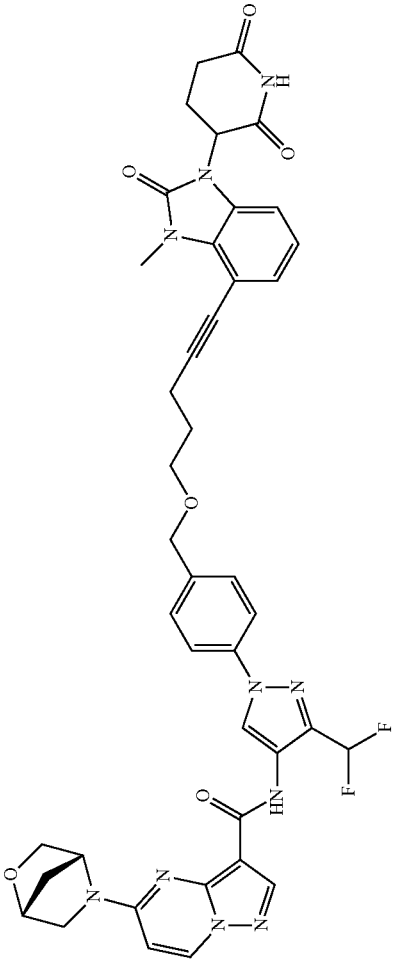 |

TABLE 1-continued
Exemplary Compounds
| I-# | Structure |
|---|---|
| I-499 | 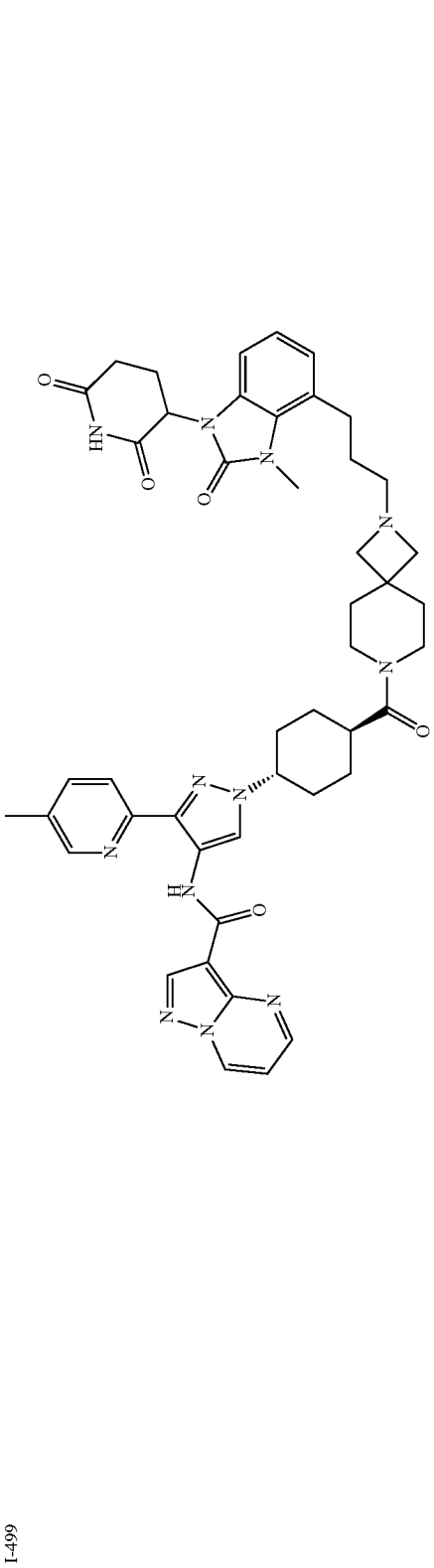 |
| I-500 | 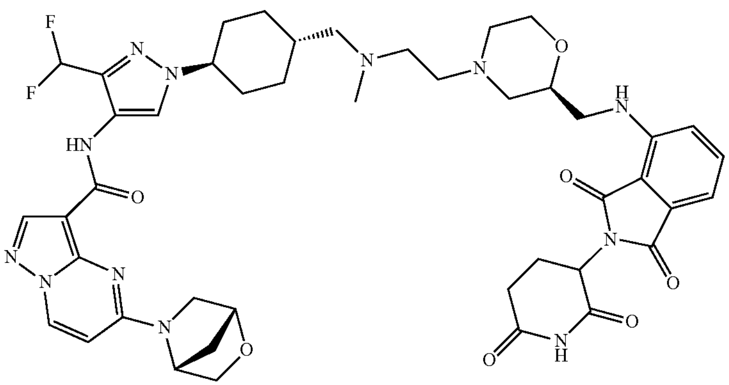 [SMILES: CN(CCN1CCO[C@@H](CNc2cccc3c2C(=O)N(C2CCC(=O)NC2=O)C3=O)C1)C[C@H]1CC[C@H](n2cc(NC(=O)c3cnn4ccc(N5C[C@H]6C[C@@H]5CO6)nc34)c(C(F)F)n2)CC1] |

TABLE 1-continued
Exemplary Compounds
| I-# | Structure |
|---|---|
| I-501 | 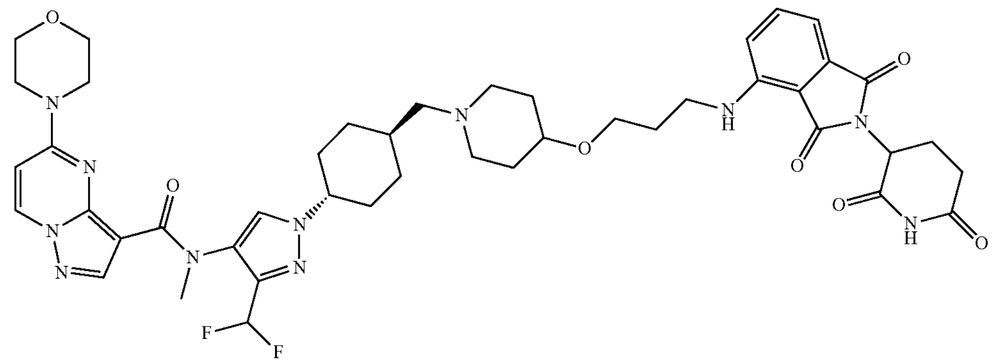 [SMILES: CN(C(=O)c1cnn2ccc(N3CCOCC3)nc12)c1cn([C@H]2CC[C@H](CN3CCC(OCCCNc4cccc5c4C(=O)N(C4CCC(=O)NC4=O)C5=O)CC3)CC2)nc1C(F)F] |
| I-502 | 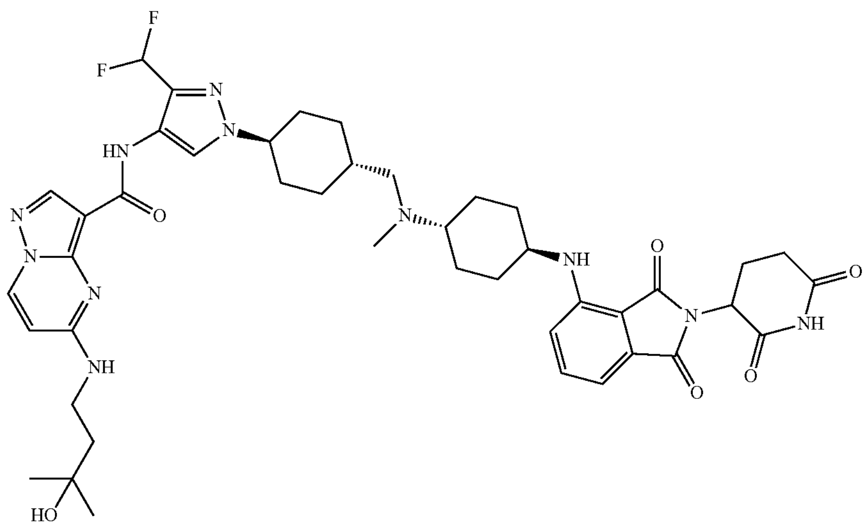 [SMILES: CN(C[C@H]1CC[C@H](n2cc(NC(=O)c3cnn4ccc(NCCC(C)(C)O)nc34)c(C(F)F)n2)CC1)[C@H]1CC[C@H](Nc2cccc3c2C(=O)N(C2CCC(=O)NC2=O)C3=O)CC1] |

TABLE 1-continued
Exemplary Compounds
| I-# | Structure |
|---|---|
| I-503 | 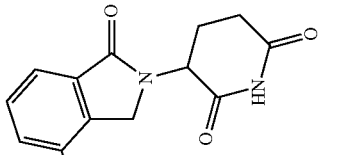 |
| I-504 | 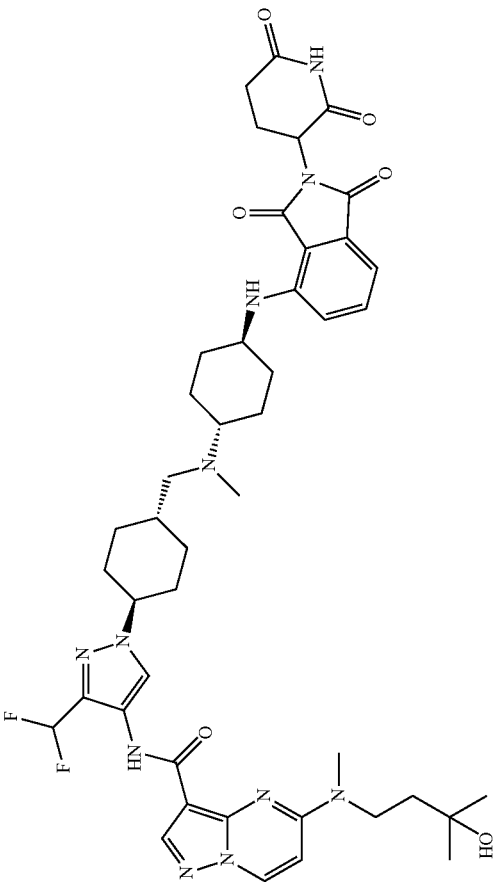 |

TABLE 1-continued
Exemplary Compounds
| I-# | Structure |
|---|---|
| I-505 | 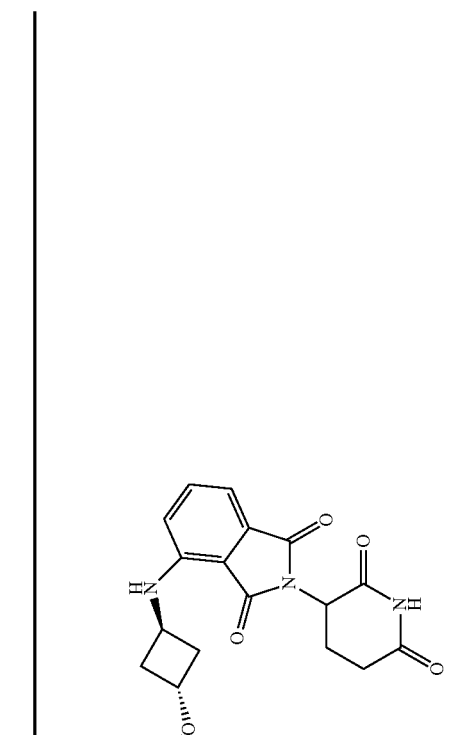 |
| I-506 | 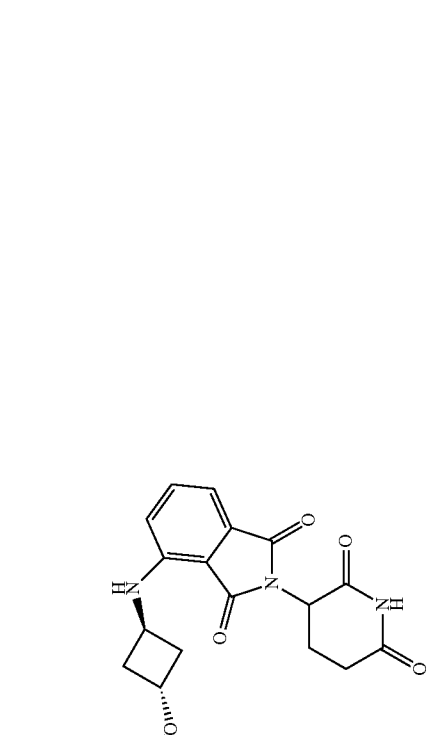 |

TABLE 1-continued

Exemplary Compounds

| I-# | Structure |
|---|---|
| I-507 | 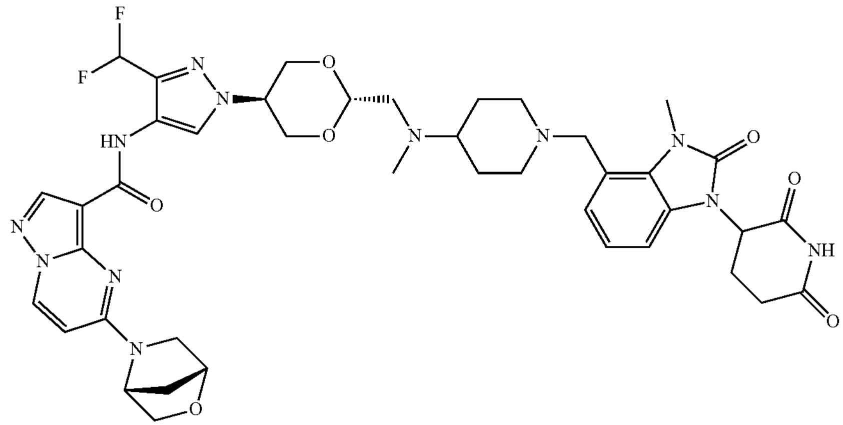 [SMILES: CN(C[C@H]1OC[C@H](n2cc(NC(=O)c3cnn4ccc(N5C[C@H]6C[C@@H]5CO6)nc34)c(C(F)F)n2)CO1)C1CCN(Cc2cccc3c2n(C)c(=O)n3C2CCC(=O)NC2=O)CC1] |
| I-508 | 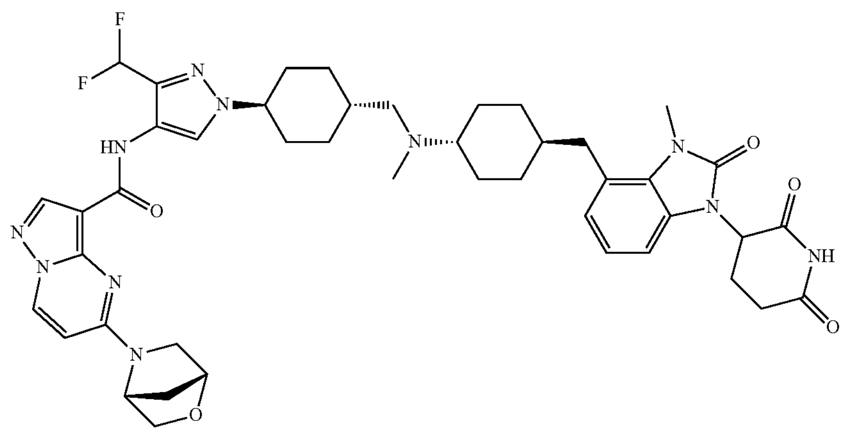 [SMILES: Cn1c(=O)n(C2CCC(=O)NC2=O)c2cccc(C[C@H]3CC[C@H](N(C)C[C@H]4CC[C@H](n5cc(NC(=O)c6cnn7ccc(N8C[C@H]9C[C@@H]8CO9)nc67)c(C(F)F)n5)CC4)CC3)c21] |

TABLE 1-continued
Exemplary Compounds
| I-# | Structure |
|---|---|
| I-509 | 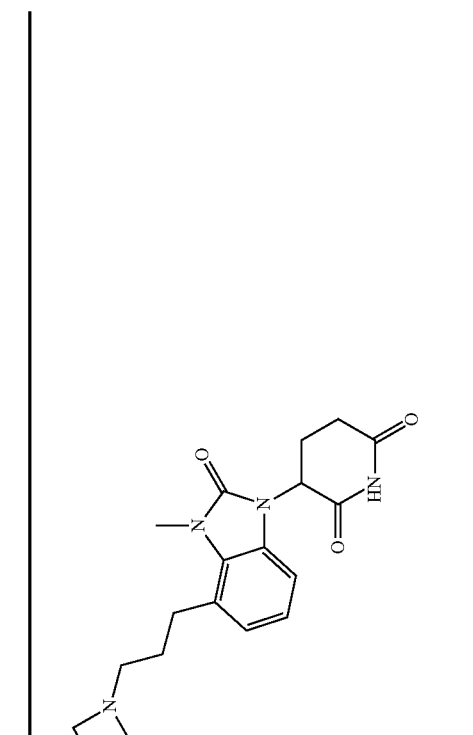 |
| I-510 | 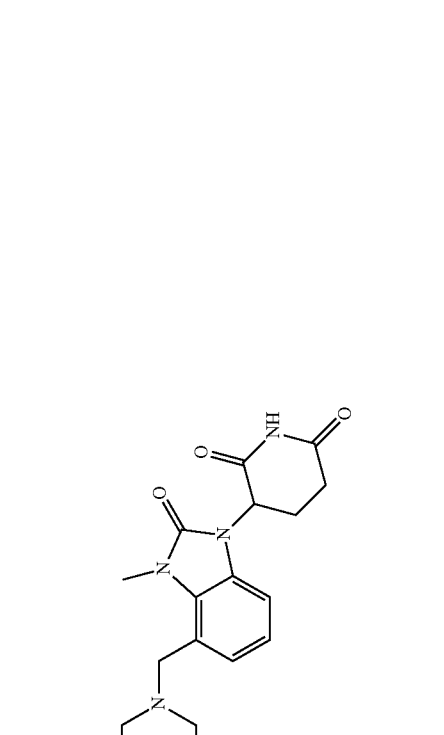 |

TABLE 1-continued
Exemplary Compounds
| I-# | Structure |
|---|---|
| I-511 | 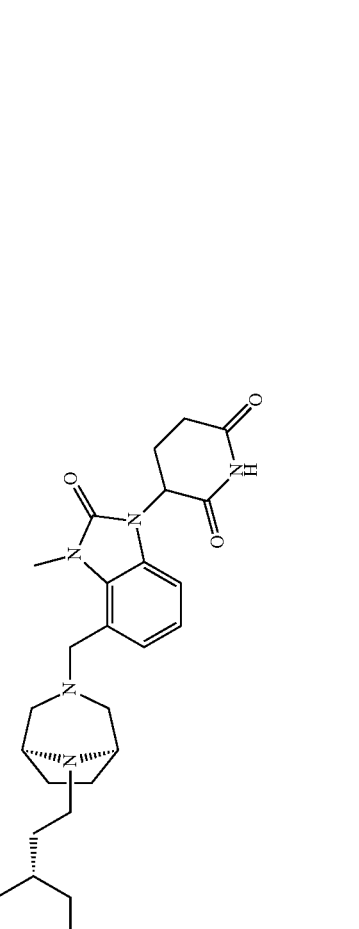 |
| I-512 | 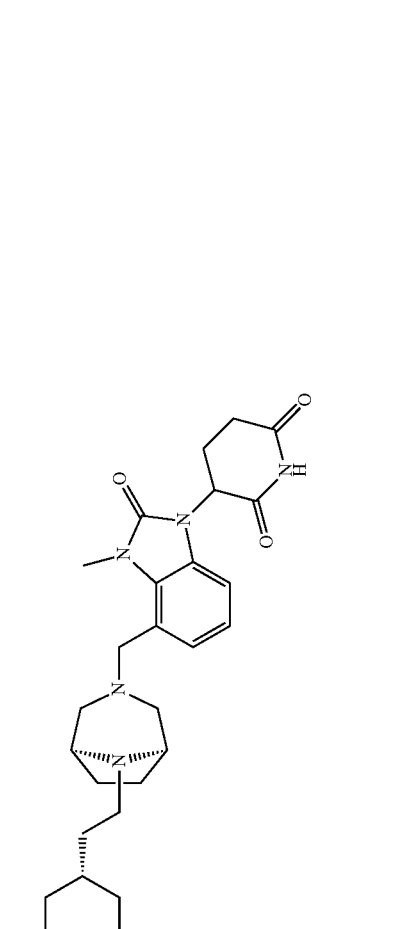 |

TABLE 1-continued
Exemplary Compounds
| I-# | Structure |
|---|---|
| I-513 | 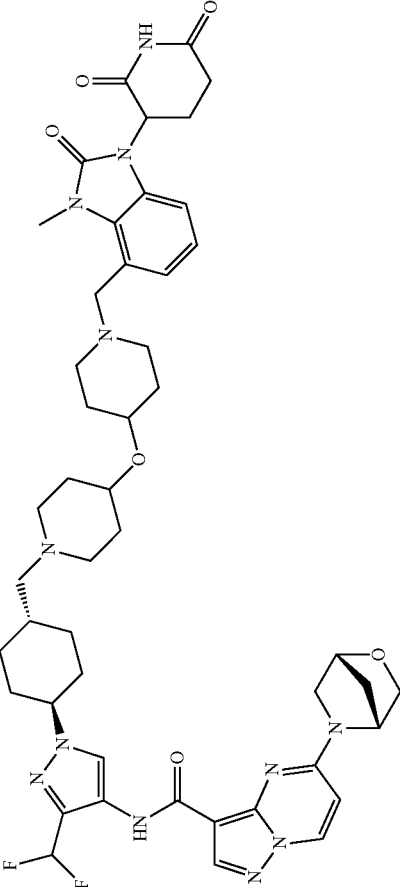 |
| I-514 | 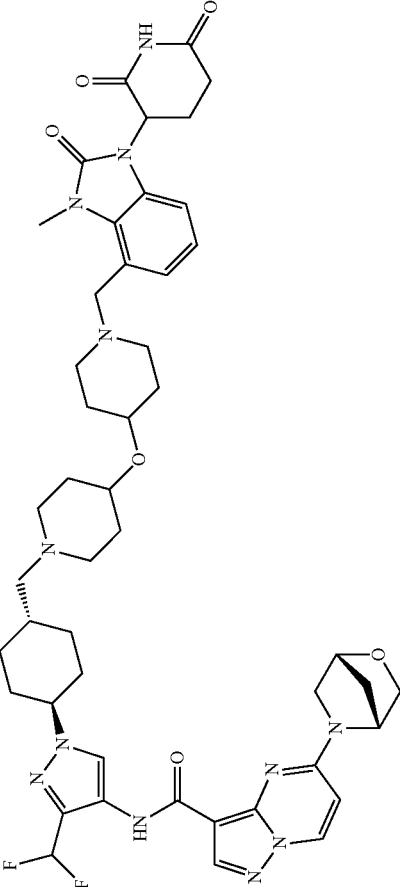 |

TABLE 1-continued

Exemplary Compounds

| I-# | Structure |
|---|---|
| I-515 | 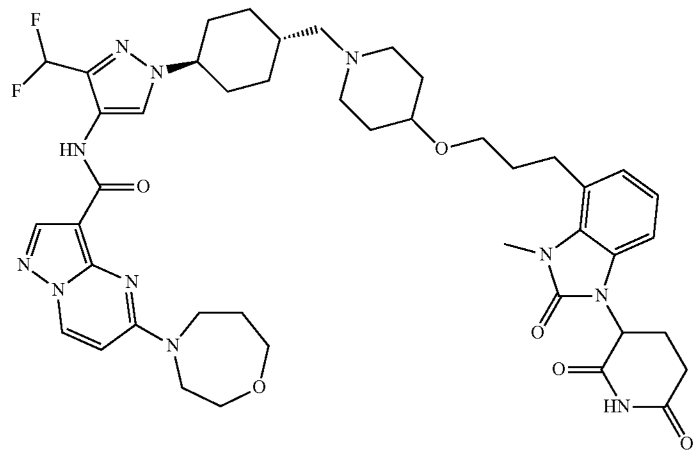 [SMILES: Cn1c(=O)n(C2CCC(=O)NC2=O)c2cccc(CCCOC3CCN(C[C@H]4CC[C@H](n5cc(NC(=O)c6cnn7ccc(N8CCCOCC8)nc67)c(C(F)F)n5)CC4)CC3)c21] |
| I-516 | 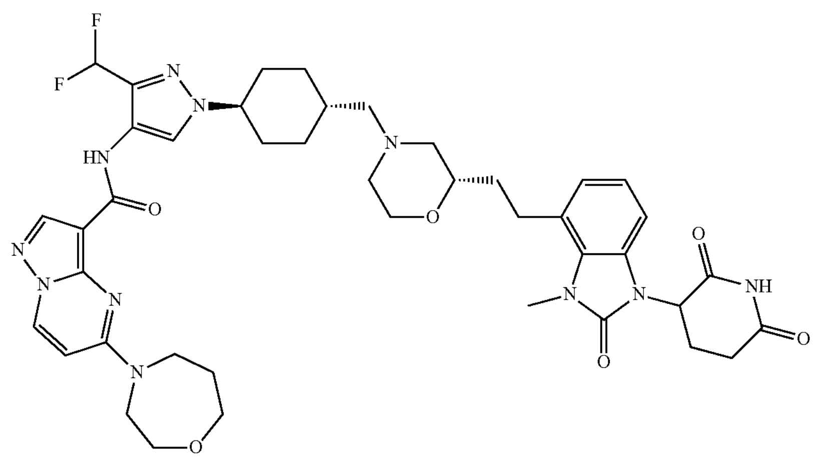 [SMILES: Cn1c(=O)n(C2CCC(=O)NC2=O)c2cccc(CC[C@H]3CN(C[C@H]4CC[C@H](n5cc(NC(=O)c6cnn7ccc(N8CCCOCC8)nc67)c(C(F)F)n5)CC4)CCO3)c21] |

TABLE 1-continued
Exemplary Compounds
| I-# | Structure |
|---|---|
| I-517 | 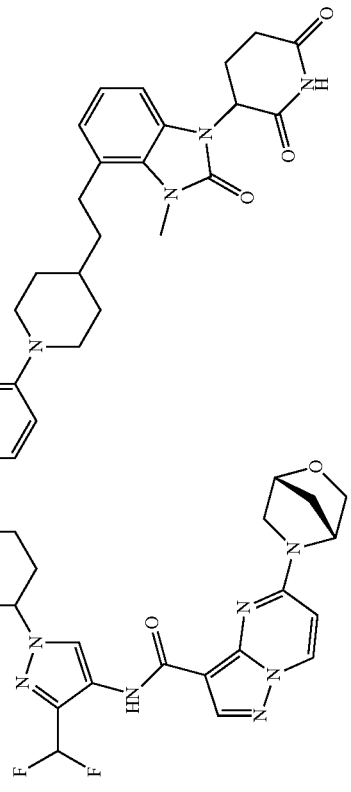 |
| I-518 | 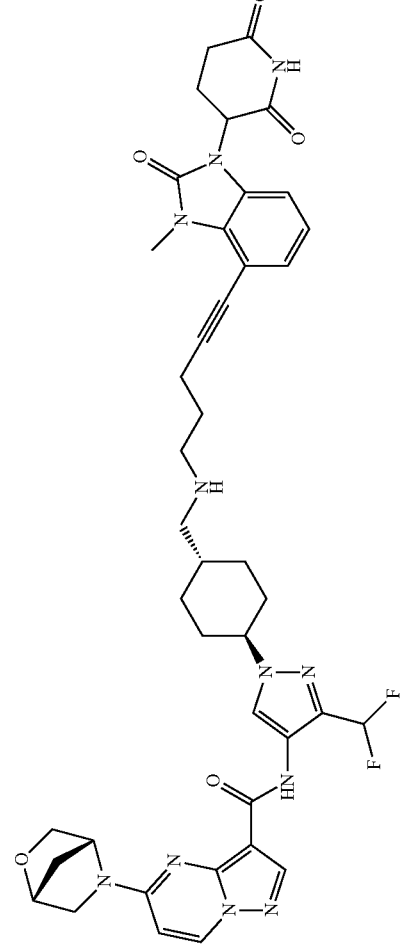 |

TABLE 1-continued
Exemplary Compounds
| I-# | Structure |
|---|---|
| I-519 | 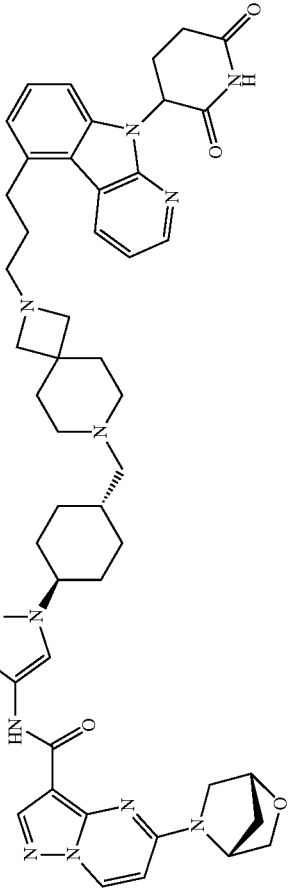 |
| I-520 | 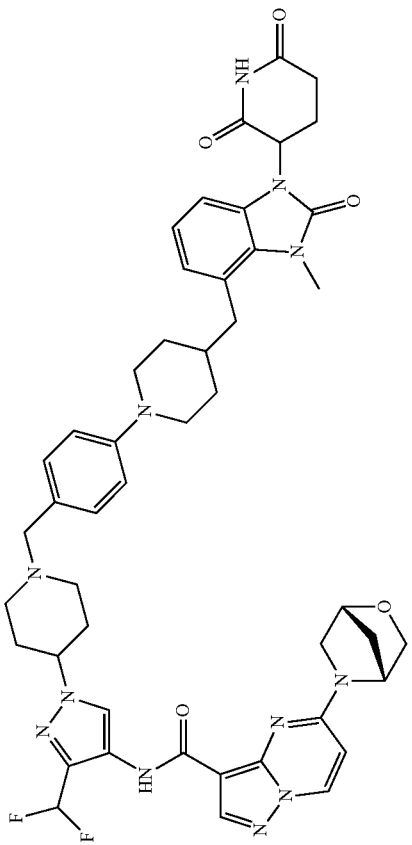 |

TABLE 1-continued
Exemplary Compounds
| I-# | Structure |
|---|---|
| I-521 | 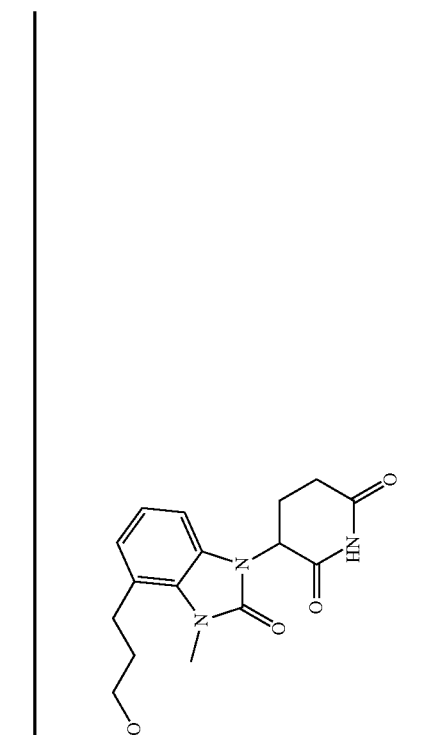 |
| I-522 | 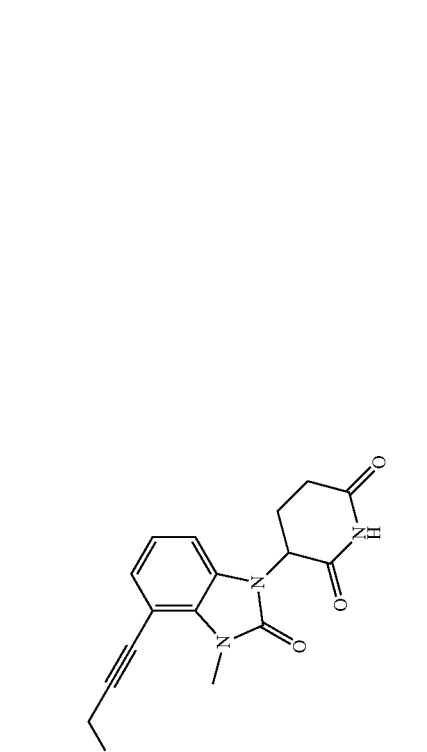 |

TABLE 1-continued
Exemplary Compounds
| I-# | Structure |
|---|---|
| I-523 | 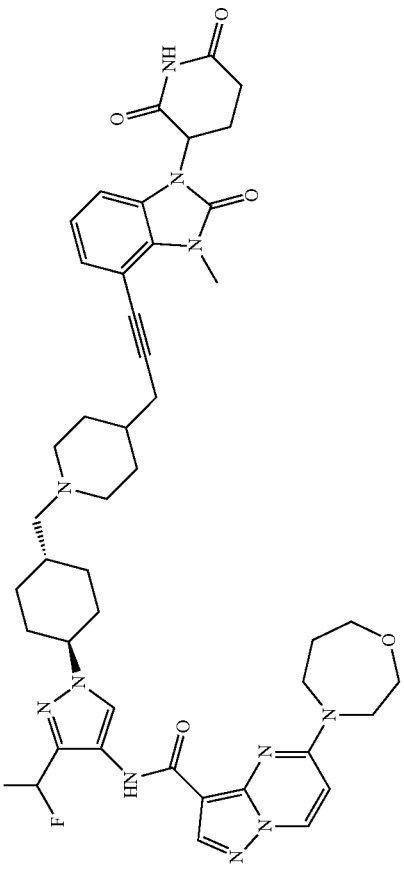 |
| I-524 | 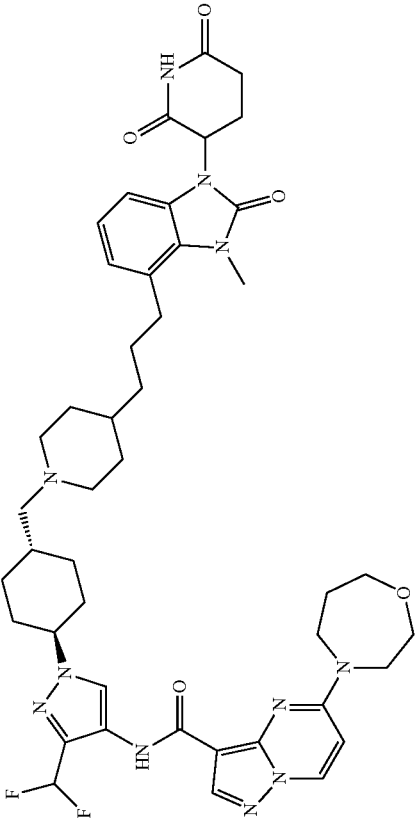 |

TABLE 1-continued
Exemplary Compounds
| I-# | Structure |
|---|---|
| I-525 | 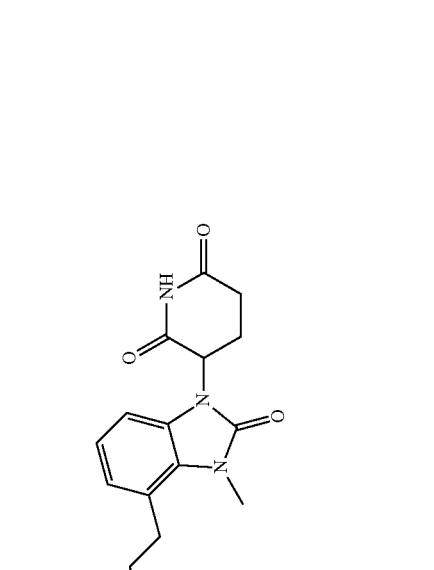 |
| I-526 | 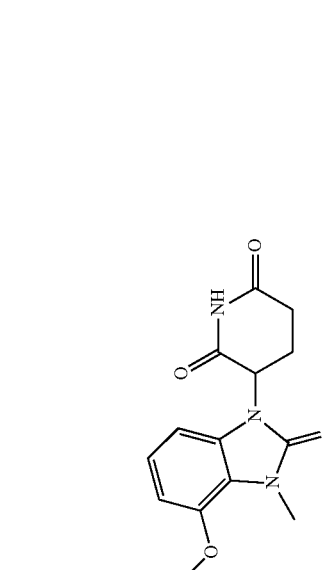 |

TABLE 1-continued
Exemplary Compounds
| I-# | Structure |
|---|---|
| I-527 | 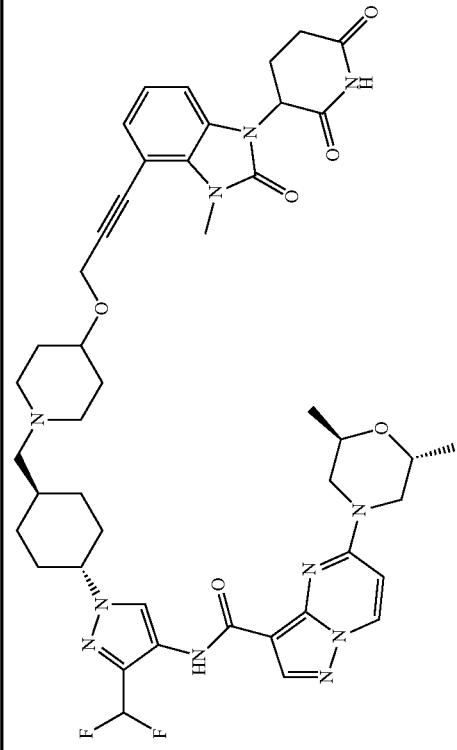 |
| I-528 | 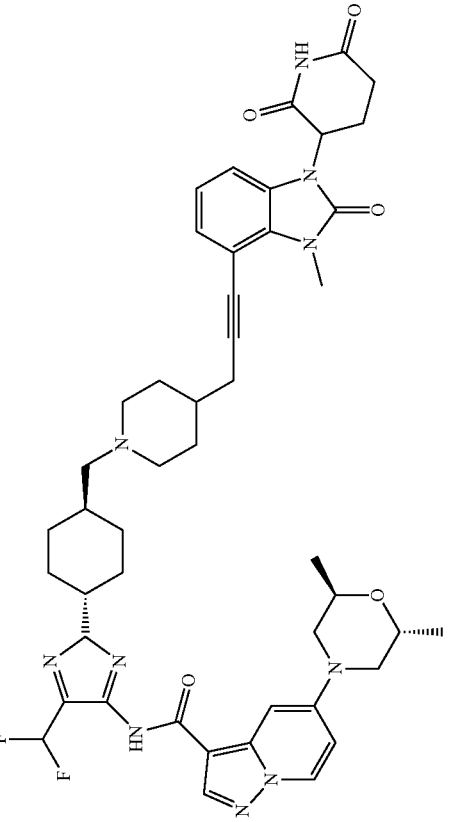 |

TABLE 1-continued
Exemplary Compounds
| I-# | Structure |
|---|---|
| I-530 | 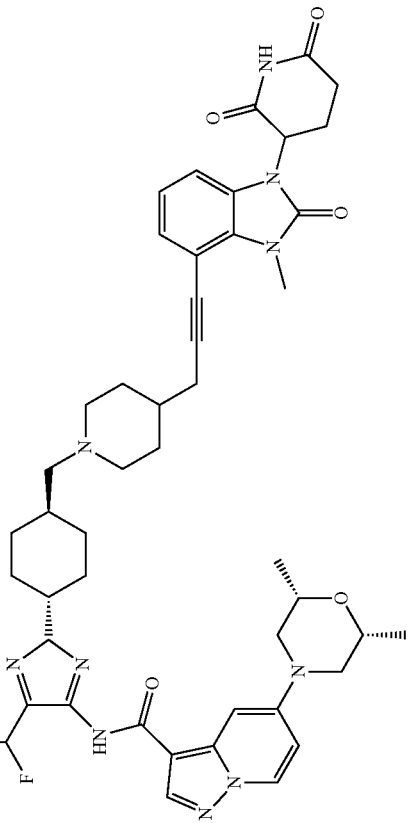 |
| I-531 | 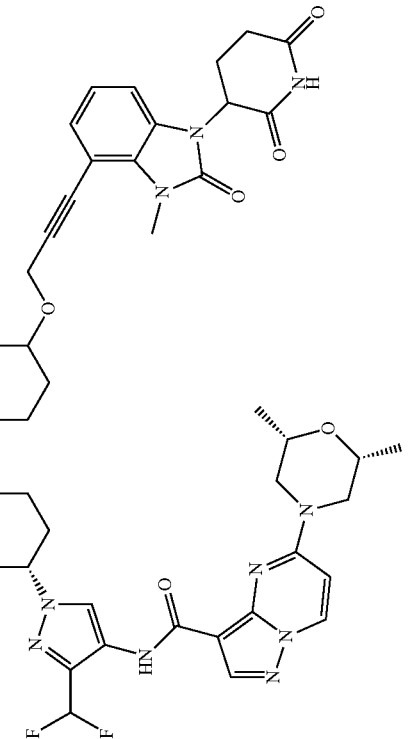 |

TABLE 1-continued
Exemplary Compounds
| I-# | Structure |
|---|---|
| I-532 | 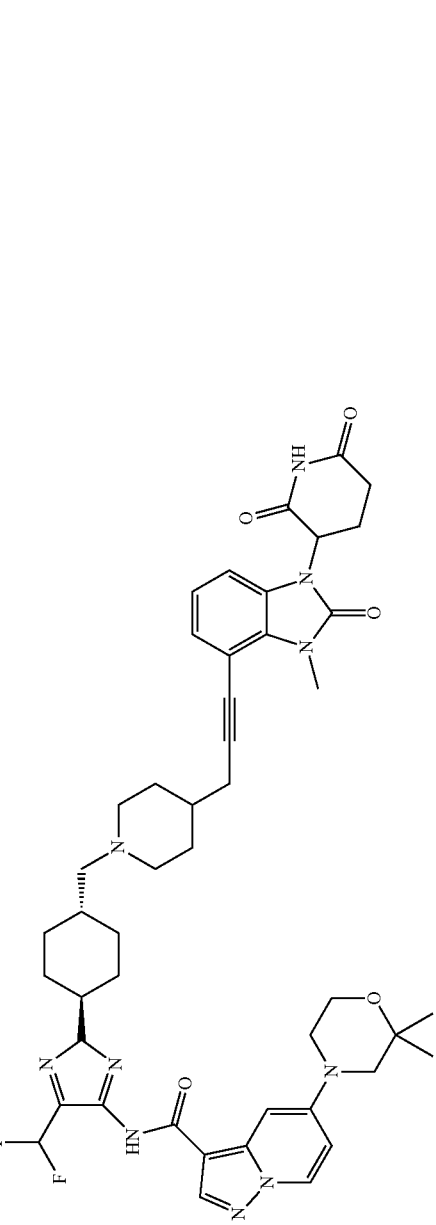 |
| I-533 | 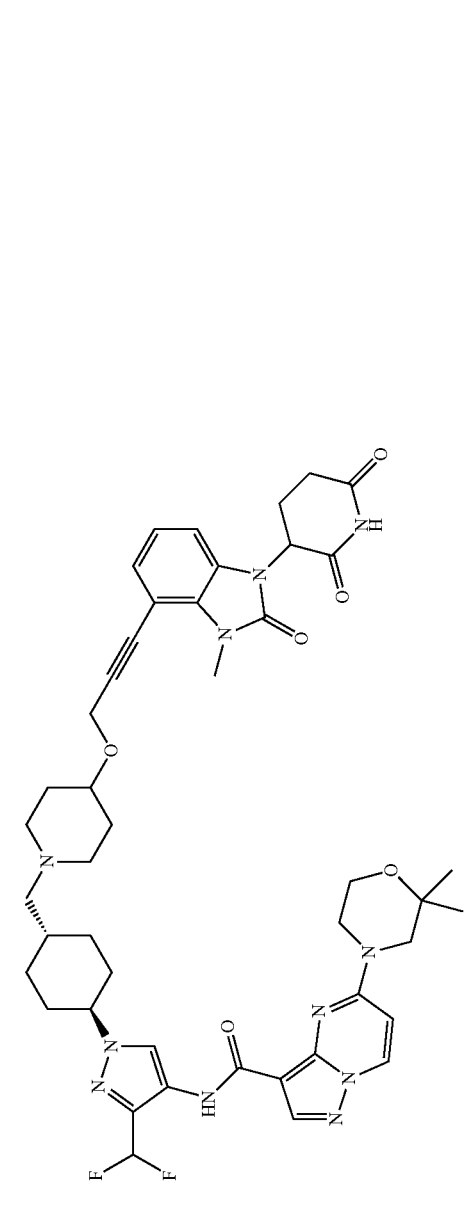 |

TABLE 1-continued
Exemplary Compounds
| I-# | Structure |
|---|---|
| I-534 | 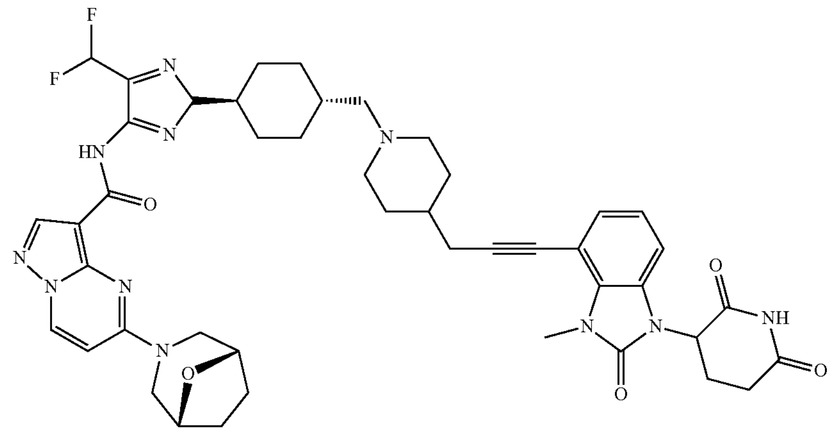 [SMILES: Cn1c(=O)n(C2CCC(=O)NC2=O)c2cccc(C#CCC3CCN(C[C@H]4CC[C@H](C5N=C(NC(=O)c6cnn7ccc(N8C[C@H]9CC[C@@H](C8)O9)nc67)C(C(F)F)=N5)CC4)CC3)c21] |
| I-535 | 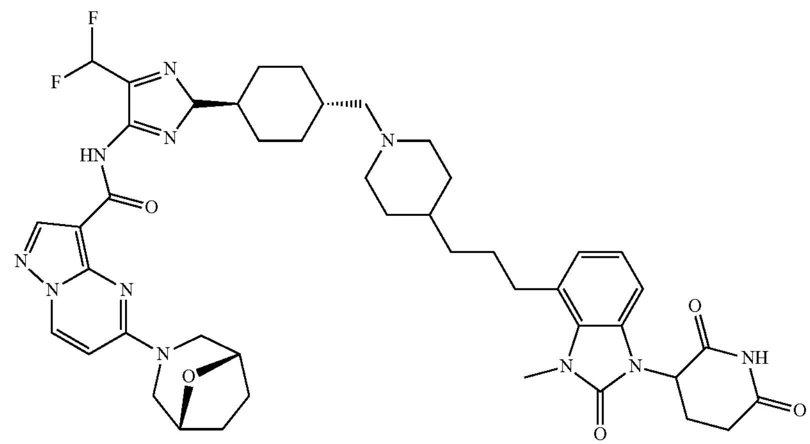 [SMILES: Cn1c(=O)n(C2CCC(=O)NC2=O)c2cccc(CCCC3CCN(C[C@H]4CC[C@H](C5N=C(NC(=O)c6cnn7ccc(N8C[C@H]9CC[C@@H](C8)O9)nc67)C(C(F)F)=N5)CC4)CC3)c21] |
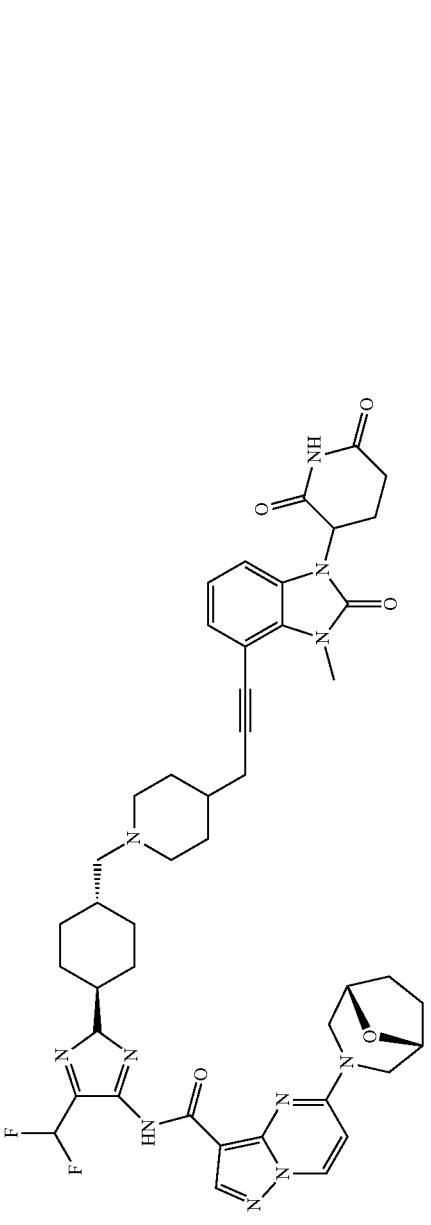

TABLE 1-continued
Exemplary Compounds
| I-# | Structure |
|---|---|
| I-536 | 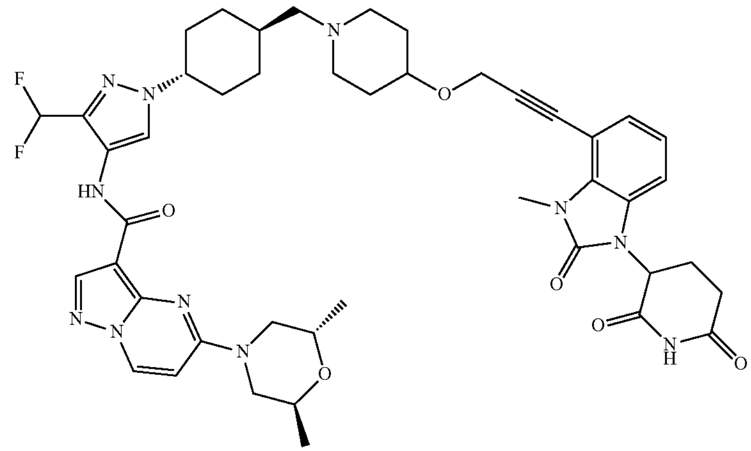 [SMILES: C[C@H]1CN(c2ccn3ncc(C(=O)Nc4cn([C@H]5CC[C@H](CN6CCC(OCC#Cc7cccc8c7n(C)c(=O)n8C7CCC(=O)NC7=O)CC6)CC5)nc4C(F)F)c3n2)C[C@H](C)O1] |
| I-537 | 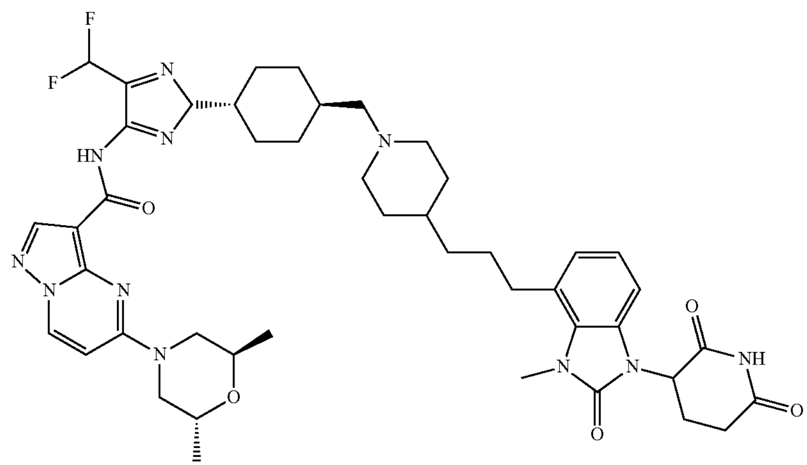 [SMILES: C[C@@H]1CN(c2ccn3ncc(C(=O)NC4=NC([C@H]5CC[C@H](CN6CCC(CCCc7cccc8c7n(C)c(=O)n8C7CCC(=O)NC7=O)CC6)CC5)N=C4C(F)F)c3n2)C[C@@H](C)O1] |

TABLE 1-continued
Exemplary Compounds
| I-# | Structure |
|---|---|
| I-538 | 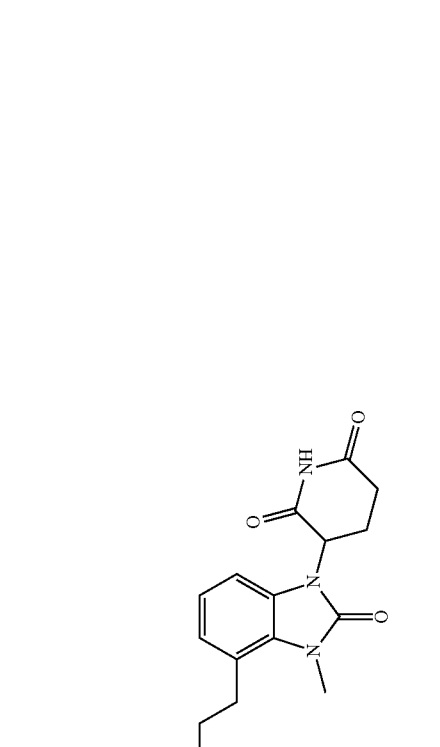 |
| I-539 | 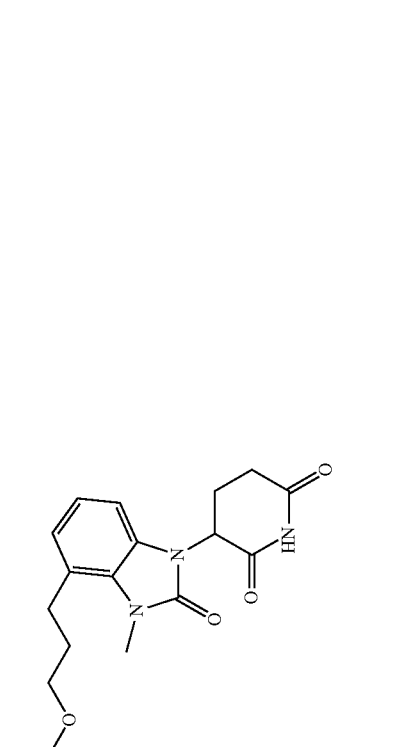 |

TABLE 1-continued
Exemplary Compounds
| I-# | Structure |
|---|---|
| I-540 | 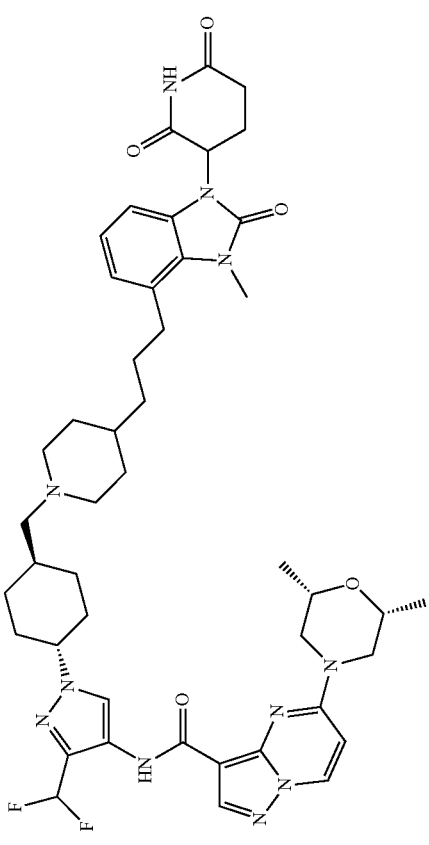 |
| I-541 | 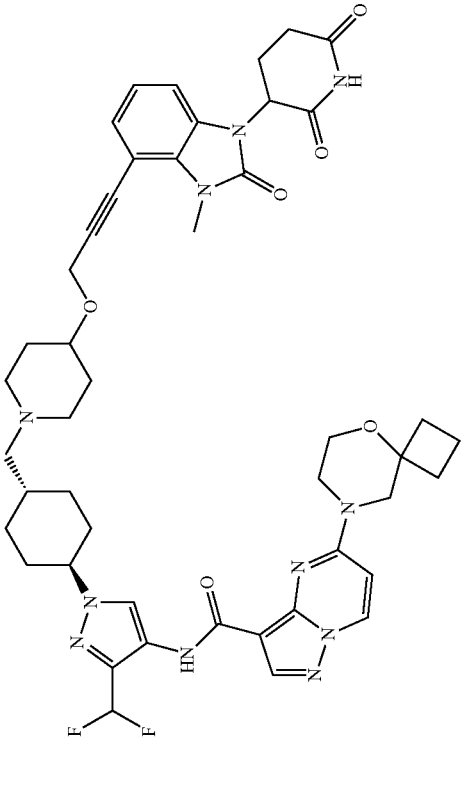 |

TABLE 1-continued
Exemplary Compounds
| I-# | Structure |
|---|---|
| I-542 | 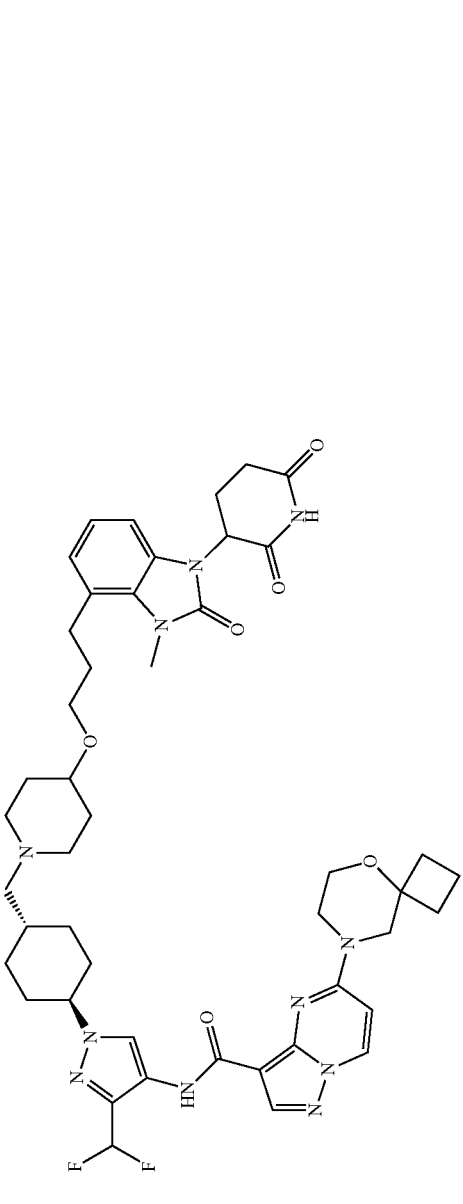 |
| I-543 | 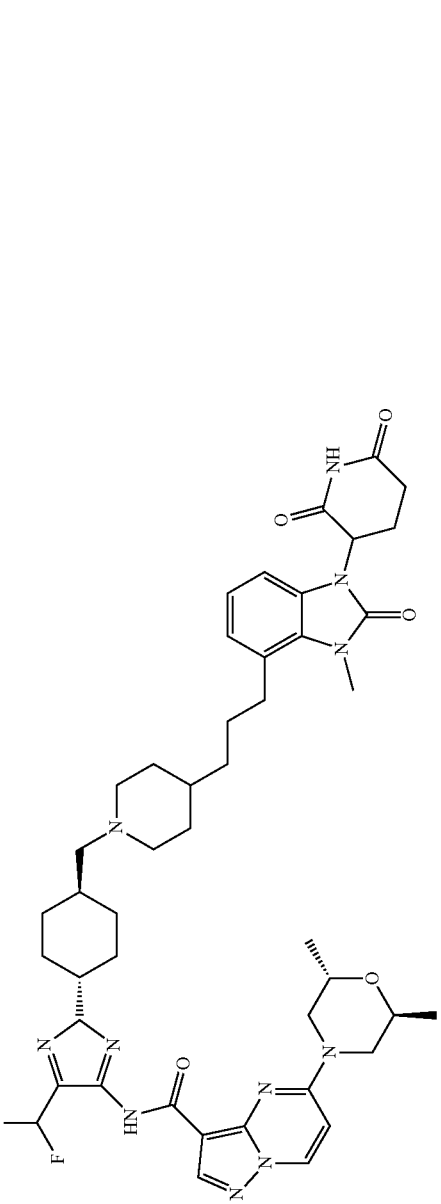 |

TABLE 1-continued
Exemplary Compounds
| I-# | Structure |
|---|---|
| I-544 | 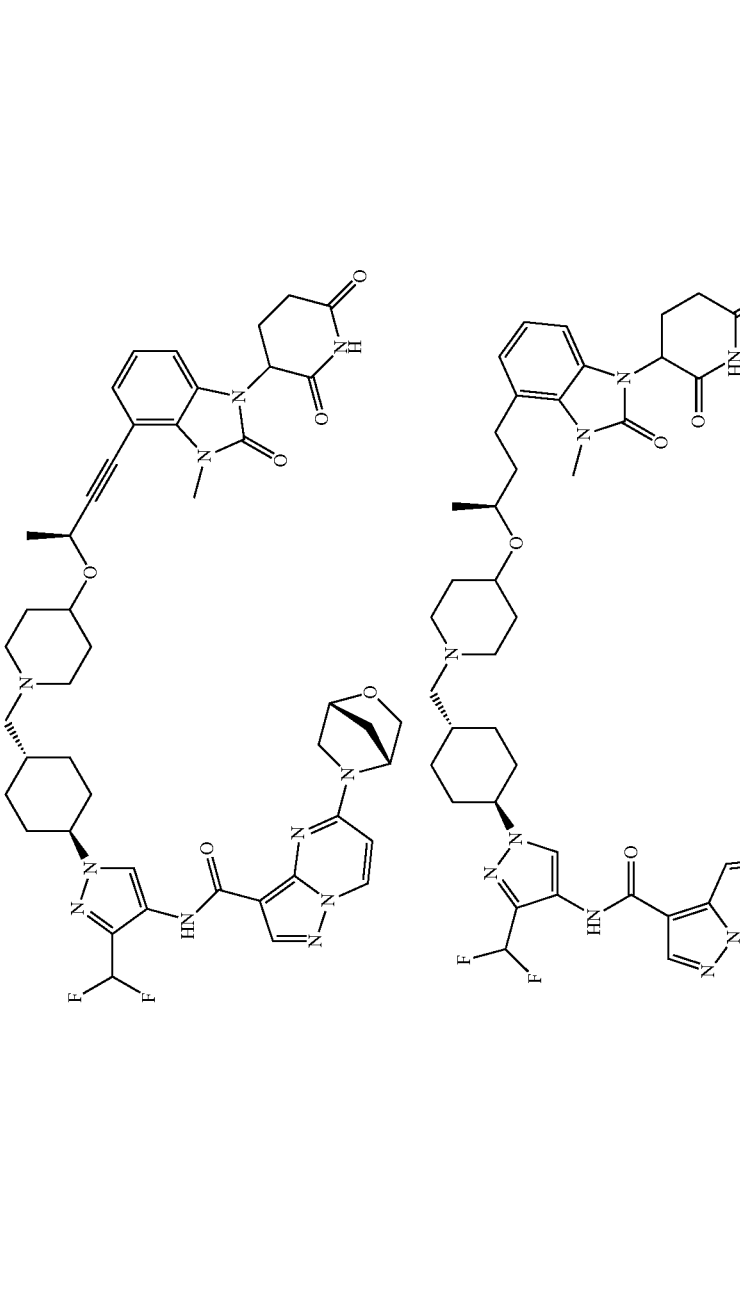 |
| I-545 | 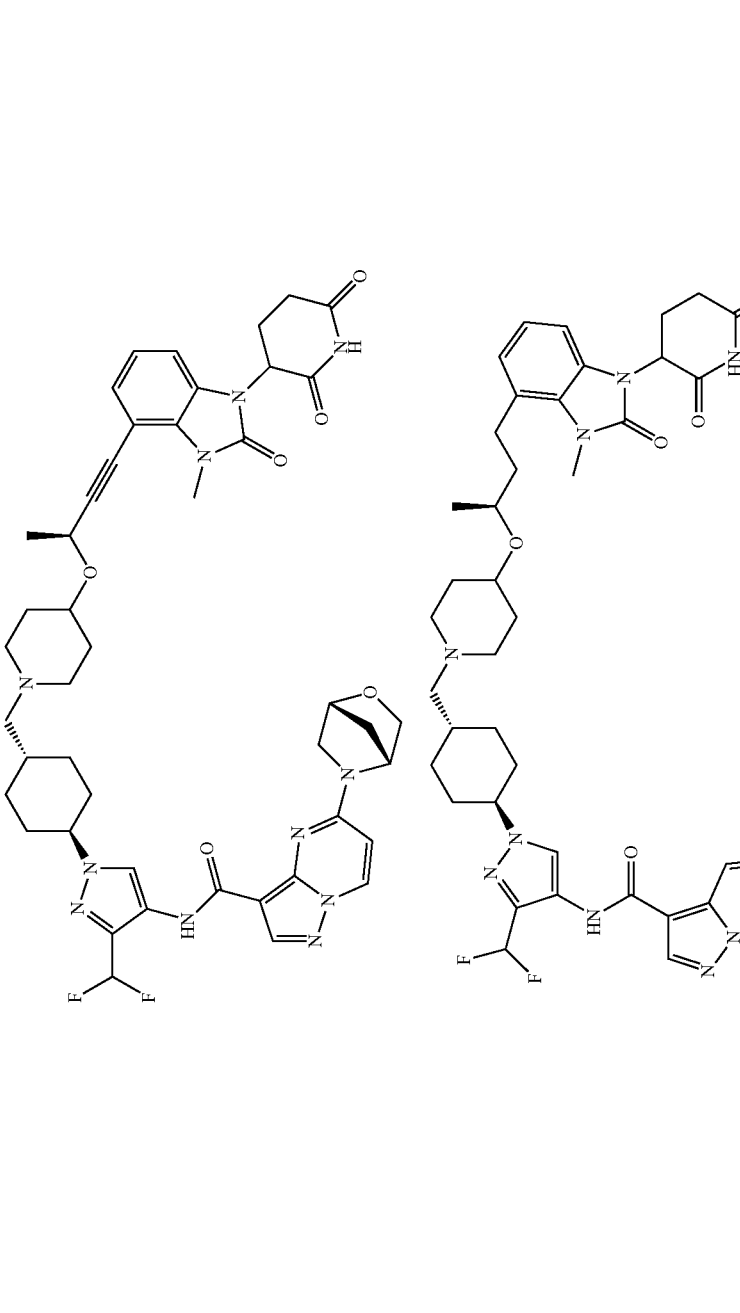 |

TABLE 1-continued
Exemplary Compounds
| I-# | Structure |
|---|---|
| I-546 | 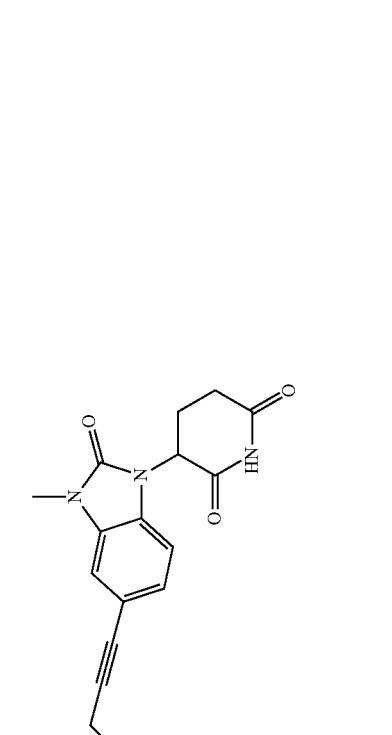 |
| I-547 | 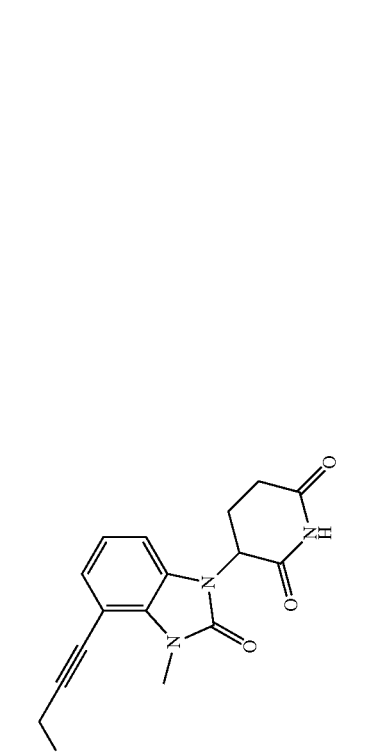 |

TABLE 1-continued
Exemplary Compounds
| I-# | Structure |
|---|---|
| I-548 | 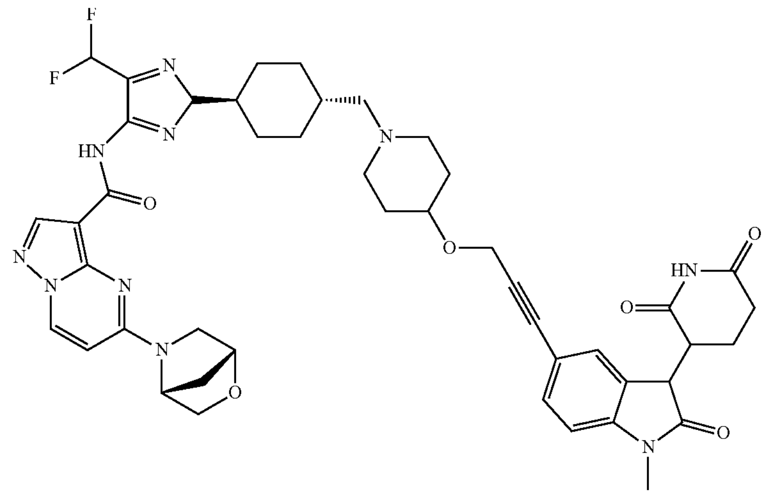 [SMILES: CN1C(=O)C(C2CCC(=O)NC2=O)c2cc(C#CCOC3CCN(C[C@H]4CC[C@H](C5N=C(NC(=O)c6cnn7ccc(N8C[C@H]9C[C@@H]8CO9)nc67)C(C(F)F)=N5)CC4)CC3)ccc21] |
| I-549 | 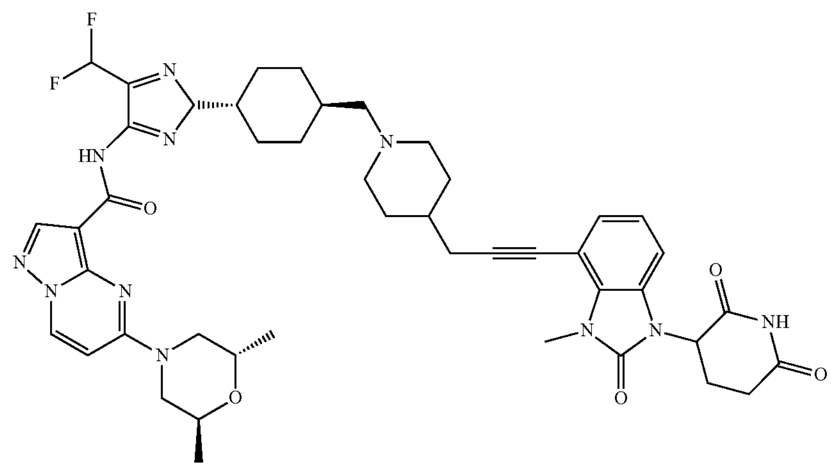 [SMILES: C[C@H]1CN(c2ccn3ncc(C(=O)NC4=NC([C@H]5CC[C@H](CN6CCC(CC#Cc7cccc8c7n(C)c(=O)n8C7CCC(=O)NC7=O)CC6)CC5)N=C4C(F)F)c3n2)C[C@H](C)O1] |

TABLE 1-continued

Exemplary Compounds

| I-# | Structure |
|---|---|
| I-550 | 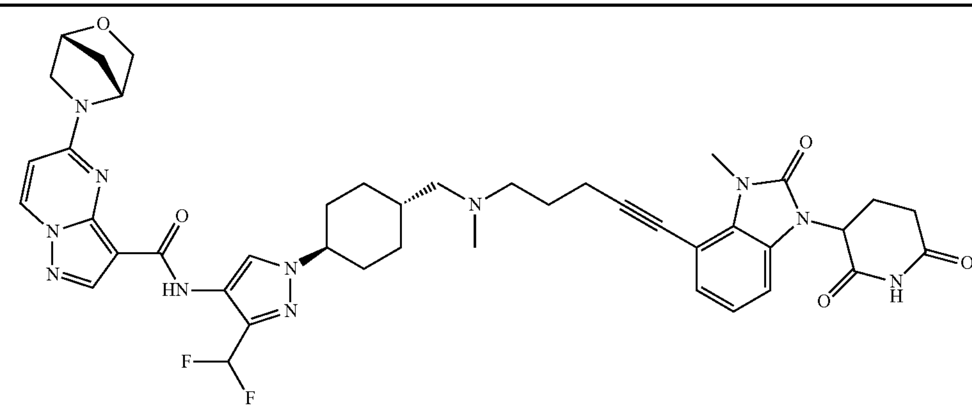 |
| I-551 | 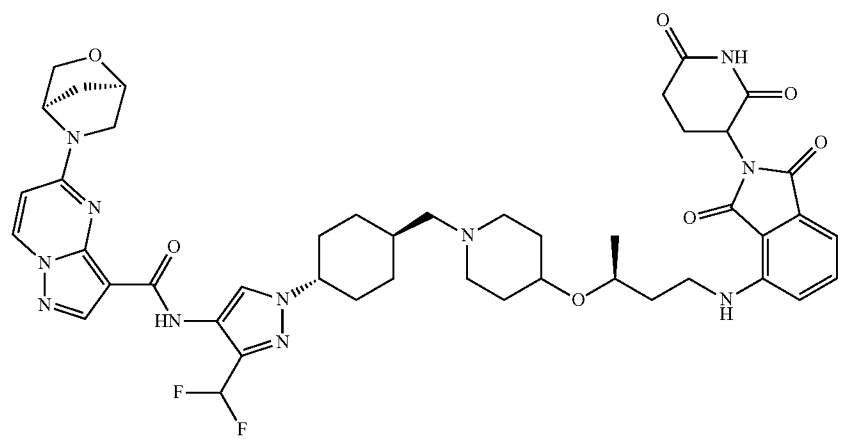 [SMILES: C[C@@H](CCNc1cccc2c1C(=O)N(C1CCC(=O)NC1=O)C2=O)OC1CCN(C[C@H]2CC[C@H](n3cc(NC(=O)c4cnn5ccc(N6C[C@H]7C[C@@H]6CO7)nc45)c(C(F)F)n3)CC2)CC1] |

TABLE 1-continued
Exemplary Compounds
| I-# | Structure |
|---|---|
| I-552 | 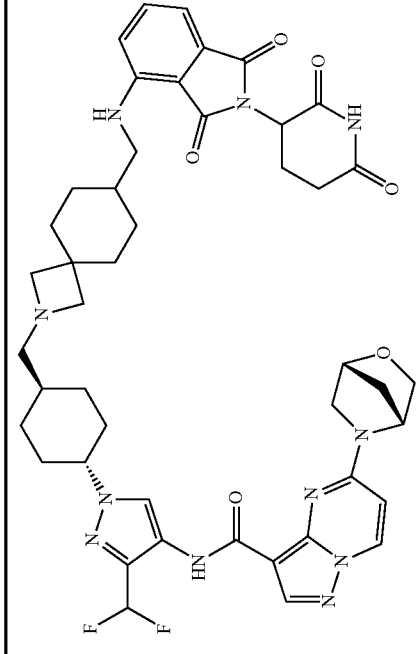 |
| I-553 | 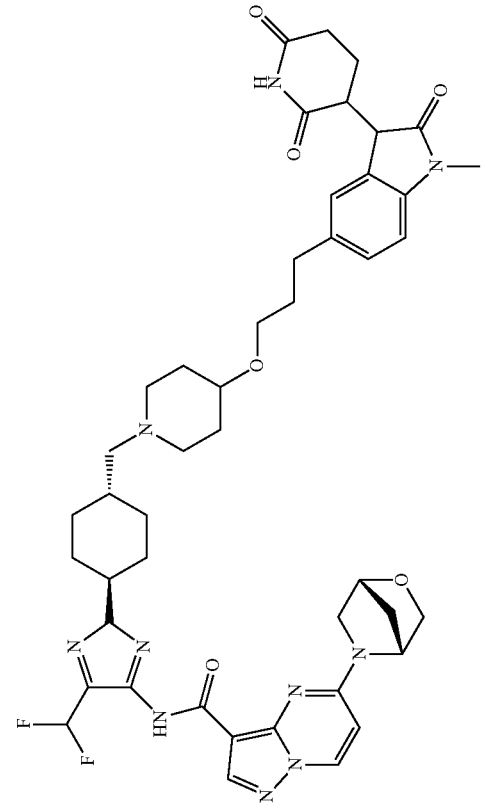 |

TABLE 1-continued
Exemplary Compounds
| I-# | Structure |
|---|---|
| I-554 | 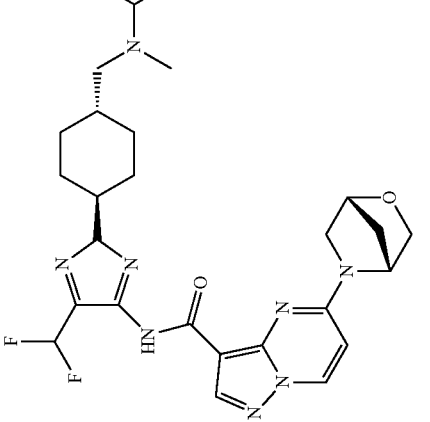 |
| I-555 | 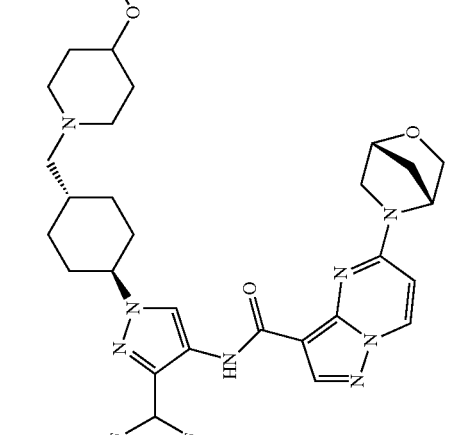 |

TABLE 1-continued
Exemplary Compounds
| I-# | Structure |
|---|---|
| I-556 | 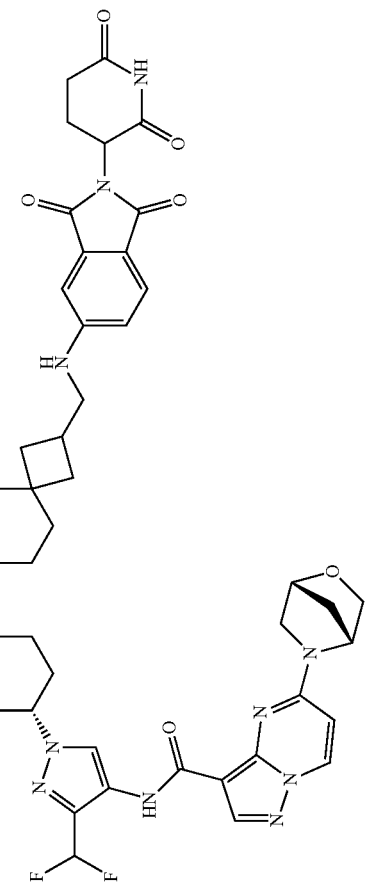 |
| I-557 | 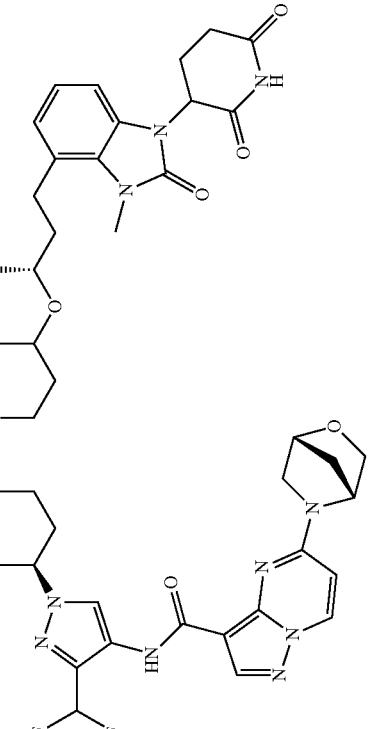 |

TABLE 1-continued
Exemplary Compounds
| I-# | Structure |
|---|---|
| I-558 | 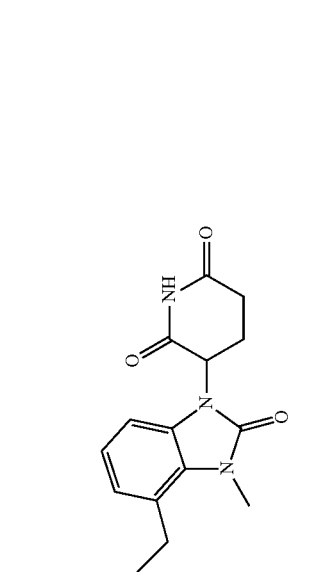 |
| I-559 | 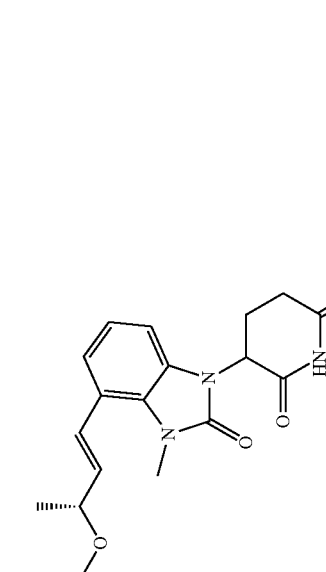 |

TABLE 1-continued
Exemplary Compounds
| I-# | Structure |
|---|---|
| I-560 | 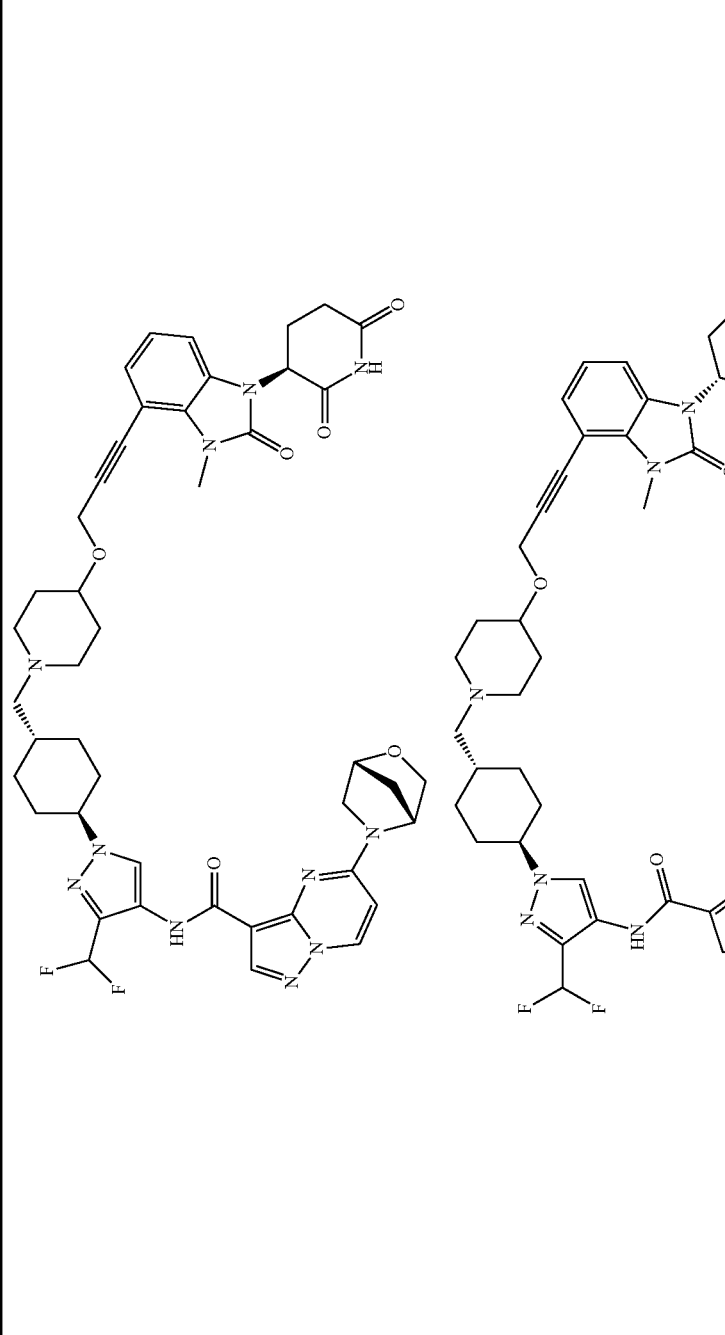 |
| I-561 | 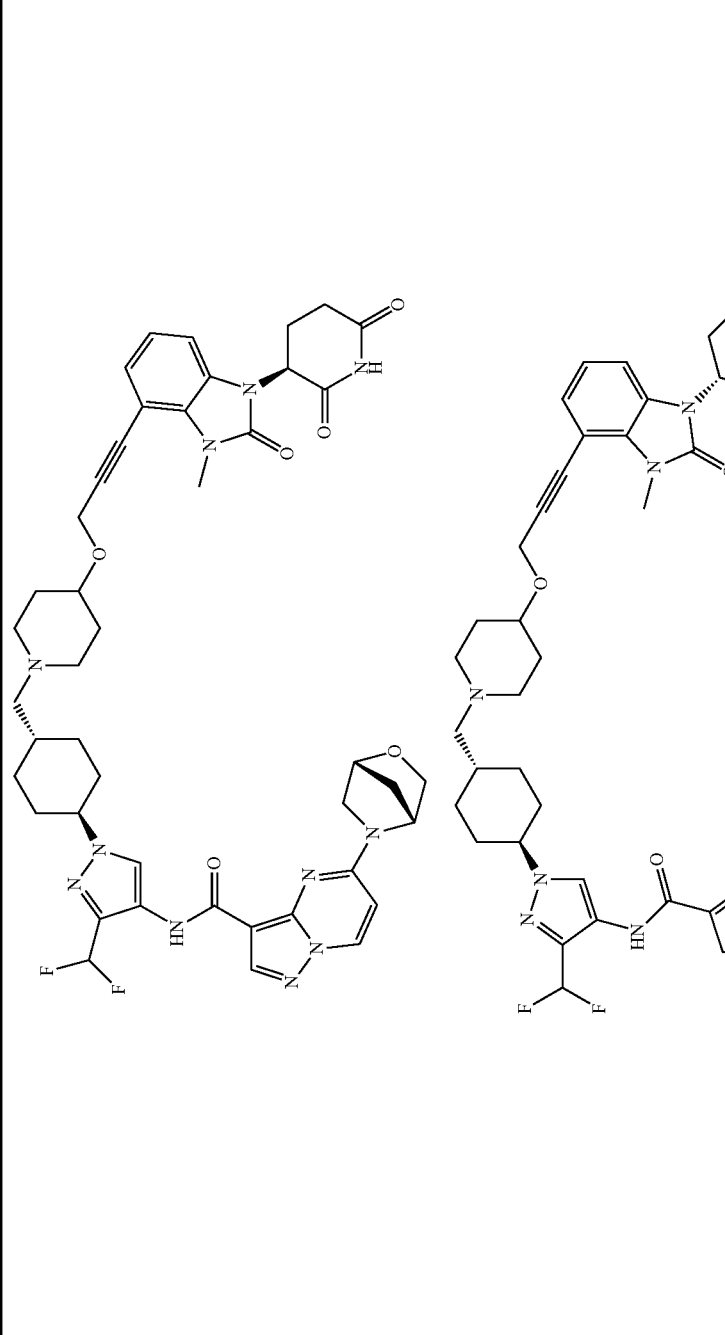 |

TABLE 1-continued
Exemplary Compounds
| I-# | Structure |
|---|---|
| I-562 | 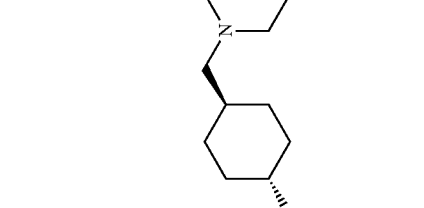 |
| I-563 | 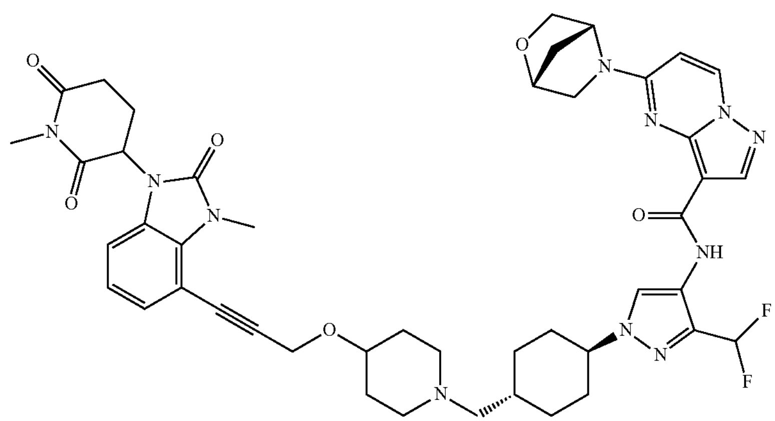 [SMILES: CN1C(=O)CCC(n2c(=O)n(C)c3c(C#CCOC4CCN(C[C@H]5CC[C@H](n6cc(NC(=O)c7cnn8ccc(N9C[C@H]%10C[C@@H]9CO%10)nc78)c(C(F)F)n6)CC5)CC4)cccc32)C1=O] |

In some embodiments, the present invention provides a compound as depicted in Table 1, above, or a pharmaceutically acceptable salt thereof.

In some embodiments, the present invention provides a compound of formula I, wherein the compound is not any of the compounds depicted in Table 1A, below.

TABLE 1A

| I-# | Structure |
| --- | --- |
| I-99 | 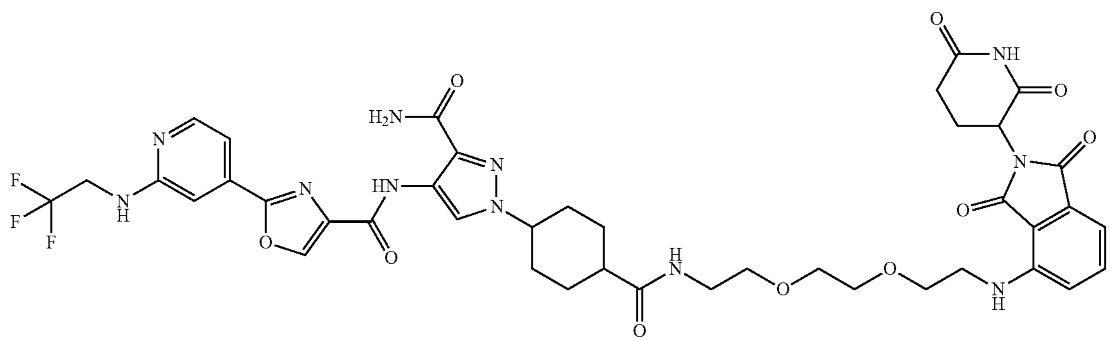 [SMILES: NC(=O)c1nn(C2CCC(C(=O)NCCOCCOCCNc3cccc4c3C(=O)N(C3CCC(=O)NC3=O)C4=O)CC2)cc1NC(=O)c1coc(-c2ccnc(NCC(F)(F)F)c2)n1] |
| I-100 | 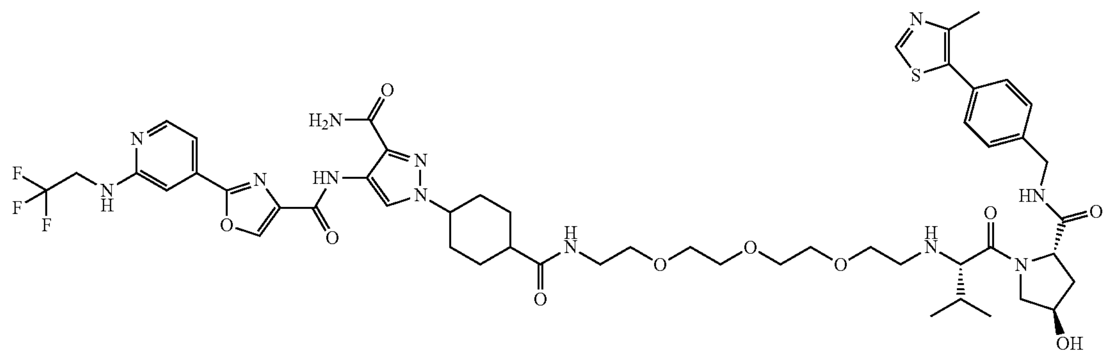 [SMILES: Cc1ncsc1-c1ccc(CNC(=O)[C@@H]2C[C@@H](O)CN2C(=O)[C@@H](NCCOCCOCCOCCNC(=O)C2CCC(n3cc(NC(=O)c4coc(-c5ccnc(NCC(F)(F)F)c5)n4)c(C(N)=O)n3)CC2)C(C)C)cc1] |
| I-101 | 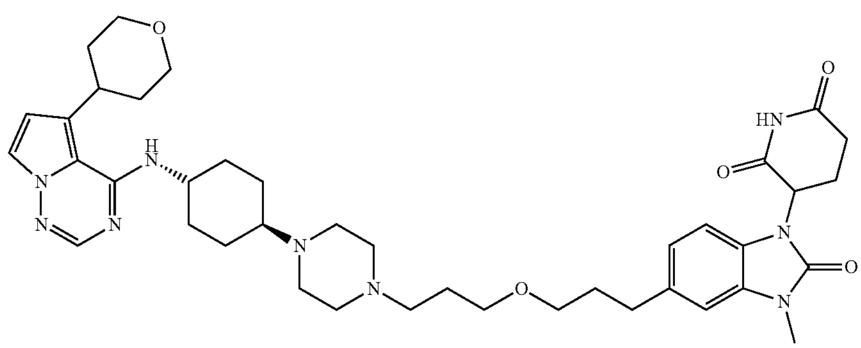 |
| I-102 | 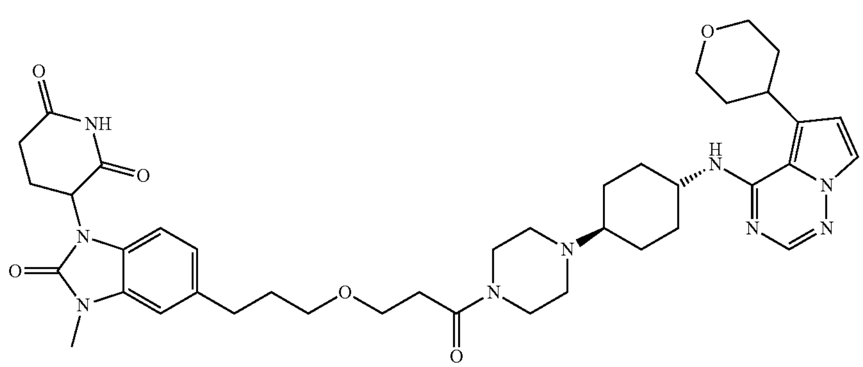 |

TABLE 1A-continued

| I-# | Structure |
|---|---|
| I-103 | 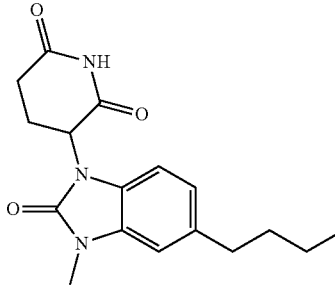 |
| I-104 | 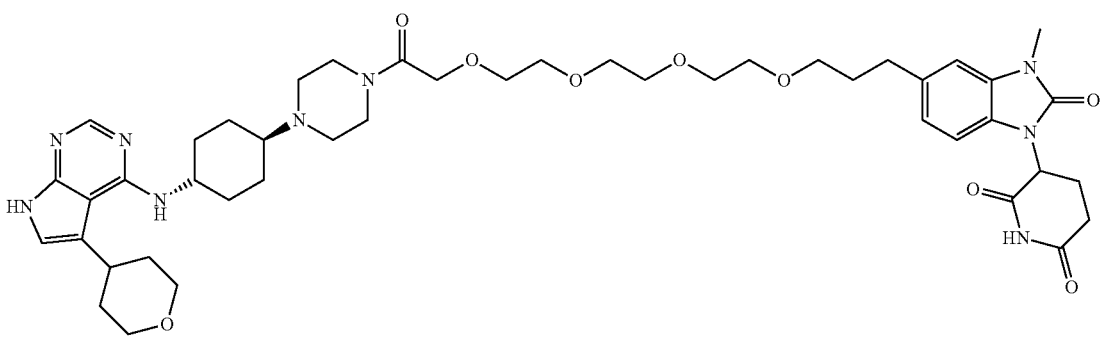 |
| I-105 | 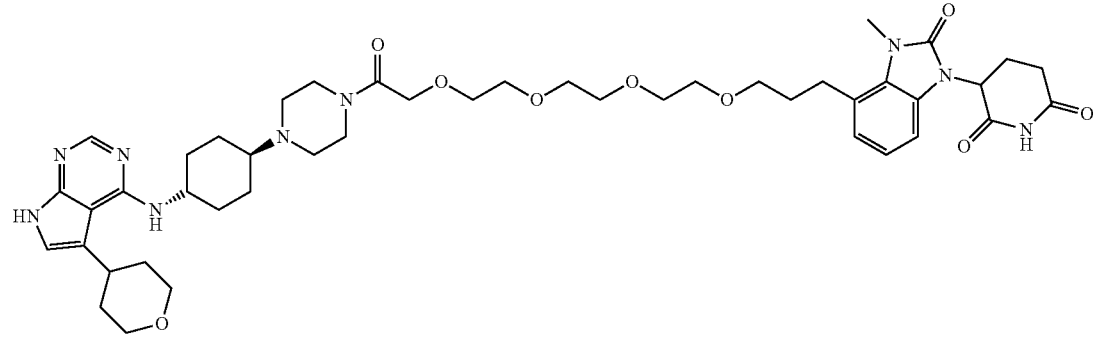 |

In some embodiments, the present invention provides a compound of formula I, wherein the compound is not any of the compounds depicted in Table 1A, above, or a pharmaceutically acceptable salt thereof.

4. General Methods of Providing the Present Compounds

The compounds of this invention may be prepared or isolated in general by synthetic and/or semi-synthetic methods known to those skilled in the art for analogous compounds and by methods described in detail in the Examples, herein.

In the Schemes below, where a particular protecting group, leaving group, or transformation condition is depicted, one of ordinary skill in the art will appreciate that other protecting groups, leaving groups, and transformation conditions are also suitable and are contemplated. Such groups and transformations are described in detail in *March's Advanced Organic Chemistry: Reactions, Mechanisms, and Structure*, M. B. Smith and J. March, 5$^{th}$ Edition, John Wiley & Sons, 2001, *Comprehensive Organic Transformations*, R. C. Larock, 2$^{nd}$ Edition, John Wiley & Sons, 1999, and *Protecting Groups in Organic Synthesis*, T. W. Greene and P. G. M. Wuts, 3$^{rd}$ edition, John Wiley & Sons, 1999, the entirety of each of which is hereby incorporated herein by reference.

As used herein, the phrase "oxygen protecting group" includes, for example, carbonyl protecting groups, hydroxyl protecting groups, etc. Hydroxyl protecting groups are well known in the art and include those described in detail in *Protecting Groups in Organic Synthesis*, T. W. Greene and P. G. M. Wuts, 3$^{rd}$ edition, John Wiley & Sons, 1999, the entirety of each of which is herein incorporated by reference. Examples of suitable hydroxyl protecting groups include, but are not limited to, esters, allyl ethers, ethers, silyl ethers, alkyl ethers, arylalkyl ethers, and alkoxyalkyl ethers. Examples of such esters include formates, acetates, carbonates, and sulfonates. Specific examples include formate, benzoyl formate, chloroacetate, trifluoroacetate, methoxyacetate, triphenylmethoxyacetate, p-chlorophenoxyacetate, 3-phenylpropionate, 4-oxopentanoate, 4,4-(ethylenedithio)

pentanoate, pivaloate (trimethylacetyl), crotonate, 4-methoxy-crotonate, benzoate, p-benylbenzoate, 2,4,6-trimethylbenzoate, carbonates such as methyl, 9-fluorenylmethyl, ethyl, 2,2,2-trichloroethyl, 2-(trimethylsilyl)ethyl, 2-(phenylsulfonyl)ethyl, vinyl, allyl, and p-nitrobenzyl. Examples of such silyl ethers include trimethylsilyl, triethylsilyl, t-butyldimethylsilyl, t-butyldiphenylsilyl, triisopropylsilyl, and other trialkylsilyl ethers. Alkyl ethers include methyl, benzyl, p-methoxybenzyl, 3,4-dimethoxybenzyl, trityl, t-butyl, allyl, and allyloxycarbonyl ethers or derivatives. Alkoxyalkyl ethers include acetals such as methoxymethyl, methylthiomethyl, (2-methoxyethoxy)methyl, benzyloxymethyl, beta-(trimethylsilyl)ethoxymethyl, and tetrahydropyranyl ethers. Examples of arylalkyl ethers include benzyl, p-methoxybenzyl (MPM), 3,4-dimethoxybenzyl, O-nitrobenzyl, p-nitrobenzyl, p-halobenzyl, 2,6-dichlorobenzyl, p-cyanobenzyl, and 2- and 4-picolyl.

Amino protecting groups are well known in the art and include those described in detail in *Protecting Groups in Organic Synthesis*, T. W. Greene and P. G. M. Wuts, 3$^{rd}$ edition, John Wiley & Sons, 1999, the entirety of each of which is herein incorporated by reference. Suitable amino protecting groups include, but are not limited to, aralkylamines, carbamates, cyclic imides, allyl amines, amides, and the like. Examples of such groups include t-butyloxycarbonyl (BOC), ethyloxycarbonyl, methyloxycarbonyl, trichloroethyloxycarbonyl, allyloxycarbonyl (Alloc), benzyloxocarbonyl (CBZ), allyl, phthalimide, benzyl (Bn), fluorenylmethylcarbonyl (Fmoc), formyl, acetyl, chloroacetyl, dichloroacetyl, trichloroacetyl, phenylacetyl, trifluoroacetyl, benzoyl, and the like.

In the schemes below, where a provided compound is formed having a reactive DIM moiety (e.g., amine, alcohol, etc.), it is not shown but it is generally appreciated and well known by those having ordinary skill in the art that the reactivity of said reactive DIM moiety may be masked by employing a suitable protecting group that can thereafter be removed in situ or during a separate synthetic step.

In certain embodiments, compounds of the present invention are generally prepared according to Scheme 1 set forth below:

Scheme 2: Synthesis of Compounds of the Invention

As depicted in Scheme 1, above, amine A-1 is coupled to acid A-2 using the coupling agent HATU in the presence of the base DIPEA in DMF to form a compound of the invention with a linker comprising an amide bond. The squiggly bond, ᴍᴍᴍ , represents the portion of the linker between IRAK and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 2 set forth below:

Scheme 2: Synthesis of Compounds of the Invention

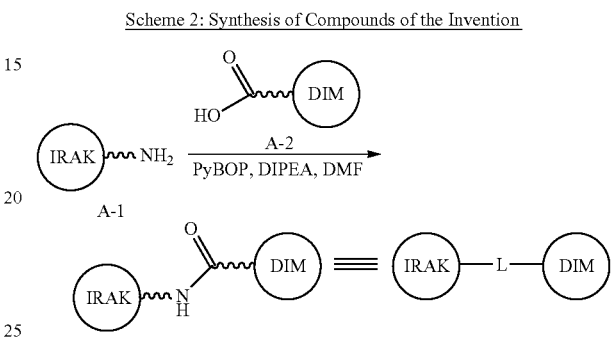

As depicted in Scheme 2, above, amine A-1 is coupled to acid A-2 using the coupling agent PyBOP in the presence of the base DIPEA in DMF to form a compound of the invention with a linker comprising an amide bond. The squiggly bond, ᴍᴍᴍ , represents the portion of the linker between IRAK and the terminal amino group of A-1 or the portion of the linker between DIM and the terminal carboxyl group of A-2, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 3 set forth below:

Scheme 3: Synthesis of Compounds of the Invention

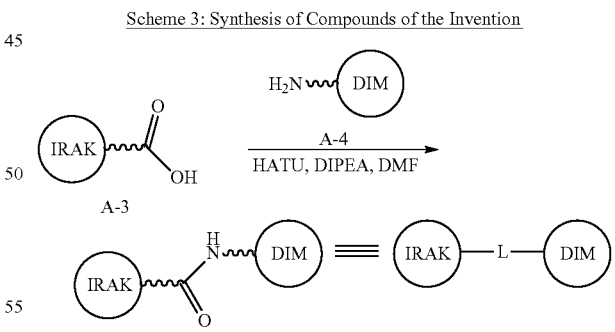

As depicted in Scheme 3, above, acid A-3 is coupled to amine A-4 using the coupling agent HATU in the presence of the base DIPEA in DMF to form a compound of the invention with a linker comprising an amide bond. The squiggly bond, ᴍᴍᴍ , represents the portion of the linker between IRAK and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 4 set forth below:

Scheme 4: Synthesis of Compounds of the Invention

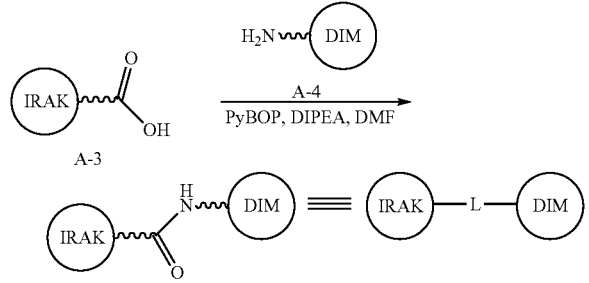

As depicted in Scheme 4, above, acid A-3 is coupled to amine A-4 using the coupling agent PyBOP in the presence of the base DIPEA in DMF to form a compound of the invention with a linker comprising an amide bond. The squiggly bond, ∿∿∿ , represents the portion of the linker between IRAK and the terminal carboxyl group of A-3 or the portion of the linker between DIM and the terminal amino group of A-4, respectively. Additionally, an amide bond can be formed using coupling reagents known in the art such as, but not limited to DCC, DIC, EDC, HBTU, HCTU, PyAOP, PyBrOP, BOP, BOP-Cl, DEPBT, T3P, TATU, TBTU, TNTU, TOTU, TPTU, TSTU, or TDBTU.

In certain embodiments, compounds of the present invention are generally prepared according to Scheme 5 set forth below:

Scheme 5: Synthesis of Compounds of the Invention

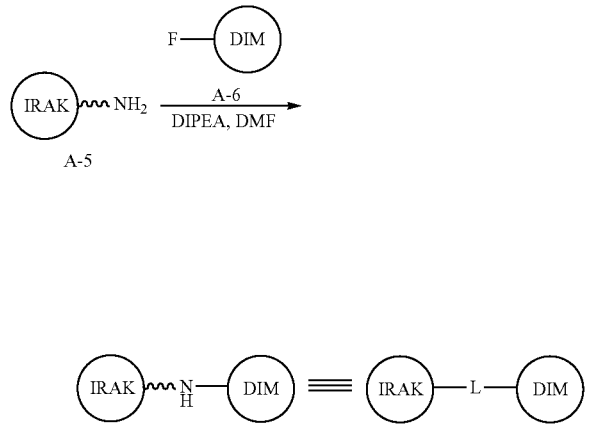

As depicted in Scheme 5, above, an SNAr displacement of fluoride A-6 by amine A-5 is effected in the presence of the base DIPEA in DMF to form a compound of the invention with a linker comprising a secondary amine. The squiggly bond, ∿∿∿ , represents the portion of the linker between IRAK and the terminal amino group of A-5.

In certain embodiments, compounds of the present invention are generally prepared according to Scheme 6 set forth below:

Scheme 6: Synthesis of Compounds of the Invention

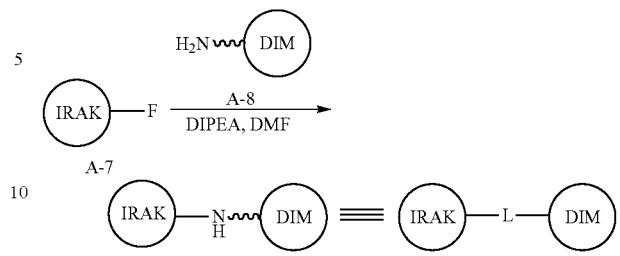

As depicted in Scheme 6, above, an SNAr displacement of fluoride A-7 by amine A-8 is effected in the presence of the base DIPEA in DMF to form a compound of the invention with a linker comprising a secondary amine. The squiggly bond, ∿∿∿ , represents the portion of the linker between DIM and the terminal amino group of A-8.

In certain embodiments, compounds of the present invention are generally prepared according to Scheme 7 set forth below:

Scheme 7: Synthesis of Compounds of The Invention

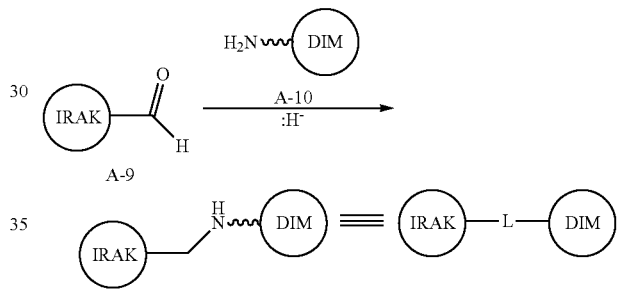

As depicted in Scheme 7, above, reductive alkylation of aldehyde A-9 by amine A-10 is effected in the presence of a mild hydride source (e.g., sodium cyanoborohydride or sodium triacetoxyborohydride) to form a provided compound with a linker comprising a secondary amine. The squiggly bond, ∿∿∿ , represents the portion of the linker between DIM and the terminal amino group of A-10.

In certain embodiments, compounds of the present invention are generally prepared according to Scheme 8 set forth below:

Scheme 8: Synthesis of Compounds of The Invention

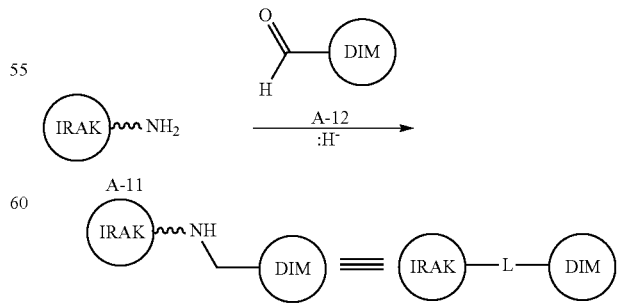

As depicted in Scheme 8, above, reductive alkylation of aldehyde A-12 by amine A-11 is effected in the presence of a mild hydride source (e.g., sodium cyanoborohydride or sodium triacetoxyborohydride) to form a provided compound with a linker comprising a secondary amine. The squiggly bond, ⌇, represents the portion of the linker between IRAK and the terminal amino group of A-11.

One of skill in the art will appreciate that various functional groups present in compounds of the invention such as aliphatic groups, alcohols, carboxylic acids, esters, amides, aldehydes, halogens and nitriles can be interconverted by techniques well known in the art including, but not limited to reduction, oxidation, esterification, hydrolysis, partial oxidation, partial reduction, halogenation, dehydration, partial hydration, and hydration. See for example, "March's Advanced Organic Chemistry", $5^{th}$ Ed., Ed.: Smith, M. B. and March, J., John Wiley & Sons, New York: 2001, the entirety of each of which is herein incorporated by reference. Such interconversions may require one or more of the aforementioned techniques, and certain methods for synthesizing compounds of the invention are described below in the Exemplification.

5. Uses, Formulation and Administration

Pharmaceutically Acceptable Compositions

According to another embodiment, the invention provides a composition comprising a compound of this invention or a pharmaceutically acceptable derivative thereof and a pharmaceutically acceptable carrier, adjuvant, or vehicle. The amount of compound in compositions of this invention is such that is effective to measurably degrade and/or inhibit an IRAK protein kinase, or a mutant thereof, in a biological sample or in a patient. In certain embodiments, the amount of compound in compositions of this invention is such that is effective to measurably degrade and/or inhibit an IRAK protein kinase, or a mutant thereof, in a biological sample or in a patient. In certain embodiments, a composition of this invention is formulated for administration to a patient in need of such composition. In some embodiments, a composition of this invention is formulated for oral administration to a patient.

The term "patient," as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A "pharmaceutically acceptable derivative" means any non-toxic salt, ester, salt of an ester or other derivative of a compound of this invention that, upon administration to a recipient, is capable of providing, either directly or indirectly, a compound of this invention or an inhibitorily or degratorily active metabolite or residue thereof.

As used herein, the term "inhibitorily active metabolite or residue thereof" means that a metabolite or residue thereof is also an inhibitor of an IRAK protein kinase, or a mutant thereof.

As used herein, the term "degratorily active metabolite or residue thereof" means that a metabolite or residue thereof is also a degrader of an IRAK protein kinase, or a mutant thereof.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of compounds of this invention include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

Most preferably, pharmaceutically acceptable compositions of this invention are formulated for oral administration. Such formulations may be administered with or without food. In some embodiments, pharmaceutically acceptable compositions of this invention are administered without food. In other embodiments, pharmaceutically acceptable compositions of this invention are administered with food.

The amount of compounds of the present invention that may be combined with the carrier materials to produce a composition in a single dosage form will vary depending upon the host treated, the particular mode of administration. Preferably, provided compositions should be formulated so that a dosage of between 0.01-100 mg/kg body weight/day of the compound can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of a compound of the present invention in the composition will also depend upon the particular compound in the composition.

Uses of Compounds and Pharmaceutically Acceptable Compositions

Compounds and compositions described herein are generally useful for the degradation and/or inhibition of kinase activity of one or more enzymes.

Examples of kinases that are degraded and/or inhibited by the compounds and compositions described herein and against which the methods described herein are useful include those of the interleukin-1 receptor-associated kinase (IRAK) family of kinases, the members of which include IRAK-1, IRAK-2, and IRAK-4, or a mutant thereof. Li et al., "IRAK-4: A novel member of the IRAK family with the properties of an IRAK-kinase," *PNAS* 2002, 99 (8), 5567-5572, Flannery et al., "The interleukin-1 receptor-associated kinases: Critical regulators of innate immune signaling" *Biochem Pharm* 2010, 80 (12), 1981-1991 incorporated by reference in its entirety.

The activity of a compound utilized in this invention as a degrader and/or inhibitor of IRAK-1, IRAK-2, and/or IRAK-4, or a mutant thereof, may be assayed in vitro, in vivo or in a cell line. In vitro assays include assays that determine inhibition of either the phosphorylation activity and/or the subsequent functional consequences, or ATPase activity of activated IRAK-1, IRAK-2, and/or IRAK-4, or a mutant thereof. Alternate in vitro assays quantitate the ability of the inhibitor to bind to IRAK-1, IRAK-2 and/or IRAK-4. Inhibitor binding may be measured by radiolabeling the inhibitor prior to binding, isolating the inhibitor/IRAK-1, inhibitor/IRAK-2, or inhibitor/IRAK-4 complex and determining the amount of radiolabel bound. Alternatively, inhibitor binding may be determined by running a competition experiment where new inhibitors are incubated with IRAK-1, IRAK-2, and/or IRAK-4 bound to known radioligands. Representative in vitro and in vivo assays useful in assaying an IRAK-4 inhibitor include those described and disclosed in, e.g., Kim et al., "A critical role for IRAK4 kinase activity in Toll-like receptor-mediated innate immunity," *J. Exp. Med.* 2007 204 (5), 1025-1036; Lebakken et al., "A Fluorescence Lifetime Based Binding Assay to Characterize Kinase Inhibitors," *J. Biomol. Screen.* 2007, 12 (6), 828-841; Maschera et al., "Overexpression of an enzymatically inactive interleukin-1-receptor-associated kinase activates nuclear factor-KB," *Biochem. J.* 1999, 339, 227-231; Song et al., "The kinase activities of interleukin-e receptor associated kinase (IRAK)-1 and 4 are redundant in the control of inflammatory cytokine expression in human cells," *Mol. Immunol.* 2009, 46, 1458-1466, each of, the entirety of each of which is herein incorporated by reference. Detailed conditions for assaying a compound utilized in this invention as a degrader and/or inhibitor of IRAK-1, IRAK-2, and/or IRAK-4, or a mutant thereof, are set forth in the Examples below.

The best characterized member of the IRAK family is the serine/threonine kinase IRAK-4. IRAK-4 is implicated in signaling innate immune responses from Toll-like receptors (TLRs) and Toll/IL-1 receptors (TIRs).

Innate immunity detects pathogens through the recognition of pathogen-associated molecular patterns by TLRs, when then links to the adaptive immune response. TLRs recognize conserved structures of both microbes and endogenous molecules. TLRs which recognize bacterial and fungal components are located on the cell surface, whereas TLRs which recognize viral or microbial nucleic acids are localized to intracellular membranes such as endosomes and phagosomes. Cell surface TLRs can be targeted by small molecules and antibodies, whereas intracellular TLRs require targeting with oligonucleotides.

TLRs mediate the innate immune response by upregulating the expression of inflammatory genes in multiple target cells. See, e.g., Sen et al., "Transcriptional signaling by double-stranded RNA: role of TLR3," *Cytokine & Growth Factor Rev.* 2005, 16, 1-14, incorporated by reference in its entirety. While TLR-mediated inflammatory response is critical for innate immunity and host defense against infections, uncontrolled inflammation is detrimental to the host leading to sepsis and chronic inflammatory diseases, such as chronic arthritis, atherosclerosis, multiple sclerosis, cancers, autoimmune disorders such as rheumatoid arthritis, lupus, asthma, psoriasis, and inflammatory bowel diseases.

Upon binding of a ligand, most TLRs recruit the adaptor molecule MyD88 through the TIR domain, mediating the MyD88-dependent pathway. MyD88 then recruits IRAK-4, which engages with the nuclear factor-κB (NF-κB), mitogen-activated protein (MAP) kinase and interferon-regulatory factor cascades and leads to the induction of pro-inflammatory cytokines. The activation of NF-κB results in the induction of inflammatory cytokines and chemokines, such as TNF-α, IL-1α, IL-6 and IL-8. The kinase activity of IRAK-4 has been shown to play a critical role in the TLR-mediated immune and inflammatory responses. IRAK4 is a key mediator of the innate immune response orchestrated by interleukin-1 receptor (IL-1R), interleukin-18 receptor (IL-18R), IL-33 receptor (IL-33R), and Toll-like receptors (TLRs). Inactivation of IRAK-1 and/or IRAK-4 activity has been shown to result in diminished production of cytokines and chemokines in response to stimulation of IL-1 and TLR ligands. See, e.g., Picard et al., "Clinical features and outcome of patients with IRAK-4 and MyD88 deficiency," *Medicine (Baltimore)*, 2010, 89 (6), 043-25; Li, "IRAK4 in TLR/IL-1R signaling: Possible clinical applications," *Eur. J. Immunology* 2008, 38:614-618; Cohen et al., "Targeting protein kinases for the development of anti-inflammatory drugs," *Curr. Opin. Cell Bio.* 2009, 21:317-324; Flannery et al., "The interleukin-1 receptor-associated kinases: Critical regulators of innate immune signalling," *Biochem. Pharm.* 2010, 80 (12), 1981-1991; Gottipati et al., "IRAK1: A critical signaling mediator of innate immunity," *Cellular Signaling* 2008, 20, 269-276; Kim et al., "A critical role for IRAK4 kinase activity in Toll-like receptor-mediated innate immunity," *J. Exp. Med.* 2007 204 (5), 1025-1036; Koziczak-Holbro et al., "IRAK-4 Kinase Activity Is Required for Interleukin-1 (IL-1) Receptor- and Toll-like Receptor 7-mediated Signaling and Gene Expression," *J. Biol. Chem.* 2007, 282 (18), 13552-13560; Kubo-Murai et al., "IRAK-4-dependent Degradation of IRAK-1 is a Negative Feedback Signal for TLR-mediated NF-κB Activation," *J. Biochem.* 2008, 143, 295-302; Maschera et al., "Overexpression of an enzymatically inactive interleukin-1-receptor-associated kinase activates nuclear factor-κB," *Biochem. J.* 1999, 339, 227-231; Lin et al., "Helical assembly in the MyD88-IRAK4-IRAK2 complex in TLR/IL-1R signalling," *Nature* 2010, 465 (17), 885-891; Suzuki et al., "IRAK-4 as the central TIR signaling mediator in innate immunity," *TRENDS in Immunol.* 2002, 23 (10), 503-506; Suzuki et al., "Severe impairment of interleukin-1 and Toll-like receptor signalling in mice lacking IRAK-4," *Nature* 2002, 416, 750-754; Swantek et al., "IL-1 Receptor-Associated Kinase Modulates Host Responsiveness to Endotoxin," *J. Immunol.* 2000, 164, 4301-4306; Hennessy, E., et al., "Targeting Toll-like receptors: emerging therapeutics?" *Nature Reviews*, vol. 9, pp: 293-307 (2010); Dinarello, C. "Interleukin-18 and the Pathogenesis of Inflammatory Diseases," *Seminars in Nephrology*, vol. 27, no. 1, pp: 98-114 (2007), each of, the entirety of each of which is herein incorporated by reference. In fact, knockdown mice that express a catalytically inactive mutant IRAK-4 protein are completely resistant to septic shock and show impaired IL-1 activity. Moreover, these mice are resistant to joint and bone inflammation/destruction in an arthritis model, suggesting that IRAK-4 may be targeted to treat chronic inflammation. Further, while IRAK-4 appears to be vital for childhood immunity against some pyogenic bacteria, it has been shown to play a redundant role in protective immunity to most infections in adults, as demonstrated by one study in which patients older than 14 lacking IRAK-4 activity exhibited no invasive infections. Cohen et al., "Targeting protein kinases for the development of anti-inflammatory drugs," *Curr. Opin. Cell Bio.* 2009, 21:317-324; Ku et al., "Selective predisposition to bacterial infections in IRAK-4-deficient children: IRAK-4-dependent TLRs are otherwise redundant in protective immunity," *J. Exp. Med.* 2007, 204 (10), 2407-2422; Picard et al., "Inherited human IRAK-4 deficiency: an update," *Immunol. Res.* 2007, 38, 347-352; Song et al., "The kinase activities of interleukin-e receptor associated kinase (IRAK)-1 and 4 are redundant in the control of inflammatory cytokine expression in human cells," *Mol. Immunol.* 2009, 46, 1458-1466; Rokosz, L. et al., "Kinase inhibitors as drugs for chronic inflammatory and immunological diseases: progress and challenges," *Expert Opinions on Therapeutic Targets*, 12 (7), pp: 883-903 (2008); Gearing, A. "Targeting toll-like receptors for drug development: a summary of commercial approaches," Immunology and Cell Biology, 85, pp: 490-494 (2007); Dinarello, C. "IL-1: Discoveries, controversies and future directions," *European Journal of Immunology*, 40, pp: 595-653 (2010), each of, the entirety of each of which is herein incorporated by reference. Because TLR activation triggers IRAK-4 kinase activity, IRAK-4 inhibition presents an attractive target for treating the underlying causes of inflammation in countless diseases.

Representative IRAK-4 inhibitors include those described and disclosed in e.g., Buckley et al., *Bioorg. Med. Chem. Lett.* 2008, 18, 3211-3214; Buckley et al., *Bioorg. Med. Chem. Lett.* 2008, 18, 3291-3295; Buckley et al., *Bioorg. Med. Chem. Lett.* 2008, 18, 3656-3660; Powers et al., "Discovery and initial SAR of inhibitors of interleukin-1 receptor-associated kinase-4," *Bioorg. Med. Chem. Lett.* 2006, 16, 2842-2845; Wng et al., "IRAK-4 Inhibitors for Inflammation," *Curr. Topics in Med. Chem.* 2009, 9, 724-737, each of, the entirety of each of which is herein incorporated by reference.

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Provided compounds are degraders and/or inhibitors of one of more of IRAK-1, IRAK-2, and/or IRAK-4 and are therefore useful for treating one or more disorders associated with activity of one or more of IRAK-1, IRAK-2, and/or IRAK-4. Thus, in certain embodiments, the present invention provides a method for treating a IRAK-1-mediated, a IRAK-2-mediated, and/or a IRAK-4-mediated disorder comprising the step of administering to a patient in need thereof a compound of the present invention, or pharmaceutically acceptable composition thereof.

As used herein, the terms "IRAK-1-mediated", "IRAK-2-mediated", and/or "IRAK-4-mediated" disorders, diseases, and/or conditions as used herein means any disease or other deleterious condition in which one or more of IRAK-1, IRAK-2, and/or IRAK-4, or a mutant thereof, are known to play a role. Accordingly, another embodiment of the present invention relates to treating or lessening the severity of one or more diseases in which one or more of IRAK-1, IRAK-2, and/or IRAK-4, or a mutant thereof, are known to play a role.

In some embodiments, the present invention provides a method for treating one or more disorders, diseases, and/or conditions wherein the disorder, disease, or condition is a cancer, a neurodegenerative disorder, a viral disease, an autoimmune disease, an inflammatory disorder, a hereditary disorder, a hormone-related disease, a metabolic disorder, conditions associated with organ transplantation, immunodeficiency disorders, a destructive bone disorder, a proliferative disorder, an infectious disease, a condition associated with cell death, thrombin-induced platelet aggregation, liver disease, pathologic immune conditions involving T cell activation, a cardiovascular disorder, or a CNS disorder.

Diseases and conditions treatable according to the methods of this invention include, but are not limited to, cancer (see, e.g., Ngo, V. et al., "Oncogenically active MYD88 mutations in human lymphoma," *Nature*, vol. 000, pp: 1-7 (2010); Lust, J. et al., "Induction of a Chronic Disease State in patients With Smoldering of Indolent Multiple Myeloma by Targeting Interleukin 1β-Induced Interleukin 6 Production and the Myeloma Proliferative Component," *Mayo Clinic Proceedings*, 84 (2), pp: 114-122 (2009)), diabetes, cardiovascular disease, viral disease, autoimmune diseases such as lupus (see, e.g., Dinarello, C. "Interleukin-18 and the Pathogenesis of Inflammatory Diseases," *Seminars in Nephrology*, vol. 27, no. 1, pp: 98-114 (2007); Cohen et al., "Targeting protein kinases for the development of antiinflammatory drugs," *Curr Opin. Cell Bio.* 2009, 21:317-324) and rheumatoid arthritis (see, e.g., Geyer, M. et al., "Actual status of antiinterleukin-1 therapies in rheumatic diseases," *Current Opinion in Rheumatology*, 22, pp: 246-251 (2010)), autoinflammatory syndromes (see, e.g., Hoffman, H. et al., "Efficacy and Safety of Rilonacept (Interleukin-1 Trap) in Patients with Cryopyrin-Associated Periodic Syndromes," *Arthritis & Rheumatism*, vol. 58, no. 8, pp: 2443-2452 (2008)), atherosclerosis, psoriasis, allergic disorders, inflammatory bowel disease (see, e.g., Cario, E. "Therapeutic Impact of Toll-like Receptors on Inflammatory Bowel Diseases: A Multiple-edged Sword," *Inflamm. Bowel Dis.*, 14, pp: 411-421 (2008)), inflammation (see, e.g., Dinarello, C. "Interleukin 1 and interleukin 18 as mediators of inflammation and the aging process," *The American Journal of Clinical Nutrition*, 83, pp: 447S-455S (2006)), acute and chronic gout and gouty arthritis (see, e.g., Terkeltaub, R. "Update on gout: new therapeutic strategies and options," *Nature*, vol. 6, pp: 30-38 (2010); Weaver, A. "Epidemiology of gout," *Cleveland Clinic Journal of Medicine*, vol. 75, suppl. 5, pp: S9-S12 (2008); Dalbeth, N. et al., "Hyperuricaemia and gout: state of the art and future perspectives," *Annals of Rheumatic Diseases*, 69, pp: 1738-1743 (2010); Martinon, F. et al., "Gout-associated uric acid crystals activate the NALP3 inflammasome," *Nature*, vol. 440, pp: 237-241 (2006); So, A. et al., "A pilot study of IL-1 inhibition by anakinra in acute gout," *Arthritis Research & Therapy*, vol. 9, no. 2, pp: 1-6 (2007); Terkeltaub, R. et al., "The interleukin 1 inhibitor rilonacept in treatment of chronic gouty arthritis: results of a placebo-controlled, monosequence crossover, non-randomised, single-blind pilot study," *Annals of Rheumatic Diseases*, 68, pp: 1613-1617 (2009); Torres, R. et al., "Hyperalgesia, synovitis and multiple biomarkers of inflammation are suppressed by interleukin 1 inhibition in a novel animal model of gouty arthritis," *Annals of Rheumatic Diseases*, 68, pp: 1602-1608 (2009)), neurological disorders, metabolic syndrome (see, e.g., Troseid, M. "The role of interleukin-18 in the metabolic syndrome," *Cardiovascular Diabetology*, 9:11, pp: 1-8 (2010)), immunodeficiency disorders such as AIDS and HIV (see, e.g., Iannello, A. et al., "Role of Interleukin-18 in the Development and Pathogenesis of AIDS," *AIDS Reviews*, 11, pp: 115-125 (2009)), destructive bone disorders (see, e.g., Hennessy, E., et al., "Targeting Toll-like receptors: emerging therapeutics?" *Nature Reviews*, vol. 9, pp: 293-307 (2010)), osteoarthritis, proliferative disorders, Waldenström's Macroglobulinemia (see, e.g., Treon, et al., "Whole genome sequencing reveals a widely expressed mutation (MYD88 L265P) with oncogenic activity in Waldenström's Macroglobulinemia" 53$^{rd}$ ASH Annual Meeting; Xu, et al., "A somatic variant in MYD88 (L256P) revealed by whole genome sequencing differentiates lymphoplasmacytic lymphoma from marginal zone lymphomas" 53$^{rd}$ ASH Annual Meeting; Yang et al., "Disruption of MYD88 pathway signaling leads to loss of constitutive IRAK1, NK-kB and JAK/STAT signaling and induces apoptosis of cells expressing the MYD88 L265P mutation in Waldenström's Macroglobulinemia" 53$^{rd}$ ASH Annual Meeting; Iriyama et al., "Clinical significance of genetic mutations of CD79B, CARD11, MYD88, and EZH2 genes in diffuse large B-cell lymphoma patients" 53$^{rd}$ ASH Annual Meeting; infectious diseases, conditions associated with cell death, pathologic immune conditions involving T cell activation, and CNS disorders in a patient. In one embodiment, a human patient is treated with a compound of the current invention and a pharmaceutically acceptable carrier, adjuvant, or vehicle, wherein said compound is present in an amount to measurably degrade and/or inhibit IRAK-1 only, IRAK-2-only, IRAK-4-only and/or IRAK1 and IRAK4 kinase activity.

Compounds of the current invention are useful in the treatment of a proliferative disease selected from a benign or malignant tumor, solid tumor, carcinoma of the brain, kidney, liver, adrenal gland, bladder, breast, stomach, gastric tumors, ovaries, colon, rectum, prostate, pancreas, lung, vagina, cervix, testis, genitourinary tract, esophagus, larynx, skin, bone or thyroid, sarcoma, glioblastomas, neuroblastomas, multiple myeloma, gastrointestinal cancer, especially colon carcinoma or colorectal adenoma, a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, Hodgkins and Non-Hodgkins, a mammary carcinoma, follicular carcinoma, undifferentiated carcinoma, papillary carcinoma, seminoma, melanoma, an IL-1 driven disorder, an MyD88 driven disorder, Smoldering of indolent multiple myeloma, or hematological malignancies (including leukemia, diffuse large B-cell lymphoma (DLBCL), ABC DLBCL, chronic lymphocytic leukemia (CLL), chronic lymphocytic lymphoma, primary effusion lymphoma, Burkitt lymphoma/leukemia, acute lymphocytic leukemia, B-cell prolymphocytic leukemia, lymphoplasmacytic lymphoma, Waldenström's macroglobulinemia (WM), splenic marginal zone lymphoma, multiple myeloma, plasmacytoma, intravascular large B-cell lymphoma, AML, MDS).

In some embodiments the proliferative disease which can be treated according to the methods of this invention is an MyD88 driven disorder. In some embodiments, the MyD88 driven disorder which can be treated according to the methods of this invention is selected from ABC DLBCL, primary CNS lymphomas, primary extranodal lymphomas, Waldenström's macroglobulinemia, Hodgkin's lymphoma, primary cutaneous T-cell lymphoma and chronic lymphocytic leukemia.

In some embodiments the proliferative disease which can be treated according to the methods of this invention is an IL-1 driven disorder. In some embodiments the IL-1 driven disorder is Smoldering of indolent multiple myeloma.

Compounds according to the invention are useful in the treatment of inflammatory or obstructive airways diseases, resulting, for example, in reduction of tissue damage, airways inflammation, bronchial hyperreactivity, remodeling or disease progression. Inflammatory or obstructive airways diseases to which the present invention is applicable include asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection. Treatment of asthma is also to be understood as embracing treatment of subjects, e.g. of less than 4 or 5 years of age, exhibiting wheezing symptoms and diagnosed or diagnosable as "wheezy infants", an established patient category of major medical concern and now often identified as incipient or early-phase asthmatics.

Compounds according to the invention are useful in the treatment of heteroimmune diseases. Examples of such heteroimmune diseases include, but are not limited to, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis.

Prophylactic efficacy in the treatment of asthma will be evidenced by reduced frequency or severity of symptomatic attack, e.g. of acute asthmatic or bronchoconstrictor attack, improvement in lung function or improved airways hyperreactivity. It may further be evidenced by reduced requirement for other, symptomatic therapy, such as therapy for or intended to restrict or abort symptomatic attack when it occurs, for example antiinflammatory or bronchodilatory. Prophylactic benefit in asthma may in particular be apparent in subjects prone to "morning dipping". "Morning dipping" is a recognized asthmatic syndrome, common to a substantial percentage of asthmatics and characterised by asthma attack, e.g. between the hours of about 4 to 6 am, i.e. at a time normally substantially distant form any previously administered symptomatic asthma therapy.

Compounds of the current invention can be used for other inflammatory or obstructive airways diseases and conditions to which the present invention is applicable and include acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy. The invention is also applicable to the treatment of bronchitis of whatever type or genesis including, but not limited to, acute, arachidic, catarrhal, croupus, chronic or phthinoid bronchitis. Further inflammatory or obstructive airways diseases to which the present invention is applicable include pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis.

With regard to their anti-inflammatory activity, in particular in relation to inhibition of eosinophil activation, compounds of the invention are also useful in the treatment of eosinophil related disorders, e.g. eosinophilia, in particular eosinophil related disorders of the airways (e.g. involving morbid eosinophilic infiltration of pulmonary tissues) including hypereosinophilia as it effects the airways and/or lungs as well as, for example, eosinophil-related disorders of the airways consequential or concomitant to Loffler's syndrome, eosinophilic pneumonia, parasitic (in particular metazoan) infestation (including tropical eosinophilia), bronchopulmonary aspergillosis, polyarteritis nodosa (including Churg-Strauss syndrome), eosinophilic granuloma, eosinophilic asthma, eosinophilic COPD, and eosinophil-related disorders affecting the airways occasioned by drug-reaction.

Compounds of the invention are also useful in the treatment of inflammatory or allergic conditions of the skin, for example psoriasis, generalized pustular psoriasis (GPP), psoriasis vulgaris, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, systemic lupus erythematosus, pemphigus vulgaris, pemphigus foliaceus, paraneoplastic pemphigus, epidermolysis bullosa acquisita, acne vulgaris, hidradenitis suppurativa, Sweet Syndrome, pyoderma gangrenosum, and other inflammatory or allergic conditions of the skin.

Compounds of the invention may also be used for the treatment of other diseases or conditions, such as diseases or conditions having an inflammatory component, for example, treatment of diseases and conditions of the eye such as ocular allergy, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, scleroderma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), irritable bowel syndrome, celiac disease, periodontitis, hyaline membrane disease, kidney disease, glomerular disease, alcoholic liver disease, multiple sclerosis, endocrine opthalmopathy, Grave's disease, sarcoidosis, alveolitis, chronic hypersensitivity pneumonitis, multiple sclerosis, primary biliary cirrhosis, uveitis (anterior and posterior), Sjogren's syndrome, keratoconjunctivitis sicca and vernal keratoconjunctivitis, interstitial lung fibrosis, psoriatic arthritis, systemic juvenile idiopathic arthritis, cryopyrin-associated periodic syndrome, nephritis, vasculitis, diverticulitis, interstitial cystitis, glomerulonephritis (with and without nephrotic syndrome, e.g. including idiopathic nephrotic syndrome or minal change nephropathy), chronic granulomatous disease, endometriosis, leptospiriosis renal disease, glaucoma, retinal disease, ageing, headache, pain, complex regional pain syndrome, cardiac hypertrophy, musclewasting, catabolic disorders, obesity, fetal growth retardation, hyperchlolesterolemia, heart disease, chronic heart failure, mesothelioma, anhidrotic ecodermal dysplasia, Behcet's disease, incontinentia pigmenti, Paget's disease, pancreatitis, hereditary periodic fever syndrome, asthma (allergic and non-allergic, mild, moderate, severe, bronchitic, and exercise-induced), acute lung injury, acute respiratory distress syndrome, eosinophilia, hypersensitivities, anaphylaxis, nasal sinusitis, ocular allergy, silica induced diseases, COPD (reduction of damage, airways inflammation, bronchial hyperreactivity, remodeling or disease progression), pulmonary disease, cystic fibrosis, acid-induced lung injury, pulmonary hypertension, polyneuropathy, cataracts, muscle inflammation in conjunction with systemic sclerosis, inclusion body myositis, myasthenia gravis, thyroiditis, Addison's disease, lichen planus, Type 1 diabetes, or Type 2 diabetes, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis.

In some embodiments the inflammatory disease which can be treated according to the methods of this invention is an disease of the skin. In some embodiments, the inflammatory disease of the skin is selected from contact dermatitits, atompic dermatitis, alopecia areata, erythema multiforma, dermatitis herpetiformis, scleroderma, vitiligo, hypersensitivity angiitis, urticaria, bullous pemphigoid, pemphigus vulgaris, pemphigus foliaceus, paraneoplastic pemphigus, epidermolysis bullosa acquisita, hidradenitis suppurativa, and other inflammatory or allergic conditions of the skin.

In some embodiments the inflammatory disease which can be treated according to the methods of this invention is selected from acute and chronic gout, chronic gouty arthritis, psoriasis, psoriatic arthritis, rheumatoid arthritis, Juvenile rheumatoid arthritis, Systemic jubenile idiopathic arthritis (SJIA), Cryopyrin Associated Periodic Syndrome (CAPS), Adult Onset Still's disease, macrophage activation syndrome (MAS), primary and secondary hemophagocytic lymphohistiocytosis (HLH), Familial Mediterranean Fever, NLRP 12 autoinflammatory syndrome, and osteoarthritis.

In some embodiments the inflammatory disease which can be treated according to the methods of this invention is a TH17 mediated disease. In some embodiments the TH17 mediated disease is selected from Systemic lupus erythematosus, Multiple sclerosis, psoriasis vulgaris, hidradenitis suppurativa, and inflammatory bowel disease (including Crohn's disease or ulcerative colitis).

In some embodiments the inflammatory disease which can be treated according to the methods of this invention is selected from Sjogren's syndrome, allergic disorders, osteoarthritis, conditions of the eye such as ocular allergy, conjunctivitis, keratoconjunctivitis sicca and vernal conjunctivitis, and diseases affecting the nose such as allergic rhinitis or chronic rhinosinusitis with nasal polyps (CR-SwNP).

Cardiovascular diseases which can be treated according to the methods of this invention include, but are not limited to, restenosis, cardiomegaly, atherosclerosis, myocardial infarction, ischemic stroke, congestive heart failure, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, and deep venous thrombosis.

In some embodiments, the neurodegenerative disease which can be treated according to the methods of this invention include, but are not limited to, Alzheimer's disease, Parkinson's disease, amyotrophic lateral sclerosis, Huntington's disease, cerebral ischemia, and neurodegenerative disease caused by traumatic injury, glutamate neurotoxicity, hypoxia, epilepsy, treatment of diabetes, metabolic syndrome, obesity, organ transplantation and graft versus host disease.

The loss of IRAK4 function results in decreased Aβ levels in an in vivo murine model of Alzheimer's disease and was associated with diminished microgliosis and astrogliosis in aged mice. Analysis of microglia isolated from the adult mouse brain revealed an altered pattern of gene expression associated with changes in microglial phenotype that were associated with expression of IRF transcription factors that govern microglial phenotype. Further, loss of IRAK4 function also promoted amyloid clearance mechanisms, including elevated expression of insulin-degrading enzyme. Finally, blocking IRAK function restored olfactory behavior (Cameron et al. "Loss of Interleukin Receptor-Associated Kinase 4 Signaling Suppresses Amyloid Pathology and Alters Microglial Phenotype in a Mouse Model of Alzheimer's Disease" Journal of Neuroscience (2012) 32 (43), 15112-15123).

In some embodiments the invention provides a method of treating, preventing or lessening the severity of Alzheimer's disease comprising administering to a patient in need thereof a provided compound or a pharmaceutically acceptable salt or composition thereof.

In some embodiments the invention provides a method of treating a disease condition commonly occurring in connection with transplantation. In some embodiments, the disease or condition commonly occurring in connection with transplantation is selected from organ transplantation, organ transplant rejection, and graft versus host disease.

In some embodiments the invention provides a method of treating a metabolic disease. In some embodiments the metabolic disease is selected from Type 1 diabetes, Type 2 diabetes, metabolic syndrome, and obesity.

In some embodiments the invention provides a method of treating a viral disease. In some embodiments, the viral infection is HIV infection.

Furthermore, the invention provides the use of a compound according to the definitions herein, or a pharmaceutically acceptable salt, or a hydrate or solvate thereof for the preparation of a medicament for the treatment of a proliferative disease, an inflammatory disease, an obstructive respiratory disease, a cardiovascular disease, a metabolic disease, a neurological disease, a neurodegenerative disease, a viral disease, or a disorder commonly occurring in connection with transplantation.

Multiple Degradation

In some embodiments, the invention provides compounds that modulate targeted ubiquitination and degradation of one or more IRAK kinase. In some embodiments, a provided compound modulates targeted ubiquitination and degradation of one or more IRAK kinase and one or more additional protein. In some instances, a provided compound modulates targeted ubiquitination and degradation of IRAK4 and one, two, three, four, or five additional proteins.

In certain embodiments, the invention provides compounds that are triple degraders. In certain embodiments, the invention provides compounds that combine IRAK kinase degradation with IKZF 1 and IKZF3 degradation. Some of the most commonly employed E3 ligase ligands are thalidomide and its derivatives, lenalidomide and pomalidomide, commonly referred to as IMiDs (immunomodulatory imide drugs). These agents are small-molecule ligands of cereblon (CRBN) (Ito et al. "Identification of a primary target of thalidomide teratogenicity" Science 2010, 327 (5971):1345-1350), a substrate adaptor for the ubiquitously expressed cullin ring ligase 4 (CUL4)-RBX1-DDB1-CRBN (CUL4CRBN) E3 ligase. It has been shown that thalidomide interacts with CRBN to form a novel surface, resulting in interactions with neosubstrates such as Ikaros (IKZF1) and Aiolos (IKZF3) and their ubiquitination and subsequent proteasomal degradation (Kronke et al. "Lenalidomide causes selective degradation of IKZF 1 and IKZF3 in multiple myeloma cells" Science 2014, 343 (6168):301-305; and Lu et al. "The myeloma drug lenalidomide promotes the cereblon-dependent destruction of Ikaros proteins" Science, 2014; 343 (6168):305-309). This activity alone has potent antitumor effects in some liquid malignancies, and lenalidomide (Revlimid®) is US Food and Drug Administration approved for the treatment of MCL, multiple myeloma, and myelodysplastic syndromes with deletion of chromosome 5q. Lenalidomide is also undergoing late-stage clinical trials for a number of lymphomas, including MCL and the activated B-cell subtype of diffuse large B-cell lymphoma (ABC DLBCL).

In some instances, degradation of IRAK4 alone is not sufficient to kill the MYD88 L265P mutant DLBCL cell line OCI-LY10 either in vitro or as a flank xenograft in vivo. Table 2 shows that several IRAK4 binding moieties coupled to non-IMiD CRBN binders mediate effective knockdown of IRAK4 but have little to no effect on the viability of MYD88 mutant ABC-DLBCL cell lines OCI-LY10 and SU-DHL-2 in vitro.

FIG. 18 shows that I-257 dosing (PO, BID) effects 90% IRAK4 degradation in OCI-LY10 tumor xenograft but without causing regression. This is consistent with literature demonstrating no effect on growth of OCI-LY10 or other MYD88 mutant lines when the gene encoding IRAK4 is removed at the DNA level using CRISPR/Cas9 editing (Phelan et al. "A multiprotein supercomplex controlling oncogenic signaling in lymphoma" Nature, 2018, 7718:387-391).

It has been shown that activating MYD88 mutations increase production of beta-IFN, a pro-apoptotic cytokine, in ABC-DLBCL cells (Yang et al. "Exploiting synthetic lethality for the therapy of ABC diffuse large B cell lymphoma" Cancer Cell 2012, 21 (6):723-737). The cells are rendered resistant to this effect by a concomitant MYD88-driven activation of NFkB signaling via IRF4 and SPIB transactivating CARD11 (Yang, Cancer Cell 2012). IMiDs are also known to increase the IFN response in MYD88 mutant ABC-DLBCL to levels sufficient to increase apoptosis (Yang, Cancer Cell 2012; and Hagner et al. "CC-122, a pleiotropic pathway modifier, mimics an interferon response and has antitumor activity in DLBCL" Blood 2015, 126: 779-789). This effect has been shown to synergize with inhibition of NFkB signaling to further drive DLBCL cell death (Yang, Cancer Cell 2012).

In some instances, the combination of an IMiD with a small molecule IRAK4 kinase inhibitor shows little to no additive effect on viability of the MYD88 mutant ABC DLBCL cell line OCI-LY10. FIG. 19 shows that the combination of an IRAK4 inhibitor with IMiD is less active than an all-in-one IMiD-based IRAK4 degrader.

In certain embodiments, the combination of IRAK kinase degradation with IKZF 1 and IKZF3 degradation in an all-in-one IMiD-based IRAK4 degrader shows potent, single agent activity versus MYD88 mutant ABC DLBCL cell lines in vitro and OCI-LY10 xenograft in vivo. FIG. 20 shows that the all-in-one combination of an IMiD-based CRBN-binder and an IRAK4 binding moiety yields IRAK4 degraders that retain degradation of Ikaros (IKZF 1) and other known IMiDs neosubstrates, while more strongly inducing an interferon response compared to pomalidomide alone. Surprisingly, these IMiD-based IRAK4 degraders are potent at killing MYD88 mutant ABD-DLBCL cell lines in vitro (Table 3), demonstrating increased activity versus that

TABLE 2

IRAK4 degradation alone is insufficient to kill MYD88 mutant DLBCL cell lines in vitro

|  | I-75 | I-257 | I-229 | I-191 |
| --- | --- | --- | --- | --- |
| IRAK4 Degradation in OCI-LY10, $DC_{50}$ (nM) | 8 | 5 | 26 | 4 |
| MYD88 Mutant Lines | | | | |
| OCI-LY10 Viability, CTG $IC_{50}$ (nM) | 11 | 1,200 | 3,500 | >10,000 |
| SU-DHL2 Viability, CTG $IC_{50}$ (nM) | 290 | 6,900 | >10,000 | >10,000 |
| MYD88 WT Lines | | | | |
| SU-DHL6 Viability, CTG $IC_{50}$ (nM) | 1,600 | 5,600 | 4,100 | 5,600 |
| U2932 Viability, CTG $IC_{50}$ (nM) | 374 | >10,000 | >10,000 | >10,000 |
| OCI-LY19 Viability, CTG $IC_{50}$ (nM) | 480 | 4,700 | >10,000 | >10,000 | obtained from combining an IRAK4 inhibitor with IMiDs as single agents as shown in FIG. 19.

TABLE 3

Substituting pomalidomide as ligase binder enables MYD88-dependent single-agent activity

|  |  | I-75 | I-168 | I-257 | I-208 |
|---|---|---|---|---|---|
| IRAK4 OCI-LY10 $DC_{50}$ (nM) |  | 8 | 20 | 5 | 20 |
| IRAK4 WB $DC_{50}$ (nM) |  | 23 | 78 | 3 | 130 |
| IKAROS OCI-LY10 $DC_{50}$ (nM) |  | >100 | 5 | — | 3 |
| AIOLOS OCI-LY10 $DC_{50}$ (nM) |  | >100 | 5 | — | <3 |
| $MYD88^{MUT}$ | OCI-LY10 CTG $IC_{50}$ (nM) | 11 | 31 | 1,200 | 36 |
|  | SU-DHL2 CTG $IC_{50}$ (nM) | 290 | 64 | 6,900 | 366 |
|  | OCI-LY3 CTG $IC_{50}$ (nM) | 180 | 290 | — | 3000 |
| $MYD88^{WT}$ | SU-DHL6 CTG $IC_{50}$ (nM) | 1,600 | 1,900 | 5,600 | 833 |
|  | U2932 CTG $IC_{50}$ (nM) | 374 | 410 | 10,000 | 1,800 |
|  | OCI-LY19 CTG $IC_{50}$ (nM) | 480 | 430 | 4,700 | 1,700 |

In certain embodiments, a provided compound comprising a IMiD-based E3 ligase (e.g., 1-208) degrades IRAK4, Ikaros, and Aiolos in OCI-LY10 xenografts in vivo, and strongly induces a signature of interferon-driven proteins exemplified by IFIT1 (interferon-inducible transcript 1) and IFIT3 (interferon-inducible transcript 3) as shown in Table 4. FIG. 21 shows that 1-208 drives regression of these OCI-LY10 tumor xenographs as a single agent.

TABLE 4

OCI-LY10 tumor xenograft regression using I-208 (regression results in bold font)

| | | | | OCI-LY10 Tumor Xenograft | | | | |
|---|---|---|---|---|---|---|---|---|
| | | | | | | | Interferon Response | |
| Dose (mg/kg) | Route | Sched | Sample time (h) | IRAK4 ↓ (% Control) | Ikaros ↓ (% Control) | Aiolos ↓ (% Control) | IFIT1 Increase (Fold) | IFIT3 Increase (Fold) |
| 24 | PO | QD | 24 | 57.8 | 46.3 | 30.9 | >24.4 | >43.1 |
| 72 | PO | QD | 24 | 78.7 | 71.0 | 62.4 | >41.5 | >64.0 |
| 240 | PO | QD | 24 | 86.5 | 81.2 | 68.6 | >38.7 | >59.7 |

In some embodiments, the provided compounds of present invention highlight a synergy obtained by combining IRAK4 degradation with IMiD induction of interferon response to drive single agent anti-tumor activity in MYD88 mutant DLBCL and possibly in other heme malignancies. In certain embodiments, a provided compound comprising an IMiD-based E3 ligase degrade IRAK4, Ikaros, and Aiolos acts synergistically. In some embodiments, a provided compound comprising an IRAK4 binder and an IMiD-based E3 ligase degrades IRAK4, Ikaros, and Aiolos with increased activity in comparison to a provided compound comprising the same IRAK4 binder and a non-IMiD-based E3 ligase and the same IMiD-based E3 ligase as a single agent.

Combination Therapies

Depending upon the particular condition, or disease, to be treated, additional therapeutic agents, which are normally administered to treat that condition, may be administered in combination with compounds and compositions of this invention. As used herein, additional therapeutic agents that are normally administered to treat a particular disease, or condition, are known as "appropriate for the disease, or condition, being treated."

In certain embodiments, a provided combination, or composition thereof, is administered in combination with another therapeutic agent.

In some embodiments, the present invention provides a method of treating a disclosed disease or condition comprising administering to a patient in need thereof an effective amount of a compound disclosed herein or a pharmaceutically acceptable salt thereof and co-administering simultaneously or sequentially an effective amount of one or more additional therapeutic agents, such as those described herein. In some embodiments, the method includes co-administering one additional therapeutic agent. In some embodiments, the method includes co-administering two additional therapeutic agents. In some embodiments, the combination of the disclosed compound and the additional therapeutic agent or agents acts synergistically.

Examples of agents the combinations of this invention may also be combined with include, without limitation: treatments for Alzheimer's Disease such as Aricept® and Excelon®; treatments for HIV such as ritonavir; treatments for Parkinson's Disease such as L-DOPA/carbidopa, entacapone, ropinrole, pramipexole, bromocriptine, pergolide, trihexephendyl, and amantadine; agents for treating Multiple Sclerosis (MS) such as beta interferon (e.g., Avonex® and Rebif®), Copaxone®, and mitoxantrone; treatments for asthma such as albuterol and Singulair®; agents for treating schizophrenia such as zyprexa, risperdal, seroquel, and haloperidol; anti-inflammatory agents such as corticosteroids, TNF blockers, IL-1 RA, azathioprine, cyclophosphamide, and sulfasalazine; immunomodulatory and immunosuppressive agents such as cyclosporin, tacrolimus, rapamycin, mycophenolate mofetil, interferons, corticosteroids, cyclophophamide, azathioprine, and sulfasalazine; neurotrophic factors such as acetylcholinesterase inhibitors, MAO inhibitors, interferons, anti-convulsants, ion channel blockers, riluzole, and anti-Parkinsonian agents; agents for treating cardiovascular disease such as beta-blockers, ACE inhibitors, diuretics, nitrates, calcium channel blockers, and statins; agents for treating liver disease such as corticosteroids, cholestyramine, interferons, and anti-viral agents; agents for treating blood disorders such as corticosteroids, anti-leukemic agents, and growth factors; agents that prolong or improve pharmacokinetics such as cytochrome P450 inhibitors (i.e., inhibitors of metabolic breakdown) and CYP3A4 inhibitors (e.g., ketokenozole and ritonavir), and agents for treating immunodeficiency disorders such as gamma globulin.

In certain embodiments, combination therapies of the present invention, or a pharmaceutically acceptable composition thereof, are administered in combination with a monoclonal antibody or an siRNA therapeutic.

Those additional agents may be administered separately from a provided combination therapy, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a combination of the present invention may be administered with another therapeutic agent simultaneously or sequentially in separate unit dosage forms or together in a single unit dosage form.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

One or more other therapeutic agent may be administered separately from a compound or composition of the invention, as part of a multiple dosage regimen. Alternatively, one or more other therapeutic agents agents may be part of a single dosage form, mixed together with a compound of this invention in a single composition. If administered as a multiple dosage regime, one or more other therapeutic agent and a compound or composition of the invention may be administered simultaneously, sequentially or within a period of time from one another, for example within 1, 2, 3, 4, 5, 6, 7, 8, 9, 10, 11, 12, 13, 14, 15, 16, 17, 18, 18, 20, 21, 22, 23, or 24 hours from one another. In some embodiments, one or more other therapeutic agent and a compound or composition of the invention are administered as a multiple dosage regimen within greater than 24 hours aparts.

In one embodiment, the present invention provides a composition comprising a provided compound or a pharmaceutically acceptable salt thereof and one or more additional therapeutic agents. The therapeutic agent may be administered together with a provided compound or a pharmaceutically acceptable salt thereof, or may be administered prior to or following administration of a provided compound or a pharmaceutically acceptable salt thereof. Suitable therapeutic agents are described in further detail below. In certain embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours before the therapeutic agent. In other embodiments, a provided compound or a pharmaceutically acceptable salt thereof may be administered up to 5 minutes, 10 minutes, 15 minutes, 30 minutes, 1 hour, 2 hours, 3 hours, 4 hours, 5, hours, 6 hours, 7 hours, 8 hours, 9 hours, 10 hours, 11 hours, 12 hours, 13 hours, 14 hours, 15 hours, 16 hours, 17 hours, or 18 hours following the therapeutic agent.

In another embodiment, the present invention provides a method of treating an inflammatory disease, disorder or condition by administering to a patient in need thereof a provided compound or a pharmaceutically acceptable salt thereof and one or more additional therapeutic agents. Such additional therapeutic agents may be small molecules or recombinant biologic agents and include, for example, acetaminophen, non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol, febuxostat (Uloric®), sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), canakinumab (Ilaris®), anti-Jak inhibitors such as tofacitinib, antibodies such as rituximab (Rituxan®), "anti-T-cell" agents such as abatacept (Orencia®), "anti-IL-6" agents such as tocilizumab (Actemra®), diclofenac, cortisone, hyaluronic acid (Synvisc® or Hyalgan®), monoclonal antibodies such as tanezumab, anticoagulants such as heparin (Calcinparine® or Liquaemin®) and warfarin (Coumadin®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot®, anticholinergics or antispasmodics such as dicyclomine (Bentyl®), Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as beclomethasone dipropionate (Beclovent®, Qvar®, and Vanceril®), triamcinolone acetonide (Azmacort®), mometasone (Asthmanex®), budesonide (Pulmocort®), and flunisolide (Aerobid®), Afviar®, Symbicort®, Dulera®, cromolyn sodium (Intal®), methylxanthines such as theophylline (Theo-Dur®, Theolair®, Slo-Bid®, Uniphyl®, Theo-24®) and aminophylline, IgE antibodies such as omalizumab (Xolair®), nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), doxorubicin (Hydrodaunorubicin®), vincristine (Oncovin®), bortezomib (Velcade®), and dexamethasone (Decadron®) in combination with lenalidomide (Revlimid®), or any combination(s) thereof.

In another embodiment, the present invention provides a method of treating gout comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, colchicine (Colcrys®), corticosteroids such as prednisone, prednisolone, methylprednisolone, hydrocortisone, and the like, probenecid, allopurinol and febuxostat (Uloric®).

In another embodiment, the present invention provides a method of treating rheumatoid arthritis comprising administering to a patient in need thereof a provided compound or a pharmaceutically acceptable salt thereof and one or more additional therapeutic agents selected from non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, sulfasalazine (Azulfidine®), antimalarials such as hydroxychloroquine (Plaquenil®) and chloroquine (Aralen®), methotrexate (Rheumatrex®), gold salts such as gold thioglucose (Solganal®), gold thiomalate (Myochrysine®) and auranofin (Ridaura®), D-penicillamine (Depen® or Cuprimine®), azathioprine (Imuran®), cyclophosphamide (Cytoxan®), chlorambucil (Leukeran®), cyclosporine (Sandimmune®), leflunomide (Arava®) and "anti-TNF" agents such as etanercept (Enbrel®), infliximab (Remicade®), golimumab (Simponi®), certolizumab pegol (Cimzia®) and adalimumab (Humira®), "anti-IL-1" agents such as anakinra (Kineret®) and rilonacept (Arcalyst®), antibodies such as rituximab (Rituxan®), "anti-T-cell" agents such as abatacept (Orencia®) and "anti-IL-6" agents such as tocilizumab (Actemra®).

In some embodiments, the present invention provides a method of treating osteoarthritis comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, diclofenac, cortisone, hyaluronic acid (Synvisc® or Hyalgan®) and monoclonal antibodies such as tanezumab.

In some embodiments, the present invention provides a method of treating lupus comprising administering to a patient in need thereof a provided compound or a pharmaceutically acceptable salt thereof and one or more additional therapeutic agents selected from acetaminophen, non-steroidal anti-inflammatory drugs (NSAIDS) such as aspirin, ibuprofen, naproxen, etodolac (Lodine®) and celecoxib, corticosteroids such as prednisone, prednisolone, methylprednisolone, hydrocortisone, and the like, antimalarials such as hydroxychloroquine (Plaquenil®) and chloroquine (Aralen®), cyclophosphamide (Cytoxan®), methotrexate (Rheumatrex®), azathioprine (Imuran®) and anticoagulants such as heparin (Calcinparine® or Liquaemin®) and warfarin (Coumadin®).

In some embodiments, the present invention provides a method of treating inflammatory bowel disease comprising administering to a patient in need thereof a provided compound or a pharmaceutically acceptable salt thereof and one or more additional therapeutic agents selected from mesalamine (Asacol®) sulfasalazine (Azulfidine®), antidiarrheals such as diphenoxylate (Lomotil®) and loperamide (Imodium®), bile acid binding agents such as cholestyramine, alosetron (Lotronex®), lubiprostone (Amitiza®), laxatives such as Milk of Magnesia, polyethylene glycol (MiraLax®), Dulcolax®, Correctol® and Senokot® and anticholinergics or antispasmodics such as dicyclomine (Bentyl®), anti-TNF therapies, steroids, and antibiotics such as Flagyl or ciprofloxacin.

In some embodiments, the present invention provides a method of treating asthma comprising administering to a patient in need thereof a provided compound or a pharmaceutically acceptable salt thereof and one or more additional therapeutic agents selected from anti-IL-33 antibodies such as REGN3500 (SAR440340) or CNTO 7160, Singulair®, beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, cromolyn sodium (Intal®), methylxanthines such as theophylline (Theo-Dur®, Theolair®, Slo-Bid®, Uniphyl®, Theo-24®) and aminophylline, and IgE antibodies such as omalizumab (Xolair®).

In some embodiments, the present invention provides a method of treating COPD comprising administering to a patient in need thereof a provided compound or a pharmaceutically acceptable salt thereof and one or more additional therapeutic agents selected from beta-2 agonists such as albuterol (Ventolin® HFA, Proventil® HFA), levalbuterol (Xopenex®), metaproterenol (Alupent®), pirbuterol acetate (Maxair®), terbutaline sulfate (Brethaire®), salmeterol xinafoate (Serevent®) and formoterol (Foradil®), anticholinergic agents such as ipratropium bromide (Atrovent®) and tiotropium (Spiriva®), methylxanthines such as theophylline (Theo-Dur®, Theolair®, Slo-Bid®, Uniphyl®, Theo-24®) and aminophylline, inhaled corticosteroids such as prednisone, prednisolone, beclomethasone dipropionate (Beclovent®, Qvar®, and Vanceril®), triamcinolone acetonide (Azmacort®), mometasone (Asthmanex®), budesonide (Pulmocort®), flunisolide (Aerobid®), Afviar®, Symbicort®, and Dulera®, In some embodiments, the present invention provides a method of treating eosinophilic COPD comprising administering to a patient in need thereof a provided compound or a pharmaceutically acceptable salt thereof and one or more additional therapeutic agents selected from an anti-IL-33 antibody such as REGN3500 (SAR440340) or CNTO 7160. In some embodiments, the present invention provides a method of treating eosinophilic asthma comprising administering to a patient in need thereof a provided compound or a pharmaceutically acceptable salt thereof and one or more additional therapeutic agents selected from an anti-IL-33 antibody such as REGN3500 (SAR440340) or CNTO 7160.

In some embodiments, the present invention provides a method of treating HIV comprising administering to a patient in need thereof a provided compound or a pharmaceutically acceptable salt thereof and one or more additional therapeutic agents selected from nucleoside reverse transcriptase inhibitors such as zidovudine (Retrovir®), abacavir (Ziagen®), abacavir/lamivudine (Epzicom®), abacavir/lamivudine/zidovudine (Trizivir®), didanosine (Videx®), emtricitabine (Emtriva®), lamivudine (Epivir®), lamivudine/zidovudine (Combivir®), stavudine (Zerit®), and zalcitabine (Hivid®), non-nucleoside reverse transcriptase inhibitors such as delavirdine (Rescriptor®), efavirenz (Sustiva®), nevairapine (Viramune®) and etravirine (Intelence®), nucleotide reverse transcriptase inhibitors such as tenofovir (Viread®), protease inhibitors such as amprenavir (Agenerase®), atazanavir (Reyataz®), darunavir (Prezista®), fosamprenavir (Lexiva®), indinavir (Crixivan®), lopinavir and ritonavir (Kaletra®), nelfinavir (Viracept®), ritonavir (Norvir®), saquinavir (Fortovase® or Invirase®), and tipranavir (Aptivus®), entry inhibitors such as enfuvirtide (Fuzeon®) and maraviroc (Selzentry®), integrase inhibitors such as raltegravir (Isentress®), and combinations thereof.

In another embodiment, the present invention provides a method of treating a hematological malignancy comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a solid tumor comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, a BTK inhibitor, a JAK/pan-JAK inhibitor, a TYK2 inhibitor, a PI3K inhibitor, a SYK inhibitor, and combinations thereof.

In another embodiment, the present invention provides a method of treating a hematological malignancy comprising administering to a patient in need thereof a provided compound or a pharmaceutically acceptable salt thereof and a Hedgehog (Hh) signaling pathway inhibitor. In some embodiments, the hematological malignancy is DLBCL (Ramirez et a!"Defining causative factors contributing in the activation of hedgehog signaling in diffuse large B-cell lymphoma" Leuk. Res. (2012), published online July 17, and incorporated herein by reference in its entirety).

In another embodiment, the present invention provides a method of treating diffuse large B-cell lymphoma (DLBCL) comprising administering to a patient in need thereof a provided compound or a pharmaceutically acceptable salt thereof and one or more additional therapeutic agents selected from rituximab (Rituxan®), cyclophosphamide (Cytoxan®), doxorubicin (Hydrodaunorubicin®), vincristine (Oncovin®), prednisone, a hedgehog signaling inhibitor, and combinations thereof.

In some embodiments, the present invention provides a method of treating DLBCL comprising administering to a patient in need thereof a provided compound or a pharmaceutically acceptable salt thereof and a CHOP (cyclophosphamide, Hydrodaunorubicin®, Oncovin®, and prednisone or prednisolone) or R-CHOP (rituximab, cyclophosphamide, Hydrodaunorubicin®, Oncovin®, and prednisone or prednisolone) chemotherapy regimen.

In some embodiments, the present invention provides a method of treating DLBCL comprising administering to a patient in need thereof a provided compound or a pharmaceutically acceptable salt thereof and a rituximab/bendamustine chemotherapy regimen.

In some embodiments, the present invention provides a method of treating DLBCL comprising administering to a patient in need thereof a provided compound or a pharmaceutically acceptable salt thereof and a BTK inhibitor (e.g., ibrutinib).

In some embodiments, the present invention provides a method of treating DLBCL comprising administering to a patient in need thereof a provided compound or a pharmaceutically acceptable salt thereof and an anti-CD20 antibody (e.g., rituximab).

In some embodiments, the present invention provides a method of treating DLBCL comprising administering to a patient in need thereof a provided compound or a pharmaceutically acceptable salt thereof and an anti-CD79B ADC (e.g., polatuzumab).

In some embodiments, the present invention provides a method of treating DLBCL comprising administering to a patient in need thereof a provided compound or a pharmaceutically acceptable salt thereof and a BCL2 inhibitor (e.g., venetoclax).

In some embodiments, the present invention provides a method of treating DLBCL comprising administering to a patient in need thereof a provided compound or a pharmaceutically acceptable salt thereof and lenalidomide or pomalidomide In some embodiments, the present invention provides a method of treating DLBCL comprising administering to a patient in need thereof a provided compound or a pharmaceutically acceptable salt thereof and a PI3K inhibitor (e.g., umbralisib).

In some embodiments, the present invention provides a method of treating a T-cell disease or deficiency describing herein comprising administering to a patient in need thereof a provided compound or a pharmaceutically acceptable salt thereof and a PI3K inhibitor (e.g., umbralisib).

In some embodiments, the present invention provides a method of treating DLBCL comprising administering to a patient in need thereof a provided compound or a pharmaceutically acceptable salt thereof and a protesome inhibitor (e.g., bortezomib)

In some embodiments, the present invention provides a method of treating a T-cell disease or deficiency describing herein comprising administering to a patient in need thereof a provided compound or a pharmaceutically acceptable salt thereof and a protesome inhibitor (e.g., bortezomib).

In another embodiment, the present invention provides a method of treating multiple myeloma comprising administering to a patient in need thereof a provided compound or a pharmaceutically acceptable salt thereof and one or more additional therapeutic agents selected from bortezomib (Velcade®), and dexamethasone (Decadron®), a hedgehog signaling inhibitor, a BTK inhibitor, a JAK/pan-JAK inhibitor, a TYK2 inhibitor, a PI3K inhibitor, a SYK inhibitor in combination with lenalidomide (Revlimid®).

In another embodiment, the present invention provides a method of treating Waldenström's macroglobulinemia comprising administering to a patient in need thereof a provided compound or a pharmaceutically acceptable salt thereof and one or more additional therapeutic agents selected from chlorambucil (Leukeran®), cyclophosphamide (Cytoxan®, Neosar®), fludarabine (Fludara®), cladribine (Leustatin®), rituximab (Rituxan®), a hedgehog signaling inhibitor, a BTK inhibitor, a JAK/pan-JAK inhibitor, a TYK2 inhibitor, a PI3K inhibitor, and a SYK inhibitor.

In some embodiments, one or more other therapeutic agent is an antagonist of the hedgehog pathway. Approved hedgehog pathway inhibitors which may be used in the present invention include sonidegib (Odomzo®, Sun Pharmaceuticals); and vismodegib (Erivedge®, Genentech), both for treatment of basal cell carcinoma.

In some embodiments, one or more other therapeutic agent is a Poly ADP ribose polymerase (PARP) inhibitor. In some embodiments, a PARP inhibitor is selected from olaparib (Lynparza®, AstraZeneca); rucaparib (Rubraca®, Clovis Oncology); niraparib (Zejula®, Tesaro); talazoparib (MDV3800/BMN 673/LT00673, Medivation/Pfizer/Biomarin); veliparib (ABT-888, AbbVie); and BGB-290 (BeiGene, Inc.).

In some embodiments, one or more other therapeutic agent is a histone deacetylase (HDAC) inhibitor. In some embodiments, an HDAC inhibitor is selected from vorinostat (Zolinza®, Merck); romidepsin (Istodax®, Celgene); panobinostat (Farydak®, Novartis); belinostat (Beleodaq®, Spectrum Pharmaceuticals); entinostat (SNDX-275, Syndax Pharmaceuticals) (NCT00866333); and chidamide (Epidaza®, HBI-8000, Chipscreen Biosciences, China).

In some embodiments, one or more other therapeutic agent is a CDK inhibitor, such as a CDK4/CDK6 inhibitor. In some embodiments, a CDK 4/6 inhibitor is selected from palbociclib (Ibrance®, Pfizer); ribociclib (Kisqali®, Novartis); abemaciclib (Ly2835219, Eli Lilly); and trilaciclib (G1T28, G1 Therapeutics).

In some embodiments, one or more other therapeutic agent is a folic acid inhibitor. Approved folic acid inhibitors useful in the present invention include pemetrexed (Alimta®, Eli Lilly).

In some embodiments, one or more other therapeutic agent is a CC chemokine receptor 4 (CCR4) inhibitor. CCR4 inhibitors being studied that may be useful in the present invention include mogamulizumab (Poteligeo®, Kyowa Hakko Kirin, Japan).

In some embodiments, one or more other therapeutic agent is an isocitrate dehydrogenase (IDH) inhibitor. IDH inhibitors being studied which may be used in the present invention include AG120 (Celgene; NCT02677922); AG221 (Celgene, NCT02677922; NCT02577406); BAY1436032 (Bayer, NCT02746081); IDH305 (Novartis, NCT02987010).

In some embodiments, one or more other therapeutic agent is an arginase inhibitor. Arginase inhibitors being studied which may be used in the present invention include AEB 1102 (pegylated recombinant arginase, Aeglea Biotherapeutics), which is being studied in Phase 1 clinical trials for acute myeloid leukemia and myelodysplastic syndrome (NCT02732184) and solid tumors (NCT02561234); and CB-1158 (Calithera Biosciences).

In some embodiments, one or more other therapeutic agent is a glutaminase inhibitor. Glutaminase inhibitors being studied which may be used in the present invention include CB-839 (Calithera Biosciences).

In some embodiments, one or more other therapeutic agent is an antibody that binds to tumor antigens, that is, proteins expressed on the cell surface of tumor cells. Approved antibodies that bind to tumor antigens which may be used in the present invention include rituximab (Rituxan®, Genentech/BiogenIdec); ofatumumab (anti-CD20, Arzerra®, GlaxoSmithKline); obinutuzumab (anti-CD20, Gazyva®, Genentech), ibritumomab (anti-CD20 and Yttrium-90, Zevalin®, Spectrum Pharmaceuticals); daratumumab (anti-CD38, Darzalex®, Janssen Biotech), dinutuximab (anti-glycolipid GD2, Unituxin®, United Therapeutics); trastuzumab (anti-HER2, Herceptin®, Genentech); ado-trastuzumab emtansine (anti-HER2, fused to emtansine, Kadcyla®, Genentech); and pertuzumab (anti-HER2, Perjeta®, Genentech); and brentuximab vedotin (anti-CD30-drug conjugate, Adcetris®, Seattle Genetics).

In some embodiments, one or more other therapeutic agent is a topoisomerase inhibitor. Approved topoisomerase inhibitors useful in the present invention include irinotecan (Onivyde®, Merrimack Pharmaceuticals); topotecan (Hycamtin®, GlaxoSmithKline). Topoisomerase inhibitors being studied which may be used in the present invention include pixantrone (Pixuvri®, CTI Biopharma).

In some embodiments, one or more other therapeutic agent is an inhibitor of anti-apoptotic proteins, such as BCL-2. Approved anti-apoptotics which may be used in the present invention include venetoclax (Venclexta®, AbbVie/Genentech); and blinatumomab (Blincyto®, Amgen). Other therapeutic agents targeting apoptotic proteins which have undergone clinical testing and may be used in the present invention include navitoclax (ABT-263, Abbott), a BCL-2 inhibitor (NCT02079740).

In some embodiments, one or more other therapeutic agent is an androgen receptor inhibitor. Approved androgen receptor inhibitors useful in the present invention include enzalutamide (Xtandi®, Astellas/Medivation); approved inhibitors of androgen synthesis include abiraterone (Zytiga®, Centocor/Ortho); approved antagonist of gonadotropin-releasing hormone (GnRH) receptor (degaralix, Firmagon®, Ferring Pharmaceuticals).

In some embodiments, one or more other therapeutic agent is a selective estrogen receptor modulator (SERM), which interferes with the synthesis or activity of estrogens. Approved SERMs useful in the present invention include raloxifene (Evista®, Eli Lilly).

In some embodiments, one or more other therapeutic agent is an inhibitor of bone resorption. An approved therapeutic which inhibits bone resorption is Denosumab (Xgeva®, Amgen), an antibody that binds to RANKL, prevents binding to its receptor RANK, found on the surface of osteoclasts, their precursors, and osteoclast-like giant cells, which mediates bone pathology in solid tumors with osseous metastases. Other approved therapeutics that inhibit bone resorption include bisphosphonates, such as zoledronic acid (Zometa®, Novartis).

In some embodiments, one or more other therapeutic agent is an inhibitor of interaction between the two primary p53 suppressor proteins, MDMX and MDM2. Inhibitors of p53 suppression proteins being studied which may be used in the present invention include ALRN-6924 (Aileron), a stapled peptide that equipotently binds to and disrupts the interaction of MDMX and MDM2 with p53. ALRN-6924 is currently being evaluated in clinical trials for the treatment of AML, advanced myelodysplastic syndrome (MDS) and peripheral T-cell lymphoma (PTCL) (NCT02909972; NCT02264613).

In some embodiments, one or more other therapeutic agent is an inhibitor of transforming growth factor-beta (TGF-beta or TGFβ). Inhibitors of TGF-beta proteins being studied which may be used in the present invention include NIS793 (Novartis), an anti-TGF-beta antibody being tested in the clinic for treatment of various cancers, including breast, lung, hepatocellular, colorectal, pancreatic, prostate and renal cancer (NCT 02947165). In some embodiments, the inhibitor of TGF-beta proteins is fresolimumab (GC1008; Sanofi-Genzyme), which is being studied for melanoma (NCT00923169); renal cell carcinoma (NCT00356460); and non-small cell lung cancer (NCT02581787). Additionally, in some embodiments, the additional therapeutic agent is a TGF-beta trap, such as described in Connolly et al. (2012) Int'l J. Biological Sciences 8:964-978. One therapeutic compound currently in clinical trials for treatment of solid tumors is M7824 (Merck KgaA—formerly MSB0011459X), which is a bispecific, anti-PD-L1/TGF trap compound (NCT02699515); and (NCT02517398). M7824 is comprised of a fully human IgG1 antibody against PD-L1 fused to the extracellular domain of human TGF-beta receptor II, which functions as a TGFβ "trap."

In some embodiments, one or more other therapeutic agent is selected from glembatumumab vedotin-monomethyl auristatin E (MMAE) (Celldex), an anti-glycoprotein NMB (gpNMB) antibody (CR011) linked to the cytotoxic MMAE. gpNMB is a protein overexpressed by multiple tumor types associated with cancer cells' ability to metastasize.

In some embodiments, one or more other therapeutic agent is an antiproliferative compound. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF 1010, CNF2024, CNF 1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZd6244 from AstraZeneca, PD181461 from Pfizer and leucovorin.

In some embodiments, the present invention provides a method of treating Alzheimer's disease comprising administering to a patient in need thereof a provided compound or a pharmaceutically acceptable salt thereof and one or more additional therapeutic agents selected from donepezil (Aricept®), rivastigmine (Excelon®), galantamine (Razadyne®), tacrine (Cognex®), and memantine (Namenda®).

In some embodiments, one or more other therapeutic agent is a taxane compound, which causes disruption of microtubules, which are essential for cell division. In some embodiments, a taxane compound is selected from paclitaxel (Taxol®, Bristol-Myers Squibb), docetaxel (Taxotere®, Sanofi-Aventis; Docefrez®, Sun Pharmaceutical), albumin-bound paclitaxel (Abraxane®; Abraxis/Celgene), cabazitaxel (Jevtana®, Sanofi-Aventis), and SID530 (SK Chemicals, Co.) (NCT00931008).

In some embodiments, one or more other therapeutic agent is a nucleoside inhibitor, or a therapeutic agent that interferes with normal DNA synthesis, protein synthesis, cell replication, or will otherwise inhibit rapidly proliferating cells.

In some embodiments, a nucleoside inhibitor is selected from trabectedin (guanidine alkylating agent, Yondelis®, Janssen Oncology), mechlorethamine (alkylating agent, Valchlor®, Aktelion Pharmaceuticals); vincristine (Oncovin®, Eli Lilly; Vincasar®, Teva Pharmaceuticals; Marqibo®, Talon Therapeutics); temozolomide (prodrug to alkylating agent 5-(3-methyltriazen-1-yl)-imidazole-4-carboxamide (MTIC) Temodar®, Merck); cytarabine injection (ara-C, antimetabolic cytidine analog, Pfizer); lomustine (alkylating agent, CeeNU®, Bristol-Myers Squibb; Gleostine®, NextSource Biotechnology); azacitidine (pyrimidine nucleoside analog of cytidine, Vidaza®, Celgene); omacetaxine mepesuccinate (cephalotaxine ester) (protein synthesis inhibitor, Synribo®; Teva Pharmaceuticals); asparaginase *Erwinia chrysanthemi* (enzyme for depletion of asparagine, Elspar®, Lundbeck; Erwinaze®, EUSA Pharma); eribulin mesylate (microtubule inhibitor, tubulin-based antimitotic, Halaven®, Eisai); cabazitaxel (microtubule inhibitor, tubulin-based antimitotic, Jevtana®, Sanofi-Aventis); capacetrine (thymidylate synthase inhibitor, Xeloda®, Genentech); bendamustine (bifunctional mechlorethamine derivative, believed to form interstrand DNA cross-links, Treanda®, Cephalon/Teva); ixabepilone (semi-synthetic analog of epothilone B, microtubule inhibitor, tubulin-based antimitotic, Ixempra®, Bristol-Myers Squibb); nelarabine (prodrug of deoxyguanosine analog, nucleoside metabolic inhibitor, Arranon®, Novartis); clorafabine (prodrug of ribonucleotide reductase inhibitor, competitive inhibitor of deoxycytidine, Clolar®, Sanofi-Aventis); and trifluridine and tipiracil (thymidine-based nucleoside analog and thymidine phosphorylase inhibitor, Lonsurf®, Taiho Oncology).

In some embodiments, one or more other therapeutic agent is a kinase inhibitor or VEGF-R antagonist. Approved VEGF inhibitors and kinase inhibitors useful in the present invention include: bevacizumab (Avastin®, Genentech/Roche) an anti-VEGF monoclonal antibody; ramucirumab (Cyramza®, Eli Lilly), an anti-VEGFR-2 antibody and ziv-aflibercept, also known as VEGF Trap (Zaltrap®; Regeneron/Sanofi). VEGFR inhibitors, such as regorafenib (Stivarga®, Bayer); vandetanib (Caprelsa®, AstraZeneca); axitinib (Inlyta®, Pfizer); and lenvatinib (Lenvima®, Eisai); Raf inhibitors, such as sorafenib (Nexavar®, Bayer AG and Onyx); dabrafenib (Tafinlar®, Novartis); and vemurafenib (Zelboraf®, Genentech/Roche); MEK inhibitors, such as cobimetanib (Cotellic®, Exelexis/Genentech/Roche); trametinib (Mekinist®, Novartis); Bcr-Abl tyrosine kinase inhibitors, such as imatinib (Gleevec®, Novartis); nilotinib (Tasigna®, Novartis); dasatinib (Sprycel®, BristolMyersSquibb); bosutinib (Bosulif®, Pfizer); and ponatinib (Inclusig®, Ariad Pharmaceuticals); Her2 and EGFR inhibitors, such as gefitinib (Iressa®, AstraZeneca); erlotinib (Tarceeva®, Genentech/Roche/Astellas); lapatinib (Tykerb®, Novartis); afatinib (Gilotrif®, Boehringer Ingelheim); osimertinib (targeting activated EGFR, Tagrisso®, AstraZeneca); and brigatinib (Alunbrig®, Ariad Pharmaceuticals); c-Met and VEGFR2 inhibitors, such as cabozanitib (Cometriq®, Exelexis); and multikinase inhibitors, such as sunitinib (Sutent®, Pfizer); pazopanib (Votrient®, Novartis); ALK inhibitors, such as crizotinib (Xalkori®, Pfizer); ceritinib (Zykadia®, Novartis); and alectinib (Alecenza®, Genentech/Roche); Bruton's tyrosine kinase inhibitors, such as ibrutinib (Imbruvica®, Pharmacyclics/Janssen); and Flt3 receptor inhibitors, such as midostaurin (Rydapt®, Novartis).

Other kinase inhibitors and VEGF-R antagonists that are in development and may be used in the present invention include tivozanib (Aveo Pharmaecuticals); vatalanib (Bayer/Novartis); lucitanib (Clovis Oncology); dovitinib (TKI258, Novartis); Chiauanib (Chipscreen Biosciences); CEP-11981 (Cephalon); linifanib (Abbott Laboratories); neratinib (HKI-272, Puma Biotechnology); radotinib (Supect®, IY5511, Il-Yang Pharmaceuticals, S. Korea); ruxolitinib (Jakafi®, Incyte Corporation); PTC299 (PTC Therapeutics); CP-547, 632 (Pfizer); foretinib (Exelexis, GlaxoSmithKline); quizartinib (Daiichi Sankyo) and motesanib (Amgen/Takeda).

In another embodiment, the present invention provides a method of treating organ transplant rejection or graft vs. host disease comprising administering to a patient in need thereof a provided compound or a pharmaceutically acceptable salt thereof and one or more additional therapeutic agents selected from a steroid, cyclosporin, FK506, rapamycin, a hedgehog signaling inhibitor, a BTK inhibitor, a JAK/pan-JAK inhibitor, a TYK2 inhibitor, a PI3K inhibitor, and a SYK inhibitor.

In another embodiment, the present invention provides a method of treating or lessening the severity of a disease comprising administering to a patient in need thereof a provided compound or a pharmaceutically acceptable salt thereof and a BTK inhibitor, wherein the disease is selected from inflammatory bowel disease, arthritis, systemic lupus erythematosus (SLE), vasculitis, idiopathic thrombocytopenic purpura (ITP), rheumatoid arthritis, psoriatic arthritis, osteoarthritis, Still's disease, juvenile arthritis, diabetes, myasthenia gravis, Hashimoto's thyroiditis, Ord's thyroiditis, Graves' disease, autoimmune thyroiditis, Sjogren's syndrome, multiple sclerosis, systemic sclerosis, Lyme neuroborreliosis, Guillain-Barre syndrome, acute disseminated encephalomyelitis, Addison's disease, opsoclonus-myoclonus syndrome, ankylosing spondylosis, antiphospholipid antibody syndrome, aplastic anemia, autoimmune hepatitis, autoimmune gastritis, pernicious anemia, celiac disease, Goodpasture's syndrome, idiopathic thrombocytopenic purpura, optic neuritis, scleroderma, primary biliary cirrhosis, Reiter's syndrome, Takayasu's arteritis, temporal arteritis, warm autoimmune hemolytic anemia, Wegener's granulomatosis, psoriasis, alopecia universalis, Behcet's disease, chronic fatigue, dysautonomia, membranous glomerulonephropathy, endometriosis, interstitial cystitis, pemphigus vulgaris, bullous pemphigoid, neuromyotonia, scleroderma, vulvodynia, a hyperproliferative disease, rejection of transplanted organs or tissues, Acquired Immunodeficiency Syndrome (AIDS, also known as HIV), type 1 diabetes, graft versus host disease, transplantation, transfusion, anaphylaxis, allergies (e.g., allergies to plant pollens, latex, drugs, foods, insect poisons, animal hair, animal dander, dust mites, or cockroach calyx), type I hypersensitivity, allergic conjunctivitis, allergic rhinitis, and atopic dermatitis, asthma, appendicitis, atopic dermatitis, asthma, allergy, blepharitis, bronchiolitis, bronchitis, bursitis, cervicitis, cholangitis, cholecystitis, chronic graft rejection, colitis, conjunctivitis, Crohn's disease, cystitis, dacryoadenitis, dermatitis, dermatomyositis, encephalitis, endocarditis, endometritis, enteritis, enterocolitis, epicondylitis, epididymitis, fasciitis, fibrositis, gastritis, gastroenteritis, Henoch-Schonlein purpura, hepatitis, hidradenitis suppurativa, immunoglobulin A nephropathy, interstitial lung disease, laryngitis, mastitis, meningitis, myelitis myocarditis, myositis, nephritis, oophoritis, orchitis, osteitis, otitis, pancreatitis, parotitis, pericarditis, peritonitis, pharyngitis, pleuritis, phlebitis, pneumonitis, pneumonia, polymyositis, proctitis, prostatitis, pyelonephritis, rhinitis, salpingitis, sinusitis, stomatitis, synovitis, tendonitis, tonsillitis, ulcerative colitis, uveitis, vaginitis, vasculitis, or vulvitis, B-cell proliferative disorder, e.g., diffuse large B cell lymphoma, follicular lymphoma, chronic lymphocytic lymphoma, chronic lymphocytic leukemia, acute lymphocytic leukemia, B-cell prolymphocytic leukemia, lymphoplasmacytic lymphoma/Waldenstrom macroglobulinemia, splenic marginal zone lymphoma, multiple myeloma (also known as plasma cell myeloma), non-Hodgkin's lymphoma, Hodgkin's lymphoma, plasmacytoma, extranodal marginal zone B cell lymphoma, nodal marginal zone B cell lymphoma, mantle cell lymphoma, mediastinal (thymic) large B cell lymphoma, intravascular large B cell lymphoma, primary effusion lymphoma, Burkitt lymphoma/leukemia, or lymphomatoid granulomatosis, breast cancer, prostate cancer, or cancer of the mast cells (e.g., mastocytoma, mast cell leukemia, mast cell sarcoma, systemic mastocytosis), bone cancer, colorectal cancer, pancreatic cancer, diseases of the bone and joints including, without limitation, rheumatoid arthritis, seronegative spondyloarthropathies (including ankylosing spondylitis, psoriatic arthritis and Reiter's disease), Behcet's disease, Sjogren's syndrome, systemic sclerosis, osteoporosis, bone cancer, bone metastasis, a thromboembolic disorder, (e.g., myocardial infarct, angina pectoris, reocclusion after angioplasty, restenosis after angioplasty, reocclusion after aortocoronary bypass, restenosis after aortocoronary bypass, stroke, transitory ischemia, a peripheral arterial occlusive disorder, pulmonary embolism, deep venous thrombosis), inflammatory pelvic disease, urethritis, skin sunburn, sinusitis, pneumonitis, encephalitis, meningitis, myocarditis, nephritis, osteomyelitis, myositis, hepatitis, gastritis, enteritis, dermatitis, gingivitis, appendicitis, pancreatitis, cholocystitus, agammaglobulinemia, psoriasis, allergy, Crohn's disease, irritable bowel syndrome, ulcerative colitis, Sjogren's disease, tissue graft rejection, hyperacute rejection of transplanted organs, asthma, allergic rhinitis, chronic obstructive pulmonary disease (COPD), autoimmune polyglandular disease (also known as autoimmune polyglandular syndrome), autoimmune alopecia, pernicious anemia, glomerulonephritis, dermatomyositis, multiple sclerosis, scleroderma, vasculitis, autoimmune hemolytic and thrombocytopenic states, Goodpasture's syndrome, atherosclerosis, Addison's disease, Parkinson's disease, Alzheimer's disease, diabetes, septic shock, systemic lupus erythematosus (SLE), rheumatoid arthritis, psoriatic arthritis, juvenile arthritis, osteoarthritis, chronic idiopathic thrombocytopenic purpura, Waldenstrom macroglobulinemia, myasthenia gravis, Hashimoto's thyroiditis, atopic dermatitis, degenerative joint disease, vitiligo, autoimmune hypopituitarism, Guillain-Barre syndrome, Behcet's disease, scleraderma, mycosis fungoides, acute inflammatory responses (such as acute respiratory distress syndrome and ischemia/reperfusion injury), and Graves' disease.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from a cancer, a neurodegenerative disorder, an angiogenic disorder, a viral disease, an autoimmune disease, an inflammatory disorder, a hormone-related disease, conditions associated with organ transplantation, immunodeficiency disorders, a destructive bone disorder, a proliferative disorder, an infectious disease, a condition associated with cell death, thrombin-induced platelet aggregation, chronic myelogenous leukemia (CML), chronic lymphocytic leukemia (CLL), liver disease, pathologic immune conditions involving T cell activation, a cardiovascular disorder, and a CNS disorder.

In another embodiment, the present invention provides a method of treating or lessening the severity of a disease comprising administering to a patient in need thereof a provided compound or a pharmaceutically acceptable salt thereof and a PI3K inhibitor, wherein the disease is selected from benign or malignant tumor, carcinoma or solid tumor of the brain, kidney (e.g., renal cell carcinoma (RCC)), liver, adrenal gland, bladder, breast, stomach, gastric tumors, ovaries, colon, rectum, prostate, pancreas, lung, vagina, endometrium, cervix, testis, genitourinary tract, esophagus, larynx, skin, bone or thyroid, sarcoma, glioblastomas, neuroblastomas, multiple myeloma or gastrointestinal cancer, especially colon carcinoma or colorectal adenoma or a tumor of the neck and head, an epidermal hyperproliferation, psoriasis, prostate hyperplasia, a neoplasia, a neoplasia of epithelial character, adenoma, adenocarcinoma, keratoacanthoma, epidermoid carcinoma, large cell carcinoma, non-small-cell lung carcinoma, lymphomas, (including, for example, non-Hodgkin's Lymphoma (NHL) and Hodgkin's lymphoma (also termed Hodgkin's or Hodgkin's disease)), a mammary carcinoma, follicular carcinoma, undifferentiated carcinoma, papillary carcinoma, seminoma, melanoma, or a leukemia, diseases include Cowden syndrome, Lhermitte-Dudos disease and Bannayan-Zonana syndrome, or diseases in which the PI3K/PKB pathway is aberrantly activated, asthma of whatever type or genesis including both intrinsic (non-allergic) asthma and extrinsic (allergic) asthma, mild asthma, moderate asthma, severe asthma, bronchitic asthma, exercise-induced asthma, occupational asthma and asthma induced following bacterial infection, acute lung injury (ALI), adult/acute respiratory distress syndrome (ARDS), chronic obstructive pulmonary, airways or lung disease (COPD, COAD or COLD), including chronic bronchitis or dyspnea associated therewith, emphysema, as well as exacerbation of airways hyperreactivity consequent to other drug therapy, in particular other inhaled drug therapy, bronchitis of whatever type or genesis including, but not limited to, acute, arachidic, catarrhal, croupus, chronic or phthinoid bronchitis, pneumoconiosis (an inflammatory, commonly occupational, disease of the lungs, frequently accompanied by airways obstruction, whether chronic or acute, and occasioned by repeated inhalation of dusts) of whatever type or genesis, including, for example, aluminosis, anthracosis, asbestosis, chalicosis, ptilosis, siderosis, silicosis, tabacosis and byssinosis, Loffler's syndrome, eosinophilic, pneumonia, parasitic (in particular metazoan) infestation (including tropical eosinophilia), bronchopulmonary aspergillosis, polyarteritis nodosa (including Churg-Strauss syndrome), eosinophilic granuloma and eosinophil-related disorders affecting the airways occasioned by drug-reaction, psoriasis, contact dermatitis, atopic dermatitis, alopecia areata, erythema multiforma, dermatitis herpetiformis, scleroderma, vitiligo, hypersensitivity angiitis, urticaria, bullous pemphigoid, lupus erythematosus, pemphisus, epidermolysis bullosa acquisita, conjunctivitis, keratoconjunctivitis sicca, and vernal conjunctivitis, diseases affecting the nose including allergic rhinitis, and inflammatory disease in which autoimmune reactions are implicated or having an autoimmune component or etiology, including autoimmune hematological disorders (e.g. hemolytic anemia, aplastic anemia, pure red cell anemia and idiopathic thrombocytopenia), systemic lupus erythematosus, rheumatoid arthritis, polychondritis, sclerodoma, Wegener granulamatosis, dermatomyositis, chronic active hepatitis, myasthenia gravis, Steven-Johnson syndrome, idiopathic sprue, autoimmune inflammatory bowel disease (e.g. ulcerative colitis and Crohn's disease), endocrine opthalmopathy, Grave's disease, sarcoidosis, alveolitis, chronic hypersensitivity pneumonitis, multiple sclerosis, primary biliary cirrhosis, uveitis (anterior and posterior), keratoconjunctivitis sicca and vernal keratoconjunctivitis, interstitial lung fibrosis, psoriatic arthritis and glomerulonephritis (with and without nephrotic syndrome, e.g. including idiopathic nephrotic syndrome or minal change nephropathy, restenosis, cardiomegaly, atherosclerosis, myocardial infarction, ischemic stroke and congestive heart failure, Alzheimer's disease, Parkinson's disease, amyotrophic lateral sclerosis, Huntington's disease, and cerebral ischemia, and neurodegenerative disease caused by traumatic injury, glutamate neurotoxicity and hypoxia.

In some embodiments, one or more other therapeutic agent is a phosphatidylinositol 3 kinase (PI3K) inhibitor. In some embodiments, a PI3K inhibitor is selected from idelalisib (Zydelig®, Gilead), alpelisib (BYL719, Novartis), taselisib (GDC-0032, Genentech/Roche); pictilisib (GDC-0941, Genentech/Roche); copanlisib (BAY806946, Bayer); duvelisib (formerly IPI-145, Infinity Pharmaceuticals); PQR309 (Piqur Therapeutics, Switzerland); and TGR1202 (formerly RP5230, TG Therapeutics).

In some embodiments, the present invention provides a method of treating AML comprising administering to a patient in need thereof a provided compound or a pharmaceutically acceptable salt thereof and one or more additional therapeutic agents selected from: FLT3 inhibitors; targeted agents such as IDH inhibitors, anti-CD33 ADCs (e.g. Mylotarg), BCL2 inhibitors, and Hedgehog inhibitors; and chemotherapy such as AraC, daunarubicin, etoposide, methotrexate, fludarabine, mitozantrone, azacytidine, and corticosteroids.

In some embodiments, the present invention provides a method of treating MDS comprising administering to a patient in need thereof a provided compound or a pharmaceutically acceptable salt thereof and one or more additional therapeutic agents selected from azacytidine, decitabine and revlimid.

In some embodiments, the present invention provides a method of treating inflammatory skin conditions such as hidradenitis suppurativa, comprising administering to a patient in need thereof a provided compound or a pharmaceutically acceptable salt thereof and one or more additional therapeutic agents selected from anti-TNF drugs.

In some embodiments, the present invention provides a method of treating inflammatory skin conditions such as atopic dermatitis, comprising administering to a patient in need thereof a provided compound or a pharmaceutically acceptable salt thereof and one or more additional therapeutic agents selected from IL-4/IL-13-targeted agents such as dupilumab. In some embodiments, the present invention provides a method of treating inflammatory skin conditions such as psoriasis, comprising administering to a patient in need thereof a provided compound or a pharmaceutically acceptable salt thereof and one or more additional therapeutic agents selected from anti-IL-17 and anti-IL-23 antibodies.

The compounds and compositions, according to the method of the present invention, may be administered using any amount and any route of administration effective for treating or lessening the severity of a cancer, an autoimmune disorder, a proliferative disorder, an inflammatory disorder, a neurodegenerative or neurological disorder, schizophrenia, a bone-related disorder, liver disease, or a cardiac disorder. The exact amount required will vary from subject to subject, depending on the species, age, and general condition of the subject, the severity of the infection, the particular agent, its mode of administration, and the like. Compounds of the invention are preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts. The term "patient", as used herein, means an animal, preferably a mammal, and most preferably a human.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, the compounds of the invention may be administered orally or parenterally at dosage levels of about 0.01 mg/kg to about 50 mg/kg and preferably from about 1 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a compound of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled gelatin capsules using such excipients as lactose or milk sugar as well as high molecular weight polethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to one embodiment, the invention relates to a method of inhibiting protein kinase activity or degading a protein kinase in a biological sample comprising the step of contacting said biological sample with a compound of this invention, or a composition comprising said compound.

According to another embodiment, the invention relates to a method of inhibiting or degrading IRAK-1, IRAK-2, and/or IRAK-4, or a mutant thereof, activity in a biological sample comprising the step of contacting said biological sample with a compound of this invention, or a composition comprising said compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Inhibition and/or degradation of a protein kinase, or a protein kinase selected from IRAK-1, IRAK-2, and/or IRAK-4, or a mutant thereof, activity in a biological sample is useful for a variety of purposes that are known to one of skill in the art. Examples of such purposes include, but are not limited to, blood transfusion, organ-transplantation, biological specimen storage, and biological assays.

Another embodiment of the present invention relates to a method of degrading a protein kinase and/or inhibiting protein kinase activity in a patient comprising the step of administering to said patient a compound of the present invention, or a composition comprising said compound.

According to another embodiment, the invention relates to a method of degrading and/or inhibiting one or more of IRAK-1, IRAK-2, and/or IRAK-4, or a mutant thereof, activity in a patient comprising the step of administering to said patient a compound of the present invention, or a composition comprising said compound. In other embodiments, the present invention provides a method for treating a disorder mediated by one or more of IRAK-1, IRAK-2, and/or IRAK-4, or a mutant thereof, in a patient in need thereof, comprising the step of administering to said patient a compound according to the present invention or pharmaceutically acceptable composition thereof. Such disorders are described in detail herein.

Depending upon the particular condition, or disease, to be treated, additional therapeutic agents that are normally administered to treat that condition, may also be present in the compositions of this invention. As used herein, additional therapeutic agents that are normally administered to treat a particular disease, or condition, are known as "appropriate for the disease, or condition, being treated."

A compound of the current invention may also be used to advantage in combination with other antiproliferative compounds. Such antiproliferative compounds include, but are not limited to aromatase inhibitors; antiestrogens; topoisomerase I inhibitors; topoisomerase II inhibitors; microtubule active compounds; alkylating compounds; histone deacetylase inhibitors; compounds which induce cell differentiation processes; cyclooxygenase inhibitors; MMP inhibitors; mTOR inhibitors; antineoplastic antimetabolites; platin compounds; compounds targeting/decreasing a protein or lipid kinase activity and further anti-angiogenic compounds; compounds which target, decrease or inhibit the activity of a protein or lipid phosphatase; gonadorelin agonists; anti-androgens; methionine aminopeptidase inhibitors; matrix metalloproteinase inhibitors; bisphosphonates; biological response modifiers; antiproliferative antibodies; heparanase inhibitors; inhibitors of Ras oncogenic isoforms; telomerase inhibitors; proteasome inhibitors; compounds used in the treatment of hematologic malignancies; compounds which target, decrease or inhibit the activity of Flt-3; Hsp90 inhibitors such as 17-AAG (17-allylaminogeldanamycin, NSC330507), 17-DMAG (17-dimethylaminoethylamino-17-demethoxy-geldanamycin, NSC707545), IPI-504, CNF1010, CNF2024, CNF1010 from Conforma Therapeutics; temozolomide (Temodal®); kinesin spindle protein inhibitors, such as SB715992 or SB743921 from GlaxoSmithKline, or pentamidine/chlorpromazine from CombinatoRx; MEK inhibitors such as ARRY142886 from Array BioPharma, AZD6244 from AstraZeneca, PD181461 from Pfizer and leucovorin.

The term "aromatase inhibitor" as used herein relates to a compound which inhibits estrogen production, for instance, the conversion of the substrates androstenedione and testosterone to estrone and estradiol, respectively. The term includes, but is not limited to steroids, especially atamestane, exemestane and formestane and, in particular, non-steroids, especially aminoglutethimide, roglethimide, pyridoglutethimide, trilostane, testolactone, ketoconazole, vorozole, fadrozole, anastrozole and letrozole. Exemestane is marketed under the trade name Aromasin™. Formestane is marketed under the trade name Lentaron™. Fadrozole is marketed under the trade name Afema™. Anastrozole is marketed under the trade name Arimidex™ Letrozole is marketed under the trade names Femara™ or Femar™. Aminoglutethimide is marketed under the trade name Orimeten™. A combination of the invention comprising a chemotherapeutic agent which is an aromatase inhibitor is particularly useful for the treatment of hormone receptor positive tumors, such as breast tumors.

In some embodiments, one or more other therapeutic agent is an mTOR inhibitor, which inhibits cell proliferation, angiogenesis and glucose uptake. In some embodiments, an mTOR inhibitor is everolimus (Afinitor®, Novartis); temsirolimus (Torisel®, Pfizer); and sirolimus (Rapamune®, Pfizer).

In some embodiments, one or more other therapeutic agent is an aromatase inhibitor. In some embodiments, an aromatase inhibitor is selected from exemestane (Aromasin®, Pfizer); anastazole (Arimidex®, AstraZeneca) and letrozole (Femara®, Novartis).

The term "antiestrogen" as used herein relates to a compound which antagonizes the effect of estrogens at the estrogen receptor level. The term includes, but is not limited to tamoxifen, fulvestrant, raloxifene and raloxifene hydrochloride. Tamoxifen is marketed under the trade name Nolvadex™. Raloxifene hydrochloride is marketed under the trade name Evista™. Fulvestrant can be administered under the trade name Faslodex™. A combination of the invention comprising a chemotherapeutic agent which is an antiestrogen is particularly useful for the treatment of estrogen receptor positive tumors, such as breast tumors.

The term "anti-androgen" as used herein relates to any substance which is capable of inhibiting the biological effects of androgenic hormones and includes, but is not limited to, bicalutamide (Casodex™). The term "gonadorelin agonist" as used herein includes, but is not limited to abarelix, goserelin and goserelin acetate. Goserelin can be administered under the trade name Zoladex™.

The term "topoisomerase I inhibitor" as used herein includes, but is not limited to topotecan, gimatecan, irinotecan, camptothecian and its analogues, 9-nitrocamptothecin and the macromolecular camptothecin conjugate PNU-166148. Irinotecan can be administered, e.g. in the form as it is marketed, e.g. under the trademark Camptosar™. Topotecan is marketed under the trade name Hycamptin™.

The term "topoisomerase II inhibitor" as used herein includes, but is not limited to the anthracyclines such as doxorubicin (including liposomal formulation, such as Caelyx™), daunorubicin, epirubicin, idarubicin and nemorubicin, the anthraquinones mitoxantrone and losoxantrone, and the podophillotoxines etoposide and teniposide. Etoposide is marketed under the trade name Etopophos™. Teniposide is marketed under the trade name VM 26-Bristol Doxorubicin is marketed under the trade name Acriblastin™ or Adriamycin™. Epirubicin is marketed under the trade name Farmorubicin™. Idarubicin is marketed. under the trade name Zavedos™. Mitoxantrone is marketed under the trade name Novantron.

The term "microtubule active agent" relates to microtubule stabilizing, microtubule destabilizing compounds and microtublin polymerization inhibitors including, but not limited to taxanes, such as paclitaxel and docetaxel; *vinca* alkaloids, such as vinblastine or vinblastine sulfate, vincristine or vincristine sulfate, and vinorelbine; discodermolides; cochicine and epothilones and derivatives thereof. Paclitaxel is marketed under the trade name Taxol™. Docetaxel is marketed under the trade name Taxotere™. Vinblastine sulfate is marketed under the trade name Vinblastin R.P™. Vincristine sulfate is marketed under the trade name Farmistin™.

The term "alkylating agent" as used herein includes, but is not limited to, cyclophosphamide, ifosfamide, melphalan or nitrosourea (BCNU or Gliadel). Cyclophosphamide is marketed under the trade name Cyclostin™. Ifosfamide is marketed under the trade name Holoxan™.

The term "histone deacetylase inhibitors" or "HDAC inhibitors" relates to compounds which inhibit the histone deacetylase and which possess antiproliferative activity. This includes, but is not limited to, suberoylanilide hydroxamic acid (SAHA).

The term "antineoplastic antimetabolite" includes, but is not limited to, 5-fluorouracil or 5-FU, capecitabine, gemcitabine, DNA demethylating compounds, such as 5-azacytidine and decitabine, methotrexate and edatrexate, and folic acid antagonists such as pemetrexed. Capecitabine is marketed under the trade name Xeloda™. Gemcitabine is marketed under the trade name Gemzar™.

The term "platin compound" as used herein includes, but is not limited to, carboplatin, cis-platin, cisplatinum and oxaliplatin. Carboplatin can be administered, e.g., in the form as it is marketed, e.g. under the trademark Carboplat™. Oxaliplatin can be administered, e.g., in the form as it is marketed, e.g. under the trademark Eloxatin™.

The term "Bcl-2 inhibitor" as used herein includes, but is not limited to compounds having inhibitory activity against B-cell lymphoma 2 protein (Bcl-2), including but not limited to ABT-199, ABT-731, ABT-737, apogossypol, Ascenta's pan-Bcl-2 inhibitors, curcumin (and analogs thereof), dual Bcl-2/Bcl-xL inhibitors (Infinity Pharmaceuticals/Novartis Pharmaceuticals), Genasense (G3139), HA14-1 (and analogs thereof; see WO 2008/118802, US 2010/0197686), navitoclax (and analogs thereof, see U.S. Pat. No. 7,390, 799), NH-1 (Shenayng Pharmaceutical University), obatoclax (and analogs thereof, see WO 2004/106328, US 2005/ 0014802), S-001 (Gloria Pharmaceuticals), TW series compounds (Univ. of Michigan), and venetoclax. In some embodiments the Bcl-2 inhibitor is a small molecule therapeutic. In some embodiments the Bcl-2 inhibitor is a peptidomimetic.

The term "compounds targeting/decreasing a protein or lipid kinase activity; or a protein or lipid phosphatase activity; or further anti-angiogenic compounds" as used herein includes, but is not limited to, protein tyrosine kinase and/or serine and/or threonine kinase inhibitors or lipid kinase inhibitors, such as a) compounds targeting, decreasing or inhibiting the activity of the platelet-derived growth factor-receptors (PDGFR), such as compounds which target, decrease or inhibit the activity of PDGFR, especially compounds which inhibit the PDGF receptor, such as an N-phenyl-2-pyrimidine-amine derivative, such as imatinib, SU101, SU6668 and GFB-111; b) compounds targeting, decreasing or inhibiting the activity of the fibroblast growth factor-receptors (FGFR); c) compounds targeting, decreasing or inhibiting the activity of the insulin-like growth factor receptor I (IGF-IR), such as compounds which target, decrease or inhibit the activity of IGF-IR, especially compounds which inhibit the kinase activity of IGF-I receptor, or antibodies that target the extracellular domain of IGF-I receptor or its growth factors; d) compounds targeting, decreasing or inhibiting the activity of the Trk receptor tyrosine kinase family, or ephrin B4 inhibitors; e) compounds targeting, decreasing or inhibiting the activity of the Axl receptor tyrosine kinase family; f) compounds targeting, decreasing or inhibiting the activity of the Ret receptor tyrosine kinase; g) compounds targeting, decreasing or inhibiting the activity of the Kit/SCFR receptor tyrosine kinase, such as imatinib; h) compounds targeting, decreasing or inhibiting the activity of the C-kit receptor tyrosine kinases, which are part of the PDGFR family, such as compounds which target, decrease or inhibit the activity of the c-Kit receptor tyrosine kinase family, especially compounds which inhibit the c-Kit receptor, such as imatinib; i) compounds targeting, decreasing or inhibiting the activity of members of the c-Abl family, their gene-fusion products (e.g. BCR-Abl kinase) and mutants, such as compounds which target decrease or inhibit the activity of c-Abl family members and their gene fusion products, such as an N-phenyl-2-pyrimidine-amine derivative, such as imatinib or nilotinib (AMN107); PD 180970; AG957; NSC 680410; PD173955 from ParkeDavis; or dasatinib (BMS-354825); j) compounds targeting, decreasing or inhibiting the activity of members of the protein kinase C (PKC) and Raf family of serine/threonine kinases, members of the MEK, SRC, JAK/ pan-JAK, FAK, PDK1, PKB/Akt, Ras/MAPK, PI3K, SYK, TYK2, BTK and TEC family, and/or members of the cyclin-dependent kinase family (CDK) including staurosporine derivatives, such as midostaurin; examples of further compounds include UCN-01, safingol, BAY 43-9006, Bryostatin 1, Perifosine; llmofosine; RO 318220 and RO 320432; GO 6976; lsis 3521; LY333531/LY379196; isochinoline compounds; FTIs; PD184352 or QAN697 (a PI3K inhibitor) or AT7519 (CDK inhibitor); k) compounds targeting, decreasing or inhibiting the activity of protein-tyrosine kinase inhibitors, such as compounds which target, decrease or inhibit the activity of protein-tyrosine kinase inhibitors include imatinib mesylate (Gleevec™) or tyrphostin such as Tyrphostin A23/RG-50810; AG 99; Tyrphostin AG 213; Tyrphostin AG 1748; Tyrphostin AG 490; Tyrphostin B44; Tyrphostin B44 (+) enantiomer; Tyrphostin AG 555; AG 494; Tyrphostin AG 556, AG957 and adaphostin (4-{[(2,5-dihydroxyphenyl)methyl]amino}-benzoic acid adamantyl ester; NSC 680410, adaphostin); 1) compounds targeting, decreasing or inhibiting the activity of the epidermal growth factor family of receptor tyrosine kinases (EGFR$_1$ ErbB2, ErbB3, ErbB4 as homo- or heterodimers) and their mutants, such as compounds which target, decrease or inhibit the activity of the epidermal growth factor receptor family are especially compounds, proteins or antibodies which inhibit members of the EGF receptor tyrosine kinase family, such as EGF receptor, ErbB2, ErbB3 and ErbB4 or bind to EGF or EGF related ligands, CP 358774, ZD 1839, ZM 105180; trastuzumab (Herceptin™), cetuximab (Erbitux™), Iressa, Tarceva, OSI-774, Cl-1033, EKB-569, GW-2016, E1.1, E2.4, E2.5, E6.2, E6.4, E2.11, E6.3 or E7.6.3, and 7H-pyrrolo-[2,3-d]pyrimidine derivatives; m) compounds targeting, decreasing or inhibiting the activity of the c-Met receptor, such as compounds which target, decrease or inhibit the activity of c-Met, especially compounds which inhibit the kinase activity of c-Met receptor, or antibodies that target the extracellular domain of c-Met or bind to HGF, n) compounds targeting, decreasing or inhibiting the kinase activity of one or more JAK family members (JAK1/JAK2/JAK3/ TYK2 and/or pan-JAK), including but not limited to PRT-062070, SB-1578, baricitinib, pacritinib, momelotinib, VX-509, AZD-1480, TG-101348, tofacitinib, and ruxolitinib; o) compounds targeting, decreasing or inhibiting the kinase activity of PI3 kinase (PI3K) including but not limited to ATU-027, SF-1126, DS-7423, PBI-05204, GSK-2126458, Z STK-474, buparlisib, pictrelisib, PF-4691502, BYL-719, dactolisib, XL-147, XL-765, and idelalisib; and; and q) compounds targeting, decreasing or inhibiting the signaling effects of hedgehog protein (Hh) or smoothened receptor (SMO) pathways, including but not limited to cyclopamine, vismodegib, itraconazole, erismodegib, and IPI-926 (saridegib).

Compounds which target, decrease or inhibit the activity of a protein or lipid phosphatase are e.g. inhibitors of phosphatase 1, phosphatase 2A, or CDC25, such as okadaic acid or a derivative thereof.

In some embodiments, one or more other therapeutic agent is a growth factor antagonist, such as an antagonist of platelet-derived growth factor (PDGF), or epidermal growth factor (EGF) or its receptor (EGFR). Approved PDGF antagonists which may be used in the present invention include olaratumab (Lartruvo®; Eli Lilly). Approved EGFR antagonists which may be used in the present invention include cetuximab (Erbitux®, Eli Lilly); necitumumab (Portrazza®, Eli Lilly), panitumumab (Vectibix®, Amgen); and osimertinib (targeting activated EGFR, Tagrisso®, AstraZeneca).

The term "PI3K inhibitor" as used herein includes, but is not limited to compounds having inhibitory activity against one or more enzymes in the phosphatidylinositol-3-kinase family, including, but not limited to PI3Kα, PI3Kγ, PI3Kδ, PI3Kβ, PI3K-C2α, PI3K-C2β, PI3K-C2γ, Vps34, p110-α, p110-β, p110-γ, p110-δ, p85-α, p85-β, p55-γ, p150, p101, and p87. Examples of PI3K inhibitors useful in this invention include but are not limited to ATU-027, SF-1126, DS-7423, PBI-05204, GSK-2126458, ZSTK-474, buparlisib, pictrelisib, PF-4691502, BYL-719, dactolisib, XL-147, XL-765, and idelalisib.

The term "BTK inhibitor" as used herein includes, but is not limited to compounds having inhibitory activity against Bruton's Tyrosine Kinase (BTK), including, but not limited to AVL-292 and ibrutinib.

The term "SYK inhibitor" as used herein includes, but is not limited to compounds having inhibitory activity against spleen tyrosine kinase (SYK), including but not limited to PRT-062070, R-343, R-333, Excellair, PRT-062607, and fostamatinib Further examples of BTK inhibitory compounds, and conditions treatable by such compounds in combination with compounds of this invention can be found in WO 2008/039218, US 2008/0108636 and WO 2011/090760, US 2010/0249092, the entirety of each of which is herein incorporated by reference.

Further examples of SYK inhibitory compounds, and conditions treatable by such compounds in combination with compounds of this invention can be found in WO 2003/063794, US 2004/0029902, WO 2005/007623, US 2005/0075306, and WO 2006/078846, US 2006/0211657, the entirety of each of which is herein incorporated by reference.

Further examples of PI3K inhibitory compounds, and conditions treatable by such compounds in combination with compounds of this invention can be found in WO 2004/019973, US 2004/0106569, WO 2004/089925, US 2004/0242631, U.S. Pat. No. 8,138,347, WO 2002/088112, US 2004/0116421, WO 2007/084786, US 2010/0249126, WO 2007/129161, US 2008/0076768, WO 2006/122806, US 2008/0194579, WO 2005/113554, US 2008/0275067, and WO 2007/044729, US 2010/0087440, the entirety of each of which is herein incorporated by reference.

Further examples of JAK inhibitory compounds, and conditions treatable by such compounds in combination with compounds of this invention can be found in WO 2009/114512, US 2009/0233903, WO 2008/109943, US 2010/0197671, WO 2007/053452, US 2007/0191405, WO 2001/0142246, US 2001/0053782, and WO 2007/070514, US 2007/0135461, the entirety of each of which is herein incorporated by reference.

Further anti-angiogenic compounds include compounds having another mechanism for their activity, e.g. unrelated to protein or lipid kinase inhibition e.g. thalidomide (Thalomid™) and TNP-470.

Examples of proteasome inhibitors useful for use in combination with compounds of the invention include, but are not limited to bortezomib, disulfiram, epigallocatechin-3-gallate (EGCG), salinosporamide A, carfilzomib, ONX-0912, CEP-18770, and MLN9708.

Compounds which target, decrease or inhibit the activity of a protein or lipid phosphatase are e.g. inhibitors of phosphatase 1, phosphatase 2A, or CDC25, such as okadaic acid or a derivative thereof.

Compounds which induce cell differentiation processes include, but are not limited to, retinoic acid, α- γ- or δ-tocopherol or α- γ- or δ-tocotrienol.

The term cyclooxygenase inhibitor as used herein includes, but is not limited to, Cox-2 inhibitors, 5-alkyl substituted 2-arylaminophenylacetic acid and derivatives, such as celecoxib (Celebrex™), rofecoxib (Vioxx™), etoricoxib, valdecoxib or a 5-alkyl-2-arylaminophenylacetic acid, such as 5-methyl-2-(2'-chloro-6'-fluoroanilino)phenyl acetic acid, lumiracoxib.

The term "bisphosphonates" as used herein includes, but is not limited to, etridonic, clodronic, tiludronic, pamidronic, alendronic, ibandronic, risedronic and zoledronic acid. Etridonic acid is marketed under the trade name Didronel™. Clodronic acid is marketed under the trade name Bonefos™. Tiludronic acid is marketed under the trade name Skelid™. Pamidronic acid is marketed under the trade name Aredia™. Alendronic acid is marketed under the trade name Fosamax™. Ibandronic acid is marketed under the trade name Bondranat™. Risedronic acid is marketed under the trade name Actonel™. Zoledronic acid is marketed under the trade name Zometa™. The term "mTOR inhibitors" relates to compounds which inhibit the mammalian target of rapamycin (mTOR) and which possess antiproliferative activity such as sirolimus (Rapamune®), everolimus (Certican™), CCI-779 and ABT578.

The term "heparanase inhibitor" as used herein refers to compounds which target, decrease or inhibit heparin sulfate degradation. The term includes, but is not limited to, PI-88. The term "biological response modifier" as used herein refers to a lymphokine or interferons.

The term "inhibitor of Ras oncogenic isoforms", such as H-Ras, K-Ras, or N-Ras, as used herein refers to compounds which target, decrease or inhibit the oncogenic activity of Ras; for example, a "farnesyl transferase inhibitor" such as L-744832, DK8G557 or R115777 (Zarnestra™). The term "telomerase inhibitor" as used herein refers to compounds which target, decrease or inhibit the activity of telomerase. Compounds which target, decrease or inhibit the activity of telomerase are especially compounds which inhibit the telomerase receptor, such as telomestatin.

The term "methionine aminopeptidase inhibitor" as used herein refers to compounds which target, decrease or inhibit the activity of methionine aminopeptidase. Compounds which target, decrease or inhibit the activity of methionine aminopeptidase include, but are not limited to, bengamide or a derivative thereof.

The term "proteasome inhibitor" as used herein refers to compounds which target, decrease or inhibit the activity of the proteasome. Compounds which target, decrease or inhibit the activity of the proteasome include, but are not limited to, Bortezomib (Velcade™), ); carfilzomib (Kyprolis®, Amgen); and ixazomib (Ninlaro®, Takeda), and MLN 341.

The term "matrix metalloproteinase inhibitor" or ("MMP" inhibitor) as used herein includes, but is not limited to, collagen peptidomimetic and nonpeptidomimetic inhibitors, tetracycline derivatives, e.g. hydroxamate peptidomimetic inhibitor batimastat and its orally bioavailable analogue marimastat (BB-2516), prinomastat (AG3340), metastat (NSC 683551) BMS-279251, BAY 12-9566, TAA211, MMI270B or AAJ996.

The term "compounds used in the treatment of hematologic malignancies" as used herein includes, but is not limited to, FMS-like tyrosine kinase inhibitors, which are compounds targeting, decreasing or inhibiting the activity of FMS-like tyrosine kinase receptors (Flt-3R); interferon, 1-β-D-arabinofuransylcytosine (ara-c) and bisulfan; and ALK inhibitors, which are compounds which target, decrease or inhibit anaplastic lymphoma kinase.

Compounds which target, decrease or inhibit the activity of FMS-like tyrosine kinase receptors (Flt-3R) are especially compounds, proteins or antibodies which inhibit members of the Flt-3R receptor kinase family, such as PKC412, midostaurin, a staurosporine derivative, SU11248 and MLN518.

The term "HSP90 inhibitors" as used herein includes, but is not limited to, compounds targeting, decreasing or inhibiting the intrinsic ATPase activity of HSP90; degrading, targeting, decreasing or inhibiting the HSP90 client proteins via the ubiquitin proteosome pathway. Compounds targeting, decreasing or inhibiting the intrinsic ATPase activity of HSP90 are especially compounds, proteins or antibodies which inhibit the ATPase activity of HSP90, such as 17-allylamino, 17-demethoxygeldanamycin (17AAG), a geldanamycin derivative; other geldanamycin related compounds; radicicol and HDAC inhibitors.

The term "antiproliferative antibodies" as used herein includes, but is not limited to, trastuzumab (Herceptin™), Trastuzumab-DM1, erbitux, bevacizumab (Avastin™), rituximab (Rituxan®), PR064553 (anti-CD40) and 2C4 Antibody. By antibodies is meant intact monoclonal antibodies, polyclonal antibodies, multispecific antibodies formed from at least 2 intact antibodies, and antibodies fragments so long as they exhibit the desired biological activity.

For the treatment of acute myeloid leukemia (AML), compounds of the current invention can be used in combination with standard leukemia therapies, especially in combination with therapies used for the treatment of AML. In particular, compounds of the current invention can be administered in combination with, for example, farnesyl transferase inhibitors and/or other drugs useful for the treatment of AML, such as Daunorubicin, Adriamycin, Ara-C, VP-16, Teniposide, Mitoxantrone, Idarubicin, Carboplatinum and PKC412.

Other anti-leukemic compounds include, for example, Ara-C, a pyrimidine analog, which is the 2'-alpha-hydroxy ribose (arabinoside) derivative of deoxycytidine. Also included is the purine analog of hypoxanthine, 6-mercaptopurine (6-MP) and fludarabine phosphate. Compounds which target, decrease or inhibit activity of histone deacetylase (HDAC) inhibitors such as sodium butyrate and suberoylanilide hydroxamic acid (SAHA) inhibit the activity of the enzymes known as histone deacetylases. Specific HDAC inhibitors include MS275, SAHA, FK228 (formerly FR901228), Trichostatin A and compounds disclosed in U.S. Pat. No. 6,552,065 including, but not limited to, N-hydroxy-3-[4-[[[2-(2-methyl-1H-indol-3-yl)-ethyl]-amino]methyl]

phenyl]-2E-2-propenamide, or a pharmaceutically acceptable salt thereof and N-hydroxy-3-[4-[(2-hydroxyethyl) {2-(1H-indol-3-yl)ethyl]-amino]methyl]phenyl]-2E-2-propenamide, or a pharmaceutically acceptable salt thereof, especially the lactate salt. Somatostatin receptor antagonists as used herein refer to compounds which target, treat or inhibit the somatostatin receptor such as octreotide, and SOM230. Tumor cell damaging approaches refer to approaches such as ionizing radiation. The term "ionizing radiation" referred to above and hereinafter means ionizing radiation that occurs as either electromagnetic rays (such as X-rays and gamma rays) or particles (such as alpha and beta particles). Ionizing radiation is provided in, but not limited to, radiation therapy and is known in the art. See Hellman, Principles of Radiation Therapy, Cancer, in Principles and Practice of Oncology, Devita et al., Eds., 4$^{th}$ Edition, Vol. 1, pp. 248-275 (1993).

Also included are EDG binders and ribonucleotide reductase inhibitors. The term "EDG binders" as used herein refers to a class of immunosuppressants that modulates lymphocyte recirculation, such as FTY720. The term "ribonucleotide reductase inhibitors" refers to pyrimidine or purine nucleoside analogs including, but not limited to, fludarabine and/or cytosine arabinoside (ara-C), 6-thioguanine, 5-fluorouracil, cladribine, 6-mercaptopurine (especially in combination with ara-C against ALL) and/or pentostatin. Ribonucleotide reductase inhibitors are especially hydroxyurea or 2-hydroxy-1H-isoindole-1,3-dione derivatives.

Also included are in particular those compounds, proteins or monoclonal antibodies of VEGF such as 1-(4-chloroanilino)-4-(4-pyridylmethyl)phthalazine or a pharmaceutically acceptable salt thereof, 1-(4-chloroanilino)-4-(4-pyridylmethyl)phthalazine succinate; Angiostatin™; Endostatin™; anthranilic acid amides; ZD4190; ZD6474; SU5416; SU6668; bevacizumab; or anti-VEGF antibodies or anti-VEGF receptor antibodies, such as rhuMAb and RHUFab, VEGF aptamer such as Macugon; FLT-4 inhibitors, FLT-3 inhibitors, VEGFR-2 IgGI antibody, Angiozyme (RPI 4610) and Bevacizumab (Avastin™).

Photodynamic therapy as used herein refers to therapy which uses certain chemicals known as photosensitizing compounds to treat or prevent cancers. Examples of photodynamic therapy include treatment with compounds, such as Visudyne™ and porfimer sodium.

Angiostatic steroids as used herein refers to compounds which block or inhibit angiogenesis, such as, e.g., anecortave, triamcinolone, hydrocortisone, 11-α-epihydrocotisol, cortexolone, 17α-hydroxyprogesterone, corticosterone, desoxycorticosterone, testosterone, estrone and dexamethasone.

Implants containing corticosteroids refers to compounds, such as fluocinolone and dexamethasone.

Other chemotherapeutic compounds include, but are not limited to, plant alkaloids, hormonal compounds and antagonists; biological response modifiers, preferably lymphokines or interferons; antisense oligonucleotides or oligonucleotide derivatives; shRNA or siRNA; or miscellaneous compounds or compounds with other or unknown mechanism of action.

The compounds of the invention are also useful as co-therapeutic compounds for use in combination with other drug substances such as anti-inflammatory, bronchodilatory or antihistamine drug substances, particularly in the treatment of obstructive or inflammatory airways diseases such as those mentioned hereinbefore, for example as potentiators of therapeutic activity of such drugs or as a means of reducing required dosaging or potential side effects of such drugs. A compound of the invention may be mixed with the other drug substance in a fixed pharmaceutical composition or it may be administered separately, before, simultaneously with or after the other drug substance. Accordingly the invention includes a combination of a compound of the invention as hereinbefore described with an anti-inflammatory, bronchodilatory, antihistamine or anti-tussive drug substance, said compound of the invention and said drug substance being in the same or different pharmaceutical composition.

Suitable anti-inflammatory drugs include steroids, in particular glucocorticosteroids such as budesonide, beclamethasone dipropionate, fluticasone propionate, ciclesonide or mometasone furoate; non-steroidal glucocorticoid receptor agonists; LTB4 antagonists such LY293111, CGS025019C, CP-195543, SC-53228, BIIL 284, ONO 4057, SB 209247; LTD4 antagonists such as montelukast and zafirlukast; PDE4 inhibitors such cilomilast (Ariflo® GlaxoSmithKline), Roflumilast (Byk Gulden), V-11294A (Napp), BAY19-8004 (Bayer), SCH-351591 (Schering-Plough), Arofylline (Almirall Prodesfarma), PD189659/PD168787 (Parke-Davis), AWD-12-281 (Asta Medica), CDC-801 (Celgene), SelCID™ CC-10004 (Celgene), VM554/UM565 (Vernalis), T-440 (Tanabe), KW-4490 (Kyowa Hakko Kogyo); A2a agonists; A2b antagonists; and beta-2 adrenoceptor agonists such as albuterol (salbutamol), metaproterenol, terbutaline, salmeterol fenoterol, procaterol, and especially, formoterol and pharmaceutically acceptable salts thereof. Suitable bronchodilatory drugs include anticholinergic or antimuscarinic compounds, in particular ipratropium bromide, oxitropium bromide, tiotropium salts and CHF 4226 (Chiesi), and glycopyrrolate.

Suitable antihistamine drug substances include cetirizine hydrochloride, acetaminophen, clemastine fumarate, promethazine, loratidine, desloratidine, diphenhydramine and fexofenadine hydrochloride, activastine, astemizole, azelastine, ebastine, epinastine, mizolastine and tefenadine.

Other useful combinations of compounds of the invention with anti-inflammatory drugs are those with antagonists of chemokine receptors, e.g. CCR-1, CCR-2, CCR-3, CCR-4, CCR-5, CCR-6, CCR-7, CCR-8, CCR-9 and CCR10, CXCR1, CXCR2, CXCR3, CXCR4, CXCR5, particularly CCR-5 antagonists such as Schering-Plough antagonists SC-351125, SCH-55700 and SCH-D, and Takeda antagonists such as N-[[4-[[[6,7-dihydro-2-(4-methylphenyl)-5H-benzo-cyclohepten-8-yl]carbonyl]amino]phenyl]-methyl] tetrahydro-N,N-dimethyl-2H-pyran-4-aminium chloride (TAK-770).

The structure of the active compounds identified by code numbers, generic or trade names may be taken from the actual edition of the standard compendium "The Merck Index" or from databases, e.g. Patents International (e.g. IMS World Publications).

A compound of the current invention may also be used in combination with known therapeutic processes, for example, the administration of hormones or radiation. In certain embodiments, a provided compound is used as a radiosensitizer, especially for the treatment of tumors which exhibit poor sensitivity to radiotherapy.

A compound of the current invention can be administered alone or in combination with one or more other therapeutic compounds, possible combination therapy taking the form of fixed combinations or the administration of a compound of the invention and one or more other therapeutic compounds being staggered or given independently of one another, or the combined administration of fixed combinations and one or more other therapeutic compounds. A compound of the current invention can besides or in addition be administered especially for tumor therapy in combination with chemotherapy, radiotherapy, immunotherapy, phototherapy, surgical intervention, or a combination of these. Long-term therapy is equally possible as is adjuvant therapy in the context of other treatment strategies, as described above. Other possible treatments are therapy to maintain the patient's status after tumor regression, or even chemopreventive therapy, for example in patients at risk.

Those additional agents may be administered separately from an inventive compound-containing composition, as part of a multiple dosage regimen. Alternatively, those agents may be part of a single dosage form, mixed together with a compound of this invention in a single composition. If administered as part of a multiple dosage regime, the two active agents may be submitted simultaneously, sequentially or within a period of time from one another normally within five hours from one another.

As used herein, the term "combination," "combined," and related terms refers to the simultaneous or sequential administration of therapeutic agents in accordance with this invention. For example, a compound of the present invention may be administered with another therapeutic agent simultaneously or sequentially in separate unit dosage forms or together in a single unit dosage form. Accordingly, the present invention provides a single unit dosage form comprising a compound of the current invention, an additional therapeutic agent, and a pharmaceutically acceptable carrier, adjuvant, or vehicle.

The amount of both an inventive compound and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of an inventive compound can be administered.

In those compositions which comprise an additional therapeutic agent, that additional therapeutic agent and the compound of this invention may act synergistically. Therefore, the amount of additional therapeutic agent in such compositions will be less than that required in a monotherapy utilizing only that therapeutic agent. In such compositions a dosage of between 0.01-1,000 µg/kg body weight/day of the additional therapeutic agent can be administered.

The amount of one or more other therapeutic agent present in the compositions of this invention may be no more than the amount that would normally be administered in a composition comprising that therapeutic agent as the only active agent. Preferably the amount of one or more other therapeutic agent in the presently disclosed compositions will range from about 50% to 100% of the amount normally present in a composition comprising that agent as the only therapeutically active agent. In some embodiments, one or more other therapeutic agent is administered at a dosage of about 50%, about 55%, about 60%, about 65%, about 70%, about 75%, about 80%, about 85%, about 90%, or about 95% of the amount normally administered for that agent. As used herein, the phrase "normally administered" means the amount an FDA approved therapeutic agent is approvided for dosing per the FDA label insert.

The compounds of this invention, or pharmaceutical compositions thereof, may also be incorporated into compositions for coating an implantable medical device, such as prostheses, artificial valves, vascular grafts, stents and catheters. Vascular stents, for example, have been used to overcome restenosis (re-narrowing of the vessel wall after injury). However, patients using stents or other implantable devices risk clot formation or platelet activation. These unwanted effects may be prevented or mitigated by pre-coating the device with a pharmaceutically acceptable composition comprising a kinase inhibitor. Implantable devices coated with a compound of this invention are another embodiment of the present invention.

Exemplary Immuno-Oncology Agents

In some embodiments, one or more other therapeutic agent is an immuno-oncology agent. As used herein, the term "an immuno-oncology agent" refers to an agent which is effective to enhance, stimulate, and/or up-regulate immune responses in a subject. In some embodiments, the administration of an immuno-oncology agent with a compound of the invention has a synergic effect in treating a cancer.

An immuno-oncology agent can be, for example, a small molecule drug, an antibody, or a biologic or small molecule. Examples of biologic immuno-oncology agents include, but are not limited to, cancer vaccines, antibodies, and cytokines. In some embodiments, an antibody is a monoclonal antibody. In some embodiments, a monoclonal antibody is humanized or human.

In some embodiments, an immuno-oncology agent is (i) an agonist of a stimulatory (including a co-stimulatory) receptor or (ii) an antagonist of an inhibitory (including a co-inhibitory) signal on T cells, both of which result in amplifying antigen-specific T cell responses.

Certain of the stimulatory and inhibitory molecules are members of the immunoglobulin super family (IgSF). One important family of membrane-bound ligands that bind to co-stimulatory or co-inhibitory receptors is the B7 family, which includes B7-1, B7-2, B7-H1 (PD-L1), B7-DC (PD-L2), B7-H2 (ICOS-L), B7-H3, B7-H4, B7-H5 (VISTA), and B7-H6. Another family of membrane bound ligands that bind to co-stimulatory or co-inhibitory receptors is the TNF family of molecules that bind to cognate TNF receptor family members, which includes CD40 and CD40L, OX-40, OX-40L, CD70, CD27L, CD30, CD30L, 4-1BBL, CD137 (4-1BB), TRAIL/Apo2-L, TRAILR1/DR4, TRAILR2/DR5, TRAILR3, TRAILR4, OPG, RANK, RANKL, TWEAKR/Fnl4, TWEAK, BAFFR, EDAR, XEDAR, TACI, APRIL, BCMA, LTβR, LIGHT, DcR3, HVEM, VEGI/TL1A, TRAMP/DR3, EDAR, EDA1, XEDAR, EDA2, TNFR1, Lymphotoxin α/TNFβ, TNFR2, TNFα, LTβR, Lymphotoxin α1β2, FAS, FASL, RELT, DR6, TROY, NGFR.

In some embodiments, an immuno-oncology agent is a cytokine that inhibits T cell activation (e.g., IL-6, IL-10, TGF-β, VEGF, and other immunosuppressive cytokines) or a cytokine that stimulates T cell activation, for stimulating an immune response.

In some embodiments, a combination of a compound of the invention and an immuno-oncology agent can stimulate T cell responses. In some embodiments, an immuno-oncology agent is: (i) an antagonist of a protein that inhibits T cell activation (e.g., immune checkpoint inhibitors) such as CTLA-4, PD-1, PD-L1, PD-L2, LAG-3, TIM-3, Galectin 9, CEACAM-1, BTLA, CD69, Galectin-1, TIGIT, CD113, GPR56, VISTA, 2B4, CD48, GARP, PD1H, LAIR1, TIM-1, and TIM-4; or (ii) an agonist of a protein that stimulates T cell activation such as B7-1, B7-2, CD28, 4-1BB (CD137), 4-1BBL, ICOS, ICOS-L, OX40, OX40L, GITR, GITRL, CD70, CD27, CD40, DR3 and CD28H.

In some embodiments, an immuno-oncology agent is an antagonist of inhibitory receptors on NK cells or an agonists of activating receptors on NK cells. In some embodiments, an immuno-oncology agent is an antagonists of KIR, such as lirilumab.

In some embodiments, an immuno-oncology agent is an agent that inhibits or depletes macrophages or monocytes, including but not limited to CSF-1R antagonists such as CSF-1R antagonist antibodies including RG7155 (WO 2011/070024, US 2011/0165156, WO 2011/0107553, US 2012/0329997, WO 2011/131407, US 2013/0005949, WO 2013/087699, US 2014/0336363, WO 2013/119716, WO 2013/132044, US 2014/0079706) or FPA-008 (WO 2011/140249, US 2011/0274683; WO 2013/169264; WO 2014/036357, US 2014/0079699).

In some embodiments, an immuno-oncology agent is selected from agonistic agents that ligate positive costimulatory receptors, blocking agents that attenuate signaling through inhibitory receptors, antagonists, and one or more agents that increase systemically the frequency of anti-tumor T cells, agents that overcome distinct immune suppressive pathways within the tumor microenvironment (e.g., block inhibitory receptor engagement (e.g., PD-L1/PD-1 interactions), deplete or inhibit Tregs (e.g., using an anti-CD25 monoclonal antibody (e.g., daclizumab) or by ex vivo anti-CD25 bead depletion), inhibit metabolic enzymes such as IDO, or reverse/prevent T cell energy or exhaustion) and agents that trigger innate immune activation and/or inflammation at tumor sites.

In some embodiments, an immuno-oncology agent is a CTLA-4 antagonist. In some embodiments, a CTLA-4 antagonist is an antagonistic CTLA-4 antibody. In some embodiments, an antagonistic CTLA-4 antibody is YERVOY (ipilimumab) or tremelimumab.

In some embodiments, an immuno-oncology agent is a PD-1 antagonist. In some embodiments, a PD-1 antagonist is administered by infusion. In some embodiments, an immuno-oncology agent is an antibody or an antigen-binding portion thereof that binds specifically to a Programmed Death-1 (PD-1) receptor and inhibits PD-1 activity. In some embodiments, a PD-1 antagonist is an antagonistic PD-1 antibody. In some embodiments, an antagonistic PD-1 antibody is OPDIVO (nivolumab), KEYTRUDA (pembrolizumab), or MEDI-0680 (AMP-514; WO2012/145493). In some embodiments, an immuno-oncology agent may be pidilizumab (CT-011). In some embodiments, an immuno-oncology agent is a recombinant protein composed of the extracellular domain of PD-L2 (B7-DC) fused to the Fc portion of IgG1, called AMP-224.

In some embodiments, an immuno-oncology agent is a PD-L1 antagonist. In some embodiments, a PD-L1 antagonist is an antagonistic PD-L1 antibody. In some embodiments, a PD-L1 antibody is MPDL3280A (RG7446; WO 2010/077634, US 2010/0203056), durvalumab (MED14736), BMS-936559 (WO 2007/005874, US 2009/0055944), and MSB0010718C (WO 2013/079174, US 2014/0341917).

In some embodiments, an immuno-oncology agent is a LAG-3 antagonist. In some embodiments, a LAG-3 antagonist is an antagonistic LAG-3 antibody. In some embodiments, a LAG3 antibody is BMS-986016 (WO 2010/019570, US 2010/0150892, WO 2014/008218, US 2014/0093511), or IMP-731 or IMP-321 (WO 2008/132601, US 2010/0233183, WO 2009/044273, US 2011/0008331).

In some embodiments, an immuno-oncology agent is a CD137 (4-1BB) agonist. In some embodiments, a CD137 (4-1BB) agonist is an agonistic CD137 antibody. In some embodiments, a CD 137 antibody is urelumab or PF-05082566 (WO12/32433).

In some embodiments, an immuno-oncology agent is a GITR agonist. In some embodiments, a GITR agonist is an agonistic GITR antibody. In some embodiments, a GITR antibody is BMS-986153, BMS-986156, TRX-518 (WO 2006/105021, US 2007/0098719, WO 2009/009116, US 2009/0136494), or MK-4166 (WO 2011/028683, US 2012/0189639).

In some embodiments, an immuno-oncology agent is an indoleamine (2,3)-dioxygenase (IDO) antagonist. In some embodiments, an IDO antagonist is selected from epacadostat (INCB024360, Incyte); indoximod (NLG-8189, NewLink Genetics Corporation); capmanitib (INC280, Novartis); GDC-0919 (Genentech/Roche); PF-06840003 (Pfizer); BMS:F001287 (Bristol-Myers Squibb); Phy906/KD108 (Phytoceutica); an enzyme that breaks down kynurenine (Kynase, Kyn Therapeutics); and NLG-919 (WO 2009/073620, US 2011/0053941, WO 2009/132238, US 2011/0136796, WO 2011/056652, US 2012/0277217, WO 2012/142237, US 2014/0066625).

In some embodiments, an immuno-oncology agent is an OX40 agonist. In some embodiments, an OX40 agonist is an agonistic OX40 antibody. In some embodiments, an OX40 antibody is MEDI-6383 or MEDI-6469.

In some embodiments, an immuno-oncology agent is an OX40L antagonist. In some embodiments, an OX40L antagonist is an antagonistic OX40 antibody. In some embodiments, an OX40L antagonist is RG-7888 (WO 2006/029879, U.S. Pat. No. 7,501,496).

In some embodiments, an immuno-oncology agent is a CD40 agonist. In some embodiments, a CD40 agonist is an agonistic CD40 antibody. In some embodiments, an immuno-oncology agent is a CD40 antagonist. In some embodiments, a CD40 antagonist is an antagonistic CD40 antibody. In some embodiments, a CD40 antibody is lucatumumab or dacetuzumab.

In some embodiments, an immuno-oncology agent is a CD27 agonist. In some embodiments, a CD27 agonist is an agonistic CD27 antibody. In some embodiments, a CD27 antibody is varlilumab.

In some embodiments, an immuno-oncology agent is MGA271 (to B7H3) (WO 2011/109400, US 2013/0149236).

In some embodiments, an immuno-oncology agent is abagovomab, adecatumumab, afutuzumab, alemtuzumab, anatumomab mafenatox, apolizumab, atezolimab, avelumab, blinatumomab, BMS-936559, catumaxomab, durvalumab, epacadostat, epratuzumab, indoximod, inotuzumab ozogamicin, intelumumab, ipilimumab, isatuximab, lambrolizumab, MED14736, MPDL3280A, nivolumab, obinutuzumab, ocaratuzumab, ofatumumab, olatatumab, pembrolizumab, pidilizumab, rituximab, ticilimumab, samalizumab, or tremelimumab.

In some embodiments, an immuno-oncology agent is an immunostimulatory agent. For example, antibodies blocking the PD-1 and PD-L1 inhibitory axis can unleash activated tumor-reactive T cells and have been shown in clinical trials to induce durable anti-tumor responses in increasing numbers of tumor histologies, including some tumor types that conventionally have not been considered immunotherapy sensitive. See, e.g., Okazaki, T. et al. (2013) Nat. Immunol. 14, 1212-1218; Zou et al. (2016) Sci. Transl. Med. 8. The anti-PD-1 antibody nivolumab (Opdivo®, Bristol-Myers Squibb, also known as ONO-4538, MDX1106 and BMS-936558), has shown potential to improve the overall survival in patients with RCC who had experienced disease progression during or after prior anti-angiogenic therapy.

In some embodiments, the immunomodulatory therapeutic specifically induces apoptosis of tumor cells. Approved immunomodulatory therapeutics which may be used in the present invention include pomalidomide (Pomalyst®, Celgene); lenalidomide (Revlimid®, Celgene); ingenol mebutate (Picato®, LEO Pharma).

In some embodiments, an immuno-oncology agent is a cancer vaccine. In some embodiments, the cancer vaccine is selected from sipuleucel-T (Provenge®, Dendreon/Valeant Pharmaceuticals), which has been approved for treatment of asymptomatic, or minimally symptomatic metastatic castrate-resistant (hormone-refractory) prostate cancer; and talimogene laherparepvec (Imlygic®, BioVex/Amgen, previously known as T-VEC), a genetically modified oncolytic viral therapy approved for treatment of unresectable cutaneous, subcutaneous and nodal lesions in melanoma. In some embodiments, an immuno-oncology agent is selected from an oncolytic viral therapy such as pexastimogene devacirepvec (PexaVec/JX-594, SillaJen/formerly Jennerex Biotherapeutics), a thymidine kinase- (TK-) deficient vaccinia virus engineered to express GM-CSF, for hepatocellular carcinoma (NCT02562755) and melanoma (NCT00429312); pelareorep (Reolysin®, Oncolytics Biotech), a variant of respiratory enteric orphan virus (reovirus) which does not replicate in cells that are not RAS-activated, in numerous cancers, including colorectal cancer (NCT01622543); prostate cancer (NCT01619813); head and neck squamous cell cancer (NCT01166542); pancreatic adenocarcinoma (NCT00998322); and non-small cell lung cancer (NSCLC) (NCT 00861627); enadenotucirev (NG-348, PsiOxus, formerly known as ColoAd1), an adenovirus engineered to express a full length CD80 and an antibody fragment specific for the T-cell receptor CD3 protein, in ovarian cancer (NCT02028117); metastatic or advanced epithelial tumors such as in colorectal cancer, bladder cancer, head and neck squamous cell carcinoma and salivary gland cancer (NCT02636036); ONCOS-102 (Targovax/formerly Oncos), an adenovirus engineered to express GM-CSF, in melanoma (NCT03003676); and peritoneal disease, colorectal cancer or ovarian cancer (NCT02963831); GL-ONC1 (GLV-1h68/GLV-1h153, Genelux GmbH), vaccinia viruses engineered to express beta-galactosidase (beta-gal)/beta-glucoronidase or beta-gal/human sodium iodide symporter (hNIS), respectively, were studied in peritoneal carcinomatosis (NCT01443260); fallopian tube cancer, ovarian cancer (NCT 02759588); or CG0070 (Cold Genesys), an adenovirus engineered to express GM-CSF, in bladder cancer (NCT02365818).

In some embodiments, an immuno-oncology agent is selected from JX-929 (SillaJen/formerly Jennerex Biotherapeutics), a TK- and vaccinia growth factor-deficient vaccinia virus engineered to express cytosine deaminase, which is able to convert the prodrug 5-fluorocytosine to the cytotoxic drug 5-fluorouracil; TG01 and TG02 (Targovax/formerly Oncos), peptide-based immunotherapy agents targeted for difficult-to-treat RAS mutations; and TILT-123 (TILT Biotherapeutics), an engineered adenovirus designated: Ad5/3-E2F-delta24-hTNFα-IRES-hIL20; and VSV-GP (ViraTherapeutics) a vesicular stomatitis virus (VSV) engineered to express the glycoprotein (GP) of lymphocytic choriomeningitis virus (LCMV), which can be further engineered to express antigens designed to raise an antigen-specific CD8$^+$ T cell response.

In some embodiments, an immuno-oncology agent is a T-cell engineered to express a chimeric antigen receptor, or CAR. The T-cells engineered to express such chimeric antigen receptor are referred to as a CAR-T cells.

CARs have been constructed that consist of binding domains, which may be derived from natural ligands, single chain variable fragments (scFv) derived from monoclonal antibodies specific for cell-surface antigens, fused to endodomains that are the functional end of the T-cell receptor (TCR), such as the CD3-zeta signaling domain from TCRs, which is capable of generating an activation signal in T lymphocytes. Upon antigen binding, such CARs link to endogenous signaling pathways in the effector cell and generate activating signals similar to those initiated by the TCR complex.

For example, in some embodiments the CAR-T cell is one of those described in U.S. Pat. No. 8,906,682, the entirety of each of which is herein incorporated by reference, which discloses CAR-T cells engineered to comprise an extracellular domain having an antigen binding domain (such as a domain that binds to CD 19), fused to an intracellular signaling domain of the T cell antigen receptor complex zeta chain (such as CD3 zeta). When expressed in the T cell, the CAR is able to redirect antigen recognition based on the antigen binding specificity. In the case of CD19, the antigen is expressed on malignant B cells. Over 200 clinical trials are currently in progress employing CAR-T in a wide range of indications. [https://clinicaltrials.gov/ct2/results?term=chimeric+antigen+receptors&pg=1].

In some embodiments, an immunostimulatory agent is an activator of retinoic acid receptor-related orphan receptor γ (RORγt). RORγt is a transcription factor with key roles in the differentiation and maintenance of Type 17 effector subsets of CD4+(Th17) and CD8+(Tc17) T cells, as well as the differentiation of IL-17 expressing innate immune cell subpopulations such as NK cells. In some embodiments, an activator of RORγt is LYC-55716 (Lycera), which is currently being evaluated in clinical trials for the treatment of solid tumors (NCT02929862).

In some embodiments, an immunostimulatory agent is an agonist or activator of a toll-like receptor (TLR). Suitable activators of TLRs include an agonist or activator of TLR9 such as SD-101 (Dynavax). SD-101 is an immunostimulatory CpG which is being studied for B-cell, follicular and other lymphomas (NCT02254772). Agonists or activators of TLR8 which may be used in the present invention include motolimod (VTX-2337, VentiRx Pharmaceuticals) which is being studied for squamous cell cancer of the head and neck (NCT02124850) and ovarian cancer (NCT02431559).

Other immuno-oncology agents that may be used in the present invention include urelumab (BMS-663513, Bristol-Myers Squibb), an anti-CD 137 monoclonal antibody; varlilumab (CDX-1127, Celldex Therapeutics), an anti-CD27 monoclonal antibody; BMS-986178 (Bristol-Myers Squibb), an anti-OX40 monoclonal antibody; lirilumab (IPH2102/BMS-986015, Innate Pharma, Bristol-Myers Squibb), an anti-KIR monoclonal antibody; monalizumab (IPH2201, Innate Pharma, AstraZeneca) an anti-NKG2A monoclonal antibody; andecaliximab (GS-5745, Gilead Sciences), an anti-MMP9 antibody; MK-4166 (Merck & Co.), an anti-GITR monoclonal antibody.

In some embodiments, an immunostimulatory agent is selected from elotuzumab, mifamurtide, an agonist or activator of a toll-like receptor, and an activator of RORγt.

In some embodiments, an immunostimulatory therapeutic is recombinant human interleukin 15 (rhIL-15). rhIL-15 has been tested in the clinic as a therapy for melanoma and renal cell carcinoma (NCT01021059 and NCT01369888) and leukemias (NCT02689453). In some embodiments, an immunostimulatory agent is recombinant human interleukin 12 (rhIL-12). In some embodiments, an IL-15 based immunotherapeutic is heterodimeric IL-15 (hetIL-15, Novartis/Admune), a fusion complex composed of a synthetic form of endogenous IL-15 complexed to the soluble IL-15 binding protein IL-15 receptor alpha chain (IL15:sIL-15RA), which has been tested in Phase 1 clinical trials for melanoma, renal cell carcinoma, non-small cell lung cancer and head and neck squamous cell carcinoma (NCT02452268). In some embodiments, a recombinant human interleukin 12 (rhIL-12) is NM-IL-12 (Neumedicines, Inc.), NCT02544724, or NCT02542124.

In some embodiments, an immuno-oncology agent is selected from those descripted in Jerry L. Adams ET. AL., "Big opportunities for small molecules in immuno-oncology," Cancer Therapy 2015, Vol. 14, pages 603-622, the content of which is incorporated herein by reference in its entirety. In some embodiments, an immuno-oncology agent is selected from the examples described in Table 1 of Jerry L. Adams ET. AL. In some embodiments, an immuno-oncology agent is a small molecule targeting an immuno-oncology target selected from those listed in Table 2 of Jerry L. Adams ET. AL. In some embodiments, an immuno-oncology agent is a small molecule agent selected from those listed in Table 2 of Jerry L. Adams ET. AL.

In some embodiments, an immuno-oncology agent is selected from the small molecule immuno-oncology agents described in Peter L. Toogood, "Small molecule immuno-oncology therapeutic agents," Bioorganic & Medicinal Chemistry Letters 2018, Vol. 28, pages 319-329, the content of which is incorporated herein by reference in its entirety. In some embodiments, an immuno-oncology agent is an agent targeting the pathways as described in Peter L. Toogood.

In some embodiments, an immuno-oncology agent is selected from those described in Sandra L. Ross et al., "Bispecific T cell engager (BiTE®) antibody constructs can mediate bystander tumor cell killing", PLoS ONE 12 (8): e0183390, the content of which is incorporated herein by reference in its entirety. In some embodiments, an immuno-oncology agent is a bispecific T cell engager (BiTE®) antibody construct. In some embodiments, a bispecific T cell engager (BiTE®) antibody construct is a CD19/CD3 bispecific antibody construct. In some embodiments, a bispecific T cell engager (BiTE®) antibody construct is an EGFR/CD3 bispecific antibody construct. In some embodiments, a bispecific T cell engager (BiTE®) antibody construct activates T cells. In some embodiments, a bispecific T cell engager (BiTE®) antibody construct activates T cells, which release cytokines inducing upregulation of intercellular adhesion molecule 1 (ICAM-1) and FAS on bystander cells. In some embodiments, a bispecific T cell engager (BiTE®) antibody construct activates T cells which result in induced bystander cell lysis. In some embodiments, the bystander cells are in solid tumors. In some embodiments, the bystander cells being lysed are in proximity to the BiTE®-activated T cells. In some embodiment, the bystander cells comprises tumor-associated antigen (TAA) negative cancer cells. In some embodiment, the bystander cells comprise EGFR-negative cancer cells. In some embodiments, an immuno-oncology agent is an antibody which blocks the PD-L1/PD1 axis and/or CTLA4. In some embodiments, an immuno-oncology agent is an ex-vivo expanded tumor-infiltrating T cell. In some embodiments, an immuno-oncology agent is a bispecific antibody construct or chimeric antigen receptors (CARs) that directly connect T cells with tumor-associated surface antigens (TAAs).

Exemplary Immune Checkpoint Inhibitors

In some embodiments, an immuno-oncology agent is an immune checkpoint inhibitor as described herein.

The term "checkpoint inhibitor" as used herein relates to agents useful in preventing cancer cells from avoiding the immune system of the patient. One of the major mechanisms of anti-tumor immunity subversion is known as "T-cell exhaustion," which results from chronic exposure to antigens that has led to up-regulation of inhibitory receptors. These inhibitory receptors serve as immune checkpoints in order to prevent uncontrolled immune reactions.

PD-1 and co-inhibitory receptors such as cytotoxic T-lymphocyte antigen 4 (CTLA-4, B and T Lymphocyte Attenuator (BTLA; CD272), T cell Immunoglobulin and Mucin domain-3 (Tim-3), Lymphocyte Activation Gene-3 (Lag-3; CD223), and others are often referred to as a checkpoint regulators. They act as molecular "gatekeepers" that allow extracellular information to dictate whether cell cycle progression and other intracellular signaling processes should proceed.

In some embodiments, an immune checkpoint inhibitor is an antibody to PD-1. PD-1 binds to the programmed cell death 1 receptor (PD-1) to prevent the receptor from binding to the inhibitory ligand PDL-1, thus overriding the ability of tumors to suppress the host anti-tumor immune response.

In one aspect, the checkpoint inhibitor is a biologic therapeutic or a small molecule. In another aspect, the checkpoint inhibitor is a monoclonal antibody, a humanized antibody, a fully human antibody, a fusion protein or a combination thereof. In a further aspect, the checkpoint inhibitor inhibits a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an additional aspect, the checkpoint inhibitor interacts with a ligand of a checkpoint protein selected from CTLA-4, PDL1, PDL2, PD1, B7-H3, B7-H4, BTLA, HVEM, TIM3, GAL9, LAG3, VISTA, KIR, 2B4, CD160, CGEN-15049, CHK 1, CHK2, A2aR, B-7 family ligands or a combination thereof. In an aspect, the checkpoint inhibitor is an immunostimulatory agent, a T cell growth factor, an interleukin, an antibody, a vaccine or a combination thereof. In a further aspect, the interleukin is IL-7 or IL-15. In a specific aspect, the interleukin is glycosylated IL-7. In an additional aspect, the vaccine is a dendritic cell (DC) vaccine.

Checkpoint inhibitors include any agent that blocks or inhibits in a statistically significant manner, the inhibitory pathways of the immune system. Such inhibitors may include small molecule inhibitors or may include antibodies, or antigen binding fragments thereof, that bind to and block or inhibit immune checkpoint receptors or antibodies that bind to and block or inhibit immune checkpoint receptor ligands. Illustrative checkpoint molecules that may be targeted for blocking or inhibition include, but are not limited to, CTLA-4, PDL1, PDL2, PD1, B7-H3, B7-H4, BTLA, HVEM, GAL9, LAG3, TIM3, VISTA, KIR, 2B4 (belongs to the CD2 family of molecules and is expressed on all NK, γδ, and memory $CD8^+$ (αβ) T cells), CD160 (also referred to as BY55), CGEN-15049, CHK 1 and CHK2 kinases, A2aR, and various B-7 family ligands. B7 family ligands include, but are not limited to, B7-1, B7-2, B7-DC, B7-H1, B7-H2, B7-H3, B7-H4, B7-H5, B7-H6 and B7-H7. Checkpoint inhibitors include antibodies, or antigen binding fragments thereof, other binding proteins, biologic therapeutics, or small molecules, that bind to and block or inhibit the activity of one or more of CTLA-4, PDL1, PDL2, PD1, BTLA, HVEM, TIM3, GAL9, LAG3, VISTA, KIR, 2B4, CD 160 and CGEN-15049. Illustrative immune checkpoint inhibitors include Tremelimumab (CTLA-4 blocking antibody), anti-OX40, PD-L1 monoclonal Antibody (Anti-B7-H1; MEDI4736), MK-3475 (PD-1 blocker), Nivolumab (anti-PD1 antibody), CT-011 (anti-PD1 antibody), BY55 monoclonal antibody, AMP224 (anti-PDL1 antibody), BMS-936559 (anti-PDL1 antibody), MPLDL3280A (anti-PDL1 antibody), MSB0010718C (anti-PDL1 antibody), and ipilimumab (anti-CTLA-4 checkpoint inhibitor). Checkpoint protein ligands include, but are not limited to PD-L1, PD-L2, B7-H3, B7-H4, CD28, CD86 and TIM-3.

In certain embodiments, the immune checkpoint inhibitor is selected from a PD-1 antagonist, a PD-L1 antagonist, and a CTLA-4 antagonist. In some embodiments, the checkpoint inhibitor is selected from the group consisting of nivolumab (Opdivo®), ipilimumab (Yervoy®), and pembrolizumab (Keytruda®). In some embodiments, the checkpoint inhibitor is selected from nivolumab (anti-PD-1 antibody, Opdivo®, Bristol-Myers Squibb); pembrolizumab (anti-PD-1 antibody, Keytruda®, Merck); ipilimumab (anti-CTLA-4 antibody, Yervoy®, Bristol-Myers Squibb); durvalumab (anti-PD-L1 antibody, Imfinzi®, AstraZeneca); and atezolizumab (anti-PD-L1 antibody, Tecentriq®, Genentech).

In some embodiments, the checkpoint inhibitor is selected from the group consisting of lambrolizumab (MK-3475), nivolumab (BMS-936558), pidilizumab (CT-011), AMP-224, MDX-1105, MEDI4736, MPDL3280A, BMS-936559, ipilimumab, lirlumab, IPH2101, pembrolizumab (Keytruda®), and tremelimumab.

In some embodiments, an immune checkpoint inhibitor is REGN2810 (Regeneron), an anti-PD-1 antibody tested in patients with basal cell carcinoma (NCT03132636); NSCLC (NCT03088540); cutaneous squamous cell carcinoma (NCT02760498); lymphoma (NCT02651662); and melanoma (NCT03002376); pidilizumab (CureTech), also known as CT-011, an antibody that binds to PD-1, in clinical trials for diffuse large B-cell lymphoma and multiple myeloma; avelumab (Bavencio®, Pfizer/Merck KGaA), also known as MSB0010718C), a fully human IgG1 anti-PD-L1 antibody, in clinical trials for non-small cell lung cancer, Merkel cell carcinoma, mesothelioma, solid tumors, renal cancer, ovarian cancer, bladder cancer, head and neck cancer, and gastric cancer; or PDR001 (Novartis), an inhibitory antibody that binds to PD-1, in clinical trials for non-small cell lung cancer, melanoma, triple negative breast cancer and advanced or metastatic solid tumors. Tremelimumab (CP-675,206; Astrazeneca) is a fully human monoclonal antibody against CTLA-4 that has been in studied in clinical trials for a number of indications, including: mesothelioma, colorectal cancer, kidney cancer, breast cancer, lung cancer and non-small cell lung cancer, pancreatic ductal adenocarcinoma, pancreatic cancer, germ cell cancer, squamous cell cancer of the head and neck, hepatocellular carcinoma, prostate cancer, endometrial cancer, metastatic cancer in the liver, liver cancer, large B-cell lymphoma, ovarian cancer, cervical cancer, metastatic anaplastic thyroid cancer, urothelial cancer, fallopian tube cancer, multiple myeloma, bladder cancer, soft tissue sarcoma, and melanoma. AGEN-1884 (Agenus) is an anti-CTLA4 antibody that is being studied in Phase 1 clinical trials for advanced solid tumors (NCT02694822).

In some embodiments, a checkpoint inhibitor is an inhibitor of T-cell immunoglobulin mucin containing protein-3 (TIM-3). TIM-3 inhibitors that may be used in the present invention include TSR-022, LY3321367 and MBG453. TSR-022 (Tesaro) is an anti-TIM-3 antibody which is being studied in solid tumors (NCT02817633). LY3321367 (Eli Lilly) is an anti-TIM-3 antibody which is being studied in solid tumors (NCT03099109). MBG453 (Novartis) is an anti-TIM-3 antibody which is being studied in advanced malignancies (NCT02608268).

In some embodiments, a checkpoint inhibitor is an inhibitor of T cell immunoreceptor with Ig and ITIM domains, or TIGIT, an immune receptor on certain T cells and NK cells. TIGIT inhibitors that may be used in the present invention include BMS-986207 (Bristol-Myers Squibb), an anti-TIGIT monoclonal antibody (NCT02913313); OMP-313M32 (Oncomed); and anti-TIGIT monoclonal antibody (NCT03119428).

In some embodiments, a checkpoint inhibitor is an inhibitor of Lymphocyte Activation Gene-3 (LAG-3). LAG-3 inhibitors that may be used in the present invention include BMS-986016 and REGN3767 and IMP321. BMS-986016 (Bristol-Myers Squibb), an anti-LAG-3 antibody, is being studied in glioblastoma and gliosarcoma (NCT02658981). REGN3767 (Regeneron), is also an anti-LAG-3 antibody, and is being studied in malignancies (NCT03005782). IMP321 (Immutep S.A.) is an LAG-3-Ig fusion protein, being studied in melanoma (NCT02676869); adenocarcinoma (NCT02614833); and metastatic breast cancer (NCT00349934).

Checkpoint inhibitors that may be used in the present invention include OX40 agonists. OX40 agonists that are being studied in clinical trials include PF-04518600/PF-8600 (Pfizer), an agonistic anti-OX40 antibody, in metastatic kidney cancer (NCT03092856) and advanced cancers and neoplasms (NCT02554812; NCT05082566); GSK3174998 (Merck), an agonistic anti-OX40 antibody, in Phase 1 cancer trials (NCT02528357); MEDI0562 (Medimmune/AstraZeneca), an agonistic anti-OX40 antibody, in advanced solid tumors (NCT02318394 and NCT02705482); MEDI6469, an agonistic anti-OX40 antibody (Medimmune/AstraZeneca), in patients with colorectal cancer (NCT02559024), breast cancer (NCT01862900), head and neck cancer (NCT02274155) and metastatic prostate cancer (NCT01303705); and BMS-986178 (Bristol-Myers Squibb) an agonistic anti-OX40 antibody, in advanced cancers (NCT02737475).

Checkpoint inhibitors that may be used in the present invention include CD137 (also called 4-1BB) agonists. CD137 agonists that are being studied in clinical trials include utomilumab (PF-05082566, Pfizer) an agonistic anti-CD137 antibody, in diffuse large B-cell lymphoma (NCT02951156) and in advanced cancers and neoplasms (NCT02554812 and NCT05082566); urelumab (BMS-663513, Bristol-Myers Squibb), an agonistic anti-CD137 antibody, in melanoma and skin cancer (NCT02652455) and glioblastoma and gliosarcoma (NCT02658981).

Checkpoint inhibitors that may be used in the present invention include CD27 agonists. CD27 agonists that are being studied in clinical trials include varlilumab (CDX-1127, Celldex Therapeutics) an agonistic anti-CD27 antibody, in squamous cell head and neck cancer, ovarian carcinoma, colorectal cancer, renal cell cancer, and glioblastoma (NCT02335918); lymphomas (NCT01460134); and glioma and astrocytoma (NCT02924038).

Checkpoint inhibitors that may be used in the present invention include glucocorticoid-induced tumor necrosis factor receptor (GITR) agonists. GITR agonists that are being studied in clinical trials include TRX518 (Leap Therapeutics), an agonistic anti-GITR antibody, in malignant melanoma and other malignant solid tumors (NCT01239134 and NCT02628574); GWN323 (Novartis), an agonistic anti-GITR antibody, in solid tumors and lymphoma (NCT 02740270); INCAGN01876 (Incyte/Agenus), an agonistic anti-GITR antibody, in advanced cancers (NCT02697591 and NCT03126110); MK-4166 (Merck), an agonistic anti-GITR antibody, in solid tumors (NCT02132754) and MEDI1873 (Medimmune/AstraZeneca), an agonistic hexameric GITR-ligand molecule with a human IgG1 Fc domain, in advanced solid tumors (NCT02583165).

Checkpoint inhibitors that may be used in the present invention include inducible T-cell co-stimulator (ICOS, also known as CD278) agonists. ICOS agonists that are being studied in clinical trials include MEDI-570 (Medimmune), an agonistic anti-ICOS antibody, in lymphomas (NCT02520791); GSK3359609 (Merck), an agonistic anti-ICOS antibody, in Phase 1 (NCT02723955); JTX-2011 (Jounce Therapeutics), an agonistic anti-ICOS antibody, in Phase 1 (NCT02904226).

Checkpoint inhibitors that may be used in the present invention include killer IgG-like receptor (KIR) inhibitors. KIR inhibitors that are being studied in clinical trials include lirilumab (IPH2102/BMS-986015, Innate Pharma/Bristol-Myers Squibb), an anti-KIR antibody, in leukemias (NCT01687387, NCT02399917, NCT02481297, NCT02599649), multiple myeloma (NCT02252263), and lymphoma (NCT01592370); IPH2101 (1-7F9, Innate Pharma) in myeloma (NCT01222286 and NCT01217203); and IPH4102 (Innate Pharma), an anti-KIR antibody that binds to three domains of the long cytoplasmic tail (KIR3DL2), in lymphoma (NCT02593045).

Checkpoint inhibitors that may be used in the present invention include CD47 inhibitors of interaction between CD47 and signal regulatory protein alpha (SIRPa). CD47/SIRPa inhibitors that are being studied in clinical trials include ALX-148 (Alexo Therapeutics), an antagonistic variant of (SIRPa) that binds to CD47 and prevents CD47/SIRPa-mediated signaling, in phase 1 (NCT03013218); TTI-621 (SIRPa-Fc, *Trillium* Therapeutics), a soluble recombinant fusion protein created by linking the N-terminal CD47-binding domain of SIRPa with the Fc domain of human IgG1, acts by binding human CD47, and preventing it from delivering its "do not eat" signal to macrophages, is in clinical trials in Phase 1 (NCT02890368 and NCT02663518); CC-90002 (Celgene), an anti-CD47 antibody, in leukemias (NCT02641002); and Hu5F9-G4 (Forty Seven, Inc.), in colorectal neoplasms and solid tumors (NCT02953782), acute myeloid leukemia (NCT02678338) and lymphoma (NCT02953509).

Checkpoint inhibitors that may be used in the present invention include CD73 inhibitors. CD73 inhibitors that are being studied in clinical trials include MEDI9447 (Medimmune), an anti-CD73 antibody, in solid tumors (NCT02503774); and BMS-986179 (Bristol-Myers Squibb), an anti-CD73 antibody, in solid tumors (NCT02754141).

Checkpoint inhibitors that may be used in the present invention include agonists of stimulator of interferon genes protein (STING, also known as transmembrane protein 173, or TMEM173). Agonists of STING that are being studied in clinical trials include MK-1454 (Merck), an agonistic synthetic cyclic dinucleotide, in lymphoma (NCT03010176); and ADU-S100 (MIW815, Aduro Biotech/Novartis), an agonistic synthetic cyclic dinucleotide, in Phase 1 (NCT02675439 and NCT03172936).

Checkpoint inhibitors that may be used in the present invention include CSF1R inhibitors. CSF1R inhibitors that are being studied in clinical trials include pexidartinib (PLX3397, Plexxikon), a CSF1R small molecule inhibitor, in colorectal cancer, pancreatic cancer, metastatic and advanced cancers (NCT02777710) and melanoma, non-small cell lung cancer, squamous cell head and neck cancer, gastrointestinal stromal tumor (GIST) and ovarian cancer (NCT02452424); and IMC-CS4 (LY3022855, Lilly), an anti-CSF-1R antibody, in pancreatic cancer (NCT03153410), melanoma (NCT03101254), and solid tumors (NCT02718911); and BLZ945 (4-[2((1R,2R)-2-hydroxycyclohexylamino)-benzothiazol-6-yloxyl]-pyridine-2-carboxylic acid methylamide, Novartis), an orally available inhibitor of CSF1R, in advanced solid tumors (NCT02829723).

Checkpoint inhibitors that may be used in the present invention include NKG2A receptor inhibitors. NKG2A receptor inhibitors that are being studied in clinical trials include monalizumab (IPH2201, Innate Pharma), an anti-NKG2A antibody, in head and neck neoplasms (NCT02643550) and chronic lymphocytic leukemia (NCT02557516).

In some embodiments, the immune checkpoint inhibitor is selected from nivolumab, pembrolizumab, ipilimumab, avelumab, durvalumab, atezolizumab, or pidilizumab.

EXEMPLIFICATION

Abbreviations
Ac: acetyl
AcOH: acetic acid
ACN: acetonitrile
Ad: adamantly
AIBN: 2,2'-azo bisisobutyronitrile
Anhyd: anhydrous
Aq: aqueous
$B_2Pin_2$: bis(pinacolato)diboron-4,4,4',4',5,5,5',5'-octamethyl-2,2'-bi(1,3,2-dioxaborolane)
BINAP: 2,2'-bis(diphenylphosphino)-1,1'-binaphthyl
$BH_3$: Borane
Bn: benzyl
Boc: tert-butoxycarbonyl
$Boc_2O$: di-tert-butyl dicarbonate
BPO: benzoyl peroxide
"BuOH: n-butanol
CDI: carbonyldiimidazole
COD: cyclooctadiene
d: days
DABCO: 1,4-diazobicyclo[2.2.2]octane
DAST: diethylaminosulfur trifluoride
dba: dibenzylideneacetone
DBU: 1,8-diazobicyclo[5.4.0]undec-7-ene
DCE: 1,2-dichloroethane
DCM: dichloromethane
DEA: diethylamine
DHP: dihydropyran
DIBAL-H: diisobutylaluminum hydride
DIPA: diisopropylamine
DIPEA or DIEA: N,N-diisopropylethylamine
DMA: N,N-dimethylacetamide
DME: 1,2-dimethoxyethane
DMAP: 4-dimethylaminopyridine
DMF: N,N-dimethylformamide
DMP: Dess-Martin periodinane
DMSO-dimethyl sulfoxide
DPPA: diphenylphosphoryl azide
dppf: 1,1'-bis(diphenylphosphino)ferrocene
EDC or EDCI: 1-(3-dimethylaminopropyl)-3-ethylcarbodiimide hydrochloride
ee: enantiomeric excess
ESI: electrospray ionization
EA: ethyl acetate
EtOAc: ethyl acetate EtOH: ethanol
FA: formic acid
h or hrs: hours
HATU: N,N,N',N'-tetramethyl-O-(7-azabenzotriazol-1-yl)uronium hexafluorophosphate
HCl: hydrochloric acid
HPLC: high performance liquid chromatography
HOAc: acetic acid
IBX: 2-iodoxybenzoic acid
IPA: isopropyl alcohol
KHMDS: potassium hexamethyldisilazide
$K_2CO_3$: potassium carbonate
LAH: lithium aluminum hydride
LDA: lithium diisopropylamide
m-CPBA: meta-chloroperbenzoic acid
M: molar
MeCN: acetonitrile
MeOH: methanol
$Me_2S$: dimethyl sulfide
MeONa: sodium methylate
MeI: iodomethane
min: minutes
mL: milliliters
mM: millimolar
mmol: millimoles
MPa: mega pascal
MOMCl: methyl chloromethyl ether
MsCl: methanesulfonyl chloride
MTBE: methyl tert-butyl ether
nBuLi: n-butyllithium
$NaNO_2$: sodium nitrite
NaOH: sodium hydroxide
$Na_2SO_4$: sodium sulfate
NBS: N-bromosuccinimide
NCS: N-chlorosuccinimide
NFSI: N-Fluorobenzenesulfonimide
NMO: N-methylmorpholine N-oxide
NMP: N-methylpyrrolidine
NMR: Nuclear Magnetic Resonance
° C.: degrees Celsius
Pd/C: Palladium on Carbon
$Pd(OAc)_2$: Palladium Acetate
PBS: phosphate buffered saline
PE: petroleum ether
$POCl_3$: phosphorus oxychloride
$PPh_3$: triphenylphosphine
PyBOP: (Benzotriazol-1-yloxy)tripyrrolidinophosphonium hexafluorophosphate
Rel: relative
R.T. or rt: room temperature
sat: saturated
SEMCl: chloromethyl-2-trimethylsilylethyl ether
SFC: supercritical fluid chromatography
$SOCl_2$: sulfur dichloride
tBuOK: potassium tert-butoxide
TBAB: tetrabutylammonium bromide
TBAI: tetrabutylammonium iodide
TEA: triethylamine
Tf: trifluoromethanesulfonate
TfAA, TFMSA or $Tf_2O$: trifluoromethanesulfonic anhydride
TFA: trifluoracetic acid
TIPS: triisopropylsilyl
THF: tetrahydrofuran
THP: tetrahydropyran
TLC: thin layer chromatography
TMEDA: tetramethylethylenediamine
pTSA: para-toluenesulfonic acid
wt: weight
Xantphos: 4,5-bis(diphenylphosphino)-9,9-dimethylxanthene General Synthetic Methods The following examples are intended to illustrate the invention and are not to be construed as being limitations thereon. Temperatures are given in degrees centigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

All reactions are carried out under nitrogen or argon unless otherwise stated.

Proton NMR ($^1$H NMR) is conducted in deuterated solvent. In certain compounds disclosed herein, one or more $^1$H shifts overlap with residual proteo solvent signals; these signals have not been reported in the experimental provided hereinafter.

TABLE 5

| Analytical instruments | |
|---|---|
| LCMS | Shimadzu UFLC MS: LCMS-2020 |
| | Agilent Technologies 1200 series MS: Agilent Technologies 6110 |
| | Agilent Technologies 1200 series MS: LC/MSD VL |
| NMR | BRUKER AVANCE III/400; Frequency (MHz) 400.13; Nucleus: 1H; Number of Transients: 8 |
| Prep-HPLC | Gilson GX-281 systems: instruments GX-A, GX-B, GX-C, GX-D, GX-E, GX-F, GX-G and GX-H |
| GCMS | SHIMADZU GCMS-QP2010 Ultra |
| Analytical cSFC | Agilent Technologies 1290 Infinity |
| Prep-cSFC | Waters SFC Prep 80 |

For acidic LCMS data: LCMS was recorded on an Agilent 1200 Series LC/MSD or Shimadzu LCMS2020 equipped with electro-spray ionization and quadruple MS detector [ES+ve to give MH$^+$] and equipped with Chromolith Flash RP-18e 25*2.0 mm, eluting with 0.0375 vol % TFA in water (solvent A) and 0.01875 vol % TFA in acetonitrile (solvent B). Other LCMS was recorded on an Agilent 1290 Infinity RRLC attached with Agilent 6120 Mass detector. The column used was BEH C18 50*2.1 mm, 1.7 micron. Column flow was 0.55 ml/min and mobile phase were used (A) 2 mM Ammonium Acetate in 0.1% Formic Acid in Water and (B) 0.1% Formic Acid in Acetonitrile.

For basic LCMS data: LCMS was recorded on an Agilent 1200 Series LC/MSD or Shimadzu LCMS 2020 equipped with electro-spray ionization and quadruple MS detector [ES+ve to give MH$^+$] and equipped with Xbridge C18, 2.1×50 mm columns packed with 5 mm C18-coated silica or Kinetex EVO C18 2.1×30 mm columns packed with 5 mm C18-coated silica, eluting with 0.05 vol % NH$_3$.H$_2$O in water (solvent A) and acetonitrile (solvent B).

HPLC Analytical Method: HPLC was carried out on X Bridge C18 150*4.6 mm, 5 micron. Column flow was 1.0 ml/min and mobile phase were used (A) 0.1% Ammonia in water and (B) 0.1% Ammonia in Acetonitrile.

Prep HPLC Analytical Method: The compound was purified on Shimadzu LC-20AP and UV detector. The column used was X-BRIDGE C18 (250*19)mm, 5. Column flow was 16.0 ml/min. Mobile phase were used (A) 0.1% Formic Acid in Water and (B) Acetonitrile Basic method used (A) 5 mM ammonium bicarbonate and 0.1% NH3 in Water and (B) Acetonitrile or (A) 0.1% Ammonium Hydroxide in Water and (B) Acetonitrile. The UV spectra were recorded at 202 nm & 254 nm.

NMR Method: The 1H NMR spectra were recorded on a Bruker Ultra Shield Advance 400 MHz/5 mm Probe (BBFO). The chemical shifts are reported in part-per-million.

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Intermediates 1,6-naphthyridin-2-amine (Intermediate M)

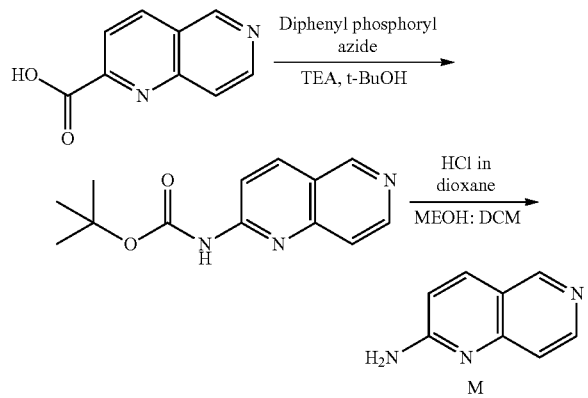

Step 1—tert-butyl (1,6-naphthyridin-2-yl)carbamate

To a stirred solution of 1,6-naphthyridine-2-carboxylic acid (20.0 g, 114 mmol) in t-BuOH (200 mL) was added Et$_3$N (16 mL, 114 mmol) and diphenyl phosphoryl azide (37.0 g, 137 mmol) respectively at rt. The resulting mixture then heated to 80° C. and stirred for 24 h. The reaction mixture was evaporated carefully under vacuum, diluted with ice water and resulting solid was collected by filtration. The solid was treated with hot ethanol and again filtered and dried under vacuum to give tert-butyl (1,6-naphthyridin-2-yl)carbamate as a light brown solid (13.1 g, 46%). $^1$H NMR (400 MHz, DMSO-d$_6$) δ 10.49 (s, 1H), 9.20 (s, 1H), 8.61 (d, J=6 Hz, 1H), 8.47 (d, J=9.2 Hz, 1H), 8.18 (d, J=8.8 Hz, 1H), 7.62 (s, 1H), 1.50 (s, 9H). LC-MS (ESI$^+$) m/z 246.2 (M+H)$^+$ Step 2—1,6-naphthyridin-2-amine To a stirred solution of tert-butyl (1,6-naphthyridin-2-yl)carbamate (4.37 g, 17.8 mmol) in MeOH:DCM (40 mL, 3:1 ratio) was added 4N HCl in dioxane (15 mL) at 0° C. The resulting reaction mixture was allowed to warm to rt and stirred for 18 h. The reaction mixture was then evaporated under vacuum and diluted with 30 mL of water. Saturated NaHCO$_3$ solution (15 mL) was added and the resulting mixture was extracted using EtOAc (2×50 mL). The combined organic layers were dried under vacuum to give 1,6-naphthyridin-2-amine as a white solid (2.45 g, 94%). $^1$H NMR (400 MHz, DMSO-d$_6$) δ 9.03 (s, 1H), 8.43 (d, J=6 Hz, 1H), 8.14 (d, J=8.8 Hz, 1H), 7.72 (bs, 2H), 7.45 (d, J=6 Hz, 1H), 6.96 (d, J=8.8 Hz, 1H); LCMS (ESI$^+$) m/z 146.4 (M+H)$^+$.

(6-((1,6-Naphthyridin-2-yl)amino)-4-(cyclopropylamino)nicotinic acid (Intermediate N)

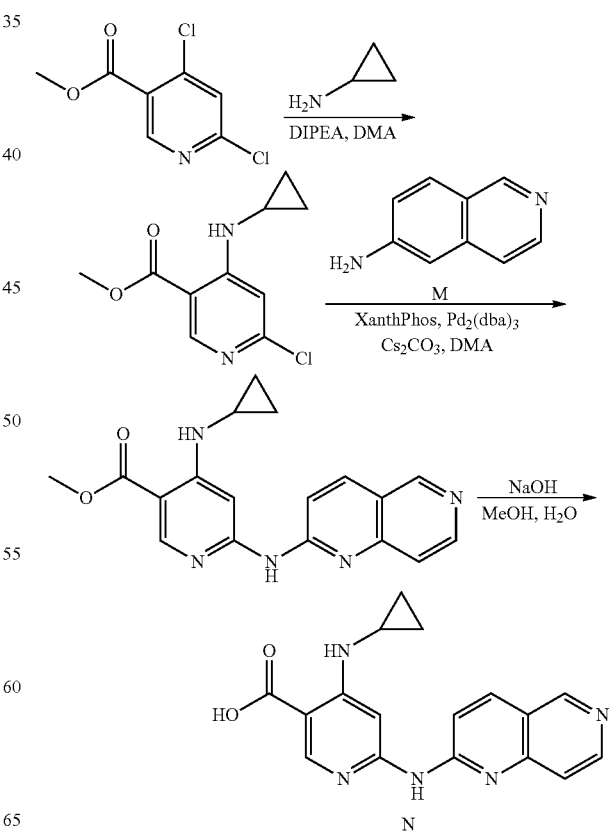

Step 1—methyl 6-chloro-4-(cyclopropylamino)nicotinate

To a stirred solution of methyl 4,6-dichloronicotinate (10.0 g, 48.5 mmol) in DMA (80 mL) was added DIPEA (6.6 mL, 48.5 mmol) and cyclopropylamine (3.7 mL, 53.0 mmol) at rt. The resulting mixture then heated at 90° C. for 3 h. After 3 h, the reaction mixture was cooled to rt and diluted with ice water. The resulting mixture was stirred for 20 min and the solid precipitate was collected by filtration and dried under vacuum. The crude product was purified by silica gel column chromatography (10% EtOAc-hexanes) to give methyl 6-chloro-4-(cyclopropylamino)nicotinate as a white solid (9.5 g, 87%). $^1$H NMR (400 MHz, CDCl$_3$) δ 8.67 (s, 1H), 8.20 (bs, 1H), 6.98 (s, 1H), 3.89 (s, 3H), 2.51 (m, 1H), 0.91 (q, J=6.8 Hz, 2H), 0.61-0.65 (m, 2H); LC-MS (ESI$^+$) m/z 227.2 (M+H)$^+$.

Step 2—methyl 6-((1,6-naphthyridin-2-yl)amino)-4-(cyclopropylamino)nicotinate To a stirred solution of methyl 6-chloro-4-(cyclopropylamino)nicotinate (2.5 g, 11.8 mmol) and 1,6-naphthyridin-2-amine (1.6 g, 11.76 mmol, Intermediate M) in DMA (50 mL) was added Xantphos (2.5 g, 4.4 mmol) and Cs$_2$CO$_3$ (5.76 g, 17.60 mmol) and resulting reaction mixture was degassed using argon for 30 min. Then of Pd$_2$(dba)$_3$ (2.0 g, 2.2 mmol) was added. The resulting mixture was heated at 120° C. for 18 h. The reaction mixture was cooled to rt and ice water was added. The resulting solid precipitate was collected by filtration and dried under vacuum. The crude product was purified by silica gel column chromatography (5% MeOH-DCM) to give methyl 6-((1,6-naphthyridin-2-yl)amino)-4-(cyclopropylamino)nicotinate as a yellow solid (2.2 g, 59%). $^1$H NMR (400 MHz, DMSO-d$_6$) δ 10.5 (s, 1H), 9.08 (s, 1H), 8.66 (s, 1H), 8.58-8.60 (m, 2H), 8.31 (d, J=8.8 Hz, 1H), 8.03 (s, 1H), 7.61 (d, J=6 Hz, 1H), 7.51 (d, J=8.8 Hz, 1H), 3.80 (s, 3H), 2.67-2.70 (m, 1H), 0.99-1.02 (m, 2H), 0.65-0.67 (m, 2H). LC-MS (ESI$^+$) m/z 336.6 (M+H)$^+$.

Step 3—6-((1,6-naphthyridin-2-yl)amino)-4-(cyclopropylamino)nicotinic acid

To a stirred solution of methyl 6-((1,6-naphthyridin-2-yl)amino)-4-(cyclopropylamino)nicotinate (1.6 g, 1.8 mmol) in methanol:water (30 mL, 1:1 ratio) was added NaOH (0.36 g, 5 mmol) at rt. The resulting reaction mixture was then heated at 70° C. for 16 h. Upon completion, the reaction mixture was in vacuo and the resulting solid was triturated using ethyl acetate and collected by filtration. The solid was taken in water and the pH was adjusted to 6-7 using dilute HCl and the resulting solid was collected by filtration and dried under vacuum to give 6-((1,6-naphthyridin-2-yl)amino)-4-(cyclopropylamino)nicotinic acid as a dark yellow solid (0.45 g, 78%). LC-MS (ESI$^+$) m/z 322.6 (M+H)$^+$

2-(2,6-Dioxopiperidin-3-yl)-4-fluoroisoindoline-1,3-dione (Intermediate R)

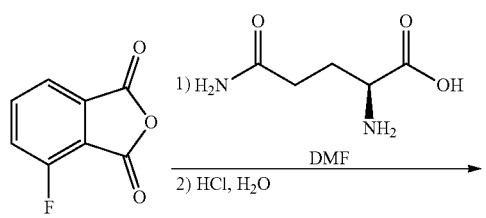

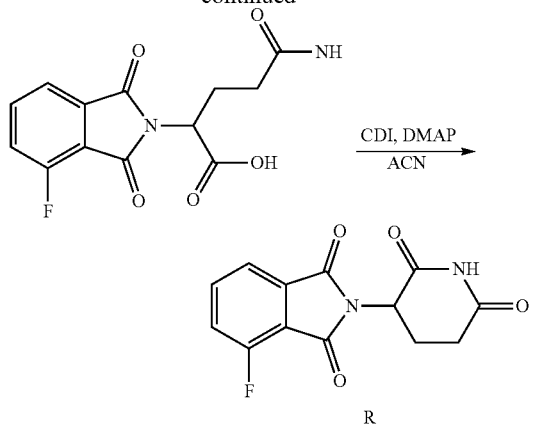

Step 1—5-amino-2-(4-fluoro-1,3-dioxoisoindolin-2-yl)-5-oxopentanoic acid

To a stirred solution of 4-fluoroisobenzofuran-1,3-dione (25 g, 150 mmol, CAS #652-39-1) in DMF (100 mL) was added L-glutamine (22 g, 150 mmol) at rt. The resulting reaction mixture was heated to at 90° C. and stirred for 2 h. The reaction mixture was then evaporated under reduced pressure, transferred into 4 N aqueous HCl solution and the resulting mixture was stirred for 36 h at rt. The solid precipitate was then filtered off, washed with cold water and dried under reduced pressure to give 5-amino-2-(4-fluoro-1,3-dioxoisoindolin-2-yl)-5-oxopentanoic acid as a white solid (28 g, 63%). LC-MS (ESI$^+$) m/z 295 (M+H)$^+$.

Step 2—2-(2,6-dioxopiperidin-3-yl)-4-fluoroisoindoline-1,3-dione

To a stirred solution of 5-amino-2-(4-fluoro-1,3-dioxoisoindolin-2-yl)-5-oxopentanoic acid (28 g, 95 mmol) in acetonitrile (200 mL) was added CDI (19 g, 110 mmol) and DMAP (0.14 g, 1.1 mmol) at rt. The resulting reaction mixture then heated to 90° C. and stirred for 5 h. The reaction mixture was then evaporated under reduced pressure. The crude product was purified using silica gel column chromatography (2% MeOH-DCM) to give 2-(2,6-dioxopiperidin-3-yl)-4-fluoroisoindoline-1,3-dione as a yellow solid (12 g, 46%). $^1$H NMR (400 MHz, DMSO) δ ppm 11.16 (s, 1H), 7.98-7.93 (m, 1H), 7.80-7.76 (m, 2H), 5.19-5.14 (m, 1H), 2.94-2.85 (m, 1H), 2.63-2.54 (m, 2H), 2.09-2.04 (m, 1H).

3-Dibenzylamino)-2-fluoro-propan-1-ol (Intermediate AH)

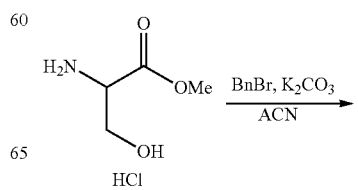

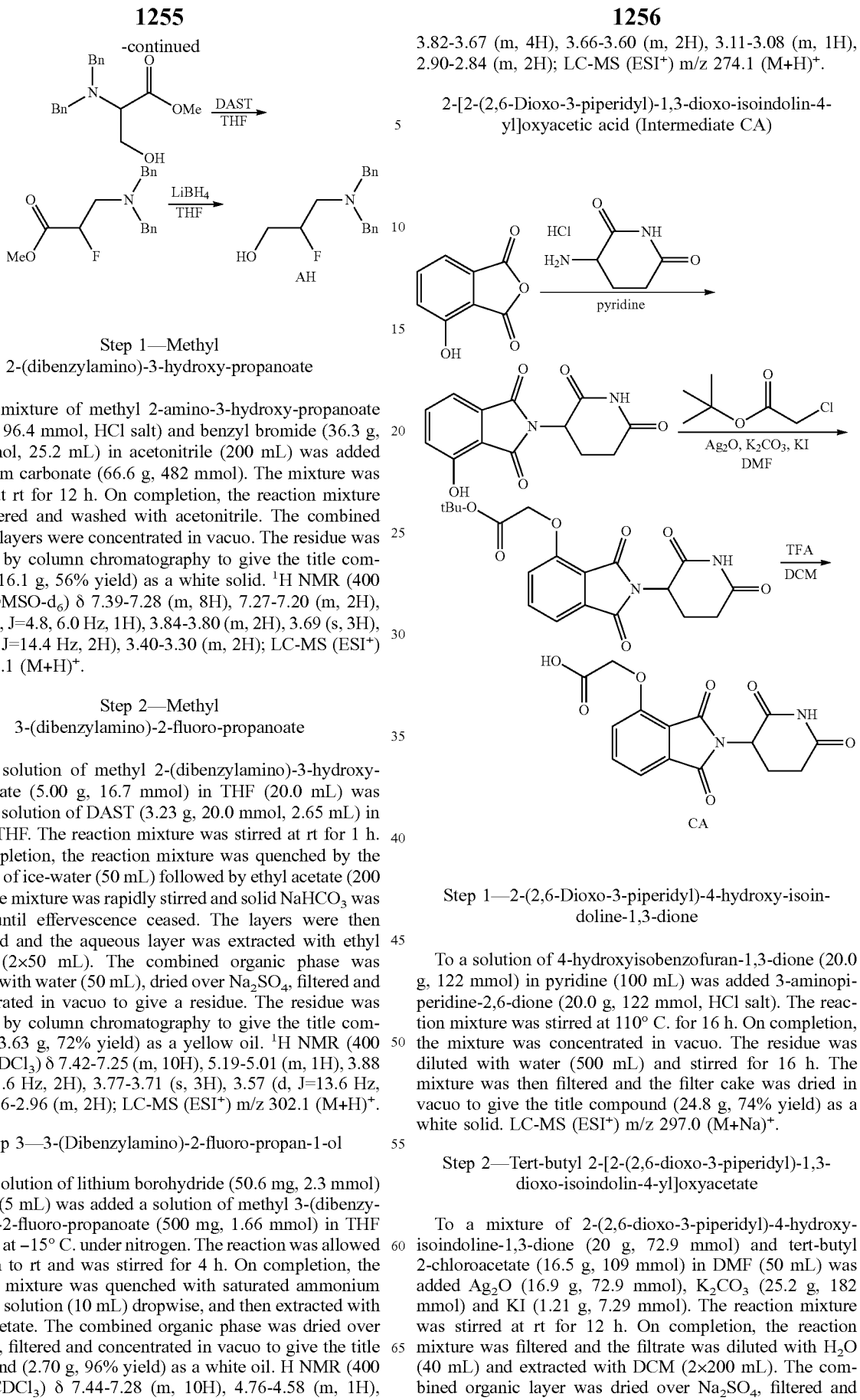

Step 1—Methyl 2-(dibenzylamino)-3-hydroxy-propanoate

To a mixture of methyl 2-amino-3-hydroxy-propanoate (15.0 g, 96.4 mmol, HCl salt) and benzyl bromide (36.3 g, 212 mmol, 25.2 mL) in acetonitrile (200 mL) was added potassium carbonate (66.6 g, 482 mmol). The mixture was stirred at rt for 12 h. On completion, the reaction mixture was filtered and washed with acetonitrile. The combined organic layers were concentrated in vacuo. The residue was purified by column chromatography to give the title compound (16.1 g, 56% yield) as a white solid. $^1$H NMR (400 MHz, DMSO-$d_6$) δ 7.39-7.28 (m, 8H), 7.27-7.20 (m, 2H), 4.80 (dd, J=4.8, 6.0 Hz, 1H), 3.84-3.80 (m, 2H), 3.69 (s, 3H), 3.56 (d, J=14.4 Hz, 2H), 3.40-3.30 (m, 2H); LC-MS (ESI$^+$) m/z 300.1 (M+H)$^+$.

Step 2—Methyl 3-(dibenzylamino)-2-fluoro-propanoate

To a solution of methyl 2-(dibenzylamino)-3-hydroxy-propanoate (5.00 g, 16.7 mmol) in THF (20.0 mL) was added a solution of DAST (3.23 g, 20.0 mmol, 2.65 mL) in 10 mL THF. The reaction mixture was stirred at rt for 1 h. On completion, the reaction mixture was quenched by the addition of ice-water (50 mL) followed by ethyl acetate (200 mL). The mixture was rapidly stirred and solid NaHCO$_3$ was added until effervescence ceased. The layers were then separated and the aqueous layer was extracted with ethyl acetate (2×50 mL). The combined organic phase was washed with water (50 mL), dried over Na$_2$SO$_4$, filtered and concentrated in vacuo to give a residue. The residue was purified by column chromatography to give the title compound (3.63 g, 72% yield) as a yellow oil. $^1$H NMR (400 MHz, CDCl$_3$) δ 7.42-7.25 (m, 10H), 5.19-5.01 (m, 1H), 3.88 (d, J=13.6 Hz, 2H), 3.77-3.71 (s, 3H), 3.57 (d, J=13.6 Hz, 2H), 3.16-2.96 (m, 2H); LC-MS (ESI$^+$) m/z 302.1 (M+H)$^+$.

Step 3—3-(Dibenzylamino)-2-fluoro-propan-1-ol

To a solution of lithium borohydride (50.6 mg, 2.3 mmol) in THF (5 mL) was added a solution of methyl 3-(dibenzylamino)-2-fluoro-propanoate (500 mg, 1.66 mmol) in THF (10 mL) at −15° C. under nitrogen. The reaction was allowed to warm to rt and was stirred for 4 h. On completion, the reaction mixture was quenched with saturated ammonium chloride solution (10 mL) dropwise, and then extracted with ethyl acetate. The combined organic phase was dried over Na$_2$SO$_4$, filtered and concentrated in vacuo to give the title compound (2.70 g, 96% yield) as a white oil. H NMR (400 MHz, CDCl$_3$) δ 7.44-7.28 (m, 10H), 4.76-4.58 (m, 1H), 3.82-3.67 (m, 4H), 3.66-3.60 (m, 2H), 3.11-3.08 (m, 1H), 2.90-2.84 (m, 2H); LC-MS (ESI$^+$) m/z 274.1 (M+H)$^+$.

2-[2-(2,6-Dioxo-3-piperidyl)-1,3-dioxo-isoindolin-4-yl]oxyacetic acid (Intermediate CA)

Step 1—2-(2,6-Dioxo-3-piperidyl)-4-hydroxy-isoindoline-1,3-dione

To a solution of 4-hydroxyisobenzofuran-1,3-dione (20.0 g, 122 mmol) in pyridine (100 mL) was added 3-aminopiperidine-2,6-dione (20.0 g, 122 mmol, HCl salt). The reaction mixture was stirred at 110° C. for 16 h. On completion, the mixture was concentrated in vacuo. The residue was diluted with water (500 mL) and stirred for 16 h. The mixture was then filtered and the filter cake was dried in vacuo to give the title compound (24.8 g, 74% yield) as a white solid. LC-MS (ESI$^+$) m/z 297.0 (M+Na)$^+$.

Step 2—Tert-butyl 2-[2-(2,6-dioxo-3-piperidyl)-1,3-dioxo-isoindolin-4-yl]oxyacetate To a mixture of 2-(2,6-dioxo-3-piperidyl)-4-hydroxy-isoindoline-1,3-dione (20 g, 72.9 mmol) and tert-butyl 2-chloroacetate (16.5 g, 109 mmol) in DMF (50 mL) was added Ag$_2$O (16.9 g, 72.9 mmol), K$_2$CO$_3$ (25.2 g, 182 mmol) and KI (1.21 g, 7.29 mmol). The reaction mixture was stirred at rt for 12 h. On completion, the reaction mixture was filtered and the filtrate was diluted with H$_2$O (40 mL) and extracted with DCM (2×200 mL). The combined organic layer was dried over Na$_2$SO$_4$, filtered and concentrated in vacuo. The residue was purified by silica gel chromatography to give the title compound (2.40 g, 8.5% yield) as a white solid. $^1$H NMR (400 MHz, DMSO-d$_6$) δ 11.13 (s, 1H), 7.84-7.78 (m, 1H), 7.49 (d, J=7.2 Hz, 1H), 7.38 (d, J=8.8 Hz, 1H), 5.12 (dd, J=5.2, 12.8 Hz, 1H), 4.98 (s, 2H), 2.60-2.54 (m, 1H), 2.52-2.50 (m, 2H), 2.10-2.01 (m, 1H), 1.43 (s, 9H).

Step 3—2-[2-(2,6-Dioxo-3-piperidyl)-1,3-dioxo-isoindolin-4-yl]oxyacetic acid

To a mixture of tert-butyl 2-[2-(2,6-dioxo-3-piperidyl)-1,3-dioxo-isoindolin-4-yl]oxyacetate (2.40 g, 6.18 mmol) in DCM (10 mL) was added TFA (61.5 g, 539 mmol). Then the reaction mixture was stirred at rt for 12 h. On completion, the reaction mixture was concentrated in vacuo to give the title compound (3.10 g, 90% yield, TFA salt) as a white solid. $^1$H NMR (400 MHz, DMSO-d$_6$) δ 11.13 (s, 1H), 7.80 (dd, J=7.2, 8.4 Hz, 1H), 7.48 (d, J=7.2 Hz, 1H), 7.40 (d, J=8.4 Hz, 1H), 5.11 (dd, J=5.2, 12.8 Hz, 1H), 5.00 (s, 2H), 2.95-2.84 (m, 1H), 2.64-2.53 (m, 2H), 2.11-1.98 (m, 1H); LC-MS (ESI$^+$) m/z 332.9 (M+H)$^+$.

(3S,4S,5S)-4-Ethyl-3-fluoro-5-(hydroxymethyl)pyrrolidin-2-one (Intermediate CB)

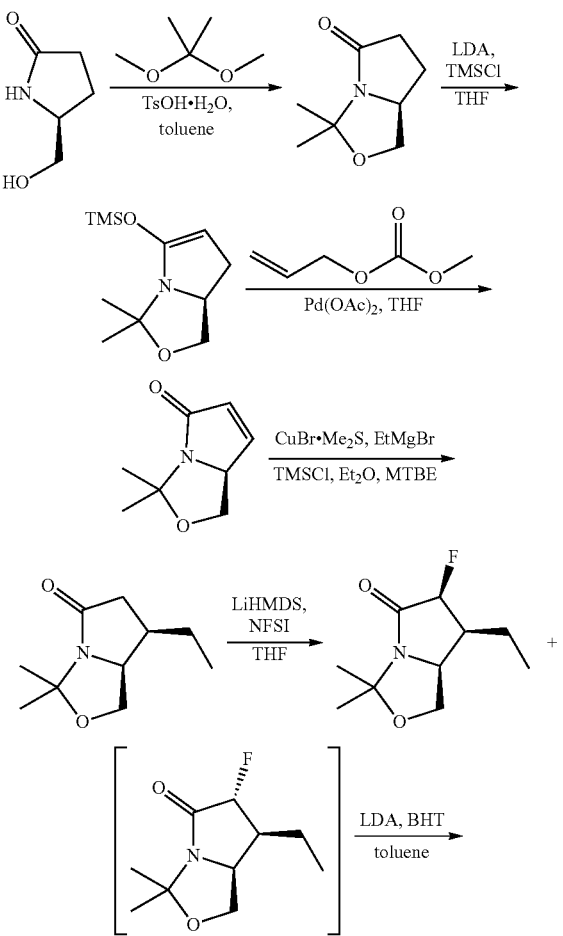

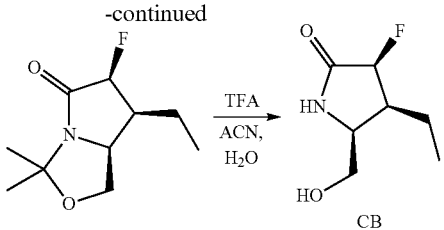

Step 1—(S)-3,3-Dimethyltetrahydropyrrolo[1,2-c]oxazol-5 (3H)-one

To a mixture of (5S)-5-(hydroxymethyl)pyrrolidin-2-one (200 g, 1.74 mol) and 2,2-dimethoxypropane (517 g, 4.97 mol) in toluene (2.4 L) was added TsOH.H$_2$O (13.2 g, 69.5 mmol). The reaction mixture was then stirred at 120° C. for 16 h. On completion, the reaction mixture was concentrated in vacuo and diluted with EA (5 L). The mixture was washed with 1N NaOH solution (2 L) and extracted with EA (8×1 L). The organic layer was dried over Na$_2$SO$_4$, filtered and concentrated in vacuo. The residue was triturated with PE (200 mL) to give the title compound (200 g, 74% yield) as a black brown crystal. $^1$H NMR (400 MHz, CDCl$_3$) δ 4.29-4.19 (m, 1H), 4.05 (dd, J=5.6, 8.4 Hz, 1H), 3.42 (t, J=8.4 Hz, 1H), 2.81-2.71 (m, 1H), 2.58-2.44 (m, 1H), 2.21-2.08 (m, 1H), 1.82-1.66 (m, 1H), 1.68 (s, 3H), 1.47 (s, 3H).

Step 2—(S)-3,3-Dimethyl-5-((trimethylsilyl)oxy)-1,3,7,7a-tetrahydropyrrolo[1,2-c]oxazole To a solution of DIPA (119 g, 1.18 mol) in THF (1.3 mL) was added n-BuLi (2.5 M, 433 mL) at −25° C. The reaction mixture was stirred for 30 min. Then, the reaction mixture was cooled to −70° C. A solution of (S)-3,3-dimethyltetrahydropyrrolo[1,2-c]oxazol-5 (3H)-one (140 g, 902 mmol) in THF (500 mL) was added dropwise. The reaction mixture was stirred at −60° C. for 5 min. Then, TMSCl (127 g, 1.17 mmol) was added dropwise at −60° C. The reaction mixture was allowed to warm to −10° C. and stirred for 25 min. On completion, the reaction mixture was concentrated in vacuo. The residue was triturated with hexane (1 L), filtered and the filtrate was concentrated in vacuo to give the title compound (140 g, 68% yield) as a colorless oil. The product was unstable and was used for the next step directly without purification.

Step 3 (7aS)-3,3-dimethyl-1,7a-dihydropyrrolo[1,2-c]oxazol-5-one

To a mixture of (S)-3,3-dimethyl-5-((trimethylsilyl)oxy)-1,3,7,7a-tetrahydropyrrolo[1,2-c]oxazole (140 g, 616 mmol) and allyl methyl carbonate (107 g, 923 mmol) in THF (1.4 L) was added Pd(OAc)$_2$ (41.5 g, 185 mmol). The reaction mixture was stirred at 65° C. for 8 h under nitrogen. On completion, the reaction mixture was concentrated in vacuo. The residue was purified by silica gel chromatography (PE:EA=5:1) to give the title compound (30 g, 32% yield) as a colorless oil. $^1$H NMR (400 MHz, CDCl$_3$) δ 7.00 (d, J=5.6 Hz, 1H), 6.04 (d, J=5.6 Hz, 1H), 4.67-4.49 (m, 1H), 4.09-4.04 (m, 1H), 3.27 (t, J=8.8 Hz, 1H), 1.61 (s, 3H), 1.50 (s, 3H).

Step 4—(7R,7aS)-7-Ethyl-3,3-dimethyltetrahydropyrrolo[1,2-c]oxazol-5 (3H)-one

To a mixture of bromocopper-methylsulfanylmethane (14.1 g, 68.6 mmol) in THF (200 mL) was added EtMgBr (3

M, 45.7 mL) at −10° C. dropwise. Then, the reaction mixture was cooled to −70° C. and TMSCl (7.45 g, 68.6 mmol) was added dropwise over 15 min. The reaction mixture was then stirred at −70° C. for an additional 15 min. Then a solution of (7aS)-3,3-dimethyl-1,7a-dihydropyrrolo[1,2-c]oxazol-5-one (6.00 g, 27.4 mmol) in THF (20 mL) was added dropwise over 10 min. Then the reaction mixture was stirred at 0° C. for 20 min. On completion, the reaction mixture was poured into cool saturated NH$_4$Cl solution (100 mL) and extracted with EA (3×500 mL). The combined layer was dried over Na$_2$SO$_4$, filtered and concentrated in vacuo. The residue was purified by silica gel chromatography (PE:EA=3:1) to give the title compound (3 g, 60% yield). $^1$H NMR (400 MHz, CDCl$_3$) δ 4.34 (td, J=6.4, 9.6 Hz, 1H), 3.90 (dd, J=6.4, 8.4 Hz, 1H), 3.72 (dd, J=8.4, 9.6 Hz, 1H), 2.91 (dd, J=8.0, 16.8 Hz, 1H), 2.31 (dd, J=1.6, 16.8 Hz, 1H), 2.28-2.18 (m, 1H), 1.64 (s, 3H), 1.55-1.49 (m, 1H), 1.48 (s, 3H), 1.37-1.27 (m, 1H), 0.91 (t, J=7.2 Hz, 3H).

Step 5—(6S,7S,7aS)-7-Ethyl-6-fluoro-3,3-dimethyl-tetrahydropyrrolo[1,2-c]oxazol-5 (3H)-one A solution of (7R,7aS)-7-ethyl-3,3-dimethyl-1,6,7,7a-tetrahydropyrrolo[1,2-c]oxazol-5-one (2.5 g, 13.6 mmol) in THF (10 mL) was treated at −78° C. with LiHMDS (1 M, 15.0 mL) and the mixture was kept for 0.5 h at −78° C. A solution of NFSI (5.60 g, 17.8 mmol) in THF (10 mL) was added slowly. The mixture was kept at approximately −78° C. for 0.5 h. On completion, the precipitated solid was filtered and washed with THF (20 mL). The filtrate was concentrated in vacuo to an oily residue. The oily residue was purified by silica gel chromatography (PE:EA=10:1). Then, the residue was repurified by reversed phase chromatography (0.1% FA) to give the title compound (575 mg, 21% yield) as a colorless oil. $^1$H NMR (400 MHz, CD3CN) δ 4.89-4.73 (m, 1H), 4.42 (td, J=6.4, 10.4 Hz, 1H), 3.95 (dd, J=5.6, 8.4 Hz, 1H), 3.59 (dd, J=8.4, 10.4 Hz, 1H), 2.49-2.33 (m, 1H), 1.59 (s, 3H), 1.58-1.51 (m, 1H), 1.45 (s, 3H), 1.44-1.37 (m, 1H), 1.00 (t, J=7.2 Hz, 3H).

Step 6—(6S,7S,7aS)-7-Eethyl-6-fluoro-3,3-dimethyltetrahydropyrrolo[1,2-c]oxazol-5 (3H)-one To a solution of diisopropylamine (322 mg, 3.18 mmol) in toluene (5 mL) was added n-BuLi (2.5 M, 1.26 mL) dropwise at −30° C. The mixture was maintained at −30° C. for an additional 30 min, then a solution of (6R,7S,7aS)-7-ethyl-6-fluoro-3,3-dimethyl-1,6,7,7a-tetrahydropyrrolo[1,2-c]oxazol-5-one (575 mg, 2.86 mmol) in toluene (2 mL) was added dropwise at −78° C. over 2 h. After the addition was completed, the mixture was kept at −78° C. for 30 min more before a solution of BHT (1.30 g, 5.91 mmol) in toluene (2 mL) was added dropwise over 0.5 h, keeping the internal temperature below −65° C. After the addition was completed, the mixture was kept at −78° C. for 30 min. The mixture was then warmed to rt and stirred for 2 hrs. On completion, the reaction was quenched with water (5 mL) and extracted with ethyl acetate (3×50 mL). The combined organic layers were washed with brine (20 mL), dried over anhydrous sodium sulfate, filtered and concentrated in vacuo. The residue was purified by silica gel chromatography (PE:EA=10:1) to give the title compound (244 mg, 40% yield) as a white solid. $^1$H NMR (400 MHz, CDCl$_3$) δ 5.36-5.15 (m, 1H), 4.12-4.01 (m, 2H), 3.79-3.68 (m, 1H), 2.78-2.64 (m, 1H), 1.80-1.70 (m, 1H), 1.69 (s, 3H), 1.50 (s, 3H), 1.42-1.32 (m, 1H), 0.98 (t, J=7.2 Hz, 3H). LC-MS (ESI$^+$) m/z 202.1 (M+H)$^+$.

Step 7—(3S,4S,5S)-4-Ethyl-3-fluoro-5-(hydroxymethyl)pyrrolidin-2-one (6S,7S,7aS)-7-ethyl-6-fluoro-3,3-dimethyl-1,6,7,7a-tetrahydropyrrolo[1,2-c]oxazol-5-one (330 mg, 1.64 mmol) in acetonitrile (1.5 mL) and H$_2$O (0.15 mL) was treated with TFA (37.4 mg, 328 umol). The mixture was warmed to −65° C. over 1 h, and held at that temperature for 3 hrs. On completion, the mixture was concentrated in vacuo. The residue was reversed phase chromatography to give the title compound (230 mg, 91% yield). $^1$H NMR (400 MHz, CDCl$_3$) δ 7.59 (s., 1H), 4.80 (dd, 1H), 3.69-3.83 (m, 2H), 3.52-3.64 (m, 1H), 3.48 (br. s, 1H), 2.27-2.52 (m, 1H), 1.57-1.73 (m, 1H), 1.49 (dt, 1H), 1.04 (t, 3H). LC-MS (ESI$^+$) m/z 162.1 (M+H)$^+$ 7-Methoxy-1-oxo-1,2-dihydroisoquinoline-6-carbonitrile (Intermediate CC)

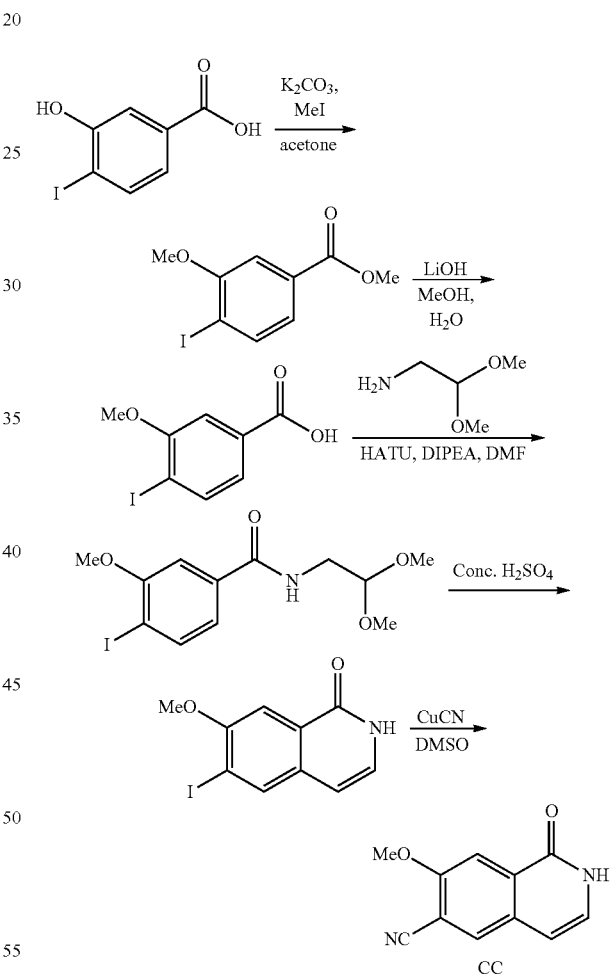

Step 1—Methyl 4-iodo-3-methoxybenzoate

To a solution of 3-hydroxy-4-iodo-benzoic acid (25.0 g, 94.7 mmol) in acetone (350 mL) was added K$_2$CO$_3$ (52.4 g, 379 mmol) and CH$_3$I (53.8 g, 379 mmol). The reaction mixture was stirred at 50° C. for 16 hours. On completion, the reaction mixture was concentrated in vacuo. The residue was dissolved with ethyl acetate (150 mL) and washed with water (150 mL). The organic phase was dried over anhydrous sodium sulfate, filtered and concentrated in vacuo to give the title compound (24.5 g, 89% yield) as a yellow oil. $^{1}$H NMR (400 MHz, CDCl$_3$) δ 7.86 (d, J=8.0 Hz, 1H), 7.46 (d, J=1.6 Hz, 1H), 7.38 (dd, J=1.6, 8.0 Hz, 1H), 3.95 (s, 3H), 3.93 (s, 3H).

Step 2—4-Iodo-3-methoxybenzoic acid

To a solution of methyl 4-iodo-3-methoxy-benzoate (3.00 g, 10.3 mmol) in a mixture of methanol (20 mL) and water (5 mL) was added LiOH.H$_2$O (1.29 g, 30.8 mmol). The reaction mixture was stirred at rt for 2 h. On completion, the reaction mixture was concentrated in vacuo to remove the methanol. The aqueous phase was acidified with 2N HCl solution until the pH=2, and filtered. The filter cake was dried in vacuo to give the title compound (2.70 g, 95% yield) as a white solid. $^{1}$H NMR (400 MHz, DMSO-d$_6$) δ 13.21 (s, 1H), 7.91 (d, J=8.0 Hz, 1H), 7.42 (d, J=1.6 Hz, 1H), 7.30 (dd, J=1.6, 8.0 Hz, 1H), 3.89 (s, 3H).

Step 3—N-(2,2-dimethoxyethyl)-4-iodo-3-methoxy-benzamide

To a mixture of 4-iodo-3-methoxy-benzoic acid (2.3 g, 8.3 mmol), HATU (3.77 g, 9.93 mmol) and DIPEA (3.21 g, 24.8 mmol) in DMF (40 mL) was added 2,2-dimethoxy-ethanamine (1.04 g, 9.93 mmol). The reaction mixture was stirred at rt for 1 h. On completion, the reaction mixture was concentrated in vacuo. The residue was diluted with water (40 mL), acidified with citric acid, and extracted with EA (3×100 mL). The organic phase was dried over anhydrous Na$_2$SO$_4$, filtered and concentrated in vacuo. The crude product was purified by silica gel chromatography (PE/EA=1/2) to give the title compound (2.80 g, 93% yield) as a white solid. $^{1}$H NMR (400 MHz, CDCl$_3$) δ 7.83 (d, J=8.0 Hz, 1H), 7.34 (d, J=2.0 Hz, 1H), 6.99 (dd, J=2.0, 8.0 Hz, 1H), 6.33 (s, 1H), 4.49 (t, J=5.6 Hz, 1H), 3.95 (s, 3H), 3.61 (t, J=5.6 Hz, 2H), 3.45 (s, 6H).

Step 4—6-Iodo-7-methoxyisoquinolin-1 (2H)-one

A mixture of N-(2,2-dimethoxyethyl)-4-iodo-3-methoxy-benzamide (3.30 g, 9.04 mmol) in concentrated H$_2$SO$_4$ (15 mL) was stirred at 60° C. for 0.5 h. On completion, the reaction mixture was pour into ice water (200 mL) and extracted with DCM (3×200 mL). The combined organic layer was dried in vacuo to give the title compound (2.50 g, 92% yield) as a white solid. $^{1}$H NMR (400 MHz, DMSO-d$_6$) δ 11.29 (s, 1H), 8.22 (s, 1H), 7.54 (s, 1H), 7.07 (d, J=7.2 Hz, 1H), 6.48 (d, J=7.2 Hz, 1H), 3.92 (s, 3H).

Step 5—7-Methoxy-1-oxo-1,2-dihydroisoquinoline-6-carbonitrile

A mixture of 6-iodo-7-methoxy-2H-isoquinolin-1-one (2.4 g, 7.97 mmol) and CuCN (2.14 g, 23.9 mmol) in DMF (50 mL) was stirred at 125° C. for 1 h under nitrogen. On completion, the reaction mixture was concentrated in vacuo. The residue was dissolved in DCM:MeOH=10:1 (100 mL), filtered and concentrated in vacuo to give the title compound (1.40 g, 88% yield) as a yellow solid. $^{1}$H NMR (400 MHz, DMSO-d$_6$) δ 11.52 (s, 1H), 8.24 (s, 1H), 7.78 (s, 1H), 7.17 (dd, J=5.6, 7.2 Hz, 1H), 6.57 (d, J=7.2 Hz, 1H), 4.02 (s, 3H).

1-(((2S,3S,4S)-3-Ethyl-4-fluoro-5-oxopyrrolidin-2-yl)methoxy)-7-methoxyisoquinoline-6-carbonitrile (Intermediate CD)

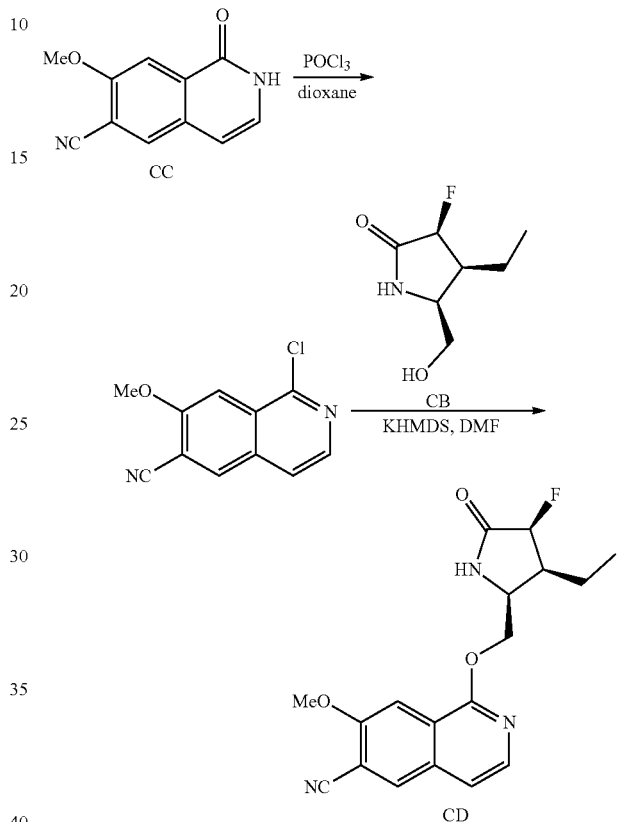

Step 1—1-Chloro-7-methoxyisoquinoline-6-carbonitrile

To a mixture of 7-methoxy-1-oxo-2H-isoquinoline-6-carbonitrile (1.25 g, 6.24 mmol, Intermediate CC) in dioxane (50 mL) was added POCl$_3$ (3.83 g, 25.0 mmol). The reaction mixture was stirred at 110° C. for 2 h. On completion, the reaction mixture was concentrated to remove the solvent. The residue was dissolved in DCM (20 mL) and washed with NaHCO$_3$ solution until the pH=8. The reaction mixture was then extracted with DCM (3×100 mL). The combined layer was dried over Na$_2$SO$_4$, filtered, and the filtrate was concentrated in vacuo. The residue was purified by silica gel chromatography (PE:DCM=1:5) to give the title compound (1.00 g, 60% yield) as an off-white solid. LC-MS (ESI$^+$) m/z 219.0 (M+H)$^+$.

Step 2—1-(((2S,3S,4S)-3-Ethyl-4-fluoro-5-oxopyrrolidin-2-yl)methoxy)-7-methoxyisoquinoline-6-carbonitrile A mixture of 1-chloro-7-methoxy-isoquinoline-6-carbonitrile (50.0 mg, 229 umol) and (3S,4S,5S)-4-ethyl-3-fluoro-5-(hydroxymethyl)pyrrolidin-2-one (36.9 mg, 229 umol, Intermediate CB) were stirred in DMF (1 mL) and cooled to approximately −10° C. A solution of KHMDS (1 M, 503.11 uL) in THF was then added into the reaction mixture over −15 minutes, maintaining the internal reaction temperature at approximately −10° C. After, the reaction was stirred at −10° C. for approximately an additional 30 minutes. On completion, the reaction mixture was quenched with saturated NaH₂PO₄ (20 mL) and extracted with ethyl acetate (3×100 mL). The combined organic layers were washed with brine (20 mL), dried over anhydrous sodium sulfate, filtered and concentrated in vacuo. The residue was purified by prep-TLC (EA) to give the title compound (50.0 mg, 49% yield) as a white solid. LC-MS (ESI⁺) m/z 344.0 (M+H)⁺.

Methyl 4-[3-(difluoromethyl)-4-(4,4,5,5-tetramethyl-1,3,2-dioxaborolan-2-yl)pyrazol-1-yl]benzoate (Intermediate EB)

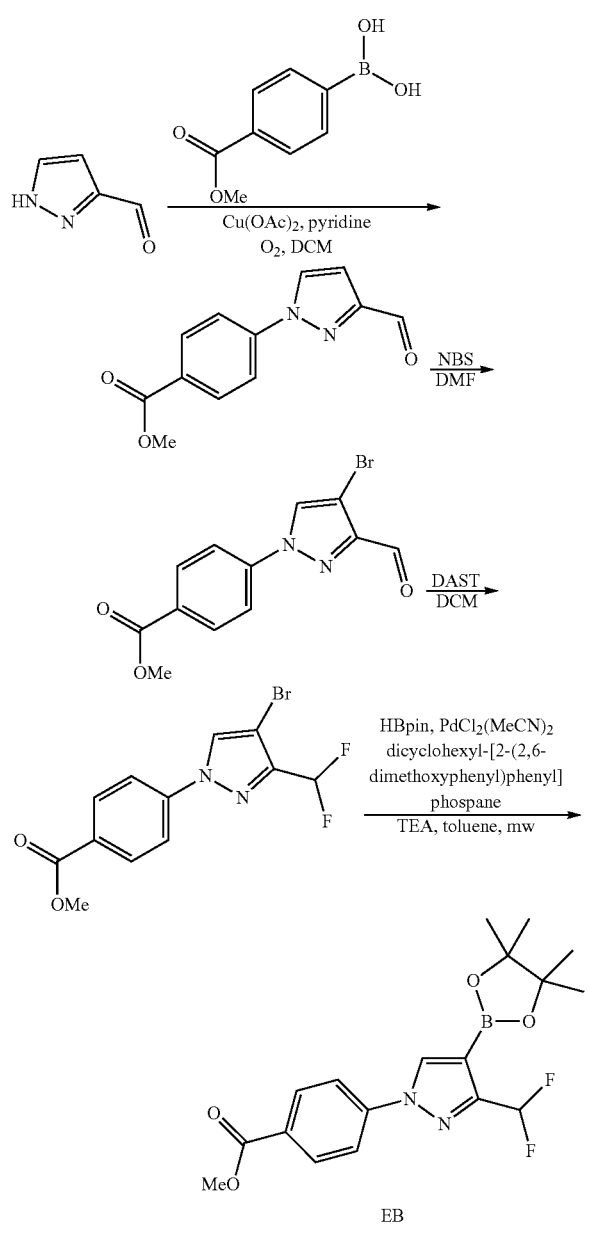

EB

Step 1—Methyl 4-(3-formyl-1H-pyrazol-1-yl)benzoate

To a solution of 1H-pyrazole-3-carbaldehyde (10.0 g, 104 mmol, CAS #3920-20-1) and (4-methoxy carbonyl-phenyl) boronic acid (22.5 g, 125 mmol, CAS #99768-12-4) in DCM (50 mL) was added Cu(OAc)₂ (22.7 g, 125 mmol) and pyridine (32.9 g, 416 mmol). The reaction mixture was stirred at rt for 18 hours under oxygen gas (balloon). On completion, the mixture was concentrated in vacuo. The residue was purified by silica gel chromatography to give the title compound (12.0 g, 50% yield) as a white solid. ¹H NMR (400 MHz, CDCl₃) δ 10.10 (s, 1H), 8.24-8.14 (m, 2H), 8.06 (d, J=2.4 Hz, 1H), 7.90-7.82 (m, 2H), 7.02 (d, J=2.4 Hz, 1H), 3.95 (s, 3H).

Step 2—Methyl 4-(4-bromo-3-formyl-1H-pyrazol-1-yl)benzoate

To a solution of methyl 4-(3-formylpyrazol-1-yl)benzoate (4.00 g, 17.4 mmol) in DMF (40 mL) was added NBS (6.18 g, 34.8 mmol). The reaction mixture was stirred at rt for 1 hour. Then, the reaction mixture was heated to 50° C. and stirred for 12 hours. On completion, the mixture was concentrated in vacuo. The residue was purified by prep-HPLC (0.1% FA) to give the title compound (4.50 g, 82% yield) as a white solid. ¹H NMR (400 MHz, CDCl₃) δ 10.02 (s, 1H), 8.12 (d, J=8.4 Hz, 2H) 8.04 (s, 1H), 7.75 (d, J=8.4 Hz, 2H), 3.89 (s, 3H); LC-MS (ESI⁺) m/z 308.9, 310.9 (M+1)⁺.

Step 3—Methyl 4-(4-bromo-3-(difluoromethyl)-1H-pyrazol-1-yl)benzoate

To a solution of methyl 4-(4-bromo-3-formyl-pyrazol-1-yl)benzoate (1.70 g, 5.50 mmol) in DCM (100 mL) was added DAST (7.98 g, 49.5 mmol) at 0° C. The reaction mixture was then allowed to warm to rt and stirred for 5 hours. On completion, the mixture was quenched with methanol (30 mL) at 0° C. then mixture was concentrated in vacuo. The residue was purified by prep-HPLC (0.1% HCl) to give the title compound (1.44 g, 78% yield) as a white solid. ¹H NMR (400 MHz, CDCl₃) δ 8.17 (d, J=8.8 Hz, 2H), 8.07 (s, 1H), 7.76 (d, J=8.8 Hz, 2H), 6.80 (t, J=53.2 Hz, 1H), 3.96 (s, 3H); LC-MS (ESI⁺) m/z 330.9 (M+H)⁺.

Step 4—Methyl 4-[3-(difluoromethyl)-4-(4,4,5,5-tetramethyl-1,3,2-dioxaborolan-2-yl)pyrazol-1-yl]benzoate Methyl 4-[4-bromo-3-(difluoromethyl)pyrazol-1-yl]benzoate (500 mg, 1.51 mmol), TEA (382 mg, 3.78 mmol), acetonitrile-dichloropalladium (58.8 mg, 227 umol), dicyclohexyl-[2-(2,6-dimethoxy phenyl)phenyl]phosphane (93.0 mg, 227 umol) and HBPin (1.93 g, 15.1 mmol) were taken up into a microwave tube in toluene (10 mL). The sealed tube was heated at 90° C. for 60 minutes under microwave. On completion, the mixture was filtered and the filtrate was concentrated in vacuo. The residue was purified by silica gel chromatography to give the title compound (440 mg, 54% yield) as a yellow solid. LC-MS (ESI⁺) m/z 379.2 (M+H)⁺.

Methyl 4-[4-amino-3-(difluoromethyl)pyrazol-1-yl]benzoate (Intermediate FW)

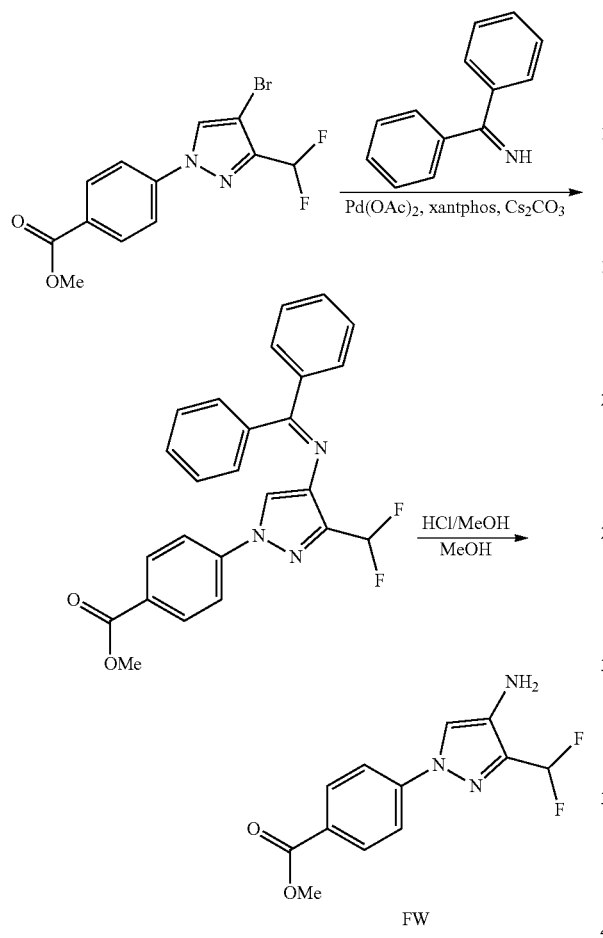

Step 1—Methyl 4-[4-(benzhydrylideneamino)-3-(difluoromethyl)pyrazol-1-yl]benzoate A mixture of methyl 4-[4-bromo-3-(difluoromethyl)pyrazol-1-yl]benzoate (0.15 g, 453 umol, synthesized via Steps 1-2 of Intermediate EB), diphenylmethanimine (205 mg, 1.13 mmol), Pd(OAc)$_2$ (20.8 mg, 92.4 umol), Xantphos (26.2 mg, 45.3 umol) and Cs$_2$CO$_3$ (448 mg, 1.38 mmol) in dioxane (3 mL) was degassed and purged with N$_2$ 3 times, and then the mixture was stirred at 120° C. for 3 hrs under N$_2$ atmosphere. On completion, the mixture was concentrated, then H$_2$O (30 mL) was added and the mixture was extracted with EtOAc (3×30 mL). The organic phase was dried with Na$_2$SO$_4$, filtrated and concentrated in vacuo. The residue was purified by flash silica gel chromatography to give the title compound (0.24 g, 50% yield) as a yellow solid. $^1$H NMR (400 MHz, CDCl$_3$) δ 8.02-7.95 (m, 2H), 7.80-7.73 (m, 2H), 7.51-7.45 (m, 3H), 7.43-7.31 (m, 5H), 7.22-7.19 (m, 2H), 7.12-6.82 (m, 1H), 6.37 (s, 1H), 3.85 (s, 3H); LC-MS (ESI$^+$) m/z 432.1 (M+H)$^+$.

Step 2—Methyl 4-[4-amino-3-(difluoromethyl)pyrazol-1-yl]benzoate

To a solution of methyl 4-[4-(benzhydrylideneamino)-3-(difluoromethyl)pyrazol-1-yl]benzoate (215 mg, 498 umol) in THF (2 mL) and MeOH (20 mL) was added HCl/MeOH (4 M, 124 uL). The mixture was stirred at 25° C. for 30 min. On completion, the mixture was concentrated to give the title compound (0.20 g, 90% yield) as a yellow solid. LC-MS (ESI$^+$) m/z 268.1 (M+H)$^+$.

2,2-Dimethyl-4-oxo-3,8,11,14,17-pentaoxa-5-azanonadecan-19-oic acid (Intermediate EN)

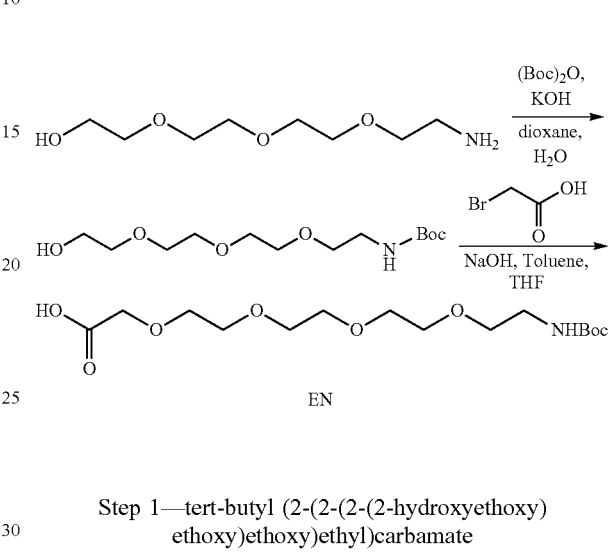

Step 1—tert-butyl (2-(2-(2-(2-hydroxyethoxy)ethoxy)ethoxy)ethyl)carbamate

To a stirred solution of 2-(2-(2-(2-aminoethoxy)ethoxy)ethoxy)ethan-1-ol (1.0 g, 5.2 mmol, CAS #86770-74-3) and KOH (0.32 g, 5.6 mmol) in 1,4 dioxane (4 mL) and water (8 mL) was added Boc-anhydride (1.24 g, 5.6 mmol) dropwise at 10° C. The resulting reaction mixture was allowed to warm to rt and stirred for 16 h. The reaction mixture was transferred into ice water and the resulting mixture was extracted using ethyl acetate (3×100 mL). The combined organic layers were dried over anhydrous sodium sulfate and filtered. The filtrate was evaporated under reduced pressure to afford crude product. The crude product was purified using silica gel column chromatography (8% MeOH-DCM) to give tert-butyl (2-(2-(2-(2-hydroxyethoxy)ethoxy)ethoxy)ethyl)carbamate as a colorless oil (1.2 g, 79%). LC-MS (ESI$^+$) m/z 293.13 (M+H)$^+$.

Step 2—2,2-dimethyl-4-oxo-3,8,11,14,17-pentaoxa-5-azanonadecan-19-oic acid

To a stirred solution of tert-butyl (2-(2-(2-(2-hydroxyethoxy)ethoxy)ethoxy)ethyl)carbamate (0.38 g, 1.29 mmol) and 2-bromoacetic acid (0.54 g, 3.8 mmol) in toluene:THF (1:1, 4 mL) was added NaOH (0.31 g, 7.7 mmol) at 45° C. The resulting reaction mixture stirred at 45° C. for 16 h. The reaction mixture was then evaporated, water (10 mL) was added and aqueous layer was acidified with 1 N HCl solution. The resulting mixture was extracted using DCM (3×50 mL) and the combined organic layer was dried over anhydrous sodium sulfate and filtered. The filtrate was evaporated under reduced pressure to give 2,2-dimethyl-4-oxo-3,8,11,14,17-pentaoxa-5-azanonadecan-19-oic acid as a colorless oil (0.24 g, 53%). LC-MS (ESI$^+$) m/z 351.4 (M+H)$^+$.

1267

4-Bromo-2-(2,6-dioxo-3-piperidyl)isoindoline-1,3-dione (Intermediate FT)

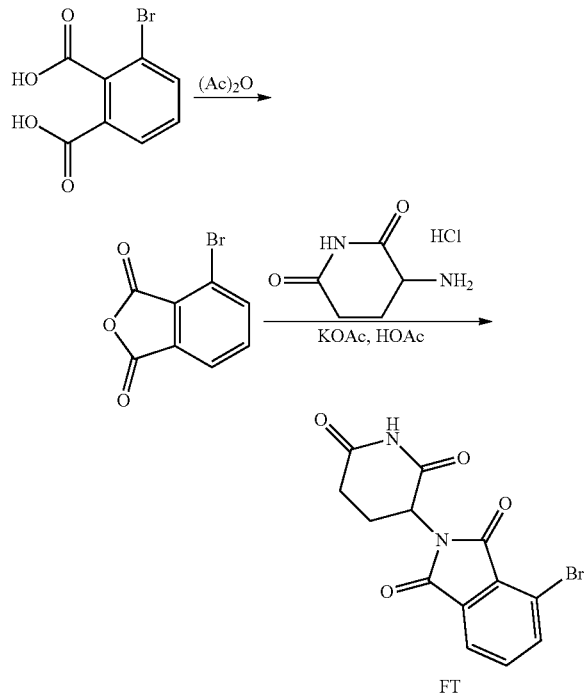

1268

Step 1—4-Bromoisobenzofuran-1,3-dione

A solution of 3-bromophthalic acid (5.00 g, 20.4 mmol, CAS #116-69-8) in $(Ac)_2O$ (20.4 mmol, 20 mL) was stirred at 120° C. for 12 hours. The reaction mixture was then stirred at 25° C. for 16 hours. On completion, the mixture was concentrated in vacuo to give the title compound (4.60 g, 99% yield) as yellow solid. LC-MS (ESI$^+$) m/z 227.1 (M+H)$^+$.

Step 2—4-Bromo-2-(2,6-dioxo-3-piperidyl)isoindoline-1,3-dione

To a solution of 4-bromoisobenzofuran-1,3-dione (4.60 g, 20.2 mmol) and 3-aminopiperidine-2,6-dione (3.67 g, 22.2 mmol, HCl, CAS #24666-56-6) in HOAc (40 mL) was added KOAc (6.16 g, 62.8 mmol), the reaction mixture was stirred at 90° C. for 16 hr. On completion, the mixture was cooled to 25° C. and diluted with ice water (800 mL), and then stirred at 0° C. for 0.5 hr. The reaction mixture was filtered and the filter cake was dried in vacuo to give the title compound (6.8 g, 99% yield) as gray solid. $^1$H NMR (400 MHz, DMSO-d$_6$) δ 11.17 (s, 1H), 8.19-7.65 (m, 3H), 5.41-4.91 (m, 1H), 3.35 (s, 1H), 3.05-2.85 (m, 1H), 2.72-2.54 (m, 2H), 2.09 (s, 1H).

Tert-butyl N-(cyclopropylmethyl)-N-[4-[4-[[3-(difluoromethyl)-1-(4-formylphenyl)pyrazol-4-yl]carbamoyl]oxazol-2-yl]-2-pyridyl]carbamate (Intermediate GF)

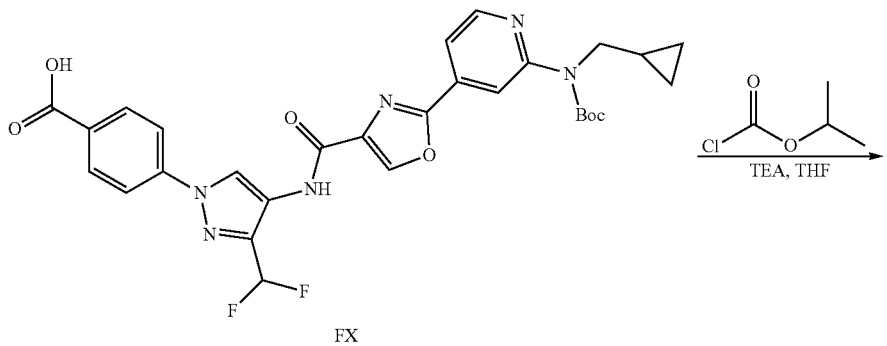

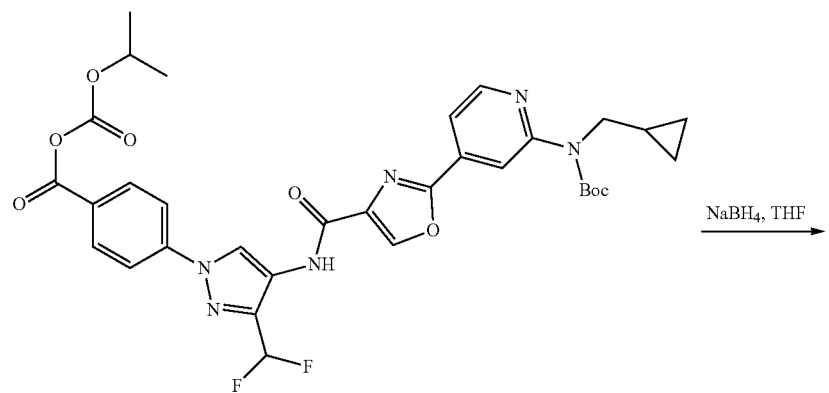

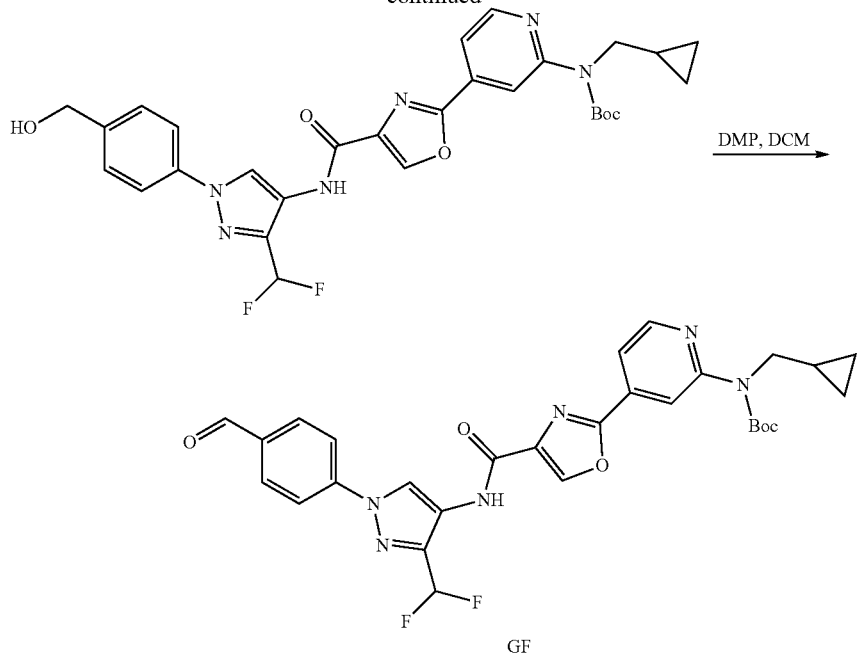

GF

Step 1—Isopropoxycarbonyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoate To a solution of 4-[4-[[2-[2-[tert-butoxycarbonyl(cyclopropylmethyl)amino]-4-pyridyl]oxazole-4-carbonyl]amino]-3-(difluoromethyl)pyrazol-1-yl]benzoic acid (250 mg, 420 umol, Intermediate FX) in THF (10 mL) was added TEA (170 mg, 1.68 mmol) and isopropyl carbonochloridate (128 mg, 1.05 mmol). The mixture was stirred at −10° C. for 1 hour. On completion, the mixture was filtered and the filtrate was concentrated in vacuo to give the title compound (280 mg, 90% yield) as yellow solid. LC-MS (ESI$^+$) m/z 681.3 (M+H)$^+$.

Step 2—Tert-butyl N-(cyclopropylmethyl)-N-[4-[4-[[3-(difluoromethyl)-1-[4-(hydroxymethyl)phenyl]pyrazol-4-yl]carbamoyl]oxazol-2-yl]-2-pyridyl]carbamate To a solution of isopropoxycarbonyl 4-[4-[[2-[2-[tert-butoxycarbonyl(cyclopropylmethyl)amino]-4-pyridyl]oxazole-4-carbonyl] amino]-3-(difluoromethyl)pyrazol-1-yl]benzoate (280 mg, 411 umol) in THF (30.0 mL) and H$_2$O (4.00 mL) was added NaBH$_4$ (62.2 mg, 1.65 mmol). The mixture was stirred at 0° C. for 1 hour. On completion, the mixture was diluted with H$_2$O (50 mL) and extracted with EtOAc (3×30 mL). The organic layers were dried over anhydrous Na$_2$SO$_4$, filtered and concentrated in vacuo. The mixture was triturated with DCM:PE=1:5 (30 mL), and filtered. The filter cake was dried in vacuo to give the title compound (200 mg, 83% yield) as white solid. LC-MS (ESI$^+$) m/z 581.3 (M+H)$^+$.

Step 3—Tert-butyl N-(cyclopropylmethyl)-N-[4-[4-[[3-(difluoromethyl)-1-(4-formylphenyl)pyrazol-4-yl]carbamoyl]oxazol-2-yl]-2-pyridyl]carbamate To a solution of tert-butyl N-(cyclopropylmethyl)-N-[4-[4-[[3-(difluoromethyl)-1-[4-(hydroxymethyl) phenyl]pyrazol-4-yl]carbamoyl]oxazol-2-yl]-2-pyridyl]carbamate (140 mg, 241 umol) in DCM (10.0 mL) was added DMP (204 mg, 482 umol). The mixture was stirred at 15° C. for 2 hours. On completion, the mixture was diluted with DCM (30 mL), and washed with saturated Na$_2$S$_2$O$_3$ (2×30 mL) and saturated NaHCO$_3$ (2×30 mL). The organic layer was dried over anhydrous Na$_2$SO$_4$, filtered and concentrated in vacuo to give the title compound (80.0 mg, 57% yield) as white solid. LC-MS (ESI$^+$) m/z 579.1 (M+H)$^+$.

3-(Difluoromethyl)-4-nitro-1H-pyrazole (Intermediate HS)

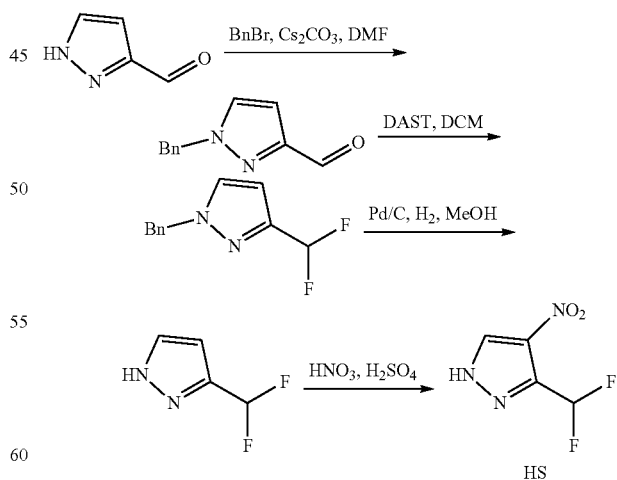

Step 1—1-Benzyl-1H-pyrazole-3-carbaldehyde

To a solution of 1H-pyrazole-3-carbaldehyde (5.00 g, 52.0 mmol, CAS #: 3920-50-1) and BnBr (9.34 g, 54.6 mmol) in DMF (50 mL) was added $Cs_2CO_3$ (42.4 g, 130 mmol). The reaction mixture was stirred at 25° C. for 1 hour. On completion, the reaction mixture was diluted with water, extracted with ethyl acetate (3×100 mL). The combined organic layers was washed with brine (50 mL), dried over anhydrous sodium sulfate, filtered and concentrated in vacuo. The crude product was purified by silica gel chromatography (Petroleum ether:Ethyl acetate=20:1) to give the title compound (8.00 g, 83% yield) as a colorless oil. $^1H$ NMR (400 MHz, $CDCl_3$) δ 10.02 (s, 1H), 7.44 (d, J=2.4 Hz, 1H), 7.43-7.33 (m, 3H), 7.29-7.24 (m, 2H), 6.85 (d, J=2.4 Hz, 1H), 5.42 (s, 2H).

Step 2—1-Benzyl-3-(difluoromethyl)-1H-pyrazole

To a solution of 1-benzylpyrazole-3-carbaldehyde (5.00 g, 26.9 mmol) in DCM (30 mL) was added DAST (17.3 g, 107 mmol) at 0° C. The reaction mixture was stirred at 25° C. for 5 hours. On completion, the reaction mixture was quenched with methanol (30 mL) at 0° C. After, the mixture was concentrated in vacuo. The crude product was purified by silica gel chromatography (petroleum ether:ethyl acetate=20:1) to give the title compound (3.30 g, 59% yield) as a white solid. $^1H$ NMR (400 MHz, $CDCl_3$) δ 7.43-7.36 (m, 3H), 7.27-7.21 (m, 2H), 6.91-6.57 (m, 1H), 6.55-6.51 (m, 1H), 5.35 (s, 2H); LC-MS ($ESI^+$) m/z 209.1 $(M+H)^+$.

Step 3—3-(Difluoromethyl)-1H-pyrazole

To a solution of 1-benzyl-3-(difluoromethyl)pyrazole (1.00 g, 4.80 mmol) in methanol (20 mL) was added $Pd(OH)_2/C$ (0.1 g, 10% purity) under $N_2$ atmosphere. The suspension was degassed and purged with $H_2$ for 3 times. The mixture was stirred at 40° C. for 12 hrs under $H_2$ (50 Psi). On completion, the reaction mixture was filtered and concentrated in vacuo to give the title compound (470 mg, 83% yield) as colorless oil. $^1H$ NMR (400 MHz, DMSO-$d_6$) δ 13.16 (s, 1H), 7.85 (s, 1H), 7.14-6.82 (m, 1H), 6.52 (s, 1H).

Step 4—3-(Difluoromethyl)-4-nitro-1H-pyrazole

To a solution of 3-(difluoromethyl)-1H-pyrazole (470 mg, 3.98 mmol) in $H_2SO_4$ (5 mL) was carefully added a 65% solution of $HNO_3$ (965 mg, 9.95 mmol) dropwise at 0° C. After stirring for 10 minutes, the reaction mixture was heated to 115° C., and stirred for 12 hrs. On completion, the reaction mixture was cooled to 25° C. Then, the reaction mixture was poured onto the (100 mL) ice, extracted with ethyl acetate (3×50 mL). The combined organic layers was washed with brine (2×50 mL), dried over with anhydrous sodium sulfate, filtered and concentrated in vacuo to give the title compound (530 mg, 82% yield). $^1H$ NMR (400 MHz, DMSO-$d_6$) δ 14.41 (s, 1H), 9.04 (s, 1H), 7.50-7.17 (m, 1H), 7.50-7.17 (m, 1H).

2,2-Dimethyl-4-oxo-3,8,11,14-tetraoxa-5-azahexadecan-16-yl 4-methylbenzenesulfonate (Intermediate LD)

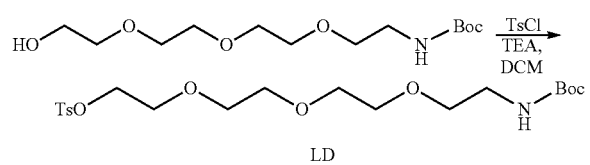

To a stirred solution of tert-butyl (2-(2-(2-(2-hydroxyethoxy)ethoxy)ethoxy)ethyl)carbamate (8 g, 27.30 mmol, synthesized via Step 1 of Intermediate EN) in DCM (100 mL) was added TEA (5.52 g, 54.60 mmol) at rt. To the above reaction mixture was added dropwise TsCl (10.41 g, 54.60 mmol) in DCM (5 mL) at 0° C. After the addition, the reaction mixture was stirred at rt overnight. The mixture was concentrated in vacuo and the residue was purified via column chromatography (Petroleum ether/EtOAc=5%-80%) to give the title compound (10.9 g, 73%) as a yellow oil. LC-MS ($ESI^+$): m/z 448.3 $(M+H)^+$.

2,2-Dimethyl-4-oxo-3,8,11,14,17-pentaoxa-5-azanonadecan-19-yl 4-methylbenzenesulfonate (Intermediate ON)

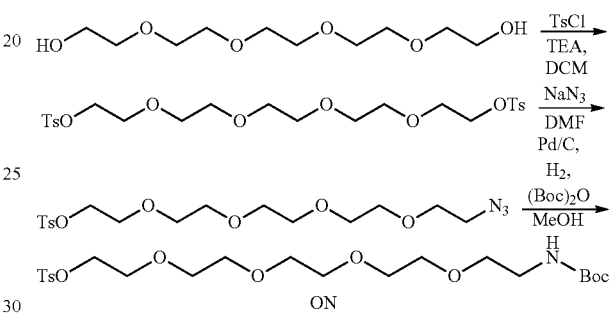

Step 1—3,6,9,12-tetraoxatetradecane-1,14-diyl bis(4-methylbenzenesulfonate)

To a mixture of 3,6,9,12-tetraoxatetradecane-1,14-diol (10 g, 42 mmol, CAS #75506-78-4) and TsCl (17.56 g, 92.4 mmol) in DCM (200 ml) was added TEA (17 g, 168 mmol) dropwise at rt and the mixture was stirred at rt overnight. Then the reaction mixture was concentrated in vacuo, the residue was dissolved in EtOAc (100 ml) and washed with water (100 ml×2), brine (100 ml), dried with $Na_2SO_4$, and filtered. The organic phase was evaporated and the residue was purified by silica gel chromatography (PE:EA=1:1) to give the title compound (19.17 g, 83.35 yield) as a yellow solid LC-MS ($ESI^+$): m/z 547.1 $(M+H)^+$.

Step 2—3,6,9,12-tetraoxatetradecane-1,14-diyl bis(4-methylbenzenesulfonate)

To a solution of 3,6,9,12-tetraoxatetradecane-1,14-diyl bis(4-methylbenzenesulfonate) (19.17 g, 35.1 mmol) in DMF (100 ml) was added $NaN_3$ (2.51 g, 38.62 mmol). The mixture was stirred rt for 2 days. The mixture was poured into water (300 ml) and extracted with EtOAc (3×300 ml). The combined organic layers were washed with water (300 ml×3) and brine (300 ml), dried with $Na_2SO_4$, and filtered. The organic phase was evaporated and the residue was purified by silica gel chromatography (PE:EA) to give the title compound as a colorless oil (6.5 g, 44% yield). LC-MS ($ESI^+$): m/z 418.2 $(M+H)^+$.

Step 3—2,2-dimethyl-4-oxo-3,8,11,14,17-pentaoxa-5-azanonadecan-19-yl 4-methylbenzenesulfonate A mixture of 14-azido-3,6,9,12-tetraoxatetradecyl 4-methylbenzenesulfonate (10 g, 20.4 mmol), Pd/C (20%, 1 g), (Boc)₂O (6.7 g, 30.6 mmol) and MeOH (200 mL) was stirred for overnight at rt under H2. The mixture was filtered and concentrated in vacuo. To the mixture was added H₂O (200 mL) then it was extracted with EA (300 mL). The organic layer was concentrated and purified by column chromatography (PE/EA=2/1 to 1/1 to EA) to give 2,2-dimethyl-4-oxo-3,8,11,14,17-pentaoxa-5-azanonadecan-19-yl 4-methylbenzenesulfonate (8.2 g, 69% yield) as a yellow oil. ¹H NMR (400 MHz, CDCl₃) δ 7.81-7.79 (d, J=8 Hz, 2H), 7.35-7.33 (d, J=8 Hz, 2H), 4.17-4.13 (t, J=4.8 Hz, 2H), 3.70-3.47 (m, 16H), 3.31-3.29 (t, J=5.2 Hz, 2H), 2.45 (s, 3H), 1.44 (s, 9H). LC-MS (ESI⁺): m/z 492.7 (M+H)⁺.

Benzyl N-[(1S)-2-[[(1S)-1-[(3S)-7-[2-[2-[2-(2-aminoethoxy)ethoxy]ethoxy]ethoxy]-3-[[(1R)-tetralin-1-yl]carbamoyl]-3,4-dihydro-1H-isoquinoline-2-carbonyl]-2,2-dimethyl-propyl] amino]-1-methyl-2-oxo-ethyl]-N-methyl-carbamate (Intermediate PF)

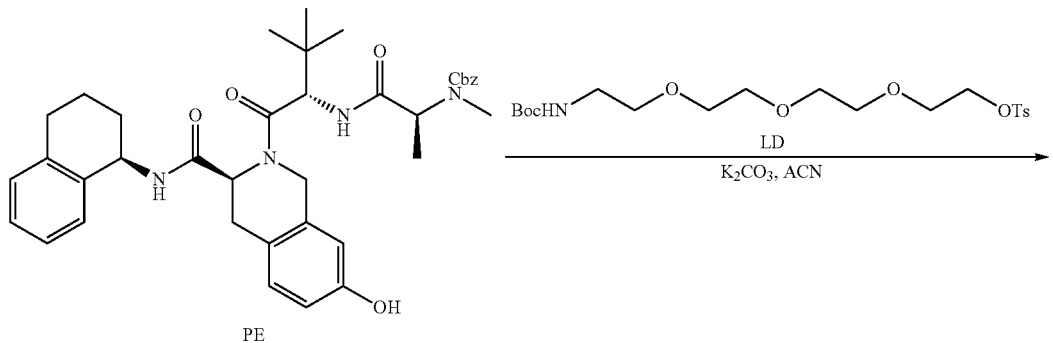

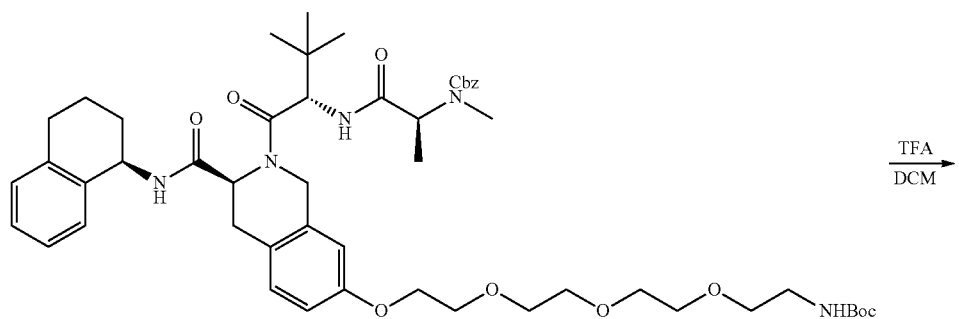

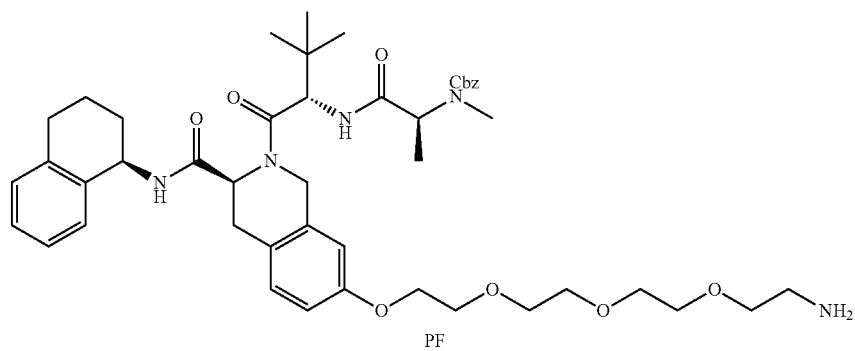

Step 1—benzyl ((S)-1-(((S)-1-((S)-7-((2,2-dimethyl-4-oxo-3,8,11,14-tetraoxa-5-azahexadecan-16-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate To a solution of benzyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (1.50 g, 2.29 mmol, Intermediate PE) in CH$_3$CN (20 mL) was added 2,2-dimethyl-4-oxo-3,8,11,14-tetraoxa-5-azahexadecan-16-yl 4-methylbenzenesulfonate (1.23 g, 2.75 mmoL, Intermediate LD), and K$_2$CO$_3$ (475 mg, 3.44 mmoL). The mixture was stirred at 82° C. overnight. The reaction mixture was then concentrated under reduced pressure and purified by silica gel chromatography eluted with DCM/EA=1:1 to give the title compound (1.64 g, 77% yield) as a yellow oil. LC/MS (ESI, m/z): [M+1]$^+$=931.4.

Step 2—benzyl ((S)-1-(((S)-1-((S)-7-(2-(2-(2-(2-aminoethoxy)ethoxy)ethoxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate A solution of benzyl ((S)-1-(((S)-1-((S)-7-((2,2-dimethyl-4-oxo-3,8,11,14-tetraoxa-5-azahexadecan-16-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (1.37 g, 1.47 mmoL) in TFA/DCM=10 mL/5 mL was stirred at rt for 1 h. The mixture was then concentrated under reduced pressure to give the title compound (900 mg, 74% yield) as a white solid. LC/MS (ESI, m/z): [M+1]$^+$=830.7. $^1$H NMR (400 MHz, DMSO-d$_6$) δ 8.23 (dd, J=49.6, 8.8 Hz, 1H), 7.81-7.56 (m, 4H), 7.35 (s, 5H), 7.16-6.71 (m, 7H), 5.29-4.58 (m, 8H), 4.06 (d, J=3.2 Hz, 2H), 3.76-3.73 (m, 2H), 3.64-3.52 (m, 10H), 3.05-2.91 (m, 3H), 2.87-2.80 (m, 2H), 2.78-2.61 (m, 3H), 1.91-1.50 (m, 4H), 1.20 (d, J=7.2 Hz, 2H), 1.12 (d, J=7.2 Hz, 1H), 0.99 (s, 6H), 0.92 (s, 3H).

Benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (Intermediate QD)

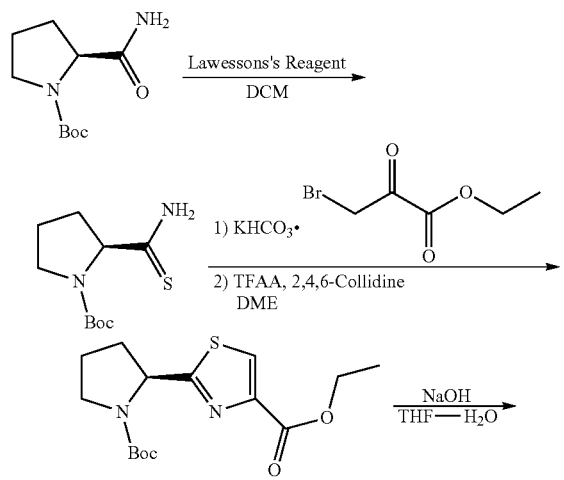

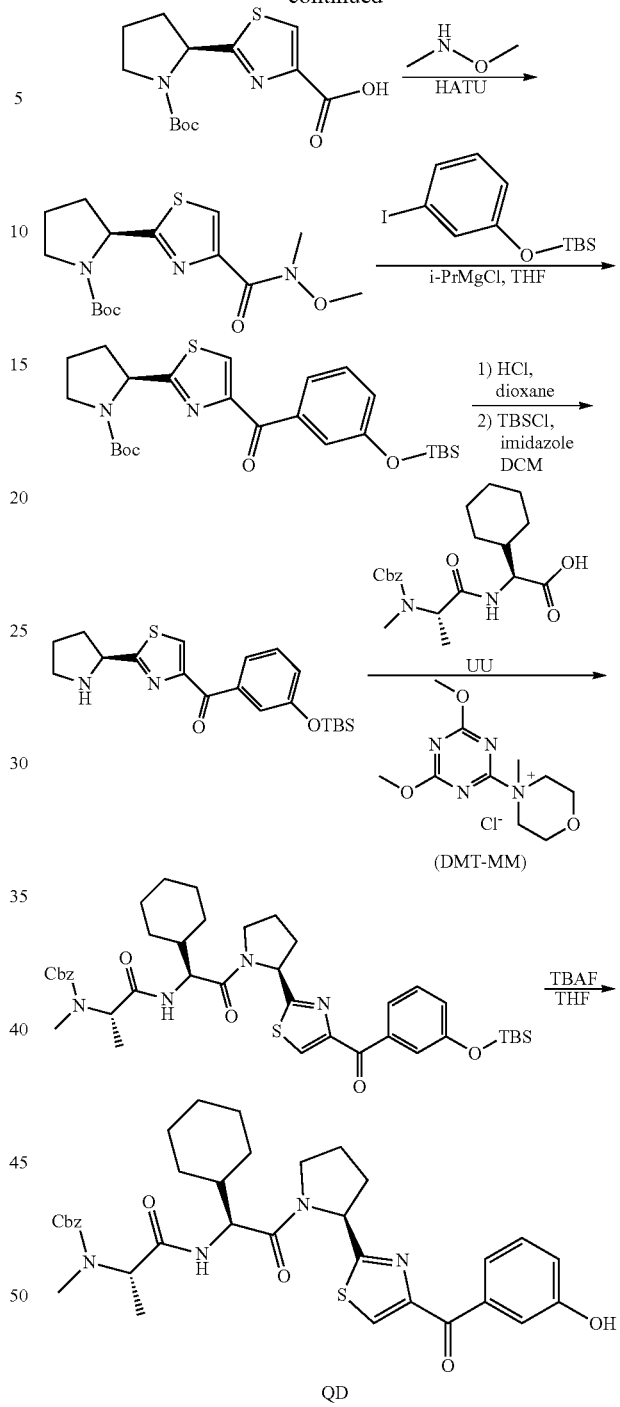

Step 1—(S)-tert-butyl 2-carbamothioylpyrrolidine-1-carboxylate

To a stirred solution Boc-D-prolinamide (50.0 g, 234.0 mmol) in CH$_2$Cl$_2$ (25 mL) at rt was added Lawesson's reagent (62.2 g, 140.0 mmol). The mixture was stirred overnight, then washed with NaHCO$_3$ (sat., 500 mL). The organic layer was washed with brine, and dried over anhydrous Na$_2$SO$_4$. The oily residue was purified by column chromatography on silica gel, eluted with a 0-10 percent MeOH in CH$_2$Cl$_2$ gradient, to afford the title compound (42 g, 7800 yield) as a white solid. $^1$H NMR (400 MHz, DMSO-d$_6$) δ 9.51 (s, 1H), 9.08 (m, 1H), 4.41 (dd, J=8.4, 3.3 Hz, 1H), 3.47-3.46 (m, 1H), 3.27 (s, 1H), 2.27-2.09 (m, 1H), 1.92-1.65 (m, 3H), 1.37 (m, 9H).

Step 2—ethyl (S)-2-(1-(tert-butoxycarbonyl)pyrrolidin-2-yl)thiazole-4-carboxylate Ethyl bromopyruvate (4.15 g, 21.3 mmol) was added dropwise via syringe to a mixture of (S)-tert-butyl 2-carbamothioylpyrrolidine-1-carboxylate (3.5 g, 15.2 mmol) and potassium bicarbonate (50.5 g, 504 mmol) in 35 mL of dimethoxyethane at 23c° C. The resulting mixture was stirred vigorously for 25 minutes, and then the mixture was cooled to 0° C. A mixture of trifluoroacetic anhydride (TFAA) (3.19 g, 15.2 mmol, 1 equiv.) and 2,4,6-collidine (2.94 g, 24.3 mmol, 1.6 equiv.) was then added dropwise via cannula to the yellow mixture prepared above at 0° C. Following this addition, an additional three portions of neat TFAA (3.19 g, 15.2 mmol, 1 equiv.) and 2,4,6-collidine (2.94 g, 24.3 mmol, 1.6 equiv.) were prepared and added in sequence dropwise via cannula to the yellow reaction mixture at 0° C. The resulting yellow mixture was stirred vigorously at 0° C. for 3 h. Then water (1,000 mL) was added and the solution was extracted with dichloromethane (2×50 mL). The organic phases were combined, washed with 0.5 N aqueous HCl (100 mL), washed with brine (100 mL), and dried over anhydrous sodium sulfate. The solution was filtered and concentrated to afford a light yellow solid. This solid was purified by flash column chromatography on silica gel (1:9 to 2:3 ethyl acetate:hexanes) providing a light yellow solid. This solid was triturated with ether (20 mL) to afford the title compound as a white solid (2.2 g, 44% yield). $^1$H NMR (400 MHz, DMSO-d$_6$) δ 8.41 (d, J=9.8 Hz, 1H), 5.08 (d, J=7.3 Hz, 1H), 4.33-4.25 (m, 2H), 3.53-3.34 (m, 2H), 2.38-2.27 (m, 1H), 2.04-1.99 (m, 1H), 1.93-1.79 (m, 2H), 1.43 (s, 6H), 1.30 (t, J=7.1 Hz, 3H), 1.24 (s, 3H). LC/MS (ESI, m/z): [M+1]$^+$=327.3.

Step 3—(S)-2-(1-(tert-butoxycarbonyl)pyrrolidin-2-yl)thiazole-4-carboxylic acid

A solution of (S)-ethyl 2-(1-(tert-butoxycarbonyl)pyrrolidin-2-yl)thiazole-4-carboxylate (14.5 g, 44.5 mmol, 1 equiv.) in tetrahydrofuran (60 mL) was added to a solution of sodium hydroxide (5.33 g, 134.5 mmol, 3 equiv.) in water (40 mL) at 23° C. The resulting mixture was stirred vigorously at 23° C. for 3 h. Then the mixture was concentrated to 20 mL. The concentrated mixture was cooled to 0° C. and the pH was adjusted to 3 by the addition of concentrated HCl solution dropwise. A lot of white solid was formed and the solid was collected by filtration to provide the title compound as a white solid (10.4 g, 74% yield). LC/MS (ESI, m/z): [M+1]$^+$=299.4.

Step 4—tert-butyl (S)-2-(4-(methoxy(methyl)carbamoyl)thiazol-2-yl)pyrrolidine-1-carboxylate (S)-2-(1-(tert-butoxycarbonyl)pyrrolidin-2-yl)thiazole-4-carboxylic acid (22.6 g, 75.8 mmol), O,N-dimethylhydroxylamine hydrochloride (11.9 g, 122.7 mmol), diisopropyl ethyl amine (45.0 mL, 243 mmol) and HATU (46.2 g, 122.0 mmol) in DMF (200 mL) were stirred at rt for 12 hours. The reaction mixture was quenched with water, and the layers were separated. The aqueous layer was extracted with EtOAc (100 mL×3), and the combined organic layers were dried, filtered and concentrated. The crude product was purified via column chromatography on silica gel, eluting with hexanes/ethyl acetate (1:1) to give the title compound as an oil (23.0 g, 89% yield). LC/MS (ESI, m/z): [M+1]$^+$=342.2. $^1$H NMR (400 MHz, DMSO-d$_6$) δ 8.11 (s, 1H), 5.08 (m, 1H), 3.72 (s, 3H), 3.52-3.35 (m, 2H), 3.29 (s, 3H), 2.32 (m, 1H), 2.06 (m, 1H), 1.96-1.77 (m, 2H), 1.50-1.20 (d, 9H).

Step 5—(S)-tert-butyl 2-(4-(3-((tert-butyldimethylsilyl)oxy)benzoyl)thiazol-2-yl)pyrrolidine-1-carboxylate To a solution of tert-butyl(3-iodophenoxy)dimethylsilane (6.9 g, 20.6 mmol) in THF (50 mL) was added isopropylmagnesium chloride solution (9.27 mL, 2.0 M in THF) dropwise at −10° C. under N$_2$. The reaction mixture was stirred at 0° C. for 30 min. Then this resulting mixture, which formed (3-((tert-butyldimethylsilyl)oxy)phenyl)magnesium iodide, was added dropwise via syringe to a solution of the weinreb amide tert-butyl (S)-2-(4-(methoxy(methyl) carbamoyl)thiazol-2-yl)pyrrolidine-1-carboxylate (3.9 g, 11.4 mmol) in THF (10 mL) at 0° C. The mixture was stirred at 0° C. for 30 min then warmed up to rt and stirred for 4 h. The mixture was then cooled to −5° C. and quenched with saturated ammonium chloride solution (20 mL). The mixture was partitioned between water (30 mL) and ethyl acetate (100 mL). The organic phase was separated and the aqueous phase was further extracted with ethyl acetate (3×100 mL). The organic phases were combined, washed with brine (50 mL) and dried over anhydrous sodium sulfate. The dried solution was filtered and concentrated to give a light yellow oil. This oil was purified by flash column chromatography on silica gel (1:30 to 1:10 ethyl acetate: hexanes) providing the title compound as a colorless oil (5.13 g, 92.1%). $^1$H NMR (400 MHz, CDCl$_3$) δ 8.10 (s, 1H), 7.76 (d, J=7.7 Hz, 1H), 7.71-7.66 (m, 1H), 7.34 (t, J=7.9 Hz, 1H), 7.07 (d, J=7.0 Hz, 1H), 5.30-5.19 (m, 1H), 3.66-3.41 (m, 2H), 2.42-2.19 (m, 2H), 2.01-1.90 (m, 2H), 1.50 (s, 3H), 1.35 (s, 6H), 1.02-0.98 (m, 9H), 0.28-0.14 (m, 6H); LC/MS (ESI, m/z): [M+1]$^+$=489.5.

Step 6—(S)-(3-((tert-butyldimethylsilyl)oxy)phenyl)(2-(pyrrolidin-2-yl)thiazol-4-yl)methanone To a solution of (S)-tert-butyl 2-(4-(3-((tert-butyldimethylsilyl)oxy)benzoyl)thiazol-2-yl)pyrrolidine-1-carboxylate (12.0 g, 20.5 mmol) in 1,4-dioxane (60 mL) was added HCl-dioxane (40 mL) (4 M in dioxane) dropwise. The reaction mixture was stirred at rt for 3 h. The reaction mixture concentrated in vacuo and used directly without further purification to afford (S)-(3-hydroxyphenyl)(2-(pyrrolidin-2-yl)thiazol-4-yl)methanone HCl salt (8.0 g). To a solution of (S)-(3-hydroxyphenyl)(2-(pyrrolidin-2-yl)thiazol-4-yl)methanone HCl salt (8.00 g, 25.7 mmol) in DCM (80 mL) was added imidazole (5.2 g, 57.2 mmol) slowly at 0° C. Then TBSCl (3.89 g, 34.3 mmol, in 20 mL DCM) was added slowly at 0° C. The resulting mixture was stirred at rt for 130 min. The reaction mixture was quenched with water, extracted with ethyl acetate (3×100 mL), washed with brine (50 mL) and dried over anhydrous sodium sulfate. The solution was filtered, concentrated, and purified by flash column chromatography on silica gel (1:100 to 1:40 methanol/DCM) to give the title compound as a yellow oil (8.0 g, 84% yield). $^1$H NMR (400 MHz, DMSO-d$_6$) δ 8.38 (s, 1H), 7.71-7.64 (m, 2H), 7.43 (t, J=8.0 Hz, 1H), 7.14 (ddd, J=8.0, 2.4, 1.1 Hz, 1H), 4.51 (dd, J=8.3, 4.9 Hz, 1H), 3.56 (s, 1H), 3.00-2.89 (m, 2H), 2.27-2.10 (m, 1H), 1.75-1.70 (m, 1H), 1.77-1.65 (m, 2H), 0.97 (s, 9H), 0.22 (s, 6H).

Step 7—benzyl ((S)-1-(((S)-2-((S)-2-(4-(3-((tert-butyldimethylsilyl)oxy)benzoyl)thiazol-2-yl)pyrrolidin-1-yl)-1-cyclohexyl-2-oxoethyl)amino)-1-oxopropan-2-yl)(methyl)carbamate In a 250-mL round-bottom flask, was placed (S)-(3-((tert-butyldimethyl silyl)oxy)phenyl)(2-(pyrrolidin-2-yl)thiazol-4-yl)methanone (7.5 g, 19.3 mmol), (S)-2-((S)-2-(((benzyloxy)carbonyl)(methyl)amino)propanamido)-2-cyclohexylacetic acid (9.5 g, 25.1 mmol, Intermediate UU), and 4-methylmorpholine (3.90 g, 38.60 mmol) in EtOAc (100 mL) at 0° C. DMT-MM (6.94 g, 25.1 mmol) was then added and the resulting solution was stirred for 3 h at 0° C. Then H$_2$O (40 mL) was added, and the resulting solution was extracted with EtOAC (3×50 mL). The combined organic layers were washed with 50 mL of brine, dried over anhydrous sodium sulfate and concentrated under vacuum. The residue was applied onto a silica gel column eluting with ethyl acetate/petroleum ether (1:2) to give the title compound as a yellow solid. (7.3 g, 60% yield). $^1$H NMR (400 MHz, DMSO-d$_6$) δ 8.49 (s, 1H), 7.95 (d, J=39.4 Hz, 1H), 7.74-7.63 (m, 2H), 7.43 (t, J=7.9 Hz, 1H), 7.35-7.31 (m, 5H), 7.16 (dd, J=8.0, 2.5 Hz, 1H), 5.37 (dd, J=7.6, 2.2 Hz, 1H), 5.08-5.01 (m, 1H), 4.66 (d, J=6.6 Hz, 1H), 4.37 (t, J=7.5 Hz, 1H), 3.83-3.75 (m, 2H), 2.83 (s, 3H), 2.33-2.14 (m, 2H), 2.07-1.98 (m, 2H), 1.67-1.48 (m, 6H), 1.25 (s, 3H), 1.07-0.89 (m, 14H), 0.22 (s, 6H). LC/MS (ESI, m/z): [M+1]$^+$=747.6.

Step 8—benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate To a stirred solution of benzyl ((S)-1-(((S)-2-((S)-2-(4-(3-((tert-butyldimethylsilyl)oxy)benzoyl)thiazol-2-yl)pyrrolidin-1-yl)-1-cyclohexyl-2-oxoethyl)amino)-1-oxopropan-2-yl)(methyl)carbamate (5.0 g, 6.68 mmol) in THF (20 mL) was added TBAF (8.0 mL, 8.0 mmol) a rt. The reaction mixture was stirred at rt for 4 h. Then H$_2$O (20 mL) was added and the mixture was extracted with EtOAc (50 mL×2). The combined organic layer was washed with brine, dried and concentrated in vacuo. The mixture was purified via column chromatography (DCM/EtOAc=5%-80%) to give the title compound (3.2 g, 76% yield) as a yellow solid. $^1$H NMR (400 MHz, MeOD-d$_4$) δ 8.26 (s, 1H), 7.59-7.53 (m, 1H), 7.51 (dd, J=2.3, 1.7 Hz, 1H), 7.37-7.28 (m, 6H), 7.05 (ddd, J=8.1, 2.6, 0.9 Hz, 1H), 5.50-5.39 (m, 1H), 5.13 (s, 2H), 4.69 (s, 1H), 4.54-4.38 (m, 1H), 4.02-3.93 (m, 1H), 3.90-3.86 (m, 1H), 2.94 (s, 3H), 2.23-2.10 (m, 4H), 1.72-1.56 (m, 6H), 1.37 (d, J=5.2 Hz, 3H), 1.16-0.88 (m, 5H); LC-MS (ESI$^+$): m/z 633.5 (M+H)$^+$.

Benzyl N-[(1S)-2-[[(1S)-2-[(2S)-2-[4-[3-[2-[2-[2-(2-aminoethoxy)ethoxy]ethoxy]ethoxy]benzoyl]thiazol-2-yl]pyrrolidin-1-yl]-1-cyclohexyl-2-oxo-ethyl]amino]-1-methyl-2-oxo-ethyl]-N-methyl-carbamate (Intermediate QG)

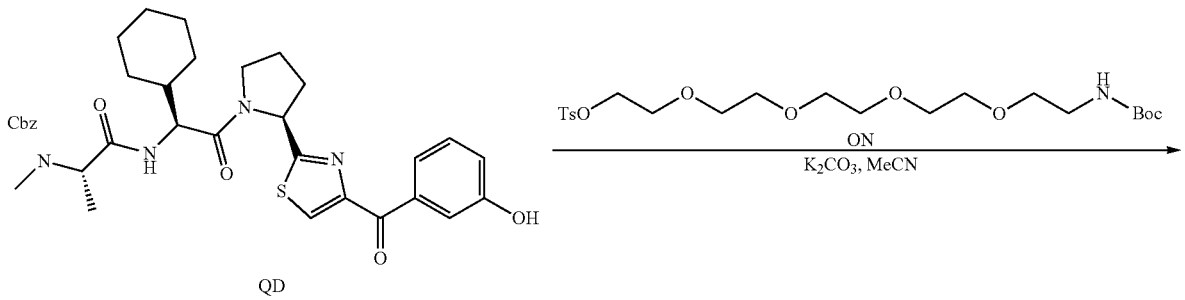

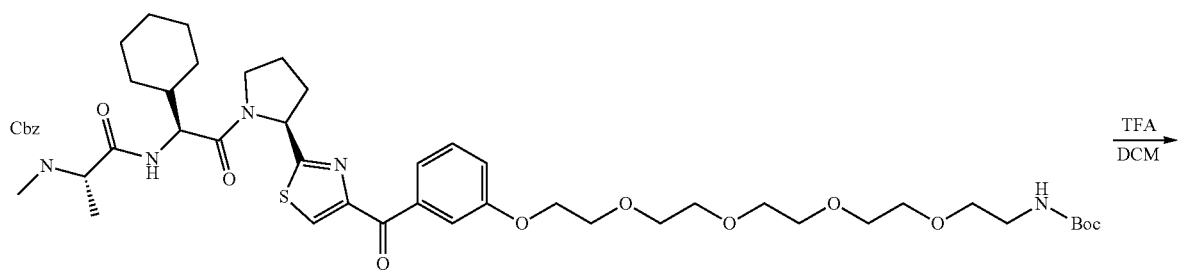

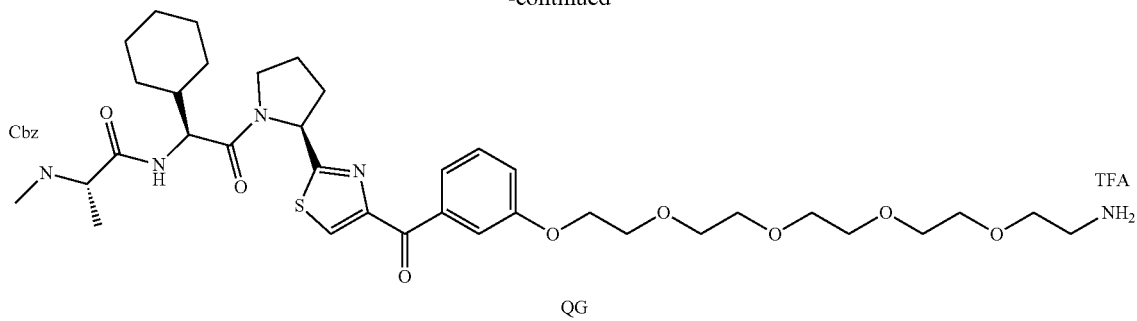

QG

Step 1—benzyl ((S)-1-(((S)-1-cyclohexyl-2-((S)-2-(4-(3-((2,2-dimethyl-4-oxo-3,8,11,14,17-pentaoxa-5-azanonadecan-19-yl)oxy)benzoyl)thiazol-2-yl)pyrrolidin-1-yl)-2-oxoethyl)amino)-1-oxopropan-2-yl)(methyl)carbamate To a solution of benzyl ((S)-1-(((S)-1-cyclohexyl-2-((S)-2-(4-(3-hydroxybenzoyl)thiazol-2-yl)pyrrolidin-1-yl)-2-oxoethyl)amino)-1-oxopropan-2-yl)(methyl)carbamate (1.32 g, 2.09 mmol, Intermediate QD) in $CH_3CN$ (100 mL) was added 2,2-dimethyl-4-oxo-3,8,11,14,17-pentaoxa-5-azanonadecan-19-yl 4-methylbenzenesulfonate (1.23 g, 2.51 mmol, Intermediate ON) and $K_2CO_3$ (346.4 mg, 2.51 mmol) at rt. Then the reaction mixture was stirred at 80° C. for 12 h. The reaction mixture was then concentrated under reduced pressure. The residue was purified via column chromatography on silica gel (EtOAc/petroleum ether) to give the title compound (1.68 g, 85% yield) as a pale yellow oil. LC/MS (ESI, m/z): $[M+1]^+=953.7$.

Step 2—benzyl ((S)-1-(((S)-2-((S)-2-(4-(3-((14-amino-3,6,9,12-tetraoxatetradecyl)oxy)benzoyl)thiazol-2-yl)pyrrolidin-1-yl)-1-cyclohexyl-2-oxoethyl)amino)-1-oxopropan-2-yl)(methyl)carbamate 2,2,2-trifluoroacetate To a solution of benzyl ((S)-1-(((S)-1-cyclohexyl-2-((S)-2-(4-(3-((2,2-dimethyl-4-oxo-3,8,11,14,17-pentaoxa-5-azanonadecan-19-yl)oxy)benzoyl)thiazol-2-yl)pyrrolidin-1-yl)-2-oxoethyl)amino)-1-oxopropan-2-yl)(methyl)carbamate (1.4 g, 1.47 mmol) in DCM (30 mL) was added TFA (30 mL) and the reaction mixture was stirred at rt for 3 h. Then the reaction mixture was concentrated under reduced pressure and the residue was purified via reverse phase column chromatography ($ACN/H_2O$) to give the title compound (1.2 g, 84% yield) as a colorless oil. $^1H$ NMR (400 MHz, CD3OD) δ: 8.33 (s, 1H), 7.90-7.68 (m, 3H), 7.50-7.40 (m, 1H), 7.40-7.19 (m, 5H), 5.67-5.30 (m, 1H), 5.13 (s, 2H), 4.73-4.67 (m, 1H), 4.50-4.40 (m, 1H), 4.29-4.12 (m, 2H), 4.05-3.79 (m, 4H), 3.78-3.52 (m, 14H), 3.10-3.07 (m, 2H), 2.94 (s, 3H), 2.57-1.95 (m, 4H), 1.85-1.46 (m, 6H), 1.40-1.29 (m, 3H), 1.27-0.86 (m, 5H). LC/MS (ESI, m/z): $[M+1]^+=852.7$.

[3-Methyl-5-[3-[3-(methylamino)propoxy]propyl]-2-oxo-benzimidazol-1-yl]piperidine-2,6-dione (Intermediate QI)

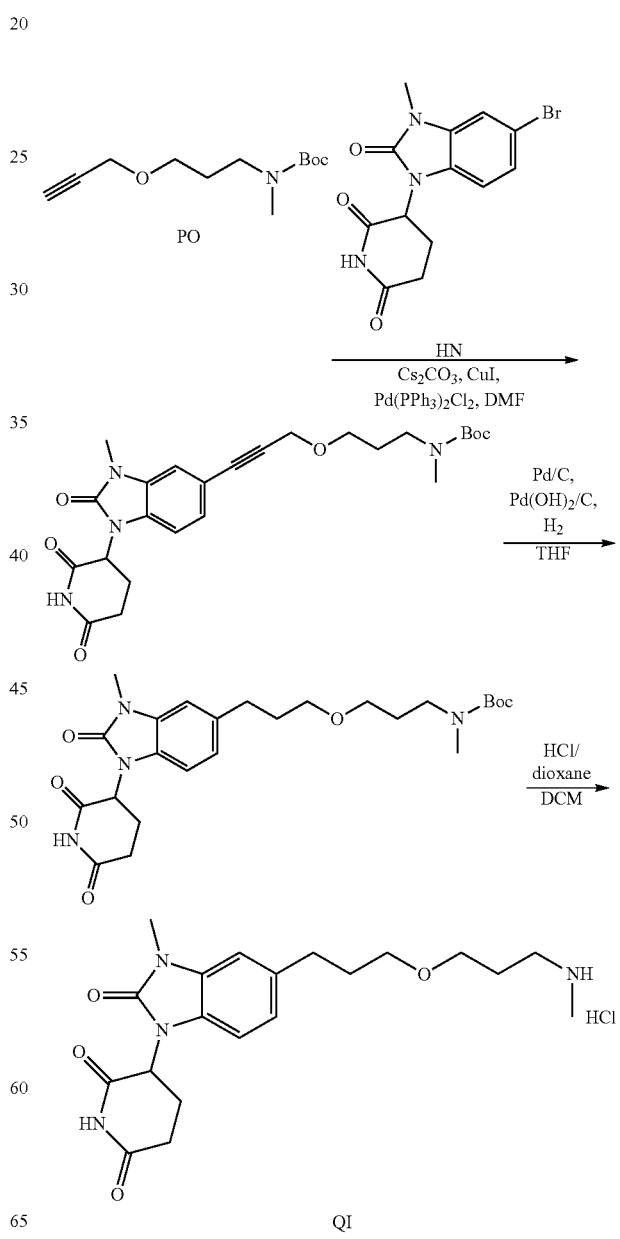

QI

Step 1—Tert-butyl N-[3-[3-[1-(2,6-dioxo-3-piperidyl)-3-methyl-2-oxo-benzimidazol-5-yl]prop-2-ynoxy]propyl]-N-methyl-carbamate To a solution of tert-butyl N-methyl-N-(3-prop-2-ynoxypropyl)carbamate (604 mg, 2.66 mmol, Intermediate PO) and 3-(5-bromo-3-methyl-2-oxo-benzimidazol-1-yl)piperidine-2,6-dione (450 mg, 1.33 mmol, Intermediate HN) in DMF (10 mL) was added Pd(PPh$_3$)$_2$Cl$_2$ (186 mg, 266 umol), CuI (50.6 mg, 266 umol) and Cs$_2$CO$_3$ (2.17 g, 6.65 mmol). The reaction mixture was stirred at 80° C. for 2 hr under N2. On completion, the mixture was filtered, and the filtrate was concentrated in vacuo to give a residue. The residue was purified by reverse phase (0.1% FA condition) to give the title compound (550 mg, 85% yield) as a yellow solid. $^1$H NMR (400 MHz, DMSO-d$_6$) δ 11.13 (s, 1H), 7.65-7.52 (m, 3H), 5.39 (dd, J=5.6, 12.8 Hz, 1H), 4.45-4.18 (m, 2H), 3.62-3.44 (m, 2H), 3.22 (t, J=7.2 Hz, 2H), 2.92-2.83 (m, 1H), 2.80-2.59 (m, 7H), 2.08-2.00 (m, 1H), 1.77-1.70 (m, 2H), 1.38 (s, 9H); LC-MS (ESI$^+$) m/z 507.1 (M+Na)$^+$.

Step 2—Tert-butyl N-[3-[3-[1-(2,6-dioxo-3-piperidyl)-3-methyl-2-oxo-benzimidazol-5-yl]propoxy]propyl]-N-methyl-carbamate To a solution of tert-butyl N-[3-[3-[1-(2,6-dioxo-3-piperidyl)-3-methyl-2-oxo-benzimidazol-5-yl]prop-2-ynoxy]propyl]-N-methyl-carbamate (530 mg, 1.09 mmol) in THF (10 mL) was added Pd(OH)$_2$/C (200 mg, 10 wt %) and Pd/C (200 mg, 10 wt %). The reaction mixture was stirred at 25° C. under H$_2$ (15 Psi) for 12 hrs. On completion, the residue was filtered and the filtrate was concentrated in vacuo to give a residue. The residue was purified by prep-HPLC (column: Phenomenex Synergi C18 150*25*10 um; mobile phase: [water (0.225% FA)-ACN]; B %: 38%-65%, 9 min) to give the title compound (300 mg, 56% yield) as yellow oil. $^1$H NMR (400 MHz, DMSO-d$_6$) δ 11.08 (s, 1H), 7.05-6.98 (m, 2H), 6.87 (d, J=8.0 Hz, 1H), 5.33 (dd, J=5.6, 12.8 Hz, 1H), 3.36-3.33 (m, 4H), 3.32 (s, 3H), 3.22 (t, J=7.2 Hz, 2H), 2.95-2.85 (m, 1H), 2.77 (s, 3H), 2.73-2.60 (m, 4H), 2.03-1.98 (m, 1H), 1.86-1.78 (m, 2H), 1.73-1.69 (m, 2H), 1.38 (s, 9H); LC-MS (ESI$^+$) m/z 389.2 (M+H-100)$^+$.

Step 3—3-[3-Methyl-5-[3-[3-(methylamino)propoxy]propyl]-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-5-yl] propoxy] propyl]-N-methyl-carbamate (50.0 mg, 102 umol) in DCM (3 mL) was added HCl/dioxane (4 M, 2 mL). The reaction mixture was stirred at 25° C. for 2 hrs. On completion, the mixture was concentrated in vacuo to give the title compound (40.0 mg, 92% yield, HCl) as a white solid. $^1$H NMR (400 MHz, DMSO-d$_6$) δ 11.09 (s, 1H), 7.06-6.97 (m, 2H), 6.90-6.84 (m, 1H), 5.34 (dd, J=5.2, 12.8 Hz, 1H), 3.56 (s, 2H), 3.43 (t, J=6.0 Hz, 2H), 3.32 (s, 3H), 2.96-2.86 (m, 3H), 2.72-2.58 (m, 4H), 2.56-2.52 (m, 3H), 2.02-1.97 (m, 1H), 1.90-1.78 (m, 4H); LC-MS (ESI$^+$) m/z 389.2 (M+H)$^+$.

(S)-7-Hydroxy-2-((S)-2-(2-methoxyacetamido)-3,3-dimethylbutanoyl)-N—((R)-1,2,3,4-tetrahydronaphthalen-1-yl)-1,2,3,4-tetrahydroisoquinoline-3-carboxamide (Intermediate MH)

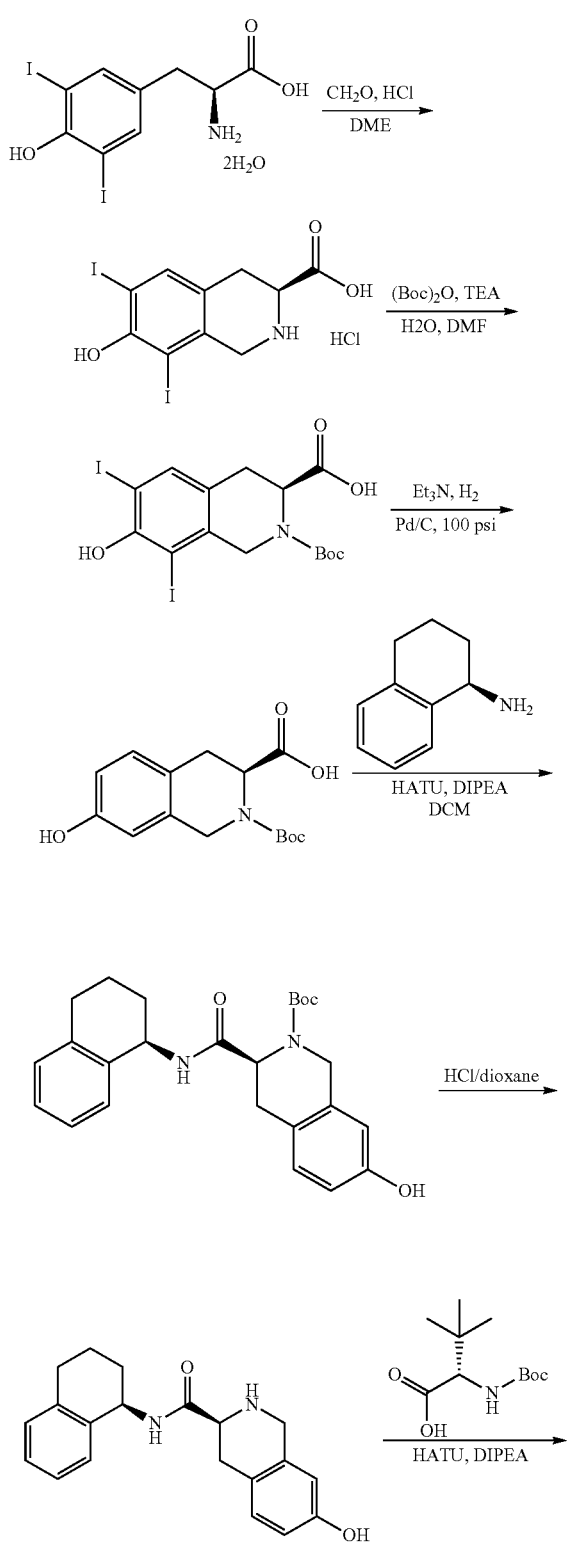

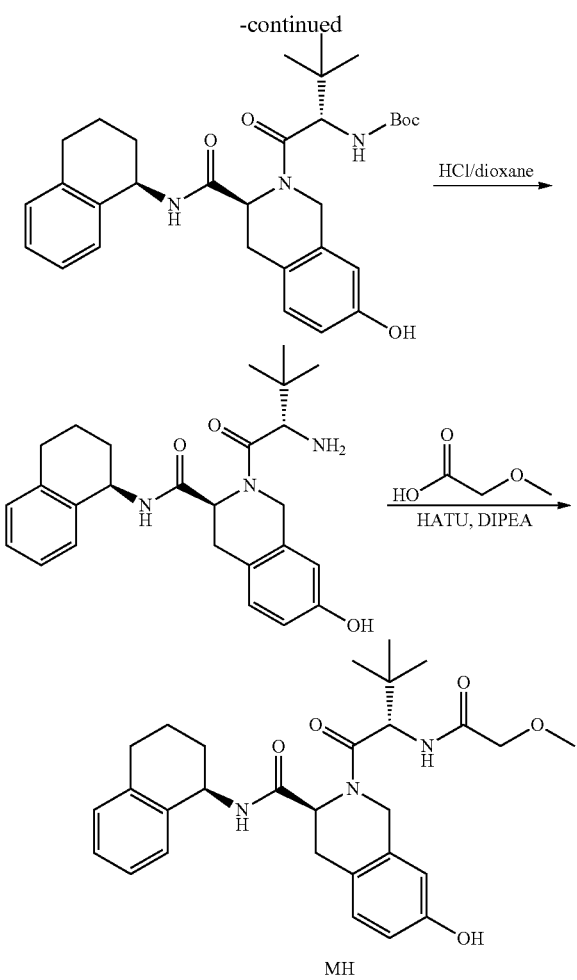

Step 1—(S)-7-hydroxy-6,8-diiodo-1,2,3,4-tetrahydroisoquinoline-3-carboxylic acid hydrochloride To concentrate HCl (780 mL) was added (S)-2-amino-3-(4-hydroxy-3,5-diiodophenyl)propanoic acid (65 g, 150 mmol, CAS #18835-59-1), $CH_2O$ (37% in $H_2O$) and DME (65 mL). The mixture was heated to 72° C. slowly, and then stirred overnight. To the mixture was added another 20 mL of $CH_2O$ (37% in $H_2O$), and the reaction was stirred for another 4 h at 72° C. The mixture was cooled to 0° C. and filtered. The filter cake was washed with DME (50 mL) give (S)-7-hydroxy-6,8-diiodo-1,2,3,4-tetrahydroisoquinoline-3-carboxylic acid hydrochloride HCl salt (32 g, 72% yield) as a yellow solid. $^1$H NMR (400 MHz, DMSO-$d_6$) δ 9.89 (s, 1H), 9.69 (s, 1H), 7.73 (s, 1H), 4.34-4.30 (dd, J=4.8 Hz, J=11.2 Hz, 1H), 4.14-4.00 (dd, J=16.4 Hz, J=40 Hz, 2H), 3.24-3.18 (m, 1H), 3.09-3.02 (m, 1H). LC-MS (ESI$^+$): m/z 482.5 (M+H)$^+$.

Step 2—(S)-2-(tert-butoxycarbonyl)-7-hydroxy-6,8-diiodo-1,2,3,4-tetrahydroisoquinoline-3-carboxylic acid A mixture of (S)-7-hydroxy-6,8-diiodo-1,2,3,4-tetrahydroisoquinoline-3-carboxylic acid hydrochloride (20 g, 41.6 mmol0, (Boc)$_2$O (13.6 g, 62.4 mmol), TEA (16.8 g, 166 mmol), $H_2O$ (40 mL) and DMF (300 mL) was stirred overnight at rt. To the mixture was added $H_2O$ (200 mL), and the solution was washed with EA (200 mL). The aqueous layer adjusted with 1 N HCl to pH<7, then extracted with EA (300 mL). The organic layer was washed with brine (100 mL), dried over $Na_2SO_4$, filtered, concentrated, and purified by column to give (S)-2-(tert-butoxycarbonyl)-7-hydroxy-6,8-diiodo-1,2,3,4-tetrahydroisoquinoline-3-carboxylic acid (15.5 g, 68% yield) as a yellow solid. $^1$H NMR (400 MHz, DMSO-$d_6$) δ 12.77 (s, 1H), 9.46 (s, 1H), 7.64 (s, 1H), 4.83-4.67 (m, 1H), 4.49-4.39 (m, 1H), 4.21-4.17 (d, J=16.8 Hz, 1H), 3.05-3.04 (d, J=4 Hz, 2H), 1.47-1.40 (d, J=24.4 Hz, 9H).

Step 3: (S)-2-(tert-butoxycarbonyl)-7-hydroxy-1,2,3,4-tetrahydroisoquinoline-3-carboxylic acid A mixture of (S)-2-(tert-butoxycarbonyl)-7-hydroxy-6,8-diiodo-1,2,3,4-tetrahydroisoquinoline-3-carboxylic acid (7 g, 12.8 mmol), Pd/C (10 wt %, 1.4 g), TEA (2.9 g, 28.3 mmol) and MeOH (100 mL) was stirred for overnight at rt under $N_2$. The mixture was filtered to remove Pd/C, concentrated to dry, then $H_2O$ (100 mL) was added and the mixture was washed with EA (100 mL). The aqueous layer was adjusted with 1N HCl to pH<7, then extracted with EA (300 mL). The organic layer was dried over $Na_2SO_4$, filtered and concentrated to give (S)-2-(tert-butoxycarbonyl)-7-hydroxy-1,2,3,4-tetrahydroisoquinoline-3-carboxylic acid (3 g, 80% yield) as a yellow solid. $^1$H NMR (400 MHz, DMSO-$d_6$) δ 12.58 (s, 1H), 9.26 (s, 1H), 6.97 (t, J=8.4 Hz, 1H), 6.58-6.52 (m, 2H), 4.83-4.25 (m, 3H), 3.01-2.96 (m, 2H), 1.45-1.39 (d, J=26.4 Hz, 9H). LC-MS (ESI$^+$): m/z 294.4 (M+H)$^+$.

Step 4—(S)-tert-butyl7-hydroxy-3-(((R)-1,2,3,4-tetrahydronaphthalen-1-yl)carbamoyl)-3,4-dihydroisoquinoline-2(1H)-carboxylate To a mixture of (S)-2-(tert-butoxycarbonyl)-7-hydroxy-1,2,3,4-tetrahydroisoquinoline-3-carboxylic acid (32 g, 109 mmol) and (R)-1,2,3,4-tetrahydronaphthalen-1-amine (19.3 g, 131 mmol, CAS #23357-46-2) in DMF (150 mL) was added HATU (54 g, 142 mmol) and DIPEA (42 g, 328 mmol), and the mixture was stirred at rt for 15 min. The solution was then poured into water (1500 mL) and extracted with EtOAc (200 mL×2). The combined organic layer was washed with brine (500 mL×3), dried over $Na_2SO_4$, filtered, concentrated in vacuo and purified via column chromatography (Petroleum ether/EtOAc=4/1) to give the title compound (40.2 g, 86.9% yield) as a white solid. LC-MS (ESI$^+$): m/z 423.1 (M+H)$^+$ Step 5—(S)-7-hydroxy-N—((R)-1,2,3,4-tetrahydronaphthalen-1-yl)-1,2,3,4-tetrahydroisoquino line-3-carboxamide hydrochloride To a mixture of (S)-tert-butyl7-hydroxy-3-(((R)-1,2,3,4-tetrahydronaphthalen-1-yl) carbamoyl)-3,4-dihy droisoquinoline-2(1H)-carboxylate (44 g, 104 mmol) in THF (300 mL) was added 4N HCl in dioxane (300 mL), and the mixture was stirred at rt overnight. The solution was concentrated under reduced pressure to give the crude product, which was recrystallized by EA to give the title compound (33.3 g, 82.0% yield) as a white solid. LC-MS (ESI$^+$): m/z 323.1 (M+H)$^+$.

Step 6—tert-butyl ((S)-1-((S)-7-hydroxy-3-(((R)-1,2,3,4-tetrahydronaphthalen-1-yl) carbamoyl)-3,4-dihydroisoquinolin-2(1H)-yl)-3,3-dimethyl-1-oxobutan-2-yl)carbamate To a mixture of (S)-7-hydroxy-N—((R)-1,2,3,4-tetrahydronaphthalen-1-yl)-1,2,3,4-tetrahydroisoquinoline-3-carboxamidehydrochloride (33.3 g, 92.8 mmol) and (S)-2-((tert-butoxy carbonyl)amino)-3,3-dimethylbutanoic acid (22.5, 97.4 mmol, CAS #62963-35-9) in DMF (400 mL) was added HATU (42.3 g, 111.3 mmol) and DIPEA (48 g, 371 mmol), and the mixture was stirred at rt for 1.5 h. The solution was then poured into water (2500 mL) and the mixture was extracted with EtOAc (200 mL×2). The combined organic layer was washed with brine (500 mL×3), dried over Na$_2$SO$_4$, filtered, concentrated in vacuo and purified via column chromatography (Petroleum ether/EtOAc=2/1) to give the title compound (21.5 g, 43.9% yield) as a white solid. LC-MS (ESI$^+$): m/z 536.2 (M+H)$^+$.

Step 7—(S)-2-((S)-2-amino-3,3-dimethylbutanoyl)-7-hydrox-N—((R)-1,2,3,4-tetrahydronaphthalen-1-yl)-1,2,3,4-tetrahydroisoquinoline-3-carboxamide hydrochloride To a mixture of tert-butyl ((S)-1-((S)-7-hydroxy-3-(((R)-1,2,3,4-tetrahydronaphthalen-1-yl) carbamoyl)-3,4-dihydroisoquinolin-2(1H)-yl)-3,3-dimethyl-1-oxobutan-2-yl) carbamate (21.5 g, 40 mmol) in THF (200 mL) was added 4N HCl in dioxane (200 mL), and the mixture was stirred at rt overnight. The solution was then poured into aq.NaHCO$_3$ (1000 mL) and the mixture was extracted with EtOAc (200 mL×2). The combined organic layer was washed with brine (500 mL×3), dried over Na$_2$SO$_4$, filtered, and concentrated in vacuo to give the title compound as the HCl salt (17 g, 97% yield) as a white solid. LC-MS (ESI$^+$): m/z 436.1 (M+H)$^+$.

Step 8—(S)-7-hydroxy-2-((S)-2-(2-methoxyacetamido)-3,3-dimethylbutanoyl)-N—((R)-1,2,34-tetrahydronaphthalen-1-yl)-1,2,3,4-tetrahydroisoquinoline-3-carboxamide To a mixture of (S)-2-((S)-2-amino-3,3-dimethylbutanoyl)-7-hydroxy-N—((R)-1,2,3,4-tetrahy dronaphthalen-1-yl)-1,2,3,4-tetrahydroisoquinoline-3-carboxamide hydrochloride (14.4 g, 33 mmol) and 2-methoxyacetic acid (2.97 g, 131 mmol) in DMF (120 mL) was added HATU (15 g, 39.6 mmol) and DIPEA (6.4 g, 49.5 mmol), and the mixture was stirred at rt for 1 h. The solution was then poured into water (1500 mL), and the mixture was extracted with EtOAc (200 mL×2). The combined organic layer was washed with brine (500 mL×3), dried over Na$_2$SO$_4$, filtered, concentrated in vacuo and purified via column chromatography (Petroleum ether/EtOAc=1/1) to give the title compound (14 g, 83.8% yield) as a white solid. LC-MS (ESI$^+$): m/z 508.2 (M+H)$^+$.

Benzyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (Intermediate PE)

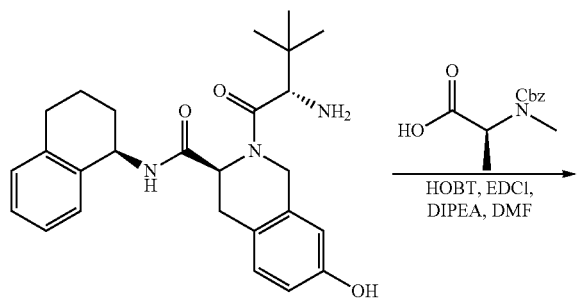

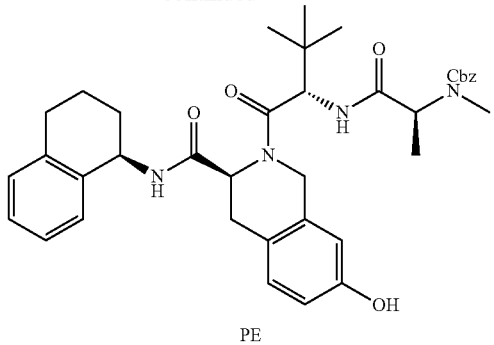

PE

To a solution of (S)-2-((S)-2-amino-3,3-dimethylbutanoyl)-7-hydroxy-N—((R)-1,2,3,4-tetrahydronaphthalen-1-yl)-1,2,3,4-tetrahydroisoquinoline-3-carboxamide (13.45 g, 30.92 mmol, synthesized via Steps 1-7 of Intermediate MH), (S)-2-(((benzyloxy)carbonyl)(methyl)amino)propanoic acid (7.70 g, 32.47 mmol, CAS #21691-41-8) in DMF (150 mL) was added HOBT (4.59 g, 34.01 mmoL), EDCI (6.53 g, 34.01 mmoL), and DIPEA (9.97 g, 77.30 mmoL) at rt. The reaction mixture was stirred at r.t. for 4 h. The mixture was then concentrated under reduce pressure. Then the mixture was poured into H$_2$O (200 mL), extracted with EA (3×100 mL), and the combined organic layers were dried over anhydrous Na$_2$SO$_4$. The solid was filtered and the filtrate was concentrated under reduced pressure. The crude product was purified by silica gel chromatography eluted with DCM/MEOH=10:1 to give the title compound (13.7 g, 63% yield) as a white solid. LC/MS (ESI, m/z): [M+1]+=655.4.

2,2-Dimethyl-4-oxo-3,8,11-trioxa-5-azatridecan-13-yl 4-methylbenzenesulfonate (Intermediate UV)

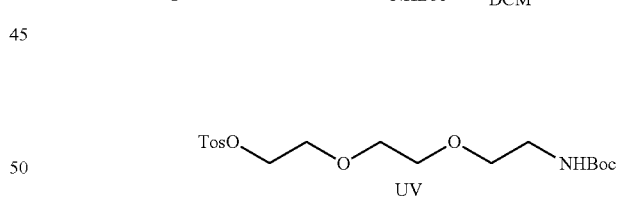

To a solution of tert-butyl (2-(2-(2-hydroxyethoxy)ethoxy)ethyl)carbamate (11 g, 44.12 mmol, CAS #139115-92-7) in DCM (100 mL) was added Et$_3$N (8.91 g, 88.24 mmol), then TosCl (16.82 g, 88.24 mmol) was added portions at room temperature. The reaction mixture was stirred at room temperature overnight. The reaction mixture was concentrated under reduced pressure, the resulting residue was purified by column chromatography on silica gel to give the product 2,2-dimethyl-4-oxo-3,8,11-trioxa-5-azatridecan-13-yl 4-methylbenzenesulfonate as an oil (17 g, yield 96%).
$^1$H NMR (400 MHz, CDCl$_3$) δ 7.81-7.79 (m, 2H), 7.34 (d, J=8.0 Hz, 2H), 4.90 (br s, 1H), 4.19-4.16 (m, 2H), 3.72-3.68 (m, 2H), 3.61-3.57 (m, 2H), 3.56-3.53 (m, 2H), 3.50 (t, J=5.2 Hz, 2H), 3.29 (t, J=5.1 Hz, 2H), 2.45 (s, 3H), 1.42 (s, 9H).

N-[6-(1-hydroxy-1-methyl-ethyl)-2H-indazol-5-yl]-6-(trifluoromethyl)pyridine-2-carboxamide (Intermediate TJ)

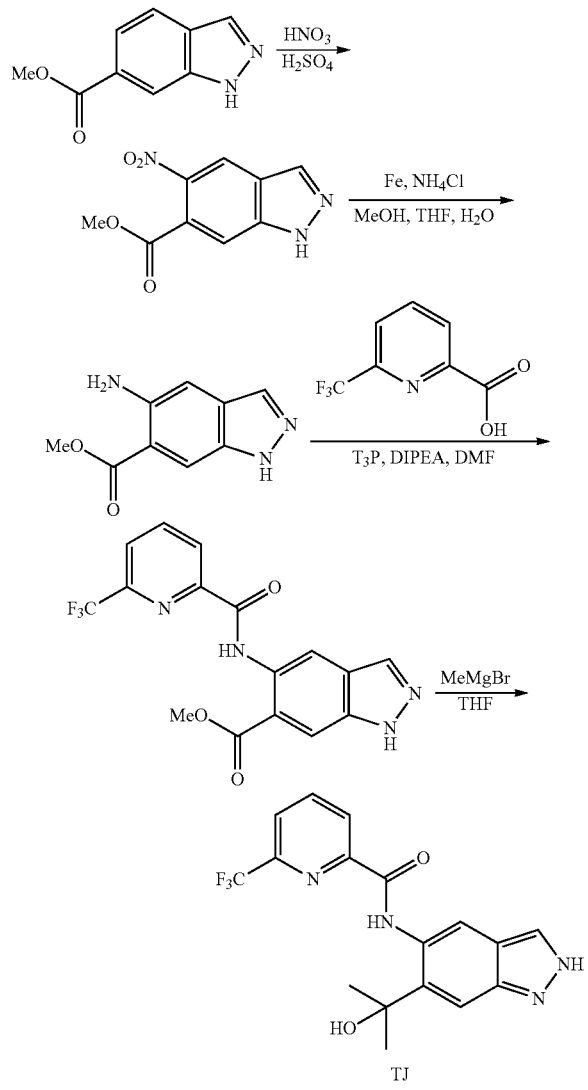

Step 1—Methyl 5-nitro-1H-indazole-6-carboxylate

To a solution of methyl 1H-indazole-6-carboxylate (10.0 g, 56.7 mmol) in $H_2SO_4$ (100 mL) was added a solution of $HNO_3$ (12.1 g, 125 mmol, 65% purity) in $H_2SO_4$ (20 mL) at −10-0° C. during 30 minutes. The mixture was stirred at −10-0° C. for 1 hour. On completion, the mixture was poured into ice/water (1.0 L) slowly. The mixture was filtered and the filter cake was washed with water (2×200 mL). Then the cake was collected and dried in vacuo to give the title compound (11.9 g, 94% yield) as yellow solid. $^1$H NMR (400 MHz, DMSO-$d_6$) δ 8.69 (s, 1H), 8.44 (s, 1H), 7.97 (s, 1H), 3.86 (s, 3H).

Step 2—Methyl 5-amino-1H-indazole-6-carboxylate

To a solution of methyl 5-nitro-1H-indazole-6-carboxylate (10.9 g, 49.2 mmol) in MeOH (100 mL) and THF (60 mL) was added a solution of $NH_4Cl$ (26.3 g, 492 mmol) in $H_2O$ (100 mL) at 25° C. Then Fe (13.7 g, 245 mmol) was added to the mixture in portions at 70° C., and the mixture was stirred at 70° C. for 1 hour. On completion, the mixture was filtered and the filter cake was washed with EA (200 mL). The filtrate was concentrated in vacuo. The residue was washed with water (100 mL), and extracted with EA (3×100 mL). The combined organic layer was washed with brine (100 mL), dried over $Na_2SO_4$, filtered and concentrated in vacuo to the title compound (7.30 g, 77% yield) as yellow solid. $^1$H NMR (400 MHz, DMSO-$d_6$) δ 12.82 (s, 1H), 7.99 (s, 1H), 7.85 (s, 1H), 6.99 (s, 1H), 6.00 (s, 2H), 3.85 (s, 3H).

Step 3—Methyl 5-[[6-(trifluoromethyl)pyridine-2-carbonyl]amino]-1H-indazole-6-carboxylate To a solution of methyl 5-amino-1H-indazole-6-carboxylate (7.20 g, 37.6 mmol), 6-(trifluoromethyl)pyridine-2-carboxylic acid (6.48 g, 33.9 mmol, CAS #131747-42-7) and DIPEA (7.35 g, 56.8 mmol) in THF (70 mL) was added T3P (47.9 g, 44.8 mL, 50 wt %) slowly at 0° C. Then the mixture was stirred at 0-5° C. for 2 hours. On completion, the reaction was quenched with cold water (0.1 mL). The mixture was diluted with water (280 mL), and stirred at 25° C. for 0.5 hour. The mixture was filtered and the filter cake was washed with water (30 mL). The filter cake was collected and dried in vacuo to give the title compound (12.3 g, 99% yield) as yellow solid. $^1$H NMR (400 MHz, DMSO-$d_6$) δ 12.58 (s, 1H), 9.15 (s, 1H), 8.47 (d, J=7.6 Hz, 1H), 8.39 (t, J=7.6 Hz, 1H), 8.30 (s, 1H), 8.25 (s, 1H), 8.20 (d, J=8.0 Hz, 1H), 3.97 (s, 3H).

Step 4—N-[6-(1-hydroxy-1-methyl-ethyl)-2H-indazol-5-yl]-6-(trifluoromethyl)pyridine-2-carboxamide To a solution of methyl 5-[[6-(trifluoromethyl)pyridine-2-carbonyl]amino]-1H-indazole-6-carboxylate (4.00 g, 10.9 mmol) in THF (40 mL) was added MeMgBr-$Et_2O$ solution (3.0 M, 29.3 mL) slowly at 0° C. The mixture was stirred at 0-25° C. for 16 hours. On completion, the reaction was quenched with sat.$NH_4Cl$ (40 mL) slowly at 0-10° C. The mixture was extracted with EA (3×40 mL). The combined organic layer was concentrated in vacuo. The residue was purified by reverse phase chromatography (FA condition) to give the title compound (1.50 g, 37% yield) as light yellow solid. $^1$H NMR (400 MHz, $CDCl_3$) δ 12.23 (s, 1H), 8.96 (s, 1H), 8.52 (d, J=7.6 Hz, 1H), 8.12 (t, J=7.6 Hz, 1H), 8.07 (s, 1H), 7.85 (d, J=7.6 Hz, 1H), 7.50 (s, 1H), 1.80 (s, 6H).

3-(4-Bromo-3-methyl-2-oxo-2,3-dihydro-1H-benzo[d]imidazol-1-yl)piperidine-2,6-dione (Intermediate HP)

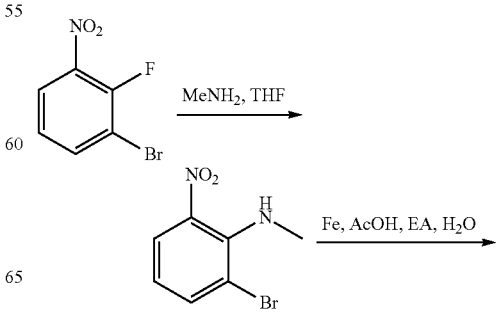

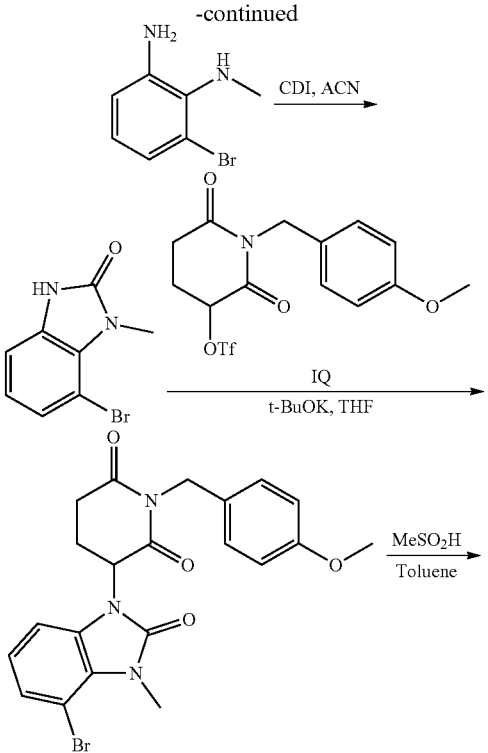

Step 1—2-Bromo-N-methyl-6-nitro-aniline

To a solution of 1-bromo-2-fluoro-3-nitro-benzene (40.0 g, 181 mmol, CAS #58534-94-4) in THF (40 mL) was added MeNH$_2$ (2 M, 400 mL). The reaction mixture was stirred at 60° C. for 12 hours. On completion, the reaction mixture was poured into sat.NaHCO$_3$ (30 mL) and extracted with EA (3×200 mL). The combined organic layers were washed with brine (2×200 mL), dried with anhydrous Na$_2$SO$_4$, filtered and concentrated in vacuo to give the title compound (40.0 g, 95% yield) as red oil. LC-MS (ESI$^+$) m/z 230.9 (M+H)$^+$.

Step 2—3-Bromo-N$_2$-methyl-benzene-1,2-diamine

To a mixture of 2-bromo-N-methyl-6-nitro-aniline (23.0 g, 99.5 mmol) in EA (300 mL) and H$_2$O (10 mL) was added AcOH (100 mL). The mixture was warmed to 50° C. Then Fe (22.2 g, 398 mmol) was added to the reaction mixture and the mixture was heated to 80° C. about 4 hours. On completion, the reaction mixture was filtered and concentrated in vacuo. The residue was diluted with water (100 mL) and extracted with EA (3×200 mL). The combined organic layers was dried over Na$_2$SO$_4$, filtered and concentrated in vacuo to give the title compound (20.0 g, 99% yield) as red oil. $^1$H NMR (400 MHz, DMSO-d$_6$) δ 6.73-6.70 (m, 1H), 6.68-6.60 (m, 2H), 5.02 (s, 2H), 3.67 (s, 1H), 2.58 (s, 3H).

Step 3—4-Bromo-3-methyl-1H-benzimidazol-2-one

To a mixture of 3-bromo-N$_2$-methyl-benzene-1,2-diamine (20.0 g, 99.4 mmol) in ACN (300 mL) was added CDI (32.2 g, 198 mmol). The reaction mixture was stirred at 85° C. for 12 hours under N$_2$ atmosphere. On completion, the reaction mixture was concentrated in vacuo. The reaction mixture was diluted with water (200 mL), where a solid precipitate was formed, which was filtered off. The solid was washed with water (1 L) and dried in vacuo to give the title compound (20.0 g, 88% yield) as white solid. $^1$H NMR (400 MHz, DMSO-d$_6$) δ 11.17 (s, 1H), 7.14 (dd, J=1.2, 8.0 Hz, 1H), 7.00-6.95 (m, 1H), 6.93-6.87 (m, 1H), 3.55 (s, 3H).

Step 4—3-(4-Bromo-3-methyl-2-oxo-benzimidazol-1-yl)-1-[(4-methoxyphenyl)methyl]piperidine-2,6-dione To a solution of 4-bromo-3-methyl-1H-benzimidazol-2-one (12.0 g, 52.8 mmol) in THF (300 mL) was added t-BuOK (7.12 g, 63.4 mmol). The reaction mixture was stirred at 0° C. for 0.5 hr. Subsequently, [1-[(4-methoxyphenyl)methyl]-2,6-dioxo-3-piperidyl]trifluoromethanesulfonate (20.1 g, 52.8 mmol, Intermediate IQ) in a solution of THF (100 mL) was added dropwise. The resulting reaction mixture was stirred at 20° C. for 0.5 hr under N$_2$. On completion, the reaction mixture was quenched with saturated NH$_4$Cl (100 mL), and extracted with ethyl acetate (200 mL). The combined organic layers were washed with brine (2×100 mL), dried over anhydrous sodium sulfate, filtered, the filtrate was concentrated in vacuo. The crude product was purified by reversed-phase HPLC (0.1% FA condition) to give the title compound (13.3 g, 55% yield) as a yellow solid. $^1$H NMR (400 MHz, CDCl$_3$) δ 7.38 (d, J=8.8 Hz, 2H), 7.22 (d, J=8.0 Hz, 1H), 6.84 (d, J=8.8 Hz, 2H), 6.80 (t, J=8.0 Hz, 1H), 6.48-6.40 (d, J=8.0 Hz, 1H), 5.22 (dd, J=5.2, 12.8 Hz, 1H), 5.04-4.93 (m, 2H), 3.81 (s, 3H), 3.80 (s, 3H), 3.12-2.98 (m, 1H), 2.93-2.77 (m, 1H), 2.62 (dq, J=4.4, 13.2 Hz, 1H), 2.20-2.17 (m, 1H).

Step 5—3-(4-bromo-3-methyl-2-oxo-2,3-dihydro-1H-benzo[d]imidazol-1-yl)piperidine-2,6-dione A mixture of 3-(4-bromo-3-methyl-2-oxo-benzimidazol-1-yl)-1-[(4-methoxyphenyl)methyl]piperidine-2,6-dione (13.3 g, 29.0 mmol) in a mixed solvent of Tol. (80 mL) and methane sulfonic acid (40 mL) was degassed and purged with N$_2$ for 3 times, and then the mixture was stirred at 120° C. for 2 hrs under N$_2$ atmosphere. On completion, the reaction mixture was concentrated in vacuo to remove toluene. The residue was added 200 mL of ice water, and then white solid precipitate formed. The mixture was filtered and the filtered cake was collected and dried over in vacuo to give the title compound (7.30 g, 74% yield) as white solid. $^1$H NMR (400 MHz, DMSO-d$_6$) δ 11.13 (s, 1H), 7.25 (d, J=8.0 Hz, 1H), 7.17 (d, J=8.0 Hz, 1H), 7.05-6.93 (m, 1H),

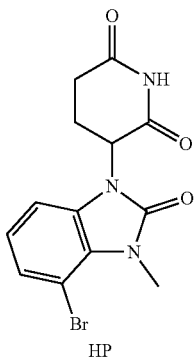
HP 5.41 (dd, J=5.2, 12.8 Hz, 1H), 3.64 (s, 3H), 2.96-2.83 (m, 1H), 2.78-2.59 (m, 2H), 2.08-2.00 (m, 1H).

[1-[(4-Methoxyphenyl) methyl]-2,6-dioxo-3-piperidyl] trifluoromethanesulfonate (Intermediate IQ)

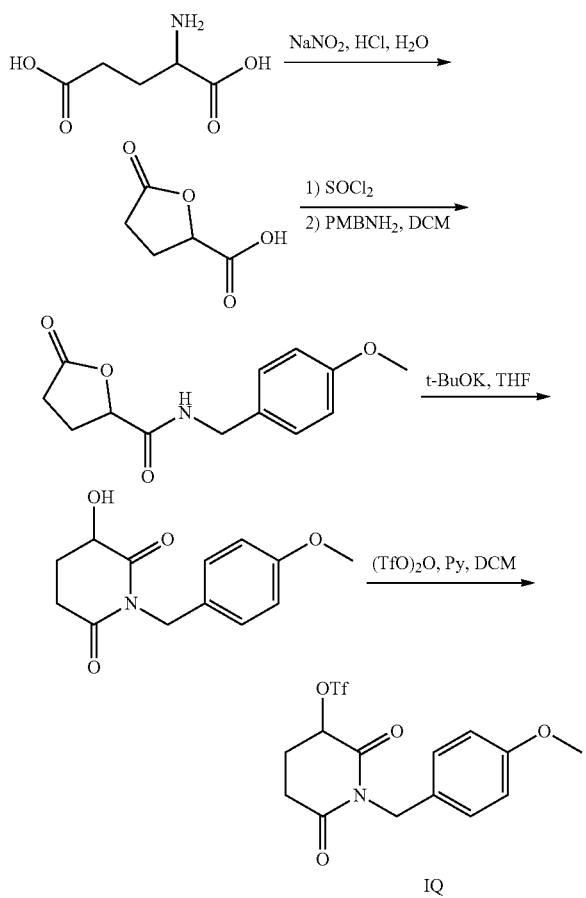

IQ

Step 1—5-Oxotetrahydrofuran-2-carboxylic acid

To a solution of 2-aminopentanedioic acid (210 g, 1.43 mol, CAS #617-65-2) in H₂O (800 mL) and HCl (12 M, 210 mL) was added a solution of NaNO₂ (147 g, 2.13 mol) in H₂O (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over Na₂SO₄, filtered and concentrated in vacuo to give the title compound (200 g, crude) as yellow oil. $^1$H NMR (400 MHz, CDCl₃) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added SOCl₂ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under N₂. After that a solution of Et₃N (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1$H NMR (400 MHz, CDCl₃) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS (ESI⁺) m/z 272.0 (M+Na)⁺.

Step 3—3-Hydroxy-1-[(4-methoxyphenyl)methyl] piperidine-2,6-dione

A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated NH₄Cl solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1$H NMR (400 MHz, CDCl₃) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl]trifluoromethanesulfonate To a solution of 3-hydroxy-1-[(4-methoxyphenyl) methyl] piperidine-2,6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under N₂. On completion, the mixture was concentrated in vacuo. The residue was purified by column chromatography on silica gel (PE:EA=20:1/8:1) to give the title compound (45.0 g, 68% yield) as light yellow gum. $^1$H NMR (400 MHz, CDCl₃) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

tert-Butyl (2-(2-(prop-2-yn-1-yloxy)ethoxy)ethyl) carbamate (Intermediate IT)

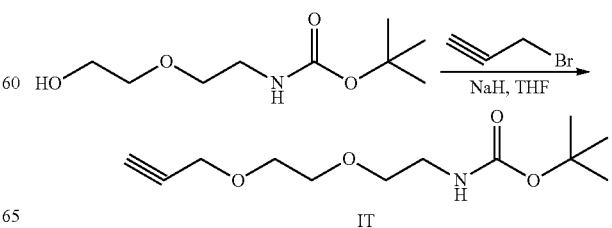

IT

To a stirred solution of tert-butyl (2-(2-hydroxyethoxy)ethyl)carbamate (2.0 g, 9.74 mmol, CAS #: 139115-91-6) in THF (50 ml) was added NaH (0.47 g, 11.70 mmol) at 0-5° C. 3-bromoprop-1-yne (2.1 ml, 14.62 mmol) was added dropwise at 0-5° C. The reaction mixture was stirred at rt for 5 h. The resulting reaction mixture was poured into ice cold water (200 ml) and extracted with ethyl acetate (3×200 ml). The combined organic layer was dried over anhydrous $Na_2SO_4$, filtered and concentrated under vacuum to afford tert-butyl (2-(2-(prop-2-yn-1-yloxy)ethoxy)ethyl)carbamate (2.1 g, 8.97 mmol). LCMS m/z: (ES+) 144.1 (M−99)$^+$.

3-[4-[3-[2-(2-Aminoethoxy)ethoxy]propyl]-3-methyl-2-oxo-benzimidazol-1-yl]piperidine-2,6-dione (Intermediate HQ)

Step 1—Tert-butyl N-[2-[2-[3-[1-(2,6-dioxo-3-piperidyl)-3-methyl-2-oxo-benzimidazol-4-yl]prop-2-ynoxy]ethoxy]ethyl]carbamate To a mixture of 3-(4-bromo-3-methyl-2-oxo-benzimidazol-1-yl)piperidine-2,6-dione (100 mg, 295 umol, Intermediate HP) and tert-butyl N-[2-(2-prop-2-ynoxyethoxy)ethyl]carbamate (93.5 mg, 384 umol, synthesized via Step 1 of Intermediate CQ) in DMF (5 mL) was added CuI (5.63 mg, 29.5 umol), $Pd(PPh_3)_2Cl_2$ (20.7 mg, 29.5 umol) and TEA (538 mg, 5.32 mmol, 740 uL). The reaction mixture was heated at 80° C. for 30 minutes under microwave. On completion, the reaction mixture was concentrated in vacuo. The residue was purified by prep-HPLC (column: Kromasil 150*25 mm*10 um; mobile phase: [water (0.225% FA)-ACN]) to give the title compound (55.0 mg, 34% yield, FA)

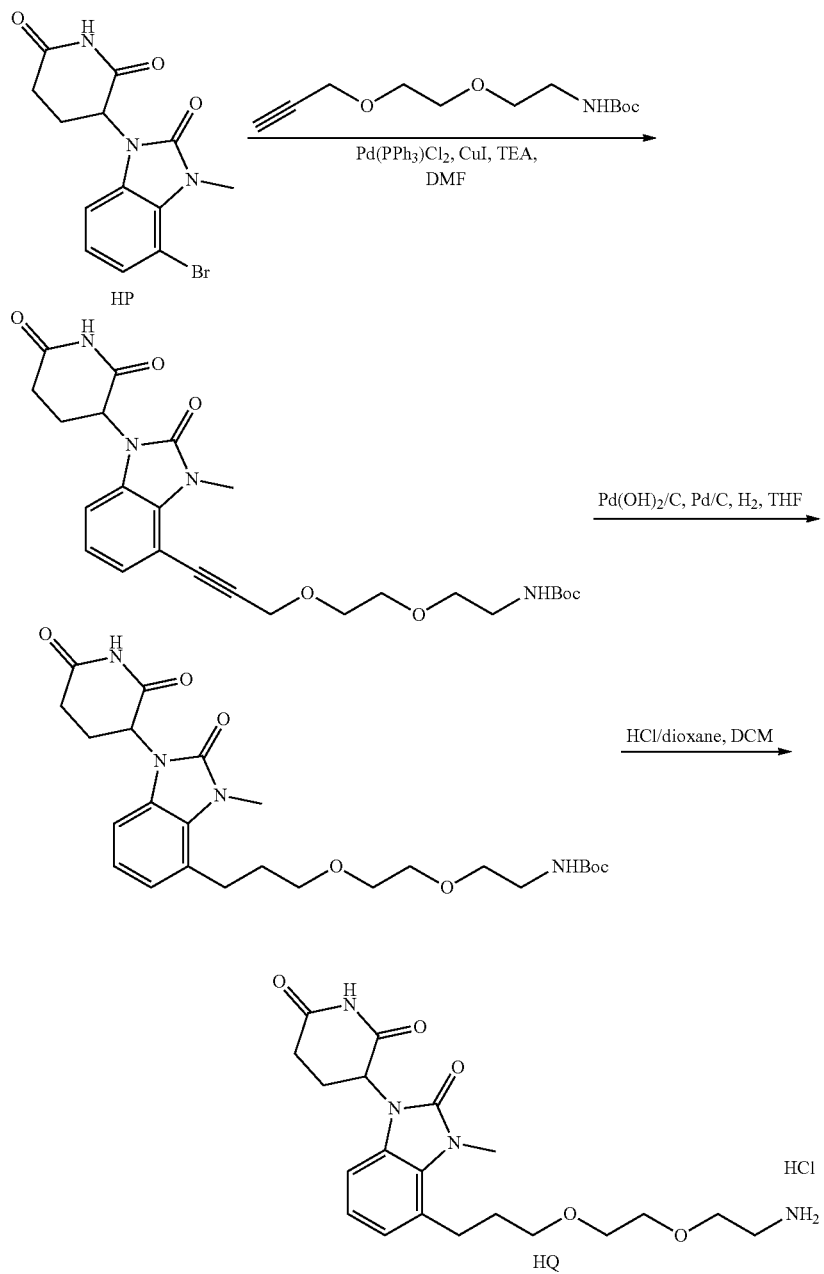

as brown solid. $^1$H NMR (400 MHz, DMSO-$d_6$) δ 11.12 (s, 1H), 7.18 (d, J=7.6 Hz, 1H), 7.13 (d, J=7.6 Hz, 1H), 7.08-7.00 (m, 1H), 6.76 (s, 1H), 5.41 (dd, J=4.4, 12.4 Hz, 1H), 4.47 (s, 2H), 3.69-3.65 (m, 2H), 3.65 (s, 3H), 3.57 (d, J=4.4 Hz, 2H), 3.40 (t, J=6.0 Hz, 2H), 3.08 (d, J=5.6 Hz, 2H), 2.96-2.84 (m, 1H), 2.77-2.63 (m, 2H), 2.09-1.97 (m, 1H), 1.37 (s, 9H). LC-MS (ESI$^+$) m/z 501.4 (M+H)$^+$.

Step 2—Tert-butyl N-[2-[2-[3-[1-(2,6-dioxo-3-piperidyl)-3-methyl-2-oxo-benzimidazol-4-yl]propoxy] ethoxy] ethyl]carbamate To a mixture of tert-butyl N-[2-[2-[3-[1-(2,6-dioxo-3-piperidyl)-3-methyl-2-oxo-benzimidazol-4-yl] prop-2-ynoxy]ethoxy]ethyl]carbamate (50.0 mg, 99.8 umol) in THF (4 mL) was added Pd/C (15 mg, 10 wt %) and Pd(OH)$_2$/C (15 mg, 10 wt %). The reaction mixture was stirred at 25° C. for 1 hour under H$_2$ (15 Psi) atmosphere. On completion, the reaction mixture was filtered and concentrated in vacuo to give the title compound (50.0 mg, 99% yield) as brown oil. LC-MS (ESI$^+$) m/z 505.4 (M+H)$^+$.

Step 3—3-[4-[3-[2-(2-Aminoethoxy)ethoxy]propyl]-3-methyl-2-oxo-benzimidazol-1-yl]piperidine-2,6-dione To a mixture of tert-butyl N-[2-[2-[3-[1-(2,6-dioxo-3-piperidyl)-3-methyl-2-oxo-benzimidazol-4-yl] propoxy] ethoxy]ethyl]carbamate (50.0 mg, 99.0 umol) in DCM (5 mL) was added HCl/dioxane (4 M, 5 mL). The reaction mixture was stirred at 25° C. for 1 hour. On completion, the reaction mixture was concentrated in vacuo to give the title compound (43.0 mg, 98% yield, HCl) as colourless oil. LC-MS (ESI$^+$) m/z 405.3 (M+H)$^+$.

(1s,4s)-Ethyl 4-(4-(2-(2-((tert-butoxycarbonyl)(cyclopropylmethyl)amino)pyridin-4-yl) oxazole-4-carboxamido)-3-(difluoromethyl)-1H-pyrazol-1-yl) cyclohexanecarboxylate (Intermediate PS) & (1r, 4r)-ethyl-4-(4-(2-(2-((tert-butoxycarbonyl) (cyclopropylmethyl)amino)pyridin-4-yl)oxazole-4-carboxamido)-3-(difluoromethyl)-1H-pyrazol-1-yl) cyclohexanecarboxylate (Intermediate PT)

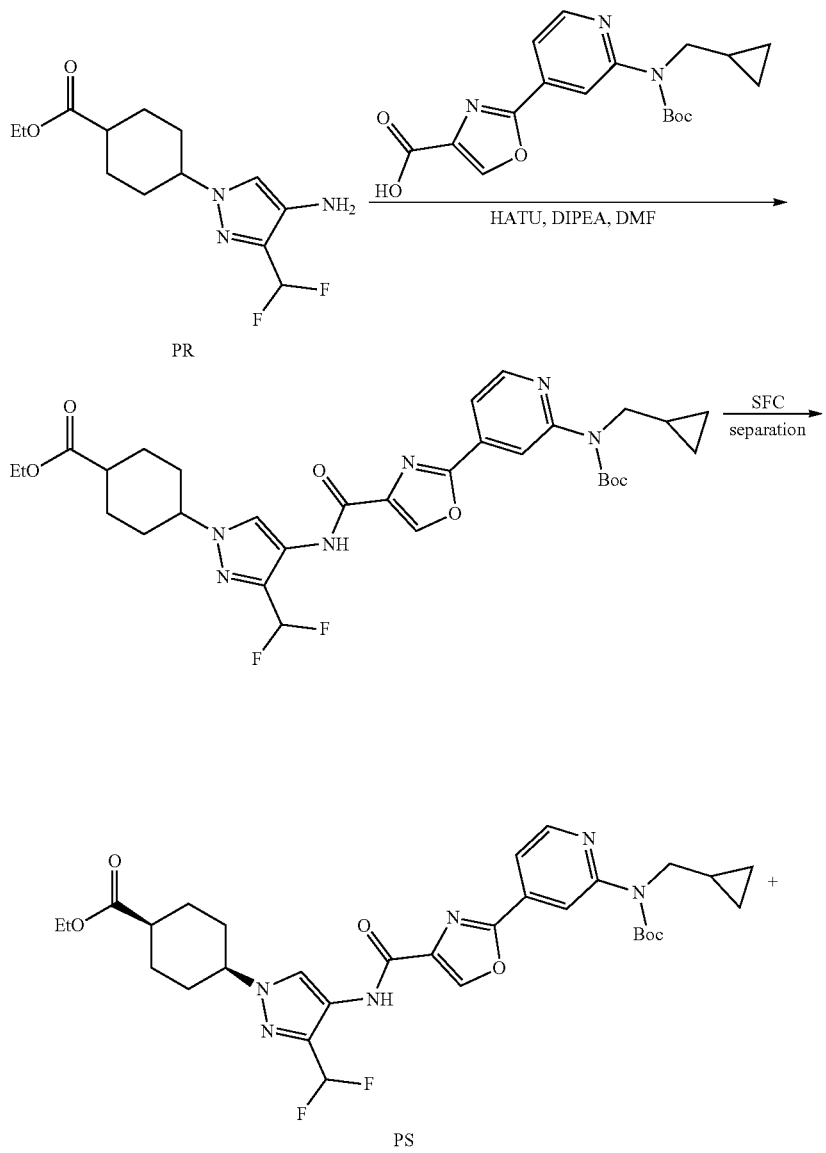

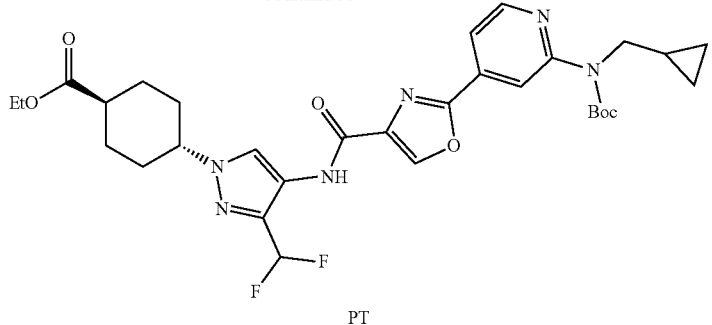

PT

Step 1—Ethyl 4-(4-(2-(2-((tert-butoxycarbonyl)(cyclopropylmethyl)amino)pyridin-4-yl)oxazole-4-carboxamido)-3-(difluoromethyl)-1H-pyrazol-1-yl)cyclohexanecarboxylate To a solution of ethyl 4-[4-amino-3-(difluoromethyl)pyrazol-1-yl]cyclohexanecarboxylate (144 mg, 501 umol, Intermediate PR) and 2-[2-[tert-butoxycarbonyl(cyclopropylmethyl)amino]-4-pyridyl]oxazole-4-carboxylic acid (180 mg, 501 umol, synthesized via Steps 1-4 of Intermediate DF) in DMF (3 mL) was added DIPEA (129 mg, 1.00 mmol) and HATU (228 mg, 601 umol). The reaction mixture was stirred at 20° C. for 1 hr. On completion, the reaction mixture was diluted with water (10 mL), then extracted with ethyl acetate (3×50 mL). The combined organic layer was washed with brine (10 mL), dried over anhydrous sodium sulfate, and filtered. The filtrate was concentrated in vacuo to give the crude product. The crude product was purified by reversed-phase HPLC (0.1% FA condition) to give the title compound (195 mg, 61% yield) as a white solid. LC-MS (ESI$^+$) m/z 629.3 (M+H)$^+$.

Step 2—(1s,4s)-ethyl 4-(4-(2-(2-((tert-butoxycarbonyl)(cyclopropylmethyl)amino)pyridin-4-yl) oxazole-4-carboxamido)-3-(difluoromethyl)-1H-pyrazol-1-yl)cyclohexanecarboxylate & (1r,4r)-ethyl-4-(4-(2-(2-((tert-butoxycarbonyl)(cyclopropylmethyl)amino)pyridin-4-yl)oxazole-4-carboxamido)-3-(difluoromethyl)-1H-pyrazol-1-yl)cyclohexanecarboxylate Ethyl-4-[4-[[2-[2-[tert-butoxycarbonyl(cyclopropylmethyl)amino]-4-pyridyl]oxazole-4-carbonyl]amino]-3-(difluoromethyl)pyrazol-1-yl]cyclohexanecarboxylate (195 mg, 310 umol) was further separated by SFC (condition: column: DAICEL CHIRALPAK AD (250 mm*30 mm, 10 um); mobile phase: [0.10% NH$_3$.H$_2$O ETOH]; B %: 30%-30%,4 min; 50 min) to give a residue which was further purified by prep-HPLC (column: Phenomenex Gemini 150*25 mm*10 um; mobile phase: [water (0.04% NH$_3$.H$_2$O+10 mM NH$_4$HCO$_3$)-ACN]; B %: 20%-44%) to give the products (1 s,4s)-ethyl 4-(4-(2-(2-((tert-butoxycarbonyl)(cyclopropylmethyl)amino)pyridin-4-yl) oxazole-4-carboxamido)-3-(difluoromethyl)-1H-pyrazol-1-yl)cyclohexanecarboxylate (33 mg, 17% yield) as a white solid: $^1$H NMR (400 MHz, CDCl$_3$) 9.05 (s, 1H), 8.58-8.48 (m, 1H), 8.50 (d, J=5.2 Hz, 1H), 8.37 (s, 1H), 8.31 (s, 2H), 7.62 (dd, J=1.2, 5.2 Hz, 1H), 6.82 (t, J=54.8, 1H), 4.26-4.09 (m, 3H), 3.93 (d, J=7.2 Hz, 2H), 2.64 (q, J=4.4 Hz, 1H), 2.30-2.20 (m, 2H), 2.12-1.97 (m, 4H), 1.77-1.66 (m, 2H), 1.56 (s, 9H), 1.28 (t, J=7.2 Hz, 3H), 1.24-1.15 (m, 1H), 0.49-0.37 (m, 2H), 0.31-0.23 (m, 2H), and & (1r,4r)-ethyl-4-(4-(2-(2-((tert-butoxycarbonyl)(cyclopropylmethyl)amino)pyridin-4-yl)oxazole-4-carboxamido)-3-(difluoromethyl)-1H-pyrazol-1-yl)cyclohexanecarboxylate (80 mg, 41% yield) as a white solid: $^1$H NMR (400 MHz, CDCl$_3$) δ 9.06 (s, 1H), 8.50 (d, J=5.2 Hz, 1H), 8.37 (s, 1H), 8.31 (s, 2H), 7.62 (dd, J=1.2, 5.2 Hz, 1H), 6.82 (t, J=54.8, 1H), 4.22-4.04 (m, 3H), 3.93 (d, J=7.2 Hz, 2H), 2.37 (tt, J=3.6, 12.0 Hz, 1H), 2.30-2.14 (m, 4H), 2.30-2.14 (m, 1H), 1.83 (q, J=3.2, 12.6 Hz, 3H), 1.71-1.59 (m, 2H), 1.27 (t, J=7.2 Hz, 3H), 1.23-1.15 (m, 1H), 1.24-1.15 (m, 1H), 0.48-0.37 (m, 2H), 0.32-0.22 (m, 2H).

(1R,4R)-4-(4-(2-(2-((tert-Butoxycarbonyl)(cyclopropylmethyl)amino)pyridin-4-yl)oxazole-4-carboxamido)-3-(difluoromethyl)-1H-pyrazol-1-yl)cyclohexanecarboxylic acid (Intermediate PU)

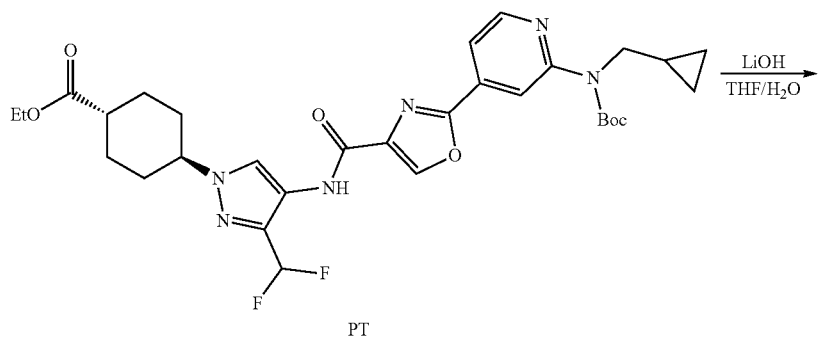

PT

-continued

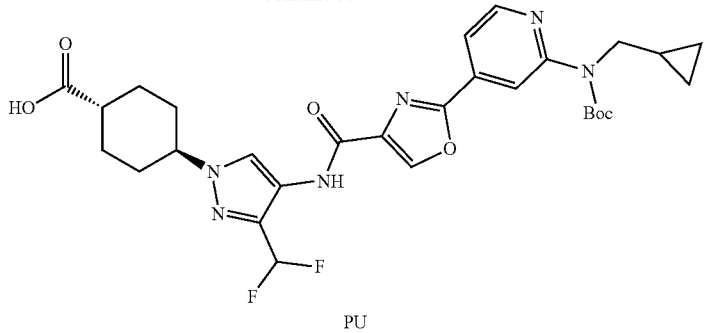

PU

To solution of ethyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl] cyclohexanecarboxylate (80.0 mg, 127 umol, Intermediate PT) in a mixed solvent of H₂O (1 mL) and THF (3 mL) was added LiOH—H₂O (10.7 mg, 255 umol). The reaction mixture was stirred at 25° C. for 12 hrs. On completion, the reaction mixture was acidified with 2N HCl (0.2 mL) to pH=5. Then, the mixture was concentrated in vacuo. To the residue was added ethyl acetate (20 mL), the mixture was then filtered and the filtrate was concentrated in vacuo. The crude product was purified by prep-HPLC (column: Phenomenex Synergi C18 150*25*10 um; mobile phase: [water (0.225% FA)-ACN]; B %: 55%-85%,10 min) to give the title compound (70 mg, 91% yield) as a white solid. ¹H NMR (400 MHz, CDCl₃) δ 9.09 (s, 1H), 8.54 (d, J=5.2 Hz, 1H), 8.40 (s, 1H), 8.34 (s, 2H), 7.65 (d, J=4.0 Hz, 1H), 6.85 (t, J=54.8 Hz, 1H), 4.21-4.10 (m, 1H), 3.96 (d, J=6.8 Hz, 2H), 2.53-2.42 (m, 1H), 2.33-2.24 (m, 4H), 1.91-1.86 (m, 2H), 1.77-1.73 (m, 4H), 1.25-1.19 (m, 1H), 0.49-0.40 (m, 2H), 0.30-0.27 (m, 2H). LC-MS (ESI⁺) m/z 601.3 (M+H)⁺.

3-(7-Bromo-2-oxo-1,3-benzoxazol-3-yl)piperidine-2,6-dione (Intermediate JF)

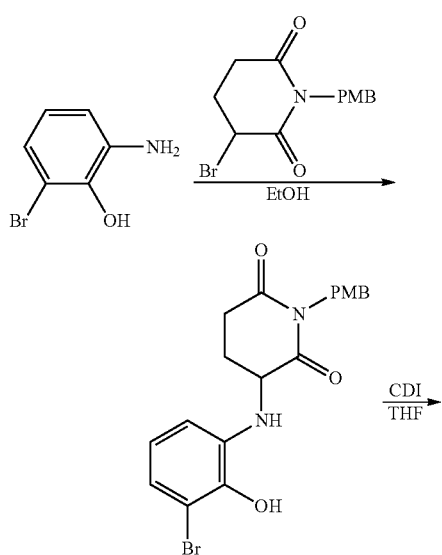

-continued

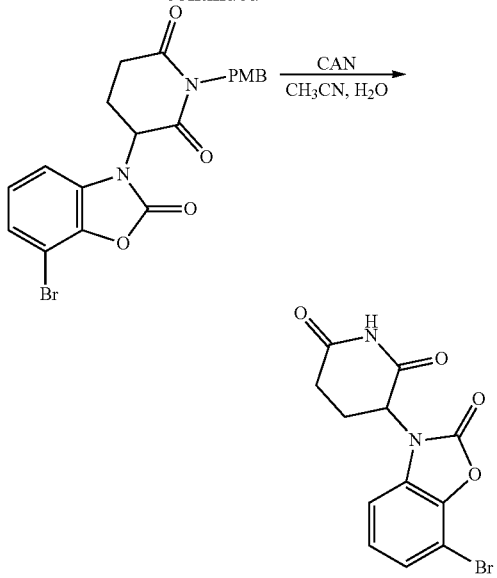

Step 1—3-(3-bromo-2-hydroxyphenylamino)-1-(4-methoxybenzyl)piperidine-2,6-dione

To a solution of 3-bromo-1-(4-methoxybenzyl)piperidine-2,6-dione (145 mg, 0.77 mmol, Intermediate LJ) in EtOH (10 mL) was added 2-amino-6-bromophenol (200 mg, 0.64 mmol) and at r.t. The reaction mixture was heated and stirred under microwave irradiation at 140° C. for 25 mins. The reaction mixture was concentrated under reduced pressure. The residue was purified via reverse phase column chromatography (ACN/H₂O with 0.1% TFA) to give title compound (80 mg, 30% yield) as a colorless oil. ¹H NMR (400 MHz, DMSO-d₆) δ 8.94 (s, 1H), 7.18 (d, J=8.6 Hz, 2H), 6.85 (d, J=8.7 Hz, 2H), 6.75 (dd, J=6.9, 2.6 Hz, 1H), 6.67-6.59 (m, 2H), 5.48 (d, J=7.1 Hz, 1H), 4.76 (q, J=14.3 Hz, 2H), 4.58-4.40 (m, 1H), 3.71 (s, 3H), 3.05-2.89 (m, 1H), 2.83-2.61 (m, 1H), 2.25-2.10 (m, 1H), 2.02-1.97 (m, 1H). LC-MS (ESI⁺): m/z 421.1 (M+H)⁺.

Step 2—3-(7-bromo-2-oxobenzo[d]oxazol-3(2H)-yl)-1-(4-methoxybenzyl)piperidine-2,6-dione To a solution of 3-(3-bromo-2-hydroxyphenylamino)-1-(4-methoxybenzyl)piperidine-2,6-dione (80 mg, 0.19 mmol)

in THF (5 mL) was added a solution of CDI (46 mg, 0.284 mmol) in THF (5 mL) at r.t. under N₂. The reaction mixture was stirred at 35° C. for 12 h. The reaction mixture was then concentrated under reduced pressure and the residue was purified via column chromatography (Petroleum ether/ EtOAc=2/1) to give title compound (70 mg, 74% yield) as a white solid. $^1$H NMR (400 MHz, DMSO-d$_6$) δ 7.39 (dd, J=8.0, 1.1 Hz, 1H), 7.23-7.16 (m, 4H), 6.86 (d, J=8.7 Hz, 2H), 5.56 (dd, J=13.3, 5.3 Hz, 1H), 4.89-4.70 (m, 2H), 3.72 (s, 3H), 3.04-3.01 (m, 1H), 2.87-2.83 (m, 1H), 2.71-2.65 (m, 1H), 2.27-2.18 (m, 1H). LC-MS (ESI⁺): m/z 445.1 (M+H)⁺.

Step 3—3-(7-bromo-2-oxobenzo[d]oxazol-3(2H)-yl) piperidine-2,6-dione

To a solution of 3-(7-bromo-2-oxobenzo[d]oxazol-3(2H)-yl)-1-(4-methoxybenzyl)piperidine-2,6-dione (80 mg, 0.180 mmol) in CH₃CN (2 mL) was added a solution of CAN (690 mg, 1.26 mmol) in 0.5 mL of water dropwise at r.t. The reaction mixture was stirred at r.t. for 2 hours. The reaction mixture was then extracted with EtOAc (15 mL×2), the organic layer washed with brine, dried over anhydrous Na₂SO₄ and concentrated under reduced pressure. The residue was purified via Pre-TLC (Petroleum ether/EtOAc=1/1) to give the title compound (9.7 mg, 17% yield) as a pale yellow solid. $^1$H NMR (400 MHz, DMSO-d$_6$) δ 11.26 (s, 1H), 7.39 (dd, J=8.2, 0.8 Hz, 1H), 7.33-7.27 (m, 1H), 7.19 (t, J=8.1 Hz, 1H), 5.42-5.38 (m, 1H), 2.97-2.79 (m, 1H), 2.75-2.60 (m, 2H), 2.27-2.12 (m, 1H). LC-MS (ESI⁺): m/z 325.1 (M+H)⁺.

3-[7-[3-(2-Aminoethoxy)propyl]-2-oxo-1,3-benzoxazol-3-yl]piperidine-2,6-dione (Intermediate QR)

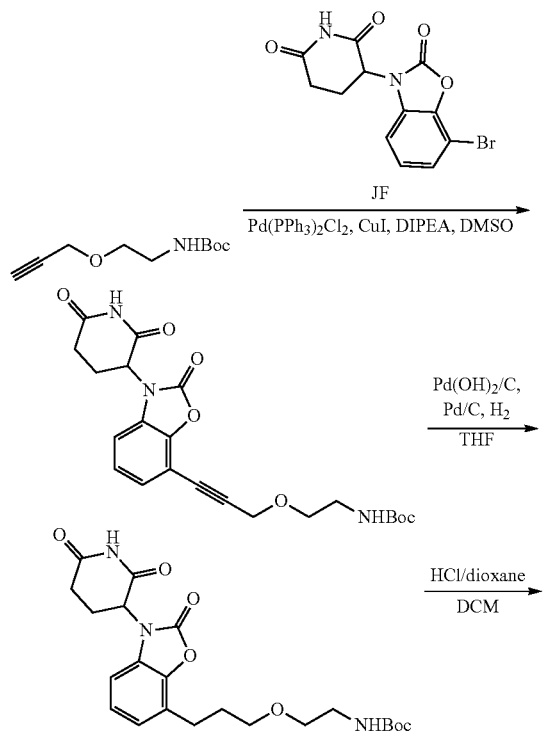

Step 1—Tert-butyl N-[2-[3-[3-(2,6-dioxo-3-piperidyl)-2-oxo-1,3-benzoxazol-7-yl]prop-2-ynoxy] ethyl]carbamate To a solution of tert-butyl N-(2-prop-2-ynoxyethyl)carbamate (689 mg, 3.46 mmol) and 3-(7-bromo-2-oxo-1,3-benzoxazol-3-yl)piperidine-2,6-dione (450 mg, 1.38 mmol, Intermediate JF) in DMF (10 mL) was added Pd(PPh₃)₂Cl₂ (194 mg, 276 umol), CuI (52.7 mg, 277 umol) and Cs₂CO₃ (2.25 g, 6.92 mmol). The reaction was stirred at 80° C. for 3 hrs under N₂. On completion, the reaction mixture was filtered and the filtrate was concentrated in vacuo to give a residue. The residue was purified by reverse phase (0.1% FA condition) to give the title compound (510 mg, 83% yield) as a brown solid. $^1$H NMR (400 MHz, DMSO-d$_6$) δ 11.23 (s, 1H), 7.31 (dd, J=7.2 Hz, 1H), 7.26-7.19 (m, 2H), 6.92-6.77 (m, 1H), 5.46-5.32 (m, 1H), 4.45 (s, 2H), 3.52 (t, J=6.0 Hz, 3H), 3.12 (q, J=5.6 Hz, 2H), 2.93-2.82 (m, 1H), 2.66-2.57 (m, 1H), 2.22-2.13 (m, 1H), 1.36 (s, 9H); LC-MS (ESI⁺) m/z 344.1 (M+H-100)⁺.

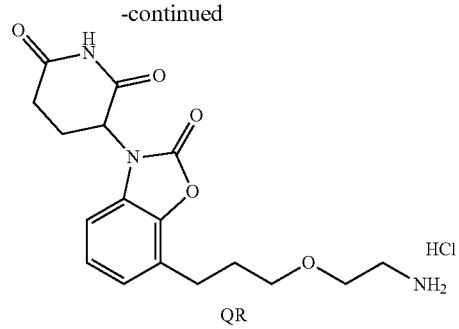

Step 2—Tert-butylN-[2-[3-[3-(2,6-dioxo-3-piperidyl)-2-oxo-1,3-benzoxazol-7-yl]propoxy]ethyl] carbamate To a solution of tert-butyl N-[2-[3-[3-(2,6-dioxo-3-piperidyl)-2-oxo-1,3-benzoxazol-7-yl]prop-2-ynoxy]ethyl]carbamate (340 mg, 766 umol) in THF (20 mL) was added Pd(OH)₂/C (150 mg, 10 wt %) and Pd/C (150 mg, 50 wt %). The reaction mixture was stirred at 25° C. for 2 hrs under H₂ (15 psi). On completion, the reaction mixture was filtered through celite and concentrated in vacuo to give the title compound (350 mg, 90% yield) as gray solid. LC-MS (ESI⁺) m/z 348.1 (M+H-100)⁺.

Step 3—3-[7-[3-(2-Aminoethoxy)propyl]-2-oxo-1,3-benzoxazol-3-yl]piperidine-2,6-dione To a solution of tert-butyl N-[2-[3-[3-(2,6-dioxo-3-piperidyl)-2-oxo-1,3-benzoxazol-7-yl]propoxy] ethyl]carbamate (70.0 mg, 156 umol) in DCM (2 mL) was added HCl/dioxane (4 M, 1 mL). The reaction mixture was stirred at 25° C. for 2 hrs. On completion, the reaction mixture was filtered and the filter cake was concentrated in vacuo to give the title compound (60.0 mg, 99% yield, HCl) as a white solid. LC-MS (ESI⁺) m/z 348.1 (M+H)⁺.

4-[4-[[2-[2-(Cyclopropylmethylamino)-4-pyridyl]oxazole-4-carbonyl]amino]-3-(difluoromethyl)pyrazol-1-yl]cyclohexanecarboxylic acid (Intermediate QT)
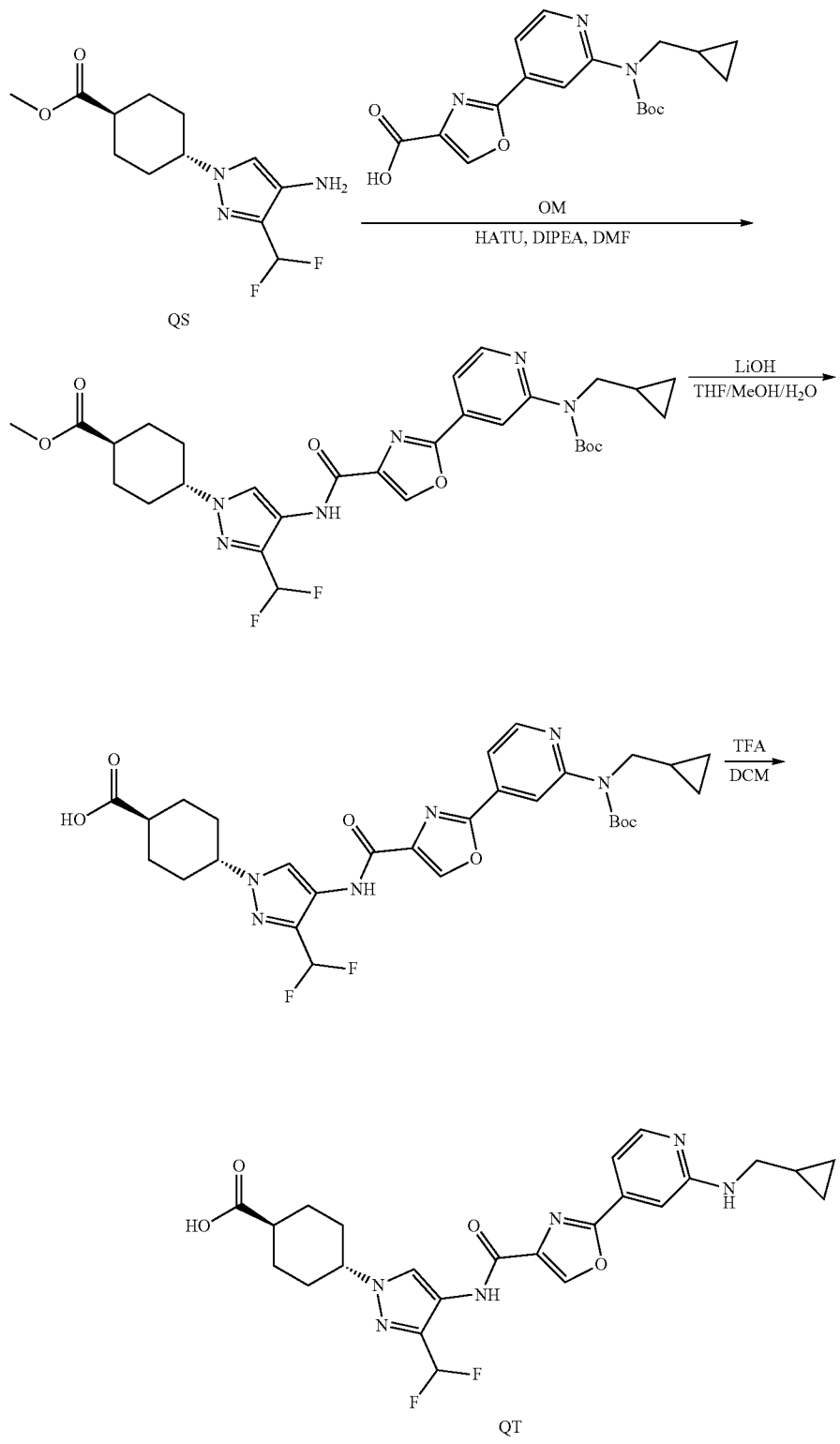

Step 1—Methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]cyclohexanecarboxlate To a mixture of methyl 4-[4-amino-3-(difluoromethyl)pyrazol-1-yl]cyclohexanecarboxylate (350 mg, 1.22 mmol, Intermediate QS) and 2-[2-[tert-butoxycarbonyl(cyclopropylmethyl)amino]-4-pyridyl]oxazole-4-carboxylic acid (437 mg, 1.22 mmol, Intermediate OM) in DMF (20 mL) was added DIPEA (471.75 mg, 3.65 mmol) and HATU (555.15 mg, 1.46 mmol). The reaction mixture was stirred at 25° C. for 1 hour. On completion, the reaction mixture was poured into water (40 mL) and stirred for 20 minutes. The mixture was filtered to give the title compound (420 mg, 52% yield) as a white solid. $^1$H NMR (400 MHz, DMSO-$d_6$) δ 9.72 (s, 1H), 8.96 (s, 1H), 8.55 (d, J=5.1 Hz, 1H), 8.25 (s, 1H), 8.15 (s, 1H), 7.91 (s, 1H), 7.64 (d, J=5.2 Hz, 1H), 7.00 (m, 1H), 4.00 (s, 1H), 3.82 (d, J=7.2 Hz, 2H), 3.58 (s, 3H), 2.85 (s, 3H), 2.69 (s, 3H), 2.35 (m, 1H), 2.01 (m, 4H), 1.74 (d, J=8.4 Hz, 3H), 1.51 (m, 1H), 1.47 (s, 9H), 1.15 (m, 1H), 0.41 (m, 2H), 0.19 (d, J=4.8 Hz, 2H).

Step 2—4-[4-[[2-[2-[Tert-butoxycarbonyl(cyclopropylmethyl)amino]-4-pyridyl]oxazole-4-carbonyl]amino]-3-(difluoromethyl)pyrazol-1-yl]cyclohexanecarboxylic To a mixture of methyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]cyclohexanecarboxylate (180 mg, 292 umol) in a mixed solvent of THF (16 mL), MeOH (4 mL) and H$_2$O (4 mL) was added LiOH (21.0 mg, 878 umol). The reaction mixture was stirred at 25° C. for 12 hours. On completion, the mixture was concentrated in vacuo to remove MeOH and THF. Then water (30 mL) was added into the mixture and adjusted to pH=4-5 with HCl (1 N), and filtered. The filter cake was dried in vacuo to give the title compound (158 mg, 89% yield, HCl) as a white solid. $^1$H NMR (400 MHz, DMSO-$d_6$) δ 12.17 (s, 1H), 9.77 (s, 1H), 9.01 (s, 1H), 8.59 (d, J=5.2 Hz, 1H), 8.30 (s, 1H), 8.20 (s, 1H), 7.69 (d, J=5.2 Hz, 1H), 7.35-6.96 (m, 1H), 4.26 (t, J=11.6 Hz, 1H), 3.93-3.81 (m, 2H), 2.38-2.23 (m, 1H), 2.14-1.97 (m, 4H), 1.92-1.71 (m, 2H), 1.52 (s, 9H), 1.48 (s, 2H), 1.17 (s, 2H), 0.41 (d, J=6.4 Hz, 2H), 0.29-0.20 (m, 2H).

Step 3—4-[4-[[2-[2-(Cyclopropylmethylamino)-4-pyridyl]oxazole-4-carbonyl]amino]-3-(difluoromethyl)pyrazol-1-yl]cyclohexanecarboxylic acid To a mixture of 4-[4-[[2-[2-[tert-butoxycarbonyl(cyclopropylmethyl)amino]-4-pyridyl]oxazole-4-carbonyl]amino]-3-(difluoromethyl)pyrazol-1-yl]cyclohexanecarboxylic acid (120 mg, 200 umol) in DCM (3 mL) was added TFA (22.8 mg, 200 umol). The reaction mixture was stirred at 25° C. for 0.1 hour. On completion, the mixture was concentrated in vacuo to give the title compound (100 mg, 100% yield) as brown oil. LC-MS (ESI$^+$) m/z 501.1 (M+H)$^+$. Absolute configuration of the stereoisomers was randomly assigned, the compound has trans configuration.

2-[2-[tert-butoxycarbonyl(cyclopropylmethyl)amino]-4-pyridyl] oxazole-4-carboxylic acid (Intermediate OM)

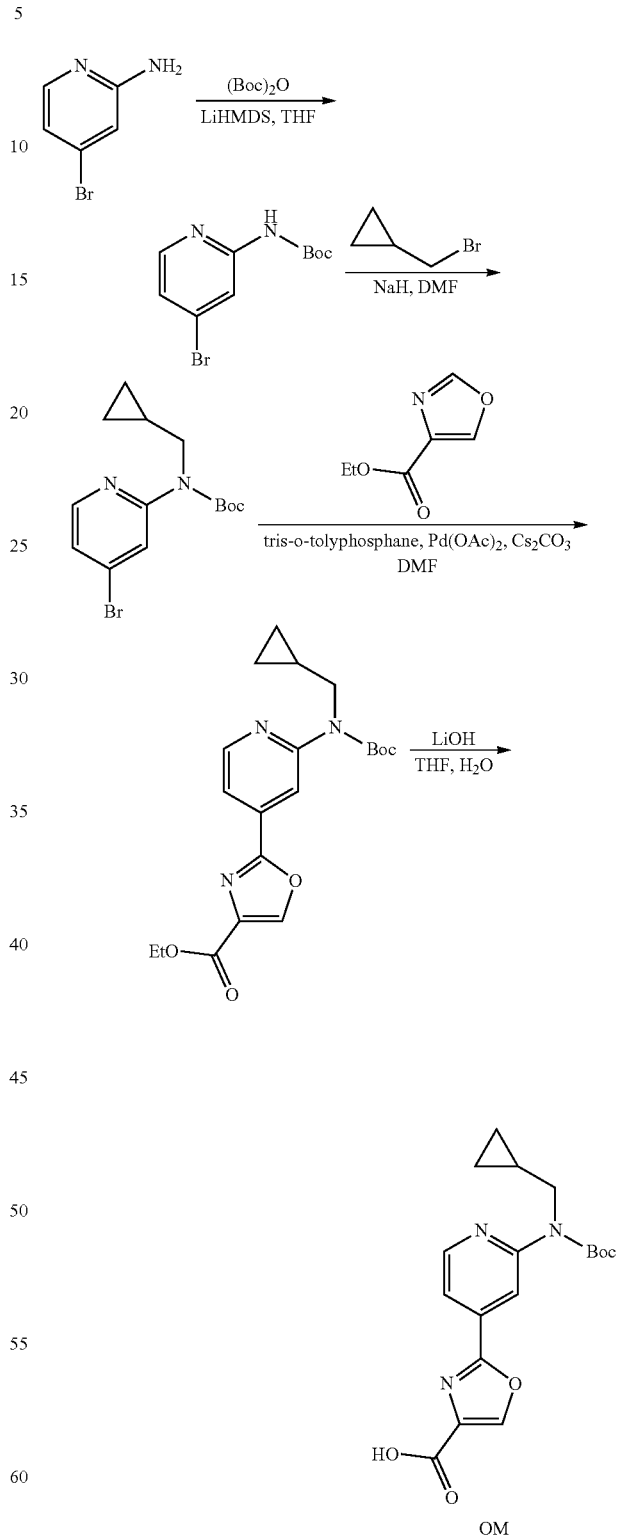

2-[2-[tert-butoxycarbonyl(cyclopropylmethyl)amino]-4-pyridyl] oxazole-4-carboxylic acid was synthesized via Steps 1-4 of Intermediate DF.

4-[4-[[2-[2-[Tert-butoxycarbonyl(cyclopropylmethyl)amino]-4-pyridyl] oxazole-4-carbonyl]amino]-3-carbamoyl-pyrazol-1-yl]benzoic acid (Intermediate DF)

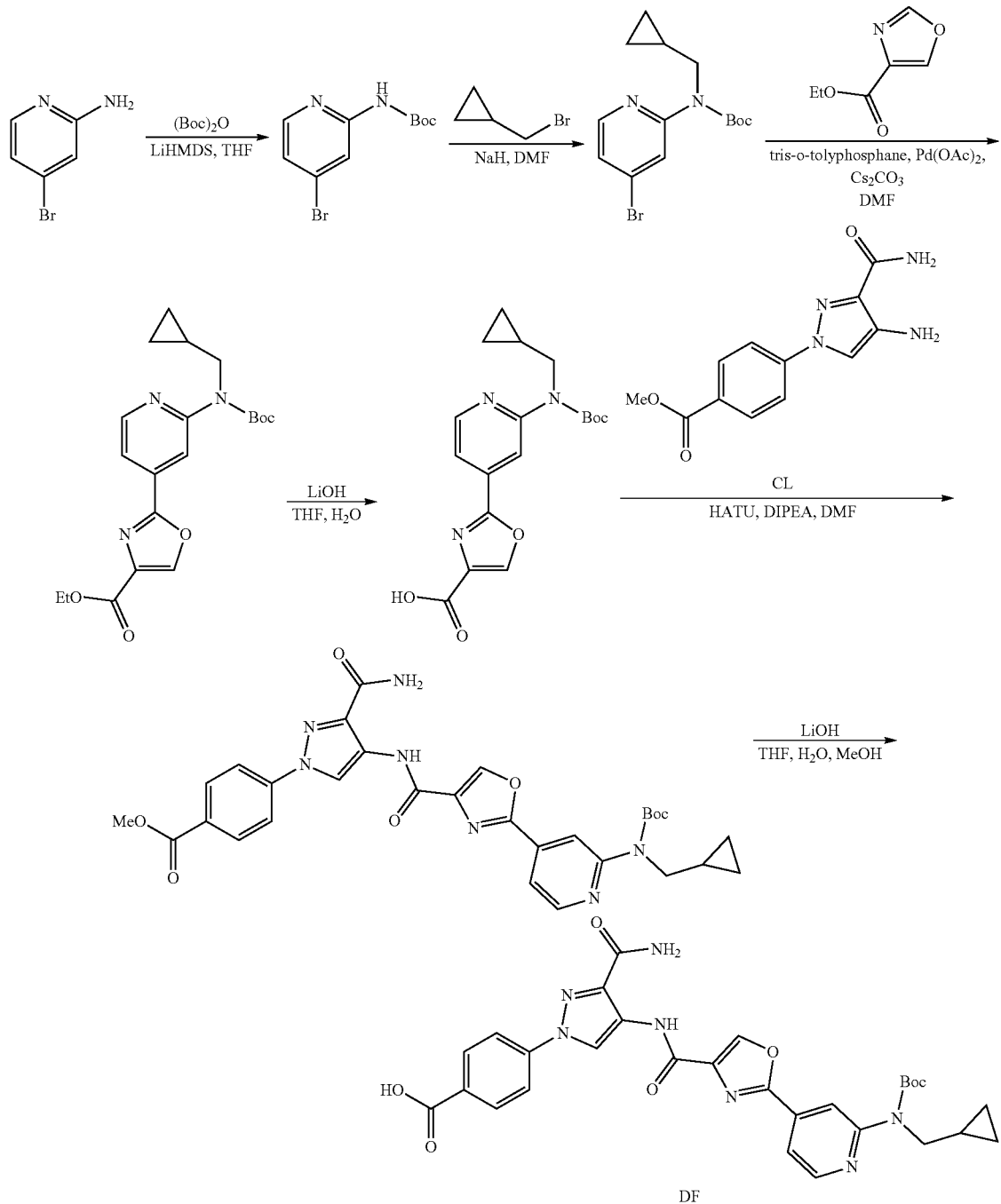

Step 1—Tert-butyl N-(4-bromo-2-pyridyl)-N-(cyclopropylmethyl)carbamate

To a solution of tert-butyl N-(4-bromo-2-pyridyl)carbamate (5.0 g, 18.3 mmol, synthesized via Step 1 of Intermediate CM) in DMF (50 mL) was added NaH (1.10 g, 27.5 mmol) at 0° C. for 30 minutes. Then bromomethylcyclopropane (2.97 g, 22.0 mmol) was added into the mixture. The reaction mixture was stirred at rt for 17 h. On completion, the mixture was quenched with water (40 mL) and extracted with EA (2×50 mL). The organic phase was washed with brine (60 mL), dried over $Na_2SO_4$, and concentrated in vacuo. The residue was purified by silica gel chromatography to give the title compound (2.7 g, 45% yield) as a white solid. $^1$H NMR (400 MHz, CDCl$_3$) δ 8.18 (d, J=5.2 Hz, 1H), 7.98 (d, J=1.6 Hz, 1H), 7.17 (dd, J=1.6, 5.2 Hz, 1H), 3.88 (d, J=7.2 Hz, 2H), 1.55 (s, 9H), 1.22-1.15 (m, 1H), 0.47-0.40 (m, 2H), 0.28-0.23 (m, 2H).

Step 2—Ethyl 2-[2-[tert-butoxycarbonyl(cyclopropylmethyl)amino]-4-pyridyl]oxazole-4-carboxylate To a solution of ethyl oxazole-4-carboxylate (1.16 g, 8.25 mmol) and tert-butyl N-(4-bromo-2-pyridyl)-N-(cyclopropylmethyl)carbamate (2.7 g, 8.25 mmol) in DMF (30 mL) was added tris-o-tolylphosphane (502 mg, 1.65 mmol), Pd(OAc)$_2$ (185 mg, 825 umol) and Cs$_2$CO$_3$ (5.38 g, 16.5 mmol). The reaction mixture was stirred at 80° C. under nitrogen for 17 h. On completion, the mixture was diluted with water (50 mL) and extracted with EA (3×50 mL). The organic layer was washed with water (100 ml), dried over Na$_2$SO$_4$, and concentrated in vacuo. The residue was purified by silica gel chromatography to give the title compound (1.8 g, 56% yield) as a white oil. $^1$H NMR (400 MHz, CDCl$_3$) δ 8.50 (dd, J=1.6, 5.2 Hz, 1H), 8.38 (s, 1H), 8.35 (s, 1H), 7.71 (dd, J=1.6, 5.2 Hz, 1H), 4.46 (q, J=7.2 Hz, 2H), 3.93 (d, J=7.2 Hz, 2H), 1.57 (s, 9H), 1.44 (t, J=7.2 Hz, 3H), 1.24-1.16 (m, 1H), 0.46-0.40 (m, 2H), 0.28-0.24 (m, 2H).

Step 3—2-[2-Tert-butoxycarbonyl(cyclopropylmethyl)amino]-4-pyridyl]oxazole-4-carboxylic acid To a solution of ethyl 2-[2-[tert-butoxycarbonyl(cyclopropylmethyl)amino]-4-pyridyl]oxazole-4-carboxylate (0.5 g, 1.29 mmol) in a mixed solvent of THF (5 mL) and H$_2$O (1 mL) was added LiOH (92.7 mg, 3.87 mmol). The reaction mixture was stirred at rt for 2 h. On completion, the mixture was acidified with 1N HCl solution until the pH=3-5, then extracted with EA (2×30 mL). The combined organic phase was dried over Na$_2$SO$_4$, filtered and concentrated in vacuo to give the title compound (460 mg, 99% yield) as a white solid. LC-MS (ESI$^+$) m/z 304.0 (M−56)$^+$.

Step 4—Methyl 4-[4-[[2-[2-[tert-butoxycarbonyl(cyclopropylmethyl)amino]-4-pyridyl]oxazole-4-carbonyl]amino]-3-carbamoyl-pyrazol-1-yl]benzoate To a solution of 2-[2-[tert-butoxycarbonyl(cyclopropylmethyl)amino]-4-pyridyl]oxazole-4-carboxylic acid (360 mg, 1.00 mmol) and methyl 4-(4-amino-3-carbamoyl-pyrazol-1-yl)benzoate (443 mg, 1.70 mmol, Intermediate CL) in DMF (5 mL) was added DIPEA (647 mg, 5.01 mmol) and HATU (457 mg, 1.20 mmol). The reaction mixture was stirred at rt for 0.5 hr. On completion, the mixture was diluted with water (40 mL) and extracted with EA (2×30 mL). The combined organic layer was washed with brine (40 mL) and concentrated in vacuo. The residue was purified by silica gel chromatography to give the title compound (190 mg, 32% yield) as a white solid. LC-MS (ESI$^+$) m/z 602.3 (M+H)$^+$.

Step 5—4-[4-[[2-[2-[Tert-butoxycarbonyl(cyclopropylmethyl)amino]-4-pyridyl]oxazole-4-carbonyl]amino]-3-carbamoyl-pyrazol-1-yl]benzoic acid To a solution of methyl 4-[4-[[2-[2-[tert-butoxycarbonyl(cyclopropylmethyl)amino]-4-pyridyl]oxazole-4-carbonyl]amino]-3-carbamoyl-pyrazol-1-yl]benzoate (190 mg, 316 umol) in a mixed solvent of THF (3 mL), MeOH (2 mL) and H$_2$O (1 mL) was added LiOH (37.8 mg, 1.58 mmol). The reaction mixture was stirred at rt for 17 h. On completion, the mixture was acidified with 1N HCl solution until the pH=5-7, concentrated in vacuo to give the title compound (180 mg, 97% yield) as a yellow solid. LC-MS (ESI$^+$) m/z 588.3 (M+H)$^+$.

Methyl 4-[4-amino-3-(difluoromethyl)pyrazol-1-yl] cyclohexanecarboxylate (Intermediate QS)

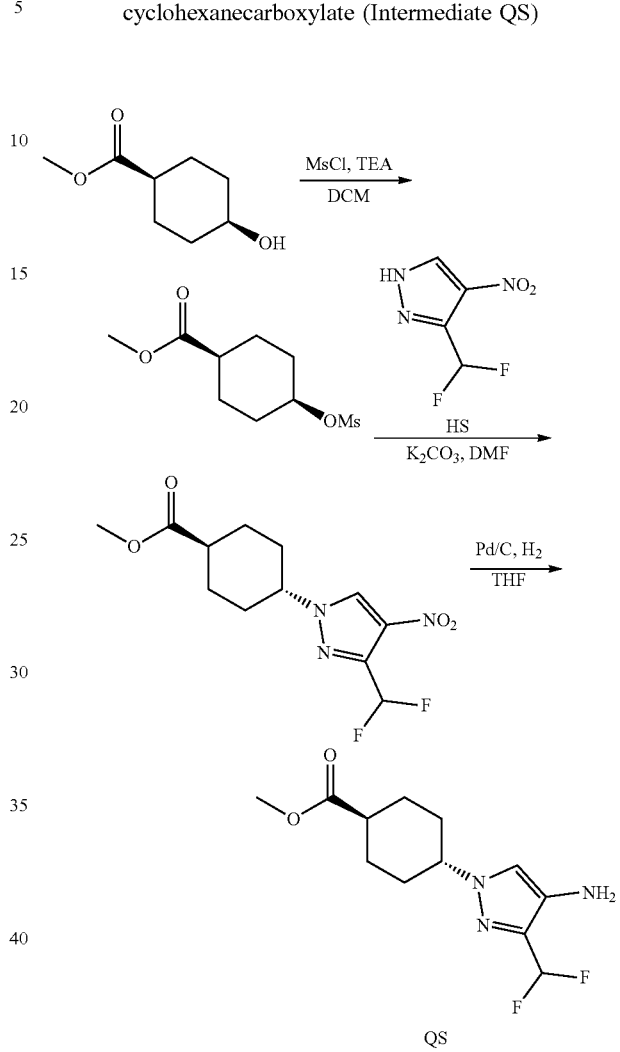

Step 1—Methyl 4-methyl sulfonyloxycyclohexanecarboxylate

To a mixture of methyl 4-hydroxycyclohexanecarboxylate (1.00 g, 6.32 mmol, CAS #3618-03-9) in DCM (10 mL) was added TEA (831 mg, 8.22 mmol) and MsCl (1.09 g, 9.48 mmol) at 0° C., the reaction mixture was stirred 0° C. for 2 hours. On completion, the mixture was poured into the ice-water (50 mL) and extracted with DCM (2×30 mL). The combined organic phase was washed with brine (2×50 mL), dried with anhydrous Na$_2$SO$_4$, filtered and concentrated in vacuo to give the title compound (1.20 g, 80% yield) as colorless oil. $^1$H NMR (400 MHz, CDCl$_3$) δ 4.91 (t, J=2.8, 5.2 Hz, 1H), 3.69 (s, 3H), 3.02 (s, 3H), 2.41-2.39 (m, 1H), 2.09-1.99 (m, 2H), 1.97-1.86 (m, 2H), 1.80 (t, J=4.4, 9.2 Hz, 2H), 1.75-1.66 (m, 2H).

Step 2—Methyl 4-[3-(difluoromethyl)-4-nitro-pyrazol-1-yl] cyclohexanecarboxylate To a mixture of 3-(difluoromethyl)-4-nitro-1H-pyrazole (555 mg, 3.40 mmol, Intermediate HS) and methyl 4-methyl sulfonyloxycyclohexanecarboxylate (1.20 g, 5.08 mmol) in DMF (30 mL) was added K₂CO₃ (2.11 g, 15.2 mmol). The reaction mixture was stirred at 80° C. for 12 hours. On completion, the mixture was poured into water (50 mL). The aqueous phase was extracted with ethyl acetate (2×30 mL). The combined organic phase was washed with brine (2×40 mL), dried with anhydrous Na₂SO₄, filtered and concentrated in vacuo. The residue was purified by column chromatography to give the title compound (480 mg, 25% yield) as brown oil. ¹H NMR (400 MHz, CDCl₃) δ 8.23 (s, 1H), 7.25-6.96 (m, 1H), 4.26-4.14 (m, 1H), 3.76-3.65 (m, 3H), 2.40 (t, J=3.6, 12.4 Hz, 1H), 2.36-2.17 (m, 4H), 1.83 (d, J=3.6, 12.8 Hz, 2H), 1.69-1.59 (m, 2H).

Step 3—Methyl 4-[4-amino-3-(difluoromethyl)pyrazol-1-yl]cyclohexanecarboxylate

To a mixture of methyl 4-[3-(difluoromethyl)-4-nitropyrazol-1-yl]cyclohexanecarboxylate (430 mg, 1.42 mmol) in THF (20 mL) was added Pd/C (100 mg, 10 wt %) under N₂. The suspension was degassed under vacuum and purged with H₂ gas three times. The mixture was stirred under H₂ (15 psi) at 25° C. for 12 hours. On completion, the mixture was filtered and the filtrate was concentrated in vacuo to give the title compound (350 mg, 90% yield) a brown solid. LC-MS (ESI⁺) m/z 274.1 (M+H)⁺.

4-[4-[[2-[2-(Cyclopropylmethylamino)-4-pyridyl]oxazole-4-carbonyl]amino]-3-(difluoromethyl)pyrazol-1-yl]cyclohexanecarboxylic acid (Intermediate QT)

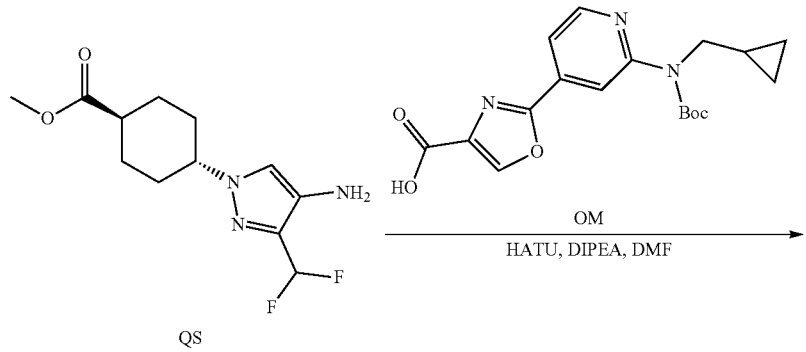

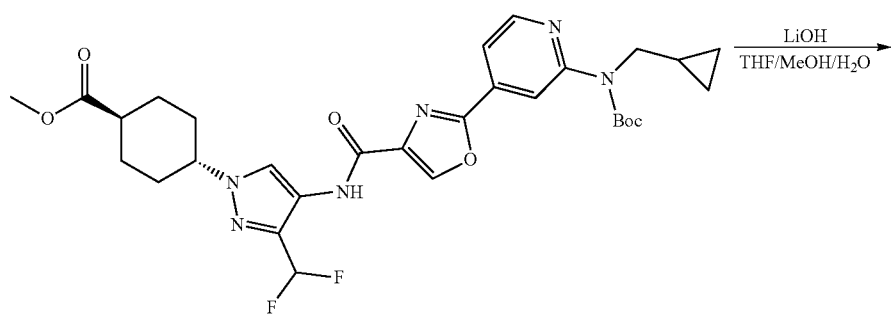

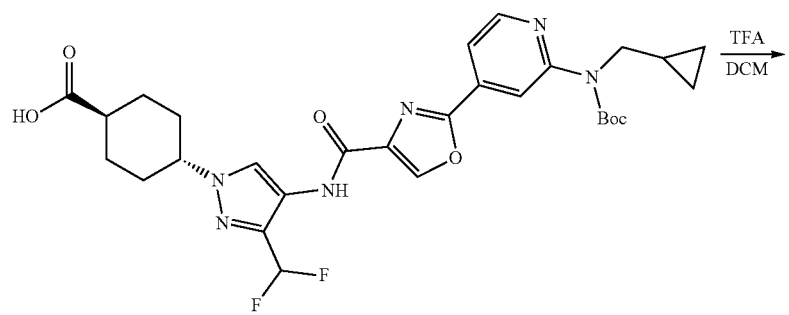

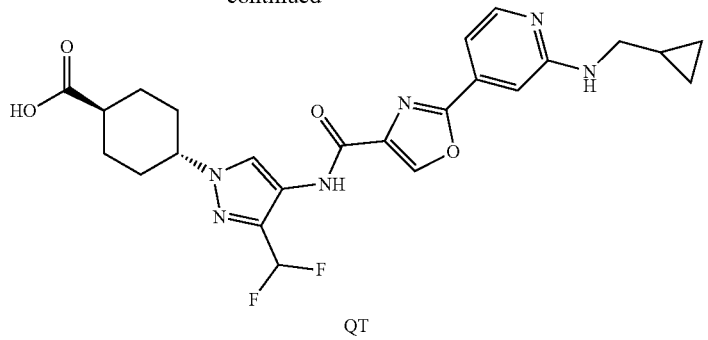

QT

Step 1—Methyl 4-[4-[[2-[2-[tert-butoxycarbonyl (cyclopropylmethyl)amino]-4-pyridyl]oxazole-4-carbonyl] amino]-3-(difluoromethyl)pyrazol-1-yl]cyclohexanecarboxylate To a mixture of methyl 4-[4-amino-3-(difluoromethyl) pyrazol-1-yl]cyclohexanecarboxylate (350 mg, 1.22 mmol, Intermediate QS) and 2-[2-[tert-butoxycarbonyl(cyclopropylmethyl)amino]-4-pyridyl]oxazole-4-carboxylic acid (437 mg, 1.22 mmol, Intermediate OM) in DMF (20 mL) was added DIPEA (471.75 mg, 3.65 mmol) and HATU (555.15 mg, 1.46 mmol). The reaction mixture was stirred at 25° C. for 1 hour. On completion, the reaction mixture was poured into water (40 mL) and stirred for 20 minutes. The mixture was filtered to give the title compound (420 mg, 52% yield) as a white solid. $^1$H NMR (400 MHz, DMSO-$d_6$) δ 9.72 (s, 1H), 8.96 (s, 1H), 8.55 (d, J=5.1 Hz, 1H), 8.25 (s, 1H), 8.15 (s, 1H), 7.91 (s, 1H), 7.64 (d, J=5.2 Hz, 1H), 7.00 (m, 1H), 4.00 (s, 1H), 3.82 (d, J=7.2 Hz, 2H), 3.58 (s, 3H), 2.85 (s, 3H), 2.69 (s, 3H), 2.35 (m, 1H), 2.01 (m, 4H), 1.74 (d, J=8.4 Hz, 3H), 1.51 (m, 1H), 1.47 (s, 9H), 1.15 (m, 1H), 0.41 (m, 2H), 0.19 (d, J=4.8 Hz, 2H).

Step 2—4-[4-[[2-[2-[Tert-butoxycarbonyl(cyclopropylmethyl)amino]-4-pyridyl]oxazole-4-carbonyl]amino]-3-(difluoromethyl)pyrazol-1-yl]]cyclohexanecarboxylic To a mixture of methyl 4-[4-[[2-[2-[tert-butoxycarbonyl (cyclopropylmethyl)amino]-4-pyridyl]oxazole-4-carbonyl] amino]-3-(difluoromethyl)pyrazol-1-yl]cyclohexanecarboxylate (180 mg, 292 umol) in a mixed solvent of THF (16 mL), MeOH (4 mL) and $H_2O$ (4 mL) was added LiOH (21.0 mg, 878 umol). The reaction mixture was stirred at 25° C. for 12 hours. On completion, the mixture was concentrated in vacuo to remove MeOH and THF. Then water (30 mL) was added into the mixture and adjusted to pH=4-5 with HCl (1 N), and filtered. The filter cake was dried in vacuo to give the title compound (158 mg, 89% yield, HCl) as a white solid. $^1$H NMR (400 MHz, DMSO-$d_6$) δ 12.17 (s, 1H), 9.77 (s, 1H), 9.01 (s, 1H), 8.59 (d, J=5.2 Hz, 1H), 8.30 (s, 1H), 8.20 (s, 1H), 7.69 (d, J=5.2 Hz, 1H), 7.35-6.96 (m, 1H), 4.26 (t, J=11.6 Hz, 1H), 3.93-3.81 (m, 2H), 2.38-2.23 (m, 1H), 2.14-1.97 (m, 4H), 1.92-1.71 (m, 2H), 1.52 (s, 9H), 1.48 (s, 2H), 1.17 (s, 2H), 0.41 (d, J=6.4 Hz, 2H), 0.29-0.20 (m, 2H).

Step 3—4-[4-[[2-[2-(Cyclopropylmethylamino)-4-pyridyl]oxazole-4-carbonyl]amino]-3-(difluoromethyl)pyrazol-1-yl]cyclohexanecarboxylic acid To a mixture of 4-[4-[[2-[2-[tert-butoxycarbonyl(cyclopropylmethyl)amino]-4-pyridyl]oxazole-4-carbonyl] amino]-3-(difluoromethyl)pyrazol-1-yl]cyclohexanecarboxylic acid (120 mg, 200 umol) in DCM (3 mL) was added TFA (22.8 mg, 200 umol). The reaction mixture was stirred at 25° C. for 0.1 hour. On completion, the mixture was concentrated in vacuo to give the title compound (100 mg, 100% yield) as brown oil. LC-MS (ESI$^+$) m/z 501.1 (M+H)$^+$. Absolute configuration of the stereoisomers was randomly assigned, the compound has trans configuration.

1-(4-Methoxyphenyl)-N-methyl-N-[[(2S)-4-prop-2-ynylmorpholin-2-yl]methyl]methanamine (Intermediate RO)

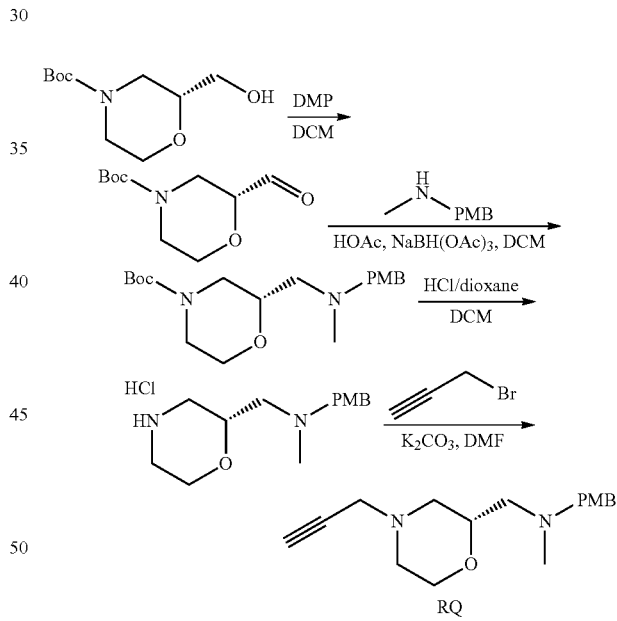

RQ

Step 1-Tert-butyl (2R)-2-formylmorpholine-4-carboxylate

To a solution of tert-butyl (2R)-2-(hydroxymethyl)morpholine-4-carboxylate (2.00 g, 9.21 mmol, CAS #135065-71-3) in DCM (40 mL) was added DMP (4.69 g, 11.0 mmol) at 0° C. The reaction mixture was stirred at 25° C. for 2 hours. On completion, the mixture was quenched with aq. $Na_2S_2O_3$ (50 mL) and aq. $NaHCO_3$ (50 mL). The mixture was stirred for 15 minutes and extracted with EA (2×50 mL). The organic layer was washed with brine (50 mL), dried with $Na_2SO_4$, and concentrated in vacuo to give the title compound (1.50 g, 76% yield) as colorless oil. $^1$H NMR (400 MHz, CDCl$_3$) δ 9.65 (s, 1H), 4.08-4.00 (m, 1H), 3.95-3.85 (m, 2H), 3.83-3.75 (m, 1H), 3.68-3.53 (m, 2H), 3.12-3.03 (m, 1H), 1.47 (s, 9H).

Step 2—Tert-butyl (2S)-2-[[(4-methoxyphenyl)methyl-methyl-amino]methyl]morpholine-4-carboxylate To a solution of tert-butyl (2R)-2-formylmorpholine-4-carboxylate (1.5 g, 6.97 mmol) and 1-(4-methoxyphenyl)-N-methyl-methanamine (1.05 g, 6.97 mmol) in DCM (30 mL) was added HOAc (418 mg, 6.97 mmol) and the reaction was stirred at 25° C. Thirty minutes later, NaBH(OAc)$_3$ (1.77 g, 8.36 mmol) was added and the reaction mixture was stirred at 25° C. for 10 hours. On completion, the mixture was concentrated in vacuo. The residue was purified by reversed phase (0.1% FA) to give the title compound (1.4 g, 57% yield) as a yellow solid. $^1$H NMR (300 MHz, CDCl$_3$) δ 7.22 (d, J=8.4 Hz, 2H), 6.85 (d, J=8.4 Hz, 2H), 4.07-3.94 (m, 1H), 3.93-3.83 (m, 2H), 3.90 (s, 3H), 3.58-3.43 (m, 4H), 3.01-2.80 (m, 1H), 2.62-2.46 (m, 2H), 2.41-2.31 (m, 1H), 2.26 (s, 3H), 1.48 (s, 9H); LC-MS (ESI$^+$) m/z 351.1 (M+H)$^+$.

Step 3—1-(4-Methoxyphenyl)-N-methyl-N-[[(2R)-morpholin-2-yl]methyl]methanamine hydrochloride To a solution of tert-butyl (2S)-2-[[(4-methoxyphenyl)methyl-methyl-amino]methyl]morpholine-4-carboxylate (1.40 g, 3.99 mmol) in HCl/dioxane (10 mL) was added DCM (10 mL). The reaction mixture was stirred at 25° C. for 2 hours. On completion, the mixture was concentrated in vacuo to give the title compound (1.15 g, 100% yield, HCl) as a yellow solid. LC-MS (ESI$^+$) m/z 251.1 (M+H)$^+$.

Step 4—1-(4-methoxyphenyl)-N-methyl-N-[[(2S)-4-prop-2-ynylmorpholin-2-yl]methyl]methanamine To a solution of 1-(4-methoxyphenyl)-N-methyl-N-[[(2R)-morpholin-2-yl]methyl]methanamine (1.15 g, 4.01 mmol, HCl) and 3-bromoprop-1-yne (525 mg, 4.41 mmol) in DMF (20 mL) was added K$_2$CO$_3$ (1.66 g, 12.0 mmol). The reaction mixture was stirred at 25° C. for 12 hours. On completion, the mixture was diluted with water (100 mL), and extracted with EA (2×50 mL). The organic layer was washed with brine (100 mL), then concentrated in vacuo. The residue was purified by reversed phase chromatography (0.1% FA condition) to give the title compound (700 mg, 61% yield) as colourless oil. LC-MS (ESI$^+$) m/z 289.2 (M+H)$^+$.

[1-[(4-Methoxyphenyl) methyl]-2,6-dioxo-3-piperidyl] trifluoromethanesulfonate (Intermediate IQ)

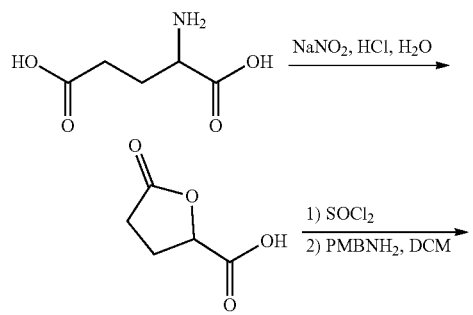

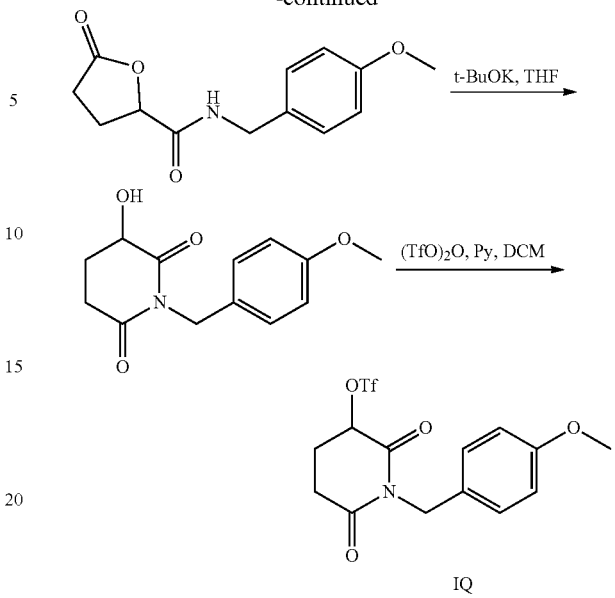

Step 1—5-Oxotetrahydrofuran-2-carboxylic acid

To a solution of 2-aminopentanedioic acid (210 g, 1.43 mol, CAS #617-65-2) in H$_2$O (800 mL) and HCl (12 M, 210 mL) was added a solution of NaNO$_2$ (147 g, 2.13 mol) in H$_2$O (400 mL) at −5° C. The mixture was stirred at 15° C. for 12 hrs. On completion, the mixture was concentrated and then dissolved in EA (500 mL) and filtered and washed with EA (3×100 mL). The filtrate and washed solution were dried over Na$_2$SO$_4$, filtered and concentrated in vacuo to give the title compound (200 g, crude) as yellow oil. $^1$H NMR (400 MHz, CDCl$_3$) δ 6.43 (s, 1H), 5.02-4.95 (m, 1H), 2.67-2.38 (m, 4H)

Step 2—N-[(4-methoxyphenyl)methyl]-5-oxo-tetrahydrofuran-2-carboxamide

To 5-oxotetrahydrofuran-2-carboxylic acid (120 g, 922 mmol) was added SOCl$_2$ (246 g, 2.07 mol) at 0° C. slowly. The mixture was stirred at 85° C. for 3 hrs, and then the mixture was stirred at 15° C. for 6 hrs. The mixture was concentrated in vacuo. The residue was dissolved in dry DCM (1 L) at 0° C. under N$_2$. After that a solution of Et$_3$N (187 g, 1.84 mol) and 4-methoxybenzylamine (101 g, 738 mmol) in DCM (400 mL) was added, then the mixture was stirred at 15° C. for 3 hrs. On completion, water (600 mL) was added and the mixture was extracted with DCM (3×300 mL). The combined organic phase was washed with 0.5 M HCl (500 mL), brine (500 mL), dried over with anhydrous sodium sulfate and filtered. The filtrate was concentrated in vacuo and the residue was purified by flash silica gel chromatography (PE:EA=1:1) to give the title compound (138 g, 60% yield) as a yellow solid. $^1$H NMR (400 MHz, CDCl$_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS (ESI$^+$) m/z 272.0 (M+Na)$^+$.

Step 3—3-Hydroxy-1-[(4-methoxyphenyl)methyl]piperidine-2,6-dione

A solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated NH₄Cl solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. ¹H NMR (400 MHz, CDCl₃) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl]trifluoromethanesulfonate To a solution of 3-hydroxy-1-[(4-methoxyphenyl) methyl] piperidine-2,6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under N₂. On completion, the mixture was concentrated in vacuo. The residue was purified by column chromatography on silica gel (PE:EA=20:1/8:1) to give the title compound (45.0 g, 68% yield) as light yellow gum. ¹H NMR (400 MHz, CDCl₃) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

5-Bromo-3-methyl-1H-benzimidazol-2-one (Intermediate IP)

d₆) δ 8.22 (s, 1H), 7.98 (d, J=9.2 Hz, 1H), 7.16 (d, J=1.6 Hz, 1H), 6.82 (dd, J=8.4, 1.6 Hz, 1H), 2.95 (d, J=4.8 Hz, 3H).

Step 2—4-Bromo-N₂-methyl-benzene-1,2-diamine

To a mixture of 5-bromo-N-methyl-2-nitro-aniline (200 g, 865 mmol) in EtOAc (1 L) and H₂O (500 mL) was added AcOH (1.00 L). The mixture was warmed to 50° C., and then Fe (174 g, 3.11 mol) was added to the reaction mixture. After that, the reaction mixture was stirred at 80° C. for 6 hours. On completion, the mixture was filtered through celite. The filtrate was concentrated in vacuo and the residue was diluted with H₂O (250 mL) and extracted with EtOAc (3×300 mL). The combined organic layers were washed with aq.NaHCO₃ and brine (300 mL), dried over Na₂SO₄, filtered and concentrated in vacuo. The residue was purified by flash silica gel chromatography to give the title compound (130 g, 75% yield) as black oil. ¹H NMR (400 MHz, DMSO-d₆) δ 6.55-6.52 (m, 1H), 6.48-6.45 (m, 1H), 6.43-6.42 (m, 1H), 4.89-4.88 (m, 1H), 4.61 (s, 2H), 2.70 (d, J=4.0 Hz, 3H).

Step 3—5-Bromo-3-methyl-1H-benzimidazol-2-one

To a solution of 4-bromo-N₂-methyl-benzene-1,2-diamine (110 g, 547 mmol) in CH₃CN (1.3 L) was added CDI (177 g, 1.09 mol). The mixture was stirred at 80° C. for 6 hours under N₂. On completion, the mixture was concentrated in vacuo. The mixture was diluted with H₂O (1.0 L) and filtered. The filter cake was washed with water (3×200 mL) and dried in vacuo to give the title compound (106 g, 85% yield) as a white solid. ¹H NMR (400 MHz, DMSO-d₆) δ 11.00 (s, 1H), 7.33 (s, 1H), 7.13 (d, J=8.0 Hz, 1H), 6.92 (d, J=8.0 Hz, 1H), 3.27 (s, 3H).

3-(5-bromo-3-methyl-2-oxo-benzimidazol-1-yl)piperidine-2,6-dione (3-(5-bromo-3-methyl-2-oxo-2,3-dihydro-1H-1,3-benzodiazol-1-yl)piperidine-2,6-dione) (Intermediate HN)

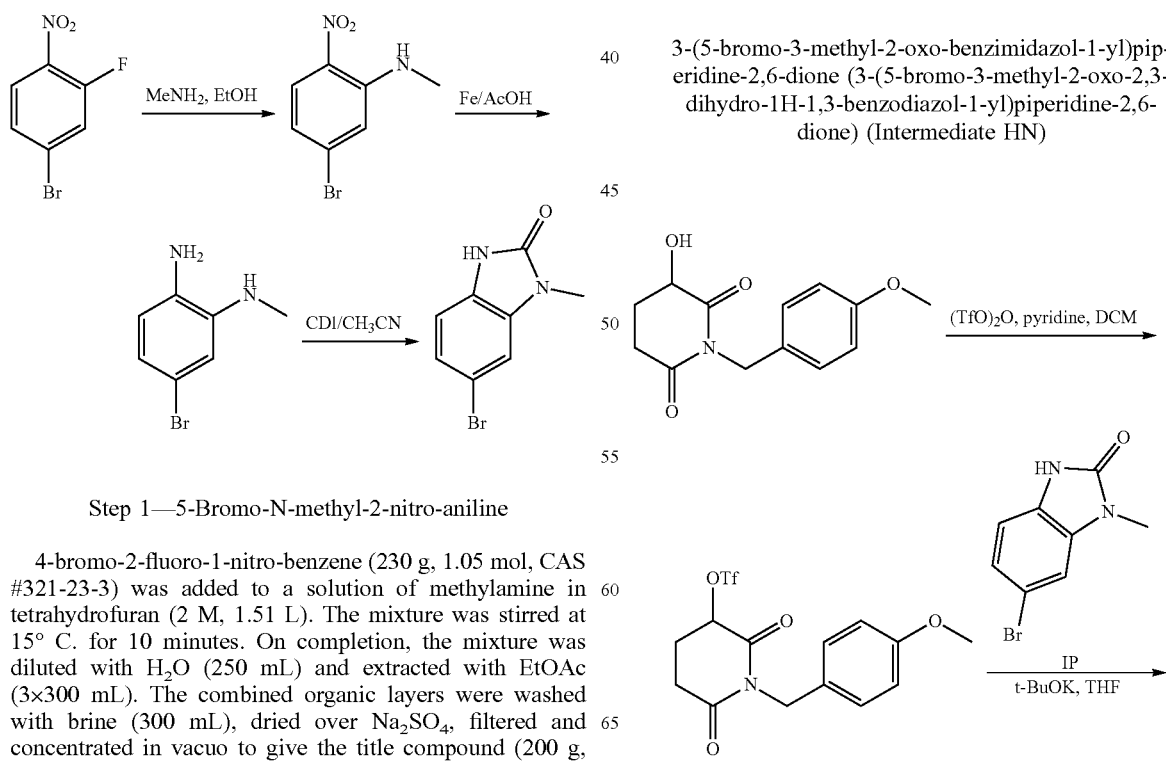

Step 1—5-Bromo-N-methyl-2-nitro-aniline 4-bromo-2-fluoro-1-nitro-benzene (230 g, 1.05 mol, CAS #321-23-3) was added to a solution of methylamine in tetrahydrofuran (2 M, 1.51 L). The mixture was stirred at 15° C. for 10 minutes. On completion, the mixture was diluted with H₂O (250 mL) and extracted with EtOAc (3×300 mL). The combined organic layers were washed with brine (300 mL), dried over Na₂SO₄, filtered and concentrated in vacuo to give the title compound (200 g, 83% yield) as a yellow solid. ¹H NMR (400 MHz, DMSO- -continued

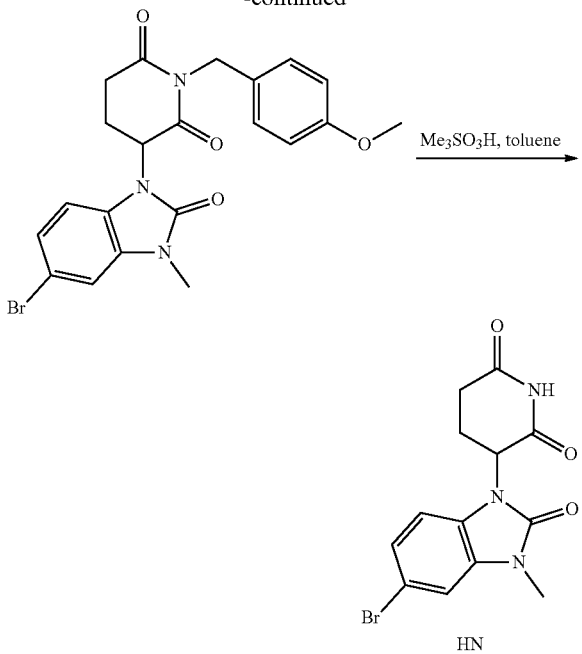

Step 1—[1-[(4-Methoxyphenyl) methyl]-2,6-dioxo-3-piperidyl]trifluoromethanesulfonate To a solution of 3-hydroxy-1-[(4-methoxyphenyl) methyl] piperidine-2,6-dione (43.0 g, 173 mmol, Intermediate IQ) and pyridine (27.3 g, 345 mmol) in DCM (500 mL) was added trifluoromethylsulfonyl trifluoromethanesulfonate (73.0 g, 258.74 mmol) dropwise at 0° C. The mixture was stirred at 0-10° C. for 1.5 hours under $N_2$. On completion, the mixture was concentrated in vacuo. The residue was purified by column chromatography on silica gel to give the title compound (45.0 g, 68% yield) as light yellow gum. $^1$H NMR (400 MHz, CDCl$_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

Step 2—3-(5-Bromo-3-methyl-2-oxo-benzimidazol-1-yl)-1-[(4-methoxyphenyl)methyl]piperidine-2,6-dione To a solution of 5-bromo-3-methyl-1H-benzimidazol-2-one (4.90 g, 21.6 mmol, Intermediate IP) in THF (300 mL) was added t-BuOK (3.63 g, 32.3 mmol) at 0° C. The mixture was stirred at 0-10° C. for 1 hour under $N_2$. Then a solution of [1-[(4-methoxyphenyl) methyl]-2,6-dioxo-3-piperidyl] trifluoromethanesulfonate (9.87 g, 25.9 mmol) in THF (100 mL) was added to the reaction mixture at 0-10° C. during 30 minutes. The mixture was stirred at 0-10° C. for 30 minutes under $N_2$. An additional solution of [1-[(4-methoxyphenyl) methyl]-2,6-dioxo-3-piperidyl]trifluoromethanesulfonate (2.47 g, 6.47 mmol) in THF (20 mL) was added to the reaction mixture at 0-10° C. dropwise. The mixture was then stirred at 0-10° C. for another 30 minutes under $N_2$. On completion, the reaction was quenched water (400 mL) and extracted with EA (3×200 mL). The combined organic layer was concentrated in vacuo. The residue was triturated with EA (80 mL) and filtered. The filter cake was collected and dried in vacuo to give the title compound (6.70 g, 67% yield)

as light yellow solid. The filtrate was also concentrated in vacuo and the residue was purified by column chromatography to give another batch title compound (1.80 g, 18% yield) as light yellow solid. $^1$H NMR (400 MHz, DMSO-d$_6$) δ 7.47 (d, J=1.6 Hz, 1H), 7.21-7.16 (m, 3H), 7.01 (d, J=8.0 Hz, 1H), 6.85 (d, J=8.8 Hz, 2H), 5.55-5.51 (m, 1H), 4.84-4.73 (m, 2H), 3.72 (s, 3H), 3.33 (s, 3H), 3.04-3.00 (m, 1H), 2.83-2.67 (m, 2H), 2.07-2.05 (m, 1H).

Step 3—3-(5-Bromo-3-methyl-2-oxo-benzimidazol-1-yl)piperidine-2,6-dione

To a mixture of 3-(5-bromo-3-methyl-2-oxo-benzimidazol-1-yl)-1-[(4-methoxyphenyl)methyl] piperidine-2,6-dione (8.50 g, 18.6 mmol) in toluene (50 mL) was added methanesulfonic acid (33.8 g, 351 mmol, 25 mL) at room temperature (15° C.). The mixture was stirred at 120° C. for 2 hours. On completion, the reaction mixture was cooled to room temperature and concentrated in vacuo. The residue was poured into ice/water (200 mL), and extracted with EA (3×100 mL). The combined organic layer was washed with brine (50 mL), dried over Na$_2$SO$_4$, filtered and concentrated in vacuo. The residue was triturated with EA (80 mL) and filtered. The filtrate cake was collected and dried in vacuo to give the title compound (4.20 g, 67% yield) as off-white solid. $^1$H NMR (400 MHz, DMSO-d$_6$) δ 11.12 (s, 1H), 7.47 (d, J=2.0 Hz, 1H), 7.22 (d, J=8.4 Hz, 1H), 7.10 (d, J=8.4 Hz, 1H), 5.40-5.35 (m, 1H), 2.34 (s, 3H), 2.92-2.88 (m, 1H), 2.71-2.60 (m, 2H), 2.03-1.99 (m, 1H).

1-(4-methoxyphenyl)-N-methyl-N-[[(2S)-4-prop-2-ynylmorpholin-2-yl]methyl]methanamine (Intermediate RQ)

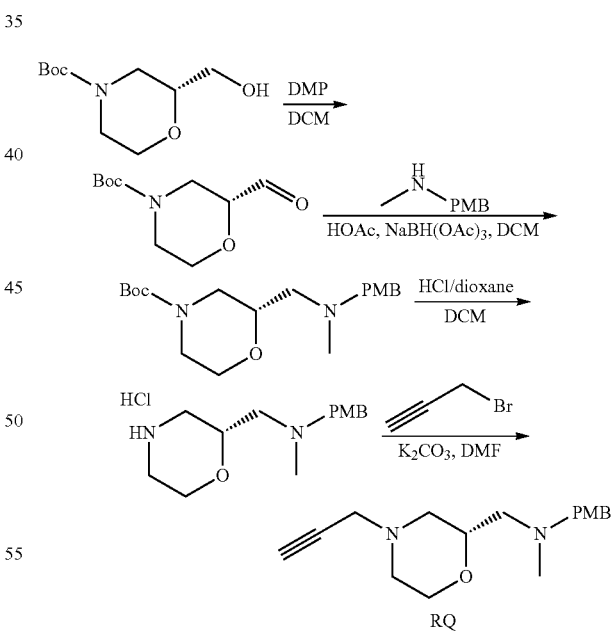

Step 1-Tert-butyl (2R)-2-formylmorpholine-4-carboxylate

To a solution of tert-butyl (2R)-2-(hydroxymethyl)morpholine-4-carboxylate (2.00 g, 9.21 mmol, CAS #135065-71-3) in DCM (40 mL) was added DMP (4.69 g, 11.0 mmol) at 0° C. The reaction mixture was stirred at 25° C. for 2 hours. On completion, the mixture was quenched with aq. Na₂S₂O₃ (50 mL) and aq. NaHCO₃ (50 mL). The mixture was stirred for 15 minutes and extracted with EA (2×50 mL). The organic layer was washed with brine (50 mL), dried with Na₂SO₄, and concentrated in vacuo to give the title compound (1.50 g, 76% yield) as colorless oil. ¹H NMR (400 MHz, CDCl₃) δ 9.65 (s, 1H), 4.08-4.00 (m, 1H), 3.95-3.85 (m, 2H), 3.83-3.75 (m, 1H), 3.68-3.53 (m, 2H), 3.12-3.03 (m, 1H), 1.47 (s, 9H).

Step 2—Tert-butyl (2S)-2-[[(4-methoxyphenyl)methyl-methyl-amino]methyl]morpholine-4-carboxylate To a solution of tert-butyl (2R)-2-formylmorpholine-4-carboxylate (1.5 g, 6.97 mmol) and 1-(4-methoxyphenyl)-N-methyl-methanamine (1.05 g, 6.97 mmol) in DCM (30 mL) was added HOAc (418 mg, 6.97 mmol) and the reaction was stirred at 25° C. Thirty minutes later, NaBH(OAc)₃ (1.77 g, 8.36 mmol) was added and the reaction mixture was stirred at 25° C. for 10 hours. On completion, the mixture was concentrated in vacuo. The residue was purified by reversed phase (0.1% FA) to give the title compound (1.4 g, 57% yield) as a yellow solid. ¹H NMR (300 MHz, CDCl₃) δ 7.22 (d, J=8.4 Hz, 2H), 6.85 (d, J=8.4 Hz, 2H), 4.07-3.94 (m, 1H), 3.93-3.83 (m, 2H), 3.90 (s, 3H), 3.58-3.43 (m, 4H), 3.01-2.80 (m, 1H), 2.62-2.46 (m, 2H), 2.41-2.31 (m, 1H), 2.26 (s, 3H), 1.48 (s, 9H); LC-MS (ESI⁺) m/z 351.1 (M+H)⁺.

Step 3—1-(4-Methoxyphenyl)-N-methyl-N-[[(2R)-morpholin-2-yl]methyl]methanamine hydrochloride To a solution of tert-butyl (2S)-2-[[(4-methoxyphenyl)methyl-methyl-amino]methyl]morpholine-4-carboxylate (1.40 g, 3.99 mmol) in HCl/dioxane (10 mL) was added DCM (10 mL). The reaction mixture was stirred at 25° C. for 2 hours. On completion, the mixture was concentrated in vacuo to give the title compound (1.15 g, 100% yield, HCl) as a yellow solid. LC-MS (ESI⁺) m/z 251.1 (M+H)⁺.

Step 4—1-(4-methoxyphenyl)-N-methyl-N-[[(2S)-4-prop-2-ynylmorpholin-2-yl]methyl]methanamine To a solution of 1-(4-methoxyphenyl)-N-methyl-N-[[(2R)-morpholin-2-yl]methyl]methanamine (1.15 g, 4.01 mmol, HCl) and 3-bromoprop-1-yne (525 mg, 4.41 mmol) in DMF (20 mL) was added K₂CO₃ (1.66 g, 12.0 mmol). The reaction mixture was stirred at 25° C. for 12 hours. On completion, the mixture was diluted with water (100 mL), and extracted with EA (2×50 mL). The organic layer was washed with brine (100 mL), then concentrated in vacuo. The residue was purified by reversed phase chromatography (0.1% FA condition) to give the title compound (700 mg, 61% yield) as colourless oil. LC-MS (ESI⁺) m/z 289.2 (M+H)⁺.

3-[3-Methyl-5-[3-[(2S)-2-(methylaminomethyl)morpholin-4-yl]propyl]-2-oxo-benzimidazol-1-yl]piperidine-2,6-dione (Intermediate RR)

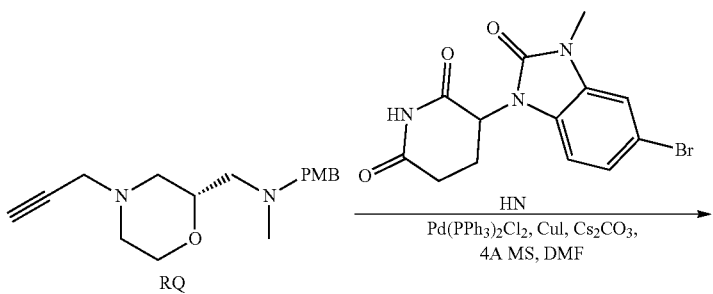

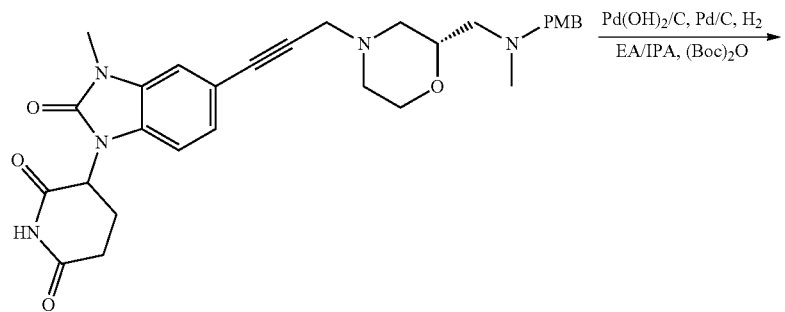

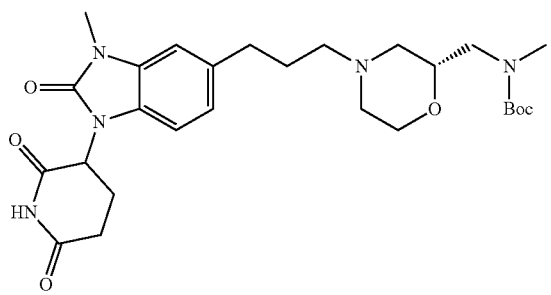

1325

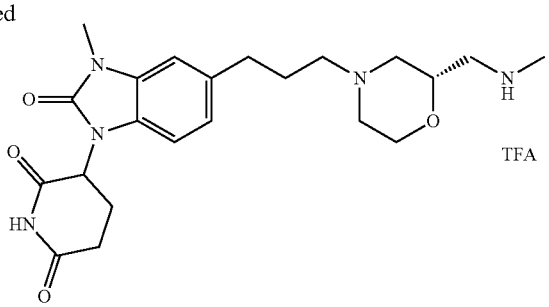

1326

-continued

RR

Step 1—3-[5-[3-[(2S)-2-[[(4-methoxyphenyl) methyl-methyl-amino]methyl]morpholin-4-yl]prop-1-ynyl]-3-methyl-2-oxo-benzimidazol-1-yl]piperidine-2,6-dione 1-(4-methoxyphenyl)-N-methyl-N-[[(2S)-4-prop-2-ynylmorpholin-2-yl]methyl]methanamine (1.01 g, 3.51 mmol, Intermediate RQ), 3-(5-bromo-3-methyl-2-oxo-benzimidazol-1-yl)piperidine-2,6-dione (660 mg, 1.95 mmol, Intermediate HN), Pd(PPh$_3$)$_2$Cl$_2$ (274 mg, 390 umol), CuI (74.3 mg, 390 umol), 4 Å molecular sieves (200 mg) and Cs$_2$CO$_3$ (2.54 g, 7.81 mmol) in DMF (12 mL) was degassed with N$_2$ and then heated at 80° C. for 2 hours under N$_2$. On completion, the mixture was filtered and the filtrate was concentrated in vacuo and purified by prep-HPLC (column: Phenomenex luna C18 250*50 mm*10 um; mobile phase: [water (0.225% FA)-ACN]; B %: 5%-35%, 28 mins) to give the title compound (850 mg, 80% yield) as a yellow solid. $^1$H NMR (400 MHz, DMSO-d$_6$) δ 11.13 (s, 1H), 7.33-7.23 (m, 3H), 7.17-7.12 (m, 2H), 6.89-6.84 (m, 2H), 5.44-5.35 (m, 1H), 3.87-3.79 (m, 1H), 3.78-3.72 (m, 1H), 3.71-3.69 (m, 3H), 3.68-3.56 (m, 4H), 3.53 (s, 2H), 3.34 (s, 3H), 2.93-2.80 (m, 1H), 2.74-2.60 (m, 2H), 2.30 (s, 3H), 2.28-2.24 (m, 1H), 2.21-2.18 (m, 1H), 2.18-2.15 (m, 1H), 2.05-2.00 (m, 2H), 1.98-1.96 (m, 1H); LC-MS (ESI$^+$) m/z 546.3 (M+H)$^+$.

Step 2—Tert-butyl N-[[(2R)-4-[3-[1-(2,6-dioxo-3-piperidyl)-3-methyl-2-oxo-benzimidazol-5-yl]propyl] morpholin-2-yl]methyl]-N-methyl-carbamate To a mixture of 3-[5-[3-[(2S)-2-[[(4-methoxyphenyl) methyl-methyl-amino]methyl]morpholin-4-yl] prop-1-ynyl]-3-methyl-2-oxo-benzimidazol-1-yl]piperidine-2,6-dione (200 mg, 367 umol) and (Boc)$_2$O (96.0 mg, 440 umol) in a mixed solvent of IPA (5 mL) and EA (10 mL) was added Pd(OH)$_2$/C (0.1 g, 20 wt %) and Pd/C (0.1 g, 10 wt %). The reaction mixture was stirred at 25° C. for 12 hours under H$_2$ (50 Psi) atmosphere. On completion, the mixture was filtered and the filtrate was concentrated in vacuo. The residue was purified by reversed phase (0.1% FA) to give the title compound (85.0 mg, 44% yield) as a white solid. LC-MS (ESI$^+$) m/z 530.3 (M+H)$^+$.

Step 3—3-[3-Methyl-5-[3-[(2S)-2-(methylaminomethyl)morpholin-4-yl]propyl]-2-oxo-benzimidazol-1-yl]piperidine-2,6-dione To a solution of tert-butyl N-[[(2R)-4-[3-[1-(2,6-dioxo-3-piperidyl)-3-methyl-2-oxo-benzimidazol-5-yl]propyl]morpholin-2-yl]methyl]-N-methyl-carbamate (85.0 mg, 160 umol) in DCM (3 mL) was added TFA (3 mL). The reaction mixture was stirred at 25° C. for 2 hours. On completion, the mixture was concentrated in vacuo to give the title compound (87.0 mg, 100% yield, TFA) as a yellow solid. LC-MS (ESI$^+$) m/z 430.3 (M+H)$^+$.

N-(4-Piperazin-1-ylcyclohexyl)-5-tetrahydropyran-4-yl-pyrrolo[2,1-f][1,2,4]triazin-4-amine (Intermediate OP)

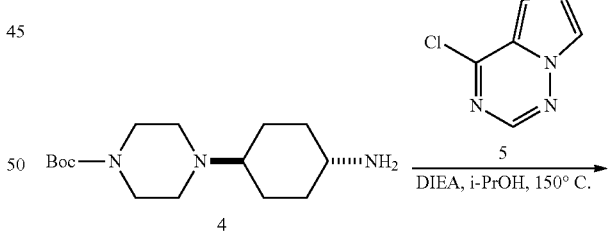

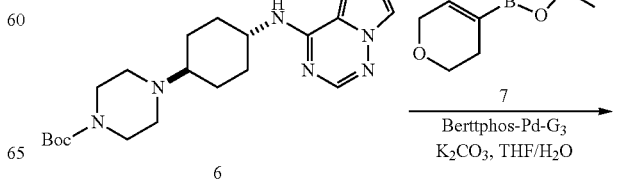

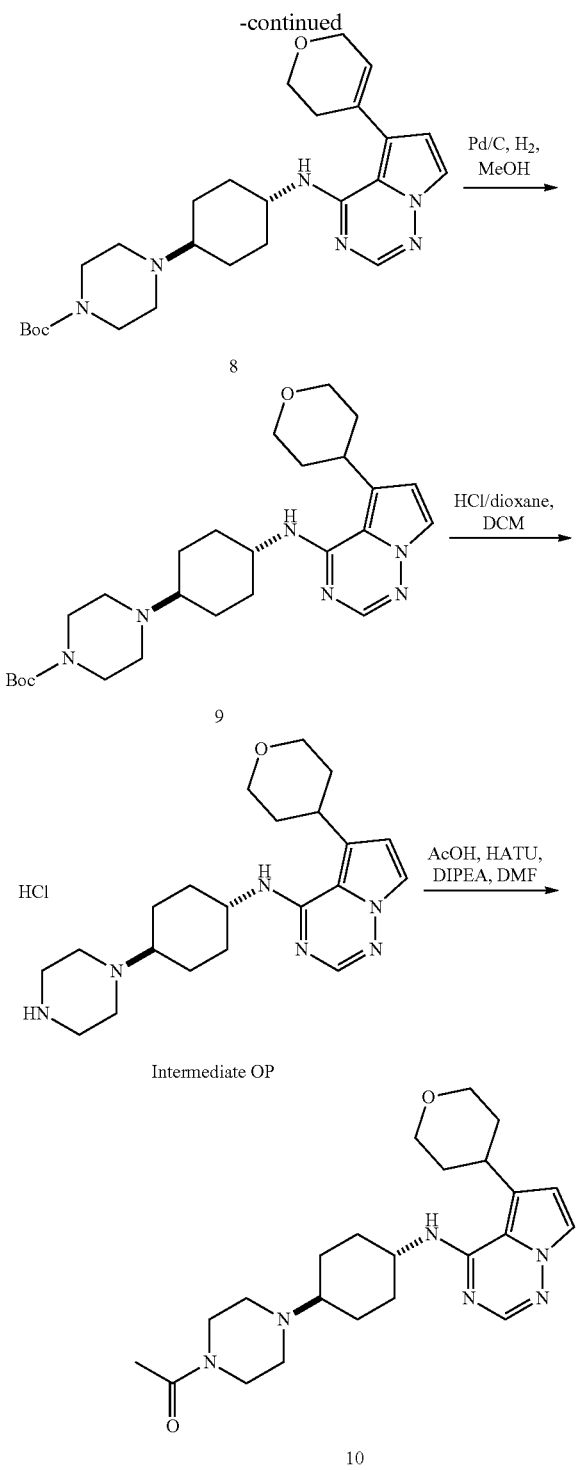

Step 1—Tert-butyl 4-(trans-4-(((benzyloxy)carbonyl)amino)cyclohexyl)piperazine-1-carboxylate (3)

The reaction was performed in parallel for two batches: to a solution of tert-butyl piperazine-1-carboxylate (24.0 g, 129 mmol) in DCM (400 mL) was added benzyl N-(4-oxocyclohexyl)carbamate (31.9 g, 129 mmol, CAS #16801-63-1), HOAc (3.15 g, 52.5 mmo) and NaBH(OAc)₃ (81.9 g, 387 mmol) successively at 0-10° C., and the mixture was stirred at 15° C. for 16 hours under N₂. On completion, the mixture of two batches was combined, basified to pH=8 with sat.aq-.NaHCO₃, and partitioned. The aqueous phase was extracted with DCM (2×200 mL). The combined organic layer was washed with brine (300 mL), dried over Na₂SO₄, filtered and concentrated in vacuum. The residue was purified by prep-HPLC (column: Phenomenex Gemini C18 250*50 mm*10 um; mobile phase: [water (0.05% ammonia hydroxide v/v)-ACN]; B %: 50%-75%,26 MIN, 40% min) to give two fractions. The first fraction is the title compound (20.0 g, 18% yield) as white solid. ¹H NMR (400 MHz, CDCl₃) δ ppm 7.46-7.29 (m, 5H), 5.09 (s, 2H), 4.57 (s, 1H), 3.43 (m, 5H), 2.50 (m, 4H), 2.28 (m, 1H), 2.10 (d, J=12.0 Hz, 2H), 1.90 (d, J=11.6 Hz, 2H), 1.46 (s, 9H), 1.40-1.27 (m, 2H), 1.22-1.08 (m, 2H). The second fraction is undesired cis-isomer (12.7 g, 11% yield).

Step 2—Tert-butyl 4-(trans-4-aminocyclohexyl)piperazine-1-carboxylate (4)

A mixture of tert-butyl 4-[4-(benzyloxycarbonylamino)cyclohexyl]piperazine-1-carboxylate (8.00 g, 16.4 mmol) and Pd/C (800 mg, 10% purity) in MeOH (80 mL) was stirred at 25° C. for 2 hours under H₂ (15 Psi). On completion, the mixture was filtered, and the cake was washed with MeOH (50 mL). The filtrate and washings were combined and concentrated in vacuum to give the title compound (5.3 g, crude) as white solid. ¹H NMR (400 MHz, CDCl₃) δ ppm 3.49-3.21 (m, 4H), 2.64-2.58 (m, 1H), 2.54 (m, 4H), 2.31-2.20 (m, 1H), 1.88 (t, J=15.2 Hz, 4H), 1.45 (s, 9H), 1.34-1.22 (m, 2H), 1.17-1.05 (m, 2H).

Step 3—Tert-butyl 4-[4-[(5-bromopyrrolo[2,1-f][1,2,4]triazin-4-yl)amino]cyclohexyl]piperazine-1-carboxylate (6)

5-bromo-4-chloro-pyrrolo[2,1-f] [1,2,4]triazine (250 mg, 1.08 mmol, CAS #1403767-33-8), DIPEA (555 mg, 4.30 mmol) and tert-butyl 4-(4-aminocyclohexyl)piperazine-1-carboxylate (350 mg, 1.23 mmol) were suspended in IPA (5 mL) under nitrogen and sealed into a microwave tube. The resulting suspension was heated to 150° C. for 3 hours under microwave irradiation. On completed, the mixture was concentrated in vacuo. The crude product was triturated with methanol (5 mL) to give the title compound (300 mg, 58% yield) as a white solid. ¹H NMR (400 MHz, DMSO-d₆) δ 7.92 (s, 1H), 7.72 (d, J=2.8 Hz, 1H), 6.80 (d, J=2.8 Hz, 1H), 6.61 (d, J=6.8 Hz, 1H), 4.08-4.00 (m, 1H), 3.32-3.20 (m, 4H), 2.93-2.91 (m, 1H), 2.45-2.41 (m, 2H), 2.11-2.07 (m, 2H), 1.84-1.80 (m, 1H), 1.57-1.16 (m, 16H); LC-MS (ESI⁺) m/z 481.2 & 479.2 (M+H)⁺.

Step 4—Tert-butyl 4-[4-[[5-(3,6-dihydro-2H-pyran-4-yl)pyrrolo[2,1-f][1,2,4]triazin-4-yl]amino] cyclohexyl]piperazine-1-carboxylate (8)

A mixture of tert-butyl 4-[4-[(5-bromopyrrolo[2,1-f][1,2,4]triazin-4-yl)amino]cyclohexyl]piperazine-1-carboxylate (300 mg, 625 umol), 2-(3,6-dihydro-2H-pyran-4-yl)-4,4,5,5-tetramethyl-1,3,2-dioxaborolane (394 mg, 1.88 mmol, CAS #287944-16-5), Brettphos-Pd-G₃ (56.7 mg, 62.5 umol) and K₂CO₃ (173 mg, 1.25 mmol) in a mixed solvent of THF (20 mL) and H₂O (4 mL) was degassed and purged with N₂ for 3 times, and then the mixture was stirred at 55° C. for 12 hrs under N₂ atmosphere. On completion, the reaction mixture was concentrated in vacuo. The residue was washed with water (60 mL), extracted with ethyl acetate (3×50 mL).

The organic layer was dried with Na₂SO₄, filtrated and concentrated in vacuo. The crude product was purified by reversed-phase HPLC (0.1% FA condition) to give the title compound (220 mg, 73% yield) as yellow oil. $^1$H NMR (400 MHz, DMSO-$d_6$) δ 7.89 (s, 1H), 7.62 (d, J=2.8 Hz, 1H), 6.66 (d, J=2.8 Hz, 1H), 6.20 (d, J=8.0 Hz, 1H), 5.82 (s, 1H), 4.22-4.19 (m, 2H), 3.98-3.94 (m, 1H), 3.84 (t, J=5.2 Hz, 2H), 3.28-3.26 (m, 4H), 2.46-2.44 (m, 4H), 2.36 (t, J=10.8 Hz, 1H), 2.10-2.07 (m, 2H), 1.83-1.80 (m, 2H), 1.39 (s, 9H), 1.37-1.23 (m, 4H); LC-MS (ESI⁺) m/z 483.4 (M+H)⁺.

Step 5—Tert-butyl 4-[4-[(5-tetrahydropyran-4-ylpyrrolo[2,1-f][1,2,4]triazin-4-yl)amino]cyclohexyl] piperazine-1-carboxylate (9)

To a solution of tert-butyl 4-[4-[[5-(3,6-dihydro-2H-pyran-4-yl)pyrrolo[2,1-f][1,2,4]triazin-4-yl] amino]cyclohexyl]piperazine-1-carboxylate (220 mg, 455 umol) in methanol (30 mL) was added Pd/C (100 mg, 10%, wt) under N₂. The suspension was degassed under vacuum and purged with H₂ several times. The mixture was stirred under H₂ (15 psi) at 25° C. for 16 hours. On completion, the reaction mixture was filtered. The filtrate was concentrated in vacuo to give the title compound (190 mg, 86% yield) as a white solid. $^1$H NMR (400 MHz, DMSO-$d_6$) δ 7.78 (s, 1H), 7.54 (d, J=2.8 Hz, 1H), 6.53 (d, J=2.8 Hz, 1H), 6.21 (d, J=8.0 Hz, 1H), 4.17-3.97 (m, 1H), 3.92-3.88 (m, 2H), 3.57-3.51 (m, 2H), 3.44-3.38 (m, 1H), 3.29-3.27 (m, 4H), 2.45-2.43 (m, 4H), 2.35-2.29 (m, 1H), 2.01-1.98 (m, 2H), 1.84-1.81 (m, 2H), 1.79-1.72 (m, 2H), 1.66-1.63 (m, 2H), 1.57-1.47 (m, 2H), 1.39 (s, 9H), 1.37-1.28 (m, 2H); LC-MS (ESI⁺) m/z 485.4 (M+H)⁺.

Step 6—N-(4-piperazin-1-ylcyclohexyl)-5-tetrahydropyran-4-yl-pyrrolo[2,1-f][1,2,4]triazin-4-amine (Intermediate OP)

To a solution of tert-butyl 4-[4-[(5-tetrahydropyran-4-ylpyrrolo[2,1-f][1,2,4]triazin-4-yl)amino] cyclohexyl]piperazine-1-carboxylate (180 mg, 345 umol) in DCM (3 mL) was added HCl/dioxane (4 M, 50 mL). The reaction mixture was stirred at 20° C. for 20 minutes. On completion, the mixture was filtered and concentrated in vacuo to give the title compound (145 mg, 99% yield) as a white solid. LC-MS (ESI⁺) m/z 385.3 (M+H)⁺.

Step 7—1-[4-[4-[(5-Tetrahydropyran-4-ylpyrrolo[2,1-f][1,2,4]triazin-4-yl)amino]cyclohexyl] piperazin-1-yl]ethanone (10)

To a solution of N-(4-piperazin-1-ylcyclohexyl)-5-tetrahydropyran-4-yl-pyrrolo[2,1-f][1,2,4]triazin-4-amine (153 mg, 363 umol, HCl salt) and AcOH (24.0 mg, 399 umol) in DMF (3 mL) was added HATU (165 mg, 436 umol). Then, DIPEA (187 mg, 1.45 mmol) was added. The reaction mixture was stirred at 20° C. for 0.5 hr. On completion, the reaction mixture was concentrated in vacuo. The crude product was purified by prep-HPLC (column: Phenomenex Synergi C18 150*25*10 um; mobile phase: [water (0.225% FA)-ACN]; B %: 3%-33%, 10 min) to give the title compound (94.0 mg, 61% yield) as white solid. $^1$H NMR (400 MHz, DMSO-$d_6$) δ 7.79 (s, 1H), 7.54 (d, J=2.8 Hz, 1H), 6.54 (d, J=2.8 Hz, 1H), 6.20 (d, J=8.0 Hz, 1H), 4.14-4.01 (m, 1H), 3.91 (dd, J=3.2, 10.8 Hz, 2H), 3.55 (t, J=10.8 Hz, 2H), 3.44-3.40 (m, 6H), 2.58-2.54 (m, 2H), 2.43-2.39 (m, 1H), 2.04-2.00 (m, 2H), 1.98 (s, 3H), 1.87-1.85 (m, 2H), 1.78-1.72 (m, 2H), 1.71-1.59 (m, 2H), 1.58-1.47 (m, 2H), 1.44-1.31 (m, 2H); LC-MS (ESI⁺) m/z 427.3 (M+H)⁺.

2-[2-[2-[2-[3-[1-(2,6-Dioxo-3-piperidyl)-3-methyl-2-oxo-benzimidazol-4-yl]propoxy] ethoxy]ethoxy] ethoxy]acetic acid (Intermediate RX)

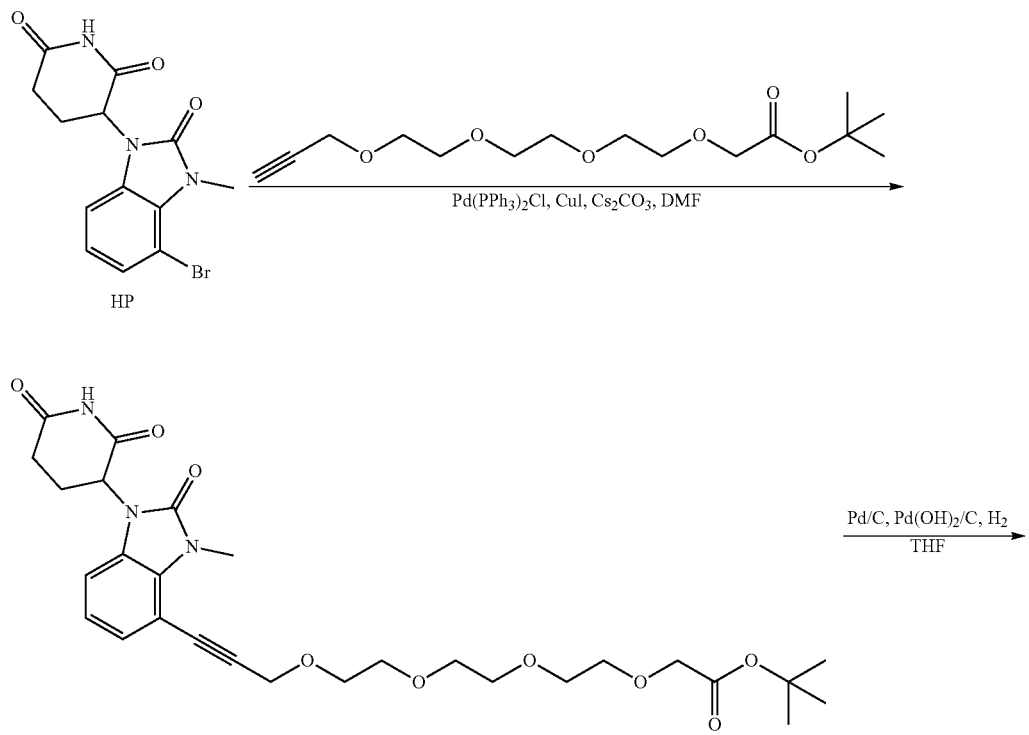

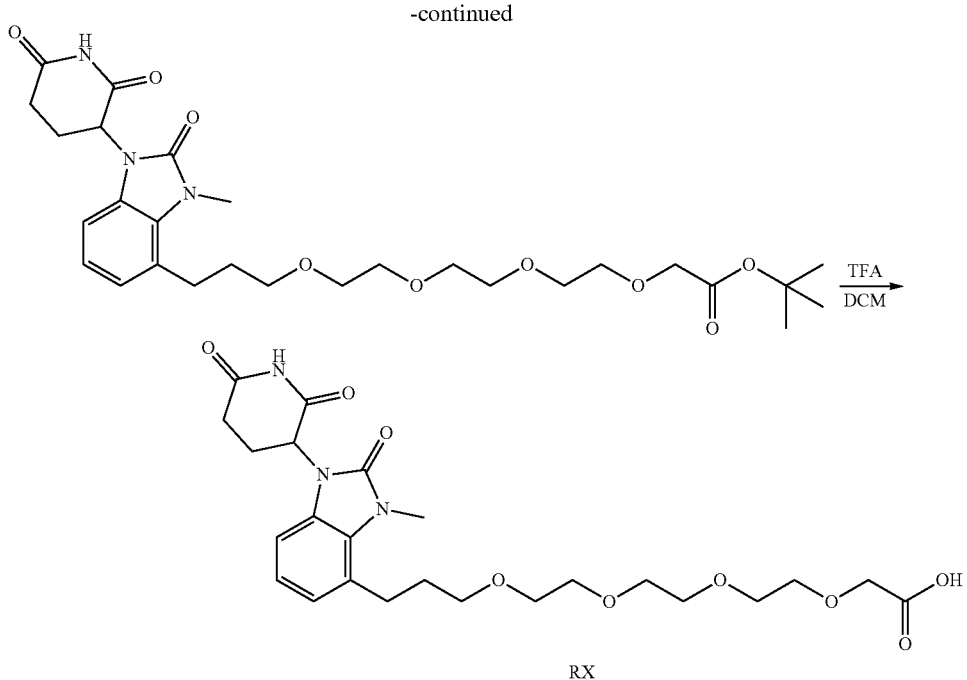

RX

Step 1—Tert-butyl 2-[2-[2-[2-[3-[1-(2,6-dioxo-3-piperidyl)-3-methyl-2-oxo-benzimidazol-4-yl]prop-2-ynoxy]ethoxy]ethoxy]ethoxy]acetate To a mixture of 3-(4-bromo-3-methyl-2-oxo-benzimidazol-1-yl)piperidine-2,6-dione (600 mg, 1.77 mmol, Intermediate HP), tert-butyl 2-[2-[2-(2-prop-2-ynoxyethoxy)ethoxy]ethoxy]acetate (1.07 g, 3.55 mmol, synthesized via Steps 1-2 of Example 441, I-447) in DMF (10 mL) was added CuI (67.6 mg, 355 umol), $Cs_2CO_3$ (2.89 g, 8.87 mmol) and $Pd(PPh_3)_2Cl_2$ (249.08 mg, 355 umol) under $N_2$. The reaction mixture was stirred at 80° C. for 3 hours. On completion, the mixture was poured into water (30 mL). The aqueous phase was extracted with ethyl acetate (2×30 mL). The combined organic phase was washed with brine (2×30 mL), dried with anhydrous $Na_2SO_4$, filtered and concentrated in vacuo to give a residue. The residue was purified by reversed-phase (0.1% FA condition) to give the title compound (598 mg, 60% yield) as brown oil. $^1$H NMR (400 MHz, $CDCl_3$) δ 8.29 (s, 1H), 7.16 (d, J=7.6 Hz, 1H), 6.97 (t, J=8.0 Hz, 1H), 6.75 (d, J=8.0 Hz, 1H), 5.23-5.15 (m, 1H), 4.46 (s, 2H), 4.01 (s, 2H), 3.76 (s, 3H), 3.76-3.66 (m, 12H), 2.99-2.68 (m, 3H), 2.29-2.16 (m, 1H), 1.46 (s, 9H).

Step 2—Tert-butyl 2-[2-[2-[2-[3-[1-(2,6-dioxo-3-piperidyl)-3-methyl-2-oxo-benzimidazol-4-yl]propoxy]ethoxy]ethoxy]ethoxy]acetate To a solution of tert-butyl 2-[2-[2-[2-[3-[1-(2,6-dioxo-3-piperidyl)-3-methyl-2-oxo-benzimidazol-4-yl] prop-2-ynoxy]ethoxy]ethoxy]ethoxy]acetate (578 mg, 1.03 mmol) in THF (5 mL) was added Pd/C (100 mg, 20 wt %) and $Pd(OH)_2$/C (100 mg, 20 wt %) under $N_2$. The suspension was degassed under vacuum and purged with $H_2$ gas three times. The mixture was stirred at 20° C. for 12 hours under $H_2$ (15 psi). On completion, the mixture was filtrated and the filtrate was concentrated in vacuo to give a title compound (540 mg, 92% yield) as brown oil. LC-MS (ESI$^+$) m/z 586.3 (M+Na)$^+$.

Step 3—2-[2-[2-[2-[3-[1-(2,6-Dioxo-3-piperidyl)-3-methyl-2-oxo-benzimidazol-4-yl]propoxy]ethoxy]ethoxy]ethoxy]acetic acid To a mixture of tert-butyl 2-[2-[2-[2-[3-[1-(2,6-dioxo-3-piperidyl)-3-methyl-2-oxo-benzimidazol-4-yl]propoxy]ethoxy]ethoxy]ethoxy]acetate (520 mg, 922 umol) in DCM (2 mL) was added TFA (210 mg, 1.85 mmol). The reaction mixture was stirred at 20° C. for 1 hour. On completion, the mixture was concentrated in vacuo to give a residue. The residue was purified by column chromatography to give the title compound (436 mg, 93% yield) as brown oil. LC-MS (ESI$^+$) m/z 508.3 (M+H)$^+$.

Tert-butyl 4-[4-[[5-bromo-7-(2-trimethylsilylethoxymethyl)pyrrolo[2,3-d]pyrimidin-4-yl] amino] cyclohexyl]piperazine-1-carboxylate (Intermediate RZ)

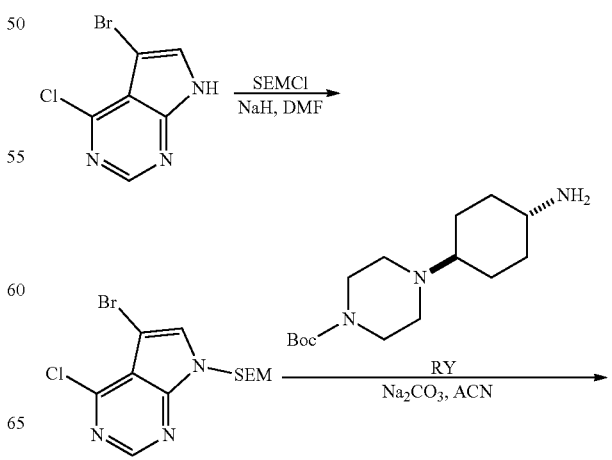

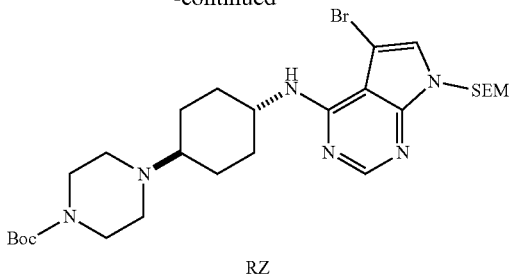

Step 1—2-[(5-Bromo-4-chloro-pyrrolo[2,3-d]pyrimidin-7-yl)methoxy]ethyl-trimethyl-silane NaH (205 mg, 5.13 mmol, 60% oil dispersion) was suspended in dimethylformamide (5 mL). The mixture was stirred for 10 min and then cooled at 0° C. in an ice bath. Then a solution of 5-bromo-4-chloro-7H-pyrrolo[2,3-d] pyrimidine (1.00 g, 4.30 mmol, CAS #22276-95-5) in dimethylformamide (5 mL) was added dropwise to the mixture, and the mixture was stirred for 30 minutes. Then a solution of 2-(chloromethoxy) ethyl-trimethyl-silane (0.900 g, 5.40 mmol) in dimethylformamide (5 mL) was added dropwise and the reaction mixture was stirred for 30 minutes at 0° C. On completion, the reaction mixture was quenched with water (30 mL), then extracted with ethyl acetate (3×30 mL). The combined organic layers were washed with brine (2×10 mL), dried over anhydrous sodium sulfate, filtered and concentrated in vacuo. The residue was purified by silica gel chromatography (PE:EA=3:1) to give the title compound (1.50 g, 96% yield) as a white solid. $^1$H NMR (400 MHz, CD3OD-d$_4$) δ 8.63 (s, 1H), 7.82 (s, 1H), 5.67 (s, 2H), 3.62-3.54 (m, 2H), 0.93-0.84 (m, 5H), −0.02-0.11 (m, 9H), LC-MS (ESI$^+$) m/z 363.9 & 361.9 (M+H)$^+$.

Step 2—Tert-butyl 4-[4-[[5-bromo-7-(2-trimethylsilylethoxymethyl)pyrrolo[2,3-d]pyrimidin-4-yl]amino] cyclohexyl]piperazine-1-carboxylate To a solution of 2-[(5-bromo-4-chloro-pyrrolo[2,3-d]pyrimidin-7-yl)methoxy]ethyl-trimethyl-silane (1.30 g, 3.58 mmol) and tert-butyl 4-(4-aminocyclohexyl)piperazine-1-carboxylate (1.02 g, 3.58 mmol, Intermediate RY) in ACN (30 mL) was added Na$_2$CO$_3$ (1.14 g, 10.7 mmol). The reaction mixture was stirred at 80° C. for 12 hours. On completion, the mixture was concentrated in vacuo, diluted with DCM (30 mL) and filtered. The filtrate was concentrated in vacuo. The residue was purified by silica gel chromatography (PE:EA=1:1) to give the title compound (1.30 g, 56% yield) as yellow oil. $^1$H NMR (400 MHz, CDCl$_3$) δ 8.34 (s, 1H), 7.05 (s, 1H), 5.89 (d, J=8.0 Hz, 1H), 5.52 (s, 2H), 4.14 (q, J=7.2 Hz, 2H), 3.58-3.49 (m, 2H), 3.45 (d, J=4.8 Hz, 5H), 2.56-2.54 (m, 4H), 2.44-2.40 (m, 1H), 2.33-2.30 (m, 2H), 1.98-1.94 (m, 2H), 1.71-1.63 (m, 1H), 1.58-1.50 (m, 2H), 1.42-1.31 (m, 2H), 1.02-0.86 (m, 2H), −0.03 (s, 9H). LC-MS (ESI$^+$) m/z 611.0 & 609.0 (M+H)$^+$.

N-(4-Piperazin-1-ylcyclohexyl)-5-tetrahydropyran-4-yl-7H-pyrrolo[2,3-d]pyrimidin-4-amine (Intermediate SA)

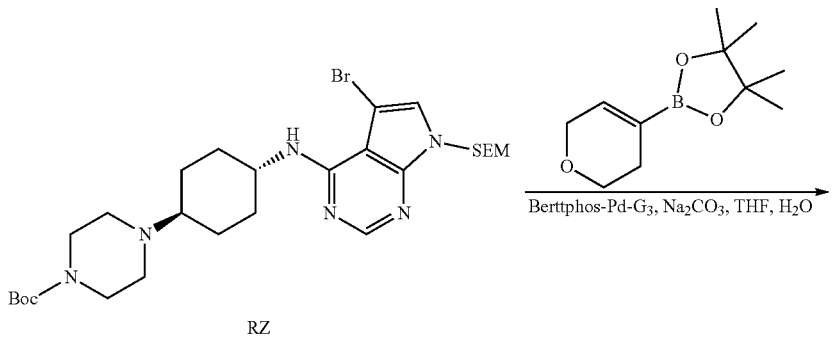

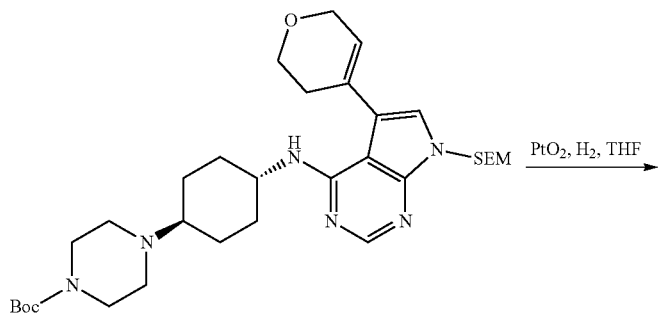

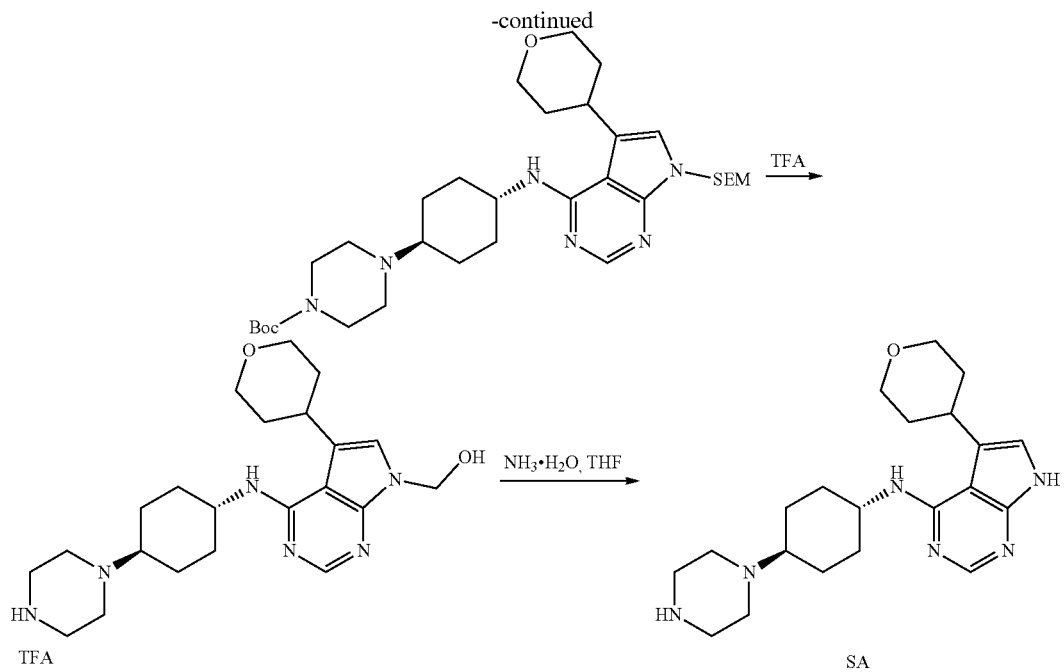

Step 1—Tert-butyl 4-[4-[[5-(3,6-dihydro-2H-pyran-4-yl)-7-(2-trimethylsilylethoxymethyl)pyrrolo[2,3-d]pyrimidin-4-yl]amino]cyclohexyl]piperazine-1-carboxylate A mixture of tert-butyl 4-[4-[[5-bromo-7-(2-trimethylsilylethoxymethyl)pyrrolo[2,3-d]pyrimidin-4-yl]amino]cyclohexyl]piperazine-1-carboxylate (1.00 g, 1.64 mmol Intermediate RZ), 2-(3,6-dihydro-2H-pyran-4-yl)-4,4,5,5-tetramethyl-1,3,2-dioxaborolane (1.03 g, 4.92 mmol), [2-(2-aminophenyl) phenyl]-methylsulfonyloxy-palladiumdicyclohexyl-[3,6-dimethoxy-2-(2,4,6-triisopropylphenyl)phenyl]phosphane (150 mg, 165 umol) and Na$_2$CO$_3$ (350 mg, 3.30 mmol) in a mixed solvent of THF (20 mL) and H$_2$O (4 mL) was stirred at 55° C. for 16 hours. On completion, the mixture was cooled to 25° C., and diluted with water (100 mL) and extracted with EA (3×50 mL). The combined organic layers were washed with brine (20 mL), dried over Na$_2$SO$_4$, filtered and the filtrate was concentrated in vacuo. The residue was purified by column chromatography (SiO$_2$, PE:EA=5:1-1:1) to give the title compound (0.95 g, 94% yield) as a light yellow gum. $^1$H NMR (400 MHz, CDCl$_3$) δ 8.36 (s, 1H), 6.96 (s, 1H), 5.85 (s, 1H), 5.54 (s, 2H), 5.35 (d, J=8.0 Hz, 1H), 4.34 (m, 2H), 3.96 (t, J=5.6 Hz, 2H), 3.59-3.51 (m, 2H), 3.44 (m, 4H), 2.53 (m, 6H), 2.27 (d, J=10.4 Hz, 2H), 1.98-1.91 (m, 2H), 1.52 (s, 2H), 1.47 (s, 9H), 1.24-1.20 (m, 4H), 0.94-0.89 (m, 2H), −0.04 (s, 9H).

Step 2—Tert-butyl 4-[4-[[5-tetrahydropyran-4-yl-7-(2-trimethylsilylethoxymethyl)pyrrolo[2,3-d]pyrimidin-4-yl]amino] cyclohexyl]piperazine-1-carboxylate A mixture of tert-butyl 4-[4-[[5-(3,6-dihydro-2H-pyran-4-yl)-7-(2-trimethylsilylethoxymethyl)pyrrolo[2,3-d]pyrimidin-4-yl]amino]cyclohexyl]piperazine-1-carboxylate (1.04 g, 1.70 mmol) and PtO$_2$ (200 mg, 880 umol) in THF (20 mL) was stirred at 25° C. for 36 hours under H$_2$ (15 Psi). On completion, the mixture was filtered and the filter cake was washed with EA (10 mL). The filtrate and washing were combined and concentrated in vacuo to give the title compound (1.00 g, 95% yield) as a light yellow gum. H NMR (400 MHz, CDCl$_3$) δ 8.34 (s, 1H), 6.81 (s, 1H), 5.52 (s, 2H), 4.73 (d, J=7.6 Hz, 1H), 4.16-4.10 (m, 4H), 3.62-3.54 (m, 2H), 3.45 (m, 4H), 2.54 (m, 4H), 2.32 (d, J=12.4 Hz, 2H), 2.01-1.92 (m, 4H), 1.83-1.73 (m, 2H), 1.53 (m, 3H), 1.47 (s, 9H), 1.25 (m, 4H), 0.92-0.86 (m, 2H), −0.05 (s, 9H).

Step 3—[4-[(4-Piperazin-1-ylcyclohexyl)amino]-5-tetrahydropyran-4-yl-pyrrolo[2,3-d]pyrimidin-7-yl] methanol A mixture of tert-butyl 4-[4-[[5-tetrahydropyran-4-yl-7-(2-trimethylsilylethoxymethyl) pyrrolo[2,3-d] pyrimidin-4-yl] amino]cyclohexyl]piperazine-1-carboxylate (1.00 g, 1.63 mmol) in TFA (10 mL) was stirred at 25° C. for 0.5 hour. On completion, the mixture was concentrated in vacuo to give the title compound (900 mg, TFA) as a yellow gum. LC-MS (ESI$^+$) m/z 415.3 (M+H)$^+$.

Step 4—N-(4-Piperazin-1-ylcyclohexyl)-5-tetrahydropyran-4-yl-7H-pyrrolo[2,3-d]pyrimidin-4-amine To a solution of [4-[(4-piperazin-1-ylcyclohexyl) amino]-5-tetrahydropyran-4-yl-pyrrolo[2,3-d] pyrimidin-7-yl] methanol (900 mg, 1.63 mmol, TFA) in THF (5 mL) was added NH$_3$.H$_2$O (10 mL) at 25° C. The mixture was stirred at 25° C. for 16 hours. On completion, the mixture was concentrated in vacuo. The residue was purified by reversed phase chromatography (FA condition) to give the title compound (300 mg, 62% yield over two steps) as a light yellow solid. $^1$H NMR (400 MHz, CDCl$_3$) δ 10.5 (s, 1H), 8.78 (s, 1H), 7.75 (s, 1H), 4.66-4.58 (m, 3H), 3.57 (t, J=10.4 Hz, 2H), 2.92-2.84 (m, 5H), 2.65-2.53 (m, 4H), 2.42-2.23 (m, 3H), 2.01-1.91 (m, 4H), 1.83-1.70 (m, 4H), 1.60-1.45 (m, 2H), 1.25-1.16 (m, 2H).

2-[4-[4-[1-(2,6-Dioxo-3-piperidyl)-3-methyl-2-oxo-benzimidazol-5-yl]butoxy]butylamino] acetic acid
(Intermediate SB)

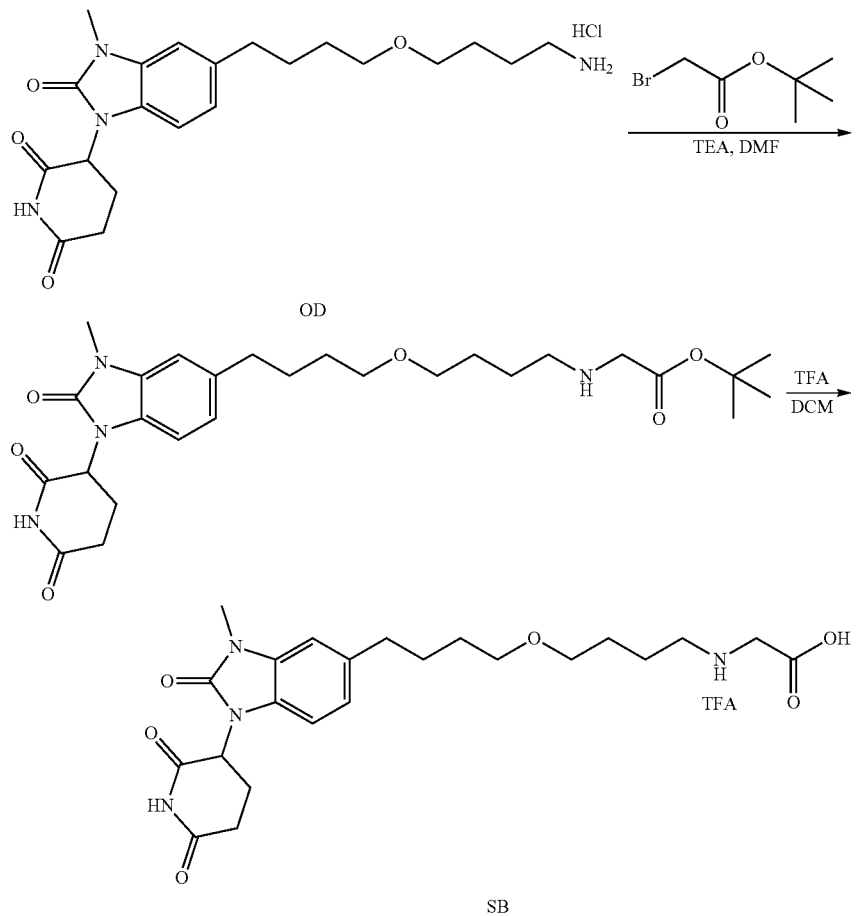

Step 1—Tert-butyl 2-[4-[4-[1-(2,6-dioxo-3-piperidyl)-3-methyl-2-oxo-benzimidazol-5-yl]butoxy]butylamino]zacetate A mixture of 3-[5-[4-(4-aminobutoxy)butyl]-3-methyl-2-oxo-benzimidazol-1-yl]piperidine-2,6-dione (200 mg, 455 umol, HCl, Intermediate OD), tert-butyl 2-bromoacetate (80.0 mg, 410 umol, CAS #5292-43-3) and TEA (100 mg, 988 umol) in DMF (2 mL) was stirred at 25° C. for 16 hours. On completion, the mixture was purified by reverse phase flash chromatography (FA condition) to give the title compound (100 mg, 31% yield) as light yellow gum. $^1$H NMR (400 MHz, DMSO-$d_6$) δ 11.09 (s, 1H), 7.02-6.98 (m, 2H), 6.86 (d, J=8.0 Hz, 1H), 5.37-5.28 (m, 1H), 3.62-3.57 (m, 2H), 3.34 (s, 3H), 3.32 (m, 4H), 2.91-2.83 (m, 1H), 2.65-2.56 (m, 6H), 2.04-1.95 (m, 1H), 1.77-1.73 (m, 1H), 1.63-1.47 (m, 8H), 1.41 (s, 9H).

Step 2—2-[4-[4-[1-(2,6-Dioxo-3-piperidyl)-3-methyl-2-oxo-benzimidazol-5-yl]butoxy]butylamino] acetic acid To a solution of tert-butyl 2-[4-[4-[1-(2,6-dioxo-3-piperidyl)-3-methyl-2-oxo-benzimidazol-5-yl] butoxy]butylamino]acetate (125 mg, 176 umol) in DCM (2 mL) was added TFA (1 mL) at 25° C. The mixture was stirred at 25° C. for 6 hours. On completion, the mixture was concentrated in vacuo to give the title compound (120 mg, crude, TFA) as yellow gum. LC-MS (ESI$^+$) m/z 461.2 (M+H)$^+$.

Tert-butyl N-[4-(but-3-yn-1-yloxy)butyl]carbamate
(Intermediate OI)

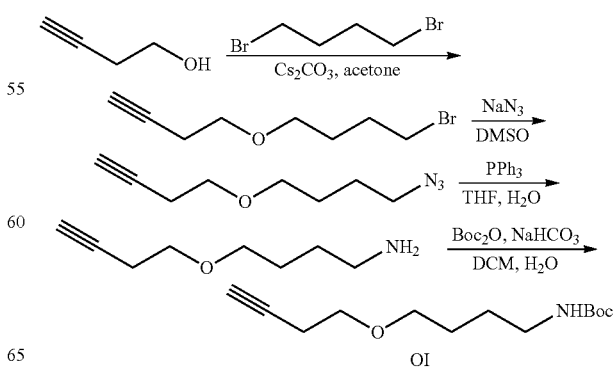

Step 1—4-(4-Bromobutoxy)but-1-yne

To a stirred solution of 1,4-dibromobutane (201 g, 933 mmol) in acetone (1 L) were added $Cs_2CO_3$ (223 g, 685 mmol) and but-3-yn-1-ol (43.6 g, 622.05 mmol) at rt. The resulting mixture was stirred for 16 h at rt under nitrogen atmosphere. After filtration, the filter cake was washed with acetone (2×50 mL). The filtrate was concentrated under reduced pressure. The residue was purified by silica gel column chromatography, eluted with 1% ethyl acetate in petroleum ether to afford 4-(4-bromobutoxy)but-1-yne (29 g, 23%) as a light yellow oil. $^1$H NMR (400 MHz, $CDCl_3$) δ 3.54 (t, J=6.9 Hz, 2H), 3.49 (t, J=6.2 Hz, 2H), 3.44 (t, J=6.6 Hz, 2H), 2.45 (td, J=7.0, 2.6 Hz, 2H), 2.02-1.88 (m, 3H), 1.80-1.65 (m, 2H).

Step 2—4-(4-Azidobutoxy)but-1-yne

A mixture of 4-(4-bromobutoxy)but-1-yne (29 g, 141 mmol) and $NaN_3$ (14 g, 212 mmol) in DMSO (300 mL) was stirred for 4 h at rt under nitrogen atmosphere. The resulting mixture was diluted with ice water (1 L) and extracted with petroleum ether/EtOAc (5/1, v/v, 2×500 mL). The combined organic layers was washed with brine (500 mL) and dried over anhydrous $Na_2SO_4$. After filtration, the filtrate was concentrated under reduced pressure to afford 4-(4-azidobutoxy)but-1-yne (22.2 g, 94%) as a light yellow oil: $^1$H NMR (400 MHz, $CDCl_3$) δ 3.53 (td, J=6.9, 1.6 Hz, 2H), 3.47 (td, J=6.0, 1.7 Hz, 2H), 3.29 (t, J=6.2 Hz, 2H), 2.44 (tt, J=7.0, 2.2 Hz, 2H), 1.97 (t, J=2.7 Hz, 1H), 1.73-1.57 (m, 4H); LC/MS (ESI, m/z): $[(2M+1)]^+$=335.25.

Step 3—4-(But-3-yn-1-yloxy)butan-1-amine

A solution of 4-(4-azidobutoxy)but-1-yne (22.2 g, 132.8 mmol) and $Ph_3P$ (52.2 g, 199.2 mmol) in THF (400 mL) and $H_2O$ (80 mL) was stirred for 4 h at 50° C. under nitrogen atmosphere. The resulting mixture was cooled and concentrated under reduced pressure to remove THF. The residue was acidified to pH=1 with 4 M aqueous HCl. The resulting mixture was extracted with EtOAc (2×500 mL). The water layer was neutralized to pH=7 with 2 M aqueous NaOH, and extracted with DCM (2×500 mL). The combined organic layers was washed with brine (500 mL) and dried over anhydrous $Na_2SO_4$. After filtration, the filtrate was concentrated under reduced pressure to afford crude product (18 g). LC/MS (ESI, m/z): $[(M+1)]^+$=142.1.

Step 4—Tert-butyl N-[4-(but-3-yn-1-yloxy)butyl]carbamate

To a stirred solution of 4-(but-3-yn-1-yloxy)butan-1-amine (18 g, 127.5 mmol) in DCM (500 mL) and $H_2O$ (500 mL) were added $NaHCO_3$ (21.4 g, 254.9 mmol) and $Boc_2O$ (33.4 g, 152.9 mmol) at rt. The resulting mixture was stirred for 16 h at rt under nitrogen atmosphere. The resulting mixture was extracted with $CH_2Cl_2$ (2×500 mL). The combined organic layers was washed with brine (500 mL) and dried over anhydrous $Na_2SO_4$. After filtration, the filtrate was concentrated under reduced pressure. The residue was purified by silica gel column chromatography, eluted with 20% ethyl acetate in petroleum ether to afford tert-butyl N-[4-(but-3-yn-1-yloxy)butyl]carbamate (30 g, 98%) as a light yellow oil. $^1$H NMR (400 MHz, $CDCl_3$) δ 4.67 (s, 1H), 3.54 (td, J=6.9, 3.6 Hz, 2H), 3.51-3.42 (m, 2H), 3.13 (q, J=5.6, 4.7 Hz, 2H), 2.45 (dh, J=7.2, 4.0, 3.5 Hz, 2H), 1.98 (q, J=2.8 Hz, 1H), 1.58 (td, J=8.7, 7.7, 4.4 Hz, 4H), 1.42 (s, 9H); LC/MS (ESI, m/z): $[(M+1)]^+$=242.3.

3-[5-[4-(4-aminobutoxy)butyl]-3-methyl-2-oxo-benzimidazol-1-yl]piperidine-2,6-dione (Intermediate OD)

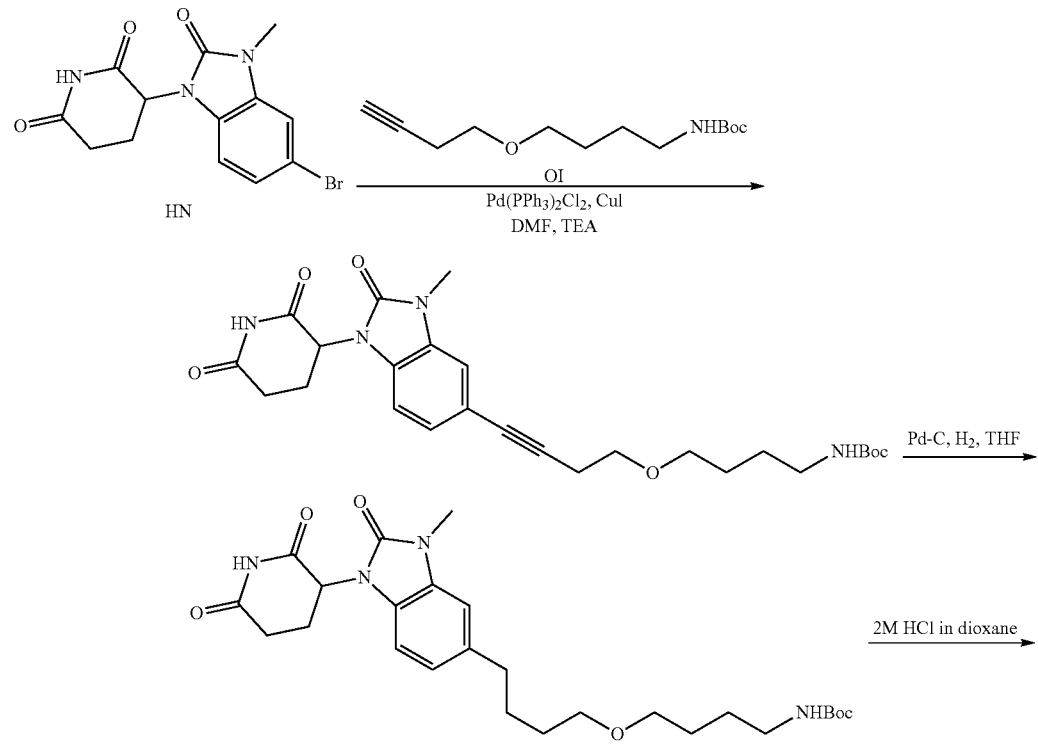

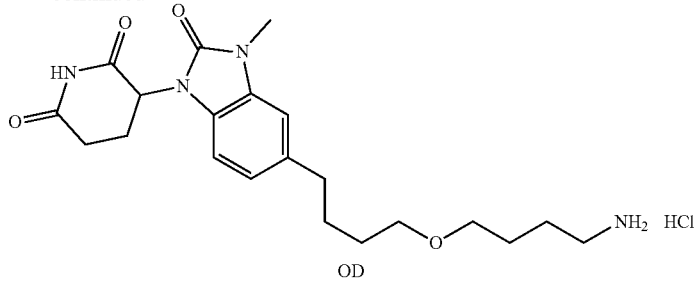

OD

Step 1-Tert-butyl N-[4-([4-[1-(2,6-dioxopiperidin-3-yl)-3-methyl-2-oxo-2,3-dihydro-1H-1,3-benzodiazol-5-yl]but-3-yn-1-yl] oxy)butyl] carbamate To a solution of 3-(5-bromo-3-methyl-2-oxo-2,3-dihydro-1H-1,3-benzodiazol-1-yl)piperidine-2,6-dione (2 g, 6 mmol, Intermediate HN) in DMSO (20 mL) were added tert-butyl N-[4-(but-3-yn-1-yloxy)butyl]carbamate (4.3 g, 18 mmol, Intermediate OI), Pd(PPh$_3$)$_4$ (683.4 mg, 0.59 mmol), CuI (225.3 mg, 1.18 mmol) and TEA (10 mL) at rt under nitrogen atmosphere. The resulting mixture was stirred for 16 h at 85° C. under nitrogen atmosphere. The reaction mixture was cooled to rt and concentrated under reduced pressure to remove the TEA. The resulting mixture was diluted with ice/water (50 ml, plus 3 ml AcOH) and extracted with EtOAc (2×50 mL). The combined organic layer was washed with brine (30 mL) and dried over anhydrous Na$_2$SO$_4$. After filtration, the filtrate was concentrated under reduced pressure. The residue was purified by reverse phase flash chromatography with the following conditions: Column: WelFlash™ C18-I, 20-40 μm, 330 g; Eluent A: Water (plus 10 mmol/L FA); Eluent B: ACN; Gradient: 5% B-5% B in 10 min; 50% B-60% B in 25 min; Flow rate: 80 mL/min; Detector: 220/254 nm; desired fractions were collected at 57% B and concentrated under reduced pressure to afford tert-butyl N-[4-([4-[1-(2,6-dioxopiperidin-3-yl)-3-methyl-2-oxo-2,3-dihydro-1H-1,3-benzodiazol-5-yl]but-3-yn-1-yl]oxy)butyl]carbamate (1.5 g, 51%) as a yellow solid. $^1$H NMR (400 MHz, DMSO-d$_6$) δ 11.12 (s, 1H), 7.24 (s, 1H), 7.10 (s, 1H), 6.79 (s, 1H), 5.41-5.34 (m, 1H), 3.55 (t, J=6.8 Hz, 2H), 3.44 (t, J=6.3 Hz, 2H), 3.32 (s, 3H), 2.96-2.88 (m, 3H), 2.71-2.65 (m, 4H), 2.11-2.00 (m, 1H), 1.49 (s, 2H), 1.48-1.40 (m, 2H), 1.37 (s, 9H); LC/MS (ESI, m/z): [M-1]$^-$=497.2.

Step 2—Tert-butyl N-(4-[4-[1-(2,6-dioxopiperidin-3-yl)-3-methyl-2-oxo-2,3-dihydro-1H-1,3-benzodiazol-5-yl]butoxy]butyl)carbamate To a solution of tert-butyl N-[4-([4-[1-(2,6-dioxopiperidin-3-yl)-3-methyl-2-oxo-2,3-dihydro-1H-1,3-benzodiazol-5-yl]but-3-yn-1-yl]oxy)butyl]carbamate (1.5 g, 3.01 mmol) in THF (50 mL) was added palladium on charcoal (0.15 g, 10% w/w) under nitrogen atmosphere. The mixture was hydrogenated at rt for 4 h using a hydrogen balloon. The resulting mixture was filtered through a celite pad and concentrated under reduced pressure to afford tert-butyl N-(4-[4-[1-(2,6-dioxopiperidin-3-yl)-3-methyl-2-oxo-2,3-dihydro-1H-1,3-benzodiazol-5-yl]butoxy]butyl)carbamate (1.2 g, 79%) as a white solid. $^1$H NMR (400 MHz, CDCl$_3$) δ 8.12 (br s, 1H), 6.94-6.89 (m, 1H), 6.87 (d, J=1.5 Hz, 1H), 6.73 (d, J=8.0 Hz, 1H), 5.23 (dd, J=12.5, 5.4 Hz, 1H), 4.73-4.60 (m, 1H), 3.49-3.36 (m, 7H), 3.15 (d, J=6.1 Hz, 2H), 2.97 (d, J=16.7 Hz, 1H), 2.87 (dd, J=13.3, 5.0 Hz, 1H), 2.70 (t, J=7.6 Hz, 2H), 2.32-2.19 (m, 1H), 1.76-1.50 (m, 9H), 1.46 (s, 9H); LC/MS (ESI, m/z): [M+1]$^+$=503.4.

Step 3—3-[5-[4-(4-Aminobutoxy)butyl]-3-methyl-2-oxo-2,3-dihydro-1H-1,3-benzodiazol-1-yl]piperidine-2,6-dione hydrochloride A solution of tert-butyl N-(4-[4-[1-(2,6-dioxopiperidin-3-yl)-3-methyl-2-oxo-2,3-dihydro-1H-1,3-benzodiazol-5-yl]butoxy]butyl)carbamate (150 mg, 0.29 mmol) in dioxane (2 mL) was treated with a solution of HCl (gas) in 1,4-dioxane (4 M, 2 mL) for 16 h at rt under nitrogen atmosphere. The resulting mixture was concentrated under reduced pressure to afford 3-[5-[4-(4-aminobutoxy)butyl]-3-methyl-2-oxo-2,3-dihydro-1H-1,3-benzodiazol-1-yl]piperidine-2,6-dione hydrochloride (100 mg, 77%) as a light yellow solid. $^1$H NMR (400 MHz, DMSO-d$_6$) δ 11.08 (s, 1H), 7.86 (br s, 3H), 7.05-6.98 (m, 2H), 6.87 (d, J=8.0 Hz, 1H), 5.35 (dd, J=12.7, 5.3 Hz, 1H), 3.74-3.63 (m, 1H), 3.57 (s, 1H), 3.49 (dd, J=11.6, 4.4 Hz, 1H), 3.42-3.33 (m, 4H), 2.97-2.85 (m, 1H), 2.82-2.59 (m, 6H), 2.06-1.96 (m, 1H), 1.67-1.48 (m, 8H); LC/MS (ESI, m/z): [(M+1)]$^+$=403.2.

5-Methyl-N-(4-piperazin-1-ylcyclohexyl)-7H-pyrrolo[2,3-d] pyrimidin-4-amine (Intermediate SC)

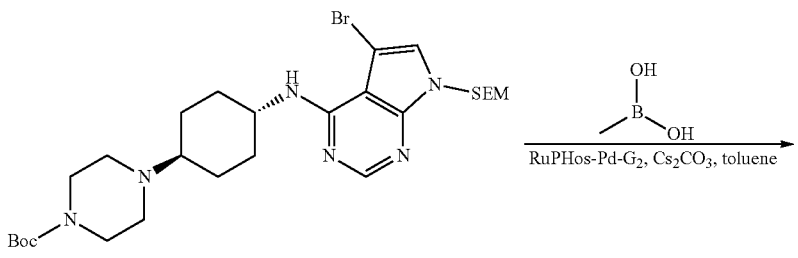

RZ

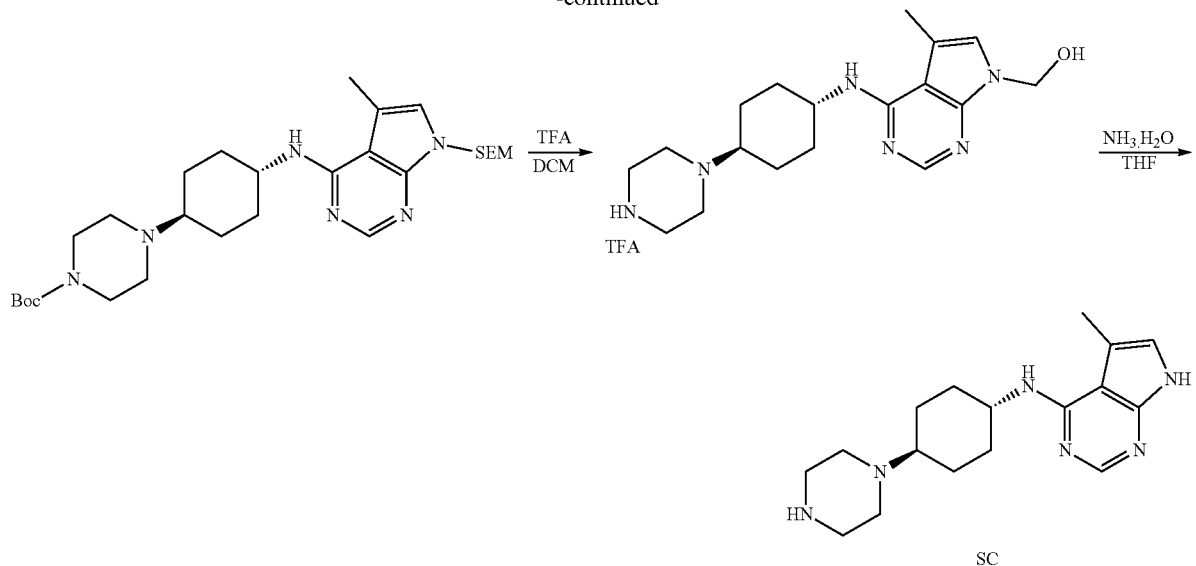

Step 1—Tert-butyl 4-[4-[[5-methyl-7-(2-trimethylsilylethoxymethyl)pyrrolo[2,3-d]pyrimidin-4-yl]amino]cyclohexyl]piperazine-1-carboxylate A mixture of tert-butyl 4-[4-[[5-bromo-7-(2-trimethylsilylethoxymethyl)pyrrolo[2,3-d]pyrimidin-4-yl] amino]cyclohexyl]piperazine-1-carboxylate (1.00 g, 1.64 mmol, Intermediate RZ), methylboronic acid (1.96 g, 32.8 mmol), $Cs_2CO_3$ (1.60 g, 4.91 mmol) and [2-(2-aminophenyl)phenyl]-chloro-palladium; dicyclohexyl-[2-(2,6-diisopropoxyphenyl)phenyl]-phosphane (140 mg, 180 umol, CAS #1375325-68-0) in toluene (20 mL) was stirred at 120° C. for 16 hours. On completion, after cooled to 25° C., the mixture was filtered and the cake was washed with EA (20 mL). The filtrate and washing were combined and concentrated in vacuo. The residue was purified by column chromatography over silica gel (PE:EA=20:1-1:1) to give the title compound (800 mg, 89% yield) as light yellow gum. $^1$H NMR (400 MHz, $CDCl_3$) δ 8.30 (s, 1H), 6.77 (s, 1H), 5.48 (s, 2H), 4.88 (d, J=8.0 Hz, 1H), 3.55-3.49 (m, 2H), 3.44-3.43 (m, 4H), 2.54 (s, 4H), 2.41 (s, 4H), 2.30 (d, J=11.2 Hz, 2H), 1.94 (d, J=12.4 Hz, 2H), 1.59-1.49 (m, 3H), 1.47 (s, 9H), 0.94-0.87 (m, 2H), −0.06 (s, 9H).

Step 2—[5-Methyl-4-[(4-piperazin-1-ylcyclohexyl)amino] pyrrolo[2,3-d]pyrimidin-7-yl] methanol To a solution of tert-butyl 4-[4-[[5-methyl-7-(2-trimethylsilylethoxymethyl) pyrrolo[2,3-d] pyrimidin-4-yl] amino] cyclohexyl]piperazine-1-carboxylate (700 mg, 1.28 mmol) in DCM (4 mL) was added TFA (4 mL) at 25° C. The mixture was stirred at 25° C. for 1 hour. On completion, the mixture was concentrated in vacuo to give the title compound (700 mg, crude, TFA) as light yellow gum. LC-MS (ESI$^+$) m/z 345.2 (M+H)$^+$.

Step 3—5-Methyl-N-(4-piperazin-1-ylcyclohexyl)-7H-pyrrolo[2,3-d] pyrimidin-4-amine To a solution of [5-methyl-4-[(4-piperazin-1-ylcyclohexyl)amino]pyrrolo[2,3-d]pyrimidin-7-yl] methanol (700 mg, TFA) in THF (4 mL) was added $NH_3H_2O$ (4 mL) at 25° C., and the mixture was stirred at 25° C. for 16 hours. On completion, the mixture was concentrated in vacuo. The residue was purified by prep-HPLC (column: Waters Xbridge 150*25 5 u; mobile phase: [water (10 mM $NH_4HCO_3$)-ACN]; B %: 5%-35%, 10 min) to give the title compound (120 mg, 40% yield) as white solid. $^1$H NMR (400 MHz, DMSO-$d_6$) δ 11.21-11.01 (m, 1H), 8.03 (s, 1H), 6.79 (s, 1H), 6.05 (m, 1H), 5.66-5.64 (m, 1H), 4.01-3.99 (m, 1H), 2.72-2.62 (m, 4H), 2.46-2.38 (m, 3H), 2.35 (s, 3H), 2.34-2.31 (m, 1H), 2.06-1.95 (m, 2H), 1.88-1.76 (m, 2H), 1.51-1.21 (m, 4H).

Tert-butyl N-[(1-but-3-ynyl-4-piperidyl)methyl]-N-methyl-carbamate (Intermediate SH)

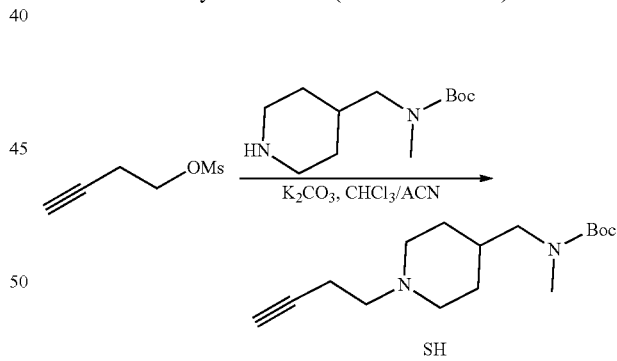

To a solution of tert-butyl N-methyl-N-(4-piperidylmethyl)carbamate (3.00 g, 13.1 mmol, CAS #138200-04-5) in a mixed solvent of $CHCl_3$ (25 mL) and ACN (25 mL) was added $K_2CO_3$ (3.63 g, 26.2 mmol) and but-3-ynyl methanesulfonate (2.53 g, 17.0 mmol, Intermediate SG). The mixture was stirred at 70° C. for 16 hours. On completion, the reaction mixture was filtered and concentrated in vacuo to give a residue. The residue was purified by column chromatography ($SiO_2$, PE/EA=6/1) to give the title compound (2.30 g, 62% yield) as light yellow oil. $^1$H NMR (400 MHz, $CDCl_3$) δ 3.09 (d, J=6.8 Hz, 2H), 2.97-2.97 (m, 2H), 2.84 (s, 3H), 2.59 (t, J=8.0 Hz, 2H), 2.45-2.32 (m, 2H), 2.04-1.93 (m, 3H), 1.65-1.55 (m, 3H), 1.45 (s, 9H), 1.30-1.20 (m, 2H).

3-[3-Methyl-5-[4-[4-(methylaminomethyl)-1-piperidyl]but-1-ynyl]-2-oxo-benzimidazol-1-yl]piperidine-2,6-dione (Intermediate SI)

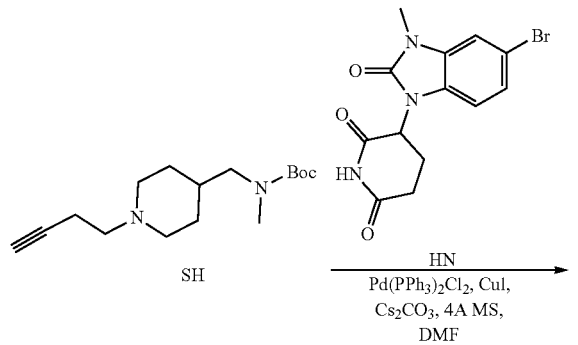

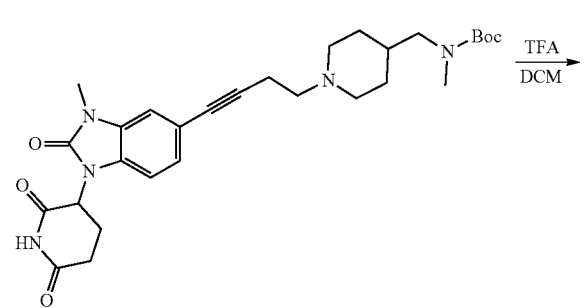

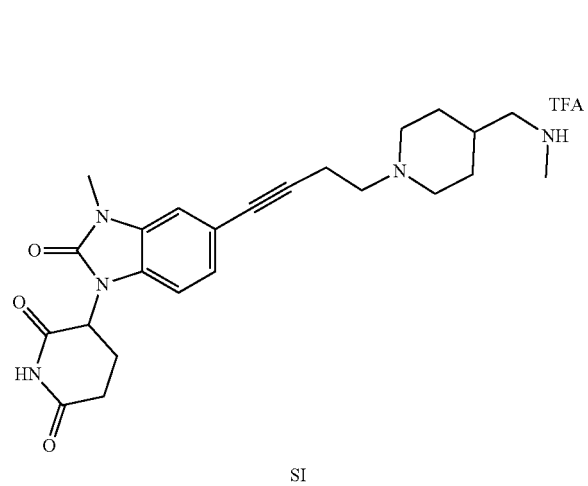

SI

Step 1—Tert-butyl N-[[1-[4-[1-(2,6-dioxo-3-piperidyl)-3-methyl-2-oxo-benzimidazol-5-yl]but-3-ynyl]-4-piperidyl]methyl]-N-methyl-carbamate To a solution of 3-(5-bromo-3-methyl-2-oxo-benzimidazol-1-yl)piperidine-2,6-dione (500 mg, 1.48 mmol, Intermediate HN) and tert-butyl N-[(1-but-3-ynyl-4-piperidyl)methyl]-N-methyl-carbamate (1.04 g, 3.70 mmol, Intermediate SH) in DMF (15 mL) was added Cs₂CO₃ (1.93 g, 5.91 mmol), CuI (56.3 mg, 295 umol), 4 Å molecular sieves (500 mg) and Pd(PPh₃)₂Cl₂ (207 mg, 295 umol). The mixture was stirred at 80° C. for 2 hours. On completion, the reaction mixture was filtered and concentrated in vacuo; the residue was diluted with water (30 mL), and then extracted with EA (3×40 mL). The combined organic layers were dried over Na₂SO₄, filtered and concentrated in vacuo to give a residue. The residue was purified by prep-HPLC (FA condition) to give the title compound (80.0 mg, 10% yield) as white solid. $^1$H NMR (400 MHz, DMSO-$d_6$) δ 8.16 (s, 1H), 7.14 (dd, J=1.6, 8.4 Hz, 1H), 7.07 (s, 1H), 6.72 (d, J=8.0 Hz, 1H), 5.19 (dd, J=5.6, 12.8 Hz, 1H), 3.42 (s, 3H), 3.12 (d, J=6.8 Hz, 2H), 3.07-2.92 (m, 3H), 2.89-2.81 (m, 4H), 2.80-2.58 (m, 5H), 2.29-2.21 (m, 1H), 2.19-2.00 (m, 2H), 1.46 (s, 9H), 1.39-1.24 (m, 2H); LC-MS (ESI$^+$) m/z 538.3 (M+H)$^+$.

Step 2—3-[3-Methyl-5-[4-[4-(methylaminomethyl)-1-piperidyl]but-1-ynyl]-2-oxo-benzimidazol-1-yl]piperidine-2,6-dione To a solution of tert-butyl N-[[1-[4-[1-(2,6-dioxo-3-piperidyl)-3-methyl-2-oxo-benzimidazol-5-yl]but-3-ynyl]-4-piperidyl]methyl]-N-methyl-carbamate (60.0 mg, 111 umol) in DCM (3 mL) was added TFA (924 mg, 8.10 mmol). The mixture was stirred at 30° C. for 1 hour. On completion, the reaction mixture was concentrated in vacuo to give the title compound (60.0 mg, 97% yield, TFA) as light yellow oil. LC-MS (ESI$^+$) m/z 438.3 (M+H)$^+$.

Tert-butyl N-methyl-N-(3-prop-2-ynoxypropyl)carbamate (Intermediate PO)

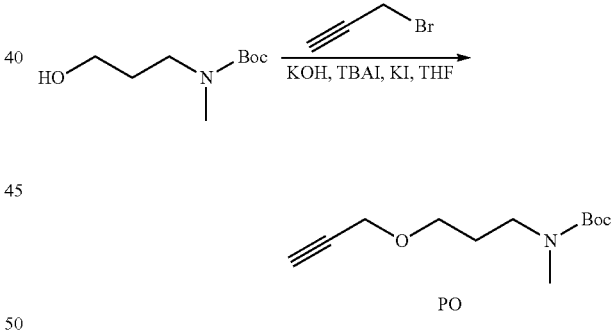

PO

To a solution of 3-bromoprop-1-yne (1.32 g, 11.1 mmol, CAS #106-96-7) and tert-butyl N-(3-hydroxypropyl)-N-methyl-carbamate (2.00 g, 10.6 mmol, CAS #98642-44-5) in THF (20 mL) was added TBAI (234 mg, 634 umol) and KI (263 mg, 1.59 mmol). Then KOH (698 mg, 10.6 mmol, 85% purity) was added into the above mixture. The reaction mixture was stirred at 25° C. for 12 hrs. On completion, the mixture was concentrated in vacuo to remove the solvent, the residue was diluted with water (30 mL), then extracted with EA (3×40 mL). The organic phase was dried over Na₂SO₄, filtered and the filtrate was concentrated in vacuo. The residue was purified by silica gel chromatography (SiO₂) to give the title compound (1.15 g, 48% yield) as colorless oil. $^1$H NMR (400 MHz, CDCl₃) δ 4.15-4.11 (m, 2H), 3.57-3.49 (m, 2H), 3.29 (t, J=6.8 Hz, 2H), 2.86 (s, 3H), 2.42 (t, J=2.4 Hz, 1H), 1.85-1.76 (m, 2H), 1.46 (s, 9H).

3-[3-Methyl-4-[3-[3-(methylamino)propoxy]propyl-2-oxo-benzimidazol-1-yl]piperidine-2,6-dione (Intermediate PP)

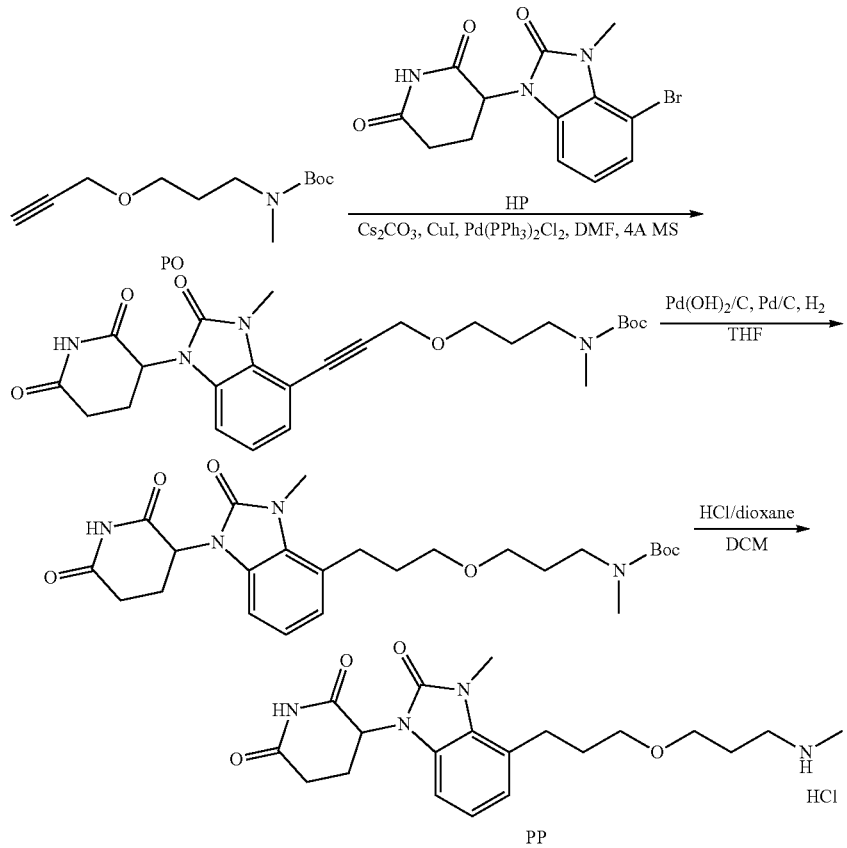

Step 1—Tert-butyl N-[3-[3-[1-(2,6-dioxo-3-piperidyl)-3-methyl-2-oxo-benzimidazol-4-yl]prop-2-ynoxy]propyl]-N-methyl-carbamate 3-(4-bromo-3-methyl-2-oxo-benzimidazol-1-yl)piperidine-2,6-dione (300 mg, 887 umol, Intermediate HP), tert-butyl N-methyl-N-(3-prop-2-ynoxypropyl)carbamate (504 mg, 2.22 mmol, Intermediate PO), Pd(PPh$_3$)$_2$Cl$_2$ (125 mg, 177 umol), Cs$_2$CO$_3$ (1.45 g, 4.44 mmol), CuI (33.8 mg, 177 umol) and 4 Å molecular sieves (150 mg) in DMF (8 mL) was heated at 80° C. for 2 hrs under N$_2$. On completion, the mixture was concentrated in vacuo. The residue was purified by reverse phase (0.1% FA condition) to give the title compound (200 mg, 40% yield) as a yellow solid. LC-MS (ESI$^+$) m/z 507.3 (M+Na)$^+$.

Step 2—Tert-butyl N-[3-[3-[1-(2,6-dioxo-3-piperidyl)-3-methyl-2-oxo-benzimidazol-4-yl]propoxy]propyl-N-methyl-carbamate To a solution of tert-butyl N-[3-[3-[1-(2,6-dioxo-3-piperidyl)-3-methyl-2-oxo-benzimidazol-4-yl] prop-2-ynoxy]propyl]-N-methyl-carbamate (200 mg, 351 umol) in THF (6 mL) was added Pd/C (0.100 g, 10% wt) and Pd(OH)$_2$/C (0.100 g, 10% wt). The reaction mixture was stirred at 25° C. for 10 hrs under H$_2$ (15 Psi) atmosphere. On completion, the mixture was filtered and the filtrate was concentrated in vacuo to give the title compound (200 mg, 93% yield) as a yellow solid. $^1$H NMR (400 MHz, DMSO-d$_6$) δ 11.10 (s, 1H), 7.00-6.92 (m, 2H), 6.90-6.84 (m, 1H), 5.44-5.24 (m, 1H), 3.56 (s, 3H), 3.44-3.40 (m, 4H), 3.22 (t, J=7.2 Hz, 2H), 2.99-2.92 (m, 2H), 2.76 (s, 3H), 2.74-2.69 (m, 1H), 2.65-2.58 (m, 2H), 2.04-1.96 (m, 1H), 1.87-1.79 (m, 2H), 1.74-1.65 (m, 2H), 1.38 (s, 9H); LC-MS (ESI$^+$) m/z 511.3 (M+Na)$^+$.

Step 3—3-[3-Methyl-4-[3-[3-(methylamino)propoxy]propyl-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-4-yl] propoxy]propyl]-N-methyl-carbamate (200 mg, 327 umol) in DCM (4 mL) was added HCl/dioxane (4 M, 3.20 mL). The reaction mixture was stirred at 25° C. for 2 hrs. On completion, the mixture was concentrated in vacuo to give the title compound (160 mg, 100% yield, HCl) as a white solid. $^1$H NMR (400 MHz, DMSO-d$_6$) δ 11.08 (s, 1H), 7.02-6.92 (m, 2H), 6.90-6.83 (m, 1H), 5.44-5.24 (dd, J=5.6, 12.4 Hz, 1H), 3.57 (s, 3H), 3.49-3.43 (m, 4H), 3.00-2.91 (m, 4H), 2.74-2.53 (m, 6H), 2.04-1.94 (m, 1H), 1.90-1.81 (m, 4H); LC-MS (ESI$^+$) m/z 389.2 (M+H)$^+$.

2-(4-Nitro-1H-pyrazol-3-yl)propan-2-ol (Intermediate TQ)

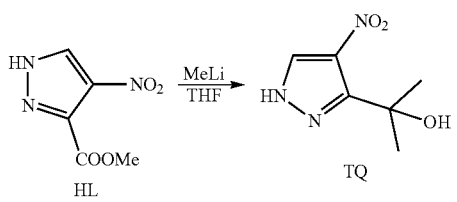

To a mixture of methyl 4-nitro-1H-pyrazole-3-carboxylate (11.0 g, 64.3 mmol, Intermediate HL) in dry THF (150 mL) was added MeLi (1.6 M in Et$_2$O, 100 mL) dropwise at −50° C. under N$_2$. The mixture was stirred and allowed to warm slowly to 0° C. After that, the reaction mixture was once more cooled to −50° C., and MeLi (1.6 M in Et$_2$O, 40.2 mL) was added, and the mixture was stirred and allowed to warm slowly to 25° C. On completion, the reaction mixture was quenched by saturated NH$_4$Cl (30 mL) at 25° C., and then extracted with EA (3×100 mL). The combined organic layers, dried over Na$_2$SO$_4$, filtered and concentrated in vacuo to give a residue. The residue was purified by column chromatography to give the title compound (2.70 g, 24% yield) as a brown solid. $^1$H NMR (400 MHz, DMSO-d$_6$) δ 13.51 (s, 1H), 8.27 (s, 1H), 5.86 (s, 1H), 1.58 (s, 6H).

2-(4-Nitro-1H-pyrazol-3-yl)propan-2-ol (Intermediate TQ)

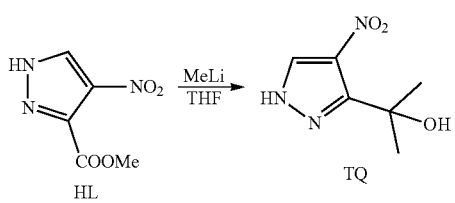

To a mixture of methyl 4-nitro-1H-pyrazole-3-carboxylate (11.0 g, 64.3 mmol, Intermediate HL) in dry THF (150 mL) was added MeLi (1.6 M in Et$_2$O, 100 mL) dropwise at −50° C. under N$_2$. The mixture was stirred and allowed to warm slowly to 0° C. After that, the reaction mixture was once more cooled to −50° C., and MeLi (1.6 M in Et$_2$O, 40.2 mL) was added, and the mixture was stirred and allowed to warm slowly to 25° C. On completion, the reaction mixture was quenched by saturated NH$_4$Cl (30 mL) at 25° C., and then extracted with EA (3×100 mL). The combined organic layers, dried over Na$_2$SO$_4$, filtered and concentrated in vacuo to give a residue. The residue was purified by column chromatography to give the title compound (2.70 g, 24% yield) as a brown solid. $^1$H NMR (400 MHz, DMSO-d$_6$) δ 13.51 (s, 1H), 8.27 (s, 1H), 5.86 (s, 1H), 1.58 (s, 6H).

Methyl 4-[4-amino-3-(1-hydroxy-1-methyl-ethyl)pyrazol-1-yl]cyclohexanecarboxylate (Intermediate TR)

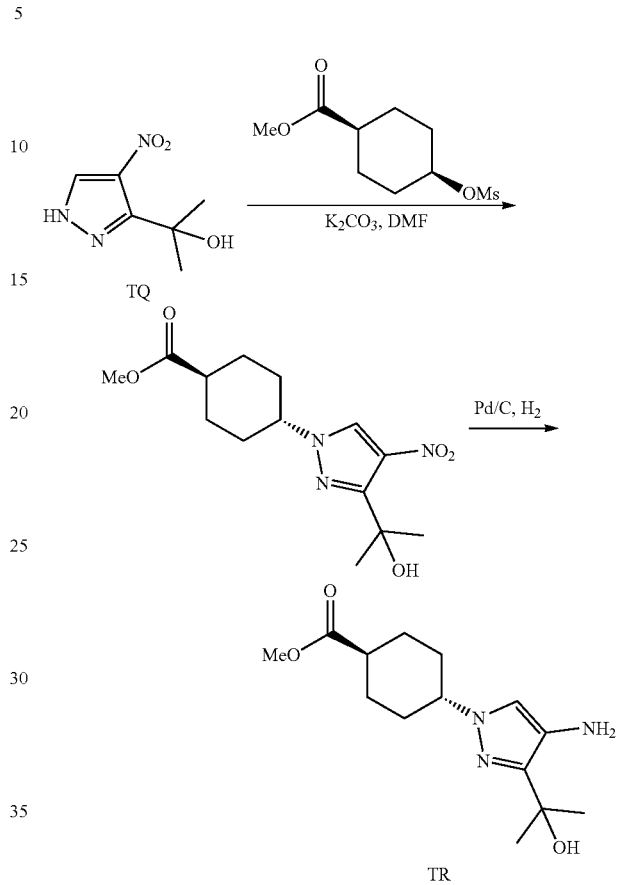

Step 1—Methyl 4-[3-(1-hydroxy-1-methyl-ethyl)-4-nitro-pyrazol-1-yl]cyclohexanecarboxylate To a mixture of 2-(4-nitro-1H-pyrazol-3-yl)propan-2-ol (100 mg, 584 umol, Intermediate TQ) and methyl 4-methylsulfonyloxycyclohexanecarboxylate (207 mg, 876 umol, synthesized via Step 1 of Intermediate QS) in DMF (3 mL) was added K$_2$CO$_3$ (323 mg, 2.34 mmol). The reaction mixture was stirred at 80° C. for 12 hours. On completion, the reaction mixture was poured into the ice-water (15 mL) and extracted with EA (2×20 mL). The combined organic phase was washed with brine (2×20 mL), dried with anhydrous Na$_2$SO$_4$, filtered and concentrated in vacuo to give residue. The residue was purified by prep-TLC (PE:EA=2:1) to give the title compound (90.0 mg, 49% yield) as brown solid. $^1$H NMR (400 MHz, CDCl$_3$) δ 8.23 (s, 1H), 4.10-4.04 (m, 1H), 3.71 (s, 3H), 2.46-2.35 (m, 1H), 2.33-2.25 (m, 2H), 2.25-2.16 (m, 2H), 1.82-1.68 (m, 3H), 1.67-1.61 (m, 8H).

Step 2—Methyl 4-[4-amino-3-(1-hydroxy-1-methyl-ethyl)pyrazol-1-yl]cyclohexanecarboxylate To a mixture of methyl 4-[3-(1-hydroxy-1-methyl-ethyl)-4-nitro-pyrazol-1-yl]cyclohexanecarboxylate (90.0 mg, 289 umol) in THF (20 mL) was added Pd/C (20 mg, 10 wt %) under N$_2$. The suspension was degassed under vacuum and purged with H$_2$ three times. The mixture was stirred at 25°

C. for 2 hours under H₂ (15 psi). On completion, the reaction mixture was filtered and the filtrate was concentrated in vacuo to give title compound (45.0 mg, 55% yield) as a brown solid. ¹H NMR (400 MHz, CDCl₃) δ 7.68 (s, 1H), 5.08 (s, 1H), 4.07-3.92 (m, 1H), 3.71 (s, 3H), 2.44-2.32 (m, 1H), 2.30-2.21 (m, 2H), 2.20-2.12 (m, 2H), 1.77-1.68 (m, 2H), 1.67-1.56 (m, 9H), 1.32-1.25 (m, 1H).

4-[4-[[2-[2-[Tert-butoxycarbonyl(cyclopropylmethyl)amino]-4-pyridyl]oxazole-4-carbonyl] amino]-3-(1-hydroxy-1-methyl-ethyl)pyrazol-1-yl]cyclohexanecarboxylic acid (Intermediate TS)

mg, 2.13 mmol). The mixture was stirred at 20° C. for 10 minutes. Then the HATU (324 mg, 853 umol) was added into the mixture. The reaction mixture was stirred at 20° C. for 1 hour. On completion, the reaction mixture quenched with 10 mL water and extracted with EtOAc (3×10 mL). The organic layer was dried with Na₂SO₄, filtrated and concentrated in vacuo to give title compound (250 mg, 56% yield) as brown solid. ¹H NMR (400 MHz, DMSO-d₆) δ 10.41 (s, 1H), 8.94 (s, 1H), 8.58 (d, J=5.2 Hz, 1H), 8.25-8.15 (m, 2H), 7.95 (s, 2H), 7.65 (d, J=1.2, 5.2 Hz, 1H), 5.83 (s, 1H), 3.85 (d, J=7.2 Hz, 2H), 3.61 (s, 3H), 2.89 (s, 6H), 2.68 (s, 3H), 1.52-1.49 (m, 15H), 0.43-0.37 (m, 2H), 0.27-0.20 (m, 2H).

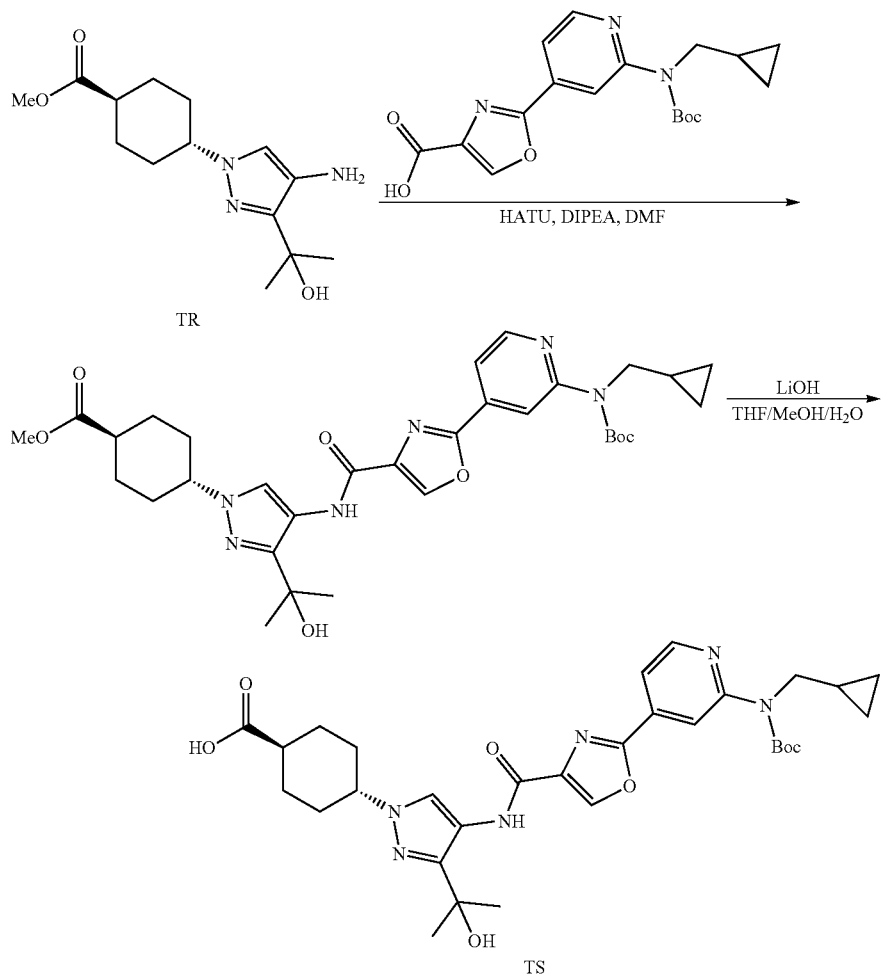

Step 1—Methyl 4-[4-[[2-[2-[tert-butoxycarbonyl(cyclopropylmethyl)amino]-4-pyridyl]oxazole-4-carbonyl] amino]-3-(1-hydroxy-1-methyl-ethyl)pyrazol-1-yl] cyclohexanecarboxylate To a mixture of methyl 4-[4-amino-3-(1-hydroxy-1-methyl-ethyl)pyrazol-1-yl]cyclohexanecarboxylate (200 mg, 710 umol, Intermediate TR), 2-[2-[tert-butoxycarbonyl(cyclopropylmethyl)amino]-4-pyridyl]oxazole-4-carboxylic acid (255 mg, 710 umol, synthesized via Steps 1-4 of Intermediate DF) in DMF (3 mL) was added DIPEA (275

Step 2—4-[4-[[2-[2-[Tert-butoxycarbonyl(cyclopropylmethyl)amino]-4-pyridyl]oxazole-4-carbonyl] amino]-3-(1-hydroxy-1-methyl-ethyl)pyrazol-1-yl] cyclohexanecarboxylic acid To a mixture of methyl 4-[4-[[2-[2-[tert-butoxycarbonyl(cyclopropylmethyl)amino]-4-pyridyl]oxazole-4-carbonyl] amino]-3-(1-hydroxy-1-methyl-ethyl)pyrazol-1-yl]cyclohexanecarboxylate (250 mg, 401 umol) in THF (12 mL), MeOH (3 mL) and H₂O (3 mL) was added LiOH (28.8 mg, 1.20 mmol). The reaction mixture was stirred at 25° C. for 3 hours. On completion, the reaction mixture was concentrated in vacuo at 45° C. to remove MeOH and THF. Then water (50 mL) was added into the mixture, and adjusted to pH=4-5 with HCl (1 N), and filtered to obtain the filter cake. The filter cake was dried in vacuo to give compound (195 mg, 79% yield) as a white solid. $^1$H NMR (400 MHz, DMSO-$d_6$) δ 10.42 (s, 1H), 8.95 (s, 1H), 8.59 (d, J=5.1 Hz, 1H), 8.25-8.15 (m, 2H), 7.66 (d, J=1.2, 5.2 Hz, 1H), 5.97-5.73 (m, 1H), 4.14-3.99 (m, 2H), 3.86 (d, J=6.8 Hz, 3H), 2.29-2.20 (m, 1H), 2.07-2.00 (m, 3H), 1.79-1.67 (m, 2H), 1.53-1.49 (m, 16H), 1.21-1.11 (m, 2H), 0.44-0.37 (m, 2H), 0.28-0.20 (m, 2H).

1-(2,6-Dioxo-3-piperidyl)-3-methyl-2-oxo-benzimidazole-5-carbaldehyde (Intermediate SK)

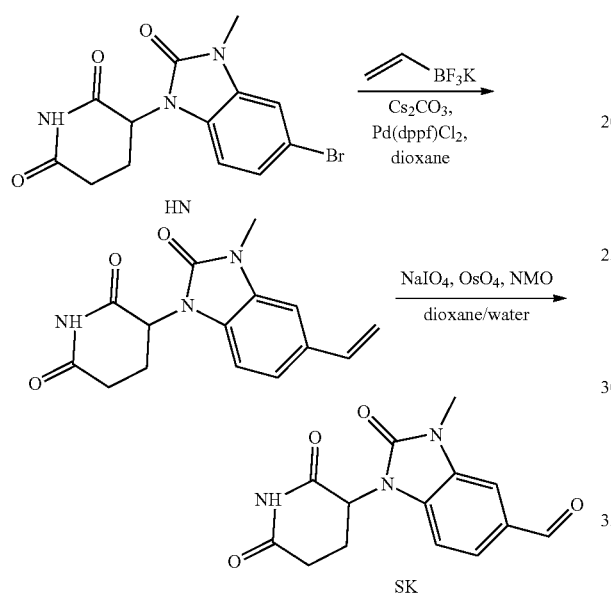

Step 1—3-(3-Methyl-2-oxo-5-vinyl-benzimidazol-1-yl)piperidine-2,6-dione

A mixture of 3-(5-bromo-3-methyl-2-oxo-benzimidazol-1-yl)piperidine-2,6-dione (3.00 g, 8.87 mmol, Intermediate HN), potassium hydride, trifluoro (vinyl)boron (3.57 g, 26.6 mmol), $Cs_2CO_3$ (2 M solution, 8.87 mL), Pd(dppf)Cl$_2$—CH$_2$Cl$_2$ (724 mg, 887 umol) and in dioxane (30 mL) was degassed and purged with N$_2$ for 3 times, and then the mixture was stirred at 80° C. for 3 hours under N$_2$ atmosphere. On completion, the reaction mixture was concentrated in vacuo to give a residue. The residue was purified by reverse phase (TFA condition) to give the title compound (1.60 g, 58% yield) as a yellow solid. LC-MS (ESI$^+$) m/z 286.0 (M+H)$^+$.

Step 2—1-(2,6-Dioxo-3-piperidyl)-3-methyl-2-oxo-benzimidazole-5-carbaldehyde

To a solution of 3-(3-methyl-2-oxo-5-vinyl-benzimidazol-1-yl)piperidine-2,6-dione (0.30 g, 1.05 mmol) in a mixed solvent of dioxane (20 mL) and H$_2$O (2 mL) was added NaIO$_4$ (449 mg, 2.10 mmol), OsO$_4$ (267 mg, 1.00 mmol) and NMO (61.0 mg, 525 umol). The mixture was stirred at 25° C. for 0.5 hr. On completion, the residue was diluted with water (10 mL) and extracted with ethyl acetate (2×20 mL). The combined organic layers were washed with brine (20 mL), dried over Na$_2$SO$_4$, filtered and concentrated in vacuo to give a residue. The residue was purified by prep-HPLC (TFA condition) to give the title compound (0.1 g, 32% yield) as a gray solid. LC-MS (ESI$^+$) m/z 288.0 (M+H)$^+$.

Tertbutyl N-methyl-N-[3-(2-piperazin-1-ylethoxy) cyclobutyl] carbamate (Intermediate SW)

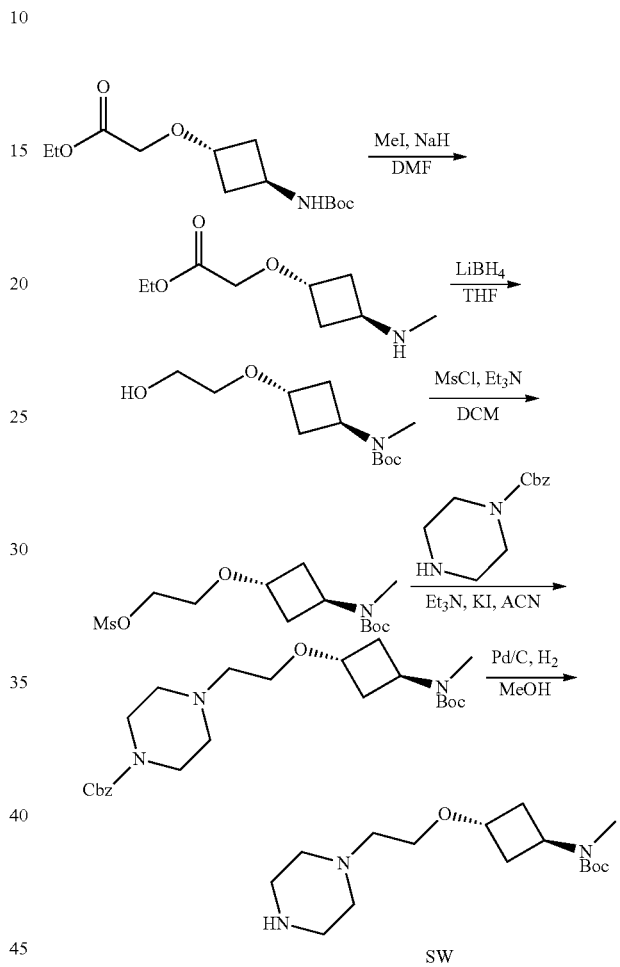

Step 1—Ethyl 2-[3-[tert-butoxycarbonyl(methyl) amino] cyclobutoxy] acetate

To a solution of ethyl 2-[3-(tert-butoxycarbonylamino) cyclobutoxy]acetate (5.00 g, 18 mmol, synthesized via Step 1 of Intermediate SJ) in DMF (50 mL) at 0° C. was added NaH (1.50 g, 36 mmol, 60% oil dispersion) and stirred at 0° C. for 0.5 hour. Then a solution of CH$_3$I (3.10 g, 22 mmol) in DMF (5 mL) was added to the reaction mixture and stirred at 0° C. for 1 hour. On completion, the reaction mixture was quenched by H$_2$O (20 mL) at 0° C., and then extracted with ethyl acetate (2×20 mL). The combined organic layers were washed with brine (2×25 mL), dried over Na$_2$SO$_4$, filtered and concentrated in vacuo to give the title compound (5.00 g, 95% yield) as yellow oil. $^1$H NMR (400 MHz, DMSO-$d_6$) δ 4.66-4.59 (m, 1H), 4.29-4.00 (m, 5H), 2.73 (s, 3H), 2.33-2.28 (m, 2H), 2.15-2.07 (m, 2H), 1.38 (s, 9H), 1.22-1.16 (m, 3H).

Step 2—Tert-butyl N-[3-(2-hydroxyethoxy)cyclobutyl]-N-methyl-carbamate

To a solution of ethyl 2-[3-[tert-butoxycarbonyl(methyl)amino]cyclobutoxy]acetate (2.50 g, 8.7 mmol) in THF (30 mL) was added LiBH$_4$ (0.57 g, 26 mmol) at 0° C., then the reaction mixture was stirred at 25° C. for 2 hour. On completion, the reaction mixture was quenched by water (20 mL) at 25° C., and then extracted with ethyl acetate (2×30 mL). The combined organic layers were washed with brine (2×40 mL), dried over Na$_2$SO$_4$, filtered and concentrated in vacuo to give the title compound (2.00 g, 93% yield) as colorless oil.

Step 3—2-[3-[Tert-butoxycarbonyl(methyl)amino]cyclobutoxy]ethyl methanesulfonate To a solution of tert-butyl N-[3-(2-hydroxyethoxy)cyclobutyl]-N-methyl-carbamate (2.00 g, 8.20 mmol) and Et$_3$N (1.7 g, 16 mmol) in DCM (20 mL) was added MsCl (1.40 g, 12 mmol), then the reaction mixture was stirred at 0° C. for 1 hour. On completion, the reaction mixture was quenched by water (25 mL) at 25° C., and extracted with DCM (2×30 mL). The combined organic layers were washed with brine (2×40 mL), dried over Na$_2$SO$_4$, filtered and concentrated in vacuo to give the title compound (2.50 g, 94% yield) as colorless oil.

Step 4—Benzyl 4-[2-[3-[tert-butoxycarbonyl(methyl)amino]cyclobutoxy]ethyl]piperazine-1-carboxylate To a solution of 2-[3-[tert-butoxycarbonyl(methyl)amino]cyclobutoxy] ethyl methanesulfonate (2.50 g, 7.70 mmol) and benzyl piperazine-1-carboxylate (3.40 g, 15.0 mmol) in ACN (30 mL) was added Et$_3$N (2.4 g) and KI (1.50 g, 9.3 mmol), then the reaction mixture was stirred at 70° C. for 12 hours. On completion, the reaction mixture was filtered and concentrated in vacuo. The crude product was purified by reverse phase HPLC (0.1% FA condition) to give the title compound (0.60 g, 16% yield) as a white solid. LC-MS (ESI$^+$) m/z 448.1 (M+H)$^+$.

Step 5—Tertbutyl N-methyl-N-[3-(2-piperazin-1-ylethoxy)cyclobutyl]carbamate

To a solution of benzyl 4-[2-[3-[tert-butoxycarbonyl(methyl)amino]cyclobutoxy]ethyl]piperazine-1-carboxylate (0.60 g, 1.3 mmol) in MeOH (5 mL) was added Pd/C (60 mg, 10% wt), then the mixture was degassed and purged with H$_2$ gas three times. The mixture was stirred at 25° C. for 2 hours under H$_2$ atmosphere. On completion, the reaction mixture was filtered and concentrated in vacuo to give the title compound (0.40 g, 95% yield) as colorless oil.

3-[3-Methyl-5-[[4-[2-[3-(methylamino)cyclobutoxy]ethyl]piperazin-1-yl]methyl]-2-oxo-benzimidazol-1-yl]piperidine-2,6-dione (Intermediate SX)

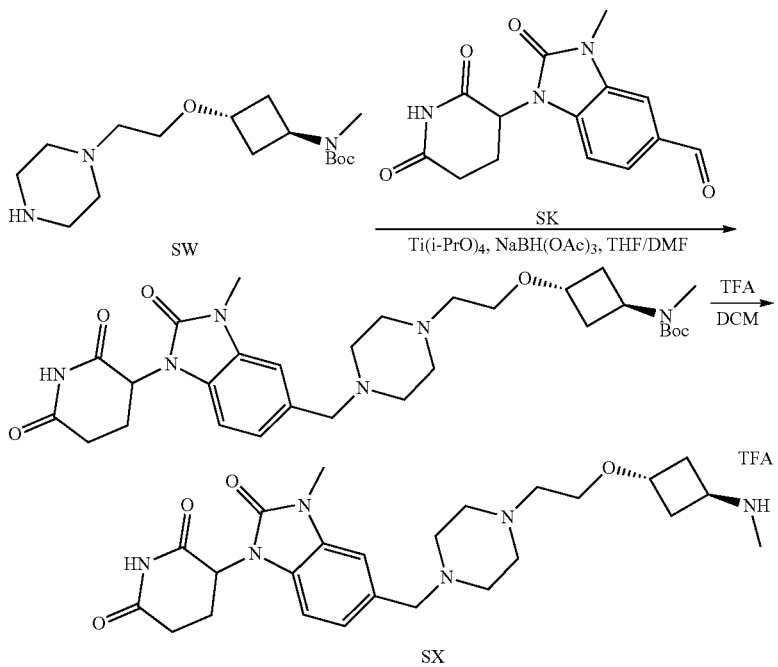

Step 1—Tert-butyl N-[3-[2-[4-[[1-(2,6-dioxo-3-piperidyl)-3-methyl-2-oxo-benzimidazol-5-yl]methyl]piperazin-1-yl]ethoxy]cyclobutyl]-N-methyl-carbamate To a solution of 1-(2,6-dioxo-3-piperidyl)-3-methyl-2-oxo-benzimidazole-5-carbaldehyde (0.15 g, 0.52 mmol, Intermediate SK) and tertbutyl N-methyl-N-[3-(2-piperazin-1-ylethoxy)cyclobutyl] carbamate (0.16 g, 0.52 mmol, Intermediate SW) in a mixed solvent of THF (2 mL) and DMF (2 mL) was added Ti(i-PrO)$_4$ (0.22 g, 0.78 mmol) and stirred at 50° C. for 4 hour, then NaBH(OAc)$_3$ (0.22 g, 1.0 mmol) was added at 25° C. The reaction mixture was stirred at 25° C. for 12 hours. On completion, the mixture was concentrated in vacuo. The crude product was purified by reverse phase HPLC (0.1% TFA condition) to give the title compound (40.0 mg, 8.7% yield) as colorless oil. LC-MS (ESI$^+$) m/z 585.4 (M+H)$^+$.

Step 2—3-[3-Methyl-5-[[4-[2-[3-(methylamino) cyclobutoxy]ethyl]piperazin-1-yl]methyl]-2-oxo-benzimidazol-1-yl]piperidine-2,6-dione To a solution of tert-butyl N-[3-[2-[4-[[1-(2,6-dioxo-3-piperidyl)-3-methyl-2-oxo-benzimidazol-5-yl] methyl]piperazin-1-yl]ethoxy]cyclobutyl]-N-methyl-carbamate (30.0 mg, 51.3 umol) in TFA (1.5 mL) was added DCM (2 mL). The reaction mixture was stirred at 25° C. for 2 hrs. On completion, the mixture was concentrated in vacuo to give the title compound (30.7 mg, 100% yield) as yellow oil. LC-MS (ESI$^+$) m/z 485.3 (M+H)$^+$.

Tert-butyl 4-(trans-4-aminocyclohexyl)piperazine-1-carboxylate (Intermediate RY)

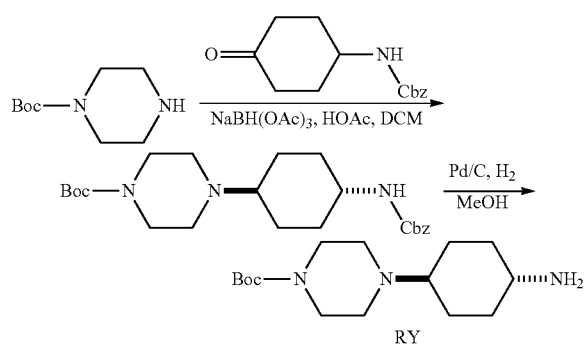

Step 1—Tert-butyl 4-(trans-4-(((benzyloxy)carbonyl)amino)cyclohexyl)piperazine-1-carboxylate To a solution of tert-butyl piperazine-1-carboxylate (24.0 g, 129 mmol) in DCM (400 mL) was added benzyl N-(4-oxocyclohexyl)carbamate (31.9 g, 129 mmol, CAS #16801-63-1), HOAc (3.15 g, 52.5 mmol) and NaBH(OAc)$_3$ (81.9 g, 387 mmol) successively at 0-10° C., and the mixture was stirred at 15° C. for 16 hours under N$_2$. On completion, the mixture was basified to pH=8 with sat. aq. NaHCO$_3$, and partitioned. The aqueous phase was extracted with DCM (2×200 mL). The combined organic layer was washed with brine (300 mL), dried over Na$_2$SO$_4$, filtered and concentrated in vacuo. The residue was diluted with a mixed solution (PE:EA=3:1) (700 mL), and the mixture was stirred at 20° C. for 16 hours. The mixture was filtered and the filter cake was collected and dried to give the crude product. The product was purified by prep-HPLC (column: Phenomenex Gemini C18 250*50 mm*10 um; mobile phase: [water (0.05% ammonia hydroxide v/v)-ACN]; B %: 50%-75%, 26 MIN, 40% min) to give the title compound (20.0 g, 18% yield) as white solid. $^1$H NMR (400 MHz, CDCl$_3$) δ 7.46-7.29 (m, 5H), 5.09 (s, 2H), 4.57 (s, 1H), 3.43 (m, 5H), 2.50 (m, 4H), 2.28 (m, 1H), 2.10 (d, J=12.0 Hz, 2H), 1.90 (d, J=11.6 Hz, 2H), 1.46 (s, 9H), 1.40-1.27 (m, 2H), 1.22-1.08 (m, 2H).

Step 2—Tert-butyl 4-(trans-4-aminocyclohexyl)piperazine-1-carboxylate

A mixture of tert-butyl 4-[4-(benzyloxycarbonylamino) cyclohexyl]piperazine-1-carboxylate (8.00 g, 16.4 mmol) and Pd/C (800 mg, 10 wt %) in MeOH (80 mL) was stirred at 25° C. for 2 hours under H$_2$ (15 Psi). On completion, the mixture was filtered, and the cake was washed with MeOH (50 mL). The filtrate and washings were combined and concentrated in vacuo to give the title compound (5.30 g, 100% crude yield) as white solid. $^1$H NMR (400 MHz, CDCl$_3$) δ 3.49-3.21 (m, 4H), 2.64-2.58 (m, 1H), 2.54 (m, 4H), 2.31-2.20 (m, 1H), 1.88 (t, J=15.2 Hz, 4H), 1.45 (s, 9H), 1.34-1.22 (m, 2H), 1.17-1.05 (m, 2H).

2-[4-[(4-Piperazin-1-ylcyclohexyl)amino]quinazolin-7-yl]acetonitrile (Intermediate UP)

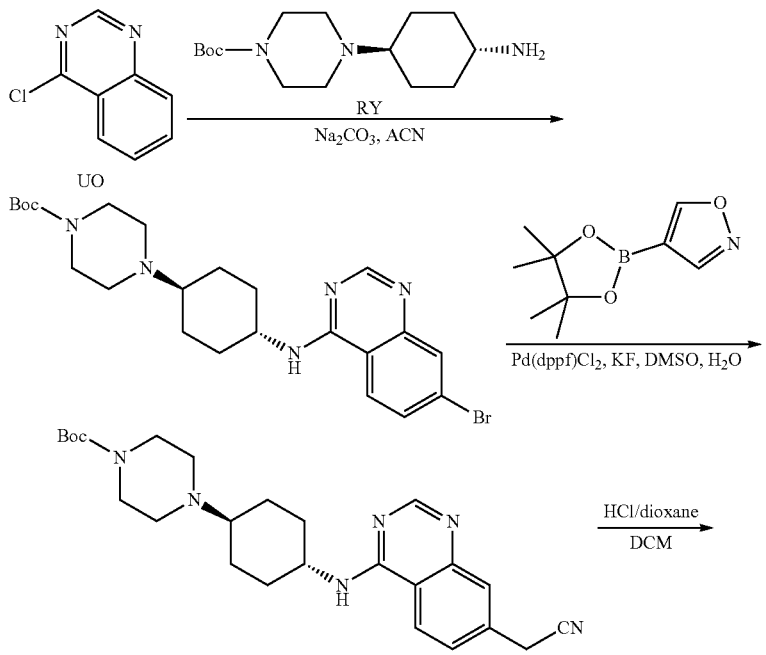

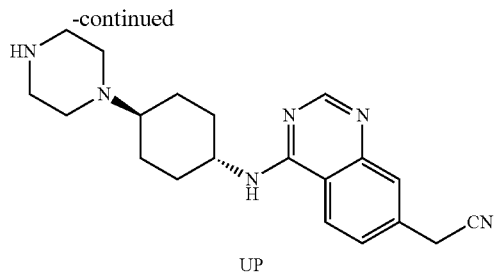

UP

Step 1—Tert-butyl 4-[4-[(7-bromoquinazoin-4-yl)amino]cyclohexyl]piperazine-1-carboxylate To a solution of 7-bromo-4-chloro-quinazoline (860 mg, 3.53 mmol, Intermediate UO) and tert-butyl 4-(4-aminocyclohexyl)piperazine-1-carboxylate (1.10 g, 3.89 mmol, Intermediate RY) in ACN (25 mL) was added $Na_2CO_3$ (1.12 g, 10.6 mmol). The reaction mixture was stirred at 85° C. for 12 hours under $N_2$. On completion, the reaction mixture was diluted with DCM/MeOH (300 mL) and filtered. The organic layer was concentrated in vacuo. The residue was purified by trituration with DCM (3×10 mL) to give the title compound (1.60 g, 61% yield) as a white solid. LC-MS (ESI$^+$) m/z 490.1 (M+H)$^+$.

Step 2—Tert-butyl 4-[4-[[7-(Cyanomethyl)quinazolin-4-yl]amino] cyclohexyl]piperazine-1-carboxylate To a solution of tert-butyl 4-[4-[(7-bromoquinazolin-4-yl)amino]cyclohexyl]piperazine-1-carboxylate (400 mg, 815 umol) and 4-(4,4,5,5-tetramethyl-1,3,2-dioxaborolan-2-yl)isoxazole (191 mg, 980 umol, CAS #928664-98-6) in DMSO (14 mL) and $H_2O$ (6 mL) was added KF (189 mg, 3.26 mmol) and ditert-butyl(cyclopentyl)phosphane; dichloropalladium; iron (53.1 mg, 81.5 umol). The reaction mixture was stirred at 130° C. for 12 hours under $N_2$. On completion, the reaction mixture was diluted with DCM (20 mL), poured into brine (10 mL) and extracted with DCM (2×20 mL). The combined organic layers were washed with brine (30 mL), dried with anhydrous $Na_2SO_4$ and filtered. The filtrate was concentrated in vacuo. The residue was purified by prep-HPLC (0.1%, FA) to give the title compound (500 mg, 67% yield) as a white solid. $^1$H NMR (400 MHz, CDCl$_3$) δ 8.62 (s, 1H), 7.96 (d, J=8.4 Hz, 1H), 7.81 (s, 1H), 7.47 (dd, J=2.0, 8.8 Hz, 1H), 6.75 (s, 1H), 4.28 (s, 1H), 3.93 (s, 2H), 3.71 (t, J=4.4 Hz, 4H), 3.10 (t, J=10.8 Hz, 1H), 2.32 (d, J=11.2 Hz, 2H), 2.17 (d, J=11.2 Hz, 2H), 1.74-1.59 (m, 2H), 1.58-1.50 (m, 2H), 1.47 (s, 9H).

Step 3—2-[4-[(4-Piperazin-1-ylcyclohexyl)amino]quinazolin-7-yl]acetonitrile

To a solution of tert-butyl 4-[4-[[7-(cyanomethyl)quinazolin-4-yl]amino]cyclohexyl]piperazine-1-carboxylate (400 mg, 887 umol) in DCM (15 mL) was added TFA (23.1 g, 202 mmol). The reaction mixture was stirred at 25° C. for 1 hour. On completion, the reaction mixture was concentrated in vacuo. The residue was purified by reversed-phase flash ($NH_3$—$H_2O$/ACN/MeOH, 1/0/0 (10 min), 0/1/0 (20 min), 0/0/1 (20 min)) to give the title compound (280 mg, 85% yield) as a yellow. $^1$H NMR (400 MHz, DMSO-d$_6$) δ 8.45 (s, 1H), 8.33 (d, J=8.4 Hz, 1H), 7.95 (d, J=7.6 Hz, 1H), 7.62 (s, 1H), 7.44 (d, J=1.6, 8.8 Hz, 1H), 4.22 (s, 2H), 4.17-4.05 (m, 1H), 2.73-2.53 (m, 4H), 2.47-2.39 (m, 4H), 2.29-2.16 (m, 1H), 2.02 (d, J=12.0 Hz, 2H), 1.85 (d, J=12.0 Hz, 2H), 1.47-1.31 (m, 4H); LC-MS (ESI$^+$) m/z 351.3 (M+H)$^+$.

2-[2-[2-[2-(2-Tert-butoxy-2-oxo-ethoxy)ethoxy]ethoxy]ethoxy]acetic acid (Intermediate UM)

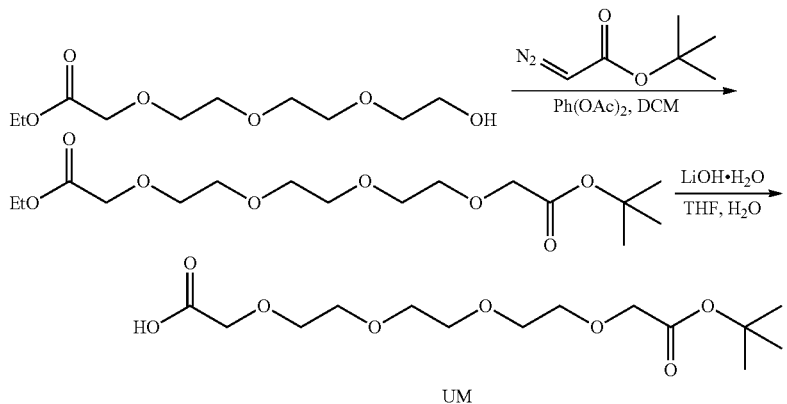

UM

Step 1—Ethyl 2-[2-[2-[2-(2-tert-butoxy-2-oxo-ethoxy)ethoxy]ethoxy]ethoxy]acetate To a solution of ethyl 2-[2-[2-(2-hydroxyethoxy)ethoxy]ethoxy]acetate (150 mg, 635 umol, synthesized via Step 1 of Intermediate BI) and diacetoxyrhodium (6.00 mg, 13.6 umol) in anhydrous DCM (4 mL) was added a solution of tert-butyl 2-diazoacetate (271 mg, 1.91 mmol, CAS #35059-50-8) in DCM (4 mL) dropwise at 0-10° C. The mixture was stirred at 25° C. for 16 hours under N₂. On completion, the reaction was quenched with HOAc (0.1 mL). The mixture was stirred at 25° C. for 15 minutes. The mixture was then concentrated in vacuo. The residue was purified over column chromatography on silica gel (PE:EA=5:1-3:1) to give the title compound (130 mg, 58% yield) as light green oil. ¹H NMR (400 MHz, CDCl₃) δ 4.22 (q, J=7.2 Hz, 2H), 4.16 (s, 2H), 4.03 (s, 2H), 3.74-3.68 (m, 12H), 1.48 (s, 9H), 1.29 (t, J=7.2 Hz, 3H).

Step 2—2-[2-[2-[2-(2-Tert-butoxy-2-oxo-ethoxy)ethoxy]ethoxy]ethoxy]acetic acid

To a solution of ethyl 2-[2-[2-[2-(2-tert-butoxy-2-oxo-ethoxy)ethoxy]ethoxy]ethoxy]acetate (130 mg, 371 umol) in THF (3 mL) was added a solution of lithium hydroxide hydrate (17.0 mg, 405 umol) in H₂O (1 mL) at 25° C. The mixture was stirred at 25° C. for 16 hours. On completion, the mixture was diluted with water (20 mL), acidified to pH=5 with 1.0 M aq. HCl, then extracted with EA (3×10 mL). The combined organic layer was washed with brine (10 mL), dried over Na₂SO₄, filtered and concentrated in vacuo to give the title compound (110 mg, 92% yield) as light green oil. ¹H NMR (400 MHz, CDCl₃) δ 4.17 (s, 2H), 4.03 (s, 2H), 3.77-3.70 (m, 12H), 1.48 (s, 9H).

(2S,4R)-1-[(2S)-2-Amino-3,3-dimethyl-butanoyl]-4-hydroxy-N-[[4-(4-methylthiazol-5-yl)-phenyl]methyl]pyrrolidine-2-carboxamide (Intermediate CI)

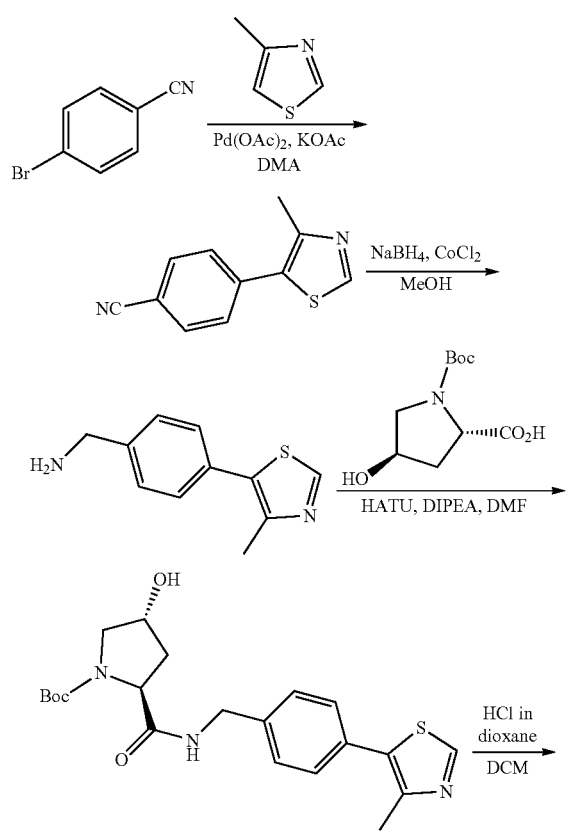

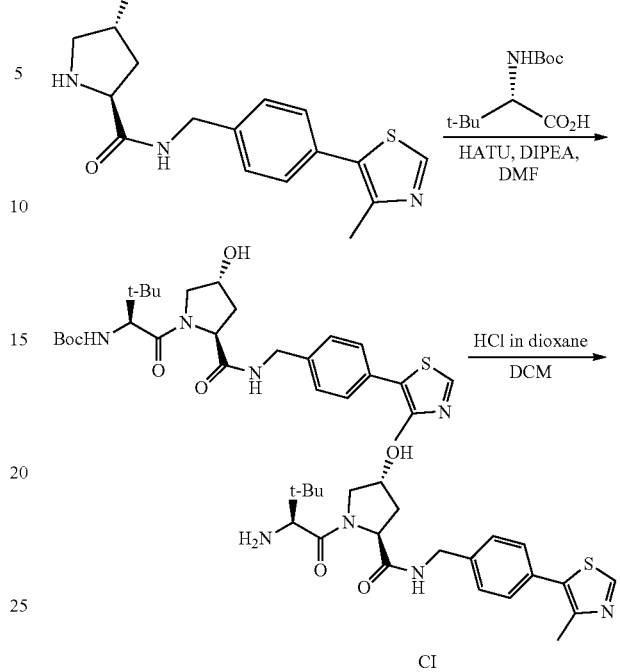

Step 1—4-(4-Methylthiazol-5-yl)benzonitrile

To a mixture of 4-bromobenzonitrile (32.0 g, 176 mmol), 4-methylthiazole (34.86 g, 352 mmol) and KOAc (34.5 g, 352 mmol) in DMA (100 mL) was added Pd(OAc)₂ (820 mg, 3.65 mmol). The mixture was stirred at 150° C. under nitrogen atmosphere for 2 hours. On completion, the mixture was diluted with water (200 mL) and extracted with ethyl acetate (3×200 mL). The combined organic layer was dried over anhydrous Na₂SO₄, filtered and concentrated in vacuo to give the crude product. The crude product was triturated with PE (100 mL) and filtered to give the title compound (28.8 g, 82% yield) as a yellow solid. ¹H NMR (400 MHz, MeOD-d₄) δ 8.98 (s, 1H), 7.85-7.81 (m, 2H), 7.71-7.66 (m, 2H), 2.53 (s, 3H); LC-MS (ESI⁺) m/z 201.0 (M+H)⁺.

Step 2—[4-(4-Methylthiazol-5-yl)phenyl]methanamine

To a solution of 4-(4-methylthiazol-5-yl)benzonitrile (14.7 g, 73.4 mmol) in MeOH (460 mL) was added dichlorocobalt (14.3 g, 110 mmol) and the mixture was cooled to 0° C. Then, NaBH₄ (13.9 g, 367 mmol) was added in portions over 0.5 hour. Finally, the mixture was allowed to warm to rt and stirred for 12 hours. On completion, the reaction mixture was quenched with NH₃—H₂O (20 mL, 30 wt %), then diluted with water (100 mL) and extracted with DCM (3×80 mL). The combined organic layer was dried over anhydrous Na₂SO₄, filtered and concentrated in vacuo to give a residue. The residue was purified by reverse phase flash column (0.1% NH₃.H₂O in water) to give the title compound (3.50 g, 23.3% yield) as a yellowish oil. LC-MS (ESI⁺) m/z 205.1 (M+H)⁺.

Step 3—Tert-butyl (2S,4R)-4-hydroxy-2-[[4-(4-methylthiazol-5-yl)phenyl]methylcarbamoyl]-pyrrolidine-1-carboxylate A solution of (2S,4R)-1-tert-butoxycarbonyl-4-hydroxy-pyrrolidine-2-carboxylic acid (3.36 g, 14.5 mmol, CAS

13726-69-7) in DMF (50 mL) was cooled to 0° C. Then, DIPEA (5.13 g, 39.7 mmol), [4-(4-methylthiazol-5-yl) phenyl] methanamine (2.70 g, 13.2 mmol) and HATU (6.03 g, 15.9 mmol) were added. Finally, the mixture was allowed to warm to rt and stirred for 12 hours. On completion, the reaction mixture was concentrated under reduced pressure to remove the DMF. The residue was diluted with water (50 mL) and extracted with DCM (3×60 mL). The combined organic layer was dried over anhydrous $Na_2SO_4$, filtered and concentrated in vacuo to give a residue. The residue was purified by reverse phase flash (0.1% $NH_3$—$H_2O$ in water) column to give the title compound (1.70 g, 30% yield) as a yellowish solid. $^1$H NMR (400 MHz, MeOD-d$_4$) δ 8.91 (s, 1H), 7.48-7.40 (m, 4H), 4.74-4.25 (m, 4H), 3.66-3.56 (m, 1H), 3.54-3.43 (m, 1H), 2.48 (s, 3H), 2.31-2.20 (m, 1H), 2.08-1.98 (m, 1H), 1.54-1.25 (m, 9H); LC-MS (ESI$^+$) m/z 418.0 (M+H)$^+$.

Step 4—(2S,4R)-4-hydroxy-N-[[4-(4-methylthiazol-5-yl)phenyl]methyl]pyrrolidine-2-carboxamide To a solution of tert-butyl (2S,4R)-4-hydroxy-2-[[4-(4-methylthiazol-5-yl)phenyl]methylcarbamoyl]-pyrrolidine-1-carboxylate (1.70 g, 4.07 mmol) in DCM (10 mL) was added HCl in dioxane (4 M, 10 mL) and the mixture was stirred at rt for 6 hours. On completion, the mixture was concentrated under reduced pressure to give the product (1.60 g, HCl salt, 96% yield) as a yellowish solid. LC-MS (ESI$^+$) m/z 318.0 (M+H)$^+$.

Step 5—Tert-butyl N-[(1S)-1-[(2S,4R)-4-hydroxy-2-[[4-(4-methylthiazol-5-yl)phenyl] methylcarbamoyl]pyrrolidine-1-carbonyl]-2,2-dimethyl-propyl] carbamate A solution of (2S,4R)-4-hydroxy-N-[[4-(4-methylthiazol-5-yl)phenyl]methyl]pyrrolidine-2-carboxamide (1.60 g, 4.52 mmol, HCl salt) in DMF (25.00 mL) was cooled to 0° C. Then, DIPEA (1.75 g, 13.6 mmol), (2S)-2-(tert-butoxycarbonylamino)-3,3-dimethyl-butanoic acid (1.31 g, 5.65 mmol) and HATU (2.06 g, 5.43 mmol) were added. Finally, the mixture was allowed to warm to rt and stirred for 12 hours. On completion, the reaction mixture was concentrated under reduced pressure to remove the DMF. The residue was diluted with water (40 mL) and extracted with DCM (3×40 mL). The combined organic layer was dried over anhydrous $Na_2SO_4$, filtered and concentrated in vacuo to give a residue. The residue was purified by reverse phase flash column (0.1% $NH_3$—$H_2O$ in water) to give the title compound (1.70 g, 70% yield) as a light yellow solid. $^1$H NMR (400 MHz, CDCl$_3$-d$_1$) δ 8.71 (s, 1H), 7.43 (s, 1H), 7.39-7.30 (m, 4H), 5.20 (d, J=8.0 Hz, 1H), 4.78 (t, J=1.6 Hz, 1H), 4.59 (m, 1H), 4.33 (m, 1H), 4.18-4.09 (m, 2H), 3.58 (m, 1H), 2.60 (m, 1H), 2.52 (s, 3H), 2.14 (m, 1H), 1.41 (s, 9H), 0.92 (s, 9H); LC-MS (ESI$^+$) m/z 531.1 (M+H)$^+$.

Step 6—(2S,4R)-1-[(2S)-2-amino-3,3-dimethyl-butanoyl]-4-hydroxy-N-[[4-(4-methylthiazol-5-yl)-phenyl]methyl]pyrrolidine-2-carboxamide To a solution of tert-butyl N-[(1S)-1-[(2S,4R)-4-hydroxy-2-[[4-(4-methylthiazol-5-yl)phenyl]-methyl carbamoyl]pyrrolidine-1-carbonyl]-2,2-dimethyl-propyl]carbamate (1.60 g, 3.01 mmol) in DCM (20 mL) was added HCl in dioxane (4 M, 20 mL). Then, the mixture was stirred at rt for 6 hours. On completion, the mixture was concentrated under reduced pressure to give the title compound as a light yellow solid (1.90 g, HCl salt, 95% yield). $^1$H NMR (400 MHz, MeOD-d$_4$) δ 9.98 (s, 1H), 7.58-7.52 (m, 4H), 4.72-4.65 (m, 1H), 4.60-4.50 (m, 2H), 4.46-4.38 (m, 1H), 4.07 (s, 1H), 3.86-3.83 (m, 1H), 3.75-3.68 (m, 1H), 3.60 (s, 1H), 2.61 (s, 3H), 2.33-2.28 (m, 1H), 2.11-2.05 (m, 1H), 1.14 (s, 9H); LC-MS (ESI$^+$) m/z 431.1 (M+H)$^+$.

2-[2-[2-[2-[2-[[(1S)-1-[(2S,4R)-4-Hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]ethoxy]acetic acid (Intermediate UN)

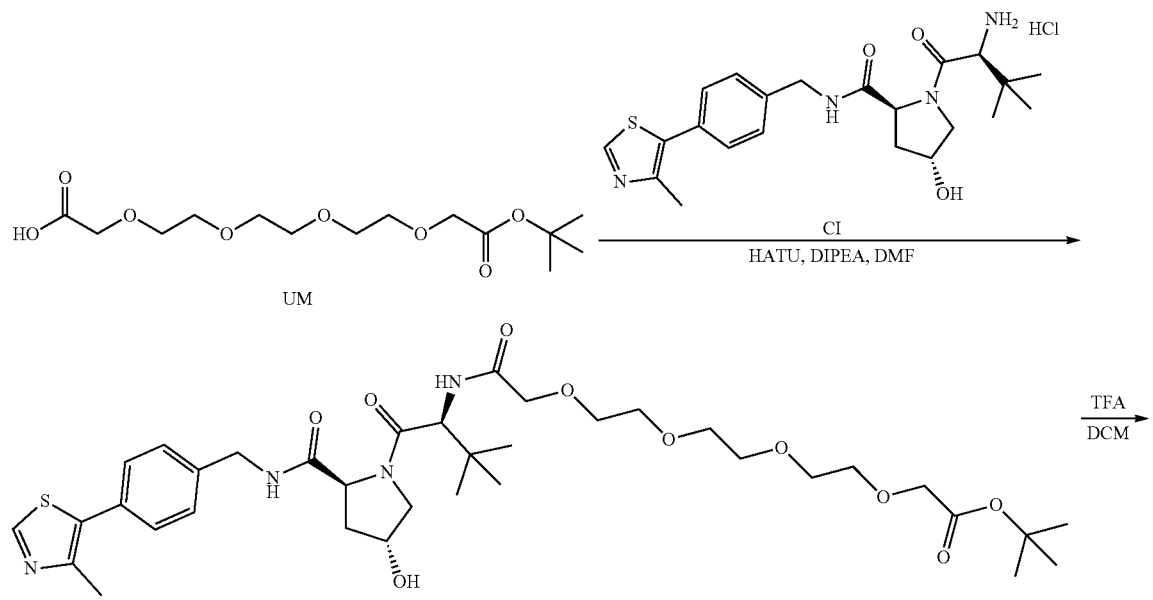

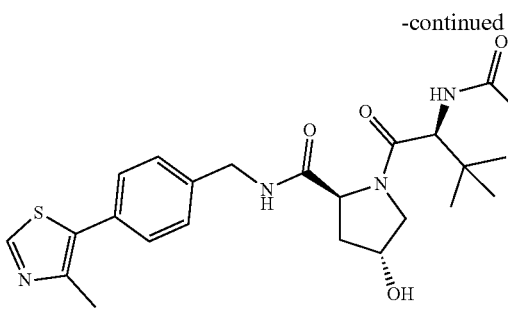

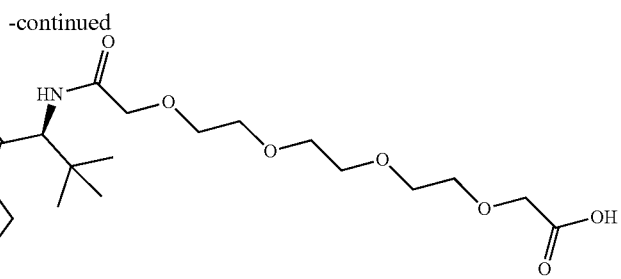

Step 1—Tert-butyl 2-[2-[2-[2-[2-[[(1S)-1-[(2S,4R)-4-hydroxy-2-[[4-(4-methylthiazol-5-yl)phenyl]methylcarbamoyl]pyrrolidine-1-carbonyl]-2,2-dimethyl-propyl]amino]-2-oxo-ethoxy] ethoxy]ethoxy] ethoxy] acetate A mixture of (2S,4R)-1-[(2S)-2-amino-3,3-dimethyl-butanoyl]-4-hydroxy-N-[[4-(4-methylthiazol-5-yl)phenyl]methyl]pyrrolidine-2-carboxamide (180 mg, HCl, Intermediate CI), 2-[2-[2-[2-(2-tert-butoxy-2-oxo-ethoxy)ethoxy]ethoxy]ethoxy]acetic acid (100 mg, 310 umol, Intermediate UM), HATU (155 mg, 408 umol) and DIPEA (121 mg, 936 umol) in DMF (5 mL) was stirred at 25° C. for 2 hours. On completion, the reaction mixture was diluted with water (50 mL), then extracted with EA (3×30 mL). The combined organic layer was washed with brine (20 mL), dried over $Na_2SO_4$, filtered and concentrated in vacuo. The residue was purified over column chromatography on silica gel (DCM:MeOH=50:1-20:1) to give the title compound (130 mg, 48% yield, 84% purity) as light yellow gum. LC-MS (ESI$^+$) m/z 735.3 (M+H)$^+$, 757.3 (M+Na)$^+$.

Step 2—2-[2-[2-[2-[2-[[(1S)-1-[(2S,4R)-4-Hydroxy-2-[[4-(4-methylthiazol-5-yl)phenyl] methylcarbamoyl]pyrrolidine-1-carbonyl]-2,2-dimethyl-propyl]amino]-2-oxo-ethoxy] ethoxy]ethoxy]ethoxy]acetic acid To a solution of tert-butyl 2-[2-[2-[2-[2-[[(1S)-1-[(2S,4R)-4-hydroxy-2-[[4-(4-methylthiazol-5-yl) phenyl]methylcarbamoyl]pyrrolidine-1-carbonyl]-2,2-dimethyl-propyl]amino]-2-oxo-ethoxy]ethoxy] ethoxy]ethoxy]acetate (110 mg, 125 umol) in DCM (4 mL) was added TFA (2 mL) at 25° C. The mixture was stirred at 25° C. for 3 hours. On completion, the mixture was concentrated in vacuo to give the title compound (140 mg, quant. crude yield, TFA) as light yellow gum. LC-MS (ESI$^+$) m/z 679.4 (M+H)$^+$.

2-[2-[2-(2-Tert-butoxy-2-oxo-ethoxy)ethoxy]ethoxy] acetic acid (Intermediate UQ)

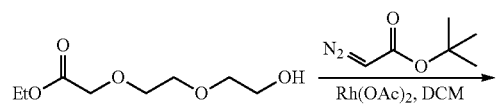

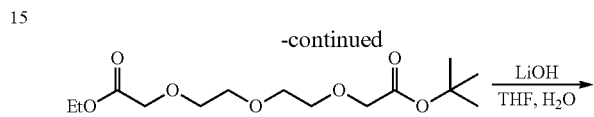

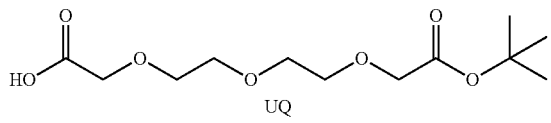

Step 1—Ethyl 2-[2-[2-(2-tert-butoxy-2-oxo-ethoxy)ethoxy]ethoxy]acetate

To a stirring mixture of ethyl 2-[2-(2-hydroxyethoxy)ethoxy]acetate (0.80 g, 4.16 mmol, synthesized via Step 1 of Intermediate BM) and diacetoxyrhodium (33.6 mg, 76.0 umol) in DCM (10 mL) was added a solution of tert-butyl 2-diazoacetate (1.78 g, 12.49 mmol, CAS #35059-50-8) in DCM (10 mL) drop-wise under ice-cooling bath (0° C.). After the addition, the resulting mixture was stirred at 20° C. for 16 hours. Diacetoxyrhodium (33.6 mg, 76.02 umol) and tert-butyl 2-diazoacetate (1.78 g, 12.49 mmol) were supplied subsequently, and the resulting mixture was stirred at 20° C. for another 4 hours. On completion, the mixture was quenched with AcOH (1.2 mL) and concentration in vacuo. The residue was purified by column chromatography (SiO$_2$, Petroleum ether/Ethyl acetate=5/1 to 3/1) to give the title compound (1.11 g, 87% yield) as blue oil. $^1$H NMR (400 MHz, CDCl$_3$) δ 4.28 (q, J=7.2 Hz, 2H), 4.02 (s, 2H), 4.15 (s, 2H), 3.73-3.70 (m, 8H), 1.48 (m, 9H), 1.28 (t, J=7.2 Hz, 3H).

Step 2—2-[2-[2-(2-Tert-butoxy-2-oxo-ethoxy)ethoxy]ethoxy]acetic acid

To a solution of ethyl 2-[2-[2-(2-tert-butoxy-2-oxo-ethoxy)ethoxy]ethoxy]acetate (1 g, 3.26 mmol) in THF (40 mL) was added a solution of LiOH.H$_2$O (170 mg, 4.05 mmol) in H$_2$O (20 mL). The mixture was stirred at 20° C. for 16 hours. On completion, the mixture was diluted with H$_2$O (30 mL), adjusted to pH=4-5 with 1M aq. HCl, extracted with EA (2×50 mL). The organic phases were combined and dried over Na$_2$SO$_4$, filtered and concentrated in vacuo to give the title compound (800 mg, 88% yield) as yellowish oil.

2-[2-[2-[2-[[(1S)-1-[(2S,4R)-4-Hydroxy-2-[[4-(4-methylthiazol-5-yl)phenyl]methylcarbamoyl] pyrrolidine-1-carbonyl]-2,2-dimethyl-propyl]amino]-2-oxo-ethoxy]ethoxy]ethoxy]acetic acid (Intermediate UR)

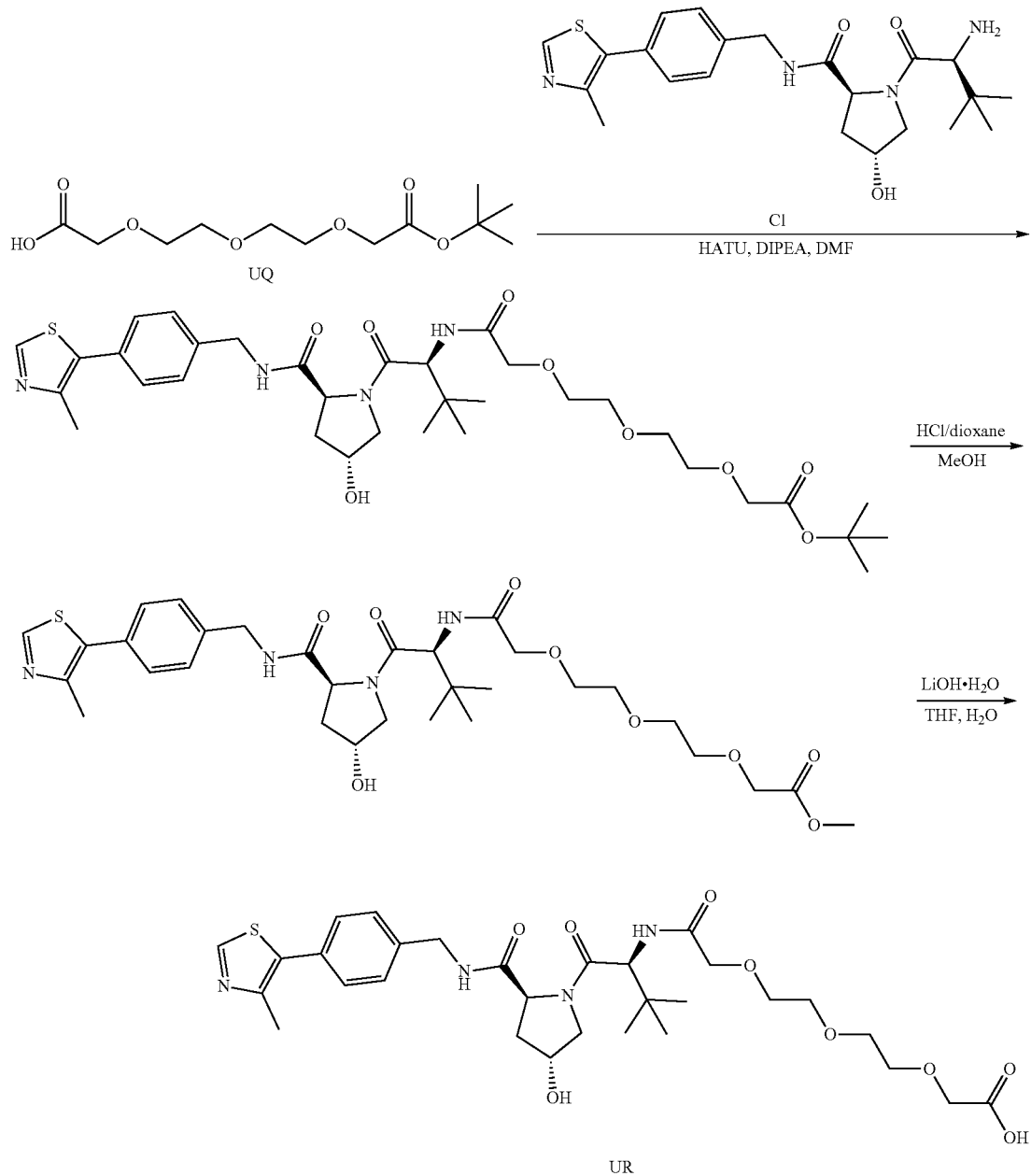

Step 1—Tert-butyl 2-[2-[2-[2-[[(1S)-1-[(2S,4R)-4-hydroxy-2-[[4-(4-methylthiazol-5-yl) phenyl] methylcarbamoyl]pyrrolidine-1-carbonyl]-2,2-dimethyl-propyl] amino]-2-oxo-ethoxy] ethoxy]ethoxy]acetate To a mixture of 2-[2-[2-(2-tert-butoxy-2-oxo-ethoxy)ethoxy]ethoxy]acetic acid (200 mg, 718 umol, Intermediate UQ) and HATU (327 mg, 862 umol) in DMF (20 mL) was added DIPEA (278 mg, 2.16 umol, 375 uL) and (2S,4R)-1-[(2S)-2-amino-3,3-dimethyl-butanoyl]-4-hydroxy-N-[[4-(4-methylthiazol-5-yl)phenyl] methyl]pyrrolidine-2-carboxamide (335 mg, 718 umol, HCl, Intermediate CI) subsequently, then the resulting mixture was stirred at 20° C. for 16 hours. On completion, the mixture was diluted with H₂O (20 mL), then extracted with EA (2×50 mL), the organic phase was concentrated in vacuo. The residue was purified by column chromatography (SiO₂, PE/EA=1/1, EA/MeOH=40/1 to 10/1) to give the title compound (400 mg, 70% yield) as yellowish solid. LC-MS (ESI⁺) m/z 691.3 (M+H)⁺.

Step 2—(S)-Methyl 13-((2S,4R)-4-hydroxy-2-((4-(4-methylthiazol-5-yl)benzyl)carbamoyl) pyrrolidine-1-carbonyl)-14,14-dimethyl-11-oxo-3,6,9-trioxa-12-azapentadecan-1-oate To a solution of tert-butyl 2-[2-[2-[2-[[(1S)-1-[(2S,4R)-4-hydroxy-2-[[4-(4-methylthiazol-5-yl)phenyl] methylcarbamoyl]pyrrolidine-1-carbonyl]-2,2-dimethyl-propyl]amino]-2-oxo-ethoxy]ethoxy]ethoxy]acetate (100 mg, 144 umol) in MeOH (5 mL) was added HCl/dioxane (4 M, 2 mL). The mixture was stirred at 20° C. for 16 hours. On completion, the reaction mixture was concentrated in vacuo to give the title compound (150 mg, quant. crude yield) as colorless oil. LC-MS (ESI$^+$) m/z 649.3 (M+H)$^+$.

Step 3—2-[2-[2-[2-[[(1S)-1-[(2S,4R)-4-Hydroxy-2-[[4-(4-methylthiazol-5-yl)phenyl]methylcarbamoyl]pyrrolidine-1-carbonyl]-2,2-dimethyl-propyl]amino]-2-oxo-ethoxy]ethoxy]ethoxy]acetic acid To a solution of (S)-methyl 13-((2S,4R)-4-hydroxy-2-((4-(4-methylthiazol-5-yl)benzyl)carbamoyl) pyrrolidine-1-carbonyl)-14,14-dimethyl-11-oxo-3,6,9-trioxa-12-azapentadecan-1-oate (150 mg) in THF (10 mL) was added a solution of LiOH.H$_2$O (200 mg, 4.77 mmol) in H$_2$O (5 mL). The mixture was stirred at 20° C. for 20 mins. On completion, the reaction mixture was concentrated in vacuo to remove THF, then diluted with H$_2$O (20 mL) and the pH was adjusted to 5 with 1.0 M aq. HCl, extracted with EA (2×40 mL). The organic phases were concentrated in vacuo to give the title compound (80 mg, 96%) as yellowish oil. LC-MS (ESI$^+$) m/z 635.4 (M+H)$^+$.

Tert-butyl N-methyl-N-[2-(2-prop-2-ynoxyethoxy)ethyl]carbamate (Intermediate

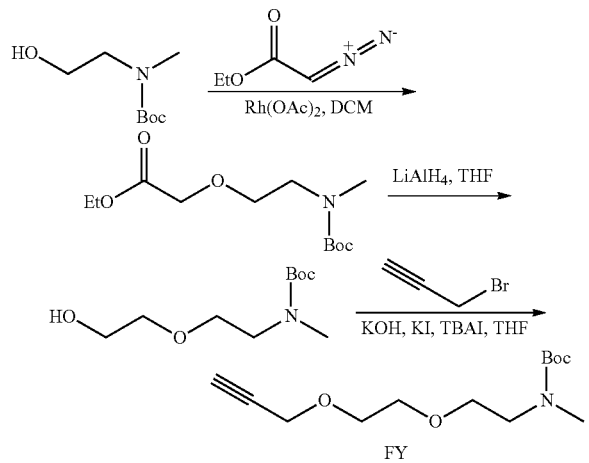

Step 1—Ethyl 2-[2-[tert-butoxycarbonyl(methyl)amino]ethoxy]acetate

To a solution of tert-butyl N-(2-hydroxyethyl)-N-methyl-carbamate (10 g, 57.0 mmol) and Rh(OAc)$_2$ (630 mg, 2.85 mmol) in DCM (100 mL) was added a solution of ethyl 2-diazoacetate (13.0 g, 114 mmol, CAS #623-73-4) in DCM (200 mL) dropwise, and the mixture was stirred at 25° C. for 16 hours. On completion, the reaction mixture was washed with water (50 mL×4), dried over Na$_2$SO$_4$, filtered and concentrated in vacuo to give the title compound (14.5 g, 97% yield) as light yellow liquid. $^1$H NMR (400 MHz, CDCl$_3$) δ 4.21 (q, J=7.2 Hz, 2H), 4.09-4.04 (m, 2H), 3.71-3.59 (m, 2H), 3.46-3.38 (m, 2H), 2.92 (s, 3H), 1.44 (s, 9H), 1.27 (t, J=7.2 Hz, 3H).

Step 2—Tert-butyl N-[2-(2-hydroxyethoxy)ethyl]-N-methyl-carbamate

To a solution of ethyl 2-[2-[tert-butoxycarbonyl(methyl)amino]ethoxy]acetate (12.4 g, 47.4 mmol) in THF (200 mL) was added LiAlH$_4$ (2.76 g, 71.1 mmol, 98% purity) at 0° C. under N$_2$ atmosphere. The reaction mixture was stirred at 20° C. for 1 hour. On completion, the mixture was quenched with water (4 mL) and NaOH aqueous solution (15%, 4 mL) at 0° C., filtered and dried over Na$_2$SO$_4$, filtered and concentrated in vacuo to give the title compound (9.40 g, 90% yield) as colorless liquid. $^1$H NMR (400 MHz, CDCl$_3$) δ 3.72-3.67 (m, 2H), 3.66-3.54 (m, 4H), 3.50-3.42 (m, 2H), 2.91 (s, 3H), 1.46 (s, 9H).

Step 3—Tert-butyl N-methyl-N-[2-(2-prop-2-ynoxyethoxy)ethyl]carbamate

To a solution of tert-butyl N-[2-(2-hydroxyethoxy)ethyl]-N-methyl-carbamate (8.70 g, 39.6 mmol) and 3-bromoprop-1-yne (5.19 g, 43.6 mmol) in THF (100 mL) was added TBAI (879 mg, 2.38 mmol), KI (987 mg, 5.95 mmol) and KOH (2.62 g, 39.6 mmol, 85%). The mixture was stirred at 20° C. for 16 hours. On completion, the reaction mixture was filtered and concentrated in vacuo to give a residue. The residue was purified by silica gel chromatography (PE: EA=3:1) to give the title compound (4.20 g, 41% yield) as colorless oil. $^1$H NMR (400 MHz, CDCl$_3$) δ 4.21 (d, J=2.4 Hz, 2H), 3.72-3.67 (m, 2H), 3.67-3.62 (m, 2H), 3.61-3.55 (m, 2H), 3.45-3.35 (m, 2H), 2.92 (s, 3H), 2.43 (t, J=2.4 Hz, 1H), 1.46 (s, 9H).

3-[3-Methyl-4-[3-[2-[2-(methylamino)ethoxy]ethoxy]propyl]-2-oxo-benzimidazol-1-yl] piperidine-2,6-dione (Intermediate SP)

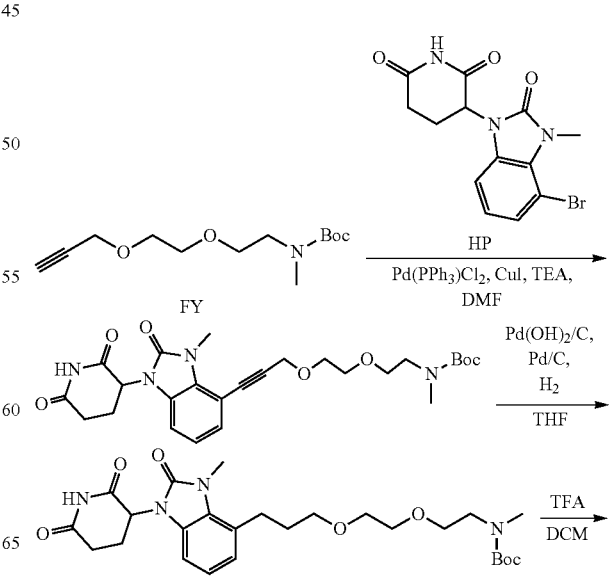

-continued

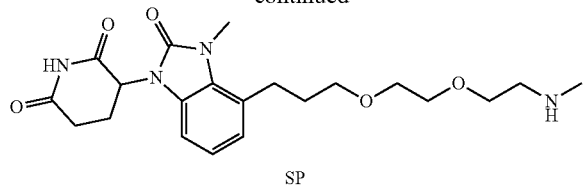

SP

Step 1—Tert-butyl N-[2-[2-[3-[1-(2,6-dioxo-3-piperidyl)-3-methyl-2-oxo-benzimidazol-4-yl]prop-2-ynoxy]ethoxy]ethyl]-N-methyl-carbamate To a mixture of tert-butyl N-methyl-N-[2-(2-prop-2-ynoxyethoxy)ethyl]carbamate (1.37 g, 5.32 mmol, Intermediate FY), 3-(4-bromo-3-methyl-2-oxo-benzimidazol-1-yl)piperidine-2,6-dione (600 mg, 1.77 mmol, Intermediate HP) in DMF (30 mL) was added $Cs_2CO_3$ (2.89 g, 8.87 mmol), $Pd(PPh_3)_2Cl_2$ (249 mg, 354 umol) and CuI (67.5 mg, 354 umol) under $N_2$. The reaction mixture was stirred at 80° C. for 2 hours. On completion, the mixture was filtered, the filtrate was poured into water (100 mL), and the aqueous phase was extracted with ethyl acetate (2×40 mL). The combined organic phase was washed with brine (2×40 mL), dried with anhydrous $Na_2SO_4$, filtered and concentrated in vacuo to get residue. The residue was purified by reverse phase (0.1% FA condition) to get title compound (480 mg, 52% yield) as a brown solid. $^1$H NMR (400 MHz, $CDCl_3$) δ 8.29 (s, 1H), 7.22-7.16 (m, 1H), 7.03-7.00 (m, 1H), 6.78 (d, J=8.0 Hz, 1H), 5.28-5.17 (m, 1H), 4.49 (s, 2H), 4.20-4.08 (m, 1H), 3.81-3.78 (m, 3H), 3.71-3.67 (m, 2H), 3.62 (s, 3H), 3.61-3.55 (m, 4H), 2.93 (s, 3H), 2.92 (s, 2H), 2.30-2.20 (m, 1H), 2.03 (s, 1H), 1.47 (s, 9H).

Step 2—Tert-butyl N-[2-[2-[3-[1-(2,6-dioxo-3-piperidyl)-3-methyl-2-oxo-benzimidazol-4-yl]propoxy]ethoxy]ethyl]-N-methyl-carbamate To a mixture of tert-butyl N-[2-[2-[3-[1-(2,6-dioxo-3-piperidyl)-3-methyl-2-oxo-benzimidazol-4-yl]prop-2-ynoxy]ethoxy]ethyl]-N-methyl-carbamate (480 mg, 933 umol) in THF (20 mL) was added Pd/C (100 mg, 1.87 mmol, 10 wt %) and $Pd(OH)_2$/C (100 mg, 1.87 mmol, 10 wt %) under $N_2$. The suspension was degassed in vacuo and purged with $H_2$ gas three times. The mixture was stirred at 20° C. for 12 hours under $H_2$ (15 psi). On completion, the mixture was filtered and concentrated in vacuo to give the title compound (360 mg, 74% yield) as brown oil. LC-MS (ESI$^+$) m/z 541.2 (M+Na)$^+$.

Step 3—3-[3-Methyl-4-[3-[2-[2-(methylamino)ethoxy]ethoxy]propyl]-2-oxo-benzimidazol-1-yl]piperidine-2,6-dione To a mixture of tert-butyl N-[2-[2-[3-[1-(2,6-dioxo-3-piperidyl)-3-methyl-2-oxo-benzimidazol-4-yl] propoxy]ethoxy]ethyl]-N-methyl-carbamate (350 mg, 675 umol) in DCM (2 mL) was added TFA (154 mg, 1.35 mmol). The reaction mixture was stirred at 25° C. for 0.1 hour. On completion, the mixture was concentrated in vacuo to get title compound (365 mg, 100% yield) as brown oil. LC-MS (ESI$^+$) m/z 419.1 (M+H)$^+$.

4-[4-[[2-[2-[Tert-butoxycarbonyl(cyclopropylmethyl)amino]-4-pyridyl]oxazole-4-carbonyl]amino]-3-(difluoromethyl)pyrazol-1-yl]cyclohexanecarboxylic acid (Intermediate PV)

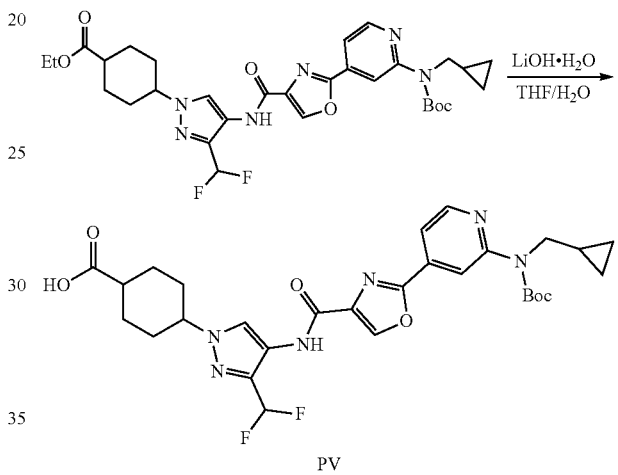

To solution of ethyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl] cyclohexanecarboxylate (4.00 g, 6.36 mmol, synthesized via Step 1 of Intermediate PS) in a mixed solvents of $H_2O$ (20 mL) and THF (60 mL) was added $LiOH·H_2O$ (534 mg, 12.7 mmol). The reaction mixture was stirred at 25° C. for 12 hours. On completion, the reaction mixture was acidified with 2N HCl (8 mL) to pH=5. Then, the mixture was concentrated in vacuo to give the title compound (3.80 g, 99% yield) as a white solid. LC-MS (ESI$^+$) m/z 601.1 (M+H)$^+$.

Tert-butyl N-(cyclopropylmethyl)-N-[4-[4-[[3-(difluoromethyl)-1-(4-formyl cyclohexyl) pyrazol-4-yl]carbamoyl]oxazol-2-yl]-2-pyridyl]carbamate (Intermediate PW)

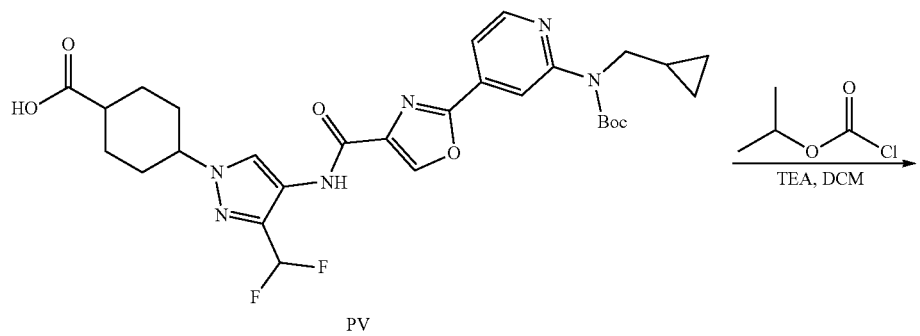

PV

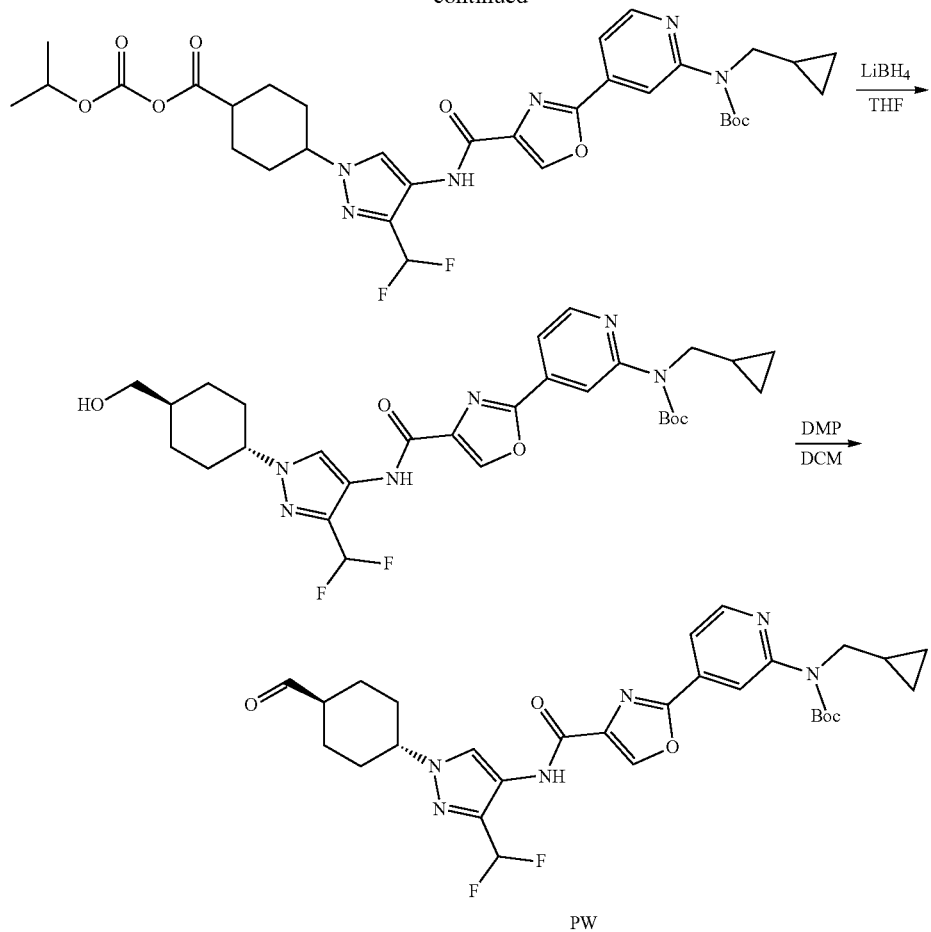

PW

Step 1—Isopropoxycarbonyl4-[4-[[2-[2-[tert-butoxycarbonyl(cyclopropylmethyl)amino]-4-pyridyl]oxazole-4-carbonyl]amino]-3-(difluoromethyl)pyrazol-1-yl]cyclohexanecarboxylate To a solution of 4-[4-[[2-[2-[tert-butoxycarbonyl(cyclopropylmethyl)amino]-4-pyridyl]oxazole-4-carbonyl]amino]-3-(difluoromethyl)pyrazol-1-yl]cyclohexanecarboxylic acid (3.80 g, 6.33 mmol, Intermediate PV) in THF (50 mL) was added TEA (1.92 g, 18.9 mmol, 2.64 mL). Then, the reaction mixture was cooled to −10° C. Isopropyl carbonochloridate (1.68 g, 13.7 mmol) was added and the resulting reaction mixture was stirred at −10° C. for 2 hours. On completion, the reaction mixture was filtered. The filtrate was concentrated in vacuo to give the title compound (4.30 g, 99% yield) as a white solid. LC-MS (ESI$^+$) m/z 687.1 (M+H)$^+$.

Step 2—Tert-butyl N-(cyclopropylmethyl)-N-[4-[4-[[3-(difluoromethyl)-1-[4-(hydroxyl methyl)cyclohexyl]pyrazol-4-yl]carbamoyl]oxazol-2-yl]-2-pyridyl]carbamate To a solution of isopropoxycarbonyl 4-[4-[[2-[2-[tert-butoxycarbonyl(cyclopropylmethyl)amino]-4-pyridyl] oxazole-4-carbonyl]amino]-3-(difluoromethyl)pyrazol-1-yl]cyclohexanecarboxylate (4.30 g, 6.26 mmol) in THF (50 mL) was added LiBH$_4$ (409 mg, 18.8 mmol) and H$_2$O (1.79 g, 99.5 mmol, 1.79 mL). The reaction mixture was stirred at 0° C. for 1 hour. On completion, the reaction mixture was quenched with water (5 mL) and the mixture was extracted with DCM (3×50 mL). The combined organic layers was washed with brine (20 mL), dried over anhydrous sodium sulfate, filtered and concentrated in vacuo to give a white solid. The crude product was purified by reversed phase (0.1% FA condition) to give title compound (1.90 g, 52% yield) as a white solid, which was further separated by SFC (condition: column: DAICEL CHIRALPAK AD (250 mm*30 mm, 10 um); mobile phase:[0.1% NH$_3$H$_2$O MEOH]; B %: 30%-30%, 6.3 min; 400 min). $^1$H NMR (400 MHz, CDCl$_3$) δ 9.07 (s, 1H), 8.52 (d, J=4.8 Hz, 1H), 8.38 (s, 1H), 8.33 (s, 2H), 7.63 (dd, J=1.2, 5.2 Hz, 1H), 6.83 (t, J=54.8 Hz, 1H), 4.19-4.04 (m, 1H), 3.94 (d, J=7.2 Hz, 2H), 3.54 (d, J=6.0 Hz, 2H), 2.25 (d, J=10.8 Hz, 2H), 2.02 (d, J=10.8 Hz, 2H), 1.87-1.77 (m, 2H), 1.68-1.63 (m, 1H), 1.57 (s, 9H), 1.41-1.39 (m, 1H), 1.28-1.23 (m, 1H), 1.22-1.16 (m, 2H), 0.49-0.39 (m, 2H), 0.33-0.23 (m, 2H).

Step 3—Tert-butyl N-(cyclopropylmethyl)-N-[4-[4-[[3-(difluoromethyl)-1-(4-formyl cyclohexyl) pyrazol-4-yl]carbamoyl]oxazol-2-yl]-2-pyridyl]carbamate To a solution of tert-butyl N-(cyclopropylmethyl)-N-[4-[4-[[3-(difluoromethyl)-1-[4-(hydroxymethyl) cyclohexyl]pyrazol-4-yl]carbamoyl]oxazol-2-yl]-2-pyridyl]carbamate (1.00 g, 1.70 mmol) in DCM (20 mL) was added DMP (1.45 g, 3.41 mmol). The reaction mixture was stirred at 25° C. for 12 hours. On completion, the reaction was concentrated in vacuo. The crude product was purified by reversed phase (0.1% FA condition) to give the title compound (380 mg, 38% yield) as a white solid. Trans compound formed, absolute stereochemistry was arbitrarily assigned. $^1$H NMR (400 MHz, CDCl$_3$) δ 9.70 (s, 1H), 9.07 (s, 1H), 8.51 (d, J=5.2 Hz, 1H), 8.35 (d, J=16.8 Hz, 3H), 7.62 (dd, J=1.4, 5.2 Hz, 1H), 7.04-6.61 (m, 1H), 4.10 (t, J=3.8, 11.8 Hz, 1H), 3.94 (d, J=7.2 Hz, 2H), 2.37-2.27 (m, 3H), 2.27-2.18 (m, 2H), 1.88 (dd, J=3.2, 12.6 Hz, 2H), 1.57-1.54 (m, 9H), 1.48 (dd, J=3.2, 12.4 Hz, 1H), 1.27-1.17 (m, 1H), 0.47-0.38 (m, 2H), 0.30-0.23 (m, 2H); LC-MS (ESI$^+$) m/z 585.2 (M+H)$^+$.

6-Bromo-3H-1,3-benzoxazol-2-one (Intermediate OY)

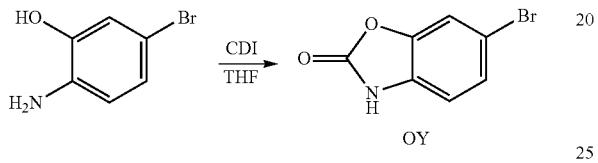

To a solution of 2-amino-5-bromo-phenol (4.50 g, 23.9 mmol, CAS #38191-34-3) in THF (120 mL) was added CDI (4.66 g, 28.7 mmol). The reaction mixture was stirred at 70° C. for 2 hours. On completion, the reaction mixture was added to water (240 mL) and the mixture was adjusted pH=6-7 with 2.0 M aq.HCl, then ethyl acetate (150 mL) was added. The organic layer was separated and washed with a saturated sodium chloride solution (20 mL), dried over anhydrous sodium sulfate, filtered, and concentrated in vacuo. The residue was recrystallized in toluene (60 mL) to give the title compound (3.75 g, 90% yield) as an off-white solid. $^1$H NMR (400 MHz, DMSO-d$_6$) δ 7.58 (d, J=1.6 Hz, 1H), 7.32 (dd, J=1.8, 8.4 Hz, 1H), 7.06 (s, 1H), 7.04-7.01 (m, 1H). LC-MS (ESI$^+$) m/z 216.0 & 214.0 (M+Na)$^+$.

3-(6-Bromo-2-oxo-1,3-benzoxazol-3-yl)piperidine-2,6-dione (Intermediate OZ)

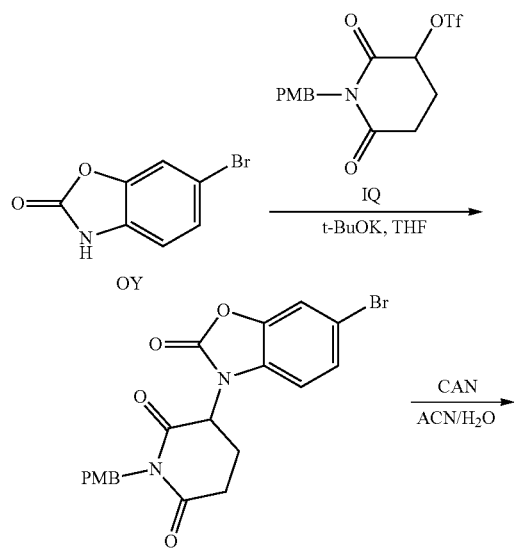

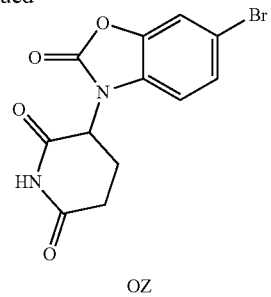

Step 1—3-(6-Bromo-2-oxo-1,3-benzoxazol-3-yl)-1-[(4-methoxyphenyl)methyl]piperidine-2,6-dione To a solution of 6-bromo-3H-1,3-benzoxazol-2-one (2.00 g, 9.35 mmol, Intermediate OY) in THF (50 mL) was added t-BuOK (1.26 g, 11.2 mmol). The reaction mixture was stirred at 0° C. for 0.5 hour. Subsequently, [1-[(4-methoxyphenyl)methyl]-2,6-dioxo-3-piperidyl] trifluoromethanesulfonate (4.81 g, 12.6 mmol, Intermediate IQ) in a solution of THF (30 mL) was added dropwise. The resulting reaction mixture was stirred at 20° C. for 0.5 hour under N$_2$. On completion, the reaction mixture was quenched with saturated NH$_4$Cl (100 mL), and extracted with ethyl acetate (100 mL). The combined organic layer was washed with brine (2×100 mL), dried over anhydrous sodium sulfate and filtered. The filtrate was concentrated in vacuo. The residue was purified by silica gel chromatography (PE:EA:DCM=5:1:2) to give the title compound (3.75 g, 90% yield) as a yellow solid. $^1$H NMR (400 MHz, CDCl$_3$) δ 7.22-7.20 (d, J=8.0 Hz, 1H), 6.89-6.87 (d, J=8.0 Hz, 1H), 4.90-4.86 (m, 1H), 4.47-4.36 (m, 2H) 3.81 (s, 3H), 2.67-2.64 (m, 1H), 2.59-2.54 (m, 2H), 2.40-2.38 (m, 1H). LC-MS (ESI$^+$) m/z 466.9 & 468.9 (M+Na)$^+$.

Step 2—3-(6-Bromo-2-oxo-1,3-benzoxazol-3-yl)piperidine-2,6-dione

To a mixture of 3-(6-bromo-2-oxo-1,3-benzoxazol-3-yl)-1-[(4-methoxyphenyl)methyl]piperidine-2,6-dione (2.00 g, 4.49 mmol) in ACN (60 mL) was added CAN (7.39 g, 13.4 mmol) in solution of H$_2$O (20 mL), and the reaction mixture was degassed and purged with N$_2$ for 3 times. Then the mixture was stirred at 20° C. for 3 hours under N$_2$ atmosphere. On completion, the reaction mixture was filtered. The filtered cake was collected and dried in vacuo to give the title compound (900 mg, 61% yield) as a white solid. $^1$HNMR (400 MHz, DMSO-d$_6$) δ 11.24 (s, 1H), 7.74 (d, J=1.6 Hz, 1H), 7.48-7.41 (m, 1H), 7.27 (d, J=8.4 Hz, 1H), 5.39 (dd, J=5.2, 12.8 Hz, 1H), 3.00-2.80 (m, 1H), 2.76-2.60 (m, 2H), 2.18-2.15 (m Hz, 1H). LC-MS (ESI$^+$) m/z 325.0 & 327.0 (M+H)$^+$.

2-3-[6-[3-[2-(2-Aminoethoxy)ethoxy]propyl]-2-oxo-1,3-benzoxazol-3-yl]piperidine-2,6-dione (Intermediate PA)

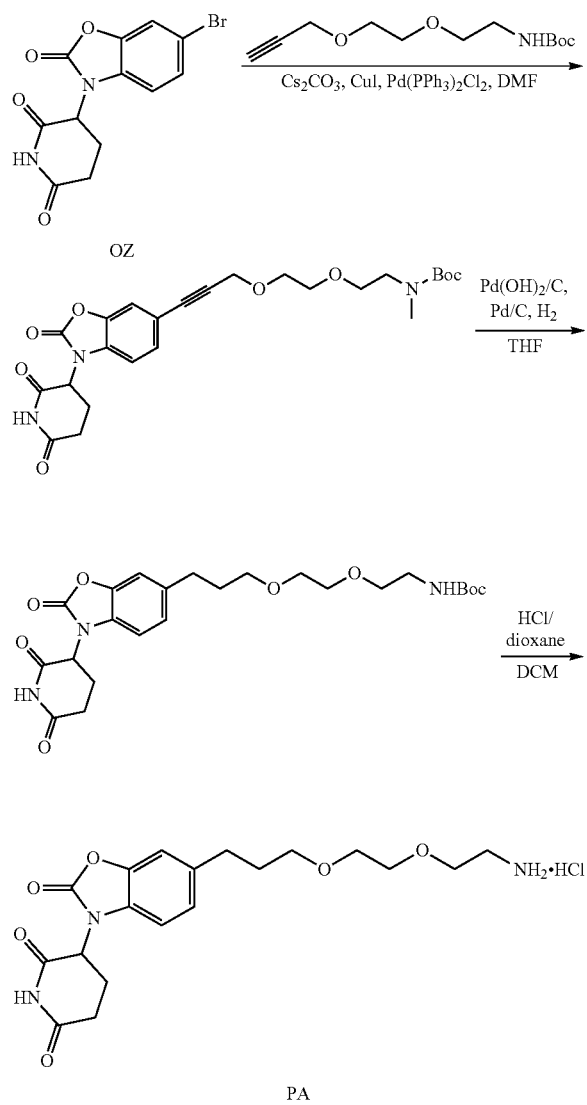

PA

Step 1—Tert-butyl N-[2-[2-[3-[3-(2,6-dioxo-3-piperidyl)-2-oxo-1,3-benzoxazol-6-yl]propoxy]ethoxy]ethyl]carbamate 3-(6-bromo-2-oxo-1,3-benzoxazol-3-yl)piperidine-2,6-dione (400 mg, 1.23 mmol, Intermediate OZ), tert-butylN-[2-(2-prop-2-ynoxyethoxy)ethyl]carbamate (898 mg, 3.69 mmol, synthesized via Step 1 of Intermediate CQ), Pd(PPh₃)₂Cl₂ (86.3 mg, 123 umol), CuI (23.4 mg, 123 umol), 4 Å MS (400 mg, 307 umol) and Cs₂CO₃ (2.00 g, 6.15 mmol) in DMF (6 mL) was stirred at 80° C. for 2 hours under N₂. On completion, the reaction mixture was filtered and the filtrate was concentrated in vacuo. The residue was purified by column chromatography (ACN) to give an impure product. The impure product was re-purified by reverse phase (0.1% FA condition) to give the title compound (340 mg, 54% yield) as yellow oil. ¹H NMR (400 MHz, DMSO-d₆) δ 11.23 (s, 1H), 7.53 (s, 1H), 7.37-7.33 (m, 1H), 7.31-7.27 (m, 1H), 6.82-6.75 (m, 1H), 5.40 (dd, J=5.2, 12.8 Hz, 1H), 4.39 (s, 2H), 3.65-3.60 (m, 2H), 3.57-3.53 (m, 2H), 3.41-3.38 (m, 2H), 3.07-3.02 (m, 2H), 2.93-2.81 (m, 1H), 2.72-2.61 (m, 2H), 2.18-2.16 (m, 1H), 1.37 (s, 9H), 1.37-1.36 (m, 1H). LC-MS (ESI⁺) m/z 510.2 (M+Na)⁺.

Step 2—Tert-butyl N-[2-[2-[3-[3-(2,6-dioxo-3-piperidyl)-2-oxo-1,3-benzoxazol-6-yl]propoxy]ethoxy]ethyl]carbamate To a solution of tert-butyl N-[2-[2-[3-[3-(2,6-dioxo-3-piperidyl)-2-oxo-1,3-benzoxazol-6-yl]prop-2-ynoxy]ethoxy]ethyl]carbamate (420 mg, 861 umol) in THF (30 mL) was added Pd/C (0.1 g, 10% wt) and Pd(OH)₂/C (0.1 g, 10% wt) under N₂. The suspension was degassed under vacuum and purged with H₂ gas several times. The mixture was stirred under H2 (15 psi) at 20° C. for 12 hours. On completion, the reaction mixture was filtered and the filtrate was concentrated in vacuo to give the title compound (440 mg, 93% yield) as yellow oil. ¹H NMR (400 MHz, DMSO-d₆) δ 11.25 (s, 1H), 7.32 (s, 1H), 7.22 (d, J=8.0 Hz, 1H), 7.11 (d, J=8.0 Hz, 1H), 6.79 (s, 1H), 5.40 (dd, J=5.2, 12.8 Hz, 1H), 3.57-3.53 (m, 4H), 3.46-3.43 (m, 4H), 3.13 (d, J=6.0 Hz, 2H), 3.00-2.89 (m, 1H), 3.00-2.89 (m, 1H), 2.80-2.67 (m, 4H), 2.25-2.20 (m, 1H), 1.88-1.83 (m, 2H), 1.43-1.42 (m, 9H). LC-MS (ESI⁺) m/z 514.2 (M+Na)⁺.

Step 3—2-3-[6-[3-[2-(2-Aminoethoxy)ethoxy]propyl]-2-oxo-1,3-benzoxazol-3-yl]piperidine-2,6-dione To a solution of tert-butyl N-[2-[2-[3-[3-(2,6-dioxo-3-piperidyl)-2-oxo-1,3-benzoxazol-6-yl]propoxy] ethoxy]ethyl]carbamate (150 mg, 305 umol) in DCM (5 mL) was added HCl/dioxane (4 M, 7.50 mL). The reaction mixture was stirred at 20° C. for 1 hour. On completion, the reaction mixture was concentrated in vacuo to give the title compound (130 mg, 99% yield, HCl salt) as a white solid. LC-MS (ESI⁺) m/z 392.2 (M+H)⁺.

Tert-butyl N-(3-prop-2-ynoxypropyl)carbamate (Intermediate PX)

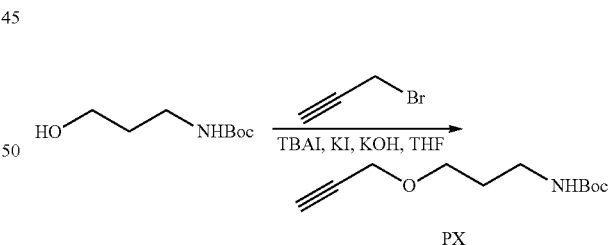

PX

To a mixture of tert-butyl N-(3-hydroxypropyl)carbamate (10.0 g, 57.1 mmol, CAS #58885-58-8), 3-bromoprop-1-yne (8.15 g, 68.5 mmol, CAS #106-96-7) in THF (150 mL) was added TBAI (1.26 g, 3.42 mmol) KOH (3.20 g, 57.07 mmol) and KI (1.42 g, 8.56 mmol). The mixture was stirred at 20° C. for 12 hours. On completion, the reaction mixture was concentrated in vacuo to give residue. The residue was purified by column chromatography to give the title compound (6.80 g, 55% yield) as yellow solid. ¹H NMR (400 MHz, CDCl₃) δ 4.76 (s, 1H), 4.10-4.05 (m, 2H), 3.51 (t, J=6.0 Hz, 2H), 3.16 (q, J=6.0 Hz, 2H), 2.37 (t, J=2.4 Hz, 1H), 1.74-1.65 (m, 2H), 1.37 (s, 9H).

3-[7-[3-(3-Aminopropoxy)propyl]-2-oxo-1,3-benzo-xazol-3-yl]piperidine-2,6-dione (Intermediate PY)

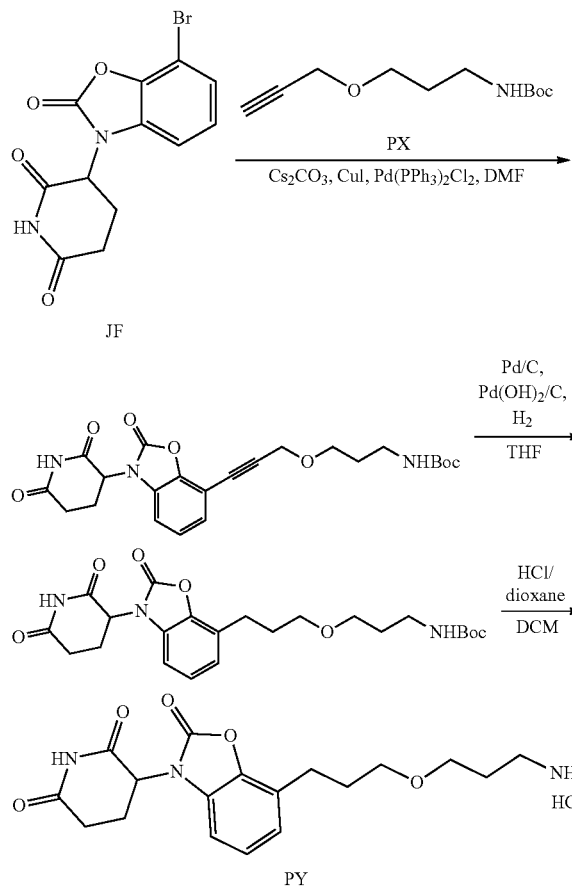

Step 1—Tert-butyl N-[3-[3-[3-(2,6-dioxo-3-piperidyl)-2-oxo-1,3-benzoxazol-7-yl]prop-2-ynoxy]propyl] carbamate To a mixture of 3-(7-bromo-2-oxo-1,3-benzoxazol-3-yl)piperidine-2,6-dione (3.00 g, 9.23 mmol, Intermediate JF) and tert-butyl N-(3-prop-2-ynoxypropyl)carbamate (4.92 g, 23.0 mmol, Intermediate PX) in DMF (30 mL) was added Cs$_2$CO$_3$ (15.0 g, 46.1 mmol), CuI (175 mg, 922 umol) and Pd(PPh$_3$)$_2$Cl$_2$ (647 mg, 922 umol). The reaction mixture was stirred at 80° C. for 2 hours. On completion, the reaction mixture was filtered and concentrated in vacuo. The residue was diluted with water (50 mL) and extracted with EA (3×100 mL). The combined organic layers was dried over Na$_2$SO$_4$, filtered and concentrated in vacuo to give a residue. The residue was purified by reverse phase (0.1% FA condition) to give the title compound (2.70 g, 63% yield) as light yellow solid. $^1$H NMR (400 MHz, DMSO-d$_6$) δ 11.23 (s, 1H), 7.32 (dd, J=2.0, 7.2 Hz, 1H), 7.27-7.19 (m, 2H), 6.81-6.77 (m, 1H), 5.39 (dd, J=5.6, 13.2 Hz, 1H), 4.43 (s, 2H), 3.53 (t, J=6.4 Hz, 2H), 3.02-2.97 (m, 2H), 2.92-2.81 (m, 1H), 2.73-2.58 (m, 2H), 2.22-2.13 (m, 1H), 1.70-1.64 (m, 2H), 1.36 (s, 9H); LC-MS (ESI$^+$) m/z 480.2 (M+Na)$^+$.

Step 2—Tert-butyl N-[3-[3-[3-(2,6-dioxo-3-piperidyl)-2-oxo-1,3-benzoxazol-7-yl]propoxy]propyl] carbamate To a mixture was tert-butyl N-[3-[3-[3-(2,6-dioxo-3-piperidyl)-2-oxo-1,3-benzoxazol-7-yl]prop-2-ynoxy]propyl] carbamate (2.30 g, 5.03 mmol) in THF (200 mL) was added Pd/C (0.6 g, 10% wt) and Pd(OH)$_2$/C (0.6 g, 10% wt). The reaction mixture was stirred at 25° C. for 12 hours under H$_2$ (15 Psi) atmosphere. On completion, the reaction mixture was filtered and concentrated in vacuo to give the title compound (2.30 g, 99% yield) as off-white solid. LC-MS (ESI$^+$) m/z 484.2 (M+Na)$^+$.

Step 3—3-[7-[3-(3-Aminopropoxy)propyl]-2-oxo-1,3-benzoxazol-3-yl]piperidine-2,6-dione To a mixture of tert-butyl N-[3-[3-[3-(2,6-dioxo-3-piperidyl)-2-oxo-1,3-benzoxazol-7-yl]propoxy] propyl]carbamate (2.30 g, 4.98 mmol) in DCM (10 mL) was added HCl/dioxane (4 M, 10 mL). The reaction mixture was stirred at 25° C. for 1 hour. On completion, the reaction mixture was concentrated in vacuo to give the title compound (1.80 g, 90% yield, HCl salt) as off-white solid. $^1$H NMR (400 MHz, DMSO-d$_6$) δ 11.20 (s, 1H), 7.86 (s, 2H), 7.17-7.09 (m, 2H), 7.04-7.00 (m, 1H), 5.37 (dd, J=5.2, 13.2 Hz, 1H), 3.47-3.43 (m, 2H), 3.43-3.41 (m, 2H), 2.90-2.84 (m, 2H), 2.83-2.79 (m, 1H), 2.78-2.72 (m, 2H), 2.70-2.61 (m, 2H), 2.20-2.10 (m, 1H), 1.91-1.84 (m, 2H), 1.83-1.78 (m, 2H).

3-[5-[3-(2-Aminoethoxy)propyl]-3-methyl-2-oxo-benzimidazol-1-yl]piperidine-2,6-dione (Intermediate RH)

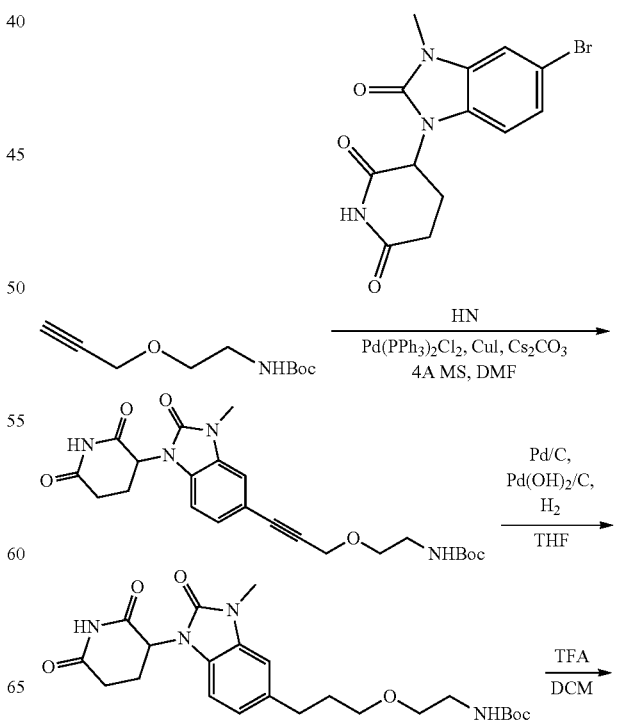

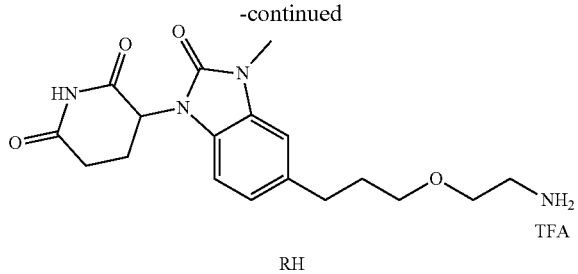

RH

Step 1—Tert-butyl N-[2-[3-[1-(2,6-dioxo-3-piperidyl)-3-methyl-2-oxo-benzimidazol-5-yl]prop-2-ynoxy]ethyl] carbamate To a solution of 3-(5-bromo-3-methyl-2-oxo-benzimidazol-1-yl)piperidine-2,6-dione (600 mg, 1.77 mmol, Intermediate HN) and tert-butyl N-(2-prop-2-ynoxyethyl)carbamate (883 mg, 4.44 mmol, synthesized via Step 1 on Intermediate CP) in DMF (10 mL) was added $Cs_2CO_3$ (2.31 g, 7.10 mmol), CuI (67.5 mg, 354 umol), 4 Å molecular sieve (20 mg) and $Pd(PPh_3)_2Cl_2$ (249 mg, 354. umol). The mixture was heated at 80° C. for 2 hours. On completion, the reaction mixture was filtered and the filtrate was concentrated in vacuo. The residue was diluted with water (30 mL), and then extracted with EA (3×40 mL). The combined organic layers were dried over $Na_2SO_4$, filtered and concentrated in vacuo to give a residue. The residue was purified by prep-HPLC (FA condition) to give the title compound (650 mg, 80% yield) as light yellow solid. $^1$H NMR (400 MHz, DMSO-$d_6$) δ 11.12 (s, 1H), 7.32 (s, 1H), 7.19-7.10 (m, 2H), 6.90-6.78 (m, 1H), 5.39 (dd, J=5.6, 12.8 Hz, 1H), 4.37 (s, 2H), 4.11 (d, J=2.4 Hz, 1H), 3.50 (t, J=6.0 Hz, 2H), 3.34 (s, 3H), 3.18-3.09 (m, 2H), 2.95-2.82 (m, 1H), 2.73-2.55 (m, 2H), 2.09-1.99 (m, 1H), 1.37 (s, 9H); LC-MS (ESI$^+$) m/z 357.2 (M+H-100)$^+$.

Step 2—Tert-butyl N-[2-[3-[1-(2,6-dioxo-3-piperidyl)-3-methyl-2-oxo-benzimidazol-5-yl]propoxy]ethyl]carbamate To a solution of tert-butyl N-[2-[3-[1-(2,6-dioxo-3-piperidyl)-3-methyl-2-oxo-benzimidazol-5-yl] prop-2-ynoxy] ethyl]carbamate (600 mg, 1.31 mmol) in THF (20 mL) was added Pd(OH)$_2$/C (150 mg, 10 wt %) and Pd/C (150 mg, 10 wt %) under $N_2$. The suspension was degassed under vacuum and purged with $H_2$ gas three times. The mixture was stirred at 25° C. for 16 hours under $H_2$ (15 PSI). On completion, the reaction mixture was filtered and the filtrate was concentrated in vacuo to give the title compound (500 mg, 82% yield) as white solid. $^1$H NMR (400 MHz, DMSO-$d_6$) δ 11.07 (s, 1H), 7.08-6.92 (m, 2H), 6.86 (dd, J=1.2, 8.4 Hz, 1H), 6.77 (t, J=5.2 Hz, 1H), 5.33 (dd, J=5.2, 12.8 Hz, 1H), 3.39-3.33 (m, 4H), 3.32 (s, 3H), 3.15-3.03 (m, 2H), 2.97-2.81 (m, 1H), 2.73-2.58 (m, 4H), 2.03-1.95 (m, 1H), 1.86-1.74 (m, 2H), 1.37 (s, 9H); LC-MS (ESI$^+$) m/z 483.1 (M+Na)$^+$.

Step 3—3-[5-[3-(2-Aminoethoxy)propyl]-3-methyl-2-oxo-benzimidazol-1-yl]piperidine-2,6-dione To a solution of tert-butyl N-[2-[3-[1-(2,6-dioxo-3-piperidyl)-3-methyl-2-oxo-benzimidazol-5-yl] propoxy]ethyl] carbamate (150 mg, 325 umol) in DCM (3 mL) was added TFA (1.54 g, 13.5 mmol). The mixture was stirred at 30° C. for 0.5 hour. On completion, the reaction mixture was concentrated in vacuo to give the title compound (150 mg, 97% yield, TFA) as light yellow solid. LC-MS (ESI$^+$) m/z 361.1 (M+H)$^+$.

3-[4-[3-Tert-butyl N-[3-(prop-2-yn-1-yloxy)propyl] carbamate (Intermediate OH)

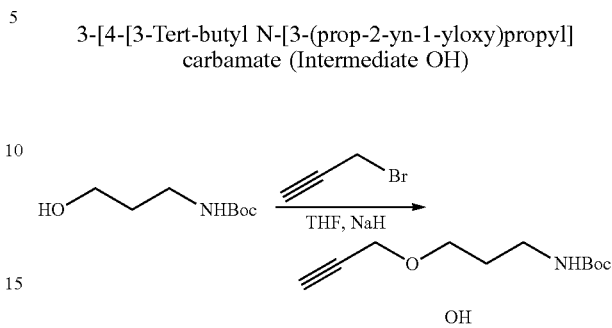

A solution of tert-butyl N-(3-hydroxypropyl)carbamate (1 g, 6 mmol, CAS #58885-58-8) in THF (40 mL) was treated with NaH (60% dispersion in mineral oil, 0.3 g, 14 mmol) for 30 min at 0° C. under nitrogen atmosphere. Next, a solution of 3-bromoprop-1-yne (0.7 g, 6.28 mmol) in THF (5 mL) was added dropwise at 0° C. The resulting mixture was stirred for 16 h at rt. The reaction was quenched with saturated aqueous $NH_4HCO_3$ (100 mL) and extracted with EtOAc (3×50 mL). The combined organic layer was washed with brine (50 mL) and dried over anhydrous $Na_2SO_4$. After filtration, the filtrate was concentrated under reduced pressure. The residue was purified by silica gel column chromatography, eluted with 5%-20% ethyl acetate in petroleum ether, to afford tert-butyl N-[3-(prop-2-yn-1-yloxy)propyl] carbamate (0.6 g, 49%) as a yellow oil: $^1$H NMR (400 MHz, DMSO-$d_6$) δ 6.77 (t, J=5.7 Hz, 1H), 4.10 (t, J=2.0 Hz, 2H), 3.44-3.39 (m, 3H), 2.99-2.91 (m, 2H), 1.64-1.59 (m, 2H), 1.38 (s, 9H); LC/MS (ESI, m/z): [(M −1)]$^-$=212.2.

(3-aminopropoxy)propyl]-3-methyl-2-oxo-benzimidazol-1-yl]piperidine-2,6-dione (Intermediate LF)

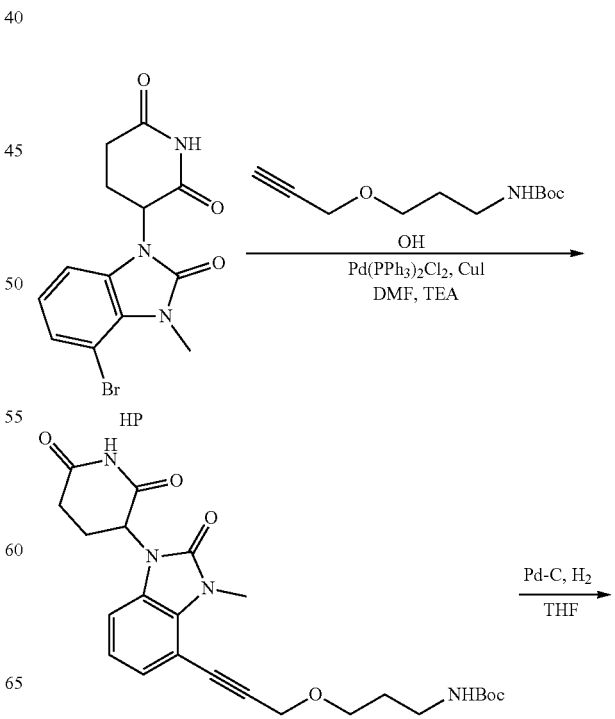

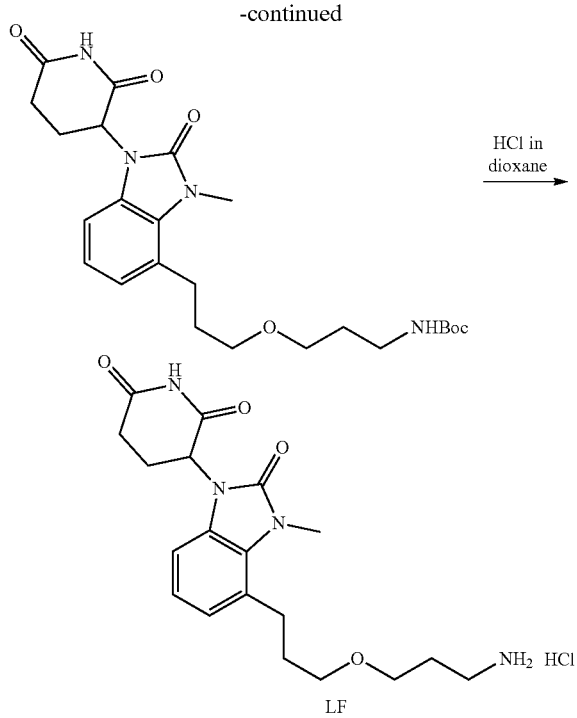

LF

Step 1—Tert-butyl N-[3-([3-[1-(2,6-dioxopiperidin-3-yl)-3-methyl-2-oxo-2,3-dihydro-1H-1,3-benzodiazol-4-yl]prop-2-yn-1-yl]oxy)propyl]carbamate To a stirred solution of 3-(4-bromo-3-methyl-2-oxo-2,3-dihydro-1H-1,3-benzodiazol-1-yl)piperidine-2,6-dione (221 mg, 0.65 mmol), tert-butyl N-[3-(prop-2-yn-1-yloxy)propyl]carbamate (209 mg, 0.98 mmol, Intermediate OH) and TEA (1 mL) in DMA (3 mL) were added CuI (12.4 mg, 0.07 mmol) and Pd(PPh$_3$)$_2$Cl$_2$ (45.9 mg, 0.07 mmol) at room temperature under nitrogen atmosphere. The resulting mixture was stirred for 2 h at 90° C. The mixture was cooled down to room temperature and concentrated under reduced pressure to remove TEA. The residue was purified by reverse phase flash chromatography with the following conditions: Column: WelFlash™ C18-I, 20-40 μm, 80 g; Eluent A: Water (plus 10 mmol/L FA); Eluent B: ACN; Gradient: 35%-55% B in 15 min; Flow rate: 50 mL/min; Detector: 220/254 nm; desired fractions were collected at 50% B and concentrated under reduced pressure to afford tert-butyl N-[3-([3-[1-(2,6-dioxopiperidin-3-yl)-3-methyl-2-oxo-2,3-dihydro-1H-1,3-benzodiazol-4-yl]prop-2-yn-1-yl]oxy)propyl]carbamate (90 mg, 29%) as a light pink solid. $^1$H NMR (400 MHz, CDCl$_3$) δ 8.12 (s, 1H), 7.20 (d, J=7.9 Hz, 1H), 7.01 (t, J=7.9 Hz, 1H), 6.78 (d, J=7.9 Hz, 1H), 5.22 (dd, J=12.5, 5.3 Hz, 1H), 4.80 (s, 1H), 4.42 (s, 2H), 3.80 (s, 3H), 3.68 (t, J=6.0 Hz, 2H), 3.30-3.24 (m, 2H), 3.02-2.95 (m, 1H), 2.91-2.69 (m, 2H), 2.28-2.26 (m, 1H), 1.85 (q, J=6.2 Hz, 2H), 1.46 (s, 9H); LC/MS (ESI, m/z): [(M−1)]$^-$=469.5.

Step 2—Tert-butyl N-(3-[3-[1-(2,6-dioxopiperidin-3-yl)-3-methyl-2-oxo-2,3-dihydro-1H-1,3-benzodiazol-4-yl]propoxy]propyl)carbamate To a stirred solution of tert-butyl N-[3-([3-[1-(2,6-dioxopiperidin-3-yl)-3-methyl-2-oxo-2,3-dihydro-1H-1,3-benzodiazol-4-yl]prop-2-yn-1-yl]oxy)propyl]carbamate (0.5 g, 1.06 mmol) in THF (10 mL) was added palladium on charcoal (100 mg, 10% w/w) at room temperature under nitrogen atmosphere. The resulting mixture was purged with H$_2$ gas 3 times and stirred for 16 h at room temperature under hydrogen atmosphere. The reaction mixture was filtered through a Celite pad. The filtrate was concentrated under reduced pressure to afford tert-butyl N-(3-[3-[1-(2,6-dioxopiperidin-3-yl)-3-methyl-2-oxo-2,3-dihydro-1H-1,3-benzodiazol-4-yl]propoxy]propyl)carbamate (430 mg, 85%) as a light green oil. $^1$H NMR (400 MHz, CDCl$_3$) δ 8.07 (s, 1H), 7.01 (t, J=7.8 Hz, 1H), 6.92 (d, J=7.8 Hz, 1H), 6.69 (d, J=7.7 Hz, 1H), 5.22 (dd, J=12.3, 5.5 Hz, 1H), 4.88 (s, 1H), 3.77 (s, 1H), 3.71 (s, 3H), 3.50 (m, 3H), 3.26 (d, J=6.3 Hz, 2H), 3.08-3.00 (m, 2H), 3.00-2.91 (m, 1H), 2.91-2.71 (m, 2H), 2.32-2.19 (m, 1H), 2.00-1.74 (m, 4H), 1.46 (s, 9H); LC/MS (ESI, m/z): [(M−1)]$^-$=473.3.

Step 3—3-[4-[3-(3-Aminopropoxy)propyl]-3-methyl-2-oxo-2,3-dihydro-1H-1,3-benzodiazol-1-yl]piperidine-2,6-dione hydrochloride To a stirred solution of tert-butyl N-(3-[3-[1-(2,6-dioxopiperidin-3-yl)-3-methyl-2-oxo-2,3-dihydro-1H-1,3-benzodiazol-4-yl]propoxy]propyl)carbamate (430 mg, 0.91 mmol) in 1,4-dioxane (5 mL) was added a solution of HCl in 1,4-dioxane (4 M, 5 mL) dropwise at 0° C. under nitrogen atmosphere. The resulting mixture was stirred for 3 h at room temperature. The resulting mixture was concentrated under reduced pressure and the residue was dissolved in 1,4-dioxane (15 mL) and re-concentrated under reduced pressure to afford 3-[4-[3-(3-aminopropoxy)propyl]-3-methyl-2-oxo-2,3-dihydro-1H-1,3-benzodiazol-1-yl]piperidine-2,6-dione hydrochloride (310 mg, 91%) as a brown yellow solid. $^1$H NMR (400 MHz, DMSO-d$_6$) δ 11.10 (s, 1H), 7.94 (s, 3H), 7.02-6.92 (m, 2H), 6.88 (dd, J=6.4, 2.5 Hz, 1H), 5.39 (dd, J=12.6, 5.4 Hz, 1H), 3.60-3.54 (s, 3H), 3.51-3.43 (m, 4H), 3.02-2.82 (m, 5H), 2.79-2.58 (m, 2H), 2.09-1.93 (m, 1H), 1.90-1.80 (m, 4H); LC/MS (ESI, m/z): [(M+1)]$^+$=375.3.

4-3-[4-[3-(2-Aminoethoxy)propyl]-3-methyl-2-oxobenzimidazol-1-yl]piperidine-2,6-dione (Intermediate RI)

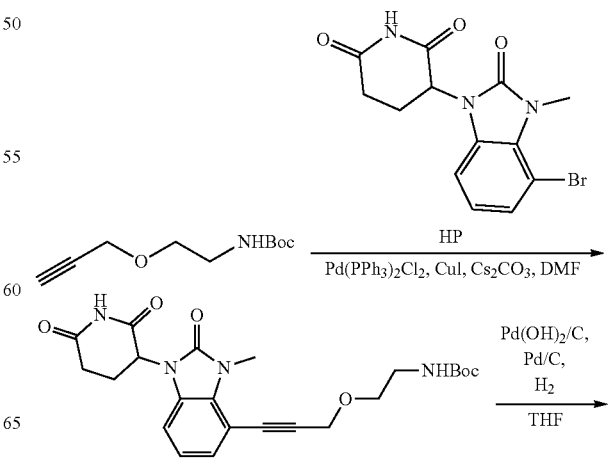

-continued

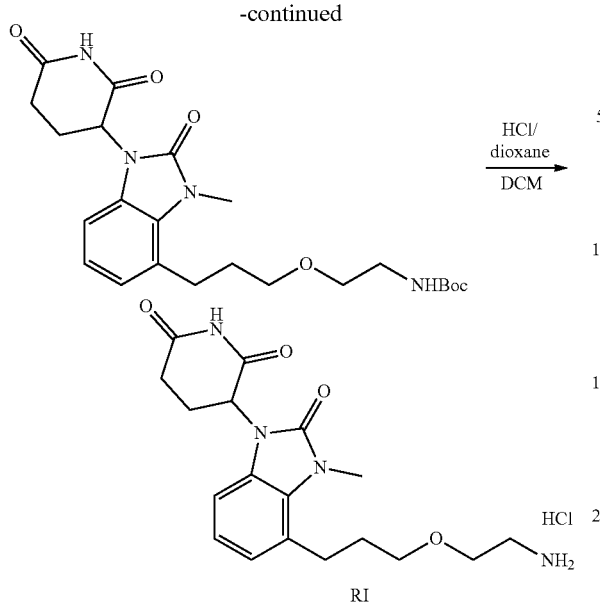

RI

Step 1—Tert-butyl N-[2-[3-[1-(2,6-dioxo-3-piperidyl)-3-methyl-2-oxo-benzimidazol-4-yl]prop-2-ynoxy]ethyl]carbamate To a mixture of tert-butyl N-(2-prop-2-ynoxyethyl)carbamate (4.42 g, 22.1 mmol, synthesized via Step 1 on Intermediate CP) and 3-(4-bromo-3-methyl-2-oxo-benzimidazol-1-yl)piperidine-2,6-dione (3.00 g, 8.87 mmol, Intermediate HP) in DMF (50 mL) was added $Cs_2CO_3$ (14.4 g, 44.3 mmol), CuI (168 mg, 887 umol) and $Pd(PPh_3)_2Cl_2$ (622 mg, 887 umol). The reaction mixture was stirred at 80° C. for 2 hours. On completion, the reaction mixture was filtered and concentrated in vacuo. The residue was diluted with water (50 mL) and extracted with EA (3×100 mL). The combined organic layers was dried over $Na_2SO_4$, filtered and concentrated in vacuo to give a residue. The residue was purified by prep-HPLC (0.1% FA condition) to give the title compound (2.70 g, 66% yield) as brown solid. $^1$H NMR (400 MHz, DMSO-$d_6$) δ 11.13 (s, 1H), 7.23-7.09 (m, 2H), 7.08-6.99 (m, 1H), 6.92-6.82 (m, 1H), 5.45-5.36 (m, 1H), 4.44 (s, 2H), 3.64 (s, 3H), 3.52 (t, J=6.0 Hz, 2H), 3.16-3.08 (m, 2H), 2.96-2.83 (m, 1H), 2.78-2.60 (m, 2H), 2.07-1.95 (m, 1H), 1.36 (s, 9H).

Step 2—Tert-butyl N-[2-[3-[1-(2,6-dioxo-3-piperidyl)-3-methyl-2-oxo-benzimidazol-4-yl]propoxy]ethyl]carbamate To a mixture of tert-butyl N-[2-[3-[1-(2,6-dioxo-3-piperidyl)-3-methyl-2-oxo-benzimidazol-4-yl]prop-2-ynoxy]ethyl]carbamate (200 mg, 438 umol) in THF (5 mL) was added Pd/C (100 mg, 10 wt %) and $Pd(OH)_2$/C (100 mg, 10 wt %). The reaction mixture was stirred at 25° C. for 12 hours under $H_2$ (15 PSI) atmosphere. On completion, the reaction mixture was filtered and concentrated in vacuo to give the title compound (200 mg, 99% yield) as light yellow oil. $^1$H NMR (400 MHz, DMSO-$d_6$) δ 11.08 (s, 1H), 7.00-6.92 (m, 2H), 6.91-6.84 (m, 1H), 6.79 (s, 1H), 5.39-5.32 (m, 1H), 3.56 (s, 3H), 3.44 (t, J=6.0 Hz, 2H), 3.40-3.38 (m, 2H), 3.09 (d, J=5.6 Hz, 2H), 2.98-2.93 (m, 2H), 2.90-2.83 (m, 1H), 2.71-2.60 (m, 2H), 2.03-1.94 (m, 1H), 1.88-1.76 (m, 2H), 1.37 (s, 9H).

Step 3—4-3-[4-[3-(2-Aminoethoxy)propyl]-3-methyl-2-oxo-benzimidazol-1-yl]piperidine-2,6-dione To a mixture of tert-butyl N-[2-[3-[1-(2,6-dioxo-3-piperidyl)-3-methyl-2-oxo-benzimidazol-4-yl] propoxy]ethyl] carbamate (200 mg, 434 umol) in DCM (3 mL) was added HCl/dioxane (4 M, 5 mL). The reaction mixture was stirred at 25° C. for 1 hour. On completion, the reaction mixture was concentrated in vacuo to give the title compound (172 mg, 99% yield) as light yellow solid. LC-MS (ESI$^+$) m/z 361.1 (M+H)$^+$.

3-[5-[3-[(2S)-2-(aminomethyl)morpholin-4-yl]propyl]-3-methyl-2-oxo-benzimidazol-1-yl] piperidine-2,6-dione (Intermediate RK)

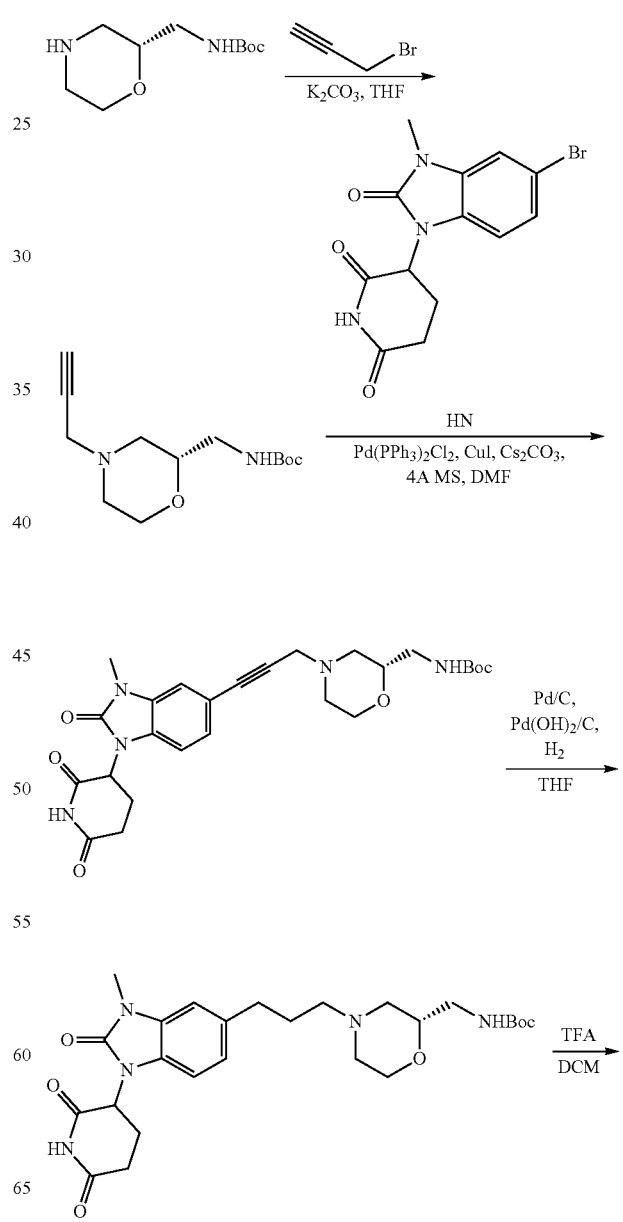

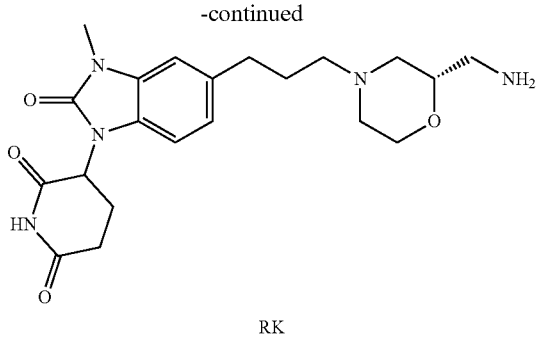

RK

Step 1—Tert-butyl N-[[(2S)-4-prop-2-ynylmorpholin-2-yl]methyl]carbamate

To a mixture of tert-butyl N-[[(2R)-morpholin-2-yl]methyl]carbamate (3 g, 13.8 mmol, CAS #186202-57-3) and 3-bromoprop-1-yne (1.98 g, 16.6 mmol) in THF (60 mL) was added $K_2CO_3$ (3.83 g, 27.7 mmol). The reaction mixture was stirred at 25° C. for 16 hours. On completion, the reaction mixture was filtered and concentrated in vacuo to give a residue. The residue was purified by column chromatography ($SiO_2$, petroleum ether/ethyl acetate=4/1) to give the title compound (2.4 g, 68% yield) as light yellow solid. $^1$H NMR (400 MHz, $CDCl_3$) δ 4.90 (s, 1H), 3.96-3.83 (m, 1H), 3.74-3.50 (m, 2H), 3.33-3.25 (m, 3H), 3.13-3.08 (m, 1H), 2.78-2.62 (m, 2H), 2.41-2.33 (m, 1H), 2.26 (t, J=2.4 Hz, 1H), 2.13 (t, J=10.4 Hz, 1H), 1.44 (s, 9H).

Step 2—Tert-butyl N-[[(2S)-4-[3-[1-(2,6-dioxo-3-piperidyl)-3-methyl-2-oxo-benzimidazol-5-yl]prop-2-ynyl]morpholin-2-yl]methyl] carbamate To a solution of 3-(5-bromo-3-methyl-2-oxo-benzimidazol-1-yl)piperidine-2,6-dione (265 mg, 784 umol, Intermediate HN) and tert-butyl N-[[(2S)-4-prop-2-ynylmorpholin-2-yl]methyl]carbamate (299 mg, 1.18 mmol) in DMF (15 mL) was added CuI (29.9 mg, 157 umol), $Pd(PPh_3)_2Cl_2$ (110 mg, 157 umol), $Cs_2CO_3$ (1.02 g, 3.13 mmol) and 4 Å molecular sieves (20 mg) at 25° C. The reaction mixture was stirred at 80° C. for 3 hours. On completion, the reaction mixture was filtered and the filtrate was concentrated in vacuo to give a residue. The residue was diluted with water (30 mL), and then extracted with EA (3×50 mL). The combined organic layers were washed with brine (50 mL), then dried over $Na_2SO_4$, filtered and the filtrate was concentrated in vacuo to give a residue. The residue was purified by reverse phase (0.1% FA condition) to give the title compound (270 mg, 67% yield) as a white solid. 1H NMR (400 MHz, $CDCl_3$) δ 8.18 (s, 1H), 7.17 (d, J=1.2 Hz, 1H), 7.10 (s, 1H), 6.73 (d, J=8.4 Hz, 1H), 5.20-5.16 (m, 1H), 4.93-4.89 (m, 1H), 3.95-3.89 (m, 1H), 3.72-3.71 (m, 1H), 3.54-3.49 (m, 2H), 3.43 (s, 3H), 3.15-3.07 (m, 1H), 2.99-2.99 (m, 1H), 2.99-2.92 (m, 1H), 2.89-2.61 (m, 6H), 2.48-2.40 (m, 1H), 2.28-2.22 (m, 1H), 2.17 (t, J=3.6 Hz, 1H), 1.43 (s, 9H); LC-MS (ESI$^+$) m/z 512.3 (M+H)$^+$.

Step 3—Tert-butyl N-[[(2S)-4-[3-[1-(2,6-dioxo-3-piperidyl)-3-methyl-2-oxo-benzimidazol-5-yl] propyl]morpholin-2-yl]methyl]carbamate To a solution of tert-butyl N-[[(2S)-4-[3-[1-(2,6-dioxo-3-piperidyl)-3-methyl-2-oxo-benzimidazol-5-yl]prop-2-ynyl]morpholin-2-yl]methyl]carbamate (270 mg, 528 umol) in THF (15 mL) was added Pd/C (120 mg, 528 umol, 10 wt %) and $Pd(OH)_2$/C (110 mg, 528 umol, 10 wt %) at 25° C. The reaction mixture was stirred at 25° C. for 2 hours under $H_2$ (15 PSI). On completion, the reaction mixture was filtered with celite and the filtrate was concentrated in vacuo to give a residue. The residue was purified by reverse phase (0.1% FA condition) to give the title compound (230 mg, 85% yield) as a brown solid. LC-MS (ESI$^+$) m/z 516.1 (M+H)$^+$.

Step 4—3-[5-[3-[(2S)-2-(aminomethyl)morpholin-4-yl]propyl]-3-methyl-2-oxo-benzimidazol-1-yl] piperidine-2,6-dione To a solution of tert-butyl N-[[(2S)-4-[3-[1-(2,6-dioxo-3-piperidyl)-3-methyl-2-oxo-benzimidazol-5-yl] propyl]morpholin-2-yl]methyl]carbamate (130 mg, 252 umol) in DCM (2 mL) was added TFA (1.67 g, 14.6 mmol). The reaction mixture was stirred at 25° C. for 2 hours. On completion, the reaction mixture was concentrated in vacuo to give the title compound (100 mg, 95% yield, TFA) as a brown oil. LC-MS (ESI$^+$) m/z 416.3 (M+H)$^+$.

3-[3-Methyl-5-[3-[(2R)-2-(methylaminomethyl)morpholin-4-yl]propyl]-2-oxo-benzimidazol-1-yl]piperidine-2,6-dione (Intermediate SZ)

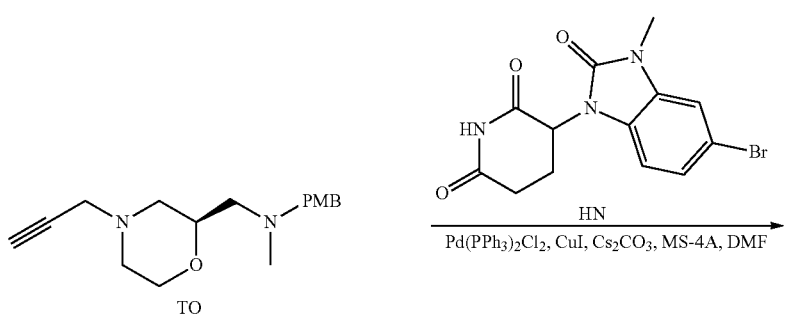

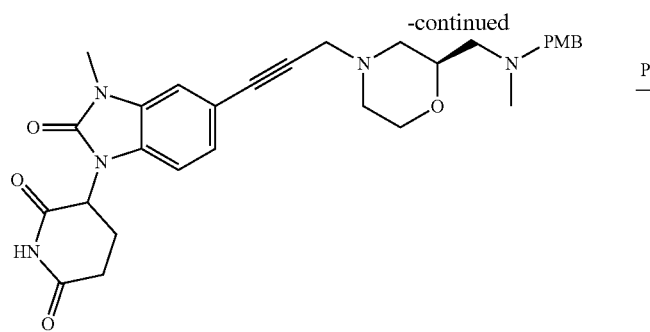

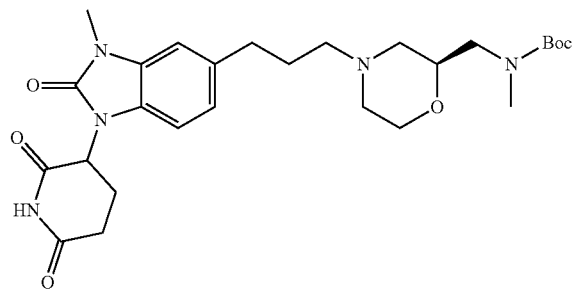

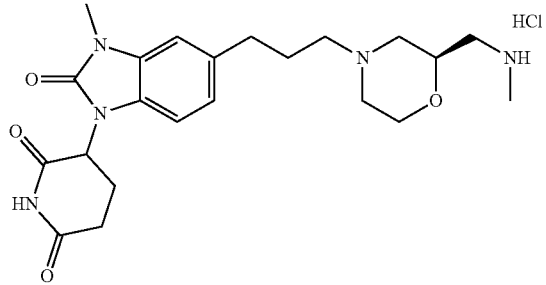

SZ

Step 1—3-[5-[3-[(2R)-2-[[(4-methoxyphenyl)methyl-methyl-amino]methyl]morpholin-4-yl]prop-1-ynyl]-3-methyl-2-oxo-benzimidazol-1-yl]piperidine-2,6-dione To a solution of 1-(4-methoxyphenyl)-N-methyl-N-[[(2R)-4-prop-2-ynylmorpholin-2-yl]methyl] methanamine (900 mg, 3.12 mmol, Intermediate TO) and 3-(5-bromo-3-methyl-2-oxo-benzimidazol-1-yl)piperidine-2,6-dione (703 mg, 2.08 mmol, Intermediate HN) in DMF (20 mL) was added 4 Å molecular sieves (300 mg), Pd(PPh$_3$)$_2$Cl$_2$ (146 mg, 208 umol), Cs$_2$CO$_3$ (2.71 g, 8.32 mmol) and CuI (39.6 mg, 208 umol). The reaction mixture was stirred at 80° C. for 2 hr under N$_2$. On completion, the mixture was filtered, and the filtrate was concentrated in vacuo to give a residue. The residue was purified by reverse phase (0.1% FA condition) to give the title compound (1.10 g, 96% yield) as a yellow solid. LC-MS (ESI$^+$) m/z 546.4 (M+H)$^+$.

Step 2—Tert-butyl N-[[(2S)-4-[3-[1-(2,6-dioxo-3-piperidyl)-3-methyl-2-oxo-benzimidazol-5-yl]propyl] morpholin-2-yl]methyl]-N-methyl-carbamate To a solution of 3-[5-[3-[(2R)-2-[[(4-methoxyphenyl)methyl-methyl-amino]methyl]morpholin-4-yl] prop-1-ynyl]-3-methyl-2-oxo-benzimidazol-1-yl]piperidine-2,6-dione (500 mg, 916 umol) in IPA (15 mL) and EA (30 mL) was added Pd(OH)$_2$/C (200 mg, 10 wt %), Pd/C (200 mg, 10 wt %) and (Boc)$_2$O (300 mg, 1.37 mmol, 315 uL). The reaction mixture was stirred at 25° C. for 48 hr under H$_2$ (50 psi). On completion, the residue was filtered and the filtrate was concentrated in vacuo to give a residue. The residue was purified by reverse phase (0.1% FA condition) to give the title compound (300 mg, 62% yield) as a yellow solid. $^1$H NMR (400 MHz, DMSO-d$_6$) δ 11.08 (s, 1H), 7.08-6.93 (m, 2H), 6.86 (d, J=8.0 Hz, 1H), 5.75 (s, 1H), 5.33 (dd, J=5.2, 12.8 Hz, 1H), 3.63-3.56 (m, 4H), 3.52-3.46 (m, 2H), 3.31 (s, 3H), 3.26-3.12 (m, 3H), 2.93-2.85 (m, 1H), 2.72-2.58 (m, 6H), 2.07-1.96 (m, 2H), 1.81-1.69 (m, 3H), 1.37 (s, 9H); LC-MS (ESI$^+$) m/z 530.3 (M+H)$^+$.

Step 3—3-[3-Methyl-5-[3-[(2R)-2-(methylaminomethyl)morpholin-4-yl]propyl]-2-oxo-benzimidazol-1-yl]piperidine-2,6-dione To a solution of tert-butyl N-[[(2S)-4-[3-[1-(2,6-dioxo-3-piperidyl)-3-methyl-2-oxo-benzimidazol-5-yl] propyl]morpholin-2-yl]methyl]-N-methyl-carbamate (300 mg, 566 umol) in DCM (8 mL) was added HCl/dioxane (4 M, 4 mL). The reaction mixture was stirred at 25° C. for 2 hr. On completion, the mixture was concentrated in vacuo to give the title compound (260 mg, 98% yield, HCl) as a white solid. LC-MS (ESI$^+$) m/z 430.2 (M+H)$^+$.

Tert-butyl N-(cyclopropylmethyl)-N-[4-[4-[[1-(4-formylcyclohexyl)-3-(1-hydroxy-1-methyl-ethyl)pyrazol-4-yl]carbamoyl]oxazol-2-yl]-2-pyridyl]carbamate (Intermediate UW)

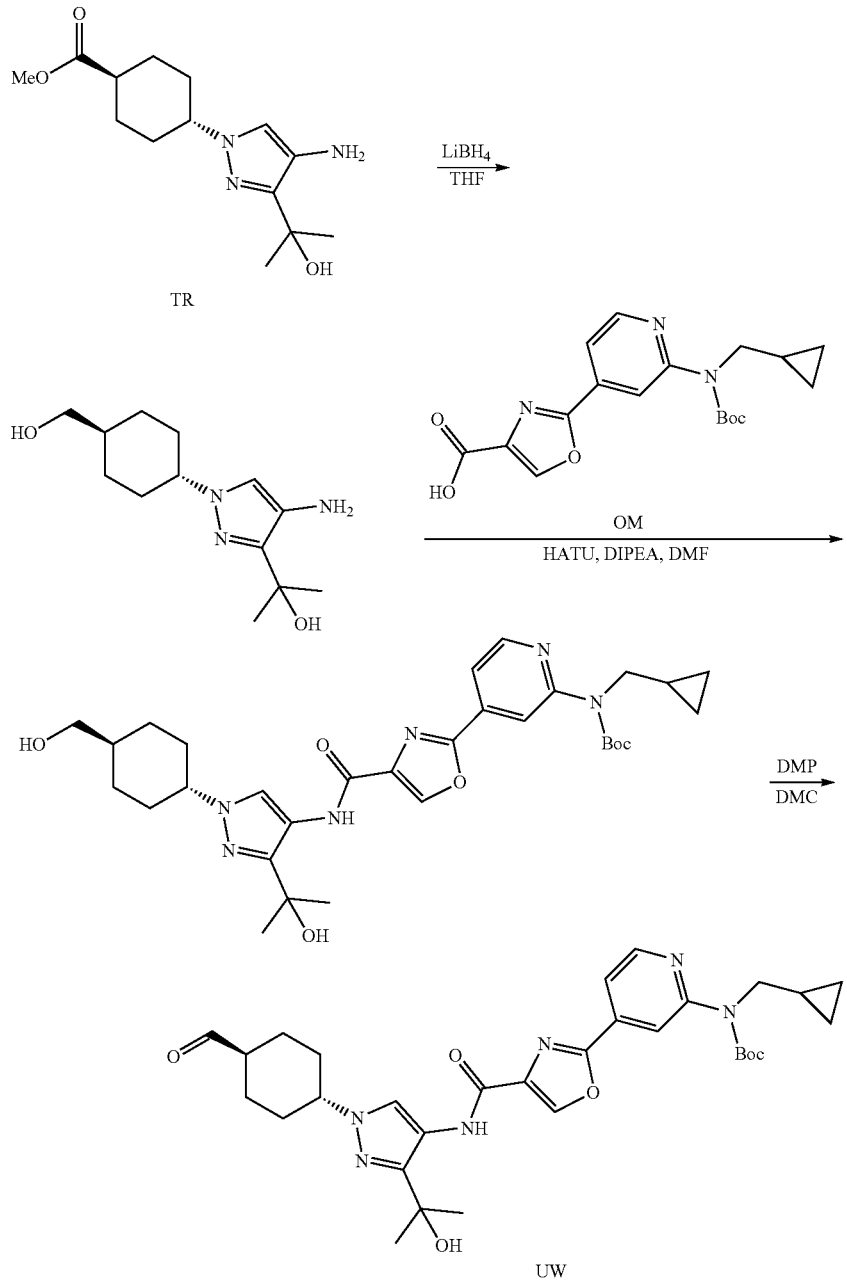

Step 1—2-[4-Amino-1-[4-(hydroxymethyl)cyclohexyl]pyrazol-3-yl]propan-2-ol

To a mixture of methyl 4-[4-amino-3-(1-hydroxy-1-methyl-ethyl) pyrazol-1-yl]cyclohexanecar boxylate (950 mg, 3.38 mmol, Intermediate TR) in THF (40 mL) and MeOH (5 mL) was added LiBH$_4$ (147 mg, 6.75 mmol) at 0° C. Then the mixture was stirred at 50° C. for 3 hours. On completion, the reaction was quenched by water (50 mL) and the aqueous phase was extracted with DCM (2×30 mL). The combined organic phase was washed with brine (2×40 mL), dried with anhydrous Na$_2$SO$_4$, filtered and concentrated in vacuo to give the title compound (720 mg, 83% yield) as a brown solid. $^1$H NMR (400 MHz, DMSO-d$_6$) δ 6.98-6.95 (m, 1H), 4.43 (t, J=5.2 Hz, 1H), 3.91-3.75 (m, 2H), 3.22 (t, J=5.6 Hz, 2H), 1.99-1.88 (m, 3H), 1.80 (d, J=13.2 Hz, 2H), 1.62-1.45 (m, 3H), 1.41-1.40 (m, 1H), 1.39 (s, 6H), 1.10-0.91 (m, 2H).

Step 2—Tert-butyl N-(cyclopropylmethyl)-N-[4-[4-[[1-[4-(hydroxymethyl)cyclohexyl]-3-(1-hydroxy-1-methyl-ethyl)pyrazol-4-yl] carbamoyl] oxazol-2-yl]-2-pyridyl]carbamate To a mixture of 2-[4-amino-1-[4-(hydroxymethyl)cyclohexyl]pyrazol-3-yl]propan-2-ol (250 mg, 888 umol) and 2-[2-[tert-butoxycarbonyl(cyclopropylmethyl)amino]-4-pyridyl]oxazole-4-carboxylic acid (271 mg, 755 umol, Intermediate OM) in DMF (5 mL) was added DIPEA (344 mg, 2.66 mmol). The mixture was stirred at 25° C. for 10 minutes. Then HATU (371 mg, 977 umol) was added into the mixture, the reaction mixture was stirred at 25° C. for 1 hour. On completion, the reaction mixture was poured into water (20 mL), then the aqueous phase was extracted with ethyl acetate (2×30 mL). The combined organic phase was washed with brine (2×40 mL), dried with anhydrous $Na_2SO_4$, filtered and concentrated in vacuo to give the title compound (450 mg, 85% yield) as a brown solid. LC-MS (ESI$^+$) m/z 595.3 (M+H)$^+$.

Step 3—Tert-butyl N-(cyclopropylmethyl)-N-[4-[4-[[1-(4-formylcyclohexyl)-3-(1-hydroxy-1-methyl-ethyl)pyrazol-4-yl] carbamoyl]oxazol-2-yl]-2-pyridyl]carbamate To a mixture of tert-butyl N-(cyclopropylmethyl)-N-[4-[4-[[1-[4-(hydroxymethyl)cyclohexyl]-3-(1-hydroxyl-1-methyl-ethyl)pyrazol-4-yl]carbamoyl]oxazol-2-yl]-2-pyridyl]carbamate (450 mg, 756 umol) in DCM (20 mL) was added DMP (385 mg, 908 umol). The reaction mixture was stirred at 25° C. for 0.5 hour. On completion, the reaction mixture was poured into the ice-water (40 mL), and extracted with EA (2×20 mL). The combined organic phase was washed with brine (2×20 mL), dried with anhydrous $Na_2SO_4$, filtered and concentrated in vacuo to give a residue. The crude product was purified by reversed-phase HPLC (0.1% FA condition) to give the title compound (140 mg, 28% yield) as a white solid. $^1$H NMR (400 MHz, CDCl$_3$) δ 10.17-10.06 (m, 1H), 9.69-9.60 (m, 1H), 8.42 (d, J=5.2 Hz, 1H), 8.34-8.23 (m, 2H), 8.19-8.08 (m, 1H), 7.55 (d, J=1.2, 5.2 Hz, 1H), 4.08-3.92 (m, 1H), 3.86 (d, J=7.2 Hz, 2H), 2.32-2.06 (m, 4H), 2.05-1.90 (m, 1H), 1.82-1.67 (m, 3H), 1.64 (s, 3H), 1.62-1.58 (m, 3H), 1.50 (s, 9H), 1.40 (d, J=3.2, 12.4 Hz, 1H), 1.22-1.07 (m, 2H), 0.40-0.31 (m, 2H), 0.25-0.13 (m, 2H).

3-[5-[3-[(2R)-2-(Aminomethyl)morpholin-4-yl]propyl]-3-methyl-2-oxo-benzimidazol-1-yl] piperidine-2,6-dione (Intermediate RJ)

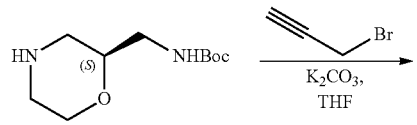

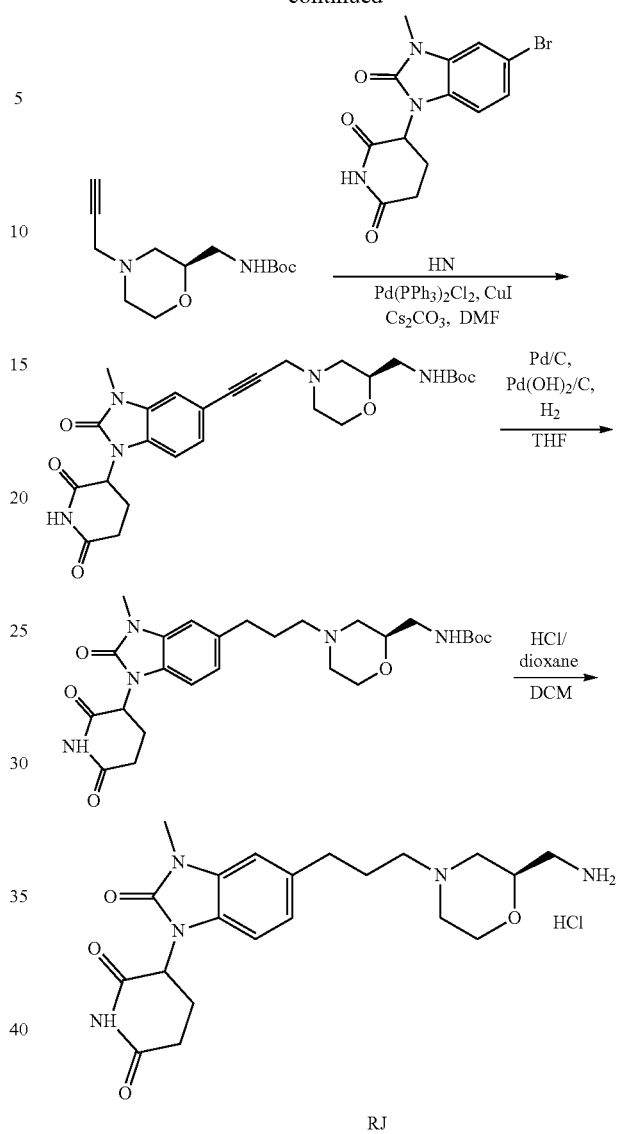

Step 1—Tert-butyl N-[[(2R)-4-prop-2-ynylmorpholin-2-yl]methyl]carbamate

To a solution of tert-butyl N-[[(2S)-morpholin-2-yl]methyl]carbamate (1.00 g, 4.62 mmol, CAS #875551-59-0) and 3-bromoprop-1-yne (550 mg, 4.62 mmol) in THF (20 mL) was added $K_2CO_3$ (1.28 g, 9.25 mmol). The reaction mixture was stirred at 25° C. for 12 hours. On completion, the mixture was diluted with water (30 mL) and extracted with EA (3×80 mL). The combined organic layers was dried over $Na_2SO_4$, filtered and concentrated in vacuo to give a residue. The residue was purified by column chromatography (SiO$_2$, Petroleum ether/Ethyl acetate=10/1 to 2/1) to give the title compound (800 mg, 68% yield) as yellow oil. $^1$H NMR (400 MHz, CDCl$_3$) δ 4.93 (s, 1H), 3.93-3.87 (m, 1H), 3.68 (dt, J=2.4, 11.2 Hz, 1H), 3.64-3.57 (m, 1H), 3.31 (d, J=2.4 Hz, 2H), 3.15-3.05 (m, 1H), 2.78-2.72 (m, 1H), 2.70-2.65 (1H), 2.39 (dt, J=3.6, 11.2 Hz, 1H), 2.27 (t, J=2.4 Hz, 1H), 2.13 (t, J=10.8 Hz, 1H), 1.87 (s, 1H), 1.45 (s, 9H).

Step 2—Tert-butyl N-[[(2R)-4-[3-[1-(2,6-dioxo-3-piperidyl)-3-methyl-2-oxo-benzimidazol-5-yl]prop-2-ynyl]morpholin-2-yl]methyl] carbamate To a solution of tert-butyl N-[[(2R)-4-prop-2-ynylmorpholin-2-yl]methyl]carbamate (846 mg, 3.33 mmol) and 3-(5-bromo-3-methyl-2-oxo-benzimidazol-1-yl)piperidine-2,6-dione (450 mg, 1.33 mmol, Intermediate HN) in DMF (15 mL) was added $Cs_2CO_3$ (2.17 g, 6.65 mmol), CuI (25.3 mg, 133 umol) and $Pd(PPh_3)_2Cl_2$ (93.4 mg, 133 umol). The reaction mixture was stirred at 80° C. for 2 hr under $N_2$. On completion, the mixture was filtered, and the filtrate was concentrated in vacuo to give a residue. The residue was purified by reverse phase (0.1% FA condition) to give the title compound (550 mg, 80% yield) as a yellow solid. $^1$H NMR (400 MHz, DMSO-$d_6$) δ 11.11 (s, 1H), 7.28 (s, 1H), 7.16-7.10 (m, 2H), 6.86-6.83 (m, 1H), 5.38 (dd, J=5.2, 12.4 Hz, 1H), 3.79 (t, J=13.2 Hz, 2H), 3.52 (s, 2H), 3.34 (s, 3H), 3.01-2.92 (m, 3H), 2.80-2.70 (m, 2H), 2.69-2.65 (m, 2H), 2.35-2.27 (m, 1H), 2.25-2.15 (m, 1H), 2.06-1.95 (m, 2H), 1.37 (s, 9H); LC-MS (ESI$^+$) m/z 512.2 (M+H)$^+$.

Step 3—Tert-butyl N-[[(2R)-4-[3-[1-(2,6-dioxo-3-piperidyl)-3-methyl-2-oxo-benzimidazol-5-yl]propyl] morpholin-2-yl]methyl] carbamate To a solution of tert-butyl N-[[(2R)-4-[3-[1-(2,6-dioxo-3-piperidyl)-3-methyl-2-oxo-benzimidazol-5-yl] prop-2-ynyl] morpholin-2-yl]methyl]carbamate (300 mg, 586 umol) in THF (10 mL) was added Pd/C (100 mg, 10 wt %) and $Pd(OH)_2$/C (100 mg, 10 wt %). The reaction mixture was stirred at 25° C. under $H_2$ (15 psi) for 12 hours. On completion, the residue was filtered and the filtrate was concentrated in vacuo to give a residue. The residue was purified by prep-HPLC (column: Phenomenex Synergi C18 150*25*10 um; mobile phase: [water (0.225% FA)-ACN]; B %: 1%-31%, 10 min) to give the title compound (120 mg, 39% yield) as a white solid. $^1$H NMR (400 MHz, DMSO-$d_6$) δ 11.08 (s, 1H), 7.04 (s, 1H), 7.00 (d, J=8.0 Hz, 1H), 6.87 (d, J=8.0 Hz, 1H), 6.82 (t, J=5.6 Hz, 1H), 5.33 (dd, J=5.2, 12.8 Hz, 1H), 3.43-3.40 (m, 3H), 3.32 (s, 3H), 3.03-2.87 (m, 3H), 2.73-2.58 (m, 6H), 2.36-2.25 (m, 2H), 2.03-1.95 (m, 2H), 1.79-1.66 (m, 3H), 1.36 (s, 9H); LC-MS (ESI$^+$) m/z 516.3 (M+H)$^+$.

Step 4—3-[5-[3-[(2R)-2-(aminomethyl)morpholin-4-yl]propyl]-3-methyl-2-oxo-benzimidazol-1-yl] piperidine-2,6-dione To a solution of tert-butyl N-[[(2R)-4-[3-[1-(2,6-dioxo-3-piperidyl)-3-methyl-2-oxo-benzimidazol-5-yl] propyl]morpholin-2-yl]methyl]carbamate (120 mg, 232 umol) in DCM (3 mL) was added HCl/dioxane (4 M, 1 mL). The reaction mixture was stirred at 25° C. for 2 hours. On completion, the mixture was concentrated in vacuo to give the title compound (100 mg, 95% yield) as a white solid. LC-MS (ESI$^+$) m/z 416.2 (M+H)$^+$.

3-[4-[3-[(2R)-2-(Aminomethyl)morpholin-4-yl]propyl]-3-methyl-2-oxo-benzimidazol-1-yl]piperidine-2,6-dione (Intermediate SQ)

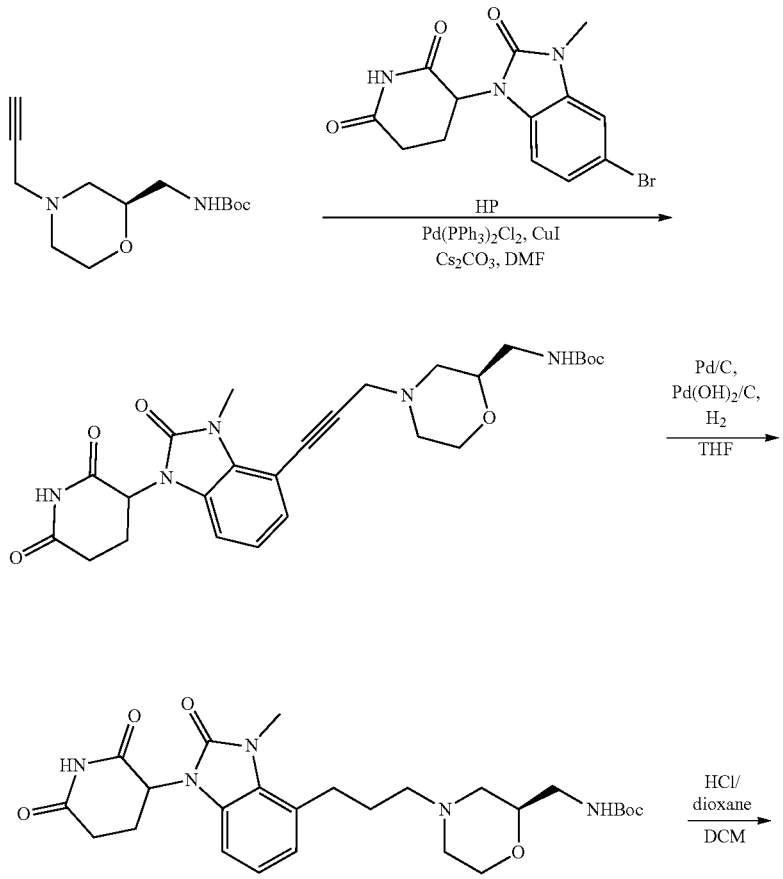

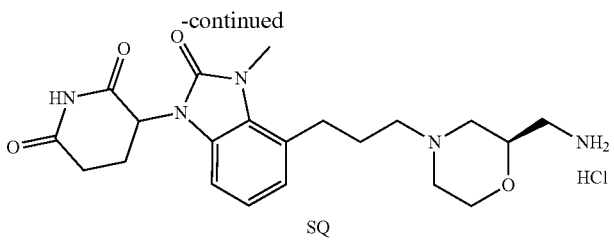

SQ

Step 1—Tert-butyl N-[[(2R)-4-[3-[1-(2,6-dioxo-3-piperidyl)-3-methyl-2-oxo-benzimidazol-5-yl]prop-2-ynyl]morpholin-2-yl]methyl] carbamate To a solution of tert-butyl N-[[(2R)-4-prop-2-ynylmorpholin-2-yl]methyl]carbamate (940 mg, 3.70 mmol, synthesized via Step 1 of Intermediate RJ) and 3-(4-bromo-3-methyl-2-oxo-benzimidazol-1-yl)piperidine-2,6-dione (500 mg, 1.48 mmol, Intermediate HP) in DMF (15 mL) was added $Cs_2CO_3$ (2.41 g, 7.39 mmol), CuI (28.1 mg, 147 umol) and $Pd(PPh_3)_2Cl_2$ (103 mg, 147 umol). The reaction mixture was stirred at 80° C. for 2 hr under $N_2$. On completion, the mixture was filtered, and the filtrate was concentrated in vacuo to give a residue. The residue was purified by reverse phase (0.1% FA condition) to give the title compound (500 mg, 66% yield) as a yellow solid. LC-MS (ESI+) m/z 512.3 (M+H)+.

Step 2—Tert-butyl N-[[(2R)-4-[3-[1-(2,6-dioxo-3-piperidyl)-3-methyl-2-oxo-benzimidazol-4-yl]propyl] morpholin-2-yl]methyl] carbamate To a solution of tert-butyl N-[[(2R)-4-[3-[1-(2,6-dioxo-3-piperidyl)-3-methyl-2-oxo-benzimidazol-4-yl]prop-2-ynyl]morpholin-2-yl]methyl]carbamate (500 mg, 977 umol) in THF (20 mL) was added Pd/C (100 mg, 10 wt %) and $Pd(OH)_2$/C (100 mg, 10 wt %). The reaction mixture was stirred at 25° C. under $H_2$ (15 psi) for 12 hrs. On completion, the residue was filtered and the filtrate was concentrated in vacuo to give a residue. The residue was purified by reverse phase (0.1% FA condition) to give the title compound (370 mg, 73% yield) as a white solid. $^1$H NMR (400 MHz, DMSO-$d_6$) δ 11.09 (s, 1H), 7.04-6.91 (m, 2H), 6.91-6.79 (m, 2H), 5.36 (dd, J=5.2, 12.4 Hz, 1H), 3.76 (d, J=10.4 Hz, 1H), 3.56 (s, 3H), 3.46 (t, J=10.8 Hz, 1H), 3.40-3.35 (m, 1H), 3.02-2.79 (m, 6H), 2.75-2.61 (m, 3H), 2.45-2.31 (m, 2H), 2.06-1.94 (m, 2H), 1.82-1.63 (m, 3H), 1.37 (s, 9H); LC-MS (ESI+) m/z 516.3 (M+H)+.

Step 3—3-[4-[3-[(2R)-2-(aminomethyl)morpholin-4-yl]propyl]-3-methyl-2-oxo-benzimidazol-1-yl] piperidine-2,6-dione To a solution of tert-butyl N-[[(2R)-4-[3-[1-(2,6-dioxo-3-piperidyl)-3-methyl-2-oxo-benzimidazol-4-yl] propyl]morpholin-2-yl]methyl]carbamate (370 mg, 717 umol) in DCM (3 mL) was added HCl/dioxane (4 M, 3.08 mL). The reaction mixture was stirred at 25° C. for 2 hrs. On completion, the mixture was concentrated in vacuo to give the title compound (320 mg, 98% yield, HCl) as a white solid. LC-MS (ESI+) m/z 416.3 (M+H)+.

3-[4-[3-[(2S)-2-(Aminomethyl)morpholin-4-yl]propyl]-3-methyl-2-oxo-benzimidazol-1-yl]piperidine-2,6-dione (Intermediate SR)

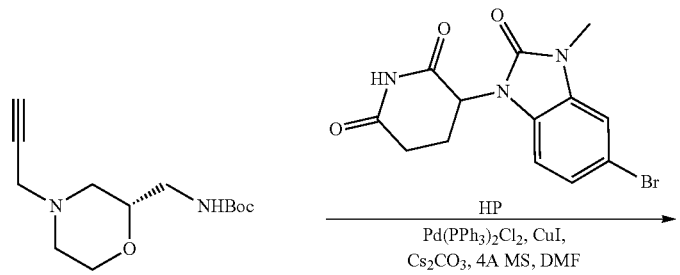

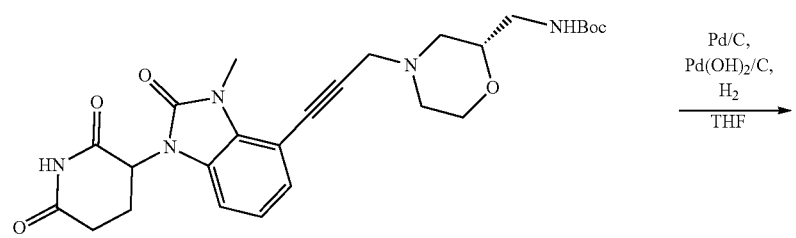

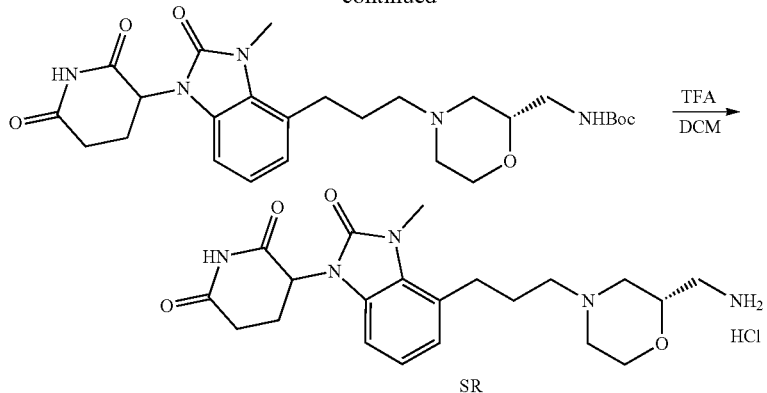

Step 1—Tert-butyl N-[[(2S)-4-[3-[1-(2,6-dioxo-3-piperidyl)-3-methyl-2-oxo-benzimidazol-4-yl] prop-2-ynyl]morpholin-2-yl]methyl]carbamate To a solution of 3-(4-bromo-3-methyl-2-oxo-benzimidazol-1-yl)piperidine-2,6-dione (500 mg, 1.48 mmol, Intermediate HP) and tert-butyl N-[[(2S)-4-prop-2-ynylmorpholin-2-yl]methyl]carbamate (564 mg, 2.22 mmol, synthesized via Step 1 of Intermediate RK) in DMF (20 mL) was added $Cs_2CO_3$ (1.93 g, 5.91 mmol), CuI (56.3 mg, 295 umol), 4 Å molecular sieves (20 mg) and $Pd(PPh_3)_2Cl_2$ (207 mg, 295 umol), and the mixture was heated at 80° C. for 2 hours. On completion, the reaction mixture was filtered and concentrated in vacuo. The residue was diluted with water (40 mL), and then extracted with EA (50 mL×3). The combined organic layers were dried over $Na_2SO_4$, filtered and concentrated in vacuo to give a residue. The residue was purified by prep-HPLC (FA condition) to give the title compound (430 mg, 56% yield) as light yellow solid. $^1H$ NMR (400 MHz, $CDCl_3$) δ 8.35 (s, 1H), 7.18 (dd, J=0.8, 8.0 Hz, 1H), 7.98 (t, J=8.0 Hz, 1H), 6.77 (dd, J=0.8, 8.0 Hz, 1H), 5.22 (dd, J=5.2, 12.8 Hz, 1H), 4.90 (s, 1H), 3.94 (dd, J=0.8, 11.6 Hz, 1H), 3.77 (s, 3H), 3.74-3.70 (m, 1H), 3.68-3.62 (m, 1H), 3.58 (d, J=2.0 Hz, 2H), 3.40-3.31 (m, 1H), 3.18-3.08 (m, 1H), 3.01-2.91 (m, 1H), 2.90-2.73 (m, 4H), 2.50-2.44 (m, 1H), 2.31-2.17 (m, 2H), 1.44 (s, 9H). LC-MS ($ESI^+$) m/z 512.3 $(M+H)^+$.

Step 2—Tert-butyl N-[[(2S)-4-[3-[1-(2,6-dioxo-3-piperidyl)-3-methyl-2-oxo-benzimidazol-4-yl]propyl] morpholin-2-yl]methyl]carbamate To a solution of tert-butyl N-[[(2S)-4-[3-[1-(2,6-dioxo-3-piperidyl)-3-methyl-2-oxo-benzimidazol-4-yl]prop-2-ynyl]morpholin-2-yl]methyl]carbamate (360 mg, 703 umol) in THF (5 mL) was added $Pd(OH)_2/C$ (40.0 mg, 10 wt %) and Pd/C (40.0 mg, 10 wt %) under $N_2$. The suspension was degassed under vacuum and purged with $H_2$ three times. The mixture was stirred under $H_2$ (15 psi) at 25° C. for 4 hours. On completion, the reaction mixture was filtered and concentrated in vacuo to give a residue. The residue was purified by prep-HPLC (FA condition) to give the title compound (280 mg, 77% yield) as light yellow solid. $^1H$ NMR (400 MHz, $CDCl_3$) δ 8.32 (s, 1H), 7.89 (t, J=8.4 Hz, 1H), 7.18 (d, J=0.8, 8.0 Hz, 1H), 6.67 (d, J=7.6 Hz, 1H), 5.22 (dd, J=5.2, 12.4 Hz, 1H), 4.90 (s, 1H), 3.87 (d, J=10.8 Hz, 1H), 3.72-3.52 (m, 5H), 3.40-3.25 (m, 1H), 3.17-3.03 (m, 1H), 3.01-2.91 (m, 3H), 2.87-2.66 (m, 4H), 2.41 (t, J=6.8 Hz, 2H), 2.26-2.08 (m, 2H), 1.94-1.83 (m, 3H), 1.45 (s, 9H); LC-MS ($ESI^+$) m/z 516.2 $(M+H)^+$.

Step 3—3-[4-[3-[(2S)-2-(aminomethyl)morpholin-4-yl]propyl]-3-methyl-2-oxo-benzimidazol-1-yl]piperidine-2,6-dione To a solution of tert-butyl N-[[(2S)-4-[3-[1-(2,6-dioxo-3-piperidyl)-3-methyl-2-oxo-benzimidazol-4-yl] propyl]morpholin-2-yl]methyl]carbamate (200 mg, 387 umol) in DCM (3 mL) was added TFA (924 mg, 8.10 mmol). The mixture was stirred at 25° C. for 1 hour. On completion, the reaction mixture was concentrated in vacuo to give the title compound (200 mg, 98% yield, TFA) as light yellow oil. LC-MS ($ESI^+$) m/z 416.3 $(M+H)^+$.

3-[(5S)-5-(3-Bromophenyl)-2-oxo-oxazolidin-3-yl]piperidine-2,6-dione (Intermediate SE)

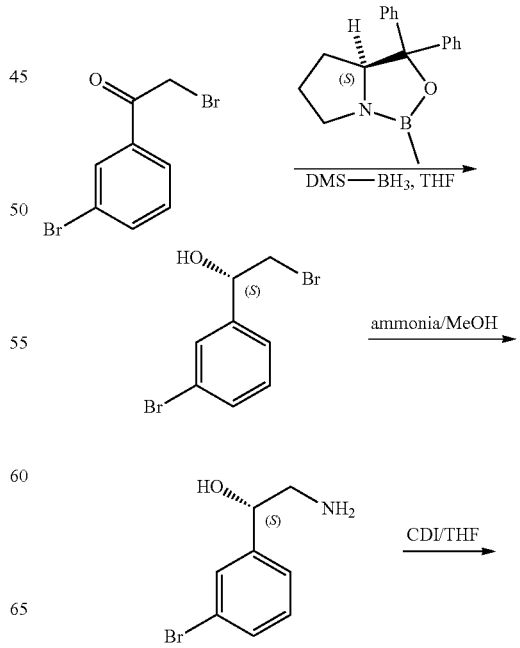

-continued

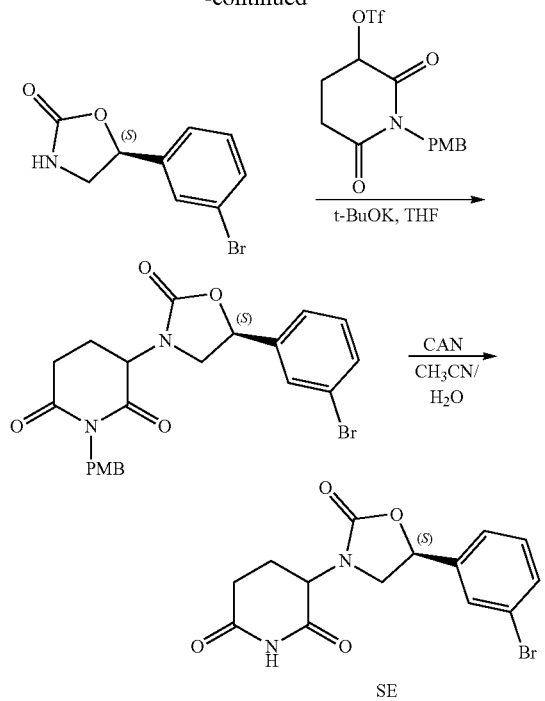

Step 1—(S)-2-bromo-1-(3-bromophenyl)ethanol

To a stirred solution of (S)-1-methyl-3,3-diphenylhexahydropyrrolo[1,2-c][1,3,2]oxazaborole (1 g, 3.61 mmol, CAS #112022-81-8) in THF (50 mL) was added $BH_3 \cdot DMS$ (10 M, 2.5 mL, 25.3 mmol) at 0° C. The mixture was stirred for 0.5 h at 0° C. To the reaction mixture was added a solution of 2-bromo-1-(3-bromophenyl)ethanone (10 g, 36.1 mmol) in THF (30 mL) dropwise at 0° C. The mixture was stirred for 12 h at rt. To the mixture was added MeOH dropwise, where the mixture released bubbles of gas. Addition of MeOH was halted after bubbling stopped. Then the mixture was concentrated and purified by column (PE/EA=50/1 to 20/1 to 10/1 to 5/1) to give the title compound (10 g, 100% yield) as a white solid. $^1$H NMR (400 MHz, $CDCl_3$) δ 7.56 (t, J=1.8 Hz, 1H), 7.47-7.45 (m, 1H), 7.32-7.30 (m, 1H), 7.26-7.22 (m, 1H), 4.90 (d, J=8.7 Hz, 1H), 3.63 (dd, J=10.5, 3.4 Hz, 1H), 3.51 (dd, J=10.5, 8.8 Hz, 1H), 2.68 (d, J=1.6 Hz, 1H).

Step 2—(S)-2-amino-1-(3-bromophenyl)ethanol

To a solution of (S)-2-bromo-1-(3-bromophenyl)ethanol (11 g, 90.3 mmol) in MeOH (80 mL) was added $NH_3$—$H_2O$ (25%, 200 mL) at 0° C. under $N_2$. The reaction mixture was stirred for 12 h under $N_2$ at room temperature. The mixture was concentrated. The solid was washed with EA to give the title compound (6.2 g, 74% yield) as a white solid. $^1$H NMR (400 MHz, DMSO-$d_6$) δ 7.70 (br s, 2H), 7.60 (t, J=1.9 Hz, 1H), 7.54-7.51 (m, 1H), 7.42-7.34 (m, 2H), 6.17 (d, J=3.8 Hz, 1H), 4.81-4.79 (m, 1H), 3.09 (dd, J=12.8, 3.2 Hz, 1H), 2.87 (dd, J=12.8, 9.6 Hz, 1H).

Step 3—(S)-5-(3-bromophenyl)oxazolidin-2-one

A mixture of (S)-2-amino-1-(3-bromophenyl)ethanol (1 g, 4.63 mmol), CDI (1.1 g, 6.94 mmol) and THF (30 mL) was heated to 80° C. and stirred for overnight at 80° C. under $N_2$. To the mixture was added $H_2O$ (20 mL), then the mixture was extracted with EA (50 mL). The organic layer was concentrated and purified by column chromatography on silica gel (PE/EA=2/1 to 1/1) to give the title compound (300 mg, 27% yield) as a yellow solid. $^1$H NMR (400 MHz, $CDCl_3$) δ 7.55-7.54 (m, 1H), 7.51 (dt, J=6.9, 2.0 Hz, 1H), 7.32-7.29 (m, 2H), 5.60 (t, J=8.0 Hz, 1H), 5.09 (br s, 1H), 4.00 (dt, J=0.6, 8.7 Hz, 1H), 3.53-3.49 (m, 1H).

Step 4—(R)-3-((S)-5-(3-bromophenyl)-2-oxooxazolidin-3-yl)-1-(4-methoxybenzyl)piperidine-2,6-dione To a solution of (S)-5-(3-bromophenyl)oxazolidin-2-one (8.1 g, 33.5 mmol) in THF (100 mL) was added t-BuOK (5.6 g, 50.3 mmol) at 0° C. under $N_2$. The mixture was stirred for 1 h at 0° C. Then to the mixture was added 1-(4-methoxybenzyl)-2,6-dioxopiperidin-3-yl trifluoromethanesulfonate (14 g, 36.8 mmol) at 0° C. under $N_2$. The mixture was stirred for 2 h at 0° C.~10° C. To the mixture was added EA (100 mL), then the solution was washed with $H_2O$ (100 mL), brine (50 mL), dried over $Na_2SO_4$, filtered, concentrated and purified by column chromatography on silica gel (PE/EA=2/1) to give a mixture of desired product and starting material. Then the mixture was re-purified by flash column chromatography (210 nm, 30% MeCN in $H_2O$) to give product (R)-3-((S)-5-(3-bromophenyl)-2-oxooxazolidin-3-yl)-1-(4-methoxybenzyl)piperidine-2,6-dione (4.0 g, 25% yield) as a white solid. $^1$H NMR (400 MHz, $CDCl_3$) δ 7.60-7.57 (m, 2H), 7.39-7.36 (m, 2H), 7.32-7.28 (m, 2H), 6.81-6.77 (m, 2H), 5.48 (t, J=8.4 Hz, 1H), 4.87 (s, 2H), 4.69 (dd, J=13.5, 5.2 Hz, 1H), 3.79 (t, J=8.4 Hz, 1H), 3.76 (s, 3H), 3.42 (t, J=8.0 Hz, 1H), 2.95 (ddd, J=17.8, 4.5, 2.4 Hz, 1H), 2.77 (ddd, J=17.8, 13.5, 5.5 Hz, 1H), 2.24-2.07 (m, 2H).

Step 5—(R)-3-((S)-5-(3-bromophenyl)-2-oxooxazolidin-3-yl)piperidine-2,6-dione

To a solution of (R)-3-((S)-5-(3-bromophenyl)-2-oxooxazolidin-3-yl)-1-(4-methoxybenzyl)piperidine-2,6-dione (4.0 g, 8.47 mmol) in MeCN (90 mL) was added dropwise a solution of CAN (18.6 g, 33.9 mmol) in $H_2O$ (20 mL) at 0° C. The mixture was stirred for 3 h at 0° C.~10° C. To the mixture was added $H_2O$ (50 mL), then the solution was extracted with EA (100 mL). The organic layer was washed with brine (30 mL), dried over $Na_2SO_4$, filtered, concentrated to give a yellow solid. The solid was washed with EA (30 mL) to give the title compound (1.2 g, 40% yield) as a white solid. The filtrate was concentrated and purified by flash (210 nm, 30% MeCN in $H_2O$) to give another portion of the title compound (0.2 g, 7% yield) as a white solid, the total yield is 47%. $^1$H NMR (400 MHz, DMSO-$d_6$) δ 11.00 (s, 1H), 7.72 (t, J=1.6 Hz, 1H), 7.63-7.60 (m, 1H), 7.50-7.49 (m, 1H), 7.42 (t, J=8 Hz, 1H), 5.63 (dd, J=7.6, 8.8 Hz, 1H), 4.71 (dd, J=5.2, 13.2 Hz, 1H), 3.94 (t, J=8.8 Hz, 1H), 3.29-3.25 (m, 1H), 2.92-2.82 (m, 1H), 2.59-2.57 (m, 1H), 2.25-2.14 (m, 1H), 2.03-2.01 (m, 1H). LC/MS (ESI, m/z): $[M+1]^+$=355.0.

3-[(5S)-5-[3-[3-[(2S)-2-(Aminomethyl)morpholin-4-yl]prop-1-ynyl]phenyl]-2-oxo-oxazolidin-3-yl]piperidine-2,6-dione (Intermediate SM)

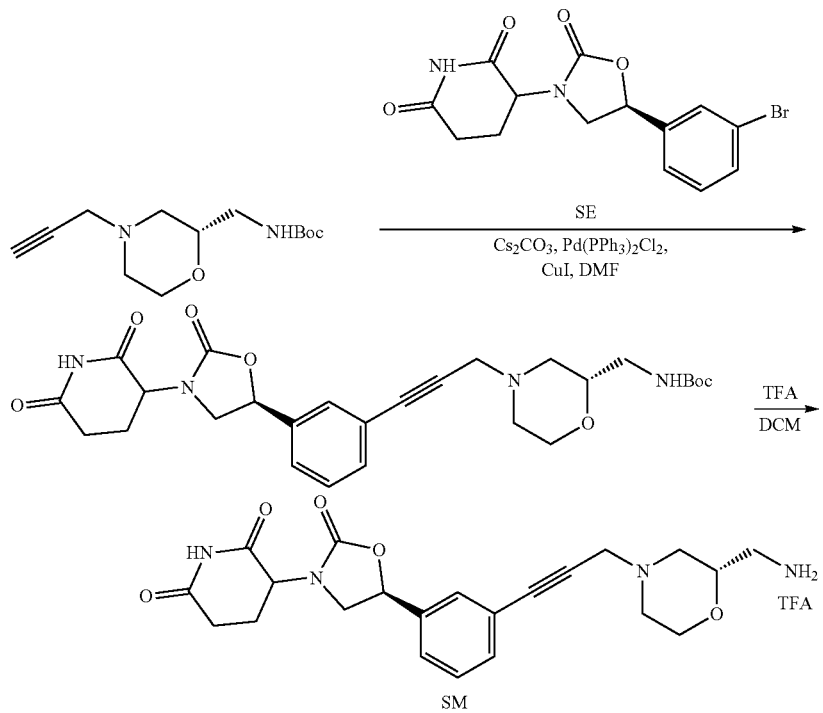

Step 1—Tert-butyl N-[[(2S)-4-[3-[3-[(5S)-3-(2,6-dioxo-3-piperidyl)-2-oxo-oxazolidin-5-yl]phenyl]prop-2-ynyl]morpholin-2-yl]methyl]carbamate To a mixture of tert-butyl N-[[(2S)-4-prop-2-ynylmorpholin-2-yl]methyl]carbamate (540 mg, 2.12 mmol, synthesized via Step 1 of Intermediate RK) and 3-[(5S)-5-(3-bromophenyl)-2-oxo-oxazolidin-3-yl]piperidine-2,6-dione (300 mg, 849 umol, Intermediate SE) in DMF (5 mL) was added Pd(PPh$_3$)$_2$Cl$_2$ (59.6 mg, 84.9 umol), CuI (16.1 mg, 84.9 umol) and Cs$_2$CO$_3$ (1.38 g, 4.25 mmol). The reaction mixture was stirred at 80° C. for 2 hours under N$_2$ atmosphere. On completion, the reaction mixture was filtered and concentrated in vacuo. The residue was diluted with water (30 mL) and extracted with EA (3×30 mL). The combined organic layers was dried over Na$_2$SO$_4$, filtered and concentrated in vacuo to give a residue. The residue was purified by reverse phase (0.1% FA condition) to give the title compound (450 mg, 95% yield) as light yellow solid. LC-MS (ESI$^+$) m/z 527.3 (M+H)$^+$.

Step 2—3-[(5S)-5-[3-[3-[(2S)-2-(aminomethyl)morpholin-4-yl]prop-1-ynyl]phenyl]-2-oxo-oxazolidin-3-yl]piperidine-2,6-dione To a mixture of tert-butyl N-[[(2S)-4-[3-[3-[(5S)-3-(2,6-dioxo-3-piperidyl)-2-oxo-oxazolidin-5-yl] phenyl]prop-2-ynyl]morpholin-2-yl]methyl]carbamate (180 mg, 341 umol) in DCM (3 mL) was added TFA (4.62 g, 40.5 mmol, 3 mL). The reaction mixture was stirred at 25° C. for 0.5 hour. On completion, the reaction mixture was concentrated in vacuo to give the title compound (184 mg, 99% yield, TFA) as red oil. LC-MS (ESI$^+$) m/z 427.1 (M+H)$^+$.

3-[(5S)-5-(4-Bromophenyl)-2-oxo-oxazolidin-3-yl]piperidine-2,6-dione (Intermediate SN)

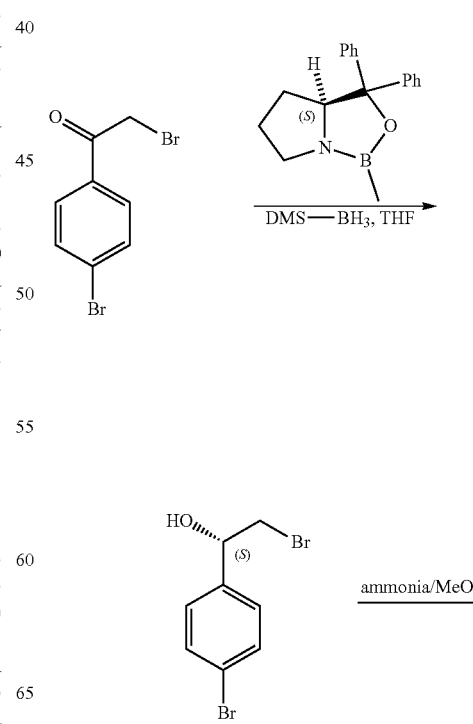

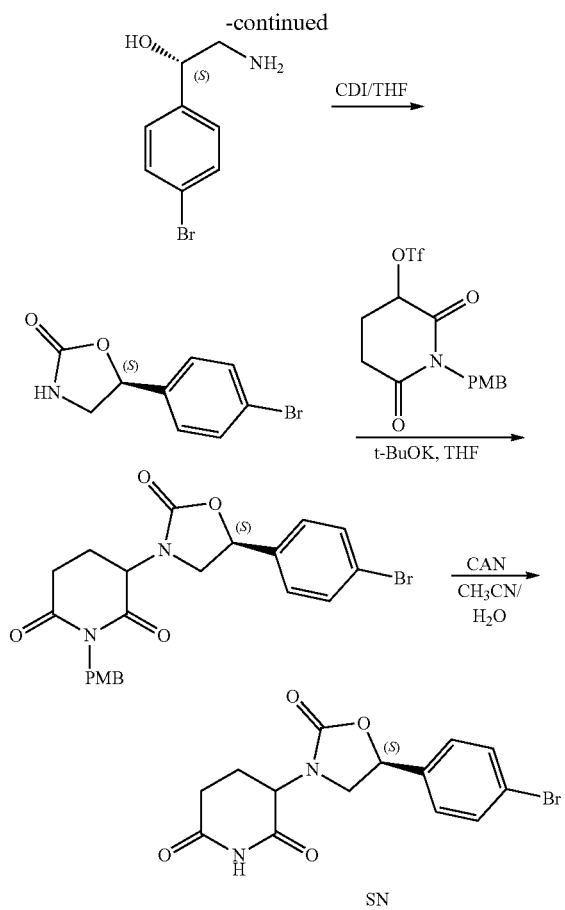

Step 1—(S)-2-bromo-1-(4-bromophenyl)ethanol

To a stirred solution of (S)-1-methyl-3,3-diphenylhexahydropyrrolo[1,2-c][1,3,2]oxazaborole (0.5 g, 1.81 mmol) in THF (25 mL) was added $BH_3 \cdot DMS$ (10 M, 1.3 mL, 12.7 mmol) at 0° C. The mixture was stirred for 0.5 h at 0° C. To the reaction mixture was then added a solution of 2-bromo-1-(4-bromophenyl)ethanone (5 g, 18.1 mmol) in THF (15 mL) dropwise at 0° C. The mixture was stirred for 12 h at rt. To the mixture was then added MeOH dropwise where gas evolved. MeOH was added until no more bubbling occurred. The mixture was concentrated and purified by column chromatography on silica gel (PE/EA=50/1 to 20/1 to 10/1 to 5/1) to give the title compound (5 g, 100% yield) as a white solid. $^1$H NMR (400 MHz, DMSO-$d_6$) δ 7.55-7.52 (m, 2H), 7.38-7.34 (m, 2H), 5.89 (d, J=4.9 Hz, 1H), 4.82-4.78 (m, 1H), 3.66 (dd, J=10.2, 4.6 Hz, 1H), 3.57 (dd, J=10.2, 6.8 Hz, 1H).

Step 2—(S)-2-amino-1-(4-bromophenyl)ethanol

To a solution of (S)-2-bromo-1-(4-bromophenyl)ethanol (15 g, 123 mmol) in MeOH (100 mL) was added $NH_3 \cdot H_2O$ (25%, 250 mL) at 0° C. under $N_2$. The reaction mixture was stirred at rt for 12 h under $N_2$. Then the mixture was concentrated. The solid was washed with EA to give the title compound (8.4 g, 74% yield) as a white solid. $^1$H NMR (400 MHz, DMSO-$d_6$) δ 7.54 (d, J=8.4 Hz, 2H), 7.32 (d, J=8.4 Hz, 2H), 5.51 (br s, 3H), 4.64 (dd, J=8.4, 3.6 Hz, 1H), 2.83 (dd, J=12.8, 3.4 Hz, 1H), 2.69 (dd, J=12.6, 6.8 Hz, 1H).

Step 3—(S)-5-(4-bromophenyl)oxazolidin-2-one

A mixture of (S)-2-amino-1-(4-bromophenyl)ethanol (22 g, 102 mmol), CDI (24.2 g, 153 mmol) and THF (500 mL) was heated to 80° C. and stirred for overnight at 80° C. under $N_2$. To the mixture was then added $H_2O$ (200 mL), and the mixture was extracted with EA (300 mL). The organic layer was concentrated and purified by column (PE/EA=2/1 to 1/1) to give the title compound (8.0 g, 33% yield) as a yellow solid.

Step 4—(R)-3-((S)-5-(4-bromophenyl)-2-oxooxazolidin-3-yl)-1-(4-methoxybenzyl)piperidine-2,6-dione To a solution of (S)-5-(3-bromophenyl)oxazolidin-2-one (8.0 g, 30.2 mmol) in THF (100 mL) was added t-BuOK (5.5 g, 49.8 mmol) at 0° C. under $N_2$. The mixture was stirred for 1 h at 0° C. Then to the mixture was added 1-(4-methoxybenzyl)-2,6-dioxopiperidin-3-yl trifluoromethanesulfonate (13.9 g, 36.8 mmol) at 0° C. under $N_2$. The mixture was stirred at 0° C.~-10 OC for 2 h. To the mixture was then added EA (100 mL), the solution was then washed with $H_2O$ (100 mL), brine (50 mL), dried over $Na_2SO_4$, filtered, concentrated and purified by column chromatography on silica gel (PE/EA=2/1) to give a mixture of desired product (R)-3-((S)-5-(4-bromophenyl)-2-oxooxazolidin-3-yl)-1-(4-methoxybenzyl)piperidine-2,6-dione and starting material. Then the mixture was re-purified by flash column chromatography (210 nm, 30% MeCN in $H_2O$) to give the title compound (4.5 g, 28% yield) as a white solid. $^1$H NMR (400 MHz, CDCl$_3$) δ 7.57-7.52 (m, 2H), 7.34-7.29 (m, 2H), 7.26-7.24 (m, 2H), 6.86-6.80 (m, 2H), 5.89 (dd, J=8.7, 7.1 Hz, 1H), 4.89 (s, 2H), 4.58 (dd, J=12.8, 6.0 Hz, 1H), 3.94 (t, J=8.4 Hz, 1H), 3.78 (s, 3H), 3.80 (dd, J=17.9, 7.1 Hz, 1H), 2.97-2.90 (m, 1H), 2.79-2.70 (m, 1H), 2.20-2.04 (m, 2H).

Step 5—(R)-3-((S)-5-(4-bromophenyl)-2-oxooxazolidin-3-yl)piperidine-2,6-dione

To a solution of (R)-3-((S)-5-(4-bromophenyl)-2-oxooxazolidin-3-yl)-1-(4-methoxybenzyl)piperidine-2,6-dione (50 mg, 0.106 mmol) in MeCN (5 mL) was added dropwise a solution of CAN (232 mg, 0.424 mmol) in $H_2O$ (1 mL) at 0° C. The mixture was stirred for 3 h at 0° C.~-10° C. To the mixture was then added $H_2O$ (100 mL), and the solution was extracted with EA (200 mL). The organic layer was washed with brine (50 mL), dried over $Na_2SO_4$, filtered, concentrated and purified by column (PE/EA=1/1) to give the title compound (5 mg, 14% yield) as a white solid. $^1$H NMR (400 MHz, CDCl$_3$) δ 8.20 (s, 1H), 7.56 (d, J=8.0 Hz, 2H), 7.35 (d, J=8.0 Hz, 2H), 5.49 (t, J=8.2 Hz, 1H), 4.74 (dd, J=13.0, 5.2 Hz, 1H), 3.84 (t, J=8.4 Hz, 1H), 3.48 (t, J=7.8 Hz, 1H), 2.91-2.87 (m, 1H), 2.82-2.73 (m, 1H), 2.22-2.11 (m, 2H). LC/MS (ESI, m/z): [M+1]$^+$=355.0.

Step 6—(S)-3-((S)-5-(4-bromophenyl)-2-oxooxazolidin-3-yl)piperidine-2,6-dione

To a solution of (S)-3-((S)-5-(4-bromophenyl)-2-oxooxazolidin-3-yl)-1-(4-methoxybenzyl)piperidine-2,6-dione (80 mg, 0.169 mmol) in MeCN (10 mL) was added dropwise a solution of CAN (372 mg, 0.678 mmol) in $H_2O$ (2 mL) at 0° C. The mixture was stirred for 3 h at 0° C.~-10° C. To the mixture was added $H_2O$ (100 mL), then the mixture was extracted with EA (200 mL). The organic layer was washed with brine (50 mL), dried over $Na_2SO_4$, filtered, concentrated and purified by column (PE/EA=1/1) to give the title compound (1.5 mg, 3% yield) as a white solid. ¹H NMR (400 MHz, CDCl₃) δ 7.86 (s, 1H), 7.56 (d, J=8.2 Hz, 2H), 7.26-7.22 (m, 2H), 5.60 (t, J=7.8 Hz, 1H), 4.64 (dd, J=12.0, 5.2 Hz, 1H), 4.00 (t, J=8.2 Hz, 1H), 3.41 (t, J=7.4 Hz, 1H), 2.91-2.86 (m, 1H), 2.78-2.73 (m, 1H), 2.24-2.20 (m, 2H). LC/MS (ESI, m/z): [M+1]⁺=355.0.

3-[(5S)-5-[4-[3-[(2S)-2-(Aminomethyl)morpholin-4-yl]prop-1-ynyl]phenyl]-2-oxo-oxazolidin-3-yl]piperidine-2,6-dione (Intermediate SO)

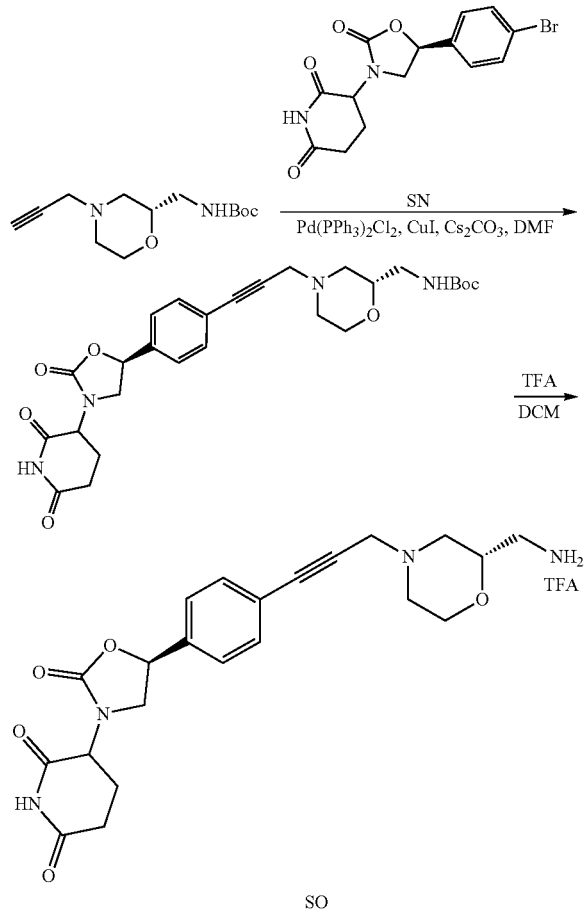

SO

Step 1—Tert-butyl N-[[(2S)-4-[3-[4-[(5S)-3-(2,6-dioxo-3-piperidyl)-2-oxo-oxazolidin-5-yl]phenyl] prop-2-ynyl]morpholin-2-yl]methyl]carbamate To a solution of tert-butyl N-[[(2S)-4-prop-2-ynylmorpholin-2-yl]methyl]carbamate (648 mg, 2.55 mmol, synthesized via Step 1 of Intermediate RK) and 3-[(5S)-5-(4-bromophenyl)-2-oxo-oxazolidin-3-yl]piperidine-2,6-dione (300 mg, 849 umol, Intermediate SN) in DMF (15 mL) was added Pd(PPh₃)₂Cl₂ (119 mg, 169 umol), CuI (32.3 mg, 169 umol) and Cs₂CO₃ (1.38 g, 4.25 mmol). The reaction mixture was stirred at 80° C. for 2 hours under N₂. On completion, the mixture was filtered and the filtrate was concentrated in vacuo to give a residue. The residue was purified by reverse phase (0.1% FA condition) to give the title compound (440 mg, 80% yield) as a yellow solid. ¹H NMR (400 MHz, DMSO-d₆) δ11.00 (d, J=6.0 Hz, 1H), 7.53-7.40 (m, 4H), 6.88-6.84 (m, 1H), 5.73-5.61 (m, 1H), 4.75-4.63 (m, 1H), 3.94 (t, J=8.8 Hz, 1H), 3.89 (t, J=8.8 Hz, 1H), 3.80 (t, J=7.2 Hz, 2H), 3.50-3.40 (m, 4H), 3.30-3.21 (m, 2H), 2.60-2.52 (m, 2H), 2.37-2.15 (m, 3H), 2.02-1.92 (m, 2H), 1.36 (s, 9H); LC-MS (ESI⁺) m/z 527.3 (M+H)⁺.

Step 2—3-[(5S)-5-[4-[3-[(2S)-2-(aminomethyl)morpholin-4-yl]prop-1-ynyl]phenyl]-2-oxo-oxazolidin-3-yl]piperidine-2,6-dione To a solution of tert-butyl N-[[(2S)-4-[3-[4-[(5S)-3-(2,6-dioxo-3-piperidyl)-2-oxo-oxazolidin-5-yl] phenyl] prop-2-ynyl]morpholin-2-yl]methyl]carbamate (150 mg, 284 umol) in DCM (3 mL) was added TFA (1.54 g, 13.5 mmol, 1 mL). The reaction mixture was stirred at 25° C. for 2 hours. On completion, the residue concentrated in vacuo to give the title compound (150 mg, 97% yield) as yellow oil. LC-MS (ESI⁺) m/z 427.2 (M+H)⁺.

2-[(E)-2-[1-(2,6-Dioxo-3-piperidyl)-3-methyl-2-oxo-benzimidazol-5-yl]vinyloxy]ethyl methanesulfonate (Intermediate TB)

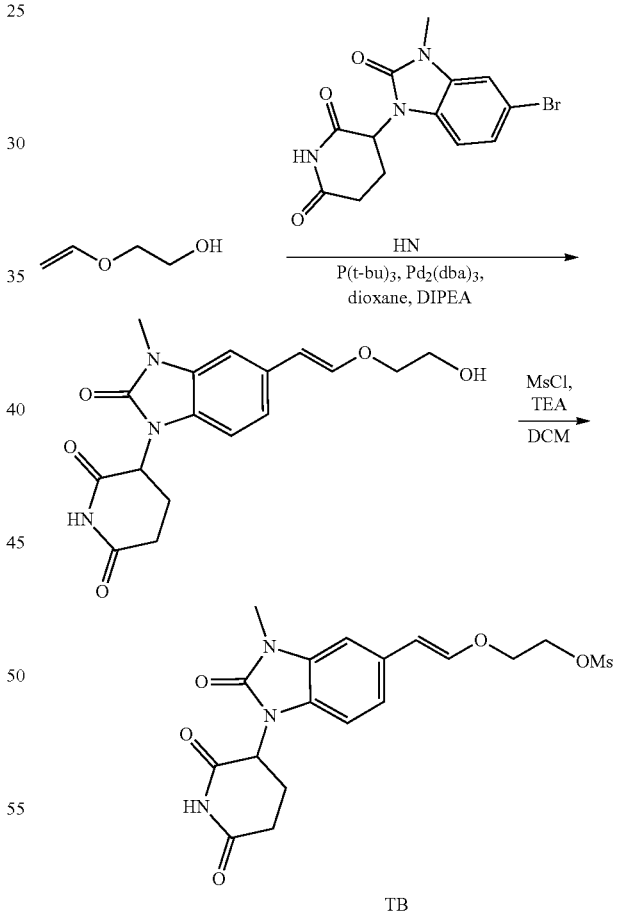

TB

Step 1—3-[5-[(E)-2-(2-Hydroxyethoxy)vinyl]-3-methyl-2-oxo-benzimidazol-1-yl]piperidine-2,6-dione To a solution of 3-(5-bromo-3-methyl-2-oxo-benzimidazol-1-yl)piperidine-2,6-dione (1.00 g, 2.96 mmol, Intermediate HN), 2-vinyloxyethanol (782 mg, 8.88 mmol, CAS #764-48-7) in dioxane (25 mL) was added P(t-Bu)₃ toluene solution (2.08 mL, 591 umol, 10 wt %), Pd₂(dba)₃ (542 mg, 591 umol) and DIPEA (497 mg, 3.84 mmol) under N₂. The mixture was stirred at 25° C. for 16 hours. On completion, the mixture was concentrated in vacuo. The residue was purified by silica gel column to give the title compound (500 mg, 49% yield) as yellow solid. ¹H NMR (400 MHz, DMSO-d₆) δ 11.08 (s, 1H), 7.25-7.19 (m, 1H), 7.19-7.09 (m, 1H), 6.99 (d, J=8.4 Hz, 1H), 6.95-6.90 (m, 1H), 6.35 (d, J=7.2 Hz, 1H), 5.88 (d, J=12.8 Hz, 1H), 5.38-5.29 (m, 1H), 5.25 (d, J=7.2 Hz, 1H), 3.99-3.83 (m, 1H), 3.85 (t, J=5.2 Hz, 1H), 3.69-3.61 (m, 2H), 3.39 (s, 3H), 2.97-2.82 (m, 1H), 2.66-2.58 (m, 1H), 2.53 (d, J=1.6 Hz, 1H), 2.06-1.99 (m, 1H).

Step 2—2-[(E)-2-[1-(2,6-Dioxo-3-piperidyl)-3-methyl-2-oxo-benzimidazol-5-yl]vinyloxy]ethyl methanesulfonate To a solution of 3-[5-[(E)-2-(2-hydroxyethoxy)vinyl]-3-methyl-2-oxo-benzimidazol-1-yl]piperidine-2,6-dione (750 mg, 2.17 mmol) in DCM (100 mL) was added TEA (659 mg, 6.52 mmol) and MsCl (373 mg, 3.26 mmol) at 0° C. The reaction mixture was stirred at 25° C. for 2 hours. On completion, the reaction mixture was poured into water (30 mL) and extracted with DCM (2×100 mL). The combined organic layers were washed with brine (80 mL) and sat. aq. NaHCO₃ (2×70 mL), dried with anhydrous Na₂SO₄, filtered and concentrated in vacuo to give the title compound (800 mg, 70% yield, 75% purity) as a brown solid. LC-MS (ESI⁺) m/z 423.9 (M+H)⁺.

3-[5-[2-[2-[(2S)-2-(Aminomethyl)morpholin-4-yl]ethoxy]ethyl]-3-methyl-2-oxo-benzimidazol-1-yl]piperidine-2,6-dione (Intermediate TC)

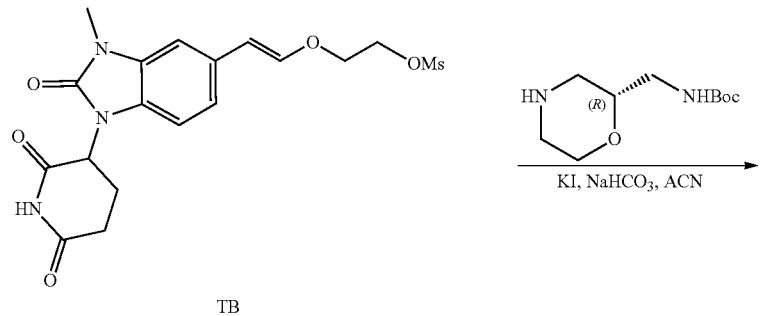

TB

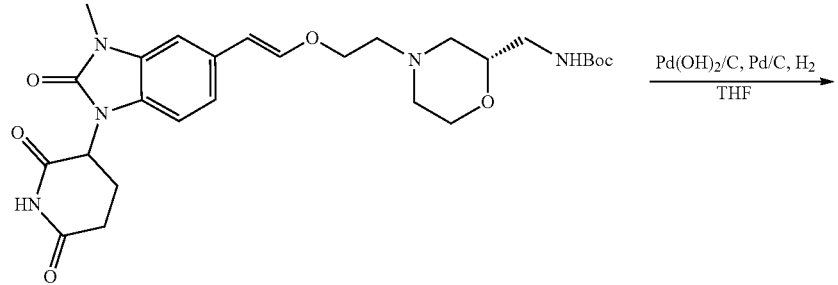

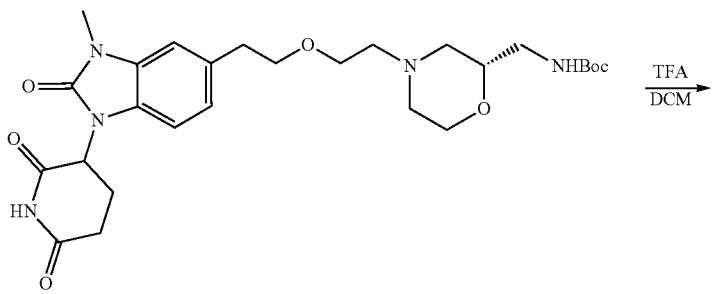

-continued

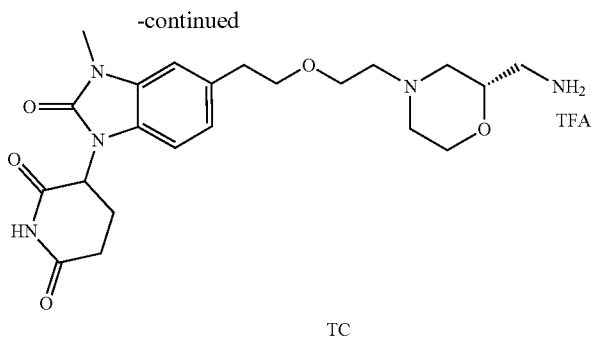

TC

Step 1—Tert-butylN-[[(2S)-4-[2-[(E)-2-[1-(2,6-di-oxo-3-piperidyl)-3-methyl-2-oxo-benzimidazol-5-yl]vinyloxy]ethyl]morpholin-2-yl]methyl] carbamate To a solution of 2-[(E)-2-[1-(2,6-dioxo-3-piperidyl)-3-methyl-2-oxo-benzimidazol-5-yl]vinyloxy]ethyl methanesulfonate (350 mg, 827 umol, Intermediate TB), tert-butyl N-[[(2R)-morpholin-2-yl]methyl]carbamate (268 mg, 1.24 mmol, CAS #186202-57-3) in DMF (5 mL) was added DIPEA (320 mg, 2.48 mmol) at 20° C. The mixture was stirred at 110° C. for 1 hour. On completion, the mixture was concentrated in vacuo. The mixture was purified by prep-HPLC (reverse phase: 0.1% FA) to give the title compound (270 mg, 60% yield) as a yellow solid. $^1$H NMR (400 MHz, CDCl$_3$) δ 8.28 (s, 1H), 6.97-6.82 (m, 2H), 6.82-6.69 (m, 1H), 6.12 (d, J=7.2 Hz, 1H), 5.95 (d, J=12.8 Hz, 1H), 5.43 (d, J=7.1 Hz, 1H), 5.26-5.18 (m, 1H), 4.89 (s, 1H), 4.39-4.18 (m, 2H), 4.06 (d, J=7.2 Hz, 2H), 3.98-3.87 (m, 1H), 3.68-3.54 (m, 2H), 3.46-3.43 (m, 3H), 3.41-3.36 (m, 2H), 3.33-3.24 (m, 2H), 2.99-2.91 (m, 2H), 2.87-2.81 (m, 1H), 2.79-2.75 (m, 1H), 2.74-2.68 (m, 1H), 2.31-2.21 (m, 1H), 1.47 (s, 9H).

Step 2—Tert-butyl N-[[(2S)-4-[2-[2-[1-(2,6-dioxo-3-piperidyl)-3-methyl-2-oxo-benzimidazol-5-yl]ethoxy] ethyl]morpholin-2-yl]methyl]carbamate To a solution of tert-butyl N-[[(2S)-4-[2-[(E)-2-[1-(2,6-dioxo-3-piperidyl)-3-methyl-2-oxo-benzimidazol-5-yl]vinyloxy]ethyl]morpholin-2-yl]methyl]carbamate (270 mg, 496 umol) in THF (20 mL) was added Pd/C (50.0 mg, 10 wt %) and Pd(OH)$_2$/C (50.0 mg, 10 wt %) at 25° C. The mixture was stirred at 25° C. for 2 hours under H$_2$ (15 psi) On completion, the mixture was filtered. The filtrate was concentrated in vacuo. The mixture was purified by prep-HPLC (reverse phase: 0.1% FA) to give the title compound (150 mg, 30% yield) as a yellow solid. $^1$H NMR (400 MHz, DMSO-d$_6$) δ 11.10 (s, 1H), 7.09 (s, 1H), 7.04-6.94 (m, 2H), 6.65 (s, 1H), 5.37-5.33 (m, 1H), 3.68 (s, 3H), 3.65-3.59 (m, 4H), 3.34 (s, 3H), 3.04-2.93 (m, 4H), 2.91-2.79 (m, 4H), 2.75-2.70 (m, 1H), 2.66-2.61 (m, 1H), 2.55-2.53 (m, 1H), 2.04-1.96 (m, 1H), 1.78-1.75 (m, 2H), 1.36 (s, 9H).

Step 3—3-[5-[2-[2-[(2S)-2-(Aminomethyl)morpholin-4-yl]ethoxy]ethyl]-3-methyl-2-oxo-benzimidazol-1-yl]piperidine-2,6-dione To a solution of tert-butyl N-[[(2S)-4-[2-[2-[1-(2,6-dioxo-3-piperidyl)-3-methyl-2-oxo-benzimidazol-5-yl]ethoxy]ethyl]morpholin-2-yl]methyl]carbamate (100 mg, 184 umol) in DCM (2 mL) was added TFA (1 mL) at 15° C. The mixture was stirred at 15° C. for 2 hours. On completion, the mixture was concentrated in vacuo to give the title compound (80.0 mg, 98% yield, TFA salt) as a white solid. LC-MS (ESI$^+$) m/z 446.3 (M+H)$^+$.

[4-[4-Amino-3-(difluoromethyl)pyrazol-1-yl]cyclohexyl]methanol (Intermediate TD)

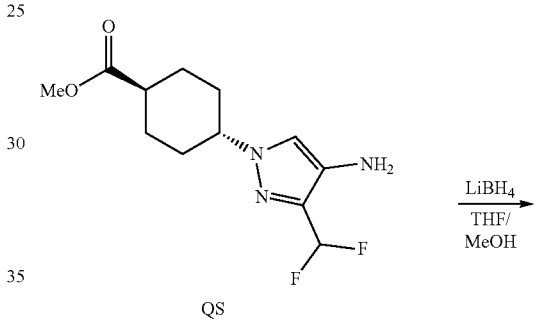

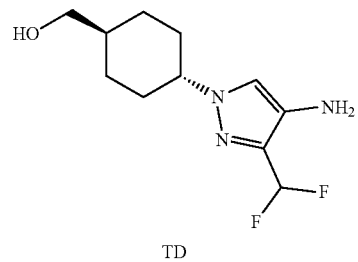

To a mixture of methyl 4-[4-amino-3-(difluoromethyl)pyrazol-1-yl]cyclohexanecarboxylate (1.20 g, 4.39 mmol, Intermediate QS) in THF (80 mL) and MeOH (10 mL) was added LiBH$_4$ (191 mg, 8.78 mmol) at 0° C., then the mixture was stirred at 60° C. for 1 hour. On completion, the reaction mixture was poured into water (120 mL), and the aqueous phase was extracted with ethyl acetate (2×50 mL). The combined organic phase was washed with brine (2×40 mL), dried with anhydrous Na$_2$SO$_4$, filtered and concentrated in vacuo to give title compound (860 mg, 79% yield) as a brown solid. $^1$H NMR (400 MHz, CDCl$_3$-d) δ 7.02 (s, 1H), 6.82-6.53 (m, 1H), 3.94 (tt, J=4.0, 12.0 Hz, 1H), 3.50 (d, J=6.4 Hz, 2H), 2.21-2.12 (m, 3H), 2.01-1.92 (m, 3H), 1.69 (d, J=3.6, 12.4 Hz, 2H), 1.56 (tt, J=3.0, 6.4, 12.0 Hz, 2H), 1.20-1.08 (m, 2H). Absolute stereochemistry randomly assigned, compound is the trans isomer.

1413

5-(4-Tert-butoxycarbonylpiperazin-1-yl)pyrazolo[1,5-a]pyrimidine-3-carboxylic acid (Intermediate RC)

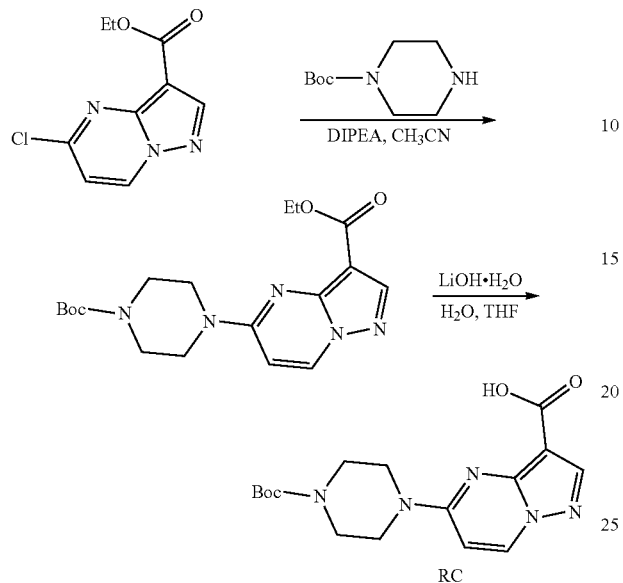

Step 1—Ethyl 5-(4-tert-butoxycarbonylpiperazin-1-yl)pyrazolo[1,5-a]pyrimidine-3-carboxylate To a mixture of ethyl 5-chloropyrazolo[1,5-a]pyrimidine-3-carboxylate (0.50 g, 2.22 mmol, CAS #1224944-77-7) and tert-butyl piperazine-1-carboxylate (619 mg, 3.32 mmol) in MeCN (6 mL) was added DIPEA (857 mg, 6.63 mmol, 1.16 mL), and the resulting mixture was stirred at 60° C. for 2 hours. On completion, the mixture was concentrated in vacuo. The residue was diluted with water (30 mL) and acidified with HCl (1 N) until the pH=5, then the mixture was extracted with EA (3×50 mL). The combined organic layers was dried over Na$_2$SO$_4$, filtered and concentrated in vacuo to give the compound (0.81 g, 97% yield) as white solid; $^1$H NMR (400 MHz, CDCl$_3$) δ 8.32-8.31 (m, 1H), 8.29 (s, 1H), 6.43-6.41 (m, 1H), 4.38-4.32 (m, 2H), 3.90-3.80 (m, 4H), 3.59-3.56 (m, 4H), 1.49 (s, 9H), 1.41-1.37 (m, 3H).

Step 2—5-(4-Tert-butoxycarbonylpiperazin-1-yl)pyrazolo[1,5-a]pyrimidine-3-carboxylic acid To a solution of ethyl 5-(4-tert-butoxycarbonylpiperazin-1-yl)pyrazolo[1,5-a]pyrimidine-3-carboxylate (0.80 g, 2.13 mmol) in THF (16.0 mL) was added a solution of LiOH.H$_2$O (223 mg, 5.33 mmol) in H$_2$O (4.00 mL). The reaction mixture was stirred at 20° C. for 16 hours, then an additional solution of LiOH.H$_2$O (1.00 g, 23.8 mmol) in H$_2$O (4.00 mL) was added, and the reaction mixture was stirred at 20° C. for 8 hours. The mixture was then heated to 45° C. and stirred for 16 hours. On completion, the mixture was concentrated in vacuo. The residue was extracted with EA (20 mL) to remove organic impurities. Then the water phase was acidified with 1 N HCl (aq.) until pH=4, and extracted with EA/MeOH (10/1, 2×20 mL). The combined organic layer was dried over Na$_2$SO$_4$, filtered and concentrated in vacuo to give the title compound (0.72 g, 97% yield) as yellowish solid. $^1$H NMR (400 MHz, CDCl$_3$) δ 8.74-8.72 (m, 1H), 8.17 (s, 1H), 6.84-6.82 (m, 1H), 3.75-3.74 (m, 4H), 3.46-3.43 (m, 4H), 1.42 (s, 9H).

Tert-butyl 4-[3-[[3-(Difluoromethyl)-1-(4-formylcyclohexyl)pyrazol-4-yl]carbamoyl] pyrazolo[1,5-a]pyrimidin-5-yl]piperazine-1-carboxylate (Intermediate TE)

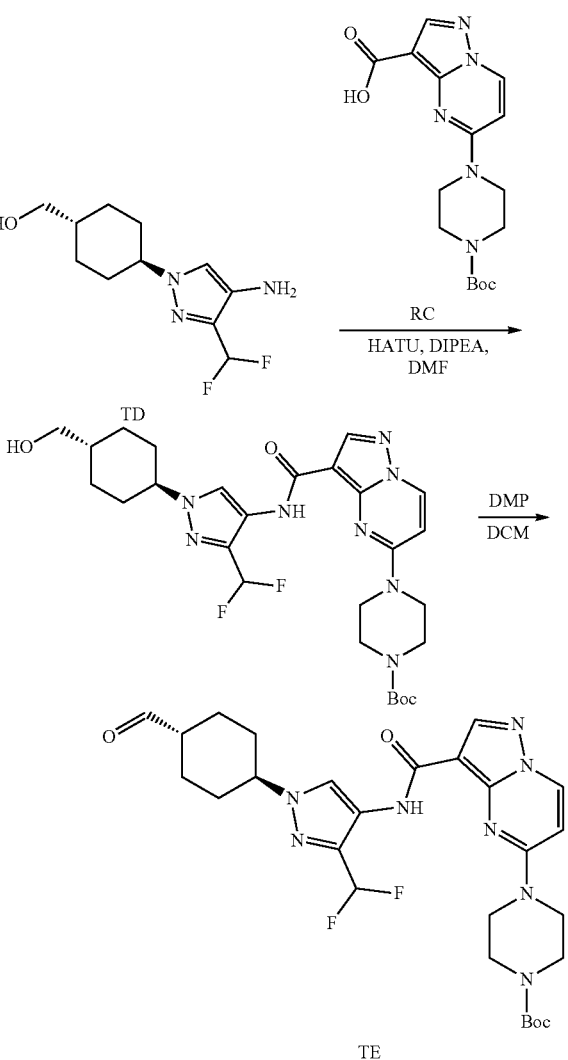

Step 1—4-[3-[[3-(Difluoromethyl)-1-[4-(hydroxymethyl)cyclohexyl]pyrazol-4-yl]carbamoyl] pyrazolo[1,5-a]pyrimidin-5-yl]piperazine-1-carboxylate To a solution of [4-[4-amino-3-(difluoromethyl)pyrazol-1-yl]cyclohexyl]methanol (190 mg, 775 umol, Intermediate TD), 5-(4-tert-butoxycarbonylpiperazin-1-yl)pyrazolo[1,5-a]pyrimidine-3-carboxylic acid (269 mg, 775 umol, Intermediate RC) and DIPEA (250 mg, 1.94 mmol) in DMF (2 mL) was added HATU (324 mg, 852 umol) at 15° C. The mixture was stirred at 15° C. for 0.5 hour. On completion, the mixture was quenched with H$_2$O (0.5 mL). The mixture was concentrated in vacuo. The residue was purified by reversed-phase HPLC (0.1% FA condition) to give the title compound (300 mg, 50% yield, 75% purity) as a brown solid. LC-MS (ESI⁺) m/z 575.4 (M+H)⁺.

Step 2—Tert-butyl 4-[3-[[3-(Difluoromethyl)-1-(4-formylcyclohexyl)pyrazol-4-yl]carbamoyl] pyrazolo[1,5-a]pyrimidin-5-yl]piperazine-1-carboxylate To a solution of tert-butyl 4-[3-[[3-(difluoromethyl)-1-[4-(hydroxymethyl)cyclohexyl]pyrazol-4-yl]carbamoyl]pyrazolo[1,5-a]pyrimidin-5-yl]piperazine-1-carboxylate (200 mg, 348 umol) in DCM (10 mL) was added DMP (221 mg, 522 umol) at 15° C. The mixture was stirred at 15° C. for 2 hours. On completion, the reaction was quenched with sat. aq. Na$_2$S$_2$O$_3$ (20 mL) and sat. aq. NaHCO$_3$ (20 mL). The mixture was extracted with DCM (3×30 mL). The combined organic layers were washed with brine (50 mL), dried over Na$_2$SO$_4$, filtered and concentrated in vacuo. The residue was purified by prep-HPLC (column: Phenomenex Synergi C18 150*25*10 um; mobile phase: [water (0.225% FA)-ACN]; B %: 38%-68%, 10 min) to give the title compound (120 mg, 30% yield) as a white solid. $^1$H NMR (400 MHz, DMSO-d$_6$) δ 9.63 (s, 1H), 9.45-9.37 (m, 1H), 8.83 (d, J=7.6 Hz, 1H), 8.41 (s, 1H), 8.30 (s, 1H), 7.35-6.98 (t, J=5.6 Hz, 1H), 6.90 (d, J=7.6 Hz, 1H), 3.82 (m, 4H), 3.53-3.43 (m, 6H), 1.44 (s, 9H); LC-MS (ESI⁺) m/z 573.4 (M+H)⁺.

3-[6-[3-[2-[2-(Methylamino)ethoxy]ethoxy]propyl]-2-oxo-1,3-benzoxazol-3-yl]piperidine-2,6-dione (Intermediate TF)

Step 1—Tert-butyl N-[2-[2-[3-[3-(2,6-dioxo-3-piperidyl)-2-oxo-1,3-benzoxazol-6-yl]prop-2-ynoxy]ethoxy]ethyl]-N-methyl-carbamate A mixture of tert-butyl N-methyl-N-[2-(2-prop-2-ynoxyethoxy)ethyl]carbamate (427 mg, 1.66 mmol, Intermediate FY), 3-(6-bromo-2-oxo-1,3-benzoxazol-3-yl)piperidine-2,6-dione (300 mg, 923 umol, Intermediate OZ), 4 Å molecular sieves (40 mg), Pd(PPh$_3$)$_2$Cl$_2$ (129 mg, 185 umol), CuI (35.2 mg, 184 umol) and Cs$_2$CO$_3$ (1.50 g, 4.61 mmol) in DMF (10 mL) was de-gassed and then heated at 80° C. for 2 hrs. On completion, the reaction mixture was concentrated in vacuo. The crude product was purified by reversed-phase HPLC (0.1% FA condition) to give the title compound (280 mg, 61% yield) as yellow oil. LC-MS (ESI$^+$) m/z 524.3 (M+Na)$^+$.

Step 2—Tert-butyl N-[2-[2-[3-[3 (2,6-dioxo-3-piperidyl)-2-oxo-1,3-benzoxazol-6-yl]propoxy]ethoxy]thyl]-N-methyl-carbamate To a solution of tert-butyl-[2-[2-[3-[3-(2,6-dioxo-3-piperidyl)-2-xo-1,3-benzoxazol-6-yl]prop-2-noxy]ethoxyethyl]-N-methyl-carbamate (280 mg, 558 umol) in THF (20 mL) was added Pd/C (50 mg, 10% wt) and Pd(OH)$_2$/C (50 mg, 10% wt) under N$_2$ atmosphere. The suspension was degassed under vacuum and purged with H$_2$ several times. The reaction mixture was stirred at 25° C. for 4 hrs under H$_2$ (15 psi). On completion, the reaction mixture was filtered and the filtrate was concentrated in vacuo to give the title compound (150 mg, 53% yield) as yellow oil. $^1$H NMR (400 MHz, DMSO-d$_6$) δ 11.19 (s, 1H), 7.25-7.23 (m, 1H), 7.15-7.11 (m, 1H), 7.03 (d, J=7.6 Hz, 1H), 5.34 (dd, J=5.2, 12 Hz, 1H), 3.5-3.48 (m, 4H), 3.42-3.39 (m, 2H), 3.37-3.35 (m, 3H), 3.31-3.27 (m, 4H), 2.81-2.80 (m, 2H), 2.69-2.61 (m, 1H), 2.63-2.61 (m, 2H), 2.13-2.10 (m, 1H), 1.80-1.75 (m, 2H), 1.37 (s, 9H); LC-MS (ESI$^+$) m/z 528.3 (M+Na)$^+$.

Step 3—3-[6-[3-[2-[2-(Methylamino)ethoxy]ethoxy]propyl]-2-oxo-1,3-benzoxazol-3-yl]piperidine-2,6-dione To a solution of tert-butyl N-[2-[2-[3-[3-(2,6-dioxo-3-piperidyl)-2-oxo-1,3-benzoxazol-6-yl]propoxy]ethoxy]ethyl]-N-methyl-carbamate (140 mg, 277 umol) in DCM (3 mL) was added TFA (2 mL). The mixture was stirred at 25° C. for 2 hrs under N$_2$ atmosphere. On completion, the reaction mixture was concentrated in vacuo to give the title compound (11.9 mg, 39% yield) as white solid. LC-MS (ESI$^+$) m/z 406.2 (M+H)$^+$.

N-[3-(Difluoromethyl)-1-(4-formylcyclohexyl)pyrazol-4-yl]-6-(trifluoromethyl)pyridine-2-carboxamide (Intermediate TG)

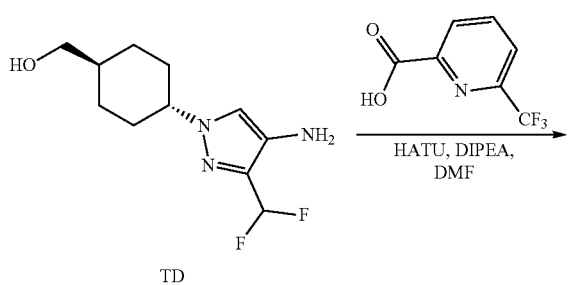

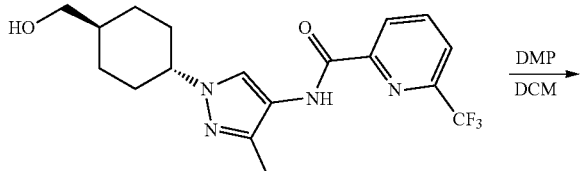

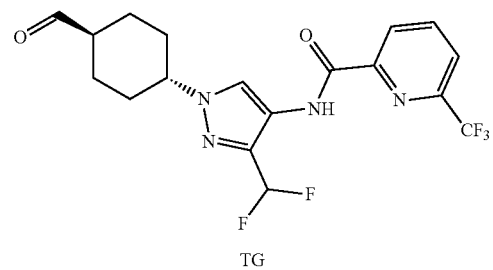

Step 1—N-[3-(difluoromethyl)-1-[4-(hydroxymethyl)cyclohexyl]pyrazol-4-yl]-6-(trifluoromethyl)pyridine-2-carboxamide To a solution of 6-(trifluoromethyl)pyridine-2-carboxylic acid (111 mg, 581 umol, CAS #131747-42-7) in DMF (3 mL) was added HATU (279 mg, 734 umol) and DIPEA (395 mg, 3.06 mmol). The reaction mixture was stirred at 25° C. for 0.5 hr. After, [4-[4-amino-3-(difluoromethyl)pyrazol-1-yl] cyclohexyl]methanol (150 mg, 612 umol, Intermediate TD) was added. The resulting reaction mixture was stirred at 25° C. for 0.5 hr. On completion, the mixture was quenched with water (0.5 mL). The mixture was filtered and the filter cake was collected and purified by reverse phase (0.1% FA condition) to give the title compound (200 mg, 78% yield) as a white solid. $^1$H NMR (400 MHz, DMSO-d$_6$) δ 10.09 (s, 1H), 8.42-8.34 (m, 2H), 8.33 (s, 1H), 8.19 (dd, J=1.6, 7.2 Hz, 1H), 7.16 (t, J=7.2, 1H), 4.55-4.41 (m, 1H), 4.28-4.13 (m, 1H), 3.27-3.23 (m, 2H), 2.11-2.00 (m, 2H), 1.93-1.83 (m, 2H), 1.80-1.67 (m, 2H), 1.50-1.35 (m, 1H), 1.17-0.99 (m, 2H).

Step 2—N-[3-(difluoromethyl)-1-(4-formylcyclohexyl)pyrazol-4-yl]-6-(trifluoromethyl)pyridine-2-carboxamide To a solution of N-[3-(difluoromethyl)-1-[4-(hydroxymethyl)cyclohexyl]pyrazol-4-yl]-6-(trifluoro methyl)pyridine-2-carboxamide (200 mg, 478 umol) in DCM (20 mL) was added DMP (243 mg, 574 umol) at 0° C. Then the reaction mixture was stirred at 25° C. for 5 hrs. On completion, the mixture was quenched with a solution of sat. Na$_2$S$_2$O$_3$ (40 mL) and a solution of sat. NaHCO$_3$ (40 mL), stirred for 15 minutes, then extracted with DCM (2×40 mL). The organic layer was washed with brine (50 mL), dried with anhydrous Na$_2$SO$_4$, filtered and the filtrate was concentrated in vacuo to give the title compound (130 mg, 65% yield) as a white solid. LC-MS (ESI$^+$) m/z 417.0 (M+H)$^+$.

3-(6-bromo-9H-pyrido[2,3-b]indol-9-yl)piperidine-2,6-dione (Intermediate UH)

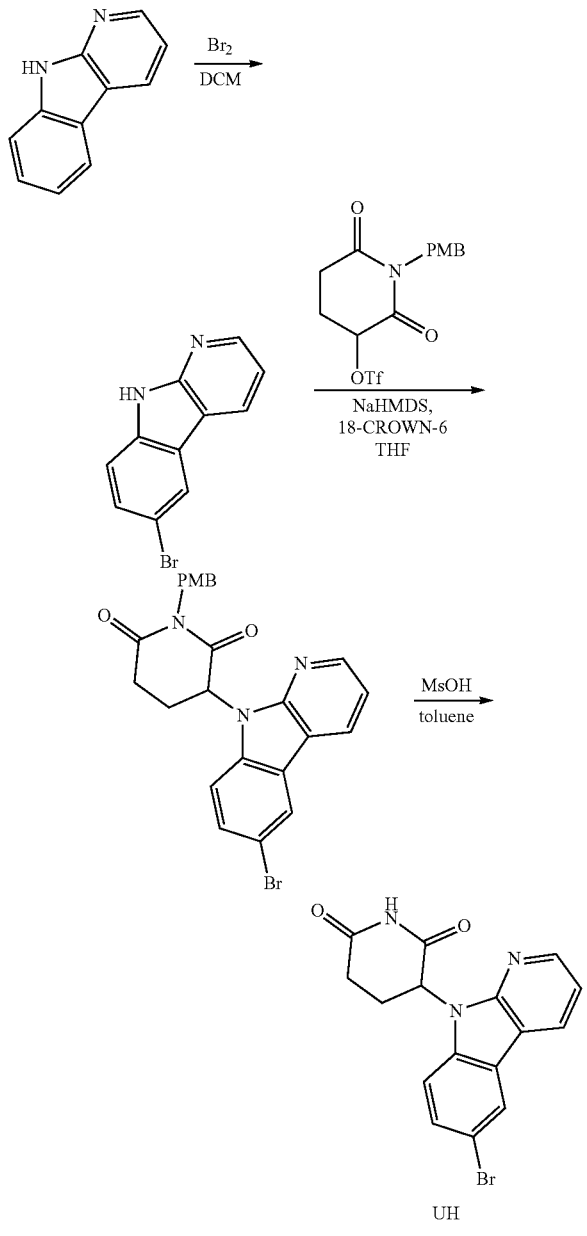

Step 1—6-bromo-9H-pyrido[2,3-b]indole

To a stirred solution of 9H-pyrido[2,3-b]indole (3 g, 17.9 mmol, CAS #26148-68-5) in DCM (50 mL) was added Br$_2$ (3.4 g, 21.4 mmol) dropwise at 0° C. The reaction mixture was stirred at 0° C. for 4 h. To the mixture was added aq. NaHCO$_3$ (100 mL), then the solution was extracted with EA (200 mL). The organic layer was washed with brine (50 mL), dried over Na$_2$SO$_4$, filtered, concentrated to give the title compound (2.7 g, 61% yield) as yellow solid. $^1$H NMR (400 MHz, DMSO-d$_6$) δ 12.02 (s, 1H), 8.60 (dd, J=1.2 Hz, J=7.6 Hz, 1H), 8.48-8.44 (m, 2H), 7.60-7.58 (m, 1H), 7.48 (d, J=8.4 Hz, 1H), 7.26 (dd, J=4.8 Hz, J=7.6 Hz, 1H). LC/MS (ESI, m/z): [M+1]$^+$=247.8

Step 2—3-(6-bromo-9H-pyrido[2,3-b]indol-9-yl)-1-(4-methoxybenzyl)piperidine-2,6-dione To a stirred solution of 6-bromo-9H-pyrido[2,3-b]indole (200 mg, 0.810 mmol) and 18-crown-6 (43 mg, 0.162 mmol) in THF (10 mL) was added NaHMDS (0.6 mL, 2 M in THF) dropwise at −30° C. under N$_2$. The mixture was stirred for 1 h at −30° C. under N$_2$. Then to the mixture was added a solution of 1-(4-methoxybenzyl)-2,6-dioxopiperidin-3-yl trifluoromethanesulfonate (463 mg, 1.21 mmol) in THF (5 mL) dropwise at −30° C. under N$_2$. The mixture was stirred for 2 h at −30° C. The mixture was added to aq. NH$_4$Cl (20 mL), then extracted with EA (50 mL). The organic layer was washed with brine (30 mL), dried over Na$_2$S04, filtered, concentrated and purified by column (PE/EA/DCM=10/1/1 to 3/1/1) to give the title compound (220 mg, 57% yield) as a yellow oil. $^1$H NMR (400 MHz, CDCl$_3$) δ 8.41 (dd, J=1.6 Hz, J=5.2 Hz, 1H), 8.29 (dd, J=1.2 Hz, J=7.6 Hz, 1H), 8.20 (d, J=1.6 Hz, 1H), 7.45 (dd, J=2.0 Hz, J=8.8 Hz, 1H), 7.40 (d, J=8.8 Hz, 2H), 7.24-7.21 (m, 1H), 6.84 (d, J=8.8 Hz, 3H), 5.90-5.87 (m, 1H), 5.01 (dd, J=13.6 Hz, J=20.4 Hz, 2H), 3.79 (s, 3H), 3.09-2.88 (m, 3H), 3.27-2.24 (m, 1H). LC/MS (ESI, m/z): [M+1]$^+$=479.1.

Step 3—3-(6-bromo-9H-pyrido[2,3-b]indol-9-yl)piperidine-2,6-dione

A mixture of 3-(6-bromo-9H-pyrido[2,3-b]indol-9-yl)-1-(4-methoxybenzyl)piperidine-2,6-dione (1.3 g, 2.72 mmol), MsOH (10 mL) and toluene (20 mL) was heated to 110° C. and stirred for 3 h under N$_2$. The solvent was concentrated to remove toluene. Then to the mixture was added EtOAc (50 mL), and the solution was washed with brine (50 mL) to remove MsOH. The organic layer was dried over Na$_2$SO$_4$. The solid was filter and the filtrate was concentrated. The resulting residue was purified by column chromatography on silica gel (PE/EA=1/1) to give the title compound (500 mg, 51% yield) as a white solid. $^1$H NMR (400 MHz, DMSO-d$_6$) δ 11.17 (s, 1H), 8.64 (dd, J=1.6 Hz, J=7.6 Hz, 1H), 8.52 (d, J=2.0 Hz, 1H), 8.47 (dd, J=1.6 Hz, J=4.8 Hz, 1H), 7.68-7.64 (m, 2H), 7.32 (dd, J=4.8 Hz, J=7.6 Hz, 1H), 6.06 (br s, 1H), 3.16-2.96 (m, 2H), 2.73-2.67 (m, 1H), 2.16-2.13 (m, 1H). LC/MS (ESI, m/z): [M+1]$^+$=358.0.

tert-Butyl methyl(3-(prop-2-yn-1-yloxy)propyl)carbamate (Intermediate UI)

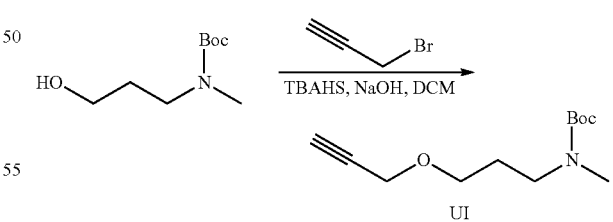

To a solution of tert-butyl (3-hydroxypropyl)(methyl)carbamate (2 g, 10.6 mmol, CAS #98642-44-5) in DCM (30 mL) was added aq. NaOH (40%, 20 mL), 3-bromoprop-1-yne (1.9 g, 15.9 mmol) and TBAHS (180 mg, 0.530 mmol) at rt. The mixture was stirred at rt for 3 h. To the mixture was added H$_2$O (100 mL), then the mixture was extracted with DCM (3×30 mL). The organic layers were washed with brine (50 mL), dried over Na$_2$SO$_4$, filtered, concentrated and purified by column (PE/EA=20/1 to 10/1 to 4/1) to give the title compound (1.4 g, 58% yield) as a yellow oil. $^1$H NMR (400 MHz, CDCl$_3$) δ 4.14 (d, J=2.4 Hz, 2H), 3.53 (t, J=6.4 Hz, 2H), 3.29 (t, J=6.8 Hz, 2H), 2.86 (s, 3H), 2.42 (t, J=2.4 Hz, 1H), 1.83-1.80 (m, 2H), 1.46 (s, 9H). LC/MS (ESI, m/z): [M+1]$^+$=227.9.

3-[6-[3-[3-(Methylamino)propoxy]propyl]pyrido[2,3-b]indol-9-yl]piperidine-2,6-dione (Intermediate TH)

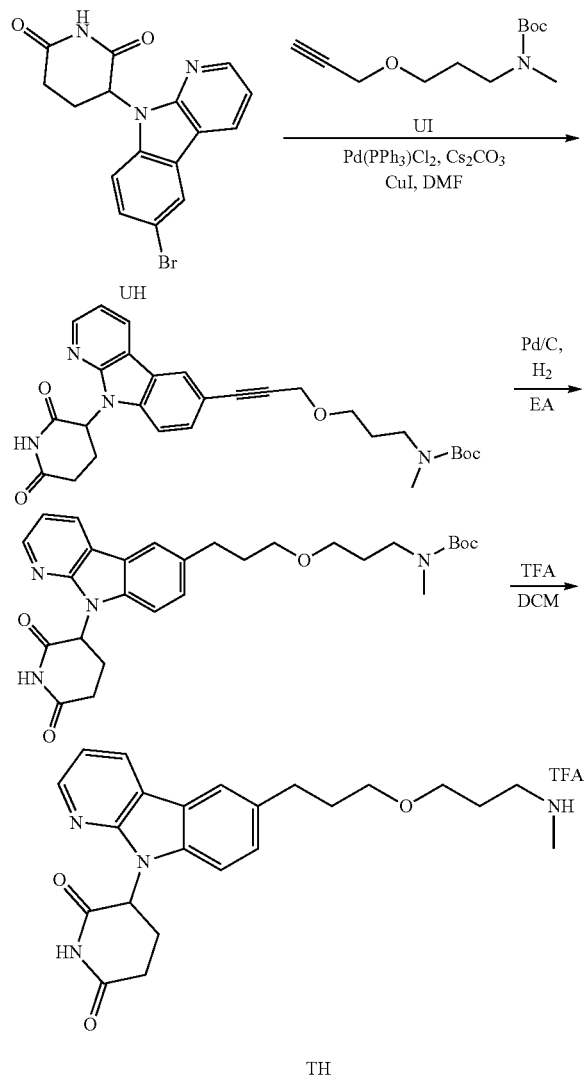

Step 1—tert-butyl (3-((3-(9-(2,6-dioxopiperidin-3-yl)-9H-pyrido[2,3-b]indol-6-yl)prop-2-yn-1-yl)oxy)propyl)(methyl)carbamate A mixture of 3-(6-bromo-9H-pyrido[2,3-b]indol-9-yl)piperidine-2,6-dione (100 mg, 0.279 mmol, Intermediate UH), tert-butyl methyl(3-(prop-2-yn-1-yloxy)propyl)carbamate (190 mg, 0.838 mmol, Intermediate UJ), Pd(PPh$_3$)$_2$Cl$_2$ (30 mg, 0.0419 mmol), CuI (4 mg, 0.0223 mmol), Cs$_2$CO$_3$ (455 mg, 1.40 mmol) and 4 Å MS (200 mg) in DMF (5 mL) was heated to 80° C. under microwave for 1.5 h under N$_2$. The mixture was then poured into 1N HCl (20 mL), then extracted with EA (3×20 mL). The organic layers were washed with brine (20 mL), dried over Na$_2$SO$_4$, filtered, concentrated and purified by column chromatography on silica gel (PE/EA=10/1 to 5/1 to 2/1) to give the title compound (50 mg, 35% yield) as a white solid. $^1$H NMR (400 MHz, CDCl$_3$) δ 8.57 (d, J=7.2 Hz, 1H), 8.46 (dd, J=1.2 Hz, J=5.6 Hz, 1H), 8.25 (d, J=1.2 Hz, 1H), 8.13 (s, 1H), 7.65 (dd, J=1.6 Hz, J=4.0 Hz, 1H), 7.25-7.19 (m, 2H), 5.90 (dd, J=2.8 Hz, J=6.0 Hz, 1H), 4.41 (s, 2H), 3.63 (t, J=6.4 Hz, 2H), 3.34 (t, J=7.2 Hz, 2H), 3.02-2.91 (m, 3H), 2.89 (s, 3H), 2.50-2.47 (m, 1H), 1.88 (t, J=6.8 Hz, 2H), 1.46 (s, 9H). LC/MS (ESI, m/z): [M+1]$^+$=505.2.

Step 2—tert-butyl (3-(3-(9-(2,6-dioxopiperidin-3-yl)-9H-pyrido[2,3-b]indol-6-yl)propoxy)propyl)(methyl)carbamate A mixture of tert-butyl (3-((3-(9-(2,6-dioxopiperidin-3-yl)-9H-pyrido[2,3-b]indol-6-yl)prop-2-yn-1-yl)oxy)propyl)(methyl)carbamate (320 mg, 0.634 mmol), Pd/C (320 mg) and EA (10 mL) was stirred for overnight at rt under H$_2$. The mixture was filtered, concentrated and purified by column (PE/EA=1/1) to give the title product (170 mg, 53% yield) as a white solid. $^1$H NMR (400 MHz, CDCl$_3$) δ 8.41 (dd, J=1.6 Hz, J=4.8 Hz, 1H), 8.32 (d, J=7.6 Hz, 1H), 8.15 (s, 1H), 7.91 (d, J=0.8 Hz, 1H), 7.33 (dd, J=1.2 Hz, J=8.0 Hz, 1H), 7.22-7.16 (m, 2H), 5.94 (br s, 1H), 3.45 (dd, J=6.4 Hz, J=11.6 Hz, 4H), 3.13 (t, J=5.8 Hz, 2H), 3.07-2.95 (m, 3H), 2.88-2.84 (m, 5H), 2.33-2.29 (m, 1H), 2.01-1.93 (m, 2H), 1.85-1.78 (m, 2H), 1.46 (s, 9H). LC/MS (ESI, m/z): [M-BOC+H]$^+$=409.2 and [M-56+H]=453.2.

Step 3—3-[6-[3-[3-(Methylamino)propoxy]propyl]pyrido[2,3-b]indol-9-yl]piperidine-2,6-dione To a solution of tert-butyl N-[3-[3-[9-(2,6-dioxo-3-piperidyl)pyrido[2,3-b]indol-6-yl]propoxy]propyl]-N-methylcarbamate (85.0 mg, 167 umol) in DCM (6 mL) was added TFA (381 mg, 3.34 mmol). The mixture was stirred at 25° C. for 2 hrs. On completion, the reaction mixture was concentrated in vacuo to give the title compound (87 mg, 95% yield, TFA salt) as light yellow oil. LC-MS (ESI$^+$) m/z 409.3 (M+H)$^+$.

3-[6-[3-[2-(2-Aminoethoxy)ethoxy]propyl]pyrido[2,3-b]indol-9-yl]piperidine-2,6-dione (Intermediate TL)

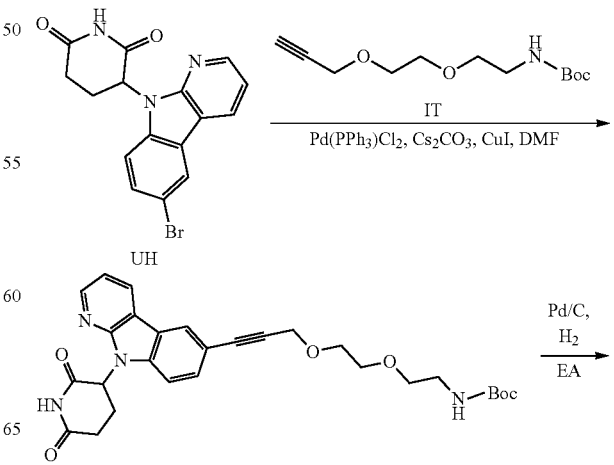

1423

-continued

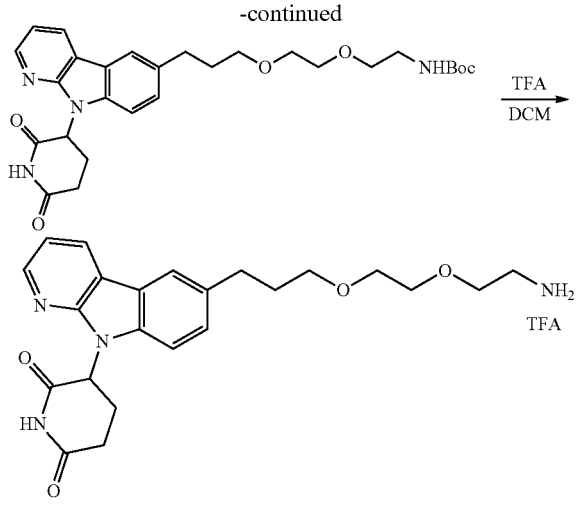

TL

Step 1—tert-butyl (2-(2-((3-(9-(2,6-dioxopiperidin-3-yl)-9H-pyrido[2,3-b]indol-6-yl)prop-2-yn-1-yl)oxy)ethoxy)ethyl)carbamate A mixture of 3-(6-bromo-9H-pyrido[2,3-b]indol-9-yl)piperidine-2,6-dione (600 mg, 1.68 mmol, Intermediate UH), tert-butyl (2-(2-(prop-2-yn-1-yloxy)ethoxy)ethyl)carbamate (1.2 g, 5.03 mmol, Intermediate IT), Pd(PPh$_3$)$_2$Cl$_2$ (179 mg, 0.252 mmol), CuI (26 mg, 0.134 mmol), Cs$_2$CO$_3$ (55 g, 16.8 mmol), 4 Å MS (1 g) and DMF (10 mL) was heated to 80° C. under microwave for 1.5 h under N$_2$. The mixture was then poured into 1N HCl (400 mL), and extracted with EA (100 mL). The organic layer was washed with brine (30 mL), dried over Na$_2$SO$_4$, filtered, concentrated and purified by column (PE/EA=10/1 to 5/1 to 2/1) to give the title compound (250 mg, 29% yield) as a white solid. $^1$H NMR (400 MHz, CDCl$_3$) δ 8.45 (dd, J=1.2 Hz, J=4.8 Hz, 1H), 8.34 (dd, J=1.2 Hz, J=7.6 Hz, 1H), 8.21 (d, J=0.8 Hz, 1H), 8.15 (s, 1H), 7.59 (dd, J=1.2 Hz, J=8.4 Hz, 1H), 7.27-7.22 (m, 2H), 5.95 (br s, 1H), 5.01 (br s, 1H), 4.47 (s, 2H), 3.81-3.79 (m, 2H), 3.71-3.69 (m, 2H), 3.58 (t, J=5.2 Hz, 2H), 3.33-3.34 (m, 2H), 3.09-2.96 (m, 2H), 2.35-2.31 (m, 1H), 2.02-1.99 (m, 1H), 1.44 (s, 9H). LC/MS (ESI, m/z): [M−Boc+1]$^+$=421.3.

Step 2—tert-butyl (2-(2-(3-(9-(2,6-dioxopiperidin-3-yl)-9H-pyrido[2,3-b]indol-6-yl)propoxy)ethoxy)ethyl)carbamate A mixture of tert-butyl (2-(2-((3-(9-(2,6-dioxopiperidin-3-yl)-9H-pyrido[2,3-b]indol-6-yl)prop-2-yn-1-yl)oxy)ethoxy)ethyl)carbamate (250 mg, 0.481 mmol), Pd/C (100 mg) and EA (15 mL) was stirred for overnight at rt under H$_2$. The mixture was filtered, concentrated and purified by column (PE/EA=1/1) to give the title compound (150 mg, 60% yield) as a white solid. $^1$H NMR (400 MHz, CDCl$_3$) δ 8.41 (dd, J=1.2 Hz, J=4.8 Hz, 1H), 8.31 (dd, J=1.6 Hz, J=7.6 Hz, 1H), 8.22 (s, 1H), 7.92 (d, J=0.8 Hz, 1H), 7.33 (dd, J=1.6 Hz, J=8.4 Hz, 1H), 7.21-7.16 (m, 2H), 5.92-5.88 (m, 1H), 5.04 (br s, 1H), 3.64-3.50 (m, 8H), 3.33 (d, J=4.8 Hz, 2H), 3.08-2.85 (m, 5H), 2.32-2.28 (m, 1H), 2.04-1.97 (m, 2H), 1.43 (s, 9H); LC/MS (ESI, m/z): [M−Boc+1]$^+$=425.2.

1424

Step 3—3-[6-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-6-yl]propoxy] ethoxy]ethyl]carbamate (54.0 mg, 102 umol) in DCM (3 mL) was added TFA (352 mg, 3.09 mmol). The mixture was stirred at 25° C. for 1 hr. On completion, the reaction mixture was concentrated in vacuo to give the title compound (55.0 mg, 95% yield, TFA salt) as light yellow oil. LC-MS (ESI$^+$) m/z 425.3 (M+H)$^+$.

Step 1—Tert-butyl 4-prop-2-ynoxypiperidine-1-carboxylate (Intermediate TM)

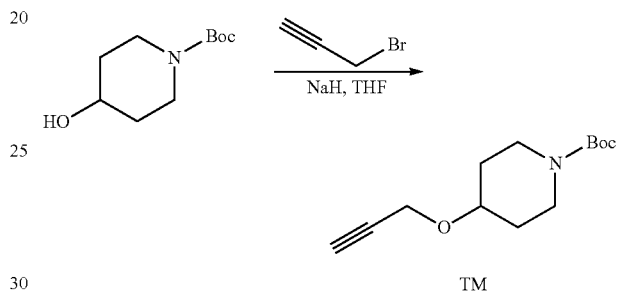

TM

To a solution of tert-butyl 4-hydroxypiperidine-1-carboxylate (2.00 g, 9.94 mmol, CAS #109384-19-2) in anhydrous THF (10 mL) was cooled to 0° C., and subsequently NaH (477 mg, 11.9 mmol, 60% oil dispersion) was added. The reaction mixture was stirred at 0° C. for 0.5 hr. Then, 3-bromoprop-1-yne (1.18 g, 9.94 mmol, 856 uL) was added. The resulting reaction mixture was stirred at 25° C. for 12 hrs. On completed, the reaction mixture was quenched with water (1 mL), then diluted with ethyl acetate (100 mL). The organic layers were washed with brine (20 mL), dried over anhydrous sodium sulfate, filtered and the filtrate was concentrated in vacuo. The residue was purified by column chromatography to give the title compound (2.38 g, 100% yield) as yellow oil. $^1$H NMR (400 MHz, CDCl$_3$) δ 4.22 (d, J=2.4 Hz, 2H), 3.84-3.75 (m, 2H), 3.73-3.70 (m, 1H), 3.15-3.09 (m, 2H), 2.43 (t, J=2.4 Hz, 1H), 1.93-1.82 (m, 2H), 1.61-1.50 (m, 2H), 1.47 (s, 9H).

3-[3-Methyl-2-oxo-4-[3-(4-piperidyloxy)propyl]benzimidazol-1-yl]piperidine-2,6-dione (Intermediate TN)

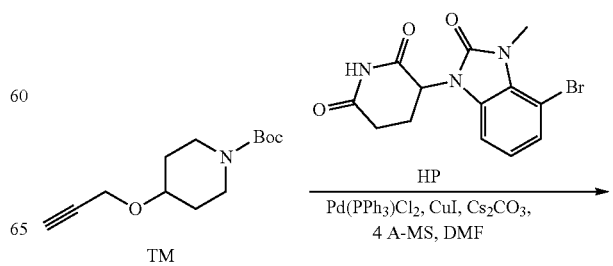

-continued

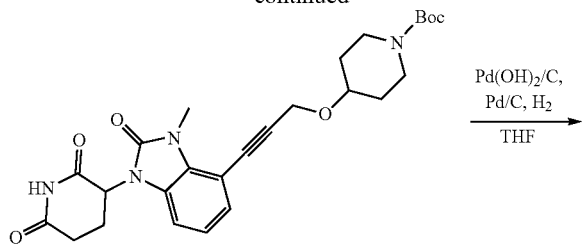

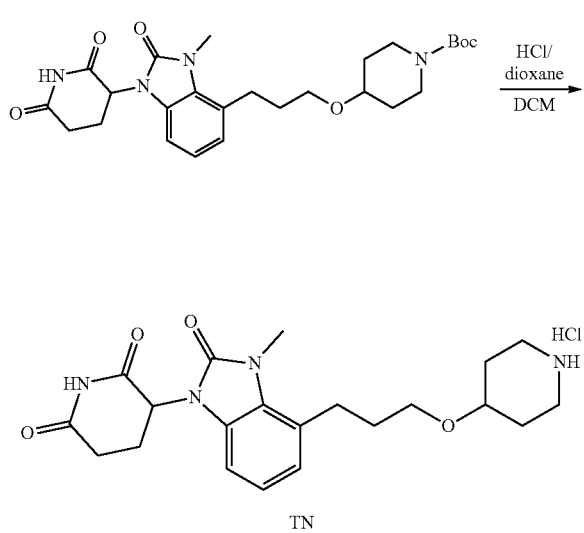

Step 1—Tert-butyl 4-[3-[1-(2,6-dioxo-3-piperidyl)-3-methyl-2-oxo-benzimidazol-4-yl]prop-2-ynoxy] piperidine-1-carboxylate A suspension of 3-(4-bromo-3-methyl-2-oxo-benzimidazol-1-yl)piperidine-2,6-dione (300 mg, 887 umol, Intermediate HP), tert-butyl 4-prop-2-ynoxypiperidine-1l-carboxylate (318 mg, 1.33 mmol, Intermediate™), Pd(PPh$_3$)$_2$Cl$_2$ (124 mg, 177 umol), CuI (33.8 mg, 177 umol), 4 Å molecular sieves (400 mg) and Cs$_2$CO$_3$ (1.16 g, 3.55 mmol) in DMF (5 mL) was de-gassed under vacuum and purged with N$_2$ several times and then heated to 80° C. for 2 hours under N$_2$. On completion, the reaction mixture was concentrated in vacuo to remove DMF. The residue was diluted with EA (50 mL) and water (20 mL). After, the organic layer was separated and washed with brine (5 mL×2), dried over anhydrous Na$_2$SO$_4$, filtered and the filtrate was concentrated in vacuo to give a residue. The residue was purified by reverse phase to give the title compound (222 mg, 48% yield) as a yellow solid. $^1$H NMR (400 MHz, CDCl$_3$) δ 8.09 (s, 1H), 7.10 (d, J=8.0 Hz, 1H), 6.92 (t, J=8.0 Hz, 1H), 6.69 (d, J=8.0 Hz, 1H), 5.13 (dd, J=5.2, 12.8 Hz, 1H), 4.39 (s, 2H), 3.76-3.66 (m, 6H), 3.09-3.03 (m, 2H), 2.94-2.84 (m, 1H), 2.82-2.71 (m, 1H), 2.71-2.59 (m, 1H), 2.22-2.11 (m, 1H), 1.83-1.78 (m, 2H), 1.57-1.49 (m, 2H), 1.39 (s, 9H), LC-MS (ESI$^+$) m/z 441.2 (M+H-56)$^+$.

Step 2—Tert-butyl4-[3-[1-(2,6-dioxo-3-piperidyl)-3-methyl-2-oxo-benzimidazol-4-yl]propoxy] piperidine-1-carboxylate To a solution of tert-butyl 4-[3-[1-(2,6-dioxo-3-piperidyl)-3-methyl-2-oxo-benzimidazol-4-yl]prop-2-ynoxy] piperidine-1-carboxylate (370 mg, 745 umol) in THF (10 mL) was added Pd/C (0.1 g, 10% wt) and Pd(OH)$_2$/C (0.1 g, 10% wt). The suspension was degassed under vacuum and purged with H$_2$ several times. The mixture was stirred under H$_2$ (15 psi) at 25° C. for 12 hours. On completion, the reaction mixture was filtered and the filtrate was concentrated in vacuo to give the title compound (330 mg, 88% yield) as a white solid. $^1$H NMR (400 MHz, CDCl$_3$) δ 8.03 (s, 1H), 6.91 (d, J=8.0 Hz, 1H), 6.83 (d, J=8.0 Hz, 1H), 6.59 (t, J=8.0 Hz, 1H), 5.20-5.09 (m, 1H), 3.70-3.64 (m, 2H), 3.62 (s, 3H), 3.44 (t, J=5.6 Hz, 2H), 3.41-3.34 (m, 1H), 3.06-3.04 (m, 2H), 2.98-2.93 (m, 2H), 2.91-2.80 (m, 1H), 2.79-2.63 (m, 2H), 2.19-2.10 (m, 1H), 1.89-1.81 (m, 2H), 1.80-1.73 (m, 2H), 1.47-1.39 (m, 2H), 1.39 (s, 9H); LC-MS (ESI$^+$) m/z 523.1 (M+Na)$^+$.

Step 3—3-[3-Methyl-2-oxo-4-[3-(4-piperidyloxy) propyl]benzimidazol-1-yl]piperidine-2,6-dione To a solution of tert-butyl 4-[3-[1-(2,6-dioxo-3-piperidyl)-3-methyl-2-oxo-benzimidazol-4-yl]propoxy] piperidine-1-carboxylate (100 mg, 199 umol) in DCM (4 mL) was added HCl/dioxane (4 M, 2 mL). The reaction mixture was stirred at 25° C. for 0.5 hr. On completion, the reaction mixture was concentrated in vacuo to give the title compound (87.0 mg, 100% yield, HCl salt) as a white solid. LC-MS (ESI$^+$) m/z 401.1 (M+H)$^+$.

2-[2-(Methylamino)ethoxy]ethanol (Intermediate WK)

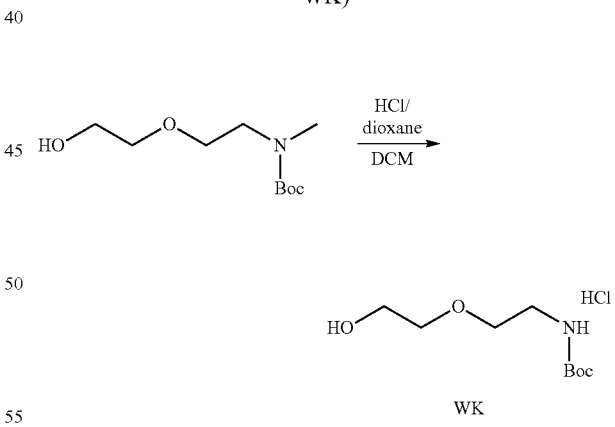

To a solution of tert-butyl N-[2-(2-hydroxyethoxy)ethyl]-N-methyl-carbamate (3.00 g, 13.7 mmol, synthesized via Steps 1-2 of Intermediate FY) in DCM (20 mL) was added HCl/dioxane (4 M, 20 mL). The reaction mixture was stirred at 25° C. for 1 hr. On completion, the mixture was concentrated in vacuo to give the title compound (2.10 g, 99% yield, HCl salt) as a white solid. $^1$H NMR (400 MHz, DMSO-d$_6$) δ 3.67 (t, J=5.2 Hz, 2H), 3.57-3.51 (m, 2H), 3.50-3.46 (m, 2H), 3.13-3.02 (m, 2H), 2.55 (t, J=5.2 Hz, 3H).

Tert-butyl N-(cyclopropylmethyl)-N-[4-[4-[[3-(difluoromethyl)-1-[4-[methyl-[2-(2-oxoethoxy) ethyl]carbamoyl]cyclohexyl]pyrazol-4-yl]carbamoyl]oxazol-2-yl]-2-pyridyl]carbamate (Intermediate WL)

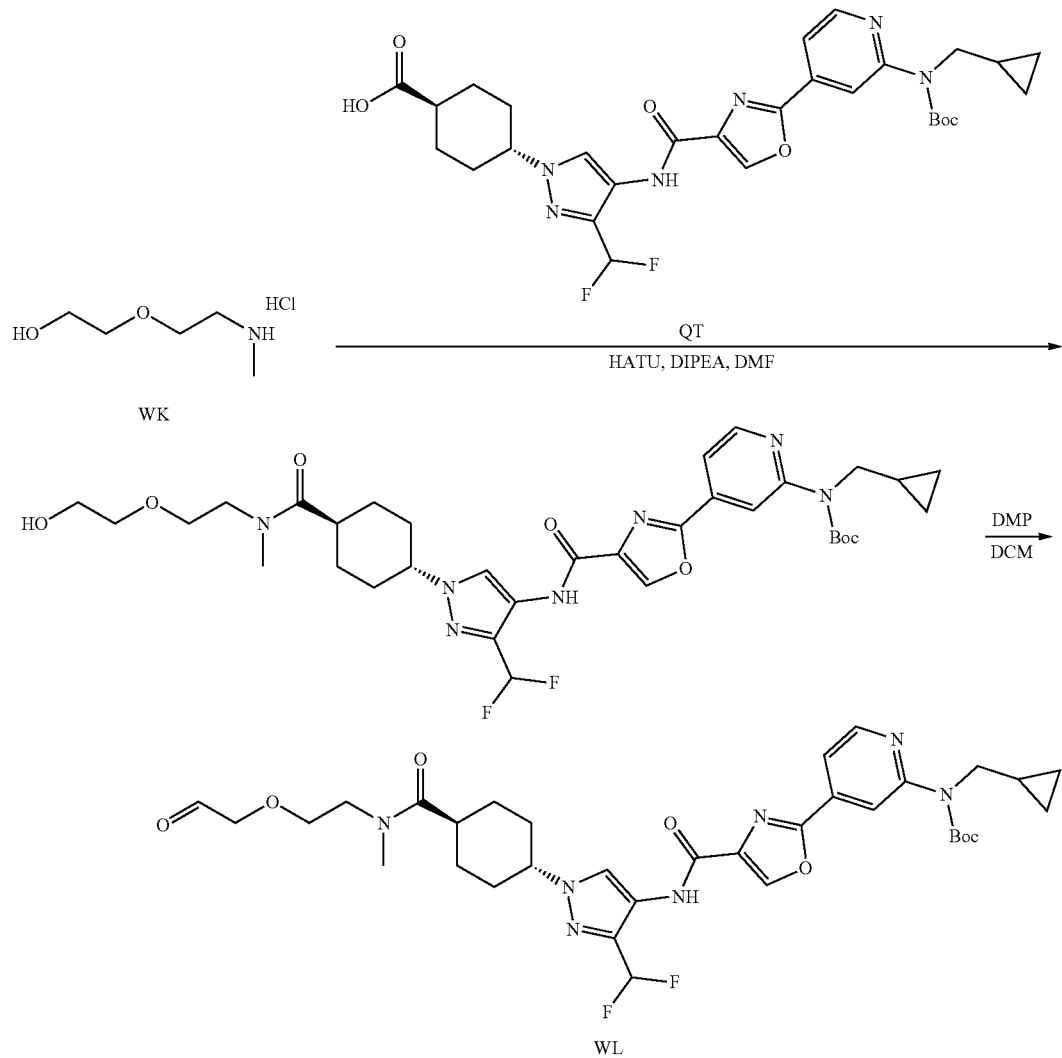

Step 1—Tert-butyl N-(cyclopropylmethyl)-N-[4-[4-[[3-(difluoromethyl)-1-[4-[2-(2-hydroxyethoxy) ethyl-methylcarbamoyl] cyclohexyl]pyrazol-4-yl]carbamoyl] oxazol-2-yl]-2-pyridyl]carbamate To a solution of 2-[2-(methylamino)ethoxy]ethanol (51.8 mg, 333 umol, HCl salt, Intermediate WK) and 4-[4-[[2-[2-[tertbutoxycarbonyl(cyclopropylmethyl)amino]-4-pyridyl]oxazole-4-carbonyl]amino]-3-(difluoromethyl)pyrazol-1-yl]cyclohexanecarboxylic acid (200 mg, 333 umol, Intermediate QT) in DMF (8 mL) was added DIPEA (129 mg, 174.00 uL). The reaction mixture was stirred at 25° C. for 0.5 hr. Then HATU (152 mg, 400 umol) was added and the resulting reaction mixture was stirred at 25° C. for 2 hrs. On completion, the mixture was quenched with water (0.2 mL) and concentrated in vacuo. The residue was purified by reverse phase (0.1% FA condition) to give the title compound (200 mg, 85% yield) as a brown solid. LC-MS (ESI$^+$) m/z 702.4 (M+H)$^+$.

Step 2—Tert-butyl N-(cyclopropylmethyl)-N-[4-[4-[[3-(difluoromethyl)-1-[4-[methyl-[2-(2-oxoethoxy) ethyl] carbamoyl] cyclohexyl]pyrazol-4-yl] carbamoyl]oxazol-2-yl]-2-pyridyl]carbamate To a solution of tert-butyl N-(cyclopropylmethyl)-N-[4-[4-[[3-(difluoromethyl)-1-[4-[2-(2-hydroxyl ethoxy)ethyl-methyl-carbamoyl]cyclohexyl]pyrazol-4-yl]carbamoyl]oxazol-2-yl]-2-pyridyl]carbamate (180 mg, 257 umol) in DCM (8 mL) was added DMP (163 mg, 385 umol). The reaction mixture was stirred at 20° C. for 2 hrs. On completion, the mixture was quenched with sat.Na$_2$S$_2$O$_3$ (20 mL) and sat.NaHCO$_3$ (20 mL), stirred for 10 minutes, then extracted with DCM (2×30 mL). The combined organic layer was washed with brine (2×50 mL), dried with anhydrous Na$_2$SO$_4$, filtered and the filtrate was concentrated in vacuo to give the title compound (140 mg, 78% yield) as a yellow solid. $^1$H NMR (400 MHz, DMSO-d$_6$) δ 9.80 (s, 1H), 9.55 (d, J=3.6 Hz, 1H), 9.01 (s, 1H), 8.58 (d, J=5.2 Hz, 1H), 8.29 (s, 1H), 8.19 (s, 1H), 7.68 (dd, J=1.2, 5.2 Hz, 1H), 7.31 (t, J=54.4 Hz 1H), 4.32-4.25 (m, 1H), 3.86 (d, J=7.2 Hz, 2H), 3.66-3.41 (m, 4H), 3.30 (s, 3H), 3.10-3.07 (m, 1H), 2.87-2.73 (m, 2H), 2.09-1.99 (m, 2H), 1.91-1.73 (m, 4H), 1.62-1.58 (m, 2H), 1.51 (s, 9H), 1.21-1.13 (m, 1H), 0.45-0.35 (m, 2H), 0.26-0.20 (m, 2H); LC-MS (ESI$^+$) m/z 700.4 (M+H)$^+$.

3-[5-(Aminomethyl)-3-methyl-2-oxo-benzimidazol-1-yl]piperidine-2,6-dione (Intermediate PH)

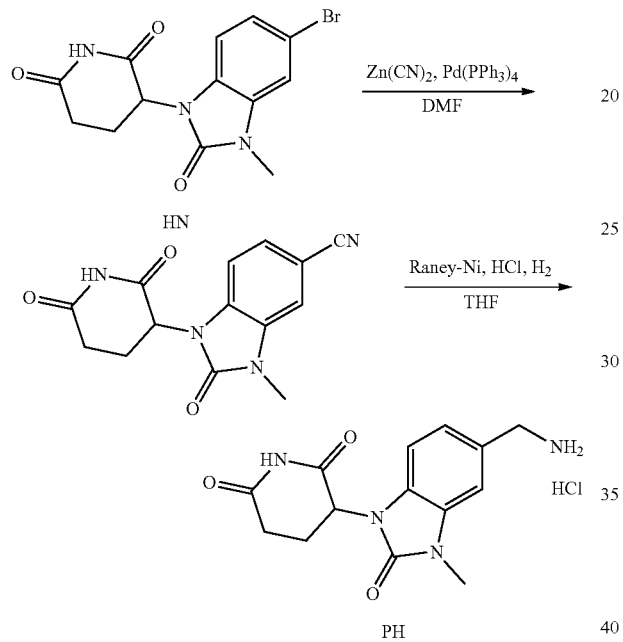

Step 1—1-(2,6-Dioxo-3-piperidyl)-3-methyl-2-oxo-benzimidazole-5-carbonitrile

To a mixture of 3-(5-bromo-3-methyl-2-oxo-benzimidazol-1-yl)piperidine-2,6-dione (3.00 g, 8.87 mmol, Intermediate HN) in DMF (30 mL) was added Zn(CN)$_2$ (1.04 g, 8.87 mmol) and Pd(PPh$_3$)$_4$ (1.03 g, 887 umol). The reaction mixture was stirred at 100° C. for 3 hours under N$_2$. On completion, the reaction mixture was filtered and the filtrate was concentrated in vacuo. The residue was diluted with water (50 mL) and extracted with EA (3×100 mL). The combined organic layers were dried over Na$_2$SO$_4$, filtered and the filtrate concentrated in vacuo. The residue was purified by prep-HPLC (0.1% FA condition) to give the title compound (1.50 g, 59% yield) as a white solid. $^1$H NMR (400 MHz, DMSO-d$_6$) δ 11.31-11.00 (m, 1H), 11.15 (s, 1H), 7.75 (d, J=1.2 Hz, 1H), 7.57-7.52 (m, 1H), 7.34 (d, J=8.4 Hz, 1H), 5.49-5.42 (m, 1H), 3.38 (s, 3H), 2.95-2.83 (m, 1H), 2.79-2.59 (m, 2H), 2.10-2.01 (m, 1H).

Step 2—3-[5-(Aminomethyl)-3-methyl-2-oxo-benzimidazol-1-yl]piperidine-2,6-dione

To a solution of 1-(2,6-dioxo-3-piperidyl)-3-methyl-2-oxo-benzimidazole-5-carbonitrile (1.40 g, 4.92 mmol) in THF (150 mL) was added Raney-Ni (421 mg, 4.92 mmol) and HCl/dioxane (4 M, 4.92 mL). The reaction mixture was stirred at 25° C. for 36 hours under H$_2$ (50 Psi). On completion, the reaction mixture was filtered. The filter cake was washed with DMF (3×10 mL). The combined organic layers were concentrated in vacuo to give the title compound (1.40 g, 98% yield) as a green solid. LC-MS (ESI$^+$) m/z 289.0 (M+H)$^+$.

2-[2-[tert-Butoxycarbonyl(2,2,2-trifluoroethyl)amino]-4-pyridyl]oxazole-4-carboxylic acid (Intermediate CM)

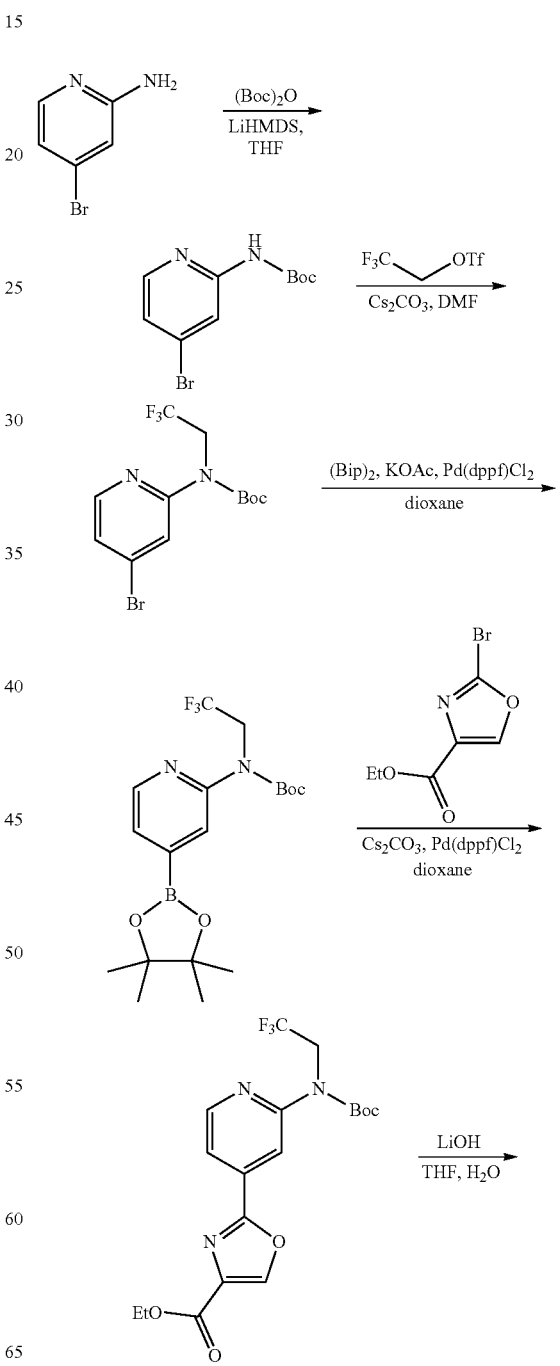

-continued

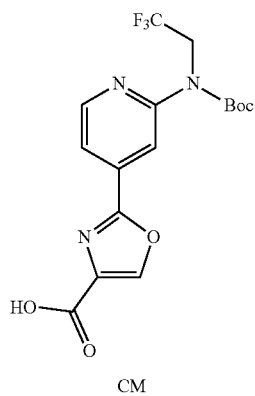 [SMILES: CC(C)(C)OC(=O)N(CC(F)(F)F)c1cc(-c2nc(C(=O)O)co2)ccn1]

CM

Step 1—Tert-butyl N-(4-bromo-2-pyridyl)carbamate

A solution of 4-bromopyridin-2-amine (5.00 g, 28.9 mmol) in dry THF (100 mL) was treated with LiHMDS (1 M, 57.8 mL) at −5° C. and the solution was stirred at −5° C. for 10 minutes. Then (Boc)$_2$O (6.31 g, 28.9 mmol) was added and the mixture was allowed to warm to rt and stirred for 1 h. On completion, the reaction mixture was quenched with saturated ammonium chloride solution (20 mL) and extracted with EtOAc (3×100 mL). The combined organic layers were washed with brine (20 mL), dried with Na$_2$SO$_4$, filtered and concentrated in vacuo. The residue was purified by silica gel column chromatography to give the title compound (6.50 g, 82% yield) as a white solid. $^1$H NMR (400 MHz, CDCl$_3$) δ=8.92 (s, 1H), 8.27 (d, J=0.8 Hz, 1H), 8.13 (d, J=5.2 Hz, 1H), 7.12 (dd, J=1.6, 5.2 Hz, 1H), 1.55 (s, 9H).

Step 2—Tert-butyl N-(4-bromo-2-pyridyl)-N-(2,2,2-trifluoroethyl)carbamate

To a mixture of tert-butyl N-(4-bromo-2-pyridyl)carbamate (6.10 g, 22.3 mmol), cesium carbonate (11.0 g, 33.7 mmol) and DMF (60 mL) was added 2,2,2-trifluoroethyl trifluoromethanesulfonate (5.18 g, 22.3 mmol). The reaction mixture was stirred at rt for 15 h. On completion, the reaction mixture was quenched with saturated aqueous ammonium chloride solution (50 mL) and extracted with ethyl acetate (3×100 mL). The organic layer was washed with saturated brine (20 mL), dried over anhydrous sodium sulfate, filtered and concentrated in vacuo. The residue was purified by silica gel column chromatography to give the title compound (5.70 g, 72% yield) as a colorless oil. $^1$H NMR (400 MHz, CDCl$_3$) δ=8.18 (d, J=5.2 Hz, 1H), 8.01-7.94 (m, 1H), 7.24 (dd, J=1.6, 5.2 Hz, 1H), 4.81 (q, J=8.8 Hz, 2H), 1.55 (s, 9H).

Step 3—Tert-butyl N-[4-(4,4,5,5-tetramethyl-1,3,2-dioxaborolan-2-yl)-2-pyridyl]-N-(2,2,2-trifluoroethyl)carbamate To a solution of tert-butyl N-(4-bromo-2-pyridyl)-N-(2,2,2-trifluoroethyl)carbamate (3.00 g, 8.45 mmol) in dioxane (60 mL) was added 4,4,5,5-tetramethyl-2-(4,4,5,5-tetramethyl-1,3,2-dioxaborolan-2-yl)-1,3,2-dioxaborolane (10.7 g, 42.2 mmol), KOAc (1.66 g, 16.9 mmol) and Pd(dppf)Cl$_2$*CH$_2$Cl$_2$ (345 mg, 423 umol) under nitrogen atmosphere. The reaction mixture was then heated to 65° C. and stirred for 2 h. On completion, the reaction mixture was diluted with ethyl acetate (100 mL) and filtered. The filtrate was concentrated in vacuo. The residue was purified by silica gel column chromatography to give the title compound (3.00 g, 96% yield) as a white solid. $^1$H NMR (400 MHz, CDCl$_3$) δ=8.38 (dd, J=0.8, 4.8 Hz, 1H), 7.91 (s, 1H), 7.42 (d, J=4.8 Hz, 1H), 4.76 (q, J=8.8 Hz, 2H), 1.52 (s, 9H), 1.35 (s, 12H).

Step 4—Ethyl 2-[2-[tert-butoxycarbonyl(2,2,2-trifluoroethyl)amino]-4-pyridyl]oxazole-4-carboxylate To a solution of tert-butyl N-[4-(4,4,5,5-tetramethyl-1,3,2-dioxaborolan-2-yl)-2-pyridyl]-N-(2,2,2-trifluoroethyl)carbamate (4.00 g, 9.94 mmol), ethyl 2-bromooxazole-4-carboxylate (2.19 g, 9.94 mmol) in dioxane (40 mL) and H$_2$O (8 mL) was added Cs$_2$CO$_3$ (6.48 g, 19.9 mmol) and Pd(dppf)Cl$_2$—CH$_2$Cl$_2$ (406 mg, 497 umol) and the mixture was stirred at 80° C. for 16 h. On completion, the reaction mixture was diluted with ethyl acetate (200 mL) and filtered. The filtrate was concentrated in vacuo. The residue was purified by silica gel column chromatography to give the title compound (2.10 g, 51% yield) as a yellow solid. $^1$H NMR (400 MHz, CDCl$_3$) δ=8.50 (d, J=5.2 Hz, 1H), 8.38 (s, 1H), 8.34 (s, 1H), 7.79 (d, J=5.2 Hz, 1H), 4.85 (q, J=8.8 Hz, 2H), 4.45 (q, J=7.2 Hz, 2H), 1.56 (s, 9H), 1.43 (t, J=7.2 Hz, 3H); LC-MS (ESI$^+$) m/z 416.1 (M+H)$^+$.

Step 5—2-[2-[Tert-butoxycarbonyl(2,2,2-trifluoroethyl)amino]-4-pyridyl]oxazole-4-carboxylic acid To a solution of ethyl 2-[2-[tert-butoxycarbonyl(2,2,2-trifluoroethyl)amino]-4-pyridyl]oxazole-4-carboxylate (100 mg, 241 umol) in THF (1 mL) and H$_2$O (200 uL) was added LiOH (11.5 mg, 482 umol). The mixture was stirred at rt for 0.5 h. On completion, the reaction mixture was acidified with 1N HCl (3 mL) to pH=5, then extracted with ethyl acetate (5×20 mL). The combined organic layers were washed with brine (20 mL), dried over anhydrous sodium sulfate, filtered and concentrated in vacuo to give the title compound (90.0 mg, 97% yield) as a white solid. $^1$H NMR (400 MHz, CDCl$_3$) δ=8.53 (dd, J=0.8, 5.2 Hz, 1H), 8.46 (s, 1H), 8.40 (s, 1H), 7.79 (dd, J=1.2, 5.2 Hz, 1H), 7.81-7.77 (m, 1H), 4.86 (q, J=8.8 Hz, 2H), 1.57 (s, 9H); LC-MS (ESI$^+$) m/z 388.1 (M+H)$^+$ Tert-butyl N-[4-[4-[[1-(4-formylcyclohexyl)-3-(1-hydroxy-1-methyl-ethyl)pyrazol-4-yl] carbamoyl]oxazol-2-yl]-2-pyridyl]-N-(2,2,2-trifluoroethyl)carbamate (Intermediate WO)

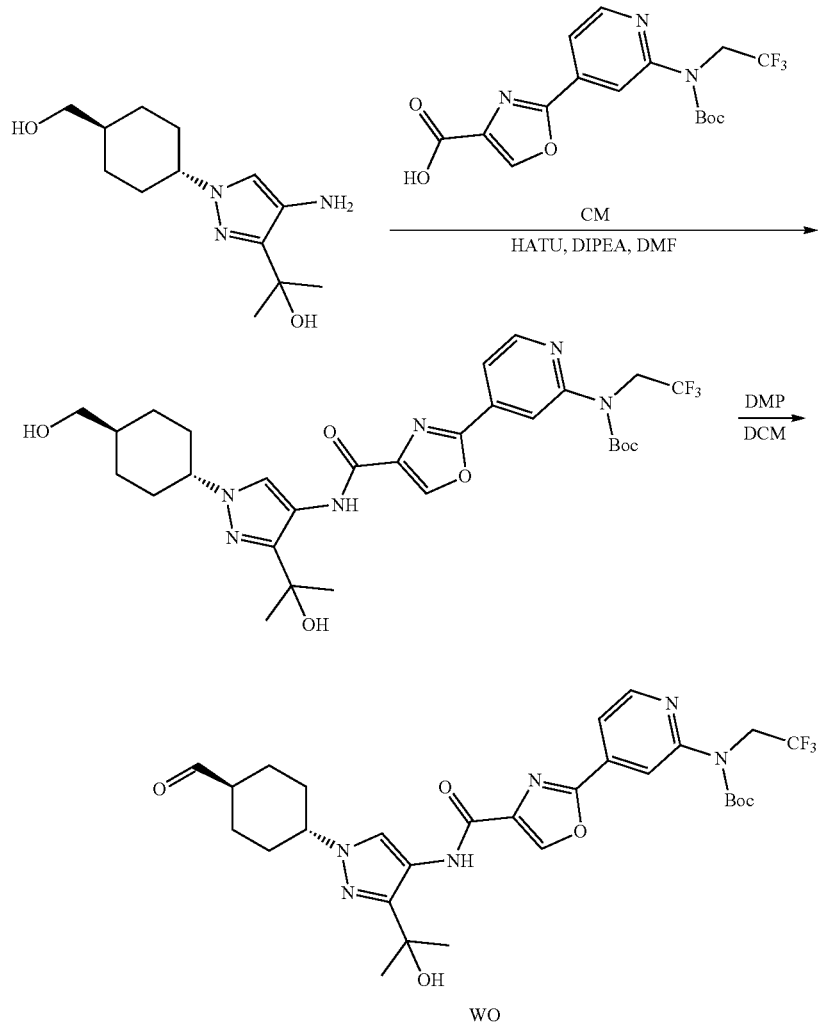

Step 1—Tert-butyl N-[4-[4-[[1-[4-(hydroxymethyl)cyclohexyl]-3-(1-hydroxy-1-methyl-ethyl)pyrazol-4-yl]carbamoyl]oxazol-2-yl]-2-pyridyl]-N-(2,2,2-trifluoroethyl)carbamate To a solution of 2-[4-amino-1-[4-(hydroxymethyl)cyclohexyl]pyrazol-3-yl]propan-2-ol (250 mg, 987 umol, synthesized via Step 1 of Intermediate UW) and 2-[2-[tert-butoxycarbonyl(2,2,2-trifluoroethyl)amino]-4-pyridyl]oxazole-4-carboxylic acid (344 mg, 888 umol, Intermediate CM) in DMF (10 mL) was added HATU (375 mg, 987 umol) and DIPEA (319 mg, 2.47 mmol) at 25° C. The reaction mixture was stirred at 25° C. for 2 hours. On completion, the reaction mixture was diluted with water (30 mL) and extracted with EA (3×20 mL). The combined organic layers were washed with water (20 mL), dried over $Na_2SO_4$, filtered and the filtrate was concentrated in vacuo to give the title compound (300 mg, 49% yield) as a purple solid. LC-MS (ESI) m/z 605.4 (M–17)$^+$.

Step 2—Tert-butyl N-[4-[4-[[1-(4-formylcyclohexyl)-3-(1-hydroxy-1-methyl-ethyl)pyrazol-4-yl]carbamoyl]oxazol-2-yl]-2-pyridyl]-N-(2,2,2-trifluoroethyl)carbamate To a solution of tert-butyl N-[4-[4-[[1-[4-(hydroxymethyl)cyclohexyl]-3-(1-hydroxy-1-methyl-ethyl) pyrazol-4-yl]carbamoyl] oxazol-2-yl]-2-pyridyl]-N-(2,2,2-trifluoroethyl)carbamate (1.00 g, 1.61 mmol) in DCM (15 mL) was added DMP (1.36 g, 3.21 mmol) at 25° C. The reaction mixture was stirred at 25° C. for 2 hours. On completion, the reaction was quenched with sat. aq. $Na_2S_2O_3$ (30 mL) and sat. aq. $NaHCO_3$ (30 mL). The mixture was extracted with DCM (3×30 mL). The combined organic layer was concentrated in vacuo. The residue was purified by reverse phase (FA condition) to give the title compound (90.0 mg, 9% yield) as a brown solid. $^1$H NMR (400 MHz, DMSO-$d_6$) δ 9.61 (s, 1H), 9.25 (s, 1H), 9.04 (s, 1H), 8.71-8.59 (m, 1H), 8.31-8.23 (m, 1H), 8.19 (s, 1H), 7.81-7.69 (m, 1H), 4.89 (q, J=8.8 Hz, 2H), 4.21-4.03 (m, 1H), 2.39 (s, 1H), 2.17-1.97 (m, 7H), 1.77 (s, 6H), 1.51 (s, 9H); LC-MS (ESI⁺) m/z 603.4 (M−17)⁺.

Tert-butyl N-methyl-N-[[(2R)-4-prop-2-ynylmorpholin-2-yl]methyl]carbamate (Intermediate WP)

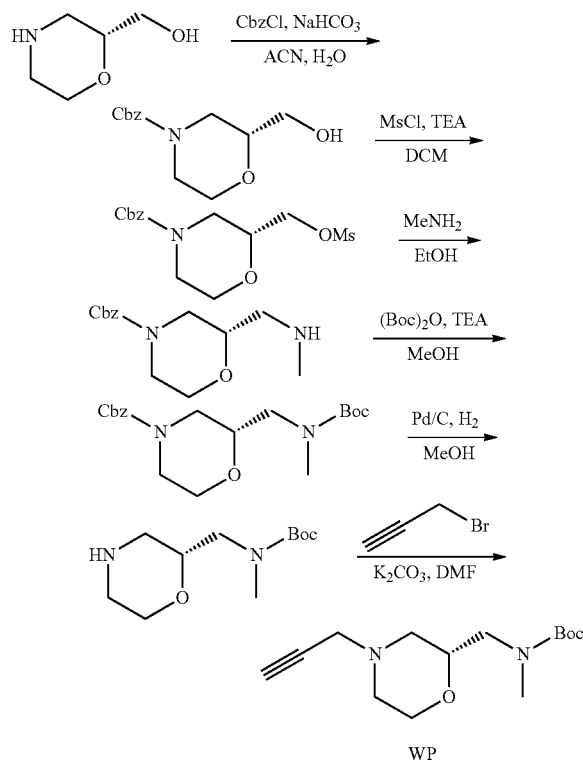

WP

Step 1—Benzyl (2R)-2-(hydroxymethyl)morpholine-4-carboxylate

To a solution of [(2R)-morpholin-2-yl]methanol (2.50 g, 16.2 mmol, HCl, CAS #156925-22-3), NaHCO₃ (4.10 g, 48.8 mmol) in a mixed solvent of ACN (80.0 mL) and H₂O (80.0 mL) was added CbzCl (4.16 g, 24.4 mmol, 3.47 mL) at 0° C. dropwise. The mixture was then stirred at 25° C. for 16 hrs. On completion, the mixture was concentrated in vacuo to remove ACN. Then the mixture was extracted with EA (2×20 mL), and the combined organic layers were concentrated in vacuo. The residue was purified by silica gel column (PE:EA=1:1) to give the title compound (3.7 g, 90% yield) as colorless oil. ¹H NMR (400 MHz, CDCl₃) δ 7.42-7.33 (m, 5H), 5.17 (d, J=2.0 Hz, 2H), 4.08-3.88 (m, 3H), 3.77-3.65 (m, 1H), 3.63-3.46 (m, 3H), 3.13-2.73 (m, 2H), 2.07-1.96 (m, 1H).

Step 2—Benzyl (2R)-2-(methyl sulfonyloxymethyl)morpholine-4-carboxylate

To a solution of benzyl (2R)-2-(hydroxymethyl)morpholine-4-carboxylate (3.70 g, 14.7 mmol), and TEA (4.47 g, 44.1 mmol) in DCM (40.0 mL) was added MsCl (2.53 g, 22.0 mmol) at 0° C., then the mixture was stirred at 25° C. for 1 hr. On completion, the mixture was diluted with DCM (20 mL) and washed with H₂O (3×30 mL). The organic layer was dried over anhydrous Na₂SO₄, filtered and concentrated in vacuo to give the title compound (4.85 g, 100% yield) as yellow oil. ¹H NMR (400 MHz, CDCl₃) δ 7.43-7.33 (m, 5H), 5.20-5.15 (m, 2H), 4.26 (d, J=4.8 Hz, 2H), 4.10-3.83 (m, 3H), 3.80-3.65 (m, 1H), 3.63-3.48 (m, 1H), 3.08 (s, 3H), 3.07-2.75 (m, 2H).

Step 3—Benzyl (2S)-2-(methylaminomethyl)morpholine-4-carboxylate

To a solution of benzyl (2R)-2-(methylsulfonyloxymethyl)morpholine-4-carboxylate (4.3 g, 13.0 mmol) in EtOH (10.0 mL) was added MeNH₂ (40.5 g, 391 mmol, 30% solution in ethanol), and the mixture was stirred at 80° C. for 16 hrs in a 100 mL of autoclave. On completion, the mixture was concentrated in vacuo to give the title compound (3.45 g, 100% yield) as yellow oil. LC-MS (ESI⁺) m/z 265.1 (M+H)⁺.

Step 4—Benzyl (2S)-2-[[tert-butoxycarbonyl(methyl)amino]methyl]morpholine-4-carboxylate To a solution of benzyl (2S)-2-(methylaminomethyl)morpholine-4-carboxylate (3.45 g, 13.0 mmol) in MeOH (50.0 mL) was added TEA (1.58 g, 15.6 mmol, 2.18 mL). Then (Boc)₂O (4.27 g, 19.5 mmol, 4.50 mL) was added into the above mixture dropwise. The mixture was stirred at 25° C. for 2 hrs. On completion, the mixture was concentrated in vacuo. The residue was purified by silica gel column (PE:EA=5:1) to give the title compound (4.10 g, 86% yield) as yellow oil. ¹H NMR (400 MHz, CDCl₃) δ 7.43-7.30 (m, 5H), 5.24-5.09 (m, 2H), 4.11-3.83 (m, 3H), 3.68-3.34 (m, 3H), 3.30-3.14 (m, 1H), 3.09-2.97 (m, 1H), 2.94 (s, 3H), 2.80-2.62 (m, 1H), 1.47 (s, 9H).

Step 5—Tert-butyl N-methyl-N-[[(2R)-morpholin-2-yl]methyl]carbamate

To a solution of benzyl (2S)-2-[[tert-butoxycarbonyl(methyl)amino]methyl]morpholine-4-carboxylate (4.10 g, 11.2 mmol) in MeOH (40.0 mL) was added Pd/C (1.00 g, 10% wt), and the mixture was stirred at 25° C. for 16 hrs under H₂ (15 psi). On completion, the mixture was filtered and the filtrate was concentrated in vacuo to give the title compound (2.54 g, 98% yield) as colorless oil. ¹H NMR (400 MHz, DMSO-d₆) δ 3.75-3.65 (m, 1H), 3.50-3.42 (m, 1H), 3.41-3.37 (m, 1H), 3.24-3.13 (m, 1H), 3.10-3.03 (m, 1H), 2.85-2.75 (m, 3H), 2.70-2.53 (m, 4H), 2.37-2.23 (m, 1H), 1.39 (s, 9H).

Step 6—Tert-butyl N-methyl-N-[[(2R)-4-prop-2-ynylmorpholin-2-yl]methyl]carbamate To a solution of tert-butyl N-methyl-N-[[(2R)-morpholin-2-yl]methyl]carbamate (1.00 g, 4.34 mmol), 3-bromoprop-1-yne (516 mg, 4.34 mmol, CAS #106-96-7) in DMF (10.0 mL) was added K₂CO₃ (3.00 g, 21.7 mmol). The mixture was stirred at 25° C. for 2 hrs. On completion, the mixture was diluted with H₂O (20 mL), then extracted with EA (2×20 mL). The combined organic layers were washed with brine (2×20 mL), dried over anhydrous Na₂SO₄, filtered and the filtrate was concentrated in vacuo. The residue was purified by silica gel column (PE:EA=5:1) to give the title compound (960 mg, 82% yield) as yellow oil. ¹H NMR (400 MHz, DMSO-d₆) δ 3.85-3.76 (m, 1H), 3.63-3.52 (m, 1H), 3.50-3.40 (m, 1H), 3.30-3.24 (m, 2H), 3.20-3.14 (m, 2H), 2.84-2.78 (m, 3H), 2.68-2.55 (m, 2H), 2.54-2.52 (m, 1H), 2.30-2.16 (m, 1H), 2.03-1.90 (m, 1H), 1.39 (s, 9H).

3-[3-Methyl-5-[3-[(2S)-2-(methylaminomethyl)morpholin-4-yl]prop-1-ynyl]-2-oxo-benzimidazol-1-yl] piperidine-2,6-dione (Intermediate WQ)

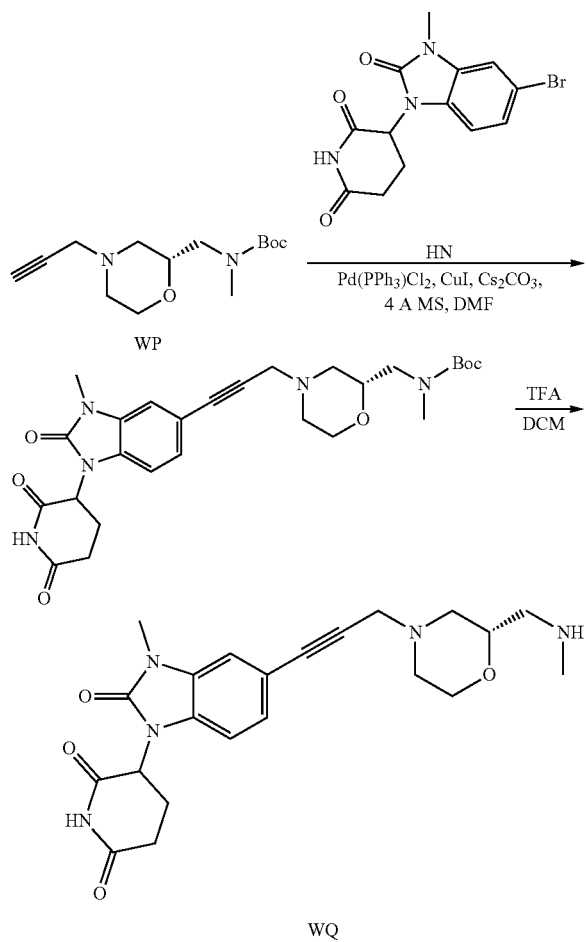

Step 1—Tert-butyl N-[[(2R)-4-[3-[1-(2,6-dioxo-3-piperidyl)-3-methyl-2-oxo-benzimidazol-5-yl] prop-2-ynyl]morpholin-2-yl]methyl]-Nmethyl-carbamate To a solution of tert-butyl N-methyl-N-[[(2R)-4-prop-2-ynylmorpholin-2-yl]methyl]carbamate (571 mg, 2.13 mmol, Intermediate WP), 3-(5-bromo-3-methyl-2-oxo-benzimidazol-1-yl)piperidine-2,6-dione (400 mg, 1.18 mmol, Intermediate HN) in DMF (15.0 mL) was added Pd(PPh₃)₂Cl₂ (83.0 mg, 118 umol), 4 Å molecular sieves (50.0 mg), Cs₂CO₃ (1.93 g, 5.91 mmol) and CuI (22.5 mg, 118 umol). The mixture was stirred at 80° C. for 2 hrs under N₂. On completion, the mixture was filtered and the filtrate was concentrated in vacuo. The residue was purified by reverse phase (0.1% FA) to give the title compound (400 mg, 64% yield) as yellow solid. ¹H NMR (400 MHz, CDCl₃) δ 8.28 (s, 1H), 7.17 (d, J=8.0 Hz, 1H), 7.10 (s, 1H), 6.74 (d, J=8.0 Hz, 1H), 5.25-5.14 (m, 1H), 3.99-3.90 (m, 1H), 3.82-3.65 (m, 2H), 3.57-3.47 (m, 2H), 3.43 (s, 3H), 3.25-3.14 (m, 1H), 3.00-2.94 (m, 1H), 2.94 (s, 3H), 2.89-2.82 (m, 2H), 2.82- 2.74 (m, 2H), 2.74-2.63 (m, 1H), 2.50-2.38 (m, 1H), 2.30-2.21 (m, 1H), 2.20-2.13 (m, 1H), 1.45 (s, 9H).

Step 2—3-[3-Methyl-5-[3-[(2S)-2-(methylaminomethyl)morpholin-4-yl]prop-1-ynyl]-2-oxo-benzimidazol-1-yl]]piperidine-2,6-dione To a solution of tert-butyl N-[[(2R)-4-[3-[1-(2,6-dioxo-3-piperidyl)-3-methyl-2-oxo-benzimidazol-5-yl] prop-2-ynyl] morpholin-2-yl]methyl]-N-methyl-carbamate (150 mg, 285 umol) in DCM (5.00 mL) was added TFA (7.70 g, 67.5 mmol, 5.00 mL). The mixture was stirred at 20° C. for 1 hr. On completion, the mixture was concentrated in vacuo to give the title compound (150 mg, 97% yield, TFA salt) as yellow solid. ¹H NMR (400 MHz, DMSO-d₆) δ 11.15 (s, 1H), 8.83 (s, 1H), 7.37 (d, J=1.2 Hz, 1H), 7.27-7.22 (m, 1H), 7.22-7.17 (m, 1H), 5.47-5.37 (m, 1H), 4.39-4.21 (m, 3H), 4.18-4.14 (m, 1H), 4.09-4.03 (m, 1H), 3.84-3.73 (m, 1H), 3.58-3.44 (m, 2H), 3.36 (s, 3H), 3.27-3.17 (m, 1H), 3.12-3.02 (m, 2H), 2.95-2.84 (m, 2H), 2.68-2.62 (m, 1H), 2.60-2.57 (m, 3H), 2.09-2.00 (m, 1H).

Tert-butyl N-(4-but-3-ynoxybutyl)carbamate (Intermediate SY)

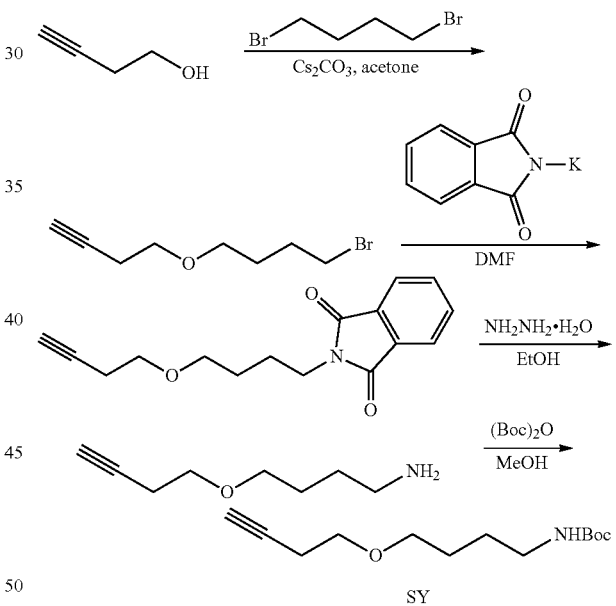

Step 1—1-bromo-4-but-3-ynoxy-butane

A mixture of but-3-yn-1-ol (40 g, 571 mmol, 43.2 mL, CAS #927-74-2), 1,4-dibromobutane (185 g, 856 mmol, 103 mL, CAS #110-52-1), Cs₂CO₃ (204 g, 627 mmol) in acetone (500 mL) was degassed and purged with N₂ for 3 times. Then the mixture was stirred at 70° C. for 72 hrs under N₂ atmosphere. On completion, the mixture was filtered and the filtrate was concentrated in vacuo. The residue was purified by silica gel chromatography to give the title compound (40.0 g, 34% yield) as colorless oil. ¹H NMR (400 MHz, CDCl₃) δ 3.57 (t, J=6.8 Hz, 2H), 3.52 (t, J=6.2 Hz, 2H), 3.49-3.45 (m, 3H), 2.48 (dt, J=2.8, 6.8 Hz, 2H), 2.08-2.04 (m, 1H), 2.03-1.96 (m, 2H), 1.80-1.71 (m, 2H).

Step 2—2-(4-But-3-ynoxybutyl)isoindoline-1,3-dione

To a solution of 1-bromo-4-but-3-ynoxy-butane (27.0 g, 131 mmol) in DMF (300 mL) was added (1,3-dioxoisoindolin-2-yl)potassium (29.3 g, 158 mmol). The mixture was stirred at 60° C. for 6 hrs. On completion, 1500 mL H$_2$O was added to the mixture, and the mixture was extracted with EA (2×800 mL). The organic layer was washed with brine (300 mL), and then concentrated in vacuo to give the title compound (30.0 g, 84% yield) as white solid. $^1$H NMR (400 MHz, CDCl$_3$) δ 7.87-7.83 (m, 2H), 7.75-7.70 (m, 2H), 3.73 (t, J=7.2 Hz, 2H), 3.53 (td, J=6.8, 19.2 Hz, 4H), 2.45 (dt, J=2.8, 7.2 Hz, 2H), 1.98 (t, J=2.8 Hz, 1H), 1.83-1.71 (m, 2H), 1.69-1.59 (m, 2H).

Step 3—4-But-3-ynoxybutan-1-amine

To a solution of 2-(4-but-3-ynoxybutyl)isoindoline-1,3-dione (50.0 g, 184 mmol) in EtOH (1000 mL) was added NH$_2$NH$_2$.H$_2$O (92.3 g, 1.84 mol, 89.6 mL). The mixture was stirred at 80° C. for 4 hrs. On completion, the mixture was filtered and the filtrate was concentrated in vacuo to give the title compound (21.0 g, 31% yield) as colorless oil. $^1$H NMR (400 MHz, CDCl$_3$) δ 3.49 (t, J=7.2 Hz, 2H), 3.43-3.38 (m, 2H), 2.65 (t, J=7.2 Hz, 2H), 2.39 (dt, J=2.8, 6.8 Hz, 2H), 1.91 (t, J=2.8 Hz, 1H), 1.89 (s, 2H), 1.60-1.52 (m, 2H), 1.49-1.40 (m, 2H).

Step 4—Tert-butyl N-(4-but-3-ynoxybutyl)carbamate

To a solution of 4-but-3-ynoxybutan-1-amine (30.0 g, 212 mmol) in MeOH (300 mL) was added (Boc)$_2$O (69.6 g, 318 mmol, 73.2 mL). The mixture was stirred at 25° C. for 4 hrs. On completion, the mixture was concentrated in vacuo. The residue was purified by silica gel chromatography to give the title compound (50.0 g, 97% yield) as colorless oil. $^1$H NMR (400 MHz, CDCl$_3$) δ 4.68 (s, 1H), 3.57 (t, J=6.8 Hz, 2H), 3.49 (t, J=6.0 Hz, 2H), 3.20-3.11 (m, 2H), 2.48 (dt, J=2.8, 6.8 Hz, 2H), 1.99 (t, J=2.8 Hz, 1H), 1.68-1.59 (m, 4H), 1.46 (s, 9H).

Tert-butyl N-(4-but-3-ynoxybutyl)-N-methyl-carbamate (Intermediate RS)

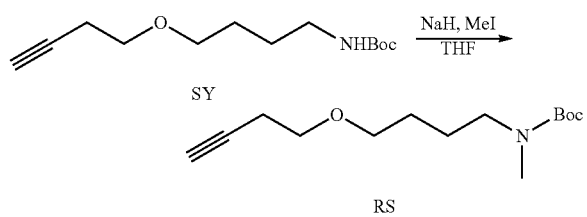

To a solution of tert-butyl N-(4-but-3-ynoxybutyl)carbamate (5.00 g, 20.7 mmol, Intermediate SY) in THF (100 mL) was added NaH (1.24 g, 31.0 mmol, 60% oil dispersion) at 0° C. The mixture was stirred 20° C. for 1 hour. Then MeI (4.41 g, 31.0 mmol) was added. The mixture was stirred at 20° C. for 15 hrs. On completion, the mixture was quenched by water (10 mL) and extracted with EA (2×250 mL). The combined organic layers were concentrated in vacuo to give the title compound (5.00 g, 94% yield) as yellow oil. $^1$H NMR (400 MHz, CDCl$_3$) δ 3.57 (t, J=7.2 Hz, 2H), 3.50 (t, J=6.0 Hz, 2H), 3.24 (s, 2H), 2.85 (s, 3H), 2.48 (dt, J=2.8, 6.8 Hz, 2H), 2.03-1.96 (m, 1H), 1.62-1.56 (m, 4H), 1.47 (s, 9H).

3-[3-Methyl-4-[4-[4-(methylamino)butoxy]butyl]-2-oxo-benzimidazol-1-yl]piperidine-2,6-dione (Intermediate WR)

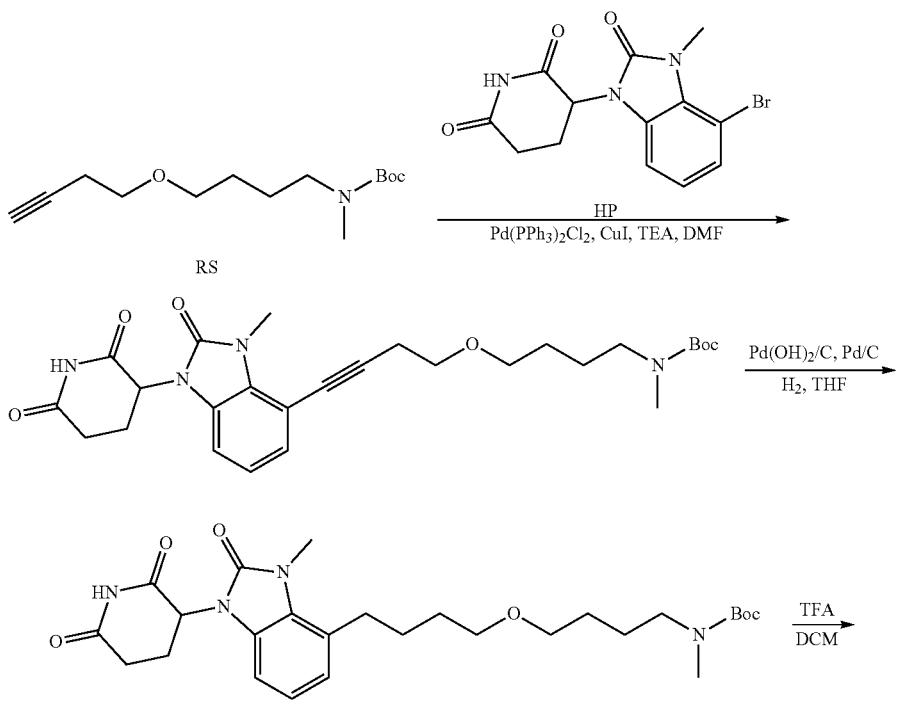

-continued

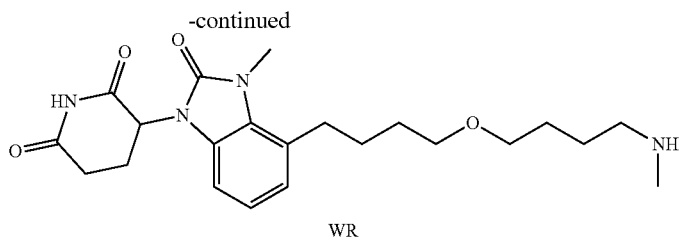

WR

Step 1—Tert-butyl N-[4-[4-[1-(2,6-dioxo-3-piperidyl)-3-methyl-2-oxo-benzimidazol-4-yl]but-3-ynoxy] butyl]-N-methyl-carbamate To a solution of tert-butyl N-(4-but-3-ynoxybutyl)-N-methyl-carbamate (500 mg, 1.96 mmol, Intermediate RS) and 3-(4-bromo-3-methyl-2-oxo-benzimidazol-1-yl)piperidine-2,6-dione (221 mg, 653 umol, Intermediate HP) in DMF (10 mL) was added CuI (24.8 mg, 131 umol), Cs₂CO₃ (213 mg, 653 umol), Pd(PPh₃)₂Cl₂ (91.6 mg, 131 umol) and 4 Å molecular sieves (200 mg, 653 umol) at 25° C. The reaction mixture was stirred at 80° C. for 2 hours. On completion, the reaction mixture was filtered and concentrated in vacuo. The residue was diluted with water (30 mL), and then extracted with EA (3×50 mL). The combined organic layers were washed with brine (30 mL), dried over Na₂SO₄, filtered and the filtrate was concentrated in vacuo. The residue was purified by reverse phase (FA condition) to give the title compound (320 mg, 95% yield) as a purple solid. LC-MS (ESI⁺) m/z 413.2 (M+H-100)⁺.

Step 2—Tert-butyl N-[4-[4-[1-(2,6-dioxo-3-piperidyl)-3-methyl-2-oxo-benzimidazol-4-yl]butoxy] butyl]-N-methyl-carbamate To a solution of tert-butyl N-[4-[4-[1-(2,6-dioxo-3-piperidyl)-3-methyl-2-oxo-benzimidazol-4-yl] but-3-ynoxy] butyl]-N-methyl-carbamate (300 mg, 585 umol) in THF (20 mL) was added Pd(OH)₂/C (500 mg, 585 umol, 20 wt %) and Pd/C (500 mg, 585 umol, 10 wt %) at 25° C. The reaction mixture was stirred at 25° C. for 2 hours under H₂ (15 psi). On completion, the reaction mixture was filtered through celite and the filtrate was concentrated in vacuo to give the title compound (280 mg, 92% yield) as colorless oil. LC-MS (ESI⁺) m/z 417.3 (M+H-100)⁺.

Step 3—3-[3-methyl-4-[4-[4-(methylamino)butoxy] butyl]-2-oxo-benzimidazol-1-yl]piperidine-2,6-dione To a solution of tert-butyl N-[4-[4-[1-(2,6-dioxo-3-piperidyl)-3-methyl-2-oxo-benzimidazol-4-yl] butoxy]butyl]-N-methyl-carbamate (140 mg, 271 umol) in DCM (10 mL) was added TFA (5 mL) at 25° C. The reaction mixture was stirred at 25° C. for 2 hours. On completion, the reaction mixture was concentrated in vacuo to give the title compound (110 mg, 97% yield) as colorless oil. LC-MS (ESI⁺) m/z 417.2 (M+H)⁺.

Methyl 4-(4-amino-3-carbamoyl-pyrazol-1-yl)cyclohexanecarboxylate (Intermediate RE)

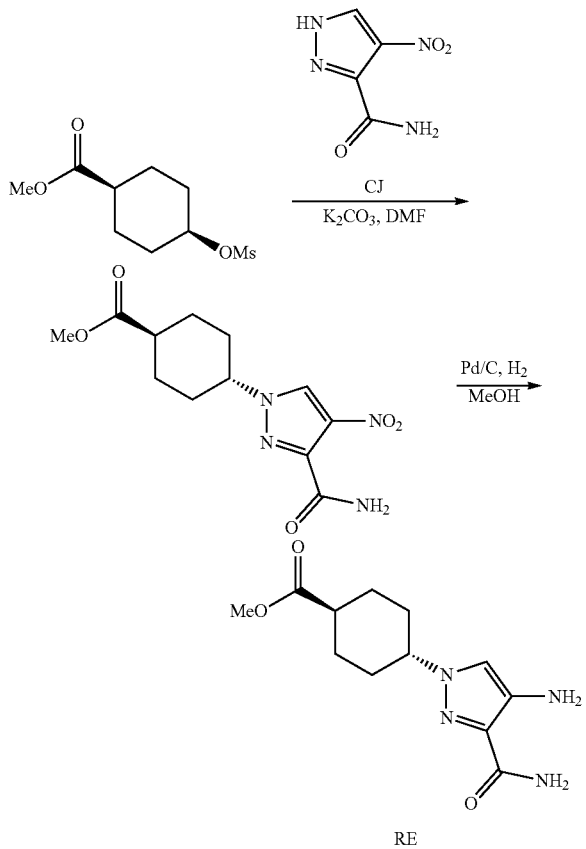

RE

Step 1—Methyl 4-(3-carbamoyl-4-nitro-pyrazol-1-yl)cyclohexanecarboxylate

To a solution of methyl 4-methylsulfonyloxycyclohexanecarboxylate (3.63 g, 15.3 mmol, synthesized via Step 1 of Intermediate QZ) and 4-nitro-1H-pyrazole-3-carboxamide (2.00 g, 12.8 mmol, Intermediate CJ) in DMF (60.0 mL) was added K₂CO₃ (5.31 g, 38.4 mmol). The mixture was stirred at 85° C. for 16 hrs. On completion, the mixture was filtered and the filtrate was diluted with water (100 mL), then the mixture was extracted with EA (2×50 mL). The organic layer was washed with brine (50 ml) and then concentrated in vacuo. The residue was purified by silica gel chromatography (PE:EA=3:1) to give the title compound (500 mg, 13% yield) as white solid. ¹H NMR (400 MHz, CDCl₃) δ 8.30 (s, 1H), 7.81 (s, 1H), 6.11 (s, 1H), 4.31-4.19 (m, 1H), 3.73 (s, 3H), 2.47-2.38 (m, 1H), 2.37-2.30 (m, 2H), 2.30-2.20 (m, 2H), 1.91-1.76 (m, 2H), 1.73-1.65 (m, 2H).

Step 2—Methyl 4-(4-amino-3-carbamoyl-pyrazol-1-yl)cyclohexanecarboxylate

To a solution of methyl 4-(3-carbamoyl-4-nitro-pyrazol-1-yl)cyclohexanecarboxylate (840 mg, 2.84 mmol) in THF (30 mL) was added Pd/C (200 mg, 10 wt %). The mixture was stirred at 25° C. for 2 hrs under H₂ (15 psi). On completion, the mixture was filtered and the filtrate was concentrated in vacuo to give the title compound (740 mg, 98% yield) as yellow solid. ¹H NMR (400 MHz, CDCl₃) δ 6.98 (s, 1H), 6.60 (s, 1H), 5.34 (s, 1H), 4.15 (s, 2H), 4.01-3.90 (m, 1H), 3.71 (s, 3H), 2.42-2.31 (m, 1H), 2.22-2.14 (m, 4H), 1.83-1.76 (m, 2H), 1.68-1.60 (m, 2H).

Tert-butyl N-[4-[4-[[3-carbamoyl-1-(4-formylcyclohexyl)pyrazol-4-yl]carbamoyl]oxazol-2-yl]-2-pyridyl]-N-(2,2,2-trifluoroethyl)carbamate (Intermediate RF)

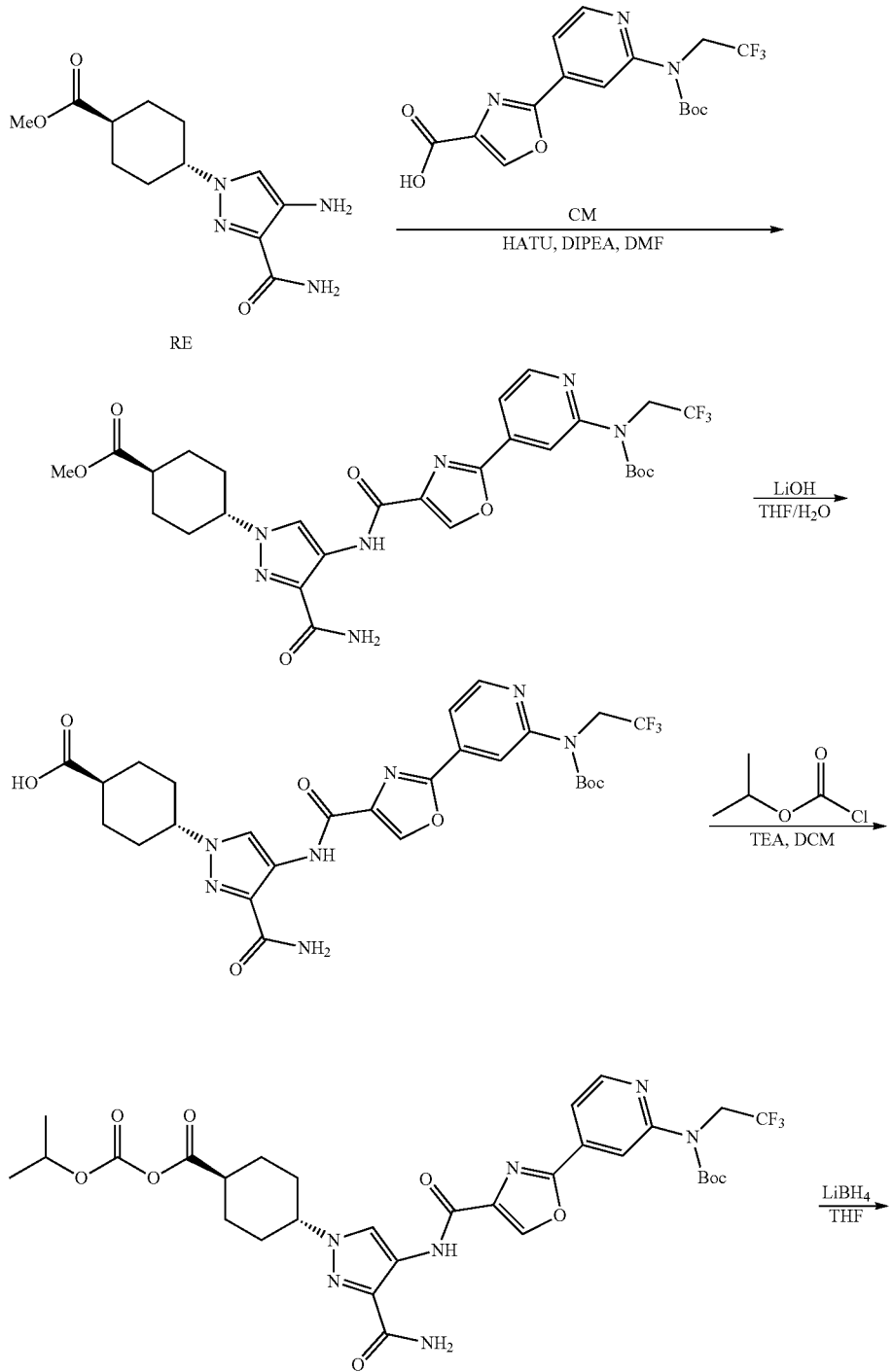

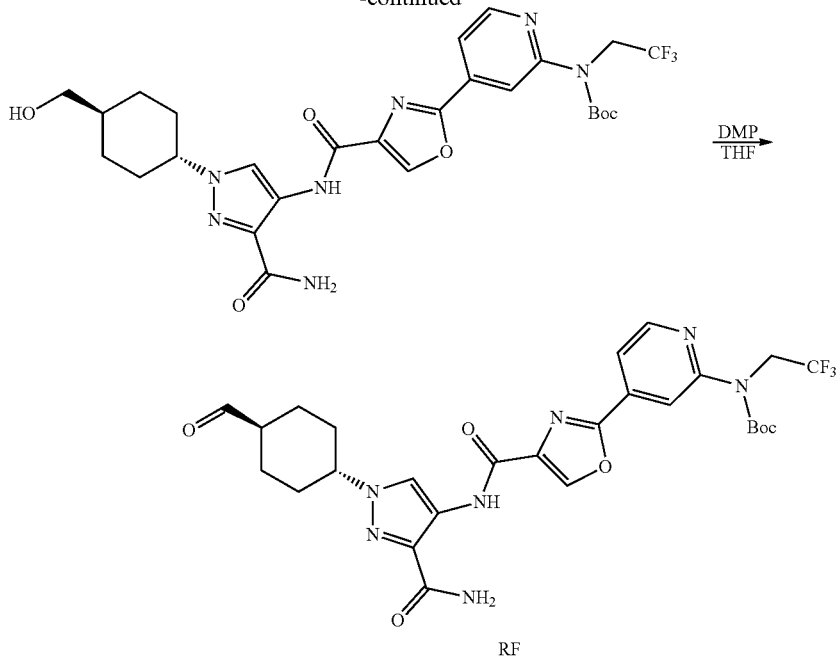

Step 1—Methyl 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]cyclohexanecarboxylate To a solution of methyl 4-(4-amino-3-carbamoyl-pyrazol-1-yl)cyclohexanecarboxylate (740 mg, 2.78 mmol, Intermediate RE) and 2-[2-[tertbutoxycarbonyl(2,2,2-trifluoroethyl)amino]-4-pyridyl]oxazole-4-carboxylic acid (1.08 g, 2.78 mmol, Intermediate CM) in DMF (20.0 mL) was added DIPEA (1.08 g, 8.34 mmol) and HATU (1.27 g, 3.33 mmol). The mixture was stirred at 25° C. for 0.5 hr. On completion, the mixture was diluted with $H_2O$ (30 mL), and extracted with EA (3×15 mL). The organic layers were washed with brine (2×20 mL), dried over anhydrous $Na_2SO_4$, filtered and concentrated in vacuo to give the title compound (1.75 g, 99% yield) as yellow solid. $^1H$ NMR (400 MHz, $CDCl_3$) δ 10.87 (s, 1H), 8.51 (d, J=5.2 Hz, 1H), 8.39 (s, 1H), 8.34 (s, 2H), 7.87-7.83 (m, 1H), 6.74 (s, 1H), 5.51 (s, 1H), 4.94-4.81 (m, 2H), 4.19-4.09 (m, 1H), 3.73 (s, 3H), 2.47-2.37 (m, 1H), 2.33-2.18 (m, 4H), 1.93-1.82 (m, 2H), 1.75-1.65 (m, 2H), 1.58 (s, 9H).

Step 2—4-[4-[[2-[2-[Tert-butoxycarbonyl(2,2,2-trifluoroethyl)amino]-4-pyridyl]oxazole-4-carbonyl]amino]-3-carbamoyl-pyrazol-1-yl] cyclohexanecarboxylic acid To a solution of methyl 4-[4-[[2-[2-[tert-butoxycarbonyl(2,2,2-trifluoroethyl)amino]-4-pyridyl] oxazole-4-carbonyl]amino]-3-carbamoyl-pyrazol-1-yl]cyclohexanecarboxylate (1.75 g, 2.75 mmol) in THF (30.0 mL) and $H_2O$ (6.00 mL) was added LiOH (329 mg, 13.7 mmol). The mixture was stirred at 25° C. for 4 hrs. On completion, the mixture was concentrated in vacuo and then diluted with $H_2O$ (50 mL). Then the mixture was adjusted with 1N HCl until the pH=5. The mixture was filtered and the solid was dried in vacuo to give the title compound (1.50 g, 87% yield) as white solid. $^1H$ NMR (400 MHz, DMSO-$d_6$) δ 11.01 (s, 1H), 9.05 (s, 1H), 8.65 (d, J 5.2 Hz, 1H), 8.37 (s, 1H), 8.24 (s, 1H), 7.79-7.74 (m, 1H), 7.68 (s, 1H), 7.50 (s, 1H), 4.99-4.80 (m, 2H), 4.32-4.17 (m, 1H), 2.14-1.98 (m, 1H), 2.10-1.98 (m, 4H), 1.89-1.78 (m, 2H), 1.53 (s, 9H), 1.51-1.43 (m, 2H).

Step 3—Isopropoxycarbonyl 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl] cyclohexanecarboxylate To a solution of 4-[4-[[2-[2-[tert-butoxycarbonyl(2,2,2-trifluoroethyl)amino]-4-pyridyl]oxazole-4-carbonyl]amino]-3-carbamoyl-pyrazol-1-yl]cyclohexanecarboxylic acid (1.50 g, 2.41 mmol), TEA (976 mg, 9.65 mmol) in THF (30.0 mL) was added isopropyl carbonochloridate (739 mg, 6.03 mmol) at −10° C. The mixture was stirred at −10° C. for 1 hr. On completion, the mixture was filtered and the filtrate was concentrated in vacuo to give the title compound (1.70 g, 99% yield) as white solid. LC-MS (ESI$^+$) m/z 708.3 (M+H)$^+$.

Step 4—Tert-butyl N-[4-[4-[[3-carbamoyl-1-[4-(hydroxymethyl)cyclohexyl]pyrazol-4-yl] carbamoyl] oxazol-2-yl]-2-pyridyl]-N-(2,2,2-trifluoroethyl) carbamate To a solution of isopropoxycarbonyl 4-[4-[[2-[2-[tert-butoxycarbonyl(2,2,2-trifluoroethyl)amino]-4-pyridyl]oxazole-4-carbonyl] amino]-3-carbamoyl-pyrazol-1-yl]cyclohexanecarboxylate (1.70 g, 2.40 mmol) in THF (50.0 mL) and $H_2O$ (5 mL) was added $LiBH_4$ (313 mg, 14.4 mmol) under 0° C. The mixture was stirred at 0° C. for 1 hr. On completion, the mixture was quenched with $H_2O$ (50 mL), then extracted with DCM (2×50 mL). The organic layers were dried over anhydrous $Na_2SO_4$, filtered concentrated in vacuo to give the title compound (1.10 g, 75% yield) as yellow solid. $^1H$ NMR (400 MHz, DMSO-$d_6$) δ 11.00 (s, 1H), 9.03 (s, 1H), 8.65 (d, J=5.2 Hz, 1H), 8.37 (s, 1H), 8.23 (s, 1H), 7.77 (d, J=5.2 Hz, 1H), 7.66 (s, 1H), 7.49 (s, 1H), 4.96-4.87 (m, 2H), 4.51 (s, 1H), 4.30-4.13 (m, 1H), 3.30-3.24 (m, 2H), 2.54-2.52 (m, 1H), 2.13-1.99 (m, 3H), 1.92-1.85 (m, 2H), 1.83-1.74 (m, 2H), 1.52 (s, 9H), 1.50-1.40 (m, 2H).

Step 5—Tert-butyl N-[4-[4-[[3-carbamoyl-1-(4-formylcyclohexyl)pyrazol-4-yl]carbamoyl]oxazol-2-yl]-2-pyridyl]-N-(2,2,2-trifluoroethyl)carbamate To a solution of tert-butyl N-[4-[4-[[3-carbamoyl-1-[4-(hydroxymethyl)cyclohexyl]pyrazol-4-yl] carbamoyl] oxazol-2-yl]-2-pyridyl]-N-(2,2,2-trifluoroethyl)carbamate (1.10 g, 1.81 mmol) in THF (30.0 mL) was added DMP (921 mg, 2.17 mmol). The mixture was stirred at 25° C. for 1 hr. On completion, the mixture was quenched with saturated Na$_2$S$_2$O$_3$ (30 mL) and washed with saturated NaHCO$_3$ (2×30 mL). The organic layer was dried over anhydrous Na$_2$SO$_4$, filtered and concentrated in vacuo to give the title compound (1.00 g, 91% yield) as yellow solid. $^1$H NMR (400 MHz, DMSO-d$_6$) δ 11.02 (s, 1H), 9.63 (s, 1H), 9.04 (s, 1H), 8.65 (d, J=5.2 Hz, 1H), 8.39 (s, 1H), 8.24 (s, 1H), 7.77 (dd, J=1.2, 5.2 Hz, 1H), 7.68 (s, 1H), 7.52 (s, 1H), 4.96-4.83 (m, 2H), 4.33-4.21 (m, 1H), 2.47-2.33 (m, 1H), 2.19-2.08 (m, 4H), 1.95-1.84 (m, 2H), 1.52 (s, 9H), 1.46-1.37 (m, 2H).

Ethyl 2-[2-[2-[2-[2-(tert-butoxycarbonylamino)ethoxy]ethoxy]ethoxy]ethoxy]acetate (Intermediate CH)

organic layers were dried over sodium sulfate and concentrated in vacuo to give a residue. The residue was purified by silica gel chromatography to give the title compound (2.60 g, 18% yield) as a colorless oil. $^1$H NMR (400 MHz, CDCl$_3$) δ 4.16 (q, J=7.2 Hz, 2H), 4.10 (s, 2H), 3.71-3.59 (m, 14H), 3.58-3.54 (m, 2H), 1.24 (t, J=7.2 Hz, 3H).

Step 2—Ethyl 2-[2-[2-[2-(2-methylsulfonyloxyethoxy)ethoxy]ethoxy]ethoxy]acetate To a solution of ethyl 2-[2-[2-[2-(2-hydroxyethoxy)ethoxy] ethoxy]ethoxy] acetate (6.86 g, 24.5 mmol) in DCM (50 mL) was added TEA (4.95 g, 48.9 mmol). The reaction mixture was cooled to 0° C. Then MsCl (3.36 g, 29.4 mmol) was added into the solution slowly. The reaction mixture was stirred at rt for 0.5 hour. On completion, the reaction mixture was quenched with H$_2$O (20 mL) and saturated citric acid solution (20 mL) was added until the pH=5-6, then they organic layer was separated. The organic layer was washed with brine (4×50 mL), dried over Na$_2$SO$_4$, filtered and concentrated in vacuo to give the title compound (8.00 g, 91% yield) as a brown oil. $^1$H NMR (400 MHz, CDCl$_3$) δ 4.43-4.37 (m, 2H), 4.23 (q, J=7.2 Hz, 2H), 4.16 (s, 2H), 3.82-3.62 (m, 14H), 3.10 (s, 3H), 1.30 (t, J=7.2 Hz, 3H).

Step 3—Ethyl 2-[2-[2-[2-(2-azidoethoxy)ethoxy]ethoxy]ethoxy]acetate

To a solution of ethyl 2-[2-[2-[2-(2-methylsulfonyloxyethoxy)ethoxy]ethoxy]ethoxy]acetate (8.00 g, 22.3 mmol)

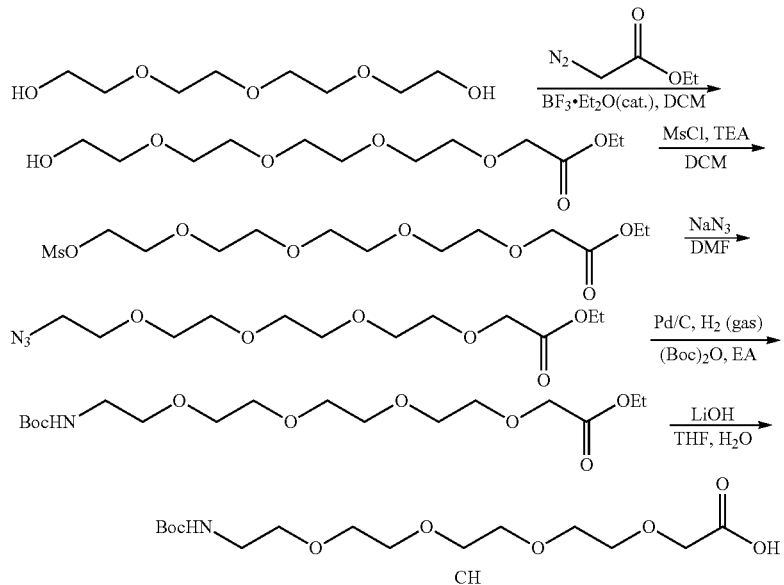

Step 1—Ethyl 14-hydroxy-3,6,9,12-tetraoxatetradecan-1-oate

To a solution of 2-[2-[2-(2-hydroxyethoxy)ethoxy]ethoxy]ethanol (10.0 g, 51.5 mmol, CAS #112-60-7) in DCM (150 mL) was added BF$_3$.Et$_2$O (159 mg, 515 umol) at 0° C. Then, ethyl 2-diazoacetate (5.87 g, 51.5 mmol) was added to the reaction mixture dropwise. After that, the mixture was allowed to warm to rt and stirred for 12 hours. On completion, the reaction mixture was quenched by ammonium chloride (5 mL), then diluted with water (100 mL), and extracted with DCM (3×50 mL). The combined in DMF (30 mL) was added NaN$_3$ (2.90 g, 44.6 mmol). The reaction mixture was stirred at 80° C. for 15 h. On completion, the solvent DMF was removed in vacuo. Then the residue was diluted with EA (150 mL) and filtered. The filtrate was used for the next step directly without further purification or concentration. LC-MS (ESI$^+$) m/z 278.1 (M+H-28)$^+$.

Step 4—Ethyl 2-[2-[2-[2-[2-(tert-butoxycarbonylamino)ethoxy]ethoxy]ethoxy]ethoxy]acetate To a solution of ethyl 2-[2-[2-[2-(2-azidoethoxy)ethoxy]ethoxy]ethoxy]acetate (6.81 g, 22.3 mmol) in EA (150 mL)

was added Pd/C (700 mg, 10 wt %) and (Boc)₂O (24.3 g, 112 mmol). The mixture was degassed and purged with hydrogen gas three times. Then the reaction mixture was stirred at rt for 15 hours. On completion, the mixture was filtered and the filtrate was concentrated in vacuo to give a residue. The residue was purified by silica gel chromatography (DCM/MeOH=10/1) to give the title compound (5.15 g, 61% yield) as a colorless oil. ¹H NMR (400 MHz, CDCl₃) δ 5.05 (s, 1H), 4.27 (q, J=7.2 Hz, 2H), 4.17 (s, 2H), 3.79-3.60 (m, 12H), 3.56 (t, J=5.2 Hz, 2H), 3.37-3.27 (m, 2H), 1.45 (s, 9H), 1.31 (t, J=7.2 Hz, 3H).

Step 5—Ethyl 2-[2-[2-[2-[2-(tert-butoxycarbonylamino)ethoxy]ethoxy]ethoxy]ethoxy]acetate To a solution of ethyl 2-[2-[2-[2-[2-(tert-butoxycarbonylamino)ethoxy]ethoxy]ethoxy]acetate (0.40 g, 1.05 mmol) in THF (10 mL) and H₂O (4 mL) was added LiOH (50.5 mg, 2.11 mmol). The reaction mixture was stirred at rt for 16 hours. On completion, the mixture was concentrated in vacuo to give a residue, then diluted with H₂O. The aqueous phase was acidified with conc. HCl until the pH=6 and concentrated in vacuo to give the title compound (350 mg, 996 umol) as a yellow solid. ¹HNMR (400 MHz, CDCl₃) δ 4.18 (m, 2H), 3.80-3.63 (m, 14H), 3.46-3.17 (m, 2H), 1.46-1.41 (s, 9H).

Ethyl 2-[2-[2-[2-(2-aminoethoxy)ethoxy]ethoxy] ethoxy]acetate (Intermediate DW)

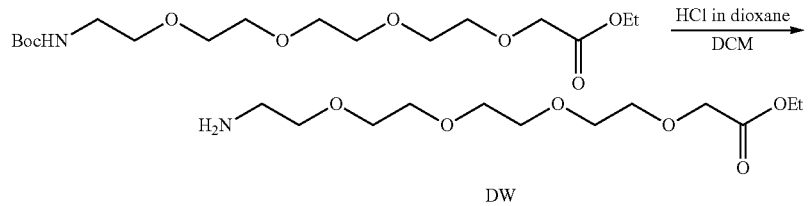

DW

To a solution of ethyl 2-[2-[2-[2-[2-(tert-butoxycarbonylamino)ethoxy]ethoxy]ethoxy]acetate (0.80 g, 2.11 mmol, synthesized via Steps 1-4 of Intermediate CH) in DCM (10 mL) was added HCl in dioxane (4 M, 2.67 mL). The reaction mixture was stirred at rt for 15 minutes. On completion, the reaction mixture was concentrated in vacuo to give the title compound (0.55 g, 83% yield, HCl) as a yellow oil.

2-(2,6-dioxopiperidin-3-yl)-4-fluoroisoindoline-1,3-dione (Intermediate R)

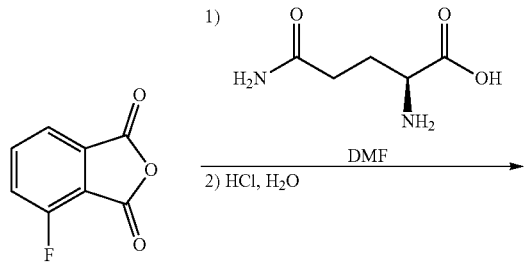

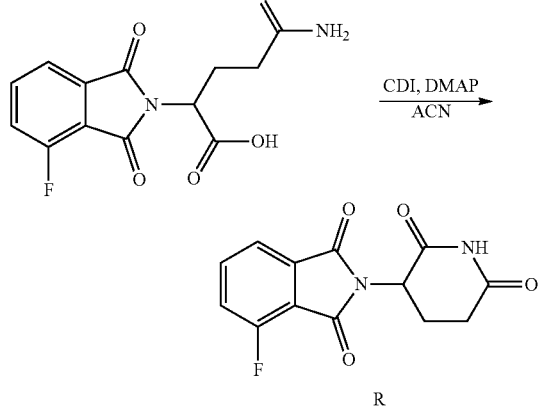

Step 1—5-amino-2-(4-fluoro-1,3-dioxoisoindolin-2-yl)-5-oxopentanoic acid

To a stirred solution of 4-fluoroisobenzofuran-1,3-dione (25 g, 150 mmol, CAS #652-39-1) in DMF (100 mL) was added L-glutamine (22 g, 150 mmol) at rt. The resulting reaction mixture was heated to at 90° C. and stirred for 2 h. The reaction mixture was then evaporated under reduced pressure, transferred into 4 N aqueous HCl solution and the resulting mixture was stirred for 36 h at rt. The solid precipitate was then filtered off, washed with cold water and dried under reduced pressure to give 5-amino-2-(4-fluoro-1,3-dioxoisoindolin-2-yl)-5-oxopentanoic acid as a white solid (28 g, 63%). LC-MS (ESI⁺) m/z 295 (M+H)⁺.

Step 2—2-(2,6-dioxopiperidin-3-yl)-4-fluoroisoindoline-1,3-dione

To a stirred solution of 5-amino-2-(4-fluoro-1,3-dioxoisoindolin-2-yl)-5-oxopentanoic acid (28 g, 95 mmol) in acetonitrile (200 mL) was added CDI (19 g, 110 mmol) and DMAP (0.14 g, 1.1 mmol) at rt. The resulting reaction mixture then heated to 90° C. and stirred for 5 h. The reaction mixture was then evaporated under reduced pressure. The crude product was purified using silica gel column chromatography (2% MeOH-DCM) to give 2-(2,6-dioxopiperidin-3-yl)-4-fluoroisoindoline-1,3-dione as a yellow solid (12 g, 46%). ¹H NMR (400 MHz, DMSO) δ ppm 11.16 (s, 1H), 7.98-7.93 (m, 1H), 7.80-7.76 (m, 2H), 5.19-5.14 (m, 1H), 2.94-2.85 (m, 1H), 2.63-2.54 (m, 2H), 2.09-2.04 (m, 1H).

(2S)-3-[(8R)-1-[4-[4-[2-[2-[2-[2-[2-[2-[[2-(2,6-di-oxo-3-piperidyl)-1,3-dioxo-isoindolin-4-yl]amino]ethoxy]ethoxy]ethoxy]ethoxy]acetyl]piperazin-1-yl]cyclohexoxy]-7,8-dihydro-6H-cyclopenta[4,5]thieno[1,2-c]pyrimidin-8-yl]-2-hydroxy-propanamide (Intermediate ZZ)

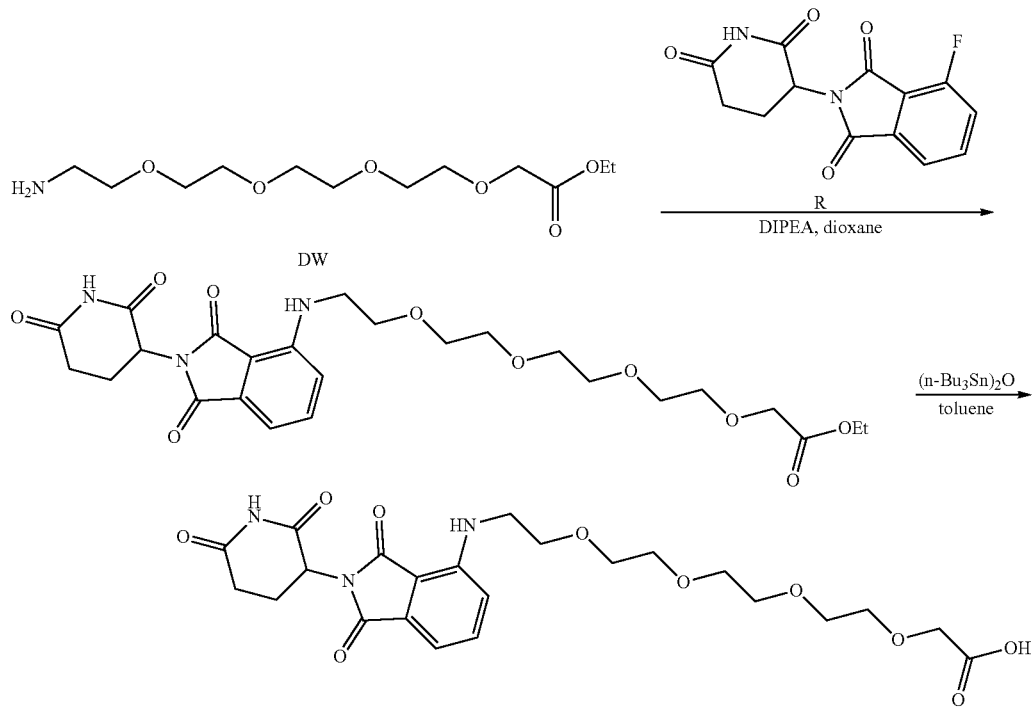

The title compound was synthesized via general scheme 7, using fluoride Intermediate R and amine Intermediate DW in the first step which was run at 115° C. for 16 hours. In Step 2, the ester was deprotected as follows: to a solution of (Bu₃Sn)₂O (779 mg, 1.31 mmol) in toluene (20 mL) was added ethyl 2-[2-[2-[2-[2-[[2-(2,6-dioxo-3-piperidyl)-1,3-dioxo-isoindolin-4-yl]amino]ethoxy]ethoxy]ethoxy]ethoxy]acetate (0.35 g, 654 umol). The reaction mixture was stirred at 115° C. for 12 hours. On completion, the reaction mixture was quenched with 1 N sodium fluoride solution. The mixture was extracted with DCM (100 mL), then dried and concentrated in vacuo. The crude was purified by reverse phase flash chromatography (0.1% FA) to give 2-[2-[2-[2-[2-[[2-(2,6-dioxo-3-piperidyl)-1,3-dioxo-isoindolin-4-yl]amino]ethoxy]ethoxy]ethoxy]ethoxy]acetic acid (0.175 g, 53% yield) as yellow oil (LCMS (M+1)⁺: 508.2).

Tert-butyl 2-(2-(2-(2-aminoethoxy)ethoxy)ethoxy)acetate (Intermediate CY)

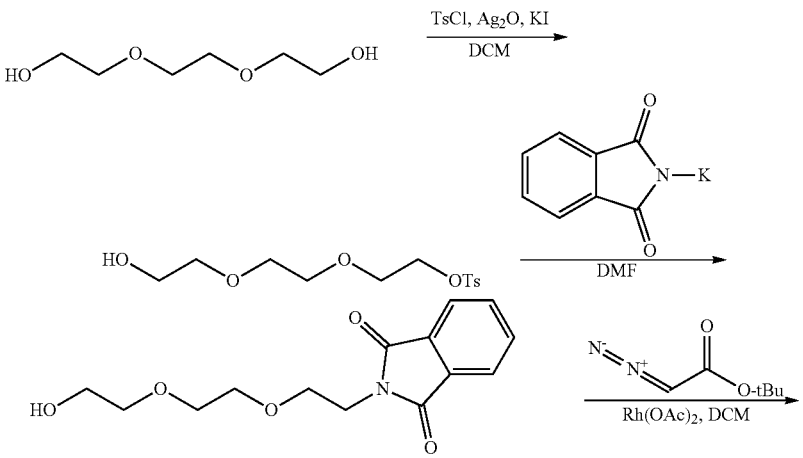

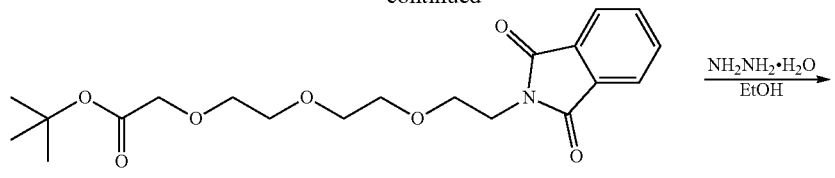

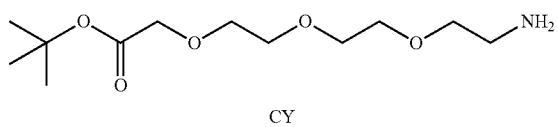

CY

Step 1—2-(2-(2-Hydroxyethoxy)ethoxy)ethyl 4-methylbenzenesulfonate

To a solution of 2-[2-(2-hydroxyethoxy)ethoxy]ethanol (50.0 g, 333 mmol, 44.6 mL) in DCM (1 L) was added Ag$_2$O (84.9 g, 366 mmol) and KI (5.53 g, 33.3 mmol) and TsCl (63.5 g, 333 mmol). The reaction mixture was stirred at rt for 18 hours. On completion, the reaction mixture was filtered and the filtrate was concentrated in vacuo. The residue was purified by silica gel chromatography to give the title compound (76.0 g, 74% yield) as a colorless oil. $^1$H NMR (400 MHz, CDCl$_3$) δ 7.81 (d, J=8.0 Hz, 2H), 7.35 (d, J=8.0 Hz, 2H), 4.20-4.15 (m, 2H), 3.74-3.69 (m, 4H), 3.64-3.56 (m, 6H), 2.45 (s, 3H); LC-MS (ESI$^+$) m/z 305.0 (M+H)$^+$.

Step 2—2-(2-(2-(2-Hydroxyethoxy)ethoxy)ethyl)isoindoline-1,3-dione

To a solution of 2-[2-(2-hydroxyethoxy)ethoxy]ethyl 4-methylbenzenesulfonate (20.0 g, 65.7 mmol) in DMF (200 mL) was added (1,3-dioxoisoindolin-2-yl)potassium (12.8 g, 69.0 mmol). The resulting reaction mixture was stirred at 80° C. for 12 hours. On completion, the reaction mixture was concentrated in vacuo. The residue was purified by silica gel chromatography to give the title compound (14.6 g, 80% yield) as a colorless oil. $^1$H NMR (400 MHz, CDCl$_3$) δ 7.89-7.83 (m, 2H), 7.75-7.69 (m, 2H), 3.95-3.90 (m, 2H), 3.79-3.74 (m, 2H), 3.69-3.64 (m, 4H), 3.63-3.59 (m, 2H), 3.56-3.52 (m, 2H).

Step 3—Tert-butyl 2-(2-(2-(2-(1,3-dioxoisoindolin-2-yl)ethoxy)ethoxy)ethoxy)acetate To a solution of 2-[2-[2-(2-hydroxyethoxy)ethoxy]ethyl]isoindoline-1,3-dione (10.0 g, 35.8 mmol) and Rh(OAc)$_2$ (396 mg, 1.79 mmol) in DCM (50 mL) was added a solution of tert-butyl 2-diazoacetate (7.63 g, 53.7 mmol) in DCM (200 mL) dropwise. The reaction mixture was stirred at rt for 18 hours. On completion, the reaction mixture was concentrated in vacuo. The residue was purified by silica gel chromatography to give the title compound (11.0 g, 78% yield) as a colorless oil. $^1$H NMR (400 MHz, CDCl$_3$) δ 7.88-7.82 (m, 2H), 7.75-7.69 (m, 2H), 3.99 (s, 2H), 3.94-3.88 (m, 2H), 3.77-3.72 (m, 2H), 3.68-3.58 (m, 8H), 1.47 (s, 9H).

Step 4—Tert-butyl 2-(2-(2-(2-aminoethoxy)ethoxy)ethoxy)acetate

To a solution of tert-butyl 2-[2-[2-[2-(1,3-dioxoisoindolin-2-yl)ethoxy]ethoxy]ethoxy]acetate (11.0 g, 28.0 mmol) in ethanol (200 mL) was added NH$_2$NH$_2$—H$_2$O (7.00 g, 140 mmol). The reaction mixture was stirred at 80° C. for 2 hours. On completion, the reaction mixture was filtered. The filtrate was concentrated in vacuo. The residue was diluted with DCM (200 mL) and filtered. The filtrate was concentrated in vacuo to give the title compound (6.40 g, 87% yield) as a colorless oil. $^1$H NMR (400 MHz, CDCl$_3$) δ 4.02 (s, 2H), 3.72-3.63 (m, 10H), 3.53-3.50 (m, 2H), 1.47 (s, 9H); LC-MS (ESI$^+$) m/z 264.0 (M+H)$^+$.

N-[3-carbamoyl-1-[1-[2-[2-[2-[2-[[2-(2,6-dioxo-3-piperidyl)-1,3-dioxo-isoindolin-4-yl] amino] ethoxy]ethoxy]ethoxy]acetyl]-4-piperidyl]pyrazol-4-yl]-2-[2-(2,2,2-trifluoroethylamino)-4-pyridyl]oxazole-4-carboxamide (Intermediate ZY)

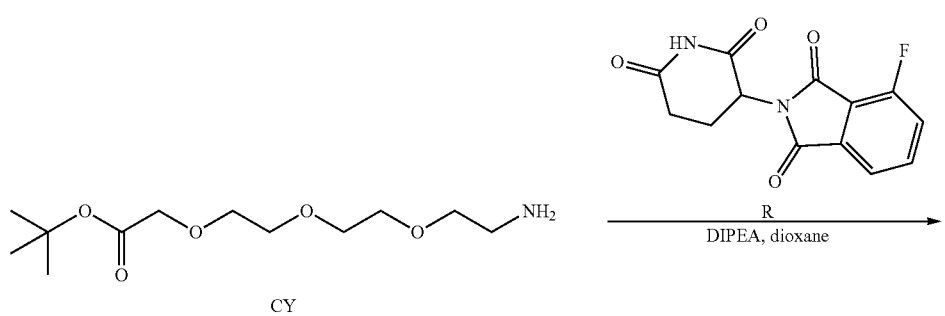

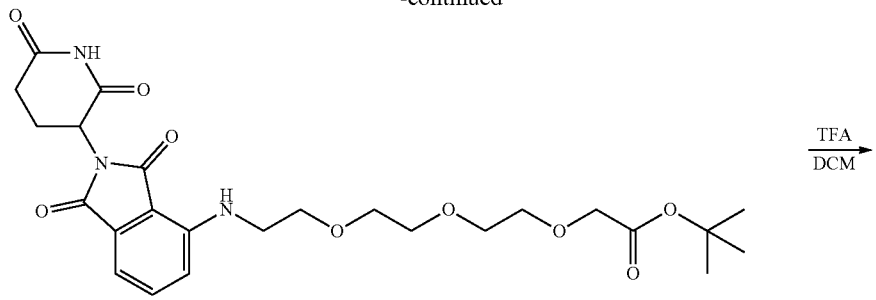

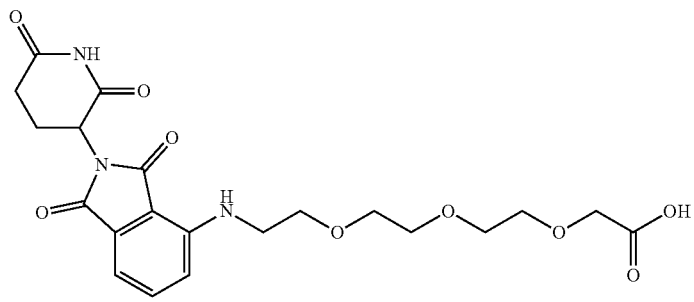

Step 1—Tert-butyl 2-(2-(2-(2-((2-(2,6-Dioxopiperidin-3-yl)-1,3-dioxoisoindolin-4-yl)amino)ethoxy)ethoxy)ethoxy)acetate To a solution of tert-butyl 2-[2-[2-(2-aminoethoxy)ethoxy]ethoxy]acetate (6.40 g, 24.3 mmol, Intermediate CY) and 2-(2,6-dioxo-3-piperidyl)-4-fluoro-isoindoline-1,3-dione (6.71 g, 24.3 mmol, Intermediate R) in dioxane (100 mL) was added DIPEA (9.42 g, 72.9 mmol). The reaction mixture was stirred at 115° C. for 24 hours. On completion, the reaction mixture was concentrated in vacuo to give yellow oil. The yellow oil was purified by prep-HPLC (water (0.1% FA)-ACN) to give the title compound (6.00 g, 48% yield) as a yellow oil. $^1$H NMR (400 MHz, CDCl$_3$) δ 8.19 (s, 1H), 7.54-7.45 (m, 1H), 7.11 (d, J=8.4 Hz, 1H), 6.93 (d, J=8.4 Hz, 1H), 6.52-6.48 (m, 1H), 4.99-4.87 (m, 1H), 4.02 (s, 2H), 3.75-3.68 (m, 10H), 3.50-3.46 (m, 2H), 2.93-2.69 (m, 3H), 2.17-2.10 (m, 1H), 1.49 (s, 9H).

Step 2—(2-(2-(2-(2-((2-(2,6-Dioxopiperidin-3-yl)-1,3-dioxoisoindolin-4-yl)amino)ethoxy)ethoxy)ethoxy)acetic acid To a solution of tert-butyl 2-[2-[2-[2-[[2-(2,6-dioxo-3-piperidyl)-1,3-dioxo-isoindolin-4-yl]amino] ethoxy]ethoxy]ethoxy]acetate (6.00 g, 11.6 mmol) in DCM (30 mL) was added TFA (30.8 g, 270 mmol). The reaction mixture was stirred at rt for 12 hours. On completion, the reaction mixture was concentrated in vacuo to give the title compound (5.60 g, 99% yield) as a yellow oil. LC-MS (ESI$^+$) m/z 464.0 (M+H)$^+$.

3-[3-Methyl-2-oxo-5-[3-[2-[2-[2-[2-oxo-2-[4-[4-[(5-tetrahydropyran-4-yl-7H-pyrrolo[2,3-d]pyrimidin-4-yl)amino]cyclohexyl]piperazin-1-yl]ethoxy]ethoxy]ethoxy]ethoxy]propyl]benzimidazol-1-yl]piperidine-26-dione (Intermediate ZX)

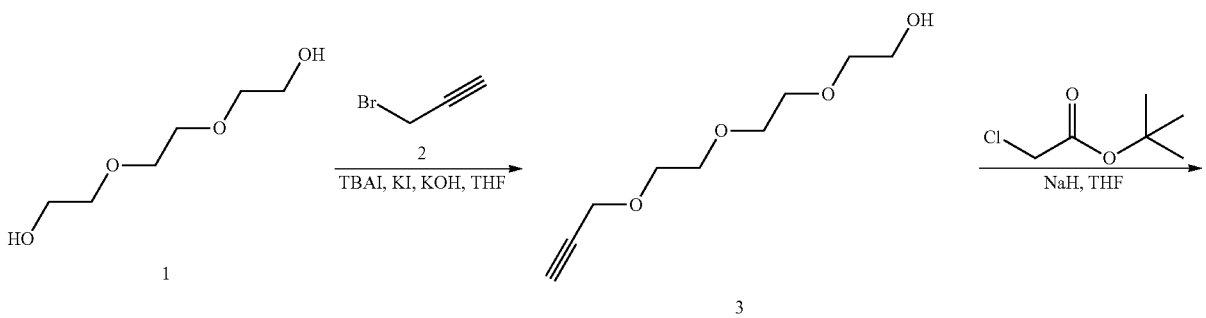

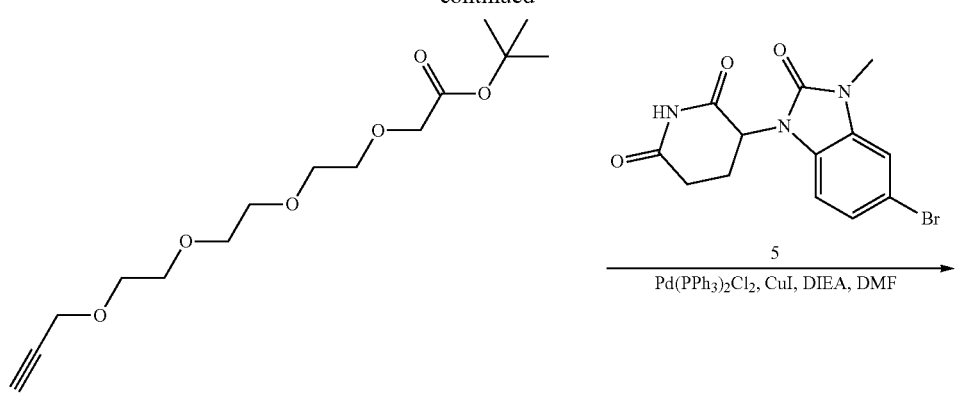
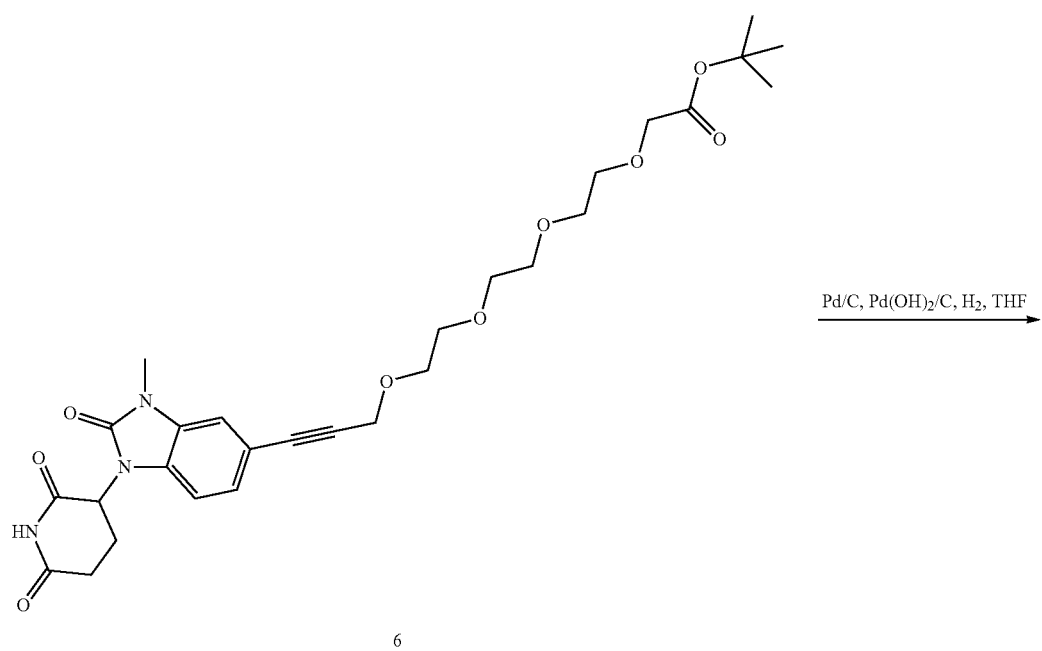
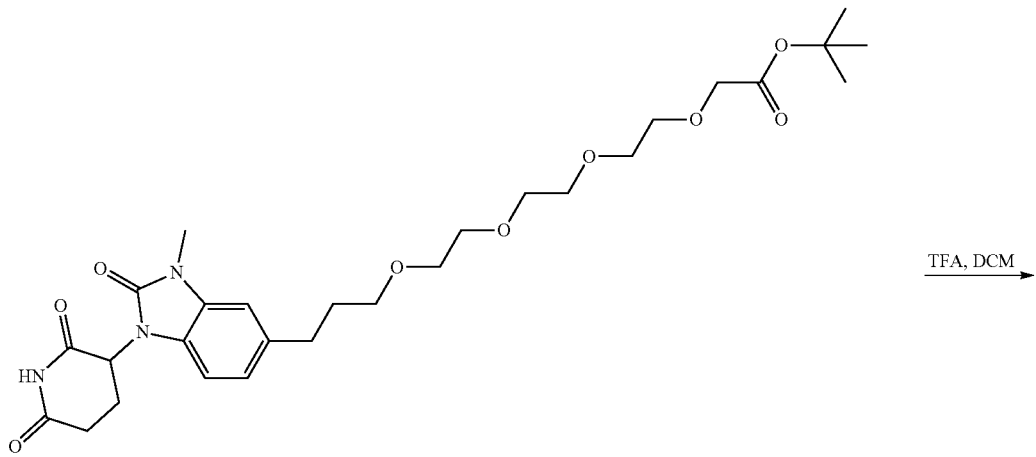

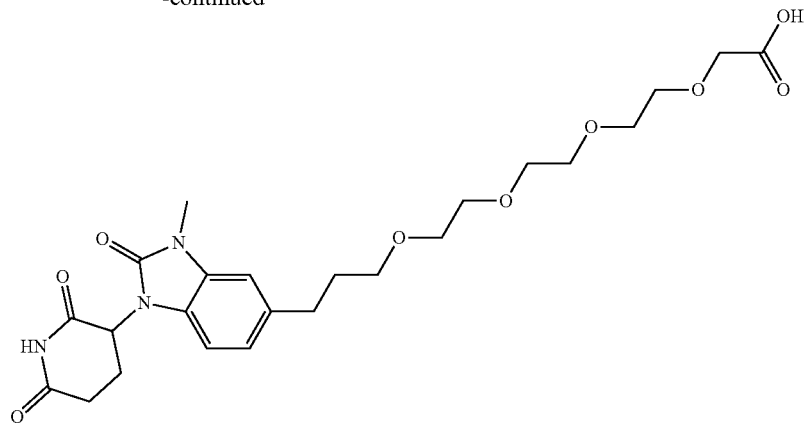

Step 1—2-[2-(2-Prop-2-ynoxyethoxy)ethoxy]ethanol (3)

To a solution of 2-[2-(2-hydroxyethoxy)ethoxy]ethanol (10.0 g, 66.5 mmol, 8.93 mL, CAS #112-27-6) and 3-bromoprop-1-yne (7.92 g, 66.5 mmol, 5.74 mL, CAS #106-96-7) in THF (100 mL) was added KI (1.66 g, 9.99 mmol), TBAI (1.48 g, 4.00 mmol) and KOH (3.74 g, 66.5 mmol). The reaction mixture was stirred at 25° C. for 16 hrs. On completion, the mixture was filtered, and the filtrate was concentrated in vacuo to give a residue, the residue was diluted with $H_2O$ (50 mL), and then extracted with EA (2×80 mL), the organic phase was concentrated in vacuo to give a residue. The residue was purified by column chromatography to give the title compound (10.0 g, 79% yield) as yellow oil. $^1H$ NMR (400 MHz, $CDCl_3$) δ 4.19-4.12 (m, 2H), 3.74-3.57 (m, 10H), 3.57-3.52 (m, 2H), 2.42 (s, 1H), 2.38 (t, J=2.4 Hz, 1H).

Step 2—Tert-butyl 2-[2-[2-(2-prop-2-ynoxyethoxy)ethoxy]ethoxy]acetate (5)

To a solution of 2-[2-(2-prop-2-ynoxyethoxy)ethoxy]ethanol (4.0 g, 21.25 mmol) in THF (50 mL) was added NaH (1.28 g, 31.8 mmol, 60% purity) at 0° C., the mixture was stirred at 25° C. for 30 min, then tert-butyl 2-chloroacetate (6.40 g, 42.5 mmol, 6.10 mL, CAS #107-59-5) was added to the mixture, the reaction mixture was stirred at 25° C. for 12 hrs. On completion, the mixture was quenched by $H_2O$ (50 mL), and extracted with EA (2×100 mL). The organic phase was concentrated in vacuo to give a residue. The residue was purified by column chromatography to give the title compound (3.60 g, 56% yield) as yellow oil. $^1H$ NMR (400 MHz, $CDCl_3$) δ 4.20 (d, J=2.4 Hz, 2H), 4.01 (s, 2H), 3.72-3.65 (m, 12H), 2.42 (t, J=2.4 Hz, 1H), 1.47 (s, 9H).

Step 3—Tert-butyl 2-[2-[2-[2-[3-[1-(2,6-dioxo-3-piperidyl)-3-methyl-2-oxo-benzimidazol-5-yl]prop-2-ynoxy]ethoxy]ethoxy]ethoxy]acetate (6)

To a solution of tert-butyl 2-[2-[2-(2-prop-2-ynoxyethoxy)ethoxy] ethoxy]acetate (1.16 g, 3.84 mmol) and 3-(5-bromo-3-methyl-2-oxo-benzimidazol-1-yl)piperidine-2,6-dione (650 mg, 1.92 mmol, Intermediate HN) in DMF (10 mL) was added CuI (73.2 mg, 384 umol), $Pd(PPh_3)_2Cl_2$ (269 mg, 384 umol) and $Cs_2CO_3$ (3.13 g, 9.61 mmol). The reaction mixture was stirred at 80° C. for 2 hrs under $N_2$. On completion, the mixture was filtered and the filtrate was concentrated in vacuo to give a residue. The residue was purified by reverse phase (0.1% FA condition) to give the title compound (550 mg, 51% yield) as a yellow solid. $^1H$ NMR (400 MHz, DMSO-$d_6$) δ 11.11 (s, 1H), 7.33 (s, 1H), 7.21-7.09 (m, 2H), 5.39 (dd, J=5.2, 12.8 Hz, 1H), 4.39 (s, 2H), 3.97 (s, 2H), 3.68-3.61 (m, 2H), 3.59-3.52 (m, 10H), 3.34 (s, 3H), 2.97-2.82 (m, 1H), 2.76-2.57 (m, 2H), 2.06-2.00 (m, 1H), 1.41 (s, 9H); LC-MS (ESI$^+$) m/z 582.3 (M+Na)$^+$.

Step 4—Tert-butyl 2-[2-[2-[2-[3-[1-(2,6-dioxo-3-piperidyl)-3-methyl-2-oxo-benzimidazol-5-yl]propoxy]ethoxy]ethoxy]ethoxy]acetate (7)

To a solution of tert-butyl 2-[2-[2-[2-[3-[1-(2,6-dioxo-3-piperidyl)-3-methyl-2-oxo-benzimidazol-5-yl]prop-2-ynoxy]ethoxy]ethoxy]ethoxy]acetate (550 mg, 982 umol) in THF (20 mL) was added $Pd(OH)_2/C$ (250 mg, 915 umol, 10% purity) and Pd/C (250 mg, 915 umol, 10% purity), the reaction mixture was stirred at 25° C. for 12 hrs under $H_2$ (15 Psi). On completion, the residue was filtered and the filtrate was concentrated in vacuo to give the title compound (500 mg, 90% yield) as a white solid. LC-MS (ESI$^+$) m/z 508.2 (M+H-56)$^+$.

Step 5—2-[2-[2-[2-[3-[1-(2,6-Dioxo-3-piperidyl)-3-methyl-2-oxo-benzimidazol-5-yl]propoxy]ethoxy]ethoxy]ethoxy]acetic acid To a solution of tert-butyl 2-[2-[2-[2-[3-[1-(2,6-dioxo-3-piperidyl)-3-methyl-2-oxo-benzimidazol-5-yl] propoxy] ethoxy]ethoxy]ethoxy]acetate (100 mg, 177 umol) in DCM (3 mL) was added TFA (1.54 g, 13.5 mmol, 1 mL), the reaction mixture was stirred at 25° C. for 12 hrs. On completion, the reaction mixture was concentrated in vacuo to give the title compound (110 mg, 95% yield) as colorless oil. LC-MS (ESI$^+$) m/z 508.3 (M+H)$^+$.

3-[3-Methyl-2-oxo-5-[7-oxo-7-[4-[4-[(5-tetrahydro-pyran-4-ylpyrrolo[2,1-f][1,2,4]triazin-4-yl)amino]cyclohexyl]piperazin-1-yl]heptyl]benzimidazol-1-yl]piperidine-2,6-dione (Intermediate ZW)

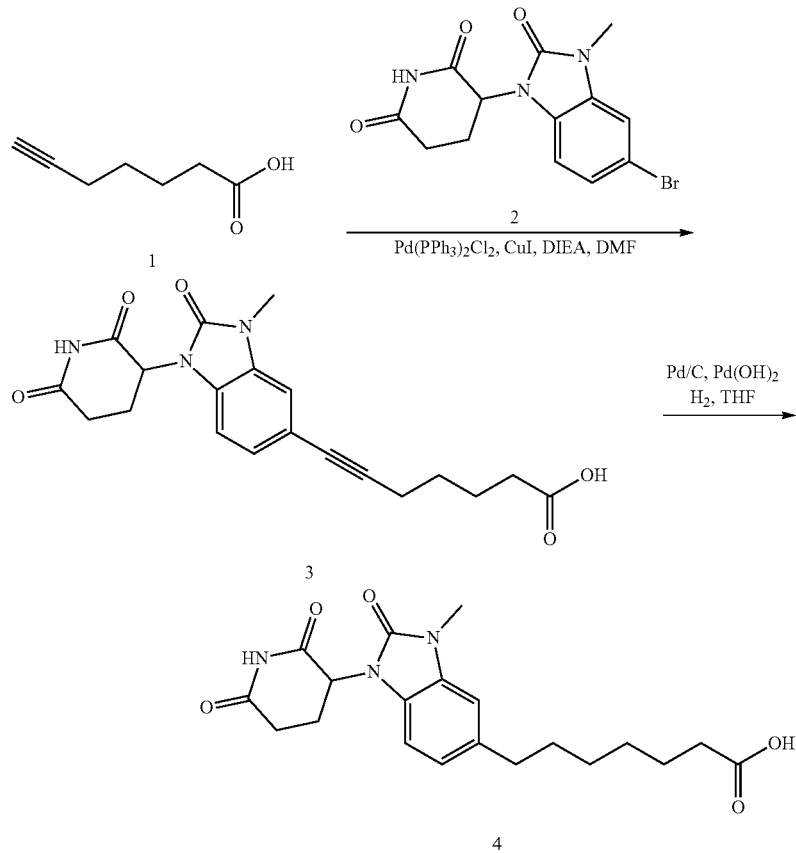

Step 1—7-[1-(2,6-Dioxo-3-piperidyl)-3-methyl-2-oxo-benzimidazol-5-yl]hept-6-ynoic acid (3)

A mixture of hept-6-ynoic acid (224 mg, 1.77 mmol, CAS #30964-00-2), 3-(5-bromo-3-methyl-2-oxo-benzimidazol-1-yl)piperidine-2,6-dione (200 mg, 591 umol, Intermediate HN), Pd(PPh$_3$)$_2$Cl$_2$ (12.5 mg, 17.7 umol), CuI (1.13 mg, 5.91 umol) and DIEA (1.53 g, 11.8 mmol) in DMSO (5 mL) was degassed and purged with N$_2$ for 3 times in glove box. The mixture was stirred at 80° C. for 2 hrs under N$_2$ atmosphere. On completion, the crude product was purified by reverse phase column (0.1% FA condition) to give the title compound (180 mg, 60% yield) as a yellow solid. $^1$H NMR (400 MHz, DMSO-d$_6$) δ=11.12 (s, 1H), 7.97-7.67 (m, 1H), 7.29-7.18 (m, 1H), 7.17-7.03 (m, 2H), 5.37 (d, J=13.2 Hz, 1H), 3.43-3.38 (m, 3H), 2.93-2.81 (m, 2H), 2.74-2.65 (m, 1H), 2.46-2.39 (m, 2H), 2.30-2.23 (m, 2H), 2.02 (d, J=4.4 Hz, 1H), 1.72-1.43 (m, 4H).

Step 2—Tert-butyl 6-[2-[2-[[2-(2,6-dioxo-3-piperidyl)-1,3-dioxo-isoindolin-4-yl]amino]ethoxy]ethyl-2,6-diazaspiro[3.3]heptane-2-carboxylate (4)

To a solution of 7-[1-(2,6-dioxo-3-piperidyl)-3-methyl-2-oxo-benzimidazol-5-yl]hept-6-ynoic acid (160 mg, 417 umol) in THF (50 mL) was added Pd/C (200 mg, 417 umol, 50% purity) and Pd(OH)$_2$/C (200 mg, 417 umol, 10% purity) under N$_2$. The suspension was degassed under vacuum and purged with H$_2$ several times. The mixture was stirred at 15° C. for 2 hours under H$_2$ (15 psi). On completion, the mixture was filtered with Clite and the filtrate was concentrated in vacuo to give the title compound (100 mg, 40% yield) as a yellow solid. LC-MS (ESI$^+$) m/z 388.2 (M+H)$^+$.

3-[3-Methyl-2-oxo-5-[3-[3-oxo-3-[4-[4-[(5-tetrahydropyran-4-ylpyrrolo[2,1-f][1,2,4]triazin-4-yl)amino]cyclohexyl]piperazin-1-yl]propoxy]propyl]benzimidazol-1-yl]piperidine-2,6-dione (Intermediate ZV)

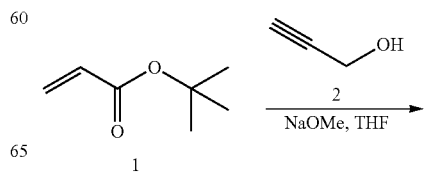

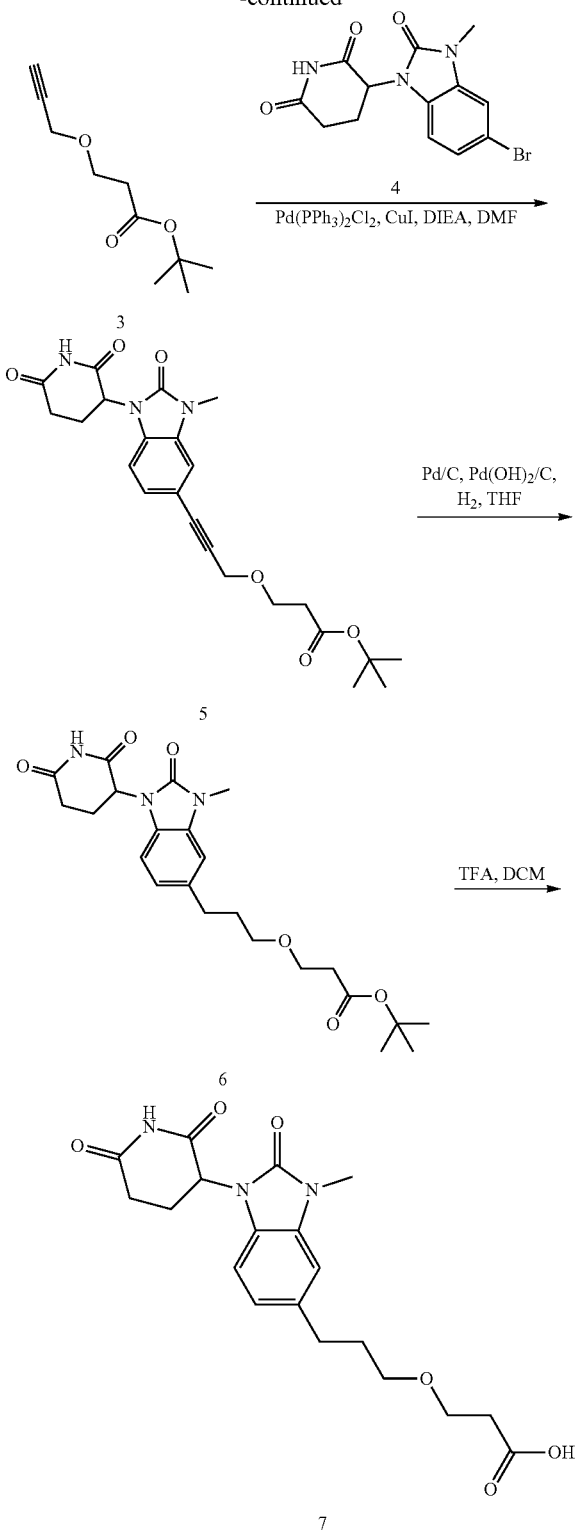

Step 1—Tert-butyl 3-prop-2-ynoxypropanoate (3)

A mixture of tert-butyl prop-2-enoate (2 g, 15.6 mmol, 2.27 mL, CAS #1663-39-4), prop-2-yn-1-ol (2.62 g, 46.8 mmol, 2.77 mL, CAS #107-19-7) in THF (10 mL) was added NaOMe (84.3 mg, 1.56 mmol), and then the mixture was stirred at 25° C. for 16 hrs under $N_2$ atmosphere. On completion, the mixture was diluted with water (30 mL), and then extracted with EA (2×100 mL). The organic layer was dried with $Na_2SO_4$, filtrated and concentrated in vacuo to give the title compound (1.80 g, 63% yield) as light yellow oil. $^1$H NMR (400 MHz, CDCl$_3$) δ 4.18 (d, J=2.4 Hz, 2H), 3.78 (t, J=6.4 Hz, 2H), 2.54 (t, J=6.4 Hz, 2H), 2.45 (s, 1H), 1.47 (s, 9H).

Step 2—Tert-butyl 3-[3-[1-(2,6-dioxo-3-piperidyl)-3-methyl-2-oxo-benzimidazol-5-yl]prop-2-ynoxy]propanoate (5)

A mixture of 3-(5-bromo-3-methyl-2-oxo-benzimidazol-1-yl)piperidine-2,6-dione (400 mg, 1.18 mmol, Intermediate HN), tert-butyl 3-prop-2-ynoxypropanoate (654 mg, 3.55 mmol), Pd(PPh$_3$)$_2$Cl$_2$ (166 mg, 236 umol), CuI (45.0 mg, 236 umol) and TEA (2.15 g, 21.0 mmol, 2.96 mL) in DMF (15 mL) was degassed and purged with $N_2$ for 3 times, and then the mixture was stirred at 85° C. for 4 hrs under $N_2$ atmosphere. On completion, the mixture was diluted with water (50 mL), and then extracted with EA (2×100 mL). The organic layer was washed with brine (20 mL), dried with $Na_2SO_4$, filtrated and concentrated in vacuo. The residue was purified by reverse phase flash to give the title compound (300 mg, 49% yield) as light yellow solid. LC-MS (ESI$^+$) m/z 386.1 (M+1-56)$^-$.

Step 3—Tert-butyl 3-[3-[1-(2,6-dioxo-3-piperidyl)-3-methyl-2-oxo-benzimidazol-5-yl]propoxy] propanoate (6)

To a solution of tert-butyl 3-[3-[1-(2,6-dioxo-3-piperidyl)-3-methyl-2-oxo-benzimidazol-5-yl]prop-2-ynoxy] propanoate (250 mg, 566 umol) in THF (50 mL) was added Pd/C (50 mg, 10% purity) and Pd(OH)$_2$/C (50 mg, 10% purity). The mixture was stirred at 25° C. for 5 hrs under $H_2$ atmosphere (15 psi). On completion, the mixture was filtered and the filtrate was concentrated in vacuo to give the title compound (200 mg, 79% yield) as white solid. $^1$H NMR (400 MHz, DMSO-d$_6$) δ 11.09 (s, 1H), 7.07-6.98 (m, 2H), 6.90-6.83 (m, 1H), 5.34 (dd, J=5.2, 12.8 Hz, 1H), 3.63-3.53 (m, 2H), 3.39-3.37 (m, 2H), 3.33 (s, 3H), 3.02-2.83 (m, 1H), 2.78-2.58 (m, 4H), 2.43 (t, J=6.0 Hz, 2H), 2.07-1.94 (m, 1H), 1.85-1.74 (m, 2H), 1.41 (s, 9H).

Step 4—3-[3-[1-(2,6-Dioxo-3-piperidyl)-3-methyl-2-oxo-benzimidazol-5-yl]propoxy]propanoic acid (7)

To a solution of tert-butyl 3-[3-[1-(2,6-dioxo-3-piperidyl)-3-methyl-2-oxo-benzimidazol-5-yl]propoxy] propanoate (150 mg, 336 umol) in DCM (4 mL) was added TFA (4.62 g, 40.0 mmol, 3.00 mL). The mixture was stirred at 25° C. for 2 hrs. On completion, the mixture was concentrated in vacuo to give the title compound (120 mg, 91% yield) as brown solid. $^1$H NMR (400 MHz, DMSO-d$_6$) δ 11.08 (s, 1H), 7.11-6.95 (m, 2H), 6.87 (dd, J=1.2, 8.0 Hz, 1H), 5.34 (dd, J=5.2, 12.8 Hz, 1H), 3.58 (t, J=6.4 Hz, 2H), 3.38 (t, J=6.4 Hz, 2H), 3.33 (s, 3H), 2.99-2.84 (m, 1H), 2.76-2.57 (m, 4H), 2.46 (t, J=6.4 Hz, 2H), 2.03-1.98 (m, 1H), 1.86-1.74 (m, 2H).

3-[3-Methyl-2-oxo-5-[3-[2-[2-[2-[2-oxo-2-[4-[4-[(5-tetrahydropyran-4-yl-7H-pyrrolo[23-d]pyrimidin-4-yl)amino]cyclohexyl]piperazin-1-yl]ethoxy]ethoxy]ethoxy]ethoxy]propyl]benzimidazol-1-yl]piperidine-2,6-dione (Intermediate HO)
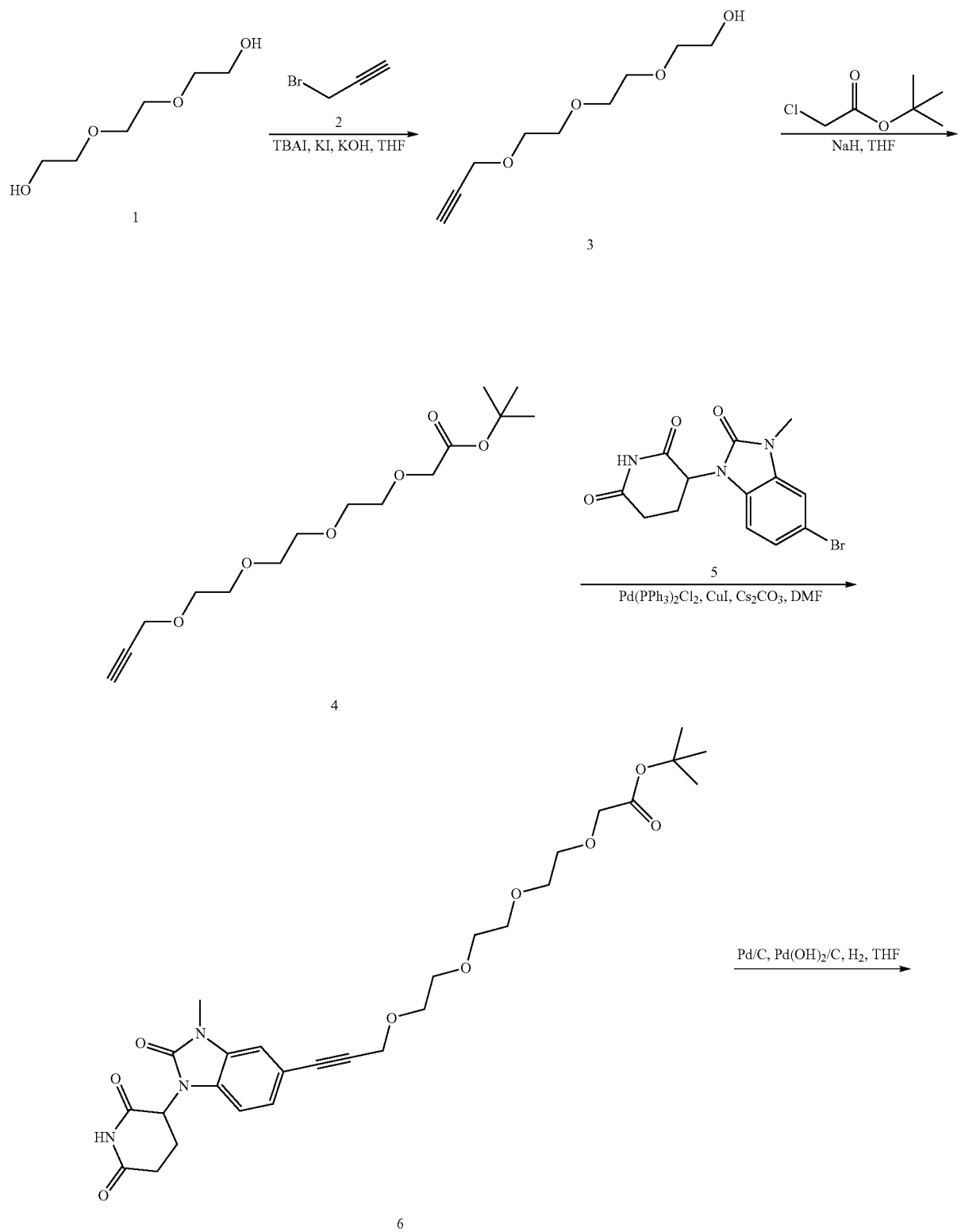

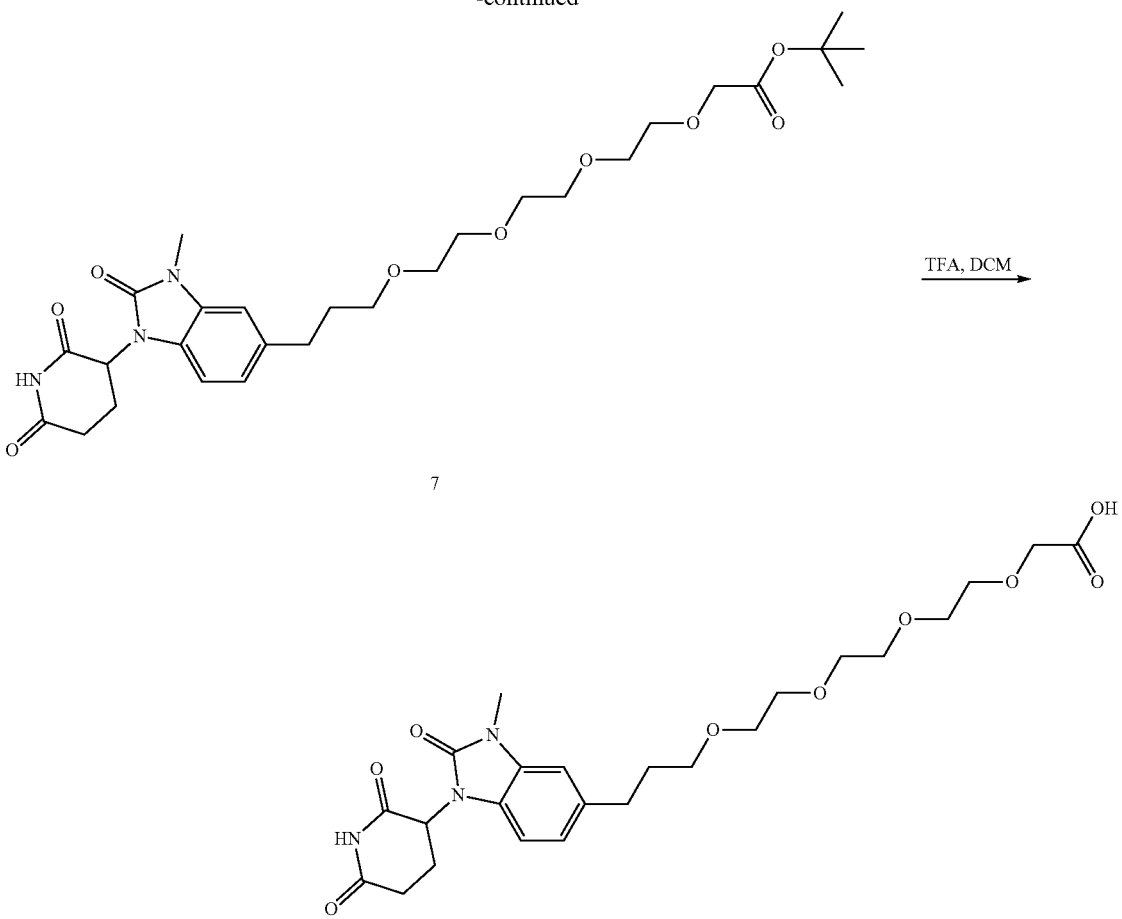

Step 1—2-[2-(2-Prop-2-ynoxyethoxy)ethoxy]ethanol (3)

To a solution of 2-[2-(2-hydroxyethoxy)ethoxy]ethanol (10.0 g, 66.5 mmol, 8.93 mL, CAS #112-27-6) and 3-bromoprop-1-yne (7.92 g, 66.5 mmol, 5.74 mL, CAS #106-96-7) in THF (100 mL) was added KI (1.66 g, 9.99 mmol), TBAI (1.48 g, 4.00 mmol) and KOH (3.74 g, 66.5 mmol). The reaction mixture was stirred at 25° C. for 16 hrs. On completion, the mixture was filtered, and the filtrate was concentrated in vacuo to give a residue, the residue was diluted with H$_2$O (50 mL), and then extracted with EA (2×80 mL), the organic phase was concentrated in vacuo to give a residue. The residue was purified by column chromatography to give the title compound (10.0 g, 79% yield) as yellow oil. $^1$H NMR (400 MHz, CDCl$_3$) δ 4.19-4.12 (m, 2H), 3.74-3.57 (m, 10H), 3.57-3.52 (m, 2H), 2.42 (s, 1H), 2.38 (t, J=2.4 Hz, 1H).

Step 2—Tert-butyl 2-[2-[2-(2-prop-2-ynoxyethoxy)ethoxy]ethoxy]acetate (5)

To a solution of 2-[2-(2-prop-2-ynoxyethoxy)ethoxy]ethanol (4.0 g, 21.25 mmol) in THF (50 mL) was added NaH (1.28 g, 31.8 mmol, 60% purity) at 0° C., the mixture was stirred at 25° C. for 30 min, then tert-butyl 2-chloroacetate (6.40 g, 42.5 mmol, 6.10 mL, CAS #107-59-5) was added to the mixture, the reaction mixture was stirred at 25° C. for 12 hrs. On completion, the mixture was quenched by H$_2$O (50 mL), and extracted with EA (2×100 mL). The organic phase was concentrated in vacuo to give a residue. The residue was purified by column chromatography to give the title compound (3.60 g, 56% yield) as yellow oil. $^1$H NMR (400 MHz, CDCl$_3$) δ 4.20 (d, J=2.4 Hz, 2H), 4.01 (s, 2H), 3.72-3.65 (m, 12H), 2.42 (t, J=2.4 Hz, 1H), 1.47 (s, 9H).

Step 3—Tert-butyl 2-[2-[2-[2-[3-[1-(2,6-dioxo-3-piperidyl)-3-methyl-2-oxo-benzimidazol-5-yl]prop-2-ynoxy]ethoxy]ethoxy]ethoxy]acetate (6)

To a solution of tert-butyl 2-[2-[2-(2-prop-2-ynoxyethoxy)ethoxy] ethoxy]acetate (1.16 g, 3.84 mmol) and 3-(5-bromo-3-methyl-2-oxo-benzimidazol-1-yl)piperidine-2,6-dione (650 mg, 1.92 mmol, Intermediate HN) in DMF (10 mL) was added CuI (73.2 mg, 384 umol), Pd(PPh$_3$)$_2$Cl$_2$ (269 mg, 384 umol) and Cs$_2$CO$_3$ (3.13 g, 9.61 mmol). The reaction mixture was stirred at 80° C. for 2 hrs under N$_2$. On completion, the mixture was filtered and the filtrate was concentrated in vacuo to give a residue. The residue was purified by reverse phase (0.1% FA condition) to give the title compound (550 mg, 51% yield) as a yellow solid. $^1$H NMR (400 MHz, DMSO-d$_6$) δ 11.11 (s, 1H), 7.33 (s, 1H), 7.21-7.09 (m, 2H), 5.39 (dd, J=5.2, 12.8 Hz, 1H), 4.39 (s, 2H), 3.97 (s, 2H), 3.68-3.61 (m, 2H), 3.59-3.52 (m, 10H), 3.34 (s, 3H), 2.97-2.82 (m, 1H), 2.76-2.57 (m, 2H), 2.06-2.00 (m, 1H), 1.41 (s, 9H); LC-MS (ESI$^+$) m/z 582.3 (M+Na)$^+$.

1469

Step 4—Tert-butyl 2-[2-[2-[2-[3-[1-(2,6-dioxo-3-piperidyl)-3-methyl-2-oxo-benzimidazol-5-yl]propoxy]ethoxy]ethoxy]ethoxy]acetate (7)

To a solution of tert-butyl 2-[2-[2-[2-[3-[1-(2,6-dioxo-3-piperidyl)-3-methyl-2-oxo-benzimidazol-5-yl]prop-2-ynoxy]ethoxy]ethoxy]ethoxy]acetate (550 mg, 982 umol) in THF (20 mL) was added Pd(OH)$_2$/C (250 mg, 915 umol, 10% purity) and Pd/C (250 mg, 915 umol, 10% purity), the reaction mixture was stirred at 25° C. for 12 hrs under H$_2$ (15 Psi). On completion, the residue was filtered and the filtrate was concentrated in vacuo to give the title compound (500 mg, 90% yield) as a white solid. LC-MS (ESI$^+$) m/z 508.2 (M+H-56)$^+$.

Step 5—2-[2-[2-[2-[3-[1-(2,6-Dioxo-3-piperidyl)-3-methyl-2-oxo-benzimidazol-5-yl]propoxy]ethoxy]ethoxy]ethoxy]acetic acid To a solution of tert-butyl 2-[2-[2-[2-[3-[1-(2,6-dioxo-3-piperidyl)-3-methyl-2-oxo-benzimidazol-5-yl] propoxy]ethoxy]ethoxy]ethoxy]acetate (100 mg, 177 umol) in DCM (3 mL) was added TFA (1.54 g, 13.5 mmol, 1 mL), the reaction mixture was stirred at 25° C. for 12 hrs. On completion, the mixture was concentrated in vacuo to give the title compound (110 mg, 95% yield) as colorless oil. LC-MS (ESI$^+$) m/z 508.3 (M+H)$^+$.

2-(2-Methyl-4-pyridyl)oxazole-4-carboxylic acid (Intermediate MO)

1470

Step 1—Ethyl 2-(2-methylpyridin-4-yl)oxazole-4-carboxylate

To a solution of 4-bromo-2-methyl-pyridine (1.50 g, 8.72 mmol, from CAS #22282-99-1) and ethyl oxazole-4-carboxylate (1.23 g, 8.72 mmol, from CAS #170487-38-4) in DMF (40 mL) was added tris-o-tolylphosphane (531 mg, 1.74 mmol), Pd(OAc)$_2$ (196 mg, 872 umol) and Cs$_2$CO$_3$ (5.68 g, 17.4 mmol). The reaction mixture was stirred at 70° C. for 12 hours under nitrogen. On completion, the reaction mixture was filtered and concentrated. The residue was purified by silica gel column chromatography to give the title compound (1.10 g, 44% yield) as a yellow solid. $^1$H NMR (400 MHz, CDCl$_3$) δ 8.65 (d, J=5.2 Hz, 1H), 8.31-8.36 (m, 1H), 7.86 (s, 1H), 7.75 (d, J=5.2 Hz, 1H), 4.44 (q, J=7.2 Hz, 2H), 2.64 (s, 3H), 1.41 (t, J=7.2 Hz, 3H); LC-MS (ESI$^+$) m/z 233.1 (M+H)$^+$.

Step 2—2-(2-Methyl-4-pyridyl)oxazole-4-carboxylic acid

To a solution of ethyl 2-(2-methyl-4-pyridyl)oxazole-4-carboxylate (1.10 g, 4.74 mmol) in THF (20 mL) was added LiOH.H$_2$O (795 mg, 19.0 mmol) in H$_2$O (4 mL). The reaction mixture was stirred at rt for 12 hours. On completion, the reaction mixture was filtered and the filter cake was dissolved in water (20 mL). The solution was acidified to pH=4 and filtered. The filter cake was washed with water (2×5 mL) and dried in vacuo. The residue was purified by prep-HPLC to give the title compound (600 mg, 52% yield) as a white solid.

N-[3-(difluoromethyl)-1-(4-formylcyclohexyl)pyrazol-4-yl]-2-(2-methyl-4-pyridyl)oxazole-4-carboxamide (Intermediate WS)

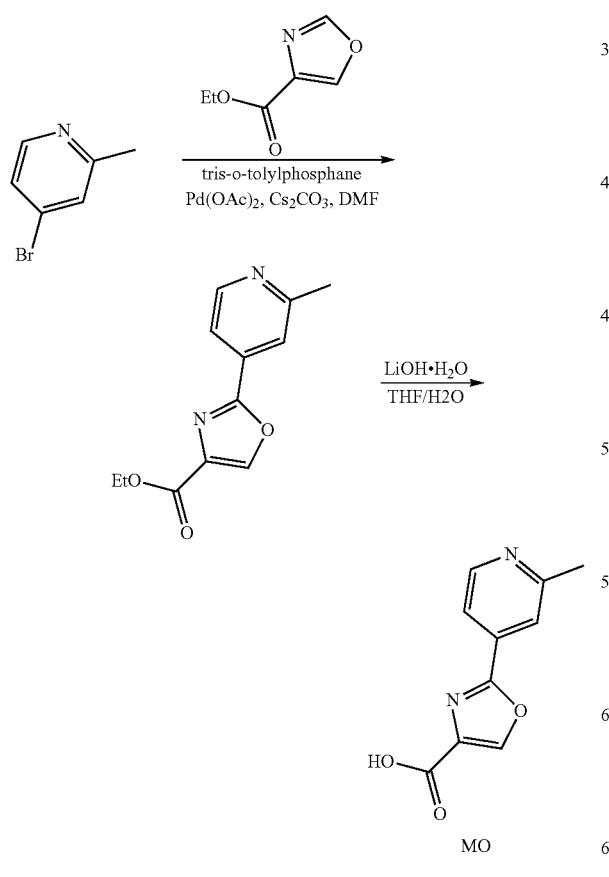

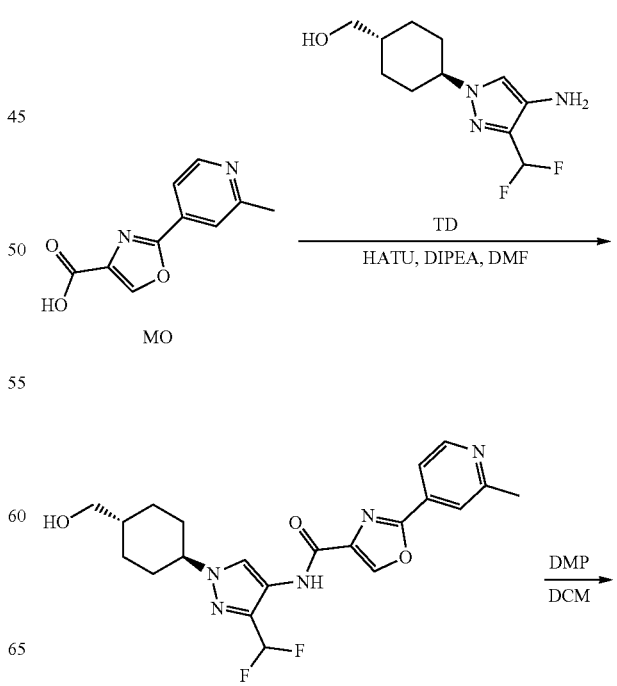

1471

-continued

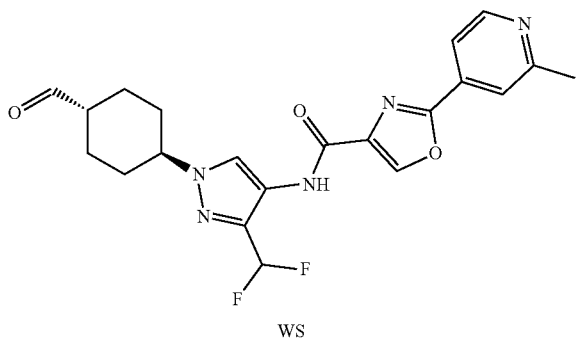

WS

Step 1—N-[3-(difluoromethyl)-1-[4-(hydroxymethyl)cyclohexyl]pyrazol-4-yl]-2-(2-methyl-4-pyridyl) oxazole-4-carboxamide To a mixture of 2-(2-methyl-4-pyridyl)oxazole-4-carboxylic acid (127 mg, 623 umol, Intermediate MO) and [4-[4-amino-3-(difluoromethyl)pyrazol-1-yl]cyclohexyl]methanol (170 mg, 693 umol, Intermediate TD) in DMF (1 mL) was added DIPEA (268 mg, 2.08 mmol, 362 uL) and HATU (316 mg, 831 umol). The reaction mixture was stirred at 25° C. for 1 hour. On completion, the reaction mixture was quenched with 2 mL water and concentrated in vacuo. The residue was purified by reverse phase (0.1% FA condition) to give the title compound (200 mg, 66% yield) as a yellow solid. $^1$H NMR (400 MHz, DMSO-$d_6$) δ 9.82 (s, 1H), 9.00 (s, 1H), 8.68 (d, J=5.1 Hz, 1H), 8.17 (s, 1H), 7.84 (s, 1H), 7.76 (d, J=4.8 Hz, 1H), 7.15 (t, J=54.4 Hz, 1H) 4.50 (t, J=5.3 Hz, 1H), 4.19 (tt, J=3.7, 11.9 Hz, 1H), 2.59 (s, 3H), 2.10-1.99 (m, 2H), 1.86 (d, J=11.9 Hz, 2H), 1.74-1.70 (m, 2H), 1.52-1.31 (m, 1H), 1.17-0.95 (m, 2H).

Step 2—N-[3-(difluoromethyl)-1-(4-formylcyclohexyl)pyrazol-4-yl]-2-(2-methyl-4-pyridyl)oxazole-4-carboxamide To a mixture of N-[3-(difluoromethyl)-1-[4-(hydroxymethyl)cyclohexyl]pyrazol-4-yl]-2-(2-methyl-4-pyridyl)oxazole-4-carboxamide (170 mg, 394 umol) in DCM (1 mL) was added DMP (200 mg, 472 umol, 146 uL) at 0° C. The reaction mixture was stirred at 25° C. for 2 hours. On completion, the reaction mixture was quenched with sat. $Na_2S_2O_3$ (2 mL) and $NaHCO_3$ (2 mL) under stirring. The residue was diluted with water (100 mL) and extracted with DCM (2×100 mL). The combined organic layers was dried over $Na_2SO_4$, filtered and concentrated in vacuo to give the title compound (110 mg, 65% yield) as a yellow solid. $^1$H NMR (400 MHz, DMSO-$d_6$) δ 9.91-9.72 (m, 1H), 9.70-9.56 (m, 1H), 9.00 (s, 1H), 8.73-8.55 (m, 1H), 8.23-8.10 (m, 1H), 7.90-7.81 (m, 1H), 7.76 (d, J=5.2 Hz, 1H), 7.49-6.85 (m, 1H), 4.35-4.12 (m, 1H), 2.59 (s, 3H), 2.44-2.38 (m, 1H), 2.16-2.02 (m, 4H), 1.83-1.80 (m, 2H), 1.44-1.33 (m, 2H).

1472

N-r 1-(4-formylcyclohexyl)-3-(1-hydroxy-1-methyl-ethyl)pyrazol-4-yl]-6-(trifluoromethyl) pyridine-2-carboxamide (Intermediate WT)

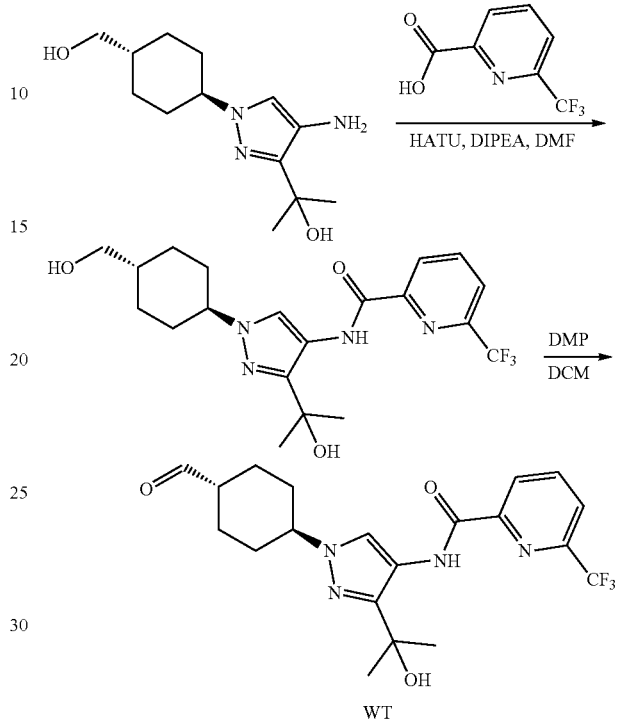

WT

Step 1—N-[1-[4-(hydroxymethyl)cyclohexyl]-3-(1-hydroxy-1-methyl-ethyl)pyrazol-4-yl]-6-(trifluoromethyl)pyridine-2-carboxamide To a mixture of 2-[4-amino-1-[4-(hydroxymethyl)cyclohexyl]pyrazol-3-yl]propan-2-ol (120 mg, 473 umol, synthesized via Step 1 of Intermediate UW) in DMF (10 mL) was added DIPEA (183 mg, 1.42 mmol, 247 uL), 6-(trifluoromethyl)pyridine-2-carboxylic acid (81.4 mg, 426 umol, CAS #131747-42-7) and HATU (216 mg, 568 umol). The reaction mixture was stirred at 25° C. for 0.5 hour. On completion, the reaction mixture was concentrated in vacuo. The residue was purified by reverse phase (0.1% FA condition) to give the title compound (160 mg, 79% yield) as yellow solid. $^1$H NMR (400 MHz, DMSO-$d_6$) δ 11.08 (s, 1H), 8.40-8.33 (m, 2H), 8.26 (s, 1H), 8.15 (dd, J=1.2, 7.2 Hz, 1H), 5.74 (s, 1H), 4.47 (t, J=5.2 Hz, 1H), 4.11-3.97 (m, 1H), 3.25 (t, J=5.6 Hz, 2H), 2.08-2.00 (m, 3H), 1.85 (d, J=12.4 Hz, 3H), 1.75-1.60 (m, 3H), 1.49 (s, 6H), 1.14-1.02 (m, 3H).

Step 2—N-[1-(4-formylcyclohexyl)-3-(1-hydroxy-1-methyl-ethyl)pyrazol-4-yl]-6-(trifluoromethyl) pyridine-2-carboxamide To a mixture of N-[1-[4-(hydroxymethyl)cyclohexyl]-3-(1-hydroxy-1-methyl-ethyl)pyrazol-4-yl]-6-(trifluoromethyl)pyridine-2-carboxamide (90.0 mg, 211 umol) in DCM (5 mL) was added DMP (107 mg, 253 umol, 78.0 uL) at 0° C. The reaction mixture was stirred at 25° C. for 0.5 hour. On completion, the mixture was diluted with water (100 mL) and extracted with DCM (2×100 mL). The combined organic layers was dried over Na₂SO₄, filtered and concentrated in vacuo to give the title compound (88.0 mg, 98% yield) as a yellow solid. $^1$H NMR (400 MHz, DMSO-d₆) δ 11.08 (s, 1H), 9.66-9.57 (m, 1H), 8.43-8.32 (m, 2H), 8.28 (s, 1H), 8.18-8.11 (m, 1H), 5.93-5.57 (m, 2H), 4.22-3.96 (m, 1H), 2.43-2.29 (m, 2H), 2.20-1.95 (m, 5H), 1.91-1.67 (m, 3H), 1.55-1.43 (m, 6H).

Tert-butyl (3R)-3-prop-2-ynoxypyrrolidine-1-carboxylate (Intermediate WU)

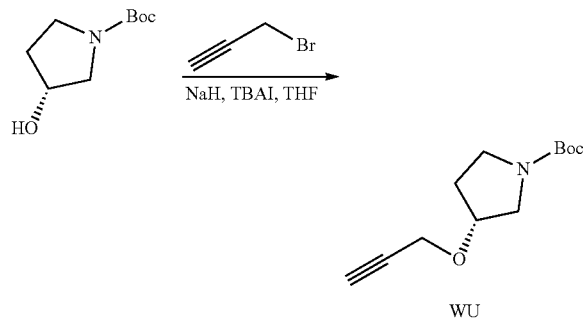

To a mixture of tert-butyl (3R)-3-hydroxypyrrolidine-1-carboxylate (5.00 g, 26.7 mmol, CAS #109431-87-0) and TBAI (493 mg, 1.34 mmol) in THF (50 mL) was added sodium hydride (1.28 g, 32.0 mmol, 60% oil dispersion) in portions at 0° C. After 0.5 hour, 3-bromoprop-1-yne (6.35 g, 53.4 mmol) was added to the mixture. The reaction mixture was stirred at 0-25° C. for 12.5 hours. On completion, the reaction was quenched with water (1.0 mL). The mixture was filtrated and the filtrate was concentrated in vacuo. The residue was purified by silica gel chromatography on silica gel to give the title compound (6.00 g, 99% yield) as yellow oil. $^1$H NMR (400 MHz, CDCl₃) δ 4.28 (s, 1H), 4.24-4.06 (m, 2H), 3.55-3.32 (m, 4H), 2.44 (t, J=2.4 Hz, 1H), 2.13-1.88 (m, 2H), 1.46 (s, 9H).

3-[3-Methyl-2-oxo-4-[3-[(3R)-pyrrolidin-3-yl]oxypropyl]benzimidazol-1-yl]piperidine-2,6-dione (Intermediate WV)

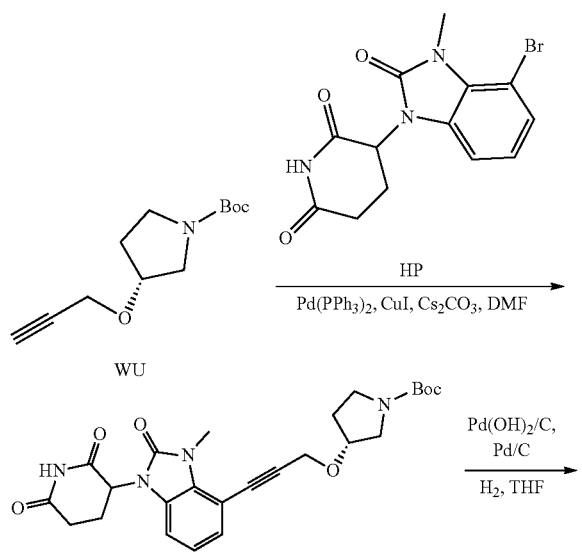

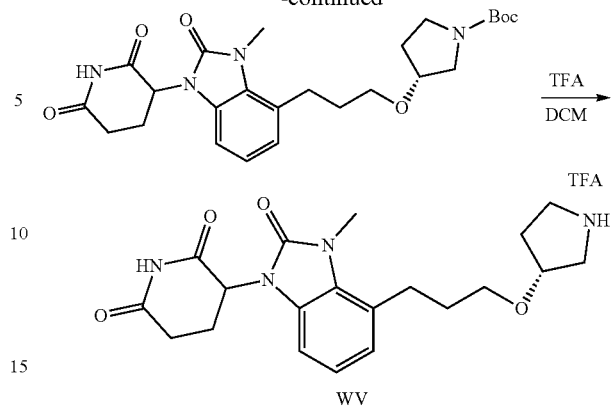

Step 1—Tert-butyl (3R)-3-[3-[1-(2,6-dioxo-3-piperidyl)-3-methyl-2-oxo-benzimidazol-4-yl]prop-2-ynoxy]pyrrolidine-1-carboxylate A mixture of tert-butyl (3R)-3-prop-2-ynoxypyrrolidine-1-carboxylate (666 mg, 2.96 mmol, Intermediate WU), 3-(4-bromo-3-methyl-2-oxo-benzimidazol-1-yl)piperidine-2,6-dione (400 mg, 1.18 mmol, Intermediate HP), Pd(PPh₃)₂Cl₂ (166 mg, 236 umol), CuI (45.0 mg, 236 umol), 4 Å MS (100 mg, 1.18 mmol) and Cs₂CO₃ (1.93 g, 5.91 mmol) in DMF (8 mL) was stirred at 80° C. for 2 hours under N₂. On completion, the reaction mixture was filtered and the filtrate was concentrated in vacuo. The residue was purified by reverse phase (FA condition) to give the title compound (330 mg, 57% yield) as brown solid. $^1$H NMR (400 MHz, DMSO-d₆) δ 11.13 (s, 1H), 7.18 (d, J=7.6 Hz, 1H), 7.13 (d, J=7.6 Hz, 1H), 7.06-7.00 (m, 1H), 5.42-5.38 (m, 1H), 4.48 (s, 2H), 4.34-4.24 (m, 1H), 3.63 (s, 3H), 3.37-3.35 (m, 1H), 3.27-3.17 (m, 2H), 2.95-2.82 (m, 1H), 2.77-2.63 (m, 2H), 2.07-1.89 (m, 4H), 1.38 (d, J=9.6 Hz, 9H).

Step 2—Tert-butyl (3R)-3-[3-[1-(2,6-dioxo-3-piperidyl)-3-methyl-2-oxo-benzimidazol-4-yl] propoxy] pyrrolidine-1-carboxylate To a solution of tert-butyl (3R)-3-[3-[1-(2,6-dioxo-3-piperidyl)-3-methyl-2-oxo-benzimidazol-4-yl] prop-2-ynoxy] pyrrolidine-1-carboxylate (300 mg, 621 umol) in THF (10 mL) was added Pd/C (150 mg, 10 wt %) and Pd(OH)₂/C (150 mg, 20 wt %) at 20° C. The reaction mixture was stirred at 20° C. for 12 hours under H₂ (15 psi). On completion, the reaction mixture was filtered and the filtrate was concentrated in vacuo to give the title compound (300 mg, 99% yield) as brown solid. $^1$H NMR (400 MHz, DMSO-d₆) δ 11.09 (s, 1H), 6.99-6.92 (m, 2H), 6.90-6.82 (m, 1H), 5.42-5.38 (m, 1H), 4.06-3.96 (m, 1H), 3.55 (s, 3H), 3.50-3.39 (m, 2H), 3.32-3.30 (m, 1H), 3.30-3.26 (m, 2H), 3.26-3.20 (m, 1H), 2.98-2.91 (m, 2H), 2.90-2.82 (m, 1H), 2.75-2.57 (m, 2H), 2.03-1.95 (m, 1H), 1.94-1.86 (m, 2H), 1.85-1.74 (m, 2H), 1.40 (s, 9H).

Step 3—3-[3-Methyl-2-oxo-4-[3-[(3R)-pyrrolidin-3-yl]oxypropyl]benzimidazol-1-yl]piperidine-2,6-dione To a solution of tert-butyl (3R)-3-[3-[1-(2,6-dioxo-3-piperidyl)-3-methyl-2-oxo-benzimidazol-4-yl] propoxy] pyrrolidine-1-carboxylate (300 mg, 616 umol) in dichloromethane (3 mL) was added TFA (3 mL) at 15° C. The reaction mixture was stirred at 15° C. for 0.5 hour. On completion, the reaction mixture was concentrated in vacuo to give the title compound (330 mg, 100% yield, TFA salt) as yellow semisolid. LC-MS (ESI$^+$) m/z 387.2 (M+H)$^+$.

1-(2,6-dioxo-3-piperidyl)-3-methyl-2-oxo-benzimidazole-4-carbaldehyde (Intermediate WW)

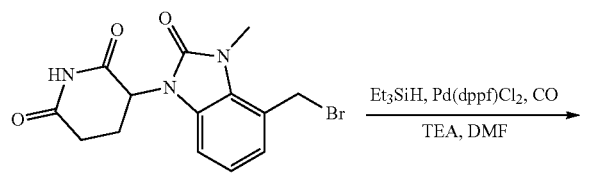

To a solution of 3-(4-(bromo-3-methyl-2-oxo-2,3-dihydro-1H-benzo[d]imidazol-1-yl)piperidine-2,6-dione (500 mg, 1.48 mmol) in DMF (20 mL) was added TEA (448 mg, 4.44 mmol), Pd(dppf)Cl$_2$ (162 mg, 221 umol) and Et$_3$SiH (515 mg, 4.44 mmol). The reaction mixture was stirred at 80° C. for 16 hours under CO (50 Psi). On completion, the reaction mixture was concentrated in vacuo and purified by reverse phase (0.1% FA) to give the title compound (400 mg, 47% yield) as a white solid. LC-MS (ESI$^+$) m/z 288.0 (M+H)$^+$.

3-[3-Methyl-4-[[4-(methylamino)-1-piperidyl]methyl]-2-oxo-benzimidazol-1-yl]piperidine-2,6-dione (Intermediate WX)

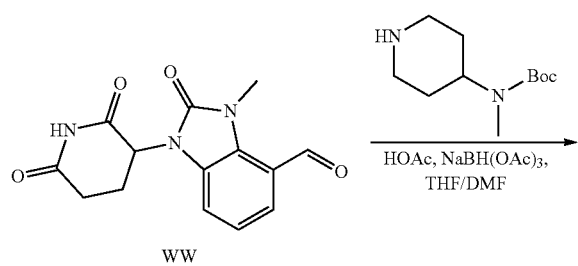

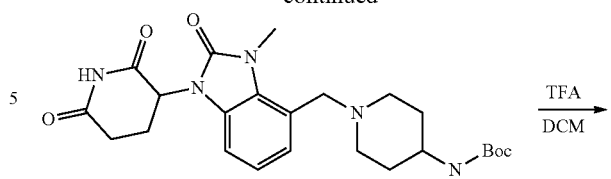

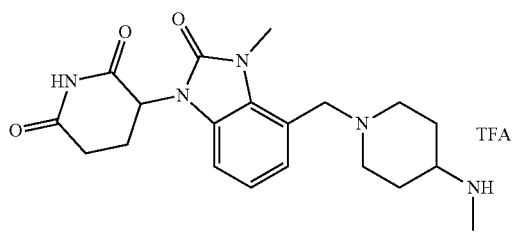

Step 1—Tert-butyl N-[1-[[1-(2,6-dioxo-3-piperidyl)-3-methyl-2-oxo-benzimidazol-4-yl]methyl]-4-piperidyl]-N-methyl-carbamate To a solution of 1-(2,6-dioxo-3-piperidyl)-3-methyl-2-oxo-benzimidazole-4-carbaldehyde (160 mg, 556 umol, Intermediate WW) and tert-butyl N-methyl-N-(4-piperidyl)carbamate (119 mg, 556 umol) in a mixed solvents of THF (3 mL) and DMF (1.5 mL) was added AcOH until the pH=5-7. After the reaction mixture was stirred at 20° C. for 3 hours. NaBH(OAc)$_3$ (177 mg, 835 umol) was added to the reaction mixture. The mixture was stirred at 20° C. for 12 hours. On completion, the reaction mixture was quenched by water (3 drops) and filtered. The filtrate was concentrated in vacuo. The residue was purified by reverse phase (FA condition) to give the title compound (220 mg, 46% yield) as white solid. LC-MS (ESI$^+$) m/z 486.2 (M+H)$^+$.

Step 2—3-[3-Methyl-4-[[4-(methylamino)-1-piperidyl]methyl]-2-oxo-benzimidazol-1-yl]piperidine-2,6-dione To a solution of tert-butyl N-[1-[[1-(2,6-dioxo-3-piperidyl)-3-methyl-2-oxo-benzimidazol-4-yl]methyl]-4-piperidyl]-N-methyl-carbamate (200 mg, 235 umol) in DCM (3 mL) was added TFA (3 mL). The reaction mixture was stirred at 15° C. for 0.5 hour. On completion, the reaction mixture was concentrated in vacuo to give the title compound (220 mg, 100% yield, TFA salt) as yellow oil. LC-MS (ESI$^+$) m/z 386.2 (M+H)$^+$.

2-[2-(Cyclopropylmethylamino)-4-pyridyl]-N-[3-(difluoromethyl)-1-[4-[[methyl-[2-(4-piperidyl)ethyl]amino]methyl] cyclohexyl]pyrazol-4-yl] oxazole-4-carboxamide (Intermediate WY)

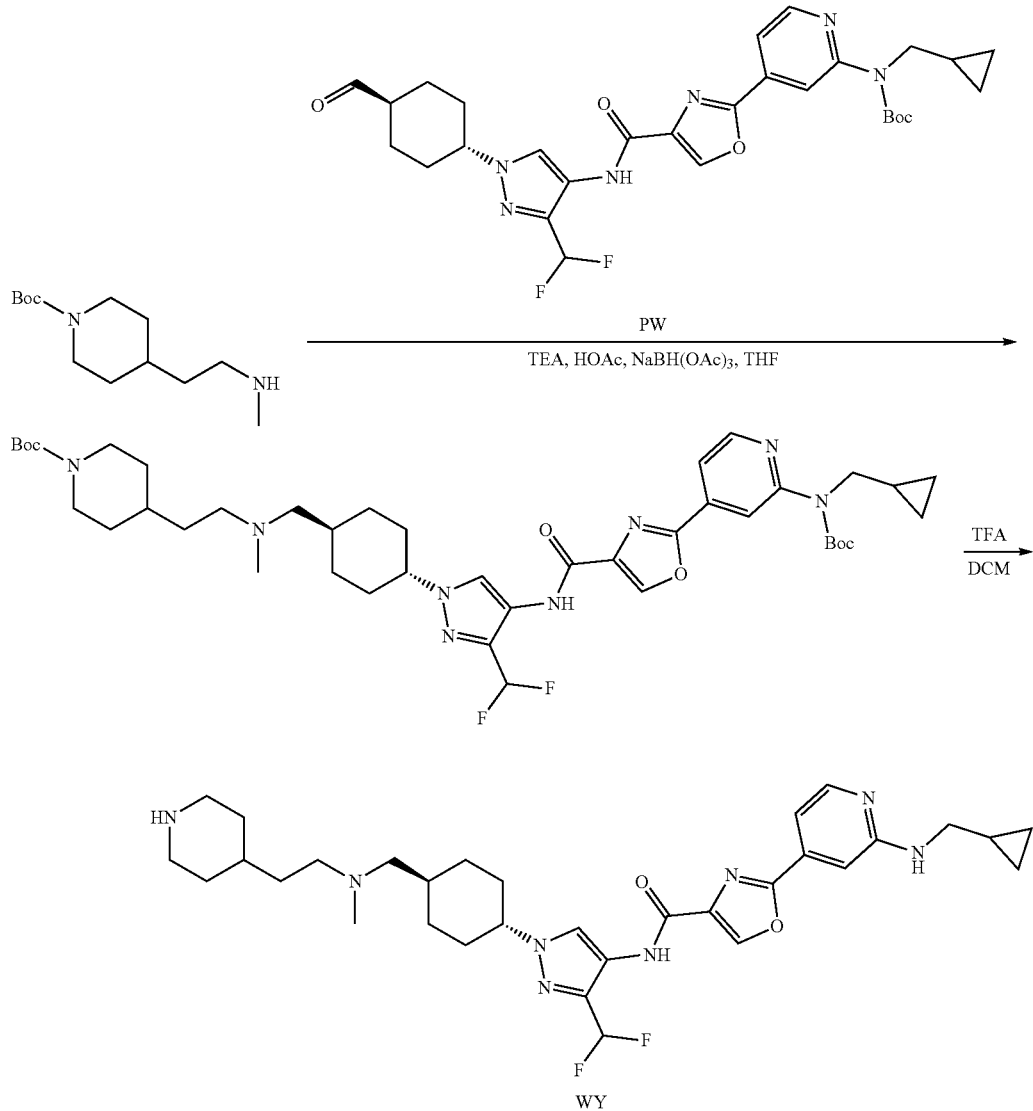

Step 1—Tert-butyl 4-[2-[[[4-[4-[[2-[2-[tert-butoxycarbonyl(cyclopropylmethyl)amino]-4-pyridyl] oxazole-4-carbonyl]amino]-3-(difluoromethyl)pyrazol-1-yl] cyclohexyl]methyl-methyl-amino] ethyl] piperidine-1-carboxylate To a solution of tert-butyl 4-[2-(methylamino)ethyl]piperidine-1-carboxylate (100 mg, 412 umol, CAS #896103-62-1) in THF (15 mL) was added TEA (41.8 mg, 412 umol) at 25° C. Then the reaction mixture was stirred at 25° C. for 10 minutes. HOAc (24.8 mg, 413 umol) and tert-butylN-(cyclopropylmethyl)-N-[4-[4-[[3-(difluoromethyl)-1-(4-formylcyclohexyl)pyrazol-4-yl]carbamoyl]oxazol-2-yl]-2-pyridyl]carbamate (241 mg, 412 umol, Intermediate PW) were added to the above mixture. The reaction mixture was stirred at 25° C. for 20 minutes. Then NaBH(OAc)₃ (175 mg, 825 umol) was added and the reaction mixture was stirred at 25° C. for 96 hours. On completion, the reaction was quenched with H$_2$O (1 mL). The mixture was concentrated in vacuo. The residue was purified by reverse phase (FA condition) to give the title compound (180 mg, 54% yield) as a purple solid. $^1$H NMR (400 MHz, DMSO-d$_6$) δ 9.76 (s, 1H), 9.00 (s, 1H), 8.59 (d, J=5.2 Hz, 1H), 8.29 (s, 1H), 8.18 (s, 1H), 7.68 (dd, J=1.2, 5.2 Hz, 1H), 7.15 (t, J=54.8 Hz, 1H), 4.27-4.13 (m, 1H), 3.95-3.82 (m, 4H), 2.54-2.51 (m, 5H), 2.28 (t, J=6.8 Hz, 2H), 2.11 (s, 3H), 2.09-1.99 (m, 3H), 1.88 (d, J=12.8 Hz, 2H), 1.81-1.69 (m, 2H), 1.62 (d, J=12.8 Hz, 2H), 1.51 (s, 9H), 1.41-1.36 (m, 9H), 1.35-1.29 (m, 2H), 1.22-1.12 (m, 1H), 1.08-0.91 (m, 4H), 0.45-0.36 (m, 2H), 0.27-0.19 (m, 2H); LC-MS (ESI⁺) m/z 811.5 (M+H)⁺.

1479

Step 2—2-[2-(Cyclopropylmethylamino)-4-pyridyl]-N-[3-(difluoromethyl)-1-[4-[[methyl-[2-(4-piperidyl)ethyl] amino]methyl]cyclohexyl]pyrazol-4-yl] oxazole-4-carboxamide To a solution of tert-butyl4-[2-[[4-[4-[[2-[2-[tert-butoxycarbonyl(cyclopropylmethyl)amino]-4-pyridyl] oxazole-4-carbonyl]amino]-3-(difluoromethyl)pyrazol-1-yl] cyclohexyl]methyl-methyl-amino] ethyl] piperidine-1-carboxylate (170 mg, 209 umol) in DCM (10 mL) was added TFA (10 mL) at 25° C. The reaction mixture was stirred at 25° C. for 1.5 hours. On completion, the reaction mixture was concentrated in vacuo to give the title compound (120 mg, 94% yield) as colorless oil. LC-MS (ESI$^+$) m/z 611.4 (M+H)$^+$.

3-[3-Methyl-4-[4-[4-(methylaminomethyl)-1-piperidyl]but-1-ynyl]-2-oxo-benzimidazol-1-yl] piperidine-2,6-dione (Intermediate WZ)

1480

Step 1—3-[4-(4-Hydroxybut-1-ynyl)-3-methyl-2-oxo-benzimidazol-1-yl]piperidine-2,6-dione To a solution of 3-(4-bromo-3-methyl-2-oxo-benzimidazol-1-yl)piperidine-2,6-dione (1.00 g, 2.96 mmol, Intermediate HP) and but-3-yn-1-ol (518 mg, 7.39 mmol, 559 uL, CAS #927-74-2) in DMSO (15 mL) was added Pd(PPh$_3$)$_2$Cl$_2$ (207 mg, 295 umol), CuI (56.3 mg, 295 umol) and DIPEA (1.91 g, 14.7 mmol, 2.58 mL). The reaction mixture was stirred at 80° C. for 2 hrs under N$_2$. On completion, the mixture was filtered, and the filtrate was concentrated in vacuo to give a residue. The residue was purified by reverse phase (0.1% FA condition) to give the title compound (600 mg, 62% yield) as a white solid. $^1$H NMR (400 MHz, DMSO-d$_6$) δ 11.13 (s, 1H), 7.15-6.97 (m, 3H), 5.39 (dd, J=4.8, 12.4 Hz, 1H), 4.94 (s, 1H), 3.65 (s, 3H), 3.34 (s, 2H), 2.95-2.84 (m, 1H), 2.69-2.59 (m, 4H), 2.06-2.00 (m, 1H); LC-MS (ESI$^+$) m/z 328.1 (M+H)$^+$.

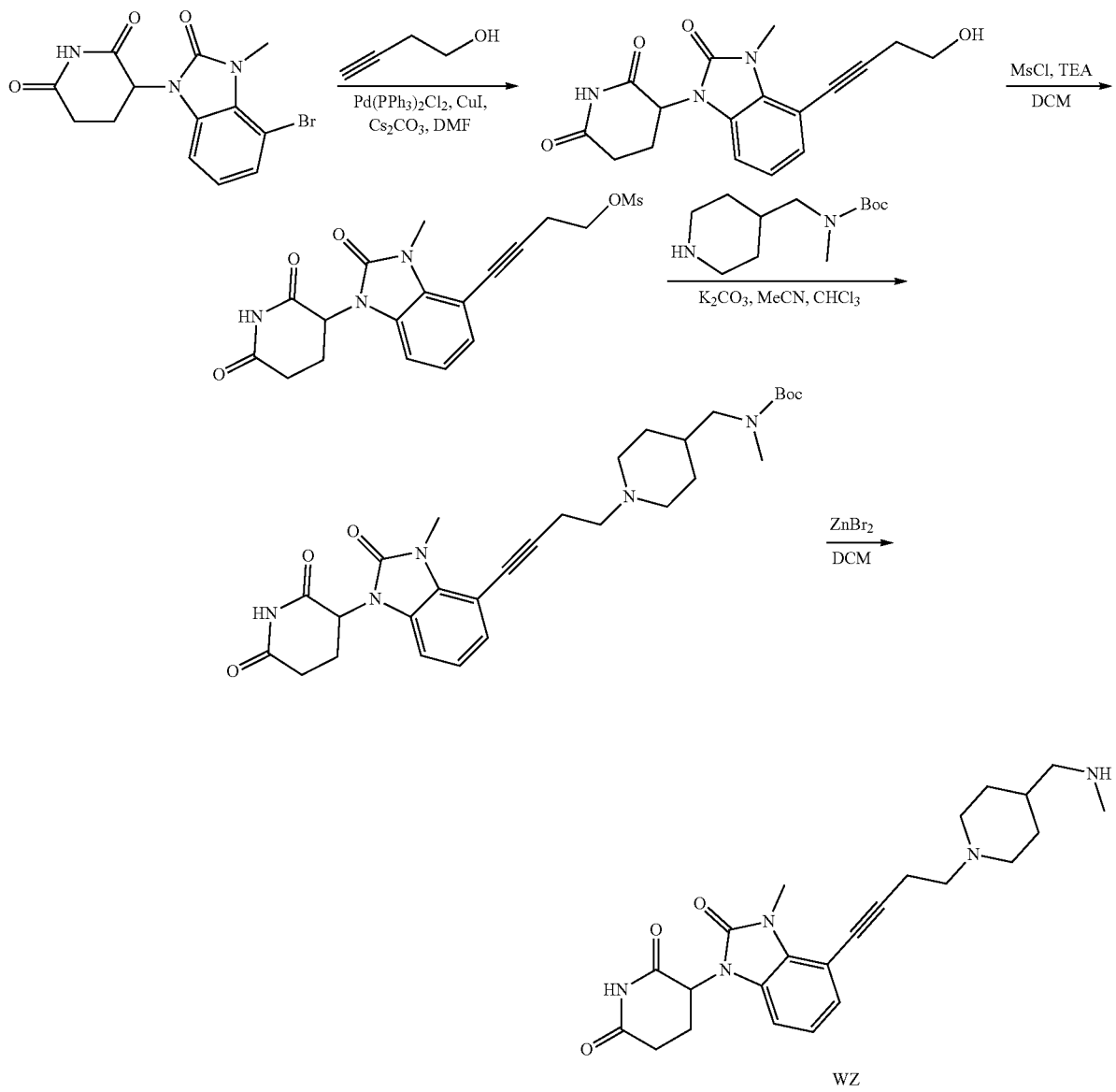

WZ

Step 2—4-[1-(2,6-Dioxo-3-piperidyl)-3-methyl-2-oxo-benzimidazol-4-yl]but-3-ynyl methanesulfonate To a solution of 3-[4-(4-hydroxybut-1-ynyl)-3-methyl-2-oxo-benzimidazol-1-yl]piperidine-2,6-dione (600 mg, 1.83 mmol) and TEA (556 mg, 5.50 mmol, 765 uL) in DCM (20 mL) was added MsCl (314 mg, 2.75 mmol, 212 uL) dropwise at 0° C. The reaction mixture was stirred at 25° C. for 2 hrs. On completion, the reaction mixture was quenched with H₂O (30 mL), then extracted with DCM (2×50 mL). The organic phase was dried with Na₂SO₄, filtrated and concentrated in vacuo to give the title compound (500 mg, 67% yield) as a yellow solid. LC-MS (ESI⁺) m/z 406.2 (M+H)⁺.

Step 3—Tert-butyl N-[[1-[4-[1-(2,6-dioxo-3-piperidyl)-3-methyl-2-oxo-benzimidazol-4-yl]but-3-ynyl]-4-piperidyl]methyl]-N-methyl-carbamate To a solution of 4-[1-(2,6-dioxo-3-piperidyl)-3-methyl-2-oxo-benzimidazol-4-yl]but-3-ynyl methanesulfonate (400 mg, 986 umol) and tert-butyl N-methyl-N-(4-piperidylmethyl)carbamate (270 mg, 1.18 mmol, CAS #138022-04-5) in MeCN (10 mL) and CHCl₃ (10 mL) was added K₂CO₃ (409 mg, 2.96 mmol). The reaction mixture was stirred at 65° C. for 16 hrs. On completion, the reaction mixture was diluted with water (30 mL) and extracted with EA (3×50 mL). The combined organic layers was dried over Na₂SO₄, filtered and concentrated in vacuo to give a residue. The residue was purified by reverse phase (0.1% FA condition) to give the title compound (140 mg, 26% yield) as a yellow solid. ¹H NMR (400 MHz, DMSO-d₆) δ 11.11 (s, 1H), 7.11 (d, J=7.2 Hz, 1H), 7.07-7.02 (m, 1H), 7.01-6.96 (m, 1H), 5.38 (dd, J=5.2, 12.8 Hz, 1H), 3.67 (s, 3H), 3.05 (d, J=6.4 Hz, 2H), 2.96-2.87 (m, 3H), 2.69-2.58 (m, 9H), 2.05-1.94 (m, 3H), 1.58-1.51 (m, 3H), 1.38 (s, 9H), 1.18-1.08 (m, 2H); LC-MS (ESI⁺) m/z 538.4 (M+H)⁺.

Step 4—3-[3-Methyl-4-[4-[4-(methylaminomethyl)-1-piperidyl]but-1-ynyl]-2-oxo-benzimidazol-1-yl]piperidine-2,6-dione To a solution of tert-butyl N-[[1-[4-[1-(2,6-dioxo-3-piperidyl)-3-methyl-2-oxo-benzimidazol-4-yl] but-3-ynyl]-4-piperidyl]methyl]-N-methyl-carbamate (140 mg, 260 umol) in DCM (3 mL) was added ZnBr₂ (293 mg, 1.30 mmol, 65.1 uL). The reaction mixture was stirred at 20° C. for 48 hrs. On completion, the reaction mixture was concentrated in vacuo to give a residue. The residue was purified by reverse phase (0.1% FA condition) to give the title compound (100 mg, 87% yield) as a white solid. LC-MS (ESI⁺) m/z 438.2 (M+H)⁺.

Tert-butyl (2,2-difluoro-3-(prop-2-yn-1-yloxy)propyl)(methyl)carbamate (Intermediate XA)

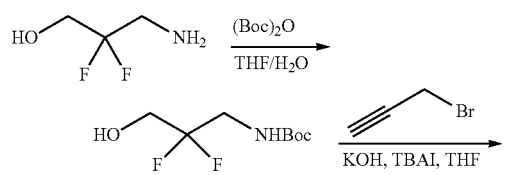

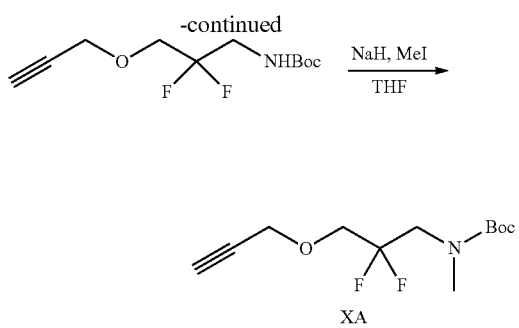

Step 1—Tert-butyl (2,2-difluoro-3-hydroxypropyl)carbamate

To a solution of 3-amino-2,2-difluoro-propan-1-ol (2.00 g, 18.0 mmol, CAS #155310-11-5) in a mixed solvents of THF (75 mL) and H₂O (75 mL) was added Boc₂O (3.93 g, 18.0 mmol) slowly at 0° C. The reaction mixture was stirred at 25° C. for 16 hours. On completion, the reaction mixture was diluted with 1.0 M aq.HCl (100 mL) and extracted with EA (2×150 mL). The combined organic phase was washed with brine (50 mL), dried over Na₂SO₄, filtered and concentrated in vacuo to give the title compound (3.76 g, 98% yield) as white solid. ¹H NMR (400 MHz, CDCl₃) δ 5.04 (s, 1H), 4.10-3.87 (m, 1H), 3.76-3.63 (m, 2H), 3.60-3.54 (m, 2H), 1.48 (s, 9H).

Step 2—Tert-butyl (2,2-difluoro-3-(prop-2-yn-1-yloxy)propyl)carbamate

To a solution of tert-butyl N-(2,2-difluoro-3-hydroxypropyl)carbamate (5.00 g, 23.7 mmol) in THF (100 mL) was added KOH (1.33 g, 23.7 mmol), KI (393 mg, 2.37 mmol), TBAI (1.31 g, 3.55 mmol) and 3-bromoprop-1-yne (4.22 g, 28.41 mmol) at 25° C. The reaction mixture was stirred at 25° C. for 16 hours. On completion, the reaction mixture was diluted with sat. aq. NH₄Cl (100 mL) and extracted with EA (2×150 mL). The combined organic phase was concentrated in vacuo. The residue was purified by silica gel chromatography (PE:EA=40:1) to give title compound (3.27 g, 55% yield) as colorless oil. ¹H NMR (400 MHz, CDCl₃) δ 4.95-4.73 (m, 1H), 4.30-4.24 (m, 2H), 3.84-3.74 (m, 2H), 3.72-3.58 (m, 2H), 2.56-2.46 (m, 1H), 1.47 (s, 9H).

Step 3—Tert-butyl (2,2-difluoro-3-(prop-2-yn-1-yloxy)propyl)(methyl)carbamate To solution of tert-butyl N-(2,2-difluoro-3-prop-2-ynoxy-propyl)carbamate (3.00 g, 12.1 mmol) in THF (50 mL) was added NaH (578 mg, 14.4 mmol, 60% dispersion in mineral oil) at 0° C. The mixture was stirred at 0° C. for 0.5 hour, then MeI (3.42 g, 24.1 mmol) was added. The reaction mixture stirred at 0-25° C. for 2 hours. On completion, the reaction was quenched with water (100 mL). The mixture was extracted with EA (2×100 mL). The combined organic phase was concentrated in vacuo to give the title compound (3.00 g, 95% yield) as yellow oil. ¹H NMR (400 MHz, CDCl₃) δ 4.25-4.18 (m, 2H), 3.72-3.58 (m, 4H), 2.89 (s, 3H), 2.42 (s, 1H), 1.40 (s, 9H).

3-(4-(3-(2,2-Difluoro-3-(methylamino)propoxy)propyl)-3-methyl-2-oxo-2,3-dihydro-1H-benzo[d]imidazol-1-yl)piperidine-2,6-dione (Intermediate XB)

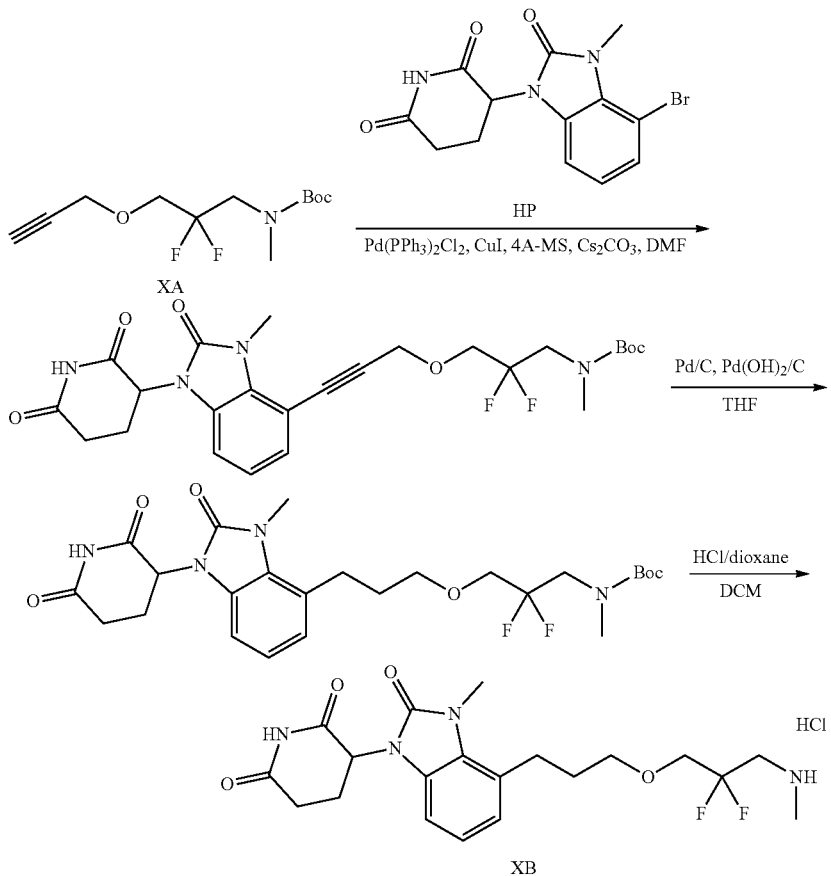

Step 1—Tert-butyl (3-((3-(1-(2,6-dioxopiperidin-3-yl)-3-methyl-2-oxo-2,3-dihydro-1H-benzo[d] imidazol-4-yl)prop-2-yn-1-yl)oxy)-2,2-difluoropropyl)(methyl)carbamate To a solution of tert-butyl N-(2,2-difluoro-3-prop-2-ynoxy-propyl)carbamate (442 mg, 1.77 mmol, Intermediate XA) and 3-(4-bromo-3-methyl-2-oxo-benzimidazol-1-yl)piperidine-2,6-dione (300 mg, 887 umol, Intermediate HP) in DMF (6 mL) was added Pd(PPh$_3$)$_2$Cl$_2$ (125 mg, 177 umol), CuI (33.8 mg, 177 umol), Cs$_2$CO$_3$ (1.45 g, 4.44 mmol) and 4 Å molecular sieves (100 mg) at 20° C. The mixture was stirred at 80° C. for 2 hours under N$_2$. On completion, the reaction mixture was cooled to 20° C. The mixture was diluted with EA (50 mL) and filtered. The filtrate was washed with brine (50 mL), dried over Na$_2$SO$_4$, filtered and concentrated in vacuo. The residue was purified by reverse phase (FA condition) to give the title compound (160 mg, 35% yield) as brown solid. $^1$H NMR (400 MHz, DMSO-d$_6$) δ 11.11 (s, 1H), 7.24-7.17 (m, 1H), 7.17-7.11 (m, 1H), 7.08-7.01 (m, 1H), 5.46-5.35 (m, 1H), 4.58 (s, 2H), 3.89-3.78 (m, 2H), 3.78-3.68 (m, 2H), 3.67-3.59 (m, 3H), 1.38 (s, 9H). LC-MS (ESI$^+$) m/z 543.1 (M+Na)$^+$.

Step 2—Tert-butyl (3-(3-(1-(2,6-dioxopiperidin-3-yl)-3-methyl-2-oxo-2,3-dihydro-1H-benzo[d] imidazol-4-yl)propoxy)-2,2-difluoropropyl)(methyl)carbamate To a solution of tert-butyl N-[3-[3-[1-(2,6-dioxo-3-piperidyl)-3-methyl-2-oxo-benzimidazol-4-yl] prop-2-ynoxy]-2,2-difluoro-propyl]-N-methyl-carbamate (200 mg, 384 umol) in THF (10 mL) was added Pd/C (50.0 mg, 10 wt %) and Pd(OH)$_2$/C (50.0 mg, 10 wt %) at 25° C. The mixture was stirred at 25° C. for 18 hours under H$_2$ (15 psi). On completion, the reaction mixture was diluted with THF (40 mL), filtrated and concentrated in vacuo to give the title compound (195 mg, 97% yield) as yellow solid. $^1$H NMR (400 MHz, DMSO-d$_6$) δ 11.08 (s, 1H), 7.01-6.94 (m, 2H), 6.91-6.84 (m, 1H), 5.40-5.33 (m, 1H), 3.64-3.58 (m, 6H), 3.58-3.56 (m, 3H), 3.02-2.93 (m, 2H), 2.87 (s, 3H), 1.91-1.82 (m, 2H), 1.79-1.74 (m, 4H), 1.40 (s, 9H); LC-MS (ESI$^+$) m/z 547.3 (M+Na)$^+$.

Step 3—3-(4-(3-(2,2-Difluoro-3-(methylamino)propoxy)propyl)-3-methyl-2-oxo-2,3-dihydro-1H-benzo[d]imidazol-1-yl)piperidine-2,6-dione To the solution of tert-butyl N-[3-[3-[1-(2,6-dioxo-3-piperidyl)-3-methyl-2-oxo-benzimidazol-4-yl] propoxy]-2,2- difluoro-propyl]-N-methyl-carbamate (180 mg, 343 umol) in DCM (3 mL) was added HCl/dioxane (3 mL) at 25° C. The reaction mixture was stirred at 25° C. for 2 hours. On completion, the mixture was concentrated in vacuo to give the title compound (155 mg, 98% yield, HCl salt). LC-MS (ESI$^+$) m/z 425.1 (M+H)$^+$.

3-[6-[3-[3-(Methylamino)propoxypropyl]-2-oxo-1,3-benzoxazol-3-yl]piperidine-2,6-dione (Intermediate XC)

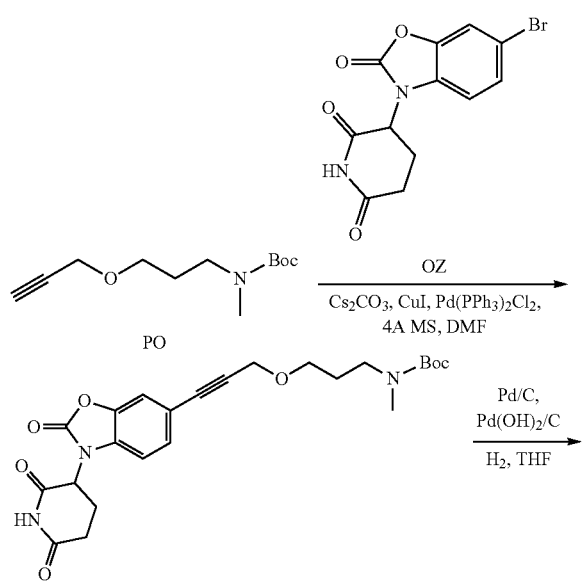

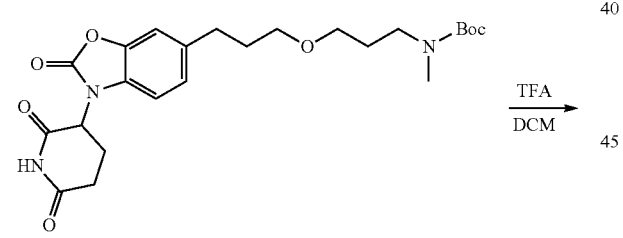

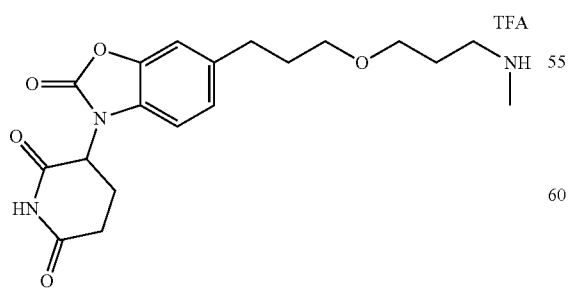

XC

Step 1—Tert-butyl N-[3-[3-[3-(2,6-dioxo-3-piperidyl)-2-oxo-1,3-benzoxazol-6-yl]prop-2-ynoxy]propyl]-N-methyl-carbamate To a mixture of 3-(6-bromo-2-oxo-1,3-benzoxazol-3-yl)piperidine-2,6-dione (450 mg, 1.38 mmol, Intermediate OZ), tert-butyl N-methyl-N-(3-prop-2-ynoxypropyl)carbamate (566 mg, 2.49 mmol, Intermediate PO) in DMF (10 mL) was added Cs$_2$CO$_3$ (2.25 g, 6.92 mmol), CuI (79.08 mg, 415.24 umol), Pd(PPh$_3$)$_2$Cl$_2$ (97.1 mg, 138 umol) and molecular sieves 4 Å (50 mg). The reaction mixture was stirred at 80° C. for 2 hours under N$_2$. On completion, the reaction was filtered. And the filtrate was poured into water (100 mL), then the aqueous phase was extracted with ethyl acetate (2×40 mL). The combined organic phase was washed with brine (2×40 mL), dried with anhydrous Na$_2$SO$_4$, filtered and concentrated in vacuo to give the residue. The residue was purified by reversed-phase HPLC (0.1% FA condition) to give the title compound (350 mg, 49% yield) as a brown solid. $^1$H NMR (300 MHz, CDCl$_3$) δ 8.24-8.11 (m, 1H), 7.35 (s, 2H), 6.78 (d, J=8.4 Hz, 1H), 5.06 (d, J=5.2, 12.8 Hz, 1H), 4.37 (s, 2H), 3.60 (d, J=6.4 Hz, 2H), 3.34 (d, J=6.8 Hz, 2H), 2.89 (s, 3H), 1.94-1.78 (m, 3H), 1.75-1.61 (m, 3H), 1.47 (s, 9H).

Step 2—Tert-butyl N-[3-[3-[3-(2,6-dioxo-3-piperidyl)-2-oxo-1,3-benzoxazol-6-yl]propoxy]propyl]-N-methyl-carbamate To a mixture of tert-butyl N-[3-[3-[3-(2,6-dioxo-3-piperidyl)-2-oxo-1,3-benzoxazol-6-yl]prop-2-ynoxy] propyl]-N-methyl-carbamate (350 mg, 742 umol) in THF (10 mL) was added Pd/C (50 mg, 10 wt %) and Pd(OH)$_2$/C (50 mg, 10 wt %) under N$_2$. The suspension was degassed under vacuum and purged with H$_2$ three times. The mixture was stirred at 25° C. for 12 hours under H$_2$ (15 psi). On completion, the reaction mixture was filtered and the filtrate was concentrated in vacuo to give the title compound (330 mg, 93% yield) as brown oil. $^1$H NMR (400 MHz, CDCl$_3$) δ 8.19 (s, 1H), 7.12 (s, 1H), 7.00 (d, J=8.0 Hz, 1H), 6.73 (d, J=8.0 Hz, 1H), 5.06 (d, J=5.6, 13.2 Hz, 1H), 3.41 (q, J=6.4 Hz, 4H), 3.30 (s, 2H), 3.03-2.94 (m, 1H), 2.89-2.84 (m, 3H), 2.78-2.68 (m, 3H), 2.37-2.26 (m, 1H), 1.94-1.72 (m, 4H), 1.63 (d, J=6.8 Hz, 2H), 1.46 (s, 8H).

Step 3—3-[6-[3-[3-(Methylamino)propoxy]propyl]-2-oxo-1,3-benzoxazol-3-yl]piperidine-2,6-dione To a mixture of tert-butyl N-[3-[3-[3-(2,6-dioxo-3-piperidyl)-2-oxo-1,3-benzoxazol-6-yl]propoxy] propyl]-N-methyl-carbamate (320 mg, 673 umol) in DCM (10 mL) was added TFA (153 mg, 1.35 mmol). The reaction mixture was stirred at 25° C. for 1 hour. On completion, the reaction mixture was concentrated in vacuo to give the title compound (320 mg, 97% yield, TFA salt) as a white solid. LC-MS (ESI$^+$) m/z 376.2 (M+H)$^+$.

3-[3-Methyl-4-[3-[3-(methylamino)propoxy]prop-1-ynyl]-2-oxo-benzimidazol-1-yl] piperidine-2,6-dione (Intermediate XD)

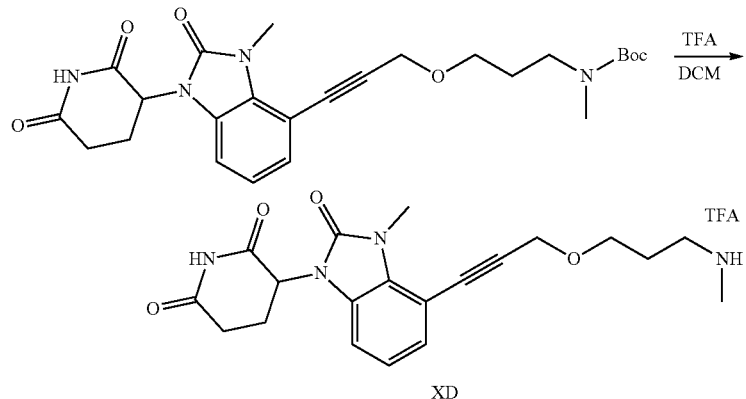

XD

To a mixture of tert-butyl N-[3-[3-[1-(2,6-dioxo-3-piperidyl)-3-methyl-2-oxo-benzimidazol-4-yl]prop-2-ynoxy]propyl]-N-methyl-carbamate (180 mg, 371 umol, synthesized via Step 1 of Intermediate PP) in DCM (5 mL) was added TFA (7.70 g, 67.5 mmol, 5.00 mL). The reaction mixture was stirred at 25° C. for 2 hours. On completion, the reaction mixture was concentrated in vacuo to give the title compound (180 mg, 97% yield, TFA salt) as a yellow solid. $^1$H NMR (400 MHz, DMSO-$d_6$) δ 11.13 (s, 1H), 8.35 (s, 2H), 7.19 (d, J=7.6 Hz, 1H), 7.14-7.11 (m, 1H), 7.06-7.01 (m, 1H), 5.40 (dd, J=12.8 Hz, 1H), 4.45 (s, 3H), 3.65 (s, 3H), 3.60 (s, 2H), 2.97 (m, 2H), 2.91-2.83 (m, 1H), 2.73-2.60 (m, 2H), 2.52-2.50 (m, 2H), 2.06-1.99 (m, 1H), 1.90-1.83 (m, 2H).

2-(Methylamino)ethyl N-[[1-(2,6-dioxo-3-piperidyl)-3-methyl-2-oxo-benzimidazol-5-yl] methyl]carbamate (Intermediate XE)

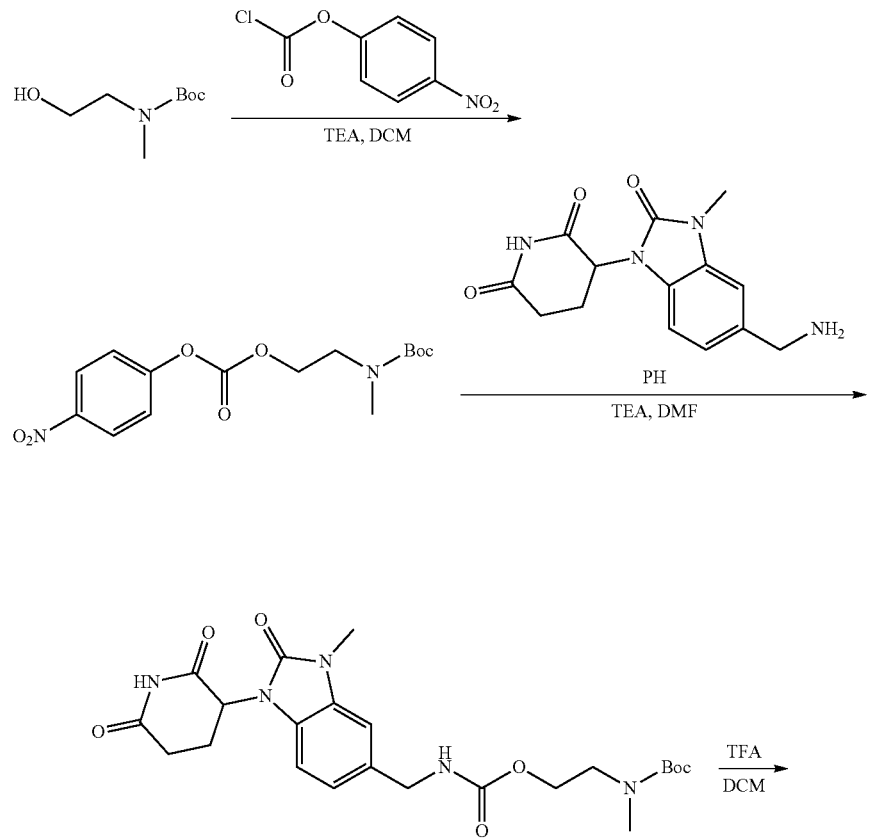

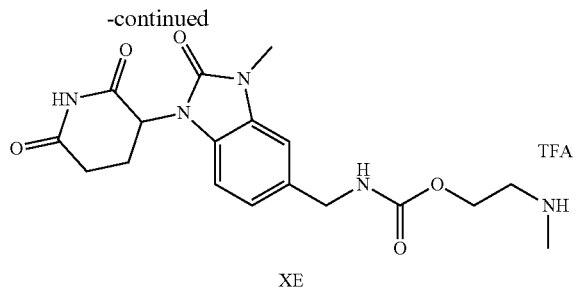

XE

Step 1—2-[Tert-butoxycarbonyl(methyl)amino]ethyl (4-nitrophenyl) carbonate

To a mixture of tert-butyl N-(2-hydroxyethyl)-N-methylcarbamate (1.00 g, 5.71 mmol, CAS #57561-39-4) and (4-nitrophenyl) carbonochloridate (1.15 g, 5.71 mmol, CAS #7693-46-1) in DCM (20 mL) was added TEA (1.44 g, 14.27 mmol) at 0° C. for 1 hour. On completion, the reaction was poured into the ice-water (50 mL) and extracted with DCM (2×30 mL). The combined organic phase was washed with brine (2×50 mL), dried with anhydrous $Na_2SO_4$, filtered and concentrated in vacuo to give the title compound (1.80 g, 92% yield) as a white solid. $^1$H NMR (300 MHz, $CDCl_3$) δ 8.30 (d, J=9.2 Hz, 2H), 7.41 (d, J=9.2 Hz, 2H), 4.41 (t, J=5.6 Hz, 2H), 3.61 (s, 2H), 2.98 (s, 3H), 1.48 (s, 9H).

Step 2—Tert-butylN-[2-[[1-(2,6-dioxo-3-piperidyl)-3-methyl-2-oxo-benzimidazol-5-yl]methylcarbamoyloxy] ethyl]-N-methyl-carbamate To a mixture of 2-[tert-butoxycarbonyl(methyl)amino] ethyl (4-nitrophenyl) carbonate (172 mg, 507 umol), 3-[5-(aminomethyl)-3-methyl-2-oxo-benzimidazol-1-yl]piperidine-2,6-dione (102 mg, 253 umol, TFA salt, Intermediate PH) in DMF (10 mL) was added TEA (128 mg, 1.27 mmol). The reaction mixture was stirred at 25° C. for 1 hour. On completion, the reaction mixture was concentrated in vacuo to give the residue. The residue was purified by reversed-phase HPLC (0.1% FA condition) to give the title compound (105 mg, 84% yield) as brown solid. $^1$H NMR (400 MHz, DMSO-$d_6$) δ 11.08 (s, 1H), 7.69 (s, 1H), 7.09-7.02 (m, 2H), 6.95 (d, J=8.4 Hz, 1H), 5.39-5.32 (m, 1H), 4.21 (d, J=6.0 Hz, 2H), 4.10-4.03 (m, 2H), 3.36 (t, J=5.6 Hz, 2H), 2.97-2.85 (m, 1H), 2.80 (s, 2H), 2.74 (d, J=4.4, 8.8 Hz, 1H), 2.67-2.59 (m, 1H), 2.10-1.59 (m, 3H), 1.37 (s, 9H).

Step 3—2-(Methylamino)ethylN-[[1-(2,6-dioxo-3-piperidyl)-3-methyl-2-oxo-benzimidazol-5-yl] methyl]carbamate To a mixture of tert-butyl N-[2-[[1-(2,6-dioxo-3-piperidyl)-3-methyl-2-oxo-benzimidazol-5-yl] methylcarbamoyloxy]ethyl]-N-methyl-carbamate (105 mg, 214 umol) in DCM (10 mL) was added TFA (24.4 mg, 214 umol). The reaction mixture was stirred at 25° C. for 0.5 hour. On completion, the reaction mixture was concentrated in vacuo to give the title compound (107 mg, 99% yield, TFA salt) as brown oil. LC-MS (ESI$^+$) m/z 390.1 (M+H)$^+$.

Tert-butyl N-methyl-N-(1-prop-2-ynyl-4-piperidyl) carbamate (Intermediate XH)

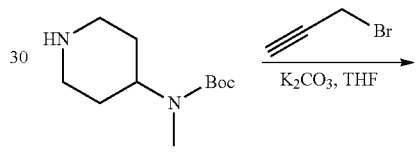

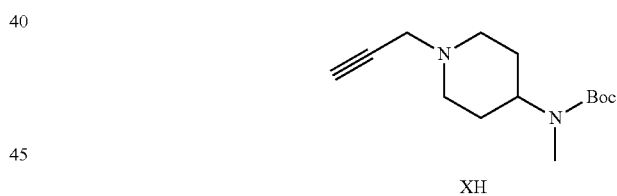

XH

To a solution of tert-butyl N-methyl-N-(4-piperidyl)carbamate (1.50 g, 7.00 mmol, CAS #108612-54-0) and 3-bromoprop-1-yne (915 mg, 7.70 mmol, 663 uL, CAS #106-96-70) in THF (30 mL) was added $K_2CO_3$ (2.90 g, 21.0 mmol). The reaction mixture was stirred at 25° C. for 16 hrs. On completion, the mixture was diluted with water (30 mL) and extracted with EA (3×80 mL). The combined organic layers was dried over $Na_2SO_4$, filtered and concentrated in vacuo to give the title compound (1.50 mg, 85% yield) as yellow solid. $^1$H NMR (400 MHz, $CDCl_3$) δ 4.16-3.61 (m, 1H), 3.29 (d, J=2.0 Hz, 2H), 3.01-2.90 (m, 2H), 2.73 (s, 3H), 2.35-2.21 (m, 3H), 1.81-1.72 (m, 2H), 1.69-1.63 (m, 2H), 1.46 (s, 9H).

3-[3-Methyl-4-[3-[4-(methylamino)-1-piperidyl]propyl]-2-oxo-benzimidazol-1-yl]piperidine-2,6-dione (Intermediate XI)

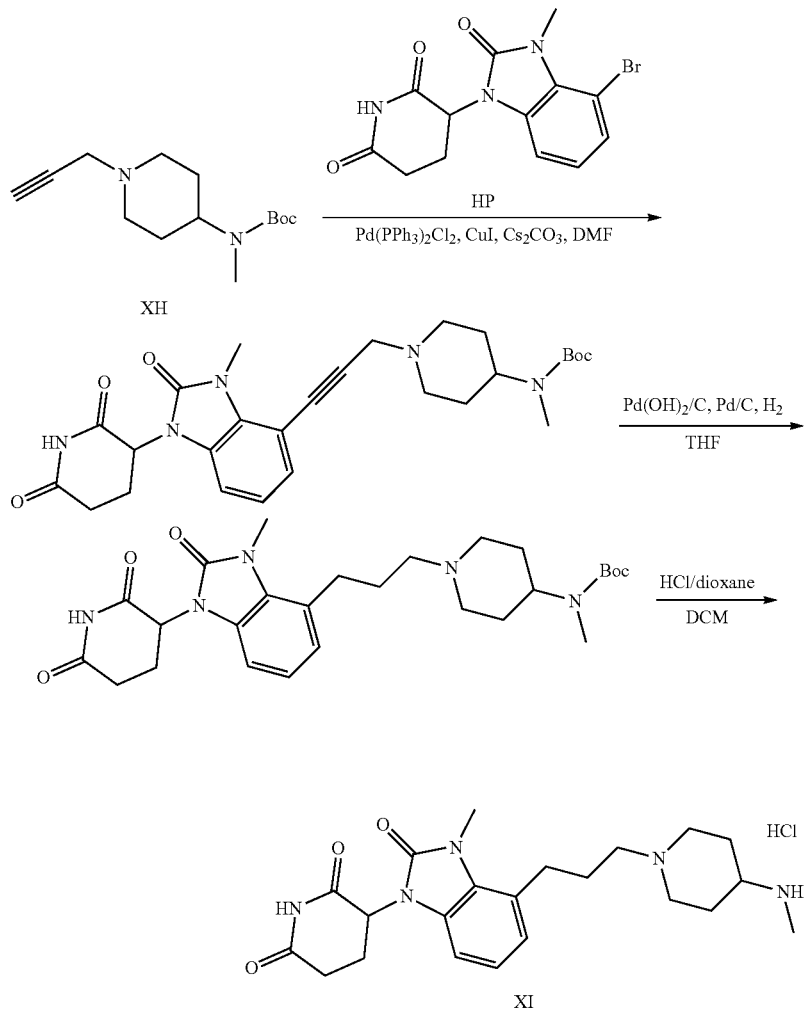

Step 1—Tert-butyl N-[1-[3-[1-(2,6-dioxo-3-piperidyl)-3-methyl-2-oxo-benzimidazol-4-yl]prop-2-ynyl]-4-piperidyl]-N-methyl-carbamate To a solution of tert-butyl N-methyl-N-(1-prop-2-ynyl-4-piperidyl)carbamate (559 mg, 2.22 mmol, Intermediate XH) and 3-(4-bromo-3-methyl-2-oxo-benzimidazol-1-yl)piperidine-2,6-dione (500 mg, 1.48 mmol, Intermediate HP) in DMF (5 mL) was added Pd(PPh$_3$)$_2$Cl$_2$ (103 mg, 147 umol), CuI (28.1 mg, 147 umol) and Cs$_2$CO$_3$ (955 mg, 2.93 mmol, 2.58 mL). The reaction mixture was stirred at 80° C. for 2 hr under N$_2$. On completion, the mixture was filtered and the filtrate was concentrated in vacuo to give a residue. The residue was purified by reverse phase (0.1% FA condition) to give the title compound (700 mg, 93% yield) as a gray solid. $^1$H NMR (400 MHz, DMSO-d$_6$) δ 11.13 (s, 1H), 7.20-6.93 (m, 3H), 5.40 (dd, J=5.2, 12.8 Hz, 1H), 3.66 (s, 3H), 3.58 (s, 2H), 2.98-2.84 (m, 3H), 2.68 (s, 3H), 2.66-2.59 (m, 2H), 2.25 (t, J=10.8 Hz, 2H), 2.07-1.99 (m, 2H), 1.75-1.50 (m, 5H), 1.40 (s, 9H); LC-MS (ESI$^+$) m/z 510.3 (M+H)$^+$.

Step 2—Tert-butyl N-[1-[3-[1-(2,6-dioxo-3-piperidyl)-3-methyl-2-oxo-benzimidazol-4-yl]propyl]-4-piperidyl]-N-methyl-carbamate To a solution of tert-butyl N-[1-[3-[1-(2,6-dioxo-3-piperidyl)-3-methyl-2-oxo-benzimidazol-4-yl] prop-2-ynyl]-4-piperidyl]-N-methyl-carbamate (650 mg, 1.28 mmol) in THF (20 mL) was added Pd/C (150 mg, 1.28 mmol, 10 wt %) and Pd(OH)$_2$/C (150 mg, 10 wt %). The reaction mixture was stirred at 25° C. under H$_2$ (15 psi) for 2 hrs. On completion, the residue was filtered and the filtrate was concentrated in vacuo to give a residue. The residue was purified by reverse phase (0.1% FA condition) to give the title compound (480 mg, 73% yield) as a white solid. $^1$H NMR (400 MHz, DMSO-d$_6$) δ 11.08 (s, 1H), 6.96 (d, J=4.8 Hz, 2H), 6.93-6.86 (m, 1H), 5.36 (dd, J=5.6, 12.8 Hz, 1H), 3.93-3.65 (m, 1H), 3.56 (s, 3H), 3.08-2.97 (m, 2H), 2.96-2.81 (m, 3H), 2.76-2.67 (m, 1H), 2.66 (s, 3H), 2.64-2.58 (m, 1H), 2.49-2.39 (m, 2H), 2.14-2.05 (m, 2H), 2.03-1.94 (m, 1H), 1.83-1.62 (m, 4H), 1.56-1.48 (m, 2H), 1.39 (s, 9H); LC-MS (ESI$^+$) m/z 514.3 (M+H)$^+$.

Step 3—3-[3-Methyl-4-[3-[4-(methylamino)-1-piperidyl]propyl]-2-oxo-benzimidazol-1-yl]piperidine-2,6-dione To a solution of tert-butyl N-[1-[3-[1-(2,6-dioxo-3-piperidyl)-3-methyl-2-oxo-benzimidazol-4-yl] propyl]-4-piperidyl]-N-methyl-carbamate (100 mg, 194 umol) in DCM (2 mL) was added HCl/dioxane (4 M, 1 mL). The reaction mixture was stirred at 20° C. for 2 hrs. On completion, the mixture was concentrated in vacuo to give the title compound (85.0 mg, 97% yield, HCl) as a white solid. LC-MS (ESI⁺) m/z 414.3 (M+H)⁺.

Tert-butyl N-methyl-N-[2-(4-piperidylmethoxy) ethyl]carbamate (Intermediate XJ)

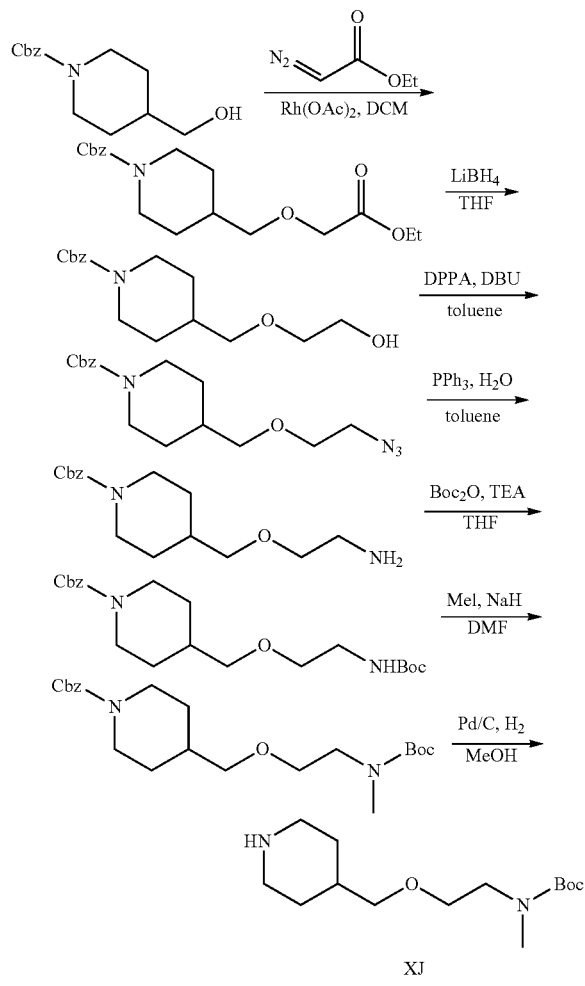

Step 1—Benzyl 4-((2-ethoxy-2-oxoethoxy)methyl) piperidine-1-carboxylate

A solution of benzyl 4-(hydroxymethyl) piperidine-1-carboxylate (15.0 g, 60.2 mmol, CAS #122860-33-7) in DCM (15 mL) was added diacetoxyrhodium (1.33 g, 3.01 mmol, CAS #623-73-4). The mixture was stirred at 25° C. for 0.5 hour. Then ethyl 2-diazoacetate (13.7 g, 120 mmol) in DCM (15 mL) was added dropwise slowly to the solution. The mixture was stirred at 25° C. for 12 hours. On completion, the reaction mixture was quenched by water (10 mL), and extracted with DCM (3×20 mL). The combined organic layers dried over Na₂SO₄, filtered and concentrated in vacuo to give a residue. The residue was purified by column chromatography to give the title compound (16.8 g, 83% yield) as yellow oil. LC-MS (ESI⁺) m/z 336.2 (M+H)⁺.

Step 2—Benzyl 4-((2-hydroxyethoxy)methyl)piperidine-1-carboxylate

To a solution of benzyl 4-[(2-ethoxy-2-oxo-ethoxy)methyl]piperidine-1-carboxylate (16.8 g, 50.1 mmol) in THF (180 mL) was added LiBH₄ (2.18 g, 100 mmol) at 0° C. The mixture was stirred at 25° C. for 12 hours. On completion, the reaction mixture was quenched with H₂O (200 mL) and then extracted with ethyl acetate (2×300 mL). Then the organic layers were washed with brine (2×150 mL). The combined organic layer was dried over anhydrous Na₂SO₄, filtered and concentrated in vacuo to give a residue. The residue was purified by column chromatography to give the title compound (13.2 g, 90% yield) as colorless oil. LC-MS (ESI⁺) m/z 294.2 (M+H)⁺.

Step 3—Benzyl 4-((2-azidoethoxy)methyl)piperidine-1-carboxylate

To a solution of benzyl 4-(2-hydroxyethoxymethyl)piperidine-1-carboxylate (4.00 g, 13.6 mmol) in toluene (40 mL) was added DPPA (4.50 g, 16.4 mmol) and DBU (2.49 g, 16.4 mmol). The mixture was stirred at 100° C. for 12 hours. On completion, the reaction mixture was diluted with H₂O (50 mL) and extracted with ethyl acetate (3×50 mL). The combined organic layers were dried over anhydrous Na₂SO₄, filtered and concentrated in vacuo to give the title compound (4.34 g, 98% yield) as yellow oil.

Step 4—Benzyl 4-(2-aminoethoxymethyl)piperidine-1-carboxylate

To a solution of benzyl 4-(2-azidoethoxymethyl)piperidine-1-carboxylate (4.34 g, 13.6 mmol) in a mixed solvent of THF (45 mL) and H₂O (5 mL) was added PPh₃ (3.58 g, 13.6 mmol). The mixture was stirred at 66° C. for 12 hours. On completion, the reaction mixture was diluted with H₂O (50 mL) and extracted with ethyl acetate (3×50 mL). The organic layers were dried over anhydrous Na₂SO₄, filtered and concentrated in vacuo to give the title compound (3.99 g, 99% yield) as yellow oil. LC-MS (ESI⁺) m/z 293.2 (M+H)⁺.

Step 5—Benzyl 4-[2-(tert-butoxycarbonylamino) ethoxymethyl]piperidine-1-carboxylate To a solution of benzyl 4-(2-aminoethoxymethyl)piperidine-1-carboxylate (3.99 g, 13.7 mmol) in THF (40 mL) was added Boc₂O (4.47 g, 20.5 mmol) and TEA (4.14 g, 40.9 mmol). The mixture was stirred at 25° C. for 12 hours. On completion, the reaction mixture was diluted with H₂O (100 mL) and extracted with (2×100 mL). The organic layers were dried over anhydrous Na₂SO₄, filtered and concentrated in vacuo to give a residue. The residue was purified by column chromatography to give the title compound (4.70 g, 80% yield) as yellow oil. LC-MS (ESI⁺) m/z 415.3 (M+Na)⁺.

Step 6—Benzyl 4-[2-[tert-butoxycarbonyl(methyl) amino]ethoxymethyl]piperidine-1-carboxylate To a solution of benzyl 4-[2-(tert-butoxycarbonylamino) ethoxymethyl]piperidine-1-carboxylate (4.60 g, 11.7 mmol) in DMF (50 mL) was added NaH (938 mg, 23.4 mmol, 60% dispersion in oil) at 0° C. Then $CH_3I$ (3.33 g, 23.4 mmol) was added dropwise to the solution. The mixture was stirred at 0-25° C. for 2 hours. On completion, the reaction mixture was quenched with saturated $NH_4Cl$ (20 mL). Then $H_2O$ (50 mL) and ethyl acetate (100 mL) was added. The aqueous layer was extracted with ethyl acetate (2×100 mL). The combined organic layers were washed with brine (50 mL). The organic layer was dried over anhydrous $Na_2SO_4$, filtered and concentrated in vacuo to give a residue. The residue was purified by column chromatography to give the title compound (3.80 g, 79% yield) as yellow oil.

Step 7—Tert-butyl N-methyl-N-[2-(4-piperidylmethoxy) ethyl]carbamate

To a solution of benzyl 4-[2-[tert-butoxycarbonyl(methyl) amino]ethoxymethyl]piperidine-1-carboxylate (3.80 g, 9.35 mmol) in MeOH (80 mL) was added Pd/C (400 mg, 377 umol, 10 wt %). The mixture was stirred at 25° C. for 12 hours. On completion, the reaction mixture was filtered and concentrated in vacuo to give the title compound (3.30 g, 98% yield) as yellowish oil. LC-MS (ESI$^+$) m/z 273.2 (M+H)$^+$.

3-(3-methyl-5-(4-((2-(methylamino)ethoxy)methyl) piperidin-1-yl)-2-oxo-2,3-dihydro-1H-benzo[d]imidazol-1-yl)piperidine-2,6-dione methanesulfonate (Intermediate XK)

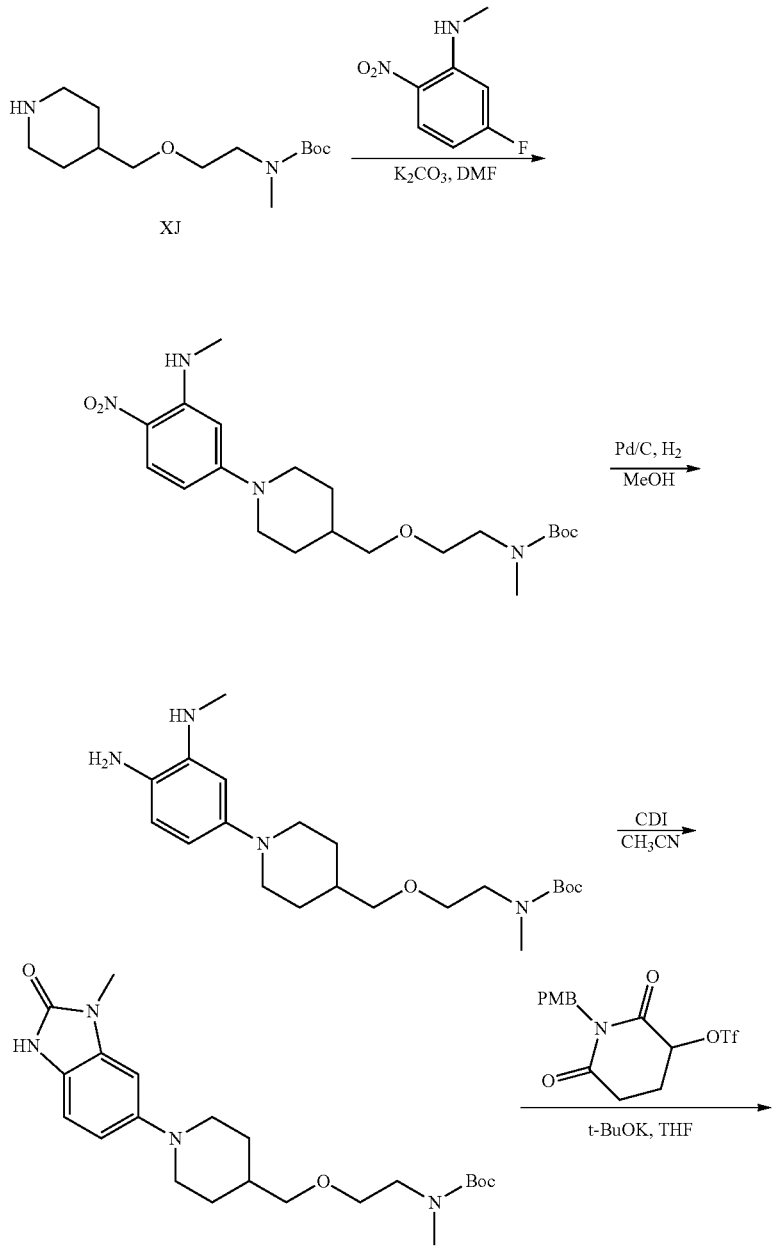

-continued

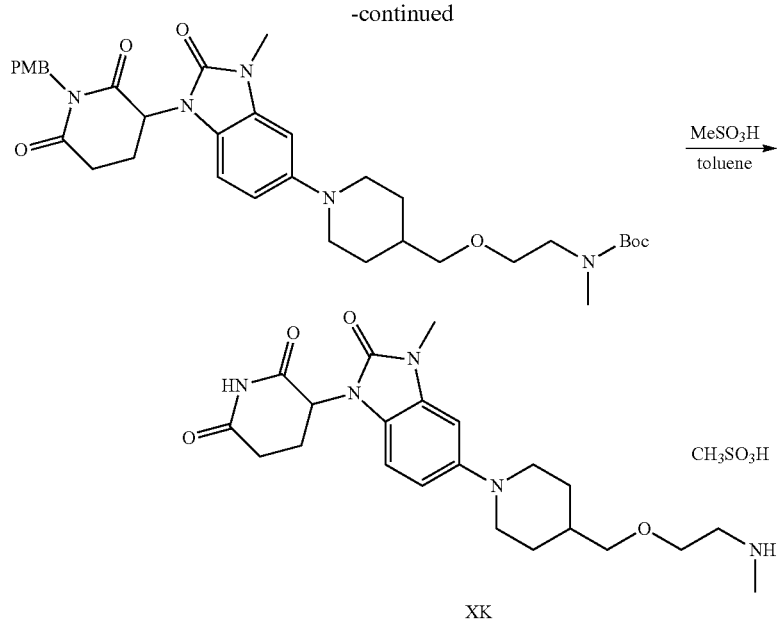

Step 1—Tert-butyl N-methyl-N-[2-[[1-[3-(methylamino)-4-nitro-phenyl]-4-piperidyl] methoxy] ethyl] carbamate To a solution of tert-butyl N-methyl-N-[2-(4-piperidylmethoxy)ethyl]carbamate (3.30 g, 12.1 mmol, Intermediate XJ) in DMF (30 mL) was added 5-fluoro-N-methyl-2-nitroaniline (2.06 g, 12.1 mmol) and K$_2$CO$_3$ (5.02 g, 36.4 mmol). Then the mixture was stirred at 80° C. for 12 hours. On completion, the reaction mixture was diluted with H$_2$O (50 mL) and extracted with ethyl acetate (3×100 mL). The organic layers were washed with brine (3×50 mL). Then the organic layer was dried over anhydrous Na$_2$SO$_4$, filtered and concentrated in vacuo to give a residue. The residue was purified by column chromatography to give the title compound (4.40 g, 85% yield) as orange oil. LC-MS (ESI$^+$) m/z 423.5 (M+H)$^+$.

Step 2—Tert-butyl (2-((1-(4-amino-3-(methylamino)phenyl)piperidin-4-yl)methoxy)ethyl) (methyl)carbamate To a solution of tert-butyl N-methyl-N-[2-[[1-[3-(methylamino)-4-nitro-phenyl]-4-piperidyl] methoxy]ethyl]carbamate (3.6 g, 8.52 mmol) in MeOH (100 mL) was added Pd/C (0.7 g, 10 wt %) under N$_2$. The suspension was degassed in vacuo and purged with H$_2$ three times. The mixture was stirred under H$_2$ (15 Psi) at 25° C. for 4 hours. On completion, the reaction mixture was filtered and concentrated in vacuo to give the title compound (3.2 g, 97% yield) as brown oil. $^1$H NMR (400 MHz, CDCl$_3$) δ 6.63 (d, J=8.2 Hz, 1H), 6.34 (d, J=2.4 Hz, 1H), 6.28 (dd, J=2.6, 8.2 Hz, 1H), 3.52 (d, J=12.0 Hz, 4H), 3.45-3.31 (m, 4H), 2.93 (s, 3H), 2.86 (s, 3H), 2.62 (dt, J=2.0, 11.6 Hz, 2H), 1.83 (d, J=12.6 Hz, 2H), 1.73-1.60 (m, 1H), 1.49-1.40 (m, 11H); LC-MS (ESI$^+$) m/z 393.2 (M+H)$^+$.

Step 3—Tert-butyl (2-((1-(4-amino-3-(methylamino)phenyl)piperidin-4-yl)methoxy)ethyl) (methyl)carbamate To a mixture of tert-butyl N-[2-[[1-[4-amino-3-(methylamino)phenyl]-4-piperidyl]methoxy] ethyl]-N-methyl-carbamate (1.5 g, 3.82 mmol) in MeCN (30 mL) was added CDI (1.24 g, 7.64 mmol) under N$_2$. The mixture was stirred for at 85° C. 16 hours. On completion, the reaction mixture was concentrated in vacuo to remove THF. The residue was diluted with water (20 mL) and extracted with EA (3×20 mL). The combined organic layers was dried over Na$_2$SO$_4$, filtered and concentrated in vacuo to give a residue. The residue was purified by reverse phase (FA condition) to give the title compound (1.10 g, 69% yield) as a purple solid. $^1$H NMR (400 MHz, CDCl$_3$) δ 9.06 (s, 1H), 6.95 (d, J=8.4 Hz, 1H), 6.74-6.69 (m, 1H), 6.62 (d, J=2.2 Hz, 1H), 3.60-3.52 (m, 4H), 3.39 (s, 3H), 3.37-3.31 (m, 2H), 2.93 (s, 3H), 2.73-2.65 (m, 2H), 1.86 (d, J=11.8 Hz, 2H), 1.77-1.67 (m, 2H), 1.47-1.33 (m, 13H; LC-MS (ESI$^+$) m/z 419.2 (M+H)$^+$.

Step 4—Tert-butyl (2-((1-(4-amino-3-(methylamino)phenyl)piperidin-4-yl)methoxy)ethyl) (methyl)carbamate To a mixture of tert-butyl N-methyl-N-[2-[[1-(3-methyl-2-oxo-1H-benzimidazol-5-yl)-4-piperidyl]methoxy]ethyl] carbamate (1.10 g, 2.63 mmol) in THF (20 mL) was added t-BuOK (442 mg, 3.94 mmol) at 0° C. under N$_2$. Then a solution of [1-[(4-methoxyphenyl)methyl]-2,6-dioxo-3-piperidyl] trifluoromethanesulfonate (1.50 g, 3.94 mmol) in THF (20 mL) was added dropwise at 0° C. The mixture was warmed slowly to 25° C. and stirred at 25° C. for 24 hours. On completion, the reaction mixture was quenched by addition water (10 mL) at 25° C., and then extracted with EA (3×20 mL). The combined organic layers, dried over Na$_2$SO$_4$, filtered and concentrated in vacuo to give a residue. The residue was purified by column chromatography to give the title compound (800 mg, 24% yield) as brown oil. LC-MS (ESI$^+$) m/z 650.2 (M+H)$^+$.

Step 5—3-(3-methyl-5-(4-((2-(methylamino)ethoxy)methyl)piperidin-1-yl)-2-oxo-2,3-dihydro-1H-benzo[d]imidazol-1-yl)piperidine-2,6-dione methanesulfonate To a mixture of tert-butyl N-[2-[[1-[1-[1-[(4-methoxyphenyl)methyl]-2,6-dioxo-3-piperidyl]-3-methyl-2-oxo-benzimidazol-5-yl]-4-piperidyl]methoxy]ethyl]-N-methyl-carbamate (500 mg, 769 umol) in toluene (10 mL) was added CH$_3$SO$_3$H (2.22 g, 23.1 mmol) at 25° C. The mixture was stirred at 120° C. for 3 hours. On completion, the reaction mixture was quenched by addition water (2 mL) at 25° C., and then neutralized by adding NEt$_3$ to pH=5. Then the mixture was filtered and concentrated in vacuo to give a residue. The residue was purified by reverse phase (FA condition) to give the title compound (100 mg, 25% yield, CH$_3$SO$_3$H) as yellow oil. LC-MS (ESI$^+$) m/z 430.1 (M+H)$^+$.

Tert-butyl 4-(2-prop-2-ynoxyethyl)piperazine-1-carboxylate (Intermediate XL)

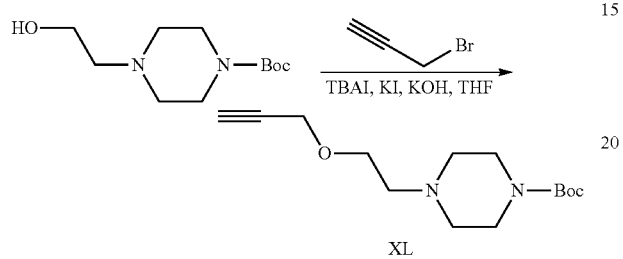

A mixture of tert-butyl 4-(2-hydroxyethyl)piperazine-1-carboxylate (5.00 g, 21.7 mmol, CAS #77279-24-4), 3-bromoprop-1-yne (2.58 g, 21.7 mmol, CAS #106-96-7) in THF (35 mL) was added TBAI (802 mg, 2.17 mmol), KI (541 mg, 3.26 mmol) and KOH (1.22 g, 21.7 mmol). The mixture was stirred at 25° C. for 12 hrs under N$_2$ atmosphere. On completion, the reaction mixture was diluted with water (2×100 mL) and extracted with ethyl acetate (3×100 mL). The combined organic layers were washed with brine, dried over anhydrous sodium sulfate, filtered and concentrated under reduced pressure to give a residue. The residue was purified by column chromatography (SiO$_2$, PE:EA=10:1 to 3:1) to give the title compound (1.30 g, 18% yield) as yellow oil. $^1$H NMR (400 MHz, DMSO-d$_6$) δ 4.12 (d, J=2.4 Hz, 2H), 3.54 (t, J=5.6 Hz, 2H), 3.41 (s, 1H), 3.30-3.26 (m, 4H), 2.49-2.47 (m, 2H), 2.36-2.33 (m, 4H), 1.39 (s, 9H).

3-[3-Methyl-2-oxo-4-[3-(2-piperazin-1-ylethoxy) propyl]benzimidazol-1-yl]piperidine-2,6-dione (Intermediate XM)

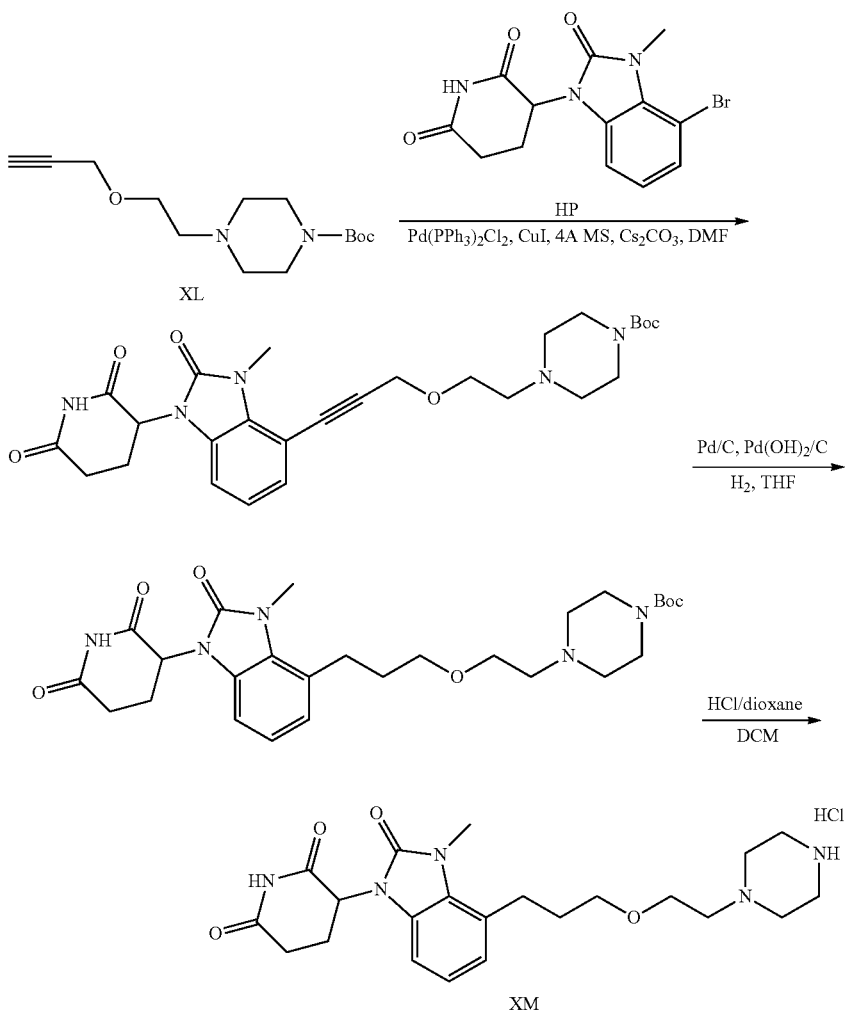

Step 1—Tert-butyl 4-[2-[3-[1-(2,6-dioxo-3-piperidyl)-3-methyl-2-oxo-benzimidazol-4-yl]prop-2-ynoxy] ethyl]piperazine-1-carboxylate A mixture of tert-butyl 4-(2-prop-2-ynoxyethyl)piperazine-1-carboxylate (476 mg, 1.77 mmol, Intermediate XL), 3-(4-bromo-3-methyl-2-oxo-benzimidazol-1-yl)piperidine-2,6-dione (300 mg, 887 umol, Intermediate HP), Cs$_2$CO$_3$ (1.45 g, 4.44 mmol), 4 Å molecular sieves (50 mg), Pd(PPh$_3$)$_2$Cl$_2$ (124 mg, 177 umol) and CuI (33.8 mg, 177 umol) in DMF (8 mL) under N$_2$ atmosphere. The mixture was de-gassed and then heated at 80° C. for 2 hrs. On completion, the reaction mixture was concentrated in vacuo. The crude product was purified by reversed-phase HPLC (0.1% FA condition) to give the title compound (400 mg, 77% yield) as brown oil. $^1$H NMR (400 MHz, DMSO-d$_6$) δ 11.12 (s, 1H), 7.19 (d, J=7.2 Hz, 1H), 7.13 (d, J=7.6 Hz, 1H), 7.06-6.94 (m, 1H), 5.41 (dd, J=4.8, 12.4 Hz, 1H), 4.47 (s, 2H), 3.74 (s, 2H), 3.64 (s, 3H), 3.56-3.52 (m, 4H), 2.94-2.89 (m, 1H), 2.85-2.71 (m, 4H), 2.63-2.58 (m, 4H), 2.09-1.97 (m, 1H), 1.39 (s, 9H); LC-MS (ESI$^+$) m/z 526.3 (M+H)$^+$.

Step 2—Tert-butyl 4-[2-[3-[1-(2,6-dioxo-3-piperidyl)-3-methyl-2-oxo-benzimidazol-4-yl]propoxy] ethyl piperazine-1-carboxylate To a solution of tert-butyl 4-[2-[3-[1-(2,6-dioxo-3-piperidyl)-3-methyl-2-oxo-benzimidazol-4-yl]prop-2-ynoxy] ethyl]piperazine-1-carboxylate (400 mg, 679 umol) in THF (20 mL) was added Pd/C (50.0 mg, 10 wt %) and Pd(OH)$_2$ (50.0 mg) under N$_2$ atmosphere. The mixture was stirred at 25° C. for 12 hrs under H$_2$ (15 Psi). On completion, the reaction mixture was concentrated in vacuo. The product was filtered under reduced pressure to give the title compound (395 mg, 99% yield) as brown solid. $^1$H NMR (400 MHz, DMSO-d$_6$) δ 11.08 (s, 1H), 6.97 (d, J=5.2 Hz, 2H), 6.90-6.85 (m, 1H), 5.37 (dd, J=5.2, 12.4 Hz, 1H), 4.26 (t, J=7.2 Hz, 1H), 4.15 (t, J=6.5 Hz, 1H), 3.69-3.62 (m, 2H), 3.56 (s, 3H), 3.50-3.45 (m, 4H), 2.98-2.95 (m, 2H), 2.75-2.71 (m, 2H), 2.69-2.66 (m, 2H), 2.65-2.59 (m, 4H), 2.19-2.13 (m, 1H), 1.88-1.82 (m, 2H), 1.77-1.71 (m, 1H), 1.40 (s, 9H). LC-MS (ESI$^+$) m/z 530.3 (M+H)$^+$.

Step 3—3-[3-Methyl-2-oxo-4-[3-(2-piperazin-1-ylethoxy)propyl]benzimidazol-1-yl]piperidine-2,6-dione To a solution of tert-butyl 4-[2-[3-[1-(2,6-dioxo-3-piperidyl)-3-methyl-2-oxo-benzimidazol-4-yl]propoxy]ethyl] piperazine-1-carboxylate (100 mg, 189 umol) in DCM (4 mL) was added HCl/dioxane (2 mL). The mixture was stirred at 25° C. for 2 hrs. On completion, the reaction mixture was concentrated in vacuo to give the title compound (87 mg, 58% yield, HCl) as brown solid. LC-MS (ESI$^+$) m/z 430.3 (M+H)$^+$.

Tert-butyl N-isopropyl-N-(3-prop-2-ynoxypropyl) carbamate (Intermediate XN)

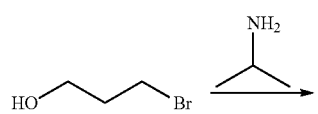

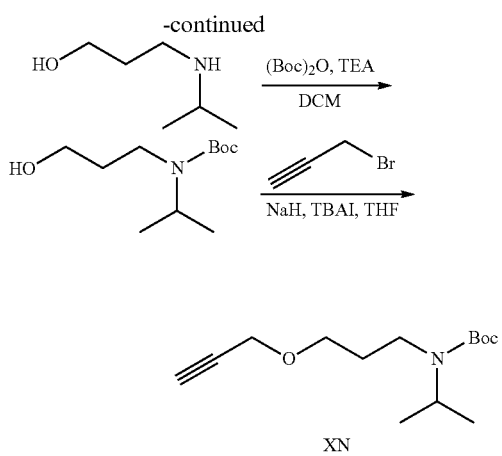

Step 1—3-(Isopropylamino)propan-1-ol

A solution of 3-bromopropan-1-ol (5.00 g, 36.0 mmol) in propan-2-amine (6.19 g, 105 mmol) was stirred at 50° C. for 12 hours. On completion, the mixture was concentrated to give the title compound (7.00 g, 90% yield, 50% purity) as colorless oil. $^1$H NMR (400 MHz, CDCl$_3$) δ 3.84 (t, J=5.6 Hz, 2H), 3.40-3.33 (m, 1H), 3.12 (t, J=6.4 Hz, 2H), 2.11-1.99 (m, 2H), 1.39 (d, J=6.6 Hz, 6H).

Step 2—Tert-butyl N-(3-hydroxypropyl)-N-isopropyl-carbamate

To a solution of 3-(isopropylamino)propan-1-ol (7.00 g, 30.0 mmol, 50% purity) in DCM (10 mL) was added (Boc)$_2$O (13.0 g, 59.7 mmol, 13.7 mL) and Et$_3$N (8.00 g, 79.0 mmol) at 15° C. The mixture was stirred at 15° C. for 6 hours. On completion, the mixture was concentrated in vacuo. The residue was purified by flash silica gel chromatography to give the title compound (3.60 g, 50% yield) as yellow oil. $^1$H NMR (400 MHz, CDCl$_3$) δ 3.58 (m, 2H), 3.35 (m, 2H), 1.67 (m, 2H), 1.48 (s, 9H), 1.16 (d, J=6.8 Hz, 6H), 0.91-0.86 (m, 1H).

Step 3—Tert-butyl N-isopropyl-N-(3-prop-2-ynoxypropyl)carbamate

To a solution of tert-butyl N-(3-hydroxypropyl)-N-isopropyl-carbamate (3.40 g, 15.7 mmol) and TBAI (57.8 mg, 156 umol) in THF (100 mL) was added NaH (750 mg, 18.7 mmol, 60% dispersion in oil) at 0° C. The mixture was stirred at 0° C. for 0.5 hour. 3-bromoprop-1-yne (2.79 g, 23.5 mmol) was added at 0° C. The mixture was stirred at 0-15° C. for 6 hours. On completion, the reaction mixture was quenched with sat. aq. NH$_4$Cl (30 mL) at 0° C. The mixture was extracted with EA (3×100 mL). The combined organic layers were washed with brine (100 ml), dried over Na$_2$SO$_4$, filtered and concentrated in vacuo. The residue was purified by flash silica gel chromatography to give the title compound (3.50 g, 80% yield) as yellow oil. $^1$H NMR (400 MHz, CDCl$_3$) δ 4.13 (d, J=2.4 Hz, 2H), 3.53 (t, J=6.4 Hz, 2H), 3.14 (m, 2H), 2.41 (t, J=2.4 Hz, 1H), 1.86-1.77 (m, 2H), 1.46 (s, 9H), 1.12 (d, J=6.8 Hz, 6H), 0.90-0.80 (m, 1H).

3-[4-[3-[3-(Isopropylamino)propoxy]propyl]-3-methyl-2-oxo-benzimidazol-1-yl]piperidine-2,6-dione (Intermediate XO)

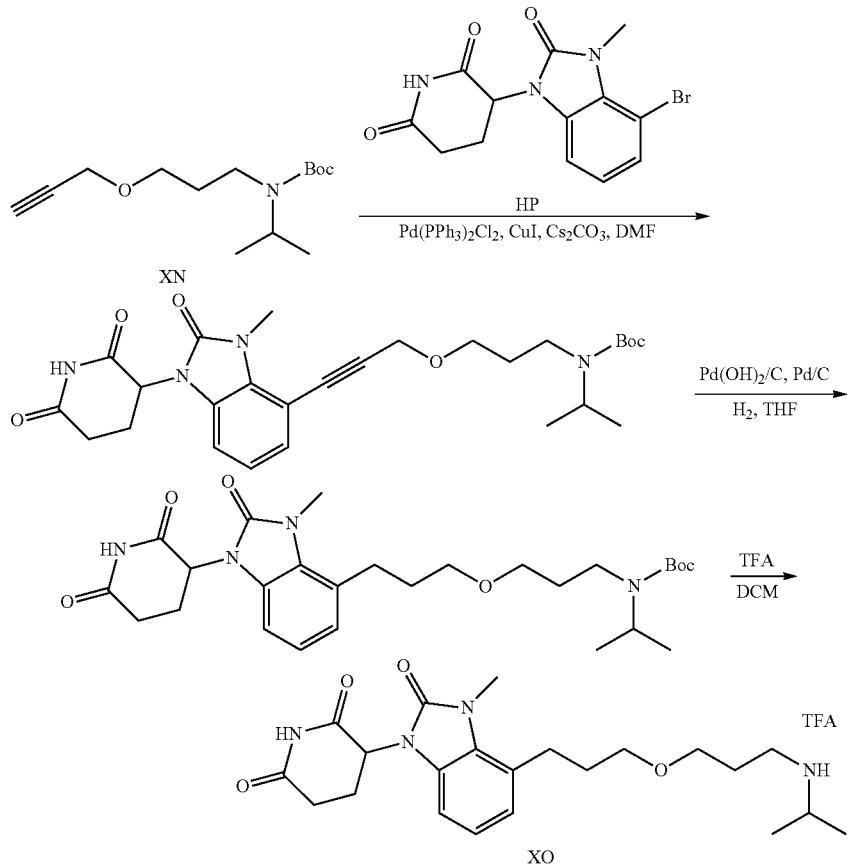

Step 1—Tert-butyl N-[3-[3-[1-(2,6-dioxo-3-piperidyl)-3-methyl-2-oxo-benzimidazol-4-yl]prop-2-ynoxy]propyl]-N-isopropyl-carbamate To a solution of tert-butyl N-isopropyl-N-(3-prop-2-ynoxypropyl)carbamate (755 mg, 2.96 mmol, Intermediate XN) and 3-(4-bromo-3-methyl-2-oxo-benzimidazol-1-yl)piperidine-2,6-dione (400 mg, 1.18 mmol, Intermediate HP) in DMF (10 mL) was added Pd(dppf)Cl$_2$ (173 mg, 237 umol) and Cs$_2$CO$_3$ (1.54 g, 4.73 mmol) and CuI (45.1 mg, 237 umol) at 20° C. The mixture was stirred at 80° C. for 2 hours under N$_2$. On completion, the mixture was filtered through celite and the filtrate was concentrated in vacuo. The residue was purified by reversed-phase HPLC (FA condition) to give the title compound (350 mg, 55% yield) as yellow solid. $^1$H NMR (400 MHz, DMSO-d$_6$) δ 11.14 (s, 1H), 7.18 (d, J=7.6 Hz, 1H), 7.14-7.10 (m, 1H), 7.08-6.99 (m, 1H), 5.43-5.38 (m, 1H), 4.44 (s, 2H), 3.09 (m, 2H), 2.95-2.84 (m, 1H), 2.09-1.97 (m, 1H), 1.82-1.69 (m, 2H), 1.38 (s, 9H), 1.08 (d, J=6.0 Hz, 6H).

Step 2—Tert-butyl N-[3-[3-[1-(2,6-dioxo-3-piperidyl)-3-methyl-2-oxo-benzimidazol-4-yl]propoxy]propyl]-N-isopropyl-carbamate To a solution of tert-butyl N-[3-[3-[1-(2,6-dioxo-3-piperidyl)-3-methyl-2-oxo-benzimidazol-4-yl] prop-2-ynoxy]propyl]-N-isopropyl-carbamate (350 mg, 683 umol) in THF (20 mL) was added Pd(OH)$_2$/C (350 mg, 683 umol, 10 wt %) and Pd/C (350 mg, 682 umol, 10 wt %). The mixture was stirred at 15° C. for 2 hours. On completion, the mixture was filtered with celite and the filtrate was concentrated in vacuo to give the title compound (350 mg, 99% yield) as yellow oil. LC-MS (ESI$^+$) m/z 539.4 (M+23)$^+$

Step 3—3-[4-[3-[3-(Isopropylamino)propoxy]propyl]-3-methyl-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-4-yl] propoxy]propyl]-N-isopropyl-carbamate (320 mg, 619 umol) in DCM (4 mL) was added TFA (10.7 mL) at 15° C. The mixture was stirred at 15° C. for 0.5 hour. On completion, the mixture was concentrated in vacuo to give the title compound (320 mg, 97% yield, TFA salt) as yellow oil. LC-MS (ESI$^+$) m/z 417.3 (M+H)$^+$.

1505

Tert-butyl N-cyclopropyl-N-(3-prop-2-ynoxypropyl) carbamate (Intermediate XP)

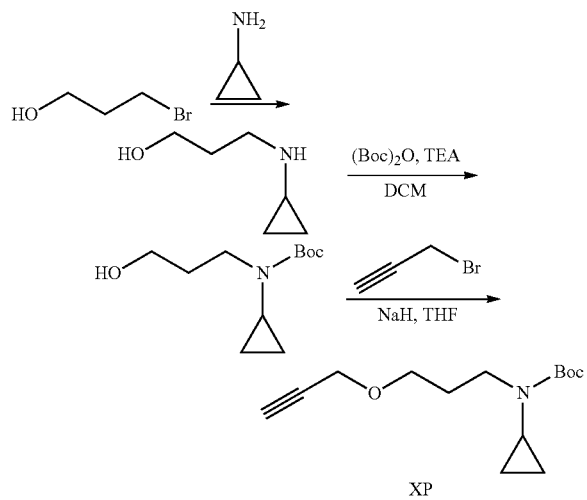

Step 1—3-(Cyclopropylamino)propan-1-ol

A mixture of 3-bromopropan-1-ol (5.00 g, 35.9 mmol, 3.25 mL, CAS #627-18-9) in cyclopropanamine (10.2 g, 179 mmol, 12.4 mL, CAS #765-30-0) was stirred at 50° C. for 12 hours. On completion, the reaction mixture was concentrated in vacuo to give the title compound (4.00 g, 96% yield) as light yellow oil. $^1$H NMR (400 MHz, DMSO-$d_6$) δ 3.45 (t, J=6.0 Hz, 2H), 3.01 (t, J=7.6 Hz, 2H), 2.75-2.68 (m, 1H), 1.81-1.73 (m, 2H), 0.88-0.82 (m, 2H), 0.74-0.70 (m, 2H).

1506

Step 2—Tert-butyl N-cyclopropyl-N-(3-hydroxypropyl)carbamate

To a mixture of 3-(cyclopropylamino)propan-1-ol (4.00 g, 34.7 mmol) in DCM (60 mL) was added TEA (10.5 g, 104 mmol, 14.5 mL) and Boc$_2$O (15.1 g, 69.4 mmol, 15.9 mL). The reaction mixture was stirred at 25° C. for 12 hours. On completion, the reaction mixture was diluted with water (30 mL) and extracted with EA (3×50 mL). The combined organic layers was dried over Na$_2$SO$_4$, filtered and concentrated in vacuo to give a residue. The residue was purified by column chromatography to give the title compound (3.70 g, 49% yield) as light yellow oil. $^1$H NMR (400 MHz, CDCl$_3$) δ 3.54 (d, J=5.0 Hz, 2H), 3.36 (t, J=6.0 Hz, 2H), 2.49-2.41 (m, 1H), 1.74-1.65 (m, 2H), 1.45 (s, 9H), 0.75-0.68 (m, 2H), 0.62-0.55 (m, 2H).

Step 3—Tert-butyl N-cyclopropyl-N-(3-prop-2-ynoxypropyl)carbamate

To a mixture of tert-butyl N-cyclopropyl-N-(3-hydroxypropyl)carbamate (3.20 g, 14.8 mmol) in THF (30 mL) was added NaH (1.19 g, 29.7 mmol, 60% dispersion in oil) at 0° C. for 0.5 hour. Then 3-bromoprop-1-yne (3.54 g, 29.7 mmol, 2.56 mL) was added to the mixture. The reaction mixture was stirred at 25° C. for 12 hours. On completion, the reaction mixture was quenched with sat. NH$_4$Cl solution (10 mL) under stirring. The mixture was diluted with water (30 mL) and extracted with EA (3×50 mL). The combined organic layers was dried over Na$_2$SO$_4$, filtered and concentrated in vacuo to give the title compound (3.70 g, 98% yield) as light yellow oil. $^1$H NMR (400 MHz, CDCl$_3$) δ 4.13 (d, J=2.4 Hz, 2H), 3.53 (t, J=6.4 Hz, 2H), 3.32-3.25 (m, 2H), 2.54-2.46 (m, 1H), 2.41 (t, J=2.4 Hz, 1H), 1.89-1.81 (m, 2H), 1.45 (s, 9H), 0.75-0.70 (m, 2H), 0.61-0.57 (m, 2H).

3-[4-[3-[3-(Cyclopropylamino)propoxy]propyl]-3-methyl-2-oxo-benzimidazol-1-yl]piperidine-2,6-dione (Intermediate XQ)

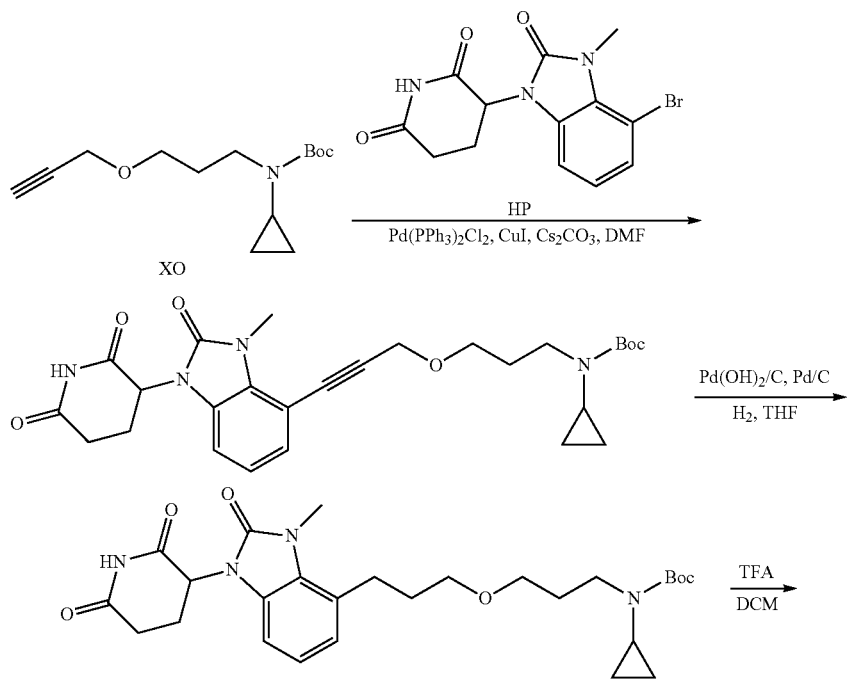

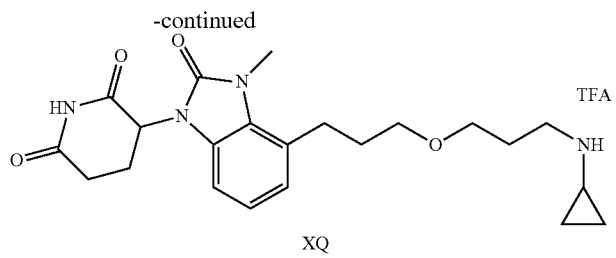

XQ

Step 1—Tert-butyl N-cyclopropyl-N-[3-[3-[1-(2,6-dioxo-3-piperidyl)-3-methyl-2-oxo-benzimidazol-4-yl]prop-2-ynoxy]propyl]carbamate To a mixture of tert-butyl N-cyclopropyl-N-(3-prop-2-ynoxypropyl)carbamate (599 mg, 2.37 mmol, Intermediate XP) and 3-(4-bromo-3-methyl-2-oxo-benzimidazol-1-yl)piperidine-2,6-dione (400 mg, 1.18 mmol, Intermediate HP) in DMF (5 mL) was added CuI (22.5 mg, 118 umol), Cs$_2$CO$_3$ (1.93 g, 5.91 mmol), Pd(PPh$_3$)$_2$Cl$_2$ (83.0 mg, 118 umol) and 4 Å molecular sieves (10 mg). The reaction mixture was stirred at 80° C. for 2 hours under N$_2$ atmosphere. On completion, the reaction mixture was filtered and concentrated in vacuo. The residue was purified by reverse phase (0.1% FA condition) to give the title compound (240 mg, 39% yield) as brown solid. $^1$H NMR (400 MHz, DMSO-d$_6$) δ 11.14 (s, 1H), 7.18 (d, J=7.6 Hz, 1H), 7.13-7.09 (m, 1H), 7.05-7.00 (m, 1H), 5.43-5.37 (m, 1H), 4.43 (s, 2H), 3.64 (s, 3H), 3.53 (t, J=6.3 Hz, 2H), 3.44-3.37 (m, 2H), 3.21 (t, J=7.2 Hz, 2H), 2.94-2.83 (m, 1H), 2.75-2.55 (m, 3H), 2.07-1.98 (m, 1H), 1.80-1.70 (m, 2H), 1.39 (s, 2H), 1.37 (s, 9H), 0.70-0.63 (m, 2H), 0.57-0.49 (m, 2H).

Step 2—Tert-butyl N-cyclopropyl-N-[3-[3-[1-(2,6-dioxo-3-piperidyl)-3-methyl-2-oxo-benzimidazol-4-yl]propoxy]propyl]carbamate To a mixture of tert-butyl N-cyclopropyl-N-[3-[3-[1-(2,6-dioxo-3-piperidyl)-3-methyl-2-oxo-benzimidazol-4-yl]prop-2-ynoxy]propyl]carbamate (180 mg, 352 umol) in THF (20 mL) was added Pd(OH)$_2$/C (30.0 mg, 10 wt %) and Pd/C (30.0 mg, 10 wt %). The reaction mixture was stirred at 25° C. for 2.5 hours under H$_2$ (15 Psi) atmosphere. On completion, the reaction mixture was filtered and concentrated in vacuo to give the title compound (181 mg, 99% yield) as light yellow solid. The residue was used to the next step directly without further purification. $^1$H NMR (400 MHz, DMSO-d$_6$) δ 11.09 (s, 1H), 6.96 (d, J=4.4 Hz, 2H), 6.89-6.84 (m, 1H), 5.39-5.33 (m, 1H), 3.56 (s, 3H), 3.41 (d, J=6.0 Hz, 2H), 3.38 (t, J=6.0 Hz, 2H), 3.21 (t, J=7.2 Hz, 2H), 2.99-2.93 (m, 2H), 2.91-2.84 (m, 1H), 2.72-2.62 (m, 3H), 2.02-1.99 (m, 1H), 1.85-1.79 (m, 2H), 1.77-1.70 (m, 2H), 1.38 (s, 9H), 0.70-0.64 (m, 2H), 0.56-0.50 (m, 2H).

Step 3—3-[4-[3-[3-(Cyclopropylamino)propoxy]propyl]-3-methyl-2-oxo-benzimidazol-1-yl]piperidine-2,6-dione To a mixture of tert-butyl N-cyclopropyl-N-[3-[3-[1-(2,6-dioxo-3-piperidyl)-3-methyl-2-oxo-benzimidazol-4-yl]propoxy]propyl]carbamate (190 mg, 369 umol) in DCM (1 mL) was added TFA (4.62 g, 40.5 mmol, 3.00 mL). The reaction mixture was stirred at 25° C. for 1 hour. On completion, the reaction mixture was concentrated in vacuo to give the title compound (195 mg, 99% yield, TFA salt) as red oil. LC-MS (ESI$^+$) m/z 415.3 (M+H)$^+$.

N-[3-(difluoromethyl)-1-(4-formylcyclohexyl)pyrazol-4-yl]-2-(4-pyridyl)oxazole-4-carboxamide (Intermediate XR)

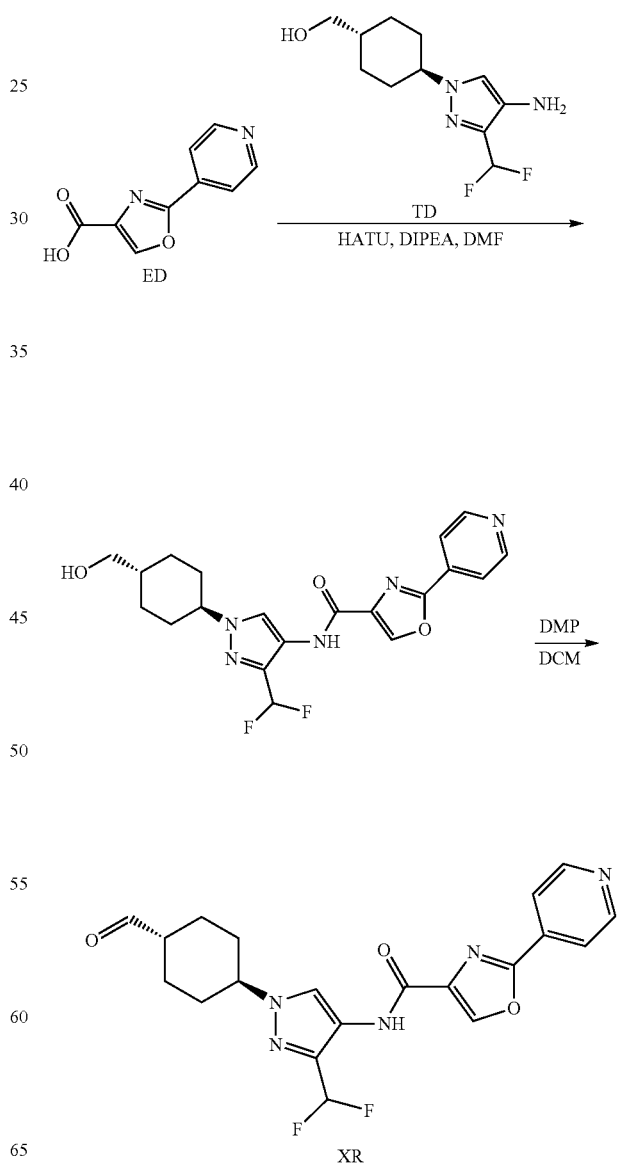

XR

1509

Step 2—N-3-(difluoromethyl)-1-(4-formylcyclohexyl)pyrazol-4-yl]-2-(4-pyridyl)oxazole-4-carboxamide

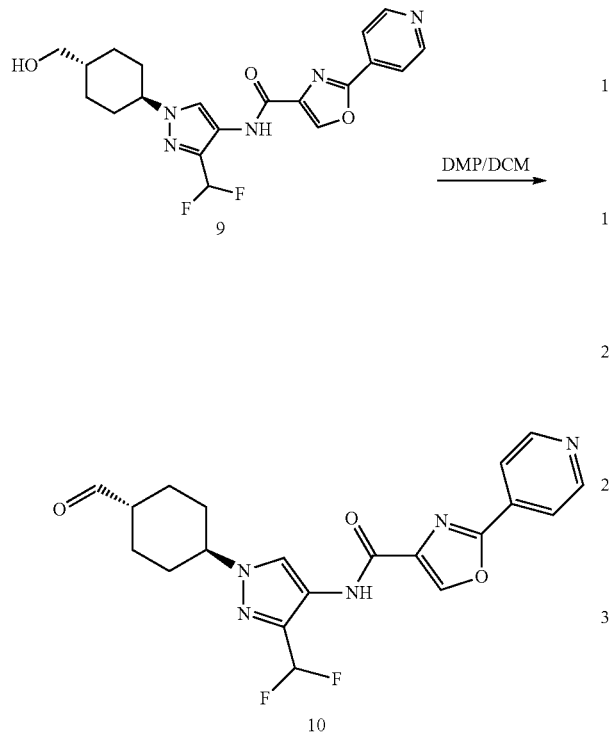

To a mixture of N-[3-(difluoromethyl)-1-[4-(hydroxymethyl)cyclohexyl]pyrazol-4-yl]-2-(4-pyridyl) oxazole-4-carboxamide (120 mg, 287 umol) in DCM (15 mL) was added DMP (146 mg, 344 umol, 106 uL) at 0° C. The reaction mixture was stirred at 25° C. for 72 hours. On compound, the reaction mixture was quenched by saturated $Na_2S_2O_3$ (20 mL) and saturated $NaHCO_3$ (20 mL) at 25° C., and then stirred for 30 minutes. The solution was diluted with water (20 mL) and extracted with DCM (3×20 mL). The combined organic layers was dried over $Na_2SO_4$, filtered and concentrated in vacuo to give the title compound (119 mg, 99% yield) as light yellow solid. The residue was used to the next step directly without further purification. LC-MS (ESI$^+$) m/z 416.2 (M+H)$^+$.

Tert-butyl 4-(4-piperidylmethyl)piperidine-1-carboxylate (Intermediate XS)

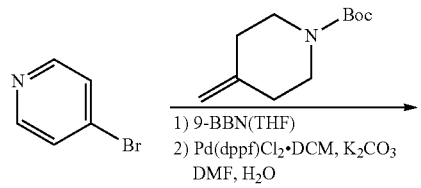

1) 9-BBN(THF)
2) Pd(dppf)Cl$_2$·DCM, K$_2$CO$_3$ DMF, H$_2$O

1510

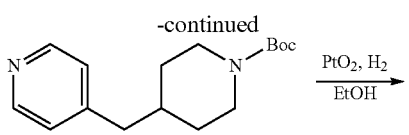

Step 1—Tert-butyl 4-(4-pyridylmethyl)piperidine-1-carboxylate

To a solution of tert-butyl 4-methylenepiperidine-1-carboxylate (6.00 g, 30.4 mmol, CAS #159635-49-1) was added 9-BBN THF solution (0.5 M, 60.5 mL) at 25° C. The reaction mixture was stirred at 80° C. for 1 hour under $N_2$. After cooling to 25° C., 4-bromopyridine (4.33 g, 27.4 mmol, CAS #1120-87-2), $K_2CO_3$ (5.04 g, 36.5 mmol), Pd(dppf)Cl$_2$·CH$_2$Cl$_2$ (683 mg, 836 umol), DMF (50 mL) and $H_2O$ (5 mL) were added to the reaction mixture was added. The reaction mixture was stirred at 60° C. for 3 hours. After cooling to 25° C., another charge of Pd(dppf)Cl$_2$·CH$_2$Cl$_2$ (683 mg, 836 umol) was added to the reaction mixture. The mixture was stirred at 60° C. for 24 hours. On completion, the mixture was cooled to 25° C. and poured into water (60 mL). The pH was adjusted to 11 with 10% aq. NaOH. The mixture was extracted with ethyl acetate (2×100 mL). The combined organic layers were dried over NaSO$_4$, filtered and concentrated in vacuo. The residue was purified by column chromatography to give the title compound (5.80 g, 76% yield) as yellow oil. $^1$H NMR (400 MHz, CDCl$_3$) δ 8.53-8.47 (m, 2H), 7.08 (d, J=6.0 Hz, 2H), 2.64 (t, J=12.0 Hz, 2H), 2.54 (d, J=7.6 Hz, 2H), 1.77-1.64 (m, 2H), 1.63-1.56 (m, 2H), 1.54-1.47 (m, 1H), 1.45 (s, 9H), 1.21-1.09 (m, 2H).

Step 2 Tert-butyl 4-(4-piperidylmethyl)piperidine-1-carboxylate

To a solution of tert-butyl 4-(4-pyridylmethyl)piperidine-1-carboxylate (5.80 g, 20.9 mmol) in EtOH (100 mL) and HOAc (1.26 g, 20.9 mmol) was added PtO$_2$ (1.02 g, 4.48 mmol) at 20° C. The reaction mixture was stirred at 20° C. for 54 hours under $H_2$ (50 Psi). On completion, the reaction mixture was filtered with celite and the filtrate was concentrated in vacuo to give the title compound (4.68 g, 79% yield) as black oil. $^1$H NMR (400 MHz, CDCl$_3$) δ 4.26-4.00 (m, 4H), 3.16 (d, J=9.6 Hz, 2H), 2.70-2.60 (m, 3H), 1.69 (d, J=12.8 Hz, 2H), 1.65-1.56 (m, 2H), 1.54-1.46 (m, 2H), 1.44 (s, 9H), 1.29-1.20 (m, 2H), 1.20-1.13 (m, 2H), 1.11-0.97 (m, 2H); LC-MS (ESI$^+$) m/z 283.0 (M+H)$^+$.

3-[3-methyl-2-oxo-4-[[4-(4-piperidylmethyl)-1-piperidyl]methyl]benzimidazol-1-yl]piperidine-2,6-dione (Intermediate XT)

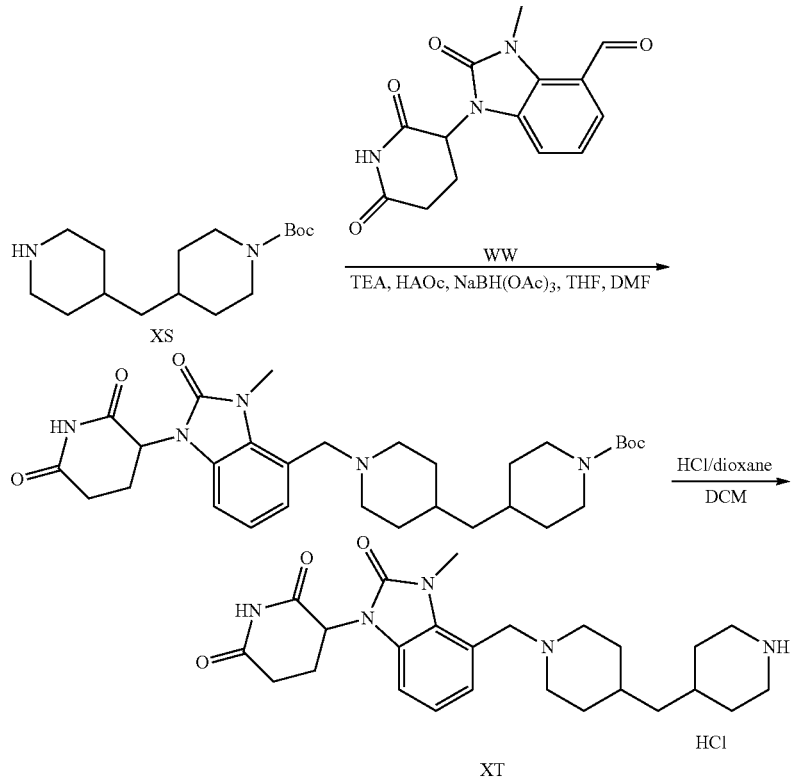

Step 1—Tert-butyl 4-[[1-[[1-(2,6-dioxo-3-piperidyl)-3-methyl-2-oxo-benzimidazol-4-yl]methyl]-4-piperidyl]methyl]piperidine-1-carboxylate To a solution of tert-butyl 4-(4-piperidylmethyl)piperidine-11-carboxylate (128 mg, 452 umol, Intermediate XS) in THF (10 mL) and DMF (5 mL) was added TEA (45.8 mg, 452 umol). The mixture was stirred at 25° C. for 10 minutes. HOAc (27.2 mg, 452 umol) and 1-(2,6-dioxo-3-piperidyl)-3-methyl-2-oxo-benzimidazole-4-carbaldehyde (195 mg, 679 umol, Intermediate WW) were added to the above mixture. The reaction mixture was stirred at 25° C. for 20 minutes. Then NaBH(OAc)$_3$ (192 mg, 905 umol) was added. The reaction mixture was stirred at 25° C. for 16 hours. On completion, the reaction was quenched with H$_2$O (1 mL). The mixture was concentrated in vacuo. The residue was purified by reverse phase (FA condition) to give the title compound (250 mg, 99% yield) as a yellow solid. $^1$H NMR (400 MHz, DMSO-d$_6$) δ 11.09 (s, 1H), 7.19 (d, J=6.4 Hz, 1H), 6.95 (t, J=7.6 Hz, 1H), 6.86 (d, J=7.2 Hz, 1H), 5.36 (d, J=5.6 Hz, 1H), 3.97-3.81 (m, 2H), 3.66 (s, 3H), 3.60 (s, 2H), 2.96-2.83 (m, 2H), 2.83-2.69 (m, 4H), 2.66-2.58 (m, 3H), 2.06-1.89 (m, 4H), 1.58 (d, J=12.4 Hz, 4H), 1.37 (s, 9H), 1.14-0.98 (m, 4H), 0.96-0.81 (m, 2H); LC-MS (ESI$^+$) m/z 554.4 (M+H)$^+$.

Step 2—3-[3-methyl-2-oxo-4-[[4-(4-piperidylmethyl)-1-piperidyl]methyl]benzimidazol-1-yl]piperidine-2,6-dione To a solution of tert-butyl 4-[[1-[[1-(2,6-dioxo-3-piperidyl)-3-methyl-2-oxo-benzimidazol-4-yl]methyl]-4-piperidyl]methyl]piperidine-1-carboxylate (100 mg, 181 umol) in DCM (2 mL) was added 4 M HCl/dioxane (1 mL) at 25° C. The reaction mixture was stirred at 25° C. for 1 hour. On completion, the reaction mixture was concentrated in vacuo. The residue was purified by reverse phase (FA condition) to give the title compound (65.0 mg, 79% yield) as a white solid. LC-MS (ESI$^+$) m/z 454.5 (M+H)$^+$.

3-[7-[3-[2-(2-Aminoethoxy)ethoxy]propyl]pyrido[2,3-b]indol-9-yl]piperidine-2,6-dione (Intermediate XV)

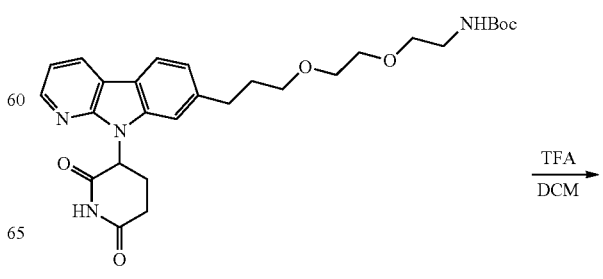

-continued

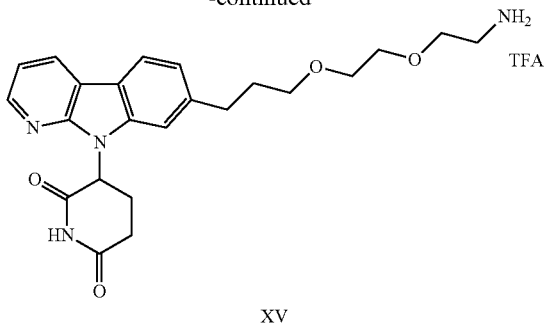

XV

To a solution of tert-butyl N-[2-[2-[3-[9-(2,6-dioxo-3-piperidyl)pyrido[2,3-b]indol-7-yl]propoxy] ethoxy]ethyl] carbamate (95.0 mg, 181 umol) in DCM (3 mL) was added TFA (722 mg, 6.34 mmol). The reaction mixture was stirred at 25° C. for 1 hr. On completion, the reaction mixture was concentrated in vacuo to give the title compound (95 mg, 95% yield, TFA) as light yellow oil. LC-MS (ESI$^+$) m/z 425.2 (M+H)$^+$.

2-[2-(Cyclopropylmethylamino)-4-pyridyl]oxazole-4-carboxylic acid (Intermediate XW)

-continued

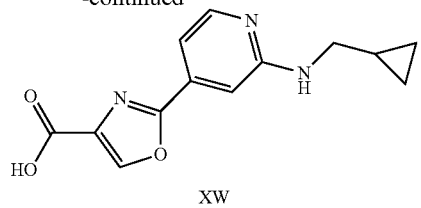

XW

To a mixture of 2-[2-[tert-butoxycarbonyl(cyclopropylmethyl)amino]-4-pyridyl]oxazole-4-carboxylic acid (400 mg, 1.11 mmol, Intermediate OM) in DCM (10 mL) was added TFA (127 mg, 1.11 mmol). The reaction mixture was stirred at 25° C. for 2 hours. On completion, the reaction mixture was concentrated in vacuo to give the title compound (397 mg, 95% yield, TFA salt) as brown oil. LC-MS (ESI$^+$) m/z 260.1 (M+H)$^+$.

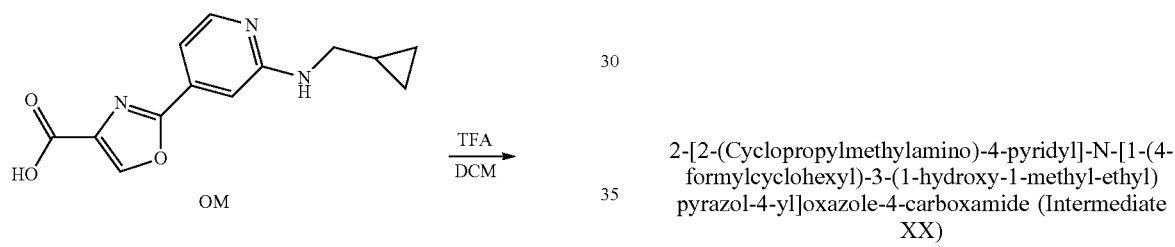

2-[2-(Cyclopropylmethylamino)-4-pyridyl]-N-[1-(4-formylcyclohexyl)-3-(1-hydroxy-1-methyl-ethyl) pyrazol-4-yl]oxazole-4-carboxamide (Intermediate XX)

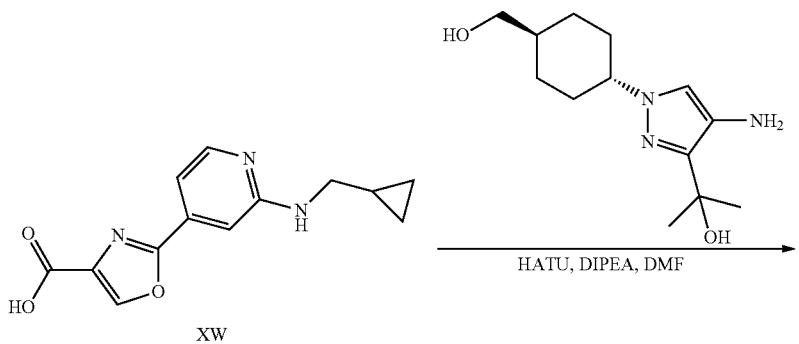

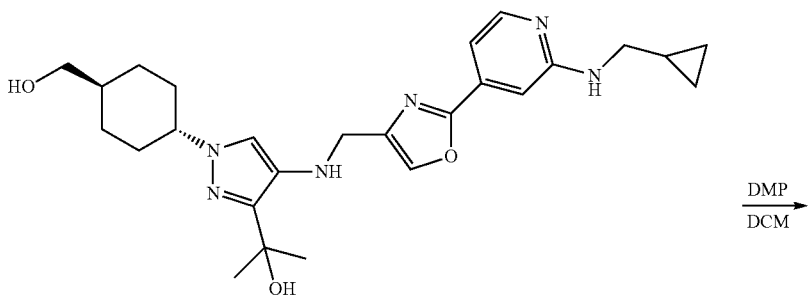

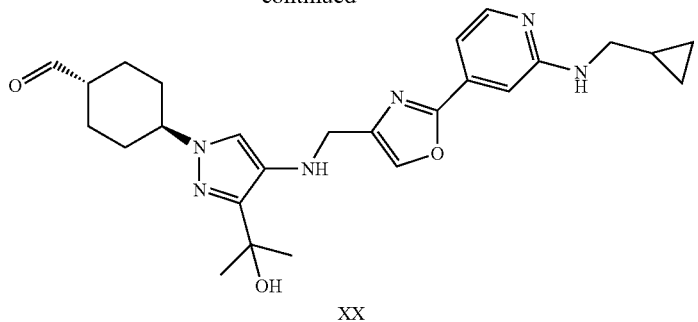

XX

Step 1—2-[2-(Cyclopropylmethylamino)-4-pyridyl]-N-[1-[4-(hydroxymethyl)cyclohexyl]-3-(1-hydroxy-1-methyl-ethyl)pyrazol-4-yl]oxazole-4-carboxamide To a mixture of 2-[4-amino-1-[4-(hydroxymethyl) cyclohexyl] pyrazol-3-yl]propan-2-ol (270 mg, 1.07 mmol, synthesized via Step 1 of Intermediate UW), and 2-[2-(cyclopropylmethylamino)-4-pyridyl]oxazole-4-carboxylic acid (397 mg, 1.07 mmol, TFA salt, Intermediate XW) in DMF (10 mL) was added DIPEA (688 mg, 5.33 mmol). The mixture was stirred at 25° C. for 0.5 hour. Then HATU (445 mg, 1.17 mmol) was added into the mixture. The reaction mixture was stirred at 25° C. for 1 hour. On completion, the reaction was quenched by water (2 mL) and concentrated in vacuo to give residue. The residue was purified by reversed-phase HPLC (0.1% FA condition) to give title compound (380 mg, 72% yield) as a brown solid. $^1$H NMR (300 MHz, DMSO-$d_6$) δ 10.37 (s, 1H), 8.86 (s, 1H), 8.22-8.07 (m, 2H), 7.06 (s, 1H), 6.98 (d, J=1.6, 5.2 Hz, 1H), 5.85 (s, 1H), 4.46 (d, J=5.2 Hz, 1H), 4.11-3.96 (m, 1H), 3.29-3.13 (m, 5H), 2.09-1.97 (m, 2H), 1.85 (d, J=11.6 Hz, 2H), 1.75-1.58 (m, 2H), 1.50 (s, 6H), 1.45-1.35 (m, 1H), 1.16-0.98 (m, 3H), 0.51-0.38 (m, 2H), 0.26-0.17 (m, 2H).

Step 2—2-[2-(Cyclopropylmethylamino)-4-pyridyl]-N-[1-(4-formylcyclohexyl)-3-(1-hydroxy-1-methyl-ethyl)pyrazol-4-yl]oxazole-4-carboxamide To a mixture of 2-[2-(cyclopropylmethylamino)-4-pyridyl]-N-[1-[4-(hydroxymethyl)cyclohexyl]-3-(1-hydroxy-1-methyl-ethyl)pyrazol-4-yl]oxazole-4-carboxamide (270 mg, 546 umol) in DCM (20 mL) was added DMP (277 mg, 655 umol). The reaction mixture was stirred at 25° C. for 2 hours. On completion, the reaction mixture was poured into the water (40 mL) and extracted with DCM (2×20 mL). The combined organic phase was washed with brine (2×20 mL), dried with anhydrous Na$_2$SO$_4$, filtered and concentrated in vacuo to give a residue. The residue was purified by reverse phase (0.1% FA condition) to give the title compound (185 mg, 68% yield) as a white solid. $^1$H NMR (400 MHz, DMSO-$d_6$) δ 10.42-10.33 (m, 1H), 9.62 (s, 1H), 8.90 (s, 1H), 8.14 (d, J=5.6 Hz, 1H), 7.24 (d, J=1.6, 7.6 Hz, 2H), 5.86 (s, 1H), 3.24-3.16 (m, 4H), 2.07 (d, J=11.6 Hz, 4H), 1.86-1.62 (m, 3H), 1.57-1.33 (m, 9H), 1.13-1.03 (m, 1H), 0.52-0.44 (m, 2H), 0.25-0.23 (m, 2H).

3-[4-[3-[2-(2-Aminoethoxy)ethoxy]propyl]pyrido[2,3-b]indol-9-yl]piperidine-2,6-dione (Intermediate XZ)

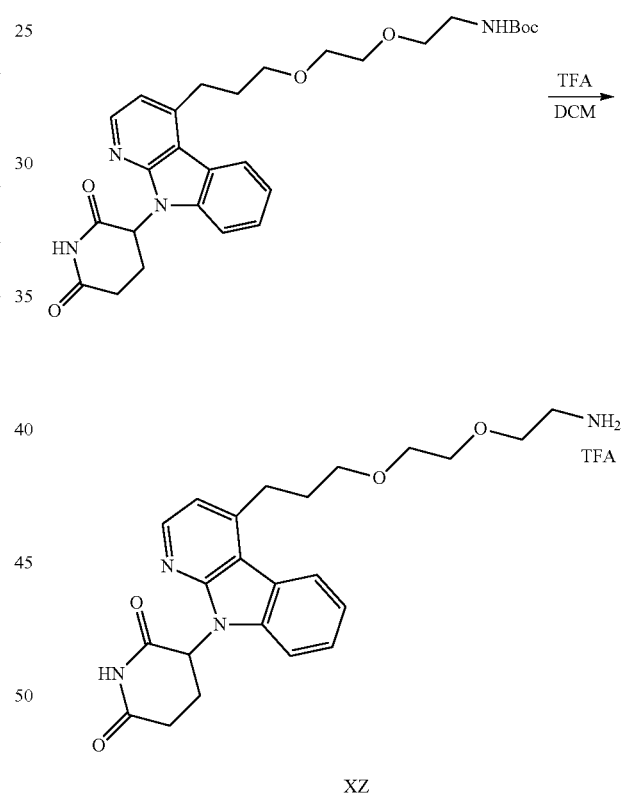

XZ

Step 1—3-[4-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-4-yl]propoxy] ethoxy]ethyl] carbamate (66.0 mg, 125 umol, Intermediate XY) in DCM (2 mL) was added TFA (573 mg, 5.03 mmol). The mixture was stirred at 25° C. for 2 hrs. On completion, the mixture was concentrated in vacuo to give the title compound (67.0 mg, 95% yield, TFA) as light yellow oil. LC-MS (ESI$^+$) m/z 425.0 (M+H)$^+$.

1517

Tert-butyl 3-(prop-2-ynoxymethyl)azetidine-1-carboxylate (Intermediate YA)

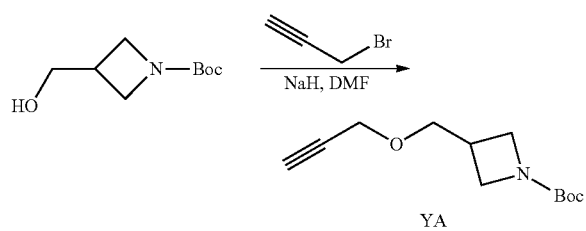

To a solution of tert-butyl 3-(hydroxymethyl)azetidine-1-carboxylate (2.00 g, 10.7 mmol, CAS #142253-56-3) in DMF (20 mL) was added NaH (641 mg, 16.0 mmol, 60% oil dispersion) at 0° C. Thirty minutes later, 3-bromoprop-1-yne (1.40 g, 11.8 mmol, 1.01 mL, CAS #106-96-7) was added and the reaction mixture was stirred at 25° C. for 12 hrs. On completion, the mixture was quenched with water (50 mL), then extracted with EA (2×30 mL). The combined organic layer was washed with brine (50 mL), dried over anhydrous sodium sulfate, filtered and concentrated in vacuo. The residue was purified by silica gel chromatography (SiO$_2$, PE:EA=15:1) to give the title compound (0.60 g, 25% yield) as yellow oil. $^1$H NMR (400 MHz, CDCl$_3$) δ 4.17 (d, J=2.4 Hz, 2H), 4.00 (t, J=8.4 Hz, 2H), 3.71-3.64 (m, 4H), 2.87-2.69 (m, 1H), 2.45 (t, J=2.4 Hz, 1H), 1.44 (s, 9H).

3-[4-[3-(Azetidin-3-ylmethoxy)propyl]-3-methyl-2-oxo-benzimidazol-1-yl]piperidine-2,6-dione (Intermediate YB)

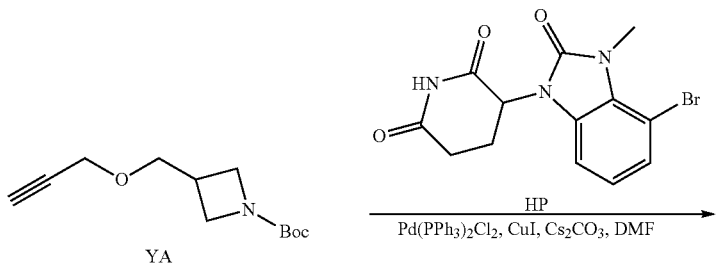

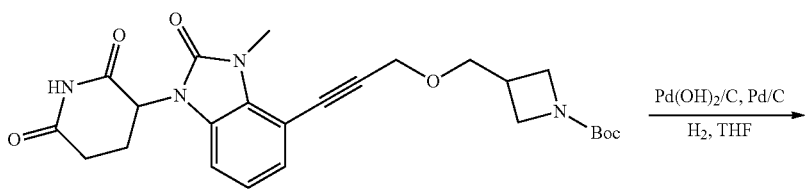

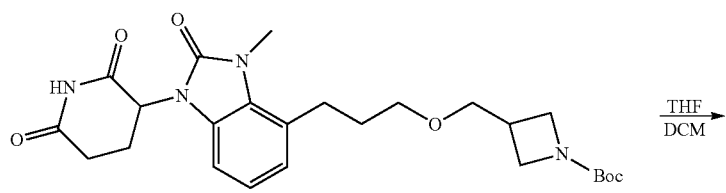

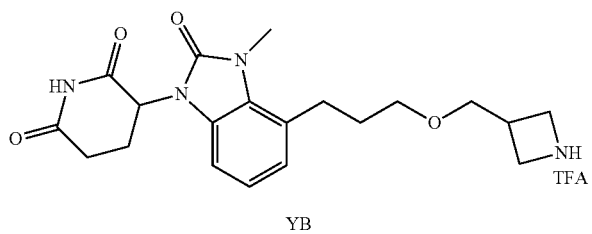

1519

Step 1—Tert-butyl 3-[3-[1-(2,6-dioxo-3-piperidyl)-3-methyl-2-oxo-benzimidazol-4-yl]prop-2-ynoxymethyl]azetidine-1-carboxylate To a solution of tert-butyl 3-(prop-2-ynoxymethyl)azetidine-1-carboxylate (480 mg, 2.13 mmol, Intermediate YA) and 3-(4-bromo-3-methyl-2-oxo-benzimidazol-1-yl)piperidine-2,6-dione (400 mg, 1.18 mmol, Intermediate HP) in DMF (8 mL) was added Pd(PPh$_3$)$_2$Cl$_2$ (166 mg, 236 umol), Cs$_2$CO$_3$ (1.93 g, 5.91 mmol), and CuI (45.1 mg, 236 umol) under N$_2$ atmosphere. The mixture was de-gassed and then heated at 80° C. for 2 hrs under N$_2$ atmosphere. On completion, the mixture was concentrated in vacuo. The residue was washed with ethyl acetate (60 mL), the filtrate was concentrated in vacuo. The residue was purified by reversed-phase HPLC (0.1% FA condition) to give the title compound (450 mg, 63% yield) as brown solid. $^1$H NMR (400 MHz, DMSO-d$_6$) δ 11.12 (m, 1H), 7.20-7.10 (m, 2H), 7.06-6.99 (m, 1H), 5.39 (dd, J=5.6, 12.8 Hz, 1H), 4.47 (s, 2H), 3.64 (s, 3H), 3.60-3.56 (m, 4H), 2.80-2.70 (m, 4H), 2.61-2.59 (m, 2H), 2.06-1.98 (m, 1H), 1.35 (s, 9H); LC-MS (ESI$^+$) m/z 505.2 (M+Na)$^+$.

Step 2—Tert-butyl 3-[3-[1-(2,6-dioxo-3-piperidyl)-3-methyl-2-oxo-benzimidazol-4-yl]propoxymethyl]azetidine-1-carboxylate To a solution of tert-butyl 3-[3-[1-(2,6-dioxo-3-piperidyl)-3-methyl-2-oxo-benzimidazol-4-yl]prop-2-ynoxymethyl]azetidine-1-carboxylate (400 mg, 829 umol) in THF (8 mL) was added Pd/C (80.0 mg, 10% wt) and Pd(OH)$_2$/C (80.0 mg, 10% wt) under N$_2$ atmosphere. The suspension was degassed under vacuum and purged with H$_2$ several times. The mixture was stirred at 25° C. for 12 hrs. On completion, the mixture was filtered and then the filtrate was concentrated in vacuo to give the title compound (400 mg, 79% yield) as brown solid. $^1$H NMR (400 MHz, DMSO-d$_6$) δ 11.09 (s, 1H), 6.99-6.95 (m, 2H), 6.87-6.85 (m, 1H), 5.37 (dd, J=5.2, 12.4 Hz, 1H), 3.56 (s, 3H), 3.52-3.46 (m, 4H), 3.33 (s, 3H), 3.00-2.92 (m, 2H), 2.91-2.84 (m, 1H), 2.78-2.55 (m, 4H), 2.04-1.96 (m, 1H), 1.89-1.77 (m, 2H), 1.38-1.36 (m, 9H). LC-MS (ESI$^+$) m/z 509.3 (M+Na)$^+$.

Step 3-3-[4-[3-(Azetidin-3-ylmethoxy)propyl]-3-methyl-2-oxo-benzimidazol-1-yl]piperidine-2,6-dione To a solution of tert-butyl 3-[3-[1-(2,6-dioxo-3-piperidyl)-3-methyl-2-oxo-benzimidazol-4-yl] propoxymethyl]azetidine-1-carboxylate (313 mg, 514 umol) in DCM (3 mL) was added TFA (3 mL). The mixture was stirred at 25° C. for 2 hrs. On completion, the mixture was concentrated in vacuo to give the title compound (230 mg, 89% yield, TFA salt) as yellow solid. LC-MS (ESI$^+$) m/z 387.2 (M+H)$^+$.

Tert-butyl N-but-3-ynyl-N-methyl-carbamate (Intermediate YC)

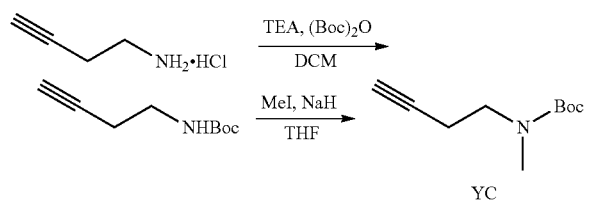

1520

Step 1—Tert-butyl N-but-3-ynylcarbamate

To a solution of but-3-yn-1-amine (4.30 g, 40.7 mmol, HCl) and TEA (4.12 g, 40.7 mmol) in DCM (150 mL) was added (Boc)$_2$O (9.16 g, 41.9 mmol) dropwise at 0° C. The reaction mixture was stirred at 0° C. for 30 minutes. Then TEA (4.12 g, 40.7 mmol) added dropwise at 0° C. The reaction mixture was stirred at 25° C. for 1 hour. On completion, the reaction mixture was diluted with DCM (400 mL) and washed with water (2×100 mL) and HCl (0.5 N, 3×300 mL). The organic layers were dried with anhydrous Na$_2$SO$_4$ and filtered. The filtrate was concentrated in vacuo. The residue was purified by silica column chromatography to give the title compound (4.00 g, 58% yield) as colorless oil. $^1$H NMR (300 MHz, CDCl$_3$) δ 4.93 (s, 1H), 3.25 (q, J=6.0 Hz, 2H), 2.35 (dt, J=2.7, 6.0 Hz, 2H), 1.98 (t, J=2.7 Hz, 1H), 1.41 (s, 9H).

Step 2—Tert-butyl N-but-3-ynyl-N-methyl-carbamate

To a solution of tert-butyl N-but-3-ynylcarbamate (1.00 g, 5.91 mmol) in THF (20 mL) was added NaH (354 mg, 8.86 mmol, 60% oil dispersion) at 0° C. The reaction mixture was stirred at 0° C. for 0.5 hour, then MeI (1.26 g, 8.86 mmol) was added. The reaction mixture was stirred at 25° C. for 12 hours. On completion, the reaction mixture was quenched with sat. NH$_4$Cl (30 mL) and extracted with EA (2×100 mL). The combined organic layers were washed with brine (50 mL), dried with anhydrous Na$_2$SO$_4$ and filtered. The filtrate was concentrated in vacuo. The residue was purified by column chromatography to give the title compound (1.00 g, 92% yield) as colorless oil. $^1$H NMR (300 MHz, CDCl$_3$) δ 3.43-3.28 (m, 2H), 2.87 (s, 3H), 2.44-2.33 (m, 2H), 1.95 (t, J=2.4 Hz, 1H), 1.44 (s, 9H).

3-[3-Methyl-4-[4-(methylamino)butyl]-2-oxo-benzimidazol-1-yl]piperidine-2,6-dione (Intermediate YD)

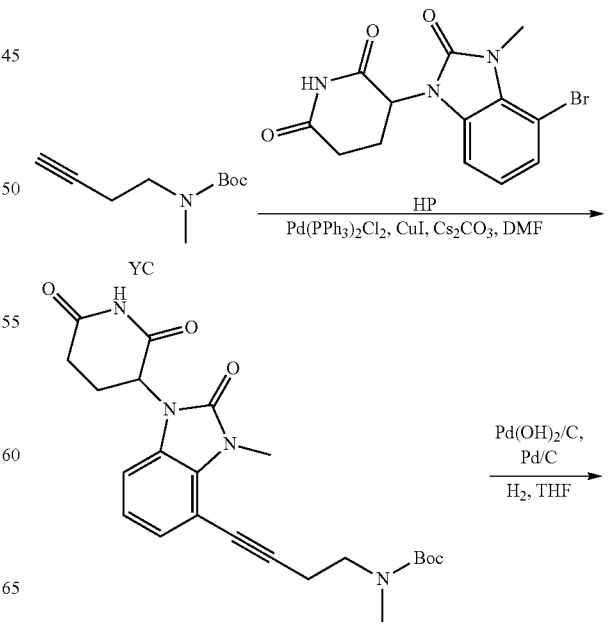

-continued

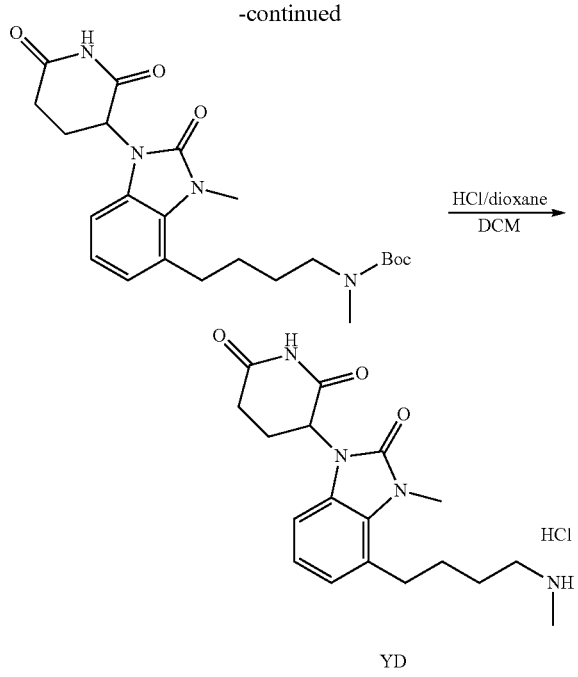

Step 1—Tert-butyl N-[4-[1-(2,6-dioxo-3-piperidyl)-3-methyl-2-oxo-benzimidazol-4-yl]but-3-ynyl]-N-methyl-carbamate To a solution of 3-(4-bromo-3-methyl-2-oxo-benzimidazol-1-yl)piperidine-2,6-dione (500 mg, 1.48 mmol, Intermediate HP) and 4 Å molecular sieves (50 mg) in DMF (5 mL) was added Pd(PPh₃)₂Cl₂ (103 mg, 147 umol), CuI (56.3 mg, 295 umol) and Cs₂CO₃ (1.93 g, 5.91 mmol). The reaction mixture was degassed with N₂ for three times. Then tert-butyl N-but-3-ynyl-N-methyl-carbamate (487 mg, 2.66 mmol, Intermediate YC) was added. The reaction mixture was stirred at 85° C. for 2 hours. On completion, the reaction mixture was filtered. The organic layer was diluted with EA (300 mL), washed with sat.NH₄Cl (2×100 mL) and brine (100 mL), dried with anhydrous Na₂SO₄ and filtered. The filtrate was concentrated in vacuo. The residue was purified by reverse phase flash (0.1%, FA) to give the title compound (400 mg, 61% yield) as a light yellow solid, LC-MS (ESI⁺) m/z 463.1 (M+Na)⁺.

Step 2—Tert-butyl N-[4-[1-(2,6-dioxo-3-piperidyl)-3-methyl-2-oxo-benzimidazol-4-yl]butyl]-N-methyl-carbamate To a solution of tert-butyl N-[4-[1-(2,6-dioxo-3-piperidyl)-3-methyl-2-oxo-benzimidazol-4-yl]but-3-ynyl]-N-methyl-carbamate (400 mg, 908 umol) in THF (25 mL) was added Pd/C (200 mg, 10 wt %) and Pd(OH)₂/C (1.28 g, 10 wt %). The reaction mixture was stirred at 25° C. under H₂ (15 psi) for 12 hours. On completion, the reaction mixture was filtered and concentrated in vacuo to give the title compound (400 mg, 99% yield) as a white solid, ¹H NMR (400 MHz, DMSO-d₆) δ 11.08 (s, 1H), 6.99-6.93 (m, 2H), 6.89-6.84 (m, 1H), 5.40-5.32 (m, 1H), 3.55 (s, 3H), 3.24-3.14 (m, 2H), 2.99-2.82 (m, 3H), 2.75 (s, 3H), 2.72-2.59 (m, 2H), 2.04-1.94 (m, 1H), 1.63-1.48 (m, 4H), 1.36 (s, 9H).

Step 3—3-[3-Methyl-4-[4-(methylamino)butyl]-2-oxo-benzimidazol-1-yl]piperidine-2,6-dione To a solution of tert-butyl N-[4-[1-(2,6-dioxo-3-piperidyl)-3-methyl-2-oxo-benzimidazol-4-yl]butyl]-N-methyl-carbamate (390 mg, 877 umol) in DCM (15 mL) was added HCl/dioxane (4 M, 15 mL). The reaction mixture was stirred at 25° C. for 1 hour. On completion, the reaction mixture was concentrated in vacuo to give the title compound (300 mg, 89% yield, HCl) as a white solid. LC-MS (ESI⁺) m/z 345.2 (M+H)⁺.

2-[2-[Tert-butoxycarbonyl(methyl)amino]-4-pyridyl]oxazole-4-carboxylic acid (Intermediate YE)

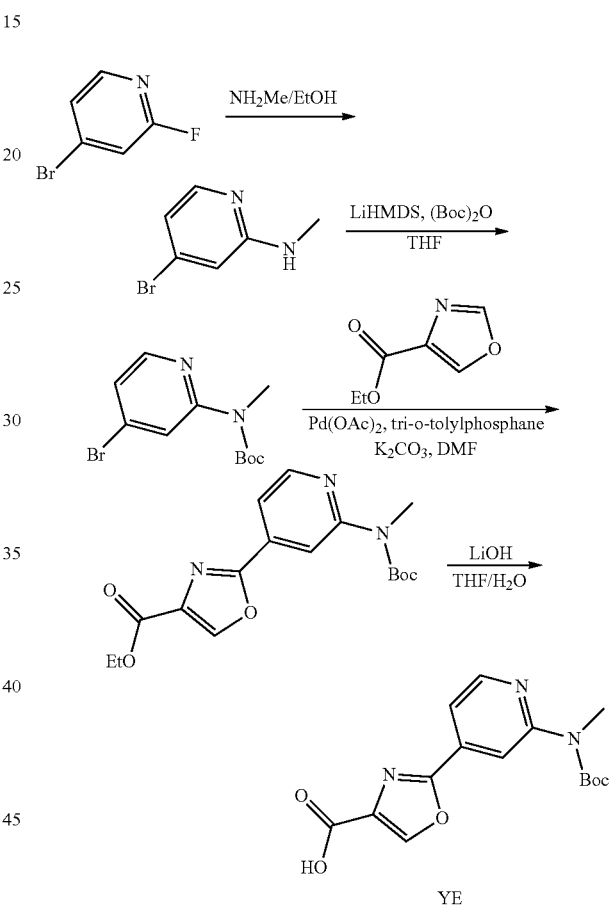

Step 1—4-Bromo-N-methyl-pyridin-2-amine

To a solution of 4-bromo-2-fluoro-pyridine (5.00 g, 28.4 mmol, CAS #128071-98-7) in THF (50.0 mL) was added a solution of MeNH₂ in EtOH (2.00 M, 42.6 mL). The mixture was stirred at 120° C. for 2 hrs under seal tube. The mixture was concentrated in vacuo. The mixture was purified by silica gel column (PE:EA=80:1) to give the title compound (4.50 g, 84% yield) as white solid. ¹H NMR (400 MHz, DMSO-d₆) δ 7.87-7.84 (m, 1H), 6.75-6.74 (m, 1H), 6.66-6.65 (m, 1H), 6.64 (s, 1H), 2.75 (s, 3H).

Step 2—Tert-butyl N-(4-bromo-2-pyridyl)-N-methyl-carbamate

To a solution of 4-bromo-N-methyl-pyridin-2-amine (4.00 g, 21.4 mmol) in THF (30.0 mL) was added LiHMDS (1.00 M, 47.1 mL) dropwise at −5° C. Then a solution of (Boc)₂O (4.67 g, 21.4 mmol, 4.91 mL) in THF (10.0 mL) was added into the above mixture slowly. The reaction mixture was stirred at −5° C. for 10 minutes, then heated to 20° C. and stirred for 1 hr. The reaction mixture was quenched with sat. NH₄Cl (100 ml), extracted with EA (2×50 mL), then concentrated in vacuo to give a residue. The residue was purified by silica gel column chromatography (PE:EA=100:1-8:1) to give the title compound (5.00 g, 81% yield) as a yellow liquid. ¹H NMR (400 MHz, DMSO-d₆) δ 8.16 (d, J 5.6 Hz, 1H), 8.02-8.01 (m, 1H), 7.13 (dd, J=5.2 Hz, J=5.6 Hz, 1H), 3.39 (s, 3H), 1.53 (s, 9H).

Step 3—Ethyl 2-[2-[tert-butoxycarbonyl(methyl) amino]-4-pyridyl]oxazole-4-carboxylate A mixture of tert-butyl N-(4-bromo-2-pyridyl)-N-methyl-carbamate (4.00 g, 13.9 mmol), ethyl oxazole-4-carboxylate (1.97 g, 13.9 mmo, CAS #170487-38-4), Pd(OAc)₂ (313 mg, 1.39 mmol), tris-o-tolylphosphane (848 mg, 2.79 mmol) and K₂CO₃ (5.78 g, 41.8 mmol) in DMF (60.0 mL) was degassed and purged with N₂ three times, and then the mixture was stirred at 70° C. for 16 hrs under N₂ atmosphere. On completion, the reaction mixture was diluted by addition H₂O (30 mL) and extracted with EA (3×50 mL). The combined organic layers were washed with saturated NaCl (2×100 mL), dried over Na₂SO₄, filtered and concentrated in vacuo to give a residue. The crude product was purified by reverse phase (0.1% FA condition) to give the title compound (2.20 g, 45% yield) as a white solid. ¹H NMR (400 MHz, CDCl₃) δ 8.49 (d, J 6.8 Hz, 1H), 8.42 (s, 1H), 8.33 (s, 1H), 7.71-7.69 (m, 1H), 4.47-4.41 (m, 2H), 3.45 (s, 3H), 1.56 (s, 9H), 1.42 (t, J 13.2 Hz, 3H).

Step 4—2-[2-[Tert-butoxycarbonyl(methyl)amino]-4-pyridyl]oxazole-4-carboxylic acid To a solution of ethyl 2-[2-[tert-butoxycarbonyl(methyl) amino]-4-pyridyl]oxazole-4-carboxylate (200 mg, 575 umol) in THF (10.0 mL) and H₂O (2.00 mL) was added LiOH (68.9 mg, 2.88 mmol). The mixture was stirred at 20° C. for 15 hrs. On completion, the reaction mixture was quenched with water (1 mL), and the mixture was acidified with 1N HCl solution until the pH=5. The aqueous phase was extracted with EA (3×10 mL). The combined organic layer was washed with brine (2×10 mL), dried with anhydrous Na₂SO₄, filtered and concentrated in vacuo to give the title compound (160 mg, 87% yield) as an off-white solid. ¹H NMR (400 MHz, DMSO-d₆) δ 8.96 (s, 1H), 8.57 (d, J 5.2 Hz, 1H), 8.35 (s, 1H), 7.65 (dd, J₁=4.8 Hz, J=5.2 Hz, 1H), 3.37 (s, 3H), 1.52 (s, 9H).

Tert-butyl N-[4-[4-[[3-(difluoromethyl)-1-(4-formyl-cyclohexyl)pyrazol-4-yl]carbamoyl] oxazol-2-yl]-2-pyridyl]-N-methylcarbamate (Intermediate YF)

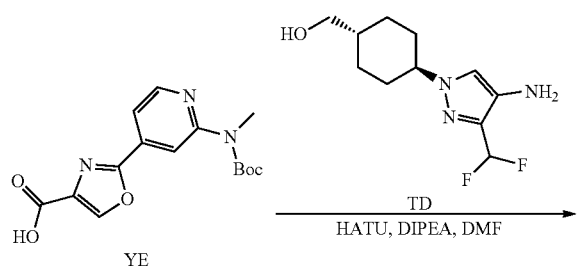

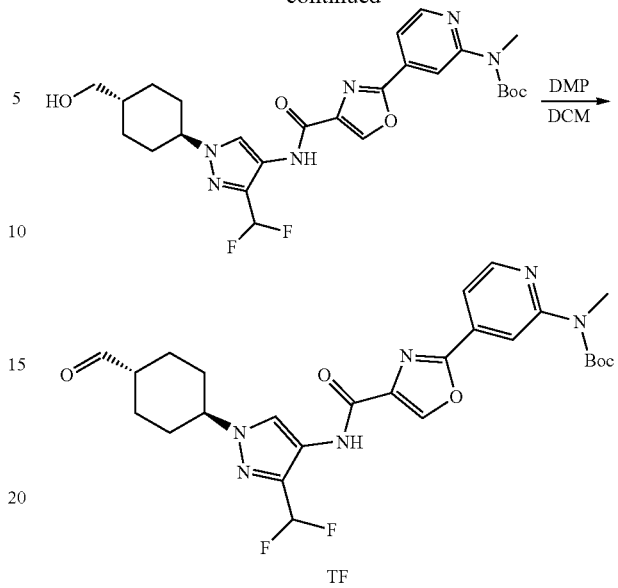

Step 1—Tert-butyl N-[4-[4-[[3-(difluoromethyl)-1-[4-(hydroxymethyl)cyclohexyl]pyrazol-4-yl] carbamoyl]oxazol-2-yl]-2-pyridyl]-N-methyl-carbamate To a solution of 2-[2-[tert-butoxycarbonyl(methyl) amino]-4-pyridyl]oxazole-4-carboxylic acid (130 mg, 407 umol, Intermediate YE) and [4-[4-amino-3-(difluoromethyl) pyrazol-1-yl]cyclohexyl]methanol (99.9 mg, 407. umol, Intermediate TD) in DMF (5.00 mL) was added DIPEA (158 mg, 1.22 mmol) and HATU (232 mg, 610 umol). The mixture was stirred at 20° C. for 0.5 hr. On completion, the reaction mixture was quenched by addition H₂O (30 mL), and then extracted with EA (3×10 mL). The combined organic layers were washed with brine (2×5 mL), dried over Na₂SO₄, filtered and concentrated in vacuo to give a residue. The residue was purified by prep-HPLC (column: Phenomenex Synergi C18 150*25*10 um; mobile phase: [water (0.225% FA)-ACN]; B %: 47%-77%, 10 min) give the title compound (200 mg, 89% yield) as white solid. ¹HNMR (400 MHz, DMSO-d₆) δ 9.76 (s, 1H), 9.01 (s, 1H), 8.60 (d, J=5.2, 1H), 8.36 (s, 1H), 8.19 (s, 1H), 7.69-7.67 (m, 1H), 7.29-7.02 (m, 1H), 4.24-4.17 (m, 1H), 3.38 (s, 3H), 3.31 (s, 1H), 3.27-3.26 (m, 2H), 2.68-2.66 (m, 1H), 2.07-2.04 (m, 2H), 1.88-1.84 (m, 2H), 1.80-1.72 (m, 2H), 1.52 (s, 9H), 1.14-1.08 (m, 2H).

Step 2—Tert-butyl N-[4-[4-[[3-(difluoromethyl)-1-(4-formylcyclohexyl)pyrazol-4-yl]carbamoyl] oxazol-2-yl]-2-pyridyl]-N-methylcarbamate To a solution of tert-butyl N-[4-[4-[[3-(difluoromethyl)-1-[4-(hydroxymethyl)cyclohexyl]pyrazol-4-yl] carbamoyl] oxazol-2-yl]-2-pyridyl]-N-methyl-carbamate (170 mg, 311 umol) in DCM (2.00 mL) was added DMP (197 mg, 466 umol). The mixture was stirred at 20° C. for 1 hr. The reaction mixture was diluted with water (5 mL) and extracted with DCM (1×5 mL). The combined organic layers were washed with brine (3×5 mL), dried over Na₂SO₄ filtered and concentrated in vacuo to give the title compound (130 mg, 76% yield) as yellow solid. ¹HNMR (400 MHz, DMSO-d₆) δ 9.78 (s, 1H), 9.63-9.63 (m, 1H), 9.02 (s, 1H), 8.61-8.59 (m, 1H), 8.36 (s, 1H), 8.21-8.20 (s, 1H), 7.69 (dd, $J_1$=5.2 Hz, $J_2$=5.2 Hz, 1H), 7.31-7.03 (m, 1H), 4.29-4.21 (m, 1H), 3.38 (s, 3H), 2.44-2.38 (m, 1H), 2.14-2.06 (m, 4H), 1.88-1.79 (m, 2H), 1.52 (s, 9H), 1.43-1.34 (m, 2H).

Tert-butyl 3-prop-2-ynoxypyrrolidine-1-carboxylate (Intermediate YG)

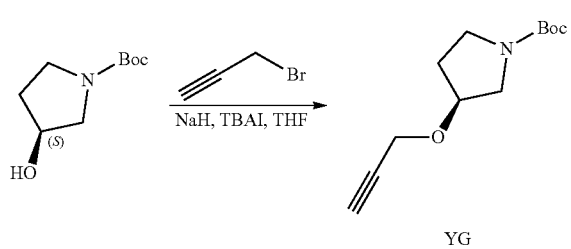

To a solution of tert-butyl (3S)-3-hydroxypyrrolidine-1-carboxylate (5.00 g, 26.7 mmol, CAS #101469-92-5) in THF (150 mL) was added NaH (1.60 g, 40.0 mmol, 60% oil dispersion) at 0° C. The reaction mixture was stirred at 0° C. for 30 minutes. Then TBAI (986 mg, 2.67 mmol) and 3-bromoprop-1-yne (4.37 g, 29.3 mmol, CAS #106-96-7) was added. The reaction mixture was stirred at 25° C. for 12 hours. On completion, the reaction mixture was diluted with EA (300 mL) and quenched with sat. NH$_4$Cl (100 mL). The organic layer was washed with water (2×30 mL) and brine (50 mL). The organic layer was dried with anhydrous Na$_2$SO4 and filtered. The filtrate was concentrated in vacuo. The residue was purified by silica column chromatography to give the title compound (5.90 g, 98% yield) as light yellow oil, $^1$H NMR (300 MHz, CDCl$_3$) δ 4.29-4.21 (m, 1H), 4.17-4.10 (m, 2H), 3.51-3.32 (m, 4H), 2.50-2.34 (s, 1H), 2.02-1.90 (m, 2H), 1.43 (s, 9H).

3-[3-Methyl-2-oxo-4-[3-[(3S)-pyrrolidin-3-yl]oxypropyl]benzimidazol-1-yl]piperidine-2,6-dione (Intermediate YH)

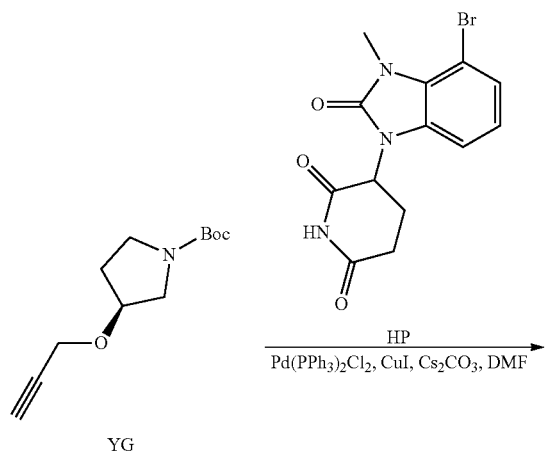

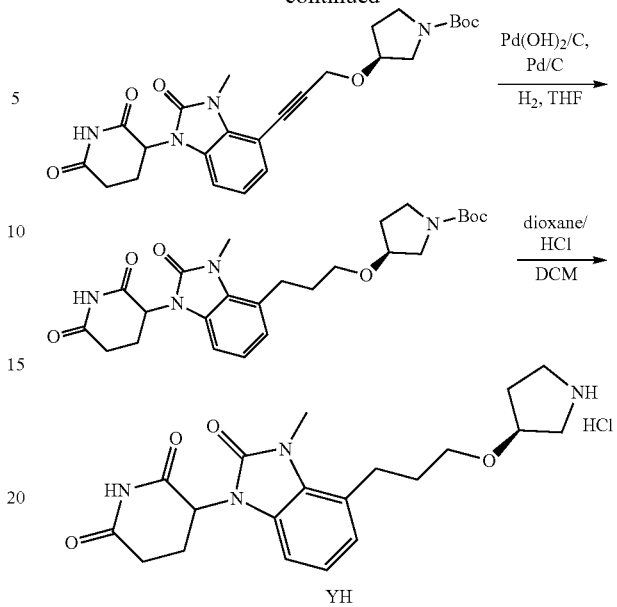

Step 1—Tert-butyl (3S)-3-[3-[1-(2,6-dioxo-3-piperidyl)-3-methyl-2-oxo-benzimidazol-4-yl]prop-2-ynoxy]pyrrolidine-1-carboxylate To a solution of 3-(4-bromo-3-methyl-2-oxo-benzimidazol-1-yl)piperidine-2,6-dione (600 mg, 1.77 mmol, Intermediate HP) in DMF (10 mL) was added Pd(PPh$_3$)$_2$Cl$_2$ (124 mg, 177 umol), CuI (33.7 mg, 177 umol) and Cs$_2$CO$_3$ (2.31 g, 7.08 mmol). The reaction mixture was degassed with N$_2$ three times. Then tert-butyl 3-prop-2-ynoxypyrrolidine-1-carboxylate (598 mg, 2.66 mmol, Intermediate YG) was added. The reaction mixture was stirred at 80° C. for 8 hours. On completion, the reaction mixture was filtered. The filtrate was concentrated in vacuo. The residue was purified by reversed-phase flash (FA, 0.1%) to give the title compound (450 mg, 52% yield) as a yellow solid, $^1$H NMR (400 MHz, DMSO-d$_6$) δ 11.13 (s, 1H), 7.19-7.10 (m, 2H), 7.04 (d, J=8.0 Hz, 1H), 5.44-5.34 (m, 1H), 4.48 (s, 2H), 4.32-4.25 (m, 1H), 3.63 (s, 3H), 3.29-3.07 (m, 4H), 2.94-2.82 (m, 1H), 2.77-2.62 (m, 2H), 2.56-2.52 (m, 1H), 2.04-1.92 (m, 3H), 1.38 (d, J=9.2 Hz, 9H).

Step 2—Tert-butyl (3S)-3-[3-[1-(2,6-dioxo-3-piperidyl)-3-methyl-2-oxo-benzimidazol-4-yl]propoxy]pyrrolidine-1-carboxylate To a solution of tert-butyl (3S)-3-[3-[1-(2,6-dioxo-3-piperidyl)-3-methyl-2-oxo-benzimidazol-4-yl] prop-2-ynoxy] pyrrolidine-1-carboxylate (400 mg, 828 umol) in THF (25 mL) was added Pd/C (200 mg, 10 wt %) and Pd(OH)$_2$/C (200 mg, 10 wt %). The reaction mixture was stirred at 25° C. for 12 hours under H$_2$ (15 psi). On completion, the reaction mixture was filtered and concentrated in vacuo to give the title compound (400 mg, 99% yield) as a yellow solid. $^1$H NMR (400 MHz, DMSO-d$_6$) δ 11.08 (s, 1H), 6.98-6.94 (m, 2H), 6.88-6.84 (m, 1H), 5.39-5.31 (m, 1H), 4.05-4.00 (m, 1H), 3.55 (s, 3H), 3.47-3.39 (m, 2H), 3.30-3.22 (m, 4H), 2.96-2.84 (m, 3H), 2.76-2.60 (m, 2H), 2.55-2.52 (m, 2H), 2.02-1.96 (m, 1H), 1.93-1.87 (m, 2H), 1.84-1.78 (m, 2H), 1.40 (s, 10H).

Step 3—3-[3-Methyl-2-oxo-4-[3-[(3S)-pyrrolidin-3-yl]oxypropyl]benzimidazol-1-yl]piperidine-2,6-dione To a solution of tert-butyl (3S)-3-[3-[1-(2,6-dioxo-3-piperidyl)-3-methyl-2-oxo-benzimidazol-4-yl] propoxy]pyrrolidine-1-carboxylate (395 mg, 811 umol) in DCM (15 mL) was added HCl/dioxane (4 M, 15 mL). The reaction mixture was stirred at 25° C. for 1 hour. On completion, the reaction mixture was concentrated in vacuo to give the title compound (300 mg, 87% yield, HCl) as a white solid. LC-MS (ESI⁺) m/z 387.2 (M+H)⁺.

[3-Methyl-4-[[4-(methylaminomethyl)-1-piperidyl]methyl]-2-oxo-benzimidazol-1-yl]piperidine-2,6-dione (Intermediate YI)

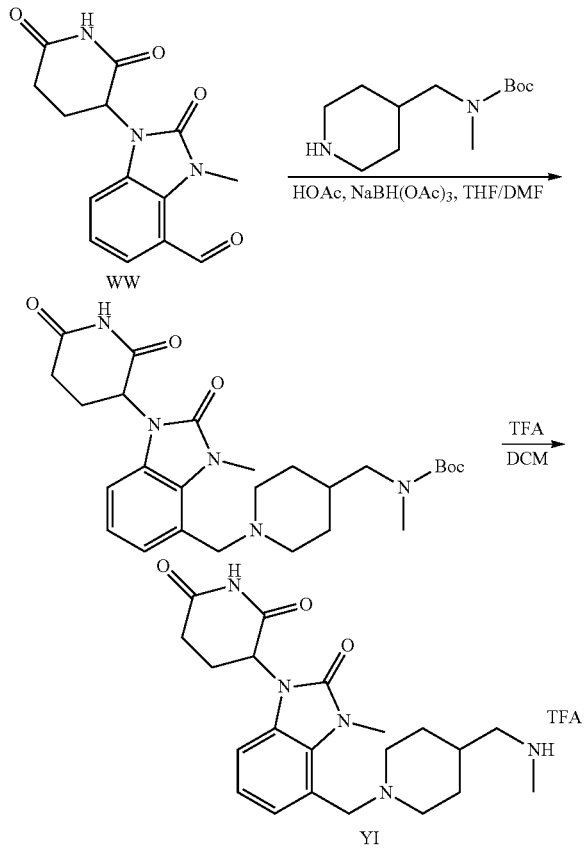

Step 1—Tert-butyl N-[[1-[[1-(2,6-dioxo-3-piperidyl)-3-methyl-2-oxo-benzimidazol-4-yl]methyl]-4-piperidyl]methyl]-N-methyl-carbamate To a solution of 1-(2,6-dioxo-3-piperidyl)-3-methyl-2-oxo-benzimidazole-4-carbaldehyde (150 mg, 522 umol, Intermediate WW) and tert-butyl N-methyl-N-(4-piperidylmethyl)carbamate (119 mg, 522 umol, CAS #138022-04-5) in THF (2 mL) and DMF (0.5 mL) was added HOAc (31.4 mg, 522 umol) at 25° C. The mixture was stirred for 0.5 hour, then NaBH(OAc)₃ (221 mg, 1.04 mmol) was added. The mixture was stirred at 25° C. for 2 hours. On completion, the mixture was quenched by water (0.2 mL), and concentrated in vacuo to give a residue. The residue was purified by reverse phase (0.1% FA condition) to give the title compound (180 mg, 69% yield) as a white solid. ¹H NMR (400 MHz, CDCl₃) δ 8.48 (s, 1H), 8.24 (s, 1H), 7.08-6.97 (m, 2H), 6.85-6.72 (m, 1H), 5.28-5.22 (m, 1H), 3.78 (d, J=5.0 Hz, 5H), 3.68-3.51 (m, 2H), 3.10 (s, 2H), 3.04-2.94 (m, 2H), 2.94-2.90 (m, 1H), 2.86 (s, 4H), 2.81-2.72 (m, 1H), 2.27-2.20 (m, 1H), 1.71-1.62 (m, 2H), 1.46 (s, 9H), 1.39-1.21 (m, 2H); LC-MS (ESI⁺) m/z 500.4 (M+H)⁺.

Step 2—[3-Methyl-4-[[4-(methylaminomethyl)-1-piperidyl]methyl]-2-oxo-benzimidazol-1-yl]piperidine 2,6-dione To a mixture of tert-butyl N-[[1-[[1-(2,6-dioxo-3-piperidyl)-3-methyl-2-oxo-benzimidazol-4-yl] methyl]-4-piperidyl]methyl]-N-methyl-carbamate (106 mg, 212 umol) in DCM (2 mL) was added TFA (483 mg, 4.24 mmol) at 25° C. The mixture was stirred at 25° C. for 2 hours. On completion, the reaction mixture was concentrated in vacuo give the title compound (108 mg, 99% yield, TFA). LC-MS (ESI⁺) m/z 399.9 (M+H)⁺.

3-[3-Methyl-4-[[(2S)-2-(methylaminomethyl)morpholin-4-yl]methyl]-2-oxo-benzimidazol-1-yl]piperidine-2,6-dione (Intermediate YJ)

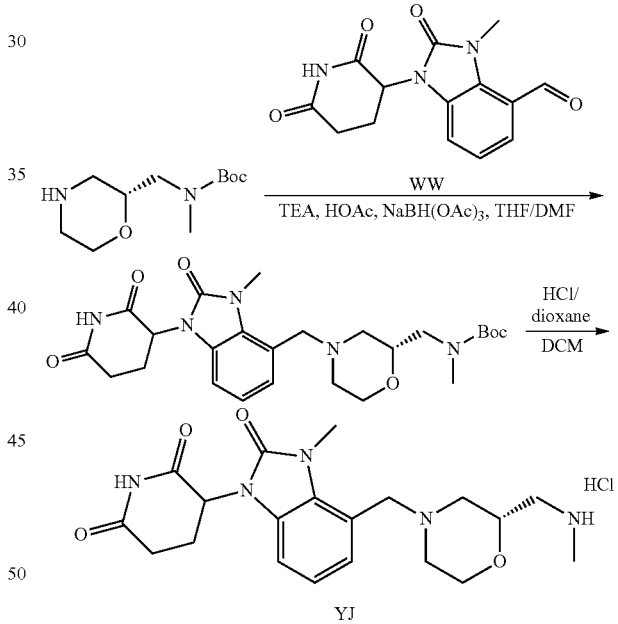

Step 1—Tert-butyl-N-[[(2R)-4-[[1-(2,6-dioxo-3-piperidyl)-3-methyl-2-oxo-benzimidazol-4-yl]methyl]morpholin-2-yl] methyl]-N-methyl-carbamate To a solution of tert-butyl N-methyl-N-[[(2R)-morpholin-2-yl]methyl]carbamate (158 mg, 689 umol, synthesized via Steps 1-5 of Intermediate WP), 1-(2,6-dioxo-3-piperidyl)-3-methyl-2-oxo-benzimidazole-4-carbaldehyde (180 mg, 626 umol, Intermediate WW) in DMF (3.00 mL) and THF (10.0 mL) was added HOAc (75.2 mg, 1.25 mmol). The mixture was stirred at 20° C. for 0.5 hr, then NaBH(OAc)₃ (265 mg, 1.25 mmol) was added, and the mixture was stirred at 20° C. for 14 hrs. On completion, the reaction mixture was quenched with H₂O (3 mL) at 20° C., and extracted with EA 60 mL (3×20 mL). The combined organic layers were washed with brine (2×10 mL), dried over Na₂SO₄, filtered and concentrated in vacuo to give a residue. The residue was purified by reversed-phase HPLC (0.1% FA condition) to give the title compound (215 mg, 68% yield) as a white solid. ¹H NMR (400 MHz, CDCl₃) δ 8.07 (s, 1H), 6.88-6.86 (m, 1H), 6.82-6.80 (m, 1H), 6.69 (d, J=7.6 Hz, 1H), 5.19-5.07 (m, 1H), 3.79-3.72 (m, 1H), 3.72-3.71 (m, 3H), 3.57 (s, 2H), 3.53-3.47 (m, 2H), 3.39-3.36 (m, 2H), 2.87 (s, 2H), 2.83 (s, 3H), 2.73-2.72 (m, 1H), 2.63-2.54 (m, 2H), 2.19-2.12 (m, 2H), 1.87-1.80 (m, 1H), 1.36 (s, 9H).

Step 2—3-[3-Methyl-4-[[(2S)-2-(methylaminomethyl)morpholin-4-yl]methyl]-2-oxo-benzimidazol-1-yl]]piperidine-2,6-dione To a solution of tert-butyl N-[[(2R)-4-[[1-(2,6-dioxo-3-piperidyl)-3-methyl-2-oxo-benzimidazol-4-yl] methyl] morpholin-2-yl] methyl]-N-methyl-carbamate (100 mg, 199 umol) in DCM (3.00 mL) was added HCl/dioxane (4.00 M, 5.00 mL). The mixture was stirred at 20° C. for 1 hr. On completion, the reaction mixture was concentrated in vacuo to give the title compound (87.0 mg, quant. crude yield, HCl) as yellow solid. LC-MS (ESI⁺) m/z 401.2 (M+H)⁺.

3-[3-Methyl-2-oxo-4-[2-(4-piperidyl)ethynyl]benzimidazol-1-yl]piperidine-2,6-dione (Intermediate YL)

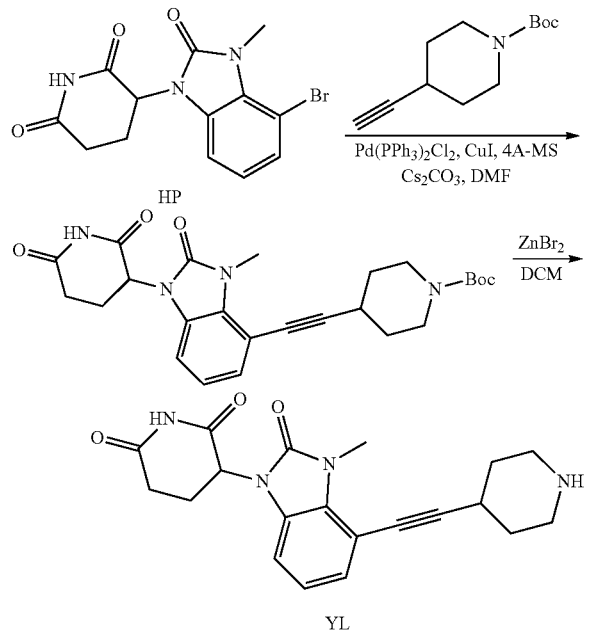

YL

Step 1—Tert-butyl 4-[2-[1-(2,6-dioxo-3-piperidyl)-3-methyl-2-oxo-benzimidazol-4-yl]ethynyl] piperidine-1-carboxylate To a solution of 3-(4-bromo-3-methyl-2-oxobenzimidazol-1-yl)piperidine-2,6-dione (400 mg, 1.18 mmol, Intermediate HP), and tert-butyl 4-ethynylpiperidine-1-carboxylate (446 mg, 2.13 mmol, CAS #287192-97-6) in DMF (5.00 mL) was added Cs₂CO₃ (1.93 g, 5.91 mmol), 4 Å molecular sieves (100 mg), Pd(PPh₃)₂Cl₂ (83.0 mg, 118 umol) and CuI (22.5 mg, 118 umol). The mixture was stirred at 80° C. for 2 hrs under N₂. On completion, the reaction mixture was filtered and the filter cake was washed with ACN (10 mL). The filtrate was concentrated in vacuo to give a residue. The residue was purified by reverse phase (0.1% FA condition) to give the title compound (330 mg, 707 umol, 60% yield) as yellow solid. ¹H NMR (400 MHz, DMSO-d₆) δ 11.11 (s, 1H), 7.13-7.11 (m, 1H), 7.07-7.05 (m, 1H), 7.01-6.97 (m, 1H), 5.40-5.36 (m, 1H), 3.72-3.66 (m, 2H), 3.63 (s, 3H), 3.12-3.07 (m, 2H), 2.93-2.87 (m, 2H), 2.75-2.68 (m, 1H), 2.65-2.60 (m, 1H), 2.04-1.99 (m, 1H), 1.88-1.85 (m, 2H), 1.8-1.50 (m, 2H), 1.40 (s, 9H).

Step 2—3-[3-Methyl-2-oxo-4-[2-(4-piperidyl)ethynyl]benzimidazol-1-yl]piperidine-2,6-dione To a solution of tert-butyl 4-[2-[1-(2,6-dioxo-3-piperidyl)-3-methyl-2-oxo-benzimidazol-4-yl]ethynyl] piperidine-1-carboxylate (300 mg, 643 umol) in DCM (3.00 mL) was added ZnBr₂ (2.17 g, 9.65 mmol). The mixture was stirred at 20° C. for 20 hrs. On completion, the reaction mixture was concentrated in vacuo to give the title compound (235 mg, 99% yield) as yellow gum. LC-MS (ESI⁺) m/z 367.2 (M+H)⁺.

1-(2,6-Dioxo-3-piperidyl)-3-methyl-2-oxo-benzimidazole-4-carbaldehyde (Intermediate WW)

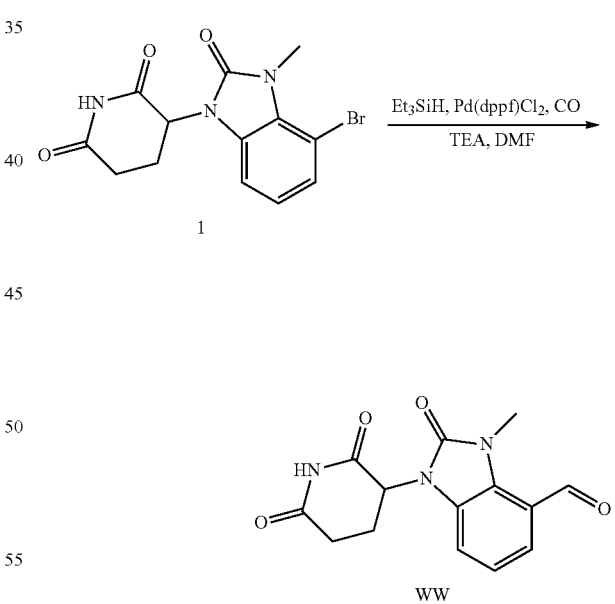

WW

To a solution of 3-(4-bromo-3-methyl-2-oxo-benzimidazol-1-yl)piperidine-2,6-dione (500 mg, 1.48 mmol, Intermediate HP) in DMF (20 mL) was added TEA (448 mg, 4.44 mmol), Pd(dppf)Cl₂ (162 mg, 221 umol) and Et₃SiH (515 mg, 4.44 mmol). The reaction mixture was stirred at 80° C. for 16 hours under CO (50 Psi). On completion, the reaction mixture was concentrated in vacuo and purified by reverse phase (0.1% FA) to give the title compound (400 mg, 47% yield) as a white solid. LC-MS (ESI⁺) m/z 288.0 (M+H)⁺.

1531

3-(5-Bromo-9H-pyrido[2,3-b]indol-9-yl)piperidine-2,6-dione (Intermediate XF)

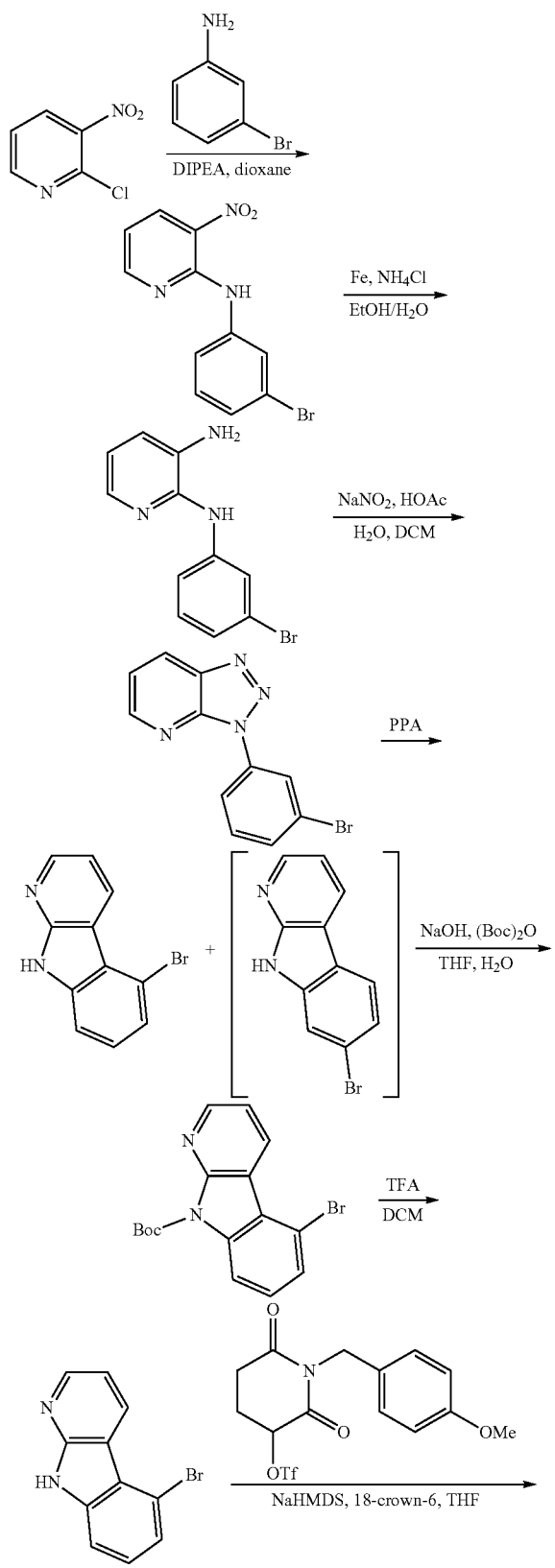

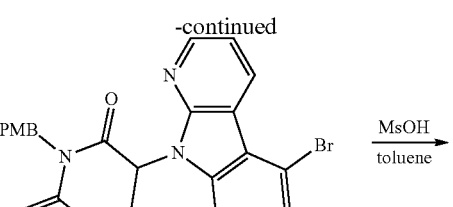

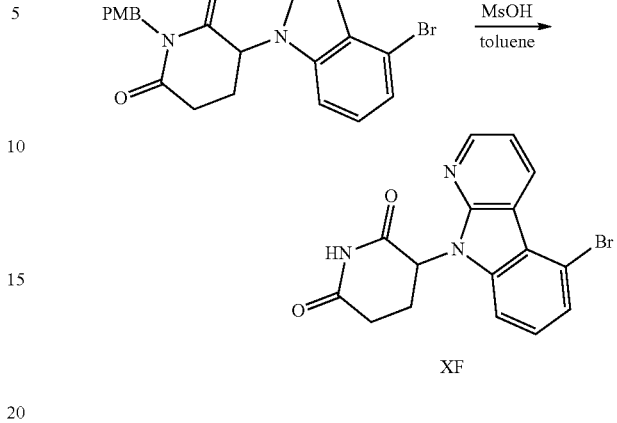

Step 1—N-(3-bromophenyl)-3-nitro-pyridin-2-amine

To a solution of 2-chloro-3-nitro-pyridine (5.00 g, 315 mmol, CAS #34515-82-7) and 3-bromoaniline (5.97 g, 34.7 mmol, CAS #591-19-5) in dioxane (40 mL) was added DIPEA (12.2 g, 94.6 mmol). The reaction mixture was stirred at 115° C. for 2 days. Then the mixture was concentrated under reduced pressure. The residue was purified by silica gel chromatography to give the title compound (8.00 g, 86% yield) as a red solid. LC/MS (ESI, m/z): [M+1]$^+$=295.1.

Step 2—N$_2$-(3-bromophenyl)pyridine-2,3-diamine

To a solution of N-(3-bromophenyl)-3-nitro-pyridin-2-amine (5.00 g, 17.0 mmol) and NH$_4$Cl (9.09 g, 170 mmol) in a mixed solvent of H$_2$O (80 mL) and EtOH (80 mL) was added Fe (9.49 g, 170 mmol). The reaction mixture was stirred at 80° C. for 1 h. The mixture was then diluted with water (80 mL) and extracted with EA (2×80 mL). The organic layers were washed with brine (2×30 mL), dried with Na$_2$SO$_4$, filtered and the filtrate was concentrated under reduced pressure to give the title compound (4.00 g, 89% yield) as a brown solid. LC/MS (ESI, m/z): [M+1]$^+$=265.1.

Step 3—3-(3-Bromophenyl)triazolo[4,5-b]pyridine

To a solution of N2-(3-bromophenyl)pyridine-2,3-diamine (4.00 g, 15.1 mmol) in a mixed solvent of HOAc (25 mL) and DCM (25 mL) was added a solution of NaNO$_2$ (1.36 g, 19.7 mmol) in H$_2$O (15 mL) dropwise at 0° C. The reaction mixture was stirred at 25° C. for 30 minutes. On completion, the mixture was diluted with water (50 mL), and extracted with DCM (2×50 mL). The organic layers were washed with brine (2×50 mL), dried with Na$_2$SO$_4$, filtered and the filtrate was concentrated under reduced pressure to give the title compound (4.10 g, 98% yield) as a brown solid. LC/MS (ESI, m/z): [M+1]$^+$=276.1.

Step 4—5-Bromo-9H-pyrido[2,3-b]indole

A mixture of 3-(3-bromophenyl)triazolo[4,5-b]pyridine (3.60 g, 13.1 mmol) in PPA (20 mL) was heated at 170° C. for 3 h. On completion, the mixture was poured into the ice water (200 mL), stirred for 1 h, then filtered. The filter cake was dried under reduced pressure. The filter cake contained two isomers 5-bromo-9H-pyrido[2,3-b]indole and its isomer 7-bromo-9H-pyrido[2,3-b]indole, which were brought on to the next step directly.

Step 5—tert-butyl 5-bromo-9H-pyrido[2,3-b]indole-9-carboxylate

To a mixture of 5-bromo-9H-pyrido[2,3-b]indole and 7-bromo-9H-pyrido[2,3-b]indole (10.0 g, 40.0 mmol) in THF/H$_2$O (100 mL/100 mL) was added Boc$_2$O (17.4 g, 80.0 mmol) and NaOH (4.8 g, 120.0 mmol), and the mixture was stirred at rt for 3 h. On completion, the mixture was poured into the water (200 mL), and extracted with EA (2×100 mL). The organic layers were washed with brine (2×100 mL), dried over Na$_2$SO$_4$, filtered and the filtrate was concentrated to give crude product which was purification by column chromatography to give tert-butyl 5-bromo-9H-pyrido[2,3-b]indole-9-carboxylate (4.10 g, 7% yield for two steps) as brown product. LC/MS (ESI, m/z): [M+1]$^+$=348.2.

Step 6—5-Bromo-9H-pyrido[2,3-b]indole

A mixture of tert-butyl 5-bromo-9H-pyrido[2,3-b]indole-9-carboxylate (9.0 g, 25.9 mmol) in DCM (20 mL) was added TFA (15 mL), and the mixture was stirred at rt for 16 h. On completion, the mixture was concentrated to give the title product (6.0 g, 94% yield) as brown solid.

Step 7—3-(5-Bromopyrido[2,3-b]indol-9-yl)-1-[(4-methoxyphenyl)methyl]piperidine-2,6-dione To a mixture of 5-bromo-9H-pyrido[2,3-b]indole (250 mg, 1.01 mmol) and 18-crown-6 (53 mg, 0.2 mmol) in THF (5 mL) was added NaHMDS (0.75 mL, 1.5 mmol) (2 M in THF) at −30° C. After stirring for 1 h at −30° C., a solution of [1-[(4-methoxyphenyl)methyl]-2,6-dioxo-3-piperidyl] trifluoromethanesulfonate (579 mg, 1.5 mmol) in THF (2 mL) was added into the above mixture dropwise at −30° C. The reaction mixture was stirred at −30° C. for 2 h. On completion, the mixture was quenched with NH$_4$Cl aqueous, then extracted with EA The combined EA layers were concentrated and purified by reverse phase (0.1% FA) to give the title compound (286 mg, 60% yield) as a brown solid. $^1$H NMR (400 MHz, DMSO-d$_6$) δ 8.91 (dd, J=1.2, 7.6 Hz, 1H), 8.59-8.46 (m, 1H), 7.57-7.50 (m, 1H), 7.49-7.42 (m, 1H), 7.41-7.35 (m, 1H), 7.33-7.23 (m, 2H), 7.22-7.05 (m, 1H), 6.94-6.86 (m, 2H), 6.32-5.97 (m, 1H), 4.92-4.75 (m, 2H), 3.75 (s, 3H), 3.24-3.06 (m, 2H), 2.97-2.84 (m, 1H), 2.27-2.15 (m, 1H).

Step 8—3-(5-Bromopyrido[2,3-b]indol-9-yl)piperidine-2,6-dione

To a solution of 3-(5-bromopyrido[2,3-b]indol-9-yl)-1-[(4-methoxyphenyl)methyl]piperidine-2,6-dione (6.0 g, 12.5 mmol) in toluene (50 mL) was added MsOH (10 mL). The reaction mixture was stirred at 110° C. for 4 h. On completion, the mixture was quenched with water (20 mL), then extracted with EA (2×20 mL). The organic layers were concentrated under reduced pressure. The residue was purified by prep-HPLC (column: Phenomenex Synergi C18 150*25*10 um; mobile phase: [water (0.225% FA)-ACN]; B %: 38%-68%, 10 min) to give the title compound (2.8 g, 62% yield) as a white solid. $^1$H NMR (400 MHz, DMSO-d$_6$) δ 11.19 (s, 1H), 8.91 (dd, J=7.8, 1.5 Hz, 1H), 8.53 (dd, J=4.7, 1.3 Hz, 1H), 7.72 (br s, 1H), 7.54-7.53 (m, 1H), 7.49-7.45 (m, 1H), 7.38 (dd, J=7.9, 4.8 Hz, 1H), 6.19-6.00 (m, 1H), 3.16-2.98 (m, 2H), 2.74-2.67 (m, 1H), 2.17-2.14 (m, 1H); LC/MS (ESI, m/z): [M+1]$^+$=358.0/360.0.

3-[5-[3-[2-(2-Aminoethoxy)ethoxy]propyl]pyrido[2,3-b]indol-9-yl]piperidine-2,6-dione (Intermediate XG)

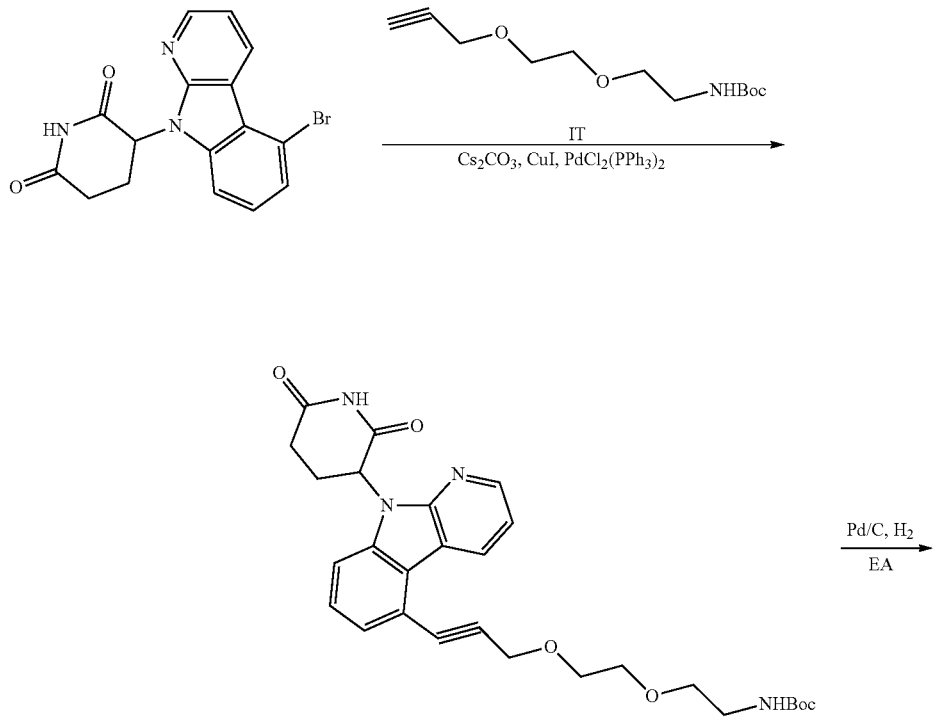

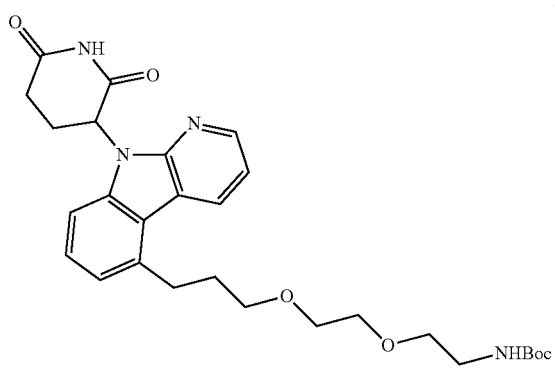

-continued

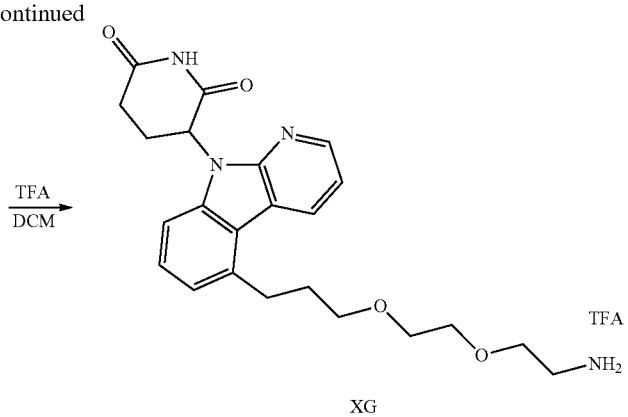

Step 1—tert-butyl (2-(2-((3-(9-(2,6-dioxopiperidin-3-yl)-9H-pyrido[2,3-b]indol-5-yl)prop-2-yn-1-yl)oxy)ethoxy)ethyl)carbamate A mixture of 3-(5-bromo-9H-pyrido[2,3-b]indol-9-yl)piperidine-2,6-dione (270 mg, 0.75 mmol), tert-butyl (2-(2-(prop-2-yn-1-yloxy)ethoxy)ethyl)carbamate (270 mg, 2.25 mmol, Intermediate IT) Cs$_2$CO$_3$ (270 mg, 2.25 mmol), PdCl$_2$(PPh$_3$)$_2$ (105 mg, 0.15 mmol) and CuI (14 mg, 0.075 mmol) in DMF (10 mL) was stirred at 80° C. for 1 h under N$_2$ with microwave. The mixture was cooled to rt, poured into water (100 mL), extracted with EtOAc (3×100 mL). The combined organic layers were concentrated under reduced pressure, the residue was purified by column chromatography on silica gel (petroleum ether:ethyl acetate=2:1) to give the title product (180 mg, 41% yield) as a white solid. LC/MS (ESI, m/z): [M+1]$^+$=360.28. $^1$H NMR (400 MHz, DMSO-d$_6$) δ 11.18 (s, 1H), 8.81 (dd, J=7.8, 1.6 Hz, 1H), 8.50 (dd, J=4.8, 1.7 Hz, 1H), 7.73-7.68 (m, 1H), 7.54 (t, J=7.9 Hz, 1H), 7.45-7.28 (m, 2H), 6.80-6.76 (m, 1H), 6.08 (s, 1H), 4.65 (s, 2H), 3.81-3.70 (m, 2H), 3.62 (dd, J=5.7, 3.6 Hz, 2H), 3.43 (t, J=6.1 Hz, 2H), 3.17-2.96 (m, 3H), 2.76-2.64 (m, 1H), 2.50-2.45 (m, 1H), 2.17-2.13 (m, 1H), 1.35 (s, 9H).

Step 2—tert-butyl (2-(2-(3-(9-(2,6-dioxopiperidin-3-yl)-9H-pyrido[2,3-b]indol-5-yl)propoxy)ethoxy)ethyl)carbamate To a mixture of tert-butyl (2-(2-((3-(9-(2,6-dioxopiperidin-3-yl)-9H-pyrido[2,3-b]indol-5-yl)prop-2-yn-1-yl)oxy)ethoxy)ethyl)carbamate (180 mg, 0.34 mmol), Pd/C (100 mg) in EA (10 mL) was stirred at rt under H$_2$ for 16 h. The mixture was filtered and the solid was washed with EA, the filtrate was concentrated under reduced pressure. Then the residue was purified by column chromatography on silica gel (petroleum ether:ethyl acetate=2:1) to give the title compound (100 mg, 56% yield) as a white solid. LC/MS (ESI, m/z): [M+1]$^+$=525.1. $^1$H NMR (400 MHz, DMSO-d$_6$) δ 11.15 (s, 1H), 8.54 (dd, J=7.9, 1.5 Hz, 1H), 8.42 (dd, J=4.9, 1.5 Hz, 1H), 7.52-7.40 (m, 2H), 7.28 (dd, J=7.8, 4.9 Hz, 1H), 7.11 (d, J=7.4 Hz, 1H), 6.77-6.74 (m, 1H), 6.10-6.00 (m, 1H), 3.61-3.50 (m, 6H), 3.43 (t, J=6.1 Hz, 2H), 3.23-3.20 (m, 2H), 3.12-2.96 (m, 4H), 2.72-2.65 (m, 1H), 2.12-2.06 (m, 1H), 1.99-1.89 (m, 2H), 1.34 (s, 9H).

Step 3—3-[5-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-5-yl]propoxy] ethoxy]ethyl]carbamate (100 mg, 190 umol) in DCM (2 mL) was added TFA (1.54 g, 13.5 mmol, 1 mL). The reaction mixture was stirred at 25° C. for 2 hrs. On completion, the mixture was concentrated in vacuo to give the title compound (100 mg, 97% yield, TFA) as a white solid. LC-MS (ESI$^+$) m/z 425.2 (M+H)$^+$.

3-(3-Methyl-5-(4-((2-(methylamino)ethoxy)methyl)piperidin-1-yl)-2-oxo-2,3-dihydro-1H-benzo[d]imidazol-1-yl)piperidine-2,6-dione methanesulfonate (Intermediate XK)

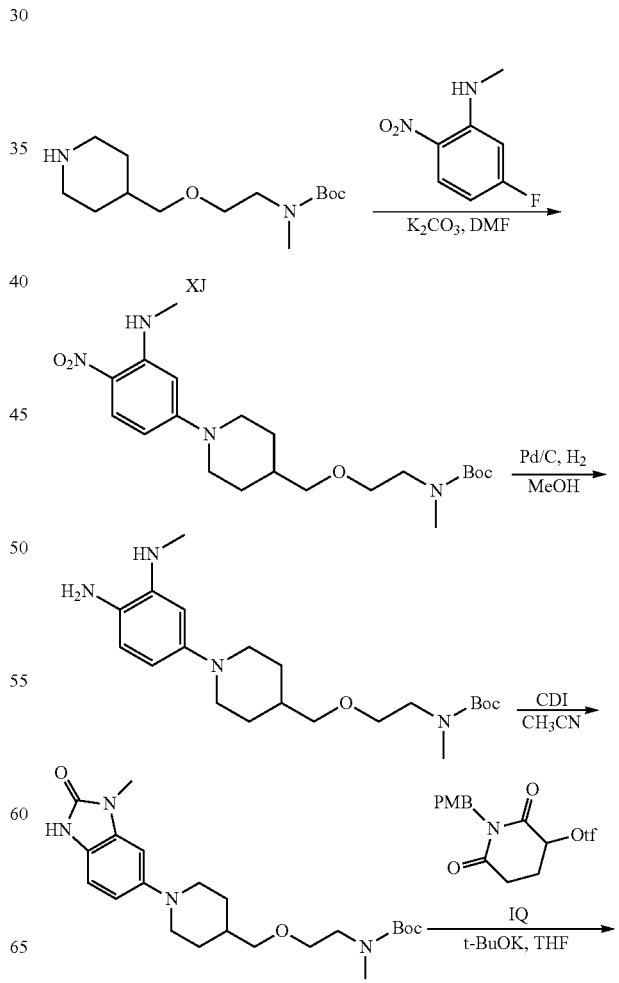

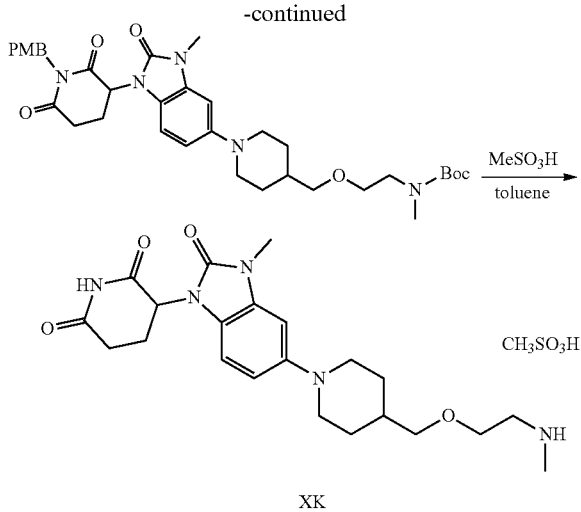

Step 1—Tert-butyl N-methyl-N-[2-[[1-[3-(methyl-amino)-4-nitro-phenyl]-4-piperidyl] methoxy] ethyl] carbamate To a solution of tert-butyl N-methyl-N-[2-(4-piperidyl-methoxy)ethyl]carbamate (3.30 g, 12.1 mmol, Intermediate XJ) in DMF (30 mL) was added 5-fluoro-N-methyl-2-nitro-aniline (2.06 g, 12.1 mmol) and $K_2CO_3$ (5.02 g, 36.4 mmol). Then the mixture was stirred at 80° C. for 12 hours. On completion, the reaction mixture was diluted with $H_2O$ (50 mL) and extracted with ethyl acetate (3×100 mL). The organic layers were washed with brine (3×50 mL). Then the organic layer was dried over anhydrous $Na_2SO_4$, filtered and concentrated in vacuo to give a residue. The residue was purified by column chromatography to give the title compound (4.40 g, 85% yield) as orange oil. LC-MS (ESI$^+$) m/z 423.5 (M+H)$^+$.

Step 2—Tert-butyl (2-((1-(4-amino-3-(methyl-amino)phenyl)piperidin-4-yl)methoxy)ethyl) (methyl)carbamate To a solution of tert-butyl N-methyl-N-[2-[[1-[3-(meth-ylamino)-4-nitro-phenyl]-4-piperidyl] methoxy]ethyl]car-bamate (3.6 g, 8.52 mmol) in MeOH (100 mL) was added Pd/C (0.7 g, 10 wt %) under $N_2$. The suspension was degassed in vacuo and purged with $H_2$ three times. The mixture was stirred under $H_2$ (15 Psi) at 25° C. for 4 hours. On completion, the reaction mixture was filtered and concentrated in vacuo to give the title compound (3.2 g, 97% yield) as brown oil. $^1$H NMR (400 MHz, CDCl$_3$) δ 6.63 (d, J=8.2 Hz, 1H), 6.34 (d, J=2.4 Hz, 1H), 6.28 (dd, J=2.6, 8.2 Hz, 1H), 3.52 (d, J=12.0 Hz, 4H), 3.45-3.31 (m, 4H), 2.93 (s, 3H), 2.86 (s, 3H), 2.62 (dt, J=2.0, 11.6 Hz, 2H), 1.83 (d, J=12.6 Hz, 2H), 1.73-1.60 (m, 1H), 1.49-1.40 (m, 11H); LC-MS (ESI$^+$) m/z 393.2 (M+H)$^+$.

Step 3—Tert-butyl (2-((1-(4-amino-3-(methyl-amino)phenyl)piperidin-4-yl)methoxy)ethyl) (methyl)carbamate To a mixture of tert-butyl N-[2-[[1-[4-amino-3-(methyl-amino)phenyl]-4-piperidyl]methoxy] ethyl]-N-methyl-car-bamate (1.5 g, 3.82 mmol) in MeCN (30 mL) was added CDI (1.24 g, 7.64 mmol) under $N_2$. The mixture was stirred for at 85° C. 16 hours. On completion, the reaction mixture was concentrated in vacuo to remove THF. The residue was diluted with water (20 mL) and extracted with EA (3×20 mL). The combined organic layers was dried over $Na_2SO_4$, filtered and concentrated in vacuo to give a residue. The residue was purified by reverse phase (FA condition) to give the title compound (1.10 g, 69% yield) as a purple solid. $^1$H NMR (400 MHz, CDCl$_3$) δ 9.06 (s, 1H), 6.95 (d, J=8.4 Hz, 1H), 6.74-6.69 (m, 1H), 6.62 (d, J=2.2 Hz, 1H), 3.60-3.52 (m, 4H), 3.39 (s, 3H), 3.37-3.31 (m, 2H), 2.93 (s, 3H), 2.73-2.65 (m, 2H), 1.86 (d, J=11.8 Hz, 2H), 1.77-1.67 (m, 2H), 1.47-1.33 (m, 13H; LC-MS (ESI$^+$) m/z 419.2 (M+H)$^+$.

Step 4—Tert-butyl (2-((1-(4-amino-3-(methyl-amino)phenyl)piperidin-4-yl)methoxy)ethyl) (methyl)carbamate To a mixture of tert-butyl N-methyl-N-[2-[[1-(3-methyl-2-oxo-1H-benzimidazol-5-yl)-4-piperidyl]methoxy]ethyl] carbamate (1.10 g, 2.63 mmol) in THF (20 mL) was added t-BuOK (442 mg, 3.94 mmol) at 0° C. under $N_2$. Then a solution of [1-[(4-methoxyphenyl)methyl]-2,6-dioxo-3-pip-eridyl] trifluoromethanesulfonate (1.50 g, 3.94 mmol, Intermediate IQ) in THF (20 mL) was added dropwise at 0° C. The mixture was warmed slowly to 25° C. and stirred at 25° C. for 24 hours. On completion, the reaction mixture was quenched by addition water (10 mL) at 25° C., and then extracted with EA (3×20 mL). The combined organic layers, dried over $Na_2SO_4$, filtered and concentrated in vacuo to give a residue. The residue was purified by column chromatography to give the title compound (800 mg, 24% yield) as brown oil. LC-MS (ESI$^+$) m/z 650.2 (M+H)$^+$.

Step 5—3-(3-methyl-5-(4-((2-(methylamino)ethoxy) methyl)piperidin-1-yl)-2-oxo-2,3-dihydro-1H-benzo[d]imidazol-1-yl)piperidine-2,6-dione methane-sulfonate To a mixture of tert-butyl N-[2-[[1-[1-[1-[(4-methoxyphe-nyl)methyl]-2,6-dioxo-3-piperidyl]-3-methyl-2-oxo-benz-imidazol-5-yl]-4-piperidyl]methoxy]ethyl]-N-methyl-car-bamate (500 mg, 769 umol) in toluene (10 mL) was added $CH_3SO_3H$ (2.22 g, 23.1 mmol) at 25° C. The mixture was stirred at 120° C. for 3 hours. On completion, the reaction mixture was quenched by addition water (2 mL) at 25° C., and then neutralized by adding NEt$_3$ to pH=5. Then the mixture was filtered and concentrated in vacuo to give a residue. The residue was purified by reverse phase (FA condition) to give the title compound (100 mg, 25% yield, $CH_3SO_3H$) as yellow oil. LC-MS (ESI$^+$) m/z 430.1 (M+H)$^+$.

N-[3-(Difluoromethyl)-1-(4-formylcyclohexyl)pyra-zol-4-yl]-2-(4-pyridyl)oxazole-4-carboxamide (Intermediate XR)

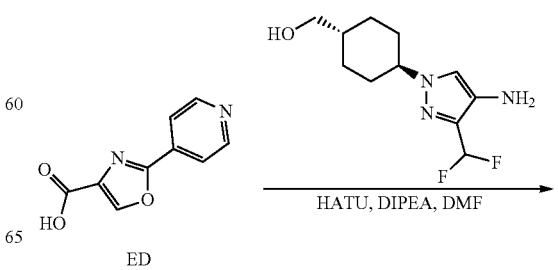

1539
-continued

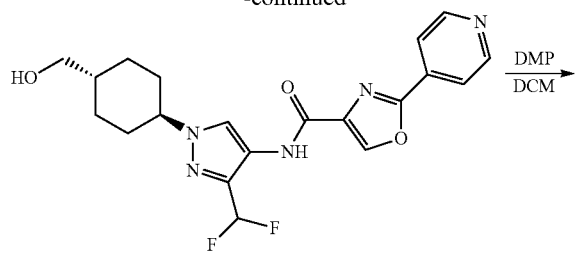

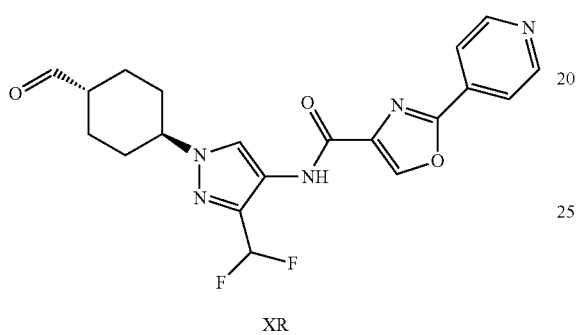

Step 1—N-[3-(difluoromethyl)-1-[4-(hydroxymethyl)cyclohexyl]pyrazol-4-yl]-2-(4-pyridyl)oxazole-4-carboxamide To a mixture of [4-[4-amino-3-(difluoromethyl)pyrazol-1-yl]cyclohexyl]methanol (170 mg, 693 umol, Intermediate TD) in DMF (2 mL) was added DIPEA (268 mg, 2.08 mmol) and 2-(4-pyridyl)oxazole-4-carboxylic acid (118 mg, 623 umol, Intermediate ED) and HATU (316 mg, 831 umol). The reaction mixture was stirred at 25° C. for 0.5 hour. On completion, the reaction mixture was quenched with water and concentrated in vacuo. The residue was purified by reverse phase to give the title compound (150 mg, 51% yield) as white solid. LC-MS (ESI+) m/z 418.2 (M+H)+.

Step 2—N-[3-(difluoromethyl)-1-(4-formylcyclohexyl)pyrazol-4-yl]-2-(4-pyridyl)oxazole-4-carboxamide To a mixture of N-[3-(difluoromethyl)-1-[4-(hydroxymethyl)cyclohexyl]pyrazol-4-yl]-2-(4-pyridyl) oxazole-4-carboxamide (120 mg, 287 umol) in DCM (15 mL) was added DMP (146 mg, 344 umol, 106 uL) at 0° C. The reaction mixture was stirred at 25° C. for 72 hours. On compound, the reaction mixture was quenched by saturated Na2S2O3 (20 mL) and saturated NaHCO3 (20 mL) at 25° C., and then stirred for 30 minutes. The solution was diluted with water (20 mL) and extracted with DCM (3×20 mL). The combined organic layers was dried over Na2SO4, filtered and concentrated in vacuo to give the title compound (119 mg, 99% yield) as light yellow solid. The residue was used to the next step directly without further purification. LC-MS (ESI+) m/z 416.2 (M+H)+.

1540
3-(7-Bromo-9H-pyrido[2,3-b]indol-9-yl)piperidine-2,6-dione (Intermediate XU)

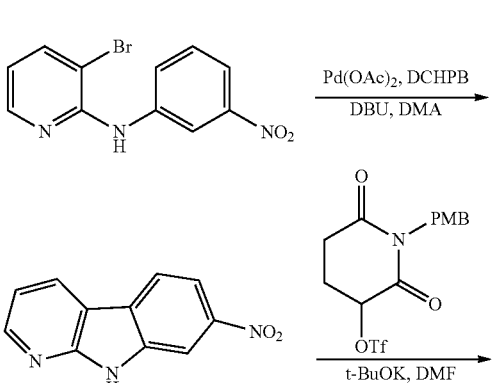

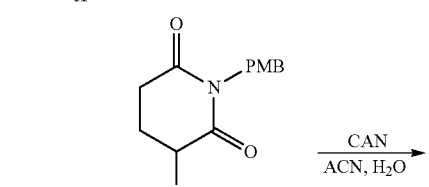

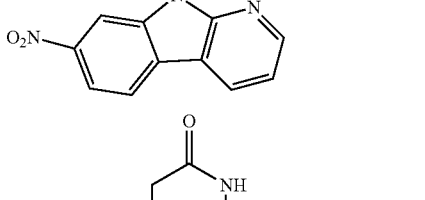

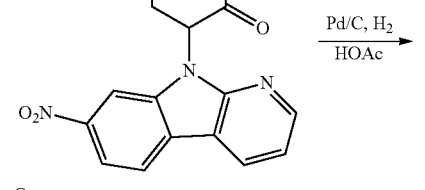

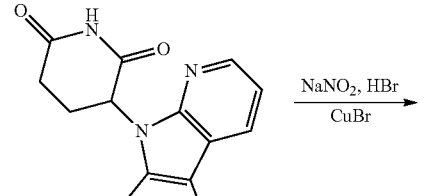

-continued

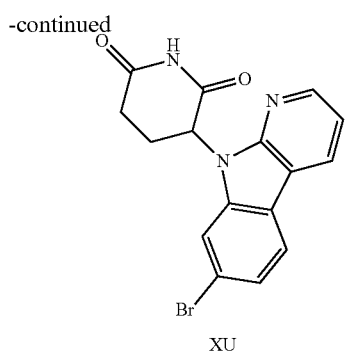

XU

Step 1—3-bromo-N-(3-nitrophenyl)pyridin-2-amine

To a mixture of 3-bromopyridin-2-amine (5 g, 28.9 mmol), 1-iodo-3-nitrobenzene (7.2 g, 28.9 mmol), Xanphos (1.07 g, 2.89 mmol), and $Cs_2CO_3$ (18.9 g, 57.8 mmol) in DMF (50 mL) was added $Pd(OAc)_2$ (323.7 mg, 1.44 mmol). The mixture was degrassed with $N_2$ and stirred at 130° C. overnight. The reaction mixture was cooled to rt, poured into water, and extracted with EtOAc (3×200 mL). The combined organic layers was washed with water (200 mL×2) and brine (200 mL×2), dried over anhydrous $Na_2SO_4$, filtered and concentrated in vacuo. The residue was purified by flash chromatography eluting with EA/PE=20% to give the title compound (5.6 g, 66% yield) as a light yellow solid. LC/MS (ESI, m/z): $[M+1]^+=294.0, 296.0$.

Step 2—7-nitro-9H-pyrido[2,3-b]indole

To a mixture of 3-bromo-N-(3-nitrophenyl)pyridin-2-amine (4 g, 6.78 mmol), DCPHB (474 mg, 1.356 mmol), and DBU (4.12 g, 27.12 mmol) in DMA (12 mL) was added $Pd(OAc)_2$ (152 mg, 0.678 mmol). The mixture was degrassed with $N_2$ and stirred at 170° C. for 1 h. The reaction mixture was cooled to rt, poured into water, and extracted with EtOAc (3×50 mL). The combined organic layers was washed with water (100 mL×2) and brine (100 mL×2), dried over anhydrous $Na_2SO_4$, filtered and concentrated in vacuo. The residue was purified by flash chromatography eluting with EA/PE=1:1 to give the title compound (1 g, 34% yield) as a light yellow solid. $^1$H NMR (400 MHz, DMSO-$d_6$) δ 12.40 (s, 1H), 8.73-8.70 (m, 1H), 8.60-8.58 (m, 1H), 8.44 (d, J=8.63 Hz, 1H), 8.33 (d, J=2.00 Hz, 1H), 8.13-8.10 (m, 1H), 7.35 (dd, J=7.75, 4.75 Hz, 1H); LC/MS (ESI, m/z): $[M+1]^+=214.1$.

Step 3—1-(4-methoxybenzyl)-3-(7-nitro-9H-pyrido[2,3-b]indol-9-yl)piperidine-2,6-dione To a solution of 7-nitro-9H-pyrido[2,3-b]indole (910 mg, 4.27 mmol) in THF (10 mL) and DMF (2 mL) was added t-BuOK (718 mg, 6.41 mmol) portion wise at 0° C. under $N_2$ atmosphere. After addition, the mixture was stirred at 0° C.-5° C. for 1 h. Then 1-(4-methoxybenzyl)-2,6-dioxopiperidin-3-yl trifluoromethanesulfonate (2.44 g, 6.41 mmol) in THF (10 mL) was added dropwise at 0° C.-5° C. over 20 min. After addition, the reaction mixture was stirred at 0° C.-5° C. for an additional 1 h. The reaction mixture was quenched by the addition of water, then extracted with EtOAc (3×20 mL). The combined organic layers was washed with brine (10 mL×2), dried over anhydrous $Na_2SO_4$, filtered and concentrated in vacuo. The residue was triturated with EtOAc and dried to give (1.3 g, 69% yield) as a light yellow solid. LC/MS (ESI, m/z): $[M+1]^+=445.2$.

Step 4—3-(7-nitro-9H-pyrido[2,3-b]indol-9-yl)piperidine-2,6-dione

To a solution of 1-(4-methoxybenzyl)-3-(7-nitro-9H-pyrido[2,3-b]indol-9-yl)piperidine-2,6-dione (1.7 g, 3.83 mmol) in $CH_3CN$ (20 mL) was added CAN (10.5 g, 19.15 mmol) in water (5 mL) at 0° C. dropwise. After addition, the mixture was stirred at rt overnight. The mixture was poured into water (50 mL), then extracted with EtOAc (3×50 mL). The combined organic layers was washed with brine (2×20 mL), dried over anhydrous $Na_2SO_4$, filtered and concentrated in vacuo. The residue was triturated with EtOAc and dried to give the title compound (850 mg, 69% yield) as a light yellow solid. LC/MS (ESI, m/z): $[M+1]^+=325.2$.

Step 5—3-(7-amino-9H-pyrido[2,3-b]indol-9-yl)piperidine-2,6-dione

To a solution of 3-(7-nitro-9H-pyrido[2,3-b]indol-9-yl)piperidine-2,6-dione (850 mg, 2.62 mmol) in EtOAc (15 mL) was added 10% palladium on activated carbon (170 mg). The mixture was hydrogened at rt overnight. The reaction mixture was filtered, the filtrate was concentrated in vacuo to give the title compound (764 mg, 99% yield) as a white solid. LC/MS (ESI, m/z): $[M+1]^+=295.2$.

Step 6—3-(7-bromo-9H-pyrido[2,3-b]indol-9-yl)piperidine-2,6-dione

To a solution of 3-(7-amino-9H-pyrido[2,3-b]indol-9-yl)piperidine-2,6-dione (661 mg, 2.26 mmol) in 40% HBr solution (10 mL) was added $NaNO_2$ (156 mg, 2.26 mmol) portion wise at 0° C. After addition, the mixture was stirred at 0° C. for 30 min. Then the diazonium solution was added dropwise to CuBr (972 mg, 6.78 mmol) in 40% HBr solution (10 mL). The mixture was stirred at rt for 2 h. Then the mixture was poured into water (50 mL), basified to pH>8 with saturated $NaHCO_3$ solution, then extracted with EtOAc (3×50 mL). The combined organic layers was washed with brine (2×30 mL), dried over anhydrous $Na_2SO_4$, filtered and concentrated in vacuo. The residue was purified by prep-HPLC to give the title compound (382 mg, 47% yield) as a yellow solid. LC/MS (ESI, m/z): $[M+1]^+=358.1, 360.1$.

3-[7-[3-[2-(2-Aminoethoxy)ethoxy]propyl]pyrido[2,3-b]indol-9-yl]piperidine-2,6-dione (Intermediate XV)

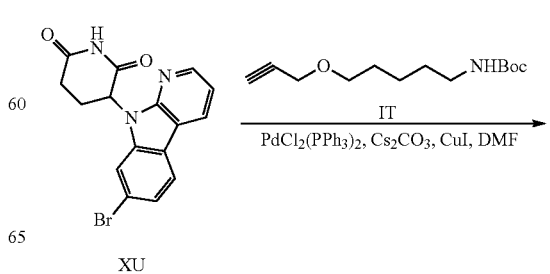

XU

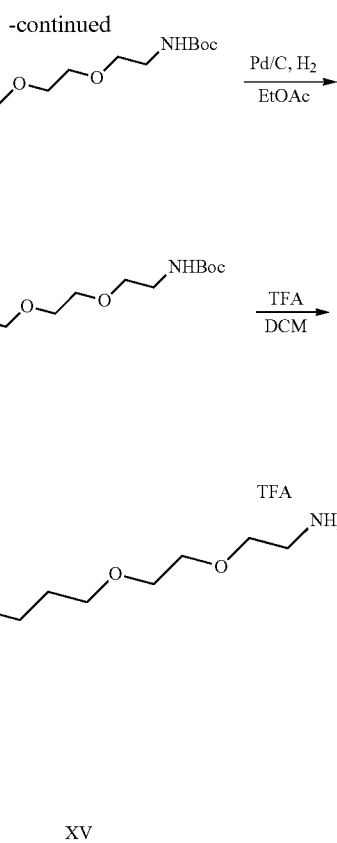

XV

Step 1—tert-butyl (2-(2-((3-(9-(2,6-dioxopiperidin-3-yl)-9H-pyrido[2,3-b]indol-7-yl)prop-2-yn-1-yl)oxy)ethoxy)ethyl)carbamate To a mixture of 3-(7-bromo-9H-pyrido[2,3-b]indol-9-yl)piperidine-2,6-dione (461 mg, 1.29 mmol, Intermediate XU), tert-butyl (2-(2-(prop-2-yn-1-yloxy)ethoxy)ethyl)carbamate (941 mg, 3.87 mmol, Intermediate IT), and Cs₂CO₃ (2.1 g, 6.45 mmol) in DMF was added CuI (49 mg, 0.258 mmol) and PdCl₂(PPh₃)₂ (181 mg, 0.258 mmol). The mixture was degrassed with N₂ and stirred at 80° C. for 1 h under microwave condition. The reaction mixture was cooled to rt, poured into water, then extracted with EtOAc (3×20 mL). The combined organic layers was washed with water (20 mL×2) and brine (2×30 mL), dried over anhydrous Na₂SO₄, filtered and concentrated in vacuo. The residue was purified by flash chromatography eluting with EA/DCM=1:1 to the title compound (410 mg, 68% yield) as yellow solid. LC/MS (ESI, m/z): [M-55+H]=466.1.

Step 2—tert-butyl (2-(2-(3-(9-(2,6-dioxopiperidin-3-yl)-9H-pyrido[2,3-b]indol-7-yl)propoxy)ethoxy)ethyl)carbamate To a solution of tert-butyl (2-(2-((3-(9-(2,6-dioxopiperidin-3-yl)-9H-pyrido[2,3-b]indol-7-yl)prop-2-yn-1-yl)oxy)ethoxy)ethyl)carbamate (400 mg, 0.77 mmol) in EtOAc (5 mL) was added 10% palladium on activated carbon (81 mg). The mixture was hydrogened at rt overnight. The reaction mixture was filtered, the filtrate was concentrated in vacuo. The residue was purified by P-TLC eluting with EA/DCM=1:2 firstly, then the crude compound was purified by prep HPLC to give the title compound (132 mg, 66% yield) as a white solid. ¹H NMR (400 MHz, DMSO-d₆) δ 11.13 (s, 1H), 8.49 (dd, J=7.63, 1.50 Hz, 1H), 8.38-8.35 (m, 1H), 8.11 (d, J=7.88 Hz, 1H), 7.47 (br. s., 1H), 7.24 (dd, J=7.63, 4.88 Hz, 1H), 7.12-7.18 (m, 1H), 6.77-6.74 (m, 1H), 6.01 (br. s., 1H), 3.47-3.55 (m, 4H), 3.45-3.37 (m, 4H), 3.15-3.02 (m, 4H), 2.80 (t, J=7.69 Hz, 2H), 2.73-2.68 (m, 1H), 2.13-2.07 (m, 1H), 1.94-1.88 (m, 2H), 1.36 (s, 9H); LC/MS (ESI, m/z): [M+1]⁺=525.3.

Step 3—3-[7-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-7-yl]propoxy] ethoxy]ethyl] carbamate (95.0 mg, 181 umol) in DCM (3 mL) was added TFA (722 mg, 6.34 mmol). The reaction mixture was stirred at 25° C. for 1 hr. On completion, the reaction mixture was concentrated in vacuo to give the title compound (95 mg, 95% yield, TFA) as light yellow oil. LC-MS (ESI⁺) m/z 425.2 (M+H)⁺.

3-(4-Bromo-9H-pyrido[2,3-b]indol-9-yl)piperidine-2,6-dione (Intermediate XY)

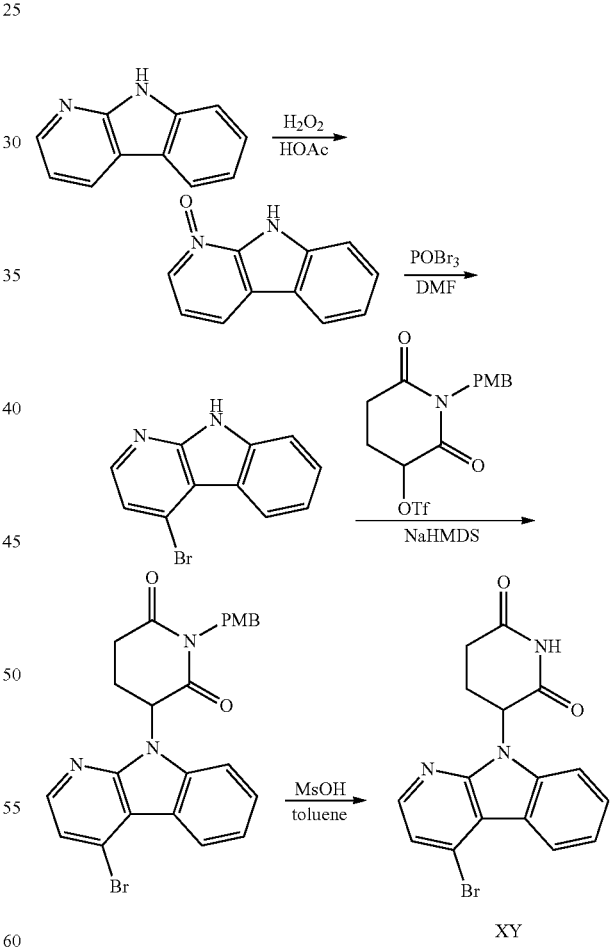

Step 1—9H-pyrido[2,3-b]indole 1-oxide

To a stirred solution of 9H-pyrido[2,3-b]indole (10 g, 59.5 mmol) in AcOH (100 mL) was added 30% H₂O₂ (50 mL) dropwise. After the addition, the reaction mixture was

1545 heated to 110° C. and stirred for 6 h. Then the reaction mixture was cooled to rt and concentrated in vacuo. To the residue was added sat. aq. K$_2$CO$_3$ to basify to pH=8. The mixture was stirred at rt overnight and filtered. The solid was washed with water and dried to afford the title compound (7.3 g, 67% yield) as a yellow solid. $^1$H NMR (400 MHz, DMSO-d$_6$) δ 12.58 (s, 1H), 8.36-8.34 (m, 1H), 8.25-8.14 (m, 2H), 7.58-7.50 (m, 2H), 7.35-7.18 (m, 2H). LC/MS (ESI, m/z): [M+1]$^+$=185.1

Step 2—4-bromo-9H-pyrido[2,3-b]indole

To a solution of 9H-pyrido[2,3-b]indole 1-oxide (9.3 g, 50.5 mmol) in DMF (100 mL) was added phosphorusoxybromide (29.0 g, 101.1 mmol) at rt. The reaction mixture was stirred at rt overnight and filtered. The solid was washed with water and dried to afford the title compound (9.0 g, 73% yield) as a yellow solid. $^1$H NMR (400 MHz, CDCl$_3$) δ 9.28 (s, 1H), 8.61 (d, J=8.0 Hz, 1H), 8.25 (d, J=5.4 Hz, 1H), 7.59-7.52 (m, 2H), 7.43-7.33 (m, 2H). LC/MS (ESI, m/z): [M+1]$^+$=247.3, 249.3.

Step 3—3-(4-bromo-9H-pyrido[2,3-b]indol-9-yl)-1-(4-methoxybenzyl)piperidine-2,6-dione To a solution of 4-bromo-9H-pyrido[2,3-b]indole (8.8 g, 35.6 mmol) and 18-crown-6 (1.9 g, 7.13 mmol) in THF (100 mL) was added NaHMDS (26.7 mL, 53.4 mmol, 2N in THF) dropwise at −30° C. under N$_2$ atmosphere. After addition, the reaction mixture was stirred at −30° C. for 1 h. Then 1-(4-methoxybenzyl)-2,6-dioxopiperidin-3-yl trifluoromethanesulfonate (20.4 g in 30 mL THF, 53.4 mmol) was added to solution dropwise. After addition, the reaction mixture was stirred at −30° C. for 2 h and quenched by sat. aq. NH$_4$Cl (100 mL), then extracted with EA (150 mL×2). The combined organic layers were washed with brine (100 mL×2), dried over anhydrous Na$_2$SO$_4$, filtered and concentrated in vacuo. The residue was purified by column to give the title compound (10.0 g, 59% yield) as a white solid. LC/MS (ESI, m/z): [M+1]$^+$=478.3.

Step 4—3-(4-bromo-9H-pyrido[2,3-b]indol-9-yl)piperidine-2,6-dione

To a solution of 3-(4-bromo-9H-pyrido[2,3-b]indol-9-yl)-1-(4-methoxybenzyl)piperidine-2,6-dione (10 g, 20.9 mmol) in toluene (50 mL) was added methanesulfonic acid (20 mL). The reaction solution was heated to 110° C. and stirred for 2 h. The reaction mixture was cooled to rt and concentrated to remove toluene. The residue was diluted with CH$_3$CN and purified via reverse phase column chromatography (CH$_3$CN/H$_2$O=5%-80%) to give the title compound (3.7 g, 50% yield) as a white solid. $^1$H NMR (400 MHz, DMSO-d$_6$) δ 11.19 (s, 1H), 8.57 (d, J=7.9 Hz, 1H), 8.30 (d, J=5.3 Hz, 1H), 7.73-7.69 (m, 1H), 7.63 (t, J=7.9 Hz, 1H), 7.56 (d, J=5.3 Hz, 1H), 7.41 (t, J=7.9 Hz, 1H), 6.10 (s, 1H), 3.14-2.98 (m, 2H), 2.73-2.68 (m, 1H), 2.18-2.12 (m, 1H). LC/MS (ESI, m/z): [M+1]$^+$=358.0.

3-[4-[3-[2-(2-Aminoethoxy)ethoxy]propyl]pyrido[2,3-b]indol-9-yl]piperidine-2,6-dione (Intermediate XZ)

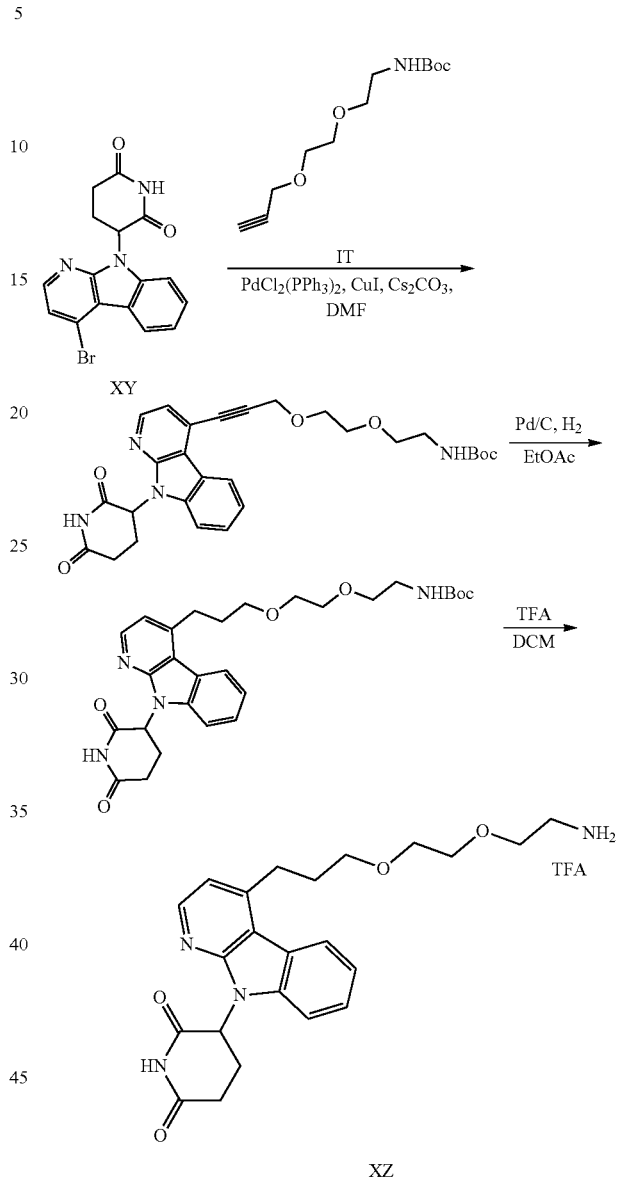

Step 1—tert-butyl (2-(2-((3-(9-(2,6-dioxopiperidin-3-yl)-9H-pyrido[2,3-b]indol-4-yl)prop-2-yn-1-yl)oxy)ethoxy)ethyl)carbamate To a mixture of 3-(4-bromo-9H-pyrido[2,3-b]indol-9-yl)piperidine-2,6-dione (0.3 g, 0.84 mmol, Intermediate XY), tert-butyl (2-(2-(prop-2-yn-1-yloxy)ethoxy)ethyl)carbamate (0.31 g, 1.26 mmol, Intermediate IT), Cs$_2$CO$_3$ (2.7 g, 8.38 mmol) in DMF (10 mL) was added CuI (16 mg, 0.084 mmol) and PdCl$_2$(PPh$_3$)$_2$ (0.12 g, 0.17 mmol). The mixture was degrassed with N$_2$ and stirred at 80° C. for 1 h under microwave condition. The reaction mixture was cooled to rt, poured into water, then extracted with EtOAc (3×20 mL). The combined organic layers was washed with water (20 mL×2) and brine, dried over anhydrous Na$_2$SO$_4$, filtered and concentrated in vacuo. The residue was purified by flash chromatography eluting with EA/DCM=1:1 to give the title compound (0.16 g, 37% yield) as yellow solid. LC/MS (ESI, m/z): [M−55+H]$^+$=466.1.

Step 2—tert-butyl (2-(2-(3-(9-(2,6-dioxopiperidin-3-yl)-9H-pyrido[2,3-b]indol-4-yl)propoxy)ethoxy)ethyl)carbamate To a solution of tert-butyl (2-(2-((3-(9-(2,6-dioxopiperidin-3-yl)-9H-pyrido[2,3-b]indol-4-yl)prop-2-yn-1-yl)oxy)ethoxy)ethyl)carbamate (0.16 g, 0.31 mmol) in EtOAc (5 mL) was added 10% palladium on activated carbon (32 mg). The mixture was hydrogened at rt overnight. Then the reaction mixture was filtered and the filtrate was concentrated in vacuo. The residue was purified by P-TLC eluting with EA/DCM=1:2 firstly, then the crude compound was purified by prep HPLC to give the title compound (60 mg, 38% yield) as a white solid. $^1$H NMR (400 MHz, CDCl$_3$) δ 8.32 (d, J=5.1 Hz, 1H), 8.20 (d, J=7.9 Hz, 1H), 8.12 (s, 1H), 7.53-7.46 (m, 1H), 7.34-7.28 (m, 2H), 7.06-7.04 (m, 1H), 5.96 (s, 1H), 5.00 (s, 1H), 3.66-3.56 (m, 8H), 3.41-3.24 (m, 4H), 3.09-2.99 (m, 3H), 2.33-2.29 (m, 1H), 2.18-2.11 (m, 2H), 1.43 (s, 9H). LC/MS (ESI, m/z): [M+1]$^+$=525.4.

Step 3—3-[4-[3-[2-(2-Aminoethoxy)ethoxy]propyl]pyrido[2,3-b]indol-9-yl]piperidine-2,6-dione To a solution of tert-butyl N-[2-[2-[3-[9-(2,6-dioxo-3-piperidyl)pyrido[2,3-b]indol-4-yl]propoxy] ethoxy]ethyl] carbamate (66.0 mg, 125 umol) in DCM (2 mL) was added TFA (573 mg, 5.03 mmol). The mixture was stirred at 25° C. for 2 hrs. On completion, the mixture was concentrated in vacuo to give the title compound (67.0 mg, 95% yield, TFA) as light yellow oil. LC-MS (ESI$^+$) m/z 425.0 (M+H)$^+$.

3-[3-Methyl-4-[[(2R)-2-(methylaminomethyl)morpholin-4-yl]methyl]-2-oxo-benzimidazol-1-yl]piperidine-2,6-dione (Intermediate YK)

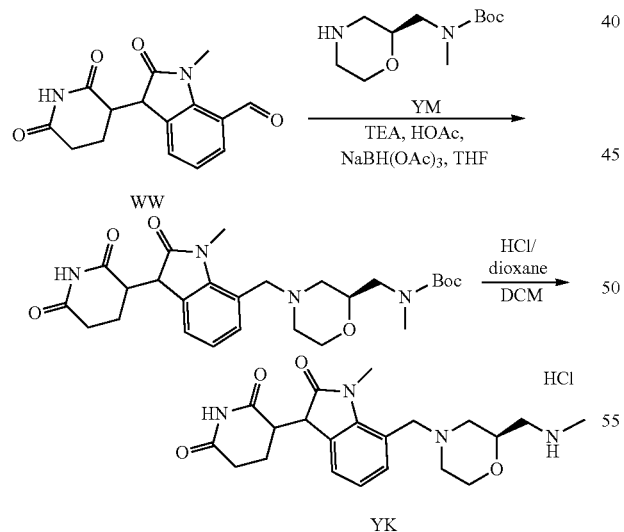

Step 1—N-[[(2S)-4-[[1-(2,6-dioxo-3-piperidyl)-3-methyl-2-oxo-benzimidazol-4-yl]methyl]morpholin-2-yl]methyl]-N-methyl-carbamate To a solution of 1-(2,6-dioxo-3-piperidyl)-3-methyl-2-oxo-benzimidazole-4-carbaldehyde (249 mg, 868 umol, Intermediate WW) and tert-butyl N-methyl-N-[[(2S)-morpholin-2-yl]methyl]carbamate (200 mg, 868 umol, Intermediate YM) in THF (15 mL) was added TEA (87.8 mg, 868 umol). The reaction mixture was stirred at 25° C. for 15 minutes. Then AcOH (156 mg, 2.61 mmol) and NaBH(OAc)$_3$ (552 mg, 2.61 mmol) was added. The reaction mixture was stirred at 25° C. for 12 hours. On completion, the reaction was quenched with water (3 mL) and the reaction mixture was concentrated in vacuo. The residue was purified by reverse phase (0.1% FA) to give the title compound (250 mg, 57% yield) as a white solid. LC-MS (ESI$^+$) m/z 502.1 (M+H)$^+$.

Step 2—3-[3-Methyl-4-[[(2R)-2-(methylaminomethyl)morpholin-4-yl]methyl]-2-oxo-benzimidazol-1-yl]piperidine-2,6-dione To a solution of tert-butyl N-[[(2S)-4-[[1-(2,6-dioxo-3-piperidyl)-3-methyl-2-oxo-benzimidazol-4-yl] methyl]morpholin-2-yl]methyl]-N-methyl-carbamate (100 mg, 199 umol) in DCM (1 mL) was added HCl/dioxane (4 M, 20.0 mL). The reaction mixture was stirred at 25° C. for 30 minutes. On completely, the reaction mixture was concentrated in vacuo to give the title compound (80.0 mg, 91% yield, HCl) as a white solid. LC-MS (ESI$^+$) m/z 402.1 (M+H)$^+$.

Tert-butyl N-methyl-N-[[(2S)-morpholin-2-yl]methyl]carbamate (Intermediate YM)

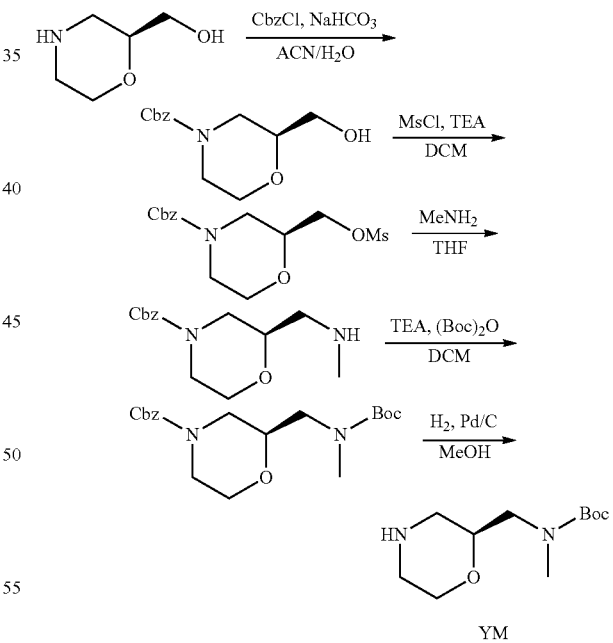

Step 1—Benzyl (2S)-2-(hydroxymethyl)morpholine-4-carboxylate

To a solution of [(2S)-morpholin-2-yl]methanol (5 g, 32.5 mmol, HCl; CAS #132073-83-7) and NaHCO$_3$ (6.84 g, 81.4 mmol) in a mixed solvent of ACN (10 mL) and H$_2$O (10 mL) was added CbzCl (8.33 g, 48.8 mmol). The reaction mixture was stirred at 25° C. for 12 hrs. On completion, the mixture was concentrated in vacuo to remove ACN. The residue was extracted with EA (2×20 mL), then the combined organic layers were concentrated in vacuo. The residue was purified by silica gel column (PE:EA=1:1) to give the title compound (7.1 g, 87% yield) as colorless oil. $^1$H NMR (400 MHz, CDCl$_3$) δ 7.42-7.33 (m, 5H), 5.17 (d, J 2.0 Hz, 2H), 4.08-3.88 (m, 3H), 3.77-3.65 (m, 1H), 3.63-3.46 (m, 3H), 3.13-2.73 (m, 2H), 2.07-1.96 (m, 1H). LC-MS (ESI$^+$) m/z 274.1 (M+Na)$^+$.

Step 2—Benzyl (2S)-2-(methylsulfonyloxymethyl)morpholine-4-carboxylate

To a solution of benzyl (2S)-2-(hydroxymethyl)morpholine-4-carboxylate (7.1 g, 28.2 mmol) and triethylamine (5.72 g, 56.5 mmol) in dichloromethane (70 mL) was added methanesulfonyl chloride (4.86 g, 42.3 mmol) at 0° C. The reaction mixture was stirred at 25° C. for 1 hr. On completion, the mixture was diluted with dichloromethane (20 mL) and washed with water (3×30 mL). The organic layer was dried over anhydrous sodium sulfate, filtered and concentrated in vacuo to give the title compound (9.31 g, 100% yield) as yellow oil. $^1$H NMR (400 MHz, CDCl$_3$) δ 7.43-7.33 (m, 5H), 5.20-5.15 (m, 2H), 4.26 (d, J 4.8 Hz, 2H), 4.10-3.83 (m, 3H), 3.80-3.65 (m, 1H), 3.63-3.48 (m, 1H), 3.08 (s, 3H), 3.07-2.75 (m, 2H).

Step 3—Benzyl (2R)-2-(methylaminomethyl)morpholine-4-carboxylate

A solution of benzyl (2S)-2-(methylsulfonyloxymethyl)morpholine-4-carboxylate (9.31 g, 28.2 mmol) in EtOH (10 mL) saturated with methanamine (58.5 g, 565 mmol) was stirred under 50 Psi at 80° C. for 12 hrs in a 100 mL of autoclave. On completion, the mixture was concentrated in vacuo to give the title compound (7.47 g, 100% yield) as yellow oil, which was used for the next step without purification.

Step 4—Benzyl (2R)-2-[[tert-butoxycarbonyl(methyl)amino]methyl]morpholine-4-carboxylate To a solution of benzyl (2R)-2-(methylaminomethyl)morpholine-4-carboxylate (7.47 g, 28.2 mmol) in MeOH (100 mL) was added (Boc)$_2$O (9.25 g, 42.4 mmol, 9.74 mL) and TEA (4.29 g, 42.4 mmol). The reaction mixture was stirred at 25° C. for 12 hrs. On completion, the mixture was concentrated in vacuo. The residue was purified by silica gel column (PE:EA=5:1) to give the title compound (9.10 g, 88% yield) as yellow oil, $^1$H NMR (400 MHz, CDCl$_3$) δ 7.43-7.30 (m, 5H), 5.24-5.09 (m, 2H), 4.11-3.83 (m, 3H), 3.68-3.34 (m, 3H), 3.30-3.14 (m, 1H), 3.09-2.97 (m, 1H), 2.94 (s, 3H), 2.80-2.62 (m, 1H), 1.47 (s, 9H).

Step 5—Tert-butyl N-methyl-N-[[(2S)-morpholin-2-yl]methyl]carbamate

To a solution of benzyl (2R)-2-[[tert-butoxycarbonyl(methyl)amino]methyl]morpholine-4-carboxylate (9.1 g, 24.9 mmol) in THF (100 mL) was added Pd/C (1.00 g, 10% wt) under N$_2$ atmosphere. The suspension was degassed and purged with H$_2$ three times. The mixture was stirred under H$_2$ (15 Psi) at 25° C. for 12 hrs. On completion, the mixture was filtered and the filtrate was concentrated in vacuo to give the title compound (5.7 g, 99% yield) as colorless oil. $^1$H NMR (400 MHz, CDCl$_3$) δ 3.91-3.83 (m, 1H), 3.68-3.55 (m, 2H), 3.48-3.33 (m, 1H), 3.12 (dd, J=6.2, 14.4 Hz, 1H), 2.94 (s, 3H), 2.92-2.88 (m, 1H), 2.86 (dd, J=3.2, 10.8 Hz, 1H), 2.84-2.78 (m, 1H), 2.57 (dd, J=10.3, 12.0 Hz, 1H), 1.47 (s, 9H).

Tert-butyl N-methyl-N-[[(2S)-morpholin-2-yl]methyl]carbamate (Intermediate YM)

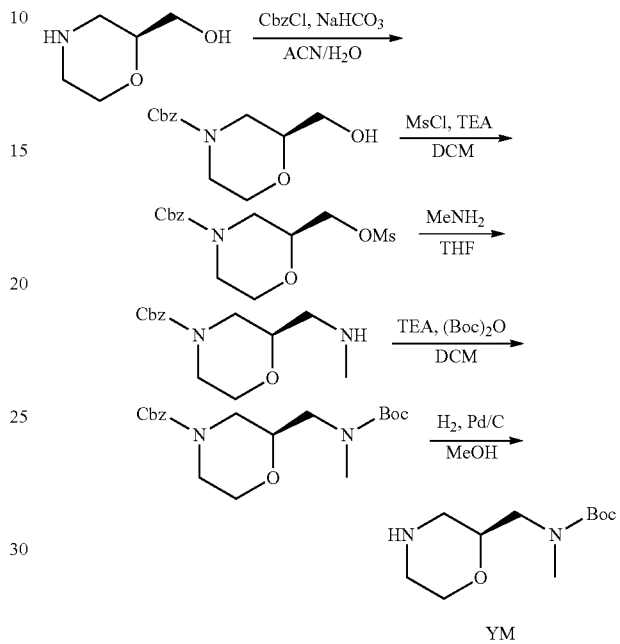

Step 1—Benzyl (2S)-2-(hydroxymethyl)morpholine-4-carboxylate

To a solution of [(2S)-morpholin-2-yl]methanol (5 g, 32.5 mmol, HCl; CAS #132073-83-7) and NaHCO$_3$ (6.84 g, 81.4 mmol) in a mixed solvent of ACN (10 mL) and H$_2$O (10 mL) was added CbzCl (8.33 g, 48.8 mmol). The reaction mixture was stirred at 25° C. for 12 hrs. On completion, the mixture was concentrated in vacuo to remove ACN. The residue was extracted with EA (2×20 mL), then the combined organic layers were concentrated in vacuo. The residue was purified by silica gel column (PE:EA=1:1) to give the title compound (7.1 g, 87% yield) as colorless oil. $^1$H NMR (400 MHz, CDCl$_3$) δ 7.42-7.33 (m, 5H), 5.17 (d, J 2.0 Hz, 2H), 4.08-3.88 (m, 3H), 3.77-3.65 (m, 1H), 3.63-3.46 (m, 3H), 3.13-2.73 (m, 2H), 2.07-1.96 (m, 1H). LC-MS (ESI$^+$) m/z 274.1 (M+Na)$^+$.

Step 2—Benzyl (2S)-2-(methylsulfonyloxymethyl)morpholine-4-carboxylate

To a solution of benzyl (2S)-2-(hydroxymethyl)morpholine-4-carboxylate (7.1 g, 28.2 mmol) and triethylamine (5.72 g, 56.5 mmol) in dichloromethane (70 mL) was added methanesulfonyl chloride (4.86 g, 42.3 mmol) at 0° C. The reaction mixture was stirred at 25° C. for 1 hr. On completion, the mixture was diluted with dichloromethane (20 mL) and washed with water (3×30 mL). The organic layer was dried over anhydrous sodium sulfate, filtered and concentrated in vacuo to give the title compound (9.31 g, 100% yield) as yellow oil. $^1$H NMR (400 MHz, CDCl$_3$) δ 7.43-

7.33 (m, 5H), 5.20-5.15 (m, 2H), 4.26 (d, J=4.8 Hz, 2H), 4.10-3.83 (m, 3H), 3.80-3.65 (m, 1H), 3.63-3.48 (m, 1H), 3.08 (s, 3H), 3.07-2.75 (m, 2H).

Step 3—Benzyl (2R)-2-(methylaminomethyl)morpholine-4-carboxylate

A solution of benzyl (2S)-2-(methyl sulfonyloxymethyl)morpholine-4-carboxylate (9.31 g, 28.2 mmol) in EtOH (10 mL) saturated with methanamine (58.5 g, 565 mmol) was stirred under 50 Psi at 80° C. for 12 hrs in a 100 mL of autoclave. On completion, the mixture was concentrated in vacuo to give the title compound (7.47 g, 100% yield) as yellow oil, which was used for the next step without purification.

Step 4—Benzyl (2R)-2-[[tert-butoxycarbonyl(methyl)amino]methyl]morpholine-4-carboxylate To a solution of benzyl (2R)-2-(methylaminomethyl)morpholine-4-carboxylate (7.47 g, 28.2 mmol) in MeOH (100 mL) was added (Boc)$_2$O (9.25 g, 42.4 mmol, 9.74 mL) and TEA (4.29 g, 42.4 mmol). The reaction mixture was stirred at 25° C. for 12 hrs. On completion, the mixture was concentrated in vacuo. The residue was purified by silica gel column (PE:EA=5:1) to give the title compound (9.10 g, 88% yield) as yellow oil, $^1$H NMR (400 MHz, CDCl$_3$) δ 7.43-7.30 (m, 5H), 5.24-5.09 (m, 2H), 4.11-3.83 (m, 3H), 3.68-3.34 (m, 3H), 3.30-3.14 (m, 1H), 3.09-2.97 (m, 1H), 2.94 (s, 3H), 2.80-2.62 (m, 1H), 1.47 (s, 9H).

Step 5—Tert-butyl N-methyl-N-[[(2S)-morpholin-2-yl]methyl]carbamate

To a solution of benzyl (2R)-2-[[tert-butoxycarbonyl(methyl)amino]methyl]morpholine-4-carboxylate (9.1 g, 24.9 mmol) in THF (100 mL) was added Pd/C (1.00 g, 10% wt) under N$_2$ atmosphere. The suspension was degassed and purged with H$_2$ three times. The mixture was stirred under H$_2$ (15 Psi) at 25° C. for 12 hrs. On completion, the mixture was filtered and the filtrate was concentrated in vacuo to give the title compound (5.7 g, 99% yield) as colorless oil. $^1$H NMR (400 MHz, CDCl$_3$) δ 3.91-3.83 (m, 1H), 3.68-3.55 (m, 2H), 3.48-3.33 (m, 1H), 3.12 (dd, J=6.2, 14.4 Hz, 1H), 2.94 (s, 3H), 2.92-2.88 (m, 1H), 2.86 (dd, J=3.2, 10.8 Hz, 1H), 2.84-2.78 (m, 1H), 2.57 (dd, J=10.3, 12.0 Hz, 1H), 1.47 (s, 9H).

3-[4-(Aminomethyl)-3-methyl-2-oxo-benzimidazol-1-yl]piperidine-2,6-dione (Intermediate YN)

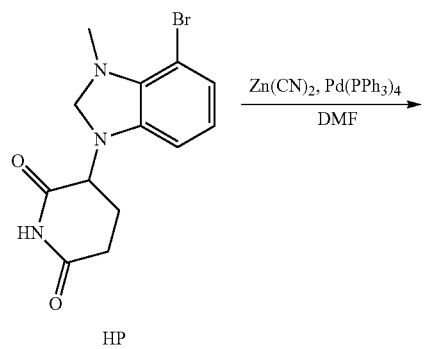

HP

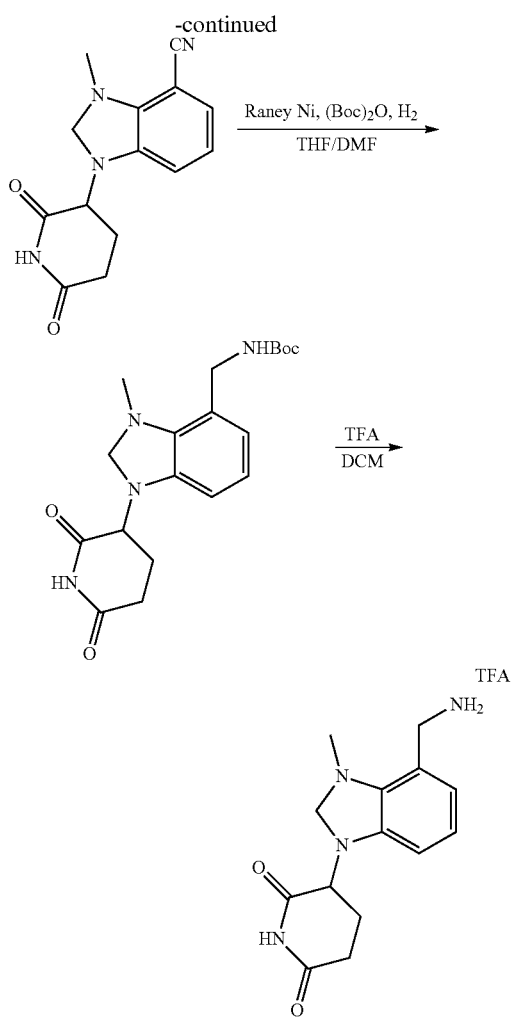

YN

Step 1—1-(2,6-Dioxo-3-piperidyl)-3-methyl-2-oxo-benzimidazole-4-carbonitrile

To a solution of 3-(4-bromo-3-methyl-2-oxo-benzimidazol-1-yl)piperidine-2,6-dione (500 mg, 1.48 mmol, Intermediate HP) in DMF (10 mL) was added Zn(CN)$_2$ (190 mg, 1.62 mmol) and Pd(PPh$_3$)$_4$ (180 mg, 155 umol) at 25° C. The mixture was stirred at 100° C. for 3 hours under N$_2$. On completion, the mixture was cooled to 25° C. The mixture was filtered, and the cake was washed with EA (30 mL). The filtrate and washing were combined and concentrated in vacuo. The residue was purified by reversed phase flash (FA condition) to give the title compound (100 mg, 24% yield) as light yellow solid. $^1$H NMR (400 MHz, DMSO-d$_6$) δ 11.17 (s, 1H), 7.48 (d, J=7.6 Hz, 2H), 7.19 (t, J=8.0 Hz, 1H), 5.47-5.44 (m 1H), 3.61 (s, 3H), 2.72-2.69 (m, 1H), 2.66-2.62 (m, 2H), 2.07-2.03 (m, 1H); LC-MS (ESI$^+$) m/z 285.1 (M+H)$^+$.

Step 2—Tert-butyl N-[[1-(2,6-dioxo-3-piperidyl)-3-methyl-2-oxo-benzimidazol-4-yl]methyl] carbamate To a solution of 1-(2,6-dioxo-3-piperidyl)-3-methyl-2-oxo-benzimidazole-4-carbonitrile (100 mg, 351 umol) and Boc$_2$O (85.0 mg, 389 umol) in THF (2 mL) and DMF (2 mL)

was added Raney-Ni (100 mg) at 20° C. The mixture was stirred at 30° C. for 16 hours under H2 (50 Psi). On completion, the mixture was filtered, and the filter cake was washed with THF (20 mL). The filtrate and washing were combined and concentrated in vacuo to give the title compound (120 mg, 87% yield) as light yellow gum. LC-MS (ESI$^+$) m/z 411.2 (M+Na)$^+$.

Step 3—3-[4-(Aminomethyl)-3-methyl-2-oxo-benzimidazol-1-yl]piperidine-2,6-dione

To a solution of tert-butyl N-[[1-(2,6-dioxo-3-piperidyl)-3-methyl-2-oxo-benzimidazol-4-yl] methyl]carbamate (120 mg, 308 umol) in DCM (2 mL) was added TFA (1 mL) at 20° C. The mixture was stirred at 20° C. for 1 hour. On completion, the mixture was concentrated in vacuo to give the title compound (120 mg, 96% yield, TFA) as light yellow solid. LC-MS (ESI$^+$) m/z 311.2 (M+Na)$^+$.

Tert-butyl N-methyl-N-(3-prop-2-ynoxycyclobutyl) carbamate (Intermediate YO)

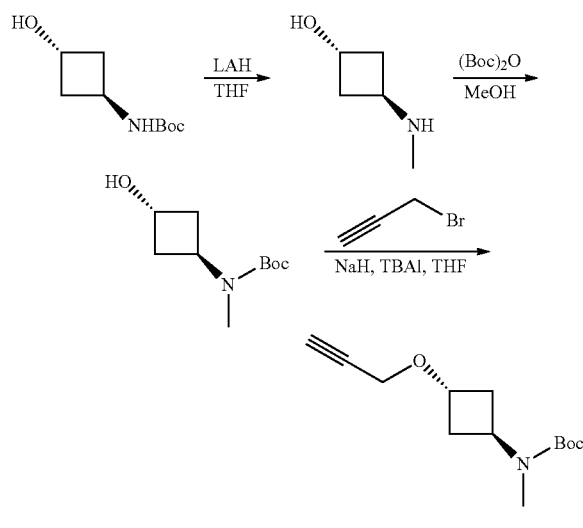

Step 1—3-(Methylamino)cyclobutanol

To a stirred solution of LAH (2.43 g, 64.1 mmol) in THF (100 mL) was added a solution of tert-butyl N-(3-hydroxycyclobutyl)carbamate (10.0 g, 53.4 mmol, CAS #389890-42-0) in THF (100 mL) at 0° C. Then the reaction mixture was stirred at 60° C. for 24 hrs. On completion, the reaction mixture was concentrated in vacuo. On completion, the mixture was cooled to 0° C., quenched with H$_2$O (2.4 mL) and added 15% NaOH (2.4 mL). After stirred for 15 minutes, H$_2$O (2.4 mL×3) was added into the above mixture. Then the mixture was warmed to rt and added anhydrous Na$_2$SO$_4$. The mixture was stirred for 10 minutes, filtered and the filtrate was concentrated in vacuo to give the title compound (4.90 g, 91% yield) as colorless oil. $^1$H NMR (400 MHz, DMSO-d$_6$) δ 5.01 (s, 1H), 4.23-4.20 (m, 1H), 3.13-3.00 (m, 1H), 2.13 (s, 3H), 1.93-1.84 (m, 4H), 1.70-1.47 (m, 1H).

Step 2—Tert-butyl N-(3-hydroxycyclobutyl)-N-methyl-carbamate

To a solution of 3-(methylamino)cyclobutanol (4.90 g, 48.4 mmol) in methyl alcohol (50 mL) was added (Boc)$_2$O (11.6 g, 53.3 mmol, 12.2 mL) for 3 hr at 25° C. Then another batch of (Boc)$_2$O (10.6 g, 48.4 mmol) was added. The mixture was stirred at 25° C. for another 19 hrs. On completion, the reaction mixture was concentrated in vacuo. The residue was purified by column chromatography (SiO$_2$, Petroleum ether/Ethyl acetate=1:1) to give the title compound (2.85 g, 30% yield) as yellow oil. $^1$H NMR (DMSO-d$_6$) δ 4.94 (s, 1H), 4.25-4.21 (m, 1H), 4.10-4.19 (m, 1H), 2.72 (s, 3H), 2.23-2.35 (m, 2H), 1.91-2.03 (m, 2H), 1.38 (s, 9H).

Step 3—Tert-butyl N-methyl-N-(3-prop-2-ynoxycyclobutyl)carbamate

To a solution of tert-butyl N-(3-hydroxycyclobutyl)-N-methyl-carbamate (450 mg, 2.24 mmol) in THF (15 mL) was added NaH (107 mg, 2.68 mmol, 60% dispersion in oil), TBAI (82.6 mg, 223 umol) at 0° C., and the mixture was stirred for 30 minutes. Then 3-bromoprop-1-yne (3.35 mmol, 289 uL) was added to the mixture at 0° C. The reaction mixture was stirred at 10° C. for 18 hrs. On completion, the reaction mixture was quenched 30 mL sat.aq NH$_4$Cl at 10° C. and diluted with 30 mL water. Then the reaction mixture was then extracted with EA (3×50 mL). The combined organic layers were washed with 50 mL brine, dried over Na$_2$SO$_4$, filtered and the filtrate was concentrated in vacuo to give the title compound (500 mg, 93% yield) as yellow oil. $^1$H NMR (400 MHz, CDCl$_3$) δ 4.68 (s, 1H), 4.27-4.19 (m, 1H), 4.08 (d, J=2.4 Hz, 2H), 2.83 (s, 3H), 2.41 (t, J=2.4 Hz, 1H), 2.38-2.26 (m, 4H), 1.46 (s, 9H).

3-[3-Methyl-4-[3-[3-(methylamino)cyclobutoxy] propyl]-2-oxo-benzimidazol-1-yl]piperidine-2,6-dione (Intermediate YP)

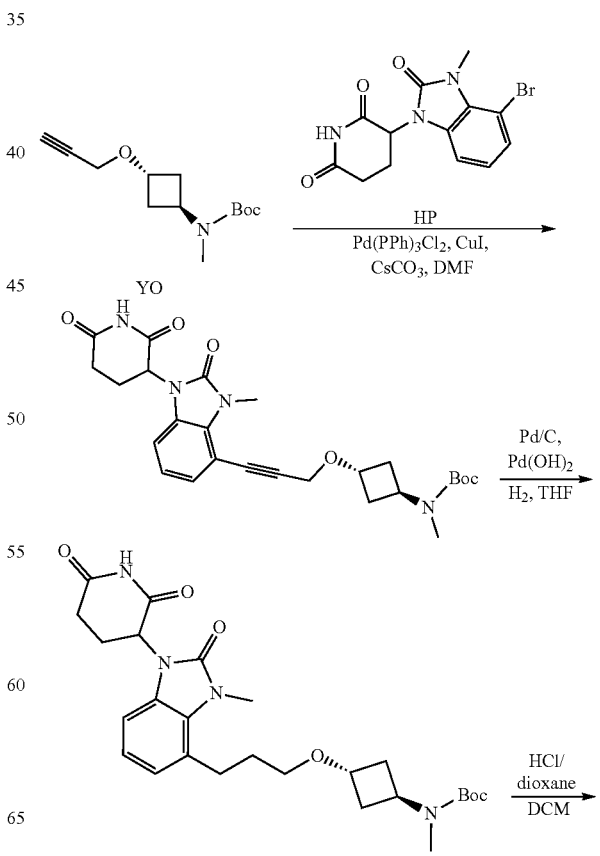

-continued

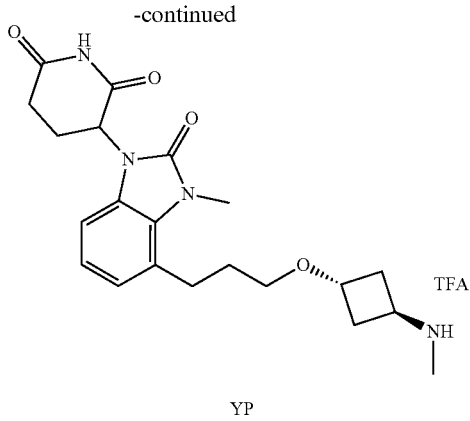

YP

Step 1—Tert-butyl N-[3-[3-[1-(2,6-dioxo-3-piperidyl)-3-methyl-2-oxo-benzimidazol-4-yl]prop-2-ynoxy] cyclobutyl]-N-methyl-carbamate To a solution of tert-butyl N-methyl-N-(3-prop-2-ynoxycyclobutyl)carbamate (500 mg, 2.09 mmol, Intermediate YO) and 3-(4-bromo-3-methyl-2-oxo-benzimidazol-1-yl)piperidine-2,6-dione (353 mg, 1.04 mmol, Intermediate HP) in DMF (15 mL) was added CuI (39.8 mg, 209 umol), $Cs_2CO_3$ (1.70 g, 5.22 mmol), $Pd(PPh_3)Cl_2$ (153 mg, 209 umol) and 4 Å molecular sieves (600 mg) at 25° C. The reaction mixture was stirred at 80° C. for 2 hrs. On completion, the reaction mixture was filtered and the filtrate was concentrated in vacuo to give a residue. The residue was diluted with 30 mL water, and then extracted with EA (3×30 mL). The combined organic layers were washed with brine (30 mL), and then dried over $Na_2SO_4$, filtered and the filtrate was concentrated in vacuo to give a residue. The residue was purified by reverse phase (0.1% FA condition) to give the title compound (380 mg, 73% yield) as a white solid. $^1H$ NMR (400 MHz, DMSO-$d_6$) δ 11.11 (s, 1H), 7.17 (d, J=7.6 Hz, 1H), 7.12 (d, J=7.6 Hz, 1H), 7.06-7.00 (m, 1H), 5.39 (dd, J=5.2, 12.8 Hz, 1H), 4.39 (s, 2H), 4.22 (t, J=6.8 Hz, 1H), 3.63 (s, 3H), 3.29 (s, 1H), 2.95-2.83 (m, 1H), 2.75 (s, 3H), 2.65-2.64 (m, 1H), 2.70-2.64 (m, 1H), 2.36-2.30 (m, 2H), 2.26-2.16 (m, 2H), 2.09-1.98 (m, 1H), 1.38 (s, 9H); LC-MS (ESI$^+$) m/z 397.0 (M+H-100)$^+$.

Step 2—Tert-butyl N-[3-[3-[1-(2,6-dioxo-3-piperidyl)-3-methyl-2-oxo-benzimidazol-4-yl]propoxy] cyclobutyl]-N-methyl-carbamate To a solution of tert-butyl N-[3-[3-[1-(2,6-dioxo-3-piperidyl)-3-methyl-2-oxo-benzimidazol-4-yl]prop-2-ynoxy] cyclobutyl]-N-methyl-carbamate (340 mg, 685 umol) in THF (15 mL) was added $Pd(OH)_2$/C (400 mg, 685 umol, 10 wt %) and Pd/C (400 mg, 685 umol, 20 wt %) at 25° C. The reaction mixture was stirred at 25° C. for 2 hrs under $H_2$ (15 psi). On completion, the reaction mixture was filtered with celite and the filtrate was concentrated in vacuo to give the title compound (330 mg, 96% yield) as black oil. LC-MS (ESI$^+$) m/z 501.2 (M+H)$^+$.

Step 3—3-[3-methyl-4-[3-[3-(methylamino)cyclobutoxy]propyl]-2-oxo-benzimidazol-1-yl]piperidine-2,6-dione To a solution of tert-butyl N-[3-[3-[1-(2,6-dioxo-3-piperidyl)-3-methyl-2-oxo-benzimidazol-4-yl] propoxy]cyclobutyl]-N-methyl-carbamate (300 mg, 599 umol) in DCM (8 mL) was added HCl/dioxane (4 M, 5 mL) at 25° C. The reaction mixture was stirred at 25° C. for 1 hr. On completion, the reaction mixture was concentrated in vacuo to give a residue. The residue was purified by reverse phase (0.1% FA condition) to give the title compound (220 mg, 91% yield) as a white solid. $^1H$ NMR (400 MHz, DMSO-$d_6$) δ 11.08 (s, 1H), 9.06 (s, 1H), 6.98-6.96 (m, 1H), 6.90-6.87 (m, 1H), 5.37 (dd, J=5.2, 12.8 Hz, 1H), 4.23-4.14 (m, 1H), 3.57 (s, 3H), 3.35 (s, 3H), 3.00-2.92 (m, 3H), 2.91-2.84 (m, 1H), 2.75-2.70 (m, 1H), 2.60 (s, 2H), 2.45 (t, J=5.6 Hz, 4H), 2.27-2.17 (m, 2H), 2.03-1.95 (m, 1H), 1.88-1.77 (m, 2H); LC-MS (ESI$^+$) m/z 401.3 (M+H)$^+$.

3-[3-Methyl-4-[3-[(2S)-2-(methylaminomethyl)morpholin-4-yl]propyl]-2-oxo-benzimidazol-1-yl]]piperidine-2,6-dione (Intermediate YQ)

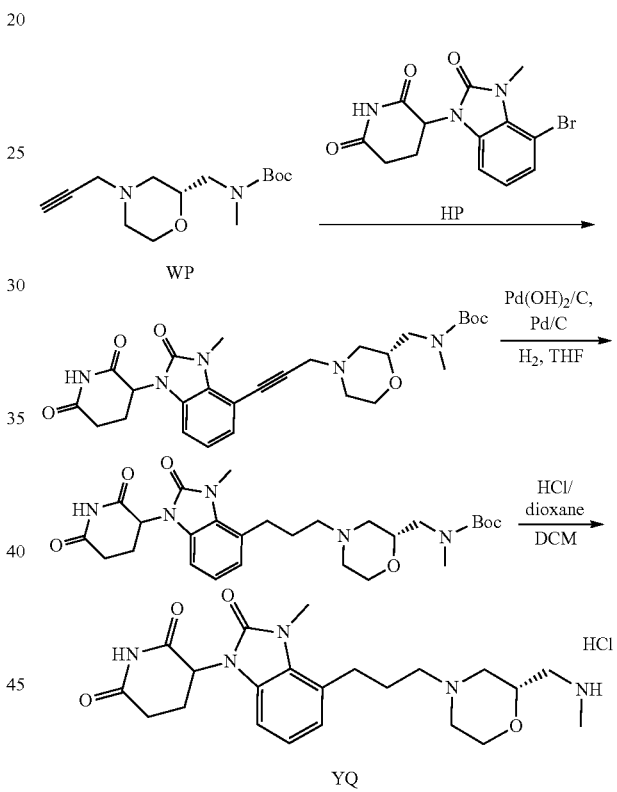

Step 1—Tert-butyl N-[[(2R)-4-[3-[1-(2,6-dioxo-3-piperidyl)-3-methyl-2-oxo-benzimidazol-4-yl]prop-2-ynyl]morpholin-2-yl]methyl]-N-methyl-carbamate To a solution of tert-butyl N-methyl-N-[[(2R)-4-prop-2-ynylmorpholin-2-yl]methyl]carbamate (400 mg, 1.49 mmol, Intermediate WP) and 3-(4-bromo-3-methyl-2-oxo-benzimidazol-1-yl)piperidine-2,6-dione (336 mg, 994 umol, Intermediate HP) in DMF (15 mL) was added $Cs_2CO_3$ (1.62 g, 4.97 mmol), 4/A molecular sieves (500 mg, 994 umol), CuI (37.8 mg, 199 umol) and $Pd(PPh_3)_2Cl_2$ (139 mg, 199 umol) at 25° C. The reaction mixture was stirred at 80° C. for 2 hrs. On completion, the reaction mixture was filtered and the filtrate was concentrated in vacuo to give a residue. The residue was diluted with water 30 mL, and then extracted with EA (3×20 mL). The combined organic layers were washed with brine (20 mL), and then dried over Na₂SO₄, filtered and the filtrate was concentrated in vacuo to give a residue. The residue was purified by reverse phase (0.1% FA condition) to give the title compound (340 mg, 65% yield) as a white solid. $^1$H NMR (400 MHz, DMSO-d$_6$) δ 11.10 (s, 1H), 7.18-7.13 (m, 1H), 7.12-7.06 (m, 1H), 7.04-6.99 (m, 1H), 5.39 (dd, J=5.2, 12.4 Hz, 1H), 3.83 (d, J=9.6 Hz, 1H), 3.64 (s, 3H), 3.62-3.46 (m, 4H), 3.34 (s, 3H), 3.15 (s, 1H), 2.86-2.78 (m, 4H), 2.75-2.66 (m, 3H), 2.11-1.98 (m, 2H), 1.35 (s, 9H); LC-MS (ESI⁺) m/z 526.3 (M+H)⁺.

Step 2—Tert-butyl N-[[(2R)-4-[3-[1-(2,6-dioxo-3-piperidyl)-3-methyl-2-oxo-benzimidazol-4-yl]propyl]morpholin-2-yl]methyl]-N-methyl-carbamate To a solution of tert-butyl N-[[(2R)-4-[3-[1-(2,6-dioxo-3-piperidyl)-3-methyl-2-oxo-benzimidazol-4-yl] prop-2-ynyl] morpholin-2-yl]methyl]-N-methyl-carbamate (300 mg, 571 umol) in THF (20 mL) and Pd/C (200 mg, 20 wt %) was added Pd(OH)₂/C (200 mg, 10 wt %) at 25° C. The reaction mixture was stirred at 25° C. for 2 hrs under H₂ (15 psi). On completion, the reaction mixture was filtered with celite and the filtrate was concentrated in vacuo to give a residue. The residue was purified by reverse phase (0.1% FA condition) to give the title compound (130 mg, 43% yield) as a white solid. $^1$H NMR (400 MHz, DMSO-d$_6$) δ 11.10 (s, 1H), 6.99-6.91 (m, 2H), 6.89-6.83 (m, 1H), 5.36 (dd, J=5.2, 12.4 Hz, 1H), 3.77 (d, J=11.2 Hz, 1H), 3.55 (s, 3H), 3.46 (t, J=10.4 Hz, 2H), 3.22 (d, J=5.2 Hz, 1H), 3.18-3.15 (m, 1H), 2.94-2.88 (m, 2H), 2.84-2.76 (m, 3H), 2.72-2.62 (m, 4H), 2.52 (s, 3H), 2.39-2.34 (m, 1H), 2.05-1.95 (m, 2H), 1.77-1.71 (m, 2H), 1.37 (s, 9H); LC-MS (ESI⁺) m/z 530.4 (M+H)⁺.

Step 3—3-[3-Methyl-4-[3-[(2S)-2-(methylaminomethyl)morpholin-4-yl]propyl]-2-oxo-benzimidazol-1-yl]]piperidine-2,6-dione To a solution of tert-butyl N-[[(2R)-4-[3-[1-(2,6-dioxo-3-piperidyl)-3-methyl-2-oxo-benzimidazol-4-yl] propyl]morpholin-2-yl]methyl]-N-methyl-carbamate (110 mg, 208 umol) in DCM (6 mL) was added HCl/dioxane (4 M, 3 mL) at 25° C. The reaction mixture was stirred at 25° C. for 1 hr. On completion, the reaction mixture was concentrated in vacuo to give the title compound (80.0 mg, 89% yield) as a white solid. LC-MS (ESI⁺) m/z 430.2 (M+H)⁺.

3-[3-Methyl-4-[3-[(2S)-2-[2-(methylamino)ethyl]morpholin-4-yl]propyl]-2-oxo-benzimidazol-1-yl]piperidine-2,6-dione (Intermediate YR)

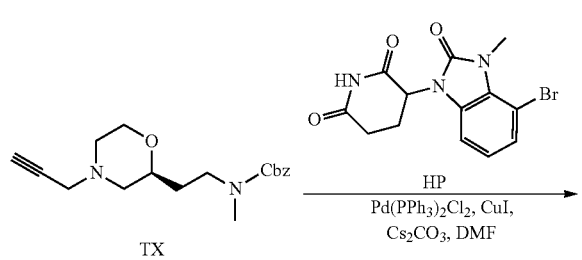

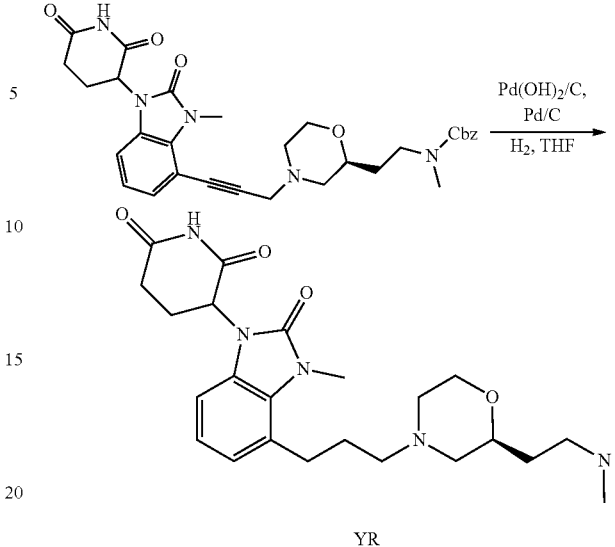

YR

Step 1—Benzyl N-[2-[(2S)-4-[3-[1-(2,6-dioxo-3-piperidyl)-3-methyl-2-oxo-benzimidazol-4-yl]prop-2-ynyl]morpholin-2-yl]ethyl]-N-methyl-carbamate To a solution of benzyl N-methyl-N-[2-[(2S)-4-prop-2-ynylmorpholin-2-yl]ethyl]carbamate (426 mg, 1.35 mmol, Intermediate TX) and 3-(4-bromo-3-methyl-2-oxo-benzimidazol-1-yl)piperidine-2,6-dione (350 mg, 1.04 mmol, Intermediate HP) in DMF (15 mL) was added Cs₂CO₃ (1.69 g, 5.18 mmol), CuI (39.4 mg, 207 umol), 4 Å molecular sieves (500 mg, 147.86 umol) and Pd(dppf)Cl₂ (151 mg, 207 umol) at 25° C. The reaction mixture was stirred at 80° C. for 2 hrs. On completion, the reaction mixture was filtered and the filtrate was concentrated in vacuo to give the residue. The residue was diluted with water 30 mL, and then extracted with EA (3×20 mL). The combined organic layers were washed with brine (20 mL), and then dried over Na₂SO₄, filtered and the filtrate was concentrated in vacuo to give a residue. The residue was purified by reverse phase (0.1% FA condition) to give the title compound (400 mg, 67% yield) as a white solid. $^1$H NMR (400 MHz, DMSO-d$_6$) δ 11.11 (s, 1H), 7.34 (d, J=2.0 Hz, 5H), 7.18-7.08 (m, 2H), 7.05-6.98 (m, 1H), 5.39 (dd, J=5.2, 12.8 Hz, 1H), 5.05 (s, 2H), 3.84-3.74 (m, 1H), 3.63 (s, 3H), 3.56 (s, 3H), 3.46-3.41 (m, 2H), 2.94-2.87 (m, 1H), 2.88-2.80 (m, 4H), 2.77-2.70 (m, 2H), 2.67-2.58 (m, 2H), 2.31-2.25 (m, 1H), 2.08-1.98 (m, 2H), 1.65-1.55 (m, 2H); LC-MS (ESI⁺) m/z 574.1 (M+H)⁺.

Step 2—3-[3-Methyl-4-[3-[(2S)-2-[2-(methylamino)ethyl]morpholin-4-yl]propyl]-2-oxo-benzimidazol-1-yl]piperidine-2,6-dione To a solution of benzyl N-[2-[(2S)-4-[3-[1-(2,6-dioxo-3-piperidyl)-3-methyl-2-oxo-benzimidazol-4-yl] prop-2-ynyl] morpholin-2-yl]ethyl]-N-methyl-carbamate (370 mg, 645 umol) in THF (15 mL) was added Pd/C (300 mg, 20 wt %) and Pd(OH)₂/C (300 mg, 10 wt %) at 25° C. The mixture was stirred at 25° C. for 2.5 hrs under H₂ (15 psi). On completion, the reaction mixture was filtered with celite and the filtrate was concentrated in vacuo to give a residue. The residue was purified by reverse phase (0.1% FA condition) to give the title compound (140 mg, 48% yield) as a brown solid. LC-MS (ESI⁺) m/z 444.3 (M+H)⁺.

1559

Tert-butyl 4-(prop-2-ynoxymethyl)piperidine-1-carboxylate (Intermediate YS)

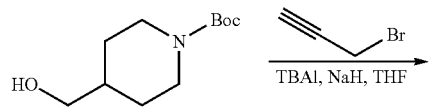

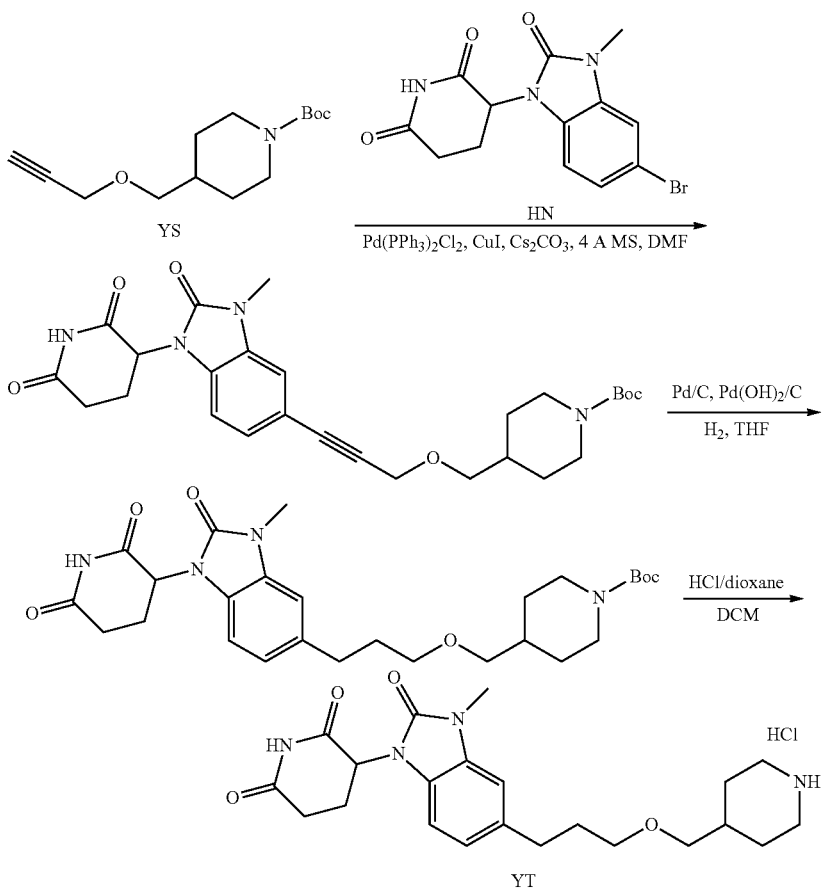

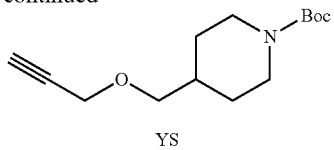

To a mixture of tert-butyl 4-(hydroxymethyl)piperidine-1-carboxylate (5.00 g, 23.2 mmol, CAS #123855-51-6) was added NaH (1.11 g, 27.8 mmol, 60% oil dispersion) at 0° C. for 0.5 hour. Then 3-bromoprop-1-yne (4.14 g, 27.8 mmol, 3.00 mL, CAS #106-96-7) and TBAI (857 mg, 2.32 mmol) was added to the mixture. The reaction mixture was stirred at 25° C. for 12 hours. On completion, the reaction mixture was quenched by addition sat. $H_2O$ (10 mL), and extracted with EA (50 mL×2). The combined organic layers were dried over $Na_2SO_4$, filtered and concentrated in vacuo to

1560 give the title compound (5.00 g, 84% yield) as yellow oil. $^1$H NMR (400 MHz, CDCl$_3$) δ 4.12 (d, J=2.4 Hz, 2H), 3.36 (d, J=6.2 Hz, 2H), 2.69 (t, J=12.2 Hz, 2H), 2.41 (t, J=2.4 Hz, 1H), 1.81-1.74 (m, 1H), 1.73-1.67 (m, 2H), 1.45 (s, 9H), 1.15-1.10 (m, 2H).

3-[3-Methyl-2-oxo-5-[3-(4-piperidylmethoxy)propyl]benzimidazol-1-yl]piperidine-2,6-dione (Intermediate YT)

Step 1—Tert-butyl 4-[3-[1-(2,6-dioxo-3-piperidyl)-3-methyl-2-oxo-benzimidazol-5-yl]prop-2-ynoxymethyl]piperidine-1-carboxylate To a mixture of tert-butyl 4-(prop-2-ynoxymethyl)piperidine-1-carboxylate (749 mg, 2.96 mmol, Intermediate YS) and 3-(5-bromo-3-methyl-2-oxo-benzimidazol-1-yl)piperidine-2,6-dione (400 mg, 1.18 mmol, Intermediate HN) in DMF (1 mL) was added Pd(PPh$_3$)$_2$Cl$_2$ (83.0 mg, 118 umol), CuI (22.5 mg, 118 umol), Cs$_2$CO$_3$ (1.93 g, 5.91 mmol) and 4 Å molecular sieves (10.0 mg, 147 umol). The reaction mixture was stirred at 80° C. for 2 hours. On completion, the reaction mixture was filtered and concentrated in vacuo. The residue was purified by reverse phase (0.1% FA condition) to give the title compound (320 mg, 52% yield) as a yellowish solid. $^1$H NMR (400 MHz, DMSO-d$_6$) δ 11.19-11.03 (m, 1H), 7.66-7.52 (m, 1H), 7.32 (d, J=0.8 Hz, 1H), 7.16-7.13 (m, 1H), 5.39 (dd, J=12.8 Hz, 1H), 4.36 (s, 2H), 3.40 (t, J=2.4 Hz, 1H), 3.37 (d, J=6.2 Hz, 2H), 3.34 (s, 3H), 3.30-3.27 (m, 2H), 2.97-2.82 (m, 1H), 2.76-2.64 (m, 4H), 2.11-1.96 (m, 1H), 1.64 (s, 2H), 1.38 (s, 9H), 1.07-1.01 (m, 2H).

Step 2—Tert-butyl 4-[3-[1-(2,6-dioxo-3-piperidyl)-3-methyl-2-oxo-benzimidazol-5-yl]propoxymethyl]piperidine-1-carboxylate To a mixture of tert-butyl 4-[3-[1-(2,6-dioxo-3-piperidyl)-3-methyl-2-oxo-benzimidazol-5-yl]prop-2-ynoxymethyl]piperidine-1-carboxylate (320 mg, 626 umol) in THF (5 mL) was added Pd/C (100 mg, 626 umol, 10% wt) and Pd(OH)$_2$/C (100 mg, 626 umol, 10% wt). The mixture was stirred at 25° C. for 12 hours under H$_2$ (15 psi). On completion, the mixture was filtered and concentrated in vacuo to give the title compound (320 mg, 99 yield) as a white solid. $^1$H NMR (400 MHz, DMSO-d$_6$) δ 11.07 (s, 1H), 7.69-7.50 (m, 1H), 7.03-7.00 (m, 1H), 6.87-6.84 (m, 1H), 5.33 (dd, J=12.8 Hz, 1H), 3.92 (d, J=12.0 Hz, 2H), 3.38-3.34 (m, 3H), 3.31-3.27 (m, 2H), 3.20 (t, J=6.6 Hz, 4H), 1.86-1.76 (m, 2H), 1.73-1.67 (m, 1H), 1.64-1.60 (m, 2H), 1.55-1.44 (m, 2H), 1.38 (s, 9H), 1.35 (s, 2H).

Step 3—3-[3-Methyl-2-oxo-5-[3-(4-piperidylmethoxy)propyl]benzimidazol-1-yl]piperidine-2,6-dione To a mixture of tert-butyl 4-[3-[1-(2,6-dioxo-3-piperidyl)-3-methyl-2-oxo-benzimidazol-5-yl] propoxymethyl]piperidine-1-carboxylate (310 mg, 602 umol) in DCM (5 mL) was added HCl/dioxane (4 M, 4.00 mL). The reaction mixture was stirred at 25° C. for 2 hours. On completion, the reaction mixture was concentrated in vacuo to give the title compound (220 mg, 88% yield) as a white solid. $^1$H NMR (400 MHz, DMSO-d$_6$) δ 11.07 (s, 1H), 7.07-6.97 (m, 2H), 6.89-6.82 (m, 1H), 5.34 (dd, J=12.8 Hz, 1H), 3.57 (s, 4H), 3.40-3.37 (m, 2H), 3.22-3.21 (m, 2H), 2.96-2.70 (m, 6H), 2.67-2.64 (m, 2H), 1.85-1.81 (m, 2H), 1.52-1.47 (m, 1H), 1.41-1.33 (m, 4H), 0.90-0.81 (m, 1H), 0.86 (t, J=7.2 Hz, 1H).

3-[3-Methyl-2-oxo-4-[3-(4-piperidylmethoxy)propyl]benzimidazol-1-yl]piperidine-2,6-dione (Intermediate YU)

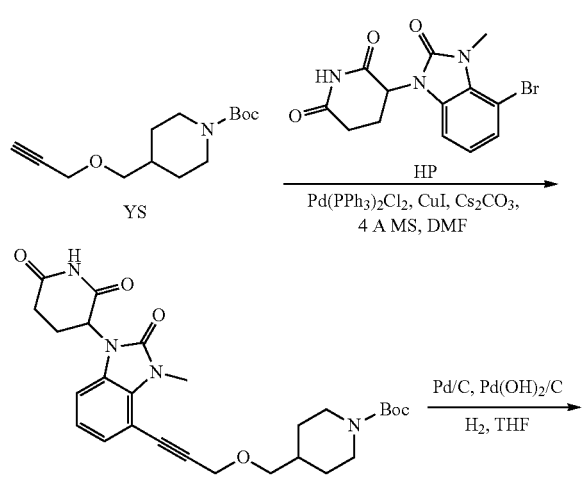

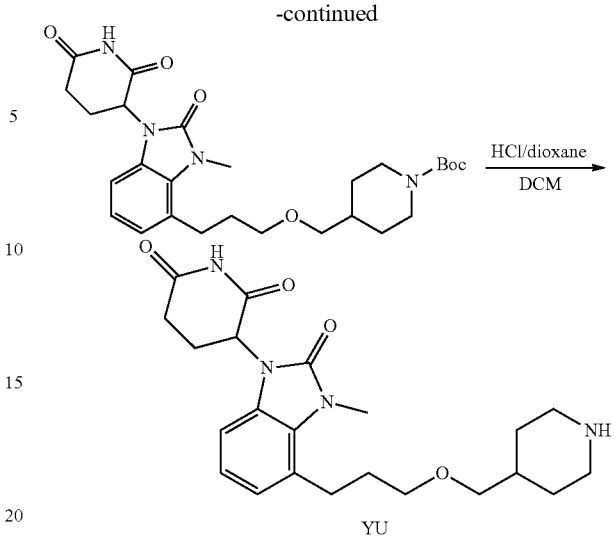

Step 1—Tert-butyl 4-[3-[1-(2,6-dioxo-3-piperidyl)-3-methyl-2-oxo-benzimidazol-4-yl]prop-2-ynoxymethyl]piperidine-1-carboxylate To a mixture of tert-butyl 4-(prop-2-ynoxymethyl)piperidine-1-carboxylate (749 mg, 2.96 mmol, Intermediate YS) and 3-(4-bromo-3-methyl-2-oxo-benzimidazol-1-yl)piperidine-2,6-dione (400 mg, 1.18 mmol, Intermediate HP) in DMF (5 mL) was added CuI (22.5 mg, 118 umol), Cs$_2$CO$_3$ (1.93 g, 5.91 mmol), Pd(PPh$_3$)$_2$Cl$_2$ (83.0 mg, 118 umol) and 4 Å molecular sieves (20.0 mg). The reaction mixture was stirred at 80° C. for 4 hours. On completion, the reaction mixture was filtered and concentrated in vacuo. The residue was purified by reverse phase (0.1% FA condition) to give the title compound (300 mg, 49% yield) as brown solid. $^1$H NMR (400 MHz, DMSO-d$_6$) δ 11.11 (s, 1H), 7.20-7.09 (m, 2H), 7.06-7.00 (m, 1H), 5.43-5.36 (m, 1H), 4.43 (s, 2H), 4.10 (d, J=2.4 Hz, 1H), 3.93 (d, J=10.8 Hz, 2H), 3.64 (s, 3H), 3.40-3.38 (m, 2H), 3.28 (d, J=6.4 Hz, 1H), 2.95-2.83 (m, 1H), 2.70-2.65 (m, 2H), 2.06-1.99 (m, 1H), 1.81-1.70 (m, 1H), 1.67-1.60 (m, 2H), 1.38 (s, 9H), 1.08-1.01 (m, 2H).

Step 2—Tert-butyl 4-[3-[1-(2,6-dioxo-3-piperidyl)-3-methyl-2-oxo-benzimidazol-4-yl]propoxymethyl]piperidine-1-carboxylate To a mixture of tert-butyl 4-[3-[1-(2,6-dioxo-3-piperidyl)-3-methyl-2-oxo-benzimidazol-4-yl]prop-2-ynoxymethyl]piperidine-1-carboxylate (300 mg, 587 umol) in THF (30 mL) was added Pd/C (100 mg, 10 wt %) and Pd(OH)$_2$/C (100 mg, 10 wt %). The reaction mixture was stirred at 25° C. for 12 hours under H$_2$ (15 psi) atmosphere. On completion, the reaction mixture was filtered and concentrated in vacuo to give the title compound (302 mg, 99% yield) as light yellow solid. $^1$H NMR (400 MHz, DMSO-d$_6$) δ 11.08 (s, 1H), 6.96 (d, J=4.4 Hz, 2H), 6.88-6.83 (m, 1H), 5.41-5.30 (m, 1H), 3.96-3.91 (m, 2H), 3.55 (s, 3H), 3.42 (t, J=5.6 Hz, 2H), 3.28-3.18 (m, 4H), 2.99-2.92 (m, 2H), 2.90-2.83 (m, 1H), 2.71-2.66 (m, 2H), 2.05-1.94 (m, 1H), 1.86-1.78 (m, 2H), 1.66-1.62 (m, 2H), 1.51-1.46 (m, 1H), 1.39 (s, 9H), 1.06-0.99 (m, 2H).

Step 3—3-[3-Methyl-2-oxo-4-[3-(4-piperidylmethoxy)propyl]benzimidazol-1-yl]piperidine-2,6-dione To a mixture of tert-butyl 4-[3-[1-(2,6-dioxo-3-piperidyl)-3-methyl-2-oxo-benzimidazol-4-yl] propoxymethyl]piperidine-1-carboxylate (290 mg, 563 umol) in DCM (2 mL) was added HCl/dioxane (4 M, 29.00 mL). The reaction mixture was stirred at 25° C. for 2 hours. On completion, the reaction mixture was concentrated in vacuo to give the title compound (254 mg, 99% yield, HCl salt) as white solid. LC-MS (ESI+) m/z 415.3 (M+H)+.

Tert-butyl 3-prop-2-ynoxyazetidine-1-carboxylate (Intermediate YV)

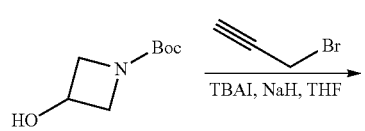

To a mixture of tert-butyl 3-hydroxyazetidine-1-carboxylate (5.00 g, 28.8 mmol, CAS #141699-55-0) in THF (5 mL) was added NaH (1.39 g, 34.6 mmol, 60% oil dispersion) at 0° C. for 0.5 hour. Then 3-bromoprop-1-yne (5.15 g, 34.6 mmol, 3.73 mL) and TBAI (1.07 g, 2.89 mmol) were added to the mixture. The reaction mixture was stirred at 25° C. for 2 hours. On completion, the reaction mixture was quenched with sat. NH4Cl (50 mL), diluted with water (100 mL) and extracted with EA (2×100 mL). The combined organic layers was dried over Na2SO4, filtered and concentrated in vacuo to give a residue. The residue was purified by column chromatography to give the title compound (5.70, 93% yield) as a yellow solid. $^1$H NMR (400 MHz, CDCl3) δ 4.45-4.37 (m, 1H), 4.13 (d, J=2.4 Hz, 2H), 4.12-4.07 (m, 2H), 3.89 (dd, J=9.6 Hz, 2H), 2.45-2.43 (m, 1H), 1.43 (s, 9H).

3-[5-[3-(Azetidin-3-yloxy)propyl]-3-methyl-2-oxo-benzimidazol-1-yl]piperidine-2,6-dione (Intermediate YW)

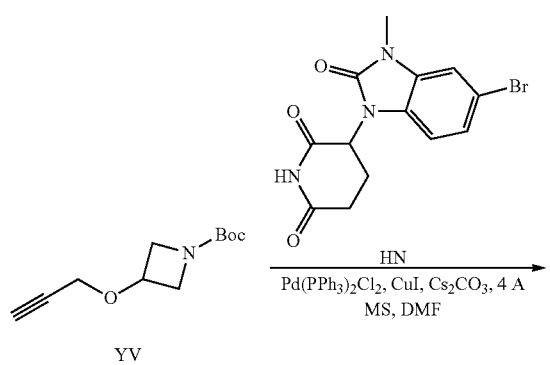

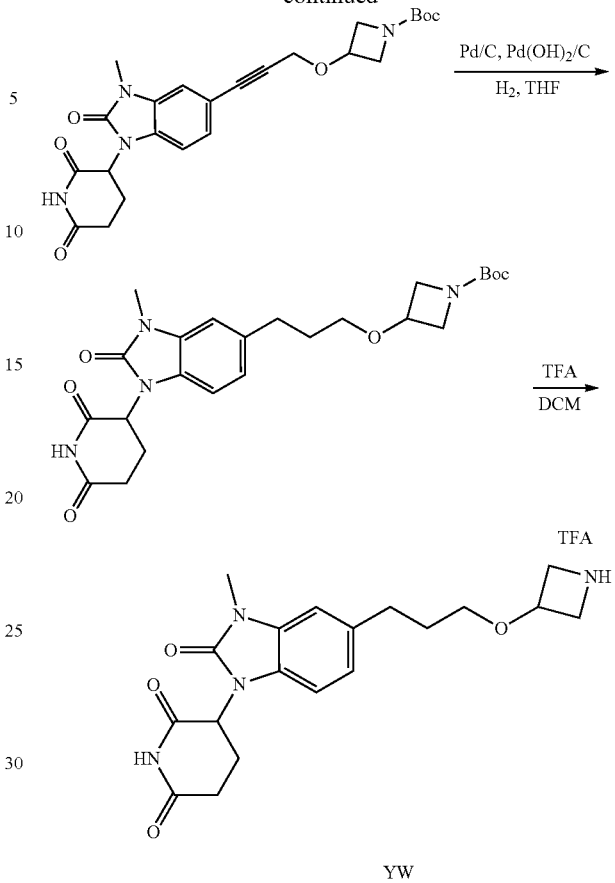

Step 1—Tert-butyl 3-[3-[1-(2,6-dioxo-3-piperidyl)-3-methyl-2-oxo-benzimidazol-5-yl]prop-2-ynoxy] azetidine-1-carboxylate To a mixture of tert-butyl 3-prop-2-ynoxyazetidine-1-carboxylate (499 mg, 2.37 mmol, Intermediate YV) and 3-(5-bromo-3-methyl-2-oxo-benzimidazol-1-yl)piperidine-2,6-dione (400 mg, 1.18 mmol, Intermediate HN) in DMF (20 mL) was added Cs2CO3 (1.93 g, 5.91 mmol), CuI (22.5 mg, 118 umol), Pd(PPh3)2Cl2 (83.0 mg, 118 umol) and 4 Å molecular sieves (100 mg). The reaction mixture was stirred at 80° C. for 2 hours. On completion, the mixture was filtered and concentrated in vacuo. The residue was purified by reverse phase (0.1% FA condition) to give the title compound (300 mg, 54% yield) as colorless oil. $^1$H NMR (400 MHz, DMSO-d6) δ 11.11 (s, 1H), 7.66-7.59 (m, 1H), 7.58-7.49 (m, 1H), 7.18-7.13 (m, 1H), 4.49-4.43 (m, 1H), 4.10-3.97 (m, 4H), 3.77-3.76 (m, 1H), 3.77-3.72 (m, 1H), 3.46 (t, J=2.4 Hz, 1H), 3.34 (s, 3H), 2.97-2.83 (m, 1H), 2.77-2.58 (m, 2H), 2.09-1.94 (m, 1H), 1.37 (s, 9H).

Step 2—Tert-butyl 3-[3-[1-(2,6-dioxo-3-piperidyl)-3-methyl-2-oxo-benzimidazol-5-yl]propoxy] azetidine-1-carboxylate To a solution of tert-butyl 3-[3-[1-(2,6-dioxo-3-piperidyl)-3-methyl-2-oxo-benzimidazol-5-yl]prop-2-ynoxy] azetidine-1-carboxylate (300 mg, 640 umol) in THF (5 mL) was added Pd/C (100 mg, 71.2 mmol, 10% w/t) and Pd(OH)2/C (100 mg, 71.2 mmol, 10% w/t) under N2. The suspension was degassed under vacuum and purged with H₂ several times. The mixture was stirred at 25° C. for 17 hours under H₂ (15 psi). On completion, the mixture was filtered and concentrated in vacuo to give the title compound (240 mg, 79% yield) as a white solid. ¹H NMR (400 MHz, DMSO-d₆) δ 11.07 (s, 1H), 7.07-6.98 (m, 2H), 6.87 (td, J=8.0 Hz, 1H), 5.33 (dd, J=12.8 Hz, 1H), 4.24-4.17 (m, 2H), 4.06-4.01 (m, 2H), 3.63 (s, 1H), 3.32 (s, 3H), 3.27-3.24 (m, 2H), 2.68-2.64 (m, 2H), 1.99 (s, 2H), 1.86-1.79 (m, 2H), 1.50 (t, J=7.2 Hz, 2H), 1.37 (s, 9H).

Step 3—3-[5-[3-(Azetidin-3-yloxy)propyl]-3-methyl-2-oxo-benzimidazol-1-yl]piperidine-2,6-dione To a mixture of tert-butyl 3-[3-[1-(2,6-dioxo-3-piperidyl)-3-methyl-2-oxo-benzimidazol-5-yl]propoxy] azetidine-1-carboxylate (220 mg, 465 umol) in DCM (5 mL) was added TFA (33.8 g, 297 mmol, 22.0 mL). The reaction mixture was stirred at 25° C. for 2 hours. On completion, the reaction mixture was concentrated in vacuo to give the title compound (150 mg, 86% yield) as a yellow solid. LC-MS (ESI⁺) m/z 373.2 (M+H)⁺.

4-(1-(2,6-Dioxopiperidin-3-yl)-3-methyl-2-oxo-2,3-dihydro-1H-benzo[d]imidazol-5-yl)but-3-yn-1-yl methanesulfonate (Intermediate YX)

Step 1—3-(5-(4-Hydroxybut-1-yn-1-yl)-3-methyl-2-oxo-2,3-dihydro-1H-benzo[d]imidazol-1-yl)piperidine-2,6-dione To a solution of 3-(5-bromo-3-methyl-2-oxo-benzimidazol-1-yl)piperidine-2,6-dione (500 mg, 1.48 mmol, Intermediate HN) and but-3-yn-1-ol (207 mg, 2.96 mmol, CAS #927-74-2) in DMF (8 mL) was added Pd(PPh₃)₂Cl₂ (207 mg, 295 umol), Cs₂CO₃ (1.93 g, 5.91 mmol), CuI (56.3 mg, 295 umol) and 4 Å molecular sieves at 25° C. under N₂. The mixture was then heated to 80° C. and stirred for 2 hours. On completion, the reaction mixture was quenched by addition water (10 mL) at 25° C., and then diluted with CH₂Cl₂ (20 mL) and extracted with CH₂Cl₂ (3×20 mL). The combined organic layers were dried over Na₂SO₄, filtered and concentrated in vacuo to give a residue. The residue was purified by reverse phase (FA condition) to give the title compound (355 mg, 73% yield) as a yellow solid. ¹H NMR (400 MHz, DMSO-d₆) δ 11.10 (s, 1H), 7.24 (s, 1H), 7.09 (s, 2H), 5.41-5.33 (m, 1H), 4.88 (s, 1H), 3.58 (t, J=7.0 Hz, 2H), 3.33 (s, 3H), 2.91-2.84 (m, 1H), 2.73-2.64 (m, 2H), 2.55 (t, J=7.0 Hz, 2H), 2.05-1.99 (m, 1H); LC-MS (ESI⁺) m/z 328.1 (M+H)⁺.

Step 2—4-(1-(2,6-Dioxopiperidin-3-yl)-3-methyl-2-oxo-2,3-dihydro-1H-benzo[d]imidazol-5-yl)but-3-yn-1-yl methanesulfonate To a mixture of 3-[5-(4-hydroxybut-1-ynyl)-3-methyl-2-oxo-benzimidazol-1-yl]piperidine-2,6-dione (350 mg, 1.07 mmol) in DCM (10 mL) was added TEA (324 mg, 3.21 mmol) and MsCl (159 mg, 1.39 mmol) at 0° C. The mixture was stirred at 0° C. for 0.5 hour. On completion, the reaction mixture was quenched by addition water (20 mL) at 25° C., and then extracted with DCM (3×30 mL). The combined organic layers were dried over Na₂SO₄, filtered and concentrated in vacuo to give the title compound (400 mg, 92% yield) as yellowish oil. ¹H NMR (400 MHz, CDCl₃) δ 8.16 (s, 1H), 7.09-7.06 (m, 1H), 7.00 (s, 1H), 6.67 (d, J=8.2 Hz, 1H), 5.14-5.09 (m, 1H), 4.33 (t, J=6.8 Hz, 2H), 3.35 (s, 3H), 3.00 (s, 3H), 2.82 (t, J=6.8 Hz, 2H); LC-MS (ESI⁺) m/z 406.3 (M+H)⁺.

3-[5-[4-[4-(Aminomethyl)-1-piperidyl]but-1-ynyl]-3-methyl-2-oxo-benzimidazol-1-yl] piperidine-2,6-dione (Intermediate YY)

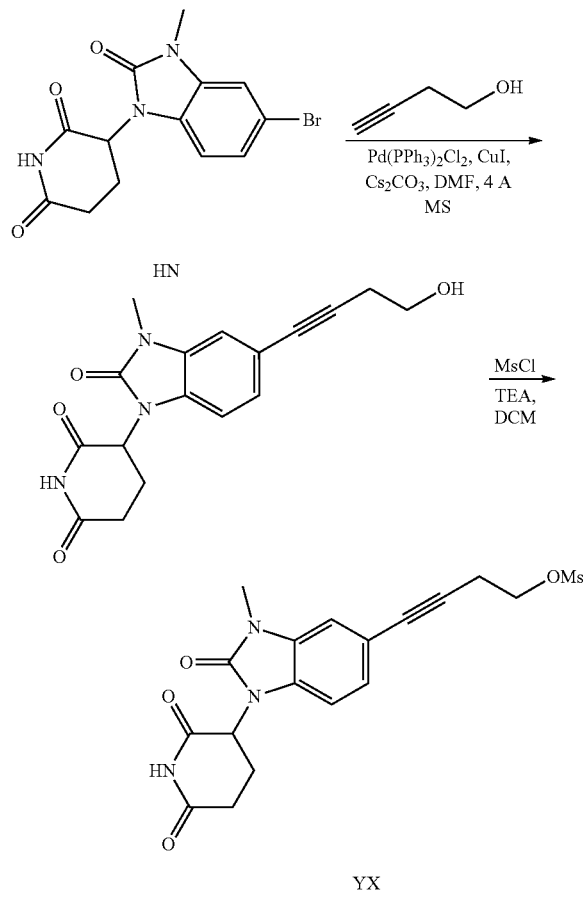

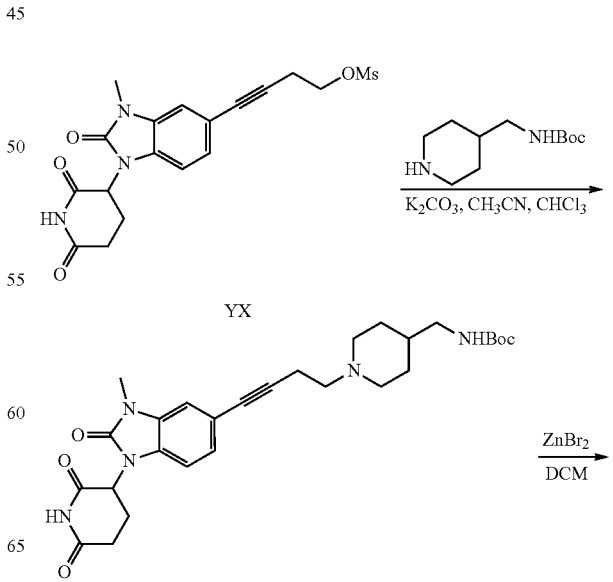

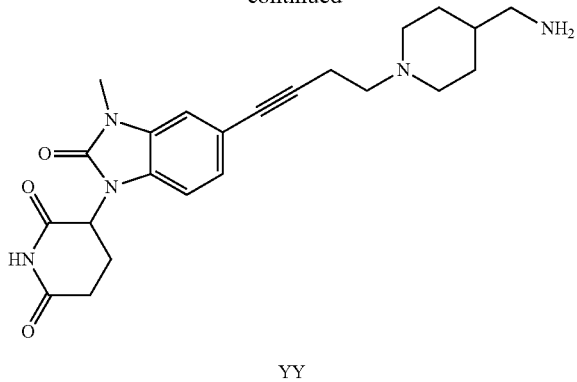

YY

Step 1—Tert-butyl N-[[1-[4-[1-(2,6-dioxo-3-piperidyl)-3-methyl-2-oxo-benzimidazol-5-yl]but-3-ynyl]-4-piperidyl methyl] carbamate To a solution of 4-[1-(2,6-dioxo-3-piperidyl)-3-methyl-2-oxo-benzimidazol-5-yl]but-3-ynyl methanesulfonate (350 mg, 863 umol, Intermediate YX) and tert-butyl N-(4-piperidylmethyl)carbamate (222 mg, 1.04 mmol, CAS #135632-53-0) in a mixed solvent of $CHCl_3$ (5 mL) and ACN (5 mL) was added $K_2CO_3$ (239 mg, 1.73 mmol). The reaction mixture was stirred at 65° C. for 12 hrs. On completion, the mixture was diluted with water (50 mL), then extracted with EA (2×50 mL). The organic layer was washed with brine (50 mL), dried with $Na_2SO_4$, filtrated and concentrated in vacuo. The residue was purified by prep-HPLC (column: Phenomenex Synergi Max-RP 150*50 mm*10 um; mobile phase: [water (0.225% FA)-ACN]; B %: 10%-40%, 10 min) to give the title compound (165 mg, 37% yield) as a yellow solid. $^1$H NMR (400 MHz, DMSO-$d_6$) δ 11.11 (s, 1H), 7.23 (s, 1H), 7.11-7.06 (m, 2H), 6.83 (t, J=5.6 Hz, 1H), 5.37 (dd, J=5.2, 12.8 Hz, 1H), 3.32 (s, 3H), 2.95-2.84 (m, 3H), 2.79 (t, J=6.4 Hz, 2H), 2.74-2.54 (m, 6H), 2.06-1.96 (m, 3H), 1.64-1.54 (m, 2H), 1.36 (s, 9H), 1.35-1.31 (m, 1H), 1.17-1.04 (m, 2H).

Step 2—3-[5-[4-[4-(Aminomethyl)-1-piperidyl]but-1-ynyl]-3-methyl-2-oxo-benzimidazol-1-yl] piperidine-2,6-dione To a solution of tert-butyl N-[[1-[4-[1-(2,6-dioxo-3-piperidyl)-3-methyl-2-oxo-benzimidazol-5-yl] but-3-ynyl]-4-piperidyl]methyl]carbamate (90.0 mg, 172 umol) in DCM (5 mL) was added $ZnBr_2$ (387 mg, 1.72 mmol). The reaction mixture was stirred at 20° C. for 10 hrs. On completion, the mixture was concentrated in vacuo to give the title compound (70.0 mg, 96% yield) as a white solid. LC-MS (ESI$^+$) m/z 424.3 (M+H)$^+$.

2-[2-[2-(Methylamino)ethoxy]ethyl]isoindoline-1,3-dione (Intermediate YZ)

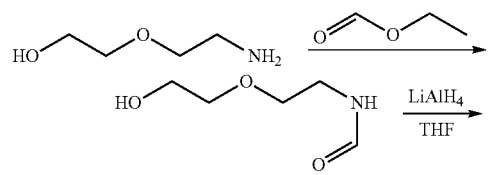

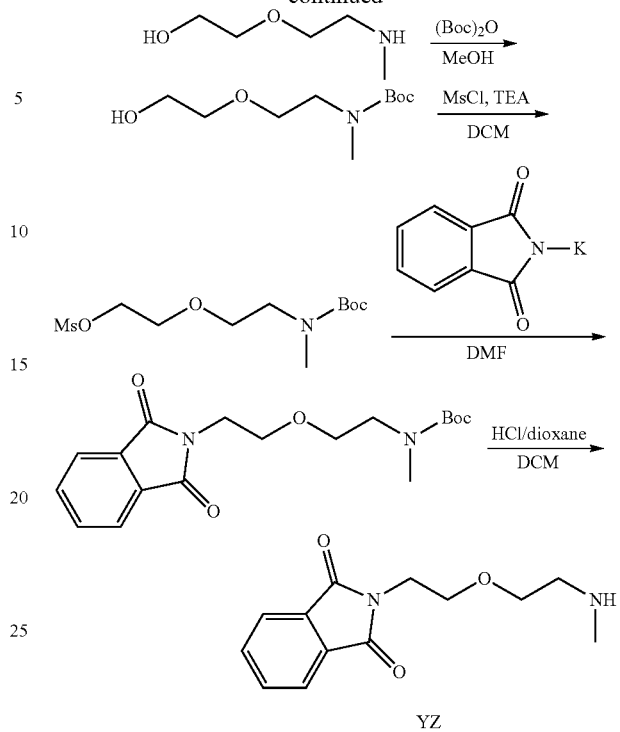

YZ

Step 1—N-[2-(2-hydroxyethoxy)ethyl]formamide

A solution of 2-(2-aminoethoxy)ethanol (5.00 g, 47.5 mmol, CAS #929-06-6) in ethyl formate (18.4 g, 248 mmol, CAS #109-94-4) was stirred at 90° C. for 6 hrs. On completion, the reaction was concentrated in vacuo to give the title compound (6.30 g, 99% yield) as yellow oil. LC-MS (ESI$^+$) m/z 134.1 (M+H)$^+$.

Step 2—2-[2-(Methylamino)ethoxy]ethanol

To a solution of $LiAlH_4$ (2.16 g, 56.7 mmol) in THF (30.0 mL) was added a solution of N-[2-(2-hydroxyethoxy)ethyl]formamide (6.30 g, 47.3 mmol) in THF (30.0 mL) dropwise at 0° C. The mixture was stirred at 80° C. for 2 hrs. On completion, the reaction mixture was quenched with a solution of 15% NaOH (20 mL). Thereafter, 50 g anhydrous sodium sulfate was added, and the mixture was filtered. The filtrate was concentrated in vacuo to give the title compound (5.64 g, 100% yield) as yellow oil.

Step 3—Tert-butyl N-[2-(2-hydroxyethoxy)ethyl]-N-methyl-carbamate

To a solution of 2-[2-(methylamino)ethoxy]ethanol (5.60 g, 46.9 mmol) in MeOH (70.0 mL) was added (Boc)$_2$O (15.3 g, 70.4 mmol), the mixture was stirred at 25° C. for 12 hrs. On completion, the mixture was concentrated in vacuo. The residue was purified by silica gel column (PE:EA=2:1) to give the title compound (8.00 g, 77% yield) as colorless oil. $^1$H NMR (400 MHz, CDCl$_3$) δ 3.80-3.68 (m, 2H), 3.67-3.52 (m, 4H), 3.48-3.33 (m, 2H), 2.92 (s, 3H), 1.47 (s, 9H).

Step 4—2-[2-[Tert-butoxycarbonyl(methyl)amino]ethoxy]ethyl methanesulfonate

To a solution of tert-butyl N-[2-(2-hydroxyethoxy)ethyl]-N-methyl-carbamate (1.00 g, 4.56 mmol), TEA (1.38 g, 13.6 mmol) in DCM (10.0 mL) was added MsCl (783 mg, 6.84 mmol) at 0° C. The mixture was stirred at 20° C. for 1 hr. On completion, the mixture was diluted with DCM (20 mL), washed with $H_2O$ (3×20 mL). The organic layer was dried over anhydrous $Na_2SO_4$, filtered and concentrated in vacuo to give the title compound (1.28 g, 94% yield) as yellow oil. $^1$H NMR (400 MHz, $CDCl_3$) δ 4.33-4.26 (m, 2H), 3.68-3.62 (m, 2H), 3.59-3.48 (m, 2H), 3.39-3.28 (m, 2H), 2.98 (s, 3H), 2.84 (s, 3H), 1.39 (s, 9H).

Step 5—Tert-butyl N-[2-[2-(1,3-dioxoisoindolin-2-yl)ethoxy]ethyl]-N-methyl-carbamate To a solution of 2-[2-[tert-butoxycarbonyl(methyl)amino]ethoxy]ethyl methanesulfonate (1.08 g, 3.63 mmol) in DMF (10.0 mL) was added (1,3-dioxoisoindolin-2-yl)potassium (1.01 g, 5.45 mmol). The mixture was stirred at 80° C. for 3 hrs. On completion, the mixture was diluted with $H_2O$ (40 mL), then extracted with EA (3×30 mL). The organic layers were washed with brine (2×30 mL) and dried over anhydrous $Na_2SO_4$, filtered and concentrated in vacuo. The residue was purified by silica gel column (PE:EA=5:1) to give the title compound (1.2 g, 94% yield) as white solid. $^1$HNMR (400 MHz, DMSO-$d_6$) δ 7.89-7.83 (m, 4H), 3.81-3.71 (m, 2H), 3.68-3.56 (m, 2H), 3.54-3.42 (m, 2H), 3.28-3.20 (m, 2H), 2.69 (s, 3H), 1.32 (s, 9H).

Step 6—2-[2-[2-(Methylamino)ethoxy]ethyl]isoindoline-1,3-dione

To a solution of tert-butyl N-[2-[2-(1,3-dioxoisoindolin-2-yl)ethoxy]ethyl]-N-methyl-carbamate (200 mg, 574 umol) in DCM (3.00 mL) was added HCl/dioxane (4.00 M, 4.00 mL). The mixture was stirred at 20° C. for 0.5 hr. On completion, the mixture was concentrated in vacuo to give the title compound (160 mg, 97% yield, HCl) as white solid. $^1$H NMR (400 MHz, DMSO-$d_6$) δ 8.84 (s, 1H), 7.92-7.84 (m, 4H), 3.84-3.76 (m, 2H), 3.73-3.65 (m, 4H), 3.10-2.92 (m, 2H), 2.49 (s, 3H).

Tert-butyl N-[[(2S)-4-(2-aminoethyl)morpholin-2-yl]methyl]-N-methyl-carbamate (Intermediate ZA)

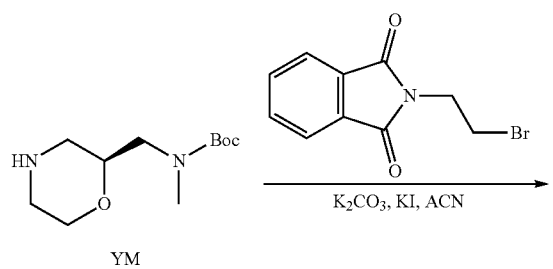

Step 1—Tert-butyl N-[[(2S)-4-[2-(1,3-dioxoisoindolin-2-yl)ethyl]morpholin-2-yl]methyl]-N-methyl-carbamate To a solution of tert-butyl N-methyl-N-[[(2S)-morpholin-2-yl]methyl]carbamate (1.00 g, 4.34 mmol, Intermediate YM) in ACN (30 mL) was added $K_2CO_3$ (535 mg, 13.0 mmol) and 2-(2-bromoethyl)isoindoline-1,3-dione (1.21 g, 4.77 mmol, CAS #574-98-1) and KI (72.1 mg, 434 umol). The reaction mixture was stirred at 80° C. for 12 hrs. On completion, the mixture was diluted with $H_2O$ (20 mL), then extracted with EA (2×20 mL). The combined organic layers were washed with brine (2×20 mL), dried over anhydrous $Na_2SO_4$, filtered and the filtrate was concentrated in vacuo. The residue was purified by silica gel column (PE:EA=1:1) to give the title compound (1.75 g, 100% yield) as yellow oil. $^1$H NMR (400 MHz, $CDCl_3$) δ 7.89-7.81 (m, 2H), 7.77-7.67 (m, 2H), 3.96-3.75 (m, 3H), 3.65-3.48 (m, 2H), 3.42-3.29 (m, 1H), 3.14 (dd, J=6.4, 14.4 Hz, 1H), 2.89 (s, 3H), 2.86-2.73 (m, 2H), 2.70-2.51 (m, 2H), 2.17 (t, J=10.4 Hz, 1H), 1.93-1.90 (m, 1H), 1.45 (s, 9H).

Step 2—Tert-butyl N-[[(2S)-4-(2-aminoethyl)morpholin-2-yl]methyl]-N-methyl-carbamate To a solution of tert-butyl N-[[(2S)-4-[2-(1,3-dioxoisoindolin-2-yl)ethyl]morpholin-2-yl]methyl]-N-methyl-carbamate (1.00 g, 2.48 mmol) in EtOH (10 mL) was added $NH_2NH_2H_2O$ (633 mg, 12.4 mmol). The reaction mixture was stirred at 80° C. for 2 hrs. On completion, the reaction mixture was filtered and the filtrate was concentrated in vacuo to give the title compound (650 mg, 96% yield) as yellow solid. $^1$H NMR (400 MHz, $CDCl_3$) δ 3.94-3.81 (m, 1H), 3.76-3.60 (m, 2H), 3.53-3.30 (m, 1H), 3.24-3.09 (m, 1H), 2.92 (s, 3H), 2.82-2.78 (m, 2H), 2.75-2.71 (m, 1H), 2.68-2.65 (m, 1H), 2.43 (t, J=6.0 Hz, 2H), 2.51-2.35 (m, 1H), 2.17-2.15 (1H), 1.88 (t, J=10.4 Hz, 1H), 1.46 (s, 9H).

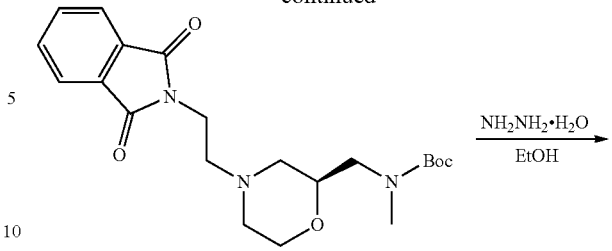

Benzyl N-[[1-(2,6-dioxo-3-piperidyl)-3-methyl-2-oxo-benzimidazol-5-yl]methyl]-N-[2-[(2R)-2-(methylaminomethyl)morpholin-4-yl]ethyl]carbamate (Intermediate ZB)

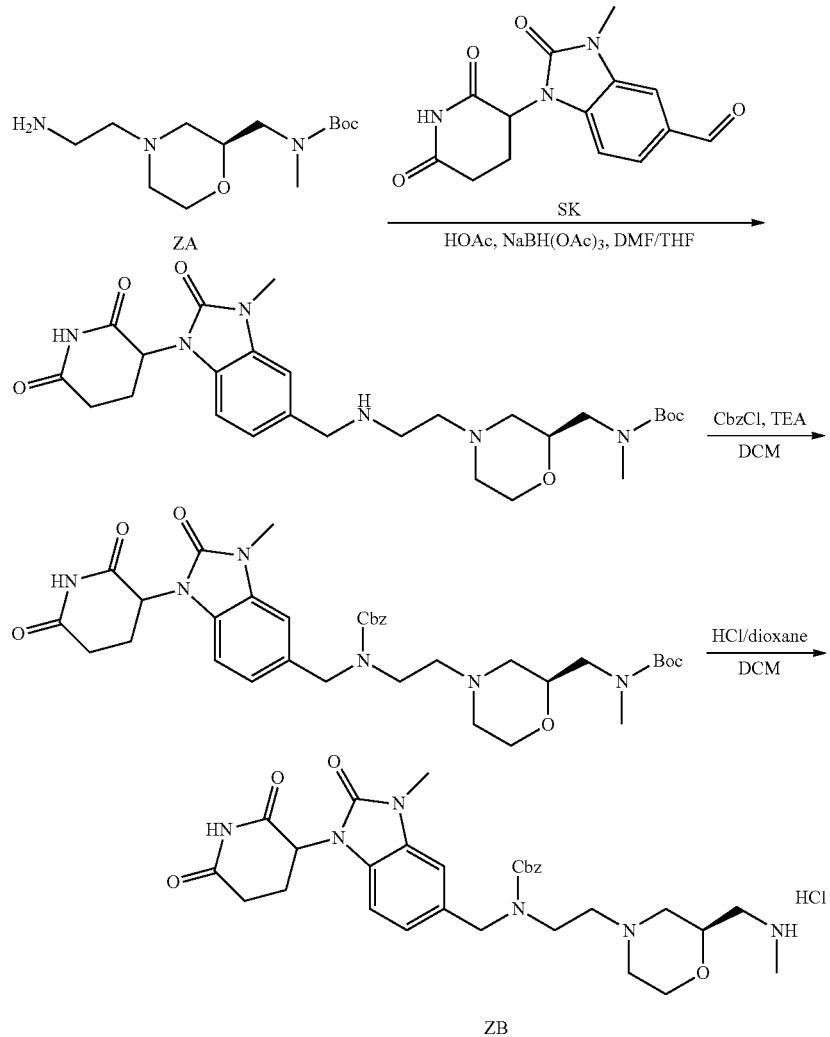

Step 1—Tert-butyl N-[[(2S)-4-[2-[[1-(2,6-dioxo-3-piperidyl)-3-methyl-2-oxo-benzimidazol-5-yl]methylamino]ethyl]morpholin-2-yl]methyl]-N-methyl-carbamate To a solution of 1-(2,6-dioxo-3-piperidyl)-3-methyl-2-oxo-benzimidazole-5-carbaldehyde (400 mg, 1.04 mmol, Intermediate SK) and tert-butyl N-[[(2S)-4-(2-aminoethyl)morpholin-2-yl]methyl]-N-methyl-carbamate (428 mg, 1.57 mmol, Intermediate ZA) in a mixed solvent of THF (5 mL) and DMF (2 mL) was added HOAc (62 mg, 1.04 mmol). The reaction mixture was stirred at 25° C. for 0.5 hr. Then, NaBH(OAc)$_3$ (266 mg, 1.25 mmol) was added. The reaction mixture was stirred at 25° C. for 12 hrs. On completion, the mixture was quenched with water (0.5 mL) and concentrated in vacuo. The crude product was purified by reverse phase HPLC (0.1% FA condition) to give the title compound (410 mg, 61% yield) as white solid. $^1$H NMR (400 MHz, DMSO-d$_6$) δ 11.10 (s, 1H), 7.24 (s, 1H), 7.16-7.02 (m, 2H), 5.37 (dd, J=5.6, 12.8 Hz, 1H), 4.53-4.50 (m, 1H), 3.91 (s, 2H), 3.80-3.75 (m, 2H), 3.35 (s, 3H), 3.23-3.17 (m, 2H), 2.92-2.87 (m, 1H), 2.80-2.73 (m, 4H), 2.69-2.58 (m, 7H), 2.06-1.98 (m, 2H), 1.82-1.74 (m, 1H), 1.36 (s, 9H).

Step 2—Tert-butyl N-[[(2S)-4-[2-[benzyloxycarbonyl-[[1-(2,6-dioxo-3-piperidyl)-3-methyl-2-oxo-benzimidazol-5-yl]methyl]amino]ethyl]morpholin-2-yl]methyl]-N-methyl-carbamate To a solution of tert-butyl N-[[(2S)-4-[2-[[1-(2,6-dioxo-3-piperidyl)-3-methyl-2-oxo-benzimidazol-5-yl]methylamino]ethyl]morpholin-2-yl]methyl]-N-methyl-carbamate (100 mg, 184 umol) in THF (5 mL) was added TEA (55.7 mg, 550 umol). Then, CbzCl (47.0 mg, 275 umol) was added. The reaction mixture was stirred at 25° C. for 1 hr. On completion, the reaction mixture was concentrated in vacuo to give the title compound (50.0 mg, 38% yield) as white solid. $^1$H NMR (400 MHz, DMSO-d$_6$) δ 11.09 (s, 1H), 7.49-7.26 (m, 5H), 7.11-6.90 (m, 3H), 5.36 (dd, J=5.2, 12.8 Hz, 1H), 5.13 (s, 2H), 4.52 (s, 2H), 3.75-3.67 (m, 1H), 3.57-3.44 (m, 5H), 3.22-3.11 (m, 4H), 2.96-2.90 (m, 1H), 2.79 (s, 2H), 2.73-2.66 (m, 2H), 2.62-2.55 (m, 3H), 2.43-2.37 (m, 2H), 2.06-1.96 (m, 2H), 1.80-1.68 (m, 1H), 1.37 (s, 9H); LC-MS (ESI+) m/z 679.2 (M+H)+.

Step 3—Benzyl N-[[1-(2,6-dioxo-3-piperidyl)-3-methyl-2-oxo-benzimidazol-5-yl]methyl]-N-[2-[(2R)-2-(methylaminomethyl)morpholin-4-yl]ethyl] carbamate To a solution of tert-butyl N-[[(2S)-4-[2-[benzyloxycarbonyl-[[1-(2,6-dioxo-3-piperidyl)-3-methyl-2-oxo-benzimidazol-5-yl]methyl]amino]ethyl]morpholin-2-yl]methyl]-N-methyl-carbamate (50.0 mg, 73.6 umol) in DCM (2 mL) was added HCl/dioxane (4 M, 1 mL). The reaction mixture was stirred at 20° C. for 1 hr. On completion, the mixture was concentrated in vacuo to give the title compound (45.0 mg, 99% yield) as white solid. LC-MS (ESI+) m/z 579.2 (M+H)+.

2-[2-(Cyclopropylmethylamino)-4-pyridyl]-N-[3-(difluoromethyl)-1-(4-formylcyclohexyl) pyrazol-4-yl]oxazole-4-carboxamide (Intermediate ZC)

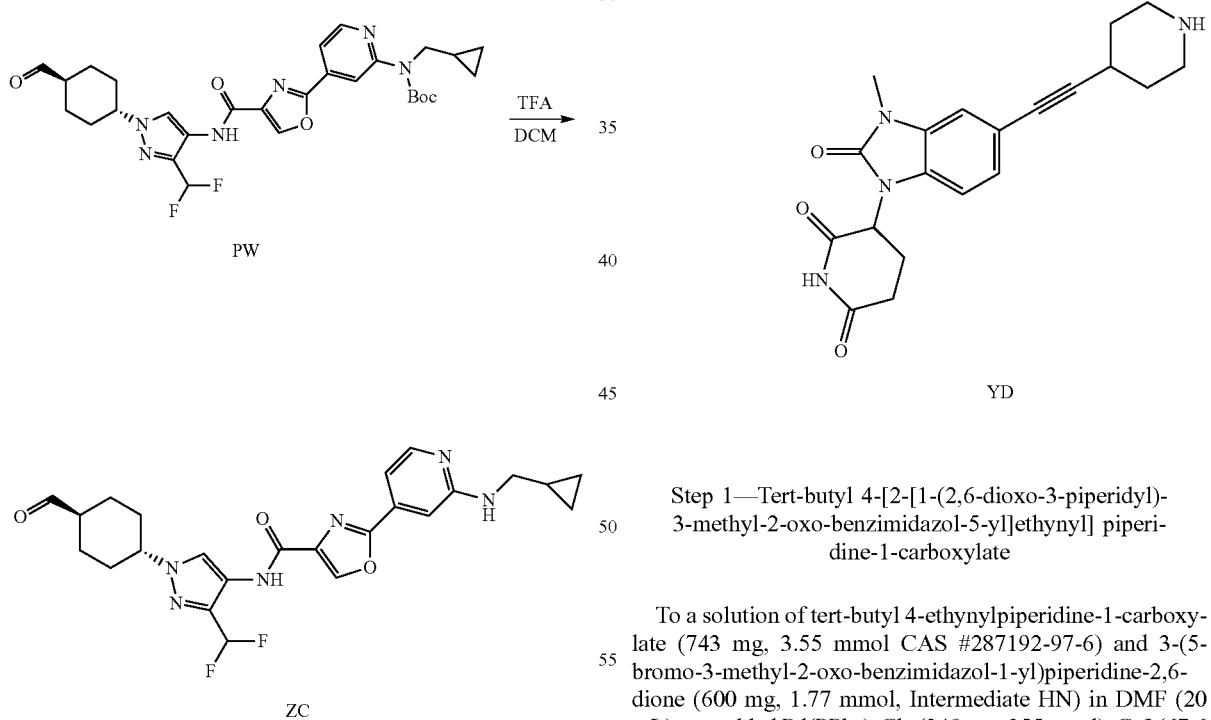

To a solution of tert-butyl N-(cyclopropylmethyl)-N-[4-[4-[[3-(difluoromethyl)-1-(4-formylcyclohexyl)pyrazol-4-yl]carbamoyl]oxazol-2-yl]-2-pyridyl]carbamate (260 mg, 445 umol) in DCM (5 mL) was added TFA (4 mL). The mixture was stirred at 25° C. for 5 hrs. On completion, the reaction mixture was concentrated in vacuo to give the title compound (220 mg, 75% yield, TFA) as brown solid. LC-MS (ESI+) m/z 485.3 (M+H)+.

3-[3-Methyl-2-oxo-5-[2-(4-piperidyl)ethynyl]benzimidazol-1-yl]piperidine-2,6-dione (Intermediate ZD)

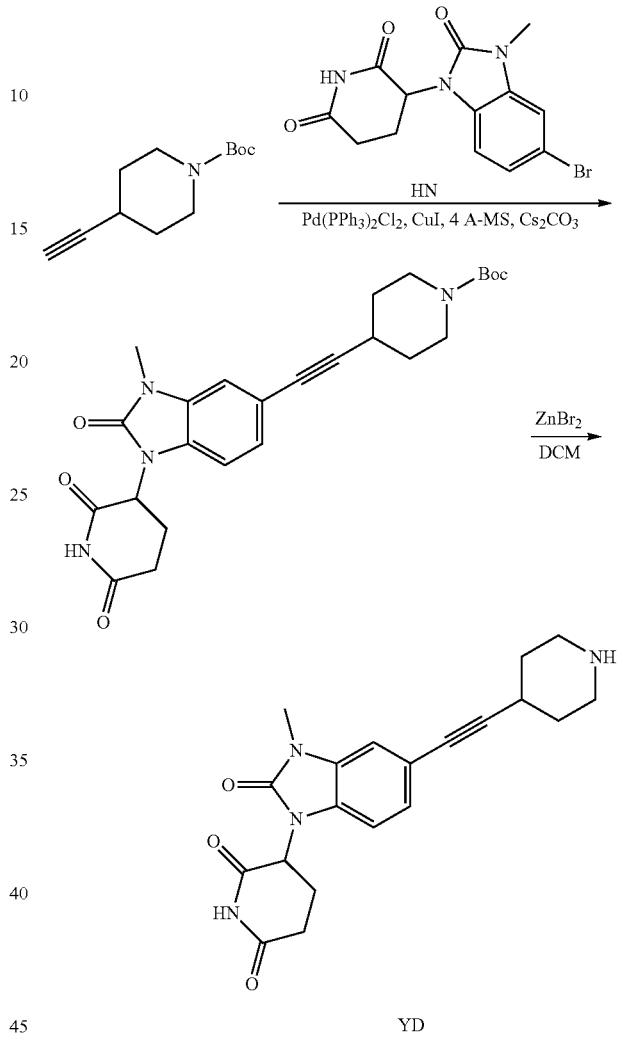

Step 1—Tert-butyl 4-[2-[1-(2,6-dioxo-3-piperidyl)-3-methyl-2-oxo-benzimidazol-5-yl]ethynyl] piperidine-1-carboxylate To a solution of tert-butyl 4-ethynylpiperidine-1-carboxylate (743 mg, 3.55 mmol CAS #287192-97-6) and 3-(5-bromo-3-methyl-2-oxo-benzimidazol-1-yl)piperidine-2,6-dione (600 mg, 1.77 mmol, Intermediate HN) in DMF (20 mL) was added Pd(PPh3)2Cl2 (249 mg, 355 umol), CuI (67.6 mg, 355 umol), 4 Å molecular sieves (80 mg) and Cs2CO3 (2.89 g, 8.87 mmol). The mixture was de-gassed and then heated at 80° C. for 2 hrs. On completion, the reaction mixture was concentrated in vacuo. The crude product was purified by reversed-phase HPLC (0.1% FA condition) to give the title compound (500 mg, 58% yield) as brown solid. 1H NMR (400 MHz, DMSO-d6) δ 11.11 (s, 1H), 7.25 (s, 1H), 7.09 (s, 2H), 5.37 (dd, J=5.6, 12.8 Hz, 1H), 3.70-3.59 (m, 2H), 3.33-3.33 (m, 3H), 3.19-3.08 (m, 2H), 2.95-2.80

(m, 2H), 2.75-2.62 (m, 2H), 2.07-1.98 (m, 1H), 2.00-1.81 (m, 2H), 1.56-1.45 (m, 2H), 1.40 (s, 9H); LC-MS (ESI+) m/z 489.3 (M+Na)+.

Step 2—3-[3-Methyl-2-oxo-5-[2-(4-piperidyl)ethynyl]benzimidazol-1-yl]piperidine-2,6-dione To a solution of tert-butyl 4-[2-[1-(2,6-dioxo-3-piperidyl)-3-methyl-2-oxo-benzimidazol-5-yl]ethynyl] piperidine-1-carboxylate (60.0 mg, 129 umol) in DCM (5 mL) was added ZnBr2 (347 mg, 1.54 mmol, 77.2 uL). The mixture was stirred at 25° C. for 24 hrs. On completion, the mixture was concentrated in vacuo to give the title compound (40.0 mg, 68% yield) as yellow solid. LC-MS (ESI+) m/z 367.1 (M+H)+.

Tert-butyl (3R)-3-piperazin-1-ylpyrrolidine-1-carboxylate (Intermediate ZE)

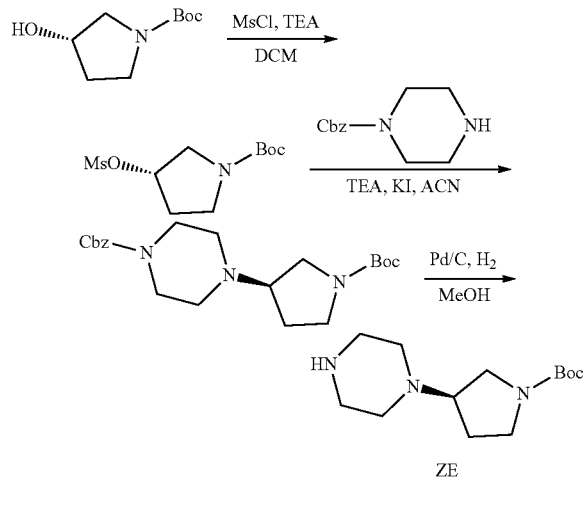

Step 1—Tert-butyl (3S)-3-methylsulfonyloxypyrrolidine-1-carboxylate

To a solution of tert-butyl (3S)-3-hydroxypyrrolidine-1-carboxylate (5.00 g, 26.7 mmol, CAS #101469-92-5) in DCM (80 mL) was added TEA (8.11 g, 80.1 mmol) and MsCl (3.98 g, 34.7 mmol) at 0° C. The mixture was then stirred at 25° C. for 0.5 hr. On completion, the reaction mixture was washed with water (3×60 mL). The organic layer was dried over Na2SO4, filtered and concentrated in vacuo to give the title compound (7.00 g, 95% yield) as light yellow oil. 1H NMR (400 MHz, CDCl3) δ 5.30-5.23 (m, 1H), 3.70-3.42 (m, 4H), 3.05 (s, 3H), 2.38-2.08 (m, 2H), 1.47 (s, 9H).

Step 2—Benzyl 4-[(3R)-1-tert-butoxycarbonylpyrrolidin-3-yl]piperazine-1-carboxylate To a solution of tert-butyl (3S)-3-methylsulfonyloxypyrrolidine-1-carboxylate (3 g, 11.3 mmol) and benzyl piperazine-1-carboxylate (4.98 g, 22.61 mmol, CAS #31166-44-6) in ACN (30 mL) was added TEA (3.43 g, 33.9 mmol) and KI (2.82 g, 16.9 mmol). The mixture was stirred as 80° C. for 40 hrs. On completion, the mixture was concentrated in vacuo to give a residue. The reaction mixture was diluted with water (30 mL) and extracted with EA (3×30 mL). The combined organic layers were dried over Na2SO4, filtered and concentrated in vacuo to give a residue. The residue was purified by column chromatography (SiO2, PE/EA=3/1) to give the title compound (1.35 g, 30% yield) as light yellow oil. 1H NMR (400 MHz, CDCl3) δ 7.43-7.28 (m, 5H), 5.14 (s, 2H), 3.75-3.38 (m, 6H), 3.34-3.20 (m, 1H), 3.09-3.05 (m, 1H), 2.86-2.70 (m, 1H), 2.61-2.31 (m, 4H), 2.12-2.05 (m, 1H), 1.85-1.75 (m, 1H), 1.46 (s, 9H).

Step 3—Tert-butyl (3R)-3-piperazin-1-ylpyrrolidine-1-carboxylate

To a solution of benzyl 4-[(3R)-1-tert-butoxycarbonylpyrrolidin-3-yl]piperazine-1-carboxylate (1.20 g, 3.08 mmol) in MeOH (20 mL) was added Pd/C (400 mg, 10 wt %) under N2. The suspension was degassed under vacuum and purged with H2 three times. The mixture was stirred at 25° C. for 16 hours under H2 (15 psi). On completion, the mixture was filtered and the filtrate was concentrated in vacuo to give the title compound (780 mg, 96% yield) as colorless oil. 1H NMR (400 MHz, CDCl3) δ 3.76-3.48 (m, 2H), 3.30-3.19 (m, 1H), 3.08 (t, J=9.2 Hz, 1H), 2.90 (t, J=4.4 Hz, 3H), 2.83-2.69 (m, 1H), 2.62-2.34 (m, 4H), 2.13-2.02 (m, 1H), 1.73-1.67 (m, 1H), 1.45 (s, 9H).

3-[3-Methyl-2-oxo-5-[[4-[(3R)-pyrrolidin-3-yl]piperazin-1-yl]methyl]benzimidazol-1-yl]piperidine-2,6-dione (Intermediate ZF)

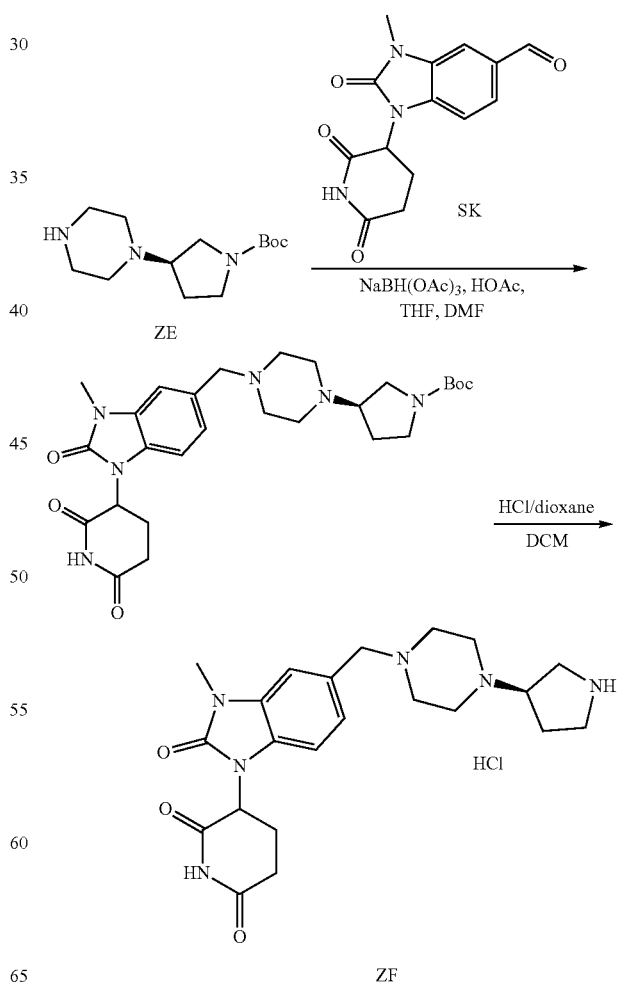

Step 1—Tert-butyl (3R)-3-[4-[[1-(2,6-dioxo-3-piperidyl)-3-methyl-2-oxo-benzimidazol-5-yl]methyl]piperazin-1-yl]pyrrolidine-1-carboxylate To a mixture of tert-butyl (3R)-3-piperazin-1-ylpyrrolidine-1-carboxylate (200 mg, 783 umol, Intermediate ZE) in a mixed solvent of THF (4 mL) and DMF (0.2 mL) was added 1-(2,6-dioxo-3-piperidyl)-3-methyl-2-oxo-benzimidazole-5-carbaldehyde (225 mg, 783 umol, Intermediate SK) and HOAc (9.41 mg, 156 umol). The mixture was stirred at 25° C. for 30 minutes. After that, NaBH(OAc)$_3$ (331 mg, 1.57 mmol) was added. The mixture was stirred 25° C. for 72 hours. On completion, the reaction mixture was quenched by water (10 mL), and then extracted with EA (3×15 mL). The combined organic layers were dried over Na$_2$SO$_4$, filtered and concentrated in vacuo to give a residue. The residue was purified by prep-HPLC (column: Phenomenex Synergi Max-RP 150*50 mm*10 um; mobile phase: [water (0.225% FA)-ACN]) to give the title compound (290 mg, 70% yield) as white solid. $^1$H NMR (400 MHz, DMSO-d$_6$) δ 11.08 (s, 1H), 7.11-6.91 (m, 3H), 5.35 (dd, J=5.2, 12.8 Hz, 1H), 3.48 (s, 2H), 3.45 (s, 1H), 3.42-3.34 (m, 1H), 3.33 (s, 3H), 3.21-3.10 (m, 1H), 2.98-2.84 (m, 2H), 2.75-2.59 (m, 3H), 2.45-2.3 (m, 8H), 2.06-1.93 (m, 2H), 1.71-1.51 (m, 1H), 1.38 (s, 9H); LC-MS (ESI$^+$) m/z 527.2 (M+H)$^+$.

Step 2—3-[3-Methyl-2-oxo-5-[[4-[(3R)-pyrrolidin-3-yl]piperazin-1-yl]methyl]benzimidazol-1-yl]piperidine-2,6-dione To a solution of tert-butyl (3R)-3-[4-[[1-(2,6-dioxo-3-piperidyl)-3-methyl-2-oxo-benzimidazol-5-yl] methyl]piperazin-1-yl]pyrrolidine-1-carboxylate (120 mg, 227 umol) in DCM (5 mL) was added HCl/dioxane (4 M, 2.28 mL). The mixture was stirred at 25° C. for 1 hr. On completion, the reaction mixture was concentrated in vacuo to give the title compound (105 mg, 99% yield, HCl) as white solid. LC-MS (ESI$^+$) m/z 427.5 (M+H)$^+$.

Tert-butyl methyl(3-oxopropyl)carbamate (Intermediate ZG)

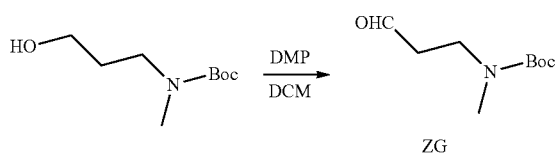

To a solution of tert-butyl N-(3-hydroxypropyl)-N-methyl-carbamate (1.00 g, 5.28 mmol, CAS #98642-44-5) in DCM (20 mL) was added DMP (3.36 g, 7.93 mmol) at 20° C. Then the reaction mixture was stirred at 20° C. for 2 hours. On completion, the reaction mixture was diluted with petroleum ether (10 mL) and stirred for 10 minutes, filtered and concentrated in vacuo. The residue was purified by flash silica gel chromatography to give the title compound (750 mg, 50% yield) as colorless oil. $^1$H NMR (400 MHz, CDCl$_3$) δ 9.78 (s, 1H), 3.53-3.47 (m, 2H), 2.85 (s, 3H), 2.66-2.62 (m, 2H), 1.43 (s, 9H).

3-(3-Methyl-2-oxo-4-(piperidin-4-yl)-2,3-dihydro-1H-benzo[d]imidazol-1-yl)piperidine-2,6-dione hydrochloride (Intermediate ZH)

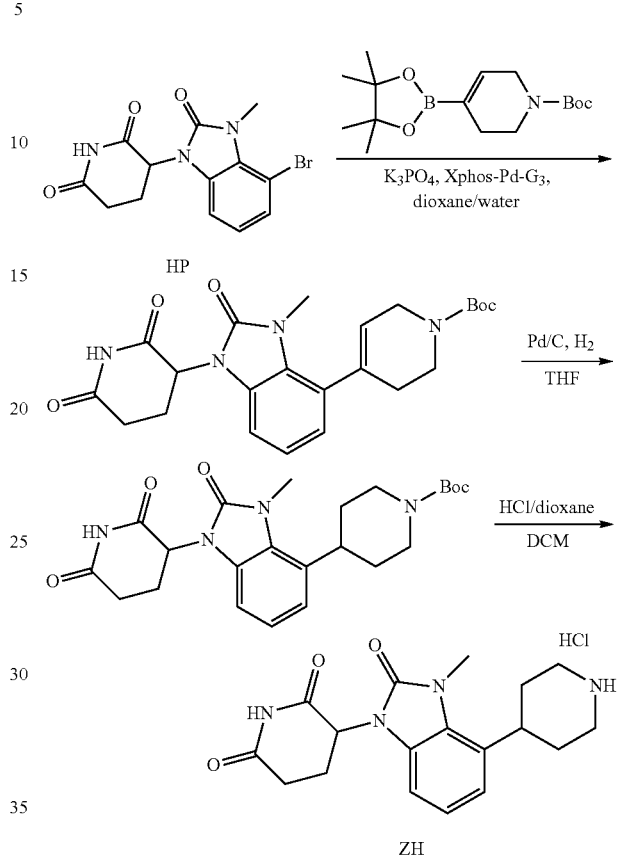

Step 1—Tert-butyl 4-(1-(2,6-dioxopiperidin-3-yl)-3-methyl-2-oxo-2,3-dihydro-1H-benzo[d]imidazol-4-yl)-5,6-dihydropyridine-1(2H)-carboxylate A mixture of 3-(4-bromo-3-methyl-2-oxo-benzimidazol-1-yl)piperidine-2,6-dione (1.00 g, 2.96 mmol, Intermediate HP), tert-butyl 4-(4,4,5,5-tetramethyl-1,3,2-dioxaborolan-2-yl)-3,6-dihydro-2H-pyridine-1-carboxylate (1.19 g, 3.84 mmol, CAS #286961-14-6), XPhos-Pd-G3 (376 mg, 0.444 mmol), K$_3$PO$_4$ (1.88 g, 8.87 mmol) in dioxane (20 mL) and water (2 mL) was degassed and purged with N$_2$ three times. The mixture was stirred at 60° C. for 3 hours under N$_2$ atmosphere. On completion, the reaction mixture was filtered and the filtrate was concentrated in vacuo. The residue was purified by reverse phase (0.1% FA condition) to give the title compound (1.00 g, 75% yield) as white solid. $^1$H NMR (400 MHz, DMSO-d$_6$) δ 11.09 (s, 1H), 7.10-6.95 (m, 2H), 6.82 (d, J=7.2 Hz, 1H), 5.40-5.35 (m, 1H), 3.99 (s, 3H), 3.67-3.50 (m, 3H), 2.95-2.83 (m, 1H), 2.80-2.55 (m, 3H), 2.43-2.30 (m, 3H), 2.05-1.95 (m, 1H), 1.44 (s, 9H); LC-MS (ESI$^+$) m/z 441.0 (M+H)$^+$.

Step 2—Tert-butyl 4-(1-(2,6-dioxopiperidin-3-yl)-3-methyl-2-oxo-2,3-dihydro-1H-benzo[d]imidazol-4-yl)piperidine-1-carboxylate To a solution of tert-butyl 4-[1-(2,6-dioxo-3-piperidyl)-3-methyl-2-oxo-benzimidazol-4-yl]-3,6-dihydro-2H-pyridine-1-carboxylate (900 mg, 2.04 mmol) in THF (270 mL) was added Pd/C (180 mg, 10 wt %) under N₂ atmosphere. The suspension was degassed and purged with H₂ three times. The mixture was stirred at 30° C. for 48 hours under H₂ (50 Psi). On completion, the reaction mixture was filtered and concentrated in vacuo to give the title compound (900 mg, 92% yield) as white solid. LC-MS (ESI⁺) m/z 387.2 (M+H−56)⁺.

Step 3—3-(3-Methyl-2-oxo-4-(piperidin-4-yl)-2,3-dihydro-1H-benzo[d]imidazol-1-yl)piperidine-2,6-dione hydrochloride To a solution of tert-butyl 4-[1-(2,6-dioxo-3-piperidyl)-3-methyl-2-oxo-benzimidazol-4-yl]piperidine-1-carboxylate (1.00 g, 2.26 mmol) in DCM (10 mL) was added HCl/dioxane (4 mol/L, 5 mL). The reaction mixture was stirred at 25° C. for 1 hour. On completion, the reaction mixture was concentrated in vacuo to give the title compound (900 mg, 88% yield) as white solid. LC-MS (ESI⁺) m/z 343.2 (M+H)⁺.

3-(3-Methyl-4-(1-(3-(methylamino)propyl)piperidin-4-yl)-2-oxo-2,3-dihydro-1H-benzo[d]imidazol-1-yl)piperidine-2,6-dione hydrochloride (Intermediate ZI)

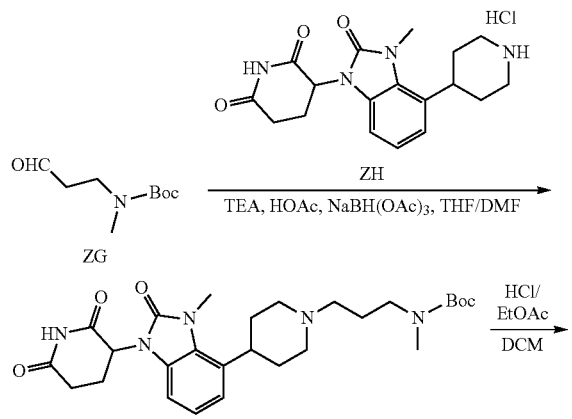

-continued

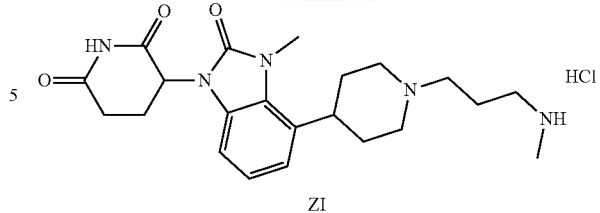

Step 1-Tert-butyl (3-(4-(1-(2,6-dioxopiperidin-3-yl)-3-methyl-2-oxo-2,3-dihydro-1H-benzo[d]imidazol-4-yl)piperidin-1-yl)propyl)(methyl)carbamate To a solution of 3-[3-methyl-2-oxo-4-(4-piperidyl)benzimidazol-1-yl]piperidine-2,6-dione (350 mg, 0.924 mmol, Intermediate ZH) in THF (5 mL) and DMF (1 mL) was added Et₃N (140 mg, 1.39 mmol). Then the reaction mixture was stirred at 20° C. for 0.5 hour. Then HOAc (83.2 mg, 1.39 mmol) and tert-butyl N-methyl-N-(3-oxopropyl)carbamate (580 mg, 2.04 mmol, Intermediate ZG) were added to the above mixture. The reaction mixture was stirred at 20° C. for 0.5 hour. NaBH(OAc)₃ (392 mg, 1.85 mmol) was added to the reaction mixture and stirred at 20° C. for 16 hours. On completion, the reaction mixture was quenched with water (0.5 mL) and concentrated in vacuo. The residue was purified by reverse phase (0.1% FA condition) to give the title compound (450 mg, 83% yield) as off-white solid. LC-MS (ESI⁺) m/z 514.4 (M+H)⁺.

Step 2—3-(3-Methyl-4-(1-(3-(methylamino)propyl)piperidin-4-yl)-2-oxo-2,3-dihydro-1H-benzo[d]imidazol-1-yl)piperidine-2,6-dione hydrochloride To a solution of tert-butyl N-[3-[4-[1-(2,6-dioxo-3-piperidyl)-3-methyl-2-oxo-benzimidazol-4-yl]-1-piperidyl]propyl]-N-methyl-carbamate (450 mg, 0.876 mmol) in DCM (5 mL) was added HCl/EA (4 mol/L, 2 mL), the the reaction mixture was stirred at 20° C. for 1 hour. On completion, the reaction mixture was concentrated in vacuo to give the title compound (390 mg, 99% yield) as a white solid. LC-MS (ESI⁺) m/z 414.3 (M+H)⁺.

Tert-butyl N-[4-[4-[[3-(difluoromethyl)-1-(4-formylcyclohexyl)pyrazol-4-yl]carbamoyl] oxazol-2-yl]-2-pyridyl]-N-(2,2,2-trifluoroethyl)carbamate (Intermediate ZJ)

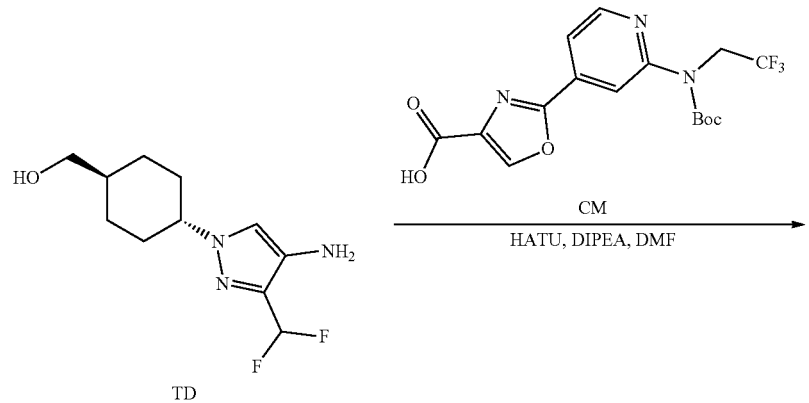

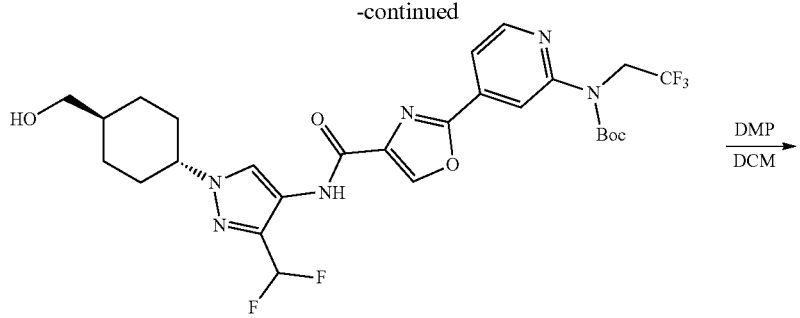

Step 1—Tert-butyl N-[4-[4-[[3-(difluoromethyl)-1-[4-(hydroxymethyl)cyclohexyl]pyrazol-4-yl] carbamoyl] oxazol-2-yl]-2-pyridyl]-N-(2,2,2-trifluoroethyl)carbamate To a mixture of [4-[4-amino-3-(difluoromethyl)pyrazol-1-yl]cyclohexyl]methanol (0.30 g, 1.22 mmol, Intermediate TD) and 2-[2-[tert-butoxycarbonyl(2,2,2-trifluoroethyl)amino]-4-pyridyl]oxazole-4-carboxylic acid (426 mg, 1.10 mmol, Intermediate CM) in DMF (80 mL) was added DIPEA (474 mg, 3.67 mmol) and stirred at 10 minutes. Then HATU (511 mg, 1.35 mmol) was added into the mixture. The reaction mixture was stirred at 25° C. for 1 hour. On completion, the reaction mixture was poured into water (200 mL) and stirred at 10 minutes. The mixture was filtered and the filter cake was dried in vacuo to give the title compound (570 mg, 75% yield) as a white solid. $^1$H NMR (400 MHz, CDCl$_3$) δ 9.06 (s, 1H), 8.53 (d, J=5.2 Hz, 1H), 8.39 (s, 1H), 8.35-8.31 (m, 2H), 7.72 (d, J=1.2, 5.2 Hz, 1H), 7.00-6.67 (m, 1H), 4.88 (d, J=8.8 Hz, 2H), 4.10 (d, J=3.6, 12.0 Hz, 1H), 3.54 (d, J=6.0 Hz, 2H), 2.30-2.21 (m, 2H), 2.06-1.97 (m, 2H), 1.82 (d, J=3.6, 12.8 Hz, 2H), 1.66-1.61 (m, 2H), 1.59-1.55 (m, 9H), 1.27-1.14 (m, 2H).

Step 2—Tert-butyl N-[4-[4-[[3-(difluoromethyl)-1-(4-formylcyclohexyl)pyrazol-4-yl]carbamoyl] oxazol-2-yl]-2-pyridyl]-N-(2,2,2-trifluoroethyl)carbamate To a mixture of tert-butyl N-[4-[4-[[3-(difluoromethyl)-1-[4-(hydroxymethyl)cyclohexyl]pyrazol-4-yl] carbamoyl] oxazol-2-yl]-2-pyridyl]-N-(2,2,2-trifluoroethyl)carbamate (570 mg, 927 umol) in DCM (20 mL) was added DMP (472 mg, 1.11 mmol). The reaction mixture was stirred at 25° C. for 1 hour. On completion, the reaction mixture was poured into the water (40 mL) and extracted with DCM (2×20 mL). The combined organic phase was washed with brine (2×20 mL), dried with anhydrous Na$_2$SO$_4$, filtered and concentrated in vacuo to give the residue. The residue was purified by reverse phase HPLC (0.1% FA condition) to give the title compound (275 mg, 48% yield) as a white solid. $^1$H NMR (400 MHz, CDCl$_3$) δ 9.63 (s, 1H), 8.99 (s, 1H), 8.45 (d, J=5.2 Hz, 1H), 8.31 (s, 1H), 8.26 (s, 2H), 7.64 (d, J=1.2, 5.2 Hz, 1H), 6.92-6.61 (m, 1H), 4.80 (d, J=8.8 Hz, 2H), 4.03 (d, J=3.6, 12.0 Hz, 1H), 2.29-2.21 (m, 2H), 2.16 (d, J=13.2 Hz, 2H), 1.81 (d, J=3.2, 12.8 Hz, 2H), 1.63-1.54 (m, 1H), 1.50 (s, 9H), 1.45-1.35 (m, 2H).

N-[3-(difluoromethyl)-1-(4-formylcyclohexyl)pyrazol-4-yl]-2-[2-(2,2,2-trifluoroethylamino)-4-pyridyl]oxazole-4-carboxamide ((Intermediate ZK)

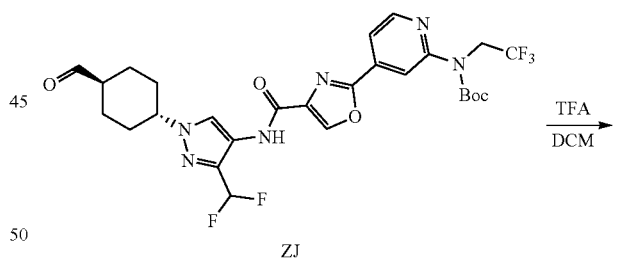

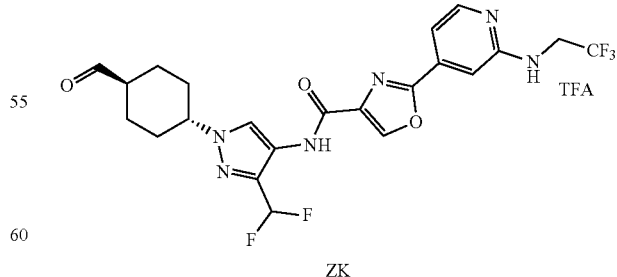

To a mixture of tert-butyl N-[4-[4-[[3-(difluoromethyl)-1-(4-formylcyclohexyl)pyrazol-4-yl]carbamoyl] oxazol-2-yl]-2-pyridyl]-N-(2,2,2-trifluoroethyl)carbamate (150 mg, 244 umol) in DCM (10 mL) was added TFA (83.7 mg, 734 umol). The reaction mixture was stirred at 25° C. for 0.5 hour. On completion, the reaction mixture was concentrated in vacuo to give the title compound (153 mg, 100% yield, TFA salt) as brown oil. LC-MS (ESI$^+$) m/z 513.3 (M+H)$^+$.

3-(3-Methyl-4-(3-((R)-2-(2-(methylamino)ethyl) morpholino)propyl)-2-oxo-2,3-dihydro-1H-benzo[d] imidazol-1-yl)piperidine-2,6-dione hydrobromide (Intermediate ZL)

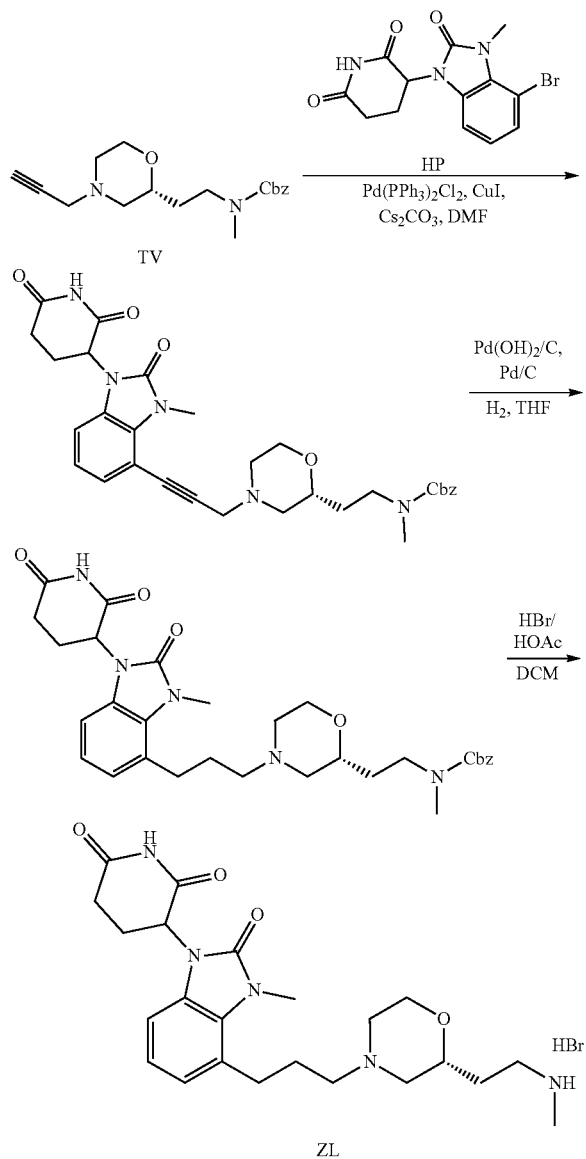

Step 1—Benzyl (2-((2R)-4-(3-(1-(2,6-dioxopiperi-din-3-yl)-3-methyl-2-oxo-2,3-dihydro-1H-benzo[d] imidazol-4-yl)prop-2-yn-1-yl)morpholin-2-yl)ethyl) (methyl)carbamate A mixture of benzyl N-methyl-N-[2-[(2R)-4-prop-2-ynylmorpholin-2-yl]ethyl]carbamate (700 mg, 2.07 mmol, Intermediate TV), 3-(4-bromo-3-methyl-2-oxo-2,3-dihydro-1H-benzo[d]imidazol-1-yl)piperidine-2,6-dione (982 mg, 3.11 mmol, Intermediate HP), Pd(PPh$_3$)$_2$Cl$_2$ (145 mg, 0.207 mmol), CuI (39.4 mg, 0.207 mmol) and Cs$_2$CO$_3$ (1.35 g, 4.14 mmol) in DMF (10 mL) was degassed and purged with N$_2$ three times. Then the mixture was stirred at 80° C. for 2 hours under N$_2$ atmosphere. On completion, the reaction mixture was filtered and the filtrate was concentrated in vacuo. The residue was purified by reverse phase (0.1% of FA condition) to give the title compound (1.10 g, 73% yield) as a yellow solid. $^1$H NMR (400 MHz, CDCl$_3$) δ11.11 (s, 1H), 7.40-7.30 (s, 5H), 7.13 (dd, J=16.0 Hz, J=7.6 Hz, 2H), 7.06-6.95 (m, 1H), 5.47-5.32 (m, 1H), 5.05 (s, 2H), 3.90-3.75 (m, 1H), 3.63 (s, 3H), 3.56 (s, 3H), 3.27-3.15 (m, 2H), 2.90-2.80 (m, 5H), 2.75-2.55 (m, 4H), 2.35-2.25 (m, 1H), 2.10-1.95 (m, 2H), 1.76-1.72 (m, 1H), 1.65-1.55 (m, 2H); LC-MS (ESI$^+$) m/z 574.1 (M+H)$^+$.

Step 2—Benzyl (2-((2R)-4-(3-(1-(2,6-dioxopiperi-din-3-yl)-3-methyl-2-oxo-2,3-dihydro-1H-benzo[d] imidazol-4-yl)propyl)morpholin-2-yl)ethyl)(methyl) carbamate To a solution of benzyl N-[2-[(2R)-4-[3-[1-(2,6-dioxo-3-piperidyl)-3-methyl-2-oxo-benzimidazol-4-yl]prop-2-ynyl] morpholin-2-yl]ethyl]-N-methyl-carbamate (1.00 g, 1.74 mmol) in THF (200 mL) was added Pd/C (200 mg, 5 wt %) and Pd(OH)$_2$/C (200 mg, 10 wt %) under N$_2$ atmosphere. The suspension was degassed and purged with H$_2$ three times. The mixture was stirred at 20° C. for 48 hours under H$_2$ (15 psi). On completion, the reaction mixture was filtered and concentrated in vacuo to give the title compound (1.00 g, 99% yield) as yellow-white solid. LC-MS (ESI$^+$) m/z 578.2 (M+H)$^+$.

Step 3—3-(3-Methyl-4-(3-((R)-2-(2-(methylamino) ethyl)morpholino)propyl)-2-oxo-2,3-dihydro-1H-benzo[d]imidazol-1-yl)piperidine-2,6-dione hydro-bromide To a solution of benzyl N-[2-[(2R)-4-[3-[1-(2,6-dioxo-3-piperidyl)-3-methyl-2-oxo-benzimidazol-4-yl] propyl]mor-pholin-2-yl]ethyl]-N-methyl-carbamate (1.00 g, 1.73 mmol) in DCM (10 mL) was added HBr/HOAc (4 mL, 40% solution). The mixture was stirred at 20° C. for 3 hours. On completion, the reaction mixture was concentrated in vacuo. Then the residue was purified by reverse phase (0.1% of FA condition) to give the title compound (700 mg, 64% yield) as off-white solid. LC-MS (ESI$^+$) m/z 444.4 (M+H)$^+$.

3-[3-Methyl-2-oxo-5-[3-(4-piperidyloxy)propyl] benzimidazol-1-yl]piperidine-2,6-dione (Intermediate ZM)

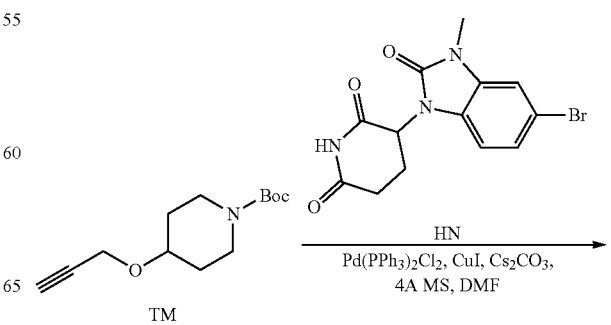

-continued

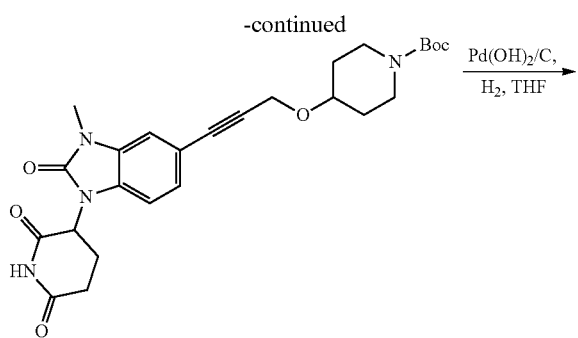

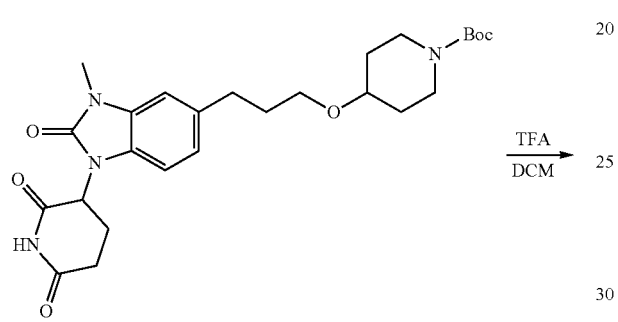

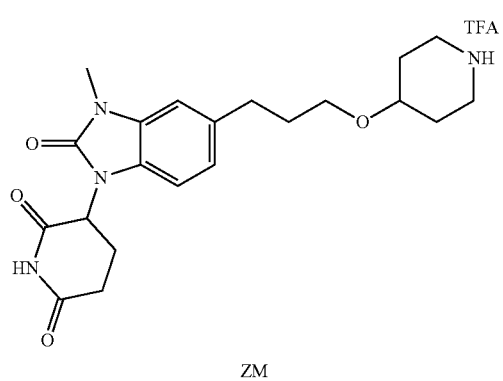

ZM

Step 1—Tert-butyl 4-[3-[1-(2,6-dioxo-3-piperidyl)-3-methyl-2-oxo-benzimidazol-5-yl]prop-2-ynoxy]piperidine-1-carboxylate To a mixture of 3-(5-bromo-3-methyl-2-oxo-benzimidazol-1-yl)piperidine-2,6-dione (350 mg, 1.04 mmol, Intermediate HN) and tert-butyl 4-prop-2-ynoxypiperidine-1-carboxylate (371 mg, 1.55 mmol, Intermediate™) in DMF (20 mL) was added Pd(PPh$_3$)$_2$Cl$_2$ (72.6 mg, 103 umol), CuI (39.4 mg, 207 umol), Cs$_2$CO$_3$ (1.35 g, 4.14 mmol) and 4 Å molecular sieves (200 mg, 1.04 mmol) in one portion at 25° C. under N$_2$. The reaction mixture was stirred at 80° C. for 2 hours. On completion, the reaction mixture was quenched by addition water (0.5 mL) at 25° C., and then extracted with EA (3×20 mL). The combined organic layers were washed with brine (20 mL), dried over Na$_2$SO$_4$, filtered and concentrated in vacuo to give a residue. The residue was purified by reverse phase (FA condition) to give the title compound (300 mg, 58% yield) as a yellow solid. $^1$H NMR (400 MHz, CDCl$_3$) δ 8.14 (s, 1H), 7.23-7.17 (m, 1H), 7.12 (d, J=1.2 Hz, 1H), 6.75 (d, J=8.1 Hz, 1H), 5.24-5.17 (m, 1H), 4.43 (s, 2H), 3.85-3.72 (m, 3H), 3.43 (s, 3H), 3.18-3.09 (m, 2H), 3.01-2.92 (m, 1H), 2.90-2.67 (m, 2H), 2.30-2.20 (m, 1H), 1.94-1.86 (m, 2H), 1.64-1.57 (m, 2H), 1.47 (s, 9H); LC-MS (ESI$^+$) m/z 519.3 (M+Na)$^+$.

Step 2—Tert-butyl 4-[3-[1-(2,6-dioxo-3-piperidyl)-3-methyl-2-oxo-benzimidazol-5-yl]propoxy]piperidine-1-carboxylate To a solution of tert-butyl 4-[3-[1-(2,6-dioxo-3-piperidyl)-3-methyl-2-oxo-benzimidazol-5-yl]prop-2-ynoxy]piperidine-1-carboxylate (300 mg, 604 umol) in THF (4 mL) was added Pd/C (50 mg, 10 wt %) and Pd(OH)$_2$/C (50 mg, 10 wt %) under N$_2$. The suspension was degassed under vacuum and purged with H$_2$ three times. The mixture was stirred at 25° C. for 2 hours under H$_2$ (15 psi). On completion, the reaction mixture was filtered and the filtrate was concentrated in vacuo to give a residue. The residue was purified by reverse phase (FA condition) to give the title compound (300 mg, 84% yield) as a yellow solid. $^1$H NMR (400 MHz, CDCl$_3$) δ 8.24 (s, 1H), 6.95-6.85 (m, 2H), 6.73 (d, J=8.2 Hz, 1H), 5.26-5.18 (m, 1H), 3.81-3.73 (m, 2H), 3.49-3.42 (m, 6H), 3.15-3.05 (m, 2H), 2.99-2.82 (m, 2H), 2.75 (t, J=7.6 Hz, 3H), 2.28-2.19 (m, 1H), 1.95-1.77 (m, 4H), 1.53 (d, J=8.8 Hz, 2H), 1.47 (s, 9H); LC-MS (ESI$^+$) m/z 401.0 (M+H−100)$^+$.

Step 3—3-[3-Methyl-2-oxo-5-[3-(4-piperidyloxy)propyl]benzimidazol-1-yl]piperidine-2,6-dione To a mixture of tert-butyl 4-[3-[1-(2,6-dioxo-3-piperidyl)-3-methyl-2-oxo-benzimidazol-5-yl]propoxy] piperidine-1-carboxylate (270 mg, 539 umol) in DCM (4 mL) was added TFA (1.84 g, 16.2 mmol) at 25° C. The mixture was stirred at 25° C. for 2 hours. On completion, the reaction mixture was concentrated in vacuo to give a residue. The residue was purified by reverse phase (TFA condition) to give the title compound (162 mg, 58% yield, TFA salt) as a yellow solid. LC-MS (ESI$^+$) m/z 401.0 (M+H)$^+$.

3-[4-[3-(Azetidin-3-yloxy)propyl]-3-methyl-2-oxo-benzimidazol-1-yl]piperidine-2,6-dione (Intermediate ZN)

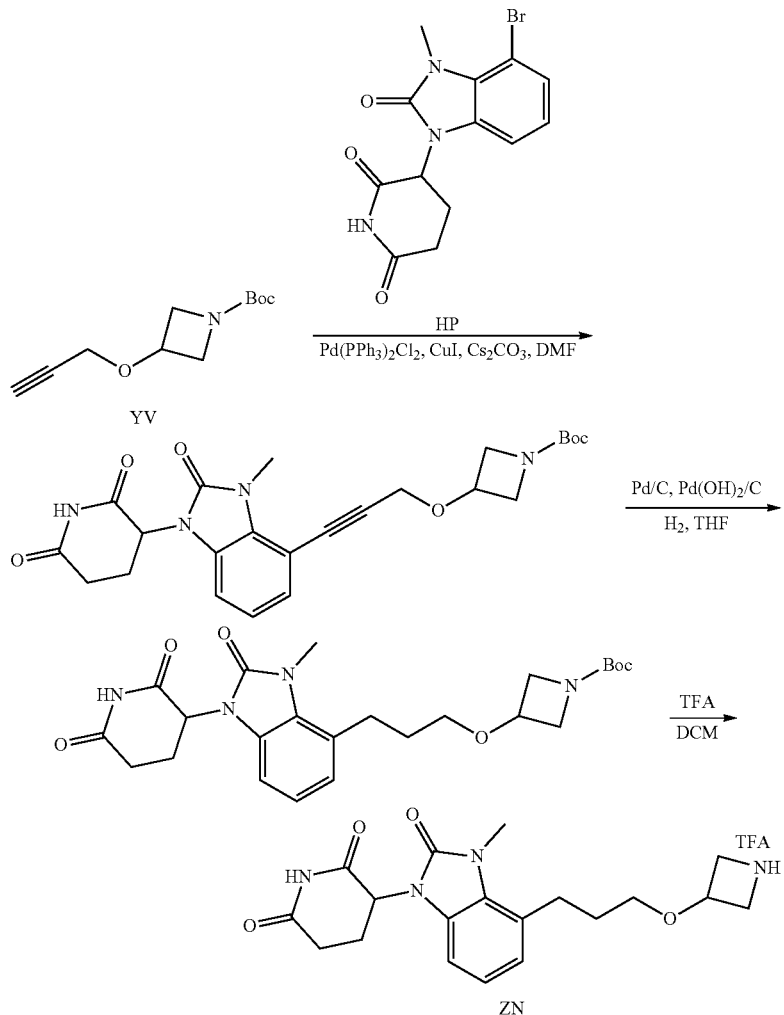

Step 1—Tert-butyl 3-[3-[1-(2,6-dioxo-3-piperidyl)-3-methyl-2-oxo-benzimidazol-4-yl]prop-2-ynoxy] azetidine-1-carboxylate To a mixture of tert-butyl 3-prop-2-ynoxyazetidine-1-carboxylate (499 mg, 2.37 mmol, Intermediate YV) and 3-(4-bromo-3-methyl-2-oxo-benzimidazol-1-yl)piperidine-2,6-dione (400 mg, 1.18 mmol, Intermediate HP) in DMF (3 mL) was added CuI (22.5 mg, 118 umol), $Cs_2CO_3$ (1.93 g, 5.91 mmol), $Pd(PPh_3)_2Cl_2$ (83.0 mg, 118 umol) and 4 Å molecular sieves (100 mg). The reaction mixture was stirred at 80° C. for 4 hours. On completion, the reaction mixture was filtered and concentrated in vacuo. The residue was purified by reverse phase (0.1% FA condition) to give the title compound (400 mg, 72% yield) as brown solid. $^1$H NMR (400 MHz, DMSO-$d_6$) δ 11.11 (s, 1H), 7.21-7.16 (m, 1H), 7.14-7.11 (m, 1H), 7.06-7.01 (m, 1H), 5.42-5.37 (m, 1H), 4.49-4.45 (m, 3H), 4.09-4.04 (m, 2H), 3.77-3.72 (m, 2H), 3.63 (s, 3H), 2.92-2.84 (m, 1H), 2.73-2.62 (m, 2H), 2.07-2.00 (m, 1H), 1.37 (s, 9H).

Step 2—Tert-butyl 3-[3-[1-(2,6-dioxo-3-piperidyl)-3-methyl-2-oxo-benzimidazol-4-yl]propoxy] azetidine-1-carboxylate To a mixture of tert-butyl 3-[3-[1-(2,6-dioxo-3-piperidyl)-3-methyl-2-oxo-benzimidazol-4-yl] prop-2-ynoxy]azetidine-1-carboxylate (400 mg, 853 umol) in THF (10 mL) was added Pd/C (150 mg, 10 wt %) and $Pd(OH)_2/C$ (150 mg, 10 wt %). The reaction mixture was stirred at 25° C. for 12 hours under $H_2$ (15 Psi). On completion, the reaction mixture was filtered and concentrated in vacuo to give the title compound (300 mg, 74% yield) as light yellow solid. LC-MS (ESI$^+$) m/z 417.2 (M+H−56)$^+$.

Step 3—3-[4-[3-(Azetidin-3-yloxy)propyl]-3-methyl-2-oxo-benzimidazol-1-yl]piperidine-2,6-dione To a mixture of tert-butyl 3-[3-[1-(2,6-dioxo-3-piperidyl)-3-methyl-2-oxo-benzimidazol-4-yl]propoxy] azetidine-1-carboxylate (290 mg, 613.71 umol) in DCM (3 mL) was added TFA (44.6 g, 391 mmol, 29.0 mL). The reaction mixture was stirred at 25° C. for 1 hour. On completion, the reaction mixture was concentrated in vacuo to give the title compound (298 mg, 99% yield, TFA salt) as red oil. LC-MS (ESI⁺) m/z 373.2 (M+H)⁺.

3-[4-[3-(4-Piperidyloxy)propyl]pyrido[2,3-b]indol-9-yl]piperidine-2,6-dione (Intermediate ZO)

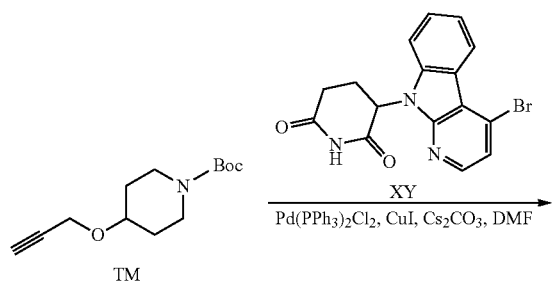

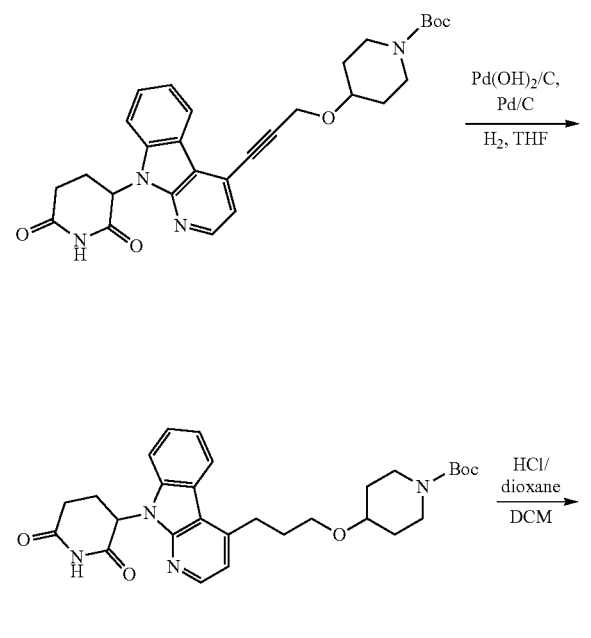

Step 1—Tert-butyl 4-[3-[9-(2,6-dioxo-3-piperidyl)pyrido[2,3-b]indol-4-yl]prop-2-ynoxy]piperidine-1-carboxylate To a solution 3-(4-bromopyrido[2,3-b]indol-9-yl)piperidine-2,6-dione (400 mg, 1.12 mmol, Intermediate XY) and tert-butyl 4-prop-2-ynoxypiperidine-1-carboxylate (534 mg, 2.23 mmol, Intermediate™) in DMF (8 mL) was added Pd(PPh₃)₂Cl₂ (157 mg, 223 umol), CuI (42.5 mg, 223 umol), Cs₂CO₃ (1.82 g, 5.58 mmol) and 4 Å molecular sieves (40 mg). The mixture was de-gassed and then heated at 80° C. for 2 hrs. On completion, the reaction mixture was concentrated in vacuo. The crude product was purified by reverse phase HPLC (0.1% FA condition) to give the title compound (200 mg, 34% yield) as brown solid. ¹H NMR (400 MHz, DMSO-d₆) δ 11.15 (s, 1H), 8.49 (d, J=7.6 Hz, 1H), 8.42 (d, J=5.2 Hz, 1H), 7.72-7.64 (m, 1H), 7.62-7.56 (m, 1H), 7.36-7.33 (m, 1H), 7.32-7.29 (m, 1H), 6.06 (s, 1H), 4.71 (s, 2H), 3.88-3.84 (m, 1H), 3.70-3.65 (m, 2H), 3.10-3.05 (m, 2H), 3.05-2.95 (m, 1H), 2.77-2.68 (m, 1H), 2.61 (s, 1H), 2.20-2.11 (m, 1H), 1.96-1.88 (m, 2H), 1.52-1.44 (m, 2H), 1.39 (s, 9H); LC-MS (ESI⁺) m/z 539.3 (M+Na)⁺.

Step 2—Tert-butyl 4-[3-[9-(2,6-dioxo-3-piperidyl)pyrido[2,3-b]indol-4-yl]propoxy]piperidine-1-carboxylate To a solution of tert-butyl 4-[3-[9-(2,6-dioxo-3-piperidyl)pyrido[2,3-b]indol-4-yl]prop-2-ynoxy] piperidine-1-carboxylate (200 mg, 387 umol in THF (5 mL) was added Pd(OH)₂ (40.0 mg, 10 wt %), Pd/C (40.0 mg, 10 wt %) under N₂. The suspension was degassed under vacuum and purged with H₂ several times. The mixture was stirred at 25° C. for 15 hours under H₂ (15 psi). On completion, the reaction mixture was filtered and the filtrate was concentrated in vacuo to give the title compound (120 mg, 59% yield) as white solid. ¹H NMR (400 MHz, DMSO-d₆) δ 11.13 (s, 1H), 8.31 (d, J=5.2 Hz, 1H), 8.24 (d, J=7.6 Hz, 1H), 7.67-7.58 (m, 1H), 7.55-7.47 (m, 1H), 7.28 (t, J=7.6 Hz, 1H), 7.10 (d, J=5.2 Hz, 1H), 6.18-5.92 (m, 1H), 3.67-3.47 (m, 6H), 3.29 (s, 1H), 3.28-3.21 (m, 2H), 3.17-2.93 (m, 4H), 2.15-2.07 (m, 1H), 2.03-1.93 (m, 2H), 1.86-1.76 (m, 2H), 1.39 (s, 9H), 1.35 (s, 1H); LC-MS (ESI⁺) m/z 521.3 (M+Na)⁺.

Step 3-3-[4-[3-(4-Piperidyloxy)propyl]pyrido[2,3-b]indol-9-yl]piperidine-2,6-dione To a mixture of tert-butyl 4-[3-[9-(2,6-dioxo-3-piperidyl)pyrido[2,3-b]indol-4-yl]propoxy]piperidine-1-carboxylate (100 mg, 192 umol) in DCM (2 mL) was added HCl/dioxane (2 mL). The reaction mixture was stirred at 25° C. for 2 hrs. On completion, the reaction mixture was concentrated in vacuo to give the title compound (80.0 mg, 91% yield) as brown solid. LC-MS (ESI⁺) m/z 421.3 (M+H)⁺.

3-[3-Methyl-4-[3-[2-(methylamino)ethoxy]propyl]-2-oxo-benzimidazol-1-yl]piperidine-2,6-dione (Intermediate ZP)

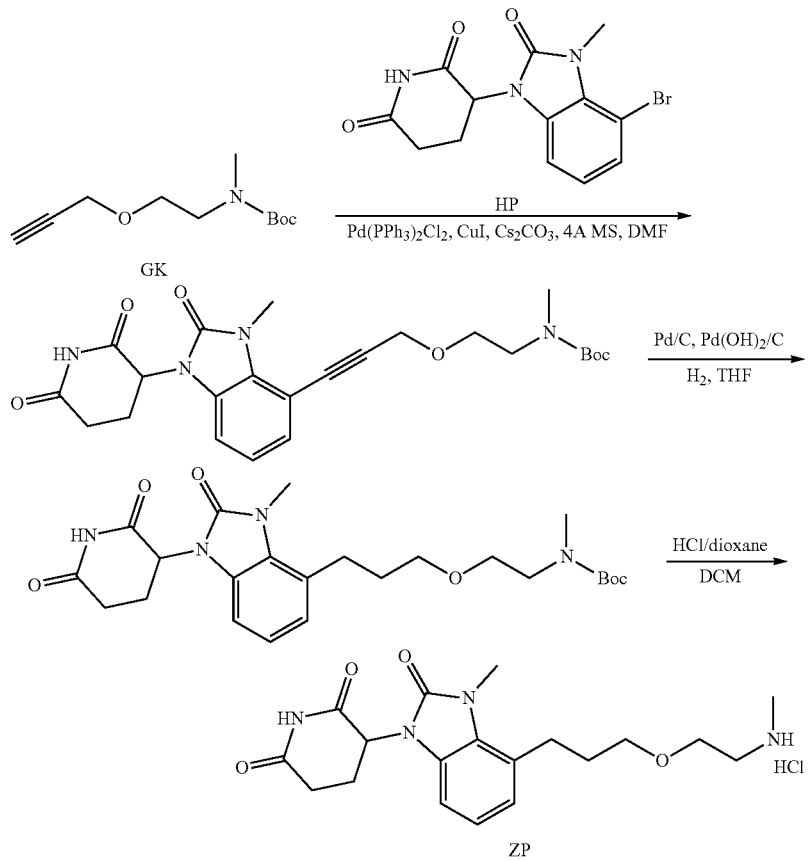

Step 1—Tert-butyl N-[2-[3-[1-(2,6-dioxo-3-piperidyl)-3-methyl-2-oxo-benzimidazol-4-yl]prop-2-ynoxy]ethyl]-N-methyl-carbamate 3-(4-bromo-3-methyl-2-oxo-benzimidazol-1-yl)piperidine-2,6-dione (400 mg, 1.18 mmol, Intermediate HP), tert-butyl N-methyl-N-(2-prop-2-ynoxyethyl)carbamate (440 mg, 2.06 mmol, Intermediate GK), Pd(PPh₃)₂Cl₂ (166 mg, 237 umol), CuI (45.1 mg, 237 umol), 4 Å molecular sieves (400 mg) and Cs₂CO₃ (1.54 g, 4.73 mmol) in DMF (5 mL) was de-gassed and then heated at 80° C. for 2 hours under N₂. On completion, the reaction mixture was filtered and the filtrate was concentrated in vacuo. The residue was purified by reversed-phase (0.1% FA condition) to give the title compound (310 mg, 39% yield) as a yellow solid. LC-MS (ESI⁺) m/z 415.1 (M+H−56)⁺.

Step 2—Tert-butyl N-[2-[3-[1-(2,6-dioxo-3-piperidyl)-3-methyl-2-oxo-benzimidazol-4-yl]propoxy]ethyl]-N-methyl-carbamate To a solution of tert-butyl N-[2-[3-[1-(2,6-dioxo-3-piperidyl)-3-methyl-2-oxo-benzimidazol-4-yl]prop-2-ynoxy]ethyl]-Nmethyl-carbamate (390 mg, 829 umol) in THF (10 mL) was added Pd/C (0.1 g, 10% wt) and Pd(OH)₂/C (0.1 g, 20% wt). The suspension was degassed under vacuum and purged with H₂ several times. The reaction mixture was stirred at 25° C. for 12 hours under H₂ (15 psi). On completion, the mixture was filtered and the filtrate was concentrated in vacuo to give the title compound (390 mg, 99% yield) as a yellow solid. ¹H NMR (400 MHz, DMSO-d₆) δ 8.25 (s, 1H), 7.12-6.96 (m, 1H), 6.95-6.86 (m, 1H), 6.72-6.60 (m, 1H), 5.30-5.15 (m, 1H), 3.48 (s, 3H), 3.65-3.58 (m, 2H), 3.52-3.45 (m, 2H), 3.45-3.35 (m, 2H), 3.08-2.95 (m, 3H), 2.92 (s, 3H), 2.85-2.60 (m, 2H), 2.25-2.15 (m, 1H), 1.96-1.85 (m, 2H), 1.50 (s, 1H); LC-MS (ESI⁺) m/z 375.1 (M+H−100)⁺.

Step 3—3-[3-Methyl-4-[3-[2-(methylamino)ethoxy]propyl]-2-oxo-benzimidazol-1-yl]piperidine-2,6-dione To a solution of tert-butyl N-[2-[3-[1-(2,6-dioxo-3-piperidyl)-3-methyl-2-oxo-benzimidazol-4-yl] propoxy]ethyl]-N-methyl-carbamate (100 mg, 211 umol) in DCM (2 mL) was added HCl/dioxane (2 mL). The reaction mixture was stirred at 20° C. for 2 hrs. On completion, the mixture was concentrated in vacuo to give the title compound (85.0 mg, 98% yield, HCl salt) as a yellow solid. LC-MS (ESI⁺) m/z 375.1 (M+H)⁺.

1593

3-[3-Methyl-5-[3-[3-(methylamino)propoxy]prop-1-ynyl]-2-oxo-benzimidazol-1-yl] piperidine-2,6-dione (Intermediate ZQ)

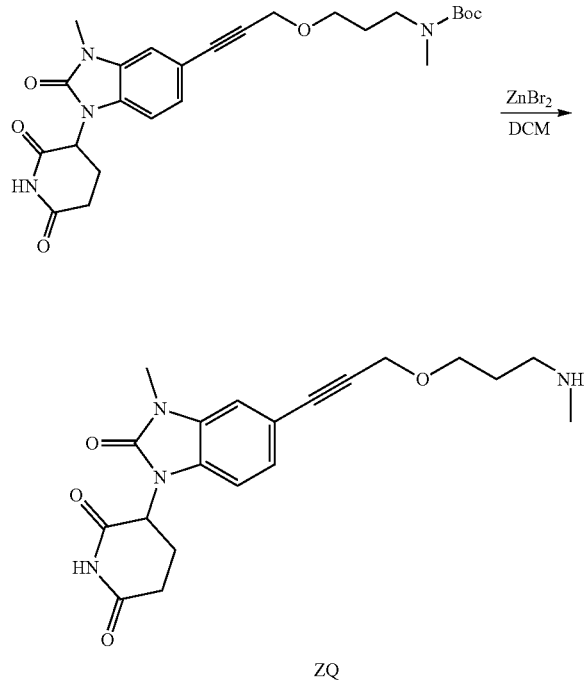

ZQ

To a solution of tert-butyl N-[3-[3-[1-(2,6-dioxo-3-piperidyl)-3-methyl-2-oxo-benzimidazol-5-yl]prop-2-ynoxy]propyl]-N-methyl-carbamate (200 mg, 412 umol, synthesized via Step 1 of Intermediate QI) in DCM (3.00 mL) was added $ZnBr_2$ (1.39 g, 6.19 mmol). The mixture was stirred at 20° C. for 20 hrs. On completion, the reaction mixture was concentrated in vacuo to give the title compound (158 mg, 99% yield) as yellow solid. LC-MS (ESI+) m/z 385.2 (M+H)+.

3-[3-Methyl-5-[[4-(methylaminomethyl)-1-piperidyl]methyl]-2-oxo-benzimidazol-1-yl] piperidine-2,6-dione (Intermediate ZR)

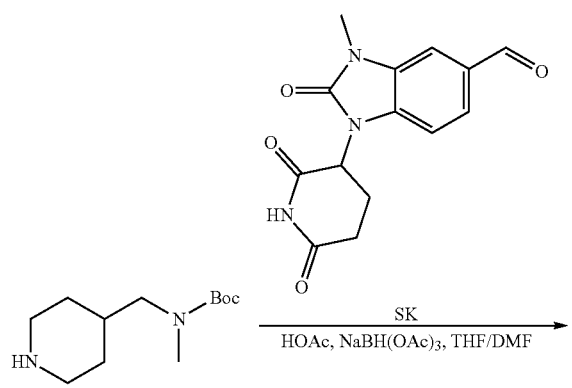

1594

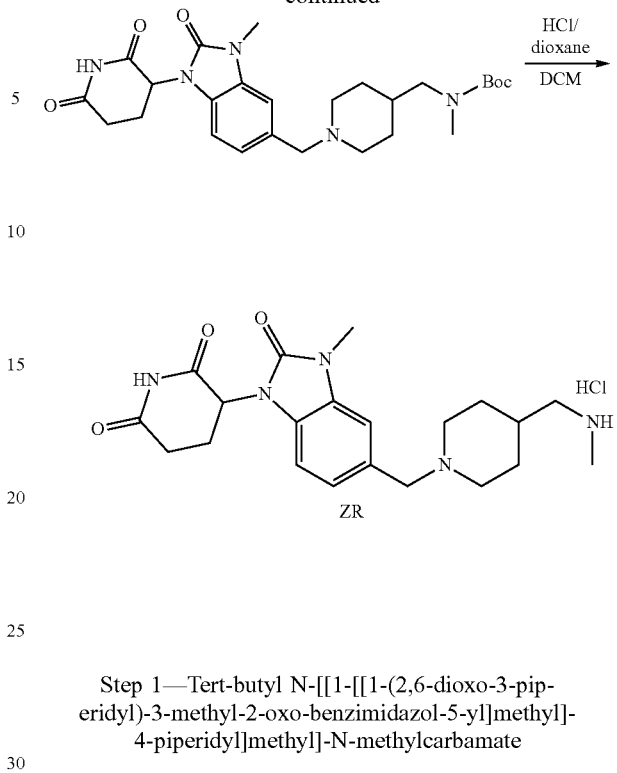

ZR

Step 1—Tert-butyl N-[[1-[[1-(2,6-dioxo-3-piperidyl)-3-methyl-2-oxo-benzimidazol-5-yl]methyl]-4-piperidyl]methyl]-N-methylcarbamate To a solution of tert-butyl N-methyl-N-(4-piperidylmethyl)carbamate (119 mg, 522 umol, CAS #138022-04-5) and 1-(2,6-dioxo-3-piperidyl)-3-methyl-2-oxo-benzimidazole-5-carbaldehyde (150 mg, 522 umol, Intermediate SK) in a mixed solvents of DMF (1.2 mL) and THF (2.4 mL) was added HOAc until the pH=5-6. After the reaction mixture was stirred at 10° C. for 1 hr, then $NaBH(OAc)_3$ (221 mg, 1.04 mmol) was added. Then the reaction mixture was stirred at 10° C. for 48 hrs. On completion, the reaction mixture was quenched by $H_2O$ (0.5 mL), filtered and the filtrate was concentrated in vacuo to give a residue. The residue was purified by reverse phase (0.1% FA condition) to give the title compound (230 mg, 88% yield) as a white solid. $^1H$ NMR (400 MHz, $CDCl_3$) δ 8.53 (s, 1H), 7.21 (d, J=16.0 Hz, 1H), 7.01 (J=8.0 Hz, 1H), 6.76 (d, J=8.0 Hz, 1H), 5.24 (dd, J=5.2, 12.8 Hz, 1H), 4.06-3.80 (m, 2H), 3.43 (s, 3H), 3.24 (d, J=8.0 Hz, 2H), 3.13 (s, 2H), 2.98-2.87 (m, 1H), 2.87 (s, 3H), 2.79 (d, J=4.8 Hz, 1H), 2.77-2.63 (m, 1H), 2.57-2.39 (m, 1H), 2.37-2.16 (m, 2H), 1.91-1.78 (m, 1H), 1.78-1.60 (m, 2H), 1.60-1.48 (m, 1H), 1.44 (s, 9H); LC-MS (ESI+) m/z 500.4 (M+H)+.

Step 2—3-[3-Methyl-5-[[4-(methylaminomethyl)-1-piperidyl]methyl]-2-oxo-benzimidazol-1-yl]] piperidine-2,6-dione To a solution of tert-butyl N-[[1-[[1-(2,6-dioxo-3-piperidyl)-3-methyl-2-oxo-benzimidazol-5-yl] methyl]-4-piperidyl]methyl]-N-methyl-carbamate (230 mg, 460 umol) in DCM (3 mL) was added HCl/dioxane (4 M, 3 mL). The reaction mixture was stirred at 20° C. for 2 hrs. On completion, the reaction mixture was concentrated in vacuo to give the title compound (200 mg, 99% yield, HCl) as a white solid. LC-MS (ESI+) m/z 400.3 (M+H)+.

3-[3-Methyl-5-[3-[2-(methylamino)ethoxy]propyl]-2-oxo-benzimidazol-1-yl]piperidine-2,6-dione (Intermediate ZS)

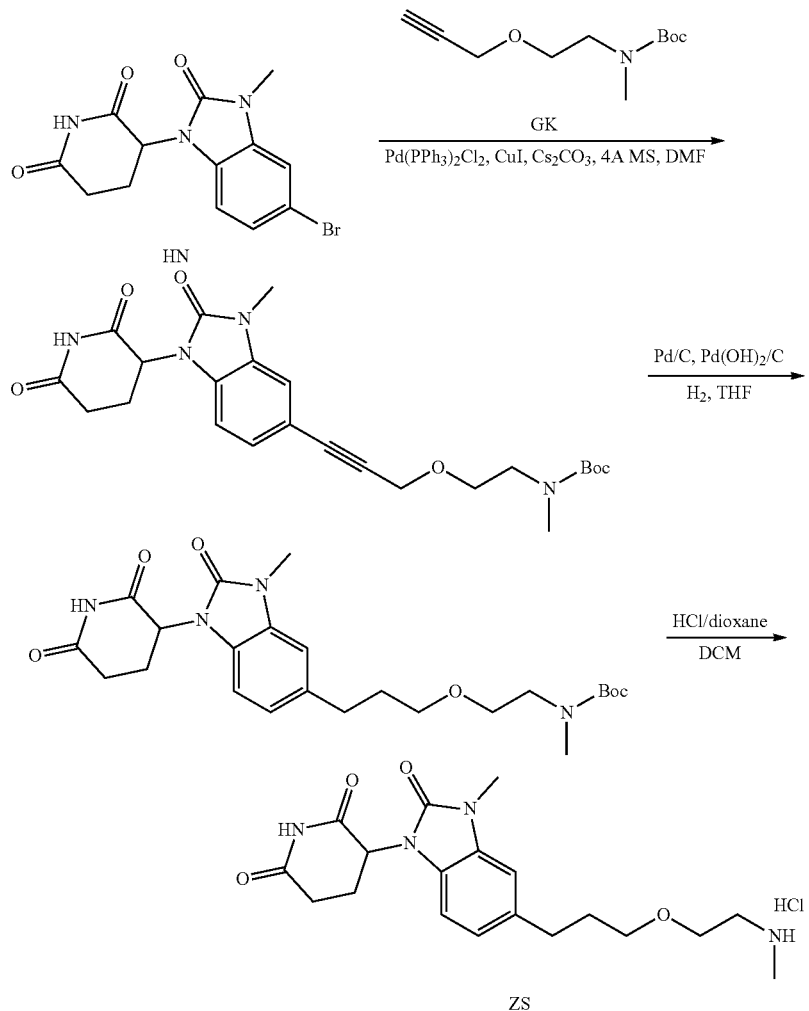

Step 1—Tert-butyl N-[2-[3-[1-(2,6-dioxo-3-piperidyl)-3-methyl-2-oxo-benzimidazol-5-yl]prop-2-ynoxy]ethyl]-N-methyl-carbamate To a solution tert-butyl N-methyl-N-(2-prop-2-ynoxyethyl)carbamate (946 mg, 4.44 mmol, Intermediate GK) and 3-(5-bromo-3-methyl-2-oxo-benzimidazol-1-yl)piperidine-2,6-dione (600 mg, 1.77 mmol, Intermediate HN) in DMF (10 mL) was added Pd(PPh$_3$)$_2$Cl$_2$ (249 mg, 355 umol), CuI (67.6 mg, 355 umol), 4 Å molecular sieves (80.0 mg, 305 umol) and Cs$_2$CO$_3$ (2.89 g, 8.87 mmol). The reaction mixture was stirred at 80° C. for 4 hrs. On completion, the reaction mixture was concentrated in vacuo. The crude product was purified by reverse phase HPLC (0.1% FA condition) to give the title compound (540 mg, 52% yield) as yellow solid. $^1$H NMR (400 MHz, DMSO-d$_6$) δ 11.10 (s, 1H), 7.31 (s, 1H), 7.18-7.12 (m, 2H), 5.38 (dd, J=5.6, 12.4 Hz, 1H), 4.39 (s, 2H), 3.62 (t, J=5.6 Hz, 2H), 3.38-3.36 (m, 2H), 3.34 (s, 3H), 2.82 (s, 3H), 2.77-2.70 (m, 1H), 2.65-2.58 (m, 2H), 2.08-2.00 (m, 1H), 1.39 (s, 9H); LC-MS (ESI$^+$) m/z 493.3 (M+Na)$^+$.

Step 2—Tert-butyl N-[2-[3-[1-(2,6-dioxo-3-piperidyl)-3-methyl-2-oxo-benzimidazol-5-yl]propoxy]ethyl]-N-methyl-carbamate To a solution of tert-butyl N-[2-[3-[1-(2,6-dioxo-3-piperidyl)-3-methyl-2-oxo-benzimidazol-5-yl] prop-2-ynoxy] ethyl]-N-methyl-carbamate (530 mg, 1.13 mmol) in THF (5 mL) was added Pd/C (40.0 mg, 10 wt %), Pd(OH)$_2$ (40.0 mg, 10 wt %) under N$_2$. The suspension was degassed under vacuum and purged with H$_2$ several times. The mixture was stirred at 25° C. for 15 hours under H$_2$ (15 psi). On completion, the reaction mixture was filtered and concentrated in vacuo to give the title compound (450 mg, 84% yield) as yellow oil. $^1$H NMR (400 MHz, DMSO-d$_6$) δ 11.07 (s, 1H), 7.04-6.97 (m, 2H), 6.85 (d, J=8.0 Hz, 1H), 5.33 (dd, J=4.8, 12.4 Hz, 1H), 3.48-3.43 (m, 2H), 3.38-3.30 (m, 3H), 2.82 (s, 3H), 2.72-2.61 (m, 4H), 2.33 (s, 1H), 2.07 (s, 4H), 2.04-1.96 (m, 1H), 1.86-1.74 (m, 2H), 1.38 (s, 9H); LC-MS (ESI$^+$) m/z 497.3 (M+Na)$^+$.

1597

Step 3-3-[3-Methyl-5-[3-[2-(methylamino)ethoxy]propyl]-2-oxo-benzimidazol-1-yl]piperidine-2,6-dione To a solution of tert-butyl N-[2-[3-[1-(2,6-dioxo-3-piperidyl)-3-methyl-2-oxo-benzimidazol-5-yl] propoxy]ethyl]-N-methyl-carbamate (430 mg, 906 umol) in DCM (2 mL) was added HCl/dioxane (2 mL). The mixture was stirred at 25° C. for 2 hrs. On completion, the reaction mixture was concentrated in vacuo to give the title compound (330 mg, 78% yield) as white solid. LC-MS (ESI+) m/z 375.2 (M+H)+.

tert-butyl N-methyl-N-(3-vinyloxypropyl)carbamate (Intermediate ZT)

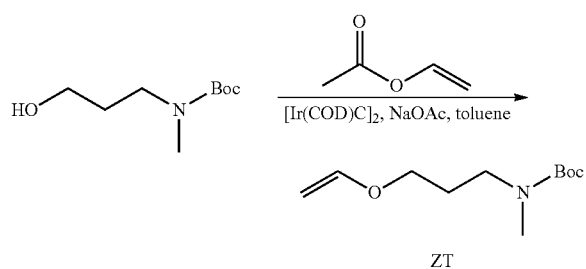

To a mixture of tert-butyl N-(3-hydroxypropyl)-N-methyl-carbamate (5.00 g, 26.4 mmol, CAS #98642-44-5) and vinyl acetate (3.41 g, 39.6 mmol, CAS #108-05-4) in toluene (20 mL) was added chloroiridium (1Z,5Z)-cyclooocta-1,5-diene (177 mg, 264 umol, CAS #12112-67-3) and Na$_2$CO$_3$ (1.68 g, 15.8 mmol) at 25° C. under N$_2$ in glove box. The mixture was stirred at 100° C. for 2 hours. On completion, the reaction mixture was quenched with water (20 mL), filtered and the filtrate was extracted with EA (2×25 mL). The combined organic layers were washed with brine (10 mL), dried over Na$_2$SO$_4$, filtered and concentrated in vacuo to give a residue. The residue was purified by column chromatography (SiO$_2$, Petroleum ether/Ethyl acetate=30/1) to afford the title compound (2.40 g, 42% yield) as a yellow oil. $^1$H NMR (400 MHz, CDCl$_3$) δ 6.51-6.42 (m, 1H), 4.21-4.13 (m, 1H), 4.02-3.96 (m, 1H), 3.69 (t, J=6.2 Hz, 2H), 3.32 (s, 2H), 2.86 (s, 3H), 1.94-1.80 (m, 2H), 1.46 (s, 9H).

3-[3-Methyl-5-[2-[3-(methylamino)propoxy] ethyl]-2-oxo-benzimidazol-1-yl]piperidine-2,6-dione (Intermediate ZU)

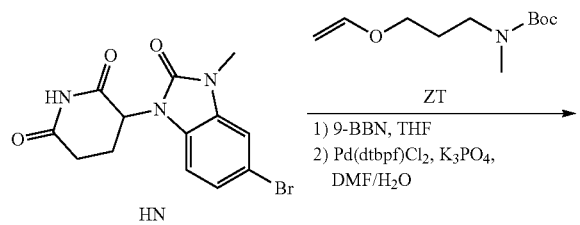

1598

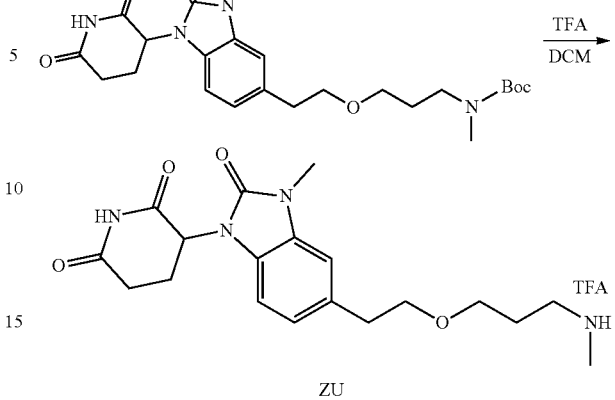

Step 1—Tert-butyl N-[3-[2-[1-(2,6-dioxo-3-piperidyl)-3-methyl-2-oxo-benzimidazol-5-yl]ethoxy]propyl]-N-methyl-carbamate To a solution of tert-butyl N-methyl-N-(3-vinyloxypropyl)carbamate (900 mg, 4.18 mmol, Intermediate ZT) in THF (10 mL) was added 9-BBN (0.5 M, 8.36 mL). The mixture was stirred at 25° C. for 2 hours. Then a solution of 3-(5-bromo-3-methyl-2-oxo-benzimidazol-1-yl)piperidine-2,6-dione (471 mg, 1.39 mmol, Intermediate HN), K$_3$PO$_4$ (739 mg, 3.48 mmol) and ditert-butyl(cyclopentyl)phosphane; dichloro palladium; iron (90.8 mg, 139 umol) in DMF (15 mL) and H$_2$O (3 mL) was added to the above mixture. The reaction mixture was stirred at 75° C. for 20 minutes under N$_2$. On completion, the reaction mixture was diluted with EA (100 mL), poured into water (50 mL) and extracted with EA (2×50 mL). The combined organic layers were dried with Na$_2$SO$_4$, filtrated and concentrated in vacuo. The residue was purified by reverse phase (0.1% FA) to give the title compound (300 mg, 45% yield) as a light yellow solid. LC-MS (ESI+) m/z 375.3 (M+H–100)+.

Step 2—3-[3-Methyl-5-[2-[3-(methylamino)propoxy]ethyl]-2-oxo-benzimidazol-1-yl]piperidine-2,6-dione To a solution of tert-butyl N-[3-[2-[1-(2,6-dioxo-3-piperidyl)-3-methyl-2-oxo-benzimidazol-5-yl] ethoxy]propyl]-N-methyl-carbamate (200 mg, 421 umol) in DCM (2 mL) was added TFA (30.8 g, 270 mmol, 20 mL). The reaction mixture was stirred at 25° C. for 1 hour. On completion, the reaction mixture was concentrated in vacuo to give the title compound (200 mg, 91% yield, 94% purity, TFA) as yellow oil. LC-MS (ESI+) m/z 375.3 (M+H)+.

3-[3-Methyl-5-[4-(methylaminomethyl)-1-piperidyl]-2-oxo-benzimidazol-1-yl]piperidine-2,6-dione (Intermediate AAA)

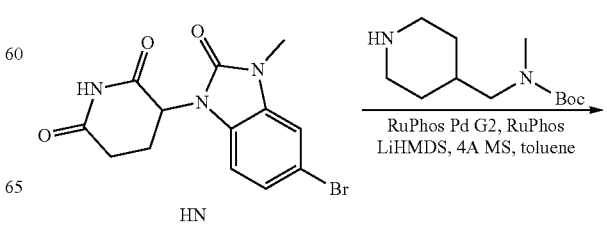

-continued

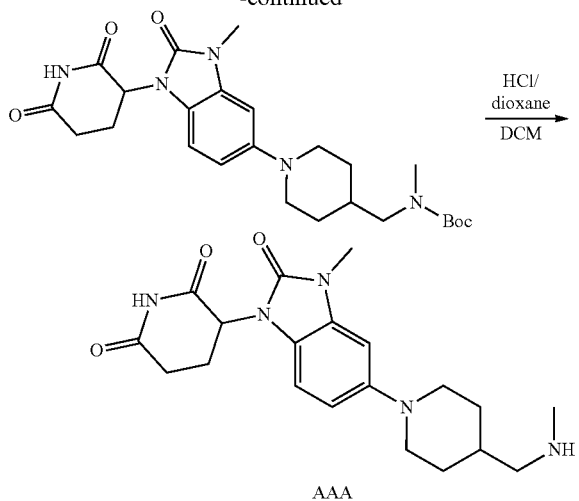

AAA

Step 1—Tert-butyl N-[[1-[1-(2,6-dioxo-3-piperidyl)-3-methyl-2-oxo-benzimidazol-5-yl]-4-piperidyl]methyl]-N-methyl-carbamate To a solution of 3-(5-bromo-3-methyl-2-oxo-benzimidazol-1-yl)piperidine-2,6-dione (500 mg, 1.48 mmol, Intermediate HN), tert-butyl N-methyl-N-(4-piperidylmethyl)carbamate (506 mg, 2.22 mmol, CAS #138022-04-5) and 4 Å molecular sieves (100 mg) in toluene (15.0 mL) was added [2-(2-aminophenyl)phenyl]-chloro-palladium; dicyclohexyl-[2-(2,6-diisopropoxyphenyl)phenyl]-phosphane (229 mg, 295 umol), RuPhos (137 mg, 295 umol) and LiHMDS (1.00 M, 5.91 mL) under $N_2$. The mixture was then stirred at 80° C. for 1 hr. On completion, the mixture was concentrated in vacuo. The residue was diluted with DMF (6 mL), filtered and the filtrate was acidified with FA until the pH=5. The filtrate was concentrated in vacuo and the residue was purified by reverse phase: (0.1% FA) to give the title compound (300 mg, 41% yield) as green solid. $^1$H NMR (400 MHz, DMSO-$d_6$) δ 11.05 (s, 1H), 6.93 (d, J=8.4 Hz, 1H), 6.84 (d, J=1.6 Hz, 1H), 6.67-6.60 (m, 1H), 5.33-5.24 (m, 1H), 3.63-3.55 (m, 2H), 3.30 (s, 3H), 3.15-3.07 (m, 2H), 2.93-2.85 (m, 1H), 2.80 (s, 3H), 2.74-2.68 (m, 1H), 2.65-2.60 (m, 2H), 2.60-2.55 (m, 1H), 2.03-1.95 (m, 1H), 1.75-1.58 (m, 3H), 1.41 (s, 9H), 1.35-1.22 (m, 2H).

Step 2—3-[3-Methyl-5-[4-(methylaminomethyl)-1-piperidyl]-2-oxo-benzimidazol-1-yl]piperidine-2,6-dione To a solution of tert-butyl N-[[1-[1-(2,6-dioxo-3-piperidyl)-3-methyl-2-oxo-benzimidazol-5-yl]-4-piperidyl]methyl]-N-methylcarbamate (270 mg, 556 umol) in DCM (7.00 mL) was added HCl/dioxane (4.00 M, 7.00 mL). The mixture was stirred at 15° C. for 0.5 hr. On completion, the mixture was concentrated in vacuo to give the title compound (230 mg, 98% yield, HCl) as yellow solid. $^1$H NMR (400 MHz, DMSO-$d_6$) δ 11.15 (s, 1H), 9.09 (s, 2H), 7.93-7.68 (m, 1H), 7.28 (d, J=6.4 Hz, 1H), 5.50-5.40 (m, 1H), 3.89-3.72 (m, 2H), 3.64-3.58 (m, 2H), 3.38 (s, 3H), 2.97-2.84 (m, 3H), 2.80-2.70 (m, 1H), 2.69-2.62 (m, 1H), 2.60-2.55 (m, 3H), 2.24-2.13 (m, 1H), 2.10-1.94 (m, 5H).

Tert-butyl N-[4-[4-[[1-[4-[[2-(2-aminoethoxy)ethyl-methyl-amino]methyl]cyclohexyl]-3-(difluoromethyl)pyrazol-4-yl]carbamoyl]oxazol-2-yl]-2-pyridyl]-N-(cyclopropylmethyl)carbamate (Intermediate AAB)

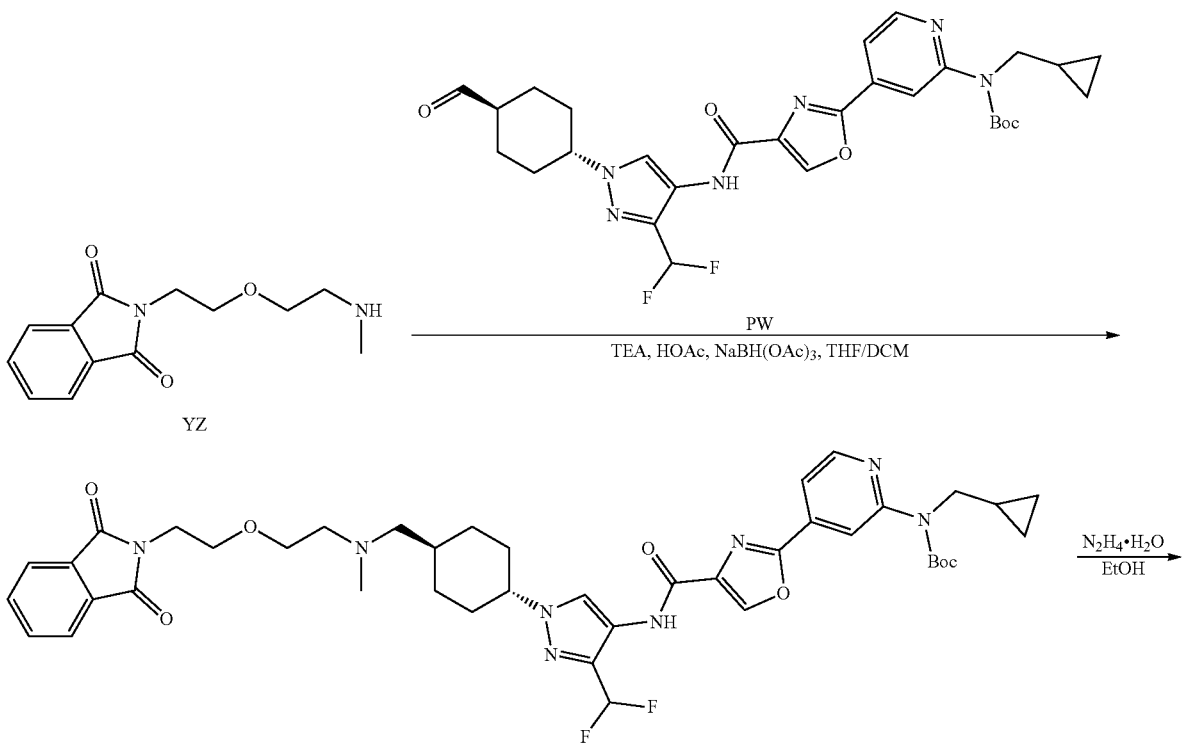

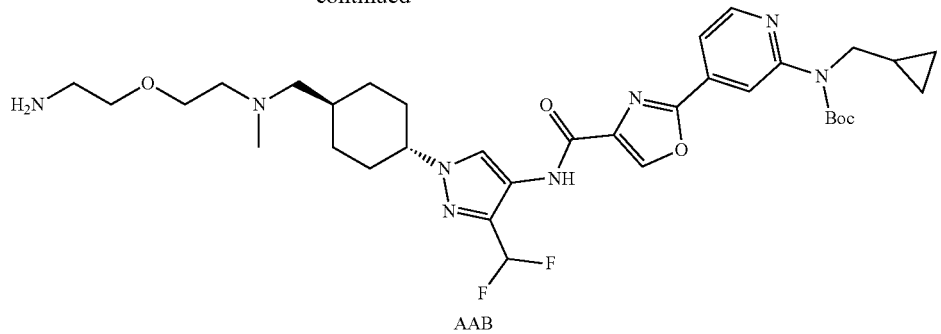

AAB

Step 1—Tert-butyl N-(cyclopropylmethyl)-N-[4-[4-[[3-(difluoromethyl)-1-[4-[[2-[2-(1,3-dioxoisoindolin-2-yl)ethoxy] ethyl-methyl-amino]methyl]cyclohexyl]pyrazol-4-yl]carbamoyl]oxazol-2-yl]-2-pyridyl]carbamate To a solution of 2-[2-[2-(methylamino)ethoxy]ethyl] isoindoline-1,3-dione (87.6 mg, 307 umol, Intermediate YN, HCl), tert-butylN-(cyclopropylmethyl)-N-[4-[4-[[3-(difluoromethyl)-1-(4-formylcyclohexyl)pyrazol-4-yl] carbamoyl] oxazol-2-yl]-2-pyridyl]carbamate (150 mg, 256 umol, Intermediate PW) in a mixture solvent of DCM (5.00 mL) and THF (5.00 mL) was added TEA (51.9 mg, 513 umol). The reaction mixture was stirred at 20° C. for 10 min. Then HOAc (46.2 mg, 769 umol) was added, and the mixture was stirred at 20° C. for 0.5 hr. Then NaBH(OAc)$_3$ (108 mg, 513 umol) was added and the mixture was stirred at 20° C. for 3 hrs. On completion, the reaction mixture was quenched with H$_2$O (2 mL) and concentrated in vacuo. The residue was purified by reverse phase: (0.1% FA) to give the title compound (150 mg, 71% yield) as yellow solid. $^1$H NMR (400 MHz, DMSO-d$_6$) δ 9.76 (s, 1H), 9.01 (s, 1H), 8.60 (d, J=5.2 Hz, 1H), 8.30 (s, 1H), 7.93-7.80 (m, 2H), 7.69 (dd, J=1.2, 5.2 Hz, 1H), 7.60-7.47 (m, 1H), 7.34-6.98 (m, 1H), 4.73-4.35 (m, 2H), 4.18-4.03 (m, 1H), 3.90-3.83 (m, 2H), 3.80-3.73 (m, 2H), 3.67-3.58 (m, 2H), 3.50-3.45 (m, 2H), 2.45-2.39 (m, 2H), 2.11-2.07 (m, 4H), 2.01-1.93 (m, 2H), 1.85-1.75 (m, 2H), 1.74-1.62 (m, 2H), 1.52 (s, 9H), 1.45-1.38 (m, 1H), 0.98-0.84 (m, 2H), 0.45-0.36 (m, 2H), 0.28-0.21 (m, 2H).

Step 2—Tert-butyl N-[4-[4-[[1-[4-[[2-(2-aminoethoxy)ethyl-methyl-amino]methyl]cyclohexyl]-3-(difluoromethyl)pyrazol-4-yl]carbamoyl]oxazol-2-yl]-2-pyridyl]-N-(cyclopropylmethyl)carbamate To a solution of tert-butyl N-(cyclopropylmethyl)-N-[4-[4-[[3-(difluoromethyl)-1-[4-[[2-[2-(1,3-dioxoisoindolin-2-yl)ethoxy] ethyl-methyl-amino]methyl]cyclohexyl]pyrazol-4-yl]carbamoyl]oxazol-2-yl]-2-pyridyl]carbamate (110 mg, 134 umol) in EtOH (1.00 mL) was added N$_2$H$_4$.H$_2$O (68.7 mg, 1.35 mmol, 98%), and the mixture was stirred at 80° C. for 2 hrs. On completion, the mixture was filtered and the filtrate was concentrated in vacuo. The residue was purified by reverse phase: (0.1% FA) to give the title compound (80.0 mg, 86% yield) as yellow solid. $^1$H NMR (400 MHz, DMSO-d$_6$) δ 9.78 (s, 1H), 9.00 (s, 1H), 8.59 (d, J=5.2 Hz, 1H), 8.35 (s, 1H), 8.29 (s, 1H), 8.18 (s, 1H), 7.68 (d, J=5.6 Hz, 1H), 7.41-6.97 (m, 1H), 4.23-4.14 (m, 1H), 3.86 (d, J=6.8 Hz, 2H), 3.51-3.45 (m, 6H), 2.91-2.75 (m, 2H), 2.19 (s, 3H), 2.18-2.14 (m, 2H), 2.10-2.01 (m, 2H), 1.96-1.86 (m, 2H), 1.83-1.67 (m, 3H), 1.51 (s, 9H), 1.22-1.13 (m, 1H), 1.10-0.96 (m, 2H), 0.45-0.36 (m, 2H), 0.27-0.20 (m, 2H).

1-[4-[4-[[2-[2-[Tert-butoxycarbonyl(cyclopropylmethyl)amino]-4-pyridyl] oxazole-4-carbonyl] amino]-3-(difluoromethyl)pyrazol-1-yl]cyclohexyl] ethylmethanesulfonate (Intermediate AAC)

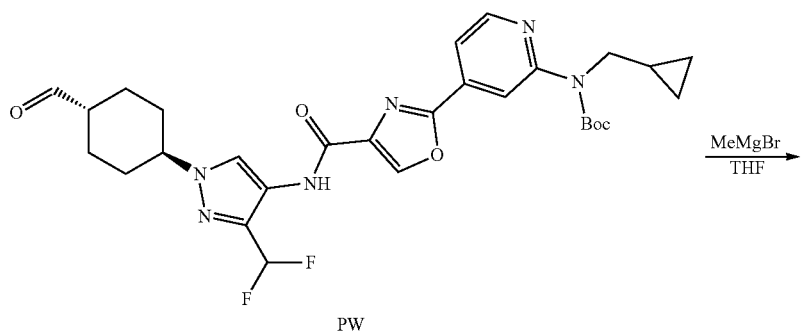

PW

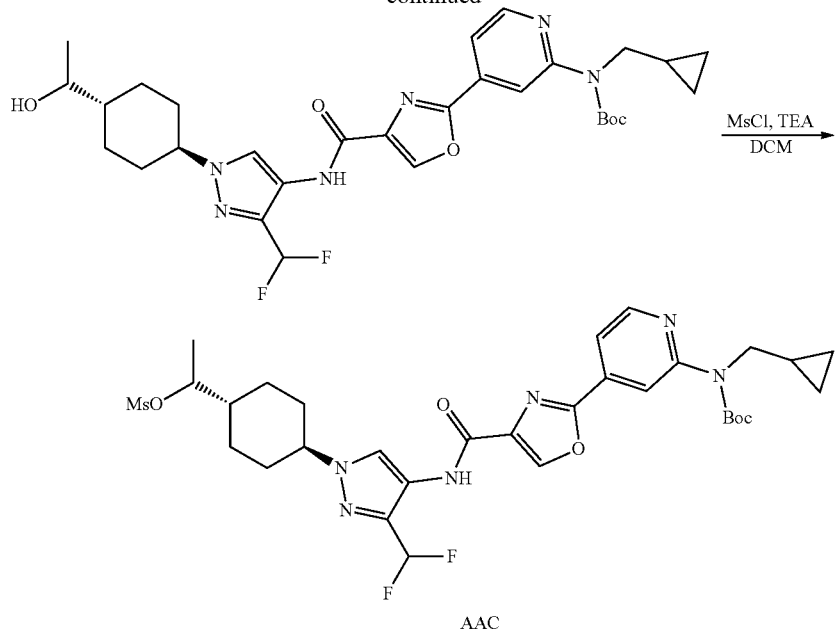

Step 1 Tert-butyl N-(cyclopropylmethyl)-N-[4-[4-[[3-(difluoromethyl)-1-[4-(1-hydroxyethyl) cyclohexyl]pyrazol-4-yl]carbamoyl] oxazol-2-yl]-2-pyridyl]carbamate To a solution of tert-butyl N-(cyclopropylmethyl)-N-[4-[4-[[3-(difluoromethyl)-1-(4-formylcyclohexyl) pyrazol-4-yl]carbamoyl]oxazol-2-yl]-2-pyridyl]carbamate (600 mg, 1.03 mmol, Intermediate PW) in THF (10 mL) was added MeMgBr (3 M, 684 uL) dropwise at −20° C., then the mixture was stirred at 10° C. for 0.5 hr. On completion, the reaction mixture was quenched with saturated NH$_4$Cl (0.5 mL) at 0° C., and then diluted with water (15 mL) and extracted with EA (3×20 mL). The combined organic layers dried over Na$_2$SO$_4$, filtered and concentrated in vacuo to give a residue. The residue was purified by prep-HPLC column: Phenomenex Synergi Max-RP 250*50 mm*10 um; mobile phase: [water (0.2% FA)-ACN]) to give the title compound (0.30 g, 48% yield) as white solid. $^1$H NMR (400 MHz, CDCl$_3$) δ 9.07 (s, 1H), 8.52 (d, J=5.2 Hz, 1H), 8.37 (s, 1H), 8.32 (s, 2H), 7.63 (dd, J=1.2, 5.2 Hz, 1H), 6.83 (d, J=54.8 Hz, 1H), 4.12-4.04 (m, 1H), 3.95 (d, J=6.8 Hz, 2H), 3.68-3.62 (m, 1H), 2.34-2.21 (m, 2H), 2.18-2.08 (m, 1H), 1.96-1.87 (m, 1H), 1.83-1.75 (m, 2H), 1.58 (s, 9H), 1.44-1.19 (m, 8H), 0.47-0.40 (m, 2H), 0.29-0.26 (m, 2H).

Step 2—1-[4-[4-[[2-[2-[Tert-butoxycarbonyl(cyclopropylmethyl)amino]-4-pyridyl]oxazole-4-carbonyl]amino]-3-(difluoromethyl)pyrazol-1-yl]cyclohexyl] ethylmethanesulfonate To a solution of tert-butyl N-(cyclopropylmethyl)-N-[4-[4-[[3-(difluoromethyl)-1-[4-(1-hydroxyethyl) cyclohexyl] pyrazol-4-yl]carbamoyl]oxazol-2-yl]-2-pyridyl]carbamate (170 mg, 283 umol) and TEA (85.9 mg, 849 umol) in DCM (3 mL) was added MsCl (48.6 mg, 424 umol) at 0° C., then the mixture was stirred at 10° C. for 0.5 hr. On completion, the reaction was diluted with water (5 mL) and extracted with DCM (4×4 mL). The combined organic layers dried over Na$_2$SO$_4$, filtered and concentrated in vacuo to give the title compound (192 mg, 99% yield) as light yellow solid. $^1$H NMR (400 MHz, CDCl$_3$) δ 9.07 (s, 1H), 8.52 (d, J=5.2 Hz, 1H), 8.37 (s, 1H), 8.32 (d, J=5.2 Hz, 2H), 7.63 (dd, J=1.6, 5.2 Hz, 1H), 6.83 (t, J=54.8 Hz, 1H), 4.73-4.67 (m, 1H), 4.13-4.05 (m, 1H), 3.95 (d, J=7.2 Hz, 2H), 3.04 (s, 3H), 2.33-2.21 (m, 2H), 2.16-2.02 (m, 1H), 2.00-1.93 (m, 1H), 1.86-1.79 (m, 2H), 1.74-1.64 (m, 1H), 1.57 (s, 9H), 1.46 (d, J=6.4 Hz, 3H), 1.39-1.27 (m, 2H), 1.25-1.18 (m, 1H), 0.47-0.40 (m, 2H), 0.31-0.25 (m, 2H).

3-[3-Methyl-5-[[4-(methylamino)-1-piperidyl] methyl]-2-oxo-benzimidazol-1-yl]piperidine-2,6-dione (Intermediate AAD)

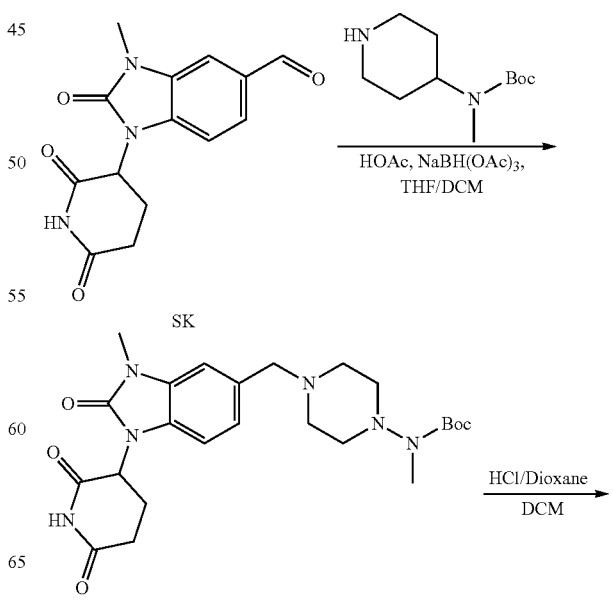

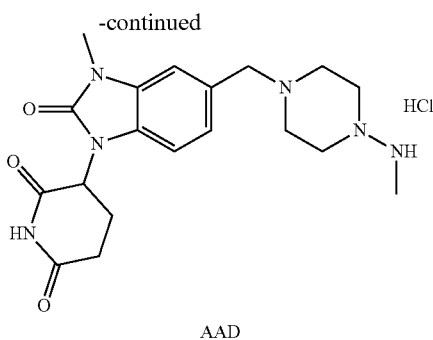

AAD

Step 1—Tert-butyl N-[1-[[1-(2,6-dioxo-3-piperidyl)-3-methyl-2-oxo-benzimidazol-5-yl]methyl]-4-piperidyl]-N-methyl-carbamate To a solution of tert butyl N-methyl-N-(4-piperidyl)carbamate (37.3 mg, 174 umol, CAS #108612-54-0) and 1-(2,6-dioxo-3-piperidyl)-3-methyl-2-oxo-benzimidazole-5-carbaldehyde (50.0 mg, 174 umol, Intermediate SK) in DMF (1.00 mL) and THF (1.00 mL) was added HOAc (20.9 mg, 348 umol). The mixture was stirred at 80° C. for 0.5 hr, then cool to 0° C., and NaBH(OAc)$_3$ (73.78 mg, 348.10 umol) was added. Then the mixture was stirred at 20° C. for 16 hrs. On completion, the reaction mixture was quenched by addition H$_2$O (0.5 mL), and then concentrated in vacuo to give a residue. The residue was purified by prep-HPLC (column: Phenomenex Synergi C18 150*25*10 um; mobile phase: [water (0.225% FA)-ACN]; B %: 17%-47%, 10 min) to give the title compound (50.0 mg, 59% yield) as a yellow solid. LC-MS (ESI$^+$) m/z 486.4 (M+H)$^+$.

Step 2—3-[3-Methyl-5-[[4-(methylamino)-1-piperidyl]methyl]-2-oxo-benzimidazol-1-yl]]piperidine-2,6-dione To a solution of tert-butyl N-[1-[[1-(2,6-dioxo-3-piperidyl)-3-methyl-2-oxo-benzimidazol-5-yl] methyl]-4-piperidyl]-N-methylcarbamate (100 mg, 205 umol) in DCM (5.00 mL) was added HCl/dioxane (4 M, 5.00 mL). The reaction mixture was stirred at 20° C. for 0.5 hr. On completion, the reaction mixture was concentrated in vacuo to give the title compound (86.0 mg, 98% yield, HCl) as a white solid. LC-MS (ESI$^+$) m/z 386.2 (M+H)$^+$.

3-[3-Methyl-4-[[3-(methylamino)azetidin-1-yl] methyl]-2-oxo-benzimidazol-1-yl]piperidine-2,6-dione (Intermediate AAE)

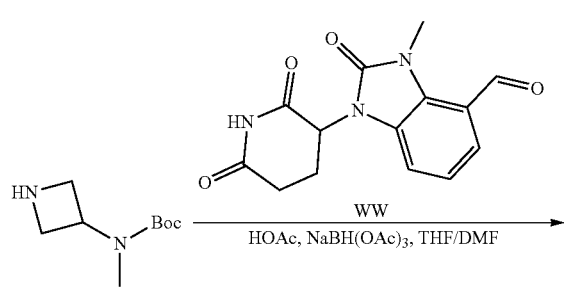

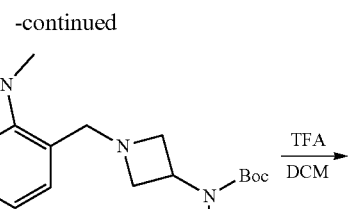

AAE

Step 1—Tert-butyl N-[1-[[1-(2,6-dioxo-3-piperidyl)-3-methyl-2-oxo-benzimidazol-4-yl]methyl] azetidin-3-yl]-N-methyl-carbamate To a solution of tert-butyl N-(azetidin-3-yl)-N-methyl-carbamate (97.2 mg, 522 umol, CAS #577777-20-9) in THF (10 mL) and DMF (3 mL) was added HOAc (522 umol, 29.86 uL). Then the mixture stirred at 25° C. for 10 minutes, 1-(2,6-dioxo-3-piperidyl)-3-methyl-2-oxo-benzimidazole-4-carbaldehyde (150 mg, 522 umol, Intermediate WW) was added to the mixture and the mixture was stirred at 80° C. for 20 minutes, then NaBH(OAc)$_3$ (221 mg, 1.04 mmol) was added at 0° C. The reaction mixture was then stirred at 25° C. for 18 hrs. On completion, the reaction mixture was quenched with 1 mL H$_2$O and concentrated in vacuo to give a residue. The residue was purified by reverse phase (0.1% FA condition) to give the title compound (140 mg, 58% yield) as a white solid. $^1$H NMR (400 MHz, DMSO-d$_6$) δ 11.09 (s, 1H), 7.11-7.01 (m, 1H), 7.01-6.91 (m, 2H), 5.36 (dd, J=6.0, 13.2 Hz, 1H), 3.82 (s, 2H), 3.64 (s, 3H), 3.52-3.37 (m, 3H), 3.30 (s, 1H), 3.17-3.00 (m, 2H), 2.97-2.84 (m, 2H), 2.79 (s, 3H), 2.06-1.92 (m, 1H), 1.37 (s, 9H); LC-MS (ESI$^+$) m/z 458.4 (M+H)$^+$.

Step 2—3-[3-Methyl-4-[[3-(methylamino)azetidin-1-yl]methyl]-2-oxo-benzimidazol-1-yl]piperidine-2,6-dione To a solution of tert-butyl N-[1-[[1-(2,6-dioxo-3-piperidyl)-3-methyl-2-oxo-benzimidazol-4-yl]methyl] azetidin-3-yl]-N-methyl-carbamate (60.0 mg, 131 umol) in DCM (5 mL) was added TFA (3 mL) at 25° C. The reaction mixture was stirred at 25° C. for 1 hr. On completion, the reaction mixture was concentrated in vacuo to give the title compound (45.0 mg, 96% yield) as colorless oil. LC-MS (ESI$^+$) m/z 358.2 (M+H)$^+$.

9-(2,6-Dioxo-3-piperidyl)pyrido[2,3-b]indole-4-carbaldehyde (Intermediate AAF)

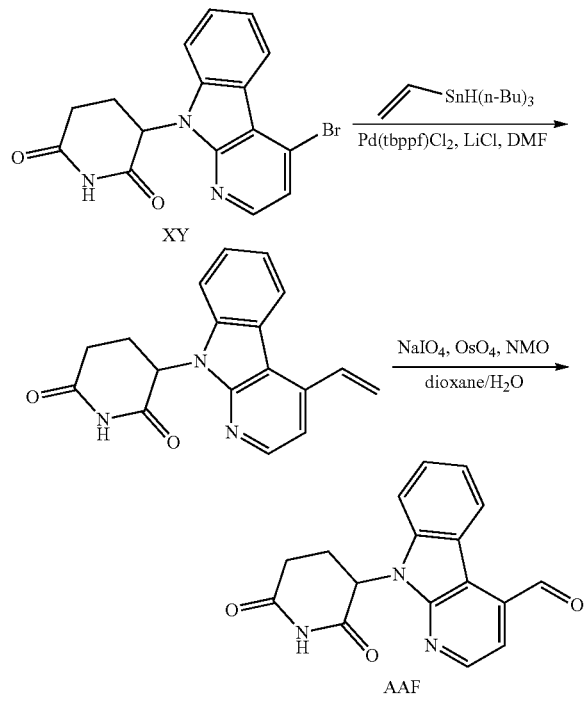

Step 1—3-(4-Vinylpyrido[2,3-b]indol-9-yl)piperidine-2,6-dione

To a solution of 3-(4-bromopyrido[2,3-b]indol-9-yl)piperidine-2,6-dione (1.00 g, 2.79 mmol, Intermediate XY) and tributyl(vinyl)stannane (1.15 g, 3.63 mmol, 1.06 mL) in DMF (15 mL) was added ditert-butyl(cyclopentyl)phosphane; iron; dichloropalladium; iron (181 mg, 279 umol) and LiCl (11.8 mg, 279 umol). The reaction mixture was stirred at 100° C. for 0.5 hr. On completion, the reaction mixture was quenched by aqueous KF solution (10 mL), and extracted with EA (2×40 mL). The organic phase was dried by $Na_2SO_4$, then filtered and the filtrate was concentrated in vacuo to give a residue. The residue was purified by reverse phase (0.1% FA condition) to give the title compound (630 mg, 74% yield) as a light yellow solid. $^1$H NMR (400 MHz, DMSO-$d_6$) δ 11.14 (s, 1H), 8.38 (d, J=5.2 Hz, 1H), 8.28 (d, J=8.0 Hz, 1H), 7.78-7.68 (m, 1H), 7.67-7.58 (m, 1H), 7.53 (t, J=7.6 Hz, 1H), 7.44 (d, J=5.2 Hz, 1H), 7.31 (t, J=7.6 Hz, 1H), 6.24 (d, J=17.2 Hz, 1H), 6.16-5.94 (m, 1H), 5.79 (d, J=11.2 Hz, 1H), 3.17-2.96 (m, 2H), 2.70-2.58 (m, 1H), 2.17-2.08 (m, 1H); LC-MS (ESI$^+$) m/z 306.2 (M+H)$^+$.

Step 2—9-(2,6-Dioxo-3-piperidyl)pyrido[2,3-b]indole-4-carbaldehyde

To a solution of 3-(4-vinylpyrido[2,3-b]indol-9-yl)piperidine-2,6-dione (530 mg, 1.74 mmol) in dioxane (1 mL) and $H_2O$ (1 mL) was added $NaIO_4$ (742 mg, 3.47 mmol, 192 uL), $OsO_4$ (44.1 mg, 173 umol, 9.01 uL) and 2,6-dimethylpyridine (372 mg, 3.47 mmol, 404 uL) at 0° C. The reaction mixture was stirred at 15° C. for 2 hrs. On completion, the reaction mixture was quenched by aqueous $Na_2S_2O_3$ solution (2 mL), and then extracted with EA (2×30 mL). The organic phase was dried by $Na_2SO_4$, filtered and the filtrate was concentrated in vacuo to give a residue. The residue was purified by reverse phase (0.1% FA condition) to give the title compound (340 mg, 63% yield) as a green solid. $^1$H NMR (400 MHz, DMSO-$d_6$) δ 11.20 (s, 1H), 10.58 (s, 1H), 8.90 (d, J=8.0 Hz, 1H), 8.75 (d, J=4.8 Hz, 1H), 7.83 (d, J=4.8 Hz, 1H), 7.80-7.68 (m, 1H), 7.64 (t, J=6.8 Hz, 1H), 7.37 (t, J=7.6 Hz, 1H), 6.40-6.01 (m, 1H), 3.24-2.97 (m, 2H), 2.82-2.69 (m, 1H), 2.24-2.11 (m, 1H); LC-MS (ESI$^+$) m/z 308.1 (M+H)$^+$.

3-[4-[[4-(Methylamino)-1-piperidyl]methyl]pyrido[2,3-b]indol-9-yl]piperidine-2,6-dione (Intermediate AAG)

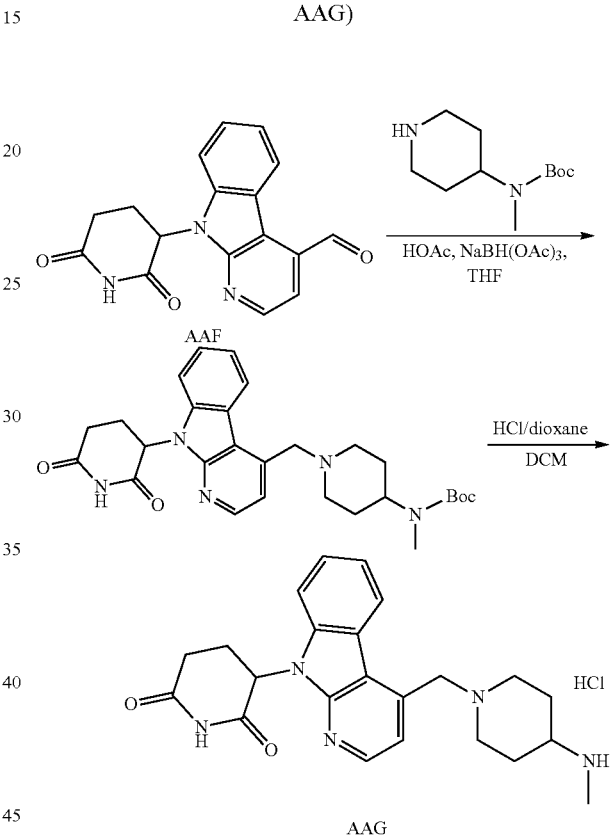

Step 1—Tert-butyl N-1-[[9-(2,6-dioxo-3-piperidyl)pyrido]2,3-b]indol-4-yl]methyl]-4-piperidyl]-N-methyl-carbamate To a solution of 9-(2,6-dioxo-3-piperidyl)pyrido[2,3-b]indole-4-carbaldehyde (100 mg, 325 umol, Intermediate AAF) and tert-butyl N-methyl-N-(4-piperidyl)carbamate (69.7 mg, 325 umol, CAS #108612-54-0) in THF (5 mL) was added HOAc (19.5 mg, 325 umol, 18.6 uL). The mixture was stirred at 20° C. for 30 minutes, then NaBH(OAc)$_3$ (137 mg, 650 umol) was added to the mixture. The reaction mixture was stirred at 20° C. for 16 hrs. On completion, the residue was filtered and the filtrate was concentrated in vacuo to give a residue. The residue was purified by prep-HPLC (column: Shim-pack C18 150*25*10 um; mobile phase: [water (0.225% FA)-ACN]; B %: 22%-43%, 7 min) to give the title compound (120 mg, 73% yield) as a white solid. $^1$H NMR (400 MHz, DMSO-$d_6$) δ 11.15 (s, 1H), 8.37 (d, J=4.0 Hz, 1H), 8.22 (d, J=7.6 Hz, 1H), 7.75-7.56 (m, 1H), 7.51 (t, J=7.2 Hz, 1H), 7.31 (t, J=7.2 Hz, 1H), 7.26 (d, J=3.6 Hz, 1H), 6.29-5.91 (m, 1H), 4.08-3.97 (m, 2H), 3.95-3.76 (m, 1H), 3.07-2.99 (m, 3H), 2.80-2.65 (m, 2H), 2.64 (s, 3H), 2.20 (t, J=10.8 Hz, 2H), 2.15-2.08 (m, 1H), 1.77-1.62 (m, 2H), 1.57-1.46 (m, 2H), 1.39 (s, 9H); LC-MS (ESI+) m/z 506.4 (M+H)+.

Step 2—3-[4-[[4-(Methylamino)-1-piperidyl]methyl]pyrido[2,3-b]indol-9-yl]piperidine-2,6-dione To a solution of tert-butyl N-[1-[[9-(2,6-dioxo-3-piperidyl)pyrido[2,3-b]indol-4-yl]methyl]-4-piperidyl]-N-methyl-carbamate (115 mg, 227 umol) in DCM (2 mL) was added HCl/dioxane (4 M, 2.22 mL). The reaction mixture was then stirred at 20° C. for 2 hrs. On completion, the mixture was concentrated in vacuo to give the title compound (100 mg, 99% yield, HCl salt) as a white solid. LC-MS (ESI+) m/z 406.2 (M+H)+.

Tert-butyl N-methyl-N-[3-(methylamino)propyl] carbamate (Intermediate AAH)

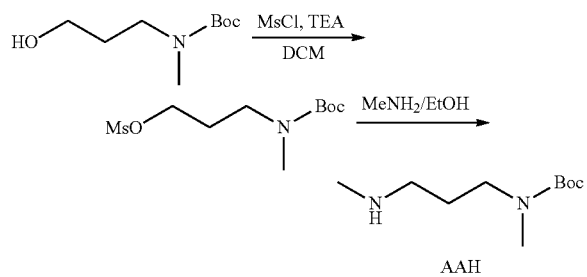

AAH

Step 1—3-[Tert-butoxycarbonyl(methyl)amino]propyl methanesulfonate

To a solution of tert-butyl N-(3-hydroxypropyl)-N-methyl-carbamate (2.00 g, 10.5 mmol, CAS #98642-44-5), and Et₃N (1.28 g, 12.6 mmol, 1.77 mL) in DCM (20 mL) was added MsCl (1.54 g, 13.4 mmol, 1.04 mL). Then the reaction mixture was stirred at 0° C. for 1 hr. On completion, the reaction mixture was quenched with water (10 mL) and extracted with DCM (3×20 mL). The combined organic layers were washed by water (2×20 mL), then dried over Na₂SO₄, filtrated and concentrated in vacuo to give title compound (2.80 g, 90% yield) as yellow oil.

Step 2—Tert-butyl N-methyl-N-[3-(methylamino)propyl]carbamate

To a mixture of 3-[tert-butoxycarbonyl(methyl)amino]propyl methanesulfonate (1.00 g, 3.74 mmol) in EtOH (8 mL) was added MeNH₂ (11.6 g, 112 mmol, 30% solution). The reaction mixture was then stirred at 80° C. for 12 hours. On completion, the reaction mixture was concentrated in vacuo. The residue was purified by column chromatography to give the title compound (300 mg, 39% yield) as yellow oil. ¹H NMR (400 MHz, CDCl₃) δ 3.25 (s, 2H), 2.81 (s, 3H), 2.54 (t, J=6.8 Hz, 2H), 2.40 (s, 3H), 1.72-1.65 (m, 2H), 1.43 (s, 9H).

3-[3-Methyl-4-[[methyl-[3-(methylamino)propyl]amino]methyl]-2-oxo-benzimidazol-1-yl]piperidine-2,6-dione (Intermediate AAI)

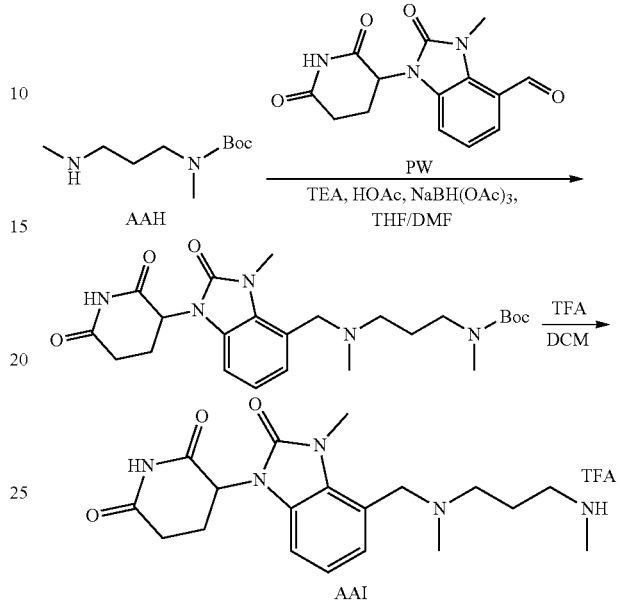

Step 1—Tert-butyl N-[3-[[1-(2,6-dioxo-3-piperidyl)-3-methyl-2-oxo-benzimidazol-4-yl]methyl-methyl-amino]propyl]-N-methyl-carbamate To a mixture of tert-butyl N-methyl-N-[3-(methylamino)propyl]carbamate (295 mg, 1.46 mmol, Intermediate AAH) in DMF (3 mL) and THF (3 mL) was added TEA (123 mg, 1.22 mmol, 169 uL) and stirred at 25° C. for 12 minutes. Then 1-(2,6-dioxo-3-piperidyl)-3-methyl-2-oxo-benzimidazole-4-carbaldehyde (350 mg, 1.22 mmol, Intermediate WW) and HOAc (73.1 mg, 1.22 mmol, 69.6 uL) were added to the mixture and stirred at 80° C. for 0.5 hour. Finally, NaBH(OAc)₃ (516 mg, 2.44 mmol) was added to the mixture at 0° C. The reaction mixture was stirred at 25° C. for 12 hours. On completion, the reaction mixture was quenched with water (0.1 mL) and concentrated in vacuo. The residue was purified by reverse phase (0.1% FA condition) to give the title compound (200 mg, 34% yield) as white solid. ¹H NMR (400 MHz, DMSO-d₆) δ 11.09 (s, 1H), 8.15 (s, 1H), 7.07 (d, J=7.6 Hz, 1H), 6.96 (t, J=7.6 Hz, 1H), 6.91-6.88 (m, 1H), 5.40-5.34 (m, 1H), 3.69-3.61 (m, 5H), 3.08 (t, J=6.8 Hz, 2H), 2.95-2.84 (m, 1H), 2.80-2.71 (m, 1H), 2.67 (s, 3H), 2.65-2.60 (m, 1H), 2.34 (t, J=7.2 Hz, 2H), 2.12 (s, 3H), 2.04-1.94 (m, 1H), 1.67-1.58 (m, 2H), 1.36 (s, 9H); LC-MS (ESI+) m/z 474.2 (M+H)+.

Step 2—3-[3-Methyl-4-[[methyl-[3-(methylamino)propyl]amino]methyl]-2-oxo-benzimidazol-1-yl]piperidine-2,6-dione To a mixture of tert-butyl N-[3-[[1-(2,6-dioxo-3-piperidyl)-3-methyl-2-oxo-benzimidazol-4-yl]methyl-methyl-amino]propyl]-N-methyl-carbamate (190 mg, 401 umol) in DCM (3 mL) was added TFA (7.70 g, 67.5 mmol, 5 mL). The reaction mixture was stirred at 25° C. for 1 hour. On completion, the reaction mixture was concentrated in vacuo to give the title compound (195 mg, 99% yield, TFA salt) as light yellow oil. LC-MS (ESI+) m/z 374.2 (M+H)+.

3-[3-Methyl-2-oxo-5-(piperazin-1-ylmethyl)benz-imidazol-1-yl]piperidine-2,6-dione (Intermediate AAJ)

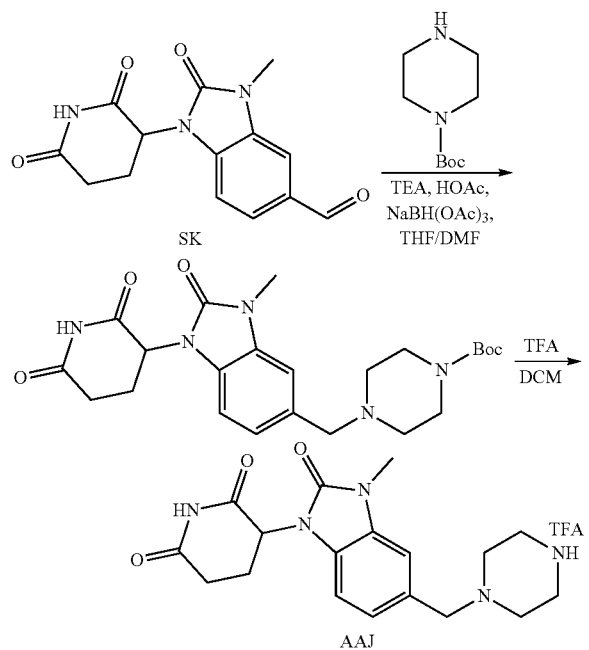

Step 1—Tert-butyl 4-[[1-(2,6-dioxo-3-piperidyl)-3-methyl-2-oxo-benzimidazol-5-yl]methyl]piperazine-1-carboxylate To a mixture of tert-butyl piperazine-1-carboxylate; hydrochloride (139 mg, 626 umol, CAS #57260-71-6) in DMF (1 mL) and THF (2 mL) was added TEA (52.8 mg, 522 umol, 72.6 uL) and the reaction mixture was stirred at 25° C. for 12 min. Then 1-(2,6-dioxo-3-piperidyl)-3-methyl-2-oxo-benzimidazole-5-carbaldehyde (150 mg, 522 umol, Intermediate SK) and HOAc (31.3 mg, 522 umol, 29.8 uL) were added to the mixture at 25° C. for 0.5 hour. Finally, NaBH(OAc)₃ (221 mg, 1.04 mmol) was added the mixture at 0° C. The reaction mixture was stirred at 25° C. for 12 hours. On completion, the reaction mixture was quenched with water (0.1 mL) and concentrated in vacuo. The residue was purified by reverse phase (0.1% FA condition) to give the title compound (150 mg, 62% yield) as white solid. ¹H NMR (400 MHz, DMSO-d₆) δ 11.08 (s, 1H), 7.11 (s, 1H), 7.07-7.03 (m, 1H), 6.99-6.95 (m, 1H), 5.39-5.31 (m, 1H), 3.49 (s, 3H), 3.32-3.27 (m, 4H), 2.97-2.86 (m, 1H), 2.76-2.60 (m, 2H), 2.32 (t, J=4.8 Hz, 4H), 2.05-1.96 (m, 1H), 1.38 (s, 9H); LC-MS (ESI+) m/z 458.4 (M+H)+.

Step 2—3-[3-Methyl-2-oxo-5-(piperazin-1-ylmethyl)benzimidazol-1-yl]piperidine-2,6-dione To a mixture of tert-butyl 4-[[1-(2,6-dioxo-3-piperidyl)-3-methyl-2-oxo-benzimidazol-5-yl]methyl] piperazine-1-carboxylate (120 mg, 262 umol) in DCM (2 mL) was added TFA (4.62 g, 40.5 mmol). The reaction mixture was stirred at 25° C. for 1 hour. On completion, the reaction mixture was concentrated in vacuo to give title compound (120 mg, TFA salt) as red oil. LC-MS (ESI+) m/z 358.2 (M+H)+.

3-[4-(2,7-Diazaspiro[3.5]nonan-7-ylmethyl)-3-methyl-2-oxo-benzimidazol-1-yl]piperidine-2,6-dione (Intermediate AAK)

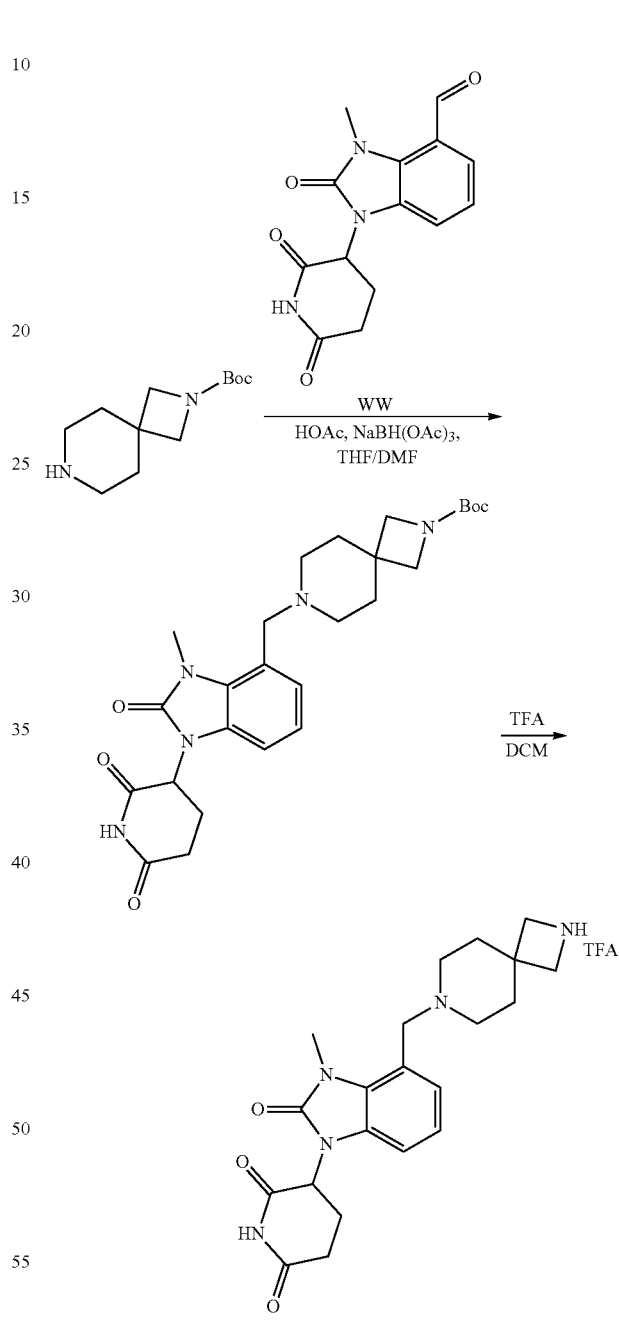

Step 1—Tert-butyl 7-[[1-(2,6-dioxo-3-piperidyl)-3-methyl-2-oxo-benzimidazol-4-yl]methyl]-2,7-diaz-aspiro[3.5]nonane-2-carboxylate To a solution of tert-butyl 2,7-diazaspiro[3.5]nonane-2-carboxylate (133 mg, 591 umol, CAS #236406-55-6) in THF (15 mL) and DMF (3 mL) was added HOAc (591 umol, 33.8 uL) and 1-(2,6-dioxo-3-piperidyl)-3-methyl-2-oxo-benzimidazole-4-carbaldehyde (170 mg, 591 umol, Intermediate WW). The reaction mixture was stirred at 80° C. for 20 minutes, then NaBH(OAc)$_3$ (250 mg, 1.18 mmol) was added to the mixture at 0° C. The reaction mixture was stirred at 25° C. for 45 hrs. On completion, the reaction mixture was quenched with 1 mL H$_2$O and concentrated in vacuo to give a residue. The residue was purified by reverse phase (0.1% FA condition) to give the title compound (115 mg, 39% yield) as a white solid. $^1$H NMR (400 MHz, DMSO-d$_6$) δ 11.10 (s, 1H), 7.06 (d, J=7.6 Hz, 1H), 6.95 (t, J=7.6 Hz, 1H), 6.86 (d, J=8.0 Hz, 1H), 5.44-5.29 (m, 1H), 3.66 (s, 3H), 3.59 (s, 2H), 3.51 (s, 6H), 2.96-2.82 (m, 1H), 2.75-2.69 (m, 1H), 2.65-2.55 (m, 2H), 2.05-1.97 (m, 1H), 1.63 (s, 5H), 1.37 (s, 9H); LC-MS (ESI$^+$) m/z 498.3 (M+H)$^+$.

Step 2—3-[4-(2,7-Diazaspiro[3.5]nonan-7-ylmethyl)-3-methyl-2-oxo-benzimidazol-1-yl]piperidine-2,6-dione To a solution of tert-butyl 7-[[1-(2,6-dioxo-3-piperidyl)-3-methyl-2-oxo-benzimidazol-4-yl]methyl]-2,7-diazaspiro[3.5]nonane-2-carboxylate (50.0 mg, 100 umol) in DCM (5 mL) was added TFA (54.0 mmol, 4 mL) at 25° C. The reaction mixture was stirred at 25° C. for 1 hr. On completion, the reaction mixture was concentrated in vacuo to give the title compound (38 mg, 95% yield) as colorless oil. LC-MS (ESI$^+$) m/z 398.2 (M+H)$^+$.

Tert-butyl 9-[[1-(2,6-dioxo-3-piperidyl)-3-methyl-2-oxo-benzimidazol-4-yl]methyl]-3,9-diazaspiro[5.5]undecane-3-carboxylate (Intermediate AAL)

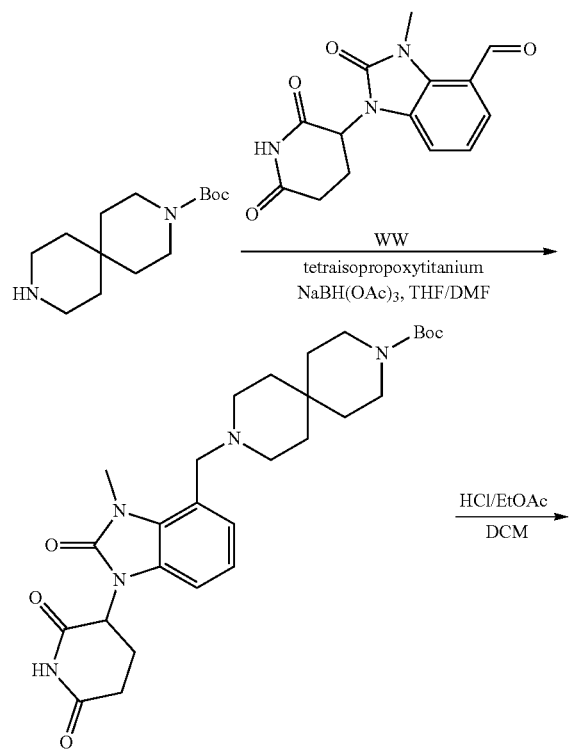

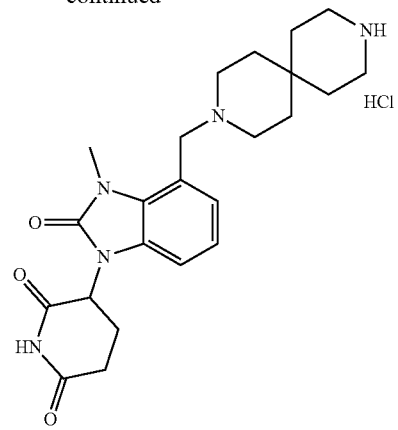

AAL

Step 1—Tert-butyl 9-[[1-(2,6-dioxo-3-piperidyl)-3-methyl-2-oxo-benzimidazol-4-yl]methyl]-3,9-diazaspiro[5.5]undecane-3-carboxylate To a solution of 1-(2,6-dioxo-3-piperidyl)-3-methyl-2-oxo-benzimidazole-4-carbaldehyde (100 mg, 348 umol, Intermediate WW) and tert-butyl 3,9-diazaspiro[5.5]undecane-3-carboxylate (88.5 mg, 348 umol, CAS #173405-78-2) in THF (3 mL) and DMF (3 mL) was added tetraisopropoxytitanium (296 mg, 1.04 mmol, 308 uL). The mixture was stirred at 80° C. for 2 hrs, then NaBH(OAc)$_3$ (147 mg, 696 umol) was added to the mixture. The reaction mixture was stirred at 20° C. for 16 hrs. On completion, the residue was filtered and the filtrate was concentrated in vacuo to give a residue. The residue was purified by reverse phase (0.1% FA condition) to give the title compound (145 mg, 79% yield) as a white solid. $^1$H NMR (400 MHz, DMSO-d$_6$) δ 11.10 (s, 1H), 7.06 (d, J=8.0 Hz, 1H), 6.95 (t, J=7.6 Hz, 1H), 6.90-6.85 (m, 1H), 5.37 (dd, J=5.2, 12.4 Hz, 1H), 3.66 (s, 3H), 3.65-3.60 (m, 2H), 3.30-3.23 (m, 4H), 2.94-2.84 (m, 1H), 2.77-2.68 (m, 1H), 2.65-2.57 (m, 1H), 2.43-2.34 (m, 4H), 2.05-1.96 (m, 1H), 1.45-1.39 (m, 4H), 1.38 (s, 9H), 1.36-1.30 (m, 4H); LC-MS (ESI$^+$) m/z 526.2 (M+H)$^+$.

Step 2—3-[4-(3,9-Diazaspiro[5.5]undecan-3-ylmethyl)-3-methyl-2-oxo-benzimidazol-1-yl]piperidine-2,6-dione To a solution of tert-butyl 9-[[1-(2,6-dioxo-3-piperidyl)-3-methyl-2-oxo-benzimidazol-4-yl]methyl]-3,9-diazaspiro[5.5]undecane-3-carboxylate (70.0 mg, 133 umol) in DCM (1.5 mL) was added HCl/EtOAc (4 M, 1.50 mL). The reaction mixture was stirred at 20° C. for 0.5 hr. On completion, the mixture was concentrated in vacuo to give the title compound (60.0 mg, 97% yield, HCl) as a white solid. LC-MS (ESI$^+$) m/z 426.3 (M+H)$^+$.

1-Methyl-3-[3-methyl-4-[[4-(methylamino)-1-piperidyl]methyl]-2-oxo-benzimidazol-1-yl] piperidine-2,6-dione (Intermediate AAM)

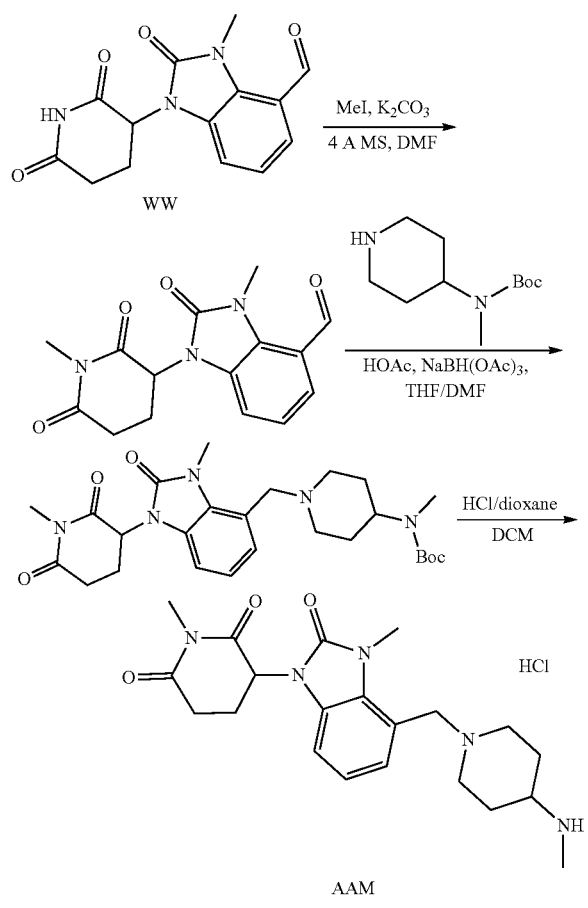

Step 1—3-Methyl-1-(1-methyl-2,6-dioxo-3-piperidyl)-2-oxo-benzimidazole-4-carbaldehyde To a solution of 1-(2,6-dioxo-3-piperidyl)-3-methyl-2-oxo-benzimidazole-4-carbaldehyde (150 mg, 522 umol, Intermediate WW), K$_2$CO$_3$ (108 mg, 783 umol), 4 A MS (50 mg) in DMF (5 mL) was added MeI (111 mg, 783 umol, 48.7 uL). The reaction mixture was stirred at 15° C. for 12 hrs. On completion, the mixture was filtered and the filtrate was concentrated in vacuo to give a residue. The residue was purified by reverse phase (0.1% FA condition) to give the title compound (120 mg, 76% yield) as a white solid. $^1$H NMR (400 MHz, DMSO-d$_6$) δ 10.40 (s, 1H), 7.61 (dd, J=0.8, 8.0 Hz, 1H), 7.46 (d, J=7.2 Hz, 1H), 7.20 (t, J=8.0 Hz, 1H), 5.53 (dd, J=5.4, 13.2 Hz, 1H), 3.68 (s, 3H), 3.04 (s, 3H), 3.01-2.93 (m, 1H), 2.84-2.72 (m, 2H), 2.11-2.03 (m, 1H); LC-MS (ESI$^+$) m/z 302.2 (M+H)$^+$.

Step 2—Tert-butyl N-methyl-N-[1-[[3-methyl-1-(1-methyl-2,6-dioxo-3-piperidyl)-2-oxo-benzimidazol-4-yl]methyl]-4-piperidyl]carbamate To a solution of 3-methyl-1-(1-methyl-2,6-dioxo-3-piperidyl)-2-oxo-benzimidazole-4-carbaldehyde (120 mg, 398 umol) and tert-butyl N-methyl-N-(4-piperidyl)carbamate (85.3 mg, 398 umol, CAS #108612-54-0) in THF (3 mL) was added HOAc (23.9 mg, 398 umol, 22.7 uL). The mixture was stirred at 20° C. for 30 minutes, then NaBH(OAc)$_3$ (168 mg, 796 umol) was added to the mixture. The reaction mixture was stirred at 20° C. for 16 hrs. On completion, the mixture was quenched by addition H$_2$O (0.2 mL), then the mixture was concentrated in vacuo to give a residue. The residue was purified by reverse phase (0.1% FA condition) to give the title compound (160 mg, 80% yield) as a white solid. LC-MS (ESI$^+$) m/z 500.2 (M+H)$^+$.

Step 3—1-Methyl-3-[3-methyl-4-[[4-(methylamino)-1-piperidyl]methyl]-2-oxo-benzimidazol-1-yl] piperidine-2,6-dione To a solution of tert-butyl N-methyl-N-[1-[[3-methyl-1-(1-methyl-2,6-dioxo-3-piperidyl)-2-oxo-benzimidazol-4-yl]methyl]-4-piperidyl]carbamate (150 mg, 300 umol) in DCM (3 mL) was added HCl/dioxane (4 M, 3 mL). The reaction mixture was stirred at 20° C. for 2 hrs. On completion, the mixture was concentrated in vacuo to give the title compound (130 mg, 99% yield, HCl salt) as a white solid. LC-MS (ESI$^+$) m/z 400.2 (M+H)$^+$.

Tert-butyl N-methyl-N-[3-(4-piperidyloxy)cyclobutyl]carbamate (Intermediate AAN)

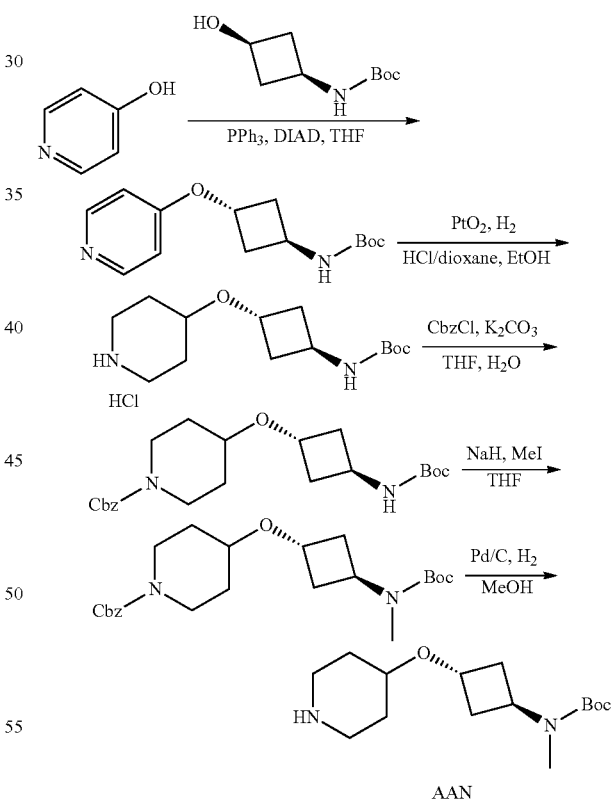

Step 1—Tert-butyl N-[3-(4-pyridyloxy)cyclobutyl]carbamate

To a solution of pyridin-4-ol (2.05 g, 21.5 mmol, CAS #626-64-2), tert-butyl N-(3-hydroxycyclobutyl) carbamate (2.70 g, 14.4 mmol, CAS #389890-43-1) and PPh$_3$ (5.67 g, 21.6 mmol) in THF (50 mL) was added DIAD (4.37 g, 21.6 mmol) slowly at 0° C. The mixture was stirred at 15° C. for 1 hour under N$_2$. Then, the mixture was stirred at 50° C. for 16 hours under N$_2$. On completion, the mixture was concentrated in vacuo. The residue was purified by reversed phase flash (FA condition) and column chromatography on silica gel to give the title compound (3.20 g, 83% yield) as white solid. $^1$H NMR (400 MHz, CDCl$_3$) δ 8.45 (m, 2H), 6.73 (d, J=4.4 Hz, 2H), 4.94-4.72 (m, 2H), 4.31 (s, 1H), 2.65-2.53 (m, 2H), 2.52-2.37 (m, 2H), 1.46 (s, 9H).

Step 2—Tert-butyl N-[3-(4-piperidyloxy)cyclobutyl]carbamate

To a solution of tert-butyl N-[3-(4-pyridyloxy)cyclobutyl]carbamate (1.00 g, 3.78 mmol) in EtOH (30 mL) was added HCl/dioxane (1.0 M, 3.8 mL) at 15° C. The mixture was stirred at 15° C. for 0.5 hour. Then PtO$_2$ (1.00 g, 4.40 mmol) was added to the mixture was at 15° C. The mixture was stirred at 40° C. for 16 hours under H$_2$ (50 Psi). On completion, the mixture was filtered, and the cake was washed with EtOH (10 mL). The filtrate and washing were combined and concentrated in vacuo to give the title compound (1.15 g, 99% yield, HCl) as white solid. $^1$H NMR (400 MHz, DMSO-d$_6$) δ 9.08-8.67 (m, 2H), 7.20-7.02 (m, 1H), 4.21-4.12 (m, 1H), 4.00-3.85 (m, 1H), 3.54-3.45 (m, 1H), 3.11 (m, 1H), 3.02-2.87 (m, 3H), 2.13-2.01 (m, 3H), 1.94-1.86 (m, 1H), 1.71-1.51 (m, 4H), 1.36 (d, J=1.2 Hz, 9H).

Step 3—Benzyl 4-[3-(tert-butoxycarbonylamino)cyclobutoxy]piperidine-1-carboxylate A solution of tert-butyl N-[3-(4-piperidyloxy)cyclobutyl]carbamate (1.15 g, 4.25 mmol), and K$_2$CO$_3$ (1.19 g, 8.62 mmol) in THF (10 mL) and H$_2$O (10 mL) was stirred at 15° C. for 0.5 hour. Then CbzCl (798 mg, 4.68 mmol) was added to the mixture at 15° C. The reaction mixture was stirred at 15° C. for 1 hour. On completion, the mixture was diluted with water (20 mL), then extracted with EA (3×20 mL). The combined organic layer was washed with brine (10 mL), dried over Na$_2$SO$_4$, filtered and concentrated in vacuo. The residue was purified by column chromatography on silica gel to give the title compound (850 mg, 49% yield) as light yellow oil. $^1$H NMR (400 MHz, CDCl$_3$) δ 7.43-7.28 (m, 5H), 5.13 (s, 2H), 4.74-4.57 (m, 1H), 4.25-4.21 (m, 1H), 4.17-4.07 (m, 1H), 3.91-3.77 (m, 2H), 3.48-3.39 (m, 1H), 3.20-3.15 (m, 2H), 2.42-2.29 (m, 2H), 2.20-2.10 (m, 2H), 1.77 (m, 2H), 1.51-1.49 m, 2H), 1.45 (s, 9H).

Step 4—Benzyl 4-[3-[tert-butoxycarbonyl(methyl)amino]cyclobutoxy]piperidine-1-carboxylate To a solution of benzyl 4-[3-(tert-butoxycarbonylamino)cyclobutoxy]piperidine-1-carboxylate (850 mg, 2.10 mmol) in THF (15 mL) was added NaH (127 mg, 3.18 mmol, 60% dispersion in oil) at 0° C. The mixture was stirred at 15° C. for 0.5 hour. Then MeI (2.74 g, 19.2 mmol) was added to the mixture at 0° C. The mixture was stirred at 15° C. for 16 hours under N$_2$. On completion, the reaction was quenched with sat. aq. NH$_4$Cl (20 mL). The mixture was extracted with EA (3×20 mL). The combined organic layer was washed with brine (10 mL), dried over Na$_2$SO$_4$, filtered and concentrated in vacuo. The residue was purified by column chromatography on silica gel to give the title compound (750 mg, 85% yield) as light yellow oil. $^1$H NMR (400 MHz, CDCl$_3$) δ 7.41-7.29 (m, 5H), 5.13 (s, 2H), 4.76-4.60 (m, 1H), 4.20-4.11 (m, 1H), 3.94-3.77 (m, 2H), 3.46-3.42 (m, 1H), 3.22-3.11 (m, 2H), 2.83 (s, 3H), 2.39-2.21 (m, 4H), 1.87-1.72 (m, 2H), 1.57-1.48 (m, 2H), 1.46 (s, 9H).

Step 5—Tert-butyl N-methyl-N-[3-(4-piperidyloxy)cyclobutyl]carbamate

To a solution of benzyl 4-[3-[tert-butoxycarbonyl(methyl)amino]cyclobutoxy]piperidine-1-carboxylate (700 mg, 1.67 mmol) in MeOH (10 mL) was added Pd/C (200 mg, 10 wt %) at 10° C. The mixture was stirred at 10° C. for 1 hour under H$_2$ (50 Psi). On completion, the mixture was filtered, and the cake was washed with MeOH (10 mL). The filtrate and washing were combined and concentrated in vacuo to give the title compound (420 mg, 88% yield) as light yellow oil. $^1$H NMR (400 MHz, CDCl$_3$) δ 4.67 (m, 1H), 4.18-4.16 (m, 1H), 3.39-3.30 (m, 1H), 3.11-3.08 (m, 2H), 2.85 (s, 1H), 2.82 (s, 3H), 2.76-2.57 (m, 3H), 2.38-2.21 (m, 4H), 1.92-1.77 (m, 2H), 1.45 (s, 9H), 1.44-1.41 (m, 2H).

3-[3-Methyl-4-[[4-[3-(methylamino)cyclobutoxy]-1-piperidyl]methyl]-2-oxo-benzimidazol-1-yl]piperidine-2,6-dione (Intermediate AAO)

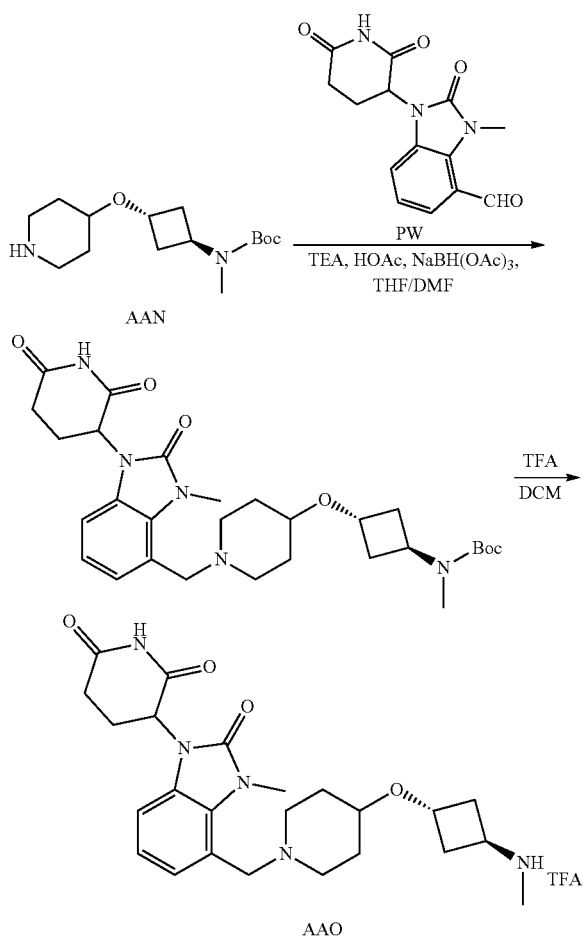

Step 1—Tert-butyl N-[3-[[1-[[1-(2,6-dioxo-3-piperidyl)-3-methyl-2-oxo-benzimidazol-4-yl]methyl]-4-piperidyl]oxy]cyclobutyl]-N-methyl-carbamate A mixture of tert-butyl N-methyl-N-[3-(4-piperidyloxy)cyclobutyl]carbamate (220 mg, 773 umol, Intermediate AAN), 1-(2,6-dioxo-3-piperidyl)-3-methyl-2-oxo-benzimidazole-4-carbaldehyde (200 mg, 696 umol, Intermediate WW) and HOAc (126 mg, 2.10 mmol) in THF (7.5 mL) and DMF (2.5 mL) was stirred at 40° C. for 0.5 hour. Then NaBH(OAc)$_3$ (295 mg, 1.39 mmol) was added to the mixture at 10° C., the mixture was stirred at 40° C. for 3 hours. On completion, the reaction was quenched with water (0.5 mL) and the mixture was concentrated in vacuo. The residue was purified by reverse phase flash (TFA condition) to give the title compound (210 mg, 54% yield) as light yellow oil. $^1$H NMR (400 MHz, CDCl$_3$) δ 8.21 (s, 1H), 7.25 (s, 1H), 7.14 (t, J=8.0 Hz, 1H), 6.90 (d, J=8.0 Hz, 1H), 5.23-5.18 (m, 1H), 4.88-4.68 (m, 1H), 4.60-4.44 (m, 2H), 4.12-4.03 (m, 1H), 3.70 (s, 3H), 3.67 (s, 1H), 3.39 (m, 2H), 3.09-3.05 (m, 2H), 3.00-2.93 (m, 1H), 2.89-2.83 (m, 1H), 2.81 (s, 3H), 2.80-2.73 (m, 1H), 2.40-2.30 (m, 2H), 2.29-2.12 (m, 5H), 1.95-1.91 (m, 2H), 1.46 (s, 9H).

Step 2—3-[3-Methyl-4-[[4-[3-(methylamino)cyclobutoxy]-1-piperidyl]methyl]-2-oxo-benzimidazol-1-yl]piperidine-2,6-dione To a solution of tert-butyl N-[3-[[1-[[1-(2,6-dioxo-3-piperidyl)-3-methyl-2-oxo-benzimidazol-4-yl] methyl]-4-piperidyl]oxy]cyclobutyl]-N-methyl-carbamate (205 mg, 368 umol) in DCM (6 mL) was added TFA (3 mL) at 10° C. The mixture was stirred at 10° C. for 3 hours. On completion, the mixture was concentrated in vacuo to give the title compound (210 mg, 99% yield, TFA salt) as light yellow gum. $^1$H NMR (400 MHz, DMSO-d$_6$) δ 11.14 (s, 1H), 8.87 (d, J=2.8 Hz, 2H), 7.27 (d, J=7.2 Hz, 1H), 7.22-7.12 (m, 2H), 5.47-5.42 (m, 1H), 4.69-4.54 (m, 2H), 4.31-4.29 (m, 1H), 3.67 (s, 2H), 3.60 (s, 3H), 3.52-3.43 (m, 1H), 3.37-3.13 (m, 3H), 2.95-2.85 (m, 1H), 2.78-2.64 (m, 2H), 2.56-2.52 (m, 3H), 2.40-2.16 (m, 4H), 2.10-1.96 (m, 2H), 1.93-1.79 (m, 2H), 1.62-1.54 (m, 1H).

[3-Methyl-4-[2-[3-(methylamino)azetidin-1-yl]ethyl]-2-oxo-benzimidazol-1-yl]piperidine-2,6-dione (Intermediate AAP)

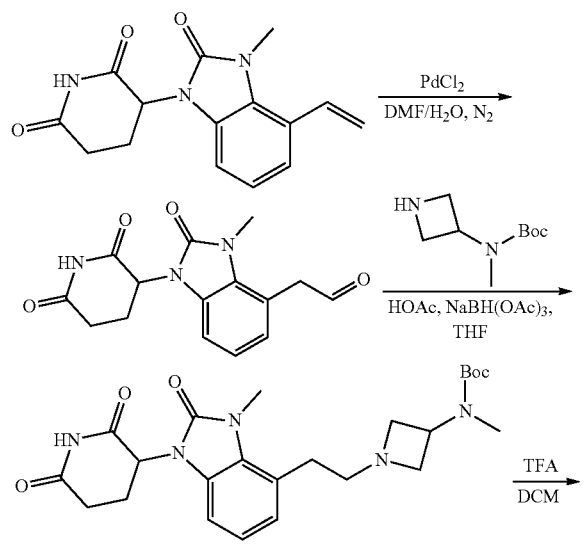

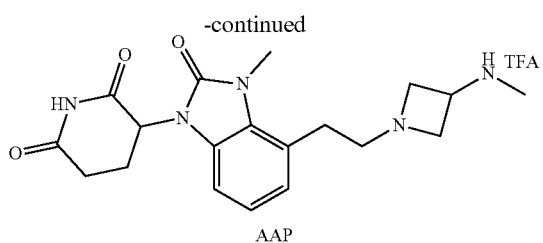

Step 1—2-[1-(2,6-Dioxo-3-piperidyl)-3-methyl-2-oxo-benzimidazol-4-yl]acetaldehyde To a solution of 3-(3-methyl-2-oxo-4-vinyl-benzimidazol-1-yl)piperidine-2,6-dione (1.00 g, 3.51 mmol, Intermediate AAV) in a mixed solvent of DMF (20 mL) and H$_2$O (2 mL) was added PdCl$_2$ (1.24 g, 7.01 mmol, CAS #7647-10-1) at 25° C. under N$_2$. The mixture was stirred at 25° C. for 18 hours. On completion, the reaction mixture was concentrated under reduced pressure to remove solvent. The residue was diluted with water (20 mL) and extracted with EA (3×20 mL). The combined organic layers were dried over Na$_2$SO$_4$, filtered and concentrated in vacuo to give the title compound (260 mg, 24% yield) as black brown oil. LC-MS (ESI$^+$) m/z 301.9 (M+H)$^+$.

Step 2—Tert-butyl N-[1-[2-[1-(2,6-dioxo-3-piperidyl)-3-methyl-2-oxo-benzimidazol-4-yl]ethyl]azetidin-3-yl]-N-methyl-carbamate To a mixture of 2-[1-(2,6-dioxo-3-piperidyl)-3-methyl-2-oxo-benzimidazol-4-yl]acetaldehyde (200 mg, 663 umol) and tert-butyl N-(azetidin-3-yl)-N-methyl-carbamate (123 mg, 663 umol, CAS #577777-20-9) in THF (5 mL) was added HOAc (39.8 mg, 663 umol, 37.9 uL) at 25° C. The mixture was stirred at 25° C. for 0.5 hour. Then, NaBH(OAc)$_3$ (281 mg, 1.33 mmol) was added, and the mixture was stirred at 25° C. for another 3.5 hours. On completion, the reaction mixture was quenched by water (0.5 mL) at 25° C., and then concentrated in vacuo to give a residue. The residue was purified by reverse phase (0.1% FA condition) to give the title compound (260 mg, 83% yield, 51% purity) as light yellow oil. LC-MS (ESI$^+$) m/z 472.1 (M+H)$^+$.

Step 3—[3-Methyl-4-[2-[3-(methylamino)azetidin-1-yl]ethyl]-2-oxo-benzimidazol-1-yl]]piperidine-2,6-dione To a solution of tert-butyl N-[1-[2-[1-(2,6-dioxo-3-piperidyl)-3-methyl-2-oxo-benzimidazol-4-yl]ethyl] azetidin-3-yl]-N-methyl-carbamate (110 mg, 233 umol) in DCM (5.5 mL) was added TFA (74.3 mmol, 5.50 mL) at 25° C. The mixture was stirred at 25° C. for 2 hours. On completion, the reaction mixture was concentrated in vacuo to give the title compound (80.0 mg, 70% yield, TFA salt) as yellow oil. LC-MS (ESI$^+$) m/z 372.1 (M+H)$^+$.

5-[[(1R,2S)-2-hydroxycyclohexyl]amino]pyrazolo[1,5-a]pyrimidine-3-carboxylic acid (Intermediate AAO)

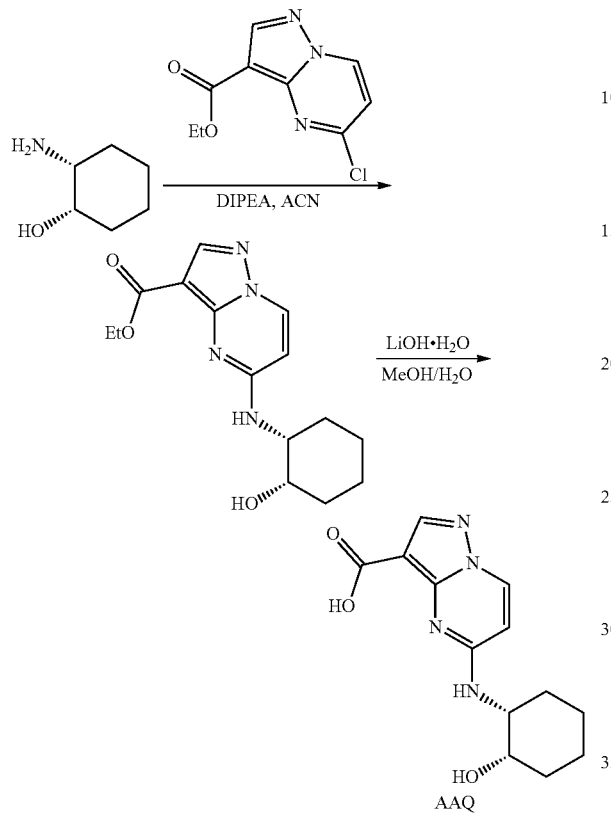

Step 1—Ethyl 5-[[(1R,2S)-2-hydroxycyclohexyl]amino]pyrazolo[1,5-a]pyrimidine-3-carboxylate To a solution of cis-2-aminocyclohexanol (504 mg, 3.32 mmol, HCl, racemic) and ethyl 5-chloropyrazolo[1,5-a]pyrimidine-3-carboxylate (500 mg, 2.22 mmol, CAS #1224944-77-7) in ACN (15.0 mL) was added DIPEA (1.15 g, 8.86 mmol). Then the mixture was stirred at 60° C. for 16 hrs. On completion, the mixture was concentrated in vacuo. The mixture was triturated with $H_2O$ (8 mL), filtered and the solid was dried in vacuo to give the title compound (620 mg, 91% yield) as yellow solid. $^1$H NMR (400 MHz, DMSO-$d_6$) δ 8.48 (d, J=7.6 Hz, 1H), 8.12 (s, 1H), 7.64 (d, J=7.2 Hz, 1H), 6.54 (d, J=7.6 Hz, 1H), 4.72 (d, J=2.8 Hz, 1H), 4.22-4.13 (m, 2H), 4.11-4.02 (m, 1H), 4.01-3.93 (m, 1H), 1.81-1.67 (m, 2H), 1.67-1.54 (m, 3H), 1.53-1.43 (m, 1H), 1.40-1.31 (m, 2H), 1.31-1.23 (m, 3H).

Step 2—5-[[(1R,2S)-2-hydroxycyclohexyl]amino]pyrazolo[1,5-a]pyrimidine-3-carboxylic acid To a solution of ethyl 5-[[(1R,2S)-2-hydroxycyclohexyl]amino]pyrazolo[1,5-a]pyrimidine-3-carboxylate (580 mg, 1.91 mmol) in a mixed solvent of MeOH (30 mL) and $H_2O$ (6 mL) was added LiOH—$H_2O$ (399 mg, 9.53 mmol). Then the mixture was stirred at 60° C. for 16 hrs. On completion, the mixture was concentrated in vacuo. The residue was diluted with $H_2O$ (15 mL) and acidified with 1N HCl solution until the pH=5. Then filtered the solid was dried in vacuo to give the title compound (470 mg, 89% yield) as white solid. $^1$H NMR (400 MHz, DMSO-$d_6$) δ 11.48 (s, 1H), 8.49 (d, J=7.2 Hz, 1H), 8.10 (s, 1H), 7.71 (d, J=7.2 Hz, 1H), 6.57 (d, J=7.6 Hz, 1H), 4.91-4.61 (m, 1H), 4.15-4.00 (m, 1H), 3.95-3.85 (m, 1H), 1.80-1.68 (m, 2H), 1.65-1.54 (m, 3H), 1.53-1.43 (m, 1H), 1.39-1.25 (m, 2H).

[4-[3-(Difluoromethyl)-4-nitro-pyrazol-1-yl]]cyclohexyl]methyl methanesulfonate (Intermediate AAR)

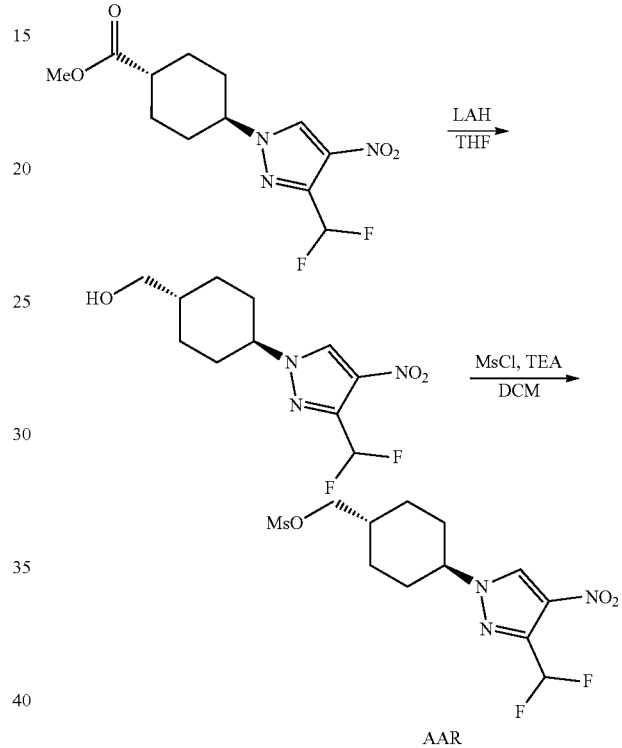

Step 1—[4-[3-(Difluoromethyl)-4-nitro-pyrazol-1-yl]cyclohexyl]methanol

To a solution of methyl 4-[3-(difluoromethyl)-4-nitro-pyrazol-1-yl]cyclohexanecarboxylate (1.2 g, 3.96 mmol, synthesized via Steps 1-2 of Intermediate QS) in THF (20 mL) was cooled to −20° C. Subsequently, LiAlH$_4$ (180 mg, 4.75 mmol) was added. The reaction mixture was stirred at −20° C. for 0.5 hr. On completion, the mixture was quenched with a solution of 15% NaOH (2 mL) and added anhydrous sodium sulfate. The mixture was filtered and concentrated in vacuo to give the title compound (1.09 g, 100% yield) as light yellow oil. $^1$H NMR (400 MHz, CDCl$_3$) δ 8.14 (s, 1H), 7.19-6.90 (m, 1H), 4.11 (tt, J=3.6, 12.4 Hz, 1H), 3.48 (d, J=6.4 Hz, 2H), 2.28-2.19 (m, 2H), 2.04-1.93 (m, 2H), 1.75-1.66 (m, 2H), 1.60-1.55 (m, 1H), 1.20-1.12 (m, 2H).

Step 2—[4-[3-(Difluoromethyl)-4-nitro-pyrazol-1-yl]cyclohexyl]methyl methanesulfonate To a solution of [4-[3-(difluoromethyl)-4-nitro-pyrazol-1-yl]cyclohexyl]methanol (500 mg, 1.82 mmol) in DCM (5 mL) was TEA (551 mg, 5.45 mmol). The reaction mixture was cooled to 0° C. Then, MsCl (312 mg, 2.72 mmol) was added. The resulting reaction mixture was stirred at 15° C. for 0.5 hr. On completion, the reaction mixture was quenched with water (3 mL) and extracted with DCM (3×15 mL). The combined organic layers were washed with brine (10 mL), dried over anhydrous sodium sulfate, filtered and the filtrate was concentrated in vacuo to give the title compound (640 mg, 99% yield) as yellow oil. $^1$H NMR (400 MHz, CDCl$_3$) δ 8.14 (s, 1H), 7.18-6.90 (m, 1H), 4.17-4.07 (m, 1H), 4.04 (d, J=6.0 Hz, 2H), 2.97 (s, 3H), 2.95 (d, J=2.8 Hz, 1H), 2.32-2.22 (m, 2H), 2.00 (d, J=12.8 Hz, 2H), 1.87-1.81 (m, 1H), 1.80-1.70 (m, 2H), 1.29-1.20 (m, 2H).

4-[3-(Difluoromethyl)-4-nitro-pyrazol-1-yl]cyclohexanecarbaldehyde (Intermediate AAS)

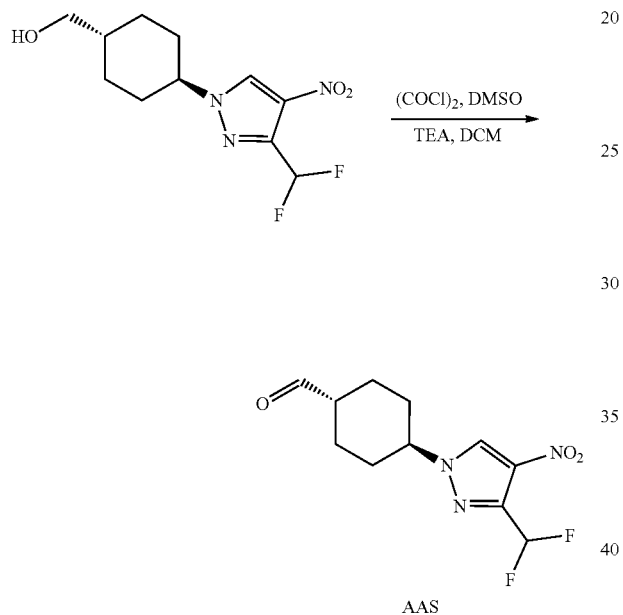

AAS

To a solution of DMSO (2.55 g, 32.7 mmol, 2.55 mL) in DCM (30.0 mL) was slowly added (COCl)$_2$ (2.08 g, 16.3 mmol) at −72° C. The cooling bath was removed and the reaction mixture was stirred at −70° C. for 5 min. A solution of [4-[3-(difluoromethyl)-4-nitro-pyrazol-1-yl]cyclohexyl]methanol (1.80 g, 6.54 mmol, synthesized via Step 1 of Intermediate AAR) in DCM (30.0 mL) was added at −65° C., and the solution was stirred for 1 hr, then TEA (6.62 g, 65.3 mmol) was added. The cooling bath was removed 25 minutes after completed addition. On completion, the reaction mixture was quenched with 1 M aqueous hydrochloric acid solution (2 ml, 2 mmol) at −10° C., and the layers were separated. The organic layer was washed with two 10 mL-portions of water and one 5 mL portion of brine, dried over anhydrous sodium sulfate and concentrated in vacuo. The residue was purified by prep-HPLC (column: Phenomenex luna C18 250*50 mm*10 um; mobile phase: [water (0.225% FA)-ACN]; B %: 25%-55%, 25 min) to give the title compound (280 mg, 15% yield) as white solid. $^1$H NMR (400 MHz, CDCl$_3$) δ 9.63 (s, 1H), 8.15 (s, 1H), 7.05 (t, J=53.2 Hz, 1H), 4.15-4.08 (m, 1H), 2.32-2.29 (m, 3H), 2.29-2.26 (m, 2H), 1.84-1.80 (m, 2H), 1.45-1.30 (m, 2H).

2-[4-[3-(Difluoromethyl)-4-nitro-pyrazol-1-yl]]cyclohexyl]acetaldehyde (Intermediate AAT)

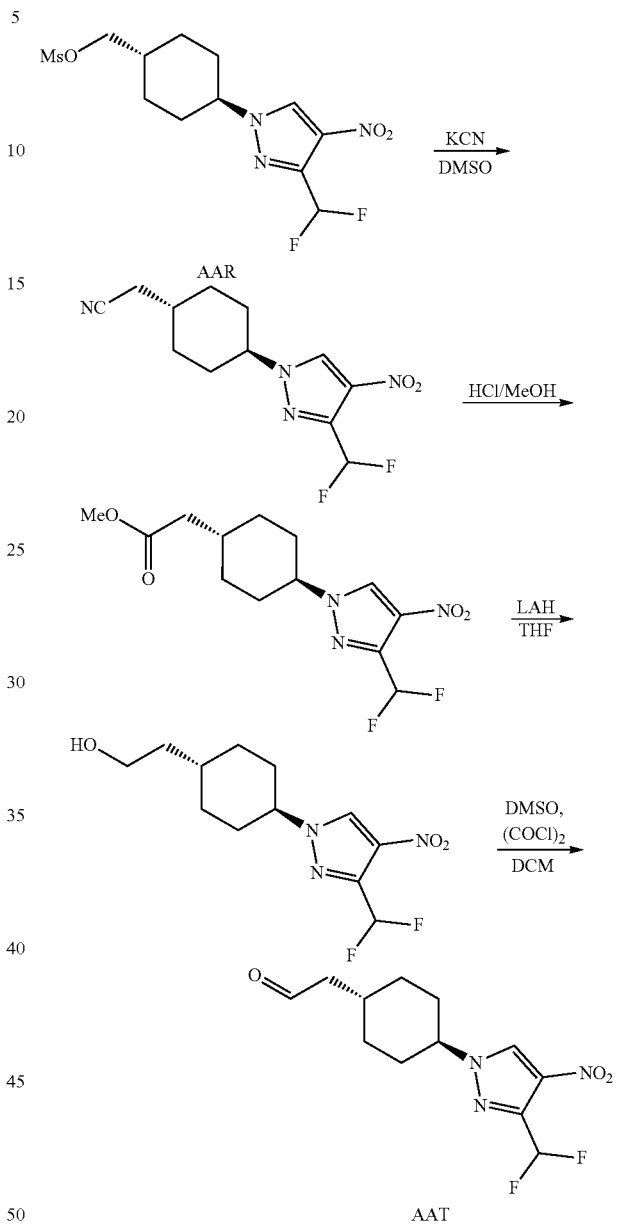

AAT

Step 1—2-[4-[3-(Difluoromethyl)-4-nitro-pyrazol-1-yl]cyclohexyl]acetonitrile

To a solution of [4-[3-(difluoromethyl)-4-nitro-pyrazol-1-yl]cyclohexyl]methyl methanesulfonate (640 mg, 1.81 mmol, Intermediate AAR) in DMSO (5 mL) was added KCN (177 mg, 2.72 mmol). The reaction mixture was heated to 80° C. for 48 hrs. On completion, the reaction mixture was diluted with water (10 mL), then extracted with ethyl acetate (3×50 mL). The combined organic layers were wash with brine (30 mL), dried over anhydrous sodium sulfate, filtered and the filtrate was concentrated in vacuo. The residue was purified by column chromatography (SiO$_2$, Petroleum ether/Ethyl acetate=5/1 to 1:1) to give the title compound (350 mg, 68% yield) as a yellow oil. $^1$H NMR (400 MHz, CDCl$_3$) δ 8.23 (s, 1H), 7.27-6.98 (m, 1H), 4.21 (tt, J=4.8, 12.4 Hz, 1H), 2.40 (d, J=6.4 Hz, 2H), 2.38-2.31 (m, 2H), 2.18-2.10 (m, 2H), 1.95-1.82 (m, 3H), 1.47-1.35 (m, 2H).

Step 2—Methyl 2-[4-[3-(difluoromethyl)-4-nitro-pyrazol-1-yl]cyclohexyl]acetate 2-[4-[3-(difluoromethyl)-4-nitro-pyrazol-1-yl]cyclohexyl]acetonitrile (140 mg, 492 umol) was dissolved in HCl/MeOH (4 M, 5.60 mL) solution. The resulting solution was heated to 75° C. to reflux for 24 hrs. On completion, the reaction mixture was concentrated in vacuo. The reaction mixture was purified by prep-TLC (PE:EA=2:1). to give the title compound (60 mg, 38% yield) as a yellow oil. $^1$H NMR (400 MHz, CDCl$_3$) δ 8.22 (s, 1H), 7.28-6.99 (m, 1H), 4.19 (tt, J=3.6, 12.0 Hz, 1H), 3.71 (s, 3H), 2.33-2.25 (m, 4H), 2.08-2.00 (m, 2H), 1.99-1.88 (m, 1H), 1.82 (dq, J=3.6, 12.8 Hz, 2H), 1.29-1.19 (m, 2H).

Step 3—2-[4-[3-(Difluoromethyl)-4-nitro-pyrazol-1-yl]cyclohexyl]ethanol

To a solution of methyl 2-[4-[3-(difluoromethyl)-4-nitro-pyrazol-1-yl]cyclohexyl]acetate (100 mg, 315 umol) in THF (10 mL) was cooled to −20° C. Subsequently, LiAlH$_4$ (14.3 mg, 378 umol) was added. The reaction mixture was stirred at −20° C. for 0.5 hr. On completion, the reaction mixture was quenched with a solution of 15% NaOH (1 mL) and added anhydrous sodium sulfate. The mixture was filtered and concentrated in vacuo to give the title compound (70 mg, 77% yield) as light yellow oil. $^1$H NMR (400 MHz, CDCl$_3$) δ 8.22 (s, 1H), 7.28-6.99 (m, 1H), 4.20 (tt, J=4.0, 12.0 Hz, 1H), 3.75 (s, 2H), 2.35-2.25 (m, 2H), 2.03 (d, J=12.0 Hz, 2H), 1.88-1.72 (m, 2H), 1.62-1.59 (m, 1H), 1.34-1.13 (m, 4H).

Step 4—2-[4-[3-(Difluoromethyl)-4-nitro-pyrazol-1-yl]cyclohexyl]acetaldehyde To a solution of DMSO (56.7 mg, 726 umol) in DCM (3 mL) was slowly added (COCl)$_2$ (46.0 mg, 362 umol) at −72° C. The cooling bath was removed and the reaction mixture was stirred at −70° C. for 5 min. A solution of 2-[4-[3-(difluoromethyl)-4-nitro-pyrazol-1-yl]cyclohexyl]ethanol (70 mg, 242 umol) in DCM (3 mL) was added at −65° C. The reaction was stirred at 1 hr then TEA (147 mg, 1.45 mmol) was added. The cooling bath was removed 25 minutes after completed addition. On completion, the reaction mixture was quenched with 1 M aqueous hydrochloric acid solution (2 ml, 2 mmol) at −10° C. The layers were separated and the organic layer was washed with two 10 ml portions of water and one 5 ml portion of brine, dried over anhydrous sodium sulfate and concentrated in vacuo to give the title compound (69 mg, 99% yield) as a yellow oil. $^1$H NMR (400 MHz, CDCl$_3$) δ 9.72 (t, J=1.6 Hz, 1H), 8.13 (d, J=0.8 Hz, 1H), 7.18-6.91 (m, 1H), 4.11 (tt, J=3.6, 12.0 Hz, 1H), 2.36 (dd, J=1.6, 6.4 Hz, 1H), 2.24-2.16 (m, 2H), 1.96-1.90 (m, 2H), 1.81-1.64 (m, 2H), 1.16-1.08 (m, 2H), 0.85-0.74 (m, 2H).

3-[4-[3-[2-[2-[4-[4-Amino-3-(difluoromethyl)pyrazol-1-yl]cyclohexyl]ethyl-methyl-amino]ethoxy]propyl]-3-methyl-2-oxo-benzimidazol-1-yl]]piperidine-2,6-dione (Intermediate AAU)

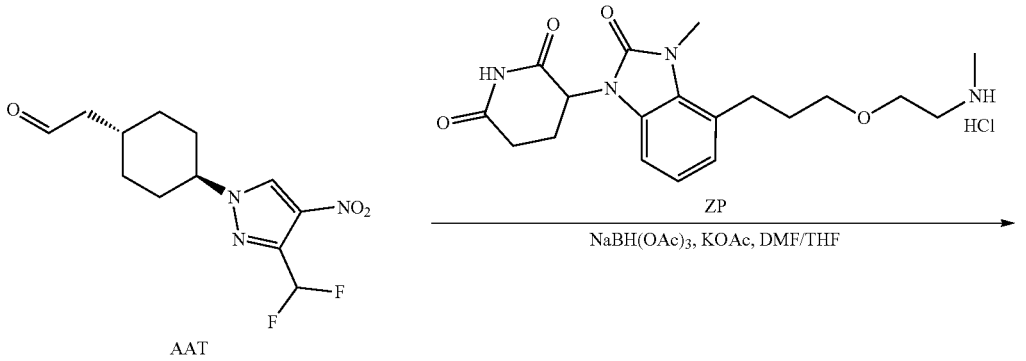

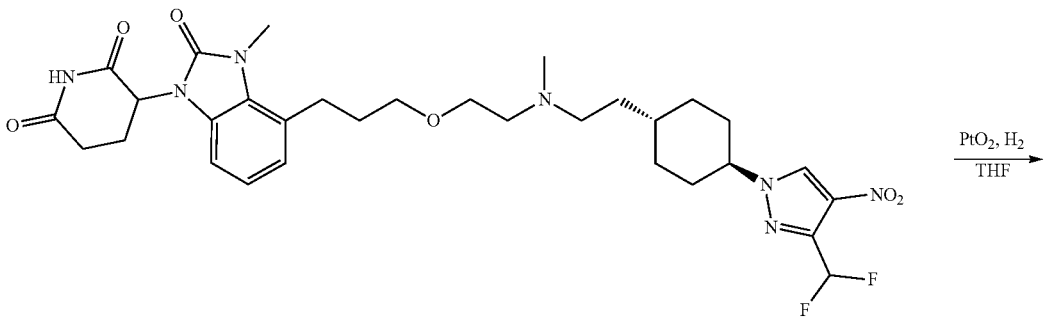

-continued

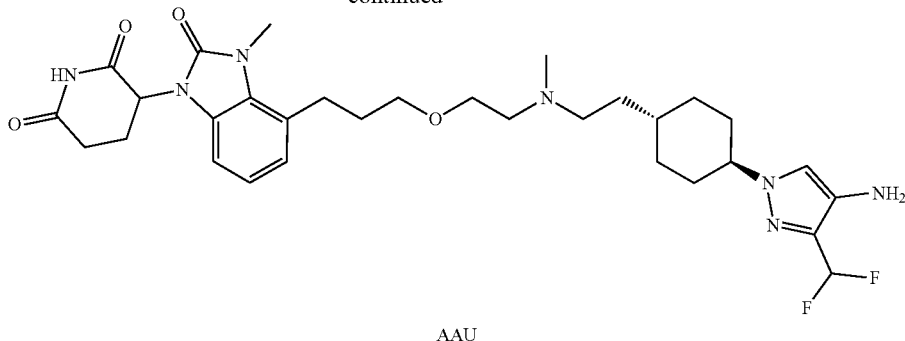

AAU

Step 1—3-[4-[3-[2-[2-[4-[3-(Difluoromethyl)-4-nitro-pyrazol-1-yl]cyclohexyl] ethyl-methyl-amino]ethoxy]propyl]-3-methyl-2-oxo-benzimidazol-1-yl] piperidine-2,6-dione To a solution of 3-[3-methyl-4-[3-[2-(methylamino)ethoxy]propyl]-2-oxo-benzimidazol-1-yl] piperidine-2,6-dione (86 mg, 209 umol, HCl salt, Intermediate ZP) and 2-[4-[3-(difluoromethyl)-4-nitro-pyrazol-1-yl] cyclohexyl] acetaldehyde (60.1 mg, 209 umol, Intermediate AAT) in a mixed solvent of THF (5 mL) and DMF (1 mL) was added KOAc (30.8 mg, 314 umol). The reaction mixture was stirred at 25° C. for 0.5 hr. Then, NaBH(OAc)$_3$ (53.2 mg, 251 umol) was added. The reaction mixture was stirred at 25° C. for 12 hrs. On completion, the reaction was concentrated in vacuo. The crude product was purified by reversed-phase HPLC (0.1% FA condition) to give the title compound (60.0 mg, 41% yield) as brown oil. $^1$H NMR (400 MHz, CDCl$_3$) δ 8.16 (s, 1H), 8.10-7.99 (m, 1H), 7.06-6.94 (m, 1H), 6.92 (d, J=8.0 Hz, 1H), 6.81 (d, J=7.6 Hz, 1H), 6.62 (d, J=8.0 Hz, 1H), 5.14 (dd, J=5.2, 12.8 Hz, 1H), 4.11-4.03 (m, 1H), 3.71 (t, J=4.8 Hz, 2H), 3.61 (s, 3H), 3.47 (t, J=6.0 Hz, 2H), 3.03-3.00 (m, 2H), 2.91-2.89 (m, 2H), 2.78-2.75 (m, 2H), 2.60 (s, 3H), 2.19-2.12 (m, 4H), 1.90-1.85 (m, 4H), 1.73-1.55 (m, 6H), 1.41-1.34 (m, 1H), 1.17-1.09 (m, 2H). LC-MS (ESI$^+$) m/z 646.2 (M+H)$^+$.

Step 2—3-[4-[3-[2-[2-[4-[4-Amino-3-(difluoromethyl)pyrazol-1-yl] cyclohexyl] ethyl-methyl-amino]ethoxy]propyl]-3-methyl-2-oxo-benzimidazol-1-yl] piperidine-2,6-dione To a solution of 3-[4-[3-[2-[2-[4-[3-(difluoromethyl)-4-nitro-pyrazol-1-yl] cyclohexyl] ethyl-methyl-amino]ethoxy]propyl]-3-methyl-2-oxo-benzimidazol-1-yl]piperidine-2,6-dione (60 mg, 92.9 umol) in THF (6 mL) was added Pd/C (15 mg, 10% wt) under N$_2$ atmosphere. The suspension was degassed and purged with H$_2$ for 7 times. The mixture was stirred under H$_2$ (15 Psi) at 20° C. for 12 hrs. On completion, the mixture filtered and the filtrate was concentrated to give the title compound (57.0 mg, 100% yield) as white solid. LC-MS (ESI$^+$) m/z 616.2 (M+H)$^+$.

3-(3-Methyl-2-oxo-4-vinyl-benzimidazol-1-yl)piperidine-2,6-dione (Intermediate AAV)

A mixture of 3-(4-bromo-3-methyl-2-oxo-benzimidazol-1-yl)piperidine-2,6-dione (10.0 g, 29.5 mmol, Intermediate HP), potassium; trifluoro(vinyl)boranuide (11.8 g, 88.7 mmol, CAS #13682-77-4), Cs$_2$CO$_3$ (2 M in water, 29.5 mL) and Pd(dppf)Cl$_2$·CH$_2$Cl$_2$ (1.69 g, 2.07 mmol) in dioxane (300 mL) was stirred at 90° C. for 2 hrs under nitrogen. On completion, the reaction mixture was filtered and the filtrated was concentrated in vacuo. The residue was purified by silica gel chromatography (petroleum ether:ethyl acetate=1:2) to give the title compound (5.70 g, 67% yield) as yellow solid. $^1$H NMR (400 MHz, DMSO-d$_6$) δ 11.10 (s, 1H), 7.40 (dd, J=10.8, 17.2 Hz, 1H), 7.18 (d, J=7.2 Hz, 1H), 7.10-6.98 (m, 2H), 5.72 (d, J=17.2 Hz, 1H), 5.47-5.31 (m, 2H), 3.54 (s, 3H), 2.96-2.82 (m, 1H), 2.79-2.57 (m, 2H), 2.06-1.94 (m, 1H).

Tert-butyl 4-but-3-enylpiperidine-1-carboxylate (Intermediate AAW)

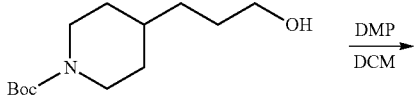

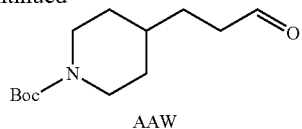

AAW

To a solution of tert-butyl 4-(3-hydroxypropyl)piperidine-1-carboxylate (2.00 g, 8.22 mmol, CAS #156185-63-6) in DCM (20 mL) was added DMP (4.18 g, 9.86 mmol) at 25° C. The reaction mixture was stirred at 25° C. for 2 hrs. On completion, the reaction mixture was quenched by addition sat.aq. $Na_2S_2O_3$ (30 mL) and $NaHCO_3$ (30 mL) and were extracted with DCM (3×30 mL). The combined organic layers were concentrated in vacuo to give a residue. The residue was purified by column chromatography ($SiO_2$, petroleum ether/ethyl acetate=20:1 to 5:1) to give the title compound (2.60 g, 99% yield, 75% purity) as a yellow solid. $^1$H NMR (400 MHz, DMSO-$d_6$) δ 9.68 (s, 1H), 3.91 (d, J=12.4 Hz, 2H), 2.67-2.56 (m, 2H), 2.46 (t, J=7.2 Hz, 2H), 1.61 (d, J=12.4 Hz, 2H), 1.46 (q, J=7.2 Hz, 3H), 1.39 (s, 9H), 0.99-0.90 (m, 2H).

2-[2-(Cyclopropylmethylamino)-4-pyridyl]-N-[3-(difluoromethyl)-1-[1-[3-(4-piperidyl) propyl]-4-piperidyl]pyrazol-4-yl]oxazole-4-carboxamide (Intermediate AAX)

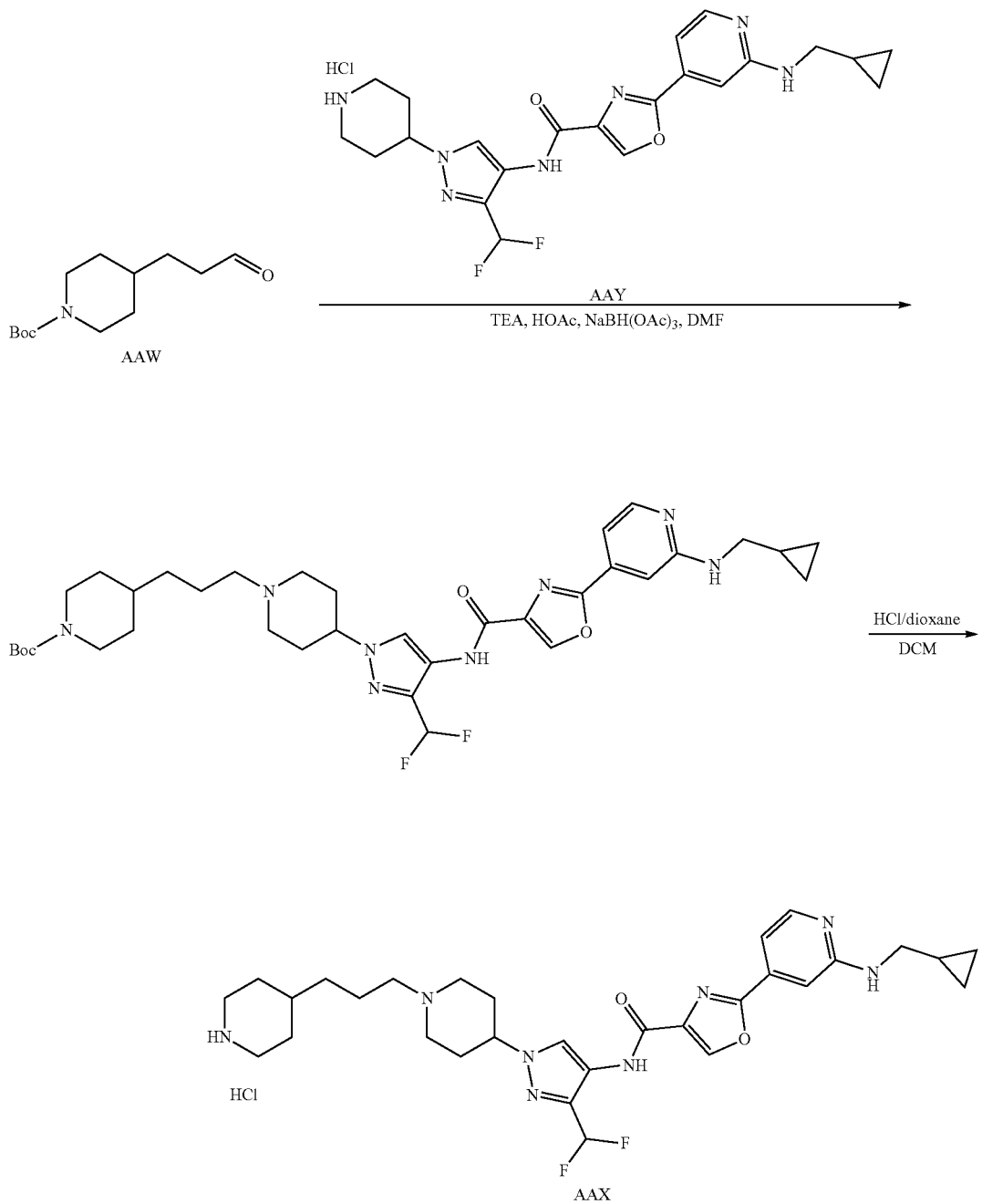

Step 1—Tert-butyl 4-[3-[4-[4-[[2-[2-[tert-butoxycarbonyl(cyclopropylmethyl)amino]-4-pyridyl] oxazole-4-carbonyl amino]-3-(difluoromethyl)pyrazol-1-yl]-1-piperidyl]propyl]piperidine-1-carboxylate To a solution of tert-butyl 4-(3-oxopropyl)piperidine-1-carboxylate (211 mg, 655 umol, Intermediate AAW) in THF (15 mL) and DMF (5 mL) was added TEA (655 umol, 91.3 uL). Then the mixture stirred at 25° C. for 10 min, HOAc (655 umol, 37.5 uL) and 2-[2-(cyclopropylmethylamino)-4-pyridyl]-N-[3-(difluoromethyl)-1-(4-piperidyl)pyrazol-4-yl] oxazole-4-carboxamide (300 mg, 655 umol, Intermediate AAY) was added to the mixture. The mixture was stirred at 25° C. for 20 minutes, then NaBH(OAc)$_3$ (278 mg, 1.31 mmol) was added to the mixture at 0° C. The reaction mixture was stirred at 25° C. for 2 hr. On completion, the reaction mixture was added H$_2$O (1 mL) and was concentrated in vacuo to give a residue. The residue was purified by reverse phase (0.1% FA condition) to give the title compound (360 mg, 80% yield) as a white solid. $^1$H NMR (400 MHz, DMSO-d$_6$) δ 9.72 (s, 1H), 8.92 (s, 1H), 8.20 (s, 1H), 8.15 (d, J=5.2 Hz, 1H), 7.15 (t, J=54.4 Hz, 1H), 7.10-7.07 (m, 1H), 7.03-7.00 (m, 1H), 4.29-4.15 (m, 1H), 3.98-3.82 (m, 2H), 3.17 (t, J=6.4 Hz, 2H), 2.95 (d, J=10.8 Hz, 2H), 2.66-2.65 (m, 1H), 2.52-2.51 (m, 3H), 2.31-2.26 (m, 2H), 2.10-1.89 (m, 6H), 1.67-1.59 (m, 2H), 1.50-1.41 (m, 2H), 1.38 (s, 9H), 1.25-1.16 (m, 2H), 1.12-1.01 (m, 1H), 1.01-0.88 (m, 2H), 0.51-0.41 (m, 2H), 0.26-0.16 (m, 2H); LC-MS (ESI$^+$) m/z 683.5 (M+H)$^+$.

Step 2—2-[2-(Cyclopropylmethylamino)-4-pyridyl]-N-[3-(difluoromethyl)-1-[1-[3-(4-piperidyl) propyl]-4-piperidyl]pyrazol-4-yl]oxazole-4-carboxamide To a solution of tert-butyl 4-[3-[4-[4-[[2-[2-(cyclopropylmethylamino)-4-pyridyl] oxazole-4-carbonyl] amino]-3-(difluoromethyl)pyrazol-1-yl]-1-piperidyl]propyl]piperidine-1-carboxylate (30.0 mg, 43.9 umol) in DCM (3 mL) was added HCl/dioxane (4 M, 2 mL). The reaction mixture was stirred at 25° C. for 2 hrs. On completion, the reaction mixture was concentrated in vacuo to give the title compound (23.0 mg, 84% yield) as a white solid. LC-MS (ESI$^+$) m/z 583.3 (M+H)$^+$.

2-[2-(cyclopropylmethylamino)-4-pyridyl]-N-[3-(difluoromethyl)-1-(4-piperidyl) pyrazol-4-yl]oxazole-4-carboxamide (Intermediate AAY)

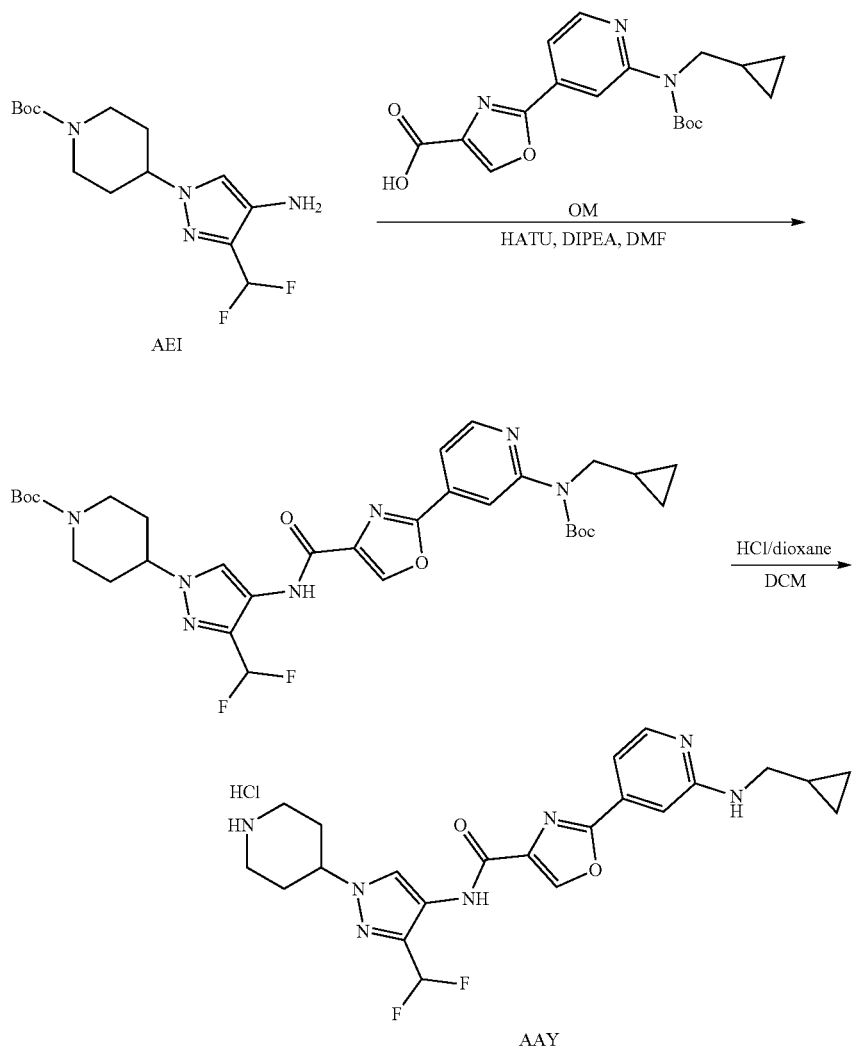

Step 1—Tert-butyl 4-[4-[[2-[2-[tert-butoxycarbonyl(cyclopropylmethyl)amino]-4-pyridyl]oxazole-4-carbonyl] amino]-3-(difluoromethyl)pyrazol-1-yl] piperidine-1-carboxylate To a solution of 2-[2-[tert-butoxycarbonyl(cyclopropylmethyl)amino]-4-pyridyl]oxazole-4-carboxylic acid (3.76 g, 10.4 mmol, Intermediate OM), DIPEA (4.50 g, 34.8 mmol) and HATU (5.30 g, 13.9 mmol) in DMF (50 mL) was added tert-butyl 4-[4-amino-3-(difluoromethyl)pyrazol-1-yl]piperidine-1-carboxylate (4.90 g, 11.6 mmol, Intermediate AEI). The reaction mixture was stirred at 10° C. for 2 hours. On completion, the reaction mixture was poured into water (400 mL) and extracted with ethyl acetate (3×150 mL). The combined organic layer was washed with brine (2×60 mL), dried over anhydrous sodium sulfate, filtered and concentrated in vacuo. The residue was purified by silica gel chromatography (petroleum ether: ethyl acetate=4:1) to give the title compound (4.20 g, 54% yield) as yellow solid. $^1$H NMR (400 MHz, CDCl$_3$) δ 9.07 (s, 1H), 8.52 (dd, J=0.8, 5.2 Hz, 1H), 8.37 (s, 1H), 8.35-8.32 (m, 2H), 7.63 (dd, J=1.2, 5.2 Hz, 1H), 6.99-6.63 (m, 1H), 4.37-4.15 (m, 3H), 3.94 (d, J=7.2 Hz, 2H), 2.98-2.82 (m, 2H), 2.20-2.08 (m, 2H), 2.04-1.89 (m, 2H), 1.57 (s, 9H), 1.49 (s, 9H), 1.31-1.11 (m, 1H), 0.51-0.37 (m, 2H), 0.34-0.22 (m, 2H).

Step 2—2-[2-(Cyclopropylmethylamino)-4-pyridyl]-N-[3-(difluoromethyl)-1-(4-piperidyl)pyrazol-4-yl] oxazole-4-carboxamide To a solution of tert-butyl 4-[4-[[2-[2-[tert-butoxycarbonyl(cyclopropylmethyl)amino]-4-pyridyl]oxazole-4-carbonyl]amino]-3-(difluoromethyl)pyrazol-1-yl]piperidine-1-carboxylate (3.90 g, 5.93 mmol) in dichloromethane (20 mL) was added HCl/dioxane (4 M, 20 mL). The reaction mixture was stirred at 10° C. for 1 hour. On completion, the reaction mixture was concentrated in vacuo to give the title compound (2.93 g, 100% yield, HCl salt) as pink solid. $^1$H NMR (400 MHz, DMSO-d$_6$) δ 9.97 (s, 1H), 9.12 (s, 1H), 8.21 (s, 1H), 8.08 (d, J=6.8 Hz, 1H), 7.62 (s, 1H), 7.42-7.05 (m, 2H), 4.70-4.51 (m, 1H), 3.35-3.32 (m, 4H), 3.10-2.99 (m, 2H), 2.52 (d, J=2.0 Hz, 1H), 2.25-2.11 (m, 4H), 1.20-1.10 (m, 1H), 0.59-0.51 (m, 2H), 0.35-0.29 (m, 2H).

2-[2-(Cyclopropylmethylamino)-4-pyridyl-N-[3-(difluoromethyl)-1-[1-[3-(4-piperidyl) propanoyl]-4-piperidyl]pyrazol-4-yl]oxazole-4-carboxamide (Intermediate AAZ)

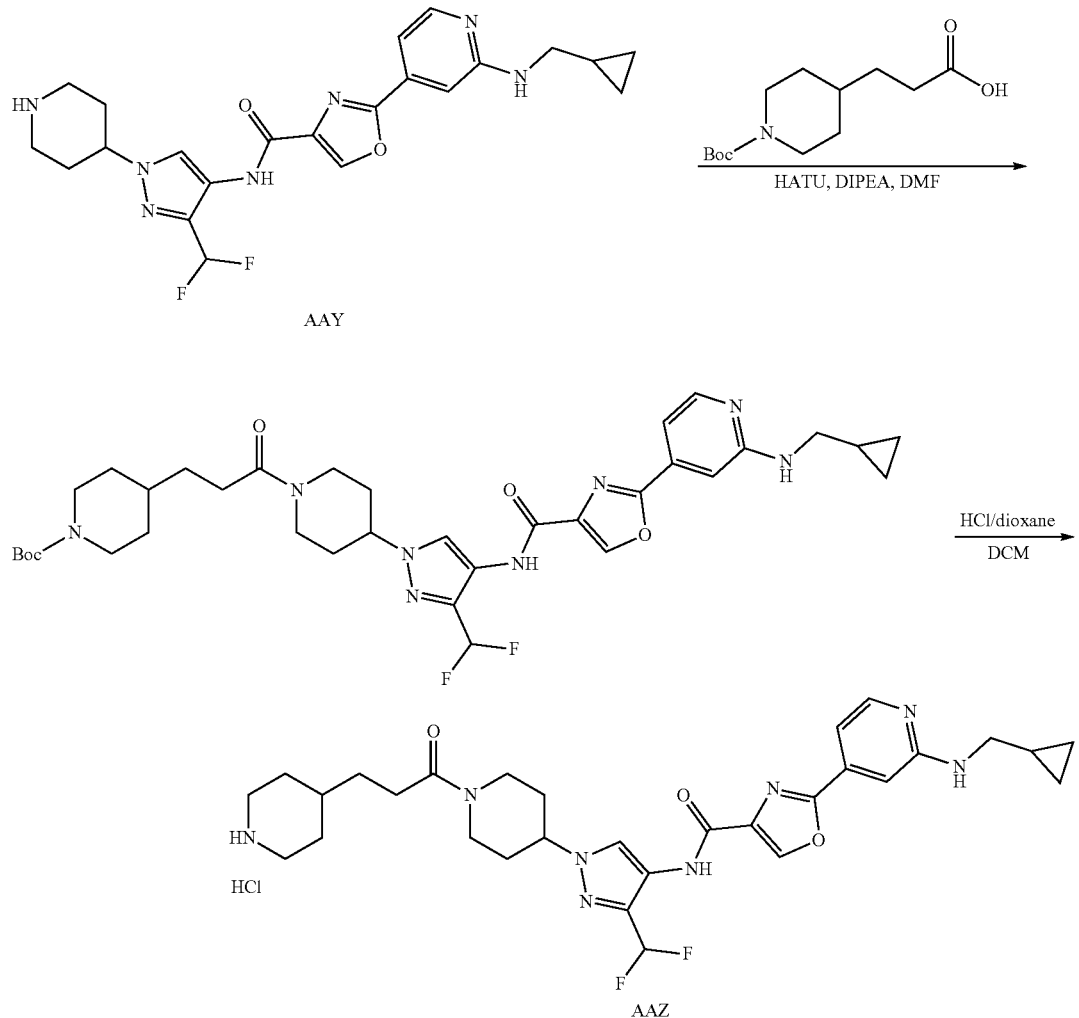

Step 1—Tert-butyl 4-[3-[4-[4-[[2-[2-(cyclopropylmethylamino)-4-pyridyl]oxazole-4-carbonylamino]-3-(difluoromethyl)pyrazol-1-yl]-1-piperidyl]-3-oxopropyl]piperidine-1-carboxylate To a solution of 2-[2-(cyclopropylmethylamino)-4-pyridyl]-N-[3-(difluoromethyl)-1-(4-piperidyl) pyrazol-4-yl]oxazole-4-carboxamide (412 mg, 777 umol, 2HCl, Intermediate AAY) and 3-(1-tert-butoxy carbonyl-4-piperidyl) propanoic acid (200 mg, 777 umol, CAS #154375-43-6) in DMF (4 mL) was added DIPEA (301 mg, 2.33 mmol, 406 uL), and HATU (355 mg, 933 umol). The mixture was stirred at 25° C. for 2 hrs. On completion, the reaction mixture was concentrated in vacuo to give the title compound (350 mg, 65% yield) was obtained as brown solid. $^1$H NMR (400 MHz, DMSO-$d_6$) δ 9.72 (s, 1H), 8.92 (s, 1H), 8.23 (s, 1H), 8.15 (d, J=5.2 Hz, 1H), 7.97-7.15 (m, 1H), 7.12-7.05 (m, 2H), 7.04-7.00 (m, 1H), 4.61-4.44 (m, 2H), 4.05-3.87 (m, 3H), 3.20-3.16 (m, 2H), 2.89 (s, 1H), 2.73 (s, 1H), 2.69 (s, 1H), 2.38 (t, J=7.2 Hz, 2H), 2.11-1.99 (m, 2H), 1.94-1.89 (m, 1H), 1.78-1.62 (m, 3H), 1.53-1.42 (m, 3H), 1.39 (s, 9H), 1.25 (dd, J=6.4, 12.4 Hz, 1H), 1.11-0.92 (m, 3H), 0.49-0.42 (m, 2H), 0.26-0.20 (m, 2H); LC-MS (ESI$^+$) m/z 697.4 (M+H)$^+$.

Step 2—2-[2-(Cyclopropylmethylamino)-4-pyridyl]-N-[3-(difluoromethyl)-1-[1-[3-(4-piperidyl) propanoyl]-4-piperidyl]pyrazol-4-yl]oxazole-4-carboxamide To a solution of tert-butyl 4-[3-[4-[4-[[2-[2-(cyclopropylmethylamino)-4-pyridyl]oxazole-4-carbonyl] amino]-3-(difluoromethyl) pyrazol-1-yl]-1-piperidyl]-3-oxo-propyl] piperidine-1-carboxylate (330 mg, 474 umol) in DCM (2 mL) was added HCl/dioxane (2 mL). The reaction mixture was stirred at 25° C. for 2 hrs. On completion, the reaction mixture was concentrated in vacuo to give the title compound (280 mg, 93% yield, HCl) as brown solid. LC-MS (ESI$^+$) m/z 597.4 (M+H)$^+$.

3-[3-Methyl-2-oxo-4-[[4-(4-piperidyloxy)-1-piperidyl]methyl]benzimidazol-1-yl]piperidine-2,6-dione (Intermediate ABA)

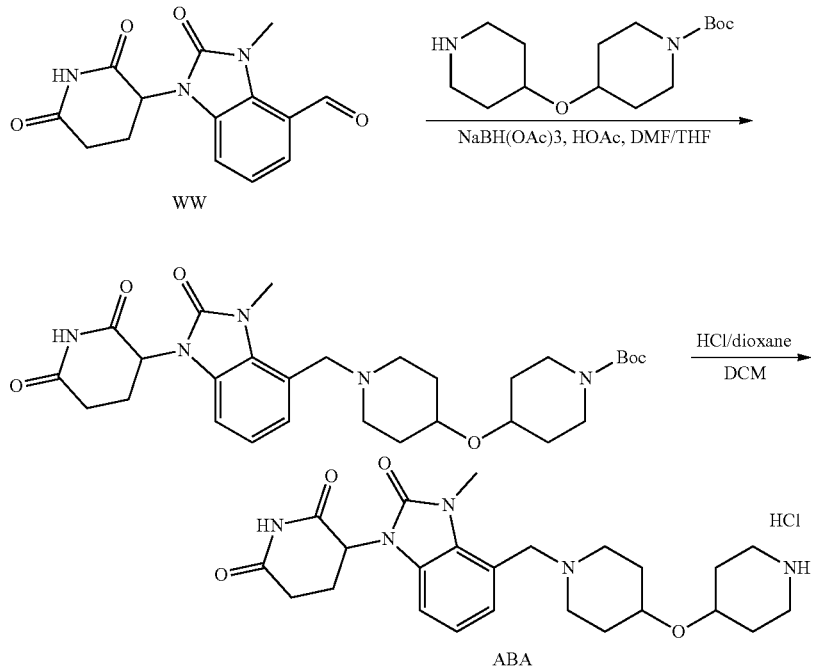

Step 1—Tert-butyl 4-[[1-[[1-(2,6-dioxo-3-piperidyl)-3-methyl-2-oxo-benzimidazol-4-yl]methyl]-4-piperidyl]oxy]piperidine-1-carboxylate To a solution of 1-(2,6-dioxo-3-piperidyl)-3-methyl-2-oxo-benzimidazole-4-carbaldehyde (200 mg, 696 umol, Intermediate WW), tertbutyl 4-(4-piperidyloxy)piperidine-1-carboxylate (218 mg, 766 umol, CAS #845305-83-1) in DMF (2.00 mL) and THF (2.00 mL) was added HOAc (83.6 mg, 1.39 mmol). The mixture was stirred at 80° C. for 0.5 hr. Then NaBH(OAc)$_3$ (295 mg, 1.39 mmol) was added, then the mixture was stirred at 20° C. for 16 hrs. On completion, the reaction was quenched by addition water (0.5 mL), and concentrated in vacuo to give a residue. The residue was purified by reverse phase (0.1% FA) to give the title compound (180 mg, 46% yield) as a yellow solid. LC-MS (ESI$^+$) m/z 556.3 (M+H)$^+$ Step 2—3-[3-Methyl-2-oxo-4-[[4-(4-piperidyloxy)-1-piperidyl]methyl]benzimidazol-1-yl]piperidine-2,6-dione To a solution of tert-butyl 4-[[1-[[1-(2,6-dioxo-3-piperidyl)-3-methyl-2-oxo-benzimidazol-4-yl]methyl]-4-piperidyl]oxy]piperidine-1-carboxylate (150 mg, 270 umol) in DCM (3.00 mL) was added HCl/dioxane (4 M, 3.00 mL), then the mixture was stirred at 20° C. for 1 hr. On completion, the reaction mixture was concentrated in vacuo to give a residue. The residue was purified by reverse phase (0.1% FA condition) to give the title compound (100 mg, 75% yield, HCl) as a white solid. $^1$H NMR (400 MHz, DMSO-$d_6$) δ 11.12 (s, 1H), 9.36-9.07 (m, 1H), 7.51-7.33 (m, 1H), 7.24 (s, 1H), 7.09 (s, 1H), 5.45 (dd, J=4.6, 12.0 Hz, 1H), 4.70-4.47 (m, 1H), 4.02-3.68 (m, 2H), 3.66 (s, 3H), 3.43-3.38 (m, 2H), 3.27-3.22 (m, 2H), 3.15-3.04 (m, 2H), 2.99-2.91 (m, 2H), 2.88 (d, J=5.8 Hz, 1H), 2.78-2.68 (m, 1H), 2.68-2.57 (m, 1H), 2.14-1.91 (m, 5H), 1.91-1.75 (m, 2H), 1.75-1.58 (m, 2H).

5-Morpholinopyrazolo[1,5-a]pyrimidine-3-carboxylic acid (Intermediate ABB)

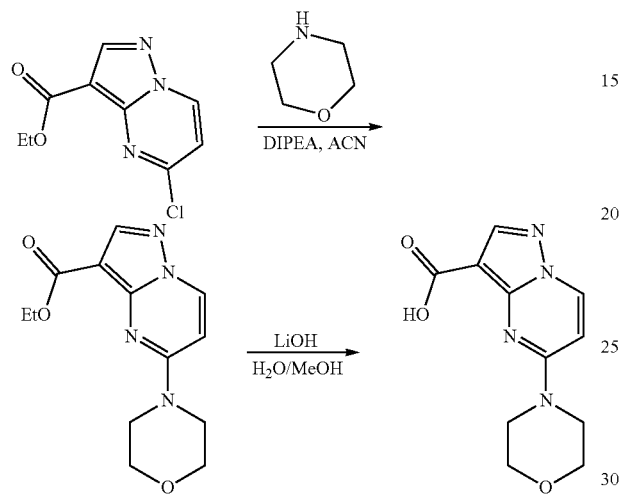

Step 1—Ethyl 5-morpholinopyrazolo[1,5-a]pyrimidine-3-carboxylate

To a solution of ethyl 5-chloropyrazolo[1,5-a]pyrimidine-3-carboxylate (1.00 g, 4.43 mmol, CAS #1224944-77-7) and morpholine (579 mg, 6.65 mmol, CAS #110-91-8) in ACN (10 mL) was added DIPEA (1.72 g, 13.3 mmol). The reaction mixture was stirred at 60° C. for 2 hrs. On completion, the mixture was concentrated in vacuo. The residue was triturated with water (20 mL), filtered and the filter cake was dried in vacuo to give the title compound (1.10 g, 90% yield) as a white powder. $^1$H NMR (400 MHz, DMSO-$d_6$) δ 8.75 (d, J=8.0 Hz, 1H), 8.21 (s, 1H), 6.85 (d, J=8.0 Hz, 1H), 4.19 (q, J=7.2 Hz, 2H), 3.82-3.61 (m, 8H), 1.27 (t, J=7.2 Hz, 3H).

Step 2—5-Morpholinopyrazolo[1,5-a]pyrimidine-3-carboxylic acid

To a solution of ethyl 5-morpholinopyrazolo[1,5-a]pyrimidine-3-carboxylate (1.35 g, 4.89 mmol) in a mixed solvent of MeOH (15 mL) and H$_2$O (3 mL) was added LiOH (585 mg, 24.43 mmol). The reaction mixture was stirred at 60° C. for 12 hrs. On completion, the mixture was acidified with 1N HCl to pH=3-4, then concentrated in vacuo. The residue was triturated with water (30 mL), filtered and the filter cake was dried in vacuo to give the title compound (1.10 g, 91% yield) as a white powder. $^1$H NMR (400 MHz, DMSO-$d_6$) δ 11.73 (s, 1H), 8.74 (d, J=8.0 Hz, 1H), 8.19 (s, 1H), 6.83 (d, J=8.0 Hz, 1H), 3.82-3.60 (m, 8H).

N-[3-(difluoromethyl)-1-(4-formylcyclohexyl)pyrazol-4-yl]-5-morpholino-pyrazolo[1,5-a]pyrimidine-3-carboxamide (Intermediate ABC)

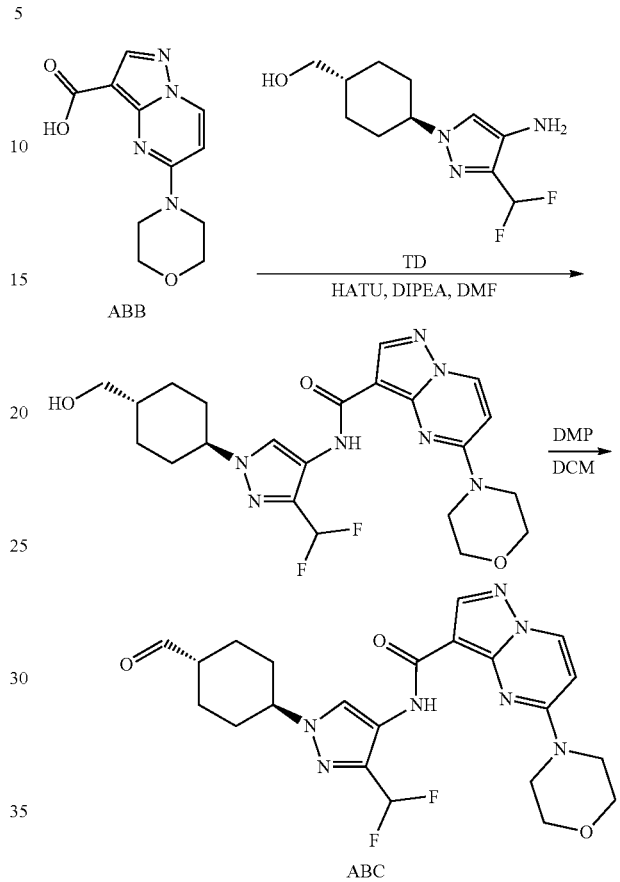

Step 1—N-[3-(difluoromethyl)-1-[4-(hydroxymethyl)cyclohexyl]pyrazol-4-yl]-5-morpholino-pyrazolo[1,5-a]pyrimidine-3-carboxamide To a solution of 5-morpholinopyrazolo[1,5-a]pyrimidine-3-carboxylic acid (50.0 mg, 201 umol, Intermediate ABB) and [4-[4-amino-3-(difluoromethyl)pyrazol-1-yl]cyclohexyl]methanol (49.4 mg, 201 umol, Intermediate TD) in DMF (3 mL) was added HATU (84.2 mg, 222 umol) and DIPEA (78.1 mg, 604 umol). The reaction mixture was stirred at 20° C. for 0.5 hr. Then the mixture was heated to 80° C. for 12 hrs. On completion, the mixture was quenched with water (0.2 mL), concentrated in vacuo. The residue was purified by reverse phase (0.1% FA condition) to give the title compound (40.0 mg, 42% yield) as a white solid. $^1$H NMR (400 MHz, DMSO-$d_6$) δ 9.39 (s, 1H), 8.82 (d, J=8.0 Hz, 1H), 8.38 (s, 1H), 8.28 (s, 1H), 7.25-6.95 (m, 1H), 6.90 (d, J=8.0 Hz, 1H), 4.47 (t, J=5.2 Hz, 1H), 4.23-4.12 (m, 1H), 3.86-3.68 (m, 8H), 3.26 (t, J=5.6 Hz, 2H), 2.11-1.96 (m, 2H), 1.92-1.81 (m, 2H), 1.79-1.66 (m, 2H), 1.52-1.35 (m, 1H), 1.16-1.02 (m, 2H).

Step 2—N-3-(difluoromethyl)-1-(4-formylcyclohexyl)pyrazol-4-yl]-5-morpholino-pyrazolo[1,5-a]pyrimidine-3-carboxamide To a solution of N-[3-(difluoromethyl)-1-[4-(hydroxymethyl)cyclohexyl]pyrazol-4-yl]-5-morpholino-pyrazolo[1,5- a]pyrimidine-3-carboxamide (90.0 mg, 189 umol) in DCM (5 mL) was added DMP (120 mg, 284 umol). The reaction mixture was stirred at 20° C. for 2 hrs. On completion, the mixture was quenched with sat. $Na_2S_2O_3$ (30 mL) and sat. $NaHCO_3$ (30 mL), stirred for 10 minutes, and extracted with DCM (2×30 mL). The organic layer was washed with brine (2×40 mL), dried with $Na_2SO_4$, filtered and the filtrate was concentrated in vacuo to give the title compound (80.0 mg, 89% yield) as a white solid. LC-MS (ESI$^+$) m/z 474.2 (M+H)$^+$ 5-(Cyclopropylmethylamino)-N-[1-(4-formylcyclohexyl)-3-(1-hydroxy-1-methyl-ethyl) pyrazol-4-yl]pyrazolo[1,5-a]pyrimidine-3-carboxamide (Intermediate ABD)

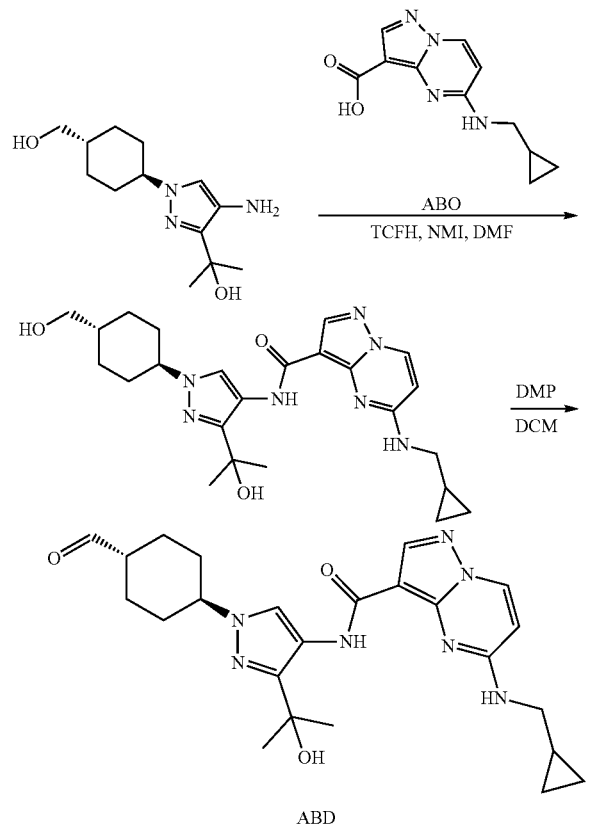

ABD

Step 1—5-(Cyclopropylmethylamino)-N-[1-[4-(hydroxymethyl)cyclohexyl]-3-(1-hydroxy-1-methyl-ethyl)pyrazol-4-yl]pyrazolo[1,5-a]pyrimidine-3-carboxamide To a mixture of 2-[4-amino-1-[4-(hydroxymethyl)cyclohexyl]pyrazol-3-yl]propan-2-ol (300 mg, 1.18 mmol, synthesized via Step 1 of Intermediate UW), 5-(cyclopropylmethylamino)pyrazolo[1,5-a]pyrimidine-3-carboxylic acid (302 mg, 1.30 mmol, Intermediate ABO) in ACN (15 mL) was added [chloro(dimethylamino) methylene]-dimethylammonium; hexafluorophosphate (399 mg, 1.42 mmol) and 1-methylimidazole (340 mg, 4.14 mmol). The reaction mixture was stirred at 25° C. for 1 hour. On completion, the reaction mixture was filtered and the filtrate was concentrated to give to give the title compound (420 mg, 75% yield) as a white solid. $^1$H NMR (400 MHz, DMSO-d$_6$) δ 9.88 (s, 1H), 8.52 (d, J=7.6 Hz, 1H), 8.24 (s, 1H), 8.14 (s, 1H), 8.05-7.99 (m, 1H), 6.42 (d, J=7.6 Hz, 1H), 5.33 (s, 1H), 4.48 (s, 1H), 3.99 (d, J=8.0 Hz, 1H), 3.51 (d, J=6.0 Hz, 2H), 3.26 (d, J=5.2 Hz, 3H), 2.03 (d, J=10.0 Hz, 2H), 1.85 (d, J=11.6 Hz, 2H), 1.65 (d, J=7.2 Hz, 2H), 1.49 (s, 6H), 1.46-1.37 (m, 1H), 1.15-1.01 (m, 3H), 0.53-0.48 (m, 2H), 0.30-0.29 (m, 2H).

Step 2—5-(Cyclopropylmethylamino)-N-[1-(4-formylcyclohexyl)-3-(1-hydroxy-1-methyl-ethyl) pyrazol-4-yl]pyrazolo[1,5-a]pyrimidine-3-carboxamide To a mixture of 5-(cyclopropylmethylamino)-N-[1-[4-(hydroxymethyl)cyclohexyl]-3-(1-hydroxy-1-methyl-ethyl) pyrazol-4-yl]pyrazolo[1,5-a]pyrimidine-3-carboxamide (200 mg, 428 umol) in DCM (20 mL) was added DMP (218 mg, 513 umol). The reaction mixture was stirred at 25° C. for 0.5 hour. On completion, the reaction mixture was quenched by water (2 mL) and concentrated in vacuo to give the residue. The residue was purified by reverse phase (0.1% FA condition) to give the title compound (130 mg, 65% yield) as a white solid. $^1$H NMR (400 MHz, DMSO-d$_6$) δ 9.88 (s, 1H), 9.61 (s, 1H), 8.52 (d, J=7.6 Hz, 1H), 8.27-8.22 (m, 1H), 8.13 (s, 1H), 6.41 (d, J=7.6 Hz, 1H), 5.35 (s, 1H), 4.09-3.99 (m, 1H), 3.50 (t, J=5.9 Hz, 2H), 2.43-2.30 (m, 1H), 2.11-2.00 (m, 4H), 1.81-1.71 (m, 2H), 1.48 (s, 6H), 1.43-1.30 (m, 2H), 1.11-0.97 (m, 1H), 0.55-0.44 (m, 2H), 0.28 (q, J=4.8 Hz, 2H).

5-Prop-2-ynoxypentan-1-ol (Intermediate ABE)

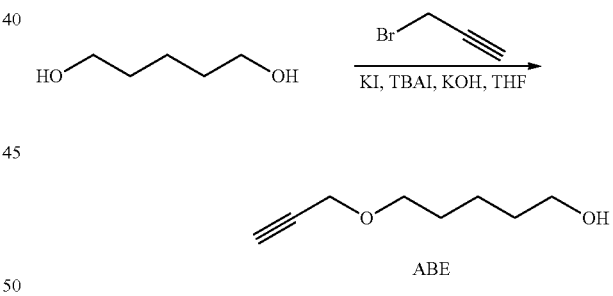

ABE

To a solution of pentane-1,5-diol (5.00 g, 48.0 mmol, 5.05 mL) and 3-bromoprop-1-yne (7.14 g, 48.0 mmol, 5.17 mL) in THF (20 mL) was added KOH (2.69 g, 48.0 mmol), TBAI (1.06 g, 2.88 mmol) and KI (1.20 g, 7.20 mmol). The reaction mixture was stirred at 25° C. for 16 hr. On completion, the mixture was filtered, and the filter was concentrated in vacuo to give a residue. The residue was diluted with H$_2$O (50 mL), and then extracted with EA (2×100 mL). The organic phase was concentrated in vacuo to give a residue. The residue was purified by flash silica gel chromatography to give the title compound (1.50 g, 85% yield) as yellow oil. $^1$H NMR (400 MHz, CDCl$_3$) δ 4.12 (d, J=2.4 Hz, 2H), 3.67-3.59 (m, 2H), 3.52 (t, J=6.8 Hz, 2H), 2.42 (t, J=2.4 Hz, 1H), 1.75-1.67 (m, 1H), 1.66-1.55 (m, 4H), 1.48-1.39 (m, 2H).

5-[3-[1-(2,6-Dioxo-3-piperidyl)-3-methyl-2-oxo-benzimidazol-5-yl]propoxy]pentanal (Intermediate ABF)

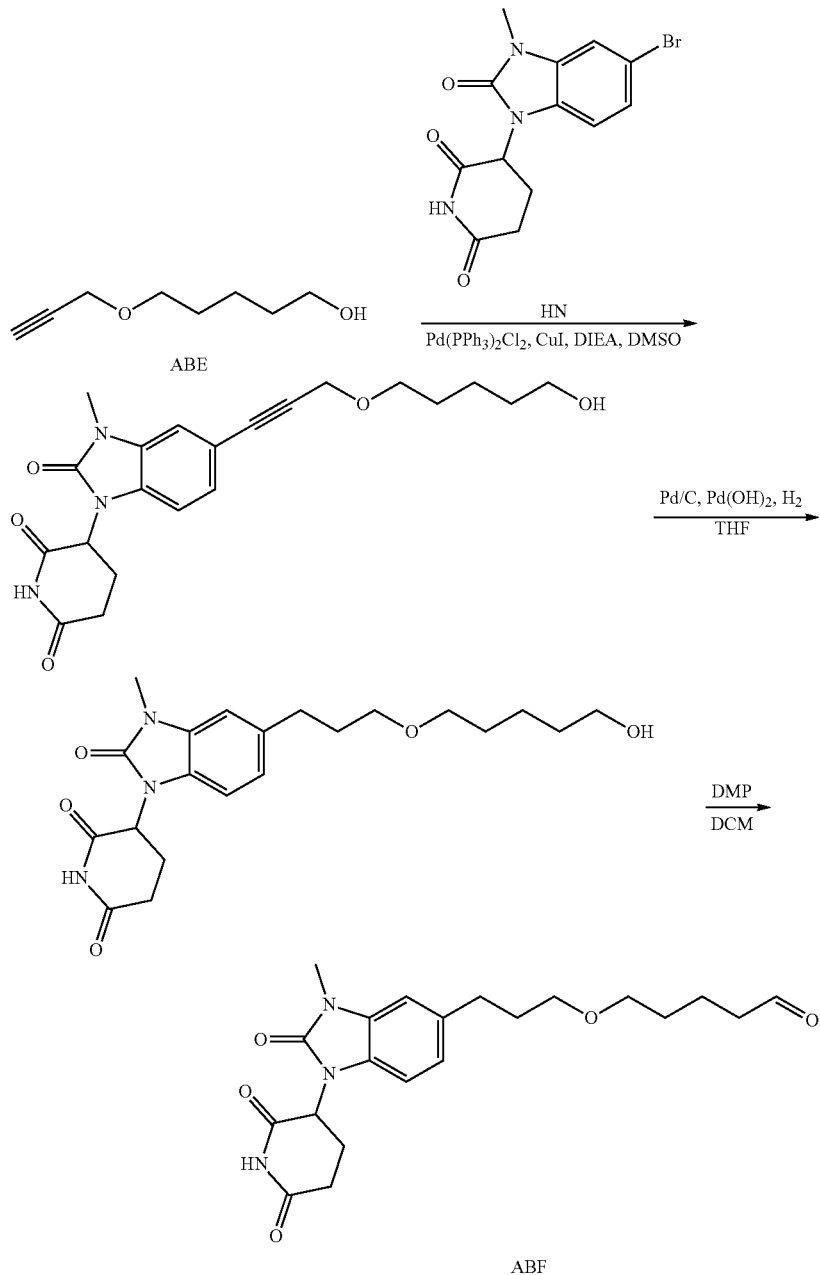

Step 1—3-[5-[3-(5-Hydroxypentoxy)prop-1-ynyl]-3-methyl-2-oxo-benzimidazol-1-yl]piperidine-2,6-dione A mixture of 3-(5-bromo-3-methyl-2-oxo-benzimidazol-1-yl)piperidine-2,6-dione (500 mg, 1.48 mmol, Intermediate HN), 5-prop-2-ynoxypentan-1-ol (421 mg, 2.96 mmol, Intermediate ABE), Pd(PPh$_3$)$_2$Cl$_2$ (104 mg, 148 umol), DIPEA (956 mg, 7.39 mmol) and CuI (28.2 mg, 148 umol) in DMSO (12 mL) was de-gassed and then heated at 80° C. for 2 hours under N$_2$ atmosphere. On completion, the mixture was filtered and the filtrate was concentrated in vacuo. The residue was purified by reverse phase (0.1% FA condition) to give the title compound (400 mg, 68% yield) as a yellowish solid. $^1$H NMR (400 MHz, DMSO-d$_6$) δ 11.11 (s, 1H), 7.32 (s, 1H), 7.24-7.05 (m, 2H), 5.38 (dd, J=5.2, 12.8 Hz, 1H), 4.35 (s, 2H), 3.50 (t, J=6.4 Hz, 2H), 3.41-3.39 (m, 2H), 3.37 (s, 3H), 2.95-2.82 (m, 1H), 2.77-2.61 (m, 2H), 2.09-1.97 (m, 1H), 1.59-1.41 (m, 6H).

Step 2—3-[5-[3-(5-Hydroxypentoxy)propyl]-3-methyl-2-oxo-benzimidazol-1-yl]piperidine-2,6-dione To a solution of 3-[5-[3-(5-hydroxypentoxy)prop-1-ynyl]-3-methyl-2-oxo-benzimidazol-1-yl] piperidine-2,6-dione (300 mg, 751 umol) in THF (10 mL) was added Pd/C (0.1 g, 10% wt) and Pd(OH)$_2$/C (0.1 g, 20% wt). The reaction mixture was stirred at 20° C. for 2 hrs under H$_2$ (15 Psi) atmosphere. On completion, the mixture was filtered and the filtrate was concentrated in vacuo. The residue was purified by prep-HPLC (column: Phenomenex Synergi Max-RP 150*50 mm*10 um; mobile phase: [water (0.225% FA)-ACN]; B %: 15%-45%, 10 min) to give the title compound (270 mg, 89% yield) as a yellow solid. LC-MS (ESI$^+$) m/z 404.1 (M+H)$^+$.

Step 3—5-[3-[1-(2,6-Dioxo-3-piperidyl)-3-methyl-2-oxo-benzimidazol-5-yl]propoxy]pentanal To a solution of 3-[5-[3-(5-hydroxypentoxy)propyl]-3-methyl-2-oxo-benzimidazol-1-yl]piperidine-2,6-dione (250 mg, 620 umol) in DCM (10 mL) was added DMP (394 mg, 929 umol). The reaction mixture was stirred at 20° C. for 2 hrs. On completion, the mixture was quenched with Na$_2$S$_2$O$_3$ (30 mL) and NaHCO$_3$ (30 mL), stirred for 10 minutes, then extracted with DCM (2×30 mL). The organic layer was washed with brine (50 mL), dried with Na$_2$SO$_4$, and concentrated in vacuo to give the title compound (210 mg, 68% yield) as a yellow solid. LC-MS (ESI$^+$) m/z 402.2 (M+H)$^+$.

5-[3-[1-(2,6-Dioxo-3-piperidyl)-3-methyl-2-oxo-benzimidazol-4-yl]propoxy]pentanal (Intermediate ABG)

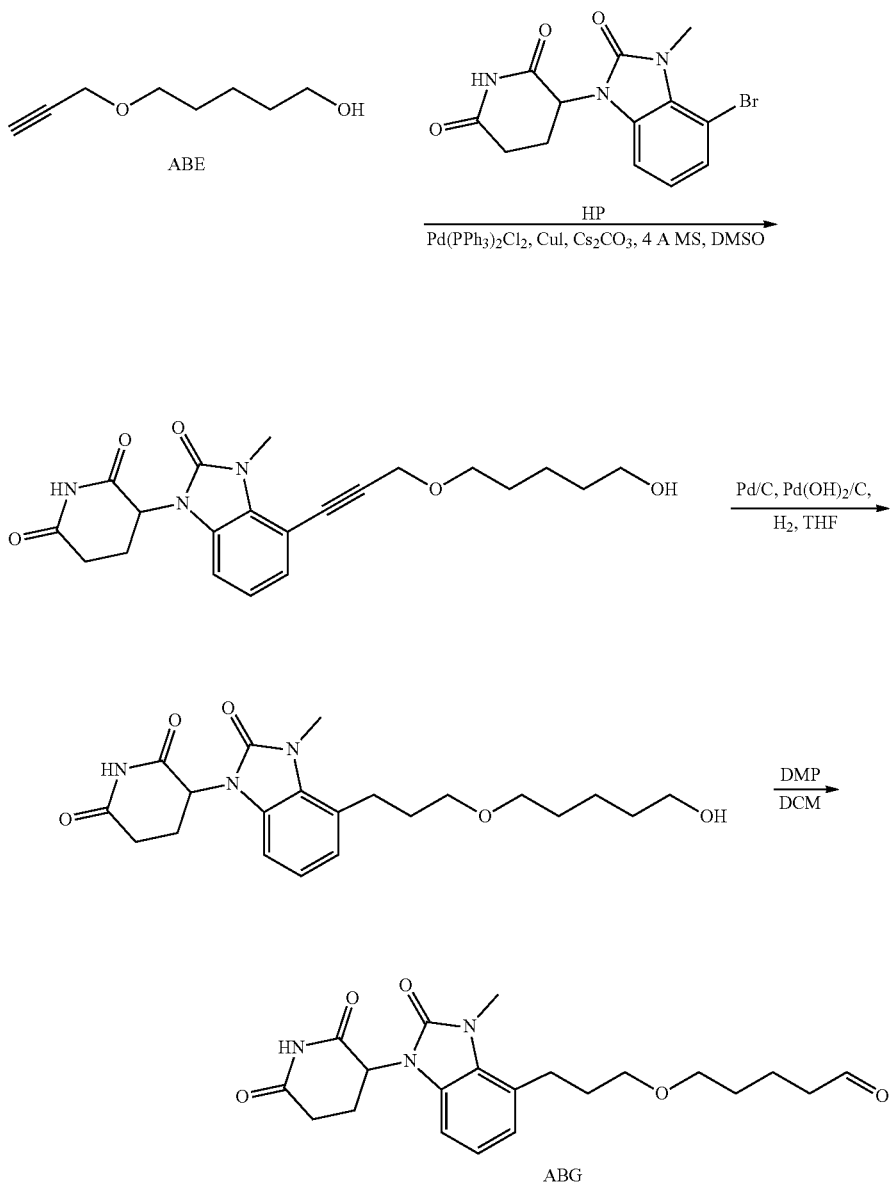

Step 1—3-[4-[3-(5-Hydroxypentoxy)prop-1-ynyl]-3-methyl-2-oxo-benzimidazol-1-yl]piperidine-2,6-dione To a solution of 3-(4-bromo-3-methyl-2-oxo-benzimidazol-1-yl)piperidine-2,6-dione (500 mg, 1.48 mmol, Intermediate HP) and 5-prop-2-ynoxypentan-1-ol (273 mg, 1.92 mmol, Intermediate ABE) in DMSO (10 mL) was added 4 Å molecular sieves (100 mg), DIPEA (955 mg, 7.39 mmol, 1.29 mL) Pd(PPh$_3$)$_2$Cl$_2$ (103 mg, 147 umol) and CuI (28.1 mg, 147 umol), and the reaction mixture was stirred at 80° C. for 2 hr under N$_2$. On completion, the mixture was filtered, and the filtrate was concentrated in vacuo to give a residue. The residue was purified by reverse phase (0.1% FA condition) to give the title compound (300 mg, 51% yield) as a yellow solid. $^1$H NMR (400 MHz, DMSO-d$_6$) δ 11.12 (s, 1H), 7.17 (d, J=8.0 Hz, 1H), 7.14-7.10 (m, 1H), 7.06-7.00 (m, 1H), 5.40 (dd, J=5.2, 12.8 Hz, 1H), 4.42 (s, 2H), 3.64 (s, 3H), 3.52 (t, J=6.4 Hz, 2H), 3.38 (t, J=6.4 Hz, 2H), 2.95-2.81 (m, 1H), 2.77-2.61 (m, 2H), 2.07-1.97 (m, 1H), 1.59-1.50 (m, 2H), 1.46-1.40 (m, 2H), 1.38-1.31 (m, 2H); LC-MS (ESI$^+$) m/z 438.1 (M+K)$^+$.

Step 2—3-[4-[3-(5-Hydroxypentoxy)propyl]-3-methyl-2-oxo-benzimidazol-1-yl]piperidine-2,6-dione To a solution of 3-[4-[3-(5-hydroxypentoxy)prop-1-ynyl]-3-methyl-2-oxo-benzimidazol-1-yl] piperidine-2,6-dione (280 mg, 700 umol) in THF (2 mL) was added Pd/C (50 mg, 10 wt %) and Pd(OH)$_2$/C (50 mg, 10 wt %). The reaction mixture was stirred at 20° C. for 2 hrs under H$_2$ (15 psi). On completion, the residue was filtered and the filtrate was concentrated in vacuo to give the title compound (250 mg, 88% yield) as a white solid. $^1$H NMR (400 MHz, DMSO-d$_6$) δ 11.09 (s, 1H), 7.05-6.92 (m, 2H), 6.90-6.81 (m, 1H), 5.36 (dd, J=5.2, 12.4 Hz, 1H), 4.34 (t, J=5.2 Hz, 1H), 3.56 (s, 3H), 3.43-3.35 (m, 6H), 3.01-2.92 (m, 2H), 2.91-2.83 (m, 1H), 2.77-2.67 (m, 1H), 2.65-2.59 (m, 1H), 2.06-1.93 (m, 1H), 1.91-1.73 (m, 2H), 1.55-1.48 (m, 2H), 1.45-1.40 (m, 2H), 1.37-1.31 (m, 2H); LC-MS (ESI$^+$) m/z 404.2 (M+H)$^+$.

Step 3—5-[3-[1-(2,6-Dioxo-3-piperidyl)-3-methyl-2-oxo-benzimidazol-4-yl]propoxy]pentanal To a solution of 3-[4-[3-(5-hydroxypentoxy)propyl]-3-methyl-2-oxo-benzimidazol-1-yl]piperidine-2,6-dione (100 mg, 247 umol) in DCM (5 mL) was added DMP (126 mg, 297 umol, 92.0 uL). The reaction mixture was stirred at 20° C. for 1 hr. On completion, the reaction mixture was poured into the ice-water (10 mL), and extracted with EA (2×20 mL). The combined organic phase was washed with brine (2×20 mL), dried with anhydrous Na$_2$SO$_4$, filtered and concentrated in vacuo to give the title compound (90.0 mg, 90% yield) as a yellow solid. LC-MS (ESI$^+$) m/z 402.2 (M+H)$^+$.

1-(Azetidin-3-yl)-3-(difluoromethyl)-4-nitro-pyrazole (Intermediate ABH)

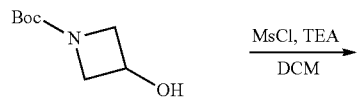

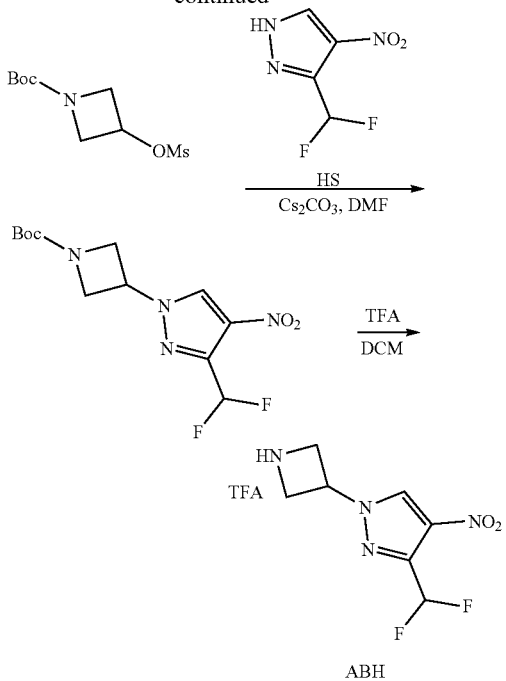

Step 1—Tert-butyl 3-methylsulfonyloxyazetidine-1-carboxylate

To a mixture of tert-butyl 3-hydroxyazetidine-1-carboxylate (5.00 g, 28.8 mmol) in DCM (50 mL) was added TEA (8.76 g, 86.6 mmol, 12.0 mL) and MsCl (3.97 g, 34.6 mmol, 2.68 mL). The reaction mixture was stirred at 25° C. for 2 hours. On completion, the reaction mixture was diluted with water (50 mL) and extracted with DCM (2×100 mL). The combined organic layers was dried over Na$_2$SO$_4$, filtered and concentrated in vacuo to give the title compound (6.10 g, 84% yield) as light yellow solid. $^1$H NMR (400 MHz, CDCl$_3$) δ 5.23-5.16 (m, 1H), 4.30-4.24 (m, 2H), 4.11-4.07 (m, 2H), 3.06 (s, 3H), 1.44 (s, 9H).

Step 2—Tert-butyl 3-[3-(difluoromethyl)-4-nitro-pyrazol-1-yl]azetidine-1-carboxylate To a mixture of 3-(difluoromethyl)-4-nitro-1H-pyrazole (2.60 g, 15.9 mmol, Intermediate HS) in DMF (50 mL) was added Cs$_2$CO$_3$ (10.3 g, 31.8 mmol) and tert-butyl 3-methylsulfonyloxyazetidine-1-carboxylate (4.81 g, 19.1 mmol). The reaction mixture was stirred at 100° C. for 12 hours. On completion, the reaction mixture was filtered and concentrated in vacuo. The residue was purified by reverse phase (0.1% FA condition) and by column chromatography to give the title compound (1.50 g, 29% yield) as white solid. $^1$H NMR (400 MHz, DMSO-d$_6$) δ 9.20 (s, 1H), 7.50-7.20 (m, 1H), 5.37-5.28 (m, 1H), 4.32 (t, J=8.8 Hz, 2H), 4.16 (s, 2H), 1.41 (s, 9H).

Step 3—1-(Azetidin-3-yl)-3-(difluoromethyl)-4-nitro-pyrazole

To a mixture of tert-butyl 3-[3-(difluoromethyl)-4-nitro-pyrazol-1-yl]azetidine-1-carboxylate (1.40 g, 4.40 mmol) in DCM (8 mL) was added TFA (7.70 g, 67.5 mmol, 5 mL). The reaction mixture was stirred at 25° C. for 1 hour. On completion, the reaction mixture was concentrated in vacuo to give the title compound (1.40 g, 95% yield, TFA salt) as red oil. LC-MS (ESI⁺) m/z 219.1 (M+H)⁺.

Tert-butyl 4-[2-[3-[4-amino-3-(difluoromethyl)pyrazol-1-yl]azetidin-1-yl] ethyl]piperidine-1-carboxylate (Intermediate ABI)

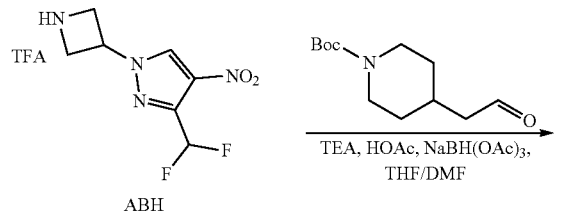

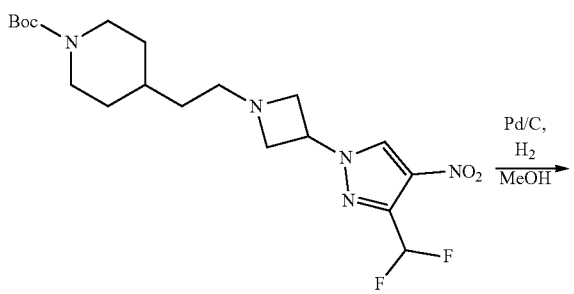

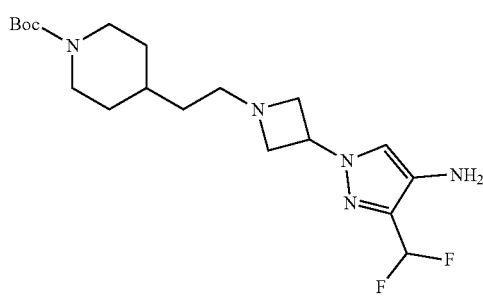

Step 1—Tert-butyl 4-[2-[3-[3-(difluoromethyl)-4-nitro-pyrazol-1-yl]azetidin-1-yl]ethylpiperidine-1-carboxylate To a mixture of 1-(azetidin-3-yl)-3-(difluoromethyl)-4-nitro-pyrazole (1.40 g, 4.21 mmol, TFA salt, Intermediate ABH) in DMF (3 mL) and THF (5 mL) was added TEA (426 mg, 4.21 mmol, 586 uL) and stirred at 25° C. for 12 min. Then tert-butyl 4-(2-oxoethyl)piperidine-1-carboxylate (957 mg, 4.21 mmol) and HOAc (253 mg, 4.21 mmol, 241 uL) was added to the mixture and stirred at 25° C. for 0.5 hour. Finally NaBH(OAc)₃ (1.79 g, 8.43 mmol) was added to the mixture at 25° C. The reaction mixture was stirred at 25° C. for 12 hours. On completion, the reaction mixture was quenched with water (0.1 mL) and concentrated in vacuo. The residue was purified by reverse phase (0.1% FA condition) to give the title compound (640 mg, 35% yield) as white solid; ¹H NMR (400 MHz, DMSO-d₆) δ 9.24 (s, 1H), 7.39 (t, J=52.4 Hz, 2H), 5.53-5.38 (m, 1H), 4.60-4.43 (m, 2H), 4.47-4.25 (m, 2H), 3.91 (d, J=12.0 Hz, 2H), 3.31-3.25 (m, 3H), 2.78-2.60 (m, 2H), 1.62 (d, J=12.8 Hz, 2H), 1.46-1.41 (m, 2H), 1.38 (s, 9H), 1.06-0.93 (m, 2H); LC-MS (ESI⁺) m/z 430.3 (M+H)⁺.

Step 2—Tert-butyl 4-[2-[3-[4-amino-3-(difluoromethyl)pyrazol-1-yl] azetidin-1-yl]ethyl]piperidine-1-carboxylate To a mixture of tert-butyl 4-[2-[3-[3-(difluoromethyl)-4-nitro-pyrazol-1-yl]azetidin-1-yl]ethyl] piperidine-1-carboxylate (590 mg, 1.37 mmol) in MeOH (10 mL) was added Pd/C (350 mg, 10 wt %). The reaction mixture was stirred at 25° C. for 0.4 hour under H₂ (15 Psi) atmosphere. On completion, the reaction mixture was filtered and concentrated in vacuo to give the title compound (540 mg, 98% yield) as light yellow solid. ¹H NMR (400 MHz, DMSO-d₆) δ 7.32 (s, 1H), 6.96 (t, J=56 Hz, 1H), 5.33-5.13 (m, 1H), 4.43 (s, 2H), 4.30-4.19 (m, 2H), 3.91 (d, J=12.0 Hz, 2H), 3.27-3.20 (m, 2H), 3.17 (s, 1H), 2.76-2.62 (m, 2H), 1.61 (d, J=12.4 Hz, 2H), 1.48-1.42 (m, 2H), 1.39 (s, 9H), 1.07-0.92 (m, 2H); LC-MS (ESI⁺) m/z 400.3 (M+H)⁺.

2-[2-(Cyclopropylmethylamino)-4-pyridyl]-N-[3-(difluoromethyl)-1-[1-[2-(4-piperidyl)ethyl] azetidin-3-yl]pyrazol-4-yl]oxazole-4-carboxamide (Intermediate ABJ)

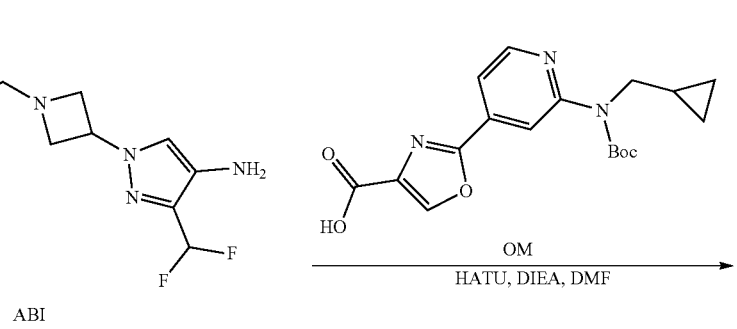

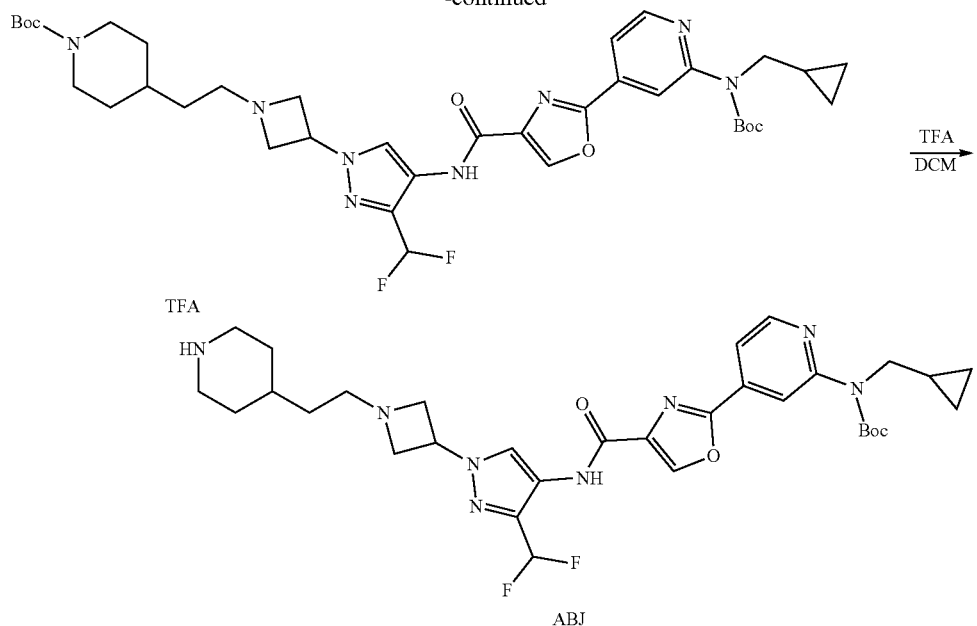

Step 1—Tert-butyl 4-[2-[3-[4-[[2-[2-[tert-butoxycarbonyl(cyclopropylmethyl)amino]-4-pyridyl]oxazole-4-carbonyl]amino]-3-(difluoromethyl)pyrazol-1-yl]azetidin-1-yl]ethyl]piperidine-1-carboxylate To a mixture of tert-butyl 4-[2-[3-[4-amino-3-(difluoromethyl)pyrazol-1-yl]azetidin-1-yl]ethyl] piperidine-1-carboxylate (530 mg, 1.33 mmol, Intermediate ABI) in DMF (3 mL) was added DIPEA (514 mg, 3.98 mmol, 693 uL), 2-[2-[tert-butoxycarbonyl(cyclopropylmethyl)amino]-4-pyridyl]oxazole-4-carboxylic acid (476 mg, 1.33 mmol, Intermediate OM) and HATU (605 mg, 1.59 mmol). The reaction mixture was stirred at 25° C. for 0.5 hour. On completion, the reaction mixture was diluted with water (10 mL). Brown solid was formed and filtered to give the compound (760 mg, 77% yield) as brown solid. $^1$H NMR (400 MHz, DMSO-$d_6$) δ 9.79 (s, 1H), 9.01 (s, 1H), 8.59 (d, J=5.2 Hz, 1H), 8.30 (d, J=8.8 Hz, 2H), 7.70-7.65 (m, 1H), 7.19 (t, J=54 Hz, 1H), 5.09-5.01 (m, 1H), 3.94-3.88 (m, 2H), 3.86 (d, J=6.8 Hz, 2H), 3.67 (t, J=7.6 Hz, 2H), 3.33 (s, 2H), 3.31-3.27 (m, 2H), 2.74-2.61 (m, 2H), 1.62 (d, J=12.4 Hz, 2H), 1.51 (s, 9H), 1.47-1.42 (m, 1H), 1.38 (s, 9H), 1.28-1.20 (m, 2H), 1.20-1.12 (m, 1H), 1.02-0.90 (m, 2H), 0.43-0.38 (m, 2H), 0.26-0.21 (m, 2H).

Step 2—2-[2-(Cyclopropylmethylamino)-4-pyridyl]-N-[3-(difluoromethyl)-1-[1-[2-(4-piperidyl)ethyl]azetidin-3-yl]pyrazol-4-yl]oxazole-4-carboxamide To a mixture of tert-butyl 4-[2-[3-[4-[[2-[2-[tert-butoxycarbonyl(cyclopropylmethyl)amino]-4-pyridyl] oxazole-4-carbonyl]amino]-3-(difluoromethyl)pyrazol-1-yl]azetidin-1-yl]ethyl]piperidine-1-carboxylate (200 mg, 269 umol) in DCM (2 mL) was added TFA (20.5 g, 180 mmol, 13.3 mL). The reaction mixture was stirred at 25° C. for 12 hours. On completion, the reaction mixture was concentrated in vacuo to give the title compound (176 mg, 99% yield, TFA salt) as brown oil. LC-MS (ESI) m z 541.4 (M+H)$^r$.

1-(2,6-Dioxo-3-piperidyl)-3-methyl-2-oxo-benzimidazole-4-carboxylic acid (Intermediate ABK)

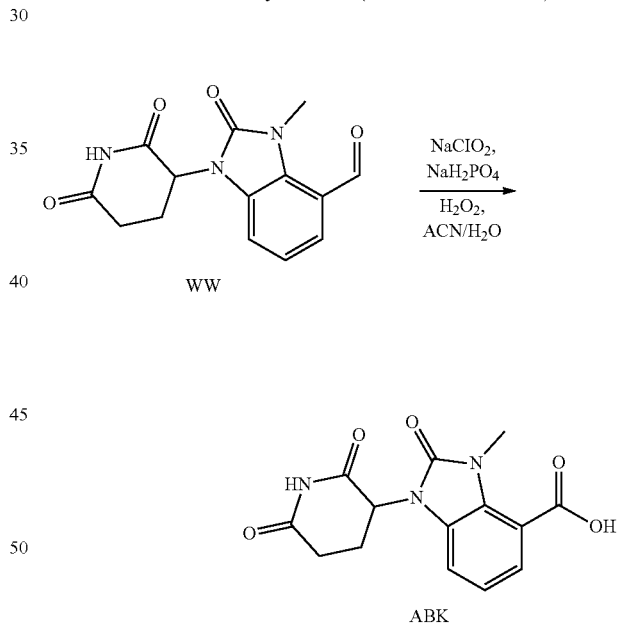

To a solution 1-(2,6-dioxo-3-piperidyl)-3-methyl-2-oxo-benzimidazole-4-carbaldehyde (200 mg, 696 umol, Intermediate WW) and NaH$_2$PO$_4$ (417.65 mg, 3.48 mmol) in ACN (3.00 mL) was added H$_2$O$_2$ (158 mg, 1.39 mmol, 30% solution) dropwise at 0° C. Then a solution of sodium; chlorite (440 mg, 4.87 mmol) in H$_2$O (3.00 mL) was added dropwise at 0° C. The reaction mixture was stirred at 25° C. for 1 hour. On completion, the reaction mixture was quenched by addition Na$_2$S$_2$O$_3$ (10 mL). The water layers was filtered and concentrated in vacuo to give a residue. The residue was purified by reverse phase (0.1% FA condition) to give the title compound (120 mg, 56% yield) as a white solid. LC-MS (ESI$^+$) m/z 304.1 (M+H)$^+$.

3-[3-Methyl-4-[4-(methylamino)piperidine-1-carbonyl]-2-oxo-benzimidazol-1-yl]piperidine-2,6-dione (Intermediate ABL)

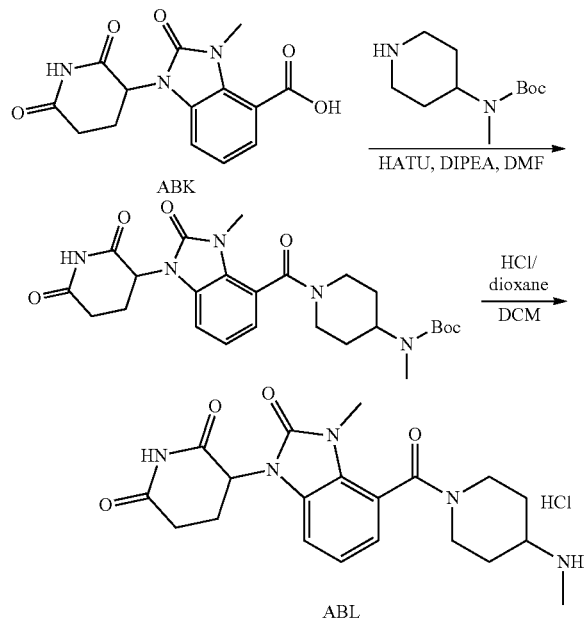

Step 1—Tert-butyl N-[1-[1-(2,6-dioxo-3-piperidyl)-3-methyl-2-oxo-benzimidazole-4-carbonyl]-4-piperidyl]-N-methylcarbamate To a solution of 1-(2,6-dioxo-3-piperidyl)-3-methyl-2-oxo-benzimidazole-4-carboxylic acid (120 mg, 395 umol, Intermediate ABK) and tert-butyl N-methyl-N-(4-piperidyl) carbamate (85.0 mg, 395 umol, CAS #108612-54-0) in DMF (5.00 mL) was added DIPEA (153 mg, 1.19 mmol, 206 uL) and HATU (225 mg, 593 umol). The mixture was stirred at 20° C. for 0.5 hr. On completion, the reaction mixture was quenched by addition water (3 mL), and then extracted with EA (4×15 mL). The combined organic layers were washed with brine (2×10 mL), dried over Na$_2$SO$_4$, filtered and concentrated in vacuo to give a residue. The residue was purified by reversed-phase (0.1% FA) to give the title compound (130 mg, 65% yield) as a white solid. $^1$H NMR (400 MHz, DMSO-d$_6$) δ 11.12 (s, 1H), 7.19 (d, J=7.8 Hz, 1H), 7.14-7.06 (m, 1H), 7.06-6.88 (m, 1H), 5.42 (dd, J=4.8, 12.4 Hz, 1H), 4.78-4.59 (m, 1H), 3.73-3.61 (m, 1H), 3.32 (s, 3H), 3.21 (s, 3H), 3.14-3.06 (m, 1H), 2.95-2.81 (m, 2H), 2.79-2.77 (m, 1H), 2.72-2.69 (m, 2H), 2.10-1.99 (m, 1H), 1.76-1.62 (m, 2H), 1.62-1.44 (m, 2H), 1.40 (s, 9H).

Step 2—3-[3-Methyl-4-[4-(methylamino)piperidine-1-carbonyl]-2-oxo-benzimidazol-1-yl]piperidine-2,6-dione To a solution of tert-butyl N-[1-[1-(2,6-dioxo-3-piperidyl)-3-methyl-2-oxo-benzimidazole-4-carbonyl]-4-piperidyl]-N-methylcarbamate (100 mg, 200 umol) in DCM (3.00 mL) was added HCl/dioxane (4 M, 3.00 mL). Then the mixture was stirred at 20° C. for 0.5 hr. On completion, the reaction mixture was concentrated in vacuo to give the title compound (87.0 mg, 99% yield, HCl) as a white solid. LC-MS (ESI$^+$) m/z 400.1 (M+H)$^+$.

Tert-butyl N-[3-(difluoromethyl)-1-(4-formylcyclohexyl)pyrazol-4-yl]carbamate (Intermediate ABM)

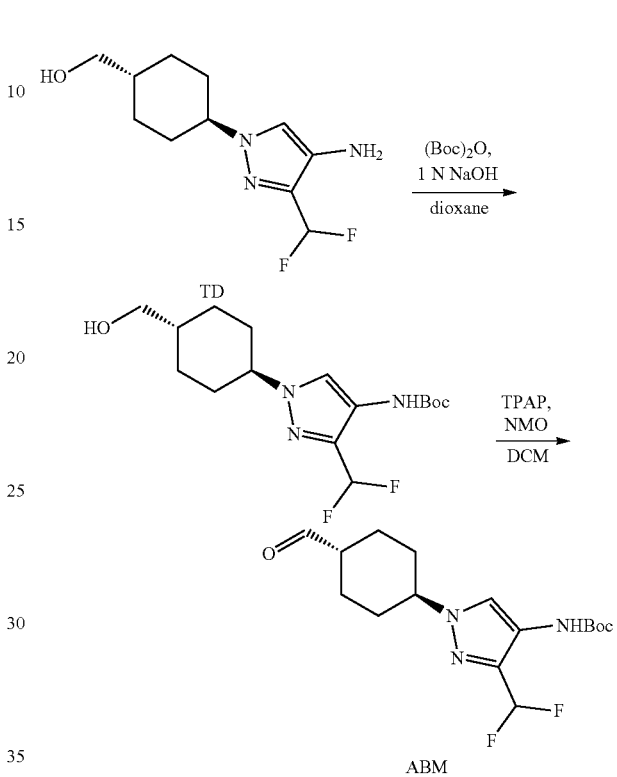

Step 1—Tert-butyl N-[3-(difluoromethyl)-1-[4-(hydroxymethyl)cyclohexyl]pyrazol-4-yl]carbamate To a solution of [4-[4-amino-3-(difluoromethyl)pyrazol-1-yl]cyclohexyl]methanol (2.50 g, 10.1 mmol, Intermediate TD), NaOH (1.00 M, 30.5 mL) in dioxane (30.0 mL) was added (Boc)$_2$O (3.34 g, 15.2 mmol, 3.51 mL). The mixture was stirred at 15° C. for 16 hrs. On completion, the mixture was diluted with H$_2$O (50 mL), and extracted with EA (3×30 mL). The organic layers were dried over anhydrous Na$_2$SO$_4$, filtered and concentrated in vacuo, the mixture was purified by silica gel column (PE:EA=1:1) to give the title compound (1.30 g, 36% yield) as white solid. $^1$H NMR (400 MHz, DMSO-d$_6$) δ 8.88 (s, 1H), 7.88 (s, 1H), 4.45 (t, J=54 Hz, 1H), 4.50-4.43 (m, 1H), 4.16-4.03 (m, 1H), 3.28-3.22 (m, 2H), 2.05-1.96 (m, 2H), 1.89-1.79 (m, 2H), 1.76-1.62 (m, 2H), 1.45 (s, 9H), 1.43-1.37 (m, 1H), 1.15-1.00 (m, 2H).

Step 2—Tert-butyl N-[3-(difluoromethyl)-1-(4-formylcyclohexyl)pyrazol-4-yl]carbamate To a solution of tert-butyl N-[3-(difluoromethyl)-1-[4-(hydroxymethyl)cyclohexyl]pyrazol-4-yl] carbamate (1.20 g, 3.47 mmol) in DCM (20.0 mL) was added NMO (610 mg, 5.21 mmol), TPAP (61.0 mg, 173 umol) and 4 Å molecular sieves (50 mg). The mixture was stirred at 15° C. for 1 hr. On completion, the mixture was diluted with DCM (30 mL) and washed with H$_2$O (3×30 mL). The organic layer was washed with brine (2×30 mL) and dried over anhydrous Na$_2$SO$_4$, filtered and concentrated in vacuo. The mixture was purified by silica gel column (PE:EA=2:1) to give the title compound (700 mg, 58% yield) as black solid. $^1$H NMR (400 MHz, CDCl$_3$) δ 9.61 (s, 1H), 7.86 (s, 1H), 6.79-6.47 (m, 2H), 4.00-3.89 (m, 1H), 2.30-2.04 (m, 5H), 1.83-1.67 (m, 2H), 1.50-1.29 (m, 11H).

3-[4-[3-[[1-[[4-[4-Amino-3-(difluoromethyl)pyrazol-1-yl]cyclohexyl]methyl]-4-piperidyl] oxy]propyl]-3-methyl-2-oxobenzimidazol-1-yl]]piperidine-2,6-dione (Intermediate ABN)

Na$_2$SO$_4$, filtered and concentrated in vacuo. The residue was purified by reverse phase: (0.1% FA) to give the title compound (1.20 g, 80% yield) as yellow solid, $^1$H NMR (400 MHz, CDCl$_3$) δ 8.65 (s, 1H), 8.41 (s, 1H), 7.90 (s, 1H), 7.05-6.94 (m, 1H), 6.90 (d, J=7.6 Hz, 1H), 6.88-6.57 (m, 3H), 5.24-5.16 (m, 1H), 4.05-3.93 (m, 1H), 3.70 (s, 3H), 3.62-3.55 (m, 1H), 3.52-3.42 (m, 2H), 3.20-3.08 (m, 2H), 3.08-3.00 (m, 2H), 2.98-2.87 (m, 2H), 2.86-2.78 (m, 2H), 2.78-2.68 (m, 3H), 2.25-2.09 (m, 5H), 2.08-2.01 (m, 2H), 1.99-1.92 (m, 2H), 1.91-1.71 (m, 5H), 1.51 (s, 9H), 1.29-1.13 (m, 2H).

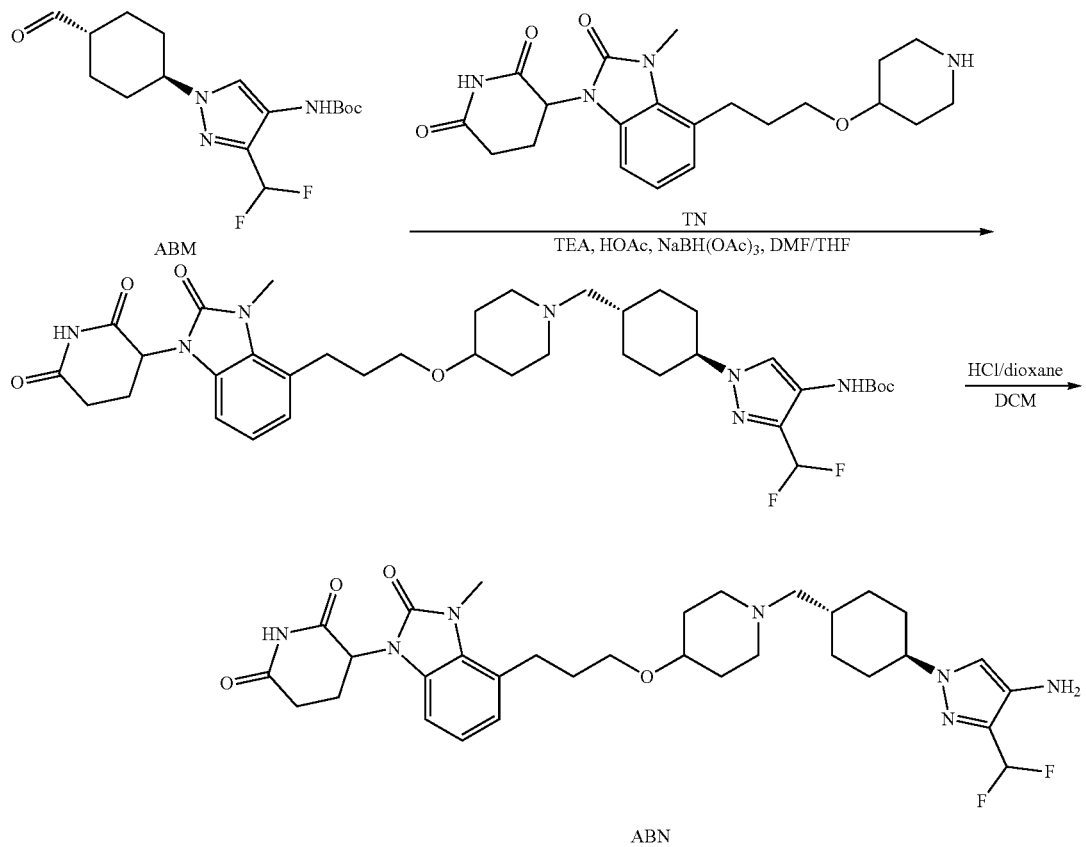

Step 1—Tert-butyl N-[3-(difluoromethyl)-1-[4-[[4-[3-[1-(2,6-dioxo-3-piperidyl)-3-methyl-2-oxo-benzimidazol-4-yl]propoxy]-1-piperidyl]methyl] cyclohexyl]pyrazol-4-yl]carbamate To a solution of tert-butyl N-[3-(difluoromethyl)-1-(4-formylcyclohexyl)pyrazol-4-yl]carbamate (700 mg, 2.04 mmol, Intermediate ABM), 3-[3-methyl-2-oxo-4-[3-(4-piperidyloxy)propyl]benzimidazol-1-yl]piperidine-2,6-dione (890 mg, 2.04 mmol, HCl, Intermediate TN) in DMF (8 mL) and THF (40 mL) was added TEA (412 mg, 4.08 mmol). The mixture was stirred at −10° C. for 0.5 hr. Then HOAc (367 mg, 6.12 mmol) and NaBH(OAc)$_3$ (864 mg, 4.08 mmol) were added, the mixture was stirred at −10° C. for 1 hr. On completion, the mixture was quenched with H$_2$O (50 mL), extracted with EA (3×40 mL), the organic layers were washed with brine (2×30 mL) and dried over anhydrous Step 2—3-[4-[3-[[1-[[4-[4-Amino-3-(difluoromethyl)pyrazol-1-yl]cyclohexyl]methyl]-4-piperidyl] oxy]propyl]-3-methyl-2-oxobenzimidazol-1-yl]piperidine-2,6-dione To a solution of tert-butyl N-[3-(difluoromethyl)-1-[4-[[4-[3-[1-(2,6-dioxo-3-piperidyl)-3-methyl-2-oxo-benzimidazol-4-yl]propoxy]-1-piperidyl]methyl]cyclohexyl]pyrazol-4-yl]carbamate (1.20 g, 1.65 mmol) in DCM (10.0 mL) was added HCl/dioxane (4.00 M, 10.0 mL). The mixture was stirred at 15° C. for 1 hr. On completion, the mixture was concentrated in vacuo to give the title compound (1.00 g, 91% yield, HCl) as yellow solid. $^1$H NMR (400 MHz, DMSO-d$_6$) δ 11.09 (s, 1H), 10.76-10.37 (m, 2H), 8.10 (s, 1H), 7.35-7.05 (m, 1H), 7.03-6.94 (m, 2H), 6.92-6.86 (m, 1H), 5.45-5.32 (m, 1H), 4.33-4.26 (m, 1H), 3.63-3.56 (m, 4H), 3.53-3.45 (m, 3H), 3.36-3.27 (m, 1H), 3.06-2.84 (m, 7H), 2.77-2.56 (m, 2H), 2.21-1.97 (m, 8H), 1.96-1.70 (m, 7H), 1.26-1.09 (m, 2H).

5-(Cyclopropylmethylamino)pyrazolo[1,5-a]pyrimidine-3-carboxylic acid (Intermediate ABO)

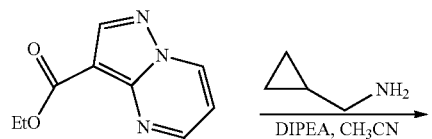

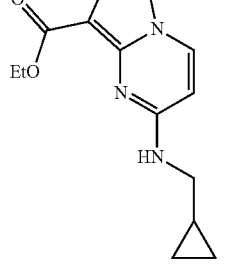

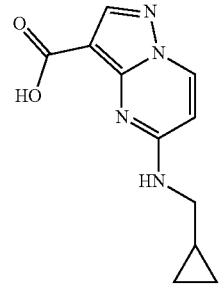

Step 1—Ethyl 5-(cyclopropylmethylamino)pyrazolo[1,5-a]pyrimidine-3-carboxylate To a solution of ethyl 5-chloropyrazolo[1,5-a]pyrimidine-3-carboxylate (1.00 g, 4.43 mmol) and DIPEA (1.72 g, 13.30 mmol, CAS #1224944-77-7) in $CH_3CN$ (15 mL) was added cyclopropylmethanamine (472 mg, 6.65 mmol, CAS #2516-47-4). The reaction mixture was stirred at 60° C. for 2 hrs. On completion, the reaction mixture was diluted with water (20 mL), and extracted with EA (2×30 mL). The combined organic phase was washed with brine (2×20 mL), dried with anhydrous $Na_2SO_4$, filtered and concentrated in vacuo to give the title compound (1.10 g, 95% yield) as a white solid. $^1H$ NMR (400 MHz, DMSO-$d_6$) δ 8.49 (d, J=7.6 Hz, 1H), 8.12 (s, 1H), 7.99 (t, J=5.2 Hz, 1H), 6.39 (d, J=7.6 Hz, 1H), 4.18 (q, J=7.2 Hz, 2H), 3.27 (t, J=6.0 Hz, 2H), 1.27 (t, J=7.2 Hz, 3H), 1.14-1.02 (m, 1H), 0.52-0.43 (m, 2H), 0.33-0.26 (m, 2H); LC-MS (ESI$^+$) m/z 261.1 (M+H)$^+$.

Step 2—5-(Cyclopropylmethylamino)pyrazolo[1,5-a]pyrimidine-3-carboxylic acid To a solution of ethyl 5-(cyclopropylmethylamino)pyrazolo[1,5-a]pyrimidine-3-carboxylate (1.00 g, 3.84 mmol) in THF (6 mL), MeOH (2 mL) and $H_2O$ (2 mL) was added LiOH·$H_2O$ (483 mg, 11.5 mmol). The reaction mixture was stirred at 60° C. for 12 hrs. On completion, the mixture was concentrated in vacuo and then diluted with $H_2O$ (20 mL). Then the mixture was adjusted with 1N HCl until the pH=5, and the mixture was concentrated in vacuo to give the title compound (890 mg, 99% yield) as a white solid. $^1H$ NMR (400 MHz, DMSO-$d_6$) δ 11.54 (s, 1H), 8.50 (d, J=7.2 Hz, 1H), 8.10 (s, 1H), 7.99 (t, J=5.2 Hz, 1H), 6.40 (d, J=7.2 Hz, 1H), 3.26 (t, J=5.2 Hz, 2H), 1.14-0.98 (m, 1H), 0.55-0.42 (m, 2H), 0.36-0.22 (m, 2H); LC-MS (ESI$^+$) m/z 255.1 (M+Na)$^+$.

5-(Cyclopropylmethylamino)-N-[1-(4-formylcyclohexyl)-3-isopropenyl-pyrazol-4-yl]pyrazolo[1,5-a]pyrimidine-3-carboxamide (Intermediate ABP)

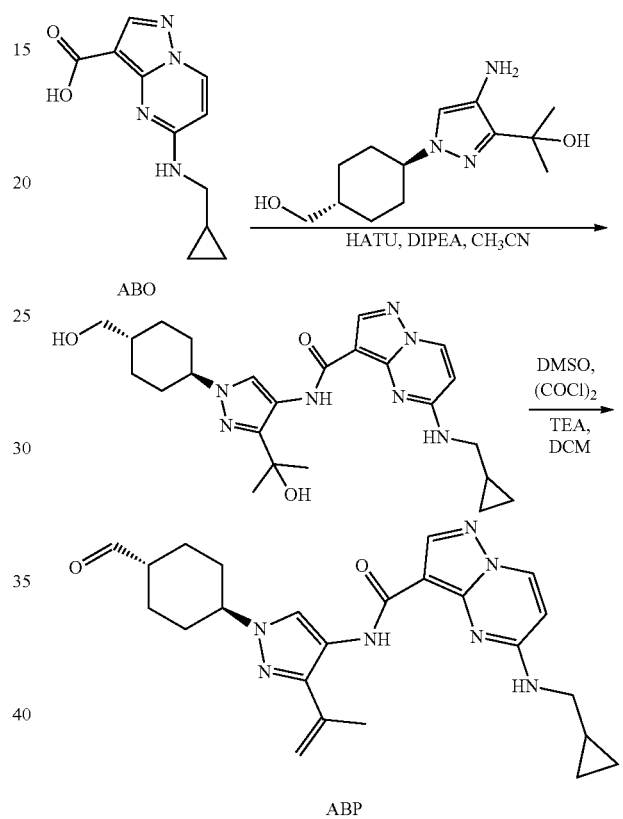

Step 1—5-(Cyclopropylmethylamino)-N-[1-[4-(hydroxymethyl)cyclohexyl]-3-(1-hydrox-1-methylethyl)pyrazol-4-yl]pyrazolo[1,5-a]pyrimidine-3-carboxamide To a mixture of 2-[4-amino-1-[4-(hydroxymethyl)cyclohexyl]pyrazol-3-yl]propan-2-ol (320 mg, 1.26 mmol, synthesized via Step 1 of Intermediate UW), 5-(cyclopropylmethylamino)pyrazolo[1,5-a]pyrimidine-3-carboxylic acid (264 mg, 1.14 mmol, Intermediate ABO) in ACN (10 mL) was added DIPEA (653 mg, 5.05 mmol). Then HATU (528 mg, 1.39 mmol) was added into the mixture. The reaction mixture was stirred at 25° C. for 1 hour. On completion, the reaction mixture was poured into water (30 mL), and the aqueous phase was extracted with ethyl acetate (2×40 mL). The combined organic phase was washed with brine (2×30 mL), dried with anhydrous $Na_2SO_4$, filtered and concentrated in vacuo to give the residue. The residue was purified by reversed-phase HPLC (0.1% FA condition) to give the title compound (328 mg, 55% yield) as a brown solid. $^1H$ NMR (400 MHz, DMSO-$d_6$) δ 9.87 (s, 1H), 8.51 (d, J=7.6

Hz, 1H), 8.23 (s, 1H), 8.13 (s, 1H), 8.00 (d, J=6.8 Hz, 1H), 6.41 (d, J=7.6 Hz, 1H), 5.32 (s, 1H), 3.98 (d, J=3.6 Hz, 1H), 3.50 (d, J=5.6 Hz, 2H), 3.25 (d, J=6.0 Hz, 2H), 2.02 (d, J=10.0 Hz, 2H), 1.85 (d, J=11.2 Hz, 2H), 1.71-1.58 (m, 2H), 1.48 (s, 6H), 1.47-1.36 (m, 2H), 1.13-1.00 (m, 3H), 0.54-0.47 (m, 2H), 0.30-0.26 (m, 2H).

Step 2—5-(Cyclopropylmethylamino)-N-[1-(4-formylcyclohexyl)-3-isopropenyl-pyrazol-4-yl]pyrazolo[1,5-a]pyrimidine-3-carboxamide To a mixture of DMSO (200 mg, 2.57 mmol) in DCM (20 mL) was slowly added (COCl)₂ (163 mg, 1.28 mmol) at −70° C. The mixture was stirred at −70° C. for 30 minutes. A solution of 5-(cyclopropylmethylamino)-N-[1-[4-(hydroxymethyl)cyclohexyl]-3-(1-hydroxy-1-methyl-ethyl)pyrazol-4-yl]pyrazolo[1,5-a]pyrimidine-3-carboxamide (200 mg, 428 umol) in DCM (10 mL) was slowly added into the mixture. The reaction mixture was stirred at −70° C. for 1 hour. Then TEA (433 mg, 4.28 mmol) was added into the mixture at −70° C. The cooling bath was removed 30 minutes after completed addition. On completion, the reaction mixture was poured into the water (100 mL), and extracted with DCM (2×80 mL). The combined organic phase was washed with brine (2×100 mL), dried with anhydrous Na₂SO₄, filtered and concentrated in vacuo to give the residue. The residue was triturated with EA:PE=8:1 to give the title compound (65.0 mg, 43% yield) as a brown solid. ¹H NMR (400 MHz, DMSO-d₆) δ 9.62 (s, 1H), 9.50-9.41 (m, 1H), 8.56 (d, J 7.6 Hz, 1H), 8.30-8.11 (m, 3H), 6.44 (d, J 7.6 Hz, 1H), 5.41 (s, 1H), 5.22 (s, 1H), 4.18-4.04 (m, 1H), 3.65-3.55 (m, 1H), 3.30-3.25 (m, 3H), 2.14-2.06 (m, 6H), 2.05 (s, 1H), 1.87-1.72 (m, 3H), 1.46-1.34 (m, 2H), 0.61-0.47 (m, 2H), 0.53-0.25 (m, 2H).

5-(4-hydroxy-1-piperidyl)pyrazolo[1,5-a]pyrimidine-3-carboxylic acid (Intermediate ABQ)

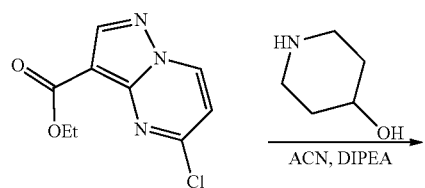

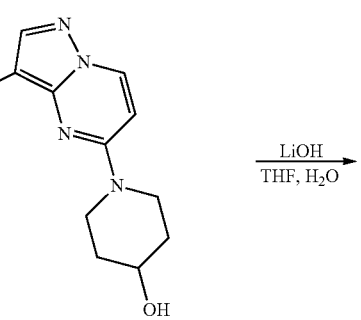

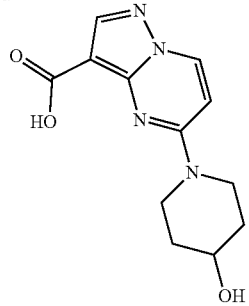

ABQ

Step 1—Ethyl 5-(4-hydroxy-1-piperidyl)pyrazolo[1,5-a]pyrimidine-3-carboxylate

To a solution of ethyl 5-chloropyrazolo[1,5-a]pyrimidine-3-carboxylate (500 mg, 2.22 mmol, CAS #1224944-77-7) and DIPEA (859 mg, 6.65 mmol, 1.16 mL) in ACN (15 mL) was added piperidin-4-ol (268 mg, 2.66 mmol, CAS #5382-16-1). The reaction mixture was stirred at 60° C. for 2 hrs. On completion, the reaction mixture was diluted with water (20 mL), and extracted with EA (2×30 mL). The combined organic phase was washed with brine (2×20 mL), dried with anhydrous Na₂SO₄, filtered and concentrated in vacuo to give the title compound (630 mg, 98% yield) as a white solid. LC-MS (ESI⁺) m/z 291.2 (M+H)⁺.

Step 2—5-(4-hydroxy-1-piperidyl)pyrazolo[1,5-a]pyrimidine-3-carboxylic acid

To a solution of ethyl 5-(4-hydroxy-1-piperidyl)pyrazolo[1,5-a]pyrimidine-3-carboxylate (600 mg, 2.07 mmol) in THF (3 mL) and H₂O (1 mL) was added LiOH.H₂O (156 mg, 3.72 mmol). The reaction mixture was stirred at 60° C. for 12 hrs. On completion, the mixture was concentrated in vacuo and then diluted with H₂O (10 mL). Then the mixture was adjusted with 1N HCl until the pH=7, and the mixture was concentrated in vacuo to give the title compound (300 mg, 55% yield) as a white solid. ¹H NMR (400 MHz, DMSO-d₆) δ 8.60 (d, J=8.0 Hz, 1H), 8.03 (s, 1H), 6.76 (d, J=8.0 Hz, 1H), 4.95-4.73 (m, 1H), 4.16-4.09 (m, 2H), 3.83-3.74 (m, 1H), 3.42-3.36 (m, 2H), 1.91-1.79 (m, 2H), 1.50-1.37 (m, 2H); LC-MS (ESI⁺) m/z 263.1 (M+H)⁺.

3-[4-[3-[[1-[[4-[4-amino-3-(difluoromethyl) pyrazol-1-yl]cyclohexyl]methyl]-4-piperidyl]oxy]propyl]-3-methyl-2-oxo-benzimidazol-1-yl]piperidine-2,6-dione (Intermediate ABR)

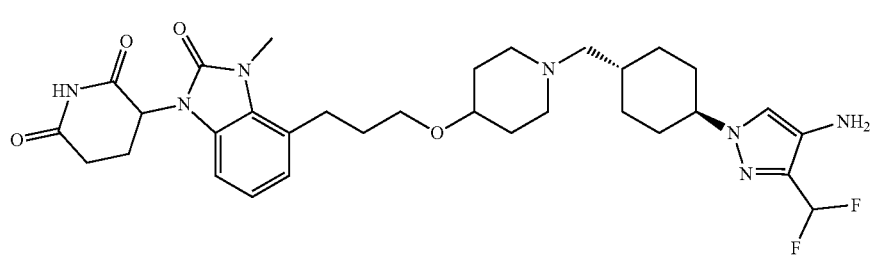

3-[4-[3-[[1-[[4-[4-amino-3-(difluoromethyl) pyrazol-1-yl]cyclohexyl]methyl]-4-piperidyl]oxy]propyl]-3-methyl-2-oxo-benzimidazol-1-yl]piperidine-2,6-dione was synthesized via Steps 1-2 of Example 18, I-302.

5-[4-(Dimethylamino)-1-piperidyl]pyrazolo[1,5-a]pyrimidine-3-carboxylic acid (Intermediate ABS)

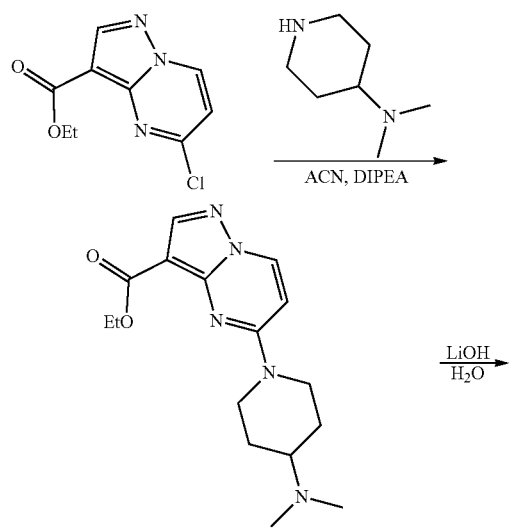

Step 1—Ethyl 5-[4-(dimethylamino)-1-piperidyl]pyrazolo[1,5-a]pyrimidine-3-carboxylate To a solution of ethyl 5-chloropyrazolo[1,5-a]pyrimidine-3-carboxylate (300 mg, 1.33 mmol, CAS #1224944-77-7) in ACN (15 mL) was added N,N-dimethylpiperidin-4-amine (170 mg, 1.33 mmol, CAS #50533-97-6) and DIPEA (2.66 mmol, 463 uL) at 25° C. The reaction mixture was stirred at 60° C. for 2 hrs. On completion, the reaction mixture was concentrated in vacuo to give the title compound (400 mg, 94% yield) as a yellow solid. $^1$H NMR (400 MHz, DMSO-$d_6$) δ 8.72 (d, J=8.0 Hz, 1H), 8.20 (s, 1H), 6.91 (d, J=8.0 Hz, 1H), 4.65 (s, 2H), 3.60-3.33 (m, 4H), 2.44 (s, 6H), 2.24 (s, 1H), 2.00 (d, J=11.6 Hz, 2H), 1.57-1.42 (m, 2H), 1.29 (t, J=7.2 Hz, 3H); LC-MS (ESI$^+$) m/z 318.2 (M+H)$^+$.

Step 2—5-[4-(Dimethylamino)-1-piperidyl]pyrazolo[1,5-a]pyrimidine-3-carboxylic acid To a solution of ethyl 5-[4-(dimethylamino)-1-piperidyl]pyrazolo[1,5-a]pyrimidine-3-carboxylate (360 mg, 1.13 mmol) in $H_2O$ (15 mL) was added LiOH·$H_2O$ (237 mg, 5.67 mmol) at 25° C. The reaction mixture was stirred at 60° C. for 2 hrs. On completion, the reaction mixture was concentrated in vacuo to give a residue. The residue was purified by reverse phase (0.1% FA condition) to give the title compound (320 mg, 97% yield) as a white solid. LC-MS (ESI$^+$) m/z 290.2 (M+H)$^+$.

5-[[(1S,2R)-2-hydroxycyclohexyl]amino]pyrazolo[1,5-a]pyrimidine-3-carboxylic acid (Intermediate ABT)

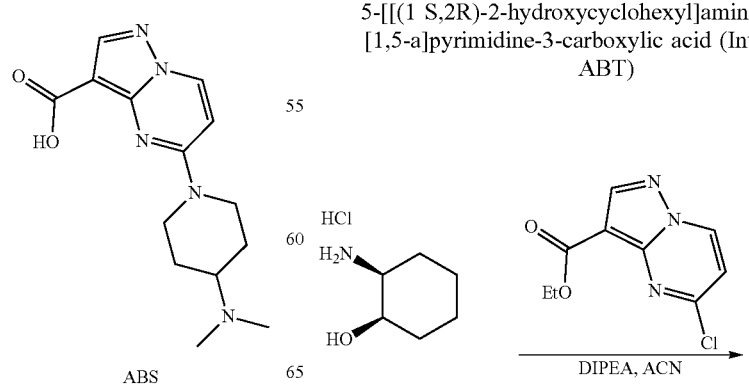

-continued

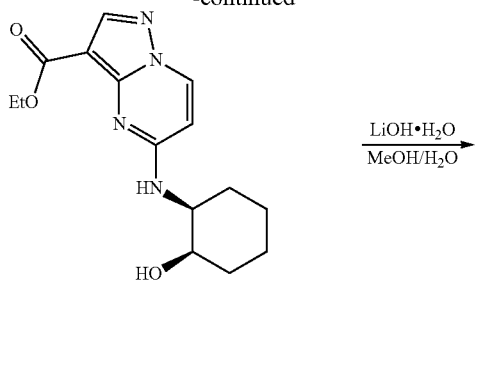

1662

5-[3-[1-(2,6-Dioxo-3-piperidyl)-3-methyl-2-oxo-benzimidazol-4-yl]propoxy]pentanoic acid (Intermediate ABU)

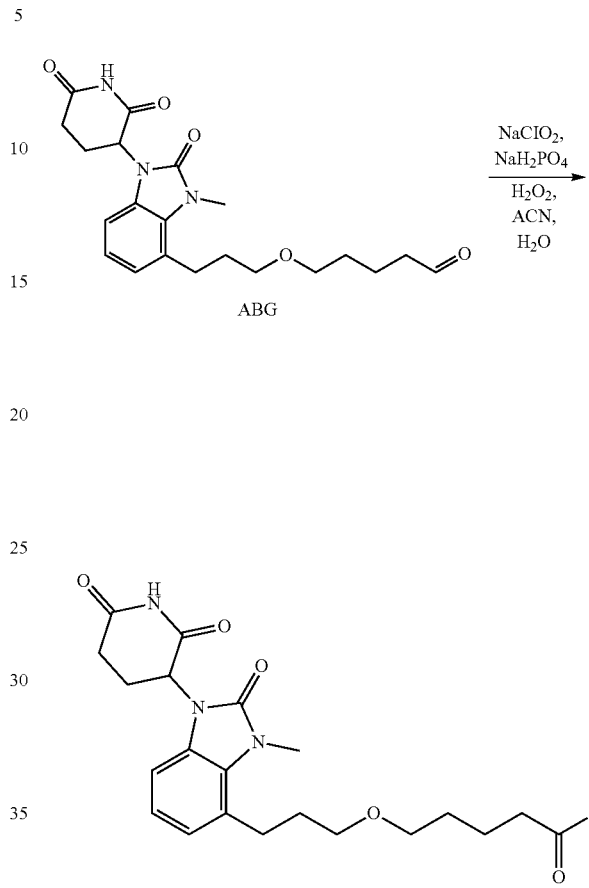

Step 1—Ethyl 5-[[(1 S,2R)-2-hydroxycyclohexyl]amino]pyrazolo[1,5-a]pyrimidine-3-carboxylate To a mixture of (1R,2S)-2-aminocyclohexanol (382 mg, 3.32 mmol, CAS #190792-72-4) and ethyl 5-chloropyrazolo[1,5-a] pyrimidine-3-carboxylate (500 mg, 2.22 mmol, CAS #1224944-77-7) in ACN (10 mL) was added DIPEA (859 mg, 6.65 mmol, 1.16 mL). The reaction mixture was stirred at 60° C. for 96 hours. On completion, the reaction mixture was concentrated in vacuo to give the title compound (800 mg, 90% yield) as light yellow oil. LC-MS (ESI$^+$) m/z 305.2 (M+H)$^+$.

Step 2—5-[[(1S,2R)-2-hydroxycyclohexyl]amino]pyrazolo[1,5-a]pyrimidine-3-carboxylic acid To a mixture of ethyl 5-[[(1S,2R)-2-hydroxycyclohexyl]amino]pyrazolo[1,5-a]pyrimidine-3-carboxylate (700 mg, 2.30 mmol) in MeOH (10 mL) and H$_2$O (2 mL) was added LiOH.H$_2$O (482 mg, 11.5 mmol). The reaction mixture was stirred at 50° C. for 12 hours. On completion, the reaction mixture was acidified with HCl (1 N) until the pH=3-4, then filtered and concentrated in vacuo to give the title compound (490 mg, 77% yield) as white solid. $^1$H NMR (400 MHz, DMSO-d$_6$) δ 11.73-11.25 (m, 1H), 8.48 (d, J=7.6 Hz, 1H), 8.09 (s, 1H), 7.66 (d, J=7.6 Hz, 1H), 6.55 (d, J=7.6 Hz, 1H), 4.75 (s, 1H), 4.07 (s, 1H), 3.90 (s, 1H), 1.71 (t, J=9.6 Hz, 2H), 1.65-1.44 (m, 4H), 1.38-1.25 (m, 2H); LC-MS (ESI$^+$) m/z 299.2 (M+Na)$^+$.

To a solution 5-[3-[1-(2,6-dioxo-3-piperidyl)-3-methyl-2-oxo-benzimidazol-4-yl]propoxy]pentanal (50.0 mg, 124 umol, Intermediate ABG) and NaH$_2$PO$_4$ (74.7 mg, 622 umol) in ACN (1 mL) was added H$_2$O$_2$ (70.6 mg, 622 umol, 30% solution) dropwise at 0° C. Then a solution of sodium-chlorite (78.8 mg, 871 umol) in H$_2$O (1 mL) was added dropwise at 0° C. After that, the reaction mixture was stirred at 15° C. for 16 hours. On completion, the mixture was quenched with saturated solution Na$_2$S$_2$O$_3$ (0.5 mL), and the mixture was concentrated in vacuo to give a residue. The residue was purified by prep-HPLC (FA condition) to give the title compound (45.0 mg, 86% yield) as white solid. $^1$H NMR (400 MHz, DMSO-d$_6$) δ 11.09 (s, 1H), 6.96 (d, J=4.8 Hz, 2H), 6.90-6.83 (m, 1H), 5.36 (dd, J=5.2, 12.8 Hz, 1H), 3.56 (s, 3H), 3.46-3.40 (m, 4H), 3.01-2.93 (m, 2H), 2.92-2.83 (m, 1H), 2.77-2.60 (m, 2H), 2.24 (t, J=7.2 Hz, 2H), 2.05-1.95 (m, 1H), 1.89-1.76 (m, 2H), 1.62-1.47 (m, 4H); LC-MS (ESI$^+$) m/z 418.1 (M+H)$^+$.

3-[2-Oxo-7-[3-(4-piperidyloxy)propyl]-1,3-benzoxazol-3-yl]piperidine-2,6-dione (Intermediate ABV)

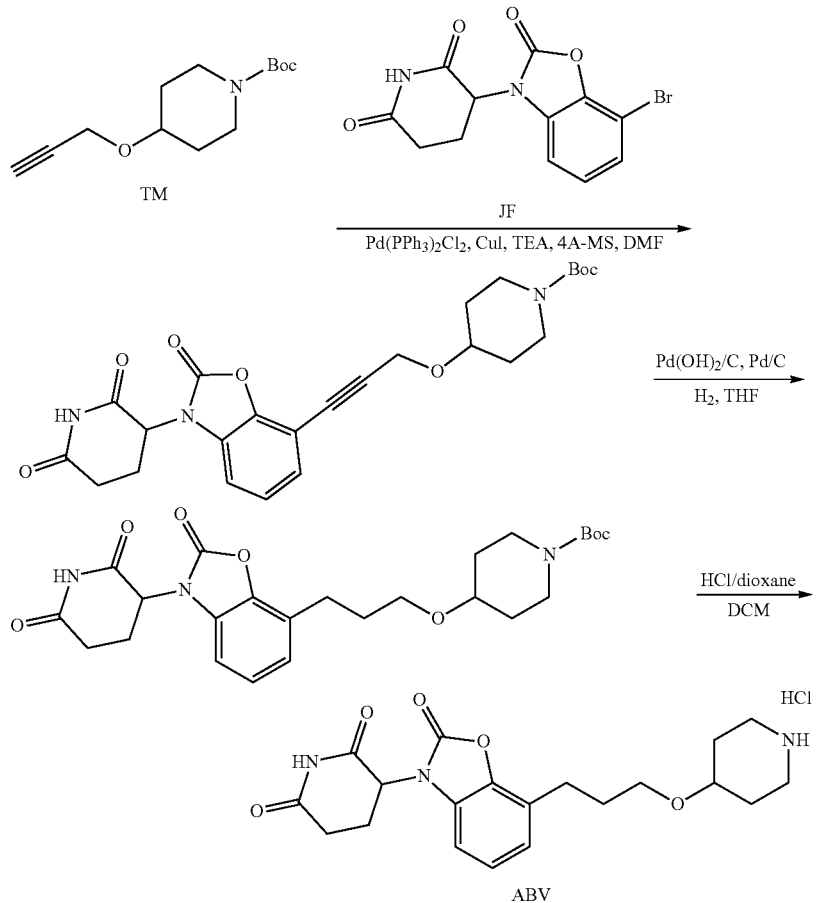

Step 1—Tert-butyl 4-[3-[3-(2,6-dioxo-3-piperidyl)-2-oxo-1,3-benzoxazol-7-yl]prop-2-ynoxy] piperidine-1-carboxylate To a solution of 3-(7-bromo-2-oxo-1,3-benzoxazol-3-yl)piperidine-2,6-dione (500 mg, 1.54 mmol, Intermediate JF) and tert-butyl 4-prop-2-ynoxypiperidine-1-carboxylate (441 mg, 1.85 mmol, Intermediate™) in DMF (10 mL) was added TEA (1.56 g, 15.3 mmol, 2.14 mL), CuI (29.3 mg, 153 umol) 4 Å molecular sieves (100 mg) and Pd(PPh$_3$)$_2$Cl$_2$ (107 mg, 153 umol). The reaction mixture was stirred at 80° C. for 2 hr under N$_2$. On completion, the mixture was diluted with H$_2$O (20 mL), then extracted with EA (2×50 mL). The organic phase was dried over by Na$_2$SO$_4$, then filtered and the filtrate was concentrated in vacuo to give a residue. The residue was purified by reverse phase (0.1% FA condition) to give the title compound (260 mg, 34.9% yield) as a yellow solid. $^1$H NMR (400 MHz, DMSO-d$_6$) δ 11.23 (s, 1H), 7.31 (dd, J=2.0, 6.8 Hz, 1H), 7.27-7.19 (m, 2H), 5.39 (dd, J=5.2, 12.8 Hz, 1H), 4.51 (s, 2H), 3.77-3.70 (m, 1H), 3.68-3.60 (m, 2H), 3.13-2.99 (m, 2H), 2.93-2.83 (m, 1H), 2.74-2.68 (m, 1H), 2.67-2.61 (m, 1H), 2.22-2.13 (m, 1H), 1.90-1.81 (m, 2H), 1.47-1.40 (m, 2H), 1.39 (s, 9H); LC-MS (ESI$^+$) m/z 506.2 (M+Na)$^+$.

Step 2—Tert-butyl 4-[3-[3-(2,6-dioxo-3-piperidyl)-2-oxo-1,3-benzoxazol-7-yl]propoxy]piperidine-1-carboxylate To a solution of tert-butyl 4-[3-[3-(2,6-dioxo-3-piperidyl)-2-oxo-1,3-benzoxazol-7-yl]prop-2-ynoxy] piperidine-1-carboxylate (240 mg, 496 umol) in THF (10 mL) was added Pd/C (100 mg, 605 umol, 10 wt %) and Pd(OH)$_2$/C (100 mg, 10 wt %). The reaction mixture was stirred at 20° C. for 2 hr under H$_2$ (15 psi). On completion, the mixture was filtered, and the filtrate was concentrated in vacuo to give the title compound (220 mg, 91% yield) as a white solid. $^1$H NMR (400 MHz, DMSO-d$_6$) δ 11.20 (s, 1H), 7.17-7.06 (m, 2H), 7.02 (d, J=7.2 Hz, 1H), 5.35 (dd, J=5.2, 12.8 Hz, 1H), 3.64-3.57 (m, 2H), 3.45-3.42 (m, 2H), 3.41-3.38 (m, 1H), 3.00 (t, J=9.0 Hz, 2H), 2.93-2.85 (m, 1H), 2.76 (t, J=7.6 Hz, 2H), 2.70-2.63 (m, 2H), 2.19-2.12 (m, 1H), 1.89-1.81 (m, 2H), 1.79-1.72 (m, 2H), 1.39 (s, 9H), 1.34-1.27 (m, 2H); LC-MS (ESI$^+$) m/z 510.1 (M+Na)$^+$.

Step 3—3-[2-Oxo-7-[3-(4-piperidyloxy)propyl]-1,3-benzoxazol-3-yl]piperidine-2,6-dione To a solution of tert-butyl 4-[3-[3-(2,6-dioxo-3-piperidyl)-2-oxo-1,3-benzoxazol-7-yl]propoxy] piperidine-1-carboxylate (220 mg, 451 umol) in DCM (4 mL) was added HCl/dioxane (4 M, 2 mL). The reaction mixture was stirred at 20° C. for 2 hrs. On completion, the mixture was concentrated in vacuo to give the title compound (190 mg, 99% yield, HCl) as a yellow solid. $^1$H NMR (400 MHz, DMSO-$d_6$) δ 11.22 (s, 1H), 7.18-7.10 (m, 2H), 7.03 (dd, J=2.0, 6.8 Hz, 1H), 5.39 (dd, J=5.2, 12.8 Hz, 1H), 3.56-3.50 (m, 1H), 3.45 (t, J=6.0 Hz, 2H), 3.18-3.06 (m, 2H), 2.99-2.88 (m, 3H), 2.77 (t, J=7.6 Hz, 2H), 2.71-2.62 (m, 2H), 2.20-2.12 (m, 1H), 1.99-1.91 (m, 2H), 1.91-1.83 (m, 2H), 1.73-1.63 (m, 2H); LC-MS (ESI$^+$) m/z 388.2 (M+H)$^+$.

2-(2,6-Dioxo-3-piperidyl)-4-[3-[3-(methylamino) propoxy]propyl]isoindoline-1,3-dione (Intermediate ABW)

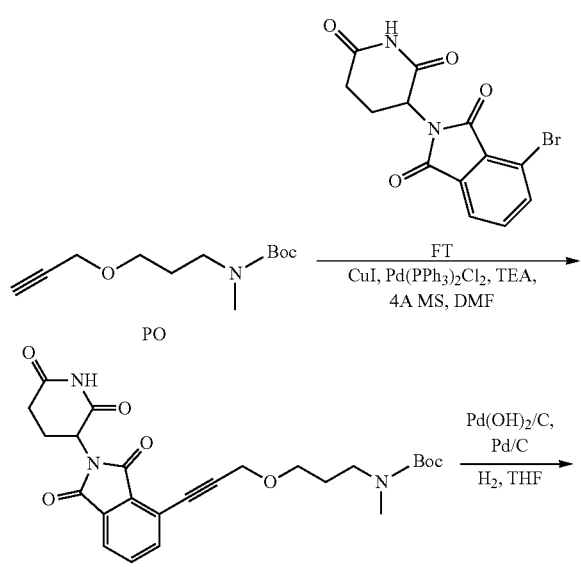

Step 1—Tert-butyl N-[3-[3-[2-(2,6-dioxo-3-piperidyl)-1,3-dioxo-isoindolin-4-yl]prop-2-ynoxy]propyl]-N-methyl-carbamate A mixture of 4-bromo-2-(2,6-dioxo-3-piperidyl)isoindoline-1,3-dione (500 mg, 1.48 mmol, Intermediate FT), tert-butyl N-methyl-N-(3-prop-2-ynoxypropyl)carbamate (539 mg, 2.37 mmol, Intermediate PO), CuI (28.2 mg, 148 umol), 4 Å molecular sieves (100 mg), TEA (2.70 g, 26.7 mmol) and Pd(PPh$_3$)$_2$Cl$_2$ (104 mg, 148 umol) in DMF (5 mL) was de-gassed and then heated at 80° C. for 2 hours under N$_2$ atmosphere. On completion, the mixture was filtered and the filtrate was concentrated in vacuo. The residue was purified by reverse phase (0.1% FA condition) to give the title compound (550 mg, 77% yield) as a slightly yellow solid. $^1$H NMR (400 MHz, DMSO-$d_6$) δ 11.12 (s, 1H), 8.00-7.81 (m, 3H), 5.15 (dd, J=5.2, 12.8 Hz, 1H), 4.47 (s, 2H), 3.60 (t, J=6.0 Hz, 2H), 3.23 (t, J=7.2 Hz, 2H), 2.97-2.83 (m, 1H), 2.77 (s, 3H), 2.70-2.55 (m, 2H), 2.11-2.01 (m, 1H), 1.80-1.70 (m, 2H), 1.37 (s, 9H).

Step 2—Tert-butyl N-[3-[3-[2-(2,6-dioxo-3-piperidyl)-1,3-dioxo-isoindolin-4-yl]propoxy]propyl]-N-methyl-carbamate To a solution of tert-butyl N-[3-[3-[2-(2,6-dioxo-3-piperidyl)-1,3-dioxo-isoindolin-4-yl]prop-2-ynoxy] propyl]-N-methyl-carbamate (500 mg, 1.03 mmol) in THF (15 mL) was added Pd/C (0.20 g, 1.25 mmol, 10% wt) and Pd(OH)$_2$/C (0.20 g, 1.25 mmol, 10% wt). The reaction mixture was stirred at 20° C. for 12 hrs under H$_2$ (15 Psi) atmosphere. On completion, the mixture was filtered and the filtrate was concentrated in vacuo to give the title compound (500 mg, 99% yield) as a yellow solid. LC-MS (ESI$^+$) m/z 510.1 (M+Na)$^+$.

Step 3—2-(2,6-Dioxo-3-piperidyl)-4-[3-[3-(methylamino)propoxy]propyl]isoindoline-1,3-dione To a solution of tert-butyl N-[3-[3-[2-(2,6-dioxo-3-piperidyl)-1,3-dioxo-isoindolin-4-yl]propoxy] propyl]-N-methyl-carbamate (580 mg, 1.19 mmol) in DCM (5 mL) was added HCl/dioxane (5 mL). The reaction mixture was stirred at 20° C. for 2 hrs. On completion, the mixture was concentrated in vacuo to give the title compound (500 mg, 99% yield, HCl salt) as a yellow solid. LC-MS (ESI$^+$) m/z 388.2 (M+H)$^+$.

2-(2,6-Dioxo-3-piperidyl)-4-[3-(4-piperidyloxy)propyl]isoindoline-1,3-dione (Intermediate ABX)

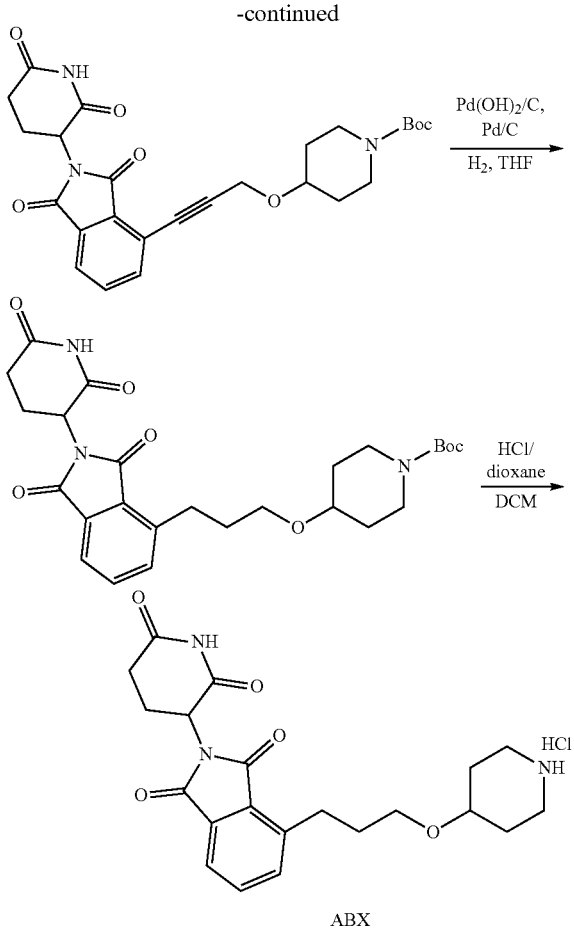

ABX

Step 1—Tert-butyl 4-[3-[2-(2,6-dioxo-3-piperidyl)-1,3-dioxo-isoindolin-4-yl]prop-2-ynoxy]piperidine-1-carboxylate To a solution of 4-bromo-2-(2,6-dioxo-3-piperidyl)isoindoline-1,3-dione (500 mg, 1.48 mmol, Intermediate FT) and tert-butyl 4-prop-2-ynoxypiperidine-1-carboxylate (461 mg, 1.93 mmol, Intermediate™) in DMF (8 mL) was added 4 Å molecular sieves (100 mg), Pd(PPh$_3$)$_2$Cl$_2$ (104 mg, 148 umol), CuI (28.2 mg, 148. umol), and TEA (1.50 g, 14.8 mmol, 2.06 mL). The reaction mixture was stirred at 80° C. for 2 hrs. On completion, the mixture was diluted with H$_2$O (20 mL), then extracted with EA (2×50 mL). The organic phase was dried over by Na$_2$SO$_4$, then filtered and the filtrate was concentrated in vacuo to give a residue. The residue was purified by reverse phase (0.1% FA condition) to give the title compound (320 mg, 44% yield) as a white solid. $^1$H NMR (400 MHz, DMSO-d$_6$) δ 11.13 (s, 1H), 7.97-7.82 (m, 3H), 5.14 (dd, J=5.2, 12.4 Hz, 1H), 4.53 (s, 2H), 3.91-3.78 (m, 1H), 3.70-3.58 (m, 2H), 3.12-2.98 (m, 2H), 2.95-2.83 (m, 1H), 2.69-2.54 (m, 2H), 2.11-2.03 (m, 1H), 1.91-1.82 (m, 2H), 1.48-1.41 (m, 2H), 1.39 (s, 9H); LC-MS (ESI$^+$) m/z 496.2 (M+H)$^+$.

Step 2—Tert-butyl 4-[3-[2-(2,6-dioxo-3-piperidyl)-1,3-dioxo-isoindolin-4-yl]propoxy]piperidine-1-carboxylate To a solution of tert-butyl 4-[3-[2-(2,6-dioxo-3-piperidyl)-1,3-dioxo-isoindolin-4-yl]prop-2-ynoxy] piperidine-1-carboxylate (300 mg, 605 umol) in THF (2 mL) was added Pd/C (100 mg, 605 umol, 10 wt %) and Pd(OH)$_2$/C (100 mg, 10 wt %). The reaction mixture was stirred at 20° C. for 2 hr under H$_2$ (15 psi). On completion, the mixture was filtered, and the filtrate was concentrated in vacuo to give the title compound (300 mg, 99% yield) as a yellow solid. $^1$H NMR (400 MHz, DMSO-d$_6$) δ 11.11 (s, 1H), 7.80-7.72 (m, 2H), 7.72-7.66 (m, 1H), 5.13 (dd, J=5.2, 12.8 Hz, 1H), 3.61 (t, J=4.8 Hz, 1H), 3.58 (t, J=4.8 Hz, 1H), 3.43 (t, J=6.4 Hz, 2H), 3.41-3.35 (m, 1H), 3.09 (t, J=7.6 Hz, 2H), 3.00 (tt, J=10.0 Hz, 2H), 2.94-2.84 (m, 1H), 2.64-2.52 (m, 2H), 2.10-2.01 (m, 1H), 1.90-1.79 (m, 2H), 1.79-1.69 (m, 2H), 1.38 (s, 9H), 1.34-1.25 (m, 2H); LC-MS (ESI$^+$) m/z 500.1 (M+H)$^+$.

Step 3—2-(2,6-Dioxo-3-piperidyl)-4-[3-(4-piperidyloxy)propyl]isoindoline-1,3-dione To a solution of tert-butyl 4-[3-[2-(2,6-dioxo-3-piperidyl)-1,3-dioxo-isoindolin-4-yl]propoxy] piperidine-1-carboxylate (300 mg, 600 umol) in DCM (6 mL) was added HCl/dioxane (4 M, 3 mL). The reaction mixture was stirred at 20° C. for 2 hr. On completion, the mixture was concentrated in vacuo to give the title compound (280 mg, 99% yield) as a yellow solid. $^1$H NMR (400 MHz, DMSO-d$_6$) δ 11.06 (s, 1H), 7.76-7.67 (m, 2H), 7.67-7.61 (m, 1H), 5.07 (dd, J=5.2, 12.8 Hz, 1H), 3.49-3.42 (m, 1H), 3.37 (t, J=6.0 Hz, 2H), 3.13-2.96 (m, 4H), 2.92-2.77 (m, 3H), 2.59-2.47 (m, 2H), 2.05-1.96 (m, 1H), 1.91-1.83 (m, 2H), 1.83-1.74 (m, 2H), 1.68-1.54 (m, 2H); LC-MS (ESI$^+$) m/z 400.1 (M+H)$^+$.

2-[1-[[1-(2,6-Dioxo-3-piperidyl)-3-methyl-2-oxobenzimidazol-5-yl]methyl]-4-piperidyl] acetaldehyde (Intermediate ABY)

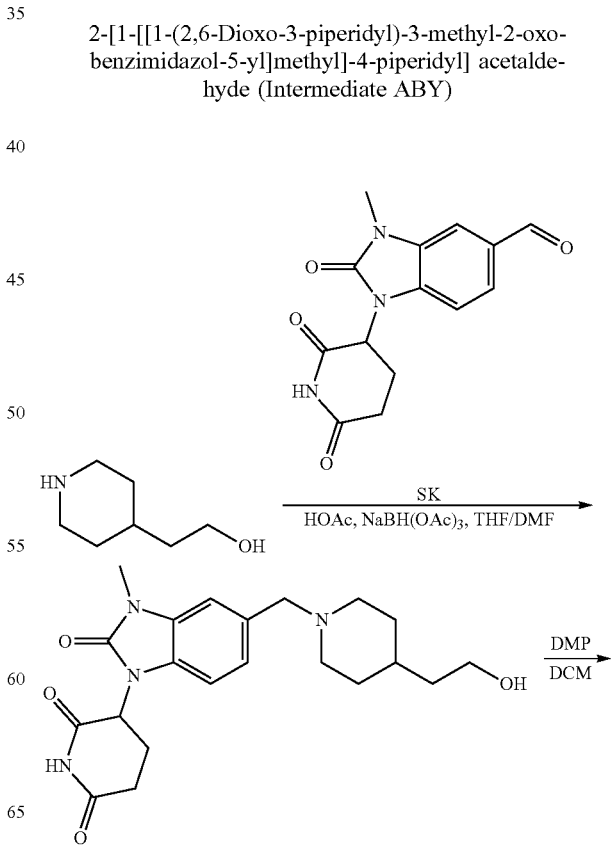

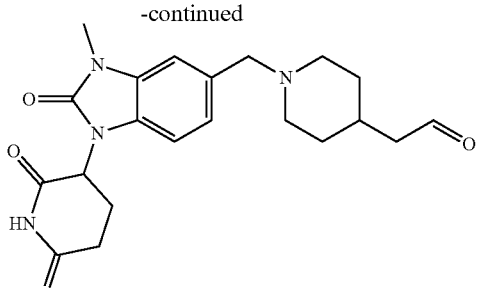

ABY

Step 1—3-[5-[[4-(2-hydroxyethyl)-1-piperidyl]methyl]-3-methyl-2-oxo-benzimidazol-1-yl]piperidine-2,6-dione To a solution of 2-(4-piperidyl)ethanol (270 mg, 2.09 mmol, CAS #622-26-4) in THF (10 mL) and DMF (3 mL) was added TEA (2.09 mmol, 290.87 uL), then the mixture stirred at 25° C. for 10 min. Next HOAc (2.09 mmol, 119 uL) and 1-(2,6-dioxo-3-piperidyl)-3-methyl-2-oxo-benzimidazole-5-carbaldehyde (660 mg, 2.30 mmol, Intermediate SK) were added to the mixture and was stirred at 80° C. for 20 minutes. Then NaBH(OAc)₃ (885 mg, 4.18 mmol) was added to the mixture at 25° C. and the reaction mixture was stirred at 25° C. for 12 hrs. On completion, the reaction mixture was added 1 mL H₂O and was concentrated in vacuo to give a residue. The residue was purified by reverse phase (0.1% FA condition) to give the title compound (250 mg, 30% yield) as a white solid. ¹H NMR (400 MHz, DMSO-d₆) δ 11.10 (s, 1H), 7.11 (s, 1H), 7.08-7.03 (m, 1H), 7.00-6.95 (m, 1H), 5.36 (dd, J=5.2, 12.8 Hz, 1H), 3.53 (s, 1H), 3.41 (t, J=6.4 Hz, 2H), 3.33 (s, 3H), 2.96-2.88 (m, 1H), 2.84 (d, J=12.0 Hz, 2H), 2.76-2.69 (m, 1H), 2.65-2.57 (m, 1H), 2.53-2.52 (m, 2H), 2.06-1.89 (m, 3H), 1.61 (d, J=12.4 Hz, 2H), 1.44-1.28 (m, 3H), 1.23-1.05 (m, 2H); LC-MS (ESI⁺) m/z 401.2 (M+H)⁺.

Step 2—2-[1-[[1-(2,6-Dioxo-3-piperidyl)-3-methyl-2-oxo-benzimidazol-5-yl]methyl]-4-piperidyl]acetaldehyde To a solution of 3-[5-[[4-(2-hydroxyethyl)-1-piperidyl]methyl]-3-methyl-2-oxo-benzimidazol-1-yl] piperidine-2,6-dione (90.0 mg, 224 umol) in DCM (5 mL) was added DMP (171 mg, 404 umol) at 25° C. The reaction mixture was stirred at 25° C. for 2 hrs. On completion, the reaction mixture was quenched by addition of sat.aq. Na₂S₂O₃ (5 mL) and NaHCO₃ (5 mL) and then the solution was extracted with DCM (3×5 mL). The combined organic layers were concentrated in vacuo to give the title compound (80.0 mg, 89% yield) as a yellow solid. LC-MS (ESI⁺) m/z 399.3 (M+H)⁺.

5-[(2S,6S)-2,6-dimethylmorpholin-4-yl]pyrazolo[1,5-a]pyrimidine-3-carboxylic acid (Intermediate ABZ)

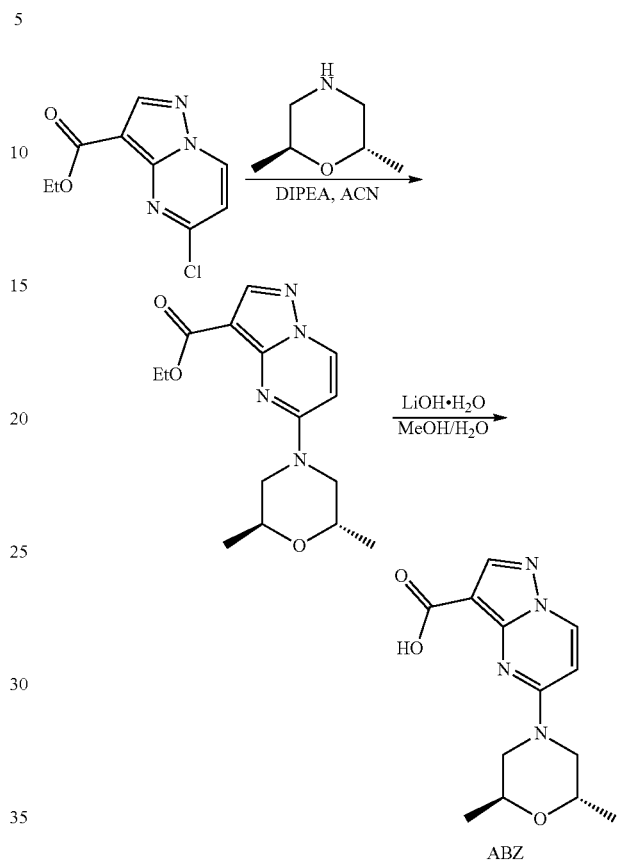

ABZ

Step 1—Ethyl 5-[(2S,6S)-2,6-dimethylmorpholin-4-yl]pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7), (2S,6S)-2,6-dimethylmorpholine (153 mg, 1.33 mmol, CAS #276252-73-4) in ACN (6 mL) was added DIPEA (458 mg, 3.55 mmol). The mixture was stirred at 60° C. for 2 hrs. On completion, the mixture was concentrated in vacuo. The mixture was diluted with H₂O (10 mL), and extracted with EA (3×10 mL). The organic layers were washed with brine (2×10 mL) and dried over anhydrous Na₂SO₄, filtered and concentrated in vacuo to give the title compound (250 mg, 92% yield) as yellow solid. ¹H NMR (400 MHz, DMSO-d₆) δ 8.73 (d, J=8.0 Hz, 1H), 8.21 (s, 1H), 6.86 (d, J=8.0 Hz, 1H), 4.24-4.16 (m, 2H), 4.09-4.01 (m, 2H), 3.99-3.80 (m, 2H), 3.54-3.42 (m, 2H), 1.29 (t, J=7.2 Hz, 3H), 1.16 (s, 3H), 1.14 (s, 3H).

Step 2—5-[(2S,6S)-2,6-dimethylmorpholin-4-yl]pyrazolo[1,5-a]pyrimidine-3-carboxylic acid To a solution of ethyl 5-[(2S,6S)-2,6-dimethylmorpholin-4-yl]pyrazolo[1,5-a]pyrimidine-3-carboxylate (250 mg, 821 umol) in a mixed solvent of MeOH (5 mL) and H₂O (1 mL) was added LiOH·H₂O (172 mg, 4.11 mmol). The mixture was stirred at 60° C. for 3 hrs. On completion, the mixture was concentrated in vacuo. The mixture was diluted with H₂O (15 mL), the mixture was acidified with 1N HCl solution until the pH=3, and extracted with EA (3×15 mL). The organic layers were dried over anhydrous Na₂SO₄, filtered and concentrated in vacuo to give the title compound (200 mg, 88% yield) as yellow solid. ¹H NMR (400 MHz, DMSO-d₆) δ 11.69 (s, 1H), 8.72 (d, J=8.0 Hz, 1H), 8.18 (s, 1H), 6.85 (d, J=8.0 Hz, 1H), 4.10-3.99 (m, 2H), 3.94-3.82 (m, 2H), 3.51-3.42 (m, 2H), 1.16 (s, 3H), 1.14 (s, 3H).

2-[2-(Cyclopropylmethylamino)-4-pyridyl]-N-[3-(difluoromethyl)-1-(4-formylcyclohexyl) pyrazol-4-yl]oxazole-4-carboxamide (Intermediate ACA)

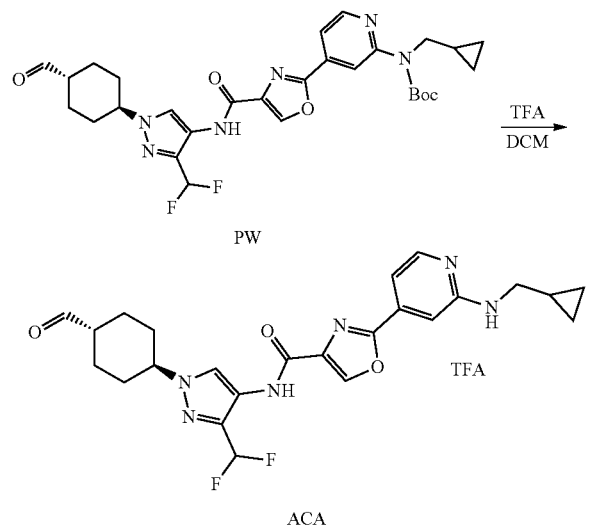

To a solution of tert-butyl N-(cyclopropylmethyl)-N-[4-[4-[[3-(difluoromethyl)-1-(4-formylcyclohexyl) pyrazol-4-yl]carbamoyl]oxazol-2-yl]-2-pyridyl]carbamate (100 mg, 171 umol, Intermediate PW) in DCM (1 mL) was added TFA (877 mg, 7.70 mmol), the mixture was stirred at 15° C. for 2 hrs. On completion, the mixture was concentrated in vacuo to give the title compound (100 mg, 98% yield, TFA) as light yellow oil. LC-MS (ESI⁺) m/z 485.2 (M+H)⁺.

Benzyl 4-hydroxypiperidine-1-carboxylate (Intermediate ACB)

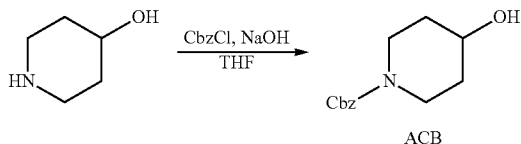 [SMILES: OC1CCNCC1 ; O=C(OCc1ccccc1)N1CCC(O)CC1 ; "THF"]

To a mixture of piperidin-4-ol (10.0 g, 98.8 mmol) and aq. NaOH (1.0 M, 120 mL) in THF (120 mL) was added CbzCl (20.2 g, 118 mmol) slowly at 0° C. The mixture was then stirred at 15° C. for 16 hours. On completion, the reaction mixture was extracted with EA (3×100 mL). The combined organic layer was washed with brine (60 mL), dried over Na₂SO₄, filtered and concentrated in vacuo. The residue was purified by column chromatography on silica gel (PE: EA=10:1 to 1:1) to give the title compound (19.0 g, 81% yield) as colorless gum. ¹H NMR (400 MHz, CDCl₃) δ 7.42-7.29 (m, 5H), 5.13 (s, 2H), 4.03-3.81 (m, 3H), 3.93-3.87 (m, 2H), 1.93-1.84 (m 2H), 1.63 (s, 1H), 1.50 (d, J=8.4 Hz, 2H).

Tert-butyl 4-(4-piperidyloxymethyl)piperidine-1-carboxylate (Intermediate ACC)

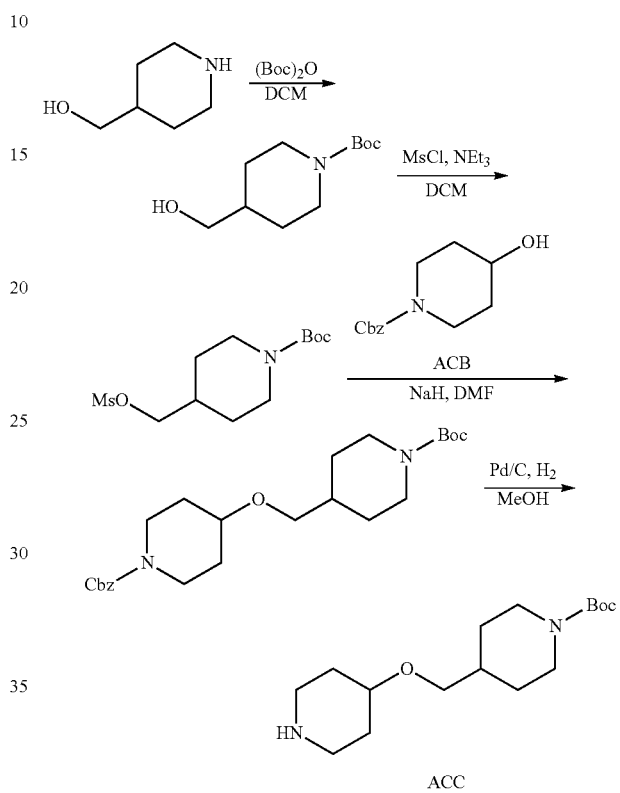

Step 1—Tert-butyl 4-(hydroxymethyl)piperidine-1-carboxylate

To a solution of 4-piperidylmethanol (5.00 g, 43.4 mmol, CAS #6457-9-4) in DCM (15 mL) was added a solution of Boc₂O (9.47 g, 43.4 mmol) in DCM (15 mL) dropwise. The mixture was stirred at 15° C. for 16 hrs. On completion, the mixture was was washed with HCl (1N) (2×20 mL). The organic layer was dried over Na₂SO₄, filtered and concentrated in vacuo to give the title compound (9.20 g, 96% yield) as white solid. ¹H NMR (400 MHz, CDCl₃) δ 4.13 (s, 2H), 3.50 (t, J=5.6 Hz, 2H), 2.71 (t, J=12.0 Hz, 2H), 1.75-1.62 (m, 3H), 1.49-1.42 (m, 9H), 1.19-1.09 (m, 2H).

Step 2—Tert-butyl 4-(methyl sulfonyloxymethyl)piperidine-1-carboxylate

To a solution of tert-butyl 4-(hydroxymethyl)piperidine-1-carboxylate (8.00 g, 37.1 mmol) in DCM (120 mL) was added TEA (11.2 g, 111 mmol) and MsCl (5.53 g, 48.3 mmol) at 0° C. The mixture was stirred at 15° C. for 0.5 hr. On completion, the mixture was washed with water (4×40 mL). The organic layer was dried over Na₂SO₄, filtered and concentrated in vacuo to give the title compound (10.0 g, 91% yield) as white solid. ¹H NMR (400 MHz, CDCl₃) δ 4.15 (d, J=5.2 Hz, 2H), 4.07 (d, J=6.4 Hz, 2H), 3.01 (s, 3H), 2.71 (t, J=12.4 Hz, 2H), 1.99-1.84 (m, 1H), 1.74 (d, J=13.6 Hz, 2H), 1.45 (s, 9H), 1.28-1.17 (m, 2H).

Step 3—Tert-butyl 4-[(1-benzyloxycarbonyl-4-piperidyl)oxymethyl]piperidine-1-carboxylate To a solution of benzyl 4-hydroxypiperidine-1-carboxylate (801 mg, 3.41 mmol, Intermediate ACB) in DMF (15 mL) was added NaH (204 mg, 5.11 mmol, 60% dispersion in mineral oil) at 0° C. The mixture was stirred at 0° C. for 0.5 hr. After that, tert-butyl 4-(methylsulfonyloxymethyl) piperidine-1-carboxylate (1.00 g, 3.41 mmol) was added, the mixture was stirred at 60° C. for 16 hrs. On completion, the reaction mixture was quenched by water (40.5 mL) at 0° C. and extracted with EA (3×15 mL). The combined organic layers were dried over Na$_2$SO$_4$, filtered and concentrated in vacuo to give a residue. The residue was by silica gel column chromatography (petroleum ether/ethyl acetate=40:1 to 15:1) to give the title compound (0.27 g, 18% yield) as light yellow oil. $^1$H NMR (400 MHz, CDCl$_3$) δ 7.41-7.28 (m, 5H), 5.13 (s, 2H), 4.22-4.02 (m, 2H), 3.81-3.70 (m, 2H), 3.46-3.42 (m, 1H), 3.35-3.21 (m, 4H), 2.70 (t, J=12.0 Hz, 2H), 1.79 (br s, 2H), 1.74-1.66 (m, 3H), 1.55 (d, J=5.6 Hz, 2H), 1.46 (s, 9H) 1.18-1.08 (m, 2H).

Step 4—Tert-butyl 4-(4-piperidyloxymethyl)piperidine-1-carboxylate

To a solution of tert-butyl 4-[(1-benzyloxycarbonyl-4-piperidyl)oxymethyl]piperidine-1-carboxylate (260 mg, 601 umol) in MeOH (4 mL) was added Pd/C (30 mg, 10 wt %) under N$_2$. The suspension was degassed under vacuum and purged with H$_2$ three times. The mixture was stirred under H$_2$ (15 psi) at 15° C. for 16 hours. On completion, the mixture was concentrated in vacuo to give the title compound (175 mg, 97% yield) as colorless oil. $^1$H NMR (400 MHz, CDCl$_3$) δ 3.91 (d, J=11.2 Hz, 2H), 3.23 (d, J=6.0 Hz, 3H), 2.88-2.83 (m, 2H), 2.73-2.65 (m, 2H), 2.46-2.29 (m, 3H), 2.77-2.74 (m, 2H), 1.68-1.54 (m, 3H), 1.38 (s, 9H), 1.29-1.15 (m, 2H), 1.06-0.92 (m, 2H).

3-[3-Methyl-2-oxo-4-[[4-(4-piperidylmethoxy)-1-piperidyl]methyl]benzimidazol-1-yl] piperidine-2,6-dione (Intermediate ACD)

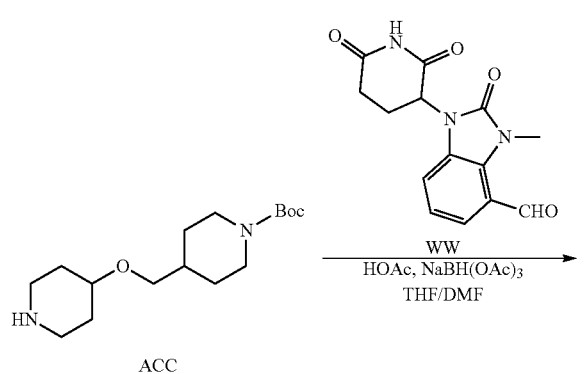

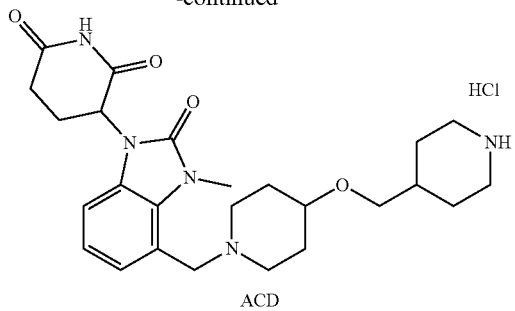

Step 1—Tert-butyl 4-[[1-[[1-(2,6-dioxo-3-piperidyl)-3-methyl-2-oxo-benzimidazol-4-yl]methyl]-4-piperidyl]oxymethyl]piperidine-1-carboxylate To a solution of tert-butyl 4-(4-piperidyloxymethyl)piperidine-1-carboxylate (165 mg, 552 umol, Intermediate ACC) and 1-(2,6-dioxo-3-piperidyl)-3-methyl-2-oxo-benzimidazole-4-carbaldehyde (158 mg, 552 umol, Intermediate WW) in mixed solvent of THF (3 mL) and DMF (0.7 mL) was added HOAc (33.2 mg, 552 umol), and the mixture was stirred at 10° C. for 0.5 hr. After that, NaBH(OAc)$_3$ (234 mg, 1.11 mmol) was added. The mixture was stirred at 10° C. for 48 hrs. On completion, the mixture was quenched with water (4 mL) and extracted with EA (4×5 mL). The combined organic layers were dried over Na$_2$SO$_4$, filtered and concentrated in vacuo to give a residue. The residue was purified by prep-HPLC (FA condition) to give the title compound (75.0 mg, 23% yield) as light yellow solid. LC-MS (ESI$^+$) m/z 570.4 (M+H)$^+$.

Step 2—3-[3-Methyl-2-oxo-4-[[4-(4-piperidylmethoxy)-1-piperidyl]methyl]benzimidazol-1-yl] piperidine-2,6-dione To a solution of tert-butyl 4-[[1-[[1-(2,6-dioxo-3-piperidyl)-3-methyl-2-oxo-benzimidazol-4-yl] methyl]-4-piperidyl]oxymethyl]piperidine-1-carboxylate (55.0 mg, 96.5 umol) in DCM (1.5 mL) was added HCl/dioxane (4 M, 1.10 mL). The mixture was stirred at 10° C. for 1.5 hrs. On completion, the reaction mixture was concentrated in vacuo to give the title compound (48.0 mg, 99% yield, HCl) as light yellow solid. LC-MS (ESI$^+$) m/z 470.3 (M+H)$^+$.

5-[(5R)-5-(tert-butoxycarbonylamino)-3,3-difluoro-1-piperidyl]pyrazolo[1,5-a]pyrimidine-3-carboxylic acid (Intermediate ACE)

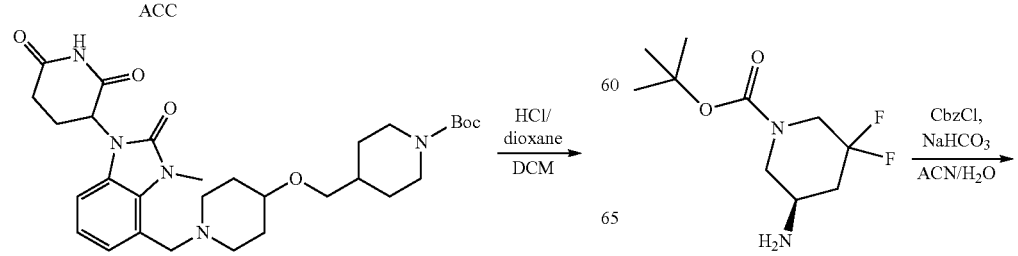

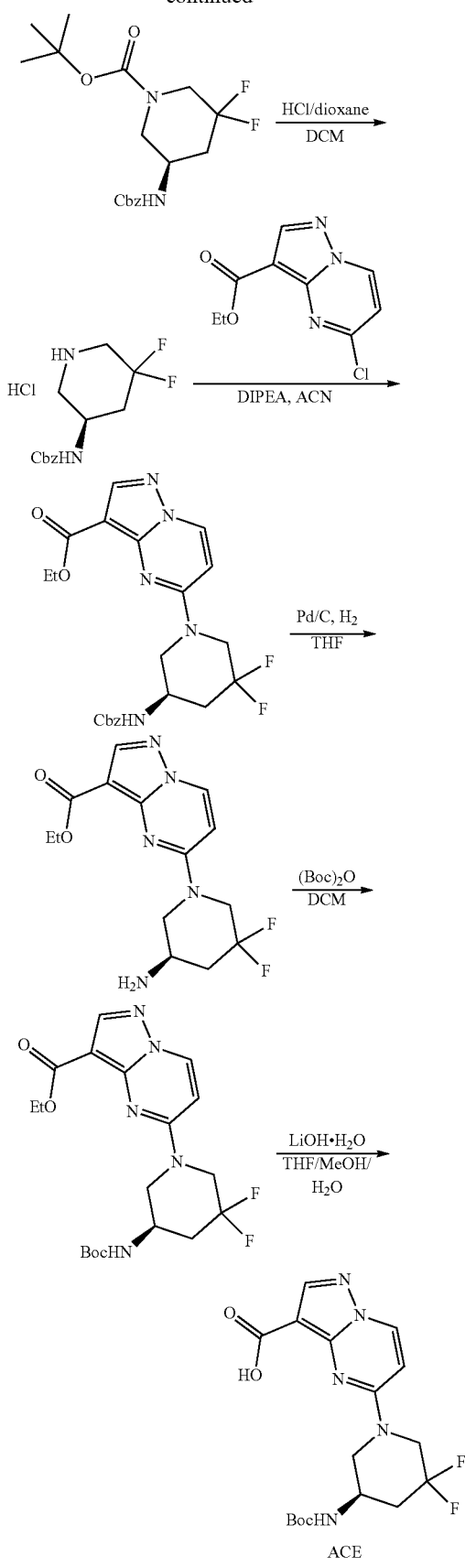

Step 1—Tert-butyl (5R)-5-(benzyloxycarbonylamino)-3,3-difluoro-piperidine-1-carboxylate To a solution of tert-butyl (5R)-5-amino-3,3-difluoro-piperidine-1-carboxylate (0.40 g, 1.69 mmol, CAS #1392473-32-3) in a mixed solvent of ACN (4 mL) and H₂O (4 mL) was added NaHCO₃ (426 mg, 5.08 mmol) and CbzCl (375 mg, 2.20 mmol). The reaction mixture was stirred at 40° C. for 48 hrs. On completion, the reaction mixture was diluted with water (20 mL) and extracted with EA (4×20 mL). The combined organic layers dried over Na₂SO₄, filtered and concentrated in vacuo to give the crude product. The crude product was triturated with (ACN/H₂O=1/10) to give the title compound (0.55 g, 88% yield) as white solid. $^1$H NMR (400 MHz, CDCl₃) δ 7.47-7.31 (m, 5H), 5.28-5.02 (m, 3H), 4.32-3.64 (m, 3H), 3.55-3.12 (m, 2H), 2.19 (t, J=11.2 Hz, 2H), 1.45 (s, 9H); LC-MS (ESI⁺) m/z 371.2 (M+H)⁺.

Step 2—Benzyl N-[(3R)-5,5-difluoro-3-piperidyl] carbamate

To a solution of tert-butyl (5R)-5-(benzyloxycarbonylamino)-3,3-difluoro-piperidine-1-carboxylate (0.94 g, 2.54 mmol) in DCM (10 mL) was added HCl/dioxane (4 M, 12.6 mL). The mixture was stirred at 15° C. for 0.5 hr. On completion, the mixture was concentrated in vacuo to give the title compound (0.77 g, 94% yield, HCl salt) as white solid; LC-MS (ESI⁺) m/z 271.1 (M+H)⁺.

Step 3—Ethyl 5-[(5R)-5-(benzyloxycarbonylamino)-3,3-difluoro-1-piperidyl]pyrazolo[1,5-a]pyrimidine-3-carboxylate To a solution of benzyl N-[(3R)-5,5-difluoro-3-piperidyl] carbamate (0.55 g, 1.79 mmol, HCl salt) in ACN (15 mL) was added DIPEA (926 mg, 7.17 mmol) and ethyl 5-chloropyrazolo[1,5-a]pyrimidine-3-carboxylate (404 mg, 1.79 mmol, CAS #1224944-77-7). The reaction mixture was stirred at 60° C. for 16 hrs. On completion, the mixture was concentrated in vacuo to give a residue. The residue was triturated with water (60 mL) filtered and the filter cake dried in vacuo to give the title compound (0.75 g, 92% yield) as light yellow solid. $^1$H NMR (400 MHz, CDCl₃) δ 8.32 (s, 1H), 8.17 (d, J=7.6 Hz, 1H), 7.43-7.29 (m, 5H), 6.37 (d, J=8.0 Hz, 1H), 5.33 (d, J=4.9 Hz, 1H), 5.19-5.11 (m, 1H), 5.08-4.98 (m, 1H), 4.67 (d, J=8.4 Hz, 1H), 4.37-4.30 (m, 2H), 4.21-4.08 (m, 2H), 3.81-3.60 (m, 2H), 2.41-2.27 (m, 2H), 1.39 (t, J=7.2 Hz, 3H); LC-MS (ESI⁺) m/z 460.2 (M+H)⁺.

Step 4—Ethyl 5-[(5R)-5-amino-3,3-difluoro-1-piperidyl]pyrazolo[1,5-a]pyrimidine-3-carboxylate To a solution of ethyl 5-[(5R)-5-(benzyloxycarbonylamino)-3,3-difluoro-1-piperidyl]pyrazolo [1,5-a]pyrimidine-3-carboxylate (600 mg, 1.31 mmol) in THF (20 mL) was added Pd/C (300 mg, 10 wt %) under N₂. The suspension was degassed under vacuum and purged with H₂ three times. The mixture was stirred under H₂ (15 psi) at 15° C. for 48 hours. On completion, the reaction mixture was filtered and concentrated in vacuo to give the title compound (0.41 g, 95% yield) as light yellow solid. $^1$H NMR (400 MHz, CDCl₃) δ 8.45-8.23 (m, 2H), 6.50 (d, J=8.0 Hz, 1H), 4.48 (d, J=11.2 Hz, 1H), 4.42-4.33 (m, 2H), 3.74-3.54 (m, 1H), 3.36-3.24 (m, 1H), 3.11 (dd, J=9.2, 13.2 Hz, 1H), 2.57-2.40 (m, 1H), 1.99-1.80 (m, 1H), 1.43-1.38 (m, 3H); LC-MS (ESI⁺) m/z 326.1 (M+H)⁺.

Step 5—Ethyl 5-[(5R)-5-(tert-butoxycarbonylamino)-3,3-difluoro-1-piperidyl]pyrazolo[1,5-a]pyrimidine-3-carboxylate To a solution of ethyl 5-[(5R)-5-amino-3,3-difluoro-1-piperidyl]pyrazolo[1,5-a]pyrimidine-3-carboxylate (400 mg, 1.23 mmol) in DCM (10 mL) was added (Boc)₂O (322 mg, 1.48 mmol). The mixture was stirred at 10° C. for 15 hrs. On completion, the mixture was concentrated in vacuo to give a residue. The residue was by silica gel column chromatography (petroleum ether/ethyl acetate=1:1) to give the title compound (380 mg, 72% yield) as light yellow solid. ¹H NMR (400 MHz, CDCl₃) δ 8.41-8.23 (m, 2H), 6.49 (d, J=7.6 Hz, 1H), 4.99 (s, 1H), 4.87-4.62 (m, 1H), 4.39-4.33 (m, 2H), 4.10-4.01 (m, 2H), 3.87-3.56 (m, 2H), 2.50-2.16 (m, 2H), 1.47-1.39 (m, 12H); LC-MS (ESI⁺) m/z 426.2 (M+H)⁺.

Step 6—5-[(5R)-5-(tert-butoxycarbonylamino)-3,3-difluoro-1-piperidyl]pyrazolo[1,5-a]pyrimidine-3-carboxylic acid To a solution of ethyl 5-[(5R)-5-(tert-butoxycarbonylamino)-3,3-difluoro-1-piperidyl]pyrazolo [1,5-a]pyrimidine-3-carboxylate (70.0 mg, 164 umol) in a mixed solvent of MeOH (0.5 mL), THF (2 mL) and H₂O (0.5 mL) was added LiOH.H₂O (17.2 mg, 411 umol). The mixture was stirred at 60° C. for 16 hrs. On completion, the mixture was concentrated in vacuo to remove THF and MeOH and then adjusted to pH=5 with HCl (1N), then concentrated in vacuo to give the title compound (65.0 mg, 99% yield, with some LiCl salt as well) as white solid. LC-MS (ESI⁺) m/z 398.1 (M+H)⁺.

N-(3-(difluoromethyl)-1-((1r,4r)-4-formylcyclohexyl)-1H-pyrazol-4-yl)pyrazolo[1,5-a]pyrimidine-3-carboxamide (Intermediate ACF)

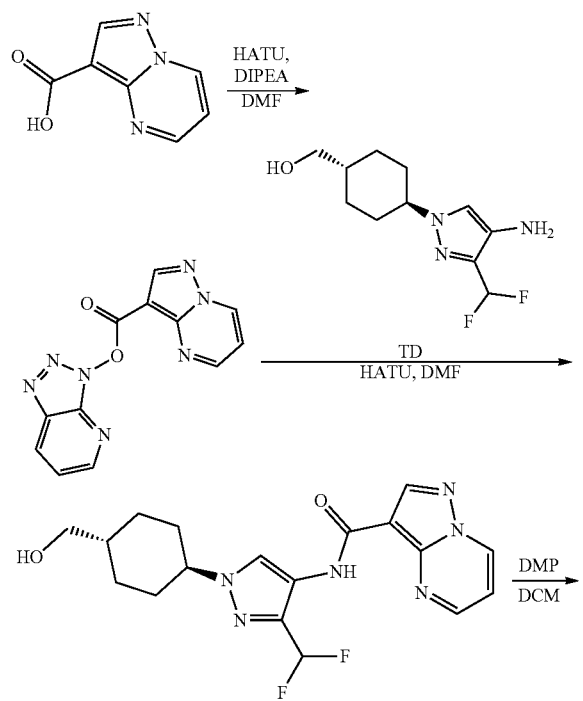

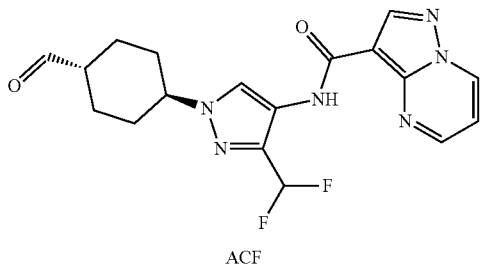

ACF

Step 1—3H-[1,2,3]triazolo[4,5-b]pyridin-3-yl pyrazolo[1,5-a]pyrimidine-3-carboxylate To a solution of pyrazolo[1,5-a]pyrimidine-3-carboxylic acid (1 g, 6.13 mmol, CAS #25940-35-6) in DMF (20 mL) was added HATU (2.33 g, 6.13 mmol) and DIPEA (1.58 g, 12.2 mmol). Then the reaction mixture was stirred at 40° C. for 2 hours. On completion, the reaction mixture was filtered. The filter cake was washed with DCM (2×4 mL) and dried in vacuo to give the title compound (1.10 g, 68% yield) as a off-white solid, LC-MS (ESI⁺) m/z 282.0 (M+H)⁺.

Step 2—N-[3-(difluoromethyl)-1-[4-(hydroxymethyl)cyclohexyl]pyrazol-4-yl]pyrazolo[1,5-a]pyrimidine-3-carboxamide To a solution of [4-[4-amino-3-(difluoromethyl)pyrazol-1-yl]cyclohexyl]methanol (468 mg, 1.91 mmol, Intermediate TD) in DMF (15 mL) was added 3H-[1,2,3]triazolo[4,5-b]pyridin-3-yl pyrazolo[1,5-a]pyrimidine-3-carboxylate (536 mg, 1.91 mmol). The reaction mixture was stirred at 40° C. for 5 hours. On completion, the reaction was quenched with sat. NH₄Cl (30 mL) and extracted with DCM (3×100 mL). The combined organic layers were washed with brine (50 mL), dried with anhydrous Na₂SO₄ and filtered. The filtrate was concentrated in vacuo. The residue was purified by reverse phase (0.1% FA) to give the title compound (400 mg, 53% yield) as a white solid, LC-MS (ESI⁺) m/z 391.2 (M+H)⁺.

Step 3—N-(3-(difluoromethyl)-1-((1r,4r)-4-formylcyclohexyl)-1H-pyrazol-4-yl)pyrazolo[1,5-a]pyrimidine-3-carboxamide To a solution of N-[3-(difluoromethyl)-1-[4-(hydroxymethyl)cyclohexyl]pyrazol-4-yl]pyrazolo [1,5-a]pyrimidine-3-carboxamide (200 mg, 512 umol) in DCM (10 mL) was added DMP (325 mg, 768 umol). The reaction mixture was stirred at 25° C. for 1 hour. On completion, the reaction was quenched with sat. NaS₂O₃ (30 mL) and extracted with DCM (2×30 mL). The combined organic layers were washed with brine (20 mL), dried with anhydrous Na₂SO₄ and filtered. The filtrate was concentrated in vacuo to give the title compound (198 mg, 509 umol, 99% yield) as a white solid, LC-MS (ESI⁺) m/z 389.2 (M+H)⁺.

5-(4-Methylpiperazin-1-yl)pyrazolo[1,5-a]pyrimidine-3-carboxylic acid (Intermediate ACG)

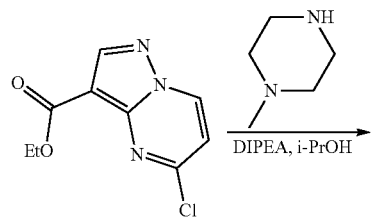

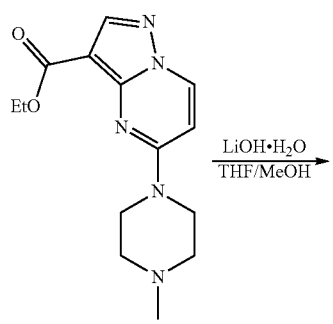

Step 1—Ethyl 5-(4-methylpiperazin-1-yl)pyrazolo[1,5-a]pyrimidine-3-carboxylate To a mixture of ethyl 5-chloropyrazolo[1,5-a]pyrimidine-3-carboxylate (1.50 g, 6.65 mmol, CAS #1224944-77-7) and 1-methylpiperazine (1.33 g, 13.3 mmol, CAS #109-01-3) in i-PrOH (30 mL) was added DIPEA (2.58 g, 19.9 mmol). The mixture was stirred at 60° C. for 2 hours. On completion, the reaction was concentrated in vacuo to give the title compound (1.20 g, 62% yield) as a white solid. $^1$H NMR (400 MHz, DMSO-$d_6$) δ 8.82 (d, J=8.0 Hz, 1H), 8.24 (s, 1H), 6.93 (d, J=8.0 Hz, 1H), 4.20 (d, J=7.2 Hz, 2H), 4.00 (s, 4H), 2.63 (s, 5H), 2.27 (s, 2H), 1.28 (d, J=7.2 Hz, 3H).

Step 2—5-(4-Methylpiperazin-1-yl)pyrazolo[1,5-a]pyrimidine-3-carboxylic acid To a mixture of ethyl 5-(4-methylpiperazin-1-yl) pyrazolo[1,5-a] pyrimidine-3-carboxylate (450 mg, 1.56 mmol) in THF (12 mL), MeOH (3 mL) and H$_2$O (3 mL) was added LiOH (112 mg, 4.67 mmol). The reaction mixture was stirred at 50° C. for 12 hours. On completion, the reaction mixture was concentrated in vacuo to remove MeOH and THF. Then water (20 mL) was added into the mixture, and adjusted to pH=4-5 with HCl (1 N), and filtered to give the title compound (350 mg, 86% yield) as a white solid. $^1$H NMR (400 MHz, DMSO-$d_6$) δ 12.26-11.23 (m, 1H), 8.83 (d, J=8.0 Hz, 1H), 8.23 (s, 1H), 6.93 (d, J=8.0 Hz, 1H), 4.45-3.79 (m, 4H), 3.53-3.21 (m, 4H), 2.72 (s, 3H).

N-[(1S)-3-(difluoromethyl)-1-(4-formylcyclohexyl)pyrazol-4-yl]-5-(4-methylpiperazin-1-yl) pyrazolo[1,5-a]pyrimidine-3-carboxamide (Intermediate ACH)

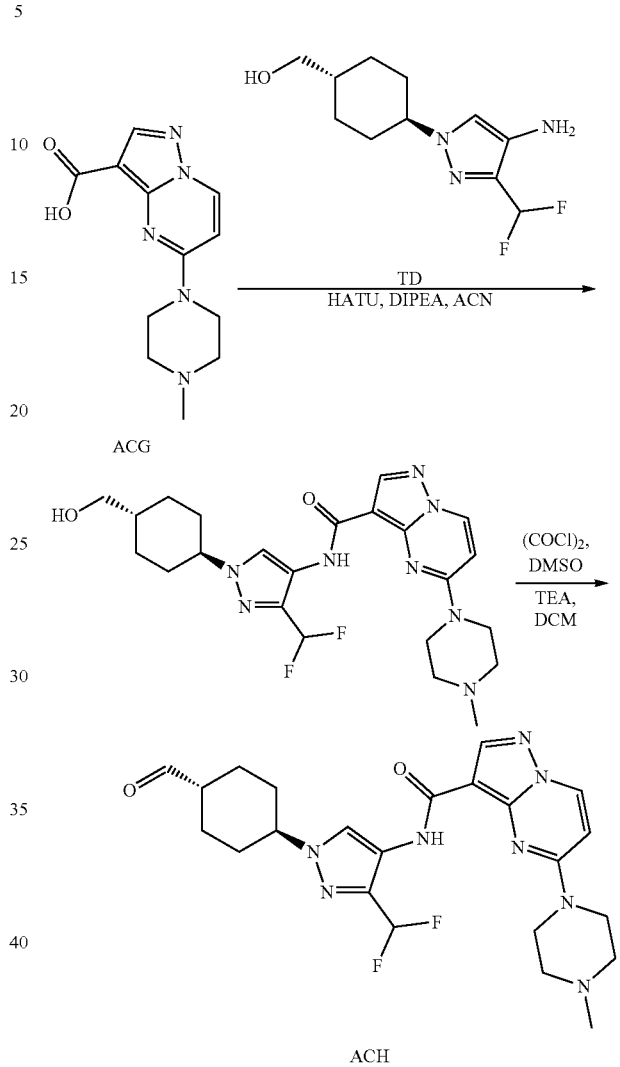

Step 1—N-[(1S)-3-(difluoromethyl)-1-[4-(hydroxymethyl)cyclohexyl]pyrazol-4-yl]-5-(4-methyl piperazin-1-yl)pyrazolo[1,5-a]pyrimidine-3-carboxamide To a mixture of 5-(4-methylpiperazin-1-yl)pyrazolo[1,5-a]pyrimidine-3-carboxylic acid (500 mg, 1.91 mmol, Intermediate ACG), [4-[(1R)-4-amino-3-(difluoromethyl)pyrazol-1-yl]cyclohexyl]methanol (515 mg, 2.10 mmol, Intermediate TD) in ACN (10 mL) was added DIPEA (740 mg, 5.73 mmol). Then HATU (799 mg, 2.10 mmol) was added into the mixture. The reaction mixture was stirred at 25° C. for 12 hours. On completion, the reaction mixture was poured into water (40 mL). The aqueous phase was extracted with ethyl acetate (2×30 mL). The combined organic phase was washed with brine (2×30 mL), dried with anhydrous Na$_2$SO$_4$, filtered and concentrated in vacuo to give the crude product. The crude product was purified by reversed-phase HPLC (0.1% FA condition) to give the title compound (650 mg, 69% yield) as a white solid. $^1$H NMR (400 MHz, DMSO-d$_6$) δ 9.78 (s, 1H), 9.33 (s, 1H), 8.97 (d, J=8.0 Hz, 1H), 8.49-8.33 (m, 2H), 7.34-6.94 (m, 2H), 4.86-4.55 (m, 2H), 4.20 (d, J=8.4 Hz, 1H), 3.57 (d, J=11.6 Hz, 3H), 3.41 (d, J=12.0 Hz, 2H), 3.27 (d, J=6.4 Hz, 2H), 2.89 (s, 3H), 2.13-2.04 (m, 3H), 1.87 (d, J=11.6 Hz, 2H), 1.74 (d, J=2.8, 12.4 Hz, 2H), 1.51-1.37 (m, 1H), 1.18-1.02 (m, 2H).

Step 2—N-[(1S)-3-(difluoromethyl)-1-(4-formylcyclohexyl)pyrazol-4-yl]-5-(4-methylpiperazin-1-yl)pyrazolo[1,5-a]pyrimidine-3-carboxamide To a mixture of DMSO (441 mg, 5.65 mmol) in DCM (30 mL) was slowly added (COCl)$_2$ (358 mg, 2.82 mmol) at −70° C. The mixture was stirred at −70° C. for 30 minutes. A solution of N-[(1S)-3-(difluoromethyl)-1-[4-(hydroxymethyl)cyclohexyl]pyrazol-4-yl]-5-(4-methylpiperazin-1-yl)pyrazolo[1,5-a]pyrimidine-3-carboxamide (460 mg, 942 umol) in DCM (20 mL) was slowly added into the mixture. The reaction mixture was stirred at −70° C. for 1 hour. Then TEA (953 mg, 9.42 mmol) was added into the mixture at −70° C. The cooling bath was removed 25 minutes later. On completion, the reaction mixture was poured into the water (100 mL) and extracted with DCM (2×80 mL). The combined organic phase was washed with brine (2×100 mL), dried with anhydrous Na$_2$SO$_4$, filtered and concentrated in vacuo to give the residue. The residue was purified by reversed-phase HPLC (0.1% FA condition) to give the title compound (248 mg, 54% yield) as a white solid. $^1$H NMR (400 MHz, DMSO-d$_6$) δ 9.62 (s, 1H), 9.41 (s, 1H), 8.79 (d, J=8.0 Hz, 1H), 8.41 (s, 1H), 8.31-8.23 (m, 1H), 8.16 (s, 1H), 7.26-6.97 (m, 1H), 6.92 (d, J=8.0 Hz, 1H), 4.27-4.18 (m, 1H), 3.81 (s, 4H), 2.50-2.42 (m, 4H), 2.27 (s, 3H), 2.17-2.01 (m, 4H), 1.89-1.76 (m, 2H), 1.46-1.32 (m, 2H).

3-[3-[1-(2,6-Dioxo-3-piperidyl)-3-methyl-2-oxo-benzimidazol-4-yl]propoxy]propanoic acid (Intermediate ACI)

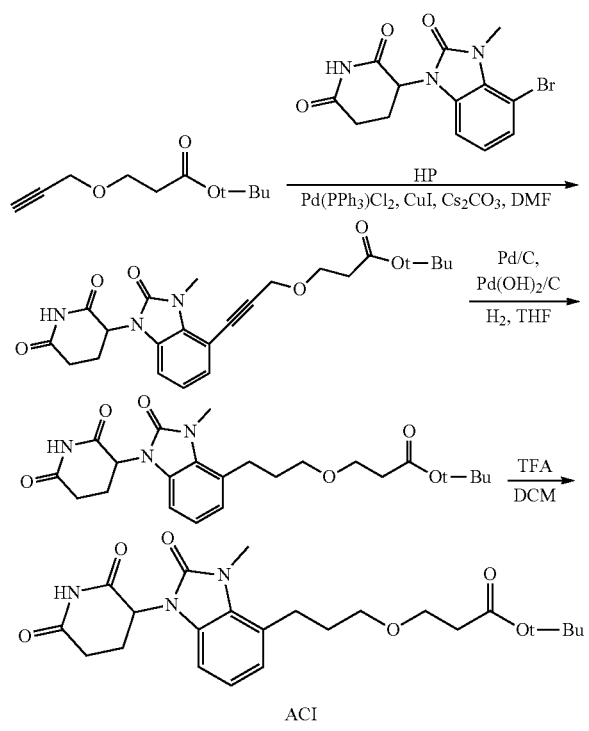

ACI

Step 1—Tert-butyl 3-[3-[1-(2,6-dioxo-3-piperidyl)-3-methyl-2-oxo-benzimidazol-4-yl]prop-2-ynoxy]propanoate A mixture of 3-(4-bromo-3-methyl-2-oxo-benzimidazol-1-yl)piperidine-2,6-dione (500 mg, 1.48 mmol, Intermediate HP), tert-butyl 3-prop-2-ynoxypropanoate (544 mg, 2.96 mmol, synthesized via Step 1 of Intermediate ZV), Pd(PPh$_3$)$_2$Cl$_2$ (103 mg, 147 umol), CuI (28.1 mg, 147 umol), 4 Å molecular sieves (30.0 mg, 1.48 mmol) and TEA (598 mg, 5.91 mmol) in DMF (10 mL) was stirred at 80° C. for 2 hours. On completion, the reaction mixture was filtered and the filtrate was concentrated in vacuo. The residue was purified by reverse phase (0.1% FA) to give the title compound (220 mg, 33% yield) as yellow solid. $^1$H NMR (400 MHz, CDCl$_3$) δ 8.12 (s, 1H), 7.22-7.14 (m, 1H), 6.99 (t, J=8.0 Hz, 1H), 6.82-6.71 (m, 1H), 5.21 (dd, J=5.6, 12.8 Hz, 1H), 4.43 (s, 2H), 3.84 (t, J=6.4 Hz, 2H), 3.79 (s, 3H), 3.00-2.91 (m, 1H), 2.89-2.67 (m, 2H), 2.56 (t, J=6.4 Hz, 2H), 2.28-2.19 (m, 1H), 1.47 (s, 9H).

Step 2—Tert-butyl 3-[3-[1-(2,6-dioxo-3-piperidyl)-3-methyl-2-oxo-benzimidazol-4-yl]propoxy] propanoate To a solution of tert-butyl 3-[3-[1-(2,6-dioxo-3-piperidyl)-3-methyl-2-oxo-benzimidazol-4-yl]prop-2-ynoxy] propanoate (200 mg, 453 umol) in THF (5 mL) was added Pd/C (20.0 mg, 10 wt %) and Pd(OH)$_2$/C (20.0 mg, 28.4 umol, 20 wt %). The reaction mixture was stirred at 10° C. for 2 hours under hydrogen (15 psi). On completion, the reaction mixture was filtered and the filtrate was concentrated in vacuo (200 mg, 99% yield) as yellow solid. $^1$H NMR (400 MHz, CDCl$_3$) δ 8.13 (s, 1H), 7.02-6.96 (m, 1H), 6.93-6.89 (m, 1H), 6.67 (d, J=7.2 Hz, 1H), 5.29-5.14 (m, 1H), 3.73-3.66 (m, 5H), 3.51 (t, J=6.0 Hz, 2H), 3.06-2.98 (m, 2H), 2.97-2.71 (m, 3H), 2.51 (t, J=6.4 Hz, 2H), 2.26-2.17 (m, 1H), 1.97-1.84 (m, 2H), 1.47 (s, 9H).

Step 3—3-[3-[1-(2,6-Dioxo-3-piperidyl)-3-methyl-2-oxo-benzimidazol-4-yl]propoxy]propanoic acid To a solution of tert-butyl 3-[3-[1-(2,6-dioxo-3-piperidyl)-3-methyl-2-oxo-benzimidazol-4-yl]propoxy]propanoate (180 mg, 404 umol) in dichloromethane (5 mL) was added TFA (3 mL). The reaction mixture was stirred at 15° C. for 1 hour. On completion, the reaction mixture was concentrated in vacuo to give the title compound (150 mg, 95% yield) as yellow solid. LC-MS (ESI$^+$) m/z 390.2 (M+H)$^+$.

Tert-butyl 4-[4-[(6-bromoquinazolin-4-yl)amino]cyclohexyl]piperazine-1-carboxylate (Intermediate ACJ)

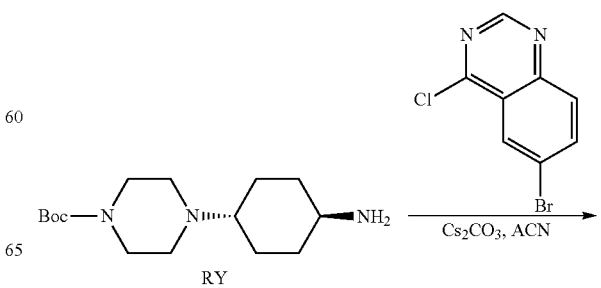

RY

1683
-continued

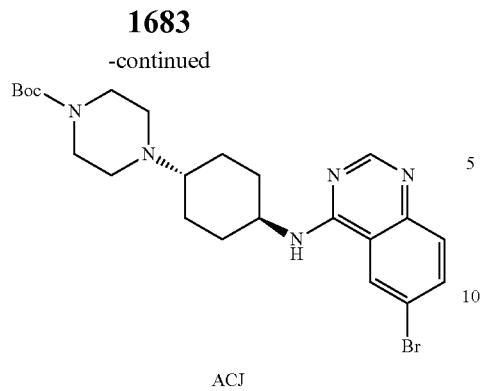

ACJ

To a mixture of tert-butyl 4-(4-aminocyclohexyl)piperazine-1-carboxylate (660 mg, 2.33 mmol, Intermediate RY) and 6-bromo-4-chloro-quinazoline (567 mg, 2.33 mmol, CAS #38267-96-8) in ACN (15 mL) was added $Cs_2CO_3$ (1.52 g, 4.66 mmol). The reaction mixture was stirred at 80° C. for 3 hours. On completion, the reaction mixture was diluted with water (10 mL). White solid was formed and filtered to give the title compound (680 mg, 59% yield) as white solid. $^1$H NMR (400 MHz, DMSO-$d_6$) δ 8.62 (d, J=2.0 Hz, 1H), 8.46 (s, 1H), 8.03 (d, J=7.6 Hz, 1H), 7.89-7.83 (m, 1H), 7.60 (d, J=8.8 Hz, 1H), 4.17-4.01 (m, 1H), 3.31-3.26 (m, 4H), 2.48-2.43 (m, 4H), 2.38-2.28 (m, 1H), 2.01 (d, J=10.4 Hz, 2H), 1.84 (d, J=10.4 Hz, 2H), 1.48-1.40 (m, 2H), 1.39 (s, 9H), 1.38-1.27 (m, 2H).

4-[(4-Piperazin-1-ylcyclohexyl)amino]quinazoline-6-carbonitrile (Intermediate ACK)

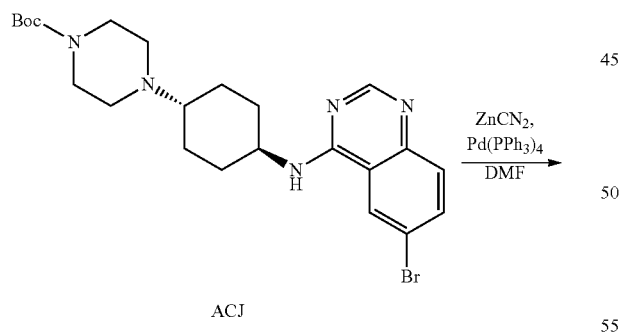

ACJ

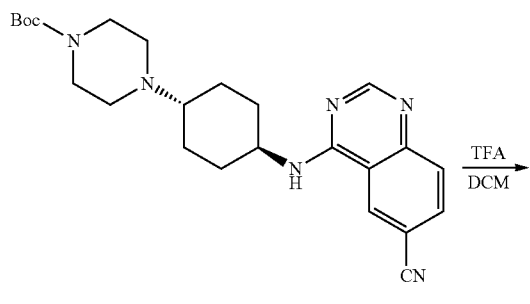

1684
-continued

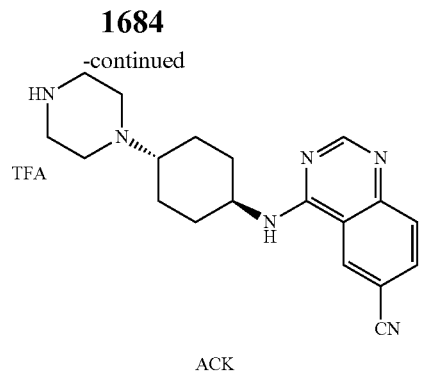

ACK

Step 1—Tert-butyl 4-[4-[(6-cyanoquinazolin-4-yl)amino]cyclohexyl]piperazine-1-carboxylate A mixture of tert-butyl 4-[4-[(6-bromoquinazolin-4-yl)amino]cyclohexyl]piperazine-1-carboxylate (100 mg, 203 umol) (Intermediate ACJ), Pd(PPh$_3$)$_4$ (23.5 mg, 20.3 umol) and Zn(CN)$_2$ (47.8 mg, 407 umol) in DMF (2 mL) was stirred at 100° C. for 16 hours. On completion, the reaction mixture was filtered and the filtrate was concentrated in vacuo. The residue was purified by reverse phase (0.1% TFA) to give the title compound (90.0 mg, 80% yield, TFA salt) as white solid. $^1$H NMR (400 MHz, DMSO-$d_6$) δ 9.01 (d, J=1.2 Hz, 1H), 8.75 (s, 1H), 8.21 (dd, J=1.2, 8.8 Hz, 1H), 7.85 (d, J=8.8 Hz, 1H), 4.34-4.20 (m, 1H), 4.16-3.99 (m, 2H), 3.55-3.42 (m, 2H), 3.41-3.30 (m, 1H), 3.17-2.99 (m, 4H), 2.53-2.51 (m, 1H), 2.21-2.10 (m, 4H), 1.73-1.48 (m, 4H), 1.43 (s, 9H).

Step 2—4-[(4-Piperazin-1-ylcyclohexyl)amino]quinazoline-6-carbonitrile

To a solution of tert-butyl 4-[4-[(6-cyanoquinazolin-4-yl)amino]cyclohexyl]piperazine-1-carboxylate (100 mg, 181 umol, TFA salt) in dichloromethane (1.5 mL) was added TFA (0.8 mL). The reaction mixture was stirred at 15° C. for 1 hour. On completion, the reaction mixture was concentrated in vacuo to give the title compound (81 mg, 99% yield, TFA salt) as yellow semisolid. LC-MS (ESI$^+$) m/z 337.2 (M+H)$^+$.

(S)-7-(2-(2-(2-aminoethoxy)ethoxy)ethoxy)-2-((S)-3,3-dimethyl-2-((S)-2-(methylamino)propanamido)butanoyl)-N—((R)-1,2,3,4-tetrahydronaphthalen-1-yl)-1,2,3,4-tetrahydroisoquinoline-3-carboxamide
(Intermediate ACL)
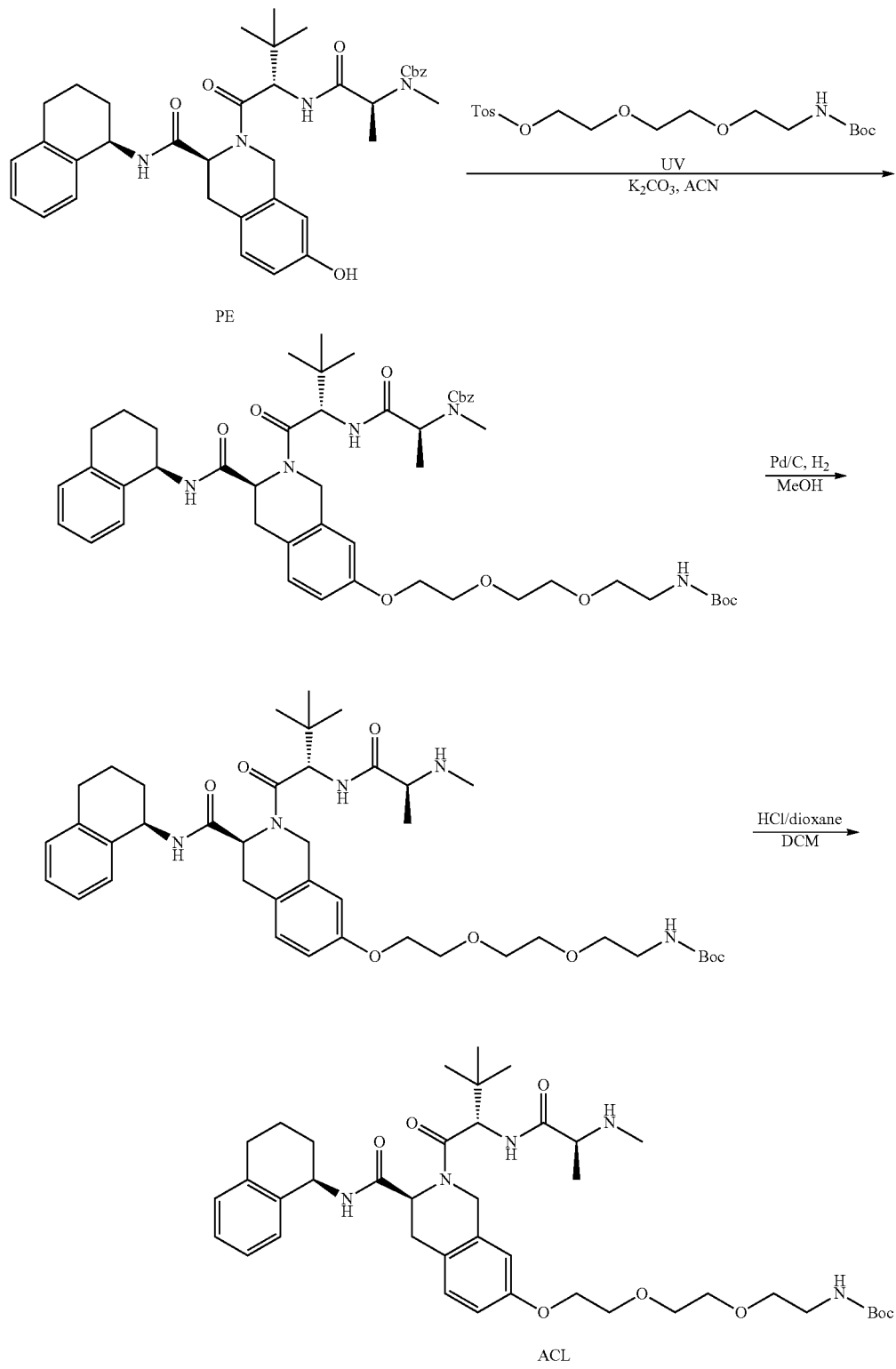

Step 1—benzyl ((S)-1-(((S)-1-((S)-7-((2,2-dimethyl-4-oxo-3,8,11-trioxa-5-azatridecan-13-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate To a solution of benzyl ((S)-1-(((S)-1-((S)-7-hydroxy-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (1.64 g, 2.51 mmol, Intermediate PE) in $CH_3CN$ (20 mL) was added 2,2-dimethyl-4-oxo-3,8,11-trioxa-5-azatridecan-13-yl 4-methylbenzenesulfonate (1.213 g, 3.01 mmoL, Intermediate UV), and $K_2CO_3$ (520 mg, 3.17 mmoL). The mixture was stirred at 82° C. overnight. The reaction mixture was then concentrated under reduced pressure and purified by silica gel chromatography eluted with PE/EA=1:1 to give the title compound (1.6 g, yield 72% yield) as a yellow oil. LC/MS (ESI, m/z): $[M+1]^+$=886.

Step 2—tert-butyl (2-(2-(2-(((S)-2-((S)-3,3-dimethyl-2-((S)-2-(methylamino)propanamido)butanoyl)-3-(((R)-1,2,3,4-tetrahydronaphthalen-1-yl)carbamoyl)-1,2,3,4-tetrahydroisoquinolin-7-yl)oxy)ethoxy)ethoxy)ethyl)carbamate To a solution of benzyl ((S)-1-(((S)-1-((S)-7-((2,2-dimethyl-4-oxo-3,8,11-trioxa-5-azatridecan-13-yl)oxy)-3-(((R)-1,2,3,4-tetrahydronaphthalen-1-yl)carbamoyl)-3,4-dihydroisoquinolin-2(1H)-yl)-3,3-dimethyl-1-oxobutan-2-yl)amino)-1-oxopropan-2-yl)(methyl)carbamate (300 mg, 0.34 mmol) in MeOH (20 mL) was added Pd/C (100 mg) at room temperature. The reaction mixture was degassed and purged with $H_2$ for three times. The reaction mixture was stirred under a $H_2$ balloon at rt overnight. The reaction mixture was then filtered and the filtrated was concentrated to give a residue. The residue was purified by column chromatography on silica gel to give the title compound (194.5 mg, 76% yield) as white solid. LC/MS (ESI, m/z): $[M+1]^+$=752.4. $^1H$ NMR (400 MHz, DMSO-$d_6$) δ 8.82-8.75 (m, 1H), 8.66-8.51 (m, 1H), 8.22-8.07 (m, 1H), 7.14-6.97 (m, 4H), 6.91-6.73 (m, 3H), 5.05-4.49 (m, 5H), 4.074-4.04 (m, 2H), 3.94-3.89 (m, 1H), 3.75-3.72 (m, 2H), 3.60-3.57 (m, 4H), 3.40-3.37 (m, 4H), 3.09-2.96 (m, 3H), 1.90-1.48 (m, 4H), 1.37 (s, 9H), 1.31-1.23 (m, 3H), 1.09-0.98 (m, 9H).

Step 3—(S)-7-(2-(2-(2-aminoethoxy)ethoxy)ethoxy)-2-((S)-3,3-dimethyl-2-((S)-2-(methylamino)propanamido)butanoyl)-N—((R)-1,2,3,4-tetrahydronaphthalen-1-yl)-1,2,3,4-tetrahydroisoquinoline-3-carboxamide To a solution of tert-butyl N-[2-[2-[2-[[(3S)-2-[(2S)-3,3-dimethyl-2-[[(2S)-2-(methylamino)propanoyl]amino]butanoyl]-3-[[(1R)-tetralin-1-yl]carbamoyl]-3,4-dihydro-1H-isoquinolin-7-yl]oxy]ethoxy]ethoxy]ethyl]carbamate (20.0 mg, 23.1 umol, TFA salt) in dichloromethane (1 mL) was added HCl/dioxane (4 M, 500 uL). The reaction mixture was stirred at 10° C. for 0.5 hour. On completion, the reaction mixture was concentrated in vacuo to give the title compound (16.0 mg, 100% yield, HCl salt) as white solid. LC-MS ($ESI^+$) m/z 652.5 $(M+H)^+$.

Tert-butyl N-[7-(methylamino)heptyl]carbamate (Intermediate ACM)

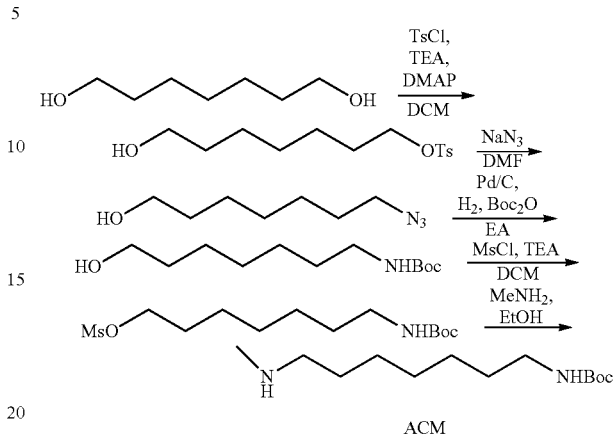

ACM

Step 1—7-Hydroxyheptyl 4-methylbenzenesulfonate

To a solution of heptane-1,7-diol (5.00 g, 37.8 mmol, CAS #629-30-1), DMAP (1.39 g, 11.3 mmol) and TEA (11.49 g, 113 mmol) in DCM (100 mL) was added p-TsCl (7.21 g, 37.8 mmol) at 10° C. The mixture was stirred at 10° C. for 16 hours. On completion, the mixture was concentrated in vacuo. The residue was purified by column chromatography on silica gel to give the title compound (4.10 g, 37% yield) as colorless gum. $^1H$ NMR (400 MHz, $CDCl_3$) δ 7.80 (d, J=8.4 Hz, 2H), 7.35 (d, J=8.4 Hz, 2H), 4.03 (t, J=6.4 Hz, 2H), 3.63 (t, J=6.4 Hz, 2H), 2.46 (s, 3H), 1.72-1.59 (m, 2H), 1.58-1.47 (m, 2H), 1.35-1.24 (m, 6H).

Step 2—7-Azidoheptan-1-ol

A mixture of 7-hydroxyheptyl 4-methylbenzenesulfonate (3.50 g, 12.2 mmol), $NaN_3$ (1.59 g, 24.4 mmol) and TBAI (450 mg, 1.22 mmol) in DMF (30 mL) was stirred at 60° C. for 16 hours under $N_2$. On completion, after cooling to 15° C., the mixture was diluted with water (100 mL), and extracted with EA (3×40 mL). The combined organic layer was concentrated in vacuo to give the title compound (1.92 g, 100% yield) EA solution (about 40 mL) as light yellow oil.

Step 3—Tert-butyl N-(7-hydroxyheptyl)carbamate

A mixture of 7-azidoheptan-1-ol (1.92 g, 12.2 mmol), Pd/C (400 mg, 10% wt) and $Boc_2O$ (2.93 g, 13.4 mmol) in EA (40 mL) was stirred at 25° C. for 16 hours under $H_2$ (50 Psi). On completion, the mixture was filtered and the cake was washed with EA (10 mL). The filtrate and washing were combined and concentrated in vacuo. The residue was purified by column chromatography on silica gel to give the title compound (1.90 g, 67% yield) as light yellow gum. $^1H$ NMR (400 MHz, DMSO-$d_6$) δ 6.74 (s, 1H), 4.31 (t, J=5.2 Hz, 1H), 3.41-3.33 (m, 2H), 2.89-2.84 (m, 2H), 1.44-1.39 (m, 2H), 1.37 (s, 9H), 1.34 (m, 2H), 1.24 (m, 6H).

Step 4—7-(Tert-butoxycarbonylamino)heptyl methanesulfonate

To a solution of tert-butyl N-(7-hydroxyheptyl)carbamate (1.90 g, 8.21 mmol) and TEA (1.66 g, 16.4 mmol) in DCM (30 mL) was added MsCl (1.41 g, 12.3 mmol) at 0° C. The mixture was stirred at 0-10° C. for 2 hours. On completion, the reaction was quenched with sat. aq. NH₄Cl (10 mL) and the mixture was partitioned. The organic layer was washed with brine (10 mL), dried over Na₂SO₄, filtered and concentrated in vacuo to give the title compound (2.54 g, 100% yield) as light yellow solid. ¹H NMR (400 MHz, DMSO-$d_6$) δ 6.75 (t, J=4.8 Hz, 1H), 4.17 (t, J=6.4 Hz, 2H), 3.15 (s, 3H), 2.91-2.86 (m, 2H), 1.69-1.60 (m, 2H), 1.37 (s, 9H), 1.36-1.16 (m, 8H).

Step 5—Tert-butyl N-[7-(methylamino)heptyl]carbamate

A solution of 7-(tert-butoxycarbonylamino)heptyl methanesulfonate (500 mg, 1.62 mmol) in MeNH₂ in EtOH (10 mL) solution was stirred at 70° C. for 16 hours. On completion, after cooling to 15° C., the mixture was concentrated in vacuo. The residue was diluted with a mixed solution (DCM:MeOH=10:1) (20 mL) and filtered. The filtrate was concentrated in vacuo to give the title compound (390 mg, 98% yield) as light yellow gum. ¹H NMR (400 MHz, DMSO-$d_6$) δ 6.77 (m, 1H), 2.92-2.85 (m, 2H), 2.81-2.77 (m, 2H), 2.34 (s, 3H), 1.58-1.48 (m, 2H), 1.36 (s, 9H), 1.35-1.30 (m, 2H), 1.25 (m, 6H).

N-[1-[4-[[7-aminoheptyl(methyl)amino]methyl]cyclohexyl]-3-(difluoromethyl)pyrazol-4-yl]-2-[2-(cyclopropylmethylamino)-4-pyridyl] oxazole-4-carboxamide (Intermediate ACN)

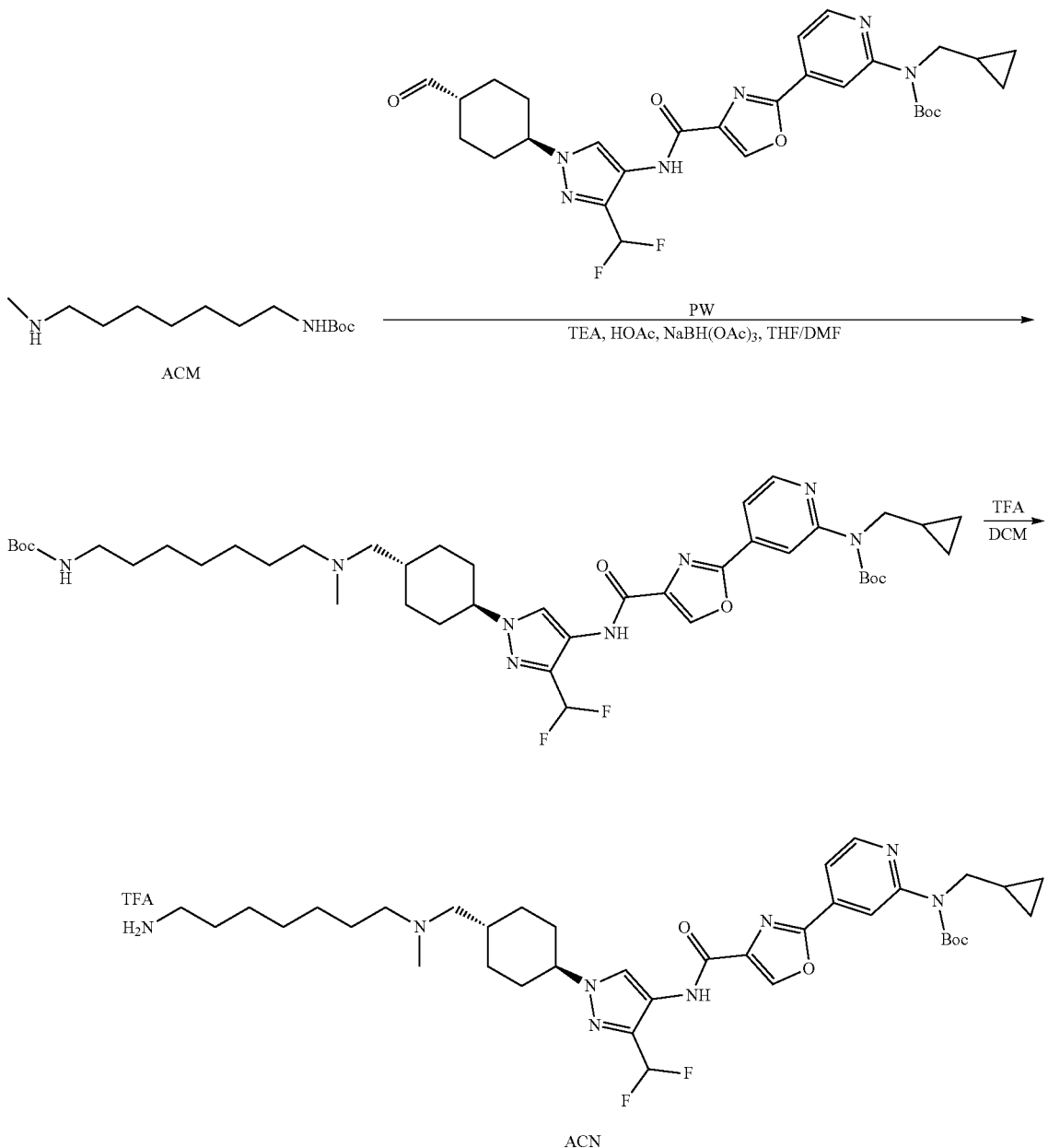

Step 1—Tert-butyl N-[4-[4-[[1-[4-[[7-(tert-butoxy-carbonylamino)heptyl-methyl-amino] methyl] cyclohexyl]-3-(difluoromethyl)pyrazol-4-yl]carbamoyl]oxazol-2-yl]-2-pyridyl]-N-(cyclopropylmethyl) carbamate To a solution of tert-butyl N-[7-(methylamino)heptyl] carbamate (30.0 mg, 122 umol, Intermediate ACM) in THF (1.50 mL) and DMF (0.50 mL) was added TEA at 0° C. until pH=8. To the mixture was added HOAc until pH=5-6 at 0° C. Then, to the mixture was added tert-butyl N-(cyclopropylmethyl)-N-[4-[4-[[3-(difluoromethyl)-1-(4-formylcyclohexyl)pyrazol-4-yl]carbamoyl]oxazol-2-yl]-2-pyridyl]carbamate (72.0 mg, 123 umol, Intermediate PW) at 0° C. The mixture was stirred at 0° C. for 0.5 hour. To the mixture was added NaBH(OAc)$_3$ (54.0 mg, 254 umol) at 0° C. The mixture was stirred at 0° C. for 1.5 hour. On completion, the reaction was quenched with water (0.2 mL). The mixture was concentrated in vacuo. The residue was purified by reversed phase flash (TFA condition) to give the title compound (38.0 mg, 38% yield) as white solid. $^1$H NMR (400 MHz, CDCl$_3$) δ 9.06 (s, 1H), 8.53 (d, J=5.2 Hz, 1H), 8.38 (s, 1H), 8.32 (d, J=5.6 Hz, 2H), 7.65-7.63 (m, 1H), 6.98-6.66 (m, 1H), 4.61-4.49 (m, 1H), 4.16-4.05 (m, 1H), 3.95 (d, J=6.8 Hz, 2H), 3.06-2.91 (m, 2H), 2.84-2.83 (m, 3H), 2.29-2.26 (m, 2H), 1.58 (s, 9H), 1.52-1.48 (m, 2H), 1.46 (s, 9H), 1.42-1.31 (m, 9H), 1.29-1.21 (m, 10H), 0.89-0.87 (m, 1H), 0.47-0.40 (m, 2H), 0.31-0.26 (m, 2H)

Step 2—N-[1-[4-[[7-aminoheptyl(methyl)amino] methyl]cyclohexyl]-3-(difluoromethyl)pyrazol-4-yl]-2-[2-(cyclopropylmethylamino)-4-pyridyl]oxazole-4-carboxamide To a solution of tert-butyl N-[4-[4-[[1-[4-[[7-(tert-butoxycarbonylamino) heptyl-methyl-amino] methyl] cyclohexyl]-3-(difluoromethyl)pyrazol-4-yl]carbamoyl]oxazol-2-yl]-2-pyridyl]-N-(cyclopropylmethyl)carbamate (35.0 mg, 43.0 umol) in DCM (1 mL) was added TFA (0.5 mL) at 15° C. The mixture was stirred at 15° C. for 1 hour. On completion, the mixture was concentrated in vacuo to give the title compound (31 mg, 99% yield, TFA salt) as light yellow solid. LC-MS (ESI$^+$) m/z 613.4 (M+H)$^+$

4-[[tert-butoxycarbonyl-[[4-[1-(cyclopropylmethyl) indazol-5-yl] phenyl] methyl]amino] methyl] benzoic acid (Intermediate ACO)

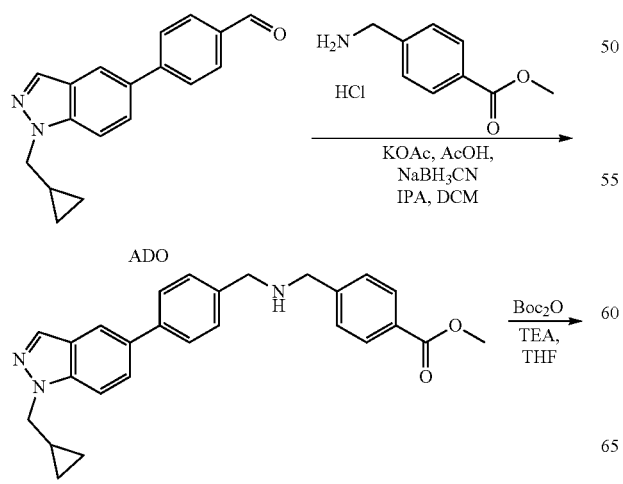

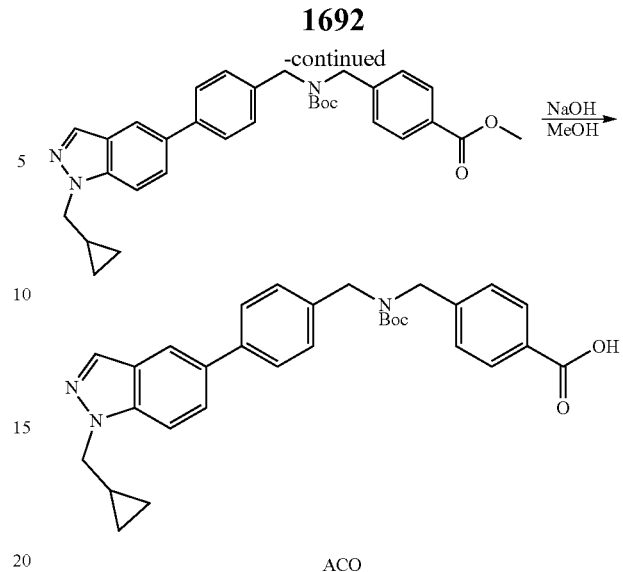

ACO

Step 1: methyl 4-[[[4-[1-(cyclopropylmethyl) indazol-5-yl]phenyl] methylamino]methyl] benzoate A mixture of 4-[1-(cyclopropylmethyl) indazol-5-yl]benzaldehyde (0.7 g, 2.53 mmol, Intermediate ADO), methyl 4-(aminomethyl)benzoate; hydrochloride (510 mg, 2.53 mmol), CH$_3$COOH (760 mg, 12.6 mmol), KOAc (994 mg, 10.1 mmol) and NaBH$_3$CN (477 mg, 7.60 mmol) in IPA (3.5 mL) and DCM (3.5 mL) was degassed and purged with N$_2$ three times and then the mixture was stirred at 25° C. for 12 hrs under N$_2$ atmosphere. The reaction mixture was quenched with H$_2$O (10 mL) at 0° C., and then filtered and concentrated under reduced pressure to give the title compound (1.0 g, crude) as a yellow solid. LC-MS (ESI$^+$) m/z 426.1 (M+H)$^+$.

Step 2: methyl 4-[[tert-butoxycarbonyl-[[4-[1-(cyclopropylmethyl) indazol-5-yl]phenyl] methyl] amino] methyl]benzoate A mixture of methyl 4-[[[4-[1-(cyclopropylmethyl) indazol-5-yl]phenyl]methylamino] methyl] benzoate (2 g, 4.70 mmol), tert-butoxycarbonyl tert-butyl carbonate (1.23 g, 5.64 mmol), and TEA (475 mg, 4.70 mmol) in THF (40 mL) was degassed and purged with N$_2$ three times, and then the mixture was stirred at 25° C. for 12 hrs under N$_2$ atmosphere. The reaction mixture was filtered and concentrated under reduced pressure to give a residue. The residue was purified by column chromatography (SiO$_2$, Petroleum ether/Ethyl acetate=20:0 to 10:1) to give the title compound (1.3 g, 58% yield) as a yellow solid. LC-MS (ESI$^+$) m/z 526.3 (M+H)$^+$.

Step 3: 4-[[tert-butoxycarbonyl-[[4-[1-(cyclopropylmethyl) indazol-5-yl] phenyl]methyl]amino]methyl] benzoic acid A mixture of methyl 4-[[tert-butoxycarbonyl-[[4-[1-(cyclopropylmethyl) indazol-5-yl]phenyl]methyl]amino] methyl]benzoate (1.8 g, 3.42 mmol), NaOH (2 M, 8.56 mL) in MeOH (20 mL) was degassed and purged with N$_2$ three times, and then the mixture was stirred at 25° C. for 12 hrs under N$_2$ atmosphere. The reaction mixture was filtered and concentrated under reduced pressure to give a residue. The residue was purified by prep-HPLC (column: Phenomenex Synergi Max-RP 150*50 mm*10 um; mobile phase: [water (0.225% FA)-ACN]; B %: 60%-90%,10 min) to give the title compound (450 mg, 23% yield, FA) as a white solid. LC-MS (ESI$^+$) m/z 510.3 (M+H)$^+$. 1H NMR (400 MHz, DMSO-d$_6$) δ=8.10 (s, 1H), 7.99 (s, 1H), 7.93 (d, J=7.6 Hz, 2H), 7.76 (d, J=8.4 Hz, 1H), 7.67 (d, J=7.6 Hz, 3H), 7.33 (s, 4H), 4.45 (d, J=13.6 Hz, 4H), 4.32 (d, J=6.4 Hz, 2H), 1.39 (s, 9H), 1.29 (d, J=4.4 Hz, 1H), 0.48 (d, J=7.2 Hz, 2H), 0.40 (d, J=3.3 Hz, 2H).

5-(4-(tert-butoxycarbonyl)piperazin-1-yl)pyrazolo[1,5-a]pyrimidine-3-carboxylic acid (Intermediate ACP)

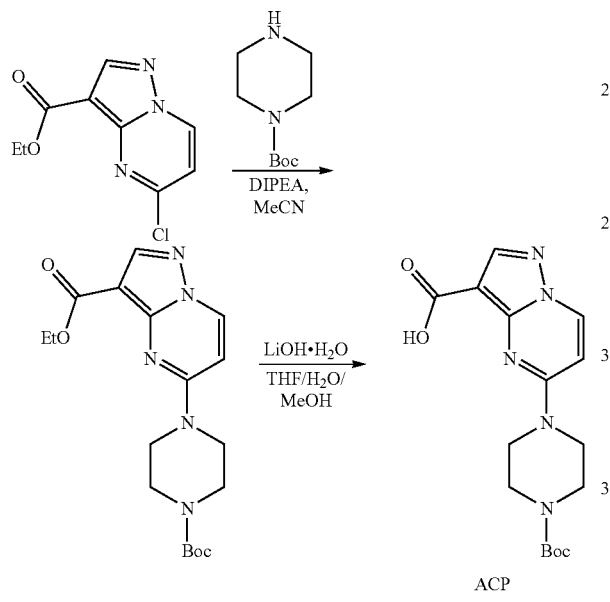

Step 1—Ethyl 5-(4-tert-butoxycarbonylpiperazin-1-yl)pyrazolo[1,5-a]pyrimidine-3-carboxylate To a mixture of ethyl 5-chloropyrazolo[1,5-a]pyrimidine-3-carboxylate (1.60 g, 7.09 mmol, CAS #1224944-77-7) and tert-butyl piperazine-1-carboxylate (2.37 g, 10.6 mmol) in MeCN (10 mL) was added DIPEA (1.83 g, 14.2 mmol, 2.47 mL) at 25° C. The mixture was stirred at 80° C. for 5 hours. On completion, the reaction mixture was concentrated in vacuo to remove MeCN. The residue was then diluted with water (30 mL) and extracted with EA (3×20 mL). The combined organic layers were washed with 100 mL brine, dried over Na$_2$SO$_4$, filtered and concentrated in vacuo to give a residue. The residue was purified by column chromatography (SiO$_2$, Petroleum ether/Ethyl acetate=3/1) to give the title compound (2.60 g, 97% yield) as white solid. $^1$H NMR (400 MHz, CDCl$_3$) δ 8.33-8.25 (m, 2H), 6.41 (d, J=7.8 Hz, 1H), 4.34 (d, J=7.2 Hz, 2H), 3.79 (s, 4H), 3.61-3.51 (m, 4H), 1.48 (s, 9H), 1.38 (s, 3H). LC-MS (ESI$^+$) m/z 376.1 (M+H)$^+$.

Step 2—5-(4-(tert-butoxycarbonyl)piperazin-1-yl)pyrazolo[1,5-a]pyrimidine-3-carboxylic acid To a mixture of ethyl 5-(4-tert-butoxycarbonylpiperazin-1-yl)pyrazolo[1,5-a]pyrimidine-3-carboxylate (2.00 g, 5.33 mmol) in THF (20 mL), H$_2$O (5 mL) and MeOH (5 mL) was added LiOH·H$_2$O (670 mg, 15.9 mmol) in one portion at 25° C. The mixture was stirred at 50° C. for 2 hours. On completion, the reaction mixture was concentrated in vacuo to remove solvent. The residue was diluted with water (10 mL) and then added HCl (1N) to adjust the pH=2.0. A white solid was appeared. The mixture was filtered, and the filter cake was collected, washed with water (10 mL) and then dried in vacuo to give the title compound (1.50 g, 81% yield) as a white solid. $^1$H NMR (400 MHz, DMSO-d$_6$) δ 12.10 (s, 1H), 8.73 (d, J=8.0 Hz, 1H), 8.19 (s, 1H), 6.82 (d, J=8.0 Hz, 1H), 3.75 (s, 4H), 3.45 (s, 4H), 1.42 (s, 9H).

4-[4-[[5-(4-Tert-butoxycarbonylpiperazin-1-yl)pyrazolo[1,5-a]pyrimidine-3-carbonyl]amino]-3-(difluoromethyl)pyrazol-1-yl]cyclohexanecarboxylic acid (Intermediate ACO)

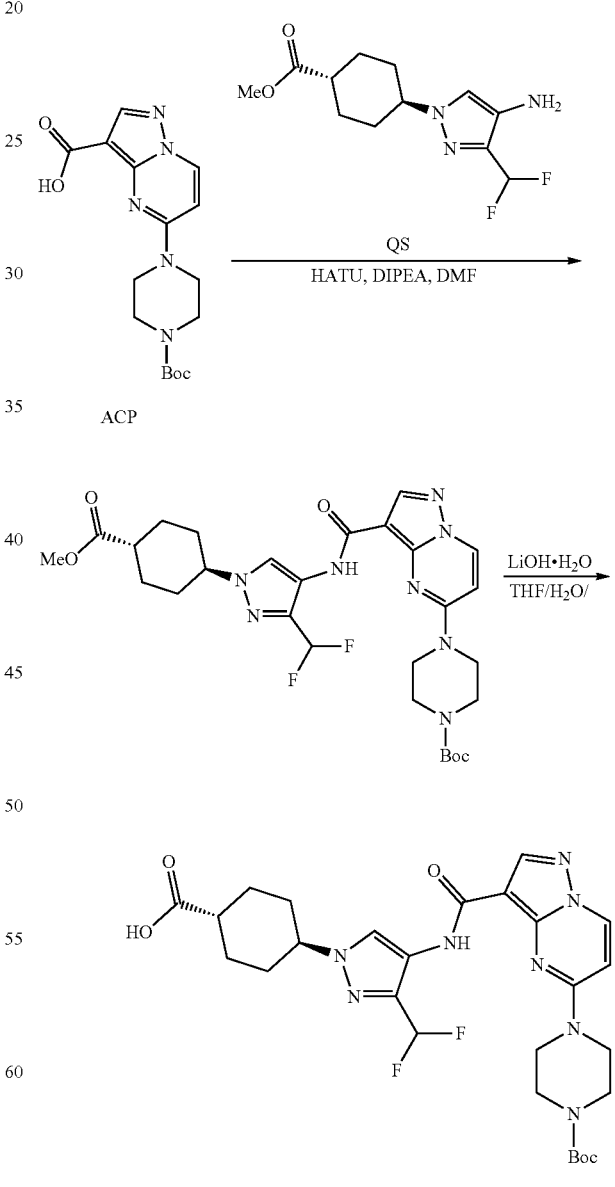

Step 1—Tert-butyl 4-[3-[[3-(difluoromethyl)-1-(4-methoxycarbonylcyclohexyl)pyrazol-4-yl] carbamoyl]pyrazolo[1,5-a]pyrimidin-5-yl]piperazine-1-carboxylate To a solution of 5-(4-tert-butoxycarbonylpiperazin-1-yl)pyrazolo[1,5-a]pyrimidine-3-carboxylic acid (500 mg, 1.44 mmol, Intermediate ACP) and methyl 4-[4-amino-3-(difluoromethyl)pyrazol-1-yl]cyclohexanecarboxylate (393 mg, 1.44 mmol, Intermediate QS) in DMF (5 mL) was added HATU (656 mg, 1.73 mmol) and DIPEA (558 mg, 4.32 mmol, 752 uL) at 25° C. The mixture was stirred at 70° C. for 16 hours. On completion, the reaction mixture was quenched by water (0.5 mL) at 25° C., and then diluted with EA (15 mL) and extracted with EA (3×20 mL). The combined organic layers were dried over Na$_2$SO$_4$, filtered and concentrated in vacuo to give a residue. The residue was purified by prep-HPLC (column: Phenomenex Luna C18 150*40 mm, 10 um; mobile phase: [water (0.225% FA)-ACN]; B %: 46%-76%, 8.5 min) to give the title compound (520 mg, 60% yield) as a white solid. $^1$H NMR (400 MHz, DMSO-d$_6$) δ 9.38 (s, 1H), 8.95-8.70 (m, 1H), 8.39 (s, 1H), 8.28 (s, 1H), 7.14 (s, 1H), 6.93-6.81 (m, 1H), 4.32-4.18 (m, 1H), 3.90-3.70 (m, 4H), 3.67-3.57 (m, 3H), 3.56-3.39 (m, 4H), 2.47-2.38 (m, 1H), 2.05 (d, J=1.8 Hz, 4H), 1.87-1.73 (m, 2H), 1.61-1.47 (m, 2H), 1.44 (s, 9H). LC-MS (ESI$^+$) m/z 603.4 (M+H)$^+$.

Step 2—4-[4-[[5-(4-Tert-butoxycarbonylpiperazin-1-yl)pyrazolo[1,5-a]pyrimidine-3-carbonyl]amino]-3-(difluoromethyl)pyrazol-1-yl]cyclohexanecarboxylic acid To a mixture of tert-butyl 4-[3-[[3-(difluoromethyl)-1-(4-methoxycarbonylcyclohexyl)pyrazol-4-yl] carbamoyl]pyrazolo[1,5-a]pyrimidin-5-yl]piperazine-1-carboxylate (460 mg, 763 umol) in THF (4 mL) and H$_2$O (1 mL) was added LiOH·H$_2$O (96.1 mg, 2.29 mmol) at 25° C. The mixture was stirred at 25° C. for 3 hours. On completion, the reaction mixture was concentrated in vacuo to remove THF. The residue was diluted with water (15 mL) and adjusted to the pH=1 with HCl (1 N). A large amount of white solid appeared, the mixture was filtered and the filter cake was collected and dry in vacuo to give the title compound (440 mg, 98% yield) as a white solid. $^1$H NMR (400 MHz, DMSO-d$_6$) δ 12.14 (s, 1H), 9.45-9.31 (m, 1H), 8.87-8.75 (m, 1H), 8.44-8.34 (m, 1H), 8.28 (s, 1H), 7.15 (t, J=53.6 Hz, 1H), 6.89 (d, J=8.0 Hz, 1H), 4.24 (s, 1H), 3.81 (s, 4H), 3.48 (d, J=4.6 Hz, 4H), 2.36-2.24 (m, 1H), 2.06 (d, J=9.4 Hz, 4H), 1.86-1.72 (m, 2H), 1.52 (d, J=12.4 Hz, 2H), 1.44 (s, 9H); LC-MS (ESI$^+$) m/z 589.2 (M+H)$^+$.

N,N-dibenzyl-2-fluoro-3-prop-2-ynoxy-propan-1-amine (Intermediate ACR)

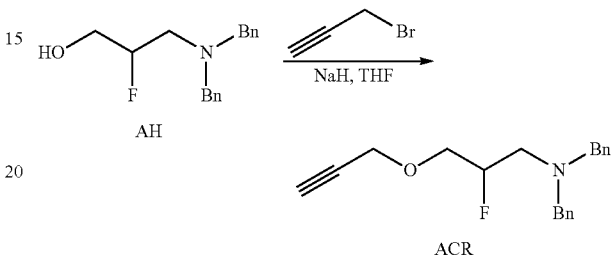

To a mixture of 3-(dibenzylamino)-2-fluoro-propan-1-ol (2.00 g, 7.32 mmol, Intermediate AH) and 3-bromoprop-1-yne (1.20 g, 8.05 mmol) in THF (30 mL) was added NaH (438 mg, 10.9 mmol, 60% dispersion in mineral oil) at 25° C. The mixture was stirred at 25° C. for 16 hours. On completion, the reaction mixture was quenched with water (15 mL) at 25° C., and then extracted with EA (3×20 mL). The combined organic layers were dried over Na$_2$SO$_4$, filtered and concentrated in vacuo to give a residue. The crude product was purified by column chromatography (SiO$_2$, Petroleum ether/Ethyl acetate=100/1 to 30/1) to afford the title compound (1.95 g, 85% yield) as yellow oil. $^1$H NMR (400 MHz, CDCl$_3$) δ 7.43-7.25 (m, 10H), 4.89-4.68 (m, 1H), 4.23-4.10 (m, 2H), 3.70 (s, 6H), 2.86-2.72 (m, 2H), 2.45 (s, 1H). LC-MS (ESI$^+$) m/z 312.2 (M+H)$^+$.

3-[4-[3-(3-Amino-2-fluoro-propoxy)propyl]-3-methyl-2-oxo-benzimidazol-1-yl]piperidine-2,6-dione (Intermediate ACS)

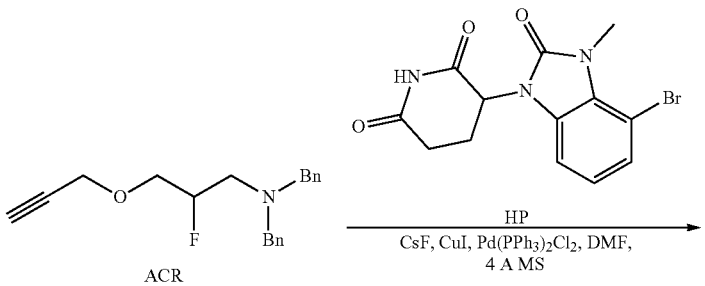

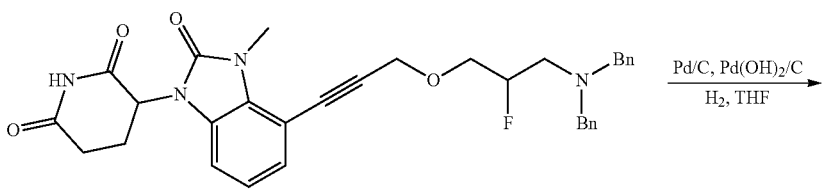

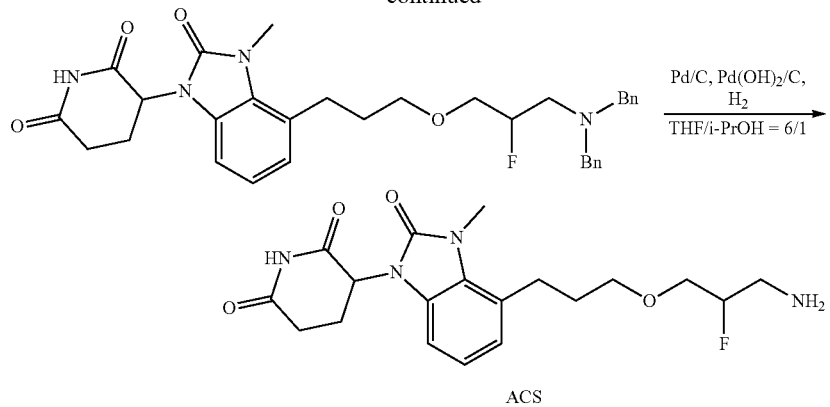

Step 1—3-[4-[3-[3-(Dibenzylamino)-2-fluoro-propoxy]prop-1-ynyl]-3-methyl-2-oxo-benzimidazol-1-yl]piperidine-2,6-dione To a mixture of 3-(4-bromo-3-methyl-2-oxo-benzimidazol-1-yl)piperidine-2,6-dione (500 mg, 1.48 mmol, Intermediate HP) and N,N-dibenzyl-2-fluoro-3-prop-2-ynoxy-propan-1-amine (690.64 mg, 2.22 mmol, 1.5 eq, Intermediate ACR) in DMF (10 mL) was added Pd(PPh$_3$)$_2$Cl$_2$ (103 mg, 147 umol), CuI (28.2 mg, 147 umol), CsF (1.12 g, 7.39 mmol) and 4 Å molecular sieves (100 mg) in one portion at 25° C. under N$_2$. The mixture was stirred at 80° C. for 2 hours. On completion, the reaction mixture was quenched with water (0.5 mL) at 25° C., then diluted with water (10 mL) and extracted with EA (3×40 mL). The combined organic layers were dried over Na$_2$SO$_4$, filtered and concentrated in vacuo to give a residue. The residue was purified by column chromatography (SiO$_2$, Petroleum ether/Ethyl acetate=10/1 to 1/1) to give the title compound (728 mg, 78% yield, 90% purity) as a yellow solid. $^1$H NMR (400 MHz, DMSO-d$_6$) δ 11.12 (s, 1H), 7.35-7.23 (m, 9H), 7.22-7.16 (m, 3H), 7.13-7.08 (m, 1H), 7.07-7.01 (m, 1H), 5.50-5.34 (m, 1H), 4.96-4.76 (m, 1H), 4.47-4.39 (m, 2H), 3.76-3.64 (m, 2H), 3.63 (s, 4H), 3.56 (s, 3H), 2.89 (s, 1H), 2.73 (s, 5H), 2.08-2.00 (m, 1H); LC-MS (ESI$^+$) m/z 569.3 (M+H)$^+$.

Step 2—Tert-butyl 4-[3-[[3-(difluoromethyl)-1-(4-methoxycarbonylcyclohexyl)pyrazol-4-yl]carbamoyl]pyrazolo[1,5-a]pyrimidin-5-yl]piperazine-1-carboxylate To a solution of 3-[4-[3-[3-(dibenzylamino)-2-fluoro-propoxy]prop-1-ynyl]-3-methyl-2-oxo-benzimidazol-1-yl]piperidine-2,6-dione (300 mg, 527 umol) in THF (3 mL) was added Pd/C (50.0 mg, 10% wt) and Pd(OH)$_2$/C (50 mg, 10% wt) under N$_2$. The suspension was degassed under vacuum and purged with H$_2$ three times. The mixture was stirred under H$_2$ (15 psi) at 25° C. for 18 hours. On completion, the mixture was filtered, and the filtrate was concentrated in vacuo to give a residue. The residue was purified by reverse phase (TFA condition) to give the title compound (266 mg, 88% yield) as yellow oil. LC-MS (ESI$^+$) m/z 573.4 (M+H)$^+$.

Step 3—3-[4-[3-(3-Amino-2-fluoro-propoxy)propyl]-3-methyl-2-oxo-benzimidazol-1-yl]piperidine-2,6-dione To a solution of 3-[4-[3-[3-(dibenzylamino)-2-fluoro-propoxy]propyl]-3-methyl-2-oxo-benzimidazol-1-yl] piperidine-2,6-dione (250 mg, 436 umol) in i-PrOH (6 mL) and THF (1 mL) was added Pd/C (50.0 mg, 10% wt) and Pd(OH)$_2$/C (50.0 mg, 10% wt) under N$_2$. The suspension was degassed under vacuum and purged with H$_2$ three times. The mixture was stirred under H$_2$ (15 psi) at 25° C. for 18 hours. On completion, the mixture was filtered and the filtrate was concentrated in vacuo to give the title compound (120 mg, 70% yield) as white solid. LC-MS (ESI$^+$) m/z 393.2 (M+H)$^+$.

Tert-butyl N-[2-[2-[2-(methylamino)ethoxy]ethoxy]ethyl]carbamate (Intermediate ACT)

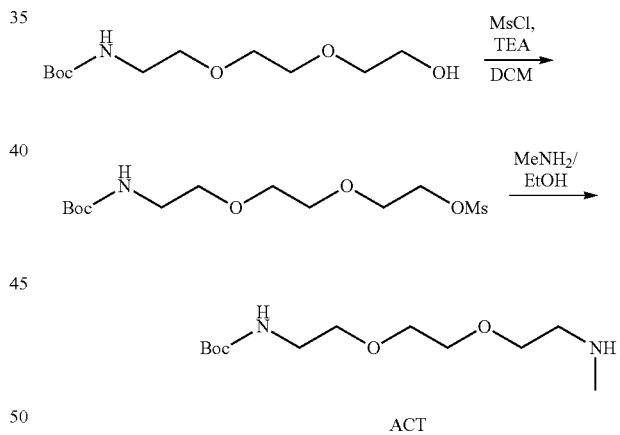

Step 1—2-[2-[2-(Tert-butoxycarbonylamino)ethoxy]ethoxy]ethyl methanesulfonate To a solution of tert-butyl N-[2-[2-(2-hydroxyethoxy)ethoxy]ethyl]carbamate (1.00 g, 4.01 mmol, CAS #139115-92-7) and TEA (608 mg, 6.02 mmol) in dichloromethane (10 mL) was added MsCl (551 mg, 4.81 mmol). The reaction mixture was stirred at 0-15° C. for 1 hour. On completion, the reaction mixture was diluted with water (20 mL) and extracted with dichloromethane (3×30 mL). The combined organic layers were washed with brine (3×30 mL), dried over Na$_2$SO$_4$, filtered and concentrated in vacuo to give the title compound (1.30 g, 98% yield) as yellow oil, which was used in the next step directly.

Step 2—Tert-butyl N-[2-[2-[2-(methylamino)ethoxy]ethoxy]ethyl]carbamate

A mixture of 2-[2-[2-(tert-butoxycarbonylamino)ethoxy]ethoxy]ethyl methanesulfonate (1.30 g, 3.97 mmol) and MeNH₂/EtOH (3.97 mmol, 10 mL, 30% solution) was stirred at 75° C. for 16 hours in a sealed tube. On completion, the reaction mixture was concentrated in vacuo. The residue was purified by silica gel chromatography (ethyl acetate:ethanol=3:1) to give the title compound (1.60 g, 84% yield) as yellow semisolid. ¹H NMR (400 MHz, DMSO-d₆) δ 6.83-6.72 (m, 1H), 3.69-3.62 (m, 2H), 3.60-3.49 (m, 4H), 3.38 (t, J=6.0 Hz, 2H), 3.16 (d, J=5.2 Hz, 3H), 3.12-3.03 (m, 4H), 1.37 (s, 9H).

N-[1-[4-[[2-[2-(2-aminoethoxy)ethoxy]ethyl-methyl-amino]methyl]cyclohexyl]-3-(difluoromethyl)pyrazol-4-yl]-2-[2-(cyclopropylmethylamino)-4-pyridyl]oxazole-4-carboxamide (Intermediate ACU)

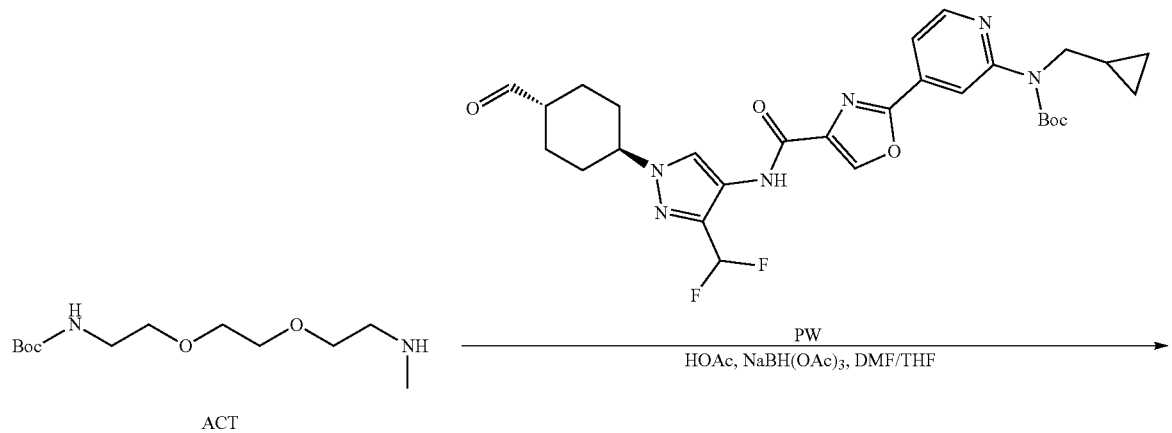

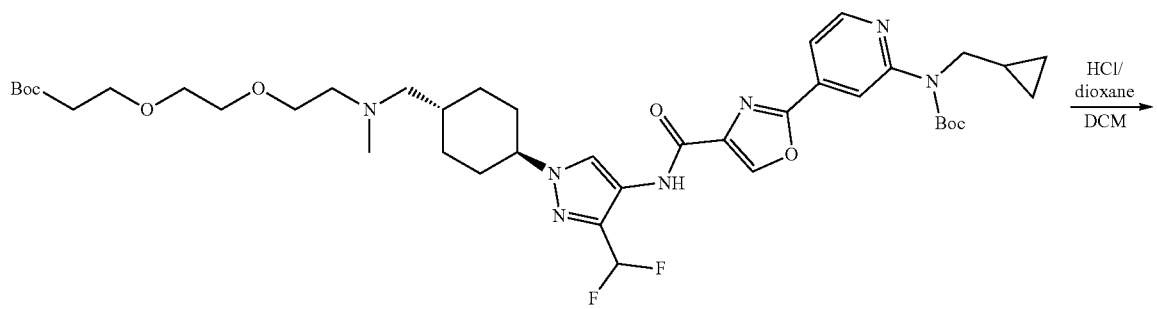

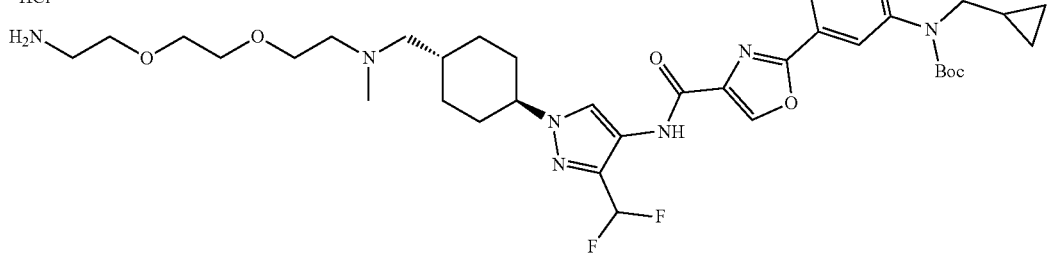

Step 1—Tert-butyl N-[4-[4-[[1-[4-[[2-[2-[2-(tert-butoxycarbonylamino)ethoxy]ethoxy]ethyl-methyl-amino]methyl]cyclohexyl]-3-(difluoromethyl)pyrazol-4-yl]carbamoyl]oxazol-2-yl]-2-pyridyl]-N-(cyclopropylmethyl)carbamate To a solution of tert-butyl N-[2-[2-[2-(methylamino)ethoxy]ethoxy]ethyl]carbamate (163 mg, 342 umol, Intermediate ACT) in DMF (1.5 mL) was added TEA until the pH=7-8, then the mixture was acidified with AcOH until the pH=5-6. A solution of tert-butyl N-(cyclopropylmethyl)-N-[4-[4-[[3-(difluoromethyl)-1-(4-formylcyclohexyl) pyrazol-4-yl]carbamoyl]oxazol-2-yl]-2-pyridyl]carbamate (200 mg, 342 umol, Intermediate PW) in THF (3 mL) was next added to the mixture at 0° C. The reaction mixture was stirred at 0° C. for 0.5 hour, then NaBH(OAc)$_3$ (145 mg, 684 umol) was added. The reaction mixture was stirred at 0-10° C. for 2 hours. On completion, the reaction mixture was quenched with water (0.2 mL), filtered and concentrated in vacuo. The residue was purified by reverse phase (0.1% FA) to give the title compound (140 mg, 46% yield, FA salt) as white solid. $^1$H NMR (400 MHz, CDCl$_3$) δ 9.06 (s, 1H), 8.52 (d, J=5.6 Hz, 1H), 8.37 (s, 1H), 8.32 (d, J=5.2 Hz, 2H), 7.63 (dd, J=1.2, 5.2 Hz, 1H), 6.99-6.66 (m, 1H), 5.13-4.99 (m, 1H), 4.17-4.03 (m, 1H), 3.95 (d, J=6.8 Hz, 2H), 3.69 (t, J=5.6 Hz, 2H), 3.62 (s, 4H), 3.55 (t, J=5.2 Hz, 2H), 3.33 (d, J=4.8 Hz, 2H), 2.79 (t, J=5.6 Hz, 2H), 2.44 (s, 3H), 2.23 (d, J=10.8 Hz, 2H), 2.06 (d, J=12.4 Hz, 2H), 1.81 (dq, J=3.2, 12.8 Hz, 2H), 1.71-1.62 (m, 1H), 1.57 (s, 9H), 1.45 (s, 9H), 1.32-1.18 (m, 2H), 1.14 (br d, J=14.0 Hz, 2H), 0.89-0.84 (m, 1H), 0.49-0.37 (m, 2H), 0.32-0.23 (m, 2H).

Step 2—N-[1-[4-[[2-[2-(2-aminoethoxy)ethoxy]ethyl-methyl-amino]methyl]cyclohexyl]-3-(difluoromethyl)pyrazol-4-yl]-2-[2-(cyclopropylmethyl-amino)-4-pyridyl]oxazole-4-carboxamide To a solution of tert-butyl N-[4-[4-[[1-[4-[[2-[2-[2-(tert-butoxycarbonylamino)ethoxy]ethoxy]ethyl-methyl-amino]methyl]cyclohexyl]-3-(difluoromethyl)pyrazol-4-yl]carbamoyl]oxazol-2-yl]-2-pyridyl]-N-(cyclopropylmethyl) carbamate (130 mg, 148 umol, FA salt) in dichloromethane (2 mL) was added HCl/dioxane (4 M, 2 mL). The reaction mixture was stirred at 15° C. for 0.5 hour. On completion, the reaction mixture was concentrated in vacuo to give the title compound (98.0 mg, 99% yield, HCl salt) as off-white solid. LC-MS (ESI$^+$) m/z 631.4 (M+H)$^+$.

3-[4-[2-(2,7-Diazaspiro[3.5]nonan-2-yl)ethyl]-3-methyl-2-oxo-benzimidazol-1-yl]piperidine-2,6-dione (Intermediate ACV)

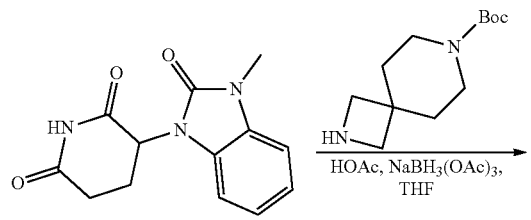

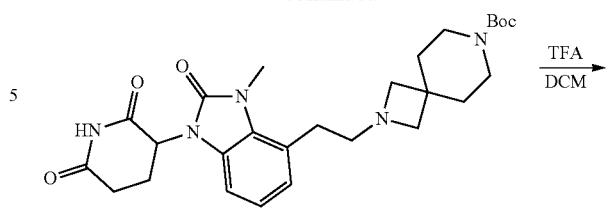

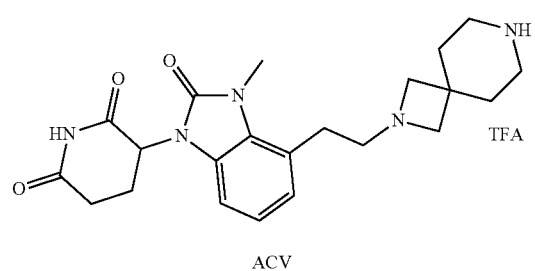

Step 1—Tert-butyl 2-[2-[1-(2,6-dioxo-3-piperidyl)-3-methyl-2-oxo-benzimidazol-4-yl]ethyl]-2,7-diazaspiro[3.5]nonane-7-carboxylate To a mixture of 2-[1-(2,6-dioxo-3-piperidyl)-3-methyl-2-oxo-benzimidazol-4-yl]acetaldehyde (200 mg, 663 umol, synthesized via Step 1 of Intermediate AAP) and tert-butyl 2,7-diazaspiro[3.5]nonane-7-carboxylate (187 mg, 663 umol, CAS #896464-16-7) in THF (5 mL) was added HOAc (39.8 mg, 663 umol) in one portion at 25° C. The mixture was stirred at 25° C. for 0.5 hour. Then NaBH(OAc)$_3$ (281 mg, 1.33 mmol) was added to the mixture. The mixture was stirred at 25° C. for 1.5 hours. On completion, the reaction mixture was quenched with water (0.5 mL) at 25° C., and then concentrated in vacuo to give a residue. The residue was purified by prep-HPLC (column: Shim-pack C18 150*25*10 um; mobile phase: [water (0.225% FA)-ACN]; B %: 6%-36%, 10 min) to give the title compound (35.0 mg, 10% yield) as a white solid. LC-MS (ESI$^+$) m/z 512.4 (M+H)$^+$.

Step 2—3-[4-[2-(2,7-Diazaspiro[3.5]nonan-2-yl)ethyl]-3-methyl-2-oxo-benzimidazol-1-yl]piperidine-2,6-dione To a mixture of tert-butyl 2-[2-[1-(2,6-dioxo-3-piperidyl)-3-methyl-2-oxo-benzimidazol-4-yl] ethyl]-2,7-diazaspiro[3.5]nonane-7-carboxylate (15.0 mg, 29.3 umol) in DCM (3 mL) was added TFA (3.00 mL) at 25° C. The mixture was stirred at 25° C. for 2 hours. On completion, the reaction mixture was concentrated in vacuo to give the title compound (15.0 mg, 97% yield, FA salt) as yellow solid. LC-MS (ESI$^+$) m/z 412.3 (M+H)$^+$.

2-[2-(Cyclopropylmethylamino)-4-pyridyl]-N-[3-(difluoromethyl)-1-[4-[[methyl-[2-(4-piperidyl)ethyl]amino]methyl] cyclohexyl]pyrazol-4-yl] oxazole-4-carboxamide (Intermediate ACW)

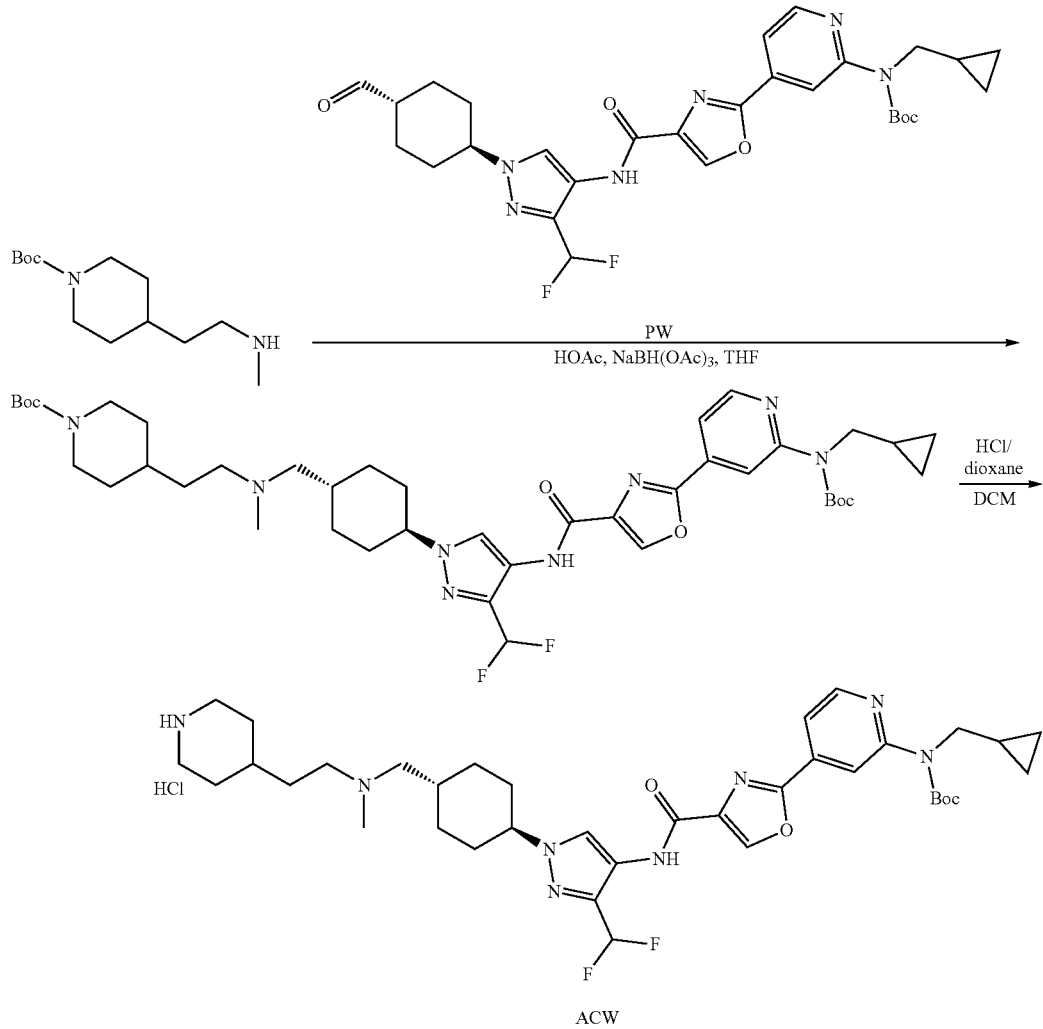

ACW

Step 1—Tert-butyl 4-[2-[[4-[4-[[2-[2-[tert-butoxycarbonyl(cyclopropylmethyl)amino]-4-pyridyl] oxazole-4-carbonyl]amino]-3-(difluoromethyl)pyrazol-1-yl] cyclohexyl]methyl-methyl-amino] ethyl] piperidine-1-carboxylate To a solution of tert-butyl 4-[2-(methylamino)ethyl]piperidine-1-carboxylate (80.0 mg, 330 umol, CAS #896103-62-1) in THF (10 mL) was added HOAc (19.8 mg, 330 umol) and tert-butylN-(cyclopropylmethyl)-N-[4-[4-[[3-(difluoromethyl)-1-(4-formylcyclohexyl)pyrazol-4-yl] carbamoyl]oxazol-2-yl]-2-pyridyl]carbamate (192 mg, 330 umol, Intermediate PW) at 25° C. The mixture was stirred at 25° C. for 30 minutes. Then, NaBH(OAc)₃ (139 mg, 660 umol) was added to the mixture at 0° C. The reaction mixture was stirred at 25° C. for 2 hours. On completion, was H₂O (1 mL) was added the reaction mixture and was concentrated in vacuo. The residue was purified by prep-HPLC (column: Phenomenex Synergi C18 150*25 mm*10 um; mobile phase: [water (0.225% FA)-ACN]; B %: 35%-65%, 11 min) to give the title compound (190 mg, 67% yield, FA salt) as a white solid. $^1$H NMR (400 MHz, DMSO-d₆) δ 9.75 (s, 1H), 9.00 (s, 1H), 8.59 (d, J=5.2 Hz, 1H), 8.29 (s, 1H), 8.19 (s, 1H), 7.68 (dd, J=1.2, 4.8 Hz, 1H), 7.32-6.99 (m, 1H), 4.26-4.16 (m, 1H), 3.91 (d, J=13.6 Hz, 2H), 3.86 (d, J=6.8 Hz, 2H), 2.66-2.55 (m, 1H), 2.53-2.51 (m, 2H), 2.45 (s, 2H), 2.29 (s, 1H), 2.24 (s, 3H), 2.09-2.01 (m, 2H), 1.89 (d, J=12.0 Hz, 2H), 1.83-1.71 (m, 2H), 1.62 (d, J=13.2 Hz, 3H), 1.51 (s, 9H), 1.48-1.44 (m, 1H), 1.41 (s, 1H), 1.38 (s, 9H), 1.36 (s, 1H), 1.23-1.12 (m, 1H), 1.12-0.93 (m, 4H), 0.46-0.35 (m, 2H), 0.30-0.18 (m, 2H); LC-MS (ESI⁺) m/z 811.5 (M+H)⁺.

Step 2—2-[2-(Cyclopropylmethylamino)-4-pyridyl]-N-[3-(difluoromethyl)-1-[4-[[methyl-[2-(4-piperidyl)ethyl]amino]methyl]cyclohexyl]pyrazol-4-yl]oxazole-4-carboxamide To a solution of tert-butyl 4-[2-[[4-[4-[[2-[2-[tert-butoxycarbonyl(cyclopropylmethyl)amino]-4-pyridyl] oxazole-4- carbonyl]amino]-3-(difluoromethyl)pyrazol-1-yl] cyclohexyl]methyl-methyl-amino] ethyl]piperidine-1-carboxylate (30.0 mg, 36.9 umol) in DCM (2 mL) was added HCl/dioxane (4 M, 1.5 mL). The mixture was stirred at 15° C. for 2 hours. On completion, the reaction mixture was concentrated in vacuo to give the title compound (23.0 mg, 96% yield, HCl salt) as a white solid. LC-MS (ESI$^+$) m/z 611.4 (M+H)$^+$.

2-[2-(Cyclopropylmethylamino)-4-pyridyl]-N-[3-(difluoromethyl)-1-[1-(4-piperidylmethyl)-4-piperidyl]pyrazol-4-yl]oxazole-4-carboxamide (Intermediate ACX)

tert-butyl 4-formylpiperidine-1-carboxylate (60.3 mg, 283 umol, CAS #137076-22-3) was added to the mixture. The mixture was stirred at 15° C. for 0.5 hour. NaBH(OAc)$_3$ (89.9 mg, 424 umol) was then added and the mixture was stirred at 15° C. for 6 hours. On completion, the mixture was concentrated and the residue was purified by reverse phase flash (0.1% FA condition) to give the title compound (230 mg, 70% yield) as a white solid. $^1$H NMR (400 MHz, DMSO-d$_6$) δ 9.69 (s, 1H), 8.91 (s, 1H), 8.19 (s, 1H), 8.15-8.13 (m, 1H), 7.30-7.09 (m, 1H), 7.06 (t, J=5.6 Hz, 1H), 7.02-6.99 (m, 1H), 4.25-4.18 (m, 1H), 3.95-3.87 (m, 2H), 3.19-3.15 (m, 2H), 2.91 (d, J=11.6 Hz, 2H), 2.15 (d, J=6.4 Hz, 2H), 2.08-1.89 (m, 6H), 1.72-1.63 (m, 3H),

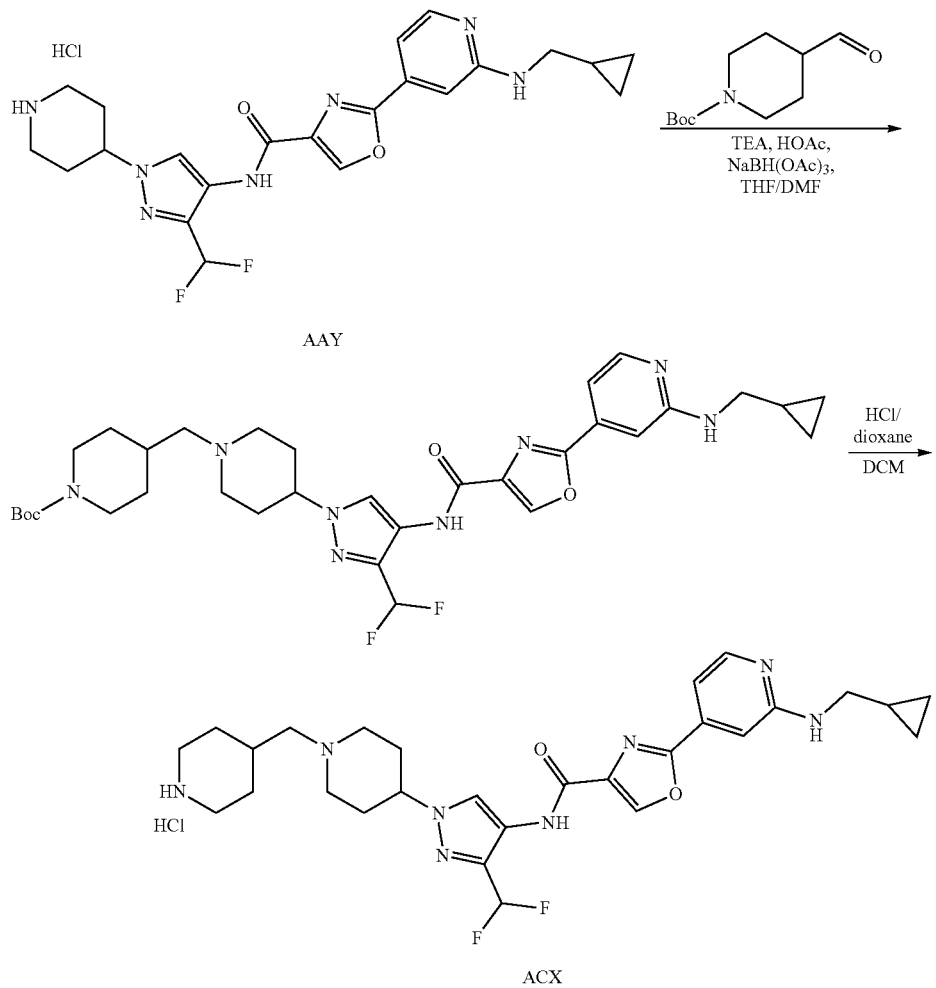

Step 1—Tert-butyl 4-[[4-[4-[4-[[22-(cyclopropylmethylamino)-4-pyridyl]oxazole-4-carbonyl]amino]-3-(difluoromethyl)pyrazol-1-yl]]-1-piperidyl]methyl]piperidine-1-carboxylate To a solution of 2-[2-(cyclopropylmethylamino)-4-pyridyl]-N-[3-(difluoromethyl)-1-(4-piperidyl) pyrazol-4-yl]oxazole-4-carboxamide (150 mg, 283 umol, 2HCl salt, Intermediate AAY) in THF (3 mL) and DMF (3 mL) was added Et$_3$N (28.6 mg, 283 umol). The mixture was stirred at 15° C. for 0.5 hour. HOAc (33.9 mg, 565 umol) and 1.10-1.01 (m, 1H), 0.99-0.88 (m, 2H), 0.47-0.41 (m, 2H), 0.24-0.19 (m, 2H); LC-MS (ESI$^+$) m/z 655.4 (M+H)$^+$.

Step 2—2-[2-(Cyclopropylmethylamino)-4-pyridyl]-N-[3-(difluoromethyl)-1-[1-(4-piperidylmethyl)-4-piperidyl]pyrazol-4-yl]oxazole-4-carboxamide To a solution of tert-butyl 4-[[4-[4-[[2-[2-(cyclopropylmethylamino)-4-pyridyl] oxazole-4-carbonyl] amino]-3-(difluoromethyl)pyrazol-1-yl]-1-piperidyl]methyl]piperidine-1-carboxylate (100 mg, 152 umol) in DCM (2 mL) was added HCl/dioxane (4 M, 1 mL). The mixture was stirred at 15° C.

for 0.5 hour. On completion, the mixture was concentrated to give the title compound (90.0 mg, 99% yield, HCl salt). LC-MS (ESI+) m/z 555.4 (M+H)+.

2-[1-[[1-(2,6-Dioxo-3-piperidyl)-3-methyl-2-oxo-benzimidazol-5-yl]methyl]-4-piperidyl] acetic acid (Intermediate ACY)

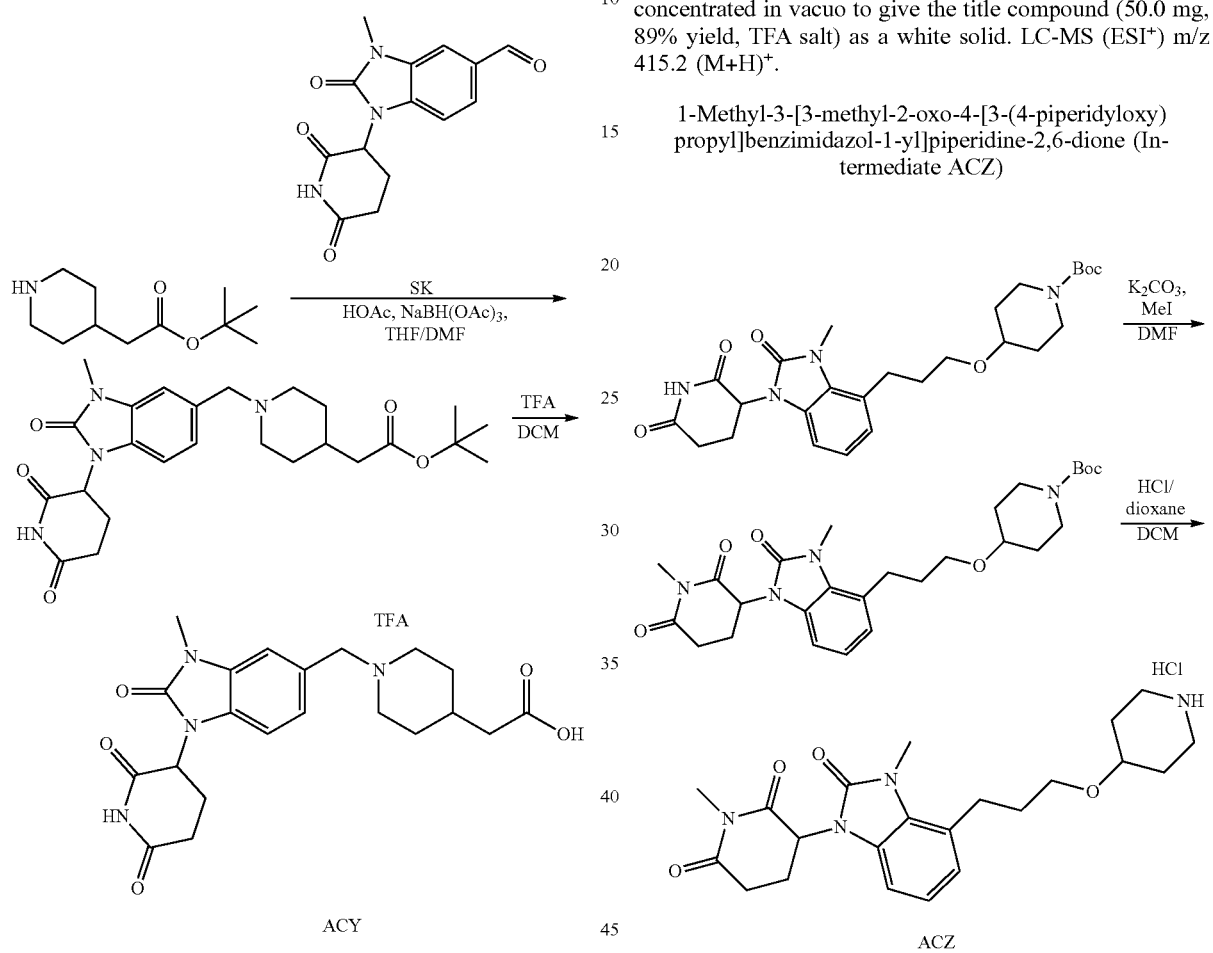

Step 1—Tert-butyl 2-[1-[[1-(2,6-dioxo-3-piperidyl)-3-methyl-2-oxo-benzimidazol-5-yl]methyl]-4-piperidyl]acetate To a solution of tert-butyl 2-(4-piperidyl)acetate (150 mg, 752 umol, CAS #180182-07-4) in DMF (3 mL) and THF (12 mL) was added TEA (76.1 mg, 752 umol). The mixture stirred at 25° C. for 10 minutes. HOAc (45.2 mg, 752 umol) and 1-(2,6-dioxo-3-piperidyl)-3-methyl-2-oxo-benzimidazole-5-carbaldehyde (237 mg, 827 umol, Intermediate SK) were then added to the mixture which was then stirred at 80° C. for 20 minutes. Next, NaBH(OAc)₃ (319 mg, 1.51 mmol) was added to the mixture at 25° C. and the reaction mixture was stirred at 25° C. for 24 hours. On completion, H₂O (0.5 mL) was added to the reaction mixture, then the mixture was concentrated in vacuo to give a residue. The residue was purified by reverse phase (0.1% FA condition) to give the title compound (58.0 mg, 16% yield) as a white solid. LC-MS (ESI+) m/z 471.3 (M+H)+.

Step 2—2-[1-[[1-(2,6-Dioxo-3-piperidyl)-3-methyl-2-oxo-benzimidazol-5-yl]methyl]-4-piperidyl] acetic acid To a solution of tert-butyl 2-[1-[[1-(2,6-dioxo-3-piperidyl)-3-methyl-2-oxo-benzimidazol-5-yl]methyl]-4-piperidyl]acetate (50.0 mg, 106 umol) in DCM (3 mL) was added TFA (27.01 mmol, 2 mL). The mixture was stirred at 15° C. for 2 hours. On completion, the reaction mixture was concentrated in vacuo to give the title compound (50.0 mg, 89% yield, TFA salt) as a white solid. LC-MS (ESI+) m/z 415.2 (M+H)+.

1-Methyl-3-[3-methyl-2-oxo-4-[3-(4-piperidyloxy) propyl]benzimidazol-1-yl]piperidine-2,6-dione (Intermediate ACZ)

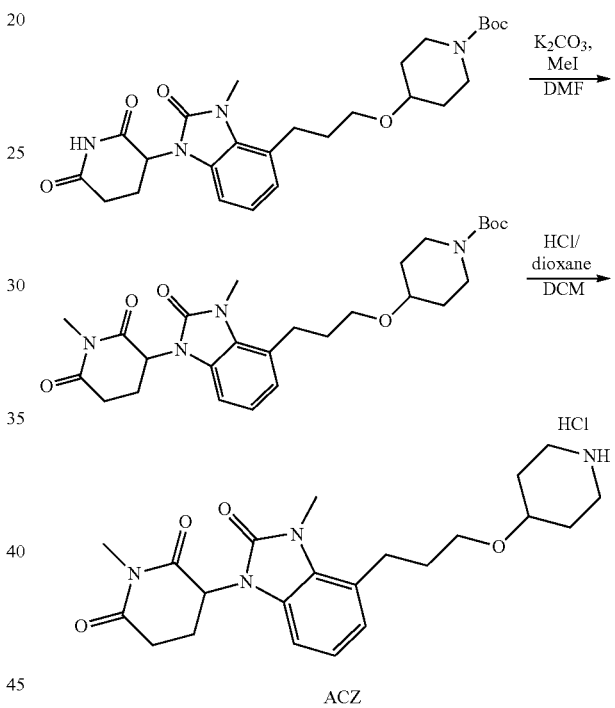

Step 1—Tert-butyl 4-[3-[3-methyl-1-(1-methyl-2,6-dioxo-3-piperidyl)-2-oxo-benzimidazol-4-yl] propoxy]piperidine-1-carboxylate To a solution of tert-butyl 4-[3-[1-(2,6-dioxo-3-piperidyl)-3-methyl-2-oxo-benzimidazol-4-yl] propoxy] piperidine-1-carboxylate (280 mg, 559 umol, synthesized via Steps 1-2 of Intermediate TN) in DMF (10 mL) was added MeI (119 mg, 839 umol, 52.2 uL) and K₂CO₃ (154 mg, 1.12 mmol) at 25° C. The mixture was stirred at 25° C. for 3 hours. On completion, the reaction mixture was quenched with H₂O (2 mL) at 25° C., then diluted with EA (10 mL) and extracted with EA (3×20 mL). The combined organic layers were dried over Na₂SO₄, filtered and concentrated in vacuo to give a residue. The residue was purified reverse phase (FA condition) to give the title compound (150 mg, 52% yield) as a white solid. ¹H NMR (400 MHz, DMSO-d₆) δ 7.01-6.83 (m, 3H), 5.48-5.35 (m, 1H), 3.65-3.58 (m, 2H), 3.57 (s, 3H), 3.51-3.41 (m, 3H), 3.03 (s, 5H), 2.99-2.90 (m, 3H), 2.82-2.63 (m, 2H), 2.06-1.95 (m, 1H), 1.87-1.72 (m, 4H), 1.39 (s, 9H); LC-MS (ESI+) m/z 537.3 (M+Na)+.

Step 2—1-Methyl-3-[3-methyl-2-oxo-4-[3-(4-piperidyloxy)propyl]benzimidazol-1-yl] piperidine-2,6-dione To a solution of tert-butyl 4-[3-[3-methyl-1-(1-methyl-2,6-dioxo-3-piperidyl)-2-oxo-benzimidazol-4-yl] propoxy]piperidine-1-carboxylate (80.0 mg, 155 umol) in DCM (1 mL) was added HCl/dioxane (4 M, 38.9 uL) at 25° C. The mixture was stirred at 25° C. for 2 hours. On completion, the reaction mixture was concentrated in vacuo to give the title compound (70.0 mg, 99% yield) as yellow oil. LC-MS (ESI+) m/z 415.3 (M+H)+.

5-[(3S)-3-Hydroxypyrrolidin-1-yl]pyrazolo[1,5-a]pyrimidine-3-carboxylic acid (Intermediate ADA)

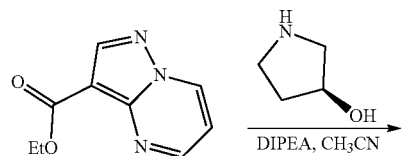

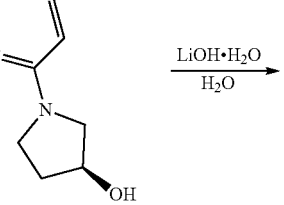

ADA

Step 1—Ethyl 5-[(3S)-3-hydroxypyrrolidin-1-yl]pyrazolo 1,5-a]pyrimidine-3-carboxylate To a solution of ethyl 5-chloropyrazolo[1,5-a]pyrimidine-3-carboxylate (360 mg, 1.60 mmol, CAS #1224944-77-7) in ACN (25 mL) was added (3S)-pyrrolidin-3-ol (208 mg, 2.39 mmol, CAS #122536-94-1) and DIPEA (412 mg, 3.19 mmol) at 25° C. The reaction mixture was stirred at 60° C. for 2 hours. On completion, the reaction mixture was concentrated in vacuo to give the title compound (440 mg, 99% yield) as yellow oil. LC-MS (ESI+) m/z 277.2 (M+H)+.

Step 2—5-[(3S)-3-Hydroxypyrrolidin-1-yl]pyrazolo [1,5-a]pyrimidine-3-carboxylic acid To a solution of ethyl 5-[(3S)-3-hydroxypyrrolidin-1-yl]pyrazolo[1,5-a]pyrimidine-3-carboxylate (400 mg, 1.45 mmol) in H2O (20 mL) was added LiOH·H2O (303 mg, 7.24 mmol) at 25° C. The reaction mixture was stirred at 60° C. for 2 hours. On completion, the reaction mixture was concentrated in vacuo. The residue was purified by reverse phase (0.1% FA condition) to give the title compound (350 mg, 97% yield) as a white solid. 1H NMR (400 MHz, DMSO-d6) δ 11.88-11.22 (m, 1H), 8.67 (d, J=7.6 Hz, 1H), 8.15 (s, 1H), 6.60-6.40 (m, 1H), 5.23-4.88 (m, 1H), 4.48-4.35 (m, 1H), 3.82-3.51 (m, 4H), 2.15-1.83 (m, 2H); LC-MS (ESI+) m/z 249.1 (M+H)+.

5-(3-Hydroxyazetidin-1-yl)pyrazolo[1,5-a]pyrimidine-3-carboxylic acid (Intermediate ADB)

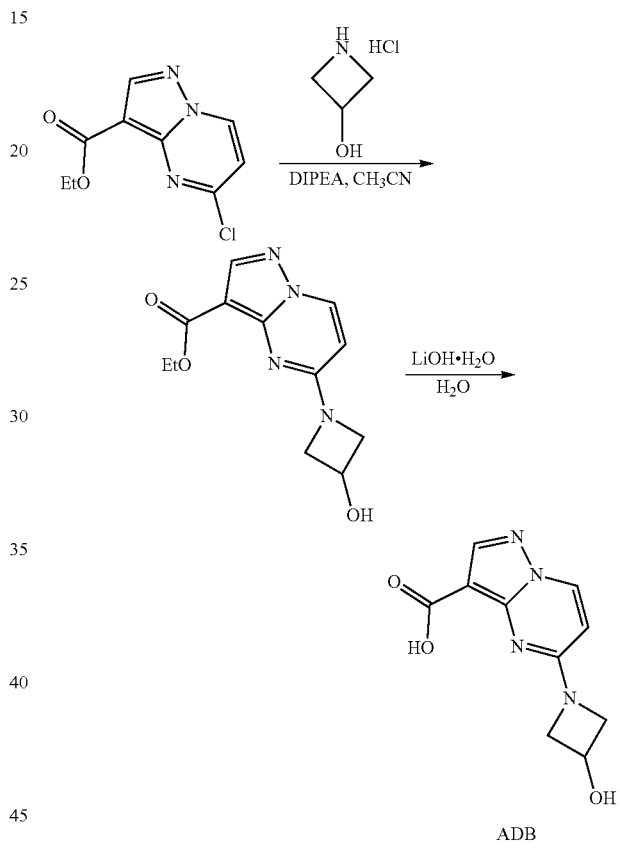

Step 1—Ethyl 5-(3-hydroxyazetidin-1-yl)pyrazolo [1,5-a]pyrimidine-3-carboxylate

A mixture of ethyl 5-chloropyrazolo[1,5-a]pyrimidine-3-carboxylate (300 mg, 1.33 mmol, CAS #1224944-77-7), azetidin-3-ol (146 mg, 1.33 mmol, HCl salt, CAS #18621-18-6) and DIPEA (516 mg, 3.99 mmol) in CH3CN (10 mL) was stirred at 60° C. for 2 hours. On completion, the mixture was concentrated in vacuo. The residue was purified by reversed phase flash (FA condition) to give the title compound (340 mg, 97% yield) as light yellow solid. 1H NMR (400 MHz, DMSO-d6) δ 8.67 (d, J=7.6 Hz, 1H), 8.17 (s, 1H), 6.35 (d, J=7.6 Hz, 1H), 4.65-4.57 (m, 1H), 4.40-4.31 (m, 2H), 4.18 (q, J=7.2 Hz, 2H), 3.90-3.87 (m, 2H), 1.77-1.74 (m, 1H), 1.25 (t, J=7.2 Hz, 3H).

Step 2—5-(3-Hydroxyazetidin-1-yl)pyrazolo[1,5-a] pyrimidine-3-carboxylic acid

A mixture of ethyl 5-(3-hydroxyazetidin-1-yl)pyrazolo[1,5-a]pyrimidine-3-carboxylate (140 mg, 533 umol) and LiOH—H₂O (112 mg, 2.67 mmol) in H₂O (2 mL) was stirred at 60° C. for 2 hours. On completion, after cooling to 15° C., the mixture was acidified to pH=6. The residue was purified by reverse phase flash (0.1% NH₃.H₂O) to give the title compound (120 mg, 96% yield) as white solid. ¹H NMR (400 MHz, DMSO-d₆) δ 8.64 (d, J=7.6 Hz, 1H), 8.05 (s, 1H), 6.26 (d, J=7.6 Hz, 1H), 4.67-4.54 (m, 1H), 4.45-4.31 (m, 2H), 3.93-3.90 (m, 2H), 1.75 (s, 1H).

1-Methyl-3-[3-methyl-4-[3-[3-(methylamino) propoxy]propyl]-2-oxo-benzimidazol-1-yl]] piperidine-2,6-dione (Intermediate ADC)

Step 2—1-Methyl-3-[3-methyl-4-[3-[3-(methylamino)propoxy]propyl]-2-oxo-benzimidazol-1-yl] piperidine-2,6-dione To a solution of tert-butyl N-methyl-N-[3-[3-[3-methyl-1-(1-methyl-2,6-dioxo-3-piperidyl)-2-oxo-benzimidazol-4-yl]propoxy]propyl]carbamate (120 mg, 191 umol) in DCM (3 mL) was added HCl/dioxane (3 mL). The reaction mixture was stirred at 25° C. for 2 hrs. On completion, the reaction mixture was concentrated in vacuo to give the title compound (83.8 mg, 99% yield, HCl) as brown solid. LC-MS (ESI⁺) m/z 403.3 (M+H)⁺.

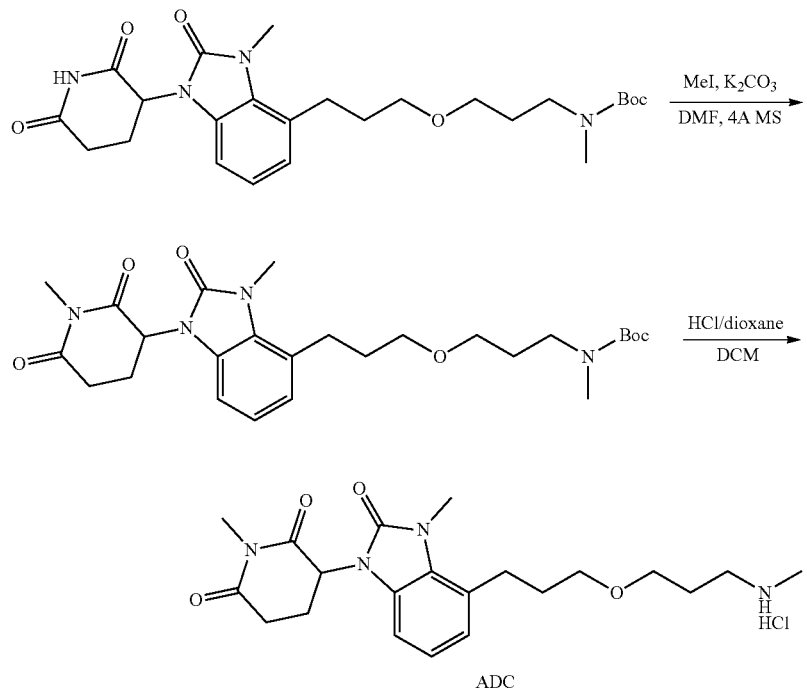

ADC

Step 1—Tert-butyl N-methyl-N-[3-[3-[3-methyl-1-(1-methyl-2,6-dioxo-3-piperidyl)-2-oxo-benzimidazol-4-yl]propoxy]propyl]carbamate To a solution of tert-butyl N-[3-[3-[1-(2,6-dioxo-3-piperidyl)-3-methyl-2-oxo-benzimidazol-4-yl] propoxy]propyl]-N-methyl-carbamate (260 mg, 532 umol, synthesized via Steps 1-2 of Intermediate PP) and 4 Å molecular sieves (40.0 mg) in DMF (5 mL) was added K₂CO₃ (88.3 mg, 638 umol), and MeI (75.5 mg, 532 umol, 33.1 uL). The reaction mixture was stirred at 25° C. for 12 hrs. On completion, the reaction mixture was quenched with water (50 ml). The aqueous phase was extracted with DCM (2×30 mL). The combined organic phase was washed with brine (2×30 mL), dried with anhydrous Na₂SO₄, filtered and concentrated in vacuo to give the title compound (140 mg, 42% yield) as white solid. ¹H NMR (300 MHz, DMSO-d₆) δ 7.00-6.91 (m, 2H), 6.90-6.81 (m, 1H), 5.43 (dd, J=5.6, 12.8 Hz, 1H), 3.57 (s, 3H), 3.45-3.38 (m, 3H), 3.37 (s, 1H), 3.32-3.28 (m, 3H), 3.22 (t, J=7.2 Hz, 2H), 3.03 (s, 3H), 2.99-2.88 (m, 3H), 2.76 (s, 3H), 1.88-1.77 (m, 2H), 1.75-1.63 (m, 2H), 1.38 (s, 9H); LC-MS (ESI⁺) m/z 503.3 (M+H)⁺.

Tert-butyl N-methyl-N-[2-(4-piperidyl)ethyl]carbamate (Intermediate ADD)

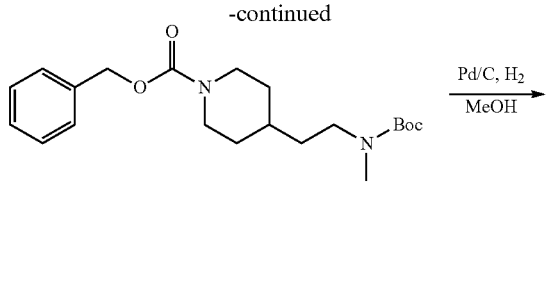

Step 1—Benzyl 4-(2-hydroxyethyl)piperidine-1-carboxylate

To a solution of 2-(4-piperidyl)ethanol (2 g, 15.5 mmol, HCl) (CAS #622-26-4) and NaHCO$_3$ (3.25 g, 38.7 mmol, 1.51 mL) in a mixed solvent of ACN (10 mL) and H$_2$O (10 mL) was added CbzCl (3.96 g, 23.2 mmol). The reaction mixture was stirred at 25° C. for 12 hrs. On completion, the reaction mixture was concentrated in vacuo to remove ACN, then extracted with ethyl acetate (2×100 mL). The combined organic layers were washed with brine (20 mL), dried over anhydrous sodium sulfate, filtered and concentrated in vacuo. The residue was purified by silica gel chromatography (PE:EA=1:1) to give the title compound (3.50 g, 86% yield) as colorless oil. $^1$H NMR (400 MHz, CDCl$_3$) δ 7.43-7.28 (m, 5H), 5.13 (s, 2H), 4.30-4.09 (m, 2H), 3.80-3.66 (m, 2H), 2.88-2.71 (m, 2H), 1.72-1.69 (m, 2H), 1.67-1.59 (m, 1H), 1.53 (q, J=6.6 Hz, 2H), 1.24-1.21 (m, 1H), 1.21-1.07 (m, 2H); LC-MS (ESI$^+$) m/z 264.1 (M+H)$^+$.

Step 2—Benzyl 4-(2-methylsulfonyloxyethyl)piperidine-1-carboxylate

To a solution of benzyl 4-(2-hydroxyethyl)piperidine-1-carboxylate (2 g, 7.59 mmol) in DCM (40 mL) was TEA (2.31 g, 22.8 mmol). The reaction mixture was cooled to 0° C. Then, MsCl (1.31 g, 11.4 mmol) was added. The resulting reaction mixture was stirred at 15° C. for 0.5 hr. On completion, the reaction mixture was quenched with water (3 mL), then extracted with DCM (3×15 mL). The combined organic layers were washed with brine (10 mL), dried over anhydrous sodium sulfate, filtered and the filtrate was concentrated in vacuo to give the title compound (2.5 g, 96% yield) as yellow solid. $^1$H NMR (400 MHz, CDCl$_3$) δ 7.40-7.29 (m, 5H), 5.13 (s, 2H), 4.29 (t, J=6.4 Hz, 2H), 4.19 (m, 2H), 3.02 (s, 3H), 2.88-2.72 (m, 2H), 1.77-1.62 (m, 5H), 1.24-1.11 (m, 2H).

Step 3—Benzyl 4-[2-[tert-butoxycarbonyl(methyl)amino]ethyl]piperidine-1-carboxylate To a solution of tert-butyl N-methylcarbamate (1.33 g, 10.1 mmol) in DMF (20 mL) was added NaH (431 mg, 10.8 mmol, 60% dispersion in mineral oil) at 0° C. for 0.5 hr. Then, benzyl 4-(2-methylsulfonyl oxyethyl)piperidine-1-carboxylate (2.3 g, 6.74 mmol) and KI (112 mg, 674 umol) was added into the above mixture. The reaction mixture was stirred at 25° C. for 12 hrs. On completion, the reaction mixture was quenched with water (2 mL), then extracted with ethyl acetate (3×50 mL). The combined organic layers were washed with brine (50 mL), dried over anhydrous sodium sulfate, filtered and the filtrate was concentrated in vacuo. The residue was purified by silica gel chromatography (PE:EA=20:1) to give the title compound (2.5 g, 99% yield) as a colorless oil. $^1$H NMR (400 MHz, CDCl$_3$) δ 7.33-7.21 (m, 5H), 5.05 (s, 2H), 4.22-3.99 (m, 2H), 3.18-3.16 (m, 2H), 2.75 (s, 3H), 2.67-2.65 (m, 3H), 1.66-1.62 (m, 2H), 1.38 (s, 9H), 1.37-1.31 (m, 2H), 1.12-1.03 (m, 2H), 0.85-0.74 (m, 1H); LC-MS (ESI$^+$) m/z 399.2 (M+Na)$^+$.

Step 4—Tert-butyl N-methyl-N-[2-(4-piperidyl)ethyl]carbamate

To a solution of benzyl 4-[2-[tert-butoxycarbonyl(methyl)amino]ethyl]piperidine-1-carboxylate (2.50 g, 6.64 mmol) in methanol (30 mL) was added Pd/C (250 mg, 10% wt) under nitrogen atmosphere. The suspension was degassed and purged with H$_2$ three times. The mixture was stirred under H$_2$ (15 Psi) at 25° C. for 12 hrs. On completion, the mixture was concentrated in vacuo to give the title compound (1.6 g, 99% yield) as colorless oil. $^1$H NMR (400 MHz, CDCl$_3$) δ 3.25-3.23 (m, 2H), 3.10-3.07 (m, 2H), 2.83 (s, 3H), 2.60 (dt, J=2.4, 12.0 Hz, 2H), 2.37-2.33 (m, 2H), 1.78-1.66 (m, 2H), 1.46 (s, 9H), 1.45-1.41 (m, 2H), 1.39-1.31 (m, 1H), 1.22-1.13 (m, 2H), 0.92-0.82 (m, 1H).

3-[3-Methyl-4-[[4-[2-(methylamino)ethyl]-1-piperidyl]methyl]-2-oxo-benzimidazol-1-yl] piperidine-2,6-dione (Intermediate ADE)

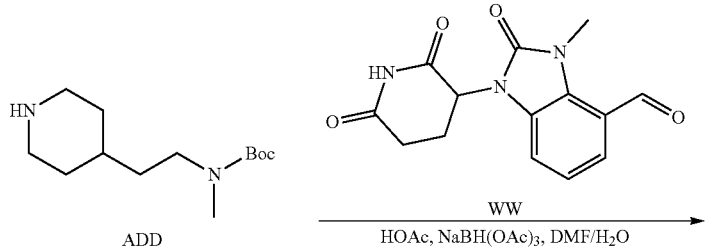

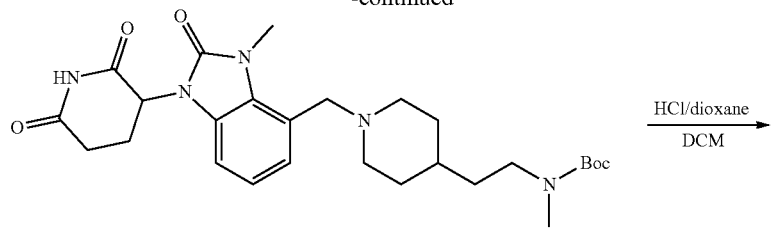

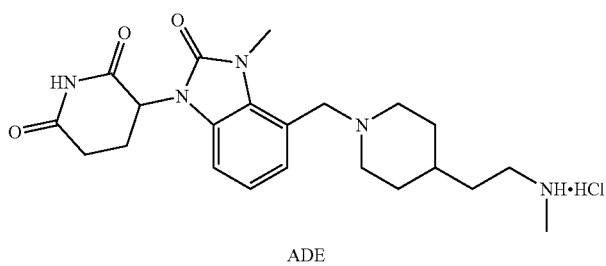

ADE

Step 1—Tert-butyl N-[2-[1-[[1-(2,6-dioxo-3-piperidyl)-3-methyl-2-oxo-benzimidazol-4-yl]methyl]-4-piperidyl]ethyl]-N-methyl-carbamate To a solution of 1-(2,6-dioxo-3-piperidyl)-3-methyl-2-oxo-benzimidazole-4-carbaldehyde (200 mg, 696 umol, Intermediate WW) and tert-butyl N-methyl-N-[2-(4-piperidyl)ethyl]carbamate (168 mg, 696 umol, Intermediate ADD) in a mixed solvent of THF (5 mL) and DMF (1 mL) was added HOAc (41.8 mg, 696 umol, 39.8 uL). The reaction mixture was stirred at 80° C. for 1 hr. Then, the reaction mixture was cooled to 20° C., and NaBH(OAc)$_3$ (177 mg, 835 umol) was added. The reaction mixture was stirred at 20° C. for 12 hrs. On completion, the reaction was concentrated in vacuo. The crude product was purified by reversed-phase HPLC (0.1% FA condition) to give the title compound (180 mg, 50% yield) as white solid. $^1$H NMR (400 MHz, CDCl$_3$) δ 8.10 (s, 1H), 7.10-6.99 (m, 2H), 6.83-6.74 (m, 1H), 5.28-5.21 (m, 1H), 3.81 (s, 2H), 3.78-3.71 (m, 2H), 3.31-3.22 (m, 2H), 3.03-2.91 (m, 4H), 2.87- 2.74 (m, 7H), 2.30-2.22 (m, 1H), 2.15-1.99 (m, 2H), 1.75-1.71 (m, 2H), 1.47 (s, 9H), 1.31-1.2 (m, 4H) LC-MS (ESI$^+$) m/z 514.3 (M+H)$^+$.

Step 2—3-[3-Methyl-4-[[4-[2-(methylamino)ethyl]-1-piperidyl]methyl]-2-oxo-benzimidazol-1-yl]piperidine-2,6-dione To a solution of tert-butyl N-[2-[1-[[1-(2,6-dioxo-3-piperidyl)-3-methyl-2-oxo-benzimidazol-4-yl] methyl]-4-piperidyl]ethyl]-N-methyl-carbamate (180 mg, 350 umol) in DCM (5 mL) was added HCl/dioxane (4 M, 4.0 mL). The reaction mixture was stirred at 20° C. for 5 hrs. On completion, the reaction mixture was concentrated in vacuo to give the title compound (150 mg, 95% yield, HCl salt) as white solid. LC-MS (ESI$^+$) m/z 414.2 (M+H)$^+$.

3-[4-[[4-[2-[[4-[4-Amino-3-(difluoromethyl)pyrazol-1-yl]cyclohexyl]methyl-methyl-amino] ethyl]-1-piperidyl]methyl]-3-methyl-2-oxo-benzimidazol-1-yl]piperidine-2,6-dione (Intermediate ADF)

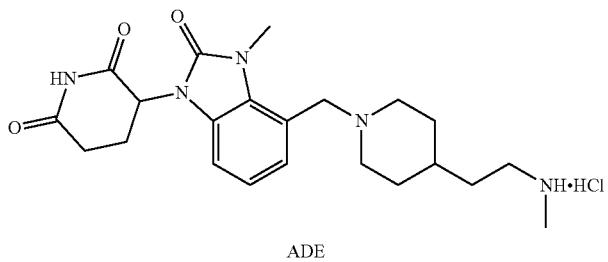

ADE

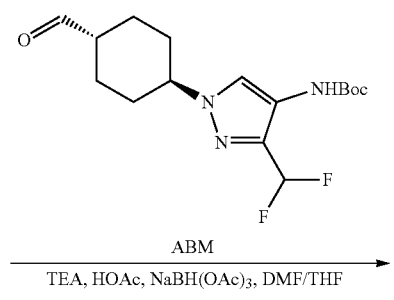

ABM

TEA, HOAc, NaBH(OAc)$_3$, DMF/THF

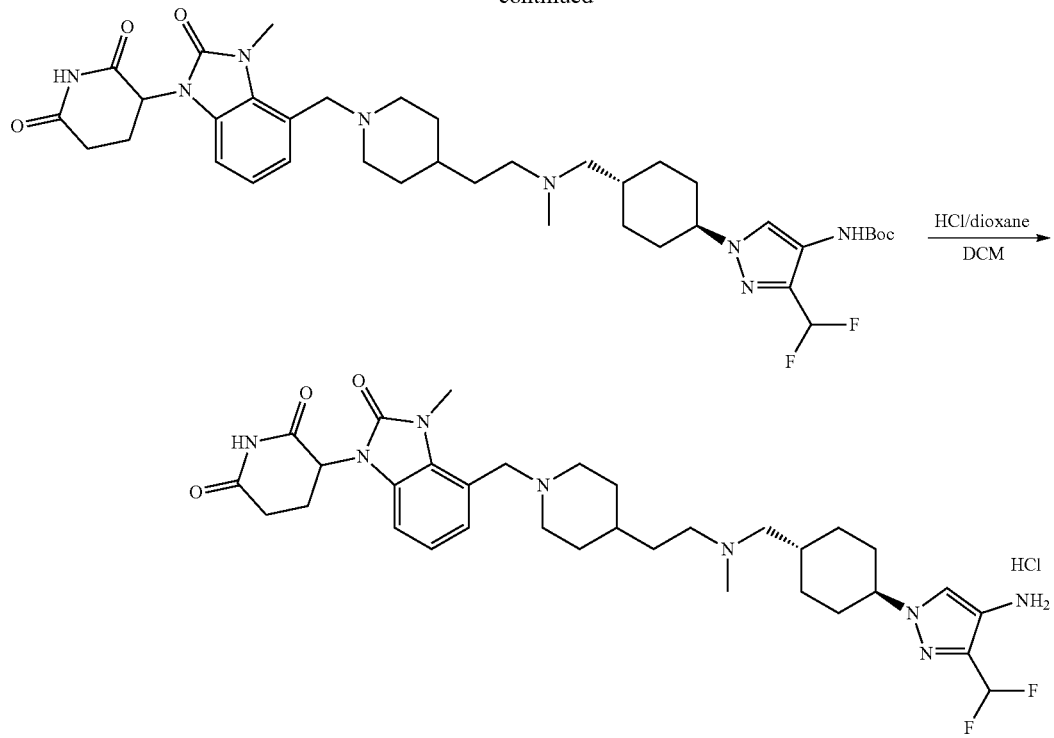

ADF

Step 1—Tert-butyl N-[3-(difluoromethyl)-1-[4-[[2-[1-[[1-(2,6-dioxo-3-piperidyl)-3-methyl-2-oxo-benzimidazol-4-yl]methyl]-4-piperidyl]ethyl-methyl-amino]methyl]cyclohexyl]pyrazol-4-yl]carbamate To a solution of 3-[3-methyl-4-[[4-[2-(methylamino)ethyl]-1-piperidyl]methyl]-2-oxo-benzimidazol-1-yl]piperidine-2,6-dione (100 mg, 222 umol, HCl, Intermediate ADE) and tert-butyl N-[3-(difluoromethyl)-1-(4-formyl cyclohexyl)pyrazol-4-yl]carbamate (70.0 mg, 204 umol, Intermediate ABM) in a mixed solvent of THF (10 mL) and DMF (2 mL) was added TEA (45.0 mg, 444 umol). Then, the reaction mixture was stirred at 25° C. for 0.5 hr. After, HOAc (40.0 mg, 666 umol) was added. 0.5 hr later, the reaction mixture was cooled to −10° C. Next, NaBH(OAc)$_3$ (47.1 mg, 222 umol) was added and the resulting reaction mixture was stirred at −10° C. for 5 hrs. On completion, the reaction mixture was concentrated in vacuo. The crude product was purified by reversed-phase HPLC (0.1% FA condition) to give the title compound (100 mg, 61% yield) as white solid. $^1$H NMR (400 MHz, CDCl$_3$) δ 8.40 (s, 1H), 7.91 (s, 1H), 7.06-6.95 (m, 2H), 6.87-6.55 (m, 3H), 5.24 (dd, J=5.2, 12.4 Hz, 1H), 4.07-3.94 (m, 1H), 3.89-3.79 (m, 2H), 3.77 (s, 3H), 3.14-2.95 (m, 5H), 2.95-2.82 (m, 4H), 2.75 (s, 3H), 2.29-2.03 (m, 7H), 1.86-1.75 (m, 3H), 1.73-1.64 (m, 4H), 1.51 (s, 9H), 1.48-1.43 (m, 1H), 1.43-1.33 (m, 2H), 1.31-1.20 (m, 2H); LC-MS (ESI$^+$) m/z 741.2 (M+H)$^+$.

Step 2—3-[4-[[4-[2-[[4-[4-Amino-3-(difluoromethyl)pyrazol-1-yl] cyclohexyl]methyl-methyl-amino] ethyl]-1-piperidyl]methyl]-3-methyl-2-oxo-benzimidazol-1-yl]piperidine-2,6-dione To a solution of tert-butyl N-[3-(difluoromethyl)-1-[4-[[2-[1-[[1-(2,6-dioxo-3-piperidyl)-3-methyl-2-oxo-benzimidazol-4-yl]methyl]-4-piperidyl] ethyl-methyl-amino]methyl] cyclohexyl]-pyrazol-4-yl]carbamate (40 mg, 54.0 umol) in DCM (2 mL) was added HCl/dioxane (4 M, 2 mL). The reaction mixture was stirred at 20° C. for 2 hrs. On completion, the reaction mixture was concentrated in vacuo to give the title compound (36 mg, 98% yield, HCl salt) as white solid. LC-MS (ESI$^+$) m/z 741.2 (M+H)$^+$.

2-[4-[(4-Piperazin-1-ylcyclohexyl)amino]quinazolin-6-yl]acetonitrile (Intermediate ADG)

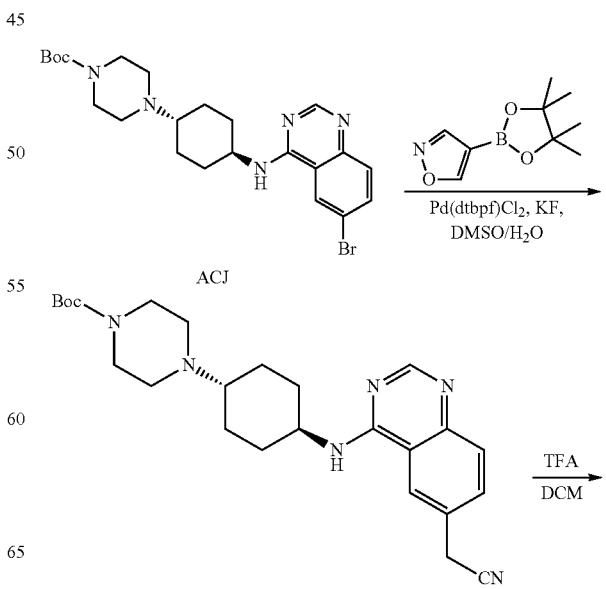

-continued

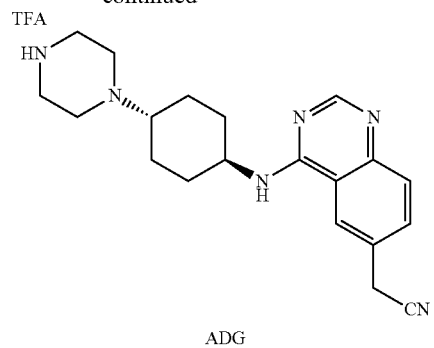

ADG

Step 1—Tert-butyl 4-[4-[[6-(cyanomethyl)quinazolin-4-yl]amino] cyclohexyl]piperazine-1-carboxylate To a mixture of tert-butyl 4-[4-[(6-bromoquinazolin-4-yl)amino]cyclohexyl]piperazine-1-carboxylate (300 mg, 611 umol, Intermediate ACJ) and 4-(4,4,5,5-tetramethyl-1,3,2-dioxaborolan-2-yl)isoxazole (143 mg, 734 umol) in DMSO (2.4 mL) and $H_2O$ (1 mL) was added ditert-butyl(cyclopentyl)phosphane; dichloropalladium; iron (39.8 mg, 61.1 umol) and KF (142 mg, 2.45 mmol, 57.3 uL). The reaction mixture was stirred at 130° C. for 12 hours under $N_2$ atmosphere. On completion, the reaction mixture was filtered and concentrated in vacuo. The residue was purified by reverse phase (0.1% FA condition) to give the title compound (170 mg, 61% yield) as light yellow solid. $^1$H NMR (400 MHz, DMSO-$d_6$) δ 8.44 (s, 1H), 8.14 (s, 1H), 8.03-7.97 (m, 1H), 7.73-7.64 (m, 2H), 4.15 (s, 2H), 4.15-4.07 (m, 1H), 3.29 (d, J=4.4 Hz, 4H), 2.47 (s, 4H), 2.38-2.31 (m, 1H), 2.08-1.97 (m, 2H), 1.86 (d, J=11.6 Hz, 2H), 1.41 (s, 3H), 1.40 (s, 9H), 1.37-1.30 (m, 1H).

Step 2—2-[4-[(4-Piperazin-1-ylcyclohexyl)amino]quinazolin-6-yl]acetonitrile

To a mixture of tert-butyl 4-[4-[[6-(cyanomethyl)quinazolin-4-yl]amino]cyclohexyl]piperazine-1-carboxylate (160 mg, 355 umol) in DCM (2 mL) was added TFA (49.2 g, 432 mmol, 32 mL). The reaction mixture was stirred at 25° C. for 1 hour. On completion, the reaction mixture was concentrated in vacuo to give the title compound (160 mg, 97% yield, TFA) as red oil. LC-MS (ESI$^+$) m/z 351.3 (M+H)$^+$.

3-Prop-2-ynoxypropan-1-ol (Intermediate ADH)

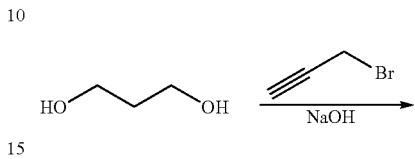

ADH

3-Bromoprop-1-yne (30.0 g, 201 mmol, 21.7 mL) and propane-1,3-diol (30.7 g, 403 mmol, 29.2 mL) were introduced at 0° C. and stirred. Then NaOH (9.68 g, 242 mmol) was added to the mixture. The reaction mixture was stirred at 25° C. for 24 hours. On completion, the reaction mixture was diluted with water (50 mL) and extracted with EA (2×100 mL). The combined organic layers was dried over $Na_2SO_4$, filtered and concentrated in vacuo to give a residue. The residue was purified by column chromatography to give the title compound (16.5 g, 71% yield) as light yellow oil. $^1$H NMR (400 MHz, CDCl$_3$) δ 4.11 (d, J=2.4 Hz, 2H), 3.70 (t, J=6.0 Hz, 2H), 3.64 (t, J=6.0 Hz, 2H), 2.52 (s, 1H), 2.42 (t, J=2.4 Hz, 1H), 1.85-1.77 (m, 2H).

3-[3-[1-(2,6-Dioxo-3-piperidyl)-3-methyl-2-oxobenzimidazol-4-yl]propoxy]propanal (Intermediate ADI)

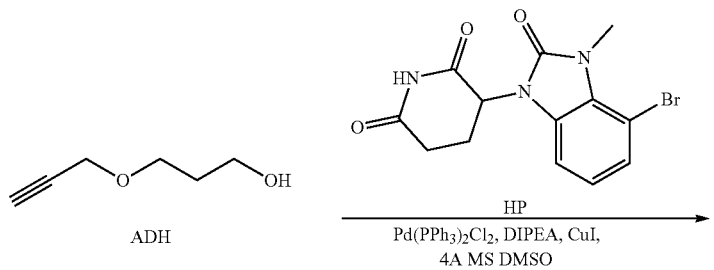

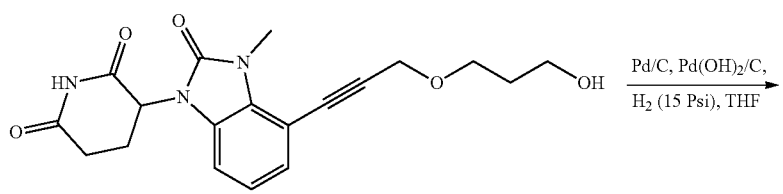

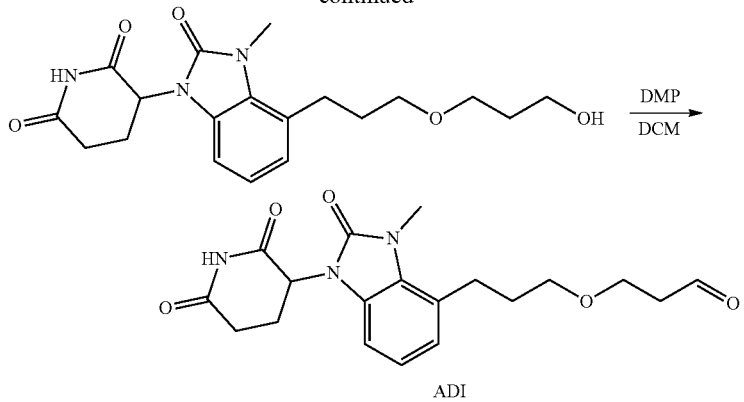

ADI

Step 1—3-[4-[3-(3-Hydroxypropoxy)prop-1-ynyl]-3-methyl-2-oxo-benzimidazol-1-yl]piperidine-2,6-dione To a mixture 3-prop-2-ynoxypropan-1-ol (675 mg, 5.91 mmol, Intermediate ADH) and 3-(4-bromo-3-methyl-2-oxo-benzimidazol-1-yl)piperidine-2,6-dione (1.00 g, 2.96 mmol, Intermediate HP) in DMSO (2 mL) was added DIPEA (1.91 g, 14.7 mmol, 2.58 mL), Pd(PPh$_3$)$_2$Cl$_2$ (207 mg, 295 umol), CuI (56.3 mg, 295 umol) and 4 Å molecular sieves (50 mg, 2.96 mmol). The reaction mixture was stirred at 80° C. for 2 hours under N$_2$ atmosphere. On completion, the reaction mixture was filtered and concentrated in vacuo. The residue was purified by reverse phase (0.1% FA condition) to give the title compound (650 mg, 59% yield) as yellow solid. $^1$H NMR (400 MHz, DMSO-d$_6$) δ 11.13 (s, 1H), 7.17 (d, J=8.0 Hz, 1H), 7.14-7.11 (m, 1H), 7.05-7.00 (m, 1H), 5.43-5.37 (m, 1H), 4.45 (t, J=5.2 Hz, 1H), 4.41 (s, 2H), 3.64 (s, 3H), 3.59 (t, J=6.4 Hz, 2H), 3.50-3.44 (m, 2H), 2.95-2.83 (m, 1H), 2.77-2.62 (m, 2H), 2.07-1.99 (m, 1H), 1.73-1.66 (m, 2H); LC-MS (ESI$^+$) m/z 372.2 (M+H)$^+$.

Step 2—3-[4-[3-(3-Hydroxypropoxy)propyl]-3-methyl-2-oxo-benzimidazol-1-yl]piperidine-2,6-dione To a mixture of 3-[4-[3-(3-hydroxypropoxy)prop-1-ynyl]-3-methyl-2-oxo-benzimidazol-1-yl] piperidine-2,6-dione (600 mg, 1.62 mmol) in THF (10 mL) was added Pd/C (250 mg, 10% wt) and Pd(OH)$_2$/C (250 mg, 10% wt). The reaction mixture was stirred at 25° C. for 3 hours under H$_2$ (15 PSI) atmosphere. On completion, the reaction mixture was filtered and concentrated in vacuo to give the title compound (600 mg, 98% yield) as brown solid. $^1$H NMR (400 MHz, DMSO-d$_6$) δ 11.08 (s, 1H), 7.05-6.92 (m, 2H), 6.92-6.83 (m, 1H), 5.41-5.32 (m, 1H), 4.38 (s, 1H), 3.56 (s, 3H), 3.48-3.40 (m, 6H), 2.99-2.91 (m, 2H), 2.91-2.83 (m, 1H), 2.72-2.60 (m, 2H), 2.05-1.96 (m, 1H), 1.88-1.76 (m, 2H), 1.71-1.61 (m, 2H); LC-MS (ESI$^+$) m/z 376.2 (M+H)$^+$.

Step 3—3-[3-[1-(2,6-Dioxo-3-piperidyl)-3-methyl-2-oxo-benzimidazol-4-yl]propoxy]propanal To a mixture of 3-[4-[3-(3-hydroxypropoxy)propyl]-3-methyl-2-oxo-benzimidazol-1-yl]piperidine-2,6-dione (590 mg, 1.57 mmol) in DCM (20 mL) was added DMP (799 mg, 1.89 mmol). The reaction mixture was stirred at 25° C. for 1.5 hours. On completion, the reaction mixture was quenched by saturated Na$_2$S$_2$O$_3$ (30 mL) and saturated NaHCO$_3$ (30 mL) at 25° C., and then stirred for 30 minutes. The mixture was extracted with DCM (2×50 mL), and then the organic layers were separated and concentrated in vacuo to give the title compound (586 mg, 99% yield) as brown solid. $^1$H NMR (400 MHz, DMSO-d$_6$) δ 11.08 (s, 1H), 9.68 (t, J=2.0 Hz, 1H), 6.99-6.93 (m, 2H), 6.88-6.84 (m, 1H), 5.40-5.32 (m, 1H), 3.72 (t, J=6.0 Hz, 2H), 3.53 (s, 3H), 3.48-3.42 (m, 2H), 2.97-2.90 (m, 2H), 2.89-2.83 (m, 1H), 2.76-2.67 (m, 1H), 2.66-2.58 (m, 3H), 2.05-1.95 (m, 1H), 1.86-1.76 (m, 2H); LC-MS (ESI$^+$) m/z 374.2 (M+H)$^+$.

4-[(4-Oxocyclohexyl)amino]quinazoline-6-carbonitrile (Intermediate ADJ)

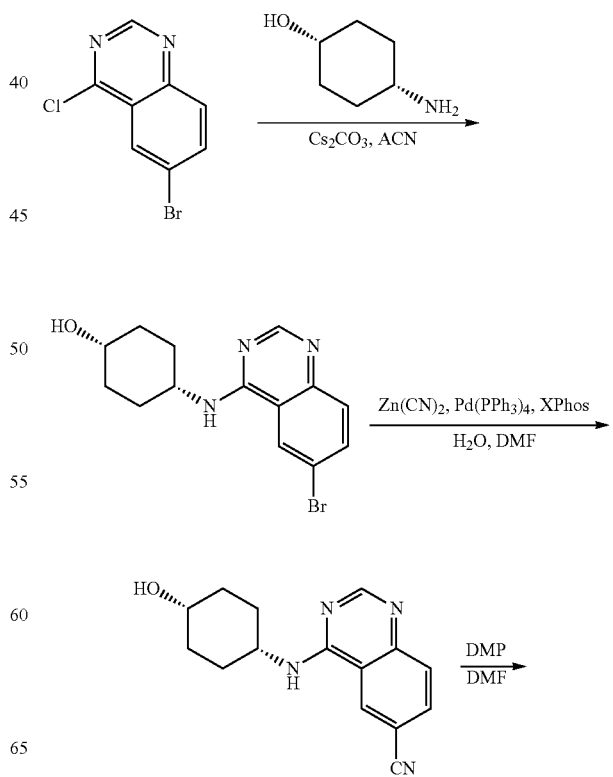

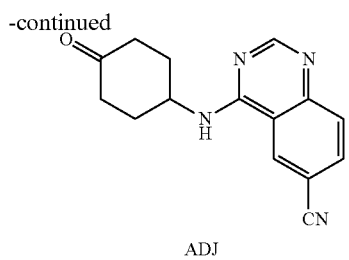

ADJ

Step 1—4-[(6-Bromoquinazolin-4-yl)amino]cyclohexanol

A mixture of 6-bromo-4-chloro-quinazoline (2.11 g, 8.68 mmol, CAS #38267-96-8), 4-aminocyclohexanol (1.00 g, 8.68 mmol, CAS #40525-78-8) and $Cs_2CO_3$ (5.66 g, 17.4 mmol) in ACN (30.0 mL) was stirred at 80° C. for 16 hrs. On completion, the reaction mixture was filtered. The filter cake was washed with water and concentrated in vacuo to give the title compound (1.40 g, 50% yield) as a white solid. $^1$H NMR (400 MHz, DMSO-$d_6$) δ 8.69 (d, J=2.0 Hz, 1H), 8.45 (s, 1H), 8.04 (d, J=7.6 Hz, 1H), 7.83 (dd, J=2.4, 8.8 Hz, 1H), 7.58 (d, J=8.8 Hz, 1H), 4.41 (d, J=2.4 Hz, 1H), 4.23-4.13 (m, 1H), 3.83 (d, J=2.0 Hz, 1H), 1.92-1.78 (m, 2H), 1.73 dd, J=2.8, 12.8 Hz, 2H), 1.68-1.59 (m, 2H), 1.58-1.44 (m, 2H).

Step 2—4-[(4-Hydroxycyclohexyl)amino]quinazoline-6-carbonitrile

A mixture of 4-[(6-bromoquinazolin-4-yl)amino]cyclohexanol (2.00 g, 6.21 mmol), $Zn(CN)_2$ (1.46 g, 12.4 mmol), $Pd(PPh_3)_4$ (717 mg, 620 umol) in DMF (15.0 mL) was degassed and purged with $N_2$ three times, and then the mixture was stirred at 100° C. for 16 hrs under $N_2$ atmosphere. On completion, the reaction mixture was quenched by addition water (10 mL), and then filtered. The filter cake was washed with water and concentrated in vacuo to give a compound (1.67 g, 100% yield) as a white solid. $^1$H NMR (400 MHz, DMSO-$d_6$) δ 9.01 (d, J=1.2 Hz, 1H), 8.53 (s, 1H), 8.28 (d, J=7.2 Hz, 1H), 8.03 (dd, J=1.6, 8.8 Hz, 1H), 7.74 (d, J=8.8 Hz, 1H), 4.43 (d, J=2.4 Hz, 1H), 4.27-4.13 (m, 1H), 3.83 (d, J=2.4 Hz, 1H), 1.95-1.80 (m, 2H), 1.78-1.60 (m, 4H), 1.59-1.46 (m, 2H).

Step 3—4-[(4-Oxocyclohexyl)amino]quinazoline-6-carbonitrile

To a solution of 4-[(4-hydroxycyclohexyl)amino]quinazoline-6-carbonitrile (200 mg, 745 umol) in DCM (10.0 mL) was added Dess-Martin (632 mg, 1.49 mmol) portionwise. The reaction mixture was stirred at 25° C. for 2 hrs. On completion, the reaction mixture was quenched by addition saturated $Na_2S_2O_3$ (1 mL) and $NaHCO_3$ (1 mL), then diluted with water (5 mL) and extracted with EA (2×10 mL). The combined organic layers were washed with brine (3×30 mL), dried over $Na_2SO_4$, the organic layers was concentrated in vacuo to give the title compound (140 mg, 70% yield) as a yellow solid. $^1$H NMR (400 MHz, CDCl$_3$) δ 8.76 (s, 1H), 8.35 (d, J=0.8 Hz, 1H), 7.97-7.93 (m, 1H), 7.93-7.88 (m, 1H), 6.31 (d, J=6.4 Hz, 1H), 4.91-4.68 (m, 1H), 2.66-2.46 (m, 6H), 1.98-1.87 (m, 2H).

Tert-butyl 4-(3-prop-2-ynoxypropoxy)piperidine-1-carboxylate (Intermediate ADK)

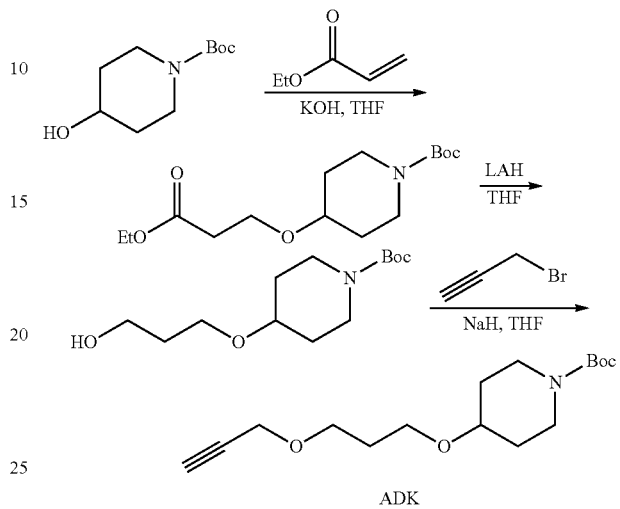

ADK

Step 1—tert-butyl 4-(3-ethoxy-3-oxo-propoxy)piperidine-1-carboxylate

To a solution of tert-butyl 4-hydroxypiperidine-1-carboxylate (10 g, 49.7 mmol) (CAS #109384-19-2) in THF (20 mL) was added KOH (320 mg, 4.97 mmol, 87%) and ethyl prop-2-enoate (15 g, 149 mmol, 16.2 mL). The reaction mixture was stirred at 20° C. for 16 hrs. On completion, the reaction mixture was concentrated in vacuo to remove THF, then water (50 mL) was added, and the mixture was extracted with ethyl acetate (2×100 mL). The combined organic layers were washed with brine (20 mL), dried over anhydrous sodium sulfate, filtered and concentrated in vacuo. The residue was purified by silica gel chromatography (PE:EA=10:1) to give the title compound (6.00 g, 40% yield) as colorless oil. $^1$H NMR (400 MHz, CDCl$_3$) δ 4.16 (q, J=7.2 Hz, 2H), 3.78-3.65 (m, 4H), 3.54-3.44 (m, 1H), 3.17-3.07 (m, 2H), 2.57 (t, J=6.4 Hz, 2H), 1.87-1.76 (m, 2H), 1.55-1.51 (m, 2H), 1.46 (s, 9H), 1.27 (t, J=7.2 Hz, 3H).

Step 2—Tert-butyl 4-(3-hydroxypropoxy)piperidine-1-carboxylate

A solution of tert-butyl 4-(3-ethoxy-3-oxo-propoxy)piperidine-1-carboxylate (3.9 g, 12.9 mmol) in THF (30 mL) was cooled to 0° C. Subsequently, LAH (540 mg, 14.2 mmol) was added and the reaction mixture was stirred at 0° C. for 0.5 hr. On completion, the reaction mixture was quenched with a solution of 15% NaOH (1 mL) and anhydrous sodium sulfate was added. The mixture was filtered and concentrated in vacuo to give the title compound (3.00 g, 89% yield) as colorless oil. $^1$H NMR (400 MHz, CDCl$_3$) δ 3.82-3.71 (m, 4H), 3.67 (t, J=5.6 Hz, 2H), 3.52-3.42 (m, 1H), 3.14-3.10 (m, 2H), 2.40 (t, J=5.6 Hz, 1H), 1.85 (quin, J=5.6 Hz, 4H), 1.55-1.51 (m, 2H), 1.46 (s, 9H).

Step 3—Tert-butyl 4-(3-prop-2-ynoxypropoxy)piperidine-1-carboxylate

To a solution of tert-butyl 4-(3-hydroxypropoxy)piperidine-1-carboxylate (3 g, 11.6 mmol) in THF (20 mL) was cooled to 0° C., then NaH (555 mg, 13.8 mmol, 60% dispersion in mineral oil) was added. The reaction mixture was stirred at 0° C. for 0.5 hr. Then, 3-bromoprop-1-yne (2.58 g, 17.3 mmol) was added. The resulting reaction mixture was stirred at 25° C. for 12 hrs. On completion, the reaction mixture was quenched with water (1 mL), and diluted with ethyl acetate (100 mL). The organic layers was washed with brine (20 mL), dried over with anhydrous sodium sulfate, filtered and concentrated in vacuo. The residue was purified by silica gel chromatography (PE: EA=20:1) to give the title compound (2.3 g, 67% yield) as yellow oil. $^1$H NMR (400 MHz, CDCl$_3$) δ 4.16 (d, J=2.4 Hz, 2H), 3.83-3.70 (m, 2H), 3.63 (t, J=6.0 Hz, 2H), 3.56 (t, J=6.0 Hz, 2H), 3.50-3.41 (m, 1H), 3.18-3.06 (m, 2H), 2.44 (t, J=2.4 Hz, 1H), 1.93-1.78 (m, 4H), 1.57-1.49 (m, 2H), 1.48 (s, 9H).

3-[3-Methyl-2-oxo-4-[3-[3-(4-piperidyloxy)propoxy]propyl]benzimidazol-1-yl]piperidine-2,6-dione (Intermediate ADL)

Step 1—Tert-butyl 4-[3-[3-[1-(2,6-dioxo-3-piperidyl)-3-methyl-2-oxo-benzimidazol-4-yl]prop-2-ynoxy]propoxy]piperidine-1-carboxylate 3-(4-bromo-3-methyl-2-oxo-benzimidazol-1-yl)piperidine-2,6-dione (500 mg, 1.48 mmol, Intermediate HP), tert-butyl 4-(3-prop-2-ynoxypropoxy)piperidine-1-carboxylate (1 g, 3.36 mmol, Intermediate ADK), Pd(PPh$_3$)$_2$Cl$_2$ (103 mg, 147 umol), CuI (28.1 mg, 147 umol), DIPEA (1.91 g, 14.7 mmol) and 4 Å molecular sieves (200 mg) in DMSO (2 mL) was de-gassed and then heated to 80° C. for 2 hours under N$_2$. On completion, the mixture was diluted with water (20 mL), extracted with ethyl acetate (3×50 mL), dried over anhydrous sodium sulfate, filtered and the filtrate was concentrated in vacuo. The residue was purified by reversed-phase HPLC (0.1% FA condition) to give the title compound (780 mg, 76% yield) as yellow solid. $^1$H NMR (400 MHz, CDCl$_3$) δ 8.12 (s, 1H), 7.10 (dd, J=0.8, 8.0 Hz, 1H), 6.92 (t, J=8.0 Hz, 1H), 6.69 (dd, J=0.8, 8.0 Hz, 1H), 5.13 (dd, J=5.2, 12.4 Hz, 1H), 4.33 (s, 2H), 3.71 (s, 3H), 3.69-3.64 (m, 2H),

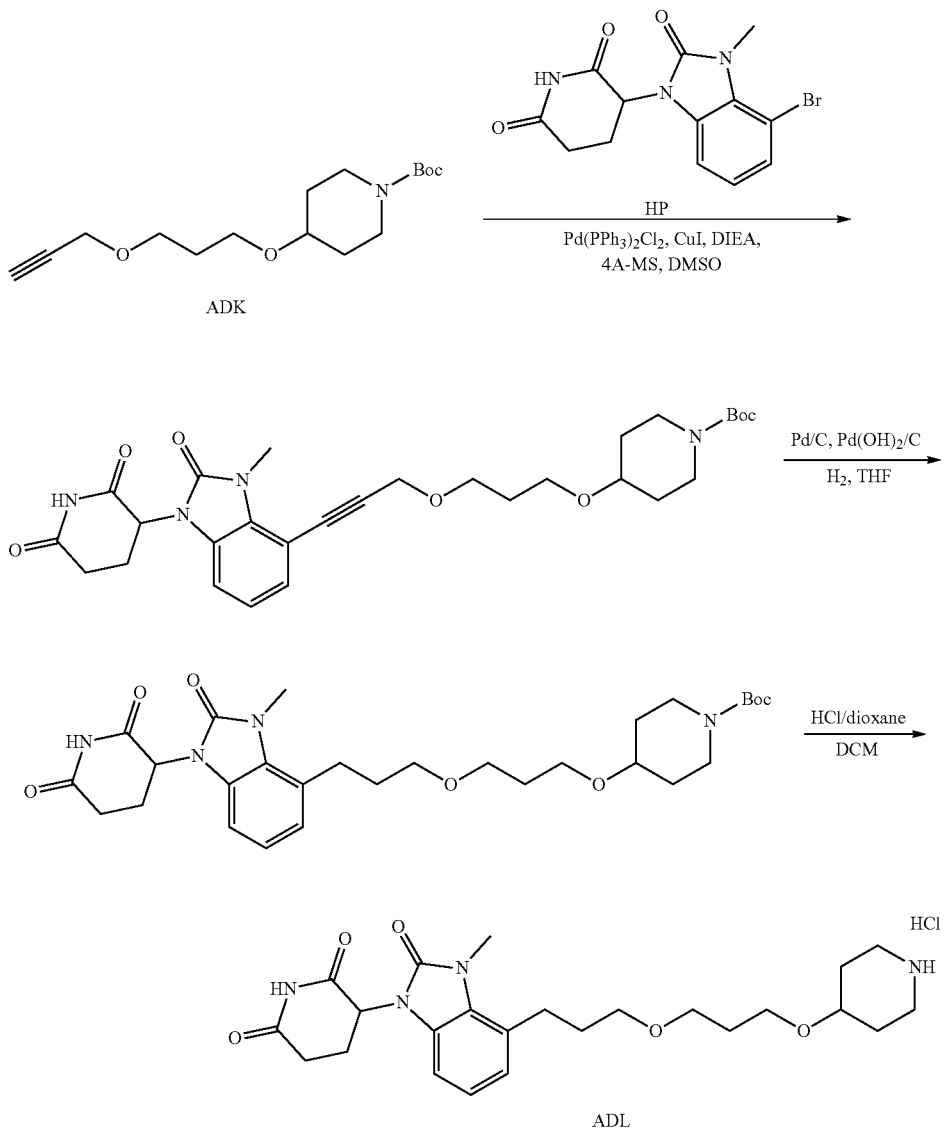

3.61 (t, J=6.4 Hz, 2H), 3.49 (t, J=6.4 Hz, 2H), 3.38-3.34 (m, 1H), 3.03-2.98 (m, 2H), 2.82-2.60 (m, 2H), 2.21-2.12 (m, 1H), 1.86-1.80 (m, 2H), 1.75-1.71 (m, 2H), 1.47-1.39 (m, 3H), 1.38 (s, 9H). LC-MS (ESI+) m/z 577.2 (M+Na)+.

Step 2—Tert-butyl 4-[3-[3-[1-(2,6-dioxo-3-piperidyl)-3-methyl-2-oxo-benzimidazol-4-yl]propoxy]propoxy]piperidine-1-carboxylate To a solution of tert-butyl 4-[3-[3-[1-(2,6-dioxo-3-piperidyl)-3-methyl-2-oxo-benzimidazol-4-yl] prop-2-ynoxy]propoxy]piperidine-1-carboxylate (700 mg, 1.26 mmol) in THF (10 mL) was added Pd/C (0.1 g, 10% wt) and Pd(OH)$_2$/C (0.1 g, 10% wt). The suspension was degassed under vacuum and purged with H$_2$ several times. The mixture was stirred under (15 psi) at 25° C. for 12 hours. On completion, the mixture was concentrated in vacuo to give the title compound (500 mg, 71% yield) as white solid. $^1$H NMR (400 MHz, CDCl$_3$) δ 8.16 (s, 1H), 7.04-6.98 (m, 1H), 6.95-6.90 (m, 1H), 6.69 (dd, J=0.8, 8.0 Hz, 1H), 5.29-5.18 (m, 1H), 3.84-3.73 (m, 2H), 3.70 (s, 3H), 3.60-3.47 (m, 6H), 3.47-3.41 (m, 1H), 3.15-3.08 (m, 2H), 3.06-3.01 (m, 2H), 3.00-2.73 (m, 3H), 2.32-2.18 (m, 1H), 1.96-1.80 (m, 6H), 1.58-1.49 (m, 2H), 1.47 (s, 9H). LC-MS (ESI+) m/z 559.4 (M+H)+.

Step 3—3-[3-Methyl-2-oxo-4-[3-[3-(4-piperidyloxy)propoxy]propyl]benzimidazol-1-yl]]piperidine-2,6-dione To a solution of tert-butyl 4-[3-[3-[1-(2,6-dioxo-3-piperidyl)-3-methyl-2-oxo-benzimidazol-4-yl] propoxy]propoxy]piperidine-1-carboxylate (500 mg, 894 umol) in DCM (10 mL) was added HCl/dioxane (4 M, 10 mL). The reaction mixture was stirred at 20° C. for 2 hrs. On completion, the reaction mixture was concentrated in vacuo to give the title compound (440 mg, 99% yield, HCl salt) as white solid. LC-MS (ESI+) m/z 459.2 (M+H)+.

Pyrazolo[1,5-a]pyrimidine-3-carbonyl chloride (Intermediate ADM)

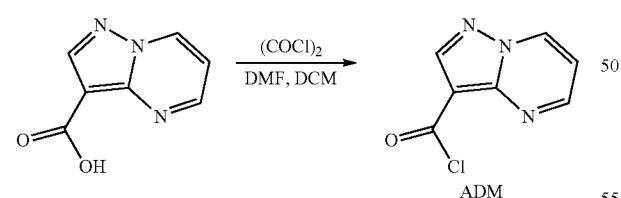

To a solution of pyrazolo[1,5-a]pyrimidine-3-carboxylic acid (200 mg, 1.23 mmol, CAS #25940-35-6) and DMF (8.96 mg, 123 umol) in DCM (4 mL) was added (COCl)$_2$ (311 mg, 2.45 mmol). The reaction mixture was stirred at 30° C. for 2 days. On completion, the mixture was concentrated in vacuo to give the title compound (200 mg, 90% yield) as a gray powder.

N-[2-(5-methyl-2-pyridyl)-5-(4-piperidyl)pyrazol-3-yl]pyrazolo[1,5-a]pyrimidine-3-carboxamide (Intermediate ADN)

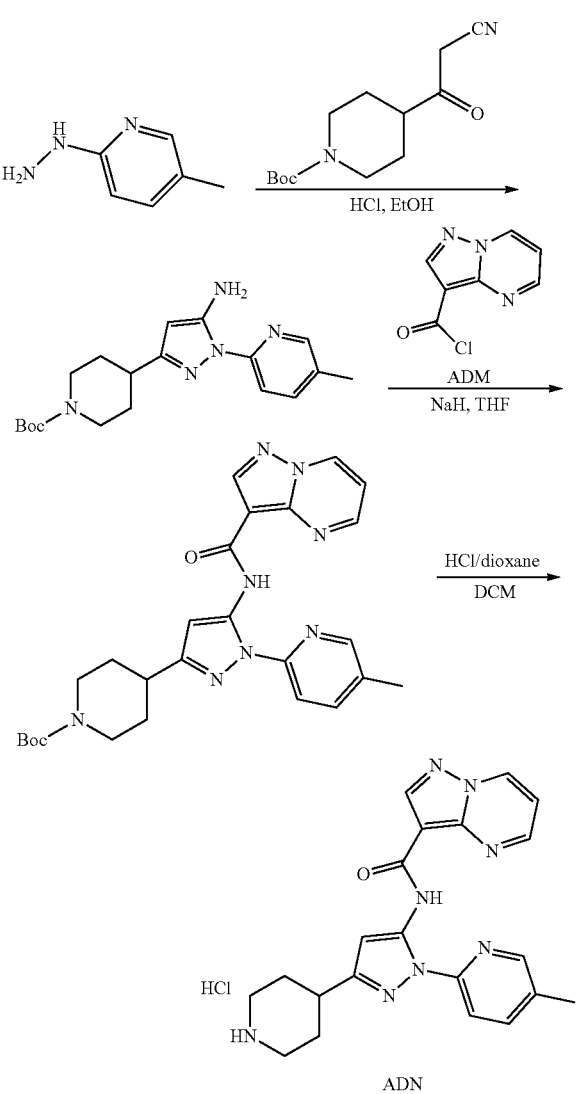

Step 1—Tert-butyl 4-[5-amino-1-(5-methyl-2-pyridyl)pyrazol-3-yl]piperidine-1-carboxylate To a solution of (5-methyl-2-pyridyl)hydrazine (488 mg, 3.96 mmol, CAS #4931-01-5) and tert-butyl 4-(2-cyanoacetyl)piperidine-1-carboxylate (1 g, 3.96 mmol, CAS #660406-84-8) in EtOH (8 mL) was added HCl (12 M, 33.0 uL). The reaction mixture was stirred at 80° C. for 6 hrs. On completion, the mixture was concentrated in vacuo and the residue was purified by reverse phase (0.1% FA condition) to give the title compound (1.00 g, 71% yield) as yellow powder. $^1$H NMR (400 MHz, DMSO-d$_6$) δ 8.19 (s, 1H), 7.76-7.66 (m, 2H), 6.67 (s, 2H), 5.27 (s, 1H), 3.97 (d, J=12.4 Hz, 2H), 2.96-2.74 (m, 2H), 2.69-2.59 (m, 1H), 2.29 (s, 3H), 1.87-1.77 (m, 2H), 1.52-1.42 (m, 2H), 1.40 (s, 9H); LC-MS (ESI+) m/z 358.1 (M+H)+.

Step 2—Tert-butyl 4-[1-(5-methyl-2-pyridyl)-5-(pyrazolo[1,5-a]pyrimidine-3-carbonylamino)pyrazol-3-yl]piperidine-1-carboxylate To a solution of tert-butyl 4-[5-amino-1-(5-methyl-2-pyridyl)pyrazol-3-yl]piperidine-1-carboxylate (295 mg, 826 umol) in THF (4 mL) was added NaH (132 mg, 3.30 mmol, 60% dispersion in mineral oil) at 0° C. After 0.5 hr later, pyrazolo[1,5-a]pyrimidine-3-carbonyl chloride (150 mg, 826 umol, Intermediate ADM) was added into the above mixture and the reaction mixture was stirred 20° C. for 17 hrs. On completion, the mixture was quenched with water (20 mL), extracted with EA (2×30 mL). The organic layer was washed with brine (50 mL), then concentrated in vacuo. The residue was purified by reverse phase (0.1% FA condition) to give the title compound (220 mg, 53% yield) as a red powder. $^1$H NMR (400 MHz, DMSO-$d_6$) δ 13.14 (s, 1H), 9.38 (dd, J=1.6, 7.2 Hz, 1H), 9.14 (dd, J=1.6, 4.4 Hz, 1H), 8.73 (s, 1H), 8.52 (s, 1H), 7.89-7.78 (m, 2H), 7.37 (dd, J=4.4, 7.2 Hz, 1H), 6.90 (s, 1H), 4.10-3.90 (m, 2H), 3.00-2.77 (m, 3H), 2.41 (s, 3H), 2.01-1.85 (m, 2H), 1.61-1.48 (m, 2H), 1.42 (s, 9H).

Step 3—N-[2-(5-methyl-2-pyridyl)-5-(4-piperidyl)pyrazol-3-yl]pyrazolo[1,5-a]pyrimidine-3-carboxamide To a solution of tert-butyl 4-[1-(5-methyl-2-pyridyl)-5-(pyrazolo[1,5-a]pyrimidine-3-carbonylamino) pyrazol-3-yl] piperidine-1-carboxylate (220 mg, 438 umol) in DCM (5 mL) was added HCl/dioxane (5 mL). The reaction mixture was stirred at 20° C. for 2 hrs. On completion, the mixture was concentrated in vacuo to give the title compound (190 mg, 99% yield, HCl salt) as a red powder. LC-MS (ESI$^+$) m/z 403.2 (M+H)$^+$.

4-[1-(Cyclopropylmethyl)indazol-5-yl]benzaldehyde (Intermediate ADO)

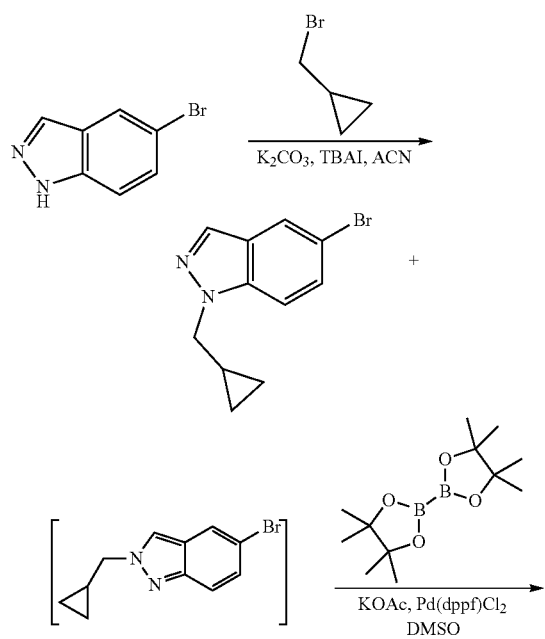

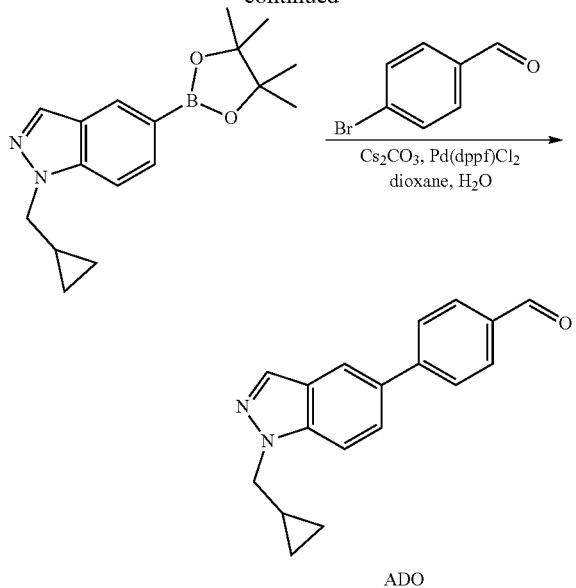

ADO

Step 1: 5-bromo-2-(cyclopropylmethyl) indazole, 5-bromo-1-(cyclopropylmethyl) indazole To a solution of 5-bromo-1H-indazole (40 g, 203 mmol) and bromomethylcyclopropane (82.2 g, 609 mmol) in ACN (500 mL) was added $K_2CO_3$ (84.1 g, 609 mmol) and TBAI (7.50 g, 20.3 mmol). Then the mixture was stirred at 80° C. for 12 hrs. The reaction mixture was then concentrated under reduced pressure. The residue was purified by column chromatography (SiO$_2$, Petroleum ether/Ethyl acetate=40/1) to give the title compound 5-bromo-2-(cyclopropylmethyl) indazole (25 g, 48% yield) as a yellow oil. LC-MS (ESI$^+$) m/z 251.0 (M+H)$^+$. 1H NMR (400 MHz, DMSO-$d_6$) δ=8.41 (s, 1H), 7.97 (d, J=1.6 Hz, 1H), 7.60 (d, J=9.2 Hz, 1H), 7.31 (dd, J=2.0, 9.0 Hz, 1H), 4.29 (d, J=7.2 Hz, 2H), 1.38 (m, 1H), 0.61-0.52 (m, 2H), 0.47-0.40 (m, 2H).

Step 2: 1-(cyclopropylmethyl)-5-(4,4,5,5-tetramethyl-1,3,2-dioxaborolan-2-yl) indazole A mixture of 5-bromo-1-(cyclopropylmethyl) indazole (10 g, 39.8 mmol), 4,4,5,5-tetramethyl-2-(4,4,5,5-tetramethyl-1,3,2-dioxaborolan-2-yl)-1,3,2-dioxaborolane (20.2 g, 79.6 mmol), KOAc (11.7 g, 119 mmol), and Pd(dppf)Cl$_2$ (1.46 g, 1.99 mmol) in DMSO (100 mL) was degassed and purged with N$_2$ three times and then the mixture was stirred at 85° C. for 12 hrs under N$_2$ atmosphere. The reaction mixture was diluted with H$_2$O (200 mL) and extracted with EA (200 mL×3). The combined organic layers were washed with brine 600 mL (200 mL×3), dried over sodium sulfate, filtered and concentrated under reduced pressure to give a residue. The residue was purified by column chromatography (SiO$_2$, Petroleum ether/Ethyl acetate=50/1 to 10/1) to give the title compound (10 g, 76% yield) as a yellow solid. LC-MS (ESI$^+$) m/z 299.2 (M+H)$^+$. 1H NMR (400 MHz, CClD$_3$) δ=8.28 (s, 1H), 8.01 (s, 1H), 7.79 (dd, J=0.8, 8.8 Hz, 1H), 7.41 (d, J=8.4 Hz, 1H), 4.27 (d, J=7.2 Hz, 2H), 1.37 (s, 12H), 0.60-0.54 (m, 2H), 0.43-0.38 (m, 2H).

Step 3: 4-[1-(cyclopropylmethyl) indazol-5-yl]benzaldehyde

A mixture of 1-(cyclopropylmethyl)-5-(4,4,5,5-tetramethyl-1,3,2-dioxaborolan-2-yl) indazole (4 g, 13.4 mmol), 4-bromobenzaldehyde (3.72 g, 20.1 mmol), Cs$_2$CO$_3$ (2 M, 20.12 mL), and Pd(dppf)Cl$_2$ (490 mg, 670 umol) in dioxane (40 mL) was degassed and purged with N$_2$ for 3 times and then the mixture was stirred at 85° C. for 12 hrs under N$_2$ atmosphere. The reaction mixture was diluted with H$_2$O (50 mL) and extracted with EA (50 mL×3). The combined organic layers were washed with brine (50 mL×3), dried over sodium sulfate, filtered and concentrated under reduced pressure. The residue was purified by column chromatography (SiO$_2$, Petroleum ether/Ethyl acetate=50/1 to 10/1) to give the title compound (2.8 g, 58% yield) as a yellow solid. LC-MS (ESI$^+$) m/z 276.9 (M+H)$^+$.

3-(2-Oxo-6-(3-(piperidin-4-yloxy)propyl)benzo[d]oxazol-3(2H)-yl)piperidine-2,6-dione (Intermediate ADP)

Step 1—Tert-butyl 4-((3-(3-(2,6-dioxopiperidin-3-yl)-2-oxo-2,3-dihydrobenzo[d]oxazol-6-yl) prop-2-yn-1-yl)oxy)piperidine-1-carboxylate A mixture of tert-butyl 4-prop-2-ynoxypiperidine-1-carboxylate (440 mg, 1.84 mmol, Intermediate™), 3-(6-bromo-2-oxo-1,3-benzoxazol-3-yl)piperidine-2,6-dione (460 mg, 1.41 mmol, Intermediate OZ), Pd(PPh$_3$)$_2$Cl$_2$ (99.3 mg, 141 umol), CsF (860 mg, 5.66 mmol), CuI (26.9 mg, 141 umol) and 4 Å molecular sieves (100 mg) in DMF (5 mL) was stirred at 80° C. for 12 hours under N$_2$ atmosphere. On completion, the reaction mixture was filtered and concentrated in vacuo. The residue was purified by reverse phase (0.1% FA) to give the title compound (340 mg, 47% yield) as a white solid. $^1$H NMR (400 MHz, DMSO-d$_6$) δ 11.23 (s, 1H), 7.53 (s, 1H), 7.40-7.23 (m, 2H), 5.40 (dd, J=5.6, 13.2 Hz, 1H), 4.43 (s, 2H), 3.71-3.58 (m, 3H), 3.10-2.99 (m, 2H),

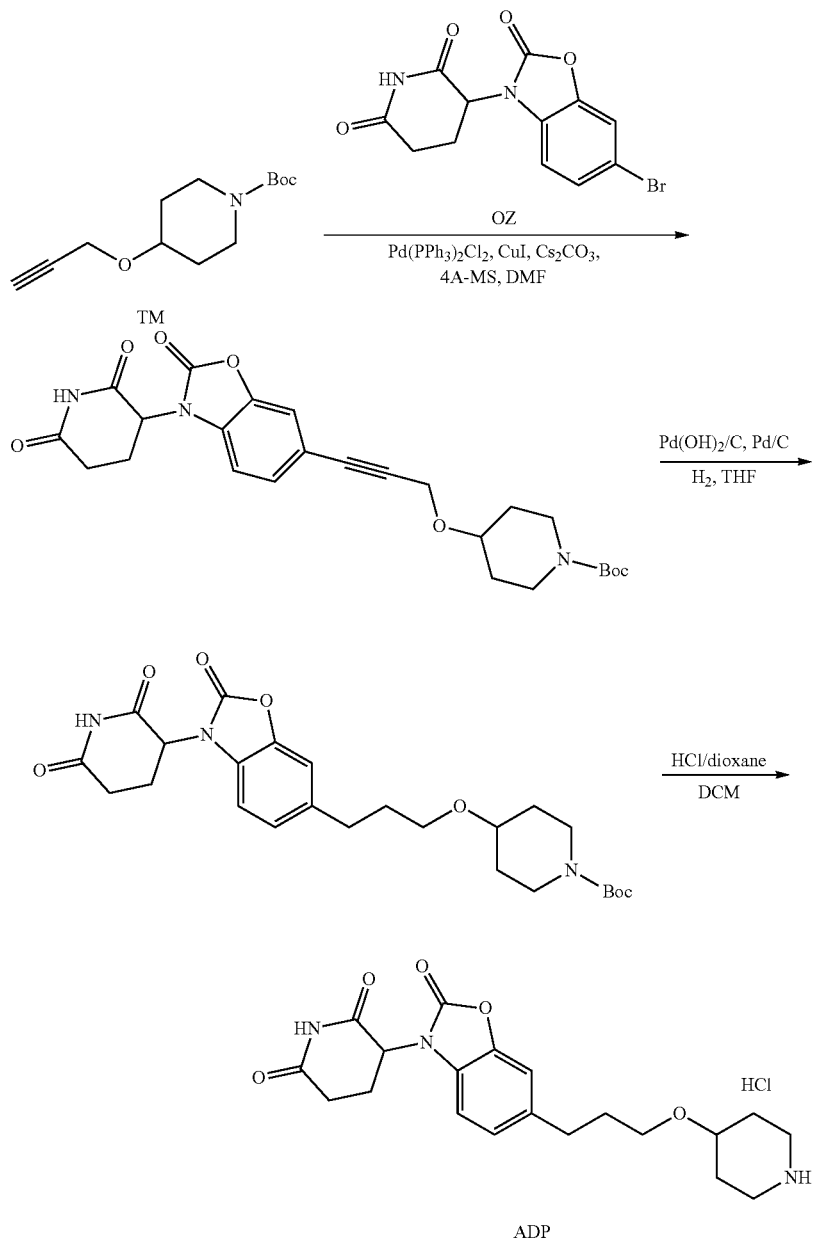

2.94-2.81 (m, 1H), 2.72-2.64 (m, 2H), 2.20-2.15 (m, 1H), 1.90-1.80 (m, 2H), 1.48-1.39 (m, 11H).

Step 2—Tert-butyl 4-(3-(3-(2,6-dioxopiperidin-3-yl)-2-oxo-2,3-dihydrobenzo[d]oxazol-6-yl) propoxy) piperidine-1-carboxylate To a solution of tert-butyl 4-[3-[3-(2,6-dioxo-3-piperidyl)-2-oxo-1,3-benzoxazol-6-yl]prop-2-ynoxy] piperidine-1-carboxylate (324 mg, 670 umol) in THF (8 mL) was added Pd/C (150 mg, 10% wt) and Pd(OH)$_2$ (150 mg, 10% wt). The reaction mixture was stirred at 25° C. for 12 hours under H$_2$ (15 psi) atmosphere. On completion, the reaction mixture was filtered and the filtrate was concentrated in vacuo to give the title compound (326 mg, 95% yield) as a white solid. $^1$H NMR (400 MHz, CDCl$_3$) δ 8.08 (s, 1H), 7.12 (s, 1H), 7.00 (d, J=8.0 Hz, 1H), 5.40 (d, J=8.0 Hz, 1H), 5.08-5.00 (m, 1H), 3.80-3.72 (m, 2H), 3.48-3.40 (m, 3H), 3.15-3.05 (m, 2H), 3.00-2.90 (m, 1H), 2.85-2.80 (m, 1H), 2.75-2.65 (m, 2H), 2.40-2.30 (m, 1H), 1.90-1.82 (m, 2H), 1.60-1.40 (m, 5H), 1.47 (s, 9H). LC-MS (ESI$^+$) m/z 388.2 (M–100)$^+$.

Step 3—3-(2-Oxo-6-(3-(piperidin-4-yloxy)propyl) benzo[d]oxazol-3(2H)-yl)piperidine-2,6-dione hydrochloride A mixture of tert-butyl 4-[3-[3-(2,6-dioxo-3-piperidyl)-2-oxo-1,3-benzoxazol-6-yl]propoxy] piperidine-1-carboxylate (326 mg, 669 umol) and HCl/dioxane (4 M, 8 mL) was stirred at 25° C. for 1 hour. On completion, the reaction mixture was concentrated in vacuo to give the title compound (250 mg, 86% yield, HCl salt) as a white solid. $^1$H NMR (400 MHz, DMSO-d$_6$) δ 11.19 (s, 1H), 9.04-8.68 (m, 2H), 7.29-6.99 (m, 3H), 5.37 (dd, J=5.2, 12.8 Hz, 1H), 3.40 (t, J=6.0 Hz, 2H), 3.35-3.25 (m, 2H), 3.15-3.05 (m, 2H), 2.95-2.80 (m, 3H), 2.70-2.65 (m, 3H), 1.94-1.64 (m, 6H).

Tert-butyl N-[3-(2-aminoethoxy)propyl]-N-methyl-carbamate (Intermediate ADQ)

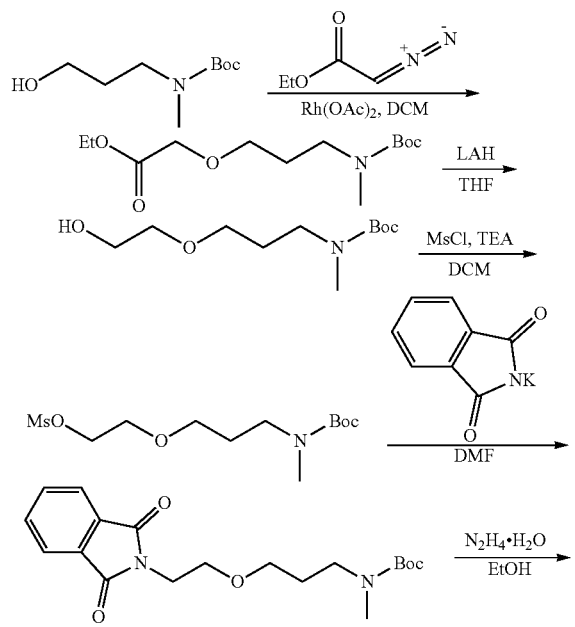

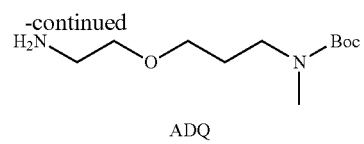

ADQ

Step 1—Ethyl 2-[3-[tert-butoxycarbonyl(methyl) amino]propoxy]acetate

To a mixture of tert-butyl N-(3-hydroxypropyl)-N-methyl-carbamate (4.50 g, 23.8 mmol, CAS #98642-44-5) and Rh(OAc)$_2$ (525 mg, 2.38 mmol) in DCM (15.0 mL) was added a solution of ethyl 2-diazoacetate (4.07 g, 35.6 mmol) in DCM (15.0 mL), and the mixture was stirred at 20° C. for 16 hrs. On completion, the reaction mixture was diluted with DCM (50 mL) and washed with water (3×100 mL). The combined organic layers were washed with brine (2×100 mL), dried over Na$_2$SO$_4$, filtered and concentrated in vacuo to give a residue. The residue was purified by silica gel column (PE:EA=8:1) to give the title compound (6.00 g, 91% yield) as a white solid. $^1$H NMR (400 MHz, DMSO-d$_6$) δ 4.14-4.09 (m, 2H), 4.06 (s, 2H), 3.44 (t, J=6.4 Hz, 2H), 3.20 (t, J=7.2 Hz, 2H), 2.76 (s, 3H), 1.73-1.66 (m, 2H), 1.38 (s, 9H), 1.20 (t, J=7.2 Hz, 3H).

Step 2—Tert-butyl N-[3-(2-hydroxyethoxy)propyl]-N-methyl-carbamate

To a mixture of LiAlH$_4$ (496.2 mg, 13.1 mmol) in THF (5.00 mL) was added a solution of ethyl 2-[3-[tertbutoxycarbonyl(methyl)amino]propoxy]acetate (3.00 g, 10.9 mmol,) in THF (5.00 mL) at 0° C., then the mixture was stirred at 0° C. for 2 hrs. On completion, the reaction mixture was quenched with water (10 mL) at 0° C., and dried over Na$_2$SO$_4$, filtered and concentrated in vacuo to give the title compound (2.11 g, 83% yield) as a white solid. $^1$H NMR (400 MHz, DMSO-d$_6$) δ 4.54 (t, J=5.2 Hz, 1H), 3.50-3.46 (m, 2H), 3.40-3.34 (m, 4H), 3.19 (t, J=6.8 Hz, 2H), 2.76 (s, 3H), 1.71-1.64 (m, 2H), 1.38 (s, 9H).

Step 3—2-[3-[Tert-butoxycarbonyl(methyl)amino] propoxy ethyl methanesulfonate

To a solution of tert-butyl N-[3-(2-hydroxyethoxy)propyl]-N-methyl-carbamate (1.50 g, 6.43 mmol,) and TEA (1.95 g, 19.3 mmol) in DCM (10.0 mL) was added MsCl (1.25 g, 10.9 mmol, 845 uL) at 0° C., and the mixture was stirred at 25° C. for 1 hr. On completion, the reaction mixture was quenched with water (2 mL), and then washed with water (3×10 mL) and brine (3×10 mL), dried over Na$_2$SO$_4$, filtered and concentrated in vacuo to give the title compound (1.80 g, 89% yield) as a white solid. $^1$H NMR (400 MHz, DMSO-d$_6$) δ 4.33-4.27 (m, 2H), 3.65-3.59 (m, 2H), 3.42 (t, J=6.4 Hz, 2H), 3.22-3.18 (m, 2H), 3.17 (s, 3H), 2.76 (s, 3H), 1.73-1.66 (m, 2H), 1.39 (s, 9H).

Step 4—Tert-butyl N-[3-[2-(1,3-dioxoisoindolin-2-yl)ethoxy]propyl]-N-methyl-carbamate To a solution of 2-[3-[tert-butoxycarbonyl(methyl)amino] propoxy] ethyl methanesulfonate (1.50 g, 4.82 mmol) in DMF (30.0 mL) was added (1,3-dioxoisoindolin-2-yl)potassium (1.34 g, 7.23 mmol). The mixture was stirred at 100° C. for 16 hrs. On completion, the reaction mixture was diluted with H$_2$O (30 mL), then extracted with EA (3×30 mL). The organic layers were washed with brine (2×30 mL) and dried over anhydrous $Na_2SO_4$, filtered and concentrated in vacuo to give a residue. The residue was purified by column chromatography to give the title compound (1.70 g, 97% yield) as yellow oil. $^1H$ NMR (400 MHz, $CDCl_3$) δ 7.86-7.81 (m, 2H), 7.71-7.21 (m, 2H), 3.88 (t, J=5.6 Hz, 2H), 3.65 (t, J=5.6 Hz, 2H), 3.45 (t, J=6.4 Hz, 2H), 3.20-3.18 (m, 2H), 2.77 (s, 3H), 1.76-1.62 (m, 2H), 1.42 (s, 9H).

Step 5—Tert-butyl N-[3-(2-aminoethoxy)propyl]-N-methyl-carbamate

To a solution of tert-butyl N-[3-[2-(1,3-dioxoisoindolin-2-yl)ethoxy]propyl]-N-methyl-carbamate (1.00 g, 2.76 mmol) in EtOH (15.0 mL) was added $N_2H_4 \cdot H_2O$ (690 mg, 13.8 mmol, 670 uL, 98%), and the mixture was stirred at 80° C. for 2 hrs. On completion, the reaction mixture was filtered and the filtrate concentrated in vacuo to give the title compound (540 mg, 84% yield) as colorless oil. $^1H$ NMR (400 MHz, $CDCl_3$) δ 3.49-3.41 (m, 4H), 3.30 (s, 2H), 2.93-2.77 (m, 5H), 1.86-1.72 (m, 2H), 1.46 (s, 9H), 1.40 (d, J=1.6 Hz, 2H).

2-(2,6-Dioxo-3-piperidyl)-4-[2-[3-(methylamino)propoxy]ethylamino]isoindoline-1,3-dione (Intermediate ADR)

Step 1—Tert-butyl N-[3-[2-[[2-(2,6-dioxo-3-piperidyl)-1,3-dioxo-isoindolin-4-yl] amino] ethoxy] propyl]-N-methyl-carbamate To a mixture of tert-butyl N-[3-(2-aminoethoxy)propyl]-N-methyl-carbamate (100 mg, 430 umol, Intermediate ADQ) and 2-(2,6-dioxo-3-piperidyl)-4-fluoro-isoindoline-1,3-dione (118 mg, 430 umol, Intermediate R) in DMSO (10.0 mL) was added DIPEA (278 mg, 2.15 mmol, 375 uL). The mixture was stirred at 130° C. for 3 hrs. On completion, the reaction mixture was quenched with water (10.0 mL), and then diluted with EA (10 mL) and extracted with EA (3×30 mL). The combined organic layers were washed with brine (3×50 mL), dried over $Na_2SO_4$, filtered and concentrated in vacuo to give a residue. The residue was purified by reversed phase (0.1% FA condition) to give the tile compound (130 mg, 61% yield) as a yellow solid. $^1H$ NMR (400 MHz, $CDCl_3$) δ 8.09-8.01 (m, 1H), 7.52-7.48 (m, 1H), 7.12 (d, J=7.2 Hz, 1H), 6.94 (d, J=8.4 Hz, 1H), 6.52-6.50 (m, 1H), 4.97-4.87 (m, 1H), 3.69-3.61 (m, 2H), 3.54-3.43 (m, 4H), 3.30 (t, J=6.4 Hz, 2H), 2.95-2.68 (m, 6H), 2.19-2.09 (m, 1H), 1.82 (m, 2H), 1.46 (s, 9H).

Step 2—2-(2,6-Dioxo-3-piperidyl)-4-[2-[3-(methylamino)propoxy] ethylamino]isoindoline-1,3-dione To a solution of tert-butyl N-[3-[2-[[2-(2,6-dioxo-3-piperidyl)-1,3-dioxo-isoindolin-4-yl] amino] ethoxy]propyl]-N-methylcarbamate (120 mg, 245 umol) in DCM (6.00 mL) was added HCl/dioxane (4 M, 6.00 mL). The mixture was stirred at 20° C. for 0.5 hr. On completion, the reaction mixture was concentrated in vacuo to give the title compound (100 mg, 95% yield, HCl) as a yellow solid. LC-MS ($ESI^+$) m/z 389.1 $(M+H)^+$.

2-(2,6-Dioxo-3-piperidyl)-1,3-dioxo-isoindoline-4-carbaldehyde (Intermediate ADS)

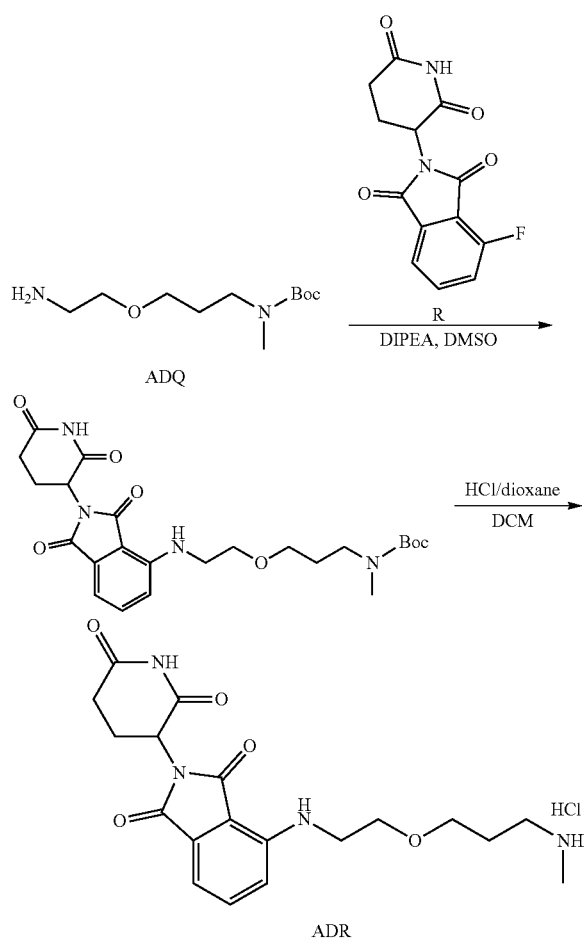

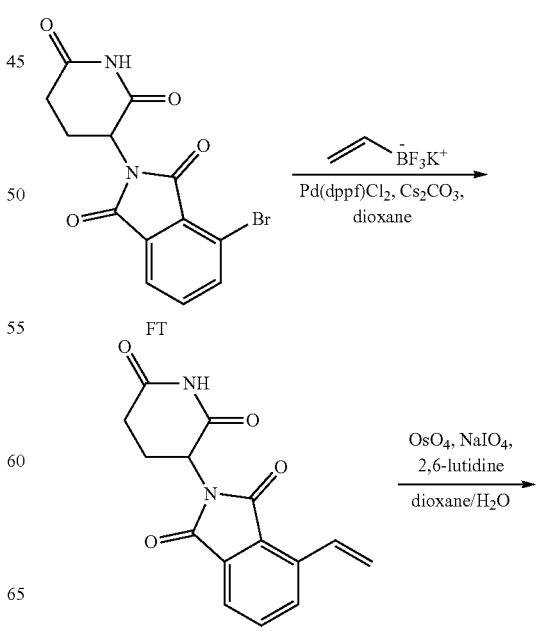

Step 1—2-(2,6-Dioxo-3-piperidyl)-4-vinyl-isoindoline-1,3-dione

To a solution of 4-bromo-2-(2,6-dioxo-3-piperidyl)isoindoline-1,3-dione (2.00 g, 5.93 mmol, Intermediate FT) and potassium hydride; trifluoro(vinyl)boron (2.38 g, 17.8 mmol) in dioxane (20 mL) was added Pd(dppf)Cl$_2$.CH$_2$Cl$_2$ (434 mg, 593 umol) and Cs$_2$CO$_3$ (3.87 g, 11.9 mmol). The reaction mixture was stirred at 90° C. for 20 hrs. The reaction mixture was filtered and concentrated in vacuo. The residue was purified by silica gel column chromatography (THF) to give the compound (1.09 g, 65% yield) as yellow solid. $^1$H NMR (400 MHz, DMSO-d$_6$) δ 11.14 (s, 1H), 8.18 (dd, J=2.8, 6.4 Hz, 1H), 7.87-7.81 (m, 2H), 7.65 (dd, J=11.2, 17.6 Hz, 1H), 6.90-6.63 (m, 1H), 6.23 (d, J=17.6 Hz, 1H), 5.66 (d, J=11.2 Hz, 1H), 5.15 (dd, J=5.2, 12.8 Hz, 1H), 2.95-2.83 (m, 1H), 2.18 (s, 1H), 2.10-2.02 (m, 1H). LC-MS (ESI$^+$) m/z 285.1 (M+H)$^+$.

Step 2—2-(2,6-Dioxo-3-piperidyl)-1,3-dioxo-isoindoline-4-carbaldehyde

A mixture of 2-(2,6-dioxo-3-piperidyl)-4-vinyl-isoindoline-1,3-dione (200 mg, 704 umol), NaIO$_4$ (602 mg, 2.81 mmol, 156 uL), OsO$_4$ (5.37 mg, 21.1 umol, 1.10 uL) and 2,6-lutidine (151 mg, 1.41 mmol, 164 uL) in a mixed solvents of dioxane (3 mL) and H$_2$O (3 mL) at 0° C. The reaction mixture was stirred at 25° C. for 5 hours. The reaction mixture was quenched by sat. aq. NaS$_2$SO$_3$ (3 mL). The aqueous phase was extracted with DCM (2×10 mL). The combined organic phase was washed with brine (2×10 mL), dried with anhydrous Na$_2$SO$_4$, filtered and concentrated in vacuo. The crude product was purified by reversed-phase HPLC (0.1% FA condition) to give the compound (60.0 mg, 25% yield) was obtained white solid. $^1$H NMR (400 MHz, DMSO-d$_6$) δ 11.17 (s, 1H), 10.82 (s, 1H), 8.21 (dd, J=3.6, 7.2 Hz, 2H), 8.06-8.00 (m, 1H), 5.23 (dd, J=5.6, 12.8 Hz, 1H), 3.64 (s, 1H), 2.98-2.84 (m, 1H), 2.62-2.53 (m, 2H), 2.13-2.09 (m, 1H).

2-(2,6-Dioxo-3-piperidyl)-4-[[4-(methylamino)-1-piperidyl] methyl] isoindoline-1,3-dione (Intermediate ADT)

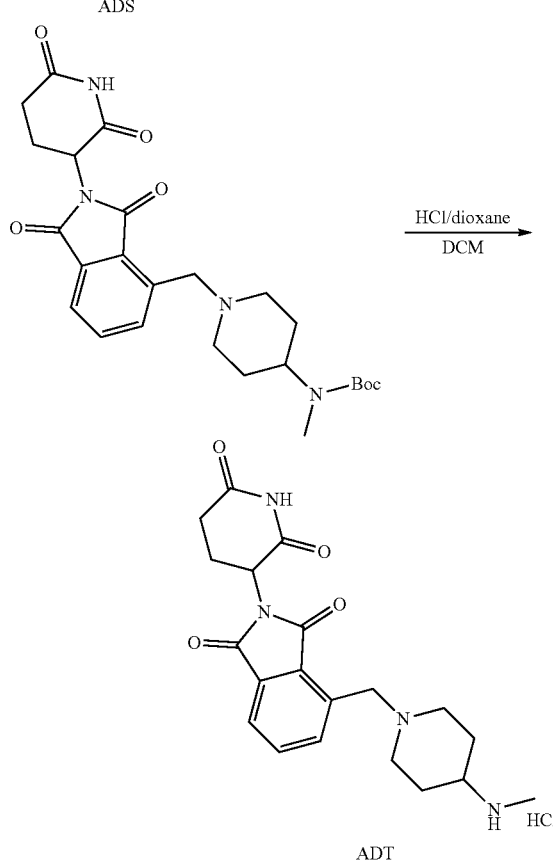

Step 1—Tert-butyl N-[1-[[2-(2,6-dioxo-3-piperidyl)-1,3-dioxo-isoindolin-4-yl] methyl]-4-piperidyl]-N-methyl-carbamate To a solution of 2-(2,6-dioxo-3-piperidyl)-1,3-dioxo-isoindoline-4-carbaldehyde (44.7 mg, 133 umol, Intermediate ADS) and tert-butyl N-methyl-N-(4-piperidyl)carbamate (28.5 mg, 133 umol, CAS #108612-54-0) in a mixed solvent of THF (1.5 mL) and DMF (1.5 mL) was added HOAc (15.9 mg, 265 umol). After 30 min, NaBH(OAc)$_3$ (42.2 mg, 199 umol) was added, then the mixture was stirred at 20° C. for 16 hrs. The reaction mixture was quenched with water (0.5 ml) and concentrated in vacuo to give the compound (40.0 mg, 49% yield) as white solid. $^1$H NMR (400 MHz, DMSO-d$_6$) δ 11.15-11.09 (m, 1H), 7.99-7.77 (m, 3H), 5.13 (dd, J=5.6, 12.8 Hz, 1H), 4.00-3.90 (m, 2H), 3.87-3.62 (m, 1H), 2.97-2.82 (m, 3H), 2.67 (s, 3H), 2.56 (d, J=10.8 Hz, 2H), 2.52-2.00 (m, 2H), 2.17-2.00 (m, 3H), 1.78-1.60 (m, 2H), 1.57-1.44 (m, 2H), 1.39 (s, 7H). LC-MS (ESI$^+$) m/z 485.3 (M+H)$^+$.

Step 2—2-(2,6-Dioxo-3-piperidyl)-4-[[4-(methylamino)-1-piperidyl] methyl]isoindoline-1,3-dione To a solution of tert-butyl N-[1-[[2-(2,6-dioxo-3-piperidyl)-1,3-dioxo-isoindolin-4-yl] methyl]-4-piperidyl]-N-methyl-carbamate (40.0 mg, 82.5 umol) in DCM (0.5 mL) was added HCl/dioxane (0.5 mL). The reaction mixture was stirred at 25° C. for 2 hrs. The reaction mixture was then filtered and concentrated in vacuo to give the compound (30.0 mg, 86% yield, HCl) as brown solid. LC-MS (ESI$^+$) m/z 385.2 (M+H)$^+$.

Benzyl 4-(4-aminobutoxy)piperidine-1-carboxylate (Intermediate ADU)

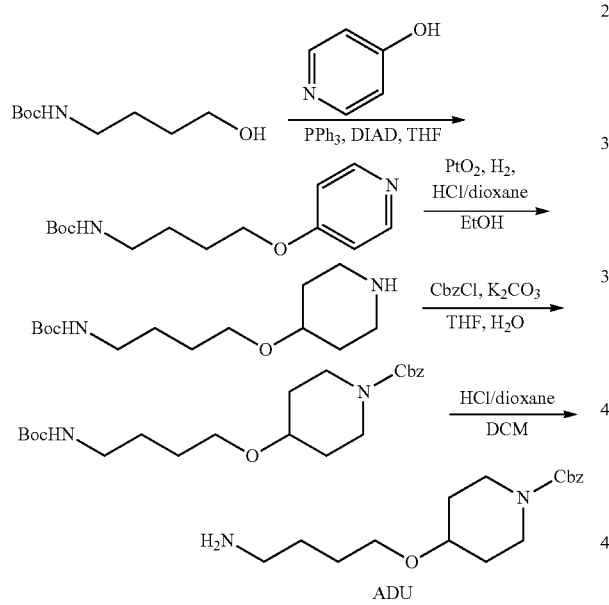

Step 1—Tert-butyl N-[4-(4-pyridyloxy)butyl]carbamate

To a solution of tert-butyl N-(4-hydroxybutyl)carbamate (300 mg, 1.59 mmol, CAS #75178-87-9), pyridin-4-ol (226 mg, 2.38 mmol, CAS #626-64-2) and PPh$_3$ (623 mg, 2.38 mmol) in THF (15 mL) was added DIAD (480 mg, 2.38 mmol) at 0° C. Then the mixture was stirred at 50° C. for 16 hrs. On completion, the mixture was diluted with EA (30 mL), washed with H$_2$O (3×15 mL), brine (2×20 mL) dried over anhydrous Na$_2$SO$_4$, filtered and concentrated in vacuo. The mixture was purified by reverse phase: (0.1% FA) to give the title compound (300 mg, 71% yield) as yellow oil. $^1$H NMR (400 MHz, CDCl$_3$) δ 8.48 (d, J=6.4 Hz, 2H), 6.93 (d, J=6.4 Hz, 2H), 4.66 (s, 1H), 4.10 (t, J=6.4 Hz, 2H), 3.27-3.11 (m, 2H), 1.92-1.81 (m, 2H), 1.73-1.61 (m, 2H), 1.44 (s, 9H)

Step 2—Tert-butyl N-[4-(4-piperidyloxy)butyl]carbamate

To a solution of tert-butyl N-[4-(4-pyridyloxy)butyl]carbamate (300 mg, 1.13 mmol) in EtOH (10.0 mL) was added HCl/dioxane (4.00 M, 281 uL) and PtO$_2$ (255 mg, 1.13 mmol). The mixture was stirred at 40° C. for 16 hrs under H$_2$ (50 psi). On completion, the mixture was filtered and concentrated in vacuo to give the title compound (260 mg, 74% yield) as white solid. $^1$H NMR (400 MHz, DMSO-d$_6$) δ 4.47-4.26 (m, 1H), 3.59-3.48 (m, 1H), 3.47-3.41 (m, 2H), 3.03-2.93 (m, 4H), 2.92-2.86 (m, 2H), 1.75-1.63 (m, 4H), 1.59-1.52 (m, 2H), 1.49-1.39 (m, 2H), 1.37 (s, 9H).

Step 3—Benzyl 4-[4-(tert-butoxycarbonylamino) butoxy]piperidine-1-carboxylate

To a solution of tert-butyl N-[4-(4-piperidyloxy)butyl] carbamate (260 mg, 841 umol, HCl), K$_2$CO$_3$ (581 mg, 4.21 mmol) in H$_2$O (6 mL) and THF (6 mL) was added CbzCl (172 mg, 1.01 mmol) at 0° C., and the mixture was stirred at 15° C. for 16 hrs. On completion, the mixture was diluted with H$_2$O (20 mL), extracted with EA (2×20 mL), the organic layers were washed with brine (2×20 mL), dried over anhydrous Na$_2$SO$_4$, filtered and concentrated in vacuo. The mixture was purified by silica gel column (PE:EA=5:1) to give the title compound (90 mg, 26% yield) as yellow oil. $^1$H NMR (400 MHz, CDCl$_3$) δ 7.41-7.30 (m, 5H), 5.14 (s, 2H), 4.73 (s, 1H), 3.89-3.76 (m, 2H), 3.52-3.42 (m, 3H), 3.28-3.19 (m, 2H), 3.19-3.11 (m, 2H), 1.91-1.78 (m, 2H), 1.64-1.56 (m, 6H), 1.46 (s, 9H).

Step 4—Benzyl 4-(4-aminobutoxy)piperidine-1-carboxylate

To a solution of benzyl 4-[4-(tert-butoxycarbonylamino) butoxy]piperidine-1-carboxylate (90.0 mg, 221 umol) in DCM (1.00 mL) was added HCl/dioxane (4.00 M, 1.00 mL). The mixture was stirred at 15° C. for 1 hr. On completion, the mixture was concentrated in vacuo to give the title compound (70 mg, 92% yield) as yellow solid. LC-MS (ESI$^+$) m/z 307.2 (M+H)$^+$.

2-(2,6-Dioxo-3-piperidyl)-4-[4-(4-piperidyloxy) butylamino]isoindoline-1,3-dione (Intermediate ADV)

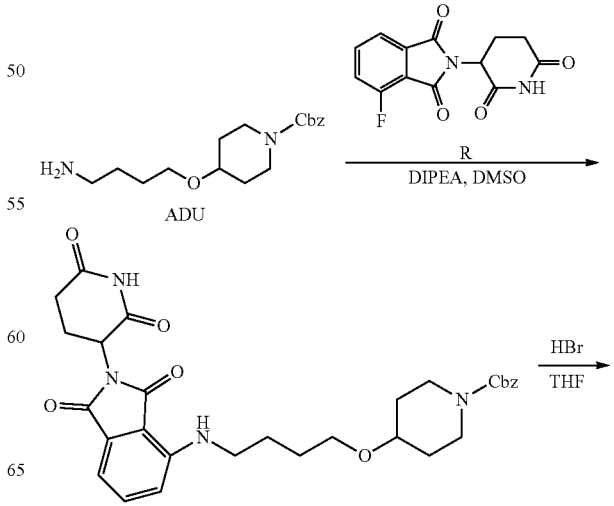

1741

-continued

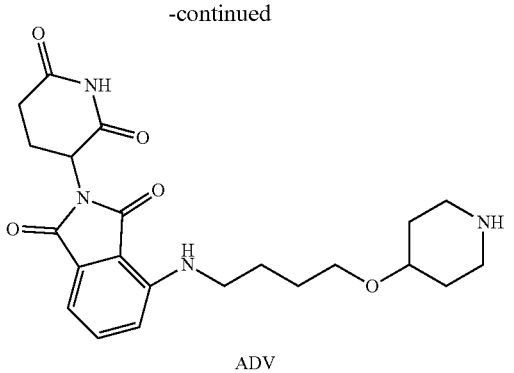

ADV

Step 1—Benzyl 4-[4-[[2-(2,6-dioxo-3-piperidyl)-1,3-dioxo-isoindolin-4-yl]amino]butoxy]piperidine-1-carboxylate To a solution of benzyl 4-(4-aminobutoxy)piperidine-1-carboxylate (70.0 mg, 204 umol, HCl, Intermediate ADU), 2-(2,6-dioxo-3-piperidyl)-4-fluoro-isoindoline-1,3-dione (47.0 mg, 170 umol, Intermediate R) in DMSO (3.00 mL) was added DIPEA (109 mg, 850 umol). The mixture was stirred at 130° C. for 3 hrs. On completion, the mixture was diluted with H$_2$O (15 mL), extracted with EA (3×15 mL), the organic layers were washed with brine (3×15 mL), dried over anhydrous Na$_2$SO$_4$, filtered and concentrated in vacuo to give the title compound (80 mg, 83% yield) as yellow solid. LC-MS (ESI$^+$) m/z 563.3 (M+H)$^+$.

Step 2—2-(2,6-Dioxo-3-piperidyl)-4-[4-(4-piperidyloxy)butylamino]isoindoline-1,3-dione To a solution of benzyl 4-[4-[[2-(2,6-dioxo-3-piperidyl)-1,3-dioxo-isoindolin-4-yl]amino]butoxy] piperidine-1-carboxylate (60 mg, 106 umol) in THF (6 mL) was added HBr (8.94 g, 36.4 mmol, 6.00 mL, 33% wt in acetic acid solution), and the mixture was stirred at 15° C. for 6 hrs. On completion, the mixture was concentrated in vacuo. The mixture was purified by reverse phase: (0.1% FA) to give the title compound (30 mg, 65% yield) as yellow solid. $^1$H NMR (400 MHz, DMSO-d$_6$) δ 11.09 (s, 1H), 8.35 (s, 1H), 7.65-7.55 (m, 1H), 7.11 (d, J=8.4 Hz, 1H), 7.04 (d, J=7.2 Hz, 1H), 6.63-6.52 (m, 1H), 5.10-5.02 (m, 1H), 3.56-3.54 (m, 2H), 3.35-3.31 (m, 2H), 3.19-3.11 (m, 2H), 3.00-2.92 (m, 2H), 2.91-2.83 (m, 1H), 2.65-2.56 (m, 2H), 2.08-1.99 (m, 1H), 1.97-1.89 (m, 2H), 1.86-1.79 (m, 2H), 1.69-1.64 (m, 2H), 1.57-1.47 (m, 3H), LC-MS (ESI$^+$) m/z 429.2 (M+H)$^+$.

N,N-dibenzyl-2-fluoro-3-(2-(prop-2-yn-1-yloxy)ethoxy)propan-1-amine (Intermediate ADW)

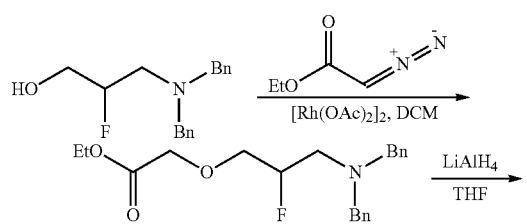

1742

-continued

ADW

Step 1—Ethyl 2-(3-(dibenzylamino)-2-fluoropropoxy)acetate

To s solution of 3-(dibenzylamino)-2-fluoro-propan-1-ol (3.00 g, 11.0 mmol, Intermediate AH) and [Rh(OAc)$_2$]$_2$ (121 mg, 549 umol) in DCM (40 mL) was added dropwise a solution of ethyl 2-diazoacetate (1.88 g, 16.5 mmol) in DCM (20 mL). The reaction mixture was stirred at 15° C. for 18 hours under N$_2$ atmosphere. On completion, the reaction mixture was concentrated in vacuo. The residue was purified by silica gel chromatography (Petroleum ether/Ethyl acetate=10/1) to give the title compound (3.00 g, 76% yield) as colorless oil. $^1$H NMR (400 MHz, CDCl$_3$) δ 7.40-7.24 (m, 10H), 4.92-4.71 (m, 1H), 4.23 (q, J=7.2 Hz, 2H), 4.09 (d, J=8.8 Hz, 2H), 3.75-3.60 (m, 6H), 2.83-2.73 (m, 2H), 1.30 (t, J=7.2 Hz, 3H); LC-MS (ESI$^+$) m/z 360.2 (M+H)$^+$.

Step 2—2-(3-(Dibenzylamino)-2-fluoropropoxy)ethanol

To a solution of ethyl 2-[3-(dibenzylamino)-2-fluoro-propoxy]acetate (3.00 g, 8.35 mmol) in THF (60 mL) was added LiAlH$_4$ (380 mg, 10.0 mmol) in portions. The reaction mixture was stirred at 15° C. for 1 hour. On completion, the reaction mixture was diluted with H$_2$O (0.5 mL) and NaOH aqueous (0.5 mL, 15% in H$_2$O) at 0° C. Then the mixture was extracted with EA (3×10 mL), the combined organic phase was filtered, the filtrate was dried over Na$_2$SO$_4$, and concentrated in vacuo to give the title compound (2.40 g, 91% yield) as colorless oil. $^1$H NMR (400 MHz, CDCl$_3$) δ 7.39-7.23 (m, 10H), 4.86-4.66 (m, 1H), 3.72-3.64 (m, 6H), 3.63-3.61 (m, 1H), 3.58-3.54 (m, 1H), 3.54-3.50 (m, 2H), 2.78-2.73 (m, 2H), 1.92-1.86 (m, 1H).

Step 3—N,N-dibenzyl-2-fluoro-3-(2-(prop-2-yn-1-yloxy)ethoxy)propan-1-amine

To a solution of 2-[3-(dibenzylamino)-2-fluoro-propoxy] ethanol (2.40 g, 7.56 mmol), 3-bromoprop-1-yne (1.08 g, 9.07 mmol) and TBAI (419 mg, 1.13 mmol) in THF (60 mL) was added NaH (605 mg, 15.1 mmol, 60% dispersion in mineral oil) in portions. The reaction mixture was stirred at 15° C. for 12 hours under N$_2$ atmosphere. On completion, the reaction mixture was diluted with H$_2$O (30 mL) and extracted with ethyl acetate (3×60 mL). The combined organic layers were dried over Na$_2$SO$_4$, filtered and concentrated in vacuo. The residue was purified by silica gel chromatography (petroleum ether/ethyl acetate=10/1) to give the title compound (2.40 g, 89% yield). LC-MS (ESI$^+$) m/z 356.2 (M+H)$^+$.

3-(5-(3-(2-(3-Amino-2-fluoropropoxy)ethoxy)pro-pyl)-3-methyl-2-oxo-2,3-dihydro-1H-benzo[d]imida-zol-1-yl)piperidine-2,6-dione (Intermediate ADX)

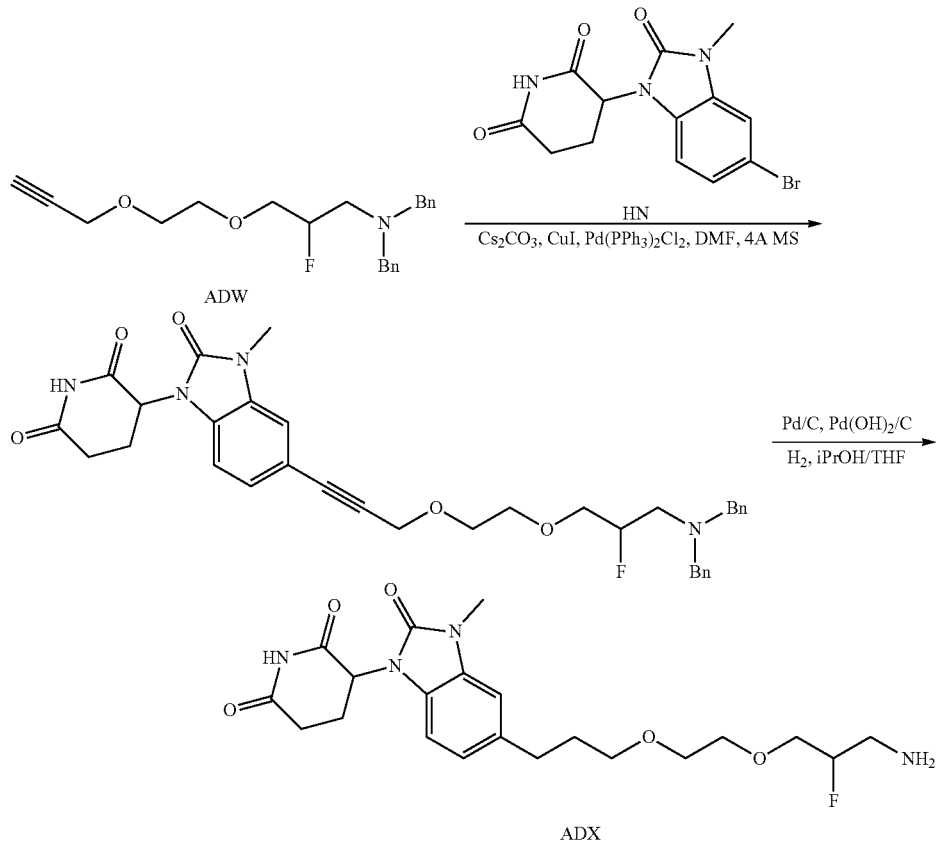

Step 1—3-(5-(3-(2-(3-(Dibenzylamino)-2-fluoro-propoxy)ethoxy)prop-1-yn-1-yl)-3-methyl-2-oxo-2,3-dihydro-1H-benzo[d]imidazol-1-yl)piperidine-2,6-dione A mixture of N,N-dibenzyl-2-fluoro-3-(2-prop-2-ynoxy-ethoxy)propan-1-amine (1.58 g, 4.44 mmol, Intermediate ADW), 3-(5-bromo-3-methyl-2-oxo-benzimidazol-1-yl)pip-eridine-2,6-dione (1.00 g, 2.96 mmol, Intermediate HN), $Cs_2CO_3$ (2.89 g, 8.87 mmol), CuI (56.3 mg, 296 umol), $Pd(PPh_3)_2Cl_2$ (208 mg, 296 umol) and 4 Å molecular sieves (10 mg) in DMF (20 mL) was stirred at 80° C. for 2 hours under $N_2$ atmosphere. On completion, the reaction mixture was diluted with ethyl acetate (60 mL). The mixture was washed with water (2×30 mL), dried over $Na_2SO_4$, concentrated in vacuo. The residue was purified by reverse phase (0.1% FA) to give the title compound (560 mg, 31% yield). $^1$H NMR (400 MHz, $CDCl_3$) δ 8.11 (s, 1H), 7.39-7.28 (m, 8H), 7.26-7.21 (m, 2H), 7.19 (dd, J=1.0, 8.2 Hz, 1H), 7.11 (s, 1H), 6.74 (d, J=8.0 Hz, 1H), 5.19 (dd, J=5.4, 12.7 Hz, 1H), 4.90-4.70 (m, 1H), 4.40 (s, 2H), 3.74-3.69 (m, 2H), 3.69-3.65 (m, 6H), 3.64-3.62 (m, 1H), 3.58 (d, J=4.6 Hz, 1H), 3.41 (s, 3H), 3.01-2.91 (m, 1H), 2.89-2.65 (m, 4H), 2.30-2.19 (m, 1H); LC-MS (ESI$^+$) m/z 613.4 (M+H)$^+$.

Step 2—3-(5-(3-(2-(3-Amino-2-fluoropropoxy)ethoxy)propyl)-3-methyl-2-oxo-2,3-dihydro-1H-benzo [d]imidazol-1-yl)piperidine-2,6-dione A mixture of 3-[5-[3-[2-[3-(dibenzylamino)-2-fluoro-propoxy]ethoxy]prop-1-ynyl]-3-methyl-2-oxo-benzimida-zol-1-yl]piperidine-2,6-dione (50.0 mg, 81.6 umol), Pd/C (25.0 mg, 10% wt) and $Pd(OH)_2$/C (25 mg, 10% wt) in a mixed solvent of i-PrOH (1 mL) and THF (0.5 mL) was stirred at 30° C. for 36 hours under $H_2$ (50 psi) atmosphere. On completion, the reaction mixture was filtered and the filtrate was concentrated in vacuo to give the title compound (40.0 mg, 90% yield) as yellowish oil. LC-MS (ESI$^+$) m/z 437.2 (M+H)$^+$.

Tert-butyl N-[6-(methylamino)hexyl]carbamate (Intermediate ADY)

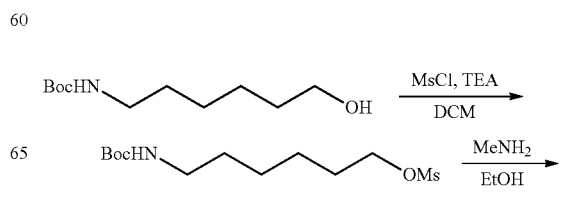

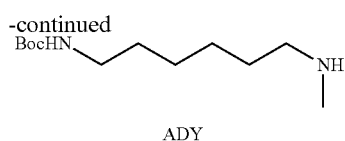

ADY

Step 1—6-(Tert-butoxycarbonylamino)hexyl methanesulfonate

To a solution of tert-butyl N-(6-hydroxyhexyl)carbamate (3.00 g, 13.8 mmol, CAS #75937-12-1) and TEA (4.19 g, 41.4 mmol) in DCM (30 mL) was added MsCl (2.37 g, 20.7 mmol) at 0° C., the mixture was stirred at 15° C. for 0.5 hr. On completion, the mixture was washed with H$_2$O (2×30 mL) and washed with brine (2×20 mL). The organic layer was dried over anhydrous Na$_2$SO$_4$, filtered and concentrated in vacuo to give the title compound (4 g, 98% yield) as yellow oil. $^1$H NMR (400 MHz, CDCl$_3$) δ 4.53 (s, 1H), 4.25 (t, J=6.4 Hz, 2H), 3.19-3.10 (m, 2H), 3.03 (s, 3H), 1.82-1.74 (m, 2H), 1.55-1.49 (m, 2H), 1.46 (s, 9H), 1.45-1.28 (m, 4H).

Step 2—Tert-butyl N-[6-(methylamino)hexyl]carbamate

To a solution of 6-(tert-butoxycarbonylamino)hexyl methanesulfonate (1.50 g, 5.08 mmol) in EtOH (15 mL) was added MeNH$_2$ (10.5 g, 101 mmol, 30% solution). The mixture was stirred at 80° C. for 16 hrs. On completion, the mixture was concentrated in vacuo. The residue was purified by silica gel column (EA:MeOH=5:1) to give the title compound (1 g, 85% yield) as yellow solid. $^1$H NMR (400 MHz, DMSO-d$_6$) δ 8.33 (s, 1H), 6.77 (s, 1H), 2.94-2.79 (m, 4H), 2.32 (s, 3H), 1.60-1.47 (m, 2H), 1.41-1.32 (m, 11H), 1.31-1.20 (m, 4H).

N-[1-[4-[[6-aminohexyl(methyl)amino]methyl]cyclohexyl]-3-(difluoromethyl) pyrazol-4-yl]-2-[2-(cyclopropylmethylamino)-4-pyridyl oxazole-4-carboxamide (Intermediate ADZ)

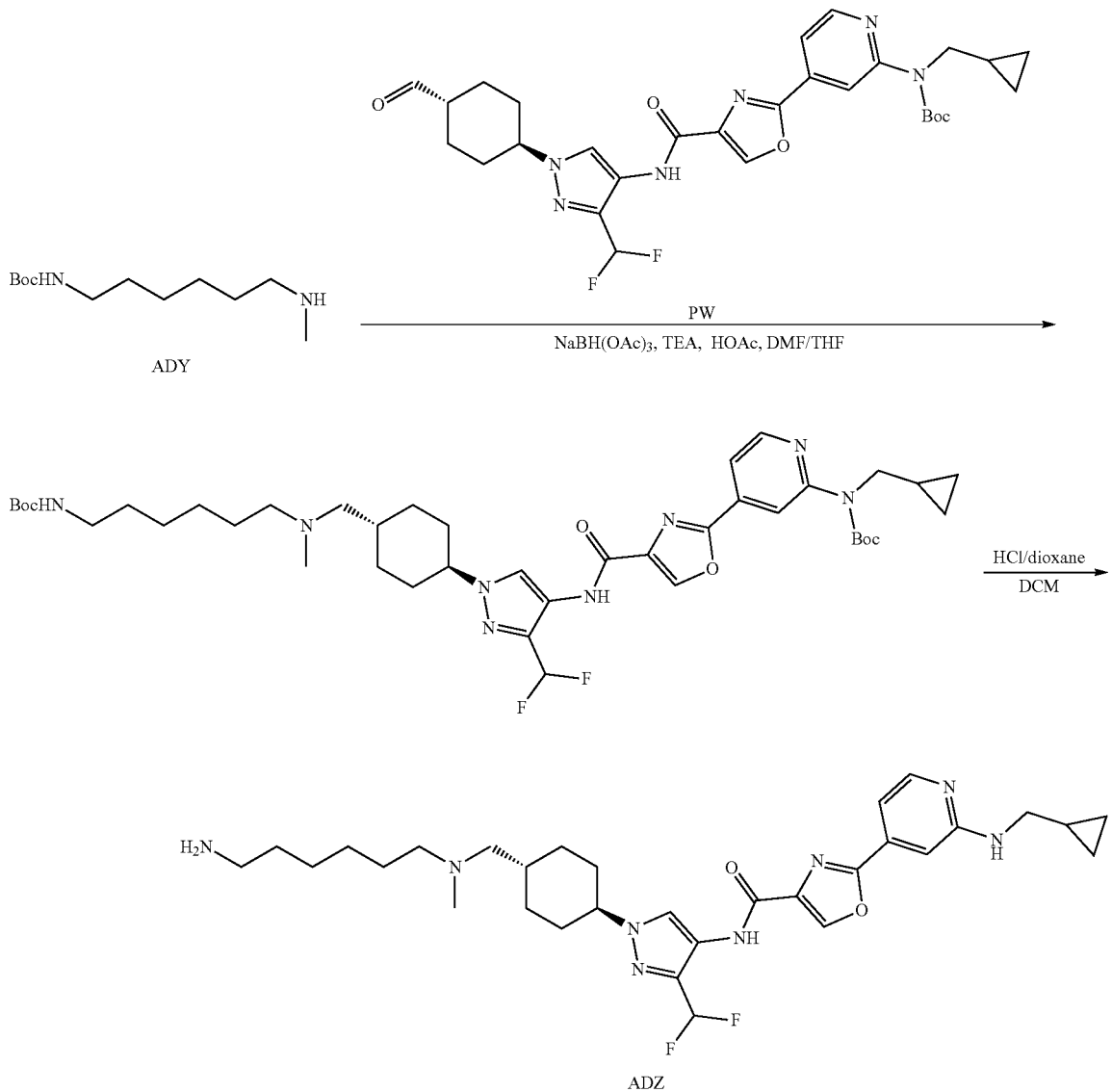

1747

Step 1—Tert-butyl N-[4-[4-[[1-[4-[[6-(tert-butoxy-carbonylamino) hexyl-methyl-amino] methyl]cyclo-hexyl]-3-(difluoromethyl)pyrazol-4-yl]carbamoyl] oxazol-2-yl]-2-pyridyl]-N-(cyclopropylmethyl)carbamate To a solution of tert-butyl N-[6-(methylamino)hexyl]carbamate (51.2 mg, 222 umol, Intermediate ADY), tert-butyl N-(cyclopropylmethyl)-N-[4-[4-[[3-(difluoromethyl)-1-(4-formylcyclohexyl)pyrazol-4-yl]carbamoyl]oxazol-2-yl]-2-pyridyl]carbamate (100 mg, 171 umol, Intermediate PW) in a mixed solvent of DMF (1.00 mL) and THF (4.00 mL) was added HOAc (30.8 mg, 513 umol) at −10° C., the mixture was stirred at −10° C. for 0.5 hr, then NaBH(OAc)$_3$ (72.5 mg, 342 umol) was added, the mixture was stirred at −10° C. for 1 hr. On completion, the mixture was quenched with H$_2$O (15 mL) and extracted with EA (2×15 mL). The organic layers were washed with brine (2×15 mL), dried over anhydrous Na$_2$SO$_4$, filtered and concentrated in vacuo to give the title compound (130 mg, 95% yield) as yellow solid, $^1$HNMR (400 MHz, DMSO-d$_6$) δ 9.81 (s, 1H), 9.02 (s, 1H), 8.62-8.58 (m, 1H), 8.30 (s, 1H), 8.20 (s, 1H), 7.96 (s, 1H), 7.69 (dd, J=1.2, 5.2 Hz, 1H), 7.32-7.01 (m, 1H), 6.79 (t, J=5.2 Hz, 1H), 4.32-4.16 (m, 1H), 3.87 (d, J=7.2 Hz, 2H), 2.95-2.90 (m, 2H), 2.90-2.87 (m, 2H), 2.68-2.66 (m, 1H), 2.53-2.52 (m, 2H), 2.11-2.03 (m, 2H), 1.96-1.74 (m, 8H), 1.70-1.55 (m, 2H), 1.52 (s, 9H), 1.42-1.34 (m, 11H), 1.31-1.21 (m, 4H), 1.20-1.11 (m, 4H), 0.44-0.38 (m, 2H), 0.27-0.22 (m, 2H).

Step 2—N-[1-[4-[[6-aminohexyl(methyl)amino] methyl]cyclohexyl]-3-(difluoromethyl) pyrazol-4-yl]-2-[2-(cyclopropylmethylamino)-4-pyridyl]oxazole-4-carboxamide To a solution of tert-butyl N-[4-[4-[[1-[4-[[6-(tert-butoxy-carbonylamino)hexyl-methyl-amino]methyl] cyclohexyl]-3-(difluoromethyl)pyrazol-4-yl]carbamoyl]oxazol-2-yl]-2-pyridyl]-N-(cyclopropylmethyl)carbamate (120 mg, 150 umol) in DCM (3.00 mL) was added HCl/dioxane (4.00 M, 3.00 mL), and the mixture was stirred at 15° C. for 1 hr. On completion, the mixture was concentrated in vacuo to give the title compound (90 mg, 94% yield, HCl salt) as yellow solid. $^1$H NMR (400 MHz, DMSO-d$_6$) δ 10.10 (s, 1H), 9.89 (s, 1H), 9.10 (s, 1H), 8.20 (s, 1H), 8.10 (d, J=6.4 Hz, 1H), 8.01-7.90 (m, 2H), 7.64-7.51 (m, 1H), 7.34-7.04 (m, 2H), 4.32-4.19 (m, 1H), 3.35-3.30 (m, 2H), 3.15-3.04 (m, 1H), 3.03-2.86 (m, 3H), 2.83-2.73 (m, 5H), 2.14-2.02 (m, 3H), 1.99-1.78 (m, 4H), 1.77-1.65 (m, 2H), 1.63-1.51 (m, 2H), 1.42-1.29 (m, 4H), 1.26-1.08 (m, 3H), 0.60-0.53 (m, 2H), 0.36-0.30 (m, 2H).

Tert-butyl 4-[3-(methylamino)propyl]piperidine-1-carboxylate (Intermediate AEA)

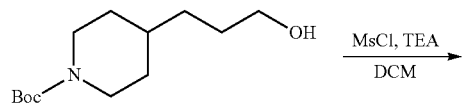

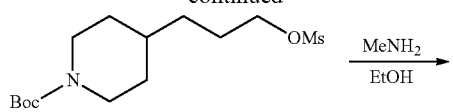

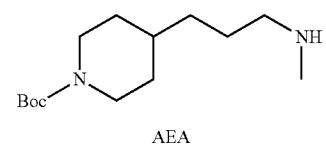

Step 1—Tert-butyl 4-(3-methylsulfonyloxypropyl) piperidine-1-carboxylate

To a solution of tert-butyl 4-(3-hydroxypropyl)piperidine-1-carboxylate (3.00 g, 12.3 mmol, CAS #156185-63-6) and TEA (2.49 g, 24.6 mmol) in DCM (30.0 mL) was added MsCl (2.12 g, 18.4 mmol) at 0° C., and the mixture was stirred at 25° C. for 1 hr. On completion, the reaction mixture was quenched with water (5 mL), then diluted with water (30 mL) and extracted with DCM (2×30 mL). The combined organic layers were washed with brine (4×50 mL), dried over Na$_2$SO$_4$, filtered and concentrated in vacuo to give the title compound (3.51 g, 88% yield) as yellow oil. $^1$H NMR (400 MHz, CDCl$_3$) δ 4.21 (t, J=6.4 Hz, 2H), 4.08-3.95 (m 2H), 3.00 (s, 3H), 2.67 (t, J=12.4 Hz, 2H), 1.83-1.72 (m, 2H), 1.65 (d, J=12.8 Hz, 2H), 1.45 (s, 9H), 1.42-1.29 (m, 3H), 1.14-1.04 (m, 2H).

Step 2—Tert-butyl 4-[3-(methylamino)propyl]piperidine-1-carboxylate

To a solution of tert-butyl 4-(3-methylsulfonyloxypropyl) piperidine-1-carboxylate (1.00 g, 3.11 mmol) in EtOH (20.0 mL) was added methylamine solution (1.61 g, 15.5 mmol, 30% wt in ethanol solution). The mixture was stirred at 80° C. for 16 hrs. On completion, the reaction mixture was concentrated in vacuo to give the title compound (797 mg, 99% yield) as a white solid. $^1$H NMR (400 MHz, CDCl$_3$) δ 3.70 (q, J=7.2 Hz, 1H), 2.92-2.84 (m, 2H), 2.76 (s, 3H), 2.67-2.59 (m, 2H), 1.82-1.71 (m, 2H), 1.65 (d, J=12.8 Hz, 2H), 1.44 (s, 9H), 1.41-1.35 (m, 1H), 1.35-1.26 (m, 2H), 1.23 (t, J=6.8 Hz, 2H), 1.12-1.02 (m, 2H).

2-[2-(cyclopropylmethylamino)-4-pyridyl]-N-[3-(difluoromethyl)-1-[4-[[methyl-[3-(4-piperidyl)propyl]amino]methyl] cyclohexyl]pyrazol-4-yl] oxazole-4-carboxamide (Intermediate AEB)

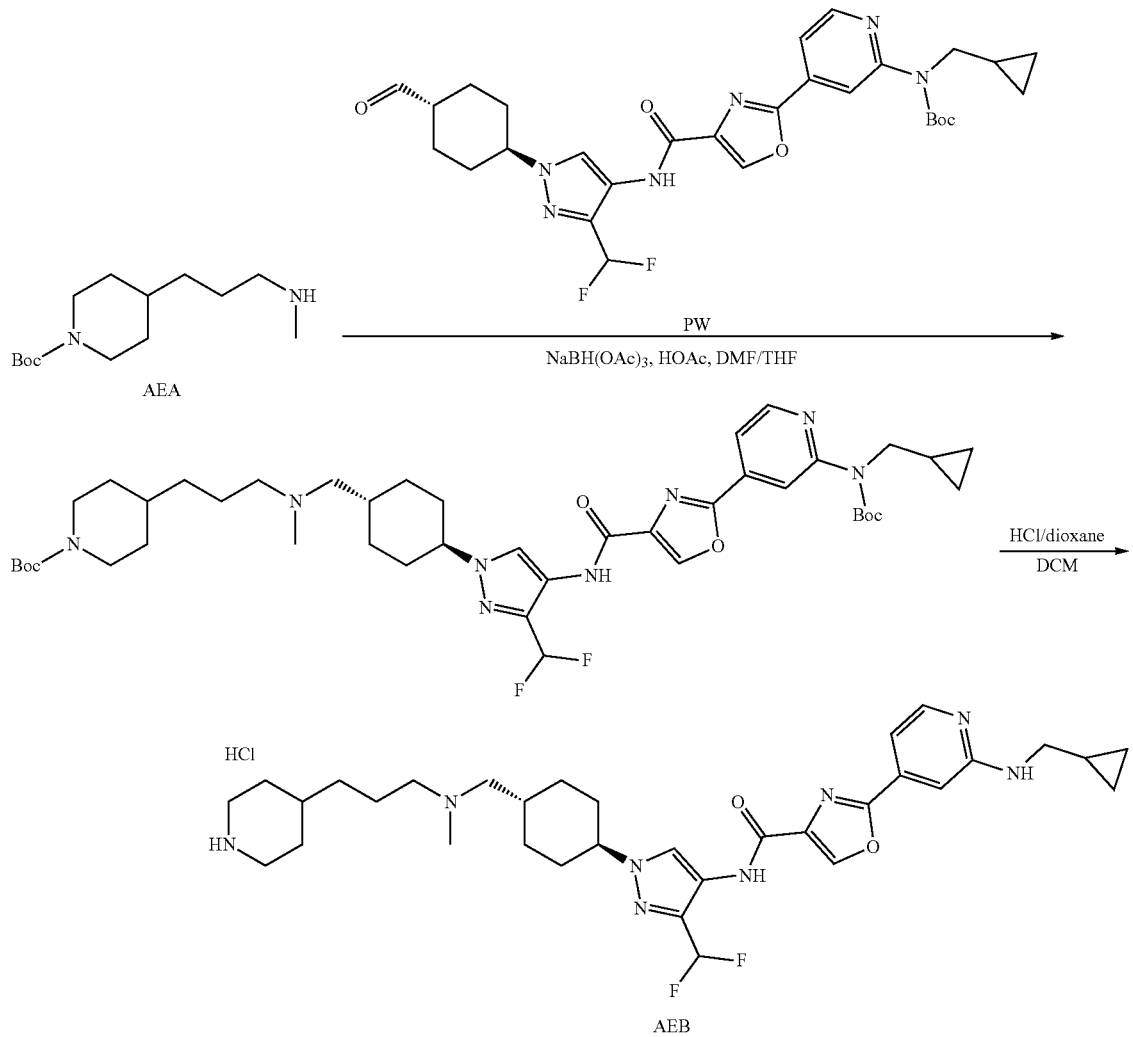

Step 1—Tert-butyl 4-[3-[[4-[4-[[2-[2-[tert-butoxycarbonyl(cyclopropylmethyl)amino]-4-pyridyl] oxazole-4-carbonyl]amino]-3-(difluoromethyl)pyrazol-1-yl] cyclohexyl]methyl-methyl-amino]propyl] piperidine-1-carboxylate To a solution of tert-butyl 4-[3-(methylamino)propyl] piperidine-1-carboxylate (43.8 mg, 171 umol, Intermediate AEA) in a mixed solvent of THF (2.00 mL) and DMF (2.00 mL) was added tert-butyl N-(cyclopropylmethyl)-N-[4-[4-[[3-(difluoromethyl)-1-(4-formylcyclohexyl)pyrazol-4-yl]carbamoyl]oxazol-2-yl]-2-pyridyl]carbamate (100 mg, 171 umol, Intermediate PW) and HOAc (20.5 mg, 342 umol) was added at −10° C., and the mixture was stirred at −10° C. for 0.5 hr. NaBH(OAc)₃ (54.4 mg, 256 umol) was then added, then the mixture was stirred at −10° C. for 1 hr. On completion, the reaction mixture was quenched with water (0.5 mL), and then concentrated in vacuo to give a residue. The residue was purified by reversed-phase (0.1% FA condition) to give the title compound (110 mg, 77% yield) as a yellow solid. ¹H NMR (400 MHz, CDCl₃) δ 9.06 (s, 1H), 8.52 (d, J=5.2 Hz, 1H), 8.41 (s, 1H), 8.37 (s, 1H), 8.31 (d, J=6.4 Hz, 2H), 7.63 (d, J=5.2 Hz, 1H), 6.82 (t, J=54.4 Hz, 1H), 4.12-4.06 (m, 2H), 3.94 (d, J=7.2 Hz, 2H), 2.86-2.76 (m, 2H), 2.75-2.63 (m, 4H), 2.61 (s, 3H), 2.24 (d, J=11.2 Hz, 2H), 2.08 (d, J=12.4 Hz, 2H), 1.94-1.76 (m, 3H), 1.74-1.62 (m, 4H), 1.57 (s, 9H), 1.46 (s, 9H), 1.43-1.36 (m, 1H), 1.31-1.17 (m, 5H), 1.15-1.05 (m, 2H), 0.50-0.39 (m, 2H), 0.34-0.22 (m, 2H).

Step 2—2-[2-(cyclopropylmethylamino)-4-pyridyl]-N-[3-(difluoromethyl)-1-[4-[[methyl-[3-(4-piperidyl)propyl]amino]methyl] cyclohexyl]pyrazol-4-yl]oxazole-4-carboxamide To a solution of tert-butyl 4-[3-[[4-[4-[[2-[2-[tert-butoxycarbonyl(cyclopropylmethyl)amino]-4-pyridyl]oxazole-4-carbonyl]amino]-3-(difluoromethyl)pyrazol-1-yl] cyclohexyl]methyl-methyl-amino]propyl]piperidine-1-carboxylate (50.0 mg, 60.6 umol) in DCM (2.00 mL) was added HCl/dioxane (4 M, 2.00 mL). The mixture was stirred at 20° C. for 0.5 hr. On completion, the reaction mixture was concentrated in vacuo to give the title compound (40.0 mg, 99% yield, HCl salt) as a yellow solid. LC-MS (ESI$^+$) m/z 625.5 (M+H)$^+$.

2-[2-(cyclopropylmethylamino)-4-pyridyl]-N-[3-(difluoromethyl)-1-[4-[methyl-[3-(4-piperidyl)propyl]carbamoyl]cyclohexyl]pyrazol-4-yl]oxazole-4-carboxamide (Intermediate AEC)

mg, 166 umol, Intermediate QT) in DMF (1.00 mL) was added HATU (75.9 mg, 199 umol) and DIPEA (64.5 mg, 499 umol). The mixture was stirred at 20° C. for 1 hr. On completion, the reaction mixture was quenched with water (0.5 mL) and then concentrated in vacuo to give a residue. The residue was purified by reversed phase (0.1% FA condition) to give the title compound (100 mg, 71% yield) as a white solid. $^1$H NMR (400 MHz, DMSO-d$_6$) δ 9.76 (s, 1H), 9.00 (s, 1H), 8.59 (d, J=5.2 Hz, 1H), 8.29 (s, 1H), 8.19 (d, J=3.2 Hz, 1H), 7.68 (dd, J=1.2, 5.2 Hz, 1H), 7.36-6.96 (m, 1H), 4.36-4.20 (m, 1H), 3.98-3.78 (m, 4H), 3.29 (s, 3H), 3.25 (J=7.2 Hz, 1H), 3.01 (s, 2H), 2.75-2.60 (m, 3H), 2.10-1.99 (m, 2H), 1.92-1.72 (m, 4H), 1.67-1.54 (m, 4H),

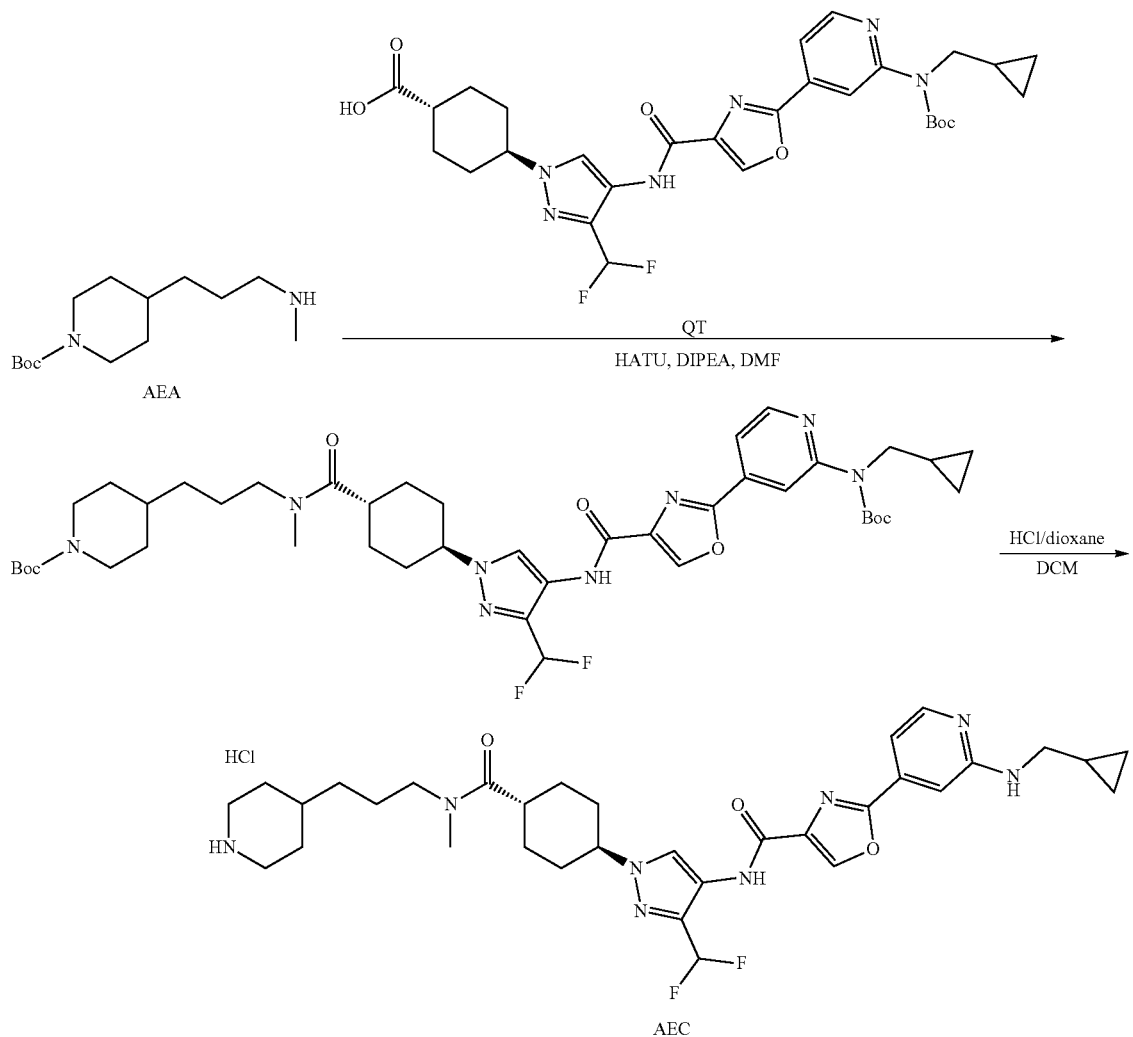

Step 1—Tert-butyl 4-[3-[[4-[4-[[2-[2-[tert-butoxycarbonyl(cyclopropylmethyl)amino]-4-pyridyl] oxazole-4-carbonyl]amino]-3-(difluoromethyl)pyrazol-1-yl]cyclohexanecarbonyl]-methyl-amino]propyl]piperidine-1-carboxylate To a solution of tert-butyl 4-[3-(methylamino)propyl]piperidine-1-carboxylate (42.6 mg, 166 umol, Intermediate AEA) and 4-[4-[[2-[2-[tertbutoxycarbonyl(cyclopropylmethyl)amino]-4-pyridyl]oxazole-4-carbonyl]amino]-3-(difluoromethyl)pyrazol-1-yl]cyclohexanecarboxylic acid (100

1.51 (s, 9H), 1.49-1.40 (m, 2H), 1.38 (s, 9H), 1.24-1.08 (m, 3H), 1.03-0.85 (m, 2H), 0.48-0.35 (m, 2H), 0.29-0.16 (m, 2H).

Step 2—2-[2-(cyclopropylmethylamino)-4-pyridyl]-N-[3-(difluoromethyl)-1-[4-[methyl-[3-(4-piperidyl)propyl]carbamoyl]cyclohexyl]pyrazol-4-yl]oxazole-4-carboxamide To a solution of tert-butyl 4-[3-[[4-[4-[[2-[2-[tert-butoxycarbonyl(cyclopropylmethyl)amino]-4-pyridyl]oxazole-4- carbonyl]amino]-3-(difluoromethyl)pyrazol-1-yl]cyclohexanecarbonyl]-methyl-amino]propyl]piperidine-1-carboxylate (50.0 mg, 59.6 umol) in DCM (3.00 mL) was added HCl/dioxane (4 M, 3.00 mL). The mixture was stirred at 20° C. for 0.5 hr. On completion, the reaction mixture was concentrated in vacuo to give the title compound (40.0 mg, 99% yield, HCl salt) as a yellow solid. LC-MS (ESI$^+$) m/z 639.4 (M+H)$^+$.

2-[2-[2-(1-Adamantyloxy)ethoxy]ethoxy]-N-methyl-ethanamine (Intermediate AED)

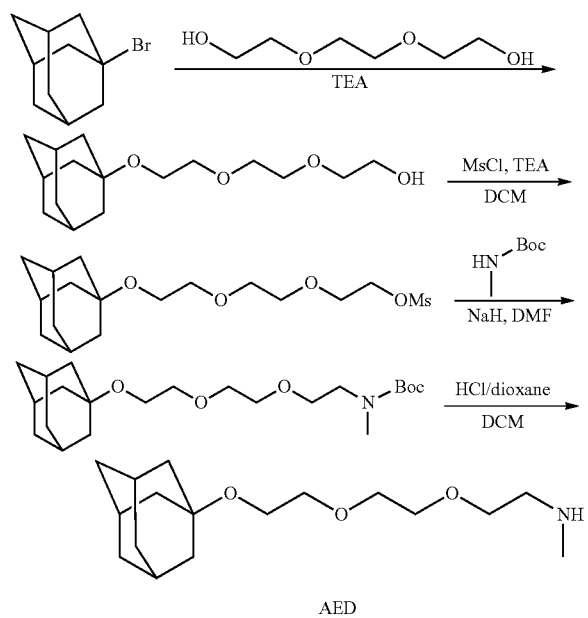

Step 1—2-[2-[2-(1-Adamantyloxy)ethoxy]ethoxy] ethanol

A solution of 1-bromoadamantane (1.00 g, 4.65 mmol, CAS #102938-79-4) and TEA (1.41 g, 14.0 mmol, CAS #112-27-6) in 2-[2-(2-hydroxyethoxy)ethoxy]ethanol (20.9 g, 139 mmol,) was heated at 110° C. for 20 hrs. On completion, the mixture was cooled to room temperature, diluted with DCM (80 mL) and water (80 mL), and separated. The organic layer was washed with 1 N HCl (80 ml), then washed with brine (50 mL), dried with Na$_2$SO$_4$, filtered and the filtrate was concentrated in vacuo to give the title compound (1.05 g, 79% yield) as brown oil. $^1$H NMR (400 MHz, CDCl$_3$-d) δ 3.78-3.55 (m, 12H), 2.63 (t, J=6.0 Hz, 1H), 2.20-2.10 (m, 3H), 1.80-1.70 (m, 6H), 1.69-1.54 (m, 6H).

Step 2—2-[2-[2-(1-Adamantyloxy)ethoxy]ethoxy] ethyl methanesulfonate

To a solution of 2-[2-[2-(1-adamantyloxy)ethoxy]ethoxy] ethanol (500 mg, 1.76 mmol) and TEA (534 mg, 5.27 mmol) in DCM (10 mL) was added MsCl (242 mg, 2.11 mmol). The reaction mixture was stirred at 20° C. for 2 hrs. On completion, the mixture was quenched with water (30 mL), and extracted with DCM (2×30 ml). The organic layer was washed with brine (2×30 mL), dried with Na$_2$SO$_4$, filtered and the filtrate was concentrated in vacuo to give the title compound (480 mg, 75% yield) as yellow oil. $^1$H NMR (400 MHz, CDCl$_3$-d) δ 4.42-4.36 (m, 2H), 3.81-3.76 (m, 2H), 3.68-3.66 (m, 4H), 3.61-3.55 (m, 4H), 3.09 (s, 3H), 2.20-2.10 (m, 3H), 1.77-1.70 (m, 6H), 1.68-1.55 (m, 6H).

Step 3—Tert-butyl N-[2-[2-[2-(1-adamantyloxy)ethoxy]ethoxy]ethyl]-N-methyl-carbamate To a solution of tert-butyl N-methylcarbamate (130 mg, 993 umol) in DMF (5 mL) was added NaH (99.3 mg, 2.48 mmol, 60% dispersion in oil) at 0° C. Thirty minutes later, 2-[2-[2-(1-adamantyloxy)ethoxy]ethoxy]ethyl methanesulfonate (360 mg, 993 umol) was added and the reaction mixture was stirred at 20° C. for 12 hrs. On completion, the mixture was quenched with water (30 mL), and extracted with EA (2×30 mL). The combined organic layer was washed with brine (50 mL), concentrated in vacuo. The residue was purified by silica gel chromatography (SiO$_2$) to give the title compound (250 mg, 63% yield) as colorless oil. $^1$H NMR (400 MHz, CDCl$_3$-d) δ 3.68-3.57 (m, 10H), 3.48-3.34 (m, 2H), 2.92 (s, 3H), 2.20-2.10 (m, 3H), 1.78-1.74 (m, 6H), 1.68-1.59 (m, 6H), 1.46 (s, 9H).

Step 4—2-[2-[2-(1-Adamantyloxy)ethoxy]ethoxy]-N-methyl-ethanamine

To a solution of tert-butyl N-[2-[2-[2-(1-adamantyloxy)ethoxy]ethoxy]ethyl]-N-methyl-carbamate (300 mg, 755 umol) in DCM (5 mL) was added HCl/dioxane (5 mL). The reaction mixture was stirred at 20° C. for 2 hrs. On completion, the mixture was concentrated in vacuo to give the title compound (250 mg, 99% yield, HCl salt) as a white powder. LC-MS (ESI$^+$) m/z 298.2 (M+H)$^+$.

5-[(2R,6S)-2,6-dimethylmorpholin-4-yl]pyrazolo[1,5-a]pyrimidine-3-carboxylic acid (Intermediate AEE)

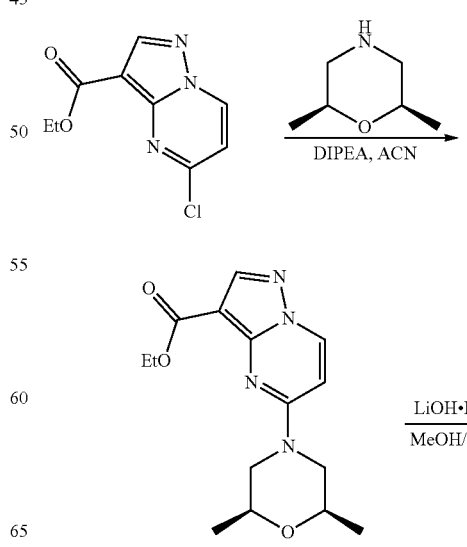

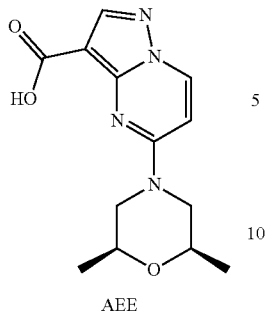

AEE

Step 1—Ethyl 5-[(2R,6S)-2,6-dimethylmorpholin-4-yl]pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7), (2R,6S)-2,6-dimethylmorpholine (153 mg, 1.33 mmol, CAS #6485-55-8) in ACN (6.00 mL) was added DIPEA (458 mg, 3.55 mmol). The mixture was stirred at 60° C. for 2 hrs. On completion, the mixture was concentrated in vacuo. The residue was triturated with $H_2O$ (3 mL), filtered and the solid was dried in vacuo to give the title compound (230 mg, 85% yield) as white solid. $^1H$ NMR (400 MHz, DMSO-$d_6$) δ 8.75 (d, J=8.0 Hz, 1H), 8.21 (s, 1H), 6.88 (d, J=8.0 Hz, 1H), 4.70-4.24 (m, 2H), 4.19 (q, J=7.2 Hz, 2H), 3.68-3.53 (m, 2H), 2.71-2.58 (m, 2H), 1.29 (t, J=7.2 Hz, 3H), 1.18 (s, 3H), 1.16 (s, 3H); LC-MS (ESI$^+$) m/z 305.2 (M+H)$^+$.

Step 2—5-[(2R,6S)-2,6-dimethylmorpholin-4-yl]pyrazolo[1,5-a]pyrimidine-3-carboxylic acid To a solution of ethyl 5-[(2R,6S)-2,6-dimethylmorpholin-4-yl]pyrazolo[1,5-a]pyrimidine-3-carboxylate (230 mg, 755 umol) in a mixed solvent of MeOH (5 mL) and $H_2O$ (1 mL) was added LiOH·$H_2O$ (158 mg, 3.78 mmol). The mixture was stirred at 60° C. for 16 hrs. On completion, the mixture was concentrated in vacuo. The residue was diluted with $H_2O$ (5 mL), the mixture was acidified with 1N HCl solution until the pH=5. The mixture was filtered and the solid was dried in vacuo to give the title compound (140 mg, 67% yield) as white solid. $^1H$ NMR (400 MHz, DMSO-$d_6$) δ 11.68 (s, 1H), 8.75 (d, J=8.0 Hz, 1H), 8.19 (s, 1H), 6.88 (d, J=8.0 Hz, 1H), 4.58-4.32 (m, 2H), 3.68-3.54 (m, 2H), 2.70-2.56 (m, 2H), 1.19 (s, 3H), 1.17 (s, 3H).

5-[(2R,6R)-2,6-dimethylmorpholin-4-ylpyrazolo[1,5-a]pyrimidine-3-carboxylic acid (Intermediate AEF)

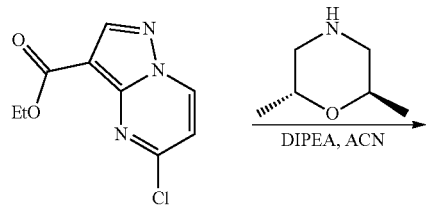

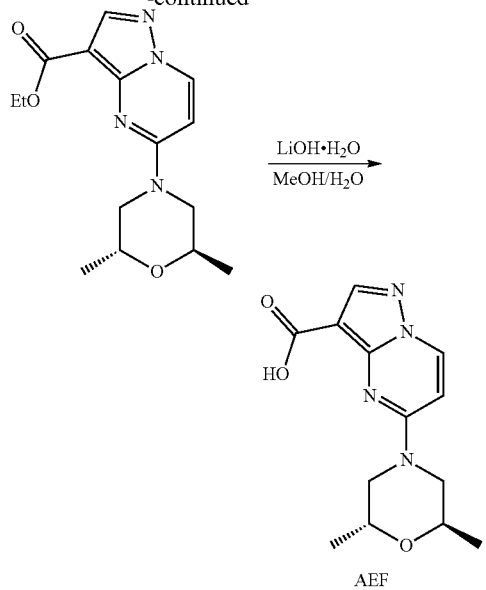

AEF

Step 1—Ethyl 5-[(2R,6R)-2,6-dimethylmorpholin-4-yl]pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7) and (2R,6R)-2,6-dimethylmorpholine (112 mg, 975 umol 1, CAS #171753-74-5) in ACN (5.00 mL) was added DIPEA (343 mg, 2.66 mmol). The mixture was stirred at 60° C. for 3 hrs. On completion, the reaction mixture was concentrated in vacuo, then diluted with water (5 mL) and extracted with EA (2×10 mL). The combined organic layers were washed with brine (2×30 mL), dried over $Na_2SO_4$ and concentrated in vacuo to give the title compound (230 mg, 85% yield) as a white solid. $^1H$ NMR (400 MHz, DMSO-$d_6$) δ 8.72 (d, J=7.6 Hz, 1H), 8.20 (s, 1H), 6.86 (d, J=8.0 Hz, 1H), 4.21-4.17 (m, 2H), 4.10-4.00 (m, 2H), 4.00-3.77 (m, 2H), 3.47 (dd, J=6.4, 13.2 Hz, 2H), 1.28 (t, J=7.2 Hz, 3H), 1.14 (d, J=6.4 Hz, 6H).

Step 2—5-[(2R,6R)-2,6-dimethylmorpholin-4-yl]pyrazolo[1,5-a]pyrimidine-3-carboxylic acid To a solution of ethyl 5-[(2R,6R)-2,6-dimethylmorpholin-4-yl]pyrazolo[1,5-a]pyrimidine-3-carboxylate (100 mg, 328 umol) in a mixed solvent of MeOH (2.00 mL) and $H_2O$ (0.50 mL) was added LiOH·$H_2O$ (41.3 mg, 985 mmol). The mixture was stirred at 60° C. for 16 hrs. On completion, the reaction mixture was quenched by water (1 mL), concentrated in vacuo to remove MeOH. Then the mixture was acidified with 1N HCl solution until the pH=5. The aqueous phase was extracted with EA (3×5 mL). The combined organic layer was washed with brine (2×10 mL), dried with anhydrous $Na_2SO_4$, filtered and the filtrate was concentrated in vacuo to give the title compound (70.0 mg, 77% yield) as a white solid. $^1H$ NMR (400 MHz, CHLOROFORM-d) δ 10.66-9.75 (m, 1H), 8.35 (d, J=8.0 Hz, 1H), 8.34 (s, 1H), 6.44 (d, J=8.0 Hz, 1H), 4.23-4.13 (m, 2H), 3.85 (d, J=10.4 Hz, 2H), 3.46 (dd, J=6.8, 12.8 Hz, 2H), 1.29 (d, J=6.4 Hz, 6H).

5-[(1S,4S)-2-oxa-5-azabicyclo[2.2.1]heptan-5-yl]
pyrazolo[1,5-a]pyrimidine-3-carboxylic acid (Intermediate AEG)

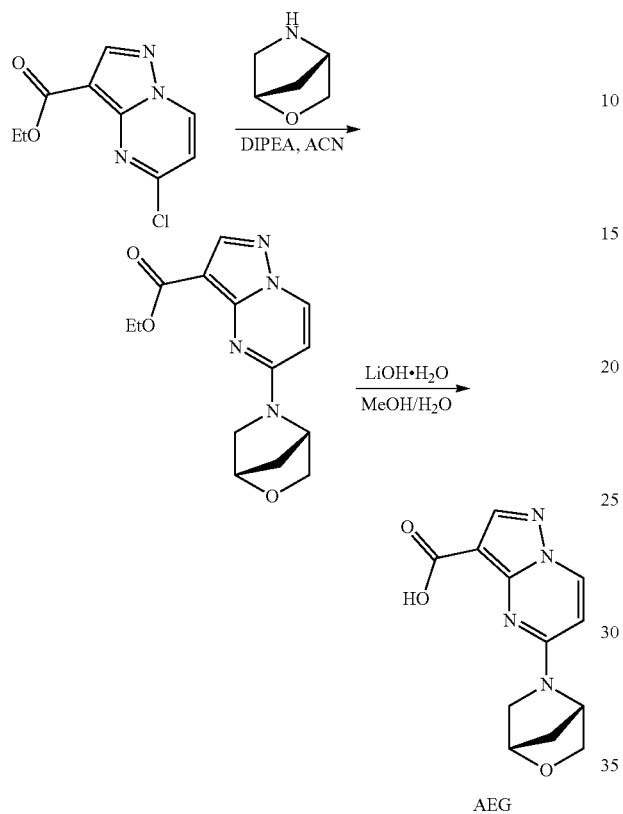

AEG

Step 1—Ethyl 5-[(1S,4S)-2-oxa-5-azabicyclo[2.2.1]heptan-5-yl]pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7) and (1S,4S)-2-oxa-5-azabicyclo[2.2.1]heptane (131 mg, 1.33 mmol, CAS #279-33-4) in ACN (6 mL) was added DIPEA (458 mg, 3.55 mmol). The mixture was stirred at 60° C. for 2 hours. On completion, the mixture was concentrated in vacuo. The residue was purified by reverse phase (0.1% FA) to give the title compound (210 mg, 82% yield) as yellow oil. $^1$H NMR (400 MHz, DMSO-d$_6$) δ 8.71 (d, J=8.0 Hz, 1H), 8.19 (s, 1H), 6.87-6.31 (m, 1H), 5.25-4.92 (m, 1H), 4.24-4.14 (m, 3H), 3.90-3.78 (m, 1H), 3.78-3.62 (m, 1H), 3.61-3.35 (m, 2H), 2.01-1.89 (m, 2H), 1.29 (t, J=7.2 Hz, 3H), LC-MS (ESI$^+$) m/z 289.1 (M+H)$^+$.

Step 2—5-[(1 S,4S)-2-oxa-5-azabicyclo[2.2.1]heptan-5-yl]pyrazolo[1,5-a]pyrimidine-3-carboxylic acid To a solution of ethyl 5-[(1S,4S)-2-oxa-5-azabicyclo[2.2.1]heptan-5-yl]pyrazolo[1,5-a] pyrimidine-3-carboxylate (210 mg, 728 umol) in a mixed solvent of MeOH (5 mL) and H$_2$O (1 mL) was added LiOH—H$_2$O (152 mg, 3.64 mmol). The mixture was stirred at 60° C. for 16 hours. On completion, the mixture was concentrated in vacuo. The residue was diluted with H$_2$O (10 mL) and acidified with 1N HCl solution until the pH=3. Then, the mixture was extracted with EA (5×20 mL), the combined organic layers dried over anhydrous Na$_2$SO$_4$, filtered and concentrated in vacuo to give the title compound (170 mg, 89% yield) as white solid. $^1$H NMR (400 MHz, DMSO-d$_6$) δ 8.71 (d, J=8.0 Hz, 1H), 8.17 (s, 1H), 7.00-6.23 (m, 1H), 5.23-4.94 (m, 1H), 4.80-4.68 (m, 1H), 3.90-3.77 (m, 1H), 3.77-3.67 (m, 1H), 3.58-3.39 (m, 2H), 2.01-1.85 (m, 2H).

5-[(1R,4R)-2-oxa-5-azabicyclo[2.2.1]heptan-5-yl]
pyrazolo[1,5-a]pyrimidine-3-carboxylic acid (Intermediate AEH)

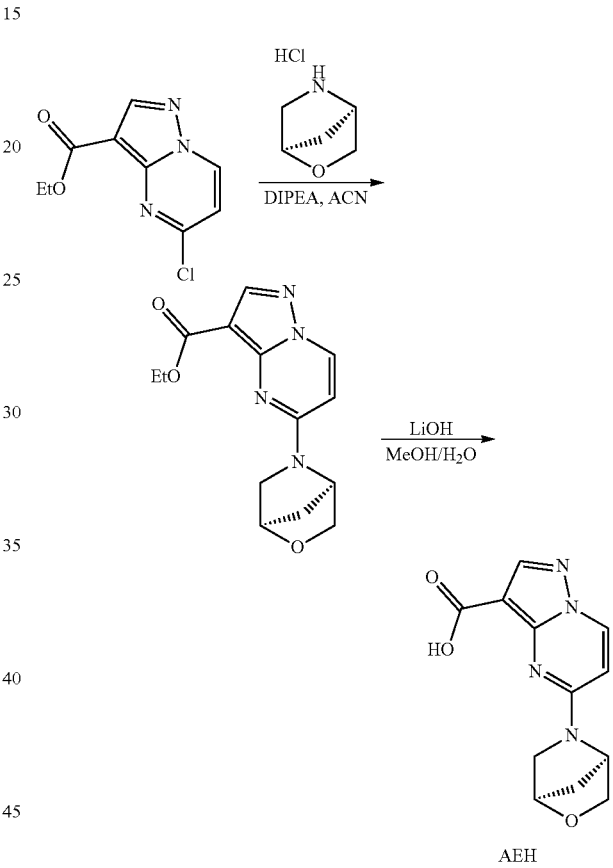

AEH

Step 1—Ethyl 5-[(1R,4R)-2-oxa-5-azabicyclo[2.2.1]heptan-5-yl]pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7) and (1R,4R)-2-oxa-5-azabicyclo[2.2.1]heptane (144 mg, 1.06 mmol, HCl salt, CAS #661470-56-0) in ACN (5.00 mL) was added DIPEA (343 mg, 2.66 mmol). The mixture was stirred at 60° C. for 3 hours. On completion, the reaction mixture was concentrated in vacuo, then diluted with water (5 mL) and extracted with EA (2×10 mL). The combined organic layers were washed with brine (2×30 mL), dried over Na$_2$SO$_4$, concentrated in vacuo to give the title compound (180 mg, 70% yield) as a white solid. $^1$H NMR (400 MHz, CDCl$_3$) δ 8.38-8.18 (m, 2H), 6.12 (s, 1H), 5.46 (s, 1H), 4.77 (s, 1H), 4.34 (q, J=7.2 Hz, 2H), 4.06-3.87 (m, 2H), 3.75-3.38 (m, 2H), 2.09-1.90 (m, 2H), 1.38 (t, J=7.2 Hz, 3H).

Step 2—5-[(1R,4R)-2-oxa-5-azabicyclo[2.2.1]heptan-5-yl]pyrazolo[1,5-a]pyrimidine-3-carboxylic acid To a solution of ethyl 5-[(1R,4R)-2-oxa-5-azabicyclo[2.2.1]heptan-5-yl]pyrazolo[1,5-a]pyrimidine-3-carboxylate (150 mg, 520 umol) in MeOH (10.0 mL) and H$_2$O (2.00 mL) was added LiOH—H$_2$O (43.6 mg, 1.04 mmol). The mixture was stirred at 60° C. for 16 hours. On completion, the reaction mixture was quenched with water (1 mL), and concentrated in vacuo to remove MeOH. Then the mixture was acidified with HCl (1 N) until the pH=5. The aqueous phase was extracted with EA (3×5 mL). The combined organic layer was washed with brine (2×10 mL), dried with anhydrous Na$_2$SO$_4$, filtered and concentrated in vacuo to give the title compound (135 mg, 99% yield) as a white solid. $^1$H NMR (400 MHz, CDCl$_3$) δ 11.31-9.30 (m, 1H), 8.32 (d, J=7.6 Hz, 1H), 8.28 (s, 1H), 6.44-6.12 (m, 1H), 5.29-4.58 (m, 2H), 4.00-3.85 (m, 2H), 3.77-3.49 (m, 2H), 2.20-1.97 (m, 2H).

Tert-butyl 4-[4-amino-3-(difluoromethyl)pyrazol-1-yl]piperidine-1-carboxylate (Intermediate AEI)

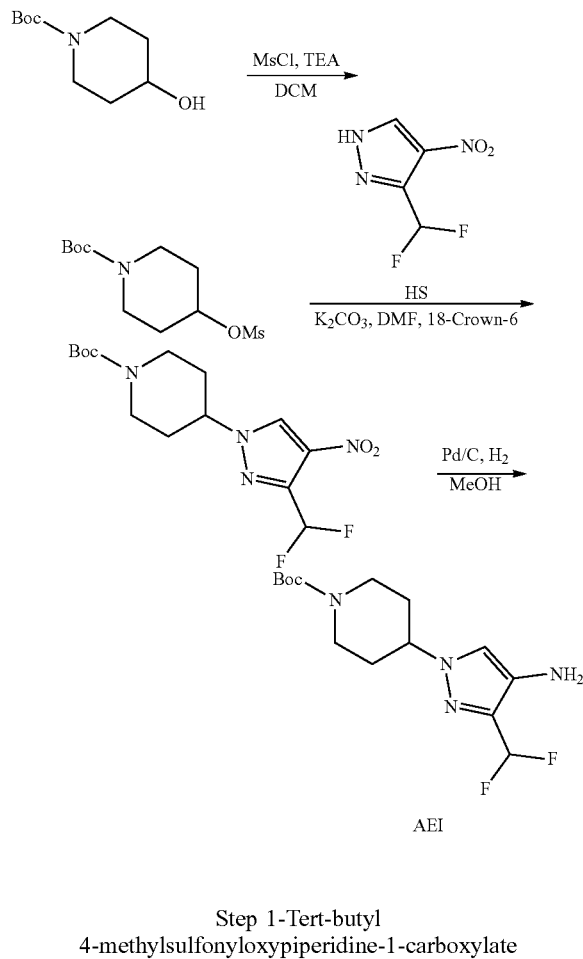

AEI

Step 1-Tert-butyl 4-methylsulfonyloxypiperidine-1-carboxylate

To a solution of tert-butyl 4-hydroxypiperidine-1-carboxylate (10.0 g, 49.6 mmol) and TEA (7.54 g, 74.5 mmol) in dichloromethane (100 mL) was added MsCl (6.83 g, 59.6 mmol) at 0° C. The reaction mixture was stirred at 0-15° C. for 1 hour. On completion, the reaction mixture was diluted with water (30 mL) and extracted with dichloromethane (3×60 mL). The combined organic layers were washed with aq. citric acid (2 N) (30 mL), saturated bicarbonate (2×30 mL), and brine (3×50 mL). The organic layer was then dried over anhydrous sodium sulfate, filtered and concentrated in vacuo to give the title compound (13.6 g, 97% yield) as yellow solid. $^1$H NMR (400 MHz, CDCl$_3$) δ 4.95-4.83 (m, 1H), 3.76-3.65 (m, 2H), 3.37-3.25 (m, 2H), 3.07-3.01 (m, 3H), 2.03-1.91 (m, 2H), 1.88-1.76 (m, 2H), 1.48-1.45 (m, 9H).

Step 2—Tert-butyl 4-[3-(difluoromethyl)-4-nitropyrazol-1-yl]piperidine-1-carboxylate A mixture of tert-butyl 4-methyl sulfonyloxypiperidine-1-carboxylate (7.00 g, 25.0 mmol), 3-(difluoromethyl)-4-nitro-1H-pyrazole (2.92 g, 17.9 mmol, Intermediate HS), K$_2$CO$_3$ (7.42 g, 53.7 mmol) and 18-Crown-6 (473 mg, 1.79 mmol) in DMF (80 mL) was stirred at 80° C. for 24 hours. On completion, the reaction mixture was diluted with water (400 mL) and extracted with ethyl acetate (3×100 mL). The combined organic layers were washed with brine (3×50 mL), dried over anhydrous sodium sulfate, filtered and concentrated in vacuo. The residue was purified by silica gel chromatography (petroleum ether:ethyl acetate=4:1) to give the title compound (3.50 g, 42% yield) as white solid. $^1$H NMR (400 MHz, CDCl$_3$) δ 8.23 (s, 1H), 7.26-6.97 (m, 1H), 4.43-4.23 (m, 3H), 2.97-2.82 (m, 2H), 2.25-2.16 (m, 2H), 1.97-1.91 (m, 2H), 1.49 (s, 9H).

Step 3—Tert-butyl 4-[4-amino-3-(difluoromethyl)pyrazol-1-yl]piperidine-1-carboxylate To a solution of tert-butyl 4-[3-(difluoromethyl)-4-nitro-pyrazol-1-yl]piperidine-1-carboxylate (5.50 g, 11.9 mmol) in MeOH (50 mL) was added Pd/C (0.500 g, 10% wt). The reaction mixture was stirred at 15° C. for 2 hours under hydrogen (15 psi). On completion, the reaction mixture was filtered and the filtrate was concentrated in vacuo to give the title compound (5.00 g, 99% yield) as yellow oil. $^1$H NMR (400 MHz, CDCl$_3$) δ 7.01 (s, 1H), 6.83-6.49 (m, 1H), 4.33-4.16 (m, 2H), 4.15-4.05 (m, 1H), 3.22 (s, 2H), 2.93-2.80 (m, 2H), 2.11-2.01 (m, 2H), 1.89-1.82 (m, 2H), 1.47 (s, 9H).

N-[3-(difluoromethyl)-1-(4-piperidyl)pyrazol-4-yl]-5-morpholino-pyrazolo[1,5-a]pyrimidine-3-carboxamide (Intermediate AEJ)

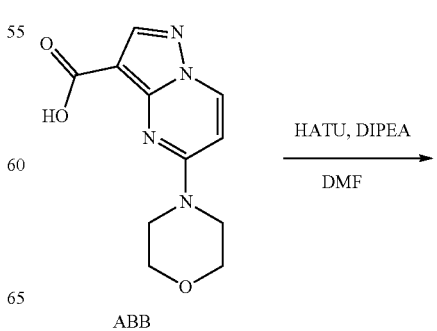

ABB

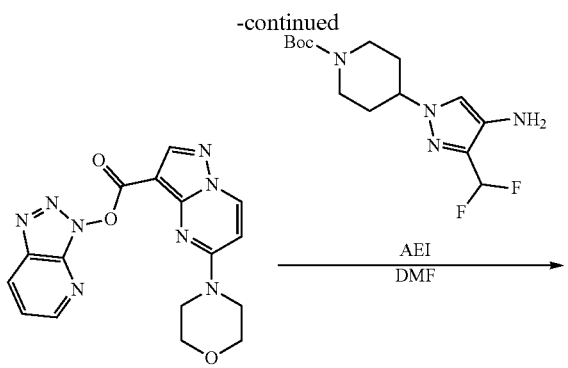

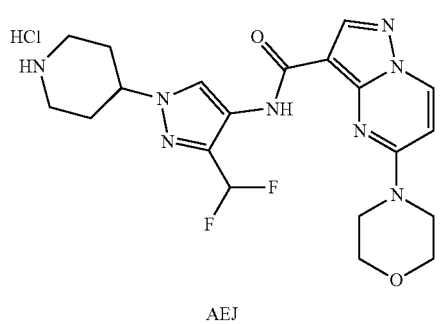

Step 1—Triazolo[4,5-b]pyridin-3-yl 5-morpholino-pyrazolo[1,5-a]pyrimidine-3-carboxylate To a solution of 5-morpholinopyrazolo[1,5-a]pyrimidine-3-carboxylic acid (2.5 g, 10.1 mmol, Intermediate ABB) in DMF (15 mL) was added DIPEA (3.90 g, 30.2 mmol, 5.26 mL) and HATU (4.60 g, 12.0 mmol), and the mixture was stirred at 20° C. for 30 mins. On completion, the reaction mixture was quenched with H$_2$O (50 mL), and a white solid was precipitated out from the solution. Then the mixture was filtered and the filter cake was dried in vacuo to give the title compound (3.1 g, 84% yield) as white solid. LC-MS (ESI$^+$) m/z 367.2 (M+H)$^+$.

Step 2—Tert-butyl 4-[3-(difluoromethyl)-4-[(5-morpholinopyrazolo[1,5-a]pyrimidine-3-carbonyl) amino] pyrazol-1-yl]piperidine-1-carboxylate A solution of triazolo[4,5-b]pyridin-3-yl 5-morpholino-pyrazolo[1,5-a]pyrimidine-3-carboxylate (3.1 g, 8.46 mmol) and tert-butyl 4-[4-amino-3-(difluoromethyl)pyrazol-1-yl]piperidine-1-carboxylate (2.68 g, 8.46 mmol, Intermediate AEI) in DMF (50 mL), the reaction mixture was stirred at 50° C. for 12 hours. On completion, the reaction mixture was quenched with H$_2$O (150 mL), and a white solid was precipitated out from the solution. Then the mixture was filtered and the filter cake was concentrated in vacuo to give the title compound (4.1 g, 88% yield) as white solid. $^1$H NMR (400 MHz, CDCl$_3$) δ 9.50 (s, 1H), 8.43 (s, 2H), 8.34 (d, J=7.6 Hz, 1H), 6.93-6.59 (m, 1H), 6.41 (d, J=8.0 Hz, 1H), 4.41-4.09 (m, 3H), 3.90-3.82 (m, 4H), 3.81-3.77 (m, 4H), 2.93-2.86 (m, 2H), 2.19-2.05 (m, 2H), 2.02-1.89 (m, 2H), 1.48 (s, 9H).

Step 3—N-[3-(difluoromethyl)-1-(4-piperidyl)pyrazol-4-yl]-5-morpholino-pyrazolo[1,5-a]pyrimidine-3-carboxamide To a solution of tert-butyl 4-[3-(difluoromethyl)-4-[(5-morpholinopyrazolo[1,5-a]pyrimidine-3-carbonyl)amino] pyrazol-1-yl]piperidine-1-carboxylate (1.1 g, 2.01 mmol) in DCM (10 mL) was added HCl/dioxane (4 M, 5.00 mL), the reaction mixture was stirred at 20° C. for 12 hours. On completion, the reaction mixture was concentrated in vacuo to give the title compound (900 mg, 92% yield, HCl salt) as a white solid. LC-MS (ESI$^+$) m/z 447.1 (M+H)$^+$.

N-[3-(difluoromethyl)-1-[1-[2-(4-piperidyl)ethyl]-4-piperidyl]pyrazol-4-yl]-5-morpholino-pyrazolo[1,5-a]pyrimidine-3-carboxamide (Intermediate AEK)

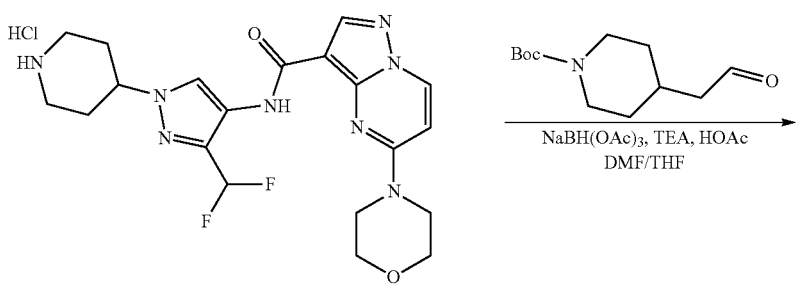

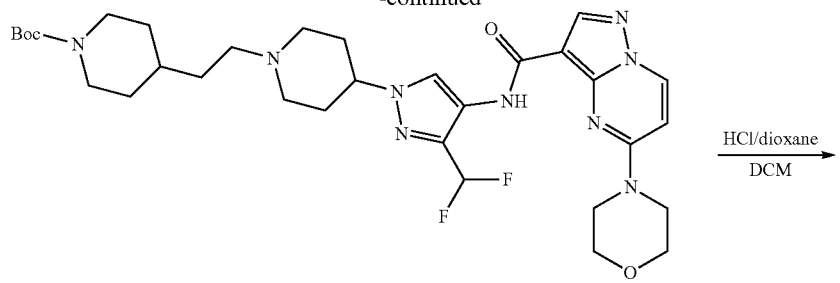

Step 1—Tert-butyl 4-[2-[4-[3-(difluoromethyl)-4-[(5-morpholinopyrazolo[1,5-a]pyrimidine-3-carbonyl)amino]pyrazol-1-yl]-1-piperidyl]ethyl]piperidine-1-carboxylate To a solution of N-[3-(difluoromethyl)-1-(4-piperidyl)pyrazol-4-yl]-5-morpholino-pyrazolo[1,5-a] pyrimidine-3-carboxamide (200 mg, 414 umol, HCl, Intermediate AEJ) in DMF (3 mL) and THF (6 mL) was added TEA (41.9 mg, 414 umol, 57.6 uL), the mixture was stirred at 20° C. for 15 mins, then tert-butyl 4-(2-oxoethyl)piperidine-1-carboxylate (94.1 mg, 414 umol, CAS #142374-19-4) and HOAc (49.7 mg, 828 umol, 47.3 uL) was added to the mixture, the reaction mixture was stirred at 20° C. for 30 mins. Then NaBH(OAc)₃ (131 mg, 621 umol) was added to the mixture, the reaction mixture was stirred at 20° C. for 12 hours. On completion, the reaction mixture was quenched with water (0.5 mL), filtered and the filtrate was concentrated in vacuo. The residue was purified by reverse phase (0.1% FA) to give title compound (210 mg, 77% yield) as white solid. ¹H NMR (400 MHz, DMSO-$d_6$) δ 9.39 (s, 1H), 8.82 (d, J=8.0 Hz, 1H), 8.39 (s, 1H), 8.29 (s, 1H), 7.26-6.95 (m, 1H), 6.90 (d, J=8.0 Hz, 1H), 4.30-4.16 (m, 1H), 3.90 (d, J=12.4 Hz, 2H), 3.84-3.76 (m, 4H), 3.75-3.67 (m, 4H), 3.00-2.90 (m, 2H), 2.75-2.60 (m, 2H), 2.35 (t, J=7.2 Hz, 2H), 2.11-1.85 (m, 6H), 1.69-1.57 (m, 2H), 1.51-1.42 (m, 1H), 1.42-1.33 (m, 11H), 1.06-0.91 (m, 2H); LC-MS (ESI⁺) m/z 658.5 (M+H)⁺.

Step 2—N-[3-(difluoromethyl)-1-[1-[2-(4-piperidyl)ethyl]-4-piperidyl]pyrazol-4-yl]-5-morpholino-pyrazolo[1,5-a]pyrimidine-3-carboxamide To a solution of tert-butyl 4-[2-[4-[3-(difluoromethyl)-4-[(5-morpholinopyrazolo[1,5-a]pyrimidine-3-carbonyl)amino]pyrazol-1-yl]-1-piperidyl]ethyl]piperidine-1-carboxylate (200 mg, 304 umol) in DCM (4 mL) was added HCl/dioxane (4 M, 2.00 mL), the reaction mixture was stirred at 20° C. for 30 mins. On completion, the reaction mixture was concentrated in vacuo to give the title compound (180 mg, 99% yield, HCl salt) as a yellow solid. LC-MS (ESI⁺) m/z 558.5 (M+H)⁺.

2-[2-(Cyclopropylmethylamino)-4-pyridyl]-N-[3-(difluoromethyl)-1-[1-[2-(4-piperidyl)ethyl]-4-piperidyl]pyrazol-4-yl]oxazole-4-carboxamide (Intermediate AEL)

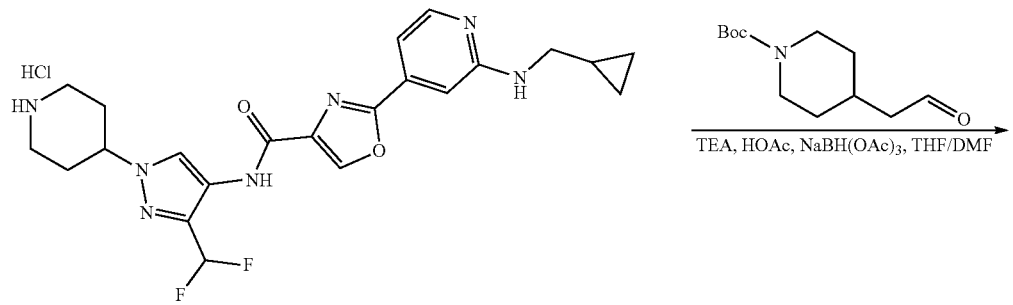

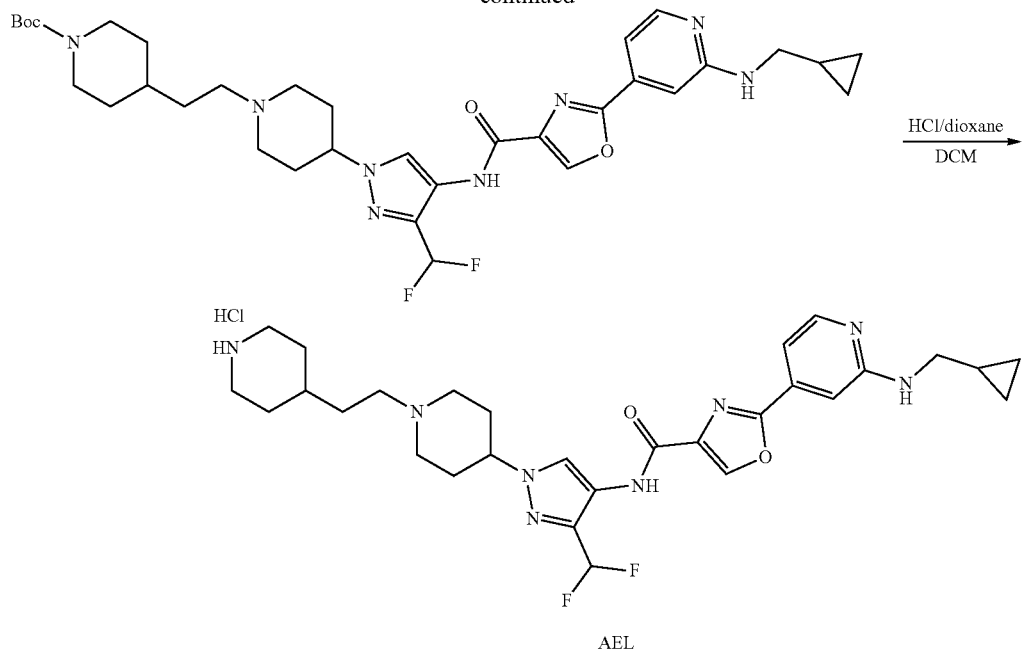

AEL

Step 1—Tert-butyl 4-[2-[4-[4-[[2-[2-(cyclopropylmethylamino)-4-pyridyl]oxazole-4-carbonyl]amino]-3-(difluoromethyl)pyrazol-1-yl]-1-piperidyl]ethyl]piperidine-1-carboxylate To a solution of 2-[2-(cyclopropylmethylamino)-4-pyridyl]-N-[3-(difluoromethyl)-1-(4-piperidyl) pyrazol-4-yl] oxazole-4-carboxamide (217 mg, 439 umol, HCl salt, Intermediate AAY) in a mixed solvents of DMF (2 mL) and THF (3 mL) was added TEA until the pH=7-8, and acidified with AcOH until the pH=5-6. Then tert-butyl 4-(2-oxoethyl)piperidine-1-carboxylate (100 mg, 439 umol, CAS #142374-19-4) was added. The reaction mixture was stirred at 10° C. for 1 hour. Then, NaBH(OAc)$_3$ (186 mg, 879 umol) was added. The reaction mixture was stirred at 10° C. for 12 hours. On completion, the reaction mixture was quenched by water (0.2 mL), filtered and the filtrate was concentrated in vacuo. The residue was purified by reverse phase (0.1% FA) to give title compound (230 mg, 78% yield) as white solid. $^1$H NMR (400 MHz, CDCl$_3$) δ 9.05 (s, 1H), 8.36-8.34 (m, 2H), 8.20 (d, J=5.2 Hz, 1H), 7.20 (dd, J=1.2, 5.2 Hz, 1H), 7.05 (s, 1H), 6.99-6.66 (m, 1H), 5.57-5.23 (m, 1H), 4.26-4.15 (m, 2H), 4.14-4.01 (m, 2H), 3.23 (d, J=6.8 Hz, 2H), 3.21-3.11 (m, 2H), 2.69 (t, J=11.6 Hz, 2H), 2.63-2.54 (m, 2H), 2.47-2.33 (m, 2H), 2.31-2.14 (m, 4H), 1.70-1.61 (m, 2H), 1.58-1.51 (m, 2H), 1.46 (s, 9H), 1.24-1.05 (m, 3H), 0.65-0.56 (m, 2H), 0.35-0.28 (m, 2H).

Step 2—2-[2-(Cyclopropylmethylamino)-4-pyridyl]-N-[3-(difluoromethyl)-1-[1-[2-(4-piperidyl)ethyl]-4-piperidyl]pyrazol-4-yl]oxazole-4-carboxamide To a solution of tert-butyl 4-[2-[4-[4-[[2-[2-(cyclopropylmethylamino)-4-pyridyl]oxazole-4-carbonyl] amino]-3-(difluoromethyl)pyrazol-1-yl]-1-piperidyl]ethyl]piperidine-1-carboxylate (220 mg, 307 umol, FA) in dichloromethane (2 mL) was added HCl/dioxane (4 M, 2.00 mL). The reaction mixture was stirred at 10° C. for 1 hour. On completion, the reaction mixture was concentrated in vacuo to give the title compound (186 mg, 99% yield, HCl salt) as off-white solid. $^1$H NMR (400 MHz, DMSO-d$_6$) δ 10.06-9.92 (m, 1H), 9.19-9.09 (m, 1H), 8.22 (s, 1H), 8.08 (d, J=6.4 Hz, 1H), 7.63 (s, 1H), 7.47-6.99 (m, 2H), 4.75-4.47 (m, 1H), 3.68-3.59 (m, 2H), 3.35-3.34 (m, 2H), 3.27-3.20 (m, 3H), 3.14-3.01 (m, 4H), 2.89-2.72 (m, 2H), 2.53-2.51 (m, 1H), 2.45-2.34 (m, 2H), 2.32-2.23 (m, 2H), 1.88-1.77 (m, 2H), 1.75-1.60 (m, 3H), 1.44-1.29 (m, 2H), 1.20-1.07 (m, 1H), 0.60-0.50 (m, 2H), 0.37-0.27 (m, 2H).

3-[3-[1-(2,6-Dioxo-3-piperidyl)-3-methyl-2-oxo-benzimidazol-5-yl]propoxy]propanal (Intermediate AEM)

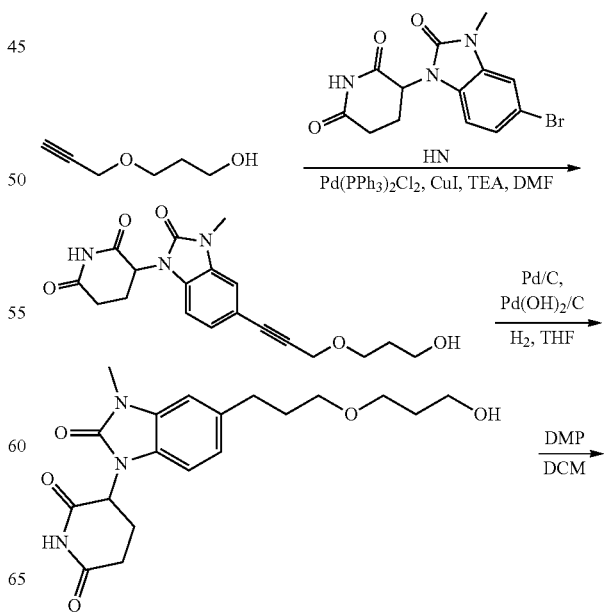

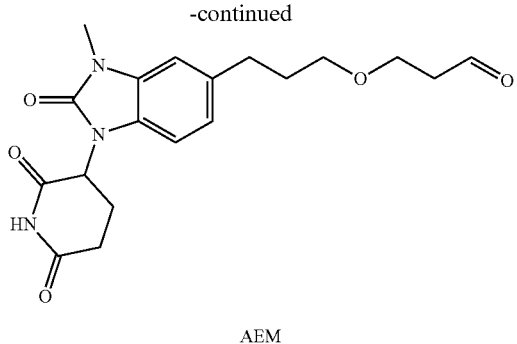

AEM

Step 1—3-[5-[3-(3-Hydroxypropoxy)prop-1-ynyl]-3-methyl-2-oxo-benzimidazol-1-yl]piperidine-2,6-dione A mixture of 3-prop-2-ynoxypropan-1-ol (202 mg, 1.77 mmol, Intermediate ADH), 3-(5-bromo-3-methyl-2-oxo-benzimidazol-1-yl)piperidine-2,6-dione (500 mg, 1.48 mmol, Intermediate HN), Pd(PPh₃)₂Cl₂ (104 mg, 147 umol), CuI (28.2 mg, 147 umol), TEA (1.50 g, 14.8 mmol,) and 4 Å molecular sieves (100 mg) in DMF (10.0 mL) was degassed and purged with N₂ three times, and then the mixture was stirred at 80° C. for 2 hours under N₂ atmosphere. On completion, the reaction mixture was concentrated in vacuo to remove DMF. The residue was diluted with EA (50 mL) and water (20 mL). The mixture was extracted with EA (3×20 mL), the organic layer was separated and washed with brine (2×50 mL), dried over anhydrous Na₂SO₄, filtered and the filtrate was concentrated in vacuo to give a residue. The residue was purified by reverse phase (0.1% FA) to give the title compound (400 mg, 72% yield) as a white solid. ¹H NMR (400 MHz, DMSO-d₆) δ 11.11 (s, 1H), 7.99-7.71 (m, 1H), 7.32 (d, J=0.8 Hz, 1H), 7.19-7.11 (m, 1H), 5.59-5.24 (m, 1H), 4.40-4.27 (m, 2H), 3.57 (t, J=6.4 Hz, 1H), 3.50-3.47 (m, 2H), 3.47-3.44 (m, 2H), 3.34 (s, 3H), 2.97-2.82 (m, 1H), 2.79-2.58 (m, 2H), 2.18-1.92 (m, 1H), 1.67-1.52 (m, 2H).

Step 2—3-[5-[3-(3-Hydroxypropoxy)propyl]-3-methyl-2-oxo-benzimidazol-1-yl]piperidine-2,6-dione To a solution of 3-[5-[3-(3-hydroxypropoxy)prop-1-ynyl]-3-methyl-2-oxo-benzimidazol-1-yl] piperidine-2,6-dione (400 mg, 1.08 mmol) in THF (15.0 mL) was added Pd/C (100 mg, 10% wt) and Pd(OH)₂ (100 mg, 20% wt) under N₂ atmosphere. The suspension was degassed and purged with H₂ three times. The mixture was stirred under H₂ (15 psi) at 20° C. for 16 hours. On completion, the reaction mixture was filtered, and the filtrate was concentrated in vacuo to give the title compound (400 mg, 98% yield) as a yellow solid. ¹H NMR (400 MHz, DMSO-d₆) δ 11.07 (s, 1H), 7.18-6.94 (m, 2H), 6.91-6.80 (m, 1H), 5.33 (dd, J=5.2, 12.8 Hz, 1H), 3.49-3.44 (m, 2H), 3.43-3.39 (m, 2H), 3.37-3.34 (m, 2H), 3.30 (s, 3H), 2.80-2.58 (m, 4H), 2.08-1.94 (m, 1H), 1.87-1.71 (m, 2H), 1.69-1.62 (m, 4H).

Step 3—3-[3-[1-(2,6-Dioxo-3-piperidyl)-3-methyl-2-oxo-benzimidazol-5-yl]propoxy]propanal To a solution of 3-[5-[3-(3-hydroxypropoxy) propyl]-3-methyl-2-oxo-benzimidazol-1-yl]piperidine-2,6-dione (200 mg, 532 umol) in DCM (6.00 mL) was added DMP (338 mg, 799 umol) in portions. The resulting solution was stirred at 25° C. for 1 hour. On completion, the reaction mixture was quenched by Na₂S₂O₃ (1 mL) and NaHCO₃ (1 mL), then diluted with water (5 mL) and extracted with DCM (2×10 mL). The combined organic layers were washed with brine (2×30 mL), dried over Na₂SO₄, The organic layers was concentrated in vacuo to give the title compound (190 mg, 95% yield) as a white solid. LC-MS (ESI⁺) m/z 374.2 (M+H)⁺.

N-[1-[4-[[5-aminopentyl(methyl)amino]methyl]cyclohexyl]-3-(difluoromethyl)pyrazol-4-yl]-2-[2-(cyclopropylmethylamino)-4-pyridyl]oxazole-4-carboxamide (Intermediate AEN)

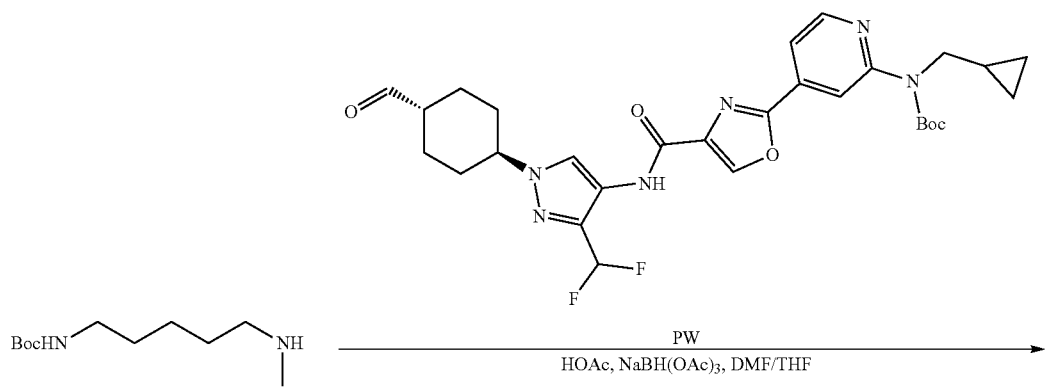

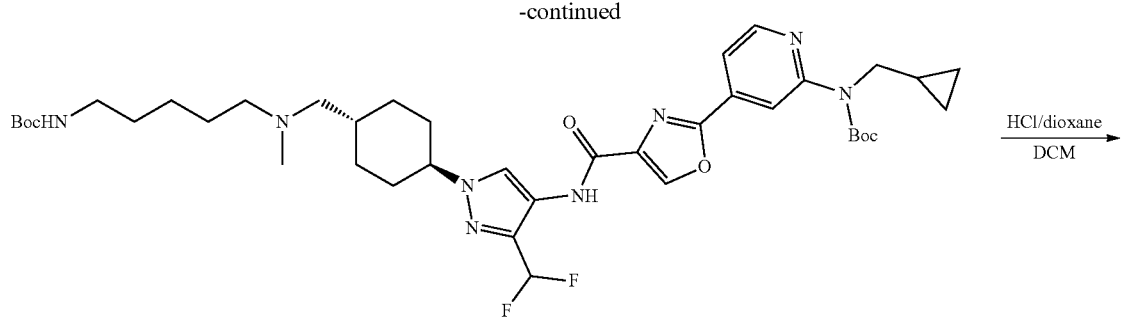

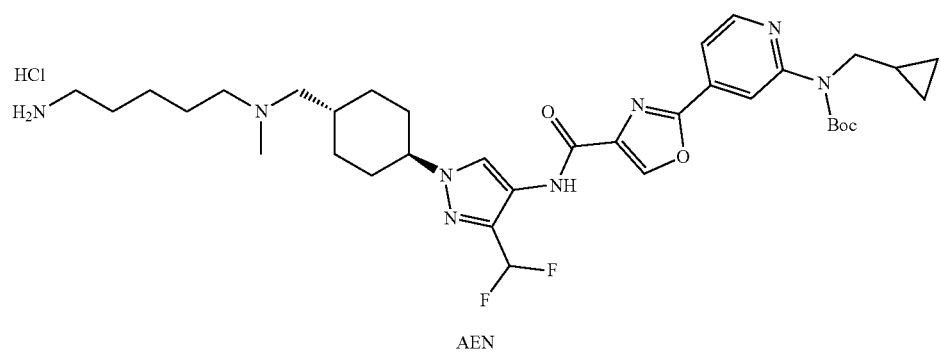

AEN

Step 1—Tert-butyl N-[4-[4-[[1-[4-[[5-(tert-butoxycarbonylamino)pentyl-methyl-amino]methyl] cyclohexyl]-3-(difluoromethyl)pyrazol-4-yl]carbamoyl] oxazol-2-yl]-2-pyridyl]-N-(cyclopropylmethyl) carbamate To a solution of tert-butyl N-[5-(methylamino)pentyl] carbamate (100 mg, 462 umol, CAS #1311458-36-2) and tert-butyl N-(cyclopropylmethyl)-N-[4-[4-[[3-(difluoromethyl)-1-(4-formylcyclo hexyl)pyrazol-4-yl]carbamoyl]oxazol-2-yl]-2-pyridyl]carbamate (270 mg, 462 umol, Intermediate PW) in a mixed of solvent DMF (2.00 mL) and THF (2.00 mL) was added HOAc (33.3 mg, 554 umol). Then 30 min later, NaBH(OAc)₃ (146 mg, 693 umol) was added. The reaction mixture was stirred at 0° C. for 3 hrs. On completion, the reaction mixture was quenched with water (0.5 ml) and concentrated in vacuo to give a residue. The residue was purified by reversed phase (0.1% FA condition) to give the title compound (300 mg, 79% yield) as white solid. LC-MS (ESI⁺) m/z 785.5 (M+H)⁺.

Step 2—N-[1-[4-[[5-aminopentyl(methyl)amino] methyl]cyclohexyl]-3-(difluoromethyl)pyrazol-4-yl]-2-[2-(cyclopropylmethylamino)-4-pyridyl]oxazole-4-carboxamide To a solution of tert-butyl N-[4-[4-[[1-[4-[[5-(tert-butoxycarbonylamino)pentyl-methyl-amino]methyl] cyclohexyl]-3-(difluoromethyl)pyrazol-4-yl]carbamoyl]oxazol-2-yl]-2-pyridyl]-N-(cyclopropylmethyl)carbamate (35.0 mg, 44.6 umol) in DCM (2.00 mL) was added HCl/dioxane (4 M, 2.00 mL). The mixture was stirred at 20° C. for 2 hrs. On completion, the reaction mixture was concentrated in vacuo to give the title compound (27.0 mg, 97% yield, HCl) as a yellow solid. LC-MS (ESI⁺) m/z 585.4 (M+H)⁺.

4-[3-(Difluoromethyl)-4-[(5-morpholinopyrazolo[1,5-a]pyrimidine-3-carbonyl)amino] pyrazol-1-yl]] cyclohexanecarboxylic acid (Intermediate AEO)

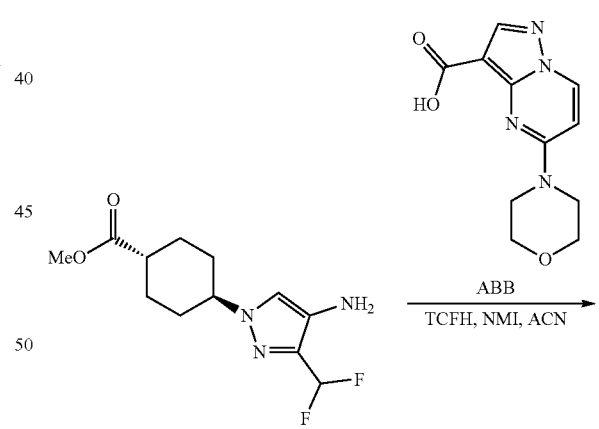

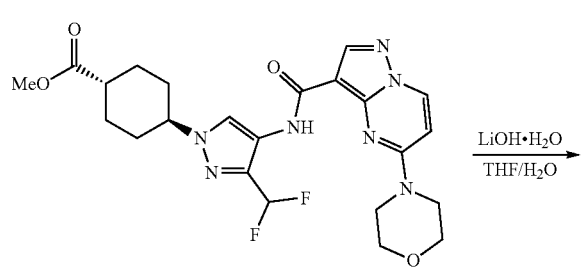

-continued

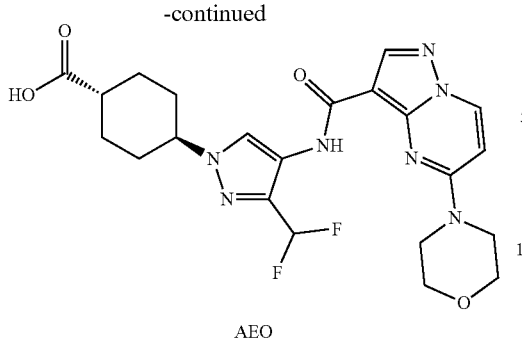

AEO

Step 1—Methyl 4-[3-(difluoromethyl)-4-[(5-morpholinopyrazolo[1,5-a]pyrimidine-3-carbonyl) amino] pyrazol-1-yl]]cyclohexanecarboxylate To a mixture of 5-morpholinopyrazolo[1,5-a]pyrimidine-3-carboxylic acid (1.00 g, 4.03 mmol, Intermediate ABB) in ACN (20 mL) was added 1-methylimidazole (1.16 g, 14.1 mmol), [chloro (dimethylamino)methylene]-dimethyl-ammonium; hexafluorophosphate (1.36 g, 4.83 mmol) and methyl 4-[4-amino-3-(difluoromethyl)pyrazol-1-yl]cyclohexanecarboxylate (1.10 g, 4.03 mmol, Intermediate QS). The reaction mixture was stirred at 25° C. for 2 hours. On completion, the reaction mixture was quenched with water (1 mL) and concentrated in vacuo. The residue was triturated with PE/EA/ACN=10/2/2 (100 mL) and filtered to give the filter cake as title compound (1.2 g, 59% yield) as white solid. $^1$H NMR (400 MHz, DMSO-$d_6$) δ 9.39 (s, 1H), 8.82 (d, J=8.0 Hz, 1H), 8.39 (s, 1H), 8.28 (s, 1H), 7.23-6.96 (m, 1H), 6.90 (d, J=8.0 Hz, 1H), 4.31-4.19 (m, 1H), 3.85-3.75 (m, 4H), 3.74-3.60 (m, 4H), 3.62 (s, 3H), 2.47-2.38 (m, 1H), 2.09-2.00 (m, 4H), 1.87-1.73 (m, 2H), 1.61-1.46 (m, 2H); LC-MS (ESI$^+$) m/z 504.3 (M+H)$^+$.

Step 2—4-[3-(Difluoromethyl)-4-[(5-morpholinopyrazolo[1,5-a]pyrimidine-3-carbonyl)amino] pyrazol-1-yl]cyclohexanecarboxylic acid To a mixture of methyl 4-[3-(difluoromethyl)-4-[(5-morpholinopyrazolo[1,5-a]pyrimidine-3-carbonyl) amino]pyrazol-1-yl]cyclohexanecarboxylate (1.10 g, 2.18 mmol) in a mixed solvent of THF (8 mL) and H$_2$O (2 mL) was added LiOH.H$_2$O (229 mg, 5.46 mmol). The reaction mixture was stirred at 25° C. for 12 hours. On completion, the reaction mixture was acidified with HCl (1 N) until the pH=5-6 and filtered to give the filter cake as title compound (1.00 g, 93% yield) as yellow solid. $^1$H NMR (400 MHz, DMSO-$d_6$) δ 9.39 (s, 1H), 8.65 (d, J=7.6 Hz, 1H), 8.27 (d, J=15.2 Hz, 2H), 7.15-6.87 (m, 1H), 6.81 (d, J=7.6 Hz, 1H), 4.11 (t, J=10.8 Hz, 1H), 3.72-3.69 (m, 8H), 2.05-1.82 (m, 5H), 1.75-1.57 (m, 2H), 1.50-1.34 (m, 2H); LC-MS (ESI$^+$) m/z 490.3 (M+H)$^+$.

1-[[(2S,3S,4S)-3-ethyl-4-fluoro-5-oxo-pyrrolidin-2-yl]methoxy]-4-[2-(4-formylcyclohexyl) ethynyl]-7-methoxy-isoquinoline-6-carboxamide (Intermediate AEP)

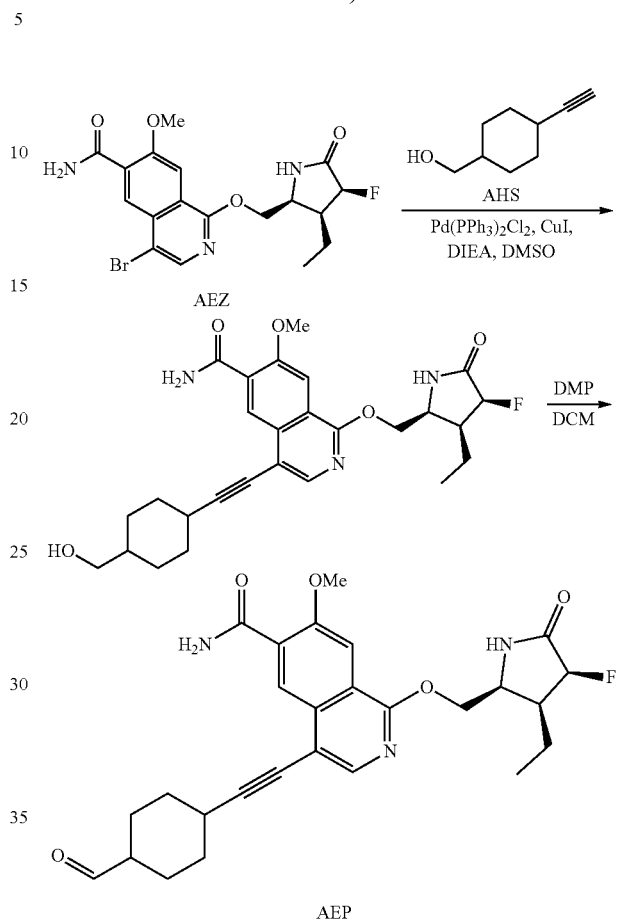

Step 1—1-[[(2S,3S,4S)-3-ethyl-4-fluoro-5-oxo-pyrrolidin-2-yl]methoxy]-4-[2-[4-(hydroxymethyl) cyclohexyl]ethynyl]-7-methoxy-isoquinoline-6-carboxamide (4-ethynylcyclohexyl)methanol (39.6 mg, 286 umol, Intermediate AHS), 4-bromo-1-[[(2S,3S,4S)-3-ethyl-4-fluoro-5-oxo-pyrrolidin-2-yl]methoxy]-7-methoxy-isoquinoline-6-carboxamide (70.0 mg, 159 umol, Intermediate AEZ), CuI (6.06 mg, 31.8 umol), Pd(PPh$_3$)$_2$Cl$_2$ (22.3 mg, 31.8 umol) and DIPEA (103 mg, 795 umol) in DMSO (2 mL) was de-gassed and then heated at 80° C. for 2 hours under N$_2$. On completion, the mixture was quenched with water (40 mL), and extracted with EA (2×50 mL). The organic layer was washed with brine (100 mL), and concentrated in vacuo. The residue was purified by reverse phase (0.1% FA) to give the title compound (60.0 mg, 76% yield) as a white solid. LC-MS (ESI$^+$) m/z 498.4 (M+H)$^+$.

Step 2—1-[[(2S,3S,4S)-3-ethyl-4-fluoro-5-oxo-pyrrolidin-2-yl]methoxy]-4-[2-(4-formylcyclohexyl) ethynyl]-7-methoxy-isoquinoline-6-carboxamide To a solution of 1-[[(2S,3S,4S)-3-ethyl-4-fluoro-5-oxo-pyrrolidin-2-yl]methoxy]-4-[2-[4-(hydroxyl methyl)cyclohexyl]ethynyl]-7-methoxy-isoquinoline-6-carboxamide (70.0 mg, 141 umol) in DCM (5 mL) was added DMP (71.6 mg, 169 umol). The reaction mixture was stirred at 20° C. for 2 hours. On completion, the mixture was quenched with sat. Na$_2$S$_2$O$_3$ (50 mL) and sat. NaHCO$_3$ (50 mL), and stirred for 10 minutes, then the mixture was extracted with DCM (2×30 mL). The organic layer was washed with brine (50 mL), dried with Na$_2$SO$_4$, filtered and the filtrate was concentrated in vacuo to give the title compound (60.0 mg, 86% yield) as yellow oil. LC-MS (ESI$^+$) m/z 496.2 (M+H)$^+$.

Tert-butyl N-methyl-N-[3-[2-(4-piperidyl)ethoxy]cyclobutyl]carbamate (Intermediate AEQ)

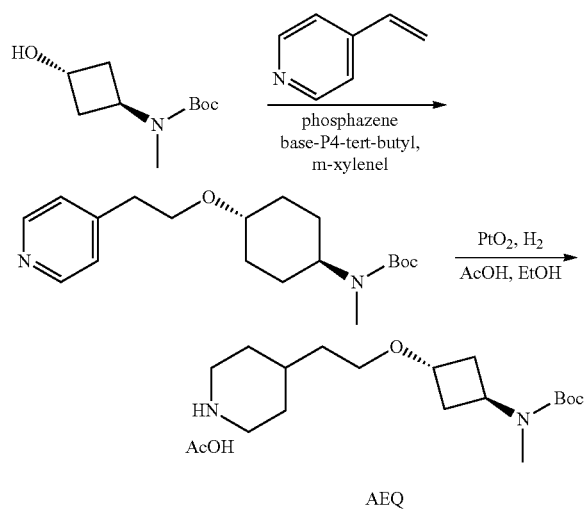

Step 1—Tert-butyl N-methyl-N-[3-[2-(4-pyridyl)ethoxy]cyclobutyl]carbamate

To a solution of tert-butyl N-(3-hydroxycyclobutyl)-N-methyl-carbamate (1.73 g, 8.60 mmol, Steps 1-2 of Intermediate YO) and 4-vinylpyridine (2.26 g, 21.4 mmol, CAS #100-43-6) in m-xylene (10 mL) was added N-[[tert-butyl-imino-bis[[tris(dimethylamino)-phosphanylidene]amino]-phosphanyl]imino-bis(dimethylamino)-phosphanyl]-N-methyl-methanamine (0.8 M, 1 mL). The reaction mixture was stirred at 80° C. for 20 hours. On completion, the reaction mixture was quenched with water (50 mL) and extracted with EA (2×100 mL). The combined organic layers were washed with brine (2×30 mL), dried with anhydrous Na$_2$SO$_4$ and filtered. The filtrate was concentrated in vacuo and the residue was purified by silica column (PE/EA, 10/1 to 2/1) to give the title compound (1.10 g 41% yield) as colorless oil. $^1$H NMR (400 MHz, CDCl$_3$) δ 8.55-8.49 (m, 2H), 7.18 (d, J=6.0 Hz, 2H), 4.65 (s, 1H), 4.08-3.95 (m, 1H), 3.56 (t, J=6.8 Hz, 2H), 2.88 (t, J=6.8 Hz, 2H), 2.81 (s, 3H), 2.37-2.18 (m, 4H), 1.46 (s, 9H).

Step 2—Tert-butyl N-methyl-N-[3-[2-(4-piperidyl)ethoxy]cyclobutyl]carbamate

To a solution of tert-butyl N-methyl-N-[3-[2-(4-pyridyl)ethoxy]cyclobutyl]carbamate (800 mg, 2.61 mmol) in EtOH (80 mL) was added AcOH (783 mg, 13.0 mmol). The reaction mixture was stirred at 25° C. for 0.5 hour. Then PtO$_2$ (59.2 mg, 261 umol) was added. The reaction mixture was stirred at 40° C. for 12 hours under H$_2$ (50 Psi). On completion, the reaction mixture was filtered and concentrated in vacuo to give the title compound (970 mg, 99% yield) as light yellow oil. LC-MS (ESI$^+$) m/z 313.0 (M+H)$^+$.

3-[3-Methyl-5-[[4-[2-[3-(methylamino)cyclobutoxy]ethyl]-1-piperidyl]methyl]-2-oxo-benzimidazol-1-yl]]piperidine-2,6-dione (Intermediate AER)

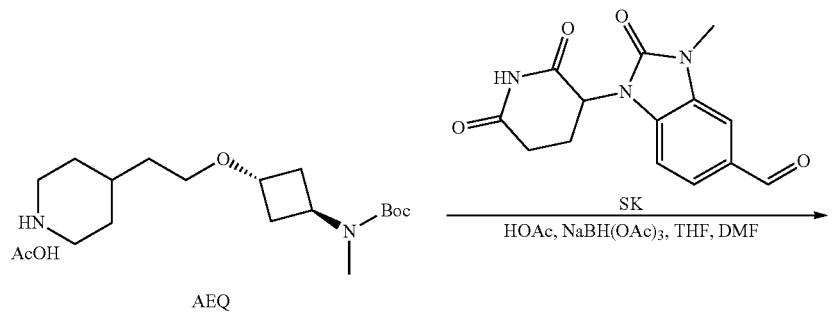

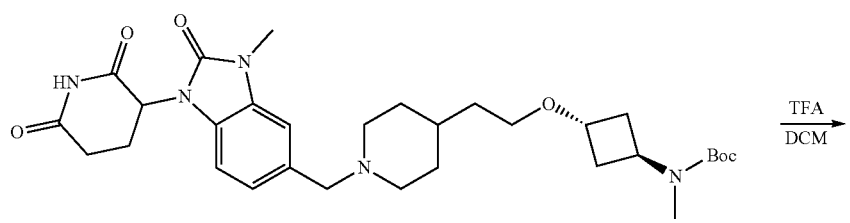

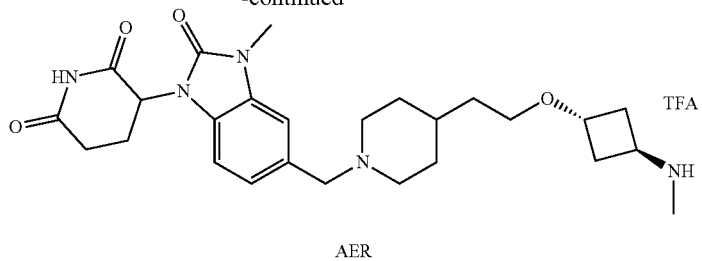

AER

Step 1—Tert-butyl N-[3-[2-[1-[[1-(2,6-dioxo-3-piperidyl)-3-methyl-2-oxo-benzimidazol-5-yl]methyl]-4-piperidyl]ethoxy]cyclobutyl]-N-methyl-carbamate To a solution of tert-butyl N-methyl-N-[3-[2-(4-piperidyl)ethoxy]cyclobutyl]carbamate (500 mg, 1.34 mmol, HOAc, Intermediate AEQ) and 1-(2,6-dioxo-3-piperidyl)-3-methyl-2-oxo-benzimidazole-5-carbaldehyde (385 mg, 1.34 mmol, Intermediate SK) in THF (10 mL) and DMF (10 mL) was added NaBH(OAc)$_3$ (284 mg, 1.34 mmol). The reaction mixture was stirred at 40° C. for 0.5 hour. Additional NaBH(OAc)$_3$ (284 mg, 1.34 mmol) was added and the reaction mixture was stirred at 40° C. for 1 hour. Another batch NaBH(OAc)$_3$ (284 mg, 1.34 mmol) was added and the reaction mixture was stirred at 40° C. for 1 hour. On completion, the reaction was quenched with water (3 mL) and concentrated in vacuo to give the residue. Then the crude product was purified by reverse phase (0.1% FA) to give the title compound (380 mg, 48% yield) as a white solid. LC-MS (ESI$^+$) m/z 584.4 (M+H)$^+$.

Step 2—3-[3-Methyl-5-[[4-[2-[3-(methylamino)cyclobutoxy]ethyl]-1-piperidyl]methyl]-2-oxo-benzimidazol-1-yl]piperidine-2,6-dione To a solution of tert-butyl N-[3-[2-[1-[[1-(2,6-dioxo-3-piperidyl)-3-methyl-2-oxo-benzimidazol-5-yl] methyl]-4-piperidyl]ethoxy]cyclobutyl]-N-methyl-carbamate (150 mg, 256 umol) in DCM (30 mL) was added TFA (27.7 g, 243 mmol, 18.0 mL). The reaction mixture was stirred at 25° C. for 1 hour. On completion, the reaction mixture was concentrated in vacuo to give the title compound (150 mg, 250 umol, 97% yield, TFA) as light yellow oil. LC-MS (ESI$^+$) m/z 484.3 (M+H)$^+$.

9H-fluoren-9-ylmethyl N-[(1R,6R)-6-amino-2,2-difluoro-cyclohexyl]carbamate (Intermediate AES)

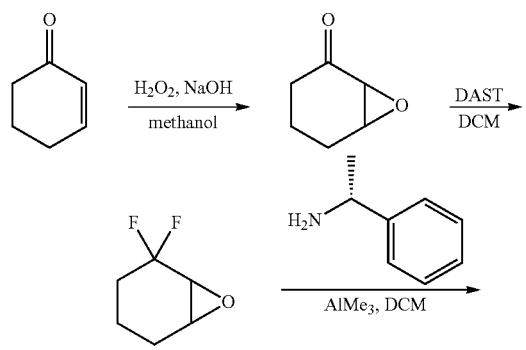

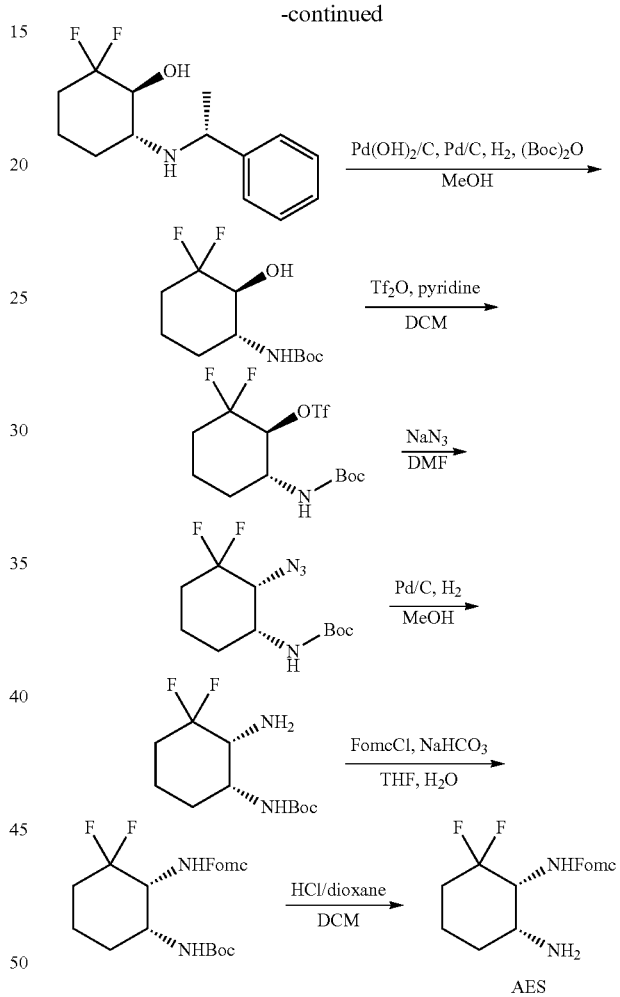

AES

Step 1—7-Oxabicyclo[4.1.0]heptan-5-one

To a solution of cyclohex-2-en-1-one (12.0 g, 124 mmol) in methanol (80 mL) was added H$_2$O$_2$ (73.9 g, 652 mmol 30% solution) at 0° C., then NaOH (6.87 g, 171 mmol) was added. The reaction mixture was stirred at 0° C. for 2 hours. On completion, the reaction was quenched with water (200 ml) and the mixture was extracted with DCM (3×200 mL). The combined organic layers were washed with water until the pH=7.0, dried over Na$_2$SO$_4$, filtered and concentrated in vacuo to give the title compound (12.0 g, crude) as a pale-yellow oil. 3.50 (s, 1H), 3.10 (d, J=2.8 Hz, 1H), 2.47-2.35 (m, 1H), 2.26-2.09 (m, 1H), 2.03-1.94 (m, 1H), 1.84-1.76 (m, 2H), 1.67-1.52 (m, 1H).

Step 2—(1R,6R)-5,5-Difluoro-7-oxabicyclo[4.1.0]heptane

To a solution of 7-oxabicyclo[4.1.0]heptan-5-one (14.6 g, 130 mmol) in DCM (60 mL) was added DAST (41.9 g, 260 mmol) at 0° C. The reaction mixture was stirred at 10° C. for 16 hours. On completion, the reaction mixture was quenched with water (6 mL) slowly at 0-10° C. The mixture was dried over $Na_2SO_4$, filtered through a pad of silica gel and the cake was washed with DCM (100 mL) to give a solution of the title compound (17.4 g, 100% yield) in DCM (150 mL) and used for next step directly.

Step 3—(1S,6R)-2,2-Difluoro-6-[[(1R)-1-phenylethyl]amino]cyclohexanol

To a solution of (1R)-1-phenylethanamine (17.9 g, 148 mmol) in DCM (80 mL) was added $Al(CH_3)_3$ (2.0 M, 68.3 mL) at 0-10° C. The mixture was stirred at 0-5° C. for 1 hour. Then, to the mixture was added a solution of (1R,6R)-5,5-difluoro-7-oxabicyclo[4.1.0]heptane (17.4 g, 130 mmol) in DCM (150 mL) at 0-10° C. The mixture was stirred at 0-5° C. for 3 hours. Then, the mixture was stirred at 15° C. for 16 hours. On completion, the reaction was quenched with saturated aq. $NH_4Cl$ (50 mL) slowly at 0-20° C. The mixture was filtered, and the cake was washed with DCM (100 mL). The mixture was partitioned and the organic layer was concentrated in vacuo. The residue was purified by column flash chromatography on silica gel (PE:EA=5:1 to 2:1) to give the title compound (8.60 g, 25% yield) as light yellow solid. $^1H$ NMR (400 MHz, $CDCl_3$) δ 3.46-3.33 (m, 1H), 2.93-2.83 (m, 1H), 2.22-2.07 (m, 1H), 1.93 (d, J=12.4 Hz, 1H), 1.80-1.64 (m, 2H), 1.63-1.48 (m, 1H), 1.34-1.20 (m, 1H).

Step 4—Tert-butyl N-[(1R,2S)-3,3-difluoro-2-hydroxy-cyclohexyl]carbamate

A mixture of (1S,6R)-2,2-difluoro-6-[[(1R)-1-phenylethyl]amino]cyclohexanol (1.50 g, 5.88 mmol), $Boc_2O$ (1.41 g, 6.46 mmol), $Pd(OH)_2/C$ (300 mg, 5.88 mmol, 10% wt) and Pd/C (300 mg, 10% wt) in methanol (30 mL) was stirred at 50° C. under hydrogen (50 psi) for 16 hours. On completion, the mixture was filtered and the cake was washed with methanol (20 mL). The filtrate and washing were combined and concentrated in vacuo. The residue was purified by column chromatography on silica gel (PE:EA=20:1 to 5:1) to give the title compound (1.00 g, 67% yield) as white solid. $^1H$ NMR (400 MHz, $CDCl_3$) δ 4.72-4.58 (m, 1H), 3.76-3.63 (m, 1H), 3.61-3.47 (m, 1H), 3.11 (m, 1H), 2.24-2.12 (m, 1H), 2.08-1.99 (m, 1H), 1.80-1.59 (m, 3H), 1.46 (s, 9H), 1.40-1.30 (m, 1H).

Step 5—[(1S,6R)-6-(Tert-butoxycarbonylamino)-2,2-difluoro-cyclohexyl]trifluoromethanesulfonate To a solution of tert-butyl N-[(1R,2S)-3,3-difluoro-2-hydroxy-cyclohexyl]carbamate (1.30 g, 5.17 mmol) and pyridine (1.23 g, 15.5 mmol) in DCM (20 mL) was added $Tf_2O$ (2.92 g, 10.3 mmol) at 0° C. The reaction mixture was stirred at 0° C. for 2 hours. On completion, the reaction was quenched with water (2 mL), the mixture was partitioned and the organic layer was concentrated in vacuo. The residue was purified by column chromatography on silica gel (PE:EA=50:1 to 10:1) to give the title compound (1.90 g, 95% yield) as white solid. $^1H$ NMR (400 MHz, $CDCl_3$) δ 4.90-4.55 (m, 2H), 4.05-3.80 (m, 1H), 2.35-2.18 (m, 1H), 2.17-2.03 (m, 1H), 1.91-1.72 (m, 2H), 1.70-1.56 (m, 2H), 1.45 (s, 9H).

Step 6—Tert-butyl N-[(1R,2R)-2-azido-3,3-difluoro-cyclohexyl]carbamate

A mixture of [(1S,6R)-6-(tert-butoxycarbonylamino)-2,2-difluoro-cyclohexyl]trifluoromethane sulfonate (2.00 g, 5.22 mmol) and $NaN_3$ (1.70 g, 26.1 mmol) in DMF (30 mL) was stirred at 100° C. for 16 hours. On completion, the mixture was diluted with water (150 mL), and extracted with a mixed solution (petroleum ether:ethyl acetate=3:1) (3×50 mL). The combined organic layer was washed with brine (50 mL), dried over $Na_2SO_4$, filtered and concentrated in vacuo. The residue was purified by column chromatography on silica gel (PE:EA=80:1) to give the title compound (900 mg, 62% yield) as white solid. $^1H$ NMR (400 MHz, $CDCl_3$) δ 4.86-4.66 (m, 1H), 4.05-3.95 (m, 1H), 3.94-3.86 (m 1H), 2.01-1.83 (m, 2H), 1.78-1.62 (m, 2H), 1.54-1.49 (m, 1H), 1.47 (s, 9H), 1.43-1.30 (m, 1H).

Step 7—Tert-butyl N-[(1R,2R)-2-amino-3,3-difluoro-cyclohexyl]carbamate

To a solution of tert-butyl N-[(1R,2R)-2-azido-3,3-difluoro-cyclohexyl]carbamate (800 mg, 2.90 mmol) in MeOH (10 mL) was added Pd/C (30.0 mg, 2.90 mmol, 10% wt). The reaction mixture was stirred at 15° C. for 1 hour under $H_2$ (15 psi). On completion, the reaction mixture was filtered and the filtrate was concentrated in vacuo to give the title compound (700 mg, 96% yield) as white solid. $^1H$ NMR (400 MHz, DMSO-$d_6$) δ 6.66 (d, J=8.0 Hz, 1H), 3.67-3.48 (m, 1H), 3.13-3.02 (m, 1H), 2.18-1.91 (m, 1H), 1.75-1.66 (m, 1H), 1.65-1.58 (m, 2H), 1.57-1.45 (m, 1H), 1.41-1.36 (m, 11H), 1.34-1.27 (m, 1H).

Step 8—9H-fluoren-9-ylmethyl N-[(1R,6R)-6-(tert-butoxycarbonylamino)-2,2-difluoro-cyclohexyl] carbamate To a solution of tert-butyl N-[(1R,2R)-2-amino-3,3-difluoro-cyclohexyl]carbamate (700 mg, 2.80 mmol) and $NaHCO_3$ (469 mg, 5.59 mmol) in a mixed solvents of water (10 mL) and THF (10 mL) was added 9H-fluoren-9-ylmethyl carbonochloridate (868 mg, 3.36 mmol). The reaction mixture was stirred at 15° C. for 16 hours. On completion, the reaction mixture was diluted with water (10 mL) and extracted with DCM (3×20 mL). The organic layer was washed with brine (2×15 mL), dried over $Na_2SO_4$, filtered and concentrated in vacuo. The residue was purified by silica gel chromatography (petroleum ether:ethyl acetate=10:1) to give the title compound (1.25 g, 94% yield) as white solid. $^1H$ NMR (400 MHz, $CDCl_3$) δ 7.78 (d, J=7.6 Hz, 2H), 7.61 (d, J=7.6 Hz, 2H), 7.48-7.39 (m, 2H), 7.37-7.29 (m, 2H), 5.20 (d, J=8.8 Hz, 1H), 4.89 (d, J=8.8 Hz, 1H), 4.53-4.36 (m, 2H), 4.32-4.21 (m, 2H), 4.20-4.06 (m, 1H), 2.18 (d, J=10.4 Hz, 1H), 1.89-1.74 (m, 2H), 1.74-1.62 (m, 2H), 1.48 (s, 9H).

Step 9—9H-fluoren-9-ylmethyl N-[(1R,6R)-6-amino-2,2-difluoro-cyclohexyl]carbamate To a solution of 9H-fluoren-9-ylmethyl N-[(1R,6R)-6-(tert-butoxycarbonylamino)-2,2-difluoro-cyclohexyl]carbamate (1.25 g, 2.65 mmol) in DCM (10 mL) was added HCl/dioxane (4 M, 10 mL). The reaction mixture was stirred at 10° C. for 1 hour. On completion, the reaction mixture was concentrated in vacuo to give the title compound (1.05 g, 97% yield, HCl salt) as yellow solid. LC-MS (ESI$^+$) m/z 373.2 (M+H)$^+$.

5-[[(1R,2R)-2-(Tert-butoxycarbonylamino)-3,3-difluoro-cyclohexyl]amino]pyrazolo[1,5-a] pyrimidine-3-carboxylic acid (Intermediate AET)

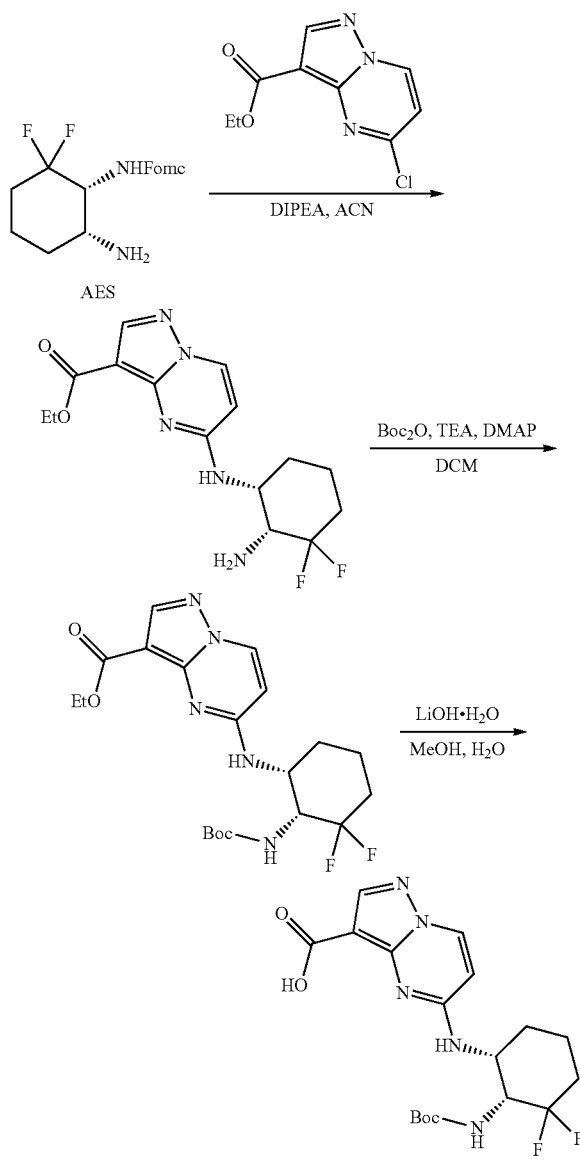

Step 1—Ethyl 5-[[(1R,2R)-2-amino-3,3-difluoro-cyclohexyl]amino]pyrazolo[1,5-a]pyrimidine-3-carboxylate To a solution of 9H-fluoren-9-ylmethyl N-[(1R,6R)-6-amino-2,2-difluoro-cyclohexyl]carbamate (1.05 g, 2.82 mmol, HCl salt, Intermediate AES) and ethyl 5-chloropyrazolo[1,5-a]pyrimidine-3-carboxylate (763 mg, 3.38 mmol) in ACN (15 mL) was added DIPEA (1.09 g, 8.46 mmol). The reaction mixture was stirred at 80° C. for 8 hours. On completion, the reaction mixture was concentrated in vacuo. The residue was purified by reverse phase (0.1% FA) to give the title compound (750 mg, 78% yield) as yellow solid. $^1$H NMR (400 MHz, DMSO-d$_6$) δ 8.53 (d, J=7.6 Hz, 1H), 8.15 (s, 1H), 7.70 (d, J=7.2 Hz, 1H), 6.52 (d, J=7.6 Hz, 1H), 4.36-4.26 (m, 1H), 4.23-4.12 (m, 2H), 3.43-3.40 (m, 1H), 2.26-2.04 (m, 1H), 1.85-1.58 (m, 4H), 1.51-1.37 (m, 1H), 1.28 (t, J=7.2 Hz, 3H).

Step 2—Ethyl 5-[[(1R,2R)-2-(tert-butoxycarbonylamino)-3,3-difluoro-cyclohexyl]amino]pyrazolo[1,5-a]pyrimidine-3-carboxylate To a solution of ethyl 5-[[(1R,2R)-2-amino-3,3-difluoro-cyclohexyl]amino]pyrazolo[1,5-a]pyrimidine-3-carboxylate (50.0 mg, 147 umol), DMAP (1.80 mg, 14.7 umol) and TEA (29.8 mg, 294 umol) in DCM (2 mL) was added Boc$_2$O (38.5 mg, 176 umol). The reaction mixture was stirred at 20-35° C. for 20 hours. On completion, the reaction mixture was quenched by water (0.5 mL) and concentrated in vacuo. The residue was purified by silica gel chromatography (petroleum ether:ethyl acetate=1:1) to give the title compound (50.0 mg, 74% yield) as yellow solid. LC-MS (ESI$^+$) m/z 440.2 (M+H)$^+$.

Step 3—5-[[(1R,2R)-2-(Tert-butoxycarbonylamino)-3,3-difluoro-cyclohexyl]amino]pyrazolo[1,5-a]pyrimidine-3-carboxylic acid To a solution of ethyl 5-[[(1R,2R)-2-(tert-butoxycarbonylamino)-3,3-difluoro-cyclohexyl]amino] pyrazolo[1,5-a]pyrimidine-3-carboxylate (30.0 mg, 68.2 umol) in a mixed solvents of methanol (0.8 mL) and water (0.2 mL) was added LiOH·H$_2$O (8.59 mg, 204 umol). The reaction mixture was stirred at 60° C. for 16 hours. On completion, the reaction mixture was acidified to pH=5-6 with 1.0 M aq.HCl and concentrated in vacuo to give the title compound (28.0 mg, crude) as white solid. LC-MS (ESI$^+$) m/z 412.2 (M+H)$^+$.

Benzyl N-[3-[3-(methylamino)propoxy]propyl]carbamate (Intermediate AEU)

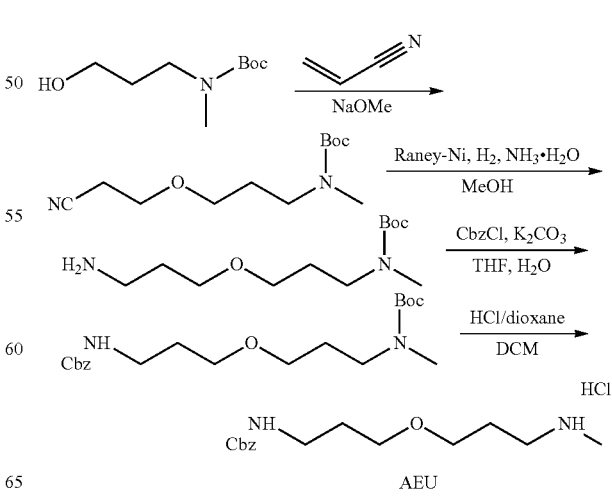

Step 1—Tert-butyl N-[3-(2-cyanoethoxy)propyl]-N-methyl-carbamate

To a mixture of NaOMe (5.71 mg, 106 umol) and tert-butyl N-(3-hydroxypropyl)-N-methyl-carbamate (2.00 g, 10.6 mmol, CAS #98642-44-5) in THF (20 mL) was added prop-2-enenitrile (1.12 g, 21.1 mmol). The reaction mixture was stirred at 20° C. for 12 hours. On completion, the mixture was concentrated in vacuo. The residue was diluted with water (40 mL), and extracted with EA (3×30 mL). The combined organic layers were washed with brine (50 mL), dried over $Na_2SO_4$, filtered and concentrated in vacuo to give the title compound (2.00 g, 78% yield) as light yellow oil. $^1$H NMR (400 MHz, $CDCl_3$) δ 3.65 (t, J=6.4 Hz, 2H), 3.52 (t, J=6.4 Hz, 2H), 3.31 (t, J=6.8 Hz, 2H), 2.87 (s, 3H), 2.61 (t, J=6.4 Hz, 2H), 1.87-1.79 (m, 2H), 1.47 (s, 9H).

Step 2—Tert-butyl N-[3-(3-aminopropoxy)propyl]-N-methyl-carbamate

To a mixture of tert-butyl N-[3-(2-cyanoethoxy)propyl]-N-methyl-carbamate (2.00 g, 8.25 mmol) in MeOH (60 mL) was added Raney-Ni (1.00 g, 11.6 mmol) and $NH_3$—$H_2O$ (6.00 mL, 25% solution). The reaction mixture was stirred at 30° C. for 12 hours under $H_2$ (50 psi). On completion, the mixture was filtered with celite and concentrated in vacuo to give the title compound (1.80 g, 88% yield) as yellow oil. $^1$H NMR (400 MHz, $CDCl_3$) δ 3.51 (t, J=6.4 Hz, 2H), 3.44 (t, J=6.4 Hz, 2H), 3.30 (s, 2H), 2.87 (s, 3H), 2.82 (t, J=6.8 Hz, 2H), 1.84-1.77 (m, 2H), 1.73 (t, J=6.4 Hz, 2H), 1.48 (s, 9H), 1.21-1.01 (m, 2H).

Step 3—Tert-butyl N-[3-[3-(benzyloxycarbonylamino)propoxy]propyl]-N-methyl-carbamate To a solution of tert-butyl N-[3-(3-aminopropoxy)propyl]-N-methyl-carbamate (1.00 g, 4.06 mmol) in THF (20 mL) and $H_2O$ (20 mL) was added $K_2CO_3$ (1.12 g, 8.12 mmol). Then CbzCl (762 mg, 4.47 mmol) was added at 0° C. The mixture was stirred at 0-15° C. for 2 hours. On completion, the mixture was diluted water (50 ml), then extracted with EA (3×50 mL). The combined organic layers were washed with brine (50 mL), dried over $Na_2SO_4$, filtered and concentrated in vacuo to give the title compound (1.50 g, 97% yield) as yellow oil. $^1$H NMR (400 MHz, $CDCl_3$) δ 7.40-7.31 (m, 5H), 5.10 (s, 2H), 3.52-3.24 (m, 8H), 2.82 (s, 3H), 1.89-1.68 (m, 4H), 1.51-1.39 (m, 9H).

Step 4—Benzyl N-[3-[3-(methylamino)propoxy]propyl]carbamate

To a solution of tert-butyl N-[3-[3-(benzyloxycarbonylamino)propoxy]propyl]-N-methyl-carbamate (30.0 mg, 78.8 umol) in DCM (2 mL) was added HCl/dioxane (4 M, 3.00 mL). The mixture was stirred at 15° C. for 2 hours. On completion, the mixture was concentrated in vacuo to give the title compound (25.0 mg, 100% yield, HCl salt) as a white solid. LC-MS (ESI$^+$) m/z 281.1 (M+H)$^+$.

N-[1-[4-[[3-(3-aminopropoxy)propyl-methyl-amino]methyl] cyclohexyl]-3-(difluoromethyl) pyrazol-4-yl]-2-[2-(cyclopropylmethylamino)-4-pyridyl]oxazole-4-carboxamide (Intermediate AEV)

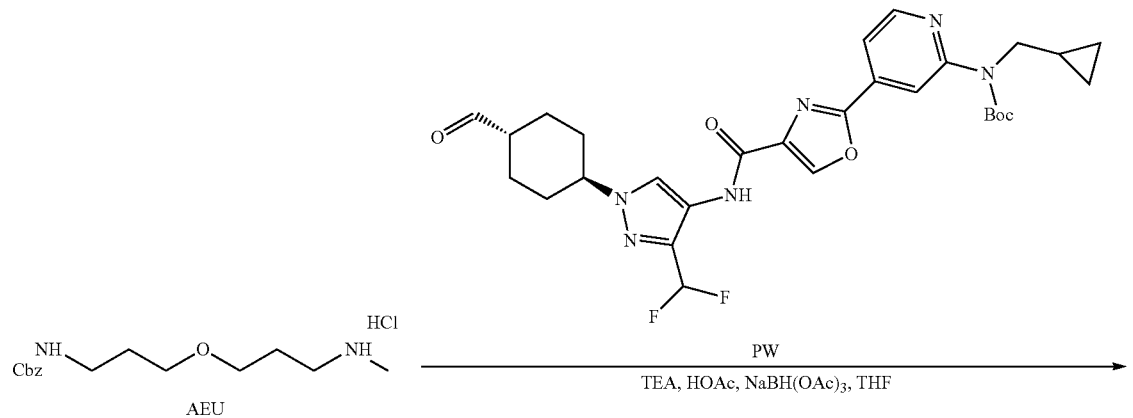

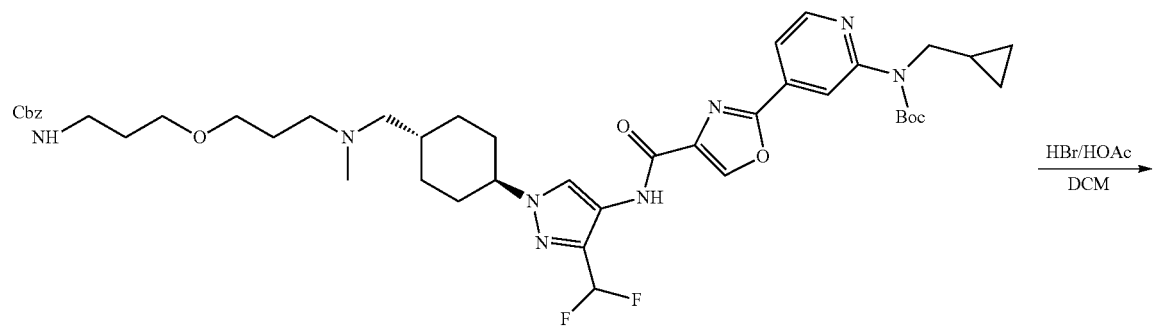

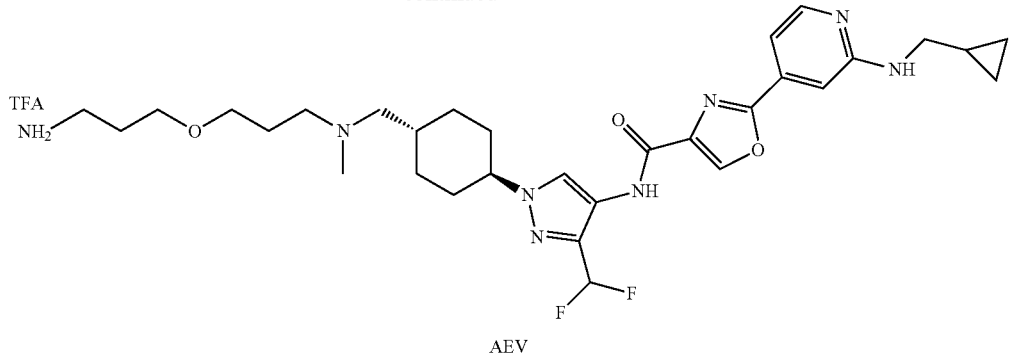

AEV

Step 1—Tert-butyl N-[4-[4-[[1-[4-[[3-[3-(benzyloxycarbonylamino)propoxy]propyl-methyl-amino]methyl] cyclohexyl]-3-(difluoromethyl)pyrazol-4-yl]carbamoyl]oxazol-2-yl]-2-pyridyl]-N-(cyclopropylmethyl)carbamate To a solution of benzyl N-[3-[3-(methylamino)propoxy]propyl]carbamate (25.0 mg, 78.9 umol, HCl salt, Intermediate AEU) in THF (3 mL) was added TEA (7.98 mg, 78.9 umol). The mixture was stirred at 15° C. for 15 minutes. Then HOAc (9.48 mg, 157 umol) and tert-butyl N-(cyclopropylmethyl)-N-[4-[4-[[3-(difluoromethyl)-1-(4-formylcyclohexyl)pyrazol-4-yl]carbamoyl]oxazol-2-yl]-2-pyridyl] carbamate (46.1 mg, 78.9 umol, Intermediate PW) were added to the mixture, and the mixture was stirred for 15 minutes. Next, NaBH(OAc)$_3$ (25.1 mg, 118 umol) was added at 0° C. and the mixture was stirred at 0° C. for 2 hours. On completion, the reaction was quenched with water (0.2 mL) and the mixture was concentrated in vacuo. The residue was purified by reversed-phase HPLC (FA condition) to give the title compound (110 mg, 20% yield) as white solid. $^1$H NMR (400 MHz, DMSO-d$_6$) δ 9.83 (s, 1H), 9.07-8.97 (m, 1H), 8.60 (d, J=5.4 Hz, 1H), 8.31 (s, 1H), 8.20 (s, 1H), 7.69 (d, J=5.2 Hz, 1H), 7.41-7.25 (m, 5H), 7.22-7.02 (m, 1H), 5.01 (s, 2H), 3.87 (d, J=7.2 Hz, 2H), 3.39-3.38 (m, 6H), 3.23-3.15 (m, 1H), 3.12-3.03 (m, 3H), 2.97 (t, J=6.0 Hz, 1H), 2.80 (d, J=4.8 Hz, 3H), 2.13-2.04 (m, 2H), 1.98-1.77 (m, 7H), 1.70-1.60 (m, 2H), 1.52 (s, 9H), 1.27-1.12 (m, 4H), 0.47-0.36 (m, 2H), 0.25-0.23 (m, 2H); LC-MS (ESI$^+$) m/z 849.5 (M+H)$^+$.

Step 2—N-[1-[4-[[3-(3-aminopropoxy)propyl-methyl-amino]methyl] cyclohexyl]-3-(difluoromethyl) pyrazol-4-yl]-2-[2-(cyclopropylmethylamino)-4-pyridyl]oxazole-4-carboxamide To a solution of tert-butyl N-[4-[4-[[1-[4-[[3-[3-(benzyloxycarbonylamino)propoxy]propyl-methyl-amino]methyl] cyclohexyl]-3-(difluoromethyl)pyrazol-4-yl]carbamoyl] oxazol-2-yl]-2-pyridyl]-N-(cyclopropylmethyl)carbamate (100 mg, 118 umol) in DCM (2 mL) was added HBr/AcOH (1 mL). The mixture was stirred at 15° C. for 2 hours. On completion, the mixture was concentrated in vacuo. The residue was purified by reversed-phase HPLC (column: Phenomenex luna C18 250*50 mm*10 um; mobile phase: [water (0.075% TFA)-ACN]; B %: 5%-35%, 9 min) to give the title compound (68.0 mg, 68% yield, 2TFA salt) as a yellow solid. LC-MS (ESI$^+$) m/z 615.3 (M+H)$^+$.

N-[1-[4-[3-(3-aminopropoxy)propyl-methyl-carbamoyl]cyclohexyl]-3-(difluoromethyl) pyrazol-4-yl]-2-[2-(cyclopropylmethylamino)-4-pyridyl]oxazole-4-carboxamide (Intermediate AEW)

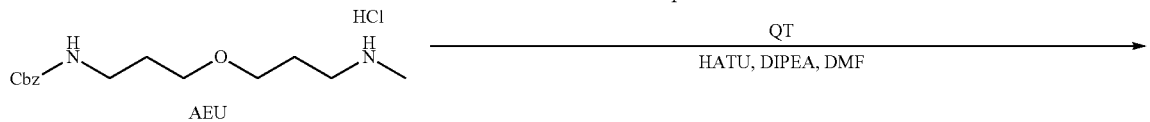

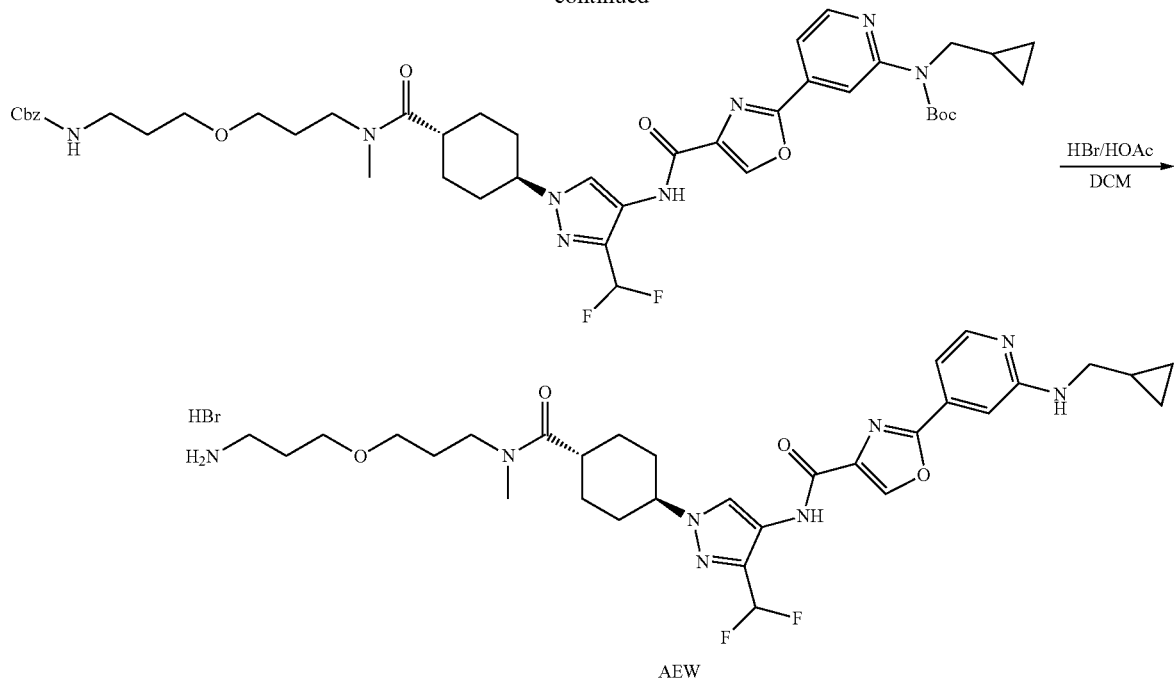

AEW

Step 1—Tert-butyl N-[4-[4-[[1-[4-[3-[3-(benzyloxy-carbonylamino)propoxy]propyl-methyl-carbamoyl]cyclohexyl]-3-(difluoromethyl)pyrazol-4-yl]carbamoyl]oxazol-2-yl]-2-pyridyl]l-N-(cyclopropylmethyl)carbamate To a solution of benzyl N-[3-[3-(methylamino)propoxy]propyl]carbamate (35.0 mg, 11.0 umol, HCl salt, Intermediate AEU) in DMF (2 mL) was added 4-[4-[[2-[2-[tert-butoxycarbonyl(cyclopropylmethyl)amino]-4-pyridyl]oxazole-4-carbonyl]amino]-3-(difluoromethyl)pyrazol-1-yl]cyclohexanecarboxylic acid (66.3 mg, 110 umol, Intermediate QT), HATU (63.0 mg, 165 umol) and DIPEA (331 umol, 57.7 uL). The mixture was stirred at 25° C. for 2 hours. On completion, the reaction mixture was quenched with H₂O (0.5 mL). The mixture was concentrated in vacuo. The residue was purified by reverse phase (0.1% FA condition) to give the title compound (70.0 mg, 73% yield) as a white solid. ¹H NMR (400 MHz, DMSO-d₆) δ 9.77 (d, J=8.8 Hz, 1H), 9.04-8.96 (m, 1H), 8.59 (d, J=4.8 Hz, 1H), 8.29 (s, 1H), 8.19 (s, 1H), 7.71-7.66 (m, 1H), 7.37-7.16 (m, 6H), 4.99 (d, J=9.6 Hz, 2H), 3.86 (d, J=6.8 Hz, 2H), 3.35-3.34 (m, 3H), 3.11-3.04 (m, 2H), 3.02 (s, 2H), 2.78 (s, 2H), 2.09-2.00 (m, 2H), 1.92-1.73 (m, 6H), 1.69-1.59 (m, 4H), 1.51 (s, 9H), 1.40-1.35 (m, 4H), 1.22-1.10 (m, 2H), 0.43-0.38 (m, 2H), 0.26-0.21 (m, 2H); LC-MS (ESI⁺) m/z 863.5 (M+H)⁺.

Step 2—N-[1-[4-[3-(3-aminopropoxy)propyl-methyl-carbamoyl]cyclohexyl]-3-(difluoromethyl)pyrazol-4-yl]-2-[2-(cyclopropylmethylamino)-4-pyridyl]oxazole-4-carboxamide To a solution of tert-butyl N-[4-[4-[[1-[4-[3-[3-(benzyloxycarbonylamino)propoxy]propyl-methyl-carbamoyl]cyclohexyl]-3-(difluoromethyl)pyrazol-4-yl]carbamoyl]oxazol-2-yl]-2-pyridyl]-N-(cyclopropylmethyl)carbamate (60.0 mg, 69.5 umol) in DCM (3 mL) was added HBr/HOAc (1 mL) at 25° C. The reaction mixture was stirred at 25° C. for 2 hours. On completion, the reaction mixture was concentrated in vacuo to give the title compound (25 mg, 57% yield) as a yellow solid. ¹H NMR (400 MHz, DMSO-d₆) δ 9.75 (s, 1H), 8.99 (s, 1H), 8.19 (s, 1H), 8.12 (d, J=6.0 Hz, 1H), 7.65 (s, 1H), 7.31-7.02 (m, 2H), 4.34-4.23 (m, 1H), 3.41 (s, 3H), 3.40-3.38 (m, 3H), 3.36-3.29 (m, 4H), 3.22 (d, J=6.8 Hz, 2H), 3.03 (s, 2H), 2.92-2.83 (m, 2H), 2.80 (s, 1H), 2.06 (d, J=10.0 Hz, 2H), 1.94-1.82 (m, 3H), 1.81-1.74 (m, 4H), 1.71-1.65 (m, 1H), 1.63-1.48 (m, 2H), 1.15-1.03 (m, 1H), 0.54-0.46 (m, 2H), 0.29-0.24 (m, 2H); LC-MS (ESI⁺) m/z 629.3 (M+H)⁺.

Tert-butyl N-methyl-N-[3-[3-(methylamino)propoxy]propyl]carbamate (Intermediate AEX)

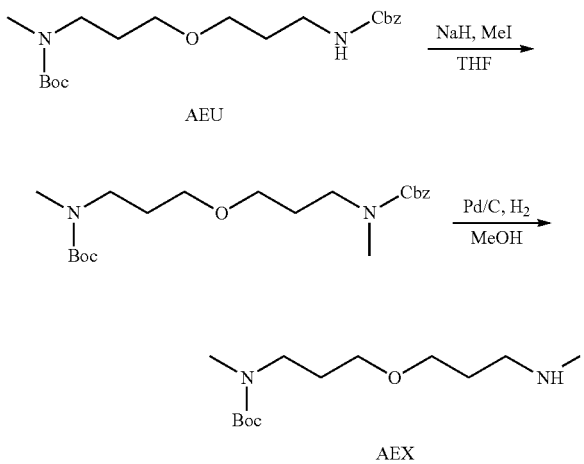

Step 1—Tert-butyl N-3-[3-benzyloxycarbonyl (methyl)amino]propoxy]propyl]-N-methyl-carbamate To a solution of tert-butyl N-[3-[3-(benzyloxycarbonylamino)propoxy]propyl]-N-methyl-carbamate (500 mg, 1.31 mmol, Intermediate AEU) in THF (50 mL) was added NaH (105 mg, 2.63 mmol, 60% dispersion in mineral oil). The mixture was stirred at 0° C. for 0.5 hour, then CH$_3$I (280 mg, 1.97 mmol) was added. The mixture was stirred at 0° C. for 6 hours. On completion, the reaction mixture was quenched with sat. aq. NH$_4$Cl (20 mL) at 0° C. Then the mixture was diluted with water (50 mL), and extracted with EA (3×50 mL). The combined organic layers were washed with brine (100 mL), dried over Na$_2$SO$_4$, filtered and concentrated in vacuo to give the title compound (500 mg, 96% yield) as yellow oil. $^1$H NMR (400 MHz, CDCl$_3$) δ 7.38 (d, J=4.4 Hz, 5H), 5.15 (s, 2H), 3.49-3.35 (m, 6H), 3.33-3.23 (m, 2H), 2.96 (s, 3H), 2.86 (s, 3H), 1.89-1.74 (m, 5H), 1.47 (s, 9H).

Step 2—Tert-butyl N-methyl-N-[3-[3-(methylamino)propoxy]propyl]carbamate

To a solution of tert-butyl N-[3-[3-[benzyloxycarbonyl (methyl)amino]propoxy]propyl]-N-methyl-carbamate (200 mg, 507 umol) in MeOH (10 mL) was added Pd/C (0.1 g, 50% wt). The mixture was stirred at 15° C. for 2 hours under H$_2$ (15 PSI). On completion, the mixture was filtered with celite and concentrated to give the title compound (130 mg, 98% yield) as colorless oil.

2-[2-(Cyclopropylmethylamino)-4-pyridyl]-N-[3-(difluoromethyl)-1-[4-[[methyl-[3-[3-(methylamino)propoxy]propyl]amino]methyl]cyclohexyl]pyrazol-4-yl]oxazole-4-carboxamide (Intermediate AEY)

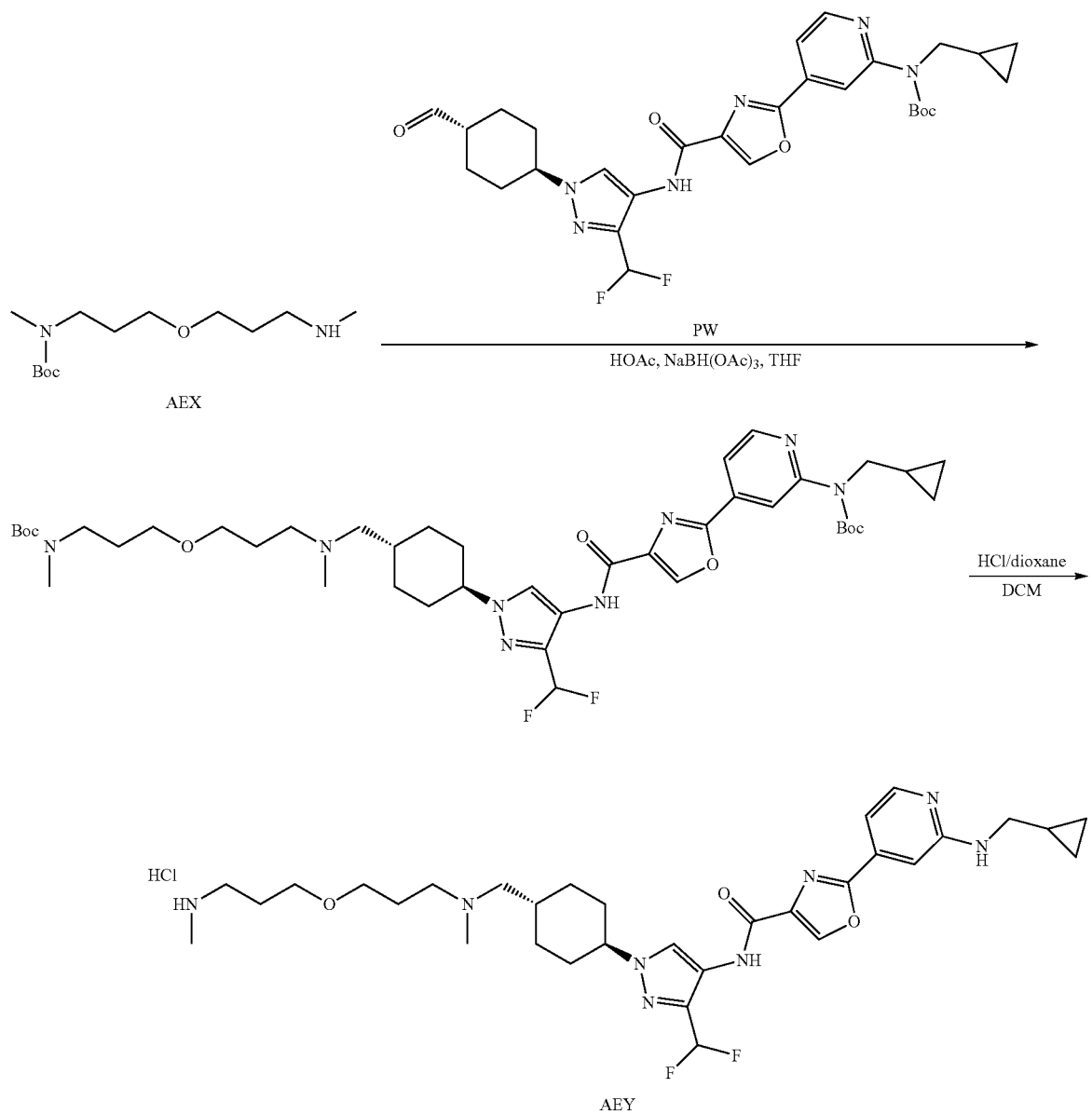

Step 1—Tert-butyl N-[3-[3-[[4-[4-[[2-[2-[tert-butoxycarbonyl(cyclopropylmethyl)amino]-4-pyridyl] oxazole-4-carbonyl]amino]-3-(difluoromethyl)pyrazol-1-yl] cyclohexyl]methyl-methyl-amino]propoxy]propyl]-N-methyl-carbamate To a solution of tert-butyl N-methyl-N-[3-[3-(methylamino)propoxy]propyl]carbamate (50.0 mg, 192 umol, Intermediate AEX) in THF (30 mL) was added AcOH (11.5 mg, 192 umol) and tert-butyl N-(cyclopropylmethyl)-N-[4-[4-[[3-(difluoromethyl)-1-(4-formylcyclohexyl)pyrazol-4-yl] carbamoyl]oxazol-2-yl]-2-pyridyl]carbamate (112 mg, 192 umol, Intermediate PW). Then NaBH(OAc)₃ (61.0 mg, 288 umol) was added at 0° C. and the mixture was stirred at 0-15° C. for 2 hours. On completion, the mixture was concentrated in vacuo. The residue was purified by prep-HPLC (column: Phenomenex luna C18 250*50 mm*10 um; mobile phase: [water (0.075% TFA)-ACN]; B %: 50%-80%, 9 min) to give the title compound (140 mg, 77% yield, TFA) as white solid. LC-MS (ESI⁺) m/z 829.5 (M+H)⁺.

Step 2—2-[2-(Cyclopropylmethylamino)-4-pyridyl]-N-[3-(difluoromethyl)-1-[4-[[methyl-[3-[3-(methylamino)propoxy]propyl] amino]methyl] cyclohexyl] pyrazol-4-yl] oxazole-4-carboxamide To a solution of tert-butyl N-[3-[3-[[4-[4-[[2-[2-[tert-butoxycarbonyl(cyclopropylmethyl)amino]-4-pyridyl] oxazole-4-carbonyl]amino]-3-(difluoromethyl)pyrazol-1-yl] cyclohexyl]methyl-methyl-amino]propoxy]propyl]-N-methyl-carbamate (130 mg, 156 umol) in DCM (5 mL) was added HCl/dioxane (4 M, 4 mL). The mixture was stirred at 25° C. for 2 hours. On completion, the reaction mixture was concentrated in vacuo to give the title compound (110 mg, crude, HCl salt) as a white solid. ¹H NMR (400 MHz, DMSO-d₆) δ 9.92 (s, 1H), 9.12 (s, 1H), 8.19 (s, 1H), 8.08 (d, J=6.4 Hz, 1H), 7.62 (s, 1H), 7.36-7.00 (m, 2H), 4.30-4.20 (m, 1H), 3.60-3.56 (m, 3H), 3.50-3.44 (m, 4H), 3.34 (d, J=6.8 Hz, 2H), 3.22-3.12 (m, 1H), 3.11-2.99 (m, 2H), 2.97-2.86 (m, 3H), 2.76 (d, J=4.8 Hz, 2H), 2.54 (s, 1H), 2.52 (s, 3H), 2.14-2.02 (m, 3H), 2.02-1.80 (m, 7H), 1.26-1.11 (m, 3H), 0.60-0.50 (m, 2H), 0.35-0.26 (m, 2H); LC-MS (ESI⁺) m/z 629.2 (M+H)⁺.

4-Bromo-1-[[(2S,3S,4S)-3-ethyl-4-fluoro-5-oxo-pyrrolidin-2-yl]methoxy]-7-methoxy-isoquinoline-6-carboxamide (Intermediate AEZ)

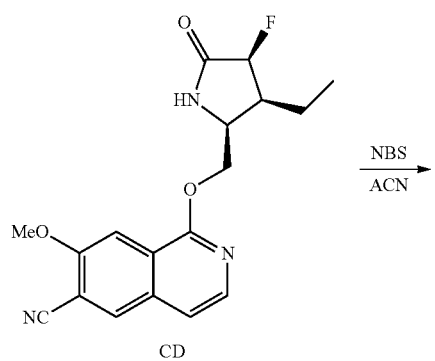

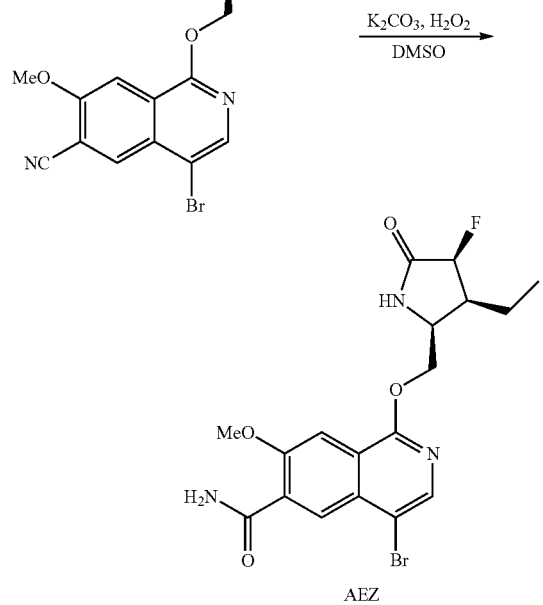

Step 1—4-Bromo-1-[[(2S,3S,4S)-3-ethyl-4-fluoro-5-oxo-pyrrolidin-2-yl]methoxy]-7-methoxy-iso quinoline-6-carbonitrile To a solution of 1-[[(2S,3S,4S)-3-ethyl-4-fluoro-5-oxo-pyrrolidin-2-yl]methoxy]-7-methoxy-iso quinoline-6-carbonitrile (200 mg, 582 umol, Intermediate CD) in ACN (7.00 mL) was added NBS (228 mg, 1.28 mmol), and the mixture was stirred at 60° C. for 2 hours. On completion, the mixture was concentrated in vacuo. The mixture was purified by prep-TLC (EA) to give the title compound (130 mg, 52% yield) as yellow solid. ¹H NMR (400 MHz, CDCl₃) δ 8.31 (s, 1H), 8.06 (s, 1H), 7.68 (s, 1H), 7.57 (s, 1H), 4.99-4.79 (m, 1H), 4.71 (d, J=11.6 Hz, 1H), 4.41-4.32 (m, 1H), 4.21-4.14 (m, 1H), 4.07 (s, 3H), 2.70-2.47 (m, 1H), 1.86-1.66 (m, 2H), 1.13 (t, J=7.2 Hz, 3H).

Step 2—4-Bromo-1-[[(2S,3S,4S)-3-ethyl-4-fluoro-5-oxo-pyrrolidin-2-yl]methoxy]-7-methoxy-isoquinoline-6-carboxamide To a solution of 4-bromo-1-[[(2S,3S,4S)-3-ethyl-4-fluoro-5-oxo-pyrrolidin-2-yl]methoxy]-7-methoxy-isoquinoline-6-carbonitrile (300 mg, 710 umol) in DMSO (3.00 mL) was added K₂CO₃ (39.2 mg, 284 umol) and H₂O₂ (241 mg, 2.13 mmol, 30% solution). The mixture was stirred at 25° C. for 16 hrs. On completion, the mixture was diluted with H₂O (30 mL), and extracted with EA (3×30 mL). The organic layers were dried over anhydrous Na₂SO₄, filtered and concentrated in vacuo to give the title compound (300 mg, 80% yield) as white solid. ¹H NMR (400 MHz, DMSO-d₆) δ 8.88 (s, 1H), 8.24 (s, 1H), 8.16 (s, 1H), 7.95 (s, 1H), 7.85 (s, 1H), 7.80 (s, 1H), 5.00-4.82 (m, 1H), 4.56-4.50 (m, 1H), 4.30-4.23 (m, 1H), 4.10 (s, 1H), 4.00 (s, 3H), 1.64-1.53 (m, 2H), 1.02 (t, J=7.2 Hz, 3H).

1H-pyrazolo[3,4-b]pyridine-5-carbonitrile (Intermediate AFA)

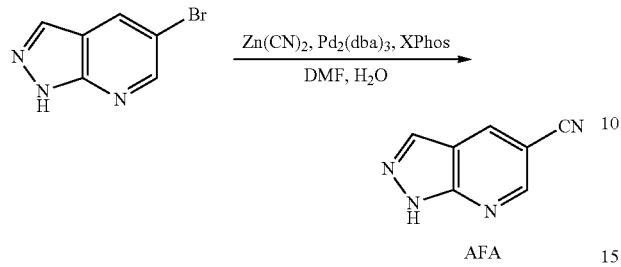

To a mixture of 5-bromo-1H-pyrazolo[3,4-b]pyridine (2.00 g, 10.1 mmol, from CAS #875781-17-2) in DMF (50 mL) was added Zn(CN)$_2$ (1.19 g, 10.1 mmol), Pd$_2$(dba)$_3$ (925 mg, 1.01 mmol), H$_2$O (364 mg, 20.2 mmol) and XPhos (481 mg, 1.01 mmol) under N$_2$. The mixture was stirred at 100° C. for 12 hours. On completion, the reaction mixture was filtered and the filter liquor concentrated in vacuo to give the residue. The residue was purified by reverse phase HPLC (0.1% FA condition) to give the title compound (1.20 g, 82% yield) as a brown solid. $^1$H NMR (400 MHz, DMSO-d$_6$) δ 14.52-14.02 (m, 1H), 8.89 (s, 2H), 8.36 (s, 1H); LC-MS (ESI$^+$) m/z 145.1 (M+H)$^+$.

6-(5-Cyanopyrazolo[3,4-b]pyridin-1-yl)-4-(cyclopropylamino)pyridine-3-carboxylic acid (Intermediate AFB)

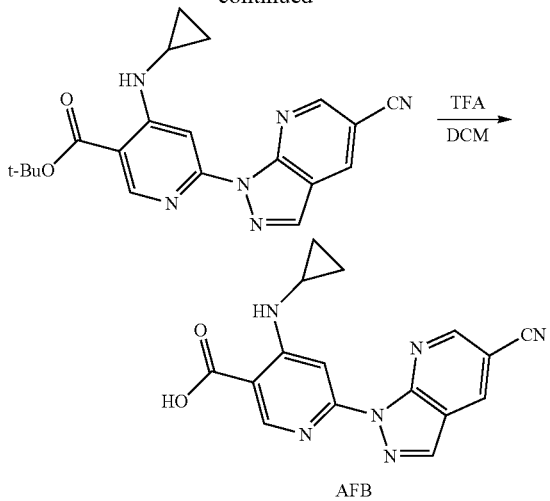

Step 1—Ethyl 6-chloro-4-(cyclopropylamino)pyridine-3-carboxylate

To a mixture of ethyl 4,6-dichloropyridine-3-carboxylate (3.00 g, 13.6 mmol, CAS #40296-46-6) in DMA (30 mL) was added DIPEA (1.76 g, 13.6 mmol) and cyclopropanamine (856 mg, 15.0 mmol, CAS #765-30-0). The mixture was heated at 90° C. for 12 hours. On completion, the reaction mixture was poured into water (120 mL), and the aqueous phase was extracted with ethyl acetate (2×80 mL). The combined organic phase was washed with brine (2×60 mL), dried with anhydrous Na$_2$SO$_4$, filtered and concentrated in vacuo to give the title compound (3.20 g, 97% yield) as a brown solid. $^1$H NMR (400 MHz, DMSO-d$_6$) δ 8.53 (s, 1H), 8.09 (s, 1H), 7.02 (s, 1H), 4.33-4.24 (m, 2H), 2.60 (s, 1H), 1.37-1.26 (m, 3H), 0.92-0.80 (m, 2H), 0.61-0.53 (m, 2H).

Step 2—6-Chloro-4-(cyclopropylamino)pyridine-3-carboxylic acid

To a mixture of ethyl 6-chloro-4-(cyclopropylamino)pyridine-3-carboxylate (1.50 g, 6.23 mmol) in THF (16 mL), MeOH (4 mL) and H$_2$O (4 mL) was added LiOH (448 mg, 18.7 mmol). The mixture was stirred at 50° C. for 12 hours. On completion, the reaction mixture was concentrated in vacuo at 45° C. to remove MeOH and THF. Then water (50 mL) was added into the mixture, and the mixture was adjusted to pH=4-5 with HCl (1 N), and filtered to get the filter cake. The solid was dried to give the title compound (1.20 g, 90% yield) as a brown solid. $^1$H NMR (400 MHz, DMSO-d$_6$) δ 8.51 (s, 1H), 8.30 (s, 1H), 6.98 (s, 1H), 3.24-3.02 (m, 1H), 2.58 (d, J=3.6, 6.4 Hz, 1H), 0.89-0.81 (m, 2H), 0.60-0.50 (m, 2H).

Step 3—Tert-butyl 6-chloro-4-(cyclopropylamino)pyridine-3-carboxylate

To a mixture of 6-chloro-4-(cyclopropylamino)pyridine-3-carboxylic acid (1.20 g, 5.64 mmol) in toluene (20 mL) was added 1,1-ditert-butoxy-N,N-dimethyl-methanamine (6.88 g, 33.9 mmol, CAS #36805-97-7). The mixture was stirred at 100° C. for 12 hours. On completion, the mixture was concentrated in vacuo to give the residue. The residue was purified by column chromatography (SiO$_2$, PE:EA=20:1 to 10:1) to give the title compound (800 mg, 52% yield) as a white solid. $^1$H NMR (400 MHz, CDCl$_3$) δ 8.59 (s, 1H), 8.24 (s, 1H), 6.95 (s, 1H), 2.51-2.44 (m, 1H), 1.57 (s, 9H), 0.91-0.86 (m, 2H), 0.65-0.60 (m, 2H).

Step 4—Tert-butyl 6-(5-cyanopyrazolo[3,4-b]pyridin-1-yl)-4-(cyclopropylamino)pyridine-3-carboxylate To a mixture of 1H-pyrazolo[3,4-b]pyridine-5-carbonitrile (268 mg, 1.86 mmol, Intermediate AFA), and tert-butyl 6-chloro-4-(cyclopropylamino)pyridine-3-carboxylate (500 mg, 1.86 mmol) in dioxane (10 mL) and H$_2$O (1 mL) was added K$_3$PO$_4$ (1.18 g, 5.58 mmol) Pd$_2$(dba)$_3$ (170 mg, 186 umol) and t-Bu Xphos (79.0 mg, 186 umol). The reaction mixture was stirred at 70° C. for 0.5 hour. On completion, the reaction mixture was poured into water (20 mL) and stirred at 10 minutes. The mixture was filtered and the filter cake was dried in vacuo to give the title compound (368 mg, 52% yield) as a yellow solid. $^1$H NMR (400 MHz, CDCl$_3$) δ 9.00 (s, 1H), 8.97 (d, J=2.0 Hz, 1H), 8.50 (d, J=2.0 Hz, 1H), 8.39 (s, 2H), 7.92 (s, 1H), 2.68-2.62 (m, 1H), 1.60 (s, 9H), 0.96-0.93 (m, 2H), 0.73-0.68 (m, 2H).

Step 5—6-(5-Cyanopyrazolo[3,4-b]pyridin-1-yl)-4-(cyclopropylamino)pyridine-3-carboxylic acid To a mixture tert-butyl 6-(5-cyanopyrazolo[3,4-b]pyridin-1-yl)-4-(cyclopropylamino)pyridine-3-carboxylate (200 mg, 531 umol) in DCM (4 mL) was added TFA (121 mg, 1.06 mmol). The mixture was stirred at 20° C. for 0.5 hour. On completion, the reaction mixture was concentrated in vacuo to give the title compound (168 mg, 98% yield) as brown oil. LC-MS (ESI$^+$) m/z 321.1 (M+H)$^+$.

N-[1-[4-[[4-aminobutyl(methyl)amino]methyl]cyclohexyl]-3-(difluoromethyl)pyrazol-4-yl]-2-[2-(cyclopropylmethylamino)-4-pyridyl]oxazole-4-carboxamide (Intermediate AFC)

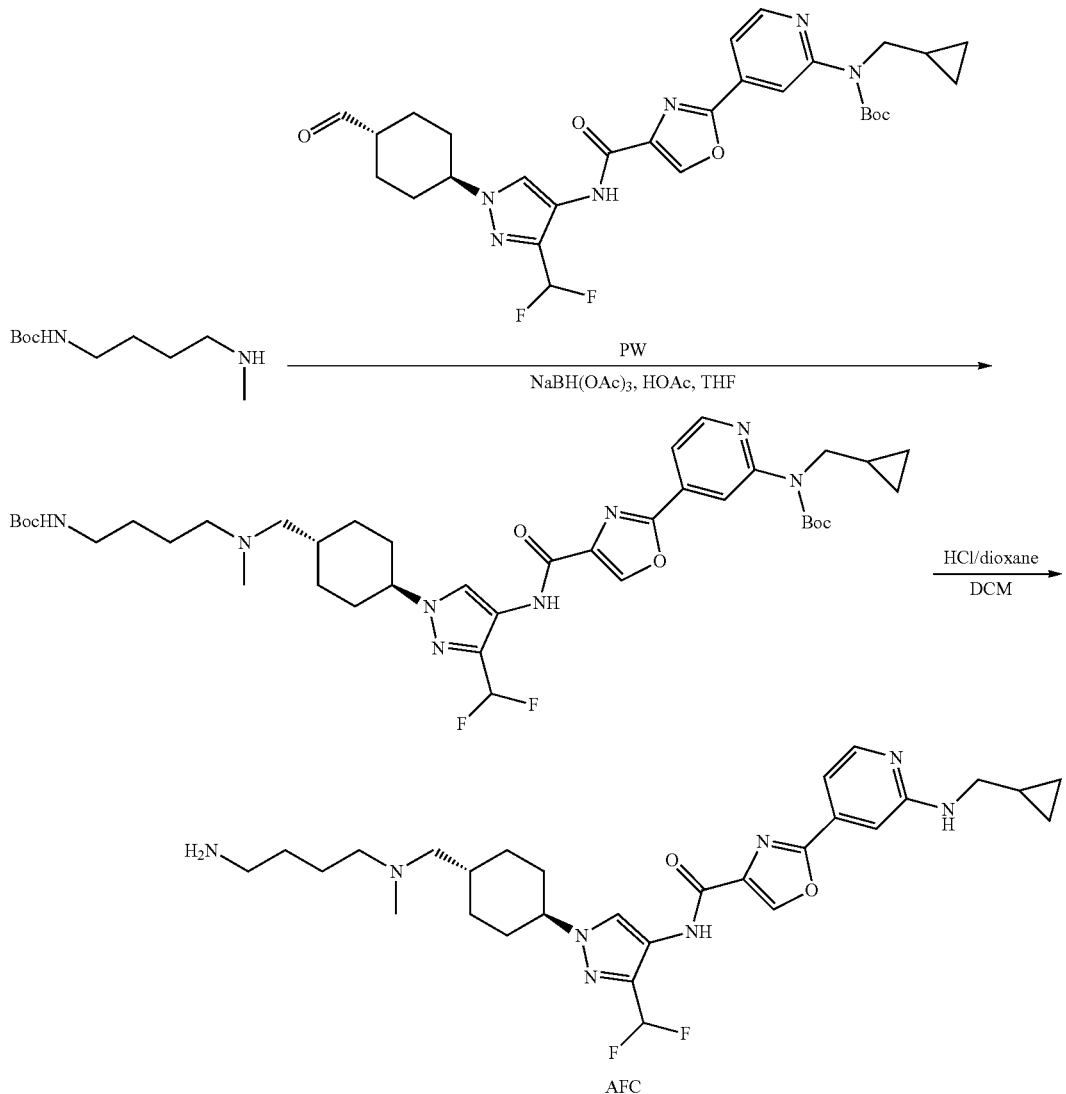

Step 1—Tert-butyl N-[4-[4-[[1-[4-[[4-(tert-butoxy-carbonylamino)butyl-methyl-amino]methyl] cyclohexyl]-3-(difluoromethyl)pyrazol-4-yl]carbamoyl] oxazol-2-yl]-2-pyridyl]-N-(cyclopropylmethyl) carbamate To a solution of tert-butyl N-[4-(methylamino)butyl]carbamate (50.0 mg, 247 umol, CAS #874831-66-0) in THF (2 mL) was added AcOH (14.8 mg, 247 umol) and tert-butyl N-(cyclopropylmethyl)-N-[4-[4-[[3-(difluoromethyl)-1-(4-formylcyclohexyl) pyrazol-4-yl]carbamoyl] oxazol-2-yl]-2-pyridyl]carbamate (144 mg, 247 umol, Intermediate PW). The mixture was stirred at 15° C. for 0.5 hour. Then, NaBH(OAc)$_3$ (78.6 mg, 370 umol) was added at 0° C. and the mixture was stirred at 0° C. for 0.5 hour. The mixture was then stirred at 15° C. for 6 hours. On completion, the reaction was quenched with water (0.5 mL). The mixture was concentrated in vacuo. The residue was purified by reverse phase flash (0.1% FA condition) to give the title compound (200 mg, 50% yield) as white solid. $^1$H NMR (400 MHz, DMSO-d$_6$) δ 9.78 (s, 1H), 9.01 (s, 1H), 8.60 (d, J=5.2 Hz, 1H), 8.30 (s, 1H), 8.18 (d, J=1.6 Hz, 2H), 7.69 (dd, J=1.6, 5.2 Hz, 1H), 7.31-7.00 (t, J=5.6 Hz, 1H), 6.81 (m, 1H), 4.28-4.14 (m, 1H), 3.87 (d, J=6.8 Hz, 2H), 2.32-2.26 (m, 2H), 2.15 (s, 5H), 2.05-2.03 (m, 2H), 1.96-1.86 (m, 2H), 1.82-1.71 (m, 2H), 1.52 (s, 9H), 1.38 (s, 12H), 1.23-1.14 (m, 1H), 1.10-0.97 (m, 2H), 0.47-0.36 (m, 2H), 0.30-0.20 (m, 2H); LC-MS (ESI$^+$) m/z 771.5 (M+H)$^+$.

Step 2—N-[1-[4-[[4-aminobutyl(methyl)amino] methyl]cyclohexyl]-3-(difluoromethyl)pyrazol-4-yl]-2-[2-(cyclopropylmethylamino)-4-pyridyl]oxazole-4-carboxamide To a solution of tert-butyl N-[4-[4-[[1-[4-[[4-(tert-butoxy-carbonylamino)butyl-methyl-amino] methyl]cyclohexyl]-3-(difluoromethyl)pyrazol-4-yl]carbamoyl]oxazol-2-yl]-2-pyridyl]-N-(cyclopropylmethyl)carbamate (20.0 mg, 25.9 umol) in DCM (3 mL) was added HCl/dioxane (4 M, 1.54 mL). The mixture was stirred at 15° C. for 0.5 hour. On completion, the mixture was concentrated in vacuo to give the title compound (14.0 mg, 95% yield) as white solid. LC-MS (ESI$^+$) m/z 571.4 (M+H)$^+$.

N-[1-[4-[6-aminohexyl(methyl)carbamoyl]cyclohexyl]-3-(difluoromethyl)pyrazol-4-yl]-2-[2-(cyclopropylmethylamino)-4-pyridyl]oxazole-4-carboxamide (Intermediate AFD)

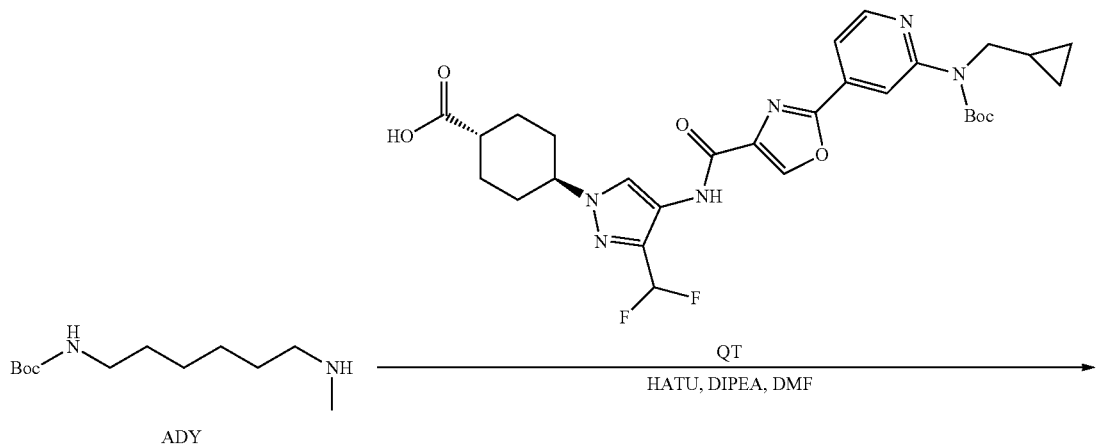

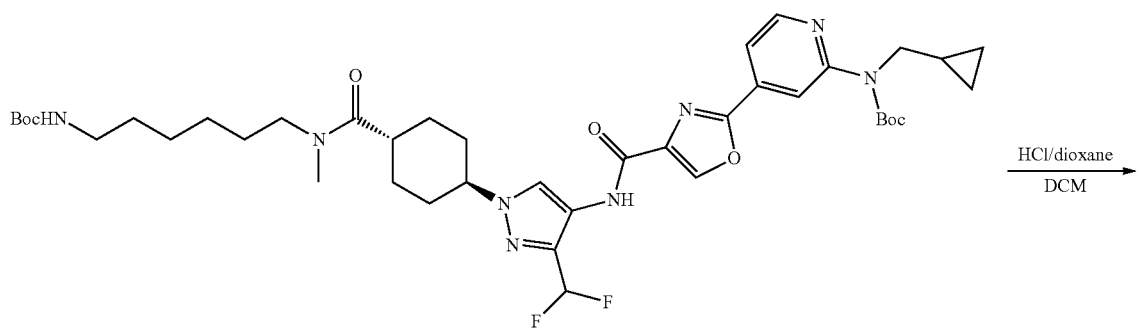

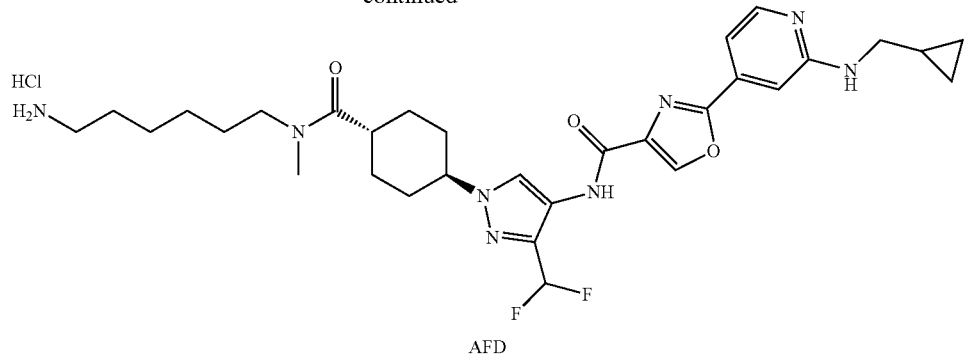

AFD

Step 1—Tert-butyl N-[4-[4-[[1-[4-[6-(tert-butoxy-carbonylamino)hexyl-methyl-carbamoyl]cyclo-hexyl]-3-(difluoromethyl)pyrazol-4-yl]carbamoyl]oxazol-2-yl]-2-pyridyl]-N-(cyclopropylmethyl) carbamate To a solution of tert-butyl N-[6-(methylamino)hexyl]carbamate (70.0 mg, 303 umol, Intermediate ADY) in DMF (6 mL) was added 4-[4-[[2-[2-[tert-butoxycarbonyl(cyclopropylmethyl)amino]-4-pyridyl] oxazole-4-carbonyl]amino]-3-(difluoromethyl)pyrazol-1-yl]cyclohexanecarboxylic acid (140 mg, 233 umol, Intermediate QT), DIPEA (90.6 mg, 701 umol) and HATU (106 mg, 280 umol). The reaction mixture was stirred at 25° C. for 2 hours. On completion, the reaction was quenched with H₂O (0.5 mL) and the mixture was concentrated in vacuo. The residue was purified by prep-HPLC (column: Phenomenex Synergi C18 150*25*10 um; mobile phase: [water (0.225% FA)-ACN]; B %: 70%-100%, 10 min) to give the title compound (190 mg, 94% yield, FA salt) as a white solid. ¹H NMR (400 MHz, DMSO-d₆) δ 9.76 (s, 1H), 9.00 (s, 1H), 8.59 (d, J=5.2 Hz, 1H), 8.29 (s, 1H), 8.22-8.15 (m, 1H), 7.68 (d, J=5.2 Hz, 1H), 7.33-6.99 (m, 1H), 6.78-6.70 (m, 1H), 4.33-4.23 (m, 1H), 3.86 (d, J=6.8 Hz, 2H), 3.36-3.31 (m, 3H), 3.25 (t, J=7.2 Hz, 1H), 3.01 (s, 2H), 2.95-2.84 (m, 2H), 2.79 (s, 1H), 2.75-2.67 (m, 1H), 2.09-2.00 (m, 2H), 1.95-1.72 (m, 4H), 1.68-1.54 (m, 2H), 1.52 (s, 9H), 1.37 (s, 9H), 1.36 (s, 2H), 1.31-1.13 (m, 5H), 0.46-0.35 (m, 2H), 0.28-0.19 (m, 2H); LC-MS (ESI⁺) m/z 813.6 (M+H)⁺.

Step 2—N-[1-[4-[6-aminohexyl(methyl)carbamoyl]cyclohexyl]-3-(difluoromethyl)pyrazol-4-yl]-2-[2-(cyclopropylmethylamino)-4-pyridyl]oxazole-4-carboxamide To a solution of tert-butyl N-[4-[4-[[1-[4-[6-(tert-butoxycarbonylamino)hexyl-methyl-carbamoyl] cyclohexyl]-3-(difluoromethyl)pyrazol-4-yl]carbamoyl]oxazol-2-yl]-2-pyridyl]-N-(cyclopropylmethyl) carbamate (30.0 mg, 36.9 umol) in DCM (2 mL) was added HCl/dioxane (4 M, 1.5 mL). The mixture was stirred at 15° C. for 2 hours. On completion, the reaction mixture was concentrated in vacuo to give the title compound (23.0 mg, 96% yield, HCl salt) as a white solid. LC-MS (ESI⁺) m/z 613.3 (M+H)⁺.

4-[[(2R,3 S,4R,5S)-3-(3-chloro-2-fluoro-phenyl)-4-(4-chloro-2-fluoro-phenyl)-4-cyano-5-(2,2-dimethyl-propyl)pyrrolidine-2-carbonyl] amino]-3-methoxy-benzoic acid (Intermediate AFE)

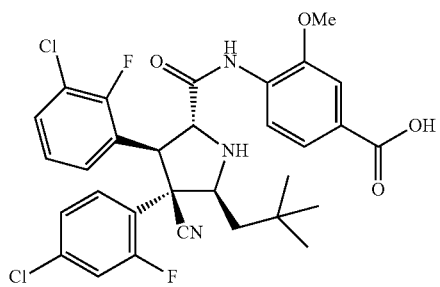 [SMILES: COc1cc(C(=O)O)ccc1NC(=O)[C@@H]1N[C@@H](CC(C)(C)C)[C@](C#N)(c2ccc(Cl)cc2F)[C@H]1c1cccc(Cl)c1F]

4-[[(2R,3 S,4R,5S)-3-(3-chloro-2-fluoro-phenyl)-4-(4-chloro-2-fluoro-phenyl)-4-cyano-5-(2,2-dimethylpropyl) pyrrolidine-2-carbonyl] amino]-3-methoxy-benzoic acid is commercially available, CAS #1229705-06-9.

3-[4-[[4-[[4-[4-Amino-3-(difluoromethyl)pyrazol-1-yl]cyclohexyl]methyl-methyl-amino]-1-piperidyl]methyl]-3-methyl-2-oxo-benzimidazol-1-yl]piperidine-2,6-dione (Intermediate AFF)

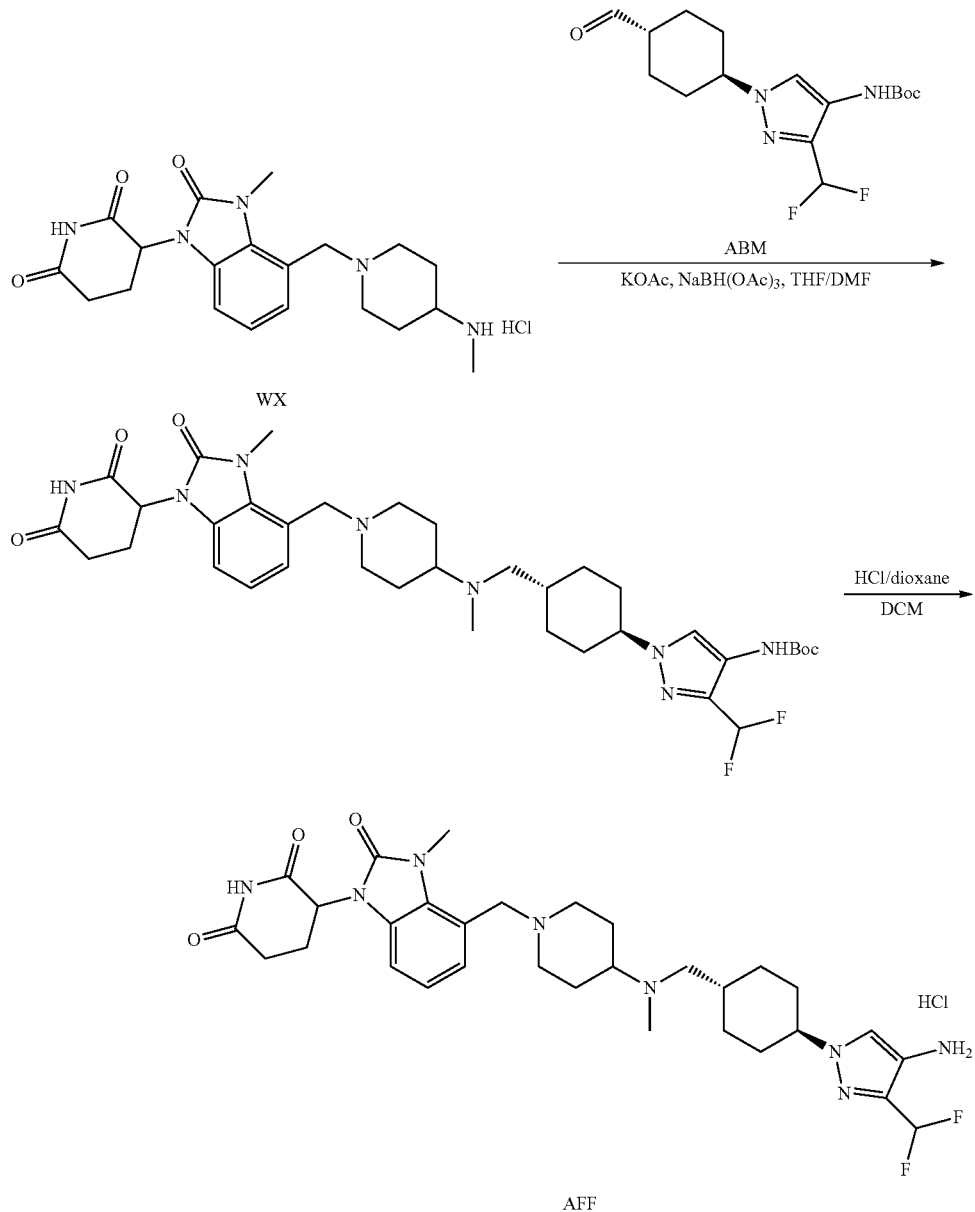

Step 1—Tert-butyl N-[3-(difluoromethyl)-1-[4-[[[1-[[1-(2,6-dioxo-3-piperidyl)-3-methyl-2-oxo-benzimidazol-4-yl]methyl]-4-piperidyl]-methyl-amino]methyl] cyclohexyl]pyrazol-4-yl] carbamate To a mixture of 3-[3-methyl-4-[[4-(methylamino)-1-piperidyl]methyl]-2-oxo-benzimidazol-1-yl] piperidine-2,6-dione (100 mg, 237 umol, HCl salt, Intermediate WX) in a mixed solvent of THF (15 mL) and DMF (5 mL) was added KOAc (69.8 mg, 711 umol) and the mixture was stirred at 25° C. for 0.5 hour. Tert-butyl N-[3-(difluoromethyl)-1-(4-formylcyclohexyl) pyrazol-4-yl]carbamate (81.4 mg, 237 umol, Intermediate ABM) and NaBH(OAc)$_3$ (60.3 mg, 284 umol) was added into the mixture. The reaction mixture was stirred at 25° C. for 1.5 hours. On completion, the reaction was quenched by water (5 mL) and CH$_3$CN (10 mL), and the mixture was concentrated in vacuo to give the residue. The residue was purified by reverse phase (0.1% FA condition) to give the title compound (120 mg, 71% yield) as a white solid. $^1$H NMR (400 MHz, CDCl$_3$) δ 8.35 (s, 2H), 7.91 (s, 1H), 7.01-6.95 (m, 1H), 6.89 (d, J=7.2 Hz, 1H), 6.85-6.58 (m, 3H), 5.22 (d, J=8.8 Hz, 1H), 4.01 (d, J=8.0 Hz, 1H), 3.77 (s, 3H), 3.71-3.65 (m, 2H), 3.21 (d, J=12.0 Hz, 1H), 3.08-2.95 (m, 2H), 2.83-2.73 (m, 3H), 2.66 (s, 3H), 2.28-2.03 (m, 7H), 1.99 (d, J=6.8 Hz, 2H), 1.87-1.73 (m, 3H), 1.71-1.58 (m, 2H), 1.51 (s, 9H), 1.30-1.14 (m, 3H).

1801

Step 2—3-4-[[4-[[4-[4-Amino-3-(difluoromethyl)pyrazol-1-yl] cyclohexyl]methyl-methyl-amino]-1-piperidyl]methyl]-3-methyl-2-oxo-benzimidazol-1-yl]piperidine-2,6-dione To a mixture of tert-butyl N-[3-(difluoromethyl)-1-[4-[[[1-[[1-(2,6-dioxo-3-piperidyl)-3-methyl-2-oxo-benzimidazol-4-yl]methyl]-4-piperidyl]-methyl-amino]methyl]cyclohexyl]pyrazol-4-yl]carbamate (120 mg, 168 umol) in DCM (10 mL) was added HCl/dioxane (4 M, 126 uL). The reaction mixture was stirred at 20° C. for 2 hours. On completion, the reaction mixture was concentrated in vacuo to give the title compound (109 mg, 99% yield) as a white solid. LC-MS (ESI$^+$) m/z 613.2 (M+H)$^+$.

3-[5-[3-[[1-[[4-[4-Amino-3-(difluoromethyl)pyrazol-1-yl]cyclohexyl]methyl]-4-piperidyl] oxy]propyl]-3-methyl-2-oxo-benzimidazol-1-yl]piperidine-2,6-dione (Intermediate AFG)

1802

Step 1—Tert-butyl N-[3-(difluoromethyl)-1-[4-[[4-[3-[1-(2,6-dioxo-3-piperidyl)-3-methyl-2-oxo-benzimidazol-5-yl]propoxy]-1-piperidyl]methyl] cyclohexyl]pyrazol-4-yl]carbamate To a mixture of 3-[3-methyl-2-oxo-5-[3-(4-piperidyloxy)propyl]benzimidazol-1-yl]piperidine-2,6-dione (152 mg, 349 umol, HCl salt, Intermediate ZM) in a mixed solvent of THF (3 mL) and DMF (0.6 mL) was added TEA (106 mg, 1.05 mmol) at −10° C., the mixture was stirred at −10° C. for 6 minutes. Then tert-butyl N-[3-(difluoromethyl)-1-(4-formylcyclohexyl)pyrazol-4-yl]carbamate (120 mg, 349 umol, Intermediate ABM) and HOAc (62.9 mg, 1.05 mmol) was added and the mixture was stirred at −10° C. for 30 minutes. Next, NaBH(OAc)$_3$ (111 mg, 524 umol) was added at −10° C., the mixture was stirred −10° C. for 1 hour. On completion, the reaction mixture was quenched with water (10 mL), and then extracted with DCM (3×15 mL). The combined organic layers were dried over Na$_2$SO$_4$, filtered and con-

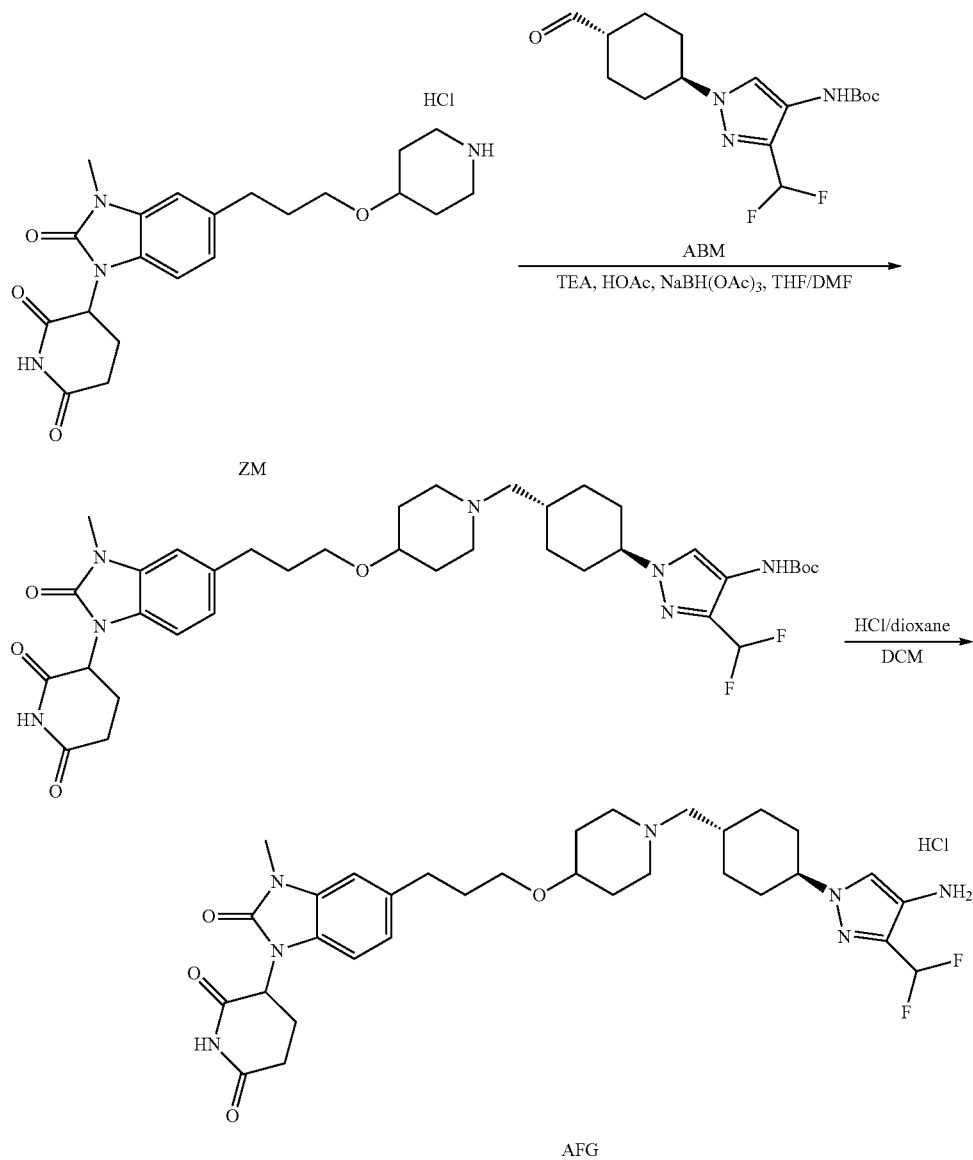

centrated in vacuo to give a residue. The residue was purified by prep-HPLC (FA condition) to give the title compound (140 mg, 55% yield) as white solid. $^1$H NMR (400 MHz, CDCl$_3$) δ 8.47 (s, 1H), 7.90 (s, 1H), 6.91-6.56 (m, 5H), 5.21 (dd, J=5.2, 12.8 Hz, 1H), 4.02-3.97 (m, 1H), 3.50-3.42 (m, 6H), 3.02-2.71 (m, 9H), 2.61-2.53 (m, 2H), 2.33-2.12 (m, 3H), 2.11-1.96 (m, 4H), 1.95-1.88 (m, 2H), 1.84-1.68 (m, 5H), 1.51 (s, 9H), 1.25-1.11 (m, 2H); LC-MS (ESI$^+$) m/z 728.3 (M+H)$^+$.

Step 2—3-[5-[3-[[1-[[4-[4-Amino-3-(difluoromethyl)pyrazol-1-yl] cyclohexyl]methyl]-4-piperidyl] oxy]propyl]-3-methyl-2-oxo-benzimidazol-1-yl] piperidine-2,6-dione To a solution of tert-butyl N-[3-(difluoromethyl)-1-[4-[[4-[3-[1-(2,6-dioxo-3-piperidyl)-3-methyl-2-oxo-benzimidazol-5-yl]propoxy]-1-piperidyl]methyl]cyclohexyl]pyrazol-4-yl]carbamate (60.0 mg, 82.4 umol) in DCM (1 mL) was added HCl/dioxane (4 M, 857 uL), and the mixture was stirred at 15° C. for 4 hours. On completion, the reaction was concentrated in vacuo to give the title compound (54 mg, 98% yield, HCl salt) as light yellow solid. LC-MS (ESI$^+$) m/z 628.2 (M+H)$^+$.

3-[5-[3-(4-Piperidyloxy)propyl]pyrido[2,3-b]indol-9-yl]piperidine-2,6-dione (Intermediate AFH)

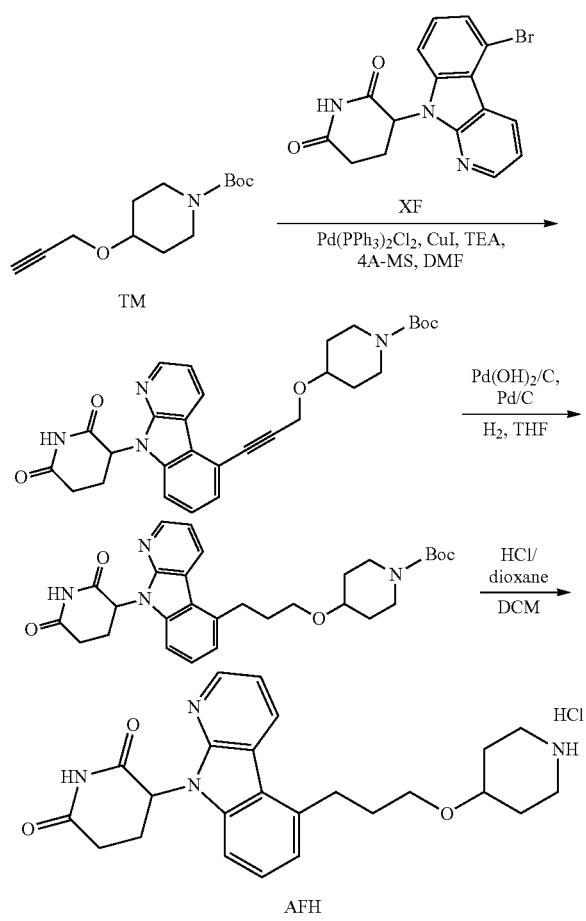

Step 1—Tert-butyl 4-[3-[9-(2,6-dioxo-3-piperidyl)pyrido[2,3-b]indol-5-yl]prop-2-ynoxy]piperidine-1-carboxylate To a mixture of 3-(5-bromopyrido[2,3-b]indol-9-yl)piperidine-2,6-dione (250 mg, 698 umol, Intermediate XF), tert-butyl 4-prop-2-ynoxypiperidine-1-carboxylate (334 mg, 1.40 mmol, Intermediate™) in DMF (5 mL) was added Pd(PPh$_3$)$_2$Cl$_2$ (147 mg, 209 umol), CuI (39.9 mg, 209 umol), TEA (706 mg, 6.98 mmol) and 4 Å molecular sieves (60 mg) under N$_2$. The reaction mixture was stirred at 80° C. for 2 hours. On completion, the residue was poured into water (50 mL) and the aqueous phase was extracted with ethyl acetate (2×30 mL). The combined organic phase was washed with brine (2×40 mL), dried with anhydrous Na$_2$SO$_4$, filtered and concentrated in vacuo to give the residue. The residue was purified by reverse phase (0.1% FA condition) to give the title compound (245 mg, 67% yield) as a brown solid. $^1$H NMR (400 MHz, CDCl$_3$) δ 8.85 (d, J=1.6 Hz, 1H), 8.47 (d, J=1.6 Hz, 1H), 7.43-7.39 (m, 2H), 7.25-7.21 (m, 1H), 7.18-7.06 (m, 2H), 5.92 (d, J=4.2 Hz, 1H), 4.64 (s, 2H), 3.87-3.77 (m, 2H), 3.19-2.89 (m, 6H), 2.31 (d, J=5.2 Hz, 1H), 1.96 (d, J=7.6 Hz, 2H), 1.70-1.60 (m, 2H), 1.47 (s, 9H).

Step 2—Tert-butyl 4-[3-[9-(2,6-dioxo-3-piperidyl)pyrido[2,3-b]indol-5-yl]propoxy]piperidine-1-carboxylate To a mixture of tert-butyl 4-[3-[9-(2,6-dioxo-3-piperidyl)pyrido[2,3-b]indol-5-yl]prop-2-ynoxy] piperidine-1-carboxylate (245 mg, 474 umol) in THF (10 mL) was added Pd/C (50.0 mg, 474 umol) and Pd(OH)$_2$/C (50.0 mg, 474 umol) under N$_2$. The suspension was degassed under vacuum and purged with H$_2$ three times. The mixture was stirred under H$_2$ (15 psi) at 25° C. for 12 hours. On completion, the reaction mixture was filtered and concentrated in vacuo to give the title compound (160 mg, 64% yield) as a brown solid. $^1$H NMR (400 MHz, CDCl$_3$) δ 8.54 (d, J=4.8 Hz, 1H), 8.47-8.39 (m, 1H), 8.16-8.09 (m, 1H), 7.48-7.38 (m, 1H), 7.21 (d, J=4.8 Hz, 1H), 7.13 (d, J=4.8 Hz, 2H), 6.04-5.83 (m, 1H), 3.86-3.76 (m, 2H), 3.60 (d, J=5.9 Hz, 2H), 3.51 (d, J=5.2 Hz, 1H), 3.33-3.26 (m, 2H), 3.21-3.13 (m, 2H), 3.12-3.02 (m, 1H), 3.02-2.93 (m, 2H), 2.30 (d, J=7.6 Hz, 1H), 2.13-2.04 (m, 2H), 1.94-1.82 (m, 2H), 1.66-1.58 (m, 2H), 1.48 (s, 9H).

Step 3—3-[5-[3-(4-Piperidyloxy)propyl]pyrido[2,3-b]indol-9-yl]piperidine-2,6-dione To a mixture of tert-butyl 4-[3-[9-(2,6-dioxo-3-piperidyl)pyrido[2,3-b]indol-5-yl]propoxy] piperidine-1-carboxylate (160 mg, 307 umol) in DCM (10 mL) was added HCl/dioxane (4 M, 230 uL). The reaction mixture was stirred at 20° C. for 2 hours. On completion, the reaction mixture was concentrated in vacuo to give the title compound (135 mg, 96% yield) as a white solid. LC-MS (ESI$^+$) m/z 421.2 (M+H)$^+$.

1805

5-[(3R)-3-Hydroxypyrrolidin-1-yl]pyrazolo[1,5-a]pyrimidine-3-carboxylic acid (Intermediate AFI)

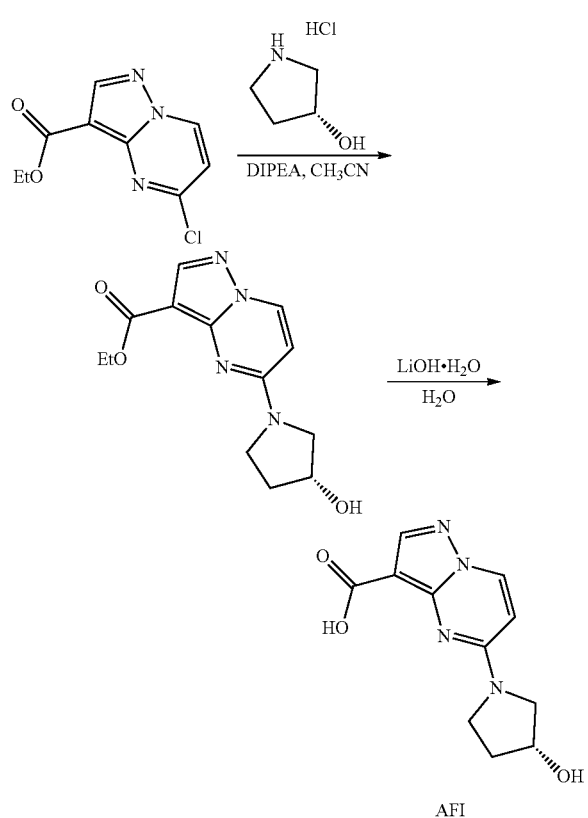

AFI

Step 1—Ethyl 5-[(3R)-3-hydroxypyrrolidin-1-yl]pyrazolo 1,5-a]pyrimidine-3-carboxylate To a solution of ethyl 5-chloropyrazolo[1,5-a]pyrimidine-3-carboxylate (330 mg, 1.46 mmol, CAS #1224944-77-7) and (3R)-pyrrolidin-3-ol (217 mg, 1.76 mmol, HCl salt, CAS #104706-47-0) in ACN (2 mL) was added DIPEA (567 mg, 4.39 mmol). The mixture was stirred at 60° C. for 1 hour. On completion, the mixture was concentrated in vacuo to give the title compound (400 mg, 98% yield) as colorless oil. LC-MS (ESI$^+$) m/z 277.2 (M+H)$^+$.

Step 2—5-[(3R)-3-Hydroxypyrrolidin-1-yl]pyrazolo[1,5-a]pyrimidine-3-carboxylic acid To a solution of ethyl 5-[(3R)-3-hydroxypyrrolidin-1-yl]pyrazolo[1,5-a]pyrimidine-3-carboxylate (300 mg, 1.09 mmol) in H$_2$O (1 mL) was added LiOH·H$_2$O (228 mg, 5.43 mmol). The mixture was stirred at 60° C. for 2 hours. On completion, the mixture was concentrated of most solvent. The crude product was purified by reversed-phase HPLC (0.1% FA condition) to give the title compound (260 mg, 80% yield, FA salt) as white solid. $^1$H NMR (400 MHz, DMSO-d$_6$) δ 8.68 (d, J=7.6 Hz, 1H), 8.16 (s, 1H), 6.56-6.48 (m, 1H), 5.14-4.99 (m, 1H), 4.49-4.37 (m, 1H), 3.63-3.56 (m, 3H), 2.10-1.89 (m, 2H); LC-MS (ESI$^+$) m/z 249.1 (M+H)$^+$.

1806

2-(2,6-Dioxo-3-piperidyl)-4-[3-(4-piperidyloxy)propylamino]isoindoline-1,3-dione (Intermediate AFJ)

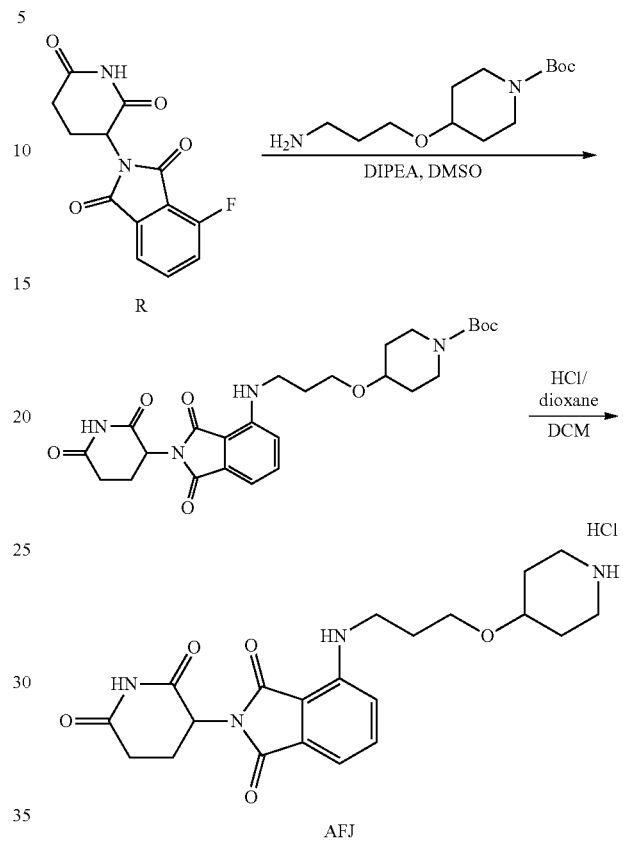

AFJ

Step 1—Tert-butyl 4-[3-[[2-(2,6-dioxo-3-piperidyl)-1,3-dioxo-isoindolin-4-yl]amino]propoxy] piperidine-1-carboxylate To a solution of 2-(2,6-dioxo-3-piperidyl)-4-fluoro-isoindoline-1,3-dione (230 mg, 832 umol, Intermediate R) and tert-butyl 4-(3-aminopropoxy)piperidine-1-carboxylate (322 mg, 1.25 mmol, CAS #771572-33-9) in DMSO (15 mL) was added DIPEA (18.7 mg, 144 umol) at 25° C. The reaction mixture was stirred at 130° C. for 2 hours. On completion, the reaction mixture was diluted with EA (30 mL), washed with H$_2$O (3×10 mL), dried over by Na$_2$SO$_4$, filtered and concentrated in vacuo. The residue was purified by reverse phase (0.1% FA condition) to give the title compound (270 mg, 63% yield) as a yellow solid. $^1$H NMR (400 MHz, DMSO-d$_6$) δ 11.07 (s, 1H), 7.61-7.55 (m, 1H), 7.10 (d, J=8.4 Hz, 1H), 7.02 (d, J=6.8 Hz, 1H), 5.04 (dd, J=5.2, 13.2 Hz, 1H), 3.64-3.58 (m, 2H), 3.51 (t, J=6.0 Hz, 2H), 3.46-3.36 (m, 4H), 3.04-2.98 (m, 2H), 2.94-2.82 (m, 1H), 2.62-2.55 (m, 2H), 2.53-2.51 (m, 2H), 1.83-1.74 (m, 4H), 1.38 (s, 9H); LC-MS (ESI$^+$) m/z 415.2 (M−100)$^+$.

Step 2—2-(2,6-Dioxo-3-piperidyl)-4-[3-(4-piperidyloxy)propylamino]isoindoline-1,3-dione To a solution of tert-butyl 4-[3-[[2-(2,6-dioxo-3-piperidyl)-1,3-dioxo-isoindolin-4-yl]amino]propoxy] piperidine-1-carboxylate (50.0 mg, 97.1 umol) in DCM (2 mL) was added HCl/dioxane (4 M, 2.50 mL). The mixture was stirred at 15° C. for 2 hours. On completion, the reaction mixture was concentrated in vacuo to give the title compound (40.0 mg, 91% yield, HCl salt) as a yellow solid. LC-MS (ESI+) m/z 415.2 (M+H)+.

1-(((2S,3S,4S)-3-ethyl-4-fluoro-5-oxopyrrolidin-2-yl)methoxy)-4-(((1 r,4S)-4-(hydroxymethyl)cyclohexyl)ethynyl)-7-methoxyisoquinoline-6-carboxamide (Intermediate AFK) and 1-(((2S,3S,4S)-3-ethyl-4-fluoro-5-oxopyrrolidin-2-yl)methoxy)-4-(((1 s,4R)-4-(hydroxymethyl)cyclohexyl)ethynyl)-7-methoxyisoquinoline-6-carboxamide (Intermediate AFL)

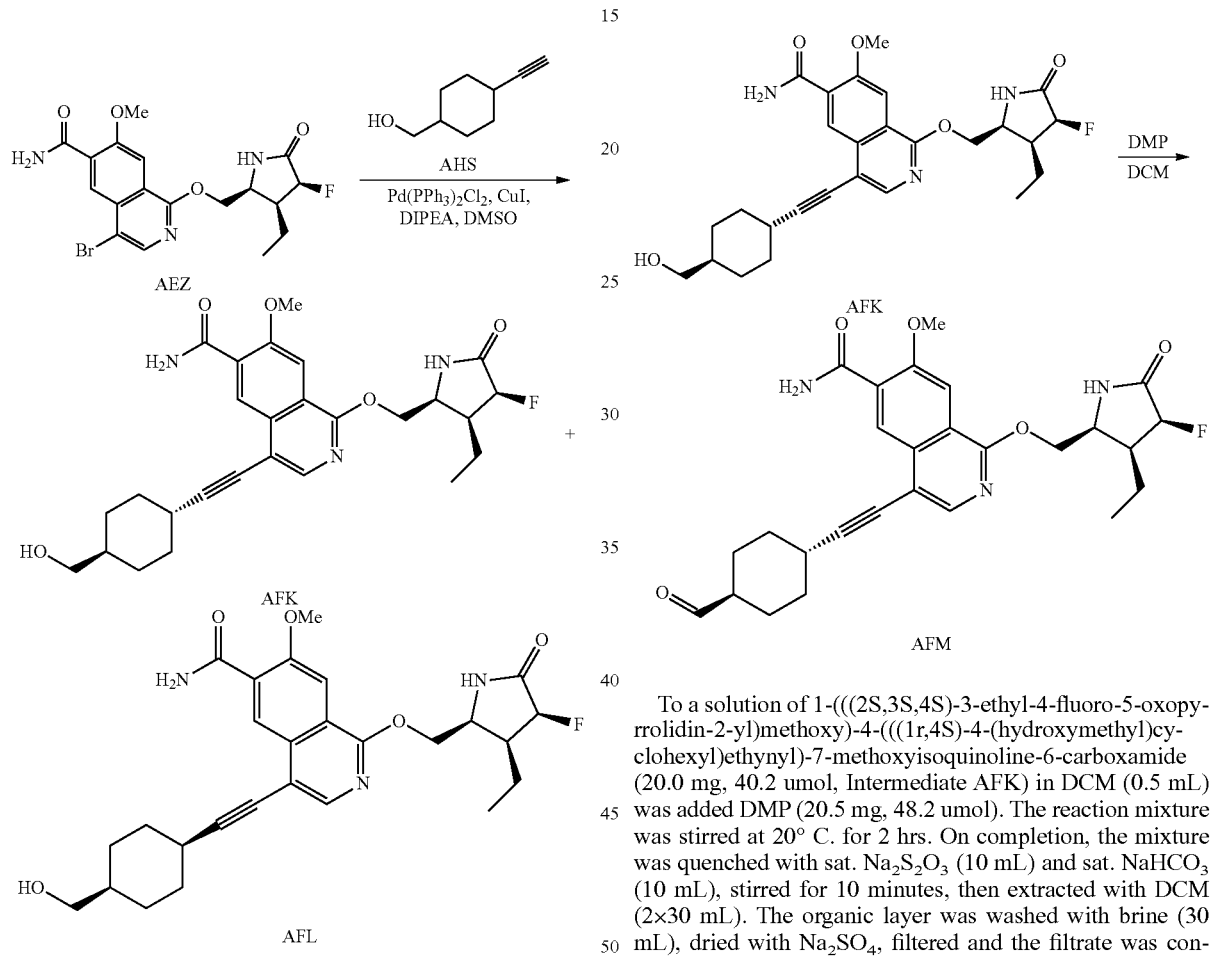

(4-Ethynylcyclohexyl)methanol (170 mg, 1.23 mmol, Intermediate AHS), 4-bromo-1-[[(2S,3S,4S)-3-ethyl-4-fluoro-5-oxo-pyrrolidin-2-yl]methoxy]-7-methoxy-isoquinoline-6-carboxamide (300 mg, 681 umol, Intermediate AEZ), CuI (25.9 mg, 136 umol), Pd(PPh3)2Cl2 (95.7 mg, 136 umol) and DIPEA (440 mg, 3.41 mmol) in DMSO (5 mL) was de-gassed and then heated at 80° C. for 3 hours under N2. On completion, the mixture was concentrated in vacuo. The residue was purified by prep-HPLC (column: Waters Xbridge 150*25 mm*5 um; mobile phase: [water (10 mM NH4HCO3)-ACN]; B %: 28%-41%, 10 min) to give 1-(((2S,3S,4S)-3-ethyl-4-fluoro-5-oxopyrrolidin-2-yl)methoxy)-4-(((1r,4S)-4-(hydroxymethyl)cyclohexyl)ethynyl)-7-methoxyisoquinoline-6-carboxamide (140 mg, 41% yield) as a white solid. The cis-isomer 1-(((2S,3S,4S)-3-ethyl-4-fluoro-5-oxopyrrolidin-2-yl)methoxy)-4-(((1 s,4R)-4-(hydroxymethyl)cyclohexyl)ethynyl)-7-methoxyisoquinoline-6-carboxamide (50.0 mg, 15% yield) was also obtained as a white solid. 1H NMR (400 MHz, CDCl3) δ 8.81 (s, 1H), 7.94 (s, 1H), 7.66 (s, 1H), 4.97-4.78 (m, 1H), 4.64 (dd, J=3.2, 11.6 Hz, 1H), 4.35 (dd, J=5.2, 11.6 Hz, 1H), 4.16-4.08 (m, 1H), 4.03 (s, 3H), 3.39 (d, J=6.4 Hz, 2H), 2.65-2.43 (m, 2H), 2.23-2.10 (m, 2H), 1.92-1.40 (m, 8H), 1.12-0.90 (m, 6H).

1-[[(2S,3S,4S)-3-ethyl-4-fluoro-5-oxo-pyrrolidin-2-yl]methoxy]-4-[2-(4-formylcyclohexyl) ethynyl]-7-methoxy-isoquinoline-6-carboxamide ((Intermediate AFM)

To a solution of 1-(((2S,3S,4S)-3-ethyl-4-fluoro-5-oxopyrrolidin-2-yl)methoxy)-4-(((1r,4S)-4-(hydroxymethyl)cyclohexyl)ethynyl)-7-methoxyisoquinoline-6-carboxamide (20.0 mg, 40.2 umol, Intermediate AFK) in DCM (0.5 mL) was added DMP (20.5 mg, 48.2 umol). The reaction mixture was stirred at 20° C. for 2 hrs. On completion, the mixture was quenched with sat. Na2S2O3 (10 mL) and sat. NaHCO3 (10 mL), stirred for 10 minutes, then extracted with DCM (2×30 mL). The organic layer was washed with brine (30 mL), dried with Na2SO4, filtered and the filtrate was concentrated in vacuo to give the title compound (15.0 mg, 75% yield) as a white solid. LC-MS (ESI+) m/z 496.3 (M+H)+.

4-[3-(Difluoromethyl)-4-nitro-pyrazol-1-yl]-1-(4-piperidylmethyl)piperidine (Intermediate AFN)

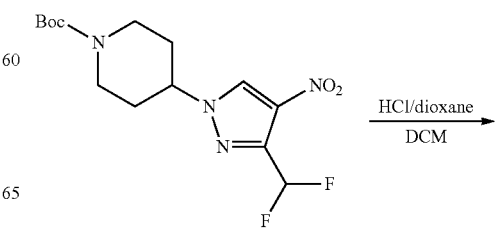

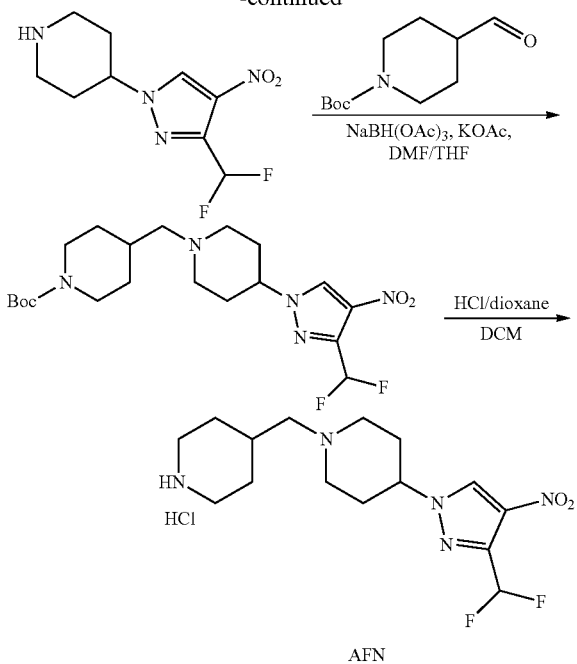

Step 1—4-[3-(Difluoromethyl)-4-nitro-pyrazol-1-yl]piperidine

To a solution of tert-butyl 4-[3-(difluoromethyl)-4-nitro-pyrazol-1-yl]piperidine-1-carboxylate (300 mg, 866 umol, synthesized via Steps 1-2 of Intermediate AEI) in DCM (6 mL) was added HCl/dioaxne (4 M, 3.00 mL). The reaction mixture was stirred at 20° C. for 30 minutes. On completion, the mixture was concentrated in vacuo to give the title compound (240 mg, 98% yield, HCl salt) as a white solid. LC-MS (ESI$^+$) m/z 247.1 (M+H)$^+$.

Step 2—Tert-butyl 4-[[4-[3-(difluoromethyl)-4-nitro-pyrazol-1-yl]-1-piperidyl]methyl]piperidine-1-carboxylate To a solution of 4-[3-(difluoromethyl)-4-nitro-pyrazol-1-yl]piperidine (240 mg, 849 umol, HCl salt) and tert-butyl 4-formylpiperidine-1-carboxylate (181 mg, 849 umol, CAS #137076-22-3) in THF (10 mL) and DMF (2 mL) was added KOAc (124 mg, 1.27 mmol). The reaction was stirred at 20° C. for 30 minutes. Then NaBH(OAc)$_3$ (269 mg, 1.27 mmol) was added to the mixture, and the reaction was stirred at 20° C. for 12 hours. On completion, the reaction mixture was quenched with H$_2$O (0.5 mL), and then concentrated in vacuo to give a residue. The residue was purified by reverse phase (0.1% FA condition) to give the title compound (330 mg, 87% yield) as a white solid. $^1$H NMR (400 MHz, CDCl$_3$) δ 8.28 (s, 1H), 7.26-6.97 (m, 1H), 4.36-4.25 (m, 1H), 4.21-4.01 (m, 2H), 3.30-3.17 (m, 2H), 2.71 (t, J=12.4 Hz, 2H), 2.51-2.37 (m, 4H), 2.34-2.26 (m, 2H), 2.25-2.14 (m, 2H), 1.83-1.69 (m, 3H), 1.48 (s, 9H), 1.22-1.04 (m, 2H); LC-MS (ESI$^+$) m/z 444.1 (M+H)$^+$.

Step 3—4-[3-(Difluoromethyl)-4-nitro-pyrazol-1-yl]-1-(4-piperidylmethyl)piperidine To a solution of tert-butyl 4-[[4-[3-(difluoromethyl)-4-nitro-pyrazol-1-yl]-1-piperidyl]methyl] piperidine-1-carboxylate (320 mg, 721 umol) in DCM (6 mL) was added HCl/dioaxne (4 M, 3 mL). The reaction mixture was stirred at 20° C. for 30 minutes. On completion, the mixture was concentrated in vacuo to give the title compound (270 mg, 98% yield, HCl salt) as a white solid. LC-MS (ESI$^+$) m/z 344.2 (M+H)$^+$.

3-[4-[[4-[4-Amino-3-(Difluoromethyl)pyrazol-1-yl]-1-piperidyl]methyl]-1-piperidyl] methyl]-3-methyl-2-oxo-benzimidazol-1-yl]]piperidine-2,6-dione (Intermediate AFO)

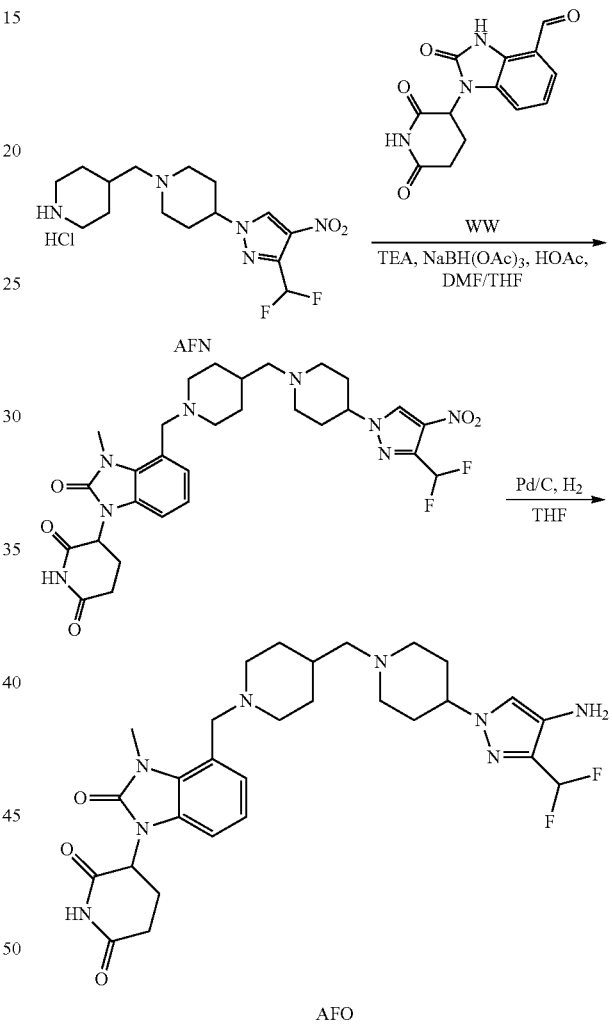

Step 1—3-[4-[[4-[[4-[3-(Difluoromethyl)-4-nitro-pyrazol-1-yl]-1-piperidyl]methyl]-1-piperidyl] methyl]-3-methyl-2-oxo-benzimidazol-1-yl]piperidine-2,6-dione To a solution of 4-[3-(difluoromethyl)-4-nitro-pyrazol-1-yl]-1-(4-piperidylmethyl)piperidine (170 mg, 447 umol, HCl, Intermediate AFN) in DMF (3 mL) and THF (12 mL) was added TEA (45.2 mg, 447 umol, 62.3 uL). The reaction mixture was stirred at 20° C. for 15 minutes, then 1-(2,6-dioxo-3-piperidyl)-3-methyl-2-oxo-benzimidazole-4-carbaldehyde (128 mg, 447 umol, Intermediate WW) and HOAc (53.7 mg, 895 umol, 51.2 uL) were added to the mixture. The reaction mixture was stirred at 20° C. for 30 minutes. Then NaBH(OAc)$_3$ (142 mg, 671 umol) was added to the mixture, and the reaction mixture was stirred at 50° C. for 16 hours. On completion, the reaction mixture quenched by addition H$_2$O (0.5 mL), then the mixture was concentrated in vacuo to give a residue. The residue was purified by reverse phase (0.1% FA condition) to give the title compound (180 mg, 65% yield) as a white solid. $^1$H NMR (400 MHz, DMSO-d$_6$) δ 11.10 (s, 1H), 9.08 (s, 1H), 7.44-7.17 (m, 1H), 7.07 (d, J=8.0 Hz, 1H), 6.96 (t, J=7.6 Hz, 1H), 6.92-6.83 (m, 1H), 5.38 (dd, J=5.2, 12.4 Hz, 1H), 4.35-4.28 (m, 1H), 3.67 (s, 3H), 3.65-3.59 (m, 2H), 3.01-2.80 (m, 6H), 2.71-2.61 (m, 2H), 2.21-2.17 (m, 2H), 2.07-1.94 (m, 8H), 1.73-1.61 (m, 2H), 1.60-1.44 (m, 1H), 1.16-0.97 (m, 2H).

Step 2—3-[4-[[4-[[4-[4-Amino-3-(difluoromethyl) pyrazol-1-yl]-1-piperidyl]methyl]-1-piperidyl] methyl]-3-methyl-2-oxo-benzimidazol-1-yl]piperidine-2,6-dione To a solution of 3-[4-[[4-[[4-[3-(difluoromethyl)-4-nitro-pyrazol-1-yl]-1-piperidyl]methyl]-1-piperidyl] methyl]-3-methyl-2-oxo-benzimidazol-1-yl]piperidine-2,6-dione (200 mg, 325 umol) in THF (5 mL) was added Pd/C (50 mg, 10% wt). The reaction mixture was stirred at 20° C. for 2 hours under H$_2$ (15 psi). On completion, the residue was filtered and the filtrate was concentrated in vacuo to give the title compound (160 mg, 84% yield) as a purple solid. $^1$H NMR (400 MHz, DMSO-d$_6$) δ 11.12 (s, 1H), 7.17 (s, 1H), 7.07 (d, J=8.0 Hz, 1H), 7.02-6.74 (m, 3H), 5.38 (dd, J=5.2, 12.4 Hz, 1H), 4.00-3.93 (m, 1H), 3.68 (s, 3H), 3.62 (s, 2H), 2.93-2.78 (m, 5H), 2.77-2.60 (m, 2H), 2.17-2.13 (m, 2H), 2.06-2.00 (m, 2H), 1.98-1.79 (m, 7H), 1.72-1.62 (m, 2H), 1.57-1.46 (m, 1H), 1.12-1.00 (m, 2H); LC-MS (ESI$^+$) m/z 585.4 (M+H)$^+$.

Tert-butyl 4-but-3-ynoxypiperidine-1-carboxylate (Intermediate AFP)

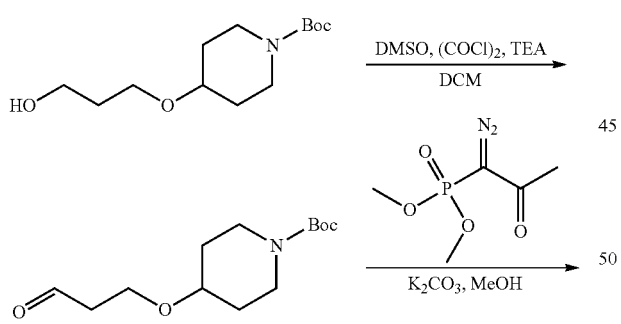

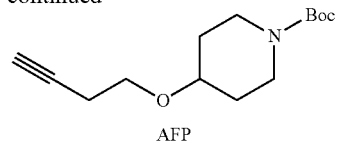

Step 1—Tert-butyl 4-(3-oxopropoxy)piperidine-1-carboxylate

To a mixture of DMSO (376 mg, 4.82 mmol, 376 uL) in DCM (20 mL) was added a solution of (COCl)$_2$ (489 mg, 3.86 mmol, 337 uL) in DCM (10 mL) dropwise at −70° C. The mixture was stirred at −70° C. for 10 minutes, then a solution of tert-butyl 4-(3-hydroxypropoxy)piperidine-1-carboxylate (500 mg, 1.93 mmol, synthesized via Steps 1-2 of Intermediate ADK) in DCM (10 mL) was added into the above mixture slowly. After stirred at −70° C. for 50 minutes, TEA (1.56 g, 15.4 mmol, 2.15 mL) was added and the reaction mixture was stirred at −70° C. for 0.5 hour. On completion, the reaction mixture was quenched with H$_2$O (40 mL), then extracted with DCM (2×80 mL). The organic layers was combined and washed with brine (2×50 mL), dried over Na$_2$SO$_4$, concentrated in vacuo to give the title compound (450 mg, 90.7% yield) as yellow oil. $^1$H NMR (400 MHz, DMSO-d$_6$) δ 9.65 (t, J=2.0 Hz, 1H), 3.74 (t, J=6.0 Hz, 2H), 3.62-3.56 (m, 2H), 3.50-3.43 (m, 1H), 3.10-3.02 (m, 2H), 2.62-2.56 (m, 2H), 1.79-1.72 (m, 2H), 1.38 (s, 9H), 1.34-1.26 (m, 2H).

Step 2—Tert-butyl 4-but-3-ynoxypiperidine-1-carboxylate

To a solution of tert-butyl 4-(3-oxopropoxy)piperidine-1-carboxylate (450 mg, 1.75 mmol) and K$_2$CO$_3$ (725 mg, 5.25 mmol) in MeOH (10 mL) was added 1-diazo-1-dimethoxy-phosphoryl-propan-2-one (436 mg, 2.27 mmol) at 0° C., and the reaction mixture was stirred at 20° C. for 16 hour. On completion, The reaction mixture was quenched with H$_2$O (20 mL), then extracted with EA (2×40 mL). The combined organic phase was filtered, the filtrate was dried over Na$_2$SO$_4$ and concentrated in vacuo give the title compound (400 mg, 90.3% yield) as yellow oil. $^1$H NMR (400 MHz, CDCl$_3$) δ 3.82-3.75 (m, 2H), 3.71-3.64 (m, 2H), 3.55-3.49 (m, 2H), 3.46-3.39 (m, 1H), 3.07-2.99 (m, 2H), 2.41-2.36 (m, 2H), 1.90 (t, J=2.8 Hz, 1H), 1.50-1.42 (m, 2H), 1.38 (s, 9H).

(3R)-3-[(5R)-2-oxo-5-[4-[4-(4-piperidyloxy)but-1-ynyl]phenyl]oxazolidin-3-yl]piperidine-2,6-dione (Intermediate AFQ)

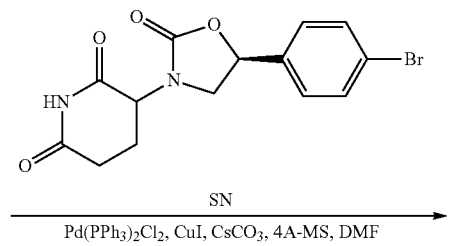

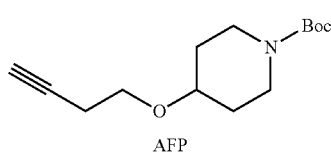

-continued

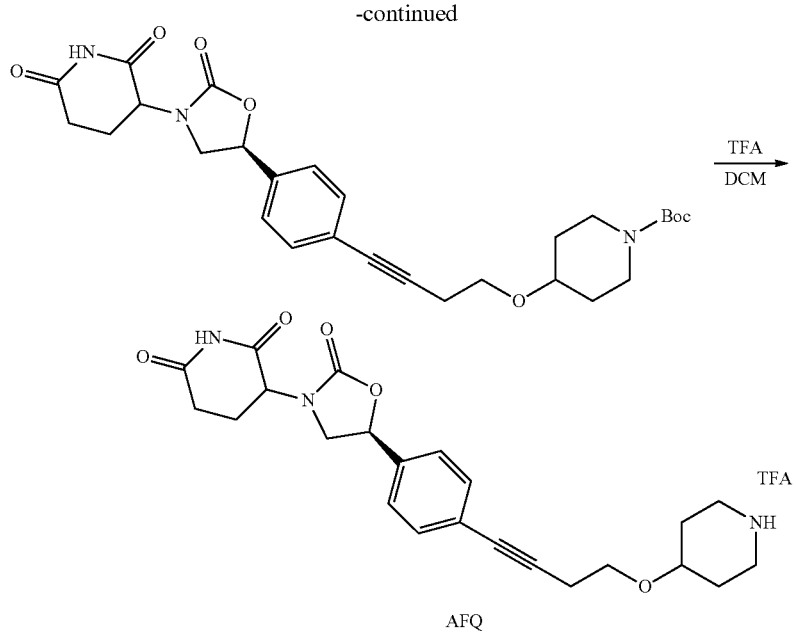

AFQ

Step 1—Tert-butyl 4-[4-[4-[(5R)-3-[(3R)-2,6-dioxo-3-piperidyl]-2-oxo-oxazolidin-5-yl]phenyl] but-3-ynoxy] piperidine-1-carboxylate To a solution of tert-butyl 4-but-3-ynoxypiperidine-1-carboxylate (358 mg, 1.42 mmol, Intermediate AFP) and (3R)-3-[(5R)-5-(4-bromophenyl)-2-oxo-oxazolidin-3-yl]piperidine-2,6-dione (250 mg, 707 umol, Intermediate SN) in DMF (8 mL) was added 4 Å molecular sieves (100 mg), Cs$_2$CO$_3$ (922 mg, 2.83 mmol), CuI (13.4 mg, 70.7 umol) and Pd(PPh$_3$)$_2$Cl$_2$ (49.6 mg, 70.7 umol). The reaction mixture was stirred at 80° C. for 2 hours. On completion, the reaction mixture was filtered and the filtrate was concentrated in vacuo to give a residue. The residue was purified by reverse phase (0.1% FA) to give title compound (205 mg, 55% yield) as yellow solid. LC-MS (ESI$^+$) m/z 426.3 (M+H−100)$^+$.

Step 2—(3R)-3-[(5R)-2-oxo-5-[4-[4-(4-piperidyloxy)but-1-ynyl]phenyl]oxazolidin-3-yl]piperidine-2,6-dione To a solution of tert-butyl 4-[4-[4-[(5R)-3-[(3R)-2,6-dioxo-3-piperidyl]-2-oxo-oxazolidin-5-yl]phenyl] but-3-ynoxy]piperidine-1-carboxylate (200 mg, 380 umol) in DCM (2 mL) was added TFA (1.54 g, 13.5 mmol, 1 mL). The reaction mixture was stirred at 20° C. for 30 minutes. On completion, the mixture was concentrated in vacuo to give a residue. The residue was purified by reverse phase (0.1% TFA condition) to give the title compound (100 mg, 48% yield, TFA salt) as a yellow solid. LC-MS (ESI$^+$) m/z 426.2 (M+H)$^+$.

(3R)-3-[(5R)-5-[4-[4-[[1-[[4-[4-amino-3-(difluoromethyl)pyrazol-1-yl]cyclohexyl]methyl]-4-piperidyl]oxy]but-1-ynyl]phenyl]-2-oxo-oxazolidin-3-yl]piperidine-2,6-dione (Intermediate AFR)

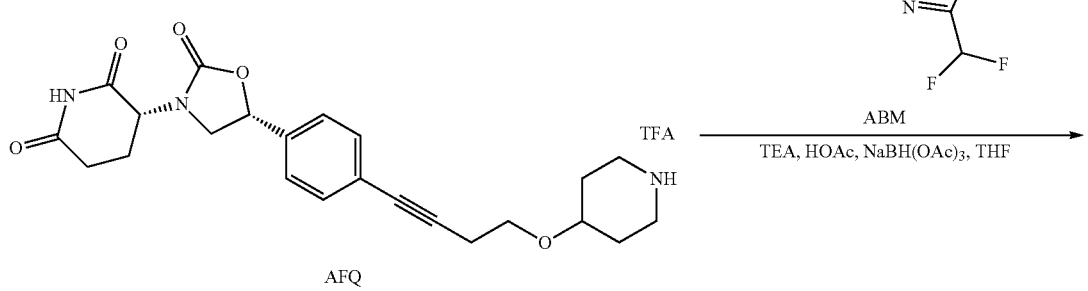

AFQ

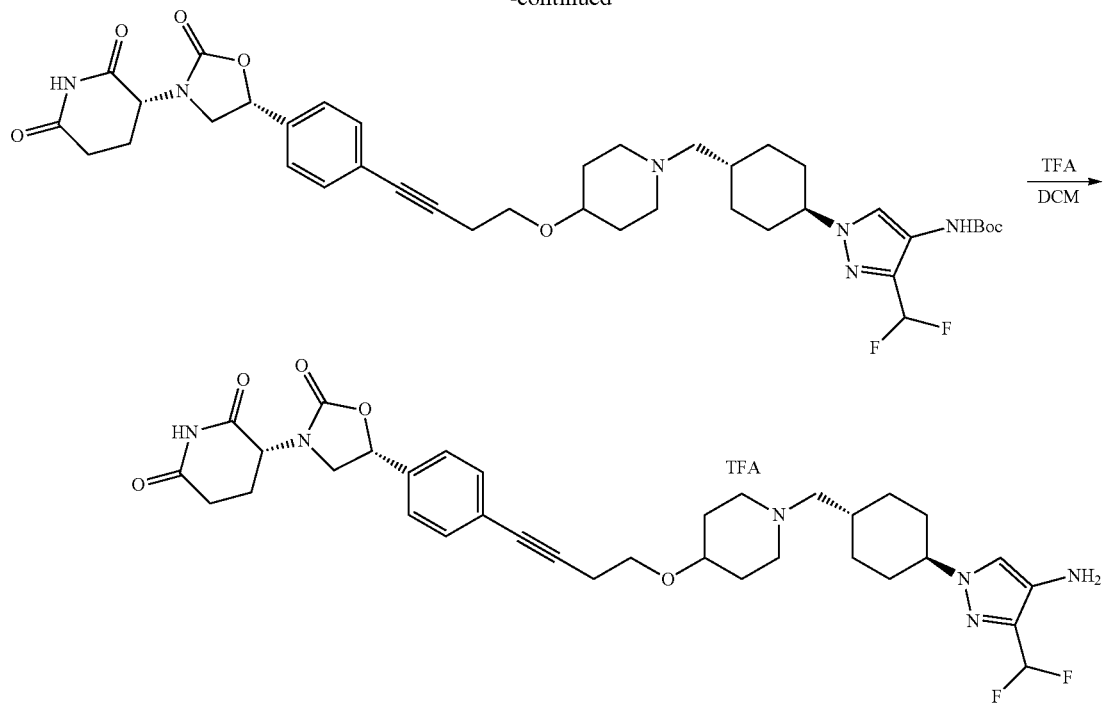

-continued

AFR

Step 1—Tert-butyl N-[3-(difluoromethyl)-1-[4-[[4-[4-[4-[(5R)-3-[(3R)-2,6-dioxo-3-piperidyl]-2-oxo-oxazolidin-5-yl]phenyl]but-3-ynoxy]-1-piperidyl]methyl]cyclohexyl]pyrazol-4-yl] carbamate To a solution of (3R)-3-[(5R)-2-oxo-5-[4-[4-(4-piperidyloxy)but-1-ynyl]phenyl]oxazolidin-3-yl]piperidine-2,6-dione (65.0 mg, 120 umol, TFA, Intermediate AFQ) in THF (3 mL) was added TEA (12.1 mg, 120 umol, 16.7 uL), and the reaction mixture was stirred at 0° C. for 10 min. Then tert-butyl N-[3-(difluoromethyl)-1-(4-formylcyclohexyl)pyrazol-4-yl]carbamate (41.3 mg, 120 umol, Intermediate ABM) and HOAc (14.4 mg, 240 umol, 13.7 uL) were added, and the mixture was stirred at 0° C. for 20 min. Next, NaBH(OAc)$_3$ (33.2 mg, 156 umol) was added to the mixture, and the mixture was stirred at 0° C. for 1 hr. On completion, the mixture was filtered and concentrated in vacuo to give a residue. The residue was purified by reverse phase (0.1% FA condition) to give the title compound (75.0 mg, 82% yield) as a white solid. $^1$H NMR (400 MHz, DMSO-d$_6$) δ 11.03-10.95 (m, 1H), 8.90 (s, 1H), 7.86 (s, 1H), 7.49-7.37 (m, 4H), 7.16-6.85 (m, 1H), 5.72-5.60 (m, 1H), 4.75-4.63 (m, 1H), 4.15-4.04 (m, 1H), 3.96-3.84 (m, 1H), 3.60 (t, J=6.4 Hz, 2H), 2.92-2.79 (m, 1H), 2.72-2.64 (m, 4H), 2.59-2.53 (m, 2H), 2.47-2.35 (m, 1H), 2.26-2.17 (m, 1H), 2.13-2.08 (m, 2H), 2.07-1.96 (m, 5H), 1.89-1.81 (m, 4H), 1.76-1.65 (m, 2H), 1.59-1.51 (m, 1H), 1.51-1.46 (m, 2H), 1.45 (s, 9H), 1.06-0.94 (m, 2H); LC-MS (ESI$^+$) m/z 753.6 (M+H)$^+$.

Step 2—(3R)-3-[(5R)-5-[4-[4-[[1-[[4-[4-amino-3-(difluoromethyl)pyrazol-1-yl]cyclohexyl]methyl]-4-piperidyl]oxy]but-1-ynyl]phenyl]-2-oxo-oxazolidin-3-yl]piperidine-2,6-dione To a solution of tert-butyl N-[3-(difluoromethyl)-1-[4-[[4-[4-[(5R)-3-[(3R)-2,6-dioxo-3-piperidyl]-2-oxo-oxazolidin-5-yl]phenyl]but-3-ynoxy]-1-piperidyl]methyl]cyclohexyl]pyrazol-4-yl]carbamate (70.0 mg, 92.9 umol) in DCM (1 mL) was added TFA (770 mg, 6.75 mmol, 500 uL). The reaction mixture was stirred at 20° C. for 2 hrs. On completion, the mixture was concentrated in vacuo to give the title compound (70.0 mg, 98% yield, TFA) as a yellow solid. LC-MS (ESI$^+$) m/z 653.4 (M+H)$^+$.

Tert-butyl N-[1-(4-formylcyclohexyl)-3-(trifluoromethyl)pyrazol-4-yl]carbamate (Intermediate AFS)

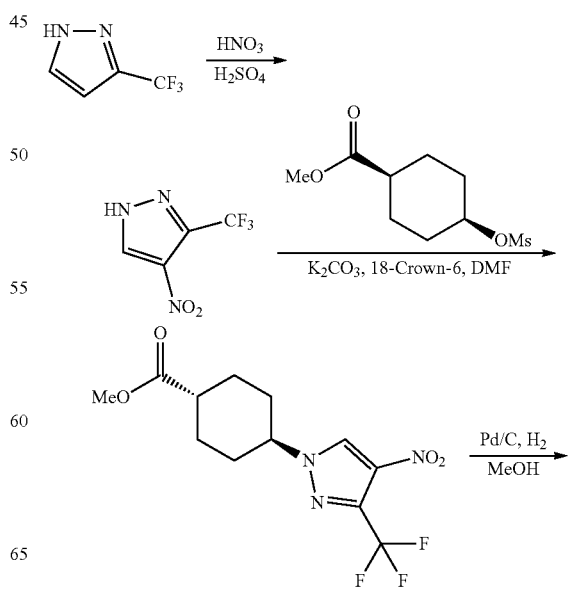

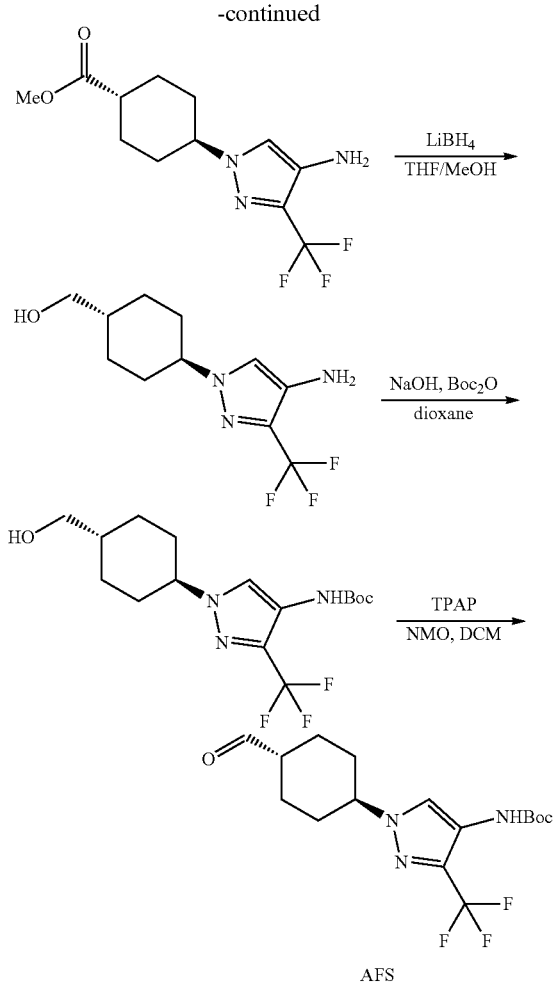

AFS

Step 1—4-Nitro-3-(trifluoromethyl)-1H-pyrazole

To a mixture of 3-(trifluoromethyl)-1H-pyrazole (3.5 g, 25.7 mmol, CAS #1087160-38-0) in $H_2SO_4$ (10 mL) was added dropwise $HNO_3$ (4.86 g, 77.2 mmol, 3.47 mL, 65% con.) at 0° C. The mixture was stirred at 0° C. for 10 min, then heated to 115° C. and stirred for 3 hours. On completion, the cooled mixture was poured into ice-water (10 mL), and extracted with EA (3×20 mL). The combined organic phase was dried with $Na_2SO_4$, filtered and the filtrate was concentrated in vacuo to give a residue. The residue was purified by column chromatography ($SiO_2$, Petroleum ether/ Ethyl acetate=20/1 to 5/1) to afford the title compound (4.40 g, 94% yield) as a white solid. $^1H$ NMR (400 MHz, DMSO-$d_6$) δ 14.69 (s, 1H), 9.13 (s, 1H).

Step 2—Methyl 4-[4-nitro-3-(trifluoromethyl)pyrazol-1-yl]cyclohexanecarboxylate To a mixture of 4-nitro-3-(trifluoromethyl)-1H-pyrazole (4.1 g, 22.6 mmol) and methyl 4-methyl sulfonyloxycyclohexanecarboxylate (5.35 g, 22.6 mmol, Step 1 of Intermediate QS) in DMF (50 mL) was added $K_2CO_3$ (9.39 g, 67.9 mmol) and 18-crown-6 (1.20 g, 4.53 mmol) in one portion at 25° C. The mixture was stirred at 85° C. for 24 hours. On completion, the mixture was filtered to remove the insoluble solid and the filtrate was concentrated to give a residue. The residue was diluted with water (50 mL) and extracted with EA (3×40 mL). The combined organic phase was dried over $Na_2SO_4$, filtered and concentrated in vacuo to give a residue. The residue was purified by column chromatography ($SiO_2$, Petroleum ether/Ethyl acetate=20/1 to 3/1) to give the title compound (2.70 g, 37% yield) as white solid. $^1H$ NMR (400 MHz, DMSO-$d_6$) δ 9.18 (s, 1H), 4.91-4.72 (m, 1H), 4.43-4.35 (m, 1H), 3.61 (s, 3H), 2.47-2.38 (m, 2H), 2.18-1.99 (m, 4H), 1.58-1.47 (m, 2H).

Step 3—Methyl 4-[4-amino-3-(trifluoromethyl)pyrazol-1-yl]cyclohexanecarboxylate To a solution of methyl 4-[4-nitro-3-(trifluoromethyl)pyrazol-1-yl]cyclohexanecarboxylate (2.40 g, 7.47 mmol) in MeOH (20 mL) was added Pd/C (80.0 mg, 10% wt) under $N_2$. The suspension was degassed under vacuum and purged with $H_2$ three times. The mixture was stirred at 25° C. for 16 hours under $H_2$ (15 psi). On completion, the mixture was filtered and the filtrate was concentrated in vacuo to give a residue. The residue was purified by column chromatography ($SiO_2$, Petroleum ether/Ethyl acetate=10/1 to 3/1) to give the title compound (900 mg, 41% yield) as red solid. $^1H$ NMR (400 MHz, DMSO-$d_6$) δ 7.22 (s, 1H), 4.30-4.14 (m, 2H), 4.12-4.00 (m, 1H), 3.61 (s, 3H), 2.40 (s, 1H), 2.07-1.91 (m, 4H), 1.79-1.64 (m, 2H), 1.58-1.42 (m, 2H); LC-MS (ESI$^+$) m/z 292.2 (M+H)$^+$.

Step 4—[4-[4-Amino-3-(trifluoromethyl)pyrazol-1-yl]cyclohexyl]methanol

To a mixture of methyl 4-[4-amino-3-(trifluoromethyl)pyrazol-1-yl]cyclohexanecarboxylate (890 mg, 3.06 mmol) in a mixed solvent of THF (15 mL) and MeOH (3 mL) was added LiBH$_4$ (166 mg, 7.64 mmol) at 25° C. The mixture was stirred at 40° C. for 3 hours. On completion, the reaction mixture was quenched by adding water (10 mL) dropwise at 0° C., then diluted with EA (15 mL) and extracted with EA (3×30 mL). The combined organic layers were washed with brine (15 mL), dried over $Na_2SO_4$, filtered and concentrated in vacuo to give the title compound (725 mg, 90% yield) as red solid. LC-MS (ESI$^+$) m/z 264.1 (M+H)$^+$.

Step 5—Tert-butyl N-[1-[4-(hydroxymethyl)cyclohexyl]-3-(trifluoromethyl)pyrazol-4-yl]carbamate To a mixture of [4-[4-amino-3-(trifluoromethyl)pyrazol-1-yl]cyclohexyl]methanol (720 mg, 2.73 mmol) in dioxane (15 mL) was added NaOH (1 M, 10.9 mL) in one portion at 25° C. The mixture was stirred at 25° C. for 30 min, then Boc$_2$O (1.79 g, 8.20 mmol) was added, and the mixture was stirred at 25° C. for 2.5 hrs. On completion, the reaction mixture was diluted with EA (20 mL) and extracted with EA (3×30 mL). The combined organic layers were washed with brine (10 mL), dried over $Na_2SO_4$, filtered and concentrated in vacuo to give the title compound (650 mg, 65% yield) as red solid. LC-MS (ESI$^+$) m/z 364.2 (M+H)$^+$.

Step 6—Tert-butyl N-[1-(4-formylcyclohexyl)-3-(trifluoromethyl)pyrazol-4-yl]carbamate To a mixture of tert-butyl N-[1-[4-(hydroxymethyl)cyclohexyl]-3-(trifluoromethyl)pyrazol-4-yl] carbamate (520 mg, 1.43 mmol) in DCM (5 mL) was added TPAP (75.4 mg, 214.65 umol) and NMO (335 mg, 2.86 mmol) in one portion at 25° C. The mixture was stirred at 25° C. for 2 hours. On completion, the mixture was filtered and the filtrate was diluted with H₂O (10 mL), and extracted with DCM (3×20 mL). The combined organic phase was dried over Na₂SO₄, filtered and concentrated in vacuo to give a residue. The residue was purified by column chromatography (SiO₂, Petroleum ether/Ethyl acetate=20/1 to 10/1) to afford the title compound (180 mg, 35% yield) as white solid. ¹H NMR (400 MHz, CDCl₃) δ 9.69 (s, 1H), 7.98 (s, 1H), 6.47 (s, 1H), 4.14-4.03 (m, 1H), 2.36-2.15 (m, 5H), 1.91-1.78 (m, 2H), 1.52 (s, 9H), 1.48-1.39 (m, 2H).

3-[4-[3-[[1-[[4-[4-Amino-3-(trifluoromethyl)pyrazol-1-yl]cyclohexyl]methyl]-4-piperidyl]oxy] propyl]-3-methyl-2-oxo-benzimidazol-1-yl]piperidine-2,6-dione (Intermediate AFT)

were added. The mixture was stirred at 0° C. for another 30 mins. Finally, NaBH(OAc)₃ (64.5 mg, 304 umol) was added, and the mixture was stirred at 0° C. for 2 hours. On completion, the mixture was quenched with H₂O (0.2 mL), and then concentrated in vacuo to give a residue. The residue was purified by reverse phase (0.1% FA condition) to afford the title compound (98.0 mg, 86% yield) as yellow solid. ¹H NMR (400 MHz, DMSO-d₆) δ 11.10 (s, 1H), 8.66 (s, 1H), 7.97 (s, 1H), 6.97 (d, J=4.8 Hz, 2H), 6.91-6.86 (m, 1H), 5.45-5.28 (m, 1H), 4.19-4.12 (m, 1H), 3.57 (s, 3H), 3.50-3.42 (m, 2H), 3.33-3.25 (m, 1H), 2.99-2.85 (m, 3H), 2.77-2.58 (m, 4H), 2.16-1.66 (m, 15H), 1.63-1.47 (m, 3H), 1.43 (s, 9H), 1.07-0.97 (m, 2H); LC-MS (ESI⁺) m/z 746.5 (M+H)⁺.

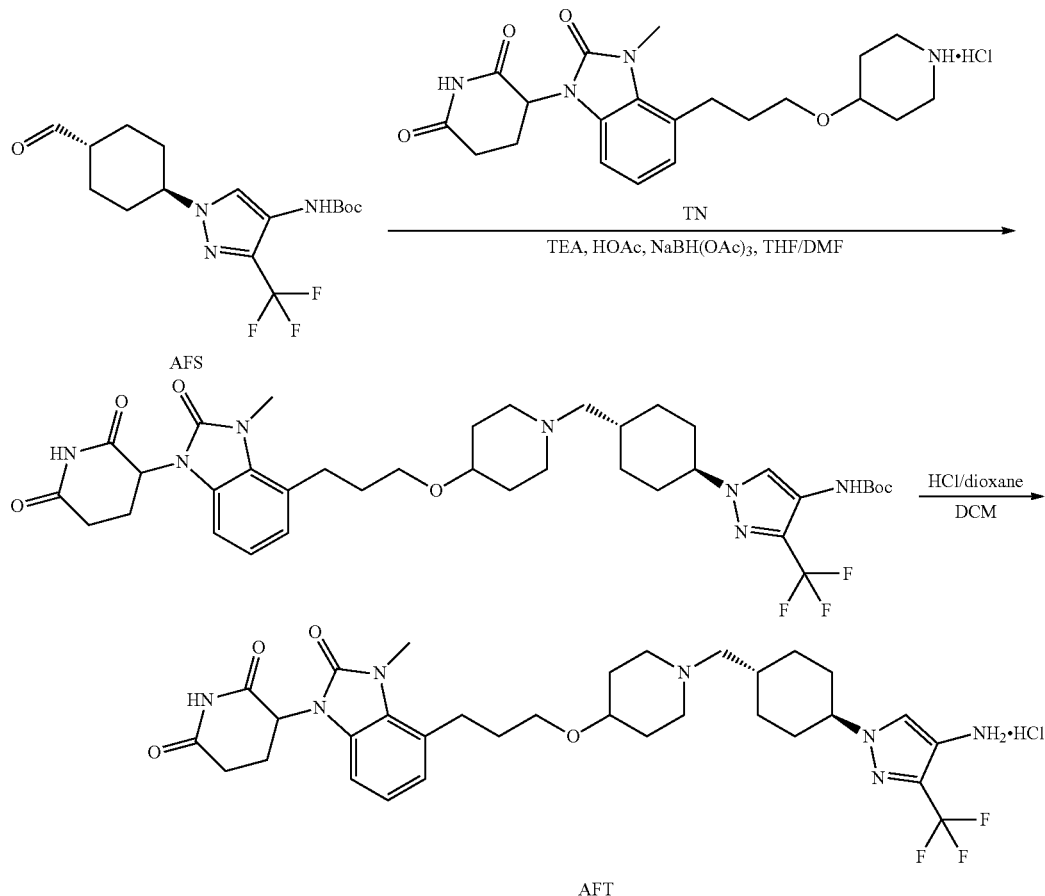

Step 1—Tert-butyl N-[1-[4-[[4-[3-[1-(2,6-dioxo-3-piperidyl)-3-methyl-2-oxo-benzimidazol-4-yl]propoxy]-1-piperidyl]methyl]cyclohexyl]-3-(trifluoromethyl)pyrazol-4-yl]carbamate To a mixture of 3-[3-methyl-2-oxo-4-[3-(4-piperidyloxy) propyl]benzimidazol-1-yl]piperidine-2,6-dione (60.9 mg, 152 umol, HCl salt, Intermediate TN) in a mixed solvent of THF (5 mL) and DMF (1 mL) was added TEA (15.4 mg, 152 umol, 21.2 uL) at 0° C. The mixture was stirred at 0° C. for 30 mins. Then, tert-butyl N-[1-(4-formylcyclohexyl)-3-(trifluoromethyl)pyrazol-4-yl]carbamate (55 mg, 152 umol, Intermediate AFS) and HOAc (9.14 mg, 152 umol, 8.70 uL)

Step 2—3-[4-[3-[[1-[[4-[4-Amino-3-(trifluoromethyl)pyrazol-1-yl] cyclohexyl]methyl]-4-piperidyl] oxy] propyl]-3-methyl-2-oxo-benzimidazol-1-yl] piperidine-2,6-dione To a mixture of tert-butyl N-[1-[4-[[4-[3-[1-(2,6-dioxo-3-piperidyl)-3-methyl-2-oxo-benzimidazol-4-yl]propoxy]-1-piperidyl]methyl]cyclohexyl]-3-(trifluoromethyl)pyrazol-4-yl]carbamate (88.0 mg, 117 umol) in DCM (3 mL) was added HCl/dioxane (4 M, 3.0 mL) at 25° C. The mixture was stirred at 25° C. for 2 hours. On completion, the mixture was concentrated in vacuo to give the title compound (80 mg, 99% yield, HCl salt) as yellow solid. LC-MS (ESI⁺) m/z 646.4 (M+H)⁺.

3-(5-Fluoro-2-methyl-4-oxo-quinazolin-3-yl)piperidine-2,6-dione (Intermediate AFU)

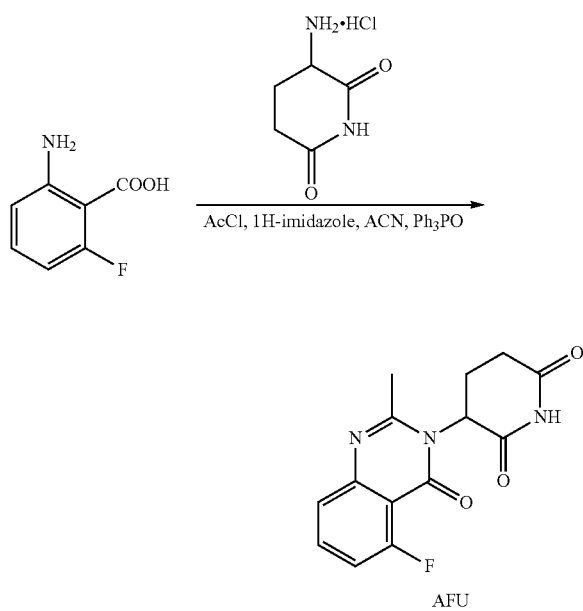

To a solution of 2-amino-6-fluoro-benzoic acid (5.00 g, 32.2 mmol, CAS #434-76-4) and 1H-imidazole (2.63 g, 38.6 mmol) in ACN (150 mL) was added acetyl chloride (3.04 g, 38.6 mmol, 2.76 mL) at 25° C. The mixture was stirred at 25° C. for 16 hours. Then 3-aminopiperidine-2,6-dione (5.84 g, 35.4 mmol, HCl salt), another batch of 1H-imidazole (4.83 g, 70.9 mmol) and triphenyl phosphite (12.0 g, 38.6 mmol, 10.2 mL) was added. The mixture was stirred at 80° C. for 22 hours. On completion, the reaction mixture was concentrated in vacuo to give a residue. The residue was diluted with H$_2$O (100 mL) and stirred until a large amount of solid appeared. The mixture was filtered and the filter cake was washed with water (100 mL) and EA (3×20 mL). Finally, the solid was collected and dried in vacuo to afford the title compound (8.50 g, 91% yield) as white solid. $^1$H NMR (400 MHz, DMSO-d$_6$) δ 11.09 (s, 1H), 7.80 (d, J=5.6 Hz, 1H), 7.44 (d, J=8.4 Hz, 1H), 7.30-7.22 (m, 1H), 5.28-5.24 (m, 1H), 2.91-2.78 (m, 1H), 2.68-2.59 (m, 5H), 2.22-2.12 (m, 1H); LC-MS (ESI$^+$) m/z 290.1 (M+H)$^+$.

3-[2-Methyl-4-oxo-5-[3-(4-piperidyloxy)propylamino]quinazolin-3-yl]piperidine-2,6-dione (Intermediate AFV)

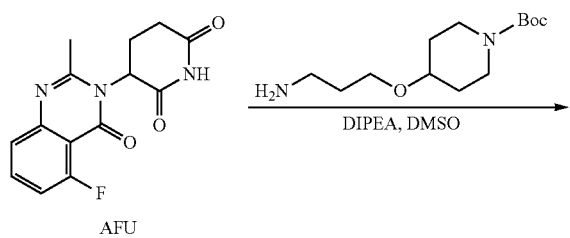

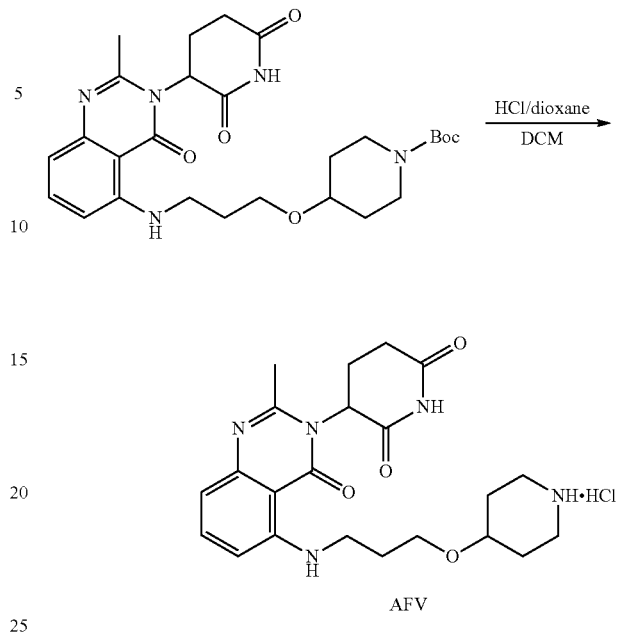

Step 1—Tert-butyl 4-[3-[[3-(2,6-dioxo-3-piperidyl)-2-methyl-4-oxo-quinazolin-5-yl]amino]propoxy]piperidine-1-carboxylate To a mixture of 3-(5-fluoro-2-methyl-4-oxo-quinazolin-3-yl) piperidine-2,6-dione (150 mg, 518 umol, Intermediate AFU) and tert-butyl 4-(3-aminopropoxy)piperidine-1-carboxylate (200 mg, 777 umol, CAS #771572-33-9) in DMSO (5 mL) was added DIPEA (167 mg, 1.30 mmol) at 25° C. The mixture was stirred at 130° C. for 3 hours. On completion, the reaction mixture was quenched by water (2 mL) at 25° C., and then diluted with DCM (10 mL) and extracted with DCM (3×20 mL). The combined organic layers were washed with brine (10 mL), dried over Na$_2$SO$_4$, filtered and concentrated in vacuo to give a residue. The residue was purified reverse phase (0.1% FA condition) to give the title compound (156 mg, 57% yield) as a yellow solid. $^1$H NMR (400 MHz, DMSO-d$_6$) δ 10.94 (s, 1H), 8.39 (s, 1H), 7.48 (s, 1H), 6.63 (d, J=7.8 Hz, 1H), 6.51 (d, J=8.4 Hz, 1H), 5.21-5.12 (m, 1H), 8.40 (s, 1H), 3.63-3.55 (m, 2H), 3.51 (t, J=5.0 Hz, 3H), 3.45-3.40 (m, 3H), 3.27-3.16 (m, 3H), 3.06-2.95 (m, 2H), 2.89-2.76 (m, 1H), 2.55 (s, 3H), 2.19-2.09 (m, 1H), 1.90-1.65 (m, 5H), 1.38 (s, 9H); LC-MS (ESI$^+$) m/z 528.2 (M+H)$^+$.

Step 2—3-[2-Methyl-4-oxo-5-[3-(4-piperidyloxy)propylamino]quinazolin-3-yl]piperidine-2,6-dione; hydrochloride To a mixture of tert-butyl 4-[3-[[3-(2,6-dioxo-3-piperidyl)-2-methyl-4-oxo-quinazolin-5-yl]amino] propoxy]piperidine-1-carboxylate (60.0 mg, 113 umol) in DCM (3 mL) was added HCl/dioxane (4 M, 3.00 mL) at 25° C. The mixture was stirred at 25° C. for 2 hours. On completion, the reaction mixture was concentrated in vacuo to give the title product (56.0 mg, 98% yield) was as yellow solid. LC-MS (ESI$^+$) m/z 428.2 (M+H)$^+$.

1823

Benzyl 4-[3-(methylamino)propoxy]piperidine-1-carboxylate (Intermediate AFW)

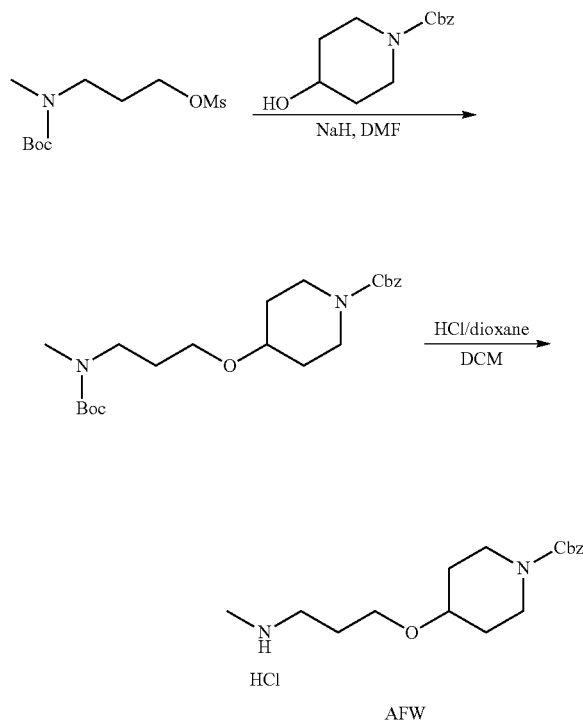

Step 1—Benzyl 4-[3-[tert-butoxycarbonyl(methyl)amino]propoxy]piperidine-1-carboxylate To a solution of benzyl 4-hydroxypiperidine-1-carboxylate (1.32 g, 5.61 mmol, Intermediate ACB) in DMF (20 mL) was added NaH (336 mg, 8.42 mmol, 60% dispersion in mineral oil) at 0° C. The mixture was stirred at 0° C. for 0.5 hr. After that, 3-[tert-butoxycarbonyl(methyl)amino]propyl methanesulfonate (1.50 g, 5.61 mmol, synthesized via Step 1 of Intermediate AAH) was added. The mixture was stirred at 60° C. for 48 hrs. On completion, the reaction mixture was quenched with water (40 mL) and extracted with EA (3×20 mL). The combined organic layers were dried over $Na_2SO_4$, filtered and concentrated in vacuo to give a residue. The residue was purified by column chromatography ($SiO_2$, PE/EA=2/1) to give the title compound (0.80 g, 34% yield) as light yellow oil. $^1$H NMR (400 MHz, $CDCl_3$) δ 7.40-7.31 (m, 4H), 5.13 (s, 2H), 3.85-3.72 (m, 2H), 3.50-3.40 (m, 3H), 3.34-3.18 (m, 4H), 2.85 (s, 3H), 1.86-1.74 (m, 4H), 1.54 (d, J=6.4 Hz, 2H), 1.46 (s, 9H).

Step 2—Benzyl 4-[3-(methylamino)propoxy]piperidine-1-carboxylate

To a solution of benzyl 4-[3-[tert-butoxycarbonyl(methyl)amino]propoxy]piperidine-1-carboxylate (0.50 g, 1.23 mmol) in DCM (7 mL) was added HCl/dioxane (4 M, 7.50 mL). The reaction mixture was stirred at 15° C. for 1.5 hrs. The mixture was concentrated in vacuo to give the title compound (0.42 g, 98% yield, HCl) as light yellow solid. LC-MS (ESI$^+$) m/z 307.2 (M+H)$^+$.

1824

2-(2,6-Dioxo-3-piperidyl)-4-[methyl-[3-(4-piperidyloxy)propyl]amino]isoindoline-1,3-dione (Intermediate AFX)

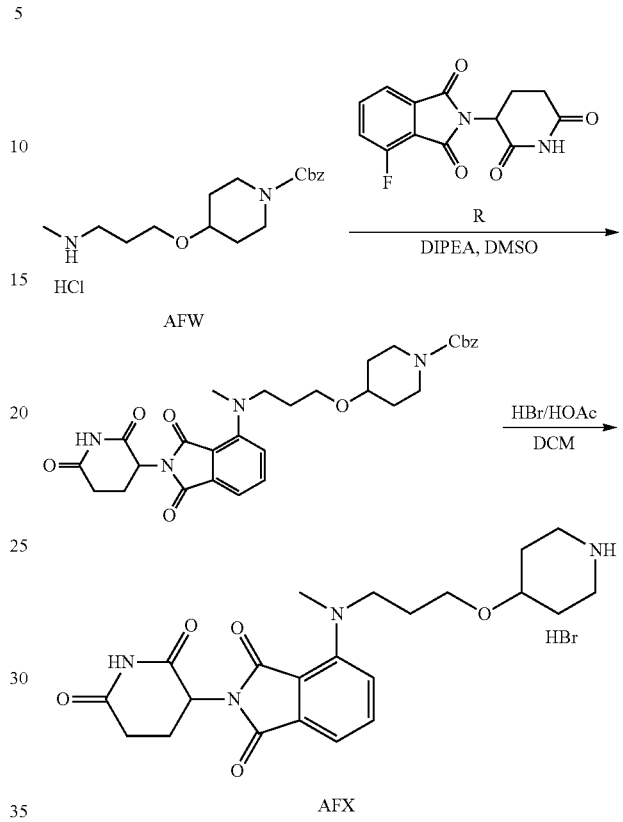

Step 1—Benzyl 4-[3-[[2-(2,6-dioxo-3-piperidyl)-1,3-dioxo-isoindolin-4-yl]-methyl-amino]propoxy]piperidine-1-carboxylate To a solution of 2-(2,6-dioxo-3-piperidyl)-4-fluoro-isoindoline-1,3-dione (160 mg, 579 umol, Intermediate R) in DMSO (3 mL) was added DIPEA (224 mg, 1.74 mmol) and benzyl 4-[3-(methylamino) propoxy]piperidine-1-carboxylate (198 mg, 579 umol, HCl, Intermediate AFW). The reaction mixture was stirred at 130° C. for 16 hrs. On completion, the reaction mixture was diluted with water (6 mL), and then extracted with EA (4×10 mL). The combined organic layers were dried over $Na_2SO_4$, filtered and concentrated in vacuo to give a residue. The residue was purified by prep-HPLC (FA condition) to give the title compound (0.24 g, 73% yield) as yellow solid. $^1$H NMR (400 MHz, $CDCl_3$) δ 8.46-8.06 (m, 1H), 7.51 (dd, J=7.2, 8.4 Hz, 1H), 7.40-7.27 (m, 6H), 7.15 (d, J=8.8 Hz, 1H), 5.12 (s, 2H), 4.94 (dd, J=5.2, 12.0 Hz, 1H), 3.80-3.67 (m, 2H), 3.65-3.55 (m, 2H), 3.46 (t, J=6.0 Hz, 2H), 3.41-7.35 (m, 1H), 3.26-3.15 (m, 2H), 3.08 (s, 3H), 2.90-2.68 (m, 3H), 2.17-2.06 (m, 1H), 1.98-1.87 (m, 2H), 1.82-1.68 (m, 2H), 1.57-1.43 (m, 2H); LC-MS (ESI$^+$) m/z 563.2 (M+H)$^+$.

Step 2—2-(2,6-Dioxo-3-piperidyl)-4-[methyl-[3-(4-piperidyloxy)propyl]amino]isoindoline-1,3-dione To a solution of benzyl 4-[3-[[2-(2,6-dioxo-3-piperidyl)-1,3-dioxo-isoindolin-4-yl]-methyl-amino] propoxy]piperidine-1-carboxylate (210 mg, 373 umol) in DCM (4 mL) was added HBr/HOAc (88.8 umol, 4 mL, 35% solution). The mixture was stirred at 15° C. for 6 hours. On completion, the reaction mixture was concentrated in vacuo to give the title compound (180 mg, 95% yield, HBr) as yellow solid. LC-MS (ESI$^+$) m/z 429.4 (M+H)$^+$.

Benzyl 4-(4-piperidylmethoxy)piperidine-1-carboxylate (Intermediate AFY)

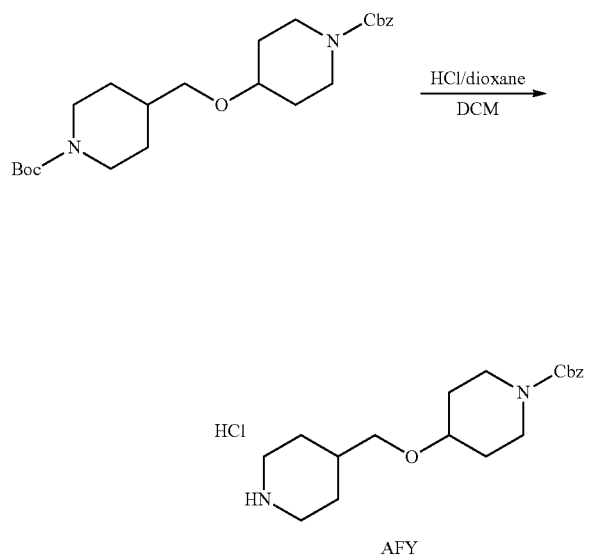

To a solution of tert-butyl 4-[(1-benzyloxycarbonyl-4-piperidyl)oxymethyl]piperidine-1-carboxylate (0.8 g, 1.85 mmol, synthesized via Steps 1-3 of Intermediate ACC) in DCM (9 mL) was added HCl/dioxane (4 M, 9 mL). The mixture was stirred at 15° C. for 2 hrs. On completion, the reaction mixture was concentrated in vacuo to give the title compound (0.68 g, 98% yield, HCl) as white solid. LC-MS (ESI$^+$) m/z 333.2 (M+H)$^+$.

2-(2,6-Dioxo-3-piperidyl)-4-[4-(4-piperidyloxymethyl)-1-piperidyl]isoindoline-1,3-dione (Intermediate AFZ)

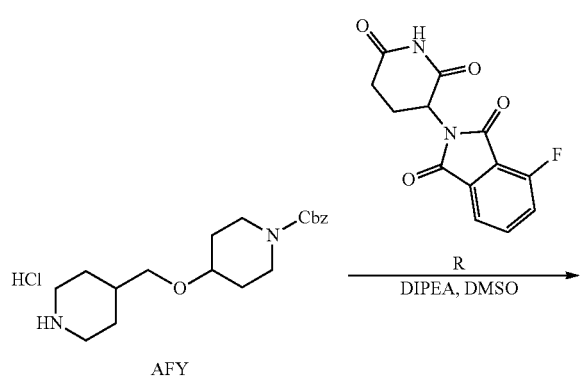

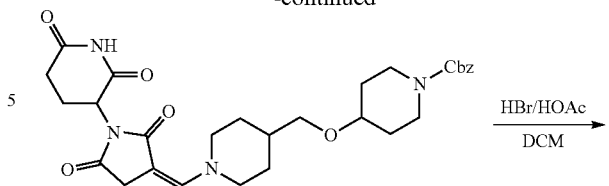

Step 1—Benzyl 4-[[1-[2-(2,6-dioxo-3-piperidyl)-1,3-dioxo-isoindolin-4-yl]-4-piperidyl]methoxy]piperidine-1-carboxylate To a solution of 2-(2,6-dioxo-3-piperidyl)-4-fluoro-isoindoline-1,3-dione (440 mg, 1.59 mmol, Intermediate R) in DMSO (8 mL) was added DIPEA (1.24 g, 9.56 mmol) and benzyl 4-(4-piperidylmethoxy) piperidine-1-carboxylate (587 mg, 1.59 mmol, HCl, Intermediate AFY). The reaction mixture was stirred at 130° C. for 16 hrs. On completion, the reaction was quenched with water (30 mL), and then extracted with EA (3×30 mL). The combined organic layers were dried over Na$_2$SO$_4$, filtered and concentrated in vacuo to give a residue. The residue was purified by prep-HPLC (FA condition) to give the title compound (0.70 g, 74% yield) as yellow solid. $^1$H NMR (400 MHz, CDCl$_3$) δ 8.21 (s, 1H), 7.58 (dd, J=7.6, 8.0 Hz, 1H), 7.41-7.29 (m, 6H), 7.20 (d, J=8.4 Hz, 1H), 5.14 (s, 2H), 4.97 (dd, J=5.2, 11.6 Hz, 1H), 3.85-3.70 (m, 4H), 3.50-3.44 (m, 1H), 3.37 (d, J=6.0 Hz, 2H), 3.33-3.23 (m, 2H), 2.97-2.70 (m, 5H), 2.15-2.07 (m, 1H), 1.91 (d, J=12.8 Hz, 2H), 1.87-1.72 (m, 3H), 1.62-1.46 (m, 4H).

Step 2—2-(2,6-Dioxo-3-piperidyl)-4-[4-(4-piperidyloxymethyl)-1-piperidyl]isoindoline-1,3-dione To a solution of benzyl 4-[[1-[2-(2,6-dioxo-3-piperidyl)-1,3-dioxo-isoindolin-4-yl]-4-piperidyl] methoxy]piperidine-1-carboxylate (0.60 g, 1.02 mmol) in DCM (6 mL) was added HBr/HOAc (6 mL, 35% solution). The mixture was stirred at 15° C. for 2 hours. On completion, the mixture was dried under nitrogen to give the title compound (0.54 g, 96% yield, HBr) as yellow solid. LC-MS (ESI$^+$) m/z 455.2 (M+H)$^+$.

4-[4-[[1-[[4-[4-Amino-3-(difluoromethyl)pyrazol-1-yl]cyclohexyl]methyl]-4-piperidyl] oxymethyl]-1-piperidyl]-2-(2,6-dioxo-3-piperidyl)isoindoline-1,3-dione (Intermediate AGA)

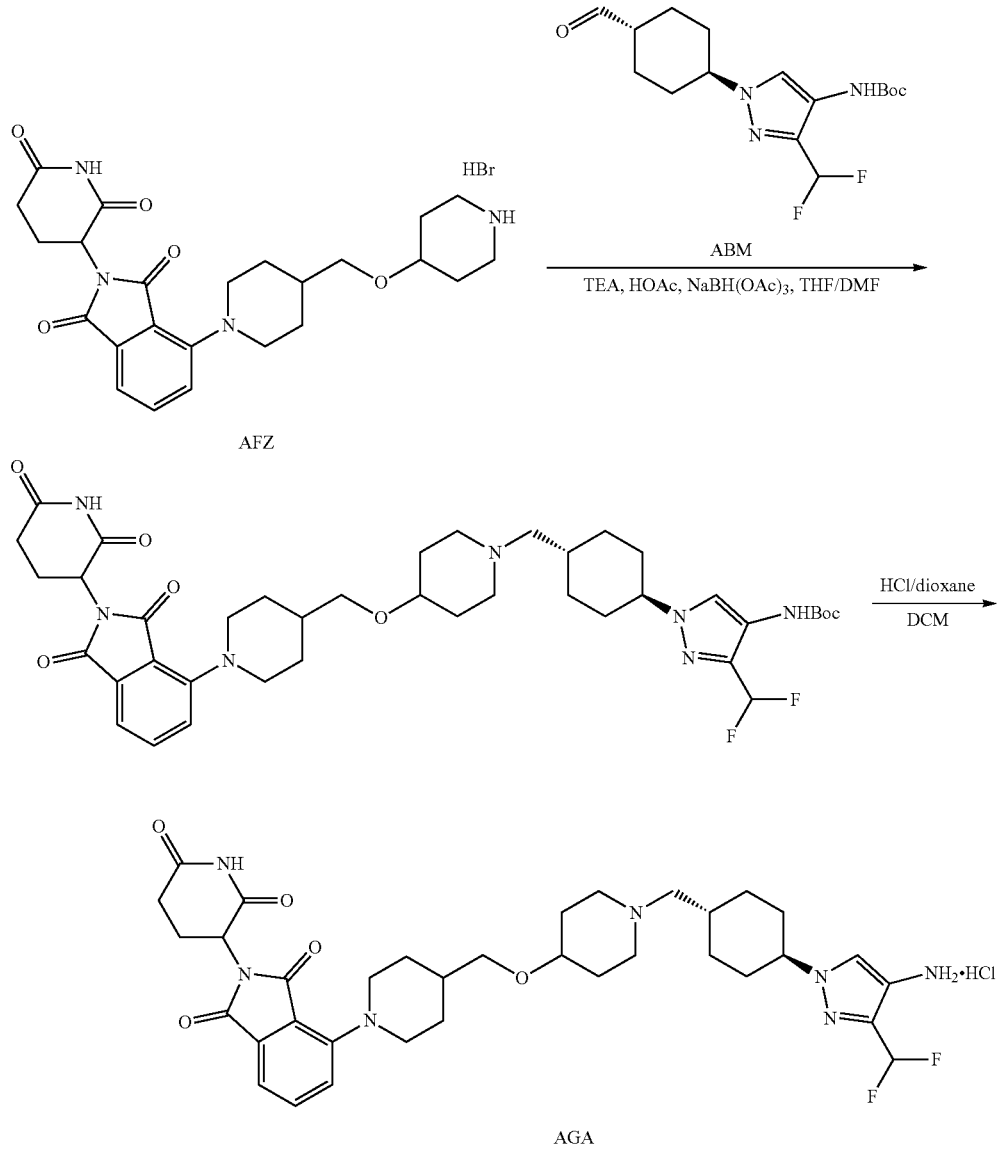

Step 1—Tert-butyl N-[3-(difluoromethyl)-1-[4-[[4-[[1-[2-(2,6-dioxo-3-piperidyl)-1,3-dioxo-isoindolin-4-yl]-4-piperidyl]methoxy]-1-piperidyl]methyl]cyclohexyl]pyrazol-4-yl]carbamate To a mixture of 2-(2,6-dioxo-3-piperidyl)-4-[4-(4-piperidyloxymethyl)-1-piperidyl]isoindoline-1,3-dione (150 mg, 280 umol, HBr, Intermediate AFZ) in a mixed solvent of THF (3 mL) and DMF (0.7 mL) was added TEA (85.0 mg, 840 umol) at −10° C. The mixture was stirred at −10° C. for 6 mins. Then HOAc (50.4 mg, 840 umol) and tert-butyl N-[3-(difluoromethyl)-1-(4-formylcyclohexyl)pyrazol-4-yl] carbamate (96.1 mg, 280 umol, Intermediate ABM) were added. The mixture was stirred at −10° C. for 30 mins. After that, NaBH(OAc)$_3$ (89.0 mg, 420 umol) was added at −10° C., the mixture was stirred −10° C. for 1 hr. On completion, the reaction was quenched by water (10 mL) and then extracted with DCM (3×15 mL). The combined organic layers were dried over Na$_2$SO$_4$, filtered and concentrated in vacuo to give a residue. The residue was purified by prep-HPLC (TFA condition) to give the title compound (170 mg, 77% yield) as yellow solid. $^1$H NMR (400 MHz, CDCl$_3$) δ 12.03-11.81 (m, 1H), 8.08 (s, 1H), 7.90 (s, 1H), 7.65-7.56 (m, 1H), 7.40 (d, J=7.2 Hz, 1H), 7.19 (d, J=8.4 Hz, 1H), 6.88-6.51 (m, 2H), 4.97 (dd, J=5.2, 11.6 Hz, 1H), 4.07-3.95 (m, 1H), 3.82-3.68 (m, 3H), 3.46 (d, J=10.4 Hz, 2H), 3.36 (d, J=6.0 Hz, 2H), 2.98-2.86 (m, 6H), 2.85-2.67 (m, 4H), 2.20-2.18 (m, 3H), 2.15-2.08 (m, 1H), 2.07-1.96 (m, 4H), 1.88 (d, J=12.0 Hz, 3H), 1.83-1.70 (m, 3H), 1.65-1.55 (m, 2H), 1.51 (s, 9H), 1.33-1.19 (m, 2H).

Step 2—4-[4-[[1-[[4-[4-Amino-3-(difluoromethyl) pyrazol-1-yl] cyclohexyl]methyl]-4-piperidyl] oxymethyl]-1-piperidyl]-2-(2,6-dioxo-3-piperidyl) isoindoline-1,3-dione To a solution of tert-butyl N-[3-(difluoromethyl)-1-[4-[[4-[[1-[2-(2,6-dioxo-3-piperidyl)-1,3-dioxo-isoindolin-4-yl]-4-piperidyl]methoxy]-1-piperidyl]methyl]cyclohexyl]pyrazol-4-yl]carbamate (160 mg, 204 umol) in DCM (3 mL) was added HCl/dioxane (4 M, 3 mL). The mixture was stirred at 15° C. for 2 hrs. On completion, the reaction was concentrated in vacuo to give the title compound (146 mg, 98% crude yield, HCl) as yellow solid. LC-MS (ESI$^+$) m/z 682.4 (M+H)$^+$.

2-(2,6-Dioxo-3-piperidyl)-4-(4-piperidylamino) isoindoline-1,3-dione (Intermediate AGB)

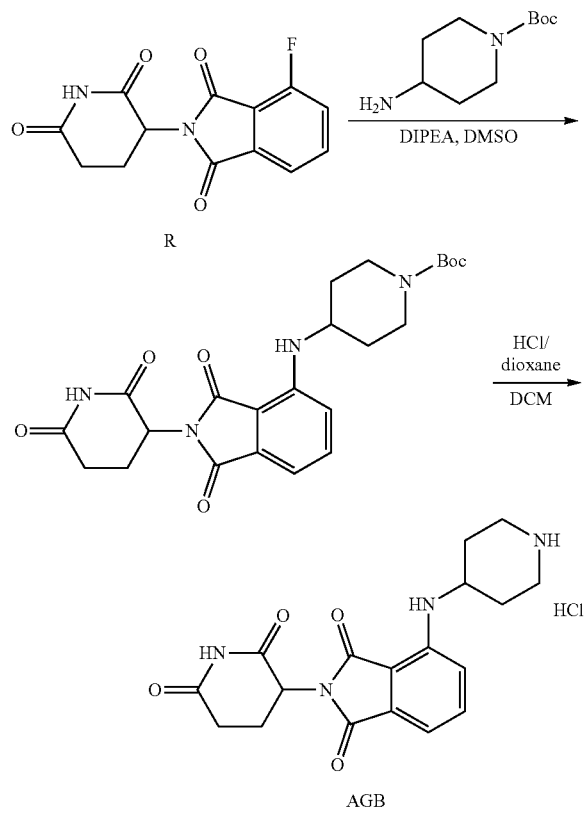

Step 1—Tert-butyl 4-((2-(2,6-dioxopiperidin-3-yl)-1,3-dioxoisoindolin-4-yl)amino)piperidine-1-carboxylate To a solution of 2-(2,6-dioxo-3-piperidyl)-4-fluoro-isoindoline-1,3-dione (500 mg, 1.81 mmol, Intermediate R) and tert-butyl 4-aminopiperidine-1-carboxylate (362 mg, 1.81 mmol, CAS #87120-72-7) in DMSO (6 mL) was added DIPEA (701 mg, 5.43 mmol, 945 uL). The reaction mixture was stirred at 130° C. for 3 hrs. On completion, the mixture was concentrated in vacuo to give a residue; the residue was purified by reverse phase (0.1% FA condition) to give the title compound (550 mg, 66.5% yield) as a yellow solid. $^1$H NMR (400 MHz, DMSO-d$_6$) δ 11.11 (s, 1H), 7.65-7.56 (m, 1H), 7.22 (d, J=8.8 Hz, 1H), 7.06 (d, J=7.2 Hz, 1H), 6.28 (d, J=8.0 Hz, 1H), 5.06 (dd, J=5.2, 12.8 Hz, 1H), 3.98-3.84 (m, 2H), 3.82-3.70 (m, 1H), 3.05-2.82 (m, 3H), 2.65-2.52 (m, 2H), 2.07-1.99 (m, 1H), 1.97-1.86 (m, 2H), 1.41 (s, 9H), 1.40-1.33 (m, 2H); LC-MS (ESI$^+$) m/z 479.2 (M+Na)$^+$.

Step 2—2-(2,6-Dioxo-3-piperidyl)-4-(4-piperidylamino)isoindoline-1,3-dione

To a solution of tert-butyl 4-[[2-(2,6-dioxo-3-piperidyl)-1,3-dioxo-isoindolin-4-yl]amino]piperidine-1-carboxylate (100 mg, 219 umol) in DCM (4 mL) was added HCl/dioxane (4 M, 2 mL). The reaction mixture was stirred at 20° C. for 1 hr. On completion, the mixture was concentrated in vacuo to give the title compound (85.0 mg, 98% yield, HCl) as a yellow solid. LC-MS (ESI$^+$) m/z 357.2 (M+H)$^+$.

3-(3-Aminopropoxy)propan-1-ol (Intermediate AGC)

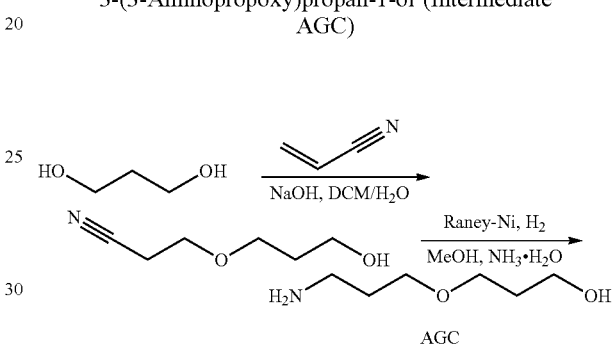

Step 1—3-(3-Hydroxypropoxy)propanenitrile

To a mixture of prop-2-enenitrile (4.0 g, 75.3 mmol, 5.00 mL, CAS #107-13-1) and propane-1,3-diol (17.2 g, 226 mmol, 16.4 mL, CAS #504-63-2) in a mixed solvent of CH$_2$Cl$_2$ (150 mL) and H$_2$O (150 mL) was added NaOH (11.5 g, 286 mmol) at 25° C. The mixture was stirred at 25° C. for 16 hours. On completion, the mixture was extracted with DCM (3×50 mL), and then washed with brine (2×15 mL). The combined organic phase was dried over Na$_2$SO$_4$, filtered and concentrated in vacuo to give a residue. The residue was purified by column chromatography (SiO$_2$, petroleum ether/ethyl acetate=3/1 to 1/1) to afford the title compound (3.3 g, 34% yield). $^1$H NMR (400 MHz, CDCl$_3$) δ 3.74 (t, J=6.0 Hz, 2H), 3.68-3.61 (m, 4H), 2.60 (t, J=6.0 Hz, 2H), 1.90-1.76 (m, 2H).

Step 2—3-(3-Aminopropoxy)propan-1-ol

To a solution of 3-(3-hydroxypropoxy)propanenitrile (2.80 g, 21.6 mmol) in MeOH (6 mL) was added NH$_3$—H$_2$O (6.08 g, 43.4 mmol, 6.68 mL, 25% solution) and Raney-Ni (2.79 g, 32.5 mmol) under N$_2$. The suspension was degassed under vacuum and purged with H$_2$ three times. The mixture was stirred at 25° C. for 16 hours under H$_2$ (50 psi). On completion, the mixture was filtered and the filtrate was concentrated in vacuo to give the title product (2.80 g, 97% yield) as colorless oil. $^1$H NMR (400 MHz, CDCl$_3$) δ 3.78 (t, J=5.6 Hz, 2H), 3.63 (t, J=5.6 Hz, 2H), 3.54 (t, J=6.0 Hz, 2H), 2.81 (t, J=6.4 Hz, 2H), 1.86-1.81 (m, 2H), 1.73 (t, J=6.4 Hz, 2H).

3-[3-[[2-(2,6-Dioxo-3-piperidyl)-1,3-dioxo-isoindolin-4-yl]amino]propoxy]propanal (Intermediate AGD)

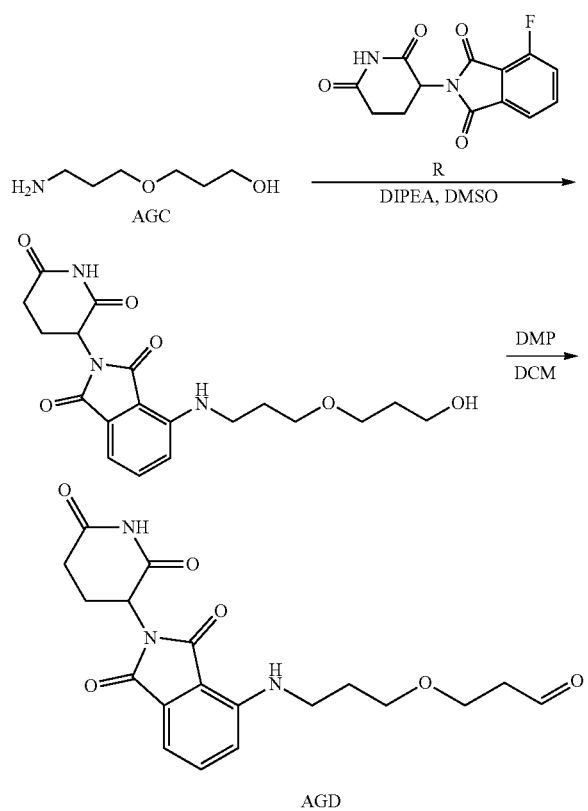

Step 1—2-(2,6-Dioxo-3-piperidyl)-4-[3-(3-hydroxypropoxy)propylamino]isoindoline-1,3-dione To a mixture of 2-(2,6-dioxo-3-piperidyl)-4-fluoro-isoindoline-1,3-dione (394 mg, 1.43 mmol, Intermediate R) and 3-(3-aminopropoxy)propan-1-ol (380 mg, 2.85 mmol, Intermediate AGC) in DMSO (15 mL) was added DIPEA (553 mg, 4.28 mmol) at 25° C. Then the mixture was stirred at 130° C. for 3 hours. On completion, the mixture was quenched with water (10 mL), and extracted with EA (3×15 mL). The combined organic phase was dried over $Na_2SO_4$, filtered and the filtrate was concentrated in vacuo to give a residue. The residue was purified by reverse phase (0.1% FA) to afford the title compound (480 mg, 86% yield) as yellow solid. $^1$H NMR (400 MHz, DMSO-$d_6$) δ 11.09 (s, 1H), 7.58 (t, J=7.8 Hz, 1H), 7.12-6.99 (m, 2H), 6.66 (t, J=5.8 Hz, 1H), 5.08-5.00 (m, 1H), 4.37 (t, J=5.2 Hz, 1H), 3.48-3.40 (m, 6H), 3.39-3.35 (m, 2H), 2.94-2.82 (m, 1H), 2.63-2.53 (m, 2H), 2.06-1.98 (m, 1H), 1.84-1.76 (m, 2H), 1.71-1.62 (m, 2H); LC-MS (ESI$^+$) m/z 390.2 (M+H)$^+$.

Step 2—3-[3-[[2-(2,6-Dioxo-3-piperidyl)-1,3-dioxo-isoindolin-4-yl] amino]propoxy]propanal To a mixture of 2-(2,6-dioxo-3-piperidyl)-4-[3-(3-hydroxypropoxy)propylamino]isoindoline-1,3-dione (150 mg, 385 umol) in DCM (3 mL) was added DMP (196 mg, 462 umol) at 25° C. The mixture was stirred at 25° C. for 2 hours. On completion, the reaction mixture was quenched with aqueous $Na_2S_2O_4$ (5 mL) and $NaHCO_3$ (5 mL) at 25° C., and then diluted with DCM (10 mL) and extracted with DCM (3×20 mL). The combined organic layers were washed with brine (10 mL), dried over $Na_2SO_4$, filtered and the filtrate was concentrated in vacuo to give the title compound (148 mg, 99% yield) as yellow solid. LC-MS (ESI$^+$) m/z 388.3 (M+H)$^+$.

2-[1-[2-(2,6-Dioxo-3-piperidyl)-1,3-dioxo-isoindolin-4-yl]-4-piperidyl]acetaldehyde (Intermediate AGE)

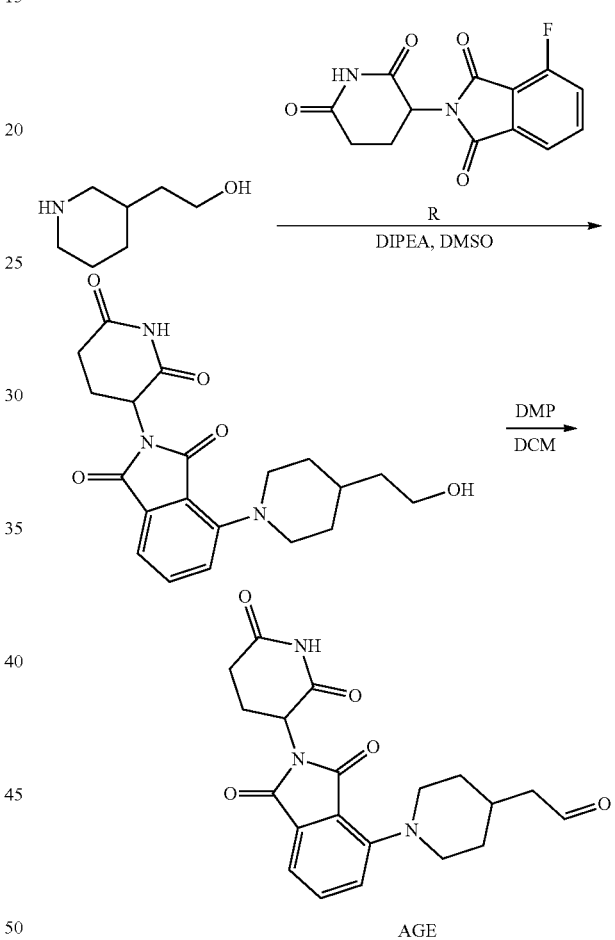

Step 1—2-(2,6-Dioxo-3-piperidyl)-4-[4-(2-hydroxyethyl)-1-piperidyl]isoindoline-1,3-dione To a solution of 2-(4-piperidyl)ethanol (280 mg, 2.17 mmol, CAS #622-26-4) in DMSO (8 mL) was added DIPEA (841 mg, 6.51 mmol) and 2-(2,6-dioxo-3-piperidyl)-4-fluoro-isoindoline-1,3-dione (0.60 g, 2.17 mmol, Intermediate R). The reaction mixture was stirred at 130° C. for 16 hrs. On completion, the reaction mixture was quenched by water (30 mL), and then extracted with EA (3×30 mL). The combined organic layers were dried over $Na_2SO_4$, filtered and concentrated in vacuo to give a residue. The residue was purified by prep-HPLC (FA condition) to give the title compound (0.55 g, 65% yield) as yellow solid. $^1$H NMR (400 MHz, CDCl$_3$) δ 8.36 (s, 1H), 7.56 (dd, J=7.2, 8.4 Hz, 1H), 7.36 (d, J=7.2 Hz, 1H), 7.17 (d, J=8.4 Hz, 1H), 4.97 (dd, J=5.2, 12.4 Hz, 1H), 3.80-3.67 (m, 4H), 2.96-2.84 (m, 3H), 2.84-2.64 (m, 2H), 2.16-2.05 (m, 1H), 1.85 (d, J=12.0 Hz, 2H), 1.74-1.57 (m, 4H), 1.54-1.46 (m, 2H).

Step 2—2-[1-[2-(2,6-Dioxo-3-piperidyl)-1,3-dioxo-isoindolin-4-yl]-4-piperidyl] acetaldehyde To a solution of 2-(2,6-dioxo-3-piperidyl)-4-[4-(2-hydroxyethyl)-1-piperidyl]isoindoline-1,3-dione (150 mg, 389 umo) in DCM (5 mL) was added DMP (198 mg, 467 umol) at 0° C. The mixture was stirred at 15° C. for 5 hrs. On completion, the reaction was quenched by saturated Na$_2$S$_2$O$_3$ (3 mL) and saturated NaHCO$_3$ (3 mL) at 0° C. and stirred for 30 minutes, and then extracted with DCM (3×5 mL). The combined organic layers was dried over Na$_2$SO$_4$, filtered and concentrated in vacuo to give the title compound (146 mg, 98% yield) as yellow solid. $^1$H NMR (400 MHz, CDCl$_3$) 9.83 (s, 1H), 8.09 (s, 1H), 7.62-7.53 (m, 1H), 7.38 (d, J=7.2 Hz, 1H), 7.18 (d, J=8.4 Hz, 1H), 4.97 (dd, J=5.2, 12.4 Hz, 1H), 3.84-3.66 (m, 2H), 3.00-2.68 (m, 5H), 2.48 (dd, J=1.2, 6.8 Hz, 2H), 2.19-2.07 (m, 2H), 1.89 (d, J=12.8 Hz, 2H), 1.66-1.60 (m, 2H).

3-[1-[2-(2,6-Dioxo-3-piperidyl)-1,3-dioxo-isoindolin-4-yl]-4-piperidyl]propanal (Intermediate AGF)

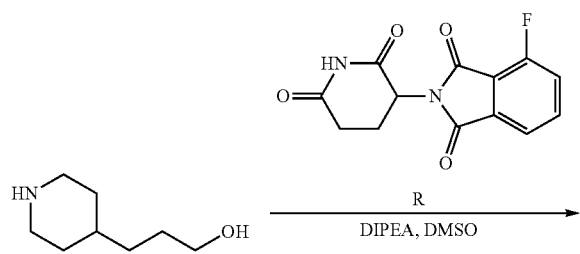

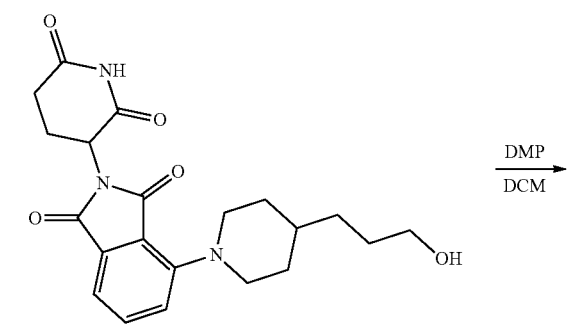

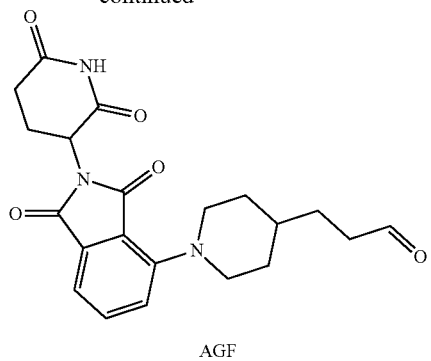

AGF

Step 1—2-(2,6-Dioxo-3-piperidyl)-4-[4-(3-hydroxypropyl)-1-piperidyl]isoindoline-1,3-dione To a solution of 2-(2,6-dioxo-3-piperidyl)-4-fluoro-isoindoline-1,3-dione (500 mg, 1.81 mmol, Intermediate R) and 3-(4-piperidyl)propan-1-ol (259.24 mg, 1.81 mmol, CAS #7037-49-2) in DMSO (6 mL) was added DIPEA (701 mg, 5.43 mmol, 945 uL). The reaction mixture was stirred at 130° C. for 3 hrs. On completion, the mixture was concentrated in vacuo to give a residue. The residue was purified by reverse phase (0.1% FA condition) to give the title compound (450 mg, 62% yield) as a yellow solid. $^1$H NMR (400 MHz, DMSO-d$_6$) δ 11.09 (s, 1H), 7.67 (dd, J=7.2, 8.4 Hz, 1H), 7.35-7.28 (m, 2H), 5.12-5.05 (m, 1H), 4.38 (t, J=5.2 Hz, 1H), 3.68 (d, J=12.0 Hz, 2H), 3.44-3.36 (m, 2H), 2.93-2.78 (m, 3H), 2.62-2.53 (m, 2H), 2.06-1.97 (m, 1H), 1.76 (d, J=11.2 Hz, 2H), 1.52-1.20 (m, 7H); LC-MS (ESI$^+$) m/z 400.3 (M+H)$^+$.

Step 2—3-r 1-[2-(2,6-Dioxo-3-piperidyl)-1,3-dioxo-isoindolin-4-yl]-4-piperidyl]propanal To a solution of 2-(2,6-dioxo-3-piperidyl)-4-[4-(3-hydroxypropyl)-1-piperidyl]isoindoline-1,3-dione (100 mg, 250 umol) in DCM (5 mL) was added DMP (127 mg, 300 umol, 93.0 uL). The reaction mixture was stirred at 20° C. for 1 hour. On completion, the reaction mixture was quenched with saturated Na$_2$S$_2$O$_3$ (10 mL) and extracted with DCM (2×30 mL). The combined organic phase was washed with NaHCO$_3$ and brine (2×20 mL), dried with anhydrous Na$_2$SO$_4$, filtered and concentrated in vacuo to give the title compound (80.0 mg, 80.4% yield) as a yellow solid. $^1$H NMR (400 MHz, DMSO-d$_6$) δ 11.07 (s, 1H), 9.70 (t, J=1.2 Hz, 1H), 7.67 (dd, J=7.2, 8.4 Hz, 1H), 7.36-7.28 (m, 2H), 5.08 (dd, J=5.2, 12.8 Hz, 1H), 3.68 (d, J=11.6 Hz, 2H), 2.93-2.77 (m, 3H), 2.64-2.52 (m, 2H), 2.49-2.45 (m, 2H), 2.08-1.99 (m, 1H), 1.76 (d, J=11.6 Hz, 2H), 1.59-1.45 (m, 2H), 1.45-1.28 (m, 3H); LC-MS (ESI$^+$) m/z 398.2 (M+H)$^+$.

4-[4-[3-[4-[4-Amino-3-(difluoromethyl)pyrazol-1-yl]-1-piperidyl]propyl]-1-piperidyl]-2-(2,6-dioxo-3-piperidyl)isoindoline-1,3-dione (Intermediate AGG)

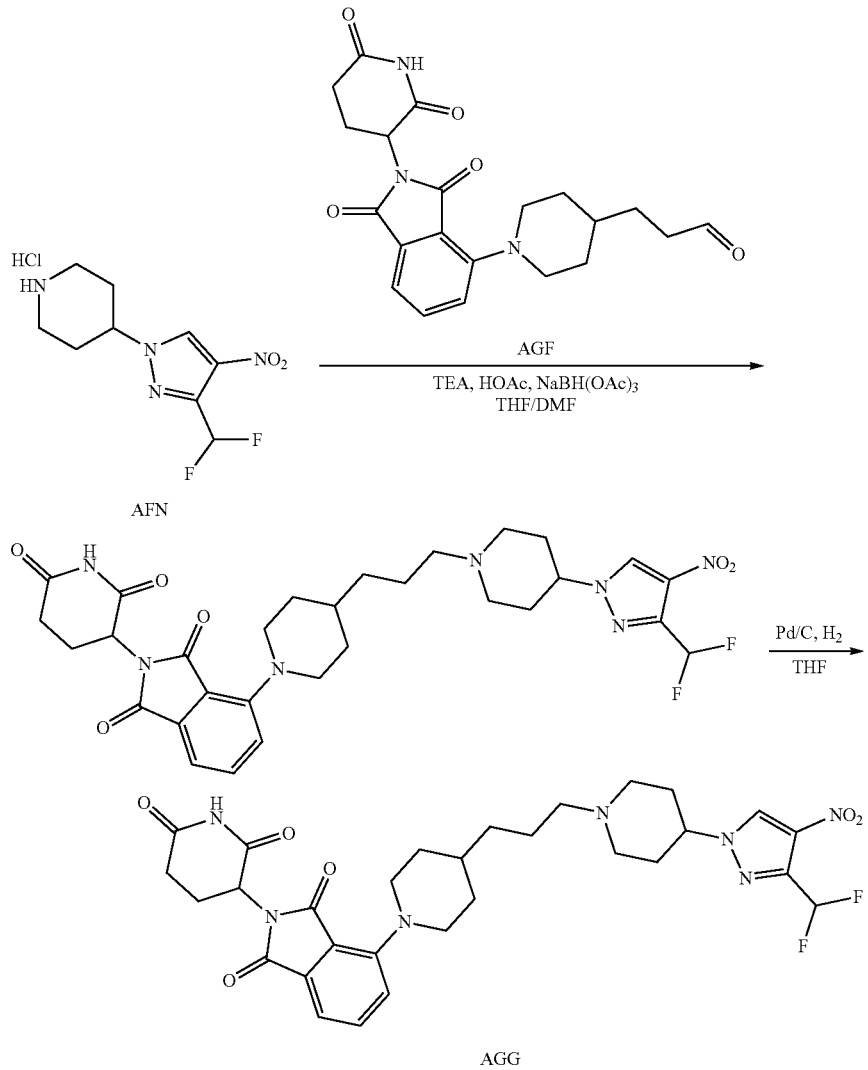

AGG

Step 1—4-[4-[3-[4-[3-(Difluoromethyl)-4-nitro-pyrazol-1-yl]-1-piperidyl]propyl]-1-piperidyl]-2-(2,6-dioxo-3-piperidyl)isoindoline-1,3-dione To a solution of 4-[3-(difluoromethyl)-4-nitro-pyrazol-1-yl]piperidine (80 mg, 283.01 umol, HCl, synthesized via Step 1 of Intermediate AFN) in THF (3 mL) and DMF (1 mL) was added TEA (28.64 mg, 283.01 umol, 39.4 uL). The reaction mixture was stirred at 20° C. for 10 min. Then 3-[1-[2-(2,6-dioxo-3-piperidyl)-1,3-dioxo-isoindolin-4-yl]-4-piperidyl]propanal (112 mg, 283 umol, Intermediate AGF) and HOAc (33.9 mg, 566 umol, 32.3 uL) were added, and the mixture was stirred at 20° C. for 20 min. Next, NaBH(OAc)$_3$ (77.9 mg, 367 umol) was added to the mixture, and the mixture was stirred at 20° C. for 12 hr. On completion, the mixture was quenched with H$_2$O (0.5 mL), and then concentrated in vacuo to give a residue. The residue was purified by reverse phase (0.1% FA condition) to give the title compound (120 mg, 67% yield) as a yellow solid. $^1$H NMR (400 MHz, DMSO-d$_6$) δ 11.08 (s, 1H), 9.09 (s, 1H), 7.67 (t, J=8.0 Hz, 1H), 7.47-7.16 (m, 3H), 5.09 (dd, J=5.2, 12.8 Hz, 1H), 4.37-4.25 (m, 1H), 3.69 (d, J=11.6 Hz, 2H), 2.98 (d, J=10.4 Hz, 2H), 2.93-2.77 (m, 3H), 2.64-2.51 (m, 2H), 2.33 (t, J=7.2 Hz, 2H), 2.12-1.89 (m, 7H), 1.78 (d, J=10.8 Hz, 2H), 1.57-1.18 (m, 7H); LC-MS (ESI$^+$) m/z 628.2 (M+H)$^+$.

Step 2—4-[4-[3-[4-[4-Amino-3-(difluoromethyl)pyrazol-1-yl]-1-piperidyl]propyl]-1-piperidyl]-2-(2,6-dioxo-3-piperidyl)isoindoline-1,3-dione To a solution of 4-[4-[3-[4-[3-(difluoromethyl)-4-nitro-pyrazol-1-yl]-1-piperidyl]propyl]-1-piperidyl]-2-(2,6-dioxo-3-piperidyl)isoindoline-1,3-dione (110 mg, 175 umol) in THF (5 mL) was added Pd/C (50 mg, 10 wt %). The reaction was stirred at 20° C. for 2 hrs under H$_2$ (15 psi). On completion, the mixture was concentrated in vacuo to give the title compound (100 mg, 95% yield) as a yellow solid. LC-MS (ESI$^+$) m/z 598.2 (M+H)$^+$.

2-(2,6-Dioxo-3-piperidyl)-4-[[1-(4-piperidyl)-4-piperidyl]amino]isoindoline-1,3-dione (Intermediate AGH)

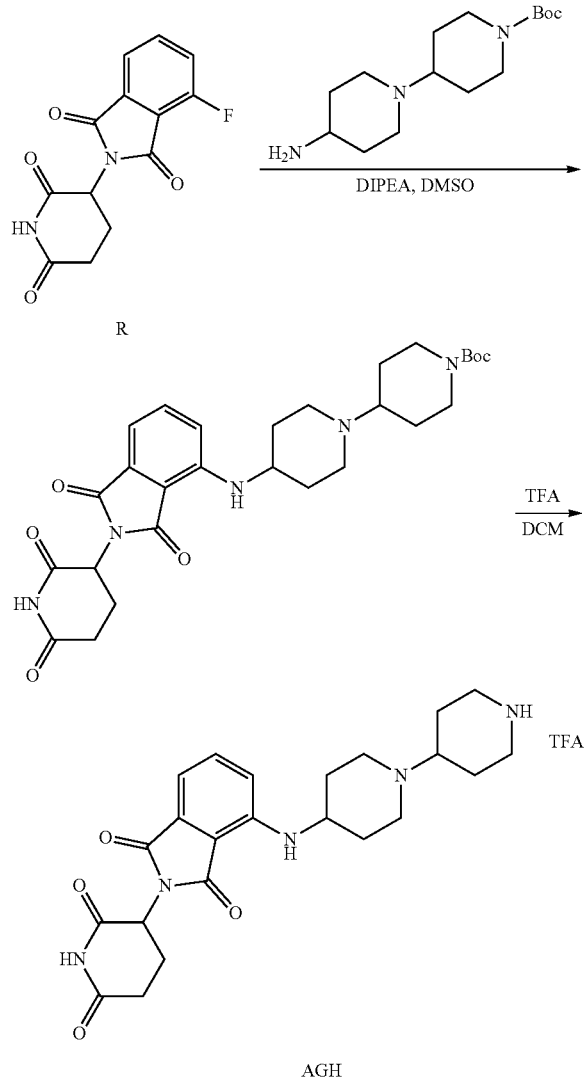

Step 1—Tert-butyl 4-[4-[[2-(2,6-dioxo-3-piperidyl)-1,3-dioxo-isoindolin-4-yl]amino]-1-piperidyl] piperidine-1-carboxylate To a mixture of 2-(2,6-dioxo-3-piperidyl)-4-fluoro-isoindoline-1,3-dione (200 mg, 724 umol, Intermediate R) and tert-butyl 4-(4-amino-1-piperidyl)piperidine-1-carboxylate (205 mg, 724 umol, CAS #959237-16-2) in DMSO (4 mL) was added DIPEA (280 mg, 2.17 mmol, 378 uL). The reaction mixture was stirred at 130° C. for 2 hours. On completion, the reaction mixture was concentrated in vacuo. The residue was purified by reverse phase (0.1% FA condition) to give the title compound (470 mg, 92% yield) as green solid. $^1$H NMR (400 MHz, DMSO-$d_6$) δ 11.09 (s, 1H), 7.62-7.54 (m, 1H), 7.16 (d, J=8.8 Hz, 1H), 7.04 (d, J=7.2 Hz, 1H), 6.24 (d, J=8.0 Hz, 1H), 5.09-5.00 (m, 1H), 3.97 (d, J=11.6 Hz, 2H), 3.65-3.52 (m, 1H), 2.93-2.81 (m, 3H), 2.78-2.63 (m, 2H), 2.63-2.51 (m, 3H), 2.43 (t, J=10.4 Hz, 2H), 2.07-2.00 (m, 1H), 1.96 (d, J=11.2 Hz, 2H), 1.74 (d, J=11.6 Hz, 2H), 1.56-1.44 (m, 2H), 1.39 (s, 9H), 1.34-1.22 (m, 2H); LC-MS (ESI$^+$) m/z 540.4 (M+H)$^+$.

Step 2—2-(2,6-Dioxo-3-piperidyl)-4-[[r-(4-piperidyl)-4-piperidyl]amino]isoindoline-1,3-dione To a mixture of tert-butyl 4-[4-[[2-(2,6-dioxo-3-piperidyl)-1,3-dioxo-isoindolin-4-yl]amino]-1-piperidyl]piperidine-1-carboxylate (120 mg, 222 umol) in DCM (2 mL) was added TFA (4.62 g, 40.5 mmol, 3.00 mL). The reaction mixture was stirred at 25° C. for 1 hour. On completion, the reaction mixture was concentrated in vacuo to give the title compound (120 mg, 97% yield, TFA) as green solid. LC-MS (ESI$^+$) m/z 440.3 (M+H)$^+$.

3-[4-(2,7-Diazaspiro[3.5]nonan-2-ylmethyl)-3-methyl-2-oxo-benzimidazol-1-yl]piperidine-2,6-dione (Intermediate AGI)

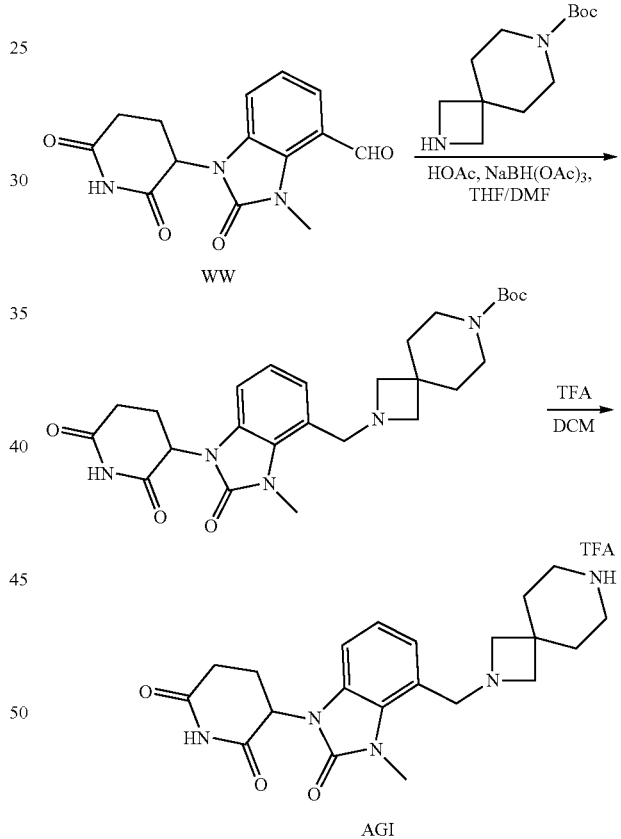

Step 1—Tert-butyl 2-[[1-(2,6-dioxo-3-piperidyl)-3-methyl-2-oxo-benzimidazol-4-yl]methyl]-2,7-diazaspiro[3.5]nonane-7-carboxylate To a mixture of tert-butyl 2,7-diazaspiro[3.5]nonane-7-carboxylate (330 mg, 1.46 mmol, CAS #896464-16-7) in THF (1 mL) and DMF (3 mL) was added 1-(2,6-dioxo-3-piperidyl)-3-methyl-2-oxo-benzimidazole-4-carbaldehyde (300 mg, 1.04 mmol, Intermediate WW) and HOAc (62.7 mg, 1.04 mmol, 59.7 uL). The mixture was stirred at 80° C.

for 1 hour. Then NaBH(OAc)$_3$ (442 mg, 2.09 mmol) was added to the mixture and stirred at 40° C. for 48 hours. On completion, the reaction mixture was quenched with water (0.1 mL) and concentrated in vacuo. The residue was purified by prep-HPLC (column: Phenomenex Synergi C18 150*25*10 um; mobile phase: [water (0.05% HCl)-ACN]; B %: 16%-36%, 12 min) to give the title compound (25.0 mg, 4% yield) as light yellow solid. $^1$H NMR (400 MHz, DMSO-d$_6$) δ 11.13 (s, 1H), 7.27-7.19 (m, 2H), 7.14-7.07 (m, 1H), 5.47-5.38 (m, 1H), 4.77 (d, J=5.6 Hz, 2H), 4.09-3.91 (m, 4H), 3.60 (s, 3H), 3.31-3.26 (m, 2H), 3.23 (s, 2H), 2.96-2.84 (m, 1H), 2.74-2.61 (m, 2H), 2.04-1.95 (m, 1H), 1.84-1.78 (m, 2H), 1.77-1.71 (m, 2H), 1.38 (s, 9H); LC-MS (ESI$^+$) m/z 498.4 (M+H)$^+$.

Step 2—3-[4-(2,7-Diazaspiro[3.5]nonan-2-ylmethyl)-3-methyl-2-oxo-benzimidazol-1-yl]piperidine-2,6-dione To a mixture of tert-butyl 2-[[1-(2,6-dioxo-3-piperidyl)-3-methyl-2-oxo-benzimidazol-4-yl]methyl]-2,7-diazaspiro[3.5]nonane-7-carboxylate (25.0 mg, 50.2 umol) in DCM (3 mL) was added TFA (1.54 g, 13.5 mmol, 1 mL). The reaction mixture was stirred at 25° C. for 0.5 hour. On completion, the reaction mixture was concentrated in vacuo to give the title compound (25.0 mg, 97% yield, TFA) as red oil. LC-MS (ESI$^+$) m/z 398.3 (M+H)$^+$.

5-[[(1R,2S)-2-hydroxycyclohexyl]amino]pyrazolo[1,5-a]pyrimidine-3-carboxylic acid (Intermediate AGJ)

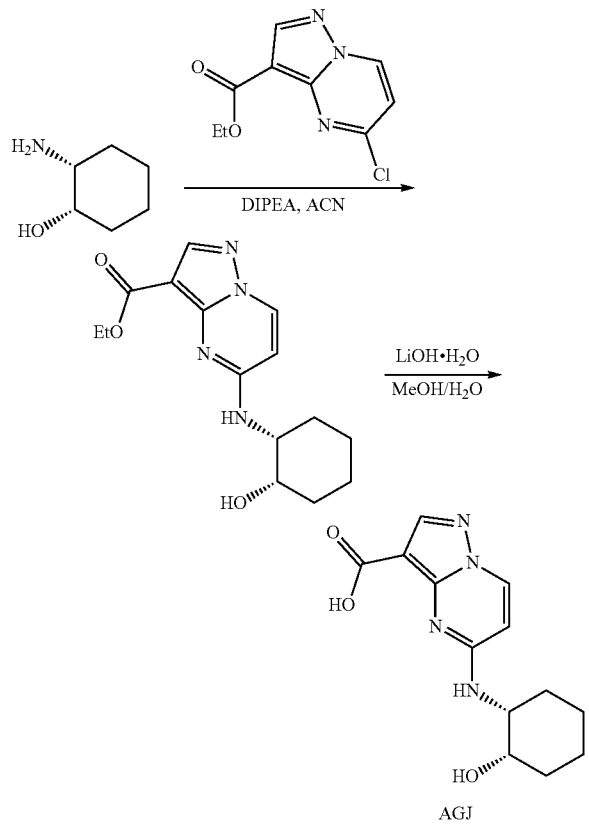

Step 1—Ethyl 5-[[(1R,2S)-2-hydroxycyclohexyl]amino]pyrazolo[1,5-a]pyrimidine-3-carboxylate To a solution of ethyl 5-chloropyrazolo[1,5-a]pyrimidine-3-carboxylate (1.50 g, 6.65 mmol, CAS #122944-77-7), and (1S,2R)-2-aminocyclohexanol; hydrochloride (1.51 g, 9.98 mmol, CAS #108267-20-5) in ACN (30 mL) was added DIPEA (2.58 g, 19.95 mmol). The mixture was stirred at 60° C. for 16 hrs. On completion, the mixture was concentrated in vacuo. The mixture was purified by reverse phase (0.1% FA) to give the title compound (2.00 g, 98% yield) as yellow solid. $^1$H NMR (400 MHz, DMSO-d$_6$) δ 8.48 (d, J=7.6 Hz, 1H), 8.12 (s, 1H), 7.63 (d, J=7.2 Hz, 1H), 6.54 (d, J=7.6 Hz, 1H), 4.18 (q, J=7.2 Hz, 2H), 4.12-4.03 (m, 1H), 4.01-3.95 (m, 1H), 1.80-1.69 (m, 2H), 1.68-1.32 (m, 6H), 1.31-1.27 (m, 3H).

Step 2—5-[[(1R,2S)-2-hydroxycyclohexyl]amino]pyrazolo[1,5-a]pyrimidine-3-carboxylic acid To a solution of ethyl 5-[[(1R,2S)-2-hydroxycyclohexyl]amino]pyrazolo[1,5-a]pyrimidine-3-carboxylate (1.55 g, 5.09 mmol) in MeOH (30 mL) and H$_2$O (6 mL) was added LiOH—H$_2$O (1.07 g, 25.4 mmol). The mixture was stirred at 60° C. for 16 hrs. On completion, the mixture was concentrated in vacuo. The residue was diluted with H$_2$O (30 mL), the mixture was acidified with 1N HCl solution until the pH=3. The mixture was filtered and the solid was dried in vacuo to give the title compound (1.00 g, 71% yield) as yellow solid. $^1$H NMR (400 MHz, DMSO-d$_6$) δ 8.47 (J=7.6 Hz, 1H), 8.10 (s, 1H), 7.66 (J=7.6 Hz, 1H), 6.54 (d, J=8.0 Hz, 1H), 4.88-4.66 (m, 1H), 4.20-4.00 (m, 1H), 3.95-3.82 (m, 1H), 1.78-1.65 (m, 2H), 1.64-1.48 (m, 4H), 1.39-1.26 (m, 2H).

Ethyl 4-(p-tolylsulfonyloxy)cyclohexanecarboxylate (Intermediate AGK)

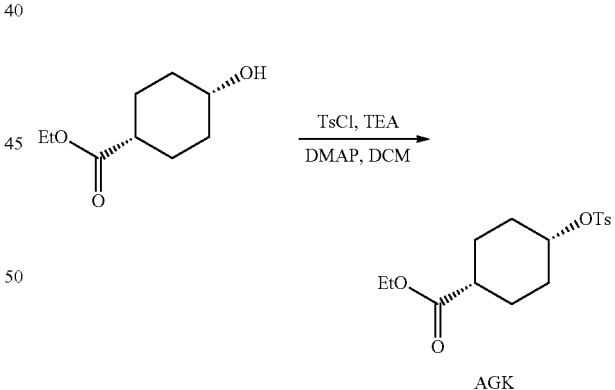

To a solution of ethyl 4-hydroxycyclohexanecarboxylate (10.0 g, 58.06 mmol, CAS #75877-66-6), DMAP (710 mg, 5.81 mmol) and TEA (17.6 g, 174 mmol) in DCM (150 mL) was added p-TsCl (22.1 g, 116 mmol) at 15° C. The mixture was stirred at 15° C. for 16 hours. On completion, the reaction was quenched with water (20 mL) and the mixture was partitioned. The organic layer was concentrated in vacuo. The residue was purified by column chromatography on silica gel to give the title compound (16.0 g, 84% yield) as white solid. $^1$H NMR (400 MHz, CDCl$_3$) δ 7.79 (d, J=8.2 Hz, 2H), 7.33 (d, J=7.9 Hz, 2H), 4.79-4.64 (m, 1H), 4.10 (q, J=7.2 Hz, 2H), 2.45 (s, 3H), 2.35-2.27 (m, 1H), 1.93-1.82 (m, 4H), 1.76-1.66 (m, 2H), 1.60-1.50 (m, 2H), 1.24 (t, J=7.2 Hz, 3H).

N-[2-(4-formylcyclohexyl)-6-(1-hydroxy-1-methyl-ethyl) indazol-5-yl]-6-(trifluoromethyl) pyridine-2-carboxamide (Intermediate AGL)

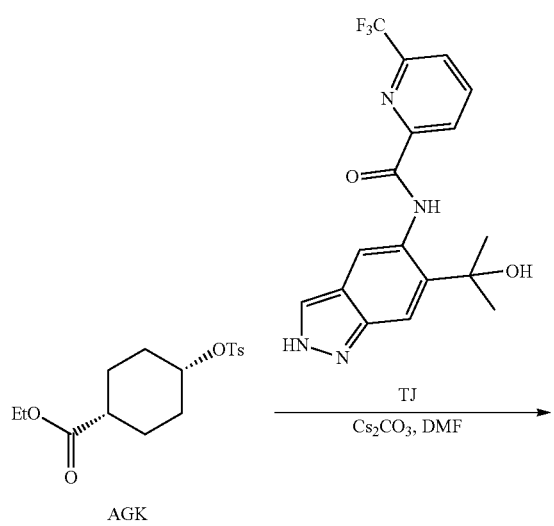

-continued

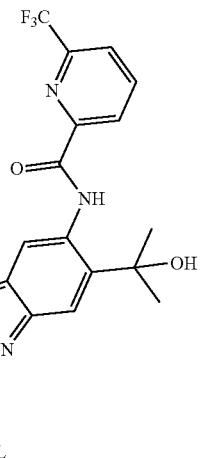

AGL

Step 1—Ethyl 4-[6-(1-hydroxy-1-methyl-ethyl)-5-[[6-(trifluoromethyl)pyridine-2-carbonyl]amino] indazol-2-yl]cyclohexanecarboxylate To a mixture of N-[6-(1-hydroxy-1-methyl-ethyl)-2H-indazol-5-yl]-6-(trifluoromethyl)pyridine-2-carboxamide (1.30 g, 3.57 mmol, Intermediate TJ), ethyl 4-(p-tolylsulfonyloxy)cyclohexane carboxylate (2.33 g, 7.14 mmol, Intermediate AGK) and Cs$_2$CO$_3$ (2.33 g, 7.14 mmol) in DMF (20 mL) was stirred at 80° C. for 16 hours. To the mixture was added ethyl 4-(p-tolylsulfonyloxy)cyclohexanecarboxylate (2.33 g, 7.14 mmol) and Cs$_2$CO$_3$ (2.33 g, 7.14 mmol) at 15° C. The mixture was stirred at 80° C. for 16 hours. On completion, after cooled to 15° C., the mixtures of two batches were combined, diluted with water (100 mL), and extracted with EA (3×60 mL). The organic layer was washed with brine (20 mL), dried over Na$_2$SO$_4$, filtered and concentrated in vacuo. The residue was purified by reverse phase flash and prep-HPLC (column: Phenomenex Synergi Max-RP 150*50 mm*10 um; mobile phase: [water (0.225% FA)-ACN]; B %: 52%-82%, 11 min) to give the title compound (530 mg, 14% yield) as white solid. $^1$H NMR (400 MHz, CDCl$_3$) δ 12.28 (s, 1H), 8.87 (s, 1H), 8.50 (d, J=7.6 Hz, 1H), 8.10 (t, J=8.0 Hz, 1H), 7.92 (s, 1H), 7.84 (d, J=7.6 Hz, 1H), 7.74 (s, 1H), 4.43-4.35 (m, 1H), 4.17 (q, J=7.2 Hz, 2H), 2.48-2.40 (m, 1H), 2.36-2.34 (m, 2H), 2.28-2.19 (m, 3H), 2.10-1.97 (m, 2H), 1.81 (s, 6H), 1.76-1.64 (m, 2H), 1.29 (t, J=7.2 Hz, 3H).

Step 2—N-[2-[4-(hydroxymethyl)cyclohexyl]-6-(1-hydroxy-1-methyl-ethyl) indazol-5-yl]-6-(trifluoromethyl)pyridine-2-carboxamide To a solution of ethyl 4-[6-(1-hydroxy-1-methyl-ethyl)-5-[[6-(trifluoromethyl)pyridine-2-carbonyl] amino]indazol-2-yl]cyclohexanecarboxylate (200 mg, 385 umol) in THF (3 mL) and MeOH (0.4 mL) was added LiBH$_4$ (21.0 mg, 964 umol) at 0° C. The mixture was stirred at 50° C. for 1 hour. On completion, the reaction was quenched with sat. aq. NH$_4$Cl (5 mL). The mixture was diluted with water (40 mL), then extracted with EA (3×20 mL). The combined organic layer was washed with brine (10 mL), dried over Na$_2$SO$_4$, filtered and concentrated in vacuo to give the title compound (180 mg, 98% yield) as light yellow solid. $^1$H NMR (400 MHz, DMSO-d$_6$) δ 12.35 (s, 1H), 8.71 (s, 1H), 8.48-8.42 (m, 1H), 8.39-8.34 (m, 2H), 8.16 (d, J=7.6 Hz, 1H), 7.58 (s, 1H), 6.51 (s, 1H), 5.93 (s, 1H), 4.46-4.35 (m, 1H), 3.29 (s, 2H), 2.19-2.10 (m, 2H), 1.92-1.89 (m, 4H), 1.62 (s, 6H), 1.25-1.11 (m, 3H).

Step 3—N-[2-(4-formylcyclohexyl)-6-(1-hydroxy-1-methyl-ethyl) indazol-5-yl]-6-(trifluoromethyl) pyridine-2-carboxamide To a solution of N-[2-[4-(hydroxymethyl)cyclohexyl]-6-(1-hydroxy-1-methyl-ethyl) indazol-5-yl]-6-(trifluoromethyl)pyridine-2-carboxamide (50.0 mg, 104 umol) in DCM (5 mL) was added DMP (89.0 mg, 209 umol) at 0° C. The mixture was stirred at 0-10° C. for 6 hours. On completion, the reaction was quenched with sat. aq. $Na_2S_2O_3$ (5 mL), and extracted with DCM (2×10 mL). The combined organic layer was washed with sat. aq. $NaHCO_3$ (5 mL), dried over $Na_2SO_4$, filtered and concentrated in vacuo to give the title compound (49.0 mg, 98% yield) as light yellow solid. LC-MS (ESI$^+$) m/z 475.2 (M+H)$^+$.

3-[5-[3-(4-Piperidyloxy)propyl]pyrido[2,3-b]indol-9-yl]piperidine-2,6-dione (Intermediate AGM)

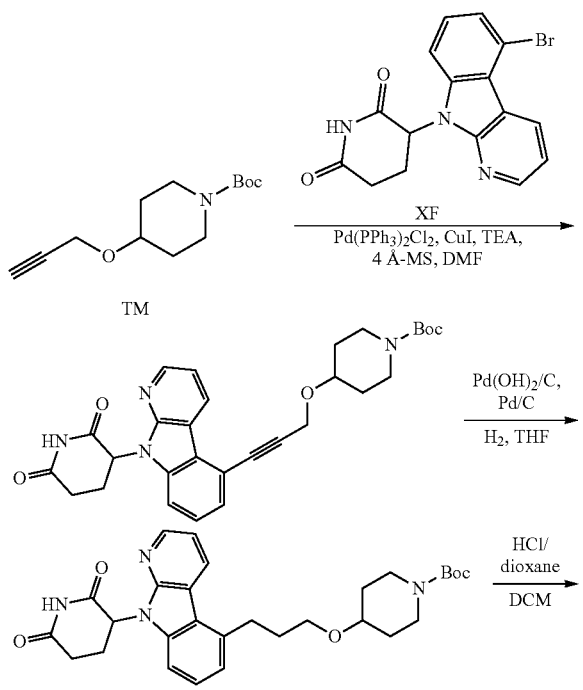

Step 1—Tert-butyl 4-[3-[9-(2,6-dioxo-3-piperidyl)pyrido[2,3-b]indol-5-yl]prop-2-ynoxy]piperidine-1-carboxylate To a mixture of 3-(5-bromopyrido[2,3-b]indol-9-yl)piperidine-2,6-dione (250 mg, 698 umol, Intermediate XF), tert-butyl 4-prop-2-ynoxypiperidine-1-carboxylate (334 mg, 1.40 mmol, Intermediate™) in DMF (5 mL) was added Pd(PPh$_3$)$_2$Cl$_2$ (147 mg, 209 umol), CuI (39.9 mg, 209 umol), TEA (706 mg, 6.98 mmol) and 4 Å molecular sieves (60 mg) under N$_2$. The reaction mixture was stirred at 80° C. for 2 hours. On completion, the residue was poured into water (50 mL) and the aqueous phase was extracted with ethyl acetate (2×30 mL). The combined organic phase was washed with brine (2×40 mL), dried with anhydrous Na$_2$SO$_4$, filtered and concentrated in vacuo to give the residue. The residue was purified by reverse phase (0.1% FA condition) to give the title compound (245 mg, 67% yield) as a brown solid. $^1$H NMR (400 MHz, CDCl$_3$) δ 8.85 (d, J=1.6 Hz, 1H), 8.47 (d, J=1.6 Hz, 1H), 7.43-7.39 (m, 2H), 7.25-7.21 (m, 1H), 7.18-7.06 (m, 2H), 5.92 (d, J=4.2 Hz, 1H), 4.64 (s, 2H), 3.87-3.77 (m, 2H), 3.19-2.89 (m, 6H), 2.31 (d, J=5.2 Hz, 1H), 1.96 (d, J=7.6 Hz, 2H), 1.70-1.60 (m, 2H), 1.47 (s, 9H).

Step 2—Tert-butyl 4-[3-[9-(2,6-dioxo-3-piperidyl)pyrido[2,3-b]indol-5-yl]propoxy]piperidine-1-carboxylate To a mixture of tert-butyl 4-[3-[9-(2,6-dioxo-3-piperidyl)pyrido[2,3-b]indol-5-yl]prop-2-ynoxy] piperidine-1-carboxylate (245 mg, 474 umol) in THF (10 mL) was added Pd/C (50.0 mg, 474 umol) and Pd(OH)$_2$/C (50.0 mg, 474 umol) under N$_2$. The suspension was degassed under vacuum and purged with H$_2$ three times. The mixture was stirred at 25° C. for 12 hours under H$_2$ (15 psi). On completion, the reaction mixture was filtered and concentrated in vacuo to give the title compound (160 mg, 64% yield) as a brown solid. $^1$H NMR (400 MHz, CDCl$_3$) δ 8.54 (d, J=4.8 Hz, 1H), 8.47-8.39 (m, 1H), 8.16-8.09 (m, 1H), 7.48-7.38 (m, 1H), 7.21 (d, J=4.8 Hz, 1H), 7.13 (d, J=4.8 Hz, 2H), 6.04-5.83 (m, 1H), 3.86-3.76 (m, 2H), 3.60 (d, J=5.9 Hz, 2H), 3.51 (d, J=5.2 Hz, 1H), 3.33-3.26 (m, 2H), 3.21-3.13 (m, 2H), 3.12-3.02 (m, 1H), 3.02-2.93 (m, 2H), 2.30 (d, J=7.6 Hz, 1H), 2.13-2.04 (m, 2H), 1.94-1.82 (m, 2H), 1.66-1.58 (m, 2H), 1.48 (s, 9H).

Step 3—3-[5-[3-(4-Piperidyloxy)propyl]pyrido[2,3-b]indol-9-yl]piperidine-2,6-dione To a mixture of tert-butyl 4-[3-[9-(2,6-dioxo-3-piperidyl)pyrido[2,3-b]indol-5-yl]propoxy] piperidine-1-carboxylate (160 mg, 307 umol) in DCM (10 mL) was added HCl/dioxane (4 M, 230 uL). The reaction mixture was stirred at 20° C. for 2 hours. On completion, the reaction mixture was concentrated in vacuo to give the title compound (135 mg, 96% yield, HCl salt) as a white solid. LC-MS (ESI$^+$) m/z 421.2 (M+H)$^+$.

3-[5-[3-[[1-[[4-[4-Amino-3-(difluoromethyl)pyrazol-1-yl]]cyclohexyl]methyl]-4-piperidyl] oy]propyl]pyrido[2,3-b]indol-9-yl]piperidine-2,6-dione (Intermediate AGN)

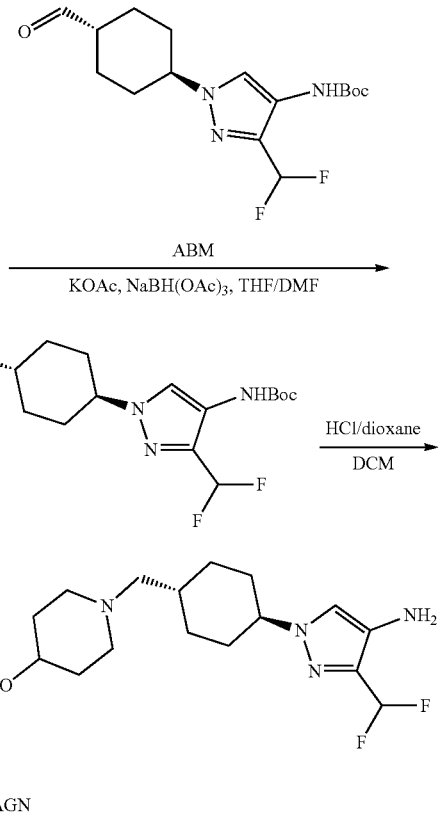

Step 1—Tert-butyl N-[3-(difluoromethyl)-1-[4-[[4-[3-[9-(2,6-dioxo-3-piperidyl)pyrido[2,3-b]indol-5-Yl]propoxy]-1-piperidyl]methyl]cyclohexyl]pyrazol-4-yl]carbamate To a mixture of 3-[5-[3-(4-piperidyloxy) propyl]pyrido[2,3-b]indol-9-yl]piperidine-2,6-dione (120 mg, 262 umol, HCl, Intermediate AGM) in THF (10 mL) and DMF (1 mL) was added KOAc (128.8 mg, 1.31 mmol). The mixture was stirred at 25° C. for 0.5 hour. Tert-butyl N-[3-(difluoromethyl)-1-(4-formyl cyclohexyl)pyrazol-4-yl]carbamate (90.2 mg, 262 umol, Intermediate ABM) and NaBH(OAc)$_3$ (66.8 mg, 315 umol) was then added into the mixture and the reaction mixture was stirred at 25° C. for 1.5 hours. On completion, the reaction was quenched with water (5 mL) and CH$_3$CN (10 mL), and the mixture was concentrated in vacuo to give the residue. The residue was purified by reversed-phase HPLC (0.1% FA condition) to give the title compound (105 mg, 53% yield) as a brown solid. $^1$H NMR (400 MHz, DMSO-d$_6$) δ 11.13 (s, 1H), 8.88 (s, 1H), 8.59 (d, J=6.8 Hz, 1H), 8.42 (d, J=4.0 Hz, 1H), 8.16 (s, 1H), 7.86 (s, 1H), 7.52-7.35 (m, 2H), 7.27 (d, J=6.0 Hz, 1H), 7.16-6.83 (m, 2H), 6.18-5.91 (m, 1H), 4.15-4.04 (m, 1H), 3.55 (d, J=6.0 Hz, 3H), 3.09-2.94 (m, 2H), 2.76-2.58 (m, 4H), 2.17-2.04 (m, 5H), 2.03-1.91 (m, 4H), 1.87 (d, J=12.8 Hz, 4H), 1.77-1.62 (m, 2H), 1.53 (d, J=8.8 Hz, 3H), 1.44 (s, 9H), 1.01 (d, J=12.0 Hz, 2H).

Step 2—3-[5-[3-[[1-[[4-[4-Amino-3-(difluoromethyl)pyrazol-1-yl]cyclohexyl]methyl]-4-piperidyl]oxy]propyl]pyrido[2,3-b]indol-9-yl]piperidine-2,6-dione To a mixture of tert-butyl N-[3-(difluoromethyl)-1-[4-[[4-[3-[9-(2,6-dioxo-3-piperidyl)pyrido[2,3-b] indol-5-yl]propoxy]-1-piperidyl]methyl]cyclohexyl]pyrazol-4-yl]carbamate (105 mg, 140 umol) in DCM (10 mL) was added HCl/dioxane (4 M, 105 uL). The reaction mixture was stirred at 20° C. for 2 hours. On completion, the reaction mixture was concentrated in vacuo to give the title compound (96 mg, 99% yield) as a white solid. LC-MS (ESI$^+$) m/z 648.5 (M+H)$^+$.

Trans-tert-butyl-dimethyl-[(4-prop-2-ynoxycyclohexyl)methoxy]silane (Intermediate AGO)

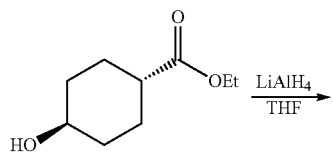

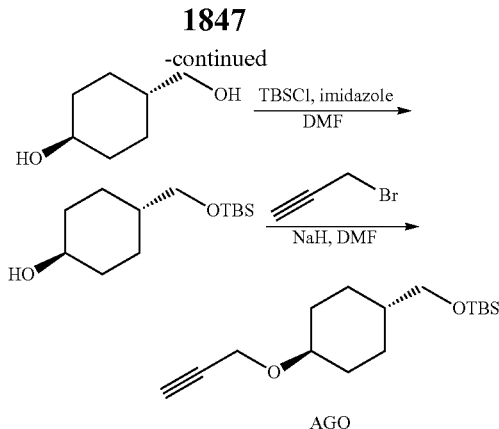

AGO

Step 1—Trans-4-(hydroxymethyl)cyclohexanol

To a solution of ethyl 4-hydroxycyclohexanecarboxylate (5.00 g, 29.0 mmol, CAS #3618-04-0) in THF (100 mL) was added LAH (1.65 g, 43.5 mmol) slowly at 0° C. The mixture was stirred at 15° C. for 16 hours. On completion, the reaction was quenched with water (1.65 mL) slowly. Then, to the mixture was added 10% aq.NaOH (1.65 mL) and water (5.0 mL). The mixture was filtered and the filtrate was concentrated in vacuo to give the title compound (3.70 g, 97% yield) as light yellow oil. $^1$H NMR (400 MHz, DMSO-$d_6$) δ 4.43 (d, J=4.4 Hz, 1H), 4.33 (t, J=5.2 Hz, 1H), 3.31-3.23 (m, 1H), 3.18 (t, J=5.6 Hz, 2H), 1.88-1.79 (m, 3H), 1.68 (d, J=12.4 Hz, 2H), 1.14-1.01 (m, 2H), 0.93-0.78 (m, 2H).

Step 2—Trans-4-[tert-butyl(dimethyl)silyl]oxymethyl]cyclohexanol

To a solution of 4-(hydroxymethyl)cyclohexanol (3.70 g, 28.4 mmol), imidazole (3.87 g, 56.8 mmol) and DMAP (348 mg, 2.85 mmol) in DMF (40 mL) was added TBSCl (3.86 g, 25.5 mmol) at 0° C. The mixture was stirred at 15° C. for 16 hours. On completion, the mixture was diluted with water (200 mL), and extracted with EA (3×80 mL). The combined organic layer was washed with brine (50 mL), dried over $Na_2SO_4$, filtered and concentrated in vacuo. The residue was purified by column chromatography on silica gel to give the title compound (3.10 g, 44% yield) as light yellow oil. $^1$H NMR (400 MHz, DMSO-$d_6$) δ 4.45 (d, J=4.4 Hz, 1H), 3.36 (d, J=6.4 Hz, 2H), 3.30-3.24 (m, 1H), 1.86-1.76 (m, 2H), 1.72-1.62 (m, 2H), 1.36-1.23 (m, 1H), 1.14-1.03 (m, 2H), 0.95-0.87 (m, 2H), 0.86 (s, 9H), 0.01 (s, 6H).

Step 3—Trans-tert-butyl-dimethyl-[(4-prop-2-ynoxycyclohexyl)methoxy]silane

To a solution of 4-[[tert-butyl(dimethyl)silyl]oxymethyl]cyclohexanol (1.00 g, 4.09 mmol) in DMF (20 mL) was added NaH (491 mg, 12.2 mmol, 60% dispersion in mineral oil) at 0° C., and the mixture was stirred at 0-10° C. for 0.5 hour. Then 3-bromoprop-1-yne (913 mg, 6.14 mmol) was added to the reaction mixture at 0° C. The mixture was stirred at 15° C. for 16 hours. On completion, the reaction was quenched with sat. aq. $NH_4Cl$ (10 mL) slowly. The mixture was diluted with water (80 mL), then extracted with EA (3×50 mL). The combined organic layer was dried over $Na_2SO_4$, filtered and concentrated in vacuo. The residue was purified by column chromatography on silica gel to give the title compound (540 mg, 46% yield) as light yellow oil. $^1$H NMR (400 MHz, $CDCl_3$) δ 4.73-4.57 (m, 1H), 4.20 (d, J=2.4 Hz, 2H), 3.41 (d, J=4.4 Hz, 2H), 2.40 (t, J=2.4 Hz, 1H), 2.14-2.05 (m, 2H), 2.03-1.96 (m, 2H), 1.83 (d, J=13.6 Hz, 2H), 1.24-1.18 (m, 2H), 0.90 (s, 9H), 0.04 (s, 6H).

Trans-4-[3-[1-(2,6-Dioxo-3-piperidyl)-3-methyl-2-oxo-benzimidazol-4-yl]propoxy] cyclohexanecarbaldehyde (Intermediate AGP)

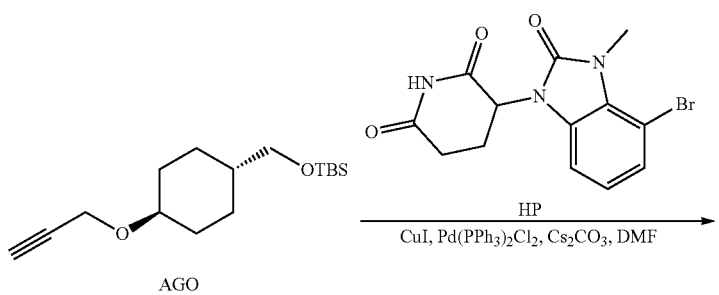

AGO

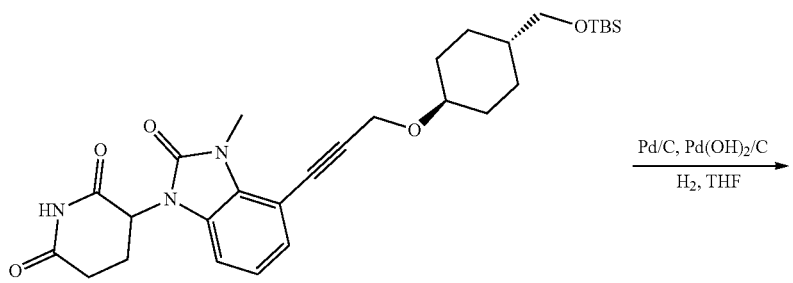

-continued

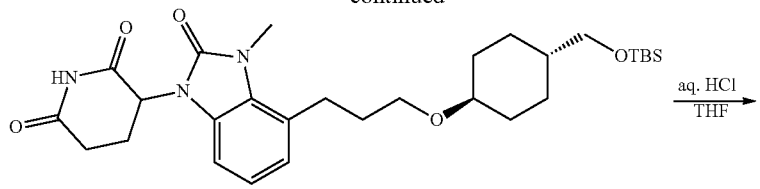

aq. HCl
―――――→
THF

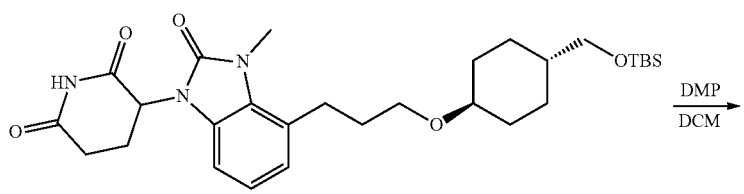

DMP
―――→
DCM

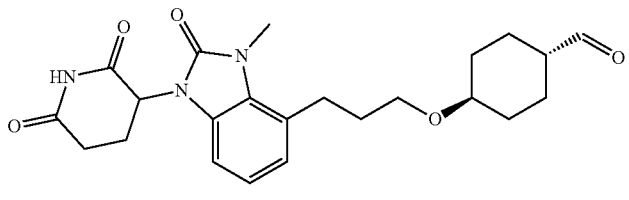

AGP

Step 1—3-[4-[3-[Trans-4-[[tert-butyl(dimethyl)silyl]oxymethyl]cyclohexoxy]prop-1-ynyl]-3-methyl-2-oxo-benzimidazol-1-yl]piperidine-2,6-dione A mixture of tert-butyl-dimethyl-[(4-prop-2-ynoxycyclohexyl)methoxy]silane (500 mg, 1.77 mmol, Intermediate AGO), 3-(4-bromo-3-methyl-2-oxo-benzimidazol-1-yl)piperidine-2,6-dione (300 mg, 887 umol, Intermediate HP), CuI (34.0 mg, 178 umol), $Pd(PPh_3)_2Cl_2$ (125 mg, 178 umol), 4 Å molecular sieves (200 mg) and $Cs_2CO_3$ (1.45 g, 4.44 mmol) in DMF (10 mL) was stirred at 80° C. for 2 hours. On completion, after cooled to 15° C., the mixture was diluted with water (60 mL), then extracted with EA (3×40 mL). The combined organic layer was washed with brine (20 mL), dried over $Na_2SO_4$, filtered and concentrated in vacuo. The residue was purified by reverse phase flash (FA condition) to give the title compound (350 mg, 73% yield) as light yellow solid. LC-MS (ESI$^+$) m/z 540.4 (M+H)$^+$.

Step 2-3-[4-[3-[Trans-4-[[tert-butyl(dimethyl)silyl]oxymethyl]cyclohexoxy]propyl]-3-methyl-2-oxo-benzimidazol-1-yl]piperidine-2,6-dione A mixture of 3-[4-[3-[4-[[tert-butyl(dimethyl)silyl]oxymethyl]cyclohexoxy]prop-1-ynyl]-3-methyl-2-oxo-benzimidazol-1-yl]piperidine-2,6-dione (320 mg, 592 umol), Pd/C (80.0 mg, 10 wt %) and $Pd(OH)_2$/C (80.0 mg, 10 wt %) in THF (20 mL) was stirred at 15° C. for 16 hours under $H_2$ (15 Psi). On completion, the mixture was filtered, and the cake was washed with THF (10 mL). The filtrate and washing were combined and concentrated in vacuo to give the title compound (320 mg, 99% yield) as light yellow solid. LC-MS (ESI$^+$) m/z 544.4 (M+H)$^+$.

Step 3—3-[4-[3-[Trans-4-(hydroxymethyl)cyclohexoxy]propyl]-3-methyl-2-oxo-benzimidazol-1-yl]piperidine-2,6-dione To a solution of 3-[4-[3-[4-[[tert-butyl(dimethyl)silyl]oxymethyl]cyclohexoxy]propyl]-3-methyl-2-oxo-benzimidazol-1-yl]piperidine-2,6-dione (300 mg, 551 umol) in THF (6 mL) was added aq. HCl (2.0 M, 3.0 mL) at 15° C. The mixture was stirred at 15° C. for 16 hours. On completion, the mixture was basified to pH=7 with TEA and the mixture was concentrated in vacuo. The residue was purified by reversed phase flash (FA condition) to give the title compound (160 mg, 67% yield) as light yellow solid. $^1$H NMR (400 MHz, DMSO-d$_6$) δ 11.08 (s, 1H), 6.96 (d, J=4.4 Hz, 2H), 6.88-6.84 (m, 1H), 5.38-5.33 (m, 1H), 3.56 (s, 3H), 3.48-3.46 (m, 4H), 3.35-3.33 (m, 1H), 3.21-3.18 (m, 2H), 2.98-2.91 (m, 2H), 2.69-2.62 (m, 1H), 2.00-1.98 (m, 2H), 1.80-1.70 (m, 4H), 1.36-1.23 (m, 2H), 1.15-1.05 (m, 2H), 0.95-0.82 (m, 3H).

Step 4—Trans-4-[3-[1-(2,6-Dioxo-3-piperidyl)-3-methyl-2-oxo-benzimidazol-4-yl]propoxy] cyclohexanecarbaldehyde To a solution of 3-[4-[3-[4-(hydroxymethyl)cyclohexoxy]propyl]-3-methyl-2-oxo-benzimidazol-1-yl] piperidine-2,6-dione (155 mg, 360 umol) in DCM (10 mL) was added DMP (232 mg, 546 umol) at 0° C. The mixture was stirred at 10° C. for 1 hour. On completion, the reaction was quenched with sat. aq. $Na_2S_2O_3$ (5 mL), and partitioned. The aqueous phase was extracted with DCM (10 mL). The combined organic layer was washed with brine (5 mL), dried over $Na_2SO_4$, filtered and concentrated in vacuo. The residue was purified by reversed phase flash (TFA condition) to give the title compound (110 mg, 71% yield) as light yellow solid. LC-MS (ESI$^+$) m/z 428.3 (M+H)$^+$.

5-(4-Hydroxy-4-methyl-1-piperidyl)pyrazolo[1,5-a]pyrimidine-3-carboxylic acid (Intermediate AGQ)

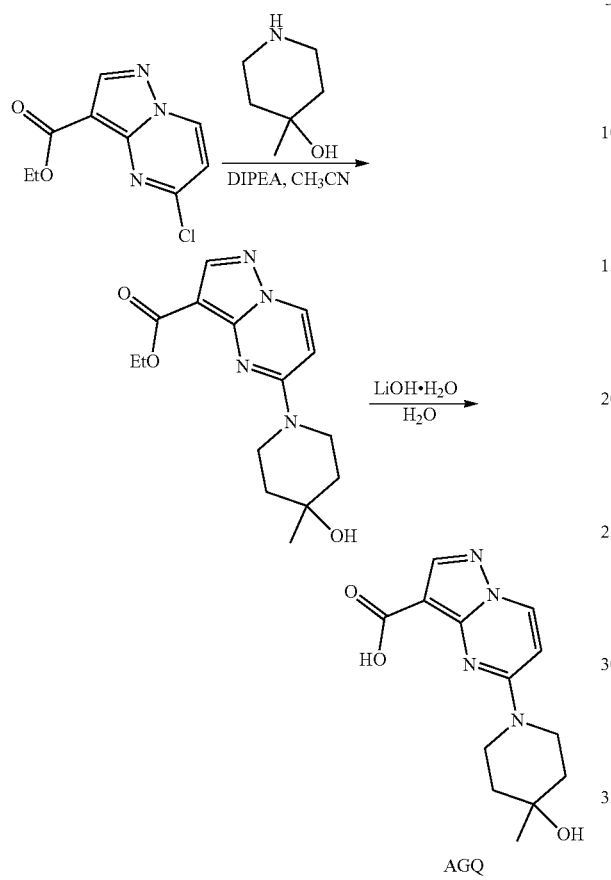

AGQ

Step 1—Ethyl 5-(4-hydroxy-4-methyl-1-piperidyl)pyrazolo[1,5-a]pyrimidine-3-carboxylate To a solution of ethyl 5-chloropyrazolo[1,5-a]pyrimidine-3-carboxylate (200 mg, 886 umol, CAS #1224944-77-7) and 4-methylpiperidin-4-ol (122 mg, 1.06 mmol, CAS #586375-35-1) in ACN (15 mL) was added DIPEA (18.7 mg, 144 umol) at 25° C. The reaction mixture was stirred at 60° C. for 2 hours. On completion, the reaction mixture was extracted with EA (3×10 mL). The combined organic layers were washed with $H_2O$ (3×10 mL), dried over by $Na_2SO_4$, filtered and concentrated in vacuo. The residue was purified by reverse phase (0.1% FA condition) to give the title compound (280 mg, 90% yield, FA salt) as a yellow solid. $^1H$ NMR (400 MHz, DMSO-$d_6$) δ 8.65 (d, J=8.0 Hz, 1H), 8.17 (s, 1H), 6.85 (d, J=8.0 Hz, 1H), 4.46 (s, 1H), 4.20-4.15 (m, 2H), 3.51-3.39 (m, 2H), 3.32 (s, 2H), 1.61-1.44 (m, 4H), 1.27 (t, J=7.2 Hz, 3H), 1.16 (s, 3H); LC-MS (ESI$^+$) m/z 305.2 (M+H)$^+$.

Step 2—5-(4-Hydroxy-4-methyl-1-piperidyl)pyrazolo[1,5-a]pyrimidine-3-carboxylic acid To a solution of ethyl 5-(4-hydroxy-4-methyl-1-piperidyl)pyrazolo[1,5-a]pyrimidine-3-carboxylate (60.0 mg, 197 umol) in $H_2O$ (3 mL) was added LiOH·$H_2O$ (41.3 mg, 985 umol) at 25° C. The reaction mixture was stirred at 60° C. for 2 hours. On completion, the reaction mixture was added of 1.0 M aq.HCl to PH 4-5 and was concentrated in vacuo to give the title compound (50.0 mg, 91% yield) as a white solid. LC-MS (ESI$^+$) m/z 259.7 (M−17)$^+$.

5-(2-Oxa-6-azaspiro[3.3]heptan-6-yl)pyrazolo[1,5-a]pyrimidine-3-carboxylic acid (Intermediate AGR)

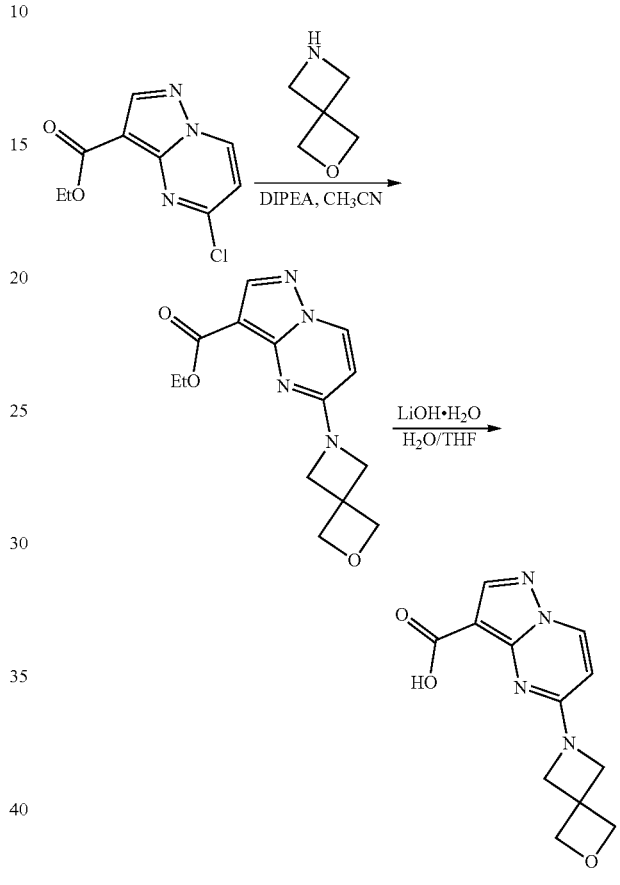

AGR

Step 1—Ethyl 5-(2-oxa-6-azaspiro[3.3]heptan-6-yl)pyrazolo[1,5-a]pyrimidine-3-carboxylate To a solution of ethyl 5-chloropyrazolo[1,5-a]pyrimidine-3-carboxylate (230 mg, 1.02 mmol, CAS #1224944-77-7) and 2-oxa-6-azaspiro[3.3]heptane (121 mg, 1.22 mmol, CAS #174-78-7) in ACN (2 mL) was added DIPEA (18.7 mg, 144 umol) at 25° C. The reaction mixture was stirred at 60° C. for 2 hours. On completion, the reaction mixture was concentrated in vacuo to give the title compound (570 mg, 96% yield, 50% purity) as a yellow solid. $^1H$ NMR (400 MHz, DMSO-$d_6$) δ 8.69 (d, J=7.6 Hz, 1H), 8.18 (s, 1H), 6.35 (d, J=7.6 Hz, 1H), 4.74 (s, 4H), 4.32 (s, 4H), 4.18 (q, J=7.2 Hz, 2H), 1.28 (s, 3H); LC-MS (ESI$^+$) m/z 289.5 (M+H)$^+$.

Step 2—5-(2-Oxa-6-azaspiro[3.3]heptan-6-yl)pyrazolo[1,5-a]pyrimidine-3-carboxylic acid To a solution of ethyl 5-(2-oxa-6-azaspiro[3.3]heptan-6-yl)pyrazolo[1,5-a]pyrimidine-3-carboxylate (140 mg, 242 umol) in $H_2O$ (5 mL) and THF (5 mL) was added LiOH—

H₂O (50.9 mg, 1.21 mmol) at 25° C. The reaction mixture was stirred at 60° C. for 2 hours. On completion, the reaction mixture was added of 1 M aq HCl to pH=4-5 and and then concentrated in vacuo. The residue was purified by reverse phase (0.1% FA condition) to give the title compound (70.0 mg, 94% yield, FA salt) as a yellow solid. $^1$H NMR (400 MHz, DMSO-d$_6$) δ 8.68 (d, J=7.6 Hz, 1H), 8.16 (s, 1H), 6.33 (d, J=7.6 Hz, 1H), 4.73 (s, 4H), 4.33 (s, 4H); LC-MS (ESI$^+$) m/z 243.1 (M−17)$^+$.

4-[3-[[1-[[4-[4-Amino-3-(difluoromethyl)pyrazol-1-yl]cyclohexyl]methyl]-4-piperidyl]oxy] propylamino]-2-(2,6-dioxo-3-piperidyl)isoindoline-1,3-dione (Intermediate AGS)

eridyloxy) propylamino]isoindoline-1,3-dione (141 mg, 342 umol, Intermediate AFJ) were added to the mixture and the mixture was stirred at 25° C. for 20 minutes. Next, NaBH(OAc)$_3$ (145 mg, 684 umol) was added to the mixture at 0° C. Then the reaction mixture was stirred at 25° C. for 2 hrs. On completion, the mixture was quenched with 1 mL H₂O and was concentrated in vacuo to give a residue. The residue was purified by reverse phase (0.1% FA condition) to give the title compound (130 mg, 51% yield) as yellow solid. $^1$H NMR (400 MHz, DMSO-d$_6$) δ 11.08 (s, 1H), 8.88 (s, 1H), 7.86 (s, 1H), 7.58 (dd, J=7.2, 8.4 Hz, 1H), 7.15-6.84 (m, 3H), 6.63 (t, J=5.6 Hz, 1H), 5.05 (dd, J=5.2, 12.8 Hz, 1H), 4.16-4.02 (m, 1H), 3.49 (t, J=5.6 Hz, 2H), 3.40-3.34 (m, 4H), 3.29-3.23 (m, 2H), 2.94-2.83 (m, 1H), 2.65-2.54 (m, 2H), 2.10 (d, J=7.2 Hz, 2H), 2.07-1.94 (m, 5H), 1.89-1.76

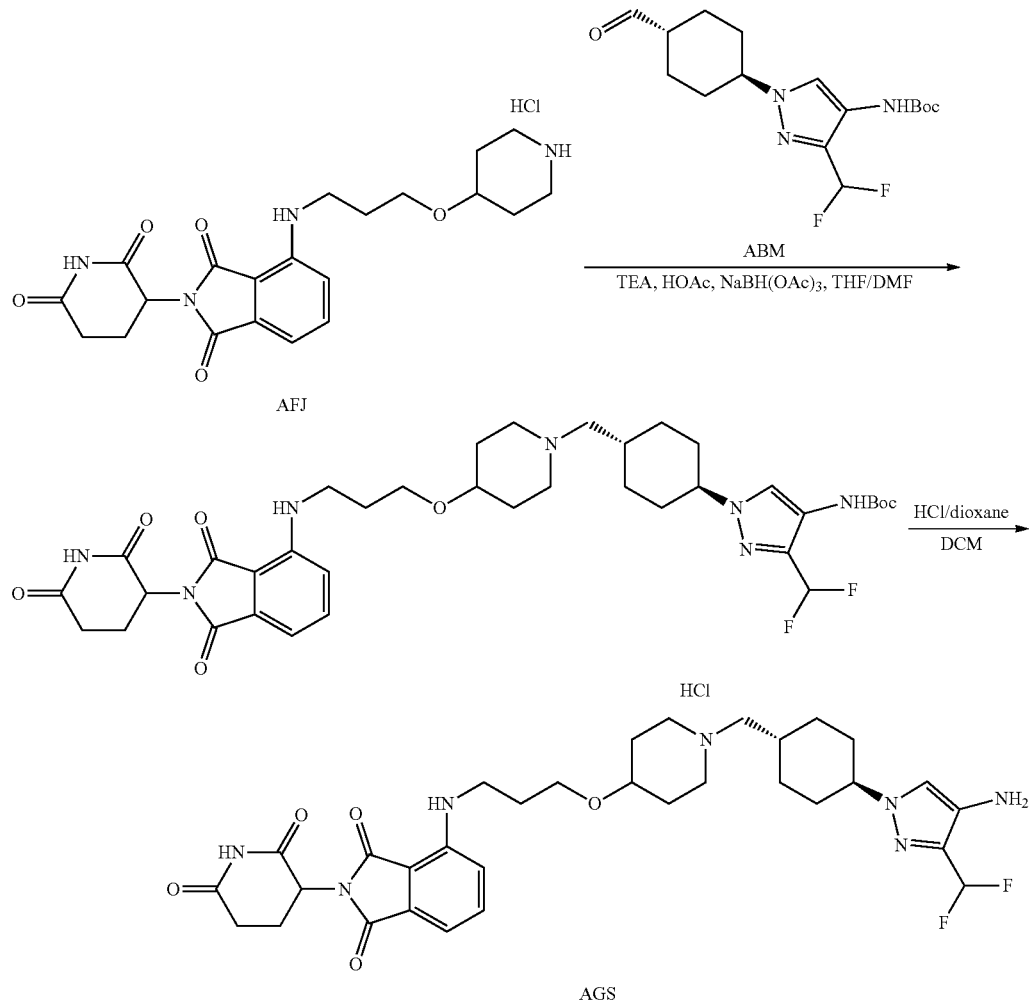

Step 1—Tert-butyl N-[3-(difluoromethyl)-1-[4-[[4-[3-[[2-(2,6-dioxo-3-piperidyl)-1,3-dioxo-isoindolin-4-yl]amino]propoxy]-1-piperidyl]methyl] cyclohexyl]pyrazol-4-yl]carbamate To a solution of tert-butyl N-[3-(difluoromethyl)-1-(4-formylcyclohexyl)pyrazol-4-yl]carbamate (130 mg, 342 umol, HCl salt, Intermediate ABM) in THF (3 mL) and DMF (1 mL) was added TEA (34.6 mg, 342 umol). Then the mixture was stirred at 25° C. for 10 minutes, HOAc (20.5 mg, 342 umol) and 2-(2,6-dioxo-3-piperidyl)-4-[3-(4-pip- (m, 6H), 1.75-1.64 (m, 2H), 1.58-1.46 (m, 2H), 1.44 (s, 9H), 1.07-0.92 (m, 2H); LC-MS (ESI$^+$) m/z 742.5 (M+H)$^+$.

Step 2—4-[3-[[1-[[4-[4-Amino-3-(difluoromethyl) pyrazol-1-yl] cyclohexyl]methyl]-4-piperidyl]oxy] propylamino]-2-(2,6-dioxo-3-piperidyl)isoindoline-1,3-dione To a solution of tert-butyl N-[3-(difluoromethyl)-1-[4-[[4-[3-[[2-(2,6-dioxo-3-piperidyl)-1,3-dioxo-isoindolin-4-yl]amino]propoxy]-1-piperidyl]methyl]cyclohexyl]pyrazol-4- yl]carbamate (60.0 mg, 80.8 umol) in DCM (3 mL) was added HCl/dioxane (4 M, 2 mL). The mixture was stirred at 15° C. for 2 hrs. On completion, the mixture was concentrated in vacuo to give the title compound (50.0 mg, 91% yield, HCl salt) as yellow solid. LC-MS (ESI$^+$) m/z 642.3 (M+H)$^+$.

Tert-butyl 4-(2-aminoethoxy)piperidine-1-carboxylate (Intermediate AGT)

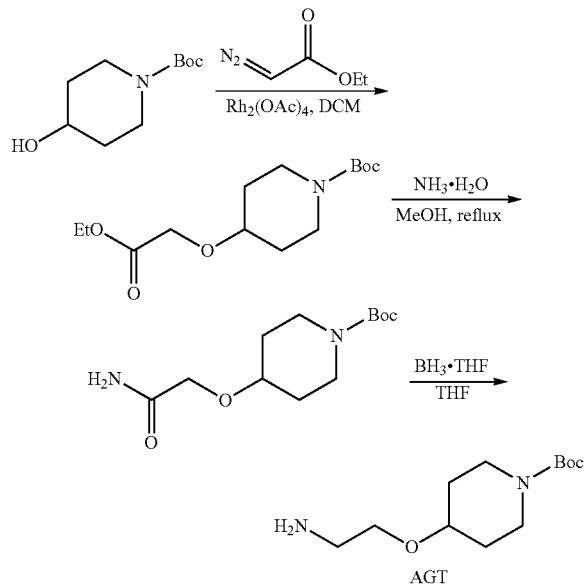

Step 1—Tert-butyl 4-(2-ethoxy-2-oxo-ethoxy)piperidine-1-carboxylate

To a solution of tert-butyl 4-hydroxypiperidine-1-carboxylate (9.00 g, 44.7 mmol, CAS #109384-19-2) and Rh$_2$(OAc)$_4$ (988 mg, 2.24 mmol) in DCM (60 mL) was added a solution of ethyl 2-diazoacetate (20.4 g, 178 mmol, CAS #623-73-4) in DCM (60 mL) at 0° C. during 2 hours. The reaction mixture was stirred at 0-25° C. for 46 hours. On completion, the reaction was quenched with HOAc (10 mL) and the mixture was concentrated in vacuo. The residue was purified by column chromatography to give the title compound (7.00 g, 54% yield) as yellow oil. $^1$H NMR (400 MHz, CDCl$_3$) δ 4.21-4.18 (m, 2H), 4.09 (s, 2H), 3.82-3.69 (m, 2H), 3.60-3.48 (m, 1H), 3.12-3.00 (m, 2H), 1.88-1.76 (m, 2H), 1.61-1.50 (m, 2H), 1.43 (s, 9H), 1.28-1.25 (m, 3H).

Step 2—Tert-butyl 4-(2-amino-2-oxo-ethoxy)piperidine-1-carboxylate

To a solution of tert-butyl 4-(2-ethoxy-2-oxo-ethoxy)piperidine-1-carboxylate (1.00 g, 3.48 mmol) in MeOH (10 mL) was added NH$_3$—H$_2$O (64.9 mmol, 10 mL, 25% solution) at 25° C. The mixture was stirred at 65° C. for 24 hours. On completion, the mixture was diluted with H$_2$O (30 mL), and extracted with EA 30 mL (3×10 mL). The combined organic layers were washed with H$_2$O (3×10 mL), dried over Na$_2$SO$_4$, filtered and concentrated in vacuo to give the title compound (640 mg, 71% yield) as yellow solid.

$^1$H NMR (400 MHz, CDCl$_3$) δ 6.52 (s, 1H), 5.89 (s, 1H), 3.98 (s, 2H), 3.85-3.71 (m, 2H), 3.61-3.50 (m, 1H), 3.18-3.05 (m, 2H), 1.91-1.81 (m, 2H), 1.61-1.49 (m, 2H), 1.46 (s, 9H).

Step 3—Tert-butyl 4-(2-aminoethoxy)piperidine-1-carboxylate

To a solution of tert-butyl 4-(2-amino-2-oxo-ethoxy)piperidine-1-carboxylate (240 mg, 929 umol) in THF (7 mL) was added BH$_3$.THF (1 M, 2.79 mL) at 25° C. The reaction mixture was stirred at 70° C. for 12 hours. On completion, to the mixture was added MeOH (20 mL) at 25° C. The mixture was stirred at 70° C. for 1 hour. Then, the mixture was concentrated in vacuo to give the title compound (220 mg, 77% yield) as white solid.

2-(2,6-Dioxo-3-piperidyl)-4-[2-(4-piperidyloxy)ethylamino]isoindoline-1,3-dione (Intermediate AGU)

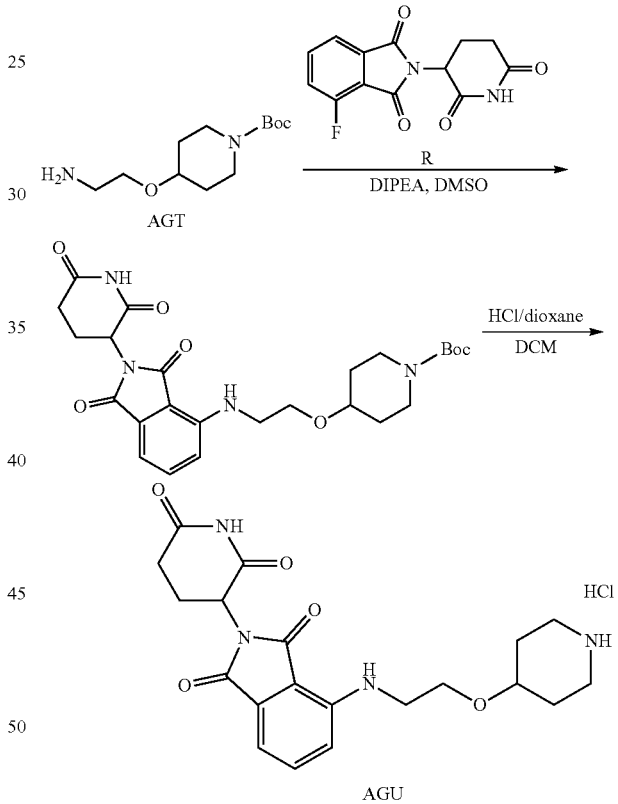

Step 1—Tert-butyl 4-[2-[[2-(2,6-dioxo-3-piperidyl)-1,3-dioxo-isoindolin-4-yl]amino]ethoxy] piperidine-1-carboxylate To a solution of tert-butyl 4-(2-aminoethoxy)piperidine-1-carboxylate (220 mg, 720 umol, Intermediate AGT) and 2-(2,6-dioxo-3-piperidyl)-4-fluoro-isoindoline-1,3-dione (198 mg, 720 umol, Intermediate R) in DMSO (6 mL) was added DIPEA (18.7 mg, 144 umol) at 25° C. The reaction mixture was stirred at 130° C. for 2 hours. On completion, the reaction mixture was concentrated in vacuo. The residue was purified by reverse phase (0.1% FA condition) to give the title compound (200 mg, 55% yield) as a yellow solid. $^1$H NMR (400 MHz, DMSO-d$_6$) δ 11.08 (s, 1H), 7.59 (dd, J=7.2, 8.4 Hz, 1H), 7.16 (d, J=8.8 Hz, 1H), 7.04 (d, J=7.2 Hz, 1H), 6.62 (t, J=5.6 Hz, 1H), 5.06 (dd, J=5.2, 12.8 Hz, 1H), 3.66-3.62 (m, 2H), 3.59-3.50 (m, 2H), 3.49-3.42 (m, 2H), 3.09-2.99 (m, 2H), 2.93-2.83 (m, 1H), 2.62-2.53 (m, 2H), 2.52 (s, 2H), 2.07-1.98 (m, 1H), 1.82-1.72 (m, 2H), 1.38 (s, 9H), 1.36-1.31 (m, 1H); LC-MS (ESI$^+$) m/z 401.5 (M+H−100)$^+$.

Step 2—2-(2,6-Dioxo-3-piperidyl)-4-[2-(4-piperidyloxy)ethylamino]isoindoline-1,3-dione To a solution of tert-butyl 4-[2-[[2-(2,6-dioxo-3-piperidyl)-1,3-dioxo-isoindolin-4-yl]amino]ethoxy] piperidine-1-carboxylate (55.0 mg, 109 umol) in DCM (3 mL) was added HCl/dioxane (4 M, 2 mL). The mixture was stirred at 15° C. for 2 hours. On completion, the reaction mixture was concentrated in vacuo to give the title compound (47.0 mg, 97% yield, HCl salt) as a yellow solid. LC-MS (ESI$^+$) m/z 401.2 (M+H)$^+$.

N-[1-(4-formylcyclohexyl)-3-(1-hydroxy-1-methyl-ethyl)pyrazol-4-yl]-5-morpholino-pyrazolo[1,5-a]pyrimidine-3-carboxamide (Intermediate AGV)

Step 1—N-[1-[4-(hydroxymethyl)cyclohexyl]-3-(1-hydroxy-1-methyl-ethyl)pyrazol-4-yl]-5-morpholino-pyrazolo[1,5-a]pyrimidine-3-carboxamide To a solution of 2-[4-amino-1-[4-(hydroxymethyl)cyclohexyl]pyrazol-3-yl]propan-2-ol (300 mg, 1.18 mmol, synthesized via Step 1 of Intermediate UW) in DMF (3 mL) and ACN (10 mL) was added [chloro(dimethylamino) methylene]-dimethyl-ammonium; hexafluorophosphate (498 mg, 1.78 mmol). The mixture stirred at 25° C. for 30 minutes. Next, 1-methylimidazole (340 mg, 4.14 mmol) was added and the mixture was stirred at 25° C. for 30 minutes. Then, 5-morpholinopyrazolo[1,5-a]pyrimidine-3-carboxylic acid (264 mg, 1.07 mmol, Intermediate ABB) was added at 25° C. The reaction mixture was stirred at 25° C. for 1 hour. On completion, the reaction was quenched with H$_2$O (0.5 mL). The mixture was concentrated in vacuo. The residue was purified by reverse phase (0.1% FA condition) to give the title compound (500 mg, 87% yield) as a white solid. $^1$H NMR (400 MHz, DMSO-d$_6$) δ 9.76 (s, 1H), 8.76 (d, J=8.0 Hz, 1H), 8.23 (s, 1H), 6.84 (d, J=8.0 Hz, 1H), 5.42 (s, 1H), 4.03-3.95 (m, 1H), 3.90-3.85 (m, 2H), 3.77 (s, 1H), 3.70 (t, J=4.8 Hz, 4H), 3.25 (d, J=6.4 Hz, 2H), 2.02 (d, J=10.4 Hz, 2H), 1.85 (d, J=11.6 Hz, 2H), 1.72-1.58 (m, 2H), 1.46 (s, 6H), 1.43-1.37 (m, 1H), 1.14-1.00 (m, 2H).

Step 2—N-[1-(4-formylcyclohexyl)-3-(1-hydroxy-1-methyl-ethyl)pyrazol-4-yl]-5-morpholino-pyrazolo[1,5-a]pyrimidine-3-carboxamide To a solution of N-[1-[4-(hydroxymethyl)cyclohexyl]-3-(1-hydroxy-1-methyl-ethyl)pyrazol-4-yl]-5-morpholino-pyrazolo[1,5-a]pyrimidine-3-carboxamide (180 mg, 372 umol) in DCM (5 mL) was added DMP (189 mg, 446 umol) at 0° C. The reaction mixture was stirred at 25° C. for 2 hours. On completion, the reaction was quenched with sat. aq. Na$_2$S$_2$O$_3$ (5 mL) and NaHCO$_3$ (5 mL). The mixture was extracted with DCM (3×5 mL) and the combined organic layers were concentrated in vacuo. The residue was purified by reverse phase (0.1% FA condition) to give the title compound (260 mg, 87% yield) as a white solid. $^1$H NMR (400 MHz, DMSO-d$_6$) δ 9.77 (s, 1H), 9.61 (s, 1H), 8.77 (d, J=8.0 Hz, 1H), 8.24 (s, 1H), 6.84 (d, J=8.0 Hz, 1H), 5.46 (s, 1H), 4.08-4.00 (m, 1H), 3.88 (s, 4H), 3.77 (s, 1H), 3.70 (t, J=4.4 Hz, 4H), 2.38 (t, J=12.8 Hz, 1H), 2.09-2.01 (m, 4H), 1.80-1.70 (m, 2H), 1.46 (s, 6H), 1.42-1.32 (m, 2H).

2-(2,6-Dioxo-3-piperidyl)-4-[4-(methylaminomethyl)-1-piperidyl]isoindoline-1,3-dione (Intermediate AGW)

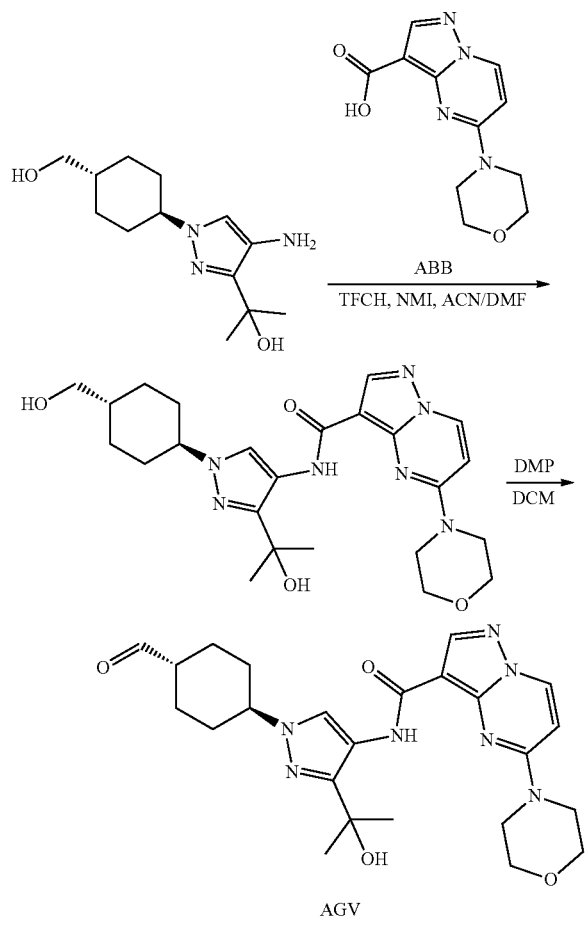

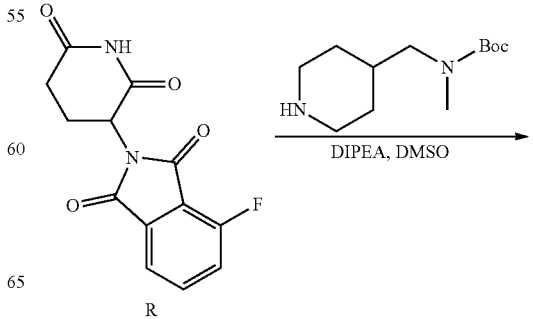

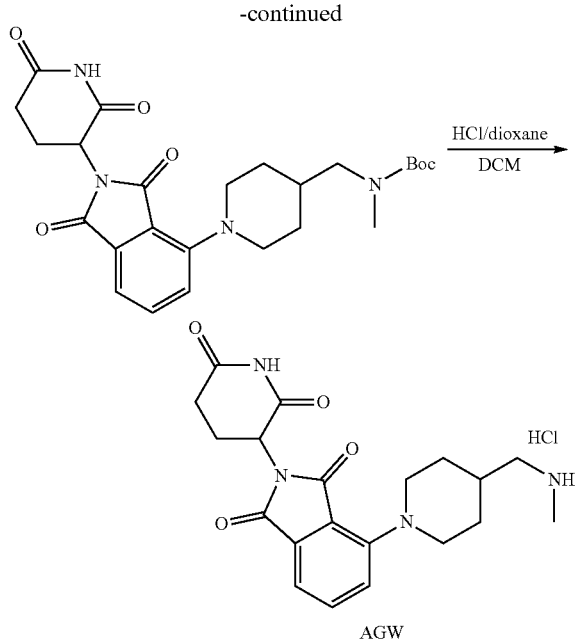

Step 1—Tert-butyl N-[[1-[2-(2,6-dioxo-3-piperidyl)-1,3-dioxo-isoindolin-4-yl]-4-piperidyl]methyl]-N-methyl-carbamate To a solution of 2-(2,6-dioxo-3-piperidyl)-4-fluoro-isoindoline-1,3-dione (302 mg, 1.09 mmol, Intermediate R) and tert-butyl N-methyl-N-(4-piperidylmethyl)carbamate (250 mg, 1.09 mmol, CAS #138022-04-5) in DMSO (12 mL) was added DIPEA (18.7 mg, 144 umol) at 25° C. The reaction mixture was stirred at 130° C. for 2 hrs. On completion, the reaction mixture was concentrated in vacuo to give a residue. The residue was purified by reverse phase (0.1% FA condition) to give the title compound (530 mg, 99% yield) as a yellow solid. $^1$H NMR (400 MHz, DMSO-d$_6$) δ 11.07 (s, 1H), 7.68 (dd, J=7.2, 8.4 Hz, 1H), 7.36-7.28 (m, 2H), 5.09 (dd, J=5.2, 12.4 Hz, 1H), 3.70 (d, J=11.6 Hz, 2H), 3.12 (d, J=6.8 Hz, 2H), 2.92-2.78 (m, 6H), 2.63-2.52 (m, 2H), 2.07-1.97 (m, 1H), 1.86-1.73 (m, 1H), 1.67 (d, J=11.2 Hz, 2H), 1.40 (s, 9H), 1.39-1.30 (m, 2H); LC-MS (ESI$^+$) m/z 485.4 (M+H)$^+$.

Step 2—2-(2,6-Dioxo-3-piperidyl)-4-[4-(methylaminomethyl)-1-piperidyl]isoindoline-1,3-dione To a solution of tert-butyl N-[[1-[2-(2,6-dioxo-3-piperidyl)-1,3-dioxo-isoindolin-4-yl]-4-piperidyl] methyl]-N-methyl-carbamate (95.0 mg, 144 umol) in DCM (5 mL) was added HCl/dioxane (4 M, 3 mL). The mixture was stirred at 25° C. for 2 hrs. On completion, the reaction mixture was concentrated in vacuo to give the title compound (80.0 mg, 98% yield, HCl salt) as a yellow solid. LC-MS (ESI$^+$) m/z 385.1 (M+H)$^+$.

N1,N4-dimethylcyclohexane-1,4-diamine (Intermediate AGX)

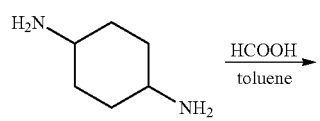

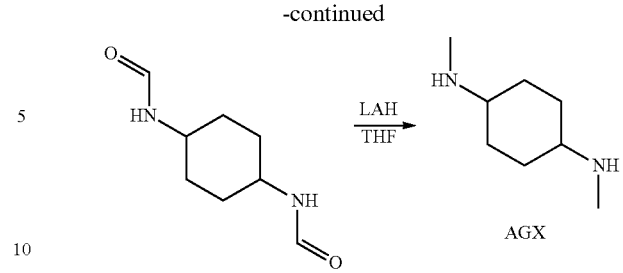

Step 1—N-(4-formamidocyclohexyl)formamide

A mixture of cyclohexane-1,4-diamine (5.00 g, 43.7 mmol) and HCOOH (8.41 g, 175 mmol) in toluene (80 mL) was stirred at 120° C. for 16 hours. On completion, the mixture was concentrated in vacuo to give the title compound (7.40 g, 99% yield) as yellow oil. $^1$H NMR (400 MHz, DMSO-d$_6$) δ 8.25 (s, 2H), 3.76-3.66 (m, 1H), 3.61-3.43 (m, 1H), 1.76-1.76 (m, 1H), 2.00-1.65 (m, 2H), 1.58-1.47 (m, 3H), 1.42-1.16 (m, 2H).

Step 2—N1,N4-dimethylcyclohexane-1,4-diamine

To a solution of N-(4-formamidocyclohexyl)formamide (3.00 g, 17.6 mmol) in THF (50 mL) was added LAH (2.01 g, 52.8 mmol) in portions at 0° C. The mixture was stirred at 15° C. for 1 hour. Then, the mixture was stirred at 70° C. for 5 hours. On completion, after cooled to 15° C., the reaction was quenched with water (2.0 mL). Then 15% aq.NaOH (2.0 mL) and water (6.0 mL) was added to the reaction mixture. The mixture was filtered and concentrated in vacuo to give the title compound (2.50 g, 99% yield) as light yellow oil.

2-(2,6-Dioxo-3-piperidyl)-4-[methyl-[4-(methylamino)cyclohexyl]amino]isoindoline-1,3-dione (Intermediate AGY)

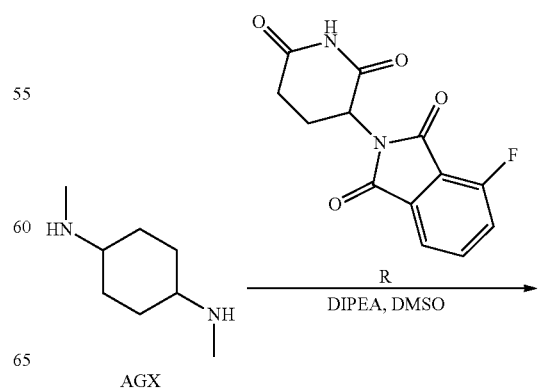

-continued

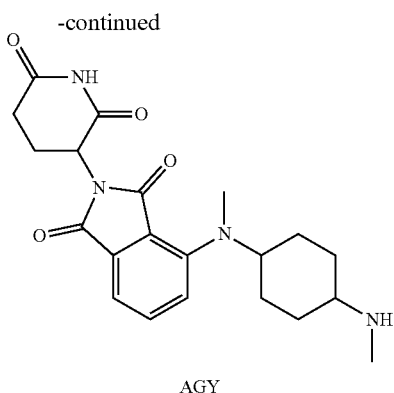

AGY

A mixture of N1,N4-dimethylcyclohexane-1,4-diamine (400 mg, 2.81 mmol, Intermediate AGX), 2-(2,6-dioxo-3-piperidyl)-4-fluoro-isoindoline-1,3-dione (200 mg, 724 umol, Intermediate R) and DIPEA (280 mg, 2.17 mmol) in DMSO (2.0 mL) was stirred at 130° C. for 2 hours. On completion, after cooled to 15° C., the reaction was quenched with water (0.5 mL). The mixture was concentrated in vacuo. The residue was purified by reverse phase flash (TFA condition) to give the title compound (70.0 mg, 18% yield, TFA salt) as light yellow gum. LC-MS (ESI⁺) m/z 399.2 (M+H)⁺.

Benzyl N-methyl-N-(3-piperazin-1-ylpropyl)carbamate (Intermediate AGZ)

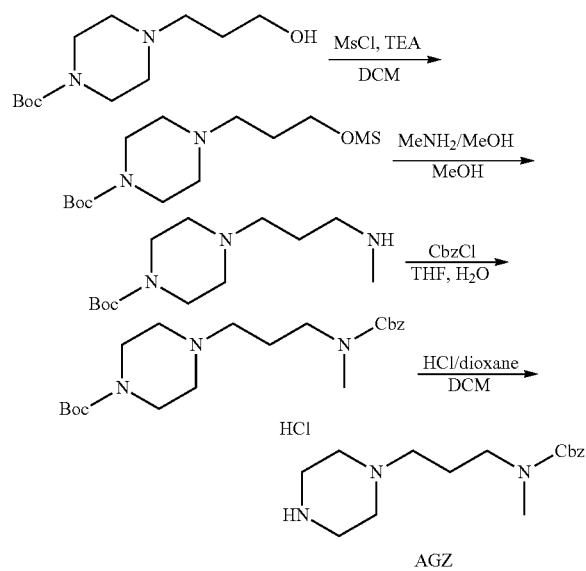

Step 1—Tert-butyl 4-(3-methylsulfonyloxypropyl) piperazine-1-carboxylate

To a solution of tert-butyl 4-(3-hydroxypropyl)piperazine-1-carboxylate (1.00 g, 4.09 mmol, CAS #132710-90-8) and TEA (621 mg, 6.14 mmol) in DCM (15 mL) was added MsCl (562 mg, 4.91 mmol) at 0° C. The reaction mixture was stirred at 0-20° C. for 1 hr. On completion, the reaction mixture was diluted with water (20 mL) and extracted with DCM (3×25 mL). The combined organic layers were washed with brine (3×30 mL), dried over Na$_2$SO$_4$, filtered and concentrated in vacuo to give the title compound (1.30 g, 98% yield) as yellow oil. $^1$H NMR (400 MHz, CDCl$_3$) δ 4.33 (t, J=6.4 Hz, 2H), 3.55-3.40 (m, 4H), 3.03 (s, 3H), 2.61-2.37 (m, 6H), 2.05-1.93 (m, 2H), 1.46 (s, 9H).

Step 2—Tert-butyl 4-[3-(methylamino)propyl]piperazine-1-carboxylate

A mixture of tert-butyl 4-(3-methylsulfonyloxypropyl) piperazine-1-carboxylate (1.30 g, 4.03 mmol) in MeNH$_2$/EtOH (4.03 mmol, 10 mL, 30% solution) was stirred at 70° C. for 16 hrs in a sealed tube. On completion, the reaction mixture was concentrated in vacuo to give the title compound (1.20 g, 98% yield) as yellow oil. $^1$H NMR (400 MHz, CDCl$_3$) δ 3.49-3.40 (m, 4H), 3.09 (t, J=6.8 Hz, 2H), 2.72 (s, 3H), 2.53 (t, J=6.4 Hz, 2H), 2.44 (t, J=4.8 Hz, 4H), 1.97 (t, J=6.8 Hz, 2H), 1.46 (s, 9H).

Step 3—Tert-butyl 4-[3-[benzyloxycarbonyl (methyl)amino]propyl]piperazine-1-carboxylate To a solution of tert-butyl 4-[3-(methylamino)propyl] piperazine-1-carboxylate (1.20 g, 3.96 mmol) and K$_2$CO$_3$ (1.10 g, 7.93 mmol) in a mixed solvent of THF (15 mL) and water (5 mL) was added CbzCl (1.01 g, 5.94 mmol). The reaction mixture was stirred at 15° C. for 2 hrs. On completion, the reaction mixture was diluted with water (30 mL) and extracted with EA (3×50 mL). The combined organic layers were washed with brine (3×30 mL), dried over Na$_2$SO$_4$, filtered and concentrated in vacuo. The residue was purified by silica gel chromatography (PE:EA=1:1) to give the title compound (1.10 g, 70% yield) as yellow oil $^1$H NMR (400 MHz, CDCl$_3$) δ 7.40-7.30 (m, 5H), 5.13 (s, 2H), 3.47-3.23 (m, 6H), 2.94 (s, 3H), 2.44-2.23 (m, 6H), 1.80-1.69 (m, 2H), 1.47 (s, 9H).

Step 4—Benzyl N-methyl-N-(3-piperazin-1-ylpropyl)carbamate

To a solution of tert-butyl 4-[3-[benzyloxycarbonyl (methyl)amino]propyl]piperazine-1-carboxylate (1.10 g, 2.81 mmol) in DCM (10 mL) was added HCl/dioxane (4 M, 10 mL). The reaction mixture was stirred at 15° C. for 0.5 hr. On completion, the reaction mixture was concentrated in vacuo to give the title compound (1.00 g, 88% yield) as yellow solid. $^1$H NMR (400 MHz, DMSO-d$_6$) δ 12.39-11.63 (m, 1H), 10.24-8.93 (m, 3H), 7.46-7.27 (m, 5H), 5.07 (s, 2H), 3.74-3.58 (m, 2H), 3.46-3.38 (m, 4H), 3.31 (t, J=6.0 Hz, 3H), 3.27-3.21 (m, 1H), 3.14-3.03 (m, 2H), 2.93-2.79 (m, 3H), 2.03-1.87 (m, 2H).

2-(2,6-Dioxo-3-piperidyl)-4-[4-[3-(methylamino) propyl]piperazin-1-yl]isoindoline-1,3-dione (Intermediate AHA)

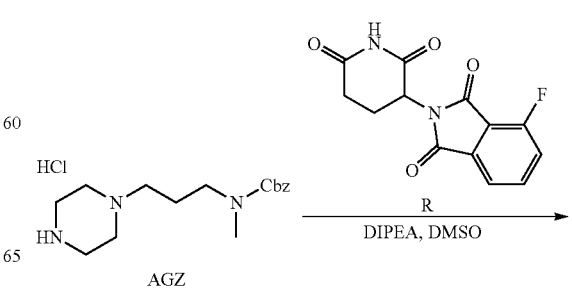

1863

-continued

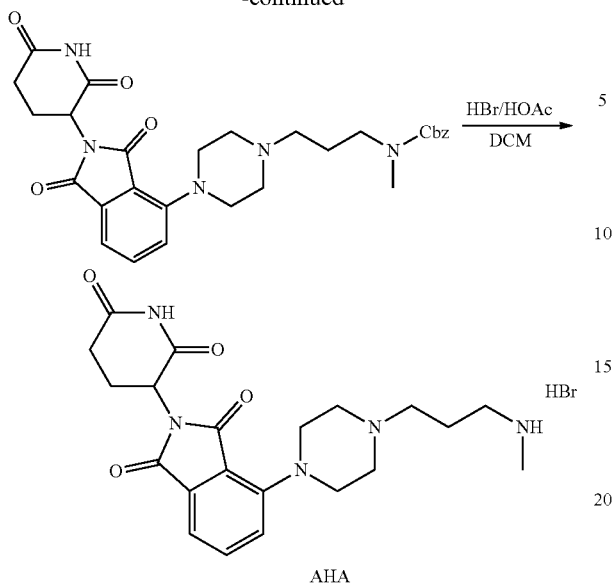

AHA

Step 1—Benzyl N-[3-4-[2-(2,6-dioxo-3-piperidyl)-1,3-dioxo-isoindolin-4-yl]piperazin-1-yl]propyl]-N-methyl-carbamate To a solution of 2-(2,6-dioxo-3-piperidyl)-4-fluoro-isoindoline-1,3-dione (300 mg, 1.09 mmol, Intermediate R) and benzyl N-methyl-N-(3-piperazin-1-ylpropyl)carbamate (391 mg, 977 umol, Intermediate AGZ) in DMSO (8 mL) was added DIPEA (1.40 g, 10.8 mmol). The reaction mixture was stirred at 130° C. for 3 hrs. On completion, the reaction mixture was diluted with water (50 mL) and extracted with EA (3×50 mL). The combined organic layers were washed with brine (3×30 mL), dried over $Na_2SO_4$, filtered and concentrated in vacuo. The residue was purified by reverse phase (0.1% FA) to give the title compound (400 mg, 62% yield, FA salt) as yellow solid. $^1$H NMR (400 MHz, $CDCl_3$) δ 8.14 (s, 1H), 7.66-7.57 (m, 1H), 7.44 (d, J=7.2 Hz, 1H), 7.40-7.29 (m, 5H), 7.20-7.11 (m, 1H), 5.14 (s, 2H), 4.97 (dd, J=5.2, 12.0 Hz, 1H), 3.52-3.25 (m, 6H), 2.95 (s, 3H), 2.92-2.84 (m, 4H), 2.83-2.76 (m, 2H), 2.75-2.72 (m, 1H), 2.67-2.59 (m, 1H), 2.53-2.45 (m, 1H), 2.19-2.07 (m, 1H), 1.96-1.76 (m, 2H).

Step 2—2-(2,6-Dioxo-3-piperidyl)-4-[4-[3-(methylamino)propyl]piperazin-1-yl]isoindoline-1,3-dione To a solution of benzyl N-[3-[4-[2-(2,6-dioxo-3-piperidyl)-1,3-dioxo-isoindolin-4-yl]piperazin-1-yl] propyl]-N-methyl-carbamate (400 mg, 673 umol, FA salt) in DCM (5 mL) was added HBr/AcOH (673 umol, 5 mL, 30% solution). The reaction mixture was stirred at 15° C. for 2 hrs. On completion, the reaction mixture was concentrated in vacuo to give the title compound (330 mg, 99% yield, HBr salt) as yellow solid. $^1$H NMR (400 MHz, DMSO-$d_6$) δ 11.10 (s, 1H), 8.66-8.53 (m, 2H), 7.78 (dd, J=7.2, 8.4 Hz, 1H), 7.45 (dd, J=8.0, 12.8 Hz, 2H), 5.11 (dd, J=5.6, 12.8 Hz, 1H), 3.88 (t, J=10.8 Hz, 2H), 3.68 (d, J=10.4 Hz, 2H), 3.48-3.14 (m, 6H), 3.08-2.96 (m, 2H), 2.95-2.83 (m, 1H), 2.64-2.51 (m, 5H), 2.16-2.07 (m, 2H), 2.07-1.99 (m, 1H).

1864

2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetic acid (CAS #13520266-68-2) (Intermediate AHB)

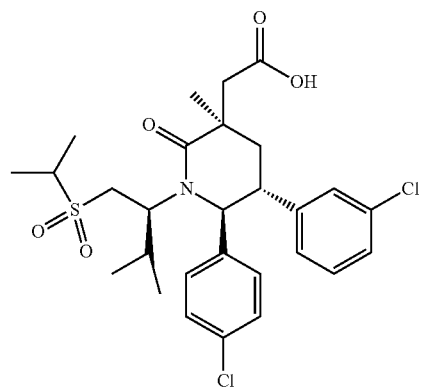

2-[(3R,5R,6S)-5-(3-chlorophenyl)-6-(4-chlorophenyl)-1-[(1S)-1-(isopropylsulfonylmethyl)-2-methyl-propyl]-3-methyl-2-oxo-3-piperidyl]acetic acid is commercially available CAS #13520266-68-2.

3-[[2-(2,6-Dioxo-3-piperidyl)-1,3-dioxo-isoindolin-4-yl]amino]propanal (Intermediate AHC)

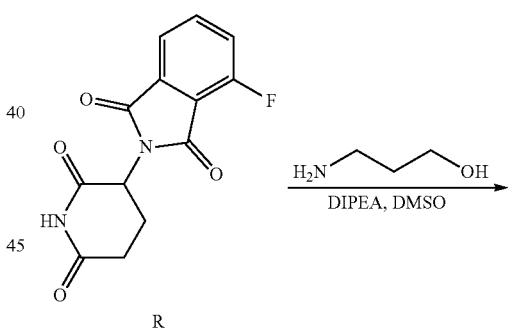

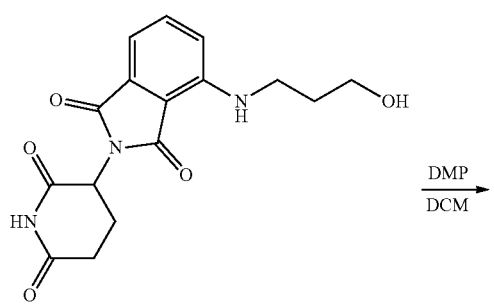

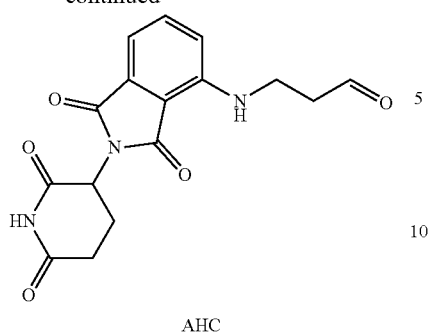

AHC

Step 1—2-(2,6-Dioxo-3-piperidyl)-4-(3-hydroxypropylamino)isoindoline-1,3-dione To a solution of 2-(2,6-dioxo-3-piperidyl)-4-fluoro-isoindoline-1,3-dione (500 mg, 1.81 mmol, Intermediate R) and 3-aminopropan-1-ol (163 mg, 2.17 mmol, 167 uL, CAS #156-87-6) in DMSO (6 mL) was added DIPEA (701 mg, 5.43 mmol, 945 uL), the reaction mixture was stirred at 130° C. for 16 hours. On completion, the mixture was concentrated in vacuo to give a residue. The residue was purified by reverse phase (0.1% FA condition) to give the title compound (400 mg, 67% yield) as a yellow solid. H NMR (400 MHz, DMSO-$d_6$) δ 11.09 (s, 1H), 7.62-7.55 (m, 1H), 7.09 (d, J=8.8 Hz, 1H), 7.01 (d, J=6.8 Hz, 1H), 6.74-6.61 (m, 1H), 5.05 (dd, J=5.2, 12.8 Hz, 1H), 4.80-4.55 (m, 1H), 3.51 (t, J=6.0 Hz, 2H), 3.38-3.34 (m, 2H), 2.93-2.83 (m, 1H), 2.63-2.54 (m, 2H), 2.07-1.98 (m, 1H), 1.75-1.70 (m, 2H); LC-MS (ESI$^+$) m/z 332.1 (M+H)$^+$.

Step 2—3-[[2-(2,6-Dioxo-3-piperidyl)-1,3-dioxo-isoindolin-4-yl]amino]propanal To a solution of 2-(2,6-dioxo-3-piperidyl)-4-(3-hydroxypropylamino)isoindoline-1,3-dione (100 mg, 301 umol) in DCM (5 mL) was added DMP (153 mg, 362 umol). The reaction mixture was stirred at 20° C. for 1 hour. On completion, the reaction mixture was quenched with saturated aqueous $Na_2S_2O_3$ (10 mL) and extracted with DCM (2×30 mL). The combined organic phase was washed with $NaHCO_3$ and brine (2×20 mL), dried with anhydrous $Na_2SO_4$, filtered and concentrated in vacuo to give the title compound (80.0 mg, 80.5% yield) as a yellow solid. $^1$H NMR (400 MHz, DMSO-$d_6$) δ 11.09 (s, 1H), 9.72 (s, 1H), 7.63-7.57 (m, 1H), 7.15 (d, J=8.8 Hz, 1H), 7.04 (d, J=7.2 Hz, 1H), 6.63 (t, J=6.0 Hz, 1H), 5.04 (dd, J=5.2, 12.8 Hz, 1H), 3.64-3.57 (m, 2H), 2.93-2.83 (m, 1H), 2.80 (t, J=6.0 Hz, 2H), 2.62-2.51 (m, 2H), 2.06-1.98 (m, 1H); LC-MS (ESI$^+$) m/z 330.0 (M+H)$^+$.

2-(2,6-Dioxo-3-piperidyl)-4-[3-[methyl(4-piperidyl)amino]propylamino]isoindoline-1,3-dione (Intermediate AHD)

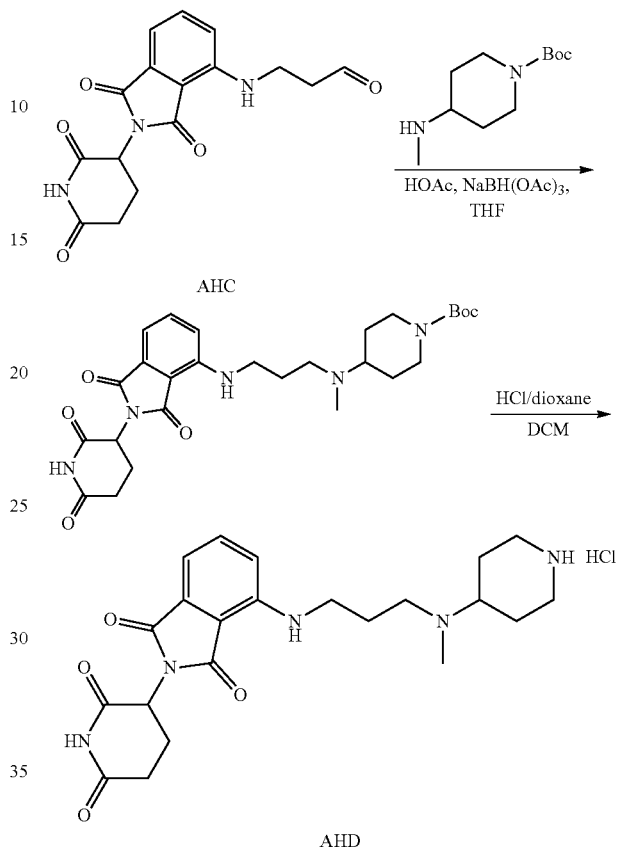

Step 1—Tert-butyl 4-[3-[[2-(2,6-dioxo-3-piperidyl)-1,3-dioxo-isoindolin-4-yl]amino]propyl-methylamino]piperidine-1-carboxylate To a solution of 3-[[2-(2,6-dioxo-3-piperidyl)-1,3-dioxo-isoindolin-4-yl]amino]propanal (75.0 mg, 227 umol, Intermediate AHC) and tert-butyl 4-(methylamino)piperidine-1-carboxylate (48.8 mg, 227 umol, CAS #147539-41-1) in THF (5 mL) was added HOAc (27.3 mg, 455 umol, 26.0 uL). The reaction mixture was stirred at 20° C. for 30 minutes. Then NaBH(OAc)$_3$ (62.7 mg, 296 umol) was added, and the mixture was stirred at 20° C. for 12 hours. On completion, the reaction mixture was quenched with $H_2O$ (0.5 mL), and then concentrated in vacuo to give a residue. The residue was purified by reverse phase (0.1% FA condition) to give the title compound (105 mg, 87.4% yield) as a yellow solid. $^1$H NMR (400 MHz, DMSO-$d_6$) δ 11.08 (s, 1H), 7.61-7.55 (m, 1H), 7.09 (d, J=8.8 Hz, 1H), 7.01 (d, J=6.8 Hz, 1H), 6.91-6.82 (m, 1H), 5.05 (dd, J=5.2, 12.8 Hz, 1H), 3.99-3.93 (m, 2H), 3.36-3.29 (m, 2H), 2.94-2.79 (m, 1H), 2.65-2.55 (m, 5H), 2.24 (s, 3H), 2.06-1.97 (m, 1H), 1.75-1.67 (m, 4H), 1.38 (s, 9H), 1.34-1.23 (m, 4H); LC-MS (ESI$^+$) m/z 528.4 (M+H)$^+$.

Step 2—2-(2,6-Dioxo-3-piperidyl)-4-[3-[methyl(4-piperidyl)amino]propylamino]isoindoline-1,3-dione To a solution of tert-butyl 4-[3-[[2-(2,6-dioxo-3-piperidyl)-1,3-dioxo-isoindolin-4-yl]amino]propyl-methylamino]piperidine-1-carboxylate (100 mg, 189 umol) in DCM (4 mL) was added HCl/dioxane (4 M, 2.00 mL). The reaction mixture was stirred at 20° C. for 30 minutes. On completion, the mixture was concentrated in vacuo to give the title compound (85.0 mg, 97% yield, HCl salt) as a yellow solid. LC-MS (ESI⁺) m/z 428.3 (M+H)⁺.

4-[2-[[1-[[4-[4-Amino-3-(difluoromethyl)pyrazol-1-yl]]cyclohexyl]methyl]-4-piperidyl]oxy] ethyl-amino]-2-(2,6-dioxo-3-piperidyl)isoindoline-1,3-dione (Intermediate AHE)

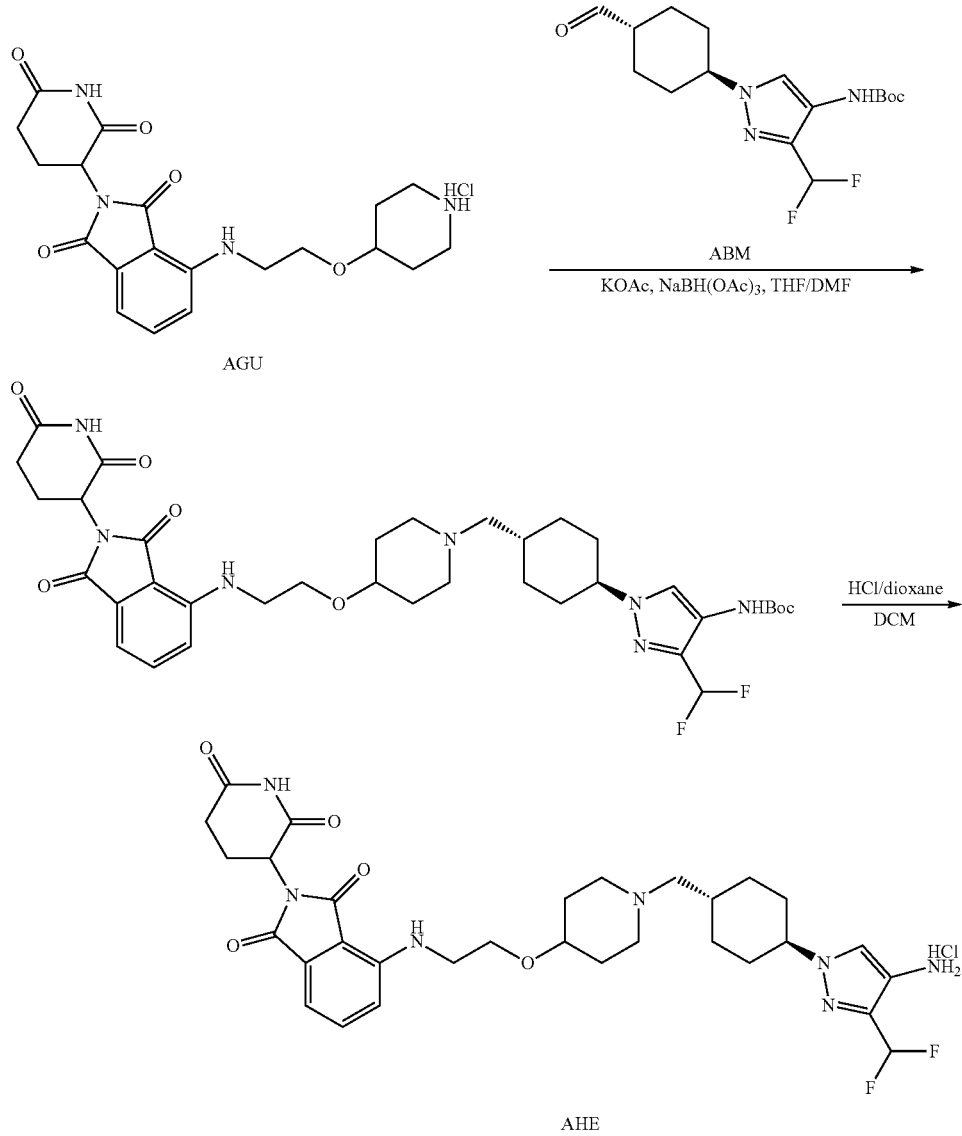

Step 1—Tert-butyl N-[3-(difluoromethyl)-1-[4-[[4-[2-[[2-(2,6-dioxo-3-piperidyl)-1,3-dioxo-isoindolin-4-yl] amino] ethoxy]-1-piperidyl]methyl]cyclohexyl]pyrazol-4-yl]carbamate To a mixture of 2-(2,6-dioxo-3-piperidyl)-4-[2-(4-piperidyloxy)ethylamino]isoindoline-1,3-dione (180 mg, 412 umol, HCl salt, Intermediate AGU) in THF (10 mL) and DMF (2 mL) was added KOAc (202 mg, 2.06 mmol). The mixture was stirred at 25° C. for 0.5 hour. Tert-butyl N-[3-(difluoromethyl)-1-(4-formylcyclohexyl)pyrazol-4-yl] carbamate (141 mg, 412 umol, Intermediate ABM) and NaBH(OAc)₃ (104 mg, 494 umol) was then added into the mixture. The reaction mixture was stirred at 25° C. for 0.5 hour. On completion, the reaction was quenched with water (5 mL) and CH₃CN (10 mL), and the mixture was concentrated in vacuo to give the residue. The residue was purified by reverse phase (0.1% FA condition) to give the title compound (250 mg, 83% yield) as a brown solid. LC-MS (ESI⁺) m/z 728.4 (M+H)⁺.

Step 2—4-[2-[[1-[[4-[4-Amino-3-(difluoromethyl) pyrazol-1-yl] cyclohexyl]methyl]-4-piperidyl]oxy] ethylamino]-2-(2,6-dioxo-3-piperidyl)isoindoline-1,3-dione To a mixture of tert-butyl N-[3-(difluoromethyl)-1-[4-[[4-[2-[[2-(2,6-dioxo-3-piperidyl)-1,3-dioxo-isoindolin-4-yl]amino] ethoxy]-1-piperidyl]methyl]cyclohexyl]pyrazol-4-yl]carbamate (250 mg, 343 umol) in DCM (20 mL) was added HCl/dioxane (4 M, 257 uL). The reaction mixture was stirred at 20° C. for 0.5 hour. On completion, the reaction mixture was concentrated in vacuo to give the title compound (220 mg, 96% yield, HCl salt) as a white solid. LC-MS (ESI$^+$) m/z 628.5 (M+H)$^+$.

4-[4-(Methylamino)cyclohexoxy]quinazoline-6-carbonitrile (Intermediate AHF)

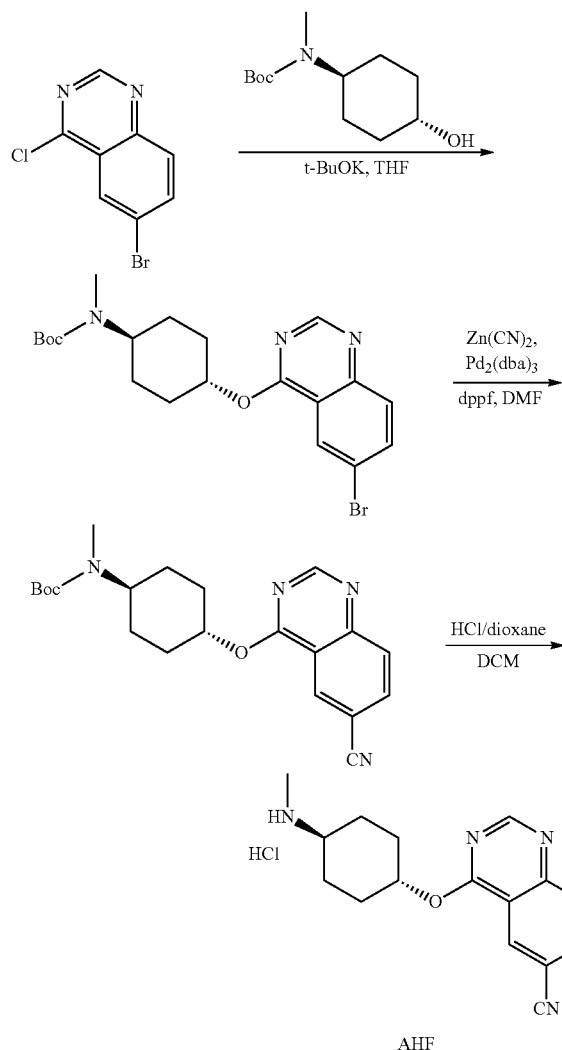

AHF

Step 1—Tert-butyl N-[4-(6-bromoquinazolin-4-yl) oxycyclohexyl]-N-methyl-carbamate To a solution of 6-bromo-4-chloro-quinazoline (1.00 g, 4.11 mmol, CAS #38267-96-8) and tert-butyl N-(4-hydroxy-cyclohexyl)-N-methyl-carbamate (965 mg, 4.21 mmol, CAS #400899-99-2) in THF (20 mL) was added t-BuOK (1 M in THF, 4.21 mL). The mixture was stirred at 50° C. for 30 minutes. On completion, the mixture was concentrated in vacuo. The residue was diluted with water (50 mL), then extracted with EA (3×50 mL). The combined organic layers were washed with brine (100 mL), dried over Na$_2$SO$_4$, filtered and concentrated in vacuo. The residue was purified by column chromatography to give the title compound (1.50 g, 80% yield) as yellow solid. $^1$H NMR (400 MHz, CDCl$_3$) δ 8.79 (s, 1H), 8.32 (d, J=2.0 Hz, 1H), 7.94-7.89 (m, 1H), 7.84-7.79 (m, 1H), 5.35-5.23 (m, 1H), 2.79 (s, 3H), 2.73 (s, 1H), 2.34 (m, 2H), 1.91-1.83 (m, 2H), 1.73 (d, J=4.0 Hz, 4H), 1.51 (s, 9H), 1.48 (s, 1H).

Step 2—Tert-butyl N-[4-(6-cyanoquinazolin-4-yl) oxycyclohexyl]-N-methyl-carbamate To a solution of tert-butyl N-[4-(6-bromoquinazolin-4-yl) oxycyclohexyl]-N-methyl-carbamate (500 mg, 1.15 mmol) in DMF (20 mL) was added Zn(CN)$_2$ (673 mg, 5.73 mmol) and Pd$_2$(dba)$_3$ (105 mg, 115 umol) and DPPF (127 mg, 229 umol). The mixture was stirred at 100° C. for 6 hours under N$_2$. On completion, the mixture was diluted with water (100 mL) and extracted with EA (3×50 mL). The combined organic layers were washed with brine (100 mL), dried over Na$_2$SO$_4$, filtered and concentrated in vacuo. The residue was purified by flash silica gel chromatography to give the title compound (475 mg, 50% yield) as yellow solid. $^1$H NMR (400 MHz, DMSO-d$_6$) δ 8.93 (s, 1H), 8.67 (d, J=1.6 Hz, 1H), 8.28-8.52 (m, 1H), 8.06 (d, J=8.4 Hz, 1H), 5.36-5.28 (m, 1H), 2.72 (s, 3H), 2.27 (d, J=7.6 Hz, 2H), 1.75-1.64 (m, 6H), 1.42 (s, 9H).

Step 3—4-[4-(Methylamino)cyclohexoxy]quinazoline-6-carbonitrile

To a solution of tert-butyl N-[4-(6-cyanoquinazolin-4-yl) oxycyclohexyl]-N-methyl-carbamate (475 mg, 1.24 mmol) in DCM (4 mL) was added HCl/dioxane (4 M, 2 mL). The mixture was stirred at 15° C. for 2 hours. On completion, the mixture was concentrated in vacuo to give the title compound (395 mg, 99% yield, HCl salt) as yellow solid. LC-MS (ESI$^+$) m/z 283.2 (M+H)$^+$.

4-[4-[Methyl(4-piperidyl)amino]cyclohexoxy]quinazoline-6-carbonitrile (Intermediate AHG)

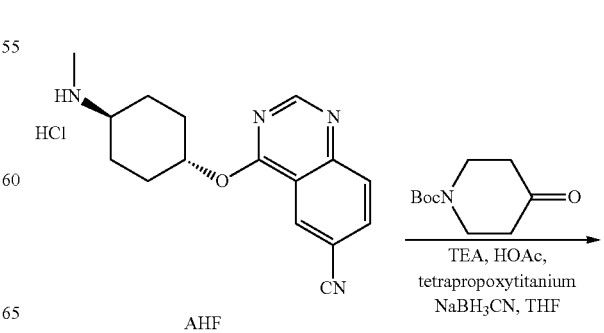

AHF

1872

1-[[(2S,3S,4S)-3-ethyl-4-fluoro-5-oxo-pyrrolidin-2-yl]methoxy]-7-methoxy-4-[2-(4-piperidyl) ethynyl] isoquinoline-6-carboxamide (Intermediate AHH)

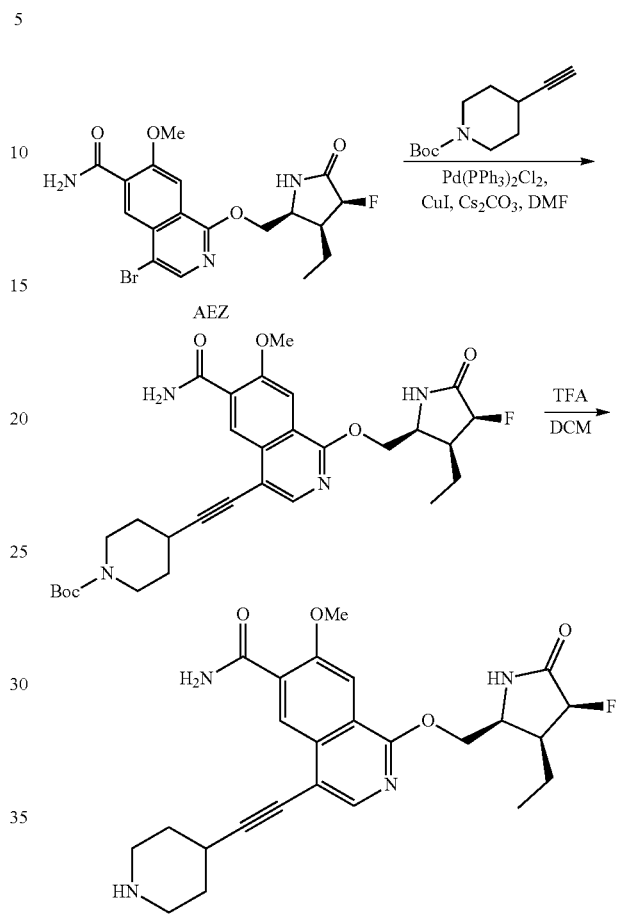

AHH

Step 1—Tert-butyl 4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]piperidine-1-carboxylate To a solution of 4-bromo-1-[[(2S,3S,4S)-3-ethyl-4-fluoro-5-oxo-pyrrolidin-2-yl]methoxy]-7-methoxy-isoquinoline-6-carboxamide (50.0 mg, 113 umol, Intermediate AEZ), and tert-butyl 4-ethynylpiperidine-1-carboxylate (71.3 mg, 340 umol, CAS #287192-97-6) in DMF (3 mL) was added Pd(PPh₃)₂Cl₂ (7.97 mg, 11.3 umol), CuI (2.16 mg, 11.3 umol) and Cs₂CO₃ (185 mg, 567 umol) under N₂. The mixture was stirred at 80° C. for 16 hrs. On completion, the mixture was filtered and the filtrate was concentrated in vacuo. The mixture was purified by reverse phase: (0.1% FA) to give the title compound (35.0 mg, 54% yield) as yellow solid. ¹H NMR (400 MHz, CDCl₃) δ 8.97 (s, 1H), 7.78-7.74 (m, 1H), 7.68 (s, 1H), 6.28 (s, 1H), 5.89 (s, 1H), 5.01-4.84 (m, 1H), 4.80-4.72 (m, 1H), 4.50-4.40 (m, 1H), 4.23-4.15 (m, 1H), 4.10 (s, 3H), 3.91-3.79 (m, 2H), 3.30-3.22 (m, 2H), 2.96-2.90 (m, 1H), 2.72-2.51 (m, 1H), 2.02-1.92 (m, 2H), 1.91-1.61 (m, 4H), 1.48 (s, 9H), 1.14 (t, J=7.2 Hz, 3H), LC-MS (ESI⁺) m/z 469.3 (M+H−100)⁺.

---

1871

-continued

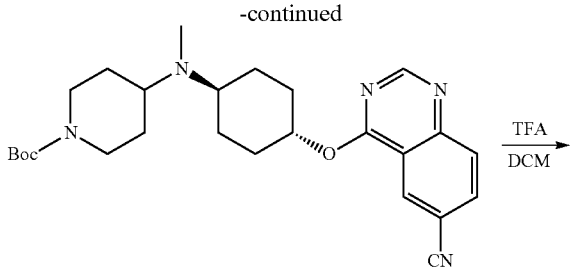

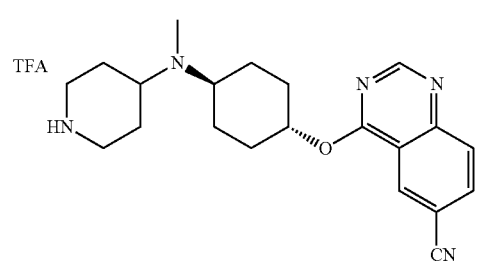

AHG

Step 1—Tert-butyl 4-[[4-(6-cyanoquinazolin-4-yl)oxycyclohexyl]-methyl-amino]piperidine-1-carboxylate To a solution of 4-[4-(methylamino)cyclohexoxy]quinazoline-6-carbonitrile (300 mg, 941 umol, HCl salt, Intermediate AHF) in THF (50 mL) was added TEA (285 mg, 2.82 mmol) and the mixture stirred at 25° C. for 30 minutes. Tert-butyl 4-oxopiperidine-1-carboxylate (375 mg, 1.88 mmol, CAS #79099-07-3) and Ti(OEt)₄ (644 mg, 2.82 mmol) was added. The mixture was stirred at 25° C. for 1 hour. Then NaBH₃CN (118 mg, 1.88 mmol) was added and the mixture was stirred at 70° C. for 2 hours. On completion, the reaction was quenched with sat. aq. NaHCO₃ (50 mL) at 15° C. The mixture was extracted with EA (3×50 mL). The combined organic layers were washed with brine (100 mL), dried over Na₂SO₄, filtered and concentrated in vacuo. The residue was purified by reversed-phase HPLC (0.1% FA condition) to give the title compound (80.0 mg, 15% yield) as yellow solid. LC-MS (ESI⁺) m/z 466.2 (M+H)⁺.

Step 2—4-[4-[Methyl(4-piperidyl)amino]cyclohexoxy]quinazoline-6-carbonitrile To a solution of tert-butyl 4-[[4-(6-cyanoquinazolin-4-yl)oxycyclohexyl]-methyl-amino] piperidine-1-carboxylate (40.0 mg, 85.9 umol) in DCM (3.0 mL) was added TFA (1.0 mL). The mixture was stirred at 15° C. for 0.5 hour. On completion, the mixture was concentrated in vacuo to give the title compound (31.0 mg, 98% yield) as yellow solid. LC-MS (ESI⁺) m/z 366.2 (M+H)⁺.

Step 2—1-[[(2S,3S,4S)-3-ethyl-4-fluoro-5-oxo-pyrrolidin-2-yl]methoxy]-7-methoxy-4-[2-(4-piperidyl)ethynyl]isoquinoline-6-carboxamide To a solution of tert-butyl 4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]piperidine-1-carboxylate (30 mg, 52.7 umol) in DCM (3 mL) was added TFA (5.78 g, 50.6 mmol). The mixture was stirred at 15° C. for 0.5 hr. On completion, the mixture was concentrated in vacuo to give the title compound (30.5 mg, 99% yield, TFA) as yellow solid. $^1$H NMR (400 MHz, DMSO-d$_6$) δ 8.87 (s, 1H), 8.57 (s, 1H), 8.30 (s, 1H), 8.10 (s, 1H), 7.93-7.88 (m, 1H), 7.79 (s, 1H), 4.99-4.82 (m, 1H), 4.58-4.52 (m, 1H), 4.33-4.25 (m, 1H), 4.13-4.07 (m, 2H), 4.00 (s, 3H), 3.34-3.26 (m, 2H), 3.18-3.02 (m, 3H), 2.20-2.09 (m, 2H), 1.93-1.80 (m, 2H), 1.64-1.53 (m, 2H), 1.02 (t, J=7.2 Hz, 3H).

3-r 1-[[1-(2,6-Dioxo-3-piperidyl)-3-methyl-2-oxo-benzimidazol-5-yl]methyl]-4-piperidyl] propanal (Intermediate AHI)

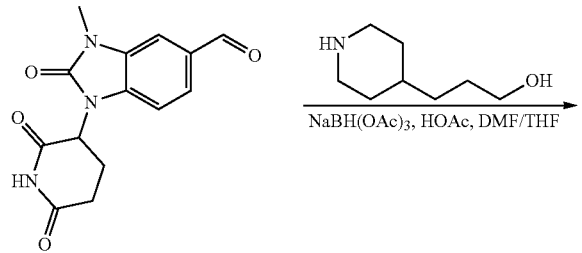

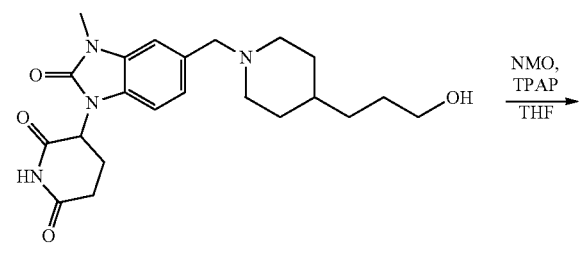

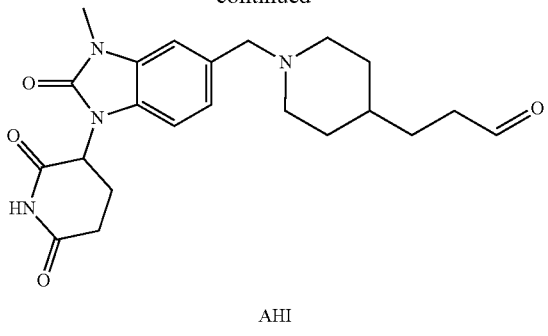

AHI

Step 1—3-[5-[[4-(3-Hydroxypropyl)-1-piperidyl]methyl]-3-methyl-2-oxo-benzimidazol-1-yl] piperidine-2,6-dione To a solution of 1-(2,6-dioxo-3-piperidyl)-3-methyl-2-oxo-benzimidazole-5-carbaldehyde (300 mg, 1.04 mmol, Intermediate SK), 3-(4-piperidyl)propan-1-ol (149 mg, 1.04 mmol, CAS #7037-49-2) in DMF (2 mL) and THF (5 mL) was added HOAc (125 mg, 2.09 mmol). The mixture was stirred at 80° C. for 1 hr. Then NaBH(OAc)$_3$ (442 mg, 2.09 mmol) was added, the mixture was stirred at 60° C. for 16 hrs. On completion, the mixture was quenched with H$_2$O (1 mL) and concentrated in vacuo. The residue was purified by reverse phase (0.1% FA) to give the title compound (45 mg, 10% yield) as yellow oil. $^1$H NMR (400 MHz, DMSO-d$_6$) δ 11.09 (s, 1H), 7.11 (s, 1H), 7.08-7.03 (m, 1H), 7.01-6.95 (m, 1H), 5.40-5.32 (m, 1H), 3.50 (s, 2H), 3.39-3.37 (m, 2H), 3.34 (s, 1H), 3.04-2.93 (m, 1H), 2.89-2.79 (m, 2H), 2.78-2.69 (m, 1H), 2.66-2.57 (m, 1H), 2.07-1.97 (m, 2H), 1.95-1.91 (m, 1H), 1.76-1.67 (m, 1H), 1.65-1.54 (m, 2H), 1.48-1.36 (m, 3H), 1.29-1.17 (m, 4H), 1.15-1.10 (m, 1H), 1.02-0.82 (m, 1H), LC-MS (ESI$^+$) m/z 415.2 (M+H)$^+$.

Step 2—3-[1-[[1-(2,6-Dioxo-3-piperidyl)-3-methyl-2-oxo-benzimidazol-5-yl]methyl]-4-piperidyl] propanal To a solution of 3-[5-[[4-(3-hydroxypropyl)-1-piperidyl]methyl]-3-methyl-2-oxo-benzimidazol-1-yl] piperidine-2,6-dione (30 mg, 72.3 umol) in THF (3 mL) was added NMO (12.7 mg, 108 umol) and TPAP (1.27 mg, 3.62 umol). The mixture was stirred at 15° C. for 16 hrs. On completion, the mixture was quenched with H$_2$O (15 mL), then extracted with EA (3×10 mL). The organic layers were washed with brine (2×10 mL) dried over anhydrous Na$_2$SO$_4$, filtered and concentrated in vacuo to give the title compound (28.0 mg, 93% yield) as yellow solid. $^1$H NMR (400 MHz, DMSO-d$_6$) δ 11.14 (s, 1H), 8.01 (s, 1H), 7.15 (s, 1H), 7.12-7.07 (m, 1H), 7.04-6.98 (m, 1H), 5.43-5.39 (m, 1H), 3.52 (s, 2H), 3.46-3.42 (m, 2H), 3.39 (s, 3H), 3.08-2.94 (m, 3H), 2.83-2.77 (m, 2H), 2.35-2.30 (m, 2H), 2.30-2.26 (m, 1H), 2.09-2.05 (m, 1H), 1.70-1.67 (m, 2H), 1.54-1.51 (m, 2H), 1.17-1.14 (m, 2H).

1-[[(2S,3S,4S)-3-ethyl-4-fluoro-5-oxo-pyrrolidin-2-yl]methoxy]-7-methoxy-4-[2-[1-(4-piperidylmethyl)-4-piperidyl]ethynyl]isoquinoline-6-carboxamide
(Intermediate AHJ)

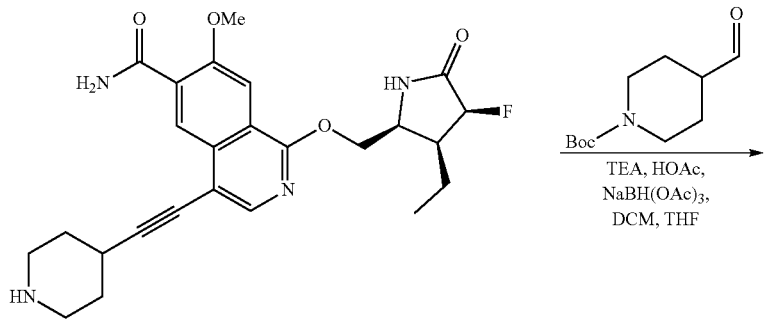

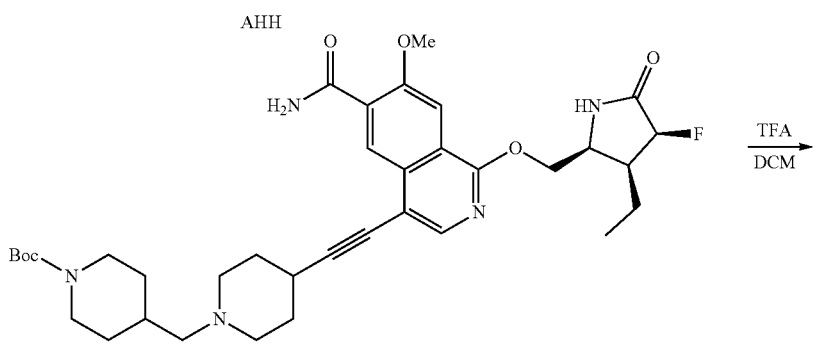

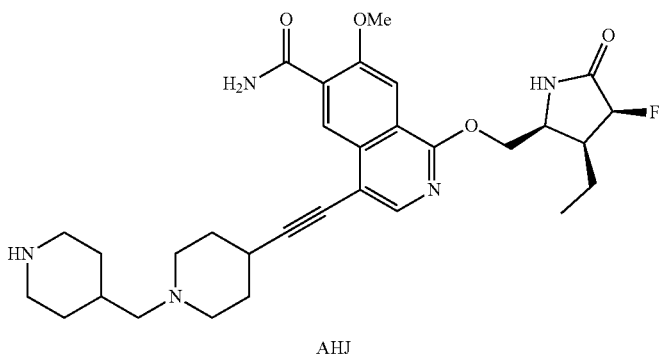

Step 1—Tert-butyl 4-[[4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]-1-piperidyl]methyl]piperidine-1-carboxylate To a solution of 1-[[(2S,3S,4S)-3-ethyl-4-fluoro-5-oxo-pyrrolidin-2-yl]methoxy]-7-methoxy-4-[2-(4-piperidyl)ethynyl]isoquinoline-6-carboxamide (30.0 mg, 51.5 umol, TFA, Intermediate AHH), in DCM (2 mL) and THF (2 mL) was added TEA (10.4 mg, 103 umol). The mixture was stirred at 15° C. for 0.5 hr. Then tert-butyl 4-formylpiperidine-1-carboxylate (10.9 mg, 51.5 umol, CAS #137076-22-3) and HOAc (9.28 mg, 154 umol) was added, and the mixture was stirred at 15° C. for 0.5 hr. Then NaBH(OAc)₃ (21.8 mg, 103 umol) was added, the mixture was stirred at 15° C. for 1 hour. On completion, the mixture was diluted with H₂O (1 mL) and concentrated in vacuo. The residue was purified by reverse phase (0.1% FA) to give the title compound (33.0 mg, 96% yield) as yellow solid. LC-MS (ESI⁺) m/z 666.4 (M+H)⁺.

Step 2—1-[[(2S,3S,4S)-3-ethyl-4-fluoro-5-oxo-pyrrolidin-2-yl]methoxy]-7-methoxy-4-[2-[1-(4-piperidylmethyl)-4-piperidyl]ethynyl]isoquinoline-6-carboxamide To a solution of tert-butyl 4-[[4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]-1-piperidyl]methyl]piperidine-1-carboxylate (33.0 mg, 49.5 umol) in DCM (2 mL) was added TFA (3.08 g, 27.0 mmol). The mixture was stirred at 15° C. for 1 hr. On completion, the mixture was concentrated in vacuo to give the title compound (33.0 mg, 97% yield, TFA) as yellow oil. LC-MS (ESI⁺) m/z 566.4 (M+H)⁺.

3-(4-Hydroxy-1-oxo-isoindolin-2-yl)piperidine-2,6-dione (Intermediate AHK)

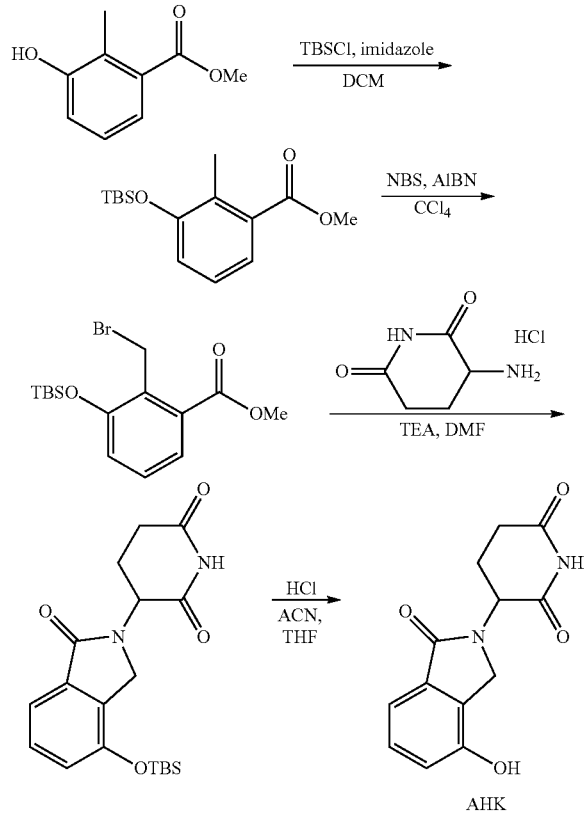

Step 1—Methyl 3-[tert-butyl(dimethyl)silyl]oxy-2-methyl-benzoate

To a solution of methyl 3-hydroxy-2-methyl-benzoate (5.00 g, 30.0 mmol, CAS #55289-05-9) in DCM (50 mL) was added TBSCl (5.90 g, 39.1 mmol) and imidazole (6.15 g, 90.2 mmol). The reaction mixture was stirred at 0-10° C. for 16 hours. On completion, the reaction mixture was diluted with water (50 mL) and extracted with DCM (3×50 mL). The combined organic layers were washed with brine (2×50 mL), dried over Na$_2$SO$_4$, filtered and concentrated in vacuo. The residue was purified by silica gel chromatography (PE:EA=100:1) to give the title compound (8.20 g, 97% yield) as colorless oil. $^1$H NMR (400 MHz, CDCl$_3$) δ 7.43 (dd, J=0.8, 8.0 Hz, 1H), 7.10 (t, J=8.0 Hz, 1H), 6.94 (dd, J=0.8, 8.0 Hz, 1H), 3.89 (s, 3H), 2.43 (s, 3H), 1.03 (s, 9H), 0.23 (s, 6H).

Step 2—Methyl 2-(bromomethyl)-3-[tert-butyl(dimethyl)silyl]oxy-benzoate

To a solution of methyl 3-[tert-butyl(dimethyl)silyl]oxy-2-methyl-benzoate (2.00 g, 7.13 mmol) and NBS (1.52 g, 8.56 mmol) in CCl$_4$ (20 mL) was added AIBN (117 mg, 713 umol) under N$_2$. The reaction mixture was stirred at 80° C. for 16 hours. On completion, the reaction mixture was filtered and washed with CCl$_4$ (30 mL). The filtrate was concentrated in vacuo to give the title compound (2.40 g, 93% yield) as yellow oil. $^1$H NMR (400 MHz, CDCl$_3$) δ 7.53 (dd, J=1.2, 8.0 Hz, 1H), 7.24 (t, J=8.0 Hz, 1H), 7.00 (dd, J=1.2, 8.0 Hz, 1H), 5.03 (s, 2H), 3.94 (s, 3H), 1.08 (s, 9H), 0.32 (s, 6H).

Step 3—3-[4-[Tert-butyl(dimethyl)silyl]oxy-1-oxo-isoindolin-2-yl]piperidine-2,6-dione A solution of methyl 2-(bromomethyl)-3-[tert-butyl(dimethyl)silyl]oxy-benzoate (2.40 g, 6.68 mmol), 3-aminopiperidine-2,6-dione (1.43 g, 8.68 mmol, HCl salt, CAS #24666-56-6) and TEA (2.03 g, 20.0 mmol) in ACN (30 mL) was stirred at 80° C. for 16 hrs. On completion, the reaction mixture was concentrated in vacuo. The residue was diluted with EA (30 mL) and water (30 mL), and filtered. The filter cake was concentrated in vacuo to give the title compound (800 mg, 31% yield) as purple solid. $^1$H NMR (400 MHz, DMSO-d$_6$) δ 10.95 (s, 1H), 7.49-7.40 (m, 1H), 7.38-7.29 (m, 1H), 7.10 (dd, J=0.8, 8.0 Hz, 1H), 5.10 (dd, J=5.2, 13.2 Hz, 1H), 4.41-4.15 (m, 2H), 2.95-2.81 (m, 1H), 2.63-2.54 (m, 1H), 2.48-2.41 (m, 1H), 2.03-1.93 (m, 1H), 0.98 (s, 9H), 0.28-0.23 (m, 6H).

Step 4—3-(4-Hydroxy-1-oxo-isoindolin-2-yl)piperidine-2,6-dione

To a solution of 3-[4-[tert-butyl(dimethyl)silyl]oxy-1-oxo-isoindolin-2-yl]piperidine-2,6-dione (700 mg, 1.87 mmol) in THF (5 mL) and ACN (5 mL) was added 2.0 M aq.HCl (10.0 mL). The reaction mixture was stirred at 20° C. for 16 hours. On completion, the reaction mixture was concentrated in vacuo. The residue was purified by reverse phase (0.1% FA) to give the title compound (450 mg, 90% yield) as black brown solid. $^1$H NMR (400 MHz, DMSO-d$_6$) δ 10.96 (s, 1H), 10.10 (s, 1H), 7.37-7.28 (m, 1H), 7.18 (d, J=7.2 Hz, 1H), 7.01 (d, J=7.6 Hz, 1H), 5.09 (dd, J=5.2, 13.2 Hz, 1H), 4.38-4.27 (m, 1H), 4.22-4.11 (m, 1H), 2.98-2.84 (m, 1H), 2.64-2.55 (m, 1H), 2.45-2.30 (m, 1H), 2.05-1.94 (m, 1H).

3-[1-Oxo-4-[3-(4-piperidyloxy)propoxy]isoindolin-2-yl]piperidine-2,6-dione (Intermediate AHL)

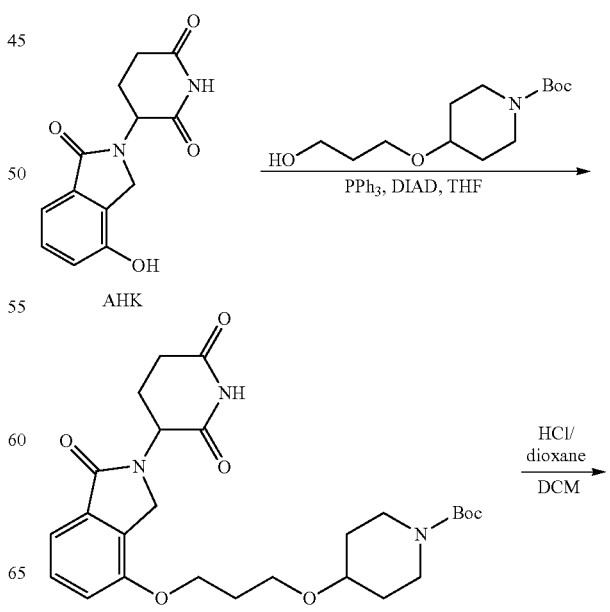

-continued

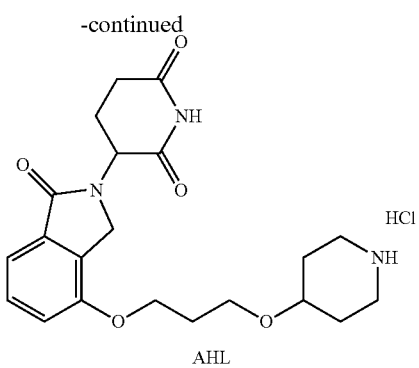

AHL

Step 1—Tert-butyl 4-[3-[2-(2,6-dioxo-3-piperidyl)-1-oxo-isoindolin-4-yl]oxypropoxy]piperidine-1-carboxylate To a solution of 3-(4-hydroxy-1-oxo-isoindolin-2-yl)piperidine-2,6-dione (250 mg, 960 umol, Intermediate AHK), tert-butyl 4-(3-hydroxypropoxy)piperidine-1-carboxylate (249 mg, 960 umol, synthesized via Steps 1-2 of Intermediate ADK) and PPh$_3$ (377 mg, 1.44 mmol) in THF (10 mL) was added DIAD (388 mg, 1.92 mmol) at 0° C. The reaction mixture was stirred at 0-15° C. for 16 hours. On completion, the reaction mixture was diluted with water (20 mL) and extracted with EA (3×40 mL). The combined organic layers were washed with brine (3×20 mL), dried over Na$_2$SO$_4$, filtered and concentrated in vacuo. The residue was purified by reverse phase (0.1% FA) to give the title compound (700 mg, 46% yield, FA salt) as gray solid. $^1$H NMR (400 MHz, DMSO-d$_6$) δ 10.97 (s, 1H), 7.47 (t, J=8.0 Hz, 1H), 7.31 (d, J=7.2 Hz, 1H), 7.25 (d, J=8.0 Hz, 1H), 5.11 (dd, J=5.2, 13.6 Hz, 1H), 4.43-4.32 (m, 1H), 4.28-4.13 (m, 3H), 3.65-3.52 (m, 4H), 3.07-2.86 (m, 3H), 2.64-2.55 (m, 1H), 2.46-2.37 (m, 2H), 2.03-1.90 (m, 3H), 1.80-1.71 (m, 2H), 1.41-1.31 (m, 11H); LC-MS (ESI$^+$) m/z 402.2 (M+H−100)$^+$.

Step 2—3-[1-Oxo-4-[3-(4-piperidyloxy)propoxy]isoindolin-2-yl]piperidine-2,6-dione To a solution of tert-butyl 4-[3-[2-(2,6-dioxo-3-piperidyl)-1-oxo-isoindolin-4-yl]oxypropoxy] piperidine-1-carboxylate (700 mg, 447 umol, FA salt) in DCM (10 mL) was added 4.0 M HCl/dioxane (6.41 mL). The reaction mixture was stirred at 15° C. for 1 hour. On completion, the reaction mixture was concentrated in vacuo. The residue was purified by reverse phase (0.1% HCl) to give the title compound (140 mg, 71% yield, HCl salt) as yellow solid. $^1$H NMR (400 MHz, DMSO-d$_6$) δ 11.00 (s, 1H), 8.90-8.58 (m, 2H), 7.54-7.44 (m, 1H), 7.31 (d, J=7.2 Hz, 1H), 7.25 (d, J=8.0 Hz, 1H), 5.12 (dd, J=5.2, 13.2 Hz, 1H), 4.42-4.30 (m, 1H), 4.27-4.13 (m, 3H), 3.61-3.56 (m, 2H), 3.10 (d, J=6.0 Hz, 2H), 2.99-2.85 (m, 3H), 2.58 (d, J=18.0 Hz, 1H), 2.54-2.52 (m, 1H), 2.44 (dd, J=4.4, 13.2 Hz, 1H), 2.04-1.88 (m, 5H), 1.73-1.58 (m, 2H).

3-[2-Methyl-5-[methyl-[3-(4-piperidyloxypropyl]amino]-4-oxo-quinazolin-3-yl]piperidine-2,6-dione (Intermediate AHM)

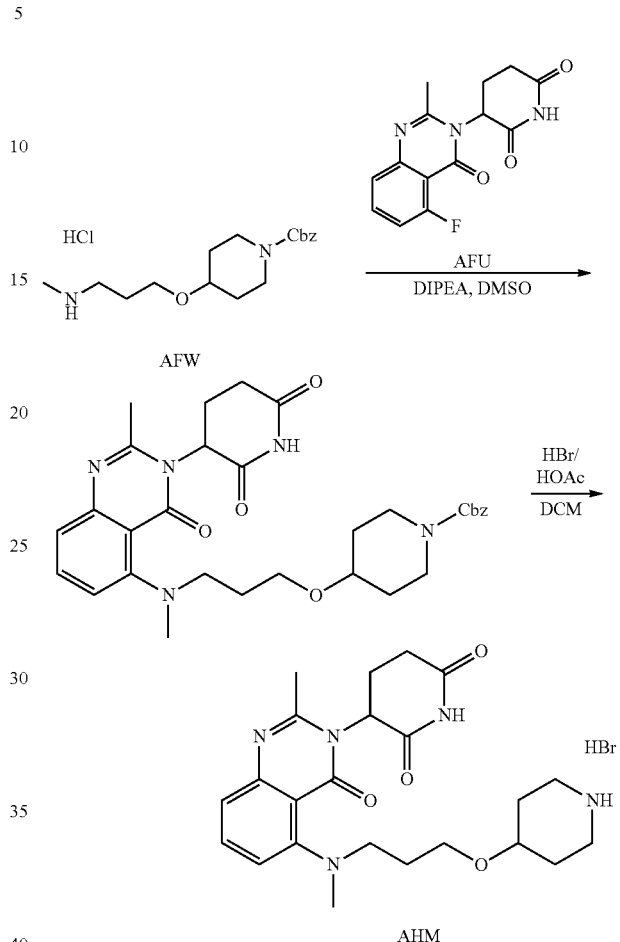

Step 1—Benzyl 4-[3-[[3-(2,6-dioxo-3-piperidyl)-2-methyl-4-oxo-quinazolin-5-yl]-methyl-amino]propoxy]piperidine-1-carboxylate To a solution of benzyl 4-[3-(methylamino)propoxy]piperidine-1-carboxylate (200 mg, 583 umol, HCl salt, Intermediate AFW) and 3-(5-fluoro-2-methyl-4-oxo-quinazolin-3-yl)piperidine-2,6-dione (168 mg, 583 umol, Intermediate AFU) in DMSO (6 mL) was added DIPEA (226 mg, 1.75 mmol). The mixture was stirred at 130° C. for 3 hours. On completion, the mixture was purified by reversed-phase (0.1% FA condition) to give the title compound (160 mg, 45% yield) as yellow solid. $^1$H NMR (400 MHz, DMSO-d$_6$) δ 10.96 (s, 1H), 7.51 (t, J=8.0 Hz, 1H), 7.40-7.28 (m, 5H), 6.95-6.84 (m, 2H), 5.15-5.07 (m, 1H), 5.04 (s, 2H), 3.53 (m, 2H), 3.24-2.99 (m, 5H), 2.76 (s, 3H), 2.64-2.57 (m, 1H), 2.54 (s, 3H), 2.52 (d, J=2.0 Hz, 3H), 2.16-2.04 (m, 2H), 1.77-1.56 (m, 4H), 1.33-1.15 (m, 2H).

Step 2—3-[2-Methyl-5-[methyl-[3-(4-piperidyloxypropyl]amino]-4-oxo-quinazolin-3-yl]piperidine-2,6-dione To a solution of benzyl 4-[3-[[3-(2,6-dioxo-3-piperidyl)-2-methyl-4-oxo-quinazolin-5-yl]-methyl-amino]propoxy]

piperidine-1-carboxylate (150 mg, 260 umol) in DCM (2 mL) was added HBr/HOAc (260 umol, 1 mL). The mixture was stirred at 15° C. for 2 hours. On completion, the mixture was concentrated in vacuo to give the title compound (110 mg, 95% yield) as yellow solid. LC-MS (ESI+) m/z 442.4 (M+1)+.

3-(5-Hydroxy-2-methyl-4-oxo-quinazolin-3-yl)piperidine-2,6-dione (Intermediate AHN)

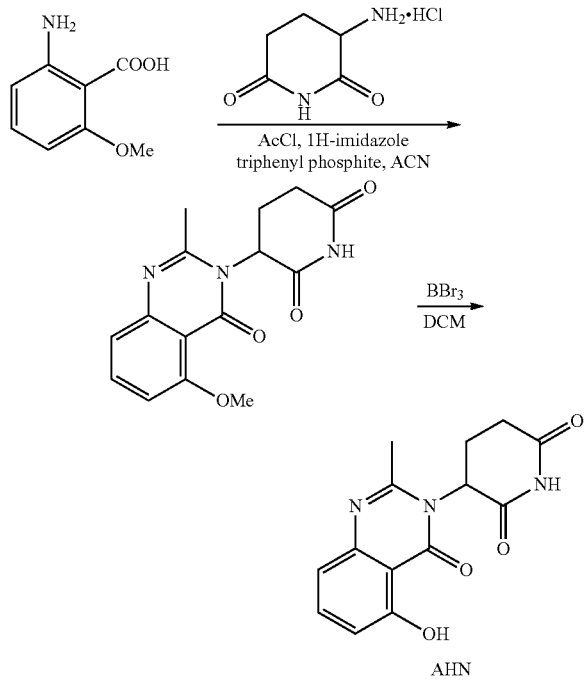

Step 1—3-(5-Methoxy-2-methyl-4-oxo-quinazolin-3-yl)piperidine-2,6-dione

To a stirred mixture of 2-amino-6-methoxy-benzoic acid (2.50 g, 15.0 mmol, CAS #53600-33-2) and 1H-imidazole (1.22 g, 17.9 mmol) in ACN (20 mL) was added AcCl (1.41 g, 17.9 mmol) at 20° C. and the mixture was stirred at 20° C. for 12 hrs. Then 3-aminopiperidine-2,6-dione (2.46 g, 15.0 mmol, CAS #24666-56-6), 1H-imidazole (2.14 g, 31.4 mmol) and triphenyl phosphite (5.57 g, 17.9 mmol) were added to the reaction mixture. The reaction mixture was heated at 80° C. for 12 hrs. On completion, the mixture was concentrated in vacuo. The residue was diluted with water (80 mL), stirred and filtered. The filter cake was washed with EA (50 mL), H2O (50 mL), NaHCO3 (50 mL), H2O (50 mL), and dried in vacuo to give the title compound (3.90 g, 87% yield) as a white solid. $^1$H NMR (400 MHz, DMSO-$d_6$) δ 10.95 (s, 1H), 7.68 (t, J=8.0 Hz, 1H), 7.14-7.08 (m, 1H), 6.98 (d, J=8.0 Hz, 1H), 5.13 (dd, J=5.6, 11.6 Hz, 1H), 3.83 (s, 3H), 2.89-2.75 (m, 1H), 2.69-2.53 (m, 5H), 2.16-2.08 (m, 1H).

Step 2—3-(5-Hydroxy-2-methyl-4-oxo-quinazolin-3-yl)piperidine-2,6-dione

To a solution of 3-(5-methoxy-2-methyl-4-oxo-quinazolin-3-yl)piperidine-2,6-dione (4.10 g, 13.6 mmol) in DCM (50 mL) was added BBr3 (10.2 g, 40.8 mmol) at −78° C. The reaction mixture was stirred at 20° C. for 12 hrs. On completion, the mixture was quenched with water (50 mL), stirred and filtered. The filter cake was dried in vacuo to give the title compound (3.20 g, 82% yield) as an off-white solid. $^1$H NMR (400 MHz, DMSO-$d_6$) δ 11.14 (s, 1H), 7.72 (t, J=8.0 Hz, 1H), 7.10 (d, J=8.0 Hz, 1H), 6.90 (d, J=8.0 Hz, 1H), 5.39 (dd, J=5.6, 11.6 Hz, 1H), 2.94-2.79 (m, 1H), 2.69 (s, 3H), 2.66-2.57 (m, 2H), 2.23 (td, J=5.2, 10.4 Hz, 1H).

3-[2-Methyl-4-oxo-5-[3-(4-piperidyloxy)propoxy]quinazolin-3-yl]piperidine-2,6-dione (Intermediate AHO)

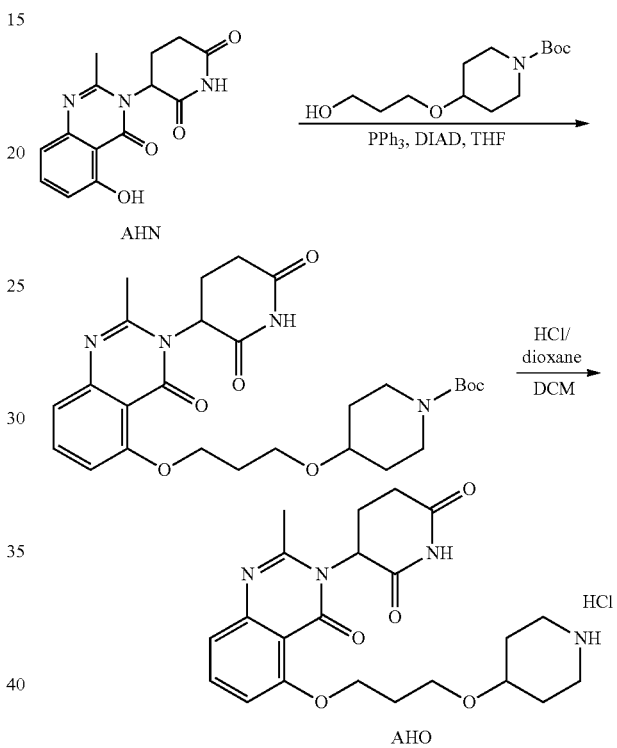

Step 1—Tert-butyl 4-[3-[3-(2,6-dioxo-3-piperidyl)-2-methyl-4-oxo-quinazolin-5-yl]oxypropoxy] piperidine-1-carboxylate To a solution of 3-(5-hydroxy-2-methyl-4-oxo-quinazolin-3-yl)piperidine-2,6-dione (330 mg, 1.15 mmol, Intermediate AHN), tert-butyl 4-(3-hydroxypropoxy)piperidine-1-carboxylate (298 mg, 1.15 mmol, synthesized via Steps 1-2 of Intermediate ADK) and PPh3 (904 mg, 3.45 mmol) in THF (5 mL) was added a solution of DIAD (813 mg, 4.02 mmol) in THF (1 mL) at 0° C. dropwise. Then the reaction mixture was stirred at 20° C. for 12 hrs. On completion, the mixture was quenched with water (50 mL), and extracted with EA (2×50 mL). The organic layer was washed with brine (50 mL), then concentrated in vacuo. The residue was purified by reverse phase (0.1% FA condition) to give the title compound (380 mg, 63% yield) as a yellow solid. LC-MS (ESI+) m/z 529.3 (M+H)+.

Step 4—3-[2-Methyl-4-oxo-5-[3-(4-piperidyloxy)propoxy]quinazolin-3-yl]piperidine-2,6-dione To a solution of tert-butyl 4-[3-[3-(2,6-dioxo-3-piperidyl)-2-methyl-4-oxo-quinazolin-5-yl] oxypropoxy]piperidine-1-carboxylate (350 mg, 662 umol) in DCM (4 mL) was added HCl/dioxane (4 mL). The reaction mixture was stirred at 20° C. for 2 hrs. On completion, the mixture was concentrated in vacuo. The residue was purified by reverse phase (column: Phenomenex Synergi C18 150*25*10 um; mobile phase: [water (0.225% FA)-ACN]; B %: 3%-33%, 10 min) to give the title compound (250 mg, 81% yield, HCl salt) as a yellow solid. LC-MS (ESI+) m/z 429.2 (M+H)+.

5-[(3aR,7aR)-4,4-difluoro-2-oxo-3,3a,5,6,7,7a-hexa-hydrobenzimidazol-1-yl]pyrazolo[1,5-a]pyrimidine-3-carboxylic acid (Intermediate AHP)

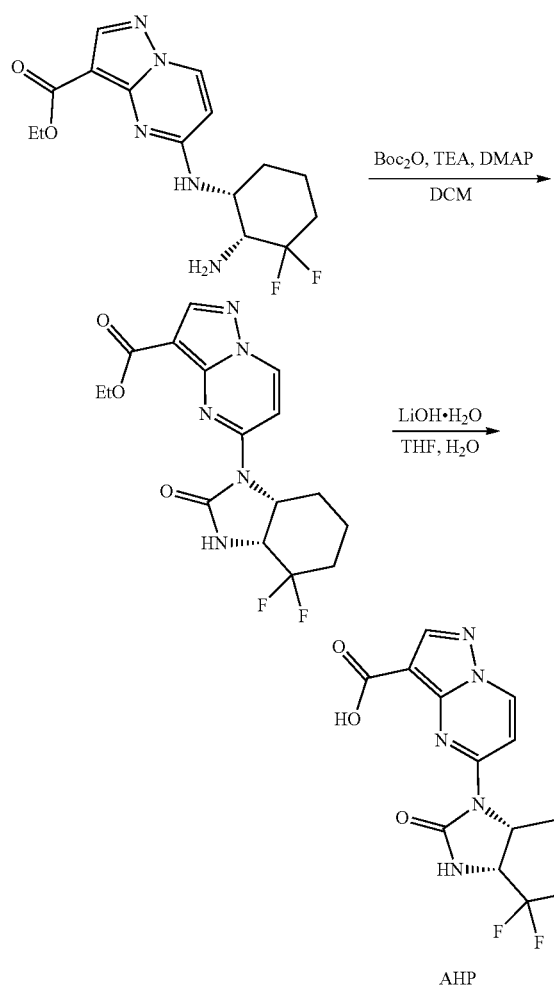

Step 1—Ethyl 5-[(3aR,7aR)-4,4-difluoro-2-oxo-3,3a,5,6,7,7a-hexahydrobenzimidazol-1-yl]pyrazolo r[1,5-a]pyrimidine-3-carboxylate To a solution of ethyl 5-[[(1R,2R)-2-amino-3,3-difluoro-cyclohexyl]amino]pyrazolo[1,5-a]pyrimidine-3-carboxylate (600 mg, 1.77 mmol, synthesized via Step 1 of Intermediate AET), DMAP (21.6 mg, 176 umol) and TEA (357 mg, 3.54 mmol) in DCM (10 mL) was added Boc₂O (463 mg, 2.12 mmol). The reaction mixture was stirred at 35° C. for 2 hours. On completion, the reaction mixture was concentrated in vacuo. The residue was purified by silica gel chromatography (PE:EA=8:1) to give the title compound (350 mg, 53% yield) as white solid. This cylized product was a side-product of Intermediate AET during Step 2. ¹H NMR (400 MHz, CDCl₃) δ 8.55 (d, J=7.6 Hz, 1H), 8.45 (s, 1H), 8.13 (d, J=7.6 Hz, 1H), 5.15 (s, 1H), 5.11-5.01 (m, 1H), 4.43-4.32 (m, 2H), 4.13-4.03 (m, 1H), 2.90-2.73 (m, 1H), 2.23-2.12 (m, 1H), 2.10-1.95 (m, 1H), 1.93-1.79 (m, 1H), 1.74-1.65 (m, 1H), 1.60-1.57 (m, 1H), 1.41 (t, J=7.2 Hz, 3H); LC-MS (ESI+) m/z 366.1 (M+H)+.

Step 2—5-[(3aR,7aR)-4,4-difluoro-2-oxo-3,3a,5,6,7,7a-hexahydrobenzimidazol-1-yl]pyrazolo[1,5-a]pyrimidine-3-carboxylic acid To a solution of ethyl 5-[(3aR,7aR)-4,4-difluoro-2-oxo-3,3a,5,6,7,7a-hexahydrobenzimidazol-1-yl] pyrazolo[1,5-a]pyrimidine-3-carboxylate (80.0 mg, 218 umol) in water (2 mL) and dioxane (1 mL) was added KOH (36.8 mg, 656 umol). The reaction mixture was stirred at 40° C. for 16 hrs. On completion, the reaction mixture was acidified with HCl (1N in water) until the pH=7 and concentrated in vacuo. The residue was purified by reverse phase (0.1% TFA) to give the title compound (25.0 mg, 33% yield) as white solid. ¹H NMR (400 MHz, DMSO-d₆) δ 9.01 (d, J=7.6 Hz, 1H), 8.39 (s, 1H), 8.32 (s, 1H), 7.99 (d, J=7.6 Hz, 1H), 4.88-4.75 (m, 1H), 4.22-4.06 (m, 1H), 2.13-1.92 (m, 2H), 1.78-1.21 (m, 4H).

5-[[(1R,2R)-2-Hydroxycyclohexyl]amino]pyrazolo[1,5-a]pyrimidine-3-carboxylic acid (Intermediate AHQ)

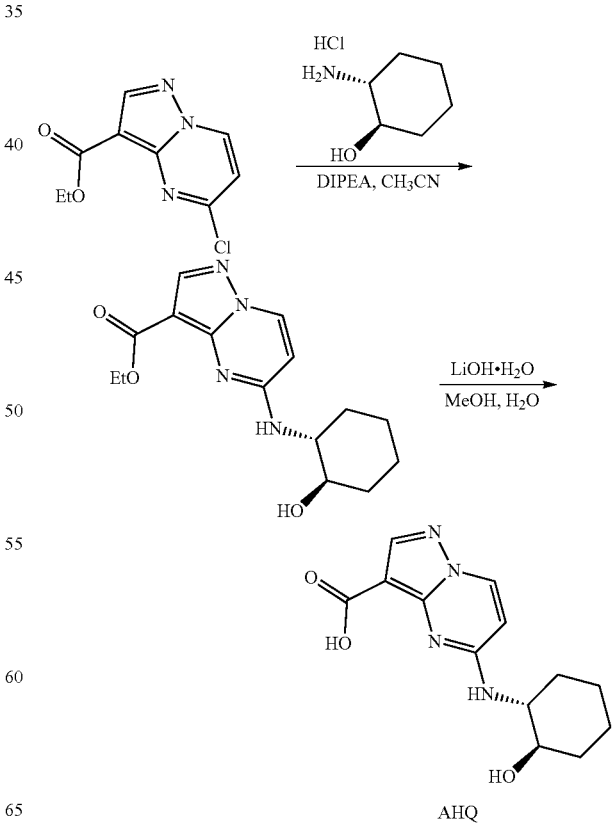

Step 1—Ethyl 5-[[(1R,2R)-2-hydroxycyclohexyl]amino]pyrazolo 1,5-a]pyrimidine-3-carboxylate To a solution of ethyl 5-chloropyrazolo[1,5-a]pyrimidine-3-carboxylate (300 mg, 1.33 mmol, CAS #1224944-77-7) and (1R,2R)-2-aminocyclohexanol (302 mg, 1.99 mmol, HCl salt, CAS #13374-31-7) in ACN (5 mL) was added DIPEA (515 mg, 3.99 mmol). The reaction mixture was stirred at 60° C. for 16 hours. On completion, the reaction mixture was concentrated in vacuo to give the title compound (329 mg, 99% yield) as yellow oil. LC-MS (ESI+) m/z 305.1 (M+H)+.

Step 2—5-[[(1R,2R)-2-Hydroxcyclohexyl]amino]pyrazolo[1,5-a]pyrimidine-3-carboxylic acid To a solution of ethyl 5-[[(1R,2R)-2-hydroxycyclohexyl]amino]pyrazolo[1,5-a]pyrimidine-3-carboxylate (329 mg, 1.33 mmol) in a mixed solvents of water (2 mL) and methanol (10 mL) was added LiOH.H2O (413 mg, 9.86 mmol). The reaction mixture was stirred at 60° C. for 19 hours. On completion, the reaction mixture was concentrated in vacuo. The residue was diluted with water (5 mL) and acidified with HCl (1 N) until the pH=6, and the solution was purified by reverse phase (0.1% FA). The residue was diluted with ACN/H2O=5/1 (60 mL), 2.0 N aq. HCl (1 mL) was added and the solution was lyophilized to give the title compound (350 mg, 38% yield) as gray solid. $^1$H NMR (400 MHz, DMSO-$d_6$) δ 11.75-11.21 (m, 1H), 8.48 (d, J=6.4 Hz, 1H), 8.09 (s, 1H), 7.80 (d, J=6.4 Hz, 1H), 6.40 (d, J=5.2 Hz, 1H), 4.91-4.65 (m, 1H), 3.93-3.70 (m, 1H), 3.40-3.35 (m, 1H), 2.10-1.98 (m, 1H), 1.96-1.85 (m, 1H), 1.73-1.57 (m, 2H), 1.39-1.10 (m, 4H).

3-1-[[(2S,3S,4S)-3-Ethyl-4-fluoro-5-oxo-pyrrolidin-2-yl]methoxy]-4-[2-(4-formylcyclohexyl) ethynyl]-7-methoxy-isoquinoline-6-carboxamide (Intermediate AHR)

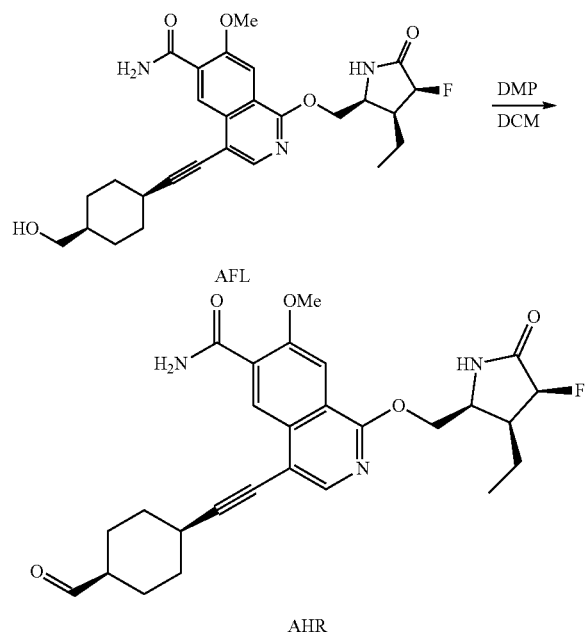

AFL

AHR

To a solution of 1-[[(2S,3S,4S)-3-ethyl-4-fluoro-5-oxo-pyrrolidin-2-yl]methoxy]-4-[2-[4-(hydroxymethyl)cyclohexyl]ethynyl]-7-methoxy-isoquinoline-6-carboxamide (30.0 mg, 60.3 umol, Intermediate AFL) in DCM (3 mL) was added DMP (30.7 mg, 72.4 umol, 22.4 uL). The reaction mixture was stirred at 25° C. for 3 hrs. On completion, the mixture was quenched with sat. Na2S2O3 (3 mL) and sat. NaHCO3 (3 mL), stirred for 10 minutes, then extracted with DCM (2×10 mL). The organic layer was washed with brine (2×10 mL), dried with Na2SO4, filtered and the filtrate was concentrated in vacuo to give the title compound (29.0 mg, 97% yield) as white solid. $^1$H NMR (400 MHz, DMSO-$d_6$) δ 9.63 (d, J=0.8 Hz, 1H), 8.85 (s, 1H), 8.33 (s, 1H), 8.04 (s, 1H), 7.88 (s, 1H), 7.76 (s, 1H), 4.99-4.81 (m, 1H), 4.54 (dd, J=3.6, 11.2 Hz, 1H), 4.27 (dd, J=6.4, 11.2 Hz, 1H), 4.13-4.06 (m, 1H), 3.98 (s, 3H), 3.05 (t, J=4.4 Hz, 1H), 2.60-2.53 (m, 1H), 2.44-2.35 (m, 1H), 1.94-1.71 (m, 8H), 1.65-1.51 (m, 3H), 1.01 (t, J=7.2 Hz, 3H). LC-MS (ESI+) m/z 496.3 (M+H)+.

(4-Ethynylcyclohexyl)methanol (Intermediate AHS)

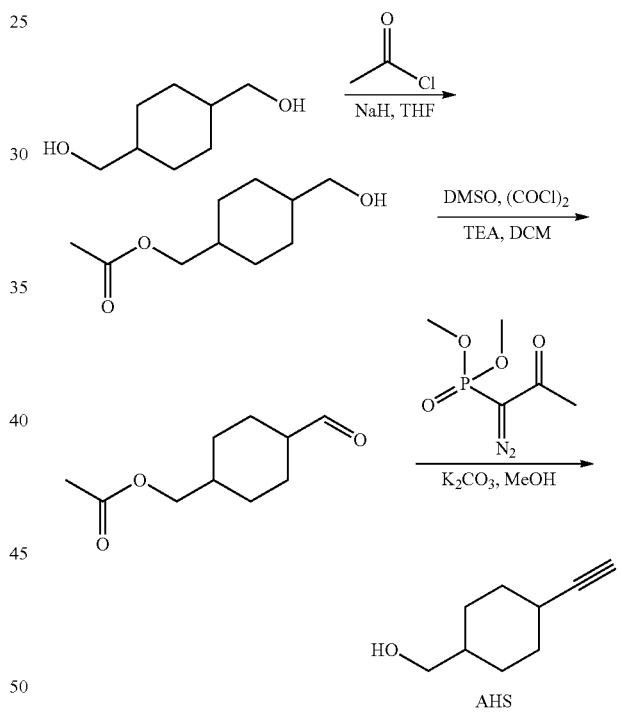

AHS

Step 1—[4-(Hydroxymethyl)cyclohexyl]methyl acetate

To a solution of [4-(hydroxymethyl)cyclohexyl]methanol (10.0 g, 69.3 mmol, CAS #105-08-8) in THF (100 mL) was added NaH (2.77 g, 69.3 mmol, 60% dispersion in mineral oil) at 0° C. for 0.5 hr. Then, acetyl chloride (5.44 g, 69.3 mmol, 4.95 mL) in a solution of THF (100 mL) was added dropwise into the above mixture. The reaction mixture was stirred at 15° C. for 3 hrs. On completion, the reaction mixture was quenched with water (0.7 mL) and then filtered. The filtrate was concentrated in vacuo. The residue was purified by column chromatography (SiO2, Petroleum ether/Ethyl acetate=8/1 to 4/1) to give the title compound (7.00 g, 54% yield) as a colorless oil. $^1$H NMR (400 MHz, CDCl$_3$) δ 4.04-3.88 (m, 2H), 3.60-3.44 (m, 2H), 2.06 (s, 3H), 1.93-1.78 (m, 3H), 1.74-1.29 (m, 6H), 1.03-0.99 (m, 2H).

Step 2—(4-Formylcyclohexyl)methyl acetate

To a solution of DMSO (6.04 g, 77.3 mmol, 6.04 mL) in DCM (100 mL) was slowly added (COCl)$_2$ (4.91 g, 38.66 mmol) at −72° C. The cooling bath was removed and the reaction mixture was stirred at −68° C. for 5 min. A solution of [4-(hydroxymethyl)cyclohexyl]methyl acetate (6 g, 32.2 mmol) in DCM (60 mL) was added at −65° C. Stirring for 1 hr was followed by addition of TEA (16.3 g, 161 mmol). The cooling bath was removed 25 minutes after completed addition. On completion, the reaction mixture was quenched with 1 M aqueous hydrochloric acid solution (152 ml, 152 mmol) at −10° C., and the layers were separated. The organic layer was washed with two 250 ml-portions of water and one 100-ml portion of brine, dried over anhydrous sodium sulfate and concentrated in vacuo to give the title compound (5.94 g, 100% yield) as a yellow oil. The product was unstable, thus was used for the next step without purification. $^1$H NMR (400 MHz, CDCl$_3$) δ 9.93-9.40 (m, 1H), 3.91-3.75 (m, 2H), 2.13-2.11 (m, 1H), 2.00-1.97 (m, 3H), 1.96-1.79 (m, 2H), 1.63-1.48 (m, 3H), 1.27-1.16 (m, 2H), 1.11-0.92 (m, 2H).

Step 3—(4-Ethynylcyclohexyl)methanol

To a solution of (4-formylcyclohexyl)methyl acetate (5.90 g, 32.0 mmol), potassium carbonate (13.3 g, 96.1 mmol) in methanol (100 mL) was added 1-diazo-1-dimethoxyphosphoryl-propan-2-one (8.00 g, 41.6 mmol, CAS #90965-06-3) at 0° C. The reaction mixture was stirred at 15° C. for 12 hrs. On completion, the reaction mixture was diluted with water (100 mL) and extracted with ethyl acetate (3×150 mL). The combined organic layers were washed with brine (2×50 mL), dried over anhydrous sodium sulfate, filtered and the concentrated in vacuo. The residue was purified by silica gel chromatography (petroleum ether:ethyl acetate=8:1 to 4:1) to give the title compound (3.80 g, 86% yield) as a white solid. $^1$H NMR (400 MHz, CDCl$_3$) δ 3.53-3.43 (m, 2H), 2.88-2.73 (m, 1H), 2.27-2.00 (m, 3H), 1.92-1.64 (m, 2H), 1.58-0.90 (m, 6H).

(4R,5S)-4-ethyl-5-(hydroxymethyl)pyrrolidin-2-one (Intermediate AHT)

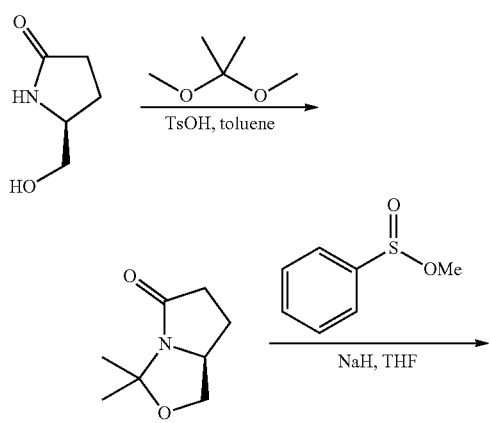

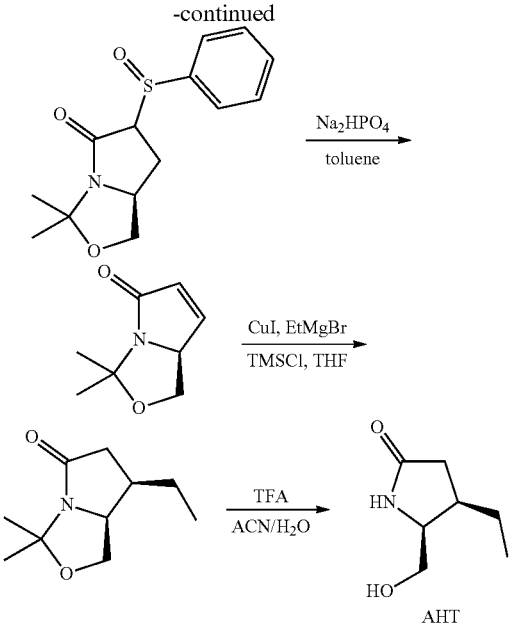

Step 1-(S)-3,3-Dimethyltetrahydropyrrolo[1,2-c]oxazol-5(3H)-one

To a mixture of (5S)-5-(hydroxymethyl)pyrrolidin-2-one (200 g, 1.74 mol, CAS #17342-08-4) and 2,2-dimethoxypropane (517 g, 4.97 mol) in toluene (2.4 L) was added TsOH.H$_2$O (13.2 g, 69.5 mmol). The reaction mixture was stirred at 120° C. for 16 hrs. On completion, the reaction mixture was concentrated in vacuo and diluted with EA (5 L). The mixture was washed with 1N NaOH solution (2 L) and extracted with EA (8×1 L). The organic layer was dried over Na$_2$SO$_4$, filtered and concentrated in vacuo. The residue was triturated with PE (200 mL) to give the title compound (200 g, 74% yield)) as as black brown crystal. $^1$H NMR (400 MHz, CDCl$_3$) δ=4.29-4.19 (m, 1H), 4.05 (dd, J=5.6, 8.4 Hz, 1H), 3.42 (t, J=8.4 Hz, 1H), 2.81-2.71 (m, 1H), 2.58-2.44 (m, 1H), 2.21-2.08 (m, 1H), 1.82-1.66 (m, 1H), 1.68 (s, 3H), 1.47 (s, 3H).

Step 2—(7aS)-6-(benzenesulfinyl)-3,3-dimethyl-1,6,7,7a-tetrahydropyrrolo[1,2-c]oxazol-5-one A solution of NaH (18.04 g, 451.05 mmol, 60% dispersion in mineral oil) in tetrahydrofuran (50 mL) was heated to 50° C. and maintained at that temperature for 1 h. A solution of (7aS)-3,3-dimethyl-1,6,7,7a-tetrahydropyrrolo[1,2-c]oxazol-5-one (35.0 g, 225 mmol, CAS #99208-71-6) in tetrahydrofuran (50 mL) was prepared in a dry 250 mL funnel under nitrogen. The mixture was stirred until it was homogeneous, then, was added into the above mixture at 50° C. at 55° C. Once the addition was complete, the mixture was maintained at 50 to 55° C. for 1 h, then, cooled to 45 to 50° C. Next, a solution of methyl benzenesulfinate (52.8 g, 338 mmol, 44.4 mL, CAS #670-98-4) in anhydrous tetrahydrofuran (50 mL) was added into the mixture in five portions at a rate sufficient to maintain the temperature at 45 to 55° C., while allowing 1 h between additions to allow hydrogen evolution to subside between additions. Once the addition was complete, the mixture was stirred at 35 to 48° C. with periodic nitrogen sparging. After about 3 h, the mixture was sampled every hour for HPLC analysis until the content of reactant 1 was consumed completely. On completion, the reaction mixture was put into 200 g ice water, then extracted with dichloromethane (3×300 mL). The combined organic layers were washed with brine (2×250 mL), dried over anhydrous sodium sulfate, filtered and the filtrate was concentrated in vacuo to give the title compound (63.0 g, 100% yield) as a white solid. LC-MS (ESI$^+$) m/z 280.1 (M+H)$^+$ Step 3—(7aS)-3,3-dimethyl-1,7a-dihydropyrrolo[1,2-c]oxazol-5-one To a solution of (7aS)-6-(benzenesulfinyl)-3,3-dimethyl-1,6,7,7a-tetrahydropyrrolo[1,2-c]oxazol-5-one (63 g, 225 mmol) in toluene (300 mL) was added Na$_2$HPO$_4$ (96.0 g, 676 mmol, 96.0 mL). The reaction mixture was heated to 85° C. for 1 hr, then heated further to 95 to 115° C. for 14 hrs. On completion, the reaction mixture was filtered and concentrated in vacuo. The oily residue was purified by silica gel chromatography (PE:EA=3:1) to give the title compound (30.0 g, 87% yield) as a yellow oil. $^1$H NMR (400 MHz, CDCl$_3$) δ 7.07 (dd, J=1.6, 5.6 Hz, 1H), 6.10 (dd, J=1.6, 5.6 Hz, 1H), 4.66 (tdd, J=1.6, 6.4, 9.6 Hz, 1H), 4.14 (dd, J=6.4, 8.0 Hz, 1H), 3.34 (dd, J=8.0, 9.6 Hz, 1H), 1.68 (s, 3H), 1.57 (s, 3H).

Step 4—(7R,7aS)-7-ethyl-3,3-dimethyl-1,6,7,7a-tetrahydropyrrolo[1,2-c]oxazol-5-one A solution of CuI (1.49 g, 7.83 mmol) in anhydrous tetrahydrofuran (100 mL) was cooled to −70 to −60° C., after which a solution of 1M EtMgBr in ether (117 mL) was added into the above mixture while maintaining the temperature at −45 to −65° C. The mixture was stirred for 1 h before being cooled to −78 to −65° C. TMSCl (9.36 g, 86.2 mmol, 10.9 mL) was added dropwise into the mixture. Then, the mixture was stirred for 1 h at −72 to −65° C. A solution of (7aS)-3,3-dimethyl-1,7a-dihydropyrrolo[1,2-c]oxazol-5-one (12.0 g, 78.3 mmol) in THF (50 mL) was added while maintaining the temperature at −72 to −65° C. The resulting reaction mixture was stirred at −60° C. for 4.5 h. On completion, the reaction was poured into the ice saturated NH$_4$Cl (200 mL) solution, and extracted with ethyl acetate (3×200 mL). The combined organic layers were washed with brine (100 mL), dried over with anhydrous sodium sulfate, filtered and the filtrate was concentrated in vacuo. The residue was purified by silica gel chromatography (PE:EA=10:1) to give the title compound (11.0 g, 77% yield) as a yellow oil. $^1$H NMR (400 MHz, CDCl$_3$) δ 4.34 (td, J=6.4, 9.6 Hz, 1H), 3.90 (dd, J=6.0, 8.4 Hz, 1H), 3.72 (dd, J=8.4, 9.6 Hz, 1H), 2.91 (dd, J=8.0, 16.8 Hz, 1H), 2.36-2.21 (m, 2H), 1.64 (s, 3H), 1.58-1.49 (m, 1H), 1.48 (s, 3H), 1.40-1.24 (m, 1H), 0.92 (t, J=7.2 Hz, 3H).

Step 5—(4R,5S)-4-ethyl-5-(hydroxymethyl)pyrrolidin-2-one (7R,7aS)-7-ethyl-3,3-dimethyl-1,6,7,7a-tetrahydropyrrolo[1,2-c]oxazol-5-one (8 g, 43.7 mmol) in acetonitrile (50 mL) and water (5 mL) was treated with TFA (995 mg, 8.73 mmol, 646 uL). The mixture was warmed to 25° C. for about 12 hrs. On completion, the mixture was concentrated in vacuo. The residue was reversed phase chromatography (neutral condition) to give the title compound (6.25 g, 100% yield) as yellow oil. $^1$H NMR (400 MHz, MeOD-d$_4$) δ 3.70-3.55 (m, 3H), 2.57-2.40 (m, 1H), 2.35-2.25 (m, 1H), 2.21-2.10 (m, 1H), 1.71-1.56 (m, 1H), 1.55-1.40 (m, 1H), 0.97 (t, J=7.2 Hz, 3H).

4-Bromo-1-[[(2S,3R)-3-ethyl-5-oxo-pyrrolidin-2-yl]methoxy]-7-methoxy-isoquinoline-6-carboxamide (Intermediate AHU)

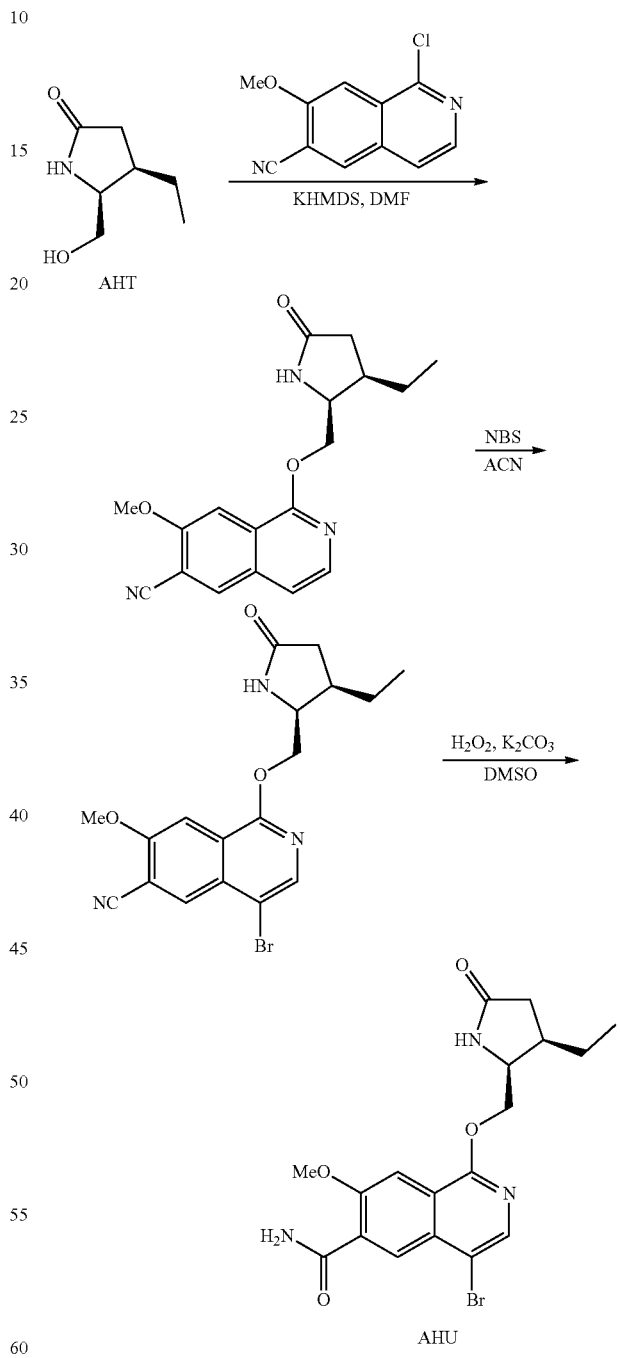

Step 1—1-[[(2S,3R)-3-ethyl-5-oxo-pyrrolidin-2-yl]methoxy]-7-methoxy-isoquinoline-6-carbonitrile To a solution of (4R,5S)-4-ethyl-5-(hydroxymethyl)pyrrolidin-2-one (3.00 g, 20.9 mmol, Intermediate AHT) and 1-chloro-7-methoxy-isoquinoline-6-carbonitrile (4.58 g, 20.9 mmol, synthesized via Step 1 of Intermediate CD) in DMF (50 mL) was cooled to −10° C. Then, KHMDS (1 M, 46.0 mL) was added dropwise into the above mixture. The reaction mixture was stirred at −10° C. for 2 hrs. On completion, the reaction mixture was diluted with EtOAc (100 mL) and added into a precooled (0 to 5° C.) solution of $NaH_2PO_4$ (10 g, 4.0 equiv) in water (100 g) over 15 min, keeping the temperature at ≤10° C. during the quenching process, then extracted with ethyl acetate (3×100 mL). After a pH check showed the pH of aqueous phase to be 7.8, the combined organic layers were washed with brine (2×50 mL), dried over anhydrous sodium sulfate, filtered and concentrated in vacuo. The residue was purified by silica gel chromatography (dichloromethane:ethyl acetate=1:1) to give the title compound (5.50 g, 80% yield) as a white solid. $^1$H NMR (400 MHz, $CDCl_3$) δ 8.04 (s, 1H), 7.95 (d, J=6.0 Hz, 1H), 7.50 (s, 1H), 7.20 (d, J=6.0 Hz, 1H), 6.45 (s, 1H), 4.65-4.51 (m, 2H), 4.15-4.09 (m, 1H), 4.04 (s, 3H), 2.73-2.58 (m, 1H), 2.55-2.45 (m, 1H), 2.25-2.18 (m, 1H), 1.74-1.63 (m, 1H), 1.57-1.45 (m, 1H), 1.02 (t, J=7.2 Hz, 3H). LC-MS (ESI$^+$) m/z 326.1 (M+H)$^+$.

Step 2—4-bromo-1-[[(2S,3R)-3-ethyl-5-oxo-pyrrolidin-2-yl]methoxy]-7-methoxy-isoquinoline-6-carbonitrile To a solution of 1-[[(2S,3R)-3-ethyl-5-oxo-pyrrolidin-2-yl]methoxy]-7-methoxy-isoquinoline-6-carbonitrile (3.5 g, 10.7 mmol) in ACN (40 mL) was added NBS (3.83 g, 21.5 mmol). The mixture was stirred at 60° C. for 0.5 hr. On completion, the reaction mixture was quenched with saturated $Na_2S_2O_3$ (50 mL). The reaction mixture was extracted with ethyl acetate (3×100 mL). The combined organic layers were washed with brine (2×50 mL), dried over anhydrous sodium sulfate, filtered and concentrated in vacuo. The residue was purified by silica gel chromatography (DCM to DCM:EA=1:1) to give the title compound (2.00 g, 46% yield) as a white solid. $^1$H NMR (400 MHz, $CDCl_3$) δ 8.27 (s, 1H), 8.05 (s, 1H), 7.49 (s, 1H), 7.44 (s, 1H), 4.56-4.42 (m, 2H), 4.14-4.07 (m, 1H), 4.05 (s, 3H), 2.70-2.58 (m, 1H), 2.53-2.40 (m, 1H), 2.15 (dd, J=10.4, 16.4 Hz, 1H), 1.68-1.57 (m, 1H), 1.44 (ddd, J=7.2, 9.2, 13.6 Hz, 1H), 1.00 (t, J=7.2 Hz, 3H).

Step 3—4-Bromo-1-[[(2S,3R)-3-ethyl-5-oxo-pyrrolidin-2-yl]methoxy]-7-methoxy-isoquinoline-6-carboxamide To a solution of 4-bromo-1-[[(2S,3R)-3-ethyl-5-oxo-pyrrolidin-2-yl]methoxy]-7-methoxy-isoquinoline-6-carbonitrile (1.5 g, 3.71 mmol) in DMSO (1 mL) was added $K_2CO_3$ (1.03 g, 7.42 mmol) and $H_2O_2$ (1.26 g, 11.1 mmol, 1.07 mL, 30% solution). The mixture was stirred at 15° C. for 0.5 hr. On completion, the reaction mixture was diluted with water (5 mL) and a solid precipitated out. Then, the reaction mixture was filtered and the filtered cake was collected, and dried over in vacuo to give the title compound (1.57 g, 100% yield) as a white solid. $^1$H NMR (400 MHz, $CDCl_3$) δ 8.76 (s, 1H), 8.03 (s, 1H), 7.63 (s, 1H), 7.46 (s, 1H), 6.76 (s, 1H), 6.28 (s, 1H), 4.65-4.45 (m, 2H), 4.16-4.09 (m, 1H), 4.05 (s, 3H), 2.73-2.61 (m, 1H), 2.56-2.45 (m, 1H), 2.23 (dd, J=10.8, 16.8 Hz, 1H), 1.71-1.60 (m, 2H), 1.49 (ddd, J=7.2, 9.2, 13.6 Hz, 1H), 1.02 (t, J=7.2 Hz, 3H).

1-[[(2S,3R)-3-ethyl-5-oxo-pyrrolidin-2-yl]methoxy]-4-[2-[4-(hydroxymethyl)cyclohexyl] ethynyl]-7-methoxy-isoquinoline-6-carboxamide (Intermediate AHV), 1-[[(2S,3R)-3-ethyl-5-oxo-pyrrolidin-2-yl]methoxy]-4-[2-[4-(hydroxymethyl)cyclohexyl]ethynyl]-7-methoxy-isoquinoline-6-carboxamide (Intermediate AHW)) and 1-[[(2S,3R)-3-ethyl-5-oxo-pyrrolidin-2-yl]methoxy]-4-[2-[4-(hydroxymethyl)cyclohexyl]ethynyl]-7-methoxy-isoquinoline-6-carboxamide (Intermediate AHX)

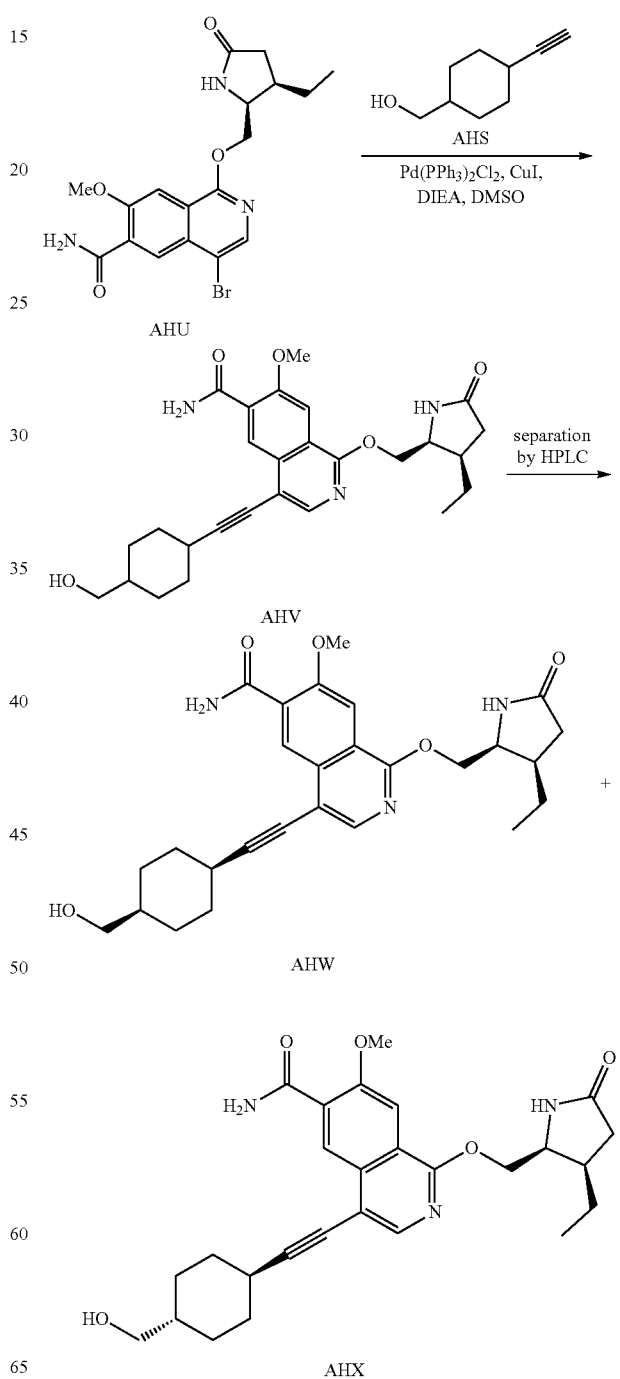

1893

Step 1—1-[[(2S,3R)-3-ethyl-5-oxo-pyrrolidin-2-yl]methoxy]-4-[2-[4-(hydroxymethyl)cyclohexyl] ethynyl]-7-methoxy-isoquinoline-6-carboxamide (4-Ethynylcyclohexyl)methanol (294 mg, 2.13 mmol, Intermediate AHS), 4-bromo-1-[[(2S,3R)-3-ethyl-5-oxo-pyrrolidin-2-yl]methoxy]-7-methoxy-isoquinoline-6-carboxamide (500 mg, 1.18 mmol, Intermediate AHU), CuI (45.1 mg, 236 umol), Pd(PPh$_3$)$_2$Cl$_2$ (166 mg, 236 umol) and DIPEA (765 mg, 5.92 mmol, 1.03 mL) in DMSO (12 mL) was de-gassed and then heated at 80° C. for 3 hours under N$_2$. On completion, the reaction mixture was quenched with water (80 mL), and extracted with EA (2×50 mL). The organic layer was washed with brine (100 mL), dried with Na$_2$SO$_4$, filtrated and concentrated in vacuo. The residue was purified by reverse phase (0.1% FA) to give the title compound (500 mg, 88% yield) as a white solid. $^1$H NMR (400 MHz, DMSO-d$_6$) δ 8.31 (s, 1H), 8.08-8.02 (m, 2H), 7.90 (s, 1H), 7.75 (s, 1H), 7.61 (s, 1H), 4.50-4.40 (m, 3H), 4.10-3.91 (m, 5H), 3.24 (t, J=5.6 Hz, 2H), 2.65-2.55 (m, 1H), 2.34-2.24 (m, 1H), 2.21-2.06 (m, 3H), 1.60-1.35 (m, 6H), 1.07-0.89 (m, 6H).

Step 2—1-[[(2S,3R)-3-ethyl-5-oxo-pyrrolidin-2-yl]methoxy]-4-[2-[4-(hydroxymethyl)cyclohexyl] ethynyl]-7-methoxy-isoquinoline-6-carboxamide and 1-[[(2S,3R)-3-ethyl-5-oxo-pyrrolidin-2-yl]methoxy]-4-[2-[4-(hydroxymethyl)cyclohexyl] ethynyl]-7-methoxy-isoquinoline-6-carboxamide 1-[[(2S,3R)-3-ethyl-5-oxo-pyrrolidin-2-yl]methoxy]-4-[2-[4-(hydroxymethyl)cyclohexyl] ethynyl]-7-methoxy-isoquinoline-6-carboxamide (500 mg, 1.46 mmol) was separated by prep-HPLC (column: Waters Xbridge C18 150*50 mm*10 um; mobile phase: [water (10 mM NH$_4$HCO$_3$)-ACN]; B %: 29%-49%,11.5 min) to give 1-[[(2S,3R)-3-ethyl-5-oxo-pyrrolidin-2-yl]methoxy]-4-[2-[4-(hydroxymethyl)cyclohexyl] ethynyl]-7-methoxy-isoquinoline-6-carboxamide (330 mg, 47% yield) as a white solid ($^1$H NMR (400 MHz, CDCl$_3$) δ 8.87 (s, 1H), 7.96 (s, 1H), 7.48 (s, 1H), 4.51 (d, J=4.4 Hz, 2H), 4.13-3.97 (m, 4H), 3.40 (d, J=6.4 Hz, 2H), 2.67-2.55 (m, 1H), 2.55-2.47 (m, 1H), 2.47-2.40 (m, 1H), 2.28-2.11 (m, 3H), 1.90-1.79 (m, 2H), 1.69-1.38 (m, 6H), 1.07-0.92 (m, 5H)) and 1-[[(2S,3R)-3-ethyl-5-oxo-pyrrolidin-2-yl]methoxy]-4-[2-[4-(hydroxymethyl)cyclohexyl] ethynyl]-7-methoxy-isoquinoline-6-carboxamide (110 mg, 16% yield) as a white solid, $^1$H NMR (400 MHz, CDCl$_3$) δ 9.03 (s, 1H), 7.96 (s, 1H), 7.74 (s, 1H), 7.42 (s, 1H), 6.14 (s, 1H), 5.95 (d, J=2.0 Hz, 1H), 4.62-4.42 (m, 2H), 4.06-3.96 (m, 4H), 3.57-3.55 (m, 2H), 3.06-3.03 (m, 1H), 2.77-2.67 (m, 1H), 2.65-2.52 (m, 1H), 2.47-2.38 (m, 1H), 2.19-2.16 (m, 1H), 1.98-1.95 (m, 2H), 1.92-1.79 (m, 2H), 1.66-1.54 (m, 5H), 1.51-1.38 (m, 2H), 0.94 (t, J=7.3 Hz, 3H). The cis-trans configuration was confirmed by 2D NMR.

1894

1-[[(2S,3R)-3-ethyl-5-oxo-pyrrolidin-2-yl]methoxy]-4-[2-(4-formylcyclohexyl)ethynyl]-7-methoxy-isoquinoline-6-carboxamide (Intermediate AHY)

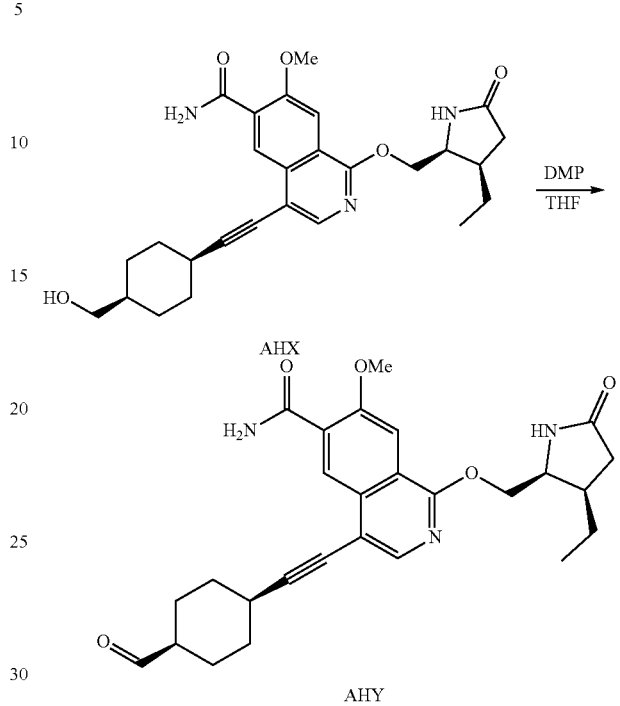

To a solution of 1-[[(2S,3R)-3-ethyl-5-oxo-pyrrolidin-2-yl]methoxy]-4-[2-[4-(hydroxymethyl) cyclohexyl]ethynyl]-7-methoxy-isoquinoline-6-carboxamide (60 mg, 125 umol, Intermediate AHV) in DCM (5 mL) was added DMP (63.6 mg, 150 umol, 46.4 uL). The reaction mixture was stirred at 0° C. for 2 hr. On completion, the reaction mixture was quenched with saturated sodium thiosulfate (3 mL), and the mixture was stirred at 0.5 hr. After, saturated sodium bicarbonate (5 mL) was added. The organic layer was separated, washed with brine (5 mL), dried over anhydrous sodium sulfate, filtered and the filtrate was concentrated in vacuo to give the title compound (50.0 mg, 49% yield) as a white solid. $^1$H NMR (400 MHz, CDCl$_3$) δ 9.71 (d, J=1.2 Hz, 1H), 9.00 (s, 1H), 8.04 (s, 1H), 7.73 (s, 1H), 7.52 (s, 1H), 5.96 (s, 1H), 5.93 (s, 1H), 4.13-4.09 (m, 4H), 2.73-2.61 (m, 1H), 2.55-2.46 (m, 1H), 2.35-2.20 (m, 2H), 2.12-1.96 (m, 4H), 1.93-1.75 (m, 4H), 1.72-1.64 (m, 2H), 1.56-1.46 (m, 2H), 1.02 (t, J=7.2 Hz, 4H). LC-MS (ESI$^+$) m/z 478.2 (M+H)$^+$.

5-[(3-Hydroxy-3-methyl-butyl)amino]pyrazolo[1,5-a]pyrimidine-3-carboxylic acid (Intermediate AHZ)

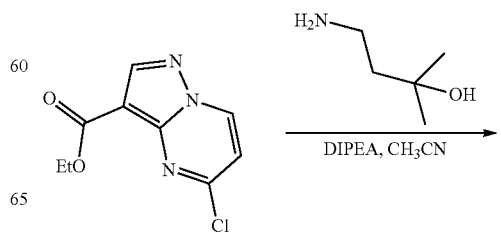

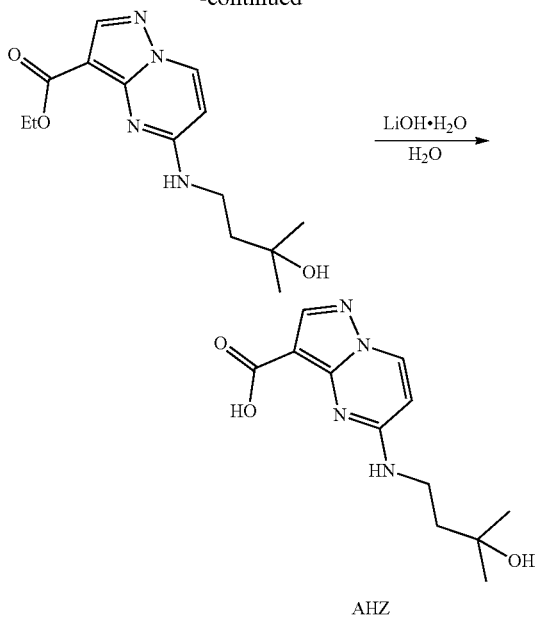

Step 1—Ethyl 5-[(3-hydroxy-3-methyl-butyl)amino]pyrazolo[1,5-a]pyrimidine-3-carboxylate To a solution of ethyl 5-chloropyrazolo[1,5-a]pyrimidine-3-carboxylate (200 mg, 886 umol, CAS #1244844-77-7) and 4-amino-2-methyl-butan-2-ol (91.4 mg, 886 umol, CAS #26734-08-7) in ACN (2 mL) was added DIPEA (229 mg, 1.77 mmol). The mixture was stirred at 60° C. for 1 hr. On completion, the mixture was concentrated in vacuo to give the title compound (250 mg, 96% yield) as colorless oil. LC-MS (ESI$^+$) m/z 293.1 (M+H)$^+$.

Step 2—5-[(3-Hydroxy-3-methyl-butyl)amino]pyrazolo[1,5-a]pyrimidine-3-carboxylic acid To a solution of ethyl 5-[(3-hydroxy-3-methyl-butyl)amino]pyrazolo[1,5-a]pyrimidine-3-carboxylate (250 mg, 855 umol) in H$_2$O (3 mL) was added LiOH—H$_2$O (179 mg, 4.28 mmol). The mixture was stirred at 60° C. for 2 hrs. On completion, the crude product was purified by reverse phase (0.1% FA condition) to give the title compound (120 mg, 45% yield, 90% purity) as white solid. $^1$H NMR (400 MHz, DMSO-d$_6$) δ 8.49 (d, J=7.2 Hz, 1H), 7.95 (s, 1H), 6.39 (d, J=7.2 Hz, 1H), 3.51-3.43 (m, 2H), 1.73-1.65 (m, 2H), 1.15 (s, 6H); LC-MS (ESI$^+$) m/z 265.0 (M+H)$^+$.

Benzyl N-methyl-N-[2-(4-piperidyl)ethyl]carbamate (Intermediate AIA)

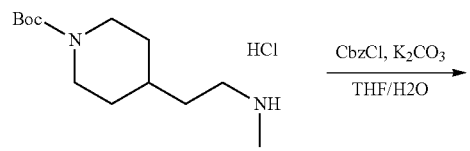

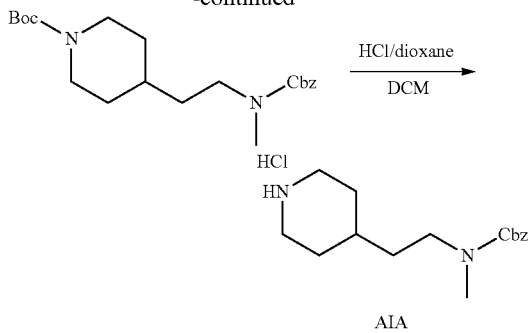

Step 1—Tert-butyl 4-[2-[benzyloxycarbonyl(methyl)amino]ethyl]piperidine-1-carboxylate To a solution of tert-butyl 4-[2-(methylamino)ethyl]piperidine-1-carboxylate (500 mg, 2.06 mmol, CAS #896103-62-1) in THF (2 mL) and H$_2$O (2 mL) was added CbzCl (422 mg, 2.48 mmol) and K$_2$CO$_3$ (570 mg, 4.13 mmol). The mixture was stirred at 0-15° C. for 2 hrs. On completion, the reaction mixture was concentrated in vacuo. The residue was diluted with 50 mL water and extracted with EA 150 mL (3×50 mL). The combined organic layers were washed with brine (50 mL), dried over Na$_2$SO$_4$, filtered and concentrated in vacuo to give the title compound (800 mg, 92% yield, 90% purity) as yellow oil. LC-MS (ESI$^+$) m/z 377.2 (M+H)$^+$.

Step 2—Benzyl N-methyl-N-[2-(4-piperidyl)ethyl]carbamate

To a solution of tert-butyl 4-[2-[benzyloxycarbonyl(methyl)amino]ethyl]piperidine-1-carboxylate (300 mg, 796 umol) in DCM (3 mL) was added HCl/dioxane (4 M, 2 mL). The mixture was stirred at 15° C. for 2 hrs. On completion, the mixture was concentrated in vacuo to give the title compound (220 mg, 99% yield) as white solid. LC-MS (ESI$^+$) m/z 277.7 (M+H)$^+$.

2-(2,6-Dioxo-3-piperidyl)-4-[4-[2-(methylamino)ethyl]-1-piperidyl]isoindoline-1,3-dione (Intermediate AIB)

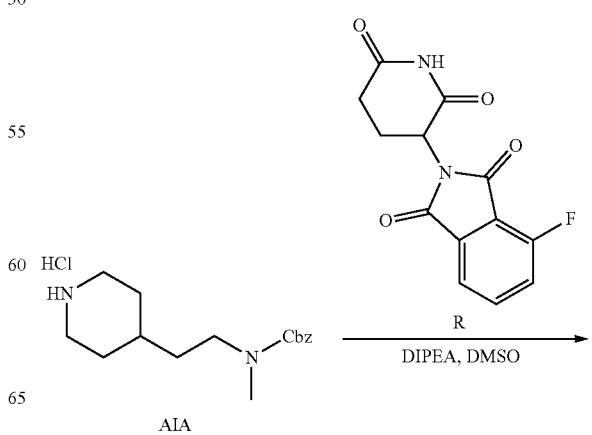

1897

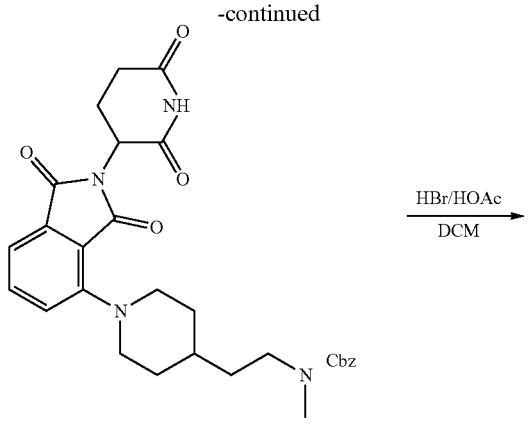

Step 1—Benzyl N-[2-[1-[2-(2,6-dioxo-3-piperidyl)-1,3-dioxo-isoindolin-4-yl]-4-piperidyl]ethyl]-N-methyl-carbamate To a solution of benzyl N-methyl-N-[2-(4-piperidyl) ethyl]carbamate (220 mg, 796 umol, Intermediate AIA) and 2-(2,6-dioxo-3-piperidyl)-4-fluoro-isoindoline-1,3-dione (219 mg, 796 umol, Intermediate R) in DMSO (5 mL) was added DIPEA (102 mg, 796 umol). The mixture was stirred at 130° C. for 6 hours. On completion, the mixture was concentrated in vacuo to give the residue. The residue was purified by reverse phase (0.1% FA condition) to give the title compound (170 mg, 40% yield) as yellow solid. LC-MS (ESI$^+$) m/z 533.3 (M+H)$^+$.

Step 2—2-(2,6-Dioxo-3-piperidyl)-4-[4-[2-(methylamino)ethyl]-1-piperidyl]isoindoline-1,3-dione To a solution of benzyl N-[2-[1-[2-(2,6-dioxo-3-piperidyl)-1,3-dioxo-isoindolin-4-yl]-4-piperidyl] ethyl]-N-methyl-carbamate (160 mg, 300 umol) in DCM (10 mL) was added HBr/AcOH (300 umoL, 5 mL). The mixture was stirred at 15° C. for 2 hours. On completion, the mixture was concentrated in vacuo to give the title compound (100 mg, 70% yield, HBr salt) as brown solid. LC-MS (ESI$^+$) m/z 399.2 (M+1)$^+$.

1898

Tert-butyl N-methyl-N-(2-oxoethyl)carbamate (Intermediate AIC)

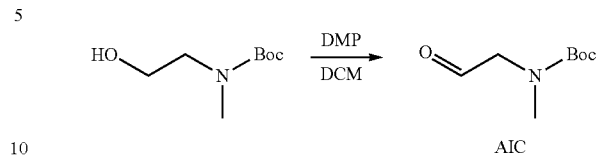

To a solution of tert-butyl N-(2-hydroxyethyl)-N-methyl-carbamate (100 mg, 570 umol) in DCM (2 mL) was added DMP (363 mg, 856 umol). The mixture was stirred at 15° C. for 2 hrs. On completion, the mixture was filtered and the filtrate was concentrated in vacuo to give the title compound (100 mg, 60% yield) as yellow oil.

2-(2,6-Dioxo-3-piperidyl)-4-piperazin-1-yl-isoindoline-1,3-dione (Intermediate AID)

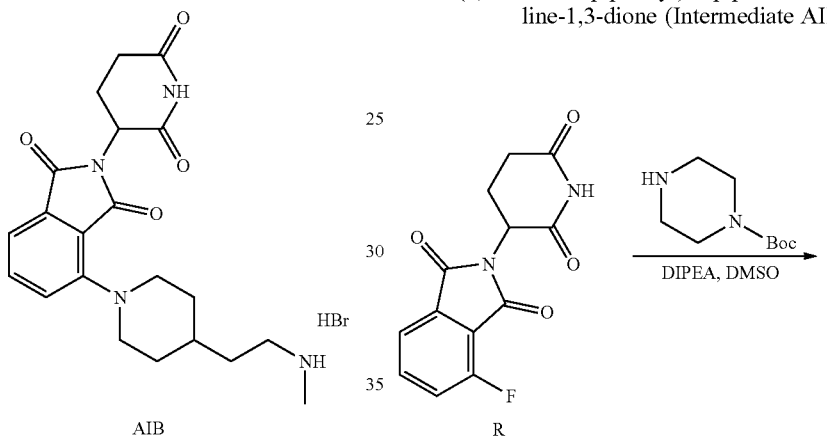

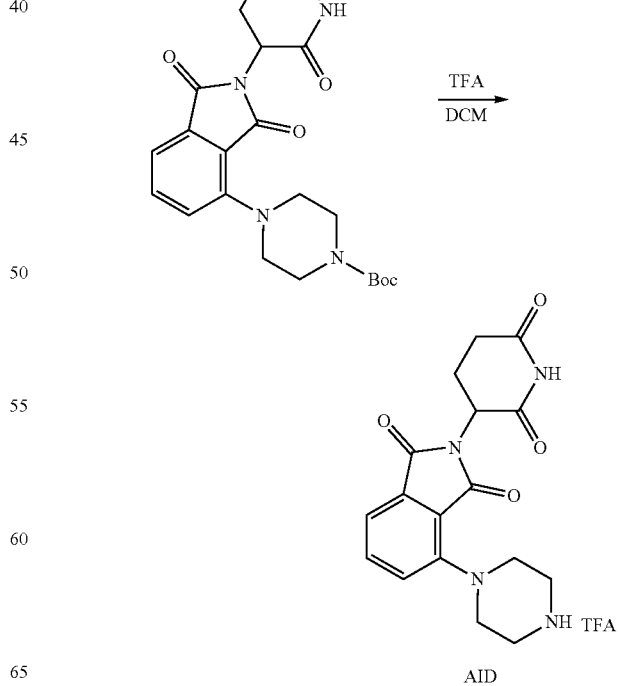

Step 1—Tert-butyl 4-[2-(2,6-dioxo-3-piperidyl)-1,3-dioxo-isoindolin-4-yl]piperazine-1-carboxylate To a solution of tert-butyl piperazine-1-carboxylate (1.62 g, 8.69 mmol, CAS #143238-38-4) and 2-(2,6-dioxo-3-piperidyl)-4-fluoro-isoindoline-1,3-dione (2.00 g, 7.24 mmol Intermediate R) in DMSO (20 mL) was added DIPEA (935 mg, 7.24 mmol). The mixture was stirred at 130° C. for 6 hrs. On completion, the mixture was added 100 mL water and most of solid was precipitated out. The reaction mixture was filtrated. The filtered cake was washed with water (3×50 mL) and dried in vacuo to give the title compound (3.00 g, 90% yield) as yellow solid. LC-MS (ESI$^+$) m/z 443.3 (M+H)$^+$.

Step 2—2-(2,6-Dioxo-3-piperidyl)-4-piperazin-1-yl-isoindoline-1,3-dione

To a solution of tert-butyl 4-[2-(2,6-dioxo-3-piperidyl)-1,3-dioxo-isoindolin-4-yl]piperazine-1-carboxylate (200 mg, 452 umol) in DCM (10 mL) was added TFA (7.70 g, 67.5 mmol). The mixture was stirred at 15° C. for 2 hrs. On completion, the mixture was concentrated in vacuo to give the title compound (200 mg, TFA salt, 99% yield) as yellow oil. LC-MS (ESI$^+$) m/z 343.6 (M+H)$^+$.

2-(2,6-Dioxo-3-piperidyl)-4-[4-[2-(methylamino)ethyl]piperazin-1-yl]isoindoline-1,3-dione (Intermediate AIE)

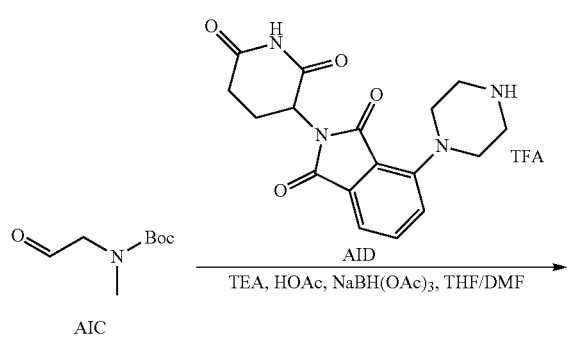

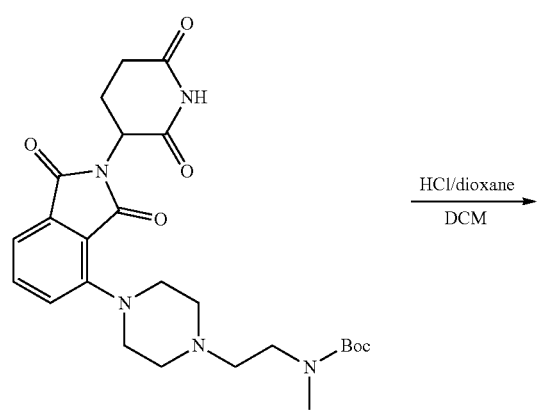

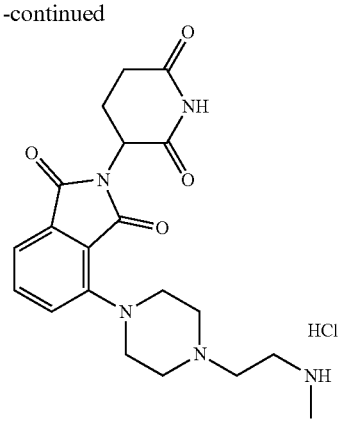

AIE

Step 1—Tert-butyl N-[2-[4-[2-(2,6-dioxo-3-piperidyl)-1,3-dioxo-isoindolin-4-yl]piperazin-1-yl]ethyl]-N-methyl-carbamate To a solution of 2-(2,6-dioxo-3-piperidyl)-4-piperazin-1-yl-isoindoline-1,3-dione (198 mg, 577 umol, Intermediate AID) in DCM (10 mL) and THF (10 mL) was added Et$_3$N (58.4 mg, 577 umol). The mixture was stirred at 0-15° C. for 0.5 hr, HOAc (34.6 mg, 577 umol) and tert-butyl N-methyl-N-(2-oxoethyl)carbamate (100 mg, 577 umol, Intermediate AIC) were added to the reaction mixture. The mixture was stirred at 0-15° C. for 0.5 hr, NaBH(OAc)$_3$ (122 mg, 577 umol) was added to the mixture at 0° C. and the mixture was stirred at 0° C. for 2 hrs. On completion, the mixture was quenched by 2 mL water and concentrated in vacuo. The residue was purified by reverse phase (0.1% FA condition) to give the title compound (60.0 mg, 20% yield) as yellow solid. $^1$H NMR (400 MHz, DMSO-d$_6$) δ 11.08 (s, 1H), 7.81-7.62 (m, 1H), 7.44-7.24 (m, 2H), 5.09 (dd, J=5.4, 13.1 Hz, 1H), 4.73-4.57 (m, 1H), 3.50-3.43 (m, 2H), 3.29 (m, 3H), 3.21-3.16 (m, 2H), 2.80 (m, 6H), 2.63-2.58 (m, 4H), 1.40 (s, 9H); LC-MS (ESI$^+$) m/z 500.2 (M+1)$^+$.

Step 2—2-(2,6-Dioxo-3-piperidyl)-4-[4-[2-(methylamino)ethyl]piperazin-1-yl]isoindoline-1,3-dione To a solution of tert-butyl N-[2-[4-[2-(2,6-dioxo-3-piperidyl)-1,3-dioxo-isoindolin-4-yl]piperazin-1-yl] ethyl]-N-methyl-carbamate (60.0 mg, 120 umol) in DCM (2 mL) was added HCl/dioxane (4 M, 1 mL). The mixture was stirred at 25° C. for 0.5 hr. On completion, the mixture was concentrated in vacuo to give title compound (48.0 mg, 90% yield) as yellow solid. LC-MS (ESI$^+$) m/z 400.3 (M+H)$^+$.

2-(2,6-Dioxo-3-piperidyl)-4-[3-(4-piperidyloxy)propoxy]isoindoline-1,3-dione (Intermediate AIF)

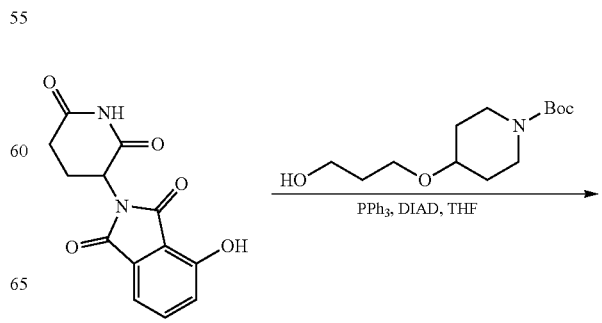

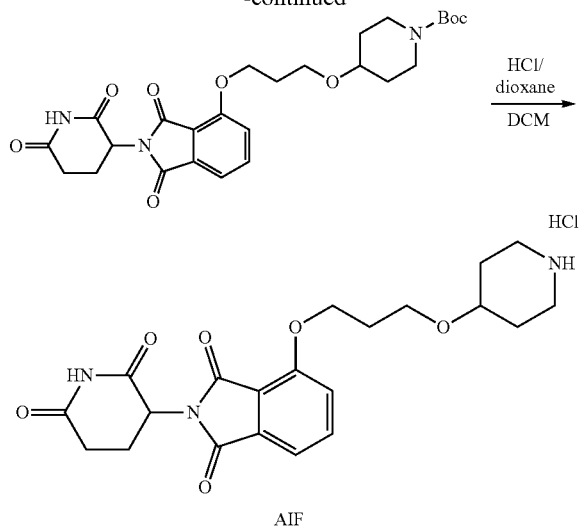

Step 1—Tert-butyl 4-[3-[2-(2,6-dioxo-3-piperidyl)-1,3-dioxo-isoindolin-4-yl]oxypropoxy]piperidine-1-carboxylate To a solution of 2-(2,6-dioxo-3-piperidyl)-4-hydroxy-isoindoline-1,3-dione (450 mg, 1.64 mmol, synthesized via Step 1 of Intermediate CA), tert-butyl 4-(3-hydroxy-propoxy)piperidine-1-carboxylate (432 mg, 1.67 mmol, synthesized via Steps 1-2 of Intermediate ADK) and PPh₃ (648 mg, 2.47 mmol) in THF (10 mL) was added DIAD (504 mg, 2.49 mmol) at 0° C. The mixture was stirred at 50° C. for 16 hours. On completion, the reaction was quenched with water (0.5 mL) and the mixture was concentrated in vacuo. The residue was purified by column chromatography on silica gel to give the title compound (1.60 g, 94% yield) as yellow gum. LC-MS (ESI⁺) m/z 416.1 (M+H−100)⁺.

Step 2—2-(2,6-Dioxo-3-piperidyl)-4-[3-(4-piperidyloxy)propoxy]isoindoline-1,3-dione To a solution of tert-butyl 4-[3-[2-(2,6-dioxo-3-piperidyl)-1,3-dioxo-isoindolin-4-yl]oxypropoxy] piperidine-1-carboxylate (1.55 g, 1.50 mmol) in DCM (10 mL) was added HCl/dioxane (4.0 M, 5 mL) at 10° C. The mixture was stirred at 10° C. for 1 hour. On completion, the mixture was concentrated in vacuo. The residue was purified by reversed phase flash (TFA condition) to give the title compound (280 mg, 44% yield) as light yellow solid. ¹H NMR (400 MHz, DMSO-d₆) δ 11.11 (s, 1H), 7.84-7.80 (m, 1H), 7.54 (d, J=8.4 Hz, 1H), 7.46 (d, J=7.2 Hz, 1H), 5.11-5.06 (m, 1H), 4.28 (t, J=6.0 Hz, 2H), 3.62 (t, J=6.0 Hz, 2H), 3.57-3.55 (m, 1H), 3.47-3.43 (m, 2H), 3.16-3.04 (m, 3H), 2.97-2.88 (m, 4H), 2.10-1.97 (m, 3H), 1.72-1.64 (m, 3H).

4-[3-[[1-[[4-[4-Amino-3-(difluoromethyl)pyrazol-1-yl]cyclohexyl]methyl]-4-piperidyl]oxy] propoxy]-2-(2,6-dioxo-3-piperidyl)isoindoline-1,3-dione (Intermediate AIG)

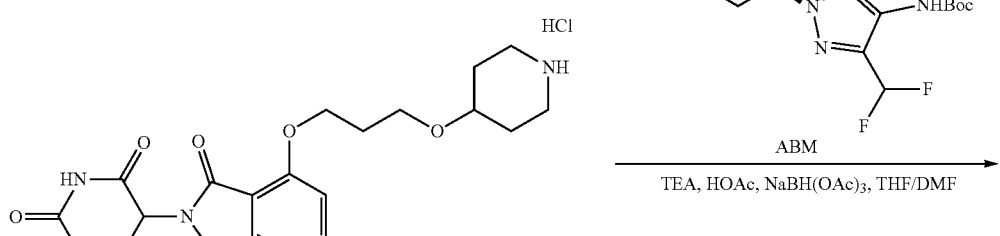

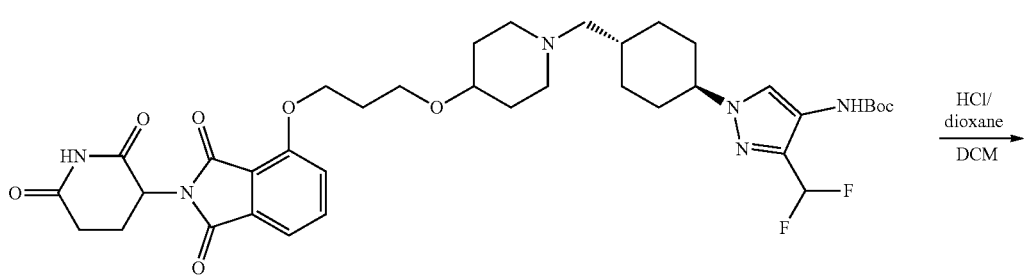

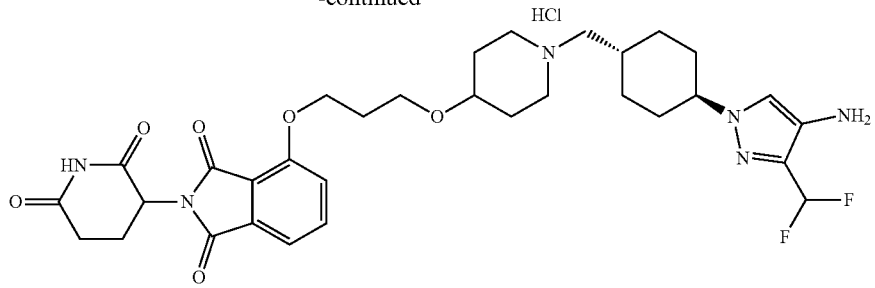

AIG

Step 1—Tert-butyl N-[3-(difluoromethyl)-1-[4-[[4-[3-[2-(2,6-dioxo-3-piperidyl)-1,3-dioxo-isoindolin-4-yl]oxypropoxy]-1-piperidyl]methyl]cyclohexyl]pyrazol-4-yl]carbamate To a solution of 2-(2,6-dioxo-3-piperidyl)-4-[3-(4-piperidyloxy)propoxy]isoindoline-1,3-dione (270 mg, 649 umol, Intermediate AIF) in THF (5 mL) and DMF (1.5 mL) was added TEA (189 mg, 1.87 mmol) at 0° C. The mixture was stirred at 0° C. for 30 minutes. Then tert-butyl N-[3-(difluoromethyl)-1-(4-formyl yclohexyl)pyrazol-4-yl]carbamate (193 mg, 562 umol, Intermediate ABM) and HOAc (108 mg, 1.80 mmol) were added to the reaction mixture. The mixture was stirred at 0° C. for 30 minutes. Next, NaBH(OAc)$_3$ (253 mg, 1.19 mmol) was added to the reaction mixture at 0° C. The mixture was stirred at 0° C. for 1 hour. On completion, the reaction was quenched with water (0.3 mL) and the mixture was concentrated in vacuo. The residue was purified by reversed phase flash (TFA condition) to give the title compound (230 mg, 45% yield) as light yellow gum. LC-MS (ESI$^+$) m/z 743.5 (M+H)$^+$.

Step 2—4-[3-[[1-[[4-[4-Amino-3-(difluoromethyl)pyrazol-1-yl]cyclohexyl]methyl]-4-piperidyl]oxy]propoxy]-2-(2,6-dioxo-3-piperidyl)isoindoline-1,3-dione To a solution of tert-butyl N-[3-(difluoromethyl)-1-[4-[[4-[3-[2-(2,6-dioxo-3-piperidyl)-1,3-dioxo-isoindolin-4-yl]oxypropoxy]-1-piperidyl]methyl]cyclohexyl]pyrazol-4-yl]carbamate (60.0 mg, 76.9 umol) in DCM (2 mL) was added HCl/dioxane (4.0 M, 1.10 mL) at 15° C. The mixture was stirred at 15° C. for 3 hours. On completion, the mixture was concentrated in vacuo to give the title compound (58.0 mg, 99% yield, TFA salt) as light yellow gum. LC-MS (ESI$^+$) m/z 643.5 (M+H)$^+$.

Tert-butyl N-[3-(3-aminopropoxy)propyl]carbamate (Intermediate AIH)

Step 1—Tert-butyl N-[3-(2-cyanoethoxy)propyl]carbamate

To a mixture of tert-butyl N-(3-hydroxypropyl)carbamate (10.0 g, 57.0 mmol, 9.80 mL, CAS #58885-58-8) and prop-2-enenitrile (6.06 g, 114 mmol, 7.57 mL, CAS #107-13-1) in THF (100 mL) was added NaOMe (308 mg, 5.71 mmol). The reaction mixture was stirred at 25° C. for 12 hours. On completion, the reaction mixture was diluted with water (100 mL) and extracted with EA (2×200 mL). The combined organic layers was dried over Na$_2$SO$_4$, filtered and concentrated in vacuo to give a residue. The residue was purified by column chromatography to give the title compound (9.70 g, 74% yield) as colorless oil. $^1$H NMR (400 MHz, CDCl$_3$) δ 4.77 (s, 1H), 3.64 (t, J=6.0 Hz, 2H), 3.54 (t, J=6.0 Hz, 2H), 3.27-3.16 (m, 2H), 2.59 (t, J=6.0 Hz, 2H), 1.81-1.72 (m, 2H), 1.43 (s, 9H).

Step 2—Tert-butyl N-[3-(3-aminopropoxy)propyl]carbamate

To a mixture of tert-butyl N-[3-(2-cyanoethoxy)propyl]carbamate (9.70 g, 42.49 mmol) in MeOH (80 mL) was added NH$_3$.H$_2$O (910 mg, 6.49 mmol, 1 mL, 25% solution) and Raney-Ni (3.68 g, 43.0 mmol). The reaction mixture was stirred at 25° C. for 12 hours under H$_2$ (50 Psi) atmosphere. On completion, the reaction mixture was filtered and concentrated in vacuo to give the title compound (9.00 g, 91% yield) as colorless oil. $^1$H NMR (400 MHz, CDCl$_3$) δ 4.97 (s, 1H), 3.51-3.45 (m, 4H), 3.26-3.17 (m, 2H), 2.80 (t, J=6.8 Hz, 2H), 2.69 (t, J=6.8 Hz, 1H), 1.79-1.68 (m, 4H), 1.44 (s, 9H).

Ethyl 4-(3-bromo-1,2,4-triazol-1-yl)cyclohexanecarboxylate (Intermediate AII) and ethyl 4-(5-bromo-1,2,4-triazol-1-yl)cyclohexanecarboxylate (Intermediate AIJ)

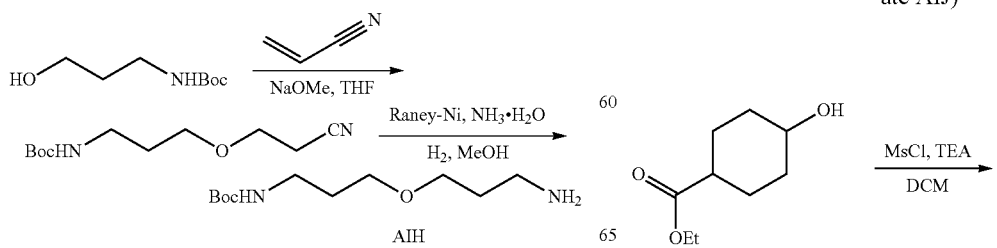

-continued

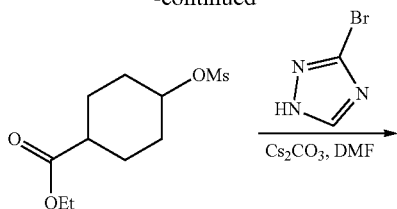

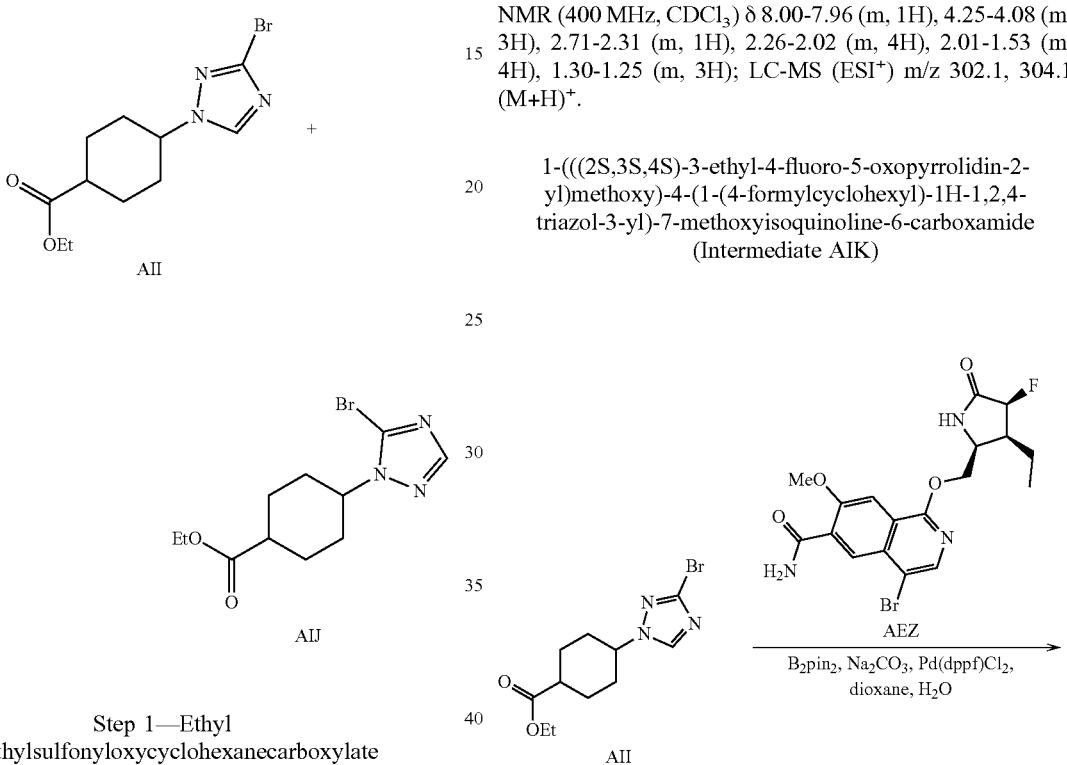

Step 1—Ethyl 4-methylsulfonyloxycyclohexanecarboxylate

To a solution of ethyl 4-hydroxycyclohexanecarboxylate (3.00 g, 17.4 mmol, CAS #17159-80-7) and TEA (3.53 g, 34.8 mmol) in DCM (30 mL) was added MsCl (2.39 g, 20.9 mmol). The reaction mixture was stirred at 10° C. for 30 minutes. On completion, the reaction mixture was washed with 0.1N HCl solution until the pH=7. The organic layer was dried over $Na_2SO_4$, filtered and concentrated in vacuo to give the title compound (4.35 g, 99% yield, a mixture of trans and cis) as colorless oil. $^1H$ NMR (400 MHz, $CDCl_3$) δ 4.97-4.60 (m, 1H), 4.19-4.10 (m, 2H), 3.05-3.00 (m, 3H), 2.48-2.27 (m, 1H), 2.25-2.01 (m, 3H), 2.00-1.58 (m, 5H), 1.50-1.22 (m, 3H).

Step 2—Ethyl 4-(3-bromo-1,2,4-triazol-1-yl)cyclohexanecarboxylate

To a mixture of ethyl 4-methylsulfonyloxycyclohexanecarboxylate (3.16 g, 12.6 mmol) and 3-bromo-1H-1,2,4-triazole (1.70 g, 11.4 mmol, CAS #7343-33-1) in DMF (30 mL) was added $Cs_2CO_3$ (7.49 g, 22.9 mmol) at 20° C. The reaction mixture was stirred at 85° C. for 19 hrs under nitrogen. On completion, the reaction mixture was concentrated in vacuo to remove DMF. The residue was diluted with water (100 mL), and extracted with EA (3×100 mL).

The combined layer was dried over $Na_2SO_4$, filtered and concentrated in vacuo. The residue was purified by silica gel chromatography (PE:EA=5:1) to give ethyl 4-(5-bromo-1,2,4-triazol-1-yl)cyclohexanecarboxylate (600 mg, 17% yield, a mixture of trans and cis) as colorless gum, which was confirmed by $^1H$ NMR and 2D NMR; $^1H$ NMR (400 MHz, $CDCl_3$) δ 7.91-7.84 (m, 1H), 4.40-4.24 (m, 1H), 4.24-4.09 (m, 2H), 2.73-2.38 (m, 1H), 2.38-1.98 (m, 4H), 1.93-1.56 (m, 4H), 1.31-1.25 (m, 3H); LC-MS ($ESI^+$) m/z 302.1, 304.1 $(M+H)^+$; and ethyl 4-(3-bromo-1,2,4-triazol-1-yl)cyclohexanecarboxylate (1.00 g, 28% yield) as colorless gum, which was confirmed by $^1H$ NMR and 2D NMR. $^1H$ NMR (400 MHz, $CDCl_3$) δ 8.00-7.96 (m, 1H), 4.25-4.08 (m, 3H), 2.71-2.31 (m, 1H), 2.26-2.02 (m, 4H), 2.01-1.53 (m, 4H), 1.30-1.25 (m, 3H); LC-MS ($ESI^+$) m/z 302.1, 304.1 $(M+H)^+$.

1-(((2S,3S,4S)-3-ethyl-4-fluoro-5-oxopyrrolidin-2-yl)methoxy)-4-(1-(4-formylcyclohexyl)-1H-1,2,4-triazol-3-yl)-7-methoxyisoquinoline-6-carboxamide (Intermediate AIK)

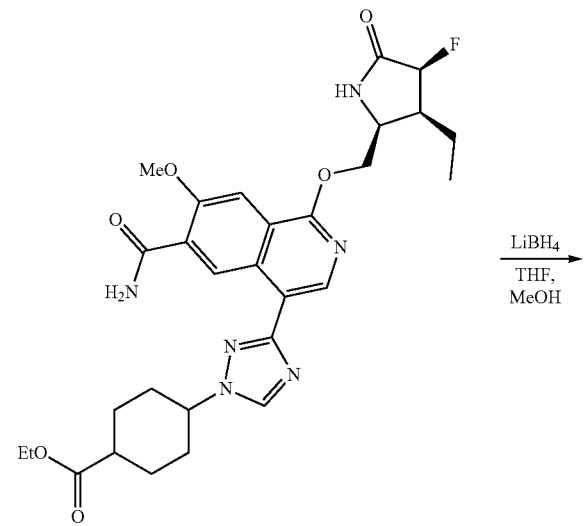

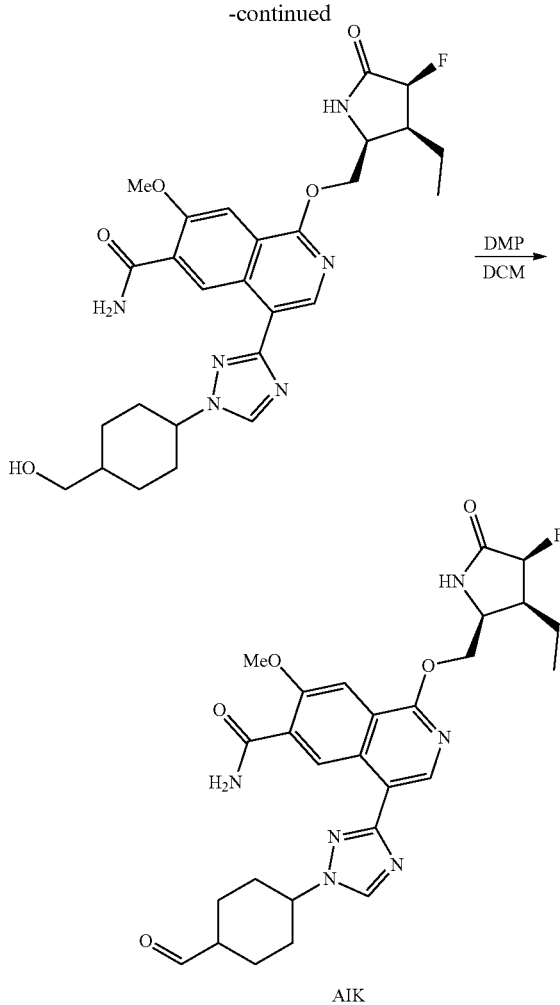

AIK

Step 1—Ethyl 4-(3-(6-carbamoyl-1-(((2S,3S,4S)-3-ethyl-4-fluoro-5-oxopyrrolidin-2-yl)methoxy)-7-methoxyisoquinolin-4-yl)-1H-1,2,4-triazol-1-yl)cyclohexanecarboxylate A mixture of 4-bromo-1-(((2S,3S,4S)-3-ethyl-4-fluoro-5-oxopyrrolidin-2-yl)methoxy)-7-methoxy isoquinoline-6-carboxamide (110 mg, 249 umol, Intermediate AEZ), ethyl 4-(3-bromo-1,2,4-triazol-1-yl) cyclohexanecarboxylate (226 mg, 749 umol, Intermediate AII), 4,4,5,5-tetramethyl-2-(4,4,5,5-tetramethyl-1,3,2-dioxaborolan-2-yl)-1,3,2-dioxaborolane (824 mg, 3.25 mmol), $Na_2CO_3$ (79.4 mg, 749 umol) and Pd(dppf)$Cl_2$ (18.2 mg, 24.9 umol) in a mixture solvent of dioxane (40 mL) and water (8 mL) was stirred at 90° C. for 5 hrs under nitrogen. On completion, the reaction mixture was concentrated in vacuo. The residue was purified by silica gel chromatography (EA/MeOH=10/1) to give impure product. The impure product was re-purified by prep-TLC (EA/MeOH=10/1) to give the title compound (30.0 mg, 20% yield, a mixture of trans and cis) as yellow solid. LC-MS (ESI$^+$) m/z 583.4 (M+H)$^+$.

Step 2—1-(((2S,3S,4S)-3-ethyl-4-fluoro-5-oxopyrrolidin-2-yl)methoxy)-4-(1-(4-(hydroxymethyl)cyclohexyl)-1H-1,2,4-triazol-3-yl)-7-methoxyisoquinoline-6-carboxamide To a mixture of ethyl 4-(3-(6-carbamoyl-1-(((2S,3S,4S)-3-ethyl-4-fluoro-5-oxopyrrolidin-2-yl) methoxy)-7-methoxyisoquinolin-4-yl)-1H-1,2,4-triazol-1-yl)cyclohexanecarboxylate (27.0 mg, 46.3 umol) in a mixture of THF (8 mL) and MeOH (1 mL) was added LiBH$_4$ (2.02 mg, 92.6 umol) at 20° C. The reaction mixture was stirred at 20° C. for 4 hrs. Then LiBH$_4$ (5.05 mg, 231 umol) was added. The reaction mixture was stirred at 20° C. for 16 hrs. On completion, the reaction mixture was quenched with a saturated NH$_4$Cl solution (1 mL) and concentrated in vacuo. The residue was diluted with water (10 mL) and extracted with DCM (3×10 mL). The combined organic layers were concentrated in vacuo to give a residue. The residue was purified by Prep-TLC (EA/MeOH=5/1) to give impure product. The impure product was re-purified by Prep-HPLC (column: Shim-pack C18 150*25*10 um; mobile phase: [water (0.225% FA)-ACN]; B %: 19%-49%,10 min) to give the title compound (5.00 mg, 20% yield, a mixture of trans and cis) as light yellow solid. LC-MS (ESI$^+$) m/z 541.4 (M+H)$^+$.

Step 3—1-(((2S,3S,4S)-3-ethyl-4-fluoro-5-oxopyrrolidin-2-yl)methoxy)-4-(1-(4-formylcyclohexyl)-1H-1,2,4-triazol-3-yl)-7-methoxyisoquinoline-6-carboxamide To a mixture of 1-(((2S,3S,4S)-3-ethyl-4-fluoro-5-oxopyrrolidin-2-yl)methoxy)-4-(1-(4-(hydroxyl methyl)cyclohexyl)-1H-1,2,4-triazol-3-yl)-7-methoxyisoquinoline-6-carboxamide (5.00 mg, 9.25 umol) in DCM (1 mL) was added DMP (7.85 mg, 18.5 umol). The reaction mixture was stirred at 20° C. for 1 hr. On completion, the reaction mixture was washed with saturated NaHCO$_3$ solution. The organic layer was concentrated in vacuo. The residue was purified by prep-TLC (EA/MeOH=10/1) to give the title compound (4.50 mg, 90% yield) as white solid. LC-MS (ESI$^+$) m/z 539.4 (M+H)$^+$.

1-[[(2S,3R)-3-ethyl-5-oxo-pyrrolidin-2-yl]methoxy]-7-methoxy-4-[2-(4-piperidyl)ethynyl] isoquinoline-6-carboxamide (Intermediate AIL)

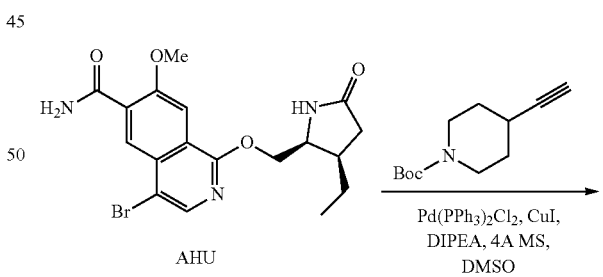

AHU

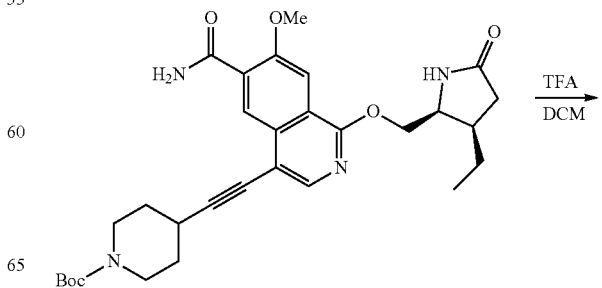

1909

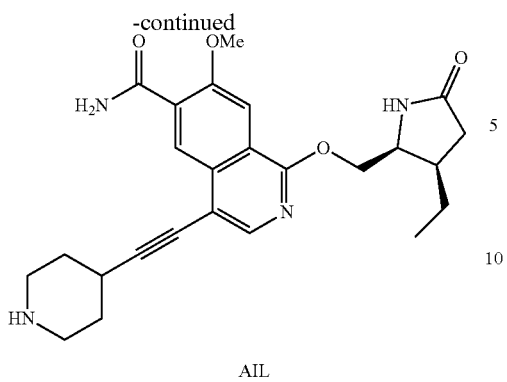

AIL

Step 1—Tert-butyl 4-[2-[6-carbamoyl-1-[[(2S,3R)-3-ethyl-5-oxo-pyrrolidin-2-yl]methoxy]-7-methoxy-4-isoquinolyl]ethynyl]piperidine-1-carboxylate A mixture of 4-bromo-1-[[(2S,3R)-3-ethyl-5-oxo-pyrrolidin-2-yl]methoxy]-7-methoxy-isoquinoline-6-carboxamide (100 mg, 236 umo, Intermediate AHU), tert-butyl 4-ethynylpiperidine-1-carboxylate (74.3 mg, 355 umol, CAS #297192-97-6), Pd(PPh$_3$)$_2$Cl$_2$ (16.6 mg, 23.7 umol), CuI (4.51 mg, 23.7 umol), 4 Å molecular sieves (100 mg) and DIPEA (153 mg, 1.18 mmol) in DMSO (2.00 mL) was degassed and purged with N$_2$ for 3 times, and then the mixture was stirred at 80° C. for 2 hrs under N$_2$ atmosphere. On completion, the reaction mixture was filtered and concentrated in vacuo to give a residue. The residue was purified by reversed phase (0.1% FA condition) to give the title compound (90.0 mg, 69% yield) as a yellow solid. LC-MS (ESI$^+$) m/z 551.3 (M+H)$^+$.

Step 2—1-[[(2S,3R)-3-ethyl-5-oxo-pyrrolidin-2-yl]methoxy]-7-methoxy-4-[2-(4-piperidyl)ethynyl]isoquinoline-6-carboxamide To a solution of tert-butyl 4-[2-[6-carbamoyl-1-[[(2S,3R)-3-ethyl-5-oxo-pyrrolidin-2-yl]methoxy]-7-methoxy-4-isoquinolyl]ethynyl]piperidine-1-carboxylate (90.0 mg, 163 umol) in DCM (1.00 mL) was added TFA (3.46 g, 30.4 mmol), then the mixture was stirred at 20° C. for 0.5 hr. On completion, the reaction mixture was concentrated in vacuo to give the title compound (90.0 mg, 97% yield, TFA) as a yellow solid. $^1$H NMR (400 MHz, CDCl$_3$) δ 9.43 (s, 1H), 8.88 (m, 2H), 8.09 (s, 1H), 8.06 (s, 1H), 8.02 (s, 1H), 7.57 (s, 1H), 4.73-4.70 (m, 1H), 4.54-4.50 (m, 1H), 4.25-4.20 (m, 1H), 4.09 (s, 3H), 3.63-3.49 (m, 2H), 3.42-3.29 (m, 2H), 3.26-3.19 (m, 1H), 2.73-2.57 (m, 2H), 2.40-2.32 (m, 1H), 2.32-2.22 (m, 2H), 2.18-2.05 (m, 2H), 1.76-1.65 (m, 1H), 1.59-1.45 (m, 1H), 1.04 (t, J=7.2 Hz, 3H).

1910

1-[[(2S,3R)-3-ethyl-5-oxo-pyrrolidin-2-yl]methoxy]-4-[2-(4-formylcyclohexyl)ethynyl]-7-methoxy-isoquinoline-6-carboxamide (Intermediate AIM)

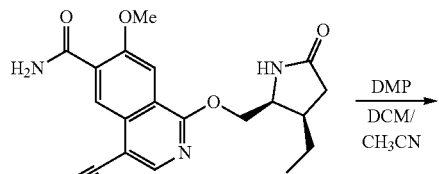

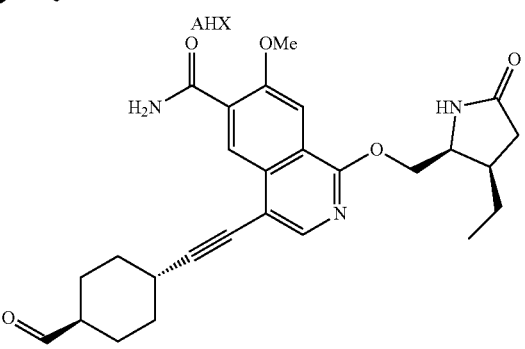

AIM

To a solution of 1-[[(2S,3R)-3-ethyl-5-oxo-pyrrolidin-2-yl]methoxy]-4-[2-[4-(hydroxymethyl) cyclohexyl]ethynyl]-7-methoxyisoquinoline-6-carboxamide (50.0 mg, 104 umol, Intermediate AHX) in DCM (5.00 mL) and ACN (5.00 mL) was added DMP (53.1 mg, 125 umol). The mixture was stirred at 20° C. for 1 hr. On completion, the reaction mixture was quenched by addition of Na$_2$S$_2$O$_3$ (1 mL) and NaHCO$_3$ (1 mL), then diluted with water (5 mL) and extracted with DCM (2×10 mL). The combined organic layers were dried over Na$_2$SO$_4$, and then concentrated in vacuo to give the title compound (49.0 mg, 98% yield) as a yellow solid. $^1$H NMR (400 MHz, DMSO-d$_6$) δ 9.59 (s, 1H), 8.30 (s, 1H), 8.08 (s, 1H), 8.04 (s, 1H), 7.94-7.74 (m, 2H), 7.60 (s, 1H), 4.45 (d, J=3.2 Hz, 2H), 4.07-3.89 (m, 5H), 2.18-1.96 (m, 6H), 1.62-1.49 (m, 4H), 1.44-1.30 (m, 4H), 0.92 (t, J=7.2 Hz, 3H).

Tert-butyl N-(4-aminocyclohexyl)-N-methyl-carbamate (Intermediate AIN)

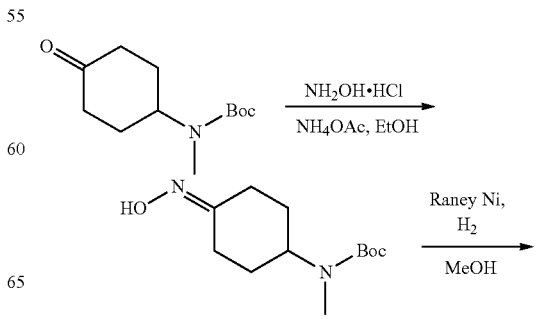

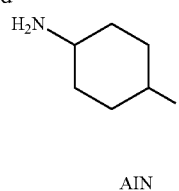

AIN

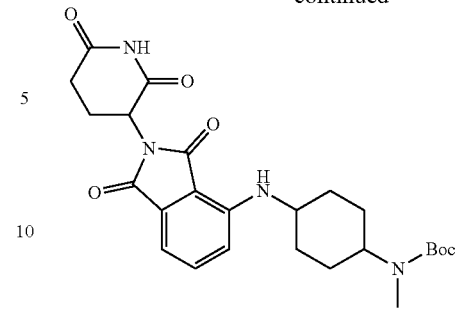

Step 1—Tert-butyl N-(4-hydroxyiminocyclohexyl)-N-methyl-carbamate

To a solution of tert-butyl N-methyl-N-(4-oxocyclohexyl) carbamate (300 mg, 1.32 mmol, CAS #400899-84-5), hydroxylamine hydrochloride (458 mg, 6.60 mmol) in ethanol (15 mL) was added NH$_4$OAc (508 mg, 6.60 mmol). The mixture was stirred at 80° C. for 16 hrs. On completion, the mixture was concentrated in vacuo. The residue was diluted with H$_2$O (20 mL), and extracted with EA (3×15 mL). The organic layers were washed with brine (2×15 mL), dried over anhydrous Na$_2$SO$_4$, filtered and concentrated in vacuo to give the title compound (300 mg, 93% yield) as yellow solid. $^1$H NMR (400 MHz, CDCl$_3$) δ 4.33-4.09 (m, 1H), 3.42-3.30 (m, 1H), 2.64 (s, 3H), 2.43-2.30 (m, 1H), 2.25-2.10 (m, 1H), 1.87-1.72 (m, 3H), 1.62-1.46 (m, 2H), 1.40 (s, 9H).

Step 2—Tert-butyl N-(4-aminocyclohexyl)-N-methyl-carbamate

To a solution of tert-butyl N-(4-hydroxyiminocyclohexyl)-N-methyl-carbamate (200 mg, 825 umol) in MeOH (8 mL) was added Raney-Ni (7.07 mg, 82.5 umol). The mixture was stirred at 50° C. for 16 hrs under H$_2$ (50 psi). On completion, the mixture was filtered and concentrated in vacuo to give the title compound (185 mg, 98% yield) as yellow oil. $^1$H NMR (400 MHz, DMSO-d$_6$) δ 3.87-3.54 (m, 1H), 2.69-2.62 (m, 3H), 2.49-2.40 (m, 1H), 1.92-1.82 (m, 1H), 1.81-1.68 (m, 2H), 1.62-1.53 (m, 1H), 1.50-1.42 (m, 3H), 1.38 (s, 9H), 1.28-1.16 (m, 1H), 1.13-0.99 (m, 1H).

2-(2,6-Dioxo-3-piperidyl)-4-[[4-(methylamino)cyclohexyl]amino]isoindoline-1,3-dione (Intermediate AIO)

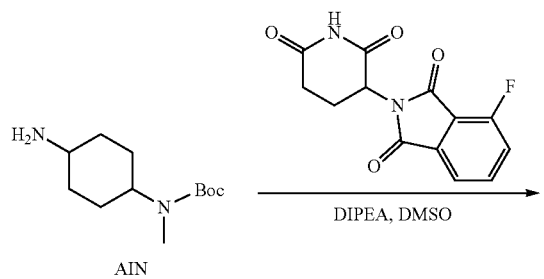

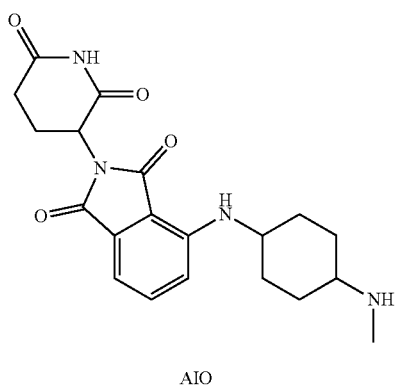

AIO

Step 1—Tert-butyl N-[4-[[2-(2,6-dioxo-3-piperidyl)-1,3-dioxo-isoindolin-4-yl]amino] cyclohexyl]-N-methyl-carbamate To a solution of tert-butyl N-(4-aminocyclohexyl)-N-methyl-carbamate (231 mg, 1.01 mmol, Intermediate AIN), 2-(2,6-dioxo-3-piperidyl)-4-fluoro-isoindoline-1,3-dione (280 mg, 1.01 mmol, Intermediate R) in DMSO (6.00 mL) was added DIPEA (655 mg, 5.07 mmol). The mixture was stirred at 130° C. for 3 hrs. On completion, the mixture was diluted with H$_2$O (40 mL), and extracted with EA (3×20 mL). The organic layers were washed with brine (2×15 mL), dried over anhydrous Na$_2$SO$_4$, filtered and concentrated in vacuo. The residue was purified by reverse phase: (0.1% FA) to give the title compound (320 mg, 65% yield) as yellow solid, $^1$H NMR (400 MHz, CDCl$_3$) δ 8.11 (s, 1H), 7.53-7.45 (m, 1H), 7.13-7.05 (m, 1H), 6.93-6.85 (m, 1H), 6.63-6.09 (m, 1H), 4.99-4.85 (m, 1H), 3.44-3.27 (m, 1H), 2.96-2.78 (m, 2H), 2.76 (s, 3H), 2.25-2.07 (m, 3H), 2.05-1.97 (m, 1H), 1.87-1.77 (m, 2H), 1.76-1.67 (m, 1H), 1.65-1.55 (m, 2H), 1.51-1.38 (m, 11H); LC-MS (ESI$^+$) m/z 385.3 (M+H−100)$^+$.

Step 2—2-(2,6-Dioxo-3-piperidyl)-4-[[4-(methylamino)cyclohexyl]amino]isoindoline-1,3-dione To a solution of tert-butyl N-[4-[[2-(2,6-dioxo-3-piperidyl)-1,3-dioxo-isoindolin-4-yl]amino] cyclohexyl]-N-methyl-carbamate (100 mg, 206 umol) in DCM (3.00 mL) was added HCl/dioxane (4.00 M, 3.00 mL). The mixture was stirred at 15° C. for 0.5 hr. On completion, the mixture concentrated in vacuo to give the title compound (85 mg, 97% yield, HCl) as yellow solid. LC-MS (ESI$^+$) m/z 385.3 (M+H)$^+$.

1913

Tert-butyl 4-[[4-(hydroxymethyl)phenyl]methyl] piperazine-1-carboxylate (Intermediate AIQ)

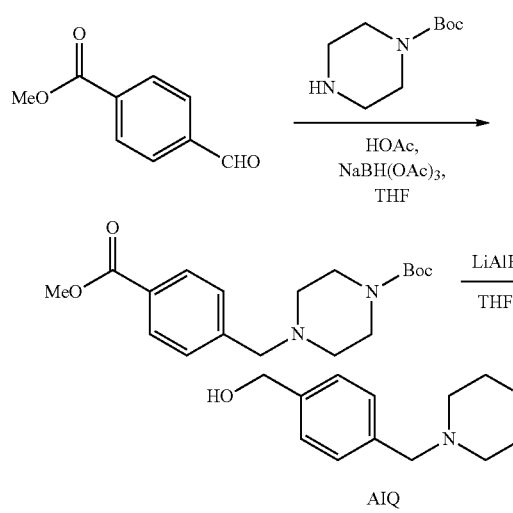

Step 1—Tert-butyl 4-[(4-methoxycarbonylphenyl) methyl]piperazine-1-carboxylate

To a solution of methyl 4-formylbenzoate (3.00 g, 18.2 mmol, CAS #1571-08-0) in THF (20 mL) was added HOAc (18.2 mmol, 1.05 mL), then the mixture stirred at 25° C. for 10 min. Next, tert-butyl piperazine-1-carboxylate (3.74 g, 20.1 mmol, CAS #143238-38-4) was added to the mixture and the mixture was stirred at 25° C. for 20 minutes, then NaBH(OAc)$_3$ (7.75 g, 36.5 mmol) was added to the mixture at 0° C. The reaction mixture was stirred at 25° C. for 2 hrs. On completion, the reaction mixture was quenched with 5 mL H$_2$O and was concentrated in vacuo to give a residue. The residue was purified by column chromatography (SiO$_2$, Petroleum ether/Ethyl acetate=I/O to 1/1) to give the title compound (5.30 g, 86% yield) as white solid. $^1$H NMR (400 MHz, CDCl$_3$) δ 8.04-7.96 (m, 2H), 7.40 (d, J=8.4 Hz, 2H), 3.91 (s, 3H), 3.56 (s, 2H), 3.47-3.40 (m, 4H), 2.42-2.34 (m, 4H), 1.46 (s, 9H); LC-MS (ESI$^+$) m/z 335.2 (M+H)$^+$.

Step 2—Tert-butyl 4-[[4-(hydroxymethyl)phenyl] methyl]piperazine-1-carboxylate

To a solution of tert-butyl 4-[(4-methoxycarbonylphenyl) methyl]piperazine-1-carboxylate (2.00 g, 5.98 mmol) in THF (20 mL) was added LiAlH$_4$ (363 mg, 9.57 mmol) at 0° C. The reaction mixture was stirred at 0-10° C. for 2 hrs. On completion, the mixture was quenched with 1 mL H$_2$O, 1 mL 15% aq NaOH and 3 mL H$_2$O at 0° C. The mixture was dried over by Na$_2$SO$_4$, filtered and concentrated in vacuo to give a residue. The residue was purified by column chromatography (SiO$_2$, Petroleum ether/Ethyl acetate=1:0 to 1:1) to give the title compound (1.20 g, 65% yield) as yellow oil. $^1$H NMR (400 MHz, CDCl$_3$) δ 7.27-7.19 (m, 4H), 4.59 (s, 2H), 3.42 (s, 2H), 3.36-3.28 (m, 4H), 2.33-2.24 (m, 4H), 1.37 (s, 9H).

1914

3-[1-Oxo-4-[[4-(piperazin-1-ylmethyl)phenyl] methoxy]isoindolin-2-yl]piperidine-2,6-dione (Intermediate AIR)

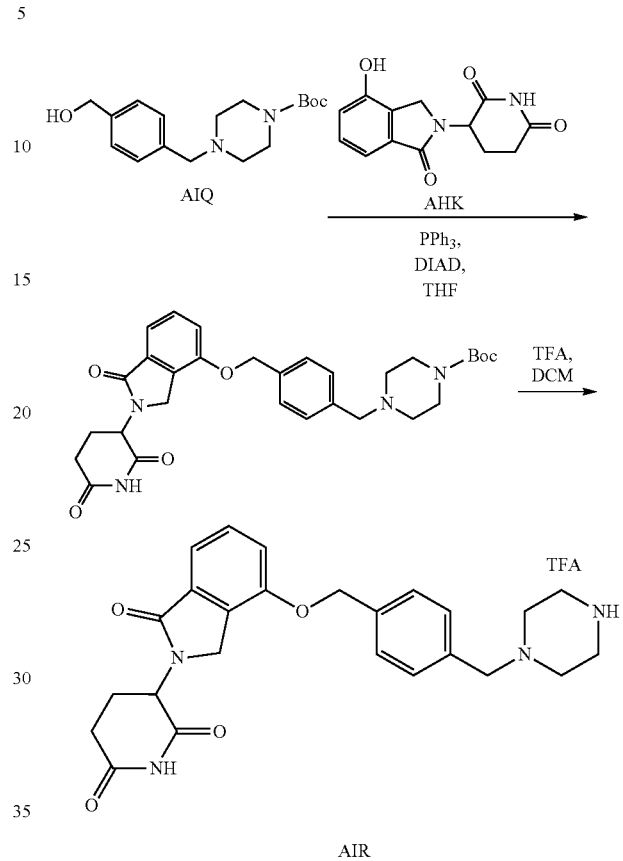

Step 1—Tert-butyl 4-[[4-[[2-(2,6-dioxo-3-piperidyl)-1-oxo-isoindolin-4-yl] oxymethyl]phenyl] methyl] piperazine-1-carboxylate To a solution of tert-butyl 4-[[4-(hydroxymethyl)phenyl] methyl]piperazine-1-carboxylate (588 mg, 1.92 mmol, Intermediate AIQ) and 3-(4-hydroxy-1-oxo-isoindolin-2-yl)piperidine-2,6-dione (500 mg, 1.92 mmol, Intermediate AHK) in THF (5 mL) was added PPh$_3$ (755 mg, 2.88 mmol) and DIAD (582 mg, 2.88 mmol) at 0° C. The reaction mixture was stirred at 0-25° C. for 12 hrs under N$_2$. On completion, the mixture was concentrated in vacuo to give the residue. The residue was purified by prep-HPLC (column: Phenomenex luna C18 150*40 mm*15 um; mobile phase: [water (0.225% FA)-ACN]; B %: 3%-33%, 8.5 min) to give the title compound (250 mg, 23% yield) as white solid. $^1$H NMR (400 MHz, DMSO-d$_6$) δ 10.98 (s, 1H), 7.45 (s, 1H), 7.40-7.37 (m, 2H), 7.25-7.15 (m, 4H), 5.13-5.06 (m, 1H), 4.74 (s, 2H), 4.43-4.13 (m, 4H), 3.89-3.78 (m, 2H), 3.53 (s, 2H), 3.47 (s, 4H), 2.47-2.35 (m, 4H), 1.38 (s, 9H); LC-MS (ESI$^+$) m/z 549.1 (M+H)$^+$.

Step 2—3-r 1-Oxo-4-[[4-(piperazin-1-ylmethyl) phenyl]methoxy]isoindolin-2-yl]piperidine-2,6-dione To a solution of tert-butyl 4-[[4-[[2-(2,6-dioxo-3-piperidyl)-1-oxo-isoindolin-4-yl]oxymethyl]phenyl] methyl]

piperazine-1-carboxylate (50.0 mg, 91.1 umol) in DCM (5 mL) was added TFA (67.5 mmol, 5 mL) at 25° C. The mixture was stirred at 25° C. for 2 hrs. On completion, the reaction mixture was concentrated in vacuo to give the title compound (50.0 mg, 97% yield, TFA salt) as a yellow solid. LC-MS (ESI⁺) m/z 449.2 (M+H)⁺.

Tert-butyl N-[3-(difluoromethyl)-1-(4-formylphenyl)pyrazol-4-yl]carbamate (Intermediate AIS)

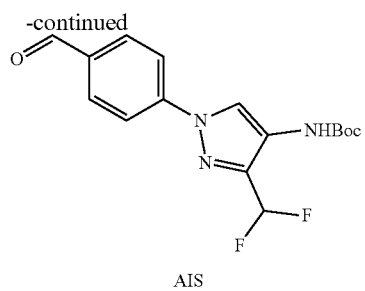

AIS

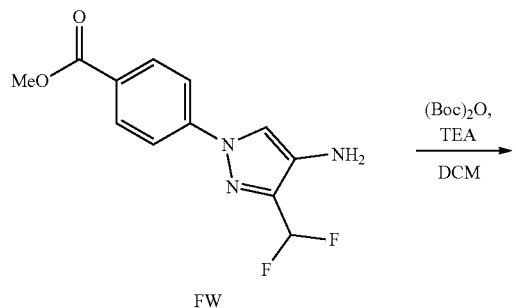

FW

Step 1—Methyl 4-[4-(tert-butoxycarbonylamino)-3-(difluoromethyl)pyrazol-1-yl]benzoate To a mixture of methyl 4-[4-amino-3-(difluoromethyl)pyrazol-1-yl]benzoate (0.5 g, 1.87 mmol, Intermediate FW) in DCM (10 mL) was added TEA (378 mg, 3.74 mmol). Then (Boc)₂O (490 mg, 2.25 mmol) was added into the mixture and stirred at 30° C. for 12 hours. On completion, the reaction mixture was poured into the water (50 mL), and extracted with EA (2×40 mL). The combined organic phase was washed with brine (2×60 mL), dried with anhydrous Na₂SO₄, filtered and concentrated in vacuo to give the residue. The residue was purified by column chromatography (PE:EA=2:1) to give the title compound (0.50 g, 72% yield) as a brown solid. ¹H NMR (400 MHz, CDCl₃) δ 8.54 (s, 1H), 8.21-8.01 (m, 2H), 7.77 (d, J=8.8 Hz, 2H), 7.00-6.61 (m, 2H), 3.95 (s, 3H), 1.55 (s, 9H).

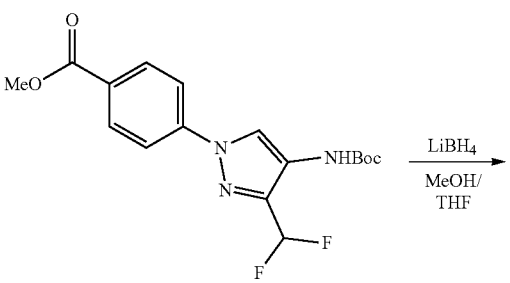

Step 2—Tert-butyl N-[3-(difluoromethyl)-1-[4-(hydroxymethyl)phenyl]pyrazol-4-yl]carbamate To a mixture of methyl 4-[4-(tert-butoxycarbonylamino)-3-(difluoromethyl)pyrazol-1-yl]benzoate (0.5 g, 1.36 mmol) in THF (20 mL) and MeOH (2.5 mL) was added LiBH₄ (59.3 mg, 2.72 mmol) at 0° C. The mixture was stirred at 50° C. for 3 hours. On completion, the reaction mixture was poured into water (60 mL). The aqueous phase was extracted with DCM (2×30 mL). The combined organic phase was washed with brine (2×60 mL), dried with anhydrous Na₂SO₄, filtered and concentrated in vacuo to give the title compound (0.45 g, 97% yield) as a brown solid. ¹H NMR (400 MHz, CDCl₃) δ 8.45 (s, 1H), 7.66 (d, J=8.4 Hz, 2H), 7.44 (d, J=8.8 Hz, 2H), 6.98-6.67 (m, 2H), 4.74 (s, 2H), 1.86 (s, 1H), 1.54 (s, 9H).

Step 3—Tert-butyl N-[3-(difluoromethyl)-1-(4-formylphenyl)pyrazol-4-yl]carbamate

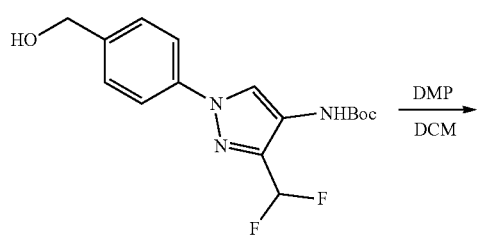

To a mixture of tert-butyl N-[3-(difluoromethyl)-1-[4-(hydroxymethyl)phenyl]pyrazol-4-yl]carbamate (380 mg, 1.12 mmol) in DCM (10 mL) was added DMP (522 mg, 1.23 mmol). The reaction mixture was stirred at 25° C. for 0.5 hour. On completion, the reaction mixture was poured into the water (80 mL), and extracted with DCM (2×60 mL). The combined organic phase was washed with brine (2×50 mL), dried with anhydrous Na₂SO₄, filtered and concentrated in vacuo to give the title compound (350 mg, 92% yield) as a white solid. ¹H NMR (400 MHz, CDCl₃) δ 10.03 (s, 1H), 8.57 (s, 1H), 8.01-7.96 (m, 2H), 7.88 (d, J=8.6 Hz, 2H), 7.03-6.61 (m, 2H), 1.55 (s, 9H).

4-[3-[[1-[[4-[4-Amino-3-(difluoromethyl)pyrazol-1-yl]phenyl]methyl]-4piperidyl]oxy] propylamino]-2-(2,6-dioxo-3-piperidyl)isoindoline-1,3-dione (Intermediate AIT)

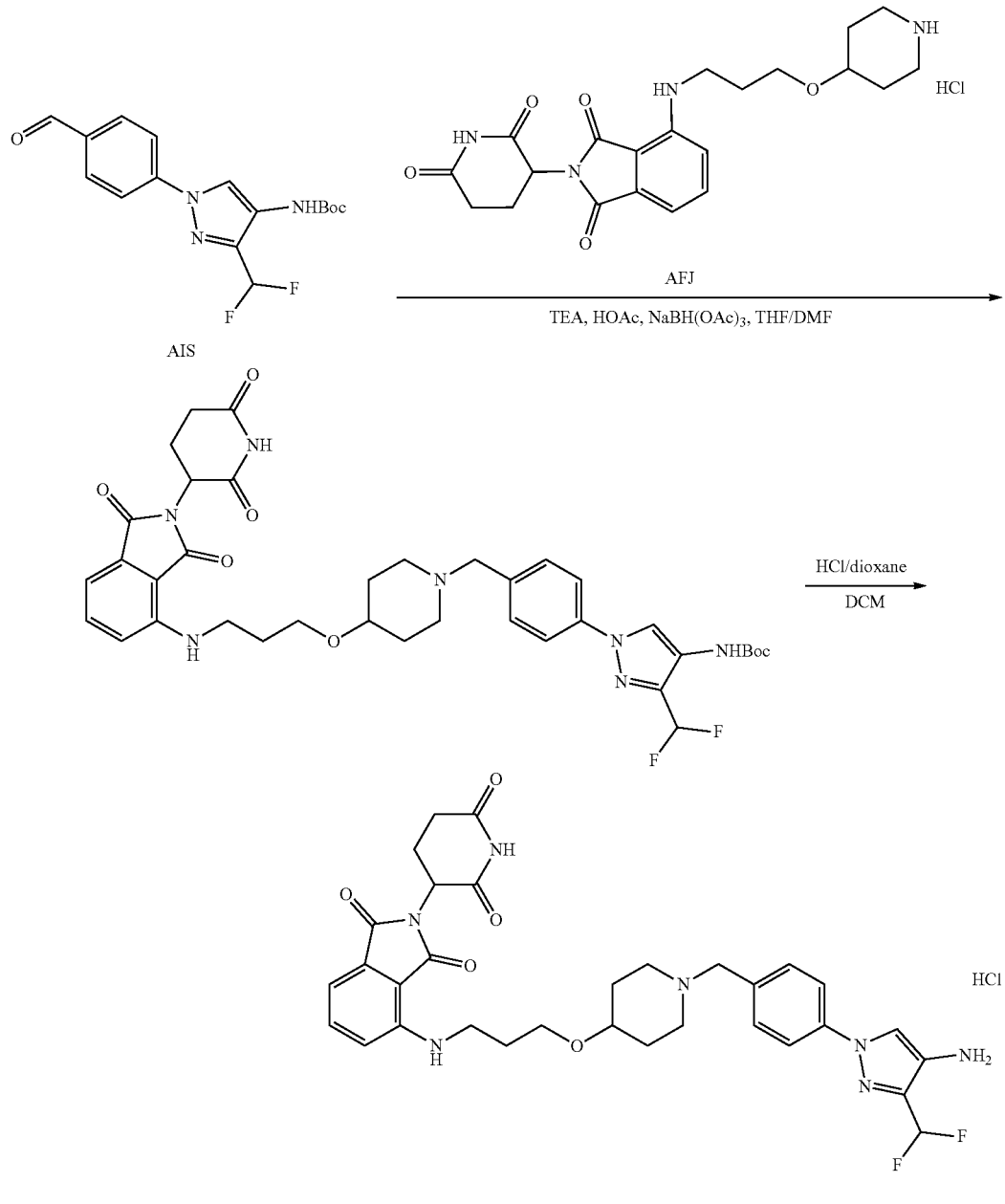

Step 1—Tert-butyl N-[3-(difluoromethyl)-1-[4-[[4-[3-[[2-(2,6-dioxo-3-piperidyl)-1,3-dioxo-isoindolin-4-yl] amino]propoxy]-1-piperidyl]methyl]phenyl] pyrazol-4-yl]carbamate To a solution of tert-butyl N-[3-(difluoromethyl)-1-(4-formylphenyl)pyrazol-4-yl]carbamate (100 mg, 296 umol, Intermediate AIS) in a mixed solvent of THF (8 mL) and DMF (2 mL) was added TEA (30.0 mg, 296 umol). The reaction mixture stirred at 25° C. for 10 min, then HOAc (17.8 mg, 296 umol) and 2-(2,6-dioxo-3-piperidyl)-4-[3-(4-piperidyloxy)propylamino]isoindoline-1,3-dione (133 mg, 296 umol, HCl salt, Intermediate AFJ) was added to the mixture and the mixture was stirred at 25° C. for 20 minutes. Then NaBH(OAc)₃ (125 mg, 592 umol) was added to the mixture at 0° C. The reaction mixture was then stirred at 25° C. for 12 hrs. On completion, the mixture was quenched by water (1 mL) and concentrated in vacuo to give a residue. The residue was purified by prep-HPLC (column: Phenomenex Synergi C18 150*25*10 um; mobile phase: [water (0.225% FA)-ACN]; B %: 21%-51%, 10 min) to give the title compound (110 mg, 50% yield) as yellow solid. LC-MS (ESI+) m/z 736.3 (M+H)+.

Step 2—4-[3-[[1-[[4-[4-amino-3-(difluoromethyl) pyrazol-1-yl]]phenyl]methyl]-4piperidyl]oxy] propylamino]-2-(2,6-dioxo-3-piperidyl)isoindoline-1,3-dione To a solution of tert-butyl N-[3-(difluoromethyl)-1-[4-[[4-[3-[[2-(2,6-dioxo-3-piperidyl)-1,3-dioxo-isoindolin-4-yl] amino]propoxy]-1-piperidyl]methyl]phenyl]pyrazol-4-yl] carbamate (100 mg, 135 umol) in DCM (8 mL) was added HCl/dioxane (4 M, 5 mL) at 25° C. The reaction mixture was stirred at 25° C. for 2 hrs. On completion, the mixture was concentrated in vacuo to give the title compound (90.0 mg, 98% yield, HCl salt) as white solid. LC-MS (ESI+) m/z 636.3 (M+H)+.

4-Chloro-2-(2,6-dioxo-3-piperidyl)pyrrolo[3,4-c] pyridine-1,3-dione (Intermediate ASQ)

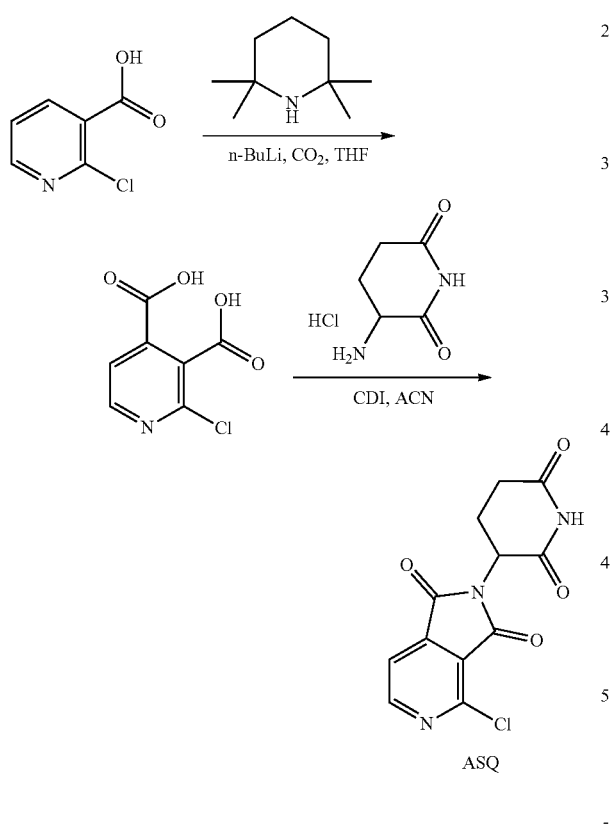

Step 1—2-chloropyridine-3,4-dicarboxylic acid

To a solution of TMP (5.38 g, 38.1 mmol) in THF (50 mL) was added n-BuLi (2.5 M, 20.3 mL) at −70° C. The mixture was stirred for 0.5 hour. Next, a solution of 2-chloropyridine-3-carboxylic acid (2.00 g, 12.7 mmol) in THF (20 mL) was added and the mixture was stirred at −70° C. for 2 hours. The mixture was poured onto an excess of freshly crushed dry ice. On completion, the mixture was concentrated. The residue was poured into 50 mL 2M aq.HCl, and extracted with ethyl acetate (3×50 mL). The combined organic layers were washed with water (20 mL) and brine (20 mL), dried over anhydrous sodium sulfate and concentrated in vacuo to give the title compound (2.00 g, 78% yield) as a yellow solid.

Step 2—4-Chloro-2-(2,6-dioxo-3-piperidyl)pyrrolo [[3,4-c]pyridine-1,3-dione

To a mixture of 2-chloropyridine-3,4-dicarboxylic acid (1.50 g, 7.44 mmol) and 3-aminopiperidine-2,6-dione (1.47 g, 8.93 mmol, HCl salt) in ACN (50 mL) was added CDI (2.41 g, 14.8 mmol). The mixture was stirred at 80° C. for 16 hours. On completion, the mixture was concentrated in vacuo. The residue was purified by silica gel column chromatography [petroleum ether:ethyl acetate=10:1 to 0:1] to give the title compound (600 mg, 27% yield) as a yellow solid.

2-(2,6-Dioxo-3-piperidyl)-4-[3-(4-piperidyloxy)propylamino]pyrrolo[3,4-c]pyridine-1,3-dione (Intermediate ASR)

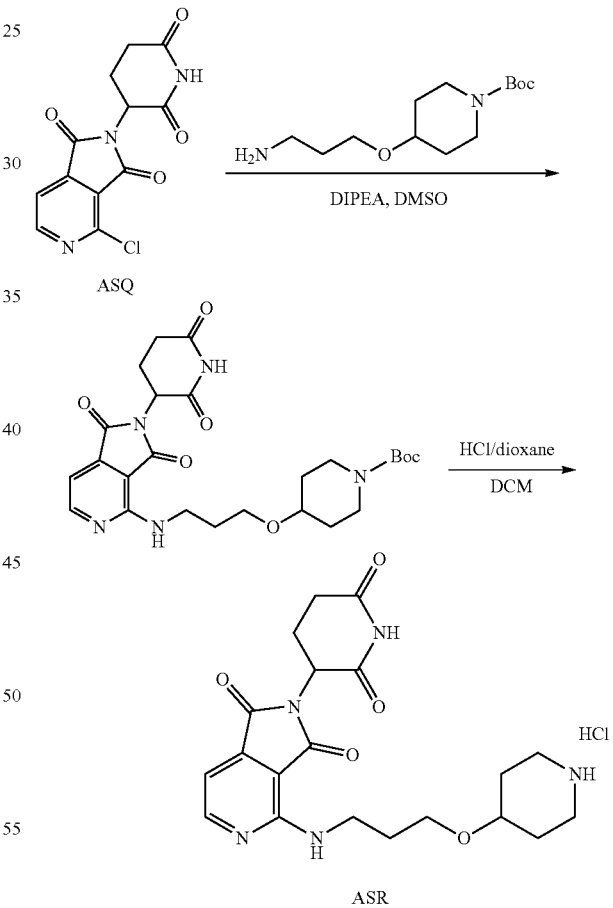

Step 1—Tert-butyl 4-[3-[[2-(2,6-dioxo-3-piperidyl)-1,3-dioxo-pyrrolo[3,4-c]pyridin-4-yl]amino] propoxylpiperidine-1-carboxylate To a solution of 4-chloro-2-(2,6-dioxo-3-piperidyl)pyrrolo[3,4-c]pyridine-1,3-dione (100 mg, 340 umol, Intermediate ASQ), tert-butyl 4-(3-aminopropoxy)piperidine-1-carboxylate (87.9 mg, 341 umol, CAS #771572-33-9) in DMSO (1 mL) was added DIPEA (88.0 mg, 681 umol). The mixture was stirred at 100° C. for 2 hours. On completion, the mixture was concentrated in vacuo. The residue was purified by reversed-phase HPLC (0.1% TFA condition, 65-70% CH₃CN) to give the title compound (50.0 mg, 28% yield) as a white solid. LC-MS (ESI⁺) m/z 516.4 (M+H)⁺.

Step 2—2-(2,6-Dioxo-3-piperidyl)-4-[3-(4-piperidyloxy)propylamino]pyrrolo[3,4-c]pyridine-1,3-dione To a solution of tert-butyl 4-[3-[[2-(2,6-dioxo-3-piperidyl)-1,3-dioxo-pyrrolo[3,4-c]pyridin-4-yl]amino]propoxy]piperidine-1-carboxylate (50.0 mg, 97.0 umol) in DCM (3 mL) was added HCl/dioxane (4 M, 1 mL). The mixture was stirred at 25° C. for 1 hour. On completion, the reaction mixture was concentrated in vacuo to give the title compound (40.0 mg, 91% yield) as yellow solid. LC-MS (ESI⁺) m/z 416.5 (M+H)⁺.

5-((Cyclopropylmethyl)amino)pyrazolo[1,5-a]pyrimidine-3-carboxylic acid (Intermediate ASS)

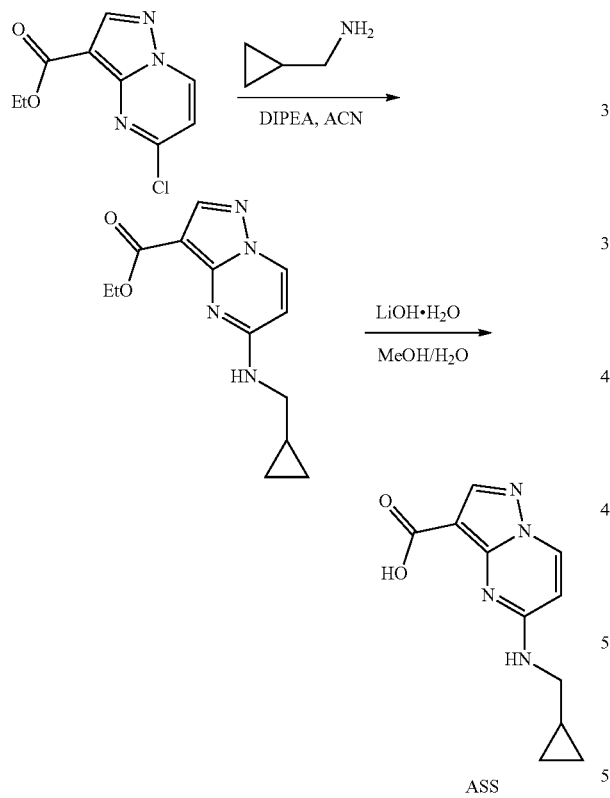

Step 1—Ethyl 5-((cyclopropylmethyl)amino)pyrazolo[1,5-a]pyrimidine-3-carboxylate To a solution of ethyl 5-chloropyrazolo[1,5-a]pyrimidine-3-carboxylate (2.00 g, 8.86 mmol) and cyclopropylmethanamine (757 mg, 10.6 mmol) in ACN (15 mL) was added DIPEA (3.44 g, 26.6 mmol). The reaction mixture was stirred at 60° C. for 2 hours. On completion, the reaction mixture was concentrated in vacuo. The residue was diluted with water (40 mL), stirred for 10 minutes, and filtered. The cake was washed with water (2×10 mL) to give the title compound (2.18 g, 94% yield) as white solid. ¹H NMR (400 MHz, DMSO-d₆) δ 8.50 (d, J=7.6 Hz, 1H), 8.12 (s, 1H), 8.03-7.95 (m, 1H), 6.40 (d, J=7.6 Hz, 1H), 4.19 (q, J=7.2 Hz, 2H), 3.31-3.24 (m, 2H), 1.28 (t, J=7.2 Hz, 3H), 1.15-1.05 (m, 1H), 0.54-0.43 (m, 2H), 0.34-0.26 (m, 2H).

Step 2—5-((Cyclopropylmethyl)amino)pyrazolo[pyrazolo[1,5-a]pyrimidine-3-carboxylic acid To a solution of ethyl 5-(cyclopropylmethylamino)pyrazolo[1,5-a]pyrimidine-3-carboxylate (1.00 g, 3.84 mmol) in MeOH (10 mL) and H₂O (2 mL) was added LiOHH₂O (806 mg, 19.2 mmol). The reaction mixture was stirred at 60° C. for 12 hours. On completion, the reaction mixture was concentrated in vacuo. The mixture was adjusted to pH=5 with 1.0 M aq.HCl, the resulting solution was filtered. The cake was washed with water (2×10 mL) and dried to give the title compound (0.705 g, 68% yield) as a white solid. ¹H NMR (400 MHz, DMSO-d₆) δ 11.56 (s, 1H), 8.51 (d, J=7.6 Hz, 1H), 8.12 (s, 1H), 8.03-7.95 (m, 1H), 6.40 (d, J=7.2 Hz, 1H), 3.28-3.20 (m, 2H), 1.13-1.01 (m, 1H), 0.54-0.43 (m, 2H), 0.34-0.26 (m, 2H).

5-((Cyclopropylmethyl)amino)-N-(3-(difluoromethyl)-1-((1r,4r)-4-formylcyclohexyl)-1H-pyrazol-4-yl)pyrazolo[1,5-a]pyrimidine-3-carboxamide (Intermediate AST)

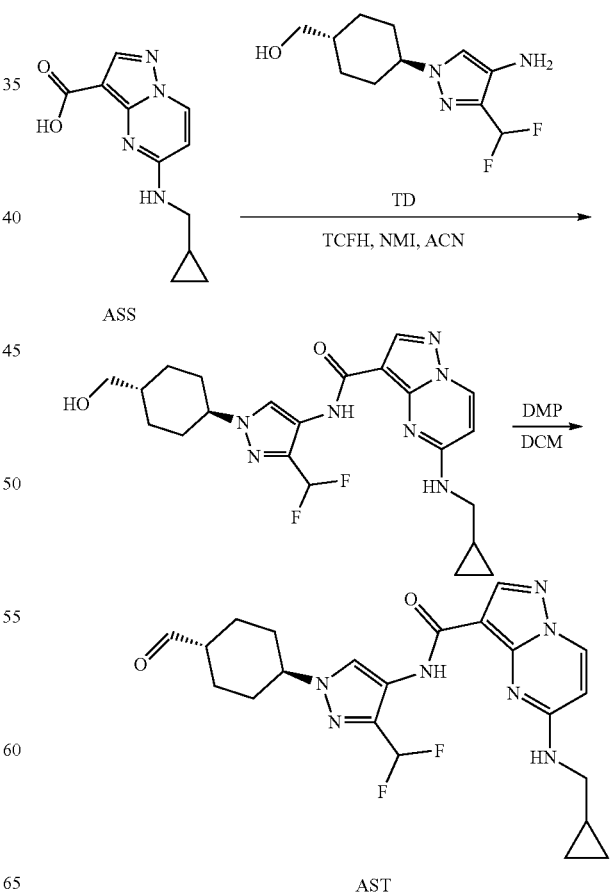

Step 1—5-((Cyclopropylmethyl)amino)-N-(3-(difluoromethyl)-1-((1r,4r)-4-(hydroxymethyl) cyclohexyl)-1H-pyrazol-4-yl)pyrazolo[1,5-a]pyrimidine-3-carboxamide To a solution of 5-(cyclopropylmethylamino)pyrazolo[1,5-a]pyrimidine-3-carboxylic acid (200 mg, 861 umol, Intermediate ASS) in ACN (10 mL) was added [chloro(dimethylamino)methylene]-dimethyl-ammonium; hexafluorophosphate (290 mg, 1.03 mmol,) and NMI (247 mg, 3.01 mmol). The reaction mixture was stirred at 20° C. for 0.1 hour. Then, [4-[4-amino-3-(difluoromethyl)pyrazol-1-yl]cyclohexyl]methanol (253 mg, 1.03 mmol, Intermediate TD) was added. The mixture was stirred at 20° C. for 2 hours. On completion, the mixture was filtered and the cake was washed with water (2×10 mL) to give the title compound (320 mg, 81% yield) as a white solid. $^1$H NMR (400 MHz, DMSO-$d_6$) δ 9.55 (s, 1H), 8.56 (d, J=7.6 Hz, 1H), 8.37 (s, 1H), 8.27-8.20 (m, 1H), 8.18 (s, 1H), 7.25-6.94 (m, 1H), 6.45 (d, J=7.6 Hz, 1H), 4.46 (t, J=5.2 Hz, 1H), 4.21-4.11 (m, 1H), 3.31-3.23 (m, 4H), 2.07-2.00 (m, 2H), 1.89-1.81 (m, 2H), 1.78-1.66 (m, 2H), 1.48-1.38 (m, 1H), 1.15-1.02 (m, 3H), 0.55-0.49 (m, 2H), 0.28-0.23 (m, 2H).

Step 2—5-((Cyclopropylmethyl)amino)-N-(3-(difluoromethyl)-1-((1r,4r)-4-formylcyclohexyl)-1H-pyrazol-4-yl)pyrazolo[1,5-a]pyrimidine-3-carboxamide To a solution of 5-(cyclopropylmethylamino)-N-[3-(difluoromethyl)-1-[4-(hydroxymethyl)cyclohexyl] pyrazol-4-yl]pyrazolo[1,5-a]pyrimidine-3-carboxamide (40.0 mg, 87.1 umol) in DCM (1 mL) was added DMP (44.3 mg, 104 umol). The reaction mixture was stirred at 20° C. for 0.5 hour. On completion, the reaction mixture was quenched with sat. aq. Na$_2$S$_2$O$_3$ (3 mL), and extracted with DCM (3×3 mL). The combined organic layers were washed with brine (2×3 mL), dried over Na$_2$SO$_4$, filtered and concentrated in vacuo to give the title compound (36.0 mg, 90% yield) as a white solid.

5-Morpholinopyrazolo[1,5-a]pyrimidine-3-carbonyl chloride (Intermediate AIU)

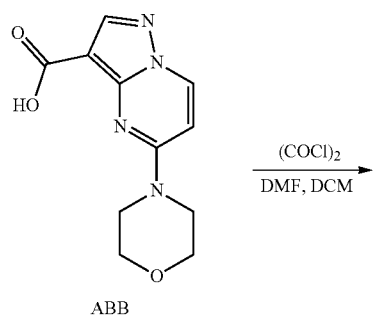

ABB

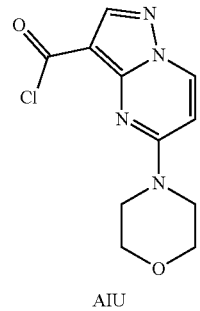

AIU

To a mixture of 5-morpholinopyrazolo[1,5-a]pyrimidine-3-carboxylic acid (0.30 g, 1.21 mmol, Intermediate ABB) and DMF (4.42 mg, 60.4 umol) in DCM (10 mL) was added (COCl)$_2$ (199 mg, 1.57 mmol). The mixture was stirred at 20° C. for 15 mins. On completion, the reaction mixture was concentrated in vacuo to give the title compound (0.3 g, 98% yield) as light yellow solid and the product was used without purification.

3-[4-(3-Bromophenyl)-3-methyl-2-oxo-benzimidazol-1-yl]piperidine-2,6-dione (Intermediate AIV)

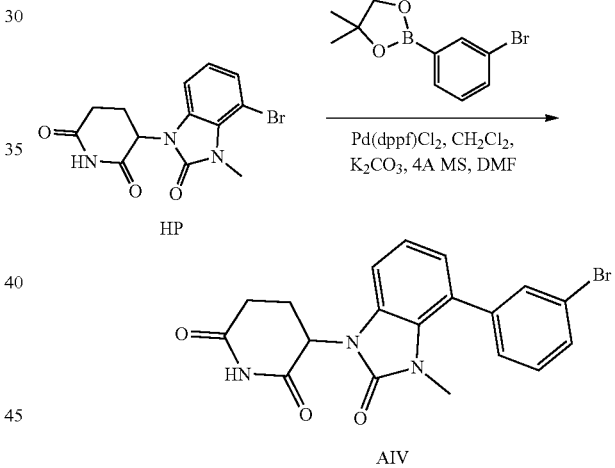

AIV

To a solution of 3-(4-bromo-3-methyl-2-oxo-benzimidazol-1-yl)piperidine-2,6-dione (2.00 g, 5.91 mmol, Intermediate HP), 2-(3-bromophenyl)-4,4,5,5-tetramethyl-1,3,2-dioxaborolane (1.17 g, 4.14 mmol, CAS #594823-67-3), 4 Å molecular sieves (2 g) and K$_2$CO$_3$ (3.27 g, 23.6 mmol) in DMF (80 mL) was added Pd(dppf)Cl$_2$*CH$_2$Cl$_2$ (482 mg, 591 umol). The mixture was stirred at 90° C. for 5 hrs. On completion, the reaction mixture was filtered and concentrated in vacuo to give a residue. The residue was diluted with water (20 mL), and then extracted with EA (3×50 mL). The combined organic layers were dried over Na$_2$SO$_4$, filtered and concentrated in vacuo to give a residue. The residue was purified by reverse phase flash (FA condition) to give the title compound (0.37 g, 15% yield) as gray solid. $^1$H NMR (400 MHz, DMSO-$d_6$) δ11.13 (s, 1H), 7.71-7.62 (m, 2H), 7.49-7.38 (m, 2H), 7.20 (d, J=8.0 Hz, 1H), 7.10 (t, J=7.6 Hz, 1H), 6.92 (d, J=7.6 Hz, 1H), 5.45 (dd, J=5.2, 12.8 Hz, 1H), 2.99-2.89 (m, 1H), 2.88 (s, 3H), 2.80-2.60 (m, 2H), 2.13-2.00 (m, 1H); LC-MS (ESI$^+$) m/z 416.0 (M+H)$^+$.

1925

Tert-butyl N-[3-(difluoromethyl)-1-[4-(prop-2-ynoxymethyl)cyclohexyl]pyrazol-4-yl] carbamate (Intermediate AIW)

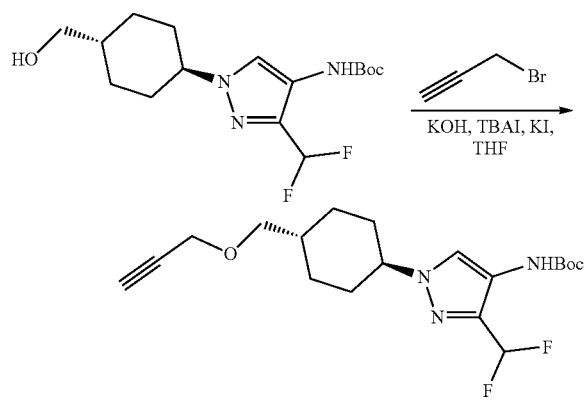

1926

To a solution of tert-butyl N-[3-(difluoromethyl)-1-[4-(hydroxymethyl)cyclohexyl]pyrazol-4-yl] carbamate (0.50 g, 1.45 mmol, synthesized via Step 1 of Intermediate ABM) and 3-bromoprop-1-yne (223 mg, 1.88 mmol) in THF (8 mL) was added KI (36.0 mg, 217 umol), TBAI (32.0 mg, 86.8 umol) and KOH (89.3 mg, 1.59 mmol). The mixture was stirred at 15° C. for 16 hrs. On completion, the reaction mixture was quenched by water (20 mL) and extracted with EA (3×30 mL). The combined organic layers were dried over $Na_2SO_4$, filtered and concentrated in vacuo to give a residue. The residue was purified by reverse phase flash (FA condition) to give the title compound (0.46 g, 82% yield) as light yellow oil. $^1$H NMR (400 MHz, $CDCl_3$) δ 7.52 (s, 1H), 6.64 (t, J=14.4 Hz, 1H), 4.28 (s, 2H), 4.11-4.03 (m, 1H), 3.53 (d, J=6.4 Hz, 2H), 2.32-2.19 (m, 3H), 2.05-1.96 (m, 2H), 1.81-1.71 (m, 2H), 1.61-1.59 (m, 1H), 1.39 (s, 9H), 1.24-1.10 (m, 2H); LC-MS (ESI$^+$) m/z 384.2 (M+H)$^+$.

3-[4-[3-[3-[[4-[4-Amino-3-(difluoromethyl)pyrazol-1-yl] cyclohexyl]methoxy]propyl] phenyl]-3-methyl-2-oxo-benzimidazol-1-yl]piperidine-2,6-dione (Intermediate AIX)

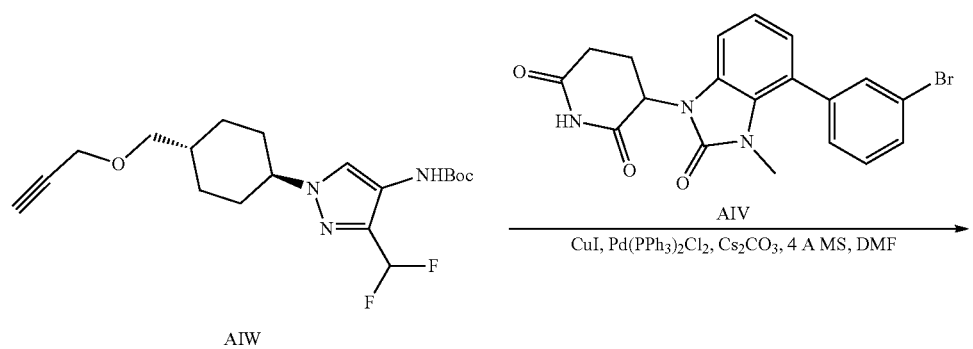

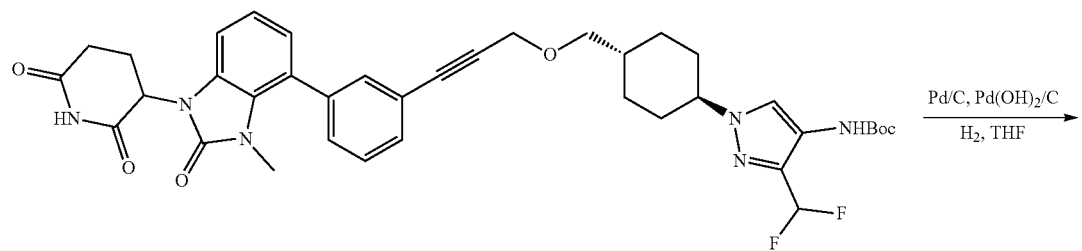

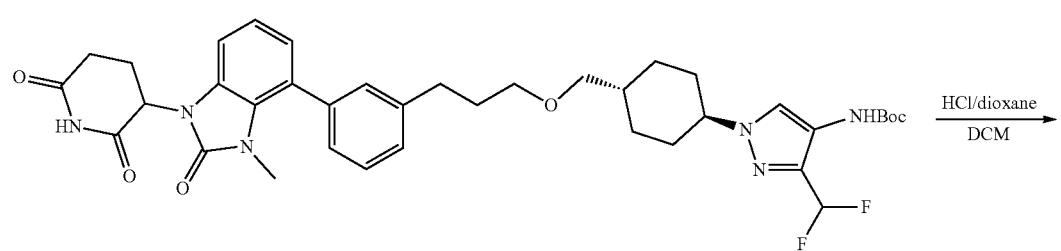

-continued

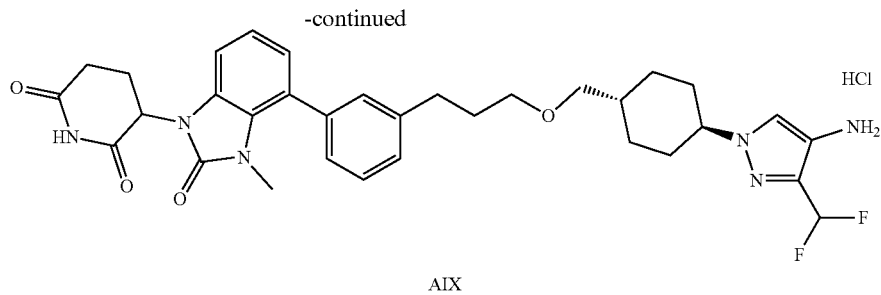

AIX

Step 1—Tert-butyl N-[3-(difluoromethyl)-1-[4-[3-[3-[1-(2,6-dioxo-3-piperidyl)-3-methyl-2-oxo-benzimidazol-4-yl]phenyl]prop-2-ynoxymethyl]cyclohexyl]pyrazol-4-yl]carbamate To a solution of 3-[4-(3-bromophenyl)-3-methyl-2-oxo-benzimidazol-1-yl]piperidine-2,6-dione (300 mg, 724 umol, Intermediate AIV) and tert-butyl N-[3-(difluoromethyl)-1-[4-(prop-2-ynoxymethyl)cyclohexyl]pyrazol-4-yl]carbamate (333 mg, 869.04 umol, Intermediate AIW) in DMF (5 mL) was added Pd(PPh$_3$)$_2$Cl$_2$ (50.8 mg, 72.4 umol), CuI (13.7 mg, 72.4 umol), 4 Å molecular sieves (100 mg) and Cs$_2$CO$_3$ (707 mg, 2.17 mmol), then the mixture was heated at 80° C. for 3 hrs. On completion, the reaction mixture was quenched with water (30 mL), and then extracted with EA (3×30 mL). The combined organic layers were dried over Na$_2$SO$_4$, filtered and concentrated in vacuo to give a residue. The residue was purified by reverse phase flash (FA condition) to give the title compound (0.3 g, 57% yield) as light yellow solid. $^1$H NMR (400 MHz, CDCl$_3$) δ 8.37 (s, 1H), 7.61-7.49 (m, 1H), 7.48-7.43 (m, 1H), 7.42-7.31 (m, 3H), 7.15-7.07 (m, 1H), 6.96 (d, J=7.2 Hz, 1H), 6.85 (d, J=7.2 Hz, 1H), 6.82-6.49 (m, 1H), 5.44-5.18 (m, 1H), 4.54 (s, 2H), 4.12-4.00 (m, 1H), 3.58-3.40 (m, 2H), 3.00 (s, 3H), 2.95 (s, 1H), 2.93-2.77 (m, 2H), 2.32-2.25 (m, 1H), 2.21 (d, J=10.4 Hz, 2H), 1.91 (d, J=12.8 Hz, 2H), 1.73-1.61 (m, 2H), 1.58-1.31 (m, 11H), 1.19-1.05 (m, 2H); LC-MS (ESI$^+$) m/z 717.5 (M+H)$^+$.

Step 2—Tert-butyl N-[3-(difluoromethyl)-1-[4-[3-[3-[1-(2,6-dioxo-3-piperidyl)-3-methyl-2-oxo-benzimidazol-4-yl]phenyl]propoxymethyl]cyclohexyl]pyrazol-4-yl]carbamate To a solution of tert-butyl N-[3-(difluoromethyl)-1-[4-[3-[3-[1-(2,6-dioxo-3-piperidyl)-3-methyl-2-oxo-benzimidazol-4-yl]phenyl]prop-2-ynoxymethyl]cyclohexyl]pyrazol-4-yl]carbamate (200 mg, 279 umol) in THF (5 mL) was added Pd(OH)$_2$/C (50 mg, 10 wt %) and Pd/C (50 mg, 10 wt %) under N$_2$. The suspension was degassed under vacuum and purged with H$_2$ three times. The mixture was stirred under H$_2$ (15 Psi) at 15° C. for 16 hrs. On completion, the reaction mixture was filtered and the filter cake was concentrated in vacuo to give the title compound (150 mg, 75% yield) as light yellow solid. $^1$H NMR (400 MHz, DMSO-d$_6$) δ 11.14 (s, 1H), 7.96 (s, 1H), 7.37 (t, J=7.6, 1H), 7.28-7.20 (m, 3H), 7.19-7.13 (m, 1H), 7.08 (t, J=7.6 Hz, 1H), 7.00-6.67 (m, 2H), 5.44 (dd, J=5.2, 12.8 Hz, 1H), 4.09-4.01 (m, 1H), 3.70-3.66 (m, 2H), 3.43 (t, J=7.2 Hz, 2H), 3.24 (d, J=6.0 Hz, 2H), 2.97-2.85 (m, 1H), 2.81 (s, 3H), 2.74 (dd, J=4.4, 12.8 Hz, 1H), 2.69-2.58 (m, 3H), 2.11-1.94 (m, 3H), 1.85-1.73 (m, 4H), 1.70-1.60 (m, 2H), 1.28 (s, 9H), 1.10-0.96 (m, 2H); LC-MS (ESI$^+$) m/z 721.5 (M+H)$^+$.

Step 3—3-[4-[3-[3-[[4-[4-Amino-3-(difluoromethyl)pyrazol-1-yl]cyclohexyl]methoxy]propyl]phenyl]-3-methyl-2-oxo-benzimidazol-1-yl]piperidine-2,6-dione To a solution of tert-butyl N-[3-(difluoromethyl)-1-[4-[3-[3-[1-(2,6-dioxo-3-piperidyl)-3-methyl-2-oxo-benzimidazol-4-yl]phenyl]propoxymethyl] cyclohexyl]pyrazol-4-yl]carbamate (100 mg, 138 umol) in DCM (1 mL) was added HCl/dioxane (4 M, 2.22 mL). The mixture was stirred at 15° C. for 0.5 hrs. On completion, the reaction was concentrated in vacuo to give the title compound (90.0 mg, 95% yield, HCl) as light yellow solid. LC-MS (ESI$^+$) m/z 621.4 (M+H)$^+$.

1-(4-Bromophenyl)-3-(difluoromethyl)pyrazol-4-amine (Intermediate AKH)

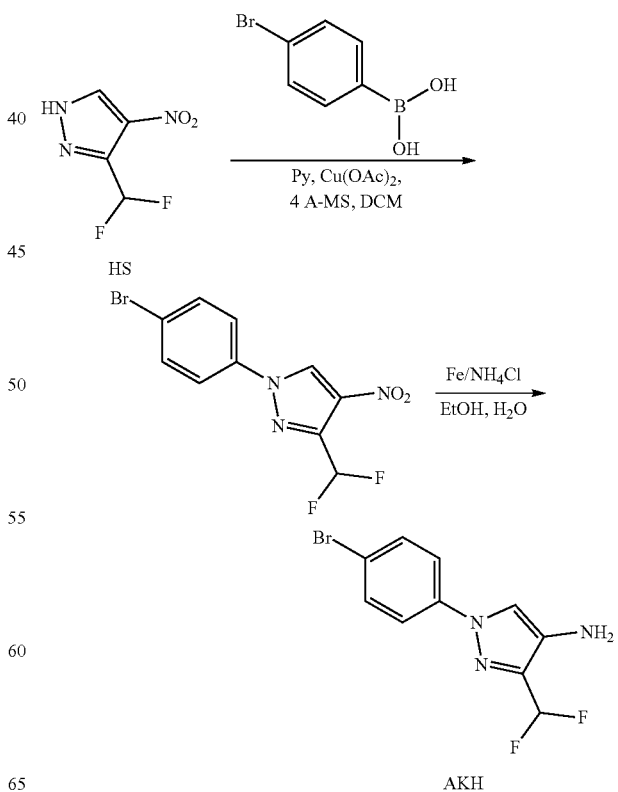

AKH

Step 1—1-(4-Bromophenyl)-3-(difluoromethyl)-4-nitro-pyrazole

A mixture of 3-(difluoromethyl)-4-nitro-1H-pyrazole (2.50 g, 15.3 mmol, Intermediate HS), (4-bromophenyl)boronic acid (3.69 g, 18.4 mmol, CAS #5467-74-3) and pyridine (4.85 g, 61.3 mmol, 4.95 mL) in DCM (100 mL) was added Cu(OAc)$_2$ (4.18 g, 23.0 mmol) and 4 Å molecular sieves (2.00 g). The mixture was stirred at 25° C. under oxygen (15 Psi) for 16 hours. On completion, the reaction mixture was filtered and the filtrate was concentrated and in vacuo to give a residue. The residue was diluted with EA (50 mL) and washed with NH$_3$.H$_2$O (3×5 mL), then washed with 1 N HCl. The organic layers was washed with brine (2×30 mL), dried over Na$_2$SO$_4$, filtered and concentrated in vacuo give a residue. The residue was purified by recrystallization from EA (5 mL) to give the title compound 1-(4-bromophenyl)-3-(difluoromethyl)-4-nitro-pyrazole (3.00 g, 61% yield) as a white solid. The title compound was confirmed by NOE spectrum. $^1$H NMR (400 MHz, CDCl$_3$) δ 8.67 (s, 1H), 7.72-7.62 (m, 4H), 7.27 (s, 1H).

Step 2—1-(4-Bromophenyl)-3-(difluoromethyl)pyrazol-4-amine

To a solution of 1-(4-bromophenyl)-3-(difluoromethyl)-4-nitro-pyrazole (1.00 g, 3.14 mmol) in a mixed solvent of EtOH (10 mL) and H$_2$O (1 mL) was added Fe (878 mg, 15.7 mmol) and NH$_4$Cl (841 mg, 15.7 mmol). The mixture was stirred at 80° C. for 3 hours. On completion, the reaction mixture was concentrated in vacuo to remove EtOH, and then diluted with ethyl acetate (20 mL). Then the mixture was washed with NH$_3$.H$_2$O, and then washed with 1N HCl. The organic layer was washed with brine (2×10 mL), dried with anhydrous Na$_2$SO$_4$, filtered and the filtrate was concentrated in vacuo to give a residue. The residue was triturated with EA (10 mL) at 20° C. for 30 mins to give the title compound 1-(4-bromophenyl)-3-(difluoromethyl)pyrazol-4-amine (800 mg, 88% yield) as a yellow solid. $^1$H NMR (400 MHz, CDCl$_3$) δ 7.58-7.53 (m, 2H), 7.51-7.45 (m, 3H), 6.97-6.60 (m, 1H), 3.40 (s, 2H).

Tert-butyl N-[4-[4-[[1-(4-bromophenyl)-3-(difluoromethyl)pyrazol-4-yl]carbamoyl]oxazol-2-yl]-2-pyridyl]-N-(cyclopropylmethyl)carbamate (Intermediate AKI)

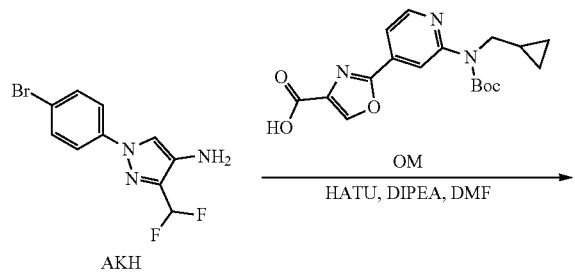

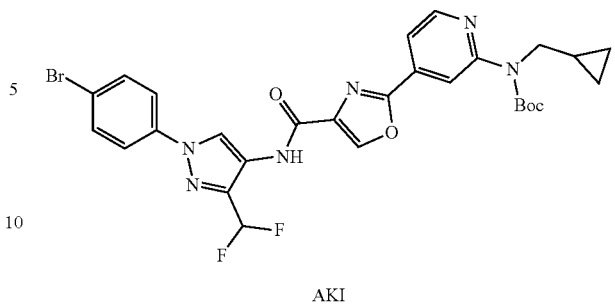

AKI

To a solution of 1-(4-bromophenyl)-3-(difluoromethyl)pyrazol-4-amine (200 mg, 694 umol, Intermediate AKH) and 2-[2-[tert-butoxycarbonyl(cyclopropylmethyl)amino]-4-pyridyl]oxazole-4-carboxylic acid (249 mg, 694 umol, Intermediate OM) in DMF (2.00 mL) was added HATU (396 mg, 1.04 mmol) and DIPEA (269 mg, 2.08 mmol, 362 uL). The mixture was stirred at 20° C. for 1 hour. On completion, the reaction mixture was quenched by water (0.5 mL), and then diluted with water (5 mL) and extracted with EA (2×10 mL). The combined organic layers were washed with brine (3×10 mL), dried over Na$_2$SO$_4$. The organic layer was concentrated in vacuo to give a residue. The residue was purified by recrystallization from EA (1.0 mL) to give the title compound (300 mg, 68% yield) as a yellow solid. $^1$H NMR (400 MHz, CDCl$_3$) δ 9.16 (s, 1H), 8.84 (s, 1H), 8.53 (dd, J=0.8, 5.2 Hz, 1H), 8.41 (s, 1H), 8.35 (s, 1H), 7.65 (dd, J=1.6, 5.2 Hz, 1H), 7.63 (s, 4H), 7.09-6.78 (m, 1H), 3.95 (d, J=7.2 Hz, 2H), 1.58 (s, 9H), 1.31-1.22 (m, 1H), 0.52-0.37 (m, 2H), 0.36-0.23 (m, 2H).

3-[1-(2,6-Dioxo-3-piperidyl)-3-methyl-2-oxo-benzimidazol-4-yl]propanoic acid (Intermediate AKM)

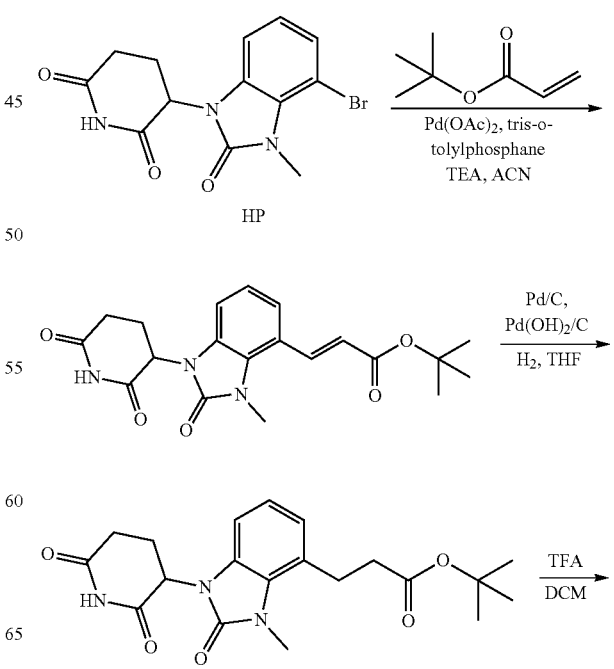

1931
-continued

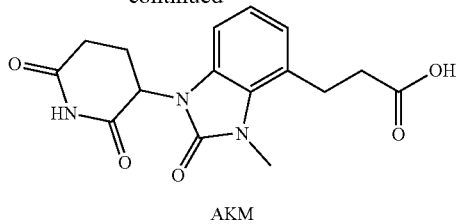

AKM

Step 1—tert-butyl (E)-3-[1-(2,6-dioxo-3-piperidyl)-3-methyl-2-oxo-benzimidazol-4-yl]prop-2-enoate To a mixture of 3-(4-bromo-3-methyl-2-oxo-benzimidazol-1-yl)piperidine-2,6-dione (1.00 g, 2.96 mmol, Intermediate HP) and tert-butyl prop-2-enoate (473 mg, 3.70 mmol, CAS #1663-39-4) in ACN (10 mL) was added TEA (4.04 g, 39.9 mmol), Pd(OAc)$_2$ (6.64 mg, 29.5 umol) and tris-o-tolylphosphane (36.0 mg, 118 umol). The reaction mixture was stirred at 100° C. for 12 hours. On completion, the mixture was concentrated in vacuo. The residue was purified by reverse phase (0.1% FA condition) to give the title compound (500 mg, 43% yield) as a white solid. $^1$H NMR (400 MHz, DMSO-d$_6$) δ 11.12 (s, 1H), 8.23 (d, J=15.6 Hz, 1H), 7.43 (d, J=8.0 Hz, 1H), 7.19 (d, J=8.0 Hz, 1H), 7.10-7.01 (m, 1H), 6.44 (d, J=15.6 Hz, 1H), 5.48-5.33 (m, 1H), 3.60 (s, 3H), 2.96-2.84 (m, 1H), 2.75-2.60 (m, 2H), 2.07-1.97 (m, 1H), 1.50 (s, 9H); LC-MS (ESI$^+$) m/z 386.2 (M+H)$^+$.

Step 2—Tert-butyl 3-[1-(2,6-dioxo-3-piperidyl)-3-methyl-2-oxo-benzimidazol-4-yl]propanoate To solution of tert-butyl (E)-3-[1-(2,6-dioxo-3-piperidyl)-3-methyl-2-oxo-benzimidazol-4-yl]prop-2-enoate (100 mg, 259 umol) in THF (10 mL) was added Pd/C (30.0 mg, 10 wt %) and Pd(OH)$_2$/C (30.0 mg, 10 wt %), the reaction mixture was stirred at 20° C. for 4 hours under H$_2$ (15 psi). On completion, the reaction mixture was filtered and the filtrate was concentrated in vacuo to give the title compound (90.0 mg, 89% yield) as a white solid. $^1$H NMR (400 MHz, DMSO-d$_6$) δ 11.09 (s, 1H), 7.01-6.93 (m, 2H), 6.91-6.86 (m, 1H), 5.37 (dd, J=5.2, 12.4 Hz, 1H), 3.57 (s, 3H), 3.16 (t, J=7.6 Hz, 2H), 2.95-2.81 (m, 1H), 2.76-2.55 (m, 4H), 2.02-1.94 (m, 1H), 1.36 (s, 9H); LC-MS (ESI$^+$) m/z 388.1 (M+H)$^+$.

Step 3—3-[1-(2,6-Dioxo-3-piperidyl)-3-methyl-2-oxo-benzimidazol-4-yl]propanoic acid To a solution of tert-butyl 3-[1-(2,6-dioxo-3-piperidyl)-3-methyl-2-oxo-benzimidazol-4-yl]propanoate (80.0 mg, 206 umol) in DCM (2 mL) was added TFA (2 mL), and the reaction mixture was stirred at 20° C. for 1 hour. On completion, the mixture was concentrated in vacuo to give the title compound (65.0 mg, 95% yield) as a white solid. LC-MS (ESI$^+$) m/z 332.2 (M+H)$^+$.

1932

3-[4-[3-(2,7-Diazaspiro[3.5]nonan-2-yl)-3-oxo-propyl]-3-methyl-2-oxo-benzimidazol-1-yl] piperidine-2,6-dione (Intermediate AKN)

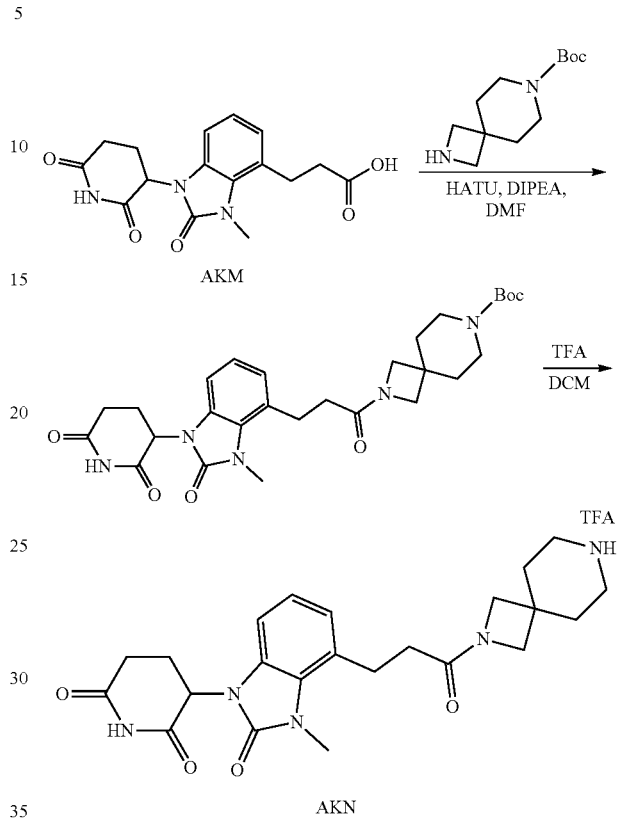

Step 1—Tert-butyl 2-[3-[1-(2,6-dioxo-3-piperidyl)-3-methyl-2-oxo-benzimidazol-4-yl]propanoyl]-2,7-diazaspiro[3.5]nonane-7-carboxylate To a solution of 3-[1-(2,6-dioxo-3-piperidyl)-3-methyl-2-oxo-benzimidazol-4-yl]propanoic acid (65.0 mg, 196 umol, Intermediate AKM) in DMF (3 mL) was added DIPEA (126 mg, 980 umol), and HATU (89.5 mg, 235 umol), and the mixture was stirred at 20° C. for 15 minutes. Then tert-butyl 2,7-diazaspiro[3.5]nonane-7-carboxylate (44.4 mg, 196 umol, CAS #896464-16-7) was added to the mixture. The reaction mixture was stirred at 20° C. for 1 hour. On completion, the reaction mixture quenched with H$_2$O (0.5 mL). Then the mixture was concentrated in vacuo. The residue was purified by reverse phase (0.1% FA condition) to give the title compound (75.0 mg, 70% yield) as a white solid. $^1$H NMR (400 MHz, DMSO-d$_6$) δ11.10 (s, 1H), 7.03-6.93 (m, 2H), 6.92-6.86 (m, 1H), 5.38 (dd, J=5.2, 12.8 Hz, 1H), 3.63 (s, 2H), 3.58 (s, 3H), 3.50 (s, 2H), 3.28-3.10 (m, 6H), 2.96-2.83 (m, 1H), 2.78-2.68 (m, 1H), 2.66-2.59 (m, 1H), 2.41 (t, J=8.0 Hz, 2H), 2.04-1.92 (m, 1H), 1.52 (t, J=5.6 Hz, 4H), 1.38 (s, 9H); LC-MS (ESI$^+$) m/z 540.2 (M+H)$^+$.

Step 2—3-[4-[3-(2,7-Diazaspiro[3.5]nonan-2-yl)-3-oxo-propyl]-3-methyl-2-oxo-benzimidazol-1-yl] piperidine-2,6-dione To a solution of tert-butyl 2-[3-[1-(2,6-dioxo-3-piperidyl)-3-methyl-2-oxo-benzimidazol-4-yl] propanoyl]-2,7- diazaspiro[3.5]nonane-7-carboxylate (70.0 mg, 129 umol) in DCM (3 mL) was added TFA (1.5 mL), and the reaction mixture was stirred at 20° C. for 1 hour. On completion, the reaction mixture was concentrated in vacuo to give the title compound (65.0 mg, 90% yield, TFA) as a yellow solid. LC-MS (ESI⁺) m/z 440.2 (M+H)⁺.

4-[3-(difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]benzoic acid (Intermediate AKT)

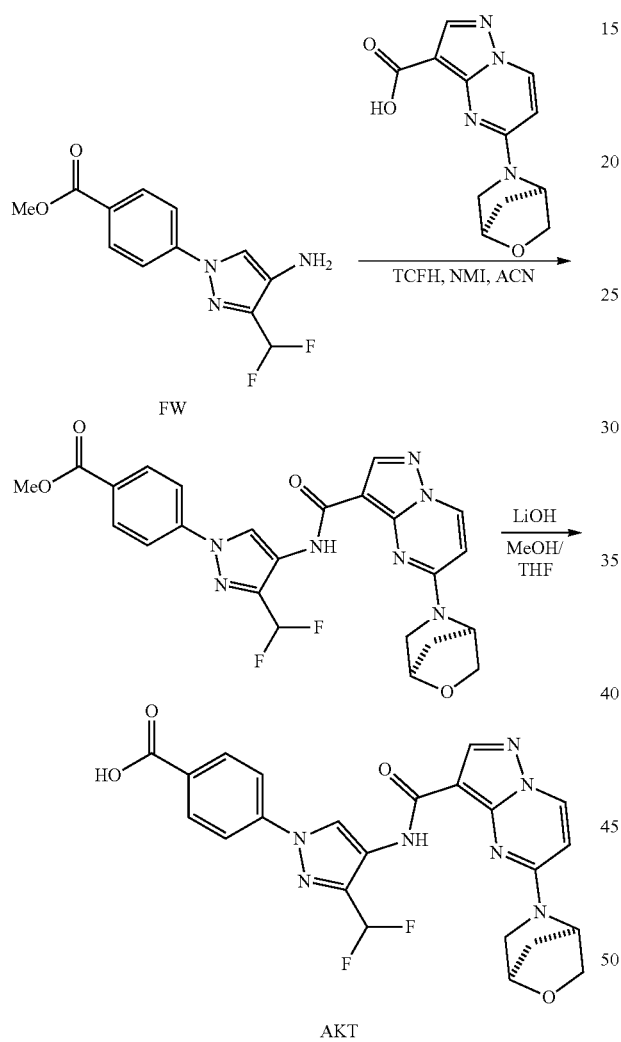

Step 1—Methyl 4-[3-(difluoromethyl)-4-[[5-[(1R)-2-oxa-5-azabicyclo[2.2.1]heptan-5-yl]pyrazolo[1,5-a]pyrimidine-3-carbonyl]amino]pyrazol-1-yl]benzoate To a mixture of 5-[(1R)-2-oxa-5-azabicyclo[2.2.1]heptan-5-yl]pyrazolo[1,5-a]pyrimidine-3-carboxylic acid (1.17 g, 4.49 mmol, Intermediate AEH) in ACN (15 mL) and DMF (2 mL) was added [chloro(dimethylamino) methylene]-dimethyl-ammonium; hexafluorophosphate (1.36 g, 4.86 mmol) and 1-methylimidazole (1.08 g, 13.1 mmol). Methyl 4-[4-amino-3-(difluoromethyl)pyrazol-1-yl]benzoate (1.00 g, 3.74 mmol, Intermediate FW) was added into the mixture. The reaction mixture was stirred at 25° C. for 1 hour. On completion, the reaction was filtered to give filter cake. The filter cake was dried to give the title compound (1.20 g, 62% yield) as a white solid. ¹H NMR (400 MHz, DMSO-d₆) δ 9.61 (s, 1H), 9.11 (s, 1H), 8.79 (d, J=4.8 Hz, 1H), 8.30 (d, J=4.8 Hz, 1H), 8.14-8.06 (m, 2H), 8.05-7.97 (m, 2H), 7.51-7.16 (m, 1H), 6.94-6.42 (m, 1H), 5.33-5.06 (m, 1H), 4.79 (d, J=12.0 Hz, 1H), 3.88 (s, 3H), 3.85-3.73 (m, 2H), 3.64-3.44 (m, 2H), 2.09-1.94 (m, 2H).

Step 2—4-[3-(Difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]benzoic acid To a mixture of methyl 4-[3-(difluoromethyl)-4-[[5-[(1R,4R)-2-oxa-5-azabicyclo[2.2.1]heptan-5-yl] pyrazolo[1,5-a]pyrimidine-3-carbonyl]amino]pyrazol-1-yl]benzoate (600 mg, 1.18 mmol) in THF (20 mL), MeOH (5 mL) and H₂O (5 mL) was added LiOH (42.4 mg, 1.77 mmol). The reaction mixture was stirred at 50° C. for 12 hours. On completion, the reaction was poured into water (20 mL) and adjusted to pH=5-6 with HCl (1 N). The mixture was filtered and the filter cake was dried to give the title compound (560 mg, 95% yield) as a white solid. ¹H NMR (400 MHz, DMSO-d₆) δ 13.42-12.86 (m, 1H), 9.62 (d, J=2.0 Hz, 1H), 9.10 (s, 1H), 8.80 (d, J=7.6 Hz, 1H), 8.30 (d, J=4.8 Hz, 1H), 8.15-8.03 (m, 2H), 7.98 (d, J=8.4 Hz, 2H), 7.50-7.14 (m, 1H), 6.94-6.41 (m, 1H), 5.33-5.07 (m, 1H), 4.79 (d, J=12.0 Hz, 1H), 3.88-3.72 (m, 2H), 3.69-3.44 (m, 2H), 2.06-1.92 (m, 2H).

Tert-butyl (2S)-2-(3-aminopropoxymethyl)morpholine-4-carboxylate (Intermediate AKZ)

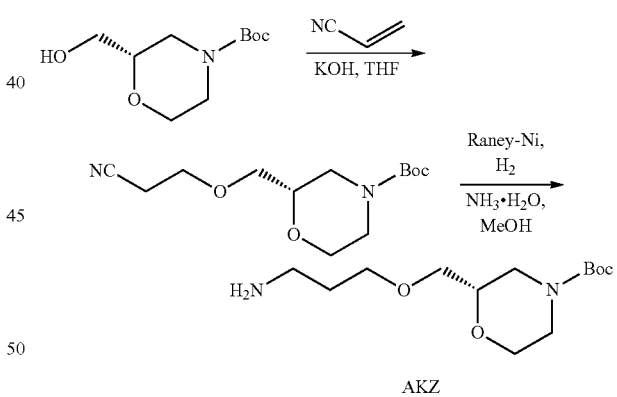

Step 1—Tert-butyl (2S)-2-(2-cyanoethoxymethyl) morpholine-4-carboxylate

To a solution of tert-butyl (2S)-2-(hydroxymethyl)morpholine-4-carboxylate (2.00 g, 9.21 mmol, CAS #135065-76-8) and prop-2-enenitrile (976 mg, 18.4 mmol) in THF (30 mL) was added KOH (51.6 mg, 920 umol). The reaction mixture was stirred at 20° C. for 12 hours. On completion, the reaction mixture was poured into water (50 mL) and extracted with EA (3×100 mL). The combined organic layers were washed with brine (2×80 mL), dried over Na₂SO₄, filtered and concentrated in vacuo. The residue was purified by silica gel chromatography (PE:EA=4:1) to give the title compound (1.80 g, 72% yield) as yellow oil. $^1$H NMR (400 MHz, CDCl$_3$) δ 4.00-3.80 (m, 3H), 3.72 (t, J=6.4 Hz, 2H), 3.62-3.47 (m, 4H), 3.02-2.86 (m, 1H), 2.84-2.68 (m, 1H), 2.63 (t, J=6.4 Hz, 2H), 1.47 (s, 9H).

Step 2—Tert-butyl (2S)-2-(3-aminopropoxymethyl) morpholine-4-carboxylate

To a solution of tert-butyl (2S)-2-(2-cyanoethoxymethyl) morpholine-4-carboxylate (1.80 g, 6.66 mmol) and NH$_3$.H$_2$O (2.0 mL, 28% solution) in MeOH (20 mL) was added Raney-Ni (57.0 mg, 665 umol). The reaction mixture was stirred at 20° C. for 16 hours under hydrogen (50 psi). On completion, the reaction mixture was filtered and the filtrate was concentrated in vacuo to give the title compound (1.80 g, 98% yield) as colorless oil. $^1$H NMR (400 MHz, DMSO-d$_6$) δ 3.88-3.56 (m, 3H), 3.46-3.17 (m, 6H), 2.77 (s, 2H), 2.64-2.54 (m, 1H), 2.46-2.39 (m, 3H), 1.55-1.42 (m, 2H), 1.34 (s, 9H).

2-(2,6-Dioxo-3-piperidyl)-4-[3-[[(2S)-morpholin-2-yl]methoxy]propylamino]isoindoline-1,3-dione (Intermediate ALA)

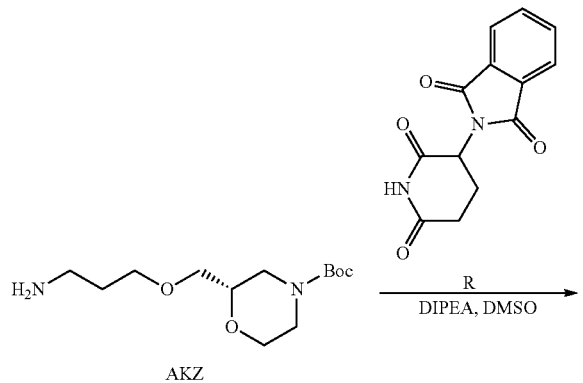

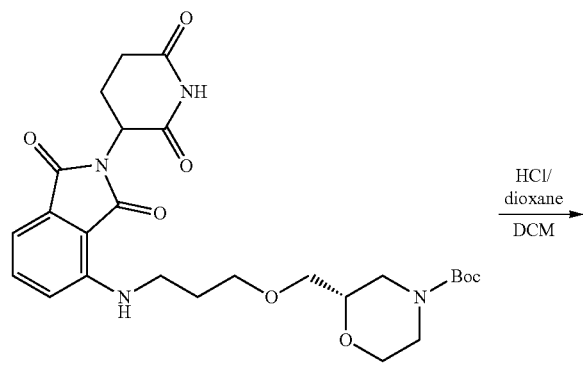

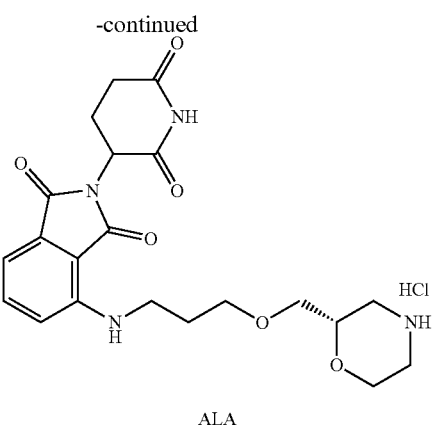

ALA

Step 1—Tert-butyl (2S)-2-[3-[[2-(2,6-dioxo-3-piperidyl)-1,3-dioxo-isoindolin-4-yl]amino] propoxymethyl]morpholine-4-carboxylate To a solution of tert-butyl (2S)-2-(3-aminopropoxymethyl)morpholine-4-carboxylate (300 mg, 1.09 mmol, Intermediate AKZ) and 2-(2,6-dioxo-3-piperidyl)-4-fluoro-isoindoline-1,3-dione (302 mg, 1.09 mmol, Intermediate R) in DMSO (5 mL) was added DIPEA (282 mg, 2.19 mmol). The reaction mixture was stirred at 130° C. for 3 hrs. On completion, the reaction mixture was diluted with water (30 mL) and extracted with EA (3×60 mL). The combined organic layers were washed with brine (2×60 mL), dried over Na$_2$SO$_4$, filtered and concentrated in vacuo. The residue was purified by reverse phase (0.1% FA) to give the title compound (410 mg, 65% yield, FA salt) as yellow solid. $^1$H NMR (400 MHz, CDCl$_3$) δ 8.28-8.09 (m, 1H), 7.57-7.44 (m, 1H), 7.09 (d, J=7.2 Hz, 1H), 6.98-6.88 (m, 1H), 6.65-6.34 (m, 1H), 4.97-4.86 (m, 1H), 4.02-3.78 (m, 3H), 3.72-3.54 (m, 5.6 Hz, 4H), 3.53-3.35 (m, 4H), 3.03-2.62 (m, 5H), 2.19-2.07 (m, 1H), 2.02-1.90 (m, 2H), 1.47 (d, J=1.2 Hz, 9H).

Step 2—2-(2,6-Dioxo-3-piperidyl)-4-[3-[[(2S)-morpholin-2-yl]methoxy]propylamino]isoindoline-1,3-dione To a solution of tert-butyl (2S)-2-[3-[[2-(2,6-dioxo-3-piperidyl)-1,3-dioxo-isoindolin-4-yl]amino] propoxymethyl]morpholine-4-carboxylate (410 mg, 711 umol, FA salt) in DCM (6 mL) was added HCl/dioxane (4 M, 4 mL). The reaction mixture was stirred at 20° C. for 1 hour. On completion, the reaction mixture was concentrated in vacuo to give the title compound (330 mg, 99% yield, HCl salt) as yellow solid. LC-MS (ESI$^+$) m/z 431.2 (M+H)$^+$.

2-(2,6-Dioxo-3-piperidyl)-4-[3-[3-(methylamino)propoxy]propylamino]isoindoline-1,3-dione (Intermediate AMC)

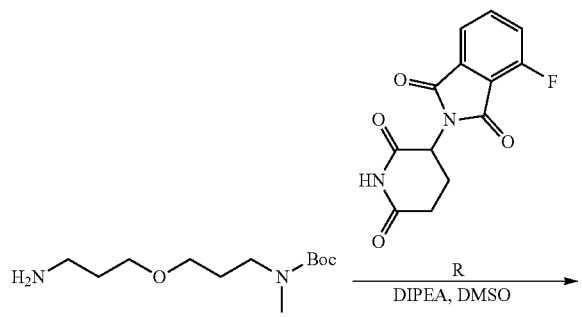

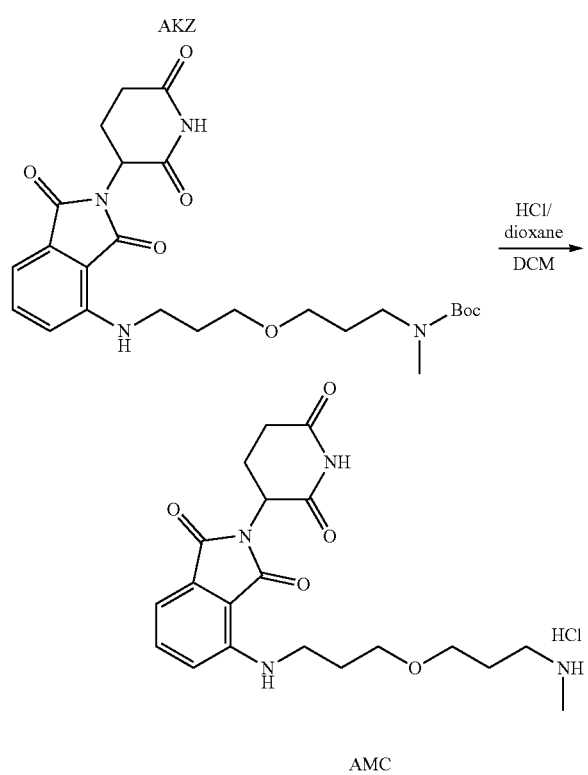

Step 1—Tert-butyl N-[3-[3-[[2-(2,6-dioxo-3-piperidyl)-1,3-dioxo-isoindolin-4-yl]amino]propoxy]propyl]-N-methyl-carbamate To a solution of tert-butyl N-[3-(3-aminopropoxy)propyl]-N-methyl-carbamate (130 mg, 527 umol, synthesized via Steps 1-2 on Intermediate AEU) and 2-(2,6-dioxo-3-piperidyl)-4-fluoro-isoindoline-1,3-dione (132 mg, 479 umol, Intermediate R) in DMSO (10 mL) was added DIPEA (18.7 mg, 144 umol) at 25° C. The reaction mixture was stirred at 130° C. for 2 hrs. On completion, the reaction mixture was concentrated in vacuo to give the residue. The residue was purified by reverse phase (0.1% FA condition) to give the title compound (160 mg, 66% yield) as a yellow solid. $^1$H NMR (400 MHz, DMSO-$d_6$) δ 11.07 (s, 1H), 7.58 (dd, J=7.2, 8.0 Hz, 1H), 7.17-6.95 (m, 2H), 6.66 (t, J=6.0 Hz, 1H), 5.04 (dd, J=5.2, 12.8 Hz, 1H), 3.46 (t, J=6.0 Hz, 2H), 3.41-3.33 (m, 4H), 3.21 (t, J=6.8 Hz, 2H), 2.94-2.82 (m, 1H), 2.75 (s, 3H), 2.63-2.53 (m, 2H), 2.08-1.96 (m, 1H), 1.86-1.76 (m, 2H), 1.71-1.66 (m, 2H), 1.37 (s, 9H); LC-MS (ESI$^+$) m/z 503.4 (M+H)$^+$.

Step 2—2-(2,6-Dioxo-3-piperidyl)-4-[3-[3-(methylamino)propoxy]propylamino]isoindoline-1,3-dione To a solution of tert-butyl N-[3-[3-[[2-(2,6-dioxo-3-piperidyl)-1,3-dioxo-isoindolin-4-yl]amino] propoxy]propyl]-N-methyl-carbamate (140 mg, 278 umol) in DCM (5 mL) was added HCl/dioxane (4 M, 4 mL) at 25° C. The mixture was stirred at 25° C. for 2 hrs. On completion, the reaction mixture was concentrated in vacuo to give the title compound (120 mg, 98% yield, HCl salt) as a yellow solid. LC-MS (ESI$^+$) m/z 403.0 (M+H)$^+$.

2-(2,6-dioxo-3-piperidyl)-4-[2-[(2S)-4-[2-(methylamino)ethyl]morpholin-2-yl]ethyl amino]isoindoline-1,3-dione (Intermediate AMD)

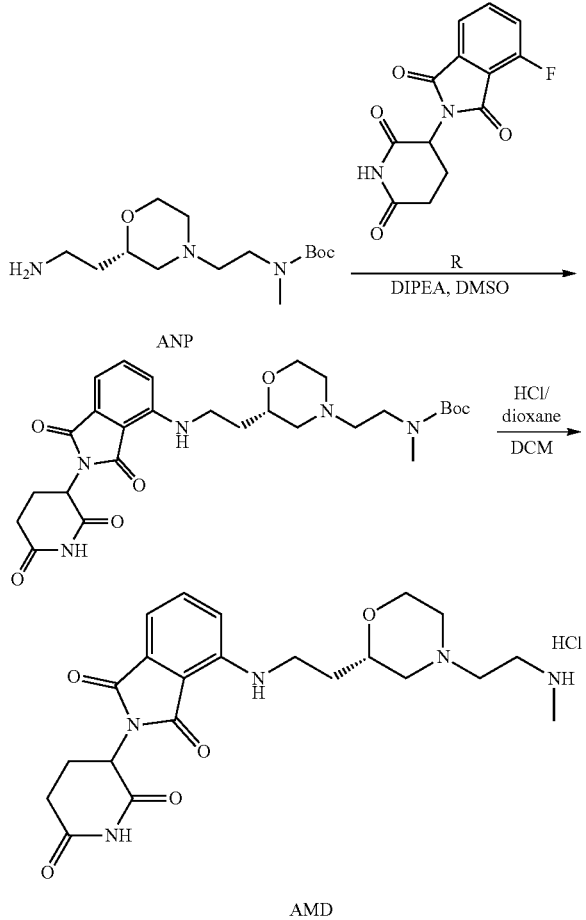

Step 1—Tert-butyl N-[2-[(2S)-2-[2-[[2-(2,6-dioxo-3-piperidyl)-1,3-dioxo-isoindolin-4-yl]amino] ethyl] morpholin-4-yl] ethyl]-N-methyl-carbamate To a solution of 2-(2,6-dioxo-3-piperidyl)-4-fluoro-isoindoline-1,3-dione (300 mg, 1.09 mmol, Intermediate R) and tert-butyl N-[2-[(2S)-2-(2-aminoethyl)morpholin-4-yl]

ethyl]-N-methyl-carbamate (312 mg, 1.09 mmol, Intermediate ANP) in DMSO (5 mL) was added DIPEA (280 mg, 2.17 mmol). The reaction mixture was stirred at 130° C. for 3 hrs. On completion, the reaction mixture was diluted with water (30 mL) and extracted with EA (3×50 mL). The combined organic layers were washed with brine (2×30 mL), dried over Na$_2$SO$_4$, filtered and concentrated in vacuo. The residue was reverse phase (0.1% FA) twice to give the title compound (350 mg, 39% yield, FA salt) as yellow solid. $^1$H NMR (400 MHz, DMSO-d$_6$) δ 11.08 (s, 1H), 7.58 (dd, J=7.2, 8.4 Hz, 1H), 7.08 (d, J=8.4 Hz, 1H), 7.02 (d, J=6.8 Hz, 1H), 6.73 (s, 1H), 5.04 (dd, J=5.6, 12.8 Hz, 1H), 3.86-3.77 (m, 1H), 3.52-3.48 (m, 2H), 3.27-3.26 (m, 2H), 2.93-2.81 (m, 2H), 2.80-2.75 (m, 3H), 2.74-2.68 (m, 2H), 2.63-2.52 (m, 3H), 2.43-2.36 (m, 2H), 2.07-1.96 (m, 2H), 1.90-1.77 (m, 1H), 1.73-1.58 (m, 2H), 1.34 (s, 9H).

Step 2—2-(2,6-Dioxo-3-piperidyl)-4-[2-[(2S)-4-[2-(methylamino)ethyl]morpholin-2-yl]ethylamino] isoindoline-1,3-dione To a solution of tert-butyl N-[2-[(2S)-2-[2-[[2-(2,6-dioxo-3-piperidyl)-1,3-dioxo-isoindolin-4-yl] amino] ethyl]morpholin-4-yl] ethyl]-N-methyl-carbamate (350 mg, 426 umol, FA salt) in DCM (5 mL) was added HCl/dioxane (4 M, 4 mL). The reaction mixture was stirred at 15° C. for 1 hr. On completion, the reaction mixture was concentrated in vacuo to give the title compound (280 mg, 98% yield, HCl salt) as yellow solid. LC-MS (ESI$^+$) m/z 444.1 (M+H)$^+$.

[4-[3-(Difluoromethyl)-4-(methylamino)pyrazol-1-yl]cyclohexyl]methanol (Intermediate AMJ)

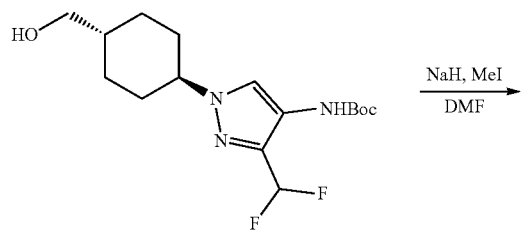

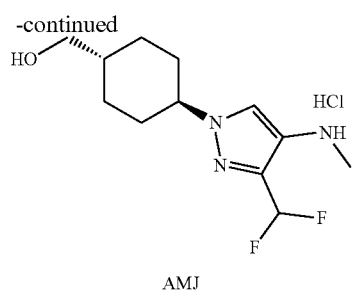

AMJ

Step 1—Tert-butyl N-[3-(difluoromethyl)-1-[4-(hydroxymethyl)cyclohexyl]pyrazol-4-yl]-N-methyl-carbamate To a solution of tert-butyl N-[3-(difluoromethyl)-1-[4-(hydroxymethyl)cyclohexyl]pyrazol-4-yl] carbamate (5.00 g, 14.4 mmol, synthesized via Step 1 of Intermediate ABM) in DMF (30 mL) was added NaH (752 mg, 18.8 mmol, 60% dispersion in mineral oil) at 0° C. The reaction mixture was stirred at 0° C. for 10 mins. Then MeI (2.67 g, 18.8 mmol) was added. The reaction mixture was stirred at 20° C. for 1 hour. On completion, the reaction mixture was quenched with saturated NH$_4$Cl aqueous (10 mL). The mixture was poured into water (100 mL), then extracted with EA (2×40 mL). The organic layer was concentrated in vacuo. The residue was purified by silica gel chromatography (petroleum ether:ethyl acetate=4:1) to give the title compound (4.00 g, 76% yield) as light yellow gum. $^1$H NMR (400 MHz, CDCl$_3$) δ 7.54-7.29 (m, 1H), 6.92-6.43 (m, 1H), 4.11-3.98 (m, 1H), 3.53 (t, J=5.2 Hz, 2H), 3.17 (s, 3H), 2.31-2.18 (m, 2H), 2.02-1.93 (m, 2H), 1.81-1.68 (m, 2H), 1.59-1.53 (m, 1H), 1.51-1.32 (m, 9H), 1.23-1.10 (m, 2H).

Step 2—[4-[3-(Difluoromethyl)-4-(methylamino) pyrazol-1-yl] cyclohexyl]methanol

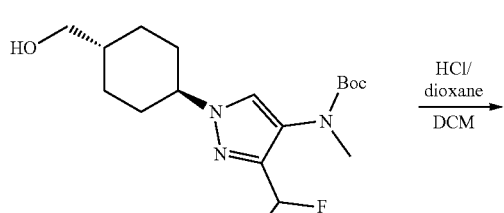

To a mixture of tert-butyl N-[3-(difluoromethyl)-1-[4-(hydroxymethyl)cyclohexyl]pyrazol-4-yl]-N-methyl-carbamate (1.00 g, 2.78 mmol) in DCM (8 mL) was added HCl/dioxane (4 M, 7.69 mL) at 0° C. The reaction mixture was stirred at 20° C. for 1 hour. On completion, the reaction mixture was concentrated in vacuo to give the title compound (800 mg, 97% yield, HCl salt) as yellow gum. $^1$H NMR (400 MHz, DMSO-d$_6$) δ 8.13 (s, 1H), 7.40-7.02 (m, 1H), 4.22-4.13 (m, 1H), 3.25 (d, J=6.4 Hz, 2H), 2.82 (s, 3H), 2.06-1.98 (m, 2H), 1.90-1.81 (m, 2H), 1.76-1.63 (m, 2H), 1.49-1.36 (m, 1H), 1.16-1.00 (m, 2H).

Tert-butyl N-(cyclopropylmethyl)-N-[4-[4-[[3-(difluoromethyl)-1-(4-formylcyclohexyl) pyrazol-4-yl]-methyl-carbamoyl]oxazol-2-yl]-2-pyridyl]carbamate
(Intermediate AMK)

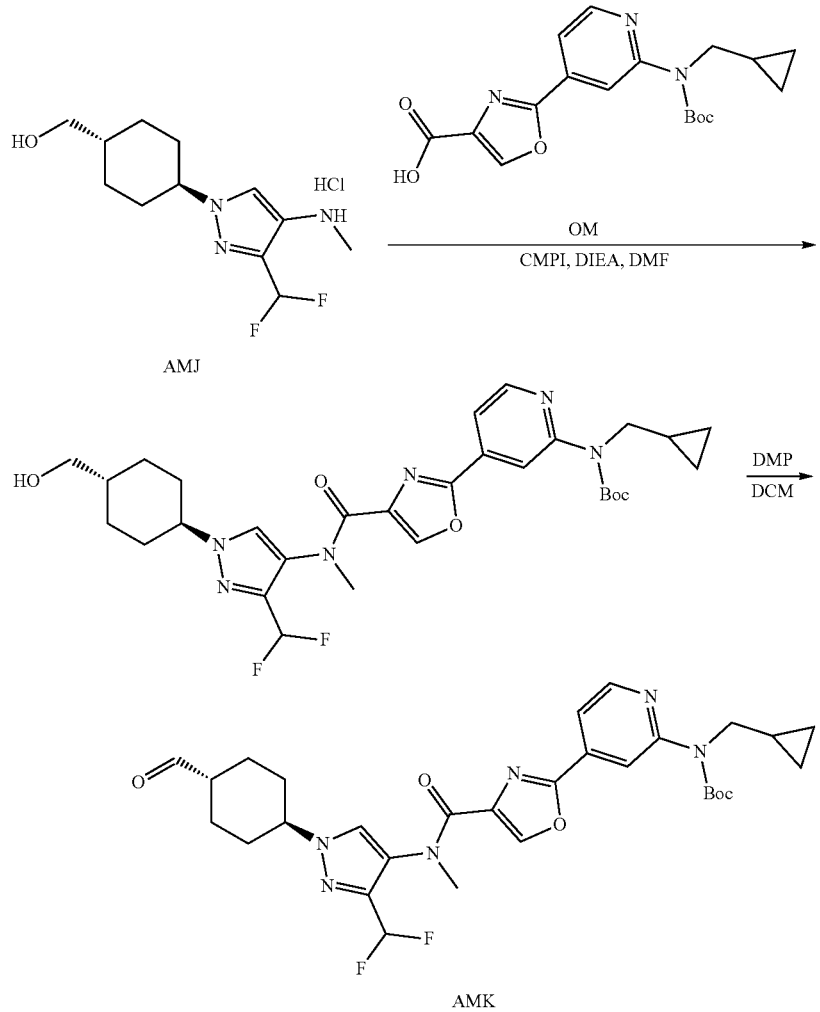

Step 1—Tert-butyl N-(cyclopropylmethyl)-N-[4-[4-[[3-(difluoromethyl)-1-[4-(hydroxymethyl) cyclohexyl]pyrazol-4-yl]-methyl-carbamoyl]oxazol-2-yl]-2-pyridyl]carbamate To a mixture of 2-[2-[tert-butoxycarbonyl(cyclopropylmethyl)amino]-4-pyridyl]oxazole-4-carboxylic acid (450 mg, 1.25 mmol, Intermediate OM) in DMF (10 mL) was added CMPI (415 mg, 1.63 mmol) and DIPEA (404 mg, 3.13 mmol). The reaction mixture was stirred at 25° C. for 0.5 hour. Then [4-[3-(difluoromethyl)-4-(methylamino)pyrazol-1-yl]cyclohexyl]methanol (407 mg, 1.38 mmol HCl salt, Intermediate AMJ) was added and the reaction mixture was stirred at 25° C. for 0.5 hour. On completion, the reaction mixture was quenched with water (5 mL), and concentrated in vacuo. The residue was diluted in water (50 mL) and the mixture was extracted with EA (2×50 mL). The organic layer was washed with brine (50 mL) and concentrated in vacuo (650 mg, 86% yield) as yellow gum. $^1$H NMR (400 MHz, CDCl$_3$) δ 8.41 (d, J=4.8 Hz, 1H), 8.19 (s, 1H), 7.60 (s, 1H), 7.52-7.37 (m, 2H), 6.88-6.50 (m, 1H), 4.11-4.01 (m, 1H), 3.89 (d, J=7.2 Hz, 2H), 3.52 (d, J=6.4 Hz, 2H), 3.40 (s, 3H), 2.26-2.13 (m, 2H), 2.01-1.95 (m, 2H), 1.80-1.70 (m, 2H), 1.63-1.59 (m, 1H), 1.54 (s, 9H), 1.22-1.12 (m, 3H), 0.47-0.34 (m, 2H), 0.29-0.19 (m, 2H).

Step 2—Tert-butyl N-(cyclopropylmethyl)-N-[4-[4-[[3-(difluoromethyl)-1-(4-formylcyclohexyl) pyrazol-4-yl]-methyl-carbamoyl] oxazol-2-yl]-2-pyridyl] carbamate To a mixture of tert-butyl N-(cyclopropylmethyl)-N-[4-[4-[[3-(difluoromethyl)-1-[4-(hydroxymethyl) cyclohexyl] pyrazol-4-yl]-methyl-carbamoyl]oxazol-2-yl]-2-pyridyl] carbamate (750 mg, 1.25 mmol) in DCM (20 mL) was added DMP (582 mg, 1.37 mmol) at 0° C. The reaction mixture was stirred at 20° C. for 0.5 hour. On completion, the reaction mixture was quenched with saturated Na$_2$SO$_3$ aqueous (2 mL) and saturated NaHCO$_3$ (10 mL) aqueous was added. The mixture was extracted with DCM (2×30 mL).

The organic layer was concentrated in vacuo. The residue was diluted in EA (20 mL) and filtered through silica gel. The filtrate was concentrated in vacuo to give the title compound (600 mg, 80% yield) as light yellow solid. $^1$H NMR (400 MHz, DMSO-$d_6$) δ 9.59 (s, 1H), 8.51 (d, J=4.8 Hz, 1H), 8.13 (s, 1H), 8.10 (s, 1H), 8.05 (s, 1H), 7.44 (d, J=4.4 Hz, 1H), 7.11-6.71 (m, 1H), 4.23-4.08 (m, 1H), 3.90-3.75 (m, 2H), 3.25 (s, 3H), 2.37-2.27 (m, 1H), 2.14-1.98 (m, 4H), 1.86-1.69 (m, 2H), 1.49 (s, 9H), 1.42-1.28 (m, 2H), 1.15-1.08 (m, 1H), 0.41-0.36 (m, 2H), 0.24-0.18 (m, 2H).

Tert-butyl N-[2-[(2S)-2-(2-aminoethyl)morpholin-4-yl]ethyl]-N-methyl-carbamate (Intermediate ANP)

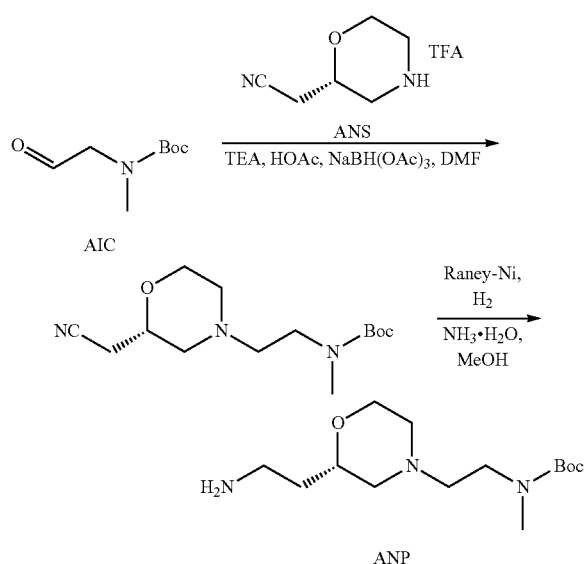

AIC

ANP

Step 1—Tert-butyl N-[2-[(2S)-2-(cyanomethyl)morpholin-4-yl]ethyl]-N-methyl-carbamate To a solution of 2-[(2S)-morpholin-2-yl]acetonitrile (900 mg, 3.75 mmol, TFA salt, Intermediate ANS) in a mixed solvents of THF (10 mL) and DMF (5 mL) was added TEA until the pH=7-8, then acidified with AcOH until the pH=5-6 and tert-butyl N-methyl-N-(2-oxoethyl)carbamate (649 mg, 3.75 mmol, Intermediate AIC) was added. After the reaction mixture was stirred at 20° C. for 0.5 hr, NaBH(OAc)$_3$ (1.19 g, 5.62 mmol) was added. The reaction mixture was stirred at 20° C. for 3 hrs. On completion, the reaction mixture was diluted with water (40 mL) and extracted EA (3×70 mL). The combined organic layers were washed with brine (2×50 mL), dried over Na$_2$SO$_4$, filtered and concentrated in vacuo. The residue was purified by silica gel chromatography (PE:EA=1:2) to give the title compound (550 mg, 51% yield) as yellow oil. $^1$H NMR (400 MHz, CDCl$_3$) δ 3.95-3.85 (m, 1H), 3.84-3.74 (m, 1H), 3.72-3.61 (m, 1H), 3.43-3.25 (m, 2H), 2.92-2.89 (m, 1H), 2.89-2.83 (m, 3H), 2.79-2.67 (m, 1H), 2.55 (d, J=6.0 Hz, 2H), 2.51 (t, J=6.8 Hz, 2H), 2.26 (dt, J=3.2, 11.2 Hz, 1H), 2.13-2.05 (m, 1H), 1.46 (s, 9H).

Step 2—Tert-butyl N-[2-[(2S)-2-(2-aminoethyl)morpholin-4-yl]ethyl]-N-methyl-carbamate To a solution of tert-butyl N-[2-[(2S)-2-(cyanomethyl)morpholin-4-yl]ethyl]-N-methyl-carbamate (550 mg, 1.94 mmol) and NH$_3$—H$_2$O (1.37 g, 10.9 mmol, 1.5 mL) in MeOH (15 mL) was added Raney-Ni (33.2 mg, 388 umol). The reaction mixture was stirred at 20° C. for 12 hrs under hydrogen (50 Psi). On completion, the reaction mixture was filtered and the filtrate was concentrated in vacuo to give the title compound (500 mg, 89% yield) as colorless oil. $^1$H NMR (400 MHz, DMSO-$d_6$) δ 3.80-3.65 (m, 1H), 3.49-3.38 (m, 2H), 3.25 (t, J=6.8 Hz, 2H), 2.82-2.73 (m, 3H), 2.73-2.64 (m, 2H), 2.63-2.56 (m, 2H), 2.56-2.53 (m, 2H), 2.40-2.34 (m, 1H), 2.07-1.94 (m, 1H), 1.80-1.67 (m, 1H), 1.51-1.31 (m, 10H).

2-(2,6-Dioxo-3-piperidyl)-4-[3-[(2R)-2-(methylaminomethyl)morpholin-4-yl]propylamino] isoindoline-1,3-dione (Intermediate ANQ)

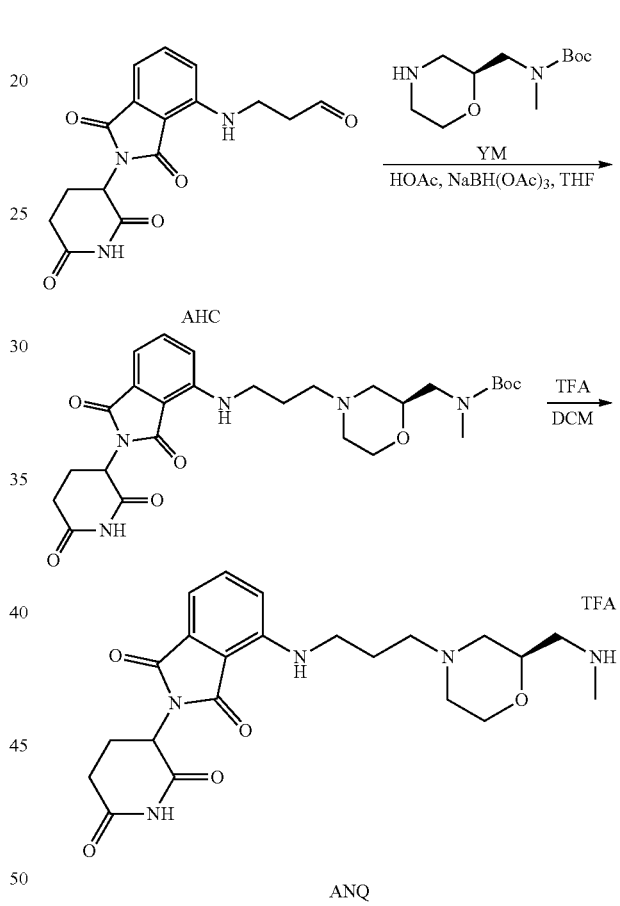

AHC

ANQ

Step 1—Tert-butyl N-[[(2S)-4-[3-[[2-(2,6-dioxo-3-piperidyl)-1,3-dioxo-isoindolin-4-yl]amino]propyl] morpholin-2-yl]methyl]-N-methyl-carbamate To a solution of 3-[[2-(2,6-dioxo-3-piperidyl)-1,3-dioxo-isoindolin-4-yl]amino]propanal (110 mg, 334 umol, Intermediate AHC) and tert-butyl N-methyl-N-[[(2S)-morpholin-2-yl]methyl]carbamate (92.3 mg, 400 umol, Intermediate YM) in THF (5 mL) was added HOAc (20.0 mg, 334 umol, 19.1 uL), and the mixture was stirred at 0° C. for 30 mins. Then NaBH(OAc)$_3$ (92.0 mg, 434 umol) was added to the mixture, and the reaction mixture was stirred at 0° C. for 2 hrs. On completion, the mixture was quenched by addition H$_2$O (0.5 mL), then the mixture was concentrated in vacuo to give a residue. The residue was purified by reverse phase (0.1% FA condition) to give the title compound (160 mg, 80% yield) as a yellow solid. $^1$H NMR (400 MHz, DMSO-$d_6$) δ 11.07 (d, J=3.2 Hz, 1H), 7.57 (dd, J=7.2, 8.4 Hz, 1H), 7.12 (d, J=8.4 Hz, 1H), 7.01 (d, J=6.8 Hz, 1H), 6.81-6.72 (m, 1H), 5.09-4.99 (m, 1H), 3.80-3.74 (m, 1H), 3.68-3.51 (m, 3H), 3.22-3.18 (m, 2H), 2.93-2.84 (m, 1H), 2.79 (s, 3H), 2.72-2.67 (m, 2H), 2.62-2.53 (m, 2H), 2.40-2.34 (m, 2H), 2.05-1.94 (m, 2H), 1.82-1.62 (m, 4H), 1.36 (s, 9H); LC-MS (ESI$^+$) m/z 544.3 (M+H)$^+$.

Step 2—2-(2,6-Dioxo-3-piperidyl)-4-[3-[(2R)-2-(methylaminomethyl)morpholin-4-yl]propylamino]isoindoline-1,3-dione To a solution of tert-butyl N-[[(2S)-4-[3-[[2-(2,6-dioxo-3-piperidyl)-1,3-dioxo-isoindolin-4-yl]amino] propyl]morpholin-2-yl]methyl]-N-methyl-carbamate (120 mg, 220 umol) in DCM (2 mL) was added TFA (3.08 g, 27.0 mmol, 2 mL), the reaction mixture was stirred at 20° C. for 1 hr. On completion, the mixture was concentrated in vacuo to give the title compound (120 mg, 98% yield, TFA salt) as a yellow solid. LC-MS (ESI$^+$) m/z 444.2 (M+H)$^+$.

2-[(2S)-Morpholin-2-yl]acetonitrile (Intermediate ANS)

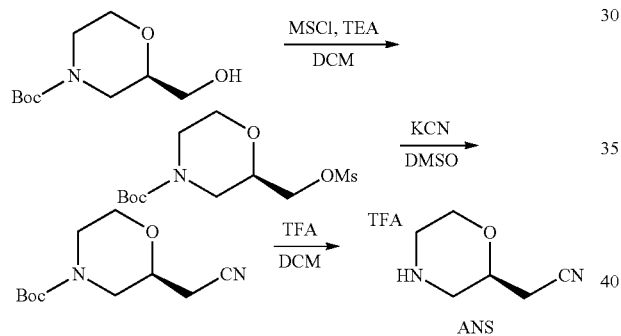

Step 1—Tert-butyl (2R)-2-(methylsulfonyloxymethyl)morpholine-4-carboxylate

To a solution of tert-butyl (2R)-2-(hydroxymethyl)morpholine-4-carboxylate (10.0 g, 46.0 mmol, CAS #135065-71-3) and TEA (9.32 g, 92.0 mmol) in DCM (100 mL) was added MsCl (6.36 g, 55.5 mmol) at 0° C. The reaction mixture was stirred at 25° C. for 2 hours. On completion, the reaction mixture was poured into sat.NaHCO$_3$ (50 mL) and extracted with EA (3×300 mL). The combined organic layers were washed with brine (300 mL), dried with anhydrous Na$_2$SO$_4$, filtered and concentrated in vacuo to give the title compound (13.5 g, 99% yield) as colorless oil, $^1$H NMR (400 MHz, CDCl$_3$) δ 4.23 (d, J=4.8 Hz, 2H), 4.06-3.77 (m, 3H), 3.74-3.64 (m, 1H), 3.59-3.49 (m, 1H), 3.06 (s, 3H), 3.01-2.88 (m, 1H), 2.81-2.67 (m, 1H), 1.49-1.42 (m, 9H).

Step 2—Tert-butyl (2S)-2-(cyanomethyl)morpholine-4-carboxylate

To a solution of tert-butyl (2R)-2-(methylsulfonyloxymethyl)morpholine-4-carboxylate (13.0 g, 44.0 mmol) and KI (10.9 g, 66.0 mmol) in DMSO (200 mL) was added KCN (3.15 g, 48.4 mmol, 2.07 mL). The reaction mixture was stirred at 80° C. for 3 hours. The reaction mixture was stirred at 100° C. for 4 hours. On completion, the reaction mixture was poured into sat.NaHCO$_3$ (100 mL) and extracted with EA (3×500 mL). The combined organic layers were washed with brine (50 mL), dried with anhydrous Na$_2$SO$_4$, filtered and concentrated in vacuo. The residue was purified by silica column chromatography (PE/EA=10/1 to 6/1) to give the title compound (8.00 g, 80% yield) as a white solid. $^1$H NMR (400 MHz, CDCl$_3$) δ 4.10-3.78 (m, 3H), 3.72-3.62 (m, 1H), 3.60-3.50 (m, 1H), 2.97 (t, J=11.2 Hz, 1H), 2.84-2.65 (s, 1H), 2.62-2.50 (m, 2H), 1.47 (s, 9H).

Step 3—2-[(2S)-Morpholin-2-yl]acetonitrile

To a solution of tert-butyl (2S)-2-(cyanomethyl)morpholine-4-carboxylate (4.50 g, 19.8 mmol) in DCM (10 mL) was added TFA (138 g, 1.22 mol). The reaction mixture was stirred at 25° C. for 1 hour. On completion, the reaction mixture was concentrated in vacuo to give the title compound (4.70 g, 98% yield) as colorless oil. $^1$H NMR (400 MHz, DMSO-$d_6$) δ 9.29-8.83 (m, 2H), 4.05-3.88 (m, 2H), 3.77-3.63 (m, 1H), 3.31-3.15 (m, 2H), 3.03-2.76 (m, 3H), 2.41-2.18 (m, 1H).

2-(2-Morpholino-4-pyridyl)oxazole-4-carboxylic acid (Intermediate APC)

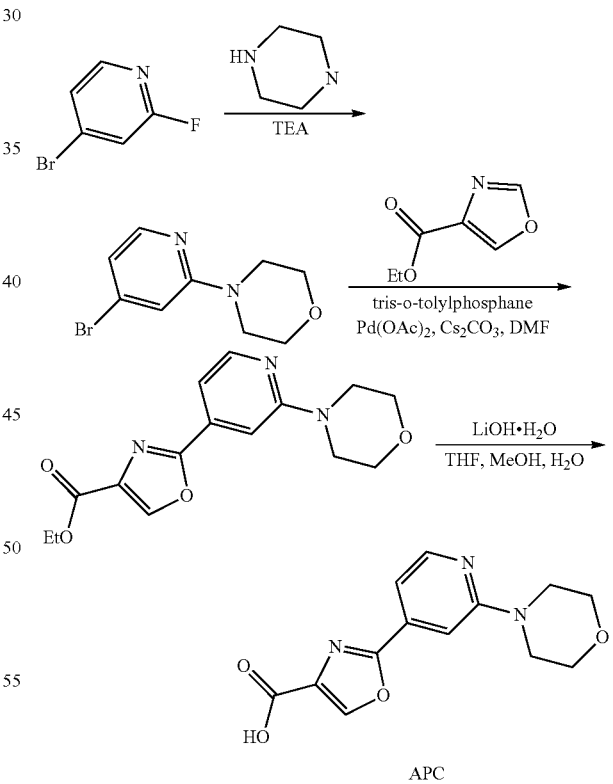

Step 1—4-(4-Dromo-2-pyridyl)morpholine

To a mixture of 4-bromo-2-fluoro-pyridine (5.00 g, 28.4 mmol, CAS #128071-98-7) in morpholine (2.48 g, 28.4 mmol, 2.50 mL, CAS #110-91-8) was added TEA (2.87 g, 28.4 mmol, 3.95 mL) at 25° C. The reaction mixture was stirred at 100° C. for 12 hours. On completion, the reaction mixture was concentrated in vacuo. The residue was purified by column chromatography ((SiO$_2$, PE:EA=30:1 to 10:1) to give the title compound (3.20 g, 46% yield) as white solid. $^1$H NMR (400 MHz, DMSO-d$_6$) δ 8.00 (d, J=5.2 Hz, 1H), 7.05 (d, J=1.2 Hz, 1H), 6.90-6.83 (m, 1H), 3.68-3.64 (m, 4H), 3.49-3.43 (m, 4H).

Step 2—Ethyl 2-(2-morpholino-4-pyridyl)oxazole-4-carboxylate

To a mixture of 4-(4-bromo-2-pyridyl)morpholine (3.00 g, 12.3 mmol) and ethyl oxazole-4-carboxylate (1.74 g, 12.3 mmol, CAS #170487-38-4) in DMF (50 mL) was added Pd(OAc)$_2$ (277 mg, 1.23 mmol), Cs$_2$CO$_3$ (12.0 g, 37.0 mmol) and tris-o-tolylphosphane (751 mg, 2.47 mmol). The reaction mixture was stirred at 70° C. for 12 hours. On completion, the reaction mixture was filtered and the filtrate was concentrated in vacuo. The residue was purified by column chromatography (SiO$_2$, PE:EA=10:1 to 5:1) to give the title compound (2.60 g, 69% yield) as white solid. $^1$H NMR (400 MHz, DMSO-d$_6$) δ 8.99 (s, 1H), 8.28 (d, J=5.2 Hz, 1H), 7.23 (s, 1H), 7.19-7.14 (m, 1H), 4.36-4.26 (m, 2H), 3.74-3.66 (m, 4H), 3.55-3.47 (m, 4H), 1.30 (t, J=7.2 Hz, 3H).

Step 3—2-(2-Morpholino-4-pyridyl)oxazole-4-carboxylic acid

To a mixture of ethyl 2-(2-morpholino-4-pyridyl)oxazole-4-carboxylate (2.00 g, 6.59 mmol) in THF (20 mL), H$_2$O (5 mL) and MeOH (5 mL) was added LiOH·H$_2$O (1.38 g, 32.9 mmol). The reaction mixture was stirred at 25° C. for 0.5 hour. On completion, the reaction mixture was acidified with HCl (1 N) until the pH=5-6, where a large amount of solid was precipitated from the solution. The mixture was filtered and the filter cake was collected and concentrated in vacuo to give the title compound (1.80 g, 99% yield) as yellow solid. $^1$H NMR (400 MHz, DMSO-d$_6$) δ 8.56 (s, 1H), 8.27 (d, J=5.2 Hz, 1H), 7.29 (s, 1H), 7.18-7.13 (m, 1H), 3.69-3.66 (m, 4H), 3.51-3.46 (m, 4H).

N-[3-(difluoromethyl)-1-(4-formylcyclohexyl)pyrazol-4-yl]-2-(2-morpholino-4-pyridyl) oxazole-4-carboxamide (Intermediate APD)

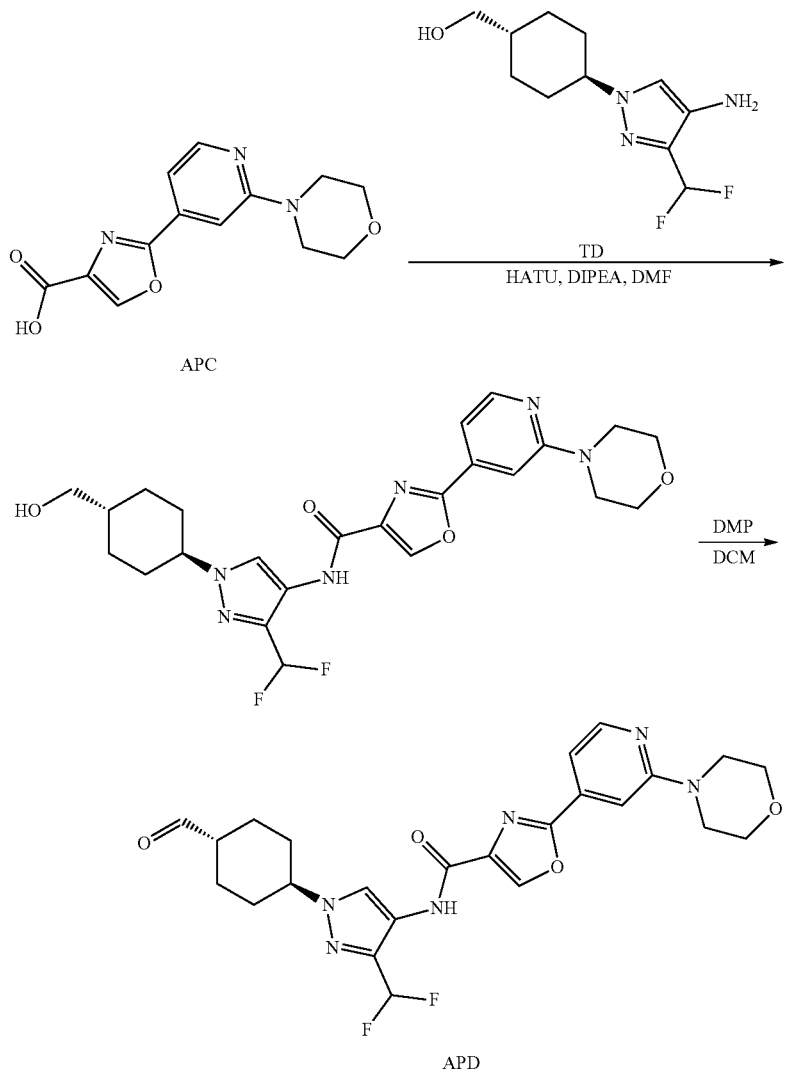

Step 1—N-[3-(difluoromethyl)-1-[4-(hydroxymethyl)cyclohexyl]pyrazol-4-yl]-2-(2-morpholino-4-pyridyl)oxazole-4-carboxamide To a mixture of [4-[4-amino-3-(difluoromethyl)pyrazol-1-yl]cyclohexyl]methanol (445 mg, 1.82 mmol, Intermediate TD), DIPEA (939 mg, 7.27 mmol, 1.27 mL) in DMF (3 mL) was added 2-(2-morpholino-4-pyridyl)oxazole-4-carboxylic acid (500 mg, 1.82 mmol, Intermediate APC) and HATU (828 mg, 2.18 mmol). The reaction mixture was stirred at 25° C. for 0.5 hour. On completion, the reaction mixture was quenched with water (0.05 mL) and concentrated in vacuo to give a residue. The residue was purified by reverse phase (0.1% FA condition) to give the title compound (420 mg, 46% yield) as white solid. $^1$H NMR (400 MHz, DMSO-$d_6$) δ 9.84 (s, 1H), 8.74 (s, 1H), 8.27 (d, J=5.2 Hz, 1H), 8.04 (s, 1H), 7.29 (s, 1H), 7.24-7.21 (m, 1H), 7.18-6.88 (m, 1H), 4.92-4.74 (m, 1H), 4.14 (s, 1H), 3.71-3.67 (m, 4H), 3.52-3.44 (m, 4H), 3.25 (d, J=6.4 Hz, 2H), 2.01 (d, J=10.0 Hz, 2H), 1.82 (d, J=12.0 Hz, 2H), 1.73-1.61 (m, 2H), 1.49-1.34 (m, 1H), 1.12-0.98 (m, 2H); LC-MS (ESI$^+$) m/z 503.3 (M+H)$^+$.

Step 2—N-[3-(difluoromethyl)-1-(4-formylcyclohexyl)pyrazol-4-yl]-2-(2-morpholino-4-pyridyl) oxazole-4-carboxamide To a mixture of N-[3-(difluoromethyl)-1-[4-(hydroxymethyl)cyclohexyl]pyrazol-4-yl]-2-(2-morpholino-4-pyridyl) oxazole-4-carboxamide (100 mg, 199 umol) in DCM (3 mL) was added DMP (109 mg, 258 umol, 80.0 uL). The reaction mixture was stirred at 25° C. for 2 hours. On completion, the reaction mixture was quenched by saturated Na$_2$S$_2$O$_3$ (8 mL) and saturated NaHCO$_3$ (8 mL) at 25° C., and then stirred for 30 minutes. The mixture was extracted with DCM (2×20 mL), the combined organic layers were dried over Na$_2$SO$_4$, filtered and the filtrate was concentrated in vacuo to give the title compound (99.0 mg, 99% yield) as brown solid. $^1$H NMR (400 MHz, DMSO-$d_6$) δ 9.82 (s, 1H), 9.62 (s, 1H), 8.95 (s, 1H), 8.34 (d, J=5.2 Hz, 1H), 8.16 (s, 1H), 7.33 (s, 1H), 7.30-7.01 (m, 2H), 4.32-4.16 (m, 1H), 3.76-3.69 (m, 4H), 3.58-3.50 (m, 4H), 2.44-2.34 (m, 1H), 2.14-2.04 (m, 4H), 1.89-1.77 (m, 2H), 1.47-1.32 (m, 2H); LC-MS (ESI$^+$) m/z 501.3 (M+H)$^+$.

3-Bromo-4-nitro-1H-pyrazole (Intermediate APE)

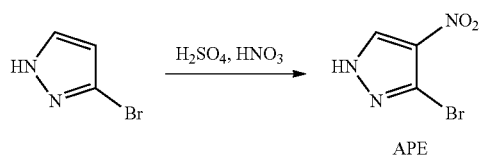 [SMILES: Brc1cc[nH]n1 ; O=[N+]([O-])c1c[nH]nc1Br]

APE

To a mixture of 3-bromo-1H-pyrazole (5.60 g, 38.1 mmol, CAS #14521-80-3) in H$_2$SO$_4$ (10 mL) was added HNO$_3$ (2.40 g, 38.1 mmol) dropwise at 15° C. The reaction mixture was stirred at 50° C. for 2 hours. On completion, the reaction mixture was poured into saturated NaHCO$_3$ under ice-cooling bath and then extracted with EA (2×400 mL). The combined organic layers were dried over Na$_2$SO$_4$, filtered and concentrated in vacuo to give the title compound (7.07 g, 96% yield) as yellow solid. $^1$H NMR (400 MHz, DMSO-$d_6$) δ 8.89 (s, 1H).

Methyl 4-(4-amino-3-morpholino-pyrazol-1-yl)cyclohexanecarboxylate (Intermediate APF)

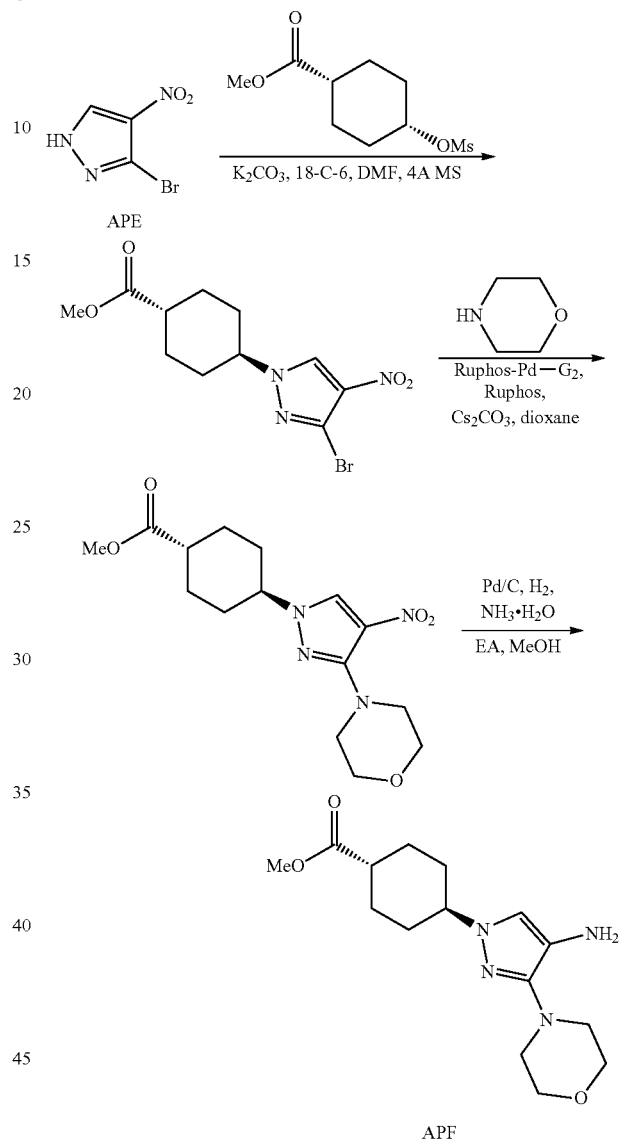

APF

Step 1—Methyl 4-(3-bromo-4-nitro-pyrazol-1-yl)cyclohexanecarboxylate

A mixture of 3-bromo-4-nitro-1H-pyrazole (4.00 g, 20.8 mmol, Intermediate APE), methyl 4-methylsulfonyloxycyclohexanecarboxylate (9.85 g, 41.6 mmol, synthesized via Step 1 of Intermediate QS), K$_2$CO$_3$ (8.64 g, 62.5 mmol), 18-crown-6 (550 mg, 2.08 mmol) and 4 Å molecular sieve (400 mg) in DMF (100 mL) was stirred at 100° C. for 16 hours. Then another batch methyl 4-methylsulfonyloxycyclohexanecarboxylate (4.92 g, 20.8 mmol) and K$_2$CO$_3$ (2.88 g, 20.8 mmol) were supplied and the reaction mixture was stirred at 100° C. for another 16 hours. On completion, the reaction mixture was quenched with saturated NH$_4$Cl (300 mL) and extracted with EA (2×400 mL). The combined organic layers were washed with brine (2×300 mL). The organic layer was dried over Na$_2$SO$_4$, filtered and concentrated in vacuo to give the title compound (2.90 g, 41% yield) as yellow solid. LC-MS (ESI$^+$) m/z 332.0, 334.0 (M+H)$^+$. $^1$H NMR (400 MHz, DMSO-d$_6$) δ 8.20 (s, 1H), 4.15-4.08 (m, 1H), 3.73-3.66 (m, 3H), 2.40-2.26 (s, 1H), 2.26-2.29 (s, 4H), 2.23-2.20 (m, 1H), 1.83-1.78 (m, 2H), 1.66-1.60 (s, 2H).

Step 2—Methyl 4-(3-morpholino-4-nitro-pyrazol-1-yl)cyclohexanecarboxylate

A mixture of methyl 4-(3-bromo-4-nitro-pyrazol-1-yl)cyclohexanecarboxylate (1.90 g, 5.72 mmol), morpholine (598 mg, 6.86 mmol, CAS #110-91-8), RuPhos (533 mg, 1.14 mmol), Cs$_2$CO$_3$ (3.73 g, 11.4 mmol) and [2-(2-aminophenyl)phenyl]-chloro-palladium; dicyclohexyl-[2-(2,6-diisopropoxyphenyl) phenyl]phosphane (444 mg, 572 umol) in dioxane (50 mL) was stirred at 100° C. for 16 hours. On completion, the mixture was diluted with water (200 mL) and extracted with EA (2×200 mL). The combined organic layers were dried over Na$_2$SO$_4$, filtered and concentrated in vacuo. The residue was purified by prep-TLC (PE:EA=3:1) to give the title compound (1.20 g, 62% yield) as orange solid. LC-MS (ESI$^+$) m/z 339.1 (M+H)$^+$.

Step 3—Methyl 4-(4-amino-3-morpholino-pyrazol-1-yl)cyclohexanecarboxylate

A mixture of methyl 4-(3-morpholino-4-nitro-pyrazol-1-yl)cyclohexanecarboxylate (1.00 g, 2.96 mmol), NH$_3$.H$_2$O (455 mg, 3.64 mmol 28% solution) and Pd/C (100 mg, 10 wt %) in a mixed solvent of EA (20 mL) and MeOH (20 mL) was stirred at 25° C. for 13 hours under H$_2$ (15 Psi). On completion, the reaction mixture was filtered. The filtrate was concentrated in vacuo to give the title compound (820 mg, 89% yield) as brown gum. $^1$H NMR (400 MHz, DMSO-d$_6$) δ 6.96 (s, 1H), 3.82-3.73 (m, 1H), 3.69-3.64 (m, 4H), 3.60 (s, 3H), 3.44-3.34 (m, 2H), 2.99-2.92 (m, 4H), 2.37-2.28 (m, 1H), 2.03-1.92 (m, 4H), 1.65-1.44 (m, 4H).

Tert-butyl 6-(aminomethyl)-2-azaspiro[3.3]heptane-2-carboxylate (Intermediate APA)

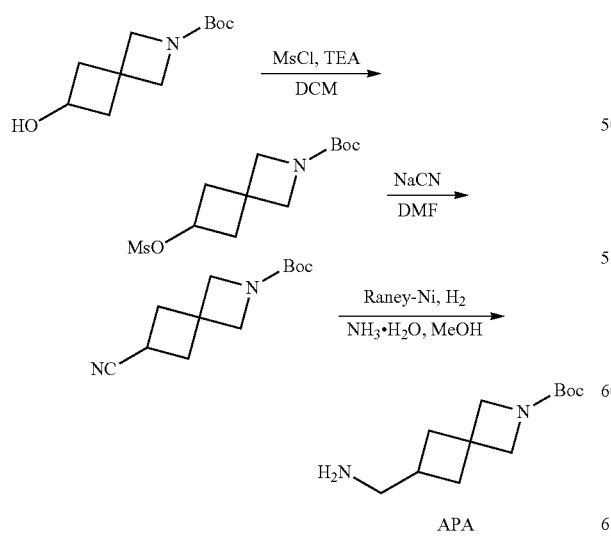

Step 1—Tert-butyl 6-((methylsulfonyl)oxy)-2-azaspiro[3.3]heptane-2-carboxylate

To a solution of tert-butyl 6-hydroxy-2-azaspiro[3.3]heptane-2-carboxylate (2.5 g, 11.7 mmol, CAS #1147557-97-8) in the DCM (20 mL) was added MsCl (2.01 g, 17.6 mmol) and TEA (3.56 g, 35.2 mmol, 4.89 mL) at 0° C. The resulting mixture was stirred at 25° C. for 2 hours. On completion, the reaction mixture was quenched with water (20 mL) and extracted with EA (100 mL). The organic layer was dried over Na$_2$SO$_4$, filtered and concentrated in vacuo to give the title compound (3.2 g, 94% yield) as yellow solid. $^1$H NMR (400 MHz, CDCl$_3$) δ 4.89 (q, J=7.2 Hz, 1H), 3.92 (d, J=1.8 Hz, 4H), 2.98 (s, 3H), 2.72-2.65 (m, 2H), 2.51-2.42 (m, 2H), 1.42 (s, 9H).

Step 2—Tert-butyl 6-cyano-2-azaspiro[3.3]heptane-2-carboxylate

To a solution of tert-butyl 6-methylsulfonyloxy-2-azaspiro[3.3]heptane-2-carboxylate (3.2 g, 11.0 mmol) in the DMF (30 mL) was added NaCN (2.15 g, 43.9 mmol). The mixture was stirred at 100° C. for 18 hours. On completion, the reaction mixture was poured into water (200 mL) and extracted with EA (2×200 mL). The organic layer was washed with brine (200 mL) and dried over Na$_2$SO$_4$, filtered and concentrated in vacuo. The residue was purified by column chromatography (SiO$_2$, PE:EA=10:1 to 5:1) to give the title compound (1.6 g, 66% yield) as white solid. $^1$H NMR (400 MHz, CDCl$_3$) δ 3.94 (d, J=4.4 Hz, 4H), 3.00 (q, J=8.3 Hz, 1H), 2.67-2.52 (m, 4H), 1.43 (s, 9H).

Step 3—Tert-butyl 6-(aminomethyl)-2-azaspiro[3.3]heptane-2-carboxylate

To a solution of tert-butyl 6-cyano-2-azaspiro[3.3]heptane-2-carboxylate (0.8 g, 3.60 mmol) in the MeOH (5.0 mL) was added Raney-Ni (200 mg) and NH$_3$H$_2$O (1.01 g, 7.20 mmol). The reaction mixture was stirred at 25° C. for 4 hours under H$_2$ (50 Psi). On completion, the reaction mixture was filtered and concentrated in vacuo to give the title compound (800 mg, 98% yield) as colorless oil. $^1$H NMR (400 MHz, CDCl$_3$) δ 3.92 (s, 2H), 3.81 (s, 2H), 2.65 (d, J=7.0 Hz, 2H), 2.30-2.22 (m, 2H), 2.22-2.11 (m, 1H), 1.85-1.77 (m, 2H), 1.43 (s, 9H).

4-((2-Azaspiro[3.3]heptan-6-ylmethyl)amino)-2-(2,6-dioxopiperidin-3-yl)isoindoline-1,3-dione (Intermediate APB)

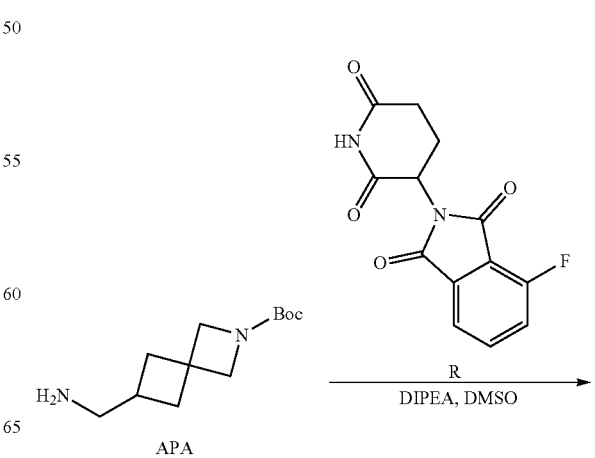

1953

-continued

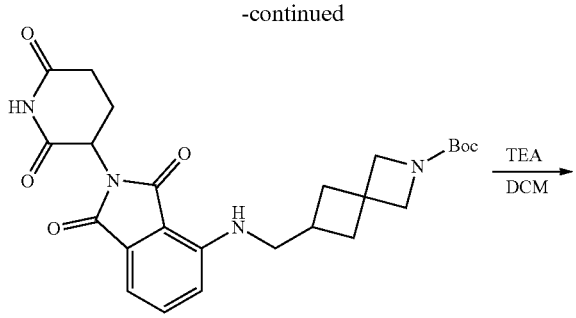

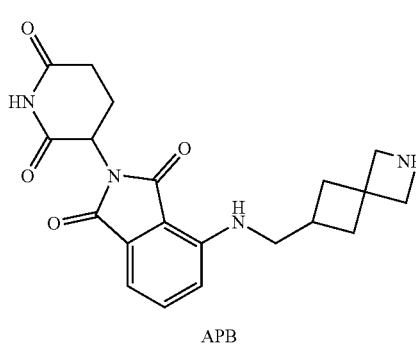

APB

Step 1—Tert-butyl 6-(((2-(2,6-dioxopiperidin-3-yl)-1,3-dioxoisoindolin-4-yl)amino)methyl)-2-azaspiro[3.3]heptane-2-carboxylate To a solution of tert-butyl 6-(aminomethyl)-2-azaspiro[3.3]heptane-2-carboxylate (100 mg, 442 umol, Intermediate APA) and 2-(2,6-dioxo-3-piperidyl)-4-fluoro-isoindoline-1,3-dione (147 mg, 530 umol, Intermediate R) in the DMSO (2 mL) was added DIPEA (171 mg, 1.33 mmol, 231 uL). The mixture was stirred at 130° C. for 1 hour. On completion, the reaction mixture was filtered and the filtrate was concentrated in vacuo to give a residue. The residue was purified by reversed phase (FA condition) to give the title compound (140 mg, 66% yield) as yellow solid. $^1$H NMR (400 MHz, CDCl$_3$) δ 7.90 (br s, 1H), 7.43 (dd, J=7.3, 8.4 Hz, 1H), 7.04 (d, J=7.0 Hz, 1H), 6.79 (d, J=8.5 Hz, 1H), 6.11 (t, J=5.4 Hz, 1H), 4.89-4.80 (m, 1H), 3.88 (s, 2H), 3.78 (s, 2H), 3.22-3.13 (m, 2H), 2.89-2.60 (m, 3H), 2.47-2.36 (m, 1H), 2.33-2.23 (m, 2H), 2.13-2.01 (m, 1H), 1.93-1.83 (m, 2H), 1.36 (s, 9H), 0.84-0.75 (m, 2H). LC-MS (ESI$^+$) m/z 483.3 (M+H)$^+$.

Step 2—4-((2-Azaspiro[3.3]heptan-6-ylmethyl)amino)-2-(2,6-dioxopiperidin-3-yl)isoindoline-1,3-dione To a solution of tert-butyl 6-[[[2-(2,6-dioxo-3-piperidyl)-1,3-dioxo-isoindolin-4-yl]amino]methyl]-2-azaspiro[3.3]heptane-2-carboxylate (70 mg, 145 umol) in the DCM (2 mL) was added TFA (1 mL). The mixture was stirred at 25° C. for 1 hour. On completion, the reaction mixture was concentrated in vacuo to give the title compound (55 mg, 99% yield) as yellow solid. LC-MS (ESI$^+$) m/z 383.2 (M+H)$^+$.

1954

N-[3-(difluoromethyl)-1-(2-piperazin-1-ylpyrimidin-5-yl)pyrazol-4-yl]-5-[(1R,4R)-2-oxa-5-azabicyclo[2.2.1]heptan-5-yl]pyrazolo[1,5-a]pyrimidine-3-carboxamide (Intermediate APH)

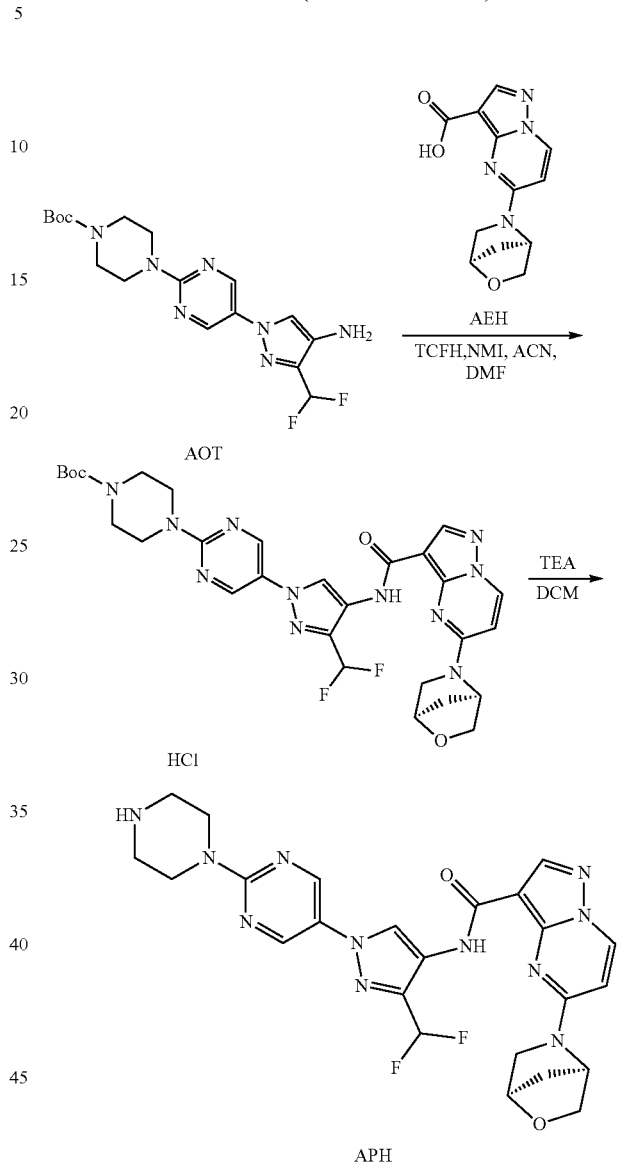

Step 1—Tert-butyl 4-[5-[3-(difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]pyrimidin-2-yl]piperazine-1-carboxylate To a mixture of 5-[(1R,4R)-2-oxa-5-azabicyclo[2.2.1]heptan-5-yl]pyrazolo[1,5-a]pyrimidine-3-carboxylic acid (85.5 mg, 328 umol, Intermediate AEH), 1-methylimidazole (94.4 mg, 1.15 mmol, 91.7 uL) and [chloro(dimethylamino)methylene]-dimethyl-ammonium; hexafluorophosphate (119 mg, 427 umol,) in DMF (0.5 mL) and ACN (1 mL) was added tert-butyl 4-[5-[4-amino-3-(difluoromethyl) pyrazol-1-yl]pyrimidin-2-yl]piperazine-1-carboxylate (130 mg, 328 umol, Intermediate AOT). The reaction mixture was stirred at 60° C. for 24 hours. On completion, the reaction mixture was concentrated in vacuo. The residue was purified by

Step 2—N-[3-(difluoromethyl)-1-(2-piperazin-1-ylpyrimidin-5-yl)pyrazol-4-yl]-5-[(1R,4R)-2-oxa-5-azabicyclo[2.2.1]heptan-5-yl]pyrazolo[1,5-a]pyrimidine-3-carboxamide To a mixture of tert-butyl 4-[5-[3-(difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-yl]pyrimidin-2-yl]piperazine-1-carboxylate (50.0 mg, 78.4 umol) in DCM (1 mL) was added TFA (7.70 g, 67.5 mmol, 5.00 mL). The reaction mixture was stirred at 25° C. for 0.5 hour. On completion, the reaction mixture was concentrated in vacuo to give the title compound (51.0 mg, 99% yield, TFA) as yellow solid. LC-MS (ESI⁺) m/z 538.2 (M+H)⁺.

3-(2-Aminoethoxy)propan-1-ol (Intermediate API)

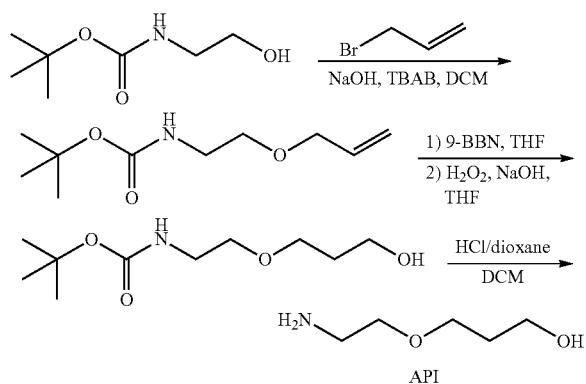

Step 1—Tert-butyl N-(2-allyloxyethyl)carbamate

To a mixture of tert-butyl N-(2-hydroxyethyl)carbamate (5.00 g, 31.0 mmol, 4.81 mL, CAS #26690-80-2) and TBAB (7.00 g, 21.7 mmol) in DCM (60 mL) was added 3-bromoprop-1-ene (4.13 g, 34.1 mmol, CAS #106-95-6) and NaOH (10 M, 31 mL). The reaction mixture was stirred at 25° C. for 12 hours. On completion, the reaction mixture was diluted with water (50 mL) and extracted with DCM (2×100 mL). The combined organic layers was dried over Na₂SO₄, filtered and concentrated in vacuo to give a residue. The residue was purified by column chromatography to give the title compound (5.40 g, 86% yield) as colorless oil. ¹H NMR (400 MHz, CDCl₃) δ 5.97-5.82 (m, 1H), 5.32-5.25 (m, 1H), 5.22-5.17 (m, 1H), 4.91 (s, 1H), 4.03-3.94 (m, 2H), 3.55-3.42 (m, 2H), 3.38-3.25 (m, 2H), 1.45 (s, 9H).

Step 2—Tert-butyl N-[2-(3-hydroxypropoxy)ethyl]carbamate

To a mixture of tert-butyl N-(2-allyloxyethyl)carbamate (1.00 g, 4.97 mmol) in THF (15 mL) was added 9-BBN (0.5 M, 14.9 mL) dropwise at 0° C. for 1 hour. After the reaction mixture was stirred at 65° C. for 2 hours. Then NaOH (3 M, 2.00 mL) and H₂O₂ (1.58 g, 13.9 mmol, 1.34 mL, 30% solution) were added to the mixture at 0° C., and the mixture was stirred at 0° C. for 1 hour. The reaction mixture was quenched with Na₂SO₄ (5 mL), diluted with water (30 mL) and extracted with EA (2×30 mL). The combined organic layers were dried over Na₂SO₄, filtered and concentrated in vacuo to give a residue. The residue was purified by column chromatography to give the title compound (270 mg, 24% yield) as colorless oil. ¹H NMR (400 MHz, CDCl₃) δ 4.90 (s, 1H), 4.80-4.65 (m, 1H), 3.76 (t, J=5.6 Hz, 2H), 3.63 (t, J=5.6 Hz, 2H), 3.53-3.48 (m, 2H), 3.35-3.23 (m, 2H), 1.85-1.80 (m, 2H), 1.45 (s, 9H).

Step 3—3-(2-Aminoethoxy)propan-1-ol

To a mixture of tert-butyl N-[2-(3-hydroxypropoxy)ethyl] carbamate (265 mg, 1.21 mmol) in DCM (3 mL) was added HCl/dioxane (4 M, 2 mL). The reaction mixture was stirred at 25° C. for 0.5 hour. On completion, the reaction mixture was concentrated in vacuo to give the compound (188 mg, 99% yield, HCl) as colorless oil. ¹H NMR (400 MHz, DMSO-d₆) δ 8.08 (s, 2H), 3.57-3.54 (m, 3H), 3.49-3.45 (m, 4H), 2.98-2.87 (m, 2H), 1.71-1.61 (m, 2H).

3-[2-[[2-(2,6-Dioxo-3-piperidyl)-1,3-dioxo-isoindolin-4-yl]amino]ethoxy]propanal (Intermediate APJ)

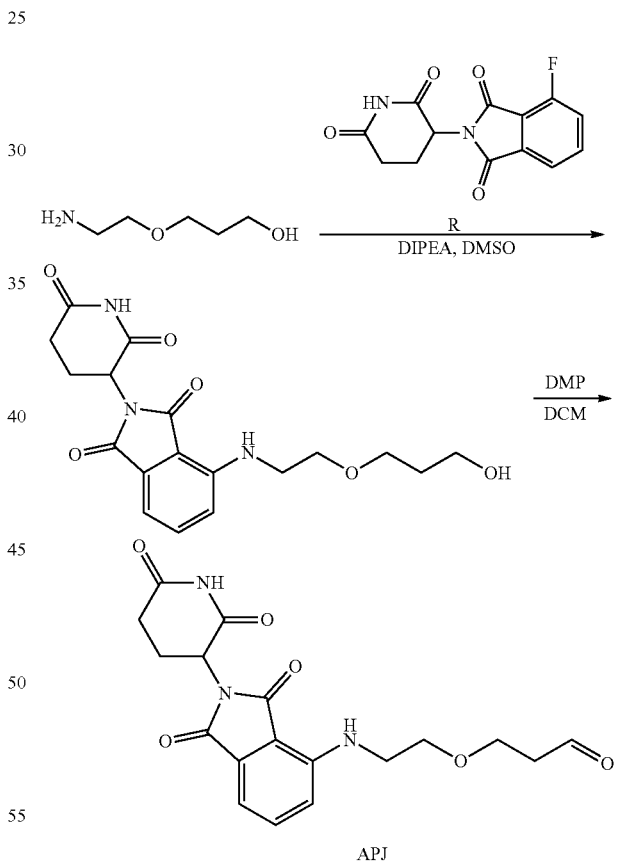

Step 1—2-(2,6-Dioxo-3-piperidyl)-4-[2-(3-hydroxypropoxy)ethylamino]isoindoline-1,3-dione To a mixture of 3-(2-aminoethoxy)propan-1-ol (157 mg, 1.01 mmol, HCl, Intermediate API) in DMSO (3 mL) was added DIPEA (393 mg, 3.04 mmol, 529 uL) and 2-(2,6-dioxo-3-piperidyl)-4-fluoro-isoindoline-1,3-dione (280 mg, 1.01 mmol, Intermediate R). The reaction mixture was stirred at 130° C. for 2 hour. On completion, the reaction mixture was concentrated in vacuo. The residue was purified by reverse phase (0.1% FA condition) to give the title compound (200 mg, 52% yield) as yellow solid. $^1$H NMR (400 MHz, DMSO-$d_6$) δ 11.09 (s, 1H), 7.61-7.55 (m, 1H), 7.14 (d, J=8.4 Hz, 1H), 7.04 (d, J=7.0 Hz, 1H), 6.60 (t, J=5.6 Hz, 1H), 5.09-5.03 (m, 1H), 4.39 (t, J=5.2 Hz, 1H), 3.61-3.54 (m, 2H), 3.50-3.43 (m, 6H), 2.94-2.82 (m, 1H), 2.64-2.52 (m, 2H), 2.08-1.98 (m, 1H), 1.70-1.60 (m, 2H); LC-MS (ESI$^+$) m/z 376.2 (M+H)$^+$.

Step 2—3-[2-[[2-(2,6-Dioxo-3-piperidyl)-1,3-dioxo-isoindolin-4-yl]amino] ethoxy]propanal To a mixture of 2-(2,6-dioxo-3-piperidyl)-4-[2-(3-hydroxypropoxy)ethylamino]isoindoline-1,3-dione (60.0 mg, 159 umol) in DCM (2 mL) was added DMP (81.3 mg, 191 umol, 59.3 uL). The reaction mixture was stirred at 25° C. for 12 hours. On completion, the reaction mixture was quenched by saturated Na$_2$S$_2$O$_3$ (8 mL) and saturated NaHCO$_3$ (8 mL) at 25° C., and then stirred for 30 minutes. The mixture was extracted with DCM (2×20 mL). The combined organic layers was dried over Na$_2$SO$_4$, filtered and concentrated in vacuo to give the title compound (59.0 mg, 98% yield) as yellow solid. LC-MS (ESI$^+$) m/z 374.2 (M+H)$^+$.

3-[3-Methyl-2-oxo-4-[3-(4-piperidyloxy)prop-1-ynyl]benzimidazol-1-yl]piperidine-2,6-dione (Intermediate APT)

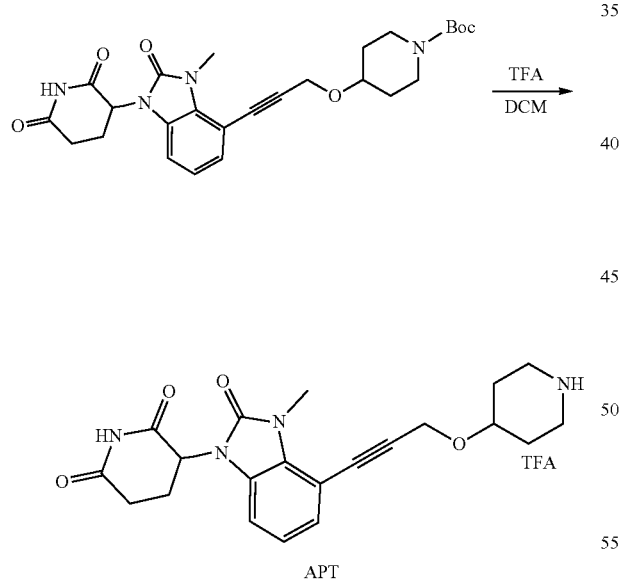

To a mixture of tert-butyl 4-[3-[1-(2,6-dioxo-3-piperidyl)-3-methyl-2-oxo-benzimidazol-4-yl]prop-2-ynoxy]piperidine-1-carboxylate (1.50 g, 3.02 mmol, synthesized via Step 1 of Intermediate TN) in DCM (30 mL) was added TFA (23.1 g, 202 mmol, 15 mL). The reaction mixture was stirred at 20° C. for 1 hr. On completion, the reaction mixture was concentrated in vacuo to give the title compound (1.50 g, 97% yield, TFA salt) as yellow oil. LC-MS (ESI$^+$) m/z 397.2 (M+H)$^+$.

Methyl 4-(4-amino-3-morpholino-pyrazol-1-yl)cyclohexanecarboxylate (Intermediate APF)

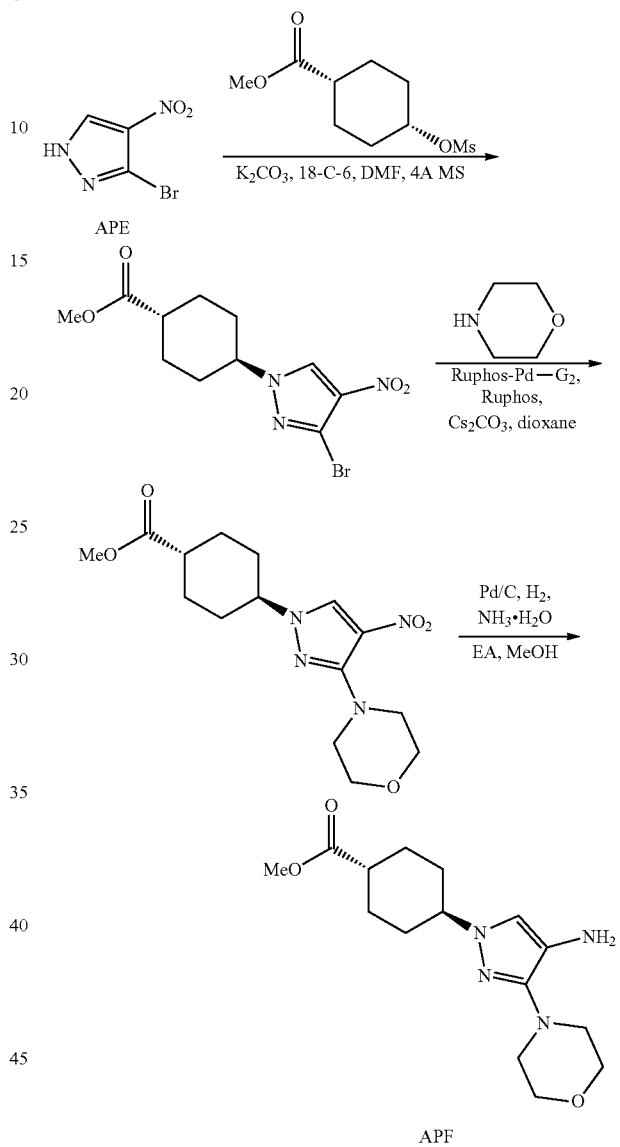

Step 1—Methyl 4-(3-bromo-4-nitro-pyrazol-1-yl) cyclohexanecarboxylate

A mixture of 3-bromo-4-nitro-1H-pyrazole (4.00 g, 20.8 mmol, Intermediate APE), methyl 4-methylsulfonyloxycyclohexanecarboxylate (9.85 g, 41.6 mmol, synthesized via Step 1 of Intermediate QS), K$_2$CO$_3$ (8.64 g, 62.5 mmol), 18-crown-6 (550 mg, 2.08 mmol) and 4 Å molecular sieve (400 mg) in DMF (100 mL) was stirred at 100° C. for 16 hours. Then another batch methyl 4-methylsulfonyloxycyclohexanecarboxylate (4.92 g, 20.8 mmol) and K$_2$CO$_3$ (2.88 g, 20.8 mmol) were supplied and the reaction mixture was stirred at 100° C. for another 16 hours. On completion, the reaction mixture was quenched with saturated NH$_4$Cl (300 mL) and extracted with EA (2×400 mL). The combined organic layers were washed with brine (2×300 mL). The organic layer was dried over Na$_2$SO$_4$, filtered and concentrated in vacuo to give the title compound (2.90 g, 41% yield) as yellow solid. LC-MS (ESI$^+$) m/z 332.0, 334.0 (M+H)$^+$. $^1$H NMR (400 MHz, DMSO-d$_6$) δ 8.20 (s, 1H), 4.15-4.08 (m, 1H), 3.73-3.66 (m, 3H), 2.40-2.26 (s, 1H), 2.26-2.29 (s, 4H), 2.23-2.20 (m, 1H), 1.83-1.78 (m, 2H), 1.66-1.60 (s, 2H).

Step 2—Methyl 4-(3-morpholino-4-nitro-pyrazol-1-yl)cyclohexanecarboxylate

A mixture of methyl 4-(3-bromo-4-nitro-pyrazol-1-yl)cyclohexanecarboxylate (1.90 g, 5.72 mmol), morpholine (598 mg, 6.86 mmol, CAS #110-91-8), RuPhos (533 mg, 1.14 mmol), Cs$_2$CO$_3$ (3.73 g, 11.4 mmol) and [2-(2-aminophenyl)phenyl]-chloro-palladium; dicyclohexyl-[2-(2,6-diisopropoxyphenyl) phenyl]phosphane (444 mg, 572 umol) in dioxane (50 mL) was stirred at 100° C. for 16 hours. On completion, the mixture was diluted with water (200 mL) and extracted with EA (2×200 mL). The combined organic layers were dried over Na$_2$SO$_4$, filtered and concentrated in vacuo. The residue was purified by prep-TLC (PE:EA=3:1) to give the title compound (1.20 g, 62% yield) as orange solid. LC-MS (ESI$^+$) m/z 339.1 (M+H)$^+$.

Step 3—Methyl 4-(4-amino-3-morpholino-pyrazol-1-yl)cyclohexanecarboxylate

A mixture of methyl 4-(3-morpholino-4-nitro-pyrazol-1-yl)cyclohexanecarboxylate (1.00 g, 2.96 mmol), NH$_3$.H$_2$O (455 mg, 3.64 mmol 28% solution) and Pd/C (100 mg, 10 wt %) in a mixed solvent of EA (20 mL) and MeOH (20 mL) was stirred at 25° C. for 13 hours under H$_2$ (15 Psi). On completion, the reaction mixture was filtered. The filtrate was concentrated in vacuo to give the title compound (820 mg, 89% yield) as brown gum. $^1$H NMR (400 MHz, DMSO-d$_6$) δ 6.96 (s, 1H), 3.82-3.73 (m, 1H), 3.69-3.64 (m, 4H), 3.60 (s, 3H), 3.44-3.34 (m, 2H), 2.99-2.92 (m, 4H), 2.37-2.28 (m, 1H), 2.03-1.92 (m, 4H), 1.65-1.44 (m, 4H).

[4-(4-Amino-3-morpholino-pyrazol-1-yl)cyclohexyl]methanol (Intermediate APM)

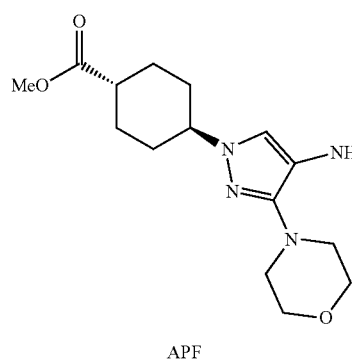

APF

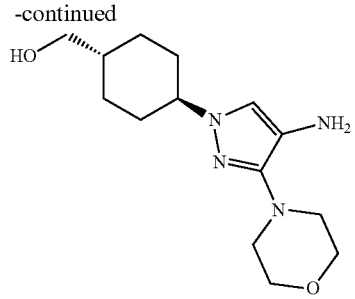

APM

To a mixture of methyl 4-(4-amino-3-morpholino-pyrazol-1-yl)cyclohexanecarboxylate (300 mg, 972 umol, Intermediate APF) in a mixed solvent of THF (8 mL) and MeOH (1 mL) was added LiBH$_4$ (63.5 mg, 2.92 mmol) at 25° C. The reaction mixture was warmed to 25° C. and stirred for 0.5 hour. Then the reaction mixture was stirred at 50° C. for 1 hour. On completion, the reaction mixture was quenched by saturated NH$_4$Cl (2 mL), and concentrated in vacuo. The residue was washed with DCM (3×40 mL). The organic phase was concentrated in vacuo to give the title compound (240 mg, 87% yield) as brown gum. $^1$H NMR (400 MHz, DMSO-d$_6$) δ 6.97 (s, 1H), 4.44-4.48 (m, 1H), 3.76-3.69 (m, 1H), 3.68-3.65 (m, 4H), 3.60-3.38 (m, 2H), 3.25-3.19 (m, 2H), 2.98-2.93 (m, 4H), 1.96-1.90 (m, 2H), 1.85-1.76 (m, 2H), 1.55-1.45 (m, 2H), 1.38-1.32 (m, 1H), 1.07-0.96 (m, 2H).

N-[1-(4-formylcyclohexyl)-3-morpholino-pyrazol-4-yl]pyrazolo[1,5-a]pyrimidine-3-carboxamide (Intermediate APN)

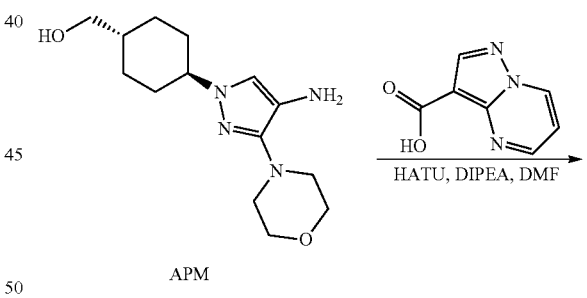

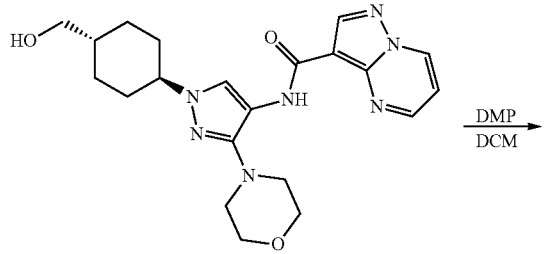

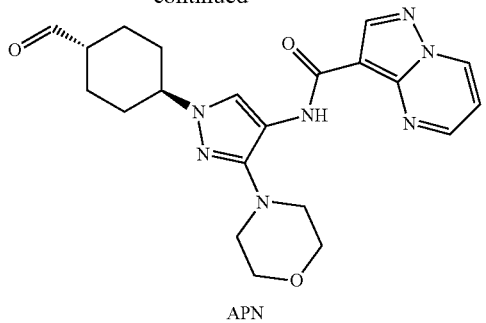

APN

Step 1—N-[1-[4-(hydroxymethyl)cyclohexyl]-3-morpholino-pyrazol-4-yl]pyrazolo[1,5-a]pyrimidine-3-carboxamide To a mixture of pyrazolo[1,5-a]pyrimidine-3-carboxylic acid (110 mg, 674 umol, CAS #25940-35-6), HATU (333 mg, 876 umol) and DIPEA (261 mg, 2.02 mmol) in DMF (10 mL) was added [4-(4-amino-3-morpholino-pyrazol-1-yl)cyclohexyl]methanol (207 mg, 741 umol, Intermediate APM). The reaction mixture was stirred at 25° C. for 1 hour. On completion, the reaction mixture was poured into water (50 mL). The mixture was acidified with saturated critic acid aqueous until the pH=7 and extracted with EA (4×30 mL). The organic phase was concentrated in vacuo to give the title compound (250 mg, 87% yield) as brown gum. $^1$H NMR (400 MHz, DMSO-$d_6$) δ 9.65 (s, 1H), 9.20 (d, J=7.2 Hz, 1H), 8.83 (d, J=3.6 Hz, 1H), 8.61 (s, 1H), 7.95 (s, 1H), 7.35-7.21 (m, 1H), 3.71-3.64 (m, 1H), 3.60-3.49 (m, 4H), 3.30-3.19 (m, 2H), 3.02-2.95 (m, 4H), 2.02-1.92 (m, 2H), 1.85-1.74 (m, 2H), 1.67-1.55 (m, 2H), 1.43-1.32 (m, 1H), 1.10-0.95 (m, 2H).

Step 2—N-[1-(4-formylcyclohexyl)-3-morpholino-pyrazol-4-yl]pyrazolo[1,5-a]pyrimidine-3-carboxamide To a mixture of N-[1-[4-(hydroxymethyl)cyclohexyl]-3-morpholino-pyrazol-4-yl]pyrazolo[1,5-a] pyrimidine-3-carboxamide (200 mg, 470 umol) in DCM (10 mL) was added DMP (219 mg, 517 umol). The reaction mixture was stirred at 25° C. for 4 hours. On completion, the reaction mixture was quenched by saturated Na$_2$SO$_3$ (10 mL) and washed with saturated NaHCO$_3$ (10 mL). The mixture was extracted with DCM (3×20 mL). The organic phase was dried over anhydrous sodium sulfate and filtered. The filtrate was concentrated in vacuo to give the (200 mg, 40% yield) as brown gum. LC-MS (ESI$^+$) m/z 424.3 (M+H)$^+$.

[5-[4-Amino-3-(difluoromethyl)pyrazol-1-yl]-1,3-dioxan-2-yl]methyl benzoate (Intermediate APS)

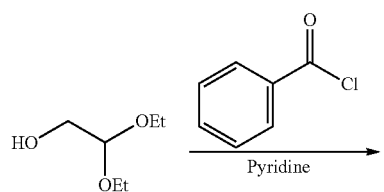

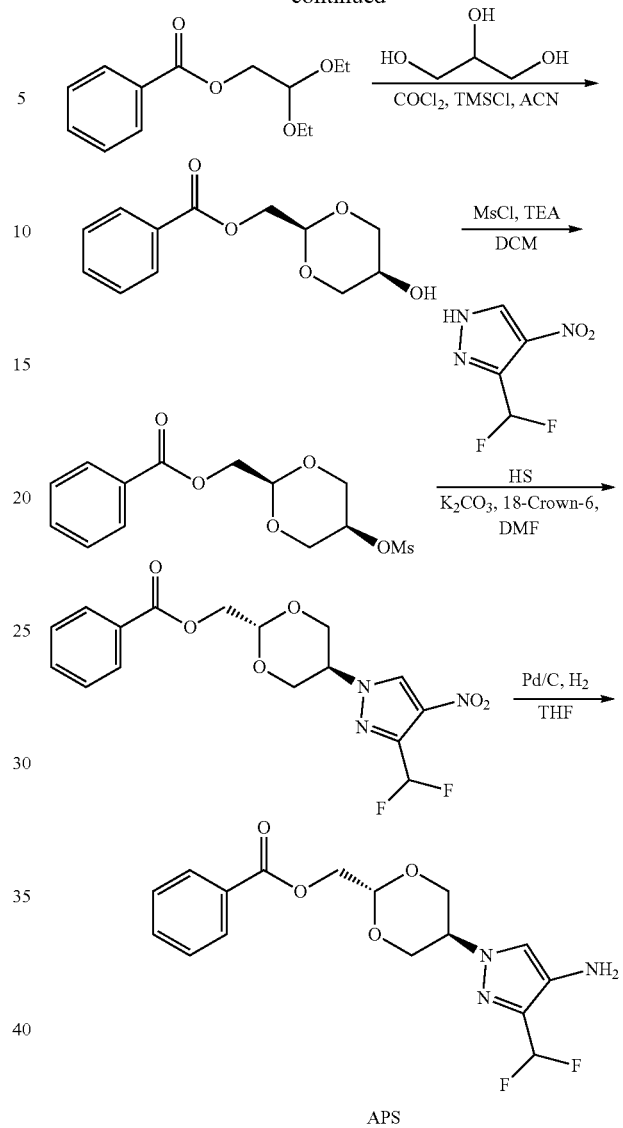

APS

Step 1—2,2-Diethoxyethyl benzoate

To a solution of 2,2-diethoxyethanol (25.0 g, 186 mmol, CAS #621-63-6) in pyridine (50 mL) was added benzoyl chloride (78.6 g, 558 mmol, 64.9 mL) at 0° C. Then the reaction mixture was stirred at 20° C. for 16 hours. On completion, the mixture was quenched with MeOH (200 mL) and water (1000 mL), and then extracted with EA (2×400 mL). The combined organic layer was washed with brine (400 mL), dried over Na$_2$SO$_4$, filtered and the filtrate was concentrated in vacuo to give the title compound (39.0 g, 87% yield) as a colorless oil. $^1$H NMR (400 MHz, CDCl$_3$) δ 8.10-8.04 (m, 2H), 7.61-7.54 (m, 1H), 7.49-7.42 (m, 2H), 4.84 (t, J=5.4 Hz, 1H), 4.35 (d, J=5.4 Hz, 2H), 3.77 (qd, J=7.0, 9.5 Hz, 2H), 3.68-3.57 (m, 2H), 1.27-1.23 (m, 6H).

Step 2—5-Hydroxy-1,3-dioxan-2-yl)methyl benzoate

To a solution of 2,2-diethoxyethyl benzoate (40 g, 167 mmol) and glycerol (29.4 g, 318 mmol, 24 mL) in ACN (150 mL) was added CoCl₂ (11.6 g, 89 mmol) and TMSCl (19.3 g, 178 mmol). The reaction mixture was stirred at 20° C. for 12 hours. On completion, the mixture was concentrated in vacuo to remove ACN, then diluted with water (500 mL), and extracted with EA (2×300 mL). The organic layer was washed with brine (2×300 mL), dried over Na₂SO₄, filtered and the filtrate was concentrated in vacuo to give a residue. The residue was purified by silica gel chromatography (SiO₂, PE:EA=30:1 to 5:1) to give the title compound (6.00 g, 15% yield) as colorless oil. ¹H NMR (400 MHz, CDCl₃) δ 8.11-8.03 (m, 2H), 7.61-7.54 (m, 1H), 7.50-7.41 (m, 2H), 4.97 (t, J=4.6 Hz, 1H), 4.39 (d, J=4.6 Hz, 2H), 4.13-4.06 (m, 2H), 4.00-3.93 (m, 2H), 3.62-3.56 (m, 1H), 3.03 (d, J=11.0 Hz, 1H).

Step 3—5-((Methylsulfonyl)oxy)-1,3-dioxan-2-yl) methyl benzoate

To a solution of (5-hydroxy-1,3-dioxan-2-yl)methyl benzoate (5.00 g, 20.9 mmol) in DCM (100 mL) was added TEA (6.37 g, 62.9 mmol, 8.76 mL) and MsCl (3.61 g, 31.4 mmol, 2.44 mL) at 0° C. The reaction mixture was stirred at 20° C. for 3 hours. On completion, the reaction mixture was quenched with water (10 mL). The organic layer was separated and then washed with brine (50 mL), dried over Na₂SO₄, filtered and concentrated in vacuo to give the title compound (6.64 g, 99% yield). ¹H NMR (400 MHz, CDCl₃) δ 8.13-8.00 (m, 2H), 7.64-7.53 (m, 1H), 7.50-7.40 (m, 2H), 4.99 (t, J=4.6 Hz, 1H), 4.64 (s, 1H), 4.41 (d, J=4.6 Hz, 2H), 4.39-4.32 (m, 2H), 4.04 (dd, J=1.2, 13.4 Hz, 2H), 3.15 (s, 3H).

Step 4—[5-[3-(Difluoromethyl)-4-nitro-pyrazol-1-yl]-1,3-dioxan-2-yl]methyl benzoate To a solution of (5-methylsulfonyloxy-1,3-dioxan-2-yl) methyl benzoate (6.60 g, 20.8 mmol) and 3-(difluoromethyl)-4-nitro-1H-pyrazole (4.08 g, 25.0 mmol, Intermediate HS) in DMF (140 mL) was added K₂CO₃ (8.65 g, 62.5 mmol) and 18-crown-6 (275 mg, 1.04 mmol). The mixture was stirred at 100° C. for 36 hours. On completion, the reaction mixture was diluted with EA (500 mL) and washed with water (3×300 mL). The organic layer was dried over Na₂SO₄, filtered and concentrated in vacuo to give a residue. The residue was purified by column chromatography (SiO₂, Petroleum ether/Ethyl acetate=20/1 to 5/1) to afford the title compound (1.36 g, 16% yield) as white solid. ¹H NMR (400 MHz, CDCl₃) δ 8.27 (s, 1H), 8.07 (dd, J=1.2, 8.3 Hz, 2H), 7.62-7.57 (m, 1H), 7.50-7.43 (m, 2H), 7.22 (s, 1H), 7.08 (s, 1H), 6.95 (s, 1H), 5.03 (t, J=4.6 Hz, 1H), 4.94 (tt, J=5.2, 10.3 Hz, 1H), 4.84 (t, J=4.6 Hz, 1H), 4.61 (dq, J=5.0, 10.4 Hz, 1H), 4.45 (d, J=4.6 Hz, 3H), 4.42 (d, J=4.8 Hz, 1H), 4.38 (d, J=4.6 Hz, 1H), 4.30 (dd, J=5.4, 11.3 Hz, 1H), 4.22-4.15 (m, 2H), 3.57-3.48 (m, 1H), 2.05 (s, 1H), 1.26 (t, J=7.2 Hz, 1H).

Step 5—[5-[4-Amino-3-(difluoromethyl)pyrazol-1-yl]-1,3-dioxan-2-yl]methyl benzoate To a solution of [5-[3-(difluoromethyl)-4-nitro-pyrazol-1l-yl]-1,3-dioxan-2-yl]methyl benzoate (300 mg, 782 umol) in MeOH (4 mL) was added Pd/C (100 mg, 10 wt %) under N₂. The mixture was purged with H₂ three times and stirred at 20° C. for 12 hours under H₂ (15 Psi). On completion, the mixture was filtered to remove Pd/C and concentrated in vacuo to give the title compound (250 mg, 90% yield) as red solid. LC-MS (ESI⁺) m/z 354.0 (M+H)⁺.

[5-[3-(Difluoromethyl)-4-[[5-[(1R,4R)-2-oxa-5-azabicyclo[2.2.1]heptan-5-yl]pyrazolo[1,5-a] pyrimidine-3-carbonyl] amino]pyrazol-1-yl]-1,3-dioxan-2-yl]methyl methanesulfonate (Intermediate APO)

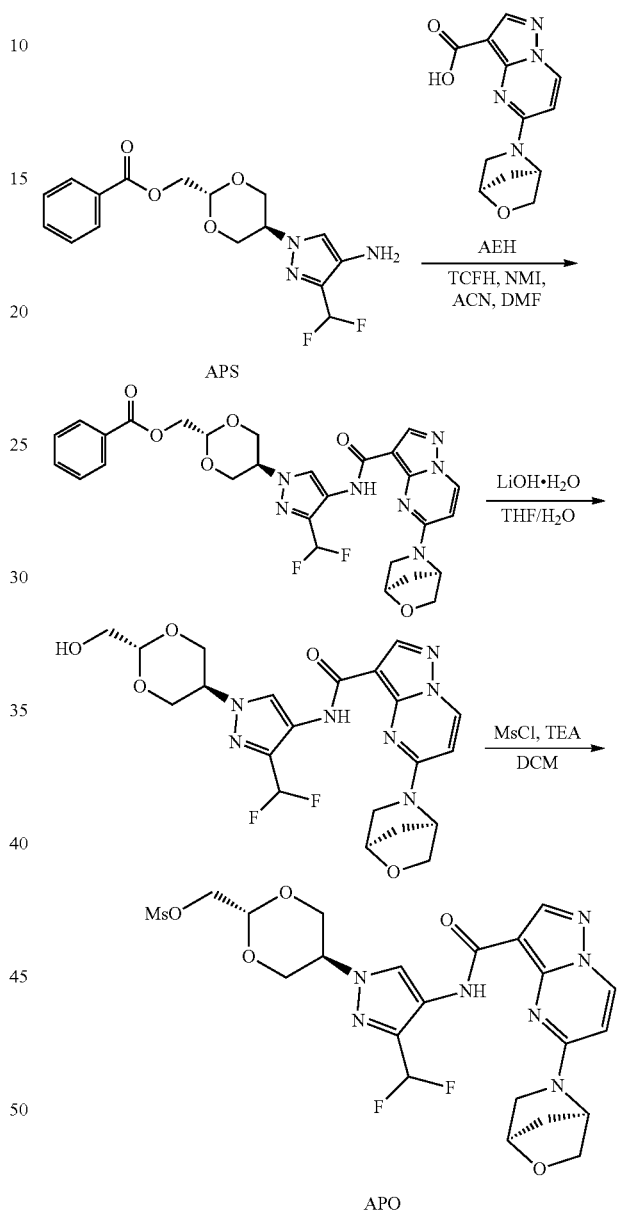

Step 1—[5-[3-(Difluoromethyl)-4-[[5-[(1R,4R)-2-oxa-5-azabicyclo[2.2.1]heptan-5-yl]pyrazolo[1,5-a] pyrimidine-3-carbonyl]amino]pyrazol-1-yl]-1,3-dioxan-2-yl]methyl benzoate To a solution of 5-[(1R,4R)-2-oxa-5-azabicyclo[2.2.1] heptan-5-yl]pyrazolo[1,5-a]pyrimidine-3-carboxylic acid (169 mg, 650 umol, Intermediate AEH) in ACN (10 mL) and DMF (1 mL) was added 1-methylimidazole (187 mg, 2.28 mmol, 181 uL), [chloro(dimethylamino)methylene]-dimethyl-ammonium; hexafluorophosphate (219 mg, 781 umol).

The reaction mixture was stirred at 20° C. for 30 min. Then [5-[4-amino-3-(difluoromethyl) pyrazol-1-yl]-1,3-dioxan-2-yl]methyl benzoate (230 mg, 650 umol, Intermediate APS) was added, and the reaction mixture was stirred at 20° C. for 12 hrs. On completion, the reaction was quenched with H₂O (10 mL) and concentrated in vacuo to give a residue. The residue was purified by reverse phase (0.1% FA condition) to give the title compound (60.0 mg, 15% yield) as a white solid. $^1$H NMR (400 MHz, DMSO-d$_6$) δ 9.49 (d, J=4.4 Hz, 1H), 8.78 (d, J=8.0 Hz, 1H), 8.54 (d, J=4.0 Hz, 1H), 8.26 (d, J=5.2 Hz, 1H), 8.00-7.97 (m, 2H), 7.69-7.67 (m, 1H), 7.58-7.54 (m, 2H), 7.30-6.99 (m, 1H), 6.87-6.43 (m, 1H), 5.28-5.06 (m, 2H), 4.80-4.66 (m, 2H), 4.38-4.32 (m, 4H), 4.08 (t, J=10.4 Hz, 2H), 3.85-3.71 (m, 2H), 3.68-3.42 (m, 2H), 2.07-1.90 (m, 2H); LC-MS (ESI⁺) m/z 596.2 (M+H)⁺.

Step 2—N-[3-(difluoromethyl)-1-[2-(hydroxymethyl)-1,3-dioxan-5-yl]pyrazol-4-yl]-5-[(1R,4R)-2-oxa-5-azabicyclo[2.2.1]heptan-5-yl]pyrazolo[1,5-a]pyrimidine-3-carboxamide To a solution of [5-[3-(difluoromethyl)-4-[[5-[(1R,4R)-2-oxa-5-azabicyclo[2.2.1]heptan-5-yl] pyrazolo[1,5-a]pyrimidine-3-carbonyl]amino]pyrazol-1-yl]-1,3-dioxan-2-yl] methyl benzoate (60.0 mg, 100 umol) in THF (2 mL) and H₂O (2 mL) was added LiOH—H₂O (6.34 mg, 151 umol). The reaction mixture was stirred at 25° C. for 16 hrs. On completion, the mixture was diluted with H₂O (15 mL) and extracted with DCM (2×30 mL). The organic layer was concentrated in vacuo to give the title compound (30.0 mg, 61% yield) as a white solid. LC-MS (ESI⁺) m/z 492.1 (M+1)⁺.

Step 3—[5-[3-(Difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]-1,3-dioxan-2-yl]methyl methanesulfonate To a solution of N-[3-(difluoromethyl)-1-[2-(hydroxymethyl)-1,3-dioxan-5-yl]pyrazol-4-yl]-5-[(1R,4R)-2-oxa-5-azabicyclo[2.2.1]heptan-5-yl]pyrazolo[1,5-a]pyrimidine-3-carboxamide (30.0 mg, 61.0 umol) and TEA (18.5 mg, 183 umol, 25.4 uL) in DCM (2 mL) was added MsCl (10.4 mg, 91.5 umol, 7.09 uL) at 0° C. The reaction mixture was stirred at 25° C. for 3 hrs. On completion, the reaction mixture was quenched with water (15 mL) and extracted with DCM (2×20 mL). The organic layer was concentrated in vacuo to give a residue. The residue was purified by purified by Prep-TLC (EA, Rf=0.6) to give the title compound (13.0 mg, 45% yield) as a white solid. LC-MS (ESI⁺) m/z 570.0 (M+1)⁺.

Tert-butyl (2S)-2-(prop-2-ynoxymethyl)morpholine-4-carboxylate (Intermediate APQ)

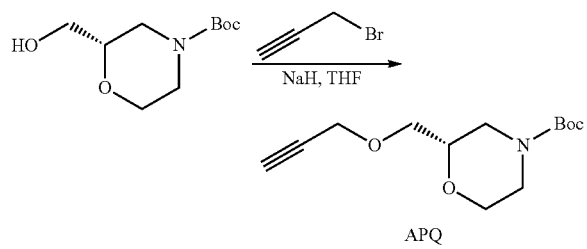

To a solution of tert-butyl (2S)-2-(hydroxymethyl)morpholine-4-carboxylate (2.00 g, 9.21 mmol, CAS #135065-76-8) in THF (20.0 mL) was added NaH (441 mg, 11.0 mmol, 60% dispersion in mineral oil) at 0° C. The mixture was stirred at 0° C. for 0.5 hr. 3-bromoprop-1-yne (2.05 g, 13.8 mmol, CAS #106-96-7) was then added. The mixture was stirred at 20° C. for 16 hrs. On completion, the reaction mixture was quenched by water (10 mL). The aqueous phase was extracted with EA (3×50 mL). The combined organic layer was washed with brine (2×60 mL), dried with anhydrous Na₂SO₄, filtered and concentrated in vacuo to give the title compound (2.30 g, 97% yield) as yellow oil. $^1$H NMR (400 MHz, CDCl₃) δ 4.21 (d, J=2.4 Hz, 2H), 4.03-3.78 (m, 3H), 3.65-3.50 (m, 4H), 3.05-2.68 (m, 2H), 2.45 (t, J=2.4 Hz, 1H), 1.47 (s, 9H).

3-[3-Methyl-4-[3-[[(2S)-morpholin-2-yl]methoxy]propyl]-2-oxo-benzimidazol-1-yl] piperidine-2,6-dione (Intermediate APR)

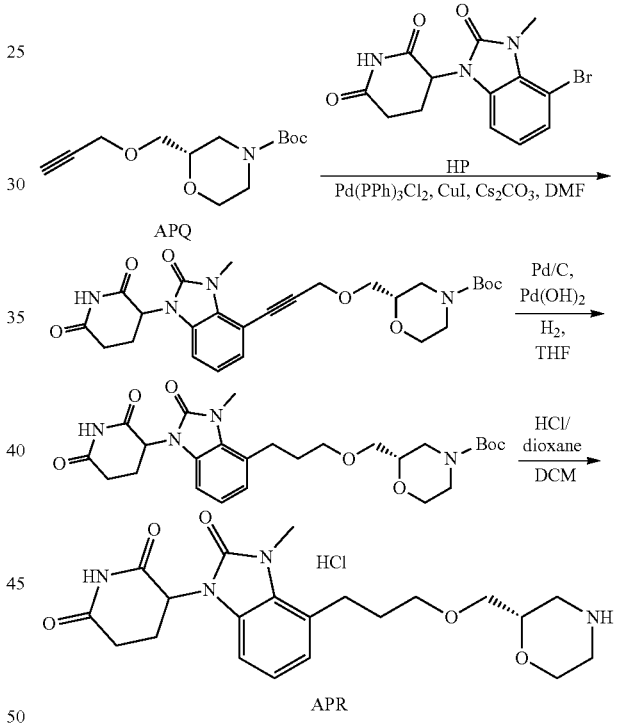

Step 1—Tert-butyl (2S)-2-[3-[1-(2,6-dioxo-3-piperidyl)-3-methyl-2-oxo-benzimidazol-4-yl]prop-2-ynoxymethyl]morpholine-4-carboxylate A mixture of tert-butyl (2S)-2-(prop-2-ynoxymethyl)morpholine-4-carboxylate (567 mg, 2.22 mmol, Intermediate APQ), 3-(4-bromo-3-methyl-2-oxo-benzimidazol-1-yl)piperidine-2,6-dione (500 mg, 1.48 mmol, Intermediate HP), Pd(PPh₃)₂Cl₂ (207 mg, 296 umol), CuI (56.3 mg, 296 umol), 4 Å MS (500 mg) and Cs₂CO₃ (1.45 g, 4.44 mmol) in DMF (6.00 mL) was degassed and purged with N₂ gas 3 times, and then the mixture was stirred at 80° C. for 2 hrs under N₂ atmosphere. On completion, the reaction mixture was filtered and concentrated in vacuo to give a residue. The residue was purified by reversed phase (FA) to give the title compound (230 mg, 30% yield) as a yellow solid. $^1$H NMR (400 MHz, CDCl$_3$) δ 8.08 (s, 1H), 7.18 (d, J=8.0 Hz, 1H), 7.00 (t, J=8.0 Hz, 1H), 6.77 (d, J=8.0 Hz, 1H), 5.20 (dd, J=5.2, 12.4 Hz, 1H), 4.48 (s, 2H), 4.03-3.82 (m, 3H), 3.78 (s, 3H), 3.68-3.62 (m, 3H), 3.61-3.50 (m, 1H), 3.03-2.91 (m, 2H), 2.90-2.69 (m, 3H), 2.30-2.20 (m, 1H), 1.47 (s, 9H).

Step 2—Tert-butyl (2S)-2-[3-[1-(2,6-dioxo-3-piperidyl)-3-methyl-2-oxo-benzimidazol-4-yl]propoxymethyl]morpholine-4-carboxylate To a solution of tert-butyl (2S)-2-[3-[1-(2,6-dioxo-3-piperidyl)-3-methyl-2-oxo-benzimidazol-4-yl] prop-2-ynoxymethyl]morpholine-4-carboxylate (60.0 mg, 117 umol) in THF (3.00 mL) was added Pd/C (10.0 mg, 10 wt %) and Pd(OH)$_2$ (10 mg, 10 wt %) under N$_2$ atmosphere. The suspension was degassed and purged with H$_2$ gas 3 times. Then the mixture was stirred at 20° C. for 16 hrs under H$_2$ (15 Psi.). On completion, the reaction mixture was filtered and the filtrate was concentrated in vacuo to give the title compound (60.0 mg, 99% yield) as a yellow solid. $^1$H NMR (400 MHz, CDCl$_3$) δ 8.12 (s, 1H), 6.99-6.96 (m, 1H), 6.93-6.87 (m, 1H), 6.70-6.65 (m, 1H), 5.26-5.17 (m, 1H), 3.99-3.80 (m, 3H), 3.69 (s, 3H), 3.58-3.43 (m, 6H), 3.05-2.70 (m, 8H), 2.00-1.90 (m, 2H), 1.48 (s, 9H).

Step 3—3-[3-Methyl-4-[3-[[(2S)-morpholin-2-yl]methoxy]propyl]-2-oxo-benzimidazol-1-yl] piperidine-2,6-dione To a solution of tert-butyl (2S)-2-[3-[1-(2,6-dioxo-3-piperidyl)-3-methyl-2-oxo-benzimidazol-4-yl] propoxymethyl]morpholine-4-carboxylate (55.0 mg, 106 umol) in DCM (0.50 mL) was added HCl/dioxane (4 M, 0.50 mL) The mixture was stirred at 20° C. for 0.5 hr. On completion, the reaction mixture was concentrated in vacuo to give the title compound (48.0 mg, 99% yield, HCl salt) as a white solid. LC-MS (ESI$^+$) m/z 417.1 (M+H)$^+$.

4-(1-(2,6-Dioxopiperidin-3-yl)-3-methyl-2-oxo-2,3-dihydro-1H-benzo[d]imidazol-4-yl) butanoic acid (Intermediate APW)

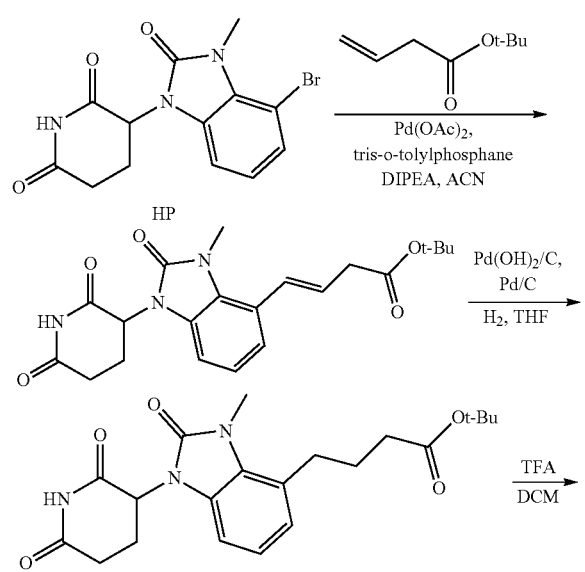

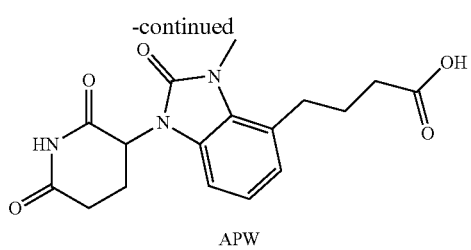

Step 1—(E)-tert-butyl 4-(1-(2,6-dioxopiperidin-3-yl)-3-methyl-2-oxo-2,3-dihydro-1H-benzo[d] imidazol-4-yl)but-3-enoate A mixture of 3-(4-bromo-3-methyl-2-oxo-benzimidazol-1-yl)piperidine-2,6-dione (3.00 g, 8.87 mmol, Intermediate HP), tert-butyl but-3-enoate (2.52 g, 17.74 mmol, CAS #14036-55-6), DIPEA (2.29 g, 17.7 mmol), tris-o-tolylphosphane (8.10 g, 26.6 mmol) and Pd(OAc)$_2$ (199 mg, 887 umol) in ACN (50 mL) was heated to 100° C. with stirring for 16 hours under N$_2$. On completion, the mixture was filtered and concentrated. The residue was purified by prep-HPLC: reverse phase (condition: 0.1% FA) to give the title compound (2.00 g, 56% yield) as yellow solid. $^1$H NMR (400 MHz, DMSO-d$_6$) δ 11.10 (s, 1H), 7.14-6.95 (m, 3H), 6.24-6.03 (m, 1H), 5.58-5.48 (m, 1H), 5.38 (d, J=5.2, 12.0 Hz, 1H), 3.88 (d, J=4.4 Hz, 1H), 3.62-3.47 (m, 3H), 3.26 (d, J=6.4 Hz, 1H), 2.99-2.84 (m, 1H), 2.79-2.63 (m, 2H), 2.06-1.94 (m, 1H), 1.44 (s, 4H), 1.41 (s, 3H), 1.25 (s, 1H). LC-MS (ESI$^+$) m/z 400.1 (M+H)$^+$.

Step 2—Tert-butyl 4-(1-(2,6-dioxopiperidin-3-yl)-3-methyl-2-oxo-2,3-dihydro-1H-benzo[d]imidazol-4-yl)butanoate To a solution of tert-butyl (E)-4-[1-(2,6-dioxo-3-piperidyl)-3-methyl-2-oxo-benzimidazol-4-yl] but-3-enoate (500 mg, 1.25 mmol) in THF (50 mL) was added Pd/C (100 mg, 10% wt) and Pd(OH)$_2$/C (100 mg, 10% wt) under N$_2$. The suspension was degassed under vacuum and purged with H$_2$ gas several times. The mixture was stirred under H$_2$ (15 psi) at 20° C. for 2 hours. On completion, the mixture was filtered and concentrated. The title compound (400 mg, 79% yield) was obtained as white solid. $^1$H NMR (400 MHz, DMSO-d$_6$) δ 11.09 (s, 1H), 7.02-6.95 (m, 2H), 6.89-6.81 (m, 1H), 5.37 (dd, J=5.2, 12.4 Hz, 1H), 3.56 (s, 3H), 2.95-2.89 (m, 2H), 2.73-2.61 (m, 2H), 2.31 (t, J=7.2 Hz, 2H), 2.05-1.94 (m, 1H), 1.87-1.74 (m, 3H), 1.41 (s, 9H).

Step 3—4-(1-(2,6-Dioxopiperidin-3-yl)-3-methyl-2-oxo-2,3-dihydro-1H-benzo[d]imidazol-4-yl) butanoic acid To a solution of tert-butyl 4-[1-(2,6-dioxo-3-piperidyl)-3-methyl-2-oxo-benzimidazol-4-yl]butanoate (400 mg, 996 umol) in DCM (10 mL) was added TFA (4.62 g, 40.5 mmol, 3.0 mL) and the mixture was stirred at 25° C. for 2 hours. On completion, the mixture was concentrated. The title compound (250 mg, 72% yield) was obtained as colorless oil. LC-MS (ESI$^+$) m/z 346.0 (M+H)$^+$.

1969

3-(3-Methyl-2-oxo-4-(4-oxo-4-(piperazin-1-yl)butyl)-2,3-dihydro-1H-benzo[d]imidazol-1-yl) piperidine-2,6-dione (Intermediate APX)

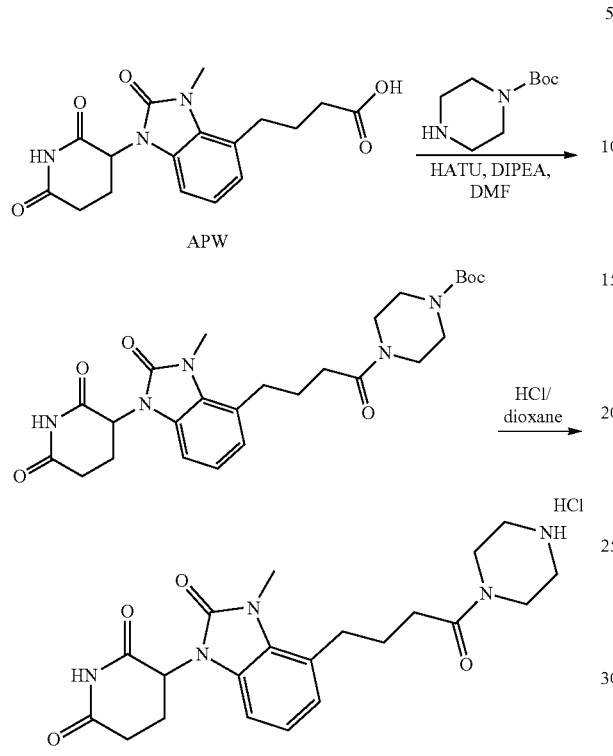

Step 1—Tert-butyl 4-(4-(1-(2,6-dioxopiperidin-3-yl)-3-methyl-2-oxo-2,3-dihydro-1H-benzo[d]imidazol-4-yl)butanoyl)piperazine-1-carboxylate A mixture of 4-[1-(2,6-dioxo-3-piperidyl)-3-methyl-2-oxo-benzimidazol-4-yl]butanoic acid (150 mg, 434 umol, Intermediate APW) and HATU (247 mg, 651 umol), DIPEA (280 mg, 2.17 mmol) in DMF (1.0 mL) was stirred at 25° C. for 10 min and then tert-butyl piperazine-1-carboxylate (161 mg, 868 umol) was added. The mixture was stirred at 25° C. for 1 hour. On completion, the mixture was quenched with water (0.1 mL) and concentrated. The residue was purified by reverse phase (condition: 0.1% FA) to give the title compound (60.0 mg, 26% yield) as yellow solid. LC-MS (ESI$^+$) m/z 414.2 (M−100+H)$^+$.

Step 2—3-(3-Methyl-2-oxo-4-(4-oxo-4-(piperazin-1-yl)butyl)-2,3-dihydro-1H-benzo[d]imidazol-1-yl)piperidine-2,6-dione To a solution of tert-butyl 4-[4-[1-(2,6-dioxo-3-piperidyl)-3-methyl-2-oxo-benzimidazol-4-yl] butanoyl]piperazine-1-carboxylate (50 mg, 97.3 umol) in DCM (3.0 mL) was added HCl/dioxane (4 M, 1.0 mL) and the mixture was stirred at 25° C. for 1 hour. On completion, the mixture was concentrated to give the title compound (40.0 mg, 91% yield, HCl) as white solid. LC-MS (ESI$^+$) m/z 414.2 (M+H)$^+$.

1970

3-[3-methyl-2-oxo-4-[2-(4-piperidyl)ethyl]benzimidazol-1-yl]piperidine-2,6-dione (Intermediate APY)

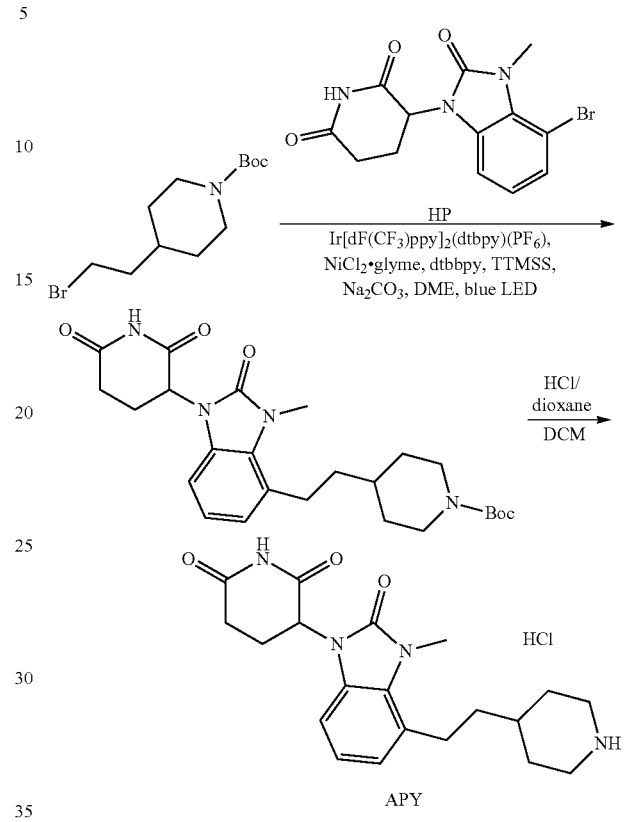

Step 1—Tert-butyl 4-[2-[1-(2,6-dioxo-3-piperidyl)-3-methyl-2-oxo-benzimidazol-4-yl]ethyl]piperidine-1-carboxylate To an 40 mL vial equipped with a stir bar was added 3-(4-bromo-3-methyl-2-oxo-benzimidazol-1-yl)piperidine-2,6-dione (868 mg, 2.57 mmol, Intermediate HP), tert-butyl 4-(2-bromoethyl) piperidine-1-carboxylate (900 mg, 3.08 mmol, CAS #169457-73-2), Ir[dF(CF$_3$)ppy]2(dtbpy)(PF$_6$) (28.8 mg, 25.7 umol), NiCl$_2$·glyme (2.82 mg, 12.8 umol), dtbbpy (4.13 mg, 15.4 umol), TTMSS (638 mg, 2.57 mmol, 792 uL) and Na$_2$CO$_3$ (544 mg, 5.13 mmol) in DME (20 mL). The reaction mixture was stirred and irradiated with a 34 W blue LED lamp at 25° C. for 14 hrs. On completion, the reaction mixture was filtered and the residue was concentrated in vacuo to give a residue. The crude product was purified by reverse phase flash (0.1% FA condition) to give the title compound (470 mg, 39% yield) as white solid. $^1$H NMR (400 MHz, DMSO-d$_6$) δ11.03 (br s, 1H), 6.98-6.92 (m, 2H), 6.90-6.83 (m, 1H), 5.35 (dd, J=5.2, 12.4 Hz, 1H), 3.96-3.92 (m, 2H), 3.55 (s, 3H), 2.95-2.83 (m, 3H), 2.75-2.57 (m, 4H), 2.03-1.95 (m, 1H), 1.74 (d, J=12.4 Hz, 2H), 1.53 (t, J=6.0 Hz, 3H), 1.39 (s, 9H), 1.13-0.99 (m, 2H); LC-MS (ESI$^+$) m/z 415.2 (M+H−56)$^+$.

Step 2—3-[3-Methyl-2-oxo-4-[2-(4-piperidyl)ethyl]benzimidazol-1-yl]piperidine-2,6-dione To a solution of tert-butyl4-[2-[1-(2,6-dioxo-3-piperidyl)-3-methyl-2-oxo-benzimidazol-4-yl]ethyl] piperidine-1-carboxylate (200 mg, 425 umol) in DCM (3.0 mL) was added HCl/dioxane (4 M, 1.0 mL). The reaction mixture was stirred at 25° C. for 1 hr. On completion, the reaction mixture was concentrated in vacuo to give the title compound (170 mg, 90% yield, HCl salt) as orange solid. LC-MS (ESI$^+$) m/z 371.2 (M+H)$^+$.

3-[4-[2-(7-azaspiro[3.5]nonan-2-yl)ethyl]-3-methyl-2-oxo-benzimidazol-1-yl]piperidine-2,6-dione (Intermediate APZ)

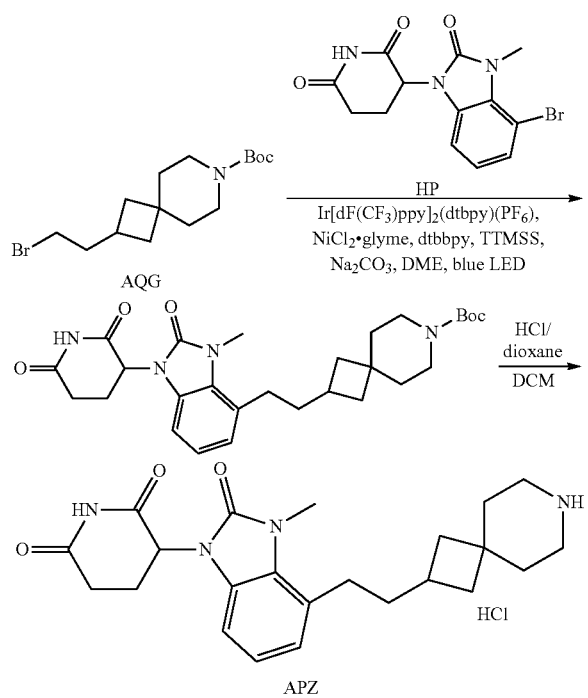

Step 1—Tert-butyl 2-(2-(1-(2,6-dioxopiperidin-3-yl)-3-methyl-2-oxo-2,3-dihydro-1H-benzo[d] imidazol-4-yl)ethyl)-7-azaspiro[3.5]nonane-7-carboxylate To an 40 mL vial equipped with a stir bar was added 3-(4-bromo-3-methyl-2-oxo-benzimidazol-1-yl)piperidine-2,6-dione (1.00 g, 2.96 mmol, Intermediate HP), tert-butyl 2-(2-bromoethyl)-7-azaspiro [3.5]nonane-7-carboxylate (1.08 g, 3.25 mmol, Intermediate AQG), bis[3,5-difluoro-2-[5-(trifluoromethyl)-2-pyridyl] phenyl]iridium(1+); 4-tert-butyl-2-(4-tert-butyl-2-pyridyl)pyridine; hexafluorophosphate (33.1 mg, 29.5 umol), NiCl$_2$.dtbbpy (5.88 mg, 14.7 umol), TTMSS (735 mg, 2.96 mmol) and Na$_2$CO$_3$ (626 mg, 5.91 mmol) in DME (24 mL). The vial was sealed and placed under nitrogen was added. The reaction was stirred and irradiated with a 34 W blue LED lamp (7 cm away), with cooling fan to keep the reaction temperature at 25° C. for 4 hr. On completion, the mixture was filtered and concentrated. The residue was purified by prep-HPLC: reverse phase (condition: 0.1% FA). The title compound (400 mg, 26% yield) was obtained as red solid. LC-MS (ESI$^+$) m/z 455.2 (M+H−56)$^+$.

Step 2—3-(4-(2-(7-azaspiro[3.5]nonan-2-yl)ethyl)-3-methyl-2-oxo-2,3-dihydro-1H-benzo[d]imidazol-1-yl)piperidine-2,6-dione To a solution of tert-butyl 2-[2-[1-(2,6-dioxo-3-piperidyl)-3-methyl-2-oxo-benzimidazol-4-yl]ethyl]-7-azaspiro[3.5]nonane-7-carboxylate (140 mg, 274 umol) in DCM (3 mL) was added HCl/dioxane (4 M, 1.08 mL) and the mixture was stirred at 25° C. for 1 hour. On completion, the mixture was concentrated. The title compound (110 mg, 89% yield, HCl) was obtained as white solid. LC-MS (ESI$^+$) m/z 411.0 (M+H)$^+$.

Tert-butyl 4-[(1S)-1-methylprop-2-ynoxy]piperidine-1-carboxylate (Intermediate AQA)

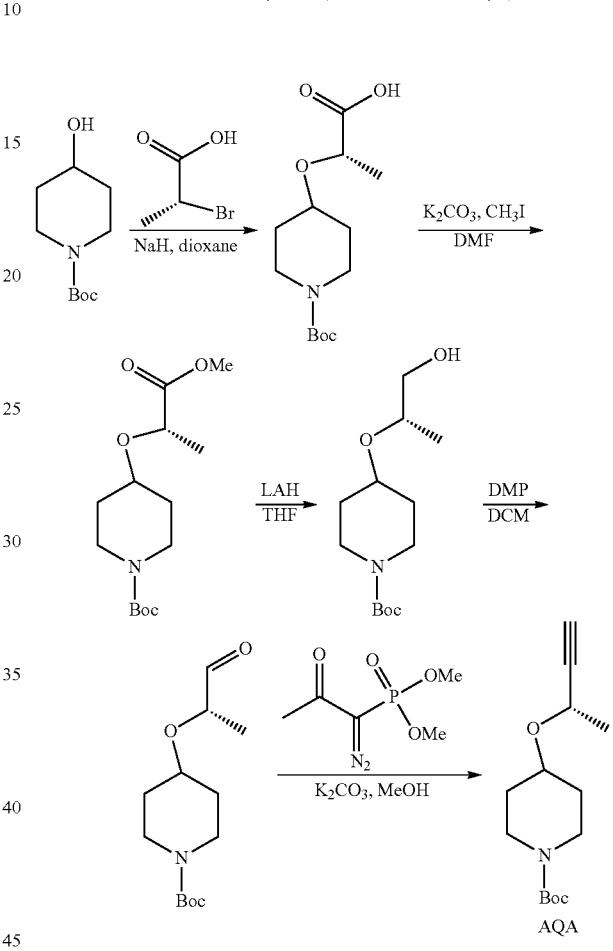

Step 1—(2S)-2-[(1-tert-butoxycarbonyl-4-piperidyl)oxy]propanoic acid

To a solution of tert-butyl 4-hydroxypiperidine-1-carboxylate (10.0 g, 49.6 mmol, CAS #109384-19-2) in dioxane (160 mL) was added NaH (7.95 g, 198 mmol, 60% purity) at 0° C. The mixture was stirred at 0° C. for 0.5 hr, then (2R)-2-bromopropanoic acid (7.60 g, 49.6 mmol, CAS #10009-70-8) was added. The mixture was stirred at 25° C. for 40 hrs. On completion, the mixture was quenched with H$_2$O (200 mL) and concentrated in vacuo to remove dioxane. Then extracted with EA (2×50 mL), the aqueous phase was acidified to pH=1 using 1 M HCl aqueous, then extracted with EA (2×80 mL). The organic layers were washed with brine (2×50 mL), dried over anhydrous Na$_2$SO$_4$, filtered and concentrated in vacuo to give the title compound (8.83 g, 65% yield) as yellow solid. $^1$H NMR (400 MHz, CDCl$_3$) δ 9.65 (s, 1H), 4.20-4.09 (m, 1H), 3.87-3.71 (m, 2H), 3.65-3.53 (m, 1H), 3.17-3.03 (m, 2H), 1.88-1.80 (m, 2H), 1.65-1.50 (m, 2H), 1.49-1.43 (m, 12H).

Step 2—Tert-butyl 4-[(1S)-2-methoxy-1-methyl-2-oxo-ethoxy]piperidine-1-carboxylate To a solution of (2S)-2-[(1-tert-butoxycarbonyl-4-piperidyl) oxy]propanoic acid (7.83 g, 28.6 mmol) and K$_2$CO$_3$ (7.92 g, 57.2 mmol) in DMF (80 mL) was added CH$_3$I (20.3 g, 143 mmol, 8.92 mL) at 0° C. The mixture was stirred at 25° C. for 16 hrs. On completion, the mixture was diluted with H$_2$O (400 mL) and extracted with EA (3×80 mL). The organic layers were washed with brine (3×60 mL), dried over anhydrous Na$_2$SO$_4$, filtered and concentrated in vacuo to give the title compound (7.9 g, 95% yield) as yellow oil. $^1$H NMR (400 MHz, CDCl$_3$) δ 4.10-3.98 (m, 1H), 3.80-3.64 (m, 5H), 3.51-3.35 (m, 1H), 3.09-2.93 (m, 2H), 1.84-1.68 (m, 2H), 1.52-1.42 (m, 2H), 1.38 (s, 9H), 1.33 (d, J=6.8 Hz, 3H).

Step 3—Tert-butyl 4-[(1S)-2-hydroxy-1-methyl-ethoxy]piperidine-1-carboxylate To a solution of LiAlH$_4$ (1.64 g, 43.3 mmol) in THF (30 mL) was added a solution of tert-butyl 4-[(1S)-2-methoxy-1-methyl-2-oxo-ethoxy] piperidine-1-carboxylate (8.30 g, 28.8 mmol) in THF (50 mL) dropwise at 0° C. The mixture was stirred at 0° C. for 0.5 hr. On completion, the mixture was quenched with H$_2$O (1.7 mL), 15% NaOH (1.7 mL) and H$_2$O (5.00 mL). The mixture was dried over anhydrous Na$_2$SO$_4$, filtered and concentrated in vacuo to give the title compound (6.9 g, 92% yield) as yellow oil. $^1$H NMR (400 MHz, CDCl$_3$) δ 3.87-3.75 (m, 2H), 3.72-3.64 (m, 1H), 3.63-3.52 (m, 2H), 3.49-3.39 (m, 1H), 3.17-3.00 (m, 2H), 2.16-1.99 (m, 1H), 1.89-1.80 (m, 2H), 1.77-1.52 (m, 2H), 1.47 (s, 9H), 1.12 (d, J=7.2 Hz, 3H).

Step 4—Tert-butyl 4-[(1S)-1-methyl-2-oxo-ethoxy]piperidine-1-carboxylate

To a solution of tert-butyl 4-[(1S)-2-hydroxy-1-methyl-ethoxy] piperidine-1-carboxylate (2.00 g, 7.71 mmol) in DCM (50 mL) was added DMP (4.91 g, 11.5 mmol). The mixture was stirred at 25° C. for 2 hrs. On completion, the mixture was quenched with saturated Na$_2$S$_2$O$_3$ (40 mL). The organic layer was separated and washed with saturated NaHCO$_3$ (2×30 mL), the organic layer was dried over anhydrous Na$_2$SO$_4$, filtered and concentrated in vacuo to give the title compound (1.65 g, 83% yield) as yellow oil. $^1$H NMR (400 MHz, CDCl$_3$) δ 9.57 (d, J=2.0 Hz, 1H), 3.90-3.80 (m, 1H), 3.78-3.66 (m, 2H), 3.57-3.44 (m, 1H), 3.10-2.95 (m, 2H), 1.83-1.74 (m, 2H), 1.55-1.46 (m, 2H), 1.39 (s, 9H), 1.22 (d, J=7.2 Hz, 3H).

Step 5—Tert-butyl 4-(1S)-1-methylprop-2-ynoxy]piperidine-1-carboxylate

To a solution of tert-butyl 4-[(1S)-1-methyl-2-oxo-ethoxy]piperidine-1-carboxylate (1.65 g, 6.41 mmol), K$_2$CO$_3$ (2.66 g, 19.2 mmol) in MeOH (30 mL) was added 1-diazo-1-dimethoxyphosphoryl-propan-2-one (1.48 g, 7.69 mmol, CAS #90965-06-3) at 0° C. The mixture was stirred at 25° C. for 16 hrs. On completion, the mixture was concentrated in vacuo. The mixture was diluted with H$_2$O (40 mL), and extracted with EA (3×30 mL). The organic layers were washed with brine (2×20 mL) dried over anhydrous Na$_2$SO$_4$, filtered and concentrated in vacuo to give the title compound (1.40 g, 86% yield) as yellow solid. $^1$H NMR (400 MHz, CDCl$_3$) δ 4.26-4.15 (m, 1H), 3.77-3.66 (m, 3H), 3.12-2.92 (m, 2H), 2.32 (d, J=2.0 Hz, 1H), 1.84-1.70 (m, 2H), 1.51-1.40 (m, 2H), 1.39-1.36 (m, 12H).

3-[3-methyl-2-oxo-4-[(3S)-3-(4-piperidyloxy)but-1-ynyl]benzimidazol-1-yl]piperidine-2,6-dione (Intermediate AOB)

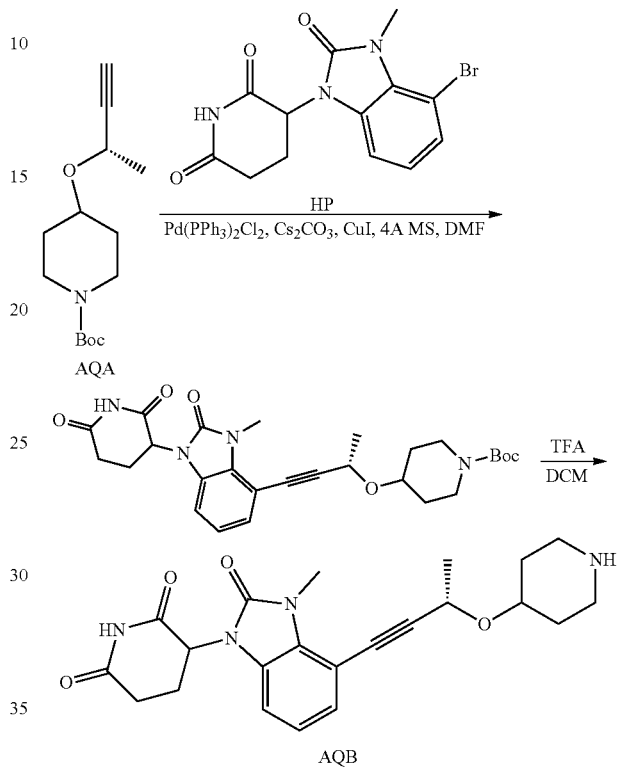

Step 1—Tert-butyl 4-[(1S)-3-[1-(2,6-dioxo-3-piperidyl)-3-methyl-2-oxo-benzimidazol-4-yl]-1-methyl-prop-2-ynoxy]piperidine-1-carboxylate To a solution of tert-butyl 4-[(1S)-1-methylprop-2-ynoxy] piperidine-1-carboxylate (524 mg, 2.07 mmol, Intermediate AQA), 3-(4-bromo-3-methyl-2-oxo-benzimidazol-1-yl)piperidine-2,6-dione (350 mg, 1.04 mmol, Intermediate HP) in DMF (8.00 mL) was added Pd(PPh$_3$)$_2$Cl$_2$ (145 mg, 207 umol), Cs$_2$CO$_3$ (1.35 g, 4.14 mmol), CuI (39.4 mg, 207 umol) and 4 Å molecular sieves (200 mg, 1.04 mmol) under N$_2$. The mixture was stirred at 80° C. for 3 hrs. On completion, the mixture was filtered and concentrated in vacuo. The mixture was purified by reverse phase (0.1% FA) to give the title compound (250 mg, 47% yield) as yellow solid. $^1$H NMR (400 MHz, CDCl$_3$) δ 8.19 (s, 1H), 7.21-7.12 (m, 1H), 7.01 (t, J=8.0 Hz, 1H), 6.78 (d, J=7.6 Hz, 1H), 5.27-5.13 (m, 1H), 4.60-4.50 (m, 1H), 3.91-3.81 (m, 2H), 3.80 (s, 3H), 3.19-3.08 (m, 2H), 3.03-2.93 (m, 1H), 2.91-2.69 (m, 2H), 2.31-2.20 (m, 1H), 1.94-1.84 (m, 3H), 1.70-1.60 (m, 2H), 1.56 (d, J=6.8 Hz, 3H), 1.48 (s, 9H), LC-MS (ESI$^+$) m/z 533.3 (M+Na)$^+$.

Step 2—3-[3-methyl-2-oxo-4-[(3S)-3-(4-piperidyloxy)but-1-ynyl]benzimidazol-1-yl]piperidine-2,6-dione To a solution of tert-butyl 4-[(1S)-3-[1-(2,6-dioxo-3-piperidyl)-3-methyl-2-oxo-benzimidazol-4-yl]-1-methyl-prop- 2-ynoxy]piperidine-1-carboxylate (80.0 mg, 156 umol) in DCM (2.00 mL) was added TFA (770 mg, 6.75 mmol). The mixture was stirred at 25° C. for 0.5 hr. On completion, the mixture was concentrated in vacuo to give the title compound (80.0 mg, 97% yield, TFA) as yellow solid. LC-MS (ESI$^+$) m/z 411.3 (M+H)$^+$.

3-[3-Methyl-2-oxo-4-[(3S)-3-(4-piperidyloxy)butyl]benzimidazol-1-yl]piperidine-2,6-dione (Intermediate AQC)

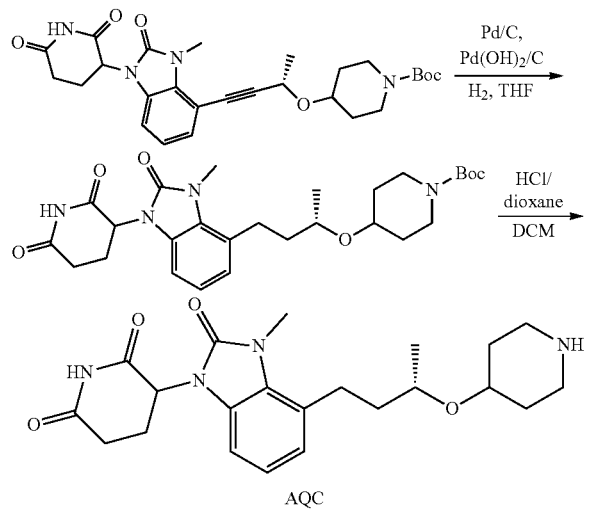

AQC

Step 1—Tert-butyl 4-[(1S)-3-[1-(2,6-dioxo-3-piperidyl)-3-methyl-2-oxo-benzimidazol-4-yl]-1-methyl-propoxylpiperidine-1-carboxylate To a solution of tert-butyl 4-[(1S)-3-[1-(2,6-dioxo-3-piperidyl)-3-methyl-2-oxo-benzimidazol-4-yl]-1-methyl-prop-2-ynoxy]piperidine-1-carboxylate (100 mg, 195 umol, synthesized via Step 1 of Intermediate AQB) in THF (10 mL) was added Pd/C (50 mg, 10% wt) and Pd(OH)$_2$/C (50 mg, 10% wt). The mixture was stirred at 25° C. for 2 hrs under H$_2$ (15 Psi). On completion, the mixture was filtered and concentrated in vacuo to give the title compound (90 mg, 89% yield) as white solid. $^1$H NMR (400 MHz, DMSO-d$_6$) δ 11.10 (s, 1H), 6.97 (d, J=4.8 Hz, 2H), 6.91-6.85 (m, 1H), 5.40-5.30 (m, 1H), 3.70-3.58 (m, 4H), 3.58 (s, 3H), 3.14-2.96 (m, 3H), 2.95-2.80 (m, 2H), 2.78-2.60 (m, 2H), 2.08-1.93 (m, 1H), 1.84-1.67 (m, 4H), 1.42-1.39 (m, 9H), 1.36-1.28 (m, 2H), 1.14 (d, J=6.0 Hz, 3H).

Step 2—3-[3-Methyl-2-oxo-4-[(3S)-3-(4-piperidyloxy)butyl]benzimidazol-1-yl]piperidine-2,6-dione To a solution of tert-butyl 4-[(1S)-3-[1-(2,6-dioxo-3-piperidyl)-3-methyl-2-oxo-benzimidazol-4-yl]-1-methylpropoxy]piperidine-1-carboxylate (90.0 mg, 174 umol) in DCM (4.00 mL) was added HCl/dioxane (4.00 M, 2.00 mL). The mixture was stirred at 25° C. for 0.5 hr. On completion, the mixture was concentrated in vacuo to give the title compound (75 mg, 95% yield, HCl salt) as white solid. LC-MS (ESI$^+$) m/z 415.3 (M+H)$^+$.

Tert-butyl 2-(2-bromoethyl)-7-azaspiro[3.5]nonane-7-carboxylate (Intermediate AQG)

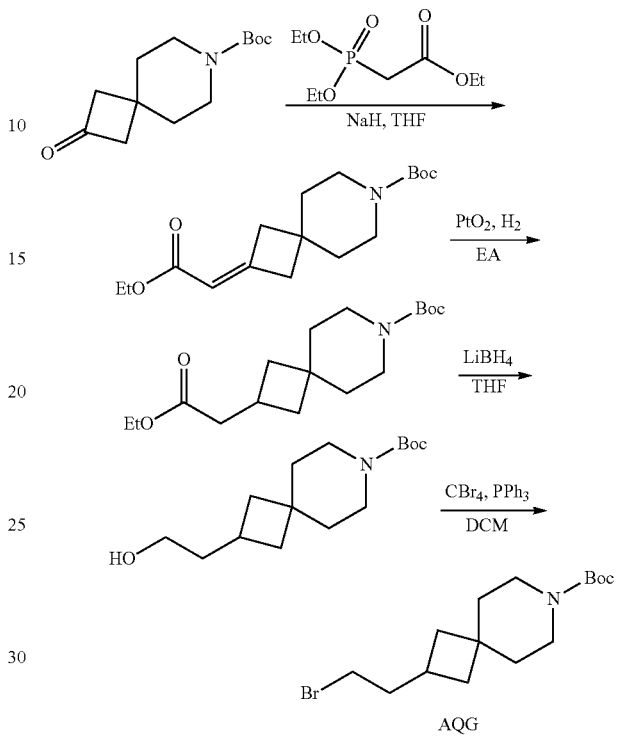

AQG

Step 1—Tert-butyl 2-(2-ethoxy-2-oxoethylidene)-7-azaspiro[3.5]nonane-7-carboxylate To a solution of methyl 2-diethoxyphosphorylacetate (2.64 g, 12.5 mmol) in DMF (30 mL) was added NaH (501 mg, 12.5 mmol, 60% dispersion in mineral oil) at 0° C. with stirring for 0.5 hour. Next was added a solution of tert-butyl 2-oxo-7-azaspiro[3.5]nonane-7-carboxylate (2.00 g, 8.36 mmol, CAS #203661-69-2) in DMF (10 mL). The mixture was warmed to 25° C. with stirring for 2 hours. On completion, the mixture was poured into 150 mL saturated ammonium chloride aqueous solution and extracted with ethyl acetate (50 mL×3). The combined organic layers were washed with brine (20 mL, dried over anhydrous sodium sulfate and concentrated in vacuo. The residue was purified by silica gel column chromatography [petroleum ether:ethyl acetate=10:1 to 3:1]. The title compound (2.00 g, 80% yield) was obtained as colorless oil. $^1$H NMR (400 MHz, CDCl$_3$) δ 5.65-5.64 (m, 1H), 3.62 (s, 3H), 3.35-3.21 (m, 4H), 2.80 (s, 2H), 2.50 (s, 2H), 1.52-1.45 (m, 2H), 1.38 (m, 9H).

Step 2—Tert-butyl 2-(2-ethoxy-2-oxoethyl)-7-azaspiro[3.5]nonane-7-carboxylate To a solution of tert-butyl 2-(2-methoxy-2-oxo-ethylidene)-7-azaspiro[3.5]nonane-7-carboxylate (1.8 g, 6.09 mmol) in EtOH (50 mL) was added Pd(OH)$_2$/C (100 mg, 10% wt) and Pd/C (100 mg, 10% wt) under N$_2$. The suspension was degassed under vacuum and purged with H$_2$ several times. The mixture was stirred under H$_2$ (15 psi) at 25° C. for 16 hours. On completion, the reaction mixture was filtered and the filter was concentrated. The title compound (1.7 g, 80% purity) was obtained as colorless oil. ¹H NMR (400 MHz, CDCl₃) δ 3.58 (s, 3H), 3.32-3.24 (m, 2H), 3.22-3.14 (m, 2H), 2.57 (td, J=8.0, 16.0 Hz, 1H), 2.36 (d, J=7.8 Hz, 2H), 2.03-1.92 (m, 2H), 1.52-1.47 (m, 2H), 1.43-1.34 (m, 14H).

Step 3—Tert-butyl 2-(2-hydroxyethyl)-7-azaspiro[3.5]nonane-7-carboxylate

To a solution of tert-butyl 2-(2-methoxy-2-oxo-ethyl)-7-azaspiro[3.5]nonane-7-carboxylate (1.70 g, 5.72 mmol) in THF (30 mL) was added LiBH₄ (373 mg, 17.1 mmol) and the mixture was stirred at 75° C. for 4 hours. On, completion, the mixture was cooled to rt and poured into 30 mL water and extracted with ethyl acetate (50 mL×3). The combined organic layers were washed with water, brine, dried over anhydrous sodium sulfate and concentrated in vacuo. The title compound (1.50 g, 97% yield) was obtained as colorless oil. ¹H NMR (400 MHz, CDCl₃) δ 3.57-3.45 (m, 2H), 3.31-3.23 (m, 2H), 3.22-3.15 (m, 2H), 2.27 (d, J=8.0, 16.0 Hz, 1H), 1.96-1.85 (m, 2H), 1.61 (q, J=6.8 Hz, 2H), 1.52-1.45 (m, 2H), 1.41-1.30 (m, 13H).

Step 4—Tert-butyl 2-(2-bromoethyl)-7-azaspiro[3.5]nonane-7-carboxylate

To a solution of tert-butyl 2-(2-hydroxyethyl)-7-azaspiro[3.5]nonane-7-carboxylate (1.50 g, 5.57 mmol) and PPh₃ (4.38 g, 16.7 mmol) in DCM (30 mL) was added CBr₄ (5.54 g, 16.7 mmol) at 0° C. and the mixture was stirred at 25° C. for 14 hours. On completion, the mixture was filtered and concentrated. The residue was purified by silica gel column chromatography [petroleum ether:ethyl acetate=100:1 to 3:1] and the title compound (1.50 g, 81% yield) was obtained as colorless oil. ¹H NMR (400 MHz, CDCl₃) δ 3.38-3.30 (m, 4H), 3.29-3.23 (m, 2H), 2.40 (J=8.0 Hz, 1H), 2.05-1.94 (m, 4H), 1.59-1.55 (m, 2H), 1.47-1.39 (m, 13H).

5-(2,2-Dimethylmorpholino)pyrazolo[1,5-a]pyrimidine-3-carboxylic acid (Intermediate AQH)

Step 1—Ethyl 5-(2,2-dimethylmorpholino)pyrazolo[1,5-a]pyrimidine-3-carboxylate

A solution of ethyl 5-chloropyrazolo[1,5-a]pyrimidine-3-carboxylate (1.87 g, 8.27 mmol, CAS 1224944-77-7), 2,2-dimethylmorpholine (1.00 g, 8.68 mmol, CAS #147688-58-2) and DIPEA (2.14 g, 16.5 mmol) in ACN (30 mL) was stirred at 25° C. for 2 hr. On completion, the reaction was diluted with 150 ml of water and extracted with EA (3×100 ml). The combined organic phase was washed with brine, dried over Na₂SO₄, filtered and concentrated in vacuo to give yellow solid (2.6 g, 97% yield). LC-MS (ESI⁺) m/z 305.1 (M+H)⁺.

Step 2—5-(2,2-Dimethylmorpholino)pyrazolo[1,5-a]pyrimidine-3-carboxylic acid

To a mixture of ethyl 5-(2,2-dimethylmorpholin-4-yl)pyrazolo[1,5-a]pyrimidine-3-carboxylate (1.3 g, 4.27 mmol) in mixed solvent of THF (6 mL), MeOH (6 mL) and H₂O (2 mL) was added LiOH.H₂O (538 mg, 12.8 mmol), then the mixture was stirred at 60° C. for 12 hrs. After cooling down to rt, the solvent was removed to give residue, and the residue was diluting with water (20 ml). Then the pH was adjusted to ~5 with HCl (1 N) and he solid was collected by filtration to give white solid (1.1 g, 93% yield). LC-MS (ESI⁺) m/z 299.2 (M+Na)⁺.

N-[3-(difluoromethyl)-1-(4-formylcyclohexyl)pyrazol-4-yl]-5-(2,2-dimethylmorpholin-4-yl)pyrazolo[1,5-a]pyrimidine-3-carboxamide (Intermediate AQD)

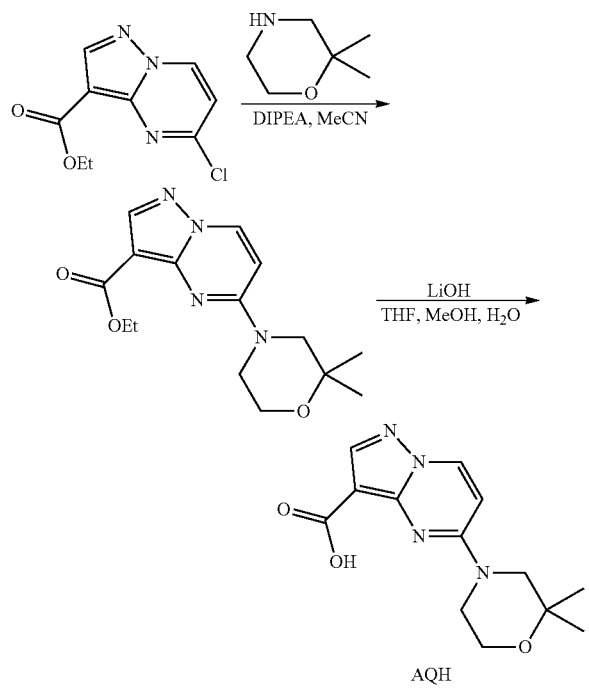

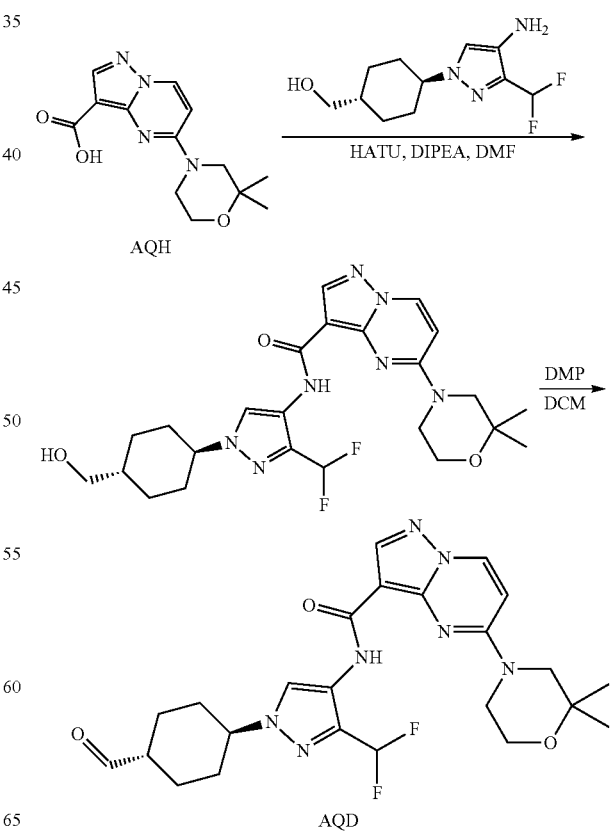

Step 1—N-(3-(Difluoromethyl)-1-((1r,4r)-4-(hydroxymethyl)cyclohexyl)-1H-pyrazol-4-yl)-5-(2,2-dimethylmorpholino)pyrazolo[1,5-a]pyrimidine-3-carboxamide To a solution of 5-(2,2-dimethylmorpholin-4-yl)pyrazolo[1,5-a]pyrimidine-3-carboxylic acid (900 mg, 3.26 mmol, Intermediate AQH), [4-[(1S)-4-amino-3-(difluoromethyl)pyrazol-1-yl]cyclohexyl]methanol (879 mg, 3.58 mmol, Intermediate TD) and 1-methylimidazole (321 mg, 3.91 mmol) in ACN (30 mL) was stirred at 25° C. Then to the reaction mixture was added [chloro(dimethylamino)methylene]-dimethyl-ammonium; hexafluorophosphate (1.10 g, 3.91 mmol) and stirred at 25° C. for 2 hrs. On completion, the mixture was quenched with water (100 mL) and extracted with ethyl acetate (3×250 mL). The combined organic phase was dried over anhydrous sodium sulfate, filtered and concentrated to give a residue. The residue was purified by silica gel chromatography (DCM:MeOH=20:1) to afford a light yellow solid (410 mg, 25% yield). $^1$H NMR (400 MHz, DMSO-$d_6$) δ 9.29 (s, 1H), 8.81 (d, J=8.0 Hz, 1H), 8.40 (s, 1H), 8.28 (s, 1H), 7.29-7.00 (m, 1H), 6.93 (d, J=8.0 Hz, 1H), 4.48 (t, J=5.2 Hz, 1H), 4.24-4.15 (m, 1H), 3.76 (s, 4H), 3.71-3.65 (m, 2H), 3.27 (s, 2H), 2.05 (d, J=9.6 Hz, 2H), 1.90-1.84 (m, 2H), 1.78-1.68 (m, 2H), 1.49-1.39 (m, 1H), 1.20 (s, 6H), 1.14-1.04 (m, 2H).

Step 2—N-(3-(Difluoromethyl)-1-((1r,4r)-4-formylcyclohexyl)-1H-pyrazol-4-yl)-5-(2,2-dimethyl morpholino)pyrazolo[1,5-a]pyrimidine-3-carboxamide To a solution of N-[3-(difluoromethyl)-1-[4-(hydroxymethyl)cyclohexyl]pyrazol-4-yl]-5-(2,2-dimethylmorpholin-4-yl)pyrazolo[1,5-a]pyrimidine-3-carboxamide (380 mg, 755 umol) and DMP (384 mg, 905 umol) in DCM (3 mL) was stirred at 25° C. for 1 hr. On completion, the reaction mixture was quenched with saturated solution of sodium thiosulfate (5 mL) and diluted with water (20 mL), then extracted with ethyl acetate (3×50 mL). The combined organic layer was washed with sodium bicarbonate solution. The combined organic phase was dried over anhydrous sodium sulfate, filtered and concentrated to give the title compound (300 mg, 75% yield) as an off-white solid. $^1$H NMR (400 MHz, DMSO-$d_6$) δ 9.63 (s, 1H), 9.31 (s, 1H), 8.82 (d, J=8.0 Hz, 1H), 8.42 (s, 1H), 8.29 (s, 1H), 7.32-6.99 (m, 1H), 6.94 (d, J=8.0 Hz, 1H), 4.31-4.15 (m, 1H), 3.94-3.55 (m, 6H), 2.40 (t, J=12.4 Hz, 1H), 2.21-2.01 (m, 4H), 1.89-1.77 (m, 2H), 1.44-1.33 (m, 2H), 1.22-1.18 (m, 6H).

5-(1,4-Oxazepan-4-yl)pyrazolo[1,5-a]pyrimidine-3-carboxylic acid (Intermediate AQE)

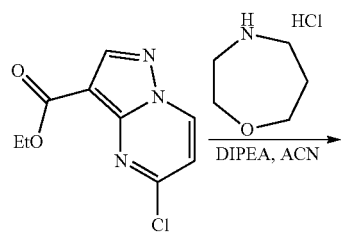

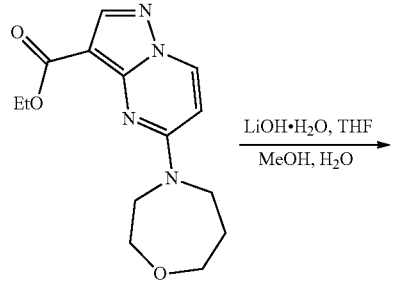

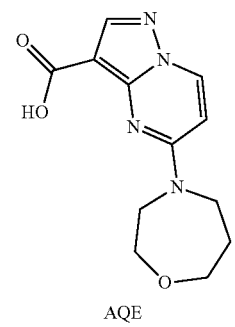

AQE

Step 1—Ethyl 5-(1,4-oxazepan-4-yl)pyrazolo[1,5-a]pyrimidine-3-carboxylate

A mixture of ethyl 5-chloropyrazolo[1,5-a]pyrimidine-3-carboxylate (2.50 g, 11.1 mmol), 1,4-oxazepane; hydrochloride (1.60 g, 11.6 mmol, HCl) and DIPEA (4.30 g, 33.2 mmol) in MeCN (35 mL) was stirred at 60° C. for 1 hr. On completion, the reaction mixture was concentrated in vacuo. The residue was diluted in ethyl acetate (50 mL) and water (80 mL). The mixture was acidified by saturated critic acid aqueous until the pH=7. The mixture was extracted with ethyl acetate (3×50 mL). The organic layer was concentrated in vacuo to give the title compound (3.00 g, 93% yield) as yellow solid. $^1$H NMR (400 MHz, DMSO-$d_6$) δ 8.70 (d, J=8.0 Hz, 1H), 8.19 (s, 1H), 6.78 (d, J=8.0 Hz, 1H), 4.21-4.15 (m, 2H), 4.06-3.69 (m, 6H), 3.64 (t, J=5.6 Hz, 2H), 1.92-1.89 (m, 2H), 1.27 (t, J=7.2 Hz, 3H).

Step 2—5-(1,4-Oxazepan-4-yl)pyrazolo[1,5-a]pyrimidine-3-carboxylic acid

To a solution of ethyl 5-(1,4-oxazepan-4-yl)pyrazolo[1,5-a]pyrimidine-3-carboxylate (3.40 g, 11.7 mmol) in THF (3 mL), MeOH (3 mL) and H$_2$O (1 mL) was added LiOH.H$_2$O (1.47 g, 35.1 mmol), and the mixture was stirred at 60° C. for 16 hrs. On completion, the reaction mixture was adjusted pH to 5~6 by HCl aq. (1 mL) and extracted with ethyl acetate (3×15 mL). The combined organic layers were washed with brine (5 mL), dried over anhydrous sodium sulfate, filtered and concentrated in vacuo to give the title compound (2.60 g, 85% yield) as white solid. $^1$H NMR (400 MHz, DMSO-$d_6$) δ 11.68 (s, 1H), 8.70 (d, J=8.0 Hz, 1H), 8.17 (s, 1H), 6.76 (d, J=8.0 Hz, 1H), 3.94-3.71 (m, 5H), 3.64 (t, J=5.6 Hz, 2H), 1.95-1.81 (m, 3H).

N-[(1S)-3-(difluoromethyl)-1-(4-formylcyclohexyl)pyrazol-4-yl]-5-(1,4-oxazepan-4-yl)pyrazolo[1,5-a]pyrimidine-3-carboxamide (Intermediate AQF)

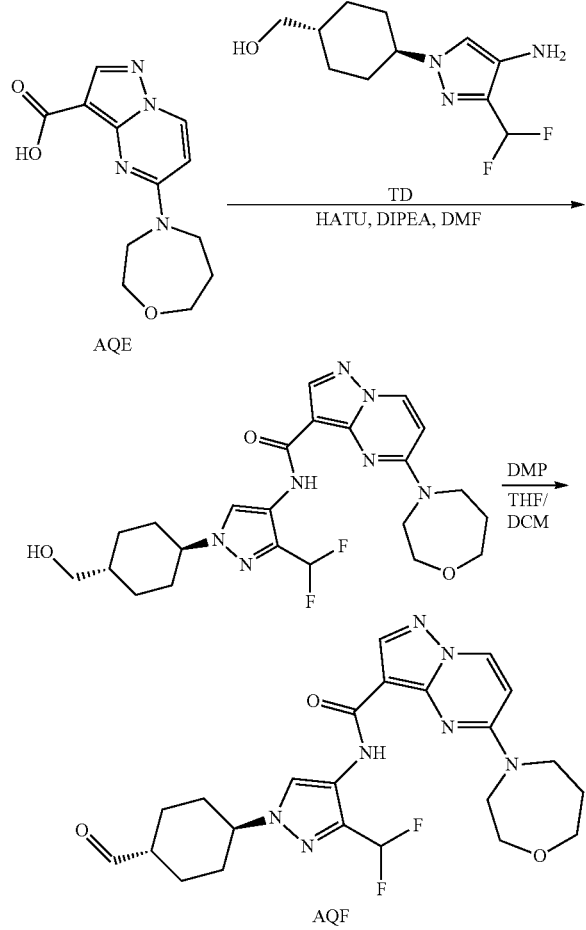

Step 1—N-(3-(difluoromethyl)-1-((1r,4r)-4-(hydroxymethyl)cyclohexyl)-1H-pyrazol-4-yl)-5-(1,4-oxazepan-4-yl)pyrazolo[1,5-a]pyrimidine-3-carboxamide To a solution of 5-(1,4-oxazepan-4-yl)pyrazolo[1,5-a]pyrimidine-3-carboxylic acid (1.00 g, 3.81 mmol, Intermediate AQE) and [4-[4-amino-3-(difluoromethyl)pyrazol-1-yl]cyclohexyl]methanol (1.22 g, 4.96 mmol, Intermediate TD) in DMF (10 mL) was added HATU (2.17 g, 5.72 mmol) and DIPEA (1.48 g, 11.4 mmol) at 25° C. Then the mixture was stirred at 60° C. for 16 hrs. On completion, the reaction mixture was diluted with water (15 mL) and extracted with ethyl acetate (3×25 mL). The combined organic layers were washed with brine (15 mL), dried over anhydrous sodium sulfate, filtered and concentrated in vacuo to give a residue. The residue was purified by silica gel chromatography (petroleum ether:ethyl acetate=20:1 to dichloromethane:methanol=20:1) to give the title compound (1.50 g, 56% yield) as white solid. $^1$H NMR (400 MHz, DMSO-d$_6$) δ 9.30 (s, 1H), 8.77 (d, J=8.0 Hz, 1H), 8.47-8.20 (m, 2H), 7.33-6.92 (m, 1H), 6.82 (d, J=8.0 Hz, 1H), 4.19-4.13 (m, 1H), 3.77 (s, 3H), 3.72-3.57 (m, 3H), 3.34 (s, 3H), 3.17-3.15 (m, 2H), 2.06-2.03 (m, 2H), 1.96-1.81 (m, 5H), 1.81-1.61 (m, 3H), 1.45-1.42 (m, 1H).

Step 2—N-(3-(difluoromethyl)-1-((1r,4r)-4-formylcyclohexyl)-1H-pyrazol-4-yl)-5-(1,4-oxazepan-4-yl)pyrazolo[1,5-a]pyrimidine-3-carboxamide To a mixture of N-[3-(difluoromethyl)-1-[4-(hydroxymethyl)cyclohexyl]pyrazol-4-yl]-5-(1,4-oxazepan-4-yl)pyrazolo[1,5-a]pyrimidine-3-carboxamide (1.60 g, 3.27 mmol) in DCM (20 mL) and THF (20 mL) was added DMP (1.52 g, 3.60 mmol) at 0° C. The reaction mixture was stirred at 20° C. for 1 hr under nitrogen atmosphere. On completion, the reaction mixture was diluted with saturated Na$_2$S$_2$O$_3$ aqueous (10 mL) and saturated NaHCO$_3$ aqueous (10 mL). The mixture was stirred at 20° C. for 0.5 hr. The mixture was diluted with water (100 mL) and extracted with DCM (3×40 mL). The organic layer was washed with saturated NaHCO$_3$ aqueous (3×40 mL) and brine (3×40 mL). The combined organic layers were dried over anhydrous sodium sulfate, filtered and concentrated in vacuo to give the title compound (1.38 g, 87% yield) as yellow solid. $^1$H NMR (400 MHz, DMSO-d$_6$) δ 9.60 (d, J=3.2 Hz, 1H), 9.31 (s, 1H), 8.78 (d, J=8.0 Hz, 1H), 8.40 (s, 1H), 8.27 (s, 1H), 7.26-6.96 (m, 1H), 6.83 (d, J=8.0 Hz, 1H), 4.27-4.16 (m, 1H), 4.09-3.95 (m, 2H), 3.93-3.81 (m, 2H), 3.80-3.75 (m, 2H), 3.67 (t, J=5.6 Hz, 2H), 2.43-2.34 (m, 1H), 2.13-2.03 (m, 4H), 1.93-1.88 (m, 2H), 1.86-1.76 (m, 2H), 1.43-1.32 (m, 2H).

3-[3-Methyl-2-oxo-4-[3-(4-piperidyl)prop-1-ynyl]benzimidazol-1-yl]piperidine-2,6-dione (Intermediate AQI)

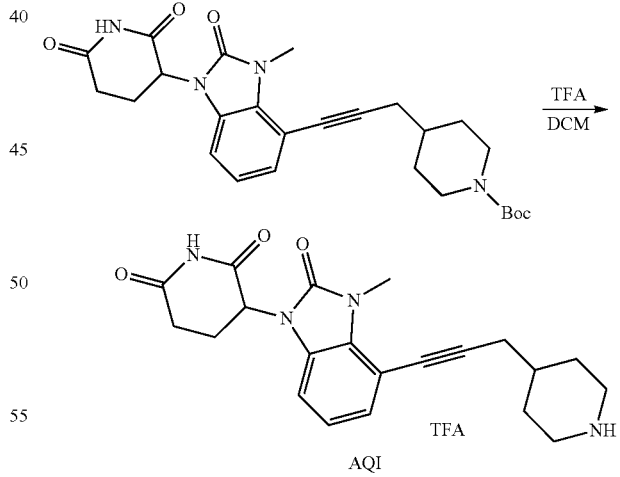

To a solution of tert-butyl 4-[3-[1-(2,6-dioxo-3-piperidyl)-3-methyl-2-oxo-benzimidazol-4-yl] prop-2-ynyl]piperidine-1-carboxylate (90.0 mg, 187 umol, synthesized via Step 1 of Intermediate AKP) in DCM (2 mL) was added TFA (2 mL). The mixture was stirred at 25° C. for 3 hours. On completion, the reaction mixture was concentrated in vacuo to give the title compound (80.0 mg, 86% yield, TFA salt) as a white solid. LC-MS (ESI$^+$) m/z 381.3 (M+H)$^+$.

3-[4-(5-aminopent-1-ynyl)-3-methyl-2-oxo-benzimi-dazol-1-yl]piperidine-2,6-dione (Intermediate AQJ)

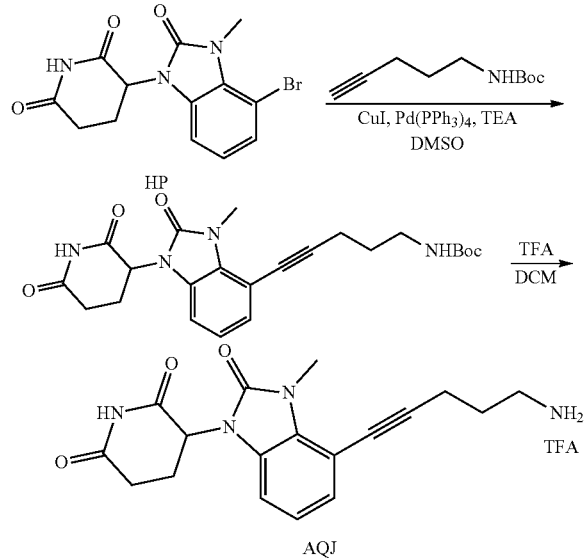

Step 1—Tert-butyl N-[5-[1-(2,6-dioxopiperidin-3-yl)-3-methyl-2-oxo-1,3-benzodiazol-4-yl]pent-4-yn-1-yl] carbamate To a stirred mixture of 3-(4-bromo-3-methyl-2-oxo-1,3-benzodiazol-1-yl)piperidine-2,6-dione (10.00 g, 29.572 mmol, Intermediate HP) and tert-butyl N-(pent-4-yn-1-yl) carbamate (8.13 g, 44.358 mmol, CAS #151978-50-6) in DMSO (100.00 mL) was added TEA (50.00 mL) and CuI (0.56 g, 2.957 mmol) at rt. To the above mixture was added Pd(PPh$_3$)$_4$ (3.42 g, 2.957 mmol) at rt and the resulting mixture was stirred for 3 h at 80° C. under nitrogen atmosphere. After being cooled down to rt, the mixture was diluted with water (200 mL) and was extracted with EtOAc (4×200 mL). The combined organic layers were washed with brine (2×200 mL), dried over anhydrous Na$_2$SO$_4$ and filtered. The filtrate was concentrated under reduced pressure. The residue was purified by silica gel column chromatography with the following conditions (Mobile Phase: EtOAc) to afford the title compound (11 g, 84%) as a brown solid. $^1$H NMR (400 MHz, Methanol-d$_4$) δ 7.15 (dd, J=7.5, 1.5 Hz, 1H), 7.10-7.01 (m, 2H), 5.34 (dd, J=12.2, 5.4 Hz, 1H), 3.78 (s, 3H), 3.23 (t, J=6.9 Hz, 2H), 3.01-2.75 (m, 3H), 2.54 (t, J=7.1 Hz, 2H), 2.19 (dp, J=10.3, 5.8, 5.2 Hz, 1H), 1.82 (p, J=7.0 Hz, 2H), 1.45 (s, 9H); LC/MS (ESI, m/z): [(M+18)]$^+$=458.20.

Step 2—3-[4-(5-Aminopent-1-yn-1-yl)-3-methyl-2-oxo-1,3-benzodiazol-1-yl]piperidine-2,6-dione; trifluoroacetic acid To a solution of tert-butyl N-[5-[1-(2,6-dioxopiperidin-3-yl)-3-methyl-2-oxo-1,3-benzodiazol-4-yl]pent-4-yn-1-yl] carbamate (3.00 g, 6.810 mmol) in DCM (40.00 mL) was added TFA (10.00 mL) at 25° C. The mixture was stirred at 25° C. for 1 h. The resulting solution was concentrated under reduced pressure to afford the title compound (2 g, 86%) as a brown solid. $^1$H NMR (400 MHz, Methanol-d$_4$) δ 7.13 (ddd, J=16.2, 7.9, 1.3 Hz, 2H), 7.04 (d, J=8.0 Hz, 1H), 5.35 (dd, J=12.2, 5.4 Hz, 1H), 3.77 (s, 3H), 3.13 (t, J=7.7 Hz, 2H), 2.99-2.75 (m, 3H), 2.68 (t, J=7.0 Hz, 2H), 2.23-2.13 (m, 1H), 2.02 (dd, J=14.7, 7.0 Hz, 2H); LC/MS (ESI, m/z): [(M+1)]$^+$=341.10.

3-[3-(3-Aminopropoxy)propoxy]propan-1-ol (Intermediate AQL)

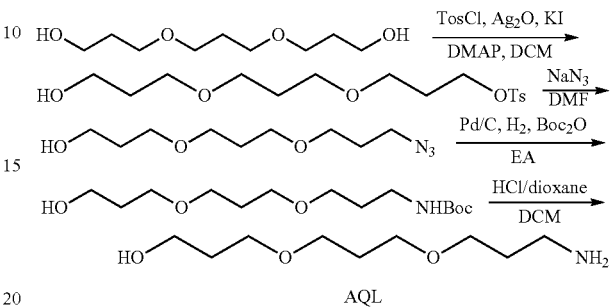

AQL

Step 1—3-[3-(3-Hydroxypropoxy)propoxy]propyl 4-methylbenzenesulfonate

To a mixture of 3-[3-(3-hydroxypropoxy)propoxy]propan-1-ol (10 g, 52.01 mmol, CAS #4146-32-4), Ag$_2$O (14.4 g, 62.4 mmol), KI (863 mg, 5.20 mmol), DMAP (1.27 g, 10.4 mmol) in DCM (1000 mL) was added TosCl (9.92 g, 52.0 mmol). The reaction mixture was stirred at 25° C. for 12 hours. On completion, the reaction mixture was filtered and concentrated in vacuo. The residue was purified by column chromatography to give the title compound (10.0 g, 55% yield) as colorless oil. $^1$H NMR (400 MHz, CDCl$_3$) δ 7.83-7.78 (m, 2H), 7.36-7.31 (m, 2H), 4.75-4.64 (m, 1H), 4.02-3.80 (m, 2H), 3.77-3.07 (m, 10H), 2.44 (s, 3H), 1.13-1.07 (m, 6H).

Step 2—3-[3-(3-Azidopropoxy)propoxy]propan-1-ol

To a mixture of 3-[3-(3-hydroxypropoxy)propoxy]propyl 4-methylbenzenesulfonate (2.00 g, 5.77 mmol) in DMF (30 mL) was added NaN$_3$ (750 mg, 11.5 mmol). The reaction mixture was stirred at 80° C. for 12 hours. On completion, the reaction mixture was diluted with water (30 mL) and extracted with EA (2×100 mL). The combined organic layer was concentrated to give the title compound (1.20 g, 100% yield) as light yellow oil.

Step 3—Tert-butyl N-[3-[3-(3-hydroxypropoxy)propoxy]propyl]carbamate

To a mixture of 3-[3-(3-azidopropoxy)propoxy]propan-1-ol (1.20 g, 5.52 mmol) in EA (10 mL) was added Boc$_2$O (1.81 g, 8.28 mmol, 1.90 mL) and Pd/C (500 mg, 10 wt %). The reaction mixture was stirred at 25° C. for 12 hours under H$_2$ (15 Psi) atmosphere. On completion, the reaction mixture was filtered and concentrated in vacuo. The residue was purified by column chromatography to give the title compound (1.20 g, 74% yield) as light yellow oil.

Step 4—3-[3-(3-Aminopropoxy)propoxy]propan-1-ol

To a mixture of tert-butyl N-[3-[3-(3-hydroxypropoxy)propoxy]propyl]carbamate (600 mg, 2.06 mmol) in DCM (5 mL) was added HCl/dioxane (4 M, 3 m). The reaction mixture was stirred at 25° C. for 2 hours. On completion, the reaction mixture was concentrated in vacuo to give the title compound (460 mg, 98% yield, HCl) as colorless oil.

3-[3-[3-[[2-(2,6-Dioxo-3-piperidyl)-1,3-dioxo-isoindolin-4-yl]amino]propoxy]propoxy] propanal (Intermediate AQM)

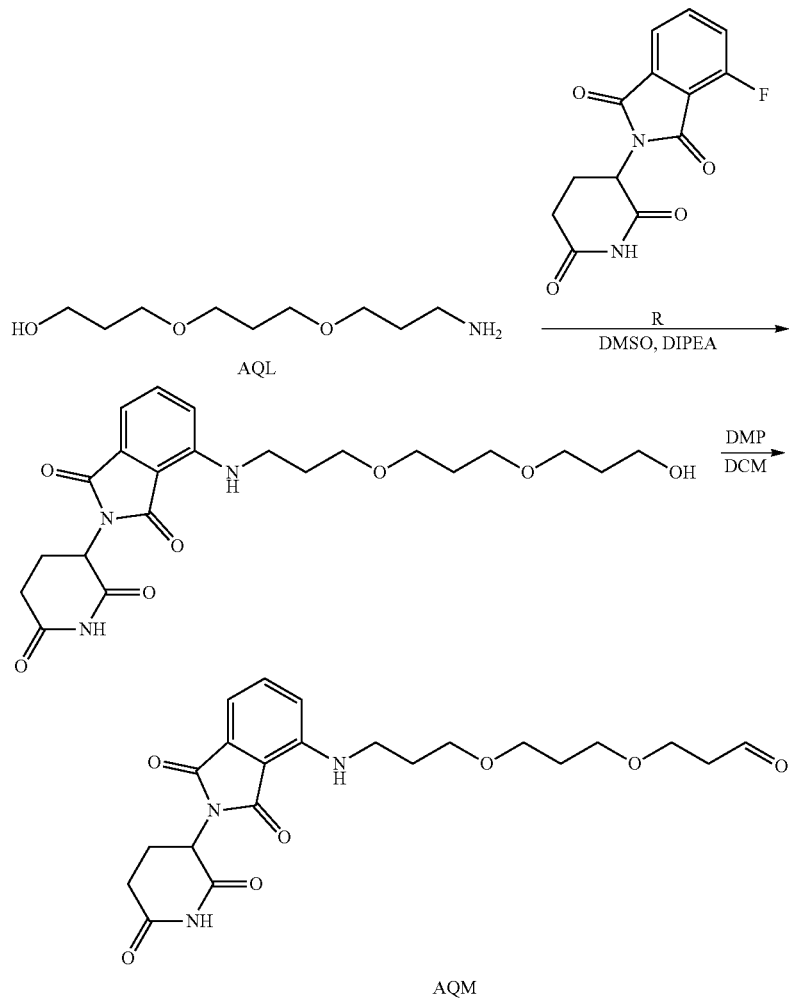

Step 1—2-(2,6-Dioxo-3-piperidyl)-4-[3-[3-(3-hydroxypropoxy)propoxy]propylamino]isoindoline-1,3-dione To a mixture of 2-(2,6-dioxo-3-piperidyl)-4-fluoro-isoindoline-1,3-dione (424 mg, 1.54 mmol, Intermediate R) and 3-[3-(3-aminopropoxy)propoxy]propan-1-ol (350 mg, 1.54 mmol, HCl, Intermediate AQL) in DMSO (5 mL) was added DIPEA (595 mg, 4.61 mmol, 803 uL). The reaction mixture was stirred at 130° C. for 2 hours. On completion, the reaction mixture was filtered and concentrated in vacuo. The residue was purified by reverse phase (0.1% FA condition) to give the title compound (650 mg, 94% yield) as yellow solid. $^1$H NMR (400 MHz, DMSO-$d_6$) δ 11.08 (s, 1H), 7.58 (t, J=7.6 Hz, 1H), 7.21-7.11 (m, 1H), 7.03 (d, J=7.2 Hz, 1H), 6.64-6.36 (m, 1H), 5.09-5.02 (m, 1H), 4.53-4.39 (m, 1H), 4.01-3.82 (m, 1H), 3.75-3.35 (m, 6H), 3.30-3.11 (m, 3H), 2.95-2.81 (m, 1H), 2.63-2.53 (m, 2H), 2.08-1.93 (m, 1H), 1.21-0.98 (m, 8H); LC-MS (ESI$^+$) m/z 448.2 (M+H)$^+$.

Step 2—3-[3-[3-[[2-(2,6-Dioxo-3-piperidyl)-1,3-dioxo-isoindolin-4-yl]amino]propoxy]propoxy] propanal To a mixture of 2-(2,6-Dioxo-3-piperidyl)-4-[3-[3-(3-hydroxypropoxy)propoxy]propylamino] isoindoline-1,3-dione (60.0 mg, 134 umol) in DCM (3 mL) was added DMP (73.9 mg, 174 umol, 53.9 uL). The reaction mixture was stirred at 25° C. for 4 hours. On completion, the reaction mixture was quenched by saturated Na$_2$S$_2$O$_3$ (15 mL) and saturated NaHCO$_3$ (15 mL) at 25° C., and then stirred for 30 minutes. Then the mixture was extracted with DCM (2×30 mL). The combined organic layers was dried over Na$_2$SO$_4$, filtered and concentrated in vacuo to give the title compound (59.0 mg, 98% yield) as yellow solid. $^1$H NMR (400 MHz, DMSO-$d_6$) δ 11.08 (s, 1H), 7.58 (t, J=7.6 Hz, 1H), 7.20-7.12 (m, 1H), 7.03 (d, J=6.8 Hz, 1H), 6.71-6.38 (m, 1H), 5.09-5.01 (m, 1H), 4.15-4.08 (m, 1H), 3.75-3.32 (m, 10H), 2.93-2.83 (m, 1H), 2.65-2.58 (m, 2H), 2.05-1.96 (m, 3H), 1.19-1.11 (m, 4H); LC-MS (ESI+) m/z 446.2 (M+H)+.

N-[3-(difluoromethyl)-1-(4-piperidyl)pyrazol-4-yl]-5-[(1R,4R)-2-oxa-5-azabicyclo[2.2.1] heptan-5-yl] pyrazolo[1,5-a]pyrimidine-3-carboxamide (Intermediate AQN)

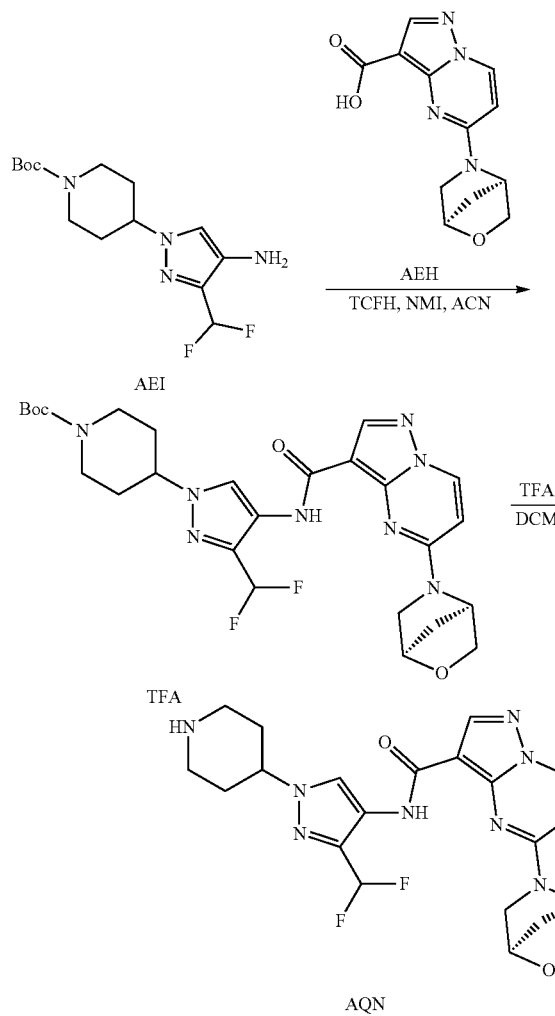

Step 1—Tert-butyl 4-[3-(difluoromethyl)-4-[[5-[(1R,4R)-2-oxa-5-azabicyclo[2.2.1]heptan-5-yl] pyrazolo[1,5-a]pyrimidine-3-carbonyl]amino]pyrazol-1-yl]piperidine-1-carboxylate To a mixture of 5-[(1R,4R)-2-oxa-5-azabicyclo[2.2.1] heptan-5-yl]pyrazolo[1,5-a]pyrimidine-3-carboxylic acid (904 mg, 3.48 mmol, Intermediate AEH), 1-methylimidazole (908 mg, 11.0 mmol, 881 uL) and [chloro(dimethylamino)methylene]-dimethyl-ammonium; hexafluorophosphate (1.06 g, 3.79 mmol) in ACN (20 mL) was added tert-butyl 4-[4-amino-3-(difluoromethyl)pyrazol-1-yl]piperidine-1-carboxylate (1.00 g, 3.16 mmol, Intermediate AEI). The reaction mixture was stirred at 25° C. for 20 hours. On completion, the reaction mixture was quenched with water (0.05 mL) and concentrated in vacuo. The residue was purified by reverse phase (0.1% FA condition) to give the title compound (600 mg, 33% yield) as light yellow solid. 1H NMR (400 MHz, DMSO-d6) δ 9.50 (d, J=5.2 Hz, 1H), 8.84-8.72 (m, 1H), 8.42 (d, J=4.0 Hz, 1H), 8.25 (d, J=5.2 Hz, 1H), 7.27-6.97 (m, 1H), 6.88-6.41 (m, 1H), 5.30-5.00 (m, 1H), 4.76 (d, J=15.2 Hz, 1H), 4.50-4.37 (m, 1H), 4.05 (d, J=11.6 Hz, 2H), 3.84-3.72 (m, 2H), 3.66-3.41 (m, 2H), 2.89 (s, 2H), 2.10-1.89 (m, 4H), 1.83-1.69 (m, 2H), 1.41 (s, 9H); LC-MS (ESI+) m/z 559.4 (M+H)+.

Step 2—N-[3-(difluoromethyl)-1-(4-piperidyl)pyrazol-4-yl]-5-[(1R,4R)-2-oxa-5-azabicyclo[2.2.1] heptan-5-yl]pyrazolo[1,5-a]pyrimidine-3-carboxamide To a mixture of tert-butyl 4-[3-(difluoromethyl)-4-[[5-[(1R,4R)-2-oxa-5-azabicyclo[2.2.1]heptan-5-yl] pyrazolo[1,5-a]pyrimidine-3-carbonyl]amino]pyrazol-1-yl]piperidine-1-carboxylate (100 mg, 179 umol) in DCM (3 mL) was added TFA (20.4 mg, 179 umol, 13.2 uL). The reaction mixture was stirred at 25° C. for 0.5 hour. On completion, the reaction mixture was concentrated in vacuo to give the title compound (100 mg, 97% yield, TFA) as light yellow oil. LC-MS (ESI+) m/z 459.1 (M+H)+.

5-[Cyclopropylmethyl(methyl)amino]-N-[3-(difluoromethyl)-1-(4-formylcyclohexyl)pyrazol-4-yl]pyrazolo[1,5-a]pyrimidine-3-carboxamide (Intermediate AQP)

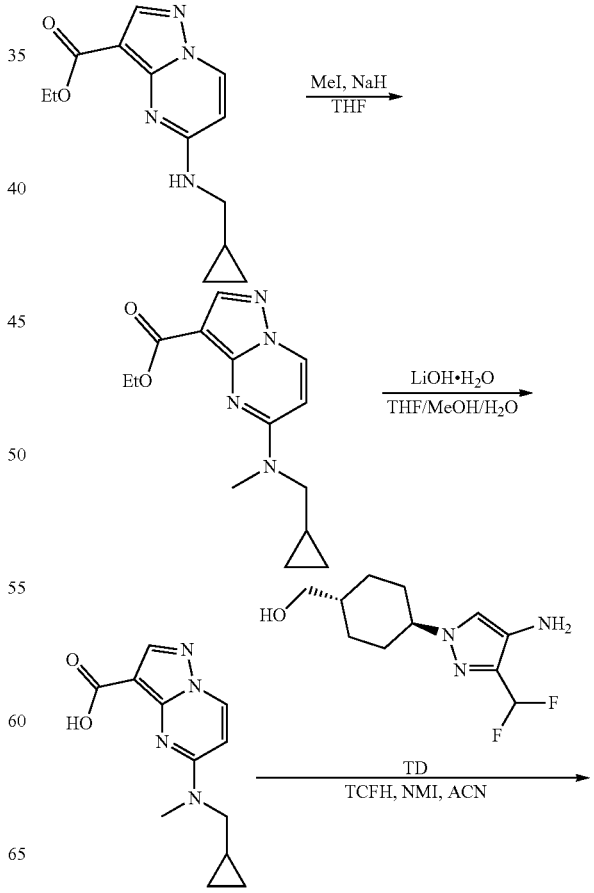

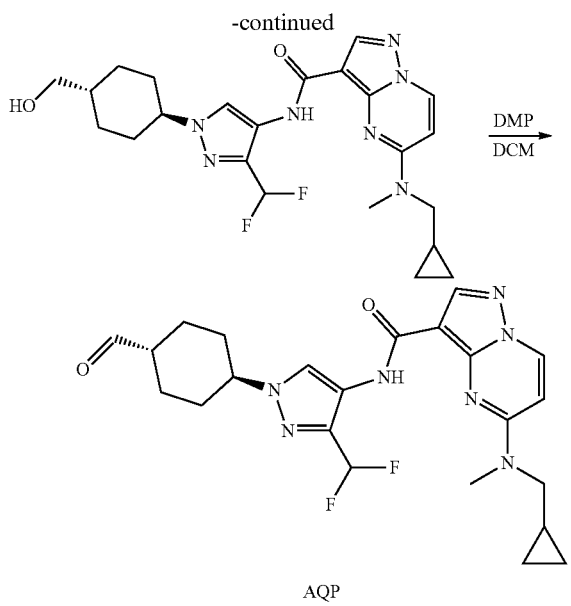

AQP

Step 1—Ethyl 5-[cyclopropylmethyl(methyl)amino]pyrazolo[1,5-a]pyrimidine-3-carboxylate To a solution of ethyl 5-(cyclopropylmethylamino)pyrazolo[1,5-a]pyrimidine-3-carboxylate (500 mg, 1.92 mmol, synthesized via Step 1 of Intermediate ABO) in THF (10 mL) was added NaH (99.8 mg, 2.50 mmol, 60% dispersion in mineral oil) at 0° C. for 30 min, then MeI (327 mg, 2.31 mmol, 143 uL) was added. The reaction mixture was stirred at 25° C. for 12 hr. On completion, the reaction was quenched with H$_2$O (10 mL), then extracted with EA (2×30 mL). The organic phase was concentrated in vacuo to give a residue. The residue was purified by reverse phase (0.1% FA condition) to give the title compound (480 mg, 91.1% yield) as a white solid. $^1$H NMR (400 MHz, DMSO-d$_6$) δ 8.66 (d, J=8.0 Hz, 1H), 8.18 (s, 1H), 6.71 (s, 1H), 4.18 (q, J=7.2 Hz, 2H), 3.68-3.41 (m, 2H), 3.33 (s, 3H), 1.28 (t, J=7.2 Hz, 3H), 1.20-1.03 (m, 1H), 0.52-0.30 (m, 4H); LC-MS (ESI$^+$) m/z 275.1 (M+H)$^+$.

Step 2—5-[Cyclopropylmethyl(methyl)amino]pyrazolo[1,5-a]pyrimidine-3-carboxylic acid To a solution of ethyl 5-[cyclopropylmethyl(methyl)amino]pyrazolo[1,5-a]pyrimidine-3-carboxylate (480 mg, 1.75 mmol) in THF (10 mL), H$_2$O (2 mL) and MeOH (2 mL) was added LiOH·H$_2$O (95.4 mg, 2.27 mmol). The reaction mixture was stirred at 60° C. for 16 hrs. On completion, the mixture was concentrated in vacuo and then diluted with H$_2$O (20 mL). Then the mixture was adjusted with 1N HCl until the pH=5, and the mixture was lyophilized to give the title compound (410 mg, 95% yield) as a yellow solid. LC-MS (ESI$^+$) m/z 247.1 (M+1)$^+$.

Step 3—5-[Cyclopropylmethyl(methyl)amino]-N-[3-(difluoromethyl)-1-[4-(hydroxymethyl) cyclohexyl]pyrazol-4-yl]pyrazolo[1,5-a]pyrimidine-3-carboxamide To a solution of 5-[cyclopropylmethyl(methyl)amino]pyrazolo[1,5-a]pyrimidine-3-carboxylic acid (150 mg, 609 umol) in ACN (8 mL) was added 1-methylimidazole (175 mg, 2.13 mmol, 169 uL), [chloro(dimethylamino)methylene]-dimethyl-ammonium; hexafluorophosphate (222 mg, 791 umol), the mixture was stirred at 25° C. for 30 min. Then [4-[4-amino-3-(difluoromethyl)pyrazol-1-yl] cyclohexyl]methanol (149 mg, 609 umol, Intermediate TD) was added to the mixture, and the reaction mixture was stirred at 25° C. for 12 hrs. On completion, the reaction was quenched with water (0.5 mL) and the mixture was concentrated in vacuo to give the residue. The residue was purified by reversed-phase (0.1% FA condition) to give the title compound (130 mg, 45% yield) as a white solid. $^1$H NMR (400 MHz, DMSO-d$_6$) δ 9.40 (s, 1H), 8.73 (d, J=8.0 Hz, 1H), 8.37 (s, 1H), 8.25 (s, 1H), 7.27-6.95 (m, 1H), 6.81 (d, J=2.4 Hz, 1H), 4.47 (t, J=5.2 Hz, 1H), 4.23-4.12 (m, 1H), 3.68-3.48 (m, 2H), 3.29-3.22 (m, 5H), 2.11-2.00 (m, 2H), 1.93-1.81 (m, 2H), 1.79-1.65 (m, 2H), 1.51-1.35 (m, 1H), 1.17-1.01 (m, 3H), 0.55-0.45 (m, 2H), 0.38-0.27 (m, 2H); LC-MS (ESI$^+$) m/z 474.3 (M+1)$^+$.

Step 4—5-[Cyclopropylmethyl(methyl)amino]-N-[3-(difluoromethyl)-1-(4-formylcyclohexyl)pyrazol-4-yl]pyrazolo[1,5-a]pyrimidine-3-carboxamide To a solution of 5-[cyclopropylmethyl(methyl)amino]-N-[3-(difluoromethyl)-1-[4-(hydroxymethyl) cyclohexyl]pyrazol-4-yl]pyrazolo[1,5-a]pyrimidine-3-carboxamide (130 mg, 274 umol) in DCM (5 mL) was added DMP (139 mg, 329 umol). The reaction mixture was stirred at 20° C. for 3 hrs. On completion, the reaction mixture was quenched with Na$_2$S$_2$O$_3$ (10 mL) and extracted with DCM (2×30 mL). The combined organic phase was washed with NaHCO$_3$ and brine (2×20 mL), dried with anhydrous Na$_2$SO$_4$, filtered and concentrated in vacuo to give the title compound (120 mg, 92.7% yield) as a yellow solid. $^1$H NMR (400 MHz, DMSO-d$_6$) δ 9.62 (s, 1H), 9.41 (s, 1H), 8.73 (d, J=8.0 Hz, 1H), 8.39 (m, 1H), 8.26 (s, 1H), 7.28-6.93 (m, 1H), 6.82 (d, J=2.8 Hz, 1H), 4.29-4.15 (m, 1H), 3.57 (s, 2H), 3.26 (s, 3H), 2.44-2.34 (m, 1H), 2.16-2.02 (m, 4H), 1.90-1.73 (m, 2H), 1.51-1.28 (m, 2H), 1.16-1.02 (m, 1H), 0.56-0.44 (m, 2H), 0.40-0.28 (m, 2H).

[4-[3-(Difluoromethyl)-4-(methylamino)pyrazol-1-yl] cyclohexyl]methanol (Intermediate AQT)

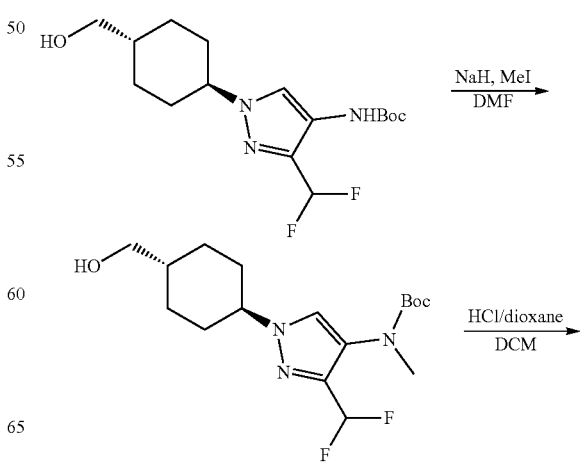

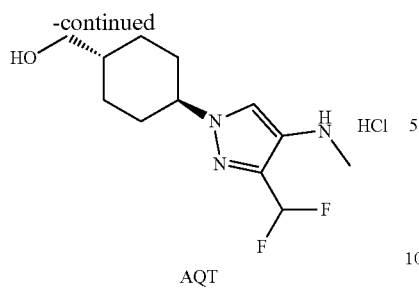

AQT

Step 1—Tert-butyl N-[3-(difluoromethyl)-1-[4-(hydroxymethyl)cyclohexyl]pyrazol-4-yl]-N-methyl-carbamate To a solution of tert-butyl N-[3-(difluoromethyl)-1-[4-(hydroxymethyl)cyclohexyl]pyrazol-4-yl]carbamate (500 mg, 1.45 mmol, synthesized via Step 1 of Intermediate ABM) in DMF (5 mL) was added NaH (86.8 mg, 2.17 mmol, 60% dispersion in mineral oil) at 0° C. for 30 min. Then MeI (308 mg, 2.17 mmol, 135 uL) was added, and the reaction mixture was stirred at 25° C. for 12 hour. On completion, the reaction was quenched with H$_2$O (10 mL), then extracted with EA (2×30 mL). The combined organic phase was dried over Na$_2$SO$_4$, filtered and the filtrate was concentrated in vacuo to give a residue. The residue was purified by reverse phase (0.1% FA condition) to give the title compound (420 mg, 81% yield) as a light yellow gum. $^1$H NMR (400 MHz, DMSO-d$_6$) δ 7.93 (s, 1H), 7.03-6.71 (m, 1H), 4.45 (t, J=5.2 Hz, 1H), 4.13-4.02 (m, 1H), 3.25 (t, J=6.0 Hz, 2H), 3.04 (s, 3H), 2.09-1.96 (m, 2H), 1.91-1.79 (m, 2H), 1.74-1.60 (m, 2H), 1.53-1.20 (m, 10H), 1.14-0.97 (m, 2H); LC-MS (ESI$^+$) m/z 360.2 (M+H)$^+$.

Step 2—[4-[3-(Difluoromethyl)-4-(methylamino)pyrazol-1-yl]cyclohexyl]methanol To a solution of tert-butyl N-[3-(difluoromethyl)-1-[4-(hydroxymethyl)cyclohexyl]pyrazol-4-yl]-N-methyl-carbamate (420 mg, 1.17 mmol) in DCM (2 mL) was added HCl/dioxane (4 M, 11.7 mL), and the reaction mixture was stirred at 25° C. for 2 hour. On completion, the mixture was concentrated in vacuo to give the title compound (340 mg, 98% yield) as yellow gum. LC-MS (ESI$^+$) m/z 260.2 (M+1)$^+$.

2-(2,6-dioxo-3-piperidyl)-4-[[3-(4-piperidyloxy)cyclobutyl]amino]isoindoline-1,3-dione (Intermediate AQS)

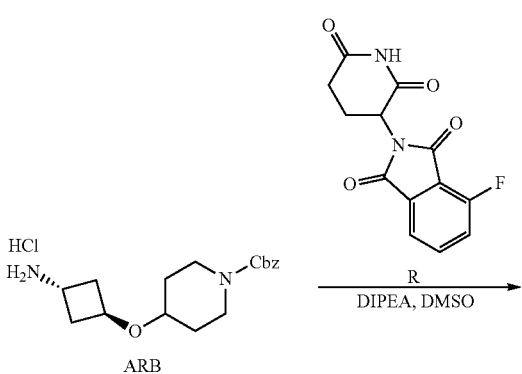

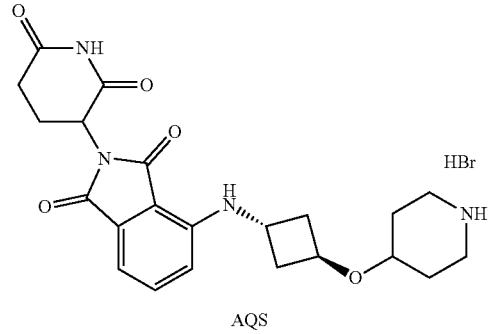

AQS

Step 1—Benzyl 4-[3-[[2-(2,6-dioxo-3-piperidyl)-1,3-dioxo-isoindolin-4-yl]amino]cyclobutoxy] piperidine-1-carboxylate To a mixture of 2-(2,6-dioxo-3-piperidyl)-4-fluoro-isoindoline-1,3-dione (259 mg, 938 umol, Intermediate R) and benzyl 4-(3-aminocyclobutoxy)piperidine-1-carboxylate (320 mg, 938 umol, HCl salt, Intermediate ARB) in DMSO (10 mL) was added DIPEA (243 mg, 1.88 mmol). The mixture was stirred at 130° C. for 2 hours. On completion, the mixture was poured into water (30 mL) and the aqueous phase was extracted with ethyl acetate (2×20 mL). The combined organic phase was washed with brine (2×30 mL), dried with anhydrous Na$_2$SO$_4$, filtered and concentrated in vacuo to give the residue. The residue was purified by reverse phase (0.1% FA condition) to give the title compound (220 mg, 41% yield) as a yellow solid. $^1$H NMR (400 MHz, DMSO-d$_6$) δ 11.12 (s, 1H), 7.67-7.53 (m, 1H), 7.43-7.27 (m, 5H), 7.09 (d, J=7.2 Hz, 1H), 6.91 (d, J=8.4 Hz, 1H), 6.51 (d, J=5.6 Hz, 1H), 5.13-5.01 (m, 3H), 4.33 (d, J=6.0 Hz, 1H), 4.12 (d, J=4.4 Hz, 1H), 3.80-3.70 (m, 2H), 3.54-3.44 (m, 1H), 3.20-3.03 (m, 2H), 2.97-2.84 (m, 1H), 2.70-2.54 (m, 2H), 2.42-2.32 (m, 2H), 2.31-2.21 (m, 2H), 2.08-1.99 (m, 1H), 1.86-1.73 (m, 2H), 1.42-1.29 (m, 2H).

Step 2—2-(2,6-Dioxo-3-piperidyl)-4-[[3-(4-piperidyloxy)cyclobutyl]amino]isoindoline-1,3-dione To a mixture of benzyl 4-[3-[[2-(2,6-dioxo-3-piperidyl)-1,3-dioxo-isoindolin-4-yl]amino] cyclobutoxy]piperidine-1-carboxylate (40 mg, 71.3 umol) in DCM (5 mL) was added HBr/HOAc (19.2 mg, 71.3 umol, 12.9 uL). The mixture was stirred at 20° C. for 0.5 hour. On completion, the mixture was concentrated in vacuo to give the title compound (32.0 mg, 100% yield) as brown oil. LC-MS (ESI$^+$) m/z 427.3 (M+H)$^+$.

5-(7-Azaspiro[3.5]nonan-2-ylmethylamino)-2-(2,6-dioxo-3-piperidyl)isoindoline-1,3-dione (Intermediate AQZ)

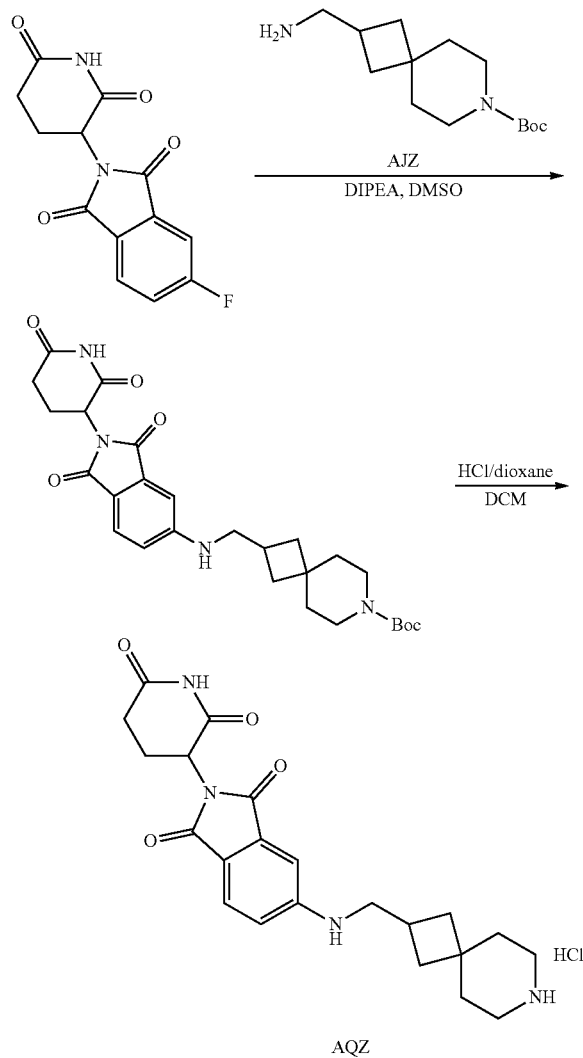

Step 1—Tert-butyl 2-[[[2-(2,6-dioxo-3-piperidyl)-1,3-dioxo-isoindolin-5-yl]amino]methyl]-7-azaspiro[3.5]nonane-7-carboxylate To a solution of tert-butyl 2-(aminomethyl)-7-azaspiro[3.5]nonane-7-carboxylate (506 mg, 1.99 mmol, Intermediate AJZ) and 2-(2,6-dioxo-3-piperidyl)-5-fluoro-isoindoline-1,3-dione (500 mg, 1.81 mmol, CAS #1160247-15-3) in DMSO (6 mL) was added DIPEA (935 mg, 7.24 mmol, 1.26 mL), and the reaction mixture was stirred at 130° C. for 3 hrs. On completion, the mixture was concentrated in vacuo to give a residue. The residue was purified by reverse phase (0.1% FA condition) to give the title compound (430 mg, 46.5% yield) as a yellow solid. $^1$H NMR (400 MHz, DMSO-$d_6$) δ 11.05 (s, 1H), 7.54 (d, J=8.4 Hz, 1H), 7.12-7.03 (m, 1H), 6.94 (s, 1H), 6.84 (d, J=8.0 Hz, 1H), 5.02 (dd, J=5.2, 12.8 Hz, 1H), 3.37-3.30 (m, 2H), 3.28-3.24 (m, 2H), 3.22-3.17 (m, 3H), 2.95-2.80 (m, 1H), 2.64-2.53 (m, 2H), 2.03-1.96 (m, 1H), 1.92 (t, J=10.2 Hz, 2H), 1.54-1.46 (m, 4H), 1.43-1.40 (m, 2H), 1.37 (s, 9H); LC-MS (ESI$^+$) m/z 411.3 (M+H−100)$^+$.

Step 2—5-(7-Azaspiro[3.5]nonan-2-ylmethylamino)-2-(2,6-dioxo-3-piperidyl)isoindoline-1,3-dione To a solution of tert-butyl 2-[[[2-(2,6-dioxo-3-piperidyl)-1,3-dioxo-isoindolin-5-yl]amino]methyl]-7-azaspiro[3.5]nonane-7-carboxylate (430 mg, 842 umol) in DCM (4 mL) was added HCl/dioxane (4 M, 4 mL), and the reaction mixture was stirred at 25° C. for 2 hr. On completion, the reaction mixture was concentrated in vacuo to give the title compound (370 mg, 98% yield, HCl salt) as a yellow solid. LC-MS (ESI$^+$) m/z 411.2 (M+H)$^+$.

N-[3-(difluoromethyl)-1-(4-formylcyclohexyl)pyrazol-4-yl]-N-methyl-5-morpholino-pyrazolo[1,5-a]pyrimidine-3-carboxamide (Intermediate AQU)

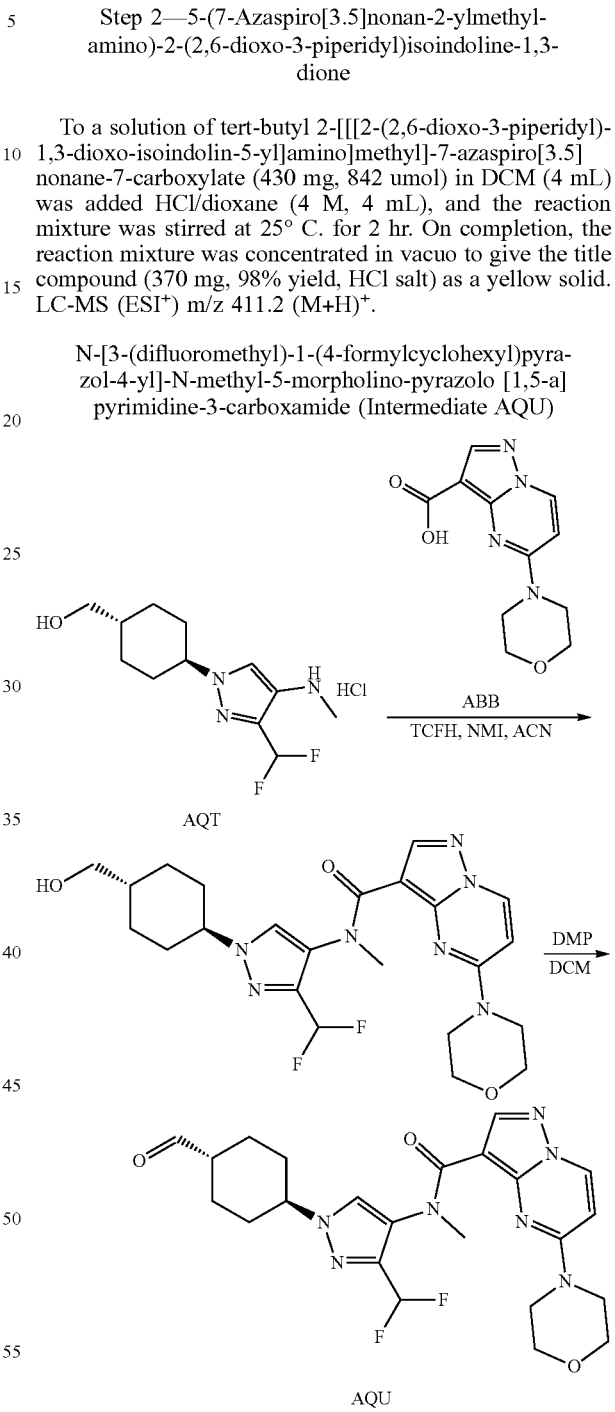

Step 1—N-[3-(difluoromethyl)-1-[4-(hydroxymethyl)cyclohexyl]pyrazol-4-yl]-N-methyl-5-morpholino-pyrazolo[1,5-a]pyrimidine-3-carboxamide To a solution of 5-morpholinopyrazolo[1,5-a]pyrimidine-3-carboxylic acid (243 mg, 980 umol, Intermediate ABB) in MeCN (10 mL) was added 1-methylimidazole (281 mg, 3.43 mmol, 273 uL) and [chloro(dimethylamino)methylene]-dimethyl-ammonium; hexafluorophosphate (357 mg, 1.27 mmol), the mixture was stirred at 25° C. for 30 min. Then [4-[3-(difluoromethyl)-4-(methylamino) pyrazol-1-yl]cyclohexyl]methanol (290 mg, 980 umol, HCl salt, Intermediate AQT) was added to the mixture, and the reaction mixture was stirred at 25° C. for 2 hours. On completion, the reaction was quenched with H₂O (2 mL) and then concentrated in vacuo to give the residue. The residue was purified by reverse phase (0.1% FA condition) to give the title compound (170 mg, 35% yield) as a white solid. ¹H NMR (400 MHz, DMSO-d₆) δ 8.62 (d, J=7.6 Hz, 1H), 7.88 (s, 1H), 7.77-7.54 (m, 1H), 6.98-6.71 (m, 2H), 4.45 (s, 1H), 4.06-3.96 (m, 1H), 3.73-3.62 (m, 8H), 3.26 (s, 3H), 3.23 (d, J=6.0 Hz, 2H), 1.91-1.77 (m, 4H), 1.65-1.50 (m, 2H), 1.45-1.29 (m, 1H), 1.10-0.96 (m, 2H); LC-MS (ESI⁺) m/z 490.3 (M+1)⁺.

Step 2—N-[3-(difluoromethyl)-1-(4-formylcyclohexyl)pyrazol-4-yl]-N-methyl-5-morpholino-pyrazolo [1,5-a]pyrimidine-3-carboxamide To a solution of N-[3-(difluoromethyl)-1-[4-(hydroxymethyl)cyclohexyl]pyrazol-4-yl]-N-methyl-5-morpholino-pyrazolo[1,5-a]pyrimidine-3-carboxamide (170 mg, 347 umol) in DCM (5 mL) was added DMP (176 mg, 416 umol, 129 uL), and the reaction mixture was stirred at 25° C. for 12 hours. On completion, the reaction mixture was quenched with Na₂S₂O₃ (10 mL) and extracted with DCM (2×30 mL). The combined organic phase was washed with NaHCO₃ (10 mL) and brine (20 mL), dried over anhydrous Na₂SO₄, filtered and the filtrate was concentrated in vacuo to give the title compound (120 mg, 71% yield) as a yellow solid. LC-MS (ESI⁺) m/z 488.1 (M+1)⁺.

4-[[4-[[4-[4-Amino-3-(difluoromethyl)pyrazol-1-yl] cyclohexyl]methyl-methyl-amino] cyclohexyl] amino]-2-(2,6-dioxo-3-piperidyl)isoindoline-1,3-dione (Intermediate AQR)

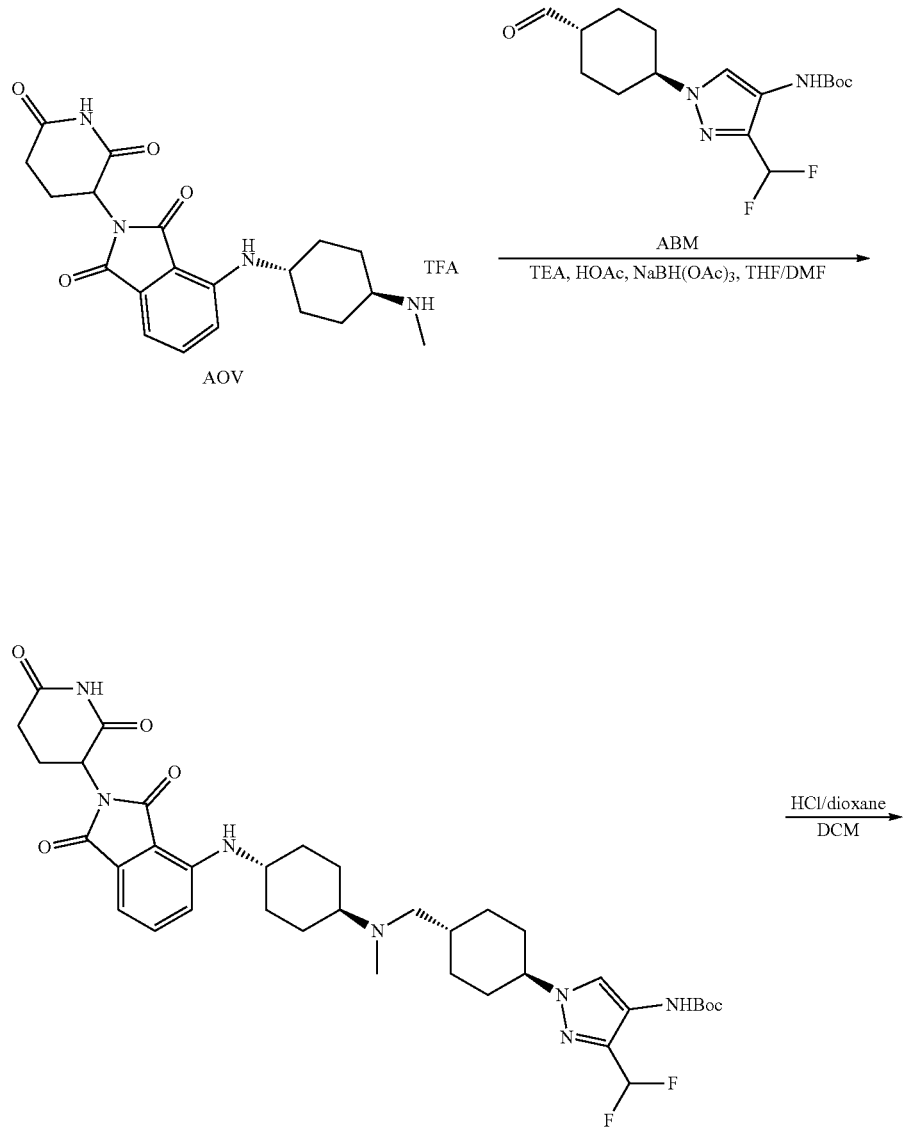

-continued

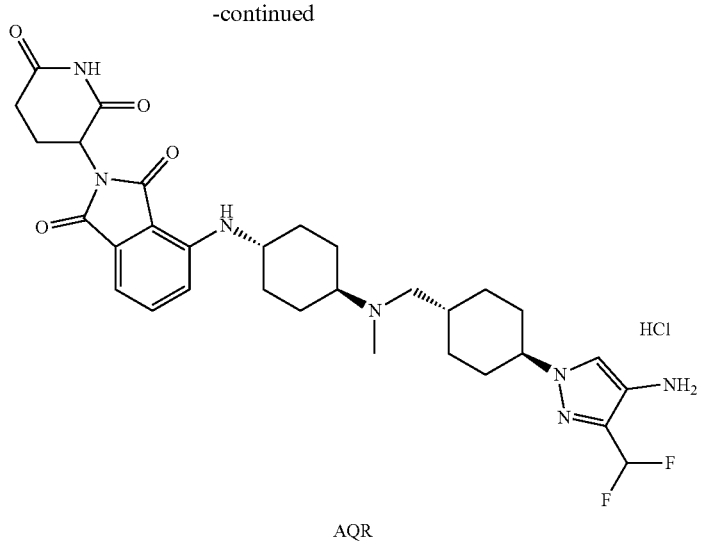

AQR

Step 1—Tert-butyl N-[3-(difluoromethyl)-1-[4-[[[4-[[2-(2,6-dioxo-3-piperidyl)-1,3-dioxo-isoindolin-4-yl]amino] cyclohexyl]-methyl-amino]methyl] cyclohexyl]pyrazol-4-yl]carbamate To a solution of 2-(2,6-dioxo-3-piperidyl)-4-[[4-(methylamino)cyclohexyl]amino]isoindoline-1,3-dione (350 mg, 702 umol, TFA salt, Intermediate AOV) in DMF (1 mL) and THF (5 mL) was added TEA (71.0 mg, 702 umol) and the mixture was stirred at 15° C. for 0.5 hour. HOAc (42.1 mg, 702 umol) and tert-butyl N-[3-(difluoromethyl)-1-(4-formylcyclohexyl)pyrazol-4-yl]carbamate (241 mg, 702 umol, Intermediate ABM) was added to the mixture. The mixture was stirred at 15° C. for 0.5 hour. Then NaBH(OAc)$_3$ (223 mg, 1.05 mmol) was added to the mixture at 0° C. and the mixture was stirred at 0° C. for 2 hours. On completion, the reaction was quenched with water (1.0 mL) and the mixture was concentrated in vacuo. The residue was purified by reverse phase (0.1% FA condition) to give the title compound (350 mg, 70% yield) as yellow solid. $^1$H NMR (400 MHz, DMSO-d$_6$) δ 11.09 (s, 1H), 8.98-8.78 (m, 1H), 7.88 (s, 1H), 7.59 (dd, J=7.2, 8.4 Hz, 1H), 7.24-6.85 (m, 3H), 6.16 (d, J=8.0 Hz, 1H), 5.05 (dd, J=5.2, 12.8 Hz, 1H), 4.19-4.06 (m, 1H), 3.57-3.47 (m, 2H), 2.97-2.83 (m, 1H), 2.11-1.97 (m, 5H), 1.45 (s, 9H), 1.38-1.28 (m, 2H), 1.08-0.96 (m, 2H); LC-MS (ESI$^+$) m/z 712.2 (M+H)$^+$.

Step 2—4-[[4-[4-[4-Amino-3-(difluoromethyl)pyrazol-1-yl]cyclohexyl]methyl-methyl-amino] cyclohexyl] amino]-2-(2,6-dioxo-3-piperidyl)isoindoline-1,3-dione To a solution of tert-butyl N-[3-(difluoromethyl)-1-[4-[[[4-[[2-(2,6-dioxo-3-piperidyl)-1,3-dioxo-isoindolin-4-yl] amino] cyclohexyl]-methyl-amino]methyl]cyclohexyl]pyrazol-4-yl]carbamate (100 mg, 140 umol) in DCM (20 mL) was added HCl/dioxane (4 M, 10.0 mL). The mixture was stirred at 15° C. for 2 hours. On completion, the mixture was concentrated in vacuo to give the title compound (85.0 mg, 98% yield, HCl salt) as yellow solid. LC-MS (ESI$^+$) m/z 612.3 (M+H)$^+$.

2-[2-[[(1 S,2R)-2-hydroxycyclohexyl]amino]-4-pyridyl]oxazole-4-carboxylic acid (Intermediate AQV)

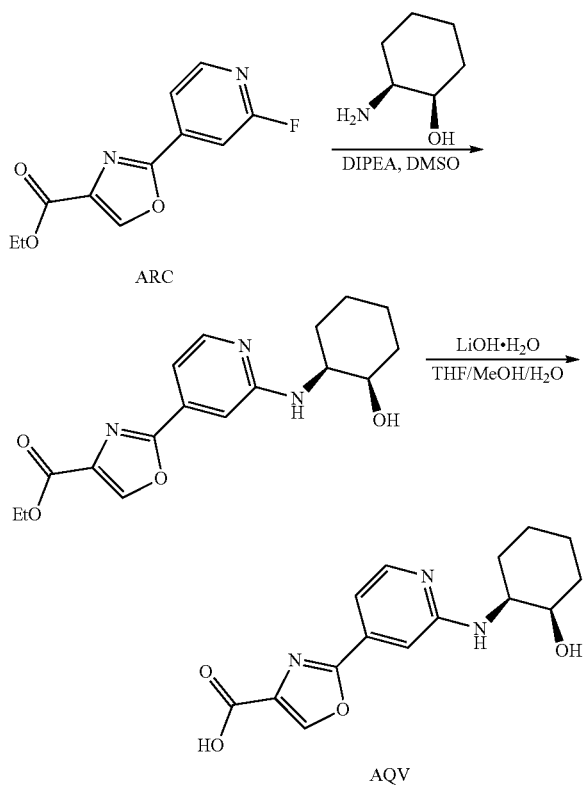

Step 1—Ethyl 2-[2-[[(1S,2R)-2-hydroxycyclohexyl] amino]-4-pyridyl]oxazole-4-carboxylate To a solution of ethyl 2-(2-fluoro-4-pyridyl)oxazole-4-carboxylate (1.0 g, 4.23 mmol, Intermediate ARC) and (1R,2S)-2-aminocyclohexanol (962 mg, 6.35 mmol, HCl salt, CAS #74111-21-0) in DMSO (10 mL) was added DIPEA (2.19 g, 16.9 mmol, 2.95 mL), and the reaction mixture was stirred at 130° C. for 16 hours. On completion, the reaction mixture was concentrated in vacuo to give a residue. The residue was purified by reverse phase (0.1% FA condition) to give the title compound (450 mg, 32% yield) as a yellow solid. $^1$H NMR (400 MHz, CDCl$_3$) δ 8.38-8.31 (m, 2H), 8.03 (d, J=5.6 Hz, 1H), 7.28 (d, J=6.4 Hz, 1H), 7.23 (dd, J=1.2, 5.6 Hz, 1H), 4.46 (q, J=7.2 Hz, 2H), 4.11-4.04 (m, 1H), 3.84-3.73 (m, 1H), 1.92-1.65 (m, 7H), 1.50-1.41 (m, 5H); LC-MS (ESI$^+$) m/z 332.2 (M+H)$^+$.

Step 2—2-[2-[[(1 S,2R)-2-hydroxycyclohexyl] amino]-4-pyridyl]oxazole-4-carboxylic acid To a solution of ethyl 2-[2-[[(1S,2R)-2-hydroxycyclohexyl]amino]-4-pyridyl]oxazole-4-carboxylate (130 mg, 392 umol) in a mixed solvents of THF (3 mL), MeOH (1 mL) and H$_2$O (1 mL) was added LiOH—H$_2$O (49.3 mg, 1.18 mmol), and the reaction mixture was stirred at 50° C. for 3 hours. On completion, the reaction mixture was quenched with H$_2$O (20 mL), then extracted with DCM (2×20 mL). The aqueous phase was acidified with citric acid until the pH=5-6, then filtered and the filter cake was concentrated in vacuo to give the title compound (60 mg, 50% yield) as a white solid. LC-MS (ESI$^+$) m/z 304.2 (M+H)$^+$.

4-[3-[3-[[4-[4-amino-3-(difluoromethyl)pyrazol-1-yl]]cyclohexyl] methyl-methyl-amino] propoxy] propylamino]-2-(2,6-dioxo-3-piperidyl)isoindoline-1,3-dione (Intermediate AQW)

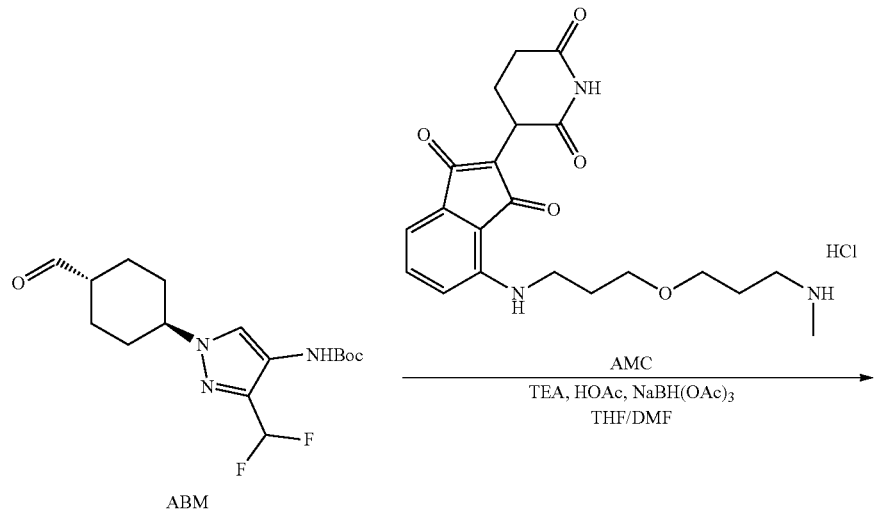

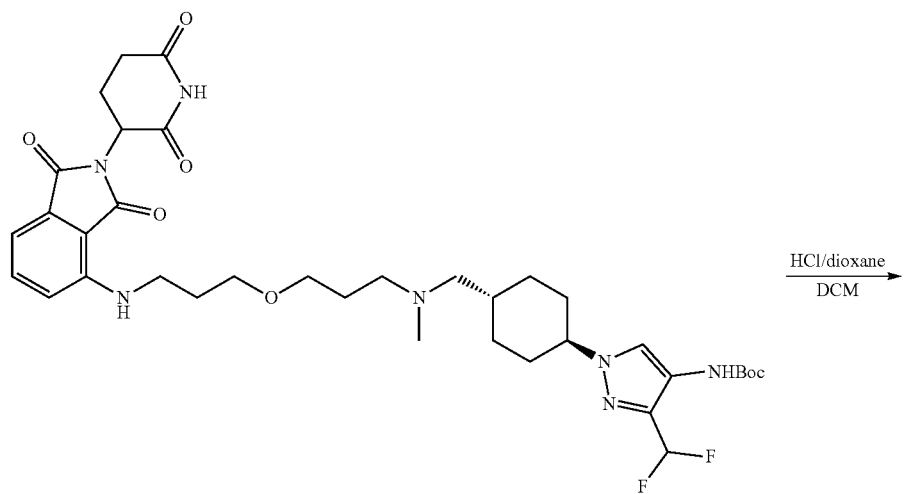

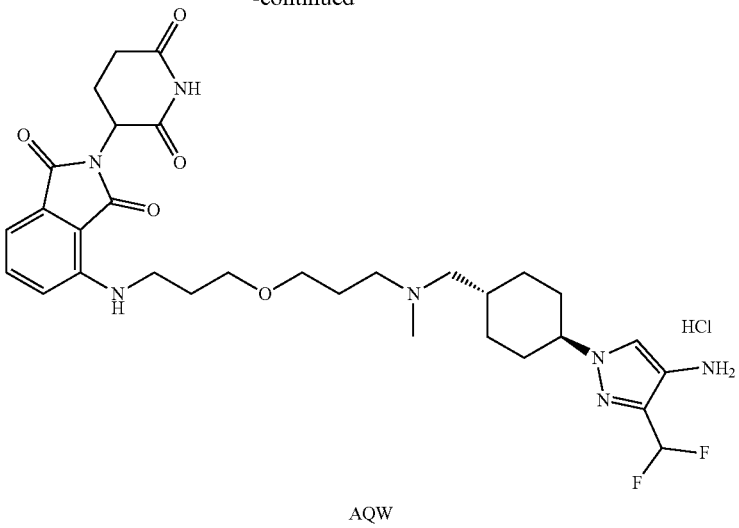

AQW

Step 1—Tert-butyl (3-(difluoromethyl)-1-((1r,4r)-4-(((3-(3-((2-(2,6-dioxopiperidin-3-yl)-1,3-dioxoisoindolin-4-yl)amino)propoxy)propyl)(methyl)amino)methyl)cyclohexl)-1H-pyrazol-4-yl)carbamate To a solution of 2-(2,6-dioxo-3-piperidyl)-4-[3-[3-(methylamino)propoxy]propylamino]isoindoline-1,3-dione (520 mg, 1.29 mmol, Intermediate AMC) and tert-butyl N-[3-(difluoromethyl)-1-(4-formylcyclohexyl)pyrazol-4-yl]carbamate (444 mg, 1.29 mmol, Intermediate ABM) in the THF (8 mL) and DMF (2 mL) was added Et$_3$N (130 mg, 1.29 mmol). The mixture was stirred at –10° C. for 5 mins. Then AcOH (155 mg, 2.58 mmol) was added to the mixture and the mixture was stirred for 25 mins at –10° C. Then NaBH(OAc)$_3$ (411 mg, 1.94 mmol) was added and the resulting mixture was stirred at –10° C. for 1 hr. On completion, the reaction mixture was concentrated in vacuo. The residue was purified by reversed phase (FA, 0.1%) to give the title compound (800 mg, 85% yield) as yellow solid.
$^1$H NMR (400 MHz, DMSO-d$_6$) δ=11.09 (s, 1H), 8.89 (s, 1H), 7.85 (s, 1H), 7.61-7.56 (m, 1H), 7.16-6.86 (m, 3H), 6.67 (br t, J=5.4 Hz, 1H), 5.05 (dd, J=5.6, 12.8 Hz, 1H), 4.13-4.02 (m, 1H), 3.48-3.46 (m, 2H), 2.90 (s, 2H), 2.85 (d, J=6.1 Hz, 1H), 2.74 (s, 2H), 2.59 (d, J=16.4 Hz, 1H), 2.33 (s, 2H), 2.12 (s, 3H), 2.10-2.06 (m, 2H), 1.98 (dd, J=2.4, 13.3 Hz, 3H), 1.90-1.79 (m, 4H), 1.74-1.62 (m, 4H), 1.51 (br s, 1H), 1.45 (s, 9H), 1.40 (s, 1H), 1.04-0.90 (m, 2H). LC-MS (ESI$^+$) m/z 730.2 (M+H)$^+$.

Step 2—4-((3-(3-((((1 r,4r)-4-(4-amino-3-(difluoromethyl)-1H-pyrazol-1-yl)cyclohexyl)methyl)(methyl)amino)propoxy)propyl)amino)-2-(2,6-dioxopiperidin-3-yl)isoindoline-1,3-dione To a solution of tert-butyl N-[3-(difluoromethyl)-1-[4-[[3-[3-[[2-(2,6-dioxo-3-piperidyl)-1,3-dioxo-isoindolin-4-yl]amino]propoxy]propyl-methyl-amino]methyl]cyclohexyl]pyrazol-4-yl]carbamate (380 mg, 521 umol) in the HCl/dioxane (4M, 4 mL) was stirred at 25° C. for 1 hr. On completion, the reaction mixture was concentrated in vacuo to give the title compound (340 mg, 98% yield) as yellow solid. LC-MS (ESI$^+$) m/z 630.2 (M+H)$^+$.

Benzyl 4-(3-aminocyclobutoxy)piperidine-1-carboxylate (Intermediate ARB)

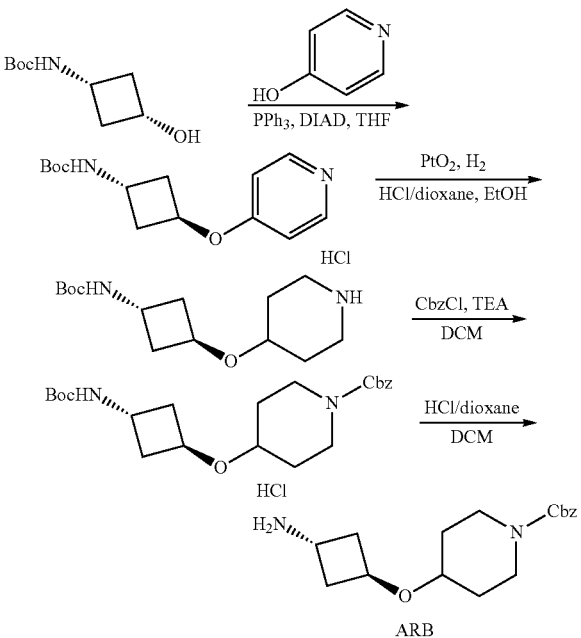

ARB

Step 1—Tert-butyl N-[3-(4-pyridyloxy)cyclobutyl]carbamate

To a mixture of tert-butyl N-(3-hydroxycyclobutyl)carbamate (500 mg, 2.67 mmol, CAS #154748-63-7) and pyridin-4-ol (253 mg, 2.67 mmol, CAS #626-64-2) in THF (2.0 mL) was added PPh$_3$ (1.05 g, 4.01 mmol). Then DIAD (810 mg, 4.01 mmol) was added into the mixture at 0° C. The mixture was stirred at 50° C. for 12 hours. On completion, the reaction was concentrated in vacuo to give a residue. The residue was purified by reverse phase (0.1% FA condition) to give the title compound (365 mg, 51% yield) as a white solid. $^1$H NMR (400 MHz, DMSO-$d_6$) δ 8.37 (br s, 2H), 7.31 (d, J=6.8 Hz, 1H), 6.83 (d, J=4.8 Hz, 2H), 4.92-4.84 (m, 1H), 4.09 (d, J=6.8 Hz, 1H), 2.46-2.28 (m, 4H), 1.38 (s, 9H).

Step 2—Tert-butyl N-[3-(4-piperidyloxy)cyclobutyl] carbamate

To a mixture of tert-butyl N-[3-(4-pyridyloxy)cyclobutyl] carbamate (450 mg, 1.70 mmol) in THF (30 mL) was added PtO$_2$ (386 mg, 1.70 mmol) and HCl/dioxane (4 M, 851 uL) under H$_2$ (50 psi). The mixture was stirred at 25° C. for 12 hours. On completion, the mixture was filtered and concentrated in vacuo to give the title compound (425 mg, 92% yield) as a white solid. $^1$H NMR (400 MHz, DMSO-$d_6$) δ 9.30-8.86 (m, 2H), 7.22-7.05 (m, 1H), 4.22-4.14 (m, 1H), 4.00-3.89 (m, 1H), 3.56-3.48 (m, 1H), 3.10 (s, 1H), 3.02-2.88 (m, 3H), 2.16-2.07 (m, 3H), 1.91 (d, J=13.6 Hz, 1H), 1.72-1.59 (m, 3H), 1.37 (d, J=1.1 Hz, 9H).

Step 3—Benzyl 4-[3-(tert-butoxycarbonylamino) cyclobutoxy]piperidine-1-carboxylate To a mixture of tert-butyl N-[3-(4-piperidyloxy)cyclobutyl]carbamate (345 mg, 1.28 mmol) in DCM (5 mL) was added TEA (387 mg, 3.83 mmol) and CbzCl (326 mg, 1.91 mmol). The mixture was stirred at 20° C. for 1 hour. On completion, the reaction mixture was concentrated to give the residue. The residue was purified by column chromatography (SiO$_2$, PE:EA=2:1) to give the title compound (430 mg, 83% yield) as brown oil. $^1$H NMR (400 MHz, CDCl$_3$) δ 7.39-7.27 (m, 5H), 5.13 (s, 2H), 4.79-4.53 (m, 1H), 4.27-4.07 (m, 2H), 3.89-3.79 (m, 2H), 3.53-3.35 (m, 1H), 3.17 (d, J=26.4 Hz, 2H), 2.43-2.26 (m, 2H), 2.23-2.09 (m, 2H), 1.77 (s, 2H), 1.57-1.47 (m, 2H), 1.44 (s, 9H).

Step 4—Benzyl 4-(3-aminocyclobutoxy)piperidine-1-carboxylate

To a mixture of benzyl 4-[3-(tert-butoxycarbonylamino) cyclobutoxy]piperidine-1-carboxylate (420 mg, 1.04 mmol) in DCM (20 mL) was added HCl/dioxane (4 M, 778 uL). The reaction mixture was stirred at 20° C. for 0.5 hour. On completion, the mixture was concentrated in vacuo to give the title compound (353 mg, 99% yield, HCl salt) as a yellow solid. LC-MS (ESI$^+$) m/z 305.2 (M+H)$^+$.

Ethyl 2-(2-fluoropyridin-4-yl)oxazole-4-carboxylate (Intermediate ARC)

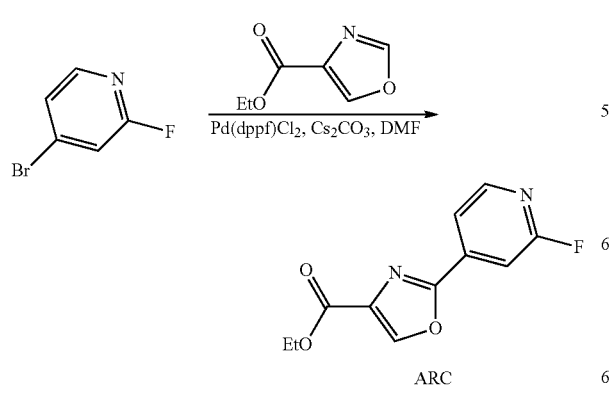

To a solution of 4-bromo-2-fluoro-pyridine (6 g, 34 mmol, CAS #128071-98-7) and ethyl oxazole-4-carboxylate (4.81 g, 34.1 mmol, CAS #170487-38-4) in the DMF (60 mL) was added Pd(dppf)Cl$_2$ (2.49 g, 3.41 mmol) and Cs$_2$CO$_3$ (33.3 g, 102 mmol). The mixture was stirred at 60° C. for 12 hrs under N$_2$. On completion, the reaction mixture was diluted with EA (300 mL) and washed with water (3×300 mL). The organic layer was dried over Na$_2$SO$_4$, filtered and concentrated in vacuo. The residue was purified by column chromatography to give the title compound (7.50 g, 93% yield) as white solid. $^1$H NMR (400 MHz, CHLOROFORM-d) δ 8.39 (d, J=5.2 Hz, 1H), 8.36 (s, 1H), 7.88 (td, J=1.6, 5.2 Hz, 1H), 7.61 (s, 1H), 4.46 (q, J=7.2 Hz, 2H), 1.43 (t, J=7.2 Hz, 3H).

3-(Difluoromethyl)-4-nitro-1-[4-(pent-4-ynoxymethyl)phenyl]pyrazole (Intermediate ARF)

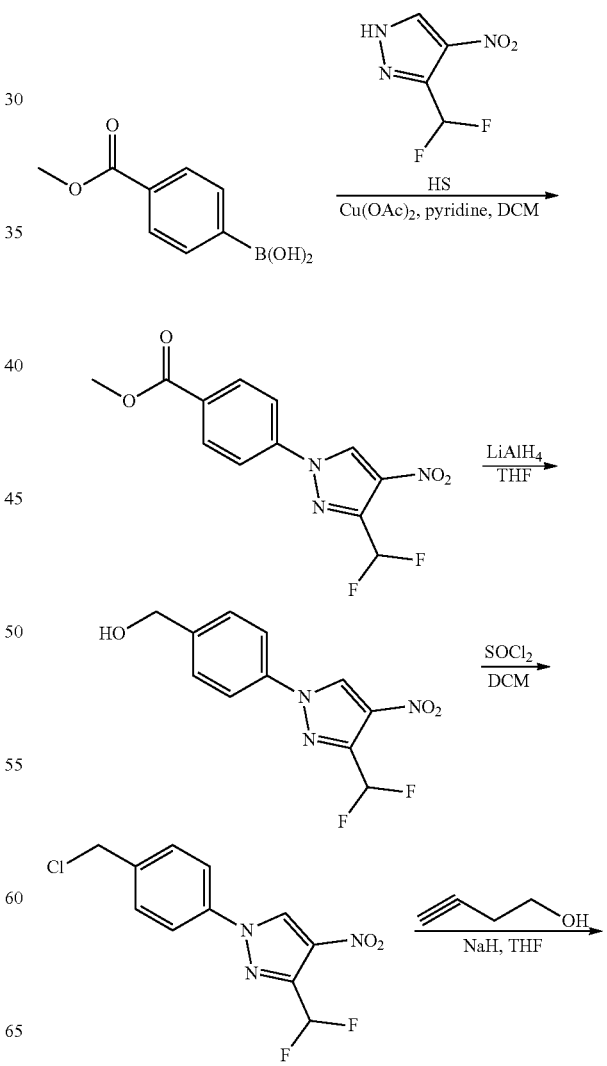

-continued

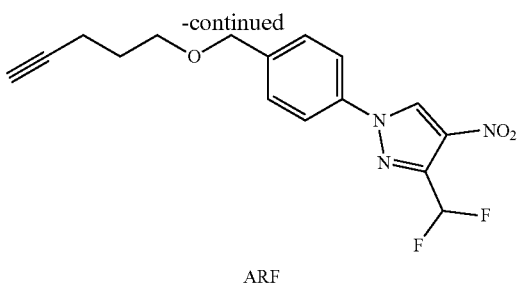

ARF

Step 1—Methyl 4-[3-(difluoromethyl)-4-nitro-pyrazol-1-yl]benzoate

To a mixture of (4-methoxycarbonylphenyl)boronic acid (5.00 g, 27.7 mmol, CAS #99768-12-4), 3-(difluoromethyl)-4-nitro-1H-pyrazole (4.53 g, 27.8 mmol, Intermediate HS) in DCM (50 mL) was added pyridine (8.79 g, 111 mmol) and Cu(OAc)$_2$ (7.57 g, 41.6 mmol). The reaction mixture was stirred at 25° C. for 12 hours under 02. On completion, the reaction was concentrated in vacuo to give the residue. The residue was purified by column chromatography (PE:EA=1:1) to give the title compound (2.60 g, 31% yield) as a brown solid. 1H NMR (400 MHz, DMSO-d$_6$) δ 9.89 (s, 1H), 8.13 (s, 4H), 7.63-7.26 (m, 1H), 3.89 (s, 3H).

Step 2—[4-[3-(Difluoromethyl)-4-nitro-pyrazol-1-yl]]phenyl]methanol

To a mixture of methyl 4-[3-(difluoromethyl)-4-nitro-pyrazol-1-yl] benzoate (730 mg, 2.46 mmol) in THF (20 mL) was added LiAlH$_4$ (140 mg, 3.68 mmol) at −20° C. The mixture was stirred at 25° C. for 0.5 hour. On completion, the reaction was quenched by water (140 mg) and 15% NaOH (140 mg). The mixture was filtered, and the filtrate was concentrated in vacuo to give the title compound (280 mg, 42% yield) as a yellow solid. 1H NMR (400 MHz, DMSO-d6) δ 9.73 (s, 1H), 8.11-8.01 (m, 2H), 7.98-7.83 (m, 3H), 7.31-6.84 (m, 1H), 5.36 (t, J=5.6 Hz, 1H), 4.57 (d, J=5.6 Hz, 2H).

Step 3—1-[4-(Chloromethyl)phenyl]-3-(difluoromethyl)-4-nitro-pyrazole

To a mixture of [4-[3-(difluoromethyl)-4-nitro-pyrazol-1-yl] phenyl] methanol (0.80 g, 2.97 mmol) in DCM (10 mL) was added SOCl$_2$ (1.06 g, 8.92 mmol). The reaction mixture was stirred at 20° C. for 12 hours. On completion, the reaction mixture was concentrated in vacuo to give the title compound (850 mg, 99% yield) as a yellow solid. LC-MS (ESI$^+$) m/z 288.3 (M+H)$^+$.

Step 4—3-(Difluoromethyl)-4-nitro-1-[4-(pent-4-ynoxymethyl)phenyl]pyrazole

To a mixture of pent-4-yn-1-ol (1.10 g, 13.0 mmol, CAS #110-63-4) in THF (5 mL) was added NaH (156 mg, 3.91 mmol, 60% dispersion in mineral oil) at 0° C. and stirred at 0.5 hour. Then 1-[4-(chloromethyl)phenyl]-3-(difluoromethyl)-4-nitro-pyrazole (750 mg, 2.61 mmol) was added into the mixture. The mixture was stirred at 20° C. for 12 hours. On completion, the reaction mixture was quenched by water (0.5 mL) and concentrated in vacuo to give the residue. The residue was purified by reverse phase (0.1% FA condition) to give the title compound (178 mg, 20% yield) as a white solid. 1H NMR (400 MHz, CDCl$_3$) δ 8.61 (s, 1H), 7.69-7.63 (m, 2H), 7.48-7.44 (m, 2H), 7.22-6.98 (m, 1H), 4.53 (s, 2H), 3.57 (t, J=6.0 Hz, 2H), 2.29 (t, J=9.6 Hz, 2H), 1.90 (d, J=2.4 Hz, 1H), 1.83-1.78 (m, 2H).

3-[4-[5-[[4-[4-Amino-3-(difluoromethyl)pyrazol-1-yl]phenyl]methoxy]pent-1-ynyl]-3-methyl-2-oxo-benzimidazol-1-yl]piperidine-2,6-dione (Intermediate ARG)

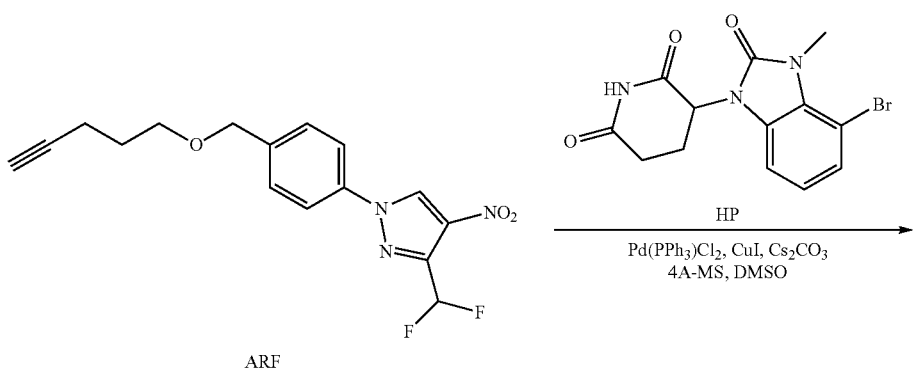

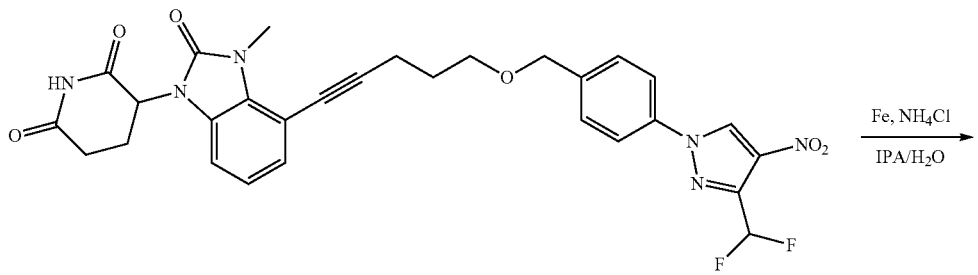

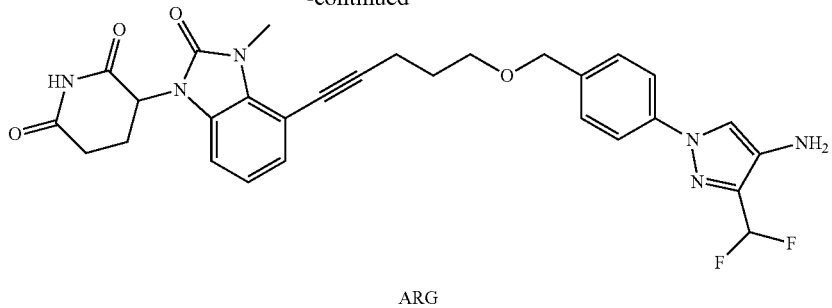

ARG

Step 1—3-[4-[5-[[4-[3-(Difluoromethyl)-4-nitro-pyrazol-1-yl]phenyl]methoxy]pent-1-ynyl]-3-methyl-2-oxo-benzimidazol-1-yl]piperidine-2,6-dione To a mixture of 3-(difluoromethyl)-4-nitro-1-[4-(pent-4-ynoxymethyl)phenyl]pyrazole (140 mg, 417 umol, Intermediate ARF), 3-(4-bromo-3-methyl-2-oxo-benzimidazol-1-yl)piperidine-2,6-dione (127 mg, 376 umol. Intermediate HP) in DMSO (2 mL) was added Pd(PPh$_3$)$_2$Cl$_2$ (29.3 mg, 41.7 umol), CuI (7.95 mg, 41.7 umol), DIPEA (270 mg, 2.09 mmol) under N$_2$. The reaction mixture was stirred at 80° C. for 2 hours. On completion, the reaction mixture was poured into water (50 mL) and the aqueous phase was extracted with ethyl acetate (2×30 mL). The combined organic layer was washed with brine (2×40 mL), dried with anhydrous Na$_2$SO$_4$, filtered and concentrated in vacuo to give the residue. The residue was purified by reverse phase (0.1% FA condition) to give the title compound (75.0 mg, 30% yield) as a brown solid. $^1$H NMR (400 MHz, DMSO-d$_6$) δ 11.11 (s, 1H), 9.74 (s, 1H), 7.94 (d, J=8.4 Hz, 2H), 7.57 (d, J=8.4 Hz, 2H), 7.60-7.29 (m, 1H), 7.11 (d, J=7.6 Hz, 1H), 7.05-7.00 (m, 1H), 6.95 (s, 1H), 5.41-5.35 (m, 1H), 4.59 (s, 2H), 3.66-3.62 (m, 3H), 3.61 (s, 2H), 2.96-2.83 (m, 1H), 2.77-2.64 (m, 2H), 2.63-2.59 (m, 2H), 2.06-1.98 (m, 1H), 1.89 (d, J=6.4 Hz, 2H).

Step 2—3-[4-[5-[[4-[4-Amino-3-(difluoromethyl)pyrazol-1-yl]phenyl]methoxy]pent-1-ynyl]-3-methyl-2-oxo-benzimidazol-1-yl]piperidine-2,6-dione To a mixture of 3-[4-[5-[[4-[3-(difluoromethyl)-4-nitro-pyrazol-1-yl]phenyl]methoxy] pent-1-ynyl]-3-methyl-2-oxo-benzimidazol-1-yl]piperidine-2,6-dione (65.0 mg, 109 umol) in IPA (10 mL) and H$_2$O (2 mL) was added Fe (61.2 mg, 1.10 mmol) and NH$_4$Cl (58.6 mg, 1.10 mmol). The mixture was stirred at 70° C. for 0.5 hour. On completion, the reaction mixture was poured into water (30 mL), and extracted with ethyl acetate (2×30 mL). The combined organic layer was washed with brine (2×30 mL), dried with anhydrous Na$_2$SO$_4$, filtered and concentrated in vacuo to give the title compound (60.0 mg, 97% yield) as a yellow solid. $^1$H NMR (400 MHz, DMSO-d$_6$) δ 11.11 (s, 1H), 7.78 (s, 1H), 7.69 (d, J=8.4 Hz, 2H), 7.44 (d, J=8.4 Hz, 2H), 7.22-6.90 (m, 4H), 5.39 (d, J=17.6 Hz, 1H), 4.53 (s, 2H), 4.40 (s, 2H), 3.63 (s, 3H), 3.61-3.57 (m, 2H), 2.99-2.81 (m, 1H), 2.69-2.65 (m, 2H), 2.60-2.56 (m, 2H), 2.08-1.97 (m, 1H), 1.93-1.84 (m, 2H).

4-Benzyloxy-3-methyl-1H-benzimidazol-2-one (Intermediate ARH)

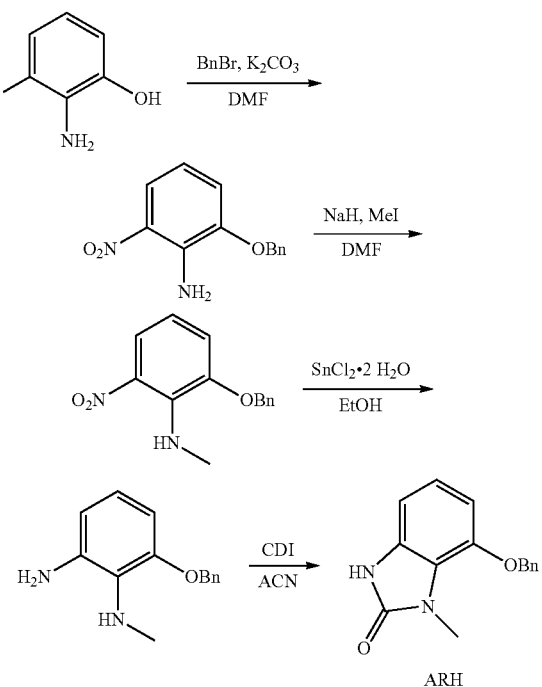

ARH

Step 1—2-Benzyloxy-6-nitro-aniline

To a solution of 2-amino-3-nitro-phenol (60.0 g, 389 mmol, CAS #2835-97-4) and K$_2$CO$_3$ (107 g, 778 mmol) in DMF (1000 mL) was added BnBr (79.9 g, 467 mmol) at −10° C. The reaction was then warmed to 25° C. and stirred for 18 hours. On completion, the reaction mixture was quenched by addition H$_2$O (1000 mL), and extracted with ethyl acetate (3×5000 mL). The combined organic layers were washed with brine (3×500 mL) and dried over Na$_2$SO$_4$, filtered and concentrated in vacuo to give a crude product. The residue was purified by silica gel column chromatography (PE:EA=3:1) to give the title compound (95.0 g, 99% yield) as brown solid. $^1$H NMR (400 MHz, CDCl$_3$) δ 7.77 (dd, J=1.2, 8.8 Hz, 1H), 7.49-7.36 (m, 5H), 7.04-6.95 (m, 1H), 6.61 (dd, J=7.6, 8.8 Hz, 1H), 6.48 (br s, 2H), 5.15 (s, 2H), LC-MS (ESI$^+$) m/z 245.6 (M+H)$^+$.

Step 2—2-Benzyloxy-N-methyl-6-nitro-aniline

To a solution of 2-benzyloxy-6-nitro-aniline (85.0 g, 348 mmol) in DMF (100 mL) was added NaH (13.9 g, 348 mmol, 60% dispersion in mineral oil) at 0° C. and stirred at 0° C. for 0.5 hr. Then MeI (49.4 g, 348 mmol, 21.6 mL) was added and the reaction mixture was stirred at 25° C. for 12 hrs. On completion, the reaction mixture was quenched by addition H$_2$O (200 mL), and extracted with ethyl acetate (3×600 mL). The combined organic layers were washed with brine (3×100 mL) and dried over Na$_2$SO$_4$, filtered and concentrated in vacuo to give the title compound (100 g, 90% yield) as yellow oil. $^1$H NMR (400 MHz, CDCl$_3$) δ 7.73 (dd, J=1.6, 8.8 Hz, 1H), 7.43-7.35 (m, 5H), 7.01-6.97 (m, 1H), 6.60 (dd, J=7.6, 8.8 Hz, 1H), 5.08 (s, 2H), 3.16 (s, 3H).

Step 3—3-Benzyloxy-N$_2$-methyl-benzene-1,2-diamine

To a solution of 2-benzyloxy-N-methyl-6-nitro-aniline (75.0 g, 290 mmol) in EtOH (1500 mL) was added SnCl$_2$.2H$_2$O (327 g, 1.45 mol). The reaction mixture was then exposed to ultrasonic radiation for approximately 30 minutes at 25° C. The reaction mixture was then basified with 1M KOH solution (5000 mL) and extracted with DCM (3×5000 mL). The combined organic layer was washed with brine (3×500 mL), dried over NaSO$_4$ and concentrated in vacuo. The residue was purified by silica gel column chromatography (PE:EA=3:1) to give the title compound (20.0 g, 30% yield) as yellow oil, $^1$H NMR (400 MHz, CDCl$_3$) δ 7.48-7.32 (m, 5H), 6.84 (t, J=8.0 Hz, 1H), 6.49-6.38 (m, 2H), 5.07 (s, 2H), 3.91 (br s, 2H), 2.70 (s, 3H), LC-MS (ESI$^+$) m/z 229.7 (M+H)$^+$.

Step 4—4-Benzyloxy-3-methyl-1H-benzimidazol-2-one

To a solution of 3-benzyloxy-N$_2$-methyl-benzene-1,2-diamine (20.0 g, 87.6 mmol) in ACN (600 mL) was added CDI (14.2 g, 87.6 mmol), and the reaction mixture was stirred at 25° C. for 16 hours. On completion, the reaction mixture was filtered and the solid was collected to give the title compound (17.0 g, 76% yield) as white solid. $^1$H NMR (400 MHz, DMSO-d$_6$) δ 10.83 (s, 1H), 7.55-7.47 (m, 2H), 7.46-7.39 (m, 2H), 7.38-7.32 (m, 1H), 6.95-6.87 (m, 1H), 6.83-6.77 (m, 1H), 6.64 (dd, J=0.8, 7.6 Hz, 1H), 5.19 (s, 2H), 3.47 (s, 3H), LC-MS (ESI$^+$) m/z 255.0 (M+H)$^+$.

3-(4-Hydroxy-3-methyl-2-oxo-benzimidazol-1-yl)piperidine-2,6-dione (Intermediate ARI)

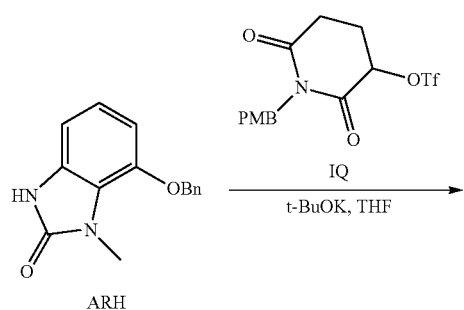

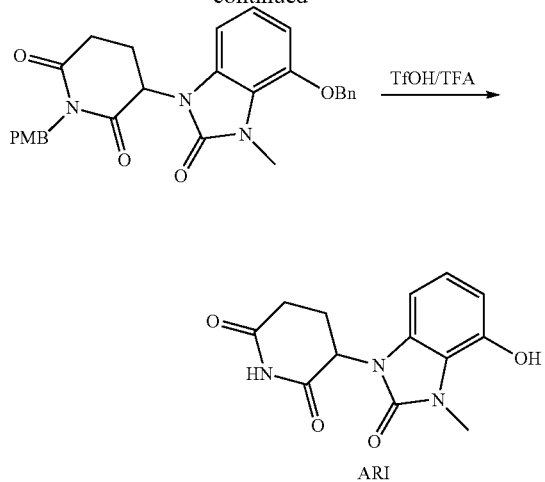

Step 1—3-(4-Benzyloxy-3-methyl-2-oxo-benzimidazol-1-yl)-1-[(4-methoxyphenyl)methyl] piperidine-2,6-dione To a mixture of 4-benzyloxy-3-methyl-1H-benzimidazol-2-one (2.00 g, 7.87 mmol, Intermediate ARH) in THF (60 mL) was added KOtBu (1.77 g, 15.7 mmol) at −10° C. for 0.5 hr under N$_2$. Then solution of [1-[(4-methoxyphenyl)methyl]-2,6-dioxo-3-piperidyl]trifluoromethanesulfonate (7.50 g, 19.6 mmol, Intermediate IQ) in THF (20 mL) was added dropwise and the mixture was stirred at −10° C. for 1 hour under N$_2$. On completion, the mixture was poured into saturated ammonium chloride aqueous solution (100 mL) and extracted with ethyl acetate (3×100 mL). The combined organic layers were washed with water, brine, dried over anhydrous sodium sulfate and concentrated in vacuo. The residue was purified by silica gel column chromatography (EA) to give the title compound (2.20 g, 57% yield) as blue solid. $^1$H NMR (400 MHz, DMSO-d$_6$) δ 7.56-7.50 (m, 2H), 7.44-7.40 (m, 2H), 7.38-7.34 (m, 1H), 7.21 (d, J=8.8 Hz, 2H), 6.92-6.83 (m, 4H), 6.66 (dd, J=7.8, 13.6 Hz, 1H), 5.49 (dd, J=5.4, 12.8 Hz, 1H), 5.22 (s, 2H), 4.87-4.73 (m, 2H), 3.73 (s, 3H), 3.54 (s, 3H), 3.10-2.98 (m, 1H), 2.89-2.64 (m, 2H), 2.10-2.02 (m, 1H).

Step 2—3-(4-Hydroxy-3-methyl-2-oxo-benzimidazol-1-yl)piperidine-2,6-dione

To a mixture of 3-(4-benzyloxy-3-methyl-2-oxo-benzimidazol-1-yl)-1-[(4-methoxyphenyl)methyl] piperidine-2,6-dione (2.00 g, 4.12 mmol) in TFA (10.0 mL) was added TfOH (17.0 g, 113 mmol). The reaction mixture was heated to 60° C. and stirred for 1 hour. On completion, the mixture was concentrated in vacuo to remove TFA. The residue was poured into water (100 mL), neutralized with saturated NaHCO$_3$ aqueous solution until the pH=5, and concentrated in vacuo. The residue was purified by reverse phase: (0.1% FA) to give the title compound (500 mg, 43% yield) as off-white solid. $^1$H NMR (400 MHz, DMSO-d$_6$) δ 11.07 (s, 1H), 9.81 (s, 1H), 6.87-6.79 (m, 1H), 6.60-6.54 (m, 2H), 5.30 (dd, J=5.4, 12.8 Hz, 1H), 3.53 (s, 3H), 2.97-2.83 (m, 1H), 2.75-2.60 (m, 2H), 2.05-1.95 (m, 1H).

3-[4-(7-Azaspiro[3.5]nonan-2-yloxy)-3-methyl-2-oxo-benzimidazol-1-yl]piperidine-2,6-dione (Intermediate ARJ)

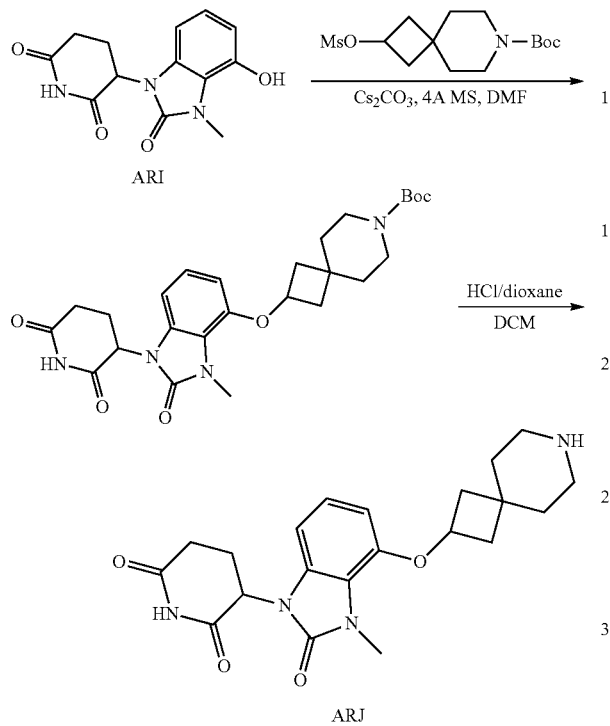

Step 1—Tert-butyl 2-[1-(2,6-dioxo-3-piperidyl)-3-methyl-2-oxo-benzimidazol-4-yl]oxy-7-azaspiro[3.5] nonane-7-carboxylate To a mixture of 3-(4-hydroxy-3-methyl-2-oxo-benzimidazol-1-yl)piperidine-2,6-dione (250 mg, 908 umol, Intermediate ARI) and 4 Å molecular sieves (250 mg) in DMF (4.00 mL) was added Cs$_2$CO$_3$ (887 mg, 2.72 mmol) and tert-butyl 2-methylsulfonyloxy-7-azaspiro[3.5]nonane-7-carboxylate (870 mg, 2.72 mmol, synthesized via Step 1 of Intermediate AJZ) and the mixture was stirred at 80° C. for 16 hours. On completion, mixture was filtered. The filtrate was acidified with formic acid (0.05 mL) and concentrated in vacuo. The residue was purified by reverse phase (0.1% FA) to give the title compound (70.0 mg, 15% yield) as white solid. $^1$H NMR (400 MHz, DMSO-d$_6$) δ 11.07 (br s, 1H), 7.00-6.86 (m, 1H), 6.75 (d, J=8.0 Hz, 1H), 6.57 (d, J=8.4 Hz, 1H), 5.34 (dd, J=5.2, 12.8 Hz, 1H), 4.86 (q, J=6.4 Hz, 1H), 3.55 (s, 3H), 3.33-3.20 (m, 4H), 2.96-2.84 (m, 1H), 2.77-2.58 (m, 2H), 2.47-2.30 (m, 3H), 2.06-1.85 (m, 4H), 1.59-1.45 (m, 2H), 1.39 (s, 9H).

Step 2—3-[4-(7-Azaspiro[3.5]nonan-2-yloxy)-3-methyl-2-oxo-benzimidazol-1-yl]piperidine-2,6-dione To a mixture of tert-butyl 2-[1-(2,6-dioxo-3-piperidyl)-3-methyl-2-oxo-benzimidazol-4-yl] oxy-7-azaspiro[3.5]nonane-7-carboxylate (70.0 mg, 140 umol) in DCM (3.00 mL) was added HCl/dioxane (4.00 M, 1.00 mL), and the mixture was stirred at 25° C. for 1 hour. On completion, the mixture was concentrated in vacuo to give the title compound (60.0 mg, 98% yield, HCl) as white solid. LC-MS (ESI$^+$) m/z 399.2 (M+H)$^+$.

2-(2-(((1R,2S)-2-hydroxycyclohexyl)amino)pyridin-4-yl)oxazole-4-carboxylic acid (Intermediate ATK)

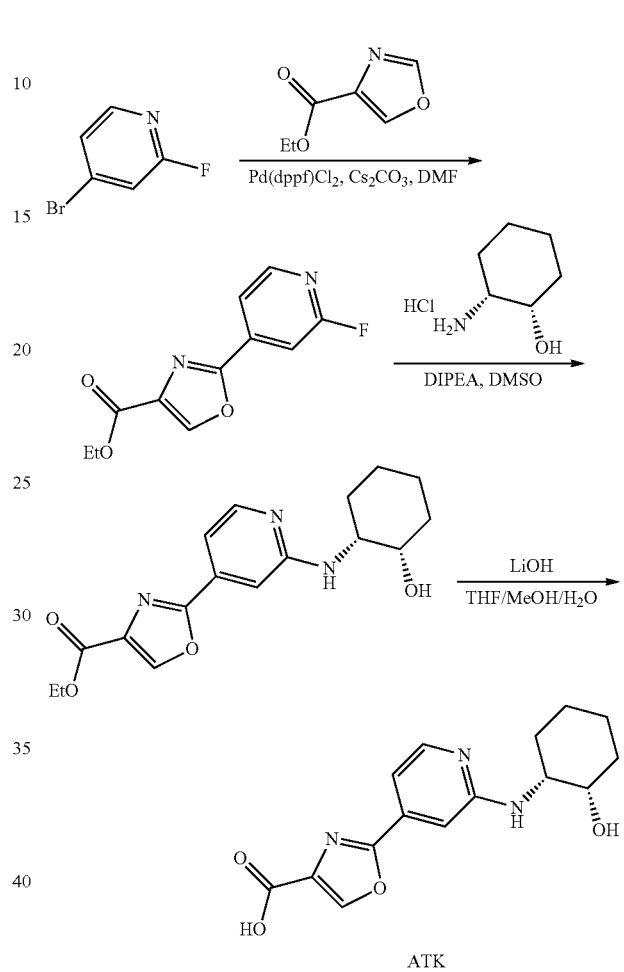

Step 1—Ethyl 2-(2-fluoropyridin-4-yl)oxazole-4-carboxylate

To a solution of 4-bromo-2-fluoro-pyridine (6 g, 34.1 mmol, CAS #128071-98-7) and ethyl oxazole-4-carboxylate (4.81 g, 34.1 mmol, CAS #170487-38-4) in the DMF (60 mL) was added Pd(dppf)Cl$_2$ (2.49 g, 3.41 mmol) and Cs$_2$CO$_3$ (33.3 g, 102 mmol). The mixture was stirred at 60° C. for 12 hrs under N$_2$. On completion, the reaction mixture was diluted with EA (300 mL) and washed with water (3×300 mL). The organic layer was dried over Na$_2$SO$_4$, filtered and concentrated in vacuo. The residue was purified by column chromatography to give the title compound (7.50 g, 93% yield) as white solid. $^1$H NMR (400 MHz, CHLOROFORM-d) δ 8.39 (d, J=5.2 Hz, 1H), 8.36 (s, 1H), 7.88 (td, J=1.6, 5.2 Hz, 1H), 7.61 (s, 1H), 4.46 (q, J=7.2 Hz, 2H), 1.43 (t, J=7.2 Hz, 3H).

Step 2—Ethyl 2-(2-(((1R,2S)-2-hydroxycyclohexyl)amino)pyridin-4-yl)oxazole-4-carboxylate To a solution of ethyl 2-(2-fluoro-4-pyridyl)oxazole-4-carboxylate (1.00 g, 4.23 mmol) and (1S,2R)-2-aminocyclohexanol (963 mg, 6.35 mmol, HCl, CAS #931-16-8) in the DMSO (10 mL) was added DIPEA (1.09 g, 8.47 mmol). The mixture was stirred at 130° C. for 4 hrs. On completion, the reaction mixture was diluted with water (100 mL) and extracted with EA (100 mL). The organic layer was dried over Na₂SO₄, filtered and concentrated in vacuo. The residue was purified by prep-HPLC (column: Phenomenex luna C18 150*40 mm*15 um; mobile phase: [water (0.225% FA)-ACN]; B %: 1%-28%, 9 min) to give the title compound (550 mg, 35% yield) as white solid. ¹H NMR (400 MHz, CHLOROFORM-d) δ=8.34 (s, 1H), 8.04 (d, J=5.6 Hz, 1H), 7.25 (s, 1H), 7.23 (dd, J=1.3, 5.7 Hz, 1H), 4.45 (q, J=7.1 Hz, 2H), 4.09-4.02 (m, 1H), 3.85-3.76 (m, 1H), 1.93-1.65 (m, 6H), 1.43 (t, J=7.2 Hz, 3H).

Step 3—2-(2-(((1R,2S)-2-hydroxycyclohexyl) amino)pyridin-4-yl)oxazole-4-carboxylic acid To a solution of ethyl 2-[2-[[(1R,2S)-2-hydroxycyclohexyl]amino]-4-pyridyl]oxazole-4-carboxylate (100 mg, 302 umol) in the THF (1.5 mL), MeOH (0.5 mL) and H₂O (0.5 mL) was added LiOH (36.1 mg, 1.51 mmol). The mixture was stirred at 50° C. for 3 hrs. On completion, the mixture was diluted with water (10 mL) and DCM (10 mL). The water phase was separated and acided with HCl (aq. 1 M, 0.5 mL) until the pH=4. The mixture was filtered and to give the title compound (90 mg, 98% yield) as red solid. ¹H NMR (400 MHz, DMSO-d₆) δ 8.88 (s, 1H), 8.10 (d, J=5.1 Hz, 1H), 7.18 (s, 1H), 6.95 (dd, J=1.4, 5.3 Hz, 1H), 6.58 (d, J=7.1 Hz, 1H), 3.95-3.82 (m, 2H), 1.77-1.59 (m, 4H), 1.58-1.50 (m, 2H), 1.37-1.27 (m, 2H).

4-[3-(Difluoromethyl)-4-[[5-[(2R,6S)-2,6-dimethylmorpholin-4-yl]pyrazolo[1,5-a]pyrimidine-3-carbonyl] amino]pyrazol-1-yl]cyclohexanecarboxylic acid (Intermediate ATA)

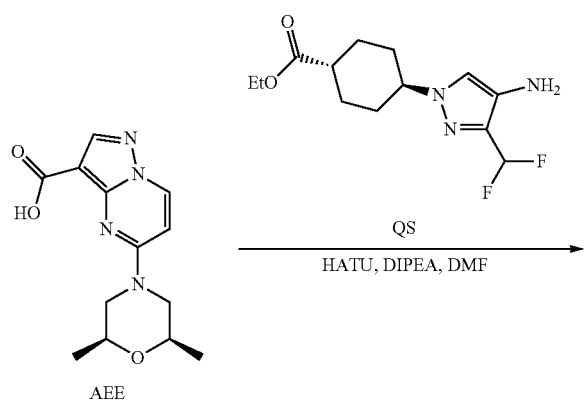

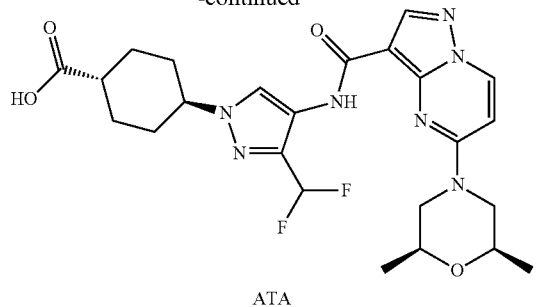

Step 1—Ethyl4-[3-(difluoromethyl)-4-[[5-[(2R,6S)-2,6-dimethylmorpholin-4-yl]pyrazolo[1,5-a]pyrimidine-3-carbonyl]amino]pyrazol-1-yl]cyclohexanecarboxylate To a mixture of 5-[(2R,6S)-2,6-dimethylmorpholin-4-yl]pyrazolo[1,5-a]pyrimidine-3-carboxylic acid (500 mg, 1.81 mmol, Intermediate AEE), HATU (894 mg, 2.35 mmol) and DIPEA (584 mg, 4.52 mmol) in DMF (15 mL) was added ethyl 4-[4-amino-3-(difluoromethyl)pyrazol-1-yl]cyclohexanecarboxylate (571 mg, 1.99 mmol, Intermediate QS) at 25° C. and stirred for 0.5 hour. Then the reaction mixture was stirred at 50° C. for 12 hours. On completion, the reaction mixture was quenched with water (10 mL) and then washed with citric acid to pH=7. Then the reaction mixture was exacted with EA (2×15 mL) and the organic layer was dried over anhydrous sodium sulfate, filtered and concentrated in vacuo. The residue was purified by silica gel chromatography (PE:EA=1:1) to give the title compound (963 mg, 97% yield) as white solid. ¹H NMR (400 MHz, DMSO-d₆) δ 9.27 (s, 1H), 8.83-8.79 (m, 1H), 8.40 (s, 1H), 8.28 (s, 1H), 7.34-7.04 (m, 1H), 6.94 (d, J=8.0 Hz, 1H), 4.62-4.31 (m, 2H), 4.30-4.18 (m, 1H), 4.11-4.05 (m, 2H), 3.73-3.60 (m, 2H), 2.71-2.59 (m, 2H), 2.40-2.27 (m, 1H), 2.12-2.00 (m, 4H), 1.86-1.71 (m, 2H), 1.61-1.45 (m, 2H), 1.22-1.17 (m, 9H).

Step 2—4-[3-(Difluoromethyl)-4-[[5-[(2R,6S)-2,6-dimethylmorpholin-4-yl]pyrazolo[1,5-a]pyrimidine-3-carbonyl]amino]pyrazol-1-yl]cyclohexanecarboxylic acid To a mixture of ethyl 4-[3-(difluoromethyl)-4-[[5-[(2R,6S)-2,6-dimethylmorpholin-4-yl]pyrazolo [1,5-a]pyrimidine-3-carbonyl] amino]pyrazol-1-yl]cyclohexanecarboxylate (963 mg, 1.77 mmol) in a mixture solution of MeOH (2 mL), H₂O (2 mL) and THF (6 mL) was added LiOH.H₂O (222 mg, 5.30 mmol) at 25° C. The reaction mixture stirred at 25° C. for 2 hours. On completion, the reaction mixture was concentrated in vacuo. Then the residue was diluted in water (10 mL) and acidified with 2M HCl aqueous until the pH=6. The mixture was filtered. The filter cake was dried in vacuo to give the title compound (595 mg, 65% yield) as white solid. ¹H NMR (400 MHz, DMSO-d₆) δ 12.16 (br s, 1H), 9.28 (s, 1H), 8.82 (d, J=8.0 Hz, 1H), 8.40 (s, 1H), 8.29 (s, 1H), 7.31-7.03 (m, 1H), 6.94 (d, J=8.0 Hz, 1H), 4.68-4.13 (m, 3H), 3.81-3.37 (m, 3H), 2.80-2.60 (m, 2H), 2.21-1.94 (m, 4H), 1.90-1.68 (m, 2H), 1.63-1.35 (m, 2H), 1.20 (d, J=6.4 Hz, 6H).

2015
3-(6-Bromo-3-methyl-2-oxo-1,3-benzodiazol-1-yl)piperidine-2,6-dione (Intermediate ATL)
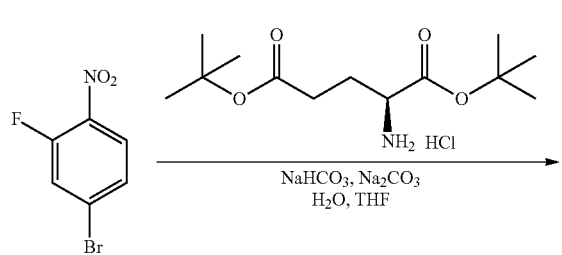
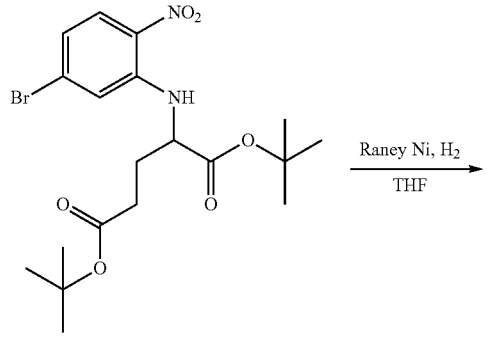
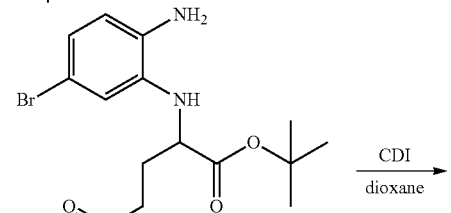
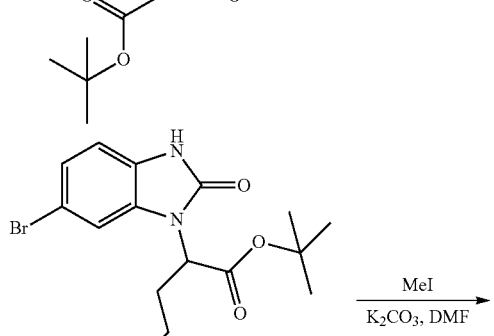
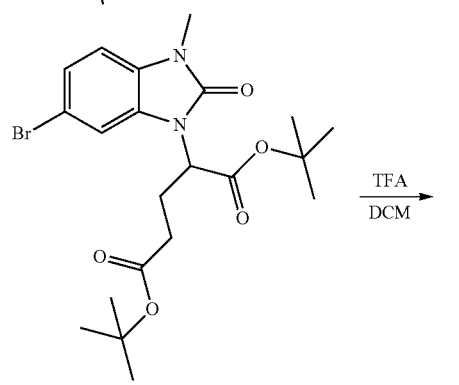
2016
-continued
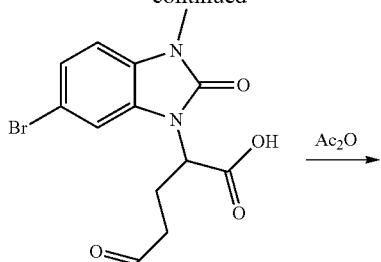
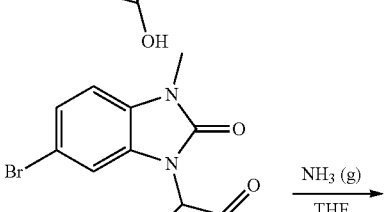
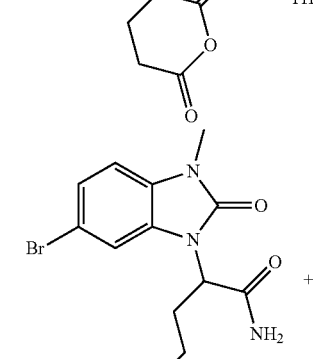
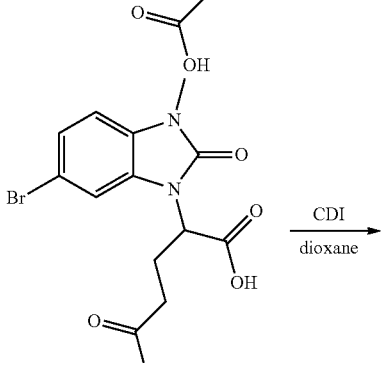
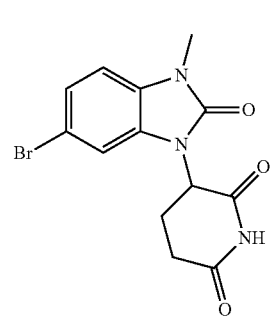
ATL
Step 1—1,5-Di-tert-butyl 2-[(5-bromo-2-nitrophenyl)amino]pentanedioate
A mixture of 4-bromo-2-fluoro-1-nitrobenzene (10.00 g, 45.45 mmol), NaHCO₃ (7.64 g, 90.9 mmol), Na₂CO₃ (14.45 g, 136.3 mmol) and 1,5-di-tert-butyl (2S)-2-aminopentanedioate hydrochloride (16.13 g, 54.54 mmol) in $H_2O$ (200.00 mL)/THF (200.00 mL) was stirred for overnight at 50° C. The mixture then cooled to room temperature and extracted with petroleum ether (2×200 mL). The combined organic phase was washed with HCl (1 M, 100 mL), brine (100 mL), dried with $Na_2SO_4$ and filtered. The filtrate was concentrated under reduced pressure. This resulted in the title compound (12 g, 57%) as an orange oil. Epimerization would occur under basic conditions. $^1H$ NMR (400 MHz, DMSO-$d_6$) δ 8.29 (d, J=7.6 Hz, 1H), 8.03 (d, J=9.1 Hz, 1H), 7.28 (d, J=2.0 Hz, 1H), 6.94 (dd, J=9.1, 2.0 Hz, 1H), 4.55 (q, J=6.5 Hz, 1H), 2.32 (td, J=7.3, 3.0 Hz, 2H), 2.08 (ddt, J=18.2, 14.2, 7.1 Hz, 2H), 1.45 (s, 9H), 1.36 (s, 9H); LC/MS (ESI, m/z): $[(M+1)]^+$=459.0, 461.0

Step 2—1,5-Di-tert-butyl 2-[(2-amino-5-bromophenyl)amino]pentanedioate

To a solution of 1,5-di-tert-butyl 2-[(5-bromo-2-nitrophenyl)amino]pentanedioate (69.00 g, 150.6 mmol) in THF (400.00 mL) was added Raney Ni (5.00 g) at room temperature under nitrogen atmosphere. The mixture was hydrogenated at room temperature under 30 psi of hydrogen pressure for 4 h. It was then filtered through a celite pad and concentrated under reduced pressure. This resulted in the title compound (64.48 g, 99%) as a light yellow solid: $^1H$ NMR (400 MHz, DMSO-$d_6$) δ 6.58 (dd, J=8.2, 2.1 Hz, 1H), 6.47 (d, J=8.2 Hz, 1H), 6.37 (d, J=2.2 Hz, 1H), 4.94 (d, J=8.8 Hz, 1H), 4.85 (s, 2H), 3.79 (td, J=8.4, 6.0 Hz, 1H), 2.41 (t, J=7.6 Hz, 2H), 1.93 (qt, J=13.6, 7.3 Hz, 2H), 1.41 (s, 18H); LC/MS (ESI, m/z): $[(M+1)]^+$=429.1, 431.1.

Step 3—1,5-Di-tert-butyl 2-(6-bromo-2-oxo-3H-1,3-benzodiazol-1-yl)pentanedioate

A solution of 1,5-di-tert-butyl 2-[(2-amino-5-bromophenyl)amino]pentanedioate (64.48 g, 150.1 mmol) and CDI (42.93 g, 300.3 mmol) in dioxane (1200.00 mL) was stirred for 4 h at 100° C. under nitrogen atmosphere. The mixture then cooled to room temperature and the resulting mixture was concentrated under reduced pressure. The residue was diluted with water (200 mL) and extracted with petroleum ether (3×200 mL). The combined organic layers were washed with brine (300 mL), and dried over anhydrous $Na_2SO_4$. After filtration, the filtrate was concentrated under reduced pressure. This resulted in the title compound (48 g, 70%) as a white powder. $^1H$ NMR (400 MHz, DMSO-$d_6$) δ 7.25 (d, J=1.9 Hz, 1H), 7.16 (dd, J=8.2, 1.9 Hz, 1H), 6.95 (d, J=8.3 Hz, 1H), 4.97 (dd, J=9.8, 5.5 Hz, 1H), 2.34-2.07 (m, 4H), 1.36 (s, 9H), 1.31 (s, 9H); LC/MS (ESI, m/z): $[(M+1)]^+$=455.1, 457.1.

Step 4—1,5-Di-tert-butyl 2-(6-bromo-3-methyl-2-oxo-1,3-benzodiazol-1-yl)pentanedioate To a stirred mixture of 1,5-di-tert-butyl 2-(6-bromo-2-oxo-3H-1,3-benzodiazol-1-yl)pentanedioate (48.00 g, 105.4 mmol) and $K_2CO_3$ (43.71 g, 316.2 mmol) in DMF (200.00 mL) was added methyl iodide (22.44 g, 158.1 mmol) dropwise at room temperature under air atmosphere and the resulting mixture was stirred for 2 h at rt. The mixture was the diluted with $H_2O$ (1200 mL) and petroleum ether (500 mL), where a lot of precipitate formed. The solids were filtered and dried under reduced pressure to give the title compound (40 g, 81%) as a white powder. $^1H$ NMR (400 MHz, DMSO-$d_6$) δ 7.33 (d, J=1.8 Hz, 1H), 7.26 (dd, J=8.3, 1.8 Hz, 1H), 7.15 (d, J=8.3 Hz, 1H), 5.03 (dd, J=8.6, 6.5 Hz, 1H), 3.32 (s, 3H), 2.41-2.24 (m, 2H), 2.24-2.07 (m, 2H), 1.36 (s, 9H), 1.31 (s, 9H); LC/MS (ESI, m/z): $[(M+1)]^+$=469.1, 471.1.

Step 5—2-(6-Bromo-3-methyl-2-oxo-1,3-benzodiazol-1-yl)pentanedioic acid

To a stirred solution of 1,5-di-tert-butyl 2-(6-bromo-3-methyl-2-oxo-1,3-benzodiazol-1-yl)pentanedioate (32.00 g, 68.38 mmol) in DCM (150.00 mL) was added TFA (200.00 mL) dropwise at rt under air atmosphere and the resulting mixture was stirred for 3 h at rt. The solution was then concentrated under reduced pressure to give the title compound (23 g, 94%) as a white solid. $^1H$ NMR (400 MHz, DMSO-$d_6$) δ 7.35 (d, J=1.9 Hz, 1H), 7.26 (dd, J=8.3, 1.8 Hz, 1H), 7.15 (d, J=8.3 Hz, 1H), 5.07 (dd, J=10.0, 5.3 Hz, 1H), 3.32 (s, 3H), 2.45-2.28 (m, 2H), 2.28-2.05 (m, 2H); LC/MS (ESI, m/z): $[(M+1)]^+$=356.9, 358.9.

Step 6—3-(6-Bromo-3-methyl-2-oxo-1,3-benzodiazol-1-yl)oxane-2,6-dione

A solution 2-(6-bromo-3-methyl-2-oxo-1,3-benzodiazol-1-yl)pentanedioic acid (23.00 g, 64.61 mmol) in acetic anhydride (150.00 mL) was stirred for 4 h at 135° C. under nitrogen atmosphere. The solution was then cooled to rt. The precipitated solids were collected by filtration, washed with $Et_2O$ (3×100 mL) and dried under reduced pressure. This resulted in the title compound (21 g, 96%) as an off-white powder. $^1H$ NMR (400 MHz, DMSO-$d_6$) δ 7.62 (d, J=1.8 Hz, 1H), 7.30 (dd, J=8.3, 1.8 Hz, 1H), 7.19 (d, J=8.4 Hz, 1H), 5.72 (dd, J=13.2, 5.8 Hz, 1H), 3.33 (s, 3H), 3.15 (ddd, J=18.6, 13.0, 6.0 Hz, 1H), 2.95 (ddd, J=17.8, 4.9, 2.2 Hz, 1H), 2.85 (qd, J=12.9, 4.7 Hz, 1H), 2.03 (ddt, J=12.2, 6.0, 2.9 Hz, 1H); LC/MS (ESI, m/z): $[(M+1)]^+$=339.1, 341.1.

Step 7—2-(6-Bromo-3-methyl-2-oxo-1,3-benzodiazol-1-yl)-4-carbamoylbutanoic acid $NH_3$ (gas) was bubbled in a stirred solution of 3-(6-bromo-3-methyl-2-oxo-1,3-benzodiazol-1-yl)oxane-2,6-dione (21.00 g, 62.13 mmol) in THF (200.00 mL) at 0° C. for 30 min. Then the mixture was stirred at room temperature for 2 h. The mixture was then concentrated under reduced pressure to give 2-(6-bromo-3-methyl-2-oxo-1,3-benzodiazol-1-yl)-4-carbamoylbutanoic acid (20 g, 91%) as an off-white solid. LC/MS (ESI, m/z): $[(M+1)]^+$=355.9, 357.9.

Step 8—3-(6-Bromo-3-methyl-2-oxo-1,3-benzodiazol-1-yl)piperidine-2,6-dione

A stirred mixture of 2-(6-bromo-3-methyl-2-oxo-1,3-benzodiazol-1-yl)pentanedioic acid (20.00 g, 55.99 mmol) and CDI (18.16 g, 112.0 mmol) in 1,4-dioxane (400 mL) was stirred for 6 h at 100° C. The solution was then cooled to rt and concentrated under 3.6 Hz, 1H), 5.39 (dd, J=12.7, 5.3 Hz, 1H), 3.33 (s, 3H), 2.97-2.70 (m, 2H), 2.63 (dd, J=16.4, 3.6 Hz, 1H), 2.05-1.90 (m, 1H); LC/MS (ESI, m z): $[(M+1)]^+$=338.0, 340.0.

2019

3-(3-Methyl-2-oxo-4-((R)-3-(piperidin-4-yloxy)butyl)-2,3-dihydro-1H-benzo[d]imidazol-1-vl)piperidine-2,6-dione (Intermediate ATO)

2020

3-[4-[3-(3,9-Diazaspiro[5.5]undecan-3-yl)propyl]-3-methyl-2-oxo-benzimidazol-1-yl] piperidine-2,6-dione (Intermediate ATP)

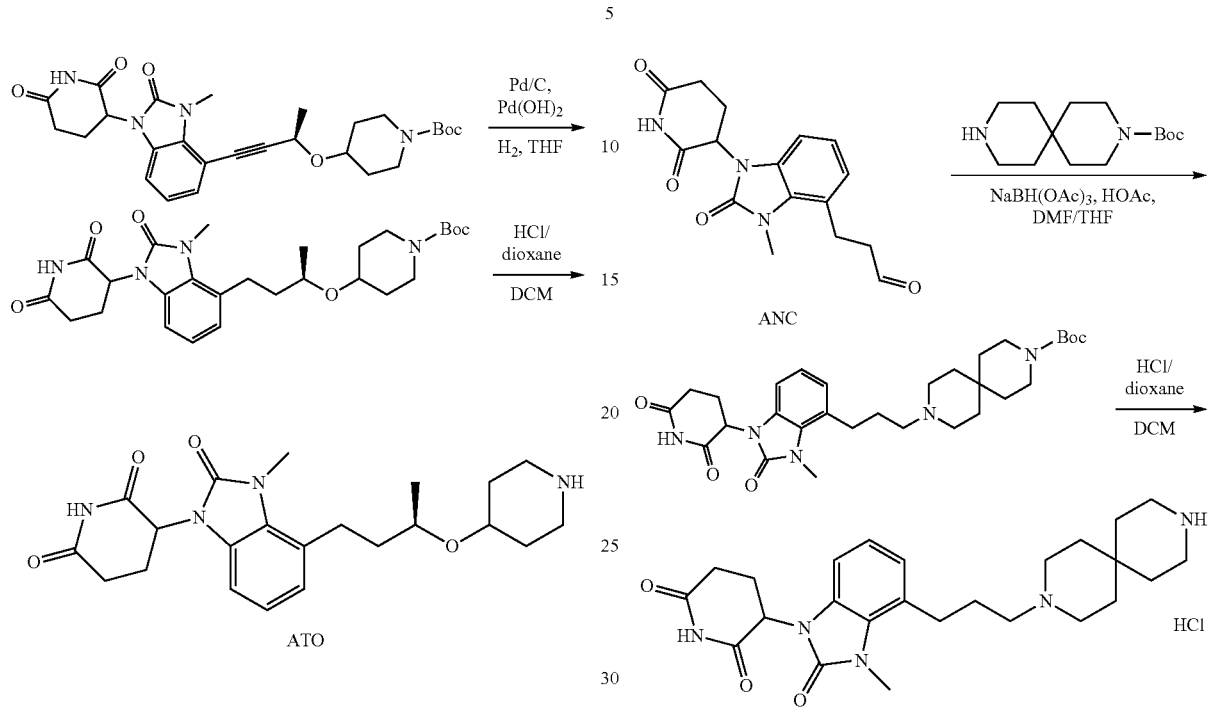

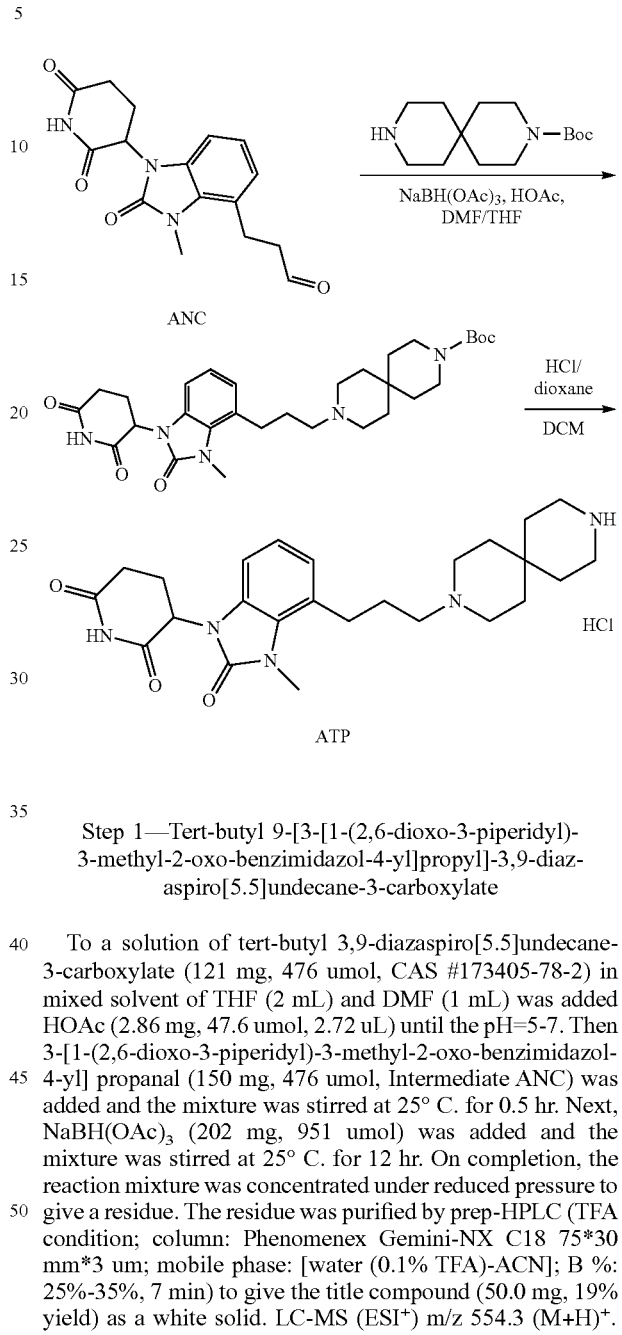

Step 1—Tert-butyl 4-(((2R)-4-(1-(2,6-dioxopiperidin-3-yl)-3-methyl-2-oxo-2,3-dihydro-1H-benzo[d]imidazol-4-yl)butan-2-yl)oxy)piperidine-1-carboxylate To a solution of tert-butyl 4-[(1R)-3-[1-(2,6-dioxo-3-piperidyl)-3-methyl-2-oxo-benzimidazol-4-yl]-1-methyl-prop-2-ynoxy]piperidine-1-carboxylate (200 mg, 392 umol, synthesized via Steps 1-2 of Intermediate AVF) in THF (5 mL) was added Pd/C (100 mg, 10 wt %) and Pd(OH)$_2$ (100 mg, 712 umol). The mixture was stirred at 25° C. for 2 h under hydrogen (15 psi) atmosphere. On completion, the reaction mixture was filtered and the filtrate was concentrated in vacuo to give the title compound (180 mg, 89% yield) as colorless oil. $^1$H NMR (400 MHz, DMSO-d$_6$) δ 11.08 (s, 1H), 6.96-6.94 (m, 2H), 6.89-6.84 (m, 1H), 3.69-3.60 (m, 3H), 3.57 (s, 3H), 3.06-3.03 (m, 3H), 2.94-2.80 (m, 2H), 2.76-2.62 (m, 2H), 2.01-1.99 (m, 4H), 1.82-1.66 (m, 4H), 1.39 (s, 9H), 1.37-1.26 (m, 4H). LC-MS (ESI$^+$) m z 537.3 (M+23)$^+$.

Step 2—3-(3-Methyl-2-oxo-4-((R)-3-(piperidin-4-yloxy)butyl)-2,3-dihydro-1H-benzo[d]imidazol-1-vl)piperidine-2,6-dione To a solution of tert-butyl 4-[(1R)-3-[1-(2,6-dioxo-3-piperidyl)-3-methyl-2-oxo-benzimidazol-4-yl]-1-methylpropoxy]piperidine-1-carboxylate (90.0 mg, 175 umol) in DCM (1 mL) was added HCl/dioxane (4 M, 43.72 uL). The mixture was stirred at 25° C. for 10 mins. On completion, the reaction mixture was concentrated in vacuo to give the title compound (74.3 mg, 94% yield, HCl salt) as colorless oil. LC-MS (ESI$^+$) m/z 415.3 (M+H)$^+$.

Step 1—Tert-butyl 9-[3-[1-(2,6-dioxo-3-piperidyl)-3-methyl-2-oxo-benzimidazol-4-yl]propyl]-3,9-diazaspiro[5.5]undecane-3-carboxylate To a solution of tert-butyl 3,9-diazaspiro[5.5]undecane-3-carboxylate (121 mg, 476 umol, CAS #173405-78-2) in mixed solvent of THF (2 mL) and DMF (1 mL) was added HOAc (2.86 mg, 47.6 umol, 2.72 uL) until the pH=5-7. Then 3-[1-(2,6-dioxo-3-piperidyl)-3-methyl-2-oxo-benzimidazol-4-yl] propanal (150 mg, 476 umol, Intermediate ANC) was added and the mixture was stirred at 25° C. for 0.5 hr. Next, NaBH(OAc)$_3$ (202 mg, 951 umol) was added and the mixture was stirred at 25° C. for 12 hr. On completion, the reaction mixture was concentrated under reduced pressure to give a residue. The residue was purified by prep-HPLC (TFA condition; column: Phenomenex Gemini-NX C18 75*30 mm*3 um; mobile phase: [water (0.1% TFA)-ACN]; B %: 25%-35%, 7 min) to give the title compound (50.0 mg, 19% yield) as a white solid. LC-MS (ESI$^+$) m/z 554.3 (M+H)$^+$.

Step 2—3-[4-[3-(3,9-Diazaspiro[5.5]undecan-3-yl)propyl]-3-methyl-2-oxo-benzimidazol-1-yl] piperidine-2,6-dione To a solution of tert-butyl 9-[3-[1-(2,6-dioxo-3-piperidyl)-3-methyl-2-oxo-benzimidazol-4-yl]propyl]-3,9-diazaspiro[5.5]undecane-3-carboxylate (50.0 mg, 90.3 umol) in DCM (3 mL) was added HCl/dioxane (4 M, 1 mL) and the mixture was stirred at 25° C. for 1 hr. On completion, the reaction mixture was concentrated under reduced pressure to give the title compound (40.0 mg, 100% yield, HCl) as yellow solid. LC-MS (ESI$^+$) m/z 454.3 (M+H)$^+$.

3-[4-(3,9-Diazaspiro[5.5]undecan-3-ylmethyl)-3-methyl-2-oxo-benzimidazol-1-yl]piperidine-2,6-dione (Intermediate ATQ)

N-[1-(4-formylcyclohexyl)-3-(5-methyl-2-pyridyl)pyrazol-4-yl]-5-[(1R,4R)-2-oxa-5-azabicyclo[2.2.1]heptan-5-yl]pyrazolo[1,5-a]pyrimidine-3-carboxamide (Intermediate ATR)

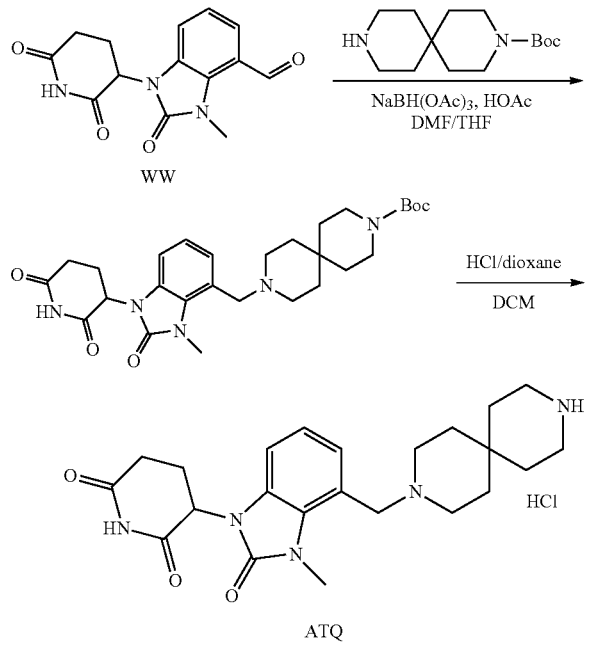

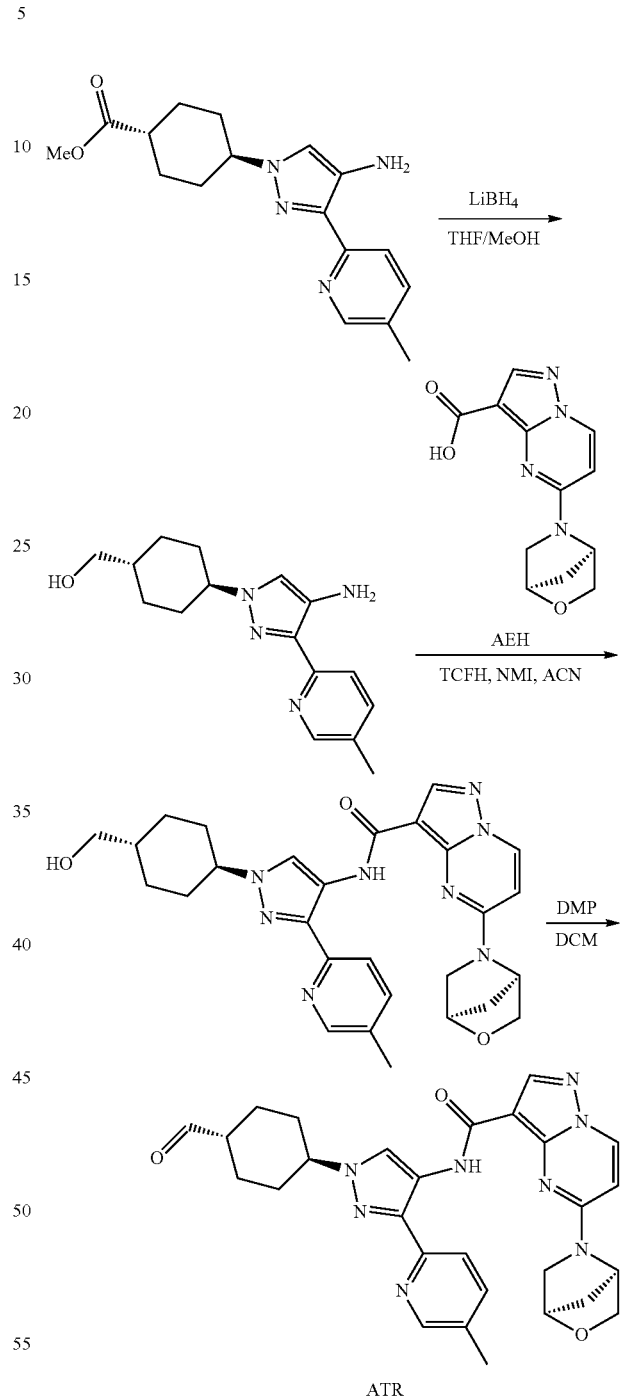

Step 1—Tert-butyl 9-[[1-(2,6-dioxo-3-piperidyl)-3-methyl-2-oxo-benzimidazol-4-yl]methyl]-3,9-iazaspiro[5.5]undecane-3-carboxylate To a solution of tert-butyl 3,9-diazaspiro[5.5]undecane-3-carboxylate (44.3 mg, 174 umol, CAS #173405-78-2) in THF (2 mL) and DMF (1 mL) was added HOAc (1.05 mg, 17.4 umol) until the pH=5-7. Then 1-(2,6-dioxo-3-piperidyl)-3-methyl-2-oxo-benzimidazole-4-carbaldehyde (50.0 mg, 174 umol, Intermediate WW) was added. The mixture was stirred at 25° C. for 0.5 hr. Then NaBH(OAc)$_3$ (73.8 mg, 348 umol) was added and stirred at 25° C. for 12 hrs. On completion, the reaction mixture was quenched with 1 mL H$_2$O and concentrated in vacuo to give a residue. The crude product was purified by reversed-phase HPLC (0.1% TFA condition, 50-60% CH$_3$CN) to give the title compound (50.0 mg, 55% yield) as a white oil. LC-MS (ESI$^+$) m/z 526.3 (M+H)$^+$.

Step 2—3-[4-(3,9-Diazaspiro[5.5]undecan-3-ylmethyl)-3-methyl-2-oxo-benzimidazol-1-yl]piperidine-2,6-dione To a solution of tert-butyl 9-[[1-(2,6-dioxo-3-piperidyl)-3-methyl-2-oxo-benzimidazol-4-yl]methyl] 3,9-diazaspiro[5.5]undecane-3-carboxylate (50.0 mg, 95.12 umol) in DCM (3 mL) was added HCl/dioxane (4 M, 1 mL). The mixture was stirred at 25° C. for 2 hrs. On completion, the reaction mixture was concentrated in vacuo to give a residue as the title compound (40 mg, 100% yield, HCl) as a white solid. LC-MS (ESI$^+$) m/z 426.2 (M+H)$^+$.

Step 1—[4-[4-Amino-3-(5-methyl-2-pyridyl)pyrazol-1-yl]cyclohexyl]methanol

To a mixture of methyl 4-[4-amino-3-(5-methyl-2-pyridyl)pyrazol-1-yl]cyclohexanecarboxylate (400 mg, 1.27 mmol, synthesized via Steps 1-2 of Intermediate ARR) in THF (4.0 mL) and MeOH (0.5 mL) was added LiBH$_4$ (222 mg, 10.2 mmol) at 0° C., then the mixture was stirred at 60°

C. for 12 hour. On completion, the reaction mixture was poured into water (10 mL), and the aqueous phase was extracted with ethyl acetate (2×10 mL). The combined organic layer was washed with brine (2×10 mL), dried with anhydrous $Na_2SO_4$, filtered and concentrated in vacuo to give the title compound (280 mg, 62% yield). $^1$H NMR (400 MHz, DMSO-$d_6$) δ=8.35 (s, 1H), 7.75 (d, J=8.4 Hz, 1H), 7.67-7.51 (m, 2H), 7.16 (s, 1H), 4.90 (s, 2H), 4.46 (s, 1H), 4.09-3.92 (m, 1H), 3.29-3.24 (m, 1H), 3.26 (d, J=6.0 Hz, 1H), 2.29 (s, 3H), 2.03 (d, J=12.4 Hz, 2H), 1.86 (d, J=12.0 Hz, 2H), 1.69 (dq, J=3.3, 12.8 Hz, 2H), 1.42 (m, 1H), 1.27-1.15 (m, 1H), 1.08 (dq, J=3.6, 12.8 Hz, 2H). LC-MS (ESI$^+$) m/z 287.1 (M+H)$^+$.

Step 2—N-[1-[4-(hydroxymethyl)cyclohexyl]-3-(5-methyl-2-pyridyl)pyrazol-4-yl]-5-[(1R,4R)-2-oxa-5-azabicyclo[2.2.1]heptan-5-yl]pyrazolo 1,5-a]pyrimidine-3-carboxamide To a solution of 5-[(1R,4R)-2-oxa-5-azabicyclo[2.2.1]heptan-5-yl]pyrazolo[1,5-a]pyrimidine-3-carboxylic acid (130 mg, 503 umol, Intermediate AEH) in ACN (3.0 mL) was added 1-methylimidazol (120 mg, 1.47 mmol), and [chloro(dimethylamino)methylene]-dimethyl-ammonium; hexafluorophosphate (141 mg, 503 umol). The reaction mixture was stirred at 25° C. for 30 min. Then [4-[4-amino-3-(5-methyl-2-pyridyl)pyrazol-1-yl]cyclohexyl]methanol (120 mg, 419 umol) was added. The reaction mixture was stirred at 25° C. for 2 hrs. On completion, the reaction mixture was concentrated in vacuo to give a residue. The residue was purified by reverse phase flash [0.1% TFA condition] to give the title compound (50.0 mg, 23% yield) as a yellow solid. $^1$H NMR (400 MHz, DMSO-$d_6$) δ=11.09-10.75 (m, 1H), 8.78 (d, J=8.0 Hz, 1H), 8.42-8.22 (m, 3H), 7.88-7.68 (m, 2H), 6.95-6.45 (m, 1H), 5.25-5.05 (m, 1H), 4.83-4.18 (m, 3H), 3.90-3.43 (m, 4H), 3.30-3.28 (m, 1H), 2.32 (s, 3H), 2.19-2.06 (m, 2H), 2.05-1.68 (m, 6H), 1.67-1.56 (m, 1H), 1.54-1.38 (m, 1H), 1.23-1.00 (m, 2H). LC-MS (ESI$^+$) m/z 529.3 (M+H)$^+$.

Step 3—N-[1-(4-formylcyclohexyl)-3-(5-methyl-2-pyridyl)pyrazol-4-yl]-5-[(1R,4R)-2-oxa-5-azabicyclo[2.2.1]heptan-5-yl]pyrazolo[1,5-a]pyrimidine-3-carboxamide To a mixture of N-[1-[4-(hydroxymethyl)cyclohexyl]-3-(5-methyl-2-pyridyl)pyrazol-4-yl]-5-[(1R,4R)-2-oxa-5-azabicyclo[2.2.1]heptan-5-yl]pyrazolo[1,5-a]pyrimidine-3-carboxamide (40.0 mg, 76.0 umol) in DCM (1.5 mL) was added DMP (48.1 mg, 114 umol) at 25° C. under $N_2$. The reaction mixture was stirred at 25° C. for 1 hr. On completion, the reaction mixture was quenched with $Na_2S_2O_3$ aqueous (5.0 mL) and extracted with DCM (2×3.0 mL). The combined organic layer was washed with $NaHCO_3$ and brine (2×3.0 mL), dried with anhydrous $Na_2SO_4$, filtered and concentrated in vacuo to give the title compound (50.0 mg, 100% yield). $^1$H NMR (400 MHz, DMSO-$d_6$) δ=11.02-10.72 (m, 1H), 9.66-9.49 (m, 1H), 8.70 (d, J=8.0 Hz, 1H), 8.37-8.11 (m, 3H), 7.97-7.91 (m, 1H), 7.82-7.76 (m, 1H), 7.65-7.60 (m, 1H), 5.36-4.87 (m, 1H), 4.73-4.37 (m, 1H), 4.20-4.12 (m, 1H), 3.80-3.50 (m, 4H), 2.25 (s, 3H), 2.16-1.96 (m, 4H), 1.96-1.82 (m, 3H), 1.78-1.60 (m, 2H), 1.39-1.35 (m, 2H). LC-MS (ESI$^+$) m/z 527.4 (M+H)$^+$.

4-[4-[[1-(2,6-dioxo-3-piperidyl)-3-methyl-2-oxo-benzimidazol-4-yl]methyl]-1-piperidyl] benzaldehyde (Intermediate ATS)

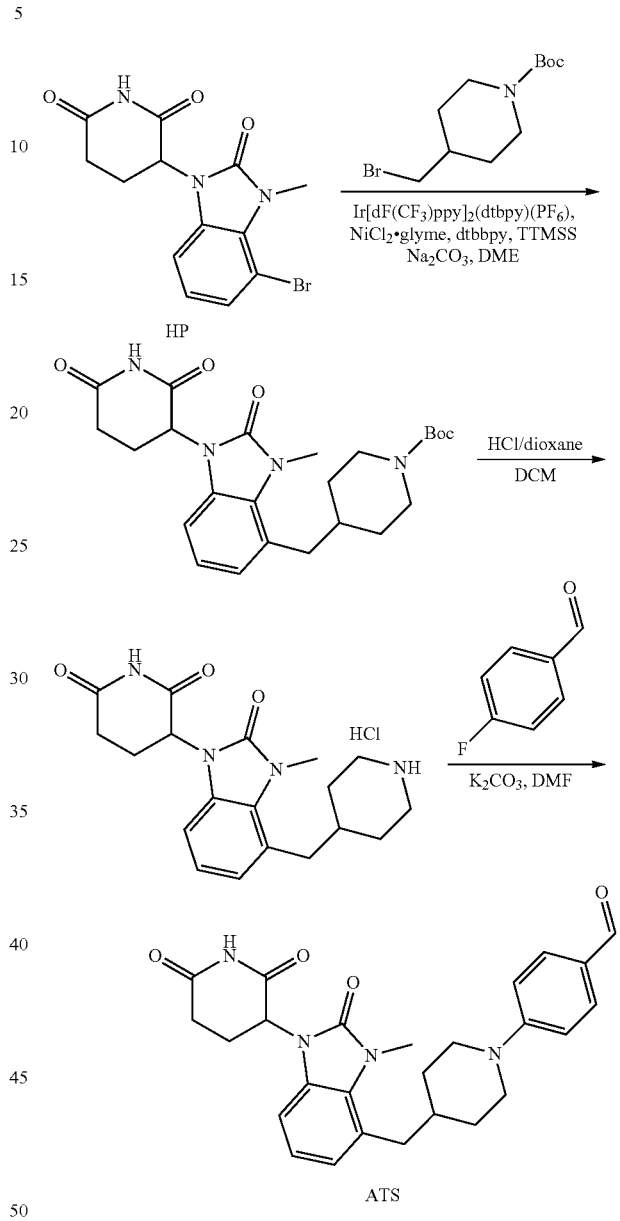

Step 1—Tert-butyl 4-[[1-(2,6-dioxo-3-piperidyl)-3-methyl-2-oxo-benzimidazol-4-yl]methyl]piperidine-1-carboxylate To an 40 mL vial equipped with a stir bar was added 3-(4-bromo-3-methyl-2-oxo-benzimidazol-1-yl) piperidine-2,6-dione (750 mg, 2.22 mmol, Intermediate HP), tert-butyl 4-(bromomethyl)piperidine-1-carboxylate (734 mg, 2.64 mmol, CAS #158407-06-6), Ir[dF(CF$_3$)ppy]2(dtbpy)(PF$_6$) (24.9 mg, 22.2 umol), NiCl$_2$.glyme (2.44 mg, 11.1 umol), dtbbpy (3.57 mg, 13.3 umol), TTMSS (552 mg, 2.22 mmol) and $Na_2CO_3$ (470 mg, 4.44 mmol) in DME (20 mL). The vial was sealed and placed under nitrogen was added. The reaction was stirred and irradiated with a 34 W blue LED lamp at 25° C. for 14 hr. On completion, the reaction mixture was filtered and the filtrate was concentrated in vacuo to give a residue. The residue was purified by reverse phase flash (0.1% TFA condition) to give the title compound (300 mg, 30% yield) as a white solid. $^1$H NMR (400 MHz, DMSO-d$_6$) δ=11.01 (s, 1H), 6.98-6.68 (m, 3H), 5.28 (dd, J=5.6, 12.4 Hz, 1H), 3.92-3.77 (m, 2H), 3.47 (s, 3H), 2.85-2.68 (m, 3H), 2.67-2.50 (m, 4H), 1.98-1.86 (m, 1H), 1.69-1.44 (m, 3H), 1.31 (s, 9H), 1.06-1.02 (m, 2H).

Step 2—[3-Methyl-2-oxo-4-(4-piperidylmethyl) benzimidazol-1-vyl]piperidine-2,6-dione To a mixture of tert-butyl 4-[[1-(2,6-dioxo-3-piperidyl)-3-methyl-2-oxo-benzimidazol-4-yl]methyl] piperidine-1-carboxylate (100 mg, 219 umol) in DCM (2.0 mL) was added HCl/dioxane (4 M, 1.0 mL) in one portion at 25° C. under N$_2$. The reaction mixture was stirred at 25° C. for 30 min. On completion, the mixture was concentrated in vacuo to give the title compound (76.5 mg, 97% yield, HCl salt) as a white solid. LC-MS (ESI$^+$) m/z 357.1 (M+H)$^+$.

Step 3—4-[4-[[1-(2,6-dioxo-3-piperidyl)-3-methyl-2-oxo-benzimidazol-4-yl]methyl]-1-piperidyl] benzaldehyde A mixture of 3-[3-methyl-2-oxo-4-(4-piperidylmethyl) benzimidazol-1-yl]piperidine-2,6-dione (150 mg, 382 umol, HCl salt) in DMF (40 mL) was added K$_2$CO$_3$ (106 mg, 764 umol) and 4 Å molecular sieves (150 mg). The reaction mixture was stirred at 80° C. for 30 min. Then 4-fluorobenzaldehyde (71.1 mg, 573 umol) was added and stirred for 12 hours. On completion, the reaction mixture was filtered and the filtrate was concentrated in vacuo to give a residue. The residue was purified by reverse phase flash (FA condition) to give the title compound (100 mg, 57% yield) as white solid. $^1$H NMR (400 MHz, DMSO-d$_6$) δ=11.10 (s, 1H), 9.69 (s, 1H), 7.69 (d, J=8.8 Hz, 2H), 7.06-6.94 (m, 4H), 6.85 (dd, J=1.6, 7.2 Hz, 1H), 5.38 (dd, J=5.6, 12.4 Hz, 1H), 4.02 (d, J=13.6 Hz, 2H), 3.58 (s, 3H), 2.97-2.81 (m, 5H), 2.78-2.59 (m, 2H), 2.07-1.95 (m, 1H), 1.84 (m, 1H), 1.71 (d, J=12.0 Hz, 2H), 1.40-1.23 (m, 2H). LC-MS (ESI$^+$) m/z 461.2 (M+H)$^+$.

Ethyl 4-[4-[4-amino-3-(difluoromethyl)pyrazol-1-yl]-1-piperidyl]benzoate (Intermediate ATT)

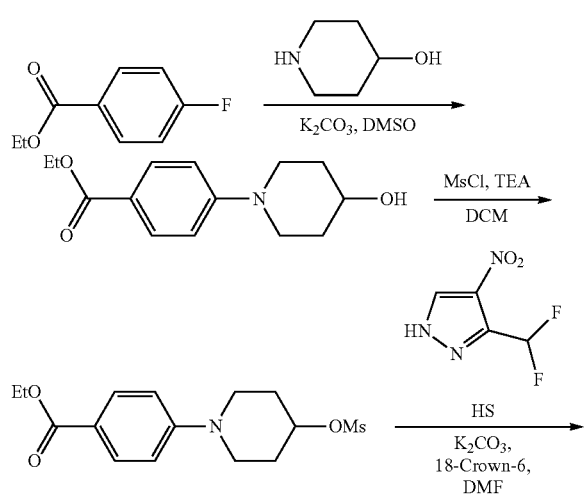

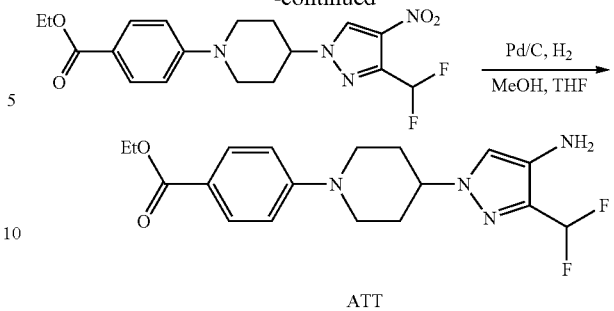

ATT

Step 1—Ethyl 4-(4-hydroxy-1-piperidyl)benzoate

A mixture of ethyl 4-fluorobenzoate (10.0 g, 59.4 mmol, CAS #451-46-7), piperidin-4-ol (7.22 g, 71.3 mmol, CAS #5382-16-1) and K$_2$CO$_3$ (8.22 g, 59.4 mmol) in DMSO (60 mL) was stirred at 120° C. for 32 hours. On completion, the mixture was cooled to 15° C. and poured into water (250 mL). The mixture was filtered, and the cake was washed with water (200 mL) and collected, and dried in vacuo to give the title compound (13.1 g, 88% yield) as a light yellow solid. $^1$H NMR (400 MHz, DMSO-d$_6$) δ 7.75 (d, J=9.2 Hz, 2H), 6.95 (d, J=9.2 Hz, 2H), 4.71 (d, J=4.0 Hz, 1H), 4.22 (q, J=7.2 Hz, 2H), 3.72-3.67 (m, 3H), 3.06-3.00 (m, 2H), 1.85-1.73 (m, 2H), 1.42-1.39 (m, 2H), 1.28 (t, J=7.2 Hz, 3H).

Step 2—Ethyl 4-(4-methylsulfonyloxy-1-piperidyl)benzoate

To a solution of ethyl 4-(4-hydroxy-1-piperidyl)benzoate (7.00 g, 28.0 mmol) and TEA (5.68 g, 56.1 mmol) in DCM (70 mL) was added MsCl (4.82 g, 42.1 mmol) at 0° C. The mixture was stirred at 0-10° C. for 2 hours. On completion, the mixture was diluted with water (20 mL) and partitioned. The aqueous phase was extracted with DCM (30 mL) and the combined organic layer was concentrated in vacuo. The residue was diluted with EA (200 mL), washed with brine (50 mL), dried over Na$_2$SO$_4$, filtered and concentrated in vacuo to give the title compound (9.00 g, 97% yield) as a light yellow solid. $^1$H NMR (400 MHz, DMSO-d$_6$) δ 7.78 (d, J=9.2 Hz, 2H), 7.00 (d, J=9.2 Hz, 2H), 4.92-4.90 (m, 1H), 4.23 (q, J=7.2 Hz, 2H), 3.72-3.60 (m, 2H), 3.30-3.23 (m, 2H), 3.22 (s, 3H), 2.08-1.98 (m, 2H), 1.77-1.73 (m, 2H), 1.28 (t, J=7.2 Hz, 3H).

Step 3—Ethyl 4-[4-[3-(difluoromethyl)-4-nitro-pyrazol-1-yl]-1-piperidyl]benzoate A mixture of 3-(difluoromethyl)-4-nitro-1H-pyrazole (2.00 g, 12.2 mmol, from Intermediate HS), ethyl 4-(4-methylsulfonyloxy-1-piperidyl)benzoate (4.01 g, 12.2 mmol), 18-crown-6 (324 mg, 1.23 mmol) and K$_2$CO$_3$ (5.08 g, 36.7 mmol) in DMF (60 mL) was stirred at 80° C. for 16 hours. To the mixture was added ethyl 4-(4-methylsulfonyloxy-1-piperidyl)benzoate (2.00 g, 6.11 mmol) at 25° C. The mixture was stirred at 80° C. for 16 hours. On completion, the mixture was cooled to 15° C. and diluted with water (300 mL), then extracted with EA (3×150 mL). The combined organic layer was washed with brine (100 mL), dried over Na$_2$SO$_4$, filtered and concentrated in vacuo. The residue was purified by reversed phase flash (TFA condition) to give the title compound (2.90 g, 46% yield) as a light yellow solid. LC-MS (ESI+) m/z 395.1 (M+H)+.

Step 4—Ethyl 4-[4-[4-amino-3-(difluoromethyl) pyrazol-1-yl]-1-piperidyl]benzoate A mixture of ethyl 4-[4-[3-(difluoromethyl)-4-nitro-pyrazol-1-yl]-1-piperidyl]benzoate (1.00 g, 1.98 mmol), and Pd/C (200 mg, 10 wt %) in THF (10 mL) and MeOH (10 mL) was stirred at 25° C. for 16 hours under H$_2$ (50 Psi). On completion, the mixture was filtered and the cake was washed with THF (10 mL). The filtrate and washing were combined and concentrated in vacuo. The residue was purified by reversed phase flash (FA condition) to give the desired compound (700 mg, 97% yield) as a light yellow solid. $^1$H NMR (400 MHz, DMSO-d$_6$) δ 7.78 (d, J=9.2 Hz, 2H), 7.19 (s, 1H), 7.05-6.69 (m, 3H), 4.36-4.27 (m, 1H), 4.24 (q, J=7.2 Hz, 2H), 4.06 (s, 2H), 4.05-3.98 (m, 2H), 3.03-2.98 (m, 2H), 2.06-1.98 (m, 2H), 1.95-1.81 (m, 2H), 1.29 (t, J=7.2 Hz, 3H).

4-[4-[3-(Difluoromethyl)-4-[[5-[(1R,4R)-2-oxa-5-azabicyclo[2.2.1]heptan-5-yl]pyrazolo [1,5-a]pyrimidine-3-carbonyl]amino]pyrazol-1-yl]-1-piperidyl]benzoic acid (Intermediate ATU)

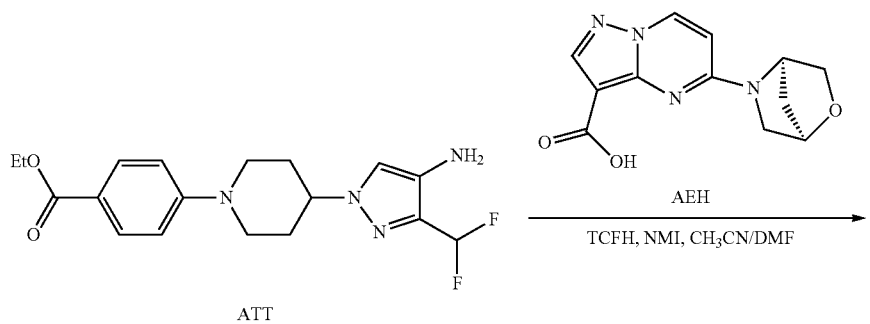

ATT

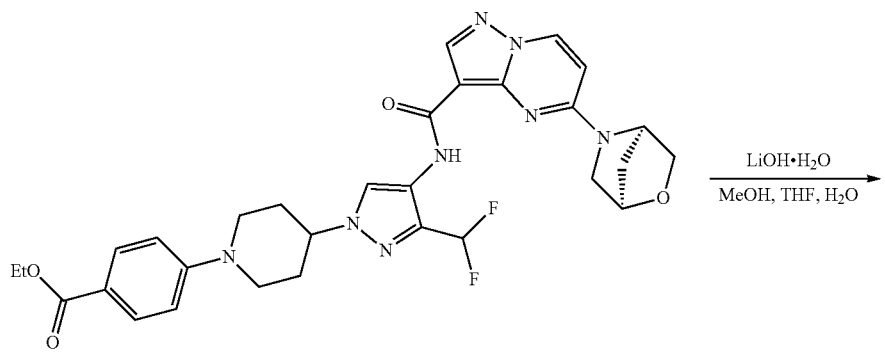

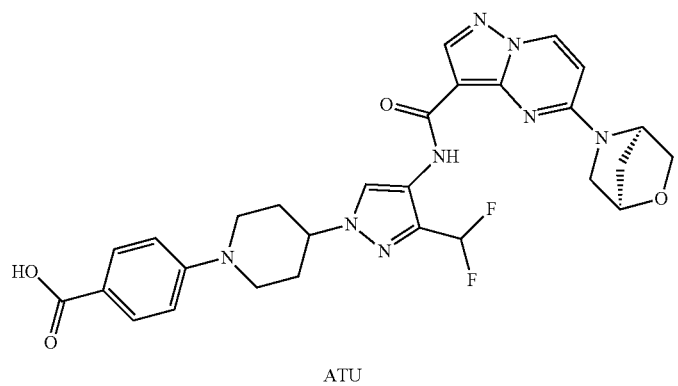

ATU

2029

Step 1—Ethyl 4-[4-[3-(difluoromethyl)-4-[[5-[(1R,4R)-2-oxa-5-azabicyclo[2.2.1]heptan-5-yl] pyrazolo[1,5-a]pyrimidine-3-carbonyl]amino]pyrazol-1-yl]-1-piperidyl]benzoate A mixture of 5-[(1R,4R)-2-oxa-5-azabicyclo[2.2.1]heptan-5-yl]pyrazolo[1,5-a]pyrimidine-3-carboxylic acid (263 mg, 1.01 mmol, Intermediate AEH), [chloro(dimethylamino)methylene]-dimethyl-ammonium; hexafluorophosphate (404 mg, 1.44 mmol) and 1-methylimidazole (280 mg, 3.41 mmol) in CH₃CN (7 mL) and DMF (0.7 mL) was stirred at 25° C. for 0.5 hour. Then ethyl 4-[4-[4-amino-3-(difluoromethyl)pyrazol-1-yl]-1-piperidyl]benzoate (350 mg, 960 umol, Intermediate ATT) was added to the mixture at 25° C. and the mixture was stirred at 25° C. for 2 hours. On completion, the reaction was quenched with water (0.2 mL) and the residue was concentrated in vacuo. The residue was purified by reversed phase flash (TFA condition) to give the title compound (400 mg, 68% yield) as a light yellow solid. $^1$H NMR (400 MHz, DMSO-d₆) δ 9.50 (d, J=5.2 Hz, 1H), 8.78 (d, J=7.6 Hz, 1H), 8.44 (d, J=4.4 Hz, 1H), 8.26 (d, J=5.6 Hz, 1H), 7.79 (d, J=9.2 Hz, 2H), 7.26-6.95 (m, 3H), 6.89-6.41 (m, 1H), 5.32-5.03 (m, 1H), 4.76 (d, J=16.4 Hz, 1H), 4.62-4.49 (m, 1H), 4.24 (q, J=7.2 Hz, 2H), 4.06 (d, J=13.2 Hz, 2H), 3.85-3.71 (m, 2H), 3.62-3.58 (m, 1H), 3.45-3.43 (m, 1H), 3.05 (t, J=11.6 Hz, 2H), 2.12-1.92 (m, 6H), 1.29 (t, J=7.2 Hz, 3H).

Step 2—4-[4-[3-(Difluoromethyl)-4-[[5-[(1R,4R)-2-oxa-5-azabicyclo[2.2.1]heptan-5-yl]pyrazolo [1,5-a]pyrimidine-3-carbonyl]amino]pyrazol-1-yl]-1-piperidyl]benzoic acid A mixture of ethyl 4-[4-[3-(difluoromethyl)-4-[[5-[(1R,4R)-2-oxa-5-azabicyclo[2.2.1]heptan-5-yl] pyrazolo[1,5-a]pyrimidine-3-carbonyl]amino]pyrazol-1-yl]-1-piperidyl]benzoate (350 mg, 576 umol) and LiOH.H₂O (121 mg, 2.88 mmol) in MeOH (2 mL), THF (6 mL) and H₂O (2 mL) was stirred at 60° C. for 2 hours. On completion, the mixture was cooled to 25° C., and acidified to pH=5 with 1.0 M aq. HCl and filtered. The cake was collected and the filtrate was extracted with DCM (3×30 mL). The organic layer and the collected cake were combined and concentrated in vacuo to give a residue. The residue was purified by reversed phase flash chromatography (FA) to give the title compound (150 mg, 44% yield) as a light yellow solid. LC-MS (ESI⁺) m/z 579.3 (M+H)⁺.

3-[5-(5-aminopent-1-ynyl)-3-methyl-2-oxo-benzimidazol-1-yl]piperidine-2,6-dione (Intermediate ATV)

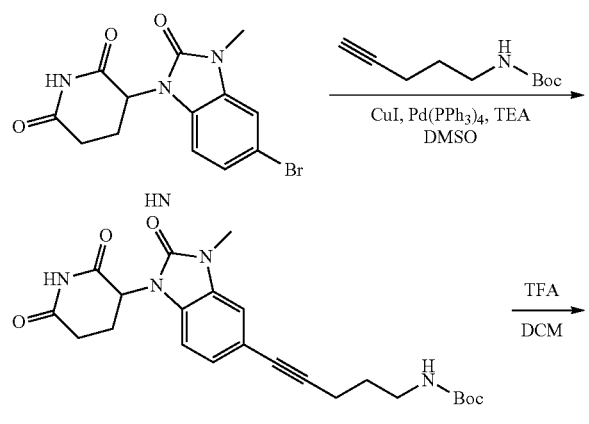

2030

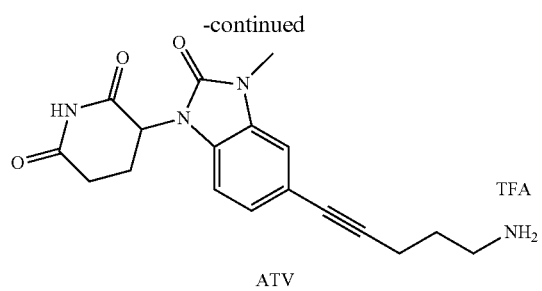

Step 1—Tert-butyl N-[5-[1-(2,6-dioxopiperidin-3-yl)-3-methyl-2-oxo-1,3-benzodiazol-5-yl]pent-4-yn-1-yl] carbamate To a stirred solution of 3-(5-bromo-3-methyl-2-oxo-1,3-benzodiazol-1-yl)piperidine-2,6-dione (3.80 g, 11.2 mmol, Intermediate HN) and tert-butyl N-(pent-4-yn-1-yl)carbamate (3.09 g, 16.8 mmol, CAS #151978-50-6) in DMSO (20.00 mL) and TEA (10.00 mL) were added Pd(PPh₃)₄ (1.30 g, 1.12 mmol) and CuI (0.21 g, 1.1 mmol) at room temperature under nitrogen atmosphere. The resulting mixture was stirred for overnight at 85° C. under nitrogen atmosphere. The resulting mixture was then cooled down to room temperature and concentrated under reduced pressure to remove TEA. The residue was diluted with water (100 mL) and extracted with EtOAc (5×200 mL). The combined organic layers were washed with brine (3×100 mL), and dried over anhydrous Na₂SO₄. After filtration, the filtrate was concentrated under reduced pressure. The residue was purified by silica gel column chromatography, eluted with petroleum ether/EtOAc (1:1) to afford the title compound (4 g, 81%) as a brown solid. $^1$H NMR (400 MHz, DMSO-d₆) δ 11.10 (s, 1H), 7.25 (s, 1H), 7.10 (s, 2H), 6.88 (s, 1H), 5.38 (dd, J=12.7, 5.3 Hz, 1H), 3.34 (s, 3H), 3.06 (q, J=6.7 Hz, 2H), 2.93-2.83 (m, 1H), 2.78-2.58 (m, 2H), 2.41 (t, J=7.1 Hz, 2H), 2.02 (dd, J=10.7, 5.7 Hz, 1H), 1.66 (p, J=7.1 Hz, 2H), 1.39 (s, 9H). LC/MS (ESI, m/z): [(M+1)]⁺=441.2.

Step 2—3-[5-(5-Aminopent-1-yn-1-yl)-3-methyl-2-oxo-1,3-benzodiazol-1-yl]piperidine-2,6-dione; trifluoroacetaldehyde To a stirred solution of tert-butyl N-[5-[1-(2,6-dioxopiperidin-3-yl)-3-methyl-2-oxo-1,3-benzodiazol-5-yl]pent-4-yn-1-yl]carbamate (4.90 g, 11.1 mmol) in DCM (50.00 mL) was added TFA (5.00 mL) dropwise at room temperature and the resulting mixture was stirred for 16 h at room temperature. The mixture was then concentrated under reduced pressure and the residue was triturated with ethyl ether (25 mL). After filtration, the filter cake was washed with ethyl ether (2×5 mL) and dried to give the title compound (4 g, crude) as a white solid. $^1$H NMR (400 MHz, Methanol-d4) δ 7.21 (d, J=1.4 Hz, 1H), 7.17 (dd, J=8.2, 1.5 Hz, 1H), 7.07 (d, J=8.2 Hz, 1H), 5.34 (dd, J=12.6, 5.4 Hz, 1H), 3.41 (s, 3H), 3.14 (t, J=7.7 Hz, 2H), 2.93 (ddd, J=18.0, 14.2, 5.1 Hz, 1H), 2.87-2.71 (m, 2H), 2.60 (t, J=6.9 Hz, 2H), 2.23-2.11 (m, 1H), 1.97 (dq, J=9.7, 7.0 Hz, 2H). LC/MS (ESI, m/z): [(M+1)]⁺=341.2.

2031

[4-[4-Amino-3-(difluoromethyl)pyrazol-1-yl]phenyl]methanol (Intermediate ATX)

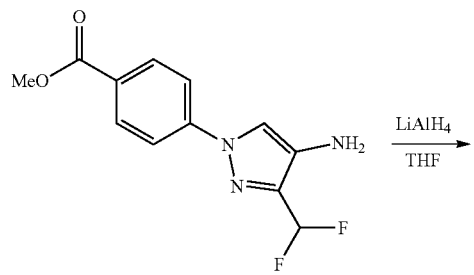

To a mixture of methyl 4-[4-amino-3-(difluoromethyl)pyrazol-1-yl]benzoate (850 mg, 3.18 mmol, Intermediate FW) in THF (20 mL) was added LiAlH$_4$ (181 mg, 4.77 mmol) at 0° C. The mixture was stirred at 25° C. for 0.5 hour. On completion, the reaction was quenched with water (1.8 mL) and 15% NaOH (1.8 mL). The mixture was extracted with DCM (3×15 mL), and washed with brine (10 mL). The combined organic phase was dried over Na$_2$SO$_4$, filtered and the filtrate was concentrated in vacuo to give the title compound (720 mg, 94% yield) as a brown solid. $^1$HNMR (400 MHz, DMSO-d$_6$) δ 7.78 (s, 1H), 7.68 (d, J=8.4 Hz, 2H), 7.41 (d, J=8.4 Hz, 2H), 7.21-6.92 (m, 1H), 5.25 (d, J=5.6 Hz, 1H), 4.52 (d, J=5.2 Hz, 2H), 4.39 (s, 2H).

N-[3-(difluoromethyl)-1-(4-formylphenyl)pyrazol-4-yl]-5-morpholino-pyrazolo[1,5-a] pyrimidine-3-carboxamide (Intermediate ATY)

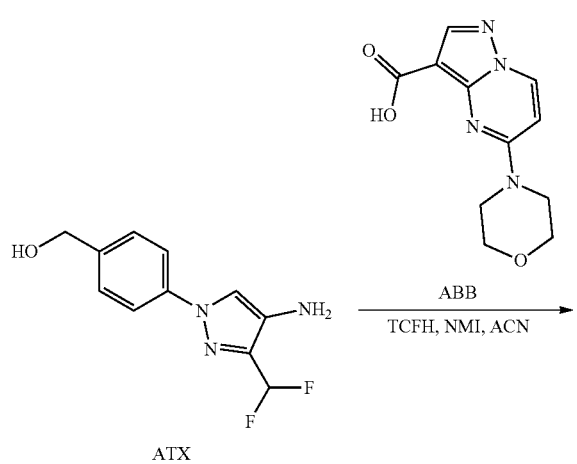

2032

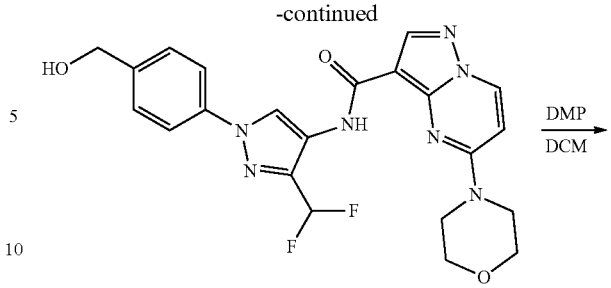

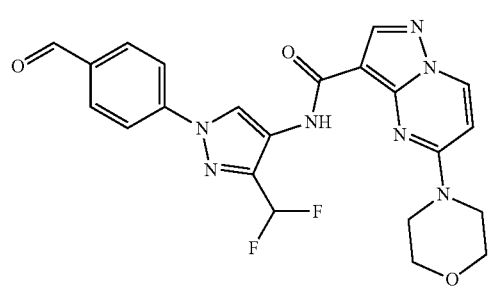

Step 1—N-[3-(difluoromethyl)-1-[4-(hydroxymethyl)phenyl]pyrazol-4-yl]-5-morpholino-pyrazolo[1,5-a]pyrimidine-3-carboxamide

To a mixture of 5-morpholinopyrazolo[1,5-a]pyrimidine-3-carboxylic acid (600 mg, 2.42 mmol, Intermediate ABB) in CH$_3$CN (10 mL) was added 1-methylimidazole (694 mg, 8.46 mmol) and [chloro(dimethylamino)methylene]-dimethyl-ammonium; hexafluorophosphate (813 mg, 2.90 mmol). The mixture was stirred at 25° C. for 0.5 hour. Then [4-[4-amino-3-(difluoromethyl)pyrazol-1-yl] phenyl]methanol (578 mg, 2.42 mmol, Intermediate ATX) was added into the mixture and the reaction mixture was stirred at 25° C. for 1 hour. On completion, the mixture was filtered. The filter cake was collected and dried in vacuo to give the title compound (1.00 g, 88% yield) as a white solid. $^1$H NMR (400 MHz, DMSO-d$_6$) δ 9.49 (s, 1H), 8.96 (s, 1H), 8.83 (d, J=8.0 Hz, 1H), 8.32 (s, 1H), 7.79 (d, J=8.4 Hz, 2H), 7.53-6.83 (m, 4H), 5.30 (d, J=5.2 Hz, 1H), 4.55 (d, J=5.2 Hz, 2H), 3.86-3.70 (m, 8H).

Step 2—N-[3-(difluoromethyl)-1-(4-formylphenyl)pyrazol-4-yl]-5-morpholino-pyrazolo[1,5-a] pyrimidine-3-carboxamide

To a mixture of N-[3-(difluoromethyl)-1-[4-(hydroxymethyl)phenyl]pyrazol-4-yl]-5-morpholino-pyrazolo[1,5-a]pyrimidine-3-carboxamide (1.00 g, 2.13 mmol) in DMF (30 mL) was added DMP (993 mg, 2.34 mmol). The reaction mixture was stirred at 70° C. for 0.5 hour. On completion, the reaction mixture was poured into the water (20 mL) and filtered. The filter cake was collected and dried in vacuo to give the title compound (750 mg, 75% yield) as white solid. LC-MS (ESI$^+$) m/z 468.1 (M+H)$^+$.

2033

Methyl 6-chloro-1,5-naphthyridine-4-carboxylate (Intermediate ATZ)

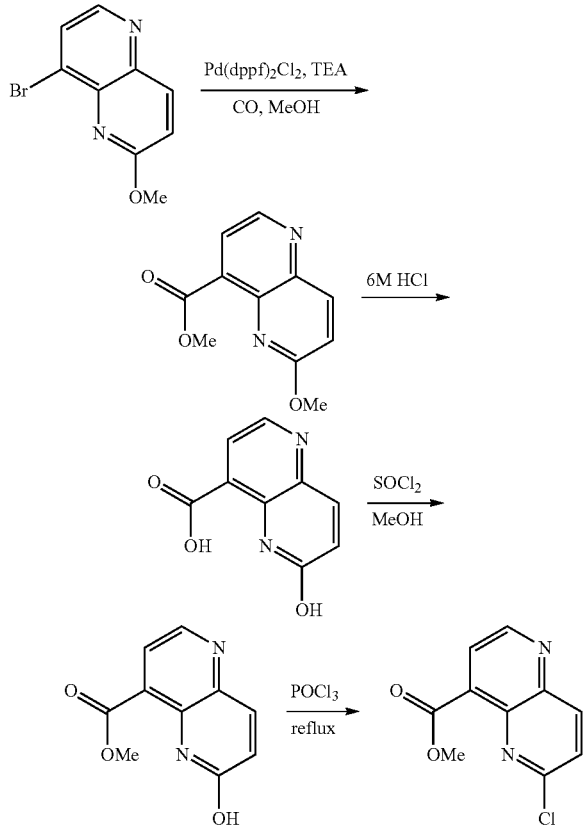

Step 1—Methyl 6-methoxy-1,5-naphthyridine-4-carboxylate

To a solution of 8-bromo-2-methoxy-1,5-naphthyridine (2.00 g, 8.37 mmol, CAS #881658-92-0) in MeOH (20 mL) was added Pd(dppf)Cl$_2$ (918 mg, 1.25 mmol) and TEA (2.54 g, 25.1 mmol) under N$_2$. The suspension was degassed under vacuum and purged with CO several times. The mixture was stirred under CO (50 psi) at 80° C. for 16 hours. On completion, the reaction mixture was concentrated in vacuo. The residue was purified by column chromatography (SiO$_2$, Petroleum ether/Ethyl acetate=10/1 to 3/1) to give the title compound (1.70 g, 88% yield) as a yellow solid. $^1$H NMR (400 MHz, DMSO-d$_6$) δ=8.88 (d, J=4.4 Hz, 1H), 8.33 (d, J=9.2 Hz, 1H), 7.84 (d, J=4.4 Hz, 1H), 7.33 (d, J=8.8 Hz, 1H), 3.99 (s, 3H), 3.96 (s, 3H).

Step 2—6-Hydroxy-1,5-naphthyridine-4-carboxylic acid

To a solution of methyl 6-methoxy-1,5-naphthyridine-4-carboxylate (800 mg, 3.48 mmol) in 6.0 M aq.HCl (5.80 mL). The mixture was stirred at 100° C. for 2 hours. On completion, the reaction mixture was concentrated in vacuo to give the title compound (800 mg, 99% yield) as a yellow solid. LC-MS (ESI$^+$) m/z 190.8 (M+H)$^+$.

2034

Step 3—Methyl 6-hydroxy-1,5-naphthyridine-4-carboxylate

To a solution of 6-hydroxy-1,5-naphthyridine-4-carboxylic acid (800 mg, 4.21 mmol) in MeOH (10 mL) was added SOCl$_2$ (10.0 g, 84.1 mmol). The mixture was stirred at 80° C. for 16 hours. On completion, the reaction mixture was concentrated in vacuo. The residue was diluted with water (30 mL), then basified to pH=7 with sat. aq. NaHCO$_3$, and extracted with EA (3×100 mL). The combined organic layers were concentrated in vacuo. The residue was purified by reversed-phase HPLC (0.1% FA condition). to give the title compound (500 mg, 58% yield) as a yellow solid. LC-MS (ESI$^+$) m/z 204.8 (M+H)$^+$.

Step 4—Methyl 6-chloro-1,5-naphthyridine-4-carboxylate

A solution of methyl 6-hydroxy-1,5-naphthyridine-4-carboxylate (500 mg, 2.45 mmol) in POCl$_3$ (5 mL) was stirred at 80° C. for 1 hour. On completion, the reaction mixture was concentrated in vacuo. The residue was added and then diluted with H$_2$O (100 mL) and sat. aq. NaHCO$_3$ (3 mL), then extracted with EA (3×100 mL). The combined organic layers were dried over Na$_2$SO$_4$, filtered and concentrated in vacuo to give the title compound (700 mg, 99% yield) as a yellow solid. LC-MS (ESI$^+$) m/z 223.6 (M+H)$^+$.

3-(4-Hydroxy-1-oxo-isoindolin-2-yl)-1-methyl-piperidine-2,6-dione (Intermediate AOB)

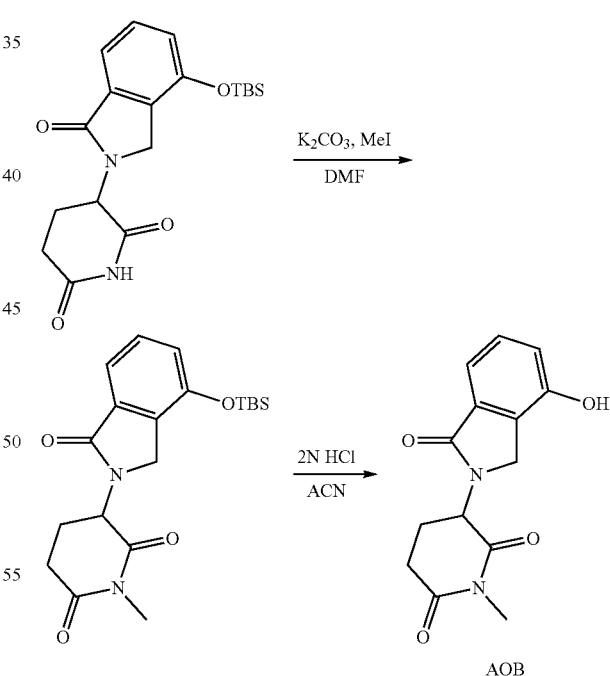

Step 1—3-[4-[Tert-butyl(dimethyl)silyl]oxy-1-oxo-isoindolin-2-yl]-1-methyl-piperidine-2,6-dione To a solution of 3-[4-[tert-butyl(dimethyl)silyl]oxy-1-oxo-isoindolin-2-yl]piperidine-2,6-dione (1.00 g, 2.67 mmol, synthesized via Steps 1-3 of Intermediate AHK) in DMF (12 mL) was added MeI (1.33 g, 9.35 mmol) and $K_2CO_3$ (553 mg, 4.01 mmol) at 0° C. The reaction mixture was stirred at 0-25° C. for 12 hrs. On completion, the reaction mixture was filtered and the filtrate was concentrated in vacuo to give a residue. The residue was purified by reverse phase (0.1% FA condition) to give the title compound (130 mg, 12% yield) as white solid. LC-MS (ESI$^+$) m/z 389.2 (M+H)$^+$.

Step 2—3-(4-Hydroxy-1-oxo-isoindolin-2-yl)-1-methyl-piperidine-2,6-dione

To a solution of 3-[4-[tert-butyl(dimethyl)silyl]oxy-1-oxo-isoindolin-2-yl]-1-methyl-piperidine-2,6-dione (130 mg, 334 umol) in ACN (4 mL) was added HCl (2 M, 1.5 mL) at 25° C. The mixture was stirred at 25° C. for 2 hrs. On completion, the mixture was concentrated in vacuo to give a residue. The residue was purified by reverse phase (0.1% FA condition) to give the title compound (80.0 mg, 87% yield) as white solid. LC-MS (ESI$^+$) m/z 275.6 (M+H)$^+$.

1-Methyl-3-[1-oxo-4-[[4-(piperazin-1-ylmethyl)phenyl]methoxy]isoindolin-2-yl]piperidine-2,6-dione (Intermediate AOC)

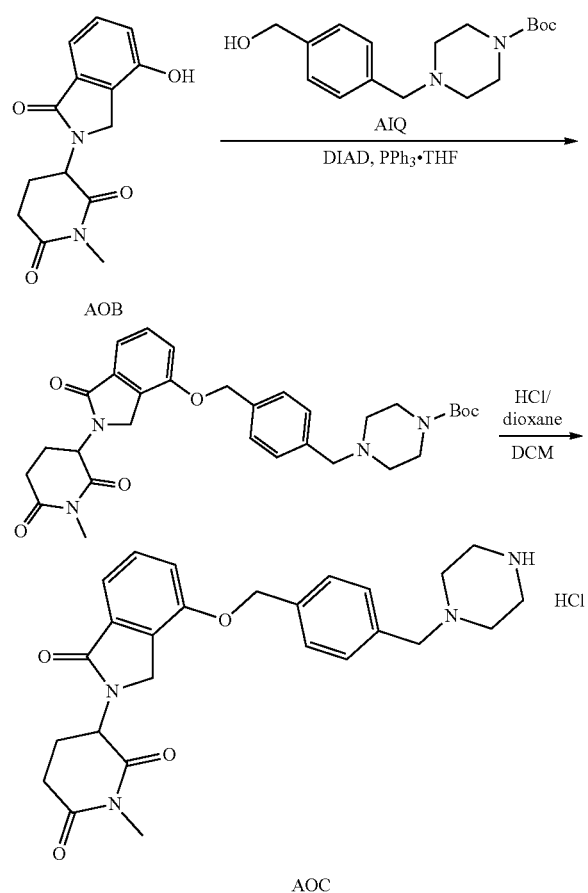

AOB

AOC

Step 1—Tert-butyl4-[[4-[[2-(1-methyl-2,6-dioxo-3-piperidyl)-1-oxo-isoindolin-4-yl]oxymethyl] phenyl] methyl] piperazine-1-carboxylate To a solution of 3-(4-hydroxy-1-oxo-isoindolin-2-yl)-1-methyl-piperidine-2,6-dione (60.0 mg, 218 umol, Intermediate AOB) and tert-butyl 4-[[4-(hydroxymethyl)phenyl]methyl]piperazine-1-carboxylate (87.1 mg, 284 umol, Intermediate AIQ) in THF (3 mL) was added DIAD (66.3 mg, 328 umol) and $PPh_3$ (86.0 mg, 328 umol) at 0° C. The reaction mixture was stirred at 0-25° C. for 12 hrs under $N_2$. On completion, the mixture was concentrated in vacuo to give the residue. The residue was purified by prep-HPLC (column: Phenomenex Synergi C18 150*25*10 um; mobile phase: [water (0.225% FA)-ACN]; B %: 10%-40%, 10 min) to give the title compound (40.0 mg, 32% yield) as white solid. $^1$H NMR (400 MHz, DMSO-$d_6$) δ 7.52-7.47 (m, 1H), 7.44 (d, J=8.0 Hz, 2H), 7.36-7.30 (m, 4H), 5.24-5.15 (m, 3H), 4.45-4.33 (m, 1H), 4.29-4.18 (m, 1H), 3.48 (s, 2H), 2.99 (s, 4H), 2.79-2.68 (m, 1H), 2.46-2.40 (m, 5H), 2.31-2.27 (m, 4H), 2.03-1.94 (m, 1H), 1.38 (s, 9H); LC-MS (ESI$^+$) m/z 563.2 (M+H)$^+$.

Step 2—1-Methyl-3-[1-oxo-4-[[4-(piperazin-1-ylmethyl)phenyl]methoxy]isoindolin-2-yl]piperidine-2,6-dione To a solution of tert-butyl 4-[[4-[[2-(1-methyl-2,6-dioxo-3-piperidyl)-1-oxo-isoindolin-4-yl] oxymethyl]phenyl]methyl]piperazine-1-carboxylate (30.0 mg, 53.3 umol) in DCM (3 mL) was added HCl/dioxane (4 M, 1.20 mL) at 25° C. The mixture was stirred at 25° C. for 2 hrs. On completion, the reaction mixture was concentrated in vacuo to give the title compound (26.0 mg, 97% yield, HCl salt) as a yellow solid. LC-MS (ESI$^+$) m/z 463.3 (M+H)$^+$.

3-[4-[3-(2,7-Diazaspiro[3.5]nonan-2-yl)propyl]-3-methyl-2-oxo-benzimidazol-1-yl]piperidine-2,6-dione (Intermediate AOD)

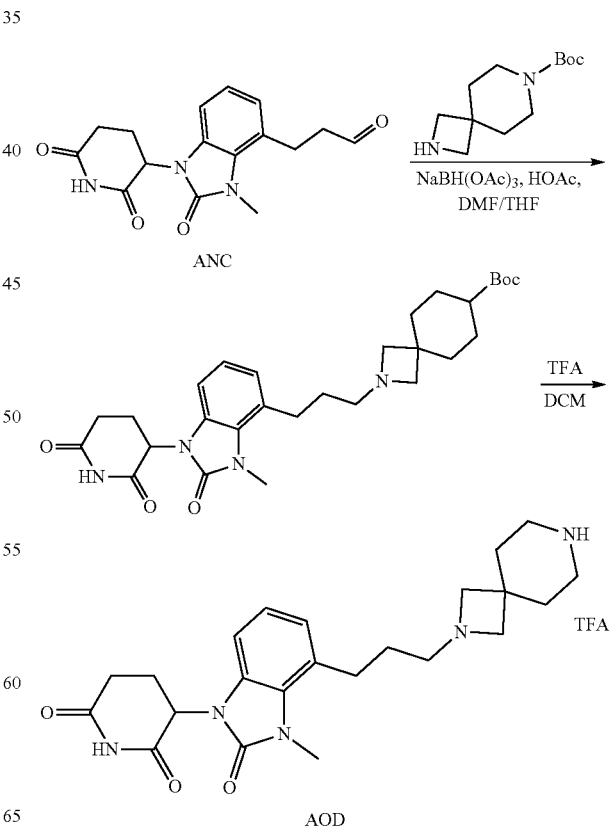

ANC

AOD

Step 1—Tert-butyl 2-[3-[1-(2,6-dioxo-3-piperidyl)-3-methyl-2-oxo-benzimidazol-4-yl]propyl]-2,7-diazaspiro[3.5]nonane-7-carboxylate To a solution of 3-[1-(2,6-dioxo-3-piperidyl)-3-methyl-2-oxo-benzimidazol-4-yl]propanal (25.0 mg, 79.3 umol, Intermediate ANC) and tertbutyl 2,7-diazaspiro[3.5]nonane-7-carboxylate (17.9 mg, 79.3 umol, CAS #896464-16-7) in THF (0.50 mL) and DMF (0.50 mL) was added HOAc (4.76 mg, 79.3 umol), and the mixture was stirred at 20° C. for 0.5 hour. Then, NaBH(OAc)$_3$ (20.2 mg, 95.1 umol) was added and the mixture was stirred at 20° C. for 1 hour. On completion, the reaction mixture was quenched with water (0.5 mL), and then concentrated in vacuo to give a residue. The residue was purified by prep-HPLC (column: Phenomenex Synergi C18 150*25*10 um; mobile phase: [water (0.225% FA)-ACN]; B %: 9%-39%, 10 min) to give the title compound (20.0 mg, 48% yield) as a white solid. LC-MS (ESI$^+$) m/z 526.4 (M+H)$^+$.

Step 2—3-[4-[3-(2,7-Diazaspiro[3.5]nonan-2-yl)propyl]-3-methyl-2-oxo-benzimidazol-1-yl] piperidine-2,6-dione To a solution of tert-butyl 2-[3-[1-(2,6-dioxo-3-piperidyl)-3-methyl-2-oxo-benzimidazol-4-yl]propyl]-2,7-diazaspiro[3.5]nonane-7-carboxylate (15.0 mg, 28.5 umol) in DCM (1.00 mL) was added TFA (117 mg, 1.03 mmol, 76.1 uL), and the mixture was stirred at 20° C. for 1 hour. On completion, the reaction mixture was concentrated in vacuo to give the title compound (15 mg, 97% yield, TFA salt) as a white solid. LC-MS (ESI$^+$) m/z 426.3 (M+H)$^+$.

Tert-butyl (2R)-2-(prop-2-ynoxymethyl)morpholine-4-carboxylate (Intermediate AOG)

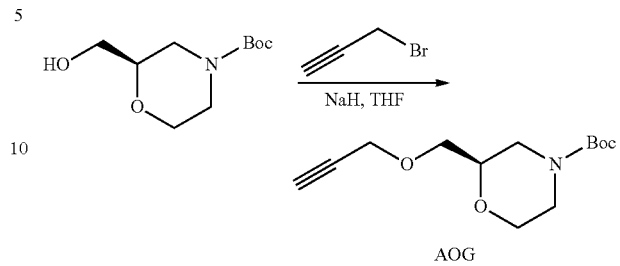

To a solution of tert-butyl (2R)-2-(hydroxymethyl)morpholine-4-carboxylate (500 mg, 2.30 mmol, CAS #135065-71-3) in THF (20 mL) was added NaH (138 mg, 3.45 mmol, 60% dispersion in mineral oil) at 0° C., and the mixture was stirred at 0° C. for 0.5 hr. Then 3-bromoprop-1-yne (513 mg, 3.45 mmol) was added and the mixture was stirred at 15° C. for 16 hrs. On completion, the reaction mixture was quenched with H$_2$O (2 mL) and concentrated in vacuo. The residue was diluted with H$_2$O (20 mL), and extracted with EA (3×20 mL). The organic layers were washed with brine (3×15 mL), dried over anhydrous Na$_2$SO$_4$, filtered and concentrated in vacuo to give the title compound (580 mg, 98% yield) as yellow oil. $^1$H NMR (400 MHz, CDCl$_3$) δ 4.14 (d, J=2.4 Hz, 2H), 3.93-3.69 (m, 3H), 3.57-3.43 (m, 4H), 2.98-2.78 (m, 1H), 2.75-2.55 (m, 1H), 2.38 (t, J=2.0 Hz, 1H), 1.40 (s, 9H).

3-[3-Methyl-4-[3-[[(2R)-morpholin-2-yl]methoxy]propyl]-2-oxo-benzimidazol-1-yl] piperidine-2,6-dione (Intermediate AOH)

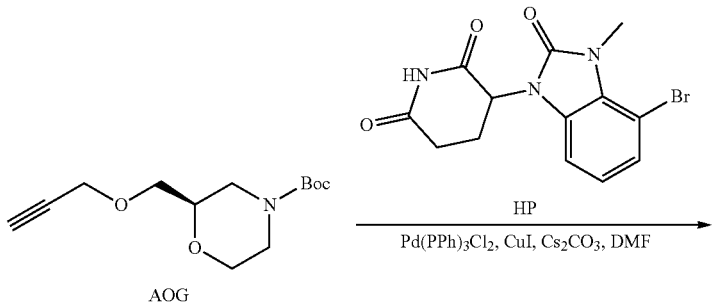

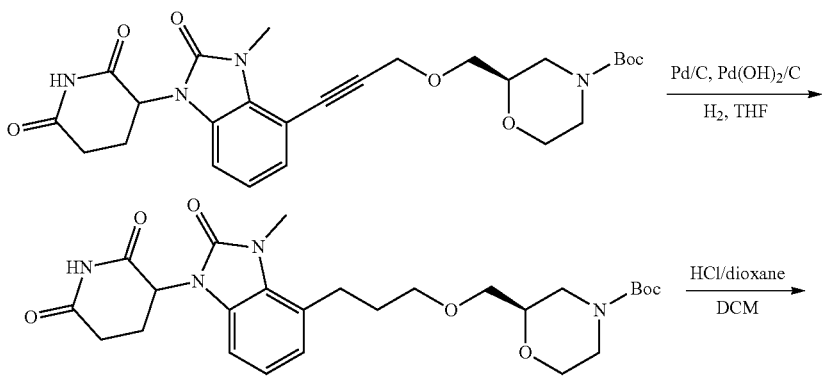

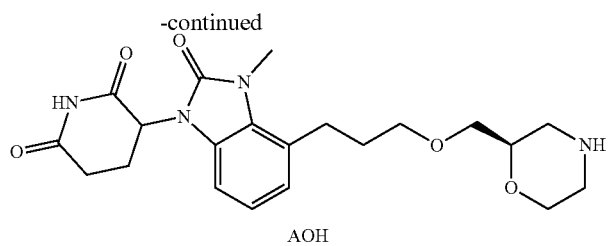

AOH

Step 1—Tert-butyl (2R)-2-[3-[1-(2,6-dioxo-3-piperidyl)-3-methyl-2-oxo-benzimidazol-4-yl]prop-2-ynoxymethyl]morpholine-4-carboxylate To a solution of tert-butyl (2R)-2-(prop-2-ynoxymethyl)morpholine-4-carboxylate (453 mg, 1.77 mmol, Intermediate AOG), 3-(4-bromo-3-methyl-2-oxo-benzimidazol-1-yl)piperidine-2,6-dione (400 mg, 1.18 mmol, Intermediate HP) in DMF (4 mL) was added Pd(PPh$_3$)$_2$Cl$_2$ (166 mg, 236 umol), CuI (45.0 mg, 236 umol) and Cs$_2$CO$_3$ (1.54 g, 4.73 mmol). The mixture was stirred at 80° C. for 3 hrs. On completion, the mixture was filtered and concentrated in vacuo. The mixture was purified by reverse phase: (0.1% FA) to give the title compound (390 mg, 64% yield) as yellow solid. $^1$H NMR (400 MHz, DMSO-d$_6$) δ 11.12 (s, 1H), 7.21-7.10 (m, 2H), 7.07-6.97 (m, 1H), 5.45-5.35 (m, 1H), 4.48 (s, 2H), 3.88-3.77 (m, 2H), 3.74-3.66 (m, 1H), 3.64 (s, 3H), 3.60-3.50 (m, 3H), 3.44-3.36 (m, 2H), 2.95-2.81 (m, 2H), 2.76-2.69 (m, 1H), 2.65-2.60 (m, 1H), 2.10-1.96 (m, 1H), 1.39 (s, 9H), LC-MS (ESI$^+$) m/z 413.1 (M+H−100)$^+$.

Step 2—Tert-butyl (2R)-2-[3-[1-(2,6-dioxo-3-piperidyl)-3-methyl-2-oxo-benzimidazol-4-yl]propoxymethyl]morpholine-4-carboxylate To a solution of tert-butyl (2R)-2-[3-[1-(2,6-dioxo-3-piperidyl)-3-methyl-2-oxo-benzimidazol-4-yl] prop-2-ynoxymethyl]morpholine-4-carboxylate (390 mg, 760 umol) in THF (20 mL) was added Pd/C (200 mg) and Pd(OH)$_2$/C (200 mg). The mixture was stirred at 25° C. for 3 hrs under H$_2$ (15 psi). On completion, the mixture was filtered and concentrated in vacuo to give the title compound (380 mg, 96% yield) as white solid. $^1$H NMR (400 MHz, DMSO-d$_6$) δ 11.09 (s, 1H), 7.00-6.92 (m, 2H), 6.90-6.85 (m, 1H), 5.45-5.25 (m, 1H), 3.88-3.76 (m, 2H), 3.75-3.65 (m, 1H), 3.64-3.58 (m, 1H), 3.56 (s, 3H), 3.51-3.43 (m, 4H), 3.41-3.34 (m, 2H), 2.99-2.92 (m, 2H), 2.90-2.85 (m, 1H), 2.76-2.68 (m, 1H), 2.65-2.55 (m, 1H), 2.04-1.95 (m, 1H), 1.90-1.79 (m, 2H), 1.79-1.72 (m, 1H), 1.40 (s, 9H)

Step 3—3-[3-Methyl-4-[3-[[(2R)-morpholin-2-yl]methoxy]propyl]-2-oxo-benzimidazol-1-yl] piperidine-2,6-dione To a solution of tert-butyl (2R)-2-[3-[1-(2,6-dioxo-3-piperidyl)-3-methyl-2-oxo-benzimidazol-4-yl] propoxymethyl]morpholine-4-carboxylate (60.0 mg, 116 umol) in DCM (2.00 mL) was added HCl/dioxane (4.00 M, 2.00 mL). The mixture was stirred at 25° C. for 0.5 hr. On completion, the mixture was concentrated in vacuo to give the title compound (50 mg, 95% yield, HCl) as white solid. LC-MS (ESI$^+$) m/z 417.3 (M+H)$^+$.

4-[3-Morpholino-4-(pyrazolo[1,5-a]pyrimidine-3-carbonylamino)pyrazol-1 yl]cyclohexanecarboxylic acid (Intermediate AOI)

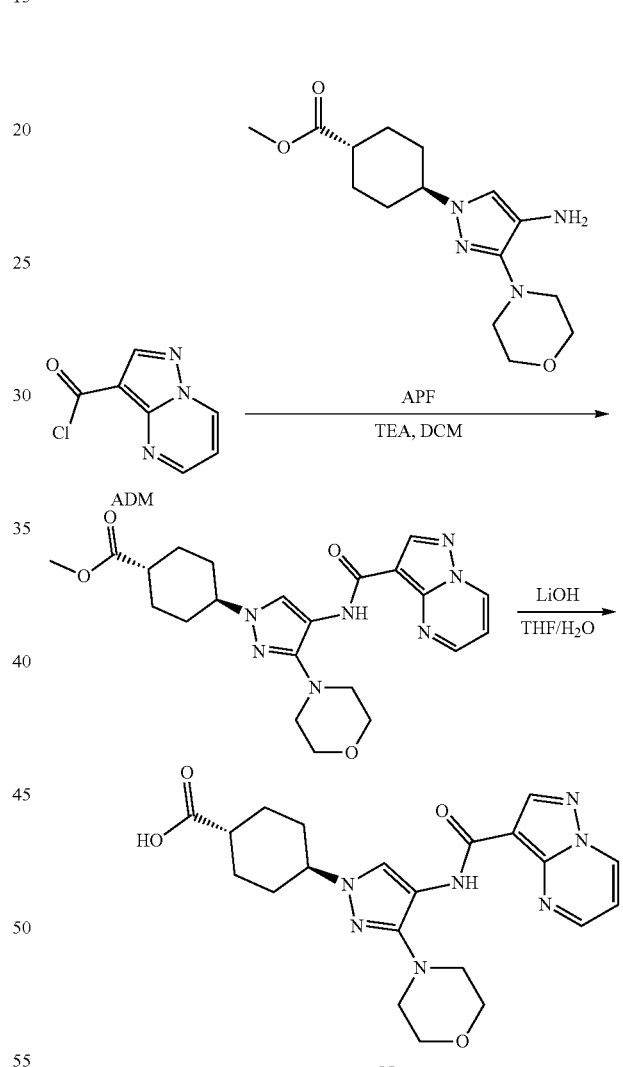

Step 1—Methyl 4-[3-morpholino-4-(pyrazolo[1,5-a]pyrimidine-3-carbonylamino)pyrazol-1-yl] cyclohexanecarboxylate To a solution of methyl 4-(4-amino-3-morpholino-pyrazol-1-yl)cyclohexanecarboxylate (400 mg, 1.04 mmol, Intermediate APF) and TEA (315 mg, 3.11 mmol) in DCM (20 mL) was added pyrazolo[1,5-a]pyrimidine-3-carbonyl chloride (376 mg, 2.08 mmol, Intermediate ADM), and the reaction mixture was stirred at 15° C. for 0.5 hr. On completion, the reaction mixture was quenched with water (30 mL), and extracted with DCM (2×20 mL). The combined organic layers were washed with water (30 mL) dried over Na$_2$SO$_4$, filtered and concentrated in vacuo to give a green residue. The residue was purified by column chromatography (PE/EA=1/6) to give the title compound (330 mg, 70% yield) as yellow solid. $^1$H NMR (400 MHz, DMSO-d$_6$) δ 9.63 (s, 1H), 9.37 (dd, J=7.2, 1.6 Hz, 1H), 8.90 (dd, J=4.0, 1.6 Hz, 1H), 8.66 (s, 1H), 8.02 (s, 1H), 7.32 (dd, J=7.2, 4.0 Hz, 1H), 4.03-3.99 (m, 1H), 3.83-3.79 (m, 4H), 3.64 (s, 3H), 3.04-2.99 (m, 4H), 2.52-2.49 (m, 1H), 2.02-1.98 (m, 4H), 1.80-1.65 (m, 2H), 1.53-1.49 (m, 2H); LC-MS (ESI$^+$) m/z 454.1 (M+H)$^+$.

Step 2—4-[3-Morpholino-4-(pyrazolo[1,5-a]pyrimidine-3-carbonylamino)pyrazol-1-yl]cyclohexanecarboxylic acid To a solution of methyl 4-[3-morpholino-4-(pyrazolo[1,5-a]pyrimidine-3-carbonylamino)pyrazol-1-yl]cyclohexanecarboxylate (70 mg, 154 umol) in a mixed solvent of THF (0.8 mL) and H$_2$O (0.2 mL) was added LiOH (11.0 mg, 463 umol) and stirred at 25° C. for 2 hrs. On completion, the mixture was extracted by EA (2×5 mL), and the aqueous phase was acidified by HCl (1N) until the pH=5 and the product precipitated out of solution. The mixture was filtrated and the filter cake was concentrated in vacuo to give the title compound (40 mg, 58% yield) as yellow solid. LC-MS (ESI$^+$) m/z 440.2 (M+H)$^+$.

3-(4-(4-((1R,5S)-3,8-diazabicyclo[3.2.1]octan-3-yl)butyl)-3-methyl-2-oxo-2,3-dihydro-1H-benzo[d]imidazol-1-yl)piperidine-2,6-dione (Intermediate AOJ)

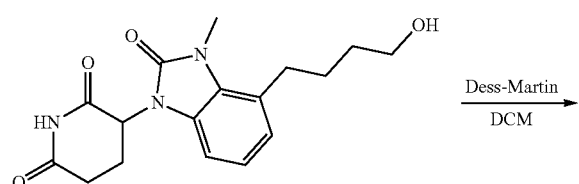

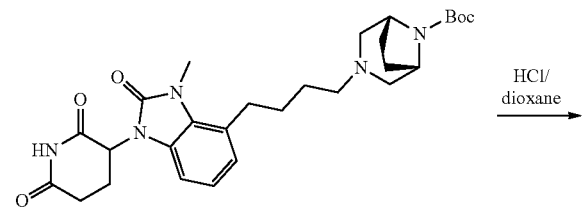

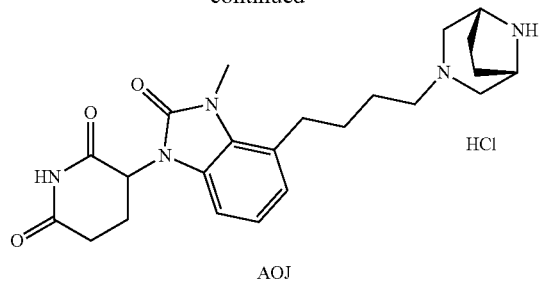

AOJ

Step 1—4-(1-(2,6-Dioxopiperidin-3-yl)-3-methyl-2-oxo-2,3-dihydro-1H-benzo[d]imidazol-4-yl) butanal To a mixture of 3-[4-(4-hydroxybutyl)-3-methyl-2-oxo-benzimidazol-1-yl]piperidine-2,6-dione (200 mg, 604 umol, synthesized via steps 1-2 of Intermediate ANH) in DCM (5.0 mL) was added Dess-Martin (384 mg, 905 umol) at 25° C. under N$_2$. The mixture was stirred at 25° C. for 2 hr. On completion, the reaction mixture was quenched with Na$_2$S$_2$O$_3$ (10.0 mL) and extracted with DCM (2×10.0 mL). The combined organic phase was washed with NaHCO$_3$ and brine (2×10.0 mL), dried with anhydrous Na$_2$SO$_4$, filtered and concentrated in vacuo to give the title compound (180 mg) as colorless oil. LC-MS (ESI$^+$) m/z 390.0 (M+H)$^+$.

Step 2—(1R,5S)-tert-butyl 3-(4-(1-(2,6-dioxopiperidin-3-yl)-3-methyl-2-oxo-2,-dihydro-1H-benzo[d]imidazol-4-yl)butyl)-3,8-diazabicyclo[3.2.1]octane-8-carboxylate To a solution of 4-[1-(2,6-dioxo-3-piperidyl)-3-methyl-2-oxo-benzimidazol-4-yl]butanal (170 mg, 516 umol) in a mixed solvents of DMF (1.0 mL) and THF (2.0 mL) was added AcOH (31.0 mg, 516 umol) until the pH=5-7. Then tert-butyl (1R,5S)-3,8-diazabicyclo[3.2.1]octane-8-carboxylate (110 mg, 516 umol, CAS #149771-44-8) was added. The reaction mixture was stirred at 25° C. for 0.5 hour. Next, NaBH(OAc)$_3$ (219 mg, 1.03 mmol) was added and the mixture was then stirred at 25° C. for 2 hours. On completion, the reaction mixture was concentrated under vacuum to give a residue. The residue was purified by reverse phase flash [0.1% TFA condition] to give the title compound (180 mg, 66% yield) as a yellow solid. $^1$H NMR (400 MHz, DMSO-d$_6$) δ 11.10 (s, 1H), 7.59-7.51 (m, 1H), 7.01 (d, J=8.0 Hz, 1H), 6.87 (d, J=8.0 Hz, 1H), 5.35 (dd, J=5.2, 12.8 Hz, 1H), 3.39-3.34 (m, 4H), 3.33 (s, 3H), 3.22 (t, J=7.2 Hz, 2H), 2.96-2.86 (m, 1H), 2.77 (s, 3H), 2.75-2.69 (m, 1H), 2.69-2.62 (m, 3H), 2.04-1.97 (m, 1H), 1.87-1.78 (m, 2H), 1.74-1.65 (m, 2H), 1.39 (s, 9H). LC-MS (ESI$^+$) m/z 526.3 (M+H)$^+$.

Step 3—3-(4-(4-((1R,5S)-3,8-diazabicyclo[3.2.1]octan-3-yl)butyl)-3-methyl-2-oxo-2,3-dihydro-1H-benzo[d]imidazol-1-yl)piperidine-2,6-dione To a mixture of tert-butyl (1R,5S)-3-[4-[1-(2,6-dioxo-3-piperidyl)-3-methyl-2-oxo-benzimidazol-4-yl]butyl]-3,8-diazabicyclo[3.2.1]octane-8-carboxylate (65.0 mg, 124 umol) in DCM (3.0 mL) was added HCl/dioxane (4 M, 1.0 mL) in one portion at 25° C. under N$_2$. The mixture was stirred at 25° C. for 30 min. On completion, the mixture was concentrated in vacuo to give the title compound (60.0 mg) as a white solid. LC-MS (ESI⁺) m/z 426.2 (M+H)⁺.

Tert-butyl 2-(aminomethyl)-7-azaspiro[3.5]nonane-7-carboxylate (Intermediate AJZ)

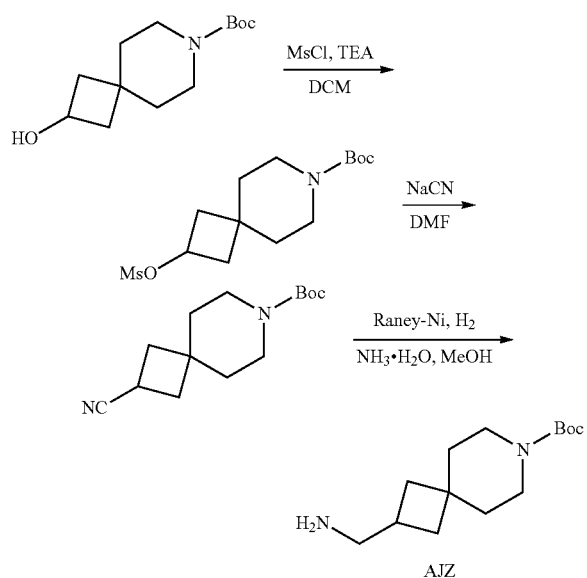

Step 1—Tert-butyl 2-methylsulfonyloxy-7-azaspiro[3.5]nonane-7-carboxylate

To a solution of tert-butyl 2-hydroxy-7-azaspiro[3.5]nonane-7-carboxylate (2.00 g, 8.29 mmol, CAS #240401-28-9) and TEA (2.10 g, 20.7 mmol) in DCM (30 mL) was added MsCl (1.14 g, 9.95 mmol) dropwise at 0° C. Then the reaction mixture was stirred at 20° C. for 2 hrs. On completion, the mixture was quenched with water (50 mL), then extracted with DCM (2×50 mL). The organic layer was washed with citric acid (100 ml), brine (2×100 mL), dried with Na₂SO₄, filtered and the filtrate was concentrated in vacuo to give the title compound (2.60 g, 98% yield) as a yellowish oil. ¹H NMR (400 MHz, CDCl₃) δ 5.04 (t, J=7.2 Hz, 1H), 3.38-3.28 (m, 4H), 2.99 (s, 3H), 2.48-2.36 (m, 2H), 2.14-2.04 (m, 2H), 1.58-1.51 (m, 4H), 1.45 (s, 9H).

Step 2—Tert-butyl 2-cyano-7-azaspiro[3.5]nonane-7-carboxylate

To a solution of tert-butyl 2-methylsulfonyloxy-7-azaspiro[3.5]nonane-7-carboxylate (2.60 g, 8.14 mmol) in DMF (20 mL) was added NaCN (598 mg, 12.2 mmol). The reaction mixture was stirred at 120° C. for 3 days. On completion, the reaction mixture was cooled to 25° C., diluted with water (100 mL), then extracted with EA (2×100 mL). The organic layer was washed with brine (2×100 mL) and concentrated in vacuo. The residue was purified by silica gel chromatography to give the title compound (1.32 g, 65% yield) as a white solid. ¹H NMR (400 MHz, CDCl₃) δ 3.36-3.29 (m, 4H), 3.13-3.02 (m, 1H), 2.30-2.14 (m, 4H), 1.66-1.62 (m, 2H), 1.58-1.53 (m, 2H), 1.45 (s, 9H).

Step 3—Tert-butyl 2-(aminomethyl)-7-azaspiro[3.5]nonane-7-carboxylate

To a solution of tert-butyl 2-cyano-7-azaspiro[3.5]nonane-7-carboxylate (200 mg, 799 umol) and NH₃.H₂O (0.2 mL) in MeOH (5 mL) was added Raney-Ni (30 mg). The reaction mixture was stirred at 20° C. for 16 hrs under H₂ (15 Psi) atmosphere. On completion, the mixture was filtered and the filtrate was concentrated in vacuo to give the title compound (200 mg, 98% yield) as a white solid. ¹H NMR (400 MHz, CDCl₃) δ 3.37-3.32 (m, 2H), 3.30-3.23 (m, 2H), 2.70 (d, J=7.2 Hz, 2H), 2.33-2.24 (m, 1H), 1.97-1.88 (m, 2H), 1.59-1.55 (m, 2H), 1.45 (s, 9H), 1.44-1.37 (m, 4H).

4-Fluoro-2-(1-methyl-2,6-dioxo-3-piperidyl)isoindoline-1,3-dione (Intermediate AJL)

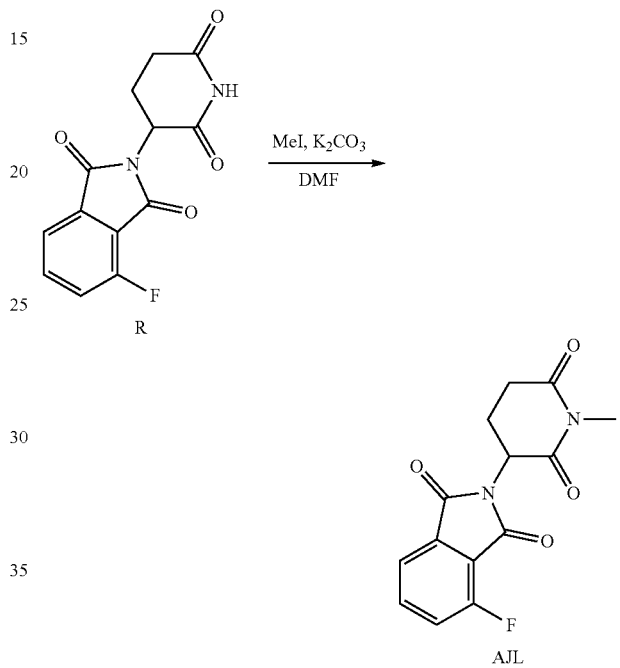

To a solution of 2-(2,6-dioxo-3-piperidyl)-4-fluoro-isoindoline-1,3-dione (500 mg, 1.81 mmol, Intermediate R) in DMF (10 mL) was added MeI (1.54 g, 10.8 mmol) and K₂CO₃ (375 mg, 2.72 mmol) at 0° C. The reaction mixture was stirred at 0-25° C. for 12 hours. On completion, the reaction mixture was concentrated in vacuo to give the title compound (500 mg, 95% yield) as a green solid. LC-MS (ESI⁺) m/z 291.0 (M+H)⁺.

4-(7-Azaspiro[3.5]nonan-2-ylmethylamino)-2-(1-methyl-2,6-dioxo-3-piperidyl)isoindoline-1,3-dione (Intermediate ATW)

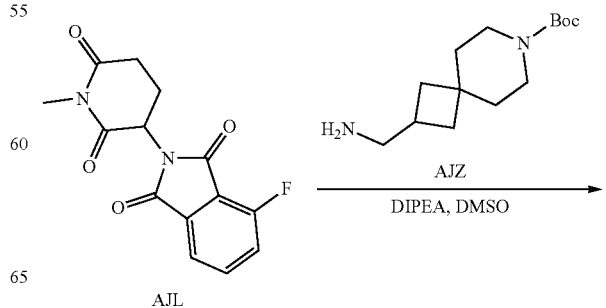

2045

-continued

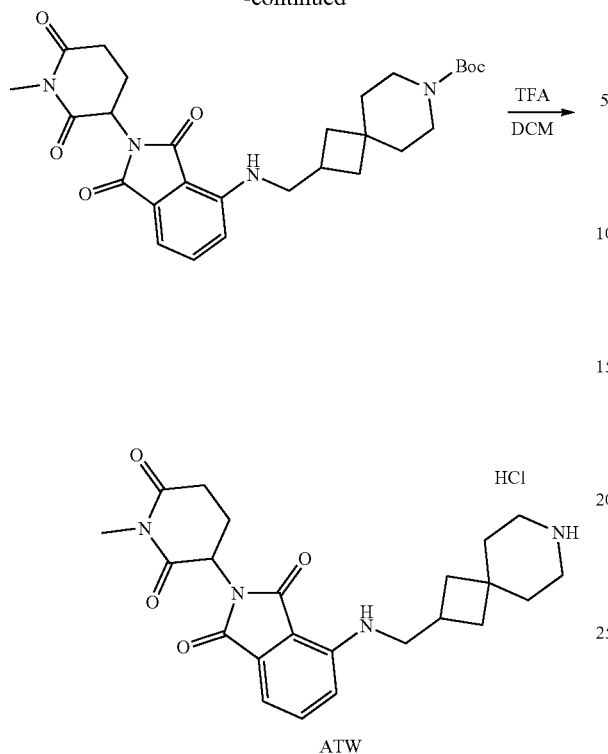

ATW

Step 1—Tert-butyl 2-[[[2-(1-methyl-2,6-dioxo-3-piperidyl)-1,3-dioxo-isoindolin-4-yl]amino]methyl]-7-azaspiro[3.5]nonane-7-carboxylate To a solution of 4-fluoro-2-(1-methyl-2,6-dioxo-3-piperidyl)isoindoline-1,3-dione (180 mg, 620 umol, Intermediate AJL) and tert-butyl 2-(aminomethyl)-7-azaspiro[3.5]nonane-7-carboxylate (150 mg, 589 umol, Intermediate AJZ) in DMSO (3.00 mL) was added DIPEA (381 mg, 2.95 mmol). The mixture was stirred at 130° C. for 3 hrs. On completion, the reaction mixture was filtered and concentrated in vacuo to give a residue. The residue was purified by reversed-phase (0.1% FA condition) to give the title compound (170 mg, 54% yield) as a yellow solid. $^1$H NMR (400 MHz, DMSO-$d_6$) δ 7.64-7.50 (m, 1H), 7.11 (d, J=8.8 Hz, 1H), 7.02 (d, J=7.2 Hz, 1H), 6.48 (t, J=5.6 Hz, 1H), 5.11 (dd, J=5.2, 12.8 Hz, 1H), 3.37-3.33 (m, 2H), 3.27-3.14 (m, 4H), 3.01 (s, 3H), 2.99-2.88 (m, 1H), 2.81-2.70 (m, 1H), 2.60-2.52 (m, 2H), 2.08-2.01 (m, 1H), 1.93-1.85 (m, 2H), 1.56-1.50 (m, 2H), 1.49-1.39 (m, 4H), 1.37 (s, 9H).

Step 2—4-(7-Azaspiro[3.5]nonan-2-ylmethylamino)-2-(1-methyl-2,6-dioxo-3-piperidyl)isoindoline-1,3-dione To a solution of tert-butyl 2-[[[2-(1-methyl-2,6-dioxo-3-piperidyl)-1,3-dioxo-isoindolin-4-yl]amino]methyl]-7-azaspiro[3.5]nonane-7-carboxylate (70.0 mg, 133 umol) in DCM (2.00 mL) was added TFA (770 mg, 6.75 mmol, 0.50 mL). The mixture was stirred at 20° C. for 0.5 hr. On completion, the reaction mixture was concentrated in vacuo to give the title compound (70 mg, 97% yield, TFA) as a yellow solid. LC-MS (ESI$^+$) m/z 425.1 (M+H)$^+$.

2046

N-[3-(difluoromethyl)-1-(4-formylcyclohexyl)pyrazol-4-yl]-5-[(1R,4R)-2-oxa-5-azabicyclo[2.2.1]heptan-5-yl]pyrazolo[1,5-a]pyrimidine-3-carboxamide (Intermediate AJB)

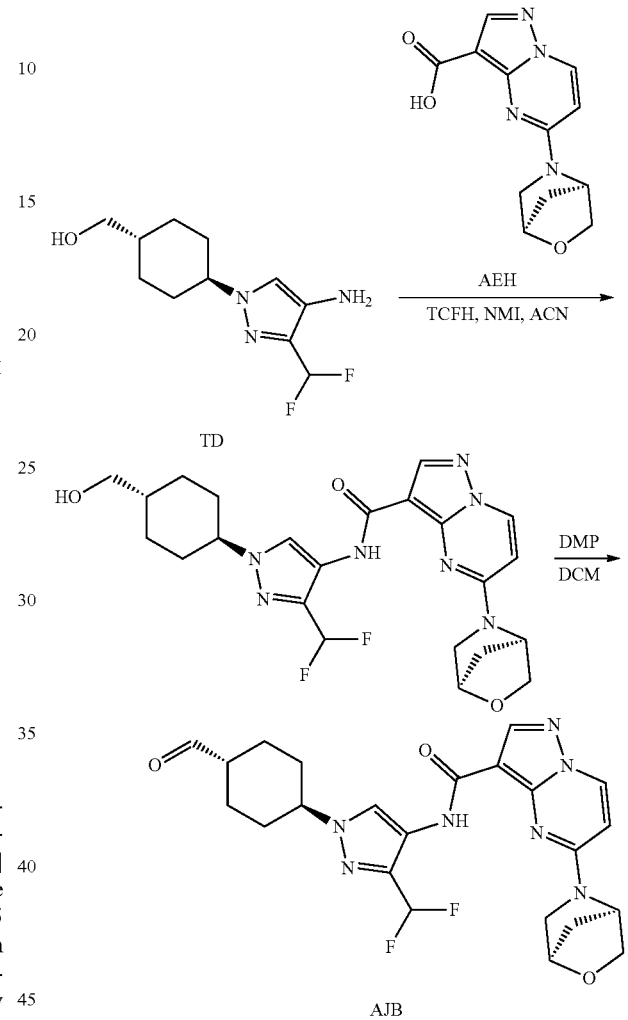

AJB

Step 1—N-[3-(difluoromethyl)-1-[4-(hydroxymethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide To a solution of 5-[(1R,4R)-2-oxa-5-azabicyclo[2.2.1]heptan-5-yl]pyrazolo[1,5-a]pyrimidine-3-carboxylic acid (3.71 g, 14.2 mmol, Intermediate AEH) in MeCN (75 mL) was added 1-methylimidazole (4.10 g, 49.9 mmol, 3.98 mL), [chloro(dimethylamino)methylene]-dimethyl-ammonium; hexafluorophosphate (4.80 g, 17.1 mmol). The mixture was stirred at 20° C. for 30 min. Then [4-[4-amino-3-(difluoromethyl)pyrazol-1-yl]cyclohexyl]methanol (3.5 g, 14.2 mmol, Intermediate TD) was added to the mixture, the reaction mixture was stirred at 20° C. for 2 hrs. On completion, the reaction mixture was filtered and the filter cake was concentrated in vacuo to give the title compound (3.80 g, 55% yield) as white solid. $^1$H NMR (400 MHz, DMSO-$d_6$) δ 9.49 (d, J=5.2 Hz, 1H), 8.77 (dd, J=2.4, 8.0 Hz, 1H), 8.39

(d, J=4.0 Hz, 1H), 8.25 (d, J=5.2 Hz, 1H), 7.27-6.95 (m, 1H), 6.88-6.40 (m, 1H), 5.32-5.01 (m, 1H), 4.76 (d, J=14.8 Hz, 1H), 4.47 (t, J=5.2 Hz, 1H), 4.23-4.10 (m, 1H), 3.84-3.72 (m, 2H), 3.65-3.42 (m, 2H), 3.25 (t, J=5.6 Hz, 2H), 2.07-1.90 (m, 4H), 1.89-1.81 (m, 2H), 1.78-1.66 (m, 2H), 1.50-1.36 (m, 1H), 1.17-1.00 (m, 2H); LC-MS (ESI$^+$) m/z 488.3 (M+H)$^+$.

Step 2—N-[3-(difluoromethyl)-1-(4-formylcyclohexyl)pyrazol-4-yl]-5-[(1R,4R)-2-oxa-5-azabicyclo[2.2.1]heptan-5-yl]pyrazolo[1,5-a]pyrimidine-3-carboxamide To a solution of N-[3-(difluoromethyl)-1-[4-(hydroxymethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide (3.80 g, 7.79 mmol) in DCM (78 mL) was added DMP (3.64 g, 8.57 mmol), the reaction mixture was stirred at 20° C. for 3 hr. On completion, the reaction mixture was quenched with Na$_2$S$_2$O$_3$ (50 mL) and extracted with DCM (2×60 mL). The combined organic phase was washed with NaHCO$_3$ and brine (2×20 mL), dried with anhydrous Na$_2$SO$_4$, filtered and concentrated in vacuo to give the title compound (3.30 g, 87% yield) as yellow solid. $^1$H NMR (400 MHz, DMSO-d$_6$) δ 9.60 (s, 1H), 9.49 (d, J=5.2 Hz, 1H), 8.76 (dd, J=4.0, 8.0 Hz, 1H), 8.40 (d, J=4.0 Hz, 1H), 8.25 (d, J=4.8 Hz, 1H), 7.27-6.94 (m, 1H), 6.88-6.40 (m, 1H), 5.30-5.02 (m, 1H), 4.76 (d, J=14.0 Hz, 1H), 4.29-4.14 (m, 1H), 3.85-3.72 (m, 2H), 3.64-3.41 (m, 2H), 2.43-2.31 (m, 1H), 2.14-1.90 (m, 6H), 1.88-1.73 (m, 2H), 1.48-1.24 (m, 2H).

Tert-butyl N-[4-(aminomethyl)cyclohexyl]-N-methyl-carbamate (Intermediate AOK)

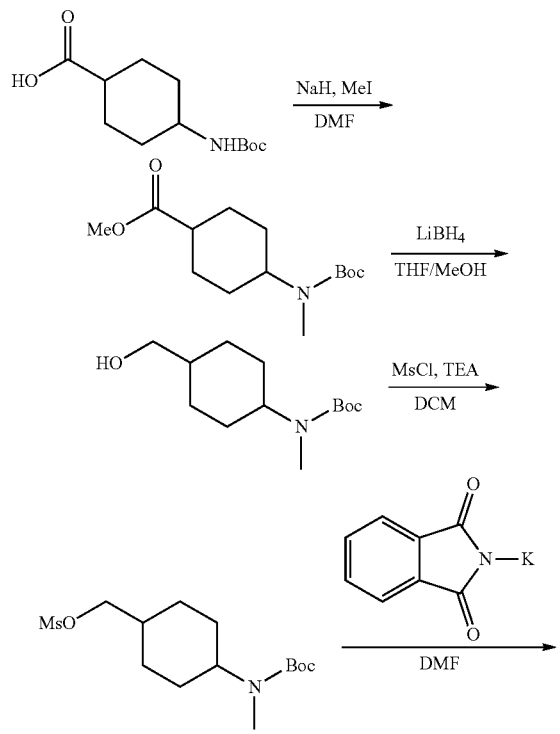

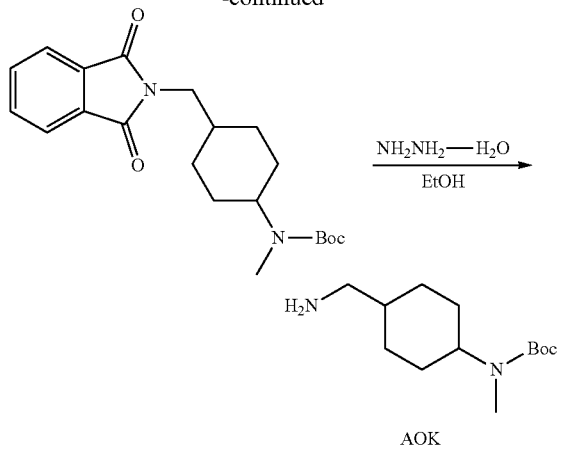

Step 1—Methyl 4-[tert-butoxycarbonyl(methyl)amino]cyclohexanecarboxylate

To a mixture of 4-(tert-butoxycarbonylamino)cyclohexanecarboxylic acid (5.00 g, 20.5 mmol) in DMF (200 mL) and NaH (3.29 g, 82.2 mmol, 60% dispersion in mineral oil) at 0° C. Then the mixture was stirred at 0° C. for 30 min. Finally MeI (14.5 g, 102 mmol) was added to the mixture and stirred at 25° C. for 12 hour. On completion, the reaction mixture was diluted with water (30 mL) and extracted with EA (2×20 mL). The combined organic layers was dried over Na$_2$SO$_4$, filtered and concentrated in vacuo to give a residue. The residue was purified by column chromatography (SiO$_2$, PE:EA=5:1) to give the title compound (3.00 g, 53% yield) as colorless oil. $^1$H NMR (400 MHz, CDCl$_3$) δ 4.07-3.81 (m, 1H), 3.67 (s, 3H), 2.72 (s, 3H), 2.24-2.16 (m, 1H), 2.09-2.01 (m, 2H), 1.76 (d, J=10.8 Hz, 2H), 1.64-1.48 (m, 4H), 1.46 (s, 9H).

Step 2—Tert-butyl N-[4-(hydroxymethyl)cyclohexyl]-N-methyl-carbamate

To a solution of methyl 4-[tert-butoxycarbonyl(methyl)amino]cyclohexanecarboxylate (2.70 g, 9.95 mmol) in a mixed solvent of THF (20 mL) and MeOH (5 mL) was added LiBH$_4$ (867 mg, 39.8 mmol) at 0° C. The mixture was stirred as 50° C. for 3 hrs. On completion, the reaction mixture was quenched by water (20 mL) and extracted with DCM (3×15 mL). The combined organic layers dried over Na$_2$SO$_4$, filtered and concentrated in vacuo to give the title compound (2.20 g, 92% yield) as colorless oil. $^1$H NMR (400 MHz, CDCl$_3$) δ 4.09-3.70 (m, 1H), 3.46 (t, J=6.0 Hz, 2H), 2.73 (s, 3H), 1.93-1.84 (m, 2H), 1.79-1.66 (m, 2H), 1.46 (s, 9H), 1.44-1.42 (m, 1H), 1.42-1.34 (m, 2H), 1.12-1.03 (m, 2H).

Step 3—[4-Tert-butoxycarbonyl(methyl)aminol cyclohexyl]methyl methanesulfonate

To a solution of tert-butyl N-[4-(hydroxymethyl)cyclohexyl]-N-methyl-carbamate (1.50 g, 6.16 mmol) in DCM (30 mL) was added MsCl (917 mg, 8.01 mmol) and TEA (1.87 g, 18.4 mmol) at 0° C. and the mixture was stirred at 25° C. for 1 hr. On completion, the reaction mixture was washed with water (4×30 mL). The organic layer was dried over with Na$_2$SO$_4$, filtered and concentrated in vacuo to give the title compound (1.90 g, 92% yield) as colorless oil. $^1$H NMR (400 MHz, CDCl$_3$) δ 4.28-4.01 (m, 2H), 3.99-3.63 (m, 1H), 3.06-2.98 (m, 3H), 2.81-2.65 (m, 3H), 1.97-1.85 (m, 2H), 1.82-1.72 (m, 2H), 1.71-1.63 (m, 1H), 1.54-1.43 (m, 11H), 1.23-1.07 (m, 2H).

Step 4—Tert-butyl N-[4-[(1,3-dioxoisoindolin-2-yl)methyl]cyclohexyl]-N-methyl-carbamate To a solution of [4-[tert-butoxycarbonyl(methyl)amino]cyclohexyl]methyl methanesulfonate (1.85 g, 5.76 mmol) in DMF (22 mL) was added (1,3-dioxoisoindolin-2-yl)potassium (1.60 g, 8.63 mmol) and the mixture was stirred at 100° C. for 16 hrs. On completion, the reaction mixture was diluted with water (100 mL) and extracted with EA (3×20 mL). The combined EA was dried over Na$_2$SO$_4$, filtered and concentrated in vacuo to give a residue. The residue was purified by column chromatography (SiO$_2$, petroleum ether/ethyl acetate=10/1) to give the title compound (1.20 g, 55% yield) as colorless oil. $^1$H NMR (400 MHz, CDCl$_3$) δ 7.85 (dd, J=3.2, 5.6 Hz, 2H), 7.72 (dd, J=3.2, 5.6 Hz, 2H), 4.13-3.74 (m, 1H), 3.55 (d, J=6.8 Hz, 2H), 2.69 (s, 3H), 1.84-1.66 (m, 5H), 1.45 (s, 9H), 1.43-1.33 (m, 2H), 1.23-1.07 (m, 2H); LC-MS (ESI$^+$) m/z 395.2 (M+Na)$^+$.

Step 5—Tert-butyl N-[4-(aminomethyl)cyclohexyl]-N-methyl-carbamate

To a solution of tert-butyl N-[4-[(1,3-dioxoisoindolin-2-yl)methyl]cyclohexyl]-N-methyl-carbamate (1.15 g, 3.09 mmol) in EtOH (20 mL) was added NH$_2$NH$_2$—H$_2$O (1.55 g, 30.8 mmol). The mixture was stirred at 80° C. for 6 hours. On completion, the mixture was filtered to give the filtrate and concentrated in vacuo to give a residue. The residue was diluted with DCM (30 mL), filtered to give the filtrate and concentrated in vacuo to give the title compound (0.70 g, 90% yield) as colorless oil. $^1$H NMR (400 MHz, CDCl$_3$) δ 4.10-3.70 (m, 1H), 2.72 (s, 3H), 2.53 (d, J=6.4 Hz, 2H), 1.91-1.81 (m, 2H), 1.75-1.68 (m, 2H), 1.46 (s, 9H), 1.45-1.36 (m, 2H), 1.25-1.16 (m, 1H), 1.10-0.94 (m, 2H).

2-(2,6-Dioxo-3-piperidyl)-4-[[4-(methylamino)cyclohexyl]methylamino]isoindoline-1,3-dione (Intermediate AOL)

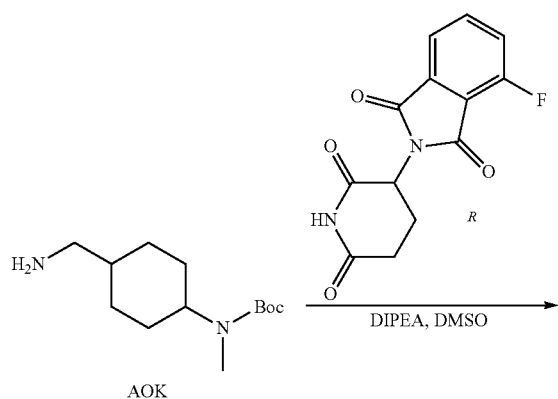

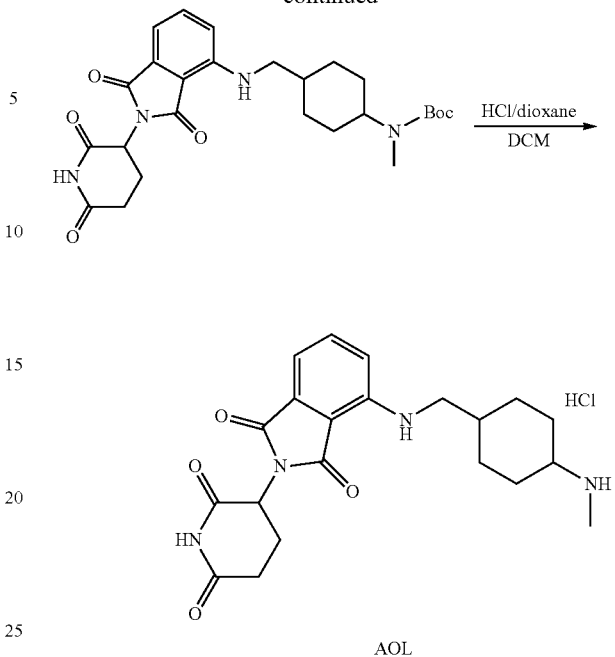

AOL

Step 1—Tert-butyl N-[4-[[[2-(2,6-dioxo-3-piperidyl)-1,3-dioxo-isoindolin-4-yl]amino]methyl]cyclohexyl]-N-methyl-carbamate To a solution of 2-(2,6-dioxo-3-piperidyl)-4-fluoro-isoindoline-1,3-dione (0.3 g, 1.09 mmol, Intermediate R) and tert-butyl N-[4-(aminomethyl)cyclohexyl]-N-methyl-carbamate (315 mg, 1.30 mmol, Intermediate AOK) in DMSOs (6 mL) was added DIPEA (701 mg, 5.43 mmol). The mixture was stirred at 130° C. for 3 hours. On completion, the reaction mixture was diluted with water (30 mL) and extracted with EA (3×20 mL). The combined organic layers were dried over Na$_2$SO$_4$, filtered and concentrated in vacuo to give a residue. The residue was purified by prep-HPLC (FA condition) to give the title compound (0.45 g, 83% yield) as yellow solid. $^1$H NMR (400 MHz, CDCl$_3$) δ 8.06 (s, 1H), 7.49 (dd, J=7.2, 8.4 Hz, 1H), 7.14-7.06 (m, 1H), 6.94-6.82 (m, 1H), 6.34 (t, J=5.6 Hz, 1H), 4.97-4.87 (m, 1H), 4.16-3.66 (m, 1H), 3.13 (t, J=6.4 Hz, 2H), 2.96-2.78 (m, 2H), 2.75-2.65 (m, 3H), 2.19-2.11 (m, 1H), 1.99-1.81 (m, 2H), 1.75 (d, J=10.0 Hz, 2H), 1.65-1.52 (m, 2H), 1.49-1.39 (m, 11H), 1.24-1.06 (m, 2H); LC-MS (ESI$^+$) m/z 499.3 (M+H)$^+$.

Step 2—2-(2,6-Dioxo-3-piperidyl)-4-[[4-(methylamino)cyclohexyl]methylamino]isoindoline-1,3-dione To a solution of tert-butyl N-[4-[[[2-(2,6-dioxo-3-piperidyl)-1,3-dioxo-isoindolin-4-yl]amino]methyl] cyclohexyl]-N-methyl-carbamate (150 mg, 300 umol) in DCM (1.5 mL) was added HCl/dioxane (4 M, 1.50 mL). The mixture was stirred at 25° C. for 1 hr. On completion, the reaction mixture was concentrated in vacuo to give the title compound (120 mg, 95% yield, HCl) as yellow solid. LC-MS (ESI$^+$) m/z 399.3 (M+H)$^+$.

3-(3-Aminopropoxy)propane-1-sulfonamide (Intermediate AOM)

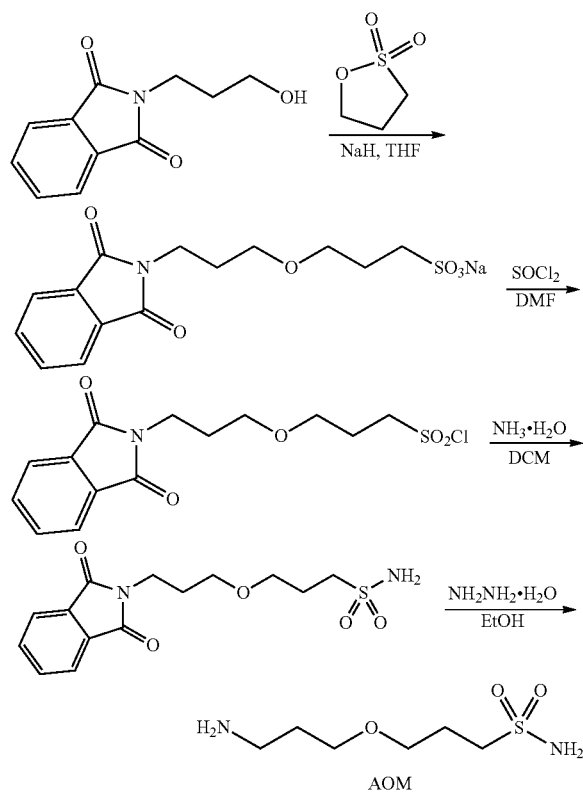

Step 1—3-[3-(1,3-Dioxoisoindolin-2-yl)propoxy]propylsulfonyloxy sodium

To a mixture of 2-(3-hydroxypropyl)isoindoline-1,3-dione (3.00 g, 14.6 mmol, CAS #883-44-3) and oxathiolane 2,2-dioxide (3.57 g, 29.2 mmol, CAS #1120-71-4) in THF (40 mL) was added t-BuOK (3.28 g, 29.2 mmol) at 25° C. The mixture was stirred at 80° C. for 24 hours. On completion, the mixture was filtered, the filter cake was collected and washed with THF (20 mL) and MeOH (20 mL), and then dried in vacuo to give the title compound (4.2 g, 82% yield) as yellow solid. LC-MS (ESI+) m/z 326.0 (M+Na)+.

Step 2—3-[3-(1,3-Dioxoisoindolin-2-yl)propoxy]propane-1-sulfonyl chloride

To a mixture of 3-[3-(1,3-dioxoisoindolin-2-yl)propoxy]propylsulfonyloxysodium (3.80 g, 10.8 mmol) in DMF (10 mL) was added SOCl$_2$ (12.9 g, 108 mmol, 7.89 mL) at 0° C. The mixture was stirred at 25° C. for 3 hours. On completion, the mixture was quenched with water (20 mL), and then extracted with DCM (3×20 mL). The combined organic phase was dried over Na$_2$SO$_4$, filtered and the filtrate was concentrated in vacuo to give the title compound (1.00 g, 26% yield).

Step 3—3-[3-(1,3-Dioxoisoindolin-2-yl)propoxy]propane-1-sulfonamide

To a mixture of 3-[3-(1,3-dioxoisoindolin-2-yl)propoxy]propane-1-sulfonyl chloride (1.00 g, 2.89 mmol) in THF (10 mL) was added NH$_3$—H$_2$O (1.22 g, 8.68 mmol, 1.34 mL, 25% solution) dropwise at 25° C. The mixture was stirred at 25° C. for 0.5 hour. On completion, the mixture was extracted with DCM (3×20 mL), and then concentrated in vacuo to give the title compound (400 mg, 42% yield). LC-MS (ESI+) m/z 327.1 (M+H)+.

Step 4—3-(3-Aminopropoxy)propane-1-sulfonamide

To a mixture of 3-[3-(1,3-dioxoisoindolin-2-yl)propoxy]propane-1-sulfonamide (200 mg, 612 umol) in EtOH (5 mL) was added NH$_2$NH$_2$—H$_2$O (153 mg, 3.06 mmol, 148 uL) at 25° C. The mixture was stirred at 80° C. for 1 hour. On completion, the mixture was filtered, and the filtrate was concentrated in vacuo to give the title compound (100 mg, 83% yield) as yellow oil.

3-(3-((2-(2,6-dioxopiperidin-3-yl)-1,3-dioxoisoindolin-4-yl)amino)propoxy)propane-1-sulfonamide (Intermediate AON)

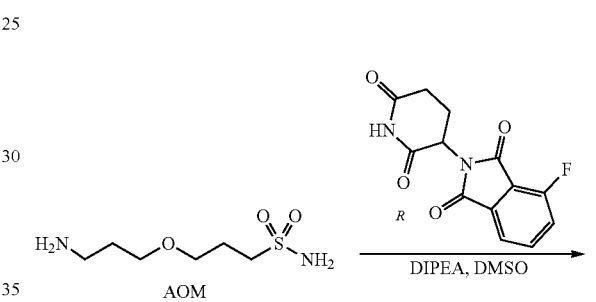

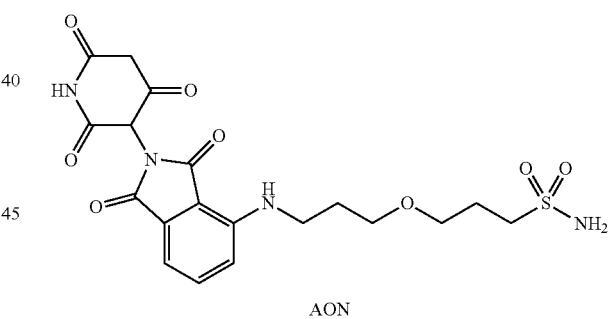

To a mixture of 2-(2,6-dioxo-3-piperidyl)-4-fluoro-isoindoline-1,3-dione (100 mg, 380 umol, Intermediate R) and 3-(3-aminopropoxy)propane-1-sulfonamide (96.9 mg, 494 umol, Intermediate AOM) in DMSO (3 mL) was added DIPEA (98.2 mg, 760 umol, 132 uL) at 25° C. under N$_2$. The mixture was stirred at 120° C. for 2 hours. On completion, the reaction mixture was quenched with H$_2$O (0.5 mL) at 25° C., and then concentrated in vacuo to give a residue. The residue was purified by reverse phase (FA condition) to give the title compound (120 mg, 70% yield) as yellow solid. $^1$H NMR (400 MHz, DMSO-d$_6$) δ 11.08 (s, 1H), 7.64-7.53 (m, 1H), 7.14-6.99 (m, 2H), 6.78 (s, 2H), 6.66 (t, J=6.0 Hz, 1H), 5.09-5.00 (m, 1H), 3.50-3.45 (m, 4H), 3.40-3.34 (m, 2H), 3.06-3.00 (m, 2H), 2.93-2.82 (m, 1H), 2.62-2.56 (m, 1H), 2.52 (s, 1H), 2.07-2.00 (m, 1H), 1.97-1.90 (m, 2H), 1.86-1.78 (m, 2H). LC-MS (ESI+) m/z 452.9 (M+H)+.

3-[3-Methyl-2-oxo-4-(4-piperazin-1-ylbutyl)benzimidazol-1-yl]piperidine-2,6-dione (Intermediate ANH)

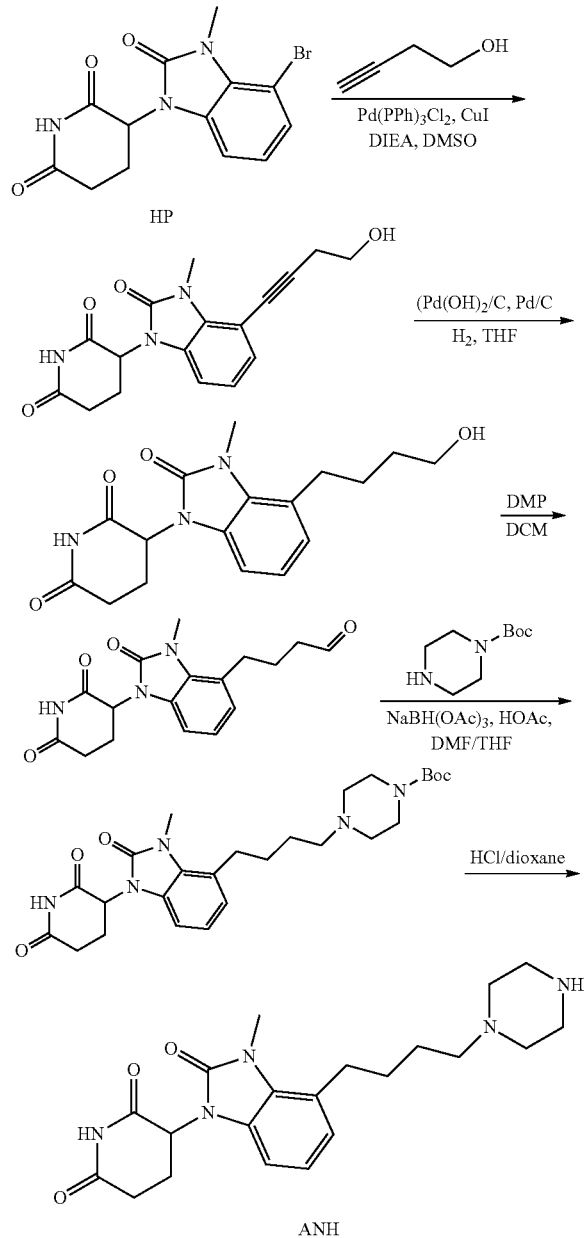

Step 1—3-[4-(4-Hydroxybut-1-ynyl)-3-methyl-2-oxo-benzimidazol-1-yl]piperidine-2,6-dione To a solution of 3-(4-bromo-3-methyl-2-oxo-benzimidazol-1-yl)piperidine-2,6-dione (500 mg, 1.48 mmol, Intermediate HP), but-3-yn-1-ol (207 mg, 2.96 mmol, 224 uL, CAS #927-74-2) in DMSO (4 mL) was added Pd(PPh₃)₂Cl₂ (207 mg, 295 umol), CuI (56.3 mg, 295 umol), and DIPEA (955 mg, 7.39 mmol, 1.29 mL). The reaction mixture was degassed and then heated to 80° C. for 2 hours under N₂. On completion, the reaction mixture was filtered and concentrated in vacuo. The crude product was purified by reversed-phase HPLC (0.1% FA condition) to give the title compound (350 mg, 63% yield) as white solid. $^1$H NMR (400 MHz, DMSO-$d_6$) δ 11.11 (s, 1H), 7.11 (d, J=7.6 Hz, 1H), 7.08-7.04 (m, 1H), 7.02-6.95 (m, 1H), 5.38 (dd, J=5.6, 12.8 Hz, 1H), 3.65 (s, 3H), 3.64-3.60 (m, 2H), 2.94-2.83 (m, 2H), 2.62 (t, J=6.8 Hz, 4H), 2.06-1.98 (m, 1H); LC-MS (ESI$^+$) m/z 328.2 (M+H)$^+$.

Step 2—3-[4-(4-Hydroxybutyl)-3-methyl-2-oxo-benzimidazol-1-yl]]piperidine-2,6-dione To a solution of 3-[4-(4-hydroxybut-1-ynyl)-3-methyl-2-oxo-benzimidazol-1-yl]piperidine-2,6-dione (350 mg, 1.07 mmol) in THF (4 mL) was added Pd/c (10 wt %), Pd(OH)₂/C (10 wt %) under N₂ atmosphere. The suspension was degassed under vacuum and purged with H₂ three times. The mixture was stirred under H₂ (15 psi) at 25° C. for 48 hours. On completion, the reaction mixture was filtered and concentrated in vacuo to give the title compound (320 mg, 82% yield) as yellow solid. LC-MS (ESI$^+$) m/z 332.1 (M+H)$^+$.

Step 3—4-[1-(2,6-Dioxo-3-piperidyl)-3-methyl-2-oxo-benzimidazol-4-yl]butanal To a solution of 3-[4-(4-hydroxybutyl)-3-methyl-2-oxo-benzimidazol-1-yl]piperidine-2,6-dione (300 mg, 905 umol) in DCM (2 mL) was added DMP (460 mg, 1.09 mmol, 336 uL). The reaction mixture was stirred at 25° C. for 2 hrs. On completion, the mixture was quenched with sat. Na₂S₂O₃ (5 mL) and sat. NaHCO₃ (5 mL), stirred for 10 minutes, then extracted with DCM (2×20 mL). The organic layer was washed with brine (2×10 mL), dried with Na₂SO₄, filtered and the filtrate was concentrated in vacuo to give the title compound (298 mg, 66% yield) as white solid. $^1$H NMR (400 MHz, DMSO-$d_6$) δ 11.09 (s, 1H), 9.70 (s, 1H), 7.02-6.92 (m, 2H), 6.91-6.82 (m, 1H), 5.37 (dd, J=5.2, 12.4 Hz, 1H), 3.56 (s, 3H), 2.93-2.87 (m, 2H), 2.74-2.62 (m, 2H), 2.57 (t, J=7.2 Hz, 3H), 2.04-1.96 (m, 1H), 1.90-1.81 (m, 2H); LC-MS (ESI$^+$) m/z 330.2 (M+H)$^+$.

Step 4—Tert-butyl 4-[4-[1-(2,6-dioxo-3-piperidyl)-3-methyl-2-oxo-benzimidazol-4-yl]butyl] piperazine-1-carboxylate To a solution of 4-[1-(2,6-dioxo-3-piperidyl)-3-methyl-2-oxo-benzimidazol-4-yl]butanal (298 mg, 905 umol), tert-butyl piperazine-1-carboxylate (185 mg, 995 umol, CAS #143238-38-4) in a mixed solvent of DMF (1 mL) and THF (4 mL) was added TEA (91.6 mg, 905 umol, 126 uL), and HOAc (109 mg, 1.81 mmol, 103 uL). Thirty minutes later, NaBH(OAc)₃ (287 mg, 1.36 mmol) was added and the reaction mixture was stirred at 25° C. for 2 hrs. On completion, the reaction mixture was filtered and concentrated in vacuo. The crude product was purified by reversed-phase HPLC (0.1% FA condition) to give the title compound (250 mg, 51% yield) as white solid. $^1$H NMR (400 MHz, DMSO-$d_6$) δ=11.09 (s, 1H), 8.14 (s, 1H), 7.00-6.91 (m, 2H), 6.89-6.83 (m, 1H), 5.36 (d, J=7.2 Hz, 1H), 3.55 (s, 3H), 3.51-3.35 (m, 7H), 2.75-2.57 (m, 3H), 2.28 (t, J=4.8 Hz, 4H), 2.03-1.95 (m, 1H), 1.65-1.51 (m, 4H), 1.38 (s, 9H); LC-MS (ESI$^+$) m/z 500.3 (M+H)$^+$.

Step 5—3-[3-Methyl-2-oxo-4-(4-piperazin-1-yl-butyl)benzimidazol-1-yl]piperidine-2,6-dione To a solution of tert-butyl 4-[4-[1-(2,6-dioxo-3-piperidyl)-3-methyl-2-oxo-benzimidazol-4-yl]butyl] piperazine-1-carboxylate (150 mg, 279 umol) in DCM (3 mL) was added HCl/dioxane (4 M, 3 mL). The mixture was stirred at 25° C. for 2 hours. On completion, the reaction mixture was concentrated in vacuo to give the title compound (120 mg, 99% yield, HCl) as yellow solid. LC-MS (ESI⁺) m/z 400.2 (M+H)⁺.

3-[4-[3-(3,9-Diazaspiro[5.5]undecan-3-yl)-3-oxo-propyl]-3-methyl-2-oxo-benzimidazol-1-yl] piperidine-2,6-dione (Intermediate ANI)

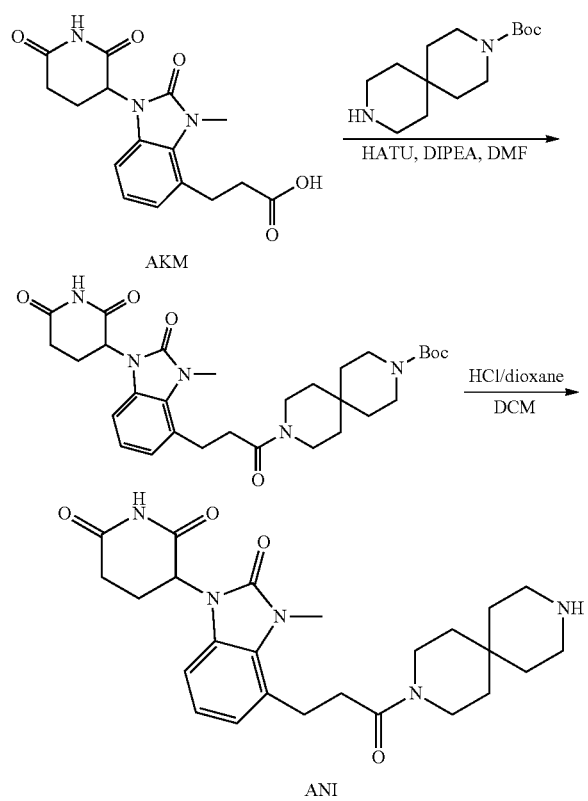

Step 1—Tert-butyl 9-[3-[1-(2,6-dioxo-3-piperidyl)-3-methyl-2-oxo-benzimidazol-4-yl] propanoyl]-3,9-diazaspiro[5.5]undecane-3-carboxylate To a solution of 3-[1-(2,6-dioxo-3-piperidyl)-3-methyl-2-oxo-benzimidazol-4-yl]propanoic acid (128 mg, 386 umol, Intermediate AKM), tert-butyl 3,9-diazaspiro[5.5]undecane-3-carboxylate (98.2 mg, 386 umol, CAS #173405-78-2) in DMF (3.00 mL) was added HATU (220 mg, 579 umol) and DIPEA (149 mg, 1.16 mmol). The mixture was stirred at 25° C. for 0.5 hr. On completion, the reaction was quenched with H₂O (1.00 mL) and concentrated in vacuo. The mixture was purified by reverse phase: (0.1% FA) to give the title compound (130 mg, 59% yield) as a white solid. ¹H NMR (400 MHz, DMSO-d₆) δ 11.11 (s, 1H), 7.03-6.88 (m, 3H), 5.43-5.31 (m, 1H), 3.58 (s, 3H), 3.47-3.40 (m, 3H), 3.34-3.32 (m, 1H), 3.31-3.25 (m, 4H), 3.18-3.11 (m, 2H), 2.97-2.83 (m, 1H), 2.78-2.62 (m, 4H), 2.03-1.92 (m, 1H), 1.39 (s, 9H), 1.36-1.24 (m, 8H).

Step 2—3-[4-[3-(3,9-Diazaspiro[5.5]undecan-3-yl)-3-oxo-propyl]-3-methyl-2-oxo-benzimidazol-1-yl] piperidine-2,6-dione To a solution of tert-butyl 9-[3-[1-(2,6-dioxo-3-piperidyl)-3-methyl-2-oxo-benzimidazol-4-yl] propanoyl]-3,9-diazaspiro[5.5]undecane-3-carboxylate (130 mg, 229 umol) in DCM (2.00 mL) was added HCl/dioxane (4.00 M, 2.00 mL). The mixture was stirred at 25° C. for 0.5 hr. On completion, the mixture was concentrated in vauco to give the title compound (110 mg, 95% yield, HCl salt) as a white solid. LC-MS (ESI⁺) m/z 468.3 (M+H)⁺.

Tert-butyl N-[[4-(2-aminoethyl)phenyl]methyl]-N-methyl-carbamate (Intermediate ANL)

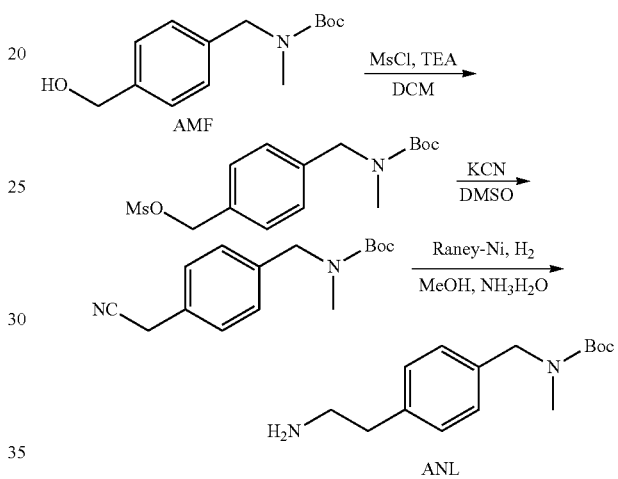

Step 1—[4-[r Tert-butoxycarbonyl(methyl)amino] methyl]phenyl]methyl methanesulfonate To a solution of tert-butyl N-[[4-(hydroxymethyl)phenyl]methyl]-N-methyl-carbamate (1.80 g, 7.16 mmol, Intermediate AMF) and TEA (1.45 g, 14.3 mmol) in DCM (30 mL) was added MsCl (1.23 g, 10.7 mmol) at 0° C. The mixture was stirred at 0-10° C. for 2 hours. On completion, the reaction was quenched with water (20 mL), and the mixture was partitioned. The aqueous phase was extracted with DCM (20 mL). The combined organic layer was concentrated in vacuo. The residue was diluted with EA (50 mL), washed with brine (20 mL), dried over Na₂SO₄, filtered and concentrated in vacuo to give the title compound (2.10 g, 89% yield) as light yellow oil. ¹H NMR (400 MHz, CDCl₃) δ 7.43-7.28 (m, 4H), 5.24 (s, 2H), 4.43 (s, 2H), 2.93 (s, 3H), 2.87-2.81 (m, 3H), 1.48 (s, 9H).

Step 2—Tert-butyl N-[[4-(cyanomethyl)phenyl] methyl]-N-methyl-carbamate

To a solution of [4-[[tert-butoxycarbonyl(methyl)amino] methyl]phenyl]methyl methanesulfonate (2.10 g, 6.38 mmol) in DMSO (20 mL) was added KCN (500 mg, 7.68 mmol) at 0° C. The mixture was stirred at 25° C. for 2 hours. On completion, the mixture was diluted with water (100 mL), and extracted with EA (3×50 mL). The combined organic layer was washed with brine (20 mL), dried over Na₂SO₄, filtered and concentrated in vacuo. The residue was purified by column chromatography on silica gel to give the title compound (390 mg, 23% yield) as light yellow oil. $^1$H NMR (400 MHz, CDCl$_3$) δ 7.36-7.30 (m, 4H), 4.43 (s, 2H), 3.75 (s, 2H), 2.84-2.82 (m, 3H), 1.49 (s, 9H).

Step 3—Tert-butyl N-[[4-(2-aminoethyl)phenyl] methyl]-N-methyl-carbamate

A mixture of tert-butyl N-[[4-(cyanomethyl)phenyl] methyl]-N-methyl-carbamate (360 mg, 1.38 mmol) and Raney-Ni (10 mg) in NH$_3$.H$_2$O (1 mL) and MeOH (10 mL) was stirred at 20° C. for 2 hours under H$_2$ (50 Psi). On completion, the mixture was filtered, and the cake was washed with MeOH (10 mL). The filtrate and washing were combined and concentrated in vacuo to give the title compound (360 mg, 98% yield) as light yellow gum. $^1$H NMR (400 MHz, DMSO-d$_6$) δ 7.20-7.15 (m, 2H), 7.14-7.09 (m, 2H), 4.32 (s, 2H), 2.77-2.73 (m, 2H), 2.72 (s, 3H), 2.65-2.58 (m, 2H), 1.41 (s, 9H).

3-(4-(Hydroxymethyl)-3-methyl-2-oxo-2,3-dihydro-1H-benzo[d]imidazol-1-yl)piperidine-2,6-dione (Intermediate ANG)

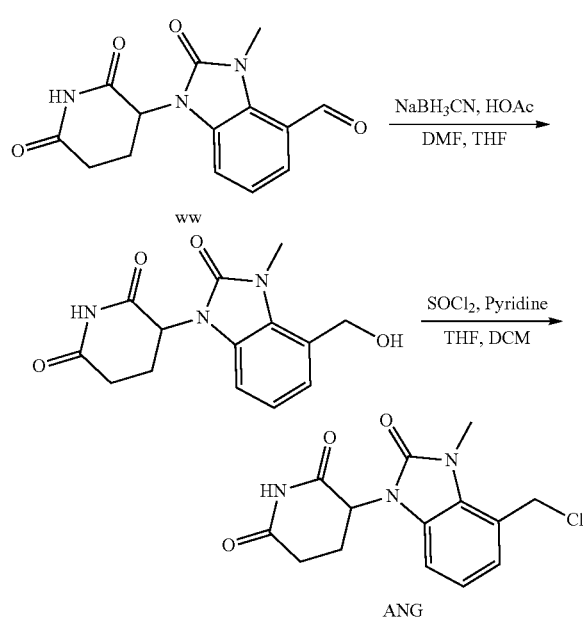

Step 1—3-(4-(Hydroxymethyl)-3-methyl-2-oxo-2,3-dihydro-1H-benzo[d]imidazol-1-yl)piperidine-2,6-dione To a solution of 1-(2,6-dioxo-3-piperidyl)-3-methyl-2-oxo-benzimidazole-4-carbaldehyde (7.00 g, 24.3 mmol, Intermediate WW) and HOAc (4.39 g, 73.1 mmol) in DMF (50 mL) and THF (50 mL) was added NaBH$_3$CN (6.13 g, 97.4 mmol) at 60° C. portion-wise, then the mixture was stirred at 60° C. for 2 hours. On completion, the reaction was quenched with 5 mL of water and filtered and the filtrate was concentrated. The residue was purified by reverse phase (FA) to give the title compound (5.00 g, 70% yield) as a white solid. $^1$H NMR (400 MHz, DMSO-d$_6$) δ 11.10 (s, 1H), 7.13-6.89 (m, 3H), 5.38 (d, J=5.4, 12.4 Hz, 1H), 4.74 (s, 2H), 3.62 (s, 3H), 2.95-2.86 (m, 1H), 2.78-2.60 (m, 2H), 2.10-1.95 (m, 1H).

Step 2—3-(4-(Hydroxymethyl)-3-methyl-2-oxo-2,3-dihydro-1H-benzo[d]imidazol-1-yl)piperidine-2,6-dione To a solution of 3-[4-(hydroxymethyl)-3-methyl-2-oxo-benzimidazol-1-yl]piperidine-2,6-dione (5.00 g, 17.2 mmol) and pyridine (273 mg, 3.46 mmol) in THF (30 mL) and DCM (30 mL) was added SOCl$_2$ (6.17 g, 51.8 mmol), then the mixture was stirred at 20° C. for 12 hrs. On completion, the reaction was concentrated to give the title compound (8.00 g, 90% yield) as a white solid. $^1$H NMR (400 MHz, DMSO-d$_6$) δ 11.08 (s, 1H), 7.19-6.99 (m, 3H), 5.32 (dd, J=5.2, 12.4 Hz, 1H), 5.03 (s, 2H), 3.65 (s, 3H), 2.92-2.80 (m, 1H), 2.73-2.59 (m, 2H), 2.10-1.98 (m, 1H).

3-[3-Methyl-2-oxo-4-(piperazin-1-ylmethyl)benzimidazol-1-yl]piperidine-2,6-dione (Intermediate ARK)

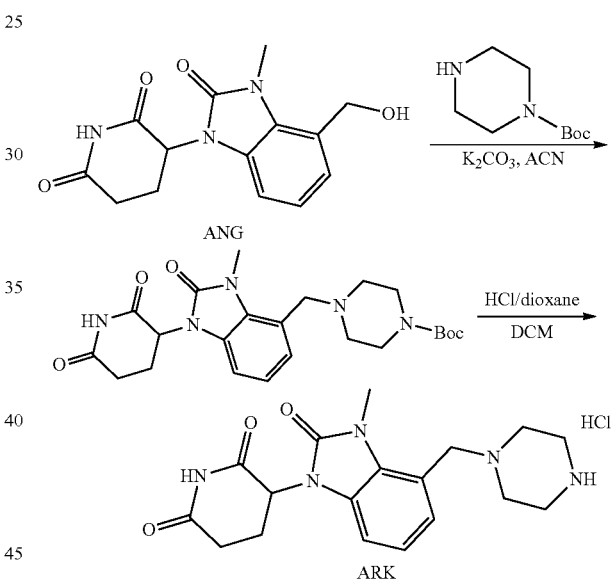

Step 1—Tert-butyl 4-[[1-(2,6-dioxo-3-piperidyl)-3-methyl-2-oxo-benzimidazol-4-yl]methyl] piperazine-1-carboxylate To a solution of 3-[4-(chloromethyl)-3-methyl-2-oxo-benzimidazol-1-yl]piperidine-2,6-dione (400 mg, 1.30 mmol, Intermediate ANG) and tert-butyl piperazine-1-carboxylate (200 mg, 1.07 mmol, CAS #143238-38-4) in ACN (5.00 mL) was added K$_2$CO$_3$ (297 mg, 2.15 mmol). The mixture was stirred at 80° C. for 3 hrs. On completion, the reaction mixture was filtered and concentrated in vacuo to give a residue. The residue was purified by reversed phase (0.1% FA condition) to give the title compound (430 mg, 87% yield) as a yellow solid. $^1$H NMR (400 MHz, CDCl$_3$) δ 8.57 (s, 1H), 7.02-6.95 (m, 1H), 6.95-6.89 (m, 1H), 6.81-6.75 (m, 1H), 5.27 (dd, J=5.2, 12.4 Hz, 1H), 3.80 (s, 3H), 3.75-3.67 (m, 2H), 3.47-3.35 (m, 4H), 2.99-2.90 (m, 1H), 2.90-2.80 (m, 1H), 2.80-2.68 (m, 1H), 2.55-2.35 (m, 4H), 2.29-2.17 (m, 1H), 1.46 (s, 9H).

Step 2—3-[3-Methyl-2-oxo-4-(piperazin-1-ylmethyl)benzimidazol-1-yl]piperidine-2,6-dione To a solution of tert-butyl 4-[[1-(2,6-dioxo-3-piperidyl)-3-methyl-2-oxo-benzimidazol-4-yl]methyl]piperazine-1-carboxylate (60.0 mg, 131 umol) in DCM (5.00 mL) was added HCl/dioxane (4 M, 1.00 mL). The reaction mixture was stirred at 20° C. for 0.5 hr. On completion, the reaction mixture was concentrated in vacuo to give the title compound (50.0 mg, 96% yield, HCl salt) as a white solid. LC-MS (ESI$^+$) m/z 358.1 (M+H)$^+$.

2-[4-[4-Amino-3-(difluoromethyl)pyrazol-1-yl]cyclohexyl]ethanol (Intermediate ARL)

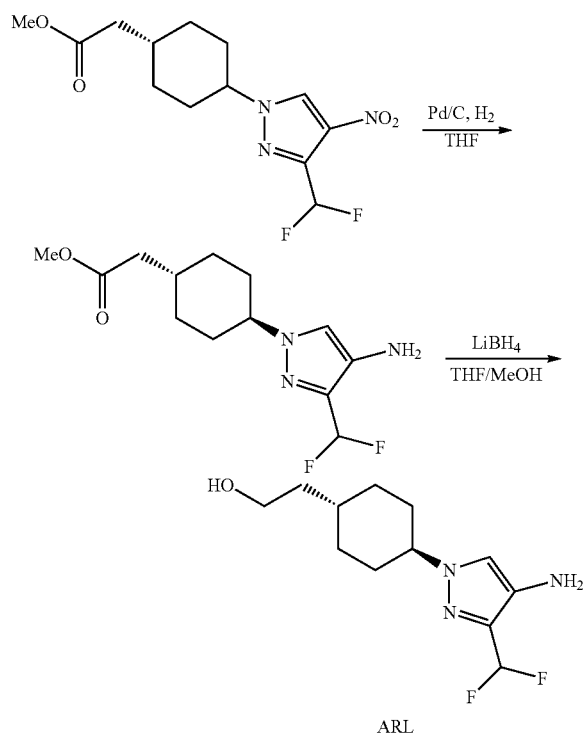

ARL

Step 1—Methyl 2-[4-[4-amino-3-(difluoromethyl)pyrazol-1-yl]]cyclohexyl]acetate To a solution of methyl 2-[4-[3-(difluoromethyl)-4-nitropyrazol-1-yl]cyclohexyl]acetate (1.60 g, 5.04 mmol, synthesized via Step 1-2 of Intermediate AAT) in THF (20.0 mL) was added Pd/C (500 mg, 10 wt %) under N$_2$ atmosphere. The suspension was degassed and purged with H$_2$ gas three times. The mixture was stirred at 25° C. for 6 hrs under H$_2$ (15 Psi). On completion, the reaction mixture was filtered and the filtrate was concentrated in vacuo to give the title compound (1.30 g, 89% yield) as red oil. $^1$H NMR (400 MHz, CDCl$_3$) δ 7.01 (s, 1H), 6.85-6.45 (m, 1H), 3.99-3.91 (m, 1H), 3.68 (s, 3H), 2.26 (d, J=6.8 Hz, 2H), 2.18-2.09 (m, 2H), 1.98-1.90 (m, 2H), 1.89-1.80 (m, 1H), 1.76-1.66 (m, 2H), 1.25-1.10 (m, 2H).

Step 2—2-[4-[4-Amino-3-(difluoromethyl)pyrazol-1-yl]cyclohexyl]ethanol

To a solution of methyl 2-[4-[4-amino-3-(difluoromethyl)pyrazol-1-yl]cyclohexyl]acetate (1.00 g, 3.48 mmol) in THF (8.00 mL) and MeOH (1.00 mL) was added LiBH$_4$ (151 mg, 6.96 mmol) at 0° C. Then the mixture was stirred at 50° C. for 1 hr. On completion, the reaction mixture was quenched by H$_2$O (50 mL) dropwise, and then diluted with EA (20 mL) and extracted with EA (2×50 mL). The combined organic layers were washed with brine (2×100 mL), dried over anhydrous Na$_2$SO$_4$, filtered and concentrated in vacuo to give a residue. The residue was purified by column chromatography (Petroleum ether/Ethyl acetate=2:1) to give the title compound (600 mg, 66% yield) as a yellow oil. $^1$H NMR (400 MHz, DMSO-d$_6$)$^1$H NMR (400 MHz, CDCl$_3$) δ 7.02 (s, 1H), 6.85-6.50 (m, 1H), 4.73 (s, 1H), 3.98-3.92 (m, 1H), 3.72 (t, J=6.4 Hz, 2H), 2.21-2.09 (m, 2H), 1.98-1.87 (m, 2H), 1.74-1.68 (m, 2H), 1.59-1.55 (m, 1H), 1.54-1.51 (m, 2H), 1.18-1.06 (m, 2H).

N-[3-(difluoromethyl)-1-[4-(2-oxoethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide (Intermediate ARM)

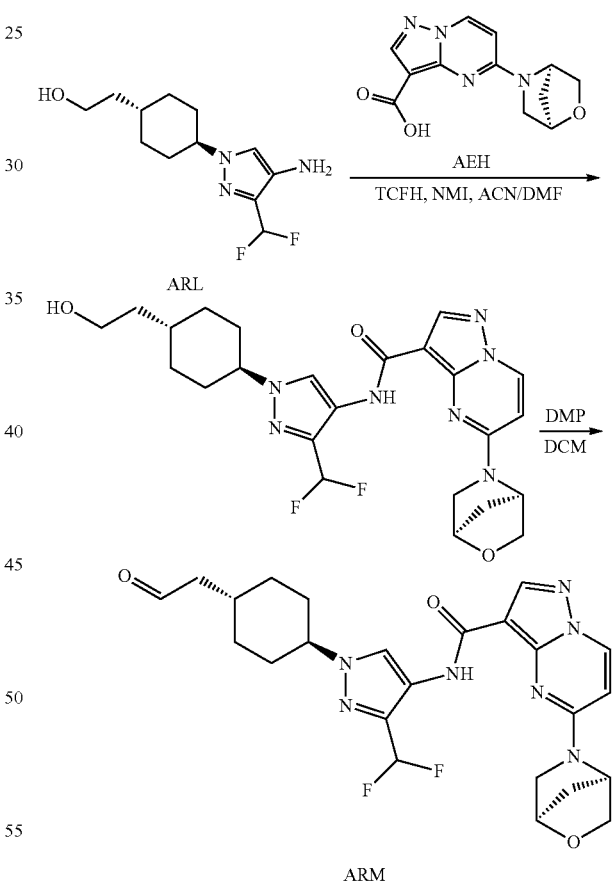

ARM

Step 1—N-[3-(difluoromethyl)-1-[4-(2-hydroxyethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide To a solution of 5-[(1R,4R)-2-oxa-5-azabicyclo[2.2.1]heptan-5-yl]pyrazolo[1,5-a]pyrimidine-3-carboxylic acid (602 mg, 2.31 mmol, Intermediate AEH) in ACN (4.00 mL)

and DMF (2.00 mL) was added [chloro(dimethylamino)methylene]-dimethylammonium; hexafluorophosphate (760 mg, 2.71 mmol) and 1-methylimidazole (664 mg, 8.10 mmol). The mixture was stirred at 20° C. for 1 hr. Then 2-[4-[4-amino-3-(difluoromethyl) pyrazol-1-yl]cyclohexyl] ethanol (600 mg, 2.31 mmol, Intermediate ARL) was added, then the reaction mixture was stirred at 25° C. for 2 hrs. On completion, the reaction mixture was quenched by addition $H_2O$ (1 mL), and concentrated in vacuo to remove ACN. The mixture was diluted with $H_2O$ (10 mL) and extracted with EA (3×10 mL). The combined organic layers were washed with brine (2×20 mL), dried over anhydrous $Na_2SO_4$, filtered and concentrated in vacuo to give a residue. The residue was purified by reversed phase (0.1% FA condition) to give the title compound (540 mg, 46% yield) as a white solid. $^1$H NMR (400 MHz, CDCl$_3$) δ 9.59 (s, 1H), 8.41 (s, 2H), 8.31 (d, J=7.6 Hz, 1H), 6.96-6.61 (m, 1H), 6.35-6.05 (m, 1H), 5.45 (s, 1H), 4.93-4.48 (m, 1H), 4.09-3.95 (m, 1H), 4.00-3.76 (m, 2H), 3.73 (t, J=6.4 Hz, 2H), 3.62-3.44 (m, 2H), 2.25-2.15 (m, 2H), 2.13-2.07 (m, 1H), 2.03-1.91 (m, 3H), 1.86-1.72 (m, 3H), 1.56-1.53 (m, 3H), 1.24-1.08 (m, 2H).

Step 2—N-[3-(difluoromethyl)-1-[4-(2-oxoethyl) cyclohexyl]pyrazol-4-yl]-5-[(1R,4R)-2-oxa-5-azabicyclo[2.2.1]heptan-5-yl]pyrazolo[1,5-a]pyrimidine-3-carboxamide To a solution of N-[3-(difluoromethyl)-1-[4-(2-hydroxyethyl)cyclohexyl]pyrazol-4-yl]-5-[(1R,4R)-2-oxa-5-azabicyclo[2.2.1]heptan-5-yl]pyrazolo[1,5-a]pyrimidine-3-carboxamide (490 mg, 977 umol) in DCM (8.00 mL) was added DMP (621 mg, 1.47 mmol). The mixture was stirred at 25° C. for 2 hrs. On completion, the reaction mixture was quenched by addition saturated solution of $Na_2S_2O_3$ (8 mL) and saturated solution of $NaHCO_3$ (2 mL), then extracted with DCM (3×10 mL). The combined organic layers was washed with brine (2×20 mL), dried over anhydrous $Na_2SO_4$, filtered and concentrated in vacuo to give a residue. The residue was purified by reversed phase (0.1% FA condition) to give the title compound (150 mg, 30% yield) as a yellow solid. $^1$H NMR (400 MHz, DMSO-d$_6$) δ 9.69 (t, J=2.0 Hz, 1H), 9.49 (d, J=5.6 Hz, 1H), 8.78 (d, J=7.6 Hz, 1H), 8.39 (d, J=4.4 Hz, 1H), 8.25 (d, J=5.6 Hz, 1H), 7.29-6.94 (m, 1H), 6.90-6.41 (m, 1H), 5.35-4.99 (m, 1H), 4.77 (d, J=16.4 Hz, 1H), 4.23-4.10 (m, 1H), 3.86-3.71 (m, 2H), 3.65-3.42 (m, 2H), 2.37 (dd, J=2.0, 6.4 Hz, 2H), 2.05-2.01 (m, 2H), 1.98-1.73 (m, 7H), 1.24-1.14 (m, 2H).

3-[4-[[(1R,5S)-3,8-diazabicyclo[3.2.1]octan-3-yl]methyl]-3-methyl-2-oxo-benzimidazol-1-yl]piperidine-2,6-dione (Intermediate ARN)

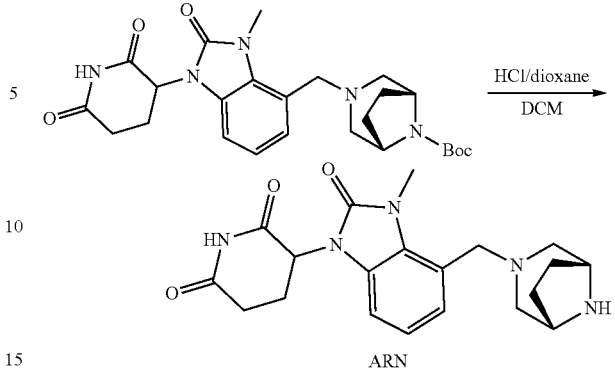

Step 1—Tert-butyl (1R,5S)-3-[[1-(2,6-dioxo-3-piperidyl)-3-methyl-2-oxo-benzimidazol-4-yl]methyl]-3,8-diazabicyclo[3.2.1]octane-8-carboxylate To a solution of 3-[4-(chloromethyl)-3-methyl-2-oxo-benzimidazol-1-yl]piperidine-2,6-dione (370 mg, 1.20 mmol, Intermediate ANG) and tert-butyl (1R,5S)-3,8-diazabicyclo[3.2.1]octane-8-carboxylate (200 mg, 942 umol, CAS #149771-44-8) in ACN (4.00 mL) was added $K_2CO_3$ (260 mg, 1.88 mmol). The reaction mixture was stirred at 80° C. for 3 hrs. On completion, the reaction mixture was filtered and the filtrate was concentrated in vacuo to give a residue. The residue was purified by reversed phase (0.1% FA condition) to give the title compound (380 mg, 83% yield) as a yellow solid. $^1$H NMR (400 MHz, DMSO-d$_6$) δ 11.08 (s, 1H), 7.07 (d, J=7.6 Hz, 1H), 6.99-6.92 (m, 1H), 6.92-6.86 (m, 1H), 5.37 (dd, J=5.2, 12.4 Hz, 1H), 4.03 (s, 2H), 3.68 (s, 3H), 3.63 (s, 2H), 2.99-2.80 (m, 1H), 2.77-2.67 (m, 1H), 2.67-2.61 (m, 1H), 2.60-2.55 (m, 2H), 2.25-2.10 (m, 2H), 2.10-1.96 (m, 1H), 1.80-1.55 (m, 4H), 1.41 (s, 9H).

Step 2—3-[4-[[(1R,5S)-3,8-diazabicyclo[3.2.1]octan-3-yl]methyl]-3-methyl-2-oxo-benzimidazol-1-yl]piperidine-2,6-dione To a solution of tert-butyl (1R,5S)-3-[[1-(2,6-dioxo-3-piperidyl)-3-methyl-2-oxo-benzimidazol-4-yl] methyl]-3,8-diazabicyclo[3.2.1]octane-8-carboxylate (60.0 mg, 124 umol) in DCM (5.00 mL) was added HCl/dioxane (4 M, 6.00 mL). The mixture was stirred at 25° C. for 1 hr. On completion, the reaction mixture was concentrated in vacuo to give the title compound (50.0 mg, 95% yield, HCl) as a yellow solid. LC-MS (ESI$^+$) m/z 384.2 (M+H)$^+$.

3-[4-[4-[(1R,5S)-3,8-diazabicyclo[3.2.1]octan-3-yl]-4-oxo-butyl]-3-methyl-2-oxo-benzimidazol-1-yl]piperidine-2,6-dione (Intermediate ARP)

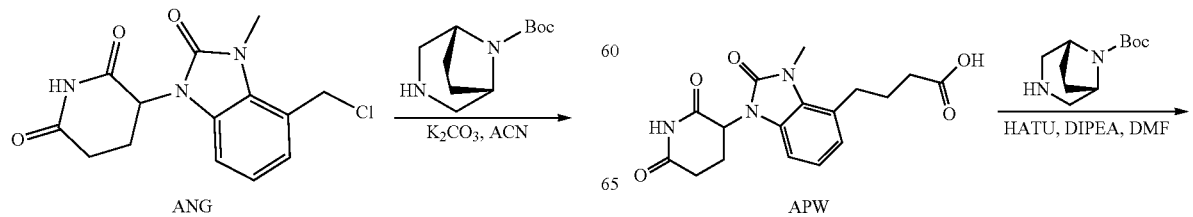

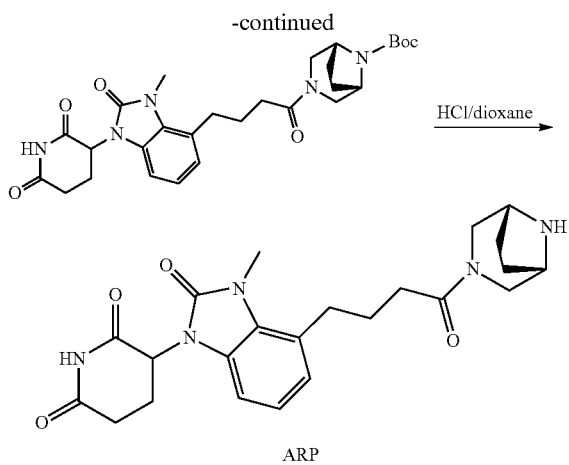

ARP

Step 1—Tert-butyl (1R,5S)-3-[4-[1-(2,6-dioxo-3-piperidyl)-3-methyl-2-oxo-benzimidazol-4-yl]butanoyl]-3,8-diazabicyclo[3.2.1]octane-8-carboxylate To a solution of 4-[1-(2,6-dioxo-3-piperidyl)-3-methyl-2-oxo-benzimidazol-4-yl]butanoic acid (150 mg, 434 umol, Intermediate APW) in DMF (3 mL) was added HATU (247 mg, 652 umol) and DIPEA (280 mg, 2.17 mmol). The mixture was stirred at 25° C. for 0.5 hr. Then tert-butyl (1R,5S)-3,8-diazabicyclo[3.2.1]octane-8-carboxylate (184 mg, 868 umol, CAS #149771-44-8) was added and the mixture was stirred at 25° C. for 1 hr. On completion, the reaction mixture was concentrated in vacuo to give a residue. The residue was purified by reversed-phase HPLC (FA) to give the title compound (130 mg, 55% yield) as a white solid. LC-MS (ESI+) m/z 440.3 (M+H−100)+.

Step 2—3-[4-[4-[(1R,5S)-3,8-diazabicyclo[3.2.1]octan-3-yl]-4-oxo-butyl]-3-methyl-2-oxo-benzimidazol-1-yl]piperidine-2,6-dione To a solution of tert-butyl (1R,5S)-3-[4-[1-(2,6-dioxo-3-piperidyl)-3-methyl-2-oxo-benzimidazol-4-yl] butanoyl]-3,8-diazabicyclo[3.2.1]octane-8-carboxylate (70 mg, 130 umol) in DCM (3 mL) was added HCl/dioxane (4 M, 1 mL). The mixture was stirred at 25° C. for 1 hr. On completion, the reaction mixture was concentrated under reduced pressure to give a residue to give the title compound (60 mg, 95% yield, HCl salt) as a white solid.

Tributyl-(5-methyl-2-pyridyl)stannane (Intermediate ARQ)

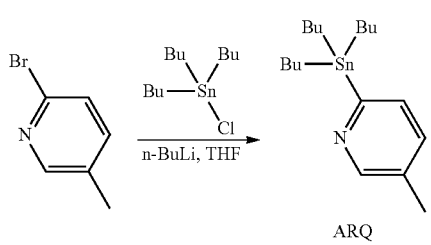

ARQ

To a solution of 2-bromo-5-methyl-pyridine (5.00 g, 29.0 mmol, CAS #3510-66-5) in THF (50 mL) was added n-BuLi (2.5 M, 11.7 mL) at −78° C. dropwise. After 1.5 h, tributylchlorostannane (11.3 g, 34.8 mmol) was added and the mixture was stirred at −78° C. for another 1 hr. On completion, the reaction mixture was quenched by H₂O (30 mL) and extracted with EA (3×40 mL). The combined organic layers were dried over Na₂SO₄, filtered and concentrated in vacuo. The residue was purified by column chromatography (PE:EA=60:1) to give the title compound (11.0 g, 89% yield) as yellow oil. ¹H NMR (400 MHz, CDCl₃) δ 8.59 (s, 1H), 7.28-7.34 (m, 2H), 2.28 (s, 3H), 1.25-1.39 (m, 12H), 1.05-1.19 (m, 6H), 0.86-0.90 (m, 9H).

4-[3-(5-Methyl-2-pyridyl)-4-(pyrazolo[1,5-a]pyrimidine-3-carbonylamino)pyrazol-1-yl] cyclohexanecarboxylic acid (Intermediate ARR)

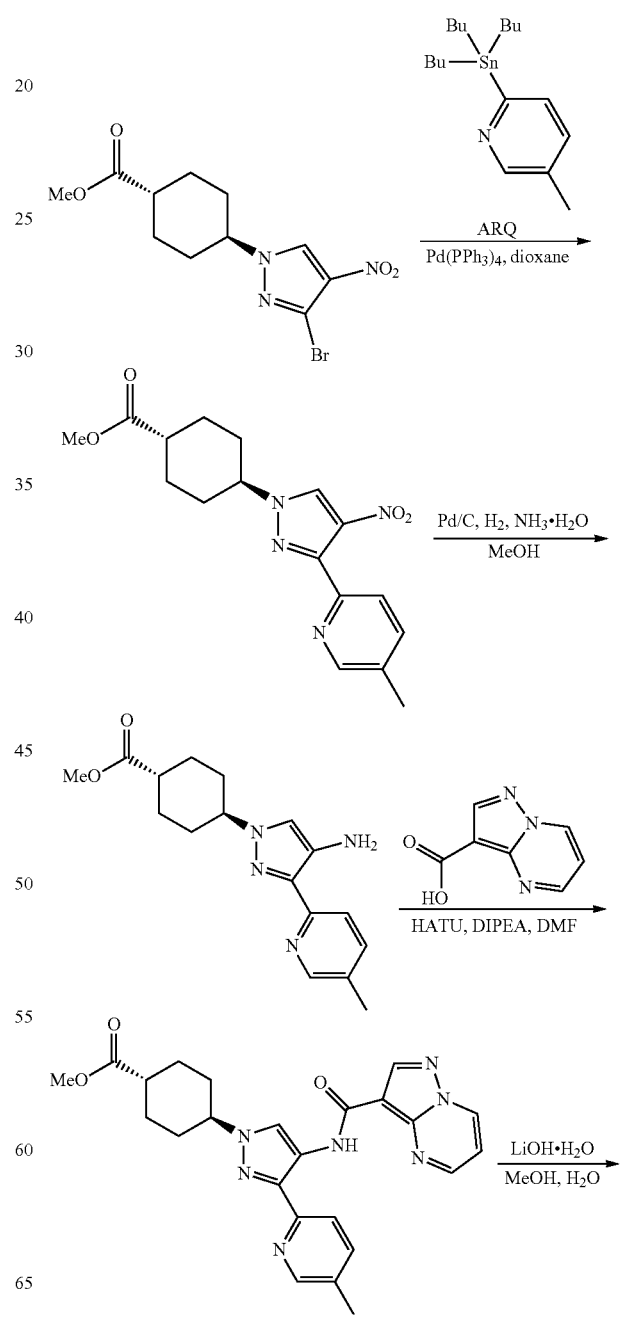

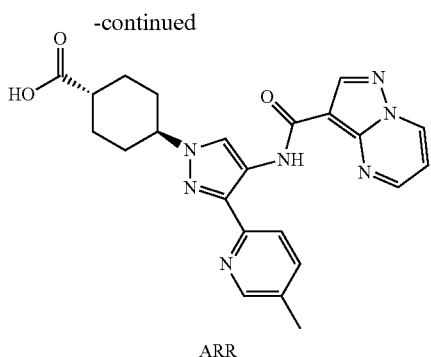

ARR

Step 1—Methyl 4-[3-(5-methyl-2-pyridyl)-4-nitro-pyrazol-1-yl] cyclohexanecarboxylate A mixture of methyl 4-(3-bromo-4-nitro-pyrazol-1-yl) cyclohexanecarboxylate (2.00 g, 6.02 mmol, synthesized via Step 1 of Intermediate APF), tributyl-(5-methyl-2-pyridyl) stannane (2.53 g, 6.62 mmol, Intermediate ARQ) and Pd(PPh$_3$)$_4$ (347 mg, 301 umol) in dioxane (60 mL) was stirred at 120° C. for 18 hrs under nitrogen atmosphere. On completion, the reaction mixture was concentrated in vacuo. The residue was purified by silica gel chromatography (PE:EA=1:1) and reversed-phase HPLC (FA) to give the title compound (1.00 g, 48% yield) as yellow oil. $^1$H NMR (400 MHz, CDCl$_3$) δ 8.58 (d, J=1.2 Hz, 1H), 8.27 (s, 1H), 7.66-7.60 (m, 2H), 4.28-4.20 (m, 1H), 3.71 (s, 3H), 2.42 (s, 3H), 2.41-2.34 (m, 3H), 2.27-2.20 (m, 2H), 1.91-1.79 (m, 2H), 1.72-1.60 (m, 2H).

Step 2—Methyl 4-[4-amino-3-(5-methyl-2-pyridyl) pyrazol-1-yl] cyclohexanecarboxylate To a mixture of methyl 4-[3-(5-methyl-2-pyridyl)-4-nitro-pyrazol-1-yl]cyclohexanecarboxylate (500 mg, 1.45 mmol) in MeOH (10 mL) was added NH$_3$—H$_2$O (0.01 mL, 30% solution) and Pd/C (50.0 mg, 5 wt %). The reaction mixture was stirred at 20° C. for 1 hr under H$_2$ (15 Psi). On completion, the reaction mixture was filtered. The filtrate was concentrated in vacuo to give the title compound (310 mg, 67% yield) as brown oil. LC-MS (ESI$^+$) m/z 315.0 (M+H)$^+$.

Step 3—Methyl 4-[3-(5-methyl-2-pyridyl)-4-(pyrazolo[1,5-a]pyrimidine-3-carbonylamino)pyrazol-1-yl]cyclohexanecarboxylate A mixture of methyl 4-[4-amino-3-(5-methyl-2-pyridyl) pyrazol-1-yl]cyclohexanecarboxylate (50.0 mg, 159 umol), pyrazolo[1,5-a]pyrimidine-3-carboxylic acid (25.9 mg, 159 umol, CAS #25940-35-6), HATU (66.5 mg, 174 umol) and DIPEA (102 mg, 795 umol) in DMF (2 mL) was stirred at 20° C. for 0.5 hour. On completion, the reaction mixture was quenched by water (0.1 mL) and the mixture was concentrated in vacuo. The residue was purified by reversed-phase HPLC (0.1% FA condition) to give the title compound (55.0 mg, 75% yield) as a yellow solid. $^1$H NMR (400 MHz, DMSO-d$_6$) δ 12.18 (s, 1H), 9.35 (dd, J=1.6, 7.2 Hz, 1H), 9.13 (dd, J=1.6, 4.0 Hz, 1H), 8.70-8.68 (m, 1H), 8.68 (s, 1H), 8.48 (s, 1H), 7.86 (d, J=8.0 Hz, 1H), 7.72 (dd, J=1.6, 8.0 Hz, 1H), 7.34 (dd, J=4.0, 7.2 Hz, 1H), 4.35-4.21 (m, 1H), 3.63 (s, 3H), 2.46-2.43 (m, 1H), 2.40 (s, 3H), 2.18-2.11 (m, 2H), 2.10-2.03 (m, 2H), 1.94-1.82 (m, 2H), 1.65-1.52 (m, 2H).

Step 4—4-[3-(5-Methyl-2-pyridyl)-4-(pyrazolo[1,5-a]pyrimidine-3-carbonylamino)pyrazol-1-yl] cyclohexanecarboxylic acid To a mixture of methyl 4-[3-(5-methyl-2-pyridyl)-4-(pyrazolo[1,5-a]pyrimidine-3-carbonylamino) pyrazol-1-yl] cyclohexanecarboxylate (55.0 mg, 119 umol) in a mixed solvent of MeOH (8 mL) and H$_2$O (2 mL) was added LiOH—H$_2$O (15.0 mg, 359 umol). The reaction mixture was stirred at 20° C. for 16 hrs, then 40° C. for 3 hrs. On completion, the reaction mixture was acidified with 1N HCl aqueous until the pH=7. The mixture was concentrated in vacuo to give the title compound (50.0 mg, 93% yield) as yellow solid. $^1$H NMR (400 MHz, DMSO-d$_6$) δ 12.17 (s, 1H), 9.32 (dd, J=1.6, 6.8 Hz, 1H), 9.11 (dd, J=1.6, 4.0 Hz, 1H), 8.68 (s, 2H), 8.44 (s, 1H), 7.87 (d, J=8.0 Hz, 1H), 7.73-7.69 (m, 1H), 7.36-7.31 (m, 2H), 4.18-4.13 (m, 1H), 2.39 (s, 3H), 2.31-2.26 (m, 1H), 2.08-2.04 (m, 2H), 1.98-1.93 (m, 2H), 1.76-1.69 (m, 2H), 1.48-1.41 (m, 2H).

4-[4-[2-[1-(2,6-Dioxo-3-piperidyl)-3-methyl-2-oxo-benzimidazol-4-yl]ethyl]-1-piperidyl] benzaldehyde (Intermediate ARS)

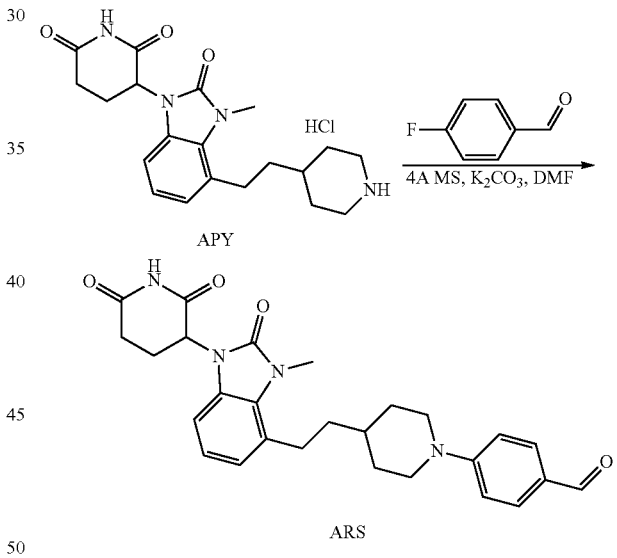

To a solution of 3-[3-methyl-2-oxo-4-[2-(4-piperidyl) ethyl]benzimidazol-1-yl]piperidine-2,6-dione (120 mg, 295 umol, HCl salt, Intermediate APY) in DMF (3.0 mL) was added K$_2$CO$_3$ (81.5 mg, 590 umol) and 4 Å molecular sieves (120 mg). Then 4-fluorobenzaldehyde (54.9 mg, 442 umol, 46.5 uL) was added and stirred at 80° C. for 12 hr. On completion, the reaction mixture was filtered. The filtrate was adjusted with FA until the pH=5-6 and concentrated in vacuo to give a residue. The residue was purified by reverse phase flash (FA condition) to give the title compound (70.0 mg, 50% yield) as a white solid. $^1$H NMR (400 MHz, DMSO-d$_6$) δ 11.06 (br s, 1H), 9.68 (s, 1H), 7.71-7.64 (m, 2H), 7.09-6.80 (m, 5H), 5.36 (dd, J=5.6, 12.4 Hz, 1H), 4.04-3.96 (m, 2H), 3.56 (s, 3H), 3.28-3.22 (m, 1H), 3.01-2.78 (m, 5H), 2.75-2.55 (m, 2H), 1.99 (t, J=5.2 Hz, 1H), 1.86 (d, J=11.6 Hz, 2H), 1.61-1.49 (m, 2H), 1.30-1.19 (m, 2H).

5-(1,4-Oxazepan-4-yl)pyrazolo[1,5-a]pyrimidine-3-carboxylic acid (Intermediate ARX)

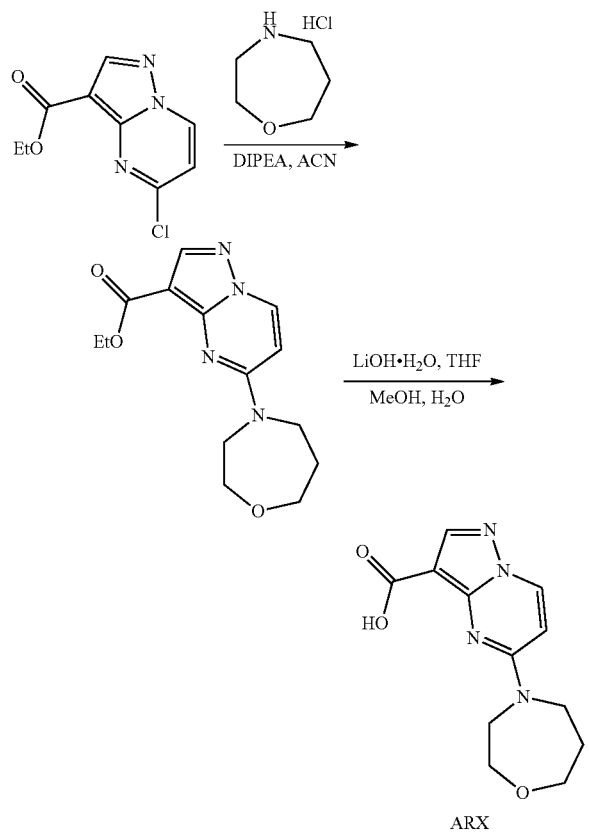

Step 1-Ethyl 5-(1,4-oxazepan-4-yl)pyrazolo [1,5-a]pyrimidine-3-carboxylate

A mixture of ethyl 5-chloropyrazolo[1,5-a]pyrimidine-3-carboxylate (2.50 g, 11.1 mmol, CAS #1224944-77-7), 1,4-oxazepane; hydrochloride (1.60 g, 11.6 mmol, HCl) and DIPEA (4.30 g, 33.2 mmol) in MeCN (35 mL) was stirred at 60° C. for 1 hr. On completion, the reaction mixture was concentrated in vacuo. The residue was diluted in ethyl acetate (50 mL) and water (80 mL). The mixture was acidified with saturated critic acid aqueous until the pH=7. The mixture was extracted with ethyl acetate (3×50 mL). The organic layer was concentrated in vacuo to give the title compound (3.00 g, 93% yield) as yellow solid. $^1$H NMR (400 MHz, DMSO-$d_6$) δ 8.70 (d, J=8.0 Hz, 1H), 8.19 (s, 1H), 6.78 (d, J=8.0 Hz, 1H), 4.21-4.15 (m, 2H), 4.06-3.69 (m, 6H), 3.64 (t, J=5.6 Hz, 2H), 1.92-1.89 (m, 2H), 1.27 (t, J=7.2 Hz, 3H).

Step 2—5-(1,4-Oxazepan-4-yl)pyrazolo[1,5-a]pyrimidine-3-carboxylic acid

To a solution of ethyl 5-(1,4-oxazepan-4-yl)pyrazolo[1,5-a]pyrimidine-3-carboxylate (3.40 g, 11.7 mmol) in THF (3 mL), MeOH (3 mL) and H$_2$O (1 mL) was added LiOH.H$_2$O (1.47 g, 35.1 mmol), and the mixture was stirred at 60° C. for 16 hrs. On completion, the reaction mixture was adjusted to pH of 5-6 with HCl (aq. 1 mL) and extracted with ethyl acetate (3×15 mL). The combined organic layers were washed with brine (5 mL), dried over anhydrous sodium sulfate, filtered and concentrated in vacuo to give the title compound (2.60 g, 85% yield) as white solid. $^1$H NMR (400 MHz, DMSO-$d_6$) δ 11.68 (s, 1H), 8.70 (d, J=8.0 Hz, 1H), 8.17 (s, 1H), 6.76 (d, J=8.0 Hz, 1H), 3.94-3.71 (m, 5H), 3.64 (t, J=5.6 Hz, 2H), 1.95-1.81 (m, 3H).

N-(3-(difluoromethyl)-1-((1r,4r)-4-formylcyclohexyl)-1H-pyrazol-4-yl)-5-(1,4-oxazepan-4-yl)pyrazolo[1,5-a]pyrimidine-3-carboxamide (Intermediate ARY)

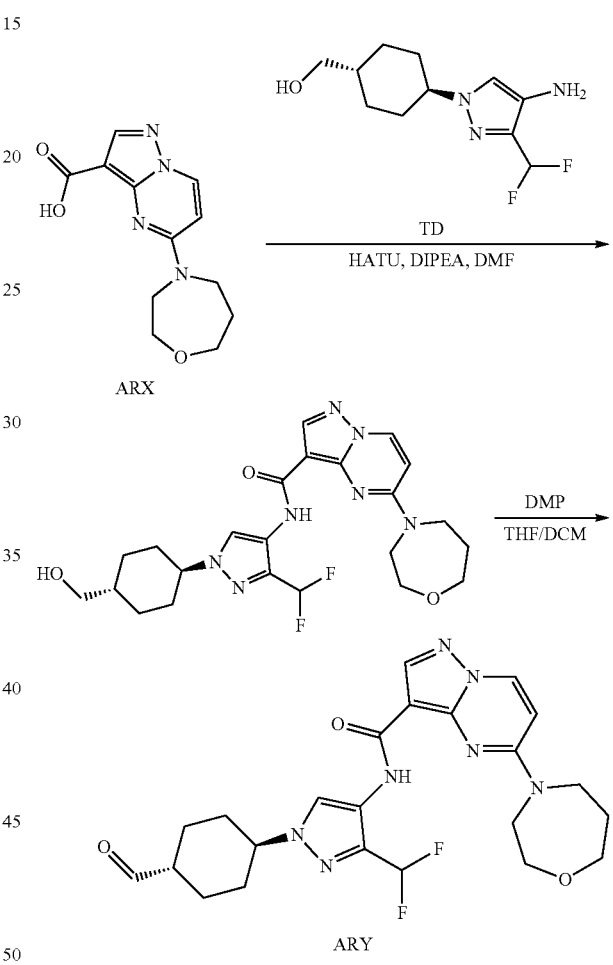

Step 1—N-(3-(difluoromethyl)-1-((1r,4r)-4-(hydroxymethyl)cyclohexyl)-1H-pyrazol-4-yl)-5-(1,4-oxazepan-4-yl)pyrazolo[1,5-a]pyrimidine-3-carboxamide To a solution of 5-(1,4-oxazepan-4-yl)pyrazolo[1,5-a]pyrimidine-3-carboxylic acid (1.00 g, 3.81 mmol, Intermediate ARX) and [4-[4-amino-3-(difluoromethyl)pyrazol-1-yl]cyclohexyl]methanol (1.22 g, 4.96 mmol, Intermediate TD) in DMF (10 mL) was added HATU (2.17 g, 5.72 mmol) and DIPEA (1.48 g, 11.4 mmol) at 25° C. Then the mixture was stirred at 60° C. for 16 hrs. On completion, the reaction mixture was diluted with water (15 mL) and extracted with ethyl acetate (3×25 mL). The combined organic layers were washed with brine (15 mL), dried over anhydrous sodium sulfate, filtered and concentrated in vacuo to give a residue. The residue was purified by silica gel chromatography (petroleum ether:ethyl acetate=20:1 to dichloromethane:methanol=20:1) to give the title compound (1.50 g, 56% yield) as white solid. $^1$H NMR (400 MHz, DMSO-d$_6$) δ 9.30 (s, 1H), 8.77 (d, J=8.0 Hz, 1H), 8.47-8.20 (m, 2H), 7.33-6.92 (m, 1H), 6.82 (d, J=8.0 Hz, 1H), 4.19-4.13 (m, 1H), 3.77 (s, 3H), 3.72-3.57 (m, 3H), 3.34 (s, 3H), 3.17-3.15 (m, 2H), 2.06-2.03 (m, 2H), 1.96-1.81 (m, 5H), 1.81-1.61 (m, 3H), 1.45-1.42 (m, 1H).

Step 2—N-(3-(difluoromethyl)-1-((1r,4r)-4-formyl-cyclohexyl)-1H-pyrazol-4-yl)-5-(1,4-oxazepan-4-yl)pyrazolo[1,5-a]pyrimidine-3-carboxamide To a mixture of N-[3-(difluoromethyl)-1-[4-(hydroxymethyl)cyclohexyl]pyrazol-4-yl]-5-(1,4-oxazepan-4-yl)pyrazolo[1,5-a]pyrimidine-3-carboxamide (1.60 g, 3.27 mmol) in DCM (20 mL) and THF (20 mL) was added DMP (1.52 g, 3.60 mmol) at 0° C. The reaction mixture was stirred at 20° C. for 1 hr under nitrogen atmosphere. On completion, the reaction mixture was diluted with saturated Na$_2$S$_2$O$_3$ aqueous (10 mL) and saturated NaHCO$_3$ aqueous (10 mL). The mixture was stirred at 20° C. for 0.5 hr. The mixture was diluted with water (100 mL) and extracted with DCM (3×40 mL). The organic layer was washed with saturated NaHCO$_3$ aqueous (3×40 mL) and brine (3×40 mL). The combined organic layers were dried over anhydrous sodium sulfate, filtered and concentrated in vacuo to give the title compound (1.38 g, 87% yield) as yellow solid. $^1$H NMR (400 MHz, DMSO-d$_6$) δ 9.60 (d, J=3.2 Hz, 1H), 9.31 (s, 1H), 8.78 (d, J=8.0 Hz, 1H), 8.40 (s, 1H), 8.27 (s, 1H), 7.26-6.96 (m, 1H), 6.83 (d, J=8.0 Hz, 1H), 4.27-4.16 (m, 1H), 4.09-3.95 (m, 2H), 3.93-3.81 (m, 2H), 3.80-3.75 (m, 2H), 3.67 (t, J=5.6 Hz, 2H), 2.43-2.34 (m, 1H), 2.13-2.03 (m, 4H), 1.93-1.88 (m, 2H), 1.86-1.76 (m, 2H), 1.43-1.32 (m, 2H).

(R)-tert-butyl 2-ethynylmorpholine-4-carboxylate (Intermediate ARZ)

mmol) at 0° C. The mixture was warmed to 25° C. and stirred for 16 hrs. On completion, the reaction mixture was quenched with saturated sodium thiosulfate solution (250 mL) and adjusted pH to 7~8 by sodium bicarbonate saturated solution (100 mL). The mixture was extracted with ethyl acetate (3×200 mL). The combined organic layers were washed with brine (150 mL), dried over anhydrous sodium sulfate, filtered and concentrated in vacuo to give the title compound (5.80 g, 85% yield) as yellow gum. $^1$H NMR (400 MHz, DMSO-d$_6$) δ 9.63-9.47 (m, 1H), 3.83-3.75 (m, 3H), 3.70-3.58 (m, 2H), 3.58-3.53 (m, 2H), 1.41 (s, 9H).

Step 2—(R)-tert-butyl 2-ethynylmorpholine-4-carboxylate

To a solution of tert-butyl (2S)-2-formylmorpholine-4-carboxylate (1.50 g, 6.97 mmol) and K$_2$CO$_3$ (2.89 g, 20.9 mmol) in MeOH (100 mL) was added 1-diazo-1-dimethoxyphosphoryl-propan-2-one (1.34 g, 6.97 mmol) dropwise at 0° C. The reaction mixture was stirred at 25° C. for 16 hrs. On completion, the reaction mixture was filtered and the filtrate was concentrated in vacuo. The residue was purified by silica gel chromatography (petroleum ether:ethyl acetate=50:1) to give the title compound (630 mg, 43% yield) as white solid. $^1$H NMR (400 MHz, DMSO-d$_6$) δ 4.37-4.30 (m, 1H), 3.83-3.75 (m, 1H), 3.60-3.50 (m, 2H), 3.49-3.33 (m, 2H), 3.30-3.15 (m, 2H), 1.40 (s, 9H).

2-(2,6-Dioxo-3-piperidyl)-4-[2-[4-(methylaminomethyl)phenyl]ethylamino]isoindoline-1,3-dione (Intermediate ANM)

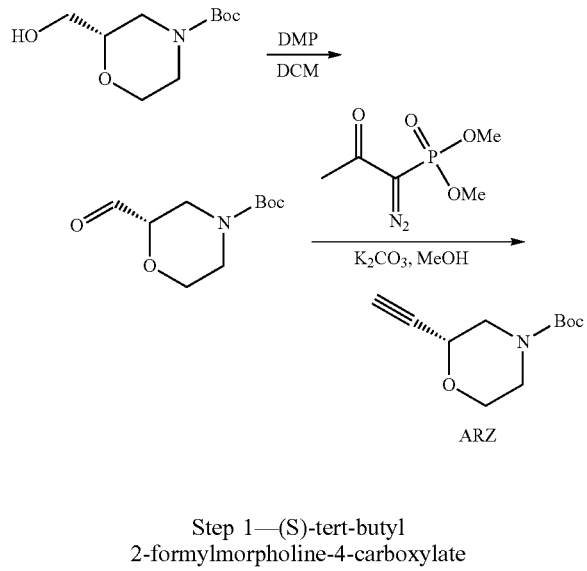

Step 1—(S)-tert-butyl 2-formylmorpholine-4-carboxylate

To a solution of tert-butyl (2S)-2-(hydroxymethyl)morpholine-4-carboxylate (5.00 g, 23.0 mmol, CAS #135065-76-8) in DCM (150 mL) was added DMP (10.7 g, 25.3

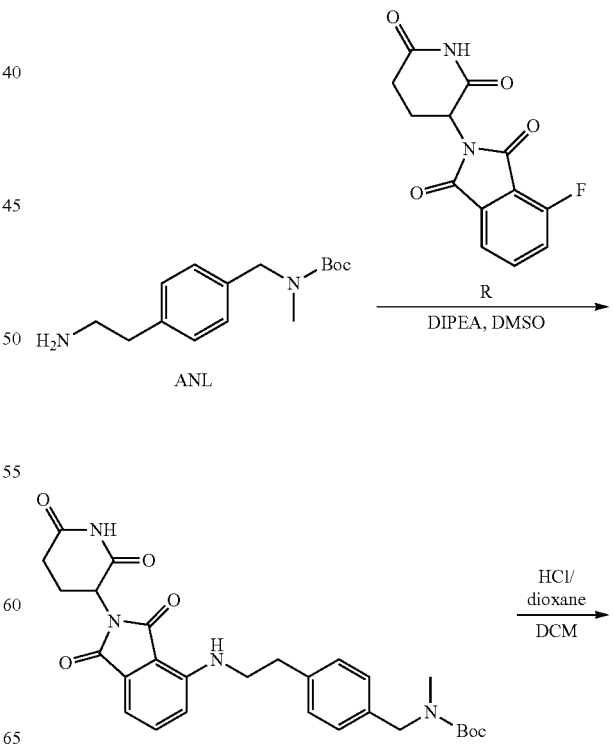

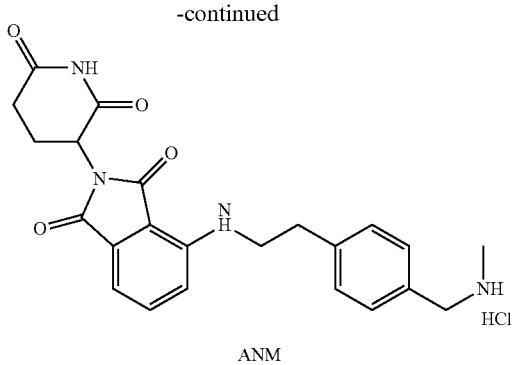

ANM

Step 1—Tert-butyl N-[[4-[2-[[2-(2,6-dioxo-3-piperidyl)-1,3-dioxo-isoindolin-4-yl]amino]ethyl]phenyl]methyl]-N-methyl-carbamate A mixture of tert-butyl N-[[4-(2-aminoethyl)phenyl]methyl]-N-methyl-carbamate (170 mg, 643 umol, Intermediate ANL), 2-(2,6-dioxo-3-piperidyl)-4-fluoro-isoindoline-1,3-dione (170 mg, 615 umol, Intermediate R) and DIPEA (255 mg, 1.97 mmol) in DMSO (3 mL) was stirred at 130° C. for 2 hours. On completion, the reaction was quenched with water (0.2 mL). The mixture was concentrated in vacuo to give a residue. The residue was purified by reversed phase (FA condition) to give the title compound (193 mg, 57% yield) as yellow solid. $^1$H NMR (400 MHz, DMSO-$d_6$) δ 11.08 (s, 1H), 7.61-7.55 (m, 1H), 7.28 (d, J=7.6 Hz, 2H), 7.19-7.12 (m, 3H), 7.03 (d, J=7.2 Hz, 1H), 6.59-6.53 (m, 1H), 5.06-5.02 (m, 1H), 4.33 (s, 2H), 3.58-3.50 (m, 2H), 2.88 (m, 3H), 2.72 (s, 3H), 2.63-2.53 (m, 2H), 2.06-1.99 (m, 1H), 1.44-1.36 (m, 9H).

Step 2—2-(2,6-Dioxo-3-piperidyl)-4-[2-[4-(methylaminomethyl)phenyl]ethylamino]isoindoline-1,3-dione To a solution of tert-butyl N-[[4-[2-[[2-(2,6-dioxo-3-piperidyl)-1,3-dioxo-isoindolin-4-yl]amino]ethyl]phenyl]methyl]-N-methyl-carbamate (33.0 mg, 63.3 umol) in DCM (2 mL) was added HCl/dioxane (4.0 M, 1.0 mL) at 15° C. The mixture was stirred at 15° C. for 0.5 hour. On completion, the mixture was concentrated in vacuo to give the title compound (27.0 mg, 93% yield, HCl salt) as light yellow solid. LC-MS (ESI$^+$) m/z 421.1 (M+H)$^+$.

4-(7-Azaspiro[3.5]nonan-2-ylamino)-2-(2,6-dioxo-3-piperidyl)isoindoline-1,3-dione (Intermediate AML)

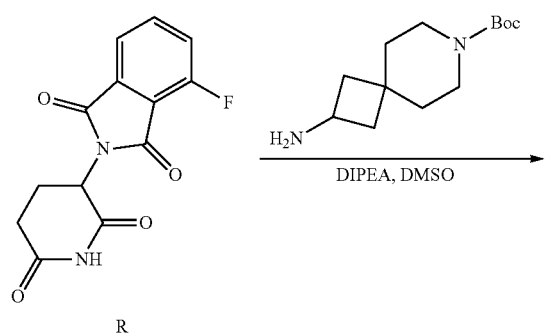

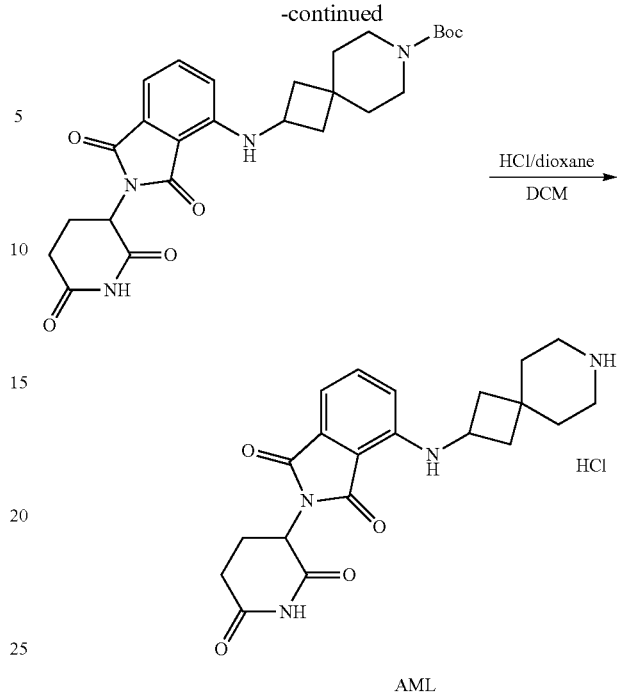

AML

Step 1—Tert-butyl 2-[[2-(2,6-dioxo-3-piperidyl)-1,3-dioxo-isoindolin-4-yl]amino]-7-azaspiro[3.5]nonane-7-carboxylate To a mixture of 2-(2,6-dioxo-3-piperidyl)-4-fluoro-isoindoline-1,3-dione (0.50 g, 1.81 mmol, Intermediate R) and tert-butyl 2-amino-7-azaspiro[3.5]nonane-7-carboxylate (478 mg, 1.99 mmol, CAS #1239319-82-4) in DMSO (10 mL) was added DIPEA (468 mg, 3.62 mmol). The mixture was stirred at 130° C. for 2 hours. On completion, the reaction mixture was poured into the water (30 mL), and extracted with EA (2×20 mL). The combined organic phase was washed with brine (2×30 mL), dried with anhydrous Na$_2$SO$_4$, filtered and concentrated in vacuo to give the title compound (0.80 g, 89% yield) as a yellow solid. $^1$H NMR (400 MHz, CDCl$_3$) δ 8.33 (s, 1H), 7.48 (d, J=7.8 Hz, 1H), 7.11 (d, J=7.2 Hz, 1H), 6.74 (d, J=8.4 Hz, 1H), 6.31 (d, J=5.6 Hz, 1H), 4.95-4.89 (m, 1H), 4.08-3.99 (m, 1H), 3.42-3.35 (m, 2H), 3.33-3.26 (m, 2H), 2.93-2.84 (m, 1H), 2.83-2.71 (m, 2H), 2.48-2.35 (m, 2H), 2.17-2.09 (m, 1H), 1.78-1.71 (m, 2H), 1.65-1.60 (m, 2H), 1.58-1.52 (m, 2H), 1.45 (s, 9H).

Step 2—4-(7-Azaspiro[3.5]nonan-2-ylamino)-2-(2,6-dioxo-3-piperidyl)isoindoline-1,3-dione To a mixture of tert-butyl 2-[[2-(2,6-dioxo-3-piperidyl)-1,3-dioxo-isoindolin-4-yl]amino]-7-azaspiro[3.5]nonane-7-carboxylate (0.80 g, 1.61 mmol) in DCM (20 mL) was added HCl/dioxane (4 M, 1.21 mL). The reaction mixture was stirred at 20° C. for 0.5 hour. On completion, the reaction mixture was concentrated in vacuo to give the title compound (690 mg, 98% yield) as a yellow solid. LC-MS (ESI$^+$) m/z 397.2 (M+H)$^+$.

2073

Tert-butyl 4-(3-aminopropoxymethyl)piperidine-1-carboxylate (Intermediate AJG)

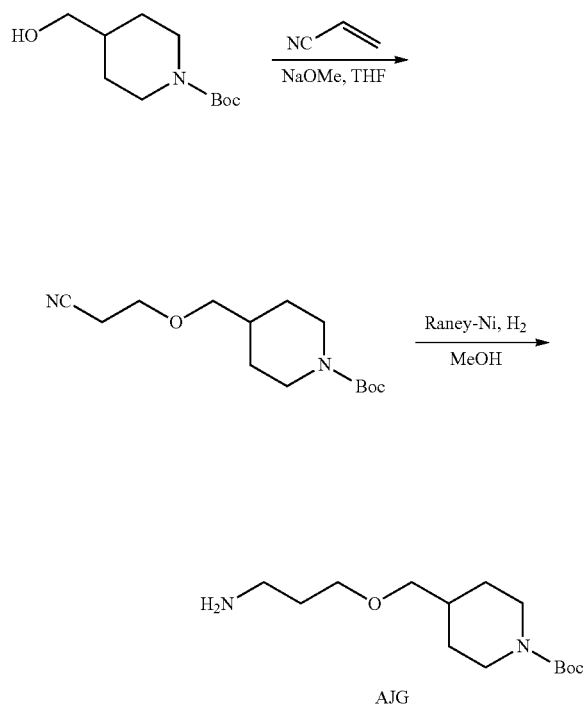

Step 1—Tert-butyl 4-(2-cyanoethoxymethyl)piperidine-1-carboxylate

To a mixture of tert-butyl 4-(hydroxymethyl)piperidine-1-carboxylate (10.0 g, 46.4 mmol, CAS #123855-51-6) and prop-2-enenitrile (4.93 g, 92.9 mmol) in THF (100 mL) was added NaOMe (250 mg, 4.64 mmol). The reaction mixture was stirred at 25° C. for 12 hours. On completion, the reaction mixture was diluted with water (100 mL) and extracted with EA (2×200 mL). The combined organic layers was dried over Na$_2$SO$_4$, filtered and concentrated in vacuo to give the title compound (8.20 g, 65% yield) as colorless oil. $^1$H NMR (400 MHz, CDCl$_3$) δ 4.19-4.04 (m, 2H), 3.64 (t, J=6.4 Hz, 2H), 3.33 (d, J=6.0 Hz, 2H), 2.78-2.63 (m, 2H), 2.59 (t, J=6.4 Hz, 2H), 1.81-1.73 (m, 1H), 1.73-1.68 (m, 2H), 1.45 (s, 9H), 1.21-1.09 (m, 2H).

Step 2—Tert-butyl 4-(3-aminopropoxymethyl)piperidine-1-carboxylate

To a mixture of tert-butyl 4-(2-cyanoethoxymethyl)piperidine-1-carboxylate (8.20 g, 30.5 mmol) in MeOH (80 mL) was added Raney-Ni (4.10 g, 47.8 mmol). The reaction mixture was stirred at 25° C. for 12 hours under H$_2$ (50 Psi). On completion, the reaction mixture was filtered. The filtrate was concentrated in vacuo to give the title compound (8.00 g, 96% yield) as colorless oil. $^1$H NMR (400 MHz, CDCl$_3$) δ 4.09 (s, 2H), 3.51-3.44 (m, 2H), 3.25 (d, J=6.0 Hz, 2H), 2.79 (t, J=6.8 Hz, 2H), 2.74-2.60 (m, 2H), 1.77-1.65 (m, 5H), 1.45 (s, 9H), 1.42-1.27 (m, 2H), 1.20-1.05 (m, 2H).

2074

2-(2,6-Dioxo-3-piperidyl)-4-[3-(4-piperidylmethoxy)propylamino]isoindoline-1,3-dione (Intermediate AJH)

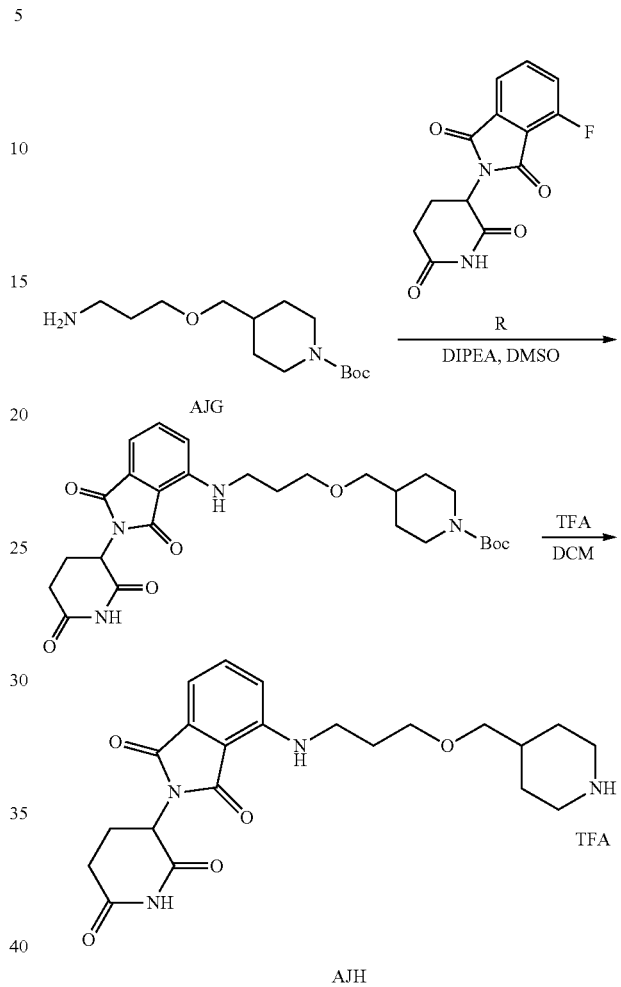

Step 1—Tert-butyl 4-[3-[[2-(2,6-dioxo-3-piperidyl)-1,3-dioxo-isoindolin-4-yl]amino]propoxymethyl]piperidine-1-carboxylate A mixture of 2-(2,6-dioxo-3-piperidyl)-4-fluoro-isoindoline-1,3-dione (300 mg, 1.09 mmol, Intermediate R), tert-butyl 4-(3-aminopropoxymethyl)piperidine-1-carboxylate (355 mg, 1.30 mmol, Intermediate AJG) and DIPEA (421 mg, 3.26 mmol) in DMSO (3 mL) was stirred at 130° C. for 2 hours. On completion, after cooled to 15° C., the reaction was quenched with water (0.2 mL). The mixture was concentrated in vacuo and the residue was purified by reversed phase flash (TFA condition) to give the title compound (200 mg, 35% yield) as light yellow solid. 1H NMR (400 MHz, DMSO-d$_6$) δ 11.09 (s, 1H), 7.63-7.54 (m, 1H), 7.09 (d, J=8.8 Hz, 1H), 7.02 (d, J=6.8 Hz, 1H), 6.66 (t, J=5.2 Hz, 1H), 5.07-5.02 (m, 1H), 3.98-3.86 (m, 2H), 3.45 (t, J=5.6 Hz, 2H), 3.41-3.35 (m, 3H), 3.22 (d, J=6.4 Hz, 2H), 2.95-2.83 (m, 1H), 2.62-2.53 (m, 3H), 2.06-1.98 (m, 1H), 1.82-1.81 (m, 2H), 1.74-1.60 (m, 3H), 1.38 (s, 9H), 1.06-0.94 (m, 2H).

2075

Step 2—2-(2,6-Dioxo-3-piperidyl)-4-[3-(4-piperidylmethoxy)propylamino]isoindoline-1,3-dione To a solution of tert-butyl 4-[3-[[2-(2,6-dioxo-3-piperidyl)-1,3-dioxo-isoindolin-4-yl]amino] propoxymethyl] piperidine-1-carboxylate (60.0 mg, 113 umol) in DCM (2 mL) was added TFA (1 mL) at 15° C. The mixture was stirred at 15° C. for 2 hours. On completion, the mixture was concentrated in vacuo to give the title compound (60.0 mg, 97% yield, TFA salt) as light yellow oil. LC-MS (ESI$^+$) m/z 429.1 (M+H)$^+$.

N-[6-(difluoromethyl)-2-(4-formylcyclohexyl) indazol-5-yl]-6-(trifluoromethyl) pyridine-2-carboxamide (Intermediate ALU)

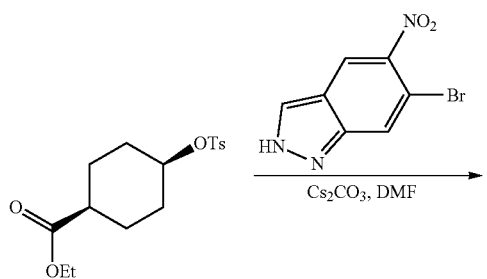

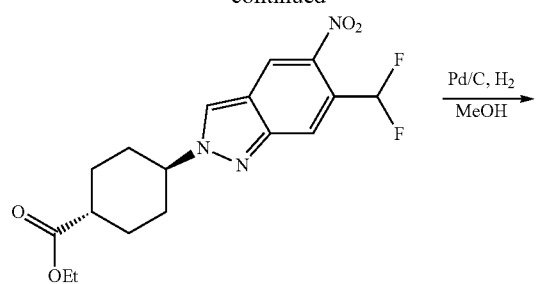

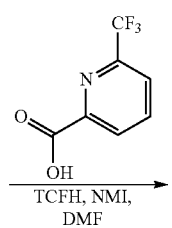

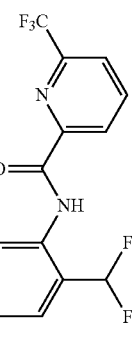

-continued

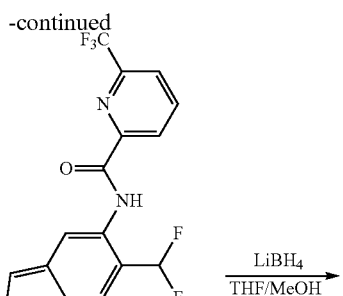

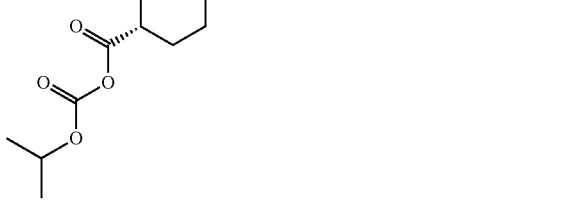

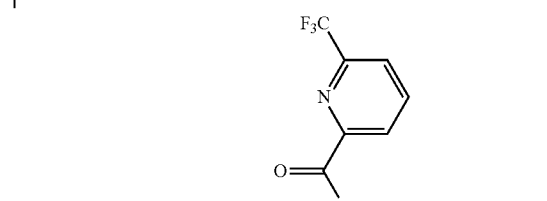

ALU

Step 1—Ethyl 4-(6-bromo-5-nitro-indazol-2-yl)cyclohexanecarboxylate

To a solution of 6-bromo-5-nitro-2H-indazole (8.30 g, 34.3 mmol, CAS #1351813-02-9) and ethyl 4-(p-tolylsulfonyloxy)cyclohexanecarboxylate (22.4 g, 68.6 mmol, Intermediate AGK) in DMF (100 mL) was added $Cs_2CO_3$ (22.4 g, 68.6 mmol). The mixture was stirred at 80° C. for 24 hrs. On completion, the reaction mixture was concentrated in vacuo to remove solvent. Then to the mixture was added 100 mL water and extracted with EA 150 mL (3×50 mL). The combined organic layers were washed with 100 mL brine, dried over $Na_2SO_4$, filtered and concentrated in vacuo to give a residue. The residue was purified by flash silica gel chromatography (PE:EA 2:1) and then the residue was purified by pre-HPLC (column: Phenomenex Synergi Max-RP 250*50 mm*10 um; mobile phase: [water (0.1% TFA)-ACN]; B %: 45ACN %-75ACN %, 29 min) to give the title compound (1.60 g, 40% yield) as yellow solid. $^1$H NMR (400 MHz, DMSO-$d_6$) δ 8.60 (s, 1H), 8.45 (s, 1H), 8.34 (s, 1H), 4.91-4.71 (m, 1H), 4.08 (q, J=7.2 Hz, 2H), 2.47-2.40 (m, 1H), 2.10-1.89 (m, 6H), 1.74-1.55 (m, 2H), 1.20 (t, J=7.2 Hz, 3H).

Step 2—2-(2,6-Dioxo-3-piperidyl)-4-[[(2R)-morpholin-2-yl]methylamino]isoindoline-1,3-dione To a solution of ethyl 4-(6-bromo-5-nitro-indazol-2-yl)cyclohexanecarboxylate (1.60 g, 4.04 mmol) and potassium; trifluoro(vinyl)boranuide (1.62 g, 12.1 mmol) and potassium; trifluoro(vinyl)boranuide (1.62 g, 12.1 mmol) in dioxane (100 mL) was added Pd(dppf)$Cl_2$ (329 mg, 403 umol) and NaHCO$_3$ (2 M, 4.04 mL). The mixture was stirred at 90° C. for 6 hrs. On completion, the mixture was filtered with celite and concentrated in vacuo. The crude product was purified by flash silica gel chromatography (PE:EA 1:1) to give the title compound (1.39 g, 50% yield) as yellow solid. LC-MS (ESI$^+$) m/z 344.1 (M+1)$^+$.

Step 3—Ethyl 4-(6-formyl-5-nitro-indazol-2-yl)cyclohexanecarboxylate

A mixture of ethyl 4-(5-nitro-6-vinyl-indazol-2-yl)cyclohexanecarboxylate (1.39 g, 4.20 mmol), NaIO$_4$ (3.74 g, 17.4 mmol), OsO$_4$ (33.3 mg, 131 umol) and 2,6-dimethylpyridine (936 mg, 8.74 mmol, 1.02 mL) in a mixed solvents of dioxane (20 mL) and H$_2$O (20 mL) was stirred at 0° C. for 1 hour. On completion, the mixture was added 10 mL Na$_2$S204 and extracted with DCM 150 mL (3×50 mL). The combined organic layers were washed with 100 mL brine, dried over Na$_2$SO$_4$, filtered and concentrated in vacuo to give the title compound (1.50 g, 80% yield) as yellow solid. LC-MS (ESI$^+$) m/z 346.0 (M+1)$^+$.

Step 4—Ethyl 4-[6-(difluoromethyl)-5-nitro-indazol-2-yl]cyclohexanecarboxylate

To a solution of ethyl 4-(6-formyl-5-nitro-indazol-2-yl)cyclohexanecarboxylate (1.50 g, 4.34 mmol) in DCM (80 mL) was added DAST (1.75 g, 10.8 mmol). The mixture was stirred at 0° C. for 2 hrs. On completion, to the mixture was added 2 mL H$_2$O slowly at 0° C., then the solution was concentrated in vacuo. The crude product was purified by reverse phase HPLC (0.1% TFA condition) to give the title compound (900 mg, 56% yield) as yellow solid. $^1$H NMR (400 MHz, DMSO-$d_6$) δ 8.87 (d, J=5.2 Hz, 2H), 8.07 (s, 1H), 7.73-7.37 (m, 1H), 4.71-4.66 (m, 1H), 4.09 (q, J=7.2 Hz, 2H), 2.24-2.15 (m, 2H), 2.13-1.92 (m, 4H), 1.61 (dq, J=3.1, 12.8 Hz, 2H), 1.20 (t, J=7.2 Hz, 3H); LC-MS (ESI$^+$) m/z 368.1 (M+1)$^+$.

Step 5—Ethyl 4-[5-amino-6-(difluoromethyl) indazol-2-yl] cyclohexanecarboxylate

To a solution of ethyl 4-[6-(difluoromethyl)-5-nitro-indazol-2-yl]cyclohexanecarboxylate (900 mg, 2.45 mmol) in THF (20 mL) was added Pd/C (500 mg, 10 wt %). The mixture was stirred at 15° C. for 2 hrs under H$_2$ (15 psi). On completion, the mixture was filtered through celite and concentrated in vacuo to give the title compound (800 mg, 96% yield) as yellow oil. $^1$H NMR (400 MHz, DMSO-$d_6$) δ 8.07 (s, 1H), 7.65 (s, 1H), 7.23-6.91 (m, 1H), 6.84 (s, 1H), 4.78 (s, 2H), 4.48-4.32 (m, 1H), 3.62 (s, 3H), 2.48-2.40 (m, 1H), 2.17-2.02 (m, 4H), 1.99-1.86 (m, 2H), 1.64-1.50 (m, 2H).

Step 6—Ethyl 4-[6-(difluoromethyl)-5-[[6-(trifluoromethyl)pyridine-2-carbonyl]amino] indazol-2-yl] cyclohexanecarboxylate To a solution of 6-(trifluoromethyl)pyridine-2-carboxylic acid (679 mg, 3.56 mmol) and ethyl 4-[5-amino-6-(difluoromethyl) indazol-2-yl]cyclohexanecarboxylate (800 mg, 2.37 mmol) in DMF (20 mL) was added HATU (1.35 g, 3.56 mmol) and DIPEA (919 mg, 7.11 mmol). The mixture was stirred at 70° C. for 2 hrs. On completion, the mixture was added 0.5 mL water, the residue was purified by prep-HPLC (column: Phenomenex luna C18 250*50 mm*10 um; mobile phase: [water (0.1% TFA)-ACN]; B %: 68%-98%, 9 min) to give the title compound (750 mg, 59% yield) as light yellow solid. $^1$H NMR (400 MHz, DMSO-$d_6$) δ 10.50 (s, 1H), 8.56 (s, 1H), 8.49 (s, 1H), 8.48-8.38 (m, 2H), 8.23 (dd, J=1.2, 7.6 Hz, 1H), 8.00 (s, 1H), 7.43-7.09 (m, 1H), 4.65-4.52 (m, 1H), 4.10 (q, J=7.2 Hz, 2H), 2.26-2.16 (m, 2H), 2.12-1.95 (m, 4H), 1.69-1.56 (m, 2H), 1.21 (t, J=7.2 Hz, 3H); LC-MS (ESI$^+$) m/z 511.1 (M+1)$^+$.

Step 7—Ethyl 4-[6-(difluoromethyl)-5-[[6-(trifluoromethyl)pyridine-2-carbonyl]amino]indazol-2-yl] cyclohexane carboxylic acid To a solution of ethyl 4-[6-(difluoromethyl)-5-[[6-(trifluoromethyl)pyridine-2-carbonyl]amino] indazol-2-yl]cyclohexanecarboxylate (300 mg, 587 umol) in THF (1 mL) and MeOH (0.1 mL) and H$_2$O (1 mL) was added LiOH—H$_2$O (123 mg, 2.94 mmol). The mixture was stirred at 15° C. for 2 hrs. On completion, the mixture was concentrated in vacuo and M HCl was added to the mixture until the pH=5-6 then the mixture was filtered. The filtered cake was dried in vacuo to give the title compound (250 mg, 88% yield) as yellow solid. LC-MS (ESI$^+$) m/z 483.2 (M+1)$^+$.

Step 8—Isopropoxycarbonyl 4-[6-(difluoromethyl)-5-[[6-(trifluoromethyl)pyridine-2-carbonyl] amino] indazol-2-yl]cyclohexanecarboxylate To a solution of 4-[6-(difluoromethyl)-5-[[6-(trifluoromethyl)pyridine-2-carbonyl]amino]indazol-2-yl] cyclohexanecarboxylic acid (100 mg, 207 umol) in THF (1 mL) was added Et$_3$N (83.9 mg, 829 umol) and isopropyl carbonochloridate (63.5 mg, 518 umol). The mixture was stirred at 0° C. for 2 hrs. On completion, the mixture was filtered and the cake was washed with THF (3×5 mL). The organic phase was concentrated in vacuo to give the title compound (100 mg, 85% yield) as yellow oil. LC-MS (ESI$^+$) m/z 569.0 (M+1)$^+$.

Step 9—N-[6-(difluoromethyl)-2-[4-(hydroxymethyl)cyclohexyl]indazol-5-yl]-6-(trifluoromethyl) pyridine-2-carboxamide To a solution of isopropoxycarbonyl 4-[6-(difluoromethyl)-5-[[6-(trifluoromethyl)pyridine-2-carbonyl] amino] indazol-2-yl]cyclohexanecarboxylate (100 mg, 175 umol) in THF (10 mL) and H$_2$O (1 mL) was added LiBH$_4$ (23.0 mg, 1.06 mmol). The mixture was stirred at 0° C. for 2 hrs. The mixture was added 10 mL NH$_4$Cl and extracted with EA (3×50 mL). The combined organic layers were washed with 50 mL brine, dried over Na$_2$SO$_4$, filtered and concentrated in vacuo to give the title compound (80.0 mg, 97% yield) as yellow solid. LC-MS (ESI$^+$) m/z 469.0 (M+1)$^+$.

Step 10—N-[6-(difluoromethyl)-2-(4-formylcyclohexyl) indazol-5-yl]-6-(trifluoromethyl) pyridine-2-carboxamide To a solution of N-[6-(difluoromethyl)-2-[4-(hydroxymethyl)cyclohexyl]indazol-5-yl]-6-(trifluoro methyl)pyridine-2-carboxamide (80.0 mg, 170 umol) in DCM (10 mL) was added DMP (108 mg, 256 umol). The mixture was stirred at 15° C. for 2 hrs. On completion, the mixture was added 10 mL sat. Na$_2$S$_2$O$_3$ and 10 mL sat. NaHCO$_3$ and extracted with DCM 150 mL (3×50 mL). The combined organic layers were washed with 100 mL brine, dried over Na$_2$SO$_4$, filtered and the organic phase was concentrated in vacuo to give the title compound (80.0 mg, 95% yield) as yellow solid. LC-MS (ESI$^+$) m/z 467.1 (M+1)$^+$.

3-[4-(7-Azaspiro[3.5]nonan-2-yloxy)-1-oxo-isoindolin-2-yl]piperidine-2,6-dione (Intermediate ALF)

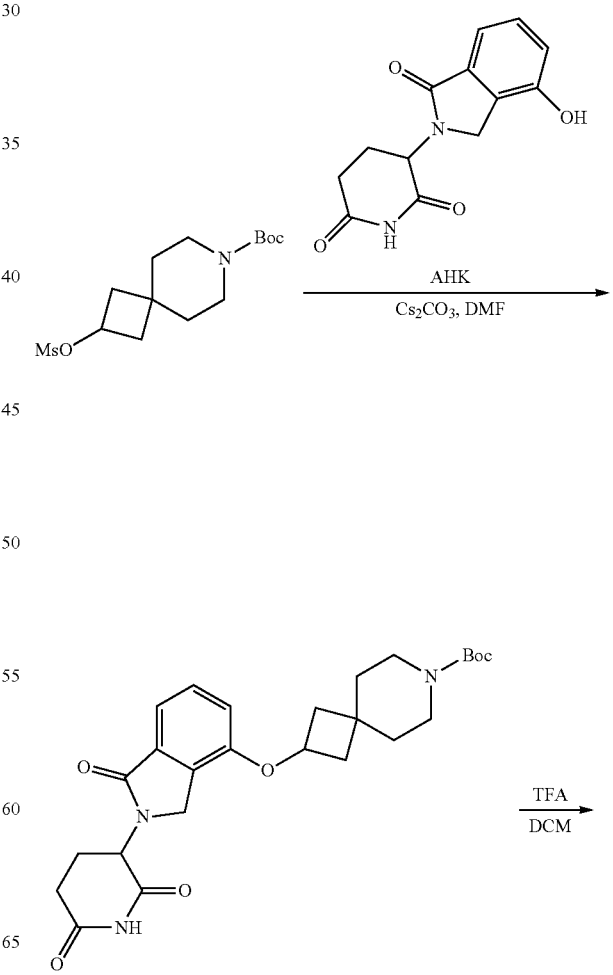

2081
-continued

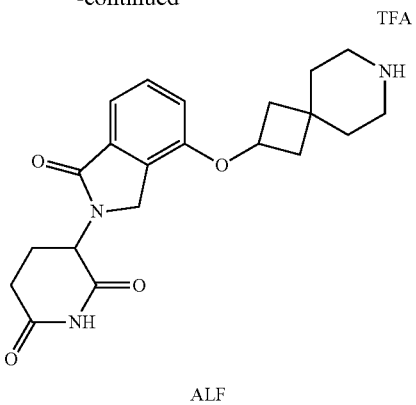

ALF

Step 1—Tert-butyl 2-[2-(2,6-dioxo-3-piperidyl)-1-oxo-isoindolin-4-yl]oxy-7-azaspiro[3.5]nonane-7-carboxylate To a solution of 3-(4-hydroxy-1-oxo-isoindolin-2-yl)piperidine-2,6-dione (100 mg, 384 umol, Intermediate AHK) and tert-butyl 2-methylsulfonyloxy-7-azaspiro[3.5]nonane-7-carboxylate (245 mg, 768 umol, synthesized via Step 1 of Intermediate AJZ) in DMF (10 mL) was added $Cs_2CO_3$ (250 mg, 768 umol) and 4 Å molecular sieves (200 mg, 384 umol) at 25° C. The reaction mixture was stirred at 60° C. for 24 hrs. On completion, the reaction mixture was filtered and the filtrate was concentrated in vacuo to give a residue. The residue was purified by prep-HPLC (column: Phenomenex Synergi C18 150*25*10 um; mobile phase: [water (0.225% FA)-ACN]; B %: 39%-69%, 10 min) to give the title compound (50.0 mg, 26% yield) as a white solid. $^1$H NMR (400 MHz, DMSO-$d_6$) δ 10.97 (s, 1H), 7.49-7.41 (m, 1H), 7.30 (d, J=7.6 Hz, 1H), 7.06 (d, J=8.0 Hz, 1H), 5.10 (dd, J=5.2, 13.2 Hz, 1H), 4.90 (t, J=6.8 Hz, 1H), 4.43-4.33 (m, 1H), 4.27-4.14 (m, 1H), 3.25-3.17 (m, 3H), 2.96-2.82 (m, 1H), 2.62-2.55 (m, 1H), 2.46-2.41 (m, 2H), 2.41-2.34 (m, 1H), 1.99-1.92 (m, 1H), 1.83 (dd, J=6.4, 12.0 Hz, 2H), 1.58-1.45 (m, 5H), 1.38 (s, 9H); LC-MS (ESI$^+$) m/z 484.1 (M+H)$^+$.

Step 2—3-[4-(7-Azaspiro[3.5]nonan-2-yloxy)-1-oxo-isoindolin-2-yl]piperidine-2,6-dione To a solution of tert-butyl 2-[2-(2,6-dioxo-3-piperidyl)-1-oxo-isoindolin-4-yl]oxy-7-azaspiro[3.5] nonane-7-carboxylate (38.0 mg, 78.5 umol) in DCM (4 mL) was added HCl/dioxane (4 M, 2 mL) at 25° C. The mixture was stirred at 25° C. for 2 hrs. On completion, the reaction mixture was concentrated in vacuo to give the title compound (32.0 mg, 96% yield, HCl salt) as a white solid. LC-MS (ESI$^+$) m/z 384.2 (M+H)$^+$.

Tert-butyl 4-(3-bromopropoxy)piperidine-1-carboxylate (Intermediate AUZ)

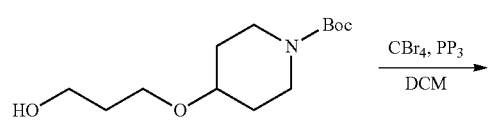

2082
-continued

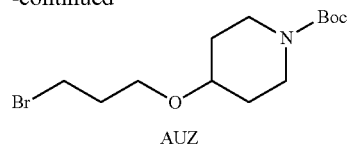

AUZ

To a mixture of tert-butyl 4-(3-hydroxypropoxy)piperidine-1-carboxylate (0.50 g, 1.93 mmol, synthesized via Steps 1-2 of ADK) and $PPh_3$ (1.52 g, 5.78 mmol) in DCM (10 mL) was added $CBr_4$ (1.92 g, 5.78 mmol) at 0° C. The reaction mixture was stirred at 25° C. for 12 hours. On completion, the reaction mixture was concentrated in vacuo. The residue was purified by column chromatography to give the title compound (160 mg, 25% yield) as colorless oil. $^1$H NMR (400 MHz, CDCl$_3$) δ 3.78-3.69 (m, 2H), 3.59 (t, J=5.6 Hz, 2H), 3.53 (t, J=6.4 Hz, 2H), 3.50-3.42 (m, 1H), 3.17-3.07 (m, 2H), 2.15-2.04 (m, 2H), 1.87-1.77 (m, 2H), 1.57-1.48 (m, 2H), 1.46 (s, 9H).

3-[1-Oxo-4-[3-(4-piperidyloxy)propylamino]isoindolin-2-yl]piperidine-2,6-dione (Intermediate AVA)

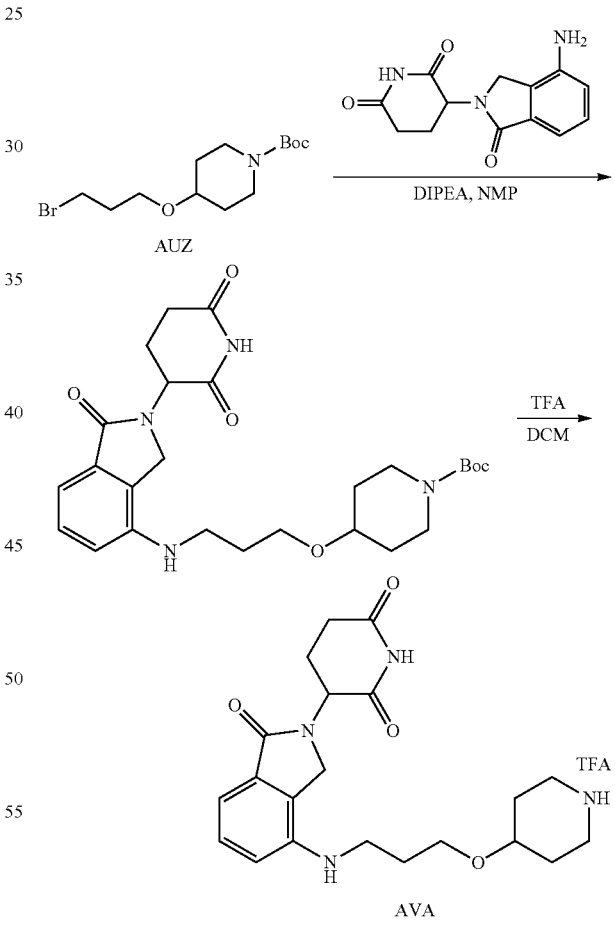

Step 1—Tert-butyl 4-[3-[[2-(2,6-dioxo-3-piperidyl)-1-oxo-isoindolin-4-yl]amino]propoxy]piperidine-1-carboxylate To a mixture of tert-butyl 4-(3-bromopropoxy)piperidine-1-carboxylate (124 mg, 385 umol, Intermediate AUZ) and 3-(4-amino-1-oxo-isoindolin-2-yl)piperidine-2,6-dione (100 mg, 385.71 umol, CAS #191732-72-6) in NMP (3 mL) was added DIPEA (149 mg, 1.16 mmol, 201 uL). The reaction mixture was stirred at 100° C. for 12 hours. The reaction mixture was concentrated in vacuo. The residue was purified by reverse phase (0.1% FA condition) to give the title compound (75.0 mg, 38% yield) as brown solid. $^1$H NMR (400 MHz, DMSO-$d_6$) δ 11.00 (s, 1H), 7.28 (t, J=7.6 Hz, 1H), 6.93 (d, J=7.4 Hz, 1H), 6.76 (d, J=8.0 Hz, 1H), 5.58 (t, J=5.6 Hz, 1H), 5.14-5.08 (m, 1H), 4.26-4.09 (m, 2H), 3.64-3.58 (m, 2H), 3.52 (t, J=6.0 Hz, 2H), 3.45-3.41 (m, 1H), 3.22-3.15 (m, 2H), 3.07-2.98 (m, 2H), 2.96-2.86 (m, 1H), 2.65-2.57 (m, 1H), 2.56-2.52 (m, 1H), 2.35-2.24 (m, 1H), 2.09-1.98 (m, 1H), 1.80-1.75 (m, 3H), 1.38 (s, 9H), 1.35-1.29 (m, 2H); LC-MS (ESI$^+$) m/z 401.3 (M−100+H)$^+$.

Step 2—3-[1-Oxo-4-[3-(4-piperidyloxy)propylamino]isoindolin-2-yl]piperidine-2,6-dione To a mixture of tert-butyl 4-[3-[[2-(2,6-dioxo-3-piperidyl)-1-oxo-isoindolin-4-yl]amino]propoxy] piperidine-1-carboxylate (70.0 mg, 139 umol) in DCM (2 mL) was added TFA (3.08 g, 27.0 mmol, 2 mL). The reaction mixture was stirred at 25° C. for 0.5 hour. On completion, the reaction mixture was concentrated in vacuo to give the title compound (71.0 mg, 98% yield, TFA) as light yellow oil. LC-MS (ESI$^+$) m/z 401.3 (M+H)$^+$.

Benzyl N-[2-(aminomethyl)spiro[3.5]nonan-7-yl]-N-methyl-carbamate (Intermediate ANJ)

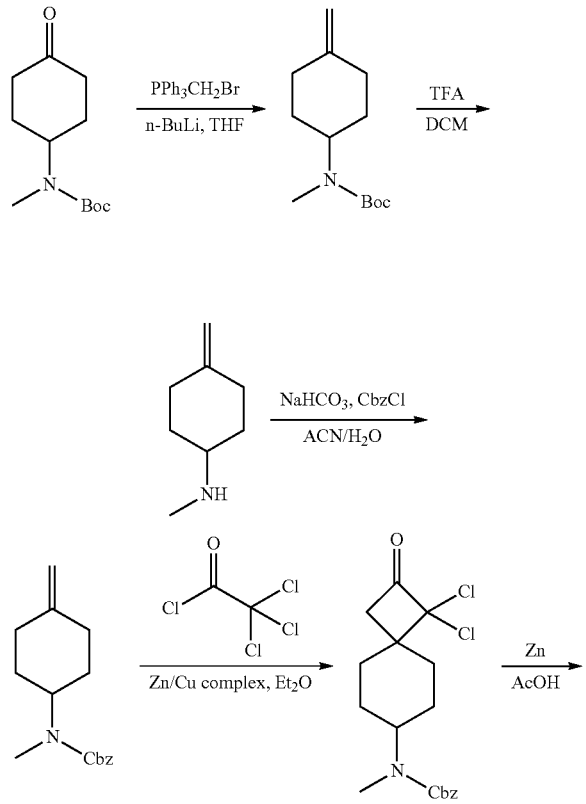

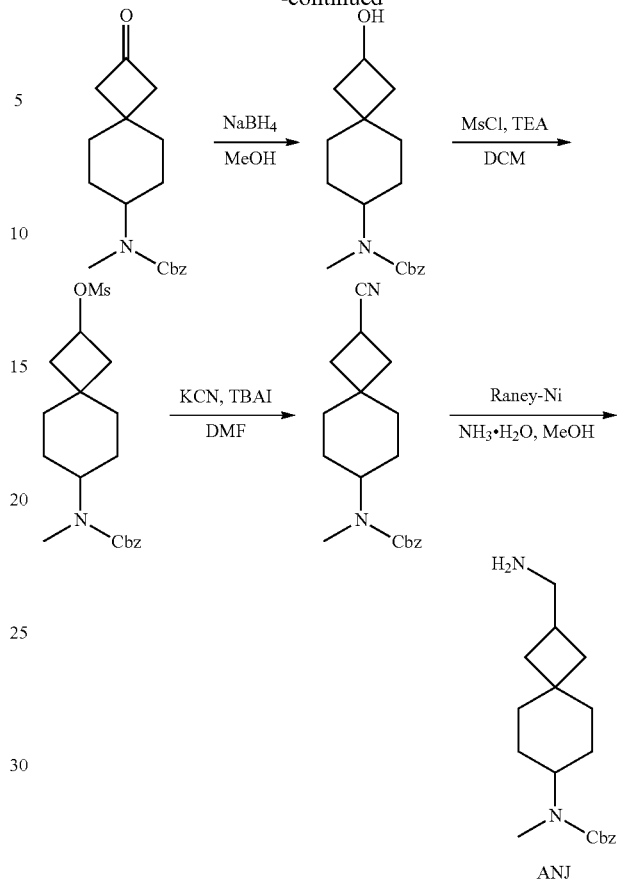

Step 1—Tert-butyl N-methyl-N-(4-methylenecyclohexyl)carbamate

A solution of n-BuLi (2.5 M, 66.0 mL) was added to a mixture of methyltriphenylphosphonium bromide (58.9 g, 165 mmol) in tetrahydrofuran (200 mL) at −10° C. After stirring for 30 min at −10° C., the yellow suspension was cooled to −78° C. and a solution of tert-butyl N-methyl-N-(4-oxocyclohexyl)carbamate (25.0 g, 110 mmol, CAS #400899-84-5) in tetrahydrofuran (100 mL) was added. After stirring for 10 min at −78° C., the reaction mixture was warmed to 25° C. slowly and stirred for 3 hrs. On completion, the reaction mixture was quenched with saturated ammonium chloride (20 mL), then extracted with ethyl acetate (3×100 mL). The combined organic layers were washed with brine (100 mL), dried over anhydrous sodium sulfate, filtered and the filtrate was concentrated in vacuo. The residue was purified by column chromatography (Petroleum ether/Ethyl acetate=40/1) to give the title compound (23.7 g, 96% yield) as a white solid. $^1$H NMR (400 MHz, CDCl$_3$) δ 4.66 (s, 2H), 4.33-3.94 (m, 1H), 2.72 (s, 3H), 2.47-2.32 (m, 2H), 2.24-2.10 (m, 2H), 1.84-1.75 (m, 2H), 1.54-1.49 (m, 2H), 1.48 (m, 9H).

Step 2—N-methyl-4-methylene-cyclohexanamine

To a solution of tert-butyl N-methyl-N-(4-methylenecyclohexyl)carbamate (5.00 g, 22.2 mmol) in DCM (10 mL) was added tertfluoroacetic acid (7.70 g, 67.5 mmol, 5.00 mL). The reaction mixture was stirred at 20° C. for 2 hrs. On completion, the reaction mixture was concentrated in vacuo to give the title compound (5.31 g, 100% yield, TFA salt) as colorless oil. The product was unstable which was used for the next step without purification. $^1$H NMR (400 MHz, CDCl$_3$) δ 4.77 (s, 2H), 3.27-3.06 (m, 1H), 2.76-2.73 (m, 3H), 2.50-2.42 (m, 2H), 2.22-2.05 (m, 4H), 1.58-1.50 (m, 2H).

Step 3—Benzyl N-methyl-N-(4-methylenecyclohexyl)carbamate

To a solution of N-methyl-4-methylene-cyclohexanamine (5.31 g, 22.2 mmol, TFA salt) and NaHCO$_3$ (6.53 g, 77.7 mmol, 3.02 mL) in a mixed solvent of ACN (50 mL) and H$_2$O (50 mL) was added CbzCl (5.68 g, 33.3 mmol, 4.73 mL). The reaction mixture was stirred at 25° C. for 12 hrs. On completion, the reaction mixture was concentrated in vacuo to remove ACN, and extracted with ethyl acetate (2×100 mL). The combined organic layer was washed with brine (20 mL), dried over anhydrous sodium sulfate, filtered and concentrated in vacuo. The residue was purified by silica gel chromatography (petroleum ether:ethyl acetate=50:1) to give the title compound (4.00 g, 68% yield) as a colorless oil. $^1$H NMR (400 MHz, CDCl$_3$) δ 7.42-7.28 (m, 5H), 5.15 (s, 2H), 4.66 (t, J=1.6 Hz, 2H), 4.33-4.01 (m, 1H), 2.79 (s, 3H), 2.37-2.34 (m, 2H), 2.18-2.15 (m, 2H), 1.87-1.73 (m, 2H), 1.57-1.48 (m, 2H). LC-MS (ESI$^+$) m/z 260.2 (M+H)$^+$.

Step 4—Benzyl N-(3,3-dichloro-2-oxo-spiro[3.5] nonan-7-yl)-N-methyl-carbamate

To a solution of benzyl N-methyl-N-(4-methylenecyclohexyl)carbamate (3.50 g, 13.5 mmol) in diethyl ether (70 mL) was added Zn/Cu complex (7 g). Then a mixture of 2,2,2-trichloroacetyl chloride (7.36 g, 40.5 mmol, 4.52 mL) in diethyl ether (140 mL) was added dropwise. The reaction mixture was stirred at 30° C. for 16 hrs. On completion, the reaction mixture was poured into saturated NaHCO$_3$ aqueous solution (100 mL) and filtered through a pad of Celite and the filtrate was collected. The organic layer was dried over anhydrous Na$_2$SO$_4$ and concentrated in vacuo to get a residue. The residue was purified by silica gel chromatography (petroleum ether/ethyl acetate=5/1) to give the title compound (3.80 g, 76% yield) as a white solid. $^1$H NMR (400 MHz, CDCl$_3$) δ 7.35-7.21 (m, 5H), 5.08 (s, 2H), 4.19-4.02 (m, 1H), 2.93 (s, 2H), 2.76 (s, 3H), 2.37-2.26 (m, 2H), 1.86-1.62 (m, 6H). LC-MS (ESI$^+$) m/z 370.0 (M+H)$^+$.

Step 5—Benzyl N-methyl-N-(2-oxospiro[3.5] nonan-7-yl)carbamate

To a solution of benzyl N-(3,3-dichloro-2-oxo-spiro[3.5] nonan-7-yl)-N-methyl-carbamate (3.30 g, 8.91 mmol) in acetic acid (10 mL) was added Zn (2.33 g, 35.6 mmol) at 15° C. The reaction mixture was stirred at 80° C. for 3 hrs. On completion, the reaction mixture was filtered and the filtrate was diluted with water (50 mL), then extracted with ethyl acetate (3×50 mL). The combined organic layers were washed saturated NaHCO$_3$ (30 mL) and brine (30 mL), dried over anhydrous sodium sulfate, filtered and concentrated in vacuo to give the title compound (2.40 g, 89% yield) as a gum oil. $^1$H NMR (400 MHz, CDCl$_3$) δ 7.46-7.28 (m, 5H), 5.15 (s, 2H), 4.20-3.84 (m, 1H), 2.90-2.68 (m, 7H), 1.86-1.68 (m, 6H), 1.55-1.42 (m, 2H); LC-MS (ESI$^+$) m/z 302.2 (M+H)$^+$.

Step 6—Benzyl N-(2-hydroxyspiro[3.5]nonan-7-yl)-N-methyl-carbamate

To a solution of benzyl N-methyl-N-(2-oxospiro[3.5] nonan-7-yl)carbamate (1.00 g, 3.32 mmol) in MeOH (10 mL) was added NaBH$_4$ (151 mg, 3.98 mmol) at 0° C., and the mixture was stirred at 25° C. for 1 h. On completion, the reaction mixture was quenched with water (5 mL). The mixture was concentrated in vacuo to remove methanol, then the solution was extracted with ethyl acetate (3×20 mL). The combined organic layers were washed with brine (10 mL), dried over anhydrous sodium sulfate, filtered and the filtrate was concentrated in vacuo to give the title compound (1.00 g, 99% yield) as a yellow oil. $^1$H NMR (400 MHz, CDCl$_3$) δ 7.44-7.28 (m, 5H), 5.14 (s, 2H), 4.28 (q, J=7.2 Hz, 1H), 4.05-3.75 (m, 1H), 2.79 (s, 3H), 2.40-2.27 (m, 1H), 2.22-2.11 (m, 1H), 1.71-1.64 (m, 3H), 1.62-1.51 (m, 4H), 1.48-1.46 (m, 3H); LC-MS (ESI$^+$) m/z 304.1 (M+H)$^+$.

Step 7—[7-[Benzyloxycarbonyl(methyl)amino]spiro [3.5]nonan-2-yl]methanesulfonate To a solution of benzyl N-(2-hydroxyspiro[3.5]nonan-7-yl)-N-methyl-carbamate (1.00 g, 3.30 mmol) in DCM (20 mL) was added TEA (1.00 g, 9.89 mmol, 1.38 mL) and MsCl (566 mg, 4.94 mmol, 383 uL) at 0° C. The reaction mixture was stirred at 20° C. for 3 hrs. On completion, the reaction mixture was quenched with water (10 mL). The organic layer was separated and washed with brine (50 mL), dried over anhydrous sodium sulfate, filtered and concentrated in vacuo to give the title compound (1.26 g, 100% yield) as yellow oil. $^1$H NMR (400 MHz, CDCl$_3$) δ 7.42-7.28 (m, 5H), 5.13 (s, 2H), 5.01-4.97 (m, 1H), 4.05-3.74 (m, 1H), 2.98 (s, 3H), 2.78 (s, 3H), 2.45 (m, 1H), 2.34-2.21 (m, 1H), 2.11-2.06 (m, 1H), 2.02-1.97 (m, 1H), 1.74-1.67 (m, 2H), 1.59-1.36 (m, 6H). LC-MS (ESI$^+$) m/z 382.1 (M+H)$^+$.

Step 8—Benzyl N-(2-cyanospiro[3.5]nonan-7-yl)-N-methyl-carbamate

To a solution of [7-[benzyloxycarbonyl(methyl)amino] spiro[3.5]nonan-2-yl]methanesulfonate (1.26 g, 3.30 mmol) in DMF (10 mL) was added KCN (430 mg, 6.61 mmol, 283 uL) and TBAI (122 mg, 330 umol). The reaction mixture was heated to 120° C. for 16 hrs. On completion, the reaction mixture was diluted with water (10 mL), and extracted with ethyl acetate (3×50 mL). The combined organic layers were wash with brine (30 mL), dried over anhydrous sodium sulfate, filtered and the filtrate was concentrated in vacuo. The residue was purified by silica gel chromatography (petroleum ether/ethyl acetate=4/1) to give the title compound (570 mg, 55% yield) as a yellow oil. $^1$H NMR (400 MHz, CDCl$_3$) δ 7.45-7.28 (m, 5H), 5.13 (s, 2H), 4.07-3.73 (m, 1H), 3.06-2.98 (m, 1H), 2.78 (s, 3H), 2.32-2.22 (m, 1H), 2.20-2.06 (m, 3H), 1.96-1.87 (m, 1H), 1.82-1.78 (m, 1H), 1.62-1.59 (m, 2H), 1.54-1.36 (m, 4H). LC-MS (ESI$^+$) m/z 313.1 (M+H)$^+$.

Step 9—Benzyl N-[2-(aminomethyl)spiro[3.5] nonan-7-yl]-N-methyl-carbamate

To a solution of benzyl N-(2-cyanospiro[3.5]nonan-7-yl)-N-methyl-carbamate (370 mg, 1.18 mmol) in MeOH (5 mL) was added Raney-Ni (101 mg, 1.18 mmol), NH$_3$.H$_2$O (3.37 g, 31.7 mmol, 3.70 mL, 33% solution) under N$_2$. The suspension was degassed under vacuum and purged with H$_2$ several times. The mixture was stirred under $H_2$ (50 psi) at 25° C. for 4 hours. On completion, the reaction mixture was filtered and concentrated in vacuo to give the title compound (300 mg, 84% yield) as colorless oil. $^1$H NMR (400 MHz, CDCl$_3$) δ 7.47-7.29 (m, 5H), 5.15 (s, 2H), 4.89-4.50 (m, 2H), 4.04-3.78 (m, 1H), 2.79 (s, 3H), 2.69 (d, J=7.2 Hz, 2H), 2.28-2.20 (m, 1H), 2.02-1.73 (m, 6H), 1.48-1.31 (m, 6H); LC-MS (ESI$^+$) m/z 317.1 (M+H)$^+$.

2-(2,6-Dioxo-3-piperidyl)-4-[[7-(methylamino)spiro [3.5]nonan-2-yl]methylamino] isoindoline-1,3-dione (Intermediate ANK)

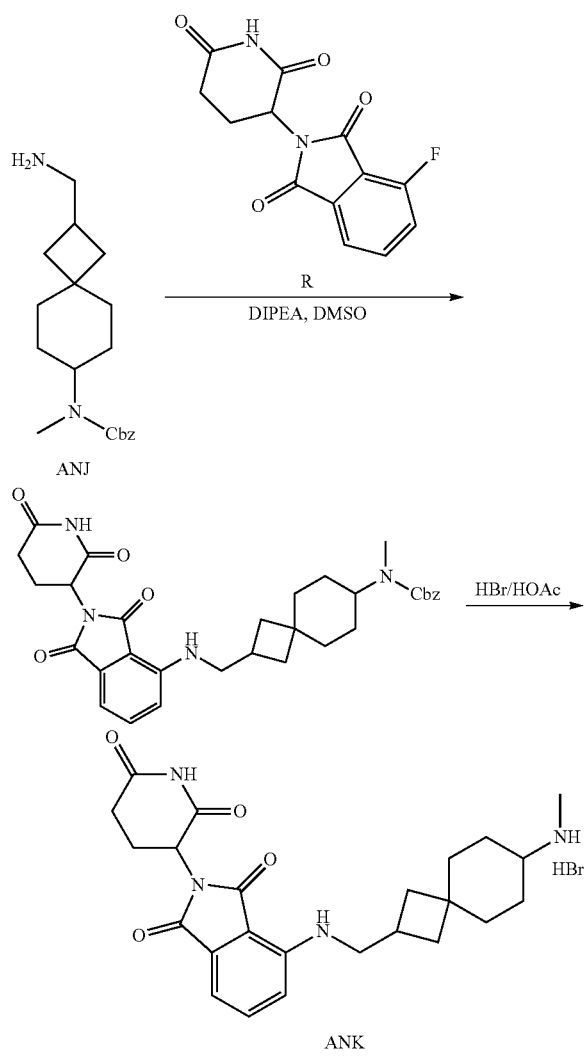

Step 1—Benzyl N-[2-[[[2-(2,6-dioxo-3-piperidyl)-1,3-dioxo-isoindolin-4-yl]amino]methyl]spiro[3.5] nonan-7-yl]-N-methyl-carbamate To a solution of benzyl N-[2-(aminomethyl)spiro[3.5] nonan-7-yl]-N-methyl-carbamate (300 mg, 948 umol, Intermediate ANJ) and 2-(2,6-dioxo-3-piperidyl)-4-fluoro-isoindoline-1,3-dione (262 mg, 948 umol, Intermediate R) in DMSO (5 mL) was added DIPEA (367 mg, 2.84 mmol). The reaction mixture was stirred at 90° C. for 3 hrs. On completion, the reaction mixture was acidified to pH=6 with formic acid (0.1 mL). The mixture was filtered and the filtrate was purified by reverse phase flash (0.1% FA condition) to give the title compound (100 mg, 18% yield) as a yellow solid. $^1$H NMR (400 MHz, CDCl$_3$) δ 7.88 (s, 1H), 7.46-7.40 (m, 1H), 7.31-7.24 (m, 5H), 7.02 (d, J=7.2 Hz, 1H), 6.80 (d, J=8.8 Hz, 1H), 6.11 (t, J=5.2 Hz, 1H), 5.06 (s, 2H), 4.84 (dd, J=5.2, 12.8 Hz, 1H), 3.99-3.66 (m, 1H), 3.32-3.11 (m, 2H), 2.85-2.65 (m, 6H), 2.53-2.41 (m, 1H), 2.10-2.01 (m, 1H), 1.89-1.74 (m, 2H), 1.61-1.52 (m, 2H), 1.46-1.33 (m, 8H). LC-MS (ESI$^+$) m/z 573.1 (M+H)$^+$.

Step 2—2-(2,6-Dioxo-3-piperidyl)-4-[[7-(methylamino)spiro[3.5]nonan-2-yl]methylamino] isoindoline-1,3-dione A mixture of benzyl N-[2-[[[2-(2,6-dioxo-3-piperidyl)-1,3-dioxo-isoindolin-4-yl]amino]methyl] spiro[3.5]nonan-7-yl]-N-methyl-carbamate (50 mg, 87.3 umol) in HBr/HOAc (1 mL) was degassed and purged with $N_2$ for 3 times, and then the mixture was stirred at 25° C. for 12 hrs under $N_2$ atmosphere. On completion, the reaction mixture was concentrated in vacuo to give the title compound (45 mg, 99% yield, HBr salt) as a white solid. LC-MS (ESI$^+$) m/z 439.2 (M+H)$^+$.

Tert-butyl (2R)-2-(3-aminopropoxymethyl)morpholine-4-carboxylate (Intermediate ALI)

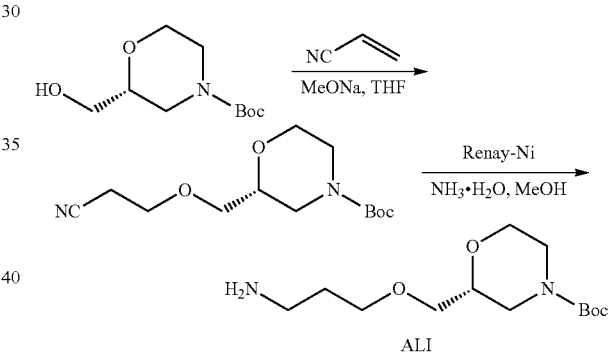

Step 1—Tert-butyl (2R)-2-(2-cyanoethoxymethyl) morpholine-4-carboxylate

To a mixture of tert-butyl (2R)-2-(hydroxymethyl)morpholine-4-carboxylate (2.00 g, 9.21 mmol, CAS #135065-71-3) and CH$_3$ONa (49.7 mg, 920 umol) in THF (20 mL) was added prop-2-enenitrile (1.47 g, 27.6 mmol, CAS #107-13-1). The reaction mixture was stirred at 20° C. for 2 hours under nitrogen atmosphere. On completion, the reaction mixture was diluted with water (60 mL) and extracted with EA (3×30 mL). The organic layer was dried over anhydrous sodium sulfate and filtered. The filtrated was concentrated in vacuo to give the title compound (2.40 g, 96% yield) as colourless oil. $^1$H NMR (400 MHz, CDCl$_3$) δ 4.05-3.77 (m, 3H), 3.73 (t, J=6.4 Hz, 2H), 3.63-3.49 (m, 4H), 3.02-2.68 (m, 2H), 2.63 (t, J=6.4 Hz, 2H), 1.47 (s, 9H).

Step 2—Tert-butyl (2R)-2-(3-aminopropoxymethyl) morpholine-4-carboxylate

To a mixture of tert-butyl (2R)-2-(2-cyanoethoxymethyl) morpholine-4-carboxylate (500 mg, 1.85 mmol) in MeOH (20 mL) was added NH₃·H₂O (108.04 mg, 924 umol, 30% solution) and Raney-Ni (316 mg, 3.70 mmol). The reaction mixture was stirred at 20° C. for 3 hours under H₂ (50 Psi). On completion, the reaction mixture was filtered. The filtrated was concentrated in vacuo to give the title compound (500 mg, 98% yield) as colourless oil. ¹H NMR (400 MHz, CDCl₃) δ 4.06-3.73 (m, 3H), 3.60-3.41 (m, 6H), 3.03-2.87 (m, 1H), 2.79 (t, J=6.8 Hz, 2H), 2.75-2.62 (m, 1H), 1.79-1.69 (m, 2H), 1.47 (s, 9H).

2-(2,6-dioxo-3-piperidyl)-4-[3-[[(2R)-morpholin-2-yl]methoxy]propylamino]isoindoline-1,3-dione (Intermediate ALJ)

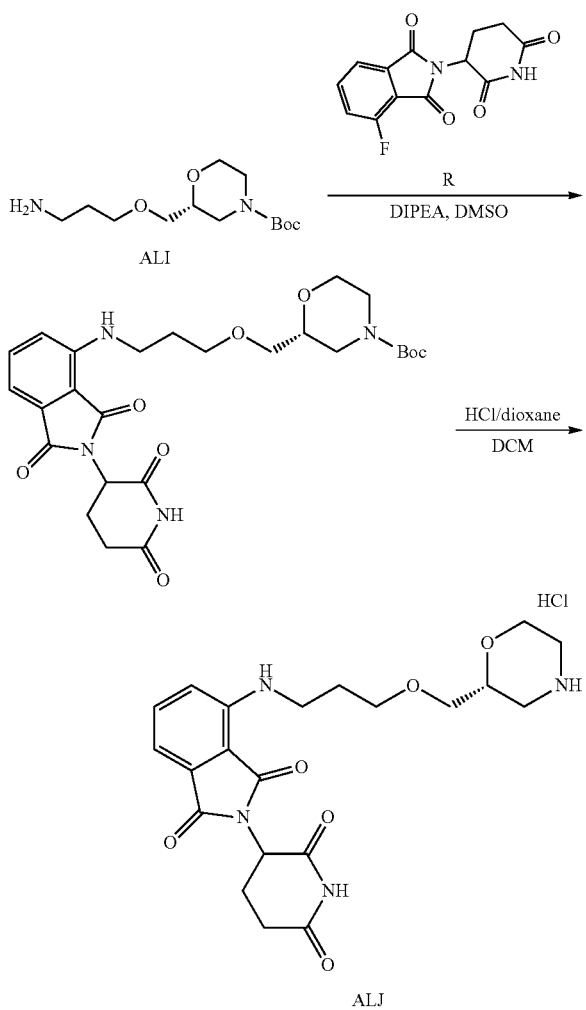

Step 1—Tert-butyl (2R)-2-[3-[[2-(2,6-dioxo-3-piperidyl)-1,3-dioxo-isoindolin-4-yl]amino]propoxy methyl]morpholine-4-carboxylate The mixture of 2-(2,6-dioxo-3-piperidyl)-4-fluoro-isoindoline-1,3-dione (100 mg, 362 umol, Intermediate R) and tert-butyl (2R)-2-(3-aminopropoxymethyl)morpholine-4-carboxylate (99.3 mg, 362 umol, Intermediate ALI) in DMSO (2 mL) was added DIPEA (233 mg, 1.81 mmol). The reaction mixture was stirred at 130° C. for 2 hours. On completion, the reaction mixture was acidified with 4M HCl/dioxane until the pH=7. The mixture was concentrated in vacuo. The mixture was purified by reversed-phase HPLC (0.1% TFA condition) to give the title compound (130 mg, 67% yield) as yellow solid. ¹H NMR (400 MHz, CDCl₃) δ 8.80-8.15 (m, 1H), 7.53-7.45 (m, 1H), 7.09 (d, J=7.2 Hz, 1H), 6.96-6.88 (m, 1H), 6.63-6.36 (m, 1H), 4.96-4.85 (m, 1H), 3.83 (s, 3H), 3.73-3.31 (m, 9H), 3.01-2.84 (m, 2H), 2.83-2.66 (m, 3H), 2.19-2.10 (m, 1H), 1.96-1.93 (m, 1H), 1.47 (d, J=1.2 Hz, 9H).

Step 2—2-(2,6-Dioxo-3-piperidyl)-4-[3-[[(2R)-morpholin-2-yl]methoxy]propylamino]isoindoline-1,3-dione To a mixture of tert-butyl (2R)-2-[3-[[2-(2,6-dioxo-3-piperidyl)-1,3-dioxo-isoindolin-4-yl]amino] propoxymethyl]morpholine-4-carboxylate (60.0 mg, 113 umol) in DCM (5 mL) was added HCl/dioxane (4 M, 5 mL). The reaction mixture was stirred at 20° C. for 1 hour. On completion, the reaction mixture was concentrated in vacuo to give the title compound (52.5 mg, 99% yield, HCl) as yellow solid. LC-MS (ESI⁺) m/z 431.3 (M+H)⁺.

2-[(2R)-Morpholin-2-yl]acetonitrile (Intermediate ANR)

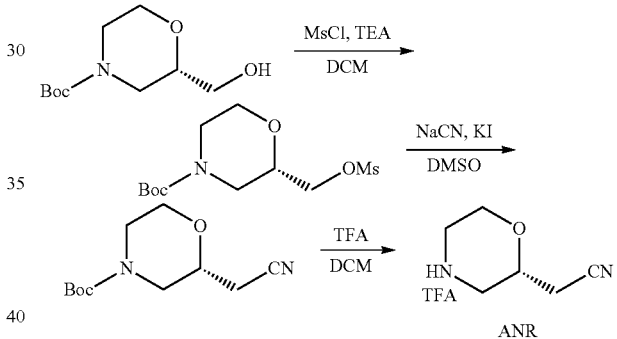

Step 1—Tert-butyl (2S)-2-(methyl sulfonyl oxymethyl)morpholine-4-carboxylate

To a mixture of tert-butyl (2S)-2-(hydroxymethyl)morpholine-4-carboxylate (5.00 g, 23.0 mmol, CAS #135065-76-8) in DCM (50 mL) was added TEA (3.03 g, 29.9 mmol) and MsCl (6.06 g, 52.9 mmol) at 0° C. Then the reaction mixture was stirred at 25° C. for 2 hours. On completion, the reaction mixture was poured into the ice-water (50 mL), and extracted with DCM (2×30 mL). The combined organic phase was washed with brine (2×50 mL), dried over anhydrous Na₂SO₄, filtered and concentrated in vacuo to give the title compound (6.50 g, 95% yield) as a white oil. ¹H NMR (400 MHz, CDCl₃) δ 4.23 (d, J=4.8 Hz, 2H), 3.92-3.85 (m, 3H), 3.69-3.65 (m, 1H), 3.57-3.51 (m, 1H), 3.06 (s, 3H), 3.01-2.95 (m, 1H), 2.82-2.76 (m, 1H), 1.46 (s, 9H).

Step 2—Tert-butyl (2R)-2-(cyanomethyl)morpholine-4-carboxylate

To a mixture of tert-butyl (2S)-2-(methylsulfonyloxymethyl)morpholine-4-carboxylate (6.50 g, 22.0 mmol) in DMSO (80 mL) was added KCN (1.50 g, 23.1 mmol) and KI (5.48 g, 33.0 mmol) at 25° C. The reaction mixture was stirred at 100° C. for 4 hours. On completion, the reaction mixture was poured into the ice-water (50 mL), and extracted with DCM (2×30 mL). The combined organic phase was washed with brine (2×50 mL), dried over anhydrous $Na_2SO_4$, filtered and concentrated in vacuo to give a residue. The residue was purified by column chromatography ($SiO_2$, Petroleum ether/Ethyl acetate=3:1) to give the title compound (2.30 g, 46% yield) as a white solid. $^1$H NMR (400 MHz, $CDCl_3$) δ 4.04-3.83 (m, 3H), 3.62-3.59 (m, 1H), 3.51-3.48 (m, 1H), 2.93-2.90 (m, 1H), 2.68 (m, 1H), 2.50-2.43 (m, 2H), 1.40 (s, 9H).

Step 3—2-[(2R)-Morpholin-2-yl]acetonitrile

To a solution of tert-butyl (2R)-2-(cyanomethyl) morpholine-4-carboxylate (1.00 g, 4.42 mmol) in DCM (6 mL) was added TFA (3 mL) at 25° C. and the mixture was stirred at 25° C. for 1 hour. On completion, the mixture was concentrated in vacuo to give the title compound (1.06 g, 95% yield, TFA) as light yellow gum. $^1$H NMR (400 MHz, DMSO-$d_6$) δ 9.11 (s, 2H), 4.04-4.01 (m, 1H), 4.00-3.91 (m, 1H), 3.79-3.67 (m, 1H), 3.34-3.16 (m, 2H), 3.07-2.89 (m, 2H), 2.87-2.73 (m, 2H).

Tert-butyl N-[2-[(2R)-2-(2-aminoethyl)morpholin-4-yl]ethyl]-N-methyl-carbamate (Intermediate ALD)

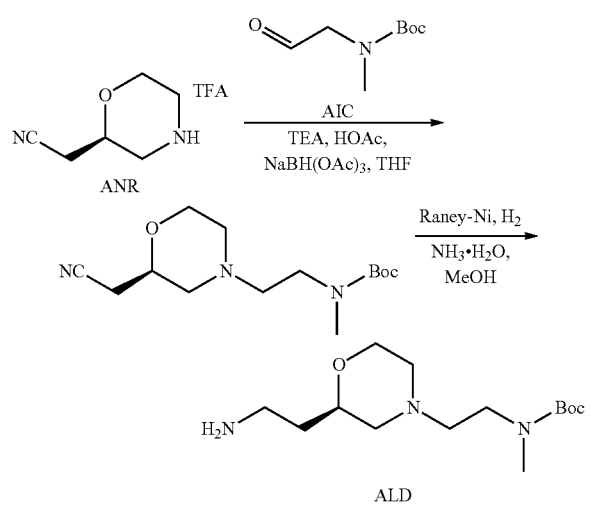

Step 1—Tert-butyl N-[2-[(2R)-2-(cyanomethyl)morpholin-4-yl]ethyl]-N-methyl-carbamate To a mixture of 2-[(2R)-morpholin-2-yl]acetonitrile (0.35 g, 1.46 mmol, TFA, Intermediate ANR) in THF (5 mL) was added TEA (442 mg, 4.37 mmol, q) at −10° C. The mixture was stirred at −10° C. for 0.1 hr. Then, HOAc (262 mg, 4.37 mmol) and tert-butyl N-methyl-N-(2-oxoethyl)carbamate (252 mg, 1.46 mmol, Intermediate AIC) was added. The mixture was stirred at −10° C. for 0.5 hr. After that, NaBH(OAc)$_3$ (463 mg, 2.19 mmol) was added at −10° C. The mixture was stirred at 25° C. for 16 hrs. On completion, the reaction mixture was diluted with water (10 mL) and extracted with EA (4×30 mL). The combined organic lays was dried over $Na_2SO_4$, filtered and concentrated in vacuo to give a residue. The residue was purified by column chromatography ($SiO_2$, Petroleum ether/Ethyl acetate=3/1) to give the title compound (0.22 g, 53% yield) as colorless oil. $^1$H NMR (400 MHz, $CDCl_3$) δ 3.90 (d, J=11.2 Hz, 1H), 3.83-3.74 (m, 1H), 3.67 (t, J=10.4 Hz, 1H), 3.35 (s, 2H), 2.91 (s, 1H), 2.87 (s, 3H), 2.73 (d, J=3.2 Hz, 1H), 2.62-2.44 (m, 4H), 2.29-2.22 (m, 1H), 2.11-2.06 (m, 1H), 1.47 (s, 9H).

Step 2—Tert-butyl N-[2-[(2R)-2-(2-aminoethyl) morpholin-4-yl]ethyl]-N-methyl-carbamate To a solution of tert-butyl N-[2-[(2R)-2-(cyanomethyl) morpholin-4-yl]ethyl]-N-methyl-carbamate (0.2 g, 705 umol) and $NH_3$—$H_2O$ (41.2 mg, 352 umol, 45.3 uL, 30% solution) in MeOH (5 mL) was added Raney-Ni (6.05 mg, 70.5 umol) under $N_2$. The suspension was degassed under vacuum and purged with $H_2$ several times. The mixture was stirred under $H_2$ (50 psi) at 25° C. for 16 hours. On completion, the reaction mixture was concentrated in vacuo to give the title compound (0.17 g, 85% yield) as colorless oil. $^1$H NMR (400 MHz, $CDCl_3$) δ 3.84 (d, J=11.2 Hz, 1H), 3.71-3.50 (m, 2H), 3.32 (dd, J=2.0, 5.2 Hz, 2H), 2.87 (s, 3H), 2.85-2.63 (m, 4H), 2.46 (t, J=6.8 Hz, 2H), 2.25-2.14 (m, 1H), 1.92 (t, J=10.8 Hz, 1H), 1.73-1.60 (m, 2H), 1.46 (s, 9H).

2-(2,6-dioxo-3-piperidyl)-4-[2-[(2R)-4-[2-(methylamino)ethyl]morpholin-2-yl]ethyl amino]isoindoline-1,3-dione (Intermediate ALE)

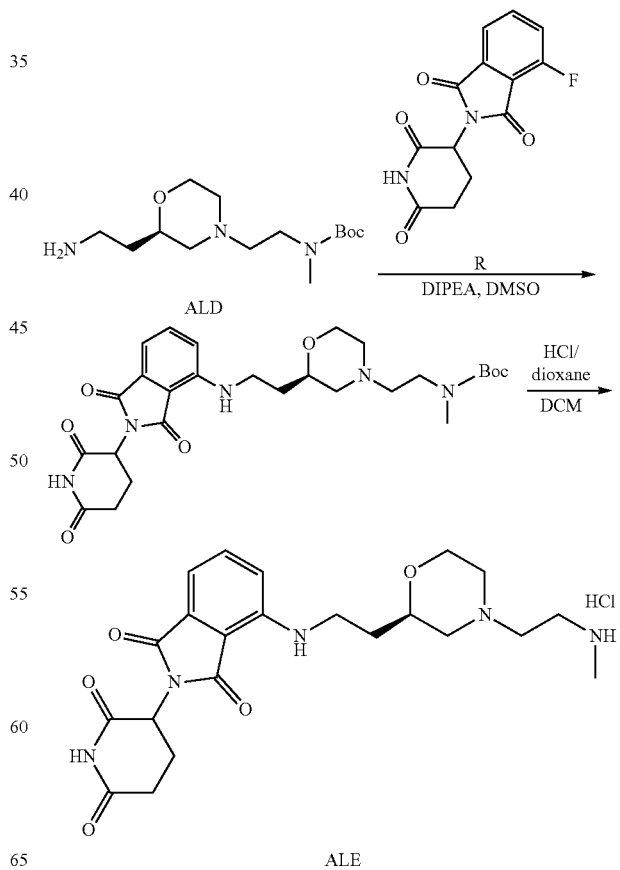

Step 1—Tert-butyl N-[2-[(2R)-2-[2-[[2-(2,6-dioxo-3-piperidyl)-1,3-dioxo-isoindolin-4-yl]amino] ethyl] morpholin-4-yl]ethyl]-N-methyl-carbamate To a solution of tert-butyl N-[2-[(2R)-2-(2-aminoethyl) morpholin-4-yl]ethyl]-N-methyl-carbamate (170 mg, 591 umol, Intermediate ALD) in DMSO (3 mL) was added DIPEA (229 mg, 1.77 mmol) and 2-(2,6-dioxo-3-piperidyl)-4-fluoro-isoindoline-1,3-dione (163 mg, 591 umol, Intermediate R). The reaction mixture was stirred at 130° C. for 3 hrs. On completion, the reaction mixture was diluted with water (15 mL) and extracted with EA (4×20 mL). The combined organic lays was dried over $Na_2SO_4$, filtered and concentrated in vacuo to give a residue. The residue was purified by reverse phase (FA condition) to give the title compound (210 mg, 65% yield) as yellow solid. $^1$H NMR (400 MHz, $CDCl_3$) δ 8.15 (s, 1H), 7.55-7.46 (m, 1H), 7.11 (d, J=7.2 Hz, 1H), 6.91 (d, J=8.4 Hz, 1H), 6.61-6.48 (m, 1H), 4.92 (dd, J=5.2, 12.0 Hz, 1H), 3.99 (s, 3H), 3.55 (s, 2H), 3.45 (d, J=6.4 Hz, 3H), 3.29-3.12 (m, 2H), 2.90 (s, 3H), 2.88-2.82 (m, 2H), 2.81-2.62 (m, 4H), 2.18-2.11 (m, 1H), 1.79 (d, J=6.4 Hz, 2H), 1.46 (s, 9H); LC-MS (ESI$^+$) m/z 544.3 (M+H)$^+$.

Step 2—2-(2,6-Dioxo-3-piperidyl)-4-[2-[(2R)-4-[2-(methylamino)ethyl]morpholin-2-yl]ethylamino] isoindoline-1,3-dione To a solution of tert-butyl N-[2-[(2R)-2-[2-[[2-(2,6-dioxo-3-piperidyl)-1,3-dioxo-isoindolin-4-yl] amino]ethyl]morpholin-4-yl]ethyl]-N-methyl-carbamate (200 mg, 367 umol) in DCM (2 mL) was added HCl/dioxane (4 M, 1.84 mL). The mixture was stirred at 20° C. for 1 hr. On completion, the mixture was concentrated in vacuo to give the title compound (172 mg, 95% yield, HCl salt) as yellow solid. LC-MS (ESI$^+$) m/z 444.1 (M+H)$^+$.

Tert-butyl N-[[4-(hydroxymethyl)phenyl]methyl]-N-methyl-carbamate (Intermediate AMF)

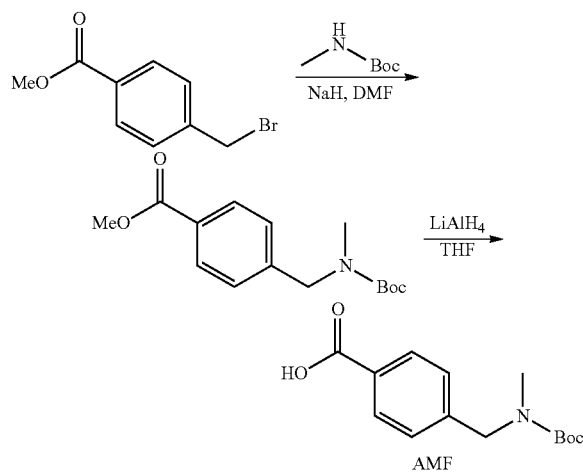

Step 1—Methyl 4-[[tert-butoxycarbonyl(methyl) amino]methyl]benzoate

To a solution of tert-butyl N-methylcarbamate (1.00 g, 7.62 mmol, CAS #16066-84-5) in DMF (15 mL) was added NaH (457 mg, 11.4 mmol, 60% dispersion in mineral oil) at 0° C. After 0.5 hr later, methyl 4-(bromomethyl)benzoate (2.27 g, 9.91 mmol, CAS #2417-72-3) was added and the reaction mixture was stirred at 20° C. for 12 hrs. On completion, the mixture was quenched with water (60 mL), then extracted with EA (2×50 mL). The organic layer was washed with brine (100 mL), concentrated in vacuo. The residue was purified by silica gel chromatography ($SiO_2$) to give the title compound (1.10 g, 52% yield) as colorless oil. $^1$H NMR (400 MHz, $CDCl_3$) δ 8.01 (d, J=8.0 Hz, 2H), 7.29 (d, J=7.6 Hz, 2H), 4.48 (s, 2H), 3.92 (s, 3H), 2.95-2.75 (m, 3H), 1.45 (s, 9H).

Step 2—Tert-butyl N-[[4-(hydroxymethyl)phenyl] methyl]-N-methyl-carbamate

To a suspension of $LiAlH_4$ (224 mg, 5.91 mmol) in THF (10 mL) was added a solution of methyl 4-[[tert-butoxycarbonyl(methyl)amino]methyl]benzoate (1.10 g, 3.94 mmol) in THF (10 mL) dropwise at 0° C. The reaction mixture was stirred at 0° C. for 1 hr. On completion, the mixture was quenched with sat. NaOH (0.23 mL, 15% wt), water (0.23 mL), stirred and dried with $Na_2SO_4$, filtered and the filtrate was concentrated in vacuo to give the title compound (0.94 g, 95% yield) as colourless oil. $^1$H NMR (400 MHz, $CDCl_3$) δ 7.34 (d, J=8.0 Hz, 2H), 7.23 (d, J=6.0 Hz, 2H), 4.70 (d, J=6.0 Hz, 2H), 4.43 (s, 2H), 2.90-2.75 (m, 3H), 1.72 (t, J=5.6 Hz, 1H), 1.49 (s, 9H).

3-[4-r[4-(Methylaminomethyl)phenyl]methoxy]-1-oxo-isoindolin-2-yl]piperidine-2,6-dione (Intermediate AMG)

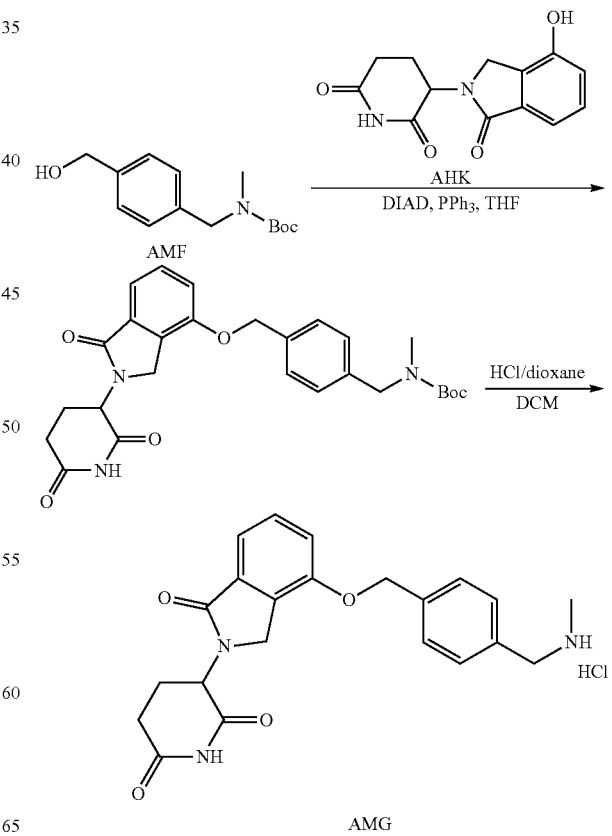

Step 1—Tert-butyl N-[[4-[[2-(2,6-dioxo-3-piperidyl)-1-oxo-isoindolin-4-yl] oxymethyl]phenyl]methyl]-N-methyl-carbamate To a solution of tert-butyl N-[[4-(hydroxymethyl)phenyl]methyl]-N-methyl-carbamate (290 mg, 1.15 mmol, Intermediate AMF), PPh$_3$ (454 mg, 1.73 mmol) and 3-(4-hydroxy-1-oxo-isoindolin-2-yl)piperidine-2,6-dione (300 mg, 1.15 mmol, Intermediate AHK) in THF (3 mL) was added DIAD (467 mg, 2.31 mmol) at 0° C. Then the reaction mixture was stirred at 20° C. for 12 hrs. On completion, the mixture was diluted with water (20 mL), then extracted with EA (50 mL). The organic layer was washed with brine (50 mL), concentrated in vacuo. The residue was purified by reverse phase (0.1% FA) to give the title compound (170 mg, 30% yield) as yellow oil. $^1$H NMR (400 MHz, DMSO-d$_6$) δ 10.96 (s, 1H), 7.50-7.45 (m, 3H), 7.32 (d, J=7.6 Hz, 2H), 7.26-7.20 (m, 2H), 5.23 (s, 2H), 5.11 (dd, J=5.2, 13.2 Hz, 1H), 4.46-4.38 (m, 1H), 4.37 (s, 2H), 4.30-4.21 (m, 1H), 2.97-2.82 (m, 1H), 2.75 (s, 3H), 2.63-2.55 (m, 1H), 2.45-2.35 (m, 2H), 1.47-1.37 (m, 9H).

Step 2—3-[4-[[4-(Methylaminomethyl)phenyl]methoxy]-1-oxo-isoindolin-2-yl]piperidine-2,6-dione To a solution of tert-butyl N-[[4-[[2-(2,6-dioxo-3-piperidyl)-1-oxo-isoindolin-4-yl]oxymethyl]phenyl] methyl]-N-methyl-carbamate (170 mg, 344 umol) in HCl/dioxane (3 mL) was added DCM (6 mL). The reaction mixture was stirred at 20° C. for 1 hr. On completion, the mixture was concentrated in vacuo to give the title compound (140 mg, 95% yield, HCl salt) as a yellow solid. LC-MS (ESI$^+$) m/z 394.2 (M+H)$^+$.

3-[4-[[4-[[Methyl-[2-(methylamino)ethyl] amino]methyl]phenyl]methoxy]-1-oxo-isoindolin-2-yl]piperidine-2,6-dione (Intermediate AMH)

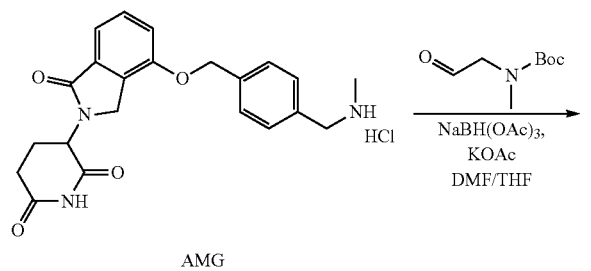

AMG

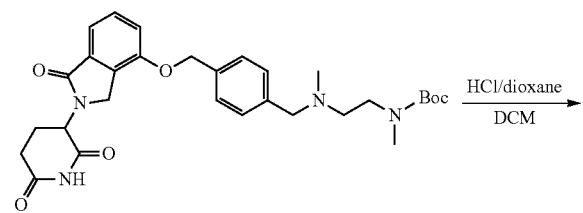

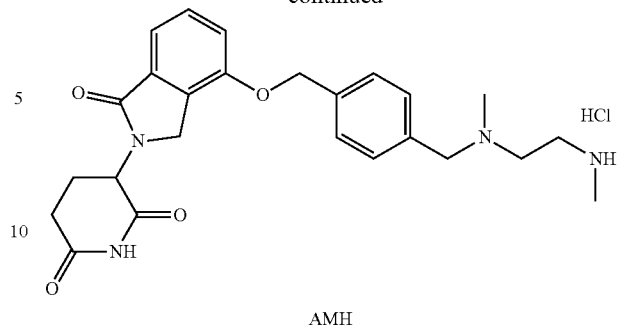

AMH

Step 1—Tert-butyl N-[2-[[4-[[2-(2,6-dioxo-3-piperidyl)-1-oxo-isoindolin-4-yl]oxymethyl]phenyl]methyl-methyl-amino] ethyl]-N-methyl-carbamate To a solution of 3-[4-[[4-(methylaminomethyl)phenyl]methoxy]-1-oxo-isoindolin-2-yl]piperidine-2,6-dione (140 mg, 326 umol, HCl salt, Intermediate AMG) and tert-butyl N-methyl-N-(2-oxoethyl)carbamate (84.6 mg, 488 umol, CAS #123387-72-4) in a mixed solvent of THF (5 mL) and DMF (2 mL) was added KOAc (47.9 mg, 488 umol). Thirty minutes later, NaBH(OAc)$_3$ (138 mg, 651 umol) was added into the above mixture and the reaction mixture was stirred at 25° C. for 12 hrs. On completion, the mixture was quenched with water (0.5 mL), concentrated in vacuo. The residue was purified by reverse phase (0.1% FA condition) to give the title compound (120 mg, 67% yield) as a yellow solid. $^1$H NMR (400 MHz, CDCl$_3$) δ 8.21-7.98 (m, 1H), 7.54-7.49 (m, 1H), 7.46-7.32 (m, 5H), 7.10 (d, J=7.9 Hz, 1H), 5.23 (dd, J=5.2, 13.2 Hz, 1H), 5.14 (s, 2H), 4.53-4.24 (m, 2H), 3.80-3.39 (m, 4H), 2.96-2.89 (m, 2H), 2.85 (s, 3H), 2.74-2.69 (m, 1H), 2.58-2.52 (m, 1H), 2.41-2.27 (m, 4H), 2.25-2.15 (m, 1H), 1.47-1.37 (m, 9H).

Step 2—3-[4-[[4-[[Methyl-[2-(methylamino)ethyl]amino]methyl]phenyl]methoxy]-1-oxo-isoindolin-2-yl]piperidine-2,6-dione To a solution of tert-butyl N-[2-[[4-[[2-(2,6-dioxo-3-piperidyl)-1-oxo-isoindolin-4-yl]oxymethyl] phenyl]methyl-methyl-amino] ethyl]-N-methyl-carbamate (120 mg, 218 umol) in DCM (3 mL) was added HCl/dioxane (3 mL). The reaction mixture was stirred at 20° C. for 1 hr. On completion, the mixture was concentrated in vacuo to give the title compound (100 mg, 94% yield, HCl salt) as a yellow solid. LC-MS (ESI$^+$) m/z 451.2 (M+H)$^+$.

Tert-butyl 2-(aminomethyl)-5-[3-[1-(2,6-dioxo-3-piperidyl)-3-methyl-2-oxo-benzimidazol-4-yl]propoxy]pentanoate (Intermediate AMP)

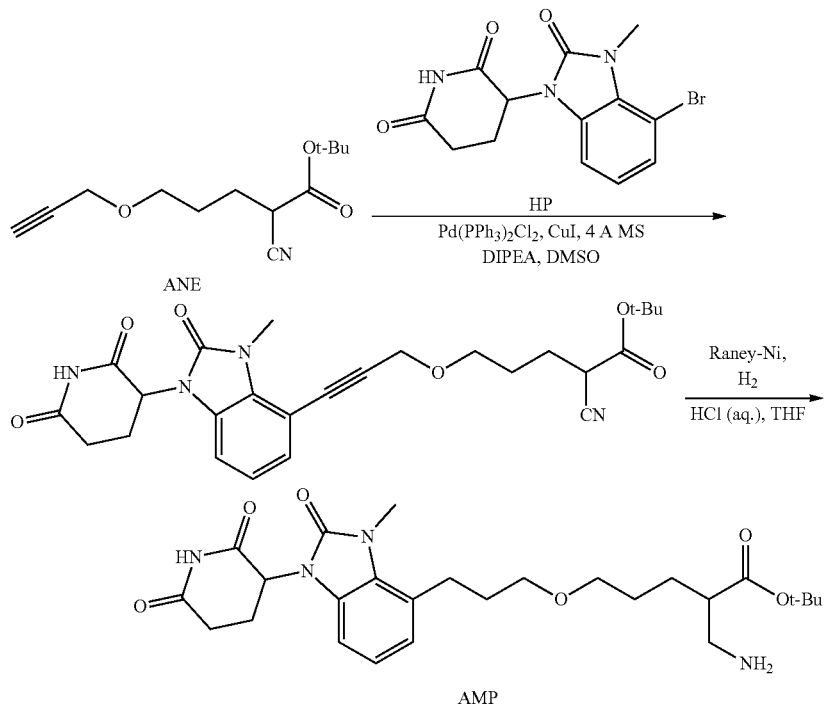

Step 1—Tert-butyl 2-cyano-5-[3-[1-(2,6-dioxo-3-piperidyl)-3-methyl-2-oxo-benzimidazol-4-yl]prop-2-ynoxy]pentanoate A mixture of tert-butyl 2-cyano-5-prop-2-ynoxy-pentanoate (3.52 g, 14.8 mmol, Intermediate ANE), 3-(4-bromo-3-methyl-2-oxo-benzimidazol-1-yl)piperidine-2,6-dione (2.00 g, 5.91 mmol, Intermediate HP), CuI (224 mg, 1.18 mmol), Pd(PPh$_3$)$_2$Cl$_2$ (840 mg, 1.20 mmol), DIPEA (7.72 g, 59.7 mmol) and 4 Å molecular sieves (500 mg) in DMSO (30 mL) was stirred at 80° C. for 2 hours under N$_2$ atmosphere. On completion, the mixture was cooled to 25° C., and diluted with EA (100 mL). The mixture was filtered and the filtrate and washing were combined and concentrated in vacuo. The residue was purified by reversed phase flash (FA condition) to give the title compound (1.65 g, 56% yield) as light yellow solid. $^1$H NMR (400 MHz, DMSO-d$_6$) δ 11.12 (s, 1H), 7.17 (d, J=7.6 Hz, 1H), 7.15-7.09 (m, 1H), 7.07-6.98 (m, 1H), 5.42-5.38 (m, 1H), 4.44 (s, 2H), 4.12-4.09 (m, 1H), 3.64 (s, 3H), 3.58 (t, J=6.0 Hz, 2H), 2.95-2.83 (m, 1H), 2.77-2.60 (m, 2H), 2.09-1.98 (m, 1H), 1.96-1.83 (m, 2H), 1.69-1.64 (m, 2H), 1.43 (s, 9H).

Step 2—Tert-butyl 2-(aminomethyl)-5-[3-[1-(2,6-dioxo-3-piperidyl)-3-methyl-2-oxo-benzimidazol-4-yl]propoxy]pentanoate A mixture of tert-butyl 2-cyano-5-[3-[1-(2,6-dioxo-3-piperidyl)-3-methyl-2-oxo-benzimidazol-4-yl] prop-2-ynoxy]pentanoate (800 mg, 1.62 mmol), aq.HCl (1.0 M, 1.62 mL) and Raney-Ni (300 mg, 3.50 mmol) in THF (20 mL) was stirred at 25° C. for 2 hours under H$_2$ (50 Psi). On completion, the mixture was filtered, and the cake was washed with THF (20 mL). The filtrate was combined and concentrated in vacuo. The residue was purified by reversed phase flash (FA condition) to give the title compound (450 mg, 55% yield) as a light yellow solid. $^1$H NMR (400 MHz, DMSO-d$_6$) δ 8.29 (s, 1H), 6.96 (d, J=4.8 Hz, 2H), 6.90-6.83 (m, 1H), 5.38-5.34 (m, 1H), 3.56 (s, 3H), 3.41 (m, 4H), 3.01-2.87 (m, 4H), 2.69-2.67 (m, 4H), 2.39-2.29 (m, 2H), 2.04-1.95 (m, 1H), 1.83-1.75 (m, 2H), 1.56-1.47 (m, 4H), 1.41 (s, 9H).

Tert-butyl 4-but-3-ynylpiperidine-1-carboxylate (Intermediate AMQ)

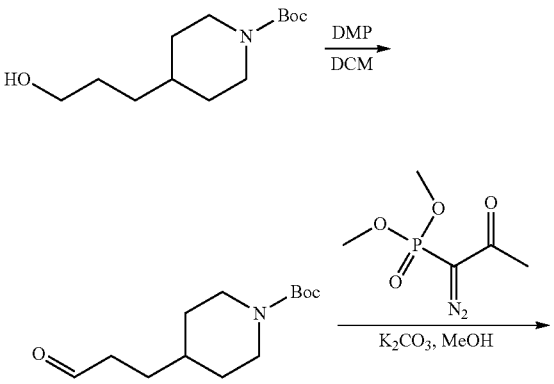

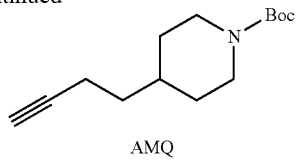

AMQ

Step 1—Tert-butyl 4-(3-oxopropyl)piperidine-1-carboxylate

To a solution of tert-butyl 4-(3-hydroxypropyl)piperidine-1-carboxylate (3.00 g, 12.3 mmol, CAS #156185-63-6) in DCM (30.0 mL) was added DMP (5.75 g, 13.5 mmol) at 0° C. The mixture was stirred at 20° C. for 1 hr. On completion, the reaction mixture was quenched by addition $Na_2S_2O_3$ (20 mL) and $NaHCO_3$ (10 mL), then diluted with DCM (10 mL) and washed with aqueous $NaHCO_3$ (2×30 mL). The organic layers was washed with brine (2×50 mL), dried over $Na_2SO_4$. The organic layers were concentrated in vacuo to give the title compound (2.98 g, 100% yield) as a white oil. $^1$H NMR (400 MHz, $CDCl_3$) δ 9.78 (t, J=1.6 Hz, 1H), 4.12-4.01 (m, 2H), 2.66 (t, J=12.0 Hz, 2H), 2.49-2.45 (m, 2H), 1.65 (d, J=13.2 Hz, 2H), 1.59 (q, J=3.6, 14.8 Hz, 2H), 1.45 (s, 9H), 1.43-1.36 (m, 1H), 1.15-1.04 (m, 2H).

Step 2—Tert-butyl 4-but-3-ynylpiperidine-1-carboxylate

To a solution of 1-diazo-1-dimethoxyphosphoryl-propan-2-one (2.37 g, 12.3 mmol), $K_2CO_3$ (5.12 g, 37.1 mmol) in MeOH (30.0 mL) was added tert-butyl 4-(3-oxopropyl)piperidine-1-carboxylate (2.98 g, 12.3 mmol) at 0° C. The reaction mixture was stirred at 20° C. for 16 hrs. On completion, the reaction mixture was diluted with water (20 mL) and extracted with EA (3×30 mL). The combined organic layers were washed with brine (2×50 mL), dried over anhydrous sodium sulfate, filtered and the concentrated in vacuo. The residue was purified by column chromatography ($SiO_2$, petroleum ether/ethyl acetate=50/1 to 40/1) to give the title compound (1.40 g, 47% yield) as a white oil. $^1$H NMR (400 MHz, $CDCl_3$) δ 4.14-4.01 (m, 2H), 2.69 (t, J=12.0 Hz, 2H), 2.25-2.20 (m, 2H), 1.95 (t, J=2.8 Hz, 1H), 1.67 (d, J=14.8 Hz, 2H), 1.61-1.53 (m, 1H), 1.49 (q, J=7.2 Hz, 14.4 Hz, 1H), 1.46 (s, 9H), 1.16-1.02 (m, 2H).

Tert-butyl 2-(bromomethyl)-7-azaspiro[3.5]nonane-7-carboxylate (Intermediate AMR)

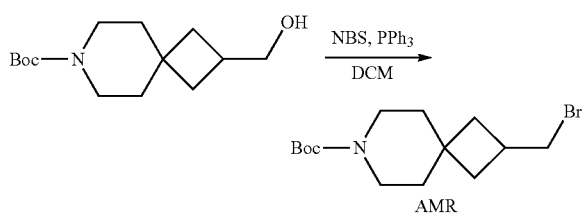

To a solution of tert-butyl 2-(hydroxymethyl)-7-azaspiro[3.5]nonane-7-carboxylate (1 g, 3.92 mmol) (CAS #1356476-27-1) in ACN (20 mL) was added NBS (1.39 g, 7.83 mmol) and $PPh_3$ (2.05 g, 7.83 mmol). The reaction mixture was stirred at 25° C. for 12 hrs under $N_2$. On completion, the reaction mixture was quenched with water (10 mL), and extracted with ethyl acetate (3×30 mL). The combined organic layers were washed with brine (10 mL), dried over anhydrous sodium sulfate, filtered and the filtrate was concentrated in vacuo. The residue was purified by silica gel chromatography (petroleum ether) to give the title compound (1.00 g, 80% yield) as a white solid. $^1$H NMR (400 MHz, $CDCl_3$) δ 3.43 (d, J=7.2 Hz, 2H), 3.38-3.32 (m, 2H), 3.31-3.22 (m, 2H), 2.66 (td, J=8.0, 16.0 Hz, 1H), 2.06-1.94 (m, 2H), 1.61-1.46 (m, 6H), 1.45 (s, 9H).

3-(4-(7-Azaspiro[3.5]nonan-2-ylmethyl)-3-methyl-2-oxo-2,3-dihydro-1H-benzo[d]imidazol-1-yl)piperidine-2,6-dione (Intermediate AMS)

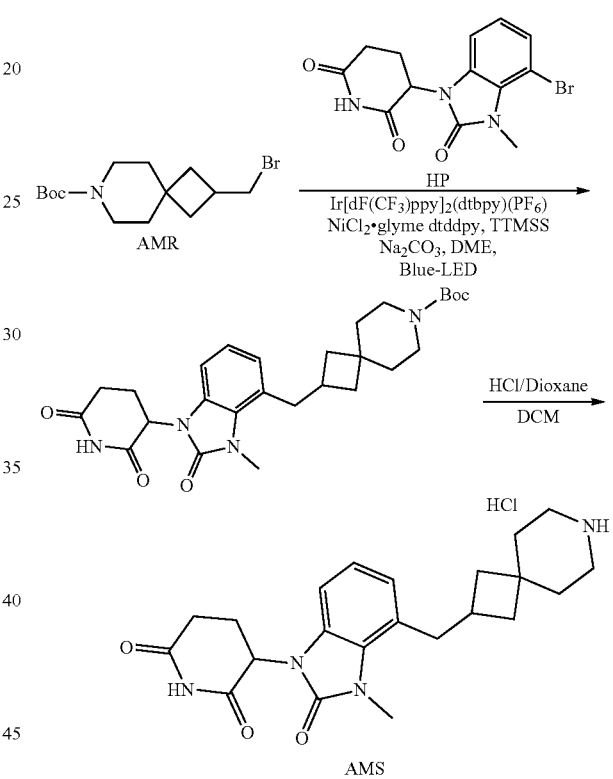

Step 1—Tert-butyl 2-[[1-(2,6-dioxo-3-piperidyl)-3-methyl-2-oxo-benzimidazol-4-yl]methyl]-7-azaspiro[3.5]nonane-7-carboxylate To an 8 mL vial equipped with a stir bar was added 3-(4-bromo-3-methyl-2-oxo-benzimidazol-1-yl)piperidine-2,6-dione (200 mg, 591 umol, Intermediate HP), tert-butyl 2-(bromomethyl)-7-azaspiro[3.5]nonane-7-carboxylate (245 mg, 769 umol, Intermediate AMR), bis[3,5-difluoro-2-[5-(trifluoromethyl)-2-pyridyl]phenyl]iridium(1+); 4-tert-butyl-2-(4-tert-butyl-2-pyridyl)pyridine; hexafluorophosphate (6.64 mg, 5.91 umol), dichloronickel; 1,2-dimethoxyethane (649 ug, 2.96 umol), 4-tert-butyl-2-(4-tert-butyl-2-pyridyl)pyridine (952 ug, 3.55 umol), bis(trimethylsilyl)silyltrimethyl-silane (147.0 mg, 591 umol, 182.47 uL) and $Na_2CO_3$ (125 mg, 1.18 mmol) in DME (6 mL). The vial was sealed and placed under nitrogen was added. The reaction was stirred and irradiated with a 34 W blue LED lamp (7 cm away), with cooling fan to keep the reaction temperature at 25° C. for 14 hrs. On completion, the reaction mixture was concentrated in vacuo. The residue was purified by reversed-phase HPLC (0.1% FA condition) to give the title compound (150 mg, 51% yield) as a white solid. $^1$H NMR (400 MHz, CDCl$_3$) δ 8.24 (s, 1H), 7.02-6.94 (m, 1H), 6.85 (d, J=7.6 Hz, 1H), 6.67 (d, J=7.6 Hz, 1H), 5.26-5.16 (m, 1H), 3.66 (s, 3H), 3.39-3.24 (m, 4H), 3.05 (d, J=7.2 Hz, 2H), 3.00-2.68 (m, 3H), 2.57 (td, J=8.0, 16.0 Hz, 1H), 2.26-2.18 (m, 1H), 2.04-1.96 (m, 2H), 1.60-1.47 (m, 6H), 1.45 (s, 9H). LC-MS (ESI$^+$) m/z 497.2 (M+H)$^+$.

Step 2—3-(4-(7-Azaspiro[3.5]nonan-2-ylmethyl)-3-methyl-2-oxo-2,3-dihydro-1H-benzo[d]imidazol-1-yl)piperidine-2,6-dione To a solution of tert-butyl 2-[[1-(2,6-dioxo-3-piperidyl)-3-methyl-2-oxo-benzimidazol-4-yl]methyl]-7-azaspiro[3.5]nonane-7-carboxylate (80 mg, 161 umol) in DCM (5 mL) was added HCl/dioxane (4 M, 3 mL). The reaction mixture was stirred at 20° C. for 2 hrs. On completion, the reaction mixture was concentrated in vacuo to give the title compound (69.0 mg, 99% yield, HCl salt) as a white solid. LC-MS (ESI$^+$) m/z 397.1 (M+H)$^+$.

N-[3-(difluoromethyl)-1-(4-formylphenyl)pyrazol-4-yl]-5-[(1R,4R)-2-oxa-5-azabicyclo[2.2.1] heptan-5-yl]pyrazolo[1,5-a]pyrimidine-3-carboxamide (Intermediate AMT)

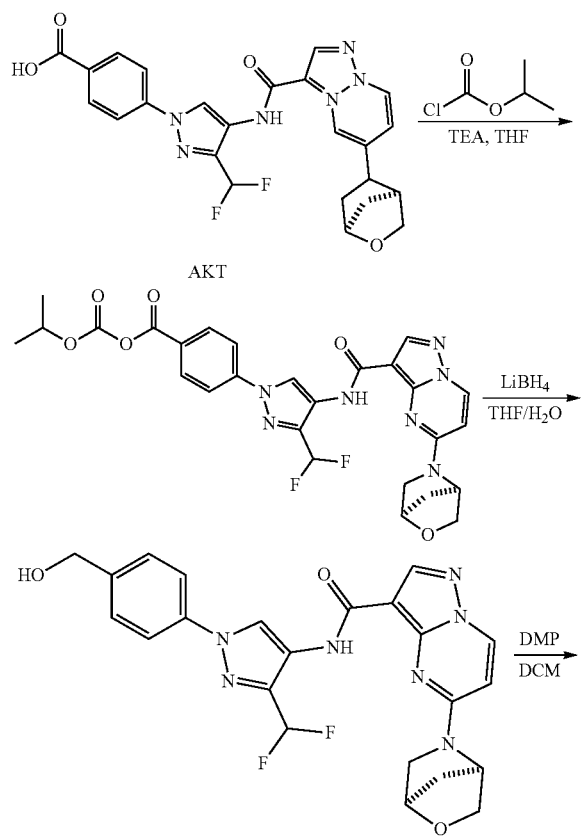

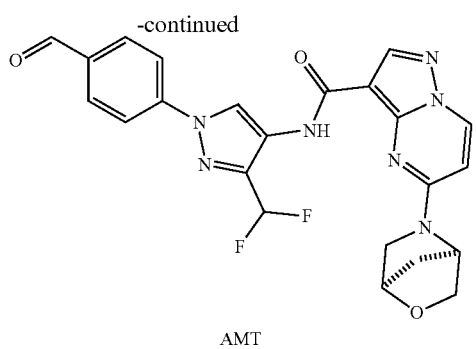

AMT

Step 1—Isopropoxycarbonyl 4-[3-(difluoromethyl)-4-[[5-[(1R)-2-oxa-5-azabicyclo[2.2.1]heptan-5-yl]pyrazolo[1,5-a]pyrimidine-3-carbonyl]amino]pyrazol-1-yl]benzoate To a mixture of 4-[3-(difluoromethyl)-4-[[5-[(1R)-2-oxa-5-azabicyclo[2.2.1]heptan-5-yl] pyrazolo [1,5-a]pyrimidine-3-carbonyl]amino]pyrazol-1-yl]benzoic acid (800 mg, 1.61 mmol, Intermediate AKT) in THF (10 mL) was added TEA (653 mg, 6.46 mmol) at 0° C. Then isopropyl carbonochloridate (494 mg, 4.04 mmol) was added into the mixture. The mixture was stirred at 0° C. for 0.5 hour. On completion, the reaction mixture was filtered to give the mother liquor. The mother liquor was used into the next step without further purification to give the title compound (939 mg, 100% yield) as brown oil. LC-MS (ESI$^+$) m/z 582.2 (M+H)$^+$.

Step 2—N-[3-(difluoromethyl)-1-[4-(hydroxymethyl)phenyl]pyrazol-4-yl]-5-[(1R)-2-oxa-5-azabicyclo [2.2.1]heptan-5-yl]pyrazolo[1,5-a]pyrimidine-3-carboxamide To a mixture of isopropoxycarbonyl 4-[3-(difluoromethyl)-4-[[5-[(1R,4R)-2-oxa-5-azabicyclo[2.2.1] heptan-5-yl]pyrazolo[1,5-a]pyrimidine-3-carbonyl]amino]pyrazol-1-yl]benzoate (939 mg, 1.61 mmol) in THF (20 mL) and H$_2$O (2 mL) was added LiBH$_4$ (70.3 mg, 3.23 mmol) at 0° C. The mixture was stirred at 25° C. for 0.5 hour. On completion, the reaction mixture was poured into the water (60 mL), and extracted with EA (2×30 mL). The combined organic phase was washed with brine (2×60 mL), dried with anhydrous Na$_2$SO$_4$, filtered and concentrated in vacuo to give the residue. The residue was purified by reversed-phase HPLC to give the title compound (260 mg, 33% yield) as a white solid. $^1$H NMR (400 MHz, DMSO-d$_6$) δ 9.61 (d, J=3.6 Hz, 1H), 8.97 (d, J=2.4 Hz, 1H), 8.80 (d, J=9.2 Hz, 1H), 8.30 (d, J=4.8 Hz, 1H), 7.80 (d, J=8.4 Hz, 2H), 7.52-7.14 (m, 3H), 6.96-6.44 (m, 1H), 5.35-5.05 (m, 1H), 4.79 (d, J=12.0 Hz, 1H), 4.56 (s, 2H), 3.87-3.74 (m, 2H), 3.68-3.62 (m, 2H), 2.09-1.93 (m, 2H), 1.04 (t, J=7.2 Hz, 1H).

Step 3—N-[3-(difluoromethyl)-1-(4-formylphenyl)pyrazol-4-yl]-5-[(1R,4R)-2-oxa-5-azabicyclo[2.2.1]heptan-5-yl]pyrazolo[1,5-a]pyrimidine-3-carboxamide To a mixture of N-[3-(difluoromethyl)-1-[4-(hydroxymethyl)phenyl]pyrazol-4-yl]-5-[(1R,4R)-2-oxa-5-azabicyclo [2.2.1]heptan-5-yl]pyrazolo[1,5-a]pyrimidine-3-carboxamide (180 mg, 373 umol) in DCM (10 mL) was added DMP (174 mg, 411 umol). The reaction mixture was stirred at 25° C. for 0.5 hour. On completion, the reaction mixture was poured into the water (80 mL), and extracted with DCM (2×60 mL). The combined organic phase was washed with brine (2×50 mL), dried with anhydrous $Na_2SO_4$, filtered and concentrated in vacuo to give title compound (152 mg, 84% yield) as a white solid. $^1$H NMR (400 MHz, DMSO-$d_6$) δ 10.04 (s, 1H), 9.64 (d, J=3.6 Hz, 1H), 9.17 (d, J=2.8 Hz, 1H), 8.81 (d, J=10.0 Hz, 1H), 8.32 (d, J=5.2 Hz, 1H), 8.18-8.02 (m, 4H), 7.55-6.39 (m, 2H), 5.34-5.07 (m, 1H), 4.80 (d, J=12.1 Hz, 1H), 3.87-3.74 (m, 2H), 3.66-3.44 (m, 2H), 2.15-1.96 (m, 2H).

3-(Difluoromethyl)-4-nitro-1-[4-(pent-4-ynoxymethyl)cyclohexyl]pyrazole (Intermediate AMU)

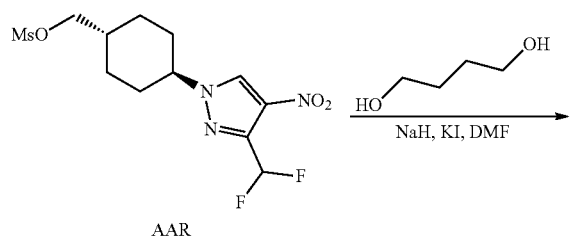

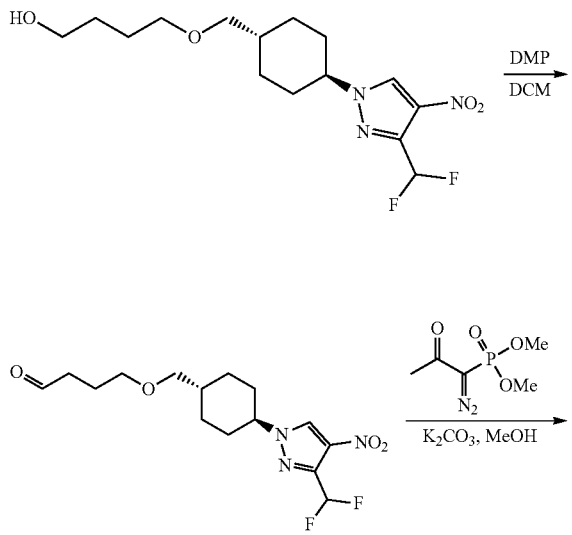

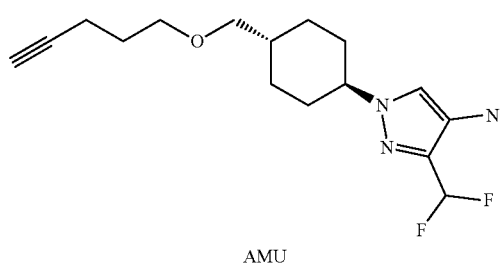

Step 1—4-[4-[3-(Difluoromethyl)-4-nitro-pyrazol-1-yl]cyclohexyl]methoxy]butan-1-ol To a mixture of butane-1,4-diol (1.61 g, 17.8 mmol, CAS #110-63-4) in DMF (20 mL) was added NaH (475 mg, 11.8 mmol, 60% purity) at 0° C. The mixture was stirred at 0° C. for 0.5 hr under nitrogen atmosphere. Then [4-[3-(difluoromethyl)-4-nitro-pyrazol-1-yl]cyclohexyl]methyl methanesulfonate (2.10 g, 5.94 mmol, Intermediate AAR) and KI (98.6 mg, 594 umol) was added to the reaction mixture. The mixture was stirred at 20° C. for 24 hrs under nitrogen atmosphere. On completion, the mixture was diluted with water (200 mL) and extracted with EA (3×50 mL). The organic layer was washed with brine (3×50 mL). The organic layer was dried over anhydrous sodium sulfate and filtered. The filtrated was concentrated in vacuo. The residue was purified by silica gel chromatography (PE:EA=2:1) to give the title compound (850 mg, 41% yield) as yellow oil. $^1$H NMR (400 MHz, CDCl$_3$) δ 8.21 (s, 1H), 7.25-6.98 (m, 1H), 4.23-4.18 (m, 1H), 4.12-4.10 (m, 1H), 3.66 (t, J=5.6 Hz, 2H), 3.48 (t, J=5.6 Hz, 2H), 3.32 (d, J=6.0 Hz, 2H), 2.31-2.27 (m, 2H), 2.11-2.03 (m, 3H), 1.79-1.74 (m, 2H), 1.70-1.67 (m, 4H), 1.24-1.16 (m, 2H).

Step 2—4-[[4-[3-(Difluoromethyl)-4-nitro-pyrazol-1-yl] cyclohexyl]methoxy]butanal To a mixture of 4-[[4-[3-(difluoromethyl)-4-nitro-pyrazol-1-yl]cyclohexyl]methoxy]butan-1-ol (850 mg, 2.45 mmol) in DCM (20 mL) was added DMP (1.56 g, 3.67 mmol) at 0° C. The reaction mixture was stirred at 20° C. for 2 hrs. On completion, the reaction mixture was diluted with saturated $Na_2S_2O_3$ aqueous (10 mL) and saturated $NaHCO_3$ aqueous (10 mL). The mixture was stirred at 20° C. for 0.5 hr. The mixture was diluted with water (100 mL) and extracted with DCM (3×40 mL). The organic layer was washed with saturated $NaHCO_3$ aqueous (3×40 mL) and brine (3×40 mL). The organic layer was dried over anhydrous sodium sulfate and filtered. The filtrated was concentrated in vacuo to give the title compound (820 mg, 97% yield) as yellow solid. LC-MS (ESI$^+$) m/z 346.1 (M+H)$^+$.

Step 3—3-(Difluoromethyl)-4-nitro-1-[4-(pent-4-ynoxymethyl)cyclohexyl]pyrazole

To a mixture of 4-[[4-[3-(difluoromethyl)-4-nitro-pyrazol-1-yl]cyclohexyl]methoxy]butanal (820 mg, 2.37 mmol) and $K_2CO_3$ (656 mg, 4.75 mmol) in MeOH (30 mL) was added 1-diazo-1-dimethoxyphosphoryl-propan-2-one (501 mg, 2.61 mmol, CAS #90965-06-3) at 0° C. The mixture was stirred at 20° C. for 20 hrs under nitrogen atmosphere. On completion, the reaction mixture was filtrated. The filter was concentrated in vacuo. The crude product was purified by reverse phase (0.1% FA condition) to give the title compound (220 mg, 27% yield) as yellow oil. $^1$H NMR (400 MHz, CDCl$_3$) δ 8.21 (s, 1H), 7.26-6.98 (m, 1H), 4.18 (tt, J=3.6, 12.0 Hz, 1H), 3.52 (t, J=6.0 Hz, 2H), 3.30 (d, J=6.4 Hz, 2H), 2.34-2.24 (m, 4H), 2.08-1.99 (m, 2H), 1.96 (t, J=2.4 Hz, 1H), 1.84-1.76 (m, 3H), 1.75 (d, J=3.6 Hz, 1H), 1.73-1.67 (m, 1H), 1.28-1.14 (m, 2H).

3-[4-[5-[[4-[4-Amino-3-(difluoromethyl)pyrazol-1-yl]cyclohexyl]methoxy]pent-1-ynyl]-3-methyl-2-oxo-benzimidazol-1-yl]]piperidine-2,6-dione (Intermediate AMV)

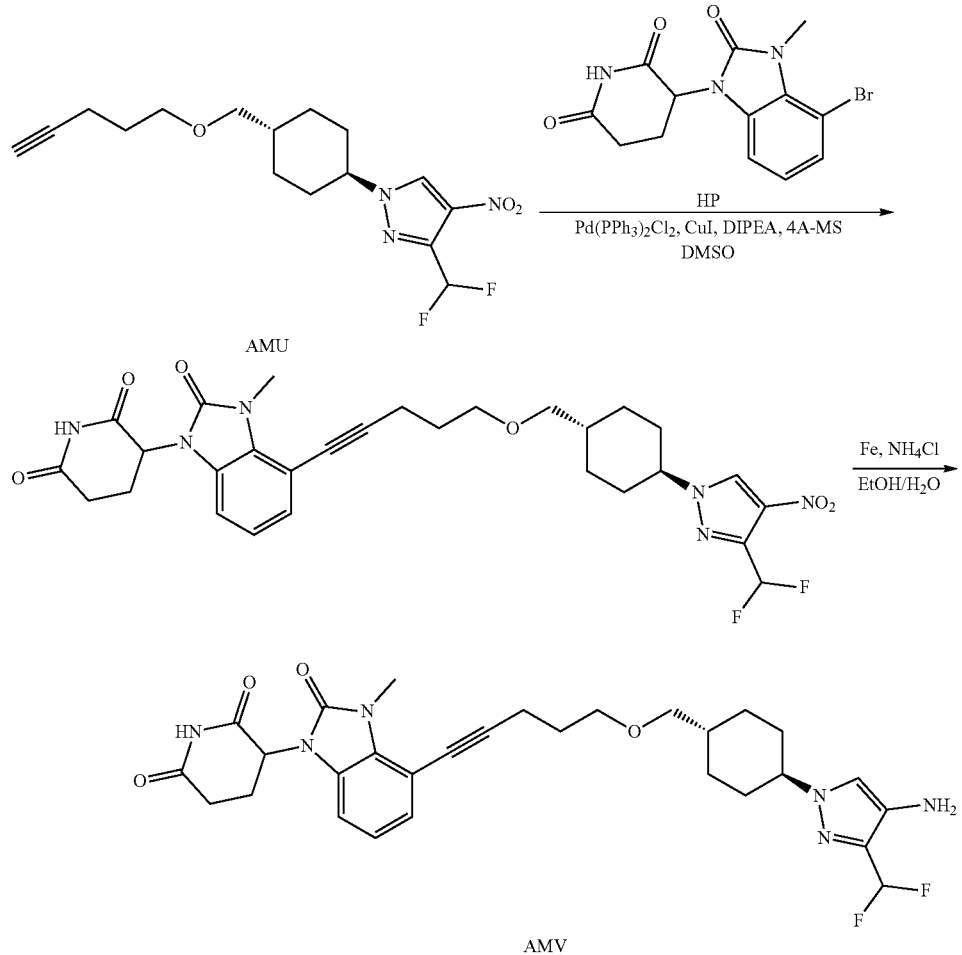

Step 1—3-[4-[5-[[4-[3-(Difluoromethyl)-4-nitropyrazol-1-yl] cyclohexyl]methoxy]pent-1-ynyl]-3-methyl-2-oxo-benzimidazol-1-yl]piperidine-2,6-dione A mixture of 3-(difluoromethyl)-4-nitro-1-[4-(pent-4-ynoxymethyl)cyclohexyl]pyrazole (120 mg, 351 umol, Intermediate AMU), 3-(4-bromo-3-methyl-2-oxo-benzimidazol-1-yl)piperidine-2,6-dione (130 mg, 386. umol, Intermediate HP), Pd(PPh$_3$)$_2$Cl$_2$ (24.6 mg, 35 umol), CuI (6.70 mg, 35.1 umol), DIPEA (227 mg, 1.76 mmol) and 4 Å molecular sieves in DMSO (3 mL) was stirred at 110° C. for 2 hrs under nitrogen atmosphere. On completion, the mixture was filtered and the filtrate was concentrated in vacuo. The crude product was purified by reverse phase (0.1% FA condition) to give the title compound (50.0 mg, 23% yield) as yellow solid. $^1$H NMR (400 MHz, CDCl$_3$) δ 8.20 (s, 1H), 7.48-7.45 (m, 2H), 7.12 (s, 1H), 7.00-6.96 (m, 1H), 6.74 (d, J=7.2 Hz, 1H), 5.19 (dd, J=5.2, 12.4 Hz, 1H), 4.19-4.10 (m, 1H), 3.79 (s, 3H), 3.57 (t, J=6.0 Hz, 2H), 3.32 (d, J=6.4 Hz, 2H), 2.58 (t, J=7.2 Hz, 2H), 2.30-2.20 (m, 4H), 2.09-1.98 (m, 3H), 1.94-1.87 (m, 2H), 1.76-1.66 (m, 4H), 1.23-1.17 (m, 2H).

Step 2—3-[4-[5-[[4-[4-Amino-3-(difluoromethyl)pyrazol-1-yl]cyclohexyl]methoxy]pent-1-ynyl]-3-methyl-2-oxo-benzimidazol-1-ylpiperidine-2,6-dione To a mixture of 3-[4-[5-[[4-[3-(difluoromethyl)-4-nitropyrazol-1-yl] cyclohexyl]methoxy]pent-1-ynyl]-3-methyl-2-oxo-benzimidazol-1-yl]piperidine-2,6-dione (50.0 mg, 83.5 umol) in a mixed solvent of IPA (10 mL) and H$_2$O (1 mL) was added Fe (23.3 mg, 417 umol) and NH$_4$Cl (22.3 mg, 417 umol). The reaction mixture was stirred at 70° C. for 16 hrs under nitrogen atmosphere. Then additional Fe (13.9 mg, 250 umol) and NH$_4$Cl (13.4 mg, 250 umol) was added. The reaction mixture was stirred at 70° C. for 3 hrs under nitrogen atmosphere. On completion, the reaction mixture was filtrated and the filtrate was concentrated in vacuo. The residue was purified by Prep-HPLC (column: UniSil 3-100 C18 Ultra (150*25 mm*3 um); mobile phase: [water (0.225% FA)-ACN]) to give the title compound (15.0 mg, 31% yield) as white solid. LC-MS (ESI$^+$) m/z 569.3 (M+H)$^+$.

2107

3-(Difluoromethyl)-1-[4-(4-piperidyloxymethyl) cyclohexyl]pyrazol-4-amine (Intermediate AMW)

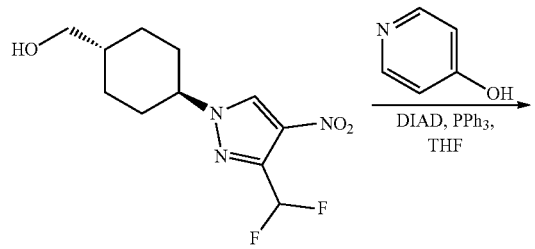

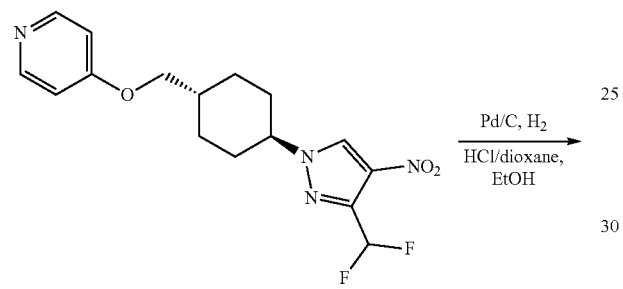

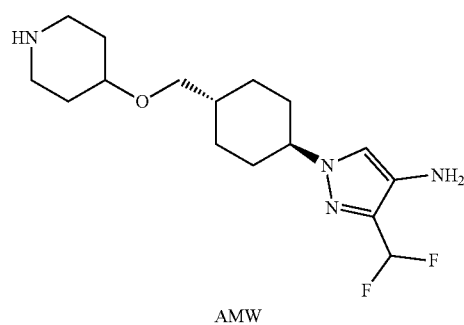

AMW

2108

Step 1—4-[[4-[3-(Difluoromethyl)-4-nitro-pyrazol-1-yl]cyclohexyl]methoxy]pyridine To a solution of [4-[3-(difluoromethyl)-4-nitro-pyrazol-1-yl]cyclohexyl]methanol (500 mg, 1.82 mmol, synthesized via Step 1 of Intermediate AAR), pyridin-4-ol (172 mg, 1.82 mmol, CAS #626-64-2) and PPh$_3$ (714 mg, 2.72 mmol) in THF (10 mL) was added and DIAD (550 mg, 2.72 mmol) at 0° C. The reaction mixture was stirred at 50° C. for 12 hrs under N$_2$. On completion, the reaction mixture was concentrated in vacuo to give a residue. The residue was purified by reverse phase (0.1% FA condition) to give the title compound (440 mg, 68% yield) as a white solid. $^1$H NMR (400 MHz, DMSO-d$_6$) δ 9.07 (s, 1H), 8.38 (d, J=5.2 Hz, 2H), 7.47-7.15 (m, 1H), 6.98 (d, J=6.0 Hz, 2H), 4.41-4.27 (m, 1H), 3.94 (d, J=6.4 Hz, 2H), 2.13 (d, J=10.8 Hz, 2H), 1.98 (d, J=12.4 Hz, 2H), 1.90-1.75 (m, 3H), 1.37-1.22 (m, 2H); LC-MS (ESI$^+$) m/z 353.1 (M+H)$^+$.

Step 2—3-(Difluoromethyl)-1-[4-(4-piperidyloxymethyl)cyclohexyl]pyrazol-4-amine To a solution of 4-[[4-[3-(difluoromethyl)-4-nitro-pyrazol-1-yl]cyclohexyl]methoxy]pyridine (340 mg, 964 umol) in EtOH (9 mL) was added PtO$_2$ (350 mg, 1.54 mmol) and HCl/dioxane (1 M, 0.9 mL) at 25° C. The reaction mixture was stirred at 25° C. for 12 hrs under H$_2$ (50 Psi). On completion, the reaction mixture was filtered through celite and the filtrate was concentrated in vacuo to give the title compound (340 mg, 96% yield) as a pink solid. LC-MS (ESI$^+$) m/z 329.6 (M+H)$^+$.

3-[4-[4-[[4-[4-Amino-3-(difluoromethyl)pyrazol-1-yl] cyclohexyl]methoxy]piperidine-1-carbonyl]-3-methyl-2-oxo-benzimidazol-1-yl]]piperidine-2,6-dione (Intermediate AMX)

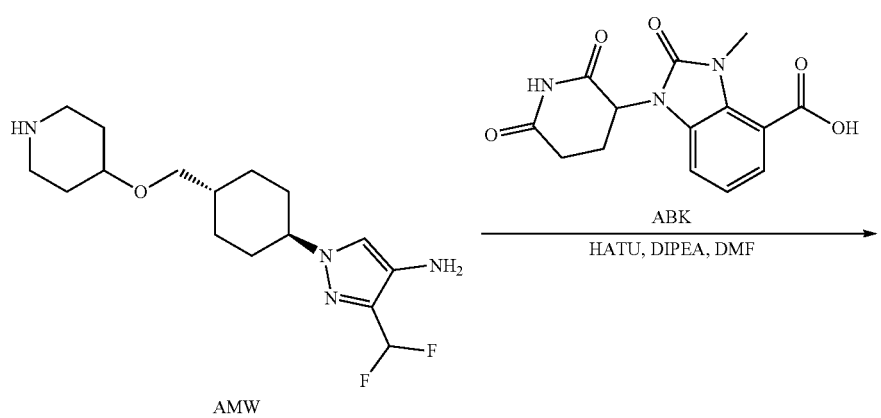

AMW

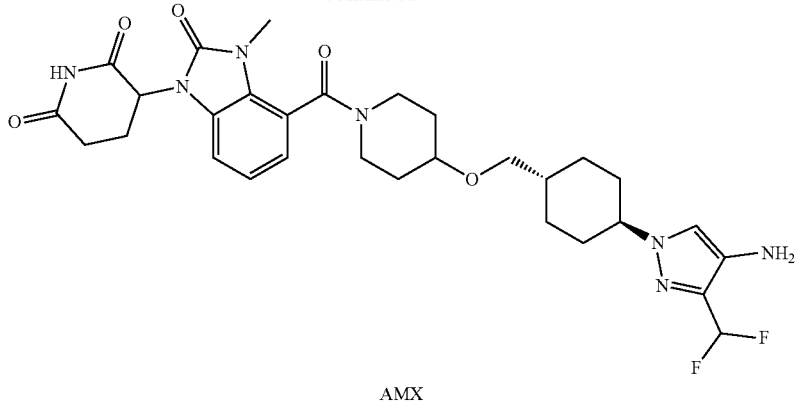

AMX

To a solution of 1-(2,6-dioxo-3-piperidyl)-3-methyl-2-oxo-benzimidazole-4-carboxylic acid (1.22 g, 401 umol, Intermediate ABK) in DMF (12 mL) was added HATU (166 mg, 438 umol) and DIPEA (94.4 mg, 730 umol). The mixture stirred at 25° C. for 30 minutes. Then 3-(difluoromethyl)-1-[4-(4-piperidyloxymethyl) cyclohexyl]pyrazol-4-amine (120 mg, 365 umol, Intermediate AMW) was added, and the mixture was stirred at 25° C. for 2.5 hrs. On completion, the reaction mixture was added H₂O (0.5 mL) and concentrated in vacuo to give a residue. The residue was purified by reverse phase (0.1% FA condition) to give the title compound (50.0 mg, 22% yield) as a white solid. ¹H NMR (400 MHz, DMSO-d₆) δ 11.13 (s, 1H), 8.87 (s, 1H), 7.23-6.82 (m, 4H), 5.42 (dd, J=5.2, 12.8 Hz, 1H), 4.88-4.69 (m, 1H), 3.78-3.58 (m, 1H), 3.31 (s, 2H), 3.27 (s, 1H), 3.25 (s, 3H), 2.92-2.84 (m, 1H), 2.78-2.69 (m, 1H), 2.61 (s, 1H), 2.53-2.51 (m, 2H), 2.10-1.71 (m, 4H), 1.69-1.29 (m, 6H), 1.21-1.12 (m, 6H); LC-MS (ESI⁺) m/z 614.3 (M+H)⁺.

4-[6-(1-hydroxy-1-methyl-ethyl)-5-[[6-(trifluoromethyl)pyridine-2-carbonyl]amino]indazol-2-yl]cyclohexanecarboxylic acid (Intermediate AMY)

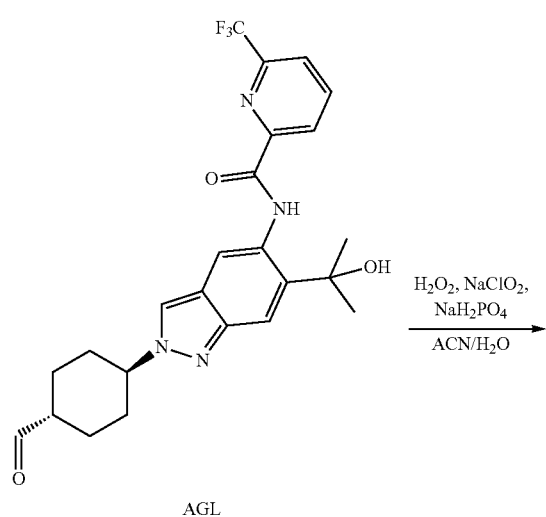

AGL

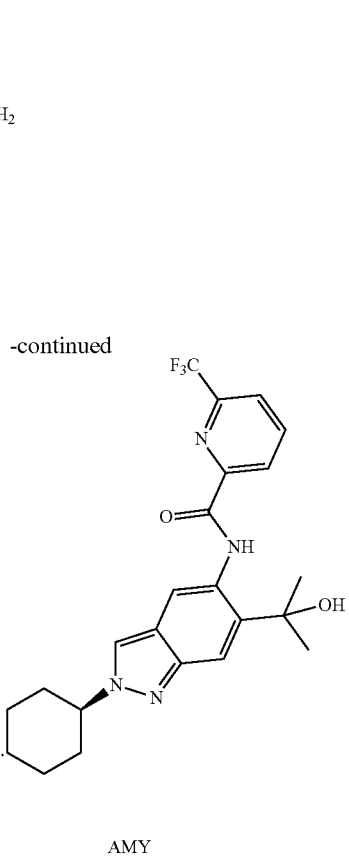

AMY

To a solution of N-[2-(4-formylcyclohexyl)-6-(1-hydroxy-1-methyl-ethyl) indazol-5-yl]-6-(trifluoro methyl) pyridine-2-carboxamide (200 mg, 421 umol, Intermediate AGL) and NaH₂PO₄ (252 mg, 2.11 mmol) in ACN (6 mL) was added H₂O₂ (95.5 mg, 843 umol, 81 uL, 30% solution) dropwise at 0° C. Then sodium chlorite (266 mg, 2.95 mmol) in H₂O (3 mL) was added to the mixture at 0° C. The reaction mixture was stirred at 25° C. for 1 hour. On completion, the reaction mixture was diluted with ACN (20 mL) and the reaction was quenched with sat.Na₂SO₃ (20 mL) at 0° C. The reaction mixture was extracted with ACN (3×10 mL). The combined organic layers were concentrated in vacuo to give the title compound (200 mg, 96% yield) as a yellow solid. LC-MS (ESI⁺) m/z 491.1 (M+1)⁺.

2111

5-(6-Oxa-3-azabicyclo[3.1.1]heptan-3-yl)pyrazolo[1,5-a]pyrimidine-3-carboxylic acid (Intermediate ALY)

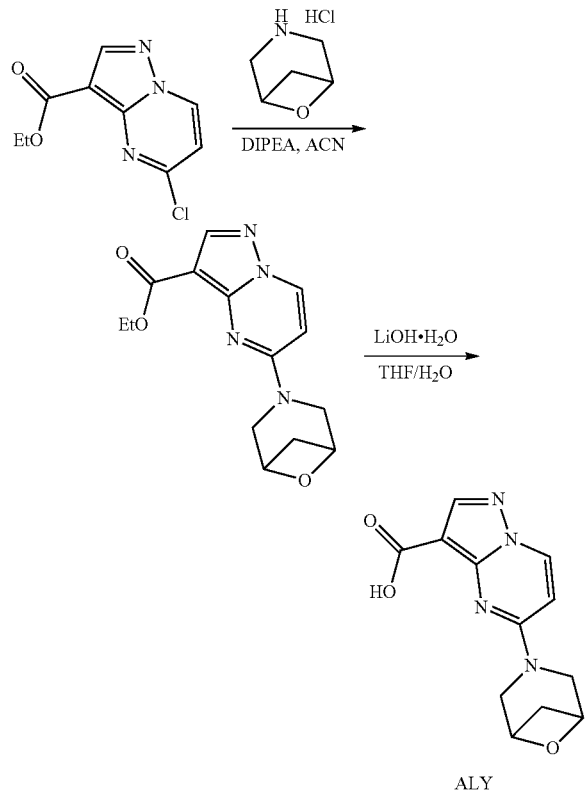

Step 1—Ethyl 5-(6-oxa-3-azabicyclo[3.1.1]heptan-3-yl)pyrazolo[1,5-a]pyrimidine-3-carboxylate To a solution of ethyl 5-chloropyrazolo[1,5-a]pyrimidine-3-carboxylate (300 mg, 1.33 mmol, CAS #1224944-77-7) and 6-oxa-3-azabicyclo[3.1.1]heptane (216.34 mg, 1.60 mmol, HCl, CAS #1414958-33-0) in ACN (5 mL) was added DIPEA (515 mg, 3.99 mmol, 694 uL). The reaction mixture was stirred at 60° C. for 2 hours. The mixture was concentrated in vacuo to give the title compound (0.85 g, 90% yield) as yellow oil. LC-MS (ESI$^+$) m/z 289.1 (M+H)$^+$.

Step 2—5-(6-Oxa-3-azabicyclo[3.1.1]heptan-3-yl)pyrazolo[1,5-a]pyrimidine-3-carboxylic acid To a solution of ethyl 5-(6-oxa-3-azabicyclo[3.1.1]heptan-3-yl)pyrazolo[1,5-a]pyrimidine-3-carboxylate (1.1 g, 3.82 mmol) in a mixed solvents of THF (8 mL) and H$_2$O (8 mL) was added LiOH·H$_2$O (320.22 mg, 7.63 mmol). The reaction mixture was stirred at 60° C. for 16 hrs. On completion, the reaction mixture was concentrated in vacuo. The residue was purified by reverse phase (0.1% TFA) to give the title compound (500 mg, 40% yield) as yellow solid. $^1$H NMR (400 MHz, DMSO-d$_6$) δ 8.77 (d, J=7.6 Hz, 1H), 8.16 (s, 1H), 6.65 (d, J=8.0 Hz, 1H), 4.74 (d, J=6.4 Hz, 2H), 3.83-3.69 (m, 4H), 3.20-3.09 (m, 2H).

2112

N-[3-(difluoromethyl)-1-(4-formylcyclohexyl)pyrazol-4-yl]-5-(6-oxa-3-azabicyclo[3.1.1] heptan-3-yl)pyrazolo[1,5-a]pyrimidine-3-carboxamide (Intermediate ALZ)

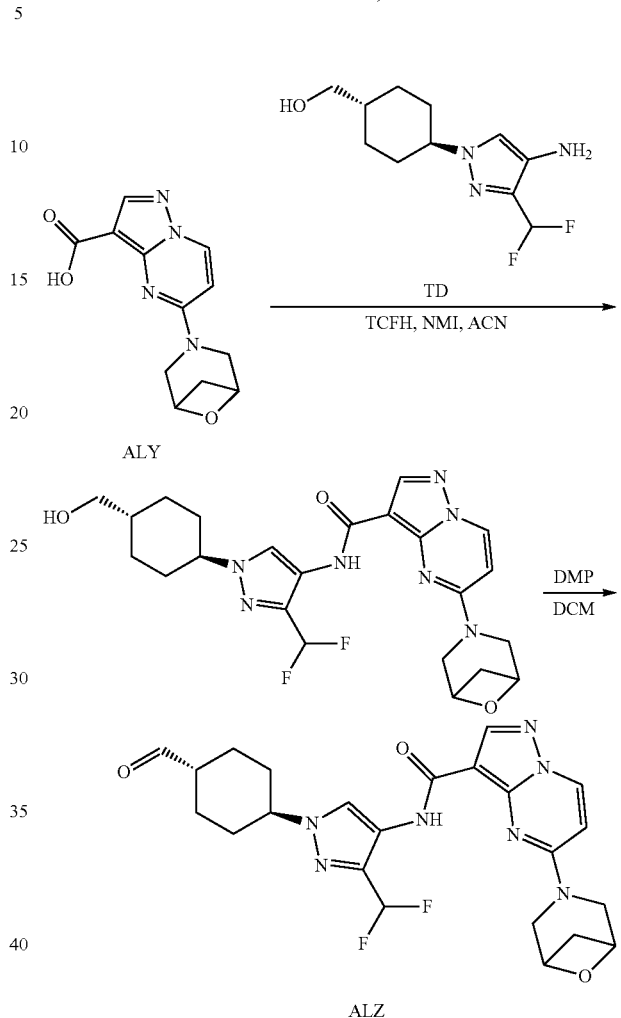

Step 1—N-[3-(difluoromethyl)-1-[4-(hydroxymethyl)cyclohexyl]pyrazol-4-yl]-5-(6-oxa-3-azabicyclo [3.1.1]heptan-3-yl)pyrazolo[1,5-a]pyrimidine-3-carboxamide To a mixture of 5-(6-oxa-3-azabicyclo[3.1.1]heptan-3-yl)pyrazolo[1,5-a]pyrimidine-3-carboxylic acid (450 mg, 1.73 mmol, Intermediate ALY), 1-methylimidazole (496 mg, 6.05 mmol, 482 uL) and [chloro(dimethylamino)methylene]-dimethyl-ammonium; hexafluorophosphate (582 mg, 2.07 mmol) in ACN (15 mL) was added [4-[4-amino-3-(difluoromethyl)pyrazol-1-yl]cyclohexyl]methanol (424 mg, 1.73 mmol, Intermediate TD). The reaction mixture was stirred at 25° C. for 12 hours. On completion, the reaction mixture was quenched with water (0.05 mL) and concentrated in vacuo. The residue was purified by reverse phase (0.1% FA condition) to give the title compound (230 mg, 27% yield) as white solid. $^1$H NMR (400 MHz, DMSO-d$_6$) δ 9.52 (s, 1H), 8.87 (d, J=7.6 Hz, 1H), 8.45-8.26 (m, 2H), 7.08 (t, J=54 Hz, 1H), 6.74 (d, J=8.0 Hz, 1H), 4.84-4.62 (m, 2H), 4.47 (s, 1H), 4.24-4.12 (m, 1H), 4.04-3.95 (m, 1H), 3.91-3.73 (m, 3H), 3.28-3.24 (m, 2H), 3.22-3.15 (m, 1H), 2.04 (d, J=10.4

Hz, 2H), 1.92 (d, J=9.2 Hz, 1H), 1.89-1.80 (m, 2H), 1.80-1.66 (m, 2H), 1.43 (s, 1H), 1.16-1.00 (m, 2H).

Step 2—N-[3-(difluoromethyl)-1-(4-formylcyclohexyl)pyrazol-4-yl]-5-(6-oxa-3-azabicyclo[3.1.1]heptan-3-yl)pyrazolo[1,5-a]pyrimidine-3-carboxamide To a mixture of N-[3-(difluoromethyl)-1-[4-(hydroxymethyl)cyclohexyl]pyrazol-4-yl]-5-(6-oxa-3-azabicyclo[3.1.1]heptan-3-yl)pyrazolo[1,5-a]pyrimidine-3-carboxamide (200 mg, 410 umol) in DCM (8 mL) was added DMP (208 mg, 492 umol, 152 uL). The reaction mixture was stirred at 25° C. for 48 hours. On completion, the reaction mixture was quenched by saturated Na$_2$S$_2$O$_3$ (80 mL) and saturated NaHCO$_3$ (80 mL) at 25° C., and then stirred for 30 minutes. The mixture was extracted with DCM (2×100 mL). The combined organic layers was dried over Na$_2$SO$_4$, filtered and concentrated in vacuo to give the title compound (199 mg, 99% yield) as light yellow solid. $^1$H NMR (400 MHz, DMSO-d$_6$) δ 9.62 (s, 1H), 9.53 (s, 1H), 8.87 (d, J=8.0 Hz, 1H), 8.40 (s, 1H), 8.30 (s, 1H), 7.09 (t, J=54 Hz, 1H), 6.74 (d, J=8.0 Hz, 1H), 4.81-4.68 (m, 2H), 4.28-4.14 (m, 1H), 4.02-3.78 (m, 4H), 3.25-3.15 (m, 1H), 2.53-2.51 (m, 1H), 2.44-2.31 (m, 1H), 2.13-2.02 (m, 4H), 1.88-1.76 (m, 2H), 1.45-1.32 (m, 2H).

5-(3-Oxa-6-azabicyclo[3.1.1]heptan-6-yl)pyrazolo[1,5-a]pyrimidine-3-carboxylic acid (Intermediate AMA)

Step 1—Ethyl 5-(3-oxa-6-azabicyclo[3.1.1]heptan-6-yl)pyrazolo[1,5-a]pyrimidine-3-carboxylate To a solution of ethyl 5-chloropyrazolo[1,5-a]pyrimidine-3-carboxylate (500 mg, 2.22 mmol, CAS #1224944-77-7) and DIPEA (859 mg, 6.65 mmol, 1.16 mL) in ACN (10 mL) was added 3-oxa-6-azabicyclo[3.1.1]heptane (241 mg, 2.44 mmol, CAS #286390-20-3). The reaction mixture was stirred at 60° C. for 3 hrs. On completion, the reaction mixture was diluted with water (20 mL), and extracted with EA (2×30 mL). The combined organic layer was washed with brine (2×20 mL), dried with anhydrous Na$_2$SO$_4$, filtered and concentrated in vacuo to give the title compound (600 mg, 94% yield) as a yellow solid. LC-MS (ESI$^+$) m/z 289.0 (M+H)$^+$.

Step 2—5-(3-Oxa-6-azabicyclo[3.1.1]heptan-6-yl)pyrazolo[1,5-a]pyrimidine-3-carboxylic acid To a solution of ethyl 5-(3-oxa-6-azabicyclo[3.1.1]heptan-6-yl)pyrazolo[1,5-a]pyrimidine-3-carboxylate (600 mg, 2.08 mmol) in a mixture of MeOH (5 mL) and H$_2$O (5 mL) was added LiOH.H$_2$O (130 mg, 3.12 mmol), and the reaction mixture was stirred at 60° C. for 16 hrs. On completion, the mixture was concentrated in vacuo and then diluted with H$_2$O (15 mL). Then the mixture was adjusted with 1N HCl until the pH 6. The mixture was lyophilized to give the title compound (500 mg, 92.3% yield) as a white solid. $^1$H NMR (400 MHz, DMSO-d$_6$) δ 8.93 (d, J=7.2 Hz, 1H), 8.23 (s, 1H), 6.61 (d, J=7.6 Hz, 1H), 5.14-4.61 (m, 1H), 4.60-4.32 (m, 1H), 4.20-3.95 (m, 4H), 3.89-3.71 (m, 2H).

N-[3-(difluoromethyl)-1-(4-formylcyclohexyl)pyrazol-4-yl]-5-(3-oxa-6-azabicyclo[3.1.1] heptan-6-yl)pyrazolo[1,5-a]pyrimidine-3-carboxamide (Intermediate AMB)

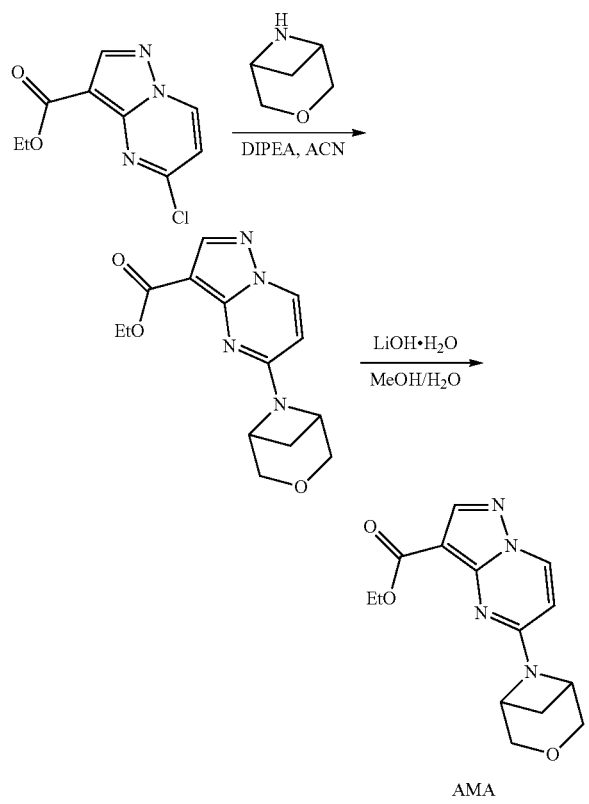

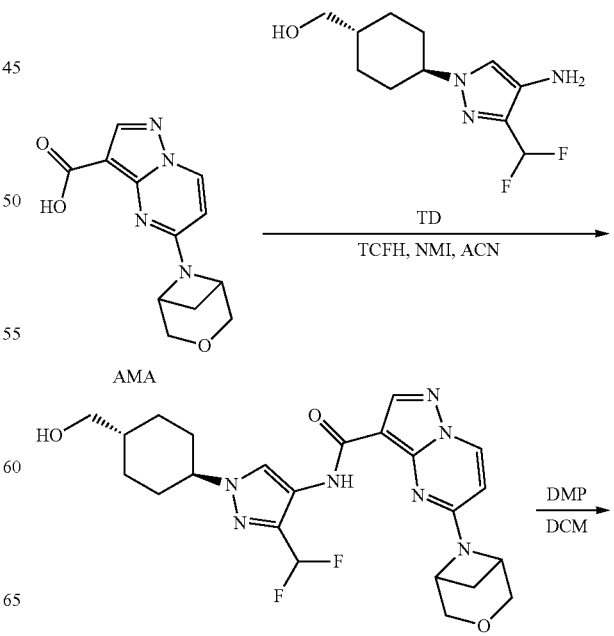

2115

-continued

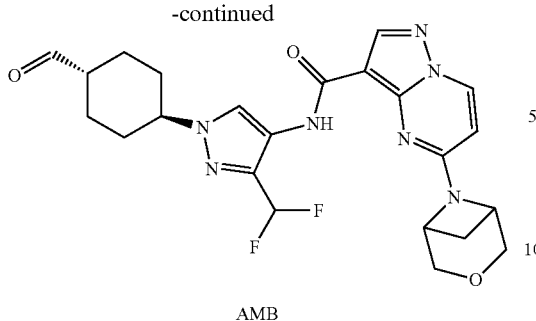

AMB

Step 1—N-[3-(difluoromethyl)-1-[4-(hydroxymethyl)cyclohexyl]pyrazol-4-yl]-5-(3-oxa-6-azabicyclo [3.1.1]heptan-6-yl)pyrazolo[1,5-a]pyrimidine-3-carboxamide To a solution of 5-(3-oxa-6-azabicyclo[3.1.1]heptan-6-yl) pyrazolo [1,5-a]pyrimidine-3-carboxylic acid (420 mg, 1.61 mmol, Intermediate AMA) in ACN (10 mL) was added 1-methylimidazole (463 mg, 5.65 mmol, 450 uL) and [chloro(dimethylamino)methylene]-dimethyl-ammonium; hexafluorophosphate (543 mg, 1.94 mmol), the mixture was stirred at 20° C. for 30 min. Then [4-[4-amino-3-(difluoromethyl)pyrazol-1-yl] cyclohexyl]methanol (395 mg, 1.61 mmol, Intermediate TD) was added to the mixture. The reaction mixture was stirred at 20° C. for 12 hrs. On completion, the reaction was quenched with water (0.5 mL) and the mixture was concentrated in vacuo to give the residue. The residue was purified by reverse phase flash (0.1% FA condition) to give the title compound (280 mg, 35.6% yield) as a white solid. LC-MS (ESI$^+$) m/z 488.1 (M+1)$^+$.

Step 2—N-[3-(difluoromethyl)-1-(4-formylcyclohexyl)pyrazol-4-yl]-5-(3-oxa-6-azabicyclo[3.1.1] heptan-6-yl)pyrazolo[1,5-a]pyrimidine-3-carboxamide To a solution of N-[3-(difluoromethyl)-1-[4-(hydroxymethyl)cyclohexyl]pyrazol-4-yl]-5-(3-oxa-6-azabicyclo [3.1.1]heptan-6-yl)pyrazolo[1,5-a]pyrimidine-3-carboxamide (90.0 mg, 184 umol) in DCM (4 mL) was added DMP (93.9 mg, 221 umol), and the reaction mixture was stirred at 20° C. for 3 hr. On completion, the reaction mixture was quenched with Na$_2$S$_2$O$_3$ (10 mL) and extracted with DCM (2×30 mL). The combined organic layer was washed with NaHCO$_3$ and brine (2×20 mL), dried with anhydrous Na$_2$SO$_4$, filtered and concentrated in vacuo to give the title compound (70.0 mg, 78.1% yield) as a yellow solid. $^1$H NMR (400 MHz, DMSO-d$_6$) δ 9.61 (d, J=0.8 Hz, 1H), 9.55 (s, 1H), 8.85 (d, J=8.0 Hz, 1H), 8.41 (s, 1H), 8.30 (s, 1H), 7.22-6.95 (m, 1H), 6.62 (d, J=7.6 Hz, 1H), 4.76-4.59 (m, 2H), 4.34 (d, J=10.4 Hz, 1H), 4.25-4.17 (m, 1H), 4.05 (d, J=11.2 Hz, 1H), 3.86 (d, J=11.2 Hz, 1H), 3.77 (d, J=10.4 Hz, 1H), 2.42-2.35 (m, 1H), 2.14-2.02 (m, 5H), 1.93 (d, J=8.4 Hz, 1H), 1.85-1.77 (m, 2H), 1.42-1.33 (m, 2H); LC-MS (ESI$^+$) m/z 486.2 (M+1)$^+$.

2116

Tert-butyl N-[[4-(aminomethyl)phenyl]methyl]-N-methyl-carbamate (Intermediate ANT)

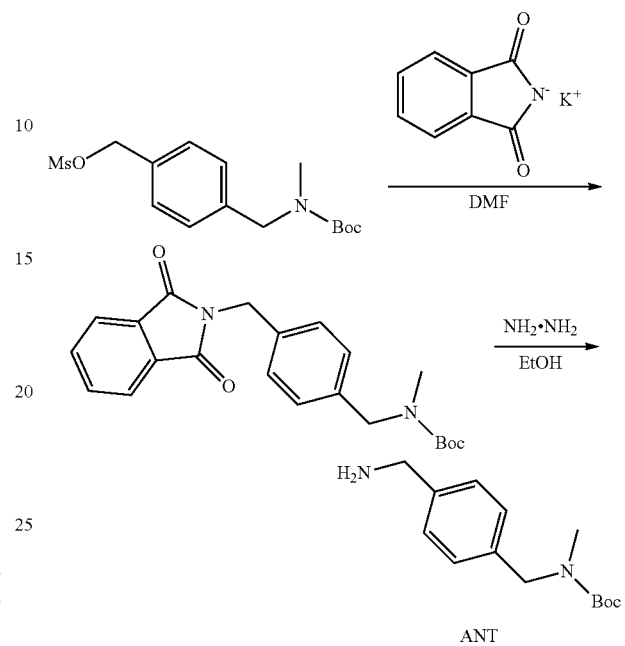

ANT

Step 1—Tert-butyl N-[[4-[(1,3-dioxoisoindolin-2-yl) methyl]phenyl]methyl]-N-methyl-carbamate To a solution of [4-[[tert-butoxycarbonyl(methyl)amino] methyl]phenyl]methylmethanesulfonate (800 mg, 2.43 mmol, synthesized via Step 1 of Intermediate ANL) in DMF (15 mL) was added (1,3-dioxoisoindolin-2-yl)potassium (674 mg, 3.64 mmol). The reaction mixture was stirred at 80° C. for 12 hrs. On completion, the mixture was diluted with water (100 mL), then extracted with EA (2×100 mL). The organic layer was washed with brine (100 mL), concentrated in vacuo. The residue was purified by reverse phase (0.1% FA condition) to give the title compound (0.500 g, 54% yield) as a yellow solid. $^1$H NMR (400 MHz, CDCl$_3$) δ 7.92-7.81 (m, 2H), 7.78-7.68 (m, 2H), 7.40 (d, J=8.0 Hz, 2H), 7.18 (d, J=7.6 Hz, 2H), 4.84 (s, 2H), 4.38 (s, 2H), 2.78 (d, J=12 Hz, 3H), 1.47 (s, 9H).

Step 2—Tert-butyl N-[[4-(aminomethyl)phenyl] methyl]-N-methyl-carbamate

To a solution of tert-butyl N-[[4-[(1,3-dioxoisoindolin-2-yl)methyl]phenyl]methyl]-N-methyl-carbamate (500 mg, 1.31 mmol) in EtOH (30 mL) was added NH$_2$NH$_2$ (358 mg, 10.5 mmol). The reaction mixture was stirred at 80° C. for 10 hrs. On completion, the mixture was filtered and the filtrate was concentrated in vacuo. The residue was triturated with DCM (50 mL), stirred and filtered. The filtrate was concentrated in vacuo to give the title compound (310 mg, 94% yield) as yellow oil. $^1$HNMR (400 MHz, CDCl$_3$) δ 7.31-7.27 (m, 2H), 7.21 (s, 2H), 4.41 (s, 2H), 3.87 (s, 2H), 2.83 (s, 3H), 1.49 (s, 9H).

2-(2,6-Dioxo-3-piperidyl)-4-[[4-(methylaminomethyl) phenyl]methylamino]isoindoline-1,3-dione (Intermediate ANU)

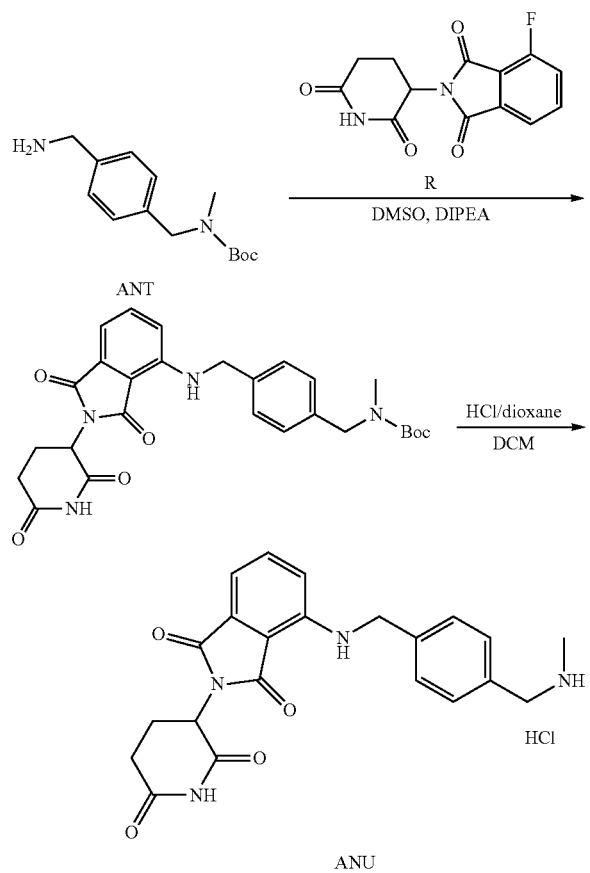

Step 1—Tert-butyl N-[[4-[[[2-(2,6-dioxo-3-piperidyl)-1,3-dioxo-isoindolin-4-yl]amino] methyl] phenyl] methyl]-N-methyl-carbamate To a solution of tert-butyl N-[[4-(aminomethyl)phenyl] methyl]-N-methyl-carbamate (200 mg, 798 umol, Intermediate ANT) and 2-(2,6-dioxo-3-piperidyl)-4-fluoro-isoindoline-1,3-dione (243 mg, 879 umol, Intermediate R) in DMSO (2 mL) was added DIPEA (413 mg, 3.20 mmol, 557 uL). The reaction mixture was stirred at 125° C. for 2 hrs. On completion, the mixture was concentrated in vacuo. The residue was purified by reverse phase (0.1% FA condition) to give the title compound (220 mg, 54% yield) as a green solid. $^1$H NMR (400 MHz, CDCl$_3$) δ 8.07 (s, 1H), 7.46 (dd, J=7.2, 8.4 Hz, 1H), 7.33-7.29 (m, 2H), 7.22 (d, J=7.6 Hz, 2H), 7.13 (d, J=7.2 Hz, 1H), 6.85 (d, J=8.4 Hz, 1H), 6.69 (t, J=5.6 Hz, 1H), 4.93 (dd, J=5.6, 12 Hz, 1H), 4.50 (d, J=5.6 Hz, 2H), 4.42 (s, 2H), 2.96-2.66 (m, 6H), 2.20-2.08 (m, 1H), 1.48 (s, 9H).

Step 2—2-(2,6-Dioxo-3-piperidyl)-4-[[4-(methylaminomethyl) phenyl]methylamino]isoindoline-1,3-dione To a solution of tert-butyl N-[[4-[[[2-(2,6-dioxo-3-piperidyl)-1,3-dioxo-isoindolin-4-ylamino]methyl] phenyl] methyl]-N-methyl-carbamate (270 mg, 533 umol) in DCM (2.5 mL) was added HCl/dioxane (4 M, 2 mL). The reaction mixture was stirred at 25° C. for 2 hrs. On completion, the reaction mixture was concentrated in vacuo to give the title compound (230 mg, 97% yield, HCl) as yellow solid. LC-MS (ESI$^+$) m/z 407.2 (M+H)$^+$.

2-(2,6-Dioxo-3-piperidyl)-4-[[4-[[methyl-[2-(methylamino)ethyl] amino]methyl]phenyl] methylamino] isoindoline-1,3-dione (Intermediate ANV)

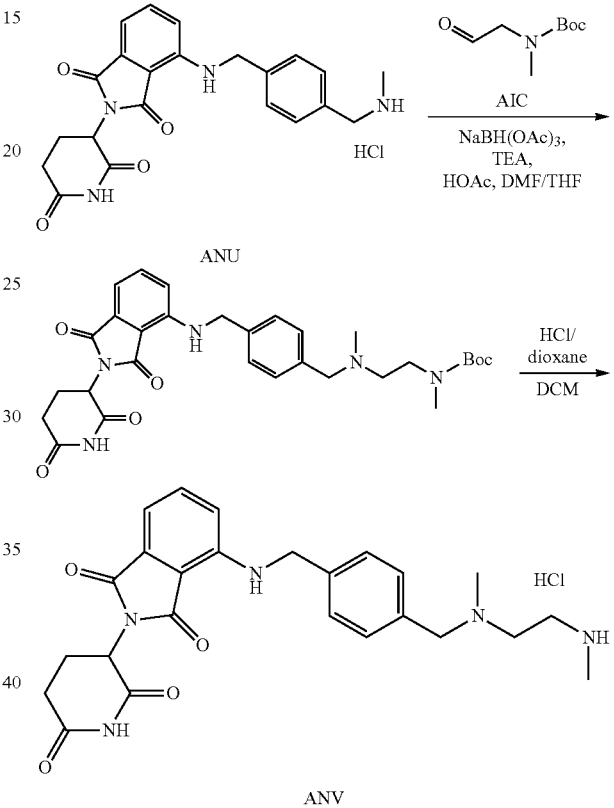

Step 1—Tert-butyl N-[2-[[4-[[[2-(2,6-dioxo-3-piperidyl)-1,3-dioxo-isoindolin-4-yl]amino]methyl] phenyl]methyl-methyl-amino] ethyl]-N-methyl-carbamate To a solution of 2-(2,6-dioxo-3-piperidyl)-4-[[4-(methylaminomethyl)phenyl]methylamino]isoindoline-1,3-dione (230 mg, 519.31 umol, HCl, Intermediate ANU) and tert-butyl N-methyl-N-(2-oxoethyl)carbamate (179 mg, 1.04 mmol, Intermediate AIC) in a mixed solvent of THF (4 mL) and DMF (1 mL) was added TEA (52.5 mg, 519 umol, 72.3 uL), HOAc (62.4 mg, 1.04 mmol, 59.4 uL). Thirty minutes later, NaBH(OAc)$_3$ (165 mg, 779 umol) was added. The reaction mixture was stirred at 25° C. for 3 hrs. On completion, the reaction mixture was quenched with water (0.5 ml) and concentrated in vacuo. The crude product was purified by reversed-phase HPLC (0.1% FA condition) to give the title compound (270 mg, 49% yield) as yellow solid. LC-MS (ESI$^+$) m/z 564.4 (M+H)$^+$.

Step 2—2-(2,6-Dioxo-3-piperidyl)-4-[[4-[[methyl-[2-(methylamino)ethyl] amino]methyl]phenyl] methylamino]isoindoline-1,3-dione To a solution of tert-butyl N-[2-[[4-[[[2-(2,6-dioxo-3-piperidyl)-1,3-dioxo-isoindolin-4-yl] amino] methyl] phenyl]methyl-methyl-amino] ethyl]-N-methyl-carbamate (200 mg, 354.83 umol) in DCM (3 mL) was added HCl/dioxane (4 M, 1.5 mL). The mixture was stirred at 25° C. for 1 hour. On completion, the reaction mixture was concentrated in vacuo to give the title compound (160 mg, 90% yield, HCl) as yellow solid. LC-MS (ESI$^+$) m/z 464.3 (M+H)$^+$.

Tert-butyl N-[2-[4-(2-aminoethyl)phenyl] ethyl] carbamate (Intermediate ANW)

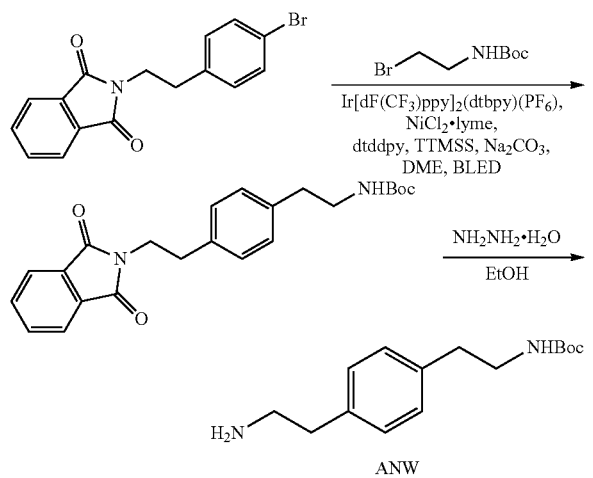

Step 1—Tert-butyl N-[2-[4-[2-(1,3-dioxoisoindolin-2-yl)ethyl]phenyl]ethyl] carbamate To an 40 mL vial equipped with a stir bar was added 2-[2-(4-bromophenyl)ethyl]isoindoline-1,3-dione (1.30 g, 3.94 mmol, synthesized via Step 1 of Intermediate AOO), tert-butyl N-(2-bromoethyl)carbamate (1.15 g, 5.12 mmol), bis[3,5-difluoro-2-[5-(trifluoromethyl)-2-pyridyl]phenyl] iridium(1+); 4-tert-butyl-2-(4-tert-butyl-2 pyridyl)pyridine; hexafluorophosphate (44.1 mg, 39.3 umol), dichloronickel; 1,2-dimethoxyethane (4.33 mg, 19.6 umol), 4-tert-butyl-2-(4-tert-butyl-2-pyridyl)pyridine (6.34 mg, 23.6 umol), bis (trimethylsilyl)silyl-trimethyl-silane (979 mg, 3.94 mmol) and Na$_2$CO$_3$ (834 mg, 7.87 mmol) in DME (24 mL). The vial was sealed and placed under nitrogen was added. The reaction was stirred and irradiated with a 34 W blue LED lamp (7 cm away), with cooling fan to keep the reaction temperature at 25° C. for 14 hrs. On completion, the mixture was purified by reverse phase (FA condition) to give the title compound (600 mg, 50% yield) as white solid. $^1$H NMR (400 MHz, DMSO-d$_6$) δ 7.92-7.73 (m, 4H), 7.09-7.06 (m, 4H), 6.89-6.78 (m, 1H), 3.76 (t, J=6.8 Hz, 2H), 3.12-3.01 (m, 2H), 2.86 (t, J=7.2 Hz, 2H), 2.63-2.59 (m, 2H), 1.34 (s, 9H).

Step 2—Tert-butyl N-[2-[4-(2-aminoethyl)phenyl] ethyl]carbamate

To a solution of tert-butyl N-[2-[4-[2-(1,3-dioxoisoindolin-2-yl)ethyl]phenyl]ethyl]carbamate (300 mg, 760 umol) in EtOH (10 mL) was added N$_2$H$_4$·H$_2$O (2.06 g, 34.9 mmol, 85% solution). The mixture was stirred at 80° C. for 2 hrs. On completion, the mixture was concentrated in vacuo and washed with DCM (3×50 mL). The organic phase was concentrated in vacuo to give the title compound (300 mg, 90% yield) as yellow oil. LC-MS (ESI$^+$) m/z 265.0 (M+1)$^+$.

4-[2-[4-(2-aminoethyl)phenyl]ethylamino]-2-(2,6-dioxo-3-piperidyl)isoindoline-1,3-dione (Intermediate ANX)

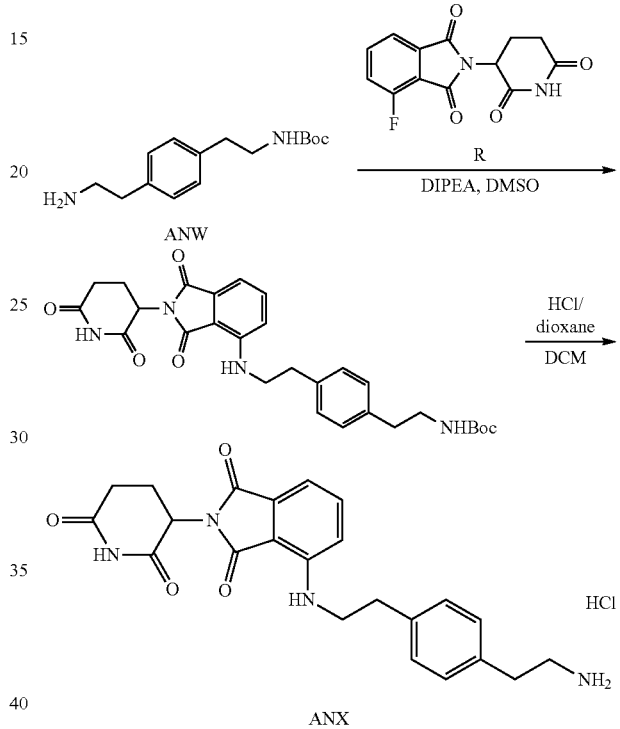

Step 1—Tert-butyl N-[2-[4-[2-[[2-(2,6-dioxo-3-piperidyl)-1,3-dioxo-isoindolin-4-yl]amino]ethyl] phenyl]ethyl]carbamate To a solution of tert-butyl N-[2-[4-(2-aminoethyl)phenyl] ethyl]carbamate (280 mg, 1.06 mmol, Intermediate ANW) and 2-(2,6-dioxo-3-piperidyl)-4-fluoro-isoindoline-1,3-dione (292 mg, 1.06 mmol, Intermediate R) in DMSO (5 mL) was added DIPEA (410 mg, 3.18 mmol). The mixture was stirred at 130° C. for 2 hrs. On completion, the residue was purified by reversed-phase HPLC (0.1% FA condition) to give the title compound (300 mg, 54% yield) as yellow solid. $^1$H NMR (400 MHz, DMSO-d$_6$) δ=11.22-10.91 (m, 1H), 7.62-7.55 (m, 1H), 7.25-7.20 (m, 2H), 7.19-7.08 (m, 4H), 7.04 (d, J=7.2 Hz, 1H), 6.91-6.83 (m, 1H), 6.57 (t, J=5.6 Hz, 1H), 5.06 (dd, J=5.6, 12.8 Hz, 1H), 3.57-3.49 (m, 2H), 3.11 (br d, J=7.6 Hz, 2H), 2.90-2.83 (m, 4H), 2.70-2.62 (m, 4H), 2.07-2.00 (m, 1H), 1.37 (s, 9H).

Step 2—4-[2-[4-(2-aminoethyl)phenyl]ethylamino]-2-(2,6-dioxo-3-piperidyl)isoindoline-1,3-dione To a solution of tert-butyl N-[2-[4-[2-[[2-(2,6-dioxo-3-piperidyl)-1,3-dioxo-isoindolin-4-yl]amino] ethyl]phenyl]

ethyl]carbamate (100 mg, 192 umol) in DCM (2 mL) was added HCl/dioxane (4 M, 48.0 uL). The mixture was stirred at 15° C. for 0.5 hr. On completion, the mixture was concentrated in vacuo to give the title compound (80.0 mg, 99% yield) as yellow oil. LC-MS (ESI⁺) m/z 421.1 (M+1)⁺.

2-(2,6-dioxo-3-piperidyl)-4-[[(2R)-morpholin-2-yl]methylamino]isoindoline-1,3-dione (Intermediate ALB)

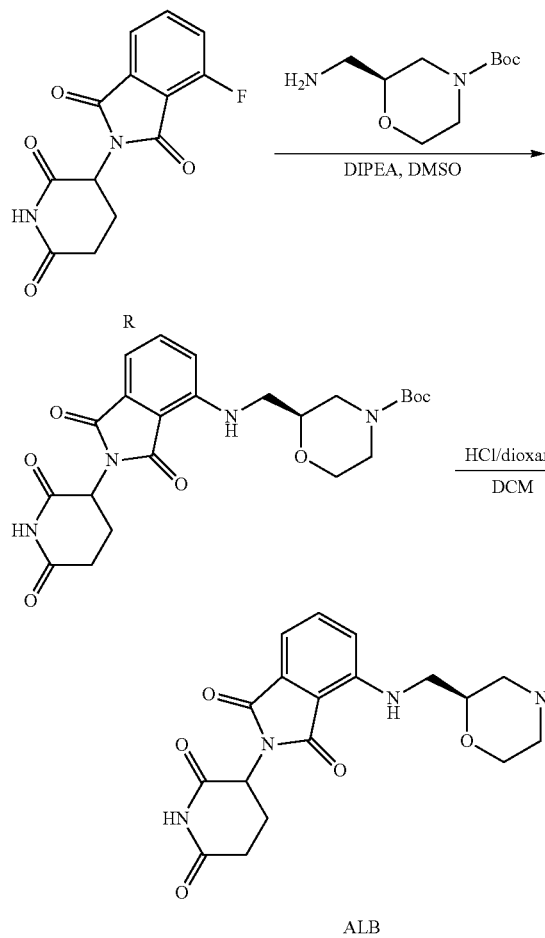

Step 1—Tert-butyl (2S)-2-[[[2-(2,6-dioxo-3-piperidyl)-1,3-dioxo-isoindolin-4-yl]amino]methyl] morpholine-4-carboxylate To a solution of 2-(2,6-dioxo-3-piperidyl)-4-fluoro-isoindoline-1,3-dione (210 mg, 762 umol, Intermediate R) and tert-butyl (2S)-2-(aminomethyl)morpholine-4-carboxylate (150 mg, 693 umol, CAS #879403-42-6) in DMSO (2.00 mL) was added DIPEA (448 mg, 3.47 mmol). The mixture was stirred at 90° C. for 3 hours. On completion, the reaction mixture was quenched with H₂O (0.5 mL), and then concentrated in vacuo to give a residue. The residue was purified by reverse phase (0.1% FA condition) to give the title compound (100 mg, 30% yield) as a white solid. ¹H NMR (400 MHz, CDCl₃) δ 8.01 (s, 1H), 7.52 (dd, J=7.2, 8.4 Hz, 1H), 7.13 (d, J=6.8 Hz, 1H), 6.93 (d, J=8.5 Hz, 1H), 6.51 (t, J=5.6 Hz, 1H), 4.95-4.90 (m, 1H), 4.12-3.81 (m, 3H), 3.68-3.60 (m, 1H), 3.59-3.52 (m, 1H), 3.47-3.27 (m, 2H), 2.96-2.90 (m, 1H), 2.89-2.68 (m, 4H), 2.22-2.05 (m, 1H), 1.48 (s, 9H).

Step 2—2-(2,6-Dioxo-3-piperidyl)-4-[[(2R)-morpholin-2-yl]methylamino]isoindoline-1,3-dione To a solution of tert-butyl (2S)-2-[[[2-(2,6-dioxo-3-piperidyl)-1,3-dioxo-isoindolin-4-yl]amino]methyl] morpholine-4-carboxylate (100 mg, 211 umol) in DCM (1.00 mL) was added TFA (1.54 g, 13.5 mmol, 1.00 mL). The mixture was stirred at 20° C. for 1 hour. On completion, the reaction mixture was concentrated in vacuo to give the title compound (100 mg, 97% yield, TFA) as a yellow solid. LC-MS (ESI⁺) m/z 373.5 (M+H)⁺.

2-(2,6-Dioxo-3-piperidyl)-4-[[(2S)-4-[3-(methylamino)propyl]morpholin-2-yl]methylamino] isoindoline-1,3-dione (Intermediate ALC)

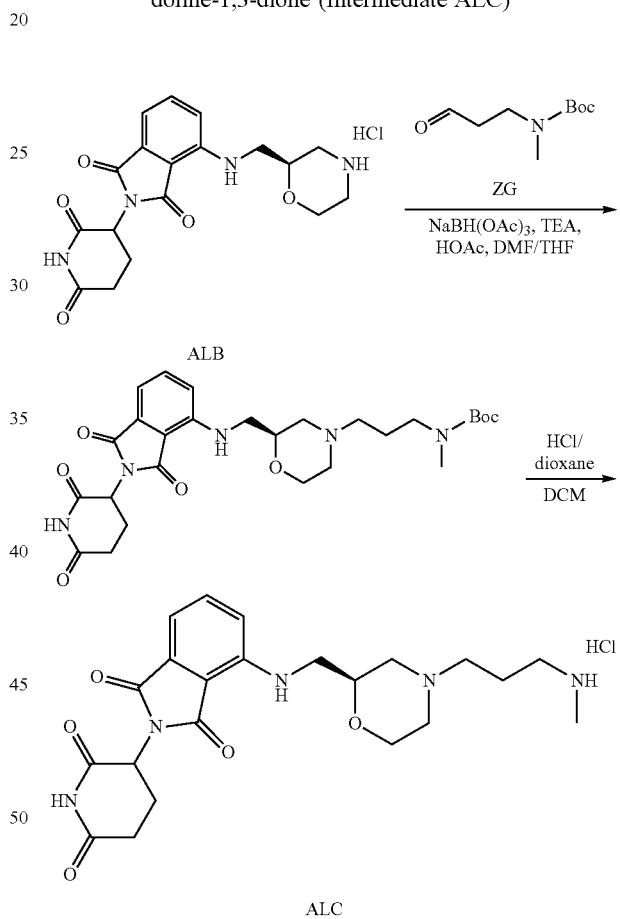

Step 1—Tert-butyl N-[3-[(2S)-2-[[[2-(2,6-dioxo-3-piperidyl)-1,3-dioxo-isoindolin-4-yl]amino]methyl] morpholin-4-yl]propyl]-N-methyl-carbamate To a solution of 2-(2,6-dioxo-3-piperidyl)-4-[[(2R)-morpholin-2-yl]methylamino]isoindoline-1,3-dione (100 mg, 205 umol, TFA salt, Intermediate ALB) in a mixed solvent of DMF (1.00 mL) and THF (1.00 mL) was added TEA (20.8 mg, 205 umol), the mixture was stirred at 20° C. for 10 minutes. Then, HOAc (24.7 mg, 411 umol) and tert-butyl N-methyl-N-(3-oxopropyl)carbamate (40.0 mg, 213 umol, Intermediate ZG) was added. The mixture was stirred at 20° C. for 0.5 hour. After that, NaBH(OAc)₃ (52.3 mg, 246 umol) was added, the mixture was stirred at 20° C. for 1 hour. On completion, the reaction mixture was quenched with H₂O (0.5 mL), and then concentrated in vacuo to give a residue. The residue was purified by reverse phase (0.1% FA condition) to give the title compound (60.0 mg, 53% yield) as a yellow solid. ¹H NMR (400 MHz, CDCl₃) δ 8.19 (s, 1H), 7.55-7.48 (m, 1H), 7.14 (d, J=7.2 Hz, 1H), 6.93 (d, J=8.8 Hz, 1H), 6.48 (t, J=5.6 Hz, 1H), 4.99-4.88 (m, 1H), 4.03-3.90 (m, 2H), 3.89-3.79 (m, 1H), 3.48-3.41 (m, 2H), 3.36-3.33 (m, 2H), 3.27 (t, J=6.4 Hz, 2H), 2.94-2.87 (m, 1H), 2.84 (s, 3H), 2.82-2.70 (m, 2H), 2.68-2.52 (m, 2H), 2.49-2.19 (m, 2H), 2.18-2.10 (m, 1H), 1.95-1.74 (m, 2H), 1.46 (s, 9H).

Step 2—2-(2,6-Dioxo-3-piperidyl)-4-[[(2S)-4-[3-(methylamino)propyl]morpholin-2-yl]methylamino]isoindoline-1,3-dione To a solution of tert-butyl N-[3-[(2S)-2-[[[2-(2,6-dioxo-3-piperidyl)-1,3-dioxo-isoindolin-4-yl]amino] methyl]morpholin-4-yl]propyl]-N-methyl-carbamate (90.0 mg, 165 umol) in DCM (1.00 mL) was added HCl/dioxane (4 M, 1.00 mL). The mixture was stirred at 20° C. for 0.5 hour. On completion, the reaction mixture was concentrated in vacuo to give the title compound (79.0 mg, 99% yield, HCl salt) as a yellow solid. LC-MS (ESI⁺) m/z 444.2 (M+H)⁺.

Tert-butyl 4-nitro-1H-pyrazole-3-carboxylate (Intermediate ANY)

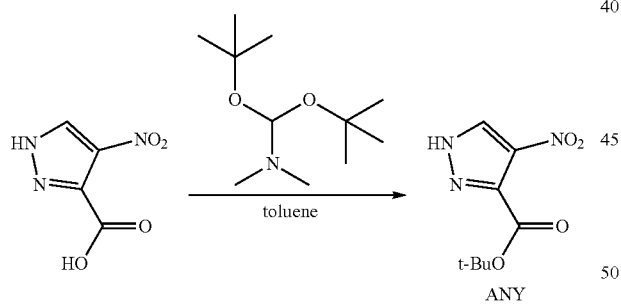

To a mixture of 1,1-ditert-butoxy-N,N-dimethyl-methanamine (11.6 g, 57.3 mmol, from CAS #36805-97-7) in toluene (20 mL) was added 4-nitro-1H-pyrazole-3-carboxylic acid (3.00 g, 19.1 mmol, from CAS #5334-40-7). The mixture was stirred at 100° C. for 12 hours. On completion, the reaction was concentrated in vacuo to give the residue. The residue was purified by column chromatography (petroleum ether/ethyl acetate=10:1) to give the title compound (2.60 g, 63% yield) as a white solid. ¹H NMR (400 MHz, CDCl₃) δ 8.38 (s, 1H), 8.27 (s, 1H), 1.62 (s, 9H).

Tert-butyl 4-amino-2-[4-(hydroxymethyl)cyclohexyl]pyrazole-3-carboxylate (Intermediate ANZ)

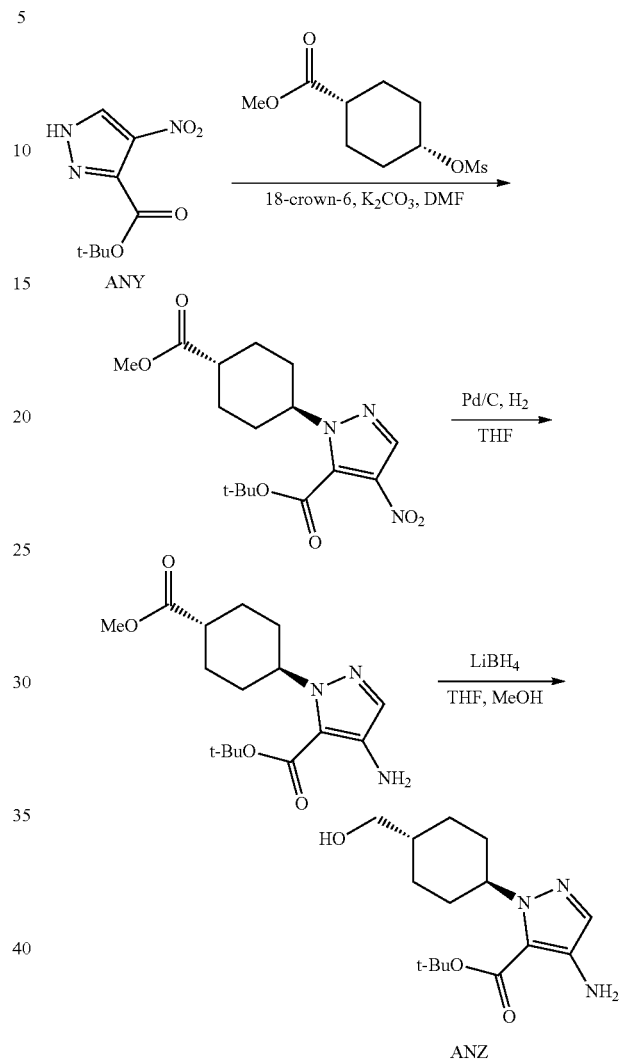

Step 1—Tert-butyl 1-(4-methoxycarbonylcyclohexyl)-4-nitro-pyrazole-3-carboxylate To a mixture of methyl 4-methylsulfonyloxycyclohexanecarboxylate (3.32 g, 14.0 mmol, synthesized via Step 1 of Intermediate QS) and tert-butyl 4-nitro-1H-pyrazole-3-carboxylate (2.00 g, 9.38 mmol, Intermediate ANY) in DMF (20 mL) was added K₂CO₃ (3.89 g, 28.1 mmol) and 1,4,7,10,13,16-hexaoxacyclooctadecane (248 mg, 938 umol, from CAS #17455-13-9). The reaction mixture was stirred at 80° C. for 12 hours. On completion, the reaction mixture was poured into the ice-water (200 mL), and extracted with EA (2×150 mL). The combined organic layer was washed with brine (2×100 mL), dried with anhydrous Na₂SO₄, filtered and concentrated in vacuo to give the residue. The residue was purified by column chromatography (petroleum ether/ethyl acetate=2:1) to give the title compound (1.80 g, 54% yield) as a brown solid. 1H NMR (400 MHz, CDCl₃) δ 8.00 (s, 1H), 4.25 (d, J=7.6 Hz, 1H), 3.70 (s, 3H), 2.45-2.36 (m, 1H), 2.24-2.16 (m, 2H), 2.15-2.08 (m, 2H), 2.08-1.96 (m, 3H), 1.66-1.63 (m, 1H), 1.63 (s, 9H).

Step 2—Tert-butyl 4-amino-1-(4-methoxycarbonyl-cyclohexyl)pyrazole-3-carboxylate To a mixture of tert-butyl 1-(4-methoxycarbonylcyclo-hexyl)-4-nitro-pyrazole-3-carboxylate (1.00 g, 2.83 mmol) in THF (20 mL) was added Pd/C (100 mg, 10 wt %). The mixture was stirred at 25° C. for 2 hours under $H_2$ (15 psi). On completion, the reaction mixture was filtered and concentrated in vacuo to give the title compound (905 mg, 98% yield) as a brown solid. $^1$H NMR (400 MHz, DMSO-$d_6$) δ 7.03 (s, 1H), 4.88 (s, 2H), 4.78-4.67 (m, 1H), 3.60 (s, 3H), 2.41-2.31 (m, 1H), 2.08-1.97 (m, 2H), 1.96-1.86 (m, 2H), 1.81-1.68 (m, 2H), 1.54 (s, 9H), 1.51-1.39 (m, 2H).

Step 3—Tert-butyl 4-amino-2-[4-(hydroxymethyl)cyclohexyl]pyrazole-3-carboxylate To a mixture of tert-butyl 4-amino-2-(4-methoxycarbo-nylcyclohexyl)pyrazole-3-carboxylate (650 mg, 2.01 mmol) in THF (20 mL) and MeOH (2.5 mL) was added $LiBH_4$ (87.5 mg, 4.02 mmol) at 0° C., the mixture was stirred at 50° C. for 3 hours. On completion, the reaction mixture was poured into the water (60 mL), and extracted with DCM (2×30 mL). The combined organic layer was washed with brine (2×60 mL), dried with anhydrous $Na_2SO_4$, filtered and concentrated in vacuo to give the title compound (458 mg, 77% yield) as a brown solid. $^1$H NMR (400 MHz, DMSO-$d_6$) δ 7.02 (s, 1H), 4.85 (s, 2H), 4.77-4.66 (m, 1H), 4.42 (d, J=5.2 Hz, 1H), 3.24 (d, J=5.6 Hz, 2H), 1.95-1.79 (m, 4H), 1.77-1.64 (m, 2H), 1.54 (s, 9H), 1.42-1.32 (m, 1H), 1.10-0.94 (m, 2H).

3-(9-(2,6-Dioxopiperidin-3-yl)-9H-pyrido[2,3-b]indol-4-yl)propanal (Intermediate ANA)

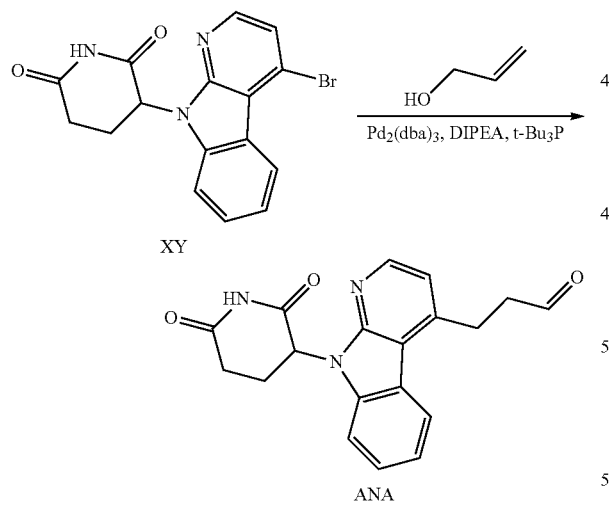

A mixture of 3-(4-bromopyrido[2,3-b]indol-9-yl)piperi-dine-2,6-dione (450 mg, 1.26 mmol, Intermediate XY), prop-2-en-1-ol (145 mg, 2.51 mmol, 170 uL), t-Bu$_3$P (762 mg, 376 umol, 884 uL, 10 wt %), DIPEA (487 mg, 3.77 mmol, 656 uL) and Pd$_2$(dba)$_3$ (115 mg, 125 umol) in dioxane (8 mL) was stirred at 80° C. for 16 hours. On completion, the reaction mixture was diluted with water (20 mL) and extracted with EA (3×30 mL). Combined organic layers were dried over $Na_2SO_4$, filtered and concentrated in vacuo to give gray oil. The gray oil was purified by column chromatography (SiO$_2$, PE/EA=3/1 to 1/1 to EA/DCM=20/1) to give the title compound (310 mg, 55% yield) as yellow solid. $^1$H NMR (400 MHz, DMSO-$d_6$) δ=11.14 (s, 1H), 9.83 (s, 1H), 8.33 (d, J=5.2 Hz, 1H), 8.14 (d, J=7.6 Hz, 1H), 7.73-7.60 (m, 1H), 7.53 (t, J=7.6 Hz, 1H), 7.33 (t, J=7.6 Hz, 1H), 7.12 (d, J=4.8 Hz, 1H), 6.15-5.93 (m, 1H), 3.51-3.43 (m, 1H), 3.47 (t, J=7.2 Hz, 1H), 3.32-3.29 (m, 2H), 3.02 (t, J=7.2 Hz, 1H), 3.08-3.02 (m, 1H), 3.09 (d, J=3.2 Hz, 1H), 2.75-2.62 (m, 1H), 2.17-2.04 (m, 1H). LC-MS (ESI$^+$) m/z 336.1 (M+H)$^+$.

Tert-butyl 2-(3-(9-(2,6-dioxopiperidin-3-yl)-9H-pyrido[2,3-b]indol-4-yl)propyl)-2,7-diazaspiro[3.5]nonane-7-carboxylate (Intermediate ANB)

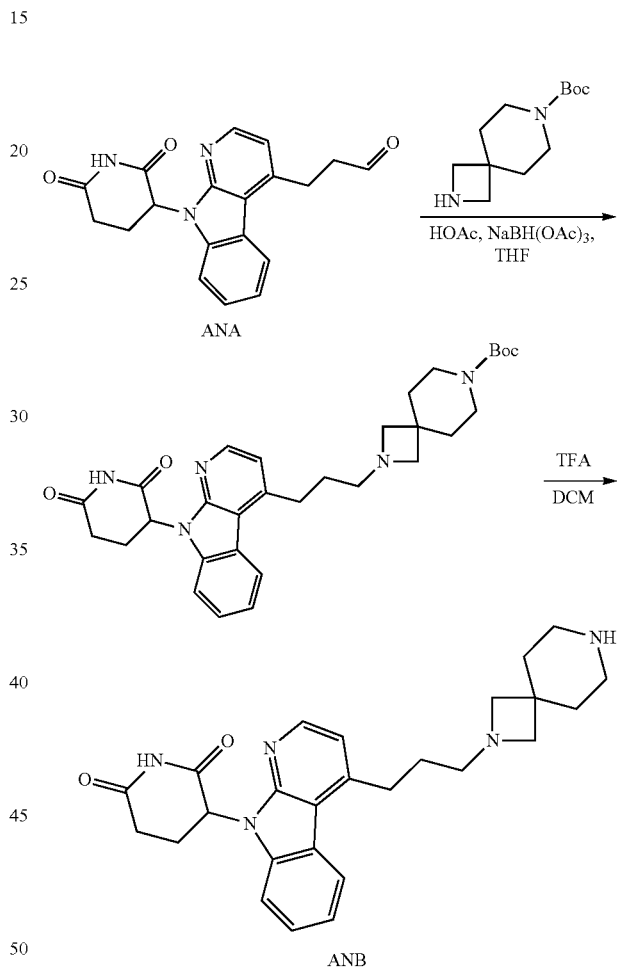

Step 1—Tert-butyl 2-(3-(9-(2,6-dioxopiperidin-3-yl)-9H-pyrido[2,3-b]indol-4-yl)propyl)-2,7-diaz-aspiro[3.5]nonane-7-carboxylate To a solution of 3-[9-(2,6-dioxo-3-piperidyl)pyrido[2,3-b]indol-4-yl]propanal (280 mg, 584 umol, Intermediate ANA) in THF (36 mL) was added and AcOH (70.2 mg, 1.17 mmol, 66.8 uL) and tert-butyl 2,7-diazaspiro[3.5]nonane-7-carboxylate (158 mg, 701 umol). The reaction mixture was stirred at 15° C. for 0.5 hour. After that, NaBH(OAc)$_3$ (148 mg, 701 umol) was added. The reaction mixture was stirred at 15° C. for 0.5 hour. On completion, the reaction was quenched with addition of water (20 mL) and extracted with EA (2×40 mL). The combined organic layers were dried over Na$_2$SO$_4$, filtered and concentrated in vacuo to give a yellow solid. The yellow solid was purified by column chromatography (SiO$_2$, EA to THF) to give the title compound (208 mg, 55% yield) as yellowish solid. $^1$H NMR (400 MHz, DMSO-d$_6$) δ 11.15 (s, 1H), 8.31 (d, J=4.8 Hz, 1H), 8.24 (d, J=7.6 Hz, 1H), 7.53 (t, J=7.6 Hz, 1H), 7.32 (t, J=7.6 Hz, 1H), 7.09 (d, J=5.2 Hz, 1H), 6.88 (s, 1H), 3.61 (ddd, J=6.4, 4.0, 2.4 Hz, 2H), 3.28-3.22 (m, 3H), 3.21 (d, J=6.8 Hz, 2H), 2.96 (s, 4H), 2.74-2.67 (m, 1H), 2.59-2.53 (m, 2H), 2.15-2.07 (m, 1H), 1.80-1.71 (m, 4H), 1.65-1.59 (m, 4H), 1.39 (s, 9H). LC-MS (ESI$^+$) m/z 546.4 (M+H)$^+$.

Step 2—Tert-butyl 2-(3-(9-(2,6-dioxopiperidin-3-yl)-9H-pyrido [2,3-b]indol-4-yl) propyl)-2,7-diazaspiro[3.5]nonane-7-carboxylate To a solution of tert-butyl 2-[3-[9-(2,6-dioxo-3-piperidyl)pyrido[2,3-b]indol-4-yl]propyl]-2,7-diazaspiro[3.5]nonane-7-carboxylate (200 mg, 366 umol) in DCM (5 mL) was added TFA (1 mL). The reaction mixture was stirred at 15° C. for 0.5 hour. On completion, the mixture was concentrated in vacuo to give the title compound (170 mg, crude) as yellow oil. LC-MS (ESI$^+$) m/z 446.3 (M+H)$^+$.

3-[1-(2,6-Dioxo-3-piperidyl)-3-methyl-2-oxo-benzimidazol-4-yl]propanal (Intermediate ANC)

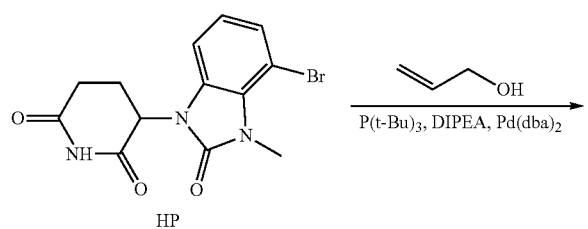

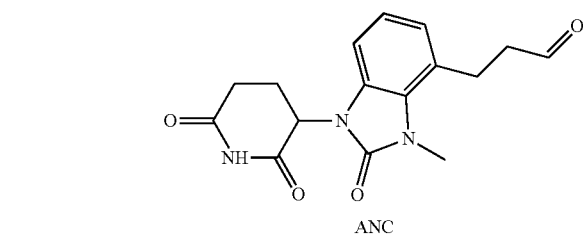

To a solution of 3-(4-bromo-3-methyl-2-oxo-benzimidazol-1-yl)piperidine-2,6-dione (2.00 g, 5.91 mmol, Intermediate HP) and prop-2-en-1-ol (687 mg, 11.8 mmol, 804 uL) in dioxane (20 mL) was added DIPEA (1.53 g, 11.8 mmol, 2.06 mL) and Pd(dba)$_2$ (340 mg, 591 umol). The reaction mixture was degassed with N$_2$ atmosphere. Then P(t-Bu)$_3$ (3.59 g, 1.77 mmol, 4.16 mL, 10 wt %) was added under N$_2$ atmosphere. The reaction mixture was stirred at 70° C. for 1 hour under N$_2$ atmosphere. On completion, the reaction mixture was filtered and the filtrate was concentrated in vacuo. The residue was purified by reverse phase (0.1% FA) to give the title compound (1.20 g, 64% yield) as light yellow solid. LC-MS (ESI$^+$) m/z 316.2 (M+H)$^+$.

3-[4-[3-(2,3,3a,4,6,6a-Hexahydro-1H-pyrrolo[3,4-c]pyrrol-5-yl)propyl]-3-methyl-2-oxo-benzimidazol-1-yl]piperidine-2,6-dione (Intermediate AND)

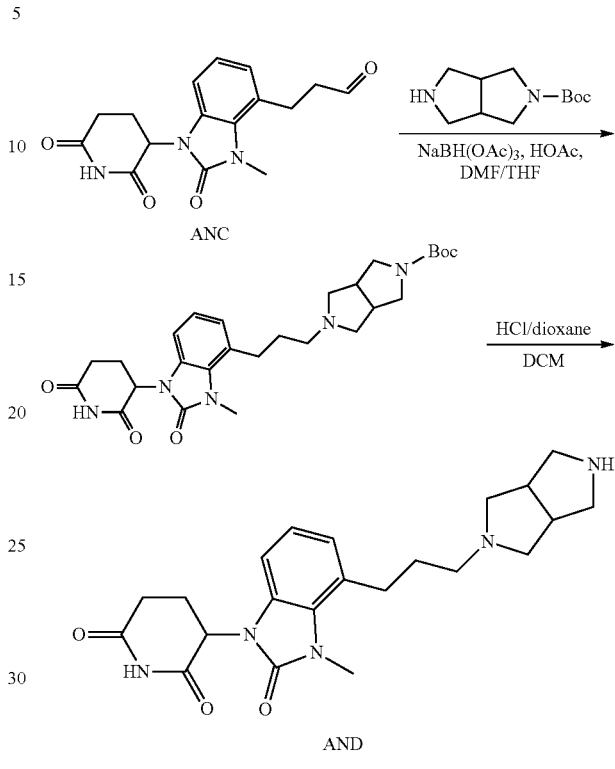

Step 1—Tert-butyl 2-[3-[1-(2,6-dioxo-3-piperidyl)-3-methyl-2-oxo-benzimidazol-4-yl]propyl]-1,3,3a,4,6,6a-hexahydropyrrolo[3,4-c]pyrrole-5-carboxylate To a solution of 3-[1-(2,6-dioxo-3-piperidyl)-3-methyl-2-oxo-benzimidazol-4-yl]propanal (89.1 mg, 282 umol, Intermediate ANC) and tert-butyl 2,3,3a,4,6,6a-hexahydro-1H-pyrrolo[3,4-c]pyrrole-5-carboxylate (50.0 mg, 235 umol, CAS #141449-85-6) in a mixed solvent of THF (2 mL) and DMF (0.5 mL) was added TEA (23.8 mg, 235 umol, 32.8 uL), HOAc (28.3 mg, 471 umol, 26.9 uL) and stirred for 0.5 hr. Then NaBH(OAc)$_3$ (74.9 mg, 353 umol) was added and the reaction mixture was stirred at 25° C. for 20 hrs. On completion, the reaction mixture was quenched with water (0.5 ml) and concentrated in vacuo. The residue was purified by reversed-phase HPLC (0.1% FA condition) to give the title compound (45.0 mg, 67% yield) as a yellow solid. $^1$H NMR (400 MHz, DMSO-d$_6$) δ 11.08-11.0 (m, 1H), 8.16 (d, J=4.8 Hz, 1H), 6.95 (t, J=4.8 Hz, 1H), 6.91-6.85 (m, 1H), 5.40-5.31 (m, 1H), 3.56-3.52 (m, 6H), 3.11 (d, J=10.4 Hz, 4H), 2.96-2.89 (m, 3H), 2.77-2.60 (m, 7H), 2.03-1.94 (m, 1H), 1.78-1.68 (d, J=5.2 Hz, 2H), 1.38 (d, J=5.2 Hz, 9H); LC-MS (ESI$^+$) m/z 512.3 (M+H)$^+$.

Step 2-3-[4-[3-(2,3,3a,4,6,6a-Hexahydro-1H-pyrrolo[3,4-c]pyrrol-5-yl)propyl]-3-methyl-2-oxo-benzimidazol-1-yl]piperidine-2,6-dione To a solution of tert-butyl 2-[3-[1-(2,6-dioxo-3-piperidyl)-3-methyl-2-oxo-benzimidazol-4-yl]propyl]-1,3,3a,4,6,6a-hexahydropyrrolo[3,4-c]pyrrole-5-carboxylate (40.0 mg, 60.1 umol) in DCM (2 mL) was added HCl (4 M, 10.0 mL). The mixture was stirred at 25° C. for 2 hours. On completion, the reaction mixture was concentrated in vacuo to give the title compound (24.0 mg, 89% yield, HCl) as yellow solid. LC-MS (ESI+) m/z 412.3 (M+H)+.

Tert-butyl 2-cyano-5-prop-2-ynoxy-pentanoate (Intermediate ANE)

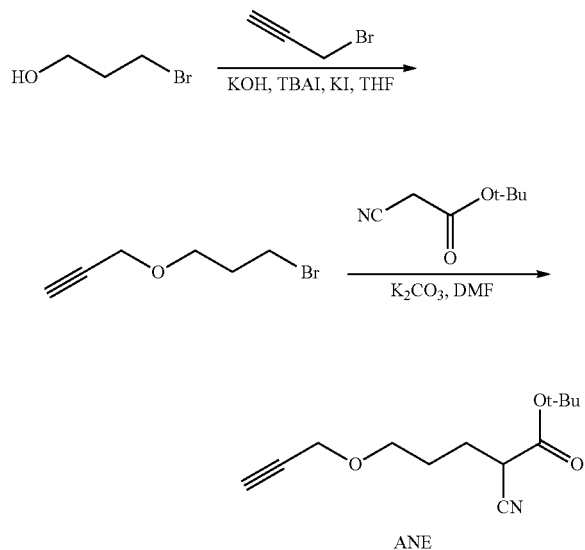

Step 1—1-Bromo-3-prop-2-ynoxy-propane

A mixture of 3-bromopropan-1-ol (25.0 g, 179 mmol, CAS #627-18-9), TBAI (6.65 g, 18.0 mmol), KI (2.99 g, 18.0 mmol), KOH (10.1 g, 180 mmol) and 3-bromoprop-1-yne (32.1 g, 215 mmol, CAS #106-96-7) in THF (300 mL) was stirred at 25° C. for 16 hours. On completion, the mixture was filtered, and the cake was washed with EA (100 mL). The filtrate was concentrated in vacuo. The residue was purified by column chromatography on silica gel to give the title compound (12.0 g, 37% yield) as light yellow oil. $^1$H NMR (400 MHz, CDCl$_3$) δ 4.16 (d, J=2.4 Hz, 2H), 3.66 (t, J=6.0 Hz, 2H), 3.52 (t, J=6.4 Hz, 2H), 2.45 (t, J=2.4 Hz, 1H), 2.17-2.11 (m, 2H).

Step 2—Tert-butyl 2-cyano-5-prop-2-ynoxy-pentanoate

A mixture of 1-bromo-3-prop-2-ynoxy-propane (7.00 g, 39.5 mmol), tert-butyl 2-cyanoacetate (6.14 g, 43.4 mmol, CAS #1116-98-9) and K$_2$CO$_3$ (11.0 g, 79.5 mmol) in DMF (70 mL) was stirred at 80° C. for 16 hours. On completion, the mixture was poured into 1.0 M aq.HCl (200 mL), diluted with water (100 mL), then extracted with a mixed solution of PE:EA=3:1 (3×100 mL). The combine organic layer was washed with brine (100 mL), dried over Na$_2$SO$_4$, filtered and concentrated in vacuo. The residue was purified by column chromatography on silica gel to give the title compound (6.60 g, 70% yield) as light yellow oil. $^1$H NMR (400 MHz, CDCl$_3$) δ 4.15 (d, J=2.4 Hz, 2H), 3.61-3.59 (m, 2H), 3.50-3.48 (m, 1H), 2.44 (t, J=2.4 Hz, 1H), 2.11-1.96 (m, 2H), 1.87-1.76 (m, 2H), 1.51 (s, 9H).

Tert-butyl 2-(4-formylcyclohexyl)-4-[[5-[(1R,4R)-2-oxa-5-azabicyclo[2.2.1]heptan-5-yl] pyrazolo[1,5-a]pyrimidine-3-carbonyl]amino]pyrazole-3-carboxylate (Intermediate AOA)

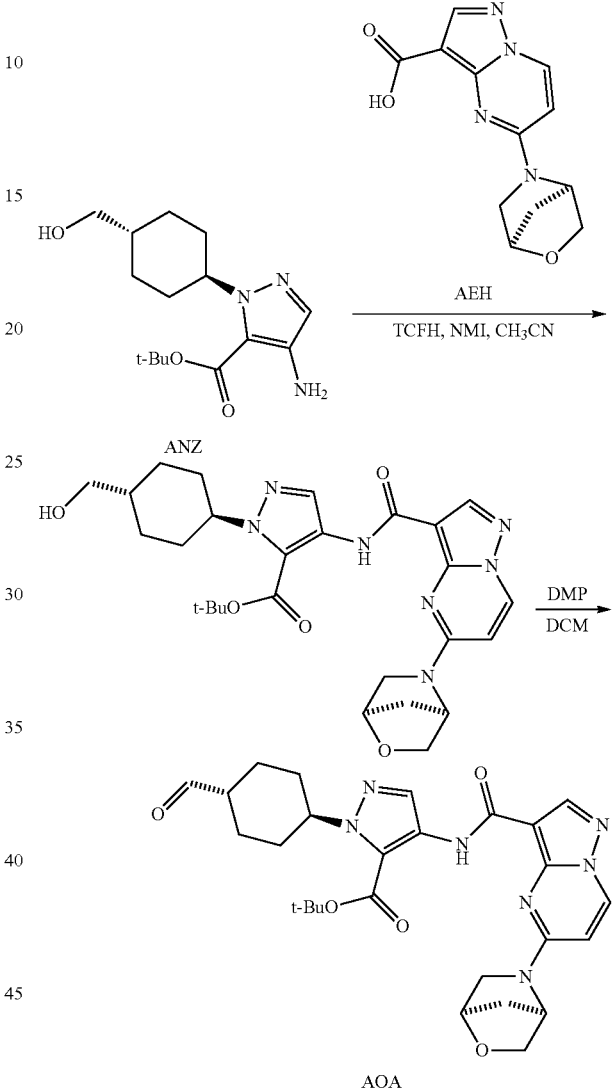

Step 1—Tert-butyl 2-[4-(hydroxymethyl)cyclohexyl]-4-[[5-[(1R)-2-oxa-5-azabicyclo[2.2.1] heptan-5-yl]pyrazolo [1,5-a]pyrimidine-3-carbonyl] amino]pyrazole-3-carboxylate To a mixture of 5-[(1R)-2-oxa-5-azabicyclo[2.2.1]heptan-5-yl]pyrazolo[1,5-a]pyrimidine-3-carboxylic acid (286 mg, 1.10 mmol, Intermediate AEH), tert-butyl 4-amino-2-[4-(hydroxymethyl)cyclohexyl] pyrazole-3-carboxylate (250 mg, 846 umol, Intermediate ANZ) in ACN (15 mL) was added [chloro (dimethylamino) methylene]-dimethyl-ammonium; hexafluorophosphate (308 mg, 1.10 mmol). Then 1-methylimidazole (243 mg, 2.96 mmol) was added into the mixture. The reaction mixture was stirred at 25° C. for 1 hour. On completion, the reaction was filtered, the filter cake was collected. The solid was purified by reverse phase (0.1%

FA condition) to give the title compound (210 mg, 46% yield) as a white solid. $^1$H NMR (400 MHz, DMSO-d$_6$) δ 10.28-10.20 (m, 1H), 8.77 (d, J=7.6 Hz, 1H), 8.40-8.30 (m, 1H), 8.29-8.24 (m, 1H), 6.90-5.95 (m, 2H), 5.12-4.60 (m, 3H), 3.88-3.74 (m, 2H), 3.62 (d, J=9.6 Hz, 1H), 3.47 (d, J=10.0 Hz, 1H), 3.27 (d, J=6.4 Hz, 2H), 2.06-1.95 (m, 3H), 1.95-1.73 (m, 5H), 1.61 (s, 9H), 1.67-1.64 (m, 1H), 1.14-0.99 (m, 2H).

Step 2—Tert-butyl 2-(4-formylcyclohexyl)-4-[[5-[(1R,4R)-2-oxa-5-azabicyclo[2.2.1]heptan-5-yl]pyrazolo[1,5-a]pyrimidine-3-carbonyl]amino]pyrazole-3-carboxylate To a mixture of tert-butyl 2-[4-(hydroxymethyl)cyclohexyl]-4-[[5-[(1R,4R)-2-oxa-5-azabicyclo [2.2.1] heptan-5-yl]pyrazolo[1,5-a]pyrimidine-3-carbonyl]amino]pyrazole-3-carboxylate (200 mg, 372 umol) in DCM (2 mL) was added DMP (173 mg, 409 umol). The reaction mixture was stirred at 25° C. for 0.5 hour. On completion, the mixture was poured into the water (80 mL), and extracted with DCM (2×60 mL). The combined organic layer was washed with brine (2×50 mL), dried with anhydrous Na$_2$SO$_4$, filtered and concentrated in vacuo to give the title compound (185 mg, 92% yield) as a white solid. $^1$H NMR (400 MHz, DMSO-d$_6$) δ 10.30-10.20 (m, 1H), 9.63 (s, 1H), 8.77 (d, J=7.6 Hz, 1H), 8.41-8.31 (m, 1H), 8.30-8.25 (m, 1H), 6.90-5.72 (m, 2H), 5.14-4.62 (m, 3H), 3.62 (d, J=10.0 Hz, 1H), 3.47 (d, J=9.6 Hz, 1H), 2.17-2.00 (m, 6H), 1.95-1.81 (m, 4H), 1.60 (s, 9H), 1.39-1.29 (m, 2H).

2-(2,6-Dioxo-3-piperidyl)-4-[3-[(2S)-2-(methylaminomethyl)morpholin-4-yl]propylamino] isoindoline-1,3-dione (Intermediate AME)

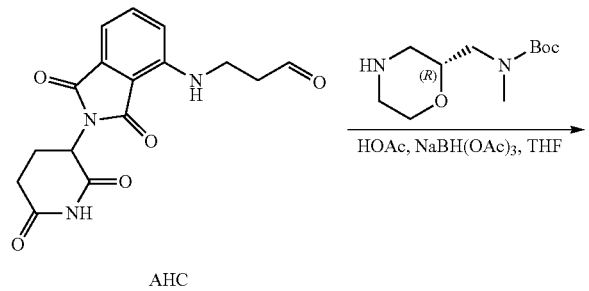

AHC

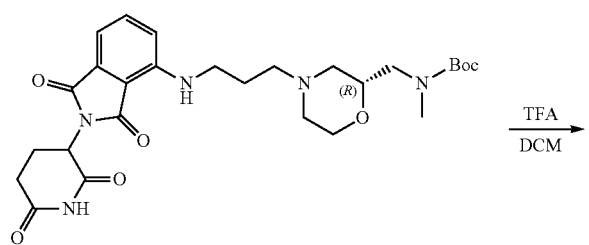

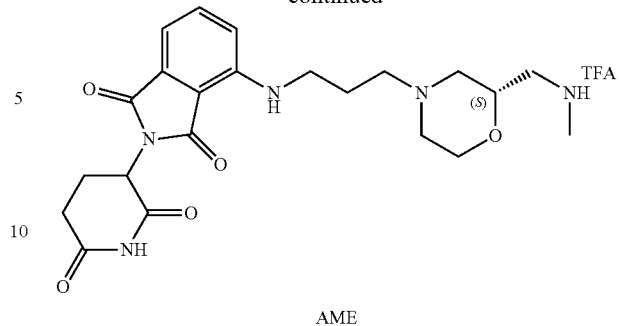

AME

Step 1—Tert-butyl N-[[(2R)-4-[3-[[2-(2,6-dioxo-3-piperidyl)-1,3-dioxo-isoindolin-4-yl]amino]propyl]morpholin-2-yl]methyl]-N-methyl-carbamate To a mixture of 3-[[2-(2,6-dioxo-3-piperidyl)-1,3-dioxo-isoindolin-4-yl]amino]propanal (70.0 mg, 212 umol, Intermediate AHC) in THF (5 mL) was added TEA (21.5 mg, 212 umol, 29.5 uL) and stirred at 25° C. for 12 min. Then tert-butyl N-methyl-N-[[(2R)-morpholin-2-yl]methyl]carbamate (48.9 mg, 212.57 umol, synthesized via Steps 1-5 of Intermediate WP) and HOAc (12.7 mg, 212 umol, 12.1 uL) was added to the mixture and stirred at 25° C. for 0.5 hour. Finally NaBH(OAc)$_3$ (67.5 mg, 318 umol) was added to the mixture at 0° C. The reaction mixture was stirred at 25° C. for 12 hours. On completion, the reaction mixture was quenched with water (0.05 mL) and concentrated in vacuo. The residue was purified by reverse phase (0.1% FA condition) to give the title compound (55.0 mg, 47% yield) as yellow solid. $^1$H NMR (400 MHz, DMSO-d$_6$) δ 11.07 (d, J=2.8 Hz, 1H), 7.60-7.54 (m, 1H), 7.12 (d, J=8.8 Hz, 1H), 7.01 (d, J=7.2 Hz, 1H), 6.81-6.73 (m, 1H), 5.08-5.01 (m, 1H), 3.77 (d, J=9.6 Hz, 1H), 3.68-3.62 (m, 1H), 3.59-3.51 (m, 2H), 3.22-3.14 (m, 5H), 2.79 (s, 3H), 2.69-2.66 (m, 2H), 2.63-2.56 (m, 2H), 2.39-2.35 (m, 2H), 2.30-2.24 (m, 1H), 2.01-1.97 (m, 1H), 1.74-1.71 (m, 2H), 1.36 (s, 9H).

Step 2—2-(2,6-Dioxo-3-piperidyl)-4-[3-[(2S)-2-(methylaminomethyl)morpholin-4-yl]propylamino] isoindoline-1,3-dione To a mixture of tert-butyl N-[[(2R)-4-[3-[[2-(2,6-dioxo-3-piperidyl)-1,3-dioxo-isoindolin-4-yl]amino] propyl]morpholin-2-yl]methyl]-N-methyl-carbamate (50.0 mg, 91.9 umol) in DCM (1 mL) was added TFA (1.54 g, 13.5 mmol, 1 mL). The reaction mixture was stirred at 25° C. for 0.5 hour. On completion, the reaction mixture was concentrated in vacuo to give the title compound (51.0 mg, 99% yield, TFA) as red oil. LC-MS (ESI$^+$) m/z 444.3 (M+H)$^+$.

2-(2,6-dioxopiperidin-3-yl)-4-(((1s,4s)-4-(methyl-amino)cyclohexyl)amino)isoindoline-1,3-dione (Intermediate ALG) & 2-(2,6-dioxopiperidin-3-yl)-4-(((r,4r)-4-(methylamino)cyclohexyl)amino)isoindoline-1,3-dione (Intermediate ALH)

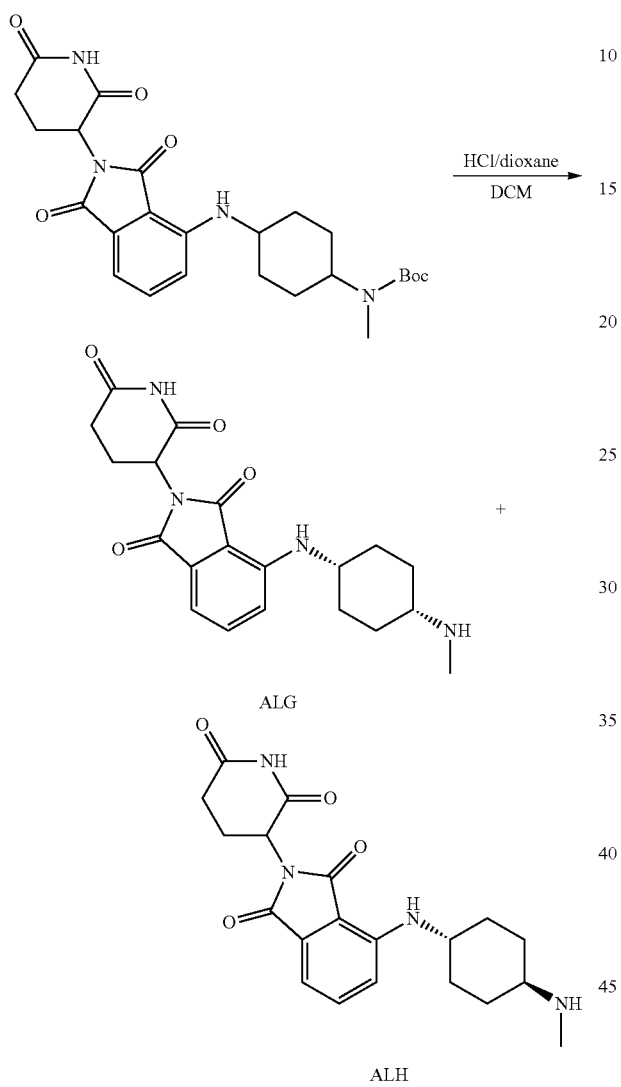

ALG

ALH

To a solution of tert-butyl N-[4-[[2-(2,6-dioxo-3-piperidyl)-1,3-dioxo-isoindolin-4-yl]amino] cyclohexyl]-N-methyl-carbamate (240 mg, 495 umol, synthesized via Step 1 of Intermediate AIO) in DCM (3.00 mL) was added HCl/dioxane (4.00 M, 7.20 mL). The mixture was stirred at 15° C. for 0.5 hr. On completion, the mixture concentrated in vacuo. The mixture was purified by prep-HPLC twice (column: Phenomenex Synergi C18 150*25*10 um; mobile phase: [water (0.225% FA)-ACN]; B %: 0%-30%, 10 min) to give the title compounds 2-(2,6-dioxopiperidin-3-yl)-4-(((1s,4s)-4-(methylamino)cyclohexyl)amino)isoindoline-1,3-dione (45.0 mg, 23% yield) as yellow solid and 2-(2,6-dioxopiperidin-3-yl)-4-(((1r,4r)-4-(methylamino)cyclohexyl)amino)isoindoline-1,3-dione (100 mg, 52% yield) as yellow solid. Characterization of 2-(2,6-dioxopiperidin-3-yl)-4-(((1s,4s)-4-(methylamino)cyclohexyl)amino)isoindoline-1,3-dione: $^1$H NMR (400 MHz, D$_2$O) δ 8.37 (s, 1H), 7.50 (dd, J=7.2, 8.4 Hz, 1H), 7.08-6.99 (m, 2H), 5.13-5.00 (m, 1H), 3.87-3.76 (m, 1H), 3.19-3.09 (m, 1H), 2.89-2.74 (m, 2H), 2.64 (s, 3H), 2.62-2.49 (m, 1H), 2.15-2.10 (m, 1H), 1.97-1.81 (m, 4H), 1.79-1.69 (m, 2H), 1.67-1.52 (m, 2H). Characterization of 2-(2,6-dioxopiperidin-3-yl)-4-(((1r,4r)-4-(methylamino)cyclohexyl)amino)isoindoline-1,3-dione: $^1$H NMR (400 MHz, D$_2$O) δ 8.37 (s, 1H), 7.50 (dd, J=7.2, 8.8 Hz, 1H), 7.11-7.01 (m, 2H), 5.11-5.00 (m, 1H), 3.57-3.44 (m, 1H), 3.12-3.00 (m, 1H), 2.88-2.70 (m, 2H), 2.64 (s, 3H), 2.61-2.43 (m, 1H), 2.19-2.06 (m, 5H), 1.56-1.42 (m, 2H), 1.40-1.26 (m, 2H).

Tert-butyl N-[[4-(2-aminoethyl)phenyl]methyl]carbamate (Intermediate AOO)

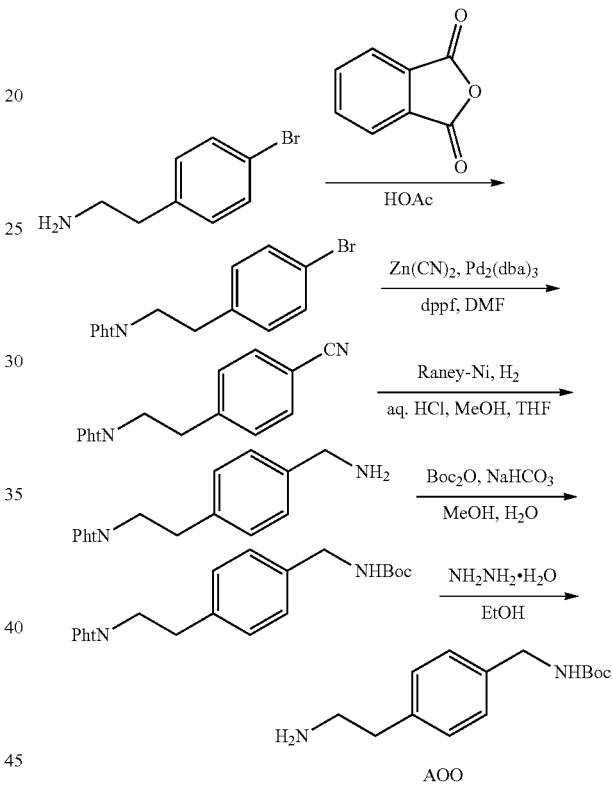

AOO

Step 1—2-[2-(4-Bromophenyl)ethyl]isoindoline-1,3-dione

A mixture of 2-(4-bromophenyl)ethanamine (2.00 g, 10.0 mmol, CAS #73918-56-6) and isobenzofuran-1,3-dione (1.63 g, 11.0 mmol) in HOAc (20 mL) was stirred at 120° C. for 16 hours. On completion, after cooled to 15° C., the mixture was diluted with water (200 mL) and the mixture was filtered. The cake was collected and dried to give the title compound (3.00 g, 90% yield) as white solid. $^1$H NMR (400 MHz, DMSO-d$_6$) δ 7.86-7.80 (m, 4H), 7.43 (d, J=8.0 Hz, 2H), 7.16 (d, J=8.0 Hz, 2H), 3.81 (t, J=7.2 Hz, 2H), 2.90 (t, J=7.2 Hz, 2H).

Step 2—4-[2-(1,3-Dioxoisoindolin-2-yl)ethyl]benzonitrile

A mixture of 2-[2-(4-bromophenyl)ethyl]isoindoline-1,3-dione (1.50 g, 4.54 mmol), Zn(CN)$_2$ (1.17 g, 9.96 mmol), Pd$_2$(dba)$_3$ (458 mg, 500 umol) and DPPF (554 mg, 999 umol) in DMF (30 mL) was stirred at 100° C. for 16 hours. On completion, the mixture was cooled to 15° C., diluted with water (150 mL), and extracted with EA (3×80 mL). The combined organic layer was washed with brine (50 mL), dried over Na$_2$SO$_4$, filtered and concentrated in vacuo to give a residue. The residue was purified by column chromatography on silica gel to give the title compound (1.20 g, 95% yield) as light yellow solid. $^1$H NMR (400 MHz, DMSO-d$_6$) δ 7.84-7.82 (m, 4H), 7.72 (d, J=8.0 Hz, 2H), 7.42 (d, J=8.0 Hz, 2H), 3.85 (t, J=7.2 Hz, 2H), 3.02 (t, J=7.2 Hz, 2H).

Step 3—2-[2-[4-(Aminomethyl)phenyl]ethyl]isoindoline-1,3-dione

A mixture of 4-[2-(1,3-dioxoisoindolin-2-yl)ethyl]benzonitrile (950 mg, 3.44 mmol), HCl (2.0 M, 5.2 mL) and Raney-Ni (300 mg, 3.50 mmol) in MeOH (20 mL) and THF (20 mL) was stirred at 25° C. for 16 hours under H$_2$ (45 Psi). On completion, the mixture was filtered and the filter cake was washed with MeOH (20 mL). The filtrate and washing were combined and concentrated in vacuo to give the title compound (1.08 g, 99% yield, HCl salt) as light yellow solid. LC-MS (ESI$^+$) m/z 264.1 (M-NH$_2$)$^+$.

Step 4—Tert-butyl N-[[4-[2-(1,3-dioxoisoindolin-2-yl)ethyl]phenyl]methyl] carbamate A mixture of 2-[2-[4-(aminomethyl)phenyl]ethyl]isoindoline-1,3-dione (1.03 g, 3.25 mmol, HCl salt), Boc$_2$O (1.08 g, 4.95 mmol) and NaHCO$_3$ (832 mg, 9.90 mmol) in MeOH (15 mL) and H$_2$O (5 mL) was stirred at 20° C. for 16 hours. On completion, the mixture was concentrated in vacuo. The residue was diluted with EA (50 mL), washed with brine (10 mL), dried over Na$_2$SO$_4$, filtered and concentrated in vacuo. The residue was purified by reversed phase flash (FA condition) to give the title compound (570 mg, 46% yield) as light yellow solid. $^1$H NMR (400 MHz, DMSO-d$_6$) δ 7.91-7.77 (m, 4H), 7.32 (t, J=6.0 Hz, 1H), 7.19-7.07 (m, 4H), 4.06 (d, J=6.0 Hz, 2H), 3.79 (t, J=7.2 Hz, 2H), 2.89 (t, J=7.2 Hz, 2H), 1.38 (s, 9H).

Step 5—Tert-butyl N-[[4-(2-aminoethyl)phenyl]methyl]carbamate

A mixture of tert-butyl N-[[4-[2-(1,3-dioxoisoindolin-2-yl)ethyl]phenyl]methyl]carbamate (570 mg, 1.50 mmol) and NH$_2$NH$_2$—H$_2$O (570 mg, 11.3 mmol) in EtOH (10 mL) was stirred at 80° C. for 2 hours. On completion, the mixture was cooled to 15° C. and then filtered. The filtrate was concentrated in vacuo to give the title compound (370 mg, 98% yield) as light yellow solid. $^1$H NMR (400 MHz, CDCl$_3$) δ 7.25-7.20 (m, 2H), 7.19-7.13 (m, 2H), 4.84 (s, 1H), 4.29 (d, J=5.6 Hz, 2H), 3.01-2.92 (m, 2H), 2.79-2.70 (m, 2H), 1.47 (s, 9H).

2-[[2-(2,6-Dioxo-3-piperidyl)-1,3-dioxo-isoindolin-4-yl]amino]acetic acid (Intermediate AOR)

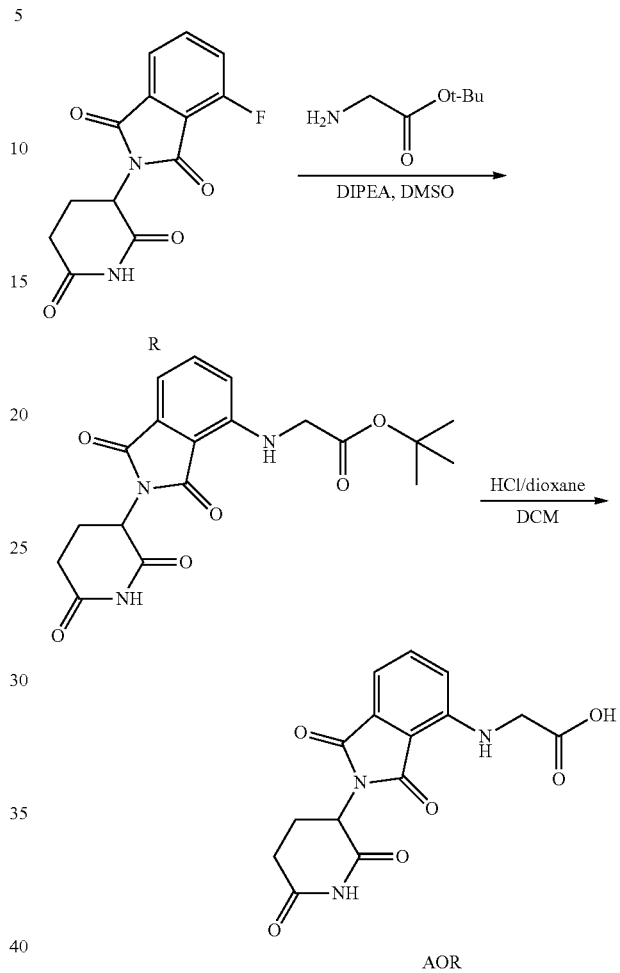

Step 1—Tert-butyl 2-[[2-(2,6-dioxo-3-piperidyl)-1,3-dioxo-isoindolin-4-yl]amino]acetate To a solution of 2-(2,6-dioxo-3-piperidyl)-4-fluoro-isoindoline-1,3-dione (350 mg, 1.27 mmol, Intermediate R) and tert-butyl 2-aminoacetate (216 mg, 1.65 mmol, CAS #6456-74-2) in DMSO (10 mL) was added DIPEA (327 mg, 2.53 mmol) at 25° C. The reaction mixture was stirred at 130° C. for 3 hrs. On completion, the reaction mixture was filtered and the filtrate was concentrated in vacuo. The residue was purified by reverse phase (0.1% FA condition) to give the title compound (360 mg, 73% yield) as yellow solid. $^1$H NMR (400 MHz, DMSO-d$_6$) δ 11.10 (s, 1H), 7.63-7.53 (m, 1H), 7.08 (d, J=7.2 Hz, 1H), 6.98 (d, J=8.4 Hz, 1H), 6.85 (t, J=6.0 Hz, 1H), 5.07 (dd, J=5.2, 12.8 Hz, 1H), 4.09 (d, J=6.0 Hz, 2H), 2.95-2.82 (m, 1H), 2.64-2.52 (m, 2H), 2.09-2.00 (m, 1H), 1.43 (s, 9H); LC-MS (ESI$^+$) m/z 388.2 (M+H)$^+$.

Step 2—2-[[2-(2,6-Dioxo-3-piperidyl)-1,3-dioxo-isoindolin-4-yl]amino]acetic acid To a solution of tert-butyl 2-[[2-(2,6-dioxo-3-piperidyl)-1,3-dioxo-isoindolin-4-yl]amino]acetate (160 mg, 413 umol) in DCM (5 mL) was added HCl/dioxane (4 M, 3 mL)

at 25° C. The mixture was stirred at 25° C. for 2 hrs. On completion, the mixture was concentrated in vacuo to give the title compound (150 mg, 98% yield, HCl salt) as yellow solid. LC-MS (ESI$^+$) m/z 332.0 (M+H)$^+$.

4-[[2-(2,7-Diazaspiro[3.5]nonan-2-yl)-2-oxo-ethyl]amino]-2-(2,6-dioxo-3-piperidyl) isoindoline-1,3-dione (Intermediate AOS)

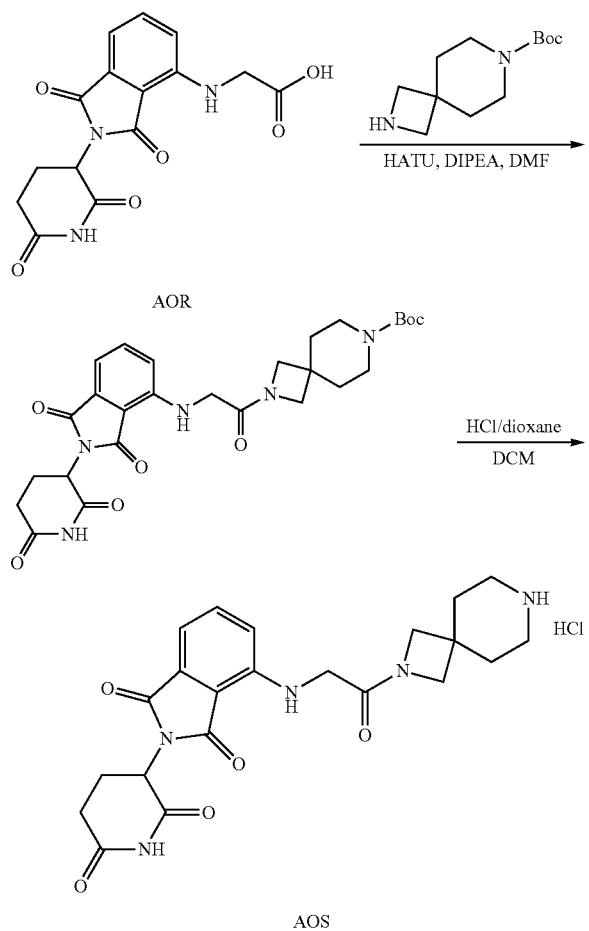

Step 1—Tert-butyl 2-[2-[[2-(2,6-dioxo-3-piperidyl)-1,3-dioxo-isoindolin-4-yl]amino]acetyl]-2,7-diazaspiro[3.5]nonane-7-carboxylate To a solution of tert-butyl 2,7-diazaspiro[3.5]nonane-7-carboxylate (102 mg, 452 umol, CAS #896464-16-7) in DMF (8 mL) was added DIPEA (117 mg, 905 umol) at 25° C. and the mixture was stirred for 0.5 hour. Then 2-[[2-(2,6-dioxo-3-piperidyl)-1,3-dioxo-isoindolin-4-yl]amino]acetic acid (150 mg, 452 umol, Intermediate AOR) and HATU (206 mg, 543 umol) were added to the mixture at 25° C. Then the reaction mixture was stirred at 25° C. for 2 hrs. On completion, the mixture was concentrated in vacuo. The residue was purified by reverse phase (0.1% FA condition) to give the title compound (150 mg, 61% yield) as yellow solid. $^1$H NMR (400 MHz, DMSO-d$_6$) δ 11.10 (s, 1H), 7.59-7.55 (m, 1H), 7.08 (dd, J=3.6, 6.8 Hz, 1H), 6.99 (t, J=6.0 Hz, 1H), 6.89-6.79 (m, 1H), 5.11-5.03 (m, 1H), 4.13-3.95 (m, 2H), 3.91 (s, 1H), 3.65 (s, 1H), 3.32-3.26 (m, 6H), 2.95-2.83 (m, 1H), 2.63-2.51 (m, 4H), 2.09-1.99 (m, 1H), 1.69-1.61 (m, 2H), 1.41 (d, J=15.6 Hz, 9H); LC-MS (ESI$^+$) m/z 540.2 (M+H)$^+$.

Step 2—4-[[2-(2,7-Diazaspiro[3.5]nonan-2-yl)-2-oxo-ethyl]amino]-2-(2,6-dioxo-3-piperidyl) isoindoline-1,3-dione To a solution of tert-butyl 2-[2-[[2-(2,6-dioxo-3-piperidyl)-1,3-dioxo-isoindolin-4-yl]amino]acetyl]-2,7-diazaspiro[3.5]nonane-7-carboxylate (50.0 mg, 92.6 umol) in DCM (3 mL) was added HCl/dioxane (4 M, 1.00 mL) at 25° C. The mixture was stirred at 25° C. for 2 hrs. On completion, the reaction mixture was concentrated in vacuo to give the title compound (44.0 mg, 99% yield, HCl salt) as a yellow solid. LC-MS (ESI$^+$) m/z 440.1 (M+H)$^+$.

Benzyl N-3-(3-aminocyclobutoxy)propyl]-N-methyl-carbamate (Intermediate AOY)

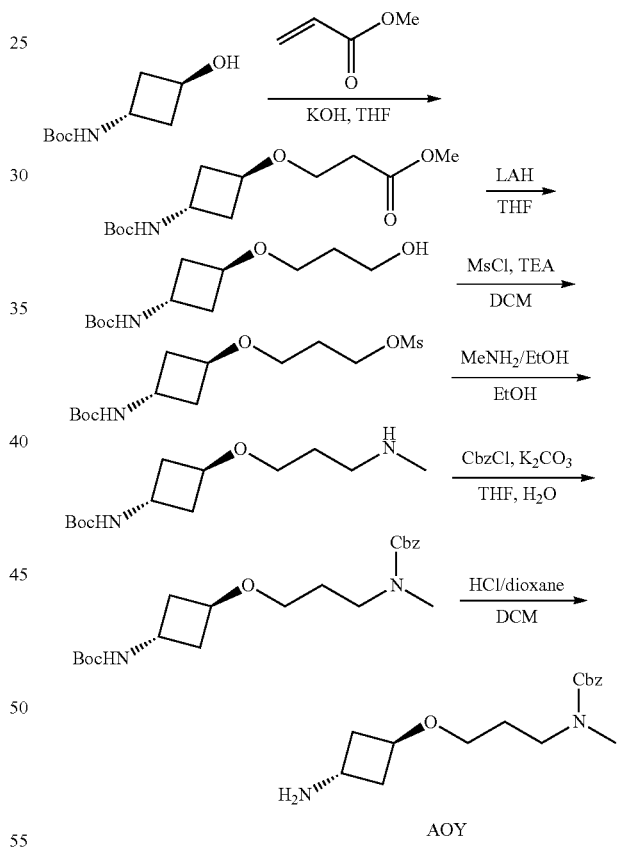

Step 1—Methyl 3-[3-(tert-butoxycarbonylamino) cyclobutoxy]propanoate

To a solution of tert-butyl N-(3-hydroxycyclobutyl)carbamate (2.50 g, 13.3 mmol, CAS #389890-42-0) and methyl prop-2-enoate (2.30 g, 26.7 mmol, CAS #96-33-3) in THF (25 mL) was added KOH (74.9 mg, 1.34 mmol). The reaction mixture was stirred at 20° C. for 16 hrs. On completion, the reaction mixture was diluted with water (80 mL) and extracted with EA (3×80 mL). The combined organic layers were washed with brine (2×50 mL), dried over Na$_2$SO$_4$, filtered and concentrated in vacuo. The residue was purified by silica gel chromatography (PE:EA=8:1) to give the title compound (1.80 g, 49% yield) as colorless oil. $^1$H NMR (400 MHz, CDCl$_3$) δ 4.81-4.59 (m, 1H), 4.26-4.03 (m, 2H), 3.70 (s, 3H), 3.59 (t, J=6.4 Hz, 2H), 2.57 (t, J=6.4 Hz, 2H), 2.42-2.30 (m, 2H), 2.19-2.06 (m, 2H), 1.44 (s, 9H).

Step 2—Tert-butyl N-[3-(3-hydroxypropoxy)cyclobutyl]carbamate

To a solution of methyl 3-[3-(tert-butoxycarbonylamino)cyclobutoxy]propanoate (1.80 g, 6.59 mmol) in THF (20 mL) was added LAH (274 mg, 7.24 mmol). The reaction mixture was stirred at 0° C. for 1 hr. On completion, the reaction mixture was quenched by water (0.25 mL), added 15% NaOH (0.3 mL), water (0.8 mL), diluted with EA (50 mL), dried over Na$_2$SO$_4$, filtered and concentrated in vacuo to give the title compound (1.50 g, 92.% yield) as yellow oil. $^1$H NMR (400 MHz, CDCl$_3$) δ 4.70 (s, 1H), 4.54-4.41 (m, 1H), 4.27-4.14 (m, 1H), 4.12-4.04 (m, 1H), 3.81-3.74 (m, 2H), 3.50 (t, J=6.0 Hz, 2H), 2.37-2.30 (m, 2H), 2.24-2.14 (m, 2H), 1.86-1.80 (m, 2H), 1.44 (s, 9H).

Step 3—3-[3-(Tert-butoxycarbonylamino)cyclobutoxy]propyl methanesulfonate

To a solution of tert-butyl N-[3-(3-hydroxypropoxy)cyclobutyl]carbamate (1.50 g, 6.11 mmol) and TEA (928 mg, 9.17 mmol) in DCM (20 mL) was added MsCl (840 mg, 7.34 mmol) at 0° C. The reaction mixture was stirred at 0° C. for 1 hr. On completion, the reaction mixture was diluted with water (20 mL) and extracted with DCM (3×40 mL). The combined organic layers were washed with brine (2×30 mL), dried over Na$_2$SO$_4$, filtered and concentrated in vacuo to give the title compound (1.90 g, crude) as yellow oil. $^1$H NMR (400 MHz, CDCl$_3$) δ 5.23-5.11 (m, 1H), 4.79-4.66 (m, 1H), 4.34 (t, J=6.0 Hz, 2H), 4.09-4.04 (m, 1H), 3.42 (t, J=6.0 Hz, 2H), 3.02 (s, 3H), 2.51-2.26 (m, 4H), 2.00 (q, J=6.0 Hz, 2H), 1.44 (s, 9H).

Step 4—Tert-butyl N-[3-[3-(methylamino)propoxy]cyclobutyl]carbamate

A mixture of 3-[3-(tert-butoxycarbonylamino)cyclobutoxy]propyl methanesulfonate (1.90 g, 5.87 mmol) and MeNH$_2$/EtOH (5.87 mmol, 10 mL, 30% solution) was stirred at 70° C. for 12 hrs in a sealed tube (15 psi). On completion, the reaction mixture was concentrated in vacuo to give the title compound (1.80 g, crude) as yellow oil and used for next step directly. LC-MS (ESI$^+$) m/z 259.0 (M+H)$^+$.

Step 5—Benzyl N-[3-[3-(tert-butoxycarbonylamino)cyclobutoxy]propyl]-N-methyl-carbamate To a solution of tert-butyl N-[3-[3-(methylamino)propoxy]cyclobutyl]carbamate (1.80 g, 6.97 mmol) and K$_2$CO$_3$ (1.93 g, 13.9 mmol) in a mixed solvents of THF (15 mL) and water (5 mL) was added CbzCl (1.78 g, 10.4 mmol). The reaction mixture was stirred at 20° C. for 2 hrs. On completion, the reaction mixture was diluted with water (30 mL) and extracted with EA (3×50 mL). The combined organic layers were washed with brine (2×30 mL), dried over Na$_2$SO$_4$, filtered and concentrated in vacuo. The residue was purified by silica gel chromatography (PE:EA=5:1) to give the title compound (1.30 g, 41% yield) as yellow oil. $^1$H NMR (400 MHz, CDCl$_3$) δ 7.39-7.29 (m, 5H), 5.13 (s, 2H), 4.79-4.58 (m, 1H), 4.32-4.14 (m, 1H), 4.07-3.92 (m, 1H), 3.42-3.21 (m, 4H), 2.94 (s, 3H), 2.39-2.23 (m, 2H), 2.14-2.05 (m, 2H), 1.87-1.72 (m, 2H), 1.45 (s, 9H).

Step 6—Benzyl N-[3-(3-aminocyclobutoxy)propyl]-N-methyl-carbamate

To a solution of benzyl N-[3-[3-(tert-butoxycarbonylamino)cyclobutoxy]propyl]-N-methyl-carbamate (1.60 g, 4.08 mmol) in DCM (20 mL) was added HCl/dioxane (4 M, 15 mL). The reaction mixture was stirred at 20° C. for 1 hour. On completion, the reaction mixture was concentrated in vacuo to give the title compound (1.30 g, 96% yield, HCl salt) as yellow semisolid. LC-MS (ESI$^+$) m/z 293.2 (M+H)$^+$.

2-(2,6-dioxo-3-piperidyl)-4-[[3-[3-(methylamino)propoxy]cyclobutyl]amino]isoindoline-1,3-dione (Intermediate AOQ)

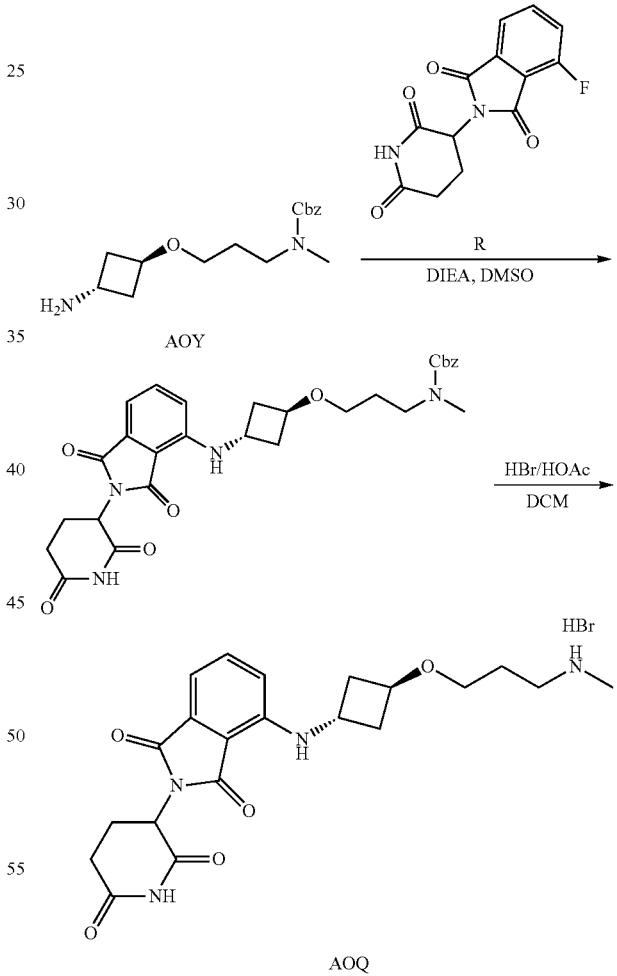

Step 1—Benzyl N-[3-[3-[[2-(2,6-dioxo-3-piperidyl)-1,3-dioxo-isoindolin-4-yl]amino] cyclobutoxy] propyl]-N-methyl-carbamate To a solution of benzyl N-[3-(3-aminocyclobutoxy)propyl]-N-methyl-carbamate (1.30 g, 3.95 mmol, HCl salt, Intermediate AOY) and 2-(2,6-dioxo-3-piperidyl)-4-fluoro-isoindoline-1,3-dione (928 mg, 3.36 mmol, Intermediate R) in DMSO (15 mL) was added DIPEA (2.55 g, 19.7 mmol). The reaction mixture was stirred at 130° C. for 3 hrs. On completion, the reaction mixture was diluted with water (50 mL) and extracted with EA (3×70 mL). The combined organic layers were washed with brine (50 mL), dried over $Na_2SO_4$, filtered and concentrated in vacuo. The residue was purified by reverse phase (0.1% FA) to give the title compound (810 mg, 37% yield) as yellow solid. $^1$H NMR (400 MHz, $CDCl_3$) δ 8.02 (s, 1H), 7.54-7.47 (m, 1H), 7.42-7.28 (m, 5H), 7.14 (d, J=7.2 Hz, 1H), 6.80-6.64 (m, 1H), 6.36-6.22 (m, 1H), 5.14 (s, 2H), 4.99-4.87 (m, 1H), 4.24-4.05 (m, 2H), 3.47-3.28 (m, 4H), 2.95 (s, 3H), 2.93-2.84 (m, 1H), 2.84-2.70 (m, 2H), 2.57-2.35 (m, 2H), 2.28-2.09 (m, 3H), 1.90-1.74 (m, 2H).

Step 2—2-(2,6-Dioxo-3-piperidyl)-4-[[3-[3-(methylamino)propoxy]cyclobutyl]amino]isoindoline-1,3-dione To a solution of benzyl N-[3-[3-[[2-(2,6-dioxo-3-piperidyl)-1,3-dioxo-isoindolin-4-yl]amino] cyclobutoxy]propyl]-N-methyl-carbamate (0.80 g, 1.46 mmol) in DCM (10 mL) was added HBr/AcOH (1.46 mmol, 10 mL, 30% solution). The reaction mixture was stirred at 20° C. for 1 hour. On completion, the reaction mixture was dried by nitrogen. The residue was diluted with ACN/$H_2O$=1/1 (100 mL) and lyophilizated to give the title compound (722 mg, 99% yield, HBr salt) as yellow solid. $^1$H NMR (400 MHz, DMSO-$d_6$) δ 11.09 (s, 1H), 8.32 (s, 2H), 7.60 (dd, J=7.2, 8.4 Hz, 1H), 7.09 (d, J=7.0 Hz, 1H), 6.91 (d, J=8.4 Hz, 1H), 6.68-6.25 (m, 1H), 5.06 (dd, J=5.6, 12.8 Hz, 1H), 4.22-4.11 (m, 2H), 3.38 (t, J=6.0 Hz, 2H), 3.04-2.80 (m, 3H), 2.63-2.55 (m, 4H), 2.54-2.52 (m, 1H), 2.44-2.33 (m, 2H), 2.29-2.18 (m, 2H), 2.12-1.97 (m, 1H), 1.90-1.76 (m, 2H).

Tert-butyl N-(4-aminocyclohexyl)-N-methyl-carbamate (Intermediate AOZ)

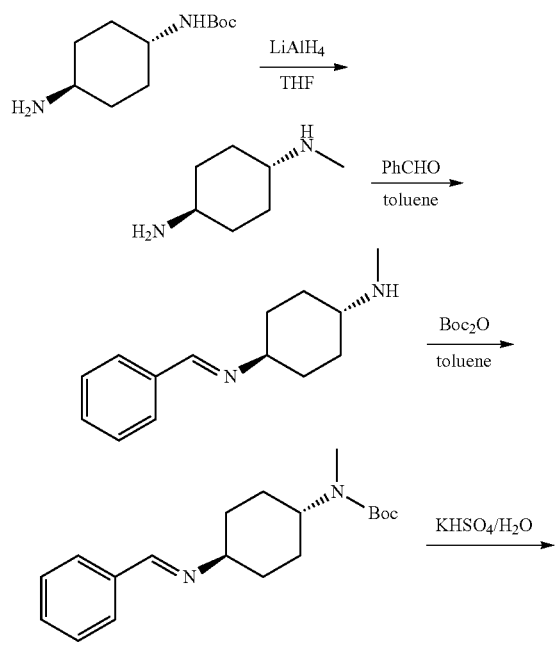

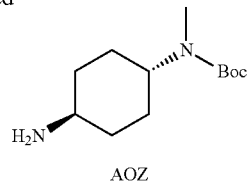

AOZ

Step 1—$N_4$-methylcyclohexane-1,4-diamine

To a solution of tert-butyl N-(4-aminocyclohexyl)carbamate (15.0 g, 70.0 mmol, CAS #177906-48-8) in THF (100 mL) was added $LiAlH_4$ (13.3 g, 350 mmol) at 0° C. The mixture was stirred at 70° C. for 3 hours. On completion, the reaction was cooled to 20° C., then it was quenched with $H_2O$ (80 mL), filtered and the filtered cake was washed with EA (3×150 mL). The combined organic was dried over $Na_2SO_4$, filtered and concentrated in vacuo to give the title compound (6.90 g, 100% yield) as a yellow solid. $^1$H NMR (400 MHz, DMSO-$d_6$) δ 2.48-2.41 (m, 1H), 2.27-2.21 (m, 3H), 2.13-2.10 (m, 1H), 1.85-1.65 (m, 4H), 1.06-0.87 (m, 4H).

Step 2—4-(Benzylideneamino)-N-methyl-cyclohexanamine

A solution of $N_4$-methylcyclohexane-1,4-diamine (3.20 g, 20.0 mmol) and benzaldehyde (2.20 g, 21.0 mmol) in toluene (50 mL) was stirred at 120° C. for 16 hours. On completion, the reaction was concentrated in vacuo to give the title compound (4.00 g, 100% yield) as yellow oil. $^1$H NMR (400 MHz, DMSO-$d_6$) δ 8.37 (s, 1H), 7.75-7.69 (m, 2H), 7.45-7.41 (m, 3H), 3.17 (br s, 1H), 2.30 (s, 4H), 1.98-1.91 (m, 2H), 1.71-1.63 (m, 2H), 1.60-1.47 (m, 2H), 1.16-1.05 (m, 2H).

Step 3—Tert-butyl N-[4-[(E)-benzylideneamino]cyclohexyl]-N-methyl-carbamate

To a solution of 4-[(E)-benzylideneamino]-N-methyl-cyclohexanamine (4.00 g, 18.5 mmol) in toluene (60 mL) was added $(Boc)_2O$ (4.80 g, 22.2 mmol, 5.1 mL). The mixture was stirred at 25° C. for 3 hours. On completion, the organic solvent was removed under vacuum to give the title compound (5.00 g, 90% yield) as yellow oil. $^1$H NMR (400 MHz, DMSO-$d_6$) δ 8.42 (s, 1H), 7.81-7.73 (m, 2H), 7.52-7.46 (m, 3H), 4.02-3.71 (m, 1H), 3.24 (d, J=4.2 Hz, 1H), 2.74 (s, 3H), 1.83-1.74 (m, 2H), 1.73-1.62 (m, 6H), 1.46 (s, 9H).

Step 4—Tert-butyl N-(4-aminocyclohexyl)-N-methyl-carbamate

A solution of $KHSO_4$ (7.5 g, 55.3 mmol) in $H_2O$ (56 mL) was added to tert-butyl N-[4-[(E)-benzylideneamino]cyclohexyl]-N-methyl-carbamate (5 g, 15.8 mmol), and the reaction was stirred at 25° C. for 3 h. On completion, the reaction was extracted with MTBE (3×50 mL) and the aqueous phase was basified with NaOH (6 N) to pH=11, then it was extracted with DCM (5×50 mL). The organic phase was dried over $Na_2SO_4$, filtered and concentrated under vacuum to give the title compound (3.00 g, 90% yield) as colorless oil. LC-MS (ESI$^+$) m/z 229.7 (M+H)$^+$.

2-(2,6-dioxo-3-piperidyl)-4-[[4-(methylamino)cyclohexyl]amino]isoindoline-1,3-dione (Intermediate AOV)

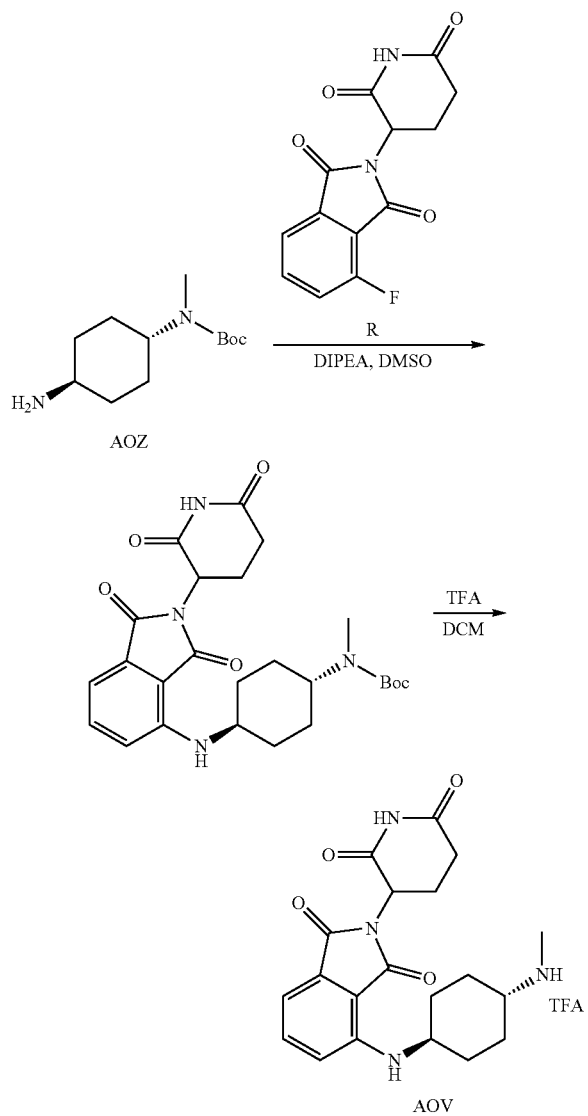

Step 1—Tert-butyl N-[4-[[2-(2,6-dioxo-3-piperidyl)-1,3-dioxo-isoindolin-4-yl]amino] cyclohexyl]-N-methyl-carbamate To a solution of tert-butyl N-(4-aminocyclohexyl)-N-methyl-carbamate (3.00 g, 13.1 mmol, Intermediate AOZ) and 2-(2,6-dioxo-3-piperidyl)-4-fluoro-isoindoline-1,3-dione (3.60 g, 13.1 mmol, Intermediate R) in DMSO (30 mL) was added DIPEA (3.40 g, 26.3 mmol, 4.6 mL). The mixture was stirred at 130° C. for 2 hour. On completion, the crude product was purified by reversed-phase HPLC (0.1% FA condition) to give the title compound (3.40 g, 48% yield) as a yellow solid. LC-MS (ESI$^+$) m/z 485.5 (M+H)$^+$.

Step 2—2-(2,6-Dioxo-3-piperidyl)-4-[[4-(methylamino)cyclohexyl]amino]isoindoline-1,3-dione To a solution of tert-butyl N-[4-[[2-(2,6-dioxo-3-piperidyl)-1,3-dioxo-isoindolin-4-yl]amino] cyclohexyl]-N-methyl-carbamate (0.60 g, 1.2 mmol) in DCM (8 mL) was added TFA (6.20 g, 54.0 mmol, 4 mL). The mixture was stirred at 25° C. for 0.5 hour. On completion, the reaction mixture was concentrated in vacuo to give the title compound (1.00 g, 100% yield, TFA) as yellow oil. LC-MS (ESI$^+$) m/z 384.9 (M+H)$^+$.

Tert-butyl 4-[5-[4-amino-3-(difluoromethyl)pyrazol-1-yl]pyrimidin-2-yl]piperazine-1-carboxylate (Intermediate AOT)

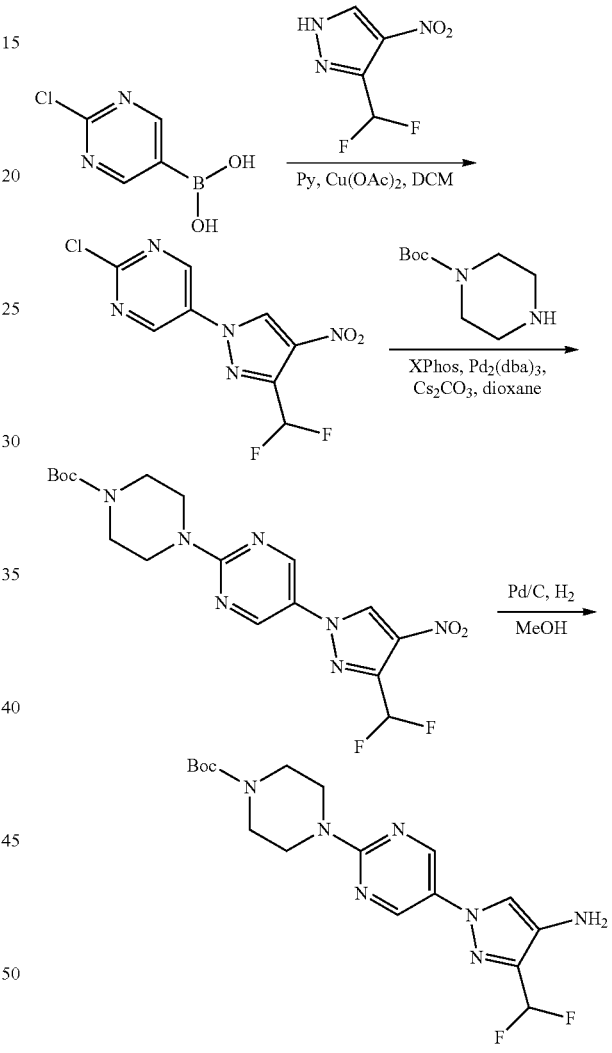

Step 1—2-Chloro-5-[3-(difluoromethyl)-4-nitropyrazol-1-yl]pyrimidine

To a mixture of 3-(difluoromethyl)-4-nitro-1H-pyrazole (5.00 g, 30.6 mmol, CAS #1003845-06-4) and (2-chloropyrimidin-5-yl)boronic acid (6.31 g, 39.8 mmol, CAS #1003845-06-4) in DCM (80 mL) was added Cu(OAc)$_2$ (1.11 g, 6.13 mmol) and pyridine (7.28 g, 91.9 mmol, 7.42 mL). The reaction mixture was stirred at 25° C. for 12 hours under O2 (15 Psi) atmosphere. On completion, the reaction mixture was quenched with NH$_4$.H$_2$O (0.05 mL) and concentrated in vacuo. The reaction mixture was filtered and diluted with water (80 mL) and extracted with DCM (2×100 mL). The combined organic layers was dried over Na₂SO₄, filtered and concentrated in vacuo to give the title compound (170 mg, 2% yield) as light yellow solid. 1H NMR (400 MHz, DMSO-d₆) δ 9.91 (s, 1H), 9.37 (s, 2H), 7.47 (t, J=52.4 Hz, 1H).

Step 2—Tert-butyl 4-[5-[3-(difluoromethyl)-4-nitro-pyrazol-1-yl]pyrimidin-2-yl]piperazine-1-carboxylate To a mixture of 2-chloro-5-[3-(difluoromethyl)-4-nitro-pyrazol-1-yl]pyrimidine (180 mg, 653 umol) and tert-butyl piperazine-1-carboxylate (182 mg, 979 umol, CAS #143238-38-4) in dioxane (3 mL) was added XPhos (155 mg, 326 umol), Cs₂CO₃ (808 mg, 2.48 mmol) and Pd₂(dba)₃ (83.7 mg, 91.4 umol). The reaction mixture was stirred at 95° C. for 12 hours. On completion, the reaction mixture was filtered and concentrated in vacuo. The residue was purified by reverse phase (0.1% FA condition) to give the title compound (180 mg, 64% yield) as brown solid. ¹H NMR (400 MHz, DMSO-d₆) δ 9.60 (s, 1H), 8.86 (s, 2H), 7.43-7.29 (m, 3H), 3.84-3.78 (m, 4H), 3.46-3.40 (m, 4H), 1.43 (s, 9H); LC-MS (ESI⁺) m/z 326.2 (M+H−100)⁺.

Step 3—Tert-butyl 4-[5-[4-amino-3-(difluoromethyl)pyrazol-1-yl]pyrimidin-2-yl]piperazine-1-carboxylate To a mixture of tert-butyl 4-[5-[3-(difluoromethyl)-4-nitro-pyrazol-1-yl]pyrimidin-2-yl]piperazine-1-carboxylate (180 mg, 423 umol) in MeOH (3 mL) was added Pd/C (150 mg, 10 wt %). The reaction mixture was stirred at 25° C. for 3 hours under H₂ (15 Psi) atmosphere. On completion, the reaction mixture was filtered and concentrated in vacuo to give the title compound (130 mg, 77% yield) as light yellow solid. ¹H NMR (400 MHz, DMSO-d₆) δ 8.72 (s, 2H), 7.68 (s, 1H), 7.14 (t, J=52.4 Hz, 1H), 3.80-3.70 (m, 4H), 3.44-3.39 (m, 4H), 1.43 (s, 9H); LC-MS (ESI⁺) m/z 418.2 (M+Na)⁺.

N-[3-(difluoromethyl)-1-(2-piperazin-1-ylpyrimidin-5-yl)pyrazol-4-yl]-5-morpholino-pyrazolo[1,5-a]pyrimidine-3-carboxamide (Intermediate AOU)

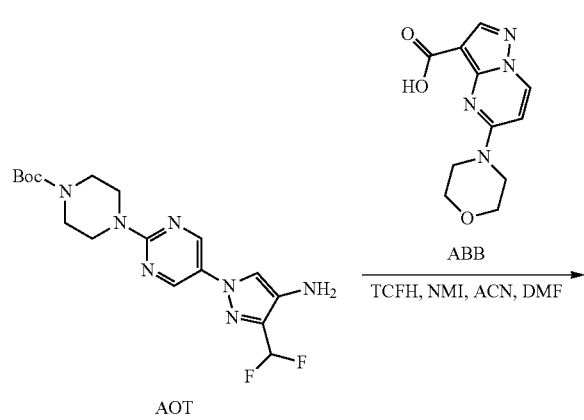

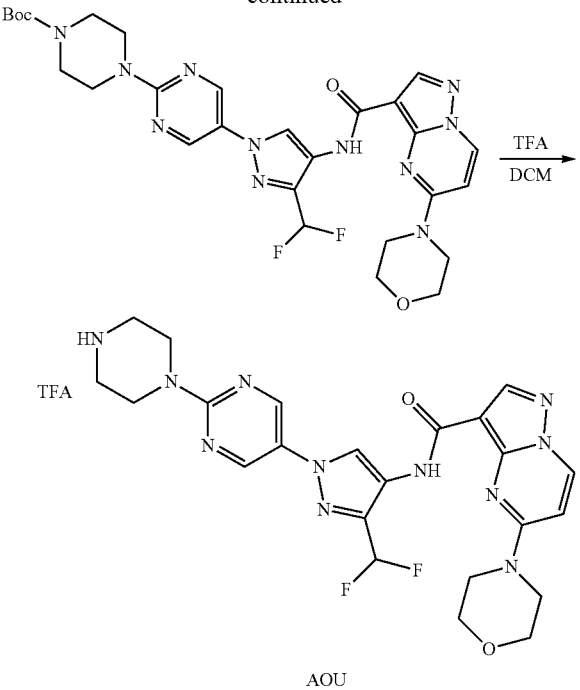

Step 1—Tert-butyl 4-[5-[3-(difluoromethyl)-4-[(5-morpholinopyrazolo[1,5-a]pyrimidine-3-carbonyl)amino]pyrazol-1-yl]pyrimidin-2-yl]piperazine-1-carboxylate To a mixture of 5-morpholinopyrazolo[1,5-a]pyrimidine-3-carboxylic acid (50.2 mg, 202 umol, Intermediate ABB), 1-methylimidazole (58.1 mg, 708 umol, 56.4 uL) and [chloro(dimethylamino)methylene]-dimethyl-ammonium; hexafluorophosphate (73.8 mg, 263 umol) in ACN (1 mL) and DMF (1 mL) was added tert-butyl 4-[5-[4-amino-3-(difluoromethyl)pyrazol-1-yl]pyrimidin-2-yl]piperazine-1-carboxylate (80.0 mg, 202 umol, Intermediate AOT). The reaction mixture was stirred at 60° C. for 72 hours. On completion, the reaction mixture was quenched with water (0.05 mL) and concentrated in vacuo. The residue was purified by reverse phase (0.1% FA condition) to give the title compound (20.0 mg, 15% yield) as white solid. LC-MS (ESI⁺) m/z 626.3 (M+H)⁺.

Step 2—N-[3-(difluoromethyl)-1-(2-piperazin-1-ylpyrimidin-5-yl)pyrazol-4-yl]-5-morpholino-pyrazolo[1,5-a]pyrimidine-3-carboxamide To a mixture of tert-butyl 4-[5-[3-(difluoromethyl)-4-[(5-morpholinopyrazolo[1,5-a]pyrimidine-3-carbonyl)amino]pyrazol-1-yl]pyrimidin-2-yl]piperazine-1-carboxylate (20.0 mg, 31.9 umol) in DCM (2 mL) was added TFA (2.31 g, 20.2 mmol, 1.5 mL). The reaction mixture was stirred at 25° C. for 0.5 hour. On completion, the reaction mixture was concentrated in vacuo to give the title compound (20.0 mg, 97% yield, TFA) as light yellow solid. LC-MS (ESI⁺) m/z 526.3 (M+H)⁺.

2-(2,6-Dioxo-3-piperidyl)-4-[[3-(methylamino)cyclobutyl]amino]isoindoline-1,3-dione (Intermediate AOW)

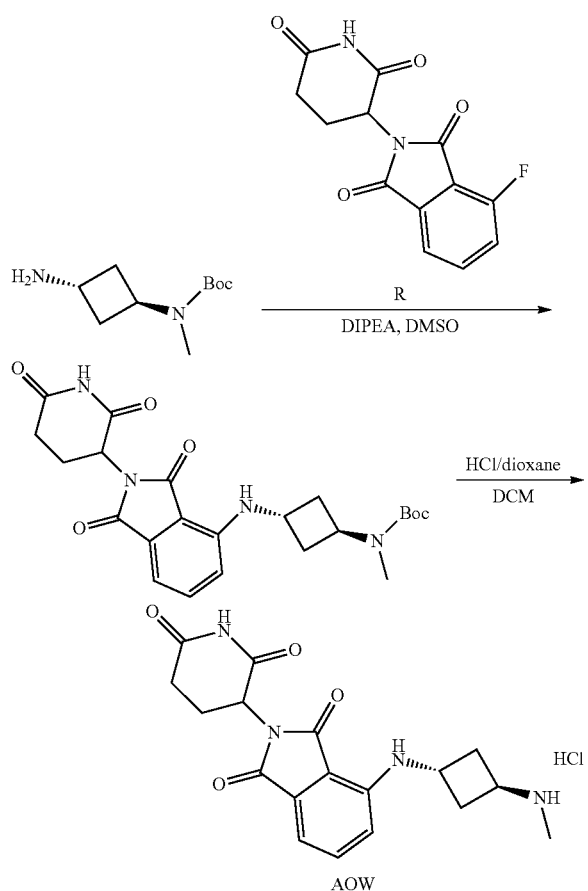

Step 1—Tert-butyl N-[3-[[2-(2,6-dioxo-3-piperidyl)-1,3-dioxo-isoindolin-4-yl]amino]cyclobutyl]-N-methyl-carbamate To a solution of tert-butyl N-(3-aminocyclobutyl)-N-methyl-carbamate (250 mg, 1.25 mmol, CAS #1392803-14-3) and 2-(2,6-dioxo-3-piperidyl)-4-fluoro-isoindoline-1,3-dione (362 mg, 1.31 mmol, Intermediate R) in DMSO (12 mL) was added DIPEA (322 mg, 2.50 mmol) at 25° C. The reaction mixture was stirred at 130° C. for 3 hrs. On completion, the reaction mixture was concentrated in vacuo. The residue was purified by reverse phase (0.1% FA condition) to give the title compound (500 mg, 87% yield) as a yellow solid. $^1$H NMR (400 MHz, DMSO-$d_6$) δ 11.09 (s, 1H), 7.60 (dd, J=7.2, 8.4 Hz, 1H), 7.09 (d, J=6.8 Hz, 1H), 6.89 (d, J=8.4 Hz, 1H), 6.55 (d, J=5.6 Hz, 1H), 5.07 (dd, J=5.2, 12.8 Hz, 1H), 4.77-4.52 (m, 1H), 4.15-3.95 (m, 1H), 2.96-2.84 (m, 1H), 2.82 (s, 3H), 2.66-2.52 (m, 4H), 2.20 (t, J=8.8 Hz, 2H), 2.10-1.97 (m, 1H), 1.39 (s, 9H); LC-MS (ESI$^+$) m/z 457.0 (M+H)$^+$.

Step 2—2-(2,6-Dioxo-3-piperidyl)-4-[[3-(methylamino)cyclobutyl] amino]isoindoline-1,3-dione To a solution of tert-butyl N-[3-[[2-(2,6-dioxo-3-piperidyl)-1,3-dioxo-isoindolin-4-yl]amino] cyclobutyl]-N-methyl-carbamate (80.0 mg, 175 umol) in DCM (5 mL) was added HCl/dioxane (4 M, 2 mL) at 25° C. The mixture was stirred at 25° C. for 2 hrs. The mixture was stirred at 25° C. for 2 hrs. On completion, the reaction mixture was concentrated in vacuo to give the title compound (68 mg, 98% yield, HCl salt) as a yellow solid. LC-MS (ESI$^+$) m/z 357.2 (M+H)$^+$.

3-[3-methyl-2-oxo-4-[4-(4-piperidyl)butyl]benzimidazol-1-yl]piperidine-2,6-dione (Intermediate ALL)

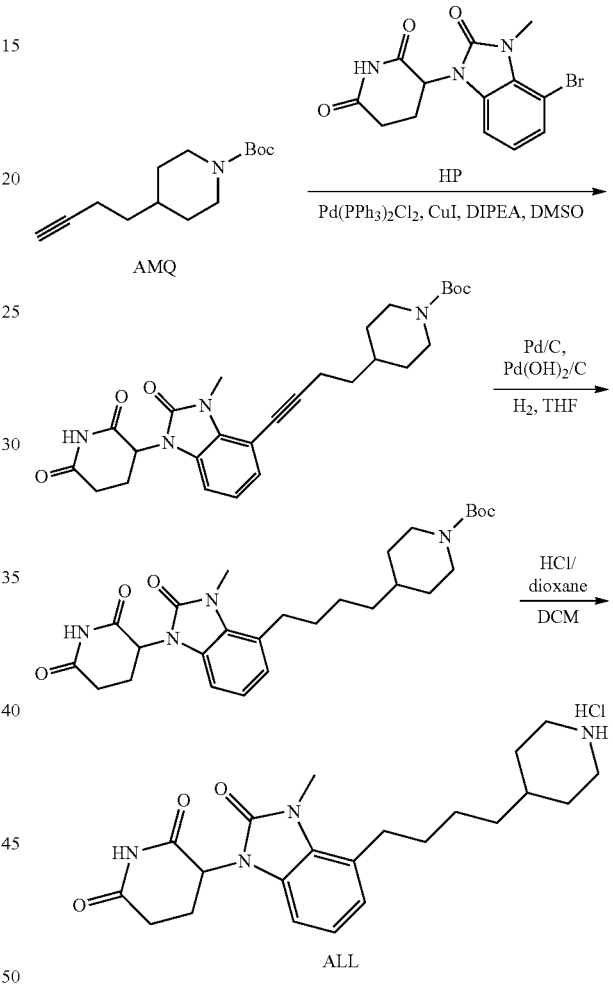

Step 1—Tert-butyl 4-[4-[1-(2,6-dioxo-3-piperidyl)-3-methyl-2-oxo-benzimidazol-4-yl]but-3-ynyl]piperidine-1-carboxylate A mixture of tert-butyl 4-but-3-ynylpiperidine-1-carboxylate (526 mg, 2.22 mmol, Intermediate AMQ), 3-(4-bromo-3-methyl-2-oxobenzimidazol-1-yl)piperidine-2,6-dione (500 mg, 1.48 mmol, Intermediate HP), Pd(PPh$_3$)$_2$Cl$_2$ (207 mg, 295 umol), CuI (56.3 mg, 295 umol), DIEA (955 mg, 7.39 mmol) and 4 Å molecular sieves (500 mg) in DMSO (6.00 mL) was degassed and purged with N$_2$ for 3 times, and then the mixture was stirred at 80° C. for 2 hrs under N$_2$ atmosphere. On completion, the reaction mixture was filtered and concentrated in vacuo to give a residue. The residue was purified by reversed-phase (0.1% FA condition)

to give the title compound (330 mg, 45% yield) as a yellow solid. ¹H NMR (400 MHz, DMSO-d₆) δ 11.11 (s, 1H), 7.11 (d, J=7.4 Hz, 1H), 7.07-7.02 (m, 1H), 7.01-6.94 (m, 1H), 5.40-5.35 (m, 1H), 3.93 (d, J=11.8 Hz, 2H), 3.64 (s, 3H), 3.30 (d, J=1.6 Hz, 2H), 2.96-2.84 (m, 1H), 2.77-2.68 (m, 2H), 2.67-2.66 (m, 2H), 2.09-1.95 (m, 1H), 1.68 (d, J=12.8 Hz, 2H), 1.62-1.49 (m, 3H), 1.39 (s, 9H), 1.08-0.94 (m, 2H).

Step 2—Tert-butyl 4-[4-[1-(2,6-dioxo-3-piperidyl)-3-methyl-2-oxo-benzimidazol-4-yl]butyl]piperidine-1-carboxylate To a solution of tert-butyl 4-[4-[1-(2,6-dioxo-3-piperidyl)-3-methyl-2-oxo-benzimidazol-4-yl]but-3-ynyl]piperidine-1-carboxylate (230 mg, 465 umol) in THF (10.0 mL) was added Pd(OH)₂/C (100 mg, 20% wt) and Pd/C (100 mg, 10% wt) under N₂ atmosphere. The suspension was degassed and purged with H₂ gas 3 times. The mixture was stirred under H₂ (15 Psi.) at 20° C. for 16 hrs. On completion, the reaction mixture was filtered and concentrated in vacuo to give the title compound (230 mg, 99% yield) as a white solid. ¹H NMR (400 MHz, DMSO-d₆) δ 11.09 (s, 1H), 6.98-6.82 (m, 3H), 5.36 (dd, J=5.2, 12.4 Hz, 1H), 3.90 (d, J=12.0 Hz, 2H), 3.54 (s, 3H), 2.96-2.82 (m, 3H), 2.77-2.57 (m, 4H), 2.05-1.93 (m, 1H), 1.65-1.51 (m, 4H), 1.40-1.34 (m, 12H), 1.28-1.20 (m, 2H), 0.99-088 (m, 2H).

Step 3—3-[3-Methyl-2-oxo-4-[4-(4-piperidyl)butyl]benzimidazol-1-yl]piperidine-2,6-dione To a solution of tert-butyl 4-[4-[1-(2,6-dioxo-3-piperidyl)-3-methyl-2-oxo-benzimidazol-4-yl]butyl] piperidine-1-carboxylate (230 mg, 461 umol) in DCM (2.00 mL) was added HCl/dioxane (4 M, 1.00 mL). The mixture was stirred at 20° C. for 1 hr. On completion, the reaction mixture was concentrated in vacuo to give the title compound (200 mg, 99% yield, HCl) as a white solid. LC-MS (ESI⁺) m/z 399.3 (M+H)⁺.

3-[4-[3-(2,7-Diazaspiro[3.5]nonan-7-yl)-3-oxo-propyl]-3-methyl-2-oxo-benzimidazol-1-yl]] piperidine-2,6-dione (Intermediate ALM)

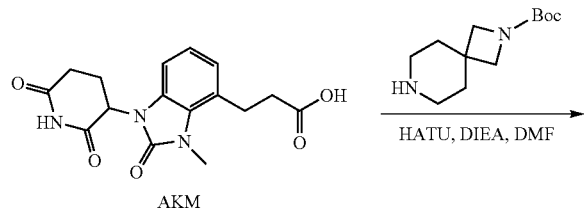

HATU, DIEA, DMF

AKM

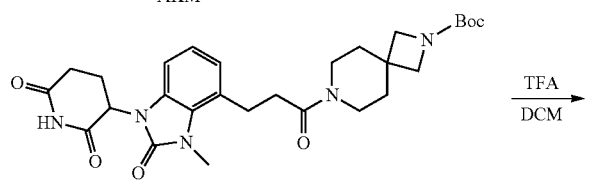

TFA DCM

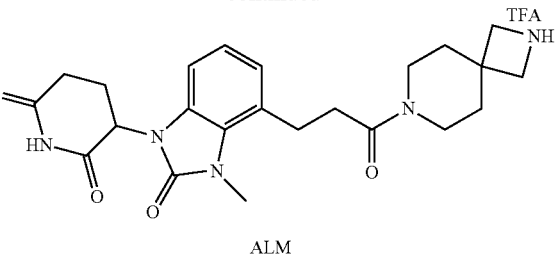

ALM

Step 1—Tert-butyl 7-[3-[1-(2,6-dioxo-3-piperidyl)-3-methyl-2-oxo-benzimidazol-4-yl]propanoyl]-2,7-diazaspiro[3.5]nonane-2-carboxylate To a solution of 3-[1-(2,6-dioxo-3-piperidyl)-3-methyl-2-oxo-benzimidazol-4-yl]propanoic acid (80.0 mg, 241 umol, Intermediate AKM) in DMF (3 mL) was added DIPEA (156 mg, 1.21 mmol, 210 uL), and HATU (110 mg, 289 umol), then the mixture was stirred at 20° C. for 15 min. Then tert-butyl 2,7-diazaspiro[3.5]nonane-2-carboxylate (54.6 mg, 241 umol, CAS #236406-55-6) was added to the mixture, and the reaction mixture was stirred at 20° C. for 1 hrs. On completion, the reaction mixture quenched by addition H₂O (0.5 mL), then the mixture was concentrated in vacuo to give a residue. The residue was purified by reverse phase (0.1% FA condition) to give the title compound (100 mg, 76.7% yield) as a white solid. LC-MS (ESI⁺) m/z 540.1 (M+H)⁺.

Step 2—3-[4-[3-(2,7-Diazaspiro[3.5]nonan-7-yl)-3-oxo-propyl]-3-methyl-2-oxo-benzimidazol-1-yl] piperidine-2,6-dione To a solution of tert-butyl 7-[3-[1-(2,6-dioxo-3-piperidyl)-3-methyl-2-oxo-benzimidazol-4-yl] propanoyl]-2,7-diazaspiro[3.5]nonane-2-carboxylate (100 mg, 185 umol,) in DCM (5 mL) was added TFA (3.08 g, 27.0 mmol, 2 mL), and the reaction mixture was stirred at 20° C. for 1 hr. On completion, the reaction mixture was concentrated in vacuo to give the title compound (100 mg, 97.5% yield, TFA salt) as a yellow solid. ¹H NMR (400 MHz, DMSO-d₆) δ 11.09 (s, 1H), 7.00-6.90 (m, 3H), 5.37 (dd, J=5.2, 12.4 Hz, 1H), 3.72 (t, J=6.0 Hz, 4H), 3.57 (s, 3H), 3.48-3.24 (m, 4H), 3.14 (t, J=7.6 Hz, 2H), 2.96-2.82 (m, 1H), 2.77-2.57 (m, 4H), 2.04-1.92 (m, 1H), 1.81-1.52 (m, 4H).

2-[1-(2,6-Dioxo-3-piperidyl)-3-methyl-2-oxo-benzimidazol-4-yl]acetic acid (Intermediate ALN)

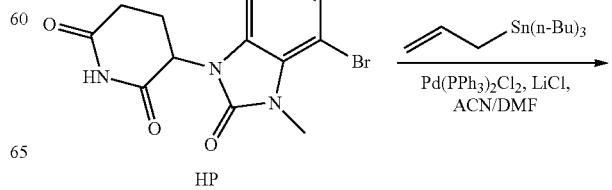

HP

-continued

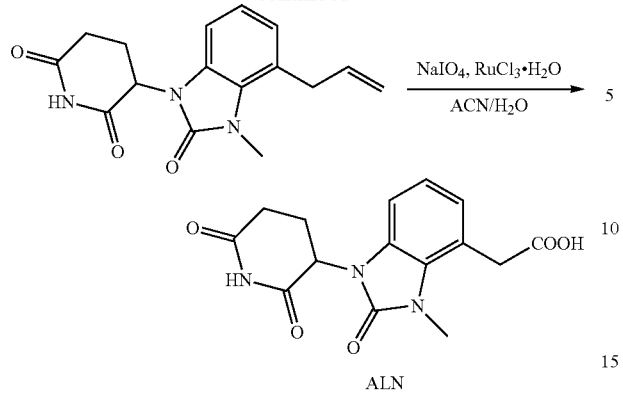

ALN

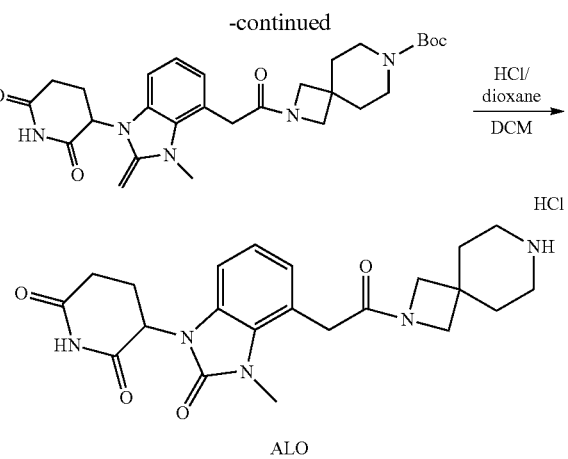

ALO

Step 1—3-(4-Allyl-3-methyl-2-oxo-benzimidazol-1-yl)piperidine-2,6-dione

To a solution of 3-(4-bromo-3-methyl-2-oxo-benzimidazol-1-yl)piperidine-2,6-dione (1.00 g, 2.96 mmol, Intermediate HP) and allyl(tributyl)stannane (1.18 g, 3.55 mmol) in the ACN (40 mL) and DMF (4 mL) was added Pd(PPh$_3$)$_2$Cl$_2$ (208 mg, 296 umol) and LiCl (251 mg, 5.91 mmol) at 20° C. under N$_2$. The mixture was stirred at 90° C. for 12 hours. On completion, the reaction was quenched by aq.KF (1 M, 20 mL). The mixture was concentrated in vacuo and extracted with DCM (2×50 mL). The combined organic layers was dried over Na$_2$SO$_4$, filtered and concentrated in vacuo. The residue was purified by reversed phase (FA, 0.1%) to give yellow solid (400 mg, 45% yield). $^1$H NMR (400 MHz, CDCl$_3$) δ 8.12 (s, 1H), 7.05-6.98 (m, 1H), 6.91 (d, J=7.6 Hz, 1H), 6.71 (d, J=7.6 Hz, 1H), 6.14-6.01 (m, 1H), 5.27-5.12 (m, 2H), 4.94 (dd, J=1.6, 17.1 Hz, 1H), 3.71 (d, J=5.6 Hz, 2H), 3.66 (s, 3H), 3.00-2.90 (m, 1H), 2.89-2.70 (m, 2H), 2.28-2.19 (m, 1H); LC-MS (ESI$^+$) m/z 300.0 (M+H)$^+$.

Step 2—2-[1-(2,6-Dioxo-3-piperidyl)-3-methyl-2-oxo-benzimidazol-4-yl]acetic acid To a solution of 3-(4-allyl-3-methyl-2-oxo-benzimidazol-1-yl) piperidine-2,6-dione (200 mg, 668 umol) in the ACN (4 mL) and CCl$_4$ (4 mL) was added the solution of NaIO$_4$ (429 mg, 2.00 mmol) and RuCl$_3$.H$_2$O (15.1 mg, 66.8 umol) in H$_2$O (8 mL). The mixture was stirred at 20° C. for 2 hours. On completion, the mixture was concentrated in vacuo. The residue was diluted with ACN (20 mL) and filtered. The filtrate was concentrated in vacuo to give the title compound (200 mg, 94% yield) as brown solid. LC-MS (ESI$^+$) m/z 318.0 (M+H)$^+$.

3-[4-[2-(2,7-Diazaspiro[3.5]nonan-2-yl)-2-oxo-ethyl]-3-methyl-2-oxo-benzimidazol-1-yl] piperidine-2,6-dione (Intermediate ALO)

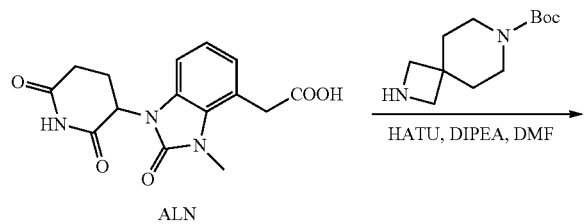

ALN

Step 1—Tert-butyl 2-[2-[1-(2,6-dioxo-3-piperidyl)-3-methyl-2-oxo-benzimidazol-4-yl]acetyl]-2,7-diazaspiro[3.5]nonane-7-carboxylate To a solution of 2-[1-(2,6-dioxo-3-piperidyl)-3-methyl-2-oxo-benzimidazol-4-yl]acetic acid (50 mg, 158 umol, Intermediate ALN) and tert-butyl 2,7-diazaspiro[3.5]nonane-7-carboxylate (35.7 mg, 158 umol, CAS #896464-16-7) in the DMF (1 mL) was added HATU (71.9 mg, 189 umol) and DIPEA (40.7 mg, 315 umol). The mixture was stirred at 20° C. for 2 hours. On completion, the reaction mixture was concentrated in vacuo. The residue was purified by reversed phase (FA, 0.1%) to give the title compound (20.0 mg, 24% yield) as brown solid. $^1$H NMR (400 MHz, CDCl$_3$) δ 8.26 (s, 1H), 7.03-6.97 (m, 1H), 6.85 (d, J=7.2 Hz, 1H), 6.74-6.72 (m, 1H), 5.22 (dd, J=5.2, 12.4 Hz, 1H), 3.91 (s, 2H), 3.77 (t, J=4.4 Hz, 4H), 3.70 (s, 3H), 3.48-3.39 (m, 2H), 3.36-3.29 (m, 2H), 2.96-2.90 (m, 1H), 2.87-2.81 (m, 1H), 2.80-2.73 (m, 1H), 2.27-2.18 (m, 1H), 1.81-1.68 (m, 4H), 1.46 (s, 9H); LC-MS (ESI$^+$) m/z 470.3 (M−45)$^+$, 426.3 (M−100+1)$^+$.

Step 2—3-[4-[2-(2,7-Diazaspiro[3.5]nonan-2-yl)-2-oxo-ethyl]-3-methyl-2-oxo-benzimidazol-1-yl] piperidine-2,6-dione To a solution of tert-butyl 2-[2-[1-(2,6-dioxo-3-piperidyl)-3-methyl-2-oxo-benzimidazol-4-yl]acetyl]-2,7-diazaspiro[3.5]nonane-7-carboxylate (20.0 mg, 38.1 umol) in the DCM (1 mL) was added HCl/dioxane (2 mL). The mixture was stirred at 20° C. for 1 hour. On completion, the reaction mixture was concentrated in vacuo to give the title compound (16.0 mg, 99% yield) as gray solid.

Tert-butyl 7-prop-2-ynyl-2,7-diazaspiro[3.5]nonane-2-carboxylate (Intermediate ALP)

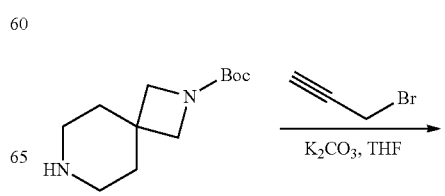

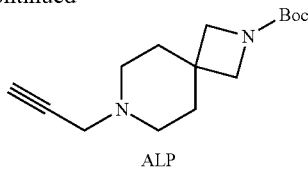

ALP

To a solution of tert-butyl 2,7-diazaspiro[3.5]nonane-2-carboxylate (200 mg, 884 umol, CAS #236406-55-6) and 3-bromoprop-1-yne (158 mg, 1.06 mmol) in the THF (5 mL) was added K$_2$CO$_3$ (244 mg, 1.77 mmol). The reaction mixture was stirred at 20° C. for 5 hrs. On completion, the reaction was filtered and concentrated in vacuo. The residue was diluted with ethyl acetate (20 mL) and washed with water (20 mL). The organic layer was dried over Na$_2$SO$_4$, filtered and concentrated in vacuo to give colorless oil (200 mg, 86% yield). $^1$H NMR (400 MHz, CDCl$_3$) δ 3.62 (s, 4H), 3.28 (d, J=2.5 Hz, 2H), 2.47 (br s, 4H), 2.24 (t, J=2.4 Hz, 1H), 1.79 (t, J=5.5 Hz, 4H), 1.45 (s, 9H).

3-[4-[3-(2,7-diazaspiro[3.5]nonan-7-yl)propyl]-3-methyl-2-oxo-benzimidazol-1-yl]piperidine-2,6-dione (Intermediate ALQ)

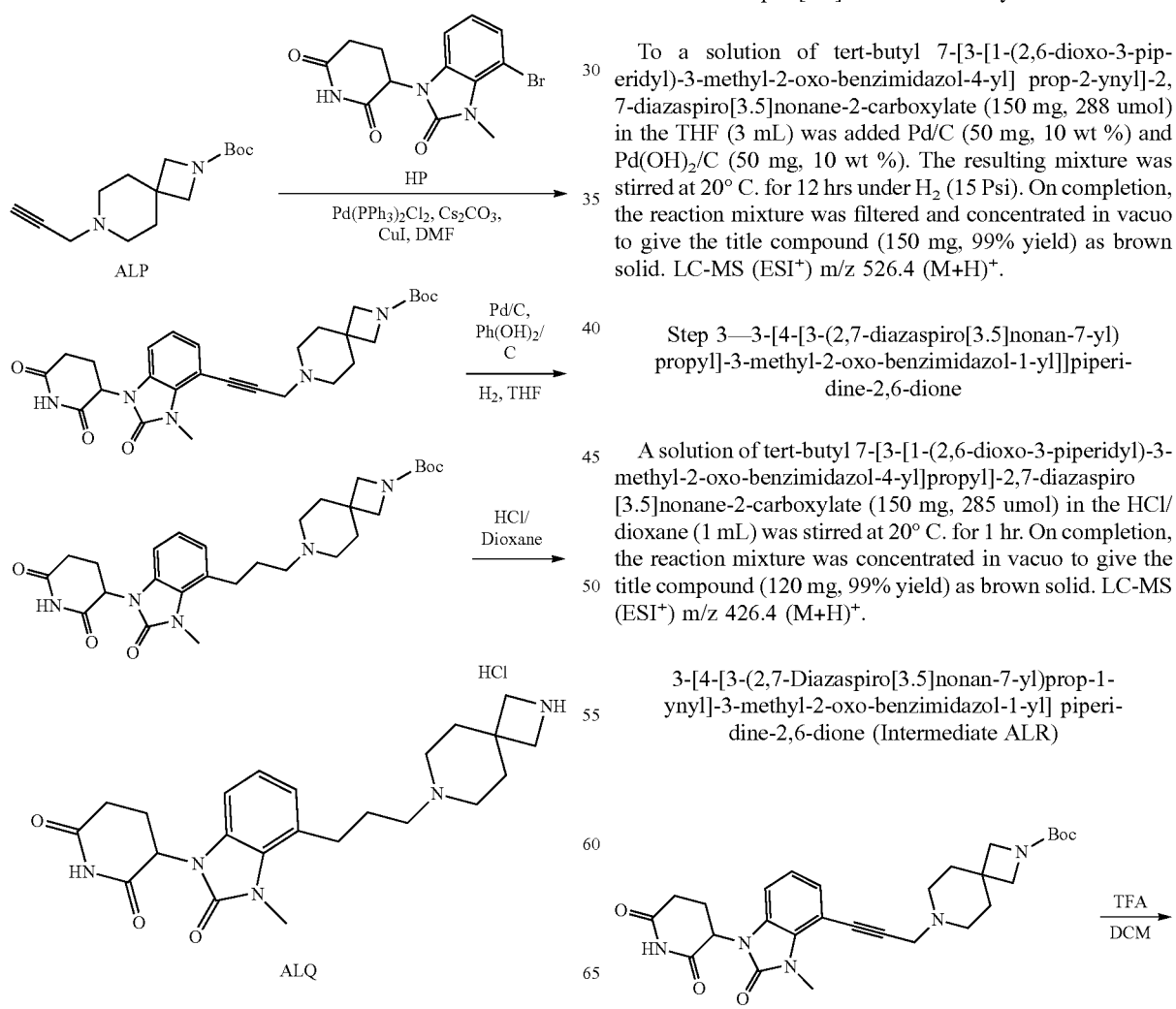

Step 1—Tert-butyl 7-[3-[1-(2,6-dioxo-3-piperidyl)-3-methyl-2-oxo-benzimidazol-4-yl]prop-2-ynyl]-2,7-diazaspiro[3.5]nonane-2-carboxylate To a solution of tert-butyl 7-prop-2-ynyl-2,7-diazaspiro[3.5]nonane-2-carboxylate (300 mg, 1.13 mmol, Intermediate ALP) and 3-(4-bromo-3-methyl-2-oxo-benzimidazol-1-yl)piperidine-2,6-dione (384 mg, 1.13 mmol, Intermediate HP) in the DMF (6 mL) was added Pd(PPh$_3$)$_2$Cl$_2$ (79.7 mg, 113 umol), Cs$_2$CO$_3$ (1.48 g, 4.54 mmol) and CuI (21.6 mg, 113 umol) under N$_2$. The resulting mixture was stirred at 80° C. for 2 hrs. On completion, the mixture was filtered and purified by reversed phase (0.1% FA) to give the title compound (450 mg, 76% yield) as yellow solid. $^1$H NMR (400 MHz, CDCl$_3$) δ 8.35 (br s, 1H), 7.16 (dd, J=0.8, 8.0 Hz, 1H), 7.00 (t, J=8.0 Hz, 1H), 6.80-6.74 (m, 1H), 5.21 (dd, J=5.6, 12.6 Hz, 1H), 3.76 (s, 3H), 3.66 (s, 4H), 3.00-2.91 (m, 1H), 2.89-2.82 (m, 1H), 2.82-2.76 (m, 1H), 2.76-2.66 (m, 4H), 2.62-2.54 (m, 1H), 2.28-2.19 (m, 1H), 1.90 (t, J=5.6 Hz, 4H), 1.84 (t, J=5.6 Hz, 1H), 1.44 (s, 9H); LC-MS (ESI$^+$) m/z 522.4 (M+H)$^+$.

Step 2—Tert-butyl 7-[3-[1-(2,6-dioxo-3-piperidyl)-3-methyl-2-oxo-benzimidazol-4-yl]propyl]-2,7-diazaspiro[3.5]nonane-2-carboxylate To a solution of tert-butyl 7-[3-[1-(2,6-dioxo-3-piperidyl)-3-methyl-2-oxo-benzimidazol-4-yl] prop-2-ynyl]-2,7-diazaspiro[3.5]nonane-2-carboxylate (150 mg, 288 umol) in the THF (3 mL) was added Pd/C (50 mg, 10 wt %) and Pd(OH)$_2$/C (50 mg, 10 wt %). The resulting mixture was stirred at 20° C. for 12 hrs under H$_2$ (15 Psi). On completion, the reaction mixture was filtered and concentrated in vacuo to give the title compound (150 mg, 99% yield) as brown solid. LC-MS (ESI$^+$) m/z 526.4 (M+H)$^+$.

Step 3—3-[4-[3-(2,7-diazaspiro[3.5]nonan-7-yl)propyl]-3-methyl-2-oxo-benzimidazol-1-yl]]piperidine-2,6-dione A solution of tert-butyl 7-[3-[1-(2,6-dioxo-3-piperidyl)-3-methyl-2-oxo-benzimidazol-4-yl]propyl]-2,7-diazaspiro[3.5]nonane-2-carboxylate (150 mg, 285 umol) in the HCl/dioxane (1 mL) was stirred at 20° C. for 1 hr. On completion, the reaction mixture was concentrated in vacuo to give the title compound (120 mg, 99% yield) as brown solid. LC-MS (ESI$^+$) m/z 426.4 (M+H)$^+$.

3-[4-[3-(2,7-Diazaspiro[3.5]nonan-7-yl)prop-1-ynyl]-3-methyl-2-oxo-benzimidazol-1-yl] piperidine-2,6-dione (Intermediate ALR)

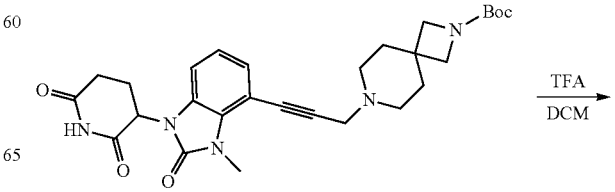

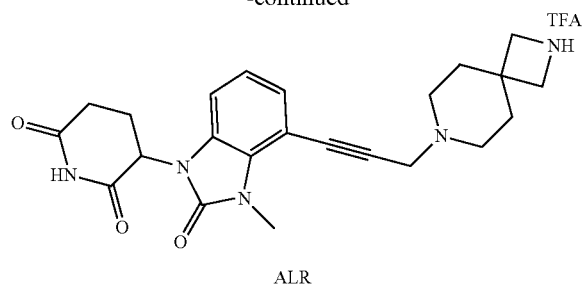

ALR

To a mixture of tert-butyl 7-[3-[1-(2,6-dioxo-3-piperidyl)-3-methyl-2-oxo-benzimidazol-4-yl] prop-2-ynyl]-2,7-diaz-aspiro[3.5]nonane-2-carboxylate (50.0 mg, 95.8 umol, synthesized via Step 1 of Intermediate ALQ) in DCM (5 mL) was added TFA (3.85 g, 33.7 mmol, 2.50 mL). The reaction mixture was stirred at 20° C. for 0.5 hr. On completion, the reaction mixture was concentrated in vacuo to give the title compound (50.0 mg, 97% yield, TFA salt) as brown oil. LC-MS (ESI+) m/z 422.3 (M+H)+.

5-(1-Piperidyl)pyrazolo[1,5-a]pyrimidine-3-carboxylic acid (Intermediate AKU)

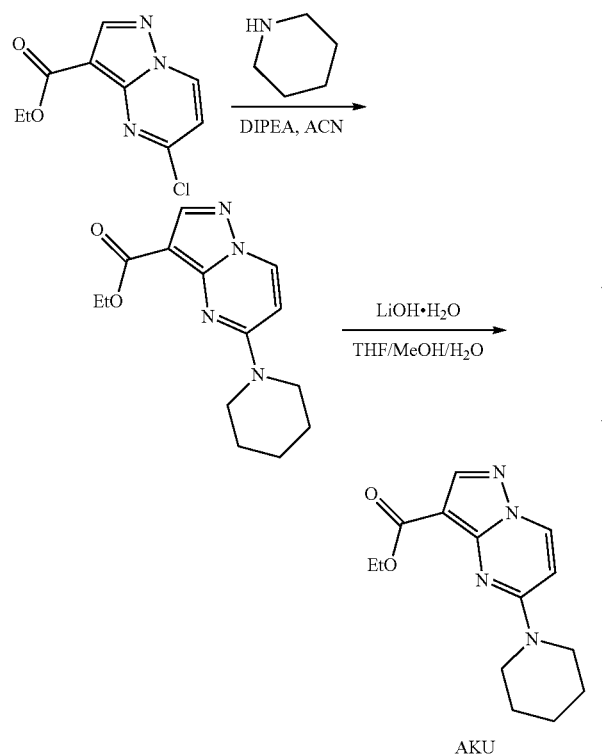

Step 1—Ethyl 5-(1-piperidyl)pyrazolo[1,5-a]pyrimidine-3-carboxylate

A mixture of ethyl 5-chloropyrazolo[1,5-a]pyrimidine-3-carboxylate (1.00 g, 4.43 mmol, CAS #1224944-77-7), piperidine (754 mg, 8.86 mmol, CAS #110-89-4) and DIPEA (1.15 g, 8.86 mmol) in ACN (25 mL) was stirred at 60° C. for 2 hrs under nitrogen atmosphere. On completion, the reaction mixture was diluted with water (60 mL). The mixture was concentrated in vacuo to remove the ACN. The mixture was extracted with EA (3×30 mL). The organic layer was dried over anhydrous sodium sulfate and filtered. The filtrated was concentrated in vacuo to give the title compound (1.20 g, 98% yield) as yellow solid. $^1$H NMR (400 MHz, CDCl$_3$) δ 8.26 (s, 1H), 8.23 (d, J=8.0 Hz, 1H), 6.42 (d, J=8.0 Hz, 1H), 4.35 (q, J=7.2 Hz, 2H), 3.78-3.76 (s, 4H), 1.76-1.66 (m, 6H), 1.39 (t, J=7.2 Hz, 3H).

Step 2—5-(1-Piperidyl)pyrazolo[1,5-a]pyrimidine-3-carboxylic acid

To a mixture of ethyl 5-(1-piperidyl)pyrazolo[1,5-a]pyrimidine-3-carboxylate (1.20 g, 4.37 mmol) in a mixed solvent of THF (30 mL) and MeOH (10 mL) was added a solution of LiOH.H$_2$O (550 mg, 13.1 mmol) in H$_2$O (10 mL). The reaction mixture was stirred at 60° C. for 16 hours under nitrogen atmosphere. On completion, the reaction mixture was concentrated in vacuo to remove the THF and MeOH. The reaction mixture was diluted with water (30 mL) and acidified with 2M HCl until the pH=4. The mixture was filtered and the filtered cake was dried in vacuo to give the title compound (850 mg, 78% yield) as yellow solid. $^1$H NMR (400 MHz, DMSO-d$_6$) δ 11.64 (br s, 1H), 8.64 (d, J=8.0 Hz, 1H), 8.15 (s, 1H), 6.82 (d, J=8.0 Hz, 1H), 3.75-3.73 (s, 4H), 1.69-1.61 (m, 2H), 1.61-1.53 (m, 4H).

N-[3-(difluoromethyl)-1-(4-formylcyclohexyl)pyrazol-4-yl]-5-(1-piperidyl)pyrazolo[1,5-a]pyrimidine-3-carboxamide (Intermediate AKV)

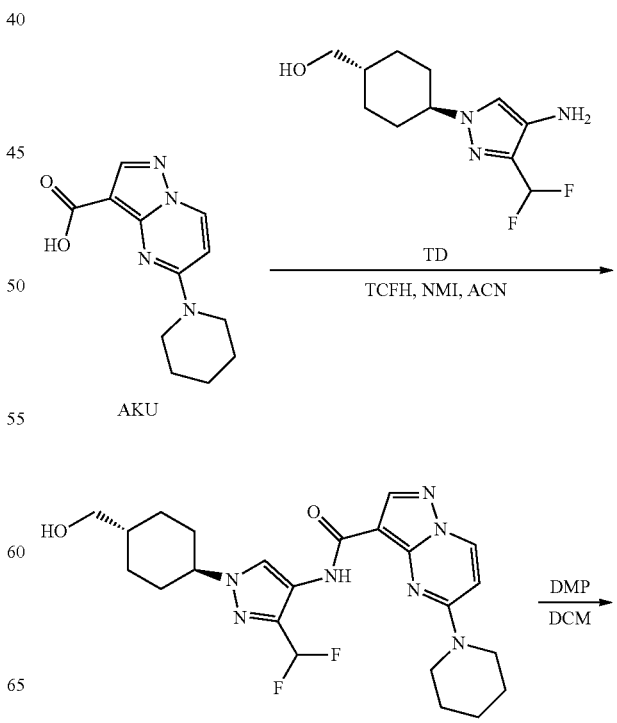

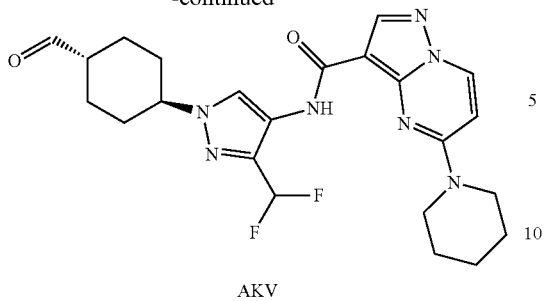

AKV

Step 1—N-[3-(difluoromethyl)-1-[4-(hydroxymethyl)cyclohexyl]pyrazol-4-yl]-5-(1-piperidyl)pyrazolo[1,5-a]pyrimidine-3-carboxamide A mixture of 5-(1-piperidyl)pyrazolo[1,5-a]pyrimidine-3-carboxylic acid (260 mg, 527 umol, Intermediate AKU), 1-methylimidazole (130 mg, 1.58 mmol) and [chloro(dimethylamino)methylene]-dimethyl-ammonium; hexafluorophosphate (177 mg, 633 umol) in ACN (10 mL) was stirred at 20° C. for 0.5 hour. Then [4-[4-amino-3-(difluoromethyl)pyrazol-1-yl]cyclohexyl]methanol (155 mg, 633 umol, Intermediate TD) was added to the reaction mixture. The reaction mixture was stirred at 20° C. for 15.5 hours. On completion, the reaction mixture was quenched by water (2 mL) and concentrated in vacuo. The crude product was purified by reverse phase flash (0.1% FA condition) to give the title compound (150 mg, 60% yield) was obtained as yellow solid. $^1$H NMR (400 MHz, DMSO-$d_6$) δ 9.39 (s, 1H), 8.72 (d, J=8.0 Hz, 1H), 8.38 (s, 1H), 8.24 (s, 1H), 7.25-6.94 (m, 1H), 6.90 (d, J=8.0 Hz, 1H), 4.47 (t, J=5.2 Hz, 1H), 4.19-4.14 (m, 1H), 3.79 (s, 4H), 3.26 (t, J=5.6 Hz, 2H), 2.10-2.00 (m, 2H), 1.91-1.81 (m, 2H), 1.78-1.64 (m, 4H), 1.64-1.55 (m, 4H), 1.49-1.35 (m, 1H), 1.16-1.01 (m, 2H).

Step 2—N-[3-(difluoromethyl)-1-(4-formylcyclohexyl)pyrazol-4-yl]-5-(1-piperidyl)pyrazolo[1,5-a]pyrimidine-3-carboxamide To a mixture of N-[3-(difluoromethyl)-1-[4-(hydroxymethyl)cyclohexyl]pyrazol-4-yl]-5-(1-piperidyl) pyrazolo[1,5-a]pyrimidine-3-carboxamide (130 mg, 274 umol) in DCM (5 mL) was added DMP (151 mg, 356 umol). The reaction mixture was stirred at 20° C. for 1 hr. On completion, the reaction mixture was diluted with saturated $Na_2S_2O_3$ aqueous (5 mL) and saturated $NaHCO_3$ aqueous (5 mL). The mixture was stirred at 20° C. for 0.5 hr. The mixture was diluted with water (50 mL) and extracted with DCM (3×20 mL). The organic layer was washed with saturated $NaHCO_3$ aqueous (3×30 mL) and brine (3×30 mL). The organic layer was dried over anhydrous sodium sulfate and filtered. The filtrated was concentrated in vacuo to give the title compound (120 mg, 92% yield) as yellow solid. $^1$H NMR (400 MHz, DMSO-$d_6$) δ 9.62 (s, 1H), 9.39 (s, 1H), 8.72 (d, J=8.0 Hz, 1H), 8.40 (s, 1H), 8.24 (s, 1H), 7.26-6.94 (m, 1H), 6.90 (d, J=8.0 Hz, 1H), 4.29-4.14 (m, 1H), 3.80-3.78 (s, 4H), 2.44-2.34 (m, 1H), 2.13-2.03 (m, 4H), 1.88-1.76 (m, 2H), 1.72-1.64 (m, 2H), 1.63-1.57 (m, 4H), 1.45-1.31 (m, 2H).

4-[2-[4-(Aminomethyl)phenyl]ethylamino]-2-(2,6-dioxo-3-piperidyl)isoindoline-1,3-dione (Intermediate AOP)

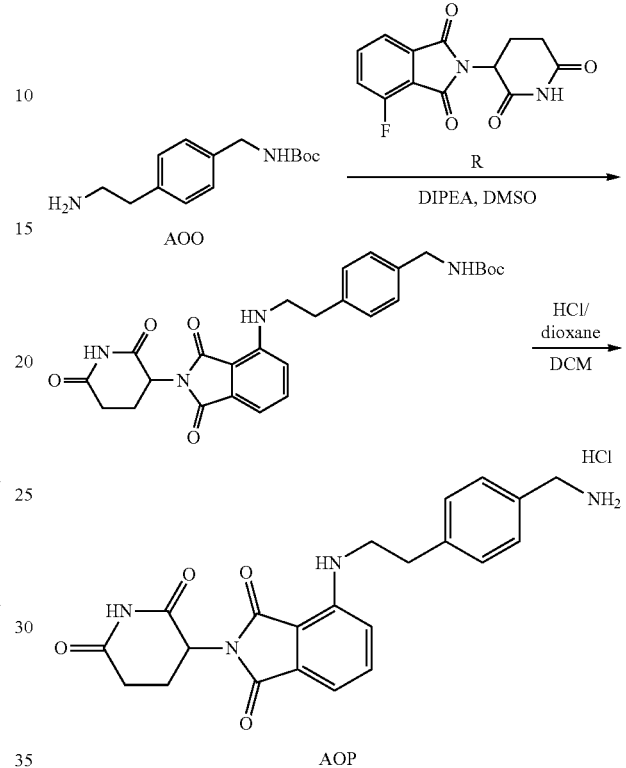

Step 1—Tert-butyl N-[[4-[2-[[2-(2,6-dioxo-3-piperidyl)-1,3-dioxo-isoindolin-4-yl]amino]ethyl]phenyl]methyl]carbamate A mixture of tert-butyl N-[[4-(2-aminoethyl)phenyl] methyl]carbamate (340 mg, 1.36 mmol, Intermediate AOO), 2-(2,6-dioxo-3-piperidyl)-4-fluoro-isoindoline-1,3-dione (340 mg, 1.23 mmol, Intermediate R) and DIPEA (532 mg, 4.12 mmol) in DMSO (3 mL) was stirred at 130° C. for 2 hours. On completion, the reaction was quenched with water (0.3 mL). The mixture was concentrated in vacuo to give a residue. The residue was purified by reversed phase (FA condition) to give the title compound (340 mg, 49% yield) as light yellow solid. $^1$H NMR (400 MHz, DMSO-$d_6$) δ 11.08 (s, 1H), 7.61-7.59 (m, 1H), 7.38-7.32 (m, 1H), 7.25 (d, J=8.0 Hz, 2H), 7.20-7.14 (m, 3H), 7.03 (d, J=7.2 Hz, 1H), 6.56 (t, J=5.6 Hz, 1H), 5.07-5.02 (m, 1H), 4.09 (d, J=5.6 Hz, 2H), 3.56-3.49 (m, 2H), 2.91-2.82 (m, 3H), 2.63-2.55 (m, 2H), 2.07-1.98 (m, 1H), 1.39 (s, 9H).

Step 2—4-[2-[4-(Aminomethyl)phenyl]ethylamino]-2-(2,6-dioxo-3-piperidyl)isoindoline-1,3-dione To a solution of tert-butyl N-[[4-[2-[[2-(2,6-dioxo-3-piperidyl)-1,3-dioxo-isoindolin-4-yl]amino]ethyl] phenyl] methyl]carbamate (330 mg, 651 umol) in DCM (5 mL) was added HCl/dioxane (4.0 M, 2 mL) at 15° C. The mixture was stirred at 15° C. for 1 hour. On completion, the mixture was concentrated in vacuo to give the title compound (280 mg, 97% yield, HCl salt) as light yellow solid. LC-MS (ESI⁺) m/z 407.1 (M+H)⁺.

(5-Cyanopentyl)triphenylphosphonium bromide (Intermediate ALV)

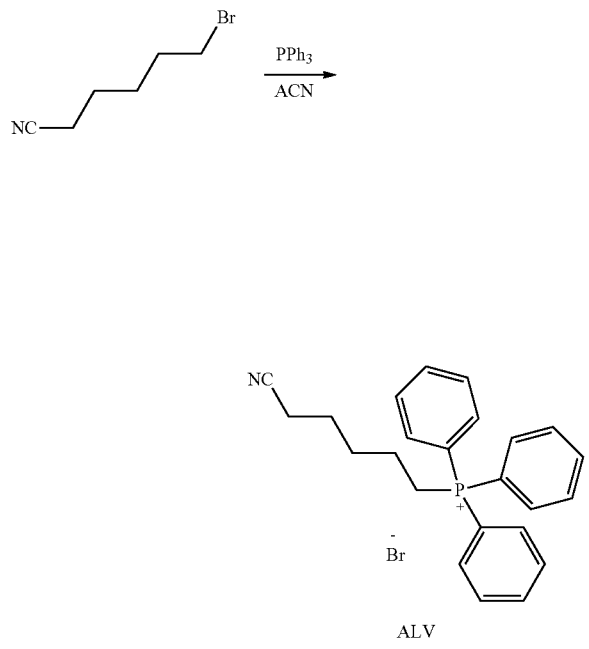

A solution of 6-bromohexanenitrile (2.00 g, 11.4 mmol, CAS #6621-59-6) and PPh₃ (8.94 g, 34.1 mmol) in the MeCN (20 mL) was stirred at 90° C. for 12 hrs. On completion, the reaction mixture was concentrated in vacuo. The residue was triturated with petrol ether (3×50 mL) to give the title compound (4.50 g, 90% yield) as white solid. ¹H NMR (400 MHz, DMSO-d₆) δ=8.00-7.68 (m, 15H), 3.76-3.57 (m, 2H), 2.50-2.44 (m, 2H), 1.59-1.58 (m, 6H).

Tert-butyl N-[1-[4-(7-aminoheptyl)cyclohexyl]-3-(difluoromethyl)pyrazol-4-yl]carbamate (Intermediate ALW)

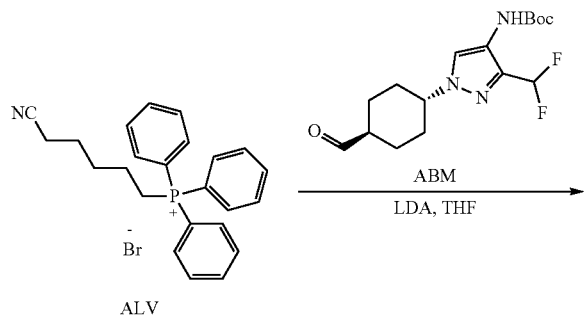

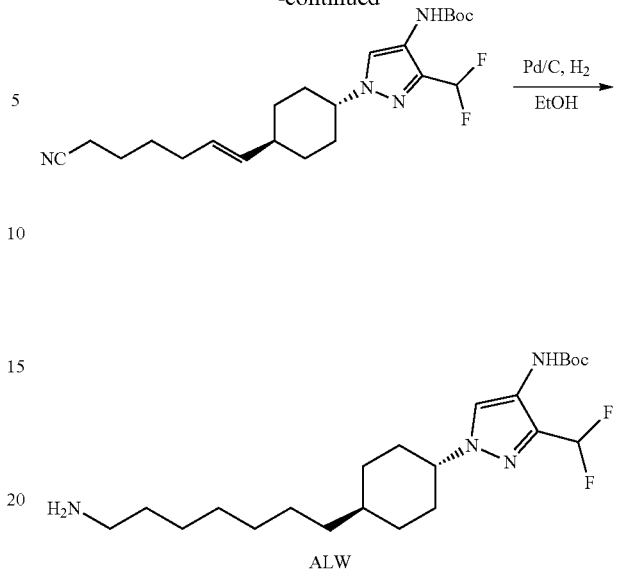

Step 1—Tert-butyl N-[1-[4-[(E)-6-cyanohex-1-enyl]cyclohexyl]-3-(difluoromethyl)pyrazol-4-yl] carbamate To a solution of (5-cyanopentyl)triphenylphosphonium bromide (230 mg, 525 umol, Intermediate ALV) in THF (5 mL) was added LDA (2 M, 394 uL) at −78° C. under N₂. The reaction mixture was stirred at −78° C. for 1 hr. Then the solution of tert-butyl N-[3-(difluoromethyl)-1-(4-formylcyclohexyl)pyrazol-4-yl]carbamate (180 mg, 525 umol, Intermediate ABM) in THF (1 mL) was added at −78° C. The mixture was slowly warmed to 20° C. and stirred for 12 hrs. On completion, the reaction mixture was quenched by saturated NH₄Cl aqueous (5 mL) and extracted with EA (2×20 mL). The organic layers was dried over Na₂SO₄, filtered and concentrated in vacuo. The residue was purified by Prep-TLC (PE:EA=2:1) to give the title compound (80.0 mg, 36% yield) as colorless oil. ¹H NMR (400 MHz, CDCl₃) δ=7.93 (s, 1H), 6.71 (t, J=54.8 Hz, 1H), 6.61 (br s, 1H) 5.36-5.19 (m, 2H), 4.06-3.98 (m, 1H), 2.37 (t, J=7.2 Hz, 2H), 2.35-2.24 (m, 1H), 2.20-2.07 (m, 4H), 1.86-1.74 (m, 4H), 1.72-1.64 (m, 2H), 1.58-1.53 (m, 2H), 1.51 (s, 9H), 1.35-1.25 (m, 2H); LC-MS (ESI⁺) m/z 423.3 (M+H)⁺.

Step 2—Tert-butyl N-[1-[4-(7-aminoheptyl)cyclohexyl]-3-(difluoromethyl)pyrazol-4-yl]carbamate To a solution of tert-butyl N-[1-[4-[(E)-6-cyanohex-1-enyl]cyclohexyl]-3-(difluoromethyl)pyrazol-4-yl] carbamate (80 mg, 189 umol) in the EtOH (2 mL) was added Pd/C (40 mg, 10 wt %). The mixture was stirred at 20° C. for 12 hrs under H₂ (15 Psi). the reactant was The mixture was further stirred at 50° C. for 2 hrs. On completion, the reaction mixture was filtered and concentrated in vacuo to give the title compound (60 mg, 62% yield) as colorless gum. LC-MS (ESI⁺) m/z 429.3 (M+H)⁺.

4-[7-[4-[4-amino-3-(difluoromethyl)pyrazol-1-yl]
cyclohexyl]heptylamino]-2-(2,6-dioxo-3-piperidyl)
isoindoline-1,3-dione (Intermediate ALX)

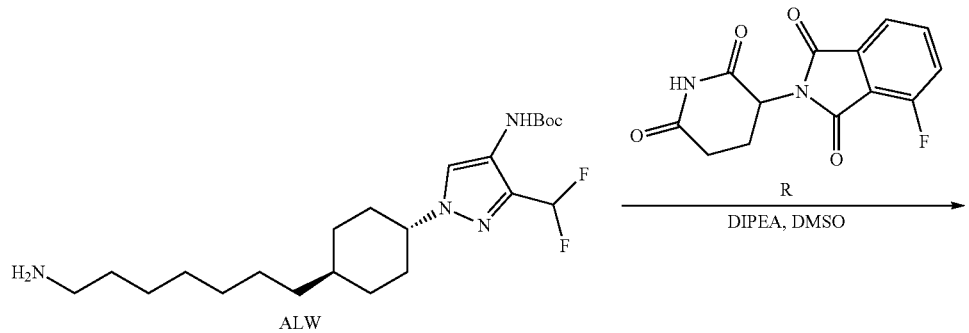

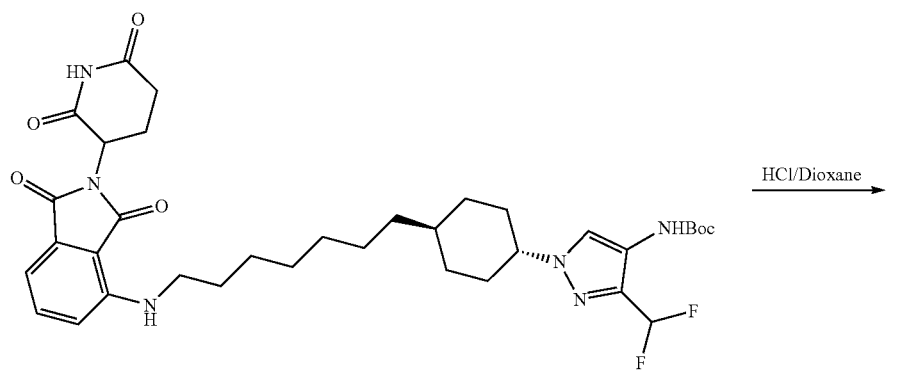

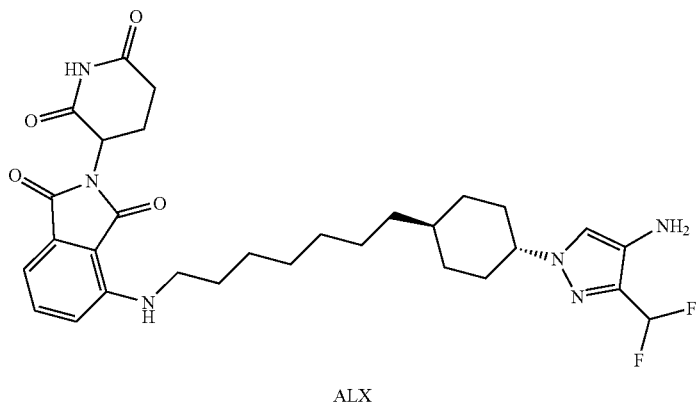

Step 1—Tert-butyl N-3-(difluoromethyl)-1-[4-[7-[[2-(2,6-dioxo-3-piperidyl)-1,3-dioxo-isoindolin-4-yl]amino]heptyl] cyclohexyl]pyrazol-4-yl]carbamate To a solution of tert-butyl N-[1-[4-(7-aminoheptyl)cyclohexyl]-3-(difluoromethyl)pyrazol-4-yl] carbamate (50.0 mg, 117 umol, Intermediate ALW) and 2-(2,6-dioxo-3-piperidyl)-4-fluoro-isoindoline-1,3-dione (32.2 mg, 117 umol, Intermediate R) in the DMSO (2 mL) was added DIPEA (45.2 mg, 350 umol, 61.0 uL). The mixture was stirred at 130° C. for 2 hrs. On completion, the reaction mixture was filtered and the filtrate was purified by reversed phase flash (0.1% FA) to give the title compound (15.0 mg, 19% yield) as yellow solid. LC-MS (ESI$^+$) m/z 685.5 (M+H)$^+$.

Step 2—4-[7-[4-[4-amino-3-(difluoromethyl)pyrazol-1-yl]cyclohexyl]heptylamino]-2-(2,6-dioxo-3-piperidyl)isoindoline-1,3-dione A solution of tert-butyl N-[3-(difluoromethyl)-1-[4-[7-[[2-(2,6-dioxo-3-piperidyl)-1,3-dioxo-isoindolin-4-yl]amino]heptyl]cyclohexyl]pyrazol-4-yl]carbamate (12.0 mg, 17.5 umol) in the HCl/dioxane (1 mL) was stirred at 20° C. for 1 hrs. On completion, the reaction mixture was concentrated in vacuo to give the title compound (10.0 mg, 98% yield) as yellow solid. LC-MS (ESI$^+$) m/z 585.4 (M+H)$^+$.

2163
Tert-butyl 4-[[4-(aminomethyl)phenyl]methyl]piperazine-1-carboxylate (Intermediate ANN)

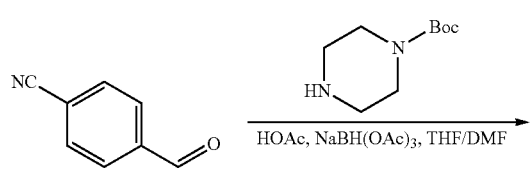

2164
2-(2,6-Dioxo-3-piperidyl)-4-[[4-(piperazin-1-ylmethyl)phenyl]methylamino]isoindoline-1,3-dione (Intermediate ANO)

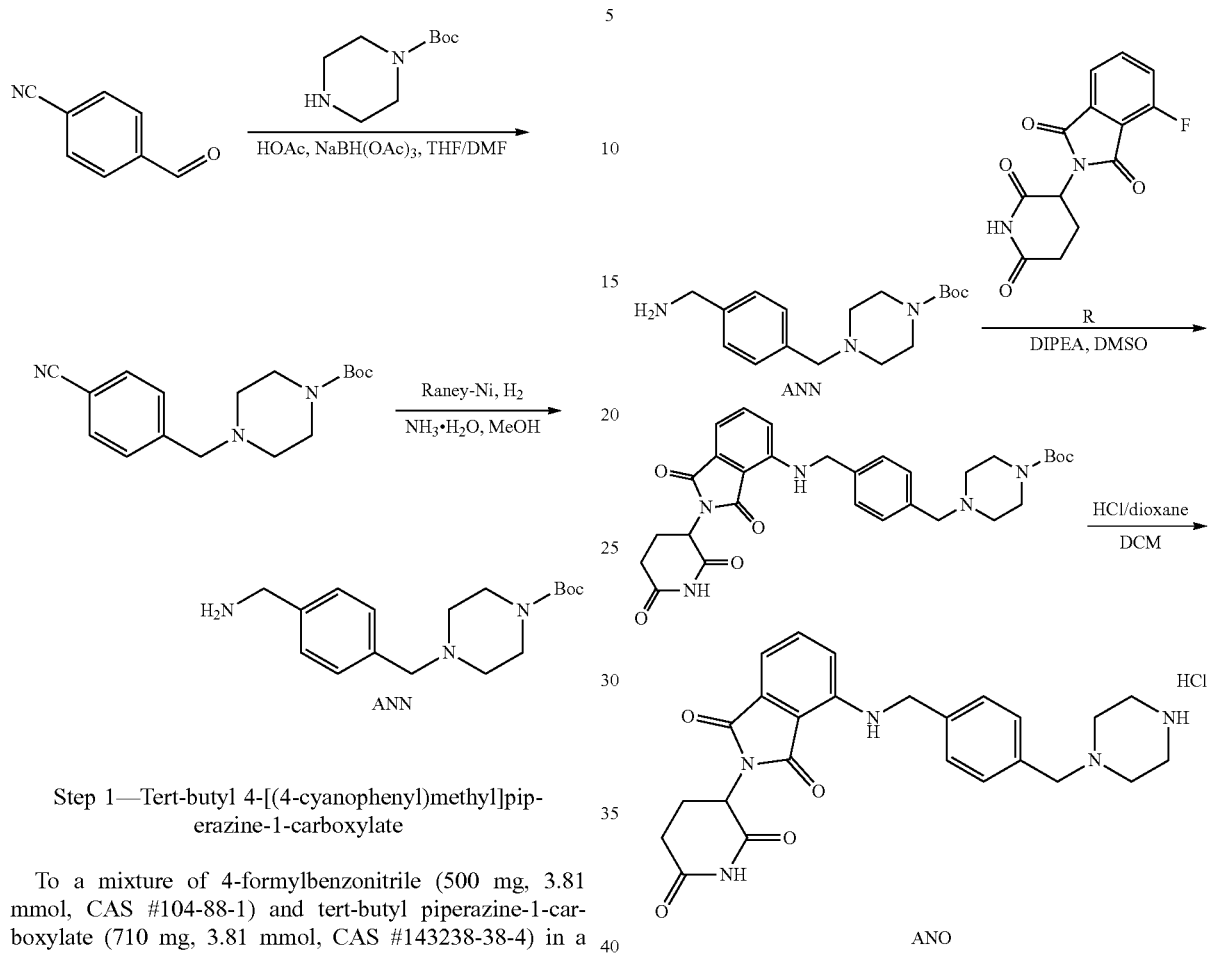

Step 1—Tert-butyl 4-[(4-cyanophenyl)methyl]piperazine-1-carboxylate

To a mixture of 4-formylbenzonitrile (500 mg, 3.81 mmol, CAS #104-88-1) and tert-butyl piperazine-1-carboxylate (710 mg, 3.81 mmol, CAS #143238-38-4) in a mixed solvent of THF (10 mL) and DMF (2 mL) was added HOAc (457 mg, 7.63 mmol). The reaction mixture was stirred at −15° C. for 0.5 hour. Then NaBH(OAc)$_3$ (969 mg, 4.58 mmol) was added to the reaction mixture and the reaction mixture was stirred at −15° C. for 1 hour. On completion, the reaction mixture was quenched by water (0.01 mL) and the mixture was concentrated in vacuo. The crude product was purified by reversed-phase HPLC (0.1% FA condition). The residue was then purified by silica gel chromatography (PE:EA=1:0 to 10:1) to give the title compound (720 mg, 62% yield) as white solid. $^1$H NMR (400 MHz, CDCl$_3$) δ 7.62 (d, J=8.0 Hz, 2H), 7.46 (d, J=8.0 Hz, 2H), 3.56 (s, 2H), 3.44 (d, J=4.4 Hz, 4H), 2.39 (s, 4H), 1.46 (s, 9H).

Step 2—Tert-butyl 4-[[4-(aminomethyl)phenyl]methyl]piperazine-1-carboxylate

To a solution of tert-butyl 4-[(4-cyanophenyl)methyl]piperazine-1-carboxylate (300 mg, 995 umol) in MeOH (20 mL) was added NH$_3$.H$_2$O (58.1 mg, 497 umol, 30% solution) and Raney-Ni (170 mg, 1.99 mmol). The reaction mixture was stirred at 20° C. for 2 hours under H$_2$ (50 Psi). On completion, the reaction mixture was filtered. The filtrated was concentrated in vacuo to give the title compound (300 mg, 98% yield) as yellow oil. LC-MS (ESI$^+$) m/z 306.1 (M+H)$^+$.

Step 1—Tert-butyl 4-[[4-[[[2-(2,6-dioxo-3-piperidyl)-1,3-dioxo-isoindolin-4-yl]amino]methyl]phenyl]methyl]piperazine-1-carboxylate To a solution of 2-(2,6-dioxo-3-piperidyl)-4-fluoro-isoindoline-1,3-dione (250 mg, 905 umol, Intermediate R) and tert-butyl 4-[[4-(aminomethyl)phenyl]methyl]piperazine-1-carboxylate (290 mg, 950 umol, Intermediate ANN) in DMSO (2 mL) was added DIPEA (584 mg, 4.53 mmol). The reaction mixture was stirred at 130° C. for 2 hours. On completion, the reaction mixture was acidified with 4M HCl/dioxane until the pH=7. The mixture was concentrated in vacuo. The mixture was purified by reversed-phase HPLC (0.1% FA condition) to give the title compound (350 mg, 68% yield) was obtained as green solid. $^1$H NMR (400 MHz, CDCl$_3$) δ 8.24 (s, 1H), 7.49-7.44 (m, 1H), 7.37-7.33 (m, 4H), 7.14 (d, J=7.2 Hz, 1H), 6.84 (d, J=8.4 Hz, 1H), 6.71 (t, J=5.6 Hz, 1H), 4.97-4.91 (m, 1H), 4.52 (d, J=5.6 Hz, 2H), 3.79 (s, 2H), 3.59-3.54 (m, 4H), 2.98-2.71 (m, 4H), 2.68 (t, J=5.2 Hz, 4H), 1.45 (s, 9H).

Step 2—2-(2,6-Dioxo-3-piperidyl)-4-[[4-(piperazin-1-ylmethyl)phenyl]methylamino]isoindoline-1,3-dione To a solution of tert-butyl 4-[[4-[[[2-(2,6-dioxo-3-piperidyl)-1,3-dioxo-isoindolin-4-yl]amino]methyl] phenyl]

2165 methyl]piperazine-1-(80 mg, 142 umol) in DCM (5 mL) was added HCl/dioxane (4 M, 5 mL). The reaction mixture was stirred at 20° C. for 1 hr. On completion, the reaction mixture was concentrated in vacuo to give the title compound (70.0 mg, 98% yield, HCl) as yellow solid. LC-MS (ESI⁺) m/z 462.3 (M+H)⁺.

2-[2-[[2-(2,6-Dioxo-3-piperidyl)-1,3-dioxo-isoindolin-4-yl]amino]ethoxy]ethyl methane-sulfonate (Intermediate AKW)

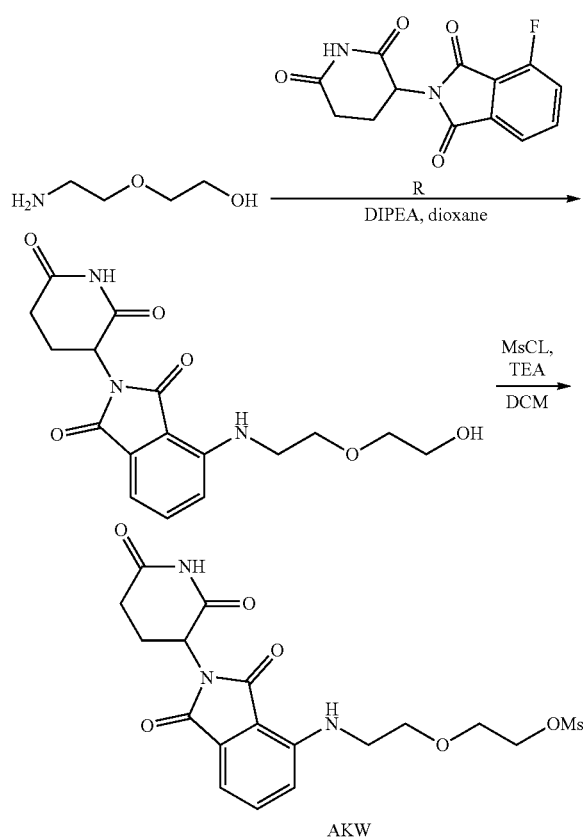

AKW

Step 1—2-(2,6-Dioxo-3-piperidyl)-4-[2-(2-hydroxyethoxy)ethylamino]isoindoline-1,3-dione To a solution of 2-(2-aminoethoxy)ethanol (500 mg, 3.53 mmol, HCl salt) in dioxane (15 mL) was added DIPEA (3.65 g, 28.2 mmol) and 2-(2,6-dioxo-3-piperidyl)-4-fluoro-isoindoline-1,3-dione (1.07 g, 3.88 mmol, Intermediate R), and the mixture was stirred at 115° C. for 16 h. On completion, the reaction mixture was concentrated in vacuo to give a residue. The residue was purified by silica gel chromatography (PE:EA=1:1) to give the title compound (500 mg, 37% yield) as a yellow solid. ¹H NMR (400 MHz, DMSO-d₆) δ 11.10 (s, 1H), 7.59 (dd, J=7.6, 8.4 Hz, 1H), 7.15 (d, J=8.8 Hz, 1H), 7.04 (d, J=6.8 Hz, 1H), 6.61 (t, J=5.6 Hz, 1H), 5.06 (dd, J=5.6, 12.8 Hz, 1H), 4.63 (t, J=5.6 Hz, 1H), 3.61 (t, J=5.6 Hz, 2H), 3.55-3.44 (m, 6H), 2.94-2.80 (m, 1H), 2.64-2.52 (m, 2H), 2.08-1.97 (m, 1H); LC-MS (ESI⁺) m/z 362.0 (M+H)⁺.

2166

Step 2—2-[2-[[2-(2,6-Dioxo-3-piperidyl)-1,3-dioxo-isoindolin-4-yl]amino]ethoxy]ethyl methanesulfonate To a solution of 2-(2,6-dioxo-3-piperidyl)-4-[2-(2-hydroxyethoxy)ethylamino]isoindoline-1,3-dione (200 mg, 525 umol) and TEA (159 mg, 1.58 mmol) in DCM (20 mL) was added MsCl (120 mg, 1.05 mmol) at 0° C. Then the mixture was allowed to warm to rt and stirred for 3 h. On completion, the reaction mixture was quenched by adding water (30 mL) at 0° C., and then the mixture was extracted with DCM (3×40 mL). The combined organic layers were washed with saturated citric acid (2×20 mL), dried over Na₂SO₄, filtered and concentrated in vacuo to give the title compound (200 mg, 86% yield) as a yellow solid. LC-MS (ESI⁺) m/z 440.0 (M+H)⁺.

4-[3-(difluoromethyl)-4-[[5-[(1R,4R)-2-oxa-5-azabi-cyclo[2.2.1]heptan-5-yl]pyrazolo 1,5-a]pyrimidine-3-carbonyl]amino]pyrazol-1-yl]cyclohexanecarboxylic acid (Intermediate ALS)

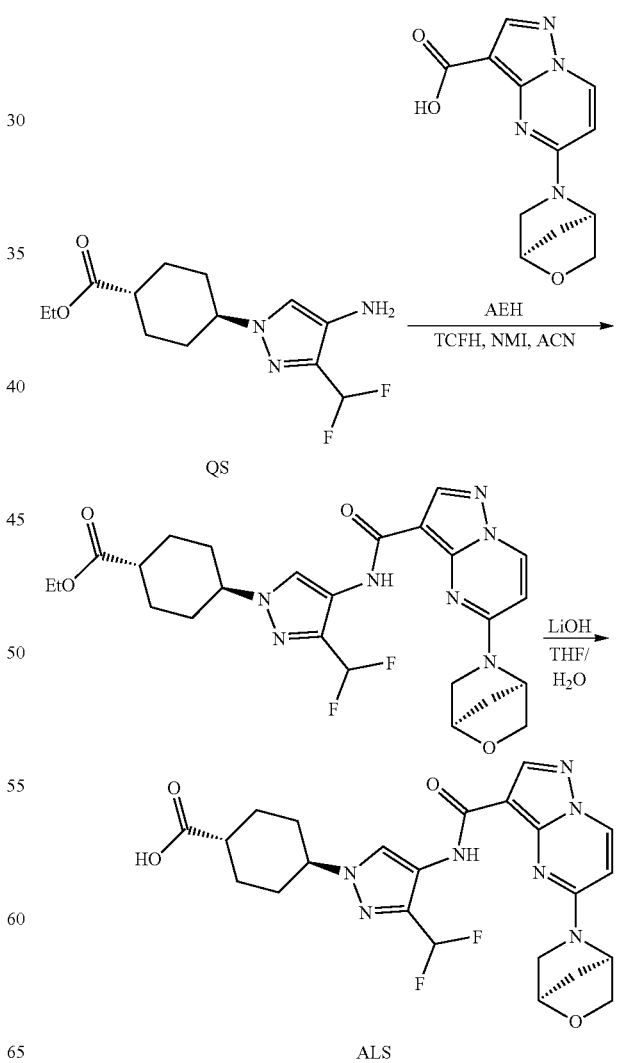

ALS

Step 1—Ethyl 4-[3-(difluoromethyl)-4-[[5-[(1R, 4R)-2-oxa-5-azabicyclo[2.2.1]heptan-5-yl] pyrazolo [1,5-a]pyrimidine-3-carbonyl]amino]pyrazol-1-yl] cyclohexanecarboxylate To a solution of 5-[(1R,4R)-2-oxa-5-azabicyclo[2.2.1]heptan-5-yl]pyrazolo[1,5-a]pyrimidine-3-carboxylic acid (200 mg, 768 umol, Intermediate AEH) in ACN (2.00 mL) was added [chloro(dimethylamino)methylene]-dimethylammonium; hexafluorophosphate (258 mg, 922 umol), 1-methylimidazole (220 mg, 2.69 mmol, 214 uL). The mixture was stirred at 20° C. for 1 hour. Then ethyl 4-[4-amino-3-(difluoromethyl)pyrazol-1-yl]cyclohexanecarboxylate (221 mg, 768 umol, Intermediate QS) was added, then the reaction mixture was stirred at 20° C. for 16 hours. On completion, the reaction mixture was quenched with water (5.0 mL), and then concentrated in vacuo to give a residue. The residue was purified by reverse phase (0.1% HCl condition) to give the title compound (220 mg, 54% yield) as a yellow solid. $^1$H NMR (400 MHz, CDCl$_3$) δ 9.61 (s, 1H), 8.43 (d, J=3.2 Hz, 2H), 8.32 (d, J=7.8 Hz, 1H), 6.96-6.58 (m, 1H), 6.13 (d, J=7.6 Hz, 1H), 5.46 (s, 1H), 4.87-4.76 (m, 1H), 4.16 (q, J=7.2 Hz, 2H), 4.13-4.04 (m, 1H), 4.03-3.94 (m, 2H), 3.63-3.46 (m, 2H), 2.41-2.33 (m, 1H), 2.30-2.23 (m, 2H), 2.22-2.16 (m, 2H), 2.12-1.98 (m, 2H), 1.83 (q, J=3.2, 12.8 Hz, 2H), 1.71-1.62 (m, 2H), 1.28 (t, J=7.2 Hz, 3H).

Step 2—4-[3-(Difluoromethyl)-4-[[5-[(1R,4R)-2-oxa-5-azabicyclo[2.2.1]heptan-5-yl]pyrazolo [1,5-a] pyrimidine-3-carbonyl]amino]pyrazol-1-yl]cyclohexanecarboxylic acid To a solution of ethyl 4-[3-(difluoromethyl)-4-[[5-[(1R, 4R)-2-oxa-5-azabicyclo[2.2.1] heptan-5-yl] pyrazolo[1,5-a] pyrimidine-3-carbonyl]amino]pyrazol-1-yl]cyclohexanecarboxylate (100 mg, 188 umol) in a mixed solvent of THF (2.00 mL) and H$_2$O (0.25 mL) was added LiOH—H$_2$O (15.9 mg, 377 umol). The mixture was stirred at 20° C. for 3 hours. On completion, the reaction mixture was concentrated in vacuo to remove THF, and then diluted with water. Then the mixture was acidified with 1N HCl solution until the pH=6. The aqueous phase was extracted with solvent (DCM: MeOH=20:1) (6×5 mL). The combined organic layer was washed with brine (10 mL), dried with anhydrous Na$_2$SO$_4$, filtered and concentrated in vacuo to give the title compound (94 mg, 99% yield) as a white solid. $^1$H NMR (400 MHz, CDCl$_3$) δ 8.03 (s, 1H), 6.91-6.85 (m, 1H), 6.85-6.80 (m, 1H), 6.76-6.69 (m, 1H), 5.22 (dd, J=5.4, 12.4 Hz, 1H), 3.47-3.42 (m, 3H), 3.01-2.92 (m, 1H), 2.90-2.79 (m, 1H), 2.68-2.78 (m, 1H), 2.68-2.55 (m, 2H), 2.45-2.20 (m, 4H), 2.08-2.03 (m, 1H), 2.02-1.98 (m, 1H), 1.79-1.65 (m, 1H), 1.53-1.41 (m, 2H), 1.38-1.24 (m, 1H).

Tert-butyl N-[2-[4-(aminomethyl)phenyl] ethyl]-N-methyl-carbamate (Intermediate AKX)

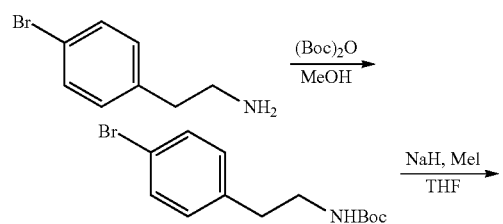

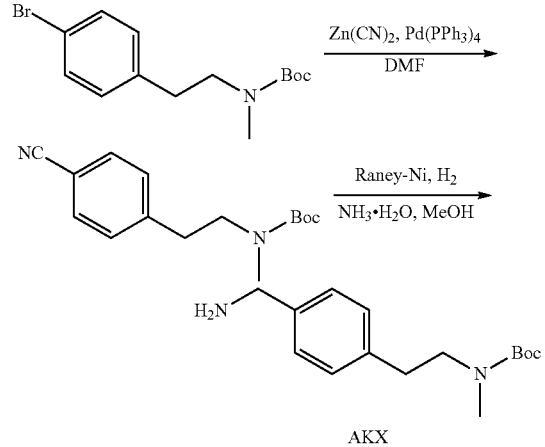

AKX

Step 1—Tert-butyl N-[2-(4-bromophenyl)ethyl]carbamate

To a solution of 2-(4-bromophenyl)ethanamine (2.00 g, 10.0 mmol, CAS #58971-11-2) in MeOH (20.0 mL) was added (Boc)$_2$O (3.27 g, 14.9 mmol, 3.44 mL), and the mixture was stirred at 20° C. for 16 hours. On completion, the reaction mixture was concentrated in vacuo to give a residue. The residue was purified by column chromatography (SiO$_2$, Petroleum ether/Ethyl acetate=I/O to 10/1) to give the title compound (2.70 g, 89% yield) as a white solid. $^1$H NMR (400 MHz, CDCl$_3$) δ 7.47-7.39 (m, 2H), 7.07 (d, J=8.4 Hz, 2H), 4.53 (s, 1H), 3.46-3.22 (m, 2H), 2.76 (t, J=6.8 Hz, 2H), 1.44 (s, 9H).

Step 2—Tert-butyl N-[2-(4-bromophenyl)ethyl]-N-methyl-carbamate

To a solution of tert-butyl N-[2-(4-bromophenyl)ethyl] carbamate (2.00 g, 6.66 mmol) in THF (20.0 mL) was added NaH (293 mg, 7.33 mmol, 60% dispersion in mineral oil), and the mixture was stirred at 0° C. for 0.5 hour. Then, MeI (10.9 g, 77.2 mmol) was added and the mixture was stirred at 20° C. for 1 hour. On completion, the reaction mixture was quenched with water (5 mL) at 0° C., dried over Na$_2$SO$_4$, filtered and the filtrate was concentrated in vacuo to give a residue. The residue was purified by column chromatography (SiO$_2$, Petroleum ether/Ethyl acetate=100/1 to 50/1) to afford the title compound (780 mg, 37% yield) as a white oil. $^1$H NMR (400 MHz, CDCl$_3$) δ 7.41 (d, J=8.4 Hz, 2H), 7.15-6.95 (m, 2H), 3.50-3.30 (m, 2H), 2.91-2.66 (m, 5H), 1.51-1.26 (m, 9H).

Step 3—Tert-butyl N-[2-(4-cyanophenyl)ethyl]-N-methyl-carbamate

A mixture of tert-butyl N-[2-(4-bromophenyl)ethyl]-N-methyl-carbamate (380 mg, 1.21 mmol), Zn(CN)$_2$ (284 mg, 2.42 mmol), Pd(PPh$_3$)$_4$ (139 mg, 120 umol) in DMF (5.00 mL) was degassed and purged with N$_2$ for 3 times, and then the mixture was stirred at 100° C. under N$_2$ atmosphere for 16 hours. On completion, the reaction mixture was filtered and the filtrate was concentrated in vacuo to give a residue. The residue was purified by reverse phase (0.1% FA condition) to give the title compound (260 mg, 82% yield) as a white solid. $^1$H NMR (400 MHz, CDCl$_3$) δ 7.59 (d, J=8.0

Hz, 2H), 7.35-7.27 (m, 2H), 3.46 (t, J=7.2 Hz, 2H), 2.87 (t, J=6.5 Hz, 2H), 2.82 (s, 3H), 1.40 (s, 9H).

Step 4—Tert-butyl N-[2-[4-(aminomethyl)phenyl]ethyl]-N-methyl-carbamate

To a solution of tert-butyl N-[2-(4-cyanophenyl)ethyl]-N-methyl-carbamate (100 mg, 384 umol) in MeOH (3.00 mL) was added Raney-Ni (50.0 mg, 58.4 umol, 10 wt %) and $NH_3$—$H_2O$ (108 mg, 768 umol, 25% solution) under $N_2$ atmosphere. The suspension was degassed and purged with $H_2$ for 3 times. The mixture was stirred under $H_2$ (50 psi) at 20° C. for 16 hours. On completion, the reaction mixture was filtered and the filtrate was concentrated in vacuo to give the title compound (100 mg, 98% yield) as colorless oil. $^1$H NMR (400 MHz, $CDCl_3$) δ 7.29 (d, J=7.6 Hz, 2H), 7.24-7.16 (m, 2H), 3.91 (s, 2H), 3.40 (t, J=7.2 Hz, 2H), 2.85-2.75 (m, 5H), 1.42 (s, 9H).

2-(2,6-Dioxo-3-piperidyl)-4-[[4-[2-(methylamino)ethyl]phenyl]methylamino]isoindoline-1,3-dione (Intermediate AKY)

line-1,3-dione (50.0 mg, 181 umol, Intermediate R) in DMSO (1.00 mL) was added DIPEA (116 mg, 905 umol). The mixture was stirred at 130° C. for 3 hours. On completion, the reaction mixture was filtered and concentrated in vacuo to give a residue. The residue was purified by reverse phase (0.1% FA condition) to give the title compound (50.0 mg, 53% yield) as a yellow solid. $^1$H NMR (400 MHz, DMSO-$d_6$) δ 8.09 (s, 1H), 7.45 (dd, J=7.2, 8.4 Hz, 1H), 7.28 (s, 1H), 7.26 (s, 1H), 7.18 (s, 2H), 7.12 (d, J=7.2 Hz, 1H), 6.84 (d, J=8.4 Hz, 1H), 6.75-6.57 (m, 1H), 4.97-4.89 (m, 1H), 4.48 (s, 2H), 3.42 (t, J=6.8 Hz, 2H), 2.96-2.86 (m, 1H), 2.84-2.70 (m, 7H), 2.21-2.11 (m, 1H), 1.41 (s, 9H).

Step 2—2-(2,6-Dioxo-3-piperidyl)-4-[[4-[2-(methylamino)ethyl]phenyl]methylamino]isoindoline-1,3-dione To a solution of tert-butyl N-[2-[4-[[[2-(2,6-dioxo-3-piperidyl)-1,3-dioxo-isoindolin-4-yl] amino] methyl]phenyl]ethyl]-N-methylcarbamate (50.0 mg, 96.0 umol) in DCM (0.50 mL) was added HCl/dioxane (4 M, 4.80 uL). The mixture was stirred at 25° C. for 0.5 hour. On completion, the reaction mixture was concentrated in vacuo to give the title compound (43.0 mg, 97% yield, HCl salt) as a white solid. LC-MS (ESI$^+$) m/z 421.2 (M+H)$^+$.

4-[(7-Azaspiro[3.5]nonan-2-ylamino)methyl]-2-(2,6-dioxo-3-piperidyl)isoindoline-1,3-dione (Intermediate ALK)

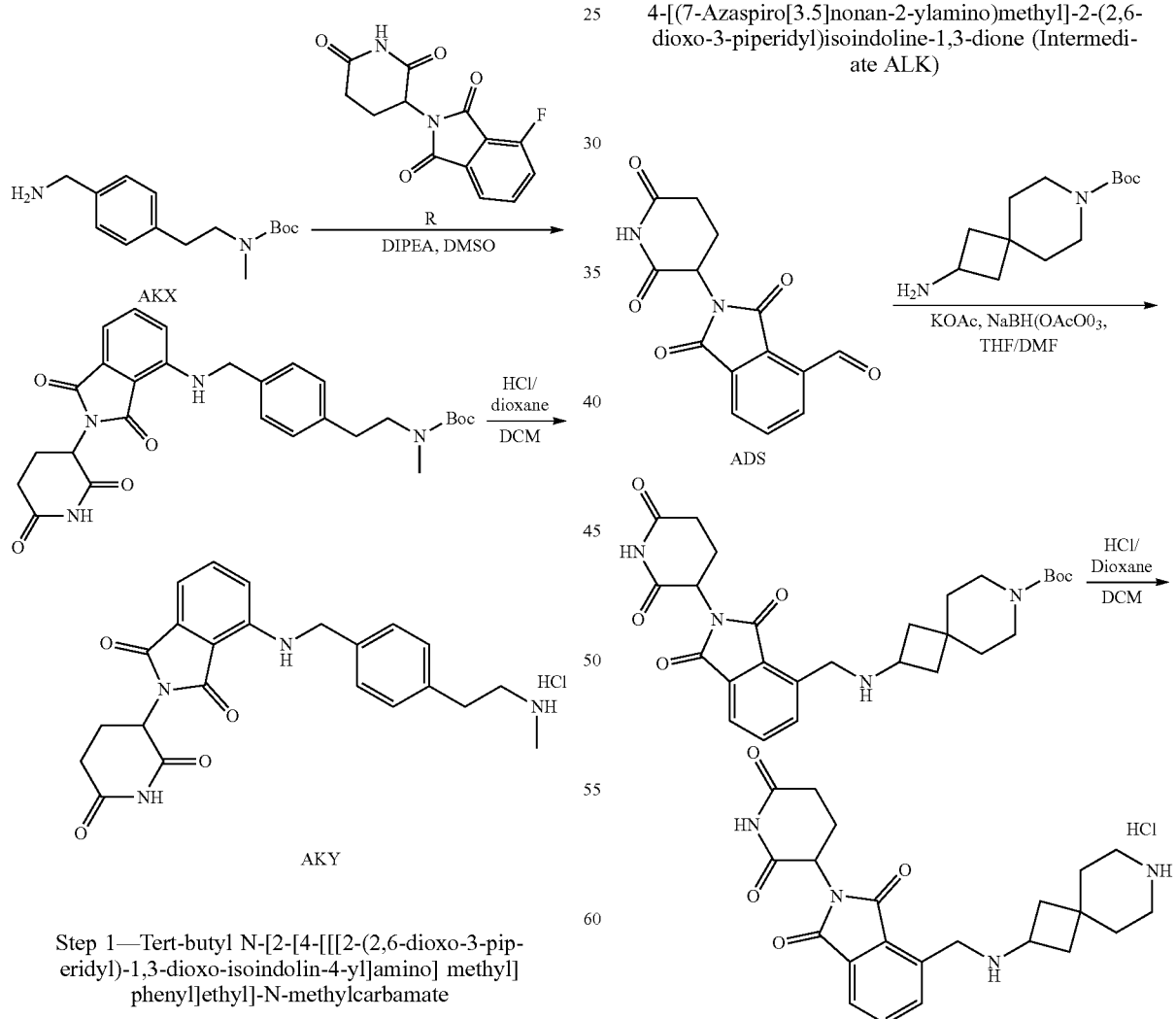

Step 1—Tert-butyl N-[2-[4-[[[2-(2,6-dioxo-3-piperidyl)-1,3-dioxo-isoindolin-4-yl]amino] methyl]phenyl]ethyl]-N-methylcarbamate To a solution of tert-butyl N-[2-[4-(aminomethyl)phenyl]ethyl]-N-methyl-carbamate (50.0 mg, 189 umol, Intermediate AKX) and 2-(2,6-dioxo-3-piperidyl)-4-fluoro-isoindo-

Step 1—2-(2,6-Dioxo-3-piperidyl)-1,3-dioxo-isoindoline-4-carbaldehyde

To a mixture of tert-butyl 2-amino-7-azaspiro[3.5]nonane-7-carboxylate (142 mg, 594 umol, CAS #1239319-82-4) in THF (10 mL) and DMF (2 mL) was added KOAc (175 mg, 1.78 mmol). Then 2-(2,6-dioxo-3-piperidyl)-1,3-dioxo-isoindoline-4-carbaldehyde (170 mg, 593 umol, Intermediate ADS) and NaBH(OAc)$_3$ (151 mg, 713 umol) was added into the mixture. The mixture was stirred at 20° C. for 2 hours. On completion, the reaction was quenched with water (5 mL). The mixture was concentrated in vacuo. The residue was purified by reversed-phase HPLC (0.1% FA condition) to give the title compound (105 mg, 34% yield) as a white solid. LC-MS (ESI$^+$) m/z 511.5 (M+H)$^+$.

Step 2—4-[(7-Azaspiro[3.5]nonan-2-ylamino)methyl]-2-(2,6-dioxo-3-piperidyl)isoindoline-1,3-dione To a mixture of tert-butyl 2-[[2-(2,6-dioxo-3-piperidyl)-1,3-dioxo-isoindolin-4-yl]methylamino]-7-azaspiro [3.5]nonane-7-carboxylate (105 mg, 205 umol) in DCM (2 mL) was added HCl/dioxane (4 M, 102 uL). The mixture was stirred at 20° C. for 0.5 hour. On completion, the reaction mixture was concentrated in vacuo to give the title compound (91 mg, 99% yield, HCl salt) as a white solid. LC-MS (ESI$^+$) m/z 411.5 (M+H)$^+$.

Tert-butyl N-[3-[4-(aminomethyl)phenyl]propyl]-N-methyl-carbamate (Intermediate AKF)

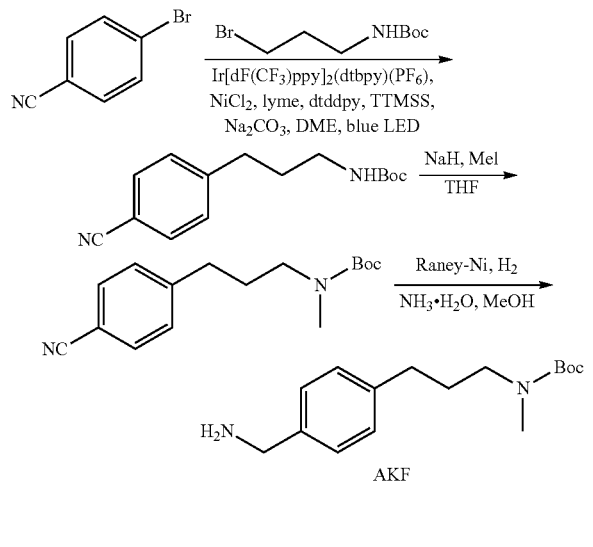

Step 1—Tert-butyl N-[3-(4-cyanophenyl)propyl]carbamate

A mixture of 4-bromobenzonitrile (0.50 g, 2.75 mmol, CAS #623-00-7), tert-butyl N-(3-bromopropyl) carbamate (851 mg, 3.58 mmol, CAS #83948-53-2), bis[3,5-difluoro-2-[5-(trifluoromethyl)-2-pyridyl]phenyl]iridium(1+); 4-tert-butyl-2-(4-tert-butyl-2-pyridyl)pyridine; hexaflorophosphate (30.8 mg, 27.5 umol), dichloronickel; 1,2-dimethoxyethane (3.02 mg, 13.7 umol), 4-tert-butyl-2-(4-tert-butyl-2-pyridyl)pyridine (3.69 mg, 13.7 umol), bis(trimethylsilyl)silyl-trimethyl-silane (4.10 mg, 16.5 umol) and Na$_2$CO$_3$ (582 mg, 5.50 mmol) in DME (15 mL) was stirred at 25° C. for 14 hours irradiated with a 34 W blue LED lamp under nitrogen. On completion, the reaction mixture was filtered. The filtrate was concentrated in vacuo. The residue was purified by silica gel chromatography (PE:EA=1:0 to 0:1) to give the title compound (900 mg, 62% yield) as colourless oil. $^1$H NMR (400 MHz, CDCl$_3$) δ 7.61-7.55 (m, 2H), 7.29 (d, J=8.0 Hz, 2H), 4.62-4.45 (m, 1H), 3.22-3.03 (m, 2H), 2.76-2.65 (m, 2H), 1.90-1.76 (m, 2H), 1.45 (s, 9H).

Step 2—Tert-butyl N-[3-(4-cyanophenyl)propyl]-N-methyl-carbamate

To a mixture of tert-butyl N-[3-(4-cyanophenyl)propyl] carbamate (900 mg, 3.46 mmol) in DMF (10 mL) was added NaH (165 mg, 4.15 mmol, 60% dispersion in mineral oil) at 0° C. The mixture was stirred at 0° C. for 0.5 hour under nitrogen atmosphere. Then MeI (1.96 g, 13.8 mmol) was added to the reaction mixture. The mixture was stirred at 0° C. for 2.5 hours under nitrogen atmosphere. On completion, the reaction mixture was quenched by water (30 mL). The mixture was extracted with EA (3×30 mL). The combined organic layer was washed with brine (3×30 mL). The organic layer was concentrated in vacuo. The residue was purified by silica gel chromatography (PE:EA=1:0 to 10:1) to give the title compound (910 mg, 95% yield) as yellow oil. $^1$H NMR (400 MHz, CDCl$_3$) δ 7.58 (d, J=8.0 Hz, 2H), 7.30 (d, J=8.0 Hz, 2H), 3.26 (s, 2H), 2.85 (s, 3H), 2.71-2.61 (m, 2H), 1.90-1.80 (m, 2H), 1.47-1.44 (m, 9H).

Step 3—Tert-butyl N-[3-[4-(aminomethyl)phenyl]propyl]-N-methyl-carbamate

To a mixture of tert-butyl N-[3-(4-cyanophenyl)propyl]-N-methyl-carbamate (350 mg, 1.28 mmol) in MeOH (20 mL) was added NH$_3$.H$_2$O (74.5 mg, 637 umol, 30% solution) and Raney-Ni (218 mg, 2.55 mmol). The reaction mixture was stirred at 20° C. for 16 hours under H$_2$ (50 Psi). On completion, the reaction mixture was filtrated. The filtrate was concentrated in vacuo to give the title compound (330 mg, 92% yield) as colourless oil. LC-MS (ESI$^+$) m/z 279.2 (M+H)$^+$.

2-(2,6-Dioxo-3-piperidyl)-4-[[4-[3-(methylamino)propyl]phenyl]methylamino]isoindoline-1,3-dione (Intermediate AKG)

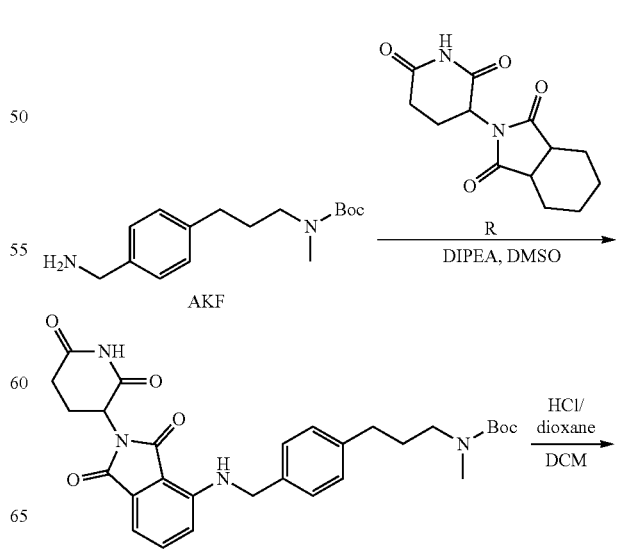

-continued

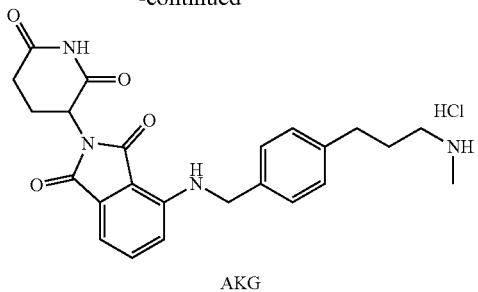

AKG

Step 1—Tert-butyl N-[3-[4-[[[2-(2,6-dioxo-3-piperidyl)-1,3-dioxo-isoindolin-4-yl]amino]methyl]phenyl]propyl]-N-methyl-carbamate To a mixture of 2-(2,6-dioxo-3-piperidyl)-4-fluoro-isoindoline-1,3-dione (100 mg, 362 umol, Intermediate R) and tert-butyl N-[3-[4-(aminomethyl)phenyl]propyl]-N-methyl-carbamate (110 mg, 398 umol, Intermediate AKF) in DMSO (3 mL) was added DIPEA (233 mg, 1.81 mmol). The reaction mixture was stirred at 130° C. for 2 hours. On completion, the reaction mixture was acidified with 4M HCl/dioxane until the pH=7. The mixture was concentrated in vacuo. The mixture was purified by reversed-phase HPLC (0.1% FA condition) to give the title compound (100 mg, 51% yield) as yellow solid. $^1$H NMR (400 MHz, CDCl$_3$) δ 7.46 (dd, J=7.2, 8.4 Hz, 1H), 7.25 (s, 1H), 7.21-7.16 (m, 2H), 7.13 (d, J=6.8 Hz, 1H), 6.86 (d, J=8.4 Hz, 1H), 6.66 (t, J=5.6 Hz, 1H), 4.96-4.89 (m, 1H), 4.48 (d, J=5.6 Hz, 2H), 3.25 (d, J=4.0 Hz, 2H), 2.96-2.66 (m, 7H), 2.63-2.56 (m, 2H), 2.19-2.10 (m, 1H), 2.0 (s, 3H), 1.91-1.77 (m, 3H), 1.45 (s, 9H).

Step 2—2-(2,6-Dioxo-3-piperidyl)-4-[[4-[3-(methylamino)propyl]phenyl]methylamino]isoindoline-1,3-dione To a solution of tert-butyl N-[3-[4-[[[2-(2,6-dioxo-3-piperidyl)-1,3-dioxo-isoindolin-4-yl]amino] methyl]phenyl]propyl]-N-methyl-carbamate (100 mg, 187 umol) in DCM (5 mL) was added HCl/dioxane (4 M, 5 mL). The reaction mixture was stirred at 20° C. for 0.5 hour. On completion, the reaction mixture was concentrated in vacuo to give the title compound (85 mg, 96% yield, HCl salt) as yellow solid. LC-MS (ESI$^+$) m/z 435.2 (M+H)$^+$.

3-[3-Methyl-4-[2-[4-(methylamino)-1-piperidyl]ethyl]-2-oxo-benzimidazol-1-yl]piperidine-2,6-dione (Intermediate AKA)

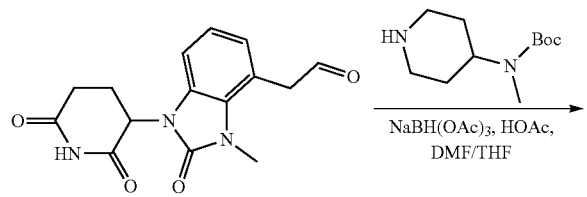

-continued

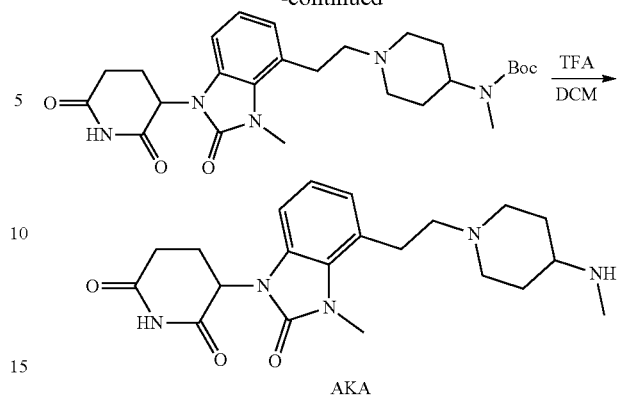

AKA

Step 1—Tert-butyl N-[1-[2-[1-(2,6-dioxo-3-piperidyl)-3-methyl-2-oxo-benzimidazol-4-yl]ethyl]-4-piperidyl]-N-methyl-carbamate To a mixture of 2-[1-(2,6-dioxo-3-piperidyl)-3-methyl-2-oxo-benzimidazol-4-yl]acetaldehyde (520 mg, 1.73 mmol, synthesized via Step 1 of Intermediate AAP) and tert-butyl N-methyl-N-(4-piperidyl)carbamate (369 mg, 1.73 mmol, CAS #108612-54-0) in a mixed solvent of DMF (3 mL) and THF (3 mL) was added HOAc (103 mg, 1.73 mmol, 98.7 uL). The mixture and stirred at 25° C. for 0.5 hour. Next, NaBH(OAc)$_3$ (731 mg, 3.45 mmol) was added to the mixture. The reaction mixture was stirred at 25° C. for 12 hours. On completion, the reaction mixture was quenched with water (0.05 mL) and concentrated in vacuo to give a residue. The residue was purified by prep-HPLC (column: Phenomenex Synergi C18 150*25*10 um; mobile phase: [water (0.225% FA)-ACN]; B %: 6%-36%, 10 min) to give the title compound (70.0 mg, 8% yield) as white solid. LC-MS (ESI$^+$) m/z 500.4 (M+H)$^+$.

Step 2—3-[3-Methyl-4-[2-[4-(methylamino)-1-piperidyl]ethyl]-2-oxo-benzimidazol-1-yl]piperidine-2,6-dione To a mixture of tert-butyl N-[1-[2-[1-(2,6-dioxo-3-piperidyl)-3-methyl-2-oxo-benzimidazol-4-yl]ethyl]-4-piperidyl]-N-methyl-carbamate (60.0 mg, 120 umol) in DCM (1 mL) was added TFA (1.54 g, 13.5 mmol, 1.0 mL). The reaction mixture was stirred at 25° C. for 0.5 hour. On completion, the reaction mixture was concentrated in vacuo to give the title compound (60.0 mg, 97% yield, TFA salt) as light yellow solid. LC-MS (ESI$^+$) m/z 400.3 (M+H)$^+$.

4-[2-(4-Bromophenyl)ethylamino]-2-(2,6-dioxo-3-piperidyl)isoindoline-1,3-dione (Intermediate AKB)

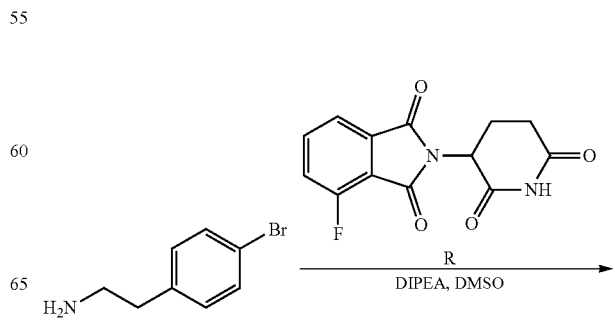

-continued

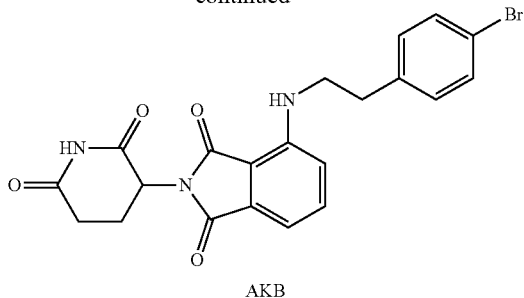

AKB

To a solution of 2-(4-bromophenyl)ethanamine (300 mg, 1.50 mmol, CAS #73918-56-6) and 2-(2,6-dioxo-3-piperidyl)-4-fluoro-isoindoline-1,3-dione (276 mg, 999 umol, Intermediate R) in DMSO (15 mL) was added DIPEA (18.7 mg, 144 umol) at 25° C. The reaction mixture was stirred at 130° C. for 2 hours. On completion, the reaction mixture was concentrated in vacuo. The residue was purified by reverse phase (0.1% FA condition) to give the title compound (360 mg, 78% yield) as a yellow solid. $^1$H NMR (400 MHz, DMSO-$d_6$) δ 11.09 (s, 1H), 7.58 (dd, J=7.2, 8.4 Hz, 1H), 7.52-7.47 (m, 2H), 7.27 (d, J=8.4 Hz, 2H), 7.16 (d, J=8.8 Hz, 1H), 7.03 (d, J=6.8 Hz, 1H), 6.56 (t, J=6.0 Hz, 1H), 5.05 (dd, J=5.6, 12.8 Hz, 1H), 3.58-3.48 (m 2H), 2.87 (t, J=7.6 Hz, 2H), 2.63-2.51 (m, 3H), 2.06-1.98 (m, 1H); LC-MS (ESI$^+$) m/z 455.9 (M+H)$^+$.

2-(2,6-Dioxo-3-piperidyl)-4-[2-[4-(4-piperidyl)phenyl]ethylamino]isoindoline-1,3-dione (Intermediate AKC)

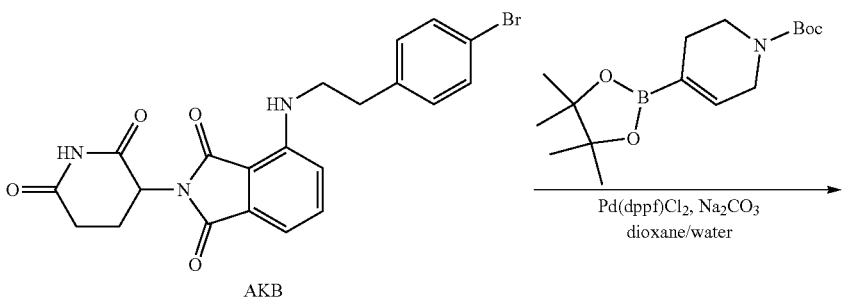

AKB

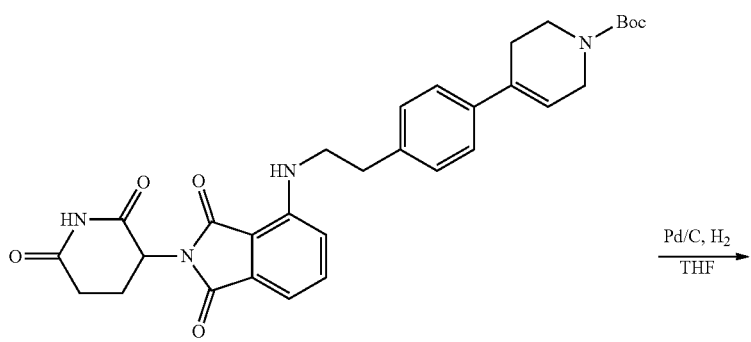

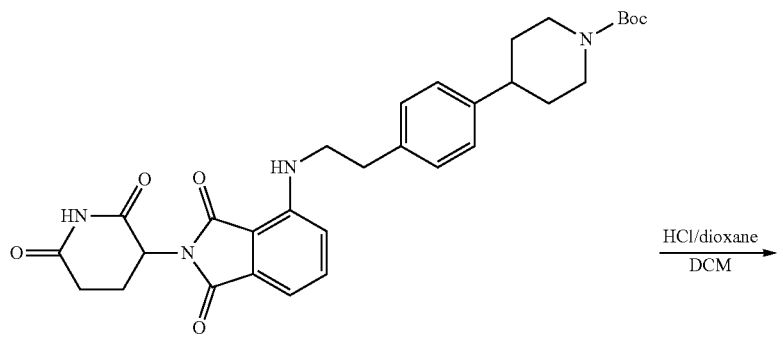

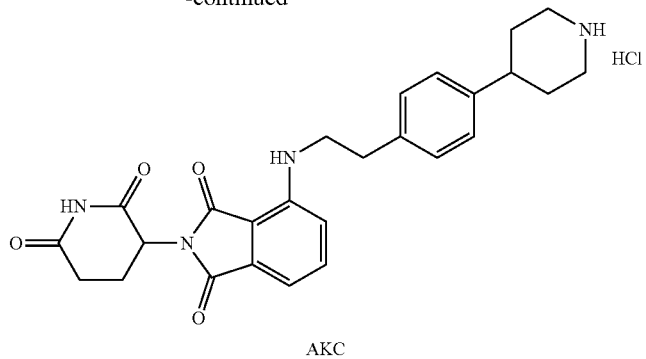

AKC

Step 1—Tert-butyl 4-[4-[2-[[2-(2,6-dioxo-3-piperidyl)-1,3-dioxo-isoindolin-4-yl]amino] ethyl]phenyl]-3,6-dihydro-2H-pyridine-1-carboxylate To a solution of 4-[2-(4-bromophenyl)ethylamino]-2-(2,6-dioxo-3-piperidyl)isoindoline-1,3-dione (250 mg, 547 umol, Intermediate AKB) and tert-butyl 4-(4,4,5,5-tetramethyl-1,3,2-dioxaborolan-2-yl)-3,6-dihydro-2H-pyridine-1-carboxylate (220 mg, 712 umol, CAS #286961-14-6) in dioxane (10 mL) and H$_2$O (1 mL) was added K$_3$PO$_4$ (348 mg, 1.64 mmol) and XPhos Pd G3 (69.5 mg, 82.1 umol) at 25° C. under N$_2$. The reaction mixture was stirred at 80° C. for 3 hours under N$_2$. On completion, the reaction mixture was diluted with H$_2$O (30 mL), and extracted with EA mL (3×10 mL). The combined organic layers were washed with H$_2$O (3×10 mL), dried over Na$_2$SO$_4$, filtered and concentrated in vacuo. The residue was purified by reverse phase (0.1% FA condition) to give the title compound (300 mg, 98% yield) as a yellow solid. $^1$H NMR (400 MHz, DMSO-d$_6$) δ 11.08 (s, 1H), 7.63-7.55 (m, 1H), 7.38 (d, J=8.0 Hz, 2H), 7.31-7.25 (m, 2H), 7.16 (d, J=8.4 Hz, 1H), 7.03 (d, J=7.2 Hz, 1H), 6.56 (t, J=6.0 Hz, 1H), 6.12 (s, 1H), 5.04 (dd, J=5.6, 12.8 Hz, 1H), 3.98 (s, 2H), 3.59-3.49 (m, 4H), 2.91-2.85 (m, 2H), 2.62-2.51 (m, 4H), 2.45 (s, 2H), 1.42 (s, 9H); LC-MS (ESI$^+$) m/z 459.0 (M−100)$^+$.

Step 2—Tert-butyl 4-[4-[2-[[2-(2,6-dioxo-3-piperidyl)-1,3-dioxo-isoindolin-4-yl]amino] ethyl]phenyl] piperidine-1-carboxylate To a solution of tert-butyl 4-[4-[2-[[2-(2,6-dioxo-3-piperidyl)-1,3-dioxo-isoindolin-4-yl]amino]ethyl] phenyl]-3,6-dihydro-2H-pyridine-1-carboxylate (160 mg, 286 umol) in THF (10 mL) was added Pd/C (200 mg, 286 umol, 10 wt %) at 25° C. The reaction mixture was stirred at 25° C. for 3 hours under H$_2$ (50 psi). On completion, the reaction mixture was filtered with celite and the filtrate was concentrated in vacuo to give the title compound (140 mg, 87% yield) as a yellow solid. LC-MS (ESI$^+$) m/z 461.3 (M−100+H)$^+$.

Step 3—2-(2,6-Dioxo-3-piperidyl)-4-[2-[4-(4-piperidyl)phenyl]ethylamino]isoindoline-1,3-dione To a solution of tert-butyl 4-[4-[2-[[2-(2,6-dioxo-3-piperidyl)-1,3-dioxo-isoindolin-4-yl]amino]ethyl] phenyl]piperidine-1-carboxylate (140 mg, 249 umol) in DCM (5 mL) was added HCl/dioxane (4 M, 2.10 mL) at 25° C. The mixture was stirred at 25° C. for 2 hours. On completion, the reaction mixture was concentrated in vacuo to give the title compound (120 mg, 96% yield, HCl salt) as a yellow solid. LC-MS (ESI$^+$) m/z 461.3 (M+H)$^+$.

Tert-butyl 4-prop-2-ynylpiperidine-1-carboxylate (Intermediate AKO)

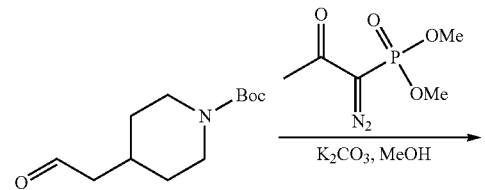

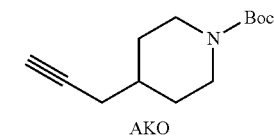

AKO

To a solution of tert-butyl 4-(2-oxoethyl)piperidine-1-carboxylate (500 mg, 2.20 mmol, CAS #142374-19-4), K$_2$CO$_3$ (912 mg, 6.60 mmol) in MeOH (15 mL) was added 1-diazo-1-dimethoxyphosphoryl-propan-2-one (507 mg, 2.64 mmol, CAS #90965-06-3) at 0° C. The mixture was stirred at 25° C. for 16 hours. On completion, the mixture was concentrated in vacuo. The mixture was diluted with H$_2$O (30 mL), then extracted with EA (3×20 mL). The organic layers were washed with brine (2×15 mL), dried over anhydrous Na$_2$SO$_4$, filtered and concentrated in vacuo to give the title compound (490 mg, 99% yield) as yellow oil. $^1$H NMR (400 MHz, CDCl$_3$) δ 4.25-4.03 (m, 2H), 2.78-2.65 (m, 2H), 2.22-2.13 (m, 2H), 2.00 (t, J=2.8 Hz, 1H), 1.85-1.72 (m, 2H), 1.72-1.60 (m, 1H), 1.48 (s, 9H), 1.30-1.15 (m, 2H).

3-[3-Methyl-2-oxo-4-[3-(4-piperidyl)propyl]benzimidazol-1-yl]piperidine-2,6-dione (Intermediate AKP)

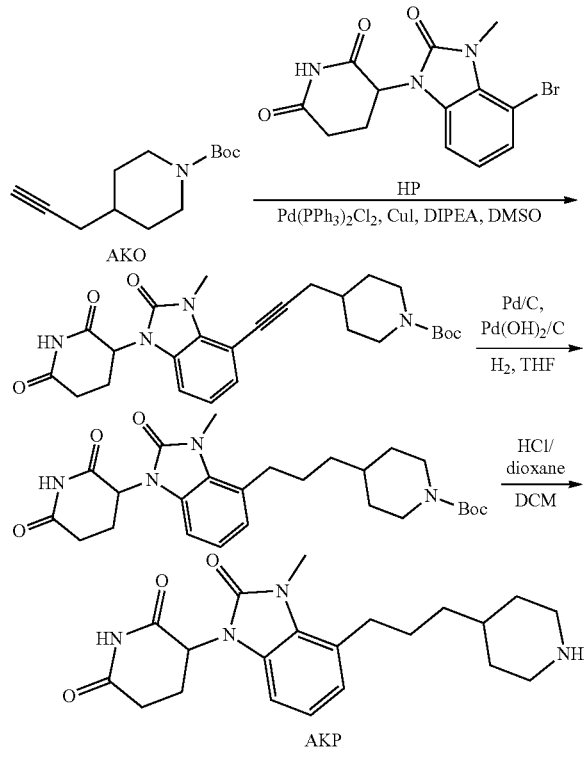

Step 1—Tert-butyl 4-[3-[1-(2,6-dioxo-3-piperidyl)-3-methyl-2-oxo-benzimidazol-4-yl]prop-2-ynyl]piperidine-1-carboxylate To a solution of tert-butyl 4-prop-2-ynylpiperidine-1-carboxylate (390 mg, 1.75 mmol, Intermediate AKO), 3-(4-bromo-3-methyl-2-oxobenzimidazol-1-yl)piperidine-2,6-dione (393 mg, 1.16 mmol, Intermediate HP) in DMSO (4 mL) was added Pd(PPh$_3$)$_2$Cl$_2$ (163 mg, 232 umol), CuI (44.3 mg, 232 umol) and DIPEA (752 mg, 5.82 mmol) under N$_2$. The mixture was stirred at 80° C. for 3 hours. On completion, the mixture was filtered and concentrated in vacuo. The mixture was purified by reverse phase: (0.1% FA) to give the title compound (450 mg, 80% yield) as yellow solid. $^1$H NMR (400 MHz, DMSO-d$_6$) δ 11.12 (s, 1H), 7.17-6.95 (m, 3H), 5.45-5.33 (m, 1H), 4.06-3.89 (m, 2H), 3.63 (s, 3H), 2.98-2.82 (m, 1H), 2.78-2.69 (m, 2H), 2.66-2.59 (m, 1H), 2.56-2.52 (m, 1H), 2.49-2.45 (m, 2H), 2.11-1.97 (m, 1H), 1.82-1.71 (m, 3H), 1.39 (s, 9H), 1.25-1.10 (m, 2H), LC-MS (ESI$^+$) m/z 503.3 (M+Na)$^+$.

Step 2—Tert-butyl 4-[3-[1-(2,6-dioxo-3-piperidyl)-3-methyl-2-oxo-benzimidazol-4-yl]propyl]piperidine-1-carboxylate To a solution of tert-butyl 4-[3-[1-(2,6-dioxo-3-piperidyl)-3-methyl-2-oxo-benzimidazol-4-yl]prop-2-ynyl]piperidine-1-carboxylate (500 mg, 1.04 mmol) in THF (50 mL) was added Pd/C (250 mg) and Pd(OH)$_2$/C (250 mg). The mixture was stirred at 15° C. for 16 hours under H$_2$ (15 psi). On completion, the mixture was filtered and the filtrate was dried in vacuo to give the title compound (500 mg, 99% yield) as white solid. $^1$H NMR (400 MHz, CDCl$_3$) δ 8.46 (s, 1H), 7.00 (s, 1H), 6.93-6.88 (m, 1H), 6.72-6.65 (m, 1H), 5.27-5.19 (m, 1H), 4.77 (s, 2H), 4.18-3.98 (m, 2H), 3.67 (s, 3H), 2.95-2.89 (m, 2H), 2.86-2.79 (m, 1H), 2.78-2.73 (m, 1H), 2.72-2.62 (m, 2H), 2.25-2.16 (m, 1H), 1.78-1.74 (m, 2H), 1.69-1.66 (m, 2H), 1.47 (s, 9H), 1.41-1.37 (m, 2H), 1.17-1.04 (m, 2H).

Step 3—3-[3-Methyl-2-oxo-4-[3-(4-piperidyl)propyl]benzimidazol-1-yl]piperidine-2,6-dione To a solution of tert-butyl 4-[3-[1-(2,6-dioxo-3-piperidyl)-3-methyl-2-oxo-benzimidazol-4-yl]propyl] piperidine-1-carboxylate (100 mg, 206 umol) in DCM (3.0 mL) was added HCl/dioxane (4.0 M, 2.0 mL). The mixture was stirred at 20° C. for 0.5 hour. On completion, the mixture was concentrated in vacuo to give the title compound (85.0 mg, 97% yield) as white solid. LC-MS (ESI$^+$) m/z 385.3 (M+H)$^+$.

Tert-butyl 4-prop-2-ynyl-1-oxa-4,9-diazaspiro[5.5]undecane-9-carboxylate (Intermediate AKR)

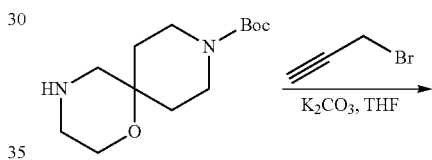

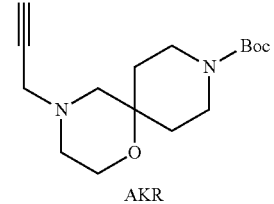

To a solution of tert-butyl 1-oxa-4,9-diazaspiro[5.5]undecane-9-carboxylate (400 mg, 1.56 mmol, CAS #930785-40-3), K$_2$CO$_3$ (646 mg, 4.68 mmo) in THF (40 mL) was added 3-bromoprop-1-yne (243 mg, 1.64 mmol). The reaction mixture was stirred at 20° C. for 24 hrs. On completion, the reaction mixture was concentrated in vacuo. The residue was diluted with H$_2$O (30 mL), and extracted with EA (3×20 mL). The organic layers were washed with brine (2×15 mL), dried over anhydrous Na$_2$SO$_4$, filtered and concentrated in vacuo to give the title compound (450 mg, 97% yield) as yellow oil. $^1$H NMR (400 MHz, CDCl$_3$) δ 3.82-3.65 (m, 4H), 3.27 (d, J=2.4 Hz, 2H), 3.22-3.10 (m, 2H), 2.55-2.50 (m, 2H), 2.37 (s, 2H), 2.29-2.26 (m, 1H), 1.99-1.90 (m, 2H), 1.53-1.45 (m, 11H).

3-[3-Methyl-4-[3-(1-oxa-4,9-diazaspiro[5.5]undecan-4-yl)propyl]-2-oxo-benzimidazol-1-yl] piperidine-2,6-dione (Intermediate AKS)

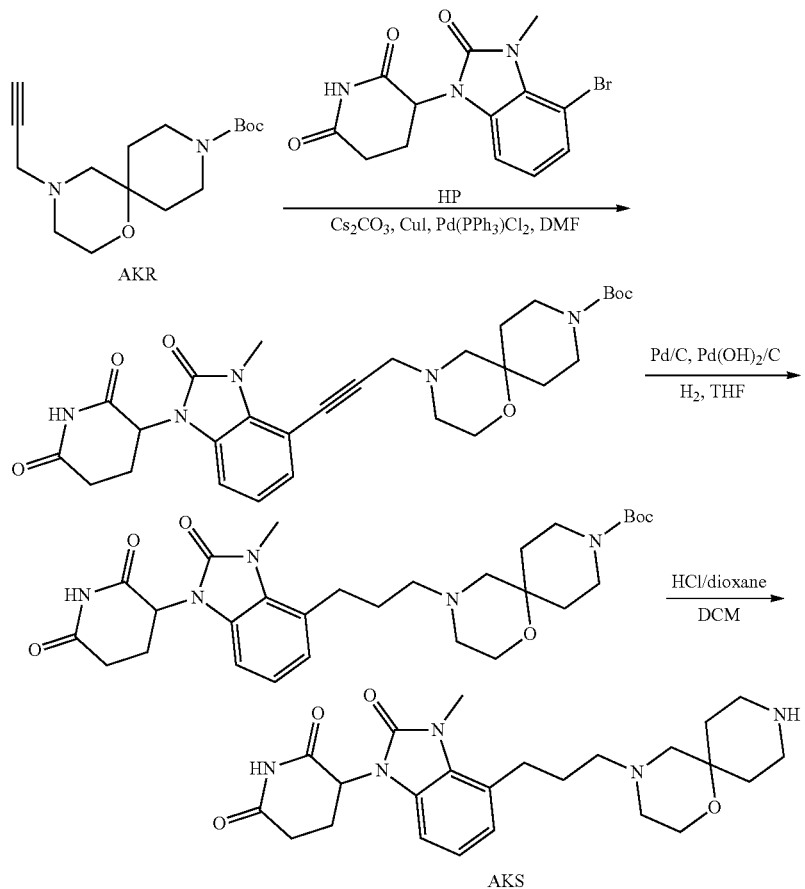

Step 1—Tert-butyl 4-[3-[1-(2,6-dioxo-3-piperidyl)-3-methyl-2-oxo-benzimidazol-4-yl]prop-2-ynyl]-1-oxa-4,9-diazaspiro[5.5]undecane-9-carboxylate To a solution of tert-butyl 4-prop-2-ynyl-1-oxa-4,9-diazaspiro[5.5]undecane-9-carboxylate (450 mg, 1.53 mmol, Intermediate AKR), 3-(4-bromo-3-methyl-2-oxo-benzimidazol-1-yl)piperidine-2,6-dione (344 mg, 1.02 mmol, Intermediate HP) in DMF (5 mL) was added Pd(PPh$_3$)$_2$Cl$_2$ (143 mg, 203 umol), CuI (38.8 mg, 203 umol) and Cs$_2$CO$_3$ (1.33 g, 4.08 mmol). The reaction mixture was stirred at 80° C. for 3 hrs. On completion, the reaction mixture was filtered and concentrated in vacuo. The residue was purified by reverse phase: (0.1% FA) to give the title compound (400 mg, 71% yield) as yellow solid. $^1$H NMR (400 MHz, DMSO-d$_6$) δ 11.12 (s, 1H), 7.20-7.09 (m, 2H), 7.06-6.99 (m, 1H), 5.47-5.32 (m, 1H), 3.70-3.62 (m, 5H), 3.61-3.54 (m, 4H), 3.11-2.99 (m, 2H), 2.94-2.83 (m, 1H), 2.78-2.68 (m, 1H), 2.66-2.57 (m, 1H), 2.43-2.35 (m, 2H), 2.08-1.98 (m, 1H), 1.89-1.75 (m, 2H), 1.46-1.28 (m, 13H), LC-MS (ESI$^+$) m/z 552.4 (M+H)$^+$.

Step 2—Tert-butyl 4-[3-[1-(2,6-dioxo-3-piperidyl)-3-methyl-2-oxo-benzimidazol-4-yl]propyl]-1-oxa-4,9-diazaspiro[5.5]undecane-9-carboxylate To a solution of tert-butyl 4-[3-[1-(2,6-dioxo-3-piperidyl)-3-methyl-2-oxo-benzimidazol-4-yl] prop-2-ynyl]-1-oxa-4,9-diazaspiro[5.5]undecane-9-carboxylate (100 mg, 181 umol) in THF (10.0 mL) was added Pd/C (50 mg) and Pd(OH)$_2$/C (50 mg). The reaction mixture was stirred at 25° C. for 3 hrs under H$_2$ (15 psi). On completion, the mixture was filtered and the filtrate was concentrated in vacuo to give the title compound (100 mg, 99% yield) as yellow solid. $^1$H NMR (400 MHz, DMSO-d$_6$) δ 11.09 (s, 1H), 7.00-6.93 (m, 2H), 6.92-6.88 (m, 1H), 5.43-5.31 (m, 1H), 3.64-3.59 (m, 3H), 3.57 (s, 3H), 3.55-3.49 (m, 1H), 3.13-2.98 (m, 2H), 2.96-2.83 (m, 3H), 2.76-2.68 (m, 1H), 2.65-2.60 (m, 1H), 2.32-2.25 (m, 3H), 2.24-2.19 (m, 2H), 2.05-1.96 (m, 1H), 1.85-1.68 (m, 5H), 1.45-1.40 (m, 2H), 1.36 (s, 9H).

Step 3—3-[3-Methyl-4-[3-(1-oxa-4,9-diazaspiro[5.5]undecan-4-yl)propyl]-2-oxo-benzimidazol-1-yl]piperidine-2,6-dione To a solution of tert-butyl 4-[3-[1-(2,6-dioxo-3-piperidyl)-3-methyl-2-oxo-benzimidazol-4-yl]propyl]-1-oxa-4, 9-diazaspiro[5.5]undecane-9-carboxylate (100 mg, 179 umol) in DCM (3.00 mL) was added HCl/dioxane (4.00 M, 3.00 mL). The reaction mixture was stirred at 25° C. for 0.5 hr. On completion, the reaction mixture was concentrated in vacuo to give the title compound (88.0 mg, 99% yield, HCl salt) as yellow solid. LC-MS (ESI$^+$) m/z 456.2 (M+H)$^+$.

1-[4-[3-(3-Aminopropoxy)propoxymethyl]cyclohexyl]-3-(difluoromethyl)pyrazol-4-amine (Intermediate AJW)

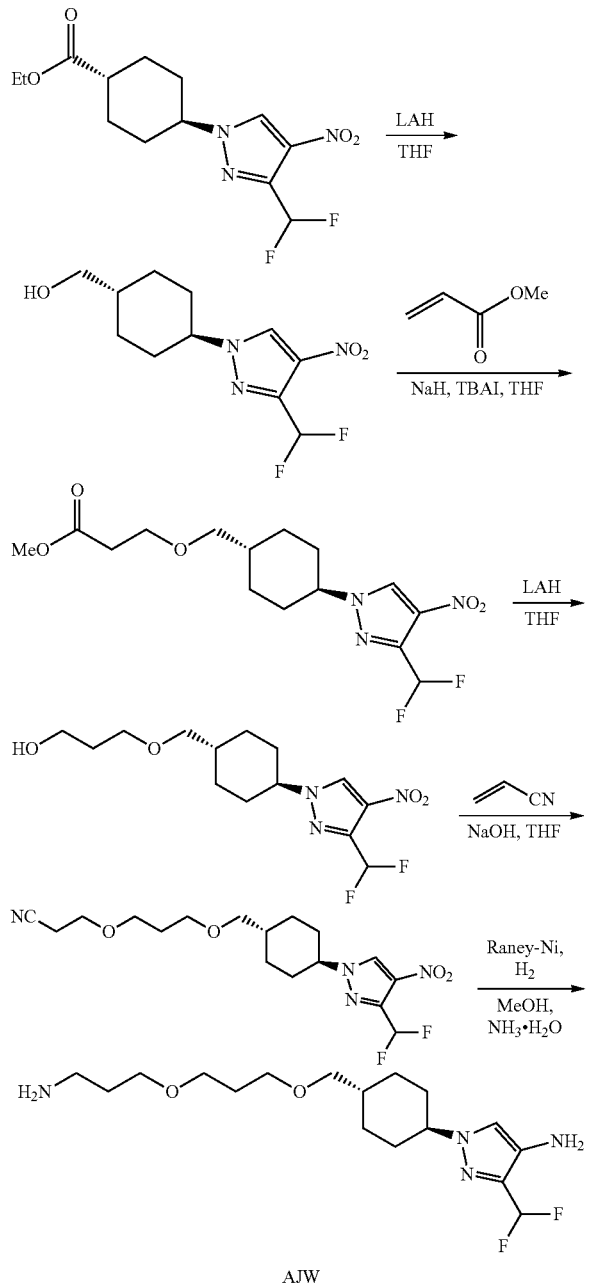

AJW

Step 1—Methyl 3-[[4-[3-(difluoromethyl)-4-nitropyrazol-1-yl] cyclohexyl]methoxy]propanoate A mixture of [4-[3-(difluoromethyl)-4-nitro-pyrazol-1-yl]cyclohexyl]methanol (1.00 g, 3.63 mmol, synthesized via Step 1 of Intermediate AAR), methyl prop-2-enoate (626 mg, 7.27 mmol) and NaH (21.0 mg, 525 umol, 60% dispersion in mineral oil) and TBAI (134 mg, 362 umol) in THF (15 mL) was stirred at 15° C. for 16 hours. On completion, the reaction was quenched with saturated aq.NH$_4$Cl (5 mL). The mixture was extracted with EA (10 mL). The combined organic layer was concentrated in vacuo. The residue was purified by reversed phase flash (FA condition) to give the title compound (350 mg, 27% yield) as light yellow oil. LC-MS (ESI$^+$) m/z 362.1 (M+H)$^+$.

Step 2—3-[4-[3-(Difluoromethyl)-4-nitro-pyrazol-1-yl] cyclohexyl]methoxy]propan-1-ol To a solution of methyl 3-[[4-[3-(difluoromethyl)-4-nitro-pyrazol-1-yl]cyclohexyl]methoxy] propanoate (350 mg, 968 umol) in THF (10 mL) was added LAH (37.0 mg, 974 umol) at −20° C. The mixture was stirred at −20° C. for 1 hour. On completion, the reaction was quenched with water (0.04 mL) slowly. Then 10% aq.NaOH (0.04 mL) and water (0.12 mL) was added. The mixture was filtered, and the filter cake was washed with THF (10 mL). The combined filtrates were concentrated in vacuo to give title compound (300 mg, 92% yield) as light yellow oil. $^1$H NMR (400 MHz, CDCl$_3$) δ 8.21 (s, 1H), 7.26-6.97 (m, 1H), 4.19-4.14 (m, 1H), 3.80-3.62 (m, 3H), 3.32-3.34 (m, 1H), 2.30-2.26 (m, 3H), 2.06-2.03 (m, 3H), 1.87-1.78 (m, 5H), 1.27-1.19 (m, 3H).

Step 3—3-[3-[[4-[3-(Difluoromethyl)-4-nitro-pyrazol-1-yl] cyclohexyl]methoxy]propoxy] propanenitrile A mixture of 3-[[4-[3-(difluoromethyl)-4-nitro-pyrazol-1-yl]cyclohexyl]methoxy]propan-1-ol (250 mg, 750 umol), prop-2-enenitrile (160 mg, 3.02 mmol) and KOH (9.00 mg, 160 umol) in THF (3 mL) was stirred at 15° C. for 32 hours. On completion, the mixture was diluted with water (10 mL), and extracted with EA (3×10 mL). The combined organic layer was washed with brine (10 mL), dried over Na$_2$SO$_4$, filtered and concentrated in vacuo. The residue was purified by column chromatography on silica gel (PE:EA=20:1-4:1) to give the title compound (250 mg, 86% yield) as light yellow oil. $^1$H NMR (400 MHz, CDCl$_3$) δ 8.21 (s, 1H), 7.26-6.98 (m, 1H), 4.23-4.12 (m, 1H), 3.66 (t, J=6.0 Hz, 2H), 3.59 (t, J=6.0 Hz, 1H), 3.52 (t, J=6.0 Hz, 1H), 3.38 (d, J=6.0 Hz, 1H), 3.30 (d, J=6.0 Hz, 1H), 2.67-2.57 (m, 3H), 2.33-2.25 (m, 2H), 2.07-2.01 (m, 2H), 1.88-1.86 (m, 1H), 1.79-1.75 (m, 4H), 1.27-1.17 (m, 3H).

Step 4—1-[4-[3-(3-Aminopropoxy)propoxymethyl] cyclohexyl]-3-(difluoromethyl)pyrazol-4-amine A mixture of 3-[3-[[4-[3-(difluoromethyl)-4-nitro-pyrazol-1-yl]cyclohexyl]methoxy]propoxy] propanenitrile (220 mg, 569 umol) and Raney-Ni (50.0 mg, 291 umol, 50%) in NH$_3$.H$_2$O (0.3 mL) and MeOH (3.0 mL) was stirred at 20° C. for 16 hours under H$_2$ (45 Psi). On completion, the mixture was filtered, and the cake was washed with MeOH (5 mL). The filtrate were concentrated in vacuo to give the title compound (200 mg, 97% yield) as light yellow gum. LC-MS (ESI$^+$) m/z 361.3 (M+H)$^+$.

4-[3-[3-[[4-[4-Amino-3-(difluoromethyl)pyrazol-1-yl] cyclohexyl]methoxy]propoxy] propylamino]-2-(2,6-dioxo-3-piperidyl)isoindoline-1,3-dione (Intermediate AJX)

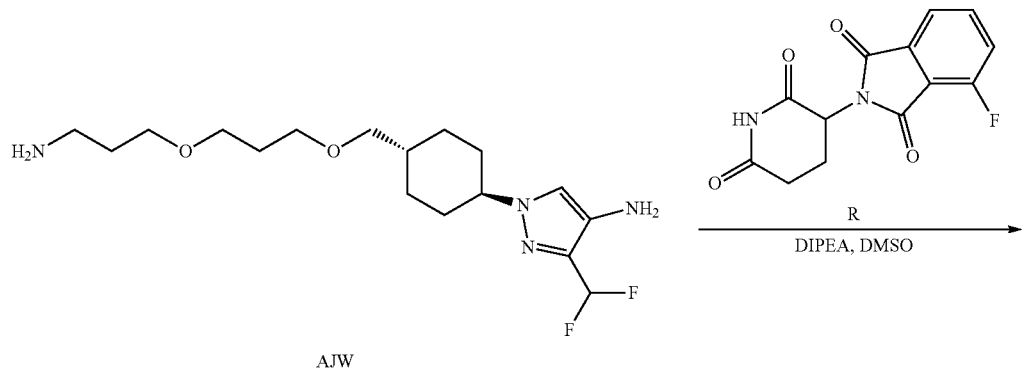

AJW

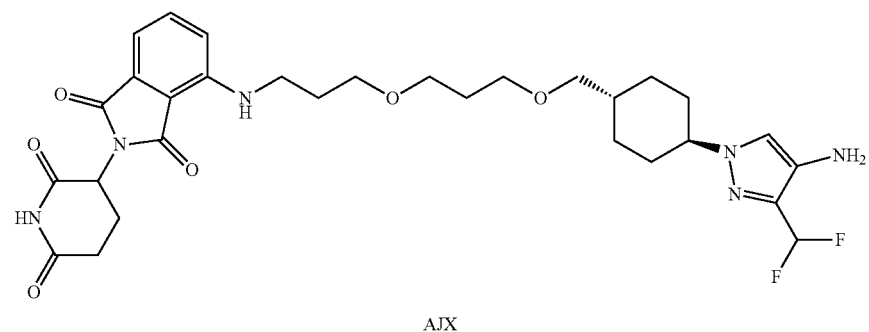

AJX

A mixture of 1-[4-[3-(3-aminopropoxy)propoxymethyl] cyclohexyl]-3-(difluoromethyl)pyrazol-4-amine (180 mg, 499 umol, Intermediate AJW), 2-(2,6-dioxo-3-piperidyl)-4-fluoro-isoindoline-1,3-dione (142 mg, 514 umol, Intermediate R) and DIPEA (253 mg, 1.96 mmol) in DMSO (3 mL) was stirred at 130° C. for 2 hours. On completion, the reaction mixture was cooled to 15° C. and quenched with water (0.2 mL). The mixture was concentrated in vacuo. The residue was purified by Prep-HPLC (column: Phenomenex Synergi Max-RP 250*50 mm*10 um; mobile phase: [water (0.1% TFA)-ACN]; B %: 32%-52%, 10 min) to give the title compound (75 mg, 24% yield) as yellow solid. $^1$H NMR (400 MHz, DMSO-$d_6$) δ 11.09 (s, 1H), 7.67-7.55 (m, 2H), 7.14-6.86 (m, 3H), 6.68-6.63 (m, 1H), 5.07-5.02 (m, 1H), 4.15-4.06 (m, 1H), 3.48-3.42 (m, 9H), 3.18 (d, J=6.4 Hz, 2H), 2.95-2.83 (m, 1H), 2.62-2.54 (m, 2H), 2.06-1.93 (m, 3H), 1.86-1.51 (m, 10H), 1.15-1.01 (m, 2H).

2187

N-[3-(difluoromethyl)-1-(4-formylcyclohexyl)pyrazol-4-yl]-5-(2-oxa-6-azaspiro[3.3]heptan-6-yl)pyrazolo[1,5-a]pyrimidine-3-carboxamide (Intermediate AJT)

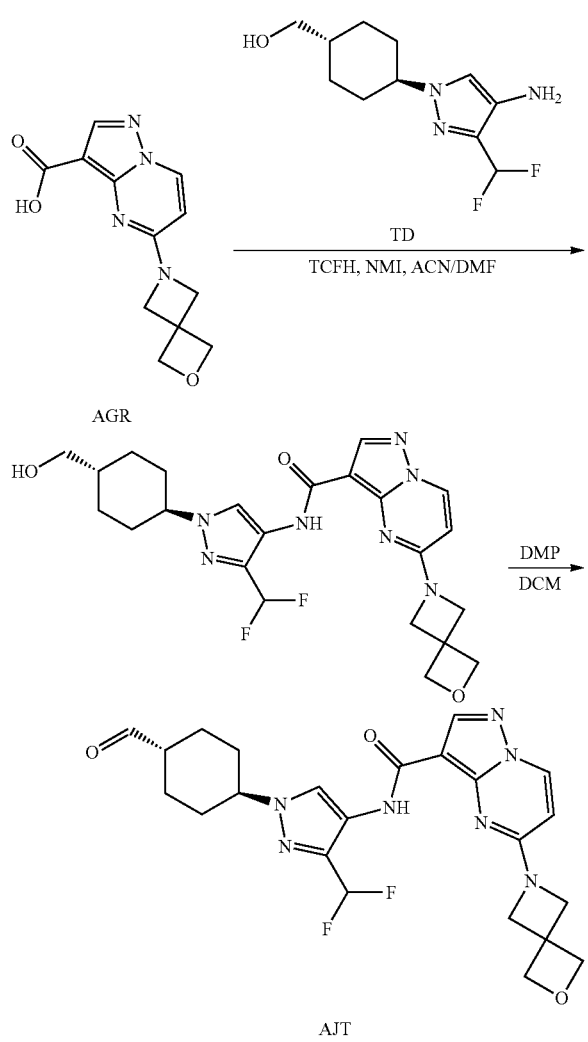

Step 1—N-[3-(difluoromethyl)-1-[4-(hydroxymethyl)cyclohexyl]pyrazol-4-yl]-5-(2-oxa-6-azaspiro[3.3]heptan-6-yl)pyrazolo[1,5-a]pyrimidine-3-carboxamide After a solution of 5-(2-oxa-6-azaspiro[3.3]heptan-6-yl)pyrazolo[1,5-a]pyrimidine-3-carboxylic acid (150 mg, 576 umol, Intermediate AGR), [chloro(dimethylamino)methylene]-dimethyl-ammonium; hexafluorophosphate (194 mg, 691 umol) and 1-methylimidazole (165 mg, 2.02 mmol) in a mixed solvents of ACN (5 mL) and DMF (0.5 mL) was stirred at 20° C. for 0.5 hr. Then [4-[4-amino-3-(difluoromethyl)pyrazol-1-yl]cyclohexyl]methanol (141 mg, 576 umol, Intermediate TD) was added. The reaction mixture was stirred at 20° C. for 18 hrs. On completion, the reaction mixture was quenched by water (0.2 mL) and concentrated in vacuo. The residue was purified by reverse phase (0.1% FA) to give the title compound (56.0 mg, 19% yield) as white solid. $^1$H NMR (400 MHz, DMSO-d$_6$) δ 9.69 (s, 1H),

2188

8.75 (d, J=7.6 Hz, 1H), 8.37 (s, 1H), 8.25 (s, 1H), 7.33-6.98 (m, 1H), 6.37 (d, J=7.6 Hz, 1H), 4.74 (s, 4H), 4.48 (t, J=5.2 Hz, 1H), 4.38 (s, 4H), 4.23-4.12 (m, 2H), 3.26 (t, J=5.6 Hz, 2H), 2.08-2.00 (m, 2H), 1.90-1.82 (m, 2H), 1.80-1.66 (m, 2H), 1.52-1.34 (m, 1H), 1.17-1.00 (m, 2H).

Step 2—N-[3-(difluoromethyl)-1-(4-formylcyclohexyl)pyrazol-4-yl]-5-(2-oxa-6-azaspiro[3.3]heptan-6-yl)pyrazolo[1,5-a]pyrimidine-3-carboxamide To a solution of N-[3-(difluoromethyl)-1-[4-(hydroxymethyl)cyclohexyl]pyrazol-4-yl]-5-(2-oxa-6-azaspiro[3.3]heptan-6-yl)pyrazolo[1,5-a]pyrimidine-3-carboxamide (43.0 mg, 88.2 umol) in a mixed solvents of DCM (1.5 mL) and DMF (0.3 mL) was added DMP (44.8 mg, 105 umol). The reaction mixture was stirred at 20° C. for 5 hrs. On completion, the reaction mixture was quenched by saturated NaS$_2$SO$_3$ (0.4 mL), diluted with water (10 mL) and extracted with DCM (3×30 mL). The combined organic layers were washed with saturated NaHCO$_3$ (2×20 mL), brine (2×30 mL), dried over Na$_2$SO$_4$, filtered and concentrated in vacuo to give the title compound (36.0 mg, 63% yield) as yellow solid. LC-MS (ESI$^+$) m/z 486.3 (M+H)$^+$.

2-(2,6-Dioxo-3-piperidyl)-4-[2-(4-piperidyl)ethylamino]isoindoline-1,3-dione (Intermediate AVB)

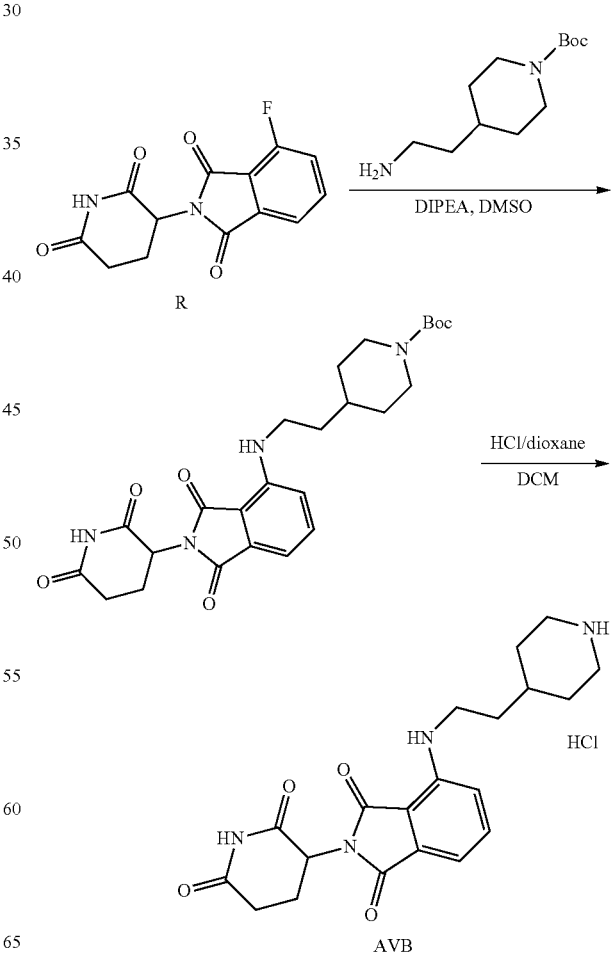

2189

Step 1—Tert-butyl 4-[2-[[2-(2,6-dioxo-3-piperidyl)-1,3-dioxo-isoindolin-4-yl]amino] ethyl]piperidine-1-carboxylate To a mixture of 2-(2,6-dioxo-3-piperidyl)-4-fluoro-isoindoline-1,3-dione (0.34 g, 1.23 mmol, Intermediate R) and tert-butyl 4-(2-aminoethyl)piperidine-1-carboxylate (281 mg, 1.23 mmol, CAS #146093-46-1) in DMSO (5 mL) was added DIPEA (318 mg, 2.46 mmol). The mixture was stirred at 130° C. for 2 hours. On completion, the reaction mixture was poured into the water (30 mL) and extracted with EA (2×20 mL). The combined organic phase was washed with brine (2×30 mL), dried with anhydrous Na$_2$SO$_4$, filtered and concentrated in vacuo to give the residue. The residue was purified by column chromatography (SiO$_2$, PE:EA=10:1 to 3:1) to give the title compound (450 mg, 75% yield) as a yellow solid. $^1$H NMR (400 MHz, CDCl$_3$) δ 7.51 (d, J=7.6 Hz, 1H), 7.11 (d, J=7.2 Hz, 1H), 6.88 (d, J=8.8 Hz, 1H), 6.19 (d, J=5.2 Hz, 1H), 4.10 (s, 1H), 3.35-3.28 (m, 2H), 2.96-2.79 (m, 2H), 2.78-2.65 (m, 4H), 1.83-1.65 (m, 4H), 1.65-1.52 (m, 4H), 1.46 (s, 9H), 1.18 (d, J=7.2 Hz, 2H).

Step 2—2-(2,6-Dioxo-3-piperidyl)-4-[2-(4-piperidyl)ethylamino]isoindoline-1,3-dione To a mixture of tert-butyl 4-[2-[[2-(2,6-dioxo-3-piperidyl)-1,3-dioxo-isoindolin-4-yl]amino]ethyl] piperidine-1-carboxylate (0.12 g, 247 umol) in DCM (20 mL) was added HCl/dioxane (4 M, 185 uL). The reaction mixture was stirred at 20° C. for 0.5 hour. On completion, the reaction mixture was concentrated in vacuo to give the title compound (95.0 mg, 91% yield) as a white solid. LC-MS (ESI$^+$) m/z 385.1 (M+H)$^+$.

4-[[2-(2,6-Dioxo-3-piperidyl)-1,3-dioxo-isoindolin-4-yl]amino]butanoic acid (Intermediate AJR)

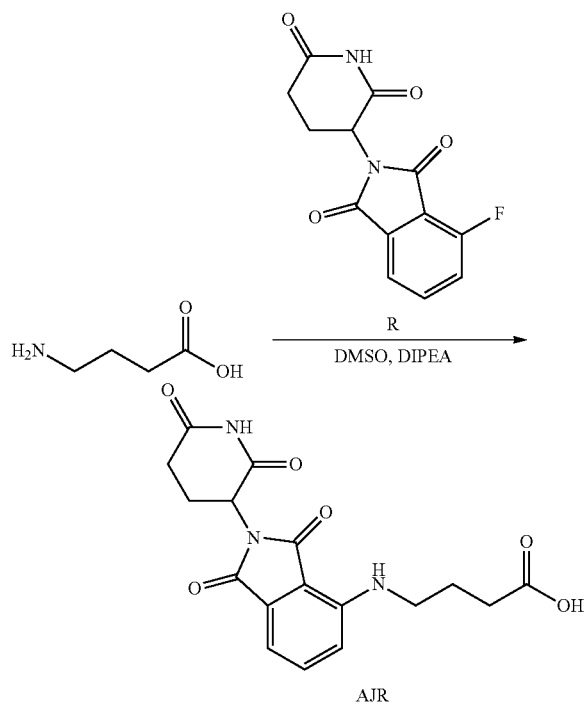

AJR

2190

A mixture was of 2-(2,6-dioxo-3-piperidyl)-4-fluoro-isoindoline-1,3-dione (200 mg, 724 umol, Intermediate R), 4-aminobutanoic acid (78.4 mg, 760 umol, CAS #20-79-1) and DIPEA (467 mg, 3.62 mmol) in DMSO (5 mL) was stirred at 130° C. for 2 hours. On completion, the reaction mixture was acidified with 4 M HCl/dioxane until the pH=7. The mixture was concentrated in vacuo. The mixture was purified by reverse phase HPLC (0.1% TFA condition) to give the title compound (160 mg, 61% yield) as green solid. LC-MS (ESI$^+$) m/z 360.2 (M+H)$^+$.

4-[[2-(2,6-Dioxo-3-piperidyl)-1,3-dioxo-isoindolin-4-yl]amino]-N-methyl-N-(4-piperidyl) butanamide (Intermediate AJS)

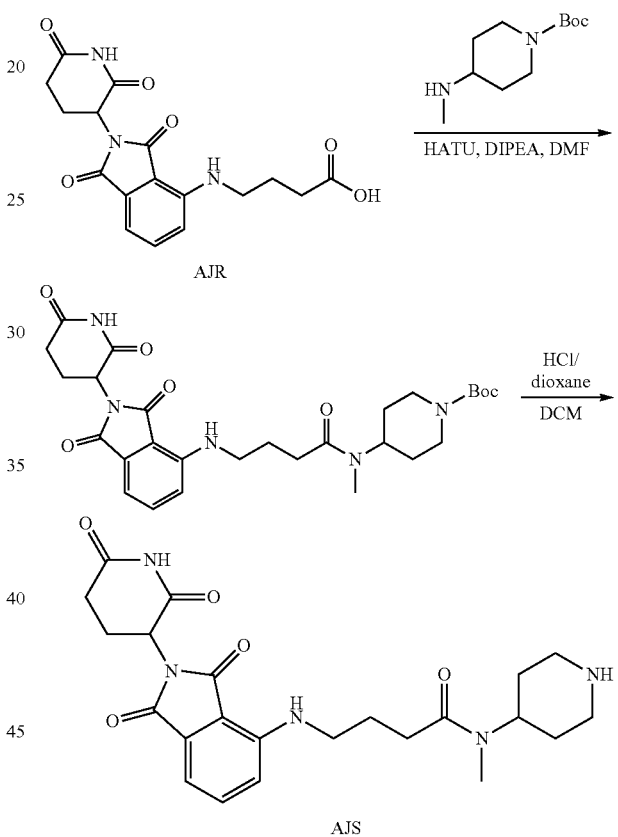

Step 1—Tert-butyl 4-[4-[[2-(2,6-dioxo-3-piperidyl)-1,3-dioxo-isoindolin-4-yl]amino]butanoyl-methyl-amino]piperidine-1-carboxylate A mixture of 4-[[2-(2,6-dioxo-3-piperidyl)-1,3-dioxo-isoindolin-4-yl]amino]butanoic acid (150 mg, 417 umol, Intermediate AJR), tert-butyl 4-(methylamino)piperidine-1-carboxylate (107 mg, 500 umol, CAS #147539-41-1), HATU (206 mg, 542 umol) and DIPEA (161 mg, 1.25 mmol) in DMF (5 mL) was stirred at 20° C. for 1 hour. On completion, the reaction mixture was quenched by water (0.5 mL). The mixture was concentrated in vacuo and the crude product was purified by reversed-phase HPLC (0.1% TFA condition). The residue was further purified by Prep-HPLC (column: Boston Green ODS 150*30 mm*5 um; mobile phase: [water (0.225% FA)-ACN]) to give the title compound (130 mg, 56% yield) as yellow solid. $^1$H NMR (400 MHz, CDCl$_3$) δ 8.45-8.34 (m, 1H), 8.29-8.17 (m, 1H), 7.51 (t, J=7.6 Hz, 1H), 7.10 (d, J=7.2 Hz, 1H), 7.04-6.95 (m, 1H), 4.97-4.87 (m, 1H), 4.72-4.58 (m, 1H), 4.20 (d, J=12.8 Hz, 2H), 3.39 (t, J=6.8 Hz, 2H), 2.94-2.84 (m, 1H), 2.83 (s, 3H), 2.81-2.66 (m, 4H), 2.57-2.38 (m, 2H), 2.17-2.09 (m, 1H), 2.08-1.97 (m, 3H), 1.63-1.52 (m, 3H), 1.47 (s, 9H).

Step 2—4-[[2-(2,6-Dioxo-3-piperidyl)-1,3-dioxo-isoindolin-4-yl]amino]-N-methyl-N-(4-piperidyl) butanamide To a mixture of tert-butyl 4-[4-[[2-(2,6-dioxo-3-piperidyl)-1,3-dioxo-isoindolin-4-yl]amino]butanoyl-methyl-amino]piperidine-1-carboxylate (65.0 mg, 116 umol) in DCM (5 mL) was added HCl/dioxane (4 M, 5 mL). The reaction mixture was stirred at 20° C. for 1 hour. On completion, the reaction mixture was concentrated in vacuo to give the title compound (55.0 mg, 95% yield, HCl) as yellow solid. LC-MS (ESI$^+$) m/z 456.3 (M+H)$^+$.

2-(Benzyloxycarbonylamino)ethyl methanesulfonate (Intermediate AIY)

To a mixture of benzyl N-(2-hydroxyethyl)carbamate (6.00 g, 30.7 mmol, CAS #77987-49-6) in DCM (50 mL) was added TEA (9.33 g, 92.2 mmol) and MsCl (4.22 g, 36.9 mmol) at 0° C. The mixture was stirred at 0° C. for 2 hours. On completion, the mixture was diluted with water (50 mL), then extracted with DCM (3×50 mL). The organic layer was washed with brine (2×15 mL), dried over Na$_2$SO$_4$, filtered and concentrated in vacuo to give the title compound (7.80 g, 92% yield) as yellow oil. LC-MS (ESI$^+$) m/z 274.1 (M+H)$^+$.

Tert-butyl N-[1-(2-aminoethyl)-4-piperidyl]-N-methyl-carbamate (Intermediate AIZ)

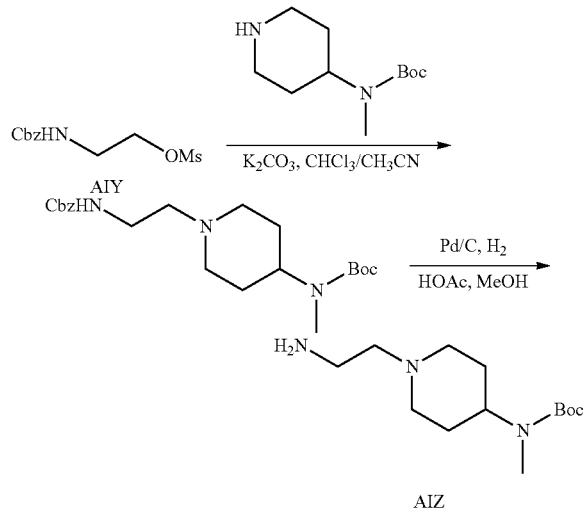

Step 1—Tert-butyl N-[1-[2-(benzyloxycarbonylamino)ethyl]-4-piperidyl]-N-methyl-carbamate To a mixture of 2-(benzyloxycarbonylamino)ethyl methanesulfonate (3.06 g, 11.2 mmol, Intermediate AIY) and tert-butyl N-methyl-N-(4-piperidyl)carbamate (2.00 g, 9.33 mmol, CAS #108612-54-0) in a mixed solvents of ACN (10 mL) and CHCl$_3$ (10 mL) was added K$_2$CO$_3$ (3.87 g, 28.0 mmol) in one portion at 25° C. The mixture was stirred at 65° C. for 16 hours. On completion, the reaction mixture was concentrated in vacuo. The residue was diluted with water (20 mL) and extracted with DCM (3×20 mL). The combined organic layers were washed with brine (10 mL), dried over Na$_2$SO$_4$, filtered and concentrated in vacuo. The residue was purified by reverse phase (FA condition) to give the title compound (1.50 g, 41% yield) as yellow oil. LC-MS (ESI$^+$) m/z 392.2 (M+H)$^+$.

Step 2—Tert-butyl N-1-(2-aminoethyl)-4-piperidyl]-N-methyl-carbamate

To a mixture of tert-butyl N-[1-[2-(benzyloxycarbonylamino)ethyl]-4-piperidyl]-N-methyl-carbamate (1.50 g, 3.83 mmol) in MeOH (20 mL) was added Pd/C (100 mg, 10 wt %) and HOAc (460 mg, 7.66 mmol) at 25° C. under N$_2$. The mixture was purged with H$_2$ three times and then stirred at 25° C. under H$_2$ (15 psi) for 20 hours. On completion, the mixture was filtered and the filtrate was concentrated in vacuo to give the title compound (700 mg, 70% yield) as yellow oil. LC-MS (ESI$^+$) m/z 258.0 (M+H)$^+$.

2-(2,6-Dioxo-3-piperidyl)-4-[2-[4-(methylamino)-1-piperidyl]ethylamino]isoindoline-1,3-dione (Intermediate AJA)

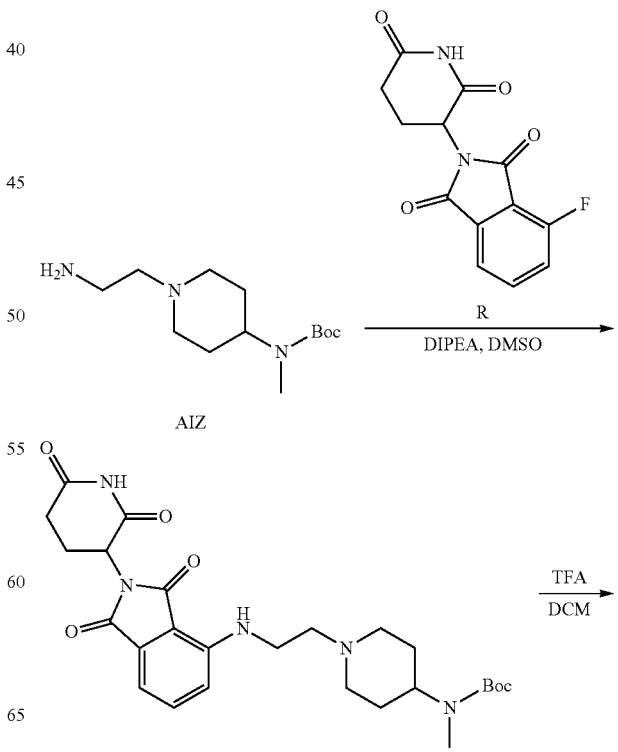

-continued

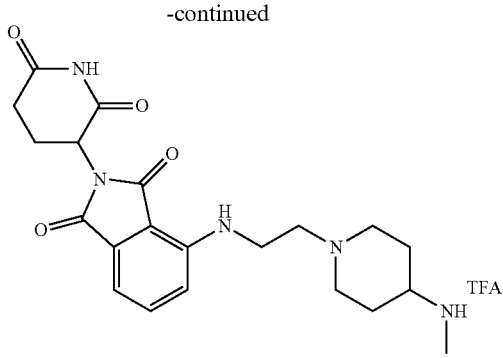

AJA

Step 1—Tert-butyl N-[1-[2-[[2-(2,6-dioxo-3-piperidyl)-1,3-dioxo-isoindolin-4-yl]amino]ethyl]-4-piperidyl]-N-methyl-carbamate To a mixture of 2-(2,6-dioxo-3-piperidyl)-4-fluoro-isoindoline-1,3-dione (200 mg, 724 umol, Intermediate R) and tert-butyl N-[1-(2-aminoethyl)-4-piperidyl]-N-methyl-carbamate (279 mg, 1.09 mmol, Intermediate AIZ) in DMSO (3 mL) was added DIPEA (187 mg, 1.45 mmol) in one portion at 25° C. The mixture was stirred at 130° C. for 2 hours. On completion, the mixture was cooled and then diluted with water (10 mL). The mixture was extracted with DCM (3×20 mL), the combined organic phase was washed with brine (10 mL), dried over Na$_2$SO$_4$, filtered and the filtrate was concentrated in vacuo. The residue was purified by reverse phase (FA condition) to give the title compound (185 mg, 49% yield) as yellow solid. LC-MS (ESI$^+$) m/z 514.4 (M+H)$^+$.

Step 2—2-(2,6-Dioxo-3-piperidyl)-4-[2-[4-(methylamino)-1-piperidyl]ethylamino]isoindoline-1,3-dione To a mixture of tert-butyl N-[1-[2-[[2-(2,6-dioxo-3-piperidyl)-1,3-dioxo-isoindolin-4-yl] amino]ethyl]-4-piperidyl]-N-methyl-carbamate (165 mg, 321 umol) in DCM (3.0 mL) was added TFA (3.0 mL) at 25° C. The mixture was stirred at 25° C. for 2 hours. On completion, the reaction mixture was concentrated in vacuo to give the title compound (110 mg, 83% yield) as yellow oil. LC-MS (ESI$^+$) m/z 414.2 (M+H)$^+$.

4-Fluoro-2-(1-methyl-2,6-dioxo-3-piperidyl)isoindoline-1,3-dione (Intermediate AJL)

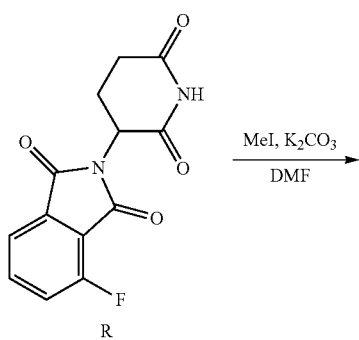

-continued

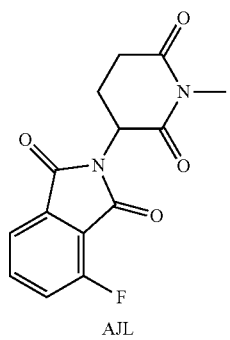

AJL

To a solution of 2-(2,6-dioxo-3-piperidyl)-4-fluoro-isoindoline-1,3-dione (500 mg, 1.81 mmol, Intermediate R) in DMF (10 mL) was added MeI (1.54 g, 10.8 mmol) and K$_2$CO$_3$ (375 mg, 2.72 mmol) at 0° C. The reaction mixture was stirred at 0-25° C. for 12 hours. On completion, the reaction mixture was concentrated in vacuo to give the title compound (500 mg, 95% yield) as a green solid. LC-MS (ESI$^+$) m/z 291.0 (M+H)$^+$.

2-(1-methyl-2,6-dioxo-3-piperidyl)-4-[3-(4-piperidyloxy)propylamino]isoindoline-1,3-dione (Intermediate AJM)

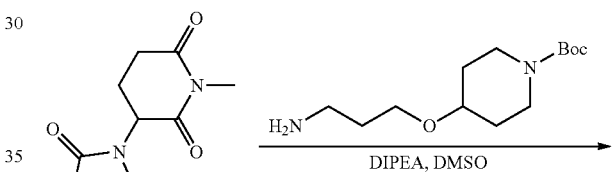

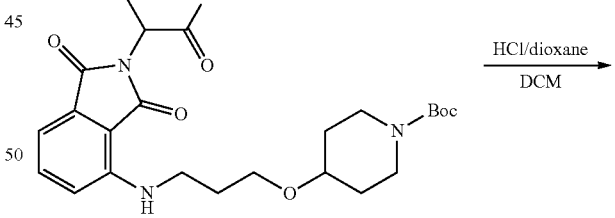

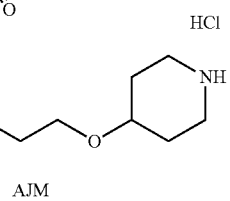

AJM

Step 1—Tert-butyl 4-[3-[[2-(1-methyl-2,6-dioxo-3-piperidyl)-1,3-dioxo-isoindolin-4-yl]amino] propoxylpiperidine-1-carboxylate To a solution of 4-fluoro-2-(1-methyl-2,6-dioxo-3-piperidyl)isoindoline-1,3-dione (250 mg, 861 umol, Intermediate AJL) and tert-butyl 4-(3-aminopropoxy)piperidine-1-carboxylate (289 mg, 1.12 mmol, CAS #771572-33-9) in DMSO (15 mL) was added DIPEA (18.7 mg, 144 umol) at 25° C. The reaction mixture was stirred at 130° C. for 2 hours. On completion, the reaction mixture was concentrated in vacuo. The residue was purified by reverse phase (0.1% FA condition) to give the title compound (350 mg, 76% yield) as a yellow solid. $^1$H NMR (400 MHz, DMSO-$d_6$) δ 7.58 (dd, J=7.2, 8.4 Hz, 1H), 7.10 (d, J=8.4 Hz, 1H), 7.02 (d, J=7.2 Hz, 1H), 6.65 (t, J=5.6 Hz, 1H), 5.11 (dd, J=5.2, 12.8 Hz, 1H), 3.60-3.56 (m, 2H), 3.51 (t, J=5.6 Hz, 2H), 3.46-3.40 (m, 1H), 3.40-3.34 (m, 2H), 3.32 (s, 2H), 3.02 (s, 3H), 2.98-2.89 (m, 1H), 2.80-2.70 (m, 1H), 2.58-2.51 (m, 1H), 2.08-1.99 (m, 1H), 1.85-1.72 (m, 4H), 1.38 (s, 9H), 1.37-1.24 (m, 2H).

Step 2—2-(1-methyl-2,6-dioxo-3-piperidyl)-4-[3-(4-piperidyloxy)propylamino]isoindoline-1,3-dione To a solution of tert-butyl 4-[3-[[2-(1-methyl-2,6-dioxo-3-piperidyl)-1,3-dioxo-isoindolin-4-yl]amino] propoxy]piperidine-1-carboxylate (100 mg, 189 umol) in DCM (5 mL) was added HCl/dioxane (4 M, 3 mL) at 25° C. The mixture was stirred at 25° C. for 2 hours. On completion, the reaction mixture was concentrated in vacuo to give the title compound (87.0 mg, 98% yield, HCl salt) as a yellow solid. LC-MS (ESI$^+$) m/z 429.2 (M+H)$^+$.

2-[[4-[3-(Difluoromethyl)-4-nitro-pyrazol-1-yl]cyclohexyl]methoxy]ethyl 4-methylbenzene sulfonate (Intermediate AJN)

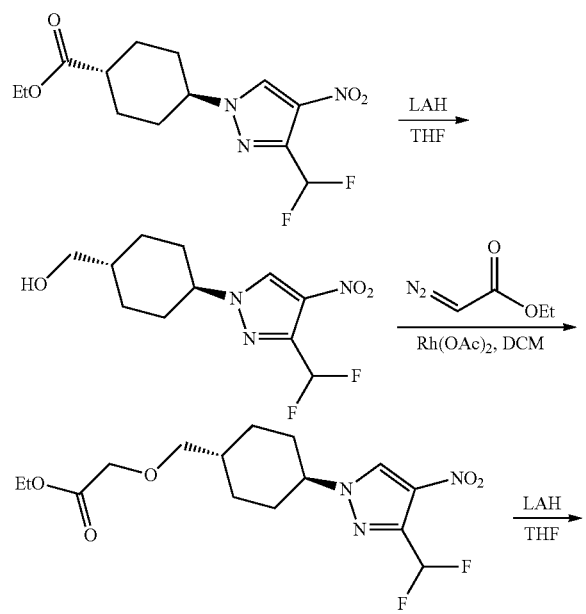

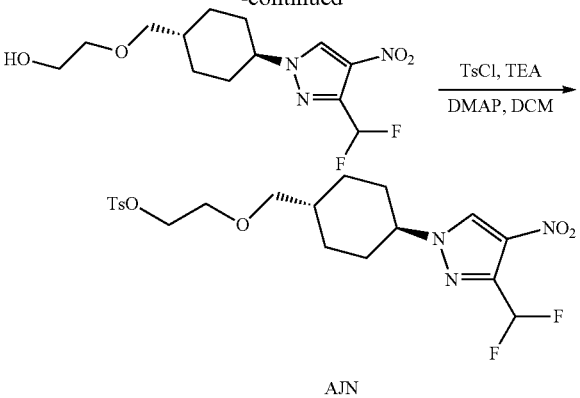

AJN

Step 1—[4-[3-(Difluoromethyl)-4-nitro-pyrazol-1-yl]cyclohexyl]methanol

To a solution of ethyl 4-[3-(difluoromethyl)-4-nitro-pyrazol-1-yl]cyclohexanecarboxylate (3.00 g, 9.46 mmol, synthesized via Steps 1-2 of Intermediate QS) in THF (30 mL) was added LiAlH$_4$ (394 mg, 10.4 mmol) at −20° C. The reaction mixture was stirred at −20° C. for 0.5 hour. On completion, the reaction mixture was quenched with water (0.4 mL), then added 15% NaOH (0.4 mL) and water (1.2 mL) were added. The solution was diluted with EA (30 mL), and dried over Na$_2$SO$_4$, filtered and the filtrate was concentrated in vacuo to give the title compound (2.60 g, 84% yield) as yellow oil. $^1$H NMR (400 MHz, CDCl$_3$) δ 8.22 (s, 1H), 7.26-6.95 (m, 1H), 4.18 (tt, J=4.0, 12.0 Hz, 1H), 3.55 (d, J=6.4 Hz, 2H), 2.38-2.23 (m, 2H), 2.12-2.00 (m, 2H), 1.90-1.67 (m, 3H), 1.63 (dt, J=3.2, 6.0 Hz, 1H), 1.30-1.15 (m, 2H).

Step 2—Ethyl 2-[[4-[3-(difluoromethyl)-4-nitro-pyrazol-1-yl] cyclohexyl]methoxy]acetate To a solution of [4-[3-(difluoromethyl)-4-nitro-pyrazol-1-yl]cyclohexyl]methanol (2.30 g, 8.36 mmol) and diacetoxyrhodium (92.3 mg, 417 umol) in DCM (20 mL) was added dropwise a solution of ethyl 2-diazoacetate (1.91 g, 16.7 mmol) in DCM (30 mL) at 15° C. for 0.25 hour. The reaction mixture was stirred at 15° C. for 16 hours. On completion, the reaction mixture was concentrated in vacuo. The residue was purified by silica gel chromatography (PE:EA=10:1) to give the title compound (1.67 g, 55% yield) as yellow oil. $^1$H NMR (400 MHz, CDCl$_3$) δ 8.22 (s, 1H), 7.26-6.97 (m, 1H), 4.28-4.12 (m, 3H), 4.08 (s, 2H), 3.42 (d, J=6.4 Hz, 2H), 2.37-2.23 (m, 2H), 2.15-2.01 (m, 2H), 1.87-1.68 (m, 3H), 1.34-1.17 (m, 5H).

Step 3—2-[4-[3-(Difluoromethyl)-4-nitro-pyrazol-1-yl] cyclohexyl]methoxy] ethanol To a solution of ethyl 2-[[4-[3-(difluoromethyl)-4-nitro-pyrazol-1-yl]cyclohexyl]methoxy]acetate (1.67 g, 4.62 mmol) in THF (20 mL) was added LiAlH$_4$ (192 mg, 5.08 mmol) at −20° C. The reaction mixture was stirred at −20° C. for 0.5 hour. On completion, the reaction mixture was quenched by water (0.2 mL) and 15% NaOH (0.2 mL). The solution was added water (0.6 mL), diluted with EA (20 mL), dried over anhydrous Na$_2$SO$_4$, filtered and the filtrate was concentrated in vacuo to give the title compound (1.43 g, 96% yield) as green oil. $^1$H NMR (400 MHz, CDCl$_3$) δ 8.22 (s, 1H), 7.26-6.98 (m, 1H), 4.25-4.14 (m, 1H), 3.84-3.70 (m, 2H), 3.60-3.52 (m, 2H), 3.43-3.32 (m, 2H), 2.39-2.22 (m, 2H), 2.08-2.05 (m, 1H), 2.04-2.01 (m, 1H), 1.96-1.89 (m, 1H), 1.85-1.68 (m, 3H), 1.24-1.15 (m, 2H).

Step 4—2-[[4-[3-(Difluoromethyl)-4-nitro-pyrazol-1-yl]cyclohexyl]methoxy]ethyl 4-methylbenzene sulfonate To a solution of 2-[[4-[3-(difluoromethyl)-4-nitro-pyrazol-1-yl]cyclohexyl]methoxy]ethanol (1.40 g, 4.38 mmol), TEA (887 mg, 8.77 mmol) and DMAP (53.5 mg, 438 umol) in DCM (20 mL) was added TsCl (1.09 g, 5.70 mmol). The reaction mixture was stirred at 20° C. for 16 hours. On completion, the reaction mixture was diluted with water (20 mL) and extracted with DCM (3×25 mL). The combined organic layers were washed with brine (3×10 mL), dried over Na$_2$SO$_4$, filtered and the filtrate was concentrated in vacuo to give a residue. The residue was purified by silica gel chromatography (PE:EA=6:1) to give the title compound (1.60 g, 77% yield) as green oil. $^1$H NMR (400 MHz, CDCl$_3$) δ 8.21 (s, 1H), 7.81 (d, J=8.4 Hz, 2H), 7.36 (d, J=8.0 Hz, 2H), 7.26-6.97 (m, 1H), 4.20-4.11 (m, 3H), 3.69-3.60 (m, 2H), 3.33-3.26 (m, 2H), 2.47 (s, 3H), 2.32-2.20 (m, 2H), 2.03-1.90 (m, 2H), 1.82-1.69 (m, 2H), 1.68-1.60 (m, 1H), 1.28-1.10 (m, 2H).

A mixture of 1-[2-[[4-[3-(difluoromethyl)-4-nitro-pyrazol-1-yl]cyclohexyl]methoxy] ethyl]-5-(4,4,5,5-tetramethyl-1,3,2-dioxaborolan-2-yl) indazole and [1-[2-[[4-[3-(difluoromethyl)-4-nitro-pyrazol-1-yl] cyclohexyl] methoxy] ethyl]indazol-5-yl]boronic acid (Intermediate AJO) and a mixture of 2-[2-[[4-[3-(difluoromethyl)-4-nitro-pyrazol-1-yl]cyclohexyl]methoxy]ethyl]-5-(4,4,5,5-tetramethyl-1,3,2-dioxaborolan-2-yl) indazole and [2-[2-[[4-[3-(difluoromethyl)-4-nitro-pyrazol-1-yl] cyclohexyl] methoxy] ethyl]indazol-5-yl]boronic acid (Intermediate AJP)

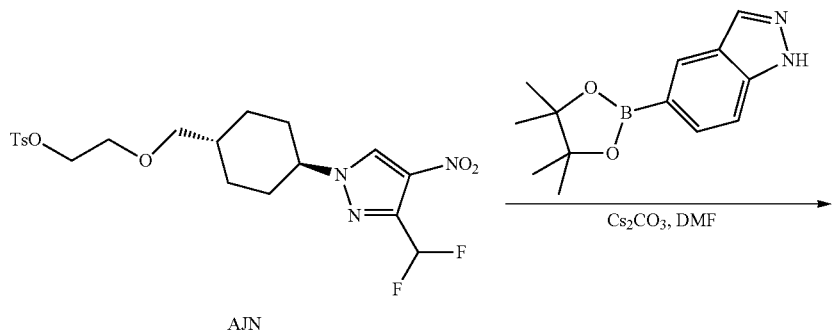

AJN

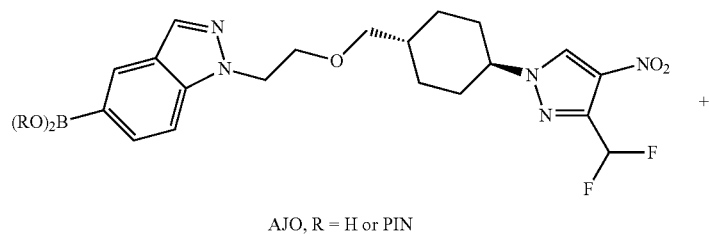

AJO, R = H or PIN

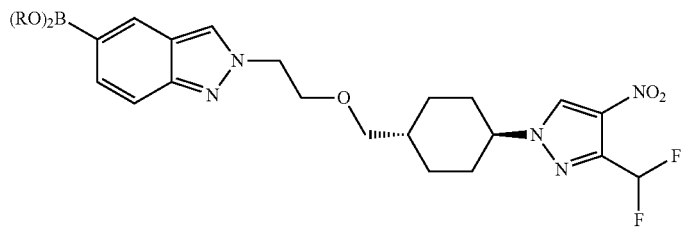

AJP, R = H or PIN

A solution of 2-[[4-[3-(difluoromethyl)-4-nitro-pyrazol-1-yl]cyclohexyl]methoxy]ethyl 4-methylbenzenesulfonate (1.51 g, 3.20 mmol, Intermediate AJN), 5-(4,4,5,5-tetramethyl-1,3,2-dioxaborolan-2-yl)-1H-indazole (650 mg, 2.66 mmol, CAS #862723-42-0) and Cs$_2$CO$_3$ (1.74 g, 5.33 mmol) in DMF (15 mL) was stirred at 80° C. for 2 hours. On completion, the reaction mixture was filtered and the filtrate was concentrated in vacuo to give a residue. The residue was purified by reverse phase (0.1% TFA) to give the title compounds Intermediate AJO (660 mg) and Intermediate AJP (300 mg). LC-MS (ESI$^+$) m/z 464.3, 546.4 (M+H)$^+$.

3-[4-[2-[2-[[4-[4-Amino-3-(difluoromethyl)pyrazol-1-yl] cyclohexyl]methoxy]ethyl]indazol-5-yl]-3-methyl-2-oxo-benzimidazol-1-yl]piperidine-2,6-dione (Intermediate AJQ)

indazol-5-yl]boronic acid (260 mg, 476 umol, Intermediate AJP), 3-(4-bromo-3-methyl-2-oxo-benzimidazol-1-yl)piperidine-2,6-dione (128 mg, 381 umol, Intermediate HP), Pd(dppf)Cl$_2$ (34.8 mg, 47.6 umol) and NaHCO$_3$ (120 mg, 1.43 mmol) in a mixed solvents of dioxane (8 mL) and water (0.8 mL) was stirred at 90° C. for 2 hrs. On completion, the reaction mixture was filtered and the filtrate was concentrated in vacuo. The residue was purified by reverse phase (0.1% TFA) to give the title compound (150 mg, 45% yield) as yellow solid. $^1$H NMR (400 MHz, DMSO-d$_6$) δ 11.13 (s, 1H), 9.03 (s, 1H), 8.42 (s, 1H), 7.75 (s, 1H), 7.67 (d, J=8.8 Hz, 1H), 7.44-6.89 (m, 5H), 5.44 (dd, J=5.2, 12.4 Hz, 1H), 4.67-4.57 (m, 2H), 4.32-4.16 (m, 1H), 3.97-3.85 (m, 2H), 3.27 (d, J=6.0 Hz, 2H), 2.98-2.89 (m, 1H), 2.86 (s, 3H), 2.82-2.71 (m, 1H), 2.69-2.61 (m, 1H), 2.12-1.94 (m, 3H), 1.80-1.63 (m, 4H), 1.62-1.46 (m, 1H), 1.14-0.93 (m, 2H).

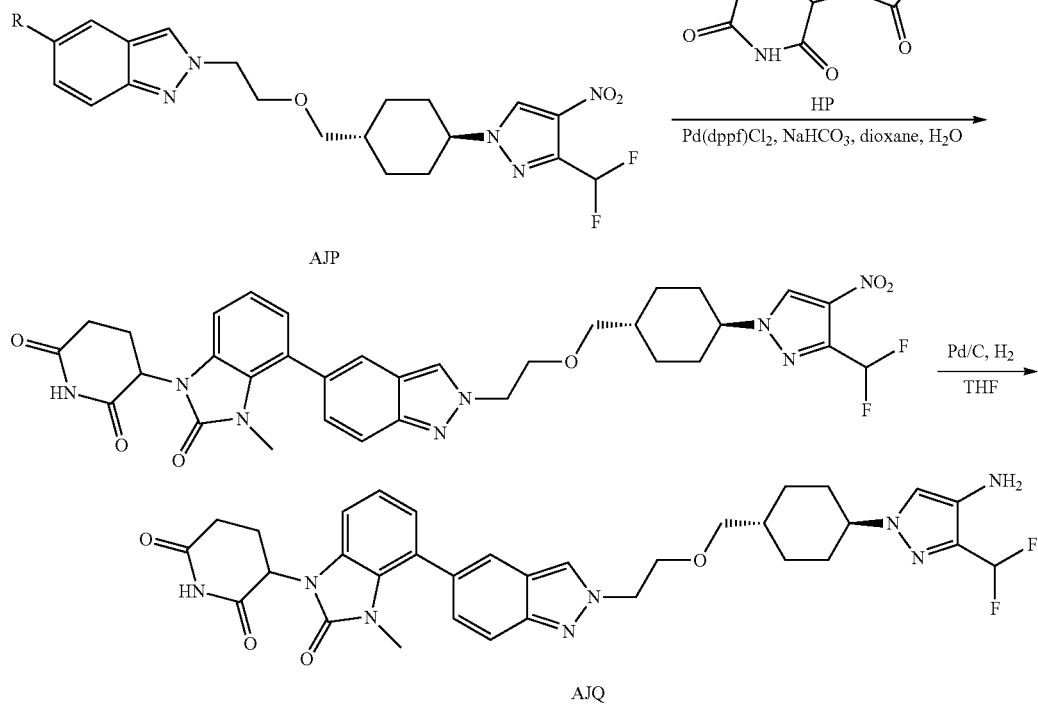

R = B(OH)$_2$ or BPin

Step 1—3-[4-[2-[2-[[4-[3-(Difluoromethyl)-4-nitro-pyrazol-1-yl]cyclohexyl]methoxy]ethyl]indazol-5-yl]-3-methyl-2-oxo-benzimidazol-1-yl]piperidine-2,6-dione A mixture of 2-[2-[[4-[3-(difluoromethyl)-4-nitro-pyrazol-1-yl]cyclohexyl]methoxy]ethyl]-5-(4,4,5,5-tetramethyl-1,3,2-dioxaborolan-2-yl) indazole and [2-[2-[[4-[3-(difluoromethyl)-4-nitro-pyrazol-1-yl] cyclohexyl]methoxy]ethyl]

Step 2—3-[4-[2-[2-[[4-[4-Amino-3-(difluoromethyl) pyrazol-1-yl]cyclohexyl]methoxy]ethyl]indazol-5-yl]-3-methyl-2-oxo-benzimidazol-1-yl]piperidine-2,6-dione To a solution of 3-[4-[2-[2-[[4-[3-(difluoromethyl)-4-nitro-pyrazol-1-yl]cyclohexyl]methoxy]ethyl] indazol-5-yl]-3-methyl-2-oxo-benzimidazol-1-yl]piperidine-2,6-dione (130 mg, 192 umol) in THF (5 mL) was added Pd/C (50.0 mg, 10 wt %). The reaction mixture was stirred at 20° C. for 1 hr under hydrogen (15 psi). On completion, the reaction mixture was filtered and the filtrate was concentrated in vacuo to give the title compound (124 mg, 99% yield) as yellow solid. LC-MS (ESI$^+$) m/z 647.2 (M+H)$^+$.

3-[4-[1-[2-[[4-[4-Amino-3-(difluoromethyl)pyrazol-1-yl] cyclohexyl]methoxy]ethyl]indazol-5-yl]-3-methyl-2-oxo-benzimidazol-1-yl]piperidine-2,6-dione (Intermediate AJY)

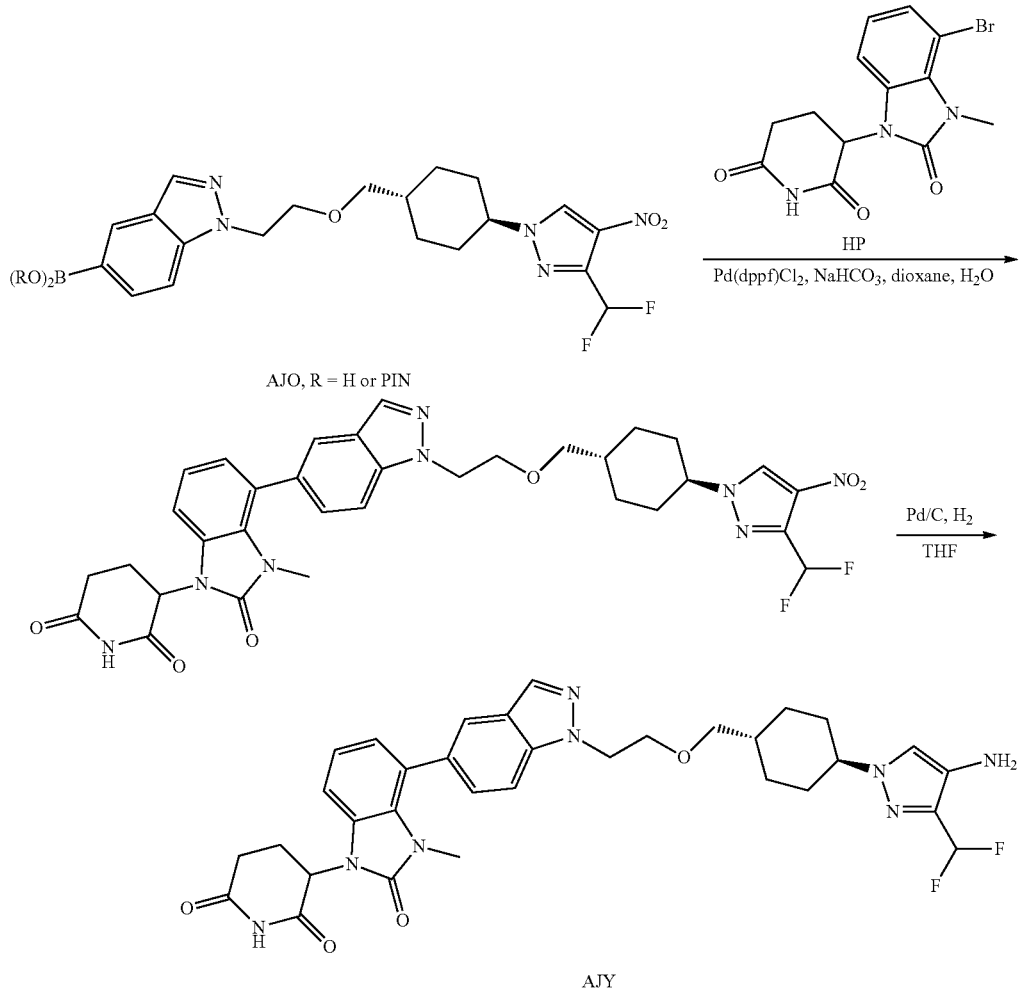

Step 1—3-[4-[1-[2-[[4-[3-(difluoromethyl)-4-nitro-pyrazol-1-yl]cyclohexyl]methoxy]ethyl]indazol-5-yl]-3-methyl-2-oxo-benzimidazol-1-yl]piperidine-2,6-dione To a mixture of 1-[2-[[4-[3-(difluoromethyl)-4-nitro-pyrazol-1-yl]cyclohexyl]methoxy]ethyl]-5-(4,4,5,5-tetramethyl-1,3,2-dioxaborolan-2-yl) indazole and [1-[2-[[4-[3-(difluoromethyl)-4-nitro-pyrazol-1-yl]cyclohexyl]methoxy] ethyl]indazol-5-yl]boronic acid (300 mg, 550 umol, Intermediate AJO), 3-(4-bromo-3-methyl-2-oxo-benzimidazol-1-yl)piperidine-2,6-dione (148 mg, 440 umol, Intermediate HP) in a mixed solvents of dioxane (8 mL) and water (0.8 mL) was added Pd(dppf)Cl$_2$ (40.2 mg, 55.0 umol) and NaHCO$_3$ (138 mg, 1.65 mmol). The mixture was stirred at 90° C. for 2 hours. On completion, the reaction mixture was filtered and the filtrate was concentrated in vacuo to give a residue. The residue was purified by reverse phase (0.1% TFA) to give the title compound (120 mg, 32% yield) as yellow solid. The compound was confirmed by NOE and HSQC spectrums. $^1$H NMR (400 MHz, DMSO-d$_6$) δ 11.13 (s, 1H), 9.01 (s, 1H), 8.13 (s, 1H), 7.87-7.70 (m, 2H), 7.53-6.83 (m, 5H), 5.44 (dd, J=5.2, 12.4 Hz, 1H), 4.62 (t, J=4.8 Hz, 2H), 4.27-4.09 (m, 1H), 3.83 (t, J=4.8 Hz, 2H), 3.20 (d, J=6.0 Hz, 2H), 2.98-2.87 (m, 1H), 2.83 (s, 3H), 2.78-2.61 (m, 2H), 2.13-1.91 (m, 3H), 1.74-1.58 (m, 4H), 1.54-1.37 (m, 1H), 1.08-0.86 (m, 2H).

Step 2—3-[4-[1-[2-[[4-[4-Amino-3-(difluoromethyl) pyrazol-1-yl]cyclohexyl]methoxy]ethyl]indazol-5-yl]-3-methyl-2-oxo-benzimidazol-1-yl]piperidine-2,6-dione To solution of 3-[4-[1-[2-[[4-[3-(difluoromethyl)-4-nitro-pyrazol-1-yl] cyclohexyl]methoxy] ethyl] indazol-5-yl]-3-methyl-2-oxo-benzimidazol-1-yl]piperidine-2,6-dione (150 mg, 221 umol) in THF (5 mL) was added Pd/C (50.0 mg, 221 umol, 10 wt %). The reaction mixture was stirred at 20° C. for 1 hour under H$_2$ (15 psi). On completion, the reaction mixture was filtered and the filtrate was concentrated in 2-[[4-[3-(Difluoromethyl)-4-nitro-pyrazol-1-yl]cy-clohexyl]methoxy]ethanamine (Intermediate AKD)

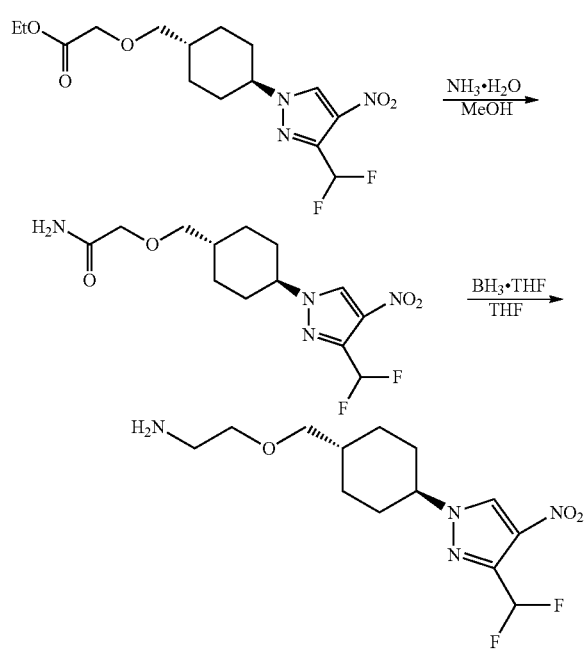

4-[2-[[4-[4-Amino-3-(difluoromethyl)pyrazol-1-yl]cyclohexyl]methoxy]ethylamino]-2-(2,6-dioxo-3-piperidyl)isoindoline-1,3-dione (Intermediate AKE)

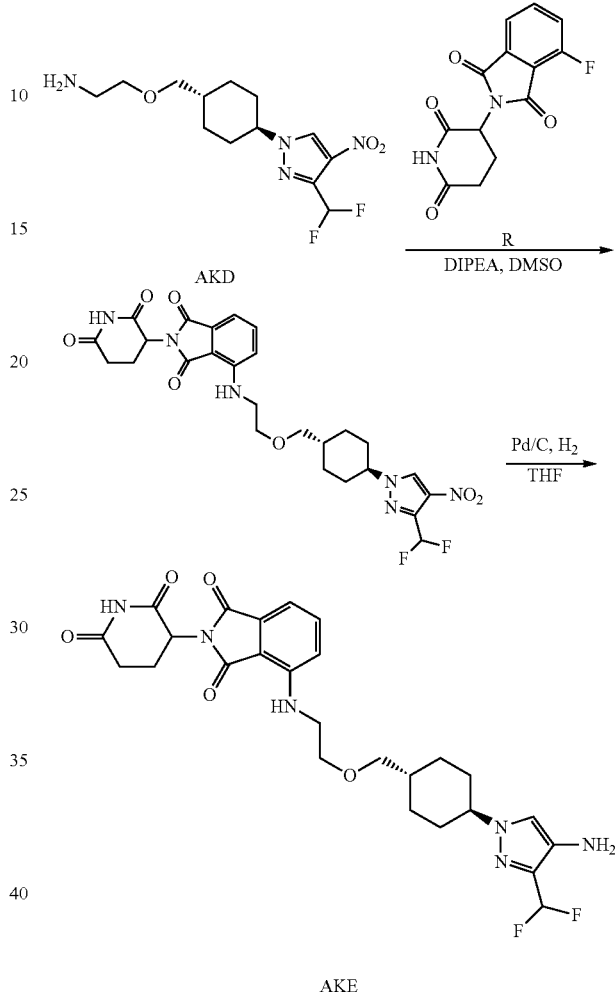

Step 1—2-[[4-[3-(Difluoromethyl)-4-nitro-pyrazol-1-yl]cyclohexyl]methoxy]acetamide A mixture of ethyl 2-[[4-[3-(difluoromethyl)-4-nitro-pyrazol-1-yl]cyclohexyl]methoxy]acetate (500 mg, 1.38 mmol, synthesized via Steps 1-2 of Intermediate AJN) and NH$_3$·H$_2$O (6 mL, 28% solution) in MeOH (6 mL) was stirred at 70° C. for 16 hours in a sealed tube (15 psi). On completion, the reaction mixture was concentrated in vacuo to give the title compound (450 mg, 97% yield) as yellow oil. $^1$H NMR (400 MHz, CDCl$_3$) δ 8.22 (s, 1H), 7.26-6.98 (m, 1H), 6.44 (s, 1H), 5.71 (s, 1H), 4.24-4.14 (m, 1H), 3.97 (s, 2H), 3.46-3.39 (m, 2H), 2.36-2.20 (m, 2H), 2.09-2.02 (m, 2H), 1.84-1.78 (m, 2H), 1.77-1.71 (m, 1H), 1.30-1.21 (m, 2H).

Step 2—2-[4-[3-(Difluoromethyl)-4-nitro-pyrazol-1-yl]cyclohexyl]methoxy]ethanamine To a solution of 2-[[4-[3-(difluoromethyl)-4-nitro-pyrazol-1-yl]cyclohexyl]methoxy]acetamide (350 mg, 1.05 mmol) in THF (8 mL) was added BH$_3$.THF (1 M, 3.16 mL) at 20° C. The mixture was stirred at 20° C. for 0.5 hour. Then, the reaction mixture was stirred at 70° C. for 12 hours. On completion, the reaction mixture was quenched with methanol (0.5 mL) and concentrated in vacuo. The residue was purified by reverse phase (0.1% TFA) to give the title compound (160 mg, 35% yield, TFA) as red oil. $^1$H NMR (400 MHz, DMSO-d$_6$) δ 9.07 (s, 1H), 7.77 (s, 3H), 7.51-7.13 (m, 1H), 4.38-4.17 (m, 1H), 3.54 (t, J=5.2 Hz, 2H), 3.29 (d, J=6.4 Hz, 2H), 3.06-2.94 (m, 2H), 2.15-2.05 (m, 2H), 1.99-1.85 (m, 2H), 1.84-1.70 (m, 2H), 1.69-1.58 (m, 1H), 1.21-1.05 (m, 2H).

Step 1—4-[2-[[4-[3-(Difluoromethyl)-4-nitro-pyrazol-1-yl]cyclohexyl]methoxy]ethylamino]-2-(2,6-dioxo-3-piperidyl)isoindoline-1,3-dione To a solution of 2-[[4-[3-(difluoromethyl)-4-nitro-pyrazol-1-yl]cyclohexyl]methoxy]ethanamine (160 mg, 370 umol, TFA salt, Intermediate AKD) and 2-(2,6-dioxo-3-piperidyl)-4-fluoro-isoindoline-1,3-dione (112 mg, 407.09 umol, Intermediate R) in DMSO (3 mL) was added DIPEA (191 mg, 1.48 mmol). The reaction mixture was stirred at 130° C. for 3 hrs. On completion, the reaction mixture was diluted with water (15 mL) and extracted with EA (3×50 mL). The combined organic layers were washed with brine (3×20 mL), dried over Na$_2$SO$_4$, filtered and concentrated in vacuo. The residue was purified by reverse phase (0.1% FA) to give the title compound (120 mg, 56% yield) as yellow solid. $^1$H NMR (400 MHz, DMSO-d$_6$) δ 11.08 (s, 1H), 9.05 (s, 1H), 7.59 (dd, J=7.2, 8.4 Hz, 1H), 7.48-7.13 (m, 2H), 7.05 (d, J=7.2 Hz, 1H), 6.62 (t, J=5.6 Hz, 1H), 5.05 (dd, J=5.2, 12.8 Hz, 1H), 4.32-4.22 (m, 1H), 3.65-3.55 (m, 2H), 3.51-3.44 (m, 2H), 3.30 (d, J=6.4 Hz, 2H), 2.96-2.79 (m, 1H), 2.62-2.52 (m, 2H), 2.13-1.98 (m, 3H), 1.92-1.83 (m, 2H), 1.81-1.70 (m, 2H), 1.67-1.55 (m, 1H), 1.21-1.05 (m, 2H).

Step 2—4-[2-[[4-[4-Amino-3-(difluoromethyl)pyrazol-1-yl]cyclohexyl]methoxy]ethylamino]-2-(2,6-dioxo-3-piperidyl)isoindoline-1,3-dione To a solution of 4-[2-[[4-[3-(difluoromethyl)-4-nitropyrazol-1-yl]cyclohexyl]methoxy]ethylamino]-2-(2,6-dioxo-3-piperidyl)isoindoline-1,3-dione (120 mg, 208 umol) in THF (5 mL) was added Pd/C (20 mg, 10 wt %). The reaction mixture was stirred at 20° C. for 1 hour under hydrogen (15 psi). On completion, the reaction mixture was filtered and the filtrate was concentrated in vacuo to give the title compound (113 mg, 99% yield) as yellow solid. LC-MS (ESI⁺) m/z 545.1.

4-(7-azaspiro[3.5]nonan-2-ylmethylamino)-2-(2,6-dioxo-3-piperidyl)isoindoline-1,3-dione (Intermediate AJF)

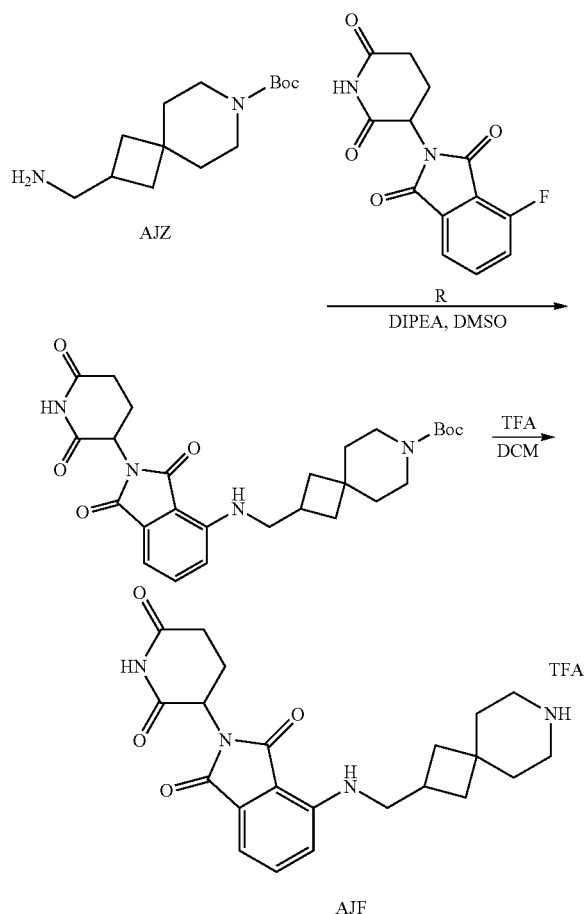

Step 1—Tert-butyl 2-[[[2-(2,6-dioxo-3-piperidyl)-1,3-dioxo-isoindolin-4-yl]amino]methyl]-7-azaspiro[3.5]nonane-7-carboxylate To a solution of tert-butyl 2-(aminomethyl)-7-azaspiro[3.5]nonane-7-carboxylate (200 mg, 786 umol, Intermediate AJZ) and 2-(2,6-dioxo-3-piperidyl)-4-fluoro-isoindoline-1,3-dione (228 mg, 825 umol, Intermediate R) in DMSO (3 mL) was added DIPEA (254 mg, 1.97 mmol). The reaction mixture was stirred at 125° C. for 3 hrs. On completion, the reaction mixture was diluted with water (50 mL), then extracted with EA (50 mL). The organic layer was concentrated in vacuo. The residue was purified by reverse phase (0.1% FA condition) to give the title compound (260 mg, 65% yield) as a yellow solid. LC-MS (ESI⁺) m/z 511.3 (M+H)⁺.

Step 2—4-(7-Azaspiro[3.5]nonan-2-ylmethylamino)-2-(2,6-dioxo-3-piperidyl)isoindoline-1,3-dione To a solution of tert-butyl 2-[[[2-(2,6-dioxo-3-piperidyl)-1,3-dioxo-isoindolin-4-yl]amino]methyl]-7-azaspiro[3.5]nonane-7-carboxylate (80.0 mg, 157 umol) in TFA (2 mL) was added DCM (2 mL). The reaction mixture was stirred at 20° C. for 2 hrs. On completion, the mixture was concentrated in vacuo to give the title compound (80 mg, 97% yield, TFA salt) as a yellow solid. LC-MS (ESI⁺) m/z 411.2 (M+H)⁺

Tert-butyl 4-(2-oxoethoxymethyl)piperidine-1-carboxylate (Intermediate AJD)

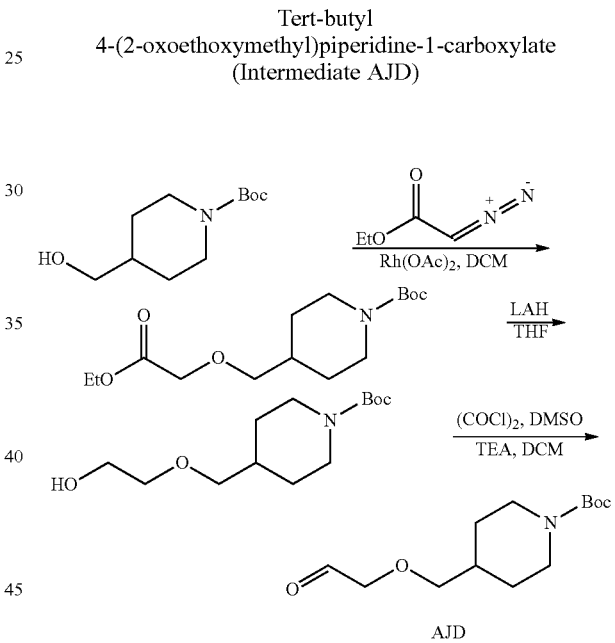

Step 1—Tert-butyl 4-[(2-ethoxy-2-oxo-ethoxy)methyl]piperidine-1-carboxylate

To a solution of tert-butyl 4-(hydroxymethyl)piperidine-1-carboxylate (5.00 g, 23.2 mmol, CAS #123855-51-6) and Rh(OAc)₂ (102 mg, 464 umol) in DCM (40 mL) was added a solution of ethyl 2-diazoacetate (3.97 g, 34.8 mmol) in DCM (20 mL) dropwise. The mixture was stirred at 15° C. for 16 hrs. On completion, the mixture was washed with H₂O (2×30 mL), the organic layer was washed with brine dried over anhydrous Na₂SO₄, filtered and concentrated in vacuo. The mixture was purified by silica gel column (PE:EA=20:1) to give the title compound (3.66 g, 52% yield) as yellow oil. ¹H NMR (400 MHz, DMSO-d₆) δ 4.24-4.17 (m, 1H), 4.15-4.11 (m, 2H), 4.07 (s, 2H), 3.99-3.86 (m, 2H), 2.78-2.64 (m, 2H), 1.78-1.67 (m, 1H), 1.67-1.58 (m, 2H), 1.39 (s, 9H), 1.28-1.23 (m, 1H), 1.21 (d, J=7.2 Hz, 3H), 1.10-0.95 (m, 2H).

Step 2—Tert-butyl 4-(2-hydroxyethoxymethyl)piperidine-1-carboxylate

To a solution of LiAlH₄ (599 mg, 15.7 mmol) in THF (20 mL) was added a solution of tert-butyl 4-[(2-ethoxy-2-oxo-ethoxy)methyl]piperidine-1-carboxylate (3.66 g, 12.1 mmol) in THF (20 mL) dropwise at 0° C., and the mixture was stirred at 0° C. for 0.5 hr. On completion, the reaction mixture was quenched with H₂O (1 mL) and a solution of 15% NaOH (1 mL). Thereafter, the mixture was dried over anhydrous Na₂SO₄, filtered and concentrated in vacuo give the title compound (2.10 g, 66% yield) as yellow oil. $^1$H NMR (400 MHz, DMSO-d$_6$) δ 4.55 (t, J=5.6 Hz, 1H), 4.00-3.82 (m, 2H), 3.52-3.46 (m, 2H), 3.41-3.36 (m, 2H), 3.27-3.22 (m, 2H), 2.78-2.58 (m, 2H), 1.80-1.68 (m, 1H), 1.68-1.58 (m, 2H), 1.40 (s, 9H), 1.09-0.93 (m, 2H).

Step 3—Tert-butyl 4-(2-oxoethoxymethyl)piperidine-1-carboxylate

To a solution of DMSO (376 mg, 4.82 mmol) in DCM (10 mL) was added a solution of (COCl)₂ (489 mg, 3.86 mmol) in DCM (5 mL) dropwise at −70° C. The mixture was stirred at this temperature for 10 minutes, then a solution of tert-butyl 4-(2-hydroxyethoxymethyl)piperidine-1-carboxylate (500 mg, 1.93 mmol) in DCM (5 mL) was added into the above mixture slowly. After stirred at −70° C. for 50 minutes, TEA (1.56 g, 15.4 mmol) was added and the reaction mixture was stirred at −70° C. for 0.5 hr. On completion, the reaction mixture was quenched by addition H₂O (20 mL), then washed with H₂O (2×20 mL). The organic layers was combined and washed with brine (2×20 mL), dried over Na₂SO₄, concentrated in vacuo to give the title compound (460 mg, 92% yield) as yellow oil.

3-[1-Oxo-4-[2-(4-piperidylmethoxy)ethylamino]isoindolin-2-yl]piperidine-2,6-dione (Intermediate AJE)

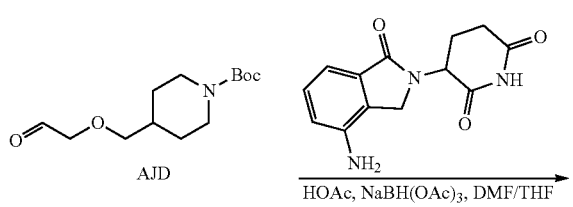

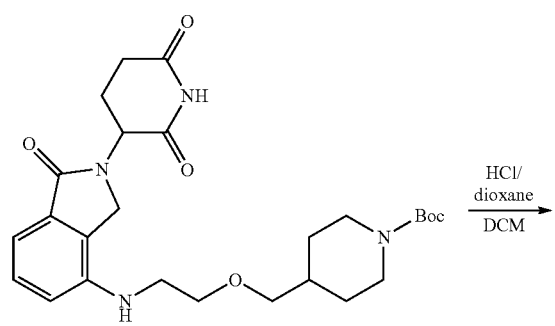

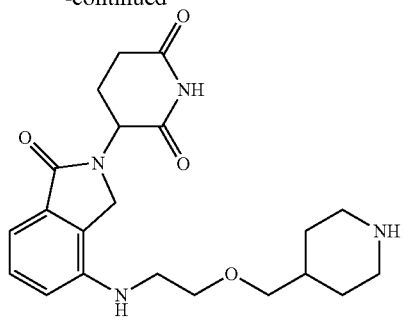

AJE

Step 1—Tert-butyl 4-[2-[[2-(2,6-dioxo-3-piperidyl)-1-oxo-isoindolin-4-yl]amino]ethoxymethyl]piperidine-1-carboxylate To a solution of tert-butyl 4-(2-oxoethoxymethyl)piperidine-1-carboxylate (297 mg, 1.16 mmol, Intermediate AJD), 3-(4-amino-1-oxoisoindolin-2-yl)piperidine-2,6-dione (100 mg, 385 umol, CAS #191732-72-6) in a mixed solvent of DMF (1.00 mL) and THF (6.00 mL) was added TEA (78.0 mg, 771 umol). The mixture was stirred at 15° C. for 0.5 hr. Then HOAc (69.4 mg, 1.16 mmol) was added, and the mixture was stirred at 15° C. for 0.5 hr. Then NaBH(OAc)₃ (163 mg, 771 umol) was added, and the mixture was stirred at 15° C. for 1 hr. On completion, the mixture was diluted with H₂O (1 mL) and concentrated in vacuo. The mixture was purified by prep-HPLC (column: Phenomenex Synergi C18 150*25*10 um; mobile phase: [water (0.225% FA)-ACN]; B %: 34%-64%, 10 min) to give the title compound (35 mg, 18% yield) as white solid. $^1$H NMR (400 MHz, DMSO-d$_6$) δ 11.01 (s, 1H), 7.32-7.24 (m, 1H), 6.95 (d, J=7.2 Hz, 1H), 6.82 (d, J=8.4 Hz, 1H), 5.58 (t, J=5.6 Hz, 1H), 5.17-5.07 (m, 1H), 4.29-4.09 (m, 2H), 4.00-3.83 (m, 2H), 3.60-3.50 (m, 2H), 3.30-3.24 (m, 3H), 2.97-2.86 (m, 1H), 2.66-2.56 (m, 2H), 2.36-2.25 (m, 2H), 2.07-2.00 (m, 1H), 1.77-1.57 (m, 4H), 1.39 (s, 9H), 1.05-0.98 (m, 2H), LC-MS (ESI⁺) m/z 501.2 (M+H)⁺.

Step 2—3-[1-Oxo-4-[2-(4-piperidylmethoxy)ethylamino]isoindolin-2-yl]piperidine-2,6-dione To a solution of tert-butyl 4-[2-[[2-(2,6-dioxo-3-piperidyl)-1-oxo-isoindolin-4-yl]amino]ethoxymethyl] piperidine-1-carboxylate (30.0 mg, 59.9 umol) in DCM (3 mL) was added HCl/dioxane (4.00 M, 3.00 mL). The mixture was stirred at 15° C. for 0.5 hr. On completion, the mixture was concentrated in vacuo to give the title compound (26.0 mg, 99% yield, HCl) as yellow solid. LC-MS (ESI⁺) m/z 401.2 (M+H)⁺.

1-[4-(3-Aminopropoxymethyl)cyclohexyl]-3-(difluoromethyl)pyrazol-4-amine (Intermediate AJJ)

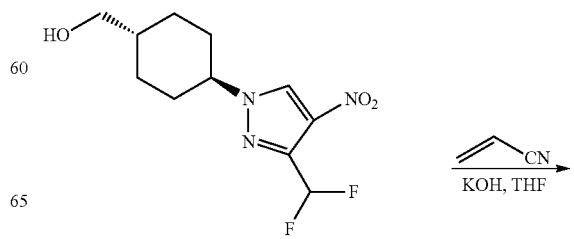

2209

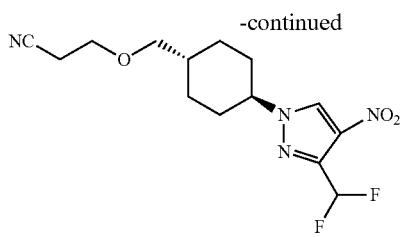

-continued

2210

4-[3-[[4-[4-Amino-3-(difluoromethyl)pyrazol-1-yl]cyclohexyl]methoxy]propylamino]-2-(2,6-dioxo-3-piperidyl)isoindoline-1,3-dione (Intermediate AJK)

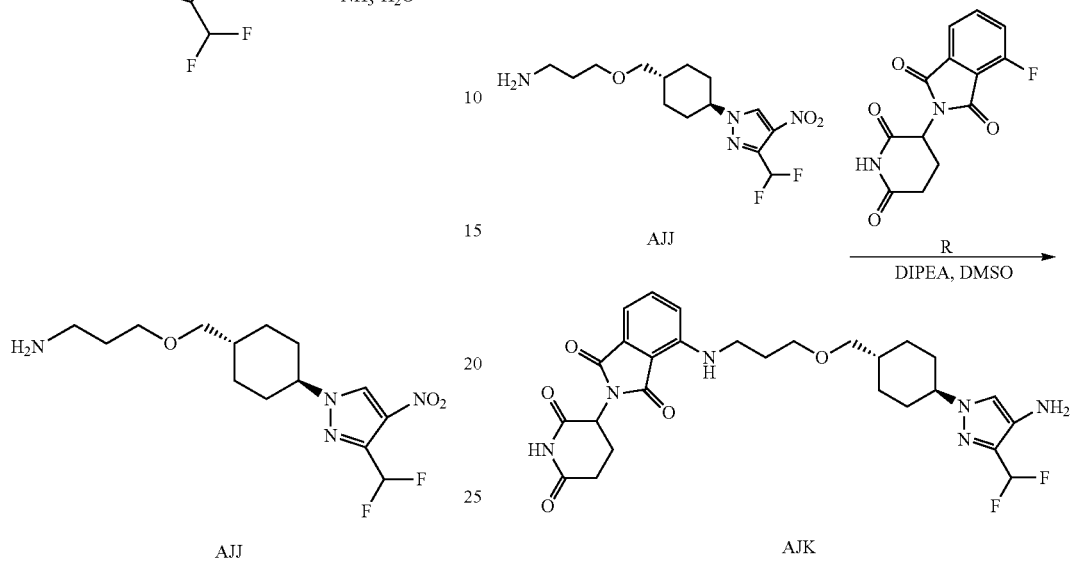

Step 1—3-[[4-[3-(Difluoromethyl)-4-nitro-pyrazol-1-yl]cyclohexyl]methoxy]propanenitrile To a solution of [4-[3-(difluoromethyl)-4-nitro-pyrazol-1-yl]cyclohexyl]methanol (1.00 g, 3.09 mmol, synthesized via Step 1 of Intermediate AAR) and prop-2-enenitrile (327 mg, 6.18 mmol) in THF (20 mL) was added KOH (17.3 mg, 308 umol). The reaction mixture was stirred at 15° C. for 16 hours. On completion, the reaction mixture was diluted with water (30 mL) and extracted with EA (3×80 mL). The combined organic layers were washed with brine (2×50 mL), dried over Na$_2$SO$_4$, filtered and concentrated in vacuo. The residue was purified by silica gel chromatography (PE:EA=7:1) to give the title compound (800 mg, 78% yield) as yellow oil. $^1$H NMR (400 MHz, CDCl$_3$) δ 8.21 (s, 1H), 7.26-6.96 (m, 1H), 4.18 (tt, J=4.0, 12.0 Hz, 1H), 3.66 (t, J=6.4 Hz, 2H), 3.38 (d, J=6.0 Hz, 2H), 2.62 (t, J=6.4 Hz, 2H), 2.35-2.24 (m, 2H), 2.10-1.99 (m, 2H), 1.85-1.68 (m, 3H), 1.33-1.17 (m, 2H).

Step 2—1-[4-(3-Aminopropoxymethyl)cyclohexyl]-3-(difluoromethyl)pyrazol-4-amine To a solution of 3-[[4-[3-(difluoromethyl)-4-nitro-pyrazol-1-yl]cyclohexyl]methoxy]propanenitrile (100 mg, 304 umol) and NH$_3$.H$_2$O (182 mg, 1.45 mmol, 28% solution) in MeOH (2 mL) was added Raney-Ni (5.22 mg, 60.9 umol). The reaction mixture was stirred at 20° C. for 16 hours under H$_2$ (50 psi). On completion, the reaction mixture was filtered. The filtrate was concentrated in vacuo to give the title compound (90.0 mg, 97% yield) as yellow oil. LC-MS (ESI$^+$) m/z 303.2 (M+H)$^+$ To a solution of 1-[4-(3-aminopropoxymethyl)cyclohexyl]-3-(difluoromethyl)pyrazol-4-amine (90.0 mg, 297 umol, Intermediate AJJ) and 2-(2,6-dioxo-3-piperidyl)-4-fluoro-isoindoline-1,3-dione (65.7 mg, 238 umol, Intermediate R) in DMSO (2 mL) was added DIPEA (76.9 mg, 595 umol). The reaction mixture was stirred at 130° C. for 3 hours. On completion, the reaction mixture was diluted with water (10 mL) and extracted with EA (3×30 mL). The combined organic layers were washed with brine (2×20 mL), dried over Na$_2$SO$_4$, filtered and concentrated in vacuo. The residue was purified by reverse phase (0.1% TFA) to give the title compound (85.0 mg, 41% yield, TFA salt) as yellow solid. $^1$H NMR (400 MHz, DMSO-d$_6$) δ 11.09 (s, 1H), 7.68 (s, 1H), 7.59 (dd, J=7.2, 8.4 Hz, 1H), 7.16-6.85 (m, 3H), 6.73-6.58 (m, 1H), 5.05 (dd, J=5.6, 12.8 Hz, 1H), 4.18-4.06 (m, 1H), 3.48-3.45 (m, 4H), 3.23 (d, J=6.0 Hz, 2H), 2.94-2.80 (m, 1H), 2.62-2.54 (m, 1H), 2.07-1.93 (m, 3H), 1.90-1.79 (m, 4H), 1.79-1.54 (m, 4H), 1.19-1.03 (m, 2H).

3-[1-Oxo-4-(4-piperidylmethylamino)isoindolin-2-yl]piperidine-2,6-dione (Intermediate AJC)

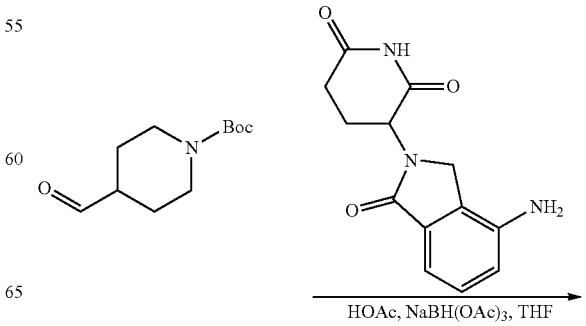

2211
-continued

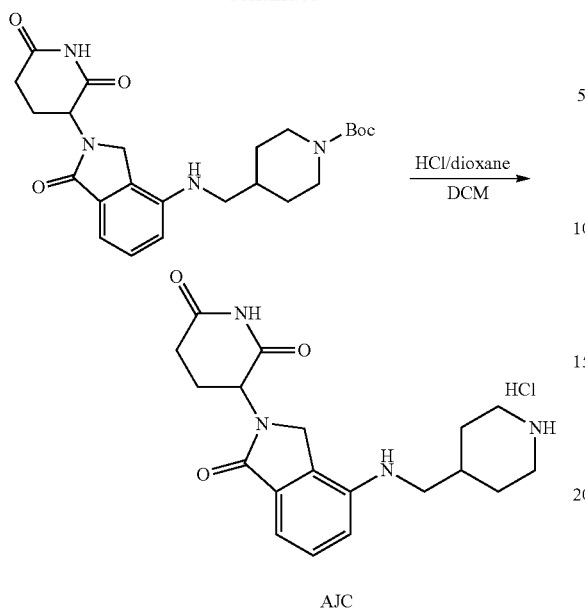

AJC

Step 1—Tert-butyl 4-[[[2-(2,6-dioxo-3-piperidyl)-1-oxo-isoindolin-4-yl]amino]methyl]piperidine-1-carboxylate To a solution of tert-butyl 4-formylpiperidine-1-carboxylate (82.2 mg, 385 umol, CAS #137076-22-3) and 3-(4-amino-1-oxo-isoindolin-2-yl)piperidine-2,6-dione (100 mg, 385 umol, CAS #191732-72-6) in THF (5 mL) was added HOAc (46.3 mg, 771 umol, 44.1 uL), the reaction mixture was stirred at 20° C. for 30 min. Then NaBH(OAc)$_3$ (106 mg, 501 umol) was added, the mixture was stirred at 20° C. for 12 hrs. On completion, the reaction mixture was quenched by water (0.5 mL), filtered and the filtrate was concentrated in vacuo. The residue was purified by prep-HPLC (column: Phenomenex Synergi C18 150*25*10 um; mobile phase: [water (0.225% FA)-ACN]; B %: 32%-62%, 10 min) to give the title compound (30.0 mg, 17% yield) as a white solid. $^1$H NMR (400 MHz, DMSO-d$_6$) δ 11.00 (s, 1H), 7.27 (t, J=8.0 Hz, 1H), 6.91 (d, J=7.2 Hz, 1H), 6.76 (d, J=8.0 Hz, 1H), 5.67 (t, J=5.6 Hz, 1H), 5.11 (dd, J=5.2, 13.2 Hz, 1H), 4.27-4.18 (m, 1H), 4.16-4.07 (m, 1H), 4.02-3.88 (m, 2H), 3.03 (t, J=6.0 Hz, 2H), 2.98-2.87 (m, 1H), 2.67-2.54 (m, 2H), 2.31-2.23 (m, 1H), 2.08-2.00 (m, 1H), 1.79-1.70 (m, 3H), 1.39 (s, 9H), 1.10-0.98 (m, 2H); LC-MS (ESI$^+$) m/z 479.3 (M+Na)$^+$.

Step 2—3-[1-Oxo-4-(4-piperidylmethylamino)isoindolin-2-yl]piperidine-2,6-dione To a solution of tert-butyl 4-[[[2-(2,6-dioxo-3-piperidyl)-1-oxo-isoindolin-4-yl]amino]methyl] piperidine-1-carboxylate (30.0 mg, 65.71 umol) in DCM (2 mL) was added HCl/dioxane (4 M, 1 mL). The reaction mixture was stirred at 20° C. for 30 min. On completion, the reaction mixture was concentrated in vacuo to give the title compound (20.0 mg, 77% yield, HCl salt) as a white solid. LC-MS (ESI$^+$) m/z 357.2 (M+H)$^+$.

2212
Benzyl N-[3-(4-amino-1-piperidyl)propyl]carbamate (Intermediate AJU)

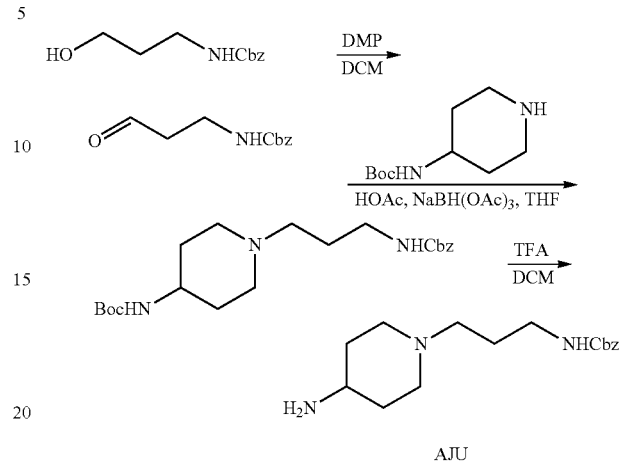

AJU

Step 1—Benzyl N-(3-oxopropyl)carbamate

To a mixture of benzyl N-(3-hydroxypropyl)carbamate (2.00 g, 9.56 mmol, CAS #17996-13-3) in DCM (20 mL) was added DMP (6.08 g, 14.3 mmol). The reaction mixture was stirred at 25° C. for 2 hours. On completion, the reaction mixture was quenched by saturated Na$_2$S$_2$O$_3$ (10 mL) and saturated NaHCO$_3$ (10 mL) at 25° C., and stirred for 30 minutes. The mixture was extracted with DCM (3×20 mL), the combined organic phase was dried over Na$_2$SO$_4$, filtered and the filtrate was concentrated in vacuo to give a residue. The residue was purified by column chromatography to give the title compound (1.00 g, 50% yield) as white solid. $^1$H NMR (400 MHz, CDCl$_3$) δ 9.80 (s, 1H), 7.38-7.30 (m, 5H), 5.22 (s, 1H), 5.09 (s, 2H), 3.54-3.42 (m, 2H), 2.74 (t, J=5.6 Hz, 2H).

Step 2—Tert-butyl N-[1-[3-(benzyloxycarbonylamino)propyl]-4-piperidyl]carbamate To a mixture of benzyl N-(3-oxopropyl)carbamate (910 mg, 4.39 mmol, CAS #73874-95-0) in THF (3 mL) was added HOAc (239 mg, 3.99 mmol, 228 uL) and tert-butyl N-(4-piperidyl)carbamate (800 mg, 3.99 mmol), the mixture stirred at 25° C. for 0.5 hour. Next, NaBH(OAc)$_3$ (1.69 g, 7.99 mmol) was added to the mixture. The reaction mixture was stirred at 25° C. for 12 hours. On completion, the reaction mixture was quenched with water (0.05 mL) and concentrated in vacuo to give a residue. The residue was purified by reverse phase (0.1% FA condition) to give the title compound (350 mg, 22% yield) as white solid. $^1$H NMR (400 MHz, CDCl$_3$) δ 12.14-11.89 (m, 1H), 7.37-7.30 (m, 5H), 5.09 (s, 2H), 4.73 (d, J=7.6 Hz, 1H), 3.77-3.60 (m, 1H), 3.55 (d, J=10.8 Hz, 2H), 3.39-3.33 (m, 2H), 2.99 (d, J=2.4 Hz, 2H), 2.66 (d, J=10.0 Hz, 2H), 2.33-2.20 (m, 2H), 2.14-2.06 (m, 4H), 1.44 (s, 9H).

Step 3—Benzyl N-[3-(4-amino-1-piperidyl)propyl]carbamate

To a mixture of tert-butyl N-[1-[3-(benzyloxycarbonylamino)propyl]-4-piperidyl]carbamate (300 mg, 766 umol) in DCM (1 mL) was added TFA (4.62 g, 40.5 mmol, 3.00 mL). The reaction mixture was stirred at 25° C. for 0.5 hour. On completion, the reaction mixture was concentrated in vacuo to give the title compound (310 mg, 99% yield, TFA salt) as colorless oil. LC-MS (ESI$^+$) m/z 292.3 (M+H)$^+$.

4-[[1-(3-Aminopropyl)-4-piperidyl]amino]-2-(2,6-dioxo-3-piperidyl)isoindoline-1,3-dione (Intermediate AJV)

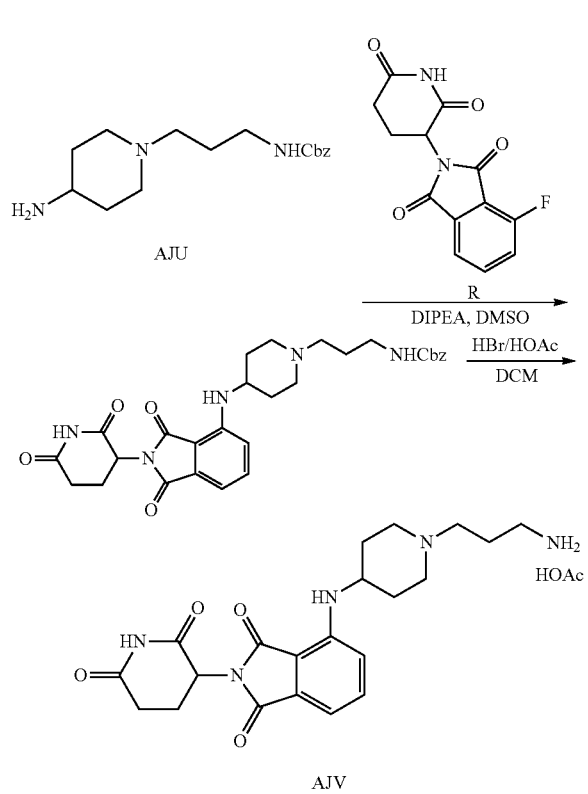

Step 1—Benzyl N-[3-[4-[[2-(2,6-dioxo-3-piperidyl)-1,3-dioxo-isoindolin-4-yl]amino]-1-piperidyl] propyl]carbamate To a mixture of benzyl N-[3-(4-amino-1-piperidyl)propyl]carbamate (193 mg, 477 umol, TFA salt, Intermediate AJU) and 2-(2,6-dioxo-3-piperidyl)-4-fluoro-isoindoline-1,3-dione (120 mg, 434 umol, Intermediate R) in DMSO (4 mL) was added DIPEA (280 mg, 2.17 mmol, 378 uL). The reaction mixture was stirred at 130° C. for 2 hours. On completion, the reaction mixture was filtered and concentrated in vacuo. The residue was purified by prep-HPLC (column: Phenomenex Synergi C18 150*25*10 um; mobile phase: [water (0.05% HCl)-ACN]; B %: 22%-42%, 11 min) to give the title compound (50.0 mg, 21% yield) as green solid. LC-MS (ESI$^+$) m/z 548.4 (M+H)$^+$.

Step 2—4-[[1-(3-Aminopropyl)-4-piperidyl]amino]-2-(2,6-dioxo-3-piperidyl)isoindoline-1,3-dione To a mixture of benzyl N-[3-[4-[[2-(2,6-dioxo-3-piperidyl)-1,3-dioxo-isoindolin-4-yl]amino]-1-piperidyl]propyl]carbamate (50.0 mg, 91.3 umol) in DCM (2 mL) was added HBr/AcOH (91.3 umol, 1 mL). The reaction mixture was stirred at 25° C. for 2 hours. On completion, the reaction mixture was concentrated in vacuo to give title compound (43.0 mg, 99% yield, HOAc salt) as red solid. LC-MS (ESI$^+$) m/z 414.3 (M+H)$^+$.

2-(2,6-Dioxo-3-piperidyl)-4-(4-piperidylmethylamino)isoindoline-1,3-dione (Intermediate AJI)

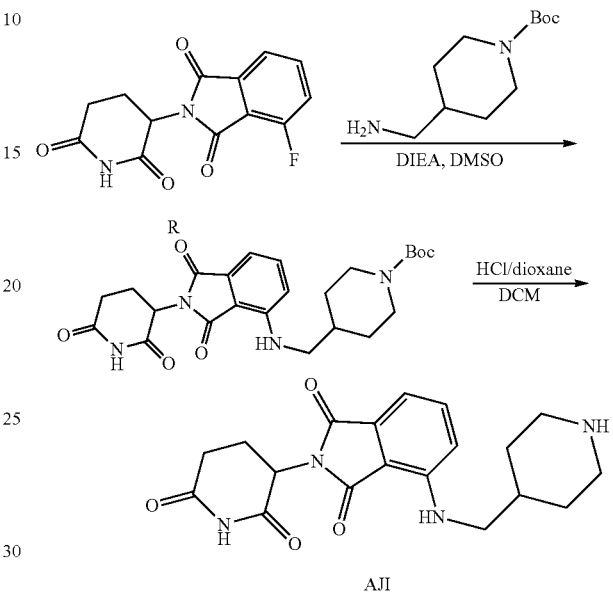

Step 1—Tert-butyl 4-[[[2-(2,6-dioxo-3-piperidyl)-1,3-dioxo-isoindolin-4-yl]amino]methyl]piperidine-1-carboxylate To a solution of 2-(2,6-dioxo-3-piperidyl)-4-fluoro-isoindoline-1,3-dione (200 mg, 724 umol, Intermediate R), tert-butyl 4-(aminomethyl)piperidine-1-carboxylate (186 mg, 868 umol) in DMSO (5.00 mL) was added DIPEA (467 mg, 3.62 mmol). The mixture was stirred at 130° C. for 3 hours. On completion, the mixture was diluted with H$_2$O (30 mL), filtered and the solid was dried in vacuo to give the title compound (320 mg, 93% yield) as yellow solid. $^1$H NMR (400 MHz, DMSO-d$_6$) δ 11.09 (s, 1H), 7.57 (dd, J=7.2, 8.4 Hz, 1H), 7.19-7.11 (m, 1H), 7.02 (d, J=7.2 Hz, 1H), 6.70-6.59 (m, 1H), 5.10-5.00 (m, 1H), 4.01-3.84 (m, 3H), 3.26-3.19 (m, 2H), 2.94-2.82 (m, 1H), 2.75-2.64 (m, 2H), 2.09-1.99 (m, 1H), 1.80-1.72 (m, 1H), 1.70-1.53 (m, 3H), 1.39 (s, 9H), 1.08-1.01 (m, 2H).

Step 2—2-(2,6-Dioxo-3-piperidyl)-4-(4-piperidylmethylamino)isoindoline-1,3-dione To a solution of tert-butyl 4-[[[2-(2,6-dioxo-3-piperidyl)-1,3-dioxo-isoindolin-4-yl]amino]methyl] piperidine-1-carboxylate (100 mg, 212 umol) in DCM (3.00 mL) was added HCl/dioxane (4.00 M, 3.00 mL). The mixture was stirred at 15° C. for 0.5 hour. On completion, the mixture was concentrated in vacuo to give the title compound (80.0 mg, 92% yield, HCl salt) as yellow solid. $^1$H NMR (400 MHz, DMSO-d$_6$) δ 11.10 (s, 1H), 7.59 (dd, J=7.2, 8.4 Hz, 1H), 7.16 (d, J=8.8 Hz, 1H), 7.07-7.02 (m, 1H), 6.81-6.70 (m, 1H), 5.10-5.00 (m, 1H), 3.30-3.26 (m, 2H), 3.26-3.22 (m, 2H), 2.95-2.87 (m, 1H), 2.87-2.75 (m, 3H), 2.64-2.53 (m, 2H), 2.09-1.98 (m, 1H), 1.88-1.79 (m, 3H), 1.44-1.37 (m, 2H).

3-(3-Methyl-4-(2-((R)-morpholin-2-yl)ethyl)-2-oxo-2,3-dihydro-1H-benzo[d]imidazol-1-yl)piperidine-2,6-dione (Intermediate ASA)

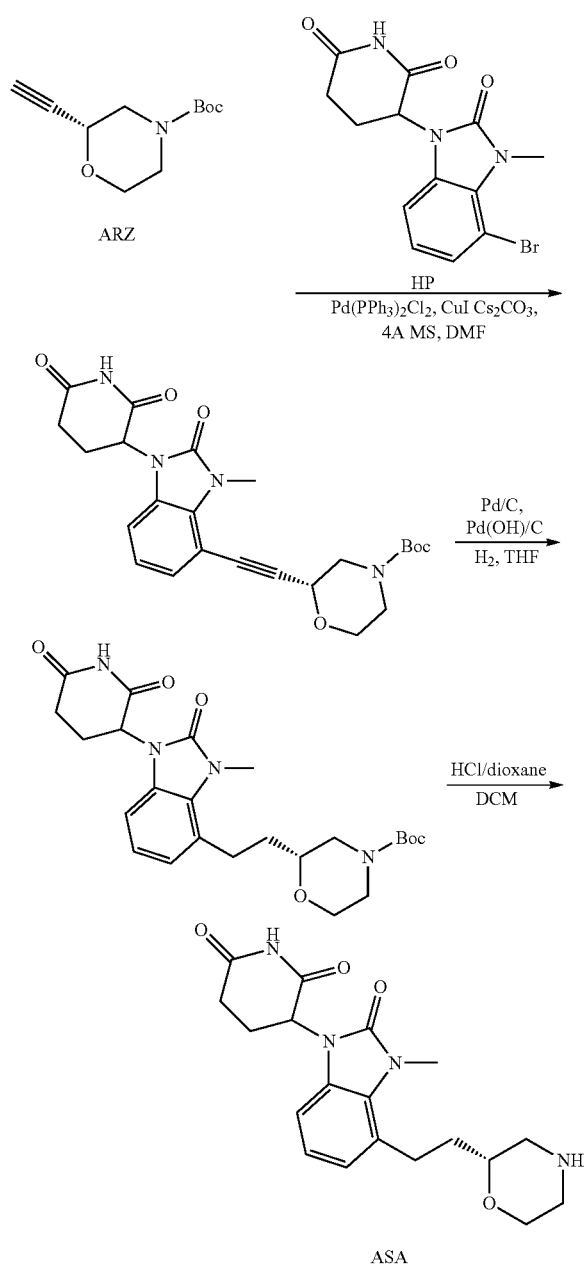

Step 1—(2R)-tert-butyl 2-((1-(2,6-dioxopiperidin-3-yl)-3-methyl-2-oxo-2,3-dihydro-1H-benzo[d]imidazol-4-yl)ethynyl)morpholine-4-carboxylate A solution of 3-(4-bromo-3-methyl-2-oxo-benzimidazol-1-yl)piperidine-2,6-dione (1.01 g, 2.98 mmol, Intermediate HP), Cs$_2$CO$_3$ (2.91 g, 8.95 mmol), CuI (56.8 mg, 298 umol), Pd(PPh$_3$)$_2$Cl$_2$ (209 mg, 298 umol) and 4 Å molecular sieves (2.98 mmol) in DMF (5 mL) was degassed and purged with nitrogen for 3 times, then a solution of tert-butyl (2R)-2-ethynylmorpholine-4-carboxylate (630 mg, 2.98 mmol, Intermediate ARZ) in DMF (5 mL) was added. The reaction mixture was stirred at 80° C. for 3 hrs under nitrogen atmosphere. On completion, the reaction mixture was filtered and the filtrate was concentrated in vacuo to give a residue. The residue was purified by silica gel chromatography (petroleum ether:ethyl acetate=1:2) to give the title compound (700 mg, 47% yield) as yellow solid. $^1$H NMR (400 MHz, DMSO-d$_6$) δ 11.12 (s, 1H), 7.19 (d, J=7.2 Hz, 1H), 7.14-7.09 (m, 1H), 7.08-6.97 (m, 1H), 5.39 (dd, J=12.8, 5.2 Hz, 1H), 4.71-4.69 (m, 1H), 3.93-3.81 (m, 1H), 3.67-3.52 (m, 5H), 3.49-3.47 (m, 1H), 3.36-3.34 (m, 2H), 2.90-2.87 (m, 1H), 2.77-2.64 (m, 2H), 2.08-1.98 (m, 1H), 1.40 (s, 9H).

Step 2—(2R)-tert-butyl 2-(2-(1-(2,6-dioxopiperidin-3-yl)-3-methyl-2-oxo-2,3-dihydro-1H-benzo[d]imidazol-4-yl)ethyl)morpholine-4-carboxylate To a solution of tert-butyl (2R)-2-[2-[1-(2,6-dioxo-3-piperidyl)-3-methyl-2-oxo-benzimidazol-4-yl]ethynyl]morpholine-4-carboxylate (150 mg, 320 umol) in THF (10 mL) was added Pd/C (50.0 mg, 10 wt %) and Pd(OH)$_2$ (50.0 mg). The mixture was stirred at 25° C. for 20 hrs under hydrogen atmosphere. On completion, the reaction mixture was filtered and the filtrate was concentrated in vacuo to give a residue. The residue was purified by silica gel chromatography (petroleum ether:ethyl acetate=1:1) to give the title compound (100 mg, 64% yield) as white solid. $^1$H NMR (400 MHz, DMSO-d$_6$) δ 11.09 (s, 1H), 7.02-6.91 (m, 2H), 6.90-6.82 (m, 1H), 5.36 (dd, J=12.8, 5.2 Hz, 1H), 3.92-3.68 (m, 3H), 3.56 (s, 3H), 3.43-3.35 (m, 2H), 3.11-3.07 (m, 1H), 2.94-2.82 (m, 2H), 2.76-2.59 (m, 3H), 2.06-1.92 (m, 2H), 1.81-1.63 (m, 2H), 1.39 (s, 9H).

Step 3—3-(3-Methyl-4-(2-((R)-morpholin-2-yl)ethyl)-2-oxo-2,3-dihydro-1H-benzo[d]imidazol-1-yl)piperidine-2,6-dione To a solution of tert-butyl (2R)-2-[2-[1-(2,6-dioxo-3-piperidyl)-3-methyl-2-oxo-benzimidazol-4-yl]ethyl]morpholine-4-carboxylate (100 mg, 212 umol) in DCM (1 mL) was added HCl/dioxane (4 M) at 25° C. and stirred for 10 mins. On completion, the reaction mixture was concentrated in vacuo to give the title compound (86.5 mg, 100% yield, HCl) as yellow solid. LC-MS (ESI$^+$) m/z 373.3 (M+H)$^+$.

3-[4-[3-(2,7-Diazaspiro[3.5]nonan-7-yl)prop-1-ynyl]-3-methyl-2-oxo-benzimidazol-1-yl] piperidine-2,6-dione (Intermediate ASB)

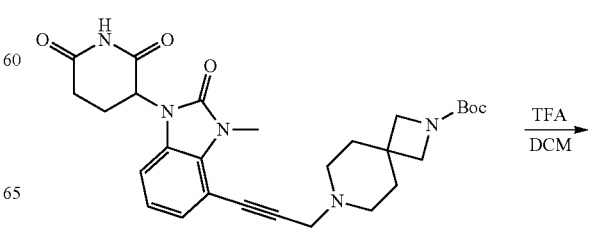

2217

-continued

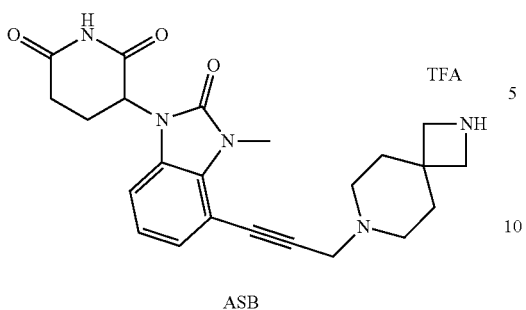

ASB

To a mixture of tert-butyl 7-[3-[1-(2,6-dioxo-3-piperidyl)-3-methyl-2-oxo-benzimidazol-4-yl]prop-2-ynyl]-2,7-diazaspiro[3.5]nonane-2-carboxylate (50.0 mg, 95.8 umol, synthesized via Step 1 of Intermediate ALQ) in DCM (2 mL) was added TFA (1.54 g, 13.5 mmol, 1 mL). The reaction mixture was stirred at 20° C. for 0.5 hr. On completion, the reaction mixture was concentrated in vacuo to give the title compound (50.0 mg, 97% yield, TFA salt) as brown oil. LC-MS (ESI$^+$) m/z 422.4 (M+H)$^+$.

3-[3-methyl-2-oxo-6-[3-(4-piperidyloxy)propyl]benzimidazol-1-yl]piperidine-2,6-dione (Intermediate ASC)

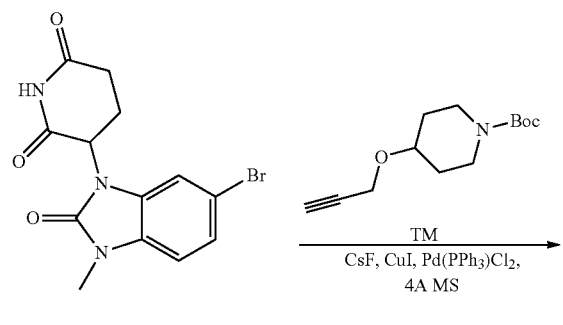

ATL

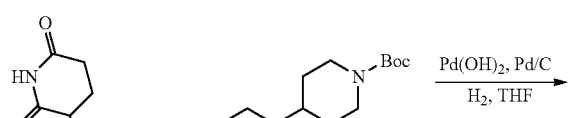

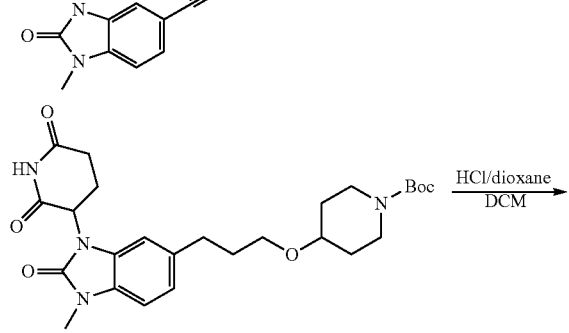

2218

-continued

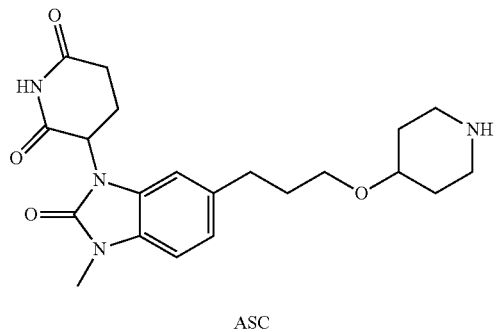

ASC

Step 1—Tert-butyl4-[3-[3-(2,6-dioxo-3-piperidyl)-1-methyl-2-oxo-benzimidazol-5-yl]prop-2-ynoxy] piperidine-1-carboxylate A mixture of 3-(6-bromo-3-methyl-2-oxo-benzimidazol-1-yl)piperidine-2,6-dione (500 mg, 1.48 mmol, Intermediate ATL) tert-butyl 4-prop-2-ynoxypiperidine-1-carboxylate (531 mg, 2.22 mmol, Intermediate™), CsF (898 mg, 5.91 mmol, 218 uL), CuI (28.2 mg, 148 umol), Pd(PPh$_3$)$_2$Cl$_2$ (103 mg, 147 umol) and 4 Å molecular sieves (100 mg) in DMF (10 mL) was stirred at 80° C. for 14 hrs under nitrogen atmosphere. On completion, the reaction mixture was filtered and the filtrate was concentrated in vacuo to give a residue. The residue was purified by Prep-HPLC (Neu: column: Waters Xbridge C18 150*50 mm*10 um; mobile phase: [water (10 mM NH$_4$HCO$_3$)-ACN]; B %: 30%-60%, 11.5 min) to give the title compound (300 mg, 38% yield) as yellow solid. LC-MS (ESI$^+$) m/z 397.2 (M+H−100)$^+$.

Step 2—Tert-butyl4-[3-[3-(2,6-dioxo-3-piperidyl)-1-methyl-2-oxo-benzimidazol-5-yl]propoxy] piperidine-1-carboxylate To a solution of tert-butyl 4-[3-[3-(2,6-dioxo-3-piperidyl)-1-methyl-2-oxo-benzimidazol-5-yl]prop-2-ynoxy] piperidine-1-carboxylate (130 mg, 262 umol) in THF (3 mL) was added Pd/C (15 mg, 10% wt) and Pd(OH)$_2$ (15 mg, 10% wt) under N$_2$ atmosphere. The suspension was degassed and purged with H$_2$ gas 3 times. The mixture was stirred under H$_2$ (15 Psi) at 25° C. for 12 hr. On completion, the reaction mixture was filtered and the filtrate was concentrated under reduced pressure to give the title compound (130 mg, 90% yield) as a white solid. LC-MS (ESI$^+$) m/z 401.3 (M+H−100)$^+$.

Step 3—3-[3-methyl-2-oxo-6-[3-(4-piperidyloxy)propyl]benzimidazol-1-yl]piperidine-2,6-dione To a solution of tert-butyl 4-[3-[3-(2,6-dioxo-3-piperidyl)-1-methyl-2-oxo-benzimidazol-5-yl] propoxy]piperidine-1-carboxylate (130 mg, 260 umol) in DCM (3 mL) was added HCl/dioxane (4 M, 1.0 mL). The mixture was stirred at 25° C. for 1 hr. On completion, the reaction mixture was concentrated under reduced pressure to give the title compound (90 mg, 100% yield, HCl) as a white solid. LC-MS (ESI$^+$) m/z 401.2 (M+H−100)$^+$.

2219

3-[3-methyl-2-oxo-6-[3-(4-piperidyloxy)prop-1-ynyl]benzimidazol-1-yl]piperidine-2,6-dione (Intermediate ASD)

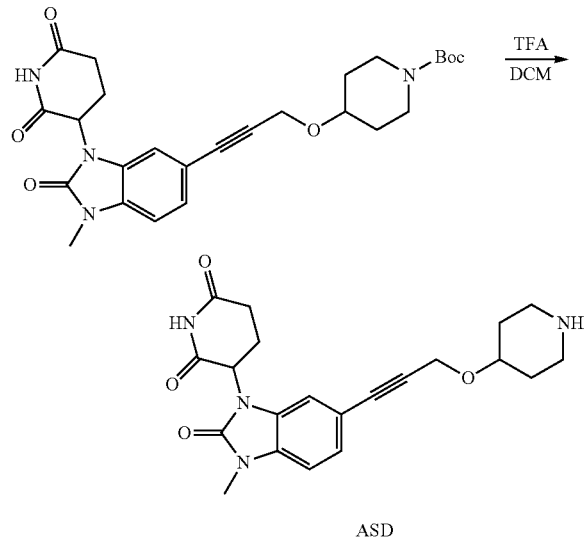

ASD

To a solution of tert-butyl 4-[3-[3-(2,6-dioxo-3-piperidyl)-1-methyl-2-oxo-benzimidazol-5-yl] prop-2-ynoxy] piperidine-1-carboxylate (70 mg, 141 umol, synthesized via Step 1 of Intermediate ASC) in DCM (3.0 mL) was added TFA (462 mg, 4.05 mmol, 0.3 mL). The mixture was stirred at 25° C. for 20 min. On completion, the reaction mixture was concentrated under reduced pressure to give the title compound (50 mg, 100% yield, TFA) as yellow oil. LC-MS (ESI+) m/z 397.2 (M+H)+.

2-(2,6-Dioxo-3-piperidyl)-4-[[(2S)-4-[2-(methylamino)ethyl]morpholin-2-yl]methylamino] isoindoline-1,3-dione (Intermediate ASU)

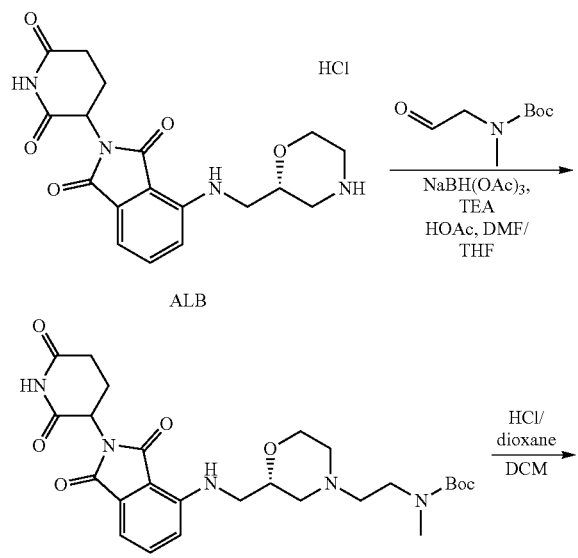

2220

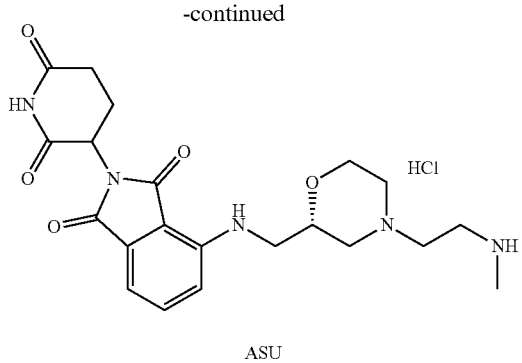

ASU

Step 1—Tert-butyl N-[2-[(2S)-2-[[[2-(2,6-dioxo-3-piperidyl-1,3-dioxo-isoindolin-4-yl]amino]methyl] morpholin-4-yl]ethyl]-N-methyl-carbamate To a solution of 2-(2,6-dioxo-3-piperidyl)-4-[[(2R)-morpholin-2-yl]methylamino]isoindoline-1,3-dione (70.0 mg, 187 umol, Intermediate ALB) in DMF (2 mL) was added Et$_3$N (19.0 mg, 187 umol) and the mixture was stirred at 15° C. for 0.5 hr. HOAc (11.3 mg, 187 umol) and tert-butyl N-methyl-N-(2-oxoethyl) carbamate (32.6 mg, 187 umol) was added to the mixture. The mixture was stirred at 15° C. for 0.5 hr. NaBH(OAc)$_3$ (39.8 mg, 187 umol) was added. The mixture was stirred at 15° C. for 2 hrs. On completion, the mixture was quenched with 0.5 mL water and the mixture was purified by reverse phase (0.1% FA condition) to give the title compound (80.0 mg, 80% yield) as yellow solid. LC-MS (ESI+) m/z 530.2 (M+1)+.

Step 2—2-(2,6-Dioxo-3-piperidyl)-4-[[(2S)-4-[2-(methylamino)ethyl]morpholin-2-yl]methylamino] isoindoline-1,3-dione To a solution of tert-butyl N-[2-[(2S)-2-[[[2-(2,6-dioxo-3-piperidyl)-1,3-dioxo-isoindolin-4-yl] amino] methyl]morpholin-4-yl]ethyl]-N-methyl-carbamate (70.0 mg, 132 umol) in DCM (2 mL) was added HCl/dioxane (4 M, 7.00 mL). The mixture was stirred at 15° C. for 0.5 hr. On completion, the mixture was concentrated in vacuo to give the title compound (56.0 mg, 98% yield) as yellow solid. LC-MS (ESI+) m/z 430.1 (M+1)+.

5-[(1 S,5R)-8-oxa-3-azabicyclo[3.2.1]octan-3-yl] pyrazolo[1,5-a]pyrimidine-3-carboxylic acid (Intermediate ASZ)

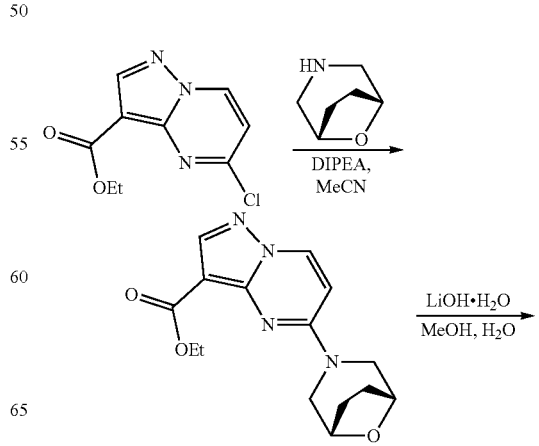

2221
-continued

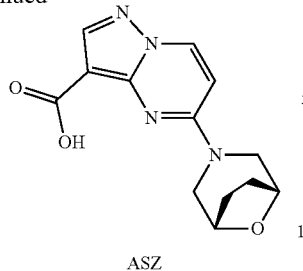

ASZ

Step 1—Ethyl 5-[(1S,5R)-8-oxa-3-azabicyclo[3.2.1]octan-3-yl]pyrazolo[1,5-a]pyrimidine-3-carboxylate To a solution of ethyl 5-chloropyrazolo[1,5-a]pyrimidine-3-carboxylate (1.80 g, 7.98 mmol, CAS #1224944-77-7), (1S,5R)-8-oxa-3-azabicyclo[3.2.1]octane (1.79 g, 12.0 mmol, CAS #280-13-7) in ACN (30 mL) was added DIPEA (4.12 g, 31.9 mmol). The mixture was stirred at 60° C. for 1 hr. On completion, the reaction mixture was concentrated in vacuo to give a residue. The residue was purified by reverse phase flash (0.1% FA condition) to give the title compound (2.20 g, 91% yield) as a yellow solid. $^1$H NMR (400 MHz, DMSO-$d_6$) δ 8.74 (d, J=8.0 Hz, 1H), 8.22 (s, 1H), 6.78 (d, J=8.0 Hz, 1H), 4.47 (d, J=2.4 Hz, 2H), 4.20 (q, J=7.2 Hz, 2H), 3.30 (s, 2H), 3.17 (d, J=12.4 Hz, 2H), 1.92-1.80 (m, 2H), 1.75-1.63 (m, 2H), 1.29 (t, J=7.2 Hz, 3H).

Step 2—5-[(1 S,5R)-8-oxa-3-azabicyclo[3.2.1]octan-3-yl]pyrazolo[1,5-a]pyrimidine-3-carboxylic acid To a solution of ethyl 5-[(1 S,5R)-8-oxa-3-azabicyclo[3.2.1]octan-3-yl]pyrazolo[1,5-a]pyrimidine-3-carboxylate (2.10 g, 6.95 mmol) in a mixed solvent of MeOH (20 mL) and H$_2$O (4.0 mL) was added LiOH.H$_2$O (1.46 g, 34.7 mmol). The mixture was stirred at 60° C. for 16 hrs. On completion, the reaction mixture was concentrated in vacuo to remove methanol. The residue was acidified with 1N HCl solution until the pH=3. Then the residue was filtered and the filter cake was washed by water and dried in vacuo to give the title compound (1.60 g, 94% yield) as a white solid. $^1$H NMR (400 MHz, DMSO-$d_6$) δ 11.7 (br s, 1H), 8.73 (d, J=8.0 Hz, 1H), 8.19 (s, 1H), 6.77 (d, J=8.0 Hz, 1H), 4.47 (d, J=2.4 Hz, 2H), 4.32-3.73 (m, 2H), 3.16 (d, J=12.8 Hz, 2H), 1.94-1.79 (m, 2H), 1.70 (d, J=7.2 Hz, 2H). LC-MS (ESI$^+$) m/z 257.0 (M+H−18)$^+$.

N-[3-(difluoromethyl)-1-(4-formylcyclohexyl)pyrazol-4-yl]-5-[(1 S,5R)-8-oxa-3-azabicyclo[3.2.1]octan-3-yl]pyrazolo[1,5-a]pyrimidine-3-carboxamide (Intermediate ASE)

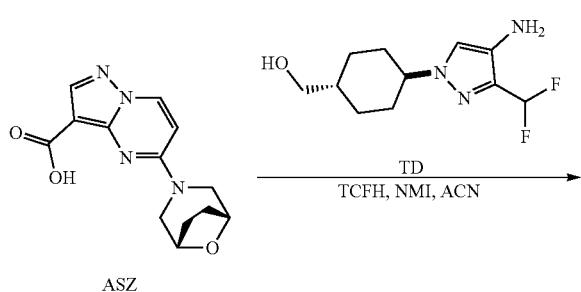

2222
-continued

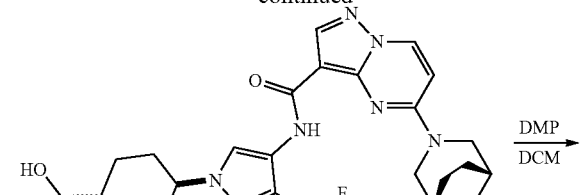

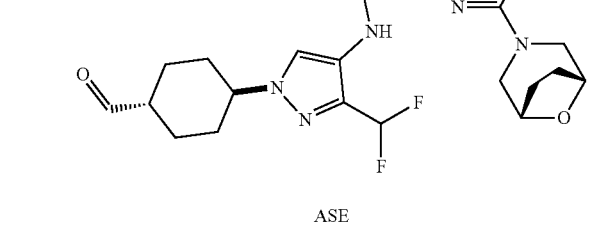

ASE

Step 1—N-[3-(difluoromethyl)-1-[4-(hydroxymethyl)cyclohexyl]pyrazol-4-yl]-5-[(1S,5R)-8-oxa-3-azabicyclo[3.2.1]octan-3-yl]pyrazolo [1,5-a]pyrimidine-3-carboxamide To a solution of 5-[(1S,5R)-8-oxa-3-azabicyclo[3.2.1]octan-3-yl]pyrazolo[1,5-a]pyrimidine-3-carboxylic acid (1.40 g, 5.10 mmol, Intermediate ASZ) in ACN (40 mL) was added 1-methylimidazole (1.47 g, 17.9 mmol), [chloro(dimethylamino)methylene]-dimethyl-ammonium; hexafluorophosphate (1.72 g, 6.13 mmol). The mixture was stirred at 25° C. for 30 min. Then [4-[4-amino-3-(difluoromethyl)pyrazol-1-yl] cyclohexyl]methanol (1.50 g, 6.13 mmol, Intermediate TD) was added to the mixture, and the reaction mixture was stirred at 25° C. for 2 hrs. On completion, the reaction mixture was filtered and the filter cake was washed by water and in vacuo to give the title compound (2.00 g, 78% yield) as a white solid. $^1$H NMR (400 MHz, DMSO-$d_6$) δ 9.41 (s, 1H), 8.81 (d, J=8.0 Hz, 1H), 8.38 (s, 1H), 8.28 (s, 1H), 7.25-6.97 (m, 1H), 6.81 (d, J=8.0 Hz, 1H), 4.61-4.33 (m, 3H), 4.29-3.80 (m, 3H), 3.31-3.12 (m, 4H), 2.13-1.99 (m, 2H), 1.89-1.85 (m, 4H), 1.80-1.62 (m, 4H), 1.50-1.31 (m, 1H), 1.13-1.07 (m, 2H).

Step 2—N-[3-(difluoromethyl)-1-(4-formylcyclohexyl)pyrazol-4-yl]-5-[(1 S,5R)-8-oxa-3-azabicyclo[3.2.1]octan-3-yl]pyrazolo[1,5-a]pyrimidine-3-carboxamide To a solution of N-[3-(difluoromethyl)-1-[4-(hydroxymethyl)cyclohexyl]pyrazol-4-yl]-5-[(1S,5R)-8-oxa-3-azabicyclo[3.2.1]octan-3-yl]pyrazolo[1,5-a]pyrimidine-3-carboxamide (1.95 g, 3.89 mmol) in DCM (30 mL) was added DMP (2.47 g, 5.83 mmol) at 25° C. under N$_2$. The mixture was stirred at 25° C. for 1 hr. On completion, the reaction mixture was quenched with Na$_2$S$_2$O$_3$ (30 mL) and extracted with DCM (2×30 mL). The combined organic layer was washed with NaHCO$_3$ and brine (2×30 mL), dried with anhydrous Na$_2$SO$_4$, filtered and concentrated in vacuo to give the title compound (2.00 g, 80% yield) as a yellow solid. LC-MS (ESI$^+$) m/z 500.2 (M+H)$^+$.

2223

N-[(1S)-3-(difluoromethyl)-1-(4-formylcyclohexyl)pyrazol-4-yl]-5-[(2R,6S)-2,6-dimethylmorpholin-4-yl]pyrazolo[1,5-a]pyrimidine-3-carboxamide (Intermediate ASF)

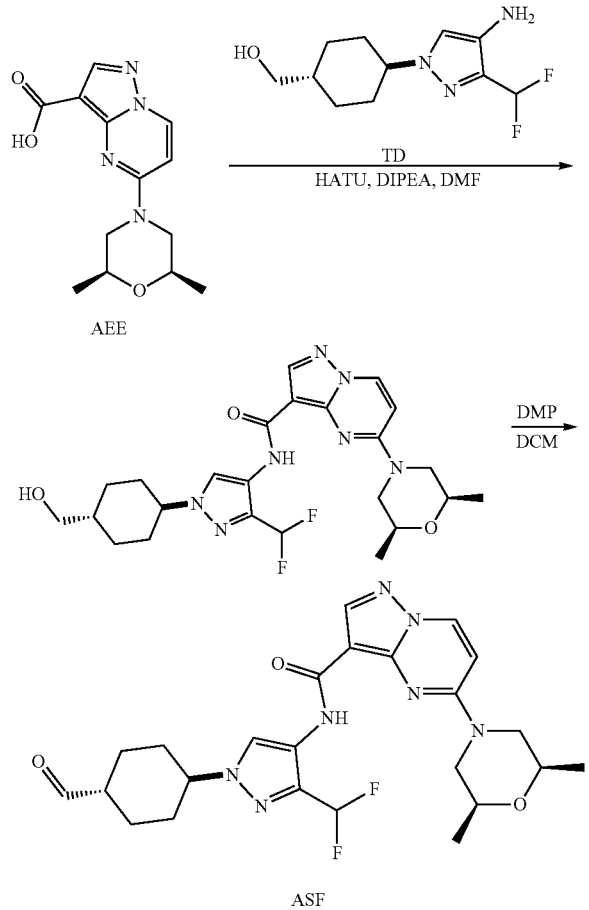

Step 1—N-[(1S)-3-(difluoromethyl)-1-[4-(hydroxymethyl)cyclohexyl]pyrazol-4-yl]-5-[(2R,6S)-2,6-dimethylmorpholin-4-yl]pyrazolo[1,5-a]pyrimidine-3-carboxamide To a mixture of 5-[(2R,6S)-2,6-dimethylmorpholin-4-yl]pyrazolo[1,5-a]pyrimidine-3-carboxylic acid (1.18 g, 4.27 mmol, Intermediate AEE) in DMF (15 mL) was added HATU (2.11 g, 5.55 mmol), DIPEA (1.38 g, 10.6 mmol). The mixture was stirred at 25° C. for 10 minutes, then [4-[(1S)-4-amino-3-(difluoromethyl)pyrazol-1-yl]cyclohexyl]methanol (1.36 g, 5.55 mmol, Intermediate TD) was added and the mixture stirred at 60° C. for 3 hours. On completion, the reaction mixture was quenched with water (10 mL) and then washed with citric acid to pH=7. The mixture was filtrated and the filter cake was dried in vacuo to give the title compound (2.00 g, 93% yield) as white solid. $^1$H NMR (400 MHz, DMSO-$d_6$) δ 9.26 (s, 1H), 8.80 (d, J=8.0 Hz, 1H), 8.39 (s, 1H), 8.27 (s, 1H), 7.38-6.98 (m, 1H), 6.93 (d, J=8.0 Hz, 1H), 4.60-4.30 (m, 3H), 4.24-4.09 (m, 1H), 3.70-3.55 (m, 2H), 3.25 (t, J=5.6 Hz, 2H), 2.78-2.56 (m, 2H), 2.11-1.96 (m, 2H), 1.92-1.80 (m, 2H), 1.77-1.65 (m, 2H), 1.50-1.35 (m, 1H), 1.19 (d, J=6.4 Hz, 6H), 1.11-1.02 (m, 2H).

2224

Step 2—N-[(1S)-3-(difluoromethyl)-1-(4-formylcyclohexyl)pyrazol-4-yl]-5-[(2R,6S)-2,6-dimethyl morpholin-4-yl]pyrazolo[1,5-a]pyrimidine-3-carboxamide To a mixture of N-[(1S)-3-(difluoromethyl)-1-[4-(hydroxymethyl)cyclohexyl]pyrazol-4-yl]-5-[(2R,6S)-2,6-dimethylmorpholin-4-yl]pyrazolo[1,5-a]pyrimidine-3-carboxamide (800 mg, 1.59 mmol) in DCM (20 mL) was added DMP (808 mg, 1.91 mmol, 590 uL) at 0° C. Then reaction mixture warm to 25° C. and stirred at 25° C. for 4 hr. On completion, the reaction mixture was quenched with saturated $Na_2S_2O_3$ (5 ml) and saturated $NaHCO_3$ (10 mL) aqueous was added. The mixture was extracted with DCM (2×10 mL). The organic phase was dried over anhydrous sodium sulfate, filtrated and concentrated in vacuo to give the title compound (790 mg, 99% yield) as white solid. $^1$H NMR (400 MHz, DMSO-$d_6$) δ 9.62 (s, 1H), 9.28 (s, 1H), 8.82 (d, J=8.0 Hz, 1H), 8.41 (s, 1H), 8.28 (s, 1H), 7.43-7.00 (m, 1H), 6.95 (d, J=8.0 Hz, 1H), 4.66-4.25 (m, 2H), 4.25-4.11 (m, 1H), 3.75-3.53 (m, 2H), 2.73-2.60 (m, 2H), 2.44-2.31 (m, 1H), 2.17-1.97 (m, 4H), 1.90-1.72 (m, 2H), 1.45-1.30 (m, 2H), 1.19 (d, J=6.0 Hz, 6H).

5-[(2R,6R)-2,6-dimethylmorpholin-4-yl]pyrazolo[1,5-a]pyrimidine-3-carboxylic acid (Intermediate ASG)

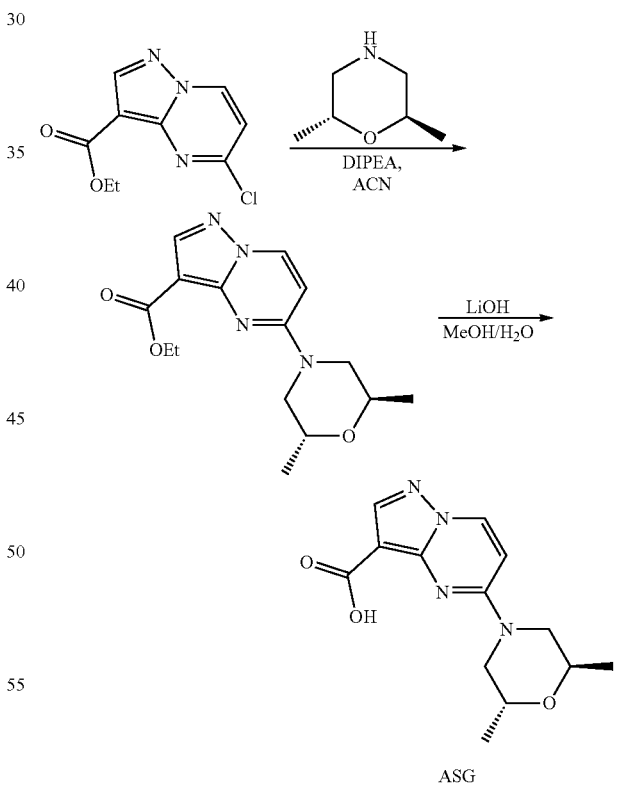

Step 1—Ethyl 5-[(2R,6R)-2,6-dimethylmorpholin-4-yl]pyrazolo[1,5-a]pyrimidine-3-carboxylate To a solution of ethyl 5-chloropyrazolo[1,5-a]pyrimidine-3-carboxylate (1.23 g, 5.45 mmol, CAS #1224944-77-7) and (2R,6R)-2,6-dimethylmorpholine (690 mg, 5.99 mmol, CAS

171753-74-5) in ACN (15.0 mL) was added DIPEA (2.11 g, 16.3 mmol, 2.85 mL). The mixture was stirred at 60° C. for 16 hrs. On completion, the reaction mixture was concentrated in vacuo to give a residue, then diluted with water (20 mL) and extracted with EA (2×20 mL). The combined organic layers were washed with brine (2×30 mL). The organic layer was dried over anhydrous $Na_2SO_4$, filtered and concentrated in vacuo to give the title compound (1.60 g, 96% yield) as a yellow solid. $^1$H NMR (400 MHz, DMSO-$d_6$) δ 8.73 (d, J=8.0 Hz, 1H), 8.20 (s, 1H), 6.86 (d, J=8.0 Hz, 1H), 4.21-4.15 (m, 2H), 4.08-4.01 (m, 2H), 4.01-3.75 (m, 2H), 3.49-3.44 (m, 2H), 1.28 (t, J=7.2 Hz, 3H), 1.14 (d, J=6.4 Hz, 6H).

Step 2—5-[(2R,6R)-2,6-dimethylmorpholin-4-yl]pyrazolo[1,5-a]pyrimidine-3-carboxylic acid To a solution of ethyl 5-[(2R,6R)-2,6-dimethylmorpholin-4-yl]pyrazolo[1,5-a]pyrimidine-3-carboxylate (1.60 g, 5.26 mmol) in methanol (15.0 mL) and water (4.00 mL) was added $LiOHH_2O$ (661 mg, 15.7 mmol). The mixture was stirred at 60° C. for 16 hrs. On completion, the reaction mixture was quenched by water (5 mL), and concentrated in vacuo to remove methanol. Then the mixture was acidified with 1N HCl solution until the pH=5. The aqueous phase was extracted with ethyl acetate (3×5 mL). The combined organic layer was washed with brine (2×10 mL), dried with anhydrous $Na_2SO_4$, filtered and concentrated in vacuo to give a residue. The residue was purified by reversed-phase (0.1% FA condition) to give the title compound (1.10 g, 75% yield) as a white solid. $^1$H NMR (400 MHz, $CDCl_3$) δ 11.77-8.72 (m, 1H), 8.35 (d, J=8.0 Hz, 1H), 8.32 (s, 1H), 6.44 (d, J=8.0 Hz, 1H), 4.21-4.14 (m, 2H), 4.03-3.70 (m, 2H), 3.48-3.42 (m, 2H), 1.28 (d, J=6.4 Hz, 6H).

N-[(1S)-3-(difluoromethyl)-1-(4-formylcyclohexyl)pyrazol-4-yl]-5-[(2R,6R)-2,6-dimethylmorpholin-4-yl]pyrazolo[1,5-a]pyrimidine-3-carboxamide (Intermediate ASH)

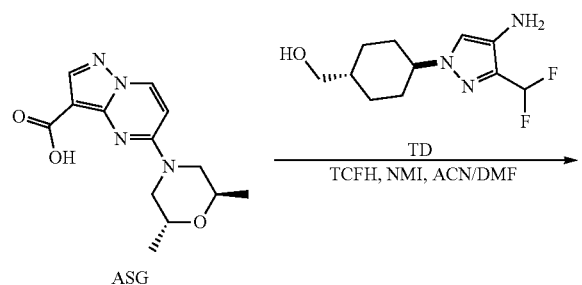

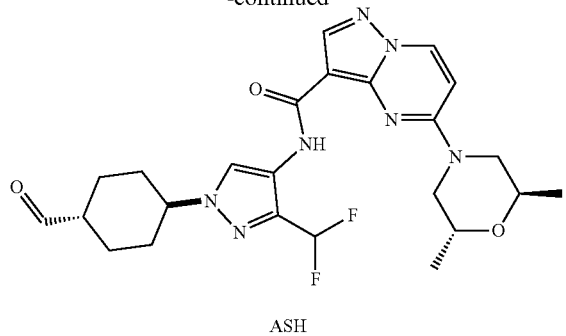

ASH

Step 1—N-[(1S)-3-(difluoromethyl)-1-[4-(hydroxymethyl)cyclohexyl]pyrazol-4-yl]-5-[(2R,6R)-2,6-dimethylmorpholin-4-yl]pyrazolo[1,5-a]pyrimidine-3-carboxamide To a solution of 5-[(2R,6R)-2,6-dimethylmorpholin-4-yl]pyrazolo[1,5-a]pyrimidine-3-carboxylic acid (500 mg, 1.81 mmol, Intermediate ASG) in ACN (6.00 mL) was added [chloro(dimethylamino)methylene]-dimethyl-ammonium; hexafluorophosphate (660 mg, 2.35 mmol) and 1-methylimidazole (520 mg, 6.33 mmol, 504 uL). The mixture was stirred at 25° C. for 1 hr. Next, [4-[(1S)-4-amino-3-(difluoromethyl)pyrazol-1-yl]cyclohexyl]methanol (577 mg, 2.35 mmol, Intermediate TD) was added and the mixture was stirred at 25° C. for 16 hrs. On completion, the reaction mixture was quenched by water (2 mL), and concentrated in vacuo to give a residue. The residue was purified by reversed phase (0.1% FA condition) to give the title compound (700 mg, 70% yield) as a white solid. $^1$H NMR (400 MHz, DMSO-$d_6$) δ 9.29 (s, 1H), 8.79 (d, J=8.0 Hz, 1H), 8.39 (s, 1H), 8.27 (s, 1H), 7.29-6.97 (m, 1H), 6.89 (d, J=8.0 Hz, 1H), 4.47 (s, 1H), 4.21-4.12 (m, 1H), 4.11-4.01 (m, 2H), 3.99-3.76 (m, 2H), 3.52-3.47 (m, 2H), 3.26 (d, J=5.2 Hz, 2H), 2.05-2.03 (m, 2H), 1.85 (d, J=12.0 Hz, 2H), 1.77-1.67 (m, 2H), 1.46-1.39 (m, 1H), 1.17 (d, J=6.4 Hz, 6H), 1.13-1.01 (m, 2H). LC-MS (ESI$^+$) m/z 504.5 (M+H)$^+$.

Step 2—N-[(1S)-3-(difluoromethyl)-1-(4-formylcyclohexyl)pyrazol-4-yl]-5-[(2R,6R)-2,6-dimethylmorpholin-4-yl]pyrazolo[1,5-a]pyrimidine-3-carboxamide To a solution of N-[(1S)-3-(difluoromethyl)-1-[4-(hydroxymethyl)cyclohexyl]pyrazol-4-yl]-5-[(2R,6R)-2,6-dimethylmorpholin-4-yl]pyrazolo[1,5-a]pyrimidine-3-carboxamide (660 mg, 1.31 mmol) in DCM (10.0 mL) was added DMP (833 mg, 1.97 mmol). The mixture was stirred at 20° C. for 1 hr. Next, $NaHCO_3$ (165 mg, 1.97 mmol) was added in portions and the mixture was stirred at 20° C. for 1 hr. On completion, the reaction mixture was quenched by addition saturated solution of $Na_2S_2O_3$ (8 mL), and saturated solution of $NaHCO_3$ (4 mL), then extracted with DCM (3×20 mL). The combined organic layers was washed with solution of $NaHCO_3$ (3×20 mL), then washed with brine (2×40 mL). The organic layer was dried over anhydrous $Na_2SO_4$, filtered and concentrated in vacuo to give the title compound (540 mg, 82% yield) as a white solid. $^1$H NMR (400 MHz, DMSO-$d_6$) δ 9.61 (s, 1H), 9.30 (s, 1H), 8.79 (d, J=8.0 Hz, 1H), 8.41 (s, 1H), 8.27 (s, 1H), 7.34-6.97 (m, 1H), 6.90 (d, J=8.0 Hz, 1H), 4.28-4.15 (m, 1H), 4.13-4.01 (m, 2H), 3.89 (s, 2H), 3.49 (dd, J=6.8, 13.2 Hz, 2H), 2.38 (t, J=12.0 Hz, 1H), 2.15-1.99 (m, 4H), 1.90-1.73 (m, 2H), 1.47-1.30 (m, 2H), 1.17 (d, J=6.4 Hz, 6H). LC-MS (ESI⁺) m/z 502.2 (M+H)⁺.

5-(5-Oxa-8-azaspiro[3.5]nonan-8-yl)pyrazolo[1,5-a]pyrimidine-3-carboxylic acid (Intermediate ASI)

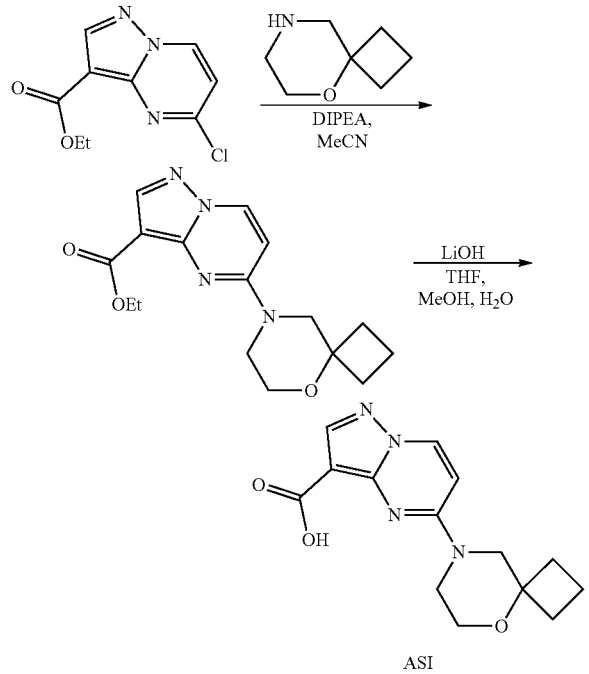

Step 1—Ethyl 5-(5-oxa-8-azaspiro[3.5]nonan-8-yl)pyrazolo[1,5-a]pyrimidine-3-carboxylate To a solution of ethyl 5-chloropyrazolo[1,5-a]pyrimidine-3-carboxylate (1.77 g, 7.86 mmol, CAS #1224944-77-7), 5-oxa-8-azaspiro[3.5]nonane (1.00 g, 7.86 mmol, CAS #220291-93-0) in ACN (30 mL), DIPEA (1.52 g, 11.8 mmol) was added. The reaction mixture was stirred at 60° C. for 12 hrs. On completion, the mixture was quenched with water (100 mL) and extracted with ethyl acetate (3×250 mL), the combined organic phase was dried over anhydrous sodium sulfate, filtered and concentrated to give a yellow solid (2.1 g, 81% yield). ¹H NMR (400 MHz, DMSO-d₆) δ 1.30 (t, J=7.2 Hz, 2H) 1.24-1.35 (m, 1H) 1.77 (d, J=4.8 Hz, 2H) 1.86-1.99 (m, 4H) 3.63 (d, J=4.8 Hz, 2H) 3.67-3.90 (m, 4H) 4.20 (d, J=7.2 Hz, 2H) 6.95 (d, J=8.0 Hz, 1H) 8.22 (s, 1H) 8.75 (d, J=7.6 Hz, 1H).

Step 2—5-(5-Oxa-8-azaspiro[3.5]nonan-8-yl)pyrazolo[1,5-a]pyrimidine-3-carboxylic acid To a solution of ethyl 5-(5-oxa-8-azaspiro[3.5]nonan-8-yl)pyrazolo[1,5-a]pyrimidine-3-carboxylate (1.00 g, 3.16 mmol) and LiOH.H₂O (265 mg, 6.32 mmol) in THF (6 mL), MeOH (6 mL) and H₂O (2 mL) was stirred at 60° C. for 12 hrs. On completion, the solvent was dried down to give residue, and the residue was diluted with water (20 ml), then the pH was adjusted to ~5 with HCl (2 N). The solid was collected by filtration to give the title compound (840 mg, 88% yield) as an off-white solid. ¹H NMR (400 MHz, DMSO-d₆) δ 11.72 (s, 1H), 8.75 (d, J=8.0 Hz, 1H), 8.19 (s, 1H), 6.96 (d, J=8.0 Hz, 1H), 3.75 (s, 4H), 3.65-3.60 (m, 2H), 1.97-1.92 (m, 4H), 1.82-1.72 (m, 2H).

N-(3-(Difluoromethyl)-1-((1r,4r)-4-formylcyclohexyl)-1H-pyrazol-4-yl)-5-(5-oxa-8-azaspiro [3.5]nonan-8-yl)pyrazolo[1,5-a]pyrimidine-3-carboxamide (Intermediate ASJ)

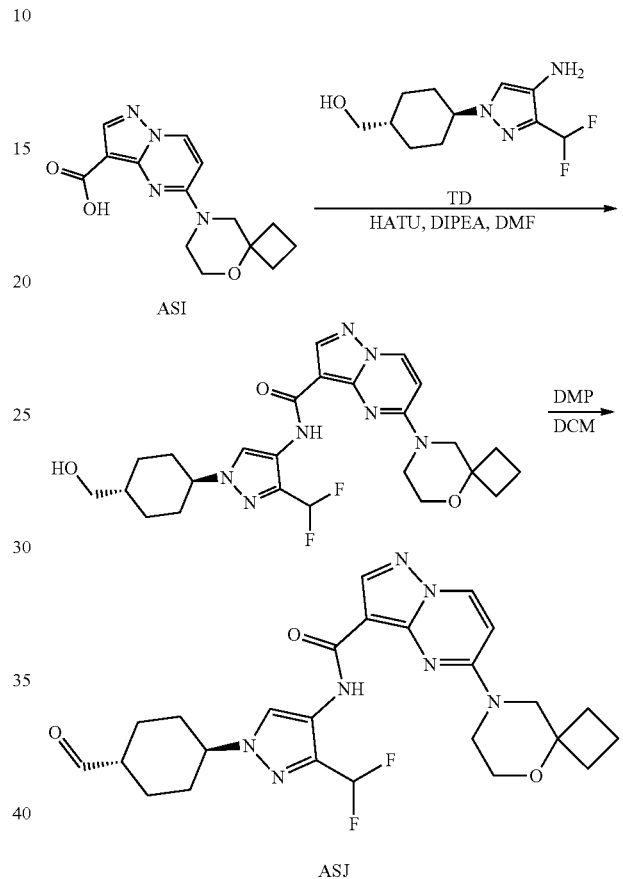

Step 1—N-(3-(Difluoromethyl)-1-((1 r,4r)-4-(hydroxymethyl)cyclohexyl)-1H-pyrazol-4-yl)-5-(5-oxa-8-azaspiro[3,5]nonan-8-yl)pyrazolo[1,5-a]pyrimidine-3-carboxamide To a solution of 5-(5-oxa-8-azaspiro[3.5]nonan-8-yl)pyrazolo[1,5-a]pyrimidine-3-carboxylic acid (770 mg, 2.67 mmol, Intermediate ASI), HATU (1.12 g, 2.94 mmol) and DIPEA (1.04 g, 8.01 mmol) in DMF (30 mL) was stirred at 25° C. Then to the reaction mixture was added [4-[(1S)-4-amino-3-(difluoromethyl)pyrazol-1-yl]cyclohexyl]methanol (851 mg, 3.47 mmol, Intermediate TD) and the reaction was stirred at 25° C. for 2 hrs. On completion, the reaction mixture was diluted with water (50 mL) and extracted with ethyl acetate (3×50 mL). The extract was washed with sodium bicarbonate solution, then the combined organic phase was dried over anhydrous sodium sulfate, filtered and concentrated to give a residue and evaporated to dryness. The crude product was triturated with EA (10 mL) at 25° C. for 10 min to give the title compound (980 mg, 67% yield) as an off-white solid. ¹H NMR (400 MHz, DMSO-d₆) δ 9.34 (s, 1H), 8.83 (d, J=8.0 Hz, 1H), 8.40 (s, 1H), 8.30 (s, 1H), 7.33-6.96 (m, 2H), 4.50 (t, J=5.2 Hz, 1H), 4.18 (s, 1H), 3.77 (s, 4H), 3.68-3.60 (m, 2H), 3.27 (t, J=5.6 Hz, 2H), 2.08-1.94 (m, 6H), 1.90-1.68 (m, 6H), 1.44 (s, 1H), 1.21-1.00 (m, 2H).

Step 2—N-(3-(Difluoromethyl)-1-((1r,4r)-4-formyl-cyclohexyl)-1H-pyrazol-4-yl)-5-(5-oxa-8-azaspiro[3.5]nonan-8-yl)pyrazolo[1,5-a]pyrimidine-3-carboxamide To a solution of N-[(1S)-3-(difluoromethyl)-1-[4-(hydroxymethyl)cyclohexyl]pyrazol-4-yl]-5-(5-oxa-8-azaspiro[3.5]nonan-8-yl)pyrazolo[1,5-a]pyrimidine-3-carboxamide (950 mg, 1.84 mmol) and DMP (937 mg, 2.21 mmol) in DCM (15 mL) was stirred at 25° C. for 1 hr. On completion, the reaction mixture was quenched with saturated solution of sodium thiosulfate (5 mL). Then the mixture was diluted with water (50 mL), extracted with ethyl acetate (3×100 mL), and washed with sodium bicarbonate solution. The combined organic phase was dried over anhydrous sodium sulfate, filtered and concentrated to give a residue and evaporated to dryness. The crude product was triturated with EA (10 mL) at 30° C. for 5 min to give the title compound (800 mg, 71% yield) as an off-white solid. ¹H NMR (400 MHz, DMSO-d₆) δ 9.63 (s, 1H), 9.39-9.33 (m, 1H), 8.83 (d, J=8.0 Hz, 1H), 8.42 (s, 1H), 8.30 (s, 1H), 7.29-7.01 (m, 2H), 4.23 (s, 1H), 3.77 (s, 4H), 3.66 (d, J=3.2 Hz, 2H), 2.46-2.31 (m, 1H), 2.14-2.05 (m, 4H), 2.00-1.95 (m, 4H), 1.86-1.75 (m, 4H), 1.45-1.33 (m, 2H).

N-[(1S)-3-(difluoromethyl)-1-(4-formylcyclohexyl)pyrazol-4-yl]-5-[(2S,6S)-2,6-dimethylmorpholin-4-yl]pyrazolo[1,5-a]pyrimidine-3-carboxamide (Intermediate ASL)

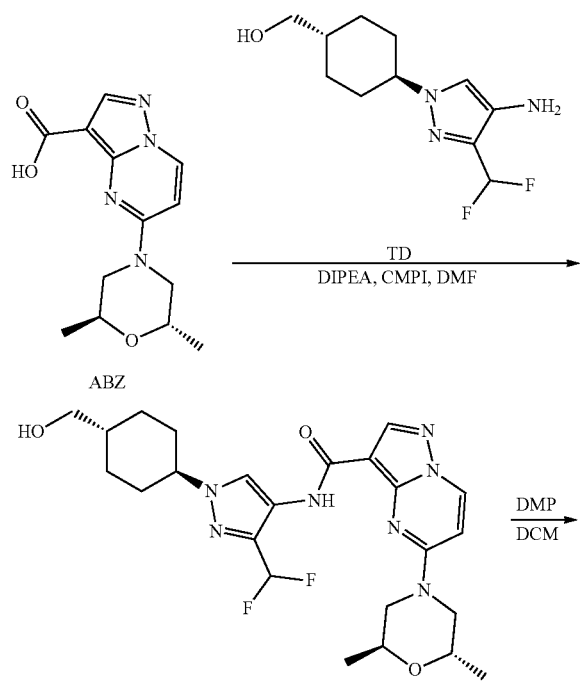

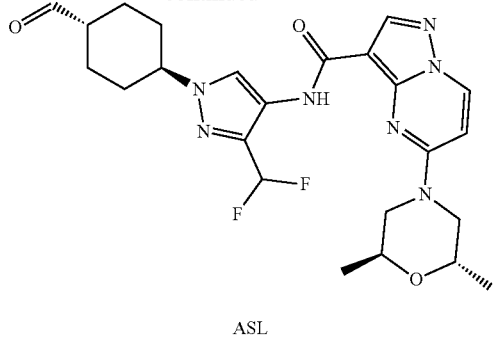

ASL

Step 1—N-(3-(difluoromethyl)-1-((1r,4S)-4-(hydroxymethyl)cyclohexyl)-1H-pyrazol-4-yl)-5-((2S,6S)-2,6-dimethylmorpholino)pyrazolo[1,5-a]pyrimidine-3-carboxamide A solution of 5-[(2S,6S)-2,6-dimethylmorpholin-4-yl]pyrazolo[1,5-a]pyrimidine-3-carboxylic acid (1.20 g, 4.34 mmol, Intermediate ABZ), DIPEA (1.68 g, 13.0 mmol) and CMPI (1.33 g, 5.21 mmol) in DMF (3 mL) was stirred at 25° C. for 30 minutes. Then a solution of [4-[(1S)-4-amino-3-(difluoromethyl)pyrazol-1-yl] cyclohexyl]methanol (1.28 g, 5.21 mmol, Intermediate TD) in DMF (3 mL) was added. The mixture was stirred at 25° C. for 90 minutes. On completion, the reaction mixture was diluted with water (50 mL) and extracted with ethyl acetate (3×25 mL). The combined organic layers were washed with brine (15 mL), dried over anhydrous sodium sulfate, filtered and concentrated in vacuo to give a residue. The residue was purified by silica gel chromatography (dichloromethane:methanol=20:1) to give an impure product. The impure product was re-purified by reverse phase (0.1% FA condition) to give the title compound (600 mg, 27% yield) as a gray solid. LC-MS (ESI⁺) m/z 504.2 (M+H)⁺.

Step 2—N-(3-(difluoromethyl)-1-((1r,4S)-4-formyl-cyclohexyl)-1H-pyrazol-4-yl)-5-((2S,6S)-2,6-dimethylmorpholino)pyrazolo[1,5-a]pyrimidine-3-carboxamide To a solution of N-[(1S)-3-(difluoromethyl)-1-[4-(hydroxymethyl)cyclohexyl]pyrazol-4-yl]-5-[(2S,6S)-2,6-dimethylmorpholin-4-yl]pyrazolo[1,5-a]pyrimidine-3-carboxamide (540 mg, 1.07 mmol) in DCM (6 mL) was added DMP (637 mg, 1.50 mmol) at 0° C., then the mixture was stirred at 25° C. for 2 hrs. On completion, the reaction mixture was filtered, the filtrate was quenched by saturated sodium thiosulfate solution (25 mL) and adjusted pH to 7~8 by sodium bicarbonate saturated solution (20 mL). The mixture was extracted with dichloromethane (3×25 mL). The combined organic layers were washed with brine (15 mL), dried over anhydrous sodium sulfate, filtered and concentrated in vacuo to give the title compound (650 mg, 90% yield) as a yellow solid. ¹H NMR (400 MHz, DMSO-d₆) δ 9.62 (s, 1H), 9.31 (s, 1H), 8.80 (d, J=8.0 Hz, 1H), 8.41 (s, 1H), 8.28 (s, 1H), 7.32-6.98 (m, 1H), 6.91 (d, J=8.0 Hz, 1H), 4.28-4.16 (m, 1H), 4.11-4.01 (m, 2H), 3.90 (m, 2H), 3.50 (dd, J=13.2, 6.8 Hz, 2H), 2.40-2.30 (m, 1H), 2.16-2.02 (m, 4H), 1.89-1.74 (m, 2H), 1.45-1.30 (m, 2H), 1.17 (d, J=6.4 Hz, 6H). LC-MS (ESI⁺) m/z 502.2 (M+H)⁺.

2-Prop-2-ynylisoindoline-1,3-dione (Intermediate ASN)

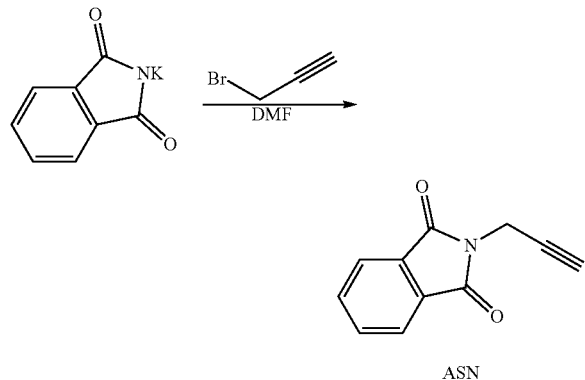

A mixture of (1,3-dioxoisoindolin-2-yl)potassium (3.00 g, 16.2 mmol) and 3-bromoprop-1-yne (2.89 g, 24.3 mmol) in DMF (20 mL) was stirred at 25° C. for 16 hours. On completion, the mixture was diluted in water (80 mL), and a large amount of yellow solid precipitated from the solution. The mixture was filtered and the filter cake was collected and dried in vacuo to afford the title compound (2.94 g, 98% yield) as a light solid. LC-MS (ESI⁺) m/z 186.0 (M+H)⁺.

Tert-butyl (2R)-2-(5-aminopentyl)morpholine-4-carboxylate (Intermediate ASO)

Step 1—Tert-butyl (2R)-2-[5-(1,3-dioxoisoindolin-2-yl)penta-1,3-diynyl]morpholine-4-carboxylate To a mixture of tert-butyl (2R)-2-ethynylmorpholine-4-carboxylate (400 mg, 1.89 mmol, Intermediate ARZ) and 2-prop-2-ynylisoindoline-1,3-dione (1.40 g, 7.57 mmol, Intermediate ASN) in THF (30 mL) was added Cu(OAc)$_2$—H$_2$O (151 mg, 757 umol) and pyridine (599 mg, 7.57 mmol) at 25° C. under N$_2$. The mixture was stirred at 70° C. for 16 hours. On completion, the reaction mixture was quenched with H$_2$O (20 mL) at 25° C., and extracted with DCM (3×30 mL). The combined organic layers were washed with brine (10 mL), dried over Na$_2$SO$_4$, filtered and concentrated in vacuo. The residue was purified by column chromatography (SiO$_2$, petroleum ether/ethyl acetate=30:1 to 5:1) to afford the title compound (186 mg, 25% yield) as a white solid. LC-MS (ESI⁺) m/z 417.2 (M+Na)⁺.

Step 2—Tert-butyl (2R)-2-[5-(1,3-dioxoisoindolin-2-yl)pentyl]morpholine-4-carboxylate To a mixture of tert-butyl (2R)-2-[5-(1,3-dioxoisoindolin-2-yl)penta-1,3-diynyl]morpholine-4-carboxylate (186 mg, 471 umol) in a mixed solvent of THF (5 mL) and MeOH (5 mL) was added Pd/C (30 mg, 10 wt %) and Pd(OH)$_2$/C (30 mg, 10 wt %) at 25° C. under N$_2$. The mixture was purged with H$_2$ gas3 times and then stirred at 25° C. under H$_2$ (15 psi) for 16 hours. On completion, the mixture was filtered and the filtrate was concentrated in vacuo to give the title compound (180 mg, 95% yield) as a white solid. LC-MS (ESI⁺) m/z 425.3 (M+Na)⁺.

Step 3—Tert-butyl (2R)-2-(5-aminopentyl)morpholine-4-carboxylate

To a mixture of tert-butyl (2R)-2-[5-(1,3-dioxoisoindolin-2-yl)pentyl]morpholine-4-carboxylate (180 mg, 447 umol) in EtOH (10 mL) was added NH$_2$NH$_2$—H$_2$O (111 mg, 2.24 mmol) in one portion at 25° C. The mixture was stirred at 80° C. for 1 hour. On completion, the mixture was concentrated in vacuo to give the title compound (120 mg, 98% yield) as colorless oil.

2-(2,6-Dioxo-3-piperidyl)-4-[5-[(2R)-morpholin-2-yl]pentylamino]isoindoline-1,3-dione (Intermediate ASP)

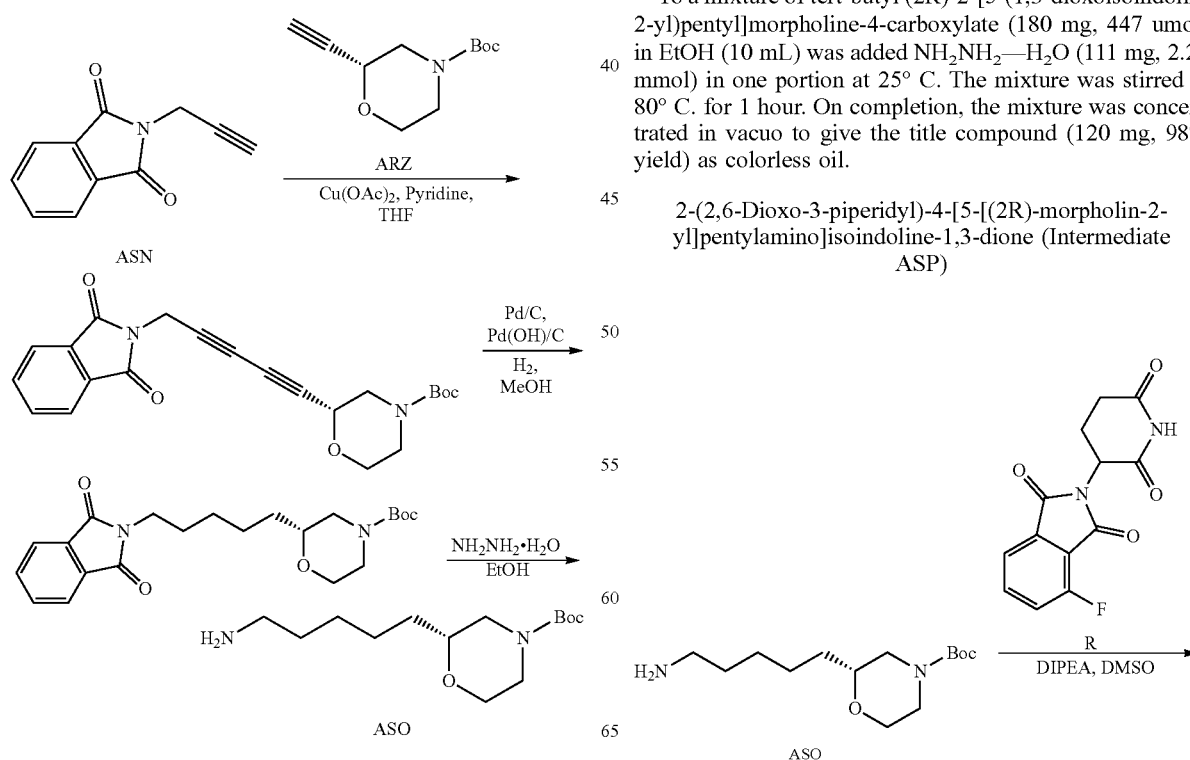

2233
-continued

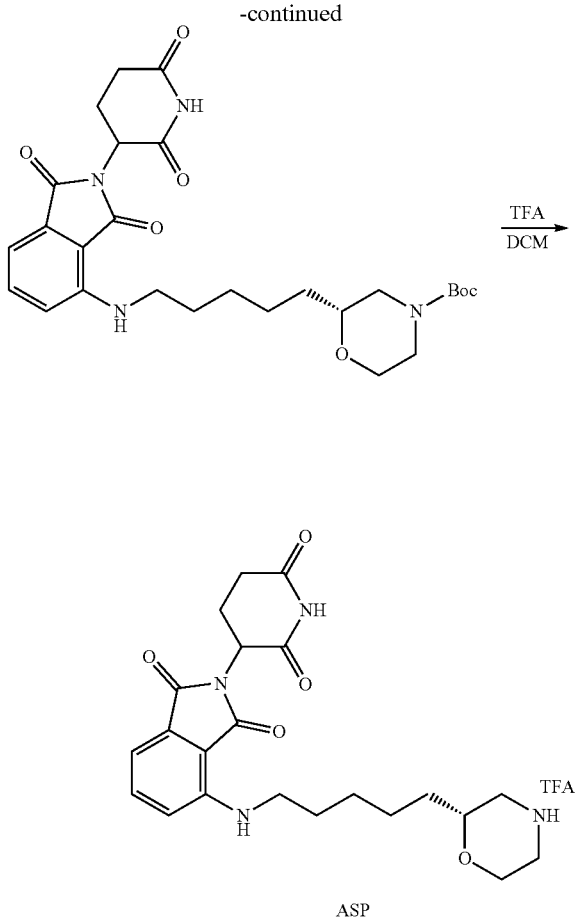

ASP

Step 1—Tert-butyl (2R)-2-[5-[[2-(2,6-dioxo-3-piperidyl)-1,3-dioxo-isoindolin-4-yl]amino]pentyl]morpholine-4-carboxylate To a mixture of 2-(2,6-dioxo-3-piperidyl)-4-fluoro-isoindoline-1,3-dione (133 mg, 484 umol, Intermediate R) and tert-butyl (2R)-2-(5-aminopentyl)morpholine-4-carboxylate (110 mg, 403 umol, Intermediate ASO) in DMSO (1 mL) was added DIEA (156 mg, 1.21 mmol) at 25° C. The mixture was stirred at 120° C. for 2 hours. On completion, the reaction mixture was quenched with water (0.2 mL) at 25° C., and then concentrated in vacuo. The residue was purified by reverse phase (FA condition) to afford the title compound (140 mg, 65% yield) as yellow solid. LC-MS (ESI+) m/z 551.3 (M+Na)+.

Step 2—2-(2,6-Dioxo-3-piperidyl)-4-[5-[(2R)-morpholin-2-yl]pentylamino]isoindoline-1,3-dione To a mixture of tert-butyl (2R)-2-[5-[[2-(2,6-dioxo-3-piperidyl)-1,3-dioxo-isoindolin-4-yl]amino]pentyl]morpholine-4-carboxylate (40.0 mg, 75.6 umol) in DCM (1 mL) was added HCl/dioxane (4 M, 4.0 mL) at 25° C. The mixture was stirred at 25° C. for 2 hours. On completion, the mixture was concentrated in vacuo to give the title compound (40.0 mg, 99% yield) as yellow solid. LC-MS (ESI+) m/z 429.2 (M+H)+.

2234

3-(9-(2,6-Dioxopiperidin-3-yl)-9H-pyrido[2,3-b]indol-6-yl)propanal (Intermediate ATM)

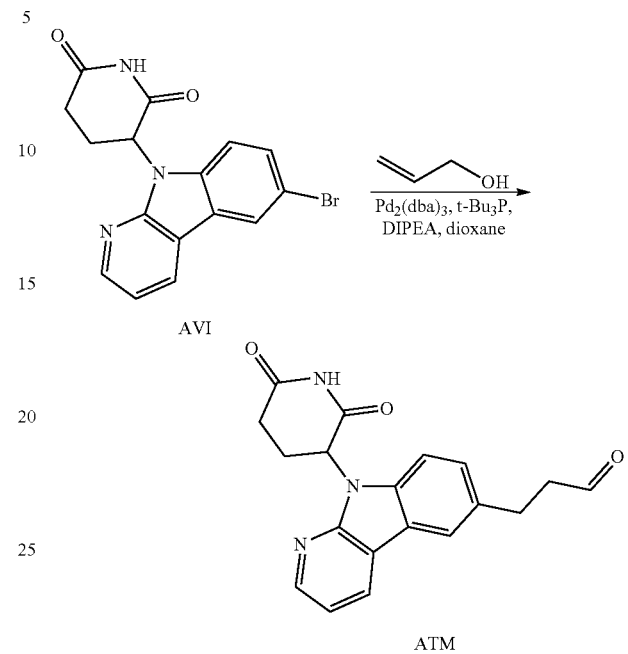

A solution of 3-(6-bromopyrido[2,3-b]indol-9-yl)piperidine-2,6-dione (500 mg, 1.40 mmol, Intermediate AVI), prop-2-en-1-ol (162 mg, 2.79 mmol, CAS #107-18-6), DIPEA (541 mg, 4.19 mmol) and Pd₂(dba)₃ (128 mg, 140 umol) in dioxane (5 mL) was degassed and purged with nitrogen gas 3 times. Next, t-Bu₃P (847 mg, 419 umol, 10 wt %) was added to the reaction mixture and the mixture was stirred at 80° C. for 16 hrs. On completion, the reaction mixture was diluted with water (20 mL) and extracted with ethyl acetate (3×25 mL). The combined organic layers were washed with sodium chloride solution (15 mL), dried over anhydrous sodium sulfate, filtered and concentrated in vacuo to give a residue. The residue was purified by silica gel chromatography (Petroleum ether:Ethyl acetate=20:1 to 1:2) to give the title compound (100 mg, 34% yield) as yellow solid. $^1$H NMR (400 MHz, CDCl₃) δ 9.87 (t, J=1.2 Hz, 1H), 8.43 (dd, J=4.8, 1.6 Hz, 1H), 8.32 (dd, J=7.6, 1.6 Hz, 1H), 8.19 (s, 1H), 7.93 (s, 1H), 7.34 (dd, J=8.4, 1.6 Hz, 1H), 7.24-7.16 (m, 2H), 5.90 (dd, J=12.4, 5.2 Hz, 1H), 3.17-2.85 (m, 7H), 2.35-2.25 (m, 1H).

3-(6-(3-(2,7-Diazaspiro[3.5]nonan-2-yl)propyl)-9H-pyrido[2,3-b]indol-9-yl)piperidine-2,6-dione (Intermediate ATN)

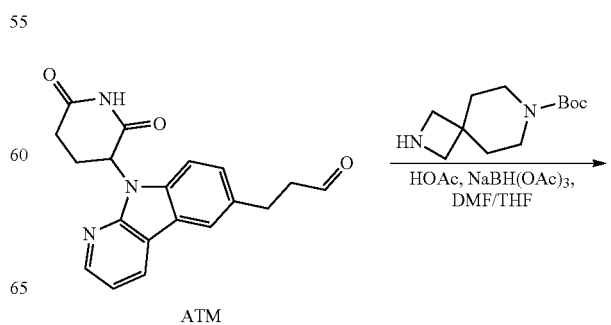

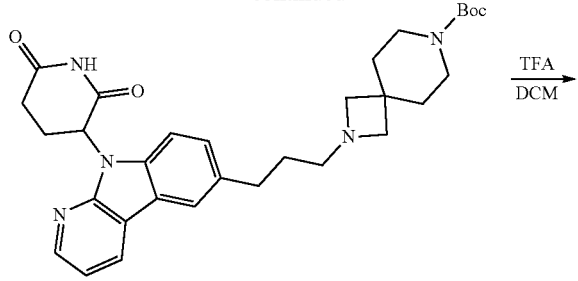

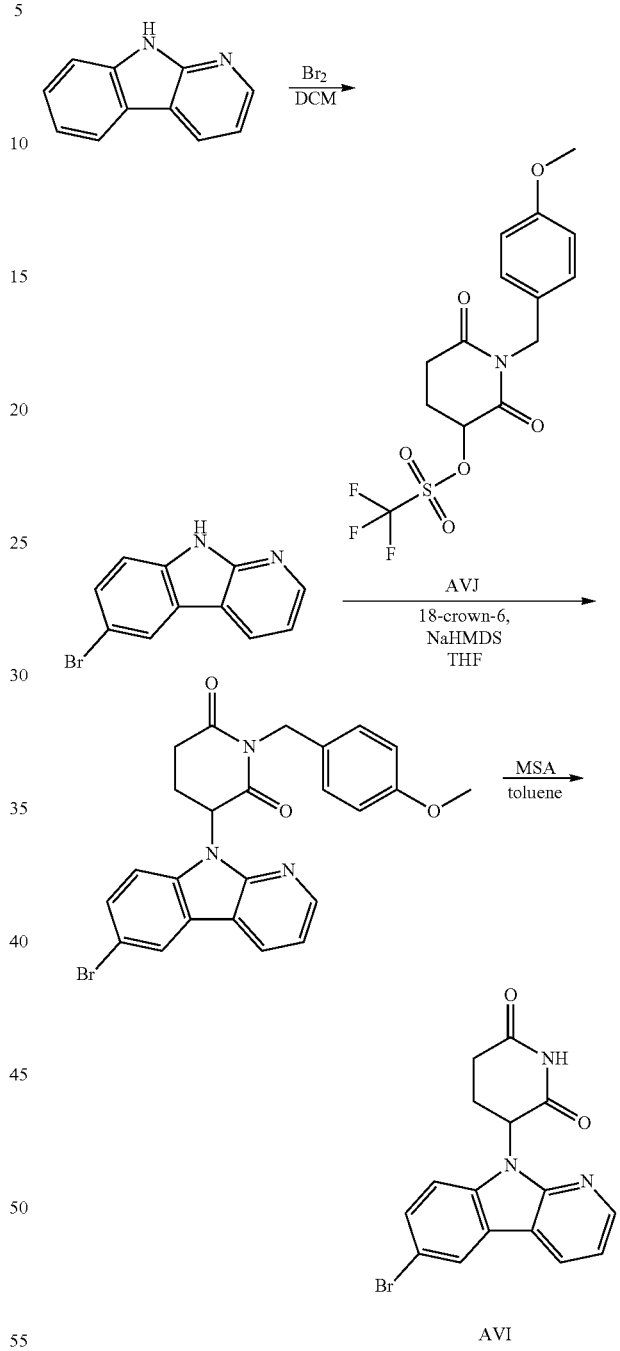

2236
3-(6-Bromo-9H-pyrido[2,3-b]indol-9-yl)piperidine-2,6-dione (Intermediate AVI)

Step 1—Tert-butyl 2-(3-(9-(2,6-dioxopiperidin-3-yl)-9H-pyrido[2,3-b]indol-6-yl)propyl)-2,7-diazaspiro[3.5]nonane-7-carboxylate To a solution of 3-[9-(2,6-dioxo-3-piperidyl)pyrido[2,3-b]indol-6-yl]propanal (50.0 mg, 149 umol, Intermediate ATM) and tert-butyl 2,7-diazaspiro[3.5]nonane-7-carboxylate (37.1 mg, 164 umol, CAS #1023301-84-9) in THF (1 mL) was added AcOH (895 ug, 14.9 umol). The mixture was stirred at 25° C. for 15 minutes, then NaBH(OAc)$_3$ (47.4 mg, 224 umol) was added at 25° C. and the mixture was stirred for 45 minutes. On completion, the reaction mixture was concentrated in vacuo to give a residue. The residue was purified by prep-TLC to give the title compound (40.0 mg, 34% yield) as yellow solid. $^1$H NMR (400 MHz, DMSO-d$_6$) δ 11.13 (s, 1H), 8.53 (dd, J=7.6, 1.6 Hz, 1H), 8.40 (dd, J=4.8, 1.2 Hz, 1H), 8.03 (s, 1H), 7.51 (d, J=7.6 Hz, 1H), 7.34 (d, J=8.4 Hz, 1H), 7.24 (dd, J=7.6, 4.8 Hz, 1H), 6.01 (s, 1H), 3.60 (m, 3H), 3.23 (d, J=5.0 Hz, 3H), 2.94 (s, 4H), 2.76-2.71 (m, 2H), 1.81-1.71 (m, 4H), 1.66-1.63 (m, 2H), 1.61-1.53 (m, 4H), 1.38 (s, 9H).

Step 2—3-(6-(3-(2,7-Diazaspiro[3.5]nonan-2-yl)propyl)-9H-pyrido[2,3-b]indol-9-yl)piperidine-2,6-dione To a solution of tert-butyl 2-[3-[9-(2,6-dioxo-3-piperidyl)pyrido[2,3-b]indol-6-yl]propyl]-2,7-diazaspiro[3.5]nonane-7-carboxylate (40.0 mg, 73.3 umol) in DCM (1 mL) was added TFA (1 mL). The mixture was stirred at 25° C. for 0.5 hr. On completion, the reaction mixture was concentrated in vacuo to give the title compound (30.0 mg, 99% yield, TFA) as yellow solid. LC-MS (ESI$^+$) m/z 446.4 (M+H)$^+$.

Step 1—6-Bromo-9H-pyrido[2,3-b]indole

To a stirred mixture of 9H-pyrido[2,3-b]indole (50.00 g, 297.3 mmol, CAS #26148-68-5) in DCM (1.00 L) was added Br$_2$ (18.32 mL, 357.6 mmol) dropwise at 0° C. under nitrogen atmosphere. The resulting mixture was stirred for 4 h at 25° C. under nitrogen atmosphere. Then it was concentrated under reduced pressure. The residue was triturated with EtOAc (250 mL) and filtered. The filter cake was triturated with acetone (200 mL) and filtered. The filter cake was then triturated with sat. Na$_2$S$_2$O$_3$ (200 mL) and the resulting mixture was filtered. The filter cake was washed with H$_2$O (3×50 mL) and dried under reduced pressure to afford the title compound (75.3 g, 89%) as a white solid. $^1$H NMR (400 MHz, DMSO-d$_6$) δ 11.97 (s, 1H), 8.57 (dd, J=7.7, 1.7 Hz, 1H), 8.48-8.41 (m, 2H), 7.59 (dd, J=8.6, 2.1 Hz, 1H), 7.48 (d, J=8.6 Hz, 1H), 7.24 (dd, J=7.8, 4.8 Hz, 1H). LC/MS (ESI, m/z): [(M+1)]$^+$=247.0, 249.0.

Step 2—3-(6-Bromo-9H-pyrido[2,3-b]indol-9-yl)-1-(4-methoxybenzyl)piperidine-2,6-dione To a stirred mixture of 6-bromo-9H-pyrido[2,3-b]indole (55.00 g, 222.6 mmol) and 18-crown-6 (11.77 g, 44.5 mmol) in THF (1.10 L) was added NaHMDS (166.94 mL, 333.88 mmol, 2 M in THF) dropwise at −30° C. under nitrogen atmosphere. The resulting mixture was stirred for 1 h at −30° C. under nitrogen atmosphere. To the above mixture was added 1-[(4-methoxyphenyl)methyl]-2,6-dioxopiperidin-3-yl trifluoromethanesulfonate (127.32 g, 333.88 mmol, Intermediate AVJ) in THF at −30° C. The resulting mixture was stirred for additional 2 h at −30° C. The resulting mixture was quenched by the addition of sat. NH$_4$Cl (300 mL) at 0° C. and extracted with EtOAc (3×300 mL). The combined organic layers were washed with brine (200 mL) and dried over anhydrous Na$_2$SO$_4$. After filtration, the filtrate was concentrated under reduced pressure. The residue was purified by silica gel column chromatography, eluted with petroleum ether/EtOAc (1:1) to afford the title compound (65 g, 61%) as a light blue solid. $^1$H NMR (400 MHz, DMSO-d$_6$) δ 8.66 (dd, J=7.7, 1.6 Hz, 1H), 8.54 (d, J=1.9 Hz, 1H), 8.48 (dd, J=4.9, 1.6 Hz, 1H), 7.33 (dd, J=7.7, 4.8 Hz, 1H), 7.27 (d, J=8.6 Hz, 2H), 7.16 (dd, J=12.6, 8.6 Hz, 1H), 6.95-6.88 (m, 2H), 6.88-6.79 (m, 1H), 6.19 (s, 1H), 4.97-4.78 (m, 2H), 3.75 (s, 3H), 3.17 (d, J=12.7 Hz, 2H), 2.97-2.86 (m, 1H), 2.24-2.16 (m, 1H). LC/MS (ESI, m/z): [(M+1)]+=478.0, 480.0.

Step 3—3-(6-Bromo-9H-pyrido[2,3-b]indol-9-yl)piperidine-2,6-dione

To a stirred solution of 3-[6-bromopyrido[2,3-b]indol-9-yl]-1-[(4-methoxyphenyl)methyl]piperidine-2,6-dione (50.00 g, 104.527 mmol, 1.00 equiv) in toluene (750.00 mL) was added methanesulfonic acid (350 mL) at room temperature under nitrogen atmosphere. The resulting mixture was stirred for 2 h at 110° C. under nitrogen atmosphere. The resulting mixture was cooled down to rt and diluted with ice/water (1.5 L). The precipitated solids were collected by filtration and washed with water (2×100 mL). The filter cake was triturated in EtOAc (1 L). The precipitated solids were collected by filtration and washed with EtOAc (100 mL) to the title compound (22 g, 59%) as a light pink solid. $^1$H NMR (400 MHz, DMSO-d$_6$) δ 11.18 (s, 1H), 8.65 (dd, J=7.7, 1.6 Hz, 1H), 8.53 (d, J=1.9 Hz, 1H), 8.48 (dd, J=4.8, 1.6 Hz, 1H), 7.70-7.59 (m, 2H), 7.32 (dd, J=7.7, 4.8 Hz, 1H), 6.12-6.00 (m, 1H), 3.22-2.95 (m, 2H), 2.79-2.66 (m, 1H), 2.19-2.09 (m, 1H). LC/MS (ESI, m/z): [(M+1)]$^+$=358.0, 360.0.

[1-[(4-Methoxyphenyl) methyl]-2,6-dioxo-3-piperidyl] trifluoromethanesulfonate (Intermediate AVJ)

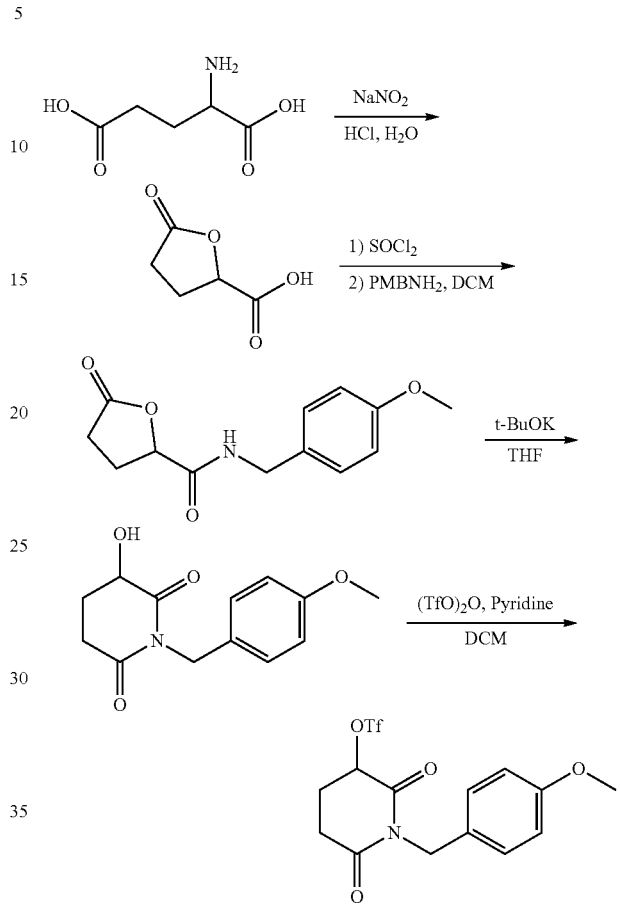

Step 1—5-Oxotetrahydrofuran-2-carboxylic acid

To a solution of 2-aminopentanedioic acid (210 g, 1.43 mol, CAS #617-65-2) in H$_2$O (800 mL) and HCl (12 M, 210 mL) was added a solution of NaNO$_2$ (147 g, 2.13 mol) in H$_2$O (400 mL) at −5° C. The mixture was stirred at 15° C. for 12 hrs. On completed, the mixture was concentrated and then dissolved in EA (500 mL) and filtered and washed with EA (3×100 mL). The filtrate and washed solution were dried over Na$_2$SO$_4$, filtered and concentrated in vacuo to give the title compound (200 g, 100% yield) as yellow oil. $^1$H NMR (400 MHz, CDCl$_3$) δ 6.43 (s, 1H), 5.02-4.95 (m, 1H), 2.67-2.38 (m, 4H).

Step 2—N-[(4-methoxphenyl)methyl]-5-oxo-tetrahydrofuran-2-carboxamide

To 5-oxotetrahydrofuran-2-carboxylic acid (120 g, 922 mmol) was added SOCl$_2$ (246 g, 2.07 mol) at 0° C. slowly. The mixture was stirred at 85° C. for 3 hrs, and then the mixture was stirred at 15° C. for 6 hrs. The mixture was concentrated in vacuo and the residue was dissolved in dry DCM (1 L) at 0° C. under N$_2$. After that a solution of Et$_3$N (187 g, 1.84 mol) and 4-methoxybenzylamine (101 g, 738 mmol) in DCM (400 mL) was added, then the mixture was stirred at 15° C. for 3 hrs. On completion, water (600 mL) was added. The mixture was extracted with DCM (3×300 mL). The combined organic phase was washed with 0.5 M HCl (500 mL), brine (500 mL), dried over with anhydrous sodium sulfate and filtered. The filtrate was concentrated in vacuo. The residue was purified by flash silica gel chromatography (PE:EA=1:1) to give the title compound (138 g, 60% yield) as a yellow solid. $^1$H NMR (400 MHz, CDCl$_3$) δ 7.22-7.20 (d, J=8.0, 1H), 6.89-6.87 (d, J=8.0, 1H), 4.90-4.86 (m, 1H), 4.47-4.4.36 (m, 2H) 3.81 (s, 3H), 2.67-2.64 (m, 1H), 2.59-2.54 (m, 2H), 2.40-2.38 (m, 1H); LC-MS (ESI$^+$) m/z 272.0 (M+Na)$^+$.

Step 3—3-Hydroxy-1-[(4-methoxyphenyl)methyl] piperidine-2,6-dione

To a solution of N-[(4-methoxyphenyl)methyl]-5-oxo-tetrahydrofuran-2-carboxamide (138 g, 553 mmol) in anhydrous THF (1500 mL) was cooled to −78° C. Then, t-BuOK (62.7 g, 559 mmol) in a solution of anhydrous THF (1000 mL) was added dropwise slowly at −78° C. under nitrogen atmosphere. The resulting reaction mixture was stirred at −40° C. for 1 hr. On completion, the reaction mixture was quenched with saturated NH$_4$Cl solution (100 mL). The mixture was extracted with ethyl acetate (3×1500 mL). The combined organic layer was washed with brine (300 mL), dried over anhydrous sodium sulfate, filtered and the filtrate was concentrated in vacuo. The residue was purified by silica gel chromatography (PE:EA=1:1) to give the title compound (128 g, 92% yield) as a white solid. $^1$H NMR (400 MHz, CDCl$_3$) δ 7.39-7.32 (m, 2H), 6.89-6.81 (m, 2H), 4.91 (s, 2H), 4.17-4.11 (m, 1H), 3.80 (s, 3H), 3.54 (s, 1H), 2.98-2.87 (m, 1H), 2.73-2.60 (m, 1H), 2.26-2.20 (m, 1H), 1.80 (dq, J=4.8, 13.1 Hz, 1H).

Step 4—[1-[(4-Methoxyphenyl) methyl]-2,6-dioxo-3-piperidyl]trifluoromethanesulfonate To a solution of 3-hydroxy-1-[(4-methoxyphenyl) methyl] piperidine-2,6-dione (43.0 g, 173 mmol) and pyridine (27.3 g, 345 mmol) in DCM (500 mL) was added trifluoromethylsulfonyl trifluoromethanesulfonate (73.0 g, 258 mmol) dropwise at 0° C. The mixture was stirred at −10° C. for 1.5 hours under N$_2$. On completion, the mixture was concentrated in vacuo. The residue was purified by column chromatography on silica gel (PE:EA=20:1/8:1) to give the title compound (45.0 g, 68% yield) as light yellow gum. $^1$H NMR (400 MHz, CDCl$_3$) δ 7.36 (d, J=8.4 Hz, 2H), 6.85-6.82 (m, 2H), 5.32-5.28 (m, 1H), 4.91 (s, 2H), 3.79 (s, 3H), 3.02-2.97 (m, 1H), 2.79-2.74 (m, 1H), 2.41-2.35 (m, 2H).

2-(2-(((1 S,2S)-2-Hydroxycyclohexyl)amino)pyridin-4-yl)oxazole-4-carboxylic acid (Intermediate AZW)

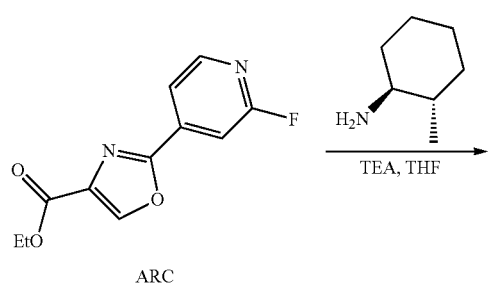

ARC

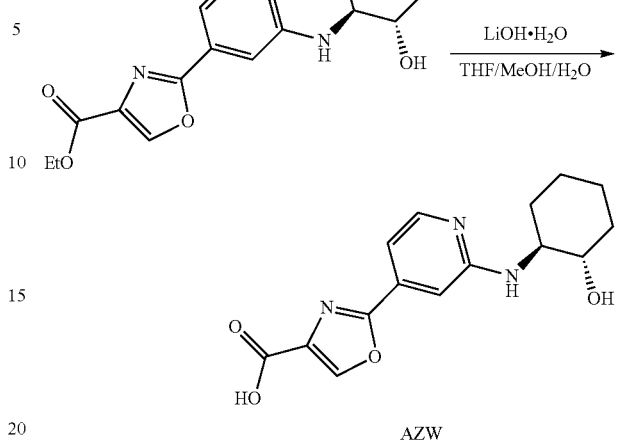

AZW

Step 1—Ethyl 2-(2-(((1 S,2S)-2-hydroxycyclohexyl)amino)pyridin-4-yl)oxazole-4-carboxylate To a solution of ethyl 2-(2-fluoro-4-pyridyl)oxazole-4-carboxylate (1.00 g, 4.23 mmol, Intermediate ARC) and (1S,2S)-2-aminocyclohexanol (731 mg, 6.35 mmol, CAS #74111-21-0) in the DMSO (5 mL) was added DIPEA (1.64 g, 12.7 mmol, 2.21 mL). The mixture was stirred at 130° C. for 4 hours. On completion, the reaction mixture was diluted with EA (50 mL) and washed with water (3×50 mL). The organic layer was dried over Na$_2$SO$_4$, filtered and concentrated in vacuo. The residue was purified by prep-HPLC (column: Phenomenex luna C18 150*40 mm*15 um; mobile phase: [water (0.225% FA)-ACN]; B %: 1%-27%, 9 min) to give the title compound (470 mg, 30% yield) as white solid. $^1$H NMR (400 MHz, CDCl$_3$) δ 8.34 (s, 1H), 8.01 (d, J=5.7 Hz, 1H), 7.31 (s, 1H), 7.23 (dd, J=1.2, 5.6 Hz, 1H), 4.45 (q, J=7.2 Hz, 2H), 3.58-3.50 (m, 2H), 1.81-1.76 (m, 2H), 1.42 (t, J=7.2 Hz, 3H), 1.39-1.28 (m, 6H); LC-MS (ESI$^+$) m/z 332.1 (M+H)$^+$.

Step 2—2-(2-(((1S,2S)-2-hydroxycyclohexyl) amino)pyridin-4-yl)oxazole-4-carboxylic acid To a solution of ethyl 2-[2-[[(1S,2S)-2-hydroxycyclohexyl]amino]-4-pyridyl]oxazole-4-carboxylate (100 mg, 302 umol) in the THF (1.5 mL), MeOH (0.5 mL) and H$_2$O (0.5 mL) was added LiOH (36.1 mg, 1.51 mmol). The mixture was stirred at 50° C. for 3 hours. On completion, the reaction mixture was concentrated in vacuo. The water phase was diluted with water (10 mL) and washed with DCM (10 mL). The water phase was separated and acidified to pH=4 to give the title compound (90.0 mg, 98% yield) as yellow solid. $^1$H NMR (400 MHz, DMSO-d$_6$) δ 8.89 (s, 1H), 8.10 (d, J=5.4 Hz, 1H), 7.11 (s, 1H), 6.95 (dd, J=1.2, 5.6 Hz, 1H), 6.74 (d, J=7.2 Hz, 1H), 3.66-3.54 (m, 2H), 2.02-1.87 (m, 2H), 1.69-1.58 (m, 2H), 1.32-1.12 (m, 4H).

2241

6-Morpholino-1,5-naphthyridine-4-carboxylic acid (Intermediate AUA)

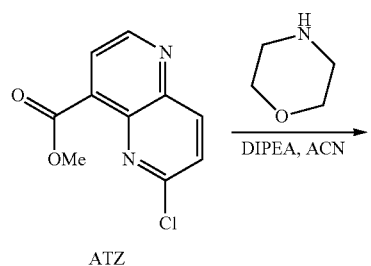

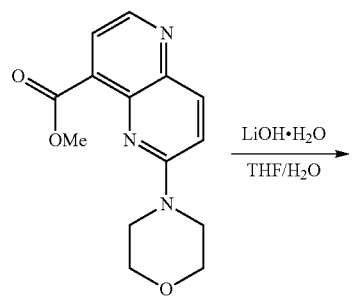

Step 1—Methyl 6-morpholino-1,5-naphthyridine-4-carboxylate

To a solution of methyl 6-chloro-1,5-naphthyridine-4-carboxylate (700 mg, 3.14 mmol, Intermediate ATZ) in ACN (10 mL) was added DIPEA (1.22 g, 9.43 mmol) and morpholine (548 mg, 6.29 mmol). The mixture was stirred at 80° C. for 16 hours. On completion, the reaction mixture was concentrated in vacuo. The reaction mixture was diluted with $H_2O$ (100 mL) and extracted with EA 300 mL (3×100 mL). The combined organic layers were dried over $Na_2SO_4$, filtered and concentrated in vacuo. The crude product was purified by reversed-phase HPLC (0.1% FA condition) to give the title compound (800 mg, 90% yield) as a yellow solid. LC-MS (ESI$^+$) m/z 274.2 (M+H)$^+$.

Step 2—6-Morpholino-1,5-naphthyridine-4-carboxylic acid

To a solution of methyl 6-morpholino-1,5-naphthyridine-4-carboxylate (600 mg, 2.11 mmol) in THF (12 mL) and $H_2O$ (3 mL) was added LiOH—$H_2O$ (106 mg, 2.53 mmol). The mixture was stirred at 25° C. for 1 hour. On completion, the reaction mixture was added 0.25 mol/L HCl (0.5 mL) and lyophilized to give the title compound (600 mg, 99% yield) as a yellow solid. LC-MS (ESI$^+$) m/z 260.6 (M+H)$^+$.

2242

N-(3-(difluoromethyl)-1-((1r,4r)-4-formylcyclohexyl)-1H-pyrazol-4-yl)-6-morpholino-1,5-naphthyridine-4-carboxamide (Intermediate AUB)

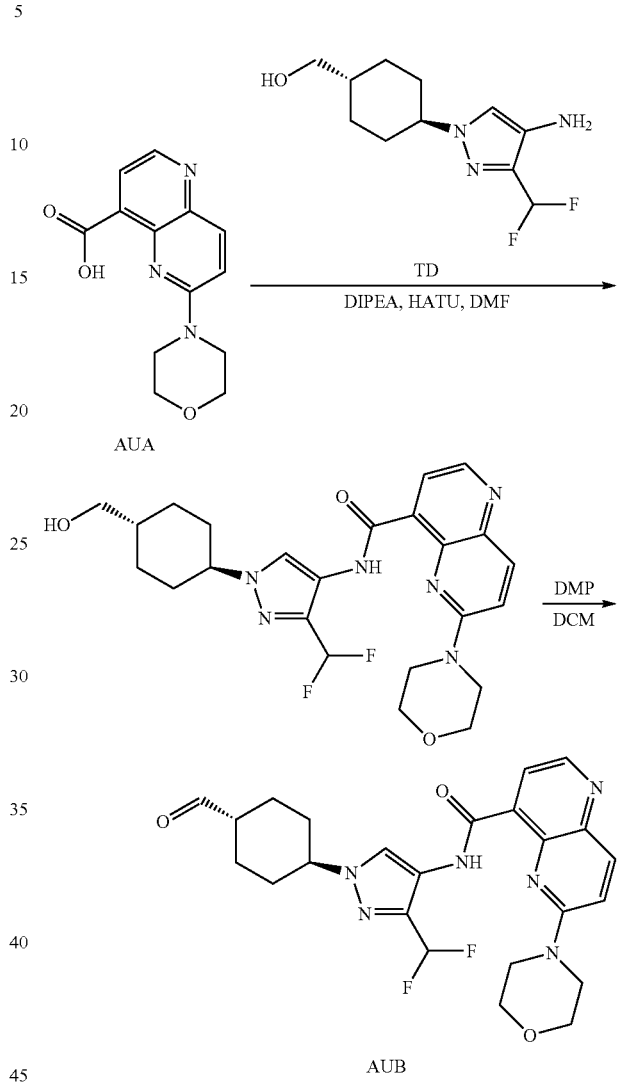

Step 1—N-(3-(difluoromethyl)-1-((1r,4r)-4-(hydroxymethyl)cyclohexyl)-1H-pyrazol-4-yl)-6-morpholino-1,5-naphthyridine-4-carboxamide To a solution of 6-morpholino-1,5-naphthyridine-4-carboxylic acid (250 mg, 964 umol, Intermediate AUA) and [4-[4-amino-3-(difluoromethyl)pyrazol-1-yl]cyclohexyl]methanol (213 mg, 868 umol, Intermediate TD) in DMF (3 mL) was added DIPEA (249 mg, 1.93 mmol) and HATU (440 mg, 1.16 mmol). The mixture was stirred at 25° C. for 16 hours. On completion, the reaction mixture was diluted with $H_2O$ (100 mL) and extracted with EA (3×100 mL). The combined organic layers were dried over $Na_2SO_4$, filtered and concentrated in vacuo. The residue was purified by prep-HPLC (TFA condition) to give the title compound (300 mg, 63% yield) as yellow solid. LC-MS (ESI$^+$) m/z 487.2 (M+H)$^+$.

2243

Step 2—N-(3-(difluoromethyl)-1-((1r,4r)-4-formyl-cyclohexyl)-1H-pyrazol-4-yl)-6-morpholino-1,5-naphthyridine-4-carboxamide To a solution of N-[3-(difluoromethyl)-1-[4-(hydroxymethyl)cyclohexyl]pyrazol-4-yl]-6-morpholino-1,5-naphthyridine-4-carboxamide (200 mg, 407 umol) in DCM (3 mL) was added DMP (207 mg, 488 umol). The mixture was stirred at 25° C. for 2 hours. On completion, the reaction mixture was quenched with sat. aq. Na$_2$S2SO$_4$ (20 mL) and sat. aq. NaHCO$_3$ (30 mL), then extracted with EA (3×50 mL). The organic phase was dried over Na$_2$SO$_4$, filtered and concentrated in vacuo to give the title compound (200 mg, 99% yield) as yellow oil. LC-MS (ESI$^+$) m/z 485.0 (M+H)$^+$.

[5-[3-(difluoromethyl)-4-[(5-morpholinopyrazolo[1,5-a]pyrimidine-3-carbonyl)amino] pyrazol-1-yl]-1,3-dioxan-2-yl]methyl methanesulfonate (Intermediate AUC)

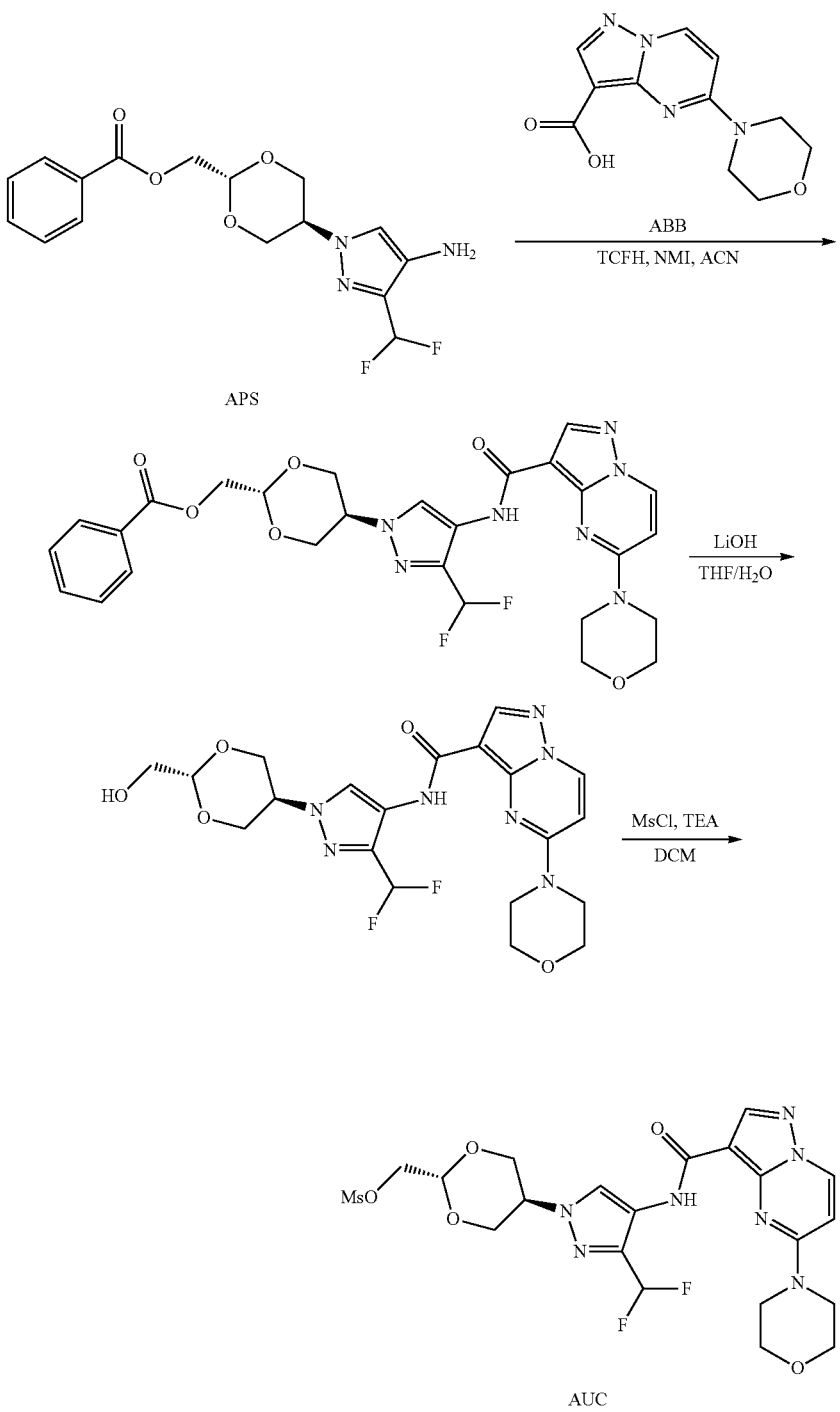

Step 1—[5-[3-(Difluoromethyl)-4-[(5-morpholino-pyrazolo[1,5-a]pyrimidine-3-carbonyl)amino] pyrazol-1-yl]-1,3-dioxan-2-yl]methylbenzoate A mixture of 5-morpholinopyrazolo[1,5-a]pyrimidine-3-carboxylic acid (175 mg, 707 umol, Intermediate ABB), 1-methylimidazole (203 mg, 2.48 mmol, 197 uL) and [chloro(dimethylamino)methylene]-dimethyl-ammonium; hexafluorophosphate (238 mg, 849 umol) in the ACN (5 mL) was stirred at 20° C. for 1 hour. Then [5-[4-amino-3-(difluoromethyl)pyrazol-1-yl]-1,3-dioxan-2-yl]methyl benzoate (250 mg, 707 umol, Intermediate APS) was added. The reaction mixture was stirred at 20° C. for 12 hours. On completion, the mixture was quenched with H$_2$O (10 mL) and a solid was precipitated out from the solution. The mixture was filtered and the filtrate cake was collected and dried in vacuo to afford the title compound (400 mg, 96% yield) as white solid. LC-MS (ESI$^+$) m/z 584.3 (M+H)$^+$.

Step 2—N-[3-(difluoromethyl)-1-[2-(hydroxymethyl)-1,3-dioxan-5-yl]pyrazol-4-yl]-5-morpholino-pyrazolo[1,5-a]pyrimidine-3-carboxamide To a solution of [5-[3-(difluoromethyl)-4-[(5-morpholino-pyrazolo[1,5-a]pyrimidine-3-carbonyl)amino] pyrazol-1-yl]-1,3-dioxan-2-yl]methyl benzoate (150 mg, 257 umol) in a mixed solvent of THF (4 mL) and H$_2$O (1 mL) was added LiOH (30.8 mg, 1.29 mmol). The mixture was stirred at 20° C. for 12 hours. On completion, the mixture was diluted with H$_2$O (10 mL), then a solid was precipitated out from the solution. The mixture was filtered and the filter cake was collected and dried in vacuo to give the title compound (120 mg, 97% yield) as white solid. LC-MS (ESI$^+$) m/z 480.2 (M+H)$^+$.

Step 3—[5-[3-(difluoromethyl)-4-[(5-morpholinopyrazolo[1,5-a]pyrimidine-3-carbonyl)amino] pyrazol-1-yl]-1,3-dioxan-2-yl]methyl methanesulfonate To a mixture of N-[3-(difluoromethyl)-1-[2-(hydroxymethyl)-1,3-dioxan-5-yl]pyrazol-4-yl]-5-morpholino-pyrazolo[1,5-a]pyrimidine-3-carboxamide (40.0 mg, 83.4 umol) in DCM (5 mL) was added TEA (25.3 mg, 250 umol, 34.8 uL) and MsCl (14.3 mg, 125 umol, 9.69 uL) at 0° C. The mixture was stirred at 0° C. for 2 hours. On completion, the reaction mixture was quenched with water (20 mL) at 25° C., and then extracted with DCM (3×20 mL). The combined organic layers were washed with brine (10 mL), dried over Na$_2$SO$_4$, filtered and concentrated in vacuo to give the title compound (43.0 mg, 93% yield) as white solid. LC-MS (ESI$^+$) m/z 558.3 (M+H)$^+$.

2-(2,6-Dioxo-3-piperidyl)-4-[[(2S)-morpholin-2-yl]methylamino]isoindoline-1,3-dione (Intermediate AUD)

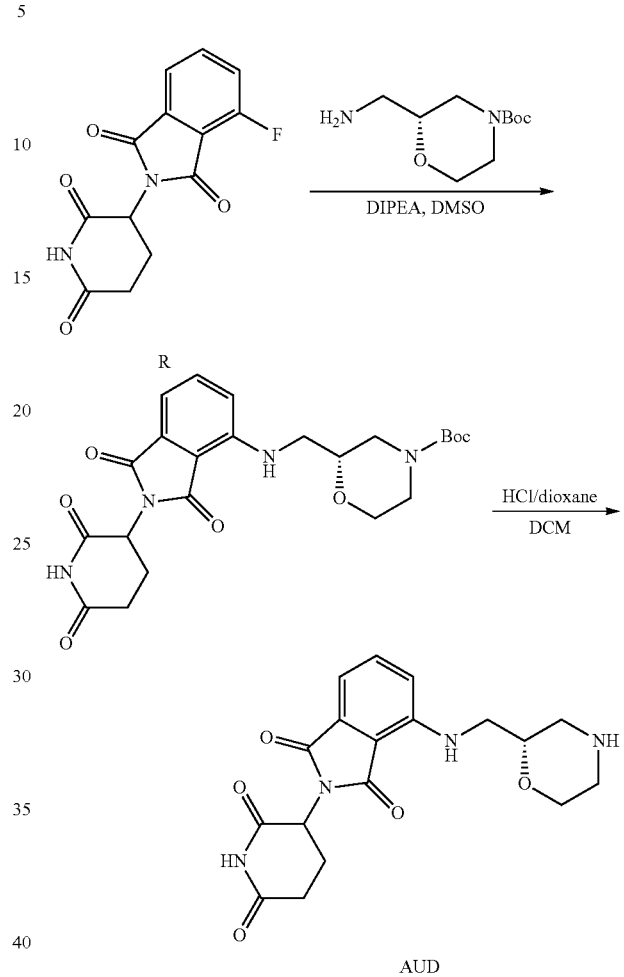

Step 1—Tert-butyl (2R)-2-[[[2-(2,6-dioxo-3-piperidyl)-1,3-dioxo-isoindolin-4-yl]amino]methyl]morpholine-4-carboxylate To a solution of tert-butyl 2-(aminomethyl)morpholine-4-carboxylate (500 mg, 2.31 mmol, CAS #140645-53-0) and 2-(2,6-dioxo-3-piperidyl)-4-fluoro-isoindoline-1,3-dione (638 mg, 2.31 mmol, Intermediate R) in DMSO (5 mL) was added DIPEA (1.49 g, 11.6 mmol, 2.01 mL). The reaction mixture was stirred at 130° C. for 12 hrs. On completion, the reaction mixture was concentrated in vacuo to give a residue. The residue was purified by reverse phase (0.1% FA condition) to give the title compound (540 mg, 49.4% yield) as a yellow solid. $^1$H NMR (400 MHz, DMSO-d$_6$) δ 11.1 (s, 1H), 7.61-7.56 (m, 1H), 7.17 (d, J=8.8 Hz, 1H), 7.05 (d, J=7.2 Hz, 1H), 6.66-6.65 (m, 1H), 5.08-5.03 (m, 1H), 3.89-3.84 (m, 2H), 3.70 (d, J=12.8 Hz, 1H), 3.56-3.49 (m, 2H), 3.44-3.38 (m, 1H), 3.33 (s, 2H), 2.93-2.84 (m, 2H), 2.73-2.61 (m, 2H), 2.54 (d, J=4.0 Hz, 1H), 1.39 (s, 9H); LC-MS (ESI$^+$) m/z 373.2 (M+H−100)$^+$.

Step 2—2-(2,6-Dioxo-3-piperidyl)-4-[[(2S)-morpholin-2-yl]methylamino]isoindoline-1,3-dione To a solution of tert-butyl (2R)-2-[[[2-(2,6-dioxo-3-piperidyl)-1,3-dioxo-isoindolin-4-yl]amino] methyl]morpholine-4-carboxylate (200 mg, 423 umol) in DCM (6 mL) was added HCl/dioxane (4 M, 2.36 mL), and the reaction mixture was stirred at 25° C. for 3 hrs. On completion, the mixture was concentrated in vacuo to give the title compound (170 mg, 98.2% yield, HCl) as a yellow solid. LC-MS (ESI$^+$) m/z 373.1 (M+H)$^+$.

2-(2,6-Dioxo-3-piperidyl)-4-[[(2R)-4-[3-(methylamino)propyl]morpholin-2-yl]methylamino] isoindoline-1,3-dione (Intermediate AUE)

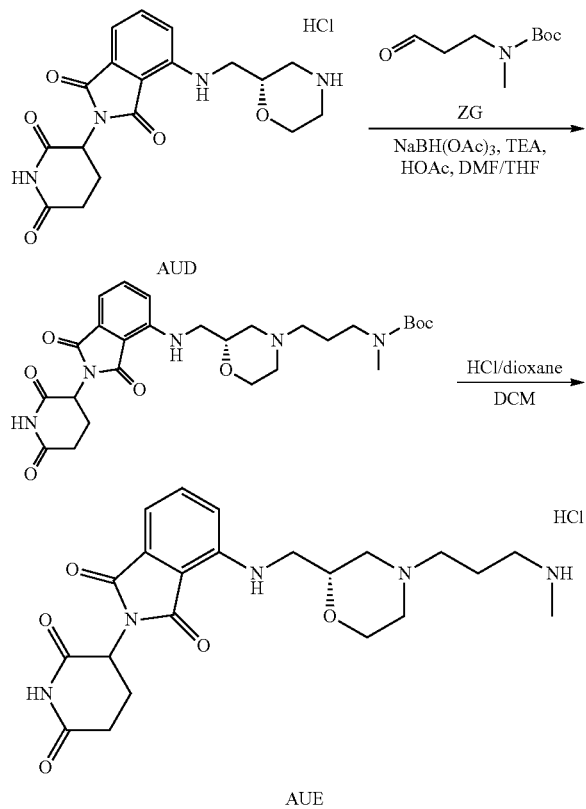

Step 1—Tert-butyl N-[3-[(2R)-2-[[[2-(2,6-dioxo-3-piperidyl)-1,3-dioxo-isoindolin-4-yl]amino]methyl]morpholin-4-yl]propyl]-N-methyl-carbamate To a solution of 2-(2,6-dioxo-3-piperidyl)-4-[[(2S)-morpholin-2-yl]methylamino]isoindoline-1,3-dione (170 mg, 416. umol, HCl, Intermediate AUD) in THF (2 mL) and DMF (2 mL) was added TEA (42.1 mg, 416 umol, 57.9 uL). The reaction mixture was stirred at 25° C. for 5 mins, then HOAc (50 mg, 832 umol, 47.6 uL) and tert-butyl N-methyl-N-(3-oxopropyl)carbamate (77.9 mg, 416 umol, Intermediate ZG) were added to the mixture, and the mixture was stirred at 25° C. for 25 min. Then NaBH(OAc)$_3$ (106 mg, 499 umol) was added and the reaction mixture was stirred at 25° C. for 1 hour. On completion, the reaction mixture was concentrated in vacuo to give a residue. Then the residue was purified by prep-HPLC (column: Phenomenex Synergi C18 150*25*10 um; mobile phase: [water (0.225% FA)-ACN]; B %: 9%-39%, 10 min) to give the title compound (156 mg, 69% yield) as a yellow solid. $^1$H NMR (400 MHz, DMSO-d$_6$) δ 11.08 (s, 1H), 7.60-7.56 (m, 1H), 7.13 (d, J=8.8 Hz, 1H), 7.04 (d, J=6.8 Hz, 1H), 6.61 (t, J=5.6 Hz, 1H), 5.07-5.03 (m, 1H), 3.83 (d, J=11.2 Hz, 1H), 3.66-3.63 (m, 1H), 3.54-3.43 (m, 2H), 3.34-3.27 (m, 1H), 3.19-3.15 (m, 2H), 2.93-2.82 (m, 2H), 2.75 (s, 3H), 2.69 (d, J=12.0 Hz, 1H), 2.61-2.52 (m, 2H), 2.27 (t, J=6.8 Hz, 2H), 2.04-1.99 (m, 2H), 1.86 (t, J=10.4 Hz, 1H), 1.65-1.58 (m, 2H), 1.37 (s, 9H); LC-MS (ESI$^+$) m/z 544.2 (M+H)$^+$.

Step 2—2-(2,6-Dioxo-3-piperidyl)-4-[[(2R)-4-[3-(methylamino)propyl]morpholin-2-yl]methylamino] isoindoline-1,3-dione To a solution of tert-butyl N-[3-[(2R)-2-[[[2-(2,6-dioxo-3-piperidyl)-1,3-dioxo-isoindolin-4-yl]amino] methyl]morpholin-4-yl]propyl]-N-methyl-carbamate (156 mg, 287 umol) in DCM (2 mL) was added to HCl/dioxane (4 M, 1.60 mL) at 25° C. for 3 hrs. On completion, the mixture was concentrated in vacuo to give the title compound (133 mg, 94.4% yield, HCl salt) as a yellow solid. LC-MS (ESI$^+$) m/z 444.2 (M+H)$^+$.

Tert-butyl ((6-(3-aminopropoxy)pyridin-3-yl) methyl)carbamate (Intermediate AUF)

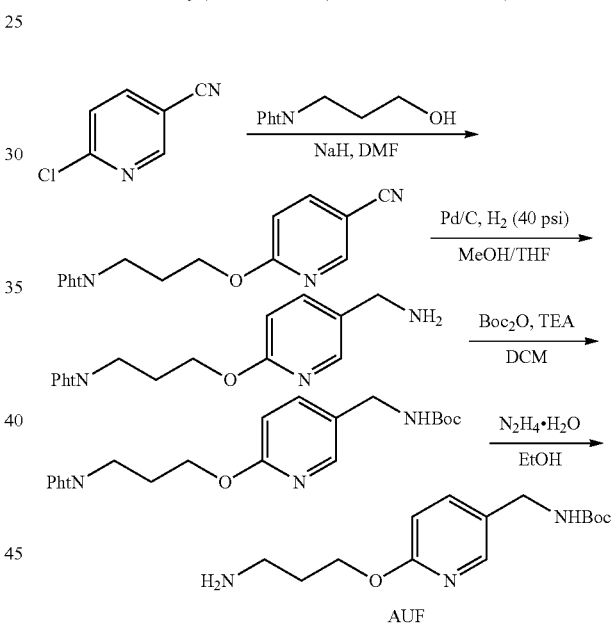

Step 1—6-(3-(1,3-Dioxoisoindolin-2-yl)propoxy) nicotinonitrile

To a solution of 2-(3-hydroxypropyl)isoindoline-1,3-dione (11.1 g, 54.1 mmol, CAS #883-44-3) in DMF (50 mL) was added NaH (2.89 g, 72.1 mmol, 60% dispersion in mineral oil) at 0° C. The mixture was stirred at 0° C. for 0.5 hour. Then 6-chloropyridine-3-carbonitrile (5.00 g, 36.0 mmol) was added and the mixture was stirred at 20° C. for 13.5 hours. On completion, the mixture was diluted with water (200 mL), and extracted with EA (6×100 mL). The combined organic layers was dried over Na$_2$SO$_4$, filtered and concentrated in vacuo. The residue was recrystallized with EA (50 mL) to give the title product (5.00 g, 45% yield) as a white solid. $^1$H NMR (400 MHz, DMSO-d$_6$) δ 8.64 (d, J=1.6 Hz, 1H), 8.10 (m, 1H), 7.90 (m, 4H), 6.70 (m, 1H), 4.40 (m, 2H), 3.76-3.73 (m, 2H), 2.09-2.06 (m, 2H).

Step 2—2-(3-((5-(Aminomethyl)pyridin-2-yl)oxy)propyl)isoindoline-1,3-dione

To a solution of 6-[3-(1,3-dioxoisoindolin-2-yl)propoxy]pyridine-3-carbonitrile (1.00 g, 3.25 mmol) in MeOH (20 mL) and THF (10 mL) was added HCl/dioxane (4 M, 0.2 mL) under N$_2$. The mixture was stirred at 20° C. for 0.2 hour. Next, Pd/C (500 mg, 10 wt %) was added and the mixture was stirred under H$_2$ (40 psi) at 40° C. for 13.8 hours. On completion, the mixture was filtered and the filtrate was concentrated in vacuo. The residue was purified by reverse-phase flash (HCl condition) to give the title product (450 mg, 37% yield, HCl salt) as a white solid. $^1$H NMR (400 MHz, DMSO-d$_6$) δ 8.41 (s, 3H), 8.34 (s, 1H), 7.86-7.79 (m, 5H), 6.66 (d, J=8.4 Hz, 1H), 4.29-4.26 (m, 2H), 3.95 (m, 2H), 3.75-3.72 (m, 2H), 2.08-2.03 (m, 2H); LC-MS (ESI$^+$) m/z 312.3 (M+H)$^+$.

Step 3—Tert-butyl ((6-(3-(1,3-dioxoisoindolin-2-yl)propoxy)pyridin-3-yl)methyl)carbamate To a solution of 2-[3-[[5-(aminomethyl)-2-pyridyl]oxy]propyl]isoindoline-1,3-dione (450 mg, 1.22 mmol) and TEA (369 mg, 3.65 mmol) in DCM (10 mL) was added Boc$_2$O (398 mg, 1.82 mmol). The mixture was stirred at 20° C. for 14 hours. On completion, the mixture was extracted with DCM (3×30 mL). The organic layers were dried over Na$_2$SO$_4$, filtered and concentrated in vacuo. The residue was washed with PE (10 mL) to give the title compound (350 mg, 65% yield) as a white solid. $^1$H NMR (400 MHz, DMSO-d$_6$) δ 7.98 (d, J=2.4 Hz, 1H), 7.82-7.73 (m, 2H), 7.72-7.71 (m, 2H), 7.70 (m, 1H), 6.57 (d, J=8.4 Hz, 1H), 4.71 (s, 3H), 3.36-3.33 (m, 2H), 3.91-3.87 (m, 2H), 2.20-2.14 (m, 2H), 1.45 (s, 9H).

Step 4—Tert-butyl ((6-(3-aminopropoxy)pyridin-3-yl)methyl)carbamate

A solution of tert-butyl N-[[6-[3-(1,3-dioxoisoindolin-2-yl)propoxy]-3-pyridyl]methyl]carbamate (350 mg, 799 umol) and NH$_2$NH$_2$H$_2$O (235 mg, 4.00 mmol) in EtOH (5 mL) was stirred at 60° C. for 2 hours. On completion, the mixture was filtered. The filtrate was concentrated to give the title compound (350 mg, 77% yield, 50% purity) as a yellow solid.

4-((3-((5-(Aminomethyl)pyridin-2-yl)oxy)propyl)amino)-2-(2,6-dioxopiperidin-3-yl) isoindoline-1,3-dione (Intermediate AUG)

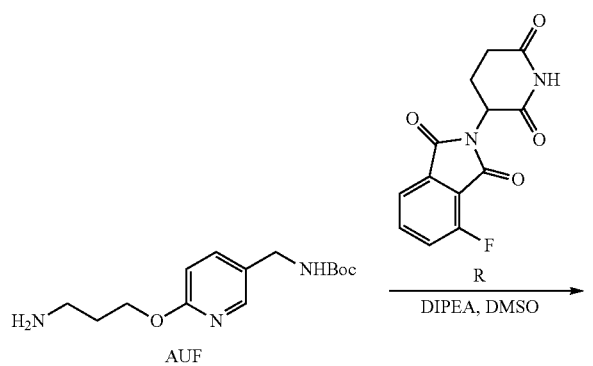

Step 1—Tert-butyl ((6-(3-((2-(2,6-dioxopiperidin-3-yl)-1,3-dioxoisoindolin-4-yl)amino)propoxy) pyridine-3-yl)methyl)carbamate To a solution of tert-butyl N-[[6-(3-aminopropoxy)-3-pyridyl]methyl]carbamate (340 mg, 604 umol, Intermediate AUF) in DMSO (5 mL) was added DIPEA (156 mg, 1.21 mmol) and 2-(2,6-dioxo-3-piperidyl)-4-fluoro-isoindoline-1,3-dione (250 mg, 906 umol, Intermediate R). The mixture was stirred at 130° C. for 0.5 hour. On completion, the mixture was filtered and the filtrate was concentrated in vacuo. The residue was purified by reverse-phase flash (FA condition) to give the title compound (100 mg, 27% yield) as a yellow oil. LC-MS (ESI$^+$) m/z 538.3 (M+H)$^+$.

Step 2—4-((3-((5-(Aminomethyl)pyridin-2-yl)oxy)propyl)amino)-2-(2,6-dioxopiperidin-3-yl) isoindoline-1,3-dione A solution of tert-butyl N-[[6-[3-[[2-(2,6-dioxo-3-piperidyl)-1,3-dioxo-isoindolin-4-yl]amino]propoxy]-3-pyridyl]methyl]carbamate (50.0 mg, 83.7 umol) in TFA (0.1 mL) and DCM (0.5 mL) was stirred at 20° C. for 14 hours. On completion, the mixture was concentrated to give the title compound (50.0 mg, 93% yield, TFA salt) as a yellow oil.

Tert-butyl (2S,6R)-4-(2-bromoethoxy)-2,6-dimethylpiperidine-1-carboxylate (Intermediate AUH)

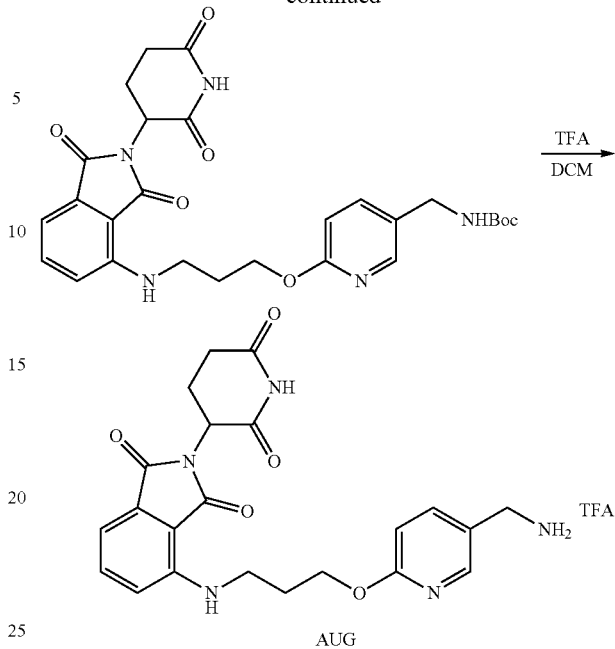

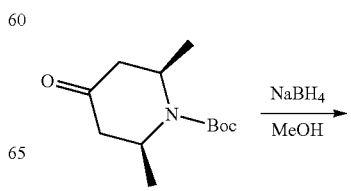

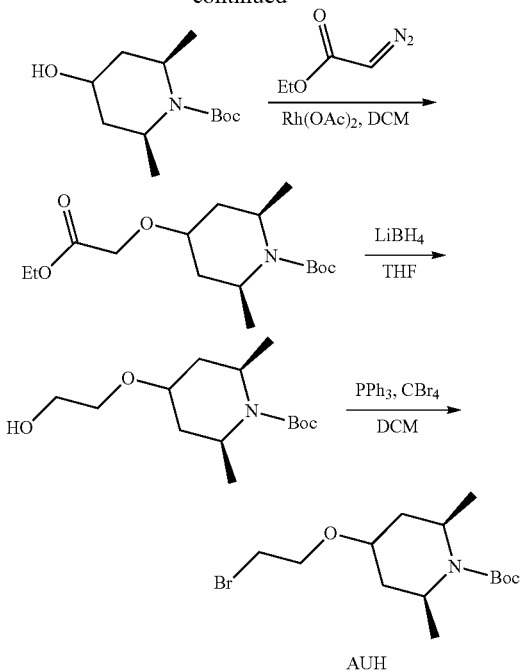

Step 1—Tert-butyl (2S,6R)-4-hydroxy-2,6-dimethyl-piperidine-1-carboxylate

To a mixture of tert-butyl (2S,6R)-2,6-dimethyl-4-oxo-piperidine-1-carboxylate (2.00 g, 8.80 mmol, CAS #: 1005397-64-7) in MeOH (20 mL) was added NaBH$_4$ (499 mg, 13.2 mmol). The reaction mixture was stirred at 25° C. for 1 hour. On completion, the reaction mixture was concentrated in vacuo. The residue was dissolved in EtOAc (60 mL), washed with saturated ammonium chloride aqueous solution, water and brine. The organic layer was dried over anhydrous sodium sulfate and concentrated in vacuo to give the title compound (2.00 g, 99% yield) as yellow oil. $^1$H NMR (400 MHz, CDCl$_3$) δ 4.18-4.08 (m, 2H), 3.87-3.78 (m, 1H), 2.19-2.10 (m, 1H), 2.03-1.95 (m, 1H), 1.84-1.73 (m, 1H), 1.55-1.45 (m, 2H), 1.40 (s, 9H), 1.31 (d, J=6.8 Hz, 3H), 1.10 (d, J=6.8 Hz, 3H).

Step 2-Tert-butyl (2S,6R)-4-(2-ethoxy-2-oxo-ethoxy)-2,6-dimethyl-piperidine-1-carboxylate To a solution of tert-butyl (2S,6R)-4-hydroxy-2,6-dimethyl-piperidine-1-carboxylate (2.00 g, 8.72 mmol) and Rh(OAc)$_2$ (193 mg, 872 umol) in DCM (30 mL) was added a solution of ethyl 2-diazoacetate (1.99 g, 17.4 mmol) in DCM (10 mL) at 0° C. The reaction mixture was stirred at 25° C. for 16 hours. On completion, the mixture was poured into ice-water (20 mL) and extracted with dichloromethane (3×50 mL). The combined organic layers were washed with water, brine, dried over anhydrous sodium sulfate and concentrated in vacuo. The residue was purified by silica gel column chromatography (petroleum ether:ethyl acetate=3:1) to give the title compound (1.50 g, 54% yield) as a yellow oil. $^1$H NMR (400 MHz, CDCl$_3$) δ 4.30-4.12 (m, 5H), 3.98-3.82 (m, 2H), 2.20-2.06 (m, 2H), 1.98-1.93 (m, 1H), 1.84-1.76 (m, 1H), 1.45 (s, 9H), 1.36-1.25 (m, 6H), 1.15 (d, J=6.8 Hz, 3H).

Step 3—Tert-butyl (2S,6R)-4-(2-hydroxyethoxy)-2,6-dimethyl-piperidine-1-carboxylate To a mixture of tert-butyl (2S,6R)-4-(2-ethoxy-2-oxo-ethoxy)-2,6-dimethyl-piperidine-1-carboxylate (1.50 g, 4.76 mmol) in THF (20 mL) was added LiBH$_4$ (414 mg, 19.1 mmol) at 0° C. The reaction was stirred at 80° C. for 2 hr under N$_2$ atmosphere. On completion, the reaction mixture was quenched by addition aqueous H$_2$O (60 mL) and extracted with EA (3×60 mL). The combined organic layers were washed with brine (3×30 mL), dried over anhydrous Na$_2$SO$_4$, filtered and concentrated in vacuo to give the title compound (1.30 g, 90% yield) as a white oil. $^1$H NMR (400 MHz, DMSO-d$_6$) δ=4.54 (t, J=5.2 Hz, 1H), 4.07-3.97 (m, 1H), 3.85-3.71 (m, 2H), 3.50-3.45 (m, 2H), 3.44-3.35 (m, 2H), 2.12-1.99 (m, 2H), 1.73-1.68 (m, 1H), 1.65-1.58 (m, 1H), 1.40 (s, 9H), 1.23 (d, J=6.4 Hz, 3H), 1.11 (d, J=6.8 Hz, 3H).

Step 4—Tert-butyl (2S,6R)-4-(2-bromoethoxy)-2,6-dimethyl-piperidine-1-carboxylate To a solution of tert-butyl (2S,6R)-4-(2-hydroxyethoxy)-2,6-dimethyl-piperidine-1-carboxylate (1.30 g, 4.76 mmol) in DCM (15 mL) was added PPh$_3$ (3.74 g, 14.3 mmol) and CBr$_4$ (4.73 g, 14.3 mmol) at 0° C. Then the mixture was stirred at 25° C. for 12 hr. On completion, the reaction mixture was filtered and concentrated under reduced pressure to give a residue. The residue was purified by column chromatography (Petroleum ether/Ethyl acetate=20/1) to give the title compound (470 mg, 29% yield) as a yellow oil. $^1$H NMR (400 MHz, DMSO-d$_6$) δ=4.02-4.00 (m, 1H), 3.88-3.78 (m, 2H), 3.74-3.66 (m, 2H), 3.60-3.54 (m, 2H), 2.13-2.02 (m, 2H), 1.76-1.72 (m, 1H), 1.66-1.57 (m, 1H), 1.39 (s, 9H), 1.24 (d, J=6.8 Hz, 3H), 1.10 (d, J=6.8 Hz, 3H).

3-[4-[2-[[(2S,6R)-2,6-dimethyl-4-piperidyl]oxy]ethyl]-3-methyl-2-oxo-benzimidazol-1-yl]]piperidine-2,6-dione (Intermediate AUI)

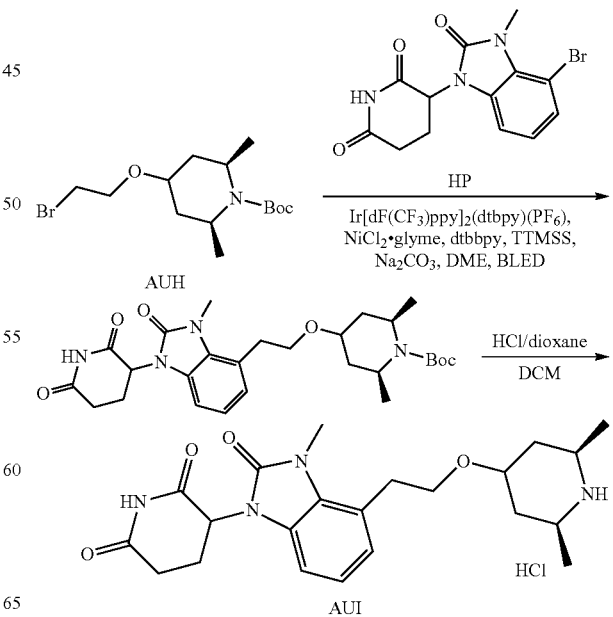

Step 1—Tert-butyl (2S,6R)-4-[2-[1-(2,6-dioxo-3-piperidyl)-3-methyl-2-oxo-benzimidazol-4-yl] ethoxy]-2,6-dimethyl-piperidine-1-carboxylate To an 40 mL vial equipped with a stir bar was added photo catalyst 3-(4-bromo-3-methyl-2-oxo-benzimidazol-1-yl)piperidine-2,6-dione (335 mg, 992 umol, Intermediate HP), tert-butyl(2S,6R)-4-(2-bromoethoxy)-2,6-dimethyl-piperidine-1-carboxylate (400 mg, 1.19 mmol, Intermediate AUH), Ir[dF(CF$_3$)ppy]2(dtbpy)(PF$_6$) (11.1 mg, 9.91 umol, CAS #2173009-61-3), NiCl$_2$.glyme (1.09 mg, 4.96 umol), dtbbpy (1.60 mg, 5.95 umol), TTMSS (247 mg, 991 umol, 305 uL) and Na$_2$CO$_3$ (210 mg, 1.98 mmol) in DME (15 mL). The reaction mixture was stirred and irradiated with a 34 W blue LED lamp at 25° C. for 14 hr. On completion, the reaction mixture was filtered and the filtrate was concentrated in vacuo to give a residue. The crude product was purified by reverse phase flash (0.1% FA condition) to give the title compound (150 mg, 29% yield) as a white solid. LC-MS (ESI$^+$) m/z 515.3 (M+H)$^+$.

Step 2—3-[4-[2-[[(2S,6R)-2,6-dimethyl-4-piperidyl]oxy]ethyl]-3-methyl-2-oxo-benzimidazol-1-yl] piperidine-2,6-dione To a solution of tert-butyl (2S,6R)-4-[2-[1-(2,6-dioxo-3-piperidyl)-3-methyl-2-oxo-benzimidazol-4-yl] ethoxy]-2,6-dimethyl-piperidine-1-carboxylate (50.0 mg, 97.2 umol) in DCM (1.0 mL) and was added HCl/dioxane (4 M, 1 mL). The mixture was stirred at 25° C. for 1 hr. On completion, the reaction mixture was concentrated in vacuo to give the title compound (40 mg, 100% yield, HCl) as a yellow solid. LC-MS (ESI$^+$) m/z 415.2 (M+H)$^+$.

Tert-butyl 7-(aminomethyl)-2-azaspiro [3.5]nonane-2-carboxylate (Intermediate AUJ)

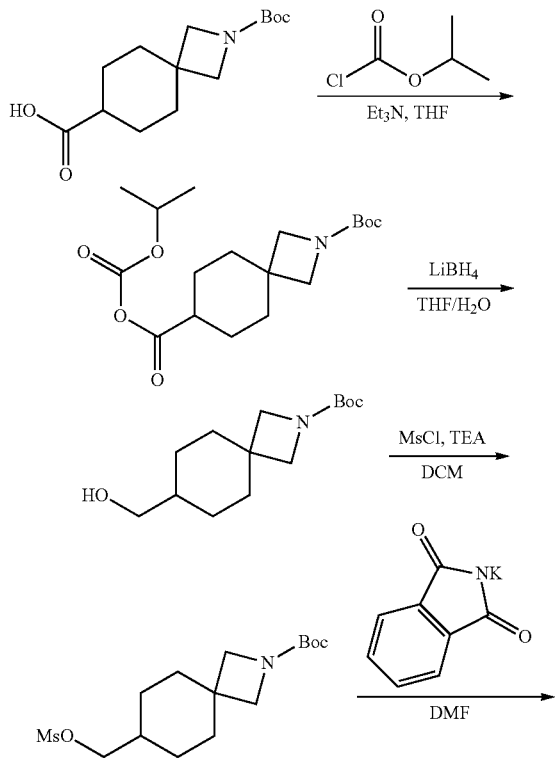

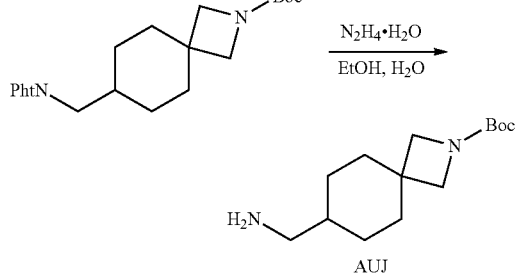

Step 1—2-Tert-butyl 7-isopropoxycarbonyl 2-azaspiro[3.5]nonane-2,7-dicarboxylate To a solution of 2-tert-butoxycarbonyl-2-azaspiro[3.5]nonane-7-carboxylic acid (840 mg, 3.12 mmol, CAS #1363381-18-3) in THF (10.0 mL) was added Et$_3$N (1.26 g, 12.5 mmol) and isopropyl carbonochloridate (573 mg, 4.68 mmol). The mixture was stirred at 0° C. for 2 hours. On completion, the mixture was filtered and the filter cake was washed with THF (30 mL). The filtrate was concentrated in vacuo to give the title compound (1.10 g, 99% yield) as yellow oil.

Step 2—Tert-butyl 7-(hydroxymethyl)-2-azaspiro [3.5]nonane-2-carboxylate

To a solution of tert-butyl-isopropoxycarbonyl 2-azaspiro [3.5]nonane-2,7-dicarboxylate (1.10 g, 3.09 mmol) in a mixed solvent of THF (20 mL) and H$_2$O (1 mL) was added LiBH$_4$ (404 mg, 18.5 mmol). The mixture was stirred at 0° C. for 2 hours. On completion, the reaction mixture was quenched with water (5.0 mL) at 0° C., and then extracted with (3×20 mL). The combined organic layers were washed with brine (50 mL), dried over Na$_2$SO$_4$, filtered and concentrated in vacuo to give the title compound (800 mg, 80% yield) as colorless oil. $^1$H NMR (400 MHz, CDCl$_3$) δ 3.57 (s, 2H), 3.54 (s, 2H), 3.42 (d, J=6.4 Hz, 2H), 1.89 (d, J=13.4 Hz, 2H), 1.76-1.67 (m, 3H), 1.45-1.39 (m, 12H), 1.01-0.89 (m, 2H).

Step 3—Tert-butyl 7-(methylsulfonyloxymethyl)-2-azaspiro[3.5]nonane-2-carboxylate To a solution of tert-butyl 7-(hydroxymethyl)-2-azaspiro [3.5]nonane-2-carboxylate (800 mg, 3.13 mmol) in DCM (10 mL) was added Et$_3$N (951 mg, 9.40 mmol). Then MsCl (43.0 mg, 3.76 mmol) was added to the mixture. The mixture was stirred at 0° C. for 2 hours. On completion, the mixture was concentrated in vacuo to give a residue. The residue was diluted with water (50 mL) and extracted with EA (3×60 mL). The combined organic layers were washed with brine (100 mL), dried over Na$_2$SO$_4$, filtered and concentrated in vacuo to give the title compound (1.00 g, 95% yield) as yellow oil. $^1$H NMR (400 MHz, CDCl$_3$) δ 4.04 (d, J=6.0 Hz, 2H), 3.60 (d, J=11.6 Hz, 4H), 3.02 (s, 3H), 1.95 (d, J=13.6 Hz, 2H), 1.82-1.72 (m, 3H), 1.46 (s, 10H), 1.11-1.02 (m, 2H).

Step 4—Tert-butyl 7-[(1,3-dioxoisoindolin-2-yl)methyl]-2-azaspiro[3.5]nonane-2-carboxylate To a solution of tert-butyl 7-(methylsulfonyloxymethyl)-2-azaspiro[3.5]nonane-2-carboxylate (1.00 g, 3.00 mmol) in DMF (10 mL) was added (1,3-dioxoisoindolin-2-yl)potassium (833 mg, 4.50 mmol, CAS #1074-82-4). The mixture was stirred at 80° C. for 2 hours. On completion, the mixture was diluted with water (50 mL) and extracted with EA (3×50 mL). The combined organic layers were washed with brine (100 mL), dried over $Na_2SO_4$, filtered and concentrated in vacuo to give a residue. The residue was triturated with PE/EA (3:1) and the filtered cake was collected and dried in vacuo to give the title compound (200 mg, 17% yield) as white solid. $^1$H NMR (400 MHz, $CDCl_3$) δ 7.81-7.76 (m, 2H), 7.70-7.62 (m, 2H), 3.53 (s, 2H), 3.48-3.44 (m, 3H), 1.82 (d, J=13.2 Hz, 2H), 1.72-1.68 (m, 1H), 1.62-1.55 (m, 3H), 1.36 (s, 9H), 1.33-1.26 (m, 2H), 1.04-0.90 (m, 2H).

Step 5—Tert-butyl 7-(aminomethyl)-2-azaspiro[3.5]nonane-2-carboxylate

To a solution of tert-butyl 7-[(1,3-dioxoisoindolin-2-yl)methyl]-2-azaspiro[3.5]nonane-2-carboxylate (200 mg, 520 umol) in EtOH (5.0 mL) was added $NH_2NH_2 \cdot H_2O$ (130 mg, 2.60 mmol). The mixture was stirred at 80° C. for 2 hours. On completion, the mixture was concentrated in vacuo to give a residue. The residue was washed with DCM (3×50 mL) then filtered, and the organic phase was concentrated in vacuo to give the title compound (100 mg, 75% yield) as colorless oil.

4-(2-Azaspiro[3.5]nonan-7-ylmethylamino)-2-(2,6-dioxo-3-piperidyl) isoindoline-1,3-dione (Intermediate AUK)

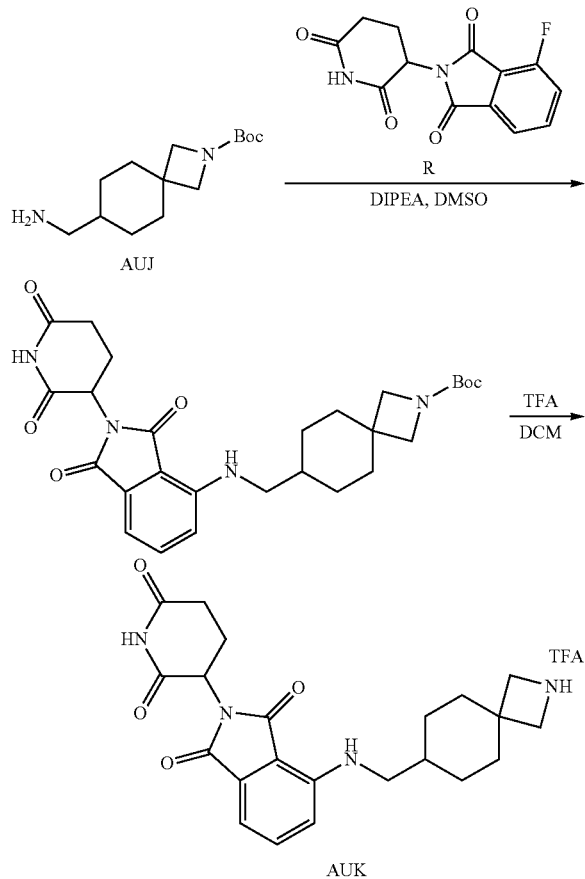

AUK

Step 1—Tert-butyl 7-[[[2-(2,6-dioxo-3-piperidyl)-1,3-dioxo-isoindolin-4-yl]amino]methyl]-2-azaspiro[3.5]nonane-2-carboxylate To a solution of tert-butyl 7-(aminomethyl)-2-azaspiro[3.5]nonane-2-carboxylate (100 mg, 393 umol, Intermediate AUJ) and 2-(2,6-dioxo-3-piperidyl)-4-fluoro-isoindoline-1,3-dione (108 mg, 393 umol, Intermediate R) in DMSO (2 mL) was added DIPEA (50.8 mg, 393 umol). The mixture was stirred at 130° C. for 2 hours. On completion, the mixture was quenched with $H_2O$ (0.2 mL) and concentrated in vacuo to give a residue. The residue was purified by reverse phase (0.1% FA condition) to give the title compound (90.0 mg, 44% yield) as yellow solid. $^1$H NMR (400 MHz, DMSO-$d_6$) δ 11.19-10.96 (m, 1H), 7.57-7.53 (m, 1H), 7.10 (d, J=8.8 Hz, 1H), 6.99 (d, J=6.8 Hz, 1H), 6.55 (t, J=6.2 Hz, 1H), 5.05-5.00 (m, 1H), 3.52-3.41 (m, 4H), 3.13 (t, J=6.4 Hz, 2H), 2.93-2.80 (m, 1H), 2.61-2.51 (m, 2H), 2.06-1.96 (m, 1H), 1.84-1.76 (m, 2H), 1.68-1.59 (m, 2H), 1.40-1.33 (m, 12H), 1.04-0.92 (m, 2H); LC-MS (ESI$^+$) m/z 511.1 (M+1)$^+$.

Step 2—4-(2-Azaspiro[3.5]nonan-7-ylmethylamino)-2-(2,6-dioxo-3-piperidyl) isoindoline-1,3-dione To a solution of tert-butyl 7-[[[2-(2,6-dioxo-3-piperidyl)-1,3-dioxo-isoindolin-4-yl]amino] methyl]-2-azaspiro[3.5]nonane-2-carboxylate (80.0 mg, 156 umol) in DCM (3 mL) was added TFA (1.54 g, 13.5 mmol). The mixture was stirred at 15° C. for 2 hours. On completion, the mixture was concentrated in vacuo to give the title compound (64.0 mg, 99.51% yield) as yellow oil. LC-MS (ESI$^+$) m/z 411.3 (M+1)$^+$.

Tert-butyl (2S)-2-ethynylmorpholine-4-carboxylate (Intermediate AUL)

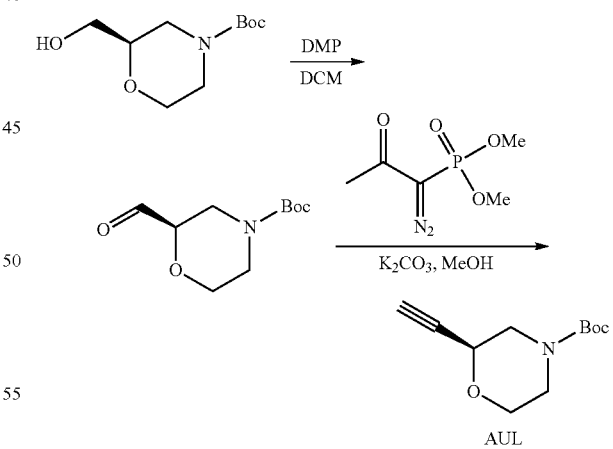

AUL

Step 1—Tert-butyl (2R)-2-formylmorpholine-4-carboxylate

To a mixture of tert-butyl (2R)-2-(hydroxymethyl)morpholine-4-carboxylate (5 g, 23.0 mmol, CAS #135065-71-3) in DCM (70 mL) was added DMP (11.7 g, 27.6 mmol) at 0° C. The reaction mixture was warm to 25° C. and stirred for 1.5 hr. On completion, the reaction mixture was quenched with saturated Na$_2$S$_2$O$_3$ aqueous (20 mL) and saturated aq. NaHCO$_3$ (50 mL) was added. The reaction mixture was extracted with DCM (2×40 mL). The organic phase was dried over anhydrous sodium sulfate, concentrated in vacuo to give the title compound (4.60 g, 92% yield) as white gum. $^1$H NMR (400 MHz, DMSO-d$_6$) δ 9.57 (s, 1H), 4.11-3.99 (m, 1H), 3.99-3.84 (m, 1H), 3.75-3.64 (m, 1H), 3.60-3.50 (m, 1H), 3.48-3.33 (m, 1H), 3.25-2.97 (m, 1H), 2.95-2.69 (m, 1H), 1.55-1.30 (m, 9H).

Step 2—Tert-butyl (2S)-2-ethynylmorpholine-4-carboxylate

To a mixture of tert-butyl (2R)-2-formylmorpholine-4-carboxylate (1.00 g, 4.65 mmol,) and K$_2$CO$_3$ (1.93 g, 13.9 mmol) in MeOH (10 mL) was added 1-diazo-1-dimethoxy-phosphoryl-propan-2-one (892 mg, 4.65 mmol, CAS 90965-06-3) at 0° C. The reaction mixture was warm to 25° C. and stirred for 17 hours. On completion, the reaction was filtered and the filtrate concentrated in vacuo. The residue was purified by silica gel chromatography (PE:EA=20:1) to give the title compound (500 mg, 50% yield) as a white solid. $^1$H NMR (400 MHz, CDCl$_3$) δ 4.30-4.21 (m, 1H), 4.02-3.91 (m, 1H), 3.88-3.72 (m, 1H), 3.64-3.49 (m, 2H), 3.37-3.19 (m, 2H), 2.49 (d, J=2.0 Hz, 1H), 1.48 (s, 9H).

3-[3-Methyl-4-[2-[(2S)-morpholin-2-yl]ethyl]-2-oxo-benzimidazol-1-yl]piperidine-2,6-dione (Intermediate AUM)

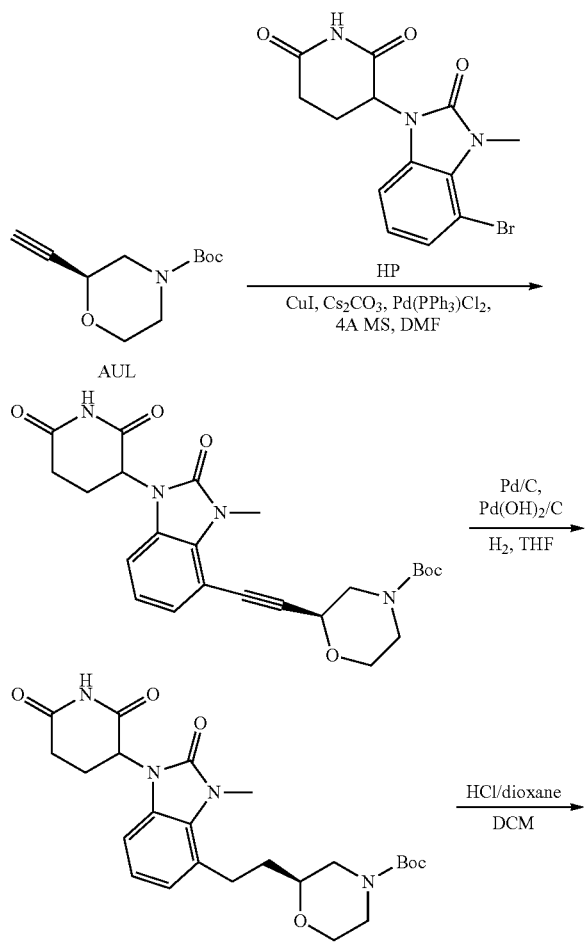

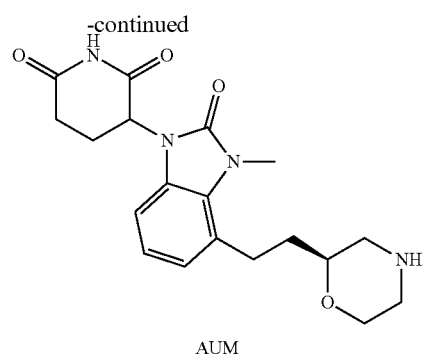

AUM

Step 1—Tert-butyl (2S)-2-[2-[1-(2,6-dioxo-3-piperidyl)-3-methyl-2-oxo-benzimidazol-4-yl]ethynyl]morpholine-4-carboxylate To a mixture of 3-(4-bromo-3-methyl-2-oxo-benzimidazol-1-yl)piperidine-2,6-dione (800 mg, 2.37 mmol, Intermediate HP), CuI (45.0 mg, 236 umol), Cs$_2$CO$_3$ (2.31 g, 7.10 mmol), Pd(PPh$_3$)$_2$Cl$_2$ (166 mg, 236 umol) and 4 Å molecular sieves (200 mg) in DMF (5 mL) was added a mixture of tert-butyl (2S)-2-ethynylmorpholine-4-carboxylate (500 mg, 2.37 mmol, Intermediate AUL) in DMF (5 mL). The reaction mixture was stirred at 80° C. for 3 hours under nitrogen atmosphere. On completion, the mixture was filtered and the filtrate was concentrated in vacuo. The residue was purified by silica gel chromatography (PE:EA=2:1) to give the title compound (330 mg, 29% yield) as a yellow solid. $^1$H NMR (400 MHz, DMSO-d$_6$) δ 11.14 (s, 1H), 7.20 (d, J=7.6 Hz, 1H), 7.15-7.10 (m, 1H), 7.08-7.01 (m, 1H), 5.50-5.30 (m, 1H), 4.75-4.68 (m, 1H), 3.94-3.81 (m, 1H), 3.67-3.41 (m, 6H), 3.40-3.36 (m, 2H), 2.90-2.83 (m, 1H), 2.74-2.60 (m, 2H), 2.10-2.00 (m, 1H), 1.41 (s, 9H).

Step 2—Tert-butyl (2S)-2-[2-[1-(2,6-dioxo-3-piperidyl)-3-methyl-2-oxo-benzimidazol-4-yl]ethyl]morpholine-4-carboxylate To a mixture of tert-butyl (2S)-2-[2-[1-(2,6-dioxo-3-piperidyl)-3-methyl-2-oxo-benzimidazol-4-yl] ethynyl]morpholine-4-carboxylate (180 mg, 384 umol) in THF (10 mL) was added Pd/C (40 mg, 384 umol, 10 wt %) and Pd(OH)$_2$/C (40 mg, 10 wt %). The reaction mixture was stirred at 25° C. for 17 hrs under H$_2$ (15 Psi). On completion, the reaction mixture was filtered. The filtrate was concentrated in vacuo to give the title compound (180 mg, 99% yield) as light yellow gum. $^1$H NMR (400 MHz, DMSO-d$_6$) δ 11.08 (s, 1H), 7.02-6.92 (m, 2H), 6.91-6.83 (m, 1H), 5.50-5.25 (m, 1H), 3.90-3.76 (m, 2H), 3.75-3.65 (m, 1H), 3.56 (s, 3H), 3.43-3.33 (m, 2H), 3.15-3.01 (m, 1H), 3.00-2.78 (m, 3H), 2.77-2.57 (m, 3H), 2.05-1.99 (m, 1H), 1.80-1.65 (m, 2H), 1.40 (s, 9H).

Step 3—3-[3-Methyl-4-[2-[(2S)-morpholin-2-yl]ethyl]-2-oxo-benzimidazol-1-yl]piperidine-2,6-dione To a mixture of tert-butyl-(2S)-2-[2-[1-(2,6-dioxo-3-piperidyl)-3-methyl-2-oxo-benzimidazol-4-yl] ethyl]morpholine-4-carboxylate (80.0 mg, 169 umol) in DCM (1 mL) was added HCl/dioxane (4 M, 1 mL) at 25° C. The reaction mixture was stirred at 25° C. for 0.5 hour. On completion, the reaction mixture was concentrated in vacuo to give the title compound (60 mg, 78% yield, HCl salt) as a white solid. LC-MS (ESI⁺) m/z 373.2 (M+H)⁺.

N-[1-(4-formylcyclohexyl)-3-(5-methyl-2-pyridyl) pyrazol-4-yl]pyrazolo [1,5-a]pyrimidine-3-carboxamide (Intermediate AUN)

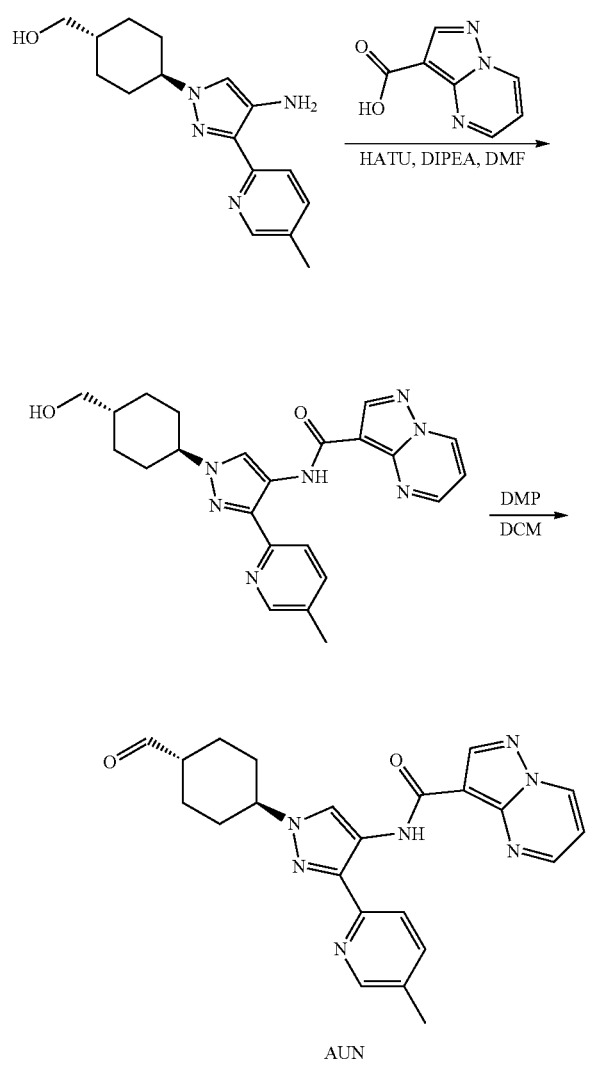

Step 1—N-[1-[4-(hydroxymethyl)cyclohexyl]-3-(5-methyl-2-pyridyl) pyrazol-4-yl]pyrazolo [1,5-a]pyrimidine-3-carboxamide A mixture of pyrazolo[1,5-a]pyrimidine-3-carboxylic acid (28.5 mg, 175 umol) and DIEA (113 mg, 873 umol, CAS #25940-35-6), HATU (99.6 mg, 262 umol) in DMF (4.0 mL) was stirred at 25° C. for 15 min, then [4-[4-amino-3-(5-methyl-2-pyridyl)pyrazol-1-yl]cyclohexyl]methanol (50.0 mg, 175 umol, synthesized via Step 1 of Intermediate ATR) was added. Then the reaction mixture was stirred at 25° C. for 1 hour. On completion, the reaction mixture was quenched by addition H₂O (0.1 mL) at 25° C., and then concentrated in vacuo to give a residue. The residue was purified by reverse phase flash (0.1% FA condition) to give the title compound (60.0 mg, 77% yield) as a white solid. ¹H NMR (400 MHz, DMSO-d₆) δ=12.18 (s, 1H), 9.67-9.00 (m, 2H), 8.82-8.30 (m, 3H), 7.93-7.68 (m, 2H), 7.35 (dd, J=4.0, 7.0 Hz, 1H), 4.48 (t, J=5.2 Hz, 1H), 4.29-4.12 (m, 1H), 3.31-3.27 (m, 2H), 2.41 (s, 3H), 2.22-2.06 (m, 2H), 1.98-1.70 (m, 4H), 1.49-1.46 (m, 1H), 1.16-1.10 (m, 2H). LC-MS (ESI⁺) m/z 432.1 (M+H)⁺.

Step 2—N-[1-(4-formylcyclohexyl)-3-(5-methyl-2-pyridyl)pyrazol-4-yl]pyrazolo [1,5-a]pyrimidine-3-carboxamide To a mixture of N-[1-[4-(hydroxymethyl)cyclohexyl]-3-(5-methyl-2-pyridyl) pyrazol-4-yl]pyrazolo [1,5-a]pyrimidine-3-carboxamide (55.0 mg, 127 umol) in DCM (2.0 mL) was added DMP (81.1 mg, 192 umol) at 25° C. under N₂. The mixture was stirred at 25° C. for 2 hr. On completion, the reaction mixture was quenched with Na₂S₂O₃ aqueous (5.0 mL) and extracted with DCM (2×3.0 mL). The combined organic layer was washed with NaHCO₃ and brine (2×3.0 mL), dried with anhydrous Na₂SO₄, filtered and concentrated in vacuo to give the title compound (50.0 mg, 91% yield) as a yellow solid. LC-MS (ESI⁺) m/z 430.1 (M+H)⁺.

N-[1-[4-(chloromethyl)phenyl]-3-(difluoromethyl) pyrazol-4-yl]-5-[(1R)-2-oxa-5-azabicyclo [2.2.1] heptan-5-yl]pyrazolo[1,5-a]pyrimidine-3-carboxamide (Intermediate AUO)

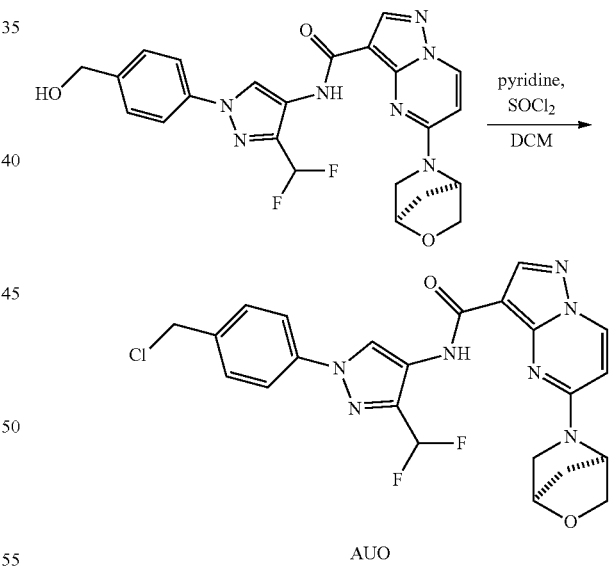

To a mixture of N-[3-(difluoromethyl)-1-[4-(hydroxymethyl)phenyl]pyrazol-4-yl]-5-[(1R)-2-oxa-5-azabicyclo [2.2.1]heptan-5-yl]pyrazolo[1,5-a]pyrimidine-3-carboxamide (200 mg, 415 umol, synthesized via Steps 1-2 of Intermediate AMT) in DCM (8 mL) was added pyridine (3.29 mg, 41.5 umol) and thionyl chloride (98.8 mg, 830 umol). The reaction mixture was stirred at 25° C. for 1.5 hour. On compound, the reaction mixture was concentrated in vacuo to give the title compound (200 mg, 96% yield) as light yellow solid. LC-MS (ESI⁺) m/z 500.2 (M+H)⁺.

N-[5-(difluoromethyl)-1H-pyrazol-4-yl]-5-morpholino-pyrazolo[1,5-a]pyrimidine-3-carboxamide (Intermediate AUP)

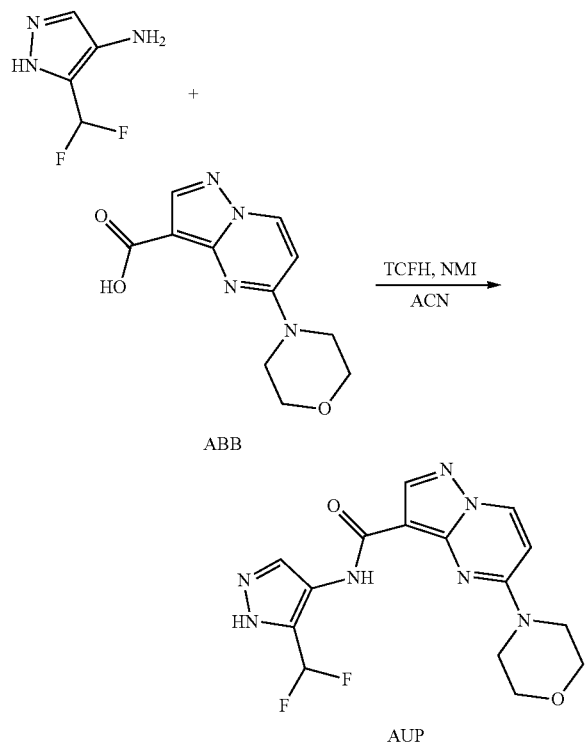

To a solution of 5-morpholinopyrazolo[1,5-a]pyrimidine-3-carboxylic acid (7.46 g, 30.0 mmol, Intermediate ABB), [chloro(dimethylamino)methylene]-dimethyl-ammonium; hexafluorophosphate (10.1 g, 36.0 mmol) and 1-methylimidazole (6.17 g, 75.1 mmol) in ACN (80 mL) was stirred at 25° C. for 1 hr. Then 3-(difluoromethyl)-1H-pyrazol-4-amine (4.00 g, 30.0 mmol, CAS 1443288-79-6) was added and the mixture was stirred at 25° C. for 16 hrs. On completion, the mixture was filtered and the cake was dried in vacuo to give the title compound (10.1 g, 92% yield) as a yellow solid. $^1$H NMR (400 MHz, DMSO-$d_6$) δ 13.20 (br s, 1H), 9.40 (s, 1H), 8.81 (d, J=7.6 Hz, 1H), 8.39-8.24 (m, 2H), 7.31-6.95 (m, 1H), 6.89 (d, J=8.0 Hz, 1H), 3.83-3.72 (m, 8H). LC-MS (ESI$^+$) m/z 364.2 (M+H)$^+$.

4-hydroxybutyl 4-methylbenzenesulfonate (Intermediate AUQ)

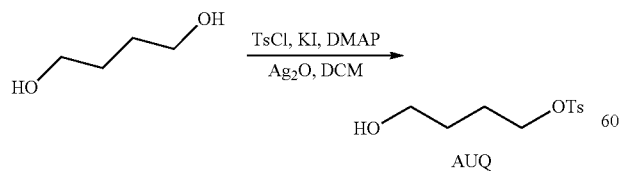

To a solution of butane-1,4-diol (10 g, 110 mmol) in DCM (1000 mL) was added Ag$_2$O (30.8 g, 133 mmol), KI (1.84 g, 11.1 mmol), DMAP (2.71 g, 22.1 mmol), then TsCl (21.1 g, 110 mmol) was added and stirred at 25° C. for 16 hrs. On completion, the mixture was filtered and the filtrate was concentrated in vacuo. The residue was purified by column chromatography (petroleum ether:ethyl acetate=1:1) to give the title compound (5.3 g, 19% yield) as colorless oil. $^1$H NMR (400 MHz, CDCl$_3$) δ 7.80-7.77 (m, 2H), 7.34 (d, J=8.4 Hz, 2H), 4.05 (t, J=6.4 Hz, 2H), 3.62 (t, J=6.4 Hz, 2H), 2.45-2.44 (m, 3H), 1.75-1.70 (m, 2H), 1.63-1.55 (m, 2H).

N-[5-(difluoromethyl)-1-(4-oxobutyl)pyrazol-4-yl]-5-morpholino-pyrazolo[1,5-a]pyrimidine-3-carboxamide (Intermediate AUR)

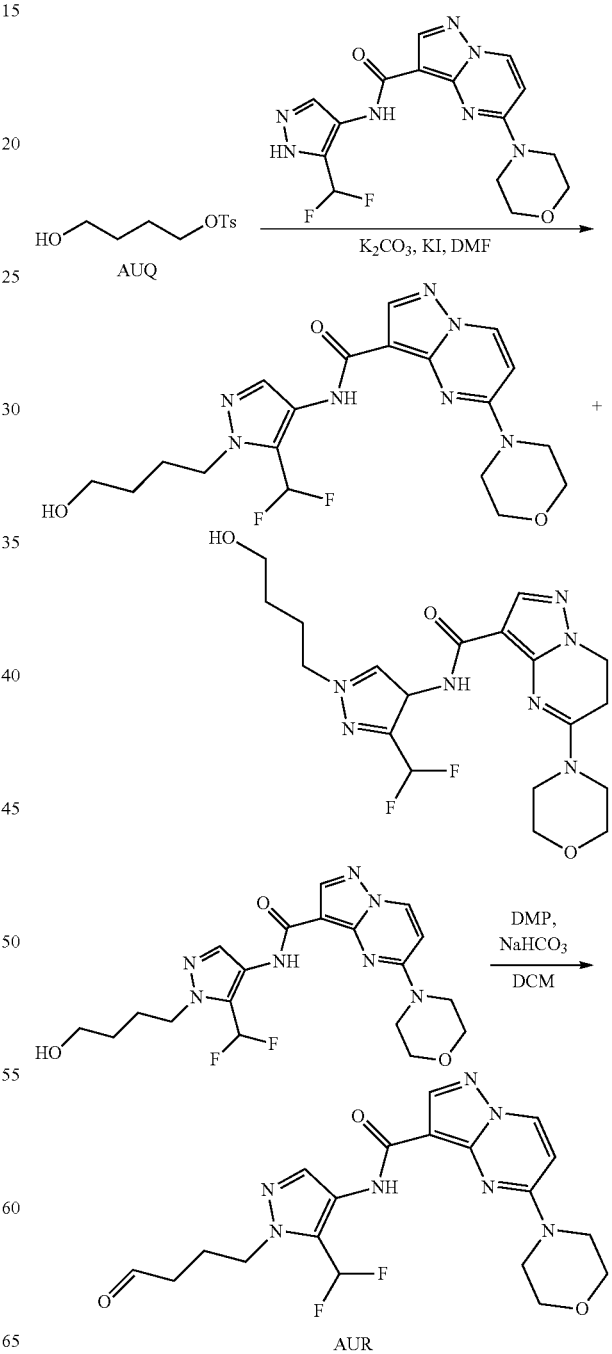

Step 1—N-[5-(difluoromethyl)-1-[4-(hydroxymethyl)cyclohexyl]pyrazol-4-yl]-5-morpholino-pyrazolo[1,5-a]pyrimidine-3-carboxamide and N-[3-(difluoromethyl)-1-(4-hydroxybutyl) pyrazol-4-yl]-5-morpholino-pyrazolo[1,5-a]pyrimidine-3-carboxamide To a mixture of N-[5-(difluoromethyl)-1H-pyrazol-4-yl]-5-morpholino-pyrazolo[1,5-a]pyrimidine-3-carboxamide (2.50 g, 6.88 mmol, Intermediate AUP), 4-hydroxybutyl 4-methylbenzenesulfonate (5.04 g, 20.6 mmol, Intermediate AUQ), KI (114 mg, 688 umol) and Cs$_2$CO$_3$ (4.48 g, 13.7 mmol) in DMF (100 mL) was stirred at 60° C. for 16 hrs. On completion, the mixture was quenched with water (50 mL) and extracted by EA (3×50 mL). The combined organic phase was dried over Na$_2$SO$_4$. The mixture was filtered and the filtrate was concentrated in vacuo. The residue was purified by Prep-HPLC (column: Phenomenex Synergi C18 150*25*10 um; mobile phase: [water (0.225% FA)-ACN]; B %: 20%-40%,10 min) to give the title compound N-[5-(difluoromethyl)-1-[4-(hydroxymethyl)cyclohexyl]pyrazol-4-yl]-5-morpholino-pyrazolo[1,5-a]pyrimidine-3-carboxamide (380 mg, 5% yield) as a white solid: $^1$H NMR (400 MHz, DMSO-d$_6$) δ 9.41 (s, 1H), 8.81 (s, 1H), 8.34 (s, 1H), 8.29 (s, 1H), 7.63-7.31 (m, 1H), 6.91-6.89 (m, 1H), 4.45 (t, J=4.8 Hz, 1H), 4.23-4.17 (m, 2H), 3.78-3.74 (m, 8H), 3.41 (d, J=4.8 Hz, 2H), 1.82-1.75 (m, 2H), 1.42-1.37 (m, 2H); and the title compound N-[3-(difluoromethyl)-1-(4-hydroxybutyl) pyrazol-4-yl]-5-morpholino-pyrazolo[1,5-a]pyrimidine-3-carboxamide (500 mg, 16% yield) as a white solid: $^1$H NMR (400 MHz, DMSO-d$_6$) δ 9.39 (s, 1H), 8.81 (d, J=8.0 Hz, 1H), 8.38 (s, 1H), 8.28 (s, 1H), 7.27-6.93 (m, 1H), 6.89 (d, J=8.0 Hz, 1H), 4.44 (t, J=5.2 Hz, 1H), 4.15 (t, J=7.2 Hz, 2H), 3.85-3.66 (m, 8H), 3.46-3.35 (m, 2H), 1.81 (q, J=7.2 Hz, 2H), 1.44-1.32 (m, 2H).

Step 2—N-[5-(difluoromethyl)-1-(4-oxobutyl)pyrazol-4-yl]-5-morpholino-pyrazolo[1,5-a]pyrimidine-3-carboxamide To a mixture of N-[5-(difluoromethyl)-1-(4-hydroxybutyl)pyrazol-4-yl]-5-morpholino-pyrazolo[1,5-a] pyrimidine-3-carboxamide (90.0 mg, 124 umol) in DCM (4 mL) was added NaHCO$_3$ (104 mg, 1.24 mmol), then DMP (52.6 mg, 124 umol) was added and the mixture was stirred at 25° C. for 1 hr. On completion, the mixture was quenched with Na$_2$SO$_3$ aqueous and extracted with EA (3×10 mL). The combined organic phase was dried over Na$_2$SO$_4$, filtered and the filtrate was concentrated in vacuo to give the title compound (96 mg, 60% yield) as a yellow solid. LC-MS (ESI$^+$) m/z 434.2 (M+H)$^+$.

3-(3-Methyl-2-oxo-5-(3-(piperidin-4-yloxy)prop-1-yn-1-yl)-2,3-dihydro-1H-benzo[d] imidazol-1-yl) piperidine-2,6-dione (Intermediate AUS)

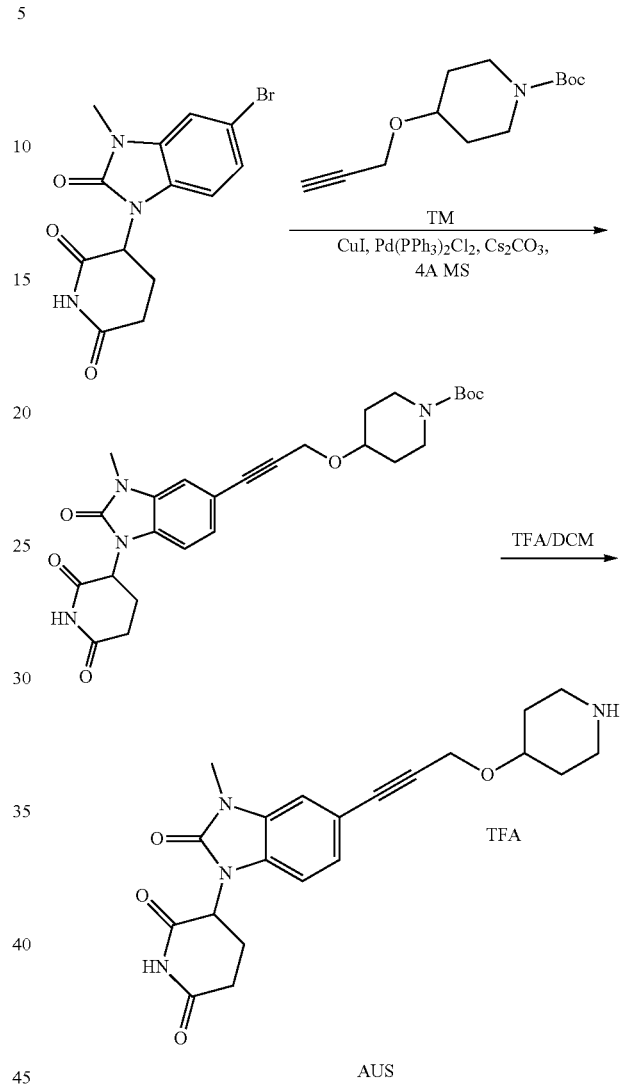

Step 1—Tert-butyl 4-((3-(1-(2,6-dioxopiperidin-3-yl)-3-methyl-2-oxo-2,3-dihydro-1H-benzo [d]imidazol-5-yl)prop-2-yn-1-yl)oxy)piperidine-1-carboxylate A solution of 3-(5-bromo-3-methyl-2-oxo-benzimidazol-1-yl)piperidine-2,6-dione (2.00 g, 5.91 mmol, Intermediate HN), tert-butyl 4-prop-2-ynoxypiperidine-1-carboxylate (2.12 g, 8.87 mmol, Intermediate TM), CuI (112 mg, 591 umol), Pd(PPh$_3$)$_2$Cl$_2$ (415 mg, 591 umol), 4 Å molecular sieves (1.00 g) and Cs$_2$CO$_3$ (7.71 g, 23.7 mmol) in DMF (30 mL) was stirred at 80° C. for 12 hr under N$_2$ atmosphere. On completion, the reaction mixture was filtrated, and the filtrate was concentrated in vacuo. The residue was purified by reverse phase (0.1% FA condition) to give title compound (1.00 g, 33% yield) as a yellow solid. $^1$H NMR (400 MHz, CDCl$_3$) δ 8.33 (s, 1H), 7.19 (dd, J=1.2, 8.0 Hz, 1H), 7.11 (d, J=1.2 Hz, 1H), 6.75 (d, J=8.0 Hz, 1H), 5.20 (dd, J=5.6, 12.8 Hz, 1H), 4.42 (s, 2H), 3.87-3.71 (m, 3H), 3.43 (s, 3H), 3.16-3.10 (m, 2H), 2.99-2.91 (m, 1H), 2.88-2.65 (m, 2H), 2.49-2.33 (m, 1H), 1.90-1.70 (m, 2H), 1.64-1.55 (m, 2H), 1.46 (s, 9H).

Step 2-3-(3-Methyl-2-oxo-5-(3-(piperidin-4-yloxy) prop-1-yn-1-yl)-2,3-dihydro-1H-benzo[d] imidazol-1-yl)piperidine-2,6-dione To a solution of tert-butyl 4-[3-[1-(2,6-dioxo-3-piperidyl)-3-methyl-2-oxo-benzimidazol-5-yl] prop-2-ynoxy] piperidine-1-caroxylate (200 mg, 402 umol) in DCM (5.0 mL) was added TFA (770 mg, 6.75 mmol). The mixture was stirred at 25° C. for 1 hr. On completion, the reaction mixture was concentrated in vacuo to give the title compound (120 mg, 50% yield, TFA) as yellow oil. LC-MS (ESI$^+$) m/z 397.4 (M+H)$^+$.

5-(Tetrahydro-2H-pyran-4-yl)pyrazolo[1,5-a]pyrimidine-3-carboxylic acid (Intermediate AUT)

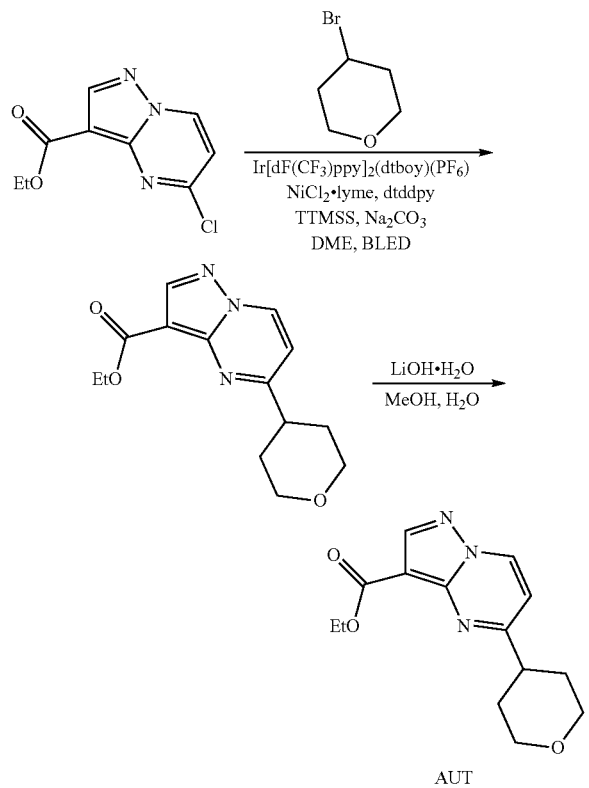

Step 1—Ethyl 5-(tetrahydro-2H-pyran-4-yl)pyrazolo[1,5-a]pyrimidine-3-carboxylate To a solution of ethyl 5-chloropyrazolo[1,5-a]pyrimidine-3-carboxylate (2.00 g, 8.86 mmol, CAS #1244844-77-7) and 4-bromotetrahydropyran (1.90 g, 11.5 mmol) in the DME (40 mL) was added bis[3,5-difluoro-2-[5-(trifluoromethyl)-2-pyridyl]phenyl]iridium(1+); 4-tert-butyl-2-(4-tert-butyl-2-pyridyl)pyridine; hexafluorophosphate (99.5 mg, 88.6 umol), dichloronickel; 1,2-dimethoxyethane (9.74 mg, 44.3 umol), 4-tert-butyl-2-(4-tert-butyl-2-pyridyl)pyridine (14.3 mg, 53.2 umol), bis(trimethylsilyl)silyl-trimethyl-silane (2.20 g, 8.86 mmol, 2.73 mL) and Na$_2$CO$_3$ (1.88 g, 17.7 mmol). The vial was sealed and placed under nitrogen was added. The reaction was stirred and irradiated with a 34 W blue LED lamp (7 cm away), with cooling fan to keep the reaction temperature at 25° C. for 48 hrs. On completion, the reaction mixture was concentrated in vacuo. The residue was purified by reversed phase (NH$_3$.H$_2$O, 0.1%) to give the title compound (250 mg, 10% yield) as colorless gum. $^1$H NMR (400 MHz, CDCl$_3$) δ 8.66 (d, J=7.3 Hz, 1H), 8.53 (s, 1H), 6.93 (d, J=7.3 Hz, 1H), 4.42 (q, J=7.1 Hz, 2H), 4.13 (td, J=3.2, 11.3 Hz, 2H), 3.62-3.53 (m, 2H), 3.24-3.14 (m, 1H), 2.02-1.93 (m, 4H), 1.43 (t, J=7.2 Hz, 3H).

Step 2—5-(Tetrahydro-2H-pyran-4-yl)pyrazolo[1,5-a]pyrimidine-3-carboxylic acid

To a solution of ethyl 5-tetrahydropyran-4-ylpyrazolo[1,5-a]pyrimidine-3-carboxylate (100 mg, 363 umol) in the THF (1.5 mL), MeOH (0.5 mL) and H$_2$O (0.5 mL) was added LiOH (43.5 mg, 1.82 mmol). The mixture was stirred at 50° C. for 3 hrs. On completion, the reaction mixture was acidified by HCl (aq, 1 M) to give the title compound (80.0 mg, 89% yield) as gray solid. LC-MS (ESI$^+$) m/z 248.2 (M+H)$^+$.

N-(3-(difluoromethyl)-1-((1r,4r)-4-formylcyclohexyl)-1H-pyrazol-4-yl)-5-(tetrahydro-2H-pyran-4-yl)pyrazolo[1,5-a]pyrimidine-3-carboxamide (Intermediate AUU

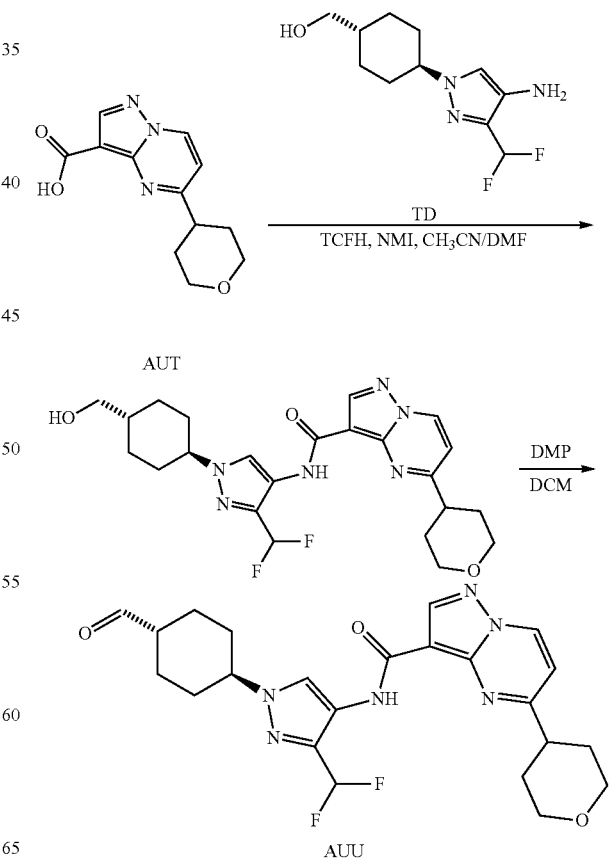

Step 1—N-(3-(difluoromethyl)-1-((1r,4r)-4-(hydroxymethyl)cyclohexyl)-1H-pyrazol-4-yl)-5-(tetrahydro-2H-pyran-4-yl)pyrazolo[1,5-a]pyrimidine-3-carboxamide To a solution of 5-tetrahydropyran-4-ylpyrazolo[1,5-a]pyrimidine-3-carboxylic acid (80 mg, 324 umol, Intermediate AUT) in the ACN (2 mL) was added [chloro(dimethylamino)methylene]-dimethyl-ammonium;hexafluorophosphate (109 mg, 388 umol) and 1-methylimidazole (93.0 mg, 1.13 mmol,). The resulting mixture was stirred at 25° C. for 0.5 hr. Then [4-[4-amino-3-(difluoromethyl)pyrazol-1-yl]cyclohexyl] methanol (79.4 mg, 324 umol, Intermediate TD) was added. The reaction mixture was stirred at 25° C. for 12 hrs. On completion, the mixture was concentrated in vacuo. The residue was purified by reversed phase (FA, 0.1%) to give the title compound (80 mg, 52% yield) as white solid. $^1$H NMR (400 MHz, CDCl$_3$-d) δ=10.11 (s, 1H), 8.72 (d, J=7.3 Hz, 1H), 8.68 (s, 1H), 8.40 (s, 1H), 7.00-6.67 (m, 2H), 4.20-4.14 (m, 2H), 4.10 (tt, J=3.9, 12.1 Hz, 1H), 3.61 (dt, J=2.4, 11.7 Hz, 2H), 3.54 (d, J=6.3 Hz, 2H), 3.15 (tt, J=4.0, 11.7 Hz, 1H), 2.29-2.22 (m, 2H), 2.07-1.94 (m, 7H), 1.83 (dq, J=3.6, 12.7 Hz, 3H), 1.26-1.14 (m, 2H); LC-MS (ESI$^+$) m/z 475.3 (M+H)$^+$.

Step 2—N-(3-(difluoromethyl)-1-((1r,4r)-4-formyl-cyclohexyl)-1H-pyrazol-4-yl)-5-(tetrahydro-2H-pyran-4-yl)pyrazolo[1,5-a]pyrimidine-3-carboxamide To a solution of N-[3-(difluoromethyl)-1-[4-(hydroxymethyl)cyclohexyl]pyrazol-4-yl]-5-tetrahydropyran-4-yl-pyrazolo[1,5-a]pyrimidine-3-carboxamide (80 mg, 169 umol) in the DCM (2 mL) was added DMP (85.8 mg, 202 umol, 62.6 uL) in portion. The mixture was stirred at 25° C. for 1 hr. On completion, the reaction mixture was poured into saturated Na$_2$SO$_3$ (aq, 50 mL) and stirred for 30 mins. Then the organic layer was separated and washed with saturated NaHCO$_3$ (aq, 50 mL). Then the organic layer was dried over Na$_2$SO$_4$, filtered and concentrated in vacuo. The residue was purified by column chromatography (PE:EA=1:1) to give the title compound (20 mg, 25% yield) as white solid. LC-MS (ESI$^+$) m/z 473.3 (M+H)$^+$.

Tert-butyl 2-(2-bromoethoxy)-7-azaspiro[3.5]nonane-7-carboxylate (Intermediate AUV)

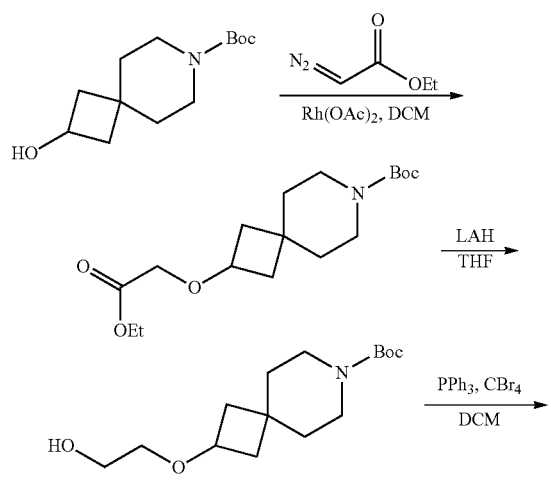

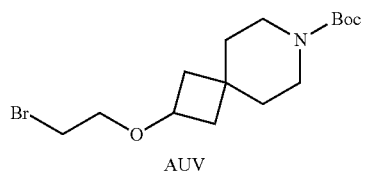

Step 1—Tert-butyl 2-(2-ethoxy-2-oxo-ethoxy)-7-azaspiro[3.5]nonane-7-carboxylate To a solution of tert-butyl 2-hydroxy-7-azaspiro [3.5] nonane-7-carboxylate (2.00 g, 8.29 mmol) and Rh(OAc)$_2$ (18.3 mg, 82.9 umol) in DCM (8.0 mL) was added a solution of ethyl 2-diazoacetate (2.84 g, 24.9 mmol, 2.60 mL) in DCM (8.0 mL) dropwise at 0° C. The mixture was stirred at 25° C. for 16 hr. On completion, the reaction mixture was diluted with water (60 mL) and extracted with EA (3×50 mL). The combined organic layers were washed with brine (3×30 mL), dried over anhydrous Na$_2$SO$_4$, filtered and concentrated in vacuo to give a residue. The residue was purified by column chromatography (petroleum ether/ethyl acetate=10/1) to give the title compound (1.60 g, 59% yield) as a white oil. $^1$H NMR (400 MHz, CDCl$_3$) δ 4.22-4.18 (m, 2H), 4.09-4.03 (m, 1H), 3.96 (s, 2H), 3.33-3.26 (m, 4H), 2.23-2.14 (m, 2H), 1.83-1.74 (m, 2H), 1.53-1.45 (m, 4H), 1.43 (s, 9H), 1.27 (t, J=7.2 Hz, 3H).

Step 2—Tert-butyl 2-(2-hydroxyethoxy)-7-azaspiro [3.5]nonane-7-carboxylate

To a mixture of tert-butyl 2-(2-ethoxy-2-oxo-ethoxy)-7-azaspiro[3.5]nonane-7-carboxylate (1.60 g, 4.89 mmol) in THF (20 mL) was added LAH (223 mg, 5.86 mmol) at 0° C. The reaction mixture was stirred at 0° C. for 2 hours. On completion, the reaction mixture was quenched by H$_2$O (0.4 mL), and then 15% NaOH aqueous (0.4 mL) was added and H$_2$O (0.4 ml) was added. The mixture was dried over anhydrous Na$_2$SO$_4$, filtered and concentrated in vacuo to give the title compound (1.20 g, 90% yield) as white oil. $^1$H NMR (400 MHz, CDCl$_3$) δ 4.78 (s, 1H), 4.03-3.98 (m, 1H), 3.74-3.66 (m, 2H), 3.46-3.39 (m, 2H), 3.33-3.26 (m, 4H), 2.22-2.15 (m, 2H), 1.75-1.67 (m, 2H), 1.53-1.45 (m, 4H), 1.43 (s, 9H).

Step 3—Tert-butyl 2-(2-bromoethoxy)-7-azaspiro [3.5]nonane-7-carboxylate

To a solution of tert-butyl 2-(2-hydroxyethoxy)-7-azaspiro[3.5]nonane-7-carboxylate (1.20 g, 4.20 mmol) and PPh$_3$ (3.31 g, 12.6 mmol) in DCM (20 mL) was added CBr$_4$ (4.18 g, 12.6 mmol) at 0° C. The mixture was stirred at 25° C. for 12 hr. On completion, the reaction mixture was concentrated in vacuo to give a residue. The residue was purified by column chromatography (petroleum ether/ethyl acetate=10/1) to give the title compound (740 mg, 51% yield) as a yellow solid. $^1$H NMR (400 MHz, CDCl$_3$) δ 4.05-4.03 (m, 1H), 3.68-3.63 (m, 2H), 3.47-3.41 (m, 2H), 3.33-3.29 (m, 4H), 2.24-2.15 (m, 2H), 1.79-1.72 (m, 2H), 1.54-1.47 (m, 4H), 1.44 (s, 9H).

3-[4-[2-(7-Azaspiro[3.5]nonan-2-yloxy)ethyl]-3-methyl-2-oxo-benzimidazol-1-yl]piperidine-2,6-dione (Intermediate AUW)

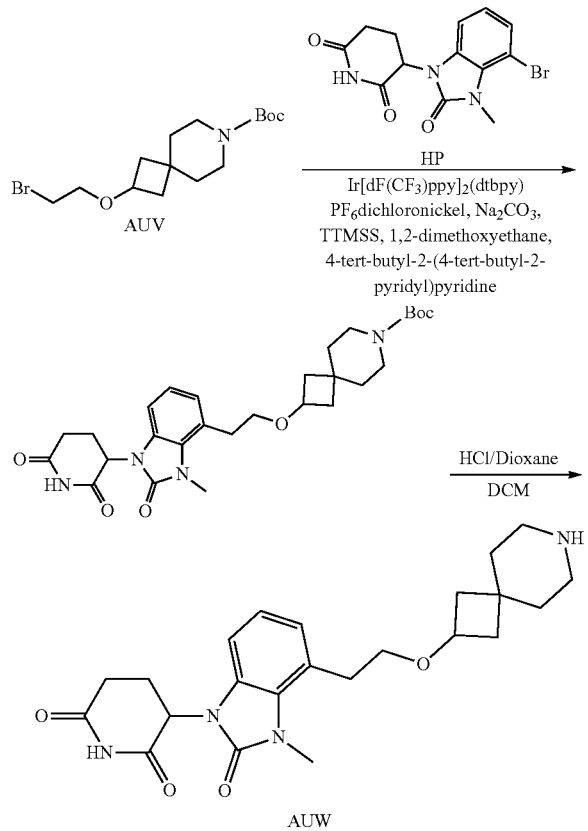

Step 1—Tert-butyl 2-[2-[1-(2,6-dioxo-3-piperidyl)-3-methyl-2-oxo-benzimidazol-4-yl]ethoxy]-7-azaspiro[3.5]nonane-7-carboxylate To an 8 mL vial equipped with a stir bar was added 3-(4-bromo-3-methyl-2-oxo-benzimidazol-1-yl)piperidine-2,6-dione (250 mg, 739.30 umol, Intermediate HP), tert-butyl2-(2-bromoethoxy)-7-azaspiro[3.5]nonane-7-carboxylate (309 mg, 887 umol, Intermediate AUV), Ir[dF(CF$_3$)ppy]2(dtbpy)(PF$_6$) (8.29 mg, 7.39 umol), dichloronickel; 1,2-dimethoxyethane (812 ug, 3.70 umol), 4-tert-butyl-2-(4-tert-butyl-2-pyridyl)pyridine (1.19 mg, 4.44 umol), TTMSS (184 mg, 739 umol, 228 uL) and Na$_2$CO$_3$ (157 mg, 1.48 mmol) in DME (3 mL). The reaction mixture was stirred and irradiated with a 34 W blue LED lamp at 25° C. for 14 hr. On completion, the reaction mixture was filtered and concentrated in vacuo to give a residue. The residue was purified by reverse phase flash (0.1% FA condition) to give the title compound (80.0 mg, 30% yield) as yellow oil. LC-MS (ESI$^+$) m/z 527.3 (M+H)$^+$.

Step 2—3-[4-[2-(7-Azaspiro[3.5]nonan-2-yloxy)ethyl]-3-methyl-2-oxo-benzimidazol-1-yl]piperidine-2,6-dione To a solution of tert-butyl 2-[2-[1-(2,6-dioxo-3-piperidyl)-3-methyl-2-oxo-benzimidazol-4-yl] ethoxy]-7-azaspiro[3.5]nonane-7-carboxylate (40.0 mg, 76.0 umol) in DCM (3.0 mL) was added HCl/dioxane (4 M, 1.0 mL). The mixture was stirred at 25° C. for 1 hr. On completion, the reaction mixture was concentrated under reduced pressure to give the title compound (30 mg, 100% yield, HCl) as yellow oil. LC-MS (ESI$^+$) m/z 427.3 (M+H)$^+$.

((1R,4R)-4-(4-amino-5-(difluoromethyl)-1H-pyrazol-1-yl)cyclohexyl)methanol (Intermediate AUX)

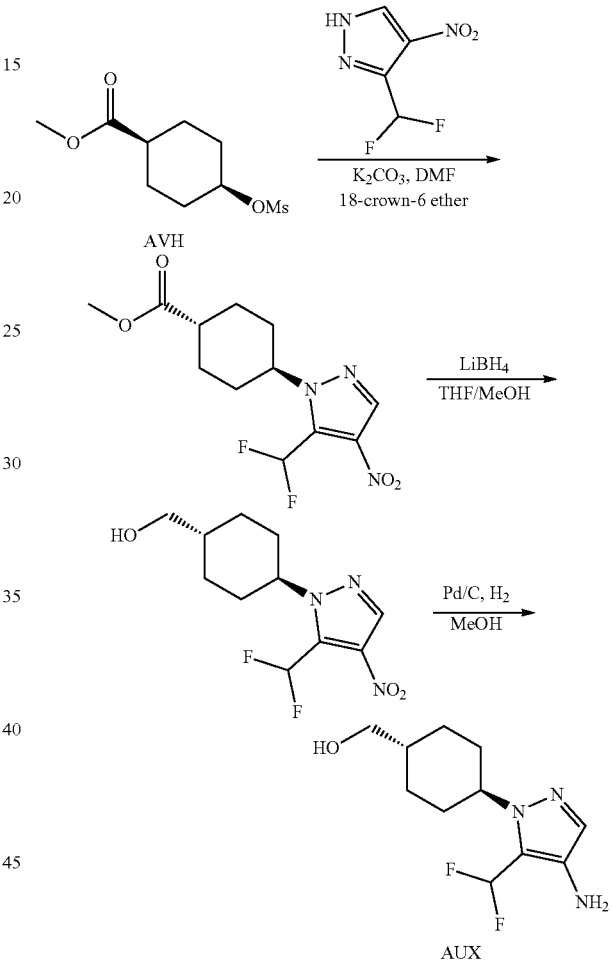

Step 1—(1R,4R)-Methyl 4-(5-(difluoromethyl)-4-nitro-1H-pyrazol-1-yl)cyclohexanecarboxylate To a mixture of 3-(difluoromethyl)-4-nitro-1H-pyrazole (30.0 g, 183 mmol) and (1s,4s)-methyl-4-((methylsulfonyl)oxy)cyclohexanecarboxylate (30.4 g, 128 mmol, Intermediate AVH) in DMF (450 mL) was added K$_2$CO$_3$ (76.2 g, 551 mmol) and and 18-crown-6 ether (4.86 g, 18.4 mmol). The reaction mixture was stirred at 80° C. for 12 hours. On completion, the reaction mixture was concentrated in vacuo to remove the DMF and the mixture was diluted with water (300 mL), then extracted with EA (2×200 mL). The combined organic phase was washed with brine (2×200 mL), dried with anhydrous Na$_2$SO$_4$, filtered and concentrated in vacuo. The residue was purified by column chromatography (petroleum ether:ethyl acetate=2:1) to give the title compound (1.5 g, 2% yield) as a yellow solid. ¹H NMR (400 MHz, DMSO-d₆) δ 8.42 (s, 1H), 7.83-7.44 (m, 1H), 4.62-4.34 (m, 1H), 3.60 (s, 3H), 2.45-2.41 (m, 1H), 2.11-1.87 (m, 6H), 1.62-1.47 (m, 2H).

Step 2—((1R,4R)-4-(5-(difluoromethyl)-4-nitro-1H-pyrazol-1-yl)cyclohexyl)methanol To a mixture of (1r,4r)-methyl 4-(5-(difluoromethyl)-4-nitro-1H-pyrazol-1-yl)cyclohexanecarboxylate (500 mg, 1.65 mmol) in THF (10 mL)/MeOH (1 mL) was added LiBH₄ (143 mg, 6.59 mmol) and the mixture was stirred at 50° C. for 3 hrs. On completion, the mixture was diluted with water (80 mL) and extracted by EA (3×50 mL). The combined organic phase was dried over anhydrous Na₂SO₄ and filtered. The filtrate was concentrated in vacuo. The residue was purified by flash silica gel chromatography (ISCO; 4 g SepaFlash, Silica Flash Column, Eluent of 0-30% ethyl acetate/petroleum ether gradient @ 40 mL/min) to give the title compound (170 mg, 37% yield) as yellow oil.

Step 3—((1R,4R)-4-(4-amino-5-(difluoromethyl)-1H-pyrazol-1-yl)cyclohexyl)methanol To a solution of ((1r,4r)-4-(5-(difluoromethyl)-4-nitro-1H-pyrazol-1-yl)cyclohexyl)methanol (210 mg, 762 umol) in MeOH (3 mL) was added Pd/C (40.0 mg, 10% wt) and the mixture was stirred at 25° C. under H₂ (15 psi) for 30 min. On completion, the mixture was filtrated and the filtrate was concentrated in vacuo to give the title compound (180 mg, 96% yield) as yellow oil. LC-MS (ESI⁺) m/z 246.1 (M+H)⁺.

N-(5-(difluoromethyl)-1-((1r,4r)-4-formylcyclohexyl)-1H-pyrazol-4-yl)-5-morpholinopyrazolo[1,5-a]pyrimidine-3-carboxamide (Intermediate AUY)

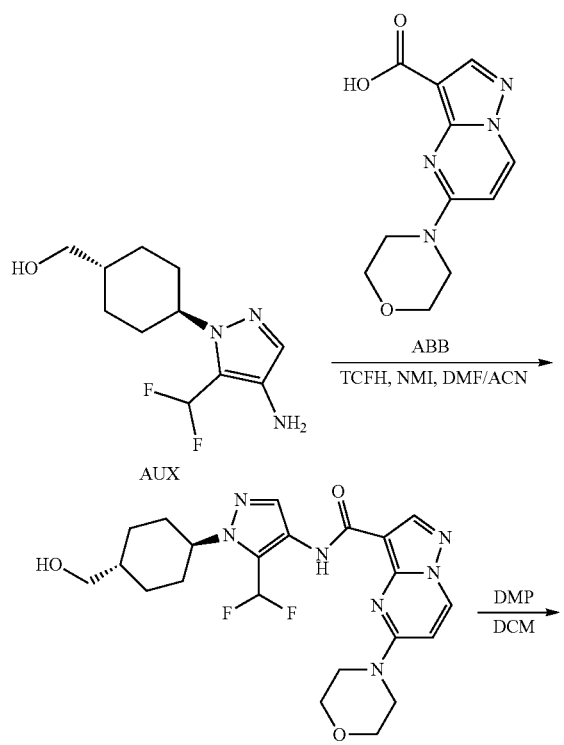

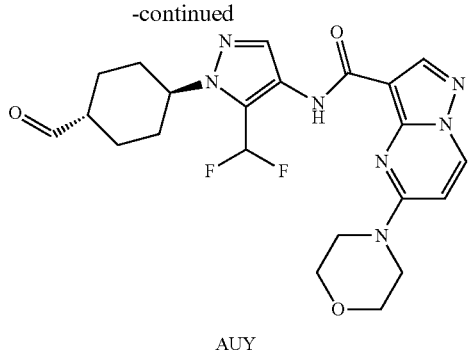

AUY

Step 1—N-(5-(difluoromethyl)-1-((1r,4r)-4-(hydroxymethyl)cyclohexyl)-1H-pyrazol-4-yl)-5-morpholinopyrazolo[1,5-a]pyrimidine-3-carboxamide To a solution of ((1r,4r)-4-(4-amino-5-(difluoromethyl)-1H-pyrazol-1-yl)cyclohexyl)methanol (182 mg, 733 umol, Intermediate AUX) in ACN (4 mL) and DMF (1 mL) was added [chloro(dimethylamino)methylene]-dimethyl-ammonium; hexafluorophosphate (247 mg, 880 umol) and 1-methylimidazole (150 mg, 1.83 mmol), then the mixture was stirred at 25° C. for 30 min. To the reaction mixture was added [5-morpholinopyrazolo[1,5-a]pyrimidine-3-carboxylic acid (180 mg, 733 umol, Intermediate ABB) then the mixture was stirred at 25° C. for 16 hrs. On completion, the mixture was concentrated in vacuo to remove the ACN. The residue was purified by flash silica gel chromatography (ISCO®; 4 g SepaFlash® Silica Flash Column, Eluent of 0-100% ethyl acetate/petroleum ether gradient @ 40 mL/min) to give the title compound (165 mg, 47% yield) as yellow oil. ¹H NMR (400 MHz, DMSO-d₆) δ 9.42 (s, 1H), 8.82 (d, J=8.0 Hz, 1H), 8.28 (s, 1H), 8.06 (s, 1H), 7.68-7.34 (m, 1H), 6.90 (d, J=8.0 Hz, 1H), 4.47 (t, J=5.2 Hz, 1H), 4.31-4.16 (m, 1H), 3.77-3.71 (m, 8H), 3.26 (t, J=5.6 Hz, 2H), 1.93-1.80 (m, 6H), 1.47-1.36 (m, 1H), 1.21-1.07 (m, 2H). LC-MS (ESI⁺) m/z 476.3 (M+H)⁺.

Step 2—N-(5-(difluoromethyl)-1-((1r,4r)-4-formylcyclohexyl)-1H-pyrazol-4-yl)-5-morpholinopyrazolo[1,5-a]pyrimidine-3-carboxamide To a solution of N-(5-(difluoromethyl)-1-((1r,4r)-4-(hydroxymethyl)cyclohexyl)-1H-pyrazol-4-yl)-5-morpholinopyrazolo[1,5-a]pyrimidine-3-carboxamide (155 mg, 325 umol) in DCM (1 mL) was added DMP (138 mg, 325 umol) and the mixture was stirred at 25° C. for 0.5 hr. On completion, the mixture was quenched with saturated solution of Na₂S₂O₃ (2 mL) and extracted by DCM (3×5 mL). The combined organic layer was dried over Na₂SO₄ and the mixture was filtered. The filtrate was concentrated in vacuo to give the title compound (150 mg, 97% yield) as yellow oil. LC-MS (ESI⁺) m/z 474.1 (M+H)*.

Tert-butyl N-methyl-N-prop-2-ynyl-carbamate (Intermediate AVC)

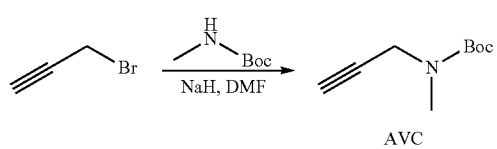

AVC

To a mixture of tert-butyl N-methylcarbamate (6.62 g, 50.4 mmol, CAS #16066-84-5) in DMF (80 mL) was added NaH (2.02 g, 50.4 mmol, 60% purity) at 0° C. for 0.5 hour. Then 3-bromoprop-1-yne (5.00 g, 42.0 mmol, 3.62 mL, CAS #106-96-7) was added to the mixture. The reaction mixture was stirred at 25° C. for 12 hours. On completion, the reaction mixture was quenched with water (50 mL) and extracted with EA (2×100 mL). The combined organic layers was dried over Na$_2$SO$_4$, filtered and concentrated in vacuo to give a residue. The residue was purified by column chromatography to give the title compound (4.50 g, 63% yield) as light yellow oil. $^1$H NMR (400 MHz, CDCl$_3$) δ 4.03 (s, 2H), 2.90 (s, 3H), 2.20 (t, J=2.4 Hz, 1H), 1.46 (s, 9H).

3-[3-Methyl-4-[3-(methylamino)propyl]-2-oxo-benzimidazol-1-yl]piperidine-2,6-dione (Intermediate AVD)

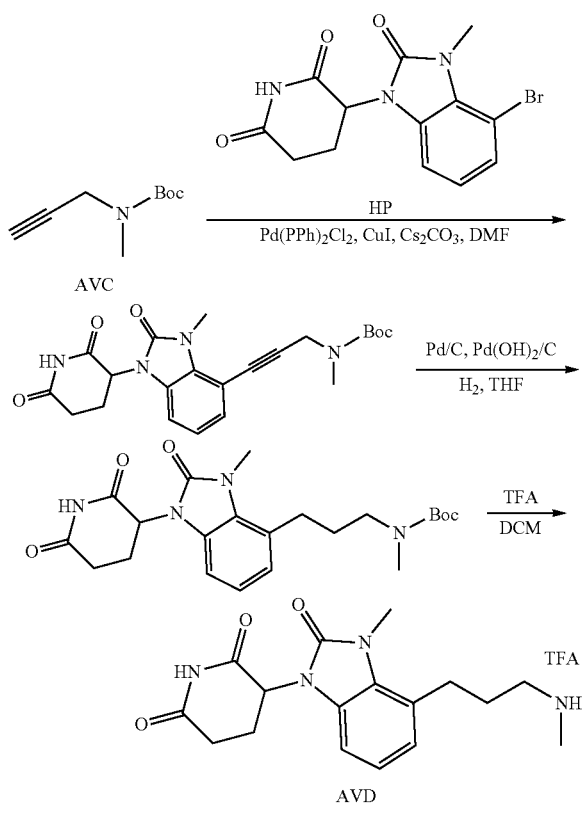

Step 1—Tert-butyl N-[3-[1-(2,6-dioxo-3-piperidyl)-3-methyl-2-oxo-benzimidazol-4-yl]prop-2-ynyl]-N-methyl-carbamate To a mixture of tert-butyl N-methyl-N-prop-2-ynyl-carbamate (400 mg, 2.37 mmol, Intermediate AVC) and 3-(4-bromo-3-methyl-2-oxo-benzimidazol-1-yl)piperidine-2,6-dione (400 mg, 1.18 mmol, Intermediate HP) in DMF (15 mL) was added CuI (22.5 mg, 118 umol), Cs$_2$CO$_3$ (1.93 g, 5.91 mmol) and Pd(PPh$_3$)$_2$Cl$_2$ (83.0 mg, 118 umol). The reaction mixture was stirred at 80° C. for 2 hours under N$_2$ atmosphere. On completion, the reaction mixture was filtered and concentrated in vacuo. The residue was purified by reverse phase (0.1% FA condition) to give the title compound (200 mg, 39% yield) as brown solid. 1H NMR (400 MHz, DMSO-d$_6$) δ 11.12 (s, 1H), 7.16 (d, J=7.6 Hz, 1H), 7.10 (d, J=7.2 Hz, 1H), 7.05-6.99 (m, 1H), 5.43-5.36 (m, 1H), 4.29 (s, 2H), 3.61 (s, 3H), 2.90 (s, 3H), 2.88-2.81 (m, 1H), 2.73-2.59 (m, 2H), 2.07-1.97 (m, 1H), 1.42 (s, 9H).

Step 2—Tert-butyl N-[3-[1-(2,6-dioxo-3-piperidyl)-3-methyl-2-oxo-benzimidazol-4-yl]propyl]-N-methyl-carbamate To a mixture of tert-butyl N-[3-[1-(2,6-dioxo-3-piperidyl)-3-methyl-2-oxo-benzimidazol-4-yl]prop-2-ynyl]-N-methyl-carbamate (200 mg, 468 umol) in THF (20 mL) was added Pd/C (100 mg, 10 wt %) and Pd(OH)$_2$/C (100 mg, 10 wt %). The reaction mixture was stirred at 25° C. for 12 hours. On completion, the reaction mixture was filtered and concentrated in vacuo to give the compound (200 mg, 99% yield) as white solid. $^1$H NMR (400 MHz, DMSO-d$_6$) δ 11.09 (s, 1H), 7.01-6.94 (m, 1H), 6.90-6.86 (m, 1H), 5.41-5.32 (m, 1H), 3.55 (s, 3H), 3.29-3.22 (m, 2H), 2.96-2.89 (m, 1H), 2.89-2.84 (m, 2H), 2.80 (s, 3H), 2.72-2.58 (m, 2H), 2.02-1.95 (m, 1H), 1.84-1.74 (m, 2H), 1.37 (d, J=10.6 Hz, 9H).

Step 3—3-[3-Methyl-4-[3-(methylamino)propyl]-2-oxo-benzimidazol-1-yl]piperidine-2,6-dione To a mixture of tert-butyl N-[3-[1-(2,6-dioxo-3-piperidyl)-3-methyl-2-oxo-benzimidazol-4-yl]propyl]-N-methyl-carbamate (190 mg, 441 umol) in DCM (4 mL) was added TFA (5.85 g, 51.3 mmol, 3.80 mL). The reaction mixture was stirred at 25° C. for 1 hour. On completion, the reaction mixture was concentrated in vacuo to give the title compound (196 mg, 99% yield, TFA salt) as red oil. LC-MS (ESI$^+$) m/z 331.2 (M+H)$^+$.

(R)-Tert-butyl 4-(but-3-yn-2-yloxy)piperidine-1-carboxylate (Intermediate AVE)

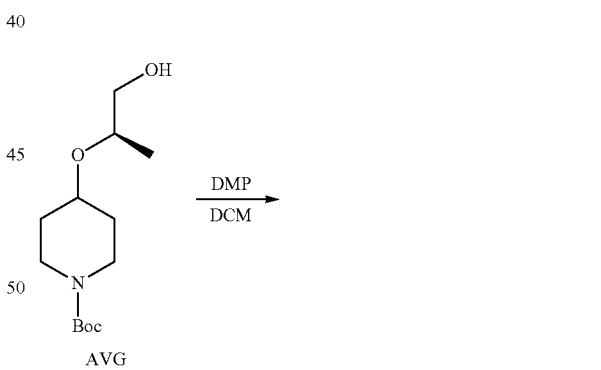

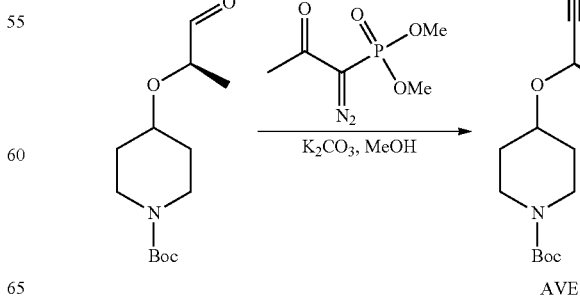

Step 1—(R)-Tert-butyl 4-((1-oxopropan-2-yl)oxy)piperidine-1-carboxylate

To a solution of tert-butyl 4-[(1R)-2-hydroxy-1-methylethoxy] piperidine-1-carboxylate (5.00 g, 19.2 mmol, Intermediate AVG) in DCM (10 mL) was added DMP (9.81 g, 23.1 mmol), and the mixture was stirred at 25° C. for 1 hr. On completion, the mixture was quenched with water (100 mL) and extracted with ethyl acetate (3×250 mL). The combined organic phase was dried over anhydrous sodium sulfate, filtered and concentrated to give a residue. The residue was purified by silica gel chromatography (PE:EA=10:1) to give the title compound (3.50 g, 63% yield) as colorless oil. $^1$H NMR (400 MHz, CDCl$_3$-d) δ 9.57 (d, J=1.6 Hz, 1H), 3.86-3.24 (m, 1H), 3.79-3.67 (m, 3H), 1.83-1.71 (m, 3H), 1.39 (s, 12H), 1.22 (d, J=7.6 Hz, 3H).

Step 2—(R)-Tert-butyl 4-(but-3-yn-2-yloxy)piperidine-1-carboxylate

To a solution of tert-butyl 4-[(1R)-1-methyl-2-oxoethoxy]piperidine-1-carboxylate (3.50 g, 13.6 mmol) and K$_2$CO$_3$ (5.64 g, 40.8 mmol) in MeOH (5 mL) was stirred at 0° C. Then to the mixture was added dimethyl (1-diazo-2-oxopropyl)phosphonate (3.14 g, 16.3 mmol) and the mixture was stirred at 0° C. for 1 hr. On completion, the mixture was quenched with water (100 mL) and extracted with ethyl acetate (3×250 mL). The combined organic phase was dried over anhydrous sodium sulfate, filtered and concentrated to give a residue. The residue was purified by silica gel chromatography (PE:EA=10:1) to give the title compound (2.1 g, 54% yield) as a white solid. $^1$H NMR (400 MHz, DMSO-d$_6$) δ 4.43-4.37 (m, 1H), 3.83-3.73 (m, 1H), 3.72-3.61 (m, 2H), 3.44 (d, J=1.6 Hz, 1H), 3.08 (d, J=10.4 Hz, 2H), 1.91-1.75 (m, 2H), 1.49-1.34 (m, 14H).

3-(3-Methyl-2-oxo-4-((R)-3-(piperidin-4-yloxy)but-1-yn-1-yl)-2,3-dihydro-1H-benzo[d] imidazol-1-yl)piperidine-2,6-dione (Intermediate AVF)

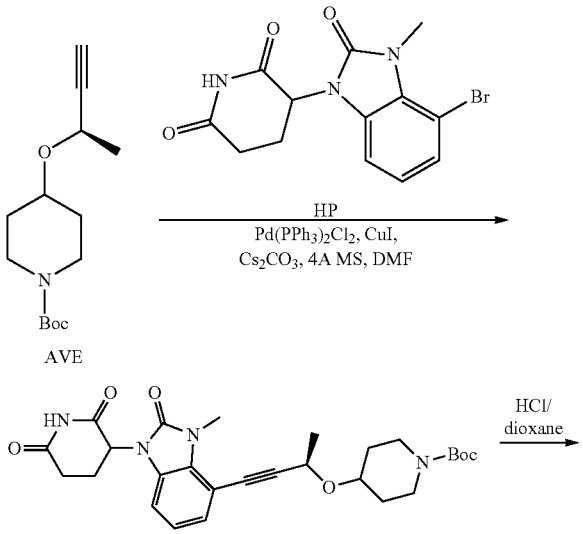

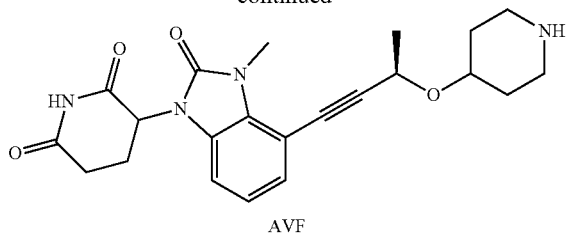

Step 1—Tert-butyl 4-(((2R)-4-(1-(2,6-dioxopiperidin-3-yl)-3-methyl-2-oxo-2,3-dihydro-1H-benzo[d]imidazol-4-yl)but-3-yn-2-yl)oxy)piperidine-1-carboxylate To a solution of 3-(4-bromo-3-methyl-2-oxo-benzimidazol-1-yl)piperidine-2,6-dione (1.60 g, 4.74 mmol, Intermediate HP), tert-butyl 4-[(1R)-1-methylprop-2-ynoxy]piperidine-1-carboxylate (1.80 g, 7.11 mmol, Intermediate AVE), Pd(PPh$_3$)$_2$Cl$_2$ (332 mg, 473 umol), CuI (180 mg, 947 umol), Cs$_2$CO$_3$ (6.17 g, 18.9 mmol) and 4 Å molecular sieves (1.00 g) in DMF (20 mL) was stirred at 80° C. for 4 hrs under nitrogen atmosphere. On completion, the mixture was quenched with water (100 mL) and extracted with ethyl acetate (3×250 mL). The combined organic phase was dried over anhydrous sodium sulfate, filtered and concentrated to give a residue. The residue was purified by Prep-HPLC (column: Water X bridge C18 330 g; mobile phase: [water-ACN]; B %: 50%-60%, 8 min) to give the title compound (1.9 g, 77% yield) as a white solid. $^1$H NMR (400 MHz, DMSO-d$_6$) δ 11.12 (s, 1H), 7.22-6.98 (m, 3H), 5.43-5.38 (m, 1H), 4.67 (q, J=6.4 Hz, 1H), 3.88-3.77 (m, 1H), 3.65 (s, 5H), 3.05 (d, J=10.4 Hz, 2H), 2.96-2.83 (m, 1H), 2.77-2.59 (m, 2H), 2.07-2.00 (m, 1H), 1.92-1.77 (m, 2H), 1.45 (d, J=6.4 Hz, 3H), 1.39 (s, 11H).

Step 2—3-(3-Methyl-2-oxo-4-((R)-3-(piperidin-4-yloxy)but-1-yn-1-yl)-2,3-dihydro-1H-benzo[d] imidazol-1-yl)piperidine-2,6-dione A solution of tert-butyl 4-[(1R)-3-[1-(2,6-dioxo-3-piperidyl)-3-methyl-2-oxo-benzimidazol-4-yl]-1-methyl-prop-2-ynoxy]piperidine-1-carboxylate (150 mg, 293 umol) in HCl-dioxane (4 M, 2 mL) was stirred at 25° C. for 0.5 hr. On completion, the reaction mixture was concentrated to give the title compound (110 mg, 86% yield) as a white solid. LC-MS (ESI$^+$) m/z 411.1 (M+H)$^+$.

(R)-tert-butyl 4-((1-hydroxypropan-2-yl)oxy)piperidine-1-carboxylate (Intermediate AVG)

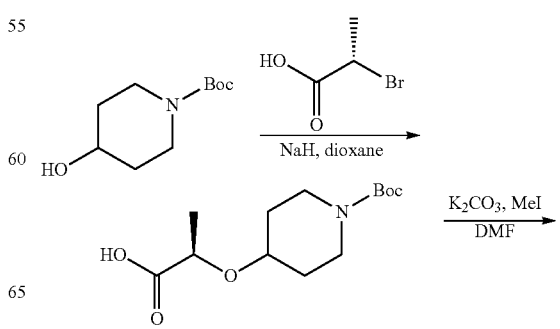

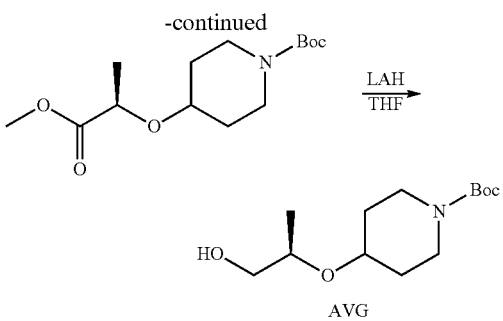

Step 1—(R)-2-((1-(tert-butoxycarbonyl)piperidin-4-yl)oxy)propanoic acid

To a solution of NaH (26.2 g, 654 mmol) in dioxane (250 mL) was added tert-butyl 4-hydroxypiperidine-1-carboxylate (28.9 g, 144 mmol) at 0° C., it was stirred at 0° C. for 0.5 h. Then (2S)-2-bromopropanoic acid (20 g, 131 mmol, CAS #32644-15-8) was added, it was stirred at 25° C. for 16 h. It was quenched with water (1.5 L) and then extracted with EA (800 mL). The aqueous layer was adjusted pH to 2, then extracted with EA (500 mL×2). The organic layers were collected, dried, filtered and concentrated to give the residue. After 16 hrs, solid had precipitated, the solution was filtered to give the crude product. The solid was washed with PE/MeOH(5/1, 20 mL) to give the title product (21 g, 73.0 mmol, 27.9% yield) as a yellow solid. $^1$H NMR (400 MHz, DMSO-$d_6$) δ 12.54 (s, 1H), 4.07 (m, 1H), 3.65 (m, 2H), 3.50 (s, 1H), 3.33 (s, 2H), 2.99 (s, 2H), 1.85 (m, 2H), 1.38 (s, 9H), 1.24 (m, 3H).

Step 2—(R)-tert-butyl 4-((1-methoxy-1-oxopropan-2-yl)oxy)piperidine-1-carboxylate To a solution of (2R)-2-[(1-tert-butoxycarbonyl-4-piperidyl)oxy]propanoic acid (21 g, 76.8 mmol) in DMF (25 mL) was added $K_2CO_3$ (21.2 g, 154 mmol) and MeI (54.5 g, 384 mmol), and the solution was stirred at 20° C. for 14 h. Upon completion, the reaction was concentrated to give the residue. The residue was diluted with water (1 L) and extracted with EA (200 mL×3). The organic layers were collected, dried, filtered and concentrated to give the title product (21 g, 69.4 mmol, 95% yield) as a yellow oil. $^1$H NMR (400 MHz, CDCl$_3$) δ 4.13 (m, 1H), 3.74-3.52 (m, 5H), 3.50 (m, 1H), 3.10-3.03 (m, 2H), 1.82-1.80 (m, 2H), 1.58 (m, 2H), 1.49-1.45 (m, 9H), 1.44-1.38 (m, 3H).

Step 3—(R)-tert-butyl 4-((1-hydroxypropan-2-yl)oxy)piperidine-1-carboxylate

To a solution of LAH (4.16 g, 110 mmol) in THF (100 mL) was dropwise added a solution of tert-butyl 4-[(1R)-2-methoxy-1-methyl-2-oxo-ethoxy]piperidine-1-carboxylate (21 g, 73.1 mmol) in THF (110 mL) at 0° C., then it was stirred at 0° C. for 1 h. Upon completion, the solution was quenched with NaOH (1N, 4.20 mL). Next, 50 g of $Na_2SO_4$ was added and 200 mL of EA under stirring. 15 minutes later, the solution was filtered to give the filtrate, which was concentrated to give the title product (15.5 g, 53.8 mmol, 82% yield). $^1$H NMR (400 MHz, CDCl$_3$) δ 3.81-7.42 (m, 7H), 3.05-3.02 (m, 2H), 2.11 (m, 1H), 1.75 (s, 1H), 1.65 (m, 2H), 1.45 (s, 9H), 1.12-1.09 (m, 3H). LC-MS (ESI$^+$) m/z 203.9 (M-COOH+H)$^+$.

Methyl 4-methylsulfonyloxycyclohexanecarboxylate (Intermediate AVH)

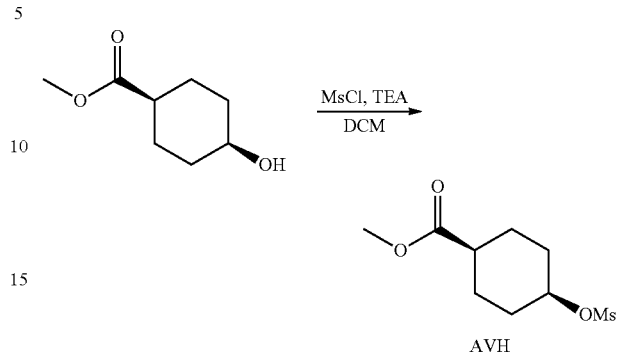

To a mixture of methyl 4-hydroxycyclohexanecarboxylate (1.00 g, 6.32 mmol, CAS #3618-03-9) in DCM (10 mL) was added TEA (831 mg, 8.22 mmol) and MsCl (1.09 g, 9.48 mmol) at 0° C., and the reaction mixture was stirred 0° C. for 2 hours. On completion, the mixture was poured into the ice-water (50 mL) and extracted with DCM (2×30 mL). The combined organic phase was washed with brine (2×50 mL), dried with anhydrous $Na_2SO_4$, filtered and concentrated in vacuo to give the title compound (1.20 g, 80% yield) as colorless oil. $^1$H NMR (400 MHz, CDCl$_3$) δ 4.91 (t, J=2.8, 5.2 Hz, 1H), 3.69 (s, 3H), 3.02 (s, 3H), 2.41-2.39 (m, 1H), 2.09-1.99 (m, 2H), 1.97-1.86 (m, 2H), 1.80 (t, J=4.4, 9.2 Hz, 2H), 1.75-1.66 (m, 2H).

Benzyl methyl(2-methylenespiro[3.5]nonan-7-yl)carbamate (Intermediate ARV)

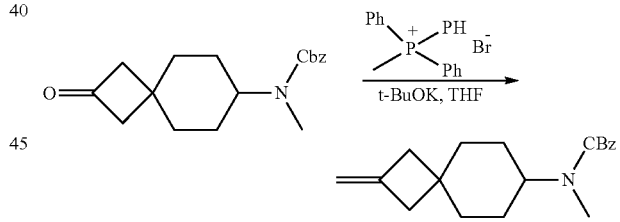

To a solution of methyl(triphenyl)phosphonium; bromide (1.69 g, 4.74 mmol) in THF (15 mL) was added t-BuOK (532 mg, 4.74 mmol) at 0° C., then the mixture was warmed to 40° C. and stirred for 3 hrs. Then benzyl N-methyl-N-(2-oxospiro[3.5]nonan-7-yl)carbamate (650 mg, 2.16 mmol, synthesized via Steps 1-5 of Intermediate ANJ) in THF (5 mL) was added at 0° C. and the mixture was warmed to 40° C. for 1 hr. On completion, the reaction was quenched with $NH_4Cl$ aqueous (10 mL). The aqueous was extracted with EA (3×20 mL). The combined organic layer was washed with brine, dried over $Na_2SO_4$ and concentrated in vacuo. The residue was purified by column chromatography (PE:EA=100:1) to give the title compound (400 mg, 62% yield) as a colorless oil. $^1$H NMR (400 MHz, CDCl$_3$) δ 7.42-7.28 (m, 5H), 5.14 (s, 2H), 4.89-4.76 (m, 2H), 4.09-3.76 (m, 1H), 2.79 (s, 3H), 2.41-2.37 (m, 4H), 1.79-1.76 (m, 2H), 1.64-1.58 (m, 2H), 1.53-1.38 (m, 4H).

3-(3-Methyl-4-((7-(methylamino)spiro[3.5]nonan-2-yl)methyl)-2-oxo-2,3-dihydro-1H-benzo[d]imidazol-1-yl)piperidine-2,6-dione (Intermediate ARW)

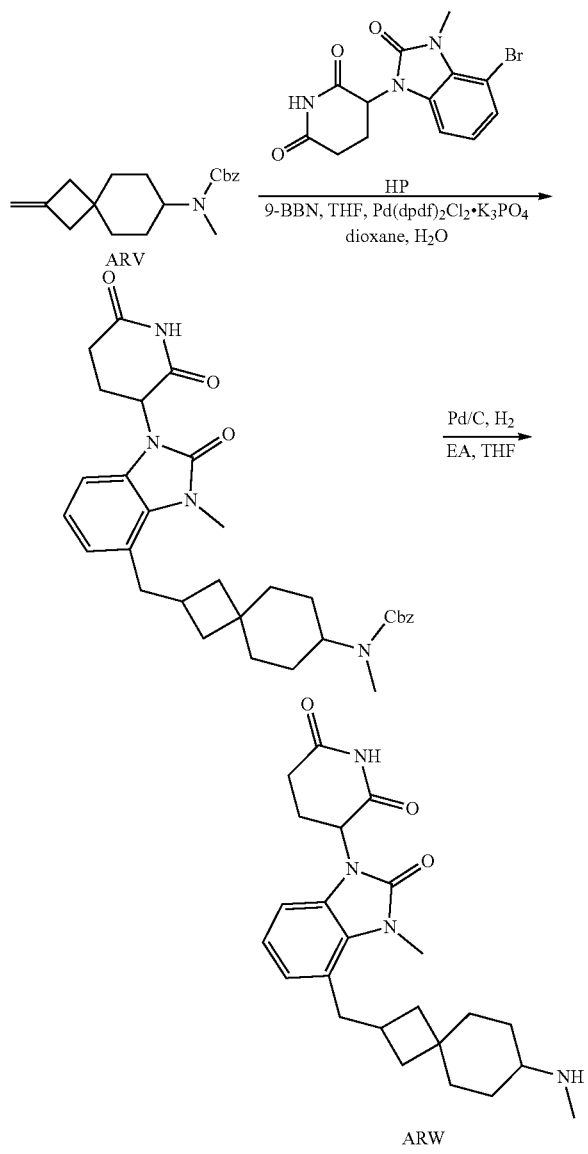

Step 1—Benzyl (2-((1-(2,6-dioxopiperidin-3-yl)-3-methyl-2-oxo-2,3-dihydro-1H-benzo[d]imidazol-4-yl)methyl)spiro[3.5]nonan-7-yl)(methyl)carbamate A mixture of benzyl N-methyl-N-(2-methylenespiro[3.5]nonan-7-yl)carbamate (1.30 g, 4.34 mmol, Intermediate ARV) and 9-BBN (0.5 M, 8.68 mL, CAS #280-64-8) in THF (10 mL) was stirred at 25° C. for 3 hrs. The above mixture was added to a mixture of 3-(4-bromo-3-methyl-2-oxo-benzimidazol-1-yl)piperidine-2,6-dione (2.20 g, 6.51 mmol, Intermediate HP); ditert-butyl(cyclopentyl)phosphane; dichloropalladium; iron (282 mg, 434 umol) and K$_3$PO$_4$ (2.30 g, 10.8 mmol) in a mixture of dioxane (20 mL) and H$_2$O (2 mL). Then the mixture was stirred at 80° C. for 4 hrs under N$_2$ atmosphere. On completion, the reaction was filtered. The filtrate was purified by reverse phase (FA) to give the title compound (1.10 g, 45% yield) as a yellow solid. $^1$H NMR (400 MHz, CDCl$_3$) δ=8.52 (s, 1H), 7.49-7.28 (m, 5H), 7.04-6.91 (m, 1H), 6.85 (d, J=7.6 Hz, 1H), 6.67 (d, J=7.6 Hz, 1H), 5.22 (dd, J=4.8, 12.0 Hz, 1H), 5.13 (s, 2H), 3.73-3.46 (m, 3H), 3.20-2.74 (m, 7H), 2.60-2.35 (m, 2H), 2.25-2.16 (m, 1H), 2.06-1.98 (m, 1H), 1.92-1.74 (m, 3H), 1.68-1.38 (m, 9H).

Step 2—3-(3-Methyl-4-((7-(methylamino)spiro[3.5]nonan-2-yl)methyl)-2-oxo-2,3-dihydro-1H-benzo[d]imidazol-1-yl)piperidine-2,6-dione To a solution of benzyl N-[2-[[1-(2,6-dioxo-3-piperidyl)-3-methyl-2-oxo-benzimidazol-4-yl]methyl] spiro[3.5]nonan-7-yl]-N-methyl-carbamate (1.00 g, 1.79 mmol) in EA (10 mL) and THF (10 mL) was added Pd/C (200 mg, 10 wt %) under N$_2$ atmosphere. The suspension was degassed and purged with H$_2$ gas 3 times. The mixture was stirred at 25° C. for 4 hrs under H$_2$ (15 psi) atmosphere. On completion, the reaction was filtered. The filtrate was concentrated to give the title compound (700 mg, 92% yield, 90% purity) as a white solid. $^1$H NMR (400 MHz, CDCl$_3$) δ 7.00-6.92 (m, 1H), 6.85 (d, J=7.6 Hz, 1H), 6.66 (d, J=7.6 Hz, 1H), 5.30-5.15 (m, 1H), 3.66 (s, 3H), 3.02 (d, J=7.2 Hz, 1H), 2.97-2.90 (m, 2H), 2.83-2.74 (m, 2H), 2.58-2.45 (m, 1H), 2.41 (s, 3H), 2.32-2.18 (m, 2H), 2.04-1.97 (m, 1H), 1.93-1.67 (m, 4H), 1.63-1.42 (m, 4H), 1.40-1.28 (m, 2H), 1.20-1.02 (m, 2H).

Tert-butyl 4-[(1S)-3-amino-1-methyl-propoxy]piperidine-1-carboxylate (Intermediate AVR)

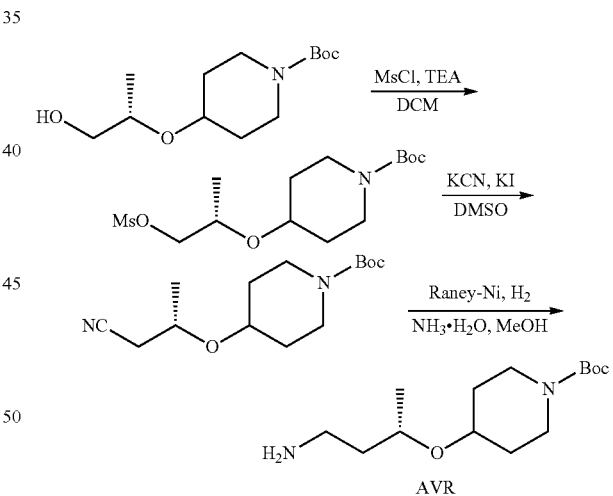

Step 1—Tert-butyl 4-[(1S)-1-methyl-2-methylsulfonyloxy-ethoxy]piperidine-1-carboxylate To a solution of tert-butyl 4-[(1S)-2-hydroxy-1-methyl-ethoxy]piperidine-1-carboxylate (1.50 g, 5.78 mmol, synthesized via Steps 1-3 of Intermediate AQA) and TEA (1.46 g, 14.46 mmol, 2.01 mL) in DCM (15 mL) was added MsCl (993 mg, 8.68 mmol) at 0° C. The mixture was stirred at 0-10° C. for 1 hr. On completion, the reaction mixture was diluted with H$_2$O 10 mL and extracted with EA 30 mL (3×10 mL). The combined organic layers were washed by brine dried over by Na$_2$SO$_4$, filtered and the filtrate was concentrated in vacuo to give the title compound (1.87 g, 86% yield, 90% purity) as black oil. $^1$H NMR (400 MHz, CDCl$_3$) δ 4.18-4.07 (m, 2H), 3.90-3.81 (m, 1H), 3.77 (d, J=13.6 Hz, 2H), 3.65-3.55 (m, 1H), 3.13-3.06 (m, 2H), 3.05 (s, 3H), 1.86-1.76 (m, 2H), 1.55-1.47 (m, 2H), 1.46 (s, 9H), 1.20 (d, J=6.4 Hz, 3H).

Step 2—Tert-butyl 4-[(1S)-2-cyano-1-methyl-ethoxy]piperidine-1-carboxylate

To a solution of tert-butyl 4-[(1S)-1-methyl-2-methyl-sulfonyloxy-ethoxy]piperidine-1-carboxylate (1.87 g, 4.99 mmol) in DMSO (20 mL) was added KI (1.24 g, 7.48 mmol) and KCN (389 mg, 5.99 mmol) at 25° C. The mixture was stirred at 100° C. for 12 hr. On completion, the mixture was diluted with 30 mL H$_2$O and extracted with EA (3×10 mL). The combined organic layers were washed by brine (20 mL), dried over by Na$_2$SO$_4$, filtered and the filtrate was concentrated in vacuo. The residue was purified by column chromatography to give the title compound (980 mg, 73% yield) as colorless oil. $^1$H NMR (400 MHz, CDCl$_3$) δ 3.91-3.82 (m, 1H), 3.76-3.66 (m, 2H), 3.65-3.55 (m, 1H), 3.20-3.09 (m, 2H), 2.48 (dd, J=2.0, 6.0 Hz, 2H), 1.84-1.73 (m, 2H), 1.56-1.49 (m, 2H), 1.45 (s, 9H), 1.28 (d, J=6.0 Hz, 3H).

Step 3—Tert-butyl 4-[(1S)-3-amino-1-methyl-propoxy]piperidine-1-carboxylate

To a solution of tert-butyl 4-[(1S)-2-cyano-1-methyl-ethoxy]piperidine-1-carboxylate (500 mg, 1.86 mmol) in NH$_3$.H$_2$O (1 mL) and MeOH (10 mL) was added Raney-Ni (79.8 mg, 931 umol) at 25° C. The reaction mixture was stirred at 25° C. for 3 hrs under H$_2$ (50 Psi). On completion, the mixture was filtered with celite and the filtrate was concentrated in vacuo to give the title compound (580 mg, 97% yield, 85% purity) as black oil.

2-(2,6-Dioxo-3-piperidyl)-4-[[(3S)-3-(4-piperidyloxy)butyl]amino]isoindoline-1,3-dione (Intermediate AVS)

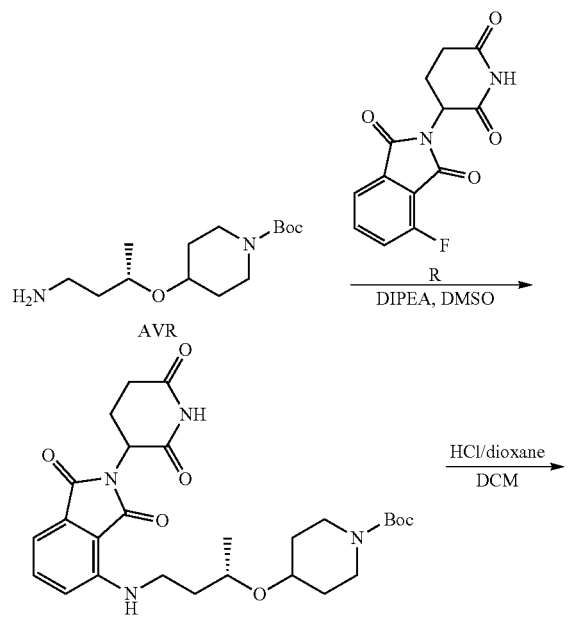

Step 1—Tert-butyl 4-[(1S)-3-[[2-(2,6-dioxo-3-piperidyl)-1,3-dioxo-isoindolin-4-yl] amino]-1-methyl-propoxy]piperidine-1-carboxylate To a solution of tert-butyl 4-[(1S)-3-amino-1-methyl-propoxy]piperidine-1-carboxylate (580 mg, 1.81 mmol, Intermediate AVR) and 2-(2,6-dioxo-3-piperidyl)-4-fluoro-isoindoline-1,3-dione (549 mg, 1.99 mmol, Intermediate R) in DMSO (15 mL) was added DIPEA (467 mg, 3.62 mmol) at 25° C. The reaction mixture was stirred at 130° C. for 3 hrs. On completion, the reaction mixture was concentrated in vacuo. The residue was purified by reverse phase (0.1% FA condition) to give the title compound (580 mg, 60% yield) as a yellow solid. $^1$H NMR (400 MHz, DMSO-d$_6$) δ 11.09 (d, J=2.4 Hz, 1H), 7.59 (dd, J=7.2, 8.4 Hz, 1H), 7.15-6.95 (m, 2H), 6.65-6.52 (m, 1H), 5.04 (dd, J=5.6, 12.8 Hz, 1H), 3.74-3.49 (m, 4H), 3.41-3.36 (m, 2H), 3.05-2.82 (m, 3H), 2.62-2.52 (m, 2H), 2.06-1.96 (m, 1H), 1.80-1.61 (m, 4H), 1.37 (d, J=1.6 Hz, 9H), 1.35-1.21 (m, 2H), 1.12 (d, J=6.0 Hz, 3H); LC-MS (ESI$^+$) m/z 529.1 (M+H)$^+$.

Step 2—2-(2,6-Dioxo-3-piperidyl)-4-[[(3S)-3-(4-piperidyloxy)butyl] amino]isoindoline-1,3-dione To a solution of tert-butyl 4-[(1S)-3-[[2-(2,6-dioxo-3-piperidyl)-1,3-dioxo-isoindolin-4-yl]amino]-1-methyl-propoxy]piperidine-1-carboxylate (100 mg, 189 umol) in DCM (2 mL) was added HCl/dioxane (4 M, 5.00 mL) at 25° C. The mixture was stirred at 25° C. for 1 hr. On completion, the reaction mixture was concentrated in vacuo to give the title compound (85.0 mg, 96% yield, HCl salt) as a yellow solid. LC-MS (ESI$^+$) m/z 429.2 (M+H)$^+$.

Tert-butyl N-[4-(bromomethyl)cyclohexyl]-N-methyl-carbamate (Intermediate AVT)

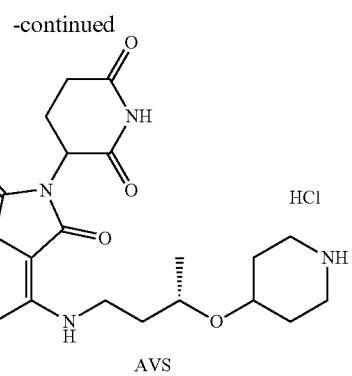

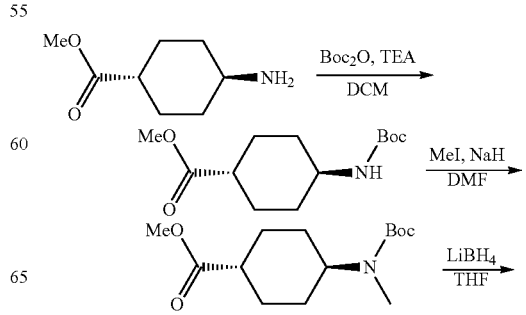

-continued

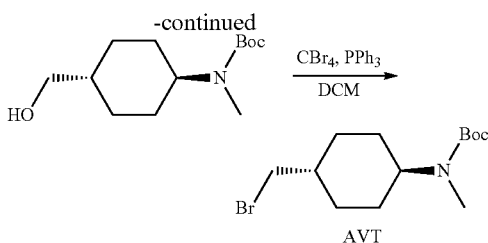

Step 1—Methyl 4-(tert-butoxycarbonylamino)cyclohexanecarboxylate

To a solution of methyl 4-aminocyclohexanecarboxylate (1.70 g, 10.8 mmol) in DCM (20 mL) was added TEA (2.41 g, 23.8 mmolL) and Boc$_2$O (2.60 g, 11.9 mmol) at 0° C. and then the mixture was stirred at 25° C. for 12 hrs. On completion, the residue was added citric acid (8 g acid in 64 ml water) and extracted with EA (3×40 ml). The combined organic layers were washed with aqueous NaCl (3×30 mL), dried over anhydrous Na$_2$SO$_4$, filtered and concentrated under reduced pressure to give the title compound (3.0 g, 95% yield) as a gray solid. $^1$H NMR (400 MHz, DMSO-d$_6$) δ 6.69 (d, J=7.6 Hz, 1H), 3.57 (s, 3H), 3.22-3.09 (m, 1H), 2.18 (tt, J=3.6, 12.0 Hz, 1H), 1.91-1.77 (m, 4H), 1.37 (s, 9H), 1.35-1.28 (m, 2H), 1.17-1.10 (m, 2H).

Step 2—Methyl 4-[tert-butoxycarbonyl(methyl)amino]cyclohexanecarboxylate

To a solution of methyl 4-(tert-butoxycarbonylamino)cyclohexanecarboxylate (3.00 g, 11.7 mmol) in DMF (100 mL) was added NaH (1.87 g, 46.6 mmol, 60% dispersion in mineral oil), the mixture was degassed and purged with N$_2$ for 3 times, and then stirred at 25° C. for 1 hr under N$_2$ atmosphere. MeI (16.6 g, 117 mmol, 7.26 mL) was added and the mixture was stirred at 25° C. for 17 hr under N$_2$ atmosphere. On completion, the mixture was adjusted pH to 7 with HCl (2 N). Then the mixture was added into 60 ml of water and extracted with EA (3×40 ml). The combined organic layers were washed with aqueous NaCl (3×40 mL), dried over anhydrous Na$_2$SO$_4$, filtered and concentrated under reduced pressure to give the title compound (3.4 g, crude) as yellow oil. $^1$H NMR (400 MHz, DMSO-d$_6$) δ 3.82-3.63 (m, 1H), 3.58 (s, 3H), 2.65 (s, 3H), 2.25 (tt, J=3.6, 12.0 Hz, 1H), 1.98-1.92 (m, 2H), 1.60-1.54 (m, 2H), 1.53-1.45 (m, 2H), 1.45-1.41 (m, 1H), 1.39 (s, 9H), 1.33 (d, J=3.6 Hz, 1H).

Step 3—Tert-butyl N-[4-(hydroxymethyl)cyclohexyl]-N-methyl-carbamate

To a solution of methyl 4-[tert-butoxycarbonyl(methyl)amino]cyclohexanecarboxylate (3.4 g, 12.5 mmol) in THF (40 mL) was added LiBH$_4$ (1.09 g, 50.1 mmol) at 0° C. under N$_2$ atmosphere. The mixture was stirred at 80° C. for 3 hr. On completion, the reaction mixture was quenched by with H$_2$O (60 mL) and extracted with EA (3×60 mL). The combined organic layers were washed with aqueous NaCl (3×40 mL), dried over anhydrous Na$_2$SO$_4$, filtered and concentrated under reduced pressure to give the title compound (3.00 g, 80% yield) as yellow oil. $^1$H NMR (400 MHz, DMSO-d$_6$) δ 4.38 (s, 1H), 3.82-3.54 (m, 1H), 3.21-3.16 (m, 2H), 2.65 (s, 3H), 1.82-1.73 (m, 2H), 1.60-1.42 (m, 4H), 1.38 (s, 9H), 1.28-1.23 (m, 1H), 0.93 (dq, J=3.2, 12.4 Hz, 2H).

Step 4—Tert-butyl N-[4-(bromomethyl)cyclohexyl]-N-methyl-carbamate

A mixture of tert-butyl N-[4-(hydroxymethyl)cyclohexyl]-N-methyl-carbamate (3.00 g, 12.3 mmol), and PPh$_3$ (9.70 g, 40.0 mmol) in DCM (40 mL) was degassed and purged with N$_2$ for 3 times. Then the mixture was stirred at 0° C. and CBr$_4$ (12.3 g, 37.0 mmol) was added, and the mixture was stirred at 25° C. for 12 hr under N$_2$ atmosphere. On completion, the reaction mixture was filtered and concentrated under reduced pressure to give a residue. The residue was purified by column chromatography (PE: EA=20:1) to give the title compound (1.00 g, 27% yield) as yellow oil. $^1$H NMR (400 MHz, DMSO-d$_6$) δ 3.84-3.59 (m, 1H), 3.42 (d, J=6.0 Hz, 2H), 2.64 (s, 3H), 1.87 (d, J=12.8 Hz, 2H), 1.61-1.45 (m, 5H), 1.38 (s, 9H), 1.14-1.04 (m, 2H).

3-[3-methyl-4-[[4-(methylamino)cyclohexyl]methyl]-2-oxo-benzimidazol-1-yl]piperidine-2,6-dione (Intermediate AVU)

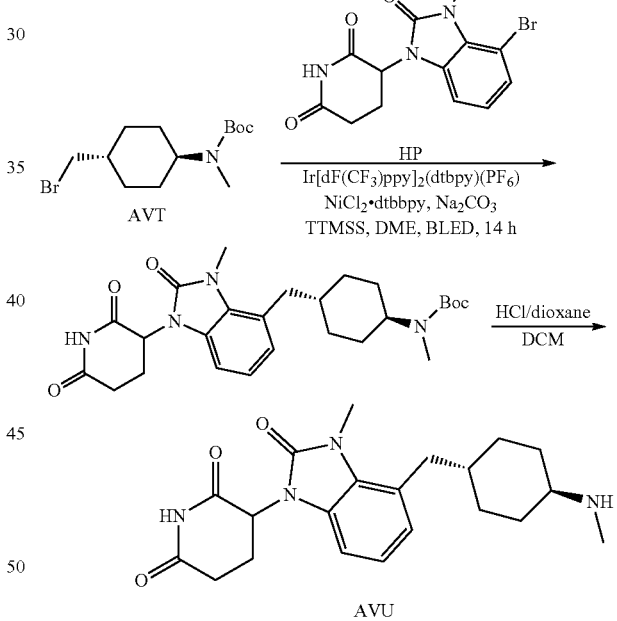

Step 1—Tert-butylN-[4-[[1-(2,6-dioxo-3-piperidyl)-3-methyl-2-oxo-benzimidazol-4-yl]methyl] cyclohexyl]-N-methyl-carbamate To an 40 mL vial equipped with a stir bar was added 3-(4-bromo-3-methyl-2-oxo-benzimidazol-1-yl)piperidine-2,6-dione (993 mg, 2.94 mmol, Intermediate HP), tert-butylN-[4-(bromomethyl) cyclohexyl]-N-methyl-carbamate (900 mg, 2.94 mmol, Intermediate AVT), Ir[dF(CF$_3$)ppy]2 (dtbpy)(PF$_6$) (33.0 mg, 29.4 umol), NiCl$_2$.dtbbpy (5.85 mg, 14.7 umol), Na$_2$CO$_3$ (623 mg, 5.88 mmol), and TTMSS (731 mg, 2.94 mmol, 907 uL) in DME (20 mL). The vial was sealed and placed under nitrogen was added. The reaction was stirred and irradiated with a 34 W blue LED lamp (7 cm away), with cooling fan to keep the reaction temperature at 25° C. for 14 hr. On completion, the reaction mixture was filtered and concentrated under reduced pressure to give a residue. The crude product was purified by reversed-phase HPLC (0.1% FA condition, 65-70% CH₃CN, 5 min) to give the title compound (150 mg, 10% yield) as a white solid. LC-MS (ESI⁺) m/z 429.2 (M+H−56)⁺.

Step 2—3-[3-methyl-4-[[4-(methylamino)cyclohexyl]methyl]-2-oxo-benzimidazol-1-yl]piperidine-2,6-dione To a solution of tert-butylN-[4-[[1-(2,6-dioxo-3-piperidyl)-3-methyl-2-oxo-benzimidazol-4-yl]methyl] cyclohexyl]-N-methyl-carbamate (50 mg, 103 umol) in DCM (3.0 mL) was added HCl/dioxane (4 M, 1.0 mL). The mixture was stirred at 25° C. for 1 hr. On completion, the reaction mixture was concentrated under reduced pressure to give the title compound (40 mg, 90% yield, HCl salt) as a white solid.

5-[(3-Hydroxy-3-methyl-butyl)-methyl-amino]pyrazolo[1,5-a]pyrimidine-3-carboxylic acid (Intermediate AVV)

To a solution of ethyl 5-[(3-hydroxy-3-methyl-butyl)amino]pyrazolo[1,5-a]pyrimidine-3-carboxylate (230 mg, 786.77 umol, Intermediate AHZ) in THF (20 mL) was added NaH (78.6 mg, 1.97 mmol, 60% dispersion in mineral oil). The mixture was stirred at 0° C. for 1 hour. Then CH₃I (134 mg, 944 umol) was added and the mixture was stirred at 0° C. for 1 hour. On completion, the reaction was quenched with ice/water (5 mL). The mixture was concentrated in vacuo. The residue was purified by reversed-phase HPLC (TFA condition) to give the title compound (80.0 mg, 35% yield) as yellow solid. ¹H NMR (400 MHz, DMSO-d₆) δ 11.87-11.23 (m, 1H), 8.68 (d, J=8.0 Hz, 1H), 8.16 (s, 1H), 6.64 (d, J=8.0 Hz, 1H), 3.78-3.55 (m, 2H), 3.16 (s, 3H), 1.74-1.63 (m, 2H), 1.17 (s, 6H); LC-MS (ESI⁺) m/z 301.2 (M+23)⁺.

(R,E)-Tert-butyl 4-((4-(9-borabicyclo[3.3.1]nonan-9-yl)but-3-en-2-yl)oxy)piperidine-1-carboxylate (Intermediate AXV)

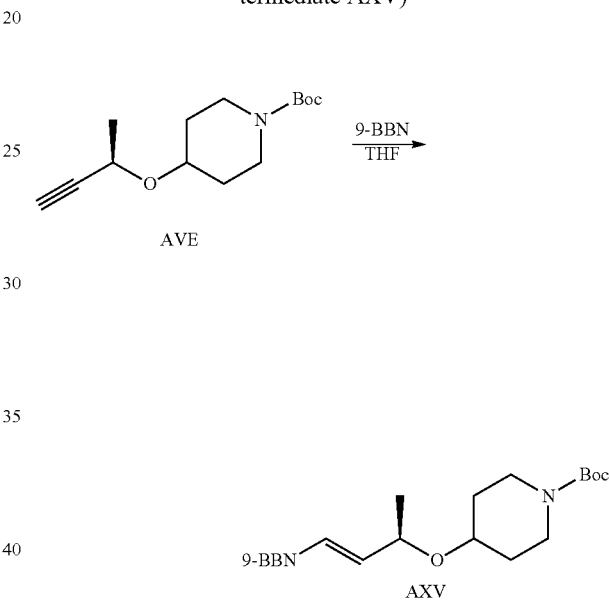

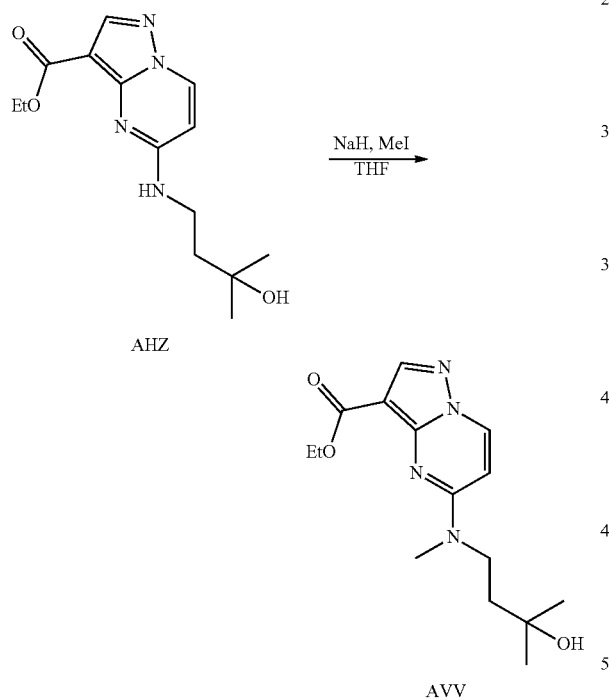

To a solution of tert-butyl 4-[(1R)-1-methylprop-2-ynoxy]piperidine-1-carboxylate (200 mg, 789 umol, Intermediate AVE) and 9-BBN (0.5 M, 2.37 mL) in THF (5 mL) was stirred at 25° C. for 16 hrs under nitrogen atmosphere. On completion, the reaction mixture was used for next step without work-up.

3-(3-Methyl-2-oxo-4-((R,E)-3-(piperidin-4-yloxy)but-1-en-1-yl)-2,3-dihydro-1H-benzo[d]imidazol-1-yl)piperidine-2,6-dione (Intermediate AXW)

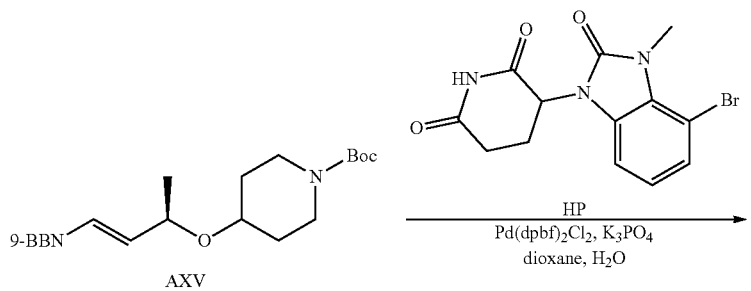

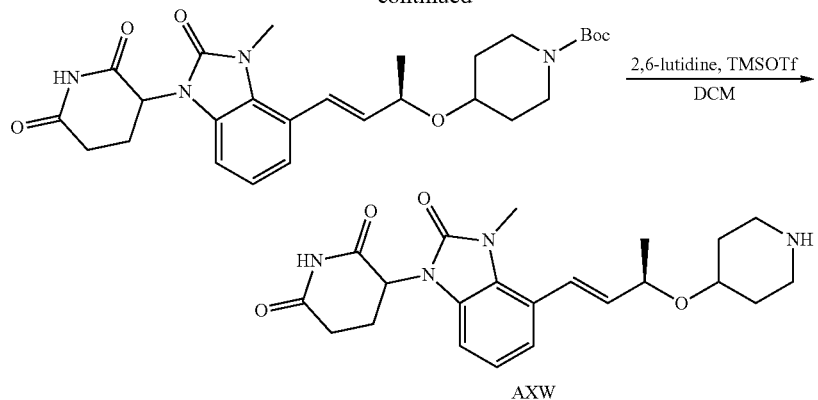

$\xrightarrow{\text{2,6-lutidine, TMSOTf}}{\text{DCM}}$

AXW

Step 1—Tert-butyl 4-(((2R,E)-4-(1-(2,6-dioxopiperidin-3-yl)-3-methyl-2-oxo-2,3-dihydro-1H-benzo[d]imidazol-4-yl)but-3-en-2-yl)oxy)piperidine-1-carboxylate A solution of 3-(4-bromo-3-methyl-2-oxo-benzimidazol-1-yl)piperidine-2,6-dione (243 mg, 719 umol, Intermediate HP), tert-butyl 4-[(E,1S)-3-(9-borabicyclo[3.3.1]nonan-9-yl)-1-methyl-allyloxy] piperidine-1-carboxylate (180 mg, 479 umol, Intermediate AXV), $K_3PO_4$ (254 mg, 1.20 mmol) and ditert-butyl(cyclopentyl) phosphane; dichloropalladium; iron (31.2 mg, 47.9 umol) in dioxane (5 mL) and $H_2O$ (0.5 mL) was stirred at 80° C. for 4 hrs under nitrogen atmosphere. On completion, the mixture was quenched with water (20 mL) and extracted with ethyl acetate (3×30 mL). The combined organic phase was dried over anhydrous sodium sulfate, filtered and concentrated to give a residue. The crude residue was purified by Prep-HPLC (column: Waters X bridge C18 330 g; mobile phase: [water-ACN]; B %: 50%-60%, 8 min) to give the title compound (110 mg, 40% yield) as a brown solid. $^1$H NMR (400 MHz, DMSO-$d_6$) δ 11.10 (s, 1H), 7.22 (d, J=15.6 Hz, 1H), 7.15-7.10 (m, 1H), 7.07-6.99 (m, 2H), 6.04 (d, J=15.6 Hz, 1H), 5.38 (d, J=12.4 Hz, 1H), 4.30 (t, J=6.4 Hz, 1H), 3.71-3.56 (m, 4H), 3.01 (s, 2H), 2.90 (s, 1H), 2.74 (s, 1H), 2.71-2.65 (m, 2H), 2.61 (s, 1H), 2.02 (d, J=6.0 Hz, 1H), 1.90-1.82 (m, 1H), 1.77-1.71 (m, 1H), 1.39 (s, 9H), 1.26 (d, J=6.4 Hz, 3H), 1.18 (t, J=7.2 Hz, 2H).

Step 2—3-(3-Methyl-2-oxo-4-((R,E)-3-(piperidin-4-yloxy)but-1-en-1-yl)-2,3-dihydro-1H-benzo [d]imidazol-1-yl)piperidine-2,6-dione To a solution of tert-butyl 4-[(E,1R)-3-[1-(2,6-dioxo-3-piperidyl)-3-methyl-2-oxo-benzimidazol-4-yl]-1-methyl-allyloxy]piperidine-1-carboxylate (110 mg, 214 umol), 2,6-lutidine (229 mg, 2.15 mmol) in DCM (1 mL) at 0° C. was added trimethylsilyl trifluoromethanesulfonate (357 mg, 1.61 mmol) dropwise. Then the mixture was stirred at 25° C. for 3 hrs. On completion, the reaction mixture was concentrated to give a residue. The residue was purified by Prep-HPLC (column: Waters X bridge C18 330 g; mobile phase: [water-ACN]; B %: 10%-25%, 8 min) to give the title compound (65 mg, 72% yield) as brown gum. $^1$H NMR (400 MHz, DMSO-$d_6$) δ 11.46-10.76 (m, 1H), 8.36 (s, 1H), 7.23 (d, J=15.6 Hz, 1H), 7.14 (d, J=7.2 Hz, 1H), 7.09-6.99 (m, 2H), 6.05 (d, J=15.6 Hz, 1H), 5.42-5.34 (m, 1H), 4.34-4.27 (m, 1H), 4.04 (q, J=6.0 Hz, 3H), 3.19-3.07 (m, 3H), 2.86 (s, 3H), 2.74-2.60 (m, 2H), 1.92-1.84 (m, 1H), 1.60 (d, J=9.2 Hz, 2H), 1.28 (d, J=6.0 Hz, 2H), 1.18 (t, J=7.2 Hz, 3H).

Tert-butyl-dimethyl-prop-2-ynoxy-silane (Intermediate AXX)

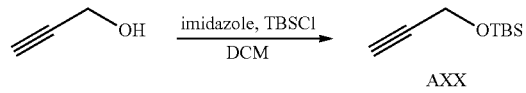

To a solution of prop-2-yn-1-ol (10.0 g, 178 mmol, 10 mL, CAS #107-19-7) and imidazole (18.2 g, 267 mmol) in DCM (500 mL) was added TBSCl (40.3 g, 267 mmol) at 0° C. The reaction mixture was stirred at 0° C. for 1.5 hours. On completion, the reaction mixture was quenched with sat. $NH_4Cl$ (400 mL). The mixture was separated and the organic layers were washed with sat. $NH_4Cl$ (200 mL) and brine (200 mL), dried with anhydrous $Na_2SO_4$ and filtered. The filtrate was concentrated in vacuo. The residue was purified by silica column (PE:EA=1:0) to give the title compound (20.0 g, 65% yield) as colorless liquid. $^1$H NMR (400 MHz, $CDCl_3$) δ 4.32 (d, J=2.4 Hz, 2H), 2.38 (t, J=2.4 Hz, 1H), 0.92 (s, 9H), 0.13 (s, 6H).

3-[9-(2,6-Dioxo-3-piperidyl)pyrido[2,3-b]indol-5-yl]propanal (Intermediate AXY)

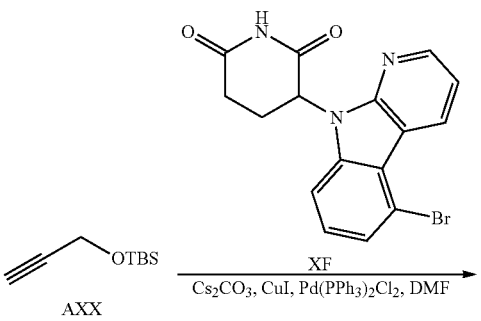

-continued

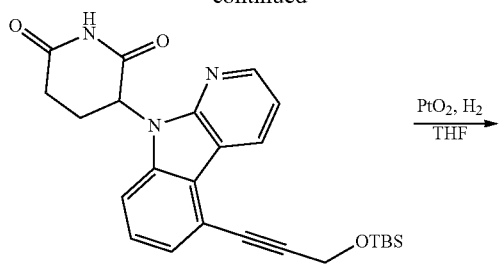

PtO₂, H₂
⎯⎯⎯→
THF

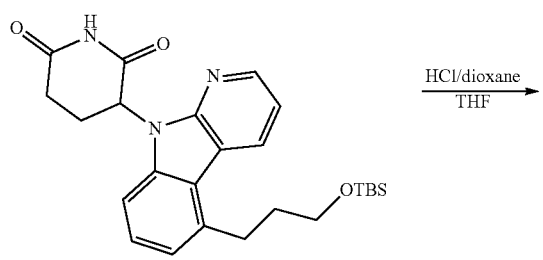

HCl/dioxane
⎯⎯⎯⎯→
THF

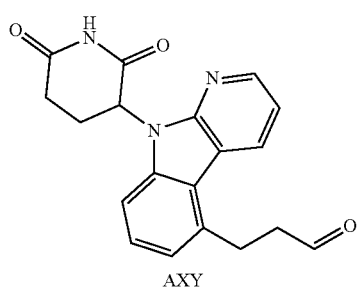

DMP
⎯⎯→
THF

AXY

Step 1—3-[5-[3-[Tert-butyl(dimethyl)silyl]oxyprop-1-ynyl]pyrido[2,3-b]indol-9-yl]piperidine-2,6-dione To a solution of 3-(5-bromopyrido[2,3-b]indol-9-yl)piperidine-2,6-dione (200 mg, 558 umol, Intermediate XF) in DMF (6 mL) was added Pd(PPh₃)₂Cl₂ (39.1 mg, 55.8 umol), CuI (10.6 mg, 55.8 umol) and Cs₂CO₃ (545.78 mg, 1.68 mmol). The reaction mixture was degassed with N₂ for three times. Then tert-butyl-dimethyl-prop-2-ynoxy-silane (190 mg, 1.12 mmol, 226 uL, Intermediate AXX) in DMF (1 mL) was added under N₂. The reaction mixture was stirred at 80° C. for 4 hrs under N₂ atmosphere. On completion, the reaction mixture was diluted with EA (50 mL) and filtered. The filtrate was washed with sat.NH₄Cl (2×20 mL) and brine (30 mL), dried with anhydrous Na₂SO₄ and filtered. The filtrate was concentrated in vacuo. The residue was purified by reverse phase (0.1%, FA) to give the title compound (100 mg, 40% yield) as a yellow solid. LC-MS (ESI⁺) m/z 448.4 (M+H)⁺.

Step 2—3-[5-[3-[Tert-butyl(dimethyl)silyl]oxypropyl]pyrido[2,3-b]indol-9-yl]piperidine-2,6-dione To a solution of 3-[5-[3-[tert-butyl(dimethyl)silyl]oxyprop-1-ynyl]pyrido[2,3-b]indol-9-yl]piperidine-2,6-dione (75.0 mg, 167 umol) in THF (5 mL) was added PtO₂ (38.0 mg, 167 umol). The reaction mixture was stirred at 25° C. for 12 hours under H₂ (15 Psi). On completion, and the reaction mixture was diluted with THF (50 mL) and filtered. The filtrate was concentrated in vacuo to give the title compound (75.0 mg, 99% yield) as a white solid. LC-MS (ESI⁺) m/z 452.3 (M+H)⁺.

Step 3—3-[5-(3-Hydroxypropyl)pyrido[2,3-b]indol-9-yl]piperidine-2,6-dione

To a solution of 3-[5-[3-[tert-butyl(dimethyl)silyl]oxypropyl]pyrido[2,3-b]indol-9-yl]piperidine-2,6-dione (70.0 mg, 154 umol) in THF (5 mL) was added HCl/dioxane (4 M, 4.67 mL). The reaction mixture was stirred at 25° C. for 1 hour. On completion, the reaction mixture was diluted with THF (50 mL) and filtered. The filtrate was concentrated in vacuo to give the title compound (52.0 mg, 99% yield) as a white solid. LC-MS (ESI⁺) m/z 338.1 (M+H)⁺.

Step 4—3-[9-(2,6-Dioxo-3-piperidyl)pyrido[2,3-b]indol-5-yl]propanal

To a solution of 3-[5-(3-hydroxypropyl)pyrido[2,3-b]indol-9-yl]piperidine-2,6-dione (50.0 mg, 148 umol) in THF (5 mL) was added DMP (62.8 mg, 148 umol). The reaction mixture was stirred at 25° C. for 1 hour. On completion, the reaction mixture was diluted with EA (70 mL) and washed with sat. NaHCO₃ (20 mL) and sat. Na₂S₂O₃ (30 mL). The organic layer was dried with anhydrous Na₂SO₄ and filtered. The filtrate was concentrated in vacuo to give the title compound (50 mg, 100% yield) as a white solid. LC-MS (ESI⁺) m/z 336.1 (M+H)⁺.

N-(1-(((1r,4R)-4-(2,7-diazaspiro[3.5]nonan-7-ylmethyl)cyclohexyl)-3-(difluoromethyl)-1H-pyrazol-4-yl)-5-((1R,4R)-2-oxa-5-azabicyclo[2.2.1]heptan-5-yl)pyrazolo[1,5-a]pyrimidine-3-carboxamide
(Intermediate AXZ)

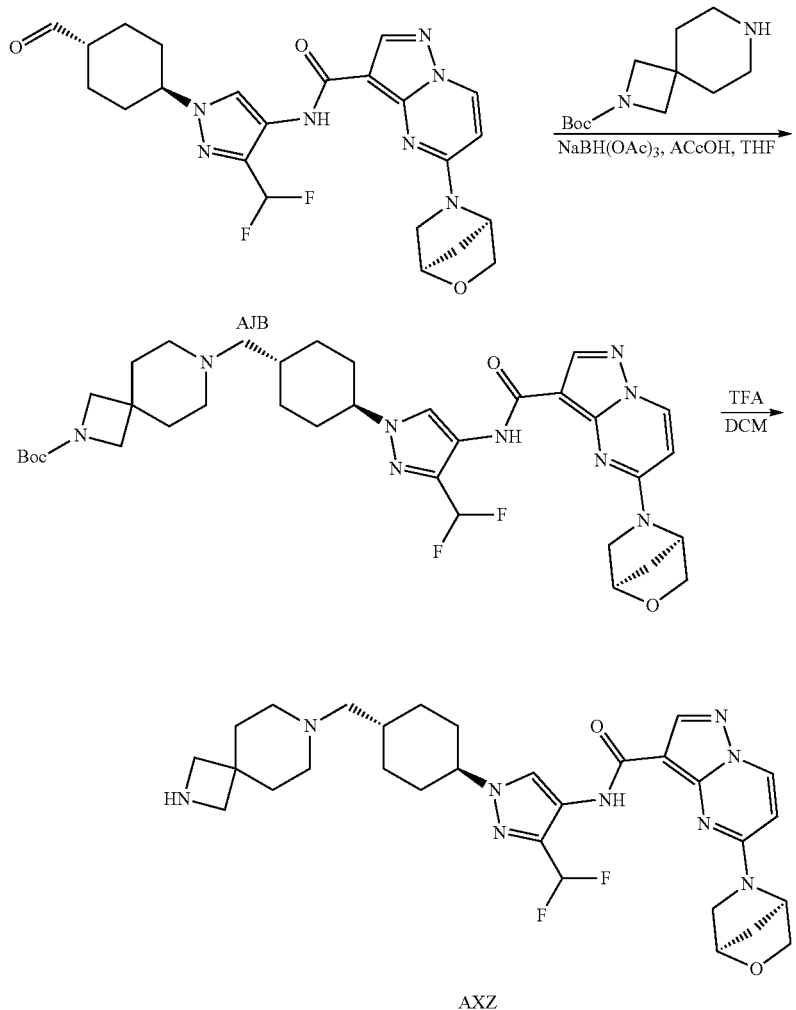

Step 1—Tert-butyl 7-(((1R,4r)-4-(4-(5-(((1R,4R)-2-oxa-5-azabicyclo[2.2.1]heptan-5-yl)pyrazolo[1,5-a]pyrimidine-3-carboxamido)-3-(difluoromethyl)-1H-pyrazol-1-yl)cyclohexyl)methyl)-2,7-diazaspiro[3.5]nonane-2-carboxylate To a solution of 5-((1R,4R)-2-oxa-5-azabicyclo[2.2.1]heptan-5-yl)-N-(3-(difluoromethyl)-1-((1r,4R)-4-formylcyclohexyl)-1H-pyrazol-4-yl)pyrazolo[1,5-a]pyrimidine-3-carboxamide (200 mg, 411 umol, Intermediate AJB) and tert-butyl 2,7-diazaspiro[3.5]nonane-2-carboxylate (93.2 mg, 411 umol, CAS #236406-55-6) in THF (10 mL) was added AcOH (24.7 mg, 411 umol, 23 uL). The reaction mixture was stirred at 25° C. for 0.25 hr. Then NaBH(OAc)$_3$ (130 mg, 617 umol) was added. The reaction mixture was stirred at 25° C. for 0.5 hr. On completion, the reaction was quenched with water (1 mL) and concentrated in vacuo. The residue was purified by reverse phase (0.1%, FA) to give the title compound (220 mg, 76% yield) as a white solid. LC-MS (ESI$^+$) m/z 696.5 (M+H)$^+$.

Step 2—N-(1-((1r,4R)-4-(2,7-diazaspiro[3.5]nonan-7-ylmethyl)cyclohexyl)-3-(difluoromethyl)-1H-pyrazol-4-yl)-5-((1R,4R)-2-oxa-5-azabicyclo[2.2.1]heptan-5-yl)pyrazolo[1,5-a]pyrimidine-3-carboxamide To a solution of tert-butyl 7-(((1R,4r)-4-(4-(5-((1R,4R)-2-oxa-5-azabicyclo[2.2.1]heptan-5-yl)pyrazolo [1,5-a]pyrimidine-3-carboxamido)-3-(difluoromethyl)-1H-pyrazol-1-yl)cyclohexyl)methyl)-2,7-diazaspiro[3.5]nonane-2-carboxylate (180 mg, 258 umol) in DCM (5 mL) was added TFA (5 mL). The reaction mixture was stirred at 25° C. for 0.5 hr. On completion, the reaction mixture was concentrated in vacuo to give the title compound (180 mg, 98% yield, TFA) as yellow oil. LC-MS (ESI$^+$) m/z 596.4 (M+H)$^+$.

Tert-butyl ((1-(aminomethyl)cyclobutyl)methyl)(methyl)carbamate (Intermediate AYA)

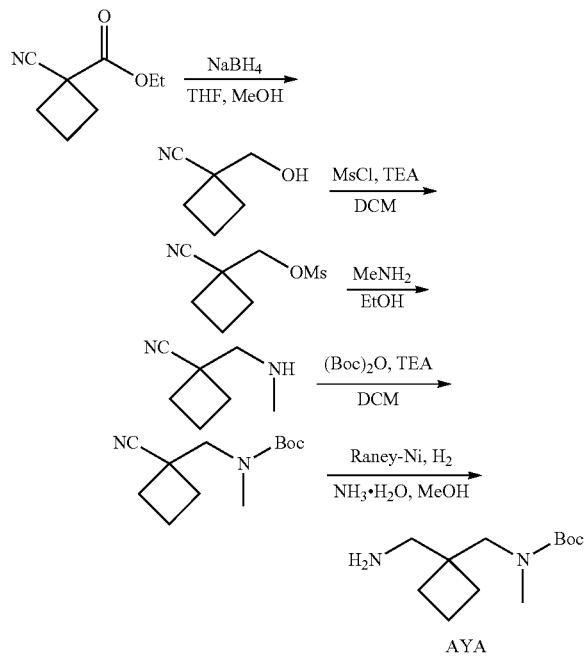

AYA

Step 1—1-(Hydroxymethyl)cyclobutanecarbonitrile

To a solution of ethyl 1-cyanocyclobutanecarboxylate (2 g, 13.1 mmol, CAS #28246-87-9) in a mixed solvent of THF (32.0 mL) and MeOH (8.0 mL) was added NaBH₄ (988 mg, 26.1 mmol) at 0° C. The mixture was stirred at 25° C. for 1 hour. On completion, the reaction mixture was quenched with water (20 mL) and extracted with EA (2×100 mL). The combined organic layer was dried over Na₂SO₄, filtered and concentrated in vacuo to give the title compound (1.4 g, 96% yield) as colorless oil. ¹H NMR (400 MHz, CDCl₃) δ 3.79 (s, 2H), 2.54-2.43 (m, 2H), 2.24-2.02 (m, 4H).

Step 2—(1-Cyanocyclobutyl)methyl methanesulfonate

To a solution of 1-(hydroxymethyl)cyclobutanecarbonitrile (1.4 g, 12.6 mmol) in the DCM (20 mL) was added MsCl (2.16 g, 18.9 mmol, 1.46 mL) and TEA (3.82 g, 37.8 mmol, 5.26 mL) at 0° C. The mixture was stirred at 25° C. for 1 hour. On completion, the reaction mixture was poured into water (20 mL) and extracted with DCM (2×100 mL). The combined organic layer was dried over Na₂SO₄, filtered and concentrated in vacuo to give the title compound (2.3 g, 98% yield) as yellow oil. ¹H NMR (400 MHz, CDCl₃) δ 4.36 (s, 2H), 3.12 (s, 3H), 2.65-2.54 (m, 2H), 2.32-2.08 (m, 4H).

Step 3—1-((Methylamino)methyl)cyclobutanecarbonitrile

To a solution of (1-cyanocyclobutyl)methyl methanesulfonate (2.35 g, 12.4 mmol) in the MeNH₂/EtOH (20 mL) was stirred at 60° C. for 12 hours. On completion, the reaction mixture was concentrated in vacuo to give the title compound (1.5 g, 97% yield) as yellow oil.

Step 4—Tert-butyl ((1-cyanocyclobutyl)methyl)(methyl)carbamate

To a solution of 1-(methylaminomethyl)cyclobutanecarbonitrile (1.5 g, 12.1 mmol) in the DCM (20 mL) was added Boc₂O (5.27 g, 24.2 mmol) and Et₃N (3.67 g, 36.2 mmol, 5.04 mL). The mixture was stirred at 25° C. for 12 hours. On completion, the reaction mixture was diluted with H₂O (80 mL) and extracted with water (3×100 mL). The combined organic layer was dried over Na₂SO₄, filtered and concentrated in vacuo to give a residue. The residue was purified by column chromatography (SiO₂, Petroleum ether/Ethyl acetate=20/1 to 5/1) to give the title compound (2.4 g, 89% yield) as colorless oil. ¹H NMR (400 MHz, CDCl₃) δ 3.68-3.55 (m, 2H), 3.01 (s, 3H), 2.52-2.40 (m, 2H), 2.32-2.06 (m, 4H), 1.48 (s, 9H).

Step 5—Tert-butyl ((1-(aminomethyl)cyclobutyl)methyl)(methyl)carbamate

To a solution of tert-butyl N-[(1-cyanocyclobutyl)methyl]-N-methyl-carbamate (1.0 g, 4.46 mmol) in MeOH (20 mL) was added NH₃.H₂O (1.25 g, 8.92 mmol, 1.37 mL, 25% purity) and Raney-Ni (191 mg, 2.23 mmol). The mixture was stirred at 25° C. for 2 hours under H₂ (50 Psi). On completion, the reaction mixture was filtered and concentrated in vacuo to give the title compound (1.0 g, 98% yield) as yellow gum. ¹H NMR (400 MHz, CDCl₃) δ 3.51-3.21 (m, 2H), 2.83 (s, 2H), 2.75-2.61 (m, 2H), 2.09-1.54 (m, 7H), 1.45 (s, 9H).

2-(2,6-Dioxopiperidin-3-yl)-4-(((1-((methylamino)methyl)cyclobutyl)methyl)amino) isoindoline-1,3-dione (Intermediate AYB)

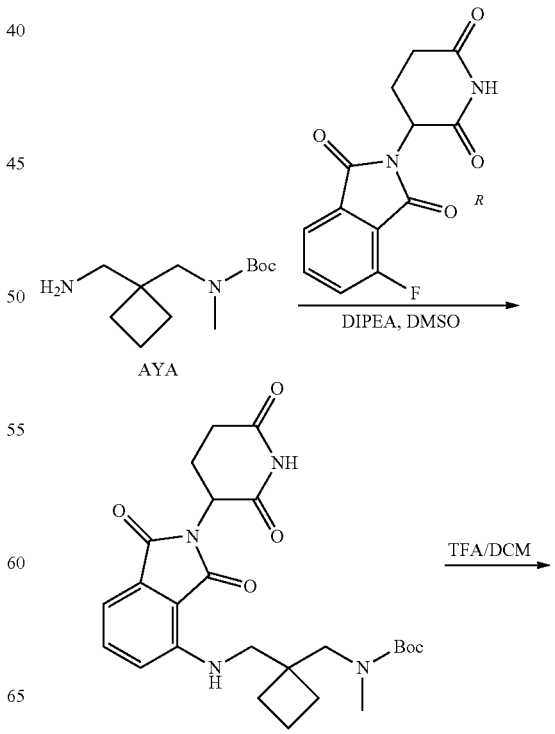

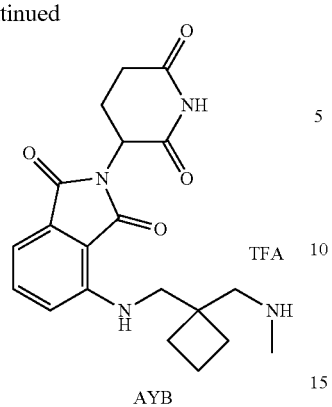

AYB

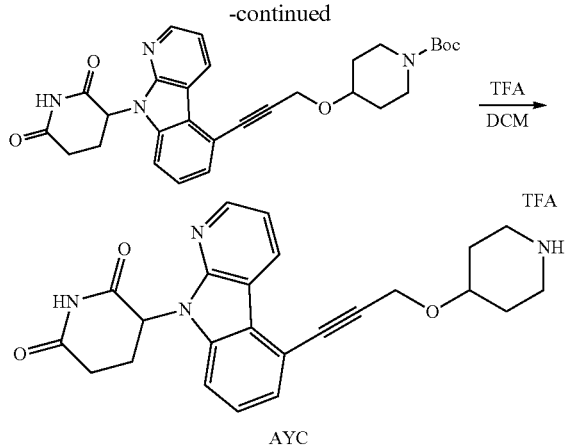

AYC

Step 1—Tert-butyl ((1-(((2-(2,6-dioxopiperidin-3-yl)-1,3-dioxoisoindolin-4-yl)amino)methyl)cyclobutyl)methyl)(methyl)carbamate A mixture of tert-butyl N-[[1-(aminomethyl)cyclobutyl]methyl]-N-methyl-carbamate (100 mg, 438 umol, Intermediate AYA), 2-(2,6-dioxo-3-piperidyl)-4-fluoro-isoindoline-1,3-dione (121 mg, 438 umol, Intermediate R) and DIPEA (170 mg, 1.31 mmol) in DMSO (2.0 mL) was stirred at 130° C. for 1 hour. On completion, the mixture was quenched with H$_2$O (0.5 mL) and the concentrated in vacuo to give a residue. The residue was purified by reverse phase (0.1% FA) to give the title compound (140 mg, 66% yield) as yellow solid. $^1$H NMR (400 MHz, DMSO-d$_6$) δ 11.08 (s, 1H), 7.60 (t, J=8.0 Hz, 1H), 7.30-7.14 (m, 1H), 7.04 (d, J=5.4 Hz, 1H), 6.82-6.22 (m, 1H), 5.07 (dd, J=5.4, 12.9 Hz, 1H), 3.40-3.34 (m, 5H), 2.86 (s, 3H), 2.64-2.55 (m, 2H), 2.07-1.75 (m, 7H), 1.34 (s, 9H).

Step 2—2-(2,6-Dioxopiperidin-3-yl)-4-(((1-((methylamino)methyl)cyclobutyl)methyl)amino) isoindoline-1,3-dione A solution of tert-butyl N-[[1-[[[2-(2,6-dioxo-3-piperidyl)-1,3-dioxo-isoindolin-4-yl]amino]methyl]cyclobutyl]methyl]-N-methyl-carbamate (70.0 mg, 144 umol) in a mixed solvent of DCM (2.0 mL) and TFA (1.0 mL) was stirred at 25° C. for 1 hour. On completion, the reaction mixture was concentrated in vacuo to give the title compound (55.0 mg, 99% yield) as yellow solid. LC-MS (ESI$^+$) m/z 385.2 (M+H)$^+$.

3-[5-(3-Hydroxypropyl)pyrido[2,3-b]indol-9-yl]piperidine-2,6-dione (Intermediate AYC)

Step 1—Tert-butyl 4-[3-[9-(2,6-dioxo-3-piperidyl)pyrido[2,3-b]indol-5-yl]prop-2-ynoxy]piperidine-1-carboxylate To a solution of 3-(5-bromopyrido[2,3-b]indol-9-yl)piperidine-2,6-dione (70.0 mg, 195 umol, Intermediate XF) in DMF (2 mL) was added Pd(PPh$_3$)$_2$Cl$_2$ (13.7 mg, 19.5 umol), CuI (3.72 mg, 19.5 umol), Cs$_2$CO$_3$ (191 mg, 586 umol) and 4 Å molecular sieves (100 mg). The reaction mixture was degassed with N$_2$ for three times. Then tert-butyl 4-prop-2-ynoxypiperidine-1-carboxylate (93.5 mg, 390 umol, Intermediate™) in DMF (0.3 mL) was added under N$_2$. The reaction mixture was stirred at 80° C. for 2 hours under N$_2$. On completion, the reaction was quenched with water (0.5 mL) and concentrated in vacuo. The residue was purified by reverse phase (0.1%, FA) to give the title compound (50.0 mg, 49% yield) as a white solid, LC-MS (ESI$^+$) m/z 517.4 (M+H)$^+$.

Step 2—3-[5-(3-Hydroxypropyl)pyrido[2,3-b]indol-9-yl]piperidine-2,6-dione

To a solution of tert-butyl 4-[3-[9-(2,6-dioxo-3-piperidyl)pyrido[2,3-b]indol-5-yl]prop-2-ynoxy] piperidine-1-carboxylate (50.0 mg, 96.7 umol) in DCM (3 mL) was added TFA (3 mL). The reaction mixture was stirred at 25° C. for 1 hour. On completion, the reaction mixture was concentrated in vacuo to give the title compound (50.0 mg, 94.2 umol, 97% yield, TFA) as a white solid. LC-MS (ESI$^+$) m/z 417.1 (M+H)$^+$.

Tert-butyl 4-(((1 r,4r)-4-(aminomethyl)cyclohexyl)oxy)piperidine-1-carboxylate (Intermediate AYD)

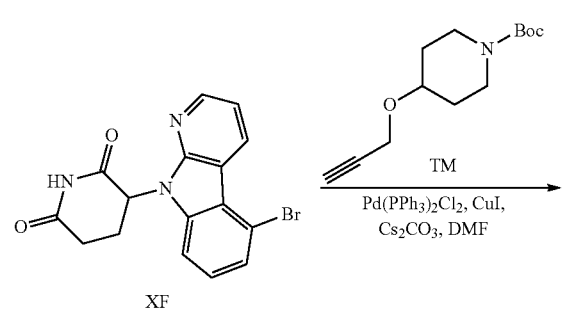

XF

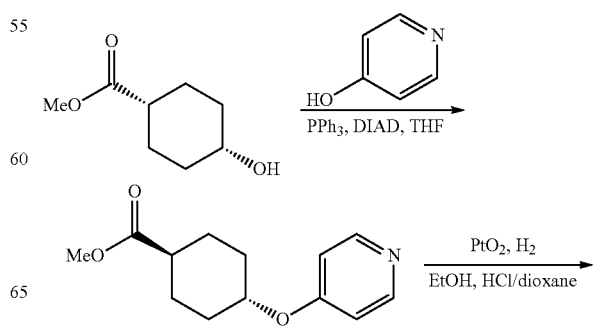

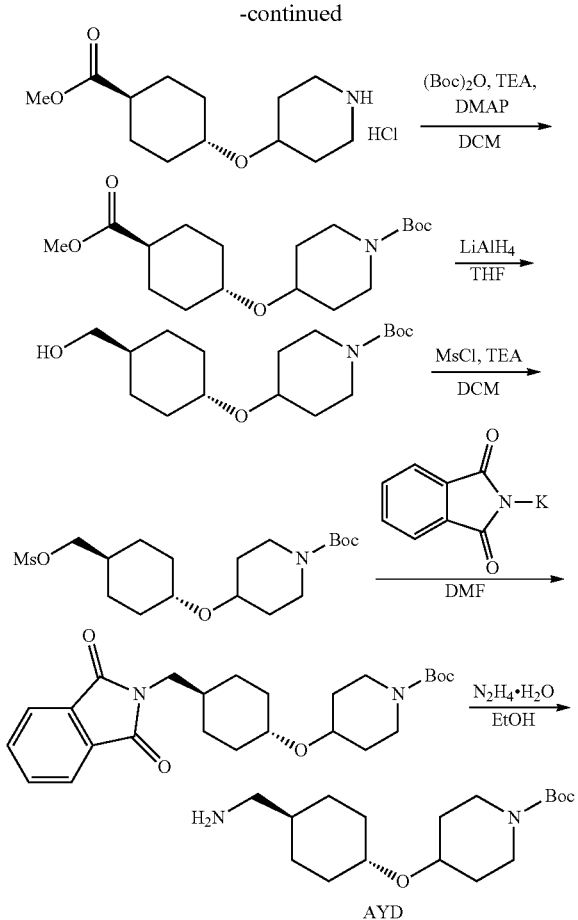

Step 1—(1R,4r)-Methyl 4-(pyridin-4-yloxy)cyclohexanecarboxylate

To a solution of methyl 4-hydroxycyclohexanecarboxylate (3.00 g, 19.0 mmol, CAS #3618-03-9), pyridin-4-ol (1.80 g, 19.0 mmol, CAS #626-64-2) and PPh$_3$ (7.46 g, 28.5 mmol) in THF (30 mL) was added DIAD (5.75 g, 28.5 mmol) at 0° C. The reaction mixture was stirred at 50° C. for 12 hours. On completion, the reaction mixture was concentrated in vacuo to give a residue. The residue was purified by reverse phase (0.1% NH$_3$.H$_2$O) to afford a crude product. Then, the crude product was further purified by prep-HPLC (column: Waters Xbridge C18 150*50 mm*10 um; mobile phase: [water (10 mM NH$_4$HCO$_3$)-ACN]; B %: 22%-52%, 11.5 min) to give the title compound (400 mg, 9% yield) as a white solid. $^1$H NMR (400 MHz, DMSO-d$_6$) δ 8.35 (d, J=4.0 Hz, 2H), 6.96 (d, J=4.4 Hz, 2H), 4.55-4.40 (m, 1H), 3.61 (s, 3H), 2.43-2.35 (m, 1H), 2.13-2.04 (m, 2H), 2.00-1.90 (m, 2H), 1.65-1.50 (m, 2H), 1.48-1.35 (m, 2H).

Step 2—(1R,4r)-Methyl 4-(piperidin-4-yloxy)cyclohexanecarboxylate hydrochloride To a solution of methyl 4-(4-pyridyloxy)cyclohexanecarboxylate (350 mg, 1.49 mmol) in EtOH (20 mL) was added HCl/dioxane (4 M, 1.49 mL). The reaction mixture was stirred at 20° C. for 0.5 hour. Then PtO$_2$ (405 mg, 1.79 mmol) was added to the reaction mixture and the mixture was degassed and purged with H$_2$ for 3 times. The mixture was stirred under H$_2$ (50 Psi) at 40° C. for 15.5 hours. On completion, the reaction mixture was filtered and the filtrate was concentrated in vacuo to give the title compound (350 mg, 95% yield, HCl salt) as a white solid. $^1$H NMR (400 MHz, DMSO-d$_6$) δ 9.10-8.80 (m, 2H), 3.74-3.65 (m, 1H), 3.61-3.55 (m, 3H), 3.17-3.04 (m, 2H), 3.02-2.85 (m, 3H), 1.95-1.82 (m, 5H), 1.75-1.50 (m, 4H), 1.43-1.30 (m, 2H), 1.20-1.10 (m, 2H).

Step 3—Tert-butyl 4-(((l1r,4r)-4-(methoxycarbonyl)cyclohexyl)oxy)piperidine-1-carboxylate To a solution of methyl 4-(4-piperidyloxy)cyclohexanecarboxylate (350 mg, 1.26 mmol, HCl salt) in EtOH (20 mL) was added TEA (637 mg, 6.30 mmol), DMAP (308 mg, 2.52 mmol) and Boc$_2$O (550 mg, 2.52 mmol). The reaction mixture was stirred at 20° C. for 12 hours. On completion, the reaction mixture was concentrated in vacuo to give a residue, which was diluted with water (20 mL) and extracted with EtOAc (3×20 mL). The combined organic layers were washed with water (2×20 mL) and brine (10 mL), dried over Na$_2$SO$_4$, filtered and concentrated in vacuo to give the title compound (430 mg, 99% yield) as a yellow solid.

Step 4—Tert-butyl 4-(((1r,4r)-4-(hydroxymethyl)cyclohexyl)oxy)piperidine-1-carboxylate To a solution of tert-butyl 4-(4-methoxycarbonylcyclohexoxy)piperidine-1-carboxylate (430 mg, 1.26 mmol) in THF (20 mL) was added LiAlH$_4$ (57.4 mg, 1.51 mmol) at 0° C. The mixture was stirred at 0° C. for 2 hours. On completion, the reaction was quenched with water (0.4 mL) at 20° C., and then filtered and concentrated in vacuo to give a residue. The residue was purified by flash silica gel chromatography (ISCO®; 12 g SepaFlash® Silica Flash column, eluent of 10-80% ethyl acetate/petroleum ether gradient @ 30 mL/min) to afford the title compound (245 mg, 62% yield) as a white solid. $^1$H NMR (400 MHz, CDCl$_3$) δ 4.73-4.63 (m, 2H), 3.77-3.67 (m, 2H), 3.55-3.45 (m, 1H), 3.38 (d, J=6.0 Hz, 2H), 3.28-3.18 (m, 1H), 3.01-2.91 (m, 2H), 1.96-1.88 (m, 2H), 1.82-1.74 (m, 2H), 1.45-1.35 (m, 12H), 1.25-1.13 (m, 2H), 0.98-0.85 (m, 2H).

Step 5—Tert-butyl 4-(((1r,4r)-4-(((methylsulfonyl)oxy)methyl)cyclohexyl)oxy)piperidine-1-carboxylate To a solution of tert-butyl 4-[4-(hydroxymethyl)cyclohexoxy]piperidine-1-carboxylate (230 mg, 734 umol) and TEA (149 mg, 1.47 mmol) in DCM (5.0 mL) was added MsCl (101 mg, 881 umol) at 0° C. The reaction mixture was stirred at 20° C. for 1 hour. On completion, the reaction mixture was diluted with water (10 mL) and extracted with DCM (3×10 mL). The combined organic layers were washed with water (2×10 mL) and brine (10 mL), dried over Na$_2$SO$_4$, filtered and concentrated in vacuo to afford the title product (245 mg, 85% yield) as a white solid. $^1$H NMR (400 MHz, DMSO-d$_6$) δ 4.04 (d, J=6.4 Hz, 2H), 3.87-3.74 (m, 2H), 3.60-3.52 (m, 1H), 3.35-3.25 (m, 1H), 3.08-2.98 (m, 5H), 2.05-1.98 (m, 2H), 1.90-1.83 (m, 2H), 1.81-1.68 (m, 3H), 1.52-1.42 (m, 11H), 1.32-1.22 (m, 2H), 1.13-1.03 (m, 2H).

Step 6—Tert-butyl 4-(((1r,4r)-4-((1,3-dioxoisoindolin-2-yl)methyl)cyclohexyl)oxy)piperidine-1-carboxylate A mixture of tert-butyl 4-[4-(methylsulfonyloxymethyl)cyclohexoxy]piperidine-1-carboxylate (230 mg, 587 umol)

and (1,3-dioxoisoindolin-2-yl)potassium (218 mg, 1.17 mmol, CAS #1074-82-4) in DMF (6.0 mL) was stirred at 100° C. for 12 hours. On completion, the reaction mixture was quenched with water (30 mL), and then filtered. The filter cake was dried in vacuo to afford the title product (210 mg, 81% yield) as a white solid. $^1$H NMR (400 MHz, DMSO-$d_6$) δ 7.90-7.81 (m, 4H), 3.65-3.52 (m, 3H), 3.42 (d, J=6.8 Hz, 2H), 3.31-3.25 (m, 1H), 3.04-2.92 (m, 2H), 1.92-1.85 (m, 2H), 1.75-1.60 (m, 5H), 1.38 (s, 9H), 1.30-1.19 (m, 2H), 1.13-0.95 (m, 4H).

Step 7—Tert-butyl 4-(((1r,4r)-4-(aminomethyl)cyclohexyl)oxy)piperidine-1-carboxylate A mixed solution of tert-butyl 4-[4-[(1,3-dioxoisoindolin-2-yl)methyl]cyclohexoxy]piperidine-1-carboxylate (200 mg, 452 umol), NH$_2$NH$_2$.H$_2$O (226 mg, 4.52 mmol) in EtOH (20 mL) was stirred at 80° C. for 1 hour. On completion, the reaction mixture was filtered and concentrated in vacuo to give a residue. The residue was diluted with DCM (20 mL), and then filtered. The filtrate was concentrated in vacuo to afford the title product (110 mg, 78% yield) as colorless oil. $^1$H NMR (400 MHz, DMSO-$d_6$) δ 4.86 (s, 2H), 3.77-3.67 (m, 2H), 3.53-3.45 (m, 1H), 3.28-3.18 (m, 1H), 3.00-2.90 (m, 2H), 1.95-1.87 (m, 2H), 1.78-1.68 (m, 7H), 1.45-1.40 (m, 1H), 1.38 (s, 9H), 1.22-1.18 (m, 1H), 0.87-0.80 (m, 1H).

2-(2,6-Dioxopiperidin-3-yl)-4-((((1r,4r)-4-(piperidin-4-yloxy)cyclohexyl)methyl)amino) isoindoline-1,3-dione (Intermediate AYE)

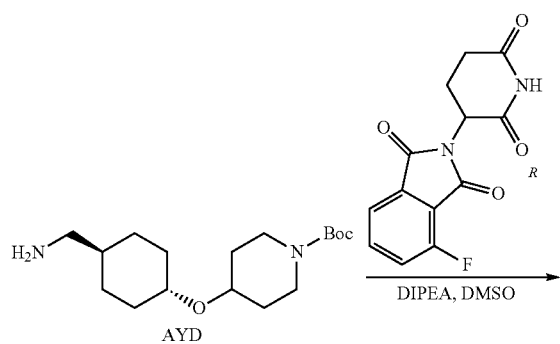

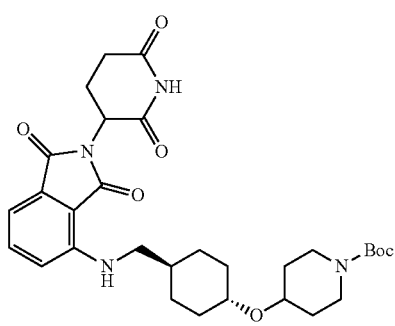

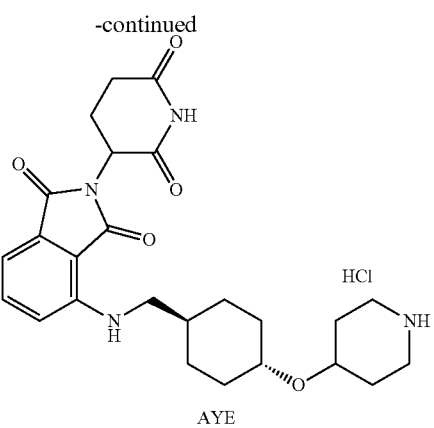

Step 1—Tert-butyl 4-(((1r,4r)-4-(((2-(2,6-dioxopiperidin-3-yl)-1,3-dioxoisoindolin-4-yl)amino)methyl)cyclohexyl)oxy)piperidine-1-carboxylate To a solution of 2-(2,6-dioxo-3-piperidyl)-4-fluoro-isoindoline-1,3-dione (90.0 mg, 326 umol, Intermediate R) and tert-butyl 4-[4-(aminomethyl)cyclohexoxy]piperidine-1-carboxylate (102 mg, 326 umol, Intermediate AYD) in DMSO (1.0 mL) was added DIPEA (211 mg, 1.63 mmol). The reaction mixture was stirred at 130° C. for 2 hours. On completion, the reaction mixture was quenched with H$_2$O (0.2 mL) and then concentrated in vacuo to give a residue. The residue was purified by prep-HPLC (FA condition: column: Phenomenex Synergi C18 150*25*10 um; mobile phase: [water (0.225% FA)-ACN]; B %: 51%-81%, 10 min) to afford the title compound (78.0 mg, 42% yield) as a yellow solid. $^1$H NMR (400 MHz, DMSO-$d_6$) δ 11.09 (s, 1H), 7.58 (dd, J=8.4, 7.2 Hz, 1H), 7.12 (d, J=8.8 Hz, 1H), 7.02 (d, J=6.8 Hz, 1H), 6.61-6.53 (m, 1H), 5.05 (dd, J=12.8, 5.2 Hz, 1H), 3.67-3.54 (m, 3H), 3.17 (t, J=6.4 Hz, 2H), 3.05-2.83 (m, 3H), 2.63-2.55 (m, 2H), 2.07-1.99 (m, 3H), 1.97-1.90 (m, 2H), 1.82-1.68 (m, 4H), 1.59-1.49 (m, 1H), 1.39 (s, 9H), 1.33-1.23 (m, 2H), 1.15-1.10 (m, 4H).

Step 2—2-(2,6-Dioxopiperidin-3-yl)-4-((((1r,4r)-4-(piperidin-4-yloxy)cyclohexyl)methyl)amino) isoindoline-1,3-dione hydrochloride To a solution of tert-butyl 4-[4-[[[2-(2,6-dioxo-3-piperidyl)-1,3-dioxo-isoindolin-4-yl]amino]methyl] cyclohexoxy]piperidine-1-carboxylate (75.0 mg, 132 umol) in DCM (5.0 mL) was added HCl/dioxane (4 M, 1.0 mL). The reaction mixture was stirred at 20° C. for 0.2 hour. On completion, the reaction mixture was concentrated in vacuo to the title product (66.0 mg, 95% yield, HCl salt) as a green solid.

Tert-butyl ((1r,4r)-4-(aminomethyl)cyclohexyl)(methyl)carbamate (Intermediate AYF)

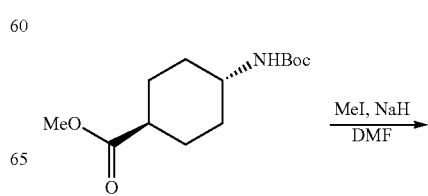

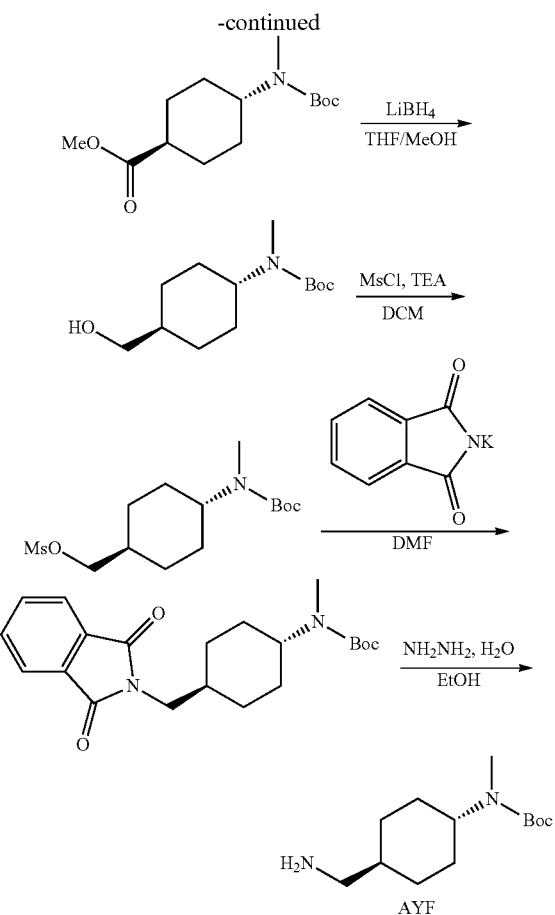

Step 1—(1R,4r)-methyl 4-((tert-butoxycarbonyl)(methyl)amino)cyclohexanecarboxylate To a solution of methyl 4-(tert-butoxycarbonylamino)cyclohexanecarboxylate (2.00 g, 7.77 mmol, CAS #146307-51-9) in DMF (20 mL) was added NaH (373 mg, 9.33 mmol, 60% dispersion in mineral oil) under 0° C. for 0.5 hr. Then CH$_3$I (1.32 g, 9.33 mmol, 581 uL) was added to the reaction mixture and the mixture was stirred at 25° C. for 2 hrs. On completion, the reaction mixture was diluted with 100 mL H$_2$O and extracted with EA (3×50 mL). The combined organic layers were washed with NaCl (50 mL×2), dried over Na$_2$SO$_4$, filtered and concentrated in vacuo to give a residue. The residue was purified by column chromatography to give the title compound (1.80 g, 85% yield) as yellow oil. $^1$H NMR (400 MHz, DMSO-d$_6$) δ 3.61-3.54 (m, 3H), 3.17 (d, J=5.3 Hz, 1H), 2.65 (s, 3H), 2.31-2.15 (m, 1H), 2.01-1.88 (m, 2H), 1.62-1.31 (m, 13H).

Step 2—Tert-butyl ((1r,4r)-4-(hydroxymethyl)cyclohexyl)(methyl)carbamate

To a solution of methyl 4-[tert-butoxycarbonyl(methyl)amino]cyclohexanecarboxylate (800 mg, 2.95 mmol) in THF (12 mL) and MeOH (3 mL) was cooled to 0° C. and slowly added LiBH$_4$ (193 mg, 8.84 mmol) under N$_2$ atmosphere. After that, the reaction mixture was warmed to 50° C. and stirred for 2 hours. On completion, the reaction mixture was diluted with 100 mL H$_2$O and extracted with EA 150 mL (50 mL×3). The combined organic layers were washed with NaCl 100 mL (50 mL×2), dried over Na$_2$SO$_4$, filtered and concentrated in vacuo to give the title compound (1.00 g, 70% purity, 97% yield) as a yellow solid. $^1$H NMR (400 MHz, DMSO-d$_6$) δ 4.39 (t, J=5.2 Hz, 1H), 4.11-3.98 (m, 1H), 3.20 (t, J=5.6 Hz, 2H), 2.65 (s, 3H), 1.77 (d, J=11.2 Hz, 2H), 1.65-1.40 (m, 4H), 1.38 (s, 9H), 1.17 (t, J=7.2 Hz, 3H).

Step 3—((1R,4r)-4-((tert-butoxycarbonyl)(methyl)amino)cyclohexyl)methyl methanesulfonate To a solution of tert-butyl N-[4-(hydroxymethyl)cyclohexyl]-N-methyl-carbamate (0.90 g, 3.70 mmol) in DCM (10 mL) was added MsCl (847 mg, 7.40 mmol, 572 uL) and TEA (1.12 g, 11.10 mmol, 1.54 mL). The mixture was stirred at 0° C. for 2 hours. On completion, the reaction mixture was quenched by addition H$_2$O 50 mL at 0° C., and then extracted with DCM (50 mL×3). The combined organic layers were washed with NaCl (50 mL×2), dried over Na$_2$SO$_4$, filtered and concentrated in vacuo to give the title compound (1.00 g, 84% yield) as a yellow oil.

Step 4—Tert-butyl ((1r,4r)-4-((1,3-dioxoisoindolin-2-yl)methyl)cyclohexyl)(methyl)carbamate To a solution of [4-[tert-butoxycarbonyl(methyl)amino]cyclohexyl]methyl methanesulfonate (1.00 g, 3.11 mmol) in DMF (10 mL) was added (1,3-dioxoisoindolin-2-yl)potassium (1.15 g, 6.22 mmol). The mixture was stirred at 40° C. for 16 hrs. On completion, the reaction mixture was diluted with 100 mL H$_2$O and extracted with EA (50 mL×3). The combined organic layers were washed with NaCl (50 mL×2), dried over Na$_2$SO$_4$, filtered and concentrated in vacuo to give a residue. The residue was purified by column chromatography to give the title compound (1.00 g, 84% purity, 72% yield) as a yellow solid. $^1$H NMR (400 MHz, DMSO-d$_6$) δ 7.90-7.81 (m, 4H), 3.85-3.64 (m, 1H), 3.43 (d, J=7.2 Hz, 2H), 2.62 (s, 3H), 1.71 (d, J=13.2 Hz, 2H), 1.63 (dd, J=3.6, 7.6 Hz, 1H), 1.58-1.42 (m, 3H), 1.38 (s, 9H), 1.26-1.15 (m, 1H), 1.12-0.99 (m, 2H).

Step 5—Tert-butyl ((1r,4r)-4-(aminomethyl)cyclohexyl)(methyl)carbamate

To a solution of tert-butyl N-[4-[(1,3-dioxoisoindolin-2-yl)methyl]cyclohexyl]-N-methyl-carbamate (1.00 g, 2.26 mmol) in EtOH (10 mL) was added NH$_2$NH$_2$.H$_2$O (266 mg, 4.51 mmol, 258 uL, 85% solution). The mixture was stirred at 60° C. for 2 hrs. On completion, the mixture was filtered and the filtrate was concentrated in vacuo to give the title compound (800 mg, 80% purity, 98% yield) as a yellow solid. $^1$H NMR (400 MHz, DMSO-d$_6$) δ 4.16 (s, 2H), 3.44 (q, J=7.2 Hz, 1H), 2.66-2.62 (m, 3H), 2.42 (d, J=6.4 Hz, 2H), 1.92-1.68 (m, 2H), 1.54 (s, 2H), 1.46-1.39 (m, 2H), 1.38 (s, 9H), 1.27-1.16 (m, 1H), 0.98-0.84 (m, 2H).

2-(2,6-Dioxopiperidin-3-yl)-4-((((1r,4r)-4-(methylamino)cyclohexyl)methyl)amino) isoindoline-1,3-dione (Intermediate AYG)

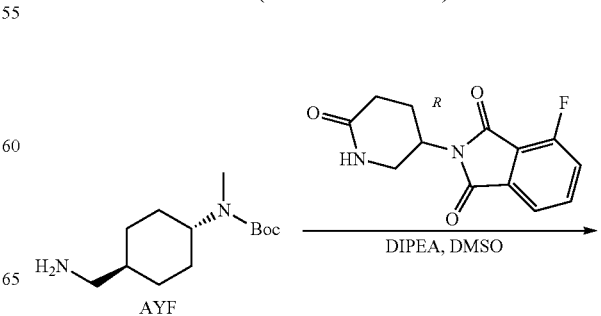

2303
-continued

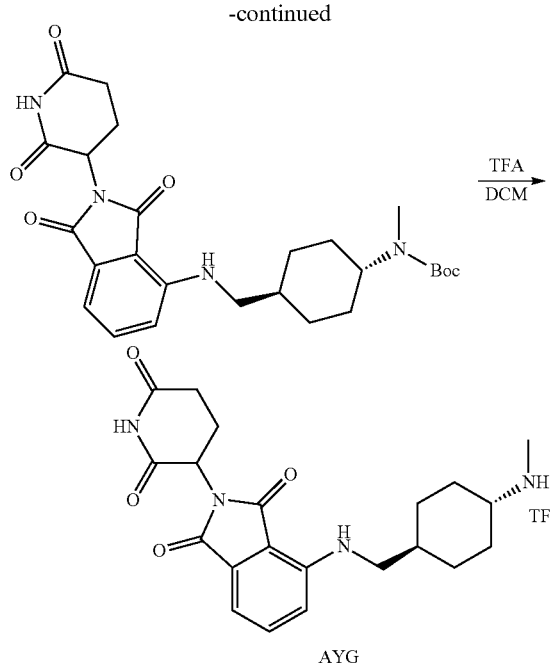

AYG

Step 1—Tert-butyl ((1r,4r)-4-(((2-(2,6-dioxopiperidin-3-yl)-1,3-dioxoisoindolin-4-yl)amino)methyl)cyclohexyl)(methyl)carbamate To a solution of tert-butyl N-[4-(aminomethyl)cyclohexyl]-N-methyl-carbamate (750 mg, 3.09 mmol, Intermediate AYF) in DMSO (10 mL) was added 2-(2,6-dioxo-3-piperidyl)-4-fluoro-isoindoline-1,3-dione (1.71 g, 6.19 mmol, Intermediate R) and DIPEA (1.20 g, 9.28 mmol, 1.62 mL). The mixture was stirred at 130° C. for 0.5 hr. On completion, the reaction mixture was filtered and concentrated in vacuo to give a residue. The residue was purified by prep-HPLC (FA condition) to give the title compound (300 mg, 18% yield, 95% purity) as yellow oil. LC-MS (ESI+) m/z 499.4 (M+H)+.

Step 2—2-(2,6-Dioxopiperidin-3-yl)-4-((((1r,4r)-4-(methylamino)cyclohexyl)methyl)amino) isoindoline-1,3-dione To a solution of tert-butyl N-[4-[[[2-(2,6-dioxo-3-piperidyl)-1,3-dioxo-isoindolin-4-yl]amino]methyl] cyclohexyl]-N-methyl-carbamate (150 mg, 286 umol) in DCM (1 mL) was added TFA (0.5 mL). The mixture was stirred at 25° C. for 0.5 hr. On completion, the reaction mixture was concentrated in vacuo to give the title compound (150 mg, TFA, 96% yield) as yellow oil. LC-MS (ESI+) m/z 399.4 (M+H)+.

Tert-butyl-4-(aminomethyl)phenethyl(methyl)carbamate (Intermediate AYH)

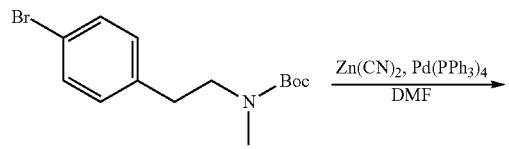

2304
-continued

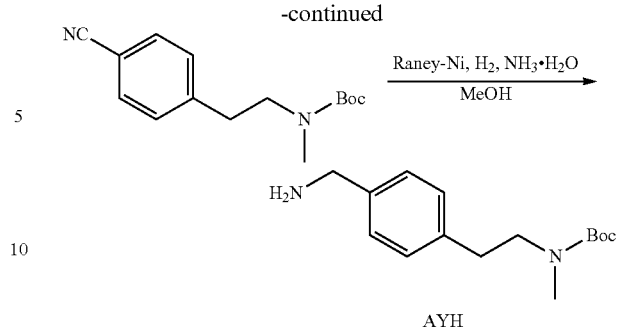

AYH

Step 1—Tert-butyl 4-cyanophenethyl(methyl)carbamate

A mixture of tert-butyl N-[2-(4-bromophenyl)ethyl]-N-methyl-carbamate (0.35 g, 1.11 mmol, CAS #1191063-30-5), Zn(CN)₂ (262 mg, 2.23 mmol), Pd(PPh₃)₄ (129 mg, 111 umol) in DMF (4.0 mL) was degassed and purged with N₂ for three times and then stirred at 100° C. under N₂ atmosphere for 12 hours. On completion, the reaction mixture was concentrated in vacuo to give a residue. The residue was purified by flash silica gel chromatography (ISCO®; 12 g SepaFlash® Silica Flash Column, Eluent of 0-40% ethyl acetate/petroleum ether gradient @ 30 mL/min) to give the title compound (0.26 g, 81% yield) as a colorless oil.

Step 2—Tert-butyl-4-(aminomethyl)phenethyl (methyl)carbamate

To a solution of tert-butyl N-[2-(4-cyanophenyl)ethyl]-N-methyl-carbamate (0.26 g, 899 umol), NH₃—H₂O (252 mg, 1.80 mmol) in MeOH (10 mL) was added Raney-Ni (41.8 mg, 488 umol) under N₂ atmosphere. The suspension was degassed and purged with H₂ three times. The mixture was stirred under H₂ (50 Psi) at 20° C. for 12 hours. On completion, the reaction mixture was filtered and concentrated in vacuo to give the title compound (0.28 g, 99% yield) as colorless oil. ¹H NMR (400 MHz, CDCl₃) δ 7.18-7.03 (m, 4H), 4.20-3.60 (m, 2H), 3.40-3.25 (m, 2H), 2.80-2.65 (m, 5H), 1.80-1.48 (m, 2H), 1.34 (s, 9H).

2-(1-Methyl-2,6-dioxopiperidin-3-yl)-4-((4-(2-(methylamino)ethyl)benzyl)amino)isoindoline-1,3-dione (Intermediate AYI)

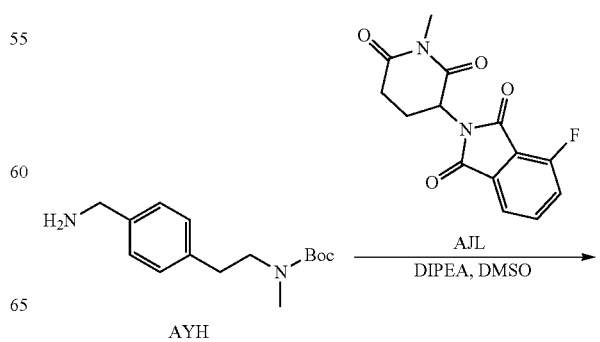

2305

-continued

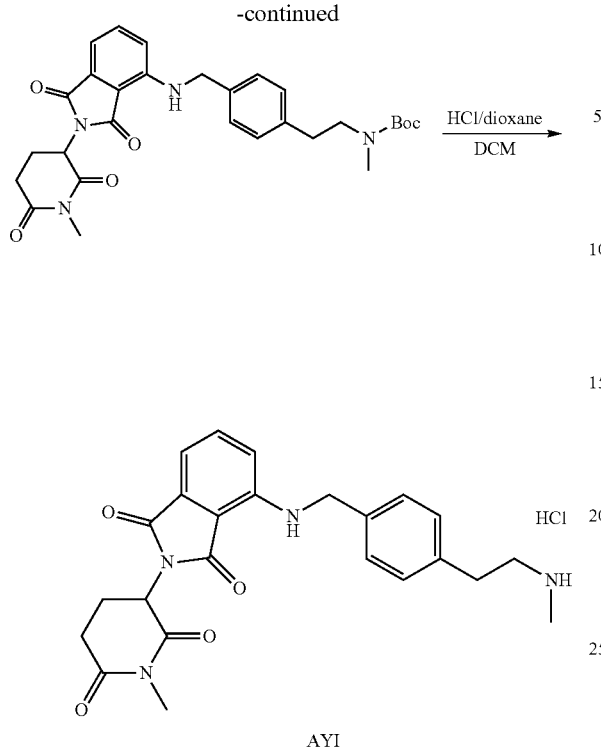

AYI

Step 1—Tert-butyl methyl(4-(((2-(1-methyl-2,6-dioxopiperidin-3-yl)-1,3-dioxoisoindolin-4-yl) amino)methyl)phenethyl)carbamate To a solution of 4-fluoro-2-(1-methyl-2,6-dioxo-3-piperidyl)isoindoline-1,3-dione (100 mg, 345 umol, Intermediate AJL) and tert-butyl N-[2-[4-(aminomethyl)phenyl] ethyl]-N-methyl-carbamate (137 mg, 413 umol, Intermediate AYH) in DMSO (1.0 mL) was added DIPEA (223 mg, 1.72 mmol). The reaction mixture was stirred at 130° C. for 2 hours. On completion, the reaction mixture was filtered and concentrated in vacuo to give a residue. The residue was purified by prep-HPLC (FA condition: column: Phenomenex Synergi C18 150*25*10 um; mobile phase: [water (0.225% FA)-ACN]; B %: 60%-90%, 9 min) to give the title compound (85 mg, 45% yield) as a green solid. $^1$HNMR (400 MHz, DMSO-$d_6$) δ 7.51 (t, J=7.6 Hz, 1H), 7.34-7.28 (m, 2H), 7.22-7.12 (m, 3H), 7.05-6.95 (m, 2H), 5.14 (dd, J=13.2, 5.2 Hz, 1H), 4.52 (d, J=6.0 Hz, 1H), 3.05-2.90 (m, 4H), 2.82-2.67 (m, 6H), 2.59-2.53 (m, 2H), 2.46-2.39 (m, 1H), 2.11-2.01 (m, 1H), 1.40-1.20 (m, 9H).

Step 2—2-(1-Methyl-2,6-dioxopiperidin-3-yl)-4-((4-(2-(methylamino)ethyl)benzyl)amino)isoindoline-1,3-dione hydrochloride To a solution of tert-butyl N-methyl-N-[2-[4-[[[2-(1-methyl-2,6-dioxo-3-piperidyl)-1,3-dioxo-iso indolin-4-yl]amino]methyl]phenyl]ethyl]carbamate (40 mg, 74.8 umol) in DCM (1.0 mL) was added HCl/dioxane (4 M, 0.5 mL). The reaction mixture was stirred at 20° C. for 1 hour. On completion, the reaction mixture was concentrated in vacuo to afford the title product (35 mg, 90% yield, HCl salt) as a white solid.

2306

3-[3-methyl-2-oxo-4-[[4-(4-piperidyloxy)-1-piperidyl]methyl]benzimidazol-1-yl]piperidine-2,6-dione (Intermediate AZX)

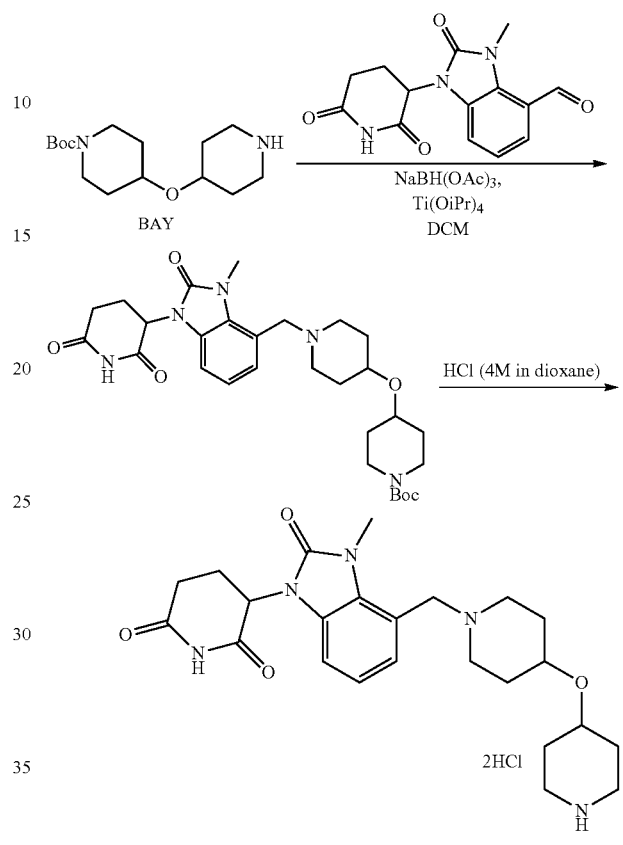

AZX

Step 1-tert-butyl 4-[(1-[[1-(2,6-dioxopiperidin-3-yl)-3-methyl-2-oxo-1,3-benzodiazol-4-yl]methyl]piperidin-4-yl)oxy]piperidine-1-carboxylate To a stirred solution of 1-(2,6-dioxopiperidin-3-yl)-3-methyl-2-oxo-1,3-benzodiazole-4-carbaldehyde (3.38 g, 11.8 mmol, Intermediate WW) and tert-butyl 4-(piperidin-4-yloxy)piperidine-1-carboxylate (4.02 g, 14.1 mmol, Intermediate BAY) in DCM (86 mL) was added Ti(Oi-Pr)$_4$ (10.03 g, 0.035 mmol) dropwise at room temperature under nitrogen atmosphere and the resulting mixture was stirred for 30 min at rt under nitrogen atmosphere. To the above mixture was added NaBH(OAc)$_3$ (4.99 g, 23.5 mmol) in portions over 1 h at 0° C. The resulting mixture was stirred at rt overnight. The reaction was then quenched by the addition of saturated aq. NH$_4$Cl (aq.) (100 mL) at 0° C. The resulting mixture was extracted with CH$_2$Cl$_2$ (3×100 mL), the combined organic layers were washed with brine (200 mL), and dried over anhydrous Na$_2$SO$_4$. After filtration, the filtrate was concentrated under reduced pressure. The residue was purified by reverse flash chromatography (column, C18 silica gel; mobile phase, MeCN in water, 10% to 40% gradient in 30 min; detector, UV 254 nm) to afford tert-butyl 4-[(1-[[1-(2,6-dioxopiperidin-3-yl)-3-methyl-2-oxo-1,3-benzodiazol-4-yl]methyl]piperidin-4-yl)oxy]piperidine-1-carboxylate (6 g, 92%) as a brown solid. 1H NMR (400

MHz, DMSO-d$_6$) δ 11.09 (s, 1H), 7.09-7.06 (m, 1H), 6.98-6.95 (m, 1H), 6.89-6.87 (m, 1H), 5.40-5.35 (m, 1H), 3.67 (s, 3H), 3.65-3.60 (m, 1H), 3.50-3.45 (m, 1H), 3.15-2.82 (m, 4H), 2.81-2.57 (m, 4H), 2.18-2.13 (m, 1H), 2.06-1.97 (m, 1H), 1.75-1.65 (m, 4H), 1.45-1.35 (m, 13H), 1.28-1.23 (m, 4H); LC/MS (ESI, m/z): [(M+1)]$^+$=556.4.

Step 2—3-(3-methyl-2-oxo-4-[[4-(piperidin-4-yloxy)piperidin-1-yl]methyl]-1,3-benzodiazol-1-yl)piperidine-2,6-dione dihydrochloride A solution of tert-butyl 4-[(1-[[1-(2,6-dioxopiperidin-3-yl)-3-methyl-2-oxo-1,3-benzodiazol-4-yl]methyl]piperidin-4-yl)oxy]piperidine-1-carboxylate (6.00 g, 10.8 mmol,) in 1,4-dioxane (60.00 mL) was added dropwise 4 M HCl in 1,4-dioxane (60.00 mL). The resulting mixture was stirred for 1 h at it. The reaction mixture was filtered, and the filter cake was washed with Et$_2$O (2×20 mL) to afford 3-(3-methyl-2-oxo-4-[[4-(piperidin-4-yloxy)piperidin-1-yl]methyl]-1,3-benzodiazol-1-yl)piperidine-2,6-dione dihydrochloride (4 g, 70%) as a brown solid; $^1$H NMR (400 MHz, DMSO-d$_6$) δ 11.13 (s, 1H), 10.57 (br, 1H), 9.06 (br, 2H), 7.43-7.22 (m, 2H), 7.12 (td, J=7.8, 4.2 Hz, 1H), 5.46 (dd, J=12.7, 5.4 Hz, 1H), 4.59 (dd, J=16.9, 5.2 Hz, 2H), 3.87-3.62 (m, 5H), 3.33-3.08 (m, 6H), 3.02-2.85 (m, 4H), 2.80-2.58 (m, 2H), 2.09-1.60 (m, 8H); LC/MS (ESI, m/z): [(M+1)]$^+$=456.3.

Tert-butyl (2-aminospiro[3.5]nonan-7-yl)(methyl)carbamate (Intermediate AWH)

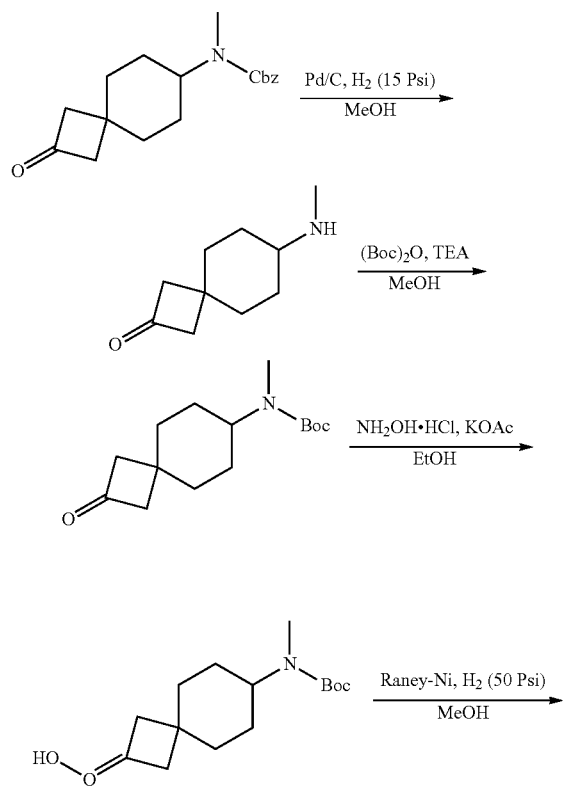

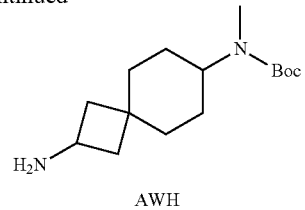

AWH

Step 1—7-(Methylamino)spiro[3.5]nonan-2-one

To a solution of benzyl N-methyl-N-(2-oxospiro[3.5]nonan-7-yl)carbamate (0.40 g, 1.33 mmol, synthesized via Steps 1-5 of Intermediate ANJ) in MeOH (10 mL) was added Pd/C (0.10 g, 10 wt %) under N$_2$ atmosphere. The suspension was degassed and purged with H$_2$ for 3 times. The mixture was stirred at 20° C. for 6 hours under H$_2$ (15 Psi). On completion, the reaction mixture was concentrated in vacuo to give the title compound (0.22 g, 100% yield) as colorless oil.

Step 2—Tert-butyl methyl(2-oxospiro[3.5]nonan-7-yl)carbamate

To a solution of 7-(methylamino)spiro[3.5]nonan-2-one (0.22 g, 1.32 mmol) in MeOH (5 mL) was added (Boc)$_2$O (574 mg, 2.63 mmol), TEA (399 mg, 3.95 mmol). The reaction mixture was stirred at 40° C. for 12 hours. On completion, the reaction mixture was diluted with water (5 mL), and extracted with EtOAc (5 mL×3). The combined organic layers were washed with brine (5 mL×2), dried over Na$_2$SO$_4$, filtered and concentrated in vacuo to give the title compound (0.23 g, 65% yield) as a yellow oil. $^1$H NMR (400 MHz, CDCl$_3$) δ 4.01-3.74 (m, 1H), 2.72-2.68 (m, 4H), 2.67-2.63 (m, 3H), 1.70-1.60 (m, 6H), 1.41-1.37 (m, 11H).

Step 3—Tert-butyl (2-(hydroxyimino)spiro[3.5]nonan-7-yl)(methyl)carbamate

A mixture solution of tert-butyl N-methyl-N-(2-oxospiro[3.5]nonan-7-yl)carbamate (0.20 g, 748 umol), NH$_2$OH—HCl (260 mg, 3.74 mmol) and KOAc (367 mg, 3.74 mmol) in EtOH (5 mL) was stirred at 80° C. for 12 hrs. On completion, the reaction mixture was diluted with water (15 mL) and extracted with EtOAc (10 mL×3). The combined organic layers were washed with brine (10 mL×2), dried over Na$_2$SO$_4$, filtered and concentrated in vacuo to give the title compound (0.20 g, 94% yield) as a yellow solid.

Step 4—Tert-butyl (2-aminospiro[3.5]nonan-7-yl)(methyl)carbamate

To a solution of tert-butyl N-(2-hydroxyiminospiro[3.5]nonan-7-yl)-N-methyl-carbamate (0.20 g, 708 umol) in MeOH (10 mL) was added Raney-Ni (6.07 mg, 70.8 umol) under N$_2$ atmosphere. The suspension was degassed and purged with H$_2$ for 3 times. The mixture was stirred at 50° C. for 12 hours under H$_2$ (50 Psi). On completion, the reaction mixture was filtered and concentrated in vacuo to afford the title product (0.14 g, 73% yield) as yellow oil. $^1$H NMR (400 MHz, CDCl$_3$) δ 4.90-4.50 (m, 4H), 3.95-3.65 (m, 1H), 2.75-2.48 (m, 4H), 2.20-1.50 (m, 10H), 1.45-1.25 (m, 12H).

2-(2,6-Dioxopiperidin-3-yl)-4-((7-(methylamino)spiro[3.5]nonan-2-yl)amino)isoindoline-1,3-dione (Intermediate AWI)

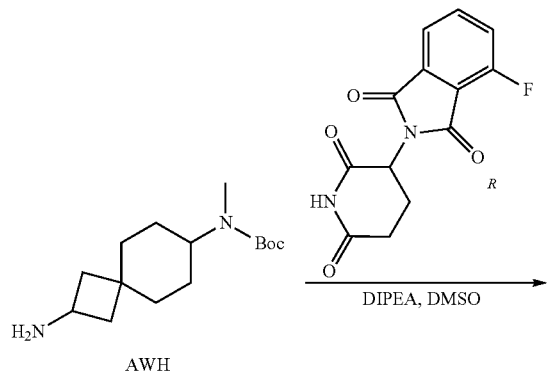

Step 1—Tert-butyl (2-((2-(2,6-dioxopiperidin-3-yl)-1,3-dioxoisoindolin-4-yl)amino)spiro[3.5]nonan-7-yl)(methyl)carbamate To a solution of 2-(2,6-dioxo-3-piperidyl)-4-fluoro-isoindoline-1,3-dione (50.0 mg, 181 umol, Intermediate R) and tert-butyl N-(2-aminospiro[3.5]nonan-7-yl)-N-methyl-carbamate (58.3 mg, 217 umol, Intermediate AWH) in DMSO (1 mL) was added DIPEA (117 mg, 905 umol). The reaction mixture was stirred at 130° C. for 2 hours. On completion, the reaction mixture was quenched by addition 0.5 N HCl to pH=5, and then filtered to afford a solution, which was purified by prep-HPLC (FA condition: column: Shim-pack C18 150*25*10 um; mobile phase: [water (0.225% FA)-ACN]; B %: 56%-86%, 10 min) to give the title product (38.0 mg, 39% yield) as a yellow solid. $^1$HNMR (400 MHz, DMSO-$d_6$) δ 8.00 (s, 1H), 7.50 (t, J=7.6 Hz, 1H), 7.13 (d, J=7.2 Hz, 1H), 6.77 (d, J=8.4 Hz, 1H), 6.32 (d, J=5.6 Hz, 1H), 4.97-4.91 (m, 1H), 4.05-3.97 (m, 1H), 2.95-2.67 (m, 6H), 2.54-2.44 (m, 1H), 2.36-2.37 (m, 1H), 2.20-2.13 (m, 1H), 1.91-1.84 (m, 1H), 1.80-1.60 (m, 5H), 1.55-1.35 (m, 13H).

Step 2—2-(2,6-Dioxopiperidin-3-yl)-4-((7-(methylamino)spiro[3.5]nonan-2-yl)amino)isoindoline-1,3-dione hydrochloride To a solution of tert-butyl N-[2-[[2-(2,6-dioxo-3-piperidyl)-1,3-dioxo-isoindolin-4-yl]amino]spiro[3.5]nonan-7-yl]-N-methyl-carbamate (35.0 mg, 66.7 umol) in DCM (3 mL) was added HCl/dioxane (4 M, 1 mL). The reaction mixture was stirred at 20° C. for 0.5 hour. On completion, the reaction mixture was concentrated in vacuo to afford the title product (30.0 mg, HCl salt, 100% yield) as a yellow solid.

3-[5-[3-(2,7-Diazaspiro[3.5]nonan-2-yl)propyl]pyrido[2,3-b]indol-9-yl]piperidine-2,6-dione (Intermediate AZY)

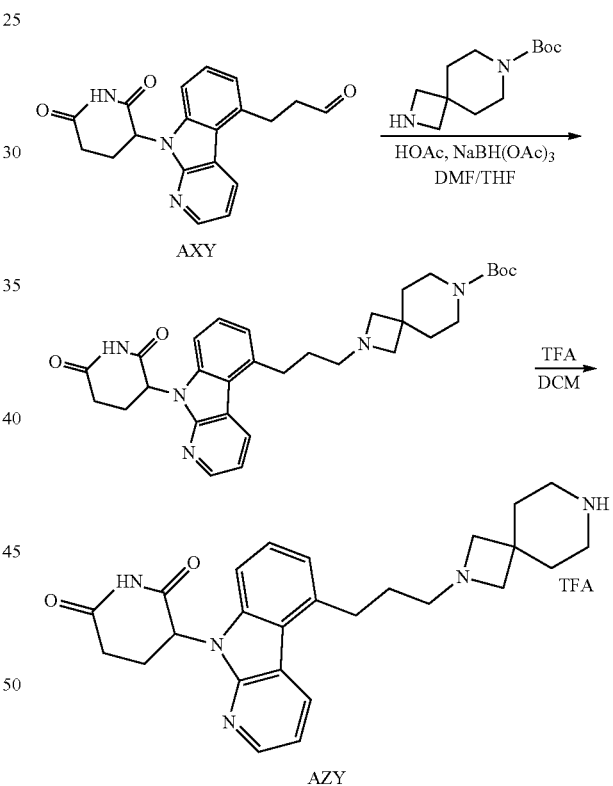

Step 1—Tert-butyl 2-[3-[9-(2,6-dioxo-3-piperidyl)pyrido[2,3-b]indol-5-yl]propyl]-2,7-diazaspiro[3.5]nonane-7-carboxylate To a solution of 3-[9-(2,6-dioxo-3-piperidyl)pyrido[2,3-b]indol-5-yl]propanal (200 mg, 596 umol, Intermediate AXY) and tert-butyl 2,7-diazaspiro[3.5]nonane-7-carboxylate (134 mg, 596 umol, CAS #896464-16-7) in THF (15 mL) was added AcOH (35.8 mg, 596 umol). The reaction mixture was stirred at 25° C. for 15 minutes, then NaBH(OAc)$_3$ (63.2 mg, 298 umol) was added. The reaction mixture was stirred at 25° C. for 15 minute then NaBH(OAc)₃ (126 mg, 596 umol) was added again. The reaction mixture was stirred at 25° C. for 30 minutes. On completion, the reaction mixture was quenched with water (2 mL) and concentrated in vacuo. The residue was purified by reverse phase (0.1%, FA) to give the title compound (100 mg, 30.7% yield) as a white solid. LC-MS (ESI⁺) m/z 546.2 (M+H)⁺.

Step 2—3-[5-[3-(2,7-Diazaspiro[3.5]nonan-2-yl)propyl]pyrido[2,3-b]indol-9-yl]piperidine-2,6-dione To a solution of tert-butyl 2-[3-[9-(2,6-dioxo-3-piperidyl)pyrido[2,3-b]indol-5-yl]propyl]-2,7-diazaspiro[3.5]nonane-7-carboxylate (90.0 mg, 164 umol) in DCM (10 mL) was added TFA (4.5 mL). The reaction mixture was stirred at 25° C. for 20 minutes. On completion, the reaction mixture was concentrated in vacuo to give the title compound (90.0 mg, 97% yield, TFA) as light yellow oil. LC-MS (ESI⁺) m/z 446.1 (M+H)⁺.

3-[1-(2,6-Dioxo-3-piperidyl)-3-methyl-2-oxo-benzimidazol-5-yl]propanal (Intermediate AZZ)

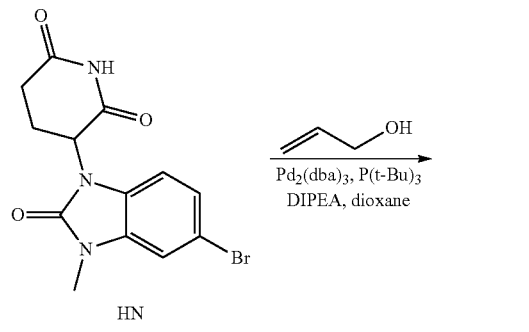

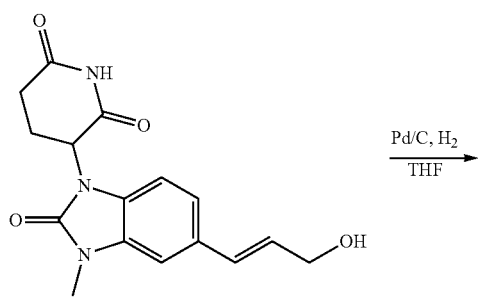

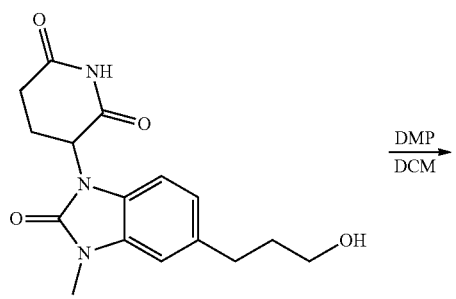

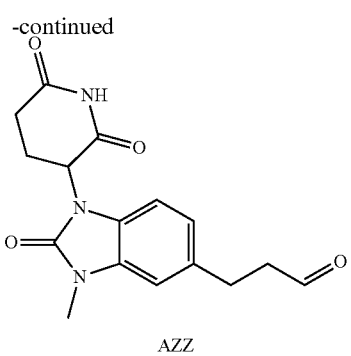

AZZ

Step 1—3-[5-[(E)-3-hydroxyprop-1-enyl]-3-methyl-2-oxo-benzimidazol-1-yl]piperidine-2,6-dione To a solution of 3-(5-bromo-3-methyl-2-oxo-benzimidazol-1-yl)piperidine-2,6-dione (1.00 g, 2.96 mmol, Intermediate HN) and prop-2-en-1-ol (257 mg, 4.44 mmol) in dioxane (15 mL) was added Pd₂(dba)₃ (270 mg, 295 umol) and DIPEA (1.15 g, 8.87 mmol). The reaction mixture was degassed with N₂ three times. Then P(t-Bu)₃ (1.20 g, 591 umol) was added under N₂. The reaction mixture was stirred at 80° C. for 1 hour under N₂. On completion, the reaction mixture was filtered and the filtrate was concentrated in vacuo. The residue was purified by reverse phase flash (0.1% FA) to give the title compound (400 mg, 21% yield) as a white solid. LC-MS (ESI⁺) m/z 316.1 (M+H)⁺.

Step 2—3-[5-(3-Hydroxypropyl)-3-methyl-2-oxo-benzimidazol-1-yl]piperidine-2,6-dione To a solution of 3-[5-[(E)-3-hydroxyprop-1-enyl]-3-methyl-2-oxo-benzimidazol-1-yl]piperidine-2,6-dione (400 mg, 1.27 mmol) in THF (10 mL) was added Pd/C (200 mg, 10 wt %). The reaction mixture was stirred at 25° C. under H₂ (15 Psi) for 12 hours. On completion, the reaction mixture was diluted with THF (30 mL) and filtered. The filtrate was concentrated in vacuo to give the title compound (400 mg, 99% yield) as a light yellow solid. LC-MS (ESI⁺) m/z 318.5 (M+H)⁺.

Step 3—3-[1-(2,6-Dioxo-3-piperidyl)-3-methyl-2-oxo-benzimidazol-5-yl]propanal

To a solution of 3-[5-(3-hydroxypropyl)-3-methyl-2-oxo-benzimidazol-1-yl]piperidine-2,6-dione (400 mg, 1.26 mmol) in THF (20 mL) was added DMP (534 mg, 1.26 mmol). The reaction mixture was stirred at 25° C. for 1 hour. On completion, the reaction mixture was diluted with DCM (50 mL) and washed with sat. NaS₂O₃ (2×30 mL) and brine (2×40 mL), dried with anhydrous Na₂SO₄ and filtered. The filtrate was concentrated in vacuo. The residue was purified by reversed phase flash (0.1% FA) to give the title compound (200 mg, 50% yield) as a white solid. LC-MS (ESI⁺) m/z 316.1 (M+H)⁺.

2313

3-[5-[3-(2,7-Diazaspiro[3.5]nonan-2-yl)propyl]-3-methyl-2-oxo-benzimidazol-1-yl] piperidine-2,6-dione (Intermediate BAA)

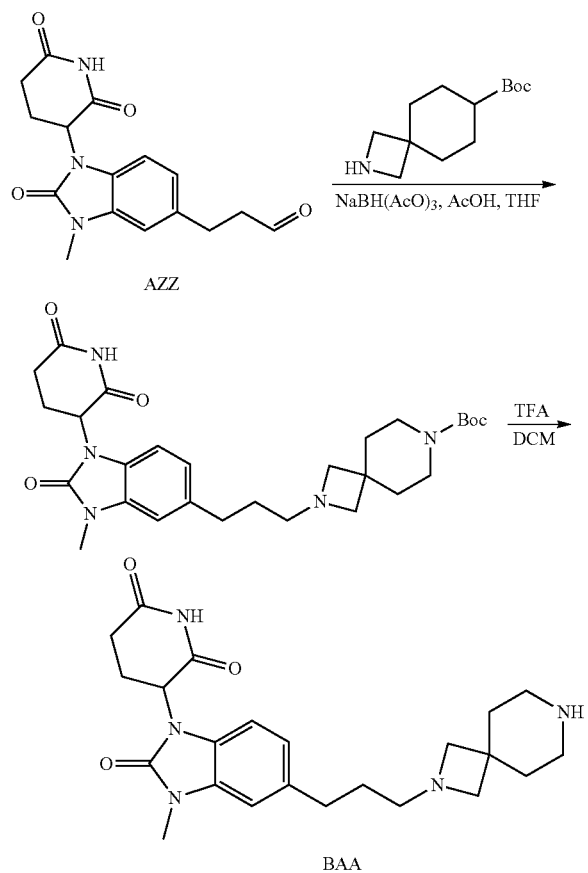

Step 1—Tert-butyl 2-[3-[1-(2,6-dioxo-3-piperidyl)-3-methyl-2-oxo-benzimidazol-5-yl]propyl]-2,7-diazaspiro[3.5]nonane-7-carboxylate To a solution of 3-[1-(2,6-dioxo-3-piperidyl)-3-methyl-2-oxo-benzimidazol-5-yl]propanal (95.0 mg, 301 umol, Intermediate AZZ) and tert-butyl 2,7-diazaspiro[3.5]nonane-7-carboxylate (68.1 mg, 301 umol) in THF (8 mL) was added AcOH (36.1 mg, 602 umol). The reaction mixture was stirred at 25° C. for 15 minutes. Then NaBH(OAc)$_3$ (63.8 mg, 301 umol) was added and the reaction mixture was stirred at 25° C. for 15 minutes. Then NaBH(OAc)$_3$ (63.8 mg, 301 umol) was added again and the reaction mixture was stirred at 25° C. for 15 minutes. On completion, the reaction mixture was diluted with water (0.2 mL) and DMF (2 mL), and concentrated in vacuo. The residue was purified by reverse phase flash (0.1% FA) to give the title compound (100 mg, 63% yield) as a white solid. LC-MS (ESI$^+$) m/z 526.3 (M+H)$^+$.

Step 2—3-[5-[3-(2,7-Diazaspiro[3.5]nonan-2-yl)propyl]-3-methyl-2-oxo-benzimidazol-1-yl] piperidine-2,6-dione To a solution of tert-butyl 2-[3-[1-(2,6-dioxo-3-piperidyl)-3-methyl-2-oxo-benzimidazol-5-yl] propyl]-2,7-di-

2314 azaspiro[3.5]nonane-7-carboxylate (50.0 mg, 95.1 umol) in DCM (10 mL) was added TFA (855 mg, 7.50 mmol). The reaction mixture was stirred at 25° C. for 1 hour. The reaction mixture was concentrated in vacuo to give the title compound (50 mg, 97% yield, TFA) as a light yellow oil. LC-MS (ESI$^+$) m/z 426.1 (M+H)$^+$.

Tert-butyl N-but-3-ynyl-N-methyl-carbamate (Intermediate BAB)

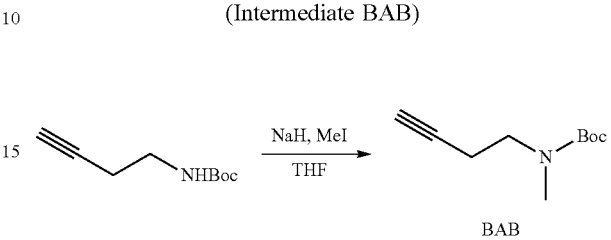

To a mixture of tert-butyl N-but-3-ynylcarbamate (3.00 g, 17.7 mmol, CAS #149990-27-2) in THF (10 mL) was added NaH (1.06 g, 26.6 mmol, 60% dispersion in mineral oil) at 0° C. under N$_2$. The mixture was stirred at 0° C. for 10 minutes. Then, MeI (3.02 g, 21.3 mmol, 1.32 mL) was added dropwise. The mixture was stirred at 25° C. for 2 hours. On completion, the mixture was quenched with water (20 mL) at 0° C., and then extracted with DCM (3×30 mL). The combined organic phase was dried over Na$_2$SO$_4$, filtered and the filtrate was concentrated in vacuo. The residue was purified by column chromatography (SiO$_2$, petroleum ether/ethyl acetate=20/1) to give the title compound (3.20 g, 98% yield) as yellow oil. $^1$H NMR (400 MHz, CDCl$_3$) δ 3.38 (m, 2H), 2.92 (s, 3H), 2.40 (m, 2H), 1.97 (t, J=2.4 Hz, 1H), 1.46 (s, 9H).

2-[5-(Methylamino)pent-2-ynyl]isoindoline-1,3-dione (Intermediate BAC)

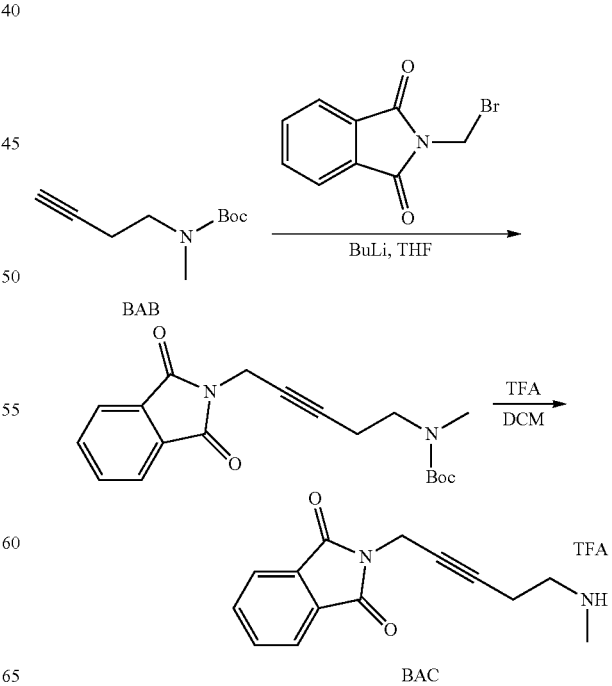

Step 1—Tert-butyl N-[5-(1,3-dioxoisoindolin-2-yl)pent-3-ynyl]-N-methyl-carbamate To a mixture of tert-butyl N-but-3-ynyl-N-methyl-carbamate (1.00 g, 5.46 mmol, Intermediate BAB) in THF (10 mL) was added n-BuLi (2.5 M, 3.27 mL) dropwise at −70° C. under $N_2$. The mixture was stirred at −70° C. for 30 minutes. Then, a solution of 2-(bromomethyl)isoindoline-1,3-dione (1.96 g, 8.19 mmol, CAS #5332-26-3) in THF (2 mL) was added. The mixture was stirred at 25° C. for 1.5 hours. On completion, the mixture was quenched with saturated aqueous $NH_4Cl$ (10 mL), and extracted with EA (3×20 mL). The combined organic phase was dried over $Na_2SO_4$, filtered and the filtrate was concentrated in vacuo. The residue was purified by reverse phase (TFA condition) to afford the title compound (268 mg, 14% yield) as white solid. LC-MS (ESI$^+$) m/z 365.2 (M+Na)$^+$.

Step 2—2-[5-(Methylamino)pent-2-ynyl]isoindoline-1,3-dione

To a mixture of tert-butyl N-[5-(1,3-dioxoisoindolin-2-yl)pent-3-ynyl]-N-methyl-carbamate (90.0 mg, 262 umol) in DCM (1.0 mL) was added TFA (1.80 mL) at 25° C. The mixture was stirred at 25° C. for 2 hours. On completion, the mixture was concentrated in vacuo to give the title compound (90.0 mg, 96% yield) as yellow oil. LC-MS (ESI$^+$) m/z 243.1 (M+H)$^+$.

tert-butyl 4-(piperidin-4-yloxy)piperidine-1-carboxylate (Intermediate BAY)

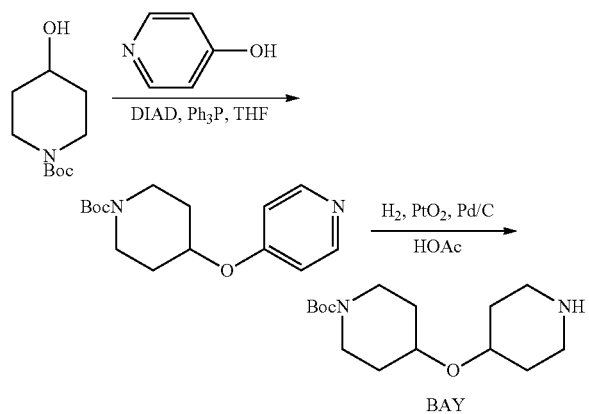

Step 1—tert-butyl 4-(pyridin-4-yloxy)piperidine-1-carboxylate

To a stirred solution of 4-hydroxypyridine (10.00 g, 105.1 mmol) and tert-butyl 4-hydroxypiperidine-1-carboxylate (26.45 g, 131.4 mmol) in THF (350.00 mL) was added $PPh_3$ (34.47 g, 131.4 mmol); then DIAD (26.58 g, 131.4 mmol) was added dropwise at room temperature. The resulting mixture was stirred overnight at 55° C. under nitrogen atmosphere. The mixture was then concentrated under reduced pressure. Next, 1 M aq. HCl (500 mL) was added and the resulting mixture was extracted with $CH_2Cl_2$ (3×150 mL). The water layers were collected and basified to pH=12 with 1M aq. NaOH. The resulting water phase was extracted with $CH_2Cl_2$ (3×150 mL). The organic layers were washed with brine (2×150 mL), and dried over anhydrous $Na_2SO_4$. After filtration, the filtrate was concentrated under reduced pressure. The residue was purified by silica gel column chromatography, eluted with $CH_2Cl_2$/MeOH (10:1) to afford tert-butyl 4-(pyridin-4-yloxy)piperidine-1-carboxylate (19 g, 65%) as a white solid; $^1$H NMR (400 MHz, DMSO-d$_6$) δ 8.41-8.33 (m, 2H), 7.03-6.97 (m, 2H), 4.78-4.67 (m, 1H), 3.72-3.65 (m, 2H), 3.25-3.16 (m, 2H), 2.02-1.92 (m, 2H), 1.53-1.45 (m, 2H), 1.41 (s, 9H); LC/MS (ESI, m/z): [(M+1)]$^+$=279.3.

Step 2—tert-butyl 4-(piperidin-4-yloxy)piperidine-1-carboxylate

To a stirred solution of tert-butyl 4-(pyridin-4-yloxy)piperidine-1-carboxylate (6.00 g, 21.6 mmol,) in AcOH (150.00 mL) were added anhydrous $PtO_2$ (900.00 mg, 3.963 mmol) and Pd/C (600.00 mg, 0.564 mmol, 10 wt %) at room temperature under nitrogen atmosphere. The mixture was hydrogenated at 55° C. for 16 h under hydrogen atmosphere using a hydrogen balloon at room temperature. The mixture was then filtered through a Celite pad and the filter cake was washed with $CH_2Cl_2$ (3×50 mL). The filtrates were evaporated under reduced pressure, and $H_2O$ was added to the residue. Then, $NH_3H_2O$ (20 wt %) was added dropwise to adjust the pH to 10, and the mixture was extracted $CH_2Cl_2$ (3×100 mL). The collected organic layers were dried, filtered, and concentrated to afford tert-butyl 4-(piperidin-4-yloxy)piperidine-1-carboxylate (6 g, 98%) as a colorless oil; $^1$H NMR (400 MHz, Chloroform-d) δ 3.96-3.67 (m, 3H), 3.62-3.56 (m, 1H), 3.51-3.45 (m, 1H), 3.15-2.97 (m, 4H), 2.65-2.58 (m, 2H), 1.95-1.70 (m, 6H), 1.54-1.38 (m, 11H); LC/MS (ESI, m/z): [(M+1)]+=285.2.

(R)-Tert-butyl 4-((4-aminobutan-2-yl)oxy)piperidine-1-carboxylate (Intermediate BBB)

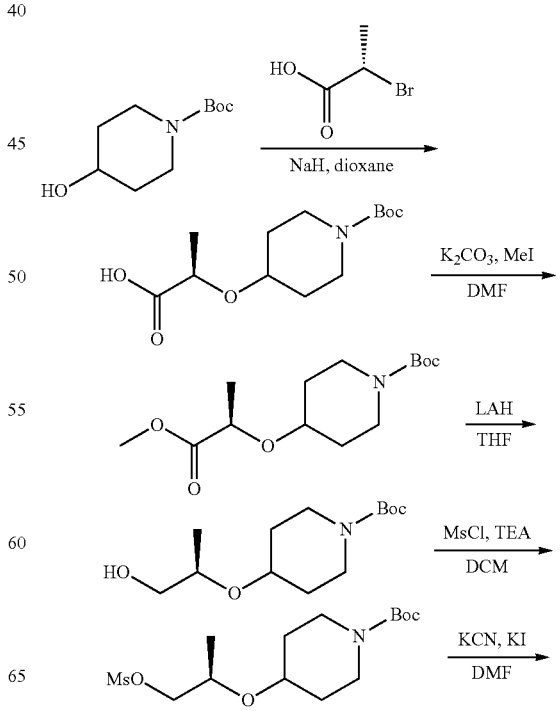

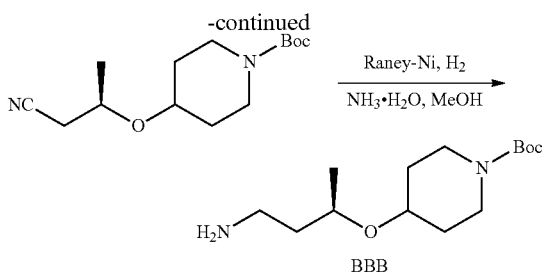

Step 1—(R)-2-((1-(Tert-butoxycarbonyl)piperidin-4-yl)oxy)propanoic acid

To a solution of NaH (26.2 g, 654 mmol) in dioxane (250 mL) was added tert-butyl 4-hydroxypiperidine-1-carboxylate (28.9 g, 144 mmol, CAS #109384-19-2) at 0° C., and the mixture was stirred at 0° C. for 0.5 hour. Then (2S)-2-bromopropanoic acid (20 g, 131 mmol, CAS #32644-15-8) was added, and the mixture was stirred at 25° C. for 16 hours. On completion, the mixture was quenched with water (1.5 L) and then extracted with EA (800 mL). The aqueous layer was acidified to pH=2, and then extracted with EA (2×500 mL). The combined organic layers were dried over $Na_2SO_4$, filtered and concentrated in vacuo to give a residue. The residue was left standing overnight where a solid precipitated from the solution. The solid was collected by filtering and washed with PE/MeOH(5/1, 20 mL) to give the title compound (21 g, 28% yield) as a yellow solid. $^1$H NMR (400 MHz, DMSO-$d_6$) δ 12.54 (s, 1H), 4.07 (m, 1H), 3.65 (m, 2H), 3.50 (s, 1H), 3.33 (s, 2H), 2.99 (s, 2H), 1.85 (m, 2H), 1.38 (s, 9H), 1.24 (m, 3H).

Step 2—(R)-Tert-butyl 4-((1-methoxy-1-oxopropan-2-yl)oxy)piperidine-1-carboxylate To a solution of (2R)-2-[(1-tert-butoxycarbonyl-4-piperidyl)oxy]propanoic acid (21.0 g, 76.8 mmol) in DMF (25.0 mL) was added $K_2CO_3$ (21.2 g, 154 mmol) and MeI (54.5 g, 384 mmol), and the mixture was stirred at 20° C. for 14 hours. On completion, the mixture was concentrated in vacuo to give a residue. The residue was then diluted with water (1.0 L), extracted with EA (3×200 mL), the combined organic phase was dried over $Na_2SO_4$, filtered and concentrated in vacuo to give the title product (21 g, 95% yield) as a yellow oil. $^1$H NMR (400 MHz, CDCl$_3$) δ 4.13 (m, 1H), 3.74-3.52 (m, 5H), 3.50 (m, 1H), 3.10-3.03 (m, 2H), 1.82-1.80 (m, 2H), 1.58 (m, 2H), 1.49-1.45 (m, 9H), 1.44-1.38 (m, 3H).

Step 3—(R)-tert-butyl 4-((1-hydroxypropan-2-yl)oxy)piperidine-1-carboxylate

To a solution of LiAlH$_4$ (4.16 g, 110 mmol) in THF (100 mL) was dropwise added a solution of tert-butyl 4-[(1R)-2-methoxy-1-methyl-2-oxo-ethoxy]piperidine-1-carboxylate (21 g, 73.1 mmol) in THF (110 mL) at 0° C., and the reaction mixture was stirred at 0° C. for 1 hour. On completion, the mixture was quenched with NaOH (1N, 4.20 mL), and saturated aq. $Na_2SO_4$ (50 mL). After that, 200 mL of EA was added and the mixture was stirred at 25° C. for 0.15 hour. Then, the mixture was separated and the organic phase was collected, dried over $Na_2SO_4$ and concentrated in vacuo to give the title product (15.5 g, 82% yield) as yellow oil. $^1$H NMR (400 MHz, CDCl$_3$) δ 3.81-3.42 (m, 7H), 3.05-3.02 (m, 2H), 2.11 (m, 1H), 1.75 (s, 1H), 1.65 (m, 2H), 1.45 (s, 9H), 1.12-1.09 (m, 3H).

Step 4—(R)-Tert-butyl 4-((1-((methylsulfonyl)oxy)propan-2-yl)oxy)piperidine-1-carboxylate To a solution of tert-butyl 4-[(1R)-2-hydroxy-1-methyl-ethoxy]piperidine-1-carboxylate (3.0 g, 10.4 mmol) in DCM (30 mL) was added TEA (2.63 g, 26.0 mmol) and MsCl (1.79 g, 15.6 mmol) at 0° C., and the mixture was stirred at 0° C. for 1 hour. On completion, the mixture was diluted with brine (100 mL) and extracted with DCM (2×50 mL). The combined organic layers were collected, dried over $Na_2SO_4$, filtered and concentrated in vacuo to give the title product (3.51 g, 100% yield) as a yellow oil.

Step 5—(R)-Tert-butyl 4-((1-cyanopropan-2-yl)oxy)piperidine-1-carboxylate

To a solution of tert-butyl 4-[(1R)-1-methyl-2-methylsulfonyloxy-ethoxy]piperidine-1-carboxylate (3.51 g, 10.4 mmol) in DMF (30 mL) was added KI (3.45 g, 20.8 mmol) and KCN (1.02 g, 15.6 mmol) at 25° C. The mixture was stirred at 60° C. for 14 hours. On completion, the mixture was quenched with brine (100 mL), and extracted with EA (2×50 mL). The combined organic layers were collected, dried over $Na_2SO_4$, filtered and concentrated in vacuo to give a residue. The residue was purified by silica gel chromatography (PE/EA=10/1) to give the title product (1.0 g, 32% yield) as a yellow oil. $^1$H NMR (400 MHz, CDCl$_3$) δ 3.87 (m, 1H), 3.74-3.72 (m, 2H), 3.60 (m, 1H), 3.18-3.12 (m, 2H), 2.49-2.47 (m, 2H), 1.79-1.78 (m, 2H), 1.56-1.53 (m, 2H), 1.45 (s, 9H), 1.30-1.28 (m, 3H).

Step 6—(R)-Tert-butyl 4-((4-aminobutan-2-yl)oxy)piperidine-1-carboxylate

To a solution of tert-butyl 4-[(1R)-2-cyano-1-methyl-ethoxy]piperidine-1-carboxylate (500 mg, 1.68 mmol) in MeOH (10 mL) and NH$_3$.H$_2$O (1.0 mL) was added Raney-Ni (143 mg, 1.68 mmol). The mixture was stirred under H$_2$ (40 psi) at 25° C. for 2 hours. On completion, the reaction mixture was filtered and the filtrate was concentrated in vacuo to give the title product (400 mg, 80% yield) as a yellow oil. $^1$H NMR (400 MHz, CDCl$_3$) δ 3.78-3.77 (m, 4H), 3.53-3.50 (m, 2H), 3.03-3.02 (m, 4H), 1.81-1.60 (m, 6H), 1.45 (s, 9H), 1.18 (s, 3H).

2-(2,6-Dioxopiperidin-3-yl)-4-(((R)-3-(piperidin-4-yloxy)butyl)amino)isoindoline-1,3-dione (Intermediate BBC)

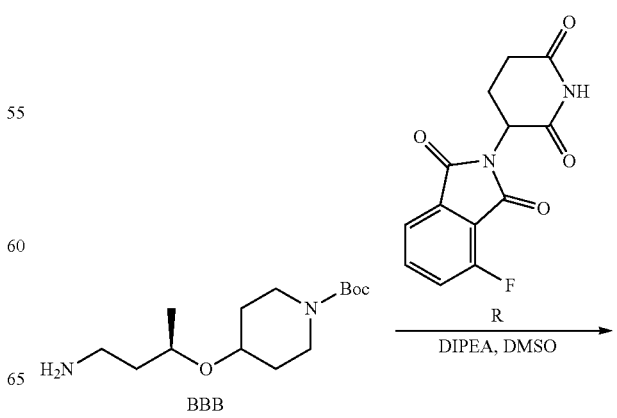

2319
-continued

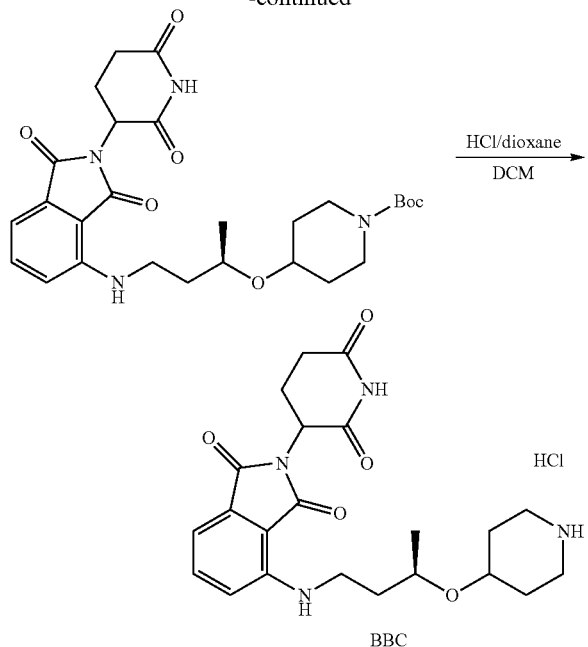

Step 1—Tert-butyl 4-(((2R)-4-((2-(2,6-dioxopiperidin-3-yl)-1,3-dioxoisoindolin-4-yl)amino)butan-2-yl)oxy)piperidine-1-carboxylate To a solution of 2-(2,6-dioxo-3-piperidyl)-4-fluoro-isoindoline-1,3-dione (400 mg, 1.45 mmol, Intermediate R) in

2320

DMSO (5.0 mL) was added DIPEA (374 mg, 2.90 mmol) and tert-butyl 4-[(1R)-3-amino-1-methyl-propoxy]piperidine-1-carboxylate (394 mg, 1.45 mmol, Intermediate BBB), and the mixture was stirred at 130° C. for 1 hour. On completion, the reaction was concentrated in vacuo to give a residue. The residue was purified by reverse phase (0.1% FA condition) to give the title product (380 mg, 49% yield) as a yellow solid. LC-MS (ESI⁺) m/z 429.2 (M−100+H)⁺.

Step 2—2-(2,6-Dioxopiperidin-3-yl)-4-(((R)-3-(piperidin-4-yloxy)butyl)amino)isoindoline-1,3-dione To a solution of tert-butyl 4-[(1R)-3-[[2-(2,6-dioxo-3-piperidyl)-1,3-dioxo-isoindolin-4-yl] amino]-1-methyl-propoxy] piperidine-1-carboxylate (380 mg, 718 umol) in DCM (2.0 mL) was added HCl/dioxane (1.0 mL) at 25° C. The mixture was stirred at 25° C. for 1 hour. On completion, the mixture was concentrated in vacuo to give the title product (340 mg, 71% yield, HCl salt) as a yellow solid. LC-MS (ESI⁺) m/z 429.2 (M+H)⁺.

Example 1 (Method 1). Synthesis of N-[3-carbamoyl-1-[4-[3-[3-[1-(2,6-dioxo-3-piperidyl)-3-methyl-2-oxo-benzimidazol-4-yl] propoxy] propyl-methyl-carbamoyl] cyclohexyl]pyrazol-4-yl-2-[2-(2,2,2-trifluoroethylamino)-4-pyridyl]oxazole-4-carboxamide (I-28)

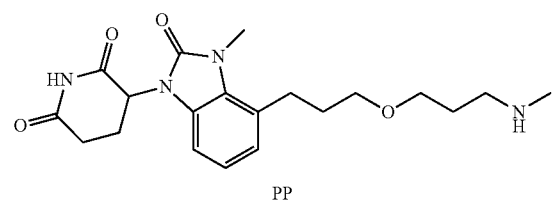

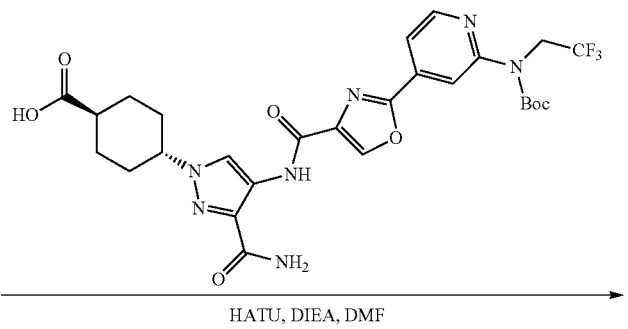

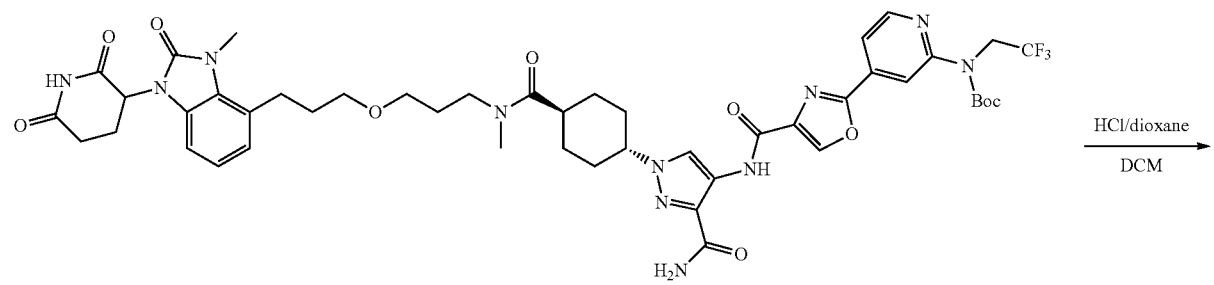

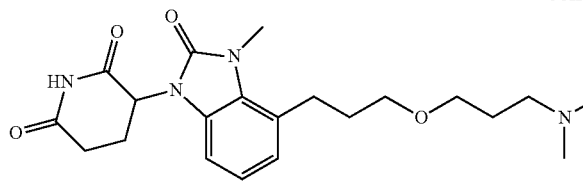
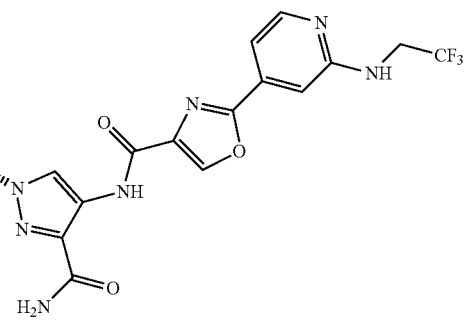

-continued

Step 1—Tert-butyl N-[4-[4-[[3-carbamoyl-1-[4-[3-[3-[1-(2,6-dioxo-3-piperidyl)-3-methyl-2-oxo-benzimidazol-4-yl]propoxy]propylmethyl-carbamoyl]cyclohexyl]pyrazol-4-yl]carbamoyl]oxazol-2-yl]-2-pyridyl-N-(2,2,2-trifluoroethyl)carbamate To a solution of 3-[3-methyl-4-[3-[3-(methylamino)propoxy]propyl]-2-oxo-benzimidazol-1-yl] piperidine-2,6-dione (40.0 mg, 94.1 umol, HCl, Intermediate PP), and 4-[4-[[2-[2-[tert-butoxycarbonyl (2,2,2-trifluoroethyl)amino]-4-pyridyl]oxazole-4-carbonyl]amino]-3-carbamoyl-pyrazol-1-yl]cyclohexanecarboxylic acid (58.5 mg, 94.1 umol, synthesized via Steps 1-2 of Intermediate RF) in DMF (3.00 mL) was added DIPEA (36.5 mg, 282 umol) and HATU (42.9 mg, 112 umol). The mixture was stirred at 25° C. for 0.5 hour. On completion, the mixture was diluted with H$_2$O (15 mL), filtered and the filter cake was collected and dried in vacuo to give the title compound (80.0 mg, 85% yield) as white solid. LC-MS (ESI$^+$) m/z 992.4 (M+H)$^+$.

Step 2—N-[3-carbamoyl-1-[4-[3-[3-[1-(2,6-dioxo-3-piperidyl)-3-methyl-2-oxo-benzimidazol-4-yl]propoxy]propyl-methylcarbamoyl]cyclohexyl]pyrazol-4-yl]-2-[2-(2,2,2-trifluoroethylamino)-4-pyridyl]oxazole-4-carboxamide To a solution of tert-butyl N-[4-[4-[[3-carbamoyl-1-[4-[3-[3-[1-(2,6-dioxo-3-piperidyl)-3-methyl-2-oxo-benzimidazol-4-yl]propoxy]propyl-methyl-carbamoyl]cyclohexyl]pyrazol-4-yl]carbamoyl]oxazol-2-yl]-2-pyridyl]-N-(2,2,2-trifluoroethyl)carbamate (80.0 mg, 80.6 umol) in DCM (3.00 mL) was added HCl in dioxane (4.00 M, 3.00 mL). The mixture was stirred at 25° C. for 0.5 hour. On completion, the mixture was concentrated in vacuo. The residue was purified by prep-HPLC (column: Phenomenex Synergi C18 150*25*10 um; mobile phase: [water (0.225% FA)-ACN]; B %: 31%-61%, 10 min) to give the title compound (19.2 mg, 25% yield) as white solid. $^1$H NMR (400 MHz, DMSO-d$_6$) δ 11.09 (s, 1H), 10.95 (s, 1H), 8.97 (s, 1H), 8.38 (s, 1H), 8.25 (d, J=5.2 Hz, 1H), 7.73-7.58 (m, 2H), 7.50 (s, 1H), 7.26 (s, 1H), 7.17 (d, J=5.2 Hz, 1H), 7.01-6.92 (m, 2H), 6.92-6.81 (m, 1H), 5.42-5.28 (m, 1H), 4.34-4.16 (m, 3H), 3.58 (s, 3H), 3.46-3.99 (m, 4H), 3.36 (s, 3H), 3.05 (s, 2H), 3.00-2.93 (m, 2H), 2.93-2.84 (m, 1H), 2.82-2.71 (m, 2H), 2.61-2.57 (m, 1H), 2.48-2.39 (m, 1H), 2.15-2.10 (m, 1H), 2.10-2.02 (m, 1H), 2.00-1.86 (m, 4H), 1.85-1.81 (m, 2H), 1.80-1.67 (m, 2H), 1.65-1.50 (m, 2H), LC-MS (ESI$^+$) m/z 892.4 (M+H)$^+$.

TABLE 6

Compounds synthesized via Method 1 with the coupling of various amines and acids in Step 1.

| I-# | Step 1 Intermediate Amine | Step 1 Intermediate Acid | LCMS (ES+) m/z (M + H)$^+$ | $^1$HNMR (400 MHz, DMSO-d$_6$) δ |
|---|---|---|---|---|
| I-1 | HQ | PU | 887.9 | 11.08 (s, 1H), 9.71 (s, 1H), 8.91 (s, 1H), 8.17 (s, 1H), 8.14 (d, J = 5.2 Hz, 1H), 7.87 (s, 1H), 7.30-7.01 (m, 4H), 6.96 (d, J = 4.0 Hz, 2H), 6.91-6.84 (m, 1H), 5.35 (dd, J = 4.8, 12.8 Hz, 1H), 4.24-4.18 (m, 1H), 3.56 (s, 3H), 3.53 (m, 8H), 3.21-3.19 (m, 2H), 3.19-3.15 (m, 2H), 2.97-2.93 (m, 2H), 2.87-2.85 (m, 1H), 2.75-2.68 (m, 1H), 2.65-2.61 (m, 1H), 2.20-2.18 (m, 1H), 2.06-1.95 (m, 3H), 1.84-1.82 (m, 4H), 1.77-1.66 (m, 2H), 1.55-1.52 (m, 2H), 1.06-1.04 (m, 1H), 0.45-0.43 (m, 2H), 0.22-0.21 (m, 2H) |
| I-5$^b$ | QR | QT | 830.5 | 11.20 (s, 1H), 9.70 (s, 1H), 8.92 (s, 1H), 8.19 (s, 1H), 8.15 (d, J = 5.2 Hz, 1H), 7.92-7.82 (m, 1H), 7.15 (d, J = 7.2 Hz, 1H), 7.13-7.08 (m, 3H), 7.02 (t, J = 5.6 Hz, 2H), 5.39-5.32 (m, 1H), 4.29-4.17 (m, 1H), 4.11-3.97 (m, 1H), 3.46-3.39 (m, 6H), 3.25-3.21 (m, 4H), 2.83-2.72 (m, 2H), 2.09-2.04 (m, 2H), 1.99 (s, 2H), 1.89-1.82 (m, 4H), 1.78-1.71 (m, 2H), 1.59-1.52 (m, 2H), 1.18 (t, J = 7.2 Hz, 1H), 1.09-1.03 (m, 1H), 0.48-0.43 (m, 2H), 0.24-0.20 (m, 2H) |
| I-15 | HQ | PU | 887.5 | 11.07 (s, 1H), 9.68 (s, 1H), 8.90 (s, 1H), 8.17-8.13 (m, 2H), 7.79 (t, J = 5.6 Hz, 1H), 7.31-7.02 (m, 3H), 7.02- |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d6) δ |
|---|---|---|---|---|
| | | | | 6.99 (m, 1H), 6.95 (d, J = 5.6 Hz, 2H), 6.89-6.83 (m, 1H), 5.35 (dd, J = 5.2, 12.8 Hz, 1H), 4.29-4.27 (m, 1H), 3.55 (s, 3H), 3.53-3.51 (m, 4H), 3.46-3.42 (m, 4H), 3.25-3.20 (m, 2H), 3.18 (t, J = 6.0 Hz, 2H), 2.97-2.91 (m, 2H), 2.91-2.81 (m, 1H), 2.75-2.67 (m, 1H), 2.64-2.57 (m, 1H), 2.42-2.38 (m, 1H), 2.18-2.14 (m, 2H), 2.03-1.94 (m, 1H), 1.89-1.77 (m, 6H), 1.64-1.53 (m, 2H), 1.12-1.00 (m, 1H), 0.50-0.41 (m, 2H), 0.27-0.16 (m, 2H) |
| I-17 | SZ | QT | 912.2 | 11.07 (s, 1H), 9.71 (s, 1H), 8.92 (m, 1H), 8.19 (s, 1H), 8.15 (d, J = 5.2 Hz, 1H), 7.30-7.15 (m, 1H), 7.10 (s, 1H), 7.09-7.05 (m, 1H), 7.04 (s, 1H), 7.03-6.98 (m, 2H), 6.91-6.84 (m, 1H), 5.32 (dd, J = 5.2, 12.8 Hz, 1H), 4.31-4.24 (m, 1H), 3.83-3.75 (m, 2H), 3.32 (s, 3H), 3.18 (t, J = 6.0 Hz, 2H), 3.08 (s, 3H), 2.94-2.89 (m, 1H), 2.86-2.82 (m, 2H), 2.76-2.71 (m, 2H), 2.64-2.57 (m, 6H), 2.27 (t, J = 7.2 Hz, 1H), 2.07-1.67 (m, 12H), 1.61-1.48 (m, 2H), 1.11-1.00 (m, 1H), 0.49-0.41 (m, 2H), 0.26-0.18 (m, 2H) |
| I-18[b] | RR | QT | 912.5 | 11.07 (s, 1H), 9.71 (s, 1H), 8.92 (s, 1H), 8.20 (s, 1H), 8.15 (d, J = 4.4 Hz, 1H), 7.32-6.97 (m, 6H), 6.87 (d, J = 7.6 Hz, 1H), 5.38-5.27 (m, 1H), 4.33-4.22 (m, 1H), 3.83-3.75 (m, 1H), 3.65-3.56 (m, Hz, 2H), 3.54-3.49 (m, 2H), 3.47-3.42 (m, 2H), 3.32 (s, 3H), 3.18 (t, J = 5.2 Hz, 2H), 3.08 (s, 3H), 2.95-2.87 (m, 1H), 2.78-2.73 (m, 1H), 2.69-2.60 (m, 5H), 2.34-2.25 (m, 2H), 2.08-1.95 (m, 4H), 1.84-1.86 (m, 1H), 1.85-1.82 (m, 1H), 1.80-1.70 (m, 4H), 1.62-1.47 (m, 2H), 1.12-1.01 (m, 1H), 0.50-0.40 (m, 2H), 0.28-0.17 (m, 2H) |
| I-19[b] | OP | RX | 874.6 | 11.08 (s, 1H), 7.95 (s, 1H), 7.77 (d, J = 2.4 Hz, 1H), 7.38-7.24 (m, 1H), 7.02-6.92 (m, 2H), 6.88 (d, J = 2.4 Hz, 1H), 6.69 (d, J = 2.4 Hz, 1H), 5.36 (d, J = 5.2 Hz, 1H), 4.43 (d, J = 12.0 Hz, 1H), 4.20 (d, J = 9.6 Hz, 2H), 4.13-3.85 (m, 5H), 3.61-3.55 (m, 21H), 3.26 (s, 3H), 3.01-2.83 (m, 4H), 2.76-2.58 (m, 3H), 2.24 (s, 2H), 2.16-2.05 (m, 2H), 2.05-1.95 (m, 1H), 1.89-1.57 (m, 10H) |
| I-20[b] | OP | HO | 874.4 | 11.08 (s, 1H), 7.77 (s, 1H), 7.53 (d, J = 2.4 Hz, 1H), 7.03 (s, 1H), 6.99 (d, J = 7.6 Hz, 1H), 6.86 (d, J = 8.0 Hz, 1H), 6.53 (d, J = 2.0 Hz, 1H), 6.19 (d, J = 8.0 Hz, 1H), 5.32 (dd, J = 5.2, 12.8 Hz, 1H), 4.11 (s, 2H), 4.08-3.99 (m, 1H), 3.94-3.83 (m, 2H), 3.57-3.49 (m, 16H), 3.41-3.37 (m, 6H), 3.36-3.35 (m, 1H), 3.31 (s, 3H), 2.97-2.82 (m, 1H), 2.70-2.62 (m, 3H), 2.60-2.52 (m, 1H), 2.46-2.42 (m, 2H), 2.38-2.27 (m, 1H), 2.04-1.93 (m, 3H), 1.92-1.69 (m, 6H), 1.69-1.57 (m, 2H), 1.50 (q, J = 12.0 Hz, 2H), 1.33 (q, J = 11.6 Hz, 2H) |
| I-21[b] | SA | ZV | 756.6 | 11.30 (s, 1H), 11.07 (s, 1H), 8.14 (s, 2H), 8.06 (s, 1H), 7.05-6.98 (m, 2H), 6.89-6.82 (m, 2H), 5.52 (d, J = 8.4 Hz, 1H), 5.37-5.27 (m, 1H), 4.02 (m, 1H), 3.91-3.89 (m, 2H), 3.62-3.38 (m, 18H), 2.93-2.80 (m, 2H), 2.65-2.55 (m, 4H), 2.00 (m, 4H), 1.88-1.74 (m, 7H), 1.55 (m, 2H), 1.45-1.32 (m, 4H) |
| I-22[b] | SA | ZW | 754.5 | 11.31 (s, 1H), 11.09 (s, 1H), 8.15 (s, 1H), 8.07 (s, 1H), 7.06-6.98 (m, 2H), 6.86 (d, J = 12.6 Hz, 2H), 5.54 (d, J = 7.6 Hz, 1H), 5.37-5.29 (m, 1H), 4.03 (s, 1H), 3.91 (d, J = 9.2 Hz, 6H), 3.56 (d, J = 11.2 Hz, 1H), 3.33 (s, 3H), 2.96-2.85 (m, 1H), 2.69 (d, J = 11.6 Hz, 4H), 2.62 (d, J = 9.2 Hz, 4H), 2.35 (d, J = 11.8 Hz, 2H), 2.28 (t, J = 6.8 Hz, 2H), 2.02 (s, 4H), 1.84 (d, J = 11.2 Hz, 4H), 1.64-1.53 (m, 4H), 1.52-1.27 (m, 10H) |
| I-23[b] | SA | SB | 827.4 | 11.31 (s, 1H), 11.08 (m, 1H), 8.6 (m, 1H), 7.32-7.22 (m, 1H), 7.04-6.95 (m, 2H), 6.89-6.81 (m, 2H), 5.57-5.50 (m, 1H), 5.37-5.28 (m, 1H), 4.06-3.98 (m, 2H), 3.94-3.86 (m, 4H), 3.70 (m, 14H), 3.32 (s, 3H), 2.88-2.81 (m, 2H), 2.69-2.68 (m, 3H), 2.65-2.59 (m, 4H), 2.07-1.96 (m, 3H), 1.89-1.78 (m, 4H), 1.66-1.40 (m, 13H) |
| I-24[b] | SC | ZV | 686.4 | 11.07 (s, 1H), 8.18 (s, 2H), 8.23-8.16 (m, 1H), 8.03 (s, 1H), 7.03 (s, 1H), 7.00 (d, J = 8.4 Hz, 1H), 6.87 (d, J = 7.6 Hz, 1H), 6.79 (s, 1H), 5.65 (d, J = 8.0 Hz, 1H) 5.32 (m, 1 H), 4.02 (s, 2H), 3.59 (t, J = 6.4 Hz, 2H), 3.44 (m, |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | $^1$HNMR (400 MHz, DMSO-d$_6$) δ |
|---|---|---|---|---|
| | | | | 6H), 2.74-2.69 (m, 2H), 2.69-2.63 (m, 4H), 2.59-2.54 (m, 7H), 2.35 (s, 3H), 1.99 (m, 4H), 1.81-1.79 (m, 4H), 1.45-1.30 (m, 4H) |
| I-25[b] | SC | RX | 804.5 | 11.16 (s, 1H), 11.09 (s, 1H), 8.04 (s, 1H), 6.96 (d, J = 4.2 Hz, 2H), 6.88 (d, J = 4.0 Hz, 1H), 6.80 (s, 1H), 5.67 (d, J = 8.0 Hz, 1H), 5.36 (d, J = 5.2, 12.4 Hz, 1H), 4.13 (s, 2H), 4.08-3.94 (m, 1H), 3.60-3.50 (m, 24H), 3.01-2.83 (m, 4H), 2.77-2.57 (m, 3H), 2.36 (s, 3H), 2.09-1.94 (m, 3H), 1.83 (d, J = 8.0 Hz, 4H), 1.50-1.29 (m, 4H) |
| I-26[b] | SC | ZX | 804.4 | 11.15 (s, 1H), 11.09 (s, 1H), 8.03 (s, 1H), 7.03 (s, 1H), 7.00 (d, J = 8.0 Hz, 1H), 6.87 (d, J = 8.0 Hz, 1H), 6.80 (s, 1H), 5.67 (d, J = 8.0 Hz, 1H), 5.32 (dd, J = 5.2. 12.8 Hz, 1H), 4.12 (s, 2H), 4.06-3.98 (m, 1H), 3.56-3.53 (m, 12H), 3.44-3.35 (m, 12H), 3.32 (s, 3H), 2.93-2.84 (m, 1H), 2.67-2.63 (m, 2H), 2.35 (s, 3H), 2.05-1.97 (m, 3H), 1.86-1.77 (m, 4H), 1.47-1.29 (m, 4H) |
| I-27 | SI | QT | 920.2 | 11.11 (s, 1H), 9.71 (s, 1H), 8.92 (s, 1H), 8.19 (d, J = 3.2 Hz, 1H), 8.15 (d, J = 5.2 Hz, 1H), 7.33-7.13 (m, 2H), 7.12-7.03 (m, 4H), 7.01 (d, J = 5.2 Hz, 1H), 5.37 (dd, J = 5.6, 12.8 Hz, 1H), 4.31-4.23 (m, 1H), 3.33 (s, 3H), 3.18 (d, J = 6.4 Hz, 2H), 3.04 (s, 2H), 3.01-2.82 (m, 4H), 2.81-2.69 (m, 3H), 2.65-2.54 (m, 5H), 2.08-1.71 (m, 10H), 1.61-1.45 (m, 5H), 1.35-1.20 (m, 1H), 1.16-1.02 (m, 2H), 0.48-0.42 (m, 2H), 0.23-0.20 (m, 2H) |
| I-29 | PP | 4-[4-[[2-[2-[tert-butoxycarbonyl (2,2,2-trifluoroethyl)amino]-4-pyridyl]oxazole-4-carbonyl]amino]-3-carbamoyl-pyrazol-1-yl]cyclohexane-carboxylic acid (synthesized via Steps 1-2 of Intermediate RF) | 892.4 | 11.09 (s, 1H), 10.95 (s, 1H), 8.97 (s, 1H), 8.38 (s, 1H), 8.25 (d. J = 5.2 Hz, 1H), 7.73-7.58 (m, 2H), 7.50 (s, 1H), 7.26 (s, 1H), 7.17 (d, J = 5.2 Hz, 1H), 7.01-6.92 (m, 2H), 6.92-6.81 (m, 1H), 5.42-5.28 (m, 1H), 4.34-4.16 (m, 3H), 3.58 (d, J = 6.4 Hz, 3H), 3.46-3.99 (m, 4H), 3.36 (s, 3H), 3.05 (s, 2H), 3.00-2.93 (m, 2H), 2.93-2.84 (m, 1H), 2.82-2.71 (m, 2H), 2.61-2.57 (m, 1H), 2.48-2.39 (m, 1H), 2.15-2.10 (m, 1H), 2.10-2.02 (m, 1H), 2.00-1.86 (m, 4H), 1.85-1.81 (m, 2H), 1.80-1.67 (m, 2H), 1.65-1.50 (m, 2H) |
| I-31 | PP | TS | 861.6 | 11.09 (s, 1H), 9.37 (d, J = 9.6 Hz, 1H), 8.88 (d, J = 1.2 Hz, 1H), 8.15 (d, J = 5.2 Hz, 1H), 8.01 (d, J = 11.6 Hz, 1H), 7.13-7.04 (m, 2H), 7.01 (d, J = 5.6 Hz, 1H), 6.96 (d, J = 4.8, 10.0 Hz, 2H), 6.90-6.84 (m, 1H), 5.42-5.30 (m, 2H), 5.21 (d, J = 8.0 Hz, 1H), 4.23-4.11 (m, 1H), 3.57 (d, J = 6.4 Hz, 3H), 3.48-3.39 (m, 8H), 3.18 (d, J = 6.0 Hz, 2H), 3.04 (s, 2H), 3.02-2.94 (m, 2H), 2.80 (s, 1H), 2.71-2.65 (m, 2H), 2.12-1.97 (m, 6H), 1.93-1.74 (m, 7H), 1.74-1.66 (m, 1H), 1.65-1.47 (m, 2H), 1.17-0.98 (m, 1H), 0.52-0.41 (m, 2H), 0.29-0.15 (m, 2H) |
| I-32[b] | SP | QT | 923.5 | 11.08 (s, 1H), 9.70 (d, J = 6.4 Hz, 1H), 8.94 (d, J = 2.0 Hz, 1H), 8.13 (d, J = 5.6 Hz, 1H), 7.17 (d, J = 5.2 Hz, 1H), 7.15-6.99 (m, 2H), 6.98-6.92 (m, 2H), 6.90-6.82 (m, 1H), 5.41-5.30 (m, 1H), 4.26 (d, J = 3.6 Hz, 1H), 3.56 (s, 3H), 3.54 (s, 3H), 3.52-3.48 (m, 4H), 3.46-3.43 (m, 3H), 3.23-3.15 (m, 3H), 3.08 (s, 2H), 2.98-2.90 (m, 2H), 2.83 (s, 2H), 2.71-2.58 (m, 3H), 2.05-1.94 (m, 3H), 1.90-1.74 (m, 7H), 1.54 (t, J = 13.6 Hz, 2H), 1.13-1.02 (m, 1H), 0.52-0.42 (m, 2H), 0.23 (m, 2H), |
| I-45[b] | SX | QT | 967.6 | 11.09 (s, 1H), 9.71 (s, 1H), 8.92 (d, J = 2.4 Hz, 1H), 8.20-8.18 (m, 1H), 8.15 (d, J = 5.2 Hz, 1H), 7.33-6.91 (m, 7H), 5.43-5.29 (m, 1H), 5.11-4.68 (m, 1H), 4.36-4.21 (m, 1H), 4.07-3.97 (m, 1H), 3.43-3.38 (m, 4H), 3.34 (s, 3H), 3.32 (s, 3H), 3.18 (t, J = 6.0 Hz, 2H), 3.04-2.95 (m, 2H), 2.94-2.86 (m, 1H), 2.84-2.74 (m, 2H), 2.70-2.58 (m, 2H), 2.46-2.37 (m, 6H), 2.35-2.32 (m, 1H), 2.32-2.21 (m, 3H), 2.11-1.98 (m, 4H), 1.95-1.84 (m, 2H), 1.82-1.70 (m, 2H), 1.62-1.48 (m, 2H), 1.13-1.01 (m, 1H), 0.50-0.40 (m, 2H), 0.26-0.19 (m, 2H) |
| I-49[b] | UP | UN | 1033.2 | 8.97 (s, 1H), 8.58 (t, J = 6.0 Hz, 1H), 8.45 (s, 1H), 8.35-8.27 (m, 1H), 8.32 (d, J = 8.4 Hz, 1H), 7.95 (d, J = 7.6 Hz, 1H), 7.63 (s, 1H), 7.48-7.42 (m, 2H), 7.41-7.38 (m, 4H), 5.15 (d, J = 3.2 Hz, 1H), 4.56 (d, J = 9.6 Hz, |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d6) δ |
|---|---|---|---|---|
| | | | | 1H), 4.48-4.32 (m, 4H), 4.29-4.19 (m, 4H), 4.16-4.06 (m, 4H), 3.97 (s, 2 H), 3.70-3.49 (m, 15H), 2.44 (s, 3H), 2.33 (d, J = 1.6 Hz, 1H), 2.10-1.97 (m, 4H), 1.94-1.81 (m, 3 H), 1.50-1.29 (m, 5H), 0.94 (s, 9H) |
| I-50[b] | UP | UR | 967.6 | 8.97 (s, 1H), 8.59 (t, J = 6.0 Hz, 1H), 8.32 (d, J = 8.4 Hz, 1H), 8.18 (s, 1H), 7.95 (d, J = 7.6 Hz, 1H), 7.62 (s, 1H), 7.52-7.35 (m, 6H), 4.57 (d, J = 9.6 Hz, 1H), 4.48-4.33 (m, 3H), 4.30-4.24 (m, 1H), 4.21 (s, 2H), 4.15-4.07 (m, 3H), 4.02-3.91 (m, 2H), 3.68-3.55 (m, 15H), 2.49-2.45 (m, 4H), 2.44 (s, 3H), 2.37-2.29 (m, 1H), 2.09-1.80 (m, 6H), 1.50-1.29 (m, 4H), 0.94 (s, 9H) |
| I-51[b] | UP | ZY | 796.2 | 11.11 (s, 1H), 8.45 (s, 1H), 8.32 (d, J = 8.8 Hz, 1H), 7.97 (br d, J = 7.6 Hz, 1H), 7.63 (s, 1H), 7.59 (t, J = 7.6 Hz, 1H), 7.45 (d, J = 8.8 Hz, 1H), 7.15 (d, J = 8.8 Hz, 1H), 7.04 (d, J = 7.2 Hz, 1H), 6.62 (s, 1H), 5.06 (dd, J = 52, 12.8 Hz, 1H), 4.23 (s, 2H), 4.16-4.10 (m, 1H), 4.12 (s, 2H), 3.66-3.60 (m, 16H), 2.96-2.82 (m, 1H), 2.62-2.60 (m, 1H), 2.59-2.55 (m, 1H), 2.49-2.43 (m, 4H), 2.39-2.29 (m, 1H), 2.02-2.00 (m, 3H), 1.84-1.82 (m, 2H), 1.53-1.28 (m, 4H) |
| I-52[b] | UP | ZZ | 840.5 | 11.08 (s, 1H), 8.45 (s, 1H), 8.32 (d, J = 8.8 Hz, 1H), 8.23 (s, 1H), 7.94 (d, J = 7.2 Hz, 1H), 7.62 (s, 1H), 7.57 (t, J = 7.6 Hz, 1H), 7.44 (d, J = 8.4 Hz, 1H), 7.14 (d, J = 8.8 Hz, 1H), 7.03 (d, J = 7.2 Hz, 1H), 6.60 (t, J = 6.0 Hz, 1H), 5.04 (s, 1H), 4.22 (s, 2H), 4.12 (s, 3H), 3.63 (t, J = 5.2 Hz, 4H), 3.57-3.49 (m, 17H), 2.94-2.80 (m, 1H), 2.63-2.54 (s, 2H), 2.49-2.42 (m, 4H), 2.08-1.95 (m, 3H), 1.88-1.78 (m, 2H), 1.51-1.28 (m, 4H) |
| I-53[b] | SA | RX | 874.5 | 11.08 (s, 1H), 9.07 (s, 1H), 8.10 (s, 1H), 7.07-6.80 (m, 4H), 5.36 (d, J = 5.2, 12.4 Hz, 1H), 4.18 (s, 2H), 3.90 (d, J = 10.4 Hz, 2H), 3.66-3.50 (m, 22H), 3.48-3.40 (m, 6H), 3.17-3.06 (m, 4H), 3.00-2.83 (m, 5H), 2.75-2.56 (m, 3H), 2.25-1.94 (m, 4H), 1.84 (d, J = 8.0 Hz, 4H), 1.60-1.46 (m, 4H) |
| I-106[c] | ZB | QT | 927.3 | 11.10 (s, 1H), 9.73 (s, 1H), 8.92 (d, J = 1.0 Hz, 1H), 8.29 (s, 1H), 8.19(s, 1H), 8.15 (d, J = 5.2 Hz, 1H), 7.33-7.01 (m, 7H), 5.40-5.31 (m, 1H), 4.32-4.23 (m, 1H), 3.82 (d, J = 3.2 Hz, 2H), 3.77 (d, J = 10.4 Hz, 1H), 3.34 (s, 3H), 3.33 (s, 3H), 3.27-3.21 (m, 2H), 3.18 (t, J = 6.0 Hz, 2H), 3.08 (s, 2H), 2.95-2.86 (m, 1H), 2.82 (s, 1H), 2.79-2.71 (m, 2H), 2.67-2.57 (m, 4H), 2.49-2.45 (m, 1H), 2.43 (d, J = 6.0 Hz, 1H), 2.10-1.97 (m, 4H), 1.92-1.72 (m, 5H), 1.65-1.47 (m, 2H), 1.39-1.37 (m, 1H), 1.11-1.02 (m, 1H), 0.50-0.41 (m, 2H), 0.26-0.18 (m, 2H) |
| I-131 | AEV | ACO | 1008.4 | (D2O) δ 8.34 (s, 1H), 7.94 (s, 1H), 7.81 (s, 1H), 7.77-7.70 (m, 4H), 7.60-7.49 (m, 6H), 7.46 (d, J = 8.4 Hz, 2H), 7.30 (d, J = 8.4 Hz, 2H), 6.95-6.89 (m, 2H), 6.84-6.67 (m, 1H), 4.18 (d, J = 7.2 Hz, 2H), 4.11 (d, J = 2.4 Hz, 2H), 3.94 (m, 2H), 3.87-3.80 (m, 1H), 3.65 (m 4H), 3.51-3.31 (m, 4H), 3.26-3.19 (m, 1H), 3.17-3.10 (m, 1H), 2.96 (d, J = 7.2 Hz, 2H), 2.85 (s, 3H), 2.12-2.03 (m, 2H), 1.92 (m, 2H), 1.81 (m, 2H), 1.62-1.52 (m, 2H), 1.27-1.15 (m, 3H), 1.13-1.01 (m, 3H), 0.59 (d, J = 7.4 Hz, 2H), 0.50 (d, J = 8.0 Hz, 2H), 0.33-0.32 (m, 2H), 0.26-0.25 (m, 2H) |
| I-132 | AEW | ACO | 1022.6 | 9.82 (d, J = 5.6 Hz, 1H), 9.68 (s, 2H), 9.04 (d, J = 0.8 Hz, 1H), 8.55 (d, J = 5.2 Hz, 1H), 8.19-8.05 (m, 4H), 7.90 (t, J = 8.0 Hz, 2H), 7.82-7.76 (m, 3H), 7.74-7.70 (m, 1H), 7.66-7.61 (m, 4H), 7.31-7.05 (m, 2H), 4.33 (d, J = 7.2 Hz, 2H), 4.26-4.19 (m, 4H), 3.46-3.44 (m, 3H), 3.26 (d, J = 6.0 Hz, 3H), 3.03 (s, 2H), 2.79 (s, 1H), 2.07-2.01 (m, 2H), 1.91-1.73 (m, 8H), 1.70-1.64 (m, 1H), 1.63-1.51 (m, 2H), 1.36-1.26 (m, 2H), 1.23 (s, 4H), 1.14-1.06 (m, 1H), 0.88-0.79 (m, 1H), 0.54-0.46 (m, 4H), 0.43-0.38 (m, 2H), 0.29 (s, 2H) |
| I-133 | AEY | ACO | 1023.5 | 9.85-9.81 (m, 1H), 9.05 (s, 1H), 8.19-8.05 (m, 4H), 7.82-7.76 (m, 3H), 7.75-7.69 (m, 1H), 7.70-7.61 (m, 4H), 7.50-7.40(m, 3H), 7.33-7.03 (m, 2H), 4.33 (d, J = 6.8 Hz, 2H), 4.23 (s, 4H), 3.47 (s, 3H), 3.30-3.25 |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | ¹HNMR (400 MHz, DMSO-d$_6$) δ |
|---|---|---|---|---|
| | | | | (m, 5H), 2.97-2.87 (m, 4H), 2.80-2.69 (m, 3H), 2.52 (s, 3H), 2.09-2.02 (m, 3H), 1.96-1.73 (m, 9H), 1.30-1.09 (m, 6H), 0.55-0.46 (m, 4H), 0.42-0.38 (m, 2H), 0.34-0.25 (m, 2H) |
| I-134 | WY | ACO | 1004.6 | 9.68 (s, 1H), 8.91 (s, 1H), 8.18 (s, 1H), 8.16-8.13 (m, 2H), 8.09 (s, 1H), 8.00 (s, 1H), 7.81-7.75 (m, 1H), 7.72-7.62 (m, 3H), 7.52-7.40 (m, 4H), 7.34 (d, J = 8.0 Hz, 2H), 7.30-6.99 (m, 4H), 4.33 (d, J = 6.8 Hz, 2H), 4.25-4.17 (m, 1H), 3.83 (s, 4H), 3.66-3.48 (m, 2H), 3.19-3.16 (m, 2H), 2.43-2.38 (m, 2H), 2.25-2.21 (m, 2H), 2.20 (s, 3H), 2.08-2.00 (m, 3H), 1.95-1.86 (m, 2H), 1.83-1.66 (m, 4H), 1.64-1.51 (m, 3H), 1.41-1.39 (m, 2H), 1.36-1.17 (m, 2H), 1.15-1.00 (m, 5H), 0.52-0.43 (m, 4H), 0.42-0.38 (m, 2H), 0.25-0.19 (m, 2H) |
| I-135 | ACN | ACO | 1006.7 | 9.81 (s, 1H), 9.78-9.64 (m, 2H), 9.01 (s, 1H), 8.56 (t, J = 6.0 Hz, 1H), 8.19 (s, 1H), 8.11 (s, 2H), 8.06 (s, 1H), 7.90 (d, J = 8.4 Hz, 2H), 7.83-7.76 (m, 3H), 7.74-7.70 (m, 1H), 7.68-7.62 (m, 4H), 7.47-7.00 (m, 3H), 4.34 (d, J = 7.2 Hz, 2H), 4.28-4.16 (m, 5H), 3.30-3.23 (m, 5H), 3.12-3.04 (m, 1H), 3.03-2.95 (m, 2H), 2.93-2.86 (m, 1H), 2.74 (m, 3H), 2.08-2.02 (m, 2H), 1.96-1.85 (m, 2H), 1.84-1.76 (m, 1H), 1.75-1.63 (m, 2H), 1.61-1.51 (m, 2H), 1.37-1.32 (m, 4H), 1.31-1.24 (m, 2H), 1.23 (s, 3H), 1.20-1.16 (m, 1H), 1.16-1.07 (m, 2H), 0.88-0.82 (m, 1H), 0.54-0.46 (m, 4H), 0.44-0.37 (m, 2H), 0.28 (m, 2H) |
| I-136 | TN | ACQ | 871.6 | 11.08 (s, 1H), 9.40 (s, 1H), 8.77 (d, J = 8.0 Hz, 1H), 8.39 (s, 1H), 8.26 (s, 1H), 7.27-6.92 (m, 3H), 6.91-6.83 (m, 2H), 5.36 (dd, J = 5.2, 12.8 Hz, 1H), 4.28-4.19 (m, 1H), 3.90-3.73 (m, 7H), 3.57 (s, 3H), 3.53-3.46 (m, 3H), 3.31-3.23 (m, 1H), 3.10 (t, J = 9.6 Hz, 1H), 3.02-2.95 (m, 2H), 2.94-2.80 (m, 5H), 2.79-2.62 (m, 3H), 2.07-1.93 (m, 3H), 1.93-1.71 (m, 8H), 1.65-1.50 (m, 2H), 1.49-1.27 (m, 2H) |
| I-137[b] | ACS | AFB | 695.4 | 11.09 (s, 1H), 9.07 (d, J = 2.0 Hz, 1H), 9.03 (d, J = 2.0 Hz, 1H), 8.88 (t, J = 5.5 Hz, 1H), 8.67 (s, 1H), 8.64 (s, 1H), 8.56 (s, 1H), 7.71 (s, 1H), 7.00-6.93 (m, 2H), 6.91-6.85 (m, 1H), 5.36 (d, J = 5.2 Hz, 1H), 4.92-4.73 (m, 1H), 3.71-3.61 (m, 2H), 3.57 (s, 3H), 3.57-3.50 (m, 4H), 3.02-2.94 (m, 2H), 2.70-2.63 (m, 5H), 2.04-1.95 (m, 1H), 1.91-1.82 (m, 2H), 0.90-0.83 (m, 2H), 0.61-0.53 (m, 2H) |
| I-138[b] | ACS | N | 696.4 | 11.21 (s, 1H), 10.36 (s, 1H), 9.05 (s, 1H), 8.64-8.52 (m, 4H), 8.47 (s, 1H), 8.31-8.23 (m, 1H), 8.21-8.14 (m, 1H), 7.62-7.44 (m, 2H), 6.96 (d, J = 5.4 Hz, 3H), 5.43-5.30 (m, 1H), 4.91-4.72 (m, 1H), 3.69-3.61 (m, 2H), 3.57 (s, 3H), 3.53 (s, 3H), 3.47 (d, J = 5.4 Hz, 1H), 2.98 (s, 2H), 2.93-2.82 (m, 2H), 2.63-2.59 (m, 2H), 1.97 (s, 1H), 1.92-1.81 (m, 2H), 1.01-0.92 (m, 2H), 0.63-0.57 (m, 2H) |
| I-139[b] | ADX | N | 740.4 | 11.18-10.84 (m, 1H), 10.35 (s, 1H), 9.05 (s, 1H), 8.61-8.51 (m, 4H), 8.46 (s, 1H), 8.27 (d, J = 8.8 Hz, 1H), 7.59-7.48 (m, 2H), 7.03 (s, 1H), 7.00-6.85 (m, 2H), 5.36-5.29 (m, 1H), 4.87-4.66 (m, 1H), 3.75-3.63 (m, 2H), 3.63-3.58 (m, 2H), 3.55-3.48 (m, 3H), 3.46 (t, J = 5.6 Hz, 1H), 3.41 (t, J = 6.4 Hz, 1H), 3.32-3.31 (m, 3H), 2.95-2.83 (m, 1H), 2.74-2.69 (m, 1H), 2.67-2.64 (m, 2H), 2.60-2.57 (m, 1H), 2.05-1.93 (m, 1H), 1.87-1.78 (m, 2H), 1.23 (s, 1H), 0.98-0.89 (m, 2H), 0.62-0.51 (m, 2H) |
| I-140[b] | ADZ | AFE | 1196.7 | 10.41 (s, 1H), 9.71 (s, 1H), 8.93 (s, 1H), 8.41 (t, J = 5.6 Hz, 1H), 8.32 (d, J = 8.4 Hz, 1H), 8.19 (d, J = 4.0 Hz, 2H), 8.15 (d, J = 5.2 Hz, 1H), 7.74 (t, J = 7.2 Hz, 1H), 7.59 (dd, J = 2.0, 12.8 Hz, 1H), 7.56-7.52 (m, 2H), 7.51-7.46 (m, 1H), 7.42-7.33 (m, 3H), 7.31-7.08 (m, 3H), 7.03-7.00 (m, 1H), 4.62-4.55 (m, 2H), 4.43-4.34 (m, 1H), 4.25-4.14 (m, 1H), 4.00-3.94 (m, 1H), 3.92 (s, 3H), 3.26-3.24 (m, 2H), 3.20-3.17 (m, 2H), 2.21-2.15 (m, 5H), 2.07-2.02 (m, 2H), 1.93-1.86 (m, 2H), 1.82-1.73 (m, 2H), 1.71-1.63 (m, 1H), 1.58-1.50 (m, 3H), 1.48-1.39 (m, 2H), 1.38-1.23 (m, 6H), 1.11-1.01 (m, 3H), 0.98 (s, 9H), 0.49-0.43 (m, 2H), 0.25-0.20 (m, 2H) |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d$_6$) δ |
|---|---|---|---|---|
| I-141[b] | AEB | AFE | 1224.7 | 10.36 (s, 1H), 9.71 (s, 1H), 8.92 (s, 1H), 8.30 (s, 1H), 8.20-8.12 (m, 2H), 7.73 (t, J = 6.8 Hz, 1H), 7.63-7.50 (m, 2H), 7.41-6.89 (m, 10H), 4.63-4.53 (m, 2H), 4.49-4.32(m, 2H), 4.25-4.14 (m, 1H), 3.97-3.90 (m, 1H), 3.88 (s, 3H), 3.17 (t, J = 6.0 Hz, 2H), 2.25 (t, J = 7.2 Hz, 2H), 2.13 (s, 3H), 2.11-2.07 (m, 2H), 2.03 (d, J = 9.8 Hz, 2H), 1.93-1.85 (m, 2H), 1.81-1.70 (m, 3H), 1.67-1.61 (m, 2H), 1.59-1.35 (m, 5H), 1.27-1.22 (m, 3H), 1.15-0.98 (m, 6H), 0.96 (s, 9H), 0.50-0.41 (m, 2H), 0.26-0.16 (m, 2H) |
| I-142[b] | AFC | AFE | 1168.5 | 10.40 (s, 1H), 9.67 (s, 1H), 8.91 (s, 1H), 8.40 (t, J = 4.4 Hz, 1H), 8.31 (d, J = 8.4 Hz, 1H), 8.17 (s, 1H), 8.16-8.13 (m, 2H), 7.73 (t, J = 7.2 Hz, 1H), 7.60-7.47 (m, 4H), 7.41-7.32 (m, 3H), 7.30-7.14 (m, 1H), 7.11-7.06 (m, 2H), 7.02-7.01 (m, 1H), 4.60-4.57 (m, 2H), 4.40-4.32 (m, 1H), 4.24-4.14 (m, 1H), 3.99-3.94 (m, 1H), 3.91 (s, 3H), 3.18 (t, J = 6.0 Hz, 3H), 2.22-2.13 (m, 5H), 2.06-1.99 (m, 2H), 1.94-1.86 (m, 2H), 1.81-1.70 (m, 2H), 1.68-1.41 (m, 8H), 1.33-1.20 (m, 2H), 1.10-1.00 (m, 4H), 0.97 (s, 9H), 0.47-0.42 (m, 2H), 0.24-0.20 (m, 2H) |
| I-143[b] | AFD | AFE | 1212.4 | 10.40 (s, 1H), 9.74 (s, 1H), 9.02 (s, 1H), 8.42-8.34 (m, 1H), 8.31 (dd, J = 2.0, 8.4 Hz, 1H), 8.19 (d, J = 6.4 Hz, 1H), 8.10 (d, J = 6.0 Hz, 1H), 7.73 (t, J = 6.8 Hz, 1H), 7.61-7.51 (m, 3H), 7.50-7.44 (m, 1H), 7.43-7.31 (m, 4H), 7.30-7.00 (m, 2H), 4.59 (s, 2H), 4.42-4.22 (m, 2H), 3.99-3.93 (m, 1H), 3.92 (s, 3H), 3.26-3.21 (m, 5H), 3.05-2.86 (m, 3H), 2.79 (s, 1H), 2.09-1.99 (m, 2H), 1.92-1.74 (m, 4H), 1.69-1.41 (m, 8H), 1.39-1.21 (m, 6H), 1.16-1.05 (m, 1H), 0.97 (s, 9H), 0.56-0.50 (m, 2H), 0.32-0.23 (m, 2H) |
| I-144[b] | AEC | AFE | 1238.7 | 10.35 (s, 1H), 9.74 (s, 1H), 8.99 (s, 1H), 8.29 (d, J = 8.0 Hz, 1H), 8.19 (d, J = 4.4 Hz, 1H), 8.15-8.07 (m, 1H), 7.73 (t, J = 7.2 Hz, 1H), 7.62-7.50 (m, 2H), 7.45-6.88 (m, 8H), 4.63-4.53 (m, 2H), 4.52-4.18 (m, 3H), 3.97-3.86 (m, 4H), 3.27 (d, J = 7.2 Hz, 2H), 3.23 (d, J = 7.2 Hz, 2H), 3.02 (s, 3H), 2.11-1.99 (m, 2H), 1.96-1.39 (m, 13H), 1.29-1.21 (m, 2H), 1.21-1.03 (m, 4H), 0.97 (d, J = 2.8 Hz, 9H), 0.56-0.43 (m, 2H), 0.28-0.25 (m, 2H) |
| I-145[b] | ACU | AFE | 1228.7 | 10.40 (s, 1H), 9.67 (s, 1H), 8.91 (s, 1H), 8.46 (t, J = 5.6 Hz, 1H), 8.32 (d, J = 8.4 Hz. 1H), 8.18 (s, 1H), 8.14 (s, 1H), 7.73 (t, J = 7.2 Hz, 1H), 7.60-7.46 (m, 4H), 7.42-7.28 (m, 3H), 7.17-6.99 (m, 4H), 4.63-4.55 (m, 2H), 4.42-4.31 (m, 1H), 4.25-4.12 (m, 1H), 3.99-3.94 (m, 1H), 3.91 (s, 3H), 3.58-3.47 (m, 8H), 3.46-3.39 (m, 2H), 3.18 (t, J = 6.0 Hz, 2H), 2.52-2.51 (m, 2H), 2.30-2.26 (m, 1H), 2.23 (s, 3H), 2.21-2.16 (m, 1H), 2.07-1.99 (m, 2H), 1.92-1.84 (m, 2H), 1.81-1.71 (m, 2H), 1.71-1.59 (m, 1H), 1.58-1.48 (m, 1H), 1.31-1.20 (m, 1H), 1.10-0.99 (m, 3H), 0.97 (s, 9H), 0.48-0.41 (m, 2H), 0.25-0.18 (m, 2H) |
| I-146[b] | AEN | AHB | 1134.6 | 9.68 (s, 1H), 8.91 (s, 1H), 8.25 (s, 1H), 8.17 (s, 1H), 8.15 (s, 1H), 7.53-6.82 (m, 12H), 5.00 (d, J = 10.8 Hz, 1H), 4.22-4.13 (m, 1H), 3.87-3.79 (m, 2H), 3.60-3.57 (m, 2H), 3.41 (s, 3H), 3.19-3.13 (m, 4H), 3.07-3.04 (m, 2H), 2.80 (d, J = 12.8 Hz, 1H), 2.37-2.32 (m, 2H), 2.20-2.11 (m, 3H), 2.07 (s, 3H), 2.04-1.96 (m, 4H), 1.87 (d, J = 11.6 Hz, 2H), 1.79-1.68 (m, 2H), 1.41-1.31 (m, 4H), 1.28 (d, J = 6.4 Hz, 6H), 1.23 (s, 4H), 1.02-0.91 (m, 2H), 0.55 (d, J = 6.4 Hz, 3H), 0.47-0.43 (m, 2H), 0.40 (d, J = 6.0 Hz, 3H), 0.22 (d, J = 4.0 Hz, 2H) |
| I-147[b] | ACW | AHB | 1160.6 | 9.69 (s, 1H), 8.91 (s, 1H), 8.18 (s, 1H), 8.14 (s, 1H), 7.46-7.19 (m, 4H), 7.19-7.13 (m, 2H), 7.10 (s, 1H), 7.09-7.05 (m, 1H), 7.03-6.99 (m, 1H), 6.98-6.89 (m, 2H), 5.02-4.89 (m, 1H), 4.59-4.45 (m, 1H), 4.26-4.15 (m, 1H), 4.10-4.01 (m, 1H), 3.85-3.75 (m, 1H), 3.62-3.52 (m, 1H), 3.21-3.14 (m, 4H), 3.14-3.00 (m, 3H), 2.84-2.72 (m, 2H), 2.52 (s, 3H), 2.30-2.20 (m, 4H), 2.17-2.01 (m, 6H), 1.95-1.85 (m, 2H), 1.83-1.68 (m, 4H), 1.65-1.52 (m, 2H), 1.46-1.34 (m, 2H), 1.29 (d, J = 6.8 Hz, 6H), 1.22 (d, J = 8.8 Hz, 3H), 1.14- |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d$_6$) δ |
|---|---|---|---|---|
| | | | | 0.93 (m, 5H), 0.58 (d, J = 5.2 Hz, 3H), 0.48-0.43 (m, 2H), 0.42-0.38 (m, 3H), 0.25-0.18 (m, 2H) |
| I-148[b] | AAY | ACY | 854.3 | 11.10 (s, 1H), 9.73 (s, 1H), 8.92 (s, 1H), 8.14 (s, 1H), 7.31-7.11 (m, 3H), 7.10-7.07 (m, 2H), 7.01 (dd, J = 1.2, 5.2 Hz, 1H), 5.38 (dd, J = 4.8, 12.4 Hz, 1H), 4.51 (d, J = 11.2 Hz, 2H), 4.01-4.00 (m, 1H), 3.90-3.74 (m, 2H), 3.35 (s, 3H), 3.22-3.13 (m, 4H), 3.08-3.00 (m, 2H), 2.95-2.85 (m, 2H), 2.78-2.68 (m, 4H), 2.12-1.97 (m, 4H), 1.91-1.68 (m, 6H), 1.41-1.26 (m, 2H), 1.16-0.98 (m, 2H), 0.49-0.41 (m, 2H), 0.25-0.18 (m, 2H) |
| I-149[b] | TN | AEO | 872.5 | 11.09 (s, 1H), 9.40 (s, 1H), 8.83 (d, J = 8.0 Hz, 1H), 8.39 (s, 1H), 8.29 (s, 1H), 7.25-6.93 (m, 3H), 6.93-6.84 (m, 2H), 5.37 (dd, J = 5.2, 12.8 Hz, 1H), 4.28-4.21 (m, 1H), 3.89-3.67 (m, 10H), 3.57 (s, 3H), 3.54-3.45 (m, 3H), 3.28-3.23 (m, 1H), 3.14-3.05 (m 1H), 3.01-2.83 (m, 3H), 2.78-2.60 (m, 3H), 2.07-1.95 (m, 3H), 1.92-1.72 (m, 8H), 1.63-1.49 (m, 2H), 1.48-1.28 (m, 2H) |
| I-150[b] | AFO | AGJ | 843.6 | 11.09 (s, 1H), 9.36 (s, 1H), 8.53 (d, J = 7.6 Hz, 1H), 8.34 (s, 1H), 8.15 (s, 1H), 7.80 (d, J = 8.8 Hz, 1H), 7.29-6.99 (m, 2H), 6.96 (t, J = 8.0 Hz, 1H), 6.91-6.83 (m, 1H), 6.62 (d, J = 7.6 Hz, 1H), 5.37 (dd, J = 5.2, 12.8 Hz, 1H), 4.85-4.66 (m, 1H), 4.32-4.14 (m, 2H), 3.88-3.80 (m, 1H), 3.67 (s, 3H), 3.64-3.60 (m, 2H), 2.97-2.79 (m, 5H), 2.74-2.58 (m, 2H), 2.18 (d, J = 6.8 Hz, 2H), 2.13-1.83 (m, 9H), 1.77-1.63 (m, 4H), 1.63-1.45 (m, 5H), 1.43-1.28 (m, 2H), 1.14-0.98 (m, 2H) |
| I-151[b] | AGN | ABQ | 892.1 | 11.14 (s, 1H), 9.40 (s, 1H), 8.74 (d, J = 8.0 Hz, 1H), 8.56 (d, J = 7.6 Hz, 1H), 8.44 (d, J = 4.8 Hz, 1H), 8.40 (s, 1H), 8.25 (s, 1H), 7.50-7.41 (m, 2H), 7.29 (d, J = 6.0 Hz, 1H), 7.25-6.96 (m, 2H), 6.92 (d, J = 8.0 Hz, 1H), 4.29-4.08 (m, 3H), 3.82 (t, J = 4.0 Hz, 1H), 3.64-3.44 (m, 7H), 3.31-3.18 (m, 4H), 3.12-3.04 (m, 2H), 3.03-2.92 (m, 4H), 2.25-2.15 (m, 1H), 2.14-2.05 (m, 3H), 2.04-1.96 (m, 3H), 1.92 (d, J = 10.4 Hz, 4H), 1.87-1.79 (m, 4H), 1.71 (d, J = 2.8 Hz, 2H), 1.45 (dq, J = 4.0, 8.4 Hz, 2H), 1.27-1.12 (m, 2H) |
| I-152[b] | AFR | ABQ | 897.6 | 10.98 (d, J = 5.2 Hz, 1H), 9.38 (s, 1H), 8.73 (d, J = 8.0 Hz, 1H), 8.38 (s, 1H), 8.25 (s, 1H), 7.47-7.38 (m, 4H), 7.25-6.95 (m, 1H), 6.91 (d, J = 8.0 Hz, 1H), 5.71-5.59 (m, 1H), 4.84-4.76 (m, 1H), 4.73-4.62 (m, 1H), 4.23-4.06 (m, 3H), 3.95-3.85 (m, 1H), 3.84-3.78 (m, 1H), 3.63-3.56 (m, 2H), 3.52-3.45 (m, 2H), 3.44-3.36 (m, 3H), 2.91-2.77 (m, 1H), 2.73-2.62 (m, 4H), 2.28-2.17 (m, 1H), 2.14-2.09 (m, 2H), 2.08-1.95 (m, 5H), 1.91-1.80 (m, 6H), 1.77-1.68 (m, 2H), 1.62-1.52 (m, 1H), 1.50-1.40 (m, 4H), 1.09-0.98 (m, 2H) |
| I-153[b] | AFT | AGJ | 904.3 | 11.10 (s, 1H), 9.29 (s, 1H), 8.54 (d, J = 7.6 Hz, 1H), 8.41 (s, 1H), 8.18 (s, 1H), 7.87 (d, J = 9.6 Hz, 1H), 6.96 (d, J = 4.8 Hz, 2H), 6.90-6.86 (m, 1H), 6.63 (d, J = 7.6 Hz, 1H), 5.40-5.32 (m, 1H), 4.83-4.80 (m, 1H), 4.28-4.13 (m, 2H), 3.89-3.80 (m, 1H), 3.57 (s, 3H), 3.46 (t, J = 6.2 Hz, 2H), 3.00-2.84 (m, 3H), 2.72-2.59 (m, 4H), 2.13-1.95 (m, 8H), 1.92-1.68 (m, 11H), 1.64-1.41 (m, 8H), 1.38-1.28 (m, 3H), 1.09-0.98 (m, 3H), 0.88-0.79 (m, 1H) |
| I-154 | AAU | OM | 857.2 | 11.07 (s, 1H), 9.68 (s, 1H), 8.91 (s, 1H), 8.25 (s, 1H), 8.18-8.13 (m, 2H), 7.31-7.00 (m, 4H), 6.96 (d, J = 4.8 Hz, 2H), 6.91-6.84 (m, 1H), 5.36 (dd, J = 5.2, 12.8 Hz, 1H), 4.23-4.14 (m, 1H), 3.56 (s, 3H), 3.44-3.46 (m, 4H), 3.18 (t, J = 6.4 Hz, 2H), 3.00-2.93 (m, 2H), 2.92-2.83 (m, 1H), 2.75-2.67 (m, 1H), 2.65-2.58 (m, 1H), 2.55-2.53 (m, 2H), 2.41 (t, J = 6.4 Hz, 2H), 2.21 (s, 3H), 2.04-1.95 (m, 3H), 1.88-1.79 (m, 4H), 1.77-1.67 (m, 2H), 1.36 (s, 3H), 1.17-1.02 (m, 3H), 0.48-0.41 (m, 2H), 0.24-0.20(m, 2H) |
| I-155 | ADF | ACE | 920.5 | 11.10 (s, 1H), 9.26 (s, 1H), 8.88 (d, J = 8.0 Hz, 1H), 8.38 (s, 1H), 8.32 (s, 1H), 7.29-6.99 (m, 3H), 6.95 (t, J = 8.0 Hz, 1H), 6.89-6.84 (m, 1H), 5.37 (dd, J = 5.2, 12.4 Hz, 1H), 4.87-4.71 (m, 1H), 4.39-4.30 (m, 1H), 4.22-4.16 (m, 1H), 3.67 (s, 2H), 3.60 (s, 3H), 3.12-3.10 (m, 2H), 3.08-3.03 (m, 2H), 2.93-2.89 (m, 1H), |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d$_6$) δ |
|---|---|---|---|---|
| | | | | 2.83-2.80 (m, 2H), 2.77-2.70 (m, 1H), 2.66-2.62 (m, 1H), 2.62-2.58 (m, 1H), 2.40-2.35 (m, 2H), 2.19-2.17 (m, 1H), 2.17 (s, 3H), 2.07-1.98 (m, 4H), 1.97-1.92 (m, 2H), 1.88-1.84 (m, 2H), 1.79-1.71 (m, 2H), 1.66-1.60 (m, 2H), 1.58-1.51 (m, 1H), 1.36-1.34 (m, 3H), 1.13-1.00 (m, 4H) |
| I-156[b, d] | ABN | ABO | 842.5 | 11.09 (s, 1H), 9.56 (s, 1H), 8.57 (d, J = 7.6 Hz, 1H), 8.37 (s, 1H), 8.29-8.22 (m, 1H), 8.19 (s, 1H), 7.26-6.93 (m, 3H), 6.91-6.84 (m, 1H), 6.46 (d, J = 7.6 Hz, 1H), 5.42-5.30 (m, 1H), 4.25-4.09 (m, 1H), 3.57 (s, 3H), 3.46-3.44 (m, 2H), 3.30-3.30 (m, 1H), 3.01-2.94 (m, 2H), 2.93-2.85 (m, 1H), 2.76-2.70 (m, 1H), 2.70-2.65 (m, 2H), 2.65-2.57 (m, 1H), 2.19-1.95 (m, 8H), 1.93-1.78 (m, 7H), 1.77-1.66 (m, 2H), 1.63-1.54 (m, 1H), 1.51-1.41 (m, 2H), 1.12-0.97 (m, 3H), 0.57-0.50 (m, 2H), 0.29-0.23 (m, 2H) |
| I-157[b] | ABR | ABQ | 872.5 | 11.08 (s, 1H), 9.39 (s, 1H), 8.73 (d, J = 8.0 Hz, 1H), 8.39 (s, 1H), 8.25 (s, 1H), 7.24-6.95 (m, 3H), 6.93-6.85 (m, 2H), 5.38 (dd, J = 5.2, 12.0 Hz, 1H), 4.29-4.07 (m, 3H), 3.86-3.78 (m, 1H), 3.71-3.64 (m, 1H), 3.59-3.56 (m, 2H), 3.50 (s, 3H), 3.38-3.31 (m, 3H), 3.09-2.82 (m, 8H), 2.78-2.62 (m, 2H), 2.15-1.75 (m, 17H), 1.50-1.39 (m, 2H), 1.24-1.13 (m, 2H) |
| I-158[b, d] | ABN | ABS | 899.5 | 11.09 (s, 1H), 9.39 (s, 1H), 8.75 (d, J = 8.0 Hz, 1H), 8.38 (s, 1H), 8.26 (s, 1H), 7.26-6.95 (m, 3H), 6.92-6.88 (m, 1H), 6.89-6.85 (m, 1H), 5.36 (dd, J = 6.0, 12.8 Hz, 1H), 4.61-4.51 (m, 1H), 4.23-4.11 (m, 1H), 3.57 (s, 3H), 3.45 (t, J = 6.0 Hz, 3H), 3.31-3.25 (m, 2H), 3.13-3.05 (m, 2H), 2.99-2.93 (m, 2H), 2.91-2.84 (m, 1H), 2.72-2.65 (m, 1H), 2.65-2.58 (m, 2H), 2.22 (s, 6H), 2.11 (d, J = 7.2 Hz, 2H), 2.08-1.96 (m, 5H), 1.92-1.68 (m, 11H), 1.62-1.52 (m, 1H), 1.49-1.40 (m, 4H), 1.10-0.98 (m, 2H) |
| I-159[b] | ACK | ACI | 708.4 | 11.07 (s, 1H), 8.94 (d, J = 1.6 Hz, 1H), 8.55 (s, 1H), 8.27 (d, J = 7.6 Hz, 1H), 8.05 (dd, J = 1.6, 8.8 Hz, 1H), 7.76 (d, J = 8.8 Hz, 1H), 6.96 (d, J = 4.8 Hz, 2H), 6.89-6.82 (m, 1H), 5.35 (dd, J = 5.2, 12.4 Hz, 1H), 4.20-4.05 (m, 1H), 3.62 (t, J = 6.4 Hz, 2H), 3.55 (s, 3H), 3.48-3.42 (m, 6H), 2.99-2.92 (m, 2H), 2.91-2.82 (m, 1H), 2.76-2.67 (m, 1H), 2.65-2.60 (m, 1H), 2.59-2.55 (m, 2H), 2.55-2.51 (m, 3H), 2.48-2.45 (m, 1H), 2.43-2.34 (m, 1H), 2.08-1.93 (m, 3H), 1.90-1.74 (m, 4H), 1.50-1.29 (m, 4H) |
| I-160[b] | ABT | ABU | 802.3 | 13.13 (s, 1H), 11.06 (s, 1H), 9.38 (dd, J = 1.6, 6.8 Hz, 1H), 9.14 (dd, J = 1.6, 4.0 Hz, 1H), 8.72 (s, 1H), 8.51 (d, J = 0.8 Hz, 1H), 7.87-7.78 (m, 2H), 731 (dd, J = 4.0, 6.8 Hz, 1H), 6.94 (d, J = 4.8 Hz, 2H), 6.90 (s, 1H), 6.88-6.83 (m, 1H), 5.34 (dd, J = 5.2, 12.8 Hz, 1H), 4.45 (d, J = 13.2 Hz, 1H), 3.95 (d, J = 12.8 Hz, 1H), 3.55 (s, 3H), 3.47-3.38 (m, 4H), 3.17 (t, J = 11.6 Hz, 1H), 2.99-2.82 (m, 4H), 2.79-2.60 (m, 3H), 2.40 (s, 3H), 2.38-2.35 (m, 2H), 2.05-1.91 (m, 3H), 1.88-1.76 (m, 2H), 1.69-1.46 (m, 6H) |
| I-351[b] | AHD | ALS | 911.4 | 11.10 (s, 1H), 9.51 (d, J = 6.8 Hz, 1H), 9.29-9.16 (m, 1H), 8.78 (d, J = 7.4 Hz, 1H), 8.40 (d, J = 4.4 Hz, 1H), 8.26 (d, J = 5.6 Hz, 1H), 7.62 (dd, J = 7.2. 8.4 Hz, 1H), 7.26-6.96 (m, 3H), 6.88-6.44 (m, 2H), 5.33-5.00 (m, 2H), 4.84-4.70 (m, 1H), 4.62-4.49 (m, 1H), 4.33-4.10 (m, 2H), 3.85-3.71 (m, 2H), 3.59 (s, 1H), 3.57-3.48 (m, 1H), 3.47-3.42 (m, 1H), 3.26-3.23 (m, 1H), 3.14-3.02 (m, 2H), 2.95-2.83 (m, 1H), 2.79-2.69 (m, 4H), 2.64-2.58 (m, 1H), 2.58-2.54 (m, 1H), 2.09-1.74 (m, 15H), 1.71-1.33 (m, 5H) |
| I-370 | AJF | ACQ | 881.5 | 11.09 (s, 1H), 9.40 (s, 1H), 8.76 (d, J = 8.0 Hz, 1H), 8.39 (s, 1H), 8.26 (s, 1H), 7.62-7.52 (m, 1H), 7.24-6.93 (m, 3H), 6.88 (d, J = 8.0 Hz, 1H), 6.50 (s, 1H), 5.08-5.01 (m, 1H), 4.29-4.18 (m, 1H), 3.74 (s, 3H), 3.39-3.37 (m, 5H), 2.94-2.86 (m, 1H), 2.82 (s, 4H), 2.63-2.53 (m, 3H), 2.52 (m, 2H), 2.07-1.70 (m, 10H), 1.63-1.36 (m, 9H) |
| I-388[b] | ATN | ALS | 928.9 | 11.14 (s, 1H), 9.50 (d, J = 6.8 Hz, 1H), 8.78 (d, J = 7.6 Hz, 1H), 8.53 (dd, J = 7.6, 1.6 Hz, 1H), 8.44-8.34 (m, 2H), 8.26 (d, J = 5.6 Hz, 1H), 8.04 (s, 1H), 7.52 (d, J = |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | ¹HNMR (400 MHz, DMSO-$d_6$) δ |
|---|---|---|---|---|
| | | | | 7.6 Hz, 1H), 7.39-7.32 (m, 1H), 7.25 (dd, J = 7.6, 4.8 Hz, 1H), 7.10 (d, J = 3.6 Hz, 1H), 7.28-6.95 (m, 1H), 6.89-6.42 (m, 1H), 6.02 (s, 1H), 5.28 (s, 1H), 5.07 (s, 1H), 4.76 (d, J = 19.2 Hz, 1H), 4.31-4.18 (m, 1H), 3.84-3.71 (m, 2H), 3.62-3.57 (m, 4H), 3.43 (s, 4H), 3.11 (d, J = 4.0 Hz, 4H), 2.81-2.70 (m, 3H), 2.58 (t, J = 6.8 Hz, 2H), 2.52 (d, J = 1.6 Hz, 1H), 2.13-1.50 (m, 18H) |
| I-407[b] | AOD | ALS | 909.6 | 11.09 (s, 1H), 9.50 (d, J = 6.6 Hz, 1H), 8.78 (d, J = 1.6 Hz, 1H), 8.39 (d, J = 4.6 Hz, 1H), 8.27-8.23 (m, 2H), 7.24-6.43 (m, 5H), 5.36 (dd, J = 5.2, 12.4 Hz, 1H), 5.30-5.03 (m, 1H), 4.77 (d, J = 18.4 Hz, 1H), 4.34-4.17 (m, 1H), 3.86-3.71 (m, 2H), 3.66-3.58 (m, 2H), 3.57 (s, 3H), 2.95-2.83 (m, 8H), 2.76-2.70 (m, 2H), 2.65-2.60 (m, 1H), 2.07-1.53 (m, 22H) |
| I-418[b] | ALR | ALS | 905.6 | 11.12 (s, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.27-6.93 (m, 4H), 6.89-6.42 (m, 1H), 5.40 (dd, J = 52, 12.8 Hz, 1H), 5.30-5.04 (m, 1H), 4.76 (d, J = 18.8 Hz, 1H), 4.30-4.17 (m, 1H), 3.89-3.72 (m, 4H), 3.66 (s, 2H), 3.65-3.49 (m, 6H), 3.44 (d, J = 9.6 Hz, 1H), 3.39-3.37 (m, 2H), 2.95-2.82 (m, 1H), 2.78-2.68 (m, 1H), 2.66-2.59 (m, 1H), 2.58-2.52 (m, 1H), 2.41-2.24 (m, 2H), 2.08-1.90 (m, 5H), 1.87-1.66 (m, 8H), 1.58-1.44 (m, 2H) |
| I-420[b] | ACV | ALS | 895.5 | 11.11 (s, 1H), 9.51 (d, J = 6.4 Hz, 1H), 8.79 (d, J = 1.6 Hz, 1H), 8.40 (d, J = 5.2 Hz, 1H), 8.26 (d, J = 5.6 Hz, 1H), 7.26-6.95 (m, 4H), 6.89-6.43 (m, 1H), 5.42-5.35 (m, 1H), 5.30-5.06 (m, 1H), 4.81-4.72 (m, 1H), 4.31-4.21 (m, 1H), 4.07-3.90 (m, 4H), 3.84-3.72 (m, 2H), 3.66-3.61 (m, 1H), 3.60 (s, 3H), 3.55-3.41 (m, 6H), 3.15-3.09 (m, 2H), 2.95-2.84 (m, 1H), 2.77-2.68 (m, 2H), 2.64-2.59 (m, 1H), 2.08-1.67 (m, 14H), 1.56 (d, J = 13.2 Hz, 2H) |
| I-422[b] | ALQ | ALS | 909.6 | 11.10 (s, 1H), 9.51 (d, J = 6.4 Hz, 1H), 8.79 (d, J = 7.6 Hz, 1H), 8.40 (d, J = 4.4 Hz, 1H), 8.26 (d, J = 5.6 Hz, 1H), 7.29-7.07 (m, 1H), 6.98 (d, J = 4.8 Hz, 2H), 6.93-6.44 (m, 2H), 5.38 (dd, J = 5.2, 12.4 Hz, 1H), 5.31-5.05 (m, 1H), 4.78 (d, J = 18.8 Hz, 1H), 4.31-4.20 (m, 1H), 3.94-3.77 (m, 4H), 3.77-3.62 (m, 2H), 3.61-3.52 (m, 6H), 2.99-2.88 (m, 3H), 2.73-2.63 (m, 4H), 2.31-2.24 (m, 1H), 2.11-1.90 (m, 6H), 1.88-1.72 (m, 10H), 1.59-1.48 (m, 2H) |
| I-423[b] | AMS | ART | 874.1 | 11.09 (s, 1H), 9.62 (d, J = 4.0 Hz, 1H), 9.05 (d, J = 3.2 Hz, 1H), 8.81 (dd, J = 1.6, 8.0 Hz, 1H), 8.31 (d, J = 52 Hz, 1H), 7.91 (d, J = 8.4 Hz, 2H), 7.52 (d, J = 8.4 Hz, 2H), 7.47-7.17 (m, 1H), 7.03-6.40 (m, 4H), 5.36 (dd, J = 5.2, 12.8 Hz, 1H), 5.32-5.06 (m, 1H), 4.84-4.76 (m, 1H), 3.89-3.61 (m, 4H), 3.55 (s, 3H), 3.49-3.45 (m 1H), 3.08-3.04 (m, 2H), 2.96-2.83 (m, 1H), 2.77-2.67 (m, 1H), 2.63-2.60 (m, 1H), 2.11-1.93 (m, 5H), 1.64-1.50 (m, 6H), 1.37-1.27 (m, 1H), 1.18-1.04 (m, 1H), 0.96-0.83 (m, 1H) |
| I-424[b] | ARS | ART | 933.5 | 11.09 (s, 1H), 9.63 (d, J = 4.0 Hz, 1H), 9.06 (d, J = 3.2 Hz, 1H), 8.85-8.77 (m, 1H), 8.31 (d, J = 5.2 Hz, 1H), 7.92 (d, J = 8.4 Hz, 2H), 7.56 (d, J = 8.8 Hz, 2H), 7.47-7.14(m, 1H), 7.00-6.45 (m, 4H), 5.42-5.33 (m, 1H), 5.32-5.08 (m, 1H), 4.84-4.75 (m, 1H), 4.24-4.00 (m, 1H), 3.88-3.80 (m, 2H), 3.79-3.71 (m, 1H), 3.70-3.60 (m, 4H), 3.57 (s, 3H), 3.51-3.39 (m, 2H), 3.27-3.11 (m, 2H), 2.98-2.87 (m, 3H), 2.79-2.68 (m, 1H), 2.65-2.57 (m, 1H), 2.40-2.19 (m, 6H), 2.12-2.02 (m, 1H), 2.00-1.92 (m, 2H), 1.81-1.71 (m, 2H), 1.58-1.45 (m, 2H) |
| I-426[b] | ALL | ART | 876.5 | 11.08 (s, 1H), 9.62 (d, J = 4.0 Hz, 1H), 9.05 (d, J = 3.2 Hz, 1H), 8.81 (dd, J = 2.0, 7.8 Hz, 1H), 8.31 (d, J = 5.4 Hz, 1H), 7.91 (d, J = 8.0 Hz, 2H), 7.53 (d, J = 8.4 Hz, 2H), 7.48-7.17 (m, 1H), 6.95 (d, J = 5.0 Hz, 2H), 6.91-6.86 (m, 1H), 6.86-6.44 (m, 1H), 5.36 (dd, J = 5.4, 12.4 Hz, 1H), 5.31 (s, 1H), 4.79 (d, J = 12.0 Hz, 1H), 4.59-4.29 (m, 1H), 3.88-3.61 (m, 4H), 3.55 (s, 3H), 3.47 (d, J = 10.0 Hz, 2H), 3.12-2.97 (m, 1H), 2.93-2.84 (m, 3H), 2.76-2.68 (m, 1H), 2.65-2.58 (m, 1H), 2.06-1.93 (m, 3H), 1.80-1.69 (m, 1H), 1.67-1.51 (m, |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d6) δ |
|---|---|---|---|---|
| | | | | 4H), 1.45-1.38 (m, 2H), 1.35-1.26 (m, 2H), 1.15-1.05 (m, 2H) |
| I-427[b] | AMX | AEH | 856.2 | 11.13 (s, 1H), 9.50 (d, J = 4.8 Hz, 1H), 8.78 (d, J = 7.6 Hz, 1H), 8.45-8.35 (m, 1H), 8.25 (d, J = 5.6 Hz, 1H), 7.73-7.62 (m, 1H), 7.19 (d, J = 7.6 Hz, 1H), 7.10 (d, J = 7.6 Hz, 1H), 6.99-6.93 (m, 1H), 6.89-6.42 (m, 1H), 5.42 (dd, J = 4.8, 12.4 Hz, 1H), 5.31-5.03 (m, 1H), 4.77 (d, J = 16.8 Hz, 1H), 4.19 (t, J = 12.0 Hz, 1H), 4.07-3.91 (m, 1H), 3.83-3.79 (m, 1H), 3.77-3.61 (m, 1H), 3.60-3.53 (m, 2H), 3.48-3.42 (m, 2H), 3.39-3.37 (m, 3H), 3.25 (d, J = 4.8 Hz, 2H), 2.95-2.71 (m, 2H), 2.06-2.01 (m, 3H), 1.98-1.71 (m, 8H), 1.67-1.35 (m, 4H), 1.29-1.08 (m, 4H) |
| I-429[b] | AGI | ALS | 881.4 | 11.10 (s, 1H), 9.50 (d, J = 6.8 Hz, 1H), 8.78 (d, J = 7.6 Hz, 1H), 8.38 (d, J = 4.8 Hz, 1H), 8.25 (d, J = 5.6 Hz, 1H), 7.62-7.00 (m, 2H), 6.97-6.92 (m, 2H), 6.89-6.42 (m, 1H), 5.37 (dd, J = 5.2, 12.4 Hz, 1H), 5.30-5.03 (m, 1H), 4.76 (d, J = 18.4 Hz, 1H), 4.29-4.17 (m, 1H), 3.82 (m, 3H), 3.75-3.57 (m, 6H), 3.45 (s, 3H), 3.05-2.97 (m, 4H), 2.93-2.85 (m, 1H), 2.76-2.58 (m, 4H), 2.06-1.93 (m, 5H), 1.91-1.80 (m, 2H), 1.75 (d, J = 12.8 Hz, 2H), 1.71-1.64 (m, 2H), 1.62-1.47 (m, 4H) |
| I-431[b] | AKS | ALS | 939.6 | 11.10 (s, 1H), 9.51 (d, J = 6.4 Hz, 1H), 8.79 (d, J = 7.6 Hz, 1H), 8.40 (d, J = 4.4 Hz, 1H), 8.26 (d, J = 5.2 Hz, 1H), 7.30-6.90 (m, 4H), 6.89-6.44 (m, 1H), 5.43-5.33 (m, 1H), 5.31-5.05 (m, 1H), 4.82-4.71 (m, 1H), 4.36-4.18 (m, 1H), 4.16-3.85 (m, 2H), 3.85-3.78 (m, 2H), 3.77-3.60 (m, 4H), 3.59 (s, 3H), 3.52-3.40 (m, 2H), 3.06-2.83 (m, 5H), 2.79-2.60 (m, 4H), 2.31-2.16 (m, 2H), 2.11-1.86 (m, 9H), 1.83-1.69 (m, 4H), 1.66-1.29 (m, 5H) |
| I-432[b] | ATQ | ALS | 909.7 | 11.17-11.05 (s, 1H), 9.51 (d, J = 6.4 Hz, 1H), 8.83-8.74 (m, 1H), 8.40 (d, J = 5.2 Hz, 1H), 8.26 (d, J = 6.4 Hz, 1H), 7.27-6.81 (m, 3H), 6.42 (m, 1H), 5.45-5.03 (m, 2H), 4.85-4.70 (m, 1H), 4.32-4.17 (m, 1H), 3.88-3.76 (m, 2H), 3.73-3.57 (m, 6H), 3.53-3.40 (m, 8H), 2.68 (s, 4H), 2.37-2.31 (m, 2H), 2.09-1.94 (m, 5H), 1.90-1.73 (m, 4H), 1.59-1.17 (m, 10H) |
| I-433[b] | BAA | ALS | 909.4 | 11.08 (s, 1H), 9.49 (d, J = 6.4 Hz, 1H), 8.76 (d, J = 8.0 Hz, 1H), 8.38 (d, J = 4.4 Hz, 1H), 8.25 (d, J = 5.6 Hz, 1H), 7.23-7.01 (m, 3H), 6.99-6.48 (m, 2H), 5.35-5.32 (m, 1H), 5.30-5.27 (m, 1H), 4.80-4.78 (m, 1H), 4.24-4.22 (m, 1H), 3.80 (s, 3H), 3.76-3.74 (m, 2H), 3.63-3.61 (m, 4H), 3.45-3.43 (m, 2H), 3.38-3.34 (m, 2H), 3.30-3.26 (m, 4H), 3.25-3.24 (m, 2H), 2.91-2.81 (m, 1H), 2.67-2.63 (m, 2H), 2.05-1.98 (m, 5H), 1.94-1.79 (m, 4H), 1.74-1.50 (m, 9H) |
| I-435[b] | ATP | ALS | 937.6 | 11.09 (s, 1H), 9.51 (d, J = 6.8 Hz, 1H), 8.78 (d, J = 7.6 Hz, 1H), 8.40 (d, J = 4.8 Hz, 1H), 8.26 (d, J = 5.6 Hz, 1H), 7.26-6.94 (m, 3H), 6.90-6.44 (m, 2H), 5.36 (dd, J = 5.2, 12.8 Hz, 1H), 5.30-5.05 (m, 1H), 4.77 (d, J = 18.4 Hz, 1H), 4.32-4.18 (m, 1H), 4.30-4.17 (m, 1H), 3.86-3.58 (m, 6H), 3.57 (s, 3H), 2.95-2.88 (m, 3H), 2.76-2.68 (m, 2H), 2.66-2.60 (m, 1H), 2.45-2.39 (m, 6H), 2.07-1.92 (m, 6H), 1.91-1.72 (m, 7H), 1.62-1.53 (m, 2H), 1.48 (m, 4H), 1.42 (m, 2H), 1.33 (m, 2H) |
| I-439[b] | AJI | ALS | 854.4 | 11.09 (s, 1H), 9.50 (d, J = 6.4 Hz, 1H), 8.78 (d, J = 7.6 Hz, 1H), 8.39 (d, J = 4.8 Hz, 1H), 8.26 (d, J = 5.6 Hz, 1H), 7.62-7.54 (m, 1H), 7.26-6.94 (m, 3H), 6.88-6.43 (m, 2H), 5.30-5.02 (m, 2H), 4.77 (d, J = 17.8 Hz, 1H), 4.42 (d, J = 12.8 Hz, 1H), 4.32-4.18 (m, 1H), 4.10-3.97 (m, 1H), 3.85-3.71 (m, 2H), 3.66-3.42 (m, 2H), 3.24 (t, J = 6.4 Hz, 2H), 3.05-2.96 (m, 1H), 2.94-2.82 (m, 1H), 2.78-2.68 (m, 1H), 2.64-2.53 (m, 2H), 2.09-1.99 (m, 4H), 1.99-1.66 (m, 9H), 1.64-1.48 (m, 2H), 1.21-0.97 (m, 2H) |
| I-440[e] | AON | ALS | 936.3 | 11.87 (s, 1H), 11.08 (s, 1H), 9.50 (d, J = 6.0 Hz, 1H), 8.78 (d, J = 7.8 Hz, 1H), 8.39 (d, J = 4.2 Hz, 1H), 8.25 (d, J = 5.6 Hz, 1H), 7.65-7.52 (m, 1H), 7.26-6.96 (m, 3H), 6.89-6.42 (m, 2H), 5.30-5.00 (m, 2H), 4.81-4.72 (m, 1H), 4.28-4.17 (m, 1H), 3.85-3.71 (m, 2H), 3.65-3.58 (m, 1H), 3.51-3.35 (m, 9H), 2.92-2.82 (m, |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d6) δ |
|---|---|---|---|---|
| | | | | 1H), 2.62-2.53 (m, 2H), 2.39-2.29 (m, 1H), 2.10-1.87 (m, 9H), 1.85-1.66 (m, 4H), 1.59-1.46 (m, 2H) |
| I-445 | AZY | ALS | 929.4 | 11.15 (s, 1H), 9.50 (d, J = 4.0 Hz, 1H), 8.78 (, J = 8.0 Hz, 1H), 8.60-8.50 (m, 1H), 8.47-8.36 (m, 2H), 8.26 (d, J = 5.6 Hz, 1H), 7.25-7.38 (m, 2H), 7.34-7.26 (m, 1H), 7.25-6.96 (m, 2H), 6.89-6.43 (m, 1H), 6.15-5.93 (m, 1H), 5.30-5.04 (m, 1H), 4.76 (d, J = 20.0 Hz, 1H), 4.30-4.18 (m, 1H), 3.84-3.71 (m, 3H), 3.68-3.57 (m, 4H), 3.23-2.98 (m, 10H), 2.73-2.69 (m, 2H), 2.11-1.37 (m, 18H) |
| I-447[b] | ANB | ALS | 929.1 | 11.15 (s, 1H), 9.50 (d, J = 6.4 Hz, 1H), 8.77 (dd, J = 7.6. 1.6 Hz, 1H), 8.39 (d, J = 4.8 Hz, 1H), 8.32 (d, J = 5.2 Hz, 1H), 8.27-8.18 (m, 3H), 7.72-7.57 (m, 1H), 7.53 (t, J = 7.6 Hz, 1H), 7.32 (t, J = 7.6 Hz, 1H), 7.10 (d, J = 5.2 Hz, 2H), 6.88-6.41 (m, 1H), 6.19-5.92 (m, 1H), 5.32-5.02 (m, 1H), 4.76 (d, J = 17.2 Hz, 1H), 4.27-4.23 (m, 1H), 3.83-3.80 (m, 2H), 3.73 (d, J = 7.6 Hz, 1H), 3.66-3.64 (m, 2H), 3.61-3.58 (m, 1H), 3.46-3.42 (m, 3H), 3.21-3.15 (m, 4H), 3.08-3.00 (m, 1H), 2.66-2.64 (m, 1H), 2.75-2.64 (m, 2H), 2.64-2.63 (m, 1H), 2.53-2.51 (m, 1H), 2.15-1.48 (m, 18H) |
| I-449[b] | AND | ALS | 895.5 | 11.07 (s, 1H), 9.49 (d, J = 6.8 Hz, 1H), 8.77 (d, J = 7.6 Hz, 1H), 8.37 (d, J = 4.4 Hz, 1H), 8.25 (d, J = 5.6 Hz, 1H), 7.24-6.96 (m, 1H), 6.94 (d, J = 4.8 Hz, 2H), 6.88-6.86 (m, 1H), 6.85-6.43 (m, 1H), 5.35 (dd, J = 4.8, 12.8 Hz, 1H), 5.29-5.04 (m, 1H), 4.76 (d, J = 18.8 Hz, 1H), 4.29-4.19 (m, 1H), 3.77-3.69 (m, 3H), 3.54 (s, 3H), 2.95-2.89 (m, 3H), 2.89-2.79 (m, 4H), 2.75-2.68 (m, 4H), 2.64-2.60 (m, 4H), 2.07-1.91 (m, 7H), 1.87-1.69 (m, 8H), 1.58-1.50 (m, 2H) |
| I-472[b] | ANH | ALS | 883.6 | 11.08 (s, 1H), 9.50 (d, J = 6.4 Hz, 1H), 8.78 (d, J = 1.6 Hz, 1H), 8.39 (d, J = 4.8 Hz, 1H), 8.25 (d, J = 5.6 Hz, 1H), 7.25-7.07 (m, 1H), 6.97 (d, J = 4.8 Hz, 2H), 6.91-6.43 (m, 2H), 5.36 (dd, J = 52, 12.4 Hz, 1H), 5.30-5.03 (m, 1H), 4.81-4.70 (m, 1H), 4.32-4.19 (m, 1H), 3.84-3.72 (m, 2H), 3.66-3.58 (m, 2H), 3.57 (s, 3H), 3.45 (d, J = 9.6 Hz, 2H), 3.40-3.35 (m, 6H), 2.98-2.82 (m, 4H), 2.77-2.68 (m, 2H), 2.66-2.62 (m, 1H), 2.59-2.55 (d, J = 1.6 Hz, 1H), 2.09-1.93 (m, 5H), 1.93-1.76 (m, 4H), 1.71-1.47 (m, 6H) |
| I-480[b] | AOD | ATA | 925.3 | 11.08 (s, 1H), 9.28 (s, 1H), 8.81 (d, J = 8.0 Hz, 1H), 8.40 (s, 1H), 8.28 (s, 1H), 7.33-7.00 (m, 1H), 6.99-6.90 (m, 3H), 6.89-6.83 (m, 1H), 5.45-5.30 (m, 1H), 4.69-4.29 (m, 2H), 4.28-4.20 (m, 1H), 3.65-3.63 (m, 2H), 3.57 (s, 3H), 3.33-3.25 (m, 2H), 3.14-3.07 (m, 4H), 2.94-2.86 (m, 3H), 2.75-2.57 (m, 8H), 2.03-2.00 (m, 3H), 2.10-1.47 (m, 13H), 1.20 (s, 3H), 1.18 (s, 3H). |
| I-496[b] | AOJ | ALS | 909.4 | 1.47-1.69 (m, 7 H), 1.71-1.94 (m, 1 H), 1.72-1.93 (m, 7 H), 1.94-2.10 (m, 7 H), 2.29-2.38 (m, 2 H), 2.59-2.72 (m, 4 H), 2.88-2.98 (m, 3 H), 3.46 (d, J = 10.4 Hz, 1 H), 3.57 (s, 3 H), 3.60-3.66 (m, 1 H), 3.71-3.90 (m, 2 H), 4.18-4.66 (m, 3 H), 4.78 (d, J = 12.0 Hz, 1 H), 5.05-5.31 (m, 1 H), 5.37 (dd, J = 12.0, 5.2 Hz, 1 H), 6.43-6.92 (m, 2 H), 6.94-7.28 (m, 3 H), 8.14 (s, 1H), 8.27 (d, J = 5.6 Hz, 1 H), 8.40 (d, J = 4.6 Hz, 1H), 8.79 (d, J = 7.2 Hz, 1 H), 9.51 (d, J = 6.8 Hz, 1H), 11.09 (s, 1H) |
| I-499[b] | AOD | ARR | 853.5 | 11.08 (s, 1H), 9.35 (dd, J = 1.6, 6.8 Hz, 1H), 9.12 (dd, J = 1.6, 4.0 Hz, 1H), 8.71-8.66 (m, 2H), 8.48 (s, 1H), 7.86 (d, J = 8.0 Hz, 1H), 7.72 (dd, J = 1.6, 8.4 Hz, 1H), 7.37-7.30 (m, 1H), 6.96 (d, J = 4.4 Hz, 2H), 6.91-6.83 (m, 1H), 5.36 (dd, J = 5.6. 12.4 Hz, 1H), 4.27 (tt, J = 3.6, 11.6 Hz, 1H), 3.57(s, 3H), 3.47-3.45 (m, 4H), |

TABLE 6-continued

Compounds synthesized via Method 1 with the coupling of various amines and acids in Step 1.

| I-# | Step 1 Intermediate Amine | Step 1 Intermediate Acid | LCMS (ES+) m/z (M + H)+ | 1HNMR (400 MHz, DMSO-d6) δ |
|---|---|---|---|---|
| | | | | 3.13-3.05 (m, 4H), 2.95-2.87 (m, 3H), 2.87-2.77 (m, 1H), 2.76-2.70 (m, 1H), 2.67-2.63 (m, 1H), 2.62-2.56 (m, 2H), 2.40 (s, 3H), 2.15-2.07 (m, 2H), 2.03-1.88 (m, 3H), 1.84-1.76 (m, 2H), 1.72-1.56 (m, 8H) |

[a] Variations in reaction time for Method 1 were as follows: Step 1 was run anywhere from 0.5-12 h, and Step 2 anywhere from 10 min-17 h. If the product of Step 1 was not a precipitate, a standard work up with water and extraction with ethyl acetate was used to isolate the product. Step 2 deprotection could also be achieved under a variety of standard conditions, including with TFA in DCM at rt. The final products were isolated under standard purification techniques including reverse HPLC, silica gel chromatography, and prep-TLC with appropriate solvent conditions.
[b] No Step 2 deprotection required.
[c] Step 2 deprotection was achieved with HBr/HOAc in DCM at rt for 12 h.
[d] PyBOP and DMAP with DIPEA in DMF at 80° C. for 16 hrs was used for the coupling in Step 1.
[e] The acid was coupled with CDI in ACN at rt for 3 hr, then the amine was added with DBU and the reaction was stirred for 2 hr at rt.

Example 2 (Method 2). Synthesis of 2-[2-(Cyclopropylmethylamino)-4-pyridyl]-N-[3-(difluoromethyl)-1-[4-[[3-[3-[1-(2,6-dioxo-3-piperidyl)-3-methyl-2-oxo-benzimidazol-4-yl]propoxy]propyl-methyl-amino]methyl]cyclohexyl]pyrazol-4-yl]oxazole-4-carboxamide (I-30)

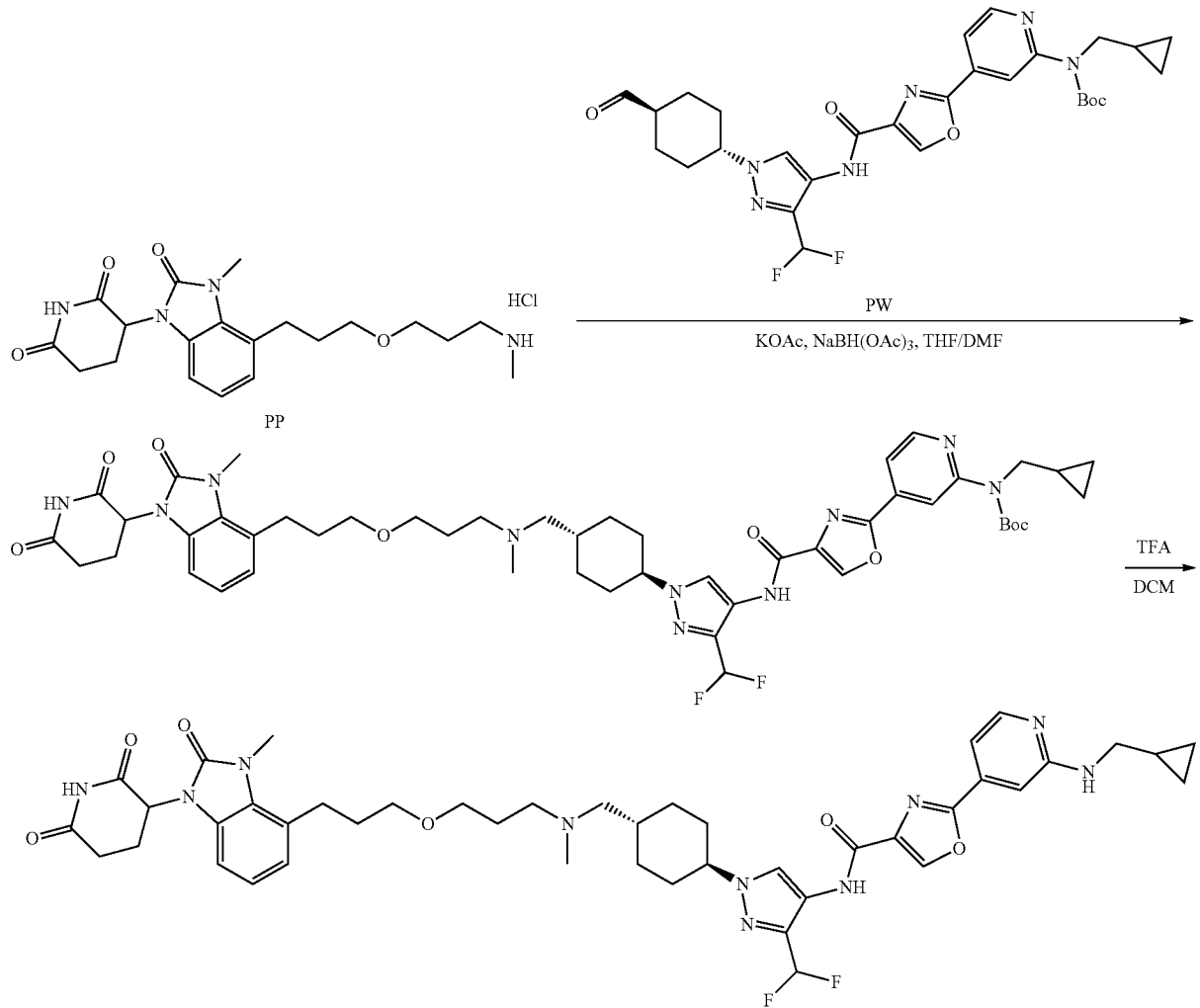

Step 1—Tert-butyl N-(cyclopropylmethyl)-N-[4-[4-[[3-(difluoromethyl)-1-[4-[[3-[3-[1-(2,6-dioxo-3-piperidyl)-3-methyl-2-oxo-benzimidazol-4-yl]propoxy]propyl-methyl-amino]methyl]cyclohexyl]pyrazol-4-yl]carbamoyl]oxazol-2-yl]-2-pyridyl]carbamate To a solution of 3-[3-methyl-4-[3-[3-(methylamino)propoxy]propyl]-2-oxo-benzimidazol-1-yl]piperidine-2,6-dione (45.0 mg, 106 umol, HCl, Intermediate PP) and tert-butyl N-(cyclopropylmethyl) —N-[4-[4-[[3-(difluoromethyl)-1-(4-formylcyclohexyl)pyrazol-4-yl]carbamoyl]oxazol-2-yl]-2-pyridyl]carbamate (61.9 mg, 106 umol, Intermediate PW) in a mixed solvent of DMF (2 mL) and THF (10 mL) was added KOAc (20.8 mg, 212 umol). Thirty minutes later, NaBH(OAc)$_3$ (44.9 mg, 212 umol) was added into the above mixture and the reaction mixture was stirred at 25° C. for 12 hours. On completion, the mixture was concentrated in vacuo. The residue was purified by reverse phase (0.1% FA) to give the title compound (50.0 mg, 49% yield) as a white solid. LC-MS (ESI$^+$) m/z 957.6 (M+H)$^+$.

Step 2—2-[2-(Cyclopropylmethylamino)-4-pyridyl]-N-[3-(difluoromethyl)-1-[4-[[3-[3-[1-(2,6-dioxo-3-piperidyl)-3-methyl-2-oxo-benzimidazol-4-yl]propoxy]propyl-methyl-amino]methyl]cyclohexyl]pyrazol-4-yl]oxazole-4-carboxamide To a solution of tert-butyl N-(cyclopropylmethyl)-N-[4-[4-[[3-(difluoromethyl)-1-[4-[[3-[3-[1-(2,6-dioxo-3-piperidyl)-3-methyl-2-oxo-benzimidazol-4-yl]propoxy]propyl-methyl-amino]methyl]cyclohexyl]pyrazol-4-yl]carbamoyl]oxazol-2-yl]-2-pyridyl]carbamate (48.0 mg, 50.2 umol) in TFA (3 mL) was added DCM (3 mL). The reaction mixture was stirred at 25° C. for 2 hrs. On completion, the mixture was concentrated in vacuo. The residue was purified by prep-HPLC (column: Phenomenex Synergi C18 150*25*10 um; mobile phase: [water (0.225% FA)-ACN]; B %: 10%-37%, 9 min) to give the title compound (35.0 mg, 77% yield) as a white solid. $^1$H NMR (400 MHz, DMSO-d$_6$) δ 11.09 (s, 1H), 9.71 (s, 1H), 8.91 (s, 1H), 8.17-8.13 (m, 2H), 7.29-7.05 (m, 3H), 7.03-7.00 (m, 1H), 6.96 (d, J=4.8 Hz, 2H), 6.89-6.84 (m, 1H), 5.35 (dd, J=5.2, 12.4 Hz, 1H), 4.25-4.13 (m, 1H), 3.56 (s, 3H), 3.43-3.38 (m, 10H), 3.17 (t, J=6.0 Hz, 2H), 2.99-2.92 (m, 2H), 2.90-2.82 (m, 1H), 2.76-2.53 (m, 4H), 2.40 (t, J=6.8 Hz, 2H), 2.22-2.19 (m, 1H), 2.18-2.16 (m, 3H), 2.17-2.14 (m, 1H), 2.07-1.94 (m, 3H), 1.59-1.46 (m, 1H), 1.12-1.05 (m, 1H), 1.05-0.95 (m, 2H), 0.48-0.41 (m, 2H), 0.25-0.18 (m, 2H); LC-MS (ESI$^+$) m/z 857.5 (M+H)$^+$.

TABLE 7

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)$^+$ | $^1$HNMR (400 MHz, DMSO-d$_6$) δ |
|---|---|---|---|---|
| I-2 | HQ | PW | 873.4 | 11.50-10.71 (m, 1H), 9.72 (s, 1H), 8.90 (s, 1H), 8.30 (s, 1H), 8.19-8.09 (m, 2H), 7.32-7.12 (m, 1H), 7.12-7.05 (m, 2H), 7.04-6.99 (m, 1H), 6.98-6.915 (m, 2H), 6.88 (t, J = 4.4 Hz, 1H), 5.41-5.29 (m, 1H), 4.22-4.09 (m, 1H), 3.62-3.56 (m, 11H), 3.21-3.13 (m, 2H), 3.00-2.92 (m, 2H), 2.90-2.80 (m, 3H), 2.69-2.56 (m, 4H), 2.06-1.94 (m, 3H), 1.93-1.78 (m, 4H), 1.76-1.63 (m, 2H), 1.63-1.48 (m, 1H), 1.17-0.97 (m, 3H), 0.50-0.40 (m, 2H), 0.30-0.12 (m, 2H) |
| I-3 | PA | PW | 860.4 | 9.70 (s, 1H), 8.93 (s, 1H), 8.23-8.06 (m, 2H), 7.31-7.14 (m, 3H), 7.12-6.98 (m, 4H), 5.35 (d, J = 5.2, 13.2 Hz, 1H), 4.34-4.07 (m, 1H), 3.58-3.50 (m, 12H), 3.19 (t, J = 6.0 Hz, 2H), 3.18-3.17 (m, 1H), 2.77 (t, J = 5.6 Hz, 2H), 2.71-2.60 (m, 4H), 2.19-2.10 (m, 1H), 2.04-2.02 (m 2H), 1.96-1.65 (m, 6H), 1.59-1.46 (m, 1H), 1.17-1.01 (m, 3H), 0.50-0.41 (m, 2H), 0.26-0.19 (m, 2H) |
| I-6 | HQ | RF | 894.4 | 11.0 (s, 1H), 10.9 (s, 1H), 8.96 (s, 1H), 8.34 (s, 1H), 8.24 (d, J = 5.2 Hz, 1H), 7.70-7.65 (m, 2H), 7.49 (s, 1H), 7.25 (s, 1H), 7.16 (d, J = 5 .2 Hz, 1H), 6.96 (d, J = 4.4 Hz, 2H), 6.88-6.86 (m, 1H), 5.40-5.31 (m, 1H), 4.29-4.21 (m, 2H), 4.20-4.13 (m, 1H), 3.57 (s, 3H), 3.55-3.48 (m, 9H), 3.00-2.94 (m, 2H), 2.86 (d, J = 5.2, 16.4 Hz, 1H), 2.72 (t, J = 5.6 Hz, 2H), 2.61 (d, J = 16.4 Hz, 2H), 2.46-2.43(m, 2H), 2.07-2.00 (m, 2H), 1.99-1.94 (m, 1H), 1.92-1.79 (m, 4H), 1.74 (d, J = 9.6 Hz, 2H), 1.53-1.42 (m, 1H), 1.13-1.00 (m, 2H) |
| I-7 | PA | RF | 860.4 | 9.70 (s, 1H), 8.93 (s, 1H), 8.23-8.06 (m, 2H), 7.31-7.14 (m, 3H), 7.12-6.98 (m, 4H), 5.35 (m, 1H), 4.34-4.07 (m, 1H), 3.58-3.50 (m, 12H), 3.19 (m, 2H), 2.77 (m, 2H), 2.71-2.60 (m, 4H), 2.19-2.10 (m, 1H), 2.04 (m, 2H), 1.96-1.65 (m, 6H), 1.59-1.46 (m, 1H), 1.17-1.01 (m, 3H), 0.50-0.41 (m, 2H), 0.26-0.19 (m, 2H) |
| I-8 | RH | RF | 850.1 | 11.08 (s, 1H), 10.94 (s, 1H), 8.98 (s, 1H), 8.82 (s, 1H), 8.37 (s, 1H), 8.24 (d, J = 5.2 Hz, 1H), 8.05 (s, 1H), 7.68 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | (s, 1H), 7.51 (s, 1H), 7.34 (s, 1H), 7.21 (dd, J = 1.2, 5.6 Hz, 1H), 7.08-6.96 (m, 2H), 6.89 (dd, J = 1.2, 8.0 Hz, 1H), 5.34 (dd, J = 5.6, 13.2 Hz, 1H), 4.37-4.19 (m, 3H), 3.69 (t, J = 5.2 Hz, 2H), 3.45-3.43 (m, 2H), 3.32 (s, 3H), 3.16-3.08 (m, 2H), 2.93-2.79 (m, 3H), 2.73-2.60 (m, 4H), 2.09 (d, J = 10.4 Hz, 2H), 2.10-1.95 (m, 3H), 1.91-1.76 (m, 5H), 1.27-1.11 (m, 2H) |
| I-9 | OD | RF | 892.5 | 10.93 (s, 1H), 8.96-8.93 (m, 1H), 8.36 (s, 1H), 8.24 (d, J = 5.2 Hz, 1H), 7.71-7.62 (m, 2H), 7.48 (s, 1H), 7.24 (s, 1H), 7.18-7.14 (m, 1H), 7.05-6.97 (m, 2H), 6.89-6.83 (m, 1H), 5.35-5.29 (m, 1H), 4.28-4.18 (m, 3H), 3.33-3.31 (m, 7H), 2.95-2.84 (m, 1H), 2.75-2.56 (m, 8H), 2.07 (d, J = 10.0 Hz, 2H), 2.03-1.96 (m, 1H), 1.90 (d, J = 11.6 Hz, 2H), 1.84-1.72 (m, 2H), 1.65-1.59 (m, 2H), 1.57-1.47 (m, 7H), 1.18-0.99 (m, 2H) |
| I-10 | LF | RF | 864.5 | 10.95 (s, 1H), 8.97 (s, 1H), 8.37 (s, 1H), 8.30 (s, 1H), 8.25 (d, J = 5.6 Hz, 1H), 7.74-7.64 (m, 2H), 7.50 (s, 1H), 7.25 (s, 1H), 7.16 (dd, J = 1.6, 5.2 Hz, 1H), 6.97 (d, J = 4.8 Hz, 2H), 6.90-6.81 (m, 1H), 5.37 (dd, J = 5.2, 12.8 Hz, 1H), 4.29-4.19 (m, 3H), 3.58 (s, 3H), 3.48-3.46 (m, 4H), 3.01-2.83 (m, 4H), 2.77-2.58 (m, 6H), 2.37-2.31 (m, 1H), 2.13-2.03 (m, 2H), 1.96-1.92 (m, 3H), 1.88-1.80 (m, 3H), 1.79-1.69 (m, 3H), 1.19-1.05 (m, 2H) |
| I-11 | RI | RF | 850.4 | 11.07 (s, 1H), 10.93 (s, 1H), 8.94 (s, 1H), 8.36 (s, 1H), 8.24 (d, J = 52 Hz, 1H), 7.70-7.62 (m, 2H), 7.48 (s, 1H), 7.25 (s, 1H), 7.16 (d, J = 5.2 Hz, 1H), 6.97 (d, J = 4.4 Hz, 2H), 6.91-6.84 (m, 1H), 5.38-5.32 (m, 1H), 4.30-4.16 (m, 3H), 3.57 (s, 3H), 3.51-3.48 (m, 4H), 2.97 (t, J = 7.6 Hz, 2H), 2.92-2.82 (m, 1H), 2.76 (t, J = 5.2 Hz, 2H), 2.72-2.63 (m, 2H), 2.61-2.54 (m, 2H), 2.07 (d, J = 10.0 Hz, 2H), 2.03-1.97 (m, 1H), 1.96-1.89 (m, 2H), 1.87-1.76 (m, 4H), 1.61-1.45 (m, 1H), 1.20-1.01 (m, 2H) |
| I-12 | PY | RF | 851.4 | 10.94 (s, 1H), 8.96 (s, 1H), 8.36 (s, 1H), 8.24 (d, J = 52 Hz, 1H), 7.71-7.64 (m, 2H), 7.50 (s, 1H), 7.24 (s, 1H), 7.17-7.08 (m, 3H), 7.03 (d, J = 7.6 Hz, 1H), 5.39-5.32 (m, 1H), 4.29-4.17 (m, 3H), 3.61-3.52 (m, 4H), 2.90-2.83 (m, 1H), 2.79-2.64 (m, 8H), 2.17-2.11 (m, 1H), 2.10-2.03 (m, 2H), 1.95-1.89 (m, 2H), 1.88-1.83 (m, 2H), 1.80-1.77 (m, 1H), 1.75-1.71 (m, 2H), 1.65-1.48 (m, 2H), 1.17-1.03 (m, 2H) |
| I-16 | RK | PW | 884.3 | 11.09 (s, 1H), 9.72 (s, 1H), 8.91 (s, 1H), 8.25 (s, 2H), 8.18 (s, 1H), 8.14 (d, J = 5.2 Hz, 1H), 7.15-7.09 (m, 2H), 7.06-6.96 (m, 3H), 6.87 (d, J = 8.0 Hz, 1H), 5.34-5.30 (m, 1H), 4.20 (t, J = 12.0 Hz, 1H), 3.80 (d, J = 10.8 Hz, 2H), 3.32 (s, 3H), 3.17 (t, J = 6.0 Hz, 2H), 2.93-2.86 (m, 1H), 2.80 (d, J = 11.2 Hz, 1H), 2.75-2.61 (m, 8H), 2.53-2.52 (m, 2H), 2.29 (t, J = 6.8 Hz, 2H), 2.07 (s, 1H), 2.05-1.94 (m, 4H), 1.89 (s, 2H), 1.81-1.67 (m, 5H), 1.58 (s, 2H), 1.16-0.99 (m, 3H), 0.48-0.42 (m, 2H), 0.25-0.18 (m, 2H) |
| I-33 | SZ | UW | 906.3 | 11.09 (s, 1H), 10.38 (s, 1H), 8.90-8.83 (m, 1H), 8.17 (s, 1H), 8.15 (d, J = 5.6 Hz, 1H), 7.12 (t, J = 5.2 Hz, 1H), 7.07 (s, 1H), 7.04 (s, 1H), 7.02-6.96 (m, 2H), 6.88 (d, J = 7.6 Hz, 1H), 6.36-5.55 (m, 1H), 5.33 (dd, J = 5.2, 12.8 Hz, 1H), 4.11-3.98 (m, 2H), 3.77-3.74 (m, 2H), 3.31 (s, 3H), 3.18 (t, J = 6.0 Hz, 2H), 2.90-2.80 (m, 2H), 2.71-2.61 (m, 4H), 2.35-2.27 (m, 4H), 2.18 (s, 3H), 2.16-2.07 (m, 2H), 2.04-1.63 (m, 12H), 1.60-1.53 (m, 1H), 1.50 (s, 6H), 1.12-0.92 (m, 3H), 0.51-0.41 (m, 2H), 0.27-0.16 (m, 2H) |
| I-34 | RR | PW | 898.6 | 11.08 (s, 1H), 9.72 (s, 1H), 8.92 (s, 1H), 8.19 (s, 1H), 8.16-8.14 (m, 1H), 7.30-7.07 (m, 3H), 7.05 (s, 1H), 7.01 (d, J = 7.2 Hz, 2H), 6.89 (d, J = 8.0 Hz, 1H), 5.37-5.31 (m, 1H), 4.28-4.18 (m, 1H), 3.90 (d, J = 9.6 Hz, 2H), 3.65 (t, J = 10.8 Hz, 1H), 3.46-3.37 (m, 3H), 3.18 (t, J = 6.0 Hz, 2H), 3.07-2.84 (m, 6H), 2.75-2.54 (m, 12H), 2.06 (d, J = 10.0 Hz, 2H), 2.10-1.97 (m, 1H), 1.91-1.75 (m, 7H), 1.21-1.09 (m, 2H), 1.08-1.03 (m, 1H), 0.48-0.42 (m, 2H), 0.24-0.20 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-35 | RJ | PW | 884.5 | 11.08 (s, 1H), 9.72 (s, 1H), 8.92 (s, 1H), 8.86-8.48 (m, 1H), 8.20 (s, 1H), 8.16-8.13 (m, 1H), 7.31-7.01 (m, 6H), 6.90 (d, J = 8.0 Hz, 1H), 5.38-5.31 (m, 1H), 4.28-4.18 (m, 1H), 3.97 (d, J = 1.2 Hz, 2H), 3.67 (s, 1H), 3.50 (s, 3H), 3.20-3.16 (m, 2H), 3.11 (s, 1H), 3.02-2.98 (m, 1H), 2.97-2.93 (m, 1H), 2.92-2.90 (m, 1H), 2.89-2.84 (m, 2H), 2.71 (t, J = 4.4 Hz, 1H), 2.69-2.65 (m, 3H), 2.62-2.58 (m, 2H), 2.54 (s, 2H), 2.12-2.06 (m, 2H), 2.04-1.96 (m, 2H), 1.94-1.85 (m, 3H), 1.81-1.69 (m, 3H), 1.68-1.56 (m, 1H), 1.24-1.11 (m, 2H), 1.10-1.01 (m, 1H), 0.49-0.43 (m, 2H), 0.25-0.19 (m, 2H) |
| I-36 | SZ | PW | 898.5 | 11.07 (s, 1H), 9.70 (s, 1H), 8.92 (s, 1H), 8.23-8.10 (m, 3H), 7.15 (t, J = 54 Hz, 1H), 7.10 (s, 1H), 7.05-6.97 (m, 3H), 6.92-6.87 (m, 1H), 5.38-5.26 (m, 1H), 4.30-4.13 (m, 1H), 3.76 (d, J = 10.8 Hz, 2H), 3.50-3.49 (m, 1H), 3.19 (s, 1H), 3.17 (s, 3H), 2.93-2.76 (m, 4H), 2.62 (m, 3H), 2.40-2.34 (m, 3H), 2.29 (s, 2H), 2.19 (s, 3H), 2.06-1.87 (m, 6H), 1.83-1.66 (m, 6H), 1.61-1.47 (m, 2H), 1.11-0.92 (m, 3H), 0.46-0.44 (m, 2H), 0.22 (m, 2H) |
| I-37 | SQ | PW | 884.2 | 11.09 (s, 1H), 9.70 (s, 1H), 8.92 (s, 1H), 8.24 (s, 2H), 8.15 (d, J = 5.2 Hz, 1H), 7.30-7.06 (m, 3H), 7.03-7.00 (m, 1H), 6.99-6.94 (m, 2H), 6.91-6.87 (m, 1H), 5.36 (dd, J = 5.2, 12.4 Hz, 1H), 4.27-4.15 (m, 1H), 3.80 (d, J = 10.8 Hz, 1H), 3.57 (s, 3H), 3.50 (m, 1H), 3.18 (t, J = 6.0 Hz, 2H), 2.95-2.89 (m, 2H), 2.86-2.81 (m, 1H), 2.72-2.64 (m, 4H), 2.60-2.52 (m, 4H), 2.10-1.87 (m, 7H), 1.83-1.68 (m, 6H), 1.65-1.49 (m, 2H), 1.16-1.03 (m, 3H), 0.48-0.42 (m, 2H), 0.22 (q, J = 4.8 Hz, 2H) |
| I-38 | SR | PW | 884.6 | 11.11 (s, 1H), 9.73 (s, 1H), 8.92 (s, 1H), 8.19 (s, 1H), 8.14 (d, J = 5.2 Hz, 1H), 7.32-7.02 (m, 3H), 7.01 (dd, J = 1.2, 5.2 Hz, 1H), 6.96 (d, J = 4.8 Hz, 2H), 6.92-6.85 (m, 1H), 5.37 (dd, J = 5.2, 12.4 Hz, 1H), 4.25-4.19 (m, 1H), 3.83-3.82 (m, 1H), 3.57 (s, 3H), 3.53-3.45 (m, 2H), 3.17 (t, J = 6.0 Hz, 2H), 2.96-2.81 (m, 4H), 2.76-2.54 (m, 7H), 2.43-2.27 (m, 2H), 2.09-1.96 (m, 4H), 1.94-1.85 (m, 2H), 1.82-1.70 (m, 5H), 1.67-1.50 (m, 2H), 1.20-0.97 (m, 3H), 0.49-0.42 (m, 2H), 0.25-0.19 (m, 2H) |
| I-39 | SM | PW | 895.5 | 9.69 (s, 1H), 8.92 (s, 1H), 8.23 (s, 1H), 8.17 (s, 1H), 8.15 (d, J = 5.2 Hz, 1H), 7.54 (s, 1H), 7.51-7.43 (m, 3H), 7.32-7.05 (m, 3H), 7.04-6.99 (m, 1H), 5.71-5.60 (m, 1H), 4.74-4.62 (m, 1H), 4.24-4.14 (m, 1H), 3.94 (t, J = 8.8 Hz, 1H), 3.91-3.82 (m, 2H), 3.55 (s, 2H), 3.27-3.24 (m, 2H), 3.19-3.16 (m, 2H), 2.84 (d, J = 12.0 Hz, 2H), 2.71 (s, 1H), 2.66-2.58 (m, 6H), 2.30-2.14 (m, 2H), 2.10-1.97 (m, 4H), 1.92-1.88 (m, 1H), 1.79-1.67 (m, 2H), 1.63-1.44 (m, 2H), 1.17-1.00 (m, 3H), 0.48-0.41 (m, 2H), 0.25-0.20 (m, 2H) |
| I-40 | SO | PW | 895.4 | 10.98 (s, 1H), 9.69 (s, 1H), 8.92 (s, 1H), 8.23-8.17 (m, 2H), 8.15 (d, J = 5.2 Hz, 1H), 7.57-7.14 (m, 5H), 7.11-7.00 (m, 3H), 5.73-5.60 (m, 1H), 4.74-4.61 (m, 1H), 4.25-4.15 (m, 1H), 3.93 (t, J = 8.8 Hz, 1H), 3.90-3.80 (m, 2H), 3.56 (s, 2H), 3.43-3.38 (m, 2H), 3.24 (t, J = 8.0 Hz, 2H), 3.18 (t, J = 6.0 Hz, 2H), 2.86-2.82 (m, 1H), 2.76-2.71 (m, 2H), 2.56-2.54 (m, 2H), 2.25-2.18 (m, 1H), 2.10-1.81 (m, 7H), 1.80-1.68 (m, 2H), 1.67-1.44 (m, 2H), 1.17-0.99 (m, 3H), 0.49-0.42 (m, 2H), 0.27-0.18 (m, 2H) |
| I-41 | TC | TE | 902.5 | 9.39 (s, 1H), 8.77 (d, J = 8.4 Hz, 1H), 8.40-8.36 (m, 1H), 8.28-8.24 (m, 1H), 8.23-8.19 (m, 3H), 7.14-7.04 (m, 2H), 7.00 (d, J = 7.6 Hz, 1H), 6.93-6.86 (m, 2H), 5.38-5.29 (m, 1H), 4.24-4.12 (m, 2H), 3.75 (m, 4H), 3.63-3.61 (m, 4H), 3.32 (s, 3H), 2.94-2.88 (m, 2H), 2.84 (d, J = 6.4 Hz, 6H), 2.79 (d, J = 12.8 Hz, 2H), 2.71 (d, J = 4.4 Hz, 1H), 2.65-2.59 (m, 4H), 2.46- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 2.43 (m, 2H), 2.09-1.97 (m, 4H), 1.88 (m, 3.7 Hz, 2H), 1.83-1.65 (m, 4H), 1.62-1.48 (m, 2H), 1.16-1.01 (m, 2H) |
| I-42 | OD | TE | 859.5 | 11.79-10.37 (m, 1H), 9.40 (s, 1H), 8.77 (d, J = 8.0 Hz, 1H), 8.28 (d, J = 18.0 Hz, 2H), 7.25-6.95 (m, 3H), 6.92-6.82 (m, 2H), 5.33 (d, J = 5.2, 12.8 Hz, 1H), 4.26-4.13 (m, 1H), 3.75 (s, 5H), 3.40-3.34 (m, 5H), 3.32 (s, 3H), 2.91-2.75 (m, 7H), 2.72-2.57 (m, 6H), 2.11-1.95 (m, 3H), 1.90 (d, J = 12.0 Hz, 2H), 1.79-1.45 (m, 11H), 1.20-1.05 (m, 2H) |
| I-43 | TF | PW | 874.5 | 11.20 (s, 1H), 9.96 (s, 1H), 9.55-9.17 (m, 1H), 9.12 (s, 1H), 8.16 (s, 1H), 8.07 (d, J = 6.4 Hz, 1H), 7.65 (s, 1H), 7.35-6.94 (m, 5H), 5.38 (dd, J = 5.2, 12.8 Hz, 1H), 4.27-4.16 (m, 1H), 3.92-3.75 (m, 3H), 3.58 (s, 3H), 3.32-3.28 (m, 4H), 3.15-3.01 (m, 2H), 2.99-2.85 (m, 2H), 2.80 (s, 3H), 2.73-2.57 (m, 4H), 2.18-2.00 (m, 4H), 1.97-1.86 (m, 2H), 1.85-1.72 (m, 4H), 1.71-1.55 (m, 1H), 1.24-1.06 (m, 3H), 0.59-0.51 (m, 2H), 0.27-0.36 (m, 2H) |
| I-44[b] | PP | TG | 789.2 | 11.09 (s, 1H), 10.10 (s, 1H), 8.42-8.27 (m, 3H), 8.22-8.18 (m, 1H), 7.16 (t, J = 12.4 Hz 1H), 6.99-6.92 (m, 2H), 6.90-6.82 (m, 1H), 5.36 (dd, J = 5.2, 12.4 Hz, 1H), 4.25-4.18 (m, 1H), 3.57 (s, 3H), 3.47-3.36 (m, 4H), 3.01-2.92 (m, 2H), 2.92-2.83 (m, 1H), 2.75-2.57 (m, 2H), 2.39 (t, J = 7.2 Hz, 2H), 2.21-2.11 (m, 5H), 2.08-1.95 (m, 3H), 1.95-1.86 (m, 2H), 1.86-1.73 (m, 4H), 1.72-1.63 (m, 2H), 1.61-1.51 (m, 1H), 1.12-0.95 (m, 2H) |
| I-46 | TH | PW | 877.5 | 11.15 (s, 1H), 9.72 (s, 1H), 8.92 (s, 1H), 8.52 (dd, J = 1.6, 7.6 Hz, 1H), 8.40 (dd, J = 1.6, 4.8 Hz, 1H), 8.20-8.13 (m, 2H), 8.05 (s, 1H), 7.51 (s, 1H), 7.36 (d, J = 7.6 Hz, 1H), 7.31-6.97 (m, 5H), 6.02 (s, 1H), 4.23-4.17 (m, 1H), 3.43 (q, 7 = 6.8 Hz, 4H), 3.18 (t, 7 = 6.0 Hz, 2H), 3.09-2.95 (m, 2H), 2.84-2.65 (m, 4H), 2.60-2.53 (m, 3H), 2.46 (s, 3H), 2.14-2.00 (m, 3H), 1.98-1.85 (m, 4H), 1.84-1.62 (m, 5H), 1.21-0.98 (m, 3H), 0.51-0.39 (m, 2H), 0.31-0.16 (m, 2H) |
| I-47 | TL | PW | 893.5 | 11.14 (s, 1H), 9.72 (s, 1H), 8.92 (s, 1H), 8.52 (dd, J = 1.2, 7.6 Hz, 1H), 8.40 (dd, J = 1.2, 4.8 Hz, 1H), 8.20-8.12 (m, 2H), 8.06 (s, 1H), 7.51 (s, 1H), 7.37 (d, J = 8.0 Hz, 1H), 7.29-7.01 (m, 5H), 6.01 (s, 1H), 4.21-4.15 (m, 1H), 3.63-3.52 (m, 7H), 3.45 (t, 7 = 6.4 Hz, 2H), 3.18 (t, 7 = 6.0 Hz, 2H), 3.07-2.95 (m, 2H), 2.91 (t, J = 5.2 Hz, 2H), 2.80 (t, 7 = 7.2 Hz, 2H), 2.69-2.61 (m, 3H), 2.13-2.00 (m, 3H), 1.96-1.84 (m, 4H), 1.79-1.66 (m, 2H), 1.62-1.52 (m, 1H), 1.18-1.02 (m, 3H), 0.50-0.41 (m, 2H), 0.23-0.20 (m, 2H) |
| I-48 | TN | PW | 869.5 | 11.11 (s, 1H), 9.79 (s, 1H), 9.02 (s, 1H), 8.59 (d, J = 5.2 Hz, 1H), 8.30 (s, 1H), 8.18 (d, J = 1.6 Hz, 1H), 7.69 (dd, J = 1.6, 5.2 Hz, 1H), 7.32-7.01 (m, 1H), 6.97 (d, J = 4.9 Hz, 2H), 6.91-6.85 (m, 1H), 5.37 (dd, J = 5.2, 12.8 Hz, 1H), 4.27-4.14 (m, 1H), 3.87 (d, J = 6.8 Hz, 2H), 3.58 (s, 3H), 3.48-3.45 (m, 2H), 3.33-3.26 (m, 2H), 3.00-2.94 (m, 2H), 2.94-2.84 (m, 1H), 2.79-2.71 (m, 1H), 2.70-2.66 (m, 2H), 2.65-2.60 (m, 1H), 2.15-2.11 (m, 2H), 2.10-1.96 (m, 5H), 1.91-1.72 (m, 8H), 1.52 (s, 1H), 1.46 (br d, J = 9.8 Hz, 2H), 1.24-1.13 (m, 1H), 1.10-0.97 (m, 2H), 0.45-0.37 (m, 2H), 0.27-0.21 (m, 2H) |
| I-55 | PH | WL | 872.5 | 11.13 (s, 1H), 9.72 (s, 1H), 8.92 (s, 1H), 8.22-8.10 (m, 2H), 7.19-6.98 (m, 7H), 5.40-5.28 (m, 1H), 4.30-4.19 (m, 1H), 3.76 (d, J = 9.6 Hz, 2H), 3.54 (s, 3H), 3.35-3.30 (m, 4H), 3.19-3.16 (m, 2H), 3.09-0.03 (m, 2H), 2.93-2.86 (m, 1H), 2.82 (s, 2H), 2.72-2.63 (m, 5H), 2.62-2.56 (m, 1H), 2.05-1.95 (m, 3H), 1.89-1.74 (m, 4H), 1.61-1.44 (m, 2H), 1.13-0.99 (m, 1H), 0.49-0.42 (m, 2H), 0.26-0.18 (m, 2H) |
| I-56 | XK | PW | 898.5 | 11.04 (s, 1H), 9.68 (s, 1H), 8.91 (s, 1H), 8.19 (d, J = 10.2 Hz, 2H), 8.15 (d, J = 5.3 Hz, 1H), 7.37-6.98 (m, 4H), 6.92 (d, J = 8.6 Hz, 1H), 6.81 (d, J = 2.1 Hz, 1H), 6.65-6.60 (m, 1H), 5.33-5.20 (m, 1H), 4.23-4.16 (m, 1H), 3.57 (s, 3H), 3.50-3.46 (m, 2H), 3.29 (s, 5H), 3.18 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | (s, 2H), 2.94-2.82 (m, 1H), 2.73-2.56 (m, 4H), 2.21 (s, 3H), 2.20-2.18 (m, 1H), 2.08-1.87 (m, 5H), 1.76 (d, J = 12.3 Hz, 7H), 1.40-1.26 (m, 2H), 1.12-0.95 (m, 3H), 0.48-0.41 (m, 2H), 0.26-0.18 (m, 2H) |
| I-57$^c$ | SI | PW | 906.3 | 11.10 (s, 1H), 9.69 (s, 1H), 8.92 (s, 1H), 8.18 (s, 1H), 8.15-8.13 (m, 1H), 7.29-7.01 (m, 8H), 5.40-5.34 (m, 1H), 4.26-4.14 (m, 1H), 3.30 (s, 3H), 3.18 (t, J = 6.1 Hz, 2H), 2.93-2.83 (m, 3H), 2.64 (s, 1H), 2.56 (s, 4H), 2.12 (s, 3H), 2.11-1.87 (m, 12H), 1.78-1.65 (m, 4H), 1.18-0.91 (m, 6H), 0.48-0.42 (m, 2H), 0.24-0.19 (m, 2H) |
| I-58 | XM | PW | 898.6 | 11.08 (s, 1H), 9.69 (s, 1H), 8.91 (s, 1H), 8.16 (s, 1H), 8.14 (d, J = 5.2 Hz, 1H), 7.30-7.04 (m, 3H), 7.03-6.94 (m, 3H), 6.90-6.84 (m, 1H), 5.35 (dd, J = 5.2, 12.4 Hz, 1H), 4.24-4.14 (m, 1H), 3.56 (s, 3H), 3.52-3.50 (m, 4H), 3.17 (t, J = 6.0 Hz, 2H), 2.97-2.92 (m, 2H), 2.89-2.82 (m, 1H), 2.76-2.66 (m, 2H), 2.65-2.57 (m, 2H), 2.41-2.37 (m, 2H), 2.11 (d, J = 7.2 Hz, 2H), 2.06 (s, 6H), 2.03-1.95 (m, 2H), 1.93-1.66 (m, 7H), 1.57 (s, 1H), 1.09-0.96 (m, 3H), 0.48-0.41 (m, 2H), 0.24-0.18 (m, 2H) |
| I-59 | SL | PW | 1039.4 | 11.1 (s, 1H), 9.78 (s, 1H), 9.00 (s, 1H), 8.59 (d, J = 5.2 Hz, 1H), 8.29 (s, 1H), 8.20 ( d, J = 1.8 Hz, 2H), 7.72-7.64 (m, 1H), 7.30-6.93 (m, 4H), 5.39-5.31 (m, 1H), 4.21 (t, J = 11.8 Hz, 1H), 4.06 (d, J = 4.8 Hz, 2H), 3.86 (d, J = 6.8 Hz, 2H), 3.47 (s, 5H), 3.37 (s, 3H), 3.33 (s, 3H), 2.95-2.84 (m, 2H), 2.76-2.58 (m, 5H), 2.44 (d, J = 6.1 Hz, 3H), 2.33 (d, J = 1.7 Hz, 1H), 2.18-1.87 (m, 10H), 1.80-1.68 (m, 2H), 1.51 (s, 9H), 1.22-1.05 (m, 3H), 0.44-0.36 (m, 2H), 0.27-0.19 (m, 2H) |
| I-60$^c$ | RK | wo | 920.6 | 11.07 (s, 1H), 10.38 (s, 1H), 8.88 (s, 1H), 8.27 (s, 1H), 8.23 (d, J = 5.6 Hz, 1H), 8.16 (s, 1H), 7.65 (t, J = 6.4 Hz, 1H), 7.21 (s, 1H), 7.15 (d, J = 5.2 Hz, 1H), 7.04 (s, 1H), 7.02-6.95 (m, 1H), 6.90-6.83 (m, 1H), 5.88 (s, 1H), 5.35-5.30 (m, 1H), 4.30-4.15 (m, 2H), 4.03 (t, J = 12 Hz, 1H), 3.81-3.74 (m, 1H), 3.53 (s, 2H), 3.32 (s, 3H), 2.96-2.84 (m, 2H), 2.80 (d, J = 10.8 Hz, 1H), 2.66-2.57 (m, 6H), 2.45 (s, 3H), 2.33 (s, 1H), 2.05-1.95 (m, 4H), 1.91-1.82 (m, 2H), 1.80-1.59 (m, 6H), 1.50 (s, 6H), 1.13-0.98 (m, 2H) |
| I-61 | WQ | PW | 894.5 | 11.14 (s, 1H), 9.76 (s, 1H), 9.06 (s, 1H), 8.94 (s, 1H), 8.20 (s, 1H), 8.15 (d, J = 5.6 Hz, 1H), 7.30(s, 1H), 7.22-7.09 (m, 4H), 7.04 (d, J = 5.2 Hz, 1H), 5.44-5.35 (m, 1H), 4.30-4.18 (m, 1H), 4.04-3.88 (m, 2H), 3.75-3.67 (m, 1H), 3.65-3.59 (m, 2H), 3.35 (s, 3H), 3.23-3.15 (m, 2H), 2.95-2.77 (m, 6H), 2.77-2.69 (m, 1H), 2.67-2.63 (m, 1H), 2.63-2.55 (m, 1H), 2.53 (s, 3H), 2.45-2.40 (m, 1H), 2.24-2.13 (m, 1H), 2.12-1.97 (m, 4H), 1.96-1.58 (m, 4H), 1.28-1.13 (m, 2H), 1.12-1.00 (m, 1H), 0.51-0.42 (m, 2H), 0.26-0.19 (m, 2H) |
| I-62 | QI | PW | 857.6 | 11.08 (s, 1H), 9.71 (s, 1H), 8.92-8.89 (m, 1H), 8.17 (s, 1H), 8.14 (d, J = 5.2 Hz, 1H), 7.31-7.06 (m, 3H), 7.03-6.97 (m, 3H), 6.89-6.84 (m, 1H), 5.36-5.29 (m, 1H), 4.20-4.15 (m, 1H), 3.41-3.38 (m, 4H), 3.31 (s, 3H), 3.19-3.15 (m, 2H), 2.93-2.83 (m, 1H), 2.75-2.62 (m, 4H), 2.60-2.55 (m, 2H), 2.42-2.29 (m, 5H), 2.07-1.95 (m, 3H), 1.89 (d, J = 11.6 Hz, 2H), 1.85-1.75 (m, 3H), 1.76-1.67 (m, 3H), 1.63 (s, 1H), 1.23-1.00 (m, 3H), 0.47-0.42 (m, 2H), 0.24-0.19 (m, 2H) |
| I-63 | XO | PW | 885.5 | 11.08 (s, 1H), 9.68 (s, 1H), 8.92 (s, 1H), 8.20-8.13 (m, 2H), 7.30-7.11 (m, 1H), 7.10 (s, 1H), 7.04-7.00 (m, 1H), 6.96 (d, J = 5.2 Hz, 2H), 6.89-6.85 (m, 1H), 5.38-5.34 (m, 1H), 4.33-4.12 (m, 1H), 3.57 (s, 3H), 3.41 (s, 5H), 3.18 (t, J = 6.0 Hz, 2H), 3.00-2.94 (m, 2H), 2.90-2.83 (m, 2H), 2.71 (d, J = 4.4 Hz, 1H), 2.63 (d, J = 4.8 Hz, 1H), 2.61-2.57 (m, 1H), 2.55-2.54 (m, 1H), 2.41 (t, J = 6.8 Hz, 2H), 2.17 (d, J = 6.8 Hz, 2H), 2.05 ( d, J = 10.8 Hz, 2H), 1.98-1.89 (m, 2H), 1.87-1.80 (m, 2H), 1.78-1.69 (m, 2H), 1.59 (t, J = 6.4 Hz, 2H), 1.11-0.98 (m, 3H), 0.92 (d, J = 6.4 Hz, 6H), 0.50-0.42 (m, 2H), 0.23-0.22 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-64 | XQ | PW | 883.6 | 11.08 (s, 1H), 9.67 (s, 1H), 8.92 (s, 1H), 8.17 (s, 1H), 8.15 (d, J = 5.6 Hz, 1H), 7.28-7.00 (m, 4H), 6.96 (d, J = 4.8 Hz, 2H), 6.89-6.85 (m, 1H), 5.39-5.33 (m, 1H), 4.29-4.08 (m, 1H), 3.57 (s, 3H), 3.43-3.38 (m, 4H), 3.18 (t, J = 6.0 Hz, 2H), 2.99-2.94 (m, 2H), 2.93-2.82 (m, 1H), 2.76-2.69 (m, 1H), 2.65-2.62 (m, 1H), 2.59 (t, J = 6.8 Hz, 2H), 2.53-2.52 (m, 1H), 2.36 (d, J = 7.2 Hz, 2H), 2.08-2.01 (m, 2H), 2.00-1.94 (m, 1H), 1.90-1.80 (m, 4H), 1.74-1.68 (m, 4H), 1.64-1.54 (m, 1H), 1.10-1.03 (m, 1H), 1.02-0.92 (m, 2H), 0.48-0.42 (m, 4H), 0.31-0.26 (m, 2H), 0.24-0.20 (m, 2H) |
| I-65 | YB | PW | 855.6 | 11.10-11.05 (m, 1H), 9.69 (s, 1H), 8.92 (s, 1H), 8.18-8.18 (m, 1H), 8.18-8.12 (m, 1H), 7.29-7.06 (m, 3H), 7.02-6.95 (m, 3H), 6.90-6.84 (m, 1H), 5.41-5.32 (m, 1H), 4.22-4.14 (m, 1H), 3.56 (s, 3H), 3.49-3.51 (m, 4H), 3.19-3.16 (m, 4H), 2.98-2.96 (m, 2H), 2.92-2.88 (m, 4H), 2.85-.2.83 (m, 1H), 2.62-2.60 (m, 2H), 2.07-1.94 (m, 4H), 1.88-1.80 (m, 4H), 1.76-1.66 (m, 2H), 1.60-1.51 (m, 1H), 1.40-1.29 (m, 1H), 1.12-0.97 (m, 3H), 0.48-0.42 (m, 2H), 0.22-0.20 (m, 2H) |
| I-66 | YD | PW | 813.4 | 11.08 (s, 1H), 9.69 (s, 1H), 8.92 (s, 1H), 8.20-8.18 (s, 1H), 8.15 (d, J = 4.8 Hz, 1H), 7.29-6.96 (m, 5H), 6.90-6.83(m, 1H), 5.42-5.31 (m, 1H), 4.25-4.13 (m, 1H), 3.60-3.52 (m, 3H), 3.30-3.29 (m, 3H), 3.21-3.15 (m, 2H), 2.94-2.86 (m, 3H), 2.63-2.56 (m, 2H), 2.55-2.52 (m, 12H), 2.17-2.09 (m, 5H), 2.06-1.97 (m, 3H), 1.88 (d, J = 11.2 Hz, 2H), 1.83-1.68 (m, 2H), 1.64-1.51 (m, 4H), 1.15-0.94 (m, 3H), 0.48-0.42 (m, 2H), 0.25-0.20 (m, 2H) |
| I-67 | WR | PW | 885.5 | 11.09 (s, 1H), 9.72 (s, 1H), 8.92 (s, 1H), 8.14 (s, 1H), 7.16 (t, J = 54.4 Hz, 1H), 7.11-7.06 (m, 2H), 7.01 (dd, J = 1.2, 5.2 Hz, 1H), 6.98-6.93 (m, 2H), 6.88-6.83 (m, 1H), 5.36 (dd, J = 5.2, 12.4 Hz, 1H), 4.26-4.14 (m, 1H), 3.57-3.54 (s, 3H), 3.44-3.40 (m, 3H), 3.37 (s, 2H), 3.18 (t, J = 6.0 Hz, 3H), 2.94-2.83 (m, 3H), 2.76-2.65 (m, 2H), 2.65-2.58 (m, 2H), 2.52 (s, 1H), 2.41 (s, 3H), 2.08-1.95 (m, 3H), 1.88 (d, J = 11.2 Hz, 2H), 1.83-1.72 (m, 2H), 1.68-1.58 (m, 5H), 1.53 (s, 4H), 1.13-0.99 (m, 3H), 0.49-0.41 (m, 2H), 0.25-0.18 (m, 2H) |
| I-68 | PP | YF | 816.9 | 11.10 (s, 1H), 9.84 (s, 1H), 9.13-9.02 (m, 2H), 8.18-8.14 (m, 2H), 7.35-7.29 (m, 1H), 7.29-7.02 (m, 2H), 6.98-6.97 (m, 2H), 6.88-6.86 (m, 1H), 5.39-5.34 (m, 1H), 4.28-4.21 (m, 1H), 3.58 (s, 3H), 3.47 (d, J = 5.2 Hz, 4H), 3.22-3.17 (m, 2H), 3.10-3.06 (m, 2H), 3.02-2.98 (m, 2H), 2.94 (s, 3H), 2.89-2.84 (m, 1H), 2.81-2.80 (m, 3H), 2.72-2.64 (m, 2H), 2.07-1.81 (m, 13H), 1.23-1.16 (m, 2H) |
| I-69[b] | WR | XR | 788.5 | 11.07 (s, 1H), 9.79 (s, 1H), 9.00 (s, 1H), 8.86-8.79 (m, 2H), 8.16 (s, 1H), 7.98-7.94 (m, 2H), 7.15 (t, J = 54.4 Hz, 1H), 6.98-6.93 (m, 2H), 6.90-6.84 (m, 1H), 5.40-5.32 (m, 1H), 4.24-4.15 (m, 1H), 3.57 (s, 3H), 3.42 (t, J = 6.0 Hz, 4H), 3.01-2.93 (m, 2H), 2.92-2.83 (m, 1H), 2.75-2.57 (m, 2H), 2.37 (t, J = 7.0 Hz, 2H), 2.15 (s, 3H), 2.13 (s, 2H), 2.07-1.99 (m, 3H), 1.99-1.95 (m, 1H), 1.90 (d, J = 11.6 Hz, 2H), 1.86-1.79 (m, 2H), 1.78-1.72 (m, 2H), 1.69-1.62 (m, 2H), 1.58-1.49 (m, 1H), 1.09-0.97 (m, 2H) |
| I-70[b] | PP | WS | 802.5 | 11.09 (s, 1H), 9.81 (s, 1H), 8.99 (s, 1H), 8.68 (d, J = 5.2 Hz, 1H), 8.15 (s, 1H), 7.84 (s, 1H), 7.76 (d, J = 5.2 Hz, 1H), 7.15 (t, J = 54.4 Hz, 1H), 6.98-6.93 (m, 2H), 6.89-6.85 (m, 1H), 5.36 (dd, J = 5.6, 12.5 Hz, 1H), 4.26-4.14 (m, 1H), 3.57 (s, 3H), 3.42 (t, J = 6.0 Hz, 4H), 2.99-2.93 (m, 2H), 2.92-2.81 (m, 1H), 2.76-2.62 (m, 2H), 2.59 (s, 3H), 2.40-2.37 (m, 1H), 2.38 (t, J = 7.2 Hz, 2H), 2.19-2.12 (m, 5H), 2.05-1.95 (m, 3H), 1.94-1.86 (m, 2H), 1.86-1.79 (m, 2H), 1.76 (d, J = 12.0 Hz, 2H), 1.69-1.62 (m, 2H), 1.55-1.54 (m, 1H), 1.59-1.49 (m, 1H), 1.10-0.97 (m, 2H) |
| I-71[b] | PP | WT | 869.5 | 11.19-11.03 (m, 1H), 7.66-7.52 (m, 1H), 7.32 (d, J = 0.8 Hz, 1H), 7.16-7.13 (m, 1H), 5.39 (dd, J = 5.2, 12.8 Hz, 1H), 4.36 (s, 2H), 4.10 (d, J = 2.4 Hz, 1H), 3.41- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | ¹HNMR (400 MHz, DMSO-d$_6$) δ |
|---|---|---|---|---|
| | | | | 3.36 (m, 1H), 3.36 (s, 1H), 3.32-3.27 (m, 6H), 2.97-2.82 (m, 1H), 2.77-2.62 (m, 5H), 2.11-1.96 (m, 1H), 1.64 (s, 2H), 1.42-1.35 (m, 1H), 1.07-1.01 (m, 2H) |
| I-72 | YH | PW | 855.4 | 11.08 (s, 1H), 9.69 (s, 1H), 9.68 (s, 1H), 8.92 (s, 1H), 8.25-8.19 (m, 1H), 8.15 (d, J = 52 Hz, 1H), 7.31-7.05 (m, 3H), 7.02-7.00 (m, 1H), 6.98-6.93 (m, 2H), 6.90-6.85 (m, 1H), 5.39-5.32 (m, 1H), 4.25-4.15 (m, 1H), 4.02-3.93 (m, 1H), 3.57 (s, 3H), 3.21-3.14 (m, 2H), 2.98-2.86 (m, 3H), 2.66-2.57 (m, 2H), 2.44-2.39 (m, 2H), 2.37-2.29 (m, 2H), 2.24 (d, J = 7.2 Hz, 2H), 2.08-1.89 (m, 6H), 1.85-1.68 (m, 5H), 1.68-1.47 (m, 3H), 1.14-0.98 (m, 3H), 0.48-0.42 (m, 2H), 0.25-0.20 (m, 2H) |
| I-73 | WV | PW | 855.5 | 11.09 (s, 1H), 9.71 (s, 1H), 8.92 (s, 1H), 8.20-8.13 (m, 2H), 7.31-6.93 (m, 6H), 6.91-6.84 (m, 1H), 5.39-5.34 (m, 1H), 4.36-4.15 (m, 1H), 4.13-3.99 (m, 1H), 3.57 (s, 3H), 3.50-3.49 (m, 1H), 3.18 (t, J = 6.0 Hz, 3H), 3.00-2.93 (m, 3H), 2.92-2.83 (m, 2H), 2.77-2.70 (m, 2H), 2.69-2.58 (m, 2H), 2.53-2.52 (m, 1H), 2.11-1.89 (m, 6H), 1.88-1.71 (m, 5H), 1.70-1.54 (m, 2H), 1.17-0.97 (m, 3H), 0.48-0.41 (m, 2H), 0.24-0.19 (m, 2H) |
| I-74 | XT | PW | 922.6 | 11.09 (s, 1H), 9.68 (s, 1H), 8.91 (s, 1H), 8.22-8.11 (m, 3H), 7.15 (t, J = 54.8 Hz, 1H), 7.10 (s, 1H), 7.03-6.98 (m, 1H), 6.95 (t, J = 7.6 Hz, 1H), 6.86 (d, J = 7.6 Hz, 1H), 5.39-5.34 (m, 1H), 4.26-4.12 (m, 1H), 3.66 (s, 3H), 3.60 (s, 2H), 3.18 (t, J = 6.0 Hz, 3H), 2.95-2.84 (m, 2H), 2.80 (d, J = 9.2 Hz, 4H), 2.76-2.69 (m, 1H), 2.65-2.58 (m, 2H), 2.10 (d, J = 6.0 Hz, 2H), 2.07-1.71 (m, 12H), 1.58 (d, J = 11.2 Hz, 5H), 1.11-1.00 (m, 8H), 0.49-0.42 (m, 2H), 0.26-0.18 (m, 2H) |
| I-75 | WX | PW | 854.5 | 11.11 (s, 1H), 9.70 (s, 1H), 8.92 (s, 1H), 8.17 (s, 1H), 8.16-8.13 (m, 2H), 7.29-7.06 (m, 3H), 7.01 (dd, J = 1.2, 5.2 Hz, 1H), 6.96 (t, J = 7.6 Hz, 1H), 6.87 (d, J = 7.2 Hz, 1H), 5.40-5.36 (m, 1H), 4.24-4.12 (m, 1H), 3.67 (s, 3H), 3.62 (s, 2H), 3.21-3.15 (m, 3H), 2.94-2.83 (m, 3H), 2.75-2.60 (m, 2H), 2.53-2.51 (m, 1H), 2.30-2.25 (m, 2H), 2.22 (s, 3H), 2.08-1.93 (m, 5H), 1.92-1.83 (m, 2H), 1.81-1.70 (m, 2H), 1.69-1.61 (m, 2H), 1.57-1.33 (m, 3H), 1.13-0.93 (m, 3H), 0.48-0.42 (m, 2H), 0.25-0.19 (m, 2H) |
| I-76 | YI | PW | 868.2 | 11.11 (s, 1H), 9.70 (s, 1H), 8.92 (s, 1H), 8.18-8.13 (m, 4H), 7.31-6.83 (m, 7H), 5.43-5.30 (m, 1H), 4.25-4.13 (m, 1H), 3.67 (s, 3H), 3.64-3.57 (m, 2H), 3.17 (t, J = 6.2 Hz, 2H), 2.95-2.57 (m, 4H), 2.16 (s, 6H), 2.06-1.42 (m, 14H), 1.12-0.93 (m, 5H), 0.50-0.38 (m, 2H), 0.26-0.15 (m, 2H) |
| I-77 | YJ | PW | 870.5 | 11.09-11.08 (m, 1H), 9.72 (s, 1H), 8.93 (s, 1H), 8.19 (d, J = 5.2 Hz,, 1H), 8.15 (d, J = 5.2 Hz, 1H), 7.31-7.17 (m, 1H), 7.10-7.08 (m, 3H), 6.97 (t, J = 7.6 Hz, 1H), 6.89 (d, J = 7.6 Hz, 1H), 5.38 (dd, J = 5.2 Hz, J = 12.0 Hz, 1H), 4.19-4.15 (m, 1H), 3.80-3.74 (m, 2H), 3.69 (s, 3H), 3.62-3.57 (m, 1H), 3.54-3.47 (m, 2H), 3.18 (t, J = 6.0 Hz, 2H), 2.92-2.82 (m, 2H), 2.75-2.71 (m, 1H), 2.63 (s, 1H), 2.59-2.56 (m, 1H), 2.54-2.52 (m, 3H), 2.26-2.25 (m, 2H), 2.17-2.12 (m, 2H), 2.00-1.99 (m, 4H), 1.82-1.73 (m, 6H), 1.58-1.44 (m, 1H), 1.10-0.98 (m, 2H), 0.94-0.84 (m, 1H), 0.48-0.43 (m, 2H), 0.24-0.21 (m, 2H) |
| I-78 | YK | PW | 870.5 | 11.06 (s, 1H), 9.69 (s, 1H), 8.92 (s, 1H), 8.20-8.14 (m, 2H), 7.20-6.99 (m, 5H), 6.98-6.86 (m, 2H), 5.40-5.32 (m, 1H), 4.21-4.06 (m, 1H), 3.79-3.59 (m, 6H), 3.51-3.42 (m, 2H), 3.18 (t, J = 5.6 Hz, 2H), 2.93-2.82 (m, 2H), 2.75-2.59 (m, 3H), 2.34-2.25 (m, 2H), 2.19-1.94 (m, 9H), 1.86-1.65 (m, 5H), 1.55-1.36 (m, 1H), 1.13-1.03 (m, 1H), 0.99-0.75 (m, 2H), 0.49-0.41 (m, 2H), 0.25-0.19 (d, 2H) |
| I-79[b] | WY | WW | 882.4 | 11.14 (s, 1H), 9.77 (s, 1H), 9.26-9.01 (m, 1H), 8.97 (d, J = 4.4 Hz, 1H), 8.20 (s, 1H), 8.13 (d, J = 5.6 Hz, 1H), 7.35-7.21 (m, 2H), 7.21-6.96 (m, 4H), 5.47-5.43 (m, 1H), 4.73-4.54 (m, 2H), 4.31-4.19 (m, 1H), 3.61 (s, 3H), 3.21 (d, J = 6.0 Hz, 3H), 3.15-2.90 (m, 6H), 2.79 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | (d, J = 4.4 Hz, 2H), 2.76-2.69 (m, 1H), 2.62 (s, 1H), 2.52 (s, 3H), 2.10-1.96 (m, 3H), 1.94-1.74 (m, 7H), 1.59 (s, 3H), 1.46-1.30 (m, 2H), 1.26-1.14 (m, 2H), 1.13-1.04 (m, 1H), 0.49 (d, J = 7.6 Hz, 2H), 0.25 (d, J = 4.4 Hz, 2H) |
| I-80[b] | WZ | ZC | 906.3 | 11.10 (s, 1H), 9.68 (s, 1H), 8.92 (s, 1H), 8.19 (s, 1H), 8.16-8.13 (m, 1H), 7.30-7.09 (m, 3H), 7.08-7.05 (m, 1H), 7.05-6.96 (m, 3H), 5.42-5.34 (m, 1H), 4.25-4.15 (m, 1H), 3.68 (s, 3H), 3.20-3.17 (m, 2H), 2.96-2.87 (m, 3H), 2.77-2.70 (m, 1H), 2.67-2.64 (m, 2H), 2.63-2.57 (m, 3H), 2.17-2.15 (m, 1H), 2.14 (s, 3H), 2.12-2.10 (m, 2H), 2.06-1.96 (m, 5H), 1.95-1.88 (m, 2H), 1.82-1.69 (m, 4H), 1.63-1.35 (m, 3H), 1.15-0.97 (m, 5H), 0.49-0.42 (m, 2H), 0.25-0.20 (m, 2H) |
| I-81 | XV | PW | 893.6 | 9.72 (s, 1H), 8.93 (s, 1H), 8.48 (dd, J = 1.2, 7.6 Hz, 1H), 8.37 (d, J = 3.6 Hz, 1H), 8.31 (s, 1H), 8.15-8.09 (m, 2H), 7.47 (s, 1H), 7.33-6.98 (m, 6H), 6.01 (s, 1H), 4.23-4.11 (m, 1H), 3.54-3.52 (m, 9H), 3.44 (t, J = 6.4 Hz, 2H), 3.17 (t, J = 6.0 Hz, 2H), 3.12-2.95 (m, 2H), 2.83-2.66 (m, 5H), 2.15-1.81 (m, 7H), 1.78-1.63 (m, 2H), 1.55-1.45 (m, 1H), 1.13-0.99 (m, 3H), 0.50-0.41 (m, 2H), 0.23-0.20 (m, 2H) |
| I-82[b] | PP | XX | 865.5 | 11.07 (s, 1H), 10.37 (s, 1H), 8.85 (s, 1H), 8.23-8.11 (m, 2H), 7.15-7.04 (m, 2H), 7.01-6.92 (m, 3H), 6.91-6.83 (m, 1H), 6.01-5.64 (m, 1H), 5.36 (d, J = 5.6, 12.4 Hz, 1H), 4.10-3.95 (m, 1H), 3.59-3.55 (m, 3H), 3.42 (d, J = 6.0 Hz, 5H), 3.18 (d, J = 6.0 Hz, 2H), 3.01-2.91 (m, 2H), 2.90-2.83 (m, 1H), 2.76-2.56 (m, 2H), 2.34 (d, J = 6.8 Hz, 2H), 2.13 (s, 3H), 2.10 (d, J = 7.2 Hz, 2H), 2.06-1.96 (m, 3H), 1.93-1.79 (m, 4H), 1.75-1.59 (m, 4H), 1.49 (s, 6H), 1.12-0.94 (m, 3H), 0.49-0.41 (m, 2H), 0.28-0.18 (m, 2H) |
| I-83[b] | QI | XX | 865.6 | 11.15-10.99 (m, 1H), 10.36 (s, 1H), 8.85 (s, 1H), 8.17-8.12 (m, 2H), 7.12-7.05 (m, 2H), 7.04-6.97 (m, 3H), 6.87 (d, J = 7.2 Hz, 1H), 5.95-5.73 (m, 1H), 5.32 (dd, 7 = 5.2, 12.6 Hz, 1H), 4.10-3.97 (m, 1H), 3.50-3.44 (m, 4H), 3.31 (s, 3H), 3.19-3.16 (m, 2H), 2.92-2.84 (m, 1H), 2.70-2.63 (m, 4H), 2.34-2.31 (m, 2H), 2.13 (s, 3H), 2.10 (d, J = 7.2 Hz, 2H), 2.05-1.96 (m, 3H), 1.91-1.78 (m, 4H), 1.74-1.53 (m, 5H), 1.49 (s, 6H), 1.11-0.93 (m, 3H), 0.50-0.40 (m, 2H), 0.26-0.18 (m, 2H) |
| I-84 | PP | TE | 845.6 | 11.10 (s, 1H), 9.37 (s, 1H), 8.85 (d, J = 8.0 Hz, 1H), 8.39 (s, 1H), 8.30 (s, 1H), 7.29-6.83 (m, 5H), 5.37 (dd, J = 5.2, 12.4 Hz, 1H), 4.25-4.10 (m, 1H), 4.00-3.80 (m, 4H), 3.57 (s, 3H), 3.46-3.38 (m, 4H), 3.12-3.00 (m, 4H), 2.99-2.82 (m, 3H), 2.77-2.51 (m, 2H), 2.32-2.22 (m, 5H), 2.08-1.51 (m, 14H), 1.12-0.97 (m, 2H) |
| I-85 | XB | PW | 893.2 | 11.08 (s, 1H), 9.68 (s, 1H), 8.92 (s, 1H), 8.21-8.12 (m, 2H), 7.15 (t, J = 54.4 Hz, 1H), 7.10(s, 1H), 7.08 (t, J = 5.6 Hz, 1H), 7.02 (m, 1H), 6.98-6.96 (m, 2H), 6.91-6.87 (m, 1H), 5.42-5.30 (m, 1H), 4.25-4.14 (m, 1H), 3.79-3.68 (m, 2H), 3.63-3.58 (m, 2H), 3.57 (s, 3H), 3.21-3.15 (m, 2H), 3.02-2.95 (m, 2H), 2.94-2.73 (m, 3H), 2.73-2.58 (m, 2H), 2.35-2.29 (m, 2H), 2.29 (s, 3H), 2.11-1.82 (m, 7H), 1.82-1.69 (m, 2H), 1.62-1.45 (m, 1H), 1.11-0.94 (m, 3H), 0.49-0.42 (m, 2H), 0.26-0.19 (m, 2H) |
| I-86[b] | YL | PW | 835.5 | 11.10 (s, 1H), 9.68 (s, 1H), 8.92 (s, 1H), 8.39 (s, 1H), 8.18 (s, 1H), 8.15 (d, J = 5.2 Hz, 1H), 7.29-6.97 (m, 8H), 5.40-5.36 (m, 1H), 4.25-4.17 (m, 1H), 3.65 (s, 3H), 3.21-3.16 (m, 5H), 2.69-2.66 (m, 7H), 2.34-2.32 (m, 4H), 2.13-2.12 (m, 3H), 2.07 (s, 1H), 2.04-2.02 (m, 2H), 1.92-1.89 (m, 5H), 1.77-1.58 (m, 6H), 1.09-1.00 (m, 4H), 0.47-0.43 (m, 3H), 0.24-0.20 (m, 2H) |
| I-87 | XC | PW | 843.8 | 11.19 (s, 1H), 9.71 (s, 1H), 8.91 (s, 1H), 8.18 (s, 1H), 8.16-8.11 (m, 1H), 7.31-6.97 (m, 7H), 5.34 (d, J = 5.2, 12.8 Hz, 1H), 4.28-4.16 (m, 1H), 3.42 (d, J = 6.0 Hz, 2H), 3.39-3.34 (m, 3H), 3.17 (d, J = 6.0 Hz, 2H), 2.97-2.81 (m, 3H), 2.71-2.58 (m, 7H), 2.34-2.30 (m, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 1H), 2.19-2.01 (m, 3H), 1.98-1.70 (m, 9H), 1.21-1.00 (m, 3H), 0.53-0.37 (m, 2H), 0.28-0.14 (m, 2H) |
| I-88 | XD | PW | 853.5 | 11.09 (s, 1H), 9.67 (s, 1H), 8.92 (s, 1H), 8.33 (s, 1H), 8.14 (s, 1H), 7.29-7.04 (m, 5H), 7.01 (d, J = 7.2 Hz, 2H), 5.42-5.35 (m, 1H), 4.43 (s, 2H), 4.16-4.01 (m, 1H), 3.65 (s, 3H), 3.59 (t, J = 6.4 Hz, 2H), 3.20-3.16 (m, 2H), 2.92-2.81 (m, 1H), 2.64-2.57 (m, 2H), 2.38-2.34 (m, 2H), 2.12 (s, 3H), 2.10 (d, J = 6.8 Hz, 2H), 2.01-1.93 (m, 3H), 1.91-1.85 (m, 2H), 1.73-1.69 (m, 4H), 1.55-1.47 (m, 1H), 1.10-0.93 (m, 3H), 0.48-0.42 (m, 2H), 0.25-0.19 (m, 2H) |
| I-91 | XE | PW | 858.2 | 11.06 (s, 1H), 9.66 (s, 1H), 8.91 (s, 1H), 8.17-8.14 (m, 2H), 7.63 (m, 1H), 7.29-7.02 (m, 4H), 7.01 (d, J = 1.6, 5.2 Hz, 1H), 6.94 (d, J = 8.0 Hz, 1H), 5.38-5.27 (m, 1H), 4.24-4.12 (m, 3H), 4.04 (d, J = 6.0 Hz, 2H), 3.22-3.13 (m, 5H), 2.93-2.82 (m, 2H), 2.70 (d, J = 4.0 Hz, 1H), 2.62 (d, J = 4.8 Hz, 3H), 2.19 (s, 3H), 2.17 (d, J = 7.6 Hz, 2H), 2.06-1.94 (m, 3H), 1.92-1.82 (m, 2H), 1.80-1.67 (m, 2H), 1.58-1.42 (m, 1H), 1.12-0.93 (m, 3H), 0.50-0.40 (m, 2H), 0.27-0.17 (m, 2H) |
| I-92 | XZ | PW | 893.5 | 11.13 (s, 1H), 9.70 (s, 1H), 8.92 (s, 1H), 8.32 (d, J = 4.8 Hz, 1H), 8.23 (d, J = 7.6 Hz, 1H), 8.18-8.10 (m, 2H), 7.63 (s, 1H), 7.53-7.49 (m, 1H), 7.32 (t, J = 7.6 Hz, 1H), 7.29-6.98 (m, 5H), 6.05 (s, 1H), 4.14-4.08 (m, 1H), 3.66-3.54 (m, 11H), 3.24 (t, J = 8.0 Hz, 2H), 3.17 (t, J = 6.0 Hz, 2H), 3.04-3.00 (m, 2H), 2.77 (t, J = 5.2 Hz, 2H), 2.71 (s, 1H), 2.11-1.91 (m, 5H), 1.83 (d, J = 11.6 Hz, 2H), 1.72-1.58 (m, 2H), 1.50-1.46 (m, 1H), 1.13-0.92 (m, 3H), 0.50-0.41 (m, 2H), 0.27-0.18 (m, 2H) |
| I-93 | XG | PW | 893.5 | 11.15 (s, 1H), 9.71 (s, 1H), 8.96-8.88 (m, 1H), 8.61-8.51 (m, 1H), 8.46-8.39 (m, 1H), 8.28-8.19 (m, 1H), 8.19-8.11 (m, 2H), 7.57-7.38 (m, 2H), 7.34-7.06 (m, 5H), 7.03-7.00 (m, 1H), 6.34-5.84 (m, 1H), 4.17-4.05 (m, 1H), 3.66-3.54 (m, 9H), 3.25-3.21 (m, 2H), 3.18 (t, J = 6.0, 2H), 3.08-2.95 (m, 2H), 2.91-2.69 (m, 4H), 2.15-2.04 (m, 1H), 2.03-1.91 (m, 4H), 1.86-1.74(m, 2H), 1.69-1.44 (m, 3H), 1.15-0.92 (m, 3H), 0.49-0.42 (m, 2H), 0.26-0.18 (m, 2H) |
| I-95 | XI | PW | 882.6 | 11.08 (s, 1H), 9.68 (s, 1H), 8.92 (s, 1H), 8.18 (s, 1H), 8.15 (d, J = 5.2 Hz, 1H), 7.31-6.93 (m, 6H), 6.92-6.85 (m, 1H), 5.36 (dd, J = 5.2, 12.4 Hz, 1H), 4.25-4.16 (m, 1H), 3.57 (s, 3H), 3.18 (t, J = 6.0 Hz, 2H), 3.00-2.83 (m, 5H), 2.76-2.68 (m, 1H), 2.65-2.60 (m, 1H), 2.40 (t, J = 6.4 Hz, 2H), 2.32-2.27 (m, 1H), 2.23 (d, J = 6.8 Hz, 2H), 2.20 (s, 3H), 2.08-1.86 (m, 7H), 1.81-1.63 (m, 6H), 1.55-1.38 (m, 3H), 1.12-0.93 (m, 3H), 0.50-0.40 (m, 2H), 0.27-0.17 (m, 2H) |
| I-96 | TY | PW | 912.3 | 11.07 (s, 1H), 9.69 (s, 1H), 8.92 (s, 1H), 8.18 (s, 1H), 8.15 (d, J = 5.2 Hz, 1H), 7.38-6.97 (m, 6H), 6.87 (d, J = 8.0 Hz, 1H), 5.33 (dd, J = 5.2, 12.8 Hz, 1H), 4.24-4.14 (m, 1H), 3.76 (d, J = 11.2 Hz, 1H), 3.52-3.42 (m, 2H), 3.31 (s, 3H), 3.18 (t, J = 6.0 Hz, 2H), 2.95-2.83 (m, 1H), 2.80-2.72 (m, 1H), 2.72-2.57 (m, 5H), 2.47-2.41 (m, 2H), 2.29 (t, J = 7.2 Hz, 2H), 2.25-2.17 (m, 5H), 2.06-1.94 (m, 4H), 1.93-1.84 (m, 2H), 1.81-1.66 (m, 5H), 1.61-1.50 (m, 3H), 1.10-0.95 (m, 3H), 0.49-0.40 (m, 2H), 0.26-0.18 (m, 2H) |
| I-97 | TW | PW | 912.2 | 11.08 (s, 1H), 9.70 (s, 1H), 8.92 (s, 1H), 8.17 (s, 1H), 8.14 (d, J = 5.2 Hz, 1H), 7.31-6.95 (m, 6H), 6.87 (d, J = 8.4 Hz, 1H), 5.35-5.30 (m, 1H), 4.24-4.14 (m, 1H), 3.77-3.74 (m, 1H), 3.45-3.43(m, 2H), 3.31 (s, 3H), 3.17 (t, J = 6.0 Hz, 3H), 2.94-2.83 (m, 1H), 2.79-2.72 (m, 1H), 2.68-2.66 (m, 1H), 2.65-2.58 (m, 3H), 2.52-2.51 (m, 1H), 2.41-2.34 (m, 2H), 2.30-2.23 (m, 2H), 2.14 (s, 3H), 2.12-2.10 (m, 1H), 2.06-1.94 (m, 4H), 1.93-1.83 (m, 2H), 1.81-1.65 (m, 5H), 1.57-1.45 (m, 3H), 1.13-0.93 (m, 3H), 0.50-0.39 (m, 2H), 0.26-0.17 (m, 2H) |
| I-107 | AAB | PW | 858.6 | 11.1 (s, 1H), 9.71 (s, 1H), 8.91 (s, 1H), 8.24 (s, 2H), 8.16-8.14 (m, 1H), 7.31-7.13 (m, 2H), 7.11-7.04 (m, 4H), 7.03-7.00 (m, 1H), 5.40-5.30 (m, 1H), 4.22- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | 4.09 (m, 1H), 3.95-3.85 (m, 2H), 3.46-3.44 (m, 6H), 3.33 (s, 3H), 3.20-3.14 (m, 2H), 2.94-2.85 (m, 1H), 2.83-2.77 (m, 2H), 2.71-2.65 (m, 1H), 2.65-2.59 (m, 1H), 2.21-2.14 (m, 5H), 2.04-1.96 (m, 3H), 1.91-1.81 (m, 2H), 1.79-1.65 (m, 2H), 1.55-1.43 (m, 1H), 1.11-0.94 (m, 3H), 0.49-0.41 (m, 2H), 0.25-0.18 (m, 2H) |
| I-108 | YN | WL | 872.5 | 11.06 (s, 1H), 9.69 (s, 1H), 8.92 (s, 1H), 8.18 (d, J = 3.2 Hz, 1H), 8.15 (d, J = 5.4 Hz, 1H), 7.31-6.99 (m, 6H), 6.98-6.91 (m, 2H), 5.38-5.32 (m, 1H), 4.30-4.19 (m, 1H), 3.93 (d, J = 4.0 Hz, 2H), 3.66 (d, J = 6.0 Hz, 2H), 3.54 (s, 2H), 3.49-3.41 (m, 3H), 3.34-3.33 (m, 3H), 3.18 (t, J = 6.0 Hz, 2H), 3.05 (s, 2H), 2.81 (s, 1H), 2.77-2.72 (m, 2H), 2.65-2.58 (m, 1H), 2.52 (s, 3H), 1.97 (m, 1H), 1.84-1.74 (m, 4H), 1.62-1.45 (m, 4H), 1.08-1.04 (m, 1H), 0.49-0.41 (m, 2H), 0.25-0.19 (m, 2H) |
| I-109$^d$ | ZB | PW | 913.6 | 11.09 (s, 1H), 9.70 (s, 1H), 8.92 (s, 1H), 8.26 (s, 1H), 8.18 (s, 1H), 8.15 (d, J = 5.2 Hz, 1H), 7.32-7.04 (m, 6H), 7.03-7.01 (m, 1H), 5.40-5.33 (m, 1H), 4.20-4.15 (m, 1H), 3.88 (s, 2H), 3.80-3.67 (m, 2H), 3.68-3.51 (m, 1H), 3.51-3.45 (m, 1H), 3.34 (s, 3H), 3.21-3.14 (m, 2H), 2.96-2.84 (m, 1H), 2.83-2.76 (m, 1H), 2.76-2.71 (m, 2H), 2.71-2.65 (m, 1H), 2.64-2.53 (m, 1H), 2.47-2.44 (m, 2H), 2.33-2.28 (m, 2H), 2.17 (s, 3H), 2.16-2.08 (m, 2H), 2.06-1.96 (m, 4H), 1.93-1.83 (m, 2H), 1.79-1.68 (m, 3H), 1.58-1.47 (m, 1H), 1.12-0.94 (m, 3H), 0.50-0.40 (m, 2H), 0.26-0.19 (m, 2H) |
| I-110 | ZF | PW | 895.2 | 11.08 (s, 1H), 9.68 (s, 1H), 8.91 (s, 1H), 8.15 (d, J = 5.2 Hz, 1H), 7.36-6.82 (m, 7H), 5.35 (dd, J = 5.4, 12.8 Hz, 1H), 4.20 (t, J = 11.6 Hz, 1H), 3.48 (s, 2H), 3.33 (s, 3H), 3.18 (t, J = 6.0 Hz, 2H), 2.96-2.59 (m, 4H), 2.46-2.21 (m, 13H), 2.06-1.97 (m, 3H), 1.95-1.69 (m, 6H), 1.67-1.48 (m, 3H), 1.12-0.90 (m, 3H), 0.51-0.38 (m, 2H), 0.28-0.14 (m, 2H) |
| I-111$^b$ | ZD | ZC | 835.6 | 11.11 (s, 1H), 10.14-9.80 (m, 2H), 9.08 (s, 1H), 8.26-8.15 (m, 1H), 8.08 (dd, J = 6.4 Hz, 1H), 7.58 (s, 1H), 7.33-7.01 (m, 4H), 5.45-5.32 (m, 1H), 4.30-4.20 (m, 1H), 3.31 (d, J = 7.6 Hz, 5H), 3.20-3.11 (m, 2H), 3.10-3.07 (m, 1H), 3.01-2.80 (m, 4H), 2.77-2.63 (m, 3H), 2.29-2.15 (m, 1H), 2.14-1.70 (m, 11H), 1.30-1.08 (m, 3H), 0.55 (d, J = 7.6 Hz, 2H), 0.32 (d, J = 4.4 Hz, 2H) |
| I-112 | YP | PW | 869.5 | 11.08 (s, 1H), 9.69 (s, 1H), 8.92 (s, 1H), 8.18 (s, 1H), 8.15 (d, J = 5.6 Hz, 1H), 7.15 (t, J = 54.4 Hz, 1H), 7.10 (s, 1H), 7.03-6.99 (m, 1H), 6.96 (d, J = 4.4 Hz, 2H), 6.90-6.84 (m, 1H), 5.36 (dd, J = 4.8, 11.6 Hz, 1H), 4.28-4.12 (m, 1H), 4.00-3.90 (m, 1H), 3.57 (s, 3H), 3.18 (t, J = 6.0 Hz, 3H), 2.96 (t, J = 8.0 Hz, 2H), 2.91-2.80 (m, 2H), 2.76-2.68 (m, 1H), 2.65-2.58 (m, 1H), 2.06 (s, 1H), 2.03 (s, 3H), 2.03-1.65 (m, 16H), 1.57-1.44 (m, 1H), 1.13-0.94 (m, 3H), 0.50-0.39 (m, 2H), 0.25-0.16 (m, 2H) |
| I-113 | YQ | PW | 898.3 | 11.06 (s, 1H), 9.68 (s, 1H), 8.91 (s, 1H), 8.20-8.12 (m, 3H), 7.15 (t, J = 54.4 Hz, 1H), 7.10 (s, 1H), 7.03-7.00 (m, 1H), 6.97-6.93 (m, 2H), 6.89-6.85 (m, 1H), 5.35 (dd, J = 5.2, 12.4 Hz, 1H), 4.23-4.14 (m, 1H), 3.75 (d, J = 10.8 Hz, 2H), 3.70-3.66 (m, 1H), 3.57 (s, 3H), 3.20-3.15 (m, 4H), 2.98-2.90 (m, 3H), 2.89-2.83 (m, 2H), 2.72-2.70 (m, 1H), 2.63-2.61 (m, 3H), 2.33 (d, J = 5.2 Hz, 2H), 2.18 (s, 3H), 2.05-1.95 (m, 4H), 1.93-1.83 (m, 2H), 1.81-1.67 (m, 5H), 1.57-1.45 (m, 1H), 1.11-0.93 (m, 3H), 0.49-0.41 (m, 2H), 0.27-0.18 (m, 2H) |
| I-114 | ZI | PW | 882.3 | 11.09 (s, 1H), 9.69 (s, 1H), 8.92 (s, 1H), 8.25-8.12 (m, 2H), 7.30-7.05 (m, 3H), 7.04-6.93 (m, 4H), 5.37 (dd, J = 12.8 Hz, J = 5.2 Hz, 1H), 4.27-4.15 (m, 1H), 3.58 (s, 3H), 3.18 (m, 3H), 3.06 (m, 3H), 2.95-2.80 (m, 2H), 2.75-2.57 (m, 1H), 2.43-2.30 (m, 3H), 2.23-2.13 (m, 7H), 2.06 (d, J = 10.4 Hz, 2H), 2.12-1.96 (m, 1H), 1.92 (d, J = 11.4 Hz, 2H), 1.86-1.70 (m, 6H), 1.69-1.50 (m, 3H), 1.15-0.97 (m, 3H), 0.49-0.40 (m, 2H), 0.25-0.18 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-115[b] | PP | ZK | 884.7 | 11.08 (s, 1H), 9.72-9.65 (m, 1H), 8.95-8.92 (m, 1H), 8.25-8.16 (m, 3H), 7.61 (d, J = 6.4 Hz, 1H), 7.30-7.00 (m, 3H), 6.96 (d, J = 4.8 Hz, 2H), 6.90-6.82 (m, 1H), 5.36 (d, J = 4.8, 12.8 Hz, 1H), 4.32-4.15 (m, 3H), 3.57 (s, 3H), 3.55 (s, 1H), 3.44-3.41 (m, 3H), 2.99-2.93 (m, 2H), 2.90-2.83 (m, 1H), 2.75-2.56 (m, 4H), 2.27 (d, J = 7.6 Hz, 1H), 2.18-2.14 (m, 3H), 2.13 (s, 1H), 2.07-1.95 (m, 3H), 1.86-1.74 (m, 4H), 1.69-1.62 (m, 2H), 1.59-1.46 (m, 2H), 1.11-0.95 (m, 2H) |
| I-116 | ZM | PW | 912.3 | 11.08 (s, 1 H), 9.68 (s, 1H), 8.91 (s, 1H), 8.30-8.10 (m, 2H), 7.30-6.80 (m, 7H), 5.50-5.30 (m, 1H), 4.30-4.10 (m, 1H), 3.75 (d, J = 11.0 Hz, 1H), 3.56 (s, 3H), 3.45 (s, 1H), 3.18 (t, J = 6.1 Hz, 2H), 2.97-2.84 (m, 3H), 2.79 (d, J = 10.8 Hz, 1H), 2.73-2.63 (m, 3H), 2.59 (m, 1H), 2.45-2.29 (m, 5H), 2.17 (m, 5H), 2.06-1.94 (m, 4H), 1.94-1.83 (m, 2H), 1.81-1.68 (m, 5H), 1.57-1.45 (m, 3H), 1.11-0.95 (m, 3H), 0.45 (d, J = 7.1 Hz, 2H), 0.22 (d, J = 4.4 Hz, 2H) |
| I-117 | YR | PW | 912.3 | 11.08 (s, 1H), 9.69 (s, 1H), 8.91 (s, 1H), 8.19-8.12 (m, 3H), 7.15 (t, J = 54.8 Hz, 1H), 7.10-7.07 (m, 1H), 7.10-7.06 (m, 1H), 6.97-6.93 (m, 1H), 6.90-6.85 (m, 1H), 5.41-5.30 (m, 1H), 4.26-4.14 (m, 1H), 3.75 (d, J = 10.4 Hz, 2H), 3.56(s, 3H), 3.47 (s, 1H), 3.20-3.15 (m, 4H), 2.95-2.87 (m, 3H), 2.79 (d, J = 11.2 Hz, 1H), 2.74-2.68 (m, 1H), 2.65-2.57 (m, 1H), 2.52 (s, 3H), 2.46-2.38 (m, 3H), 2.36-2.34 (m, 1H), 2.19 (s, 3H), 2.06-1.95 (m, 4H), 1.93-1.83 (m, 2H), 1.80-1.69 (m, 4H), 1.59-1.47 (m, 3H), 1.12-0.93 (m, 3H), 0.50-0.40 (m, 2H), 0.26-0.17 (m, 2H) |
| I-118 | ZM | PW | 869.2 | 11.09 (s, 1H), 9.71 (s, 1H), 8.92 (s, 1H), 8.25-8.19 (m, 1H), 8.17 (s, 1H), 8.16-8.13 (m, 1H), 7.32-6.97 (m, 6H), 6.89-6.83 (m, 1H), 5.37-5.29 (m, 1H), 4.23-4.14 (m, 1H), 3.42-3.36 (m, 4H), 3.32 (s, 3H), 3.17 (s, 2H), 2.96-2.83 (m, 1H), 2.67 (s, 6H), 2.17-1.95 (m, 7H), 1.93-1.67 (m, 8H), 1.44 (d, J = 9.2 Hz, 3H), 1.12-0.96 (m, 3H), 0.48-0.42 (m, 2H), 0.24-0.19 (m, 2H) |
| I-119 | YT | PW | 883.7 | 11.08 (s, 1H), 9.69 (s, 1H), 8.92 (s, 1H), 8.17 (s, 1H), 8.15 (d, J = 5.4 Hz, 1H), 7.31-7.02 (m, 4H), 7.02-6.98 (m, 2H), 6.86 (d, J = 8.2 Hz, 1H), 5.33 (dd, J = 12.8 Hz, 1H), 4.24-4.14 (m, 1H), 3.35 (br s, 2H), 3.32 (s, 3H), 3.22-3.19 (m, 3H), 3.18-3.15 (m, 2H), 2.94-2.84 (m, 3H), 2.67-2.63 (m, 2H), 2.14 (d, J = 6.4 Hz, 2H), 2.04 (d, J = 12.4 Hz, 2H), 1.99 (d, J = 5.2 Hz, 1H), 1.93-1.85 (m, 4H), 1.84-1.78 (m, 2H), 1.78-1.71 (m, 2H), 1.69-1.54 (m, 4H), 1.54-1.48 (m, 1H), 1.26-1.14 (m, 2H), 1.11-0.97 (m, 3H), 0.48-0.42 (m, 2H), 0.22 (q, J = 4.8 Hz, 2H) |
| I-120 | YU | PW | 883.7 | 11.10 (s, 1H), 9.71 (s, 1H), 8.93 (s, 1H), 8.16-8.12 (m, 2H), 7.30-7.01 (m, 4H), 6.96 (d, J = 4.4 Hz, 2H), 6.88-6.84 (m, 1H), 5.40-5.33 (m, 1H), 4.26-4.15 (m, 1H), 3.56 (s, 3H), 3.42 (t, J = 6.0 Hz, 2H), 3.25 (d, J = 6.0 Hz, 2H), 3.17 (t, J = 6.0 Hz, 2H), 2.99-2.93 (m, 4H), 2.91-2.82 (m, 1H), 2.74-2.67 (m, 1H), 2.59 (s, 1H), 2.30-2.24 (m, 2H), 2.08-2.00 (m, 4H), 2.00-1.95 (m, 1H), 1.92-1.86 (m, 2H), 1.85-1.80 (m, 2H), 1.78-1.64 (m, 5H), 1.60-1.53 (m, 1H), 1.33-1.20 (m, 2H), 1.13-1.01 (m, 3H), 0.48-0.40 (m, 2H), 0.25-0.16 (m, 2H) |
| I-121 | YW | PW | 841.5 | 11.07 (s, 1H), 9.69 (s, 1H), 8.91 (s, 1H), 8.18 (s, 1H), 8.16-8.12 (m, 1H), 7.30-7.03 (m, 4H), 7.03-6.99 (m, 2H), 6.87 (d, J = 7.6 Hz, 1H), 5.34 (dd, J = 12.8 Hz, 1H), 4.20-4.14 (m, 1H), 3.94-3.83 (m, 1H), 3.37-3.33 (m, 7H), 3.18 (t, J = 6.0 Hz, 2H), 2.94-2.85 (m, 1H), 2.75-2.54 (m, 8H), 2.09-2.01 (m, 2H), 2.01-1.95 (m, 1H), 1.88-1.81 (m, 3H), 1.80-1.68 (m, 2H), 1.63-1.54 (m, 1H), 1.53-1.42 (m, 1H), 1.17-1.00 (m, 3H), 0.51-0.40 (m, 2H), 0.26-0.17 (m, 2H) |
| I-122 | ZN | PW | 841.5 | 11.08 (s, 1H), 9.67 (s, 1H), 8.91 (s, 1H), 8.18 (d, J = 5.6 Hz, 1H), 8.15 (d, J = 5.2 Hz, 1H), 7.29-7.00 (m, 4H), 6.97 (d, J = 4.4 Hz, 2H), 6.90-6.85 (m, 1H), 5.40-5.31 (m, 1H), 4.23-4.12 (m, 1H), 4.10-3.99 (m, 1H), 3.57 (s, 3H), 3.56-3.53 (m, 2H), 3.36 (t, J = 6.0 Hz, 2H), |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 3.18 (t, J = 6.0 Hz, 2H), 2.97-2.92 (m, 2H), 2.91-2.84 (m, 1H), 2.84-2.78 (m, 2H), 2.74-2.59 (m, 2H), 2.31 (d, J = 6.8 Hz, 2H), 2.06-2.00 (m, 2H), 1.99-1.90 (m, 1H), 1.87-1.80 (m, 3H), 1.78-1.65 (m, 2H), 1.59-1.51 (m, 1H), 1.42-1.30 (m, 1H), 1.14-0.99 (m, 3H), 0.48-0.42 (m, 2H), 0.25-0.19 (m, 2H) |
| I-123 | ZO | PW | 889.6 | 11.14 (s, 1H), 9.69 (s, 1H), 8.92 (s, 1H), 8.35-8.23 (m, 2H), 8.18 (s, 2H), 8.15 (d, J = 5.2 Hz, 1H), 7.68-7.60 (m, 1H), 7.56-7.49 (m, 1H), 7.33-7.27 (m, 1H), 7.18-6.99 (m, 5H), 6.06 (s, 1H), 4.25-4.14 (m, 1H), 3.56 (t, J = 5.6 Hz, 2H), 3.24-3.22(m, 2H), 3.18 (t, J = 6.0 Hz, 3H), 3.11-2.96 (m, 2H), 2.15-1.96 (m, 10H), 1.94-1.82 (m, 5H), 1.82-1.82 (m, 1H), 1.80-1.70 (m, 2H), 1.61-1.48 (m, 3H), 1.11-0.96 (m, 3H), 0.48-0.42 (m, 2H), 0.25-0.20 (m, 2H) |
| I-124 | ZP | PW | 843.5 | 11.08 (s, 1H), 9.69 (s, 1H), 8.92 (s, 1H), 8.20-8.10 (m, 2H), 7.29-6.95 (m, 6H), 6.90-6.85 (m, 1H), 5.36 (dd, J = 5.2, 12.4 Hz, 1H), 4.24-4.14 (m, 1H), 3.56 (s, 3H), 3.48-3.44 (m, 4H), 3.18 (t, J = 6.0 Hz, 2H), 3.00-2.93 (m, 2H), 2.92-2.82 (m, 1H), 2.77-2.59 (m, 3H), 2.25-2.15 (m, 5H), 2.09-1.67 (m, 10H), 1.60-1.44 (m, 1H), 1.13-0.95 (m, 3H), 0.51-0.38 (m, 2H), 0.27-0.17 (m, 2H) |
| I-125 | TN | TE | 857.6 | 11.01 (s, 1H), 9.38 (s, 1H), 8.80 (d, J = 8.0 Hz, 1H), 8.38 (s, 1H), 8.28 (s, 1H), 8.23 (d, J = 1.2 Hz, 2H), 7.25-6.94 (m, 3H), 6.92-6.85 (m, 2H), 5.36 (d, J = 5.2, 12.6 Hz, 1H), 4.21-4.12 (m, 3H), 3.57 (s, 3H), 3.45 (d, J = 6.0 Hz, 2H), 3.28 (d, J = 3.6 Hz, 1H), 3.01-2.82 (m, 7H), 2.77-2.57 (m, 4H), 2.18-2.07 (m, 4H), 2.06-1.96 (m, 3H), 1.93-1.77 (m, 7H), 1.76-1.67 (m, 2H), 1.57 (s, 1H), 1.52-1.40 (m, 2H), 1.11-0.96 (m, 2H) |
| I-126 | ZQ | ZC | 853.4 | 11.10 (s, 1H), 9.67 (s, 1H), 8.90 (s, 1H), 8.15-8.14 (m, 2H), 7.31 (s, 1H), 7.17-7.01 (m, 6H), 5.39-5.34 (m, 1H), 4.35 (s, 2H), 4.17-4.11 (m, 1H), 3.57 (t, J = 6.0 Hz, 2H), 3.33 (s, 1H), 3.17 (t, J = 6.0 Hz, 2H), 2.90-2.83 (m, 1H), 2.63-2.59 (m, 2H), 2.37-2.35 (m, 2H), 2.15-2.10 (m, 5H), 2.02-1.99 (m, 3H), 1.90-1.87 (m, 2H), 1.78-1.65 (m, 4H), 1.53-1.50 (m, 1H), 1.09-0.96 (m, 3H), 0.47-0.43 (m, 2H), 0.24-0.20 (m, 2H) |
| I-127 | ZR | PW | 868.3 | 11.08 (s, 1H), 9.68 (s, 1H), 8.91 (s, 1H), 8.17 (s, 1H), 8.15 (d, J = 5.2 Hz, 1H), 7.31-7.08 (m, 3H), 7.08-6.95 (m, 4H), 5.35 (dd, J = 5.2, 12.8 Hz, 1H), 4.24-4.13 (m, 1H), 3.55 (s, 2H), 3.33 (s, 3H), 3.18 (t, J = 6.0 Hz, 2H), 2.95-2.84 (m, 2H), 2.59-2.76 (m, 1H), 2.47-2.38 (m, 2H), 2.17-2.11 (m, 4H), 2.11-2.08 (m, 2H), 2.06-1.97 (m, 5H), 1.94-1.86 (m, 2H), 1.81-1.66 (m, 4H), 1.62-1.40 (m, 3H), 1.19-0.89 (m, 5H), 0.48-0.39 (m, 2H), 0.25-0.16 (m, 2H) |
| I-128 | ZS | PW | 843.6 | 11.07 (s, 1H), 9.69 (s, 1H), 8.92 (s, 1H), 8.17 (s, 1H), 8.14 (d, J = 5.6 Hz, 1H), 7.29-7.05 (m, 3H), 7.03-6.99 (m, 3H), 6.87 (d, J = 8.4 Hz, 1H), 5.33 (dd, J = 5.2, 12.8 Hz, 1H), 4.25-4.13 (m, 1H), 3.48-3.45 (m, 4H), 3.31 (s, 3H), 3.17 (t, J = 6.4 Hz, 2H), 2.94-2.83 (m, 1H), 2.75-2.61 (m, 4H), 2.53-2.51 (m, 2H), 2.22-2.16 (m, 5H), 2.07-1.96 (m, 3H), 1.91 (d, J = 11.6 Hz, 2H), 1.86-1.70 (m, 4H), 1.60-1.47 (m, 1H), 1.11-0.95 (m, 3H), 0.48-0.42 (m, 2H), 0.24-0.19 (m, 2H) |
| I-129 | ZU | PW | 843.5 | 11.06 (s, 1H), 9.69-9.65 (m, 1H), 8.91 (s, 1H), 8.18-8.12 (m, 2H), 7.30-6.99 (m, 5H), 6.91 (d, J = 8.0 Hz, 1H), 5.35-5.31 (m, 1H), 4.21-4.15 (m, 1H), 3.57 (t, J = 7.2 Hz, 2H), 3.43 (t, J = 7.2 Hz, 2H), 3.31 (s, 3H), 3.18 (t, J = 7.0 Hz, 2H), 2.93-2.80 (m, 3H), 2.76-2.68 (m, 2H), 2.63-2.58 (m, 2H), 2.16-2.08 (m, 5H), 2.05-1.96 (m, 3H), 1.92-1.81 (m, 2H), 1.80-1.70 (m, 2H), 1.67-1.60 (m, 2H), 1.55-1.48 (m, 1H), 1.08-0.97 (m, 3H), 0.48-0.42 (m, 2H), 0.25-0.20 (m, 2H) |
| I-130 | VD | PW | 799.5 | 11.07 (s, 1H), 9.68 (s, 1H), 8.91 (s, 1H), 8.18 (s, 1H), 8.16-8.14 (m, 1H), 7.29-7.00 (m, 4H), 6.97 (d, J = 4.4 Hz, 2H), 6.92-6.87 (m, 1H), 5.40-5.33 (m, 1H), 4.26-4.14 (m, 1H), 3.57 (s, 3H), 3.18 (t, J = 6.0 Hz, 2H), 2.93 (t, J = 7.6 Hz, 2H), 2.90-2.83 (m, 1H), 2.76-2.68 (m, 1H), 2.64-2.59 (m, 1H), 2.45 (t, J = 6.4 Hz, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 2H), 2.22 (s, 3H), 2.22-2.18 (m, 2H), 2.08-2.02 (m, 2H), 2.01-1.95 (m, 1H), 1.94-1.87 (m, 2H), 1.82-1.68 (m, 4H), 1.61-1.51 (m, 1H), 1.11-0.98 (m, 3H), 0.48-0.42 (m, 2H), 0.25-0.19 (m, 2H) |
| I-161 | ACL | PW | 1120.8 | 9.68 (s, 1H), 8.91 (s, 1H), 8.19 (s, 1H), 8.17 (s, 1H), 8.14 (d, J = 5.2 Hz, 1H), 8.02-7.88 (m, 1H), 7.31-6.75 (m, 11H), 4.99-4.80 (m, 2H), 4.79-4.61 (m, 2H), 4.23-4.13 (m, 1H), 4.11-4.03 (m, 2H), 3.79-3.73 (m, 2H), 3.64-3.60 (m, 3H), 3.59-3.56 (m, 4H), 3.18 (s, 2H), 3.04 (d, J = 7.2 Hz, 2H), 3.01-2.95 (m, 2H), 2.89-2.82 (m, 2H), 2.70 (d, J = 8.0 Hz, 2H), 2.59 (d, J = 6.4 Hz, 2H), 2.52 (d, J = 2.0 Hz, 3H), 2.20-2.14 (m, 3H), 2.08-2.01 (m, 2H), 1.89 (d, J = 13.2 Hz, 2H), 1.77 (d, J = 2.4 Hz, 1H), 1.75-1.67 (m, 2H), 1.64-1.51 (m, 3H), 1.15-1.05 (m, 5H), 1.05-0.92 (m, 9H), 0.49-0.41 (m, 2H), 0.25-0.18 (m, 2H) |
| I-162 | ZM | TE | 857.5 | 11.07 (s, 1H), 9.36 (s, 1H), 8.85 (d, J = 8.0 Hz, 1H), 8.39 (s, 1H), 8.30 (s, 1H), 8.17 (s, 1H), 7.28-6.96 (m, 3H), 6.93 (d, J = 8.0 Hz, 1H), 6.87 (dd, J = 0.8, 8.0 Hz, 1H), 5.34 (dd, J = 5.2, 12.8 Hz, 1H), 4.23-4.13 (m, 1H), 3.95-3.85 (m, 4H), 3.40 (t, J = 6.4 Hz, 2H), 3.32 (s, 3H), 3.31-3.25 (m, 1H), 3.07 (t, J = 4.4 Hz, 4H), 2.95-2.85 (m, 1H), 2.82-2.73 (m, 2H), 2.72-2.58 (m, 4H), 2.31-2.11 (m, 4H), 2.08-1.96 (m, 3H), 1.94-1.68 (m, 8H), 1.67-1.43 (m, 3H), 1.13-0.94 (m, 2H) |
| I-163 | YT | TE | 871.6 | 11.09 (s, 1H), 9.38 (s, 1H), 8.82 (d, J = 8.0 Hz, 1H), 8.38 (s, 1H), 8.28 (s, 1H), 8.19 (s, 1H), 7.25-6.97 (m, 3H), 6.91 (d, J = 8.0 Hz, 1H), 6.86 (d, J = 7.6 Hz, 1H), 5.39-5.29 (m, 1H), 4.24-4.13 (m, 1H), 3.83 (s, 4H), 3.38-3.33 (m, 2H), 3.32 (s, 3H), 3.21 (d, J = 6.0 Hz, 2H), 2.98-2.93 (m, 4H), 2.89-2.80 (m, 1H), 2.76-2.55 (m, 4H), 2.21 (d, J = 6.8 Hz, 2H), 2.08-1.93 (m, 6H), 1.88 (d, J = 12.0 Hz, 2H), 1.84-1.78 (m, 2H), 1.77-1.71 (m, 2H), 1.66 (d, J = 13.6 Hz, 2H), 1.62-1.45 (m, 3H), 1.29-1.16 (m, 2H), 1.13-0.96 (m, 2H) |
| I-164 | YU | TE | 871.6 | 11.09 (s, 1H), 9.39 (s, 1H), 8.78 (d, J = 8.0 Hz, 1H), 8.38 (s, 1H), 8.26 (s, 1H), 8.21 (s, 1H), 7.24-6.93 (m, 3H), 6.89 (d, J = 8.0 Hz, 1H), 6.87-6.84 (m, 1H), 5.41-5.32 (m, 1H), 4.21-4.14 (m, 1H), 3.76 (s, 4H), 3.56 (s, 3H), 3.42 (t, J = 6.0 Hz, 2H), 3.23 (d, J = 6.0 Hz, 2H), 3.02-2.91 (m, 2H), 2.91-2.88 (m, 1H), 2.88-2.82 (m, 6H), 2.73-2.59 (m, 2H), 2.13 (d, J = 6.8 Hz, 2H), 2.08-1.94 (m, 3H), 1.92-1.77 (m, 6H), 1.76-1.68 (m, 2H), 1.67-1.46 (m, 4H), 1.28-1.13 (m, 2H), 1.11-0.96 (m, 2H) |
| I-165 | ABV | TE | 844.4 | 11.20 (s, 1H), 9.40 (s, 1H), 8.79 (d, J = 8.0 Hz, 1H), 8.38 (m, 1H), 8.29-8.21 (m, 2H), 7.26-6.94 (m, 4H), 6.90 (d, J = 8.0 Hz, 1H), 5.36 (dd, J = 5.2, 12.8 Hz, 1H), 4.21-4.14 (m, 1H), 3.89-3.75 (m, 4H), 3.43 (t, J = 6.0 Hz, 2H), 3.30-3.20 (m, 2H), 3.01-2.82 (m, 5H), 2.76 (t, J = 7.6 Hz, 2H), 2.72-2.61 (m, 4H), 2.30-2.01 (m, 7H), 1.94-1.67 (m, 8H), 1.61-1.53 (m, 1H), 1.44 (q, J = 9.2 Hz, 2H), 1.22-0.75 (m, 2H) |
| I-166 | ADP | TE | 844.4 | 11.21 (s, 1H), 10.11 (s, 1H), 9.61 (s, 1H), 9.35 (s, 1H), 8.91 (d, J = 7.6 Hz, 1H), 8.40 (s, 1H), 8.33 (s, 1H), 7.30-6.96 (m, 5H), 5.38 (dd, J = 3.2, 12.2 Hz, 1H), 4.23 (t, J = 12.0 Hz, 1H), 4.08 (s, 4H), 3.55-3.37 (m, 4H), 3.22 (s, 4H), 3.01-2.84 (m, 5H), 2.75-2.62 (m, 4H), 2.12-1.98 (m, 6H), 1.94-1.76 (m, 7H), 1.25-1.12 (m, 2H) |
| I-167 | ABW | PW | 856.5 | 11.11 (s, 1H), 9.68 (s, 1H), 8.92 (s, 1H), 8.18-8.12 (m, 2H), 7.80-7.65 (m, 3H), 7.33-6.92 (m, 4H), 5.12 (dd, J = 5.2, 12.8 Hz, 1H), 4.24-4.12 (m, 1H), 3.42-3.38 (m, 4H), 3.18 (t, J = 6.0 Hz, 2H), 3.11-3.05 (m, 2H), 2.95-2.83 (m, 1H), 2.64-2.52 (m, 2H), 2.35-2.29 (m, 2H), 2.16-2.08 (m, 5H), 2.08-1.99 (m, 3H), 1.93-1.80 (m, 4H), 1.80-1.68 (m, 2H), 1.66-1.58 (m, 2H), 1.57-1.46 (m, 1H), 1.15-0.87 (m, 3H), 0.49-0.41 (m, 2H), 0.26-0.18 (m, 2H) |
| I-168 | ADR | PW | 857.5 | 11.09 (s, 1H), 9.68 (s, 1H), 8.92 (s, 1H), 8.18 (s, 1H), 8.17-8.12 (m, 2H), 7.59 (dd, J = 7.2, 8.4 Hz, 1H), 7.29-7.00 (m, 6H), 6.62 (t, J = 5.6 Hz, 1H), 5.06 (dd, J = 5.2, 12.8 Hz, 1H), 4.22-4.04 (m, 1H), 3.61-3.55 (m, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 2H), 3.50-3.45 (m, 4H), 3.18 (t, J = 6.0 Hz, 2H), 2.94-2.82 (m, 1H), 2.64-2.53 (m, 2H), 2.34-2.30 (m, 2H), 2.10 (s, 3H), 2.09-1.98 (m, 5H), 1.88-1.82 (m, 2H), 1.77-1.60 (m, 4H), 1.57-1.46 (m, 1H), 1.13-0.90 (m, 3H), 0.49-0.40 (m, 2H), 0.25-0.18 (m, 2H) |
| I-169 | ADT | PW | 853.6 | 11.17-11.04 (m, 1H), 9.68 (s, 1H), 8.91 (s, 1H), 8.20-8.12 (m, 2H), 7.94-7.89 (m, 1H), 7.87-7.77 (m, 2H), 7.30-7.04 (m, 3H), 7.03-6.99 (m, 1H), 5.13 (dd, J = 5.6, 12.8 Hz, 1H), 4.23-4.15 (m, 1H), 3.93 (s, 2H), 3.18-3.16 (m, 2H), 2.94-2.85 (m, 4H), 2.25-2.16 (m, 6H), 2.10-1.99 (m, 6H), 1.94-1.85 (m, 2H), 1.75 (d, J = 12.0 Hz, 2H), 1.68-1.60 (m, 2H), 1.53-1.42 (m, 3H), 1.10-0.94 (m, 3H), 0.48-0.42 (m, 2H), 0.22-0.19 (m, J = 4.6 Hz, 2H) |
| I-170 | ADV | PW | 897.5 | 11.03 (s, 1H), 9.80 (s, 1H), 9.65 (s, 1H), 9.04 (s, 1H), 8.13 (s, 1H), 8.02 (d, J = 6.4 Hz, 1H), 7.58-7.50 (m, 2H), 7.27-7.09 (m, 2H), 7.08-7.02 (m, 1H), 7.00-6.95 (m, 1H), 6.59-6.44 (m, 1H), 5.02-4.96 (m, 1H), 4.22-4.15 (m, 1H), 3.79-3.72 (m, 2H), 3.68-3.62 (m, 2H), 3.28-3.26 (m, 2H), 2.92-2.86 (m, 3H), 2.84-2.79 (m, 1H), 2.58-2.47 (m, 1H), 2.05-1.99 (m, 3H), 1.87-1.73 (m, 4H), 1.64-1.48 (m, 5H), 1.26-1.04 (m, 11H), 0.80-0.75 (m, 1H), 0.55-0.47 (m, 2H), 0.30-0.24 (m, 2H) |
| I-171 | ABX | PW | 868.2 | 11.12 (s, 1H), 9.70 (s, 1H), 8.92 (s, 1H), 8.17 (s, 1H), 8.14 (d, J = 5.2 Hz, 1H), 7.81-7.66 (m, 3H), 7.33-6.97 (m, 4H), 5.13 (dd, J = 5.2, 12.8 Hz, 1H), 4.24-4.13 (m, 1H), 3.41 (t, J = 6.0 Hz, 2H), 3.25-3.21 (m, 1H), 3.17 (t, J = 6.0 Hz, 2H), 3.09 (t, J = 7.2 Hz, 2H), 2.94-2.85 (m, 1H), 2.66-2.60 (m, 2H), 2.58-2.52 (m, 2H), 2.13-1.94 (m, 7H), 1.91-1.67 (m, 8H), 1.60-1.50 (m, 1H), 1.46-1.33 (m, 2H), 1.13-0.94 (m, 3H), 0.50-0.40 (m, 2H), 0.26-0.17 (m, 2H) |
| I-172[b] | TN | ABP | 832.6 | 11.10 (s, 1H), 9.47 (s, 1H), 9.21-9.09 (m, 1H), 8.57(d, J = 7.6 Hz, 1H), 8.25 (s, 1H), 8.16 (d, J = 2.8 Hz, 2H), 7.00-6.95 (m, 3H), 6.92-6.86 (m, 1H), 6.45 (d, J = 7.6 Hz, 1H), 5.42 (s, 1H), 5.37 (d, J = 4.8 Hz, 1H), 5.23 (s, 1H), 4.19-4.08 (m, 1H), 3.68 (s, 1H), 3.59 (d, J = 9.2 Hz, 4H), 3.55-3.46 (m, 6H), 3.03-2.93 (m, 9H), 2.11 (s, 4H), 1.95 (s, 9H), 1.29-1.13 (m, 4H), 0.56-0.50 (m, 2H), 0.29-0.22 (m, 2H) |
| I-173[b] | WX | ABP | 817.3 | 11.11 (s, 1H), 9.44 (s, 1H), 8.56 (d, J = 7.6 Hz, 1H), 8.25-8.21 (m, 1H), 8.16 (s, 1H), 8.12 (s, 1H), 7.10-7.03 (m, 1H), 6.95 (t, J = 8.0 Hz, 1H), 6.90-6.83 (m, 1H), 6.43 (d, J = 7.6 Hz, 1H), 5.43-5.34 (m, 2H), 5.20 (s, 1H), 4.09-4.01 (m, 1H), 3.67 (s, 3H), 3.61 (s, 2H), 3.29-3.25 (m, 2H), 2.91-2.83 (m, 3H), 2.77-2.69 (m, 1H), 2.65-2.59 (m, 1H), 2.37-2.33 (m, 1H), 2.20 (d, J = 6.8 Hz, 2H), 2.17 (s, 3H), 2.10 (s, 3H), 2.04-1.93 (m, 5H), 1.87 (d, J = 12.0 Hz, 2H), 1.76-1.67 (m, 2H), 1.63 (d, J = 12.0 Hz, 2H), 1.52-1.44 (m, 1H), 1.43-1.33 (m, 2H), 1.10-0.95 (m, 3H), 0.55-0.49 (m, 2H), 0.27-0.22 (m, 2H) |
| I-174 | AED | PW | 766.5 | 9.68 (s, 1H), 8.92 (s, 1H), 8.18 (s, 1H), 8.15 (d, J = 5.2 Hz, 1H), 7.31-6.97 (m, 4H), 4.23-4.15 (m, 1H), 3.56-3.38 (m, 11H), 3.18 (t, J = 6.0 Hz, 2H), 2.24-2.16 (m, 5H), 2.10-2.01 (m, 5H), 1.95-1.85 (m, 2H), 1.81-1.49 (m, 16H), 1.11-0.96 (m, 3H), 0.48-0.42 (m, 2H), 0.25-0.20 (m, 2H) |
| I-175 | AED | TE | 754.6 | 9.82 (s, 2H), 9.34 (s, 1H), 8.90 (d, J = 7.6 Hz, 1H), 8.39 (s, 1H), 8.32 (s, 1H), 7.33-6.85 (m, 2H), 4.27-4.18 (m, 1H), 4.15-4.03 (m, 4H), 3.87-3.76 (m, 2H), 3.61-3.53 (m, 4H), 3.47 (s, 3H), 3.37-3.16 (m, 6H), 3.15-3.04 (m, 1H), 2.99-2.89 (m, 1H), 2.79 (d, J = 4.4 Hz, 3H), 2.11-1.76 (m, 10H), 1.67-1.49 (m, 12H), 1.25-1.10 (m, Hz, 2H) |
| I-176 | ZM | ABC | 858.6 | 11.07 (s, 1H), 9.39 (s, 1H), 8.82 (d, J = 7.8 Hz, 1H), 8.37 (s, 1H), 8.28 (s, 1H), 7.26-6.94 (m, 3H), 6.90-6.85 (m, 2H), 5.33 (dd, J = 5.2, 12.8 Hz, 1H), 4.17 (t, J = 11.6 Hz, 1H), 3.82-3.77 (m, 4H), 3.74-3.72 (m,, 4H), 3.39 (t, J = 6.0 Hz, 2H), 3.32 (s, 3H), 3.24 (s, 1H), 2.94-2.84 (m, 1H), 2.73-2.56 (m, 6H), 2.13 (br d, J = 6.8 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | Hz, 2H), 2.10-1.95 (m, 5H), 1.91-1.68 (m, 8H), 1.56 (s, 1H), 1.50-1.39 (m, 2H), 1.07-0.98 (m, 2H) |
| I-177[b] | AEK | WW | 829.5 | 11.09 (s, 1H), 9.39 (s, 1H), 8.82 (d, J = 7.6 Hz, 1H), 8.39 (s, 1H), 8.28 (s, 1H), 7.24-6.85 (m, 5H), 5.37 (dd, J = 5.2, 12.4 Hz, 1H), 4.26-4.13 (m, 1H), 3.82-3.75 (m, 4H), 3.74-3.70 (m, 4H), 3.67 (s, 3H), 3.60 (s, 2H), 2.99-2.62 (m, 6H), 2.38-2.33 (m, 2H), 2.10-1.85 (m, 10H), 1.66-1.59 (m, 2H), 1.39-1.33 (m, 2H), 1.32-1.25 (m, 1H), 1.17-1.04 (m, 2H) |
| I-178[b] | AEK | SK | 829.4 | 11.12 (s, 1H), 9.42 (s, 1H), 8.82 (d, J = 8.0 Hz, 1H), 8.53-8.41 (m, 1H), 8.29 (s, 1H), 7.53-7.44 (m, 1H), 7.33-7.11 (m, 3H), 6.91 (d, J = 8.0 Hz, 1H), 5.42 (dd, J = 5.2, 12.8 Hz, 1H), 4.61-4.52 (m, 1H), 4.29 (s, 2H), 3.79 (s, 3H), 3.74-3.70 (m, 4H), 3.64-3.58 (m, 4H), 3.16-2.96 (m, 6H), 2.95-2.79 (m, 4H), 2.77-2.70 (m, 2H), 2.34-2.22 (m, 5H), 2.07-1.99 (m, 1H), 1.90-1.82 (m, 2H), 1.71-1.48 (m, 5H) |
| I-179[b] | AEJ | AEM | 804.5 | 11.06 (s, 1H), 9.40 (s, 1H), 8.81 (d, J = 8.0 Hz, 1H), 8.38 (s, 1H), 8.29 (s, 1H), 7.24-6.95 (m, 3H), 6.92-6.85 (m, 2H), 5.32 (dd, J = 5.2, 12.4 Hz, 1H), 4.27-4.14 (m, 1H), 3.78-3.78 (m, 1H), 3.84-3.67 (m, 9H), 3.46-3.41 (m, 2H), 3.41-3.40 (m, 4H), 3.32 (s, 3H), 2.98-2.83 (m, 4H), 2.71-2.70 (m, 1H), 2.09-1.95 (m, 6H), 1.90 (d, J = 8.4 Hz, 2H), 1.85-1.78 (m, 2H), 1.71-1.63 (m, 2H) |
| I-180[b] | AEJ | ADI | 804.5 | 11.09 (s, 1H), 9.43 (s, 1H), 8.84 (d, J = 7.6 Hz, 1H), 8.45 (s, 1H), 8.30 (s, 1H), 7.27-6.95 (m, 3H), 6.92 (d, J = 8.0 Hz, 1H), 6.90-6.85 (m, 1H), 5.37 (dd, J = 5.2, 12.4 Hz, 1H), 4.62-4.49 (m, 1H), 3.80 (s, 4H), 3.73 (d, J = 4.4 Hz, 4H), 3.67 (d, J = 11.6 Hz, 2H), 3.61-3.56 (m, 3H), 3.48-3.46 (m, 5H), 3.21-3.07 (m, 4H), 3.04-2.94 (m, 2H), 2.93-2.83 (m, 1H), 2.77-2.68 (m, 1H), 2.66-2.58 (m, 1H), 2.29 (s, 1H), 2.23-2.13 (m, 2H), 2.05-1.82 (m, 5H) |
| I-181[b] | AAY | ABY | 840.6 | 11.09 (s, 1H), 9.71 (s, 1H), 8.92 (s, 1H), 8.20-8.18 (m, 2H), 8.15 (d, J = 4.8 Hz, 1H), 7.30-7.05 (m, 4H), 7.03-7.00 (m, 1H), 5.35 (dd, J = 4.8, 12.4 Hz, 1H), 4.29-4.16 (m, 1H), 3.49 (s, 3H), 3.20-3.15 (m, 4H), 3.00-2.92 (m, 3H), 2.92-2.85 (m, 1H), 2.84-2.78 (m, 2H), 2.65-2.57 (m, 1H), 2.52-2.52 (m, 2H), 2.09-1.84 (m, 10H), 1.64 (d, J = 12.4 Hz, 2H), 1.42-1.33 (m, 2H), 1.32-1.24 (m, 1H), 1.23-1.11 (m, 2H), 1.10-1.01 (m, 1H), 0.48-0.42 (m, 2H), 0.26-0.18 (m, 2H) |
| I-182[b] | ACX | SK | 826.6 | 11.11 (s, 1H), 10.94 (d, J = 2.8 Hz, 1H), 10.64 (d, J = 4.0 Hz, 1H), 10.00 (s, 1H), 9.13 (s, 1H), 8.37-8.01 (m, 2H), 7.64 (s, 1H), 7.54 (s, 1H), 7.39-7.06 (m, 4H), 5.43 (dd, J = 5.6, 12.8 Hz, 1H), 4.68-4.50 (m, 1H), 4.43-4.21 (m, 2H), 3.72-3.63 (m, 2H), 3.38-3.36 (m, 2H), 3.36 (s, 3H), 3.35-3.32 (m, 3H), 3.10 (d, J = 11.6 Hz, 2H), 3.06-2.98 (m, 2H), 2.97-2.90 (m, 1H), 2.90-2.78 (m, 2H), 2.76-2.59 (m, 2H), 2.57-2.52 (m, 1H), 2.40-2.31 (m, 1H), 2.30-2.19 (m, 2H), 2.17-1.94 (m, 4H), 1.77-1.57 (m, 2H), 1.24-1.09 (m, 1H), 0.59-0.52 (m, 2H), 0.36-0.30 (m, 2H) |
| I-183 | ACV | ABC | 869.3 | 11.09 (s, 1H), 9.41 (s, 1H), 8.83 (d, J = 8.0 Hz, 1H), 8.39 (s, 1H), 8.29 (s, 1H), 7.24-6.88 (m, 5H), 5.43-5.34 (m, 1H), 4.28-4.19 (m, 1H), 4.10-4.02 (m, 1H), 4.00-3.87 (m, 3H), 3.80 (s, 4H), 3.73 (d, J = 4.6 Hz, 4H), 3.61 (s, 3H), 3.49 (s, 1H), 3.22-3.16 (m, 2H), 3.11-2.99 (m, 2H), 2.92 (d, J = 6.8 Hz, 5H), 2.77-2.71 (m, 1H), 2.22-1.76 (m, 12H), 1.26-1.12 (m, 3H) |
| I-184[b] | PP | AEP | 868.6 | 11.07 (s, 1H), 8.85 (s, 1H), 8.38-8.27 (m, 1H), 8.04-8.00 (m, 1H), 7.88 (s, 1H), 7.79-7.74 (m, 1H), 7.74-7.66 (m, 1H), 6.99-6.91 (m, 2H), 6.90-6.78 (m, 1H), 5.35 (dd, J = 5.2, 12.4 Hz, 1H), 5.02-4.80 (m, 1H), 4.54 (dd, J = 3.2, 11.2 Hz, 1H), 4.26 (dd, J = 6.0, 11.2 Hz, 1H), 4.15-4.05 (m, 1H), 3.98 (s, 3H), 3.56 (s, 3H), 3.43-3.40 (m, 4H), 2.98-2.84 (m, 3H), 2.76-2.55 (m, 4H), 2.36-2.30 (m, 2H), 2.17-1.97 (m, 8H), 1.88- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|
| | | | | 1.78 (m, 4H), 1.68-1.58 (m, 4H), 1.54-1.41 (m, 3H), 1.01 (t, J = 7.4 Hz, 3H), 0.97-0.87 (m, 2H) |
| I-185[b] | QI | AFM | 868.6 | 11.07 (s, 1H), 8.86 (s, 1H), 8.29 (s, 1H), 8.01 (s, 1H), 7.89 (s, 1H), 7.76 (s, 1H), 7.73 (s, 1H), 7.05-6.96 (m, 2H), 6.87 (d, J = 8.0 Hz, 1H), 5.32 (dd, J = 5.2, 12.8 Hz, 1H), 5.01-4.76 (m, 1H), 4.54 (dd, J = 3.2, 11.2 Hz, 1H), 4.27 (dd, J = 6.4, 11.2 Hz, 1H), 4.15-4.05 (m, 1H), 3.98 (s, 3H), 3.43-3.38 (m, 4H), 3.31 (s, 3H), 2.96-2.82 (m, 1H), 2.76-2.54 (m, 6H), 2.34 (t, J = 6.8 Hz, 2H), 2.13 (s, 3H), 2.11-1.94 (m, 5H), 1.88-1.75 (m, 4H), 1.69-1.41 (m, 7H), 1.08-0.79 (m, 5H) |
| I-186[b] | TN | AFM | 880.6 | 11.10 (s, 1H), 8.88 (s, 1H), 8.28 (s, 1H), 8.02 (s, 1H), 7.92-7.84 (m, 1H), 7.80-7.68 (m, 2H), 6.96 (d, J = 4.8 Hz, 2H), 6.90-6.83 (m, 1H), 5.36 (dd, J = 5.2, 12.4 Hz, 1H), 4.99-4.81 (m, 1H), 4.54 (dd, J = 3.6, 11.2 Hz, 1H), 4.26 (dd, J = 6.4, 11.2 Hz, 1H), 4.12-4.05 (m, 1H), 3.97 (s, 3H), 3.57 (s, 3H), 3.44 (d, J = 6.4 Hz, 4H), 2.99-2.93 (m, 2H), 2.70-2.54 (m, 6H), 2.10-1.95 (m, 7H), 1.86-1.76 (m, 6H), 1.62-1.39 (m, 7H), 1.04-0.87 (m, 5H) |
| I-187[b] | ZM | AFM | 880.6 | 11.08 (s, 1H), 8.86 (s, 1H), 8.28 (s, 1H), 8.01 (s, 1H), 7.89 (s, 1H), 7.80-7.67 (m, 2H), 7.07-6.96 (m, 2H), 6.87 (d, J = 8.0 Hz, 1H), 5.33 (dd, J = 5.2, 12.8 Hz, 1H), 5.00-4.81 (m, 1H), 4.54 (dd, J = 3.6, 11.2 Hz, 1H), 4.29-4.20 (m, 1H), 4.13-4.05 (m, 1H), 3.98 (s, 3H), 3.47-3.43 (m, 2H), 3.32 (s, 3H), 3.26-3.20 (m, 2H), 2.93-2.84 (m, 1H), 2.71-2.61 (m, 6H), 2.12-1.94 (m, 7H), 1.88-1.73 (m, 6H), 1.65-1.34 (m, 7H), 1.10-0.86 (m, 6H) |
| I-188[b] | PP | AIK | 911.6 | 11.08 (s, 1H), 9.30-9.25 (m, 1H), 8.86 (s, 1H), 8.77-8.68 (m, 1H), 8.53-8.47 (m, 1H), 7.88-7.79 (m, 2H), 7.69-7.60 (m, 1H), 6.98-6.78 (m, 4H), 5.39-5.31 (m, 1H), 5.00-4.83 (m, 1H), 4.62-4.55 (m, 1H), 4.40-4.28 (m, 2H), 4.15-4.07 (m, 1H), 3.98 (s, 3H), 3.82-3.74 (m, 2H), 3.56 (s, 3H), 2.97 (d, J = 7.2 Hz, 2H), 2.64-2.57 (m, 2H), 2.40-2.35 (m, 2H), 2.25-2.17 (m, 3H), 2.14 (s, 3H), 2.03-1.89 (m, 4H), 1.86-1.75 (m, 4H), 1.68-1.61 (m, 4H), 1.58-1.47 (m, 2H), 1.14-0.99 (m, 5H) |
| I-189 | AFM | WX | 865.6 | 11.10 (s, 1H), 8.86 (s, 1H), 8.28 (s, 1H), 8.01 (s, 1H), 7.89 (s, 1H), 7.76 (s, 1H), 7.73 (s, 1H), 7.07 (d, J = 7.6 Hz, 1H), 6.95 (t, J = 7.6 Hz, 1H), 6.86 (d, J = 7.6 Hz, 1H), 5.38 (dd, J = 5.2, 12.8 Hz, 1H), 4.99-4.81 (m, 1H), 4.54 (dd, J = 3.2, 11.2 Hz, 1H), 4.26 (dd, J = 6.0, 10.8 Hz, 1H), 4.09-4.06 (m, 1H), 3.97 (s, 3H), 3.67 (s, 3H), 3.61 (s, 2H), 2.91-2.83 (m, 3H), 2.73-2.64 (m, 2H), 2.62-2.53 (m, 2H), 2.36-2.29 (m, 1H), 2.18 (d, J = 7.2 Hz, 2H), 2.16 (s, 3H), 2.09-1.92 (m, 5H), 1.80 (d, J = 12.0 Hz, 2H), 1.66-1.54 (m, 4H), 1.51-1.32 (m, 5H), 1.03-0.97 (m, 3H), 0.96-0.84 (m, 2H) |
| I-190[b] | AAD | AFM | 865.5 | 11.11 (s, 1H), 8.87 (s, 1H), 8.29 (s, 1H), 8.01 (s, 1H), 7.89 (s, 1H), 7.76 (s, 1H), 7.73 (s, 1H), 7.12-6.93 (m, 3H), 5.35 (dd, J = 5.2, 12.8 Hz, 1H), 5.00-4.81 (m, 1H), 4.54 (dd, J = 3.6, 11.2 Hz, 1H), 4.26 (dd, J = 6.4, 11.2 Hz, 1H), 4.12-4.05 (m, 1H), 3.97 (s, 3H), 3.46 (s, 2H), 3.34 (s, 3H), 2.88-2.84 (m, 2H), 2.74-2.53 (m, 4H), 2.31-2.13 (m, 6H), 2.10-1.76 (m, 8H), 1.66-1.54 (m, 4H), 1.50-1.37 (m, 5H), 1.01 (t, J = 7.2 Hz, 3H), 0.97-0.86 (m, 2H) |
| I-191 | WX | AGL | 844.3 | 12.37 (s, 1H), 11.14 (s, 1H), 8.72 (s, 1H), 8.49-8.42 (m, 1H), 8.40-8.33 (m, 2H), 8.17 (d, J = 8.0 Hz, 1H), 7.55 (s, 1H), 7.35-6.84 (m, 3H), 6.02-5.88 (m, 1H), 5.50-5.36 (m, 1H), 4.71-4.56 (m, 1H), 4.52-4.41 (m, 1H), 3.64 (s, 3H), 3.36-3.15 (m, 3H), 3.10-2.85 (m, 4H), 2.83-2.69 (m, 4H), 2.64-2.53 (m, 3H), 2.23-2.12 (m, 3H), 2.10-1.80 (m, 9H), 1.62 (s, 6H), 1.38-1.13 (m, 2H) |
| I-192[b] | ZO | ABC | 878.3 | 11.15 (s, 1H), 9.40 (s, 1H), 8.82 (d, J = 8.0 Hz, 1H), 8.38 (s, 1H), 8.32 (d, J = 5.2 Hz, 1H), 8.29 (s, 1H), 8.26 (d, J = 8.0 Hz, 1H), 7.78-7.57 (m, 1H), 7.52 (t, J = 8.0 Hz, 1H), 7.30 (t, J = 8.0 Hz, 1H), 7.25-6.95 (m, 2H), 6.90 (d, J = 7.6 Hz, 1H), 6.31-5.78 (m, 1H), 4.21- |

TABLE 7-continued

Compounds synthesized via Method 2 with the reductive
amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 4.13 (m, 1H), 3.86-3.76 (m, 4H), 3.75-3.69 (m, 4H), 3.55 (t, J = 6.0 Hz, 2H), 3.28-3.23 (m, 2H), 3.15-2.95 (m, 3H), 2.74-2.65 (m, 3H), 2.19-1.94 (m, 9H), 1.93-1.81 (m, 4H), 1.80-1.68 (m, 2H), 1.64-1.44 (m, 3H), 1.10-0.96 (m, 2H) |
| I-193[b] | AHH | AHI | 865.6 | 11.05 (s, 1H), 8.85 (s, 1H), 8.32 (s, 1H), 8.03 (s, 1H), 7.88 (s, 1H), 7.76 (s, 1H), 7.72 (s, 1H), 7.08 (s, 1H), 7.05-7.00 (m, 1H), 6.98-6.93 (m, 1H), 5.40-5.27 (m, 1H), 5.02-4.79 (m, 1H), 4.60-4.49 (m, 1H), 4.33-4.21 (m, 1H), 4.13-4.05 (m, 1H), 3.98 (s, 3H), 3.43 (m, 3H), 2.95-2.87 (m, 1H), 2.82-2.75 (m, 3H), 2.75-2.68 (m, 3H), 2.65-2.58 (m, 2H), 2.29-2.22 (m, 2H), 2.20-2.11 (m, 2H), 2.05-1.98 (m, 1H), 1.94-1.84 (m, 4H), 1.73-1.66 (m, 2H), 1.65-1.52 (m, 5H), 1.46-1.37 (m, 2H), 1.25-1.15 (m, 4H), 1.15-1.05 (m, 2H), 1.04-0.98 (m, 3H) |
| I-194[b] | AHJ | WW | 837.6 | 11.11 (s, 1H), 8.88 (s, 1H), 8.32 (s, 1H), 8.04 (s, 1H), 7.90 (s, 1H), 7.77 (s, 1H), 7.74 (s, 1H), 7.07 (d, J = 8.0 Hz, 1H), 6.96 (t, J = 7.6 Hz, 1H), 6.88 (d, J = 7.2 Hz, 1H), 5.45-5.34 (m, 1H), 5.02-4.80 (m, 1H), 4.60-4.50 (m, 1H), 4.33-4.20 (m, 1H), 4.15-4.05 (m, 1H), 3.98 (s, 3H), 3.68 (s, 3H), 3.62 (s, 2H), 3.32-3.30 (m, 2H), 2.97-2.73 (m, 5H), 2.66-2.54 (m, 2H), 2.21-2.16 (m, 1H), 2.15-2.10 (m, 2H), 2.07-1.98 (m, 2H), 1.98-1.91 (m, 3H), 1.74-1.47 (m, 8H), 1.10-0.99 (m, 5H) |
| I-195[b] | ACZ | ABC | 872.5 | 9.46-9.29 (m, 1H), 8.87-8.73 (m, 1H), 8.42-8.34 (m, 1H), 8.30-8.25 (m, 1H), 7.24-6.83 (m, 5H), 5.49-5.34 (m, 1H), 4.17(s, 1H), 3.79 (s, 4H), 3.72 (d, J = 4.6 Hz, 4H), 3.57 (s, 3H), 3.51-3.42 (m, 3H), 3.06-3.01 (m, 3H), 3.00 (s, 3H), 2.82-2.61 (m, 4H), 2.15-1.95 (m, 7H), 1.81 (s, 8H), 1.62-1.36 (m, 3H), 1.11-0.94 (m, 2H) |
| I-196[b] | AFH | ABC | 878.3 | 11.14 (s, 1H), 9.39 (s, 1H), 8.82 (d, J = 8.0 Hz, 1H), 8.64-8.56 (m, 1H), 8.43 (d, J = 4.0 Hz, 1H), 8.37 (s, 1H), 8.29 (s, 1H), 7.53-7.38 (m, 2H), 7.27 (d, J = 5.6 Hz, 1H), 7.24-6.95 (m, 2H), 6.90 (d, J = 8.0 Hz, 1H), 6.19-5.84 (m, 1H), 4.22-4.13 (m, 1H), 3.84-3.68 (m, 8H), 3.56 (d, J = 6.0 Hz, 3H), 3.25-3.17 (m, 4H), 2.73-2.64 (m, 3H), 2.17-2.00 (m, 7H), 1.99-1.83 (m, 6H), 1.80-1.67 (m, 2H), 1.64-1.47 (m, 3H), 1.11-0.96 (m, 2H) |
| I-197[b] | AFQ | ABC | 883.5 | 11.00 (s, 1H), 9.40 (s, 1H), 8.83 (d, J = 8.0 Hz, 1H), 8.38 (s, 1H), 8.29 (s, 1H), 7.50-7.39 (m, 4H), 7.25-6.96 (m, 1H), 6.91 (d, J = 8.0 Hz, 1H), 5.72-5.60 (m, 1H), 4.74-4.62 (m, 1H), 4.24-4.11 (m, 1H), 3.96-3.85 (m, 1H), 3.83-3.77 (m, 4H), 3.75-3.70 (m, 4H), 3.60 (t, J = 6.4 Hz, 2H), 2.91-2.81 (m, 1H), 2.71-2.60 (m, 5H), 2.37-2.30 (m, 2H), 2.27-2.17 (m, 1H), 2.11-2.07 (m, 2H), 2.06-1.96 (m, 5H), 1.91-1.81 (m, 4H), 1.79-1.68 (m, 2H), 1.61-1.52 (m, 1H), 1.51-1.40 (m, 2H), 1.09-0.97 (m, 2H) |
| I-198[b] | TN | ABC | 872.5 | 11.08 (s, 1H), 9.39 (s, 1H), 8.82 (d, J = 8.0 Hz, 1H), 8.37 (s, 1H), 8.28 (s, 1H), 7.23-6.96 (m, 2H), 6.96 (s, 1H), 6.91 (d, J = 8.0 Hz, 1H), 6.88-6.85 (m, 1H), 5.42-5.32(m, 1H), 4.22-4.13 (m, 1H), 3.79 (s, 4H), 3.74-3.70 (m, 4H), 3.56 (s, 3H), 3.42 (t, J = 6.0 Hz, 2H), 3.24 (d, J = 6.4 Hz, 2H), 2.99-2.92 (m, 2H), 2.85-2.80 (m, 2H), 2.76-2.68 (m, 1H), 2.11-2.09 (m, 2H), 2.04-2.02 (m, 3H), 1.90-1.79 (m, 7H), 1.74 (d, J = 10.8 Hz, 2H), 1.66-1.61 (m, 2H), 1.54-1.45 (m, 2H), 1.26-1.12 (m, 3H), 1.08-0.99 (m, 2H) |
| I-199[b] | ZH | ABC | 800.3 | 11.08 (s, 1H), 9.40 (s, 1H), 8.82 (d, J = 8.0 Hz, 1H), 8.39 (s, 1H), 8.29 (s, 1H), 7.27-6.94 (m, 4H), 6.91 (d, J = 8.0 Hz, 1H), 5.37 (dd, J = 5.2, 12.4 Hz, 1H), 4.26-4.14 (m, 1H), 3.83-3.76 (m, 4H), 3.75-3.69 (m, 4H), 3.58 (s, 3H), 3.26-3.17 (m, 2H), 3.04-2.82 (m, 3H), 2.76-2.59 (m, 2H), 2.22-2.14 (m, 2H), 2.10-2.01 (m, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|
| | | | | 4H), 2.01-1.96 (m, 1H), 1.96-1.89 (m, 2H), 1.83-1.75 (m, 4H), 1.75-1.70 (m, 1H), 1.67-1.55 (m, 1H), 1.15-1.00 (m, 2H) |
| I-200[b] | AEJ | AGP | 858.5 | 11.10 (s, 1H), 9.40 (s, 1H), 8.83 (d, J = 8.0 Hz, 1H), 8.39 (s, 1H), 8.29 (s, 1H), 7.25-6.83 (m, 5H), 5.39-5.34 (m, 1H), 4.27-4.15 (m, 1H), 3.79 (m, 4H), 3.72 (m, 4H), 3.56 (s, 3H), 3.46 (t, J = 6.0 Hz, 2H), 3.17-3.15 (m, 1H), 2.99-2.84 (m, 5H), 2.76-2.59 (m, 2H), 2.14-2.06 (m, 2H), 2.06-1.88 (m, 9H), 1.85-1.73 (m, 4H), 1.50-1.39 (m, 1H), 1.20-1.06 (m, 2H), 0.94-0.80 (m, 2H) |
| I-201[b] | PP | AHY | 850.3 | 11.09 (s, 1H), 8.38 (s, 1H), 8.23 (s, 1H), 8.08-8.03 (m, 2H), 7.88 (s, 1H), 7.71 (s, 1H), 7.59 (s, 1H), 6.99-6.90 (m, 2H), 6.82 (dd, J = 2.4, 6.8 Hz, 1H), 5.36 (dd, J = 5.2, 12.8 Hz, 1H), 4.45 (br d, J = 3.9 Hz, 2H), 3.99 (s, 3H), 3.98-3.94 (m, 1H), 3.54 (s, 3H), 3.45-3.44 (m, 2H), 3.12 (d, J = 3.6 Hz, 2H), 2.95-2.88 (m, 3H), 2.78-2.64 (m, 2H), 2.36 (t, J = 7.2 Hz, 2H), 2.32-2.25 (m, 1H), 2.21 (d, J = 6.8 Hz, 2H), 2.18-2.12 (m, 4H), 2.04-1.97 (m, 1H), 1.87-1.76 (m, 4H), 1.75-1.47 (m, 9H), 1.46-1.32 (m, 3H), 0.93 (t, J = 7.2 Hz, 3H) |
| I-202[b] | TN | AHY | 862.3 | 11.08 (s, 1H), 8.37 (s, 1H), 8.07-8.02 (m, 2H), 7.88 (s, 1H), 7.72 (s, 1H), 7.60 (s, 1H), 6.96 (d, J = 4.8 Hz, 2H), 6.91-6.84 (m, 1H), 5.36 (dd, J = 5.2, 12.8 Hz, 1H), 4.46 (d, J = 4.4 Hz, 2H), 3.99 (s, 3H), 3.97-3.94 (m, 1H), 3.57 (s, 3H), 3.47-3.45 (m, 2H), 3.28-3.26 (m, 2H), 3.14-3.10 (m, 1H), 2.99-2.93 (m, 2H), 2.91-2.83 (m, 1H), 2.74-2.65 (m, 3H), 2.32-2.24 (m, 1H), 2.24-2.20 (m, 2H), 2.17-2.11 (m, 1H), 2.10-2.03 (m, 2H), 2.02-1.96 (m, 1H), 1.87-1.76 (m, 6H), 1.68-1.66 (m, 4H), 1.61-1.55 (m, 2H), 1.54-1.29 (m, 6H), 0.92 (t, J = 7.2 Hz, 3H) |
| I-203[b] | AIL | ADI | 808.5 | 11.09 (s, 1H), 8.33 (s, 1H), 8.07-8.01 (m, 2H), 7.90 (s, 1H), 7.73 (s, 1H), 7.59 (s, 1H), 6.97-6.94 (m, 2H), 6.90-6.83 (m, 1H), 5.35 (dd, J = 5.2, 12.8 Hz, 1H), 4.45 (d, J = 4.4 Hz, 2H), 4.02-3.92 (m, 4H), 3.56 (s, 3H), 3.45-3.44 (m, 6H), 3.00-2.93 (m, 2H), 2.92-2.80 (m, 2H), 2.78-2.69 (m, 3H), 2.69-2.57 (m, 2H), 2.37 (t, J = 6.8 Hz, 2H), 2.31-2.24 (m, 1H), 2.16-2.05 (m, 1H), 2.03-1.88 (m, 3H), 1.87-1.77 (m, 2H), 1.74-1.63 (m, 4H), 1.61-1.51 (m, 1H), 1.42-1.31 (m, 1H), 0.92 (t, J = 7.2 Hz, 3H) |
| I-204[b] | AHH | ADI | 826.5 | 11.09 (s, 1H), 8.88 (s, 1H), 8.32 (s, 1H), 8.04 (s, 1H), 7.90 (s, 1H), 7.80-7.70 (m, 2H), 6.97-6.96 (m, 2H), 6.90-6.84 (m, 1H), 5.36 (dd, J = 5.2, 12.4 Hz, 1H), 5.04-4.78 (m, 1H), 4.54 (dd, J = 3.2, 11.2 Hz, 1H), 4.26 (dd, J = 6.4, 11.2 Hz, 1H), 4.15-4.03 (m, 1H), 3.98 (s, 3H), 3.56 (s, 3H), 3.43-3.40 (m, 4H), 2.99-2.93 (m, 2H), 2.91-2.70 (m, 5H), 2.67-2.58 (m, 2H), 2.37 (t, J = 7.2 Hz, 2H), 2.24-2.11 (m, 2H), 2.03-1.90 (m, 3H), 1.87-1.77 (m, 2H), 1.75-1.56 (m, 6H), 1.01 (t, J = 7.2 Hz, 3H) |
| I-205[b] | AFH | AFM | 900.7 | 11.15 (s, 1H), 8.87 (s, 1H), 8.60 (d, J = 4.0 Hz, 1H), 8.43 (d, J = 4.8 Hz, 1H), 8.29 (s, 1H), 8.02 (s, 1H), 7.90 (s, 1H), 7.80-7.69 (m, 2H), 7.45 (d, J = 7.2 Hz, 1H), 7.28 (d, J = 6.4 Hz, 1H), 7.12 (d, J = 8.0 Hz, 1H), 6.30-5.90 (m, 1H), 5.00-4.81 (m, 1H), 4.54 (d, J = 7.2 Hz, 1H), 4.27 (d, J = 8.0 Hz, 1H), 4.15-4.05 (m, 1H), 3.98 (s, 3H), 3.56 (d, J = 6.0 Hz, 2H), 3.26-3.17 (m, 5H), 3.10-2.94 (m, 2H), 2.76-2.62 (m, 4H), 2.15-2.03 (m, 7H), 1.95 (d, J = 7.6 Hz, 2H), 1.91-1.78 (m, 4H), 1.63-1.43 (m, 7H), 1.02 (d, J = 7.2 Hz, 3H), 0.99-0.89 (m, 2H) |
| I-206[b] | AFQ | AFM | 905.6 | 11.00 (s, 1H), 8.88 (s, 1H), 8.29 (s, 1H), 8.03 (s, 1H), 7.90 (s, 1H), 7.80-7.70 (m, 2H), 7.50-7.39 (m, 4H), 5.73-5.60 (m, 1H), 5.00-4.82 (m, 1H), 4.76-4.63 (m, 1H), 4.59-4.51 (m, 1H), 4.31-4.24 (m, 1H), 4.14-4.05 (m, 1H), 3.99 (s, 3H), 3.97-3.86 (m, 1H), 3.60 (t, J = 6.4 Hz, 2H), 3.29-3.18 (m, 2H), 2.94-2.77 (m, 1H), 2.67-2.55 (m, 5H), 2.26-2.19 (m, 1H), 2.12-1.91 (m, 8H), 1.87-1.79 (m, 4H), 1.66-1.37 (m, 8H), 1.02 (t, J = 7.2 Hz, 3H), 0.98-0.86 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| I-207[b] | ABX | ABC | 857.3 | 11.11 (s, 1H), 9.39 (s, 1H), 8.82 (d, J = 7.6 Hz, 1H), 8.37 (s, 1H), 8.31-8.25 (m, 1H), 7.80-7.68 (m, 3H), 7.23-6.95 (t, J = 5.2 Hz 1H), 6.90 (d, J = 7.6 Hz, 1H), 5.13 (m, 1H), 4.22-4.12 (m, 1H), 3.79 (s, 4H), 3.75-3.68 (m, 4H), 3.43-3.39 (m, 5H), 3.09 (m, 2H), 2.89 (m, 1H), 2.64-2.56 (m, 2H), 2.13-1.96 (m, 7H), 1.92-1.67 (m, 8H), 1.61-1.49 (m, 1H), 1.46-1.33 (m, 2H), 1.11-0.94 (m, 2H) |
| I-208[b] | AFJ | ABC | 872.3 | 11.08 (s, 1H), 9.39 (s, 1H), 8.82 (d, J = 8.0 Hz, 1H), 8.37 (s, 1H), 8.29 (s, 1H), 7.62-7.55 (m, 1H), 7.24-6.94 (m, 3H), 6.90 (d, J = 8.0 Hz, 1H), 6.63 (t, J = 5.6 Hz, 1H), 5.0 (dd, J = 4.2, 12.8 Hz, 1H), 4.22-4.11 (m, 1H), 3.79 (s, 4H), 3.74-3.71 (m, 4H), 3.49 (t, J = 6.0 Hz, 4H), 3.37 (d, J = 6.0 Hz, 3H), 2.90-2.80 (m, 1H), 2.62-2.53 (m, 3H), 2.09-1.99 (m, 6H), 1.90-1.66 (m, 8H), 1.59-1.38 (m, 3H), 1.09-0.93 (m, 2H) |
| I-209[b] | AHL | ABC | 859.6 | 10.99 (s, 1H), 9.40 (s, 1H), 8.83 (d, J = 8.0 Hz, 1H), 8.37 (s, 1H), 8.29 (s, 1H), 7.53-7.42 (m, 1H), 7.35-6.85 (m, 4H), 5.12 (dd, J = 52, 13.2 Hz, 1H), 4.44-4.33 (m, 1H), 4.27-4.09 (m, 4H), 3.87-3.76 (m, 4H), 3.75-3.66 (m, 4H), 3.58-3.53 (m, 2H), 3.29-3.27 (m, 1H), 2.98-2.85 (m, 1H), 2.63-2.54 (m, 3H), 2.48-2.40 (m, 1H), 2.11-1.90 (m, 9H), 1.88-1.66 (m, 6H), 1.59-1.35 (m, 3H), 1.06-0.91 (m, 2H) |
| I-210[b] | AGU | ABC | 858.2 | 11.09 (s, 1H), 9.40 (s, 1H), 8.83 (d, J = 8.0 Hz, 1H), 8.37 (s, 1H), 8.29 (s, 1H), 7.59 (dd, J = 7.2, 8.4 Hz, 1H), 7.24-6.95 (m, 3H), 6.91 (d, J = 8.0 Hz, 1H), 6.62 (t, J = 5.6 Hz, 1H), 5.07 (dd, J = 6.0, 13.2 Hz, 1H), 4.24-4.11 (m, 1H), 3.79 (s, 3H), 3.75-3.68 (m, 4H), 3.62 (t, J = 5.2 Hz, 2H), 3.48-3.40 (m, 2H), 2.94-2.82 (m, 1H), 2.62-2.54 (m, 3H), 2.52 (s, 3H), 2.11-1.96 (m, 7H), 1.90-1.67 (m, 6H), 1.59-1.39 (m, 3H), 1.10-0.93 (m, 2H) |
| I-211[b] | AFV | ABC | 885.5 | 11.06 (s, 1H), 9.39 (s, 1H), 8.82 (d, J = 8.0 Hz, 1H), 8.44 (t, J = 5.0 Hz, 1H), 8.37 (s, 1H), 8.28 (s, 1H), 7.48 (t, J = 8.2 Hz, 1H), 7.24-6.94 (m, 1H), 6.90 (d, J = 8.0 Hz, 1H), 6.63 (d, J = 7.6 Hz, 1H), 6.50 (d, J = 8.4 Hz, 1H), 5.16 (d, J = 11.2 Hz, 1H), 4.21-4.11 (m, 1H), 3.79 (s, 4H), 3.72 (d, J = 4.4 Hz, 4H), 3.53-3.46 (m, 2H), 3.22 (d, J = 5.6 Hz, 4H), 2.88-2.79 (m, 1H), 2.69-2.63 (m, 2H), 2.59 (s, 1H), 2.55 (s, 3H), 2.19-2.11 (m, 1H), 2.11-1.94 (m, 6H), 1.93-1.64 (m, 9H), 1.59-1.41 (m, 3H), 1.08-0.95 (m, 2H) |
| I-212[b] | AFX | ABC | 886.7 | 11.09 (s, 1H), 9.40 (s, 1H), 8.83 (d, J = 8.0 Hz, 1H), 8.38 (s, 1H), 8.29 (s, 1H), 7.61 (dd, J = 7.2, 8.4 Hz, 1H), 7.29 (d, J = 8.8 Hz, 1H), 7.24-6.86 (m, 3H), 5.09 (dd, J = 5.2, 12.8 Hz, 1H), 4.22-4.11 (m, 1H), 3.83-3.68 (m, 8H), 3.55 (t, J = 6.0 Hz, 2H), 3.40-3.36 (m, 1H), 3.33-3.30 (m, 2H), 3.07 (s, 1H), 3.00 (s, 3H), 2.93-2.82 (m, 1H), 2.62-2.53 (m, 3H), 2.19-1.93 (m, 7H), 1.89-1.66 (m, 8H), 1.58-1.47 (m, 1H), 1.35 (d, J = 9.2 Hz, 2H), 1.09-0.94 (m, 2H) |
| I-213[b] | WX | ABC | 843.3 | 11.09 (s, 1H), 9.39 (s, 1H), 8.82 (d, J = 8.0 Hz, 1H), 8.37 (s, 1H), 8.23 (s, 1H), 7.24-6.82 (m, 5H), 5.38 (dd, J = 5.6. 12.8 Hz, 1H), 4.20-4.11 (m, 1H), 3.81-3.76 (m, 4H), 3.74-3.69 (m, 4H), 3.67 (s, 3H), 3.61 (s, 2H), 2.95-2.88 (m, 1H), 2.88-2.82 (m, 2H), 2.74-2.59 (m, 1H), 2.53-2.51 (m, 1H), 2.35-2.28 (m, 1H), 2.23-2.18 (m, 2H), 2.17 (s, 3H), 2.06-1.98 (m, 3H), 1.98-1.91 (m, 2H), 1.91-1.83 (m, 2H), 1.79-1.68 (m, 2H), 1.67-1.58 (m, 2H), 1.52-1.43 (m, 1H), 1.42-1.29 (m, 2H), 1.12-0.86 (m, 2H) |
| I-214[b] | AHM | ABC | 899.4 | 10.98 (s, 1H), 9.40 (s, 1H), 8.84 (d, J = 7.6 Hz, 1H), 8.38 (s, 1H), 8.30 (s, 1H), 7.53 (t, J = 8.0 Hz, 1H), 7.24-6.96 (m, 1H), 6.92 (m, 3H), 5.17-5.10 (m, 1H), 4.22-4.12 (m, 1H), 3.80 (d, J = 2.8 Hz, 4H), 3.73 (d, J = 4.4 Hz, 4H), 3.27-3.25 (m, 1H), 3.19 (t, J = 6.4 Hz, 2H), 3.10-3.01 (m, 2H), 2.89-2.80 (m, 1H), 2.76 (s, 3H), 2.66-2.59 (m, 1H), 2.56 (s, 3H), 2.18-2.09 (m, 1H), 2.07-1.99 (m, 4H), 1.98-1.82 (m, 5H), 1.79-1.61 (m, 7H), 1.54-1.44 (m, 1H), 1.37-1.25 (m, 2H), 1.07-0.94 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-215[b] | AHO | ABC | 886.6 | 11.20 (s, 1H), 9.34 (s, 1H), 8.73 (d, J = 7.6 Hz, 1H), 8.36 (s, 1H), 8.26 (s, 1H), 7.70 (t, J = 8.0 Hz, 1H), 7.19-7.01 (m, 2H), 6.92-6.82 (m, 2H), 5.49-5.32 (m, 1H), 4.86-7.74 (m, 1H), 4.25-4.14 (m, 1H), 3.84-3.78 (m, 8H), 3.58-3.44 (m, 4H), 3.38-3.23 (m, 1H), 3.18-3.06 (m, 1H), 3.04-2.90 (m, 4H), 2.82-2.60 (m, 5H), 2.30-2.22 (m, 1H), 2.15-2.10 (m, 2H), 2.00-1.90 (m, 4H), 1.85-1.75 (m, 4H), 1.21-1.18 (m, 6H) |
| I-216[b] | TN | AGV | 866.4 | 11.08 (s, 1H), 9.78 (s, 1H), 8.94-8.82 (m, 1H), 8.77 (d, J = 8.0 Hz, 1H), 8.24 (d, J = 6.4 Hz, 2H), 7.01-6.95 (m, 2H), 6.91-6.86 (m, 1H), 6.84 (d, J = 8.4 Hz, 1H), 5.47-5.40 (m, 1H), 5.40-5.33 (m, 1H), 4.10-4.02 (m, 1H), 3.88 (s, 4H), 3.72-3.69 (m, 4H), 3.60 (s, 3H), 3.53-3.47 (m, 4H), 3.40-3.34 (m, 1H), 3.07-2.92 (m, 6H), 2.91-2.83 (m, 1H), 2.74-2.57 (m, 2H), 2.19-1.99 (m, 4H), 1.98-1.81 (m, 7H), 1.78-1.59 (m, 3H), 1.46 (s, 6H), 1.26-1.11 (m, 2H) |
| I-217[b] | AGU | AGV | 866.4 | 11.08 (s, 1H), 9.76 (s, 1H), 8.76 (d, J = 8.0 Hz, 1H), 8.23 (s, 1H), 7.59 (dd, J = 7.2, 8.4 Hz, 1H), 7.15 (d, J = 8.8 Hz, 1H), 7.04 (d, J = 6.8 Hz, 1H), 6.84 (d, J = 8.0 Hz, 1H), 6.62 (t, J = 6.0 Hz, 1H), 5.42 (s, 1H), 5.07 (dd, J = 5.2, 12.8 Hz, 1H), 4.04-3.95 (m, 1H), 3.94-3.81 (m, 4H), 3.70 (t, J = 4.8 Hz, 4H), 3.62 (t, J = 4.8 Hz, 2H), 3.48-3.41 (m, 4H), 3.36-3.32 (m, 4H), 2.95-2.82 (m, 1H), 2.65-2.57 (m, 2H), 2.57-2.53 (m, 1H), 2.10-1.97 (m, 7H), 1.90-1.78 (m, 4H), 1.72-1.59 (m, 2H), 1.46 (s, 6H), 1.08-0.95 (m, 2H) |
| I-218[b] | AGB | ABC | 814.2 | 11.09 (s, 1H), 9.39 (s, 1H), 8.82 (d, J = 8.0 Hz, 1H), 8.38 (s, 1H), 8.28 (s, 1H), 7.63-7.54 (m, 1H), 7.24-6.94 (m, 3H), 6.90 (d, J = 8.0 Hz, 1H), 6.25 (d, J = 8.0 Hz, 1H), 5.05 (dd, J = 5.2, 12.8 Hz, 1H), 4.23-4.13 (m, 1H), 3.84-3.76 (m, 4H), 3.75-3.67 (m, 4H), 3.63-3.56 (m, 1H), 2.93-2.83 (m, 1H), 2.80-2.68 (m, 2H), 2.64-2.51 (m, 2H), 2.22-2.09 (m, 4H), 2.08-2.00 (m, 3H), 1.98-1.85 (m, 4H), 1.81-1.68 (m, 2H), 1.65-1.45 (m, 3H), 1.12-0.97 (m, 2H) |
| I-219[b] | PP | AIM | 850.6 | 11.07 (s, 1H), 8.30 (s, 1H), 8.10-7.97 (m, 2H), 7.88 (s, 1H), 7.73 (s, 1H), 7.59 (s, 1H), 7.01-6.91 (m, 2H), 6.90-6.84 (m, 1H), 5.35 (dd, J = 5.2, 12.4 Hz, 1H), 4.50-4.39 (m, 2H), 4.01-3.92 (m, 4H), 3.56 (s, 3H), 3.43-3.42 (m, 4H), 2.99-2.93 (m, 2H), 2.92-2.83 (m, 1H), 2.75-2.66 (m, 1H), 2.65-2.60 (m, 1H), 2.58 (s, 1H), 2.37-2.22 (m, 3H), 2.18-2.13 (m, 1H), 2.13 (s, 3H), 2.11-2.03 (m, 4H), 2.02-1.95 (m, 1H), 1.89-1.77 (m, 4H), 1.71-1.23 (m, 8H), 1.02-0.88 (m, 5H) |
| I-220[b] | AGW | ABC | 842.3 | 11.08 (s, 1H), 9.39 (s, 1H), 8.82 (d, J = 8.0 Hz, 1H), 8.38 (s, 1H), 8.28 (s, 1H), 7.67 (dd, J = 7.2, 8.4 Hz, 1H), 7.36-7.28 (m, 2H), 7.25-6.94 (m, 1H), 6.91 (d, J = 8.0 Hz, 1H), 5.09 (dd, J = 5.2, 12.4 Hz, 1H), 4.25-4.12 (m, 1H), 3.83-3.75 (m, 4H), 3.74-3.70 (m, 4H), 3.39-3.36 (m, 2H), 2.93-2.81 (m, 3H), 2.64-2.53 (m, 2H), 2.28-2.09 (m, 7H), 2.08-1.65 (m, 10H), 1.61-1.50 (m, 1H), 1.39-1.21 (m, 2H), 1.14-0.93 (m, 2H) |
| I-221[b] | AIO | ABC | 842.5 | 11.09 (s, 1H), 9.40 (s, 1H), 8.83 (d, J = 8.0 Hz, 1H), 8.40-8.37 (m, 1H), 8.29 (s, 1H), 7.63-7.54 (m, 1H), 7.26-7.12 (m, 1H), 7.11-6.94 (m, 2H), 6.91 (d, J = 8.0 Hz, 1H), 6.53-6.12 (m, 1H), 5.12-5.00 (m, 1H), 4.25-4.12 (m, 1H), 3.82-3.77 (m, 4H), 3.75-3.70 (m, 4H), 3.54-3.47 (m, 2H), 2.93-2.81 (m, 1H), 2.63-2.53 (m, 2H), 2.27-2.22 (m, 2H), 2.22-2.18 (m, 3H), 2.10-1.97 (m, 5H), 1.95-1.87 (m, 2H), 1.84-1.71 (m, 4H), 1.67-1.57 (m, 1H), 1.53-1.43 (m, 2H), 1.39-1.22 (m, 2H), 1.10-0.92 (m, 2H) |
| I-222[b] | AGY | ABC | 856.5 | 11.09-11.07 (m, 1H), 9.40 (s, 1H), 8.82 (d, J = 8.0 Hz, 1H), 8.41-8.37 (m, 1H), 8.29 (s, 1H), 7.65-7.55 (m, 1H), 7.33-6.95 (m, 3H), 6.91 (d, J = 8.0 Hz, 1H), 5.15-5.00 (m, 1H), 4.23-4.13 (m, 1H), 3.79 (m, 4H), 3.72 (m, 4H), 3.59-3.49 (m, 6H), 2.89-2.81 (m, 2H), 2.62-2.56 (m, 1H), 2.25-2.13 (m, 4H), 2.09-1.68 (m, 12H), 1.53-1.25 (m, 4H), 1.18-0.92 (m, 2H) |
| I-223[b] | AIB | ABC | 856.3 | 11.08 (s, 1H), 9.39 (s, 1H), 8.82 (d, J = 7.6 Hz, 1H), 8.38 (s, 1H), 8.28 (s, 1H), 7.67 (t, J = 7.6 Hz, 1H), 7.37- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 7.29 (m, 2H), 7.25-6.95 (m, 1H), 6.91 (d, J = 7.6 Hz, 1H), 5.13-5.04 (m, 1H), 4.25-4.14 (m, 1H), 3.79 (br s, 4H), 3.74-3.65 (m, 7H), 2.89-2.81 (m, 3H), 2.61 (br d, J = 2.4 Hz, 1H), 2.39-2.33 (m, 2H), 2.18-2.12 (m, 5H), 2.08-1.99 (m, 3H), 1.95-1.87 (m, 2H), 1.82-1.71 (m, 4H), 1.61-1.48 (m, 2H), 1.46-1.32 (m, 4H), 1.11-0.98 (m, 2H) |
| I-224[b] | AIE | ABC | 857.3 | 11.07 (s, 1H), 9.38 (s, 1H), 8.82 (d, J = 8.0 Hz, 1H), 8.37 (s, 1H), 8.17 (s, 1H), 7.69 (dd, J = 7.2, 1H), 7.33-7.21 (m, 2H), 7.03 (t, J = 5.2 Hz, 1H), 6.90 (d, J = 8.1 Hz, 1H), 5.12-5.04 (m, 1H), 4.24-4.13 (m, 1H), 3.78-3.75 (m, 4H), 3.74-3.69 (m, 4H), 3.29-3.20 (m, 8H), 2.60 (br s, 4H), 2.46 (s, 3H), 2.21-2.14 (m, 5H), 2.05-1.97 (m, 3H), 1.94-1.85 (m, 2H), 1.82-1.69 (m, 2H), 1.59-1.50 (m, 1H), 1.11-0.96 (m, 2H) |
| I-225 | AHA | ABC | 871.6 | 11.09 (s, 1H), 9.39 (s, 1H), 8.83 (d, J = 8.0 Hz, 1H), 8.38 (s, 1H), 8.28 (s, 1H), 7.70 (dd, J = 7.2, 8.4 Hz, 1H), 7.35 (dd, J = 6.0, 7.6 Hz, 2H), 7.23-6.94 (m, 1H), 6.91 (d, J = 8.0 Hz, 1H), 5.09 (dd, J = 5.2, 12.8 Hz, 1H), 4.26-4.14 (m, 1H), 3.85-3.76 (m, 4H), 3.75-3.68 (m, 4H), 3.30-3.29 (m, 4H), 2.94-2.78 (m, 1H), 2.63-2.58 (m, 1H), 2.58-2.52 (m, 5H), 2.38 (t, J = 6.8 Hz, 4H), 2.23-2.20 (m, 1H), 2.19 (s, 3H), 2.18-2.16 (m, 1H), 2.08-1.98 (m, 3H), 1.95-1.86 (m, 2H), 1.82-1.69 (m, 2H), 1.67-1.49 (m, 3H), 1.13-0.95 (m, 2H) |
| I-226[b] | AEJ | AGD | 818.5 | 11.09 (s, 1H), 9.39 (s, 1H), 8.82 (d, J = 8.0 Hz, 1H), 8.39 (s, 1H), 8.29 (s, 1H), 7.62-7.55 (m, 1H), 7.24-6.95 (m, 3H), 6.90 (d, J = 8.0 Hz, 1H), 6.67 (t, J = 5.8 Hz, 1H), 5.09-5.01 (m, 1H), 4.24-4.14 (m, 1H), 3.79 (s, 4H), 3.75-3.68 (m, 4H), 3.47 (t, J = 5.8 Hz, 2H), 3.44-3.33 (m, 5H), 2.96-2.82 (m, 3H), 2.62-2.52 (m, 2H), 2.37 (t, J = 7.2 Hz, 2H), 2.09-1.77 (m, 9H), 1.75-1.64 (m, 2H) |
| I-227[b] | AEJ | AGE | 814.2 | 11.08 (s, 1H), 9.40 (s, 1H), 8.82 (d, J = 8.0 Hz, 1H), 8.40 (s, 1H), 8.29 (s, 1H), 7.67 (dd, J = 7.2, 8.4 Hz, 1H), 7.32 (dd, J = 4.8, 7.6 Hz, 2H), 7.26-6.95 (m, 1H), 6.90 (d, J = 8.0 Hz, 1H), 5.09 (dd, J = 5.2, 12.8 Hz, 1H), 4.28-4.17 (m, 1H), 3.81-3.76 (m, 4H), 3.73-3.66 (m, 6H), 2.98 (d, J = 11.2 Hz, 2H), 2.91-2.78 (m, 3H), 2.64-2.51 (m, 2H), 2.39 (t, J = 7.2 Hz, 2H), 2.11-1.88 (m, 7H), 1.84-1.73 (m, 2H), 1.56-1.30 (m, 5H) |
| I-228[b] | AEJ | AGF | 828.3 | 11.08 (s, 1H), 9.40 (s, 1H), 8.82 (d, J = 8.0 Hz, 1H), 8.40 (s, 1H), 8.29 (s, 1H), 7.71-7.60 (m, 1H), 7.32 (t, J = 7.2 Hz, 2H), 7.25-6.95 (m, 1H), 6.90 (d, J = 8.0 Hz, 1H), 5.09 (dd, J = 5.2, 12.8 Hz, 1H), 4.27-4.15 (m, 1H), 3.83-3.76 (m, 4H), 3.74-3.67 (m, 6H), 3.00-2.93 (m, 2H), 2.90-2.79 (m, 3H), 2.64-2.51 (m, 2H), 2.33 (t, J = 7.2 Hz, 2H), 2.10-1.89 (m, 7H), 1.82-1.73 (m, 2H), 1.56-1.24 (m, 7H) |
| I-229[b] | TN | AIM | 862.4 | 11.08 (s, 1H), 8.29 (s, 1H), 8.07-7.99 (m, 2H), 7.89 (s, 1H), 7.73 (s, 1H), 7.59 (s, 1H), 6.96 (d, J = 4.8 Hz, 2H), 6.90-6.83 (m, 1H), 5.36 (dd, J = 5.2, 12.4 Hz, 1H), 4.45 (d, J = 4.0 Hz, 2H), 4.03-3.94 (m, 4H), 3.57 (s, 3H), 3.48-3.44 (m, 3H), 3.01-2.83 (m, 4H), 2.75-2.58 (m, 5H), 2.33-2.24 (m, 1H), 2.18-2.07 (m, 3H), 2.06-1.95 (m, 4H), 1.86-1.76 (m, 6H), 1.67-1.24 (m, 8H), 0.99-0.88 (m, 5H) |
| I-230[b] | QI | AHR | 868.6 | 11.06 (s, 1H), 8.85 (s, 1H), 8.35 (s, 1H), 8.03 (s, 1H), 7.88-7.84 (s, 1H), 7.75 (s, 1H), 7.70-7.68 (m, 1H), 6.99-6.95 (m, 2H), 6.84-6.81 (m, 1H), 5.32 (dd, J = 5.2, 12.8 Hz, 1H), 4.98-4.81 (m, 1H), 4.53 (dd, J = 3.2, 11.2 Hz, 1H), 4.26 (dd, J = 5.6, 11.2 Hz, 1H), 4.12-4.05 (m, 1H), 3.97 (s, 3H), 3.38 (s, 2H), 3.30 (s, 3H), 3.12-3.06 (m, 2H), 2.71-2.56 (m, 4H), 2.34-2.31 (m, 2H), 2.18 (d, J = 7.2 Hz, 2H), 2.13 (s, 3H), 2.03-1.97 (m, 1H), 1.87-1.73 (m, 5H), 1.72-1.52 (m, 10H), 1.46-1.33 (m, 3H), 1.00 (t, J = 7.2 Hz, 3H) |
| I-231[b] | AHD | ABC | 885.6 | 11.08 (s, 1H), 9.39 (s, 1H), 8.83 (d, J = 8.0 Hz, 1H), 8.37 (s, 1H), 8.29 (s, 1H), 7.57 (dd, J = 7.2, 8.4 Hz, 1H), 7.25-6.87 (m, 5H), 5.05 (dd, J = 5.2, 12.8 Hz, 1H), 4.21-4.12 (m, 1H), 3.82-3.76 (m, 4H), 3.74-3.70 (m, 4H), 3.35-3.30 (m, 3H), 2.91-2.81 (m, 3H), 2.62- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | 2.52 (m, 2H), 2.33-2.27 (m, 1H), 2.20 (s, 3H), 2.09-1.99 (m, 5H), 1.93-1.59 (m, 11H), 1.57-1.50 (m, 1H), 1.48-1.38 (m, 2H), 1.08-0.96 (m, 2H) |
| I-232[b] | AGH | ABC | 897.5 | 11.09 (s, 1H), 9.39 (s, 1H), 8.82 (d, J = 7.6 Hz, 1H), 8.37 (s, 1H), 8.29 (s, 1H), 7.58 (t, J = 7.6 Hz, 1H), 7.24-6.95 (m, 3H), 6.91 (d, J = 8.0 Hz, 1H), 6.24 (d, J = 7.6 Hz, 1H), 5.08-5.02 (m, 1H), 4.23-4.12 (m, 1H), 3.79 (s, 4H), 3.72 (s, 4H), 2.93-2.86 (m, 3H), 2.85-2.80 (m, 2H), 2.63-2.53 (m, 2H), 2.35 (d, J = 12.0 Hz, 2H), 2.28-2.21 (m, 1H), 2.10 (d, J = 6.4 Hz, 2H), 2.06-2.00 (m, 3H), 2.00-1.79 (m, 7H), 1.76-1.66 (m, 4H), 1.61-1.53 (m, 1H), 1.50-1.39 (m, 4H), 1.10-0.94 (m, 2H) |
| I-233[b] | AGI | ABC | 855.7 | 11.09 (s, 1H), 9.39 (s, 1H), 8.82 (d, J = 8.0 Hz, 1H), 8.36 (s, 1H), 8.28 (s, 1H), 7.22-6.96 (m, 2H), 6.96-6.89 (m, 3H), 5.41-5.32 (m, 1H), 4.22-4.11 (m, 1H), 3.79 (s, 6H), 3.72 (d, J = 4.4 Hz, 4H), 3.65 (s, 3H), 2.92 (s, 4H), 2.89-2.83 (m, 1H), 2.72-2.60 (m, 2H), 2.23 (s, 3H), 2.12-1.94 (m, 6H), 1.86 (d, J = 11.6 Hz, 2H), 1.77-1.69 (m, 2H), 1.69-1.62 (m, 4H), 1.58-1.49 (m, 1H), 1.09-0.95 (m, 2H) |
| I-234[b] | AHH | AGF | 850.6 | 11.10 (s, 1H), 8.89 (s, 1H), 8.33 (s, 1H), 8.05 (s, 1H), 7.91 (s, 1H), 7.77 (s, 1H), 7.76 (s, 1H), 7.71-7.63 (m, 1H), 7.33 (t, J = 8.0 Hz, 2H), 5.16-5.04 (m, 1H), 5.02-4.81 (m, 1H), 4.62-4.50 (m, 1H), 4.35-4.20 (m, 1H), 4.16-4.04 (m, 1H), 3.98 (s, 3H), 3.73-3.65 (m, 2H), 2.97-2.68 (m, 7H), 2.64-2.54 (m, 2H), 2.33-2.28 (m, 2H), 2.26-2.15 (m, 2H), 2.07-1.99 (m, 1H), 1.98-1.89 (m, 2H), 1.83-1.75 (m, 2H), 1.75-1.65 (m, 2H), 1.64-1.55 (m, 2H), 1.53-1.41 (m, 3H), 1.39-1.24 (m, 4H), 1.05-0.98 (m, 3H) |
| I-235 | AIH | PW | 601.4 | 9.73 (s, 1H), 8.92 (s, 1H), 8.34 (s, 2H), 8.19 (s, 1H), 8.15 (d, J = 5.6 Hz, 1H), 7.30-7.06 (m, 3H), 7.01 (d, J = 5.6 Hz, 1H), 4.27-4.16 (m, 1H), 3.43-3.42 (m, 3H), 3.17 (t, J = 6.0 Hz, 3H), 2.81 (t, J = 7.6 Hz, 2H), 2.72-2.67 (m, 2H), 2.55 (s, 2H), 2.09-2.02 (m, 2H), 1.96-1.88 (m, 2H), 1.80-1.69 (m, 6H), 1.63-1.54 (m, 1H), 1.18-1.01 (m, 3H), 0.48-0.42 (m, 2H), 0.24-0.19 (m, 2H) |
| I-236 | AAA | PW | 854.2 | 11.07 (s, 1H), 9.71 (s, 1H), 8.93 (s, 1H), 8.19 (s, 1H), 8.15 (d, J = 5.2 Hz, 1H), 7.32-7.05 (m, 3H), 7.04-6.98 (m, 1H), 6.92 (d, J = 8.6 Hz, 1H), 6.83 (d, J = 1.8 Hz, 1H), 6.63 (dd, J = 2.0, 8.4 Hz, 1H), 5.33-5.24 (m, 1H), 4.26-4.15 (m, 1H), 3.59 (d, J = 12.0 Hz, 2H), 3.30 (s, 3H), 3.20-3.15 (m, 2H), 2.97-2.68 (m, 1H), 2.65-2.59 (m, 2H), 2.22-2.10 (m, 7H), 2.09-1.87 (m, 6H), 1.85-1.73 (m, 4H), 1.68-1.47 (m, 3H), 1.31-1.17 (m, 2H), 1.12-0.97 (m, 3H), 0.49-0.41 (m, 2H), 0.26-0.18 (m, 2H) |
| I-237 | AAB | WW | 858.5 | 11.07 (s, 1H), 9.69 (s, 1H), 8.91 (s, 1H), 8.22 (s, 2H), 8.15 (d, J = 2.4 Hz, 1H), 7.30-6.95 (m, 7H), 5.36 (dd, J1 = 5.4 Hz, J2 = 12.4 Hz, 1H), 4.17-4.09 (m, 1H), 3.96 (s, 2H), 3.73-3.63 (m, 5H), 3.52-3.51 (m, 2H), 3.20-3.16 (m, 2H), 2.93-2.82 (m, 1H), 2.76 (t, J = 5.4 Hz, 2H), 2.72-2.67 (m, 1H), 2.61 (d, J = 17.2 Hz, 1H), 2.53-2.52 ( m, 2H), 2.21-2.13 (m, 5H), 2.04-1.93 (m, 3H), 1.86 (d, J = 10.4 Hz, 2H), 1.78-1.63 (m, 2H), 1.56-1.44 (m, 1H), 1.12-0.90 (m, 3H), 0.49-0.40 (m, 2H), 0.25-0.18 (m, 2H) |
| I-238 | AER | PW | 952.7 | 11.11 (s, 1H), 9.71 (s, 1H), 8.92 (s, 1H), 8.18 (s, 1H), 8.14 (d, J = 5.2 Hz, 1H), 7.30-7.04 (m, 5H), 7.03-6.98 (m, 2H), 5.36 (dd, J = 4.8, 12.4 Hz, 1H), 4.21-4.20 (m, 1H), 3.90-3.86 (m, 1H), 3.61 (s, 2H), 3.44 (q, J = 6.8 Hz, 2H), 3.33 (s, 3H), 3.28 (t, J = 5.6 Hz, 2H), 3.17 (t, J = 6.0 Hz, 2H), 2.99-2.82 (m, 4H), 2.79-2.60 (m, 3H), 2.05 (s, 3H), 2.04-1.98 (m, 7H), 1.89 (d, J = 12.0 Hz, 2H), 1.81-1.70 (m, 2H), 1.64 (d, J = 12.0 Hz, 2H), 1.55-1.49 (m, 1H), 1.42-1.41 (m, 2H), 1.25-1.14 (m, 2H), 1.05 (t, J = 7.2 Hz, 4H), 1.02-0.96 (m, 1H), 0.54-0.36 (m, 2H), 0.28-0.16 (m, 2H) |
| I-239 | AAD | PW | 854.5 | 11.10 (s, 1H), 9.71 (s, 1H), 8.91 (s, 1H), 8.21 (s, 1H), 8.17 (s, 1H), 8.14 (d, J = 5.6 Hz, 1H), 7.30-6.95 (m, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 7H), 5.35 (dd, J = 5.2, 12.8 Hz, 1H), 4.25-4.12 (m, 1H), 3.61-3.59 (m, 2H), 3.33 (s, 3H), 3.17 (t, J = 6.0 Hz, 2H), 2.96-2.84 (m, 3H), 2.78-2.68 (m, 1H), 2.68-2.63 (m, 1H), 2.63-2.60 (s, 1H), 2.41-2.34 (m, 1H), 2.26 (d, J = 5.6 Hz, 2H), 2.21 (s, 3H), 2.06-2.01 (m, 2H), 2.00-1.93 (m, 2H), 1.89 (d, J = 11.6 Hz, 2H), 1.81-1.69 (m, 2H), 1.65 (d, J = 11.2 Hz, 2H), 1.57-1.38 (m, 3H), 1.11-0.93 (m, 3H), 0.48-0.41 (m, 2H), 0.23-0.20 (m, 2H) |
| I-240 | AAE | PW | 826.3 | 11.08 (s, 1H), 9.68 (s, 1H), 8.91 (s, 1H), 8.18 (s, 1H), 8.15 (s, 1H), 7.31-7.11 (m, 1H), 7.11-7.08 (m, 1H), 7.07-7.04 (m, 1H), 7.03-6.99 (m, 1H), 6.98-6.93 (m, 2H), 5.36 (dd, J = 5.2, 12.8 Hz, 1H), 4.25-4.15 (m, 1H), 3.83 (s, 2H), 3.63 (s, 3H), 3.20-3.16 (m, 4H), 2.97-2.84 (m, 5H), 2.77-2.70 (m, 1H), 2.65-2.58 (m, 2H), 2.07 (s, 2H), 2.03 (s, 3H), 2.02-1.97 (m, 2H), 1.91 (d, J = 10.8 Hz, 2H), 1.81-1.70 (m, 2H), 1.56-1.45 (m, 1H), 1.11-0.94 (m, 3H), 0.49-0.42 (m, 2H), 0.25-0.19 (m, 2H) |
| I-241 | AAG | PW | 874.3 | 11.14 (s, 1H), 9.68 (s, 1H), 8.91 (s, 1H), 8.37 (d, J = 4.8 Hz, 1H), 8.25-8.20 (s, 1H), 8.17 (s, 1H), 8.14 (d, J = 5.2 Hz, 1H), 7.70-7.56 (m, 1H), 7.51 (t, J = 7.6 Hz, 1H), 7.32 (t, J = 7.6 Hz, 1H), 7.29-6.99 (m, 5H), 6.27-5.83 (m, 1H), 4.21-4.15 (m, 1H), 4.04-3.96 (m, 2H), 3.18 (t, J = 6.0 Hz, 2H), 3.10-3.05 (m, 1H), 3.04-2.95 (m, 3H), 2.75-2.68 (m, 1H), 2.39-2.34 (m, 1H), 2.21 (d, J = 6.8 Hz, 2H), 2.18 (s, 3H), 2.16-2.07 (m, 3H), 2.06-1.99 (m, 2H), 1.89 (d, J = 12.0 Hz, 2H), 1.80-1.71 (m, 2H), 1.67 (d, J = 11.2 Hz, 2H), 1.56-1.37 (m, 3H), 1.13-0.91 (m, 3H), 0.49-0.41 (m, 2H), 0.25-0.19 (m, 2H) |
| I-242 | AAI | PW | 842.6 | 11.10 (s, 1H), 9.72 (s, 1H), 8.93 (s, 1H), 8.14 (d, J = 5.2 Hz, 1H), 7.30-6.99 (m, 5H), 6.96 t, J = 7.6 Hz, 1H), 6.92-6.88 (m, 1H), 5.42-5.34 (m, 1H), 4.21-4.13 (m, 1H), 3.68 (s, 3H), 3.65 (s, 2H), 3.17 (t, J = 6.0 Hz, 2H), 2.94-2.84 (m, 1H), 2.76-2.58 (m, 2H), 2.39 (t, J = 6.8 Hz, 2H), 2.26 (t, J = 5.6 Hz, 2H), 2.12 (s, 3H), 2.10 (s, 3H), 2.10-2.06 (m, 2H), 2.04-1.96 (m, 3H), 1.81 (d, J = 11.6 Hz, 2H), 1.76-1.66 (m, 2H), 1.62-1.53 (m, 2H), 1.52-1.42 (m, 1H), 1.10-1.03 (m, 1H), 1.02-0.89 (m, 2H), 0.48-0.42 (m, 2H), 0.25-0.19 (m, 2H) |
| I-243 | AAJ | PW | 826.6 | 11.10 (s, 1H), 9.70 (s, 1H), 8.92 (s, 1H), 8.17 (s, 1H), 8.14 (s, 1H), 7.30-7.03 (m, 5H), 7.01 (d, J = 5.6 Hz, 1H), 6.99-6.95 (m, 1H), 5.39-5.32 (m, 1H), 4.24-4.15 (m, 1H), 3.50 (s, 2H), 3.33 (s, 3H), 3.17 (t, J = 6.0 Hz, 2H), 2.96-2.84 (m, 1H), 2.76-2.68 (m, 1H), 2.65-2.58 (m, 1H), 2.48-2.31 (m, 8H), 2.14 (d, J = 6.4 Hz, 2H), 2.07-1.97 (m, 3H), 1.88 (d, J = 12.4 Hz, 2H), 1.81-1.68 (m, 2H), 1.63-1.50 (m, 1H), 1.10-0.98 (m, 3H), 0.48-0.42 (m, 2H), 0.24-0.19 (m, 2H) |
| I-244 | AAK | PW | 866.4 | 11.10 (s, 1H), 9.69 (s, 1H), 8.92 (s, 1H), 8.18-8.11 (m, 2H), 7.30-7.09 (m, 2H), 7.07-7.04 (m, 1H), 7.01 (d, J = 4.4 Hz, 1H), 6.95 (t, J = 7.6 Hz, 1H), 6.86 (d, J = 7.6 Hz, 1H), 5.37 (dd, J = 4.8, 12.0 Hz, 1H), 4.24-4.12 (m, 1H), 3.66 (s, 3H), 3.58 (s, 2H), 3.21-3.15 (m, 4H), 2.98 (s, 4H), 2.91-2.83 (m, 2H), 2.76-2.69 (m, 3H), 2.65-2.62 (m, 2H), 2.06-1.97 (m, 3H), 1.89-1.81 (m, 2H), 1.78-1.68 (m, 2H), 1.63 (s, 4H), 1.58-1.52 (m, 1H), 1.41-1.31 (m, 1H), 1.14-0.96 (m, 3H), 0.50-0.39 (m, 2H), 0.27-0.18 (m, 2H) |
| I-245 | AAL | PW | 894.3 | 11.09 (s, 1H), 9.68 (s, 1H), 8.92 (s, 1H), 8.17 (s, 1H), 8.15 (d, J = 5.2 Hz, 1H), 7.31-6.98 (m, 5H), 6.95 (t, J = 8.0 Hz, 1H), 6.90-6.84 (m, 1H), 5.42-5.31 (m, 1H), 4.23-4.15 (m, 1H), 3.66 (s, 3H), 3.63 (s, 2H), 3.18 (t, J = 6.0 Hz, 2H), 2.94-2.84 (m, 1H), 2.78-2.68 (m, 1H), 2.65-2.58 (1H), 2.43-2.33 (m, 8H), 2.18 (d, J = 6.4 Hz, 2H), 2.07-1.98 (m, 3H), 1.88 (d, J = 12.0 Hz, 2H), 1.80-1.69 (m, 2H), 1.63-1.54 (m, 1H), 1.51-1.28 (m, 8H), 1.12-0.97 (m, 3H), 0.50-0.40 (m, 2H), 0.26-0.18 (m, 2H) |
| I-246 | ADC | PW | 871.6 | 9.67 (s, 1H), 8.91 (s, 1H), 8.18-8.12 (m, 2H), 7.29-7.04 (m, 3H), 7.01 (dd, J = 1.6, 5.2 Hz, 1H), 6.98-6.92 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | (m, 2H), 6.89-6.85 (m, 1H), 5.42 (dd, J = 5.2, 12.0 Hz, 1H), 4.24-4.14 (m, 1H), 3.57 (s, 3H), 3.42 (t, J = 6.4 Hz, 4H), 3.18 (t, J = 6.4 Hz, 2H), 3.02 (s, 3H), 2.98-2.94 (m, 2H), 2.81-2.68 (m, 2H), 2.37 (t, J = 7.2 Hz, 2H), 2.18-2.11 (m, 5H), 2.08-1.61 (m, 12H), 1.59-1.48 (m, 1H), 1.11-0.96 (m, 3H), 0.48-0.42 (m, 2H), 0.25-0.19 (m, 2H) |
| I-247 | AAM | PW | 868.3 | 9.68 (s, 1H), 8.91 (s, 1H), 8.17 (s, 1H), 8.14 (d, J = 5.2 Hz, 1H), 7.29-7.00 (m, 5H), 6.94 (t, J = 7.6 Hz, 1H), 6.90-6.84 (m, 1H), 5.44 (dd, J = 5.2, 12.8 Hz, 1H), 4.24-4.12 (m, 1H), 3.68 (s, 3H), 3.62 (s, 2H), 3.18 (t, J = 6.0 Hz, 2H), 3.04 (s, 3H), 2.99-2.92 (m, 1H), 2.87 (d, J = 10.0 Hz, 2H), 2.82-2.69 (m, 2H), 2.40-2.35 (m, 1H), 2.24 (d, J = 6.8 Hz, 2H), 2.19 (s, 3H), 2.06-1.93 (m, 5H), 1.88 (d, J = 11.2 Hz, 2H), 1.80-1.70 (m, 2H), 1.65 (d, J = 10.8 Hz, 2H), 1.54-1.45 (m, 1H), 1.44-1.34 (m, 2H), 1.11-0.96 (m, 3H), 0.49-0.41 (m, 2H), 0.26-0.18 (m, 2H) |
| I-248[b] | ACD | ACA | 938.4 | 11.09 (s, 1H), 9.69 (s, 1H), 8.92 (s, 1H), 8.19-8.11 (m, 2H), 7.31-6.99 (m, 5H), 6.95 (t, J = 7.6 Hz, 1H), 6.87 (d, J = 7.6 Hz, 1H), 5.37 (dd, J = 5.2, 12.4 Hz, 1H), 4.26-4.12 (m, 1H), 3.67 (s, 3H), 3.61 (s, 2H), 3.25-3.12 (m, 4H), 2.88 (d, J = 11.2 Hz, 2H), 2.77-2.58 (m, 3H), 2.26-2.09 (m, 4H), 2.09-1.83 (m, 8H), 1.82-1.70 (m, 4H), 1.64 (d, J = 11.6 Hz, 4H), 1.54-1.29 (m, 4H), 1.23-1.15 (m, 2H), 1.10-0.96 (m, 3H), 0.51-0.39 (m, 2H), 0.26-0.18 (m, 2H) |
| I-249[b] | AAO | PW | 924.6 | 11.10 (s, 1H), 9.72 (s, 1H), 8.92 (s, 1H), 8.20 (s, 1H), 8.15 (d, J = 52 Hz, 1H), 7.32-6.85 (m, 7H), 5.44-5.33 (m, 1H), 4.28-4.16 (m, 2H), 3.95-3.84 (m, 1H), 3.73-3.57 (m, 5H), 3.35-3.33 (m, 3H), 3.18 (t, J = 6.0 Hz, 2H), 2.97-2.79 (m, 3H), 2.72-2.69 (m, 4H), 2.61 (m, 1H), 2.52 (s, 3H), 2.29-2.19 (m, 2H), 2.16-1.96 (m, 6H), 1.91-1.73 (m, 6H), 1.46-1.37 (m, 1H), 1.26-1.02 (m, 3H), 0.49-0.41 (m, 2H), 0.25-0.19 (m, 2H) |
| I-250 | AAP | PW | 840.5 | 11.09 (s, 1H), 9.70 (s, 1H), 8.92 (s, 1H), 8.34-8.22 (m, 1H), 8.18 (s, 1H), 8.16-8.12 (m, 1H), 7.31-6.86 (m, 7H), 5.39-5.32 (m, 1H), 4.24-4.15 (m, 1H), 3.56 (s, 3H), 3.43 (s, 2H), 3.18 (s, 2H), 2.89 (d, J = 7.6 Hz, 4H), 2.76-2.58 (m, 7H), 2.08-2.01 (m, 2H), 1.99 (s, 3H), 1.97-1.86 (m, 4H), 1.81-1.68 (m, 2H), 1.05 (s, 4H), 0.49-0.41 (m, 2H), 0.25-0.18 (m, 2H) |
| I-251[b] | TN | ACF | 773.5 | 11.10 (s, 1H), 10.04 (s, 1H), 9.37 (dd, J = 1.2, 6.8 Hz, 1H), 8.86 (dd, J = 1.2, 4.0 Hz, 1H), 8.70 (s, 1H), 8.37 (s, 1H), 7.35-7.26 (m, 1H), 7.14 (s, 1H), 7.03-6.93 (m, 2H), 6.89-6.82 (m, 1H), 5.41-5.32 (m, 1H), 4.36-4.07 (m, 1H), 3.57 (s, 3H), 3.44 (t, J = 6.0 Hz, 2H), 3.30-3.25 (m, 1H), 2.99-2.84 (m, 3H), 2.77-2.70 (m, 1H), 2.69-2.60 (m, 3H), 2.14-1.98 (m, 7H), 1.90-1.72 (m, 8H), 1.62-1.55 (m, 1H), 1.50-1.42 (m, 2H), 1.09-0.97 (m, 2H) |
| I-252 | SX | PW | 953.6 | 11.11 (s, 1H), 9.73 (s, 1H), 8.92 (s, 1H), 8.17-8.11 (m, 2H), 7.32-6.98 (m, 7H), 5.37 (dd, J = 5.2, 12.8 Hz, 1H), 4.25-4.18 (m, 1H), 4.03-3.96 (m, 2H), 3.66 (s, 3H), 3.47-3.44 (m, 5H), 3.34 (s, 3H), 3.20-3.15 (m, 3H), 2.96-2.88 (m, 2H), 2.77-2.63 (m, 7H), 2.32 (s, 3H), 2.26-1.97 (m, 8H), 1.90 (d, J = 12.4 Hz, 2H), 1.84-1.72 (m, 2H), 1.66 (s, 1H), 1.17-0.99 (m, 3H), 0.48-0.41 (m, 2H), 0.25-0.18 (m, 2H) |
| I-253[b] | AAX | WW | 854.5 | 11.10 (s, 1H), 9.71 (s, 1H), 8.92 (s, 1H), 8.27 (s, 1H), 8.14 (d, J = 5.2 Hz, 1H), 7.31-7.11 (m, 1H), 7.10-7.06 (m, 2H), 7.03-6.99 (m, 1H), 6.95 (t, J = 7.6 Hz, 1H), 6.87 (d, J = 7.9 Hz, 1H), 5.37 (dd, J = 5.6, 13.2 Hz, 1H), 4.25-4.17 (m, 1H), 3.67 (s, 3H), 3.60 (s, 2H), 3.20-3.15 (m, 3H), 2.98-2.78 (m, 6H), 2.77-2.69 (m, 1H), 2.66-2.55 (m, 3H), 2.27 (t, J = 7.6 Hz, 2H), 2.07-1.86 (m, 9H), 1.62 (d, J = 12.0 Hz, 2H), 1.48-1.37 (m, 2H), 1.27-1.14 (m, 3H), 0.50-0.40 (m, 2H), 0.28-0.17 (m, 2H) |
| I-254[b] | AAX | SK | 854.3 | 11.10 (s, 1H), 9.73 (s, 1H), 8.92 (s, 1H), 8.19 (s, 1H), 8.14 (d, J = 5.2 Hz, 1H), 7.30-7.12 (m, 1H), 7.11-7.07 (m, 2H), 7.05-6.99 (m, 2H), 6.99-6.95 (m, 1H), |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | 5.36 (dd, J = 5.2, 12.8 Hz, 1H), 4.26-4.20 (m, 1H), 3.53 (s, 2H), 3.33 (s, 3H), 3.17 (t, J = 6.0 Hz, 2H), 3.02-2.81 (m, 5H), 2.68 (s, 1H), 2.65-2.56 (m, 1H), 2.53-2.52 (m, 1H), 2.30 (s, 1H), 2.13-1.87 (m, 10H), 1.63 (d, J = 11.2 Hz, 2H), 1.45 (s, 2H), 1.26-1.10 (m, 5H), 1.10-1.01 (m, 1H), 0.49-0.39 (m, 2H), 0.30-0.22 (m, 2H) |
| I-255 | AAZ | SK | 868.6 | 11.18-11.03 (m, 1H), 9.73 (s, 1H), 8.91 (s, 1H), 8.18-8.12 (m, 2H), 7.30-7.03 (m, 5H), 7.03-6.96 (m, 2H), 5.35 (dd, J = 5.2, 12.8 Hz, 1H), 4.56-4.45 (m, 2H), 3.98 (d, J = 12 Hz, 2H), 3.33 (s, 3H), 3.19-3.15 (m, 3H), 2.93-2.81 (m, 4H), 2.37-2.32 (m, 2H), 2.09-1.62 (m, 11H), 1.49-1.40 (m, 2H), 1.32-1.01 (m, 5H), 0.48-0.40 (m, 2H), 0.24-0.16 (m, 2H) |
| I-256 | ABA | PW | 924.6 | 11.12 (s, 1H), 9.71 (s, 1H), 8.93 (s, 1H), 8.17 (s, 1H), 8.14 (d, J = 5.2 Hz, 1H), 7.32-6.82 (m, 7H), 5.40-5.36 (m, 1H), 4.23-4.14 (m, 1H), 3.67 (s, 3H), 3.60 (s, 2H), 3.42-3.40 (m, 3H), 3.17 (t, J = 6.2 Hz, 2H), 2.96-2.82 (m, 1H), 2.77-2.57 (m, 6H), 2.15 (d, J = 6.8 Hz, 2H), 2.12-2.07 (m, 2H), 2.03 (d, J = 9.2 Hz, 4H), 1.88 (d, J = 11.2 Hz, 2H), 1.82-1.66 (m, 6H), 1.65-1.28 (m, 5H), 1.14-0.93 (m, 3H), 0.50-0.40 (m, 2H), 0.27-0.17 (m, 2H) |
| I-257[b] | TN | ABC | 858.5 | 11.11 (s, 1H), 9.40 (s, 1H), 8.83 (d, J = 8.0 Hz, 1H), 8.38 (s, 1H), 8.30 (s, 1H), 7.24-6.95 (m, 3H), 6.93-6.86 (m, 2H), 5.44-5.32 (m, 1H), 4.22-4.13 (m, 1H), 3.82-3.77 (m, 4H), 3.75-3.70 (m, 4H), 3.58 (s, 3H), 3.47.3.44 (m, 2H), 3.29-3.27 (m, 1H), 3.00-2.94 (m, 2H), 2.92-2.84 (m, 1H), 2.77-2.70 (m, 1H), 2.67-2.59 (m, 3H), 2.16-2.10 (m, 2H), 2.08-1.97 (m, 5H), 1.91-1.79 (m, 6H), 1.78-1.67 (m, 2H), 1.61-1.52 (m, 1H), 1.51-1.40 (m, 2H), 1.11-0.93 (m, 2H) |
| I-258[b] | TN | ACH | 871.6 | 11.78 (s, 1H), 11.09 (s, 1H), 10.43 (s, 1H), 9.33 (s, 1H), 8.93 (d, J = 7.6 Hz, 1H), 8.40 (s, 1H), 8.34 (s, 1H), 7.31-6.93 (m, 4H), 6.91-6.84 (m, 1H), 5.48-5.34 (m, 1H), 4.88-4.54 (m, 2H), 4.31-4.16 (m, 1H), 3.73 (s, 3H), 3.70-3.62 (m, 2H), 3.60-3.57 (m, 2H), 3.52-3.47 (m, 4H), 3.36-3.28 (m, 1H), 3.22-3.10 (m, 2H), 3.05-2.85 (m, 7H), 2.80 (d, J = 3.2 Hz, 3H), 2.75-2.67 (m, 1H), 2.66-2.58 (m, 1H), 2.22-2.12 (m, 1H), 2.10-1.97 (m, 6H), 1.94-1.72 (m, 7H), 1.26-1.12 (m, 2H) |
| I-259[b] | PP | ABC | 846.5 | 11.07 (s, 1H), 9.39 (s, 1H), 8.81 (d, J = 8.0 Hz, 1H), 8.37 (s, 1H), 8.28 (s, 1H), 7.24-6.82 (m, 5H), 5.36 (dd, J = 5.2, 12.4 Hz, 1H), 4.21-4.12 (m, 1H), 3.82-3.76 (m, 4H), 3.74-3.70 (m, 4H), 3.56 (s, 3H), 3.44-3.38 (m, 4H), 2.99-2.82 (m, 3H), 2.75-2.58 (m, 2H), 2.38-2.31 (m, 2H), 2.16-2.08 (m, 5H), 2.07-1.94 (m, 3H), 1.91-1.60 (m, 8H), 1.57-1.45 (m, 1H), 1.12-0.90 (m, 2H) |
| I-260[b] | PP | ACH | 859.6 | 11.07 (s, 1H), 9.40 (s, 1H), 8.78 (d, J = 8.0 Hz, 1H), 8.38 (s, 1H), 8.27 (s, 1H), 7.24-6.93 (m, 3H), 6.93-6.84 (m, 2H), 5.36 (d, J = 12.8 Hz, 1H), 4.24-4.12 (m, 3H), 3.80 (s, 5H), 3.57 (s, 3H), 3.42 (d, J = 6.0 Hz, 4H), 3.00-2.92 (m, 2H), 2.87 (d, J = 12.8 Hz, 1H), 2.76-2.57 (m, 3H), 2.43 (d, J = 5.2 Hz, 5H), 2.25 (s, 3H), 2.19 (s, 4H), 2.09-1.95 (m, 3H), 1.94-1.79 (m, 4H), 1.77-1.64 (m, 3H), 1.13-0.96 (m, 2H) |
| I-261[b] | AAY | ABF | 843.5 | 11.10 (s, 1H), 9.74 (s, 1H), 8.92 (s, 1H), 8.20-8.18 (m, 1H), 8.14 (d, J = 5.2 Hz, 1H), 7.31-7.06 (m, 3H), 7.05-6.97 (m, 3H), 6.86 (d, J = 8.0 Hz, 1H), 5.33 (dd, J = 5.2, 12.8 Hz, 1H), 4.29-4.20 (m, 1H), 3.40-3.28 (m, 7H), 3.17 (1. J = 6.0 Hz, 2H), 3.03-2.84 (m, 3H), 2.75-2.59 (m, 4H), 2.36 (t, J = 7.2 Hz, 2H), 2.16-2.06 (m, 2H), 2.04-1.88 (m, 5H), 1.86-1.74 (m, 2H), 1.58-1.40 (m, 4H), 1.37-1.24 (m, 2H), 1.12-0.99 (m, 1H), 0.50-0.39 (m, 2H), 0.27-0.16 (m, 2H) |
| I-262[b] | AAY | ABG | 843.4 | 11.86 (s, 1H), 9.72 (s, 1H), 8.93 (s, 1H), 8.20 (s, 1H), 8.15 (d, J = 5.6 Hz, 1H), 7.33-7.00 (m, 4H), 6.97 (d, J = 4.8 Hz, 2H), 6.91-6.85 (m, 1H), 5.37 (dd, J = 5.2, 12.4 Hz, 1H), 4.26-4.19 (m, 1H), 3.57 (s, 3H), 3.45-3.41 (m, 2H), 3.39 (t, J = 6.4 Hz, 2H), 3.21-3.17 (m, 2H), 3.01-2.92 (m, 4H), 2.91-2.83 (m, 1H), 2.76- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-263[b] | ABJ | WW | 812.5 | 2.68 (m, 1H), 2.65-2.59 (m, 1H), 2.34-2.29 (m, 2H), 2.08-1.90 (m, 7H), 1.87-1.79 (m, 2H), 1.59-1.51 (m, 2H), 1.50-1.41 (m, 2H), 1.39-1.31 (m, 2H), 1.12-1.02 (m, 1H), 0.51-0.38 (m, 2H), 0.30-0.16 (m, 2H) 11.10 (s, 1H), 9.74 (s, 1H), 8.93 (s, 1H), 8.18-8.13 (m, 2H), 7.34-7.04 (m, 4H), 7.01 (d, J = 5.2 Hz, 1H), 6.98-6.92 (m, 1H), 6.88-6.84 (m, 1H), 5.41-5.32 (m, 1H), 5.08-5.00 (m, 1H), 3.70-3.67 (m, 1H), 3.67 (s, 3H), 3.65-3.63 (m, 1H), 3.60 (s, 2H), 3.33-3.29 (m, 2H), 3.19-3.16 (m, 2H), 2.94-2.87 (m, 1H), 2.83-2.77 (m, 2H), 2.73-2.60 (m, 4H), 2.06-1.99 (m, 1H), 1.99-1.90 (m, 2H), 1.66-1.57 (m, 2H), 1.38-1.27 (m, 1H), 1.27-1.18 (m, 2H), 1.14-1.02 (m, 3H), 0.48-0.41 (m, 2H), 0.24-0.19 (m, 2H) |
| I-264[b] | AEL | WW | 840.6 | 11.09 (s, 1H), 9.70 (s, 1H), 8.91 (s, 1H), 8.19 (s, 1H), 8.15 (d, J = 5.6 Hz, 1H), 7.31-7.04 (m, 4H), 7.03-7.00 (m, 1H), 6.95 (t, J = 7.8 Hz, 1H), 6.87 (d, J = 7.2 Hz, 1H), 5.37 (dd, J = 5.2, 12.8 Hz, 1H), 4.28-4.18 (m, 1H), 3.67 (s, 3H), 3.61 (s, 2H), 3.20-3.16 (m, 2H), 3.01-2.94 (m, 2H), 2.93-2.85 (m, 1H), 2.85-2.77 (m, 2H), 2.77-2.69 (m, 1H), 2.65-2.60 (m, 1H), 2.52-2.51 (m, 1H), 2.39-2.33 (m, 2H), 2.11-2.07 (m, 1H), 2.07-2.03 (m, 1H), 2.03-2.00 (m, 1H), 2.00-1.97 (m, 2H), 1.97-1.93 (m, 2H), 1.93-1.87 (m, 1H), 1.69-1.57 (m, 2H), 1.42-1.24 (m, 3H), 1.18-1.01 (m, 3H), 0.51-0.40 (m, 2H), 0.26-0.17 (m, 2H) |
| I-265[b] | ACX | WW | 826.5 | 11.10 (s, 1H), 9.71 (s, 1H), 8.92 (s, 1H), 8.19 (s, 1H), 8.15 (d, J = 5.4 Hz, 1H), 7.30-7.04 (m, 4H), 7.01 (dd, J = 5.4 Hz, 1H), 6.95 (t, J = 7.6 Hz, 1H), 6.87 (d, J = 7.6 Hz, 1H), 5.38 (dd, J = 5.4, 1H), 4.27-4.19 (m, 1H), 3.67 (s, 3H), 3.62 (s, 2H), 3.19-3.16 (m, 2H), 2.91 (d, J = 11.6 Hz, 3H), 2.86-2.79 (m, 2H), 2.76-2.68 (m, 1H), 2.65-2.58 (m, 1H), 2.15 (d, J = 6.4 Hz, 2H), 2.05-1.89 (m, 9H), 1.74-1.62 (m, 2H), 1.58-1.46 (m, 1H), 1.14-0.98 (m, 3H), 0.48-0.42 (m, 2H), 0.25-0.19 (m, 2H) |
| I-266 | ABL | PW | 868.2 | 11.12 (s, 1H), 9.68 (s, 1H), 8.91 (s, 1H), 8.19 (s, 1H), 8.14 (d, J = 5.2 Hz, 1H), 7.31-6.88 (m, 7H), 5.44-5.40 (m, 1H), 4.61 (t, J = 11.2 Hz, 1H), 4.23-4.16 (m, 11.6 Hz, 1H), 3.60 (d, J = 2.8 Hz, 2H), 3.31 (s, 3H), 3.21 (s, 2H), 3.18 (t, J = 6.0 Hz, 2H), 3.05-2.99 (m, 1H), 2.95-2.87 (m, 1H), 2.85-2.82 (m, 1H), 2.79-2.69 (m, 1H), 2.63-2.58 (m, 1H), 2.25 (d, J = 7.2 Hz, 1H), 2.22-2.17 (m, 3H), 2.06-2.02 (m, 2H), 1.95-1.86 (m, 2H), 1.85-1.68 (m, 3H), 1.62 (d, J = 11.2 Hz, 1H), 1.53-1.22 (m, 3H), 1.13-0.92 (m, 3H), 0.49-0.40 (m, 2H), 0.26-0.17 (m, 2H) |
| I-267[b] | TN | ABD | 850.2 | 11.10 (s, 1H), 9.87 (s, 1H), 8.52 (d, J = 7.6 Hz, 1H), 8.23 (s, 1H), 8.13 (s, 1H), 6.97 (d, J = 4.8 Hz, 2H), 6.91-6.85 (m, 1H), 6.41 (d, J = 7.6 Hz, 1H), 5.37 (d, J = 9.2 Hz, 1H), 5.32 (s, 1H), 4.05-3.93 (m, 1H), 3.57 (s, 3H), 3.53-3.43 (m, 6H), 3.01-2.93 (m, 2H), 2.92-2.84 (m, 1H), 2.77-2.58 (m, 6H), 2.10 (d, J = 6.8 Hz, 2H), 2.05-1.97 (m, 5H), 1.91-1.77 (m, 7H), 1.49 (s, 6H), 1.46-1.39 (m, 2H), 1.10-0.96 (m, 3H), 0.54-0.47 (m, 2H), 0.32-0.26 (m, 2H) |
| I-268[b] | WX | ABD | 835.2 | 11.11 (s, 1H), 9.86 (s, 1H), 8.51 (d, J = 7.6 Hz, 1H), 8.22 (s, 1H), 8.18 (s, 1H), 7.07 (d, J = 7.6 Hz, 1H), 6.96 (d, J = 7.6 Hz, 1H), 6.86 (d, J = 7.6 Hz, 1H), 6.41 (d, J = 7.6 Hz, 1H), 5.38 (d, J = 9.2 Hz, 1H), 5.31 (s, 1H), 4.02-3.93 (m, 1H), 3.67 (s, 4H), 3.61 (s, 2H), 3.54-3.47 (m, 3H), 2.87 (d, J = 10.0 Hz, 3H), 2.78-2.58 (m, 2H), 2.22 (d, J = 6.8 Hz, 2H), 2.18 (s, 3H), 2.05-1.92 (m, 5H), 1.86 (d, J = 11.2 Hz, 2H), 1.72-1.58 (m, 4H), 1.48 (s, 6H), 1.46-1.31 (m, 3H), 1.09-0.92 (m, 3H), 0.54-0.47 (m, 2H), 0.31-0.25 (m, 2H) |
| I-269[b] | ADG | ADI | 708.5 | 11.09 (s, 1H), 8.44 (s, 1H), 8.18(s, 1H), 8.01 (d, J = 7.6 Hz, 1H), 7.74-7.66 (m, 2H), 6.99-6.92 (m, 2H), 6.90-6.83 (m, 1H), 5.40-5.33 (m, 1H), 4.16 (s, 2H), 4.13 (s, 1H), 3.56 (s, 3H), 3.45-3.37 (m, 4H), 3.02-2.93 (m, 2H), 2.92-2.81 (m, 1H), 2.77-2.61 (m, 2H), 2.58 (s, 4H), 2.42-2.29 (m, 7H), 2.06-1.98 (m, 3H), 1.89 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | (d, J = 10.4 Hz, 2H), 1.85-1.78 (m, 2H), 1.71-1.63 (m, 2H), 1.49-1.33 (m, 4H) |
| I-270[b] | AHG | WW | 637.4 | — |
| I-271[b, e] | ADL | ADJ | 709.5 | 11.08 (s, 1H), 9.16-8.84 (m, 1H), 8.55 (s, 1H), 8.32-8.10 (m, 1H), 8.09-7.71 (m, 2H), 7.10-6.82 (m, 3H), 5.35 (dd, J = 4.8, 12.4 Hz, 1H), 4.36-4.04 (m, 1H), 3.56 (s, 3H), 3.46-3.41 (m, 6H), 2.95 (t, J = 7.2 Hz, 2H), 2.90-2.80 (m, 2H), 2.78-2.68 (m, 2H), 2.65-2.57 (m, 2H), 2.31-2.17 (m, 2H), 2.15-2.08 (m, 1H), 2.04-1.96 (m, 2H), 1.91-1.78 (m, 7H), 1.76-1.69 (m, 2H), 1.67-1.59 (m, 1H), 1.56-1.48 (m, 1H), 1.46-1.34 (m, 4H) |
| I-272[b] | ABT | ADN | 788.2 | 13.14 (s, 1H), 11.08 (s, 1H), 9.38 (dd, J = 1.6, 7.2 Hz, 1H), 9.13 (dd, J = 1.6, 4.4 Hz, 1H), 8.73 (s, 1H), 8.51 (s, 1H), 7.88-7.76 (m, 2H), 7.37 (dd, J = 4.4, 7.2 Hz, 1H), 6.96 (d, J = 4.4 Hz, 2H), 6.91-6.84 (m, 2H), 5.36 (dd, J = 5.2, 12.4 Hz, 1H), 3.56 (s, 3H), 3.44-3.36 (m, 4H), 3.06-2.81 (m, 5H), 3.06-2.81 (m, 1H), 2.64-2.57 (m, 1H), 2.54-2.51 (m, 1H), 2.40 (s, 3H), 2.39-2.36 (m, 2H), 2.13 (t, J = 10.8 Hz, 2H), 2.02-1.92 (m, 3H), 1.87-1.79 (m, 2H), 1.76-1.66 (m, 2H), 1.58-1.46 (m, 4H), 1.39-1.29 (m, 2H) |
| I-273[b] | AND | ABF | 788.5 | 13.14 (s, 1H), 11.08 (s, 1H), 9.37 (dd, J = 1.6. 7.2 Hz, 1H), 9.13 (dd, J = 1.6, 4.4 Hz, 1H), 8.73 (s, 1H), 8.50 (s, 1H), 7.88-7.74 (m, 2H), 7.36 (dd, J = 4.4. 7.2 Hz, 1H), 7.09-6.96 (m, 2H), 6.92-6.83 (m, 2H), 5.33 (dd, J = 5.2, 12.8 Hz, 1H), 3.36 (t, J = 6.4 Hz, 4H), 3.32 (s, 3H), 3.03-2.95 (m, 2H), 2.94-2.83 (m, 1H), 2.74-2.62 (m, 3H), 2.41-2.32 (m, 6H), 2.16-2.06 (m, 2H), 2.03-1.90 (m, 3H), 1.87-1.63 (m, 5H), 1.56-1.15 (m, 4H), 1.37-1.29 (m, 2H) |
| I-274[f] | QG | PW | 1186.6 | 9.70 (s, 1H), 8.92 (s, 1H), 8.48 (s, 1H), 8.26 (s, 2H), 8.18 (s, 1H), 8.14 (d, J = 5.6 Hz, 1H), 7.98 (d, J = 8.4 Hz, 1H), 7.68 (d, J = 7.6 Hz, 1H), 7.64 (d, J = 2.4 Hz, 1H), 7.46 (t, J = 8.0 Hz, 1H), 7.31-7.08 (m, 4H), 7.08-6.98 (m, 2H), 5.39 (dd, J = 3.2, 8.0 Hz, 1H), 4.51-4.49 (m, 1H), 4.18-4.15 (m, 2H), 3.82-3.76 (m, 6H), 3.62-3.59 (m, 10H), 3.19-3.17 (m, 2H), 3.06-3.04 (m, 1H), 2.79-2.77 (m, 2H), 2.20 (s, 3H), 2.07 (s, 4H), 2.05-2.03 (m, 4H), 1.93-1.86 (m, 2H), 1.80-1.49 (m, 11H), 1.13 (s, 3H), 0.99 (m, 7H), 0.94 (m, 1H), 0.47-0.42 (m, 2H), 0.24-0.20 (m, 2H) |
| I-317[b] | AGW | AGL | 843.5 | 12.36 (s, 1H), 11.08 (s, 1H), 8.71 (s, 1H), 8.48-8.42 (m, 1H), 8.40-8.31 (m, 2H), 8.16 (d, J = 7.6 Hz, 1H), 7.71-7.63 (m, 1H), 7.57 (s, 1H), 7.38-7.27 (m, 2H), 5.94 (s, 1H), 5.09 (dd, J = 5.6, 12.8 Hz, 1H), 4.50-4.35 (m, 1H), 3.78-3.59 (m, 2H), 2.97-2.79 (m, 3H), 2.63-2.53 (m, 2H), 2.24-1.80 (m, 16H), 1.76-1.63 (m, 2H), 1.62 (s, 6H), 1.39-1.25 (m, 2H), 1.18-1.05 (m, 2H) |
| I-318[b] | ANY | AJB | 933.5 | 11.16-11.02 (m, 1H), 9.49 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.48 (dd, J = 7.2, 8.4 Hz, 1H), 7.34-7.29 (m, 2H), 7.28-7.09 (m, 4H), 7.02-6.94 (m, 2H), 6.88-6.43 (m, 1H), 5.30-5.02 (m, 2H), 4.76 (d, J = 17.6 Hz, 1H), 4.53 (d, J = 6.0 Hz, 2H), 4.15 (t, J = 2.4, 11.6 Hz, 1H), 3.80 (s, 1H), 3.74 (d, J = 7.6 Hz, 1H), 3.65-3.57 (m, 2H), 3.45 (s, 3H), 2.95-2.88 (m, 1H), 2.62-2.55 (m, 1H), 2.41 (s, 4H), 2.12 (s, 6H), 2.10-2.07 (m, 2H), 2.05-1.97 (m, 5H), 1.85 (br d, J = 11.2 Hz, 2H), 1.76-1.66 (m, 2H), 1.54-1.43 (m, 1H), 1.04-0.91 (m, 2H) |
| I-320[b] | AMC | AMT | 866.4 | 11.12-10.99 (m, 1H), 9.63-9.55 (m, 1H), 8.94 (d, J = 3.2 Hz, 1H), 8.80 (d, J = 7.6 Hz, 1H), 8.30 (d, J = 5.6 Hz, 1H), 7.75 (d, J = 8.4 Hz, 2H), 7.56-7.50 (m, 1H), 7.42 (d, J = 8.4 Hz, 2H), 7.29-7.11 (m, 1H), 7.02 (d, J = 8.4 Hz, 1H), 6.98 (d, J = 7.2 Hz, 1H), 6.91-6.45 (m, 2H), 5.32-5.07 (m, 1H), 5.06-4.97 (m, 1H), 4.83-4.74 (m, 1H), 3.87-3.73 (m, 2H), 3.68-3.60 (m, 2H), 3.47 (s, 2H), 3.45 (s, 1H), 3.44 (s, 1H), 3.42 (s, 1H), |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 3.41 (s, 1H), 3.40 (s, 1H), 2.92-2.80 (m, 2H), 2.57 (d, J = 2.0 Hz, 1H), 2.39 (t, J = 7.0 Hz, 2H), 2.12 (s, 3H), 2.09-1.93 (m, 4H), 1.80-1.75 (m, 2H), 1.75-1.69 (m, 2H) |
| I-321[b] | AQN | AQM | 888.5 | 11.31-10.74 (m, 1H), 9.50 (d, J = 5.6 Hz, 1H), 8.78 (d, J = 7.6 Hz, 1H), 8.41-8.32 (m, 1H), 8.25 (d, J = 5.6 Hz, 1H), 7.62-7.52 (m, 1H), 7.26-6.94 (m, 3H), 6.89-6.39 (m, 2H), 5.29-5.00 (m, 2H), 4.77 (d, J = 16.0 Hz, 1H), 4.25-4.06 (m, 1H), 4.02-3.84 (m, 1H), 3.84-3.71 (m, 2H), 3.70-3.42 (m, 4H), 3.19-3.10 (m, 2H), 2.96-2.79 (m, 4H), 2.62-2.55 (m, 2H), 2.13-1.80 (m, 10H), 1.25-0.87 (m, 11H) |
| I-322[b] | AOC | ABC | 920.2 | 9.39 (s, 1H), 8.82 (d, J = 7.9 Hz, 1H), 8.37 (s, 1H), 8.28 (s, 1H), 7.52-7.46 (m, 1H), 7.43 (d, J = 8.0 Hz, 2H), 7.36-7.28 (m, 4H), 7.24-6.94 (m, 1H), 6.90 (d, J = 7.6 Hz, 1H), 5.25-5.20 (m, 2H), 5.20-5.15 (m, 1H), 4.44-4.37(m, 1H), 4.28-4.22 (m, 1H), 4.21-4.11 (m, 1H), 3.79 (s, 4H), 3.74-3.68 (m, 4H), 3.45 (s, 2H), 3.03-2.93 (m, 4H), 2.78-2.69 (m, 1H), 2.53-2.51 (m, 1H), 2.48-2.34 (m, 8H), 2.10 (d, J = 6.8 Hz, 2H), 2.06-1.94 (m, 3H), 1.87 (d, J = 12.8 Hz, 2H), 1.79-1.65 (m, 2H), 1.60-1.49 (m, 1H), 1.09-0.95 (m, 2H) |
| I-323[b] | ATW | AJB | 894.6 | 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.64-7.51 (m, 1H), 7.26-6.94 (m, 3H), 6.90-6.41 (m, 2H), 5.33-5.02 (m, 2H), 4.76 (d, J = 17.2 Hz, 1H), 4.24-4.09 (m, 1H), 3.85-3.55 (m, 4H), 3.37-3.34 (m, 4H), 3.02 (s, 3H), 2.99-2.88 (m, 1H), 2.81-2.71 (m, 1H), 2.59-2.52 (m, 2H), 2.29-2.18 (m, 2H), 2.13-2.10 (m, 2H), 2.06-1.91 (m, 5H), 1.90-1.80 (m, 4H), 1.79-1.66 (m, 2H), 1.61-1.52 (s, 3H), 1.53-1.44 (m, 4H), 1.10-0.92 (m, 2H) |
| I-324[b] | AOL | AJB | 868.5 | 11.10 (s, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.57 (dd, J = 7.2, 8.4 Hz, 1H), 7.27-6.91 (m, 3H), 6.90-6.40 (m, 2H), 5.33-4.98 (m, 2H), 4.76 (d, J = 16.8 Hz, 1H), 4.23-4.10 (m, 1H), 3.83-3.74 (m, 2H), 3.65-3.59 (m, 2H), 3.46-3.44 (m, 1H), 3.16 (t, J = 6.0 Hz, 2H), 2.93-2.83 (m, 1H), 2.64-2.56 (m, 1H), 2.40-2.34 (m, 1H), 2.24 (d, J = 6.8 Hz, 2H), 2.19 (s, 3H), 2.08-1.98 (m, 4H), 1.97-1.79 (m, 5H), 1.78-1.66 (m, 4H), 1.55-1.42 (m, 2H), 1.29-1.12 (m, 2H), 1.09-0.88 (m, 4H) |
| I-325[b] | ANM | ABC | 878.3 | 11.08 (s, 1H), 9.39 (s, 1H), 8.82 (d, J = 8.0 Hz, 1H), 8.37 (s, 1H), 8.28 (s, 1H), 7.57 (dd, J = 7.2, 8.4 Hz, 1H), 7.28-6.88 (m, 8H), 6.57 (t, J = 6.0 Hz, 1H), 5.04 (dd, J = 5.6, 12.8 Hz, 1H), 4.22-4.09 (m, 1H), 3.83-3.75 (m, 4H), 3.75-3.68 (m, 4H), 3.59-3.51 (m, 2H), 3.41 (s, 2H), 2.94-2.81 (m, 3H), 2.62-2.53 (m, 2H), 2.15-2.11 (m, 2H), 2.10 (s, 3H), 2.06-1.97 (m, 3H), 1.97-1.89 (m, 2H), 1.81-1.68 (m, 2H), 1.66-1.54 (m, 1H), 1.07-0.87 (m, 2H) |
| I-326[b] | AML | AGL | 855.5 | 12.36 (s, 1H), 11.10 (s, 1H), 8.71 (s, 1H), 8.47-8.42 (m, 1H), 8.39-8.33 (m, 2H), 8.17-8.13 (m, 1H), 7.64-7.53 (m, 2H), 7.06 (d, J = 7.2 Hz, 1H), 7.00 (d, J = 8.4 Hz, 1H), 6.45 (d, J = 6.4 Hz, 1H), 5.94 (s, 1H), 5.06 (dd, J = 5.2, 12.8 Hz, 1H), 4.47-4.35 (m, 1H), 4.17-4.06 (m, 1H), 2.94-2.83 (m, 1H), 2.63-2.52 (m, 2H), 2.48-2.44 (m, 1H), 2.39-2.20 (m, 6H), 2.17-2.09 (m, 4H), 2.06-1.99 (m, 1H), 1.97-1.85 (m, 4H), 1.72-1.64 (m, 4H), 1.62 (s, 6H), 1.58-1.54 (m, 2H), 1.18-1.03 (m, 2H) |
| I-327[b] | AJH | ALU | 879.2 | 11.08 (s, 1H), 10.48 (s, 1H), 8.55 (s, 1H), 8.48 (s, 1H), 8.47-8.38 (m, 2H), 8.22 (dd, J = 7.6 Hz, 1H), 7.98 (s, 1H), 7.58 (dd, J = 8.4 Hz, 1H), 7.40-7.07 (m, 2H), 7.03 (d, J = 6.8 Hz, 1H), 6.67 (t, J = 3.2 Hz, 1H), 5.08-5.03 (m, 1H), 4.58-4.43 (m, 1H), 3.48-3.45 (m, 2H), 3.41-3.37 (m, 3H), 3.22 (br d, J = 6.8 Hz, 2H), 2.94-2.80 (m, 4H), 2.21-2.12 (m, 4H), 2.07-1.82 (m, 9H), 1.70-1.54 (m, 4H), 1.23-1.06 (m, 4H) |
| I-328[b] | ALF | AJB | 853.0 | 10.96 (s, 1H), 9.49 (d, J = 6.0 Hz, 1H), 8.78 (d, J = 8.0 Hz, 1H), 8.38 (d, J = 4.4 Hz, 1H), 8.25 (d, J = 5.6 Hz, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 1H), 7.49-7.41 (m, 1H), 7.30 (d, J = 7.6 Hz, 1H), 7.24-6.96 (m, 2H), 6.90-6.41 (m, 1H), 5.30-5.05 (m, 2H), 4.91-4.84 (m, 1H), 4.76 (d, J = 18.4 Hz, 1H), 4.42-4.33 (m, 1H), 4.26-4.14 (m, 2H), 3.80 (s, 2H), 3.63 (d, J = 11.2 Hz, 1H), 3.59(s, 1H), 3.47-3.42 (m, 2H), 2.97-2.84 (m, 2H), 2.30-2.23 (m, 2H), 2.10-1.70 (m, 15H), 1.65-1.50 (m, 6H), 1.10-0.97 (m, 2H) |
| I-329[b] | ANM | AFM | 900.4 | 11.09 (s, 1H), 8.86 (s, 1H), 8.30 (s, 1H), 8.01 (s, 1H), 7.89 (s, 1H), 7.76 (s, 1H), 7.73 (s, 1H), 7.61-7.54 (m, 1H), 7.28-7.20 (m, 4H), 7.15 (d, J = 8.4 Hz, 1H), 7.02 (d, J = 6.8 Hz, 1H), 6.57(t, J = 6.0 Hz, 1H), 5.06-5.02 (m, 1H), 4.99-4.81 (m, 1H), 4.55-4.53 (m, 1H), 4.28-4.26 (m, 1H), 4.09 (s, 1H), 3.97 (s, 3H), 3.58-3.51 (m, 3H), 3.40 (s, 2H), 2.88 (m, 3H), 2.62-2.54 (m, 3H), 2.12-2.10 (m, 2H), 2.09 (s, 3H), 2.08-1.98 (m, 3H), 1.91-1.81 (m, 2H), 1.64-1.43 (m, 5H), 1.01 (t, J = 7.2 Hz, 3H), 0.96-0.83 (m, 2H) |
| I-330[b] | AVA | ABC | 858.4 | 11.01 (s, 1H), 9.40 (s, 1H), 8.83 (d, J = 8.0 Hz, 1H), 8.38 (s, 1H), 8.29 (s, 1H), 7.29 (t, J = 7.6 Hz, 1H), 7.09(t, J = 53.6 Hz, 1H), 6.95-6.89 (m, 2H), 6.77 (d, J = 8.0 Hz, 1H), 5.58 (t, J = 5.6 Hz, 1H), 5.16-5.09 (m, 1H), 4.26-4.09 (m, 3H), 3.83-3.76 (m, 4H), 3.75-3.70 (m, 4H), 3.52 (t, J = 6.0 Hz, 2H), 3.46-3.37 (m, 2H), 3.23-3.17 (m, 2H), 3.00-2.79 (m, 3H), 2.65-2.56 (m, 2H), 2.46-2.37 (m, 2H), 2.31-2.24 (m, 1H), 2.08-2.01 (m, 3H), 1.88 (d, J = 10.0 Hz, 4H), 1.81 (t, J = 6.4 Hz, 2H), 1.78-1.70 (m, 2H), 1.70-1.51 (m, 3H), 1.15-1.03 (m, 2H) |
| I-331[b] | ANK | AGL | 897.4 | 11.10 (s, 1H), 8.71 (s, 1H), 8.50-8.33 (m, 3H), 8.18-8.15 (m, 1H), 7.64-7.53 (m, 2H), 7.15-7.01 (m, 2H), 6.47 (t, J = 5.2 Hz, 1H), 5.95 (s, 1H), 5.06 (dd, J = 5.2, 12.8 Hz, 1H), 4.46-4.36 (m, 1H), 2.94-2.83 (m, 2H), 2.64-2.57 (m, 2H), 2.25-2.23 (m, 2H), 2.20 (s, 3H), 2.16-2.10 (m, 2H), 2.07-2.01 (m, 1H), 1.98-1.75 (m, 8H), 1.68-1.67 (m, 1H), 1.65-1.62 (m, 6H), 1.60-1.42 (m, 6H), 1.33-1.00 (m, 7H) |
| I-332[b] | ALJ | ABC | 888.3 | 11.09 (s, 1H), 9.40 (s, 1H), 8.83 (d, J = 8.0 Hz, 1H), 8.37 (d, J = 2.0 Hz, 1H), 8.29 (d, J = 0.4 Hz, 1H), 7.62-7.53 (m, 1H), 7.28-6.94 (m, 3H), 6.91 (d, J = 8.0 Hz, 1H), 6.66 (q, J = 5.6 Hz, 1H), 5.05 (dd, J = 5.2, 12.8 Hz, 1H), 4.23-4.11 (m, 1H), 3.83-3.69 (m, 9H), 3.64-3.56(m, 1H), 3.51-3.48 (m, 3H), 3.44-3.34 (m, 4H), 2.95-2.83 (m, 1H), 2.76-2.57 (m, 3H), 2.18-1.95 (m, 6H), 1.94-1.65 (m, 8H), 1.61-1.50 (m, 1H), 1.10-0.96 (m, 2H) |
| I-333[b] | AMC | AGL | 861.3 | 12.37 (s, 1H), 11.10 (s, 1H), 8.72 (s, 1H), 8.48-8.43 (m, 1H), 8.41-8.31 (m, 2H), 8.21-8.16 (m, 1H), 7.61-7.56 (m, 2H), 7.11 (d, J = 8.8 Hz, 1H), 7.03 (d, J = 6.8 Hz, 1H), 6.68 (t, J = 5.6 Hz, 1H), 5.97 (s, 1H), 5.05 (dd, J = 12.8, 5.4 Hz, 1H), 4.45-4.43 (m, 1H), 3.50-3.40 (m, 5H), 2.93-2.83 (m, 1H) 2.62-2.52 (m, 2H), 2.38-2.33(m, 2H), 2.16-2.10 (m, 6H), 2.05-1.97 (m, 1H), 1.95-1.80 (m, 6H), 1.70-1.65 (m, 2H), 1.64-1.52 (m, 7H), 1.14-1.03 (m, 2H) |
| I-334[b] | ALE | AFM | 923.6 | 11.08 (s, 1H), 8.85 (s, 1H), 8.28 (s, 1H), 8.01 (s, 1H), 7.89 (s, 1H), 7.82-7.67 (m, 2H), 7.57 (t, J = 7.8 Hz, 1H), 7.13-6.94 (m, 2H), 6.73 (s, 1H), 5.08-5.00 (m, 1H), 4.99-4.78 (m, 1H), 4.53 (d, J = 9.8 Hz, 1H), 4.32-4.22 (m, 1H), 4.09 (s, 1H), 3.97 (s, 3H), 3.83-3.76 (m, 1H), 2.92-2.77 (m, 3H), 2.73-2.64 (m, 3H), 2.38-2.30 (m, 5H), 2.13 (s, 3H), 2.11-1.93 (m, 8H), 1.80 (s, 3H), 1.72-1.52 (m, 5H), 1.51-1.39 (m, 3H), 1.22-1.12 (m, 1H), 1.01 (t, J = 6.8 Hz, 3H), 0.96-0.86 (m, 2H) |
| I-335[b] | AMH | AJB | 920.5 | 10.96 (s, 1H), 9.49 (d, J = 6.0 Hz, 1H), 8.78 (d, J = 8.0 Hz, 1H), 8.38 (d, J = 4.4 Hz, 1H), 8.25-8.24 (m, 1H), 7.49-6.94 (m, 8H), 6.89-6.38 (m, 1H), 5.32-5.03 (m, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | 1HNMR (400 MHz, DMSO-d$_6$) δ |
|---|---|---|---|---|
| | | | | 4H), 4.85-4.72 (m, 1H), 4.47-4.36 (m, 1H), 4.32-4.21 (m, 1H), 4.21-4.10 (m, 1H), 3.86-3.76 (m, 2H), 3.66-3.59 (m, 4H), 2.95-2.84 (m, 1H), 2.62-2.53 (m, 2H), 2.47-2.37 (m, 5H), 2.16-2.10 (m, 7H), 2.07-1.92 (m, 5H), 1.92-1.82 (m, 2H), 1.78-1.65 (m, 2H), 1.56-1.44 (m, 1H), 1.08-0.90 (m, 2H) |
| I-337[b] | AMD | AJB | 913.2 | 11.08 (s, 1H), 9.95 (s, 1H), 8.96 (s, 1H), 8.77 (s, 1H), 8.16 (d, J = 5.2 Hz, 1H), 7.78 (d, J = 8.4 Hz, 2H), 7.58-7.50 (m, 1H), 7.43 (d, J = 8.4 Hz, 2H), 7.31-7.01 (m, 5H), 6.99 (d, J = 12 Hz, 1H), 6.63 (t, J = 6.0 Hz, 1H), 5.03 (dd, J = 5.2, 12.4 Hz, 1H), 3.49 (s, 2H), 3.45-3.41 (m, 4H), 3.33-3.31 (m, 2H), 3.18 (t, J = 6.0 Hz, 2H), 2.92-2.80 (m, 1H), 2.61-2.52 (m, 2H), 2.40 (t, J = 6.8 Hz, 2H), 2.13 (s, 3H), 2.06-1.96 (m, 1H), 1.84-1.66 (m, 4H), 1.15-0.98 (m, 1H), 0.51-0.36 (m, 2H), 0.27-0.14 (m, 2H) |
| I-339[b] | AMD | PW | 912.4 | 11.07 (s, 1H), 9.69 (s, 1H), 8.91 (s, 1H), 8.19-8.11 (m, 2H), 7.57 (dd, J = 7.2, 8.4 Hz, 1H), 7.30-6.97 (m, 6H), 6.77-6.70 (m, 1H), 5.04 (dd, J = 5.2, 12.8 Hz, 1H), 4.24-4.12 (m, 1H), 3.82-3.75 (m, 1H), 3.53-3.45 (m, 2H), 3.44-3.38 (m, 2H), 3.18 (t, J = 6.4 Hz, 2H), 2.93-2.76 (m, 2H), 2.73-2.68 (m, 1H), 2.62-2.54 (m, 2H), 2.42-2.35 (m, 4H), 2.14 (s, 3H), 2.12 (br d, J = 12 Hz, 2H), 2.09-1.98 (m, 4H), 1.92-1.85 (m, 2H), 1.84-1.75 (m, 2H), 1.74-1.63 (m, 3H), 1.57-1.45 (m, 1H), 1.11-0.93 (m, 3H), 0.49-0.39 (m, 2H), 0.27-0.16 (m, 2H) |
| I-340[b] | ALE | AJB | 913.1 | 11.08 (s, 1H), 9.49 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.57 (dd, J = 12, 8.4 Hz, 1H), 7.26-6.91 (m, 3H), 6.90-6.42 (m, 2H), 5.32-4.99 (m, 2H), 4.77 (d, J = 16.8 Hz, 1H), 4.21-4.10 (m, 1H), 3.87-3.67 (m, 4H), 3.66-3.51 (m, 5H), 2.94-2.77 (m, 2H), 2.73-2.52 (m, 3H), 2.43-2.37 (m, 4H), 2.16 (s, 3H), 2.13 (s, 2H), 2.09-1.93 (m, 6H), 1.93-1.80 (m, 3H), 1.79-1.65 (m, 4H), 1.58-1.44 (m, 1H), 1.09-0.91 (m, 2H) |
| I-342[b] | ALJ | AFM | 910.4 | 11.08 (s, 1H), 8.86 (s, 1H), 8.28 (s, 1H), 8.01 (s, 1H), 7.89 (s, 1H), 7.76 (s, 1H), 7.73 (s, 1H), 7.57 (dd, J = 12, 8.4 Hz, 1H), 7.11 (d, J = 8.4 Hz, 1H), 7.02 (d, J = 7.2 Hz, 1H), 6.69-6.61 (m, 1H), 5.05 (dd, J = 52, 12.8 Hz, 1H), 4.99-4.81 (m, 1H), 4.54 (dd, J = 3.2, 11.2 Hz, 1H), 4.26 (dd, J = 6.0, 11.2 Hz, 1H), 4.10 (d, J = 6.4 Hz, 1H), 3.98 (s, 3H), 3.74 (d, J = 11.2 Hz, 1H), 3.64-3.55 (m, 1H), 3.49 (t, J = 5.6 Hz, 3H), 3.43-3.37 (m, 2H), 3.37-3.35 (m, 2H), 2.94-2.82 (m, 1H), 2.73-2.68 (m, 1H), 2.65-2.53 (m, 4H), 2.10-1.99 (m, 5H), 1.97-1.90 (m, 1H), 1.85-1.72 (m, 5H), 1.69-1.36 (m, 6H), 1.01 (t, J = 12 Hz, 3H), 0.98-0.84 (m, 2H) |
| I-343[b] | ANQ | PW | 912.5 | 11.09 (s, 1H), 9.68 (s, 1H), 8.92 (s, 1H), 8.16-8.13 (m, 2H), 7.57 (t, J = 8.0 Hz, 1H), 7.30-6.98 (m, 6H), 6.91-6.79 (m, 1H), 5.04 (dd, J = 52, 12.8 Hz, 1H), 4.15-4.11 (m, 1H), 3.76 (d, J = 10.8 Hz, 1H), 3.69-3.61 (m, 2H), 3.59 (d, J = 10.8 Hz, 1H), 3.40-3.33 (m, 2H), 3.18 (t, J = 6.0 Hz, 2H), 2.86 (d, J = 11.6 Hz, 2H), 2.74-2.59 (m, 2H), 2.43-2.33 (m, 4H), 2.24-2.13 (m, 5H), 2.06-1.94 (m, 4H), 1.91-1.81 (m, 2H), 1.79-1.66 (m, 5H), 1.55-1.54 (m, 1H), 1.10-0.91 (m, 3H), 0.50-0.41 (m, 2H), 0.27-0.17 (m, 2H) |
| I-344[b] | AFJ | ALZ | 884.5 | 11.09 (s, 1H), 9.53 (s, 1H), 8.87 (d, J = 8.0 Hz, 1H), 8.38 (s, 1H), 8.30 (s, 1H), 7.62-7.55 (m, 1H), 7.23-6.94 (m, 3H), 6.74 (d, J = 8.0 Hz, 1H), 6.63 (t, J = 5.6 Hz, 1H), 5.09-5.01 (m, 1H), 4.80-4.68 (m, 2H), 4.22-4.11 (m, 1H), 4.03-3.77 (m, 4H), 3.49 (t, J = 5.6 Hz, 2H), 3.40-3.35 (m, 2H), 3.30-3.22 (m, 2H), 3.22-3.16 (m, 1H), 2.97-2.82 (m, 1H), 2.68-2.53 (m, 4H), 2.10-2.00 (m, 6H), 1.93-1.67 (m, 9H), 1.61-1.52 (m, 1H), 1.50-1.38 (m, 2H), 1.11-0.94 (m, 2H) |
| I-345[b] | AFJ | AMB | 884.2 | 11.09 (s, 1H), 9.54 (s, 1H), 8.85 (d, J = 7.6 Hz, 1H), 8.38 (s, 1H), 8.30 (s, 1H), 7.58 (dd, J = 7.2, 8.4 Hz, 1H), 7.23-6.57 (m, 5H), 5.05 (dd, J = 52, 12.8 Hz, 1H), 4.77-4.58 (m, 2H), 4.34 (d, J = 10.8 Hz, 1H), 4.22-4.11 (m, 1H), 4.05 (d, J = 10.4 Hz, 1H), 3.86 (d, J = |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 11.2 Hz, 1H), 3.76 (d, J = 10.8 Hz, 1H), 3.49 (t, J = 6.0 Hz, 2H), 3.28-3.22 (m, 3H), 2.94-2.79 (m, 2H), 2.66-2.53 (m, 4H), 2.09-1.91 (m, 8H), 1.89-1.66 (m, 8H), 1.56-1.39 (m, 3H), 1.10-0.94 (m, 2H) |
| I-346[b] | ANX | AJB | 890.2 | 9.49 (d, J = 5.6 Hz, 1H), 8.78 (d, J = 7.6 Hz, 1H), 8.40-8.25 (m, 2H), 7.59-7.57 (m, 1H), 7.26-6.77 (m, 8H), 6.56-6.44 (m, 1H), 5.32-4.95 (m, 2H), 4.77 (br d, J = 1.2 Hz, 1H), 4.21-4.07 (m, 1H), 3.87-3.61 (m, 3H), 3.59-3.42 (m, 6H), 2.90-2.82 (m, 3H), 2.70-2.63 (m, 4H), 2.61-2.55 (m, 1H), 2.24-2.14 (m, 6H), 2.04-2.00 (m, 2H), 1.88-1.79 (m, 2H), 1.70 (br d, J = 2.4 Hz, 1H), 1.05-0.95 (m, 2H) |
| I-347[b] | ALC | AJB | 913.5 | 11.09 (s, 1H), 9.49 (d, J = 6.0 Hz, 1H), 8.78 (d, J = 7.8 Hz, 1H), 8.38 (d, J = 4.0 Hz, 1H), 8.25 (d, J = 5.6 Hz, 1H), 8.20-8.15 (m, 1H), 7.57 (t, J = 7.8 Hz, 1H), 7.26-6.94 (m, 3H), 6.92-6.40 (m, 2H), 5.31-5.07 (m, 1H), 5.07-4.99 (m, 1H), 4.76 (d, J = 18.4 Hz, 1H), 4.23-4.12 (m, 1H), 3.86-3.78 (m, 3H), 3.67-3.59 (m, 3H), 3.55-3.47 (m, 3H), 3.46 (s, 1H), 3.29 (d, J = 7.2 Hz, 1H), 2.92-2.79 (m, 2H), 2.70-2.64 (m, 1H), 2.63-2.56 (m, 1H), 2.32-2.28 (m, 2H), 2.17 (s, 5H), 2.08-1.95 (m, 6H), 1.95-1.80 (m, 4H), 1.77-1.66 (m, 2H), 1.62-1.50 (m, 3H), 1.02 (q, J = 11.4 Hz, 2H) |
| I-348[b] | AFJ | AOA | 878.3 | 11.11 (s, 1H), 10.90-10.58 (m, 1H), 8.69 (d, J = 7.6 Hz, 1H), 8.20-8.15 (m, 1H), 8.13-8.04 (m, 1H), 7.61-7.50 (m, 1H), 7.08 (d, J = 8.0 Hz, 1H), 7.01 (d, J = 6.0 Hz, 1H), 6.81-6.02 (m, 3H), 5.56-5.41 (m, 1H), 5.09-4.63 (m, 3H), 3.93-3.64 (m, 4H), 3.50 (d, J = 5.2 Hz, 4H), 2.95-2.62 (m, 6H), 2.08-1.70 (m, 20H), 1.20-1.06 (m, 2H) |
| I-349[b] | AME | AJB | 913.6 | 11.08 (d, J = 3.2 Hz, 1H), 9.50 (d, J = 6.4 Hz, 1H), 8.78 (d, J = 7.6 Hz, 1H), 8.36 (t, J = 4.2 Hz, 1H), 8.26 (d, J = 5.6 Hz, 1H), 7.61-7.53 (m, 1H), 7.25-6.95 (m, 3H), 6.91-6.43 (m, 2H), 5.31-5.00 (m, 2H), 4.77 (d, J = 17.6 Hz, 1H), 4.17-4.02 (m, 1H), 3.84-3.72 (m, 3H), 3.67-3.56 (m, 3H), 3.47-3.37 (m, 3H), 2.94-2.82 (m, 2H), 2.74-2.68 (m, 1H), 2.62-2.52 (m, 2H), 2.42-2.33 (m, 4H), 2.23-2.08 (m, 5H), 2.05-1.91 (m, 6H), 1.90-1.79 (m, 2H), 1.78-1.64 (m, 5H), 1.59-1.38 (m, 1H), 1.06-0.86 (m, 2H) |
| I-350[b] | ALG | ABC | 842.5 | 11.10 (s, 1H), 9.40 (s, 1H), 8.83 (d, J = 8.0 Hz, 1H), 8.38 (s, 1H), 8.29 (s, 1H), 7.63-7.55 (m, 1H), 7.24-6.95 (m, 3H), 6.91 (d, J = 8.0 Hz, 1H), 6.49 (d, J = 8.0 Hz, 1H), 5.12-5.05 (m, 1H), 4.23-4.13 (m, 1H), 3.92-3.85 (m, 1H), 3.83-3.76 (m, 4H), 3.75-3.70 (m, 4H), 2.93-2.83 (m, 1H), 2.63-2.56 (m, 1H), 2.43-2.43 (m, 1H), 2.44-2.35 (m, 1H), 2.26-2.22 (m, 2H), 2.20 (s, 3H), 2.07-2.00 (m, 3H), 2.08-1.99 (m, 2H), 1.85-1.72 (m, 4H), 1.69-1.57 (m, 4H), 1.55-1.42 (m, 3H), 1.10-0.94 (m, 2H) |
| I-351[b] | AOP | AJB | 876.5 | 11.34-10.82 (m, 1H), 9.49 (d, J = 5.6 Hz, 1H), 8.77 (d, J = 7.6 Hz, 1H), 8.38 (d, J = 4.0 Hz, 1H), 8.25 (t, J = 2.8 Hz, 1H), 7.59-7.57 (m, 1H), 7.35-7.22 (m, 4H), 7.18-6.95 (m, 3H), 6.88-6.43 (m, 2H), 5.29-5.00 (m, 2H), 4.76 (d, J = 16.8 Hz, 1H), 4.17 (t, J = 11.2 Hz, 1H), 3.81-3.75 (m, 4H), 3.62 (m, 6H), 2.95-2.81 (m, 3H), 2.62-2.53 (m, 1H), 2.45-2.43 (m, 2H), 2.09-1.87 (m, 7H), 1.80-1.66 (m, 2H), 1.54 (m, 1H), 1.17-1.01 (m, 2H) |
| I-352[b] | ALA | AJB | 900.3 | 11.09 (s, 1H), 9.50 (d, J = 6.4 Hz, 1H), 8.78 (d, J = 7.6 Hz, 1H), 8.40-8.34 (m, 1H), 8.26 (d, J = 5.2 Hz, 1H), 7.62-7.52 (m, 1H), 7.25-6.94 (m, 3H), 6.89-6.41 (m, 2H), 5.30-5.02 (m, 2H), 4.76 (d, J = 18.0 Hz, 1H), 4.22-4.10(m, 1H), 3.84-3.71 (m, 3H), 3.66-3.57 (m, 2H), 3.49 (t, J = 6.0 Hz, 3H), 3.46-3.37 (m, 4H), 2.95-2.83 (m, 1H), 2.71 (d, J = 10.8 Hz, 1H), 2.65-2.53 (m, 3H), 2.19-1.64 (m, 16H), 1.60-1.49 (m, 1H), 1.11-0.93 (m, 2H) |
| I-353[b] | ALA | PW | 899.4 | 11.09 (s, 1H), 9.69 (s, 1H), 8.92 (s, 1H), 8.21-8.11 (m, 2H), 7.62-7.53 (m, 1H), 7.33-6.95 (m, 6H), 6.66 (d, J = 4.4 Hz, 1H), 5.05 (dd, J = 5.6, 12.8 Hz, 1H), 4.24-4.13 (m, 1H), 3.79-3.71 (m, 1H), 3.64-3.55 (m, 1H), |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 3.53-3.46 (m, 3H), 3.43-3.40 (m, 1H), 3.39-3.36 (m, 3H), 3.18 (t, J = 6.0 Hz, 2H), 2.95-2.83 (m, 1H), 2.76-2.68 (m, 1H), 2.65-2.53 (m, 3H), 2.14-1.99 (m, 5H), 1.98-1.84 (m, 3H), 1.83-1.66 (m, 5H), 1.63-1.49 (m, 1H), 1.12-0.95 (m, 3H), 0.48-0.41 (m, 2H), 0.25-0.19 (m, 2H) |
| I-354 | ALX | AEH | 827.5 | (CDCl$_3$) 9.62 (s, 1H), 8.45 (s, 2H), 8.34 (d, J = 7.5 Hz, 1H), 8.31 (br s, 1H), 7.56-7.48 (m, 1H), 7.11 (d, J = 7.0 Hz, 1H), 6.91 (d, J = 8.5 Hz, 1H), 6.81 (t, J = 54.4 Hz, 1H), 6.33-6.23 (m, 1H), 6.14 (d, J = 7.8 Hz, 1H), 5.48 (s, 1H), 4.97-4.87 (m, 1H), 4.82-4.60 (m, 1H), 4.12-4.03 (m, 1H), 4.00 (s, 2H), 3.77-3.57 (m, 1H), 3.54-3.48 (m, 1H), 3.30 (q, J = 6.4 Hz, 2H), 2.95-2.74 (m, 3H), 2.22-2.09 (m, 4H), 2.05-1.98 (m, 1H), 1.97-1.65 (m, 8H), 1.50-1.37 (m, 4H), 1.36-1.30 (m, 3H), 1.27-1.20 (m, 2H), 1.16-1.04 (m, 2H) |
| I-355[b] | ALH | ABC | 842.5 | 11.08 (s, 1H), 9.39 (s, 1H), 8.81 (d, J = 8.0 Hz, 1H), 8.37 (s, 1H), 8.28 (s, 1H), 7.57 (dd, J = 7.2, 8.4 Hz, 1H), 7.23-6.86 (m, 4H), 6.14 (d, J = 8.4 Hz, 1H), 5.10-4.95 (m, 1H), 4.24-4.11 (m, 1H), 3.81-3.75 (m, 4H), 3.74-3.68 (m, 4H), 2.91-2.82 (m, 1H), 2.62-2.55 (m, 2H), 2.46-2.35 (m, 2H), 2.27-2.23 (m, 2H), 2.20 (s, 3H), 2.10-1.99 (m, 5H), 1.95-1.84 (m, 2H), 1.80-1.68 (m, 4H), 1.55-1.38 (m, 3H), 1.35-1.19 (m, 2H), 1.07-0.92 (m, 2H) |
| I-356[b] | ANO | ABC | 919.5 | 11.10 (s, 1H), 9.39 (s, 1H), 8.82 (d, J = 8.0 Hz, 1H), 8.37 (s, 1H), 8.28 (s, 1H), 7.51 (dd, J = 7.2, 8.4 Hz, 1H), 7.34-7.29 (m, 2H), 7.27-7.23 (m, 2H), 7.19 (t, J = 6.4 Hz, 1H), 7.11-6.94 (m, 3H), 6.90 (d, J = 8.0 Hz, 1H), 5.07 (dd, J = 5.2, 12.8 Hz, 1H), 4.54 (d, J = 6.0 Hz, 2H), 4.22-4.11 (m, 1H), 3.81-3.75 (m, 4H), 3.74-3.70 (m, 4H), 3.41 (s, 2H), 2.94-2.83 (m, 1H), 2.64-2.54 (m, 2H), 2.43-2.28 (m, 7H), 2.14-1.94 (m, 6H), 1.86 (d, J = 11.4 Hz, 2H), 1.77-1.64 (m, 2H), 1.61-1.47 (m, 1H), 1.09-0.94 (m, 2H) |
| I-359[b] | AKY | AJB | 890.5 | 11.10 (s, 1H), 9.50 (d, J = 6.8 Hz, 1H), 8.76 (d, J = 7.6 Hz, 1H), 8.36 (d, J = 4.4 Hz, 1H), 8.25 (d, J = 5.4 Hz, 1H), 7.54-7.43 (m, 1H), 7.30-7.24 (m, 2H), 7.24-6.94 (m, 6H), 6.91-6.39 (m, 1H), 5.32-4.97 (m, 2H), 4.84-4.69 (m, 1H), 4.50 (d, J = 6.0 Hz, 2H), 4.21-4.07 (m, 1H), 3.85-3.54 (m, 5H), 2.91-2.81 (m, 1H), 2.73-2.52 (m, 5H), 2.20 (s, 3H), 2.16 (d, J = 6.8 Hz, 2H), 2.05-1.92 (m, 5H), 1.81 (d, J = 11.8 Hz, 2H), 1.75-1.63 (m, 2H), 1.57-1.43 (m, 1H), 1.04-0.91 (m, 2H) |
| I-360[b] | ALK | AJB | 880.6 | 11.22-11.14 (m, 1H), 9.87-9.70 (m, 1H), 9.55-9.46 (m, 1H), 8.82-8.74 (m, 1H), 8.44-8.35 (m, 1H), 8.26 (d, J = 3.6 Hz, 1H), 8.12 (d, J = 6.0 Hz, 1H), 8.03-7.90 (m, 2H), 7.28-6.96 (m, 1H), 6.90-6.41 (m, 1H), 5.32-5.05 (m, 2H), 4.81-4.72 (m, 1H), 4.46 (s, 2H), 4.28-4.16 (m, 1H), 3.84-3.76 (m, 3H), 3.42-3.29 (m, 3H), 2.99-2.86 (m, 4H), 2.82-2.58 (m, 3H), 2.16-1.77 (m, 19H), 1.24-1.12 (m, 2H) |
| I-361[b] | AKG | AJB | 904.6 | 11.10 (s, 1H), 9.49 (d, J = 5.6 Hz, 1H), 8.78 (d, J = 7.6 Hz, 1H), 8.38 (d, J = 4.4 Hz, 1H), 8.25 (d, J = 5.6 Hz, 1H), 7.49 (dd, J = 7.2, 8.4 Hz, 1H), 7.28 (d, J = 8.0 Hz, 2H), 7.25-7.07 (m, 4H), 7.01 (d, J = 7.2 Hz, 1H), 6.99-6.95 (m, 1H), 6.89-6.41 (m, 1H), 5.30-5.02 (m, 2H), 4.76 (d, J = 17.2 Hz, 1H), 4.52 (d, J = 6.0 Hz, 2H), 4.23-4.10 (m, 1H), 3.84-3.72 (m, 2H), 3.65-3.40 (m, 1H), 3.59 (s, 1H), 2.93 (s, 1H), 2.62-2.54 (m, 3H), 2.28 (t, J = 6.8 Hz, 2H), 2.13 (s, 3H), 2.10 (d, J = 7.2 Hz, 2H), 2.07-1.99 (m, 4H), 1.99-1.82 (m, 4H), 1.79-1.62 (m, 4H), 1.57-1.42 (m, 1H), 1.10-0.93 (m, 2H) |
| I-362[b] | ARC | AJB | 930.2 | 11.09 (s, 1H), 9.50 (d, J = 6.0 Hz, 1H), 8.78 (d, J = 8.0 Hz, 1H), 8.39 (d, J = 4.4 Hz, 1H), 8.26 (d, J = 6.0 Hz, 1H), 7.58 (dd, J = 7.2, 8.4 Hz, 1H), 7.26-6.96 (m, 7H), 6.89-6.43 (m, 2H), 5.31-5.00 (m, 2H), 4.77 (d, J = 16.8 Hz, 1H), 4.26-4.12 (m, 1H), 3.84-3.72 (m, 2H), 3.66-3.56 (m, 2H), 3.55-3.49 (m, 2H), 3.46 (s, 1H), 3.00-2.92 (m, 2H), 2.87-2.82 (m, 2H), 2.64-2.55 (m, 1H), 2.16 (s, 2H), 2.11-1.86 (m, 10H), 1.83-1.54 (m, 8H), 1.15-0.98 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-364[b] | AFJ | AJT | 884.5 | 11.10 (s, 1H), 9.69 (s, 1H), 8.75 (d, J = 7.6 Hz, 1H), 8.37 (s, 1H), 8.25 (s, 1H), 7.58 (dd, J = 7.2, 8.4 Hz, 1H), 7.32-6.98 (m, 3H), 6.64 (t, J = 6.0 Hz, 1H), 6.37 (d, J = 7.6 Hz, 1H), 5.05 (dd, J = 5.6, 12.8 Hz, 1H), 4.74 (s, 4H), 4.38 (s, 4H), 4.24-4.10 (m, 1H), 3.50-3.48 (m, 2H), 3.40-3.39 (m, 2H), 3.27-3.24 (m, 2H), 2.94-2.84 (m, 1H), 2.66-2.59 (m, 2H), 2.59-2.53 (m, 1H), 2.12-1.94 (m, 7H), 1.92-1.66 (m, 8H), 1.62-1.38 (m, 3H), 1.10-0.94 (m, 2H) |
| I-365[b] | AVB | ABC | 842.2 | 11.10 (s, 1H), 9.40 (s, 1H), 8.82 (d, J = 8.0 Hz, 1H), 8.39 (s, 1H), 8.28 (s, 1H), 7.59 (d, J = 7.6 Hz, 1H), 7.18-6.81 (m, 4H), 5.05 (d, J = 8.4 Hz, 1H), 4.28-4.17 (m, 1H), 3.79 (s, 4H), 3.72 (d, J = 4.8 Hz, 4H), 3.49 (d, J = 11.2 Hz, 3H), 3.35 (d, J = 6.4 Hz, 2H), 2.95-2.82 (m, 5H), 2.69-2.53 (m, 2H), 2.08-1.95 (m, 5H), 1.92-1.73 (m, 5H), 1.68-1.58 (m, 3H), 1.55 (s, 2H), 1.26-1.11 (m, 2H) |
| I-366[b] | AJS | AJB | 925.5 | 11.09 (s, 1H), 9.50 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.58 (t, J = 7.6 Hz, 1H), 7.26-6.95 (m, 3H), 6.89-6.42 (m, 2H), 5.31-5.00 (m, 2H), 4.76 (d, J = 18.0 Hz, 1H), 4.43-4.03 (m, 2H), 3.87-3.77 (m, 2H), 3.73 (d, J = 7.6 Hz, 1H), 3.63 (d, J = 10.4 Hz, 1H), 3.59 (s, 1H), 2.95-2.82 (m, 3H), 2.80-2.68 (m, 3H), 2.67-2.59 (m, 1H), 2.59-2.53 (m, 1H), 2.45-2.34 (m, 2H), 2.19-2.12 (m, 1H), 2.11-1.46 (m, 19H), 1.46-1.37 (m, 1H), 1.11-0.94 (m, 2H) |
| I-367[b] | AJA | AJB | 883.5 | 11.10 (s, 1H), 9.50 (d, J = 6.4 Hz, 1H), 8.78 (d, J = 8.0 Hz, 1H), 8.40 (d, J = 4.4 Hz, 1H), 8.25 (d, J = 5.6 Hz, 1H), 7.60 (t, J = 8.0 Hz, 1H), 7.28-6.36 (m, 6H), 5.30-5.02 (m, 2H), 4.76 (d, J = 18.4 Hz, 1H), 4.24-4.13 (m, 1H), 3.84-3.78 (m, 2H), 3.73 (d, J = 7.6 Hz, 1H), 3.66-3.57 (m, 3H), 3.03 (d, J = 92 Hz, 3H), 2.95-2.82 (m, 2H), 2.62 (d, J = 5.6 Hz, 3H), 2.57 (s, 1H), 2.55 (s, 1H), 2.17-1.69 (m, 16H), 1.66-1.48 (m, 3H), 1.13-1.01 (m, 2H) |
| I-368[b] | AJM | ABC | 886.3 | 9.39 (s, 1H), 8.82 (d, J = 8.0 Hz, 1H), 8.37 (s, 1H), 8.28 (s, 1H), 7.59 (t, J = 8.0 Hz, 1H), 7.25-6.94 (m, 3H), 6.90 (d, J = 8.0 Hz, 1H), 6.65 (t, J = 5.6 Hz, 1H), 5.12 (dd, J = 5.2, 13.2 Hz, 1H), 4.21-4.12 (m, 1H), 3.79 (s, 4H), 3.72 (s, 4H), 3.50-3.46(m, 2H), 3.38-3.36 (m, 2H), 3.02 (s, 3H), 2.98-2.87 (m, 2H), 2.74-2.61 (m, 4H), 2.13-1.99 (m, 7H), 1.88-1.67 (m, 8H), 1.60-1.41 (m, 3H), 1.10-0.93 (m, 2H) |
| I-371[b] | AFJ | AJB | 884.5 | 11.10 (s, 1H), 9.50 (d, J = 6.4 Hz, 1H), 8.79 (d, J = 7.6 Hz, 1H), 8.39 (d, J = 4.0 Hz, 1H), 8.26 (d, J = 5.6 Hz, 1H), 8.15 (s, 1H), 7.59 (dd, J = 7.2, 8.4 Hz, 1H), 7.27-7.08 (m, 2H), 7.05-6.97 (m, 1H), 6.90-6.42 (m, 2H), 5.31-5.02 (m, 2H), 4.77 (d, J = 16.8 Hz, 1H), 4.25-4.09 (m, 1H), 3.86-3.74 (m, 2H), 3.74-3.62 (m, 1H), 3.61-3.58 (m, 1H), 3.50 (t, J = 5.6 Hz, 2H), 3.45 (d, J = 9.6 Hz, 1H), 3.41-3.38 (m, 2H), 2.95-2.84 (m, 1H), 2.66-2.60 (m, 1H), 2.59-2.56 (m, 1H), 2.20-1.92 (m, 10H), 1.91-1.65 (m, 9H), 1.60-1.42 (m, 3H), 1.10-0.97 (m, 2H) |
| I-372[b] | AJF | AFM | 890.6 | 11.09 (s, 1H), 8.87 (s, 1H), 8.28 (s, 1H), 8.01 (s, 1H), 7.89 (s, 1H), 7.76 (s, 1H), 7.73 (s, 1H), 7.60-7.54 (m, 1H), 7.10 (d, J = 8.8 Hz, 1H), 7.02 (d, J = 7.2 Hz, 1H), 6.46 (t, J = 5.6 Hz, 1H), 5.08-5.02 (m, 1H), 4.98-4.82 (m, 1H), 4.56-4.51 (m, 1H), 4.29-4.23 (m, 1H), 4.09 (s, 1H), 3.97 (s, 3H), 3.35-3.30 (m, 4H), 2.95-2.83 (m, 1H), 2.65-2.56 (m, 2H), 2.56-2.52 (m, 2H), 2.31-2.13 (m, 4H), 2.09-2.00 (m, 5H), 1.91-1.76 (m, 4H), 1.62-1.54 (m, 4H), 1.52-1.43 (m, 6H), 1.01 (t, J = 7.2 Hz, 3H), 0.98-0.85 (m, 2H) |
| I-373[b] | AJF | AJB | 880.5 | 11.09 (s, 1H), 9.49 (d, J = 6.4 Hz, 1H), 8.77 (d, J = 7.6 Hz, 1H), 8.37 (d, J = 4.4 Hz, 1H), 8.24 (d, J = 5.6 Hz, 1H), 7.56 (dd, J = 7.2, 8.4 Hz, 1H), 7.25-6.94 (m, 3H), 6.89-6.38 (m, 2H), 5.31-4.95 (m, 2H), 4.82-4.70 (m, 1H), 4.21-4.09 (m, 1H), 3.85-3.74 (m, 2H), 3.61-3.56 (m, 2H), 3.35-3.30 (m, 4H), 2.90-2.81 (m, 1H), 2.63-2.52 (m, 2H), 2.30-2.15 (m, 3H), 2.11-1.82 (m, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 11H), 1.78-1.64 (m, 2H), 1.61-1.40 (m, 7H), 1.08-0.93 (m, 2H) |
| I-374[b] | AJE | AJB | 870.6 | 11.00 (s, 1H), 9.50 (d, J = 5.2 Hz, 1H), 8.78 (d, J = 6.8 Hz, 1H), 8.38 (s, 1H), 8.29-8.21 (m, 1H), 7.33-6.92 (m, 3H), 6.88-6.40 (m, 2H), 5.65-5.50 (m, 1H), 5.35-5.02 (m, 2H), 4.85-4.68 (m, 1H), 4.28-4.16 (m, 2H), 4.16-4.06 (m, 2H), 3.87-3.78 (m, 2H), 3.70-3.57 (m, 4H), 2.98-2.92 (m, 1H), 2.88-2.80 (m, 2H), 2.69-2.56 (m, 2H), 2.36-2.29 (m, 1H), 2.20-2.10 (m, 2H), 2.09-1.95 (m, 6H), 1.92-1.83 (m, 4H), 1.77-1.69 (m, 2H), 1.67-1.42 (m, 5H), 1.23-1.12 (m, 2H), 1.07-0.96 (m, 2H) |
| I-376[b] | AJH | AGL | 887.5 | 12.36 (s, 1H), 11.10 (s, 1H), 8.71 (s, 1H), 8.48-8.43 (m, 1H), 8.40-8.33 (m, 2H), 8.16 (d, J = 8.4 Hz, 1H), 7.62-7.55 (m, 2H), 7.10 (d, J = 8.6 Hz, 1H), 7.03 (d, J = 7.2 Hz, 1H), 6.67 (t, J = 6.0 Hz, 1H), 5.94 (s, 1H), 5.08-5.03 (m, 1H), 4.49-4.38 (m, 1H), 3.48 (t, J = 5.2 Hz, 2H), 3.41-3.37 (m, 3H), 3.25-3.24 (m, 2H), 2.95-2.80 (m, 2H), 2.62-2.55 (m, 5H), 2.18-2.09 (m, 2H), 2.08-1.88 (m, 6H), 1.85-1.65 (m, 6H), 1.62 (s, 6H), 1.38-1.09 (m, 4H) |
| I-377[b] | AIR | ABC | 906.3 | 10.97 (s, 1H), 9.39 (s, 1H), 8.83 (d, J = 8.0 Hz, 1H), 8.37 (s, 1H), 8.28 (s, 1H), 7.51-7.46 (m, 1H), 7.44 (d, J = 7.6 Hz, 2H), 7.35-7.29 (m, 4H), 7.23-6.95 (m, 1H), 6.91 (d, J = 8.4 Hz, 1H), 5.22 (s, 2H), 5.11 (dd, J = 4.8, 12.8 Hz, 1H), 4.45-4.38 (m, 1H), 4.30-4.22 (m, 1H), 4.21-4.12 (m, 1H), 3.84-3.68 (m, 10H), 3.46 (s, 4H), 2.13-1.94 (m, 8H), 1.93-1.82 (m, 3H), 1.79-1.66 (m, 3H), 1.62-1.46 (m, 2H), 1.11-0.92 (m, 3H) |
| I-379[b] | AIR | ACA | 917.3 | 10.13 (s, 1H), 9.70 (s, 1H), 8.92 (s, 1H), 8.19-8.12 (m, 2H), 7.37-7.14 (m, 7H), 7.09 (s, 1H), 7.04-6.99 (m, 2H), 5.34-5.21 (m, 1H), 4.88-4.76 (m, 2H), 4.40-4.31 (m, 1H), 4.23-4.11 (m, 2H), 3.57-3.47 (m, 1H), 3.39-3.33 (m, 8H), 3.20-3.15 (m, 2H), 3.13-3.06 (m, 1H), 2.87-2.72 (m, 1H), 2.28-2.16 (m, 2H), 2.11-1.97 (m, 4H), 1.93-1.84 (m, 2H), 1.81-1.68 (m, 2H), 1.65-1.49 (m,2H), 1.14-0.91 (m, 3H), 0.50-0.40 (m, 2H), 0.26-0.18 (m, 2H) |
| I-380[b] | AJC | AJB | 826.5 | 11.01 (s, 1H), 9.50 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.27 (t, J = 8.0 Hz, 1H), 7.25-6.95 (m, 1H), 6.91 (d, J = 7.2 Hz, 1H), 6.88-6.43 (m, 2H), 5.63 (t, J = 5.6 Hz, 1H), 5.31-5.05 (m, 2H), 4.84-4.70 (m, 1H), 4.28-4.08 (m, 3H), 3.83-3.72 (m, 2H), 3.02 (t, J = 6.0 Hz, 2H), 2.97-2.92 (m, 1H), 2.90-2.84 (m, 2H), 2.65-2.58 (m, 2H), 2.31-2.24 (m, 1H), 2.13 (d, J = 7.2 Hz, 2H), 2.07-1.68 (m, 14H), 1.63-1.53 (m, 2H), 1.27-1.14 (m, 2H), 1.09-0.97 (m, 2H) |
| I-381[b] | AML | AJB | 866.4 | 11.10 (s, 1H), 9.50 (d, J = 6.4 Hz, 1H), 8.78 (d, J = 8.0 Hz, 1H), 8.38 (d, J = 4.4 Hz, 1H), 8.25 (d, J = 5.6 Hz, 1H), 7.58 (d, J = 7.8 Hz, 1H), 7.26-6.40 (m, 5H), 5.30-5.01 (m, 2H), 4.77 (d, J = 16.8 Hz, 1H), 4.23-4.07 (m, 2H), 3.85-3.71 (m, 2H), 3.66-3.56 (m, 2H), 2.94-2.82 (m, 1H), 2.69-2.52 (m, 2H), 2.39-2.27 (m, 4H), 2.21 (s, 2H), 2.11-1.93 (m, 7H), 1.93-1.83 (m, 2H), 1.79-1.60 (m, 6H), 1.55 (d, J = 5.2 Hz, 3H), 1.10-0.95 (m, 2H) |
| I-384[b] | AJV | ABC | 871.6 | 9.40 (s, 1H), 8.83 (d, J = 8.0 Hz, 1H), 8.39 (s, 1H), 8.34-8.27 (m, 2H), 7.62-7.55 (m, 1H), 7.25-6.95 (m, 3H), 6.91 (d, J = 8.0 Hz, 1H), 6.25 (d, J = 8.0 Hz, 1H), 5.08-5.01 (m, 1H), 4.24-4.16 (m, 1H), 3.82-3.78 (m, 4H), 3.74-3.71 (m, 4H), 2.92-2.84 (m, 1H), 2.83-2.75 (m, 4H), 2.69-2.63 (m, 2H), 2.61-2.56 (m, 3H), 2.38 (t, J = 6.4 Hz, 2H), 2.21-2.12 (m, 2H), 2.10-2.00 (m, 3H), 1.94 (t, J = 10.4 Hz, 4H), 1.80-1.68 (m, 4H), 1.66-1.59 (m, 1H), 1.54-1.45 (m, 2H), 1.22-1.07 (m, 2H) |
| I-385[b] | AJI | ABC | 828.5 | 11.09 (s, 1H), 9.39 (s, 1H), 8.82 (d, J = 8.0 Hz, 1H), 8.37 (s, 1H), 8.29 (s, 1H), 7.57 (t, J = 8.0 Hz, 1H), 7.24-6.94 (m, 3H), 6.90 (d, J = 8.0 Hz, 1H), 6.63-6.56 (m, 1H), 5.11-5.00 (m, 1H), 4.21-4.12 (m, 1H), 3.82-3.77 (m, 4H), 3.75-3.70 (m, 4H), 3.25-3.20 (m, 2H), 2.94-2.83 (m, 3H), 2.64-2.55 (m, 2H), 2.16-2.09 (m, |

US 11,352,350 B2

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | 2H), 2.08-2.00 (m, 3H), 1.93-1.82 (m, 4H), 1.79-1.65 (m, 4H), 1.63-1.52 (m, 2H), 1.33-1.19 (m, 2H), 1.08-0.94 (m, 2H) |
| I-386[b] | AGU | AFM | 880.1 | 11.09 (s, 1H), 8.86 (s, 1H), 8.28 (s, 1H), 8.16 (s, 1H), 8.02 (s, 1H), 7.89 (s, 1H), 7.76 (s, 1H), 7.73 (s, 1H), 7.59 (t, J = 8.0 Hz, 1H), 7.15 (d, J = 8.0 Hz, 1H), 7.04 (d, J = 7.2 Hz, 1H), 6.62 (t, J = 5.2 Hz, 1H), 5.07 (dd, J = 5.2, 12.8 Hz, 1H), 4.99-4.81 (m, 1H), 4.54 (dd, J = 3.2, 11.2 Hz, 1H), 4.28-4.24 (m, 1H), 4.13-4.06 (m, 1H), 3.98 (s, 3H), 3.65-3.59 (m, 2H), 3.46-3.44 (m, 2H), 2.92-2.84 (m, 1H), 2.65-2.63 (m, 1H), 2.61-2.57 (m, 4H), 2.10-2.04 (m, 8H), 1.81-1.78 (m, 4H), 1.62-1.41 (m, 8H), 1.01 (t, J = 7.2 Hz, 3H), 0.98-0.88 (m, 2H) |
| I-387[b] | ADR | AFM | 868.2 | 11.10 (s, 1H), 8.87 (s, 1H), 8.29 (s, 1H), 8.20 (s, 1H), 8.01 (s, 1H), 7.90 (s, 1H), 7.77 (s, 1H), 7.75 (s, 1H), 7.62-7.55 (m, 1H), 7.16 (d, J = 8.4 Hz, 1H), 7.04 (d, J = 7.2 Hz, 1H), 6.62 (t, J = 5.6 Hz, 1H), 5.06 (dd, J = 5.2, 12.8 Hz, 1H), 5.00-4.81 (m, 1H), 4.55 (dd, J = 3.2, 11.2 Hz, 1H), 4.27 (dd, J = 6.4. 11.2 Hz, 1H), 4.12-4.08 (m, 1H), 3.98 (s, 3H), 3.60-3.57 (m, 2H), 3.49-3.46 (m, 6H), 2.92-2.85 (m, 1H), 2.62-2.59 (m, 1H), 2.58-2.56 (m, 1H), 2.34-2.30 (m, 2H), 2.10 (s, 3H), 2.07-1.98 (m, 5H), 1.83-1.75 (m, 2H), 1.68-1.56 (m, 4H), 1.50-1.37 (m, 3H), 1.02 (t, J = 7.2 Hz, 3H), 0.93-0.82 (m, 2H) |
| I-389 | WX | GF | 848.2 | 11.10 (s, 1H), 9.98 (s, 1H), 8.96 (s, 1H), 8.78 (s, 1H), 8.15 (s, 1H), 7.79 (d, J = 8.8 Hz, 2H), 7.45 (d, J = 8.8 Hz, 2H), 7.43-7.14 (m, 1H), 7.12-7.05 (m, 3H), 7.05-7.02 (m, 1H), 6.96 (t, J = 7.6 Hz, 1H), 6.87 (d, J = 7.2 Hz, 1H), 5.38 (dd, J = 5.6, 12.4 Hz, 1H), 3.68 (s, 3H), 3.62 (s, 2H), 3.59 (s, 2H), 3.21-3.15 (m, 4H), 2.95-2.84 (m, 3H), 2.77-2.68 (m, 1H), 2.11 (s, 3H), 2.06-1.92 (m, 3H), 1.74 (d, J = 12.0 Hz, 2H), 1.56-1.42 (m, 2H), 1.13-1.01 (m, 1H), 0.54-0.39 (m, 2H), 0.28-0.14 (m, 2H) |
| I-390[g] | PF | PW | 1164.5 | 9.75 (s, 1H), 8.95 (s, 1H), 8.25-8.18 (m, 2H), 8.15 (d, J = 5.2 Hz, 1H), 7.33-6.99 (m, 11H), 6.92 (d, J = 2.4 Hz, 1H), 6.84-6.77 (m, 2H), 5.01 (d, J = 9.6 Hz, 1H), 4.91-4.83 (m, 2H), 4.73-4.65 (m, 2H), 4.29-4.19 (m, 2H), 4.07-4.05 (m, 3H), 3.80-3.73 (m, 4H), 3.70-3.68 (m, 4H), 3.60 (s, 9H), 3.20 (d, J = 5.2 Hz, 2H), 3.16-3.12 (m, 2H), 2.86 (d, J = 4.4 Hz, 3H), 1.99-1.89 (m, 3H), 1.80-1.72 (m, 4H), 1.29 (d, J = 6.8 Hz, 1H), 1.25 (d, J = 6.8 Hz, 3H), 1.20-1.15 (m, 3H), 1.09 (s, 9H), 0.98 (s, 3H), 0.51-0.45 (m, 2H), 0.25-0.23 (m, 2H) |
| I-392 | AMC | GF | 865.3 | 11.08 (s, 1H), 9.95 (s, 1H), 8.96 (s, 1H), 8.77 (s, 1H), 8.16 (d, J = 5.2 Hz, 1H), 7.78 (d, J = 8.4 Hz, 2H), 7.58-7.50 (m, 1H), 7.43 (d, J = 8.4 Hz, 2H), 7.31-7.01 (m, 5H), 6.99 (d, J = 7.2 Hz, 1H), 6.63 (t, J = 6.0 Hz, 1H), 5.03 (dd, J = 5.2, 12.8 Hz, 1H), 3.49 (s, 2H), 3.45-3.41 (m, 4H), 3.36-3.32 (m, 2H), 3.18 (t, J = 6.0 Hz, 2H), 2.93-2.80 (m, 1H), 2.61-2.52 (m, 2H), 2.40 (t, J = 6.8 Hz, 2H), 2.13 (s, 3H), 2.06-1.96 (m, 1H), 1.84-1.66 (m, 4H), 1.15-0.98 (m, 1H), 0.51-0.36 (m, 2H), 0.28-0.14(m, 2H) |
| I-393 | ALA | GF | 893.4 | 11.09 (s, 1H), 9.98 (s, 1H), 8.97 (s, 1H), 8.78 (s, 1H), 8.16 (d, J = 5.2 Hz, 1H), 7.80 (d, J = 8.8 Hz, 2H), 7.59-7.50 (m, 1H), 7.45 (d, J = 8.4 Hz, 2H), 7.43-7.14 (m, 1H), 7.13-6.98 (m, 5H), 6.67-6.55 (m, 1H), 5.04 (dd, J = 5.2, 12.8 Hz, 1H), 3.81-3.73 (m, 1H), 3.67-3.59 (m, 1H), 3.51 (s, 3H), 3.48-3.45 (m, 2H), 3.42-3.39 (m, 1H), 3.37-3.34 (m, 3H), 3.18 (t, J = 6.0 Hz, 2H), 2.93-2.81 (m, 1H), 2.76-2.70 (m, 1H), 2.65-2.53 (m, 3H), 2.13-1.97 (m, 2H), 1.88 (t, J = 10.8 Hz, 1H), 1.83-1.71 (m, 2H), 1.12-1.00 (m, 1H), 0.50-0.41 (m, 2H), 0.27-0.17 (m, 2H) |
| I-395 | WX | AMK | 868.4 | 11.13 (s, 1H), 11.10-10.96 (m, 1H), 10.74 (br s, 1H), 9.73-8.90 (m, 1H), 8.20 (br s, 1H), 8.11 (s, 1H), 8.01 (d, J = 5.3 Hz, 1H), 7.54 (br s, 1H), 7.38 (d, J = 7.8 Hz, 1H), 7.31-7.21 (m, 1H), 7.18-7.09 (m, 1H), 7.08-6.72 (m, 2H), 5.46 (dd, J = 5.4, 12.5 Hz, 1H), 4.87- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|
| | | | | 4.49 (m, 2H), 4.25-4.15 (m, 1H), 3.67 (s, 3H), 3.62-3.45 (m, 3H), 3.34 (d, J = 6.7 Hz, 2H), 3.25 (br s, 4H), 3.11-2.99 (m, 1H), 2.98-2.80 (m, 2H), 2.78-2.59 (m, 5H), 2.37-2.23 (m, 4H), 2.21-2.09 (m, 1H), 2.08-1.91 (m, 4H), 1.90-1.63 (m, 3H), 1.29-1.04 (m, 3H), 0.61-0.47 (m, 2H), 0.32 (q, J = 4.6 Hz, 2H) |
| I-397[b] | AMC | APD | 887.5 | 9.85-9.79 (m, 1H), 8.78-8.75 (m, 1H), 8.28 (d, J = 5.2 Hz, 1H), 8.02 (s, 1H), 7.58-7.50 (m, 1H), 7.31-7.27 (m, 1H), 7.24-7.20 (m, 1H), 7.19-6.90 (m, 3H), 6.60 (t, J = 5.6 Hz, 1H), 5.00-4.93 (m, 1H), 4.12 (s, 1H), 3.70-3.68 (m, 4H), 3.51-3.47 (m, 4H), 3.44 (t, J = 5.8 Hz, 2H), 3.38 (t, J = 6.0 Hz, 2H), 3.35-3.29 (m, 2H), 2.86-2.76 (m, 1H), 2.63-2.51 (m, 2H), 2.48-2.42 (m, 2H), 2.22 (d, J = 7.2 Hz, 2H), 2.20 (s, 3H), 2.04-1.92 (m, 3H), 1.85-1.75 (m, 4H), 1.74-1.58 (m, 4H), 1.57-1.43 (m, 1H), 1.06-0.90 (m, 2H) |
| I-400 | WX | PW | 854.3 | 11.10 (s, 1H), 9.69 (s, 1H), 8.92 (s, 1H), 8.18 (s, 1H), 7.31-6.82 (m, 7H), 5.40-5.36 (m, 1H), 4.27-4.11 (m, 1H), 3.67 (s, 3H), 3.62 (s, 2H), 3.23-3.11 (m, 3H), 2.97-2.81 (m, 3H), 2.78-2.69 (m, 1H), 2.68-2.59 (m, 2H), 2.36-2.30 (m, 2H), 2.27 (s, 3H), 2.08-2.00 (m, 3H), 2.00-1.94 (m, 2H), 1.93-1.84 (m, 2H), 1.82-1.63 (m, 4H), 1.60-1.50 (m, 1H), 1.48-1.34 (m, 2H), 1.11-0.95 (m, 3H), 0.50-0.40 (m, 2H), 0.25-0.16 (m, 2H) |
| I-401 | AMC | AMK | 885.5 | 11.08 (s, 1H), 8.15-7.91 (m, 3H), 7.61-7.52 (m, 1H), 7.09-6.73 (m, 6H), 6.66 (t, J = 5.6 Hz, 1H), 5.04 (dd, J = 5.2, 12.8 Hz, 1H), 4.13-4.04 (m, 1H), 3.48-3.41 (m, 6H), 3.23 (s, 3H), 3.13 (t, J = 6.0 Hz, 2H), 2.92-2.83 (m, 1H), 2.62-2.52 (m, 2H), 2.30 (t, J = 7.2 2H), 2.10 (s, 3H), 2.07 (d, J = 6.8 Hz, 2H), 2.03-1.95 (m, 3H), 1.86-1.77 (m, 4H), 1.71-1.60 (m, 4H), 1.50-1.41 (m, 1H), 1.07-0.91 (m, 3H), 0.46-0.39 (m, 2H), 0.22-0.17 (m, 2H) |
| I-404[b] | AKA | ABC | 857.6 | 11.09 (s, 1H), 9.39 (s, 1H), 8.82 (d, J = 8.0 Hz, 1H), 8.38 (s, 1H), 8.29 (s, 1H), 8.19 (s, 1H), 7.24-6.93 (m, 3H), 6.92-6.88 (m, 1H), 5.42-5.32 (m, 1H), 4.23-4.12 (m, 1H), 3.83-3.76 (m, 4H), 3.75-3.70 (m, 4H), 3.57 (s, 3H), 3.11-2.97 (m, 4H), 2.93-2.84 (m, 1H), 2.76-2.68 (m, 1H), 2.66-2.61 (m, 1H), 2.60-2.54 (m, 3H), 2.31-2.26 (m, 1H), 2.26-2.15 (m, 5H), 2.06-1.95 (m, 4H), 1.90 (d, J = 11.2 Hz, 2H), 1.80-1.61 (m, 4H), 1.55-1.37 (m, 3H), 1.08-0.93 (m, 2H) |
| I-410[b] | AKN | AJB | 909.1 | 11.09 (s, 1H), 9.49 (d, J = 6.0 Hz, 1H), 8.78 (d, J = 7.6 Hz, 1H), 8.37 (d, J = 4.0 Hz, 1H), 8.25 (d, J = 5.6 Hz, 1H), 7.24-6.94 (m, 3H), 6.91-6.43 (m, 2H), 5.37 (dd, J = 5.2, 12.8 Hz, 1H), 5.30-5.04 (m, 1H), 4.76 (d, J = 17.6 Hz, 1H), 4.22-4.10 (m, 1H), 3.89-3.69 (m, 3H), 3.65-3.63 (m, 1H), 3.58 (s, 2H), 3.57 (s, 3H), 3.45 (s, 2H), 3.12 (t, J = 7.6 Hz, 2H), 2.93-2.85 (m, 1H), 2.76-2.65 (m, 2H), 2.41 (t, J = 7.6 Hz, 2H), 2.27-2.12 (m, 3H), 2.09-1.91 (m, 8H), 1.86 (d, J = 12.0 Hz, 2H), 1.77-1.68 (m, 2H), 1.61-1.50 (m, 5H), 1.07-0.94 (m, 2H) |
| I-411[b] | YK | AJB | 871.6 | 11.07 (s, 1H), 9.60-9.41 (m, 1H), 8.78 (d, J = 7.6 Hz, 1H), 8.40 (dd, J = 3.6, 14.8 Hz, 1H), 8.27 (t, J = 4.8 Hz, 1H), 7.29-7.10 (m, 1H), 7.08 (d, J = 7.8 Hz, 1H), 7.02-6.87 (m, 2H), 6.87-6.41 (m, 1H), 5.42-5.33 (m, 1H), 5.32-5.03 (m, 1H), 4.77 (d, J = 15.8 Hz, 1H), 4.19-4.02 (m, 1H), 3.84-3.78 (m, 2H), 3.78-3.73 (m, 2H), 3.69 (s, 3H), 3.67-3.55 (m, 3H), 3.54-3.50 (m, 1H), 3.45-3.40 (m, 2H), 2.94-2.82 (m, 2H), 2.75-2.65 (m, 2H), 2.65-2.57 (m, 1H), 2.36-2.27 (m, 2H), 2.13 (s, 3H), 2.08-1.91 (m, 7H), 1.82-1.62 (m, 5H), 1.48-1.32 (m, 1H), 1.02-0.88 (m, 1H), 0.86-0.69 (m, 1H) |
| I-413[b] | ADC | AJB | 858.3 | 11.09 (s, 1H), 9.51 (d, J = 6.0 Hz, 1H), 8.80 (d, J = 7.6 Hz, 1H), 8.39 (d, J = 4.0 Hz, 1H), 8.27 (d, J = 5.2 Hz, 1H), 8.16 (s, 1H), 7.26-6.96 (m, 2H), 6.91-6.44 (m, 2H), 5.41-5.06 (m, 1H), 4.78 (br d, J = 18.4 Hz, 1H), 4.24-4.13 (m, 1H), 3.85-3.62 (m, 5H), 3.58 (s, 3H), 3.46 (s, 2H), 3.02-2.91 (m, 4H), 2.63-2.56 (m, 2H), 2.25 (m, 4H), 2.09-1.97 (m, 6H), 1.95-1.83 (m, 6H), 1.72 (dd, J = 5.6, 12.8 Hz, 4H), 1.63-1.54 (m, 2H), 1.10-1.01 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-414[b] | ALM | AJB | 909.3 | 11.09 (s, 1H), 9.49 (d, J = 6.0 Hz, 1H), 8.77 (d, J = 7.6 Hz, 1H), 8.37 (d, J = 4.0 Hz, 1H), 8.25 (d, J = 5.6 Hz, 1H), 7.25-6.89 (m, 4H), 6.88-6.43 (m, 1H), 5.36 (dd, J = 5.2, 12.4 Hz, 1H), 5.29-5.05 (m, 1H), 4.76 (d, J = 17.6 Hz, 1H), 4.19-4.12 (m, 1H), 3.81-3.74 (m, 2H), 3.59 (s, 2H), 3.57 (s, 3H), 3.40-3.37 (m, 2H), 3.33-3.28 (m, 2H), 3.13 (t, J = 7.6 Hz, 2H), 3.05-2.96 (m, 4H), 2.93-2.84 (m, 1H), 2.72-2.59 (m, 4H), 2.34 (d, J = 6.4 Hz, 2H), 2.06-1.91 (m, 5H), 1.84 (d, J = 11.2 Hz, 2H), 1.75-1.63 (m, 2H), 1.59-1.50 (m, 4H), 1.42-1.28 (m, 1H), 1.13-0.94 (m, 2H) |
| I-415[b] | AMS | AJB | 886.2 | 11.09 (s, 1H), 9.50 (d, J = 6.0 Hz, 1H), 8.78 (d, J = 7.6 Hz, 1H), 8.38 (d, J = 4.8 Hz, 1H), 8.26 (d, J = 5.6 Hz, 1H), 7.27-6.97 (m, 1H), 6.97-6.90 (m, 2H), 6.89-6.42 (m, 2H), 5.36 (dd, J = 5.2, 12.8 Hz, 1H), 5.30-5.05 (m, 1H), 4.83-4.72 (m, 1H), 4.17-4.15 (m, 1H), 3.84-3.58 (m, 4H), 3.54 (s, 3H), 3.46-3.42 (m, 1H), 3.05-3.01 (m, 2H), 2.95-2.84 (m, 1H), 2.76-2.67 (m, 1H), 2.64-2.54 (m, 1H), 2.32-2.18 (m, 3H), 2.16-2.10 (m, 2H), 2.09-1.80 (m, 10H), 1.78-1.68 (m, 2H), 1.60-1.44 (m, 7H), 1.10-0.94 (m, 2H) |
| I-416[b] | AKP | AJB | 854.5 | 11.09 (s, 1H), 9.49 (d, J = 6.0 Hz, 1H), 8.77 (d, J = 7.8 Hz, 1H), 8.38 (d, J = 4.0 Hz, 1H), 8.25 (d, J = 5.6 Hz, 1H), 7.27-6.94 (m, 3H), 6.90-6.42 (m, 2H), 5.44-5.32 (m, 1H), 5.30-5.02 (m, 1H), 4.85-4.70 (m, 1H), 4.21-4.11 (m, 1H), 3.85-3.78 (m, 2H), 3.65-3.60 (m, 2H), 3.54 (s, 3H), 2.91-2.81 (m, 5H), 2.76-2.69 (m, 1H), 2.65-2.57 (m, 1H), 2.18-2.09 (m, 2H), 2.08-1.95 (m, 5H), 1.93-1.85 (m, 4H), 1.79-1.68 (m, 2H), 1.67-1.55 (m, 5H), 1.37-1.29 (m, 5H), 1.28-1.20 (m, 1H), 1.19-1.10 (m, 2H), 1.09-0.96 (m, 2H) |
| I-417[b] | APT | AJB | 866.5 | 11.12 (s, 1H), 9.50 (d, J = 6.4 Hz, 1H), 8.78 (d, J = 7.6 Hz, 1H), 8.39 (d, J = 4.4 Hz, 1H), 8.25 (d, J = 5.6 Hz, 1H), 7.26-6.96 (m, 4H), 6.88-6.43 (m, 1H), 5.40 (dd, J = 5.2, 12.8 Hz, 1H), 5.31-5.04 (m, 1H), 4.79-4.77 (m, 1H), 4.52 (s, 2H), 4.27-4.14 (m, 1H), 3.84-3.71 (m, 3H), 3.65 (s, 3H), 3.62-3.58 (m, 1H), 3.46-3.43 (m, 1H), 3.13-2.97 (m, 2H), 2.97-2.79 (m, 2H), 2.78-2.68 (m, 2H), 2.68-2.53 (m, 3H), 2.09-1.86 (m, 9H), 1.84-1.60 (m, 5H), 1.16-1.10 (m, 2H) |
| I-419[b] | PP | AKV | 844.6 | 11.08 (s, 1H), 9.39 (s, 1H), 8.72 (d, J = 8.0 Hz, 1H), 8.38 (s, 1H), 8.24 (s, 1H), 7.22-6.97 (m, 1H), 6.97-6.85 (m, 4H), 5.36 (dd, J = 5.6, 12.4 Hz, 1H), 4.22-4.12 (m, 1H), 3.79 (s, 4H), 3.57 (s, 3H), 3.44-3.40 (m, 4H), 3.00-2.93 (m, 2H), 2.90-2.83 (m, 1H), 2.76-2.68 (m, 1H), 2.65-2.57 (m, 1H), 2.41 (t, J = 7.2 Hz, 2H), 2.19 (s, 5H), 2.06-1.95 (m, 3H), 1.93-1.86 (m, 2H), 1.86-1.80 (m, 2H), 1.80-1.71 (m, 2H), 1.70-1.64 (m, 4H), 1.63-1.51 (m, 5H), 1.11-0.96 (m, 2H) |
| I-421[b] | ALO | AJB | 895.5 | 11.11 (s, 1H), 9.52 (d, J = 6.8 Hz, 1H), 8.80 (d, J = 7.6 Hz, 1H), 8.41 (d, J = 3.6 Hz, 1H), 8.27 (d, J = 5.6 Hz, 1H), 7.29-6.94 (m, 3H), 6.91-6.43 (m, 2H), 5.40-5.38 (m, 1H), 5.31-5.06 (m, 1H), 4.83-4.72 (m, 1H), 4.32-4.19 (m, 1H), 4.09 (s, 1H), 4.04 (s, 1H), 3.84-3.78 (m, 3H), 3.77-3.70 (m, 2H), 3.69-3.58 (m, 3H), 3.53 (s, 3H), 3.06-2.84 (m, 5H), 2.79-2.67 (m, 2H), 2.15-1.75 (m, 14H), 1.26-1.16 (m, 2H) |
| I-425[b] | ALL | AJB | 868.5 | 11.09 (s, 1H), 9.50 (d, J = 6.4 Hz, 1H), 8.76 (d, J = 7.8 Hz, 1H), 8.37 (d, J = 4.4 Hz, 1H), 8.25 (d, J = 5.2 Hz, 1H), 7.26-6.85 (m, 4H), 6.85-6.37 (m, 1H), 5.35 (dd, J = 5.4, 12.4 Hz, 1H), 5.30-5.00 (m, 1H), 4.76 (d, J = 16.8 Hz, 1H), 4.23-4.10 (m, 1H), 3.83-3.72 (m, 2H), 3.65-3.59 (m, 2H), 3.54 (s, 3H), 2.93-2.83 (m, 5H), 2.69-2.58 (m, 2H), 2.17 (d, J = 6.4 Hz, 2H), 2.09-1.83 (m, 10H), 1.80-1.68 (m, 2H), 1.66-1.53 (m, 5H), 1.45-1.32 (m, 2H), 1.30-1.20 (m, 2H), 1.19-1.12 (m, 2H), 1.09-0.96 (m, 2H) |
| I-428[b] | AKP | AMT | 848.5 | 11.07 (s, 1H), 9.60 (d, J = 4.0 Hz, 1H), 8.95 (d, J = 3.2 Hz, 1H), 8.79 (d, J = 6.8 Hz, 1H), 8.29 (d, J = 5.2 Hz, 1H), 7.77 (d, J = 8.0 Hz, 2H), 7.42 (d, J = 8.4 Hz, 2H), 7.35-6.42 (m, 5H), 5.39-5.31 (m, 1H), 5.30-5.04 (m, 1H), 4.85-4.70 (m, 1H), 3.85-3.71 (m, 2H), 3.68- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | 3.58 (m, 2H), 3.53 (s, 3H), 3.49-3.46 (m, 2H), 2.88-2.84 (m, 2H), 2.82-2.77 (m, 2H), 2.75-2.68 (m, 1H), 2.64-2.54 (m,2H), 2.08-2.00 (m, 1H), 1.99-1.86 (m, 4H), 1.68-1.56 (m, 4H), 1.37-1.29 (m, 2H), 1.27-1.20 (m, 1H), 1.18-1.10 (m, 2H) |
| I-430[b] | AOH | ABC | 874.5 | 11.08 (s, 1H), 9.39 (s, 1H), 8.82 (d, J = 8.0 Hz, 1H), 8.37 (s, 1H), 8.28 (s, 1H), 7.25-6.82 (m, 5H), 5.42-5.25 (m, 1H), 4.24-4.12 (m, 1H), 3.83-3.77 (m, 4H), 3.77-3.69 (m, 5H), 3.61-3.47 (m, 5H), 3.49-3.44 (m, 2H), 3.43-3.37 (m, 2H), 2.99-2.92 (m, 2H), 2.92-2.83 (m, 1H), 2.78-2.68 (m, 2H), 2.66-2.56 (m, 2H), 2.16-2.08 (m,2H), 2.07-1.94 (m, 4H), 1.94-1.86 (m, 2H), 1.85-1.80 (m, 2H), 1.79-1.68 (m, 3H), 1.67-1.51 (m, 1H), 1.15-0.97 (m, 2H) |
| I-434[b] | AKS | AJB | 925.5 | 11.09 (s, 1H), 9.50 (d, J = 6.8 Hz, 1H), 8.78 (d, J = 7.6 Hz, 1H), 8.38 (d, J = 4.4 Hz, 1H), 8.26 (d, J = 5.6 Hz, 1H), 7.27-6.40 (m, 5H), 5.40-5.33 (m, 1H), 5.31-5.05 (m, 1H), 4.77 (d, J = 18.0 Hz, 1H), 4.24-4.12 (m, 1H), 3.84-3.72 (m, 3H), 3.66-3.59 (m, 4H), 3.57 (s, 3H), 2.93 (d, J = 7.6 Hz, 3H), 2.75-2.61 (m, 4H), 2.33-2.28 (m, 5H), 2.19 (s, 4H), 2.09-1.94 (m, 6H), 1.89 (d, J = 12.0 Hz, 2H), 1.84-1.72 (m, 6H), 1.57-1.50 (m, 2H), 1.10-0.99 (m, 2H) |
| I-436[b] | ALL | AMT | 862.5 | 11.08 (s, 1H), 9.61 (d, J = 4.8 Hz, 1H), 8.96 (d, J = 3.6 Hz, 1H), 8.79 (d, J = 7.6 Hz, 1H), 8.30 (d, J = 5.2 Hz, 1H), 7.93-7.75 (m, 2H), 7.46-7.14 (m, 3H), 6.95 (d, J = 4.8 Hz, 2H), 6.91-6.43 (m, 2H), 5.39-5.05 (m, 2H), 4.78 (d, J = 13.2 Hz, 1H), 3.84-3.73 (m, 3H), 3.67-3.60 (m, 3H), 3.54 (s, 3H), 2.90-2.86 (m, 2H), 2.79 (d, J = 10.8 Hz, 2H), 2.66-2.56 (m, 2H), 2.02-1.87 (m, 5H), 1.63-1.53 (m, 4H), 1.43-1.33 (m, 2H), 1.30-1.13 (m, 6H) |
| I-437[b] | AMC | AST | 844.4 | 11.09 (s, 1H), 9.56 (s, 1H), 8.57 (d, J = 7.6 Hz, 1H), 8.36 (s, 1H), 8.28-8.16 (m, 2H), 7.58 (dd, J = 8.4, 7.2 Hz, 2H), 7.24-6.94 (m, 3H), 6.68 (t, J = 5.6 Hz, 1H), 6.47 (d, J = 7.6 Hz, 1H),5.05 (dd, J = 12.8, 5.4 Hz, 1H), 4.20-4.10 (m, 1H), 3.50-3.40 (m, 4H), 2.95-2.83 (m, 1H), 2.62-2.52 (m, 7H), 2.32-2.30 (m, 1H), 2.12 (s, 3H), 2.08 (d, J = 6.8 Hz, 2H), 2.05-1.97 (m, 3H), 1.91-1.78 (m, 4H), 1.77-1.62 (m, 4H), 1.55-1.43 (m, 1H), 1.14-0.93 (m, 3H), 0.57-0.50 (m, 2H), 0.29-0.23 (m, 2H) |
| I-438[h] | AFJ | AMT | 878.4 | 11.09 (s, 1H), 9.62 (d, J = 4.8 Hz, 1H), 8.98 (d, J = 3.2 Hz, 1H), 8.81 (d, J = 7.6 Hz, 1H), 8.31 (d, J = 5.2 Hz, 1H), 7.79 (d, J = 8.4 Hz, 2H), 7.59 (d, J = 15.6 Hz, 1H), 7.44 (d, J = 8.4 Hz, 2H), 7.32-6.47 (m, 5H), 5.34-5.09 (m, 1H), 5.05 (d, J = 13.2 Hz, 1H), 4.80 (d, J = 14.4 Hz, 1H), 3.87-3.75 (m, 2H), 3.64 (s, 2H), 3.54-3.47 (m, 7H), 2.89 (d, J = 22.8 Hz, 1H), 2.71-2.56 (m, 4H), 2.34 (d, J = 5.2 Hz, 1H), 2.15-2.07 (m, 2H), 2.06-1.96 (m, 3H), 1.86-1.77 (m, 4H), 1.56-1.44 (m, 2H) |
| I-441[b] | ASR | ABC | 873.5 | 11.13 (s, 1H), 9.39 (s, 1H), 8.82 (d, J = 7.6 Hz, 1H), 8.59 (d, J = 4.8 Hz, 1H), 8.37 (s, 1H), 8.29 (s, 1H), 8.17 (s, 1H), 7.10-7.05 (m, 1H), 7.00-6.95 (m, 1H), 7.24-6.94 (m, 1H), 6.90 (d, J = 8.0 Hz, 1H), 5.09 (dd, J = 12.8, 5.2 Hz, 1H), 4.23-4.12 (m, 1H), 3.83-3.69 (m, 9H), 3.63-3.53 (m, 4H), 2.93-2.83 (m, 1H), 2.71-2.55 (m, 3H), 2.14-2.00 (m, 7H), 1.89-1.68 (m, 8H), 1.59-1.39 (m, 3H), 1.09-0.94 (m, 2H) |
| I-442[b] | AJI | AJB | 840.4 | 11.09 (s, 1H), 9.49 (d, J = 6.4 Hz, 1H), 8.78 (d, J = 7.6 Hz, 1H), 8.38 (d, J = 4.4 Hz, 1H), 8.25 (d, J = 5.6 Hz, 1H), 7.58 (t, 7 = 7.6 Hz, 1H), 7.26-6.95 (m, 3H), 6.89-6.43 (m, 2H), 5.29-5.01 (m, 2H), 4.76 (d, J = 20.0 Hz, 1H), 4.26-4.11 (m, 1H), 3.84-3.72 (m, 2H), 3.65-3.54 (m, 2H), 3.24-3.21 (m, 2H), 3.00-2.90 (m, 2H), 2.89-2.82 (m, 1H), 2.63-2.52 (m, 2H), 2.30-2.20 (m, 2H), 2.08-1.85 (m, 9H), 1.79-1.58 (m, 6H), 1.36-1.23 (m, 2H), 1.12-0.99 (m, 2H) |
| I-443[b] | AOS | ABC | 897.2 | 11.21-10.99 (m, 1H), 9.40 (s, 1H), 8.82 (d, J = 7.6 Hz, 1H), 8.37 (s, 1H), 8.29 (s, 1H), 7.60 (t, 7 = 7.6 Hz, 1H), 7.23-6.95 (m, 3H), 6.90 (d, J = 8.0 Hz, 1H), 6.85 (t, 7 = 4.8 Hz, 1H), 5.06 (dd, J = 5.2, 12.8 Hz, 1H), 4.23- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | ¹HNMR (400 MHz, DMSO-d$_6$) δ |
|---|---|---|---|---|
| | | | | 4.14 (m, 1H), 3.98 (d, J = 4.8 Hz, 2H), 3.88 (s, 2H), 3.79 (s, 4H), 3.75-3.70 (m, 4H), 3.61 (s, 2H), 2.95-2.82 (m, 1H), 2.63-2.54 (m, 2H), 2.31-2.17 (m, 3H), 2.12-1.99 (m, 6H), 1.88 (d, J = 12.0 Hz, 2H), 1.80-1.67 (m, 6H), 1.63-1.53 (m, 1H), 1.10-0.96 (m, 2H) |
| I-444[b] | AOQ | AJB | 884.2 | 11.09 (s, 1H), 9.49 (d, J = 6.0 Hz, 1H), 8.78 (d, J = 7.6 Hz, 1H), 8.38 (d, J = 4.0 Hz, 1H), 8.25 (d, J = 5.6 Hz, 1H), 7.58 (t, 7 = 8.0 Hz, 1H), 7.25-6.94 (m, 2H), 6.93-6.41 (m, 3H), 5.32-4.99 (m, 2H), 4.77 (d, J = 18.4 Hz, 1H), 4.23-4.09 (m, 3H), 3.83-3.61 (m, 3H), 3.59 (s, 1H), 3.44 (d, J = 11.6 Hz, 2H), 2.94-2.83 (m, 1H), 2.58 (d, J = 18.0 Hz, 1H), 2.42-2.31 (m, 5H), 2.27-2.20 (m, 2H), 2.13 (s, 3H), 2.11 (d, J = 7.6 Hz, 2H), 2.05-1.87 (m, 7H), 1.81-1.69 (m, 2H), 1.68-1.59 (m, 2H), 1.57-1.46 (m, 1H), 1.11-0.95 (m, 2H) |
| I-448[b] | APR | ABC | 874.5 | 11.09 (s, 1H), 9.39 (s, 1H), 8.82 (d, J = 8.0 Hz, 1H), 8.38 (s, 1H), 8.28 (s, 1H), 7.23-6.85 (m, 5H), 5.36 (dd, 7 = 5.2, 12.4 Hz, 1H), 4.26-4.11 (m, 1H), 3.86-3.74 (m, 5H), 3.74-3.69 (m, 4H), 3.57 (s, 5H), 3.51-3.43 (m, 3H), 3.43-3.36 (m, 2H), 3.00-2.92 (m, 2H), 2.92-2.84 (m, 1H), 2.81-2.67(m, 2H), 2.67-2.53 (m, 2H), 2.23-2.10 (m, 1H), 2.09-2.05 (m, 1H), 2.04-2.00 (m, 2H), 1.99-1.95 (m, 1H), 1.91 (d, J = 12.4 Hz, 2H), 1.87-1.78 (m, 3H), 1.78-1.68 (m, 2H), 1.68-1.56 (m, 1H), 1.15-0.96 (m, 2H) |
| I-449[i] | AKS | AMT | 919.4 | 11.09 (s, 1H), 9.61 (d, J = 4.0 Hz, 1H), 8.97 (d, J = 3.2 Hz, 1H), 8.80 (d, J = 9.2 Hz, 1H), 8.30 (d, J = 52 Hz, 1H), 7.78 (d, J = 8.4 Hz, 2H), 7.45 (d, J = 8.4 Hz, 2H), 7.31-6.45 (m, 5H), 5.36 (d, J = 17.6 Hz, 1H), 5.32-5.07 (m, 1H), 4.83-4.76 (m, 1H), 3.84 (s, 2H), 3.75 (d, J = 7.6 Hz, 1H), 3.63 (s, 2H), 3.58 (s, 3H), 3.56 (s, 3H), 3.52 (s, 4H), 2.97-2.87 (m, 3H), 2.73-2.62 (m, 2H), 2.29 (d, J = 6.4 Hz, 4H), 2.20 (s, 2H), 2.09-2.02 (m, 1H), 2.01-1.95 (m, 2H), 1.86-1.70 (m, 4H), 1.59-1.48 (m, 2H) |
| I-452 | AYI | AJB | 904.4 | 9.50 (d, J = 6.0 Hz, 1H), 8.79 (d, J = 7.6 Hz, 1H), 8.38 (d, J = 4.4 Hz, 1H), 8.26 (d, J = 5.6 Hz, 1H), 7.53-7.44 (m, 1H), 7.32-7.10 (m, 6H), 7.03-6.95 (m, 2H), 6.90-6.43 (m, 1H), 5.30-5.06 (m, 2H), 4.82-4.73 (m, 1H), 4.52 (d, J = 6.0 Hz, 2H), 4.22-4.10 (m, 1H), 3.85-3.73 (m, 2H), 3.68-3.63 (m, 1H), 3.48-3.43 (m, 1H), 3.05-2.89 (m, 4H), 2.80-2.72 (m, 1H), 2.69-2.64 (m, 2H), 2.60-2.53 (m, 2H), 2.21 (s, 3H), 2.18-2.14 (m, 2H), 2.10-1.90 (m, 6H), 1.86-1.78 (m, 2H), 1.77-1.67 (m, 2H), 1.55-1.45 (m, 1H), 1.03-0.93 (m, 2H) |
| I-453[b] | A1H | AST | 825.3 | 11.10 (s, 1H), 9.57 (m, 1H), 8.57 (d, J = 7.6 Hz, 1H), 8.38 (s, 1H), 8.29-8.23 (m, 1H), 8.19 (s, 1H), 7.59 (dd, J = 8.4, 7.2 Hz, 1H), 7.24-6.95 (m, 3H), 6.47 (d, J = 7.6 Hz, 1H), 6.16(d, J = 8.2 Hz, 1H), 5.05 (dd, J = 12.8, 5.6 Hz, 1H), 4.24-4.13 (m, 1H), 3.56-3.45 (m, 2H), 2.93-2.83 (m, 1H), 2.63-2.55 (m, 1H), 2.30-2.20 (m, 5H), 2.13-1.85 (m, 8H), 1.83-1.72 (m, 4H), 1.63-1.38 (m, 4H), 1.35-1.25 (m, 2H), 1.20-0.95 (m, 4H), 0.57-0.48 (m, 2H), 0.29-0.23 (m, 2H) |
| I-454 | AWI | AJB | 894.3 | 11.09 (s, 1H), 9.50 (d, J = 6.0 Hz, 1H), 8.78 (d, J = 1.6 Hz, 1H), 8.39 (d, J = 4.4 Hz, 1H), 8.26 (d, J = 5.6 Hz, 1H), 7.62-7.55 (m, 1H), 7.25-6.95 (m, 3H), 6.90-6.40 (m, 2H), 5.31-5.03 (m, 2H), 4.82-4.72 (m, 1H), 4.23-4.14 (m, 1H), 4.12-4.05 (m, 1H), 3.85-3.72 (m, 2H), 3.66-3.56 (m, 2H), 2.93-2.85 (m, 1H), 2.65-2.56 (m, 1H), 2.45-2.40 (m, 1H), 2.30-2.16 (m, 7H), 2.08-1.85 (m, 9H), 1.77-1.65 (m, 4H), 1.63-1.48 (m, 4H), 1.40-1.33 (m, 3H), 1.24-1.16 (m, 1H), 1.08-0.95 (m, 2H) |
| I-455[b] | AOV | AQP | 840.1 | 11.09 (s, 1H), 9.40 (s, 1H), 8.72 (d, J = 8.0 Hz, 1H), 8.37 (s, 1H), 8.25 (s, 1H), 7.58 (dd, J = 7.2, 8.4 Hz, 1H), 7.25-6.95 (m, 3H), 6.88-6.75 (m, 1H), 6.15 (d, J = 8.4 Hz, 1H), 5.04 (dd, J = 5.2, 12.8 Hz, 1H), 4.23-4.12 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | (m, 1H), 3.56 (s, 2H), 3.25 (s, 3H), 2.93-2.83 (m, 1H), 2.62-2.52 (m, 2H), 2.48-2.45 (m, 1H), 2.43-2.35 (m, 1H), 2.22 (d, J = 6.8 Hz, 2H), 2.20 (s, 3H), 2.08-1.99 (m, 5H), 1.90 (d, J = 11.6 Hz, 2H), 1.80-1.69 (m, 4H), 1.52-1.36 (m, 3H), 1.34-1.23 (m, 2H), 1.12-0.96 (m, 3H), 0.54-0.45 (m, 2H), 0.38-0.28 (m, 2H) |
| I-456[b] | AOU | AGD | 897.3 | 11.09 (s, 1H), 9.48 (s, 1H), 8.87 (s, 1H), 8.84 (d, J = 8.0 Hz, 1H), 8.78 (s, 2H), 8.32 (s, 1H), 7.62-7.56 (m, 1H), 7.26 (t, J = 53.2 Hz, 1H), 7.10 (d, J = 8.4 Hz, 1H), 7.02 (d, J = 7.2 Hz, 1H), 6.92 (d, J = 8.0 Hz, 1H), 6.67 (t, J = 6.0 Hz, 1H), 5.08-5.01 (m, 1H), 3.87-3.68 (m, 12H), 3.49-3.38 (m, 8H), 2.95-2.82 (m, 1H), 2.63-2.52 (m, 2H), 2.42 (t, J = 4.4 Hz, 2H), 2.38 (t, J = 7.6 Hz, 2H), 2.07-1.98 (m, 1H), 1.86-1.78 (m, 2H), 1.77-1.69 (m, 2H) |
| I-457[b] | AOW | AJB | 826.2 | 11.10 (s, 1H), 9.50 (d, J = 6.4 Hz, 1H), 8.78 (d, J = 1.6 Hz, 1H), 8.39 (d, J = 4.4 Hz, 1H), 8.26 (d, J = 5.6 Hz, 1H), 7.66-7.53 (m, 1H), 7.27-6.96 (m, 2H), 6.93-6.40 (m, 3H), 5.31-4.72 (m, 3H), 4.25-4.00 (m, 2H), 3.85-3.42 (m, 4H), 3.33-3.33 (m, 3H), 3.30-3.30 (m, 1H), 2.95-2.84 (m, 1H), 2.64-2.52 (m, 2H), 2.15-1.89 (m, 14H), 1.82-1.71 (m, 2H), 1.13-0.99 (m, 2H) |
| I-458[b] | AOW | ABC | 814.1 | 11.11 (s, 1H), 9.40 (s, 1H), 8.83 (d, J = 8.0 Hz, 1H), 8.39 (s, 1H), 8.29 (s, 1H), 7.61 (t, J = 7.2 Hz, 1H), 7.28-6.86 (m, 4H), 6.52-6.49 (m, 1H), 5.06 (dd, J = 5.6, 12.8 Hz, 1H), 4.26-4.14 (m, 1H), 4.10-3.99 (m, 1H), 3.86-3.68 (m, 8H), 3.37-3.34 (m, 3H), 2.96-2.81 (m, 1H), 2.64-2.52 (m, 2H), 2.21-1.85 (m, 12H), 1.82-1.71 (m, 2H), 1.63-1.46 (m, 1H), 1.13-0.98 (m, 2H) |
| I-459 | AYG | ABC | 856.4 | 11.10 (s, 1H), 9.40 (s, 1H), 8.83 (d, J = 8.0 Hz, 1H), 8.38 (s, 1H), 8.31-8.24 (m, 2H), 7.58 (dd, J = 7.2, 8.4 Hz, 1H), 7.24-6.96 (m, 3H), 6.93-6.89 (m, 1H), 6.58 (t, J = 6.4 Hz, 1H), 5.10-5.02 (m, 1H), 4.23-4.09 (m, 1H), 3.84-3.69 (m, 9H), 2.89 (s, 2H), 2.24-2.15 (m, 5H), 2.10-1.63 (m, 13H), 1.52 (s, 2H), 1.28-0.93 (m, 7H) |
| I-460[b] | ASP | AJB | 898.4 | 11.08 (s, 1H), 9.49 (d, J = 6.4 Hz, 1H), 8.77 (d, J = 8.0 Hz, 1H), 8.37 (d, J = 4.4 Hz, 1H), 8.25 (d, J = 5.6 Hz, 1H), 7.61-7.54 (m, 1H), 7.27-6.94 (m, 3H), 6.89-6.41 (m, 2H), 5.30-5.00 (m, 2H), 4.76 (d, J = 17.2 Hz, 1H), 4.17(t, J = 11.2 Hz, 1H), 3.84-3.56 (m, 5H), 3.50-3.41 (m, 2H), 3.28-3.25 (m, 2H), 2.93-2.82 (m, 1H), 2.69 (d, J = 10.4 Hz, 1H), 2.65-2.54 (m, 2H), 2.52 (d, J = 2.0 Hz, 1H), 2.12-1.82 (m, 10H), 1.80-1.52 (m, 6H), 1.45-1.28 (m, 6H), 1.10-0.96 (m, 2H) |
| I-461[b] | APB | AJB | 852.5 | 11.10 (s, 1H), 9.50 (d, J = 5.9 Hz, 1H), 8.79 (d, J = 7.8 Hz, 1H), 8.44-8.35 (m, 1H), 8.26 (d, J = 5.6 Hz, 1H), 7.58 (t, J = 7.8 Hz, 1H), 7.27-6.96 (m, 3H), 6.89-6.44 (m, 2H), 5.30-5.02 (m, 2H), 4.77 (br d, J = 17.6 Hz, 1H), 4.22-4.12 (m, 1H), 3.86-3.77 (m, 2H), 3.74 (br d, J = 7.8 Hz, 1H), 3.64 (br d, J = 10.0 Hz, 1H), 3.60 (s, 1H), 3.21 (br s, 3H), 2.95-2.87 (m, 1H), 2.63-2.56 (m, 1H), 2.53 (d, J = 2.0 Hz, 2H), 2.43-2.38 (m, 1H), 2.31-2.27 (m, 1H), 2.19 (br t, J = 10.4 Hz, 2H), 2.08-1.78 (m, 10H), 1.77-1.64 (m, 2H), 1.57-1.46 (m, 1H), 1.43-1.25 (m, 1H), 1.13-0.98 (m, 2H) |
| I-462[b] | AJF | AMT | 874.2 | 11.07 (s, 1H), 9.59 (d, J = 5.2 Hz, 1H), 9.03-8.90 (m, 1H), 8.79 (d, J = 6.4 Hz, 1H), 8.28 (d, J = 5.2 Hz, 1H), 7.85-7.70 (m, 1H), 7.59-7.52 (m, 1H), 7.48-7.39 (m, 2H), 7.30-6.89 (m, 3H), 6.46-6.43 (m, 1H), 5.31-5.02 (m, 2H), 4.82-4.73 (m, 1H), 3.86-3.74 (m, 2H), 3.66-3.58 (m, 2H), 3.48-3.40 (m, 2H), 3.29-3.27 (m, 3H), 2.93-2.77 (m, 2H), 2.61-2.51 (m, 6H), 2.09-1.78 (m, 5H), 1.66-1.45 (m, 6H) |
| I-463[b] | AOV | AJB | 854.0 | 11.09 (s, 1H), 9.50 ( d, J = 6.0 Hz, 1H), 8.78 (d, J = 7.6 Hz, 1H), 8.39 (d, J = 4.4 Hz, 1H), 8.25 (d, J = 5.6 Hz, 1H), 7.58 (t, J = 8.0 Hz, 1H), 7.27-6.94 (m, 3H), 6.90-6.41(m, 1H), 6.15 (d, J = 8.0 Hz, 1H), 5.31-4.99 (m, 2H), 4.77 (d, J = 16.8 Hz, 1H), 4.23-4.12 (m, 1H), 3.83-3.72 (m, 2H), 3.66-3.57 (m, 2H), 3.52-3.49 (m, 1H), 2.92-2.83 (m, 1H), 2.64-2.52 (m, 2H), 2.42-2.36 (m, 1H), 2.22 (d, J = 6.8 Hz, 2H), 2.20 (s, 3H), 2.07-1.98 |

TABLE 7-continued

Compounds synthesized via Method 2 with the reductive
amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | (m, 6H), 1.96-1.85 (m, 3H), 1.79-1.68 (m, 4H), 1.52-1.36 (m, 3H), 1.35-1.22 (m, 2H), 1.08-0.94 (m, 2H) |
| I-465$^b$ | WX | AJB | 855.1 | 11.10 (s, 1H), 9.60 (d, J = 6.0 Hz, 1H), 8.78 (d, J = 7.6 Hz, 1H), 8.37 (d, J = 4.4 Hz, 1H), 8.25 (d, J = 5.6 Hz, 1H), 7.25-6.42 (m, 5H), 5.38 (dd, J = 5.2. 12.8 Hz, 1H), 5.30-5.03 (m, 1H), 4.77 (d, J = 17.6 Hz, 1H), 4.24-4.09 (m, 1H), 3.85-3.72 (m, 2H), 3.67 (s, 3H), 3.63-3.58 (m, 3H), 3.46-3.42 (m, 2H), 2.92-2.81 (m, 4H), 2.20 (d, J = 6.8 Hz, 2H), 2.17 (s, 3H), 2.06-1.83 (m, 10H), 1.75-1.60 (m, 4H), 1.55-1.43 (m, 1H), 1.41-1.30 (m, 2H), 1.08-0.93 (m, 2H) |
| I-466$^i$ | AMS | AMT | 860.5 | 11.09 (s, 1H), 9.61 (d, J = 4.4 Hz, 1H), 8.96 (d, J = 3.2 Hz, 1H), 8.80 (d, J = 7.6 Hz, 1H), 8.30 (d, J = 5.2 Hz, 1H), 7.77 (d, J = 8.4 Hz, 2H), 7.42 (d, J = 8.4 Hz, 2H), 7.32-7.12 (m, 1H), 6.98-6.46 (m, 4H), 5.35 (dd, J = 5.2, 12.8 Hz, 1H), 5.31-5.05 (m, 1H), 4.78 (d, J = 13.6 Hz, 1H), 4.45-4.30 (m, 1H), 3.83 (s, 1H), 3.78-3.70 (m, 1H), 3.63 (s, 1H), 3.53 (s, 3H), 3.45-3.42 (m, 2H), 3.02 (d, J = 7.2 Hz, 2H), 2.93-2.83 (m, 1H), 2.75-2.68 (m, 1H), 2.64-2.59 (m, 1H), 2.30-2.21 (m, 2H), 2.06-1.93 (m, 3H), 1.87 (t, J = 9.6 Hz, 2H), 1.59-1.47 (m, 5H), 1.05 (t, J = 6.8 Hz, 4H) |
| I-467$^b$ | ANI | AJB | 937.6 | 11.09 (s, 1H), 9.50 (d, J = 6.4 Hz, 1H), 8.78 (d, J = 7.6 Hz, 1H), 8.38 (d, J = 4.4 Hz, 1H), 8.26 (d, J = 5.6 Hz, 1H), 7.27-6.89 (m, 4H), 6.89-6.42 (m, 1H), 5.43-5.31 (m, 1H), 5.30-5.05 (m, 1H), 4.82-4.70 (m, 1H), 4.24-4.11 (m, 1H), 3.84-3.74 (m, 2H), 3.67-3.59 (m, 2H), 3.58 (s, 3H), 3.48-3.46 (m, 2H), 3.16-3.12 (m, 2H), 2.93-2.84 (m, 1H), 2.76-2.63 (m, 4H), 2.35-2.28 (m, 4H), 2.19-2.10 (m, 2H), 2.08-1.82 (m, 8H), 1.79-1.67 (m, 2H), 1.63-1.52 (m, 1H), 1.48-1.38 (m, 4H), 1.34-1.23 (m, 4H), 1.17-0.93 (m, 3H) |
| I-468 | TN | AUY | 858.5 | 11.09 (s, 1H), 9.42 (s, 1H), 8.83 (d, J = 8.0 Hz, 1H), 8.28 (s, 1H), 8.05 (s, 1H), 7.65-7.36 (m, 1H), 6.98-6.85 (m, 4H), 5.36 (dd, J = 5.2 Hz, 12.8 Hz, 1H), 4.23 (m, 1H), 3.77 (d, J = 4.4 Hz, 4H), 3.72 (br d, J = 4.8 Hz, 4H), 3.57 (s, 3H), 3.47-3.44 (m, 3H), 2.98-2.93 (m, 2H), 2.92-2.84 (m, 1H), 2.77-2.69 (m, 1H), 2.65-2.56 (m, 2H), 2.12-1.77 (m, 16H), 1.58-1.40 (m, 3H), 1.09-0.97 (m, 2H) |
| I-469 | AUW | AJB | 896.5 | 11.09 (s, 1H), 9.49 (d, J = 6.4 Hz, 1H), 8.78 (d, J = 7.6 Hz, 1H), 8.37 (d, J = 4.4 Hz, 1H), 8.25 (d, J = 5.6 Hz, 1H), 7.25-6.89 (m, 4H), 6.88-6.42 (m, 1H), 5.37 (dd, J = 5.6, 12.4 Hz, 1H), 5.28-5.07 (m, 1H), 4.81-4.73 (m, 1H), 4.22-4.11 (m, 1H), 3.94 (t, J = 6.8 Hz, 1H), 3.83-3.74 (m, 2H), 3.66-3.48 (m, 9H), 3.14-3.10 (m, 2H), 2.85-2.71 (m, 2H), 2.25-2.15 (m, 3H), 2.09-1.98 (m, 8H), 1.86 (d, J = 11.6 Hz, 2H), 1.77-1.67 (m, 2H), 1.59-1.38 (m, 8H), 1.06-0.96 (m, 2H) |
| I-470 | AMP | AJB | 916.4 | 11.08 (s, 1H), 9.50 (d, J = 5.6 Hz, 1H), 8.78 (d, J = 7.6 Hz, 1H), 8.39 (d, J = 4.0 Hz, 1H), 8.26 (d, J = 5.6 Hz, 1H), 7.25-6.43 (m, 5H), 5.41-5.05 (m, 2H), 4.77 (d, J = 18.4 Hz, 1H), 4.23-4.15 (m, 1H), 3.85-3.78 (m, 2H), 3.74 (d, J = 7.6 Hz, 1H), 3.65-3.58 (m, 3H), 3.57 (s, 3H), 3.00-2.93 (m, 3H), 2.89-2.81 (m, 2H), 2.74-2.70 (m, 1H), 2.64-2.57 (m, 2H), 2.25-2.23 (m, 2H), 2.08-1.66 (m, 15H), 1.59-1.49 (m, 3H), 1.46-1.37 (m, 1H), 1.20-1.10 (m, 2H) |
| I-471$^b$ | ANH | AJB | 869.6 | 11.08 (s, 1H), 9.49 (d, J = 6.4 Hz, 1H), 8.77 (d, J = 7.6 Hz, 1H), 8.37 (d, J = 4.4 Hz, 1H), 8.25 (d, J = 5.6 Hz, 1H), 7.10 (d, J = 3.6 Hz, 1H), 6.96 (d, J = 4.8 Hz, 2H), 6.89-6.43 (m, 2H), 5.36 (dd, J = 5.6, 12.4 Hz, 1H), 5.29-5.05 (m, 1H), 4.81-4.72 (m, 1H), 4.22-4.11 (m, 1H), 3.84-3.72 (m, 3H), 3.65-3.59 (m, 2H), 3.57 (s, 3H), 2.93-2.86 (m, 3H), 2.73-2.58 (m, 3H), 2.52 (d, J = 2.0 Hz, 1H), 2.40-2.32 (m, 6H), 2.11 (d, J = 7.6 Hz, 2H), 2.07-1.83 (m, 8H), 1.79-1.68 (m, 2H), 1.63-1.50 (m, 5H), 1.08-0.097 (m, 2H) |
| I-473 | AYE | ABC | 926.6 | 11.09 (s, 1H), 9.39 (s, 1H), 8.82 (d, J = 8.0 Hz, 1H), 8.37 (s, 1H), 8.29 (s, 1H), 7.57 (dd, J = 8.4, 7.2 Hz, 1H), 7.25-6.95 (m, 3H), 6.90 (d, J = 8.0 Hz, 1H), 6.57 (t, J = 6.0 Hz, 1H), 5.05 (dd, J = 12.8, 5.2 Hz, 1H), 4.23- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | 4.13 (m, 1H), 3.83-3.76 (m, 4H), 3.75-3.69 (m, 4H), 3.43-3.39 (m, 1H), 3.30-3.37 (m, 1H), 3.16 (t, J = 6.4 Hz, 2H), 2.95-2.83 (m, 1H), 2.72-2.65 (m, 2H), 2.63-2.53 (m, 2H), 2.13-2.00 (m, 6H), 1.95-1.83 (m, 4H), 1.81-1.68 (m, 6H), 1.61-1.47 (m, 2H), 1.45-1.34 (m, 2H), 1.15-0.95 (m, 6H) |
| I-474[b] | APH | APJ | 895.3 | 11.09 (s, 1H), 10.89-10.78 (m, 1H), 9.60 (d, J = 3.2 Hz, 1H), 8.95 (d, J = 3.6 Hz, 1H), 8.90 (s, 2H), 8.80 (d, J = 7.2 Hz, 1H), 8.29 (d, J = 5.2 Hz, 1H), 7.64-7.57 (m, 1H), 7.44-7.14 (m, 2H), 7.05 (d, J = 7.2 Hz, 1H), 6.91-6.46 (m, 2H), 5.31-5.03 (m, 2H), 4.78 d, J = 16.0 Hz, 1H), 4.71 (d, J = 13.6 Hz, 2H), 3.87-3.72 (m, 3H), 3.66-3.61 (m, 5H), 3.52-3.43 (m, 6H), 3.21-3.12 (m, 2H), 3.11-3.00 (m, 2H), 2.94-2.83 (m, 1H), 2.63-2.53 (m, 2H), 2.10-1.92 (m, 5H) |
| I-475 | AUE | AJB | 913.5 | 11.1 (s, 1H), 9.49 (d, J = 6.4 Hz, 1H), 8.78 (d, J = 8.0 Hz, 1H), 8.37 (d, J = 4.4 Hz, 1H), 8.25 (d, J = 5.6 Hz, 1H), 7.60-7.55 (m, 1H), 7.23-6.96 (m, 3H), 6.87-6.44 (m, 2H), 5.28-5.02 (m, 2H), 4.76 (d, J = 18.4 Hz, 1H), 4.20-4.14 (m, 1H), 3.83-3.59 (m, 6H), 3.54-3.44 (m, 3H), 2.92-2.80 (m, 2H), 2.65-2.56 (m, 2H), 2.30-2.26 (m, 4H), 2.11 (s, 3H), 2.09 (d, J = I2 Hz, 2H), 2.04-1.80 (m, 10H), 1.78-1.67 (m, 2H), 1.57-1.49 (m, 3H), 1.06-0.97 (m, 2H) |
| I-476[j] | AOV | ATY | 836.4 | 11.08 (s, 1H), 9.50 (s, 1H), 8.96 (s, 1H), 8.84 (d, J = 8.0 Hz, 1H), 8.32 (s, 1H), 7.77 (d, J = 8.4 Hz, 2H), 7.58 (d, J = 15.6 Hz, 1H), 7.45 (d, J = 8.4 Hz, 2H), 7.41-7.13 (m, 2H), 7.02 (d, J = 6.8 Hz, 1H), 6.92 (d, J = 8.0 Hz, 1H), 6.16 (d, J = 8.0 Hz, 1H), 5.04 (d, J = 16.0 Hz, 1H), 3.81 (s, 4H), 3.74 (d, J = 4.4 Hz, 4H), 3.60 (s, 2H), 2.93-2.78 (m, 1H), 2.69-2.51 (m, 3H), 2.14 (s, 3H), 2.10-1.94 (m, 4H), 1.87 (d, J = 12.0 Hz, 2H), 1.53 (d, J = 11.2 Hz, 2H), 1.37-1.21 (m, 2H) |
| I-478 | AOV | AUU | 841.2 | 11.09 (s, 1H), 9.90 (s, 1H), 9.29 (d, J = 7.1 Hz, 1H), 8.64 (s, 1H), 8.41 (s, 1H), 7.59 (dd, J = 7.2. 8.4 Hz, 1H), 7.33 (d, J = 7.3 Hz, 1H), 7.30-7.01 (m, 3H), 6.16 (d, J = 8.1 Hz, 1H), 5.05 (dd, J = 5.4. 12.7 Hz, 1H), 4.28-4.17 (m, 1H), 4.04-3.98 (m, 2H), 3.51-3.47 (m, 2H), 3.19-3.14 (m, 1H), 2.94-2.84 (m, 1H), 2.63-2.56 (m, 1H), 2.43 (d, J = 1.1 Hz, 1H), 2.26 (d, J = 6.8 Hz, 2H), 2.23 (s, 3H), 2.11-1.99 (m, 6H), 1.96-1.88 (m, 6H), 1.78 (d, J = 11.6 Hz, 4H), 1.52-1.39 (m, 3H), 1.38-1.22 (m, 3H), 1.10-0.96 (m, 2H) |
| I-481[b] | TN | APN | 808.2 | 11.09 (s, 1H), 9.63 (s, 1H), 9.38 (dd, J = 1.6, 7.2 Hz, 1H), 8.90 (dd, J = 1.6, 4.4 Hz, 1H), 8.66 (s, 1H), 8.03 (s, 1H), 7.33 (dd, J = 4.4. 7.2 Hz, 1H), 7.01-6.94 (m, 2H), 6.92-6.84 (m, 1H), 5.40-5.31 (m, 1H), 4.08-3.97 (m, 1H), 3.87-3.76 (m, 4H), 3.71-3.64 (m, 1H), 3.58 (d, J = 9.6 Hz, 3H), 3.53-3.48 (m, 2H), 3.40-3.34 (m, 1H), 3.05-2.83 (m, 11H), 2.75-2.61 (m, 2H), 2.20-1.55 (m, 15H), 1.31-1.05 (m, 2H) |
| I-482[b] | AYC | AJB | 886.5 | 11.18 (s, 1H), 9.50 (s, 1H), 8.91-8.74 (m, 2H), 8.55-8.23 (m, 3H), 7.71 (s, 1H), 7.60-7.50 (m, 1H), 7.45-7.30 (m, 2H), 7.26-6.94 (m, 1H), 6.88-6.40 (m, 1H), 6.10 (s, 1H), 5.30-5.03 (m, 1H), 4.82-4.72 (m, 1H), 4.71-4.61 (m, 2H), 4.22-4.12 (m, 1H), 3.81 (s, 1H), 3.75-3.67 (m, 2H), 3.61-3.58 (m, 1H), 3.09-2.96 (m, 2H), 2.78-2.68 (m, 3H), 2.21-2.14 (m, 4H), 2.09-1.53 (m, 15H), 1.10-0.96 (m, 2H) |
| I-483 | AUS | AJB | 866.0 | 11.13 (s, 1H), 9.51 (d, J = 6.0 Hz, 1H), 8.80 (d, J = 7.6 Hz, 1H), 8.39 (d, J = 4.0 Hz, 1H), 8.27 (d, J = 5.6 Hz, 1H), 7.34 (s, 1H), 7.30-6.95 (m, 3H), 6.94-6.40 (m, 1H), 5.40 (dd, J = 5.2. 12.8 Hz, 1H), 5.32-5.05 (m, 1H), 4.78 (d, J = 17.2 Hz, 1H), 4.40 (s, 2H), 4.18 (d, J = 2.8 Hz, 1H), 3.85-3.73 (m, 2H), 3.66-3.36 (m, 3H), 3.32 (s, 3H), 2.97-2.85 (m, 1H), 2.78-2.61 (m, 4H), 2.15-1.99 (m, 8H), 1.98-1.83 (m, 5H), 1.80-1.68 (m, 2H), 1.68-1.49 (m, 3H), 1.10-0.98 (m, 2H) |
| I-484 | TN | ATR | 911.5 | 11.19-10.80 (m, 2H), 8.78 (d, J = 7.8 Hz, 1H), 8.49-8.11 (m, 3H), 7.94-7.60 (m, 2H), 6.97 (d, J = 4.6 Hz, 2H), 6.92-6.43 (m, 2H), 5.37 (dd, J = 5.6, 12.4 Hz, 1H), 5.24-5.05 (m, 1H), 4.81-4.10 (m, 2H), 3.87- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 3.60 (m, 2H), 3.58 (s, 3H), 3.52-3.42 (m, 3H), 3.28-3.22 (m, 1H), 3.01-2.83 (m, 3H), 2.74-2.60 (m, 4H), 2.36-2.30 (m, 3H), 2.14-2.06 (m, 4H), 2.06-1.95 (m, 4H), 1.93-1.91 (m, 2H), 1.88-1.70 (m, 7H), 1.67-1.35 (m, 4H), 1.19-0.98 (m, 2H) |
| I-485[b] | ASB | AJB | 891.6 | 11.13 (s, 1H), 9.50 (d, J = 6.4 Hz, 1H), 8.79 (d, J = 7.6 Hz, 1H), 8.39 (d, J = 4.0 Hz, 1H), 8.25 (d, J = 5.6 Hz, 1H), 7.26-6.96 (m, 4H), 6.90-6.43 (m, 1H), 5.40 (dd, J = 5.6, 12.4 Hz, 1H), 5.30-5.05 (m, 1H), 4.83-4.70 (m, 1H), 4.31-4.13 (m, 1H), 3.85-3.77 (m, 2H), 3.76-3.71 (m, 1H), 3.65 (s, 3H), 3.63-3.51 (m, 6H), 3.47-3.42 (m, 1H), 2.95-2.74 (m, 3H), 2.73-2.67 (m, 1H), 2.65-2.58 (m, 1H), 2.45-2.39 (m, 2H), 2.09-1.89 (m, 6H), 1.88-1.48 (m, 10H), 1.20-1.04 (m, 2H) |
| I-486[b] | APZ | AJB | 880.4 | 11.09 (s, 1H), 9.50 (d, J = 6.0 Hz, 1H), 8.78 (d, J = 7.6 Hz, 1H), 8.38 (d, J = 4.8 Hz, 1H), 8.26 (d, J = 5.6 Hz, 1H), 7.28-6.93 (m, 3H), 6.88-6.43 (m, 2H), 5.36 (J = 5.2, 12.8 Hz, 1H), 5.30-5.06 (m, 1H), 4.80-4.76 (m, 1H), 4.22-4.14 (m, 1H), 3.83-3.67 (m, 3H), 3.56 (s, 3H), 2.93-2.60 (m, 6H), 2.31-2.19 (m, 4H), 2.10-1.86 (m, 11H), 1.79-1.67 (m, 4H), 1.60-1.35 (m, 7H), 1.10-0.97 (m, 2H) |
| I-487[b] | APY | AJB | 840.5 | 11.08 (s, 1H) 9.49 (d, J = 5.6 Hz, 1H) 8.78 (d, J = 7.6 Hz, 1H) 8.38 (d, J = 4.0 Hz, 1H) 8.25 (d, J = 5.6 Hz, 1H) 7.10 (d, J = 3.2 Hz, 1H) 6.43-6.89 (m, 2H) 5.36 (dd, J = 12.4, 5.6 Hz, 1H) 5.04-5.30 (m, 1H) 4.71-4.82 (m, 1H) 4.12-4.22 (m, 1H) 3.60-3.80 (m, 3H) 3.56 (s, 3H) 2.70-2.95 (m, 6H) 1.94-2.13 (m, 8H) 1.68-1.91 (m, 9H) 1.48-1.58 (m, 3H) 1.14-1.32 (m, 3H) 0.98-1.09 (m, 2H) |
| I-488 | TN | AUR | 818.5 | 11.08 (s, 1H), 9.42 (s, 1H), 8.82 (d, J = 8.0 Hz, 1H), 8.28 (s, 1H), 8.06 (s, 1H), 7.63-7.29 (m, 1H), 6.95 (d, J = 4.8 Hz, 2H), 6.90 (d, J = 8.0 Hz, 1H), 6.87-6.83 (m, 1H), 5.38-5.31 (m, 1H), 4.23-4.17 (m, 2H), 3.80-3.68 (m, 9H), 3.55 (s, 3H), 3.49-3.39 (m, 3H), 3.29 (s, 3H), 2.94 (t, J = 7.2 Hz, 2H), 2.63-2.57 (m, 1H), 2.06-1.88 (m, 3H), 1.87-1.70 (m, 7H), 1.68-1.23 (m, 5H) |
| I-491[b] | AYB | AJB | 854.5 | 11.08 (s, 1H), 9.49 (d, J = 5.8 Hz, 1H), 8.79 (d, J = 7.8 Hz, 1H), 8.34 (d, J = 4.4 Hz, 1H), 8.26 (d, J = 5.6 Hz, 1H), 7.64-7.56 (m, 1H), 7.29 (d, J = 8.8 Hz, 1H), 7.24-6.93 (m, 2H), 6.90-6.43 (m, 2H), 5.32-5.03 (m, 2H), 4.78 (d, J = 16.8 Hz, 1H), 4.17-4.05 (m, 1H), 3.85-3.72 (m, 2H), 3.67-3.57 (m, 2H), 3.53 (d, J = 5.4 Hz, 2H), 3.45 (d, J = 10.0 Hz, 2H), 2.93-2.83 (m, 1H), 2.59 (d, J = 2.6 Hz, 1H), 2.56-2.53 (m, 2H), 2.42 (s, 2H), 2.15 (s, 3H), 2.12 (d, J = 7.0 Hz, 2H), 1.97-1.77 (m, 10H), 1.72-1.58 (m, 2H), 1.56-1.45 (m, 1H), 0.98 (q, J = 11.8 Hz, 2H) |
| I-492[b] | AOJ | AJB | 895.4 | 1.02-1.17 (m, 2 H), 1.43-1.55 (m, 3 H), 1.57-1.68 (m, 4 H), 1.71-1.83 (m, 4 H), 1.89-1.91 (m, 1 H), 1.90-2.10 (m, 7 H), 2.15-2.25 (m, 4 H), 2.29-2.34 (m, 2 H), 2.58-2.75 (m, 3 H), 2.80-3.00 (m, 3 H), 3.16 (s, 2 H), 3.52-3.68 (m, 5 H), 3.70-3.90 (m, 2 H), 4.18 (t, J = 10.0 Hz, 1 H), 4.77 (d, J = 14.0 Hz, 1 H), 5.05-5.31 (m, 1 H), 5.37 (dd, J = 12.0, 6.0 Hz, 1 H), 6.41-6.91 (m, 2 H), 6.91-7.30 (m, 3 H), 8.10-8.48 (m, 2 H), 8.79 (d, J = 8.0 Hz, 1 H), 9.50 (d, J = 6.0 Hz, 1 H), 11.09 (s, 1 H) |
| I-493[b] | ARP | AJB | 909.5 | 11.08 (s, 1H), 9.50 (d, J = 6.4 Hz, 1H), 8.77 (d, J = 7.8 Hz, 1H), 8.39 (d, J = 4.0 Hz, 1H), 8.26 (d, J = 5.4 Hz, 1H), 7.26-7.00 (m, 1H), 6.99-6.94 (m, 2H), 6.89-6.42 (m, 2H), 5.36 (dd, J = 5.2, 12.4 Hz, 1H), 5.30-5.05 (m, 1H), 4.77 (d, J = 16.4 Hz, 1H), 4.17 (t, J = 10.4 Hz, 1H), 3.98 (d, J = 11.6 Hz, 1H), 3.82-3.73 (m, 2H), 3.66-3.54 (m, 6H), 3.48-3.42 (m, 3H), 3.22-3.15 (m, 2H), 2.96-2.83 (m, 3H), 2.75-2.65 (m, 2H), 2.44-2.25 (m, 2H), 2.18-1.93 (m, 9H), 1.85-1.68 (m, 6H), 1.52-1.38 (m, 2H), 1.08-1.04 (m, 2H) |
| I-497[b] | APX | AJB | 883.6 | 11.08 (s, 1H), 9.50 (d, J = 6.0 Hz, 1H), 8.78 (d, J = 7.8 Hz, 1H), 8.39 (d, J = 4.4 Hz, 1H), 8.26 (d, J = 5.6 Hz, 1H), 7.28-6.94 (m, 3H), 6.91-6.41 (m, 2H), 5.37 (dd, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | J = 5.4, 12.3 Hz, 1H), 5.31-5.05 (m, 1H), 4.77 (d, J = 16.8 Hz, 1H), 4.26-4.12 (m, 1H), 3.86-3.72 (m, 2H), 3.68-3.51 (m, 5H), 3.48-3.42 (m, 4H), 2.97-2.84 (m, 3H), 2.70-2.59 (m, 2H), 2.43 (t, J = 7.2 Hz, 2H), 2.36-2.27 (m, 4H), 2.14 (d, J = 7.2 Hz, 2H), 2.07-1.70 (m, 11H), 1.67-1.54 (m, 1H), 1.13-0.99 (m, 2H) |
| I-500[b] | ASU | AJB | 899.3 | 11.08 (s, 1H), 9.49 (d, J = 5.6 Hz, 1H), 8.78 (d, J = 7.6 Hz, 1H), 8.37 (d, J = 4.4 Hz, 1H), 8.25 (d, J = 5.4 Hz, 1H), 7.62-7.54 (m, 1H), 7.25-6.95 (m, 3H), 6.89-6.43 (m, 2H), 5.31-5.00 (m, 2H), 4.81-4.72 (m, 1H), 4.21-4.11 (m, 1H), 3.84-3.71 (m, 3H), 3.66-3.57 (m, 3H), 3.53-3.41 (m, 6H), 2.91-2.83 (m, 2H), 2.73-2.68 (m, 1H), 2.61-2.56 (m, 1H), 2.41 (d, J = 4.0 Hz, 4H), 2.15 (s, 3H), 2.12-1.86 (m, 10H), 1.81-1.68 (m, 2H), 1.08-0.96 (m, 2H) |
| I-501[b] | AFJ | AQU | 886.6 | 11.09 (s, 1H), 8.63 (d, J = 7.6 Hz, 1H), 7.87 (s, 1H), 7.78-7.35 (m, 2H), 7.10 (d, J = 8.8 Hz, 1H), 7.02 (d, J = 6.8 Hz, 1H), 6.99-6.69 (m, 2H), 6.63 (t, J = 5.2 Hz, 1H), 5.05 (dd, J = 5.2, 13.2 Hz, 1H), 4.07-3.97 (m, 1H), 3.71-3.67 (m, 4H), 3.66-3.63 (m, 4H), 3.52-3.46 (m, 2H), 3.40-3.36 (m, 4H), 3.25 (s, 3H), 2.94-2.84 (m, 1H), 2.65-2.55 (m, 3H), 2.07-1.95 (m, 5H), 1.90-1.74 (m, 8H), 1.65-1.52 (m, 2H), 1.51-1.38 (m, 3H), 1.04-0.89 (m, 2H) |
| I-503[b] | AIR | AQU | 920.3 | 10.98 (s, 1H), 8.63 (d, J = 8.0 Hz, 1H), 7.87 (s, 1H), 7.73-7.52 (m, 1H), 7.52-7.40 (m, 3H), 7.35-7.28 (m, 4H), 7.01-6.69 (m, 2H), 5.22 (s, 2H), 5.11 (dd, J = 4.8, 13.2 Hz, 1H), 4.44-4.22 (m, 2H), 4.08-3.97 (m, 1H), 3.70-3.62 (m, 8H), 3.45 (s, 2H), 3.25 (s, 3H), 3.00-2.82 (m, 2H), 2.62-2.53 (m, 2H), 2.45-2.30 (m, 7H), 2.08 (d, J = 6.8 Hz, 2H), 2.03-1.93 (m, 1H), 1.92-1.78 (m, 4H), 1.65-1.43 (m, 3H), 1.03-0.91 (m, 2H) |
| I-505 | AQS | AJB | 896.3 | 11.10 (s, 1H), 9.49 (d, J = 6.0 Hz, 1H), 8.78 (d, J = 7.6 Hz, 1H), 8.38 (d, J = 4.4 Hz, 1H), 8.27-8.22 (m, 1H), 7.59 (d, J = 15.6 Hz, 1H), 7.26-6.42 (m, 5H), 5.30-5.02 (m, 2H), 4.81-4.73 (m, 1H), 4.30 (d, J = 6.0 Hz, 1H), 4.23-4.07 (m, 2H), 3.83-3.72 (m, 2H), 3.66-3.57 (m, 2H), 2.89 (d, J = 35.6 Hz, 1H), 2.73-2.66 (m, 2H), 2.66-2.55 (m, 2H), 2.41-2.31 (m, 3H), 2.30-2.20 (m, 2H), 2.12-1.93 (m, 9H), 1.87 (d, J = 10.4 Hz, 2H), 1.83-1.67 (m, 4H), 1.60-1.49 (m, 1H), 1.47-1.36 (m, 2H), 1.09-0.96 (m, 2H) |
| I-506[b] | AQS | ABC | 884.5 | 11.10 (s, 1H), 9.39 (s, 1H), 8.82 (d, J = 8.0 Hz, 1H), 8.37 (s, 1H), 8.28 (s, 1H), 7.63-7.54 (m, 1H), 7.24-6.94 (m, 2H), 6.90 (dd, J = 4.0, 8.0 Hz, 2H), 6.49 (d, J = 5.6 Hz, 1H), 5.06 (dd, J = 5.2. 12.8 Hz, 1H), 4.34-4.25 (m, 1H), 4.21-4.06 (m, 2H), 3.82-3.76 (m, 4H), 3.74-3.70 (m, 4H), 2.93-2.85 (m, 1H), 2.71-2.65 (m, 2H), 2.64-2.53 (m, 2H), 2.40-2.34 (m, 2H), 2.28-2.21 (m, 2H), 2.08 (d, J = 7.2 Hz, 2H), 2.06-1.66 (m, 12H), 1.59-1.50 (m, 1H), 1.47-1.36 (m, 2H), 1.11-0.93 (m, 2H) |
| I-508 | AVU | AJB | 854.6 | 11.09 (s, 1H), 9.49 (d, J = 6.0 Hz, 1H), 8.77 (d, J = 7.8 Hz, 1H), 8.37 (d, J = 4.4 Hz, 1H), 8.25 (d, J = 5.6 Hz, 1H), 7.25-6.98 (m, 1H), 6.97-6.90 (m, 2H), 6.87-6.43 (m, 2H), 5.36 (dd, J = 5.6. 12.6 Hz, 1H), 5.29-5.02 (m, 1H), 4.76 (d, J = 17.6 Hz, 1H), 4.16(t, J = 10.0 Hz, 1H), 3.82-3.60 (m, 4H), 3.53 (s, 3H), 2.99-2.79 (m, 2H), 2.79-2.56 (m, 5H), 2.42-2.30 (m, 2H), 2.23 (d, J = 6.4 Hz, 2H), 2.18 (s, 3H), 2.04-1.86 (m, 6H), 1.72 (t, 7 = 13.2 Hz, 6H), 1.50-1.39 (m, 2H), 1.24-0.94 (m, 6H) |
| I-509 | AOD | AUN | 839.1 | 12.19 (s, 1H), 11.11 (s, 1H), 9.37 (dd, J = 1.6, 7.2 Hz, 1H), 9.14 (dd, J = 1.6, 4.4 Hz, 1H), 8.72-8.65 (m, 2H), 8.48 (s, 1H), 7.86 (d, J = 8.4 Hz, 1H), 7.76-7.68 (m, 1H), 7.35 (dd, J = 4.4, 6.4 Hz, 1H), 6.9-6.83 (m, 3H), 5.37 (dd, J = 6.4, 12.4 Hz, 1H), 4.25-4.18 (m, 1H), |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | 3.58 (s, 3H), 3.09-3.01 (m, 4H), 2.96-2.84 (m, 4H), 2.65 (d, J = 4.4 Hz, 3H), 2.41 (s, 3H), 2.36-2.32 (m, 2H), 2.16-2.07 (m, 4H), 2.04-1.97 (m, 1H), 1.96-1.87 (m, 2H), 1.85-1.75 (m, 2H), 1.71-1.58 (m, 7H), 1.14-1.00 (m, 2H) |
| I-510[b] | ARK | ARM | 841.6 | 11.10 (s, 1H), 9.49 (d, J = 6.4 Hz, 1H), 8.76 (d, J = 7.6 Hz, 1H), 8.36 (d, J = 4.8 Hz, 1H), 8.30-8.20 (m, 1H), 7.25-6.93 (m, 3H), 6.88 (d, J = 7.6 Hz, 1H), 6.86-6.36 (m, 1H), 5.38-5.26 (m, 1H), 5.30-5.01 (m, 1H), 4.76 (d, J = 15.6 Hz, 1H), 4.24-4.09 (m, 1H), 3.86-3.72 (m, 2H), 3.66 (s, 3H), 3.64-3.56 (m, 4H), 3.44-3.44 (m, 2H), 2.93-2.83 (m, 1H), 2.78-2.58 (m, 3H), 2.45-2.35 (m, 4H), 2.31-2.24 (m, 3H), 2.04-1.90 (m, 5H), 1.82 (d, J = 12.4 Hz, 2H), 1.76-1.63 (m, 2H), 1.36-1.25 (m, 3H), 1.14-1.01 (m, 2H) |
| I-511[b] | ARN | ARM | 867.6 | 11.10 (s, 1H), 9.50 (d, J = 6.0 Hz, 1H), 8.76 (d, J = 7.6 Hz, 1H), 8.37 (d, J = 4.4 Hz, 1H), 8.25-8.21 (m, 1H), 7.26-6.97 (m, 2H), 6.96 (s, 1H), 6.88 (d, J = 7.6 Hz, 1H), 6.86-6.40 (m, 1H), 5.36 (dd, J = 5.2, 12.4 Hz, 1H), 5.30-5.00 (m, 1H), 4.76 (d, J = 16.4 Hz, 1H), 4.17 (t, J = 10.4 Hz, 1H), 3.83-3.72 (m, 2H), 3.68 (s, 3H), 3.64-3.56 (m, 4H), 3.48-3.46 (m, 2H), 3.19 (s, 2H), 2.87 (dd, J = 4.8, 16.4 Hz, 1H), 2.74-2.59 (m, 2H), 2.38-2.31 (m, 2H), 2.27 (d, J = 9.6 Hz, 2H), 2.05-1.90 (m, 5H), 1.84 (d, J = 12.8 Hz, 2H), 1.79-1.64 (m, 4H), 1.55 (d, J = 7.6 Hz, 2H), 1.36 (s, 3H), 1.18-1.04 (m, 2H) |
| I-512 | ATV | AJB | 810.1 | 11.61-10.64 (m, 1H), 9.50 (d, J = 6.0 Hz, 1H), 8. 78 (d, J = 8.0 Hz, 1H), 8. 40 (d, J = 4.4 Hz, 1H), 8. 25 (d, J = 5. 6 Hz, 1H), 7.24 (s, 1H), 7.14-6.95 (m, 3H), 6.45 (d, J = 8.0 Hz, 1H), 6.87 (d, J = 8.0 Hz, 1H), 5.37 (dd, J = 5.6, 12.8 Hz, 1H), 5.27 (s, 1H), 5.08 (s, 1H), 4.81-4.73 (m, 1H), 4.24-4.15 (m, 1H), 3.84-3.73 (m, 2H), 3.59 (s, 3H), 3.33 (s, 3H), 2.83 (d, J = 6.4 Hz, 3H), 2.75-2.66 (m, 1H), 2.74-2.57 (m, 1H), 2.07-1.90 (m, 7H), 1.86-1.53 (m, 6H), 1.15-1.11 (m, 2H) |
| I-513[b] | AZX | AJB | 925.0 | 11.10 (s, 1H), 9.49 (d, J = 6.4 Hz, 1H), 8.78 (d, J = 7.6 Hz, 1H), 8.38 (d, J = 4.4 Hz, 1H), 8.25 (d, J = 5.6 Hz, 1H), 8.18 (s, 2H), 7.24-6.85 (m, 5H), 5.38-5.35 (m, 1H), 5.30-5.27 (m, 1H), 4.79-4.74 (m, 1H), 4.17-4.13 (m, 2H), 3.80-3.75 (m, 2H), 3.74-3.71 (m, 1H), 3.45-3.44 (m, 3H), 3.43-3.40 (m, 2H), 2.73-2.70 (m, 1H), 2.71-2.65 (m, 6H), 2.14-1.39 (m, 26H), 1.06-1.03 (m, 2H) |
| I-514[b] | ASA | ARY | 844.1 | 11.09 (s, 1H), 9.30 (s, 1H), 8.78 (d, J = 8.0 Hz, 1H), 8.37 (s, 1H), 8.27 (s, 1H), 8.14 (s, 1H), 7.24-6.94 (m, 3H), 6.90-6.79 (m, 2H), 5.39-5.34 (m, 1H), 4.24-4.11 (m, 1H), 4.10-3.73 (m, 7H), 3.68-3.65 (m, 2H), 3.56 (s, 3H), 3.50-3.41 (m, 1H), 3.10-3.05 (m, 1H), 2.97-2.84 (m, 2H), 2.80-2.68 (m, 2H), 2.67-2.57 (m, 2H), 2.11 (m, 2H), 2.02-1.99 (m, 4H), 1.94-1.84 (m, 4H), 1.81-1.66 (m, 5H), 1.61-1.59 (m, 1H), 1.12-0.96 (m, 2H) |
| I-515[b] | TN | AQF | 872.1 | 11.09 (s, 1H), 9.30 (m, 1H), 8.77 (d, J = 8.0 Hz, 1H), 8.37 (s, 1H), 8.27 (s, 1H), 8.18 (s, 1H), 7.25-6.97 (m, 1H), 6.96 (d, J = 4.8 Hz, 2H), 6.89-6.79 (m, 2H), 5.36 (dd, J = 5.6, 12.4, 1H), 4.24-4.12 (m, 1H), 4.09-3.70 (m, 8H), 3.70-3.61 (m, 3H), 3.57 (s, 3H), 3.01-2.84 (m, 3H), 2.70-2.66 (m, 2H), 2.16-1.95 (m, 8H), 1.94-1.74 (m, 10H), 1.67-1.34 (m, 4H), 1.11-0.94 (m, 2H) |
| I-516 | AUM | AQF | 844.4 | 11.10 (s, 1H), 9.31 (s, 1H), 8.79 (d, J = 8.0 Hz, 1H), 8.38 (s, 1H), 8.28 (s, 1H), 7.27-6.92 (m, 3H), 6.90-6.77 (m, 2H), 5.43-5.29 (m, 1H), 4.26-4.13 (m, 1H), 4.05-3.76 (m, 7H), 3.67 (t, J = 5.6 Hz, 2H), 3.57 (s, 3H), 3.55-3.48 (m, 2H), 3.09-3.04 (m, 1H), 2.99-2.86 (m, 2H), 2.81-2.69 (m, 2H), 2.68-2.58 (m, 2H), 2.21-2.09 (m, 2H), 2.07-1.94 (m, 4H), 1.93-1.82 (m, 4H), 1.80-1.66 (m, 5H), 1.65-1.51 (m, 1H), 1.12-0.94 (m, 2H) |
| I-517[b] | AQN | ARS | 917.5 | 11.09 (s, 1H), 9.50 (d, J = 6.0 Hz, 1H), 8.78 (d, J = 7.6 Hz, 1H), 8.39 (d, J = 4.0 Hz, 1H), 8.25 (d, J = 5.6 Hz, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| | | | | 1H), 7.27-7.07 (m, 3H), 6.99-6.94 (m, 2H), 6.91-6.43 (m, 4H), 5.40-5.32 (m, 1H), 5.30-5.03 (m, 1H), 4.76 (d, J = 17.2 Hz, 1H), 4.25-4.15 (m, 1H), 3.84-3.72 (m, 2H), 3.70-3.64 (m, 2H), 3.57 (s, 3H), 3.02-2.79 (m, 6H), 2.75-2.58 (m, 6H), 2.09-1.84 (m, 12H), 1.60-1.54 (m, 2H), 1.38-1.27 (m, 2H) |
| I-518[b] | AQJ | AJB | 810.1 | 11.39-10.86 (m, 1H), 9.49 (d, J = 6.0 Hz, 1H), 8.78 (d, J = 7.6 Hz, 1H), 8.45-8.16 (m, 2H), 7.38-6.33 (m, 5H), 5.38 (dd, J = 5.2, 12.8 Hz, 1H), 5.30-5.02 (m, 1H), 4.77 (d, J = 17.6 Hz, 1H), 4.16(s, 1H), 3.86-3.70 (m, 2H), 3.66-3.41 (m, 5H), 2.94-2.82 (m, 1H), 2.76-2.53 (m, 7H), 2.40 (d, J = 6.4 Hz, 2H), 2.08-1.86 (m, 7H), 1.71 (t, J = 6.8 Hz, 4H), 1.51-1.38 (m, 1H), 1.17-1.00 (m, 2H) |
| I-519[b] | AXZ | AXY | 915.5 | 11.15 (s, 1H), 9.50 (d, J = 6.4 Hz, 1H), 8.78 (d, J = 1.6 Hz, 1H), 8.55 (d, J = 8.0 Hz, 1H), 8.44 (d, J = 4.0 Hz, 1H), 8.38 (d, J = 4.0 Hz, 1H), 8.25 (d, J = 5.6 Hz, 1H), 7.53-7.42 (m, 2H), 7.32-7.27 (m, 1H), 7.25-6.95 (m, 2H), 6.90-6.43 (m, 1H), 6.19-5.91 (m, 1H), 5.31-5.03 (m, 1H), 4.76 (d, J = 18.8 Hz, 1H), 4.22-4.12 (m, 1H), 3.92-3.72 (m, 3H), 3.67-3.56 (m, 3H), 3.46-3.43 (m, 2H), 3.20-3.17 (m, 2H), 3.06-3.02 (m, 1H), 2.90-2.33 (m, 2H), 2.71 (d, J = 14.0 Hz, 1H), 2.53-2.52 (m, 1H), 2.31-2.23 (m, 3H), 2.13-1.69 (m, 19H), 1.61-1.53 (m, 1H), 1.08-0.96 (m, 2H) |
| I-520 | AQN | ATS | 903.5 | 11.10 (s, 1H), 9.50 (d, J = 5.6 Hz, 1H), 8.79 (d, J = 7.6 Hz, 1H), 8.40 (d, J = 4.0 Hz, 1H), 8.31-8.22 (m, 1H), 7.31-7.01 (m, 3H), 7.01-6.94 (m, 2H), 6.91-6.85 (m, 3H), 6.85 (s, 1H), 5.38 (dd, J = 5.6, 12.4 Hz, 1H), 5.30-5.02 (m, 1H), 4.77 (d, J = 18.4 Hz, 1H), 4.35-4.14 (m, 1H), 3.84-3.72 (m, 2H), 3.70-3.60 (m, 3H), 3.58 (s, 3H), 3.49-3.43 (m, 2H), 3.04-2.84 (m, 5H), 2.80-2.69 (m, 1H), 2.68-2.56 (m, 4H), 2.26-2.09 (m, 2H), 2.08-1.90 (m, 7H), 1.78-1.64 (m, 3H), 1.46-1.30 (m, 2H) |
| I-521[b] | TN | ASE | 884.4 | 11.10 (s, 1H), 9.42 (s, 1H), 8.82 (d, J = 8.0 Hz, 1H), 8.38 (s, 1H), 8.29 (s, 1H), 7.30-6.94 (m, 3H), 6.91-6.79 (m, 2H), 5.37 (dd, J = 5.6, 12.4 Hz, 1H), 4.46 (d, J = 0.8 Hz, 2H), 4.29-4.07 (m, 2H), 3.58 (s, 3H), 3.46 (t, J = 6.4 Hz, 2H), 3.30-3.16 (m, 4H), 3.00-2.85 (m, 3H), 2.74-2.69 (m, 1H), 2.67-2.60 (m, 2H), 2.22-1.95 (m, 7H), 1.95-1.65 (m, 13H), 1.63-1.41 (m, 3H), 1.14-0.93 (m, 2H), LC-MS (ESI+) m/z 884.4 (M + H)+. |
| I-522 | APT | AQF | 868.6 | 11.13 (s, 1H), 9.30 (s, 1H), 8.78 (d, J = 8.0 Hz, 1H), 8.27 (s, 1H), 7.24-6.96 (m, 4H), 6.83 (d, J = 8.0 Hz, 1H), 5.40 (dd, J = 5.6, 12.4 Hz, 1H), 4.48 (s, 2H), 4.24-4.12 (m, 1H), 4.06-3.82 (m, 4H), 3.80-3.75 (m, 2H), 3.68-3.65 (m, 2H), 3.64 (s, 3H), 3.61-3.53 (m, 1H), 2.93-2.84 (m, 1H), 2.78-2.68 (m, 3H), 2.65-2.59 (m, 1H), 2.19-2.09 (m, 3H), 2.08-1.98 (m, 4H), 1.93-1.85 (m, 6H), 1.78-1.67 (m, 2H), 1.62-1.44 (m, 3H), 1.12-0.97 (m, 2H) |
| I-523[b] | AQI | AQF | 852.5 | 11.11 (s, 1H), 9.30 (s, 1H), 8.78 (d, J = 8.0 Hz, 1H), 8.38 (s, 1H), 8.27 (s, 1H), 7.25-6.95 (m, 4H), 6.83 (d, J = 8.0 Hz, 1H), 5.38 (dd, J = 5.6, 12.8 Hz, 1H), 4.24-4.10 (m, 1H), 4.08-3.81 (m, 4H), 3.80-3.75 (m, 2H), 3.69-3.65 (m, 2H), 3.63 (s, 3H), 2.92-2.83 (m, 3H), 2.76-2.68 (m, 1H), 2.65-2.59 (m, 1H), 2.45 (d, J = 6.4 Hz, 2H), 2.13 (d, J = 7.2 Hz, 2H), 2.07-1.99 (m, 3H), 1.94-1.85 (m, 6H), 1.80-1.68 (m, 4H), 1.62-1.50 (m, 2H), 1.40-1.28 (m, 2H), 1.10-0.97 (m, 2H) |
| I-524[b] | AKP | AQF | 856.5 | 11.10 (s, 1H), 9.31 (s, 1H), 8.78 (d, J = 8.0 Hz, 1H), 8.38 (s, 1H), 8.28 (s, 1H), 7.26-6.92 (m, 3H), 6.90-6.80 (m, 2H), 5.41-5.33 (m, 1H), 4.27-4.12 (m, 1H), 4.08-3.84 (m, 4H), 3.81-3.76 (m, 2H), 3.69-3.65 (m, 2H), 3.55 (s, 3H), 2.91-2.78 (m, 5H), 2.77-2.68 (m, 1H), 2.66-2.57 (m, 1H), 2.15-2.08 (m, 2H), 2.07-1.98 (m, 3H), 1.95-1.82 (m, 6H), 1.79-1.69 (m, 2H), 1.67-1.54 (m, 5H), 1.39-1.29 (m, 2H), 1.28-1.20 (m, 1H), 1.19-1.10 (m, 2H), 1.07-0.95 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-d$_6$) δ |
|---|---|---|---|---|
| I-525$^b$ | AKP | AQD | 870.6 | 11.11 (s, 1H), 9.30 (s, 1H), 8.81 (d, J = 8.0 Hz, 1H), 8.39 (s, 1H), 8.31-8.25 (m, 1H), 7.30-7.00 (m, 1H), 6.99-6.91 (m, 3H), 6.90-6.83 (m, 1H), 5.37 (dd, J = 5.6, 12.4 Hz, 1H), 4.23-4.13 (m, 1H), 3.83-3.75 (m, 5H), 3.67 (s, 3H), 3.55 (s, 3H), 2.93-2.83 (m, 5H), 2.76-2.62 (m, 2H), 2.19 (d, J = 6.8 Hz, 2H), 2.07-1.85 (m, 7H), 1.77-1.56 (m, 7H), 1.36-1.29 (m, 2H), 1.20 (s, 6H), 1.19-1.16 (m , 1H), 1.10-1.04 (m, 2H) |
| I-526$^b$ | ARJ | AJB | 868.4 | 11.08 (s, 1H), 9.50 (d, J = 6.4 Hz, 1H), 8.78 (d, J = 1.6 Hz, 1H), 8.38 (d, J = 4.4 Hz, 1H), 8.26 (d, J = 5.6 Hz, 1H), 7.27-6.96 (m, 1H), 6.95-6.90 (m, 1H), 6.87-6.43 (m, 3H), 5.33 (dd, J = 5.6, 12.8 Hz, 1H), 5.28 (s, 1H), 4.86-4.73 (m, 2H), 4.22-4.11 (m, 1H), 3.84-3.73 (m, 2H), 3.66-3.57 (m, 2H), 3.54 (s, 3H), 2.92-2.84 (m, 1H), 2.71-2.59 (m, 2H), 2.41-2.36 (m, 2H), 2.29-2.20 (m, 2H), 2.11 (d, J = 6.4 Hz, 2H), 2.06-1.96 (m, 5H), 1.94-1.80 (m, 5H), 1.78-1.53 (m, 8H), 1.08-0.97 (m, 2H) |
| I-527$^b$ | APT | ASH | 882.6 | 11.12 (s, 1H), 9.30 (s, 1H), 8.79 (d, J = 8.0 Hz, 1H), 8.38 (s, 1H), 8.27 (s, 1H), 7.29-6.97 (m, 4H), 6.90 (d, J = 8.0 Hz, 1H), 5.46-5.34 (m, 1H), 4.47 (s, 2H), 4.17 (t, 7 = 11.6 Hz, 1H), 4.11-4.02 (m, 2H), 3.98-3.83 (m, 2H), 3.64 (s, 3H), 3.61-3.54 (m, 2H), 3.53-3.46 (m, 2H), 2.91-2.84 (m, 1H), 2.77-2.70 (m, 2H), 2.65-2.58 (m, 1H), 2.23-2.08 (m, 4H), 2.07-1.99 (m, 3H), 1.96-1.83 (m, 4H), 1.81-1.67 (m, 2H), 1.64-1.45 (m, 3H), 1.17 (d, J = 6.4 Hz, 6H), 1.10-0.97 (m, 2H) |
| I-528$^b$ | AQI | ASH | 891.6 | 11.11 (s, 1H), 9.30 (s, 1H), 8.79 (d, J = 7.6 Hz, 1H), 8.38 (s, 1H), 8.27 (s, 1H), 7.29-6.95 (m, 4H), 6.90 (d, J = 8.0 Hz, 1H), 5.38 (dd, J = 5.2, 12.4 Hz, 1H), 4.24-4.12 (m, 1H), 4.10-4.01 (m, 2H), 3.99-3.82 (m, 2H), 3.63 (s, 3H), 3.53-3.46 (m, 2H), 2.97-2.90 (m, 2H), 2.90-2.82 (m, 1H), 2.75-2.68 (m, 1H), 2.65-2.58 (m, 1H), 2.47-2.44 (m, 2H), 2.28-2.16 (m, 2H), 2.08-1.97 (m, 5H), 1.88 (d, J = 11.6 Hz, 2H), 1.83-1.67 (m, 4H), 1.66-1.51 (m, 2H), 1.43-1.30 (m, 2H), 1.17 (d, J = 6.4 Hz, 6H), 1.11-0.98 (m, 2H) |
| I-529 | AQI | ASH | 866.5 | 11.11 (s, 1H), 9.31 (s, 1H), 8.80 (d, J = 8.0 Hz, 1H), 8.40 (s, 1H), 8.27 (s, 1H), 8.14 (s, 1H), 7.29-6.97 (m, 4H), 6.91 (d, J = 8.0 Hz, 1H), 5.38 (dd, J = 5.2, 12.8 Hz, 1H), 4.26-4.14 (m, 1H), 4.12-4.02 (m, 2H), 4.00-3.79 (m, 2H), 3.64 (s, 3H), 3.50 (dd, J = 6.8, 13.2 Hz, 2H), 3.20-3.12 (m, 2H), 2.95-2.82 (m, 1H), 2.77-2.67 (m, 1H), 2.65-2.59 (m, 1H), 2.54-2.51 (m, 2H), 2.47-2.21 (m, 3H), 2.17-1.57 (m, 12H), 1.56-1.41 (m, 2H), 1.17 (d, J = 6.4 Hz, 6H), 1.14-1.01 (m, 2H) |
| I-530$^b$ | AQI | ASF | 866.5 | 11.11 (s, 1H), 9.27 (s, 1H), 8.82 (d, J = 8.0 Hz, 1H), 8.39 (s, 1H), 8.28 (s, 1H), 7.41-6.71 (m, 5H), 5.47-5.28 (m, 1H), 4.58-4.29 (m, 2H), 4.22-4.17 (m, 1H), 3.69-3.65 (m, 1H), 3.64 (s, 3H), 3.62-3.59 (m, 1H), 2.98-2.85 (m, 3H), 2.77-2.62 (m, 4H), 2.47-2.45 (m, 2H), 2.30-2.13 (m, 2H), 2.12-1.94 (m, 5H), 1.94-1.85 (m, 2H), 1.83-1.67 (m, 4H), 1.66-1.49 (m, 2H), 1.45-1.29 (m, 2H), 1.20 (s, 3H), 1.18 (s, 3H), 1.11-0.96 (m, 2H) |
| I-531$^b$ | APT | ASF | 882.6 | 11.14 (s, 1H), 9.29 (s, 1H), 8.97-8.74 (m, 1H), 8.50-8.39 (m, 1H), 8.29 (s, 1H), 7.36-7.16 (m, 2H), 7.15-7.10 (m, 1H), 7.09-7.01 (m, 1H), 7.00-6.91 (m, 1H), 5.51-5.34 (m, 1H), 4.53 (s, 2H), 4.51-4.09 (m, 3H), 3.84-3.67 (m, 2H), 3.66 (s, 3H), 3.10-3.00 (m, 2H), 2.96-2.86 (m, 2H), 2.79-2.68 (m, 4H), 2.15-1.46 (m, 16H), 1.21 (s, 3H), 1.20 (s, 3H), 1.17-1.07 (m, 2H) |
| I-532$^b$ | AQI | AQD | 866.5 | 11.11 (s, 1H), 9.29 (s, 1H), 8.80 (d, J = 7.6 Hz, 1H), 8.41-8.24 (m, 2H), 7.29-7.09 (m, 2H), 7.08-7.04 (m, 1H), 7.02-6.97 (m, 1H), 6.93 (d, J = 8.0 Hz, 1H), 5.38 (dd, J = 5.2, 12.8 Hz, 1H), 4.23-4.13 (m, 1H), 3.82-3.75 (m, 4H), 3.67 (s, 2H), 3.63 (s, 3H), 2.93-2.82 (m, 3H), 2.69-2.58 (m, 2H), 2.45 (d, J = 6.4 Hz, 2H), 2.14 |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| | | | | (d, J = 6.4 Hz, 2H), 2.06-1.98 (m, 3H), 1.96-1.84 (m, 4H), 1.80-1.70 (m, 4H), 1.62-1.51 (m, 2H), 1.40-1.28 (m, 2H), 1.19 (s, 6H), 1.10-0.96 (m, 2H) |
| I-533[b] | APT | AQD | 882.6 | 11.13 (s, 1H), 9.29 (s, 1H), 8.80 (d, J = 8.0 Hz, 1H), 8.39 (s, 1H), 8.28 (s, 1H), 7.29-7.08 (m, 3H), 7.07-6.99 (m, 1H), 6.93 (d, J = 8.0 Hz, 1H), 5.40 (dd, J = 5.2, 12.8 Hz, 1H), 4.50 (s, 2H), 4.26-4.13 (m, 1H), 3.75-3.70 (s, 4H), 3.67 (s, 2H), 3.64 (s, 3H), 3.48 (s, 1H), 3.00-2.79 (m, 3H), 2.77-2.70 (m, 1H), 2.67-2.55 (m, 2H), 2.61 (s, 1H), 2.15-1.85 (m, 8H), 1.84-1.44 (m, 6H), 1.19 (s, 6H), 1.15-1.00 (m, 2H) |
| I-534[b] | AQI | ASE | 864.5 | 11.11 (s, 1H), 9.41 (s, 1H), 8.81 (d, J = 8.0 Hz, 1H), 8.38 (s, 1H), 8.28 (s, 1H), 7.25-6.95 (m, 4H), 6.82 (d, J = 8.0 Hz, 1H), 5.38 (dd, J = 5.2, 12.8 Hz, 1H), 4.45 (s, 2H), 4.28-4.11 (m, 2H), 3.64 (s, 3H), 3.28-3.16 (m, 4H), 3.04 (d, J = 6.8 Hz, 2H), 2.93-2.58 (m, 4H), 2.40-2.34 (m, 1H), 2.28-2.09 (m, 2H), 2.07-1.98 (m, 3H), 1.96-1.55 (m, 13H), 1.49-1.36 (m, 2H), 1.14-1.00 (m, 2H) |
| I-535[b] | AKP | ASE | 868.6 | 11.09 (s, 1H), 9.41 (s, 1H), 8.80 (d, J = 8.0 Hz, 1H), 8.37 (s, 1H), 8.28 (s, 1H), 7.24-6.93 (m, 3H), 6.88-6.78 (m, 2H), 5.36 (dd, J = 5.6, 12.4 Hz, 1H), 4.44 (s, 2H), 4.18-4.14 (m, 2H), 3.54 (s, 3H), 3.27-3.18 (m, 2H), 2.92-2.78 (m, 5H), 2.74-2.60 (m, 2H), 2.13-1.97 (m, 5H), 1.91-1.54 (m, 16H), 1.35-1.20 (m, 3H), 1.17-0.96 (m, 4H) |
| I-536 | APT | ASL | 882.1 | 11.13 (s, 1H), 9.31 (s, 1H), 8.81 (d, J = 8.0 Hz, 1H), 8.40 (s, 1H), 8.28 (s, 1H), 7.29-7.00 (m, 4H), 6.91 (d, J = 8.0 Hz, 1H), 5.40 (dd, J = 12.8, 5.2 Hz, 1H), 4.51 (s, 2H), 4.22-4.18 (m, 1H), 4.09-4.06 (m, 2H), 3.93-3.89 (m, 2H), 3.80-3.68 (m, 1H), 3.65 (s, 3H), 3.50 (dd, J = 13.2, 6.8 Hz, 2H), 2.96-2.83 (m, 2H), 2.78-2.63 (m, 3H), 2.52 (d, J = 2.0 Hz, 3H), 2.12-1.83 (m, 8H), 1.82-1.46 (m, 5H), 1.17 (d, J = 6.4 Hz, 6H), 1.16-1.12 (m, 2H) |
| I-537[b] | AKP | ASH | 870.6 | 11.09 (s, 1H), 9.30 (s, 1H), 8.80 (d, J = 8.0 Hz, 1H), 8.38 (s, 1H), 8.27 (s, 1H), 7.31-6.98 (m, 1H), 6.98-6.84 (m, 4H), 5.36 (dd, J = 5.2, 12.8 Hz, 1H), 4.22-4.12 (m, 1H), 4.09-4.05 (m, 2H), 3.98-3.84 (m, 2H), 3.54 (s, 3H), 3.50 (d, J = 6.4 Hz, 2H), 2.90-2.77 (m, 5H), 2.76-2.68 (m, 1H), 2.65-2.57 (m, 1H), 2.11 (d, J = 7.2 Hz, 2H), 2.07-1.97 (m, 3H), 1.92-1.80 (m, 4H), 1.78-1.68 (m, 2H), 1.67-1.55 (m, 5H), 1.37-1.28 (m, 2H), 1.27-1.20 (m, 1H), 1.17 (d, J = 6.4 Hz, 6H), 1.15-1.08 (m, 2H), 1.07-0.96 (m, 2H) |
| I-538[b] | AKP | ASJ | 882.5 | 11.18-10.99 (m, 1H), 9.34 (s, 1H), 8.83 (d, J = 7.6 Hz, 1H), 8.39 (s, 1H), 8.3 (s, 1H), 7.29-6.84 (m, 5H), 5.39-5.35 (m, 1H), 4.23-4.11 (m, 1H), 3.77 (s, 4H), 3.70-3.61 (m, 2H), 3.55 (s, 3H), 2.92-2.58 (m, 8H), 2.11-1.96 (m, 8H), 1.92-1.56 (m, 13H), 1.39-0.96 (m, 7H) |
| I-539[b] | TN | AQD | 886.5 | 11.17-11.00 (m, 1H), 9.30 (s, 1H), 8.81 (d, J = 8.0 Hz, 1H), 8.40 (s, 1H), 8.29 (s, 1H), 7.32-7.00 (m, 1H), 6.99-6.86 (m, 4H), 5.39-5.35 (m, 1H), 4.24-4.12 (m, 1H), 3.83-3.72 (m, 4H), 3.68 (s, 2H), 3.58 (s, 3H), 3.46 (t, J = 5.6 Hz, 2H), 3.03-2.82 (m, 4H), 2.78-2.58 (m, 5H), 2.14-2.03 (m, 4H), 1.95-1.41 (m, 13H), 1.20 (s, 6H), 1.06-1.02 (m, 2H) |
| I-540 | AKP | ASF | 870.6 | 9.38 (s, 1H), 8.44 (s, 1H), 8.40 (s, 1H), 8.34 (d, J = 8.0 Hz, 1H), 7.02-6.95 (m, 1H), 6.93-6.63 (m, 3H), 6.44 (d, J = 8.0 Hz, 1H), 5.28-5.13 (m, 1H), 4.48-4.12 (m, 2H), 4.11-4.01 (m, 1H), 3.82-3.68 (m, 2H), 3.66 (s, 3H), 3.08-3.01 (m, 2H), 2.98-2.72 (m, 8H), 2.37-2.33 (m, 2H), 2.25-2.17 (m, 4H), 2.05-1.99 (m, 4H), 1.82-1.78 (m, 2H), 1.72-1.67 (m, 3H), 1.46-1.34 (m, 5H), 1.33 (s, 3H), 1.32 (s, 3H), 1.18-1.09 (m, 2H) |
| I-541 | APT | ASJ | 894.6 | 11.14 (s, 1H), 9.35 (s, 1H), 8.84 (d, J = 8.0 Hz, 1H), 8.39 (s, 1H), 8.30 (s, 1H), 7.31-6.99 (m, 5H), 5.51-5.30 (m, 1H), 4.49 (s, 2H), 4.27-4.09 (m, 1H), 3.77 (s, 4H), 3.69-3.55 (m, 6H), 2.96-2.72 (m, 3H), 2.69-2.59 (m, 2H), 2.29-2.12 (m, 3H), 2.10-1.85 (m, 12H), 1.81-1.69 (m, 4H), 1.65-1.48 (m, 3H), 1.14-0.98 (m, 2H) |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | $^1$HNMR (400 MHz, DMSO-$d_6$) δ |
|---|---|---|---|---|
| I-542[b] | TN | ASJ | 898.1 | 11.21-10.93 (m, 1H), 9.34 (s, 1H), 8.81 (d, J = 8.0 Hz, 1H), 8.38 (s, 1H), 8.29 (s, 1H), 7.27-7.03 (m, 1H), 7.01 (d, J = 1.2 Hz, 1H), 6.96 (d, J = 4.8 Hz, 2H), 6.87 (m, 1H), 5.36 (dd, J = 5.2, 12.4 Hz, 1H), 4.20-4.13 (m, 1H), 3.79-3.72 (m, 5H), 3.67-3.61 (m, 3H), 3.57 (s, 4H), 3.51 (s, 1H), 3.45 (s, 2H), 2.99-2.92 (m, 3H), 2.92-2.83 (m, 2H), 2.70-2.66 (m, 2H), 2.09 (d, J = 6.8 Hz, 2H), 1.96 (m, 3H), 1.92-1.69 (m, 13H), 1.59-1.51 (m, 1H), 1.48-1.40 (m, 2H), 1.06-0.97 (m, 2H) |
| I-543[b] | AKP | ASL | 870.5 | 11.09 (s, 1H), 9.30 (s, 1H), 8.80 (d, J = 8.0 Hz, 1H), 8.38 (s, 1H), 8.27 (s, 1H), 7.29-6.99 (m, 1H), 6.95 (d, J = 5.2 Hz, 2H), 6.91 (d, J = 8.0 Hz, 1H), 6.89-6.83 (m, 1H), 5.36 (dd, J = 5.6, 12.4 Hz, 1H), 4.23-4.12 (m, 1H), 4.07 (m, 2H), 3.97-3.85 (m, 2H), 3.54 (s, 3H), 3.50 (d, J = 6.4 Hz, 2H), 2.92-2.77 (m, 6H), 2.67-2.58 (m, 2H), 2.08 (d, J = 6.8 Hz, 2H), 1.97-1.77 (m, 6H), 1.75-1.68 (m, 2H), 1.68-1.56 (m, 6H), 1.37-1.26 (m, 3H), 1.17 (d, J = 6.4 Hz, 6H), 1.08-0.95 (m, 3H) |
| I-544[b] | AQB | AJB | 880.6 | 11.12 (s, 1H), 9.50 (d, J = 6.4 Hz, 1H), 8.78 (d, J = 8.0 Hz, 1H), 8.38 (d, J = 4.0 Hz, 1H), 8.25 (d, J = 5.6 Hz, 1H), 7.29-6.95 (m, 4H), 6.92-6.40 (m, 1H), 5.44-5.34 (m, 1H), 5.30-5.03 (m, 1H), 4.82-4.70 (m, 1H), 4.70-4.60 (m, 1H), 4.27-4.12 (m, 1H), 3.84-3.69 (m, 3H), 3.64 (s, 3H), 3.61-3.42 (m, 3H), 2.97-2.78 (m, 3H), 2.76-2.68 (m, 1H), 2.65-2.58 (m, 1H), 2.11-1.82 (m, 11H), 1.81-1.50 (m, 6H), 1.44 (d, J = 6.4 Hz, 3H), 1.14-1.01 (m, 2H) |
| I-545[b] | AQC | AJB | 884.6 | 11.09 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.27-6.43 (m, 5H), 5.41-5.32 (m, 1H), 5.30-5.05 (m, 1H), 4.83-4.71 (m, 1H), 4.28-4.14 (m, 1H), 3.83-3.73 (m, 2H), 3.68-3.60 (m, 2H), 3.58 (s, 3H), 3.48-3.45 (m, 2H), 3.12-3.03 (m, 2H), 2.96-2.78 (m, 3H), 2.76-2.69 (m, 1H), 2.65-2.59 (m, 1H), 2.16-2.06 (m, 4H), 2.05-1.97 (m, 4H), 1.95-1.85 (m, 3H), 1.84-1.76 (m, 2H), 1.76-1.64 (m, 4H), 1.61-1.53 (m, 1H), 1.51-1.41 (m, 2H), 1.12 (d, J = 6.0 Hz, 3H), 1.09-0.98 (m, 2H) |
| I-547 | APT | ASE | 880.4 | 11.14 (s, 1H), 9.42 (s, 1H), 8.82 (d, J = 8.0 Hz, 1H), 8.4 (s, 1H), 8.29 (s, 1H), 8.17 (s, 1H), 7.25 (s, 1H), 7.18 (d, J = 7.6 Hz, 1H), 7.06-7.02 (m, 1H), 6.98 (s, 1H), 6.83 (d, J = 8.0 Hz, 1H), 5.41 (dd, J = 5.6, 12.8 Hz, 1H), 4.48 (s, 2H), 4.46 (s, 2H), 4.24-4.12 (m, 2H), 3.65 (s, 3H), 2.95-2.83 (m, 2H), 2.74-2.66 (m, 4H), 2.17-2.00 (m, 8H), 1.88 (d, J = 4.4 Hz, 7H), 1.81-1.71 (m, 4H), 1.70-1.44 (m, 4H), 1.09-0.99 (m, 2H) |
| I-548[b] | ASD | AJB | 866.5 | 11.11 (s, 1H), 9.51 (d, J = 6.0 Hz, 1H), 8.79 (d, J = 7.6 Hz, 1H), 8.39 (d, J = 4.0 Hz, 1H), 8.26 (d, J = 5.6 Hz, 1H), 7.30 (s, 1H), 7.25-7.19 (m, 2H), 7.14-6.96 (m, 1H), 6.89-6.43 (m, 1H), 5.40 (dd, J = 5.6, 12.8 Hz, 1H), 5.31-5.06 (m, 1H), 4.77 (d, J = 17.6 Hz, 1H), 4.40 (s, 2H), 4.21-4.14 (m, 1H), 3.85-3.74 (m, 3H), 3.64 (d, J = 10.0 Hz, 2H), 3.36 (s, 3H), 2.94-2.59 (m, 6H), 2.21 (d, J = 6.4 Hz, 4H), 2.07-1.99 (m, 4H), 1.91-1.87 (m, 4H), 1.80-1.70 (m, 2H), 1.63-1.48 (m, 3H), 1.05 (q, J = 12.0 Hz, 2H) |
| I-549[b] | AQI | ASL | 866.2 | 11.12 (s, 1H), 9.31 (s, 1H), 8.81 (d, J = 8.0 Hz, 1H), 8.39 (s, 1H), 8.28 (s, 1H), 7.31-6.85 (m, 5H), 5.47-5.30 (m, 1H), 4.23-4.13 (m, 1H), 4.11-4.04 (m, 2H), 4.00-3.84 (m, 2H), 3.64 (s, 3H), 3.51-3.47 (m, 2H), 2.91-2.81 (m, 3H), 2.74-2.63 (m, 2H), 2.46 (d, J = 6.4 Hz, 2H), 2.13 (d, J = 7.2 Hz, 2H), 2.07-1.97 (m, 3H), 1.95-1.85 (m, 4H), 1.82-1.70 (m, 4H), 1.63-1.51 (m, 2H), 1.42-1.23 (m, 2H), 1.18 (s, 3H), 1.17 (s, 3H), 1.10-0.98 (m, 2H) |
| I-551 | AVS | AJB | 898.3 | 11.09 (s, 1H), 9.50 (d, J = 6.0 Hz, 1H), 8.78 (d, J = 8.0 Hz, 1H), 8.43-8.33 (m, 1H), 8.26 (d, J = 5.6 Hz, 1H), 8.20-8.13 (m, 1H), 7.65-7.53 (m, 1H), 7.27-6.92 (m, 3H), 6.90-6.36 (m, 2H), 5.32-4.99 (m, 2H), 4.76 (d, J = 18.4 Hz, 1H), 4.22-4.11 (m, 1H), 3.84-3.72 (m, 3H), 3.68-3.57 (m, 5H), 2.94-2.84 (m, 1H), 2.65- |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | ¹HNMR (400 MHz, DMSO-d$_6$) δ |
|---|---|---|---|---|
| | | | | 2.52 (m, 3H), 2.11-1.94 (m, 9H), 1.89-1.81 (m, 2H), 1.78-1.61 (m, 6H), 1.58-1.39 (m, 3H), 1.11 (d, J = 6.0 Hz, 3H), 1.06-0.94 (m, 2H) |
| I-552 | AUK | AJB | 880.3 | 11.10 (s, 1H), 9.50 (d, J = 5.6 Hz, 1H), 8.79 (d, J = 7.6 Hz, 1H), 8.43-8.36 (m, 1H), 8.27-8.21 (m, 2H), 7.61-7.54 (m, 1H), 7.27-6.96 (m, 3H), 6.90-6.44 (m, 2H), 5.32-5.00 (m, 2H), 4.77 (br d, J = 17.2 Hz, 1H), 4.23-4.10 (m, 1H), 3.84-3.73 (m, 3H), 3.66-3.58 (m, 3H), 3.18-3.13 (m, 3H), 3.02-2.85 (m, 6H), 2.07-1.92 (m, 6H), 1.90-1.81 (m, 4H), 1.77-1.61 (m, 4H), 1.41-1.29 (m, 3H), 1.12-0.93 (m, 4H) |
| I-553[b] | ASC | AJB | 870.6 | 11.08 (s, 1H), 9.50 ( d, J = 5.6 Hz, 1H), 8.77 ( d, J = 7.6 Hz, 1H), 8.38 (d, J = 4.0 Hz, 1H), 8.26 (d, J = 5.2 Hz, 1H), 7.25-7.00 (m, 2H), 7.00-6.90 (m, 2H), 6.86-6.43 (m, 1H), 5.35 ( dd, J = 5.2, 12.8 Hz, 1H), 5.29-5.05 (m, 1H), 4.76 ( d, J = 16.4 Hz, 1H), 4.16 (t, J = 10.0 Hz, 1H), 3.65-3.57 (m, 3H), 3.37 (t, J = 6.0 Hz, 2H), 3.31 (s, 3H), 3.26-3.22 (m, 1H), 2.95-2.83 (m, 1H), 2.74-2.58 (m, 6H), 2.16-1.93 (m, 10H), 1.89-1.71 (m, 8H), 1.55 (s, 1H), 1.48-1.44 (m, 2H), 1.07-0.97 (m, 2H) |
| I-554 | ARW | AJB | 894.6 | 11.11 (s, 1H), 9.50 (d, J = 6.0 Hz, 1H), 8.80 (d, J = 7.6 Hz, 1H), 8.39 (d, J = 4.4 Hz, 1H), 8.26 (d, J = 5.6 Hz, 1H), 7.28-6.41 (m, 5H), 5.41-5.32 (m, 1H), 5.29 (s, 1H), 4.82-4.73 (m, 1H), 4.21-4.12 (m, 1H), 3.81 (s, 1H), 3.77-3.72 (m, 1H), 3.66-3.62 (m, 1H), 3.60 (s, 1H), 3.55 (s, 3H), 3.05-2.99 (m, 2H), 2.93-2.84 (m, 1H), 2.67-2.59 (m, 1H), 2.28-2.20 (m, 3H), 2.18 (s, 3H), 2.07-1.62 (m, 15H), 1.55-1.48 (m, 3H), 1.47-1.38 (m, 2H), 1.31-1.15 (m, 4H), 1.05-0.94 (m, 2H) |
| I-555[b] | AVF | AJB | 880.4 | 11.13 (s, 1H), 9.51 (d, J = 6.8 Hz, 1H), 8.77 (d, J = 7.6 Hz, 1H), 8.38 (d, J = 4.4 Hz, 1H), 8.26 (d, J = 5.6 Hz, 1H), 7.31-6.94 (m, 4H), 6.90-6.40 (m, 1H), 5.40 (d, J = 12.8 Hz, 1H), 5.29-5.05 (m, 1H), 4.77 (d, J = 16.4 Hz, 1H), 4.65 (q, J = 6.8 Hz, 1H), 4.22-4.12 (m, 1H), 3.81 (s, 1H), 3.65-3.58 (m, 5H), 2.92-2.82 (m, 1H), 2.77-2.59 (m, 5H), 2.39-2.31 (m, 1H), 2.11-1.85 (m, 13H), 1.74 (d, J = 12.4 Hz, 2H), 1.58-1.50 (m, 2H), 1.44 (d, J = 6.4 Hz, 4H), 1.08-0.98 (m, 2H) |
| I-556[b] | AQZ | AJB | 800.2 | 11.06 (s, 1H), 9.49 (d, J = 6.0 Hz, 1H), 8.77 (d, J = 7.6 Hz, 1H), 8.38 (d, J = 4.8 Hz, 1H), 8.25 (d, J = 5.6 Hz, 1H), 7.55 (d, J = 8.4 Hz, 1H), 7.26-6.91 (m, 3H), 6.89-6.42 (m, 2H), 5.30-5.06 (m, 1H), 5.03 (dd, J = 5.2, 12.8 Hz, 1H), 4.76 (d, J = 16.4 Hz, 1H), 4.19-4.12 (m, 1H), 3.83-3.79 (m, 2H), 3.64-3.58 (m, 2H), 3.19 (t, J = 6.0 Hz, 2H), 2.93-2.82 (m, 1H), 2.63-2.52 (m, 2H), 2.36-2.17 (m, 4H), 2.10 (d, J = 6.8 Hz, 2H), 2.07-1.80 (m, 10H), 1.77-1.67 (m, 2H), 1.59-1.43 (m, 7H), 1.07-0.95 (m, 2H) |
| I-557 | ATO | AJB | 884.4 | 11.09 (s, 1H), 9.50 (d, J = 6.0 Hz, 1H), 8.78 (d, J = 7.6 Hz, 1H), 8.38 (d, J = 4.4 Hz, 1H), 8.25 (d, J = 5.6 Hz, 1H), 7.26-6.98 (m, 1H), 6.96 (d, J = 4.8 Hz, 2H), 6.90-6.41 (m, 2H), 5.36 (dd, J = 5.6. 12.8 Hz, 1H), 5.31-5.03 (m, 1H), 4.77 (m, 1H), 4.22-4.12 (m, 1H), 3.85-3.71 (m, 2H), 3.64-36.0 (m, 2H), 3.58 (s, 3H), 3.43 (m, 2H), 3.15-3.01 (m, 1H), 2.93-2.80 (m, 2H), 2.72-2.64 (m, 3H), 2.15-1.43 (m, 21H), 1.12 (d, J = 6.0 Hz, 3H), 1.09-0.97 (m, 2H) |
| I-558 | AUI | AJB | 884.6 | 11.09 (s, 1H), 9.50 (d, J = 6.4 Hz, 1H), 8.78 (d, J = 1.6 Hz, 1H), 8.37 (d, J = 4.4 Hz, 1H), 8.26 (d, J = 5.6 Hz, 1H), 7.25-6.96 (m, 3H), 6.95-6.91 (m, 1H), 6.88-6.43 (m, 1H), 5.37 (dd, J = 5.2, 12.8 Hz, 1H), 5.29-5.06 (m, 1H), 4.77 (d, J = 17.6 Hz, 1H), 4.21-4.11 (m, 1H), 3.86-3.77 (m, 2H), 3.76-3.64 (m, 3H), 3.58 (s, 4H), 3.48-3.43 (m, 4H), 3.12 (t, J = 6.8 Hz, 2H), 3.04 (d, J = 4.0 Hz, 1H), 2.95-2.83 (m, 1H), 2.77-2.67 (m, 2H), 2.28 (dd, J = 6.8, 12.8 Hz, 2H), 2.15 (dd, J = 6.4, 13.2 Hz, 1H), 2.04-1.94 (m, 4H), 1.93-1.86 (m, 2H), 1.80-1.63 (m, 4H), 1.46-1.32 (m, 2H), 1.02-0.90 (m, 8H) |
| I-559[b] | AXW | AJB | 882.2 | 11.11 (s, 1H), 9.50 (d, J = 6.0 Hz, 1H), 8.79 (d, J = 8.0 Hz, 1H), 8.38 (d, J = 4.4 Hz, 1H), 8.26 (d, J = 5.6 Hz, |

TABLE 7-continued

Compounds synthesized via Method 2 with the reductive amination of various amines and aldehydes in Step 1.

| I-# | Step 1 Intermediate Amine | Step 1 Intermediate Aldehyde | LCMS (ES+) m/z (M + H)+ | 1HNMR (400 MHz, DMSO-d6) δ |
|---|---|---|---|---|
| | | | | 1H), 7.25-7.20 (m, 1H), 7.15-6.95 (m, 4H), 6.92-6.43 (m, 1H), 6.03 (d, J = 15.6 Hz, 1H), 5.39 (d, J = 12.8 Hz, 1H), 5.30-5.05 (m, 1H), 4.78 (d, J = 16.4 Hz, 1H), 4.28 (q, J = 6.4 Hz, 1H), 4.17 (t, J = 11.2 Hz, 1H), 3.81 (s, 1H), 3.76-3.62 (m, 1H), 3.60 (s, 1H), 3.56 (s, 3H), 3.50-3.36 (m, 2H), 2.96-2.84 (m, 1H), 2.74-2.59 (m, 4H), 2.11-1.95 (m, 9H), 1.89 (d, J = 10.8 Hz, 3H), 1.80-1.69 (m, 3H), 1.57-1.39 (m, 3H), 1.26 (d, J = 6.4 Hz, 3H), 1.10-0.96 (m, 2H) |
| I-562[b] | BBC | AJB | 898.0 | 11.09 (s, 1H), 9.50 (d, J = 6.0 Hz, 1H), 8.78 (d, J = 1.6 Hz, 1H), 8.38 (s, J = 2.8 Hz, 1H), 8.26 (m, 1H), 8.16 (s, 1H), 7.59 (m, 1H), 7.09-7.02 (m, 3H), 6.85-6.44 (m, 2H), 5.27-5.02 (m, 2H), 4.78 (m, 1H), 4.12 (m, 1H), 3.80-3.59 (m, 6H), 2.60 (m, 2H), 2.50 (m, 4H), 2.00 (m, 10H), 1.98-1.67 (m, 11H), 1.11 (m, 3H), 1.02 (m, 2H) |

[a] For Method 2, when the amine is the HCl salt, TEA was added to free base the salt, followed by HOAc to adjust the pH to 3-4. KOAc could also be used in place of the TEA/HOAc combination. Step 2 deprotection could also be achieved under a variety of standard conditions, including with HCl in Dioxane with DCM as the solvent at rt. Steps 1 and 2 were run anywhere from 0.5-48 hrs The final products were isolated under standard purification techniques including reverse HPLC, silica gel chromatography, and prep-TLC with appropriate solvent conditions.
[b] No deprotection Step 2 required.
[c] ZnBr2 in DCM was used in Step 2 for the deprotection.
[d] Step 2 deprotection was achieved using HBr/HOAc in DCM at rt for 16 h.
[e] A ketone was used in place of an aldehyde for the coupling in Step 1.
[f] Step 2 deprotection was achieved using HBr/HOAc in DCM at rt for 100 h.
[g] Step 2 deprotection was achieved using HBr/HOAc in DCM in DCM at rt for 2 h.
[h] TEA in THF was added to the amine, then the aldehyde and tetraethoxytitanium were added and the reaction was stirred at 80 C. for 2 hrs. Then the mixture was cooled to rt and NaBH4 was added and the mixture was stirred for 2 h at rt. No deprotection Step 2 required.
[i] Tetraethoxytitanium and optionally TEA was used for the coupling, which was run at 80 C. for 12-16 hrs. Then NaBH4 was added and the reaction was stirred at 25 C. for 1-2 h. No deprotection Step 2 required.
[j] The coupling of the amine and aldehyde was achieved by first free basing the amine with TEA at rt for 30 min. Next the aldehyde and tetraethoxytitanium was added into the mixture and the reaction was heated at 80° C. for 12 hours. After cooled to 25° C., NaBH3CN (75.6 mg, 1.20 mmol) was added and the reaction mixture was stirred at 25° C. for 0.5 hour.

Examples 3. Synthesis of N-(3-carbamoyl-1-((1r,4r)-4-((2-(2-(2-((2-(2,6-dioxo piperidin-3-yl)-1,3-dioxoisoindolin-4-yl)amino)ethoxy)ethoxy)ethyl)carbamoyl)cyclohexyl)-1H-pyrazol-4-yl)-2-(2-((2,2,2-trifluoroethyl)amino)pyridin-4-yl)oxazole-4-carboxamide (I-13) and N-(3-carbamoyl-1-((1s,4s)-4-((2-(2-(2-((2-(2,6-dioxopiperidin-3-yl)-1,3-dioxoisoindolin-4-yl)amino)ethoxy)ethoxy)ethyl)carbamoyl)cyclohexyl)-1H-pyrazol-4-yl)-2-(2-((2,2,2-trifluoroethyl)amino)pyridin-4-yl)oxazole-4-carboxamide (I-14)

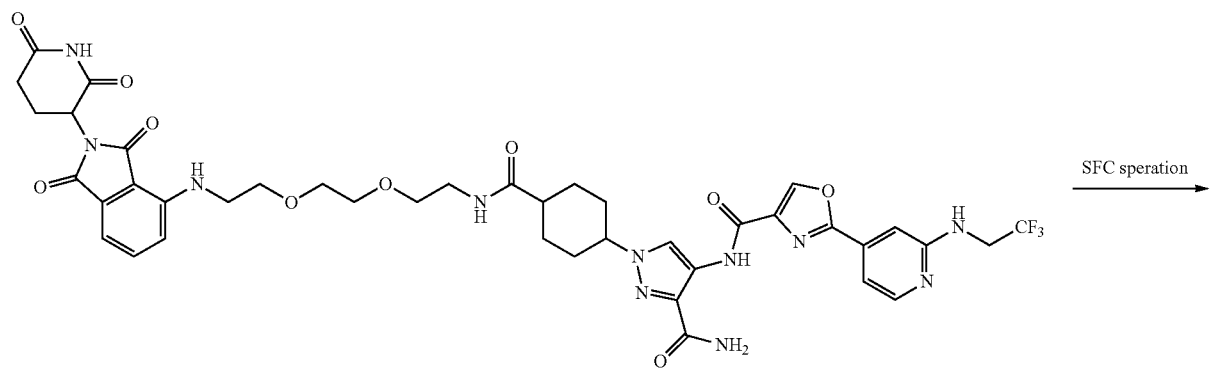

SFC speration

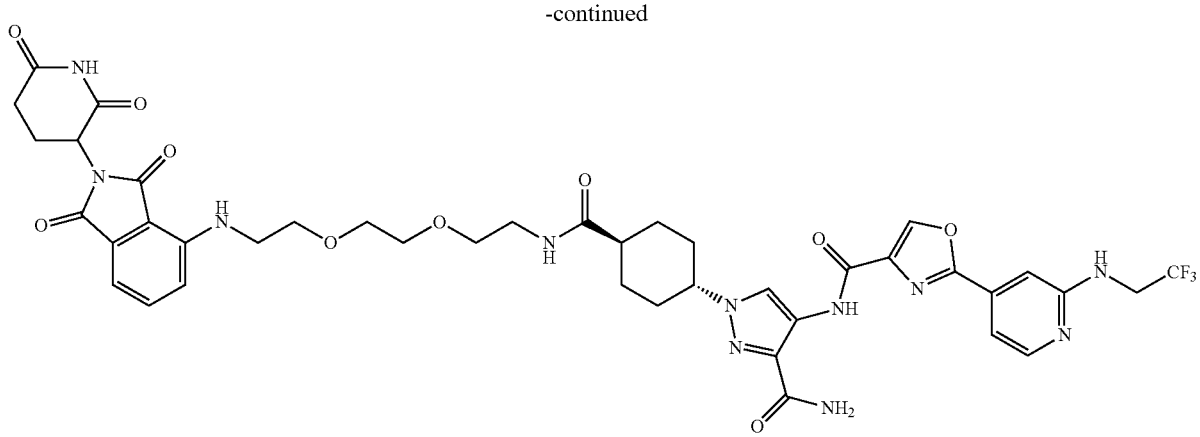

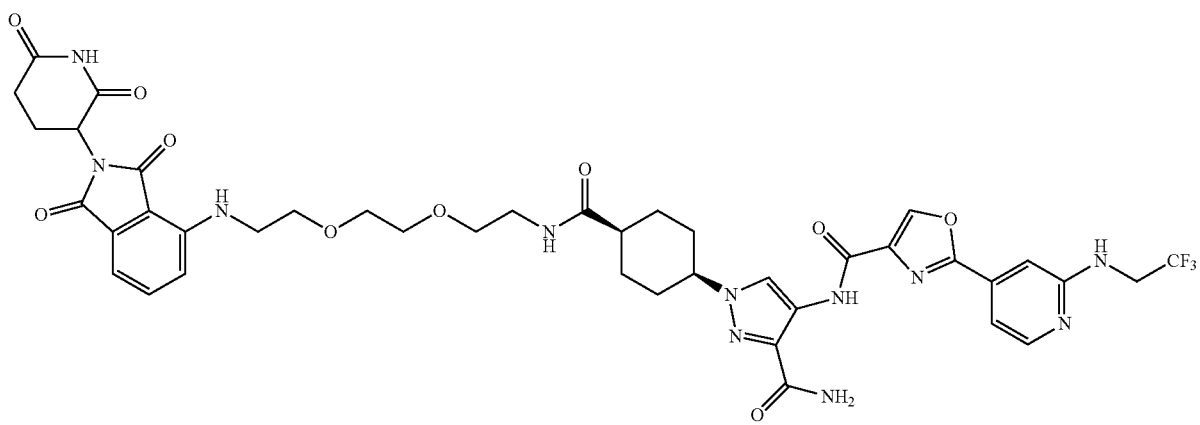

N-(3-carbamoyl-1-(4-((2-(2-(2-((2-(2,6-dioxopiperidin-3-yl)-1,3-dioxoisoindolin-4-yl)amino)ethoxy)ethoxy)ethyl)carbamoyl)cyclohexyl)-1H-pyrazol-4-yl)-2-(2-((2,2,2-trifluoroethyl)amino)pyridin-4-yl)oxazole-4-carboxamide (13.0 mg 14.3 umol) was separated by SFC (column: DAICEL CHIRALCEL OD(250 mm*50 mm, 10 um); mobile phase: [0.1% NH₃.H₂O MEOH]; B %: 60%-60%, 7.0 min; 130 mi) to give the title compound N-(3-carbamoyl-1-((1r,4r)-4-((2-(2-(2-((2-(2,6-dioxo piperidin-3-yl)-1,3-dioxoisoindolin-4-yl)amino)ethoxy)ethoxy)ethyl)carbamoyl)cyclohexyl)-1H-pyrazol-4-yl)-2-(2-((2,2,2-trifluoroethyl)amino)pyridin-4-yl)oxazole-4-carboxamide (5.00 mg, 38% yield, 100% purity) as yellow solid and N-(3-carbamoyl-1-((1s,4s)-4-((2-(2-(2-((2-(2,6-dioxopiperidin-3-yl)-1,3-dioxoisoindolin-4-yl)amino)ethoxy)ethoxy)ethyl)carbamoyl)cyclohexyl)-1H-pyrazol-4-yl)-2-(2-((2,2,2-trifluoroethyl)amino)pyridin-4-yl)oxazole-4-carboxamide (5.00 mg, 33% yield, 87% purity) as yellow solid. Absolute stereochemistry of the diastereomers was arbitrarily assigned. Characterization of N-(3-carbamoyl-1-((1r,4r)-4-((2-(2-(2-((2-(2,6-dioxo piperidin-3-yl)-1,3-dioxoisoindolin-4-yl)amino)ethoxy)ethoxy)ethyl)carbamoyl)cyclohexyl)-1H-pyrazol-4-yl)-2-(2-((2,2,2-trifluoroethyl)amino)pyridin-4-yl)oxazole-4-carboxamide: $^1$H NMR (400 MHz, MeOD-d₄) δ 8.46 (s, 1H), 8.25 (s, 1H), 8.10-8.08 (m, 1H), 7.42-7.38 (m, 1H), 7.24-7.21 (m, 2H), 6.90-6.94 (m, 2H), 4.96-4.94 (m, 1H), 4.10-4.05 (m, 2H), 3.61-3.59 (m, 2H), 3.48-3.44 (m, 4H), 3.37-3.35 (m, 2H), 3.29-3.27 (m, 2H), 2.72-2.62 (m, 3H), 2.36-2.34 (m, 1H), 2.20-2.18 (m, 2H), 1.95-1.91 (m, 4H), 1.86-1.83 (m, 2H), 1.64-1.60 (m, 2H); LC-MS (ESI⁺) m/z 908.5 (M+H)⁺. Characterization of N-(3-carbamoyl-1-((1s,4s)-4-((2-(2-(2-((2-(2,6-dioxopiperidin-3-yl)-1,3-dioxoisoindolin-4-yl)amino)ethoxy)ethoxy)ethyl)carbamoyl)-cyclohexyl)-1H-pyrazol-4-yl)-2-(2-((2,2,2-trifluoroethyl)amino)pyridin-4-yl)oxazole-4-carboxamide: $^1$H NMR (400 MHz, MeOD-d₄) δ 8.74 (s, 1H), 8.30 (s, 1H), 8.17-8.15 (m, 1H), 7.72 (s, 1H), 7.64-7.63 (m, 1H), 7.58-7.54 (m, 1H), 7.09-7.06 (m, 2H), 5.09-5.05 (m, 1H), 4.96-4.90 (m, 1H), 4.37-4.32 (m, 2H), 4.28-4.24 (m, 1H), 3.76-3.74 (m, 2H), 3.69-3.64 (m, 4H), 3.57-3.51 (m, 4H), 2.76-2.69 (m, 3H), 2.25-2.22 (m, 1H), 2.13-2.10 (m, 3H), 1.98-1.94 (m, 2H), 1.80-1.77 (m, 2H), 1.69-1.63 (m, 2H); LC-MS (ESI⁺) m/z 908.5 (M+H)⁺.

Example 4. Synthesis of 2-[2-(Cyclopropylmethyl-amino)-4-pyridyl]-N-[1-[4-[[2-[2-[3-[1-(2,6-dioxo-3-piperidyl)-3-methyl-2-oxo-benzimidazol-4-yl]propoxy] ethoxy] ethyl-methyl-amino] methyl] cyclohexyl]-3-isopropyl-pyrazol-4-yl] oxazole-4-carboxamide (I-54)

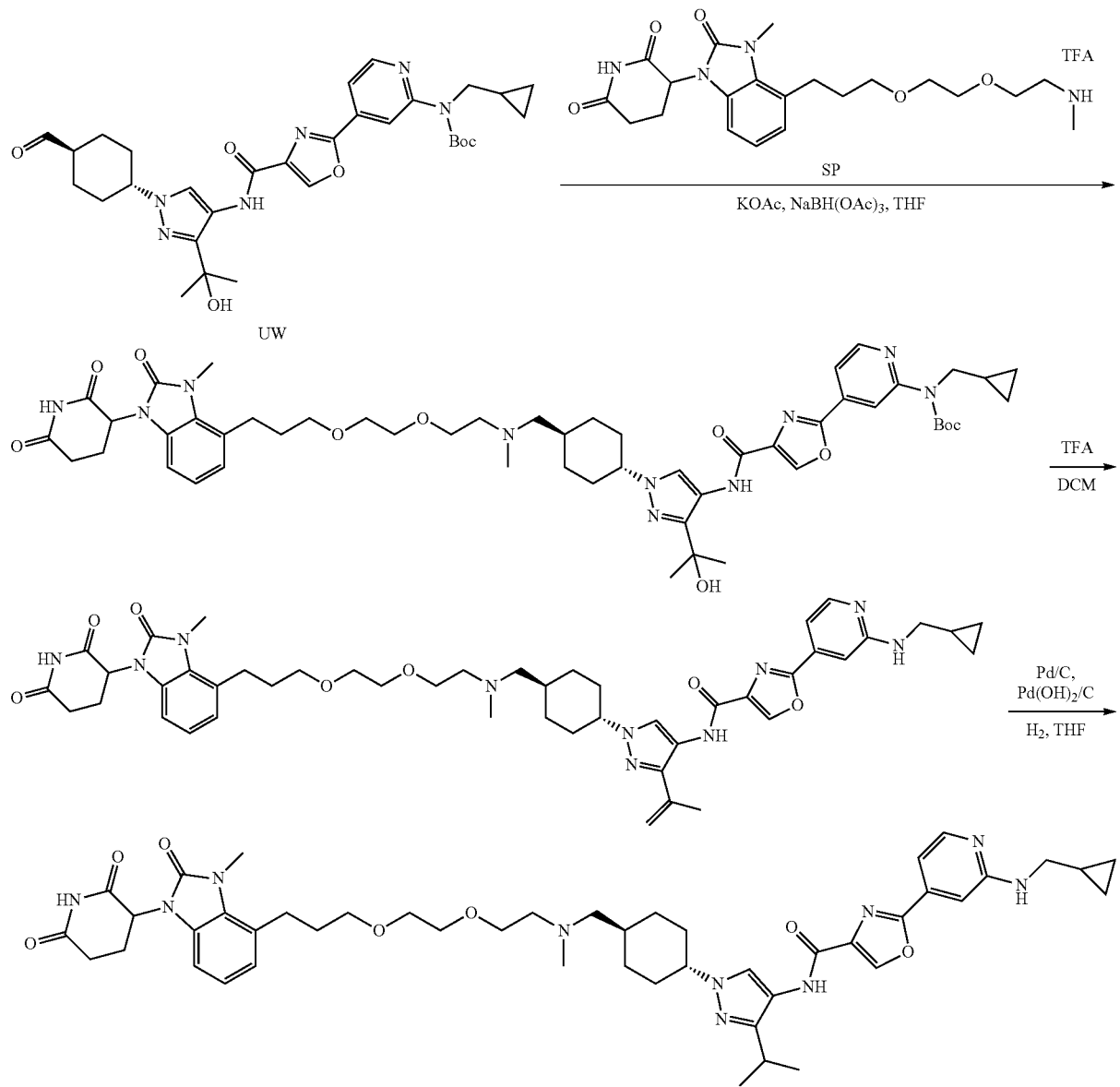

Step 1—Tert-butyl N-(cyclopropylmethyl)-N-[4-[4-[[1-[4-[[2-[2-[3-[1-(2,6-dioxo-3-piperidyl)-3-methyl-2-oxo-benzimidazol-4-yl]propoxy] ethoxy] ethyl-methyl-amino]methyl]cyclohexyl]-3-(1-hydroxy-1-methyl-ethyl)pyrazol-4-yl]carbamoyl] oxazol-2-yl]-2-pyridyl]carbamate To a mixture of 3-[3-methyl-4-[3-[2-[2-(methylamino)ethoxy]ethoxy]propyl]-2-oxo-benzimidazol-1-yl]piperidine-2,6-dione (49.4 mg, 92.8 umol, TFA salt, Intermediate SP) in THF (10 mL) was added KOAc (57.9 mg, 590 umol). The mixture was stirred at 25° C. for 20 minutes. Then tert-butyl N-(cyclopropylmethyl)-N-[4-[4-[[1-(4-formylcyclohexyl)-3-(1-hydroxy-1-methyl-ethyl)pyrazol-4-yl]carbamoyl]oxazol-2-yl]-2-pyridyl]carbamate (70.0 mg, 118 umol, Intermediate UW) and NaBH(OAc)$_3$ (50.0 mg, 236 umol) was added into the mixture. The reaction mixture was stirred at 25° C. for 12 hours. On completion, the reaction was quenched by water (2 mL) and concentrated in vacuo to give a residue. The residue was purified by reversed-phase HPLC (0.1% FA condition) to give the title compound (75.0 mg, 61% yield) as a white solid. LC-MS (ESI$^+$) m/z 877.0 (M−100−17)$^+$.

Step 2—2-[2-(Cyclopropylmethylamino)-4-pyridyl]-N-[1-[4-[[2-[2-[3-[1-(2,6-dioxo-3-piperidyl)-3-methyl-2-oxo-benzimidazol-4-yl]propoxy] ethoxy] ethyl-methyl-amino]methyl]cyclohexyl]-3-isopropenyl-pyrazol-4-yl]oxazole-4-carboxamide To a mixture of tert-butyl N-(cyclopropylmethyl)-N-[4-[4-[[1-[4-[[2-[2-[3-[1-(2,6-dioxo-3-piperidyl)-3-methyl-2-oxo-benzimidazol-4-yl]propoxy]ethoxy] ethyl-methyl-amino]methyl]cyclohexyl]-3-(1-hydroxy-1-methyl-ethyl) pyrazol-4-yl]carbamoyl]oxazol-2-yl]-2-pyridyl]carbamate (75.0 mg, 75.4 umol) in DCM (5 mL) was added TFA (17.2 mg, 150 umol). The reaction mixture was stirred at 25° C. for 1 hour. On completion, the reaction mixture was concentrated in vacuo to give a residue. The residue was purified by prep-HPLC (column: Phenomenex Synergi C18 150*25*10 um; mobile phase: [water (0.225% FA)-ACN] B %: 7%-37%) to give a title compound (39.8 mg, 57% yield, FA salt). $^1$H NMR (400 MHz, DMSO-$d_6$) δ 11.10 (s, 1H), 9.38 (s, 1H), 8.95-8.77 (m, 1H), 8.18 (s, 1H), 8.14 (d, J=5.6 Hz, 1H), 8.06-7.97 (m, 1H), 7.10-7.07 (m, 1H), 7.01 (d, J=1.2, 5.2 Hz, 1H), 6.98-6.92 (m, 2H), 6.88 (d, J=4.2 Hz, 1H), 5.41-5.30 (m, 2H), 5.20 (s, 1H), 4.12-4.01 (m, 1H), 3.57-3.49 (m, 18H), 3.20-3.15 (m, 3H), 3.00-2.82 (m, 4H), 2.75-2.59 (m, 3H), 2.25-2.15 (m, 5H), 2.08 (s, 3H), 2.05-1.94 (m, 3H), 1.93-1.78 (m, 4H), 1.75-1.65 (m, 2H), 1.63-1.46 (m, 2H), 1.10-0.97 (m, 2H), 0.50-0.39 (m, 2H), 0.26-0.18 (m, 2H).

Step 3—2-[2-(Cyclopropylmethylamino)-4-pyridyl]-N-[1-[4-[[2-[2-[3-[1-(2,6-dioxo-3-piperidyl)-3-methyl-2-oxo-benzimidazol-4-yl]propoxy]ethoxy] ethyl-methyl-amino]methyl]cyclohexyl]-3-isopropyl-pyrazol-4-yl]oxazole-4-carboxamide To a mixture of 2-[2-(cyclopropylmethylamino)-4-pyridyl]-N-[1-[4-[[2-[2-[3-[1-(2,6-dioxo-3-piperidyl)-3-methyl-2-oxo-benzimidazol-4-yl]propoxy] ethoxy] ethyl-methyl-amino]methyl]cyclohexyl]-3-isopropenyl-pyrazol-4-yl]oxazole-4-carboxamide (39.8 mg, 43.1 umol, FA salt) in THF (5 mL) was added Pd/C (20.0 mg, 10 wt %) and Pd(OH)$_2$/C (20.0 mg, 10 wt %) under N$_2$. The suspension was degassed under vacuum and purged with H$_2$ several times. The mixture was stirred at 25° C. for 2 hours under H$_2$ (15 psi). On completion, the reaction mixture was filtered and the filtrate was concentrated in vacuo to give a residue. The residue was purified by prep-HPLC (column: Phenomenex Synergi C18 150*25*10 um; mobile phase: [water (0.225% FA)-ACN]; B %: 10%-40%) to give the title compound (2.80 mg, 6% yield, FA salt) as a white solid. $^1$H NMR (400 MHz, DMSO-$d_6$) δ 11.08 (s, 1H), 9.38 (s, 1H), 8.89-8.80 (m, 1H), 8.36 (s, 1H), 8.14 (d, J=5.2 Hz, 1H), 7.90-7.77 (m, 1H), 7.10 (s, 1H), 7.08-7.00 (m, 2H), 6.96 (d, J=4.4 Hz, 2H), 6.92-6.82 (m, 1H), 5.36 (d, J=4.8, 12.4 Hz, 1H), 4.04-3.92 (m, 1H), 3.56 (s, 2H), 3.54-3.46 (m, 11H), 3.18 (s, 2H), 3.02 (d, J=6.4 Hz, 2H), 2.96 (s, 2H), 2.90-2.81 (m, 2H), 2.18 (s, 3H), 1.99 (d, J=2.8, 7.8 Hz, 3H), 1.91-1.78 (m, 4H), 1.72-1.59 (m, 2H), 1.57-1.43 (m, 2H), 1.21-1.16 (m, 6H), 1.10-0.95 (m, 3H), 0.49-0.40 (m, 2H), 0.22 (d, J=4.2 Hz, 2H). LC-MS (ESI$^+$) m/z 879.6 (M+H)$^+$.

Example 5. Synthesis of 2-[2-(Cyclopropylmethylamino)-4-pyridyl]-N-[3-(difluoromethyl)-1-[4-[[3-[3-[1-[(3S)-2,6-dioxo-3-piperidyl]-3-methyl-2-oxo-benzimidazol-4-yl] propoxy] propyl-methyl-amino] methyl]cyclohexyl]pyrazol-4-yl]oxazole-4-carboxamide (I-89) and 2-[2-(cyclopropylmethylamino)-4-pyridyl]-N-[3-(difluoromethyl)-1-[4-[[3-[3-[1-[(3R)-2,6-dioxo-3-piperidyl]-3-methyl-2-oxo-benzimidazol-4-yl] propoxy] propyl-methyl-amino]methyl] cyclohexyl] pyrazol-4-yl]oxazole-4-carboxamide (I-90)

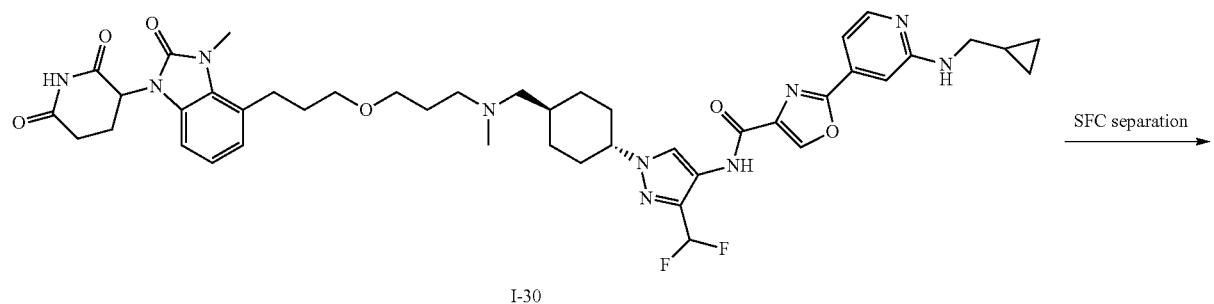

I-30

SFC separation →

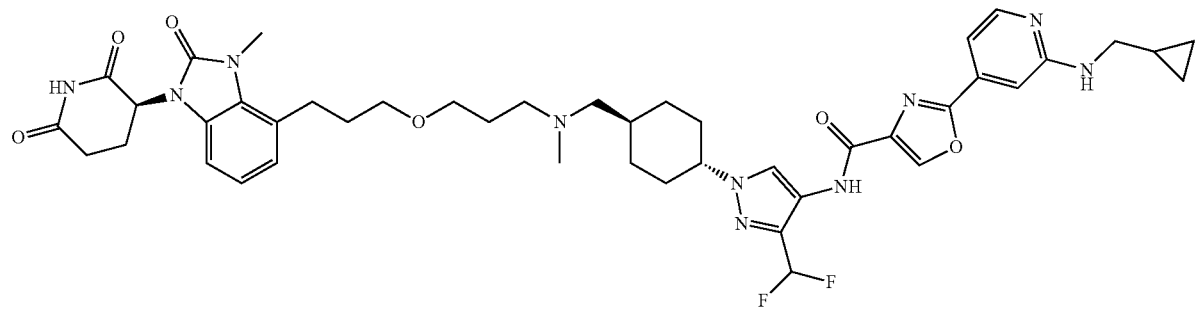

+

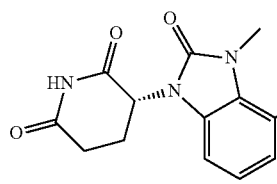
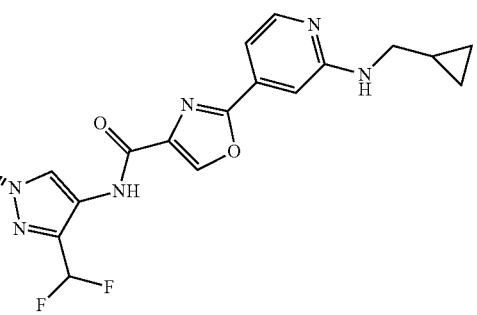

2-[2-(Cyclopropylmethylamino)-4-pyridyl]-N-[3-(difluoromethyl)-1-[4-[[3-[3-[1-(2,6-dioxo-3-piperidyl)-3-methyl-2-oxo-benzimidazol-4-yl]propoxy]propyl-methyl-amino]methyl]cyclohexyl]pyrazol-4-yl]oxazole-4-carboxamide (190 mg, 221 umol, I-30) was carried out on a super-fluid chromatography unit using sample preparation (add CH$_3$CN 25 mL into sample, Instrument: Thar 80 SFC Mobile Phase: 70% IPA+ACN (0.1% DEA) in Supercritical CO$_2$ Flow Rate: 70 g/min Cycle Time: 5.0 min, total time: 170 min Single injection volume: 0.8 ml Back Pressure: 100 bar to keep the CO$_2$ in Supercritical flow). This afforded two enantiomers with retention times of 1.1 minutes: 2-[2-(Cyclopropylmethylamino)-4-pyridyl]-N-[3-(difluoromethyl)-1-[4-[[3-[3-[1-[(3S)-2,6-dioxo-3-piperidyl]-3-methyl-2-oxo-benzimidazol-4-yl]propoxy]propyl-methyl-amino]methyl]cyclohexyl]pyrazol-4-yl]oxazole-4-carboxamide (36.4 mg, 33% yield, >87% ee value) as white solid; and 1.6 minutes: 2-[2-(cyclopropylmethylamino)-4-pyridyl]-N-[3-(difluoromethyl)-1-[4-[[3-[3-[1-[(3R)-2,6-dioxo-3-piperidyl]-3-methyl-2-oxo-benzimidazol-4-yl]propoxy]propyl-methyl-amino]methyl]cyclohexyl]pyrazol-4-yl]oxazole-4-carboxamide (28.21 mg, 25% yield, >80% ee value) as white solid. The absolute configurations of the two enantiomers was arbitrarily assigned.

2-[2-(Cyclopropylmethylamino)-4-pyridyl]-N-[3-(difluoromethyl)-1-[4-[[3-[3-[1-[(3S)-2,6-dioxo-3-piperidyl]-3-methyl-2-oxo-benzimidazol-4-yl]propoxy]propyl-methyl-amino]methyl]cyclohexyl]pyrazol-4-yl]oxazole-4-carboxamide: $^1$H NMR (400 MHz, DMSO-d$_6$) δ 11.07 (s, 1H), 9.67 (s, 1H), 8.91 (s, 1H), 8.17 (s, 1H), 8.15 (d, J=5.2 Hz, 1H), 7.29-7.00 (m, 5H), 6.96 (d, J=5.2 Hz, 1H), 6.88-6.86 (m, 1H), 5.38-5.33 (m, 1H), 4.25-4.13 (m, 1H), 3.57 (s, 3H), 3.42 (t, J=6.0 Hz, 4H), 3.18 (t, J=6.0 Hz, 2H), 2.99-2.93 (m, 2H), 2.93-2.83 (m, 1H), 2.75-2.67 (m, 1H), 2.65-2.58 (m, 1H), 2.56-2.52 (m, 2H), 2.14-2.10 (m, 4H), 2.06-1.97 (m, 4H), 1.77-1.73 (m, 1H), 1.67-1.63 (m, 2H), 1.36 (s, 3H), 1.23 (s, 3H), 0.87-0.80 (m, 3H), 0.48-0.42 (m, 2H), 0.25-0.20 (m, 2H); LC-MS (ESI$^+$) m/z 857.5 (M+H)$^+$.

2-[2-(cyclopropylmethylamino)-4-pyridyl]-N-[3-(difluoromethyl)-1-[4-[[3-[3-[1-[(3R)-2,6-dioxo-3-piperidyl]-3-methyl-2-oxo-benzimidazol-4-yl]propoxy]propyl-methyl-amino]methyl]cyclohexyl]pyrazol-4-yl]oxazole-4-carboxamide: $^1$H NMR (400 MHz, DMSO-d$_6$) δ 11.07 (s, 1H), 9.67 (s, 1H), 8.91 (s, 1H), 8.17 (s, 1H), 8.15 (d, J=5.6 Hz, 1H), 7.30-6.93 (m, 6H), 6.89-6.85 (m, 1H), 5.42-5.30 (m, 1H), 4.25-4.15 (m, 1H), 3.57 (s, 3H), 3.42 (t, J=6.0 Hz, 4H), 3.18 (t, J=6.0 Hz, 2H), 3.00-2.92 (m, 2H), 2.90-2.83 (m, 1H), 2.66-2.59 (m, 4H), 2.15-2.10 (m, 4H), 2.07-1.95 (m, 4H), 1.77-1.73 (m, 1H), 1.69-1.61 (m, 2H), 1.36 (s, 3H), 1.24 (s, 3H), 0.88-0.81 (m, 3H), 0.49-0.41 (m, 2H), 0.26-0.19 (m, 2H); LC-MS (ESI$^+$) m/z 857.6 (M+H)$^+$.

Example 6. Synthesis of 2-[2-(Cyclopropylmethylamino)-4-pyridyl]-N-[1-[4-[[[(2R)-4-[3-[1-(2,6-dioxo-3-piperidyl)-3-methyl-2-oxo-benzimidazol-5-yl]propyl] morpholin-2-yl] methyl-methyl-amino]methyl] cyclohexyl]-3-isopropyl-pyrazol-4-yl] oxazole-4-carboxamide (I-94)

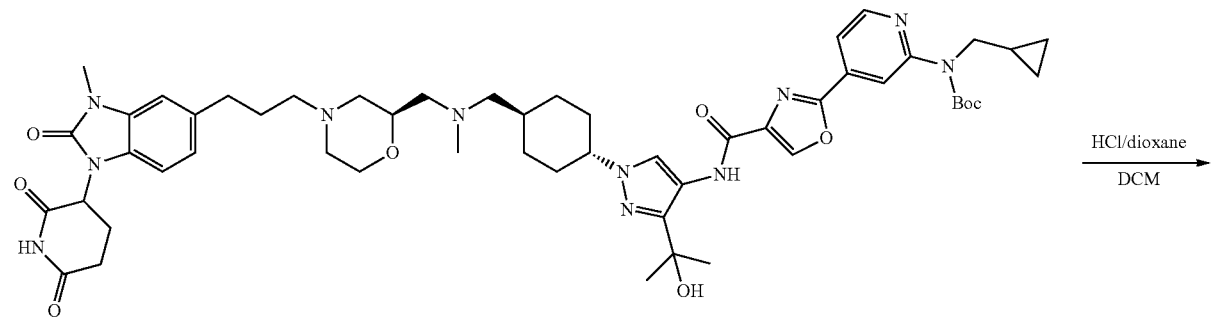

2455

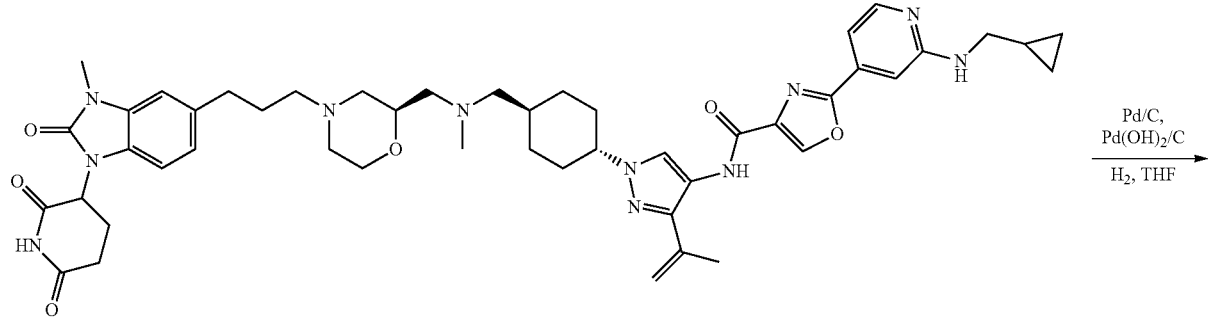

2456

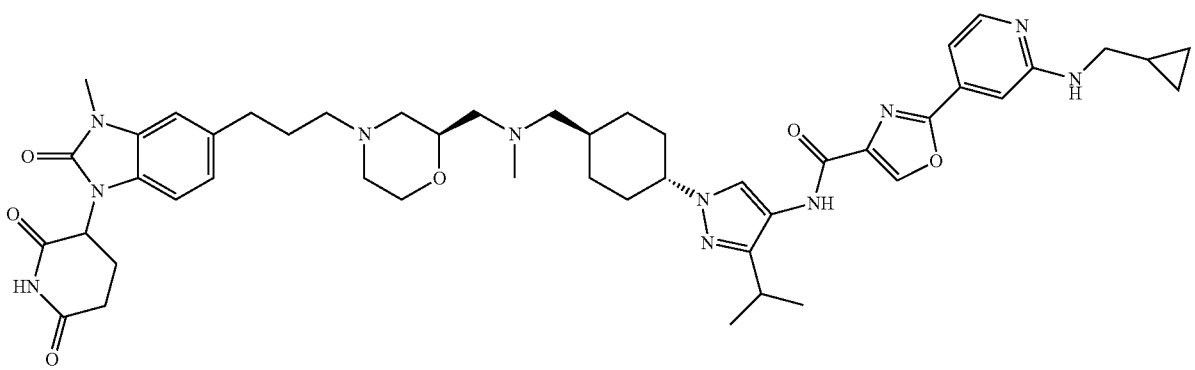

Step 1—2-[2-(Cyclopropylmethylamino)-4-pyridyl]-N-[1-[4-[[[(2R)-4-[3-[1-(2,6-dioxo-3-piperidyl)-3-methyl-2-oxo-benzimidazol-5-yl]propyl]morpholin-2-yl]methyl-methyl-amino]methyl]cyclohexyl]-3-isopropenyl-pyrazol-4-yl]oxazole-4-carboxamide To a solution of tert-butyl N-(cyclopropylmethyl)-N-[4-[4-[[1-[4-[[[(2R)-4-[3-[1-(2,6-dioxo-3-piperidyl)-3-methyl-2-oxo-benzimidazol-5-yl]propyl]morpholin-2-yl]methyl-methyl-amino]methyl]cyclohexyl]-3-(1-hydroxy-1-methyl-ethyl)pyrazol-4-yl]carbamoyl] oxazol-2-yl]-2-pyridyl]carbamate (70.0 mg, 69.57 umol, synthesized via Step 1 of I-33) in DCM (4 mL) was added HCl/dioxane (4 M, 1.75 mL). The reaction mixture was stirred at 25° C. for 2 hrs. On completion, the mixture was concentrated in vacuo to give a residue. The residue was purified by prep-HPLC (column: Phenomenex Synergi C18 150*25*10 um; mobile phase: [water (0.225% FA)-ACN]; B %: 5%-35%, 10 min) to give the title compound (25.0 mg, 38% yield) as a white solid. LC-MS (ESI$^+$) m/z 888.3 (M+H)$^+$.

Step 2—2-[2-(Cyclopropylmethylamino)-4-pyridyl]-N-[1-[4-[[[(2R)-4-[3-[1-(2,6-dioxo-3-piperidyl)-3-methyl-2-oxo-benzimidazol-5-yl]propyl]morpholin-2-yl]methyl-methyl-amino]methyl]cyclohexyl]-3-isopropyl-pyrazol-4-yl]oxazole-4-carboxamide To a solution of 2-[2-(cyclopropylmethylamino)-4-pyridyl]-N-[1-[4-[[[(2R)-4-[3-[1-(2,6-dioxo-3-piperidyl)-3-methyl-2-oxo-benzimidazol-5-yl]propyl]morpholin-2-yl]methyl-methyl-amino]methyl]cyclohexyl]-3-isopropenyl-pyrazol-4-yl]oxazole-4-carboxamide (20.0 mg, 22.5 umol) in THF (1 mL) was added Pd/C (5 mg, 10 wt %) and Pd(OH)$_2$/C (5 mg, 10 wt %). The reaction mixture was stirred at 25° C. for 12 hrs under H$_2$ (15 psi). On completion, the reaction mixture was concentrated in vacuo to give a residue. The residue was purified by prep-HPLC (column: Phenomenex Synergi C18 150*25*10 um; mobile phase: [water (0.225% FA)-ACN]; B %: 7%-27%, 10 min) to give the title compound (3.50 mg, 16% yield) as a yellow solid. $^1$H NMR (400 MHz, DMSO-d$_6$) δ 11.07 (s, 1H), 9.39 (s, 1H), 8.83 (s, 1H), 8.14 (d, J=5.2 Hz, 1H), 7.81 (s, 1H), 7.10 (s, 1H), 7.07-6.94 (m, 4H), 6.87 (d, J=8.0 Hz, 1H), 5.31 (dd, J=5.2, 12.8 Hz, 1H), 4.08-3.95 (m, 1H), 3.86-3.66 (m, 2H), 3.30 (s, 3H), 3.19-3.16 (m, 2H), 3.06-2.98 (m, 2H), 2.93-2.80 (m, 3H), 2.64-2.61 (m, 2H), 2.32-2.24 (m, 4H), 2.16 (s, 3H), 2.15-2.06 (m, 2H), 2.05-1.93 (m, 4H), 1.92-1.82 (m, 2H), 1.81-1.59 (m, 6H), 1.58-1.43 (m, 2H), 1.18 (d, J=6.8 Hz, 6H), 1.10-0.95 (m, 3H), 0.49-0.41 (m, 2H), 0.25-0.18 (m, 2H); LC-MS (ESI$^+$) m/z 890.6 (M+H)$^+$.

Example 7. Synthesis of 2-[2-(Cyclopropylmethyl-amino)-4-pyridyl]-N-[3-(difluoromethyl)-1-[4-[[[1-[4-[1-(2,6-dioxo-3-piperidyl)-3-methyl-2-oxo-benzimidazol-4-yl] butyl]-4-piperidyl] methyl-methyl-amino] methyl] cyclohexyl] pyrazol-4-yl] oxazole-4-carboxamide (I-98)

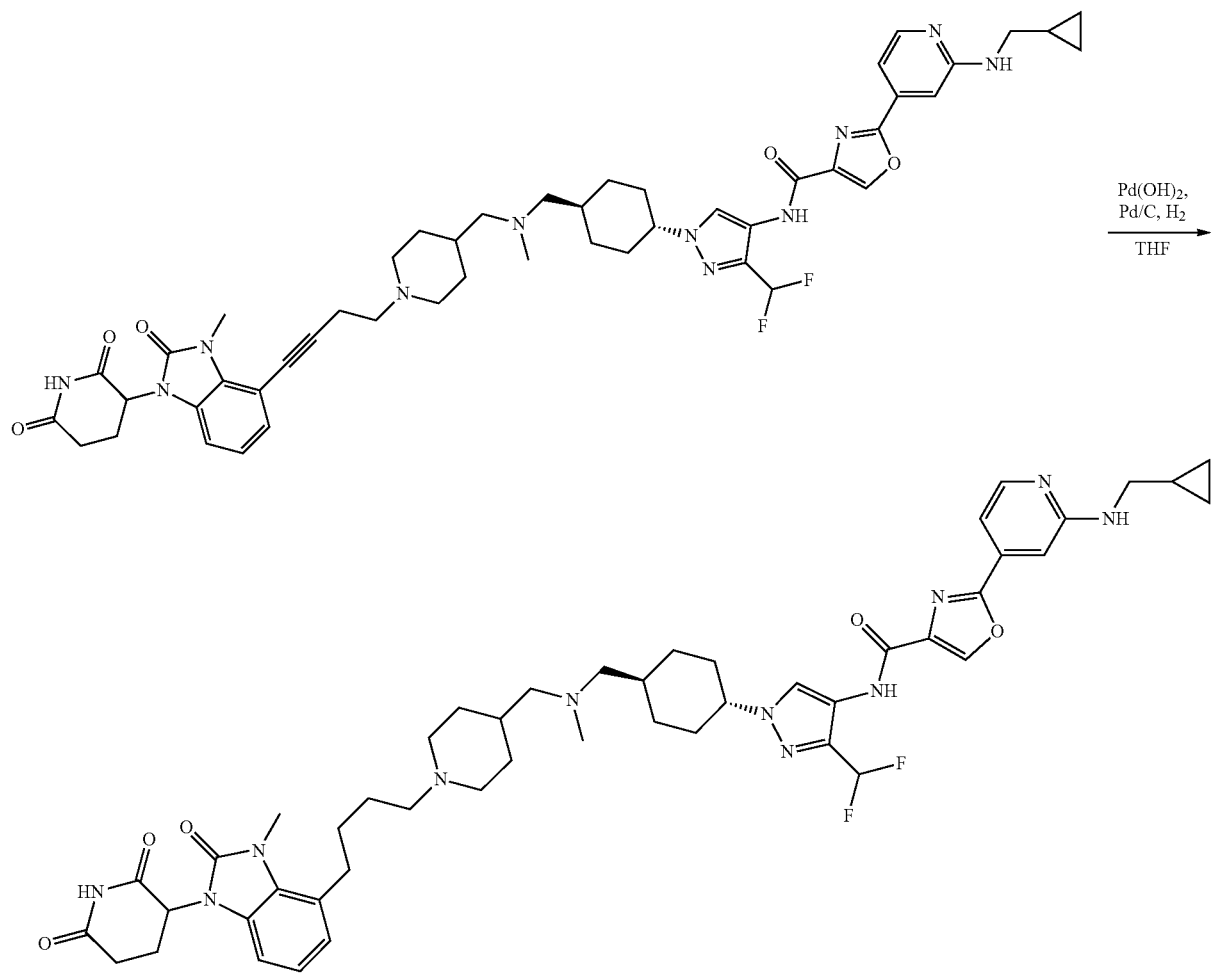

To a solution of 2-[2-(cyclopropylmethylamino)-4-pyridyl]-N-[3-(difluoromethyl)-1-[4-[[[1-[4-[1-(2,6-dioxo-3-piperidyl)-3-methyl-2-oxo-benzimidazol-4-yl]but-3-ynyl]-4-piperidyl]methyl-methyl-amino]methyl]cyclohexyl]pyrazol-4-yl] oxazole-4-carboxamide (60.0 mg, 63 umol, FA, I-80) in THF (20 mL) was added Pd/C (20.0 mg, 63.0 umol, 10 wt) and Pd(OH)$_2$/C (20.0 mg, 10 wt %). The reaction mixture was stirred at 25° C. for 24 hrs under H$_2$ (15 psi). On completion, the mixture was filtered and the filtrate was concentrated in vacuo to give a residue. The residue was purified by prep-HPLC (column: Phenomenex Synergi C18 150*30 mm*4 um; mobile phase: [water (0.225% FA)-ACN]; B %: 5%-35%, 10 min) to give the title compound (24.8 mg, 40% yield) as a white solid. $^1$H NMR (400 MHz, DMSO-d$_6$) δ 11.09 (s, 1H), 9.69 (s, 1H), 8.92 (s, 1H), 8.18 (s, 1H), 8.15 (d, J=5.2 Hz, 1H), 7.29-7.00 (m, 4H), 6.98-6.92 (m, 2H), 6.89-6.84 (m, 1H), 5.36 (dd, J=5.2, 12.8 Hz, 1H), 4.24-4.15 (m, 1H), 3.56 (s, 3H), 3.19-3.16 (m, 2H), 2.93-2.85 (m, 5H), 2.77-2.70 (m, 1H), 2.65-2.56 (m, 3H), 2.45-2.36 (m, 3H), 2.11 (s, 3H), 2.09-2.06 (m, 2H), 2.06-1.95 (m, 5H), 1.93-1.88 (m, 2H), 1.79-1.67 (m, 4H), 1.62-1.52 (m, 5H), 1.13-0.96 (m, 5H), 0.48-0.42 (m, 2H), 0.25-0.18 (m, 2H); LC-MS (ESI$^+$) m/z 910.6 (M+1)$^+$.

Example 8. IRAK OCI-LY10 Degradation in Whole Blood

Methods

Compound treatment: Compounds were reconstituted in DMSO to make the stock at concentration of 60 mM. OCI-LY10 cells were maintained in RPMI-1640 medium containing 10% FBS, 0.5 μM 2-ME or 20% FBS, 55 μM 2-ME, and 1% L-Glutamine respectively.

Cells were seeded into 6-well plates with 5e6 cells per well. 200 μL of diluted compounds were added to cells to the final concentration of 0.003-10 μM. After 4 or 24 hour-incubation at 37° C., cells were collected into 2 mL Eppendorf tubes and centrifuged at 1,000 rpm for 5 min. The cell pellets were washed with 1×DPBS once and resuspended in 60 μL lysis buffer. The cells were lysed on ice for 10 min, then centrifuged at 14,000 rpm for 10 min at 4° C. and the supernatants were collected for western blots. RIPA buffer (Thermo Fisher, 89900) with Halt Protease and Phophatase Inhibitor Cocktail (Thermo Fisher, 78446) was applied.

Protein concentration determination: The protein concentration of cell lysates was quantified with Pierce™ BCA Protein Assay Kit (Pierce, 23227). Albumin standards at different concentrations were prepared, involving 2,000 ug/mL, 1,500 ug/mL, 1,000 ug/mL, 750 ug/mL, 500 ug/mL, 250 ug/mL, 125 ug/mL, and 25 ug/mL. BCA working reagents were prepared by mixing BCA reagent A with reagent B in 50:1 ratio. 200 µL of the BCA working reagents were added to 25 µL of BCA standard or cell lysates in microplate, and mixed thoroughly on a plate shaker for 30 seconds. After incubation at 37° C. for 30 min, the absorbance of samples at 562 nm were measured with EnVision Plate Reader.

Western blot assay: Protein lysates were prepared in NuPAGE™ LDS sample buffer and NuPAGE™ sample reducing agent, and incubated at 95° C. for 5 min. For western blots, 20-25 pg of total proteins were resolved in 4-12% Bis-Tris gels (Introgen, WG1403A) or 10% Bis-Tris Midi gels (Invitrogen, WG1202BOX) running with 1×MOPS SDS running buffer (Invitrogen, NP0001) or 1×MES SDS running buffer (Invitrogen, NP0002). The proteins were transferred to low fluorescence PVDF membranes using the Trans-Blot Turbo Transfer System. Membranes were then blocked in Odyssey blocking buffer at RT for 1 h followed by primary incubation at 4° C. overnight. The primary antibodies were IRAK1 rabbit monoclonal antibody (CST, #4504S, 1:500), IRAK3 rabbit polyclonal antibody (CST, #4369, 1:500), IRAK4 rabbit polyclonal antibody (CST, #4363S, 1:1,000), MyD88 rabbit monoclonal antibody (Abcam, A$^b$133739, 1:2,000), (3-actin mouse monoclonal antibody (Sigma, A5441, 10,000), and Gapdh mouse monoclonal antibody (Millipore, MAB374, 1:5,000). Membranes were washed three times with 1×TBST, and then incubated with IR Dye 800 CW Goat anti-rabbit (Licor, #926-32211) and IR Dye 700 CW Goat anti-mouse (Licor, #926-68070) secondary antibodies in 1:10,000 dilution at RT for 1 h. The western blot images were obtained using Odyssey Imaging System.

Figure 1:
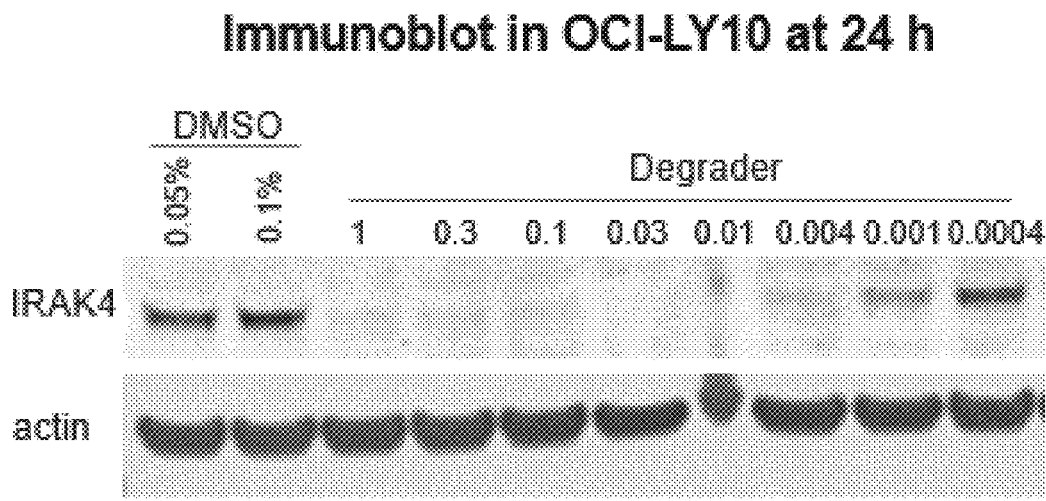
FIG. 1 is an image showing a western blot of degrader I-30 in OCI-LY10 at 24 h.

FIG. 1 shows an immunblot in OCI-LY10 at 24 h using I-30.

Example 9. IRAK4 Degradation in OCI-LY10 (MSD) and hPBMC (Flow Assay)

Degradation of IRAK4 in OCI-LY10 was quantitatively measured using Meso Scale Discovery technology. OCI-LY10 cells were seeded in 96-well plates (Corning 3799) with a density of 300,000 cells per well in 100 µL fresh media. Compounds were then added to the assay plates with a final top concentration of 1 to 10 µM in a 1:3 dilution series with total of 8 doses. The assay plates were then incubated for 4 to 24 hours at 37° C. under 5% $CO_2$. The assay plates were then centrifuged for 5 minutes and the cell pellets were treated with 100 µL/well RIPA lysis buffer (Boston Bio-Products BP-115D) with proteinase inhibitors. To prepare MSD assay plates (Meso Scale Discovery Catalog number L15XA-3), the plates were coated with 2 g/mL capture antibody (mouse Anti-IRAK4 antibody [2H9], ab119942) in PBS, at 40 µL/well. The plates were then incubated overnight at 4° C., washed 3 times with 150 µL/well TBST buffer (Cell Signaling Technology, Catalog number 9997S) and blocked with 150 µL/well blocking buffer (Meso Scale Discovery Catalog number R93BA-4). Cell lysates were then added to MSD assay plates and the plates were incubated at room temperature for 1 hour. The plates were then washed 3 times with 150 µL/well TBST buffer and 25 µL/well primary detection antibody (rabbit Anti-IRAK4 antibody [Y279], from Abcam. Catalog number ab32511, 1 pg/mL). The assay plates were then incubated at room temperature for 1 hour, washed 3 times with 150 µL/well TBST buffer and 25 L/well secondary detection antibody, SULFO-TAG anti-rabbit antibody were added (anti rabbit antibody from Meso Scale Discovery, Catalog number R32AB-1, 1 µg/mL). The assay plates were then incubated at room temperature for 1 hour, washed 3 times with 150 µL/well TB ST buffer, and 150 µL/well MSD reading buffer (Meso Scale Discovery catalog number R92TC-2) was added. The plates were then analyzed by a MSD reader (Meso Scale Discovery, Model Quick Plex SQ 120). The data was then analyzed by software Prism 7.0 from Graph-Pad and the dose-depended IRAK4 degradation were fit using a three-parameter logistic equation to calculate $DC_{50}$.

hPBMC IRAK4 degradation flow assay. Frozen PBMCs were thawed into RPMI with 10% FBS and allowed to recover. On the same day as thawed, PBMCs were plated in 96 well plate, 90 uL per well. Compound plates were prepared and a 10 point, 5-fold dilution was performed with a final DMSO concentration of 0.1%. Compound 10 µL per well was added, sealed and incubated at 37° C., 5% C02 for 20 hours (for 4 hour treatment, compounds were prepared and added the following day). Following the treatment incubation period (day 1), 1.6% PFA was added to PBMC plate and placed on plate shaker for 30 seconds and incubated for 10 mins at room temperature. Cells were spun down and washed two times with PBS/0.5% BSA, aspirated to pellet and placed into −80° C. freezer until further processing for flow. On the flow run day, PBMC plates were thawed and samples were transferred to PCR plates. The pre-perm staining cocktail (CD3 Ax488/CD8 BUV805/CD14 BUV395/CD16/56 BV711/CD19 BV785) was added to samples and incubated for 30 minutes at room temperature. Samples were washed two times and permeabilized with methanol for 10 minutes at 4° C. Samples were washed two times and the post-perm staining cocktail (CD4 PE/IRAK4 Ax647 BD #560315) was added and incubated for 30 minutes at room temperature. Samples were washed two times with PBS/BSA and run on a BD LSRFortessa. Mononuclear cells are gated by SSCH/FSCH and single cells. Monocytes are then gated through CD14 positive gate and lymphocytes are gated through CD14 negative gate. To determine absolute $DC_{50}$s and max degradation values, MFI values were normalized to DMSO max and 20 hour 10 µM min control. Twenty hour dose curves were calculated using a 4 parameter logistic regression curve fit, no constraints (Top doses were removed if hook effects were observed and the bottom was constrained to 0).

Figure 2:
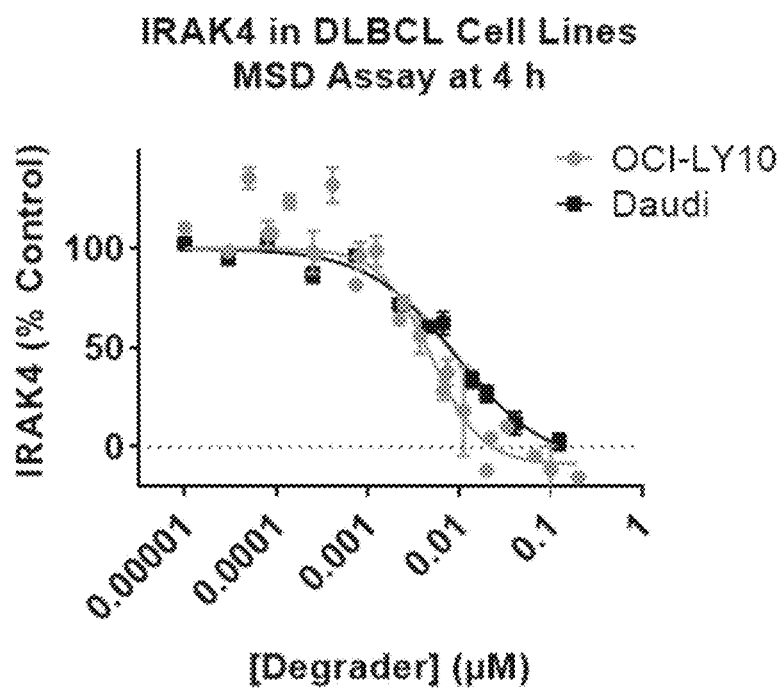
FIG. 2 is an image of a dose response curve for IKAK4 (% control)(y-axis) versus degrader I-30 concentration (μM) (x-axis) for OCI-LY10 and TMD8 cell lines and in vitro degradation results ($DC_{90}$, μM).
Figure 10:
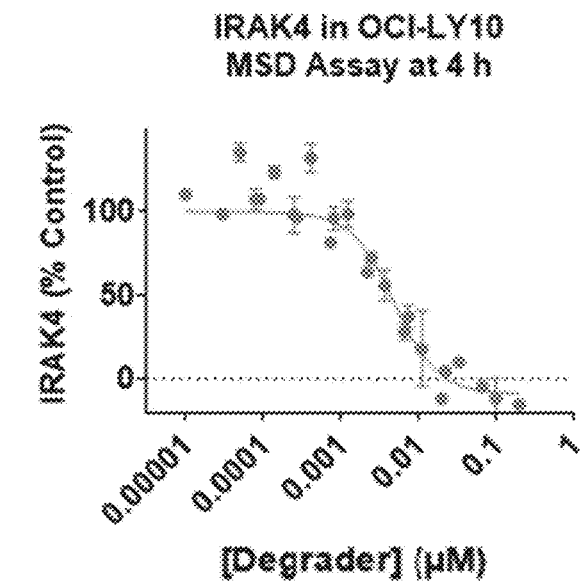
FIG. 10 is an image of a dose response curve for IKAK4 (% control) (y-axis) versus degrader I-30 concentration (uM) (x-axis) for OCI-LY10 cell lines and in vitro degradation results ($DC_{90}$, μM).

FIGS. 2 and 10 show a dose response curves for I-30 in the MSD assay for DLBCL cell lines OCI-LY10 and TMD8 at 4h with in vitro degradation results ($DC_{90}$, µM) depicted.

IRAK4 MSD degradation in OCI-LY10 results at 4 and 24 hrs and hPBMC at 20 hrs for compounds of the invention are presented in Table 8. The letter codes for IRAK4 $DC_{50}$ include: A (<0.01 µM), B (0.01-0.1 µM), C (0.1-1.0 µM), and D (>1.0 µM).

TABLE 8

IRAK4 MSD degradation in OCI-LY10 and hPMBC Results.

| Compound # | IRAK4 MSD degradation in OCI-LY10 at 4 hrs: Average external-Abs $DC_{50}$ (μM) | IRAK4 MSD degradation in OCI-LY10 at 24 hrs: Average external-Abs $DC_{50}$ (μM) | IRAK4 degradation in hPBMC monocyte at 20 hr: Average external Abs $DC_{50}$ (μM) |
|---|---|---|---|
| I-1 | A | B | — |
| I-2 | C | — | — |
| I-3 | A | — | — |
| I-5 | A | — | — |
| I-6 | A | — | — |
| I-7 | A | — | — |
| I-8 | B | — | — |
| I-9 | A | — | — |
| I-10 | A | — | — |
| I-11 | A | — | — |
| I-12 | B | — | — |
| I-13 | D | — | — |
| I-14 | B | — | — |
| I-15 | B | B | — |
| I-16 | A | — | — |
| I-17 | A | — | — |
| I-18 | A | — | — |
| I-19 | D | D | — |
| I-20 | D | D | — |
| I-21 | D | D | — |
| I-22 | D | D | — |
| I-23 | B | A | — |
| I-24 | D | D | — |
| I-25 | D | D | — |
| I-26 | D | D | — |
| I-27 | A | — | — |
| I-28 | A | — | — |
| I-29 | A | — | — |
| I-30 | A | — | — |
| I-31 | C | — | — |
| I-32 | A | — | — |
| I-33 | A | — | — |
| I-34 | A | — | — |
| I-35 | B | — | — |
| I-36 | B | — | — |
| I-37 | B | — | — |
| I-38 | A | — | — |
| I-39 | B | — | — |
| I-40 | B | — | — |
| I-41 | A | — | — |
| I-42 | B | — | — |
| I-43 | B | — | — |
| I-44 | D | D | — |
| I-45 | A | — | — |
| I-46 | B | B | — |
| I-47 | B | B | — |
| I-48 | A | — | — |
| I-49 | D | — | — |
| I-50 | D | — | — |
| I-51 | D | — | — |
| I-52 | D | — | — |
| I-53 | C | B | — |
| I-54 | C | — | — |
| I-55 | A | — | — |
| I-56 | C | — | — |
| I-57 | A | — | — |
| I-58 | A | — | — |
| I-59 | A | — | — |
| I-60 | B | — | — |
| I-61 | B | — | — |
| I-62 | A | — | — |
| I-63 | B | — | — |
| I-64 | C | — | — |
| I-65 | A | — | — |
| I-66 | A | — | — |
| I-67 | A | — | — |
| I-68 | B | — | — |
| I-69 | C | — | — |
| I-71 | C | — | — |
| I-72 | B | — | — |
| I-73 | A | — | — |
| I-74 | A | — | — |
| I-75 | A | — | — |
| I-76 | A | — | — |
| I-77 | B | — | — |
| I-78 | B | — | — |
| I-79 | B | — | — |
| I-81 | C | — | — |
| I-83 | C | — | — |
| I-84 | B | — | — |
| I-87 | A | — | — |
| I-88 | C | — | — |
| I-91 | C | — | — |
| I-92 | B | — | — |
| I-93 | B | — | — |
| I-96 | B | — | — |
| I-97 | A | — | — |
| I-107 | A | — | — |
| I-108 | A | — | — |
| I-118 | A | — | — |
| I-120 | A | — | — |
| I-127 | A | A | — |
| I-129 | A | — | — |
| I-130 | A | — | — |
| I-131 | D | D | — |
| I-132 | D | D | — |
| I-133 | D | D | — |
| I-134 | D | D | — |
| I-135 | C | D | — |
| I-136 | A | — | — |
| I-138 | D | D | — |
| I-139 | D | D | — |
| I-140 | D | D | — |
| I-141 | D | D | — |
| I-142 | D | D | — |
| I-143 | D | D | — |
| I-144 | D | D | — |
| I-145 | D | D | — |
| I-146 | D | D | — |
| I-147 | D | D | — |
| I-148 | C | — | — |
| I-149 | A | — | — |
| I-150 | B | — | — |
| I-151 | B | — | — |
| I-152 | B | — | — |
| I-153 | B | — | — |
| I-154 | B | B | — |
| I-155 | B | — | — |
| I-156 | B | — | — |
| I-157 | A | — | — |
| I-159 | D | D | — |
| I-160 | D | D | — |
| I-161 | D | D | — |
| I-162 | A | — | — |
| I-163 | A | — | — |
| I-164 | A | — | — |
| I-165 | B | — | — |
| I-166 | B | — | — |
| I-167 | C | — | — |
| I-168 | B | A | — |
| I-169 | A | — | — |
| I-170 | B | — | — |
| I-171 | B | — | — |
| I-172 | C | — | — |
| I-173 | C | — | — |
| I-174 | D | D | — |
| I-175 | D | D | — |
| I-176 | B | — | — |
| I-177 | A | — | — |
| I-179 | C | — | — |
| I-180 | B | — | — |
| I-181 | C | — | — |

TABLE 8-continued

IRAK4 MSD degradation in OCI-LY10 and hPMBC Results.

| Compound # | IRAK4 MSD degradation in OCI-LY10 at 4 hrs: Average external-Abs DC$_{50}$ (μM) | IRAK4 MSD degradation in OCI-LY10 at 24 hrs: Average external-Abs DC$_{50}$ (μM) | IRAK4 degradation in hPBMC monocyte at 20 hr: Average external Abs DC$_{50}$ (μM) |
|---|---|---|---|
| I-182 | C | — | — |
| I-183 | A | A | — |
| I-184 | B | B | — |
| I-185 | B | B | A |
| I-186 | B | A | — |
| I-187 | D | A | — |
| I-188 | C | C | — |
| I-189 | B | A | — |
| I-190 | C | B | — |
| I-191 | A | — | A |
| I-192 | B | — | — |
| I-193 | C | B | — |
| I-194 | B | — | — |
| I-195 | C | — | — |
| I-196 | B | — | — |
| I-197 | B | — | — |
| I-198 | A | — | — |
| I-199 | C | — | — |
| I-200 | A | — | — |
| I-201 | D | C | — |
| I-202 | C | B | — |
| I-203 | D | C | — |
| I-204 | C | B | — |
| I-205 | C | B | — |
| I-206 | B | B | — |
| I-207 | B | — | — |
| I-208 | B | — | — |
| I-209 | B | A | — |
| I-210 | B | B | — |
| I-211 | D | D | — |
| I-212 | B | — | — |
| I-213 | A | — | — |
| I-214 | D | D | — |
| I-215 | D | D | — |
| I-216 | C | — | — |
| I-217 | C | D | — |
| I-218 | C | C | — |
| I-219 | B | B | — |
| I-220 | D | C | — |
| I-221 | A | — | — |
| I-222 | B | — | — |
| I-223 | B | — | — |
| I-224 | C | — | — |
| I-225 | B | — | — |
| I-226 | C | B | — |
| I-227 | C | — | — |
| I-228 | D | — | — |
| I-229 | B | B | — |
| I-230 | C | C | — |
| I-231 | B | — | — |
| I-232 | A | — | — |
| I-233 | A | — | — |
| I-234 | C | B | — |
| I-235 | D | D | — |
| I-236 | A | — | — |
| I-237 | A | — | — |
| I-238 | B | — | — |
| I-239 | B | — | — |
| I-240 | A | — | — |
| I-241 | B | — | — |
| I-242 | A | — | — |
| I-243 | A | — | — |
| I-244 | A | — | — |
| I-245 | B | — | — |
| I-246 | C | — | — |
| I-247 | C | — | — |
| I-248 | A | — | — |
| I-249 | B | — | — |
| I-250 | A | — | — |
| I-251 | C | — | — |
| I-252 | A | — | — |
| I-253 | B | — | — |
| I-254 | B | — | — |
| I-255 | B | A | — |
| I-256 | A | — | — |
| I-257 | A | A | A |
| I-258 | B | B | — |
| I-259 | A | A | — |
| I-260 | C | — | — |
| I-261 | A | A | — |
| I-262 | A | A | — |
| I-263 | B | — | — |
| I-264 | A | A | — |
| I-265 | B | — | — |
| I-266 | A | A | — |
| I-267 | C | — | — |
| I-268 | C | — | — |
| I-269 | D | D | — |
| I-270 | D | D | — |
| I-271 | D | D | — |
| I-272 | D | D | — |
| I-273 | D | D | — |
| I-274 | C | C | — |
| I-275 | B | — | — |
| I-276 | A | — | — |
| I-277 | A | — | — |
| I-278 | A | A | — |
| I-279 | A | — | — |
| I-280 | B | — | — |
| I-282 | A | — | — |
| I-283 | A | — | — |
| I-284 | A | — | — |
| I-285 | B | — | — |
| I-286 | B | — | — |
| I-287 | A | — | — |
| I-288 | A | — | — |
| I-291 | B | B | — |
| I-292 | B | — | — |
| I-293 | B | — | — |
| I-294 | B | — | — |
| I-296 | B | — | — |
| I-297 | B | — | — |
| I-298 | C | — | — |
| I-299 | B | — | — |
| I-300 | C | — | — |
| I-301 | B | — | — |
| I-302 | B | — | — |
| I-303 | B | — | — |
| I-304 | D | D | — |
| I-305 | D | D | — |
| I-306 | A | — | — |
| I-307 | B | — | — |
| I-308 | A | — | — |
| I-309 | B | — | — |
| I-310 | A | — | — |
| I-311 | B | — | — |
| I-312 | D | D | — |
| I-313 | D | D | — |
| I-314 | D | D | — |
| I-315 | D | D | — |
| I-316 | D | D | — |
| I-317 | B | B | B |
| I-320 | D | — | B |
| I-321 | C | — | — |
| I-322 | C | D | — |
| I-323 | C | D | — |
| I-324 | C | — | — |
| I-325 | C | B | — |
| I-326 | A | A | A |
| I-327 | B | B | B |
| I-328 | B | A | — |
| I-329 | C | — | — |

TABLE 8-continued

IRAK4 MSD degradation in OCI-LY10 and hPMBC Results.

| Compound # | IRAK4 MSD degradation in OCI-LY10 at 4 hrs: Average external-Abs $DC_{50}$ (μM) | IRAK4 MSD degradation in OCI-LY10 at 24 hrs: Average external-Abs $DC_{50}$ (μM) | IRAK4 degradation in hPBMC monocyte at 20 hr: Average external Abs $DC_{50}$ (μM) |
|---|---|---|---|
| I-330 | 0 | A | — |
| I-331 | B | A | B |
| I-332 | C | B | — |
| I-333 | B | B | A |
| I-334 | C | — | — |
| I-335 | C | — | — |
| I-336 | C | B | — |
| I-337 | C | B | — |
| I-338 | C | — | — |
| I-339 | B | B | — |
| I-340 | C | B | — |
| I-341 | C | B | — |
| I-342 | C | — | — |
| I-343 | B | — | — |
| I-344 | C | — | — |
| I-345 | C | B | — |
| I-346 | D | — | — |
| I-347 | C | B | — |
| I-348 | D | D | — |
| I-349 | C | B | — |
| I-350 | C | B | — |
| I-351 | D | — | — |
| I-352 | D | B | — |
| I-353 | B | B | — |
| I-354 | D | — | — |
| I-355 | B | A | — |
| I-356 | D | B | — |
| I-357 | D | — | — |
| I-358 | D | B | — |
| I-359 | D | D | — |
| I-360 | B | — | — |
| I-361 | D | B | — |
| I-362 | C | B | — |
| I-363 | D | — | — |
| I-364 | — | B | — |
| I-365 | B | — | — |
| I-366 | A | — | — |
| I-367 | B | — | — |
| I-368 | D | — | — |
| I-369 | D | D | — |
| I-370 | B | — | — |
| I-371 | — | B | — |
| I-372 | D | — | — |
| I-373 | D | B | — |
| I-374 | D | B | — |
| I-375 | D | — | — |
| I-376 | B | B | A |
| I-377 | D | A | — |
| I-379 | D | D | — |
| I-380 | C | B | — |
| I-381 | B | A | — |
| I-384 | B | — | — |
| I-385 | D | B | — |
| I-386 | C | B | — |
| I-387 | C | — | — |
| I-388 | B | — | — |
| I-389 | B | B | — |
| I-390 | D | — | — |
| I-391 | D | D | — |
| I-392 | C | B | — |
| I-393 | C | B | — |
| I-395 | C | — | — |
| I-396 | B | — | B |
| I-397 | C | C | — |
| I-398 | B | B | — |
| I-399 | B | A | — |
| I-400 | A | — | — |
| I-401 | C | D | — |
| I-403 | D | B | — |
| I-404 | A | — | — |
| I-407 | A | — | A |
| I-408 | D | D | — |
| I-409 | D | — | — |
| I-410 | B | — | A |
| I-411 | D | — | B |
| I-412 | D | D | — |
| I-413 | C | — | A |
| I-414 | A | — | A |
| I-415 | A | — | A |
| I-416 | A | — | A |
| I-417 | A | — | A |
| I-418 | B | — | B |
| I-419 | B | — | A |
| I-420 | A | — | A |
| I-421 | A | — | A |
| I-422 | B | — | A |
| I-423 | C | — | A |
| I-424 | A | — | A |
| I-425 | B | — | A |
| I-426 | C | — | A |
| I-427 | — | — | C |
| I-428 | — | — | A |
| I-429 | — | — | A |
| I-430 | — | — | A |
| I-431 | — | — | A |
| I-432 | — | — | A |
| I-433 | — | — | A |
| I-434 | — | — | A |
| I-435 | — | — | A |
| I-436 | — | — | C |
| I-427 | — | — | C |
| I-437 | B | B | — |
| I-438 | C | B | — |
| I-439 | C | D | — |
| I-440 | C | D | — |
| I-441 | B | B | — |
| I-442 | C | — | C |
| I-443 | A | A | — |
| I-444 | C | A | A |
| I-445 | B | — | A |
| I-447 | B | — | A |
| I-448 | B | — | A |
| I-449 | A | — | A |
| I-450 | B | — | A |
| I-451 | B | B | — |
| I-452 | C | D | — |
| I-453 | B | A | — |
| I-454 | C | B | — |
| I-455 | B | B | — |
| I-456 | C | C | — |
| I-457 | C | D | — |
| I-458 | C | D | — |
| I-459 | C | B | — |
| I-460 | C | B | — |
| I-461 | C | — | — |
| I-462 | C | D | — |
| I-463 | B | A | — |
| I-464 | B | — | B |
| I-465 | A | — | A |
| I-466 | C | — | A |
| I-467 | A | — | A |
| I-468 | C | — | C |
| I-469 | A | — | A |
| I-470 | C | — | C |
| I-471 | A | — | A |
| I-472 | A | — | A |
| I-473 | B | A | — |
| I-474 | C | B | — |
| I-475 | B | A | — |
| I-476 | B | B | — |
| I-477 | B | B | — |
| I-478 | C | B | — |

TABLE 8-continued

IRAK4 MSD degradation in OCI-LY10 and hPMBC Results.

| Compound # | IRAK4 MSD degradation in OCI-LY10 at 4 hrs: Average external-Abs $DC_{50}$ (μM) | IRAK4 MSD degradation in OCI-LY10 at 24 hrs: Average external-Abs $DC_{50}$ (μM) | IRAK4 degradation in hPBMC monocyte at 20 hr: Average external Abs $DC_{50}$ (μM) |
|---|---|---|---|
| I-479 | C | — | C |
| I-480 | B | — | A |
| I-481 | C | — | C |
| I-482 | B | — | C |
| I-483 | C | — | A |
| I-484 | C | — | C |
| I-485 | B | — | A |
| I-486 | A | — | A |
| I-487 | B | — | A |
| I-488 | C | — | C |
| I-489 | C | D | — |
| I-490 | C | D | — |
| I-491 | C | D | — |
| I-492 | A | — | A |
| I-493 | A | — | A |
| I-494 | C | — | C |
| I-495 | C | — | B |
| I-496 | B | — | A |
| I-497 | B | — | A |
| I-498 | C | — | C |
| I-499 | A | — | A |
| I-500 | C | B | — |
| I-501 | D | D | — |
| I-502 | A | A | — |
| I-503 | D | D | — |
| I-504 | D | B | — |
| I-505 | B | A | — |
| I-506 | B | A | — |
| I-507 | — | — | A |
| I-508 | — | — | A |
| I-509 | B | — | B |
| I-510 | — | — | A |
| I-511 | B | — | A |
| I-512 | D | — | C |
| I-513 | A | — | A |
| I-514 | A | — | A |
| I-515 | A | — | A |
| I-516 | B | — | A |
| I-517 | B | — | A |
| I-518 | B | — | A |
| I-519 | B | — | C |
| I-520 | B | — | A |
| I-521 | B | — | A |
| I-522 | A | — | A |
| I-523 | A | — | A |
| I-524 | A | — | A |
| I-525 | B | — | A |
| I-526 | A | — | A |
| I-527 | B | — | A |
| I-528 | B | — | A |
| I-530 | B | — | A |
| I-531 | B | — | A |
| I-532 | B | — | B |
| I-533 | B | — | A |
| I-534 | B | — | A |
| I-535 | A | — | A |
| I-536 | B | — | A |
| I-537 | A | — | A |
| I-538 | B | — | A |
| I-539 | B | — | A |
| I-540 | B | — | A |
| I-541 | B | — | A |
| I-542 | B | — | A |
| I-543 | B | — | A |
| I-544 | B | — | C |
| I-545 | A | — | A |
| I-546 | C | — | B |
| I-547 | A | — | A |
| I-548 | C | — | C |
| I-549 | B | — | A |
| I-550 | B | — | A |
| I-551 | C | — | — |
| I-552 | C | — | — |
| I-553 | C | — | B |
| I-554 | B | — | A |
| I-555 | A | — | A |
| I-556 | B | A | — |
| I-557 | A | — | A |
| I-558 | — | — | A |
| I-559 | — | — | A |
| I-560 | A | — | — |
| I-561 | B | — | — |

Example 10. Proteomics Protocol

Total protein was isolated from OCI-LY10 cells treated with 10 nM I-30, 30 nM I-30 and 30 nM 2-{2-[(cyclopropylmethyl)amino]pyridin-4-yl}-N-[3-(difluoromethyl)-1-[4-({[2-(2-{3-[3-methyl-1-(1-methyl-2,6-dioxopiperidin-3-yl)-2-oxo-2,3-dihydro-1H-1,3-benzodiazol-4-yl]propoxy}ethoxy)ethyl]amino}methyl)phenyl]-1H-pyrazol-4-yl]-1,3-oxazole-4-carboxamide for 8 hours. Vehicle (DMSO)-treated cells were used as controls. Protein lysates, 2 biological replicates per condition, were prepared at 4 C in 8M urea, 75 mM NaCl, 1 mM EDTA in 50 mM Tris HCl (pH 8), 10 mM NaF, phosphatase inhibitor cocktail 2 (1:100; Sigma, P5726) and cocktail 3 (1:100; Sigma, P0044), 2 μg/mL aprotinin (Sigma, A6103), 10 μg/mL Leupeptin (Roche, 11017101001), and 1 mM PMSF (Sigma, 78830). Lysates were spun at 20,000 rcf for 10 min and supernatant (containing extracted proteins) was transferred to a clean microcentrifuge tube. Protein concentrations were determined using the Pierce BCA assay. Protein lysates were reduced with 5 mM dithiothreitol (Thermo Scientific, 20291) for 45 min at room temperature and alkylated with 10 mM iodoacetamide (Sigma, A3221) for an additional 45 min. Protein digests were diluted 1:4 with 50 mM Tris HCl (pH 8) before digestion with LysC (Wako, 100369-826) for 2 h and with trypsin (Promega, V511X) overnight. Both lysis steps were performed at a 1:50 enzyme-to-protein ratio and at room temperature. Digested samples were acidified with formic acid (FA; Fluka, 56302) to a final concentration of 1% (final pH of <3), and then centrifuged at 2,000 rcf for 5 min to clear precipitated urea. Peptide lysates were desalted on C18 SepPak columns (Waters, 100 mg/1 cc) and dried down using a SpeedVac Concentrator (Savant SC210A). Desalted peptides were then labeled with tandem mass tag (TMT, Thermo Fisher Scientific) reagents according to the manufacturer's instructions. TMT labeling was quenched and TMT11-plex was combined, desalted on a C18 SepPak column (Waters, 500 mg/6 cc) and fractionated by high-pH reversed phase off-line chromatography into 24 fractions. Briefly, desalted TMT labelled peptides were loaded on a 4.6 mm×250 mm column RP Zorbax 300 A Extend-C18 column (Agilent, 3.5 μm bead size), and separated on an Agilent 1100 Series HPLC instrument using basic reversed-phase chromatography. Ninety-six fractions were collected and subsequently concatenated as described earlier into 24 fractions. Each fraction was dried down and resuspended in 3% MeCN/0.1% FA to a peptide concentration of 1 µg/µL for LC-MS/MS analyses of the proteome. Online fractionation was performed using a nanoflow Proxeon EASY-nLC 1200 UHPLC system (Thermo Fisher Scientific) and separated peptides were analyzed on a benchtop Orbitrap Q Exactive plus mass spectrometer (Thermo Fisher Scientific). All data were analyzed using Spectrum Mill software package (Agilent Technologies). Identities interpreted for individual spectra were automatically designated as confidently assigned using the Spectrum Mill autovalidation module to use target-decoy based false discovery rate (FDR) estimates to apply score threshold at the spectral and protein levels. In total, 10,992 proteins were quantified. Downstream bioinformatic analysis was performed in Perseus software (developed by Max Planck Institute of Biochemistry, Munich, Germany)."

Figure 3:
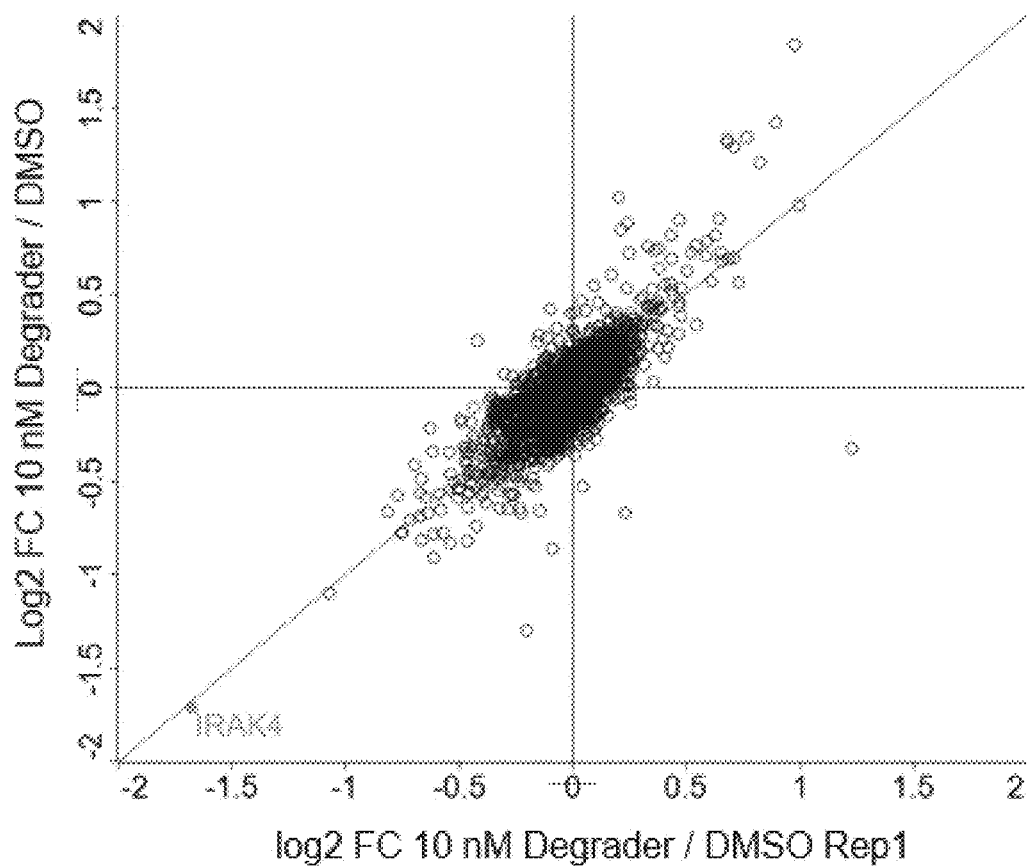
FIG. 3 is an image of a deep TMT proteomics scatterplot in OCI-LY10 at 8 h showing Log 2 FC 10 nM degrader I-30 in DMSO (y-axis) and Log 2 FC 10 nM degrader in DMSO Rep1 (x-axis).

FIG. 3 shows the results of the deep tamdem mass tag (TMT) proteomics protocol.

FIGS. 1-3 and 10 show that I-30 causes potent depletion of IRAK4 in MYD88 mutant lymphoma cell lines and is highly selective for IRAK4 vs. >10,000 other proteins in OCI-LY10.

Example 11. OCI-LY10 Flow Staining Experiments

OC1-LY10 cell line was cultured in IMDM medium supplemented with 20% FBS, B-ME and pen/strep. On Day 1, cells were plated at 200K per well in 96 well plates. Compounds were diluted to 1000× in DMSO, then further diluted to 100× in media, and added to cells at 4 concentrations over 4 different timepoints (24h, 48h, 72h and 96h). Timepoints were staggered so all cells were harvested and stained at the same time. Paclitaxel was added as a positive control and a DMSO control for each timepoint was also included. On day 5, plates were harvested and cells were fixed, permeabilized, and stored at −4 C until further processing. On day 8, the Ki67 plates were stained using KI-67-APC antibody (Biolegend, Cat #350514). The Caspase 3 plates were stained using the PE Active Caspase-3 Apoptosis Kit (BD Biosciences, Cat #550914) and the IRAK 4 plates were stained with Hu IRAK4 A$^b$ Alexa 647 Clone: L29-525 antibody (BD, Cat #560315). Cells were resuspended in staining buffer and run on a Beckman Coulter CytoFlex 13 color Cytometer (Model #A00-1-1102, Serial #AS10086).

Figure 4:
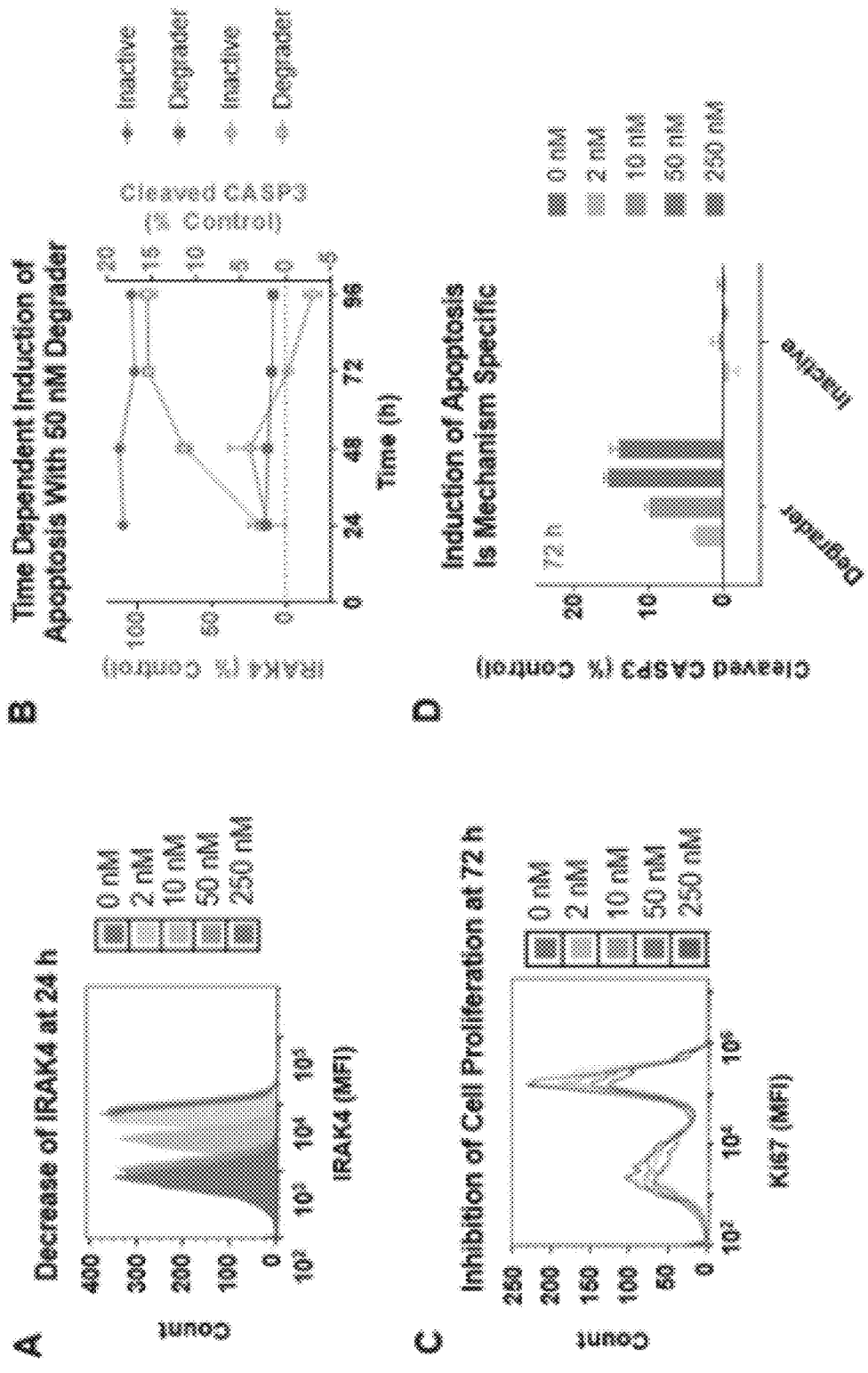
FIG. 4 includes graphical images showing the decrease of IRAK4 at 24 h with count (y-axis) versus IRAK (MFI) (x-axis) using several concentrations of degrader I-30 (A); the time dependent induction of apoptosis with 50 nM degrader I-30 showing IRAK4 (% control) (left y-axis) and cleaved CASP3 (% control) (right y-axis) versus time (h) (x-axis) (B); the inhibition of cell proliferation at 72 h showing count (y-axis) versus Ki67 (MFI) (x-axis) at several concentrations of degrader I-30 (C); and the induction of apoptosis is mechanism specific showing cleaved CASP3 (% control) (y-axis) for degrader I-30 and inactive (x-axis) at several concentrations respectively (D).

FIG. 4 shows the results of the staining experiments using I-30.

Example 12. Cell Viability Assay with OCI-LY10 and TMD8

Compound-mediated viability effect on OCI-LY10 or TMD8 was quantitatively determined using the CellTiter-Glo® Luminescent Cell Viability Assay kit from Promega (Catalog number G7570) following manufacturer's recommended procedures. Briefly, OCI-LY10 or TMD8 cells were seeded into 384 well plates (Grenier Bio-One, Catalog number 781080) with a density of 10,000 cells per well. Compounds were then added to the assay plate with final top concentration of 10 µM and 1:3 dilution series with total of 9 doses. The final DMSO concentration was normalized to 0.2%. The assay plates were incubated at 37° C. for 4 days under 5% $CO_2$. Then the assay plate was equilibrated at room temperature for 10 minutes. To determine cell viability, 30 µL CellTiter Glo reagent was added to each well and the assay plate was centrifuged at 1000 rpm for 30 second, incubated at room temperature for 10 min, and analyzed by detecting the luminescence using a multimode plate reader (EnVision 2105, PerkinElmer). The data was then analyzed by software Prism 7.0 from GraphPad and the dose response curves were fit using a three-parameter logistic equation to calculate $IC_{50}$.

FIG. 5 depicts the cellular viability results using I-30. FIGS. 4 and 5 show that I-30 treatment is cytotoxic and induces apoptosis in OCI-LY10 lymphoma line.

CTG Cell Viability Assay—OCI-LY10 results for compounds of the invention are presented in Table 9. The letter codes for IRAK4 $IC_{50}$ include: A (<0.05 µM), B (0.05-0.1 µM), C (0.1-0.5 µM), D (0.5-1.0 µM), and E (>1.0 µM).

TABLE 9

CTG Cell Viability Assay Results.

| Compound # | CTG Cell Viability Assay - OCI-LY10: Average external-$IC_{50}$ (µM) |
|---|---|
| I-1 | B |
| I-2 | C |
| I-3 | E |
| I-5 | A |
| I-6 | E |
| I-7 | E |
| I-8 | E |
| I-9 | E |
| I-10 | E |
| I-11 | E |
| I-12 | D |
| I-13 | E |
| I-14 | C |
| I-15 | E |
| I-16 | C |
| I-17 | C |
| I-18 | B |
| I-20 | E |
| I-21 | D |
| I-22 | C |
| I-23 | B |
| I-24 | E |
| I-25 | E |
| I-26 | E |
| I-27 | A |
| I-28 | A |
| I-29 | E |
| I-30 | C |
| I-31 | C |
| I-32 | C |
| I-33 | E |
| I-34 | E |
| I-35 | A |
| I-36 | D |
| I-37 | A |
| I-38 | A |
| I-39 | B |
| I-40 | A |
| I-41 | E |
| I-42 | E |
| I-43 | E |
| I-44 | E |
| I-45 | A |
| I-46 | D |
| I-47 | C |
| I-48 | A |
| I-49 | E |
| I-50 | E |
| I-51 | E |
| I-52 | C |
| I-53 | E |
| I-58 | B |
| I-59 | A |
| I-61 | C |
| I-62 | B |
| I-65 | A |
| I-67 | A |

TABLE 9-continued

CTG Cell Viability Assay Results.

| Compound # | CTG Cell Viability Assay - OCI-LY10: Average external-IC$_{50}$ (μM) |
|---|---|
| I-75 | A |
| I-76 | A |
| I-81 | E |
| I-92 | C |
| I-106 | E |
| I-107 | E |
| I-108 | E |
| I-109 | E |
| I-110 | E |
| I-111 | E |
| I-112 | E |
| I-113 | E |
| I-114 | C |
| I-115 | E |
| I-116 | E |
| I-117 | E |
| I-118 | E |
| I-119 | E |
| I-120 | E |
| I-121 | E |
| I-122 | E |
| I-123 | D |
| I-124 | E |
| I-125 | E |
| I-126 | E |
| I-127 | E |
| I-128 | E |
| I-129 | E |
| I-130 | E |
| I-131 | E |
| I-132 | E |
| I-133 | E |
| I-134 | E |
| I-135 | E |
| I-136 | E |
| I-137 | E |
| I-138 | E |
| I-139 | E |
| I-140 | E |
| I-141 | E |
| I-142 | E |
| I-143 | E |
| I-144 | E |
| I-145 | E |
| I-146 | E |
| I-147 | E |
| I-148 | C |
| I-149 | E |
| I-150 | A |
| I-151 | E |
| I-152 | E |
| I-153 | E |
| I-155 | E |
| I-156 | E |
| I-157 | E |
| I-159 | E |
| I-160 | E |
| I-161 | E |
| I-162 | E |
| I-163 | E |
| I-164 | E |
| I-165 | D |
| I-166 | E |
| I-167 | C |
| I-168 | A |
| I-169 | E |
| I-170 | A |
| I-171 | C |
| I-172 | E |
| I-173 | E |
| I-174 | E |
| I-175 | E |
| I-176 | E |
| I-177 | C |
| I-179 | E |
| I-180 | E |
| I-181 | C |
| I-182 | E |
| I-183 | A |
| I-184 | E |
| I-185 | E |
| I-186 | E |
| I-187 | E |
| I-188 | E |
| I-189 | E |
| I-190 | E |
| I-191 | E |
| I-192 | E |
| I-193 | E |
| I-194 | E |
| I-195 | E |
| I-196 | E |
| I-197 | E |
| I-198 | E |
| I-199 | E |
| I-200 | B |
| I-201 | E |
| I-202 | E |
| I-203 | E |
| I-204 | E |
| I-205 | E |
| I-206 | E |
| I-207 | E |
| I-208 | A |
| I-209 | E |
| I-210 | E |
| I-211 | B |
| I-212 | E |
| I-213 | E |
| I-214 | E |
| I-215 | E |
| I-216 | E |
| I-217 | B |
| I-218 | E |
| I-219 | E |
| I-220 | E |
| I-221 | B |
| I-222 | C |
| I-223 | E |
| I-224 | E |
| I-225 | E |
| I-226 | A |
| I-227 | A |
| I-228 | E |
| I-229 | E |
| I-230 | E |
| I-231 | A |
| I-232 | A |
| I-233 | C |
| I-234 | E |
| I-235 | E |
| I-236 | E |
| I-237 | E |
| I-239 | E |
| I-240 | E |
| I-241 | D |
| I-242 | D |
| I-243 | E |
| I-244 | C |
| I-245 | A |
| I-246 | E |
| I-247 | E |
| I-249 | A |
| I-250 | A |
| I-252 | C |
| I-254 | C |

TABLE 9-continued

CTG Cell Viability Assay Results.

| Compound # | CTG Cell Viability Assay - OCI-LY10: Average external-IC$_{50}$ (μM) |
|---|---|
| I-257 | E |
| I-259 | E |
| I-260 | E |
| I-263 | A |
| I-265 | A |
| I-267 | E |
| I-268 | E |
| I-269 | E |
| I-270 | E |
| I-271 | E |
| I-272 | E |
| I-273 | E |
| I-274 | D |
| I-275 | E |
| I-276 | E |
| I-277 | E |
| I-278 | E |
| I-279 | E |
| I-280 | E |
| I-282 | E |
| I-283 | E |
| I-284 | E |
| I-285 | E |
| I-286 | E |
| I-287 | E |
| I-288 | E |
| I-289 | E |
| I-302 | E |
| I-290 | E |
| I-291 | A |
| I-292 | E |
| I-293 | E |
| I-294 | A |
| I-296 | E |
| I-297 | E |
| I-298 | C |
| I-299 | B |
| I-300 | D |
| I-301 | A |
| I-303 | E |
| I-304 | E |
| I-305 | E |
| I-306 | E |
| I-307 | E |
| I-308 | A |
| I-309 | A |
| I-310 | E |
| I-311 | E |
| I-312 | E |
| I-313 | E |
| I-314 | E |
| I-315 | E |
| I-316 | E |
| I-317 | E |
| I-320 | E |
| I-321 | E |
| I-322 | E |
| I-323 | E |
| I-324 | A |
| I-325 | E |
| I-326 | A |
| I-327 | D |
| I-328 | A |
| I-329 | E |
| I-330 | E |
| I-331 | A |
| I-332 | C |
| I-333 | C |
| I-334 | C |
| I-335 | D |
| I-336 | B |
| I-337 | B |
| I-338 | A |
| I-339 | B |
| I-340 | C |
| I-341 | E |
| I-342 | B |
| I-343 | A |
| I-344 | A |
| I-345 | A |
| I-346 | A |
| I-347 | A |
| I-348 | E |
| I-349 | A |
| I-350 | E |
| I-351 | E |
| I-352 | D |
| I-353 | C |
| I-354 | E |
| I-355 | C |
| I-356 | A |
| I-357 | E |
| I-358 | B |
| I-359 | A |
| I-360 | E |
| I-361 | D |
| I-362 | D |
| I-363 | E |
| I-364 | B |
| I-365 | A |
| I-366 | A |
| I-367 | C |
| I-368 | E |
| I-369 | C |
| I-370 | C |
| I-371 | B |
| I-372 | A |
| I-373 | A |
| I-374 | E |
| I-375 | D |
| I-376 | C |
| I-377 | A |
| I-379 | C |
| I-380 | E |
| I-381 | B |
| I-384 | A |
| I-385 | A |
| I-386 | A |
| I-387 | A |
| I-389 | A |
| I-390 | E |
| I-391 | E |
| I-392 | C |
| I-393 | B |
| I-395 | E |
| I-396 | B |
| I-397 | B |
| I-398 | B |
| I-399 | A |
| I-400 | A |
| I-401 | D |
| I-403 | B |
| I-404 | A |
| I-405 | E |
| I-406 | E |
| I-407 | E |
| I-408 | E |
| I-409 | E |
| I-410 | E |
| I-411 | E |
| I-412 | E |
| I-413 | E |
| I-414 | E |
| I-415 | E |
| I-416 | E |
| I-417 | E |

TABLE 9-continued

CTG Cell Viability Assay Results.

| Compound # | CTG Cell Viability Assay - OCI-LY10: Average external-IC$_{50}$ (μM) |
|---|---|
| I-418 | E |
| I-419 | E |
| I-420 | A |
| I-421 | E |
| I-422 | E |
| I-423 | E |
| I-424 | E |
| I-425 | E |
| I-426 | E |
| I-437 | C |
| I-438 | B |
| I-439 | A |
| I-440 | E |
| I-441 | E |
| I-442 | A |
| I-443 | A |
| I-444 | A |
| I-445 | E |
| I-447 | E |
| I-448 | E |
| I-449 | E |
| I-450 | E |
| I-451 | C |
| I-452 | E |
| I-453 | B |
| I-454 | B |
| I-455 | B |
| I-456 | A |
| I-457 | E |
| I-458 | E |
| I-459 | A |
| I-460 | B |
| I-461 | A |
| I-462 | A |
| I-463 | C |
| I-473 | A |
| I-474 | A |
| I-475 | A |
| I-476 | E |
| I-477 | D |
| I-478 | E |
| I-479 | E |
| I-480 | E |
| I-481 | E |
| I-482 | E |
| I-483 | E |
| I-484 | E |
| I-485 | E |
| I-486 | E |
| I-487 | E |
| I-488 | E |
| I-489 | A |
| I-490 | E |
| I-491 | E |
| I-492 | E |
| I-493 | E |
| I-494 | E |
| I-495 | E |
| I-496 | E |
| I-497 | E |
| I-498 | E |
| I-499 | E |
| I-500 | B |
| I-501 | B |
| I-502 | A |
| I-503 | A |
| I-504 | C |
| I-505 | E |
| I-506 | D |
| I-508 | E |
| I-509 | E |
| I-510 | E |
| I-511 | E |
| I-512 | E |
| I-513 | E |
| I-514 | E |
| I-515 | E |
| I-516 | E |
| I-517 | E |
| I-518 | E |
| I-519 | C |
| I-520 | E |
| I-521 | E |
| I-522 | C |
| I-523 | E |
| I-524 | E |
| I-525 | E |
| I-526 | E |
| I-532 | E |
| I-544 | E |
| I-551 | A |
| I-552 | A |
| I-553 | E |
| I-554 | E |
| I-555 | E |
| I-557 | E |
| I-558 | E |
| I-559 | E |
| I-563 | E |

Example 13. Evaluation of Efficacy in OCI-LY10 or TMD8 Large B Lymphoma Xenograft Models in Female C.B. 17 SCID Mice Cell Culture: The OCI-LY10 or TMD8 tumor cells were maintained as suspension in RPMI1640 medium supplemented with 10% fetal bovine serum, 100 U/mL penicillin and 100 μg/mL streptomycin at 37° C. in an atmosphere of 5% $CO_2$ in air. The tumor cells were routinely subcultured twice weekly by trypsin-EDTA treatment. The cells growing in an exponential growth phase were harvested and counted for tumor inoculation.

Animals: C.B. 17 SCID, female, 6-8 weeks, weighing approximately 16-18 g were used. Animals were housed and maintained according to IACUC protocols.

Tumor Inoculation: Each mouse was inoculated subcutaneously at the right flank with OCI-LY10 or TMD8 tumor cells ($10 \times 10^6$) in 0.2 mL of PBS with matrigel for tumor development. The treatments were started when the tumor sizes reached approximately 150-450 mm$^3$ for the studies.

Assignment to Groups: Before commencement of treatment, all animals were weighed and the tumor volumes were measured. Since the tumor volume can affect the compound PK/PD, mice are assigned into groups using an Excel-based randomization procedure performing stratified randomization based upon their tumor volumes.

Observation: After tumor inoculation, the animals were checked daily for morbidity and mortality. During routine monitoring, the animals were checked for any effects of tumor growth and treatments on behavior such as mobility, food and water consumption, body weight gain/loss, eye/hair matting and any other abnormalities. Mortality and observed clinical signs were recorded for individual animals in detail.

Data Collection: Tumor volumes were measured in two dimensions using a caliper, and the volumes were expressed in mm$^3$ using the formula: "V=(L×W×W)/2, where V is tumor volume, L is tumor length (the longest tumor dimension) and W is tumor width (the longest tumor dimension perpendicular to L).

At termination: At pre-determined time points based on study design, animals were humanely sacrificed by $CO_2$. Blood was obtained by cardiac puncture for isolation of plasma, any residual tumor was removed and divided in 2 portions, 1 (minimal) for terminal compound exposure and 1 to determine IRAK4 and actin. Compound was determined in tumor and plasma using LC/MS with calibrated standards.

Interleukin-1 receptor-associated kinase 4 (IRAK4) was quantified in human OCI-LY10 and TMD8 xenograft tumors, together with mouse splenocytes and peripheral blood mononuclear cells (PBMCs), by ultra-performance liquid chromatography-tandem mass spectrometry (UPLC-MS/MS). The concentrations of IRAK4 were normalized by the concentrations of actin in the respective samples. The tumors, splenocytes and PBMCs were lysed in tissue protein extraction reagent (T-PER, ThermoFisher). The samples were centrifuged at 10,000 rpm for 10 minutes. The supernatant (cell lysate) was transferred to another tube. The cell lysates were denatured, reduced, and alkylated with iodoacetamide. The alkylated samples were treated with trypsin to generate the IRAK4 peptide LAVAIK and the actin peptide GYSFTTTAER. These peptides are unique and specific to IRAK4 and actin, respectively, in human, rat and mouse cells and tissues due to sequence conservation between these species.

Signature peptide concentrations were quantitated using a sensitive and specific targeted LC-MS/MS method. Corresponding mass-shifted, stable isotope-labeled peptides (LAV(d8)AIK and GYSF(d8)TTTAE(d6)R) were used as internal standards (ISs). Calibration standards and were prepared fresh on the day of analysis by diluting synthetic LAVAIK and GYSF(d8)TTTAER peptides into 0.1% formic acid in 90/10 water acetonitrile (v/v). The standards and study samples) were aliquoted into a 96-well plate and mixed with IS spiking solution. The sample plate was covered with heating foil.

Signature peptide levels (LAVAIK, GYSFTTTAER) were quantified by UPLC-MS/MS. Injections were made using a Shimadzu ultra performance liquid chromatograph (UPLC) platform. Mobile phase A was 0.1% formic acid in water. Mobile phase B was 0.1% formic acid in 90:10 acetonitrile/water (v/v). A SCIEX TripleTOF 6600 LC-MS/MS system was used for the detection and quantitation of analytes. The intensities of the analytes and ISs were determined by integration of extracted ion peak areas using Analyst and MultiQuant 3.0 software. Calibration curves were prepared by plotting the analyte to IS peak area ratio vs. concentration. The model for the calibration curves was linear with $1/x^2$ weighting. The working range of the assay was 0.02-50 ng/mL for LAVAIK and 1-2500 ng/mL for GYSFTTTAER in digested cell lysate. Measured peptide levels were corrected for sample work up and converted to actual protein concentrations in ng/mg total protein of cell lysate. The concentrations of IRAK4 were normalized across samples by actin concentration.

Figure 6:
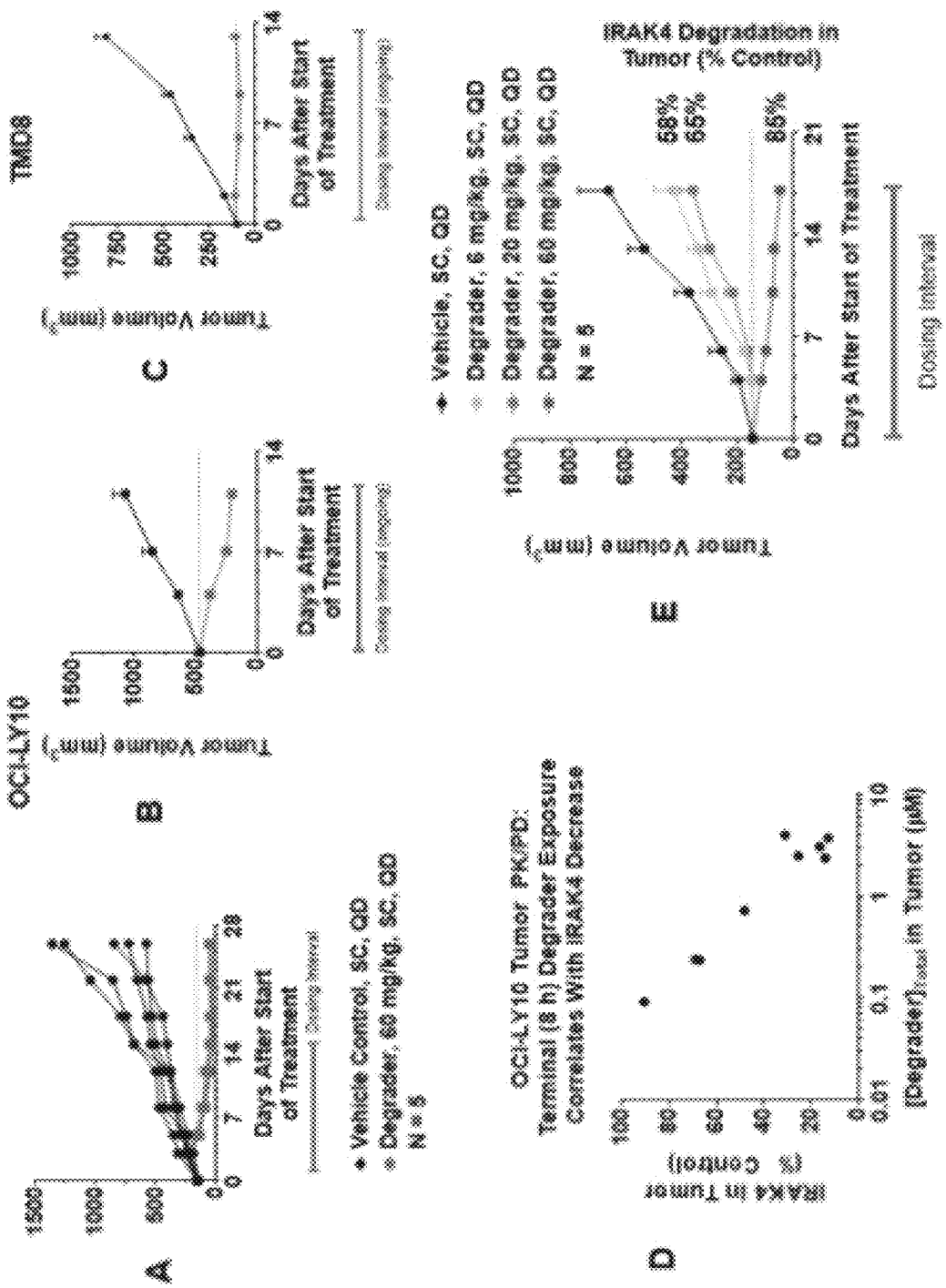
FIG. 6 includes graphical images of xenograft results for control (SC, QD) and degrader I-30 (60 mg/kg SC, QD, N=5) showing tumor volume ($mm^3$) (y-axis) versus dosing interval (days after start of treatment) (x-axis) for OCI-LY10 (A and B) and TMD8 cells (C); data showing terminal (8 h) degrader I-30 exposure correlates with IRAK4 decrease in OCI-LY10 tumor PK/PD with IRAK4 in tumor (% control) (y-axis) versus total degrader concentration in tumor (μM) (D); and data showing tumor volume ($mm^3$) (left y-axis) and IRAK4 I-30 degradation in tumor (% control) (right y-axis) versus dosing interval (days after start of treatment) (E).
Figure 7:
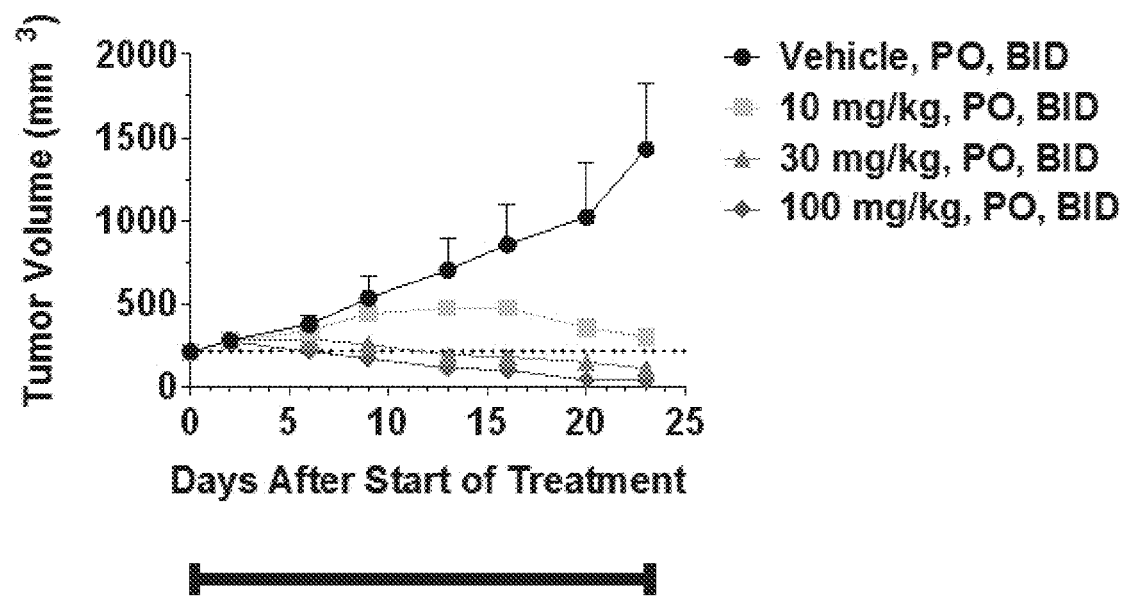
FIG. 7 is a graphical image of xenograph results for vehicle (PO, BID) and degrader I-30 (PO, BID: 10 mg/kg; 30 mg/kg; and 100 mg/kg) showing tumor volume ($mm^3$) (y-axis) versus dosing interval (days after start of treatment) (x-axis) for OCI-LY10 (MYD88 mutant) cells.
Figure 11:
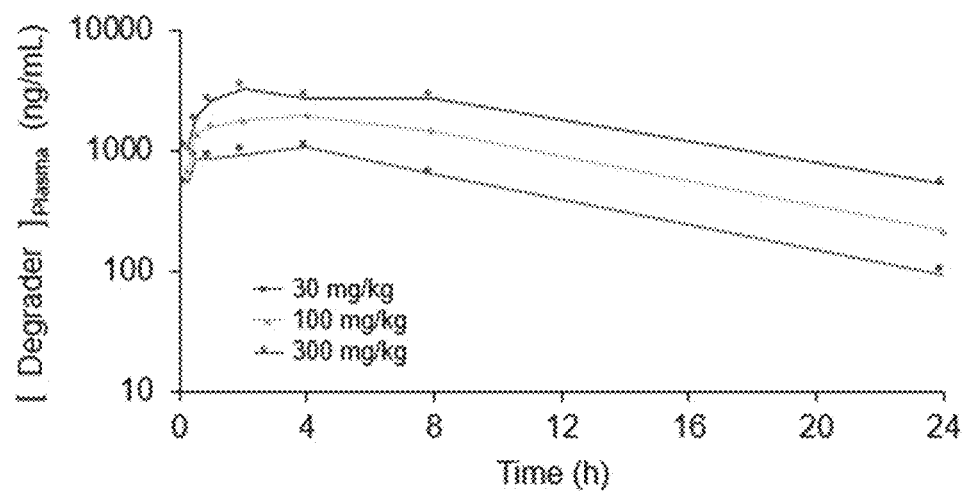
FIG. 11 is a graphical image showing oral degrader I-75 exposure in mouse with degrader concentration in plasma (ng/mL) (y-axis) over time (hours) (x-axis) at doses of 30 mg/kg, 100 mg/kg, and 300 mg/kg (A), PK characteristics in CD1 mice (B), and oral bioavailability across species (C).
Figure 13:
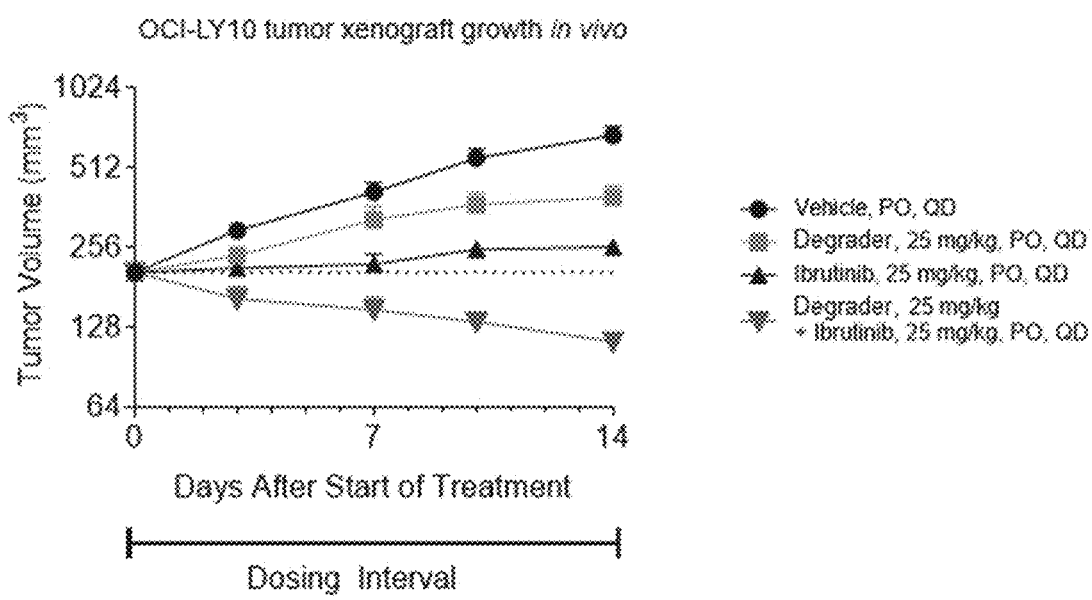
FIG. 13 is a graphical image of in vivo xenograph results for vehicle (PO, QD), degrader I-30 (PO, QD, 25 mg/kg), ibrutinib (PO, QD, 25 mg/kg), and degrader+ibrutinib (PO, QD: 25+25 mg/kg), showing tumor volume ($mm^3$) (y-axis) versus dosing interval (days after start of treatment) (x-axis) for OCI-LY10 (MYD88 L265P, CD79 mutant) cells.
Figure 14:
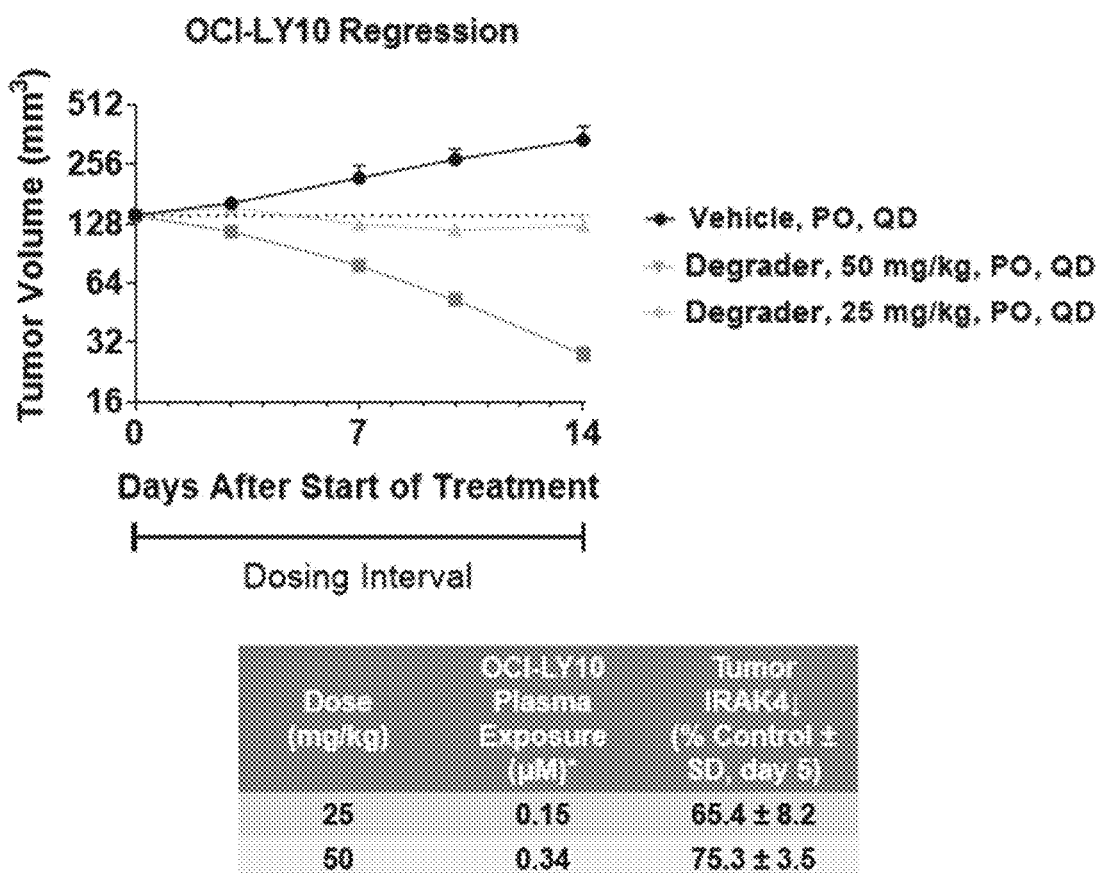
FIG. 14 is a graphical image of in vivo xenograph results for vehicle (10% TPGS in water, PO, QD) and degrader I-75 (PO, QD: 25 mg/kg and 50 mg/kg) showing tumor volume ($mm^3$)(y-axis) versus dosing interval (days after start of treatment) (x-axis) for OCI-LY10 (MYD88 mutant) cells.

FIG. 6 A-C show that I-30 causes tumor regression in OCI-LY10 and is active in TMD8 xenograft models. FIG. 6 D-E shows I-30 tumor PK/PD and relationship to antitumor effect. FIG. 7 shows results from a xenograph model showing that PO BID administration of I-30 inhibits in vivo tumor growth of implanted OCI-LY10 (MYD88 mutant) cells. FIG. 11 shows that I-75 shows dose proportional oral exposure in plasma up to 300 mg/kg and is oral bioavailable in rat, dog, and monkey. FIG. 13 shows the results from a xenograph model showing the synergistic in vivo tumor growth inhibition of implanted OCI-LY10 (MYD88 L265P, CD79 mutant) cells using a combination of I-30 and ibrutinib at concentrations that are sub-optimal for single agent administration alone. FIG. 14 shows oral dosing of I-75 showed dose-dependent antitumor activity against OCI-LY10, with >75% degradation of IRAK4 correlating with tumor regression in xenograft-bearing mice. FIGS. 23-30 show additional results for compounds of the invention in OCI-LY10 xenographs. FIG. 31 shows results for compounds of the invention in SUDHL-2 xenographs. SUDHL-2 xenographs are prepared substantially as described above using OCI-LY10.

Example 14. In Vitro Degrader Potency Data

Human whole blood IRAK4 degradation flow assay. Whole blood was collected in heparinized tubes and plated on the same day as draw (day 0). Whole blood was aliquoted into deep well plates. Compound plates were prepared and a 10 point, 5-fold dilution was performed with a final DMSO concentration of 0.1%. Compound was added to whole blood deep well plate, sealed and incubated at 37° C., 5% $CO_2$ for 20 hours (for 4 hour treatment, compounds were prepared and added the following day). Following the treatment incubation period (day 1), BD lyse fix (BD #558049) was added to the whole blood plate, placed on plate shaker for 30 seconds and incubated for 10 mins at room temperature. Whole blood was then spun down and washed two times with PBS/0.5% BSA, aspirated to pellet and placed into −80° C. freezer until further processing for flow. On the flow run day, whole blood plates were thawed and samples were transferred to PCR plates. The pre-perm staining cocktail (CD3 Ax488/CD8 BUV805/CD14 BUV395/CD16/56 BV711/CD19 BV785) was added to samples and incubated for 30 minutes at room temperature. Samples were washed two times and permeabilized with Methanol for 10 minutes at 4° C. Samples were washed two times and the post-perm staining cocktail (CD4 PE/IRAK4 Ax647 BD #560315) was added and incubated for 30 minutes at room temperature. Samples were washed two times with PBS/BSA and run on a BD LSRFortessa. Mononuclear cells are gated by SSCH/FSCH and single cells. Monocytes are then gated through CD14 positive gate and lymphocytes are gated through CD14 negative gate. To determine absolute $DC_{50}$ and max degradation values, MFI values were normalized to DMSO max and 20 hour 10 µM min control. Twenty hour dose curves were calculated using a 4 parameter logistic regression curve fit, no constraints (Top doses were removed if hook effects were observed and the bottom was constrained to 0).

Human PBMC LPS TNFα assay. Frozen PBMCs were thawed into RPMI with 10% FBS/1% penicillin/streptomycin and same day plated into 96 well plates at 200,000 PBMC/2298.8 uL media per well. Compound plates were prepared in DMSO with D300 cassette as 8-point dose curves in duplicate, starting dose 2 µM, 5-fold. Compounds are added 200 nL into cells for final 200 µL per well. Compound and cells were incubated at 37° C., 5% $CO_2$ for 20 hours. After twenty hours of pretreatment with the compounds, LPS (01 1 1:B4) (Sigma #L2637) was added at 100 ng/ml final concentration and PBMCs incubated an additional five hours at 37° C., 5% $CO_2$. Following assay completion, PBMC plates were spun down at 2000 rpm for 10 minutes. 100 uL of supernatant was carefully removed and placed into a new 96 well Costar (#3879) plate and stored at −80° C. until further analysis. Meso scale Discovery (MSD) human V-plex assays were used to measure cytokine levels. On day of cytokine analysis, supernatant samples were thawed, diluted with V-plex diluent #2, and directly to MSD plates. Assay was further completed per standard manufacturer's protocol. Cytokine data was normalized to LPS stimulated and unstimulated controls. Prism Graphpad was used to generate $IC_{50}$ using 4 parameter logistic regression curve, free-fit.

Human Whole blood LPS TNFα assay. Whole blood was collected fresh and plated same day into 96 well plates at 180 μL per well. Compound plates were prepared in DMSO as 8-point dose curves in duplicate, starting dose 2 μM, 5-fold. Compounds are added 20 μL into blood for final 200 μL per well. Compound and cells were incubated at 37° C., 5% $CO_2$ for 20 hours. After twenty hours of pretreatment with the compounds, LPS (01 1 1:B4) (Sigma #L2637) was added at 100 ng/ml final concentration and blood incubated an additional five hours at 37° C., 5% $CO_2$. Following assay completion, whole blood plates were spun down at 2000 rpm for 15 minutes at 4° C. 50 μL of plasma was carefully removed and placed into a new 96 well Costar (#3879) plate and stored at −80° C. until further analysis. Meso scale Discovery (MSD) human V-plex assays were used to measure cytokine levels. On day of cytokine analysis, plasma samples were thawed, diluted with V-plex diluent #2, and directly to MSD plates. Assay was further completed per standard manufacturer's protocol. Cytokine data was normalized to LPS stimulated and unstimulated controls. Prism Graphpad was used to generate $IC_{50}$ using 4 parameter logistic regression curve, free-fit.

IRAK4 degradation in whole blood monocyte-Flow cytometry results for compounds of the invention are presented in Table 10. The letter codes for IRAK4 $IC_{50}$ include: A (<0.05 μM), B (0.05-0.1 μM), C (0.1-0.5 μM), D (0.5-1.0 μM), and E (>1.0 μM).

TABLE 10

IRAK4 degradation in whole blood monocyte-Flow cytometry Results.

| Compound # | IRAK4 degradation in whole blood monocyte-Flow cytometry: Average external Abs $IC_{50}$ (uM) |
|---|---|
| I-1 | C |
| I-2 | A |
| I-3 | A |
| I-5 | C |
| I-6 | A |
| I-7 | A |
| I-8 | A |
| I-9 | A |
| I-10 | A |
| I-11 | A |
| I-12 | D |
| I-16 | A |
| I-17 | A |
| I-18 | A |
| I-27 | A |
| I-28 | B |
| I-29 | D |
| I-30 | A |
| I-31 | B |
| I-32 | A |
| I-33 | D |
| I-34 | A |
| I-35 | A |
| I-36 | A |

TABLE 10-continued

IRAK4 degradation in whole blood monocyte-Flow cytometry Results.

| Compound # | IRAK4 degradation in whole blood monocyte-Flow cytometry: Average external Abs $IC_{50}$ (uM) |
|---|---|
| I-37 | A |
| I-38 | A |
| I-39 | B |
| I-40 | A |
| I-41 | A |
| I-42 | A |
| I-43 | B |
| I-45 | A |
| I-46 | D |
| I-47 | D |
| I-48 | A |
| I-58 | A |
| I-59 | A |
| I-61 | B |
| I-62 | A |
| I-65 | A |
| I-67 | B |
| I-75 | B |
| I-76 | B |
| I-81 | E |
| I-92 | C |
| I-94 | C |

IRAK4 human whole blood LPS TNFα inhibition results for compounds of the invention are reported in Table 11. The letter codes for IRAK4 $IC_{50}$ include: A (<0.05 μM), B (0.05-0.1 μM), C (0.1-0.5 μM), D (0.5-1.0 μM), and E (>1.0 μM).

TABLE 11

IRAK4 human whole blood LPS TNFa inhibition Results.

| Compound # | IRAK4 human whole blood LPS TNFa inhibition: Average external-$IC_{50}$ (uM) |
|---|---|
| I-2 | E |
| I-5 | E |
| I-6 | E |
| I-7 | E |
| I-8 | E |
| I-9 | E |
| I-10 | E |
| I-11 | E |
| I-12 | D |
| I-16 | E |
| I-17 | D |
| I-18 | C |
| I-27 | C |
| I-28 | E |
| I-29 | E |
| I-30 | C |
| I-31 | E |
| I-32 | E |
| I-34 | C |
| I-35 | D |
| I-36 | C |
| I-37 | C |
| I-38 | C |
| I-39 | C |
| I-40 | C |
| I-41 | D |
| I-42 | E |
| I-43 | C |
| I-44 | E |

TABLE 11-continued

IRAK4 human whole blood LPS TNFa inhibition Results.

| Compound # | IRAK4 human whole blood LPS TNFa inhibition: Average external-IC$_{50}$ (uM) |
|---|---|
| I-45 | D |
| I-46 | E |
| I-47 | E |
| I-48 | C |
| I-58 | E |
| I-59 | E |
| I-61 | E |
| I-62 | E |
| I-65 | E |
| I-75 | E |

IRAK4 hPBMC LPS TNF-α inhibition results for compounds of the invention are reported in Table 12. The letter codes for IRAK4 IC$_{50}$ include: A (<0.05 µM), B (0.05-0.1 µM), C (0.1-0.5 µM), D (0.5-1.0 µM), and E (>1.0 µM).

TABLE 12

IRAK4 hPBMC LPS TNFa inhibition Results.

| Compound # | IRAK4 hPBMC LPS TNF-α inhibition: Average external-IC$_{50}$ (µM) |
|---|---|
| I-2 | C |
| I-11 | A |
| I-16 | C |
| I-17 | A |
| I-30 | B |
| I-31 | C |
| I-32 | B |
| I-33 | D |
| I-34 | C |
| I-35 | C |
| I-36 | C |
| I-37 | A |
| I-38 | A |
| I-39 | B |
| I-40 | A |
| I-41 | C |
| I-42 | C |
| I-43 | C |
| I-44 | E |
| I-45 | A |
| I-46 | C |
| I-47 | C |
| I-48 | C |
| I-58 | C |
| I-59 | A |
| I-61 | C |
| I-62 | C |
| I-65 | A |
| I-67 | B |
| I-75 | A |
| I-76 | A |
| I-81 | D |

IRAK4 degradation in whole blood lymphocyte-Flow cytometry results for compounds of the invention are reported in Table 13. The letter codes for IRAK4 IC$_{50}$ include: A (<0.05 µM), B (0.05-0.1 µM), C (0.1-0.5 µM), D (0.5-1.0 µM), and E (>1.0 µM).

TABLE 13

IRAK4 degradation in whole blood lymphocyte-Flow cytometry Results.

| Compound # | IRAK4 degradation in whole blood lymphocyte-Flow cytometry: Average external Abs IC$_{50}$ (µM) |
|---|---|
| I-1 | C |
| I-2 | A |
| I-3 | A |
| I-5 | C |
| I-6 | A |
| I-7 | C |
| I-8 | A |
| I-9 | B |
| I-10 | C |
| I-11 | A |
| I-12 | C |
| I-16 | B |
| I-17 | B |
| I-18 | C |
| I-27 | A |
| I-28 | C |
| I-29 | D |
| I-30 | A |
| I-31 | C |
| I-32 | B |
| I-33 | A |
| I-34 | A |
| I-35 | B |
| I-36 | A |
| I-37 | A |
| I-38 | B |
| I-39 | C |
| I-40 | C |
| I-41 | A |
| I-42 | A |
| I-43 | C |
| I-45 | B |
| I-46 | C |
| I-47 | C |
| I-48 | A |
| I-58 | B |
| I-59 | B |
| I-61 | C |
| I-62 | A |
| I-65 | B |
| I-67 | B |
| I-75 | B |
| I-76 | B |
| I-81 | E |
| I-92 | D |
| I-94 | C |

Example 15. Evaluation of Efficacy of I-30 in Murine Model of Monosodium Urate (MSU) Crystal-Induced Inflammatory Cell Infiltration into the Six-Day Air Pouch; a Model of Human Gout in Male BALB/c Mice Animals: BALB/c mice, male, 5-6 weeks, weighing approximately 19-23 g were used. Animals were housed and maintained according to IACUC protocols.

Air Pouch: Each mouse was anesthetized and injected with 6 mL of sterile air subcutaneously (SC) at the nape of the neck and the injection site was sealed with flexible colloidon to create an air pouch. Three days later, the mice were injected with 3 mL of sterile air SC at the same site and the injection site was sealed with flexible colloidon.

Preparation of MSU Crystals: 10 g uric acid (Sigma, Cat. U2625, lot BCBM5312V) was heated to 60° C. in 2 L purified water, containing 5.8 mL 10 N NaOH. The pH of the heated mixture was adjusted to 8.9, yielding a clear solution which was stored overnight at 4-8° C. to allow MSU crystals to form and precipitate. The MSU crystals were washed three times with 1 L purified water and stored at 37° C. to dry.

Formulation of Degrader: 0.5% CMC/0.25% Tween-80 was prepared by dissolving 0.5 g carboxymethylcellulose (Sigma, Cat. C4888, lot 101K0185) in 100 mL de-ionized water followed by the addition of 0.25 mL Tween-80 (Sigma, Cat. P1754, lot 073K0064). I-30 was sonicated in 0.5% CMC/0.25% Tween-80 to prepare a 10 mg/ml suspension and this was diluted in 0.5% CMC/0.25% Tween-80 to prepare a 3 mg/mL suspension and a 1 mg/mL suspension for dosing.

Formulation of Reference Compounds: Colchicine was dissolved in sterile saline to prepare a 0.1 mg/mL solution. Anakinra was diluted in sterile saline to prepare 10 mg/mL solution.

Preparation of MSU Crystal Suspension: MSU crystals were suspended in sterile 0.9% saline for injection, USP (Baxter, lot 256131, exp. JUN19). The mixture was placed on a stir plate to maintain a constant 10 mg/mL homogenous suspension.

Dosing of Degrader: Mice were dosed orally at 10 mL/kg with suspensions above, giving 10 mg/kg, 30 mg/kg and 100 mg/kg final dose levels, three times at 8-hour intervals.

Dosing of Reference Compounds: Mice were dosed subcutaneously with colchicine at 1 mg/kg final and with Anakinra at 100 mg/kg final.

MSU Challenge: One hour after dosing with reference compounds or four hours after dosing the third time with degrader, mice were injected into the air pouch with 3 mL MSU (30 mg/mouse) and the injection sites were sealed with flexible collodion. The mice were returned to their cages, no adverse effects were observed.

Termination, Cell Collection and Data: Four hours after MSU/saline injection, the mice were anesthetized and humanely exsanguinated. The spleens were removed, halved, flash frozen in labeled Eppendorf tubes in liquid nitrogen, and stored at –80° C. for determination of IRAK4 using targeted MS/MS with labeled peptide internal standard. Immediately after the bleed, 3 ml 10 U/mL heparinized saline was injected into the air pouch. The air pouch was gently massaged, the contents immediately removed, and the exudate volume recorded. After allowing the MSU crystals to settle out for fifteen minutes in an ice bath, an aliquot of the exudate was transferred to labeled Eppendorf tubes for differential white blood cell counts, including neutrophils.

Figure 8:
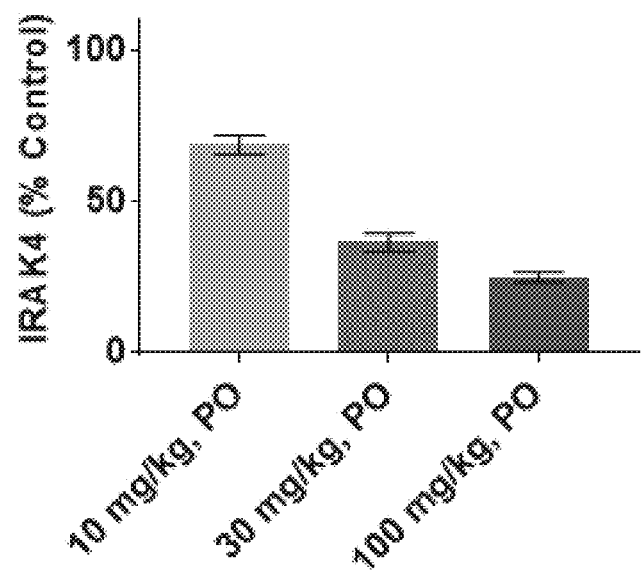
FIG. 8 is a graphical image showing in vivo degradation of IRAK4 in BALB/c mouse spleen following three PO doses of degrader I-30 depicted as IRAK4 (% control) (y-axis) and PO doses (10 mg/kg; 30 mg/kg; and 100 mg/kg) (x-axis).
Figure 9:
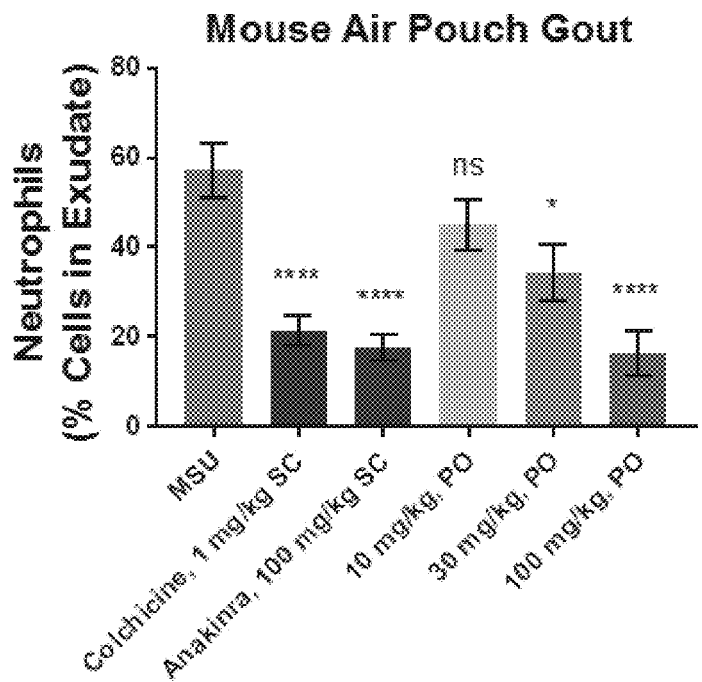
FIG. 9 is a graphical image depicting neotrophils in exudate collected from air pouch in mouse following MSU crystal challenge using showing neutrophiles count (% cells in extrudate) (y-axis) and (MSU; colchicine, 1 mg/kg SC; anakinra, 100 mg/kg SC; and PO I-30 doses: 10 mg/kg; 30 mg/kg; and 100 mg/kg) (x-axis).
Figure 15:
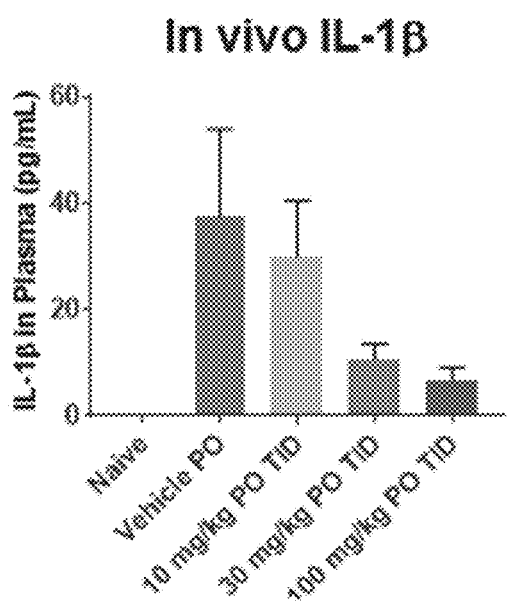
FIG. 15 is a graphical image of in vivo IL-1β testing following MSU crystal challenge showing IL-1β in plasma (pg/mL) (y-axis) and (Naive, Vehicle PO; and degrader I-30 PO TID: 10 mg/kg; 30 mg/kg; and 100 mg/kg) (x-axis).

FIG. 8 shows in vivo degradation of IRAK4 in BALB/c mouse spleen following three PO doses of I-30. FIG. 9 shows the results of neotrophils count in exudate collected from air pouch in mouse following MSU crystal challenge using PO TID dosing of I-30. FIG. 15 shows that orally dosed I-30 mediates a dose-dependent decrease in IL-1β in plasma.

FIGS. 32-34 show results of additional MSU crystal challenges using I-257 and I-417 in place of I-30 above. Compounds of the invention significantly reduce cellular infiltration and IL-1 production in the exudate in air pouch following MSU crystal injection. FIG. 35 shows the effect of pretreatment with I-417 exudate TNFα content in the MSU model. Compounds of the invention significantly reduce TNFα production in the exudate and systemic IL-6 in the plasma following MSU crystal injection into an air pouch.

Example 16. Human Whole Blood Cytokine Release Assays

Fresh human whole blood was collected in Na Heparin tubes and received from ALLCELLS same day as collection. 200 uL of whole blood was aliquoted per well into a 96 well plate. Whole blood was pre-incubated with compounds overnight at 37° C., 5% $CO_2$. Following compound incubation, samples were stimulated with I-75 0.25 g/mL (invivogen #tlrl-r848), LPS 10 ng/mL (Sigma #L2637) or IL-1β 25 ng/mL (R&D systems 201-LB) and incubated for an additional 5 hours. At the end of the assay, blood was spun down for 15 min at 4° C. and plasma was collected and immediately stored at –80° C. Cytokine and chemokine levels were measured by custom ordered U-plex MSD panels (panel 1: IFNy, IL-10, IL-1β, IL-6, IL-8, TNFα) and (panel 2: IP-10, MIP1-α, MIP-1β, IL-12/IL-23p40, GROα).

Figure 16:
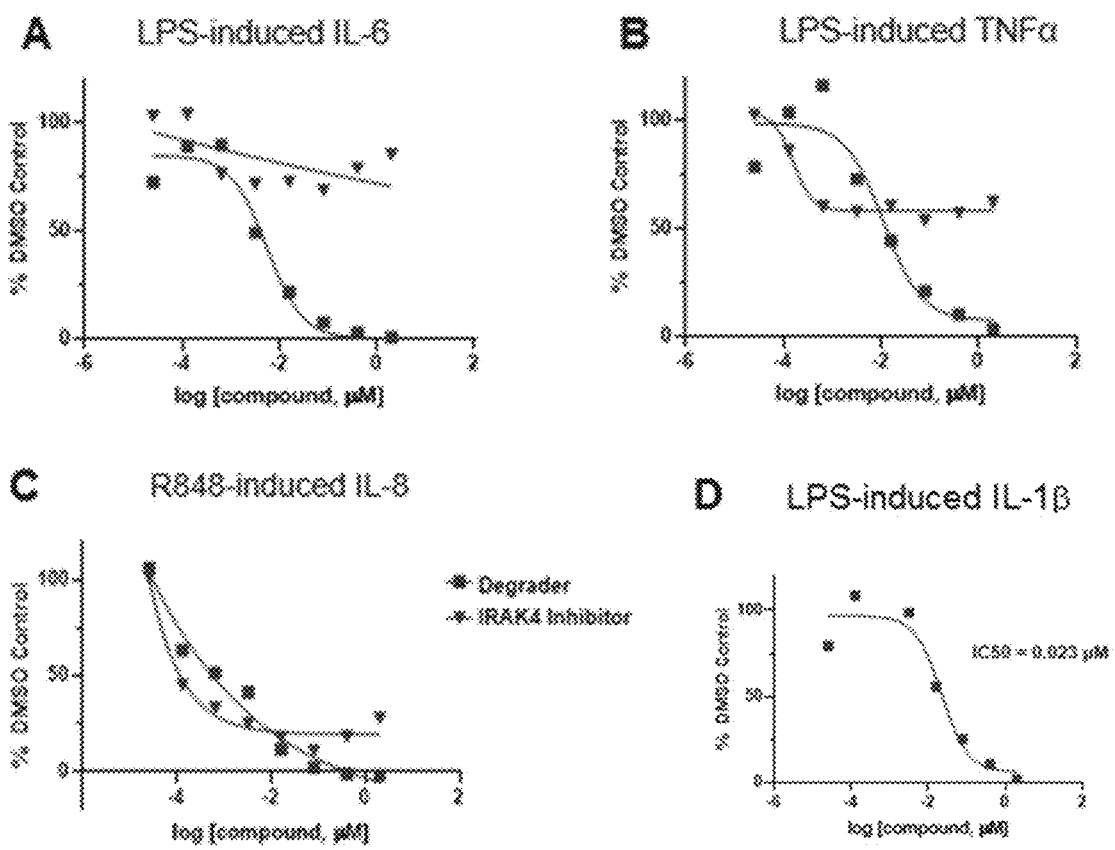
FIG. 16 includes graphical images of comparative TLR-stimulated pro-inflammatory cytokine inhibition results in vitro using a degrader I-75 and IRAK4 inhibitor PF-06550833 for LPS (TLR4)-induced IL-6 (A), LPS (TLR4)-induced TNFα (B), R848 (TLR7/8)-induced IL-8

FIG. 16 depicts the in vitro results of the cytokine release assays showing that IRAK4 degradation using I-75 inhibits a broader range of cytokines induced by different TLR stimuli than IRAK4 inhibition with PF-06550833.

Results of IL-6 secretion in hPBMC using R848 stimulation for compounds of the invention are reported in Table 13b. The letter codes for $IC_{50}$ include: A (<0.001 μM), B (0.001-0.01 μM), C (0.01-0.1 μM), DE (>0.1 μM).

TABLE 13b

IL-6 secretion in hPBMC results.

| I-# | IL-6 Secretion in hPBMC, R848 as stim, t = 20 h: $IC_{50}$ (μM) |
|---|---|
| I-185 | A |
| I-191 | B |
| I-257 | A |
| I-317 | B |
| I-396 | B |
| I-411 | A |
| I-413 | A |
| I-414 | A |
| I-415 | A |
| I-416 | A |
| I-417 | A |
| I-418 | B |
| I-419 | B |
| I-420 | A |
| I-421 | A |
| I-422 | A |
| I-423 | B |
| I-424 | B |
| I-425 | B |
| I-426 | B |
| I-428 | B |
| I-430 | B |
| I-431 | A |
| I-432 | B |
| I-433 | A |
| I-434 | A |
| I-446 | C |
| I-447 | B |
| I-448 | B |
| I-450 | B |
| I-464 | B |
| I-465 | A |
| I-466 | B |
| I-467 | A |
| I-468 | D |
| I-469 | A |
| I-470 | D |
| I-471 | A |
| I-472 | A |
| I-479 | C |
| I-480 | A |
| I-481 | C |
| I-482 | B |
| I-483 | B |
| I-484 | D |
| I-485 | B |
| I-486 | A |

TABLE 13b-continued

IL-6 secretion in hPBMC results.

| I-# | IL-6 Secretion in hPBMC, R848 as stim, t = 20 h: $IC_{50}$ ($\mu M$) |
|---|---|
| I-487 | A |
| I-488 | D |
| I-492 | A |
| I-493 | A |
| I-494 | D |
| I-495 | C |
| I-496 | A |
| I-497 | A |
| I-498 | C |
| I-499 | B |
| I-508 | B |
| I-509 | B |
| I-510 | B |
| I-511 | B |
| I-512 | D |
| I-513 | A |
| I-514 | A |
| I-515 | A |
| I-516 | B |
| I-517 | B |
| I-518 | B |
| I-519 | D |
| I-525 | A |
| I-526 | A |
| I-528 | B |
| I-530 | A |
| I-532 | B |
| I-537 | B |
| I-540 | B |
| I-543 | A |
| I-547 | B |
| I-549 | B |
| I-553 | B |
| I-554 | A |
| I-555 | B |

Example 17. In Vitro Combination Studies

The ABC-DLBCL cell line OCI-LY10 was MV4-11 cells were maintained in IMDM (Invitrogen, supplemented with 20% heat inactivated fetal bovine serum (Life Technologies, Grand Island, N.Y) plus+BME. Cultures were maintained in a humidified atmosphere including 5% $CO_2$. Studies were performed using OCI-LY10 cells in vitro to evaluate the anti-proliferative effect of a combination of two agents together on cell growth. The cell counts were measured by ATP quantitation using the Promega Cell Titer Glo kit and luminescence values corresponded to the amount of ATP in a given well. Compounds evaluated for synergy were tested in a range which was bracketed around the $IC_{50}$'s. The compounds were plated to a 384 well plate in a matrix format which includes increasing concentrations of each drug in the combination in a constant ratio, in addition to the effect of each compound alone in the study. Cells were seeded and grown in the log-linear phase for 4 days. DMSO concentration was less than 0.2% v/v.

The drug combination analysis was performed utilizing the Chou-Talalay method [Chou TC Pharmacological Reviews 2006]. Maximum and minimum inhibition (DMSO alone) controls were used in each plate to calculate fraction affected (Fa) of a test well. The combination index (CI) is the term used to describe the level of synergy or antagonism in a given test system. A combination index less than one indicates synergy, and a CI greater than one indicates antagonism. Synergy was determined using the software package Calcusyn by Biosoft. Graphs representing values of combination index (CI) versus Fractional effect (Fa) known as Fa-CI plots were generated and synergy was evaluated.

Figure 12:
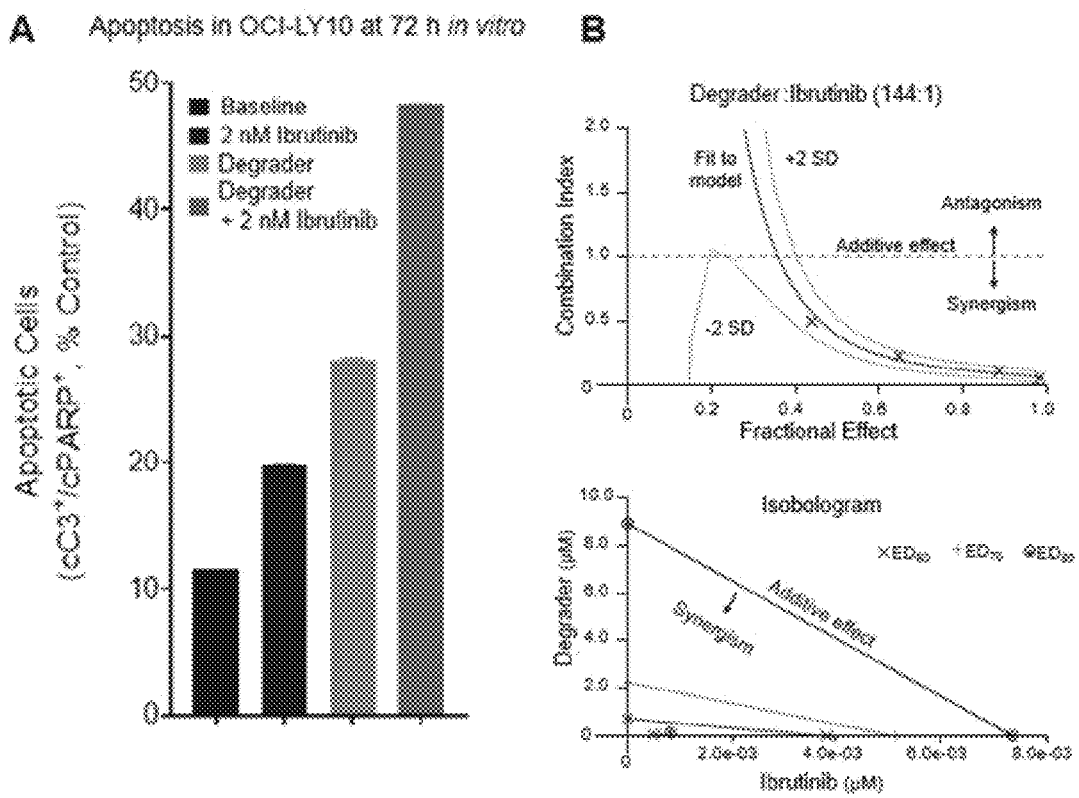
FIG. 12 is are graphical image showing apoptosis in OCI-LY10 at 72 h with Apoptotic Cells ($CC3^+/CPARP^+$, % Control) (y-axis) over several concentrations of 2 nM ibrutinib, degrader I-30, and the combination of 2 nM ibrutinib and degrader I-30 (μM) (x-axis) (A); and the graphical results of a Cell Titer Glo assay showing synergism (B).

FIG. 12 depicts the results of a cell viability assay showing that the combined activity of I-30 and a BTK inhibitor leads to a greater than additive increase in apoptosis within 72 h in n OCI-LY10 bearing both MYD88 L265P and CD79 mutations. Further, I-30 is synergistic with BTK inhibition in vitro vs cell viability, assessed with four day Cell Titer Glo read out.

Example 18. MSU Induced Gouty Arthritis in Rats

The anti-inflammatory efficacy and pain reduction for prophylactic treatment in an MSU-induced knee inflammation rat model of human gout was evaluated. See Kou, Y-Y et al., *Evid-Based Compl. Alt.* (doi: http://dx.doi.org/10.1155/2015/527019).

Preparation of MSU crystals: 4 g uric acid is dissolved in 800 ml 0.03N NaOH and heated to 60° C. NaOH is added as required to maintain pH 8.9. The solution is stored overnight at 4-8° C. Crystals are filtered, washed and dried. Crystals are suspended in sterile saline just prior to use.

Efficacy Study: Receive and quarantine 70 Wistar Strain rats (male, 250-300 g). Following quarantine, rats are accepted for the Study if no signs of clinical distress are noted during the 3-day quarantine period. The rats are maintained on certified laboratory diet and water ad libitum. The rats are ear-notched for individual identification. The rat weights are recorded. The rats are distributed to 7 groups of 10 rats per group such that each group has a similar mean weight. Baseline readings are taken on DAY −3. Baseline knee diameters are measured by digital caliper. Baseline responses to mechanical allodynia, as measured by von Frey fibers, are recorded.

Day −2 and day −1: The rats are weighed and dosed by oral gavage with I-75 in groups 2, 3, 4 and with vehicle in group 1.

DAY 0: The rats are weighed and dosed daily by oral gavage or intraperitoneal or subcutaneous as in Table 14. One hour after dosing, rats in Groups 1-7 are anesthetized and injected IA into the left knee with 2 mg MSU in 50 μl PBS.

TABLE 14

| Group | Treatment | Dose | ROA | Frequency* | MSU | No. Rats |
|---|---|---|---|---|---|---|
| 1 | Vehicle | 5 ml/kg | PO | QD | YES | 10 |
| 2 | I-75 | 10 mg/kg | PO | QD X 5 days | YES | 10 |
| 3 | I-75 | 30 mg/kg | PO | QD X 5 days | YES | 10 |
| 4 | I-75 | 100 mg/kg | PO | QD x 5 days | YES | 10 |
| 5 | PF06650883 | 30 mg/kg | PO | QD x 1 day | YES | 10 |
| 6 | Anakinra | 50 mg/kg | IP | QD x 3 days | YES | 10 |
| 7 | Colchicine | 0.5 mg/kg | SC | Day 0, Day 2 | YES | 10 |

*Dose regime: Group 1 (vehicle), Groups 2-4: Dose on day −2, −1, day 0, day 1 and day 2; Group 5 (PF06650883): Dose on day 0; Group 6 (Anakinra): Dose on day 0, day 1 and day 2; Group 7 (Colchicine): Dose on day 0 and day 2

DAY 1: Rats are weighed and dosed as in Table 14. One hour after dosing, mechanical allodynia and knee diameters are measured and recorded.

DAY 2: Rats are weighed and dosed as in Table 14 One hour after dosing, mechanical allodynia and knee diameters are measured and recorded.

Groups 1-4: 4 hours after final dosing, rats in groups 1-4 are sedated with ketamine and are exsanguinated into pre-chilled EDTA-treated tubes: The whole blood is processed to plasma which is stored in labeled 15 ml conical tubes at −80° C. The cell pellet is processed to PBMCs within two hours and stored at −80° C. Spleens are removed, divided into two portions and each half is snap frozen in tubes. Tubes are stored at −80° C. until quantification of IRAK4 by targeted MS/MS.

Groups 5-7 (Group 5: only one dose on day 0, there is no dose on day 2): 4 hours after final dosing, rats are sedated with ketamine and are exsanguinated into pre-chilled EDTA-treated tubes: The whole blood is processed to plasma which is stored in labeled 15 ml conical tubes at −80° C. The cell pellet is processed to PBMCs within two hours and stored at −80° C. Spleens are removed, divided into two portions and each half is snap frozen in tubes. Tubes are stored at −80° C. until quantification of IRAK4 by targeted MS/MS.

Results are tabulated, graphed and statistically analyzed for anti-inflammatory efficacy and pain reduction. FIG. 17. shows that the prophylactic treatment of I-75 results in a dramatic anti-inflammatory and analgesic effect of decreasing knee joint swelling (A) and pain sensitivity (B) in a MSU-induced knee inflammation rat model of human gout.

Example 19 (Method 3). Synthesis of N-[3-(difluoromethyl)-1-[4-[[4-[3-[1-(2,6-dioxo-3-piperidyl)-3-methyl-2-oxo-benzimidazol-4-yl]propoxy]-1-piperidyl] methyl] cyclohexyl] pyrazol-4-yl]-5-[(2R, 6S)-2,6-dimethylmorpholin-4-yl] pyrazolo[1,5-a]pyrimidine-3-carboxamide (I-275)

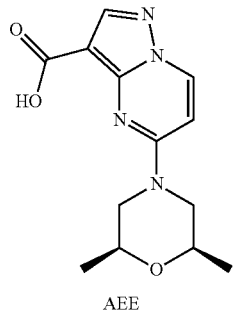

AEE

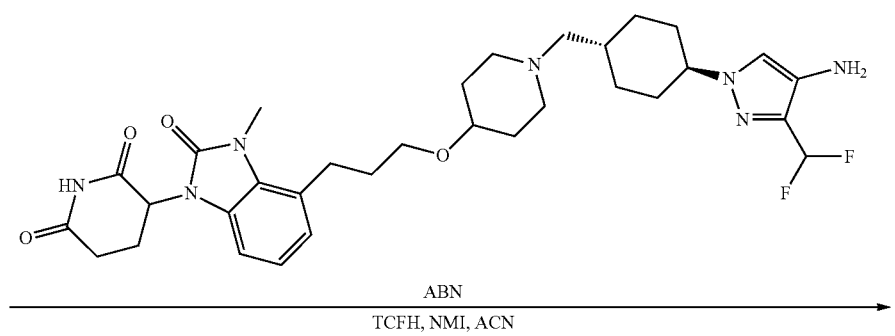

ABN
TCFH, NMI, ACN

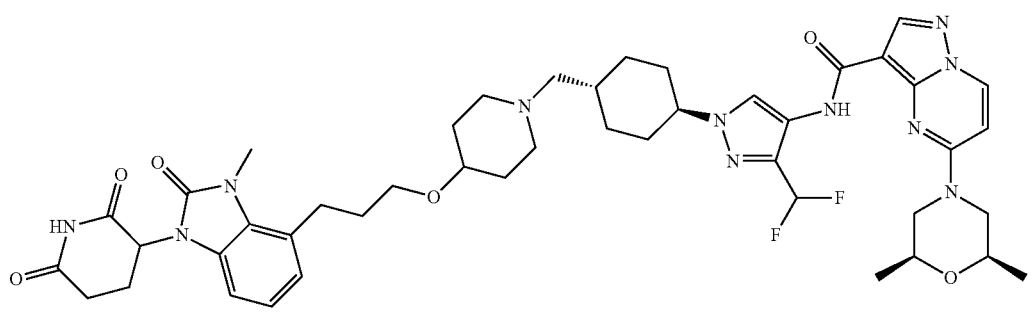

To a solution of 5-[(2R,6S)-2,6-dimethylmorpholin-4-yl] pyrazolo[1,5-a]pyrimidine-3-carboxylic acid (16.6 mg, 60.2 umol, Intermediate AEE) in ACN (1 mL) was added [chloro (dimethylamino)methylene]-dimethyl-ammonium; hexafluorophosphate (20.2 mg, 72.2 umol), 1-methylimidazole (17.3 mg, 210 umol) and the mixture was stirred at 15° C. for 1 hr. Next, 3-[4-[3-[[1-[[4-[4-amino-3-(difluoromethyl) pyrazol-1-yl] cyclohexyl]methyl]-4-piperidyl]oxy] propyl]-3-methyl-2-oxobenzimidazol-1-yl]piperidine-2,6-dione (40.0 mg, 60.2 umol, HCl, Intermediate ABN) was added into the above mixture. The mixture was stirred at 15° C. for 1 hr. On completion, the mixture was quenched with H$_2$O (0.5 mL) and concentrated in vacuo. The residue was purified by prep-HPLC (column: Phenomenex Synergi C18 150*25*10 um; mobile phase: [water (0.225% FA)-ACN]; B %: 18%-48%, 10 min) to give the title compound (23.0 mg, 40% yield) as white solid. $^1$H NMR (400 MHz, DMSO-d$_6$) δ 11.09 (s, 1H), 9.28 (s, 1H), 8.82 (d, J=8.0 Hz, 1H), 8.39 (s, 1H), 8.29 (s, 1H), 7.31-7.02 (m, 1H), 7.00-6.92 (m, 3H), 6.92-6.85 (m, 1H), 5.41-5.31 (m, 1H), 4.60-4.32 (m, 2H), 4.23-4.12 (m, 1H), 3.68-3.63 (m, 2H), 3.58 (s, 3H), 3.48-3.46 (m, 2H), 3.01-2.94 (m, 2H), 2.93-2.83 (m, 1H), 2.78-2.70 (m, 1H), 2.67-2.63 (m, 2H), 2.63-2.55 (m, 1H), 2.14-1.94 (m, 9H), 1.92-1.70 (m, 9H), 1.62-1.53 (m, 1H), 1.51-1.41 (m, 2H), 1.21 (s, 3H), 1.19 (s, 3H), 1.09-0.99 (m, 2H); LC-MS (ESI$^+$) m/z 886.6 (M+H)$^+$.

TABLE 15

Compounds synthesized via Method 3 with the coupling of various amines and acids.

| I-#[a] | Intermediate Amine | Intermediate Acid | LCMS (ES+) m/z (M + H)$^+$ | $^1$HNMR (400 MHz, DMSO-d$_6$) δ |
|---|---|---|---|---|
| I-276 | ABN | AEF | 886.6 | 11.08 (s, 1H), 9.31 (s, 1H), 8.80 (d, J = 8.0 Hz, 1H), 8.40 (s, 1H), 8.27 (s, 1H), 7.29-6.85 (m, 5H), 5.36 (dd, J = 5.2, 12.8 Hz, 1H), 4.28-4.15 (m, 1H), 4.11-4.02 (m, 2H), 3.98-3.82 (m, 2H), 3.58 (s, 3H), 3.52 (d, J = 6.8 Hz, 2H), 3.48 (t, J = 6.4 Hz, 4H), 3.06-2.81 (m, 6H), 2.78-2.67 (m, 2H), 2.67-2.60 (m, 2H), 2.12-2.04 (m, 2H), 2.01-1.96 (m, 1H), 1.96-1.86 (m, 4H), 1.86-1.72 (m, 5H), 1.70-1.56 (m, 2H), 1.17 (d, J = 6.4 Hz, 6H), 1.14-1.02 (m, 2H). |
| I-277 | ABN | AEG | 870.6 | 11.09 (s, 1H), 9.51 (d, J = 6.0 Hz, 1H), 8.78 (d, J = 8.0 Hz, 1H), 8.39 (d, J = 4.0 Hz, 1H), 8.26 (d, J = 5.6 Hz, 1H), 7.28-6.96 (m, 3H), 6.92-6.88 (m, 1H), 6.87-6.44 (m, 1H), 5.42-5.33 (m, 1H), 5.30-5.05 (m, 1H), 4.83-4.72 (m, 1H), 4.28-4.13 (m, 1H), 3.85-3.79 (m, 2H), 3.76-3.61 (m, 2H), 3.58 (s, 3H), 3.50-3.47 (m, 2H), 3.00-2.96 (m, 2H), 2.94-2.84 (m, 3H), 2.77-2.69 (m, 1H), 2.66-2.60 (m, 1H), 2.45-2.38 (m, 2H), 2.07-1.95 (m, 5H), 1.95-1.86 (m, 5H), 1.86-1.80 (m, 3H), 1.79-1.73 (m, 2H), 1.71-1.51 (m, 4H), 1.15-1.04 (m, 2H) |
| I-278 | ABN | AEH | 870.5 | 11.08 (s, 1H), 9.51 (d, J = 6.8 Hz, 1H), 8.78 (d, J = 7.6 Hz, 1H), 8.40 (d, J = 4.4 Hz, 1H), 8.25 (d, J = 5.4 Hz, 1H), 7.26-6.43 (m, 5H), 5.36 (dd, J = 5.2, 12.0 Hz, 1H), 5.31-5.02 (m, 1H), 4.83-4.70 (m, 1H), 4.32-4.16 (m, 1H), 3.87-3.57 (m, 7H), 3.57-3.46 (m, 4H), 3.45 (d, J = 9.6 Hz, 2H), 3.08-2.82 (m, 7H), 2.79-2.68 (m, 1H), 2.66-2.59 (m, 1H), 2.17-2.08 (m, 2H), 2.04-1.77 (m, 12H), 1.71-1.57 (m, 1H), 1.28-1.11 (m, 2H) |
| I-279 | AFF | AAQ | 871.1 | 11.09 (s, 1H), 9.35 (s, 1H), 8.52 (d, J = 7.6 Hz, 1H), 8.31 (s, 1H), 8.20 (s, 1H), 8.16 (s, 1H), 7.79 (d, J = 8.8 Hz, 1H), 7.29-6.92 (m, 3H), 6.86 (d, J = 7.2 Hz, 1H), 6.61 (d, J = 7.6 Hz, 1H), 5.37 (d, J = 7.6 Hz, 1H), 4.26 (d, J = 8.8 Hz, 1H), 4.20-4.09 (m, 1H), 3.82 (s, 2H), 3.67 (s, 4H), 3.61 (s, 3H), 2.93-2.82 (m, 3H), 2.77-2.58 (m, 2H), 2.21 (d, J = 6.4 Hz, 2H), 2.17 (s, 3H), 2.04-1.91 (m, 5H), 1.87 (d, J = 12.8 Hz, 2H), 1.74-1.54 (m, 10H), 1.42-1.31 (m, 4H), 1.08-0.93 (m, 2H) |
| I-280 | AFG | AAQ | 886.6 | 11.08 (s, 1H), 9.65 (s, 1H), 9.37 (s, 1H), 8.53 (d, J = 7.6 Hz, 1H), 8.35 (s, 1H), 8.17 (s, 1H), 7.84 (d, J = 8.4 Hz, 1H), 7.31-6.99 (m, 3H), 6.93-6.84 (m, 1H), 6.63 (d, J = 7.6 Hz, 1H), 5.34 (dd, J = 4.0, 12.0 Hz, 1H), 4.30-4.18 (m, 2H), 3.64 (s, 1H), 3.55-3.37 (m, 4H), 3.33 (s, 3H), 3.09-2.87 (m, 5H), 2.76-2.62 (m, 4H), 2.16-1.91 (m, 9H), 1.89-1.65 (m, 9H), 1.63-1.52 (m, 4H), 1.42-1.30 (m, 2H), 1.24-1.13 (m, 2H) |
| I-282[b] | ABN | ADA | 858.3 | 11.08 (s, 1H), 9.57 (d, J = 10.4 Hz, 1H), 8.74 (t, J = 7.2 Hz, 1H), 8.38 (d, J = 2.8 Hz, 1H), 8.24 (s, 1H), 7.25-6.97 (m, 1H), 6.96 (s, 1H), 6.89-6.85 (m, 1H), 6.57 (dd, J = 8.0, 12.0 Hz, 1H), 5.36 (dd, J = 5.2, 12.4 Hz, 1H), 5.19-5.01 (m, 1H), 4.50-4.40 (m, 1H), 4.25-4.12 (m, 1H), 3.85-3.73 (m, 1H), 3.64 (s, 2H), 3.57 (s, 3H), 3.49-3.44 (m, 4H), 3.00-2.94 (m, 2H), 2.91-2.70 (m, 4H), 2.66-2.57 (m, 2H), 2.53-2.51 (m, 2H), 2.11-1.95 (m, 5H), 1.94-1.70 (m, 9H), 1.68-1.49 (m, 3H), 1.16-1.01 (m, 2H) |
| I-283 | ABN | AFI | 858.3 | 11.08 (s, 1H), 9.57 (d, J = 10.8 Hz, 1H), 8.74 (t, J = 7.2 Hz, 1H), 8.38 (d, J = 2.8 Hz, 1H), 8.24 (s, 1H), 7.25-7.00 |

TABLE 15-continued

Compounds synthesized via Method 3 with the coupling of various amines and acids.

| I-#[a] | Intermediate Amine | Intermediate Acid | LCMS (ES+) m/z (M + H)+ | $^1$HNMR (400 MHz, DMSO-d$_6$) δ |
|---|---|---|---|---|
| | | | | (t, J = 5.2 Hz 1H), 6.96 (d, J = 4.8 Hz, 2H), 6.90-6.85 (m, 1H), 6.57 (dd, J = 8.0, 12.0 Hz, 1H), 5.40-5.32 (m, 1H), 5.18-5.06 (m, 1H), 4.50-4.39 (m, 1H), 4.23-4.13 (m, 1H), 3.83-3.75 (m, 1H), 3.64 (d, J = 2.8 Hz, 2H), 3.57 (s, 3H), 3.49-3.44 (m, 4H), 3.00-2.94 (m, 2H), 2.91-2.84 (m, 1H), 2.79-2.70 (m, 2H), 2.64 (br s, 1H), 2.28-2.16 (m, 3H), 2.09-1.97 (m, 4H), 1.93-1.69 (m, 9H), 1.64-1.46 (m, 3H), 1.12-1.00 (m, 2H) |
| I-284[c] | ABN | ADB | 844.3 | 11.08 (s, 1H), 9.70 (s, 1H), 8.74 (d, J = 7.6 Hz, 1H), 8.38 (s, 1H), 8.24 (s, 1H), 7.25-6.98 (m, 1H), 6.96 (d, J = 4.4 Hz, 2H), 6.89-6.86 (m, 1H), 6.38 (d, J = 7.6 Hz, 1H), 5.89-5.87 (m, 1H), 5.37-5.34 (m, 1H), 4.71-4.59 (m, 1H), 4.47-4.35 (m, 2H), 4.24-4.12 (m, 1H), 4.01-3.89 (m, 2H), 3.57 (s, 3H), 3.46 (t, J = 6.0 Hz, 2H), 2.97 (t, J = 7.6 Hz, 2H), 2.89-2.85 (m, 1H), 2.79-2.69 (m, 2H), 2.66-2.58 (m, 1H), 2.27-2.14 (m, 4H), 2.09-1.96 (m, 4H), 1.92-1.72 (m, 9H), 1.63-1.46 (m, 3H), 1.12-0.98 (m, 2H) |
| I-285 | ABN | ABZ | 886.7 | 11.09 (s, 1H), 9.31 (s, 1H), 8.81 (d, J = 8.0 Hz, 1H), 8.41 (s, 1H), 8.28 (s, 1H), 7.29-6.97 (m, 3H), 6.94-6.86 (m, 2H), 5.43-5.34 (m, 1H), 4.29-4.17 (m, 1H), 4.11-4.04 (m, 2H), 3.98-3.85 (m, 2H), 3.60 (s, 3H), 3.55-3.50 (m, 3H), 3.50-3.48 (m, 2H), 3.37-3.30 (m, 1H), 3.07-2.83 (m, 8H), 2.77-2.68 (m, 1H), 2.66-2.59 (m, 1H), 2.16-2.04 (m, 4H), 2.03-1.95 (m, 4H), 1.93-1.86 (m, 2H), 1.86-1.77 (m, 4H), 1.21-1.15 (m, 8H) |
| I-286[b] | ABN | AGQ | 886.4 | 11.09 (s, 1H), 9.40 (s, 1H), 8.73 (d, J = 8.0 Hz, 1H), 8.41 (s, 1H), 8.24 (s, 1H), 7.25-6.94 (m, 3H), 6.91 (d, J = 8.0 Hz, 1H), 6.89-6.85 (m, 1H), 5.36 (dd, J = 5.2, 12.4 Hz, 1H), 4.27-4.19 (m, 1H), 3.71-3.64 (m, 2H), 3.60 (s, 1H), 3.57 (s, 3H), 3.06-2.92 (m, 7H), 2.91-2.85 (m, 1H), 2.76-2.69 (m, 2H), 2.65-2.57 (m, 2H), 2.54 (s, 1H), 2.18-2.07 (m, 4H), 2.01-1.75 (m, 12H), 1.68-1.49 (m, 5H), 1.25-1.13 (m, 5H) |
| I-287[c] | ABN | AGR | 870.3 | 11.10 (s, 1H), 9.71 (s, 1H), 8.76 (d, J = 7.6 Hz, 1H), 8.39 (s, 1H), 8.25 (s, 1H), 7.31-7.01 (m, 1H), 6.98 (d, J = 3.2 Hz, 2H), 6.92-6.84 (m, 1H), 6.38 (d, J = 7.6 Hz, 1H), 5.43-5.30 (m, 1H), 4.74 (s, 4H), 4.39 (s, 4H), 4.29-4.18 (m, 1H), 3.59 (d, J = 8.8 Hz, 3H), 3.53-3.47 (m, 3H), 3.35-3.35 (m, 3H), 3.04-2.92 (m, 6H), 2.71-2.63 (m, 1H), 2.19-2.05 (m, 3H), 2.02-1.78 (m, 11H), 1.69-1.56 (m, 1H), 1.25-1.11 (m, 2H) |
| I-288[d] | ABN | AHZ | 874.3 | 10.98 (s, 1H), 9.40 (s, 1H), 8.84 (d, J = 7.6 Hz, 1H), 8.38 (s, 1H), 8.30 (s, 1H), 7.53 (t, J = 8.2 Hz, 1H), 7.24-6.96 (m, 1H), 6.92 (m, 3H), 5.17-5.10 (m, 1H), 4.22-4.12 (m, 1H), 3.80 (m, 4H), 3.73 (m, 4H), 3.27-3.25 (m, 1H), 3.19 (m, 3H), 3.10-3.01 (m, 2H), 2.89-2.80 (m, 1H), 2.76 (s, 3H), 2.66-2.59 (m, 1H), 2.56 (s, 3H), 2.18-2.09 (m, 1H), 2.07-1.99 (m, 4H), 1.98-1.82 (m, 5H), 1.79-1.61 (m, 7H), 1.54-1.44 (m, 1H), 1.37-1.25 (m, 2H), 1.07-0.94 (m, 2H) |
| I-289 | ABN | AGJ | 886.6 | 11.09 (s, 1H), 9.37 (s, 1H), 8.53 (d, J = 7.6 Hz, 1H), 8.35 (s, 1H), 8.17 (s, 1H), 7.86 (d, J = 8.8 Hz, 1H), 7.30-7.00 (m, 1H), 7.00-6.93 (m, 2H), 6.92-6.82 (m, 1H), 6.63 (d, J = 8.0 Hz, 1H), 5.45-5.33 (m, 1H), 4.24-4.20 (m, 2H), 3.86-3.80 (m, 1H), 3.58 (d, J = 9.6 Hz, 3H), 3.53-3.45 (m, 3H), 3.38-3.29 (m, 1H), 3.06-2.89 (m, 7H), 2.77-2.58 (m, 2H), 2.14-2.03 (m, 4H), 2.02-1.87 (m, 6H), 1.85-1.65 (m, 7H), 1.63-1.42 (m, 5H), 1.41-1.29 (m, 2H), 1.24-1.11 (m, 2H) |
| I-290 | ABN | ABT | 886.6 | 11.11 (s, 1H), 9.38 (s, 1H), 8.54 (d, J = 7.6 Hz, 1H), 8.36 (s, 1H), 8.17 (s, 1H), 7.83 (d, J = 8.8 Hz, 1H), 7.15 (t, J = 54 Hz, 1H), 7.00-6.95 (m, 2H), 6.92-6.85 (m, 1H), 6.62 (d, J = 7.6 Hz, 1H), 5.43-5.32 (m, 1H), 4.93-4.64 (m, 1H), 4.34-4.18 (m, 2H), 3.82 (s, 1H), 3.52-3.46 (m, 5H), 3.40-3.33 (m, 2H), 3.09-2.92 (m, 7H), 2.91-2.84 (m, 1H), 2.73-2.67 (m, 1H), 2.65-2.60 (m, 1H), 2.18-2.12 (m, 1H), 2.08 (d, J = 11.6 Hz, 2H), 2.03-1.76 (m, 11H), 1.76-1.64 (m, 3H), 1.61-1.54 (m, 3H), 1.41-1.30 (m, 2H), 1.24-1.13 (m, 2H) |
| I-291[e] | ABN | AHP | 946.4 | 11.08 (s, 1H), 9.20-9.11 (m, 1H), 9.09 (d, J = 7.6 Hz, 1H), 9.04 (s, 1H), 8.50 (s, 1H), 8.46 (s, 1H), 8.40 (s, 1H), 8.18 (d, J = 8.0 Hz, 1H), 7.31-6.83 (m, 4H), 5.37 (dd, J = |

TABLE 15-continued

Compounds synthesized via Method 3 with the coupling of various amines and acids.

| I-#[a] | Intermediate Amine | Intermediate Acid | LCMS (ES+) m/z (M + H)+ | 1HNMR (400 MHz, DMSO-d6) δ |
|---|---|---|---|---|
| | | | | 5.6, 12.4 Hz, 1H), 5.04 (d, J = 7.2 Hz, 1H), 4.30-4.12 (m, 2H), 3.59 (d, J = 8.0 Hz, 3H), 3.54-3.46 (m 3H), 3.39-3.33 (m, 1H), 3.05-2.85 (m, 7H), 2.76-2.67 (m, 1H), 2.65-2.59 (m, 1H), 2.37-2.32 (m, 1H), 2.18-2.05 (m, 4H), 2.04-1.91 (m, 7H), 1.89-1.76 (m, 5H), 1.75-1.64 (m, 2H), 1.61-1.52 (m, 1H), 1.51-1.40 (m, 1H), 1.27-1.12 (m, 2H) |
| I-292 | AGA | AGJ | 940.3 | 11.08 (s, 1H), 9.37 (s, 1H), 8.53 (d, J = 7.6 Hz, 1H), 8.34 (s, 1H), 8.17 (s, 1H), 7.80 (d, J = 8.8 Hz, 1H), 7.68 (dd, J = 7.2, 8.4 Hz, 1H), 7.33 (dd, J = 4.4, 7.6 Hz, 2H), 7.29-6.98 (m, 1H), 6.62 (d, J = 7.8 Hz, 1H), 5.09 (dd, J = 5.2, 12.8 Hz, 1H), 4.77 (s, 1H), 4.31-4.13 (m, 2H), 3.83 (s, 1H), 3.70 (d, J = 11.2 Hz, 2H), 3.32 (d, J = 6.0 Hz, 4H), 2.94-2.81 (m, 5H), 2.65-2.52 (m, 2H), 2.42 (s, 3H), 2.09-1.97 (m, 3H), 1.89 (d, J = 11.2 Hz, 4H), 1.83-1.65 (m, 8H), 1.62-1.48 (m, 6H), 1.45-1.29 (m, 4H), 1.15-1.02 (m, 2H) |
| I-293[f] | ABR | AHQ | 886.6 | 11.08 (s, 1H), 9.40 (s, 1H), 8.51 (d, J = 7.6 Hz, 1H), 8.32 (s, 1H), 7.90 (d, J = 8.0 Hz, 1H), 7.33-7.00 (m, 1H), 6.96 (d, J = 4.8 Hz, 2H), 6.90-6.84 (m, 1H), 6.39 (d, J = 7.6 Hz, 1H), 5.36 (dd, J = 5.6, 12.4 Hz, 1H), 4.68 (s, 1H), 4.24-4.11 (m, 1H), 4.08-3.95 (m, 1H), 3.57 (s, 3H), 3.50-3.43 (m, 3H), 3.35-3.32 (m, 2H), 3.03-2.93 (m, 2H), 2.92-2.81 (m, 1H), 2.77-2.68 (m, 2H), 2.68-2.57 (m, 2H), 2.22-2.11 (m, 3H), 2.11-2.00 (m, 3H), 2.00-1.95 (m, 1H), 1.94-1.87 (m, 3H), 1.86-1.77 (m, 4H), 1.77-1.63 (m, 3H), 1.63-1.53 (m, 2H), 1.53-1.42 (m, 2H), 1.41-1.29 (m, 2H), 1.29-1.12 (m, 2H), 1.12-0.97 (m, 2H) |
| I-294[g] | AGS | AGJ | 900.4 | 11.10 (s, 1H), 9.37 (s, 1H), 8.96-8.71 (m, 1H), 8.53 (d, J = 7.6 Hz, 1H), 8.35 (s, 1H), 8.17 (s, 1H), 7.80 (d, J = 8.8 Hz, 1H), 7.65-7.56 (m, 1H), 7.30-6.95 (m, 3H), 6.62 (d, J = 7.6 Hz, 1H), 5.10-4.99 (m, 1H), 4.86-4.65 (m, 1H), 4.34-4.14 (m, 2H), 3.83 (s, 1H), 3.57-3.50 (m, 3H), 3.45-3.41 (m, 5H), 3.09-2.83 (m, 5H), 2.65-2.51 (m, 2H), 2.19-1.95 (m, 5H), 1.94-1.65 (m, 11H), 1.63-1.47 (m, 4H), 1.43-1.28 (m, 2H), 1.25-1.10 (m, 2H) |
| I-296 | AIG | AGJ | 901.6 | 11.12 (s, 1H), 9.37 (s, 1H), 8.89-8.78 (m, 1H), 8.54 (d, J = 8.0 Hz, 1H), 8.35 (d, J = 3.2 Hz, 1H), 8.17 (d, J = 3.6 Hz, 1H), 7.88-7.78 (m, 2H), 7.58-7.51 (m, 1H), 7.49-7.46 (m, 1H), 7.30-6.99 (m, 1H), 6.62 (d, J = 8.0 Hz, 1H), 5.14-5.05 (m, 1H), 4.85-4.71 (m, 1H), 4.36-4.34 (m, 1H), 4.27-4.26 (m, 2H), 3.82 (m, 1H), 3.71-3.61 (m, 2H), 3.53-3.48 (m, 1H), 3.06-2.83 (m, 5H), 2.65-2.56 (m, 1H), 2.17-1.96 (m, 7H), 1.96-1.65 (m, 11H), 1.64-1.47 (m, 6H), 1.43-1.28 (m, 2H), 1.25-1.11 (m, 2H) |
| I-297 | AIG | ABB | 873.6 | 11.12 (s, 1H), 9.43-9.38 (m, 1H), 8.83 (d, J = 8.0 Hz, 2H), 8.40 (d, J = 2.4 Hz, 1H), 8.31-8.26 (m, 1H), 7.85-7.83 (m, 1H), 7.60-7.52 (m, 1H), 7.49-7.47 (m, 1H), 7.24-6.95 (m, 1H), 6.91 (d, J = 8.0 Hz, 1H), 5.15-5.05 (m, 1H), 4.37-4.30 (m, 1H), 4.30-4.16 (m, 2H), 3.79 (m, 4H), 3.73 (m, 4H), 3.69-3.59 (m, 2H), 3.54-3.47 (m, 1H), 3.03-2.84 (m, 4H), 2.64-2.56 (m, 1H), 2.52 (m, 2H), 2.16-1.96 (m, 7H), 1.95-1.70 (m, 8H), 1.58 (m, 1H), 1.24-1.09 (m, 2H) |
| I-298 | AGG | AGJ | 856.6 | 11.09 (s, 1H), 9.41 (s, 1H), 8.58-8.50 (m, 1H), 8.41 (s, 1H), 8.18 (s, 1H), 7.87 (d, J = 8.4 Hz, 1H), 7.72-7.05 (m, 4H), 6.64 (d, J = 7.8 Hz, 1H), 5.10 (dd, J = 5.2, 12.8 Hz, 1H), 4.68-4.52 (m, 1H), 4.32-4.23 (m, 1H), 4.12-4.01 (m, 3H), 3.74-3.63 (m, 4H), 3.24-3.02 (m, 4H), 2.95-2.80 (m, 3H), 2.64-2.55 (m, 2H), 2.33-2.20 (m, 3H), 2.08-2.00 (m, 1H), 1.85-1.67 (m, 6H), 1.62-1.28 (m, 11H) |
| I-299 | AHE | AEH | 870.5 | 11.11 (d, J = 6.4 Hz, 1H), 9.56-9.42 (m, 1H), 8.78 (d, J = 7.6 Hz, 1H), 8.44-8.38 (m, 1H), 8.26 (d, J = 4.4 Hz, 1H), 7.67-7.56 (m, 1H), 7.29-6.96 (m, 3H), 6.91-6.42 (m, 2H), 5.34-5.00 (m, 2H), 4.82-4.71 (m, 1H), 4.29-4.16 (m, 1H), 3.88-3.56 (m, 7H), 3.52 (s, 3H), 3.02-2.81 (m, 5H), 2.70-2.54 (m, 2H), 2.19-1.72 (m, 14H), 1.71-1.58 (m, 1H), 1.27-1.08 (m, 2H) |
| I-300[h] | ABN | AET | 921.3 | 11.10 (s, 1H), 9.74 (br s, 1H), 9.33 (s, 1H), 8.77-8.60 (m, 4H), 8.33-8.21 (m, 2H), 7.84 (d, J = 7.6 Hz, 1H), 7.34-6.83 (m, 4H), 6.72 (d, J = 7.6 Hz, 1H), 5.37 (dd, J = 5.2, |

TABLE 15-continued

Compounds synthesized via Method 3 with the coupling of various amines and acids.

| I-#[a] | Intermediate Amine | Intermediate Acid | LCMS (ES+) m/z (M + H)+ | 1HNMR (400 MHz, DMSO-d$_6$) δ |
|---|---|---|---|---|
| | | | | 12.0 Hz, 1H), 5.11-4.97 (m, 1H), 4.31-4.14 (m, 1H), 4.05-3.89 (m, 1H), 3.58 (d, J = 9.2 Hz, 3H), 3.54-3.46 (m, 4H), 3.32-3.30 (m, 1H), 3.05-2.99 (m, 2H), 2.98-2.95 (m, 2H), 2.95-2.91(m, 2H), 2.91-2.84 (m, 1H), 2.78-2.68 (m, 1H), 2.65-2.59 (m, 1H), 2.52-2.51 (m, 2H), 2.30-2.18 (m, 1H), 2.14-2.07 (m, 2H), 2.07-2.03 (m, 2H), 2.02-1.98 (m, 2H), 1.97-1.93(m, 2H), 1.92-1.86 (m, 2H), 1.86-1.83 (m, 2H), 1.83-1.78 (m, 3H), 1.77-1.75 (m, 1H), 1.73-1.65 (m, 1H), 1.29-1.07 (m, 2H) |
| I-369 | AKE | AEH | 787.4 | 11.09 (s, 1H), 9.50 (d, J = 6.0 Hz, 1H), 8.78 (d,J = 7.6 Hz, 1H), 8.38 (d, J = 4.4 Hz, 1H), 8.26 (d, J = 5.6 Hz, 1H), 7.60 (dd, J = 7.2, 8.4 Hz, 1H), 7.25-6.94 (m, 3H), 6.90-6.38 (m, 2H), 5.31-5.00 (m, 2H), 4.81-4.71 (m, 1H), 4.24-4.09 (m, 1H), 3.86-3.71 (m, 2H), 3.66-3.56 (m, 3H), 3.52-3.39 (m, 3H), 3.30 (d, J = 6.4 Hz, 2H), 2.94-2.81 (m, 1H), 2.63-2.54 (m, 2H), 2.08-1.91 (m, 5H), 1.90-1.80 (m, 2H), 1.79-1.66 (m, 2H), 1.64-1.55 (m, 1H), 1.21-1.06 (m, 2H) |
| I-375 | AJK | AEH | 801.4 | 11.09 (s, 1H), 9.50 (d, J = 6.4 Hz, 1H), 8.78 (d, J = 8.0 Hz, 1H), 8.39 (d, J = 4.0 Hz, 1H), 8.26 (d, J = 5.6 Hz, 1H), 7.59 (dd, J = 7.6, 8.4 Hz, 1H), 7.26-6.41 (m, 5H), 5.31-5.00(m, 2H), 4.77 (d, J = 16.4 Hz, 1H), 4.24-4.12 (m, 1H), 3.85-3.72 (m, 2H), 3.65-3.58 (m, 1H), 3.52-3.45 (m, 2H), 3.44-3.37 (m, 2H), 3.24 (d, J = 6.4 Hz, 2H), 2.94-2.81 (m, 1H), 2.63-2.53 (m, 2H), 2.08-1.99 (m, 4H), 1.98-1.88 (m, 2H), 1.88-1.77 (m, 4H), 1.76-1.59 (m, 3H), 1.25-1.06 (m, 2H) |
| I-398 | AQW | AQV | 915.6 | 11.11 (s, 1H), 9.76 (s, 1H), 9.04 (s, 1H), 8.88-8.72 (m, 1H), 8.19 (s, 1H), 8.08 (d, J = 6.0 Hz, 1H), 7.76-7.44 (m, 2H), 7.32-7.00 (m, 4H), 6.73-6.60 (m, 1H), 5.05 (dd, J = 5.2, 12.8 Hz, 1H), 4.30-4.18 (m, 1H), 3.92-3.81 (m, 2H), 3.52-3.46 (m, 4H), 3.25-3.18 (m, 2H), 3.12-3.02 (m, 2H), 2.98-2.84 (m, 2H), 2.80 (d, J = 4.4 Hz, 3H), 2.64-2.53 (m, 2H), 2.14-1.89 (m, 7H), 1.88-1.47 (m, 13H), 1.41-1.31 (m, 2H), 1.24-1.13 (m, 2H) |
| I-399 | AQW | ATK | 915.6 | 11.09 (s, 1H), 9.67 (s, 1H), 8.93 (s, 1H), 8.27-8.13 (m, 2H), 7.63-7.54 (m, 1H), 7.31-7.02 (m, 4H), 7.00 (dd, J = 1.3, 5.3 Hz, 1H), 6.72-6.61 (m, 2H), 5.05 (dd, J = 5.3, 12.8 Hz, 1H), 4.22-4.13 (m, 1H), 3.92-3.84 (m, 2H), 3.49-3.46 (m, 3H), 2.92-2.80 (m, 2H), 2.61 (d, J = 2.9 Hz, 1H), 2.58-2.54 (m, 2H), 2.34-2.29 (m, 2H), 2.12 (s, 3H), 2.09 (d, J = 7.3 Hz, 2H), 2.06-1.99 (m, 3H), 1.91-1.80 (m, 4H), 1.78-1.60 (m, 8H), 1.59-1.45 (m, 4H), 1.37-1.28 (m, 2H), 1.05-0.94 (m, 2H) |
| I-402 | AQW | AZW | 915.6 | 11.09 (s, 1H), 9.68 (s, 1H), 8.93 (s, 1H), 8.23-8.18 (m, 1H), 8.13 (d, J = 5.2 Hz, 1H), 7.62-7.54 (m, 1H), 7.32-7.02 (m, 4H), 7.00 (dd, J = 1.2, 5.2 Hz, 1H), 6.80 (d, J = 7.2 Hz, 1H), 6.71-6.64 (m, 1H), 5.05 (dd, J = 5.2, 12.8 Hz, 1H), 4.22-4.13 (m, 1H), 3.67-3.58 (m, 3H), 2.96-2.82 (m, 2H), 2.63-2.59 (m, 1H), 2.59-2.55 (m, 2H), 2.35-2.31 (m, 2H), 2.15-2.07 (m, 5H), 2.06-1.97 (m, 4H), 1.94-1.73 (m, 7H), 1.72-1.46 (m, 7H), 1.36-1.10 (m, 5H), 1.07-0.93 (m, 2H) |
| I-403[i] | AIT | ABB | 866.5 | 11.10 (s, 1H), 9.52 (s, 1H), 9.10-9.03 (m, 1H), 8.86 (d, J = 8.0 Hz, 1H), 8.34 (s, 1H), 8.02-7.92 (m, 2H), 7.66 (d, J = 8.4 Hz, 2H), 7.58 (t, J = 7.6 Hz, 1H), 7.44-7.13 (m, 1H), 7.08 (d, J = 8.8 Hz, 1H), 7.03 (d, J = 7.2 Hz, 1H), 6.94 (d, J = 8.0 Hz, 1H), 6.68-6.59 (m, 1H), 5.10-4.97 (m, 1H), 4.45-4.26 (m, 2H), 3.82 (s, 3H), 3.77-3.68 (m, 4H), 3.66 (s, 1H), 3.55-3.48 (m, 2H), 3.27-3.18 (m, 2H), 3.17-3.05 (m, 2H), 3.04-2.92 (m, 1H), 2.92-2.79 (m, 1H), 2.62-2.54 (m, 1H), 2.48-2.41 (m, 2H), 2.23-2.12 (m, 1H), 2.06-1.96 (m, 2H), 1.91-1.69 (m, 4H), 1.63-1.49 (m, 1H) |
| I-405[j] | AJY | ABB | 877.5 | 11.12 (s, 1H), 9.38 (s, 1H), 8.82 (d, J = 8.0 Hz, 1H), 8.35 (s, 1H), 8.28 (s, 1H), 8.13 (s, 1H), 7.82-7.70 (m, 2H), 7.47 (dd, J = 1.6, 8.4 Hz, 1H), 7.27-6.85 (m, 5H), 5.44 (dd, J = 5.6, 12.8 Hz, 1H), 4.62 (t, J = 5.2 Hz, 2H), 4.15-4.02 (m, 1H), 3.84 (t, J = 5.2 Hz, 2H), 3.81-3.75 (m, 4H), |

TABLE 15-continued

Compounds synthesized via Method 3 with the coupling of various amines and acids.

| I-#[a] | Intermediate Amine | Intermediate Acid | LCMS (ES+) m/z (M + H)+ | 1HNMR (400 MHz, DMSO-d6) δ |
|---|---|---|---|---|
| | | | | 3.75-3.68 (m, 4H), 3.20 (d, J = 6.4 Hz, 2H), 2.99-2.87 (m, 1H), 2.84 (s, 3H), 2.80-2.68 (m, 1H), 2.66-2.60 (m, 1H), 2.10-1.99 (m, 1H), 1.98-1.88 (m, 2H), 1.72-1.57 (m, 4H), 1.51-1.38 (m, 1H), 1.04-0.87 (m, 2H) |
| I-406 | AJQ | ABB | 877.5 | 11.12 (s, 1H), 9.38 (s, 1H), 8.82 (d, J = 8.0 Hz, 1H), 8.42 (s, 1H), 8.35 (s, 1H), 8.27 (s, 1H), 7.75 (s, 1H), 7.67 (d, J = 8.8 Hz, 1H), 7.30 (dd, J = 1.6, 8.8 Hz, 1H), 7.24-6.84 (m, 5H), 5.43 (dd, J = 5.6, 12.8 Hz, 1H), 4.62 (t, J = 4.8 Hz, 2H), 4.20-4.03 (m, 1H), 3.91 (t, J = 5.2 Hz, 2H), 3.83-3.63 (m, 8H), 3.26 (d, J = 6.4 Hz, 2H), 2.98-2.88 (m, 1H), 2.87 (s, 3H), 2.74 (dd, J = 4.4, 12.8 Hz, 1H), 2.66-2.59 (m, 1H), 2.09-2.01 (m, 1H), 2.00-1.92 (m, 2H), 1.78-1.70 (m, 2H), 1.70-1.60 (m, 2H), 1.59-1.46 (m, 1H), 1.12-0.97 (m, 2H) |
| I-446 | AMV | AEH | 811.4 | 11.11 (s, 1H), 9.50 (d, J = 5.6 Hz, 1H), 8.78 (d, J = 7.6 Hz, 1H), 8.37 (d, J = 4.0 Hz, 1H), 8.26 (d, J = 5.6 Hz, 1H), 7.28-6.93 (m, 4H), 6.45 (d, J = 7.6 Hz, 1H), 5.43-5.34 (m, 1H), 5.28 (s, 1H), 4.77 (d, J = 18.4 Hz, 1H), 4.23-4.11 (m, 1H), 3.85-3.71 (m, 2H), 3.65 (s, 1H), 3.63-3.57 (m, 1H), 3.51 (t, J = 6.0 Hz, 1H), 3.48-3.40 (m, 10H), 3.26 (d, J = 6.4 Hz, 1H), 2.95-2.83 (m, 1H), 2.76-2.69 (m, 1H), 2.55 (s, 1H), 2.07-1.93 (m, 3H), 1.92-1.78 (m, 3H), 1.77-1.65 (m, 2H), 1.64-1.54 (m, 1H), 1.25-1.11 (m, 2H) |
| I-479 | AVD | ATU | 891.5 | 11.12-11.02 (m, 1H), 9.51 (d, J = 5.2 Hz, 1H), 8.78 (d, J = 7.6 Hz, 1H), 8.45 (d, J = 4.0 Hz, 1H), 8.26 (d, J = 5.6 Hz, 1H), 7.27 (d, J = 9.2 Hz, 2H), 7.16-6.42 (m, 7H), 5.41-5.03 (m, 2H), 4.83-4.72 (m, 1H), 4.56-4.47 (m, 1H), 4.00-3.89 (m, 2H), 3.84-3.72 (m, 2H), 3.65-3.58 (m, 2H), 3.54-3.45 (m, 4H), 3.29 (s, 3H), 2.98 (s, 3H), 2.96-2.82 (m, 4H), 2.60 (m, 1H), 2.12-1.89 (m, 9H) |
| I-494 | AOD | AOI | 847.5 | 11.08 (s, 1H), 9.63 (s, 1H), 9.37 (dd, J = 7.2, 1.6 Hz, 1H), 8.90 (dd, J = 4.0, 1.6 Hz, 1H), 8.66 (s, 1H), 8.02 (s, 1H), 7.33 (dd, J = 7.2, 4.0 Hz, 1H), 6.97 (d, J = 4.4 Hz, 2H), 6.91-6.83 (m, 1H), 5.36 (dd, J = 12.8, 5.2 Hz, 1H), 4.06-3.99 (m, 1H), 3.83-3.79 (m, 4H), 3.57 (s, 3H), 3.20-3.16 (m, 4H), 3.07-2.99 (m, 5H), 2.96-2.83 (m, 4H), 2.76-2.60 (m, 6H), 2.04-1.96 (m, 3H), 1.86-1.51 (m, 13H) |
| I-502 | AQR | AHZ | 858.3 | 11.20-10.98 (m, 1H), 9.62-9.36 (m, 1H), 8.55 (d, J = 7.6 Hz, 1H), 8.32 (s, 1H), 8.18 (s, 1H), 8.00-7.87 (m, 1H), 7.64-7.51 (m, 1H), 7.23-6.92 (m, 3H), 6.43 (d, J = 7.6 Hz, 1H), 6.15 (d, J = 8.4 Hz, 1H), 5.09-4.98 (m, 1H), 4.43-4.28 (m, 1H), 4.24-4.08 (m, 1H), 3.52-3.44 (m, 3H), 2.97-2.79 (m, 1H), 2.62-2.55 (m, 1H), 2.43-2.35 (m, 2H), 2.23-2.17 (m, 5H), 2.07-1.99 (m, 5H), 1.95-1.87 (m, 2H), 1.79-1.70 (m, 6H), 1.50-1.37 (m, 3H), 1.34-1.23 (m, 2H), 1.14 (s, 6H), 1.07-0.96 (m, 2H) |
| I-504 | AQR | AVV | 872.6 | 11.11 (s, 1H), 9.55-9.33 (m, 1H), 8.76 (d, J = 7.6 Hz, 1H), 8.25 (s, 1H), 7.59 (dd, J = 7.2, 8.4 Hz, 1H), 7.30-6.94 (m, 3H), 6.69 (d, J = 8.0 Hz, 1H), 6.16 (d, J = 7.2 Hz, 1H), 5.05 (dd, J = 5.2, 12.8 Hz, 1H), 4.50-4.48 (m, 1H), 4.25-4.13 (m, 1H), 3.76-3.59 (m, 3H), 3.56-3.47 (m, 2H), 3.22 (s, 3H), 2.27-2.18 (m, 5H), 2.10-1.98 (m, 6H), 1.96-1.87 (m, 2H), 1.80-1.65 (m, 7H), 1.52-1.22 (m, 7H), 1.16 (s, 6H), 1.06-0.97 (m, 2H) |

[a]The reaction for Method 3 was run anywhere from 2-48 hrs at room temperature. A mixed solvent of ACN:DMF could be used for the reaction as well. The final products were isolated under standard purification techniques including reverse HPLC, silica gel chromatography, and prep-TLC with appropriate solvent conditions.
[b]A mixed solvent of ACN:DMF (4:1) was utilized for the reaction.
[c]A mixed solvent of ACN:DMF (3:1) was utilized for the reaction.
[d]A mixed solvent of ACN:DMF (1:1) was utilized for the reaction.
[e]A mixed solvent of ACN:DMF (10:1) was utilized for the reaction.
[f]A mixed solvent of ACN:DMF (5:1) was utilized for the reaction.
[g]A mixed solvent of ACN:DMF (2:1) was utilized for the reaction.
[h]The product of Step 1 was then deprotected with HCl/dioxane in DCM at rt for 16 h.
[i]12 hr at rt, ACN/DMF 6:1.
[j]3 hr at rt, ACN/DMF 10:1.

Example 20. Synthesis of 2-[2-(Cyclopropylmethyl-amino)-4-pyridyl]-N-[3-(difluoromethyl)-1-[4-[1-[4-[3-[1-(2,6-dioxo-3-piperidyl)-3-methyl-2-oxo-benzimidazol-4-yl]propoxy]-1-piperidyl] ethyl] cyclohexyl] pyrazol-4-yl] oxazole-4-carboxamide
(I-301)

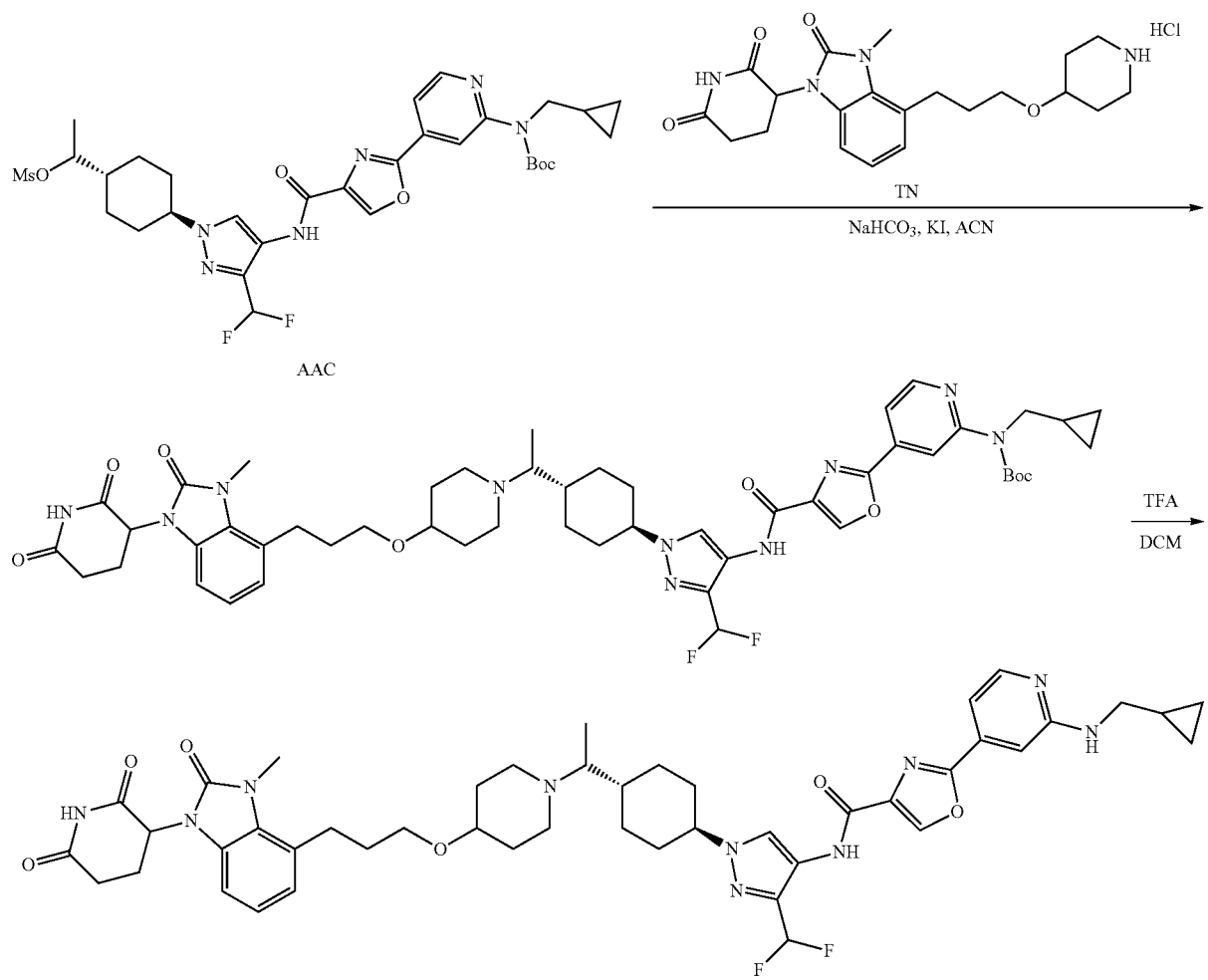

Step 1—Tert-butyl N-(cyclopropylmethyl)-N-[4-[4-[[3-(difluoromethyl)-1-[4-[1-[4-[3-[1-(2,6-dioxo-3-piperidyl)-3-methyl-2-oxo-benzimidazol-4-yl]propoxy]-1-piperidyl]ethyl] cyclohexyl]pyrazol-4-yl] carbamoyl] oxazol-2-yl]-2-pyridyl] carbamate To a solution of 3-[3-methyl-2-oxo-4-[3-(4-piperidyloxy)propyl]benzimidazol-1-yl]piperidine-2,6-dione (218 mg, 500 umol, HCl, Intermediate TN) in ACN (6 mL) was added NaHCO₃ (105 mg, 1.25 mmol), KI (4.16 mg, 25.0 umol) and 1-[4-[4-[[2-[2-[tert-butoxycarbonyl(cyclopropylmethyl)amino]-4-pyridyl] oxazole-4-carbonyl]amino]-3-(difluoromethyl)pyrazol-1-yl]cyclohexyl]ethylmethanesulfonate (170 mg, 250 umol, Intermediate AAC), and the mixture was stirred at 80° C. for 48 hrs. On completion, the reaction mixture was filtered and concentrated under reduced pressure to give a residue. The residue was purified by prep-HPLC (FA condition) to give the title compound (58 mg, 23% yield) as white solid. ¹H NMR (400 MHz, DMSO-d₆) δ 11.08 (s, 1H), 9.75 (s, 1H), 9.00 (s, 1H), 8.59 (d, J=5.2 Hz, 1H), 8.29 (s, 1H), 8.17 (s, 1H), 7.68 (d, J=5.2 Hz, 1H), 7.66-7.49 (m, 2H), 7.17-6.99 (m, 1H), 6.96 (br d, J=4.4 Hz, 2H), 6.89-6.84 (m, 1H), 5.36 (dd, J=4.4, 11.6 Hz, 1H), 4.26-4.12 (m, 1H), 3.86 (d, J=7.2 Hz, 2H), 3.57 (s, 3H), 2.98-2.94 (m, 2H), 2.69-2.62 (m, 3H), 2.23-2.18 (m, 2H), 2.13-1.96 (m, 6H), 1.85-1.72 (m, 7H), 1.52 (s, 9H), 1.41-1.33 (m, 2H), 1.25-0.98 (m, 5H), 0.89 (d, J=6.4 Hz, 3H), 0.41-0.39 (m, 2H), 0.27-0.21 (m, 2H).

Step 2—2-[2-(Cyclopropylmethylamino)-4-pyridyl]-N-[3-(difluoromethyl)-1-[4-[1-[4-[3-[1-(2,6-dioxo-3-piperidyl)-3-methyl-2-oxo-benzimidazol-4-yl]propoxy]-1-piperidyl]ethyl] cyclohexyl]pyrazol-4-yl] oxazole-4-carboxamide To a solution of tert-butyl N-(cyclopropylmethyl)-N-[4-[4-[[3-(difluoromethyl)-1-[4-[1-[4-[3-[1-(2,6-dioxo-3-piperidyl)-3-methyl-2-oxo-benzimidazol-4-yl]propoxy]-1-piperidyl]ethyl]cyclohexyl]pyrazol-4-yl]carbamoyl]oxazol-2-yl]-2-pyridyl] carbamate (55 mg, 55.9 umol) in DCM (1.2 mL) was added TFA (924 mg, 8.10 mmol), and the mixture was stirred at 10° C. for 3 hrs. On completion, the mixture was concentrated in vacuo to give a residue. The residue was purified by prep-HPLC (column: Phenomenex Synergi C18 150*25*10 um; mobile phase: [water (0.225% FA)-ACN]) to give the title compound (6.33 mg, 11% yield, FA) as white solid. $^1$H NMR (400 MHz, DMSO-$d_6$) δ 11.09 (s, 1H), 9.70 (s, 1H), 8.92 (s, 1H), 8.20-8.12 (m, 2H), 7.33-6.99 (m, 4H), 6.96 (d, J=4.8 Hz, 2H), 6.90-6.84 (m, 1H), 5.36 (dd, J=5.2, 12.8 Hz, 1H), 4.21-4.12 (m, 1H), 3.57 (s, 3H), 3.44 (t, J=5.2 Hz, 2H), 3.25-3.23 (m, 1H), 3.18 (t, J=6.0 Hz, 2H), 2.99-2.94 (m, 2H), 2.91-2.82 (m, 1H), 2.67-2.58 (m, 3H), 2.44-2.36 (m, 1H), 2.26-2.14 (m, 2H), 2.11-1.96 (m, 4H), 1.89-1.68 (m, 7H), 1.51-1.31 (m, 3H), 1.13-0.96 (m, 3H), 0.89 (d, J=6.4 Hz, 3H), 0.49-0.41 (m, 2H), 0.26-0.19 (m, 2H); LC-MS (ESI$^+$) m/z 883.3 (M+H)$^+$.

Example 21. Synthesis of N-[3-(difluoromethyl)-1-[4-[[4-[3-[1-(2,6-dioxo-3-piperidyl)-3-methyl-2-oxo-benzimidazol-4-yl] propoxy]-1-piperidyl]methyl] cyclohexyl] pyrazol-4-yl]-5-[[(1R,2S)-2-hydroxycyclohexyl]amino]pyrazolo [1,5-a] pyrimidine-3-carboxamide (I-302)

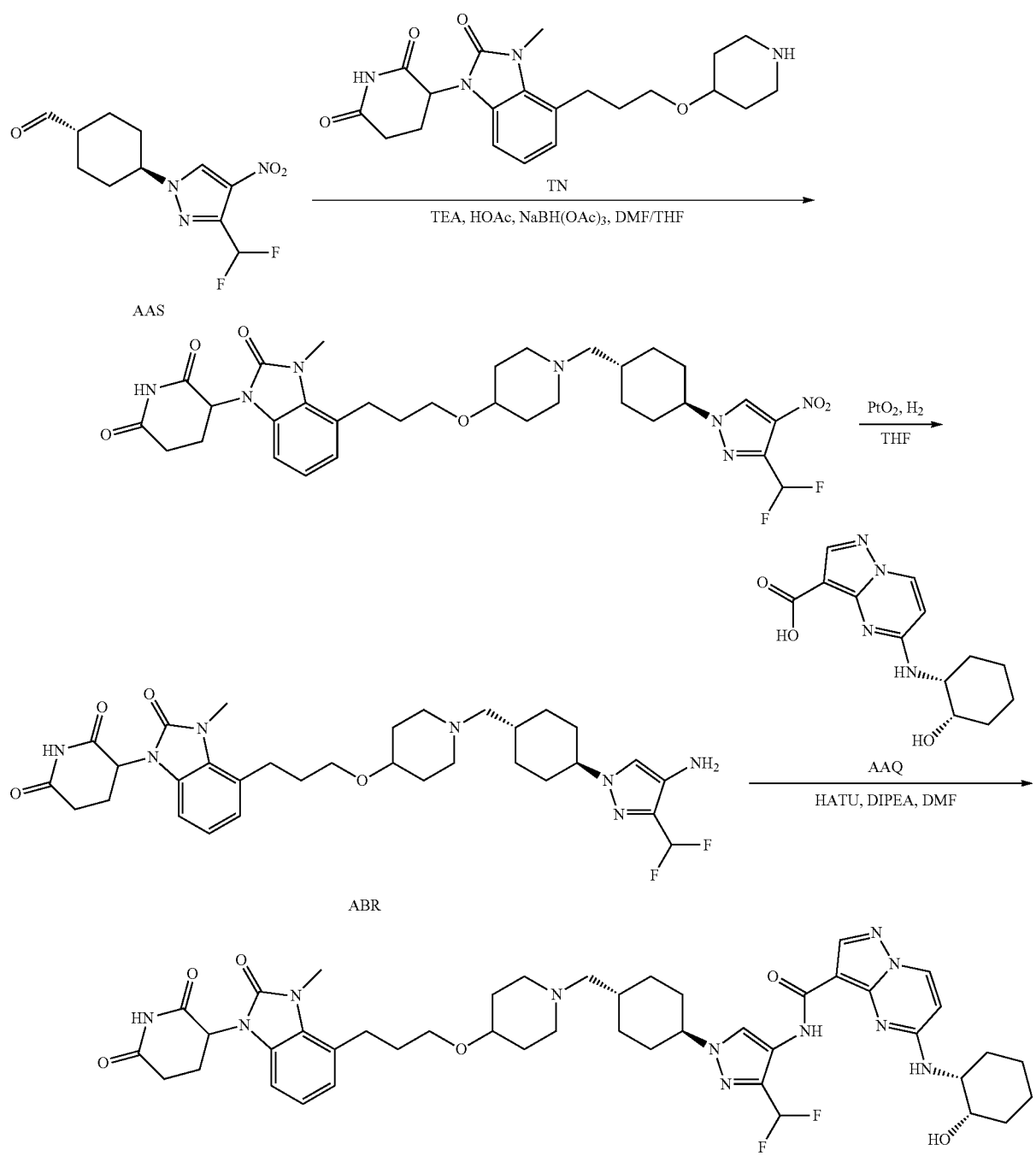

Step 1—3-[4-[3-[[1-[[4-[3-(Difluoromethyl)-4-nitro-pyrazol-1-yl] cyclohexyl]methyl]-4-piperidyl] oxy] propyl]-3-methyl-2-oxo-benzimidazol-1-yl]piperidine-2,6-dione To a solution of 3-[3-methyl-2-oxo-4-[3-(4-piperidyloxy) propyl]benzimidazol-1-yl]piperidine-2,6-dione (271 mg, 622 umol, HCl, Intermediate TN) in DMF (1.00 mL) and THF (2.00 mL) was added TEA (62.9 mg, 622 umol), the mixture was stirred at 20° C. for 15 mins. Then 4-[3-(difluoromethyl)-4-nitro-pyrazol-1-yl] cyclohexanecarbaldehyde (170 mg, 622 umol, Intermediate AAS) and HOAc (74.7 mg, 1.24 mmol) were added to the mixture, and the reaction mixture was stirred at 20° C. for 30 minutes. Then NaBH(OAc)$_3$ (197 mg, 933 umol) was added to the mixture, the reaction mixture was stirred at 25° C. for 12 hrs. On completion, the mixture was quenched by addition H$_2$O (0.5 mL), then the mixture was concentrated in vacuo to give a residue. The residue was purified by prep-HPLC (column: Phenomenex Synergi Max-RP 250*50 mm*10 um; mobile phase: [water (0.2% FA)-ACN]; B %: 12%-42%, 11 min) to give the title compound (290 mg, 70% yield) as white solid. $^1$H NMR (400 MHz, DMSO-d$_6$) δ 11.09 (s, 1H), 9.05 (s, 1H), 7.31 (t, J=53.2 Hz, 1H), 6.97 (d, J=4.4 Hz, 2H), 6.92-6.84 (m, 1H), 5.37 (dd, J=5.2, 12.4 Hz, 1H), 4.34-4.25 (m, 1H), 3.58 (s, 3H), 3.47 (t, J=5.2 Hz, 2H), 3.36-3.31 (m, 1H), 2.98 (t, J=7.6 Hz, 2H), 2.94-2.85 (m, 1H), 2.78-2.59 (m, 4H), 2.27-2.14 (m, 4H), 2.13-2.05 (m, 2H), 2.04-1.97 (m, 1H), 1.94-1.73 (m, 8H), 1.67-1.57 (m, 1H), 1.55-1.46 (m, 2H), 1.11-0.99 (m, 2H).

Step 2—3-[4-[3-[[1-[[4-[4-Amino-3-(difluoromethyl)pyrazol-1-yl]cyclohexyl]methyl]-4-piperidyl] oxy]propyl]-3-methyl-2-oxobenzimidazol-1-yl]piperidine-2,6-dione (Intermediate ABR)

To a solution of 3-[4-[3-[[1-[[4-[3-(difluoromethyl)-4-nitro-pyrazol-1-yl] cyclohexyl]methyl]-4-piperidyl]oxy] propyl]-3-methyl-2-oxo-benzimidazol-1-yl]piperidine-2,6-dione (290 mg, 440 umol) in THF (10.0 mL) was added PtO$_2$ (10.0 mg, 44.0 umol). The mixture was stirred at 15° C. for 2 hrs under H$_2$ (15 psi). On completion, the mixture was filtered and concentrated in vacuo to give the title compound (260 mg, 93% yield) as white solid. $^1$H NMR (400 MHz, DMSO-d$_6$) δ 11.09 (s, 1H), 7.13 (s, 1H), 7.03-6.91 (m, 2H), 6.90-6.65 (m, 2H), 5.40-5.33 (m, 1H), 4.03 (s, 2H), 4.00-3.90 (m, 1H), 3.62-3.58 (m, 1H), 3.57 (s, 3H), 3.48-3.42 (m, 2H), 3.30-3.21 (m, 1H), 3.00-2.92 (m, 2H), 2.91-2.83 (m, 1H), 2.77-2.68 (m, 1H), 2.66-2.56 (m, 3H), 2.12-2.04 (m, 2H), 2.03-1.91 (m, 5H), 1.88-1.78 (m, 6H), 1.77-1.72 (m, 1H), 1.70-1.56 (m, 2H), 1.55-1.48 (m, 1H), 1.04-0.90 (m, 2H).

Step 3—N-[3-(difluoromethyl)-1-[4-[[4-[3-[1-(2,6-dioxo-3-piperidyl)-3-methyl-2-oxo-benzimidazol-4-yl]propoxy]-1-piperidyl]methyl]cyclohexyl]pyrazol-4-yl]-5-[[(1R,2S)-2-hydroxycyclohexyl]amino] pyrazolo[1,5-a]pyrimidine-3-carboxamide To a solution of 3-[4-[3-[[1-[[4-[4-amino-3-(difluoromethyl)pyrazol-1-yl] cyclohexyl]methyl]-4-piperidyl] oxy]propyl]-3-methyl-2-oxo-benzimidazol-1-yl]piperidine-2,6-dione (50.0 mg, 79.6 umol), 5-[[(1R,2S)-2-hydroxycyclohexyl]amino]pyrazolo[1,5-a]pyrimidine-3-carboxylic acid (20.8 mg, 75.2 umol, Intermediate AAQ) in DMF (1.00 mL) was added PYBOP (62.1 mg, 119 umol), DIEA (51.4 mg, 398 umol) and DMAP (973 ug, 7.97 umol). The mixture was stirred at 50° C. for 16 hrs. On completion, the mixture was quenched with H$_2$O (1 mL) and concentrated in vacuo. The mixture was purified by prep-HPLC (column: Phenomenex Synergi C18 150*25*10 um; mobile phase: [water (0.225% FA)-ACN]; B %: 13%-43%, 10 min) to give the title compound as cis-racemic (30.7 mg, 41% yield) as white solid. $^1$H NMR (400 MHz, DMSO-d$_6$) δ 11.09 (s, 1H), 9.37 (s, 1H), 8.54 (d, J=7.6 Hz, 1H), 8.33 (s, 1H), 8.17 (s, 1H), 7.83 (d, J=8.8 Hz, 1H), 7.29-7.00 (m, 1H), 6.97 (d, J=4.8 Hz, 2H), 6.91-6.84 (m, 1H), 6.63 (d, J=7.6 Hz, 1H), 5.41-5.32 (m, 1H), 4.32-4.24 (m, 1H), 4.22-4.15 (m, 1H), 3.86-3.82 (m, 1H), 3.58 (s, 3H), 3.48-3.45 (m, 2H), 3.32-3.24 (m, 2H), 3.00-2.94 (m, 2H), 2.92-2.83 (m, 1H), 2.77-2.70 (m, 1H), 2.67-2.59 (m, 3H), 2.15-2.08 (m, 2H), 2.08-1.98 (m, 5H), 1.95-1.86 (m, 2H), 1.85-1.79 (m, 4H), 1.78-1.65 (m, 4H), 1.64-1.52 (m, 5H), 1.50-1.32 (m, 4H), 1.12-0.97 (m, 2H); LC-MS (ESI$^+$) m/z 886.5 (M+H)$^+$.

Example 22. Synthesis of 5-[(5R)-5-amino-3,3-difluoro-1-piperidyl]-N-[3-(difluoromethyl)-1-[4-[[4-[3-[1-(2,6-dioxo-3-piperidyl)-3-methyl-2-oxo-benzimidazol-4-yl]propoxy]-1-piperidyl]methyl] cyclohexyl] pyrazol-4-yl] pyrazolo [1,5-a] pyrimidine-3-carboxamide (I-303)

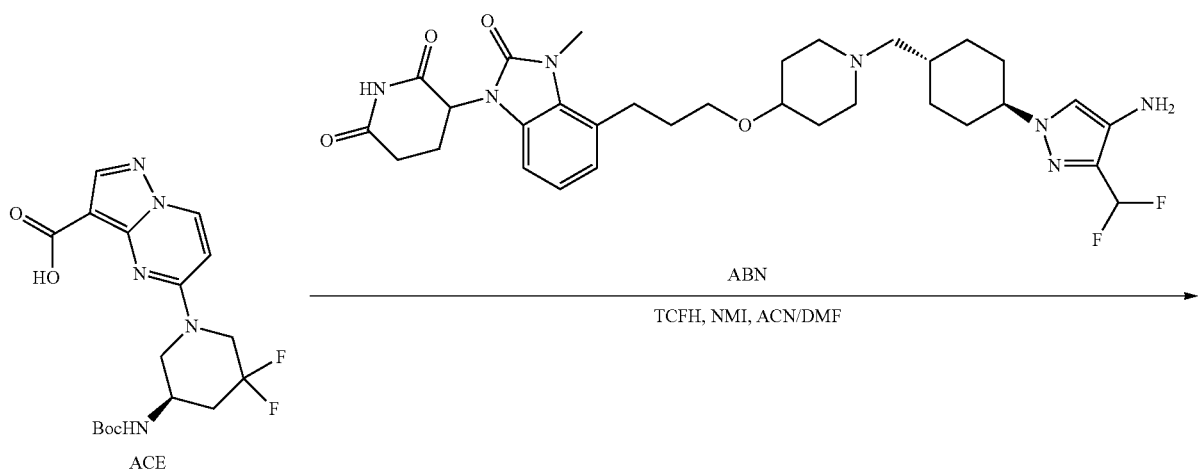

2505

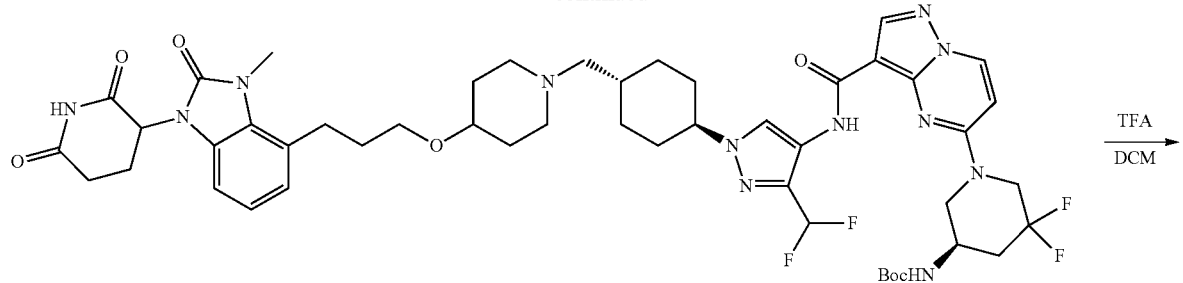

2506

-continued

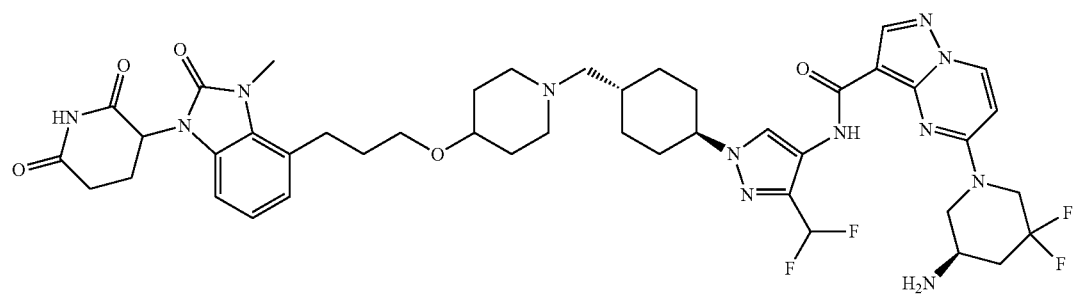

Step 1—Tert-butyl N-[(3R)-1-[3-[[3-(difluoromethyl)-1-[4-[[4-[3-[1-(2,6-dioxo-3-piperidyl)-3-methyl-2-oxo-benzimidazol-4-yl]propoxyl-1-piperidyl]methyl]cyclohexyl]pyrazol-4-yl]carbamoyl]pyrazolo[1,5-a]pyrimidin-5-yl]-5,5-difluoro-3-piperidyl]carbamate To a solution of and 5-[(5R)-5-(tert-butoxycarbonylamino)-3,3-difluoro-1-piperidyl]pyrazolo[1,5-a] pyrimidine-3-carboxylic acid (50.0 mg, 125 umol, Intermediate ACE) and [chloro(dimethylamino)methylene]-dimethyl-ammonium; hexafluorophosphate (42.3 mg, 150 umol) in ACN (2 mL) was added 1-methylimidazole (36.1 mg, 440 umol), and the mixture was stirred at 15° C. for 0.1 hr. After that, 3-[4-[3-[[1-[[4-[4-amino-3-(difluoromethyl)pyrazol-1-yl] cyclohexyl]methyl]-4-piperidyl] oxy]propyl]-3-methyl-2-oxo-benzimidazol-1-yl]piperidine-2,6-dione (78.9 mg, 125 umol, Intermediate ABN) was added, and the mixture was stirred at 15° C. for 40 hrs. On completion, the reaction mixture was quenched with water (0.2 mL). Then the residue was purified by prep-HPLC (FA condition) to give the title compound (70.0 mg, 55% yield) as white solid. LC-MS (ESI$^+$) m/z 1007.3 (M+H)$^+$.

Step 2—5-[(5R)-5-amino-3,3-difluoro-1-piperidyl]-N-[3-(difluoromethyl)-1-[4-[[4-[3-[1-(2,6-dioxo-3-piperidyl)-3-methyl-2-oxo-benzimidazol-4-yl]propoxy]-1-piperidyl]methyl]cyclohexyl]pyrazol-4-yl]pyrazolo[1,5-a]pyrimidine-3-carboxamide To a solution of tert-butyl N-[(3R)-1-[3-[[3-(difluoromethyl)-1-[4-[[4-[3-[1-(2,6-dioxo-3-piperidyl)-3-methyl-2-oxo-benzimidazol-4-yl]propoxy]-1-piperidyl]methyl]cyclohexyl]pyrazol-4-yl]carbamoyl]pyrazolo[1,5-a]pyrimidin-5-yl]-5,5-difluoro-3-piperidyl]carbamate (55.0 mg, 54.6 umol) in DCM (2 mL) was added TFA (3.08 g, 27.0 mmol). The mixture was stirred at 10° C. for 0.5 hr. On completion, the mixture was concentrated in vacuo to give a residue. The residue was purified by prep-HPLC (column: Phenomenex Synergi C18 150*25*10 um; mobile phase: [water (0.225% FA)-ACN]) to give the title compound (21.1 mg, 42% yield) as white solid. $^1$H NMR (400 MHz, DMSO-d$_6$) δ 11.09 (s, 1H), 9.27 (s, 1H), 8.88 (d, J=8.0 Hz, 1H), 8.38 (s, 1H), 8.32 (s, 1H), 7.31-6.99 (m, 2H), 6.98-6.93 (m, 2H), 6.90-6.84 (m, 1H), 5.36 (dd, J=5.2, 12.8 Hz, 1H), 4.86-4.71 (m, 1H), 4.42-4.30 (m, 1H), 4.20-4.14 (m, 1H), 3.65 (d, J=14.5 Hz, 1H), 3.57 (s, 3H), 3.45 (t, J=6.0 Hz, 2H), 3.30-3.27 (m, 1H), 3.14-2.83 (m, 6H), 2.73-2.62 (m, 4H), 2.37 (d, J=8.8 Hz, 1H), 2.17-1.94 (m, 8H), 1.92-1.68 (m, 9H), 1.62-1.53 (m, 1H), 1.51-1.40 (m, 2H), 1.10-0.96 (m, 2H); LC-MS (ESI$^+$) m/z 907.6 (M+H)$^+$.

Examples 23. Syntheses of 4-[[4-[4-[3-[1-(2,6-di-oxo-3-piperidyl)-3-methyl-2-oxo-benzimidazol-4-yl]propoxy]-1-piperidyl]cyclohexyl]amino]quinazoline-6-carbonitrile (I-304) and 4-[[4-[4-[3-[1-(2,6-dioxo-3-piperidyl)-3-methyl-2-oxo-benzimidazol-4-yl]propoxy]-1-piperidyl]cyclohexyl]amino]quinazoline-6-carbonitrile (I-305)

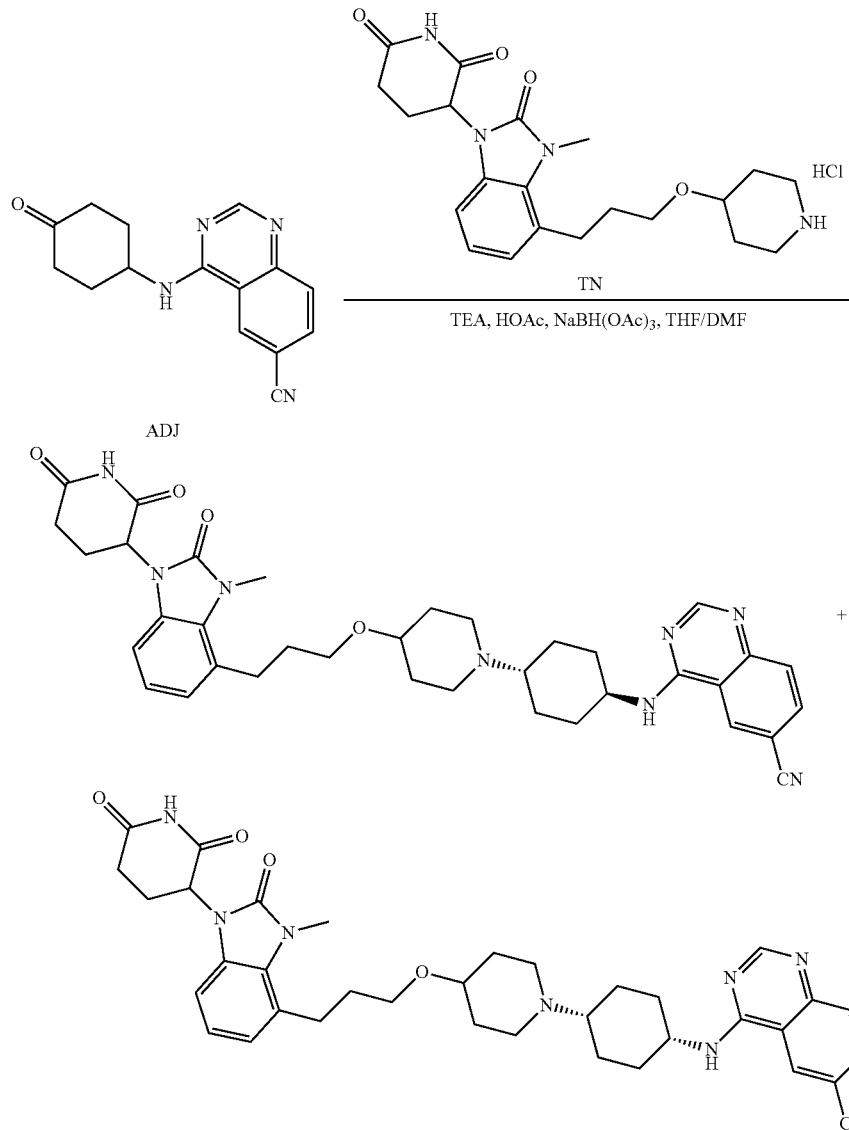

To a solution of 4-[(4-oxocyclohexyl)amino]quinazoline-6-carbonitrile (60.0 mg, 225 umol, Intermediate ADJ) and 3-[3-methyl-2-oxo-4-[3-(4-piperidyloxy)propyl]benzimidazol-1-yl]piperidine-2,6-dione (98.5 mg, 225 umol, HCl, Intermediate TN) in a mixed solvent of DMF (1.00 mL) and THF (2.00 mL) was added TEA (22.8 mg, 225 umol), and the mixture was stirred at 20° C. for 10 minutes. Then HOAc (27.1 mg, 450 umol) was added, and the mixture was stirred at 20° C. for 0.5 hr. Next, NaBH(OAc)₃ (57.3 mg, 270 umol) was added, then the mixture was stirred at 20° C. for 16 hrs. On completion, the reaction mixture was quenched by addition water (0.5 mL), and then concentrated in vacuo to give a residue. The residue was purified by prep HPLC (column: Phenomenex Luna C18 150*25 mm*10 um; mobile phase: [water (0.1% TFA)-ACN]; B %: 15%-35%, 10 min) to give 4-[[4-[4-[3-[1-(2,6-dioxo-3-piperidyl)-3-methyl-2-oxo-benzimidazol-4-yl]propoxy]-1-piperidyl]cyclohexyl]amino]quinazoline-6-carbonitrile (4.24 mg, 3% yield) as a white solid and 4-[[4-[4-[3-[1-(2,6-dioxo-3-piperidyl)-3-methyl-2-oxo-benzimidazol-4-yl]propoxy]-1-piperidyl]cyclohexyl]amino]quinazoline-6-carbonitrile (4.21 mg, 6.47 umol, 3% yield) as a yellow solid. Characterization of 4-[[4-[4-[3-[1-(2,6-dioxo-3-piperidyl)-3-methyl-2-oxo-benzimidazol-4-yl]propoxy]-1-piperidyl]cyclohexyl]amino]quinazoline-6-carbonitrile:

¹H NMR (400 MHz, DMSO-d₆) δ 11.08 (s, 1H), 8.99 (s, 1H), 8.70 (s, 1H), 8.16 (d, J=8.8 Hz, 1H), 7.82 (d, J=8.8 Hz, 1H), 7.03-6.94 (m, 2H), 6.93-6.85 (m, 1H), 5.36 (dd, J=5.2, 12.4 Hz, 1H), 4.35-4.15 (m, 1H), 3.70 (s, 1H), 3.59 (d, J=10.8 Hz, 3H), 3.51 (d, J=3.2 Hz, 2H), 3.15-2.83 (m, 8H), 2.76-2.68 (m, 1H), 2.65-2.60 (m, 1H), 2.22-2.10 (m, 5H), 2.03-1.95 (m, 2H), 1.95-1.78 (m, 4H), 1.74-1.59 (m, 3H), 1.59-1.47 (m, 2H). LC-MS (ESI⁺) m/z 651.4 (M+H)⁺. Characterization of 4-[[4-[4-[3-[1-(2,6-dioxo-3-piperidyl)-3-methyl-2-oxo-benzimidazol-4-yl]propoxy]-1-piperidyl]cyclohexyl]amino]quinazoline-6-carbonitrile: ¹H NMR (400 MHz, DMSO-d₆) δ 11.08 (s, 1H), 9.16 (s, 1H), 8.71 (s, 1H), 8.17 (d, J=8.8 Hz, 1H), 7.84 (d, J=8.8 Hz, 1H), 7.01-6.93 (m, 2H), 6.91-6.83 (m, 1H), 5.35 (dd, J=5.2, 12.4 Hz, 1H), 4.39 (s, 1H), 3.76-3.65 (m, 1H), 3.58 (d, J=6.4 Hz, 3H), 3.50 (d, J=6.0 Hz, 2H), 3.24-2.83 (m, 8H), 2.76-2.68 (m, 1H), 2.65-2.59 (m, 1H), 2.28-2.15 (m, 3H), 2.06-1.54 (m, 13H). LC-MS (ESI⁺) m/z 651.4 (M+H)⁺.

Examples 24. Syntheses of 2-[2-(cyclopropylmethylamino)-4-pyridyl]-N-[3-(difluoromethyl)-1-[4-[[3-[3-[1-[(3S)-2,6-dioxo-3-piperidyl]-3-methyl-2-oxo-benzimidazol-4-yl] propoxy] propyl-methyl-amino] methyl] cyclohexyl] pyrazol-4-yl] oxazole-4-carboxamide (I-306) and 2-[2-(cyclopropylmethylamino)-4-pyridyl]-N-[3-(difluoromethyl)-1-[4-[[3-[3-[1-[(3R)-2,6-dioxo-3-piperidyl]-3-methyl-2-oxo-benzimidazol-4-yl] propoxy] propyl-methyl-amino] methyl] cyclohexyl] pyrazol-4-yl]oxazole-4-carboxamide (I-307)

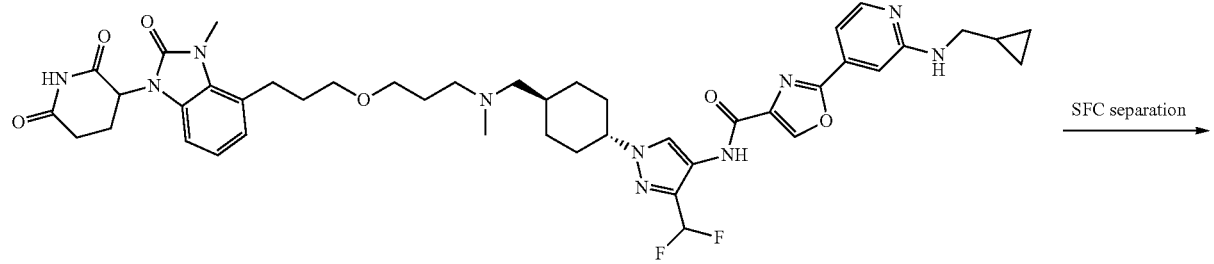

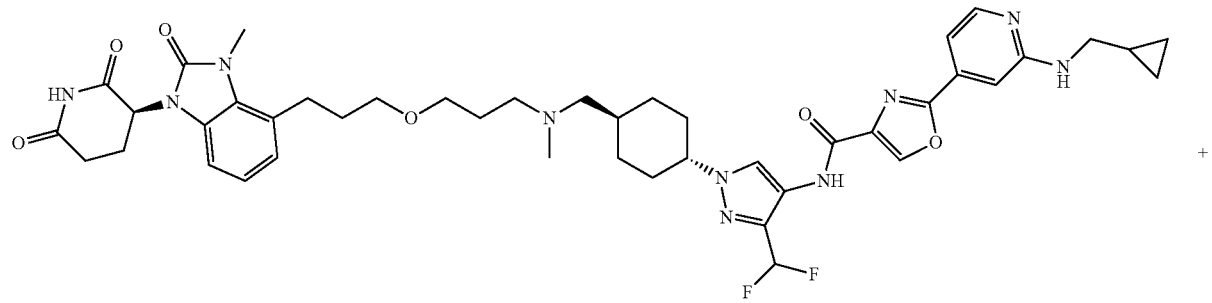

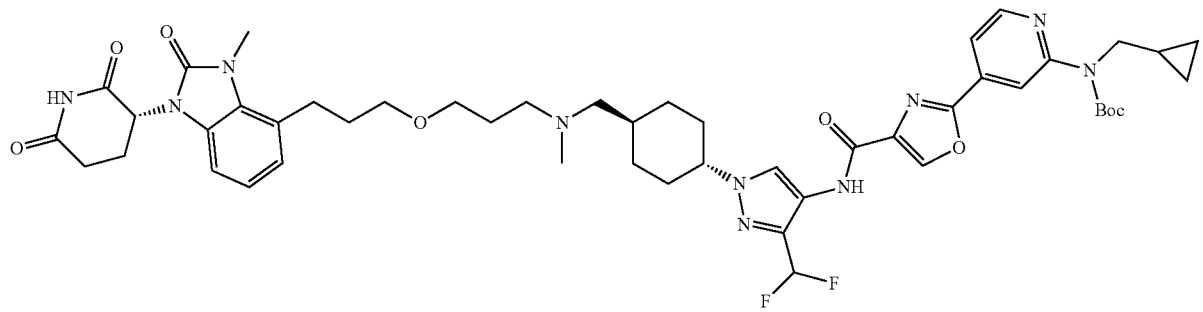

2-[2-(Cyclopropylmethylamino)-4-pyridyl]-N-[3-(difluoromethyl)-1-[4-[[3-[3-[1-(2,6-dioxo-3-piperidyl)-3-methyl-2-oxo-benzimidazol-4-yl]propoxy]propyl-methyl-amino]methyl]cyclohexyl]pyrazol-4-yl]oxazole-4-carboxamide (500 mg, 583 umol, Example 2, I-30) was separated by SFC. The residue was purified by SFC (Sample preparation: Add $CH_3CN$ 200 ml into sample Instrument: Waters 80Q Mobile Phase: 70% IPA+ACN (0.1% DEA) in Supercritical C02 Flow Rate: 70 g/min Cycle Time: 4 min, total time: 350 min Single injection volume: 3.0 ml Back Pressure: 100 bar to keep the C02 in Supercritical flow) to give peak 1 (72% ee value) and peak 2 (81% ee value). The fraction was received in a solution of 2.5% hydrochloride in isopropanol and concentrated in vacuo. Peak 1 was re-purified by SFC (Sample preparation: Add $CH_3CN$ and $CH_2CL_2$ 40 ml into sample Instrument: Waters 80Q Mobile Phase: 70% IPA (0.1% DEA) in Supercritical C02 Flow Rate: 70 g/min Cycle Time: 6 min, total time: 110 min Single injection volume: 2.5 ml Back Pressure: 100 bar to keep the C02 in Supercritical flow). Peak 2 was also re-purified by SFC (Sample preparation: Add $CH_3CN$ and $CH_2CL_2$ 80 ml into sample Instrument: Waters 80Q Mobile Phase: 70% IPA+CAN (0.1% DEA) in Supercritical C02 Flow Rate: 70 g/min Cycle Time: 4 min, total time: 80 min Single injection volume: 4.0 ml Back Pressure: 100 bar to keep the C02 in Supercritical flow). The fraction was received in a solution of 2.5% hydrochloride in isopropanol and concentrated in vacuo. After that, Peak 1 was purified by prep-HPLC (column: Phenomenex Synergi C18 150*25*10 um; mobile phase: [water (0.225% FA)-ACN]; B %: 9%-39%, 10 min) to give 2-[2-(cyclopropylmethylamino)-4-pyridyl]-N-[3-(difluoromethyl)-1-[4-[[3-[3-[1-[(3S)-2,6-dioxo-3-piperidyl]-3-methyl-2-oxo-benzimidazol-4-yl]propoxy]propyl-methyl-amino]methyl] cyclohexyl]pyrazol-4-yl] oxazole-4-carboxamide (122 mg, 23% yield, FA) as white solid; $^1$H NMR (400 MHz, DMSO-$d_6$) δ 11.08 (s, 1H), 9.69 (s, 1H), 8.92 (s, 1H), 8.17 (s, 1H), 8.15 (d, J=5.2 Hz, 1H), 7.29-7.00 (m, 4H), 6.96 (d, J=5.2 Hz, 2H), 6.89-6.84 (m, 1H), 5.39-5.33 (m, 1H), 4.25-4.15 (m, 1H), 3.57 (s, 3H), 3.42 (t, J=6.0 Hz, 4H), 3.18 (t, J=6.0 Hz, 2H), 2.99-2.93 (m, 2H), 2.92-2.82 (m, 1H), 2.75-2.57 (m, 2H), 2.56-2.51 (m, 2H), 2.39 (t, J=7.2 Hz, 2H), 2.19-2.14 (m, 5H), 2.07-1.97 (m, 3H), 1.90 (d, J=12.4 Hz, 2H), 1.86-1.79 (m, 2H), 1.78-1.73 (m, 1H), 1.68-1.65 (m, 1H), 1.60-1.49 (m, 1H), 1.10-0.97 (m, 3H), 0.48-0.42 (m, 2H), 0.25-0.20 (m, 2H); LC-MS (ESI$^+$) m/z 857.6 (M+H)$^+$. Peak 2 was purified by prep-HPLC (column: Phenomenex Synergi C18 150*25*10 um; mobile phase: [water (0.225% FA)-ACN]; B %: 9%-39%, 10 min) to give 2-[2-(cyclopropylmethylamino)-4-pyridyl]-N-[3-(difluoromethyl)-1-[4-[[3-[3-[1-[(3R)-2,6-dioxo-3-piperidyl]-3-methyl-2-oxo-benzimidazol-4-yl]propoxy]propyl-methyl-amino]methyl]cyclohexyl]pyrazol-4-yl]oxazole-4-carboxamide (99.2 mg, 18% yield, FA) as white solid; $^1$H NMR (400 MHz, DMSO-$d_6$) δ 11.08 (s, 1H), 9.69 (s, 1H), 8.92 (s, 1H), 8.17 (s, 1H), 8.15 (d, J=5.2 Hz, 1H), 7.29-7.00 (m, 4H), 6.96 (d, J=5.2 Hz, 2H), 6.89-6.85 (m, 1H), 5.39-5.33 (m, 1H), 4.24-4.14 (m, 1H), 3.57 (s, 3H), 3.42 (t, J=6.0 Hz, 4H), 3.18 (t, J=6.0 Hz, 2H), 3.00-2.93 (m, 2H), 2.92-2.84 (m, 1H), 2.75-2.68 (m, 1H), 2.65-2.58 (m, 1H), 2.52 (s, 2H), 2.37 (t, J=6.8 Hz, 2H), 2.16 (s, 3H), 2.13 (s, 2H), 2.03 (d, J=12.8 Hz, 2H), 2.00-1.95 (m, 1H), 1.90 (d, J=11.2 Hz, 2H), 1.85-1.80 (m, 2H), 1.75 (d, J=12 Hz, 1H), 1.66 (t, J=6.8 Hz, 1H), 1.59-1.48 (m, 1H), 1.11-0.97 (m, 3H), 0.48-0.42 (m, 2H), 0.25-0.19 (m, 2H); LC-MS (ESI$^+$) m/z 857.6 (M+H)$^+$.

Examples 25. Syntheses of 2-(2-((cyclopropylmethyl)amino)pyridin-4-yl)-N-(3-(difluoromethyl)-1-((1S,4r)-4-(((1-((1-((S)-2,6-dioxopiperidin-3-yl)-3-methyl-2-oxo-2,3-dihydro-1H-benzo [d] imidazol-4-yl)methyl)piperidin-4-yl)(methyl)amino)methyl)cyclohexyl)-1H-pyrazol-4-yl)oxazole-4-carboxamide (I-308) and 2-(2-((cyclopropylmethyl)amino)pyridin-4-yl)-N-(3-(difluoromethyl)-1-((1R,4r)-4-(((1-((1-((R)-2,6-dioxopiperidin-3-yl)-3-methyl-2-oxo-2,3-dihydro-1H-benzo [d]imidazol-4-yl)methyl) piperidin-4-yl)(methyl)amino)methyl)cyclohexyl)-1H-pyrazol-4-yl)oxazole-4-carboxamide (I-309)

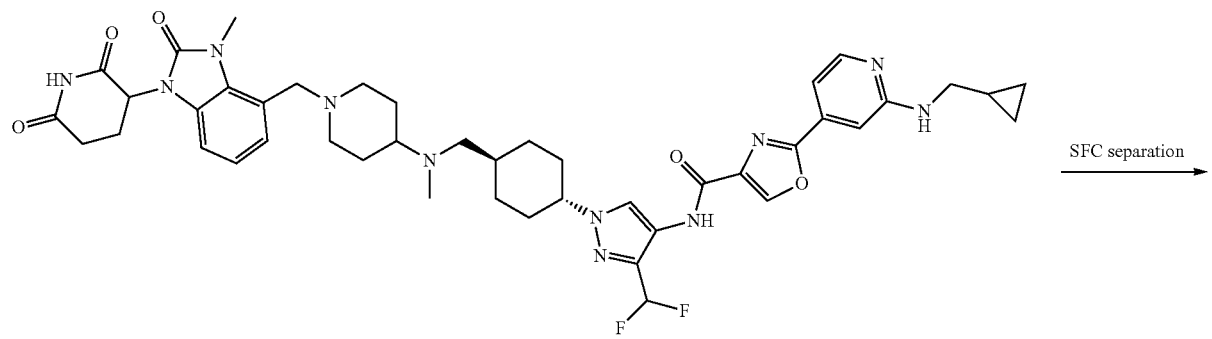

I-75

SFC separation

2513

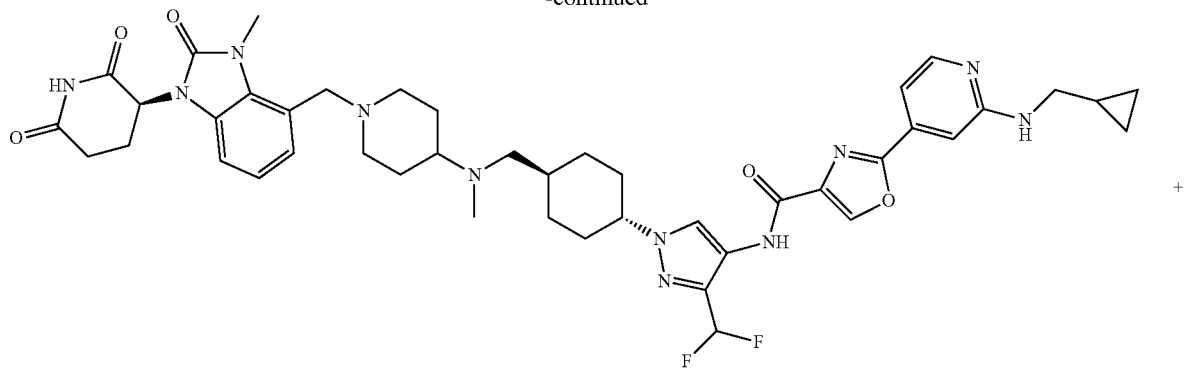

2514

-continued

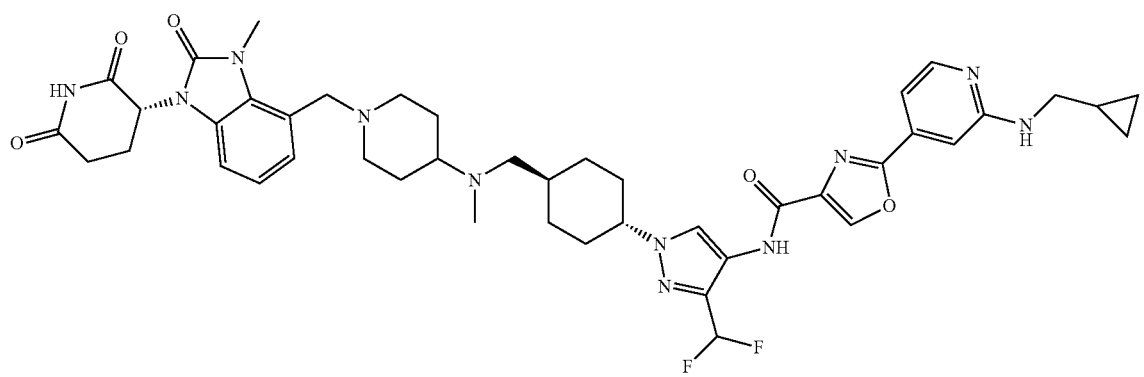

The trans diastereomer 2-(2-((cyclopropylmethyl)amino)pyridin-4-yl)-N-(3-(difluoromethyl)-1-((1r,4r)-4-(((1-((1-(2,6-dioxopiperidin-3-yl)-3-methyl-2-oxo-2,3-dihydro-1H-benzo[d]imidazol-4-yl)methyl)piperidin-4-yl)(methyl)amino)methyl)cyclohexyl)-1H-pyrazol-4-yl)oxazole-4-carboxamide (1.00 g, Example 1-75) was separated by SFC (column: DAICEL CHIRALPAK AD (250 mm*30 mm, 10 um); mobile phase: [0.1% NH$_3$H$_2$O IPA]) twice and purified by Prep-HPLC (column: Phenomenex Synergi C18 150*25*10 um; mobile phase: [water (0.225% FA)-ACN]) to give the two title compounds.

The first peak, 2-(2-((cyclopropylmethyl)amino)pyridin-4-yl)-N-(3-(difluoromethyl)-1-((1S,4r)-4-(((1-((1-((S)-2,6-dioxopiperidin-3-yl)-3-methyl-2-oxo-2,3-dihydro-1H-benzo[d]imidazol-4-yl)methyl)piperidin-4-yl)(methyl)amino)methyl)cyclohexyl)-1H-pyrazol-4-yl)oxazole-4-carboxamide (128 mg, 24% yield, 100% ee, FA salt) was obtained as white solid. $^1$H NMR (400 MHz, DMSO-d$_6$) δ 11.09 (s, 1H), 9.68 (s, 1H), 8.91 (s, 1H), 8.17 (s, 1H), 7.33-6.92 (m, 6H), 6.87 (d, J=7.2 Hz, 1H), 5.38 (dd, J=5.2, 12.8 Hz, 1H), 4.25-4.11 (m, 1H), 3.67 (s, 3H), 3.62 (s, 2H), 3.18 (t, J=6.0 Hz, 3H), 2.95-2.82 (m, 3H), 2.71 (dd, J=4.4, 12.8 Hz, 1H), 2.66-2.59 (m, 1H), 2.52 (d, J=2.0 Hz, 1H), 2.40 (t, J=11.2 Hz, 1H), 2.27 (d, J=6.0 Hz, 1H), 2.22 (s, 3H), 2.08-1.98 (m, 4H), 1.97-1.84 (m, 3H), 1.74 (d, J=9.6 Hz, 2H), 1.66 (d, J=11.2 Hz, 2H), 1.50 (s, 1H), 1.47-1.35 (m, 2H), 1.11-0.95 (m, 3H), 0.51-0.41 (m, 2H), 0.26-0.19 (m, 2H); LC-MS (ESI$^+$) m/z 854.5 (M+H)$^+$.

The second peak, 2-(2-((cyclopropylmethyl)amino)pyridin-4-yl)-N-(3-(difluoromethyl)-1-((1R,4r)-4-(((1-((1-((R)-2,6-dioxopiperidin-3-yl)-3-methyl-2-oxo-2,3-dihydro-1H-benzo[d]imidazol-4-yl)methyl)piperidin-4-yl)(methyl)amino)methyl)cyclohexyl)-1H-pyrazol-4-yl)oxazole-4-carboxamide (185 mg, 36% yield, 94.3% ee, FA salt) was obtained as white solid. $^1$H NMR (400 MHz, DMSO-d$_6$) δ 11.09 (s, 1H), 9.67 (s, 1H), 8.91 (s, 1H), 8.17 (s, 1H), 7.30-6.99 (m, 5H), 6.96 (t, J=7.6 Hz, 1H), 6.87 (d, J=7.2 Hz, 1H), 5.38 (dd, J=5.6, 12.8 Hz, 1H), 4.24-4.12 (m, 1H), 3.67 (s, 3H), 3.62 (s, 2H), 3.18 (t, J=6.0 Hz, 3H), 2.88 (d, J=11.2 Hz, 3H), 2.71 (dd, J=4.4, 13.2 Hz, 1H), 2.66-2.59 (m, 1H), 2.52 (d, J=2.0 Hz, 1H), 2.37 (s, 1H), 2.25 (d, J=6.8 Hz, 1H), 2.20 (s, 3H), 2.07-2.00 (m, 3H), 2.00-1.93 (m, 2H), 1.92-1.84 (m, 2H), 1.74 (d, J=10.0 Hz, 2H), 1.65 (d, J=11.6 Hz, 2H), 1.57-1.33 (m, 3H), 1.13-0.95 (m, 3H), 0.50-0.41 (m, 2H), 0.25-0.19 (m, 2H); LC-MS (ESI$^+$) m/z 854.5 (M+H)$^+$.

Examples 26. Syntheses of N-(3-(difluoromethyl)-1-((1r,4r)-4-((4-(3-(1-((S)-2,6-dioxopiperidin-3-yl)-3-methyl-2-oxo-2,3-dihydro-1H-benzo [d] imidazol-4-yl)propoxy)piperidin-1-yl)methyl)cyclohexyl)-1H-pyrazol-4-yl)-5-morpholinopyrazolo[1,5-a]pyrimidine-3-carboxamide (I-310) and N-(3-(difluoromethyl)-1-((1r,4r)-4-((4-(3-(1-((R)-2,6-dioxopiperidin-3-yl)-3-methyl-2-oxo-2,3-dihydro-1H-benzo [d] imidazol-4-yl)propoxy)piperidin-1-yl)methyl)cyclohexyl)-1H-pyrazol-4-yl)-5-morpholinopyrazolo[1,5-a] pyrimidine-3-carboxamide (I-311)

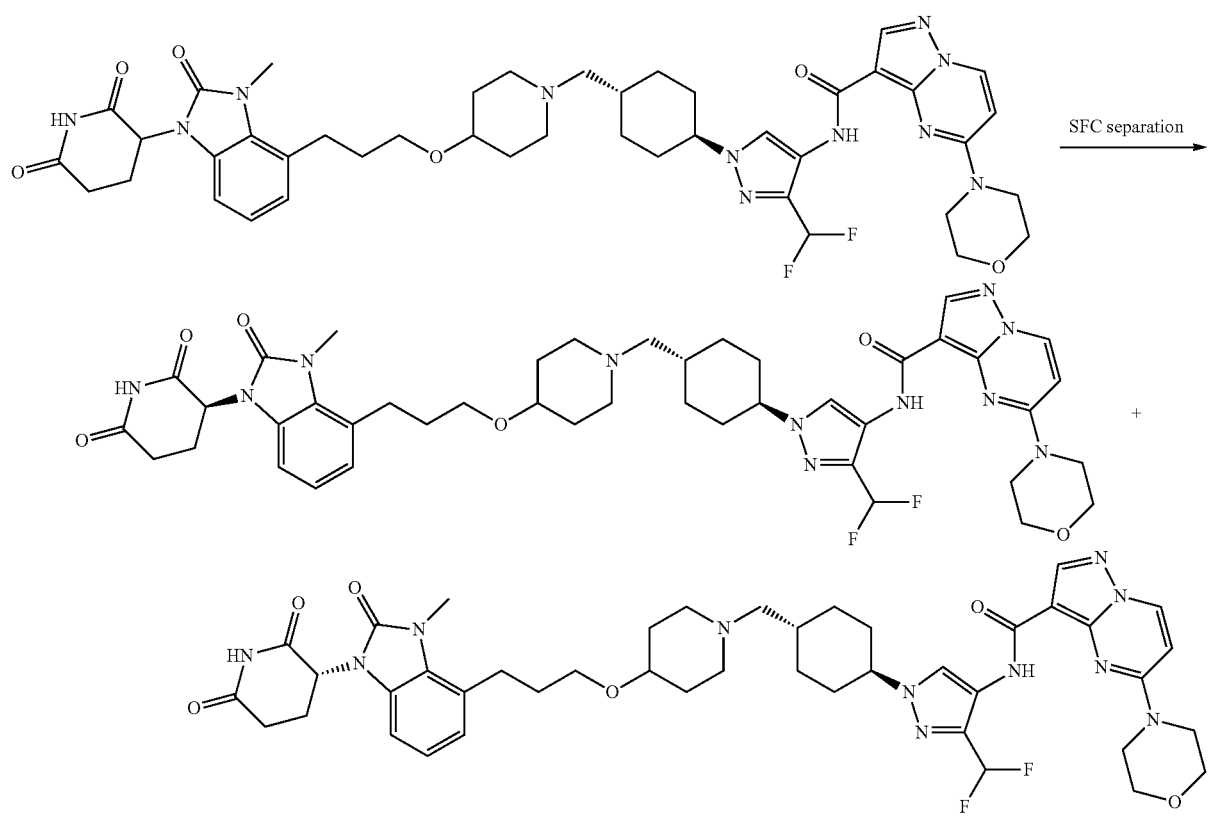

N-[3-(difluoromethyl)-1-[4-[[4-[3-[1-[(3S)-2,6-dioxo-3-piperidyl]-3-methyl-2-oxo-benzimidazol-4-yl] propoxy]-1-piperidyl]methyl]cyclohexyl]pyrazol-4-yl]-5-morpholino-pyrazolo[1,5-a]pyrimidine-3-carboxamide (200 mg, 223 umol, Compound 1-257, HCl salt) was separated by SFC (Add CH$_3$CN and CH$_2$Cl$_2$, IPA+01% DEA 150 mL into sample; Instrument: Waters 80Q SFC; Mobile Phase: 65% (IPA+20% ACN (0.1% DEA)) in Supercritical CO$_2$; Flow Rate: 70 g/min; Cycle Time: 6.1 min, total time: 240 min; Single injection volume: 4.0 ml; Back Pressure: 100 bar to keep the CO$_2$ in Supercritical flow) to give peak 1, N-(3-(difluoromethyl)-1-((1r,4r)-4-((4-(3-(1-(((S)-2,6-dioxopiperidin-3-yl)-3-methyl-2-oxo-2,3-dihydro-1H-benzo[d]imidazol-4-yl)propoxy)piperidin-1-yl)methyl)cyclohexyl)-1H-pyrazol-4-yl)-5-morpholinopyrazolo[1,5-a]pyrimidine-3-carboxamide (99% ee value) and peak 2, N-(3-(difluoromethyl)-1-((1r,4r)-4-((4-(3-(1-((R)-2,6-dioxopiperidin-3-yl)-3-methyl-2-oxo-2,3-dihydro-1H-benzo[d]imidazol-4-yl)propoxy)piperidin-1-yl)methyl)cyclohexyl)-1H-pyrazol-4-yl)-5-morpholinopyrazolo[1,5-a] pyrimidine-3-carboxamide (93% ee value). The fractions were added to a solution of 2.5% HCl in MeCN solution and then concentrated in vacuo respectively. Peak 2 was further purified by SFC (Sample preparation: Add CH$_3$CN and IPA+0.1% DEA 60 ml into sample; Instrument: Waters 80Q SFC; Mobile Phase: 65% (IPA+20% ACN (0.1% DEA)) in Supercritical CO$_2$; Flow Rate: 75 g/min; Cycle Time: 5.5 min, total time: 100 min; Single injection volume: 3.0 mL; Back Pressure: 100 bar to keep the CO$_2$ in Supercritical flow.") to afford N-(3-(difluoromethyl)-1-((1r,4r)-4-((4-(3-(1-((R)-2,6-dioxopiperidin-3-yl)-3-methyl-2-oxo-2,3-dihydro-1H-benzo[d]imidazol-4-yl)propoxy)piperidin-1-yl)methyl)cyclohexyl)-1H-pyrazol-4-yl)-5-morpholinopyrazolo[1,5-a]pyrimidine-3-carboxamide (99% ee value).

Peak 1 was then purified by prep-HPLC (column: Phenomenex Synergi C18 150*25*10 um; mobile phase: [water (0.05% HCl)-ACN]; B %: 25%-45%, 12 min) to afford N-(3-(difluoromethyl)-1-((1r,4r)-4-((4-(3-(1-((S)-2,6-dioxopiperidin-3-yl)-3-methyl-2-oxo-2,3-dihydro-1H-benzo

[d]imidazol-4-yl)propoxy)piperidin-1-yl)methyl)cyclohexyl)-1H-pyrazol-4-yl)-5-morpholinopyrazolo[1,5-a]pyrimidine-3-carboxamide (42.8 mg, 14% yield, 99% ee value, HCl salt) as an off-white solid; ¹H NMR (400 MHz, DMSO-d₆) δ 11.12 (s, 1H), 9.42 (s, 1H), 8.88-8.78 (m, 1H), 8.40 (s, 1H), 8.30 (s, 1H), 7.26-6.84 (m, 5H), 5.44-5.32 (m, 1H), 4.24 (t, J=11.6 Hz, 1H), 3.80 (s, 4H), 3.73 (d, J=3.6 Hz, 4H), 3.61-3.60 (m, 3H), 3.51 (s, 3H), 3.41 (s, 2H), 3.34 (d, J=10.6 Hz, 1H), 3.06-2.84 (m, 7H), 2.77-2.59 (m, 2H), 2.16-1.74 (m, 15H), 1.25-1.12 (m, 2H); LC-MS (ESI⁺) m/z 858.6 (M+H)⁺.

Peak 2 was purified by prep-HPLC (column: Phenomenex Synergi C18 150*25*10 um; mobile phase: [water (0.05% HCl)-ACN]; B %: 25%-45%, 12 min) to afford N-(3-(difluoromethyl)-1-((1r,4r)-4-((4-(3-(1-((R)-2,6-dioxopiperidin-3-yl)-3-methyl-2-oxo-2,3-dihydro-1H-benzo[d]imidazol-4-yl)propoxy)piperidin-1-yl)methyl)cyclohexyl)-1H-pyrazol-4-yl)-5-morpholinopyrazolo[1,5-a]pyrimidine-3-carboxamide (23.6 mg, 8% yield, 99% ee value, HCl salt) as an off-white solid; ¹H NMR (400 MHz, DMSO-d₆) δ 11.12 (s, 1H), 9.42 (s, 1H), 8.87-8.81 (m, 1H), 8.41 (s, 1H), 8.30 (s, 1H), 7.26-6.86 (m, 5H), 5.46-5.28 (m, 1H), 4.30-4.19 (m, 1H), 3.80 (s, 4H), 3.74-3.71 (m, 6H), 3.59 (d, J=9.2 Hz, 3H), 3.54-3.48 (m, 3H), 3.35 (d, J=10.0 Hz, 1H), 3.06-2.85 (m, 7H), 2.78-2.59 (m, 2H), 2.16-1.73 (m, 14H), 1.27-1.12 (m, 2H); LC-MS (ESI⁺) m/z 858.6 (M+H)⁺.

Example 27. Synthesis of N-[1-[4-(aminomethyl)cyclohexyl]-3-(difluoromethyl)pyrazol-4-yl]-2-[2-(cyclopropylmethyl amino)-4-pyridyl]oxazole-4-carboxamide (I-312)

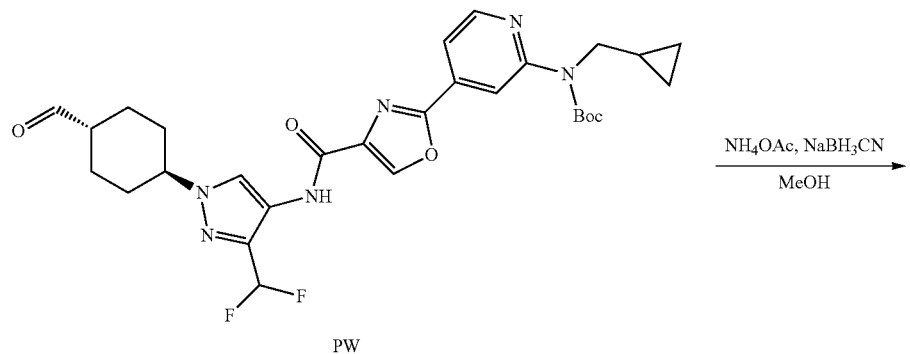

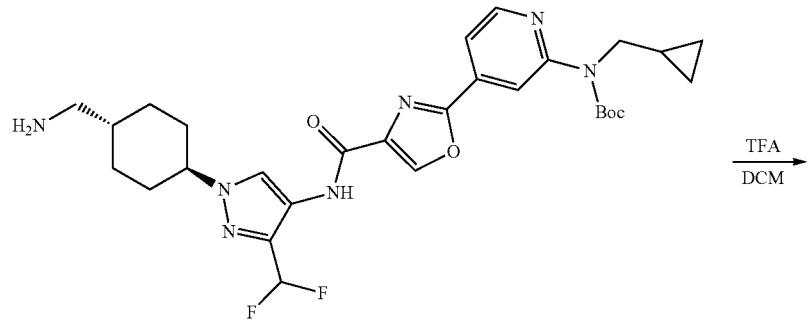

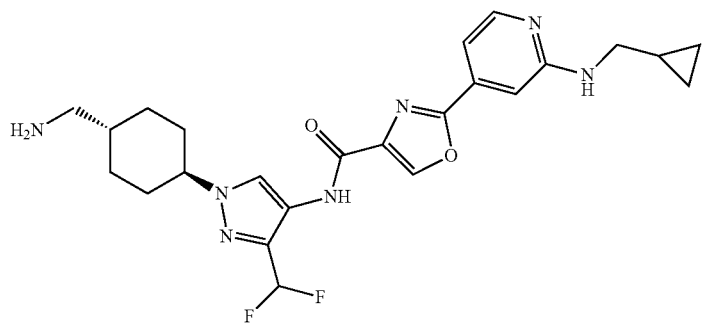

Step 1—Tert-butyl N-[4-[4-[[1-[4-(aminomethyl) cyclohexyl]-3-(difluoromethyl)pyrazol-4-yl] carbamoyl] oxazol-2-yl]-2-pyridyl]-N-(cyclopropylmethyl)carbamate To a mixture of tert-butyl N-(cyclopropylmethyl)-N-[4-[4-[[3-(difluoromethyl)-1-(4-formylcyclohexyl) pyrazol-4-yl]carbamoyl]oxazol-2-yl]-2-pyridyl]carbamate (500 mg, 855 umol, Intermediate PW) and NH₄OAc (1.32 g, 17.1 mmol) in MeOH (10 mL) was added NaBH₃CN (80.6 mg, 1.28 mmol). The reaction mixture was stirred at 25° C. for 12 hours. On completion, the reaction mixture was filtered and concentrated in vacuo. The residue was purified by reverse phase (0.1% FA condition) to give the title compound (120 mg, 23% yield) as white solid. LC-MS (ESI⁺) m/z 586.4 (M+H)⁺.

Step 2—N-[1-[4-(aminomethyl)cyclohexyl]-3-(difluoromethyl)pyrazol-4-yl]-2-[2-(cyclopropylmethyl amino)-4-pyridyl]oxazole-4-carboxamide To a mixture of tert-butyl N-[4-[4-[[1-[4-(aminomethyl) cyclohexyl]-3-(difluoromethyl)pyrazol-4-yl] carbamoyl] oxazol-2-yl]-2-pyridyl]-N-(cyclopropylmethyl)carbamate (110 mg, 187 umol) in DCM (2 mL) was added TFA (3.08 g, 27.0 mmol, 2 mL). The reaction mixture was stirred at 25° C. for 0.5 hour. On completion, the reaction mixture was concentrated in vacuo. The residue was purified by prep-HPLC (column: Phenomenex Synergi C18 150*25*10 um; mobile phase: [water (0.225% FA)-ACN]; B %: 2%-32%, 10 min) to give the title compound (41.1 mg, 40% yield, 98% purity) as white solid. ¹H NMR (400 MHz, DMSO-d₆) δ 9.73 (s, 1H), 8.92 (s, 1H), 8.33 (s, 1H), 8.15 (d, J=5.2 Hz, 1H), 7.32-7.04 (m, 3H), 7.03-6.99 (m, 1H), 4.25-4.19 (m, 1H), 3.18 (t, J=6.0 Hz, 2H), 2.75-2.65 (m, 2H), 2.08 (d, J=10.4 Hz, 2H), 1.91 (d, J=12.4 Hz, 2H), 1.81-1.69 (m, 2H), 1.67-1.57 (m, 1H), 1.21-1.09 (m, 2H), 1.09-1.01 (m, 1H), 0.48-0.42 (m, 2H), 0.24-0.19 (m, 2H); LC-MS (ESI⁺) m/z 486.3 (M+H)⁺.

Example 28. Synthesis of N-[1-[4-(aminomethyl) cyclohexyl]-3-(difluoromethyl)pyrazol-4-yl]-5-morpholino-pyrazolo [1,5-a]pyrimidine-3-carboxamide (I-313)

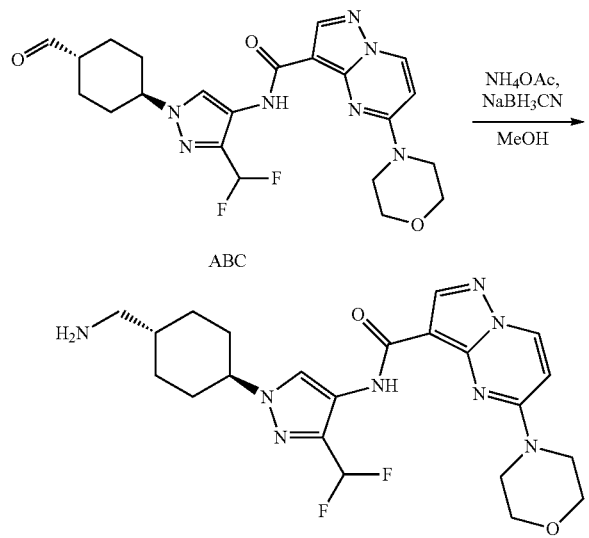

To a mixture of N-[3-(difluoromethyl)-1-(4-formylcyclohexyl)pyrazol-4-yl]-5-morpholino-pyrazolo [1,5-a]pyrimidine-3-carboxamide (0.20 g, 422 umol, Intermediate ABC) in MeOH (100 mL) was added NH₄OAc (6.51 g, 84.5 mmol) and the mixture was stirred for 1 hour. Then NaBH₃CN (39.8 mg, 634 umol) was added into the mixture and the mixture was stirred at 20° C. for 13 hours. On completion, the reaction mixture was quenched with water (5 mL) and filtered to give the filtrate. The filtrate was concentrated in vacuo to give the residue. The residue was purified by prep-HPLC column: Phenomenex Synergi C18 150*30 mm*4 um; mobile phase: [water (0.225% FA)-ACN]; B %: 8%-38%) to give the title compound (18.6 mg, 9% yield) as a off-white solid. ¹H NMR (400 MHz, DMSO-d₆) δ 9.39 (s, 1H), 8.83 (d, J=8.0 Hz, 1H), 8.46-8.37 (m, 2H), 7.27-6.95 (m, 1H), 6.91 (d, J=8.0 Hz, 1H), 4.25-4.14 (m, 1H), 3.79 (s, 4H), 3.75-3.69 (m, 4H), 2.69-2.51 (m, 4H), 2.06 (d, J=10.4 Hz, 2H), 1.91 (d, J=12.0 Hz, 2H), 1.80-1.65 (m, 2H), 1.55 (d, J=3.6 Hz, 1H), 1.20-1.06 (m, 2H); LC-MS (ESI⁺) m/z 475.2 (M+H)⁺.

Example 29. Synthesis of 4-[2-[4-(Aminomethyl) cyclohexyl]ethynyl]-1-[[(2S,3S,4S)-3-ethyl-4-fluoro-5-oxo-pyrrolidin-2-yl]methoxy]-7-methoxy-isoquinoline-6-carboxamide (I-314)

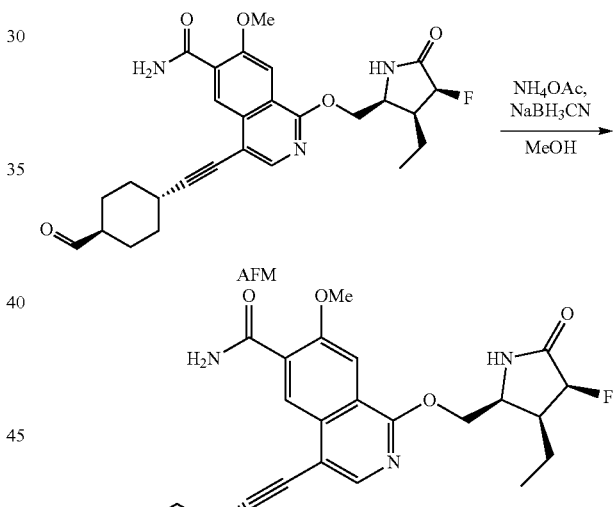

To a solution of 1-[[(2S,3S,4S)-3-ethyl-4-fluoro-5-oxo-pyrrolidin-2-yl]methoxy]-4-[2-(4-formyl cyclohexyl)ethynyl]-7-methoxy-isoquinoline-6-carboxamide (50.0 mg, 100 umol, Intermediate AFM) in methanol (2 mL) was added NH₄OAc (1.56 g, 20.1 mmol). After the reaction mixture was stirred at 20° C. for 3 hr, NaBH₃CN (9.51 mg, 151 umol) was added. The reaction mixture was stirred at 20° C. for 16 hrs. On completion, the reaction mixture was quenched by water (0.2 mL) and concentrated in vacuo. The residue was purified by prep-HPLC (column: Phenomenex Synergi C18 150*25*10 um; mobile phase: [water (0.225% FA)-ACN]; B %: 15%-35%, 10 min) to give the title compound (10.5 mg, 18% yield, FA salt) as off-white solid. ¹H NMR (400 MHz, DMSO-d₆) δ 8.87 (s, 1H), 8.40 (s, 1H), 8.02 (s, 1H), 7.95-7.68 (m, 3H), 7.33-6.42 (m, 2H), 4.99-

4.81 (m, 1H), 4.53 (dd, J=3.2, 11.2 Hz, 1H), 4.26 (dd, J=6.4, 11.2 Hz, 1H), 4.12-4.05 (m, 1H), 3.98 (s, 3H), 2.66-2.62 (m, 1H), 2.62-2.59 (m, 2H), 2.58-2.52 (m, 2H), 2.17-2.02 (m, 2H), 1.90-1.76 (m, 2H), 1.68-1.55 (m, 2H), 1.55-1.40 (m, 3H), 1.10-0.97 (m, 4H); LC-MS (ESI$^+$) m/z 497.2 (M+H)$^+$.

Example 30. Synthesis of N-[1-[4-[[3-(3-amino-propoxy)propyl-methyl-amino]methyl] cyclohexyl]-3-(difluoromethyl) pyrazol-4-yl]-5-morpholino-pyrazolo[1,5-a] pyrimidine-3-carboxamide (I-315)

(10 mL) was added KOAc (186 mg, 1.90 mmol). The mixture was stirred at 25° C. for 0.5 hour. N-[3-(difluoromethyl)-1-(4-formylcyclohexyl) pyrazol-4-yl]-5-morpholino-pyrazolo [1,5-a]pyrimidine-3-carboxamide (300 mg, 633 umol, Intermediate ABC) and NaBH(OAc)$_3$ (161 mg, 760 umol) were added into the mixture. The reaction mixture was stirred at 25° C. for 11.5 hours. On completion, the reaction was quenched by water (5 mL) and CH$_3$CN (10 mL), the mixture was concentrated in vacuo to give the residue. The residue was purified by reverse phase HPLC (0.1% FA condition) to give the title compound (340 mg,

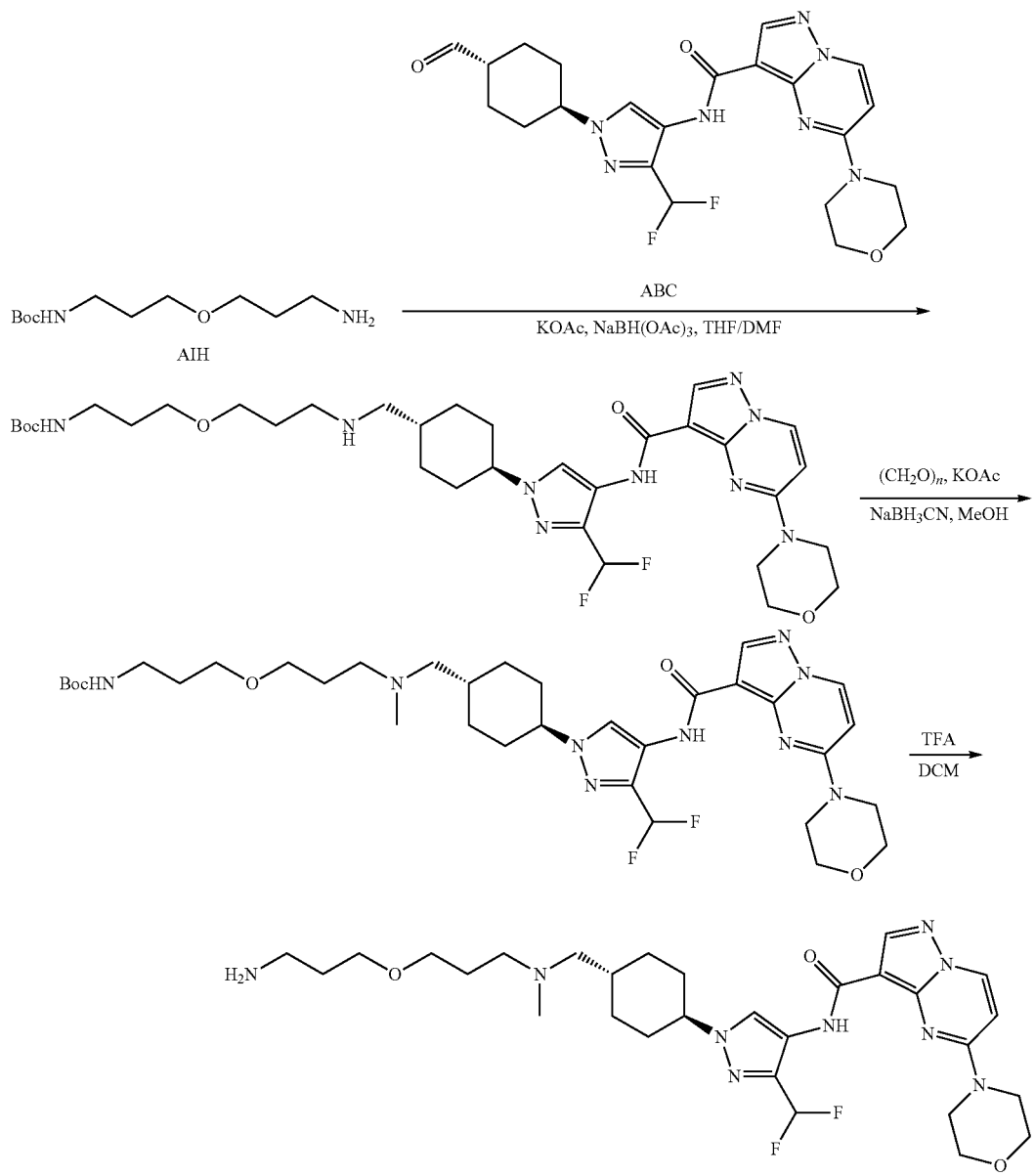

Step 1—Tert-butyl N-[3-[3-[[4-[3-(difluoromethyl)-4-[(5-morpholinopyrazolo[1,5-a]pyrimidine-3-carbonyl)amino]pyrazol-1-yl] cyclohexyl]methylamino] propoxy]propyl] carbamate To a mixture of tert-butyl N-[3-(3-aminopropoxy)propyl] carbamate (294 mg, 1.27 mmol, Intermediate AIH) in THF 77% yield) as a white solid. $^1$H NMR (400 MHz, CDCl$_3$) δ 9.51 (s, 1H), 8.48-8.31 (m, 4H), 6.91-6.59 (m, 1H), 6.45-6.37 (m, 1H), 4.06 (d, J=7.6 Hz, 1H), 3.88-3.83 (m, 3H), 3.82 (s, 3H), 3.57 (d, J=5.6 Hz, 2H), 3.46 (d, J=5.6 Hz, 2H), 3.27-3.14 (m, 4H), 2.93 (d, J=6.8 Hz, 1H), 2.27-2.17 (m, 2H), 2.11-2.04 (m, 2H), 2.02 (s, 2H), 1.93-1.78 (m, 2H), 1.77-1.68 (m, 2H), 1.45 (s, 9H), 1.31-1.17 (m, 2H); LC-MS (ESI$^+$) m/z 690.2 (M+H)$^+$.

Step 2—Tert-butyl N-[3-[3-[[4-[3-(difluoromethyl)-4-[(5-morpholinopyrazolo[1,5-a]pyrimidine-3-carbonyl)amino]pyrazol-1-yl]]cyclohexyl]methyl-methyl-amino]propoxy]propyl]carbamate To a mixture of tert-butyl N-[3-[3-[[4-[3-(difluoromethyl)-4-[(5-morpholinopyrazolo[1,5-a] pyrimidine-3-carbonyl)amino]pyrazol-1-yl]cyclohexyl]methylamino]propoxy]propyl]carbamate (73.0 mg, 105.8 umol) in MeOH (2 mL) was added KOAc (31.2 mg, 317 umol). The mixture was stirred at 25° C. for 0.5 hour. HCHO (31.7 mg, 1.06 mmol) and NaBH₃CN (7.98 mg, 127 umol) was added into the mixture. The reaction mixture was stirred at 25° C. for 0.5 hour. On completion, the reaction was quenched by water (5 mL) and CH₃CN (10 mL), the mixture was concentrated in vacuo to give the residue. The residue was purified by reverse phase (0.1% FA condition) to give the title compound (70.0 mg, 93% yield) as a white solid. LC-MS (ESI$^+$) m/z 704.2 (M+H)$^+$.

Step 3—N-[1-[4-[[3-(3-aminopropoxy)propyl-methyl-amino]methyl]cyclohexyl]-3-(difluoromethyl) pyrazol-4-yl]-5-morpholino-pyrazolo[1,5-a] pyrimidine-3-carboxamide To a mixture of tert-butyl N-[3-[3-[[4-[3-(difluoromethyl)-4-[(5-morpholinopyrazolo[1,5-a] pyrimidine-3-carbonyl)amino]pyrazol-1-yl]cyclohexyl]methyl-methyl-amino]propoxy]propyl]carbamate (700 mg, 99.4 umol) in DCM (10 mL) was added TFA (34.0 mg, 298 umol). The reaction mixture was stirred at 20° C. for 0.5 hour. On completion, the reaction mixture was concentrated in vacuo to give the residue. The residue was purified by prep-HPLC (column: Phenomenex Synergi C18 150*30 mm*4 um; mobile phase: [water (0.225% FA)-ACN]; B %: 4%-34%) to give the title compound (12.8 mg, 21% yield) as a yellow gum. ¹H NMR (400 MHz, DMSO-d₆) δ 9.40 (s, 1H), 8.83 (d, J=8.0 Hz, 1H), 8.38 (s, 1H), 8.29 (s, 1H), 7.24-6.95 (m, 1H), 6.91 (d, J=8.0 Hz, 1H), 4.18 (d, J=10.4 Hz, 1H), 3.79 (s, 4H), 3.74-3.70 (m, 4H), 3.69 (s, 1H), 3.41 (s, 2H), 2.81 (d, J=7.6 Hz, 2H), 2.34-2.28 (m, 3H), 2.12 (s, 3H), 2.11-2.01 (m, 4H), 1.89 (d, J=7.2 Hz, 2H), 1.80-1.70 (m, 4H), 1.67-1.58 (m, 2H), 1.56-1.47 (m, 1H), 1.28 (s, 2H), 1.09-0.95 (m, 2H). ¹H NMR (400 MHz, MeOH-d4) δ 8.60-8.51 (m, 2H), 8.35 (d, J=15.6 Hz, 2H), 7.03-6.72 (m, 2H), 4.27-4.16 (m, 1H), 3.93-3.79 (m, 8H), 3.58 (d, J=9.2 Hz, 4H), 3.07 (d, J=7.2 Hz, 2H), 2.85 (d, J=7.2 Hz, 2H), 2.66 (d, J=7.2 Hz, 2H), 2.58 (s, 3H), 2.22 (d, J=7.6 Hz, 2H), 2.09-2.00 (m, 2H), 1.99-1.86 (m, 6H), 1.84-1.75 (m, 1H), 1.39 (s, 2H), 1.33-1.19 (m, 2H); LC-MS (ESI$^+$) m/z 604.2 (M+H)$^+$.

Example 31. Synthesis of 4-[2-[4-[[3-(3-Aminopropoxy)propyl-methyl-amino] methyl] cyclohexyl] ethynyl]-1-[[(2S, 3S, 4S)-3-ethyl-4-fluoro-5-oxo-pyrrolidin-2-yl]methoxy]-7-methoxy-isoquinoline-6-carboxamide (I-316)

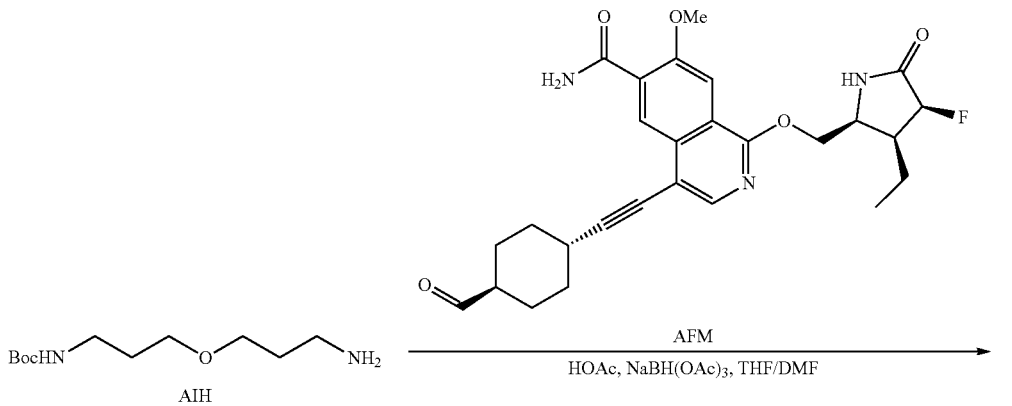

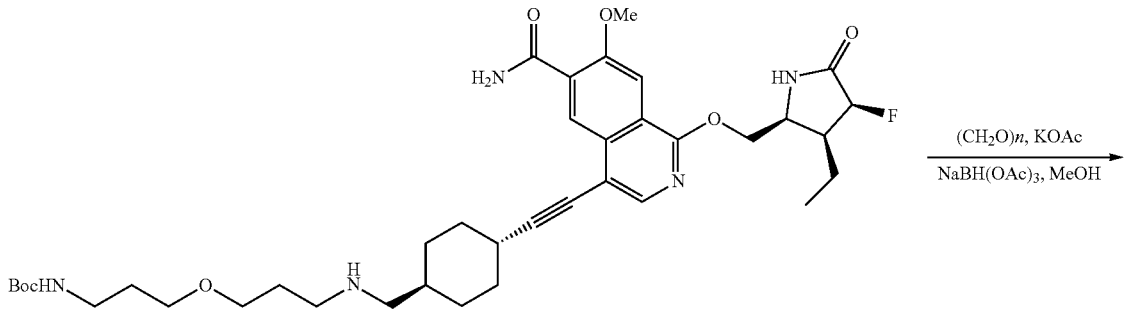

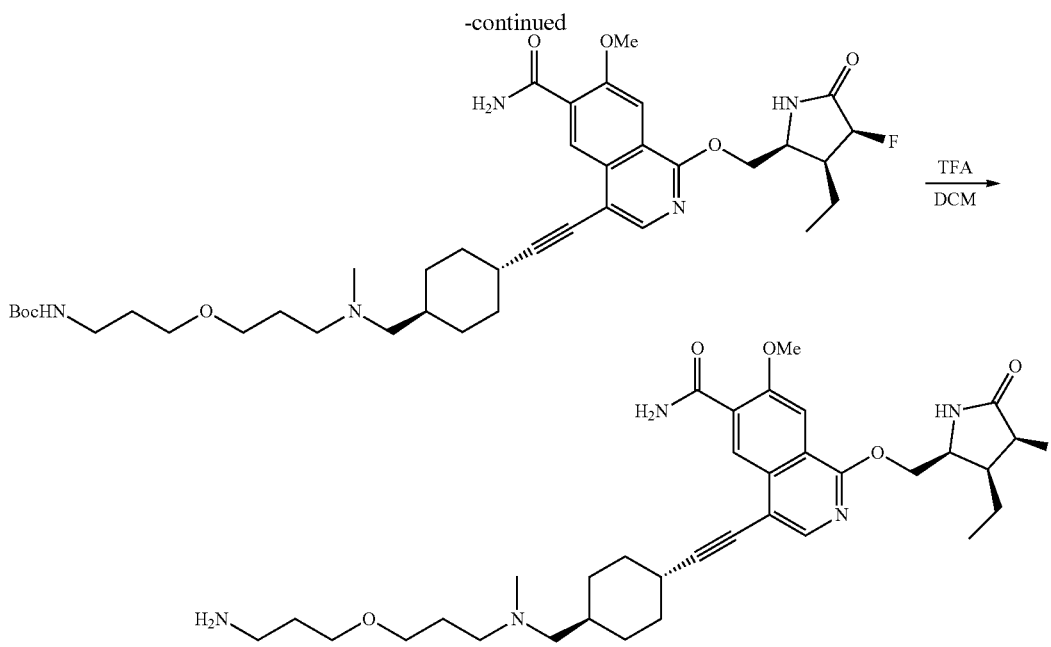

Step 1—Tert-butyl N-[3-[3-[[4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]cyclohexyl]methylamino]propoxy]propyl]carbamate To a mixture of tert-butyl N-[3-(3-aminopropoxy)propyl]carbamate (37.5 mg, 161 umol, Intermediate AIH) and 1-[[(2S,3S,4S)-3-ethyl-4-fluoro-5-oxo-pyrrolidin-2-yl]methoxy]-4-[2-(4-formyl cyclo hexyl)ethynyl]-7-methoxy-isoquinoline-6-carboxamide (40 mg, 80.7 umol, Intermediate AFM) in a mixed solvent of THF (2.0 mL) and DMF (0.5 mL) was added HOAc (4.85 mg, 80.7 umol) at 0° C. The mixture was stirred at 0° C. for 0.5 hour. Then, NaBH(OAc)$_3$ (34.2 mg, 161 umol) was added, and the mixture was stirred at 0° C. for 1.5 hours. On completion, the mixture was quenched with H$_2$O (5 mL) and then extracted with DCM (4×10 mL). The combined organic phase was dried over Na$_2$SO$_4$, filtered and the filtrate was concentrated in vacuo to give the title compound (67.0 mg, 96% yield) as a yellow solid. LC-MS (ESI$^+$) m/z 712.2 (M+H)$^+$.

Step 2—Tert-butyl N-[3-[3-[[4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]cyclohexyl]methyl-methyl-amino]propoxy]propyl]carbamate To a mixture of tert-butyl N-[3-[3-[[4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl]cyclohexyl]methylamino]propoxy]propyl]carbamate (67.0 mg, 94.1 umol) and HCHO (28.3 mg, 941 umol) in MeOH (5 mL) was added KOAc (27.7 mg, 282 umol) at 25° C. The mixture was stirred at 25° C. for 0.5 hour. Then, NaBH$_3$CN (11.8 mg, 188 umol) was added, and the mixture was stirred at 25° C. for 16 hours. On completion, the reaction mixture was quenched with water (0.2 mL) at 25° C., and then extracted with DCM (2×20 mL). The combined organic layers were dried over Na$_2$SO$_4$, filtered and concentrated in vacuo to give the title compound (40.0 mg, 59% yield) as yellow solid. LC-MS (ESI$^+$) m/z 726.5 (M+H)$^+$.

Step 3—4-[2-[4-[[3-(3-Aminopropoxy)propyl-methyl-amino]methyl]cyclohexyl]ethynyl]-1-[[(2S, 3S, 4S)-3-ethyl-4-fluoro-5-oxo-pyrrolidin-2-yl]methoxy]-7-methoxy-isoquinoline-6-carboxamide To a mixture of tert-butyl N-[3-[3-[[4-[2-[6-carbamoyl-1-[[(2S,3S,4S)-3-ethyl-4-fluoro-5-oxo-pyrrolidin-2-yl]methoxy]-7-methoxy-4-isoquinolyl]ethynyl] cyclohexyl] methyl-methyl-amino]propoxy]propyl]carbamate (40.0 mg, 55.1 umol) in DCM (2 mL) was added TFA (3.08 g, 2 mL) at 25° C. The mixture was stirred at 25° C. for 2 hours. On completion, the mixture was concentrated in vacuo to give a residue. The residue was purified by prep-HPLC (column: Phenomenex luna C18 150*25 mm*10 um; mobile phase: [water (0.1% TFA)-ACN]; B %: 11%-41%, 10 min) to afford the title compound (13.6 mg, 33% yield, TFA salt) as white solid. $^1$H NMR (400 MHz, DMSO-d$_6$) δ 8.89 (s, 1H), 8.30 (s, 1H), 8.03 (s, 1H), 7.92 (br s, 1H), 7.78 (s, 1H), 7.76 (br s, 1H), 7.67-7.61 (m, 2H), 4.99-4.83 (m, 1H), 4.56-4.51 (m, 1H), 4.29-4.23 (m, 1H), 4.13-4.07 (m, 1H), 3.99 (s, 3H), 3.45 (t, J=6.2 Hz, 4H), 2.88-2.82 (m, 2H), 2.80 (d, J=4.8 Hz, 3H), 2.16-2.10 (m, 3H), 1.93-1.84 (m, 5H), 1.82-1.75 (m, 4H), 1.61-1.52 (m, 4H), 1.25-1.23 (m, 1H), 1.19-1.18 (m, 1H), 1.17-1.06 (m, 4H), 1.02 (t, J=7.4 Hz, 3H). LC-MS (ESI$^+$) m/z 626.3 (M+H)$^+$.

Example 32. Quantification of Ikaros and Aiolos Degradation

Degradation of Ikaros (protein product of gene IKZF 1) and Aiolos (protein product of gene IKZF3) were determined by quantitative immunoblotting as follows. OCI-LY10 cells, 2×10$^6$ cells/well, were treated with listed concentrations of IRAK4 degraders or control compounds in 6 well plates for 6 h. Cells were collected, washed with cold PBS, lysed in RIPA buffer (Boston BioProducts BP-115D) with protease/phosphatase inhibitor cocktail (Roche 05892791001/Roche 04906837001) and centrifuged at 13000 RPM for 20 min to precipitate insoluble material. The supernatant fraction was diluted in SDS-PAGE loading buffer (Beyotime Bio P0015) and 20 μL of each sample was resolved on 4-12% Bis-Tris SDS-PAGE gels (Novex, WG1402BOX). Resolved samples were transferred to nitrocellulose membranes by wet electro-transfer method at 250 mV for 1.5 h. The membrane was blocked with LICOR blocking buffer (LI-COR, 927-50000) for 1 hour, washed three times with TBST (CST #9997S) for 5 minutes each and incubated with primary antibody prepared in block buffer with 0.1% Tween-20 (Solarbio, P8220) at 4° C. overnight. Ikaros antibody was rabbit monoclonal D6N9Y (CST #14859), at 1:1000 dilution. Aiolos antibody was rabbit monoclonal D1C1E (CST #15103), at 1:1000 dilution. Signal was normalized to mouse anti-beta-Actin monoclonal 8H10D10 (CST #3700) used at 1:10,000 dilution. After incubation in primary antibodies, membranes were washed three times with TBST, 5 minutes each, incubated with fluorescently labeled secondary antibodies anti-rabbit IgG (Licor, 926-32211) at 1:5000 dilution; anti-mouse IgG (LI-COR, 926-68070) at 1:5000 dilution, for 1 hour at RT. After incubation in secondary, membranes were washed three times with TBST, 5 minutes each and read on LICOR Odyssey imager. Data are reported as signal for Ikaros or Aiolos relative to signal for actin, and normalized to DMSO-treated control.

Example 33. Synthesis of N-[1-[4-(3-aminoprop-1-ynyl)phenyl]-3-(difluoromethyl)pyrazol-4-yl]-2-[2-(cyclopropyl methylamino)-4-pyridyl]oxazole-4-carboxamide (I-391)

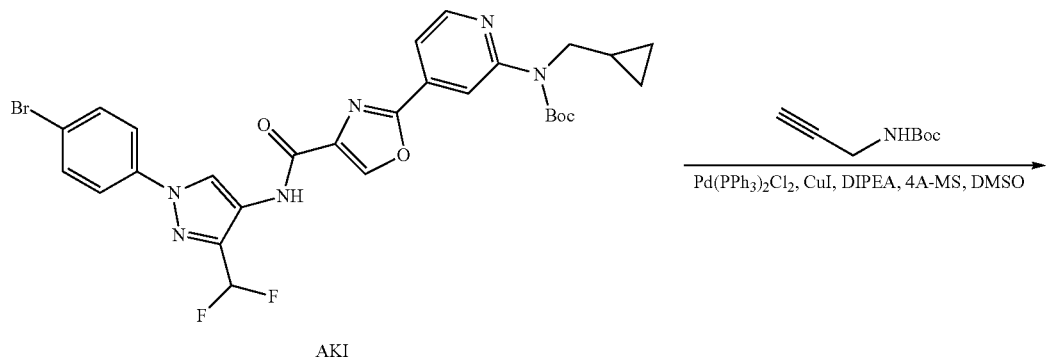

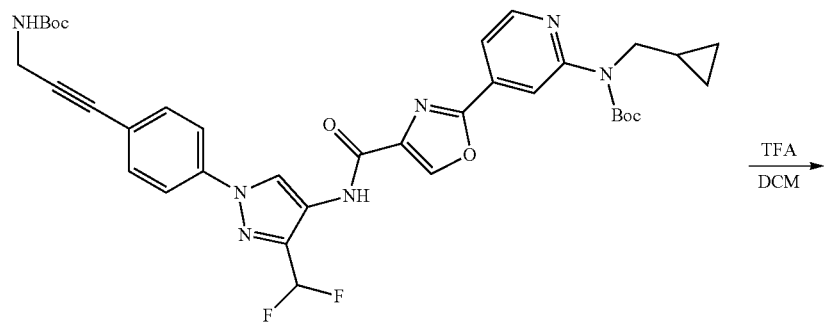

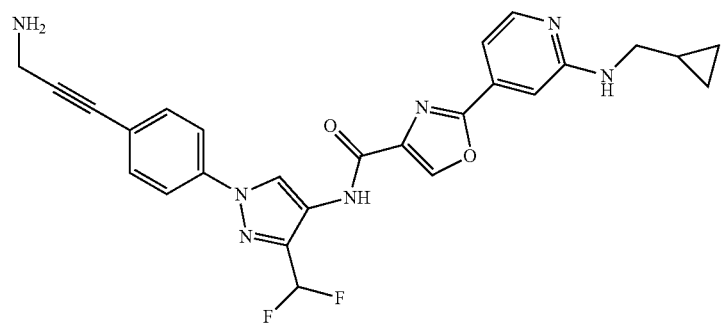

I-391

Step 1—Tert-butyl N-[4-[4-[[1-[4-[3-(tert-butoxycarbonylamino)prop-1-ynyl]phenyl]-3-(difluoromethyl)pyrazol-4-yl]carbamoyl]oxazol-2-yl]-2-pyridyl]-N-(cyclopropylmethyl)carbamate A mixture of tert-butyl N-[4-[4-[[1-(4-bromophenyl)-3-(difluoromethyl)pyrazol-4-yl]carbamoyl] oxazol-2-yl]-2-pyridyl]-N-(cyclopropylmethyl)carbamate (100 mg, 158 umol, Intermediate AKI), tert-butyl N-prop-2-ynylcarbamate (49.3 mg, 318 umol, CAS #92136-39-5), Pd(PPh$_3$)$_2$Cl$_2$ (11.2 mg, 15.9 umol), CuI (3.03 mg, 15.9 umol), DIPEA (103 mg, 794 umol, 138 uL) and 4 Å molecular sieves (100 mg) in DMSO (4.00 mL) was degassed and purged with N$_2$ for 3 times, and then the mixture was stirred at 80° C. for 2 hours under N$_2$ atmosphere. On completion, the reaction mixture was filtered and concentrated in vacuo to give a residue. The residue was purified by reversed-phase (0.1% FA condition) to give the title compound (90.0 mg, 80% yield) as a yellow solid. $^1$H NMR (400 MHz, Chloroform-d) δ 9.16 (s, 1H), 8.85 (s, 1H), 8.54 (d, J=4.8 Hz, 1H), 8.42 (s, 1H), 8.36 (s, 1H), 7.73-7.65 (m, 3H), 7.58-7.52 (m, 2H), 7.12-6.76 (m, 1H), 4.18 (d, J=4.8 Hz, 2H), 3.97 (d, J=7.0 Hz, 2H), 1.58 (s, 9H), 1.49 (s, 9H), 1.33-1.18 (m, 2H), 0.50-0.38 (m, 2H), 0.35-0.21 (m, 2H).

Step 2—N-[1-[4-(3-aminoprop-1-ynyl)phenyl]-3-(difluoromethyl)pyrazol-4-yl]-2-[2-(cyclopropylmethylamino)-4-pyridyl]oxazole-4-carboxamide To a solution of tert-butyl N-[4-[4-[[1-[4-[3-(tert-butoxycarbonylamino)prop-1-ynyl]phenyl]-3-(difluoromethyl)pyrazol-4-yl]carbamoyl]oxazol-2-yl]-2-pyridyl]-N-(cyclopropylmethyl)carbamate (80.0 mg, 113 umol) in DCM (2 mL) was added TFA (1.54 g, 13.5 mmol, 1.00 mL). The mixture was stirred at 20° C. for 1 hour. On completion, the reaction mixture was concentrated in vacuo to give a residue. The residue was purified by prep-HPLC (column: Waters Xbridge 150*25 mm*5 um; mobile phase: [water (0.05% ammoniahydroxide v/v)-ACN]; B %: 40%-70%, 0 min]; B %: 40%-70%,10 min) to give the title compound (26.8 mg, 46% yield) as a white solid. $^1$H NMR (400 MHz, DMSO-d$_6$) δ 10.46-9.62 (m, 1H), 8.97 (s, 1H), 8.84 (s, 1H), 8.16 (d, J=5.2 Hz, 1H), 7.87 (d, J=8.8 Hz, 2H), 7.55 (d, J=8.8 Hz, 2H), 7.46-7.14 (m, 1H), 7.13-7.06 (m, 2H), 7.04 (dd, J=1.3, 5.3 Hz, 1H), 3.53 (s, 2H), 3.18 (t, J=6.4 Hz, 2H), 2.15-1.62 (m, 2H), 1.14-0.99 (m, 1H), 0.51-0.41 (m, 2H), 0.26-0.17 (m, 2H). LC-MS (ESI$^+$) m/z 504.3 (M+H)$^+$.

Example 34. Synthesis of 2-[[[4-[4-[[2-[2-(Cyclopropylmethylamino)-4-pyridyl]oxazole-4-carbonyl] amino]-3-(difluoromethyl)pyrazol-1-yl] cyclohexyl] methyl-methyl-amino] methyl]-5-[3-[1-(2,6-dioxo-3-piperidyl)-3-methyl-2-oxo-benzimidazol-4-yl] propoxy]pentanoic acid (I-396)

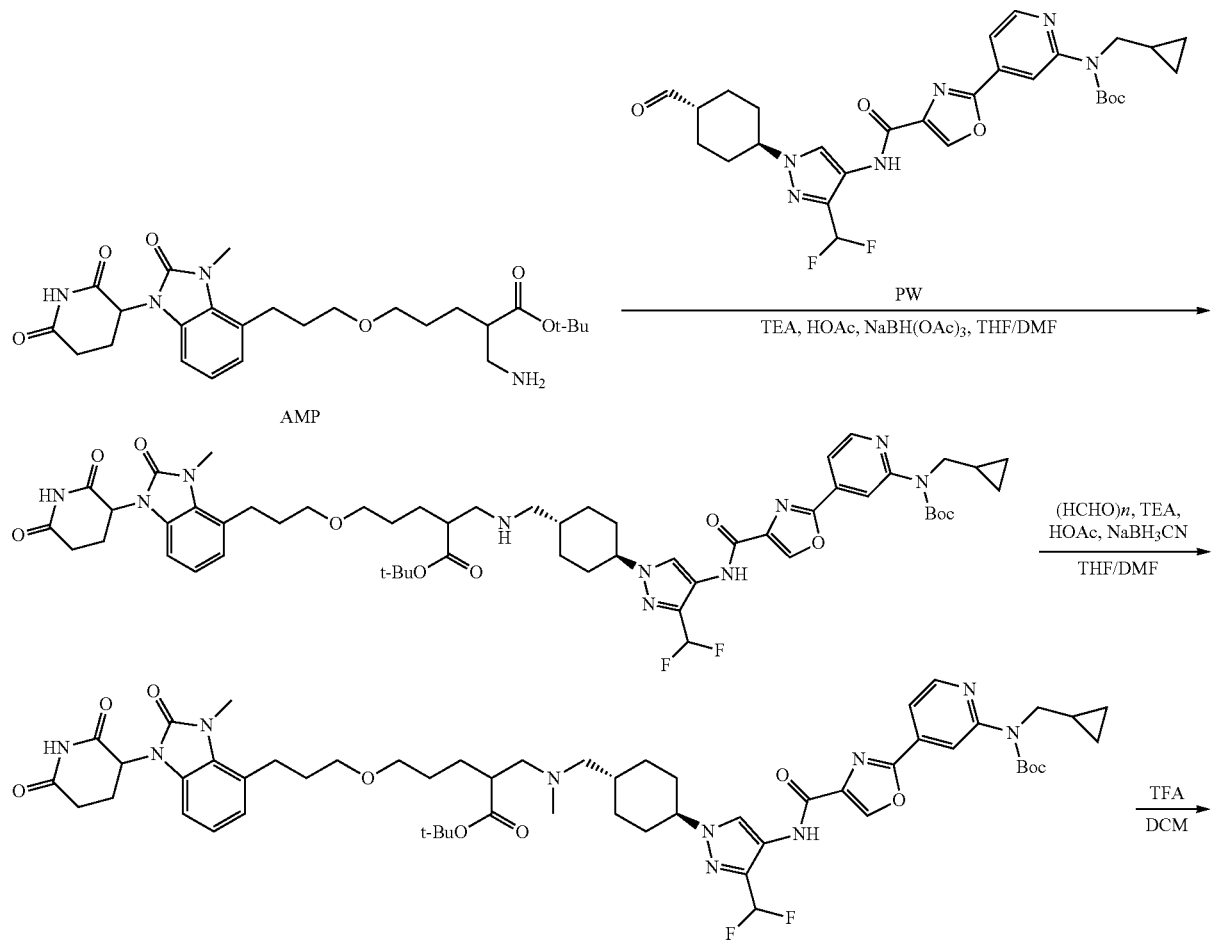

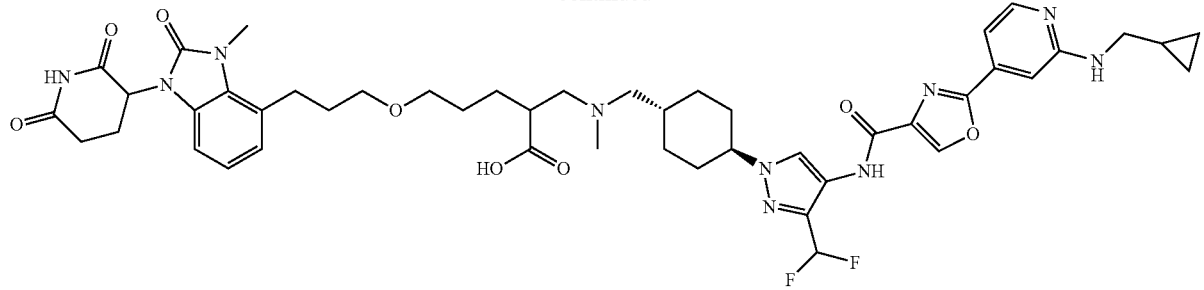

I-396

Step 1—Tert-butyl 2-[[[4-[4-[[2-[2-[tert-butoxycarbonyl(cyclopropylmethyl)amino]-4-pyridyl] oxazole-4-carbonyl amino]-3-(difluoromethyl)pyrazol-1-yl]cyclohexyl]methylamino]methyl]-5-[3-[1-(2,6-dioxo-3-piperidyl)-3-methyl-2-oxo-benzimidazol-4-yl]propoxy]pentanoate A mixture of tert-butyl 2-(aminomethyl)-5-[3-[1-(2,6-dioxo-3-piperidyl)-3-methyl-2-oxo-benzimidazol-4-yl]propoxy]pentanoate (100 mg, 198 umol, Intermediate AMP), tert-butylN-(cyclopropylmethyl)-N-[4-[4-[[3-(difluoromethyl)-1-(4-formylcyclohexyl)pyrazol-4-yl]carbamoyl]oxazol-2-yl]-2-pyridyl]carbamate (65.0 mg, 111 umol, Intermediate PW) and HOAc (35.8 mg, 596 umol) in THF (3 mL) and DMF (1 mL) was stirred at 0° C. for 0.5 hour. Then NaBH(OAc)$_3$ (51.0 mg, 240 umol) was added at 0° C. The mixture was stirred at 0-25° C. for 16 hours. On completion, the reaction was quenched with water (0.2 mL). The mixture was concentrated in vacuo. The residue was purified by reversed phase flash (FA condition) to give the title compound (90.0 mg, 42% yield) as light yellow solid. $^1$H NMR (400 MHz, DMSO-d$_6$) δ 11.09 (s, 1H), 9.76 (s, 1H), 9.00 (s, 1H), 8.59 (d, J=5.2 Hz, 1H), 8.29 (s, 1H), 8.17 (s, 1H), 7.69-7.68 (m, 1H), 7.29-7.00 (m, 1H), 6.96 (d, J=5.2 Hz, 2H), 6.89-6.81 (m, 1H), 5.43-5.31 (m, 1H), 4.23-4.12 (m, 1H), 3.86 (d, J=7.2 Hz, 2H), 3.56 (s, 3H), 3.41 (m, 4H), 2.98-2.83 (m, 3H), 2.77-2.69 (m, 1H), 2.65-2.52 (m, 4H), 2.42-2.34 (m, 4H), 2.05-1.94 (m, 3H), 1.92-1.79 (m, 5H), 1.77-1.66 (m, 2H), 1.51 (s, 9H), 1.50-1.48 (m, 2H), 1.40 (s, 9H), 1.27-1.12 (m, 2H), 1.11-0.98 (m, 2H), 0.42-0.41 (m, 2H), 0.24-0.23 (m, 2H).

Step 2—Tert-butyl 2-[[[4-[4-[[2-[2-[tert-butoxycarbonyl(cyclopropylmethyl)amino]-4-pyridyl] oxazole-4-carbonyl]amino]-3-(difluoromethyl)pyrazol-1-yl]cyclohexyl]methyl-methyl-amino]methyl]-5-[3-[1-(2,6-dioxo-3-piperidyl)-3-methyl-2-oxo-benzimidazol-4-yl]propoxy]pentanoate A mixture of tert-butyl 2-[[[4-[4-[[2-[2-[tert-butoxycarbonyl(cyclopropylmethyl)amino]-4-pyridyl] oxazole-4-carbonyl]amino]-3-(difluoromethyl)pyrazol-1-yl]cyclohexyl]methylamino]methyl]-5-[3-[1-(2,6-dioxo-3-piperidyl)-3-methyl-2-oxo-benzimidazol-4-yl]propoxy]pentanoate (90.0 mg, 84.0 umol), paraformaldehyde (8.00 mg, 88.0 umol, CAS #30525-89-4) and KOAc (2.05 mg, 254 umol) in THF (1.5 mL) and DMF (0.5 mL) was stirred at 25° C. for 0.5 hour. Then NaBH$_3$CN (8.00 mg, 127 umol) was added at 25° C. The mixture was stirred at 25° C. for 2 hours. On completion, the reaction was quenched with water (0.2 mL). The mixture was concentrated in vacuo. The residue was purified by reversed phase flash (FA condition) to give the title compound (65.0 mg, 71% yield) as light yellow solid. LC-MS (ESI$^+$) m/z 1085.2 (M+H)$^+$.

Step 3—2-[[[4-[4-[[2-[2-(Cyclropropylmethylamino)-4-pyridyl]oxazole-4-carbonyl]amino]-3-(difluoromethyl)pyrazol-1-yl]cyclohexyl]methyl-methylamino]methyl]-5-[3-[1-(2,6-dioxo-3-piperidyl)-3-methyl-2-oxo-benzimidazol-4-yl]propoxy]pentanoic acid To a solution of tert-butyl 2-[[[4-[4-[[2-[2-[tert-butoxycarbonyl(cyclopropylmethyl)amino]-4-pyridyl] oxazole-4-carbonyl]amino]-3-(difluoromethyl)pyrazol-1-yl]cyclohexyl]methyl-methyl-amino]methyl]-5-[3-[1-(2,6-dioxo-3-piperidyl)-3-methyl-2-oxo-benzimidazol-4-yl]propoxy] pentanoate (60.0 mg, 55.2 umol) in DCM (2 mL) was added TFA (1 mL) at 25° C. The mixture was stirred at 25° C. for 6 hours. On completion, the mixture was concentrated in vacuo. The residue was purified by prep-HPLC (column: Waters Xbridge 150*25 mm*5 um; mobile phase: [water (10 mM NH$_4$HCO$_3$)-ACN]; B %: 22%-52%, 10 min) to give the title compound (28.6 mg, 54% yield) as white solid. $^1$H NMR (400 MHz, DMSO-d$_6$) δ 11.07 (m, 1H), 9.67 (s, 1H), 8.91 (s, 1H), 8.17 (s, 1H), 8.15 (d, J=5.2 Hz, 1H), 7.30-6.83 (m, 8H), 5.38-5.33 (m, 1H), 4.22-4.13 (m, 1H), 3.56 (s, 3H), 3.44 (m, 2H), 3.20-3.16 (m, 4H), 2.99-2.83 (m, 4H), 2.65-2.57 (m, 2H), 2.25 (m, 1H), 2.22 (s, 3H), 2.20-2.15 (m, 1H), 2.07-1.88 (m, 5H), 1.87-1.72 (m, 5H), 1.65-1.43 (m, 6H), 1.12-0.98 (m, 3H), 0.49-0.41 (m, 2H), 0.26-0.17 (m, 2H); LC-MS (ESI$^+$) m/z 929.6 (M+H)$^+$.

Example 35. Synthesis of 5-((1R,4R)-2-oxa-5-azabicyclo [2.2.1]heptan-5-yl)-N-(3-(difluoromethyl)-1-((1r,4R)-4-(((4-(2-((2-(2,6-dioxopiperidin-3-yl)-1,3-dioxoisoindolin-4-yl)amino)ethyl)phenethyl)(methyl)amino)methyl)cyclohexyl)-1H-pyrazol-4-yl)pyrazolo 1,5-a] pyrimidine-3-carboxamide (I-336)

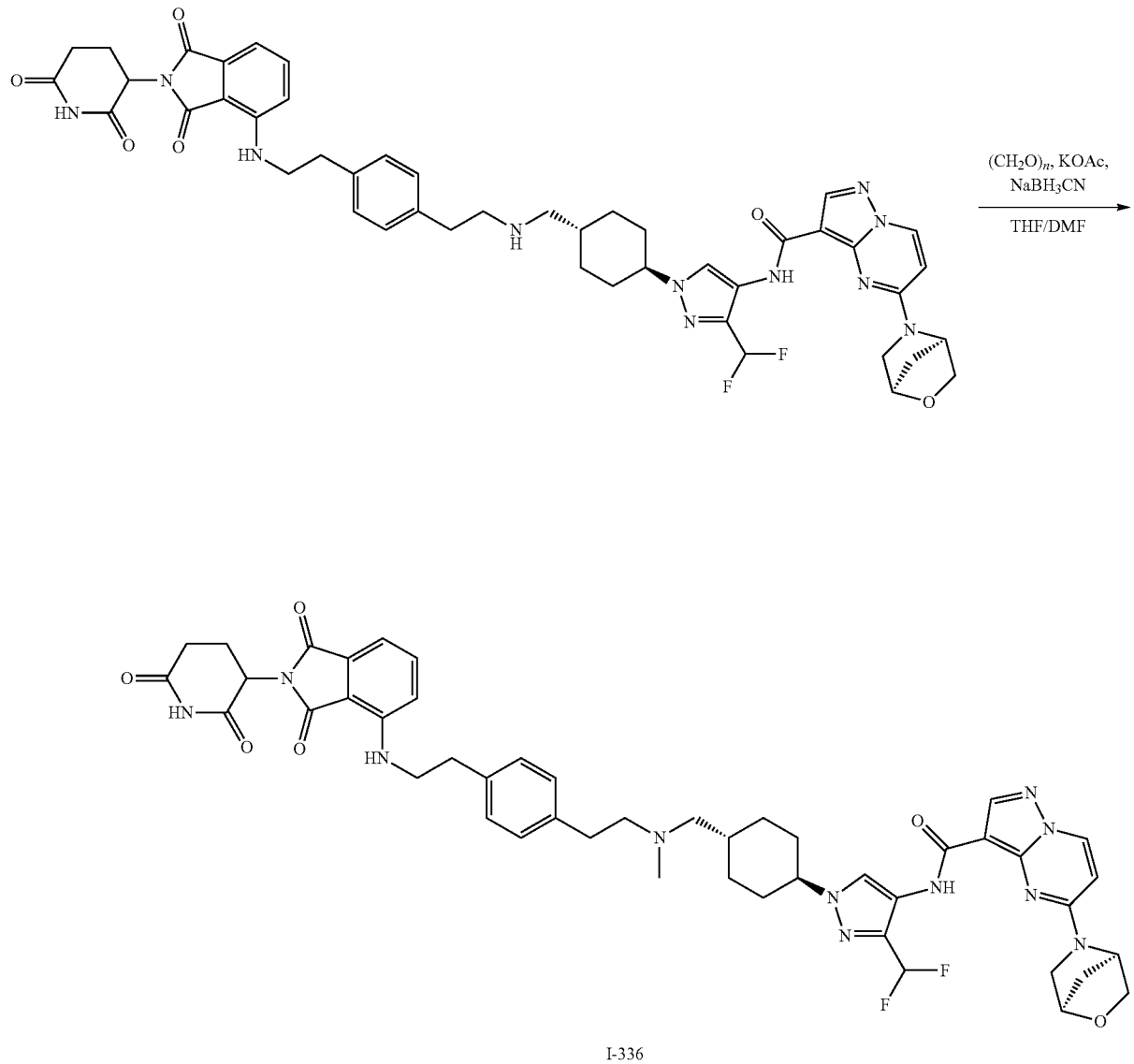

I-336

To a solution of N-[3-(difluoromethyl)-1-[4-[[2-[4-[2-[[2-(2,6-dioxo-3-piperidyl)-1,3-dioxo-isoindolin-4-yl]amino]ethyl]phenyl]ethylamino]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (30.0 mg, 33.7 umol, I-346) in DMF (1 mL) and THF (1 mL) was added $(CH_2O)_n$ (3.24 mg, 101 umol) and KOAc (16.5 mg, 168 umol). The mixture was stirred at 15° C. for 0.5 hr, then $NaBH_3CN$ (2.12 mg, 33.7 umol) was added to the mixture. The mixture was stirred at 15° C. for 2.5 hrs. On completion, the mixture was added 0.5 mL of water and concentrated to remove most of solvent in vacuo. The residue was purified by pre-HPLC (column: Phenomenex Synergi C18 150*25*10 um; mobile phase: [water (0.225% FA)-ACN]; B %: 22%-52%,10 min) to give the title compound (20.5 mg, 64% yield) as yellow solid. $^1H$ NMR (400 MHz, DMSO-$d_6$) δ 11.08 (s, 1H), 9.49 (d, J=6.4 Hz, 1H), 8.78 (d, J=7.6 Hz, 1H), 8.40-8.22 (m, 2H), 7.57 (dd, J=7.6, 8.4 Hz, 1H), 7.26-6.77 (m, 8H), 6.56-6.44 (m, 1H), 5.32-4.95 (m, 2H), 4.21-4.07 (m, 1H), 3.87-3.61 (m, 4H), 3.59-3.42 (m, 4H), 2.90-2.82 (m, 3H), 2.70-2.63 (m, 2H), 2.61-2.55 (m, 2H), 2.24-2.14 (m, 5H), 2.04-2.00 (m, 6H), 1.88-1.79 (m, 2H), 1.72-1.60 (m, 2H), 1.70 (br d, J=2.4 Hz, 1H), 1.05-0.95 (m, 2H); LC-MS (ESI$^+$) m/z 904.2 (M+1)$^+$.

Example 36. Synthesis of N-[3-(difluoromethyl)-1-[4-[[[4-[2-[[2-(2,6-dioxo-3-piperidyl)-1,3-dioxo-isoindolin-4-yl] amino] ethyl] phenyl] methyl-methyl-amino] methyl] cyclohexyl] pyrazol-4-yl]-5-[(1R,4R)-2-oxa-5-azabicyclo [2.2.1] heptan-5-yl] pyrazolo [1,5-a] pyrimidine-3-carboxamide (I-341)

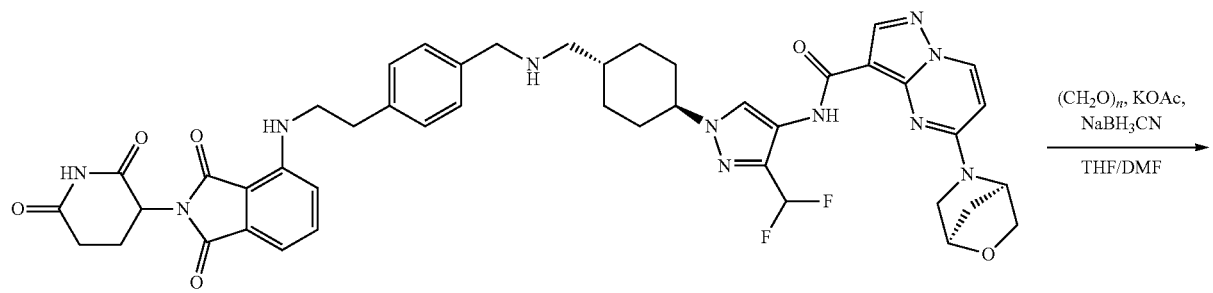

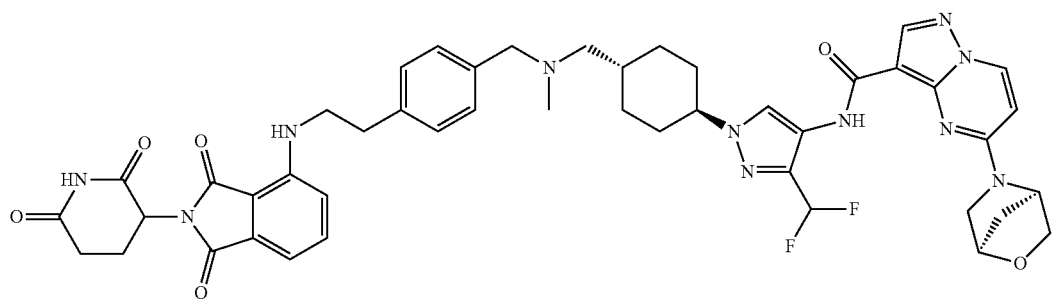

I-341

A mixture of N-[3-(difluoromethyl)-1-[4-[[[4-[2-[[2-(2,6-dioxo-3-piperidyl)-1,3-dioxo-isoindolin-4-yl] amino] ethyl] phenyl]methylamino]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (60.0 mg, 68.5 umol, I-351), and paraformaldehyde (6.20 mg, 205 umol, CAS #30525-89-4), KOAc (20.0 mg, 203 umol) in THF (1.2 mL) and DMF (0.4 mL) was stirred at 25° C. for 1 hour. Then NaBH$_3$CN (6.46 mg, 102 umol) was added to the reaction mixture at 25° C. The mixture was stirred at 25° C. for 2 hours. On completion, the reaction was quenched with water (0.2 mL). The mixture was concentrated in vacuo. The residue was purified by prep-HPLC (column: Waters Xbridge 150*25 mm*5 um; mobile phase: [water (10 mM NH$_4$HCO$_3$)-ACN]; B %: 43%-73%, 10 min) to give the title compound (38.2 mg, 60% yield) as yellow solid. $^1$H NMR (400 MHz, DMSO-d$_6$) δ 11.08 (s, 1H), 9.49 (d, J=6.0 Hz, 1H), 8.78 (d, J=7.6 Hz, 1H), 8.37 (d, J=4.0 Hz, 1H), 8.25 (d, J=5.6 Hz, 1H), 7.57 (t, J=8.0 Hz, 1H), 7.28-7.21 (m, 4H), 7.14 (d, J=8.8 Hz, 1H), 7.12-6.95 (m, 2H), 6.86 (d, J=8.0 Hz, 2H), 5.31-4.98 (m, 2H), 4.77 (d, J=16.4 Hz, 1H), 4.23-4.10 (m, 1H), 3.84-3.72 (m, 2H), 3.65-3.52 (m, 3H), 3.47-3.38 (m, 3H), 2.88 (t, J=6.8 Hz, 3H), 2.62-2.53 (m, 2H), 2.14-2.12 (m, 2H), 2.10 (s, 3H), 2.06-1.91 (m, 7H), 1.79-1.57 (m, 3H), 1.05-0.91 (m, 2H); LC-MS (ESI$^+$) m/z 890.4 (M+H)$^+$.

Example 37. Synthesis of 4-[2-[1-[2-[2-[[2-(2,6-dioxo-3-piperidyl)-1,3-dioxo-isoindolin-4-yl]amino]ethoxy]ethyl]-4-piperidyl]ethynyl]-1-[[(2S,3S,4S)-3-ethyl-4-fluoro-5-oxo-pyrrolidin-2-yl]methoxy]-7-methoxy-isoquinoline-6-carboxamide (I-357)

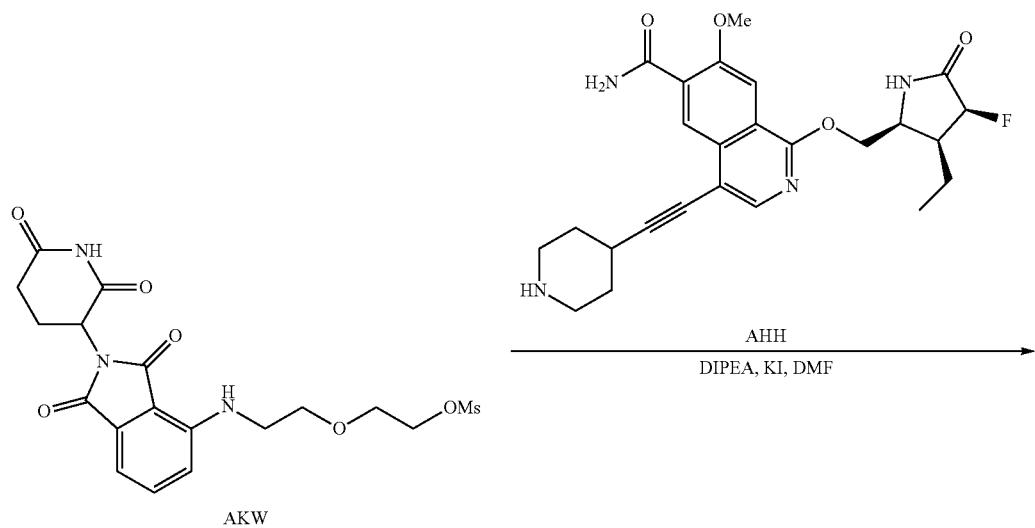

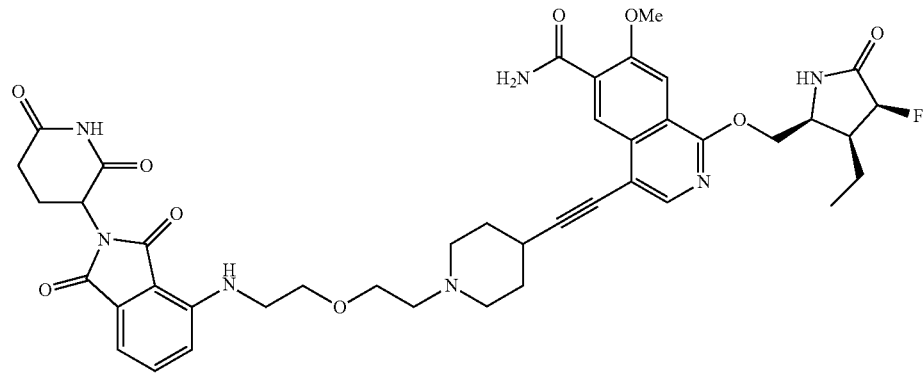

I-357

To a solution of 2-[2-[[2-(2,6-dioxo-3-piperidyl)-1,3-dioxo-isoindolin-4-yl]amino]ethoxy]ethyl methanesulfonate (75.4 mg, 171 umol, Intermediate AKW), 1-[[(2S,3S,4S)-3-ethyl-4-fluoro-5-oxo-pyrrolidin-2-yl]methoxy]-7-methoxy-4-[2-(4-piperidyl)ethynyl]isoquinoline-6-carboxamide (50.0 mg, 85.8 umol, TFA salt, Intermediate AHH) in DMF (2.00 mL) was added DIPEA (55.4 mg, 429 umol) and KI (1.42 mg, 8.58 umol). The reaction mixture was stirred at 80° C. for 3 hrs. On completion, the reaction mixture was concentrated in vacuo. The residue was purified by Prep-HPLC (column: Phenomenex Synergi C18 150*25*10 um; mobile phase: [water (0.225% FA)-ACN]; B %: 12%-42%, 10 min) to give the title compound (16.4 mg, 22% yield) as yellow solid. $^1$H NMR (400 MHz, DMSO-d$_6$) δ 11.09 (s, 1H), 8.88 (s, 1H), 8.33 (s, 1H), 8.25 (s, 1H), 8.04 (s, 1H), 7.90 (s, 1H), 7.77 (s, 1H), 7.75 (s, 1H), 7.62-7.52 (m, 1H), 7.15 (d, J=8.4 Hz, 1H), 7.03 (d, J=7.2 Hz, 1H), 6.65-6.58 (m, 1H), 5.10-5.02 (m, 1H), 5.00-4.82 (m, 1H), 4.60-4.50 (m, 1H), 4.32-4.22 (m, 1H), 4.16-4.07 (m, 1H), 3.99 (s, 3H), 3.64-3.60 (m, 2H), 3.60-3.57 (m, 2H), 3.51-3.48 (m, 2H), 3.46-3.45 (m, 2H), 2.91-2.83 (m, 1H), 2.81-2.70 (m, 3H), 2.66-2.54 (m, 2H), 2.32-2.23 (m, 2H), 2.06-1.99 (m, 1H), 1.95-1.85 (m, 2H), 1.71-1.56 (m, 4H), 1.02 (t, J=7.2 Hz, 3H), LC-MS (ESI$^+$) m/z 812.5 (M+H)$^+$.

Example 38. Synthesis of N-[3-(difluoromethyl)-1-[4-[3-[3-[1-(2,6-dioxo-3-piperidyl)-3-methyl-2-oxo-benzimidazol-4-yl]phenyl] propoxymethyl] cyclohexyl] pyrazol-4-yl]-5-morpholino-pyrazolo [1,5-a] pyrimidine-3-carboxamide

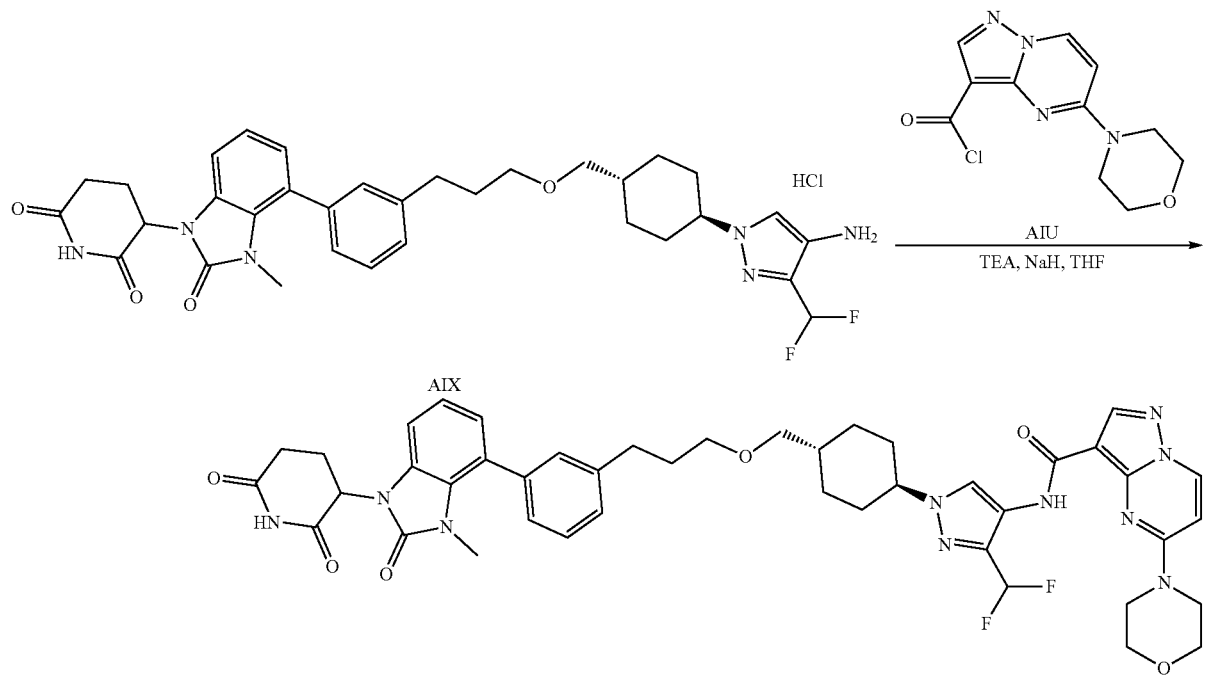

To a solution of 3-[4-[3-[3-[[4-[4-amino-3-(difluoromethyl)pyrazol-1-yl] cyclohexyl]methoxy] propyl]phenyl]-3-methyl-2-oxo-benzimidazol-1-yl]piperidine-2,6-dione (40.0 mg, 60.8 umol, HCl salt, Intermediate AIX) and TEA (18.4 mg, 182 umol) in THF (1 mL) was added NaH (9.74 mg, 243 umol, 60% dispersion in mineral oil) at 0° C. The mixture was stirred at 0° C. for 0.5 hr, then 5-morpholinopyrazolo [1,5-a]pyrimidine-3-carbonyl chloride (24.3 mg, 91.3 umol, Intermediate AIU) was added. The mixture was stirred at 20° C. for 2 hrs. On completion, the reaction was quenched with water (0.1 mL) and concentrated in vacuo to give a residue. The residue was purified by prep-HPLC (column: Phenomenex Synergi C18 150*25*10 um; mobile phase: [water (0.05% HCl)-ACN]) to give the title compound (1.78 mg, 3% yield, HCl salt) as yellow solid. $^1$H NMR (400 MHz, DMSO-d$_6$) δ11.13 (s, 1H), 8.76 (d, J=8.0 Hz, 1H), 8.26 (s, 1H), 7.85 (s, 1H), 7.43-7.36 (m, 1H), 7.32-7.24 (m, 3H), 7.23-6.95 (m, 3H), 6.90-6.85 (m, 2H), 5.44 (dd, J=5.2, 12.8 Hz, 1H), 4.19-4.10 (m, 1H), 4.03 (d, J=6.0 Hz, 2H), 3.78-3.68 (m, 8H), 3.08 (s, 2H), 2.89 (t, J=8.8 Hz, 2H), 2.84 (s, 3H), 2.77-2.70 (m, 3H), 2.68-2.64 (m, 1H), 2.08-1.90 (m, 7H), 1.81-1.65 (m, 3H), 1.34-1.19 (m, 2H); LC-MS (ESI$^+$) m/z 851.4 (M+H)$^+$.

Example 39. Synthesis of 2-[[[4-[3-(Difluoromethyl)-4-[[5-[(1R,4R)-2-oxa-5-azabicyclo [2.2.1] heptan-5-yl]pyrazolo [1,5-a]pyrimidine-3-carbonyl] amino] pyrazol-1-yl] cyclohexyl] methyl-methyl-amino] methyl]-5-[3-[1-(2,6-dioxo-3-piperidyl)-3-methyl-2-oxo-benzimidazol-4-yl]propoxy]pentanoic acid (I-495)

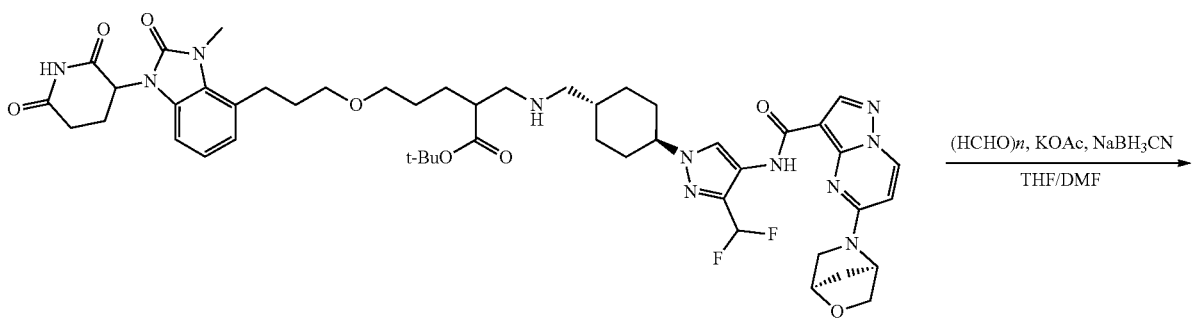

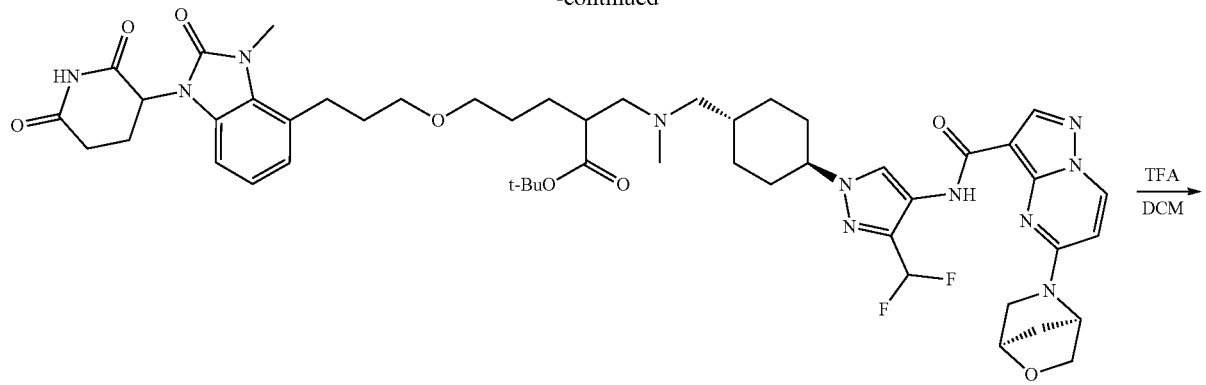

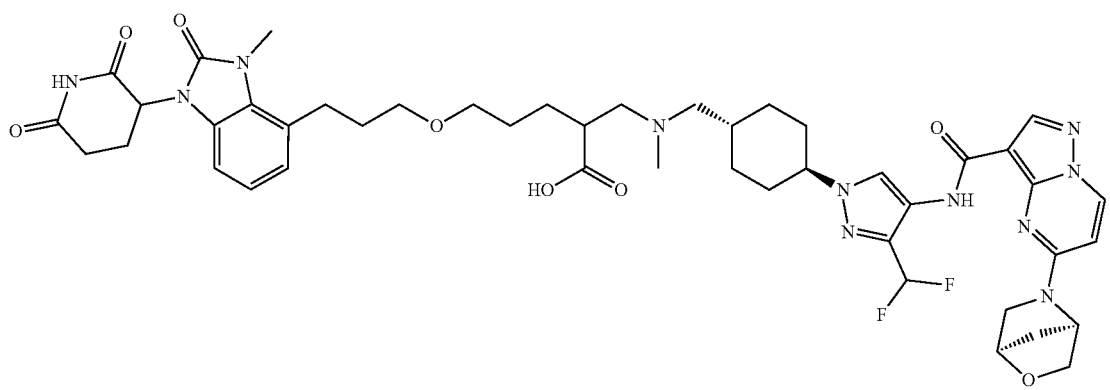

Step 1—Tert-butyl 2-[[[4-[3-(difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]cyclohexyl]methyl-methyl-amino]methyl]-5-[3-[1-(2,6-dioxo-3-piperidyl)-3-methyl-2-oxo-benzimidazol-4-yl]propoxy]pentanoate A mixture of tert-butyl 2-[[[4-[3-(difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]cyclohexyl]methylamino]methyl]-5-[3-[1-(2,6-dioxo-3-piperidyl)-3-methyl-2-oxo-benzimidazol-4-yl]propoxy]pentanoate (50.0 mg, 51.4 umol, synthesized via Step 1 of Method 2 using I-470), KOAc (15.0 mg, 152 umol) and paraformaldehyde (5.00 mg, 154 umol) in THF (1.2 mL) and DMF (0.4 mL) was stirred at 25° C. for 0.5 hour. Then NaBH$_3$CN (5.00 mg, 79.5 umol) was added at 25° C. and stirred for 2 hours. On completion, the reaction was quenched with water (0.2 mL). The mixture was concentrated in vacuo. The residue was purified by reversed phase flash (FA condition) to give the title compound (35.0 mg, 69% yield) as light yellow solid. LC-MS (ESI$^+$) m/z 986.5 (M+H)$^+$.

Step 2—2-[[[4-[3-(Difluoromethyl)-4-[[5-[(1R,4R)-2-oxa-5-azabicyclo[2.2.1]heptan-5-yl]pyrazolo[1,5-a]pyrimidine-3-carbonyl]amino]pyrazol-1-yl]cyclohexyl]methyl-methyl-amino]methyl]-5-[3-[1-(2,6-dioxo-3-piperidyl)-3-methyl-2-oxo-benzimidazol-4-yl]propoxy]pentanoic acid To a solution of tert-butyl 2-[[[4-[3-(difluoromethyl)-4-[[5-[(1R,4R)-2-oxa-5-azabicyclo[2.2.1] heptan-5-yl]pyrazolo[1,5-a]pyrimidine-3-carbonyl]amino]pyrazol-1-yl]cyclohexyl]methyl-methyl-amino]methyl]-5-[3-[1-(2,6-dioxo-3-piperidyl)-3-methyl-2-oxo-benzimidazol-4-yl]propoxy] pentanoate (35.0 mg, 35.4 umol) in DCM (1.5 mL) was added TFA (0.5 mL) at 25° C. The mixture was stirred at 25° C. for 3 hours. On completion, the mixture was concentrated in vacuo. The residue was purified by prep-HPLC (Phenomenex Synergi C18 150*25*10 um; mobile phase: [water (0.225% FA)-ACN]; B %: 21%-51%, 10 min) to give the title compound (10.8 mg, 33% yield) as white solid. $^1$H NMR (400 MHz, DMSO-d$_6$) δ 11.07 (s, 1H), 9.49 (d, J=6.4 Hz, 1H), 8.78 (d, J=8.0 Hz, 1H), 8.37 (d, J=4.0 Hz, 1H), 8.25 (d, J=5.6 Hz, 1H), 7.26-6.41 (m, 5H), 5.42-5.02 (m, 2H), 4.77 (d, J=16.4 Hz, 1H), 4.24-4.09 (m, 1H), 3.85-3.71 (m, 2H), 3.66-3.58 (m, 2H), 3.56 (s, 3H), 3.43 (m, 2H), 2.99-2.83 (m, 4H), 2.64-2.62 (m, 1H), 2.31-2.24 (m, 2H), 2.21 (s, 3H), 2.17-2.15 (m, 2H), 2.04-1.92 (m, 6H), 1.89-1.68 (m, 7H), 1.62-1.46 (m, 6H), 1.02-1.00 (m, 2H); LC-MS (ESI$^+$) m/z 930.6 (M+H)$^+$.

Example 40. Synthesis of N-[3-(difluoromethyl)-1-[2-[[[1-[[1-(2,6-dioxo-3-piperidyl)-3-methyl-2-oxo-benzimidazol-4-yl] methyl]-4-piperidyl]-methyl-amino] methyl]-1,3-dioxan-5-yl] pyrazol-4-yl]-5-[(1R,4R)-2-oxa-5-azabicyclo [2.2.1]heptan-5-yl] pyrazolo[1,5-a] pyrimidine-3-carboxamide (I-507)

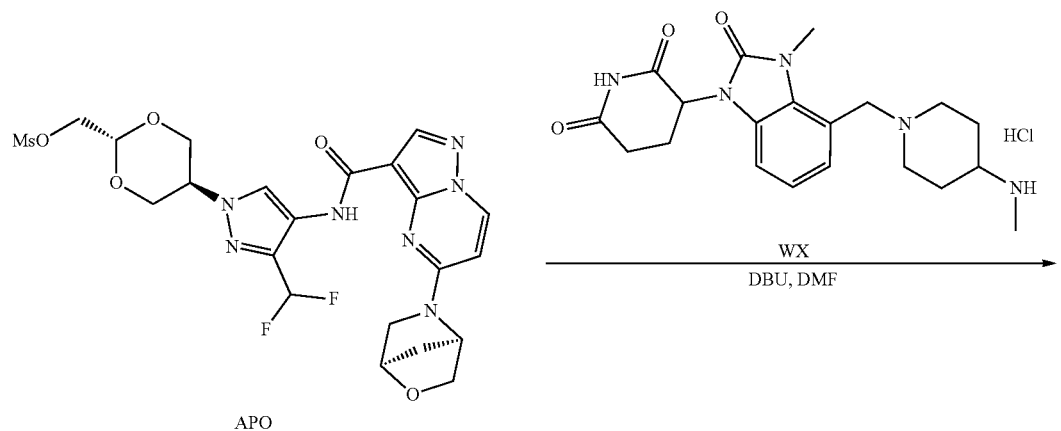

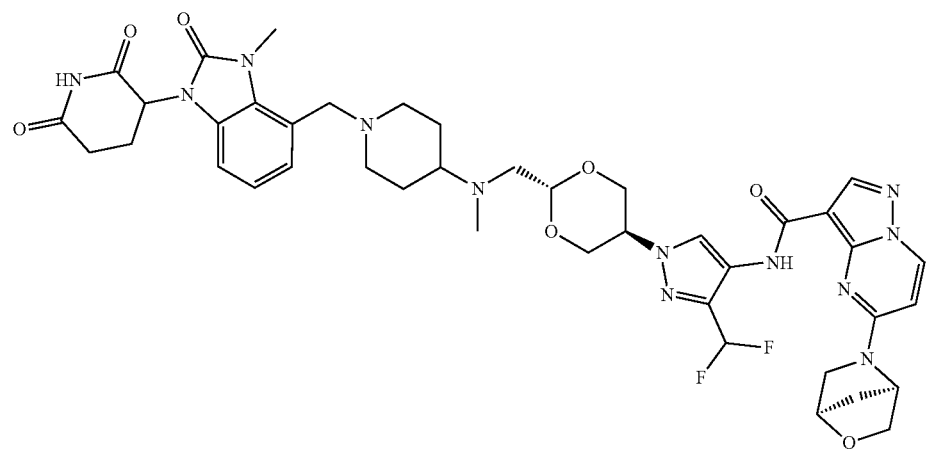

To a solution of 3-[3-methyl-4-[[4-(methylamino)-1-piperidyl]methyl]-2-oxo-benzimidazol-1-yl] piperidine-2,6-dione (18.5 mg, 43.9 umol, HCl, Intermediate WX) and [5-[3-(difluoromethyl)-4-[[5-[(1R,4R)-2-oxa-5-azabicyclo [2.2.1]heptan-5-yl]pyrazolo[1,5-a]pyrimidine-3-carbonyl] amino]pyrazol-1-yl]-1,3-dioxan-2-yl]methyl methanesulfonate (25.0 mg, 43.9 umol, Intermediate APO) in DMF (2 mL) was added DBU (13.4 mg, 87.7 umol, 13.2 uL). The reaction mixture was stirred at 100° C. for 12 hrs. On completion, the reaction mixture was quenched with water (0.5 mL) and concentrated in vacuo to give the residue. The residue was purified by Prep-HPLC (column: Waters Xbridge 150*25 mm*5 um; mobile phase: [water (10 mM NH$_4$HCO$_3$)-ACN]) (3 times) to give the title compound (1.02 mg, 2% yield) as a off-white solid. LC-MS (ESI$^+$) m/z 859.4 (M+1)$^+$.

Example 41. Synthesis of N-[3-(difluoromethyl)-1-[4-[5-[1-(2,6-dioxo-3-piperidyl)-3-methyl-2-oxo-benzimidazol-4-yl] pent-4-ynoxymethyl] phenyl] pyrazol-4-yl]-5-[(1R,4R)-2-oxa-5-azabicyclo [2.2.1] heptan-5-yl] pyrazolo[1,5-a]pyrimidine-3-carboxamide (I-498)

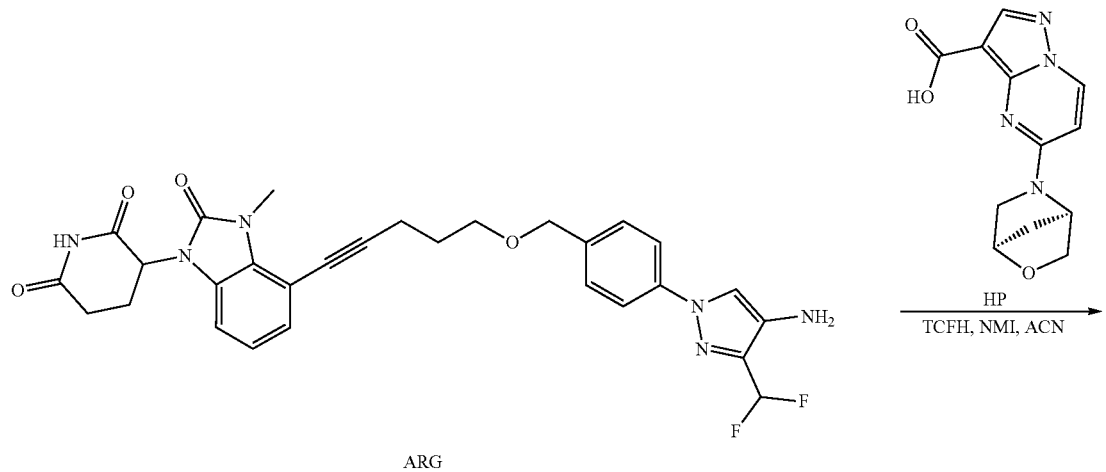

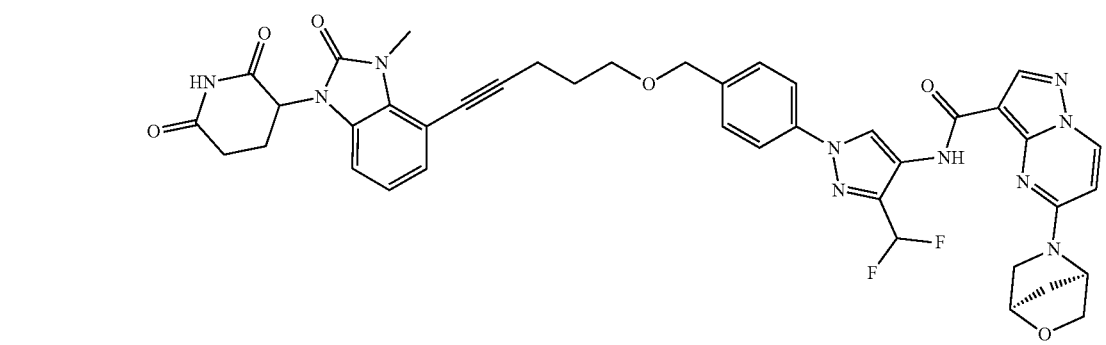

To a mixture of 5-[(1R)-2-oxa-5-azabicyclo[2.2.1]heptan-5-yl]pyrazolo[1,5-a]pyrimidine-3-carboxylic acid (23.1 mg, 88.8 umol, Intermediate AEH) in ACN (10 mL) was added [chloro (dimethylamino) methylene]-dimethyl-ammonium; hexafluorophosphate (32.4 mg, 115 umol) and 1-methylimidazole (25.5 mg, 311 umol). Then 3-[4-[5-[[4-[4-amino-3-(difluoromethyl)pyrazol-1-yl]phenyl]methoxy] pent-1-ynyl]-3-methyl-2-oxo-benzimidazol-1-yl]piperidine-2,6-dione (50.0 mg, 88.8 umol, Intermediate ARG) was added. The reaction mixture was stirred at 25° C. for 0.5 hour. On completion, the reaction mixture was concentrated in vacuo to give the residue. The residue was as purified by Prep-HPLC (column: Phenomenex Synergi C18 150*25*10 um; mobile phase: [water (0.225% FA)-ACN]; B %: 44%-74%) to give the title compound (24.3 mg, 34% yield) as a white solid. LC-MS (ESI⁺) m/z 805.4 (M+H)⁺; $^1$H NMR (400 MHz, DMSO-$d_6$) δ 11.09 (s, 1H), 9.61 (d, J=4.0 Hz, 1H), 8.96 (d, J=2.0 Hz, 1H), 8.80 (d, J=7.6 Hz, 1H), 8.31 (d, J=4.8 Hz, 1H), 7.79 (d, J=8.4 Hz, 2H), 7.49 (d, J=8.4 Hz, 2H), 7.45-7.14 (m, 1H), 7.10 (d, J=8.0 Hz, 1H), 7.06-7.01 (m, 1H), 7.00-6.94 (m, 1H), 6.91-6.45 (m, 1H), 5.38 (d, J=18.0 Hz, 1H), 5.33-5.06 (m, 1H), 4.79 (d, J=12.8 Hz, 1H), 4.55 (s, 2H), 3.84 (s, 2H), 3.67-3.63 (m, 2H), 3.62 (s, 3H), 3.61-3.44 (m, 2H), 2.93-2.82 (m, 1H), 2.67 (s, 1H), 2.64-2.56 (m, 3H), 2.09-1.95 (m, 3H), 1.88 (d, J=6.4 Hz, 2H).

Example 42. Synthesis of N-[3-(difluoromethyl)-1-[4-[[2-[[1-(2,6-dioxo-3-piperidyl)-3-methyl-2-oxo-benzimidazol-4-yl]methyl]-2,7-diazaspiro [3.5]nonan-7-yl]methyl]phenyl]pyrazol-4-yl]-5-[(1R)-2-oxa-5-azabicyclo [2.2.1]heptan-5-yl pyrazolo[1,5-a]pyrimidine-3-carboxamide (I-464)

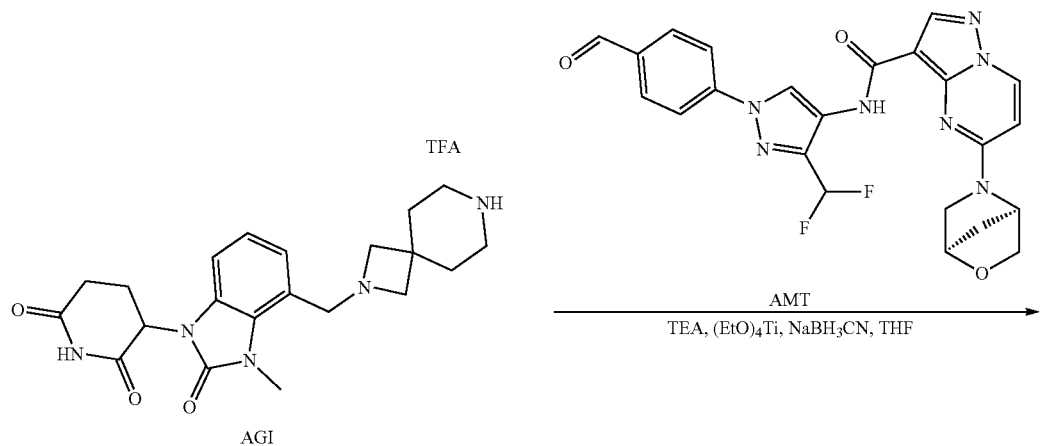

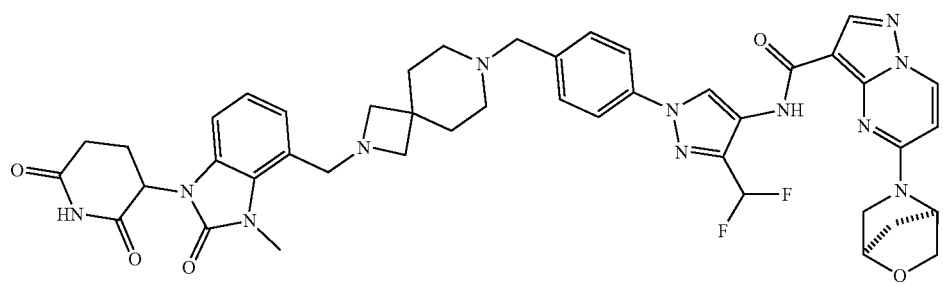

To a mixture of 3-[4-(2,7-diazaspiro[3.5]nonan-2-ylmethyl)-3-methyl-2-oxo-benzimidazol-1-yl] piperidine-2,6-dione (45.8 mg, 89.7 umol, TFA, Intermediate AGI) in THF (10 mL) was added TEA (27.2 mg, 269 umol). The mixture was stirred at 25° C. for 0.5 hour. N-[3-(difluoromethyl)-1-(4-formylphenyl)pyrazol-4-yl]-5-[(1R)-2-oxa-5-azabicyclo [2.2.1]heptan-5-yl]pyrazolo[1,5-a]pyrimidine-3-carboxamide (43.0 mg, 89.7 umol, Intermediate AMT) and tetraethoxytitanium (61.4 mg, 269 umol) was added. The reaction mixture was stirred at 80° C. for 11.5 hours. Then the reaction mixture was cooled to 25° C., and NaBH$_3$CN (16.9 mg, 269 umol) was added and stirred at 25° C. for 2 hours. On completion, the reaction was quenched with water (2 mL) and filtered. The filtrate was concentrated in vacuo to give the residue. The residue was purified by Prep-HPLC (column: Phenomenex Synergi C18 150*25*10 um; mobile phase: [water (0.225% FA)-ACN]; B %: 4%-34%) to give the title compound (8.28 mg, 9% yield) as a white slid. LC-MS (ESI$^+$) m/z 861.5 (M+H)$^+$. $^1$H NMR (400 MHz, DMSO-d$_6$) δ 11.09 (s, 1H), 9.60 (d, J=4.4 Hz, 1H), 8.96 (d, J=3.6 Hz, 1H), 8.80 (d, J=7.6 Hz, 1H), 8.30 (d, J=5.2 Hz, 1H), 7.77 (d, J=8.4 Hz, 2H), 7.42 (d, J=8.4 Hz, 2H), 7.30-6.45 (m, 5H), 5.36 (d, J=18.0 Hz, 1H), 5.32-5.07 (m, 1H), 4.78 (d, J=13.6 Hz, 1H), 3.83 (s, 2H), 3.80-3.73 (m, 3H), 3.67-3.62 (m, 5H), 2.93 (s, 4H), 2.90-2.83 (m, 1H), 2.77-2.58 (m, 3H), 2.28 (s, 3H), 2.08-1.92 (m, 4H), 1.67 (s, 4H).

Example 43. Synthesis of N-[3-(difluoromethyl)-1-[4-[methyl-[3-[3-[[2-(1-methyl-2,6-dioxo-3-piperidyl)-1,3-dioxo-isoindolin-4-yl] amino] propoxy] propylsulfonyl] carbamoyl] cyclohexyl] pyrazol-4-yl]-5-(2-oxa-5-azabicyclo [2.2.1]heptan-5-yl)pyrazolo [1,5-a]pyrimidine-3-carboxamide (I-490)
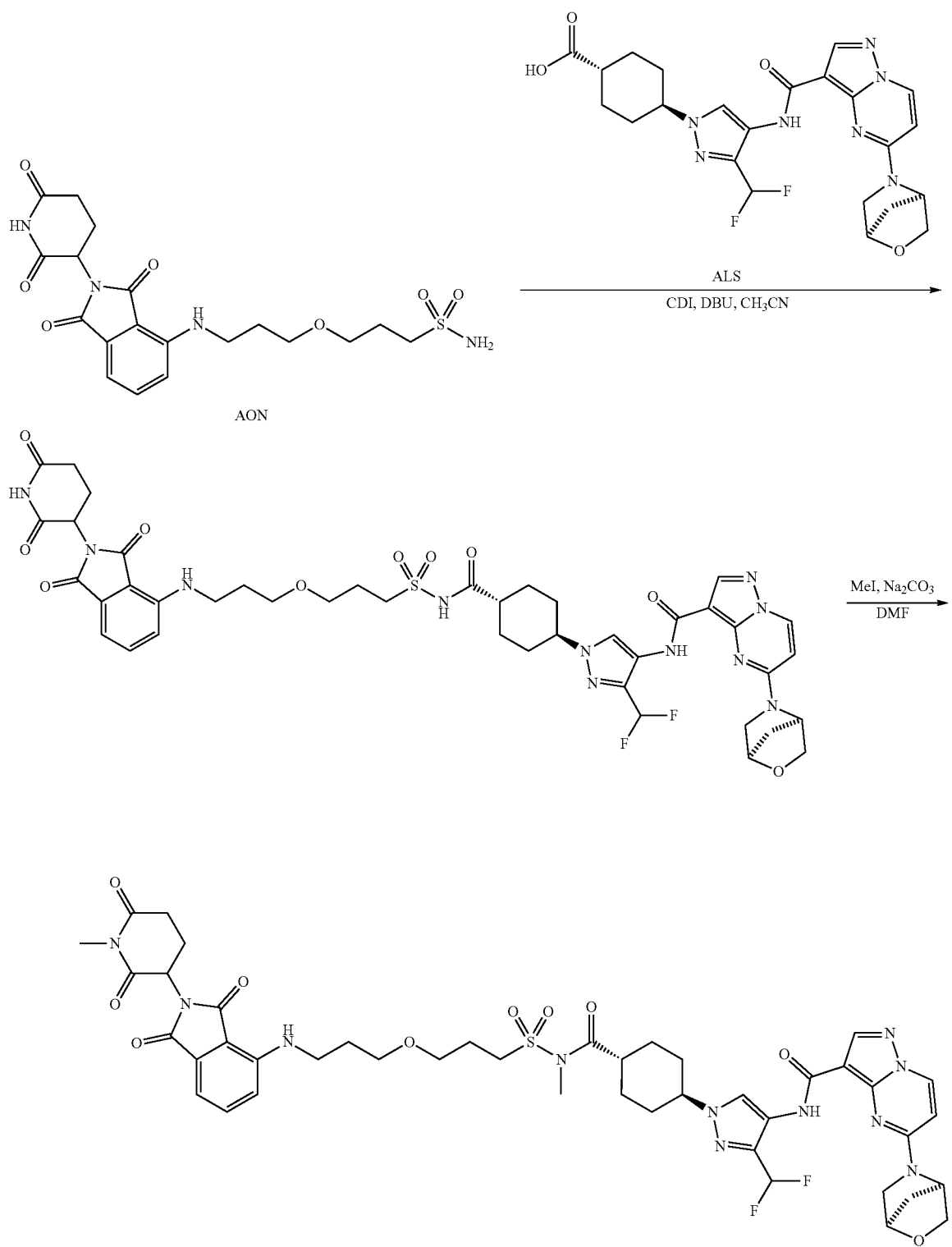

Step 1—N-[3-(difluoromethyl)-1-[4-[3-[3-[[2-(2,6-dioxo-3-piperidyl)-1,3-dioxo-isoindolin-4-yl]amino]propoxy]propylsulfonylcarbamoyl]cyclohexyl]pyrazol-4-yl]-5-(2-oxa-5-azabicyclo[2.2.1]heptan-5-yl)pyrazolo[1,5-a]pyrimidine-3-carboxamide To a mixture of 4-[3-(difluoromethyl)-4-[[5-(2-oxa-5-azabicyclo[2.2.1]heptan-5-yl)pyrazolo [1,5-a] pyrimidine-3-carbonyl]amino]pyrazol-1-yl]cyclohexanecarboxylic acid (44.3 mg, 88.4 umol, Intermediate ALS) in CH$_3$CN (10 mL) was added CDI (43.0 mg, 265 umol) at 25° C. The mixture was stirred at 25° C. for 3 hours. Then, a solution of 3-[3-[[2-(2,6-dioxo-3-piperidyl)-1,3-dioxo-isoindolin-4-yl]amino]propoxy]propane-1-sulfonamide (40 mg, 88.4 umol, Intermediate AON) in CH$_3$CN (2 mL) and DBU (26.9 mg, 176 umol) were added to the mixture. The reaction mixture was stirred at 25° C. for 2 hours. On completion, the reaction mixture was quenched with water (0.5 mL) at 25° C., and then concentrated in vacuo to give a residue. The residue was purified by reverse phase (FA conditions) to afford the title compound (15 mg, 18% yield) as a yellow solid. LC-MS (ESI$^+$) m/z 936.2 (M+H)$^+$.

Step 2—N-[3-(difluoromethyl)-1-[4-[methyl-[3-[3-[[2-(1-methyl-2,6-dioxo-3-piperidyl)-1,3-dioxo-isoindolin-4-yl]amino]propoxy]propylsulfonyl]carbamoyl] cyclohexyl]pyrazol-4-yl]-5-(2-oxa-5-azabicyclo[2.2.1]heptan-5-yl)pyrazolo[1,5-a]pyrimidine-3-carboxamide To a mixture of N-[3-(difluoromethyl)-1-[4-[3-[3-[[2-(2,6-dioxo-3-piperidyl)-1,3-dioxo-isoindolin-4-yl]amino]propoxy]propylsulfonylcarbamoyl] cyclohexyl]pyrazol-4-yl]-5-(2-oxa-5-azabicyclo[2.2.1]heptan-5-yl)pyrazolo[1,5-a]pyrimidine-3-carboxamide (15.0 mg, 16.0 umol) in DMF (1.0 mL) was added Na$_2$CO$_3$ (3.40 mg, 32.0 umol) at 25° C. Then MeI (22.7 mg, 160 umol) was added to the reaction mixture. The mixture was stirred at 25° C. for 2 hours. On completion, the reaction mixture was quenched with water (0.2 mL) at 25° C., and then concentrated in vacuo to give a residue. The residue was purified by prep-HPLC (column: Phenomenex Synergi C18 150*25*10 um; mobile phase: [water (0.225% FA)-ACN]; B %: 46%-76%, 10 min) to afford the title compound (3.0 mg, 19% yield) as a yellow solid. $^1$H NMR (400 MHz, DMSO-d$_6$) δ 9.50 (d, J=6.6 Hz, 1H), 8.77 (d, J=7.8 Hz, 1H), 8.39 (d, J=5.0 Hz, 1H), 8.25 (d, J=5.6 Hz, 1H), 7.62-7.54 (m, 1H), 7.25-6.93 (m, 3H), 6.88-6.42 (m, 2H), 5.29-5.04 (m, 2H), 4.76 (d, J=18.0 Hz, 1H), 4.33-4.20 (m, 1H), 3.85-3.71 (m, 2H), 3.63-3.58 (m, 3H), 3.51-3.45 (m, 5H), 3.24 (s, 3H), 3.01 (s, 3H), 2.98-2.95 (m, 1H), 2.94-2.91 (m, 1H), 2.89 (d, J=4.2 Hz, 1H), 2.79-2.74 (m, 1H), 2.74-2.69 (m, 1H), 2.61-2.55 (m, 1H), 2.09-1.99 (m, 4H), 1.99-1.91 (m, 5H), 1.88-1.78 (m, 4H), 1.60-1.49 (m, 2H). LC-MS (ESI$^+$) m/z 964.5 (M+H)$^+$.

Example 44. Synthesis of 5-((1R,4R)-2-oxa-5-azabicyclo[2.2.1]heptan-5-yl)-N-(3-(difluoromethyl)-1-((1r,4R)-4-(((5-(1-(2,6-dioxopiperidin-3-yl)-3-methyl-2-oxo-2,3-dihydro-1H-benzo [d] imidazol-4-yl)pent-4-yn-1-yl)(methyl)amino)methyl) cyclohexyl)-1H-pyrazol-4-yl)pyrazolo[1,5-a]pyrimidine-3-carboxamide (I-550)

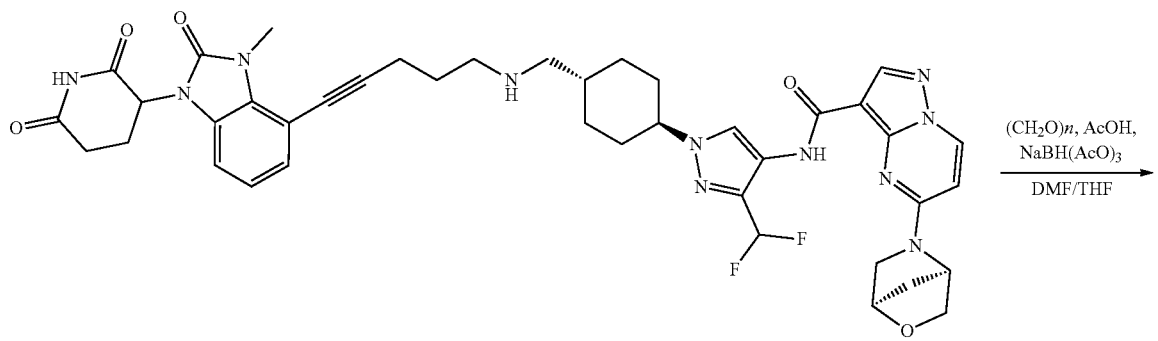

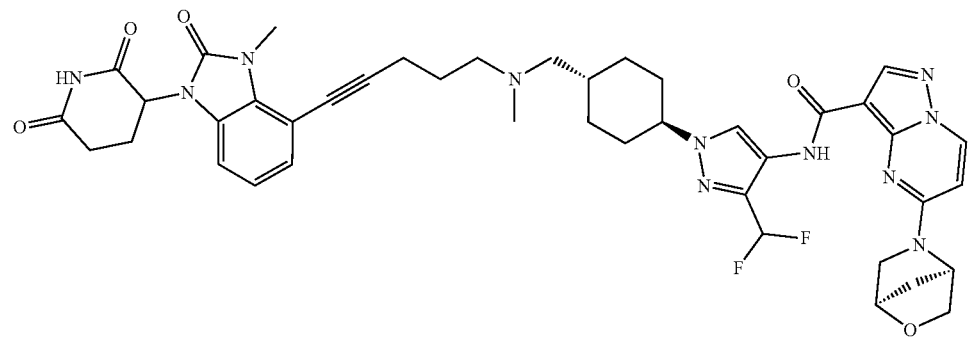

To a solution of N-[3-(difluoromethyl)-1-[4-[[5-[1-(2,6-dioxo-3-piperidyl)-3-methyl-2-oxo-benz imidazol-4-yl]pent-4-ynylamino]methyl]cyclohexyl]pyrazol-4-yl]-5-[(1R)-2-oxa-5-azabicyclo[2.2.1]heptan-5-yl]pyrazolo[1,5-a]pyrimidine-3-carboxamide (0.18 g, 216 umol, I-518) in DMF (2 mL) and THF (8 mL) was added HOAc (13.0 mg, 216 umol) and HCHO (130 mg, 4.31 mmol, 119 uL) under N$_2$. The mixture was stirred at 0° C. for 0.5 hr, then NaBH(OAc)$_3$ (1.14 g, 5.39 mmol) was added to the reaction mixture. The mixture was stirred at 0° C. for 1.5 hrs. On completion, the reaction mixture was quenched by addition H$_2$O (0.2 mL) and concentrated in vacuo to give a residue. The residue was purified by prep-HPLC (column: Waters Xbridge 150*25 mm*5 um; mobile phase: [water (10 mM NH$_4$HCO$_3$)-ACN]; B %: 36%-66%, 10 min) to give the title compound (81.9 mg, 46% yield) as a white solid. $^1$H NMR (400 MHz, DMSO-d$_6$) δ 11.10 (s, 1H), 9.49 (d, J=6.0 Hz, 1H), 8.78 (d, J=7.6 Hz, 1H), 8.43-8.19 (m, 2H), 7.27-6.40 (m, 5H), 5.38 (dd, J=5.6, 12.8 Hz, 1H), 5.30-4.94 (m, 1H), 4.79 (s, 1H), 4.16 (s, 1H), 3.86-3.38 (m, 8H), 2.92-2.80 (m, 1H), 2.70-2.65 (m, 1H), 2.41 (t, J=6.4 Hz, 2H), 2.29-1.46 (m, 19H), 1.17-0.91 (m, 2H); LC-MS (ESI$^+$) m/z 824.5 (M+H)$^+$.

Example 45. Synthesis of 5-((1R,4R)-2-oxa-5-azabicyclo[2.2.1]heptan-5-yl)-N-(3-(difluoromethyl)-1-((1r,4R)-4-(((5-(1-(2,6-dioxopiperidin-3-yl)-3-methyl-2-oxo-2,3-dihydro-1H-benzo[d]imidazol-5-yl)pent-4-yn-1-yl)(methyl)amino)methyl)cyclohexyl)-1H-pyrazol-4-yl)pyrazolo[1,5-a]pyrimidine-3-carboxamide (I-546)

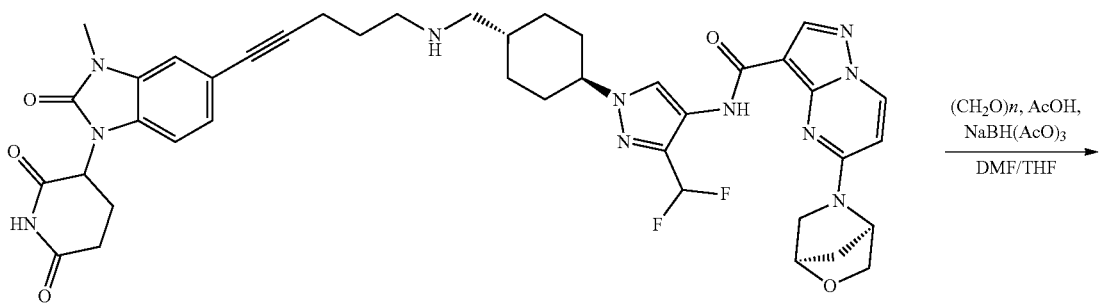

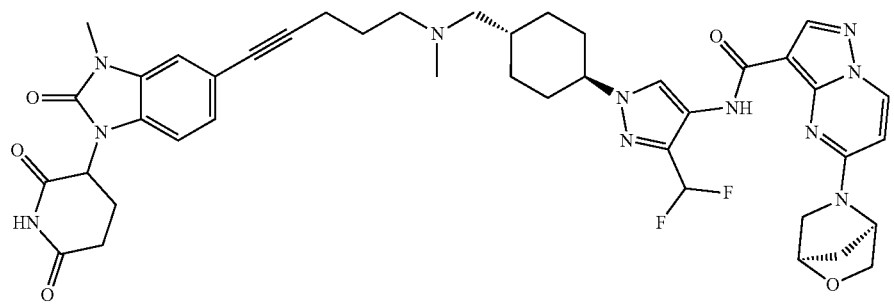

A solution of N-[3-(difluoromethyl)-1-[4-[[5-[1-(2,6-dioxo-3-piperidyl)-3-methyl-2-oxo-benzimidazol-5-yl]pent-4-ynylamino]methyl]cyclohexyl]pyrazol-4-yl]-5-(2-oxa-5-azabicyclo[2.2.1]heptan-5-yl)pyrazolo[1,5-a]pyrimidine-3-carboxamide (130 mg, 160 umol, I-512), Formaldehyde (24.1 mg, 802 umol) in a mixture solvent of THF (9.0 mL) and DMF (3 mL) was added TEA (16.2 mg, 160 umol). The mixture was stirred at 20° C. for 0.5 hr. Then HOAc (19.2 mg, 321 umol) was added into the above mixture. The mixture was stirred at 40° C. for 0.5 hr. Next, NaBH(OAc)$_3$ (170 mg, 802 umol) was added and the resulting reaction was stirred at 25° C. for 12 hrs. On completion, the reaction mixture was quenched with water (0.1 mL) and concentrated in vacuo. The residue was purified by prep-HPLC (column: Waters Xbridge 150*25 mm*5 um; mobile phase: [water (10 mM NH$_4$HCO$_3$)-ACN]; B %: 34%-64%, 10 min) to give the title compound (22.0 mg, 16% yield) as off-white solid. $^1$H NMR (400 MHz, DMSO-d$_6$) δ 11.11 (s, 1H), 9.50 (d, J=6.0 Hz, 1H), 8.79 (d, J=7.6 Hz, 1H), 8.37 (d, J=4.0 Hz, 1H), 8.27 (d, J=5.6 Hz, 1H), 7.10 (s, 2H), 7.27-6.93 (m, 2H), 6.91-6.40 (m, 1H), 5.37 (dd, J=5.2, 12.8 Hz, 1H), 5.30-5.07 (m, 1H), 4.78 (d, J=18.0 Hz, 1H), 4.24-4.13 (m, 1H), 3.87-3.72 (m, 2H), 3.66-3.44 (m, 2H), 3.33 (s, 3H), 2.94-2.82 (m, 1H), 2.68 (s, 2H), 2.46-2.38 (m, 4H), 2.21-2.11 (m, 5H), 2.08-1.91 (m, 7H), 1.79-1.65 (m, 4H), 1.62-1.51 (m, 1H), 1.11-0.99 (m, 2H); LC-MS (ESI$^+$) m/z 824.4 (M+H)$^+$.

Example 46. Synthesis of N-[3-(difluoromethyl)-1-[2-[[4-[3-[[2-(2,6-dioxo-3-piperidyl)-1,3-dioxo-isoindolin-4-yl] amino] propoxy]-1-piperidyl] methyl]-1,3-dioxan-5-yl]pyrazol-4-yl]-5-morpholino-pyrazolo [1,5-a] pyrimidine-3-carboxamide (I-451)

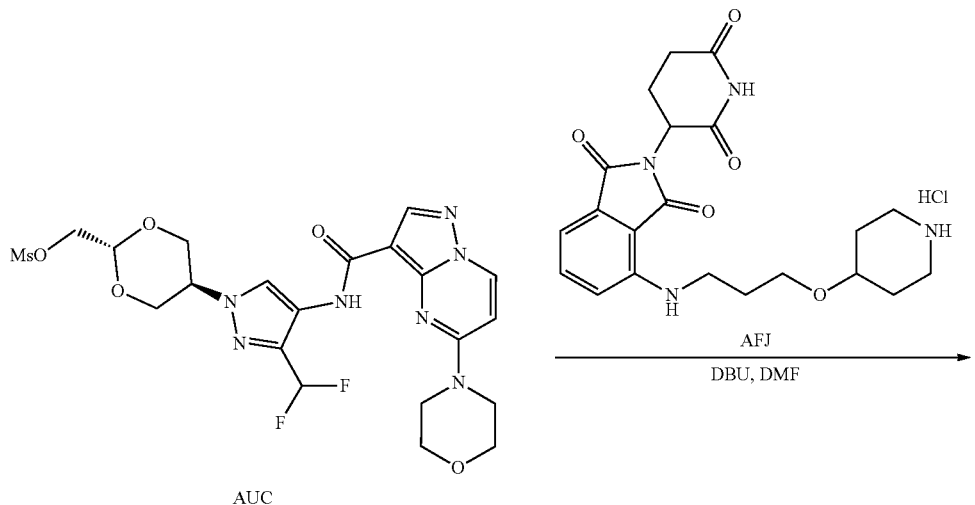

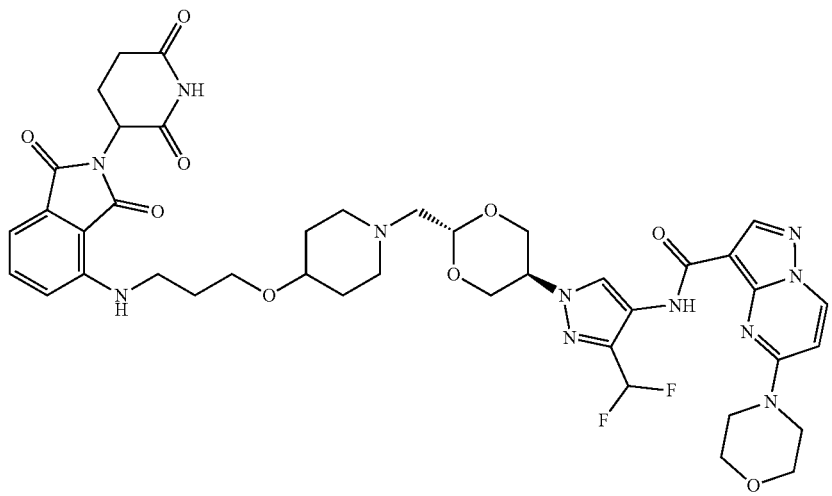

To a mixture of [5-[3-(difluoromethyl)-4-[(5-morpholino-pyrazolo[1,5-a]pyrimidine-3-carbonyl)amino] pyrazol-1-yl]-1,3-dioxan-2-yl]methylmethanesulfonate (35.0 mg, 62.7 umol, Intermediate AUC) and 2-(2,6-dioxo-3-piperidyl)-4-[3-(4-piperidyloxy)propylamino]isoindoline-1,3-dione (31.2 mg, 75.3 umol, Intermediate AFJ) in DMF (5 mL) was added DBU (19.1 mg, 125 umol, 18.9 uL) at 25° C. The mixture was stirred at 100° C. for 20 hours. On completion, the reaction mixture was quenched by water (0.5 mL) at 25° C., and then concentrated in vacuo to give a residue. The residue was purified by prep-HPLC (column: Waters Xbridge 150*25 mm*5 um; mobile phase: [water (10 mM $NH_4HCO_3$)-ACN]; B %: 27%-57%, 10 min) to afford the title compound (0.75 mg, 1.4% yield) as a yellow solid. $^1$H NMR (400 MHz, ACN-$d_3$) δ 9.46 (s, 1H), 8.46-8.41 (m, 2H), 8.29 (s, 1H), 7.60-7.51 (m, 1H), 7.06-7.01 (m, 2H), 6.99-6.71 (m, 1H), 6.63 (d, J=8.0 Hz, 1H), 6.55 (t, J=4.8 Hz, 1H), 4.96-4.90 (m, 1H), 4.87 (s, 1H), 4.58-4.49 (m, 1H), 4.34-4.28 (m, 2H), 4.08-3.99 (m, 2H), 3.77 (s, 8H), 3.56 (t, J=5.8 Hz, 2H), 3.45-3.35 (m, 3H), 3.03-2.88 (m, 2H), 2.79-2.49 (m, 6H), 1.90-1.86 (m, 4H), 1.79-1.75 (m, 1H), 1.72-1.62 (m, 3H), 1.24 (t, J=7.4 Hz, 1H); LC-MS (ESI$^+$) m/z 876.3 (M+H)$^+$.

Example 47. Synthesis of N-(3-(difluoromethyl)-1-((1r,4r)-4-(((((6-(3-((2-(2,6-dioxopiperidin-3-yl)-1,3-dioxoisoindolin-4-yl)amino)propoxy)pyridin-3-yl)methyl)(methyl)amino)methyl)cyclohexyl)-1H-pyrazol-4-yl)-5-morpholinopyrazolo[1,5-a]pyrimidine-3-carboxamide (I-477)

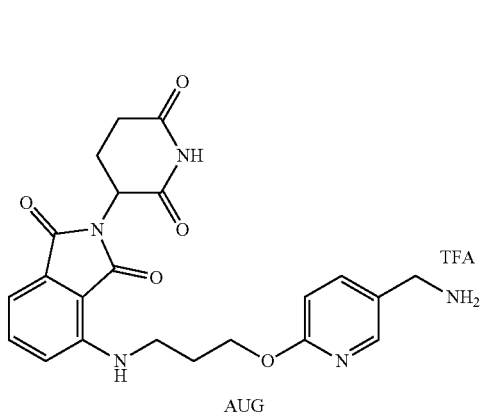
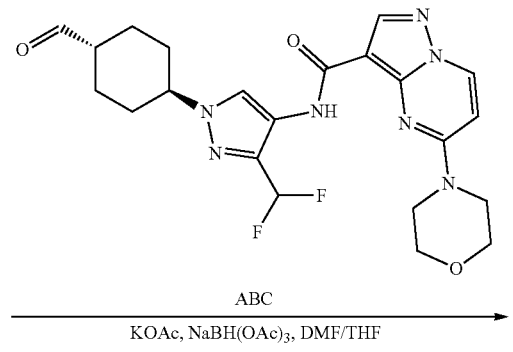
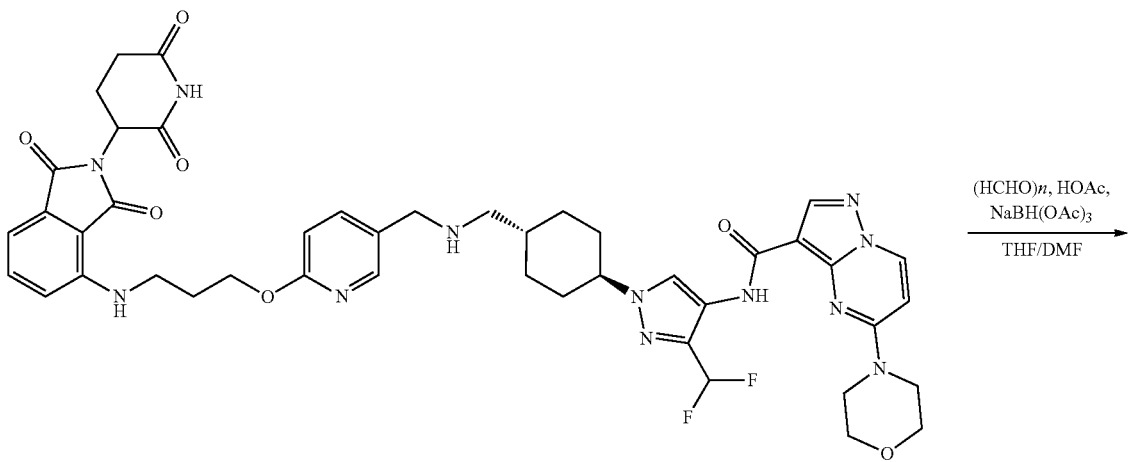

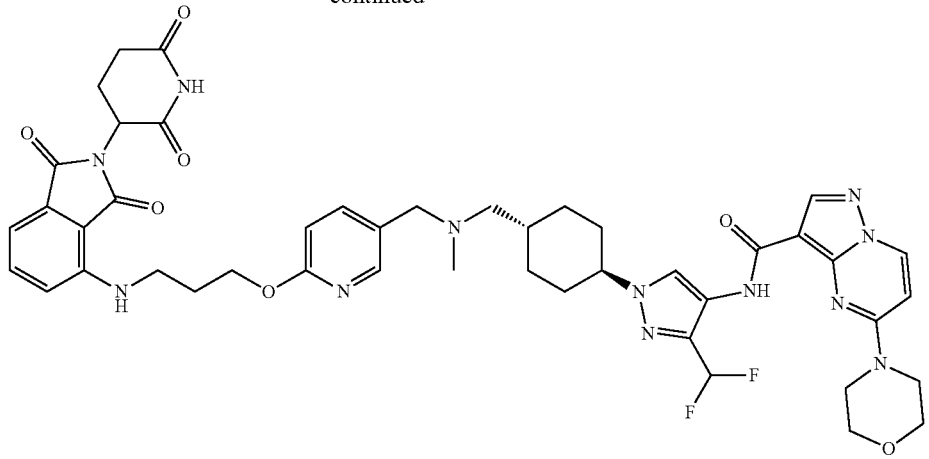

Step 1—N-(3-(difluoromethyl)-1-((1r,4r)-4-(((((6-(3-((2-(2,6-dioxopiperidin-3-yl)-1,3-dioxoisoindolin-4-yl)amino)propoxy)pyridin-3-yl)methyl)amino)methyl)cyclohexyl)-1H-pyrazol-4-yl)-5-morpholinopyrazolo[1,5-a]pyrimidine-3-carboxamide To a solution of 4-[3-[[5-(aminomethyl)-2-pyridyl]oxy]propylamino]-2-(2,6-dioxo-3-piperidyl) isoindoline-1,3-dione (50.0 mg, 77.9 umol, Intermediate AUG) in DMF (1 mL) and THF (4 mL) was added KOAc (11.4 mg, 116 umol). N-[3-(difluoromethyl)-1-(4-formylcyclohexyl)pyrazol-4-yl]-5-morpholino-pyrazolo[1,5-a]pyrimidine-3-carboxamide (36.9 mg, 77.9 umol, Intermediate ABC) was added at −10° C. The mixture was stirred at −10° C. for 0.5 hour. Next, NaBH(OAc)$_3$ (49.5 mg, 233 umol) was added and the mixture was stirred at 0° C. for 2 hours. The reaction was quenched with water (0.1 mL) and the mixture was concentrated in vacuo. The residue was purified by Prep-HPLC(Neu: column: Waters Xbridge 150*25 mm*5 um; mobile phase: [water (10 mM NH$_4$HCO$_3$)-ACN]; B %: 30%-60%, 10 min) to give the title compound (40.0 mg, 56% yield) as a yellow solid. $^1$H NMR (400 MHz, DMSO-d$_6$) δ 9.39 (s, 1H), 8.78 (d, J=7.6 Hz, 1H), 8.35 (s, 1H), 8.28 (s, 1H) 8.08-8.01 (m, 1H), 7.70-7.51 (m, 2H), 7.24-6.69 (m, 7H), 5.04 (d, J=7.2 Hz, 1H), 4.33 (s, 2H), 3.77 (d, J=4.8 Hz, 7H), 3.71 (s, 8H), 2.07-1.97 (m, 5H), 1.95-1.84 (m, 3H), 1.76-1.64 (m, 3H), 1.49-1.35 (m, 2H), 1.10-0.99 (m, 2H); LC-MS (ESI$^+$) m/z 894.9 (M+H)$^+$.

Step 2—N-(3-(difluoromethyl)-1-((1r,4r)-4-(((((6-(3-((2-(2,6-dioxopiperidin-3-yl)-1,3-dioxoisoindolin-4-yl)amino)propoxy)pyridin-3-yl)methyl)(methyl)amino)methyl)cyclohexyl)-1H-pyrazol-4-yl)-5-morpholinopyrazolo[1,5-a]pyrimidine-3-carboxamide To a solution of N-[3-(difluoromethyl)-1-[4-[[[6-[3-[[2-(2,6-dioxo-3-piperidyl)-1,3-dioxo-isoindolin-4-yl]amino]propoxy]-3-pyridyl]methylamino]methyl]cyclohexyl]pyrazol-4-yl]-5-morpholino-pyrazolo[1,5-a]pyrimidine-3-carboxamide (30.0 mg, 33.5 umol) in DMF (0.5 mL) and THF (2 mL) was added AcOH (402 ug, 6.70 umol). Paraformaldehyde (10.0 mg, 335 umol) was added and the mixture was stirred at 0° C. for 0.2 hour. Next, NaBH(OAc)$_3$ (85.2 mg, 402 umol) was added and the mixture was stirred at 0° C. for 2 hours. On completion, the mixture was filtered and the filtrate was concentrated in vacuo. The residue was purified by prep-HPLC (Neu: column: Waters Xbridge 150*25 mm*5 um; mobile phase: [water (10 mM NH$_4$HCO$_3$)-ACN]; B %: 55%-75%, 10 min) to give the title compound (7.00 mg, 23% yield) as a yellow solid. $^1$H NMR (400 MHz, DMSO-d$_6$) δ 9.39 (s, 1H), 8.82 (d, J=8.0 Hz, 1H), 8.36 (s, 1H), 8.28 (s, 1H), 8.02 (s, 1H), 7.61-7.54 (m, 2H), 7.13-6.82 (m, 6H), 5.07 (m, 1H), 4.36-4.33 (m, 2H), 4.16 (m, 1H), 3.79-3.71 (m, 8H), 3.48-3.38 (m, 5H), 2.60 (m, 1H), 2.57-2.55 (m, 2H), 2.13-2.11 (m, 5H), 2.04-2.01 (m, 5H), 1.93-1.90 (m, 2H), 1.73 (m, 2H), 1.60 (m, 1H), 1.01-0.92 (m, 2H); LC-MS (ESI$^+$) m/z 908.9 (M+H)$^+$.

Examples 48. Synthesis of N-[3-(difluoromethyl)-1-[4-[[4-[3-[1-[(3S)-2,6-dioxo-3-piperidyl]-3-methyl-2-oxo-benzimidazol-4-yl] prop-2-ynoxy]-1-piperidyl]methyl] cyclohexyl]pyrazol-4-yl]-5-[(1R,4R)-2-oxa-5-azabicyclo [2.2.1] heptan-5-yl] pyrazolo [1,5-a] pyrimidine-3-carboxamide (I-560) and N-[3-(difluoromethyl)-1-[4-[[4-[3-[1-[(3R)-2,6-dioxo-3-piperidyl]-3-methyl-2-oxo-benzimidazol-4-yl]prop-2-ynoxy]-1-piperidyl]methyl cyclohexyl]pyrazol-4-yl]-5-[(1R,4R)-2-oxa-5-azabicyclo [2.2.1] heptan-5-yl] pyrazolo [1,5-a] pyrimidine-3-carboxamide (I-561)

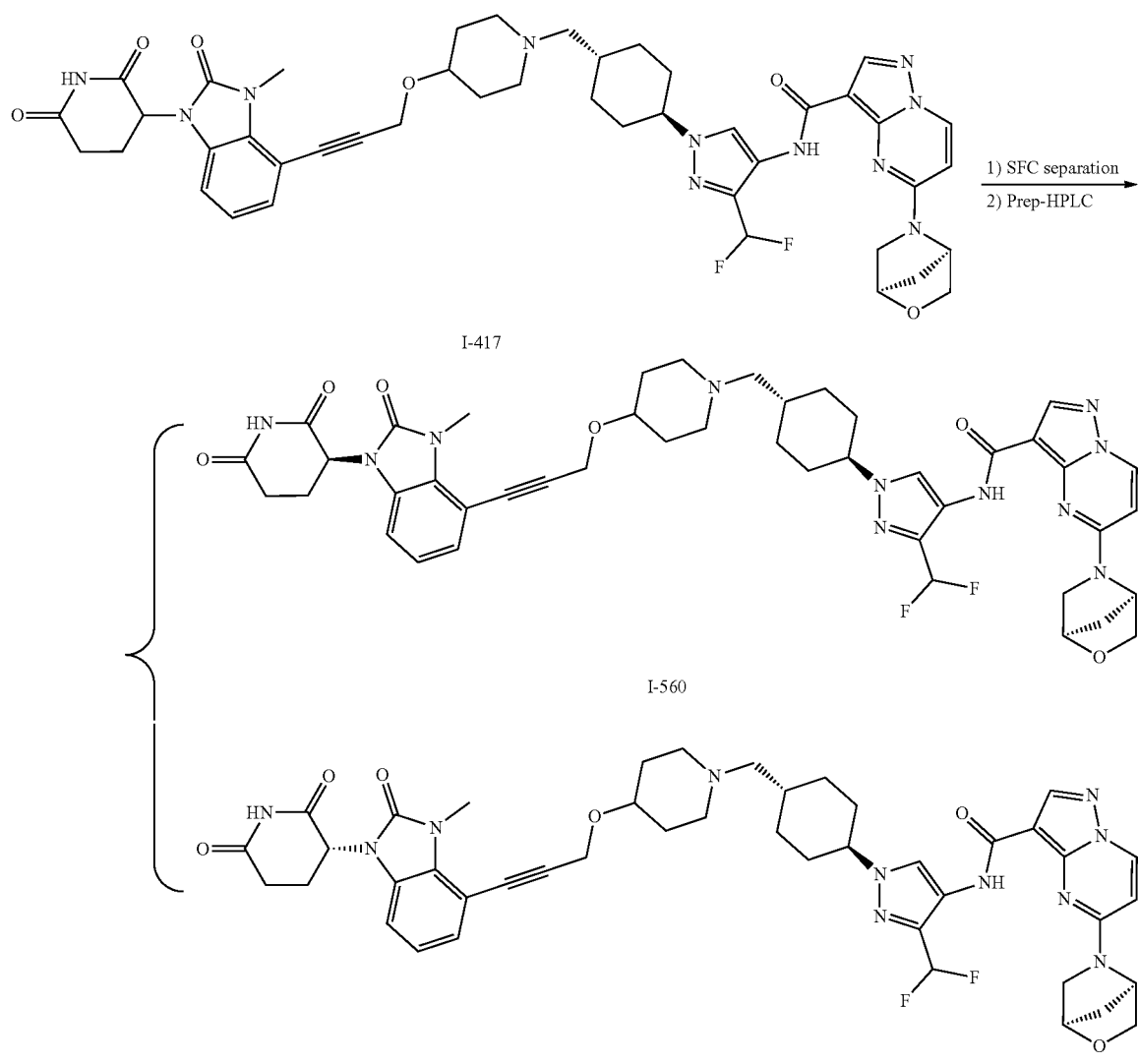

The compound N-[3-(difluoromethyl)-1-[4-[[4-[3-[1-(2,6-dioxo-3-piperidyl)-3-methyl-2-oxo-benzimidazol-4-yl]prop-2-ynoxy]-1-piperidyl]methyl] cyclohexyl]pyrazol-4-yl]-5-[(1R,4R)-2-oxa-5-azabicyclo[2.2.1]heptan-5-yl] pyrazolo[1,5-a]pyrimidine-3-carboxamide (1.00 g, 1.15 mmol, I-417) was carried out on a super-fluid chromatography unit using Sample preparation (Add ACN+DCM+THF 80 mL into sample Instrument: Waters 80 SFC Mobile Phase: 80% IPA+ACN (0.1% $NH_3 \cdot H_2O$) in Supercritical $CO_2$ Flow Rate: 80 g/min Cycle Time: 3.25 min, total time: 422 min Single injection volume: 0.8 mL Back Pressure: 100 bar to keep the $CO_2$ in Supercritical flow). This afforded two enantiomers: N-[3-(difluoromethyl)-1-[4-[[4-[3-[1-[(3S)-2,6-dioxo-3-piperidyl]-3-methyl-2-oxo-benzimidazol-4-yl]prop-2-ynoxy]-1-piperidyl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (612 mg, 57% yield, 98% ee, FA salt, retention time of 4.96 min) as white solid and N-[3-(difluoromethyl)-1-[4-[[4-[3-[1-[(3R)-2,6-dioxo-3-piperidyl]-3-methyl-2-oxo-benzimidazol-4-yl]prop-2-ynoxy]-1-piperidyl]methyl]cyclohexyl]pyrazol-4-yl]-5-[(1R,4R)-2-oxa-5-azabicyclo[2.2.1]heptan-5-yl] pyrazolo[1,5-a]pyrimidine-3-carboxamide (552 mg, 51% yield, 95% ee, FA salt, retention time of 6.44 min) as white solid. The absolute configuration of the stereoisomers was randomly assigned. Characterization of N-[3-(difluoromethyl)-1-[4-[[4-[3-[1-[(3S)-2,6-dioxo-3-piperidyl]-3-methyl-2-oxo-benzimidazol-4-yl]prop-2-ynoxy]-1-piperidyl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide: $^1$H NMR (400 MHz, DMSO-$d_6$) δ 11.12 (s, 1H), 9.49 (d, J=6.0 Hz, 1H), 8.77 (d, J=7.6 Hz, 1H), 8.38 (d, J=4.4 Hz, 1H), 8.25 (d, J=5.6 Hz, 1H), 7.27-6.95 (m, 4H), 6.89-6.41 (m, 1H), 5.40 (dd, J=5.2, 12.8 Hz, 1H), 5.30-5.04 (m, 1H), 4.76 (d, J=16.0 Hz, 1H), 4.47 (s, 2H), 4.21-4.12 (m, 1H), 3.84-3.78 (m, 1H), 3.73 (d, J=7.6 Hz, 1H), 3.64 (s, 3H), 3.62-3.58 (m, 2H), 3.58-3.41 (m, 1H), 2.94-2.83 (m, 1H), 2.78-2.67 (m, 3H), 2.65-2.59 (m, 1H), 2.15-1.85 (m, 13H), 1.80-1.67 (m, 2H), 1.63-1.44 (m, 3H), 1.09-0.95 (m, 2H); LC-MS (ESI$^+$) m/z 866.5 (M+H)$^+$. Characterization of N-[3-(difluoromethyl)-1-[4-[[4-[3-[1-[(3R)-2,6-dioxo-3-piperidyl]-3-methyl-2-oxo-benzimidazol-4-yl]prop-2-ynoxy]-1-piperidyl]methyl] cyclohexyl]pyrazol-4-yl]-5-[(1R,4R)-2-oxa-5-azabicyclo[2.2.1]heptan-5-yl]pyrazolo[1,5-a] pyrimidine-3-carboxamide: $^1$H NMR (400 MHz, DMSO-$d_6$) δ 11.12 (s, 1H), 9.50 (d, J=6.0 Hz, 1H), 8.78 (d, J=7.6 Hz, 1H), 8.38 (d, J=4.4 Hz, 1H), 8.25 (d, J=5.6 Hz, 1H), 7.26-6.95 (m, 4H), 6.88-6.42 (m, 1H), 5.40 (dd, J=5.2, 12.8 Hz, 1H), 5.31-5.01 (m, 1H), 4.76 (d, J=16.4 Hz, 1H), 4.47 (s, 2H), 4.21-4.11 (m, 1H), 3.84-3.78 (m, 1H), 3.74 (d, J=7.6 Hz, 1H), 3.64 (s, 3H), 3.62-3.58 (m, 2H), 3.58-3.41 (m, 1H), 2.94-2.84 (m, 1H), 2.78-2.67 (m, 3H), 2.66-2.59 (m, 1H), 2.16-1.85 (m, 13H), 1.80-1.66 (m, 2H), 1.61-1.43 (m, 3H), 1.05-1.02 (m, 2H); LC-MS (ESI$^+$) m/z 866.5 (M+H)$^+$.

Example 49. Synthesis of N-[3-(difluoromethyl)-1-[4-[[4-[[[2-(2,6-dioxo-3-piperidyl)-1,3-dioxo-isoindolin-4-yl] amino] methyl]-1-piperidyl] methyl] phenyl] pyrazol-4-yl]-5-[(1R)-2-oxa-5-azabicyclo[2.2.1]heptan-5-yl] pyrazolo[1,5-a]pyrimidine-3-carboxamide (I-439)

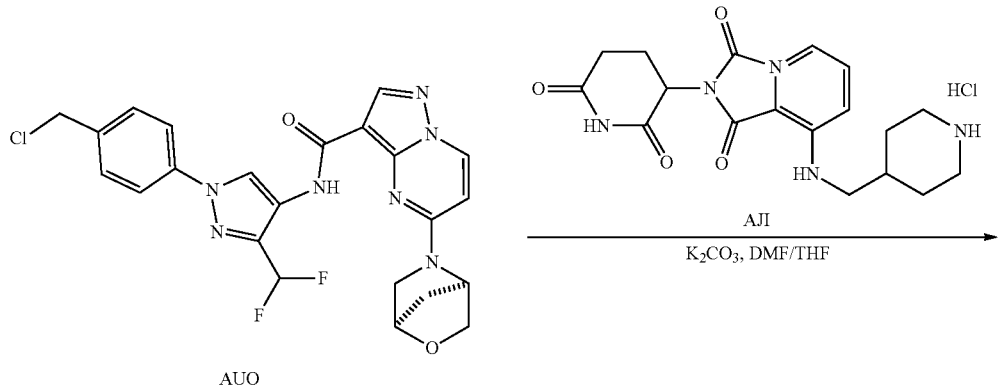

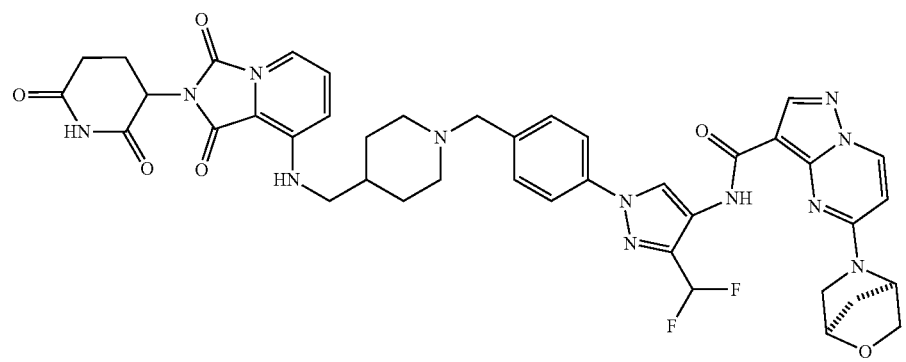

To a mixture of N-[1-[4-(chloromethyl)phenyl]-3-(difluoromethyl)pyrazol-4-yl]-5-[(1R)-2-oxa-5-azabicyclo[2.2.1]heptan-5-yl]pyrazolo[1,5-a]pyrimidine-3-carboxamide (200 mg, 400 umol, Intermediate AUO) and 2-(2,6-dioxo-3-piperidyl)-4-(4-piperidylmethylamino)isoindoline-1,3-dione (162 mg, 400 umol, HCl salt, Intermediate AJI) in THF (5 mL) and DMF (1 mL) was added K$_2$CO$_3$ (165 mg, 1.20 mmol). The reaction mixture was stirred at 60° C. for 12 hours. On completion, the reaction mixture was filtered and concentrated in vacuo. The residue was purified by prep-HPLC (column: Phenomenex Synergi C18 150*25*10 um; mobile phase: [water (0.225% FA)-ACN]; B %: 19%-49%, 10 min) to give the title compound (35.1 mg, 9% yield) as yellow solid. $^1$H NMR (400 MHz, DMSO-d$_6$) δ 11.09 (s, 1H), 9.61 (d, J=4.4 Hz, 1H), 8.96 (d, J=2.8 Hz, 1H), 8.80 (d, J=7.6 Hz, 1H), 8.34-8.27 (m, 1H), 7.78 (d, J=8.4 Hz, 2H), 7.61-7.50 (m, 1H), 7.44 (d, J=8.4 Hz, 2H), 7.30-7.00 (m, 3H), 6.93-6.43 (m, 2H), 5.32-5.01 (m, 2H), 4.78 (d, J=13.6 Hz, 1H), 3.83 (s, 1H), 3.76-3.61 (m, 2H), 3.53-3.45 (m, 4H), 3.25-3.18 (m, 2H), 2.94-2.79 (m, 3H), 2.63-2.53 (m, 2H), 2.08-1.86 (m, 4H), 1.73-1.62 (m, 2H), 1.62-1.52 (m, 1H), 1.33-1.18 (m, 2H); LC-MS (ESI$^+$) m/z 834.4 (M+H)$^+$.

Example 50. Synthesis of N-[3-(difluoromethyl)-1-[4-[[[4-[3-(difluoromethyl)-4-[(5-morpholinopyrazolo[1,5-a] pyrimidine-3-carbonyl)amino]pyrazol-1-yl]cyclohexyl]methylamino]methyl]cyclohexyl]pyrazol-4-yl]-5-morpholino-pyrazol [1,5-a] pyrimidine-3-carboxamide (I-408)

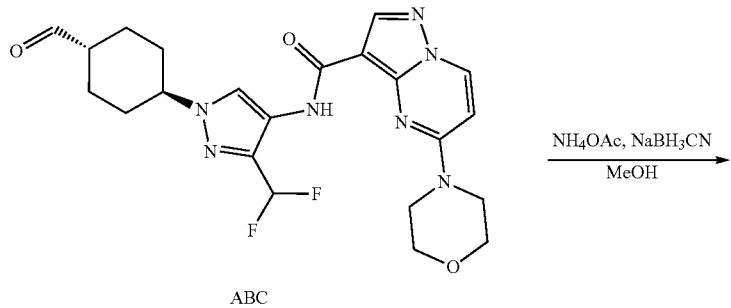

ABC

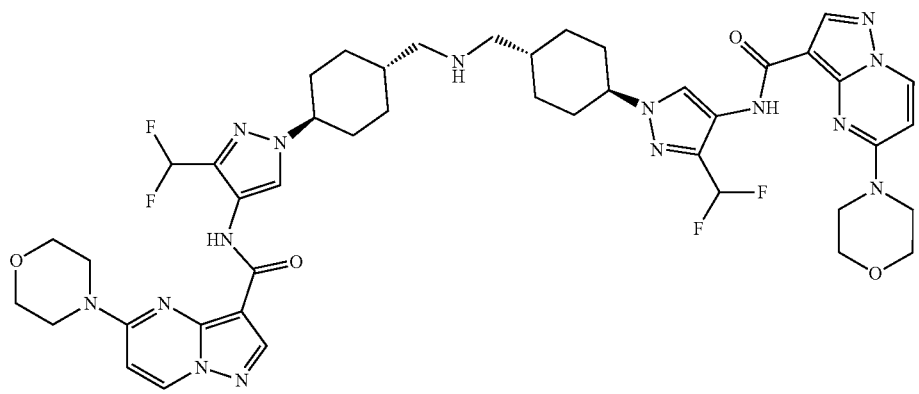

To a mixture of N-[3-(difluoromethyl)-1-(4-formylcyclohexyl)pyrazol-4-yl]-5-morpholino-pyrazolo [1,5-a]pyrimidine-3-carboxamide (0.50 g, 1.06 mmol, Intermediate ABC) in MeOH (100 mL) was added NH$_4$OAc (814 mg, 10.56 mmol). The mixture was stirred at 20° C. for 1 hour. Then NaBH$_3$CN (99.5 mg, 1.58 mmol) was added into the mixture. The mixture was stirred at 20° C. for 12 hours. On completion, the reaction mixture was quenched by water (5 mL) and filtered to give the filtrate. The filtrate was concentrated in vacuo to give the residue. The residue was purified by prep-HPLC (column: Shim-pack C18 150*25*10 um; mobile phase: [water (0.225% FA)-ACN]; B %: 22%-52%) to give the title compound (87.0 mg, 8% yield) as an off-white solid. $^1$H NMR (400 MHz, DMSO-d$_6$) δ 9.40 (s, 2H), 8.82 (d, J=8.0 Hz, 2H), 8.46-8.37 (m, 2H), 8.31-8.22 (m, 2H), 7.28-6.95 (m, 2H), 6.90 (d, J=8.0 Hz, 2H), 4.26-4.15 (m, 2H), 3.79 (s, 8H), 3.74-3.70 (m, 8H), 2.67 (d, J=2.8 Hz, 1H), 2.62 (d, J=6.4 Hz, 3H), 2.11-2.03 (m, 4H), 1.93 (d, J=12.0 Hz, 4H), 1.80-1.69 (m, 4H), 1.63 (s, 3H), 1.25-1.03 (m, 4H); LC-MS (ESI$^+$) m/z 931.9 (M+H)$^+$.

Example 51. Synthesis of N-[1-[4-[[5-aminopent-3-ynyl(methyl)amino]methyl]cyclohexyl]-3-(difluoromethyl)pyrazol-4-yl]-5-morpholino-pyrazolo [1,5-a]pyrimidine-3-carboxamide (I-412)

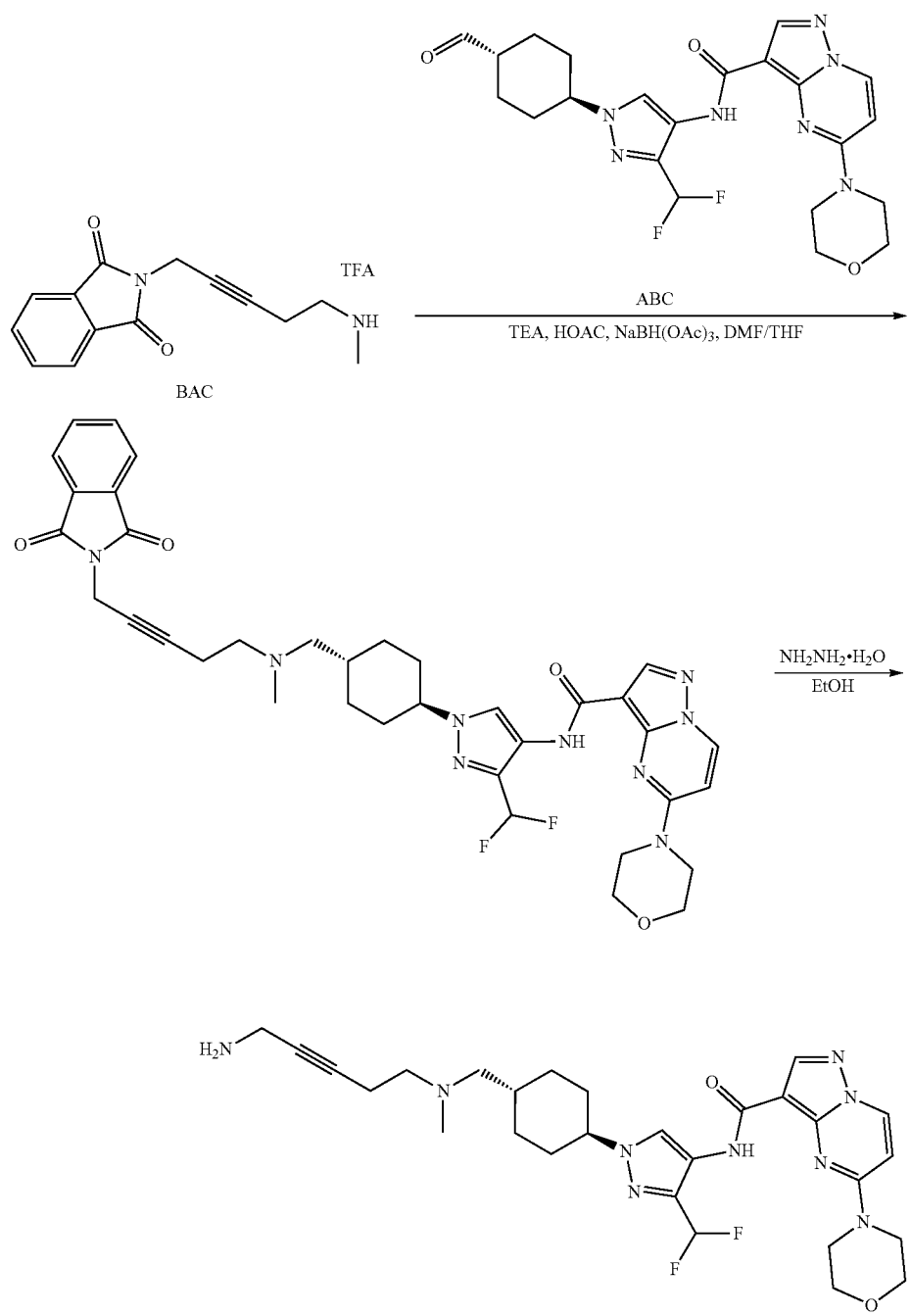

Step 1—N-[3-(difluoromethyl)-1-[4-[[5-(1,3-dioxoisoindolin-2-yl)pent-3-ynyl-methyl-amino] methyl] cyclohexyl]pyrazol-4-yl]-5-morpholino-pyrazolo[1,5-a]pyrimidine-3-carboxamide To a mixture of 2-[5-(methylamino)pent-2-ynyl]isoindoline-1,3-dione (90.0 mg, 252 umol, TFA salt, Intermediate BAC) in a mixed solvent of THF (2 mL) and DMF (0.5 mL) was added TEA (51.1 mg, 505 umol) at 0° C. The mixture was stirred at 0° C. for 30 minutes. Then N-[3-(difluoromethyl)-1-(4-formylcyclohexyl) pyrazol-4-yl]-5-morpholino-pyrazolo[1,5-a]pyrimidine-3-carboxamide (119 mg, 252 umol, Intermediate ABC) and HOAc (30.3 mg, 505 umol) was added. The mixture was at 0° C. for 30 minutes. After that, NaBH(OAc)$_3$ (107 mg, 505 umol) was added. The mixture was stirred at 0° C. for 2 hours. On completion, the reaction mixture was quenched with water (0.2 mL) at 0° C. and concentrated in vacuo. The residue was purified by prep-HPLC (column: Phenomenex Gemini-NX C18 75*30 mm*3 um; mobile phase: [water (0.1% TFA)-ACN]; B %: 20%-50%, 7 min) to afford the title compound (55 mg, 31% yield) as a white solid. $^1$H NMR (400 MHz, DMSO-d$_6$) δ 9.41 (s, 1H), 9.14 (d, J=3.2 Hz, 1H), 8.84 (d, J=8.0 Hz, 1H), 8.39 (s, 1H), 8.30 (s, 1H), 7.96-7.85 (m, 4H), 7.27-6.95 (m, 1H), 6.92 (d, J=8.0 Hz, 1H), 4.40 (s, 2H), 4.23-4.12 (m, 1H), 3.80 (s, 4H), 3.73 (d, J=4.4 Hz, 4H), 3.34-3.16 (m, 2H), 3.06 (d, J=4.0 Hz, 1H), 2.99-2.88 (m, 1H), 2.81 (d, J=4.0 Hz, 3H), 2.72 (d, J=7.2 Hz, 2H), 2.07-1.72 (m, 7H), 1.22-1.05 (m, 2H). LC-MS (ESI$^+$) m/z 700.4 (M+H)$^+$.

Step 2—N-[1-[4-[[5-aminopent-3-ynyl(methyl)amino]methyl]cyclohexyl]-3-(difluoromethyl)pyrazol-4-yl]-5-morpholino-pyrazolo[1,5-a]pyrimidine-3-carboxamide To a mixture of N-[3-(difluoromethyl)-1-[4-[[5-(1,3-dioxoisoindolin-2-yl)pent-3-ynyl-methyl-amino] methyl]cyclohexyl]pyrazol-4-yl]-5-morpholino-pyrazolo[1,5-a]pyrimidine-3-carboxamide (40.0 mg, 57.2 umol) in EtOH (2.0 mL) was added NH$_2$NH$_2$H$_2$O (14.3 mg, 285 umol) at 25° C. The mixture was stirred at 80° C. for 2 hours. On completion, the mixture was filtered and the filtrate was concentrated in vacuo. The residue was purified by prep-HPLC (column: Phenomenex Gemini-NX C18 75*30 mm*3 um; mobile phase: [water (0.1% TFA)-ACN]; B %: 8%-38%, 7 min) to afford the title compound (30.6 mg, 94% yield) as a yellow solid. $^1$H NMR (400 MHz, DMSO-d$_6$) δ 9.41 (s, 1H), 8.83 (d, J=8.0 Hz, 1H), 8.40 (s, 1H), 8.28 (s, 1H), 8.21-8.10 (m, 2H), 7.23-6.95 (m, 1H), 6.92 (d, J=8.0 Hz, 1H), 4.28-4.18 (m, 1H), 3.79 (d, J=3.2 Hz, 4H), 3.74-3.70 (m, 5H), 3.09-2.97 (m, 2H), 2.87-2.74 (m, 5H), 2.10-2.07 (m, 3H), 1.98-1.74 (m, 6H), 1.29-1.07 (m, 3H). LC-MS (ESI$^+$) m/z 570.2 (M+H)$^+$.

Example 52. Synthesis of N-[3-(difluoromethyl)-1-[4-[[4-[3-[3-methyl-1-(1-methyl-2,6-dioxo-3-piperidyl)-2-oxo-benzimidazol-4-yl]prop-2-ynoxy]-1-piperidyl]methyl] cyclohexyl] pyrazol-4-yl]-5-[(1R,4R)-2-oxa-5-azabicyclo [2.2.1]heptan-5-yl] pyrazolo[1,5-a] pyrimidine-3-carboxamide (I-563)

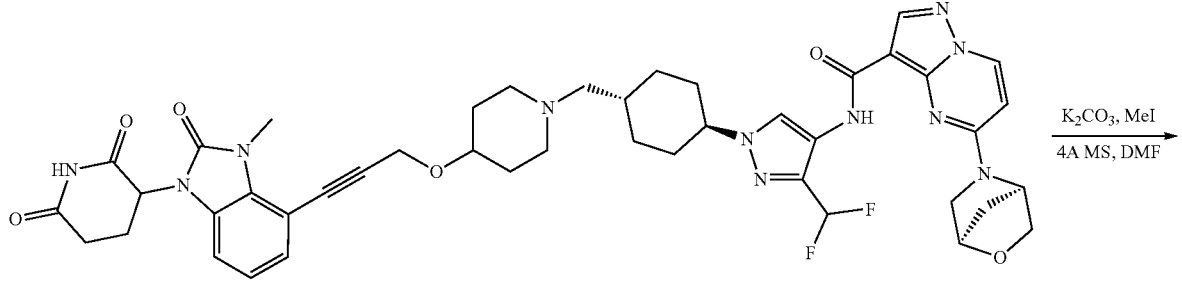

K$_2$CO$_3$, MeI
4A MS, DMF

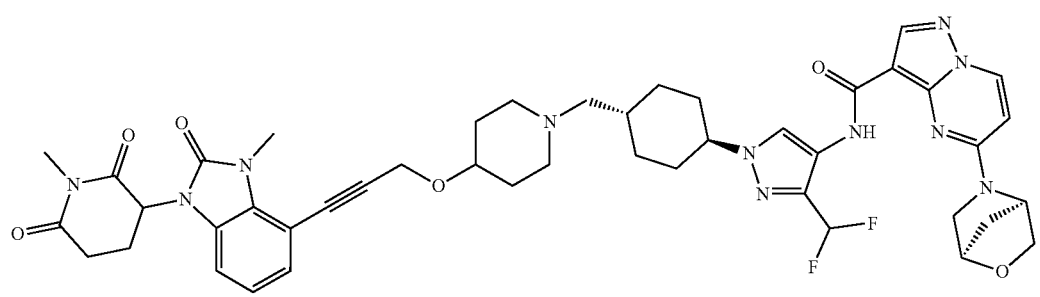

To a solution of N-[3-(difluoromethyl)-1-[4-[[4-[3-[1-(2,6-dioxo-3-piperidyl)-3-methyl-2-oxo-benzimidazol-4-yl]prop-2-ynoxy]-1-piperidyl]methyl]cyclohexyl]pyrazol-4-yl]-5-[(1R,4R)-2-oxa-5-azabicyclo[2.2.1]heptan-5-yl]pyrazolo[1,5-a]pyrimidine-3-carboxamide (300 mg, 346 umol, I-417) and 4 Å molecular sieves (60 mg) in DMF (1 mL) was added K$_2$CO$_3$ (95.8 mg, 693 umol) at 0° C. Thirty minutes later, MeI (54.1 mg, 381 umol) was added and the reaction mixture was stirred at 20° C. for 1 hr. On completion, the reaction mixture was filtered and the filtrate was concentrated in vacuo. The residue was purified by prep-HPLC (column: Waters Xbridge C18 150*50 mm*10 um; mobile phase: [water (10 mM NH$_4$HCO$_3$)-ACN]; B %: 32%-62%, 10 min) to give the title compound (29.0 mg, 9.5% yield) as a white solid. $^1$H NMR (400 MHz, DMSO-d$_6$) 9.50 (d, J=6.0 Hz, 1H), 8.78 (d, J=7.6 Hz, 1H), 8.38 (d, J=4.4 Hz, 1H), 8.26 (d, J=5.6 Hz, 1H), 7.26-6.96 (m, 4H), 6.90-6.43 (m, 1H), 5.47 (dd, J=5.2, 12.8 Hz, 1H), 5.31-5.04 (m, 1H), 4.77 (d, J=17.2 Hz, 1H), 4.48 (s, 2H), 4.25-4.09 (m, 1H), 3.88-3.72 (m, 2H), 3.65 (s, 3H), 3.63-3.42 (m, 3H), 3.04 (s, 3H), 3.01-2.93 (m, 1H), 2.82-2.64 (m, 4H), 2.12-1.86 (m, 13H), 1.80-1.67 (m, 2H), 1.59-1.39 (m, 3H), 1.11-0.92 (m, 2H); LC-MS (ESI$^+$) m/z 880.5 (M+H)$^+$.

Example 53. IMQ (Imiquimod) Induced Psoriasis

A model of psoriasis includes the effects of degrader on epidermal hyperplasia development induced by daily topical application of 5% imiquimod in C57BL/6 mice. On each of Days 0 to 6, mice had 5% imiquimod cream administered topically on left ear and shaved back skin. Control mice (no imiquimod group) received control cream without imiquimod. Mice were dosed orally with degrader I-417 2 to 4 hours before the imiquimod application that day. The last dosing was on Day 6 for all mice. All dosing was at the same time (+/−1 hour) each day. For the BID groups there was no less than 9 and no more than 15 hours between doses. Readouts were body weight, PASI score, and skin thickness. Body weight was measured 3 times/week, starting on Day −3. Once on each of Days 0, 3, 5, 6, and 7, back and ear thickness was measured with calipers. Each measurement was performed blind, by a person unaware of the group or previous measurement. On Day 7, approximately 24 hours after the last imiquimod application, all mice were euthanized and blood collected via cardiac bleed into EDTA tubes. Plasma was isolated, and frozen. Tissues of interest were removed, weighed, recorded and frozen.

FIG. 36 shows that I-417 significantly reduced skin thickening in mice treated with topical imiquimod.

Example 54. MSU Peritonitis

C57BL/6 mice were dosed with vehicle, positive control or I-30 30 minutes prior to intraperitoneal injection of 3 mg of monosodium urate crystals in 0.5-ml sterile PBS. After 4 hours, mice were sacrificed and plasma taken by cardiac puncture, peritoneal cavities were washed with PBS and the lavage Fluid collected. Plasma and lavage fluid were analyzed for IL-1beta via ELISA (in duplicate). Lavage fluid was also analyzed for PMN recruitment by FACS using Ly6G, CD45 and L/D dye.

FIG. 37 shows that compounds of the invention significantly reduce IL-1b in peritoneal lavage and plasma IL-6 levels following IP injection of MSU crystals.

Example 55. PD Study of I-417 in Wild Type Mice

Based on the body weight, mice were randomly assigned to respective groups such that the body weights for each treatment groups are the same. All mice had starting body weight greater than 18 grams. For routine monitoring, all study animals were monitored behavior such as mobility, food and water consumption (by cage side checking only), body weight (BW), eye/hair matting and any other abnormal effect. Any mortality and/or abnormal clinical signs were recorded. Body weights of all animals were measured daily throughout the study. Body weight change, expressed in %, was calculated using the following formula:

BW change (%)=(BW$_{Day\,X}$/BW$_{Day\,1}$)×100, where BW$_{Day\,X}$ is BW on a given day, and BW$_{Day\,1}$ was BW on Day 1 (initiation of treatment).

Animals were dosed orally with 30, 100 or 300 mg/kg compound formulated in 20% HPBCD in water. At termination plasma skin and spleen were collected for analysis. Whole blood was harvested plasma by terminal bleeding into tubes containing anticoagulant, plasma harvest by centrifugation at 4500 rpm @ 5 min and store at −80° C. until analysis. Skin and Spleen were snap frozen for PD analysis.

FIG. 38 shows that dose-dependent IRAK4 knockdown was observed in wild-type mouse skin and spleen with treatment of I-417.

All of the U.S. patents, U.S. patent application publications, U.S. patent applications, foreign patents, foreign patent applications, and non-patent publications referred to in this specification are incorporated herein by reference in their entireties.

While we have described a number of embodiments of this invention, it is apparent that our basic examples may be altered to provide other embodiments that utilize the compounds and methods of this invention. Therefore, it will be appreciated that the scope of this invention is to be defined by the appended claims rather than by the specific embodiments that have been represented by way of example.

We claim:
1. A compound of formula II-a or formula II-d:

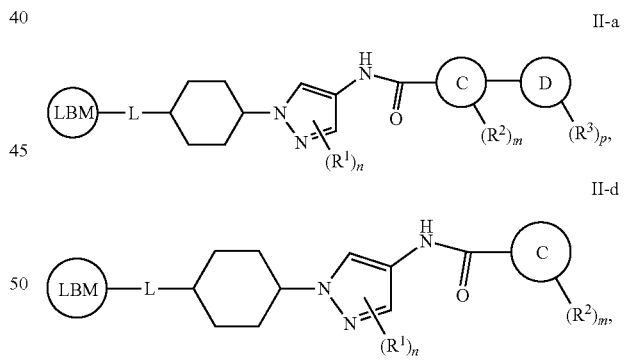

or a pharmaceutically acceptable salt thereof, wherein:
Ring C is phenyl, a 4-7 membered saturated or partially unsaturated carbocyclic ring or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;
each $R^1$ is independently hydrogen, deuterium, —$R^5$, halogen, —CN, —NO$_2$, —OR, —SR, —NR$_2$, —S(O)$_2$R, —S(O)$_2$NR$_2$, —S(O)R, —CF$_2$(R), —CF$_3$, —CR$_2$(OR), —CR$_2$(NR$_2$), —C(O)R, —C(O)OR, or —C(O)NR$_2$, or two $R^1$ on the same carbon together form =O or =S;

each R is independently hydrogen, deuterium, or an optionally substituted group selected from $C_{1-6}$ aliphatic, phenyl, a 4-7 membered saturated or partially unsaturated heterocyclic having 1-2 heteroatoms independently selected from nitrogen, oxygen, and sulfur, and a 5-6 membered heteroaryl ring having 1-4 heteroatoms independently selected from nitrogen, oxygen, and sulfur, or:
  two R groups on the same nitrogen are optionally taken together with their intervening atoms to form a 4-7 membered saturated, partially unsaturated, or heteroaryl ring having 0-3 heteroatoms, in addition to the nitrogen, independently selected from nitrogen, oxygen, and sulfur;
each $R^2$ is independently hydrogen, deuterium, —$R^5$, halogen, —CN, —$NO_2$, —OR, —SR, —$NR_2$, —$S(O)_2R$, —$S(O)_2NR_2$, —S(O)R, —$CF_2(R)$, —$CF_3$, —$CR_2(OR)$, —$CR_2(NR_2)$, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —$N(R)S(O)_2R$, or two $R^2$ on the same carbon together form =O or =S;
Ring D is phenyl, a 4-10 membered saturated or partially unsaturated mono- or bicyclic carbocyclic or heterocyclic ring having 1-3 heteroatoms independently selected from nitrogen, oxygen, and sulfur, or a 5-6 membered heteroaryl ring having 1-4 heteroatoms independently selected from nitrogen, oxygen, and sulfur;
each $R^3$ is independently hydrogen, deuterium, —$R^5$, halogen, —CN, —$NO_2$, —OR, —SR, —$NR_2$, —$S(O)_2R$, —$S(O)_2NR_2$, —S(O)R, —$CF_2(R)$, —$CF_3$, —$CR_2(OR)$, —$CR_2(NR_2)$, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —$N(R)S(O)_2R$, or two $R^3$ on the same carbon together form =O or =S;
each $R^5$ is independently an optionally substituted group selected from $C_{1-6}$ aliphatic, phenyl, a 4-7 membered saturated or partially unsaturated heterocyclic ring having 1-2 heteroatoms independently selected from nitrogen, oxygen, and sulfur, and a 5-6 membered heteroaryl ring having 1-4 heteroatoms independently selected from nitrogen, oxygen, and sulfur;
each n is 0, 1, or 2;
each m is 0, 1, 2, 3 or 4;
each p is 0, 1, 2, 3 or 4;
L is a covalent bond or a bivalent, saturated or unsaturated, straight or branched $C_{1-50}$ hydrocarbon chain, wherein 0-6 methylene units of L are independently replaced by —C(D)(H)—, —$C(D)_2$—, -Cy-, —O—, —N(R)—, —$Si(R)_2$—, —Si(OH)(R)—, —$Si(OH)_2$—, —P(O)(OR)—, —P(O)(R)—, —$P(O)(NR_2)$—, —S—, —OC(O)—, —C(O)O—, —C(O)—, —S(O)—, —$S(O)_2$—, —$N(R)S(O)_2$—, —$S(O)_2N(R)$—, —N(R)C(O)—, —C(O)N(R)—, —OC(O)N(R)—, —N(R)C(O)O—,

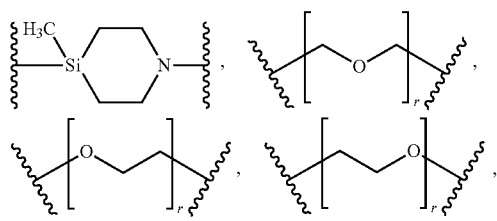

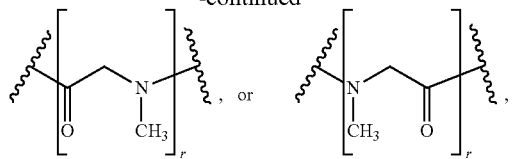

wherein
  each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur, and wherein r is 0, 1, 2, 3, 4, 5, 6, 7, 8, 9, or 10; and
LBM is a ligase binding moiety, wherein the ligase binding moiety is:

(a)

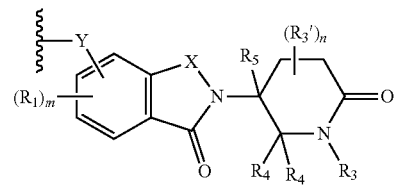

wherein:
  Y is a bond;
  X is C(O) or $CH_2$;
  each $R_1$ is independently halogen, $C_{1-4}$ alkyl, or $C_{1-4}$ alkoxy;
  each $R_3$ is H;
  two $R_4$, together with the carbon atom to which they are attached, form C(O);
  $R_5$ is H or $C_{1-3}$ alkyl;
  m is 0, 1, 2 or 3; and
  n is 0, or (b)

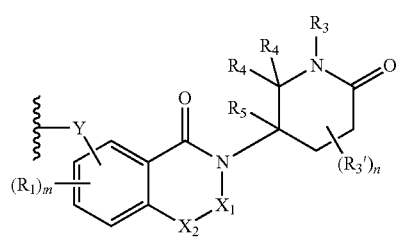

wherein:
  Y is a bond;
  X is C(O) or C(R$_3$)$_2$ CH$_2$;
  X$_1$-X$_2$ is C(H)=N, C(C$_1$-C$_4$ alkyl)=N, or C(C$_1$-C$_4$ haloalkyl);
  each R$_1$ is independently hydrogen, halogen, —NH$_2$, —OH, C$_1$-C$_6$ alkyl, C$_1$-C$_6$ haloalkyl, C$_1$-C$_6$ alkoxy, or C$_1$-C$_6$ haloalkoxy;
  R$_3$ is hydrogen;
  two R$_4$, together with the carbon atom to which they are attached, form C(O);
  R$_5$ is hydrogen or C$_1$-C$_3$ alkyl;
  m is 0, 1, 2 or 3;
  n is 0, and
wherein the compound of formula II-a is not compound I-99 in Table 1A.

2. The compound of claim 1, wherein said compound is formula II-b or II-c:

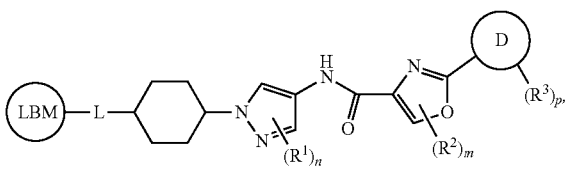

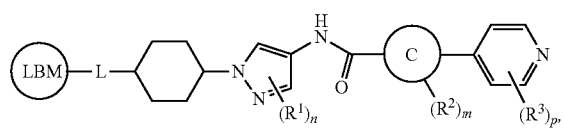

or a pharmaceutically acceptable salt thereof.

3. The compound of claim 1, wherein said compound is of formula II-o or II-q:

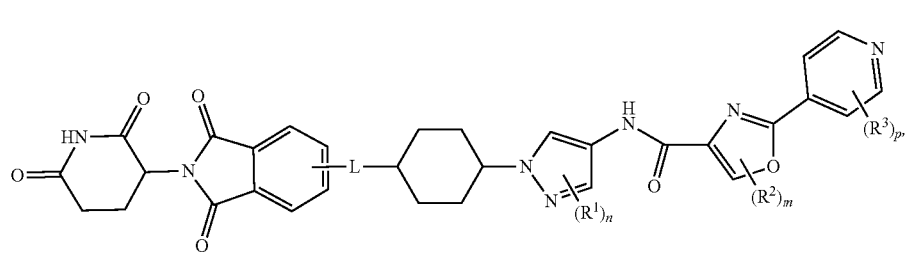

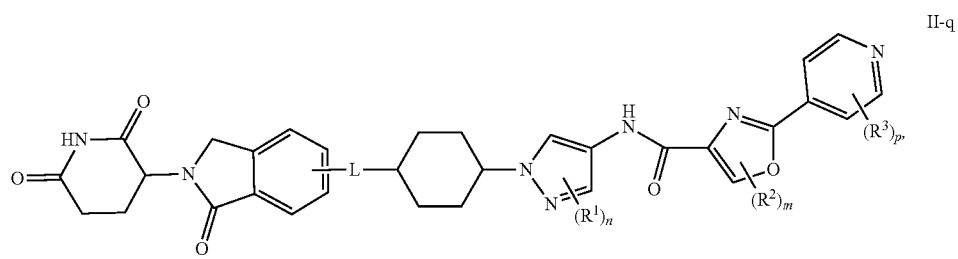

or a pharmaceutically acceptable salt thereof.

4. The compound of claim 1, wherein L is a covalent bond or a bivalent, saturated or unsaturated, straight or branched C$_{1-50}$ hydrocarbon chain, wherein 0-6 methylene units of L are independently replaced by -Cy-, —O—, —N(R)—, —C(O)—, —S(O)—, —S(O)$_2$—, —N(R)S(O)$_2$—, —S(O)$_2$N(R)—, —N(R)C(O)—, —C(O)N(R)—, —OC(O)N(R)—, —N(R)C(O)O—, wherein
  each -Cy- is independently an optionally substituted bivalent ring selected from phenylenyl, an 8-10 membered bicyclic arylenyl, a 4-7 membered saturated or partially unsaturated carbocyclylenyl, a 4-11 membered saturated or partially unsaturated spiro carbocyclylenyl, an 8-10 membered bicyclic saturated or partially unsaturated carbocyclylenyl, a 4-7 membered saturated or partially unsaturated heterocyclylenyl having 1-2 heteroatoms independently selected from nitrogen, oxygen, and sulfur, a 4-11 membered saturated or partially unsaturated spiro heterocyclylenyl having 1-2 heteroatoms independently selected from nitrogen, oxygen, and sulfur, an 8-10 membered bicyclic saturated or partially unsaturated heterocyclylenyl having 1-2 heteroatoms independently selected from nitrogen, oxygen, and sulfur, a 5-6 membered heteroarylenyl having 1-4 heteroatoms independently selected from nitrogen, oxygen, and sulfur, and an 8-10 membered bicyclic heteroarylenyl having 1-5 heteroatoms independently selected from nitrogen, oxygen, and sulfur.

5. The compound of claim 1, wherein said compound is selected from:

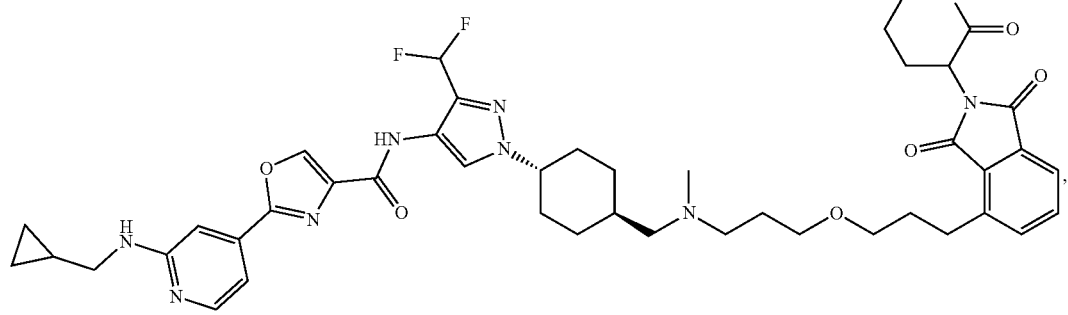

I-167

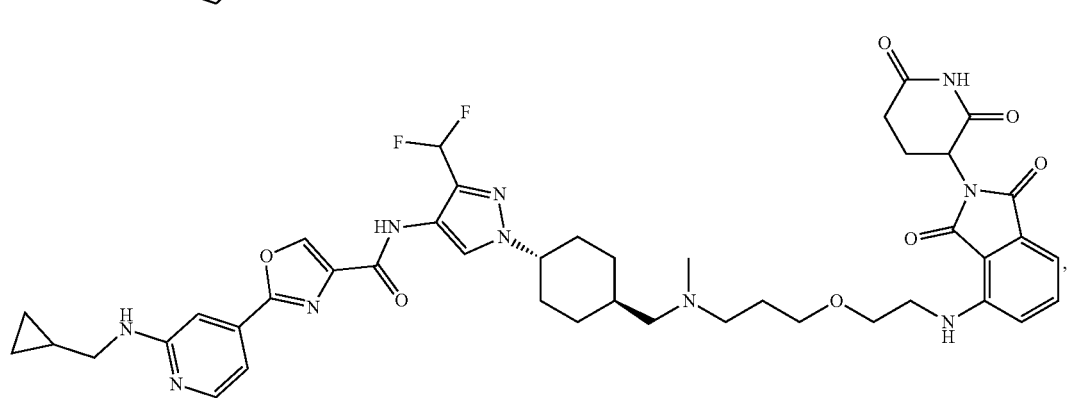

I-168

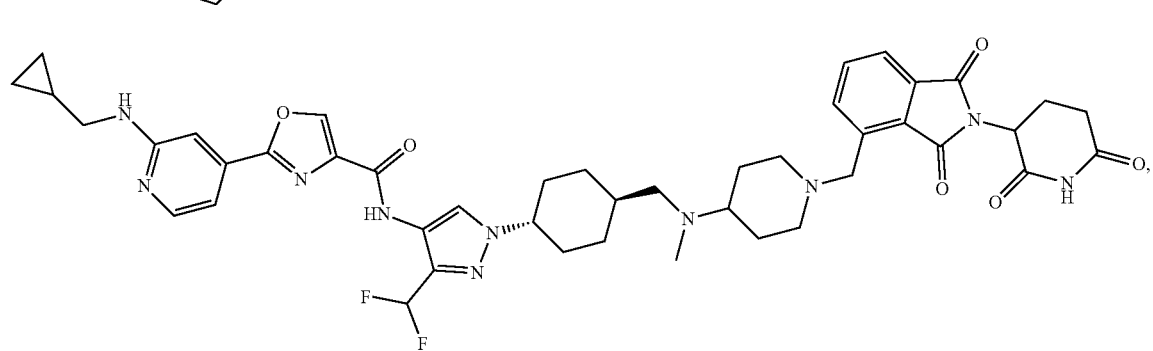

I-169

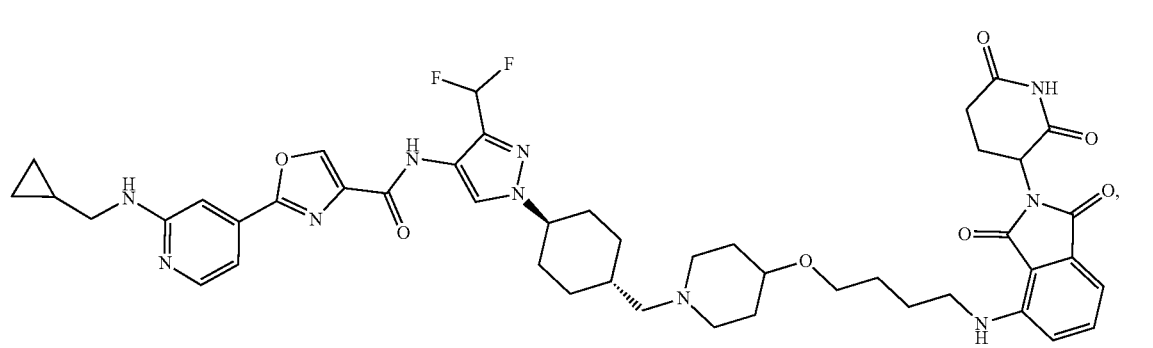

I-170

-continued
I-171
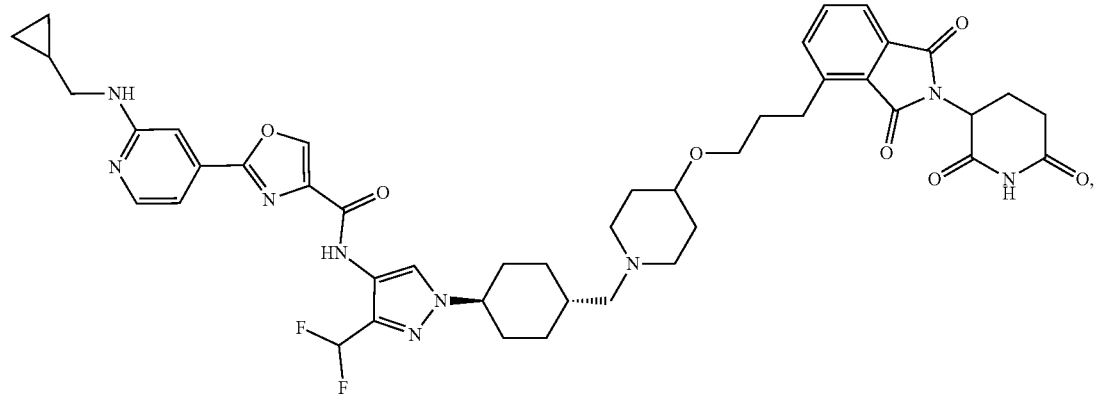
I-339
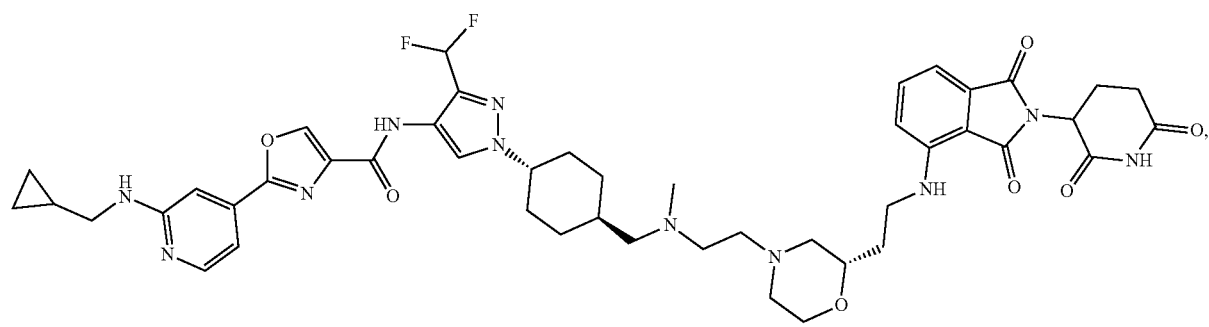
I-343
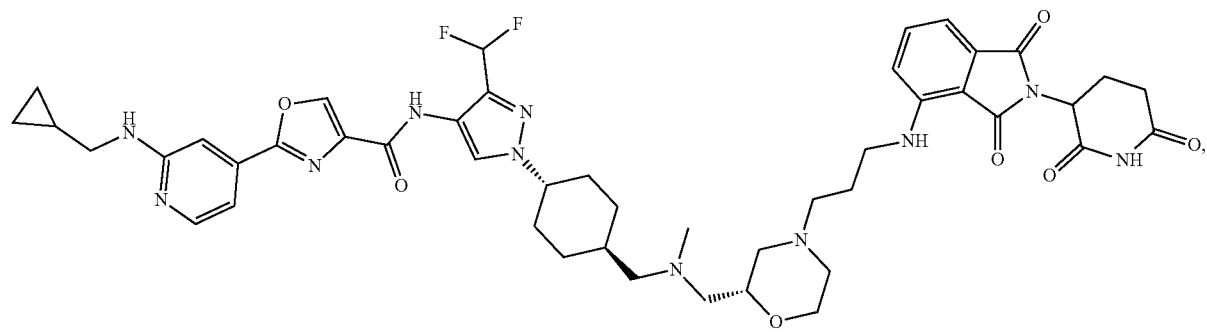
I-353
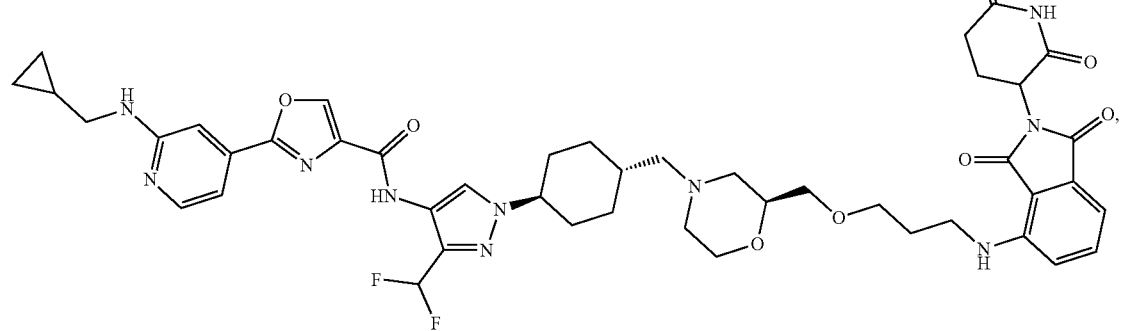

-continued
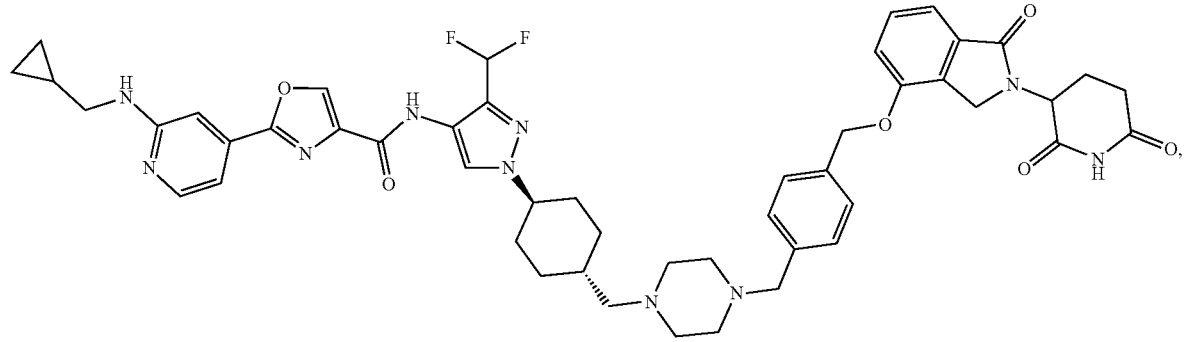
I-379
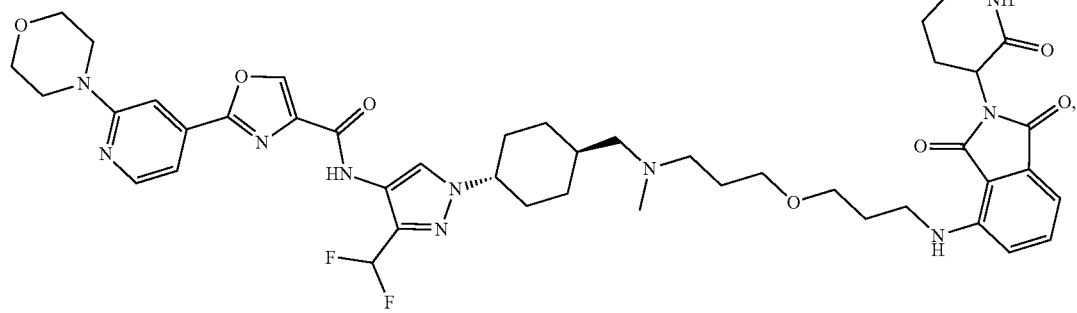
I-397
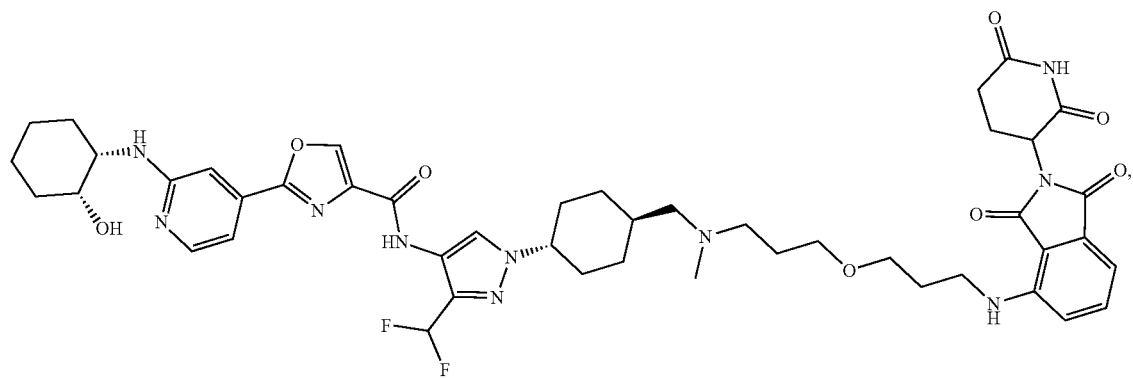
I-398
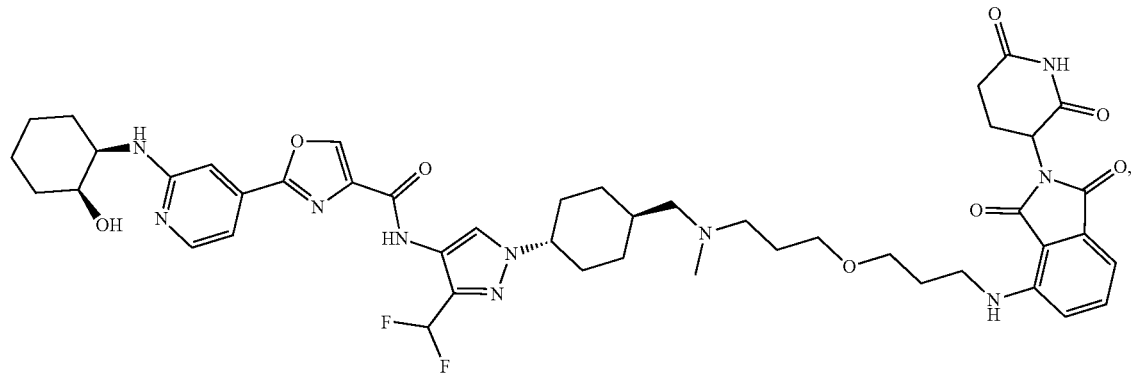
I-399

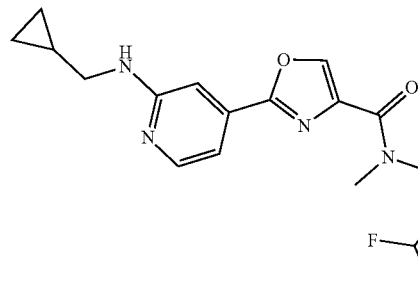
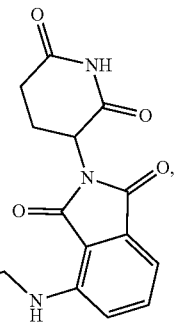

I-401

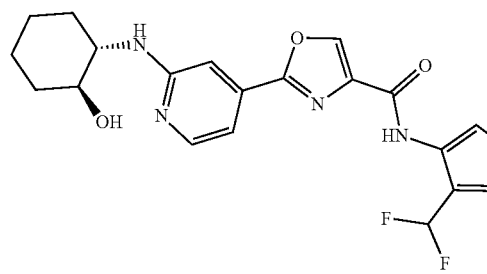
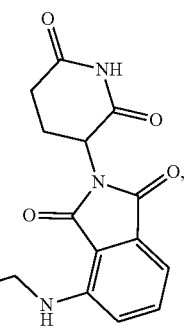

I-402 or a pharmaceutically acceptable salt thereof.

6. A pharmaceutical composition comprising a compound of claim 1, and a pharmaceutically acceptable carrier, adjuvant, or vehicle.

7. The compound of claim 1, wherein Ring C is a 5-6 membered heteroaryl ring having 1-4 heteroatoms independently selected from nitrogen, oxygen, and sulfur.

8. The compound of claim 1, wherein each $R^1$ is independently hydrogen, —$R^5$, halogen, —CN, —$NO_2$, —OR, —SR, —$NR_2$, —$S(O)_2R$, —$S(O)_2NR_2$, —$S(O)R$, —$CF_2(R)$, —$CF_3$, —$CR_2(OR)$, —$CR_2(NR_2)$, —C(O)R, —C(O)OR, or —$C(O)NR_2$.

9. The compound of claim 1, wherein each $R^2$ is independently hydrogen, —$R^5$, halogen, —CN, —$NO_2$, —OR, —SR, —$NR_2$, —$S(O)_2R$, —$S(O)_2NR_2$, —$S(O)R$, —$CF_2(R)$, —$CF_3$, —$CR_2(OR)$, —$CR_2(NR_2)$, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R.

10. The compound of claim 1, wherein Ring D is a 5-6 membered heteroaryl ring having 1-4 heteroatoms independently selected from nitrogen, oxygen, and sulfur.

11. The compound of claim 1, wherein each $R^3$ is independently hydrogen, —$R^5$, halogen, —CN, —$NO_2$, —OR, —SR, —$NR_2$, —$S(O)_2R$, —$S(O)_2NR_2$, —$S(O)R$, —$CF_2(R)$, —$CF_3$, —$CR_2(OR)$, —$CR_2(NR_2)$, —C(O)R, —C(O)OR, —$C(O)NR_2$, —C(O)N(R)OR, —OC(O)R, —OC(O)$NR_2$, —N(R)C(O)OR, —N(R)C(O)R, —N(R)C(O)$NR_2$, or —N(R)S(O)$_2$R.

* * * * *